US012709643B2

(12) United States Patent
Julia et al.

(10) Patent No.: US 12,709,643 B2
(45) Date of Patent: Aug. 18, 2026

(54) TREATMENTS FOR PRURIGO NODULARIS

(71) Applicants: GALDERMA HOLDING S.A., Zug (CH); Chugai Seiyaku Kabushiki Kaisha, Tokyo (JP)

(72) Inventors: Valerie Julia, Biot (FR); Jayendra Kumar Krishnaswamy, Pully (CH); Christophe Piketty, Montargis (FR); Francois Rousseau, Publier (FR)

(73) Assignee: Galderma Holding SA, Zug (CH)

( * ) Notice: Subject to any disclaimer, the term of this patent is extended or adjusted under 35 U.S.C. 154(b) by 637 days.

(21) Appl. No.: 17/714,847

(22) Filed: Apr. 6, 2022

(65) Prior Publication Data

US 2022/0411518 A1 Dec. 29, 2022

Related U.S. Application Data

(60) Provisional application No. 63/323,409, filed on Mar. 24, 2022, provisional application No. 63/172,020, filed on Apr. 7, 2021.

(51) Int. Cl.

*C07K 16/28* (2006.01)
*A61P 17/04* (2006.01)

(52) U.S. Cl.

CPC .......... *C07K 16/2866* (2013.01); *A61P 17/04* (2018.01)

(58) Field of Classification Search

None

See application file for complete search history.

(56) References Cited

U.S. PATENT DOCUMENTS

| | | | | |
|---|---|---|---|---|
| 10,544,227 | B2 * | 1/2020 | Kaneko | A61K 45/00 |
| 11,236,157 | B2 * | 2/2022 | Piketty | C07K 16/244 |
| 2007/0160611 | A1 * | 7/2007 | Yao | A61P 25/00 514/18.3 |
| 2011/0229459 | A1 * | 9/2011 | Kuramochi | A61P 29/00 530/387.5 |
| 2020/0239563 | A1 | 7/2020 | Piketty | |

FOREIGN PATENT DOCUMENTS

| | | | | |
|---|---|---|---|---|
| WO | WO-2006088855 A1 * | 8/2006 | | A61P 17/00 |
| WO | WO-2020/089470 A1 | 5/2020 | | |
| WO | WO-2020/157636 | 8/2020 | | |
| WO | WO-2022/215017 A1 | 10/2022 | | |

OTHER PUBLICATIONS

Oxford English Dictionary, s.v. ănormalize (v.), sense 1.a,ă Mar. 2024, https://doi.org/10.1093/OED/4420327570. Accessed Oct. 22, 2024. (Year: 2024).*

Geifman, et. al, BMC Bioinformatics, 2010, 11, 1-14 (Year: 2010).*

Yang, et. al, Open Chemistry, 2020, 18, supplemental (Year: 2020).*

Lindberg, et. al, Arth Res & Ther, 2006, 8, 1-12 (Year: 2006).*

UniProt database, https://www.uniprot.org/uniprotkb/Q8NI17/entry#names_and_taxonomy, accessed on Oct. 28, 2024 (Year: 2024).*

Pardo, et. al, Sci Rep, 2017, 7, 1-14 (Year: 2017).*

Tang, et. al, Drug Disc Today, 2021, 26, 1980-1990 (Year: 2021).*

Kwatra, et al., NEJM, 2023, 389, 1579-1589 (Year: 2023).*

Maier, et. al, J Bio Chem, 2015, 290, 24747-24759 (Year: 2015).*

Yang, et al., J Clin Pharmacol, 2019, 10, 1309-1318 (Year: 2019).*

Yang et. al, Open Chemistry, 2020, 18, 463-471 (Year: 2020).*

Yang et. al, Open Chemistry, 2020, 18, 463-471, Supplementary Material (Year: 2020).*

International Search Report and Written Opinion issued in connection with PCT International Patent Application No. PCT/IB2023/058450 dated Feb. 2, 2024 (18 pages).

Anonymous: "45th Annual Meeting of the Arbeitsgemeinschaft Oermatologische Forschung (ADF)", Experimental Dermatology, Jan. 1, 2018 (Jan. 1, 2018), XP55944648, Retrieved from the Internet: URL:https://onlinelibrary.wiley.com/doi/ep df/10.1111/exd.13486.

Belzberg Micah et al: "Prurigo Nodularis Is Characterized by Systemic and Cutaneous T Helper 22 Immune Polarization", Journal of Investigative Dermatology, vol. 141, No. 9, Mar. 23, 2021, pp. 2208-2218.

International Search Report and Written Opinion mailed for PCT PCT/IB2022/053250 on Aug. 1, 2022.

Krull C. et al: "Increased angiogenesis and VEGF expression correlates with disease severity in prurigo patients", JEADV. Journal of the European Academy of Dermatology and Venereology., vol. 30, No. 8, Aug. 1, 2016, pp. 1357-1361.

Stander Sonja et al: "Trial of Nemolizumab in Moderate-to-severe Prurigo Nodularis", The New England Journal of Medicine, vol. 382, No. 8, Feb. 20, 2020, pp. 706-716.

Tsoi Lam C et al,"Transcriptomic characterization of prurigo nodularis and the therapeutic response to nemolizumab", Journal of Allergy and Clinical Immunology, Elsevier, Amsterdam, NL, vol. 149, No. 4, Nov. 29, 2021, pp. 1329-1339.

* cited by examiner

*Primary Examiner* — Michael Szperka
*Assistant Examiner* — Samantha Lake Hopkins
(74) *Attorney, Agent, or Firm* — Sunit Talapatra; Foley & Lardner LLP

(57) ABSTRACT

Described herein are treatments and preventions for prurigo nodularis (PN), antibodies and pharmaceutical compositions for use in the treatment or prevention of PN, and uses of an anti-IL-31RA antibody (e.g., nemolizumab) in the manufacture of a medicament for the treatment or prevention of PN. Also described herein are biomarkers of PN and methods of altering or improving these biomarkers via treatments with an antibody that binds to IL-31RA (e.g., nemolizumab).

28 Claims, 16 Drawing Sheets
(11 of 16 Drawing Sheet(s) Filed in Color)
Specification includes a Sequence Listing.

FIG. 1 CON'T

FIG. 6A
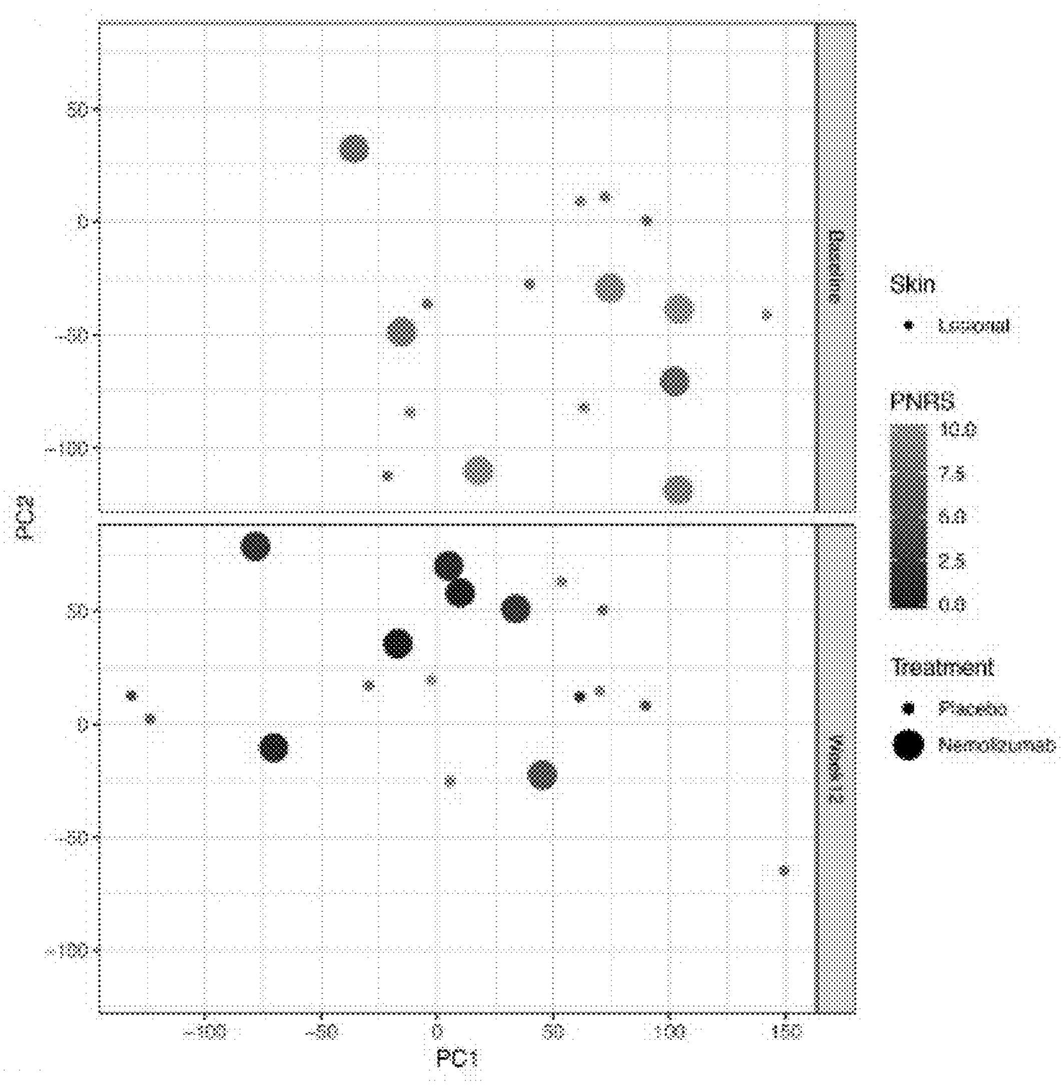
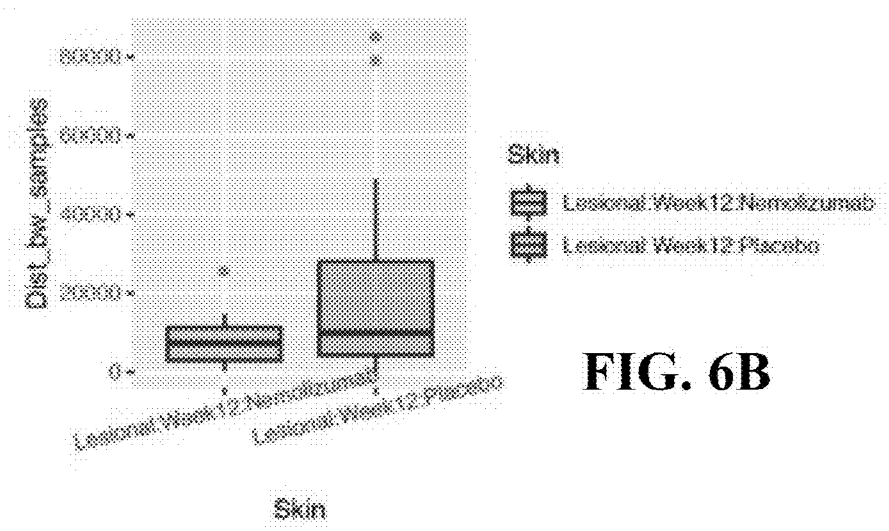
FIG. 6B

SEQUENCE LISTING

```
<160> NUMBER OF SEQ ID NOS: 14

<210> SEQ ID NO 1
<211> LENGTH: 662
<212> TYPE: PRT
<213> ORGANISM: Homo sapiens

<400> SEQUENCE: 1

Met Lys Leu Ser Pro Gln Pro Ser Cys Val Asn Leu Gly Met Met Trp
1               5                   10                  15

Thr Trp Ala Leu Trp Met Leu Pro Ser Leu Cys Lys Phe Ser Leu Ala
            20                  25                  30

Ala Leu Pro Ala Lys Pro Glu Asn Ile Ser Cys Val Tyr Tyr Tyr Arg
        35                  40                  45

Lys Asn Leu Thr Cys Thr Trp Ser Pro Gly Lys Glu Thr Ser Tyr Thr
    50                  55                  60

Gln Tyr Thr Val Lys Arg Thr Tyr Ala Phe Gly Glu Lys His Asp Asn
65                  70                  75                  80

Cys Thr Thr Asn Ser Ser Thr Ser Glu Asn Arg Ala Ser Cys Ser Phe
```

-continued

```
                85                  90                  95

Phe Leu Pro Arg Ile Thr Ile Pro Asp Asn Tyr Thr Ile Glu Val Glu
            100                 105                 110

Ala Glu Asn Gly Asp Gly Val Ile Lys Ser His Met Thr Tyr Trp Arg
        115                 120                 125

Leu Glu Asn Ile Ala Lys Thr Glu Pro Pro Lys Ile Phe Arg Val Lys
    130                 135                 140

Pro Val Leu Gly Ile Lys Arg Met Ile Gln Ile Glu Trp Ile Lys Pro
145                 150                 155                 160

Glu Leu Ala Pro Val Ser Ser Asp Leu Lys Tyr Thr Leu Arg Phe Arg
                165                 170                 175

Thr Val Asn Ser Thr Ser Trp Met Glu Val Asn Phe Ala Lys Asn Arg
            180                 185                 190

Lys Asp Lys Asn Gln Thr Tyr Asn Leu Thr Gly Leu Gln Pro Phe Thr
        195                 200                 205

Glu Tyr Val Ile Ala Leu Arg Cys Ala Val Lys Glu Ser Lys Phe Trp
    210                 215                 220

Ser Asp Trp Ser Gln Glu Lys Met Gly Met Thr Glu Glu Glu Ala Pro
225                 230                 235                 240

Cys Gly Leu Glu Leu Trp Arg Val Leu Lys Pro Ala Glu Ala Asp Gly
                245                 250                 255

Arg Arg Pro Val Arg Leu Leu Trp Lys Lys Ala Arg Gly Ala Pro Val
            260                 265                 270

Leu Glu Lys Thr Leu Gly Tyr Asn Ile Trp Tyr Tyr Pro Glu Ser Asn
        275                 280                 285

Thr Asn Leu Thr Glu Thr Met Asn Thr Thr Asn Gln Gln Leu Glu Leu
    290                 295                 300

His Leu Gly Gly Glu Ser Phe Trp Val Ser Met Ile Ser Tyr Asn Ser
305                 310                 315                 320

Leu Gly Lys Ser Pro Val Ala Thr Leu Arg Ile Pro Ala Ile Gln Glu
                325                 330                 335

Lys Ser Phe Gln Cys Ile Glu Val Met Gln Ala Cys Val Ala Glu Asp
            340                 345                 350

Gln Leu Val Val Lys Trp Gln Ser Ser Ala Leu Asp Val Asn Thr Trp
        355                 360                 365

Met Ile Glu Trp Phe Pro Asp Val Asp Ser Glu Pro Thr Thr Leu Ser
    370                 375                 380

Trp Glu Ser Val Ser Gln Ala Thr Asn Trp Thr Ile Gln Gln Asp Lys
385                 390                 395                 400

Leu Lys Pro Phe Trp Cys Tyr Asn Ile Ser Val Tyr Pro Met Leu His
                405                 410                 415

Asp Lys Val Gly Glu Pro Tyr Ser Ile Gln Ala Tyr Ala Lys Glu Gly
            420                 425                 430

Val Pro Ser Glu Gly Pro Glu Thr Lys Val Glu Asn Ile Gly Val Lys
        435                 440                 445

Thr Val Thr Ile Thr Trp Lys Glu Ile Pro Lys Ser Glu Arg Lys Gly
    450                 455                 460

Ile Ile Cys Asn Tyr Thr Ile Phe Tyr Gln Ala Glu Gly Gly Lys Gly
465                 470                 475                 480

Phe Ser Lys Thr Val Asn Ser Ser Ile Leu Gln Tyr Gly Leu Glu Ser
                485                 490                 495

Leu Lys Arg Lys Thr Ser Tyr Ile Val Gln Val Met Ala Ser Thr Ser
            500                 505                 510
```

```
Ala Gly Gly Thr Asn Gly Thr Ser Ile Asn Phe Lys Thr Leu Ser Phe
        515                 520                 525

Ser Val Phe Glu Ile Ile Leu Ile Thr Ser Leu Ile Gly Gly Gly Leu
    530                 535                 540

Leu Ile Leu Ile Ile Leu Thr Val Ala Tyr Gly Leu Lys Lys Pro Asn
545                 550                 555                 560

Lys Leu Thr His Leu Cys Trp Pro Thr Val Pro Asn Pro Ala Glu Ser
                565                 570                 575

Ser Ile Ala Thr Trp His Gly Asp Asp Phe Lys Asp Lys Leu Asn Leu
            580                 585                 590

Lys Glu Ser Asp Asp Ser Val Asn Thr Glu Asp Arg Ile Leu Lys Pro
        595                 600                 605

Cys Ser Thr Pro Ser Asp Lys Leu Val Ile Asp Lys Leu Val Val Asn
    610                 615                 620

Phe Gly Asn Val Leu Gln Glu Ile Phe Thr Asp Glu Ala Arg Thr Gly
625                 630                 635                 640

Gln Glu Asn Asn Leu Gly Gly Glu Lys Asn Gly Thr Arg Ile Leu Ser
                645                 650                 655

Ser Cys Pro Thr Ser Ile
            660


<210> SEQ ID NO 2
<211> LENGTH: 732
<212> TYPE: PRT
<213> ORGANISM: Homo sapiens

<400> SEQUENCE: 2

Met Met Trp Thr Trp Ala Leu Trp Met Leu Pro Ser Leu Cys Lys Phe
1               5                   10                  15

Ser Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Val Lys Arg Thr Tyr Ala Phe Gly Glu Lys
    50                  55                  60

His Asp Asn Cys Thr Thr Asn Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser His Met Thr
            100                 105                 110

Tyr Trp Arg Leu Glu Asn Ile Ala Lys Thr Glu Pro Pro Lys Ile Phe
        115                 120                 125

Arg Val Lys Pro Val Leu Gly Ile Lys Arg Met Ile Gln Ile Glu Trp
    130                 135                 140

Ile Lys Pro Glu Leu Ala Pro Val Ser Ser Asp Leu Lys Tyr Thr Leu
145                 150                 155                 160

Arg Phe Arg Thr Val Asn Ser Thr Ser Trp Met Glu Val Asn Phe Ala
                165                 170                 175

Lys Asn Arg Lys Asp Lys Asn Gln Thr Tyr Asn Leu Thr Gly Leu Gln
            180                 185                 190

Pro Phe Thr Glu Tyr Val Ile Ala Leu Arg Cys Ala Val Lys Glu Ser
        195                 200                 205

Lys Phe Trp Ser Asp Trp Ser Gln Glu Lys Met Gly Met Thr Glu Glu
```

-continued

```
    210                 215                 220

Glu Ala Pro Cys Gly Leu Glu Leu Trp Arg Val Leu Lys Pro Ala Glu
225                 230                 235                 240

Ala Asp Gly Arg Arg Pro Val Arg Leu Leu Trp Lys Lys Ala Arg Gly
                245                 250                 255

Ala Pro Val Leu Glu Lys Thr Leu Gly Tyr Asn Ile Trp Tyr Tyr Pro
            260                 265                 270

Glu Ser Asn Thr Asn Leu Thr Glu Thr Met Asn Thr Thr Asn Gln Gln
        275                 280                 285

Leu Glu Leu His Leu Gly Gly Glu Ser Phe Trp Val Ser Met Ile Ser
    290                 295                 300

Tyr Asn Ser Leu Gly Lys Ser Pro Val Ala Thr Leu Arg Ile Pro Ala
305                 310                 315                 320

Ile Gln Glu Lys Ser Phe Gln Cys Ile Glu Val Met Gln Ala Cys Val
                325                 330                 335

Ala Glu Asp Gln Leu Val Val Lys Trp Gln Ser Ser Ala Leu Asp Val
            340                 345                 350

Asn Thr Trp Met Ile Glu Trp Phe Pro Asp Val Asp Ser Glu Pro Thr
        355                 360                 365

Thr Leu Ser Trp Glu Ser Val Ser Gln Ala Thr Asn Trp Thr Ile Gln
    370                 375                 380

Gln Asp Lys Leu Lys Pro Phe Trp Cys Tyr Asn Ile Ser Val Tyr Pro
385                 390                 395                 400

Met Leu His Asp Lys Val Gly Glu Pro Tyr Ser Ile Gln Ala Tyr Ala
                405                 410                 415

Lys Glu Gly Val Pro Ser Glu Gly Pro Glu Thr Lys Val Glu Asn Ile
            420                 425                 430

Gly Val Lys Thr Val Thr Ile Thr Trp Lys Glu Ile Pro Lys Ser Glu
        435                 440                 445

Arg Lys Gly Ile Ile Cys Asn Tyr Thr Ile Phe Tyr Gln Ala Glu Gly
    450                 455                 460

Gly Lys Gly Phe Ser Lys Thr Val Asn Ser Ser Ile Leu Gln Tyr Gly
465                 470                 475                 480

Leu Glu Ser Leu Lys Arg Lys Thr Ser Tyr Ile Val Gln Val Met Ala
                485                 490                 495

Ser Thr Ser Ala Gly Gly Thr Asn Gly Thr Ser Ile Asn Phe Lys Thr
            500                 505                 510

Leu Ser Phe Ser Val Phe Glu Ile Ile Leu Ile Thr Ser Leu Ile Gly
        515                 520                 525

Gly Gly Leu Leu Ile Leu Ile Ile Leu Thr Val Ala Tyr Gly Leu Lys
    530                 535                 540

Lys Pro Asn Lys Leu Thr His Leu Cys Trp Pro Thr Val Pro Asn Pro
545                 550                 555                 560

Ala Glu Ser Ser Ile Ala Thr Trp His Gly Asp Asp Phe Lys Asp Lys
                565                 570                 575

Leu Asn Leu Lys Glu Ser Asp Asp Ser Val Asn Thr Glu Asp Arg Ile
            580                 585                 590

Leu Lys Pro Cys Ser Thr Pro Ser Asp Lys Leu Val Ile Asp Lys Leu
        595                 600                 605

Val Val Asn Phe Gly Asn Val Leu Gln Glu Ile Phe Thr Asp Glu Ala
    610                 615                 620

Arg Thr Gly Gln Glu Asn Asn Leu Gly Gly Glu Lys Asn Gly Tyr Val
625                 630                 635                 640
```

```
Thr Cys Pro Phe Arg Pro Asp Cys Pro Leu Gly Lys Ser Phe Glu Glu
                645                 650                 655

Leu Pro Val Ser Pro Glu Ile Pro Pro Arg Lys Ser Gln Tyr Leu Arg
            660                 665                 670

Ser Arg Met Pro Glu Gly Thr Arg Pro Glu Ala Lys Glu Gln Leu Leu
        675                 680                 685

Phe Ser Gly Gln Ser Leu Val Pro Asp His Leu Cys Glu Glu Gly Ala
    690                 695                 700

Pro Asn Pro Tyr Leu Lys Asn Ser Val Thr Ala Arg Glu Phe Leu Val
705                 710                 715                 720

Ser Glu Lys Leu Pro Glu His Thr Lys Gly Glu Val
                725                 730


<210> SEQ ID NO 3
<211> LENGTH: 716
<212> TYPE: PRT
<213> ORGANISM: Mus sp.

<400> SEQUENCE: 3

Met Trp Thr Leu Ala Leu Trp Ala Phe Ser Phe Leu Cys Lys Phe Ser
1               5                   10                  15

Leu Ala Val Leu Pro Thr Lys Pro Glu Asn Ile Ser Cys Val Phe Tyr
            20                  25                  30

Phe Asp Arg Asn Leu Thr Cys Thr Trp Arg Pro Glu Lys Glu Thr Asn
        35                  40                  45

Asp Thr Ser Tyr Ile Val Thr Leu Thr Tyr Ser Tyr Gly Lys Ser Asn
    50                  55                  60

Tyr Ser Asp Asn Ala Thr Glu Ala Ser Tyr Ser Phe Pro Arg Ser Cys
65                  70                  75                  80

Ala Met Pro Pro Asp Ile Cys Ser Val Glu Val Gln Ala Gln Asn Gly
                85                  90                  95

Asp Gly Lys Val Lys Ser Asp Ile Thr Tyr Trp His Leu Ile Ser Ile
            100                 105                 110

Ala Lys Thr Glu Pro Pro Ile Ile Leu Ser Val Asn Pro Ile Cys Asn
        115                 120                 125

Arg Met Phe Gln Ile Gln Trp Lys Pro Arg Glu Lys Thr Arg Gly Phe
    130                 135                 140

Pro Leu Val Cys Met Leu Arg Phe Arg Thr Val Asn Ser Ser Arg Trp
145                 150                 155                 160

Thr Glu Val Asn Phe Glu Asn Cys Lys Gln Val Cys Asn Leu Thr Gly
                165                 170                 175

Leu Gln Ala Phe Thr Glu Tyr Val Leu Ala Leu Arg Phe Arg Phe Asn
            180                 185                 190

Asp Ser Arg Tyr Trp Ser Lys Trp Ser Lys Glu Glu Thr Arg Val Thr
        195                 200                 205

Met Glu Glu Val Pro His Val Leu Asp Leu Trp Arg Ile Leu Glu Pro
    210                 215                 220

Ala Asp Met Asn Gly Asp Arg Lys Val Arg Leu Leu Trp Lys Lys Ala
225                 230                 235                 240

Arg Gly Ala Pro Val Leu Glu Lys Thr Phe Gly Tyr His Ile Gln Tyr
                245                 250                 255

Phe Ala Glu Asn Ser Thr Asn Leu Thr Glu Ile Asn Asn Ile Thr Thr
            260                 265                 270

Gln Gln Tyr Glu Leu Leu Leu Met Ser Gln Ala His Ser Val Ser Val
```

-continued

```
        275                 280                 285

Thr Ser Phe Asn Ser Leu Gly Lys Ser Gln Glu Ala Ile Leu Arg Ile
    290                 295                 300

Pro Asp Val His Glu Lys Thr Phe Gln Tyr Ile Lys Ser Met Lys Ala
305                 310                 315                 320

Tyr Ile Ala Glu Pro Leu Leu Val Val Asn Trp Gln Ser Ser Ile Pro
                325                 330                 335

Ala Val Asp Thr Trp Ile Val Glu Trp Leu Pro Glu Ala Ala Met Ser
            340                 345                 350

Lys Phe Pro Ala Leu Ser Trp Glu Ser Val Ser Gln Val Thr Asn Trp
        355                 360                 365

Thr Ile Glu Gln Asp Lys Leu Lys Pro Phe Thr Cys Tyr Asn Ile Ser
    370                 375                 380

Val Tyr Pro Val Leu Gly His Arg Val Gly Glu Pro Tyr Ser Ile Gln
385                 390                 395                 400

Ala Tyr Ala Lys Glu Gly Thr Pro Leu Lys Gly Pro Glu Thr Arg Val
                405                 410                 415

Glu Asn Ile Gly Leu Arg Thr Ala Thr Ile Thr Trp Lys Glu Ile Pro
            420                 425                 430

Lys Ser Ala Arg Asn Gly Phe Ile Asn Asn Tyr Thr Val Phe Tyr Gln
        435                 440                 445

Ala Glu Gly Gly Lys Glu Leu Ser Lys Thr Val Asn Ser His Ala Leu
    450                 455                 460

Gln Cys Asp Leu Glu Ser Leu Thr Arg Arg Thr Ser Tyr Thr Val Trp
465                 470                 475                 480

Val Met Ala Ser Thr Arg Ala Gly Gly Thr Asn Gly Val Arg Ile Asn
                485                 490                 495

Phe Lys Thr Leu Ser Ile Ser Val Phe Glu Ile Val Leu Leu Thr Ser
            500                 505                 510

Leu Val Gly Gly Gly Leu Leu Leu Leu Ser Ile Lys Thr Val Thr Phe
        515                 520                 525

Gly Leu Arg Lys Pro Asn Arg Leu Thr Pro Leu Cys Cys Pro Asp Val
    530                 535                 540

Pro Asn Pro Ala Glu Ser Ser Leu Ala Thr Trp Leu Gly Asp Gly Phe
545                 550                 555                 560

Lys Lys Ser Asn Met Lys Glu Thr Gly Asn Ser Gly Asp Thr Glu Asp
                565                 570                 575

Val Val Leu Lys Pro Cys Pro Val Pro Ala Asp Leu Ile Asp Lys Leu
            580                 585                 590

Val Val Asn Phe Glu Asn Phe Leu Glu Val Val Leu Thr Glu Glu Ala
        595                 600                 605

Gly Lys Gly Gln Ala Ser Ile Leu Gly Gly Glu Ala Asn Glu Tyr Val
    610                 615                 620

Thr Ser Pro Ser Arg Pro Asp Gly Pro Pro Gly Lys Ser Phe Lys Glu
625                 630                 635                 640

Pro Ser Val Leu Thr Glu Val Ala Ser Glu Asp Ser His Ser Thr Cys
                645                 650                 655

Ser Arg Met Ala Asp Glu Ala Tyr Ser Glu Leu Ala Arg Gln Pro Ser
            660                 665                 670

Ser Ser Cys Gln Ser Pro Gly Leu Ser Pro Pro Arg Glu Asp Gln Ala
        675                 680                 685

Gln Asn Pro Tyr Leu Lys Asn Ser Val Thr Thr Arg Glu Phe Leu Val
    690                 695                 700
```

```
His Glu Asn Ile Pro Glu His Ser Lys Gly Glu Val
705                 710                 715

<210> SEQ ID NO 4
<211> LENGTH: 735
<212> TYPE: PRT
<213> ORGANISM: Macaca fascicularis

<400> SEQUENCE: 4

Met Met Trp Thr Trp Ala Leu Trp Met Phe Pro Leu Leu Cys Lys Phe
1               5                   10                  15

Gly Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Ala Lys Arg Thr Tyr Ala Phe Gly Lys Lys
    50                  55                  60

His Asp Asn Cys Thr Thr Ser Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser Asp Met Thr
            100                 105                 110

Cys Trp Arg Leu Glu Asp Ile Ala Lys Thr Glu Pro Pro Glu Ile Phe
        115                 120                 125

Ser Val Lys Pro Val Leu Gly Ile Lys Arg Met Ile Arg Ile Glu Trp
    130                 135                 140

Ile Lys Pro Glu Leu Ala Pro Val Ser Ser Asp Leu Lys Tyr Ala Leu
145                 150                 155                 160

Arg Phe Arg Thr Val Asn Ser Thr Ser Trp Met Glu Val Asn Phe Ala
                165                 170                 175

Lys Asn Arg Lys Asp Thr Asn Gln Thr Tyr Asn Leu Met Gly Leu Gln
            180                 185                 190

Ala Phe Thr Glu Tyr Val Val Ala Leu Arg Cys Ala Val Lys Glu Ser
        195                 200                 205

Lys Phe Trp Ser Asp Trp Ser Gln Glu Lys Met Gly Met Thr Glu Glu
    210                 215                 220

Glu Ala Pro Cys Gly Leu Glu Leu Trp Arg Val Leu Lys Pro Thr Glu
225                 230                 235                 240

Val Asp Gly Arg Arg Pro Val Arg Leu Leu Trp Lys Lys Ala Arg Gly
                245                 250                 255

Ala Pro Val Leu Glu Lys Thr Leu Gly Tyr Asn Ile Trp Tyr Phe Pro
            260                 265                 270

Glu Asn Asn Thr Asn Leu Thr Glu Thr Val Asn Thr Thr Asn Gln Gln
        275                 280                 285

Leu Glu Leu His Leu Gly Gly Glu Ser Tyr Trp Val Ser Met Ile Ser
    290                 295                 300

Tyr Asn Ser Leu Gly Lys Ser Pro Val Thr Thr Leu Arg Ile Pro Ala
305                 310                 315                 320

Ile Gln Glu Lys Ser Phe Arg Cys Ile Glu Val Met Gln Ala Cys Leu
                325                 330                 335

Ala Glu Asp Gln Leu Val Val Lys Trp Gln Ser Ser Ala Leu Asp Val
            340                 345                 350

Asn Thr Trp Met Ile Glu Trp Phe Pro Asp Met Asp Ser Glu His Pro
```

```
        355                 360                 365

Thr Leu Ser Trp Glu Ser Val Ser Gln Ala Thr Asn Trp Thr Ile Gln
    370                 375                 380

Gln Asp Lys Leu Lys Pro Phe Trp Cys Tyr Asn Ile Ser Val Tyr Pro
385                 390                 395                 400

Met Leu His Asp Lys Val Gly Glu Pro Tyr Ser Ile Gln Ala Tyr Ala
                405                 410                 415

Lys Glu Gly Ile Pro Ser Lys Gly Pro Glu Thr Lys Val Glu Asn Ile
            420                 425                 430

Gly Val Lys Thr Val Thr Ile Thr Trp Lys Glu Ile Pro Lys Ser Glu
        435                 440                 445

Arg Lys Gly Ile Ile Cys Asn Tyr Thr Ile Phe Tyr Gln Ala Glu Gly
    450                 455                 460

Gly Lys Gly Phe Ser Lys Thr Val Asn Ser Ser Ile Leu Gln Tyr Gly
465                 470                 475                 480

Leu Glu Ser Leu Lys Arg Lys Thr Ser Tyr Thr Val Arg Val Met Ala
                485                 490                 495

Ser Thr Ser Ala Gly Gly Ile Asn Gly Thr Ser Ile Asn Phe Lys Thr
            500                 505                 510

Leu Ser Phe Ser Val Phe Glu Ile Ile Leu Ile Thr Ser Leu Ile Gly
        515                 520                 525

Gly Gly Leu Leu Ile Leu Ile Ile Leu Thr Val Ala Tyr Gly Leu Lys
    530                 535                 540

Lys Pro Asn Lys Leu Thr His Leu Cys Trp Pro Ser Val Pro Asn Pro
545                 550                 555                 560

Ala Glu Ser Ser Ile Ala Thr Trp Arg Gly Asp Asp Phe Lys Asp Lys
                565                 570                 575

Leu Asn Leu Lys Glu Ser Asp Asp Ser Val Asn Thr Glu Asp Arg Ile
            580                 585                 590

Leu Lys Pro Cys Ser Thr Pro Ser Asp Lys Leu Val Ile Asp Lys Ser
        595                 600                 605

Val Val Asn Phe Gly Asn Val Leu Gln Glu Met Phe Thr Asp Glu Ala
    610                 615                 620

Arg Thr Gly Gln Glu Asn Asn Leu Gly Gly Glu Lys Asn Glu Tyr Val
625                 630                 635                 640

Thr His Pro Phe Arg Ala Asp Cys Pro Leu Gly Lys Ser Phe Glu Glu
                645                 650                 655

Leu Pro Val Ser Pro Glu Ile Pro Pro Arg Lys Ser Gln Tyr Leu Arg
            660                 665                 670

Ser Arg Met Pro Glu Gly Thr Cys Leu Glu Ala Glu Glu Gln Leu Leu
        675                 680                 685

Val Ser Gly Gln Ser Leu Glu Ser Leu Ala Pro Asp His Val Arg Glu
    690                 695                 700

Ala Ala Ala Pro Asn Pro Tyr Leu Lys Asn Ser Val Thr Thr Arg Glu
705                 710                 715                 720

Phe Leu Val Ser Gln Lys Leu Pro Glu His Thr Lys Gly Glu Val
                725                 730                 735
```

<210> SEQ ID NO 5
<211> LENGTH: 445
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Asp Tyr Asn Pro Gln Phe
    50                  55                  60

Gln Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Leu Glu Thr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg

-continued

```
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro
        435                 440                 445


<210> SEQ ID NO 6
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asp Ile Tyr Ser Phe
            20                  25                  30

Val Ala Trp Tyr Gln Gln Lys Pro Gly Lys Ala Pro Lys Leu Leu Ile
        35                  40                  45

Tyr Asn Ala Gln Thr Glu Ala Gln Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Asp Ser Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 7
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
```

35 40 45

Gly Leu Ile Asn Pro Tyr Asn Gly Gly Thr Asp Tyr Asn Pro Gln Phe
50 55 60

Gln Asp Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Gly Tyr Asp Asp Gly Pro Tyr Thr Leu Glu Thr Trp Gly
100 105 110

Gln Gly Thr Leu Val Thr Val Ser Ser
115 120

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

Gly Tyr Ile Met Asn
1 5

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

Leu Ile Asn Pro Tyr Asn Gly Gly Thr Asp Tyr Asn Pro Gln Phe Gln
1 5 10 15

Asp

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

Asp Gly Tyr Asp Asp Gly Pro Tyr Thr Leu Glu Thr
1 5 10

<210> SEQ ID NO 11
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

Asp Ile Gln Met Thr Gln Ser Pro Ser Ser Leu Ser Ala Ser Val Gly
1 5 10 15

Asp Arg Val Thr Ile Thr Cys Gln Ala Ser Glu Asp Ile Tyr Ser Phe
20 25 30

Val Ala Trp Tyr Gln Gln Lys Pro Gly Lys Ala Pro Lys Leu Leu Ile

-continued

```
        35                  40                  45

Tyr Asn Ala Gln Thr Glu Ala Gln Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Asp Ser Pro Leu
                85                  90                  95

Thr Phe Gly Gly Gly Thr Lys Val Glu Ile Lys Arg
            100                 105


<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Ala Ser Glu Asp Ile Tyr Ser Phe Val Ala
1               5                   10


<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asn Ala Gln Thr Glu Ala Gln
1               5


<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln His His Tyr Asp Ser Pro Leu Thr
1               5
```

TREATMENTS FOR PRURIGO NODULARIS

CROSS-REFERENCE STATEMENT

This application claims priority under 35 U.S.C. § 119(e) to U.S. Provisional Application 63/172,020 filed Apr. 7, 2021, and U.S. Provision Application 63/323,409 filed Mar. 24, 2022. The entire contents of these provisional applications are incorporated herein by reference.

SEQUENCE LISTING

The instant application contains a Sequence Listing which has been submitted electronically in ASCII format and is hereby incorporated by reference in its entirety. Said ASCII copy, created on Jun. 24, 2022, is named 105153-0352_SL.txt and is 120,521 bytes in size.

STATEMENT OF GOVERNMENT SUPPORT

This invention was made with government support under Grant Nos. R01-AR069071, R01-AR073196, P30-AR075043, and K01-AR072129 awarded by the National Institutes of Health (NIH). The United States government has certain rights in the invention.

FIELD

Described herein are treatments and preventions prurigo nodularis (PN), antibodies and pharmaceutical compositions for use in the treatment or prevention of PN, and uses of an anti-IL-31RA antibody (e.g., nemolizumab) in the manufacture of a medicament for the treatment or prevention of PN. Also described herein are biomarkers of PN and methods of altering or improving these biomarkers via treatments with an antibody that binds to IL-31RA (e.g., nemolizumab).

BACKGROUND

The following discussion is provided to aid the reader in understanding the disclosure and is not admitted to describe or constitute prior art thereto.

Chronic prurigo (CP) is a skin disease due to neuronal sensitization to itch and development of an itch-scratch cycle. Prurigo nodularis (PN), a subtype of CP, is a skin disease that causes hard, itchy lumps (nodules) to form on the skin. The itching (pruritus) can be intense, causing people to scratch themselves to the point of bleeding or pain. Scratching can cause more skin lesions to appear. The itching is worsened by heat, sweating, or irritation from clothing. In some cases, people with PN have a history of other diseases including eczema (atopic dermatitis), diabetes, lymphoma, HIV infection, severe anemia, or kidney disease.

The exact cause of PN is unknown, and diagnosis of the disease is based on observing signs such as extremely itchy skin with the formation of nodules. In some cases, a skin biopsy is used to confirm the diagnosis. Currently treatment may include corticosteroid creams, oral medications, cryotherapy, or photochemotherapy.

There remains a need for treatments for PN and identifying whether patients are likely to respond or are responding to such treatments.

SUMMARY

Described herein are treatments and preventions for prurigo nodularis (PN) that achieve particular therapeutic results. In general, the treatments and preventions comprise administering to a subject with PN an anti-IL-31RA antibody (e.g., nemolizumab). Also described herein are biomarkers of PN and methods of using the disclosed biomarkers to determine whether a subject is responsive to treatment.

In a first aspect, the present disclosure provides methods of treating or preventing prurigo nodularis (PN) in a subject, comprising administering to a subject with PN an anti-IL-31RA antibody, wherein the subject differentially expresses at least one gene selected from the genes disclosed in Table 1 compared to a reference level of expression for the at least one gene.

In a second aspect, the present disclosure provides methods of normalizing differentially expressed genes (DEGs) in a subject with PN, comprising administering to a subject with PN an anti-IL-31RA antibody, wherein the subject differentially expresses at least one gene selected from the genes disclosed in Table 1 compared to a reference level of expression for the at least one gene and wherein administration of the anti-IL-31RA antibody normalizes the expression level of the at least one gene.

In some embodiments of these aspects, normalization can be determined about 4 weeks, about 8 weeks, or about 12 weeks after administration of the anti-IL-31RA antibody.

In some embodiments of these aspects, differential expression of the at least one gene can be determined by RT-qPCR, RT-PCR, RNA-seq, Northern blotting, Serial Analysis of Gene Expression (SAGE), or DNA or RNA microarrays; or differential expression of the at least one gene can be determined at protein level by Western blotting, ELISA, surface plasmon resonance, or mass spectrometry.

In some embodiments of these aspects, at least two, at least three, at least four, or at least five genes disclosed in Table 1 can be differentially expressed.

In some embodiments of these aspects, the differentially expressed gene(s) may be selected from KRT6C (keratin 6C; NCBI Entrez Gene: 286887; UniProt: P48668), DEFB4A (defensin beta 4A; NCBI Entrez Gene: 1673; UniProt: 015263), KRT16 (keratin 16; NCBI Entrez Gene: 3868; UniProt: P08779), LCE5A (late cornified envelope 5A; NCBI Entrez Gene: 254910; UniProt: Q5TCM9), AQP7 (aquaporin 7; NCBI Entrez Gene: 364; UniProt: 014520), IL36A (interleukin 36 alpha; NCBI Entrez Gene: 27179; UniProt: Q9UHA7), IL36G (interleukin 36 gamma; NCBI Entrez Gene: 56300; UniProt: Q9NZH8), IL19 (interleukin 19; NCBI Entrez Gene: 29949; UniProt: Q9UHD0), IL20 (interleukin 20; NCBI Entrez Gene: 50604; UniProt: Q9NYY1), IL22 (interleukin 22; NCBI Entrez Gene: 50616; UniProt: Q9GZX6), IL24 (interleukin 24; NCBI Entrez Gene: 11009; UniProt: Q13007), and IL26 (interleukin 26; NCBI Entrez Gene: 55801; UniProt: Q9NPH9).

In some embodiments of these aspects, KRT6C, DEFB4A, and/or KRT16 are overexpressed compared to a reference level of expression. In some embodiments of these aspects, LCE5A and/or AQP7 are under expressed compared to a reference level of expression. In some embodiments of these aspects, IL1A, IL1B, and/or IL4R are overexpressed compared to a reference level of expression. In some embodiments of these aspects, Ki67 (MKI67), CDKN1A, and/or IL-1 and IL-36 are overexpressed in the skin of the subject compared to a reference level of expression. In some embodiments of these aspects, the reference level is the level of expression in a person that does not have PN.

In some embodiments of these aspects, the subject may possess a gene ontology disclosed in Table 2.

In some embodiments of these aspects, the anti-IL-31RA antibody can be administered subcutaneously.

In some embodiments of these aspects, the anti-IL-31RA antibody can be administered once per week, once every two weeks, once every three weeks, once every four weeks, once every five weeks, once every six weeks, once every seven weeks, or once every eight weeks.

In some embodiments of these aspects, the anti-IL-31RA antibody can be administered at a dose of about 0.01 mg/kg to about 0.1 mg/kg, about 0.1 mg/kg to about 0.5 mg/kg, about 0.5 mg/kg to about 1.5 mg/kg, about 1.5 mg/kg to about 2.5 mg/kg, or about 2.5 mg/kg to about 10 mg/kg.

In some embodiments of these aspects, the anti-IL-31RA antibody can be administered at a dose of about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg.

In some embodiments of these aspects, the anti-IL-31RA antibody is administered according to a flat dosing regimen. In some embodiments of these aspects, the anti-IL-31RA antibody is administered according to a loading dose regimen.

In some embodiments of these aspects, pruritus scoring is improved in the subject.

In some embodiments of these aspects, the anti-IL-31RA antibody comprises a heavy chain variable region comprising a HCDR1 comprising SEQ ID NO: 8, a HCDR2 comprising SEQ ID NO: 9, and a HCDR3 comprising SEQ ID NO: 10, and a light chain variable region comprising a LCDR1 comprising SEQ ID NO: 12, a LCDR2 comprising SEQ ID NO: 13, and a LCDR3 comprising SEQ ID NO: 14. In some embodiments of these aspects, the anti-IL-31RA antibody is nemolizumab or a fragment or variant thereof. In some embodiments of these aspects, the anti-IL-31RA antibody is nemolizumab.

In a third aspect, the present disclosure provides methods of normalizing epidermal hyperproliferation and/or normalizing epidermal differentiation in a subject with prurigo nodularis (PN), comprising administering to a subject with PN an anti-IL-31RA antibody, thereby normalizing epidermal hyperproliferation and/or normalizing epidermal differentiation as compared to a person that does not have PN. In some embodiments, normalization can be determined about 4 weeks, about 8 weeks, or about 12 weeks after administration of the anti-IL-31RA antibody.

In a fourth aspect, the present disclosure provides methods of decreasing an inflammatory responses in the skin of a subject with prurigo nodularis (PN), comprising administering to a subject with PN an anti-IL-31RA antibody, thereby decreasing an inflammatory responses in the skin. In some embodiments, the inflammatory response can be a Th2 response and, optionally, comprises overexpression of IL-13, IL-17A, IL-1, and/or IL-36. In some embodiments, the inflammatory response can be a Th1 response In some embodiments of the third and fourth aspect, the subject may differentially express at least one gene selected from the genes disclosed in Table 1 compared to a reference level of expression for the at least one gene. In some embodiments, at least two, at least three, at least four, or at least five genes disclosed in Table 1 are differentially expressed. In some embodiments, the differentially expressed gene(s) are selected from KRT6C, DEFB4A, KRT16, LCE5A, AQP7, IL36A, IL36G, IL19, IL20, IL22, IL24, and IL26. In some embodiments, KRT6C, DEFB4A, and/or KRT16 are overexpressed compared to a reference level of expression. In some embodiments, LCE5A and/or AQP7 are under expressed compared to a reference level of expression. In some embodiments, IL1A, IL1B, and/or IL4R are overexpressed compared to a reference level of expression. In some embodiments, Ki67 (MKI67), CDKN1A, and/or IL-1 and IL-36 are overexpressed in the skin of the subject compared to a reference level of expression. In some embodiments, the reference level is the level of expression in a person that does not have PN.

In some embodiments of the third and fourth aspect, the subject may possess a gene ontology disclosed in Table 2.

In some embodiments of the third and fourth aspect, the anti-IL-31RA antibody is administered subcutaneously.

In some embodiments of the third and fourth aspect, the anti-IL-31RA antibody is administered once per week, once every two weeks, once every three weeks, once every four weeks, once every five weeks, once every six weeks, once every seven weeks, or once every eight weeks.

In some embodiments of the third and fourth aspect, the anti-IL-31RA antibody is administered at a dose of about 0.01 mg/kg to about 0.1 mg/kg, about 0.1 mg/kg to about 0.5 mg/kg, about 0.5 mg/kg to about 1.5 mg/kg, about 1.5 mg/kg to about 2.5 mg/kg, or about 2.5 mg/kg to about 10 mg/kg.

In some embodiments of the third and fourth aspect, the anti-IL-31RA antibody is administered at a dose of about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg.

In some embodiments of the third and fourth aspect, the anti-IL-31RA antibody is administered according to a flat dosing regimen. In some embodiments of the third and fourth aspect, the anti-IL-31RA antibody is administered according to a loading dose regimen.

In some embodiments of the third and fourth aspect, pruritus scoring is improved in the subject.

In some embodiments of the third and fourth aspect, the anti-IL-31RA antibody comprises a heavy chain variable region comprising a HCDR1 comprising SEQ ID NO: 8, a HCDR2 comprising SEQ ID NO: 9, and a HCDR3 comprising SEQ ID NO: 10, and a light chain variable region comprising a LCDR1 comprising SEQ ID NO: 12, a LCDR2 comprising SEQ ID NO: 13, and a LCDR3 comprising SEQ ID NO: 14. In some embodiments, the anti-IL-31RA antibody is nemolizumab or a fragment or variant thereof. In some embodiments, the anti-IL-31RA antibody is nemolizumab.

In a fifth aspect, the present disclosure provides methods of diagnosing prurigo nodularis (PN), comprising detecting in a sample obtained from a subject suspected of having PN the expression level of at least one, at least two, at least three, at least four, or at least five of the differentially expressed genes (DEGs) in Table 1, and comparing the expression level of the DEGs to a reference level, wherein the reference level is the corresponding level of gene expression for each DEG in a sample from an individual that does not have PN.

In some embodiments of the fifth aspect, the sample obtained from the subject suspected of having PN can be a skin sample, which optionally comprises a lesion or a nodule.

In some embodiments of the fifth aspect, the expression level of the DEG(s) is determined by RT-qPCR, RT-PCR, RNA-seq, Northern blotting, Serial Analysis of Gene Expression (SAGE), or DNA or RNA microarray.

In some embodiments of the fifth aspect, the DEG(s) are selected from KRT6C, DEFB4A, KRT16, LCE5A, AQP7, IL36A, IL36G, IL19, IL20, IL22, IL24, and IL26. In some embodiments, the DEG(s) comprise overexpression of KRT6C, DEFB4A, and/or KRT16 compared to the reference level of expression is indicative of PN. In some embodiments, under expression of LCE5A and/or AQP7 compared to the reference level of expression is indicative of PN. In some embodiments, the DEG(s) comprise overexpression of IL1A, IL1B, and/or IL4R compared to the reference level of expression is indicative of PN. In some embodiments, the DEG(s) comprise overexpression of Ki67 (MKI67), CDKN1A, and/or IL-1 and IL-36 compared to the reference level of expression is indicative of PN.

In some embodiments of the fifth aspect, the subject possesses a gene ontology disclosed in Table 2.

In a sixth aspect, the present disclosure provides methods of determining whether a subject with prurigo nodularis (PN) will respond to treatment with an anti-IL-31RA antibody, comprising detecting in a sample obtained from a subject with PN the expression level of at least one, at least two, at least three, at least four, or at least five of the differentially expressed genes (DEGs) in Table 1, and comparing the expression level of the DEGs to a reference level, wherein the reference level is the corresponding level of gene expression for each DEG in a sample from an individual that does not have PN.

In some embodiments of the sixth aspect, the sample obtained from the subject with PN is a skin sample, which optionally comprises a lesion or a nodule.

In some embodiments of the fifth aspect, the expression level of the DEG(s) is determined by RT-qPCR, RT-PCR, RNA-seq, Northern blotting, Serial Analysis of Gene Expression (SAGE), or DNA or RNA microarray.

In some embodiments of the sixth aspect, the DEG(s) are selected from KRT6C, DEFB4A, KRT16, LCE5A, AQP7, IL36A, IL36G, IL19, IL20, IL22, IL24, and IL26. In some embodiments, the DEG(s) comprise overexpression of KRT6C, DEFB4A, and/or KRT16 compared to the reference level of expression is indicative of PN. In some embodiments, under expression of LCE5A and/or AQP7 compared to the reference level of expression is indicative of PN. In some embodiments, the DEG(s) comprise overexpression of IL1A, IL1B, and/or IL4R compared to the reference level of expression is indicative of PN. In some embodiments, the DEG(s) comprise overexpression of Ki67 (MKI67), CDKN1A, and/or IL-1 and IL-36 compared to the reference level of expression is indicative of PN.

In some embodiments of the sixth aspect, the anti-IL-31RA antibody comprises a heavy chain variable region comprising a HCDR1 comprising SEQ ID NO: 8, a HCDR2 comprising SEQ ID NO: 9, and a HCDR3 comprising SEQ ID NO: 10, and a light chain variable region comprising a LCDR1 comprising SEQ ID NO: 12, a LCDR2 comprising SEQ ID NO: 13, and a LCDR3 comprising SEQ ID NO: 14. In some embodiments, the anti-IL-31RA antibody is nemolizumab or a fragment or variant thereof. In some embodiments, the anti-IL-31RA antibody is nemolizumab.

In a seventh aspect, the present disclosure provides methods of determining whether a subject with prurigo nodularis (PN) is responding to treatment with an anti-IL-31RA antibody, comprising detecting in a post-treatment sample obtained from a subject with PN that has been administered at least one dose of an anti-IL-31RA antibody the expression level of at least one, at least two, at least three, at least four, or at least five of the differentially expressed genes DEGs in Table 1, and comparing the expression level of the DEGs to a baseline level of expression, wherein the baseline level of gene expression is from a sample from the same individual before treatment was commenced.

In some embodiments of the seventh aspect, the sample obtained from the subject with PN is a skin sample, which optionally comprises a lesion or a nodule.

In some embodiments of the seventh aspect, the expression level of the DEG(s) is determined by RT-qPCR, RT-PCR, RNA-seq, Northern blotting, Serial Analysis of Gene Expression (SAGE), or DNA or RNA microarray.

In some embodiments of the seventh aspect, the DEG(s) are selected from KRT6C, DEFB4A, KRT16, LCE5A, AQP7, IL36A, IL36G, IL19, IL20, IL22, IL24, and IL26. In some embodiments, the DEG(s) comprise overexpression of KRT6C, DEFB4A, and/or KRT16 compared to the reference level of expression is indicative of PN. In some embodiments, under expression of LCE5A and/or AQP7 compared to the reference level of expression is indicative of PN. In some embodiments, the DEG(s) comprise overexpression of IL1A, IL1B, and/or IL4R compared to the reference level of expression is indicative of PN. In some embodiments, the DEG(s) comprise overexpression of Ki67 (MKI67), CDKN1A, and/or IL-1 and IL-36 compared to the reference level of expression is indicative of PN.

In some embodiments of the seventh aspect, the post-treatment sample is obtained about 4 weeks, about 8 weeks, or about 12 weeks after administration of the anti-IL-31RA antibody.

In some embodiments of the seventh aspect, the anti-IL-31RA antibody comprises a heavy chain variable region comprising a HCDR1 comprising SEQ ID NO: 8, a HCDR2 comprising SEQ ID NO: 9, and a HCDR3 comprising SEQ ID NO: 10, and a light chain variable region comprising a LCDR1 comprising SEQ ID NO: 12, a LCDR2 comprising SEQ ID NO: 13, and a LCDR3 comprising SEQ ID NO: 14. In some embodiments, the anti-IL-31RA antibody is nemolizumab or a fragment or variant thereof. In some embodiments, the anti-IL-31RA antibody is nemolizumab.

In an eighth aspect, the present disclosure provides methods of treating or preventing prurigo nodularis (PN) in a subject, comprising administering to a subject with PN an anti-IL-31RA antibody, wherein treatment with the anti-IL-31RA antibody results in: (a) a decrease in migration of leukocytes or cell movement of leukocytes; (b) an inhibition of a STAT3 pathway; (c) an inhibition of a STAT5b pathway; (d) a downregulation of IL-6 or an IL-6 pathway; (e) a downregulation of VEGF or a VEGF pathway; (f) a decrease in TGFB1 pathway activation, or (g) a combination thereof.

In an ninth aspect, the present disclosure provides methods of altering an immune response in a subject with PN, comprising administering to a subject with PN an anti-IL-31RA antibody, wherein administration of the anti-IL-31RA antibody results in: (a) a decrease in migration of leukocytes or cell movement of leukocytes; (b) an inhibition of a STAT3 pathway; (c) an inhibition of a STAT5b pathway; (d) a downregulation of IL-6 or an IL-6 pathway; (e) a downregulation of VEGF or a VEGF pathway; (f) a decrease in TGFB1 pathway activation, or (g) a combination thereof.

In some embodiments of the eighth and ninth aspects, (a) the decrease in migration of leukocytes or cell movement of leukocytes; (b) the inhibition of a STAT3 pathway; (c) the inhibition of a STAT5b pathway; (d) the downregulation of IL-6 or an IL-6 pathway; (e) the downregulation of VEGF or a VEGF pathway; (f) the decrease in TGFB1 pathway activation, or (g) the combination thereof is determined relative to (i) a control sample obtained from an individual or individuals without PN or (ii) a biological sample obtained from the subject prior to administration of the anti-IL-31RA antibody.

In some embodiments of the eighth and ninth aspects, (a) the decrease in migration of leukocytes or cell movement of leukocytes; (b) the inhibition of a STAT3 pathway; (c) the inhibition of a STAT5b pathway; (d) the downregulation of IL-6 or an IL-6 pathway; (e) the downregulation of VEGF or a VEGF pathway; (f) the decrease in TGFB1 pathway activation, or (g) the combination thereof is assessed after about 2 weeks, about 4 weeks, about 6 weeks, about 8 weeks, about 10 weeks, or about 12 weeks after the administration of the anti-IL-31RA antibody.

In some embodiments of the eighth and ninth aspects, (a) the decrease in migration of leukocytes or cell movement of leukocytes; (b) the inhibition of a STAT3 pathway; (c) the inhibition of a STAT5b pathway; (d) the downregulation of IL-6 or an IL-6 pathway; (e) the downregulation of VEGF or a VEGF pathway; (f) the decrease in TGFB1 pathway activation, or (g) the combination thereof is determined by mass spectrometry performed on one or more biological sample(s) obtained from the subject. In some embodiments, the biological sample is a plasma sample.

In some embodiments of the eighth and ninth aspects, the subject exhibits at least two of, at least three of, at least four of, at least five of, or all six of (a) the decrease in migration of leukocytes or cell movement of leukocytes; (b) the inhibition of a STAT3 pathway; (c) the inhibition of a STAT5b pathway; (d) the downregulation of IL-6 or an IL-6 pathway; (e) the downregulation of VEGF or a VEGF pathway; (f) the decrease in TGFB1 pathway activation.

In a tenth aspect, the present disclosure provides methods of decreasing an inflammatory response in the plasma of a subject with prurigo nodularis (PN), comprising administering to a subject with PN an anti-IL-31RA antibody, thereby decreasing the inflammatory response in the skin. In some embodiments, decreasing the inflammatory response comprises decreasing the plasma concentration of IL-6, VEGF, or a combination thereof compared to a reference level. In some embodiments, the reference level is determined from (i) a control sample obtained from an individual or individuals without PN or (ii) a biological sample obtained from the subject prior to administration of the anti-IL-31RA antibody. In some embodiments, after administration of the anti-IL-31RA antibody, the subject additionally exhibits (a) a decrease in migration of leukocytes or cell movement of leukocytes; (b) an inhibition of a STAT3 pathway; (c) an inhibition of a STAT5b pathway; (d) a decrease in TGFB1 pathway activation; or (e) a combination thereof. In some embodiments, at least 4 weeks, at least 8 weeks, or at least 12 weeks after administration of the anti-IL-31RA antibody, the subject additionally exhibits at least two, at least three, or all four of (a) a decrease in migration of leukocytes or cell movement of leukocytes; (b) an inhibition of a STAT3 pathway; (c) an inhibition of a STAT5b pathway; (d) a decrease in TGFB1 pathway activation.

In some embodiments of the eighth, ninth, or tenth aspects, the subject may also exhibit a downregulation in a neuronal ontology selected from CREB signaling in neurons, Synaptogenesis signaling pathway, Cell death of neuroglia and Apoptosis of neuroglia, and a combination thereof following administration of the anti-IL-31RA antibody.

In some embodiments of the eighth, ninth, or tenth aspects, the anti-IL-31RA antibody is administered subcutaneously. In some embodiments of the eighth, ninth, or tenth aspects, the anti-IL-31RA antibody is administered once per week, once every two weeks, once every three weeks, once every four weeks, once every five weeks, once every six weeks, once every seven weeks, or once every eight weeks.

In some embodiments of the eighth, ninth, or tenth aspects, the anti-IL-31RA antibody is administered at a dose of about 0.01 mg/kg to about 0.1 mg/kg, about 0.1 mg/kg to about 0.5 mg/kg, about 0.5 mg/kg to about 1.5 mg/kg, about 1.5 mg/kg to about 2.5 mg/kg, or about 2.5 mg/kg to about 10 mg/kg. In some embodiments of the eighth, ninth, or tenth aspects, the anti-IL-31RA antibody is administered at a dose of about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg.

In some embodiments of the eighth, ninth, or tenth aspects, the anti-IL-31RA antibody is administered according to a flat dosing regimen. In some embodiments of the eighth, ninth, or tenth aspects, the anti-IL-31RA antibody is administered according to a loading dose regimen.

In some embodiments of the eighth, ninth, or tenth aspects, pruritus scoring is improved in the subject.

In some embodiments of the eighth, ninth, or tenth aspects, the anti-IL-31RA antibody comprises a heavy chain variable region comprising a HCDR1 comprising SEQ ID NO: 8, a HCDR2 comprising SEQ ID NO: 9, and a HCDR3 comprising SEQ ID NO: 10, and a light chain variable region comprising a LCDR1 comprising SEQ ID NO: 12, a LCDR2 comprising SEQ ID NO: 13, and a LCDR3 comprising SEQ ID NO: 14. In some embodiments, the anti-IL-31RA antibody is nemolizumab or a fragment or variant thereof. In some embodiments, the anti-IL-31RA antibody is nemolizumab.

In an eleventh aspect, the present disclosure provides methods of determining whether a subject with prurigo nodularis (PN) is responding to treatment with an anti-IL-31RA antibody, comprising detecting in a post-treatment plasma sample obtained from a subject with PN that has been administered at least one dose of an anti-IL-31RA antibody the amount of at least one, at least two, at least three, at least four, or at least five of: (a) a decrease in migration of leukocytes or cell movement of leukocytes; (b) an inhibition of a STAT3 pathway; (c) an inhibition of a STAT5b pathway; (d) a downregulation of IL-6 or an IL-6 pathway; (e) a downregulation of VEGF or a VEGF pathway; (f) a decrease in TGFB1 pathway activation, or (g) a combination thereof; where the decrease or inhibition is measured relative to a baseline amount and the decrease or inhibition indicates responsiveness to treatment, wherein the baseline amount was determined from a plasma sample obtained from the same subject before treatment was commenced. In some embodiments, the decrease or inhibition is determined by mass spectrometry. In some embodiments, the subject may also exhibit a downregulation in a neuronal ontology selected from CREB signaling in neurons, Synaptogenesis signaling pathway, Cell death of neuroglia and Apoptosis of neuroglia, and a combination thereof following administration of the anti-IL-31RA antibody.

In some embodiments of the eleventh aspect, the post-treatment sample is obtained about 2 weeks, about 4 weeks, about 6 weeks, about 8 weeks, about 10 weeks, or about 12 weeks after administration of the anti-IL-31RA antibody.

In some embodiments of the eleventh aspect, the anti-IL-31RA antibody comprises a heavy chain variable region comprising a HCDR1 comprising SEQ ID NO: 8, a HCDR2 comprising SEQ ID NO: 9, and a HCDR3 comprising SEQ ID NO: 10, and a light chain variable region comprising a LCDR1 comprising SEQ ID NO: 12, a LCDR2 comprising SEQ ID NO: 13, and a LCDR3 comprising SEQ ID NO: 14. In some embodiments, the anti-IL-31RA antibody is nemolizumab or a fragment or variant thereof. In some embodiments, the anti-IL-31RA antibody is nemolizumab.

The foregoing general description and following detailed description are exemplary and explanatory and are intended to provide further explanation of the disclosure as claimed. Other objects, advantages, and novel features will be readily apparent to those skilled in the art from the following brief description of the drawings and detailed description of the disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 6A-6B shows nemolizumab driven decrease in pruritus scoring was accompanied by tighter clustering of PN samples on PCA analyses after 12 weeks of treatment. The peak pruritus numeric rating scale (PP-NRS) was superimposed on transcriptomic data from PN lesional skin and assessed using PCA analyses. Nemolizumab group is shown as large dots, whereas placebo group is shown as small dots. Baseline (top) and week 12 of treatment (bottom) are shown. (A). Nemolizumab treatment led to tighter clustering of PN samples on PCA analyses compared to biopsy samples from the placebo treated cohort (B).

DETAILED DESCRIPTION

Figure 1B:
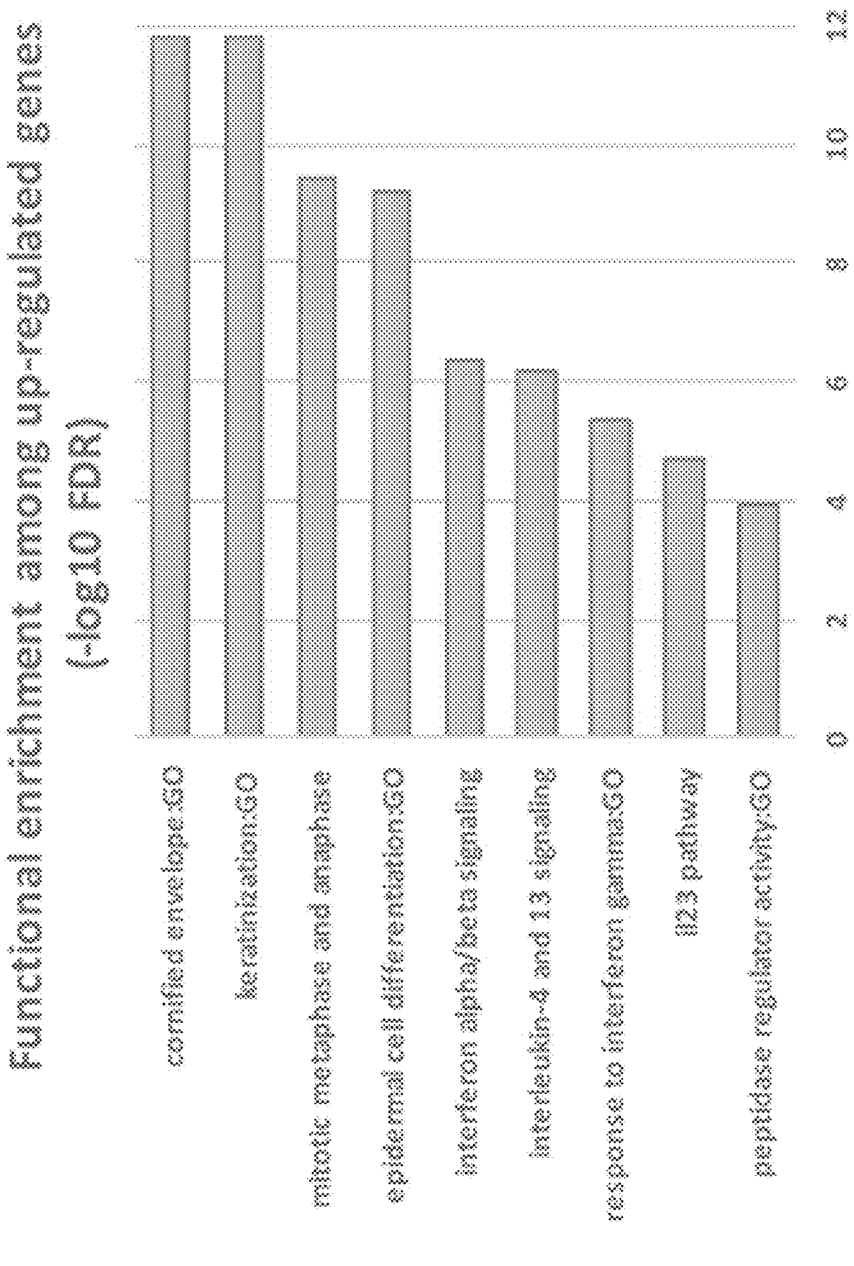
FIGS. 1A-1E shows that prurigo nodularis (PN) is characterized by immune activation and abnormal keratinocyte differentiation. Number of differentially expressed genes (DEGs) in PN lesional vs. non-lesional skin (n=62, FC>=2 or FC<=−2, FDR<=0.1) (A). Enriched GO categories in PN lesional skin (B). Literature-based gene network obtained from the top 1,000 DEGs in PN skin, generated using Genomatix Pathway System (GePS, Genomatix.de). The picture displays the top 50 best connected genes co-cited in PubMed abstracts in the same sentence linked to a function word (most relevant genes/interactions). Orange represent the genes that are upregulated and green represent the genes that are downregulated in PN lesional vs. non-lesional skin. Critical nodes included the proliferation markers Ki67 (MKI67), IL-1 family members IL36G and IL1A, and CXCL8 and CDKN1A (C). Number of genes and within cluster correlation in the modules identified from the weighted gene co-expression gene networks (WCGNA) analysis of non-lesional and lesional PN skin (D). Functions enriched in key co-expression modules from PN skin (module #5, #6 and #8) (E).

Described herein are treatments and preventions of prurigo nodularis (PN) using an anti-IL-31RA antibody (e.g., nemolizumab), as well as biomarkers and gene signatures associated with PN that were never previously known. The disclosed biomarkers, which include differentially expressed genes (DEGs), PN-specific gene ontologies (GOs), and other inflammatory and hyperproliferative markers, can be used to identify a subject with PN, determine whether a subject is likely to respond to treatment (e.g., with an anti-IL-31RA antibody), and track a subject's responsiveness to treatment. The disclosed treatments and preventions achieve therapeutic endpoints (e.g., normalizing DEGs, normalizing epidermal hyperproliferation, normalizing epidermal differentiation, and/or decreasing inflammatory responses in the skin) that were not previously known or obtainable with conventional treatments for PN.

I. Definitions

It is to be understood that the terminology used herein is for the purpose of describing particular embodiments only, and is not intended to be limiting.

Technical and scientific terms used herein have the meanings commonly understood by one of ordinary skill in the art, unless otherwise defined. Unless otherwise specified, materials and/or methodologies known to those of ordinary skill in the art can be utilized in carrying out the methods described herein, based on the guidance provided herein.

As used herein, the singular terms "a," "an," and "the" include plural referents unless the context clearly dictates otherwise. Reference to an object in the singular is not intended to mean "one and only one" unless explicitly so stated, but rather "one or more."

As used herein, "about" when used with a numerical value means the numerical value stated as well as plus or minus 10% of the numerical value. For example, "about 10" should be understood as both "10" and "9-11."

Also as used herein, "and/or" refers to and encompasses any and all possible combinations of one or more of the associated listed items, as well as the lack of combinations when interpreted in the alternative ("or").

As used herein, a phrase in the form "A/B" or in the form "A and/or B" means (A), (B), or (A and B); a phrase in the form "at least one of A, B, and C" means (A), (B), (C), (A and B), (A and C), (B and C), or (A, B, and C).

As used herein, the phrase "therapeutically effective amount" with reference to an anti-IL31R antibody (e.g. nemolizumab) means that dose of the antibody that provides the specific pharmacological effect for which the drug is administered in a subject in need of such treatment. A therapeutically effective amount may be effective to reduce, ameliorate, or eliminate itching, scratching, and/or lesion or nodule formation and/or improve quality of life in a subject with PN. It is emphasized that a therapeutically effective amount of an anti-IL31R antibody (e.g. nemolizumab) will not always be effective in treating PN in every individual subject, even though such dose is deemed to be a therapeutically effective amount by those of skill in the art. Those skilled in the art can adjust what is deemed to be a therapeutically effective amount in accordance with standard practices as needed to treat a specific subject. A therapeutically effective amount may vary based on, for example, the age and weight of the subject, and/or the subject's overall health, and/or the severity of the subject's PN.

The terms "treat," "treatment" or "treating" as used herein with reference to PN refer to reducing, ameliorating, or eliminating itching, scratching, and/or lesion or nodule formation and/or improving quality of life in a subject with PN.

The terms "prevent," "preventing" or "prevention" as used herein with reference to a PN refer to precluding or reducing the risk of developing lesions or nodules or preventing the development of the disclosed biomarker signatures that are associated with PN. Prevention may also refer to the prevention of a PN flare or recurrence once an initial flare has been treated or cured.

The terms "individual," "subject," and "patient" are used interchangeably herein, and refer to any individual mammalian subject, e.g., bovine, canine, feline, equine, or human. In specific embodiments, the subject, individual, or patient is a human.

II. Prurigo Nodularis (PN) and Biomarkers

Prurigo nodularis (or "PN") is a skin disease that causes hard, itchy lumps (nodules) to form on the skin. The itching (pruritus) can be intense, causing people to scratch themselves to the point of bleeding or pain. Scratching can cause more skin lesions to appear. The itching is worsened by heat, sweating, or irritation from clothing. In some cases, people with PN have a history of other diseases including eczema (atopic dermatitis), diabetes, lymphoma, HIV infection, severe anemia, or kidney disease. The exact cause of PN was not previously well-understood. It was thought that nodules were more likely to form when skin has been scratched or irritated in some way. Therefore, the act of a person scratching skin can cause the nodules to form. However, the cause of the skin to originally become intensely itchy was unclear.

Roughly 50% of people with PN have a history of atopy. The main symptom of PN is the formation of hard, very itchy lumps (nodules) on the skin. The nodules can range in size from very small to about half an inch in diameter. The nodules often have a rough, dry top and can range in number from a few to hundreds. Nodules most commonly form on the outer arms, shoulders, and legs. Nodules can also form on the neck and trunk, and they rarely form on the face and palms. They may be lighter or darker in color than the surrounding skin. Scarring may occur after nodules begin to heal. The symptoms of PN can begin at any age but are most common in adults after 50 years. People who have PN may become very concerned about the appearance of the nodules, and the intensely itchy skin may interfere with sleep or with everyday activities. This can cause people with PN to develop stress and depression.

Pruritus refers to itchy skin and/or an itch sensation. Pruritus may be caused by PN or other diseases or conditions such as dry skin. In some cases, pruritus involves generalized itchy skin over the whole body. In some cases, pruritus is localized to specific regions of the body such as on an arm or leg. Pruritus can be chronic or acute. Symptoms of pruritus include but are not limited to skin excoriations, redness, bumps, spots, blisters, dry skin, cracked skin, and leathery or scaly texture to the skin. In some cases, pruritus does not result in detectable changes to the skin. Behavioral responses to pruritus include but are not limited to skin scratching and/or skin massage. In some cases, skin scratching can result in excoriations that range from mild to severe. In some cases, patients with pruritus abstain from scratching and/or massaging the skin. Traditional treatments for PN include, but are not limited to, skin moisturizers, topical emollients, antihistamines such as diphenhydramine, topical corticosteroids, topical calcineurin inhibitors, and phototherapy. With narrow banded UVB and systemic immunosuppressive drugs like cyclosporine or methotrexate.

The present disclosure for the first time illuminates underlying gene expression patterns that are associates with PN and may be used to diagnose PN, identify a subject that is likely to respond to treatment (such as treatment with an anti-IL-31RA antibody), and determine whether a subject is properly responding to a treatment.

Figure 1A:
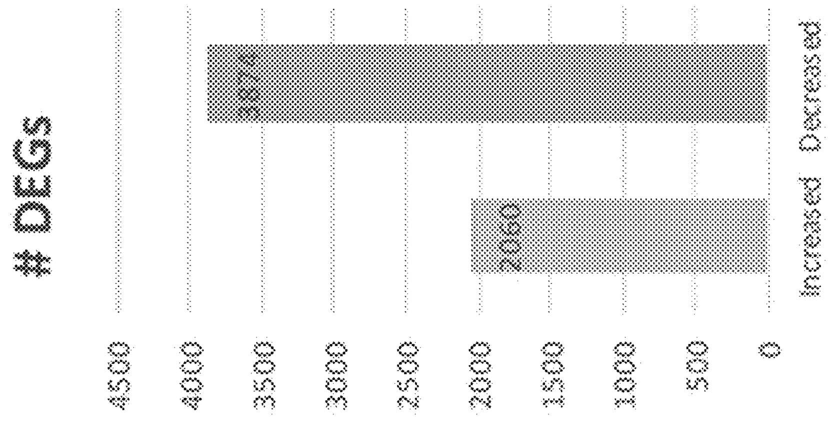

In particular, the present disclosure shows that a subject with PN may differentially express at least 5,934 genes (known as differentially expressed genes or DEGs), which are shown in FIG. 1A and Table 1 below. This differential gene expression may be observed in the skin of the subject and, in particular, in a skin sample comprising or consisting of a nodule or lesion. In some embodiments, at least 1, at least 2, at least 3, at least 4, at least 5, at least 10, at least 20, at least 30, at least 40, at least 50, at least 60, at least 70, at least 80, at least 90, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, at least 1000, at least 1100, at least 1200, at least 1300, at least 1400, at least 1500, at least 1600, at least 1700, at least 1800, at least 1900, at least 2000, at least 2100, at least 2200, at least 2300, at least 2400, or at least 2500 and up to 2500, 3000, 3500, 4000, 4500, 5000, 5500, or about 6000 of the disclosed DEGs may be differentially expressed in a subject with PN. Of these DEG, 2,060 may be increased (i.e., overexpressed) and 3,874 may be decreased (i.e., under expressed). Genes that may be increased the most include:

KRT6C, which may be increased at least 100-fold, at least 150 fold, at least 200-fold, at least 250-fold, at least 300-fold, at least 350-fold, at least 400-fold, at least 450-fold, at least 500-fold, at least 550-fold, or 588-fold compared to the expression level in a sample (e.g., a skin sample) from an individual that does not have PN;

DEFB4A, which may be increased at least 25-fold, at least 50-fold, at least 75-fold, at least 100-fold, at least 125-fold, or at least 150 fold compared to the expression level in a sample (e.g., a skin sample) from an individual that does not have PN; and KRT16, which may be increased at least 10-fold, at least 20-fold, at least 30-fold, at least 40-fold, at least 50-fold, at least 60-fold, at least 70-fold, at least 80-fold, or at least 90 fold compared to the expression level in a sample (e.g., a skin sample) from an individual that does not have PN.

Decreased genes include:

LCE5A, which may be decreased at least 2-fold, at least 3-fold, at least 4-fold, at least 5-fold, at least 6-fold, at least 7-fold, at least 8-fold, at least 9-fold, at least 10-fold, or at least 11 fold compared to the expression level in a sample (e.g., a skin sample) from an individual that does not have PN; and AQP7, which may be decreased at least 2-fold, at least 3-fold, at least 4-fold, at least 5-fold, at least 6-fold, at least 7-fold, or at least 7.9 fold compared to the expression level in a sample (e.g., a skin sample) from an individual that does not have PN.

Genes that encode cytokines may also be overexpressed in subjects suffering from PN. For the cytokine genes, the most prominent up-regulated genes are IL-36 family members and IL-20 family members. These upregulated or overexpressed genes may include:

IL36A (e.g., about 6.8-fold, FDR=$1.8\times10^{-4}$);
IL36G (e.g., about 8.4-fold, FDR=$3.9\times10^{-25}$);
IL19 (e.g., about 5.1-fold, FDR=$7.4\times10^{-4}$);
IL20 (e.g., about 3.5-fold, FDR=$1.7\times10^{-3}$);
IL22 (e.g., about 2.7-fold, FDR=$2.9\times10^{-2}$);
IL24 (e.g., about 5.8-fold, FDR=$3.8\times10^{-10}$); and
IL26 (e.g., about 4.9-fold, FDR=$3.3\times10^{-3}$).

Each of these IL-36 and IL-20 family member cytokine genes may be overexpressed by at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, or at least about 8-5-fold compared to the expression level in a sample (e.g., a skin sample) from an individual that does not have PN.

Other factors that may be upregulated or overexpressed include IL1A (e.g., about 4.7-fold, FDR=$1.0\times10^{-12}$) and IL1B (e.g., about 4.1-fold, FDR=$3.7\times10^{-6}$). Additionally, the IL4R gene may be increased by e.g., about 2.6-fold (FDR=$6.3\times10^{-19}$). Table 1 at the end of the examples section of the specification provides a more exhaustive list of the DEGs.

In addition to the foregoing genes, the present disclosure also shows that certain plasma markers or signatures may be altered as a result of successful treatment of PN with an anti-IL-31RA antibody, such as nemolizumab. Such markers or signatures are detectable by, for example, by mass spectrometry and other methods of protein assessment (e.g., ELISA, Western blot, etc.). Circulating plasma protein markers or signatures that may be modulated as a result of treatment with an anti-IL-31RA antibody, such as nemolizumab, can include leukocyte migration and cell movement, the IL-6 pathway, the vascular endothelial growth factor (VEGF) pathway, the STAT3 (signal transducer and activator of transcription 3) pathway, the STAT5b (signal transducer and activator of transcription 5b) pathway, the TGFB1 (transforming growth factor beta-1) pathway, and neuronal ontologies.

The STAT3 pathway, a direct target of IL-31 signaling is also inhibited in the disclosed nemolizumab responder signature, this suggesting target engagement. STAT3 activity and expression may be comparatively high in a subject with PN relative to an individual or population without PN or in the subject prior to commencing treatment with an anti-IL-31RA antibody, such as nemolizumab.

The amount of circulating pro-inflammatory cytokines may also be comparatively high in a subject with PN relative to an individual or population without PN or in the subject prior to commencing treatment with an anti-IL-31RA antibody, such as nemolizumab. Such pro-inflammatory cytokine signatures can include, but are not limited to, IL-6 and VEGF. In a PN subject that receives treatment with an anti-IL-31RA antibody, such as nemolizumab, the treatment may result in a decrease in one or both of IL-6 and VEGF, or decreases or inhibtio of the IL-6, VEGF, or both signaling pathways relative to a baseline level. The baseline level may be determined relative to (i) a control sample obtained from an individual or individuals (i.e., a population) without PN or (ii) a biological sample obtained from the subject prior to administration of the anti-IL-31RA antibody.

TGFB1 activity is also inhibited in the disclosed nemolizumab responder signature. TGFB1 activity and expression may be comparatively high in a subject with PN relative to an individual or population without PN or in the subject prior to commencing treatment with an anti-IL-31RA antibody, such as nemolizumab.

For the purposes of the disclosed plasma protein markers, the amount of the disclosed protein markers in the plasma of a subject with PN may be at least 2-fold, at least 3-fold, at least 4-fold, at least 5-fold, at least 6-fold, at least 7-fold, at least 8-fold, at least 9-fold, at least 10-fold, at least 15-fold, at least 20-fold, at least 25-fold, at least 30-fold, at least 35-fold, at least 40-fold, at least 45-fold, or at least 50-fold higher than a baseline level. The baseline level may be determined relative to (i) a control sample obtained from an individual or individuals (i.e., a population) without PN or (ii) a biological sample obtained from the subject prior to administration of the anti-IL-31RA antibody. Similarly, after a subject with PN is treated with an anti-IL-31RA antibody, such as nemolizumab (e.g., 2 weeks, 4 weeks, 6 weeks, 8 weeks, 10 weeks, or 12 weeks after administration of the antibody), the amount of the disclosed plasma protein markers in the subject may decrease at least 2-fold, at least 3-fold, at least 4-fold, at least 5-fold, at least 6-fold, at least 7-fold, at least 8-fold, at least 9-fold, at least 10-fold, at least 15-fold, at least 20-fold, at least 25-fold, at least 30-fold, at least 35-fold, at least 40-fold, at least 45-fold, or at least 50-fold relative to a baseline level. The baseline level may be determined relative to (i) a control sample obtained from an individual or individuals (i.e., a population) without PN or (ii) a biological sample obtained from the subject prior to administration of the anti-IL-31RA antibody.

Additionally, neuronal ontologies (e.g., CREB signaling in neurons, Synaptogenesis signaling pathway, Cell death of neuroglia and Apoptosis of neuroglia) may be upregulated in subject with PN, and subsequently downregulated in nemolizumab responders subjects, thus emphasizing the impact of IL-31 as a neuro-inflammatory cytokine in PN.

Thus, the present disclosure provides methods of diagnosing PN, comprising detecting in a sample obtained from a subject suspected of having PN the expression level of at least one, at least two, at least three, at least four, or at least five of the differentially expressed genes (DEGs) in Table 1 (e.g., KRT6C, DEFB4A, KRT16, LCE5A, AQP7, IL-36 family members, IL-20 family members, etc.) and comparing the expression level of the DEGs to a reference level, which may be based on the gene expression level in a sample (e.g., a skin sample) from an individual that does not have PN. In some embodiments, the sample obtained from the subject suspected of having PN is a skin sample, which may comprise a lesion or a nodule. If certain genes are upregulated or overexpressed (e.g., KRT6C, DEFB4A, KRT16) and/or if other genes are down regulated or under expressed (e.g., LCE5A, AQP7) then the subject may be diagnosed with PN.

The present disclosure also provides methods of determining the likelihood of a positive response to treatment (e.g., treatment with an anti-IL-31RA antibody, such as nemolizumab) in a subject with PN, comprising detecting in a sample obtained from a subject with PN the expression level of at least one, at least two, at least three, at least four, or at least five of the differentially expressed genes (DEGs) in Table 1 (e.g., KRT6C, DEFB4A, KRT16, LCE5A, AQP7, IL-36 family members, IL-20 family members, etc.) and comparing the expression level of the DEGs to a reference level, which may be based on the gene expression level in a sample (e.g., a skin sample) from an individual that does not have PN. In some embodiments, the sample obtained from the subject with PN is a skin sample, which may comprise a lesion or a nodule. If certain genes are upregulated or overexpressed (e.g., KRT6C, DEFB4A, KRT16) and/or if other genes are down regulated or under expressed (e.g., LCE5A, AQP7) then the subject is likely to respond to the treatment.

The present disclosure also provides methods of determining whether a subject with PN is responding to treatment (e.g., treatment with an anti-IL-31RA antibody, such as nemolizumab), comprising detecting in a sample obtained from a subject with PN the expression level of at least one, at least two, at least three, at least four, or at least five of the differentially expressed genes (DEGs) in Table 1 (e.g., KRT6C, DEFB4A, KRT16, LCE5A, AQP7, IL-36 family members, IL-20 family members, etc.) and comparing the expression level of the DEGs to a baseline level of expression, wherein baseline level of gene expression is from a sample (e.g., a skin sample) from the same individual before treatment was commenced. In some embodiments, the samples may be skin samples, which may comprise a lesion or a nodule. If the expression levels of certain genes decreases (e.g., KRT6C, DEFB4A, KRT16) and/or if the expression level of other genes increases (e.g., LCE5A, AQP7) then the subject is responding to the treatment.

The present disclosure also provides methods of determining whether a subject with PN is responding to treatment (e.g., treatment with an anti-IL-31RA antibody, such as nemolizumab), comprising detecting in a post-treatment plasma sample obtained from a subject with PN that has been administered at least one dose of an anti-IL-31RA antibody one or more biomarkers selected from leukocyte migration and cell movement, the IL-6 pathway, the VEGF pathway, the STAT3 pathway, the STAT5b pathway, the TGFB1 pathway, and the disclosed neuronal ontologies; wherein a decrease in leukocyte migration and cell movement, a decrease in IL-6 or a decrease in IL-6 pathway signaling, a decrease in VEGF or a decrease in VEGF pathway signaling, a decrease in STAT3 or a decrease in STAT3 pathway signaling, a decrease in STAT5b or a decrease in STAT5b pathway signaling, a decrease in TGFB1 or a decrease in TGFB1 pathway signaling, or an increase in the disclosed neuronal ontologies relative to a baseline amount indicates responsiveness to treatment, wherein the baseline amount was determined from a plasma sample obtained from the same subject before treatment was commenced.

The present disclosure also defines for the first time the biological processes that are enriched in PN skin gene ontology (GO). The most prominent GO categories associated with PN are:

"cornified envelope" (FDR=$1.5\times10^{-12}$),
"epidermal cell differentiation" (FDR=$6.4\times10^{-10}$),
"keratinization" (FDR=$1.6\times10^{-12}$),
"peptidase regulator activity" (FDR=$1.1\times10^{-4}$),
"interleukin-4 and 13 signaling" (FDR=$6.8\times10^{-7}$),
"interferon alpha/beta signaling" and "response to interferon gamma" (FDR=$4.1\times10^{-7}$, and FDR=$4.1\times10^{-6}$, respectively),
"IL23 pathway" (FDR=$2\times10^{-5}$), and
"mitotic metaphase and anaphase" (FDR=$3.8\times10^{-10}$).

Figure 1C:
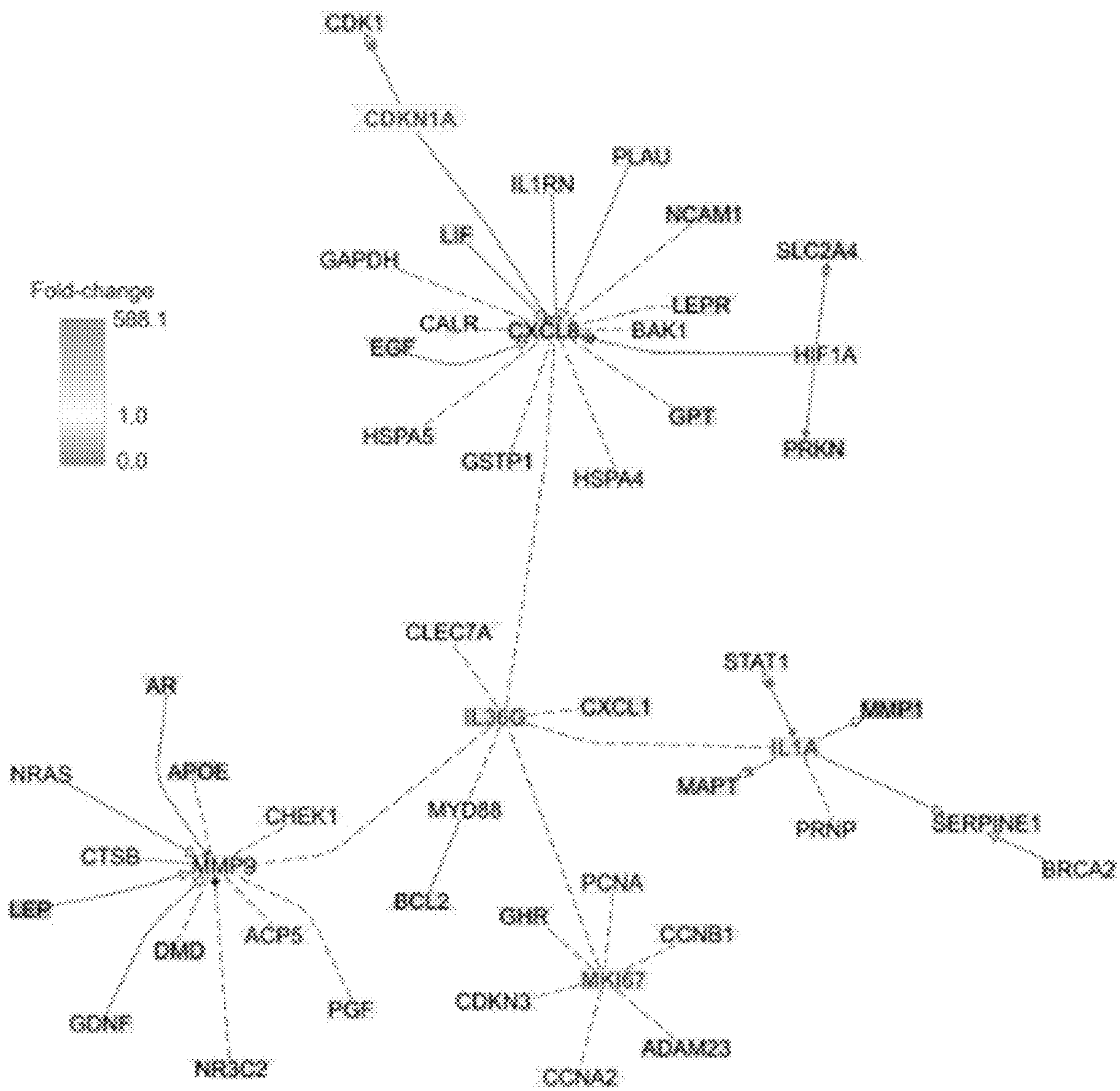

These GO categories are defined in more detail by FIG. 1B and Table 2 at the end of the examples section of the specification. These categories reflect the hyperproliferative nature of PN, which was discovered to be associated with altered epidermal differentiation and inflammatory components. For example, the proliferative marker Ki67 (MKI67), the cell cycle gene CDKN1A, and inflammatory networks involving IL-1 and IL-36 have now been revealed as potentially associated with PN pathogenesis as shown in FIG. 1C.

Figures 1D, 1E:
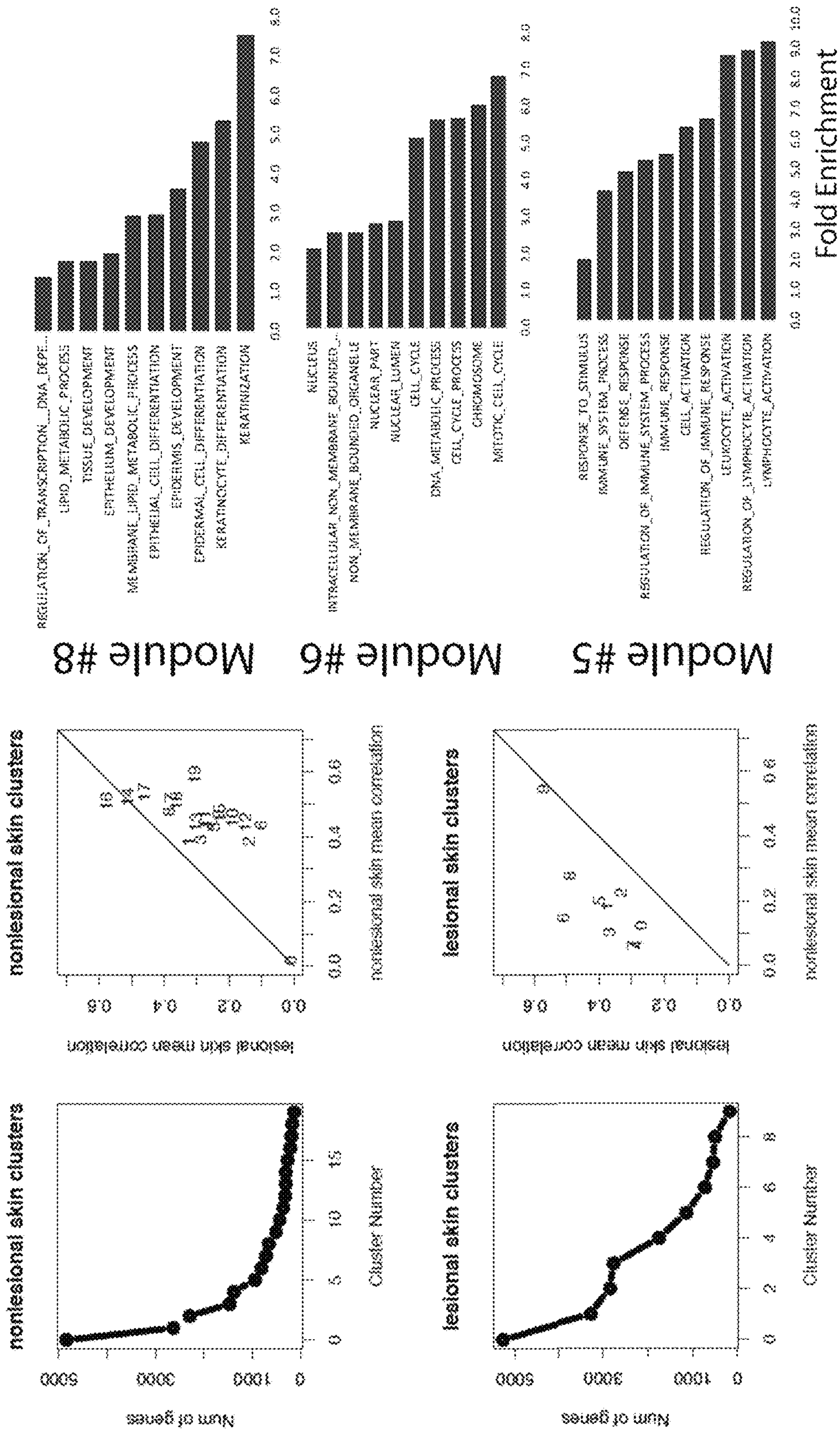

The present disclosure also discloses 20 co-expression modules that were identified in non-lesional skin and 10 clusters in lesional PN skin, as shown in FIG. 1D and Table 3 at the end of the examples section of the specification. Distinct functions could be defined for these co-expressing gene modules, especially for the co-expression modules in PN lesional skin, with the most prominent involved immunological processes (module #8) including "immune-response" (FDR=$1.8\times10^{-47}$), "defense response" (FDR=$1.2\times10^{-39}$); cell proliferation (module #6) including "cell cycle"

Figure 2A:
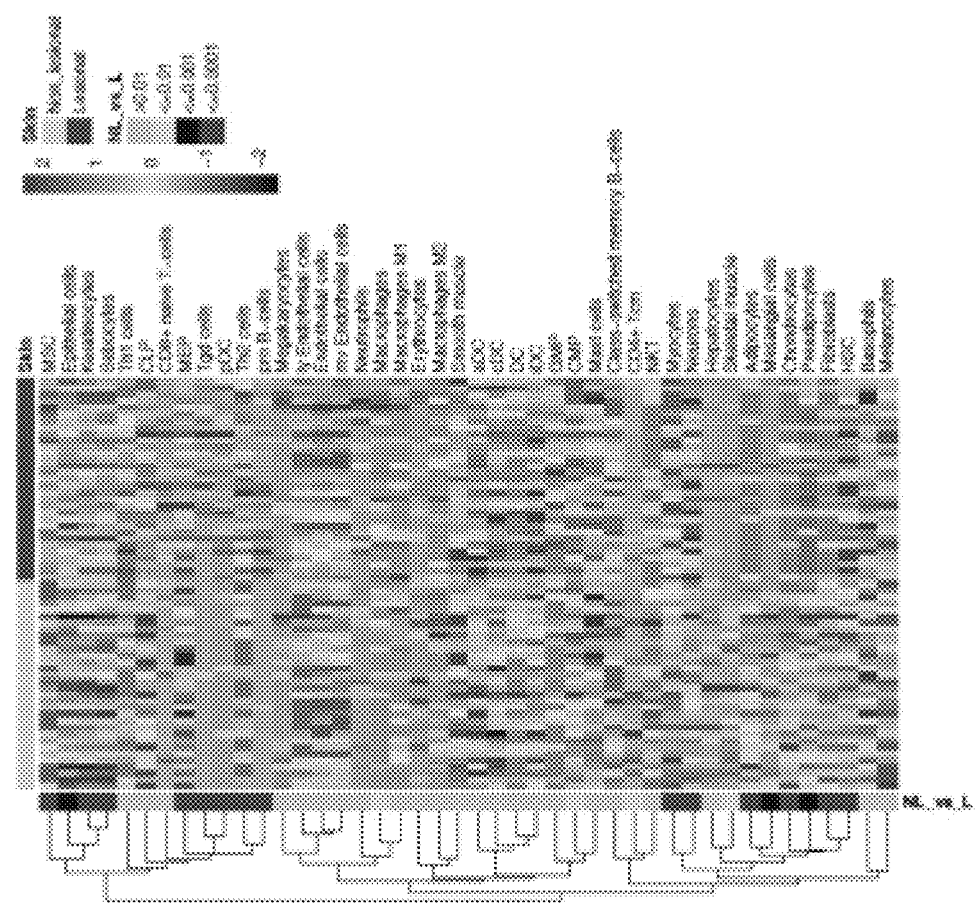
FIGS. 2A-2C shows enriched transcriptomic cellular signatures and overlap with psoriasis and AD. Cell type inference analysis on non-lesional (NL) and lesional (L) PN skin samples using xCell. Enriched cellular signatures are shown as red but underrepresented cellular signatures are shown in blue. The bar on the left side shows statistical difference in the enrichment between lesional and non-lesional PN skin with the colors representing different p-value thresholds (A). Comparison of PN associated DEGs against DEGs in Psoriasis (Pso) and atopic dermatitis (AD) for increased and decreased DEGs (B). Correlation analysis between the effect sizes in PN lesion versus those in psoriasis (Pso) and atopic dermatitis (AD). Spearman's rank-order correlation was included. The genes significant in the x-axis, y-axis, and both axes are colored in red/blue/purple respectively (C).

(FDR=$2.9\times10^{-94}$), "DNA metabolic process" (FDR=$8.7\times10^{-67}$); and epidermal processes (module #5), such as "epidermis development" (FDR $3.5\times10^{-10}$), "keratinization" (FDR=$1.7\times10^{-6}$). See also FIG. 1E. Other notable findings were changes in "extracellular matrix" (FDR=$1.16\times10^{-59}$; module #2) and included genes such as MMP14, MMP16, COL1A1, COL1A2, and COL3A1, which were modestly elevated (FC≥1.4; FDR≤$6\times10^{-2}$) in the lesional skin, consistent with the association of PN with skin fibrosis The present disclosure also provides specific cell-type signatures for non-lesional and lesional PN skin samples. Enrichment for transcriptomic signature associated with epithelial cells and keratinocytes was observed ($p<0.001$ and $p<0.0001$, respectively), as shown in FIG. 2A. A subject with PN may show a Th2 associated signature ($p<0.0001$), consistent with the enriched GO categories for IL-4/IL-13 (as discussed above and shown FIG. 1B). Other inflammatory signatures, such as macrophages ($p<0.01$), may be more variable.

Figure 2B:
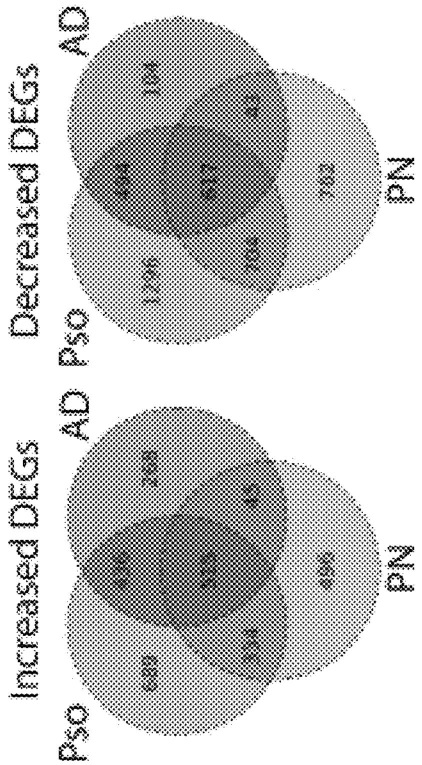

As shown in FIG. 2B, a 3-way comparison of the PN transcriptome with that of atopic dermatitis (AD) and Psoriasis indicated that all three diseases share significant overlap for both up-regulated and down-regulated genes. However, the correlation of the effect sizes in the lesional skin was more pronounced between PN and psoriasis (spearman correlation $\rho=0.64$) than between PN and AD ($\rho=0.55$). Genes that are commonly up-regulated in both psoriasis and PN include those participating in cytokine activity (CCL3, CXCL10, IFNG, IL12B, IL19, IL1B, IL20, etc.) and keratinization (KRT16, KRT17, LCE3A, LCE3E, etc.) (Table 4).

Thus, the present disclosure provides methods of identifying or diagnosing PN based on gene ontology, co-expression module, and/or gene signature. For example, a subject may present with a PN skin gene ontology (GO) shown in FIG. 1B or Table 2. Additionally or alternatively, the skin sample may also show upregulation or overexpression of Ki67 (MKI67), CDKN1A, and/or inflammatory networks involving IL-1 and IL-36. Additionally or alternatively, a subject may present with a co-expression module as shown in FIG. 1D or Table 3. Additionally or alternatively, a subject with PN may present (e.g., in a skin sample) with the transcriptomic or Th2 signature disclosed in FIG. 2A.

The expression levels of the genes and markers disclosed herein can be determined by any suitable methods known in the art, including but not limited to RT-qPCR, RT-PCR, RNA-seq, Northern blotting, Serial Analysis of Gene Expression (SAGE), DNA or RNA microarrays, and in situ hybridization. At the protein level, the disclosed biomarkers may be detected or measured using, for example, Western blotting, ELISA (Enzyme-Linked ImmunoSorbent Assay), surface plasmon resonance, and mass spectrometry.

Subjects with PN or suspected of having PN that present with any of the disclosed DEGs, gene ontologies, co-expression modules, or gene signatures are suitable for treatment or preventions with an anti-IL-31RA antibody, such as nemolizumab, as described in further detail herein.

The present disclosure provides a combination of (1) a pharmaceutical composition for use in the treatment or prevention of prurigo nodularis (PN), comprising an anti-IL31RA antibody (e.g., nemolizumab or a fragment or variant thereof), as an active ingredient; and (2) a diagnostic agent which detects in a subject suspected of having PN the expression level of at least one gene selected from the genes disclosed in Table 1 compared to a reference level of expression for the at least one gene.

III. Therapeutic Antibodies and Interleukin 31 Receptor Subunit Alpha (IL-31RA)

Interleukin-31 (IL-31) is a neuro-inflammatory cytokine that could activate both structural, immune cells and peripheral nerves. It has been involved in a number of chronic inflammatory diseases, including atopic dermatitis. IL-31 is produced by a variety of cells, including type 2 helper (Th2) T-cells. IL-31 sends signals through a receptor complex made of IL-Interleukin 31 receptor subunit alpha ("IL-31RA," also known as NR10, glm-r, and GPL) and oncostatin M receptor β (OSMRβ) expressed in immune and epithelial cells, as well as in a subset of neurons.

IL-31RA forms a heterodimer with oncostatin M receptor (OSMR) when functioning as an IL-31 receptor. There are multiple known splicing variants of human-derived IL-31RA (WO 00/075314): NR10.1 consists of 662 amino acids and contains a transmembrane domain. NR10.2 is a soluble receptor-like protein consisting of 252 amino acids without the transmembrane domain. Further, known IL-31RA splicing variants that function as transmembrane receptor proteins include NR10.3 and IL-31RAv3. Preferred IL-31RA variants include NR10.3 (also referred to as ILRAv4 (Nat Immunol 5, 752-60, 2004) and IL-31RAv3. NR 10.3 (IL31RAv4) consists of 662 amino acids (WO 00/075314; Nat Immunol 5, 752-60, 2004) and IL31RAv3 consists of 732 amino acids (GenBank Accession No: NM-139017).

The amino acid sequence of IL31RAv4 is:

```
                                    (SEQ ID NO: 1)
MKLSPQPSCVNLGMMWTWALWMLPSLCKFSLAALP

AKPENISCVYYYRKNLTCTWSPGKETSYTQYTVKR

TYAFGEKHDNCTTNSSTSENRASCSFFLPRITIPD

NYTIEVEAENGDGVIKSHMTYWRLENIAKTEPPKI

FRVKPVLGIKRMIQIEWIKPELAPVSSDLKYTLRF

RTVNSTSWMEVNFAKNRKDKNQTYNLTGLQPFTEY

VIALRCAVKESKFWSDWSQEKMGMTEEEAPCGLEL

WRVLKPAEADGRRPVRLLWKKARGAPVLEKTLGYN

IWYYPESNTNLTETMNTTNQQLELHLGGESFWVSM

ISYNSLGKSPVATLRIPAIQEKSFQCIEVMQACVA

EDQLVVKWQSSALDVNTWMIEWFPDVDSEPTTLSW

ESVSQATNWTIQQDKLKPFWCYNISVYPMLHDKVG

EPYSIQAYAKEGVPSEGPETKVENIGVKTVTITWK

EIPKSERKGIICNYTIFYQAEGGKGFSKTVNSSIL

QYGLESLKRKTSYIVQVMASTSAGGTNGTSINFKT

LSFSVFEIILITSLIGGGLLILIILTVAYGLKKPN

KLTHLCWPTVPNPAESSIATWHGDDFKDKLNLKES

DDSVNTEDRILKPCSTPSDKLVIDKLVVNFGNVLQ

EIFTDEARTGQENNLGGEKNGTRILSSCPTSI
```

The amino acid sequence of IL31RAv3 is:

```
                                    (SEQ ID NO: 2)
MMWTWALWMLPSLCKFSLAALPAKPENISCVYYYR
```

-continued

KNLTCTWSPGKETSYTQYTVKRTYAFGEKHDNCTT

NSSTSENRASCSFFLPRITIPDNYTIEVEAENGDG

VIKSHMTYWRLENIAKTEPPKIFRVKPVLGIKRMI

QIEWIKPELAPVSSDLKYTLRFRTVNSTSWMEVNF

AKNRKDKNQTYNLTGLQPFTEYVIALRCAVKESKF

WSDWSQEKMGMTEEEAPCGLELWRVLKPAEADGRR

PVRLLWKKARGAPVLEKTLGYNIWYYPESNTNLTE

TMNTTNQQLELHLGGESFWVSMISYNSLGKSPVAT

LRIPAIQEKSFQCIEVMQACVAEDQLVVKWQSSAL

DVNTWMIEWFPDVDSEPTTLSWESVSQATNWTIQQ

DKLKPFWCYNISVYPMLHDKVGEPYSIQAYAKEGV

PSEGPETKVENIGVKTVTITWKEIPKSERKGIICN

YTIFYQAEGGKGFSKTVNSSILQYGLESLKRKTSY

IVQVMASTSAGGTNGTSINFKTLSFSVFEIILITS

LIGGGLLILIIILTVAYGLKKPNKLTHLCWPTVPNP

AESSIATWHGDDFKDKLNLKESDDSVNTEDRILKP

CSTPSDKLVIDKLVVNFGNVLQEIFTDEARTGQEN

NLGGEKNGYVTCPFRPDCPLGKSFEELPVSPEIPP

RKSQYLRSRMPEGTRPEAKEQLLFSGQSLVPDHLC

EEGAPNPYLKNSVTAREFLVSEKLPEHTKGEV

Mouse-derived IL-31RA comprises the amino acid sequence:

(SEQ ID NO: 3)

MWTLALWAFSFLCKFSLAVLPTKPENISCVFYFDR

NLTCTWRPEKETNDTSYIVTLTYSYGKSNYSDNAT

EASYSFPRSCAMPPDICSVEVQAQNGDGKVKSDIT

YWHLISIAKTEPPIILSVNPICNRMFQIQWKPREK

TRGFPLVCMLRFRTVNSSRWTEVNFENCKQVCNLT

GLQAFTEYVLALRFRFNDSRYWSKWSKEETRVTME

EVPHVLDLWRILEPADMNGDRKVRLLWKKARGAPV

LEKTFGYHIQYFAENSTNLTEINNITTQQYELLLM

SQAHSVSVTSFNSLGKSQEAILRIPDVHEKTFQYI

KSMKAYIAEPLLVVNWQSSIPAVDTWIVEWLPEAA

MSKFPALSWESVSQVTNWTIEQDKLKPFTCYNISV

YPVLGHRVGEPYSIQAYAKEGTPLKGPETRVENIG

LRTATITWKEIPKSARNGFINNYTVFYQAEGGKEL

SKTVNSHALQCDLESLTRRTSYTVWVMASTRAGGT

NGVRINFKTLSISVFEIVLLTSLVGGGLLLLSIKT

VTFGLRKPNRLTPLCCPDVPNPAESSLATWLGDGF

KKSNMKETGNSGDTEDVVLKPCPVPADLIDKLVVN

-continued

FENFLEVVLTEEAGKGQASILGGEANEYVTSPSRP

DGPPGKSFKEPSVLTEVASEDSHSTCSRMADEAYS

ELARQPSSSCQSPGLSPPREDQAQNPYLKNSVTTR

EFLVHENIPEHSKGEV

Cynomolgus monkey-derived IL-31RA comprises the amino acid sequence:

(SEQ ID NO: 4)

MMWTWALWMFPLLCKFGLAALPAKPENISCVYYYR

KNLTCTWSPGKETSYTQYTAKRTYAFGKKHDNCTT

SSSTSENRASCSFFLPRITIPDNYTIEVEAENGDG

VIKSDMTCWRLEDIAKTEPPEIFSVKPVLGIKRMI

RIEWIKPELAPVSSDLKYALRFRTVNSTSWMEVNF

AKNRKDTNQTYNLMGLQAFTEYVVALRCAVKESKF

WSDWSQEKMGMTEEEAPCGLELWRVLKPTEVDGRR

PVRLLWKKARGAPVLEKTLGYNIWYFPENNTNLTE

TVNTTNQQLELHLGGESYWVSMISYNSLGKSPVTT

LRIPAIQEKSFRCIEVMQACLAEDQLVVKWQSSAL

DVNTWMIEWFPDMDSEHPTLSWESVSQATNWTIQQ

DKLKPFWCYNISVYPMLHDKVGEPYSIQAYAKEGI

PSKGPETKVENIGVKTVTITWKEIPKSERKGIICN

YTIFYQAEGGKGFSKTVNSSILQYGLESLKRKTSY

TVRVMASTSAGGINGTSINFKTLSFSVFEIILITS

LIGGGLLILIIILTVAYGLKKPNKLTHLCWPSVPNP

AESSIATWRGDDFKDKLNLKESDDSVNTEDRILKP

CSTPSDKLVIDKSVVNFGNVLQEMFTDEARTGQEN

NLGGEKNEYVTHPFRADCPLGKSFEELPVSPEIPP

RKSQYLRSRMPEGTCLEAEEQLLVSGQSLESLAPD

HVREAAAPNPYLKNSVTTREFLVSQKLPEHTKGEV

For the purposes of the present disclosure, an anti-IL-31RA antibody (i.e., a therapeutic antibody), such as nemolizumab, must bind to at least human IL-31RA or a splice variant thereof.

As used herein, the term "antibody" collectively refers to immunoglobulins or immunoglobulin-like molecules including IgA, IgD, IgE, IgG and IgM, combinations thereof or fragments thereof. Fragments of antibodies may include, for example, Fab fragments and single chain variable fragments (scFv). An antibody generally comprises heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. Each heavy and light chain contains a constant region and a variable region (also known as "domains"). In combination, the heavy and the light chain variable regions, also called the "Fab region," specifically bind to a given antigen. Light and heavy chain variable regions contain a "framework" region interrupted by three hypervariable regions, also called "complementarity-determining regions" or "CDRs." The extent of the framework region and CDRs has been defined (see Kabat et al., Sequences of Proteins of Immunological Interest, U.S. Department of Health and Human Services, 1991). The Kabat database is now maintained online. The sequences of the framework regions of different light or heavy chains are relatively conserved within a species, and framework regions act to form a scaffold that provides for positioning the CDRs in correct orientation by inter-chain, non-covalent interactions.

The CDRs are primarily responsible for binding to an epitope on an antigen. The CDRs of each chain are typically referred to as CDR1, CDR2, and CDR3, numbered sequentially starting from the N-terminus, and are also typically identified by the chain in which the particular CDR is located. Thus, a HCDR3 is located in the variable domain of the heavy chain of the antibody in which it is found, whereas a LCDR1 is the CDR1 from the variable domain of the light chain of the antibody in which it is found. An antibody that binds IL-31RA will have a specific $V_H$ region and the $V_L$ region sequence, and thus specific CDR sequences. Antibodies with different specificities generally have different CDRs. Although it is the CDRs that vary from antibody to antibody, only a limited number of amino acid positions within the CDRs are directly involved in antigen binding. These positions within the CDRs are called specificity determining residues (SDRs).

The Fc fragment region (Fc) of an antibody plays a role in modulating immune cell activity. The Fc region functions to guarantee that each antibody generates an appropriate immune response for a given antigen, by binding to a specific class of proteins found on certain cells, such as B lymphocytes, follicular dendritic cells, natural killer cells, macrophages, neutrophils, etc. and are called "Fc receptors." Because the constant domains of the heavy chains make up the Fc region of an antibody, the classes of heavy chain in antibodies determine their class effects. The heavy chains in antibodies include alpha, gamma, delta, epsilon, and mu, and correlate to the antibody's isotypes IgA, IgG, IgD, IgE, and IgM, respectively. Thus, different isotypes of antibodies have different class effects due to their different Fc regions binding and activating different types of receptors.

There are four subclasses of IgG, which is the most abundant antibody isotype found in human serum. The four subclasses, IgG1, IgG2, IgG3, and IgG4, which are highly conserved. The amino acid sequence of the constant regions of these peptides are known in the art, e.g., see Rutishauser, U. et al. (1968) "Amino acid sequence of the Fc region of a human gamma G-immunoglobulin" PNAS 61(4):1414-1421; Shinoda et al. (1981) "Complete amino acid sequence of the Fc region of a human delta chain" PNAS 78(2):785-789; and Robinson et al. (1980) "Complete amino acid sequence of a mouse immunoglobulin alpha chain (MOPC 511)" PNAS 77(8):4909-4913.

All therapeutic antibodies, for the purposes of the disclosed methods and pharmaceutical uses, are antibodies or fragments thereof that bind to IL-31RA, but the specific anti-IL-31RA antibody is not limited. Nemolizumab is a preferred anti-IL-31RA antibody, but other anti-IL-31RA antibodies can be used as well. A therapeutic antibody suitable for use in the disclosed methods and pharmaceutical uses may be human, humanized, or chimeric, and it may be an IgA, IgG (i.e., IgG1, IgG2, IgG3, and IgG4), IgD, IgE, or IgM.

Nemolizumab is a humanized monoclonal antibody that binds to IL-31RA. Nemolizumab is annotated as follows: immunoglobulin G2-kappa, anti-[*Homo sapiens* IL31RA (interleukin 31 receptor subunit alpha)], humanized monoclonal antibody; gamma2 heavy chain (1-445) [humanized VH (*Homo sapiens* IGHV1-2*02 (83.70%)-(IGHD)-IGHJ5*01) [8.8.14] (1-121)-*Homo sapiens* IGHG2*01 (CH1 C10>S (135), R12>K (137), E16>G (141), S17>G (142) (122-219), hinge C4>S (223) (220-231), CH2 H30>Q (268) (232-340), CH3 R11>Q (355), Q98>E (419) (341-445)) (122-445)], (224-214')-disulfide with kappa light chain (1'-214') [humanized V-KAPPA (*Homo sapiens* IGKV1-39*01 (82.10%)-IGKJ4*01) [6.3.9] (1'-107')-*Homo sapiens* IGKC*01 (108'-214')]; dimer (227-227":230-230")-bisdisulfide. Nemolizumab has disulfide bridges at the following locations: Intra-H (C23-C104) 22-96 148-204 261-321 367-425 22"-96" 148"-204" 261"-321" 367"-425"; Intra-L (C23-C104) 23'-88' 134'-194' 23'"-88'" 134'"-194'"; Inter-H-L (h 5-CL 126) 224-214' 224"-214'"; Inter-H-H (h 8, h 11) 227-227" 230-230". Nemolizumab has N-glycosylation sites at the following locations: H CH2 N84.4: 297, 297". Nemolizumab lacks H chain C-terminal glycine and lysine (CHS G1>del, K2>del).

Nemolizumab comprises the following heavy chain amino acid sequence:

```
                                (SEQ ID NO: 5)
QVQLVQSGAEVKKPGASVKVSCKASGYTFTGYIMN
WVRQAPGQGLEWMGLINPYNGGTDYNPQFQDRVTI
TADKSTSTAYMELSSLRSEDTAVYYCARDGYDDGP
YTLETWGQGTLVTVSSASTKGPSVFPLAPSSKSTS
GGTAALGCLVKDYFPEPVTVSWNSGALTSGVHTFP
AVLQSSGLYSLSSVVTVPSSNFGTQTYTCNVDHKP
SNTKVDKTVERKSCVECPPCPAPPVAGPSVFLFPP
KPKDTLMISRTPEVTCVVVDVSQEDPEVQFNWYVD
GVEVHNAKTKPREEQFNSTFRVVSVLTVVHQDWLN
GKEYKCKVSNKGLPAPIEKTISKTKGQPREPQVYT
LPPSQEEMTKNQVSLTCLVKGFYPSDIAVEWESNG
QPENNYKTTPPMLDSDGSFFLYSKLTVDKSRWQEG
NVFSCSVMHEALHNHYTQKSLSLSP.
```

Nemolizumab comprises the following light chain amino acid sequence:

```
                                (SEQ ID NO: 6)
DIQMTQSPSSLSASVGDRVTITCQASEDIYSFVAW
YQQKPGKAPKLLIYNAQTEAQGVPSRFSGSGSGTD
FTLTISSLQPEDFATYYCQHHYDSPLTFGGGTKVE
IKRTVAAPSVFIFPPSDEQLKSGTASVVCLLNNFY
PREAKVQWKVDNALQSGNSQESVTEQDSKDSTYSL
SSTLTLSKADYEKHKVYACEVTHQGLSSPVTKSFN
RGEC.
```

The heavy chain variable region of nemolizumab comprises the amino acid sequence:

(SEQ ID NO: 7)
QVQLVQSGAEVKKPGASVKVSCKASGYTFTGYIMN

WVRQAPGQGLEWMGLINPYNGGTDYNPQFQDRVTI

TADKSTSTAYMELSSLRSEDTAVYYCARDGYDDGP

YTLETWGQGTLVTVSS.

The HCDR1 of nemolizumab comprises the amino acid sequence GYIMN (SEQ ID NO: 8), the HCDR2 comprises the amino acid sequence LINPYNGGTDYNPQFQD (SEQ ID NO: 9), and the HCDR3 comprises the amino acid sequence DGYDDGPYTLET (SEQ ID NO: 10).

The light chain variable region of nemolizumab comprises the amino acid sequence:

(SEQ ID NO: 11)
DIQMTQSPSSLSASVGDRVTITCQASEDIYSFVAW

YQQKPGKAPKLLIYNAQTEAQGVPSRFSGSGSGTD

FTLTISSLQPEDFATYYCQHHYDSPLTFGGGTKVE

IKR.

The LCDR1 of nemolizumab comprises the amino acid sequence QASEDIYSFVA (SEQ ID NO: 12), the LCDR2 comprises the amino acid sequence NAQTEAQ (SEQ ID NO: 13), and the LCDR3 comprises the amino acid sequence QHHYDSPLT (SEQ ID NO: 14).

For the purposes of this disclosure "variant antibodies" or "variant" of nemolizumab may include, but are not limited to: (i) antibodies with heavy chains comprising at least 55%, at least 65%, at least 70%, at least 75%, at least 80%, at least 85%, at least 90%, at least 95%, at least 97%, at least 98%, at least 99%, or 100% amino acid sequence identity to nemolizumab's heavy chain sequence, (ii) antibodies with light chains comprising at least 55%, at least 65%, at least 70%, at least 75%, at least 80%, at least 85%, at least 90%, at least 95%, at least 97%, at least 98%, at least 99%, or 100% amino acid sequence identity to nemolizumab's light chain sequence, (iii) antibodies with variable regions comprising at least 55%, at least 65%, at least 70%, at least 75%, at least 80%, at least 85%, at least 90%, at least 95%, at least 97%, at least 98%, at least 99%, or 100% amino acid sequence identity to nemolizumab's variable region sequences, (iv) antibodies with CDRs comprising at least 55%, at least 65%, at least 70%, at least 75%, at least 80%, at least 85%, at least 90%, at least 95%, at least 97%, at least 98%, at least 99%, or 100% amino acid sequence identity to nemolizumab's CDR sequences, and (v) combinations thereof. For example, suitable variants include immunoglobulins or immunoglobulin-like molecules with the same or substantially similar heavy and light chain amino acid sequences as nemolizumab. Other suitable therapeutic antibodies may bind to the same isoform of IL-31RA as nemolizumab (e.g., IL31-RAv3), optionally the same epitope of IL-31RA, block or neutralize IL-31RA, or combinations thereof. Additional exemplary therapeutic antibodies are described, for example, in WO 2010/064697.

Variants of nemolizumab and suitable therapeutic antibodies may be monoclonal or polyclonal antibodies. Such monoclonal antibodies having IL31-RA-binding and/or neutralizing activity can be obtained, for example, by the following procedure: anti-IL31-RA monoclonal antibodies are prepared by using as an antigen IL31-RA or a fragment thereof that is derived from a mammal such as human or mouse by known methods, and then antibodies having IL31-RA-binding and/or neutralizing activity are selected from the thus obtained anti-IL31-RA monoclonal antibodies. Specifically, a desired antigen or cells expressing the desired antigen are used as a sensitizing antigen for immunization according to conventional immunization methods. Anti-IL31-RA monoclonal antibodies can be prepared by fusing the obtained immune cells with known parental cells using conventional cell fusion methods, and screening them for monoclonal antibody-producing cells (hybridomas) by conventional screening methods. Animals to be immunized include, for example, mammals such as mice, rats, rabbits, sheep, monkeys, goats, donkeys, cows, horses, and pigs. The antigen can be prepared using the known IL31-RA gene sequence according to known methods, for example, by methods using baculovirus (for example, WO 98/46777). Variants of nemolizumab and suitable therapeutic antibodies may also include intrabodies, peptibodies, nanobodies, single domain antibodies, multi-specific antibodies (e.g., bispecific antibodies, diabodies, triabodies, tetrabodies, tandem di-scFV, tandem tri-scFv), darpins, heavy chain monomers, heavy chain dimers, or single-domain antibodies (i.e., a $V_H$H fragment or a "camelid-like" antibody), any of which may be derived from the sequence and/or binding domain of nemolizumab.

Hybridomas can be prepared, for example, according to the method of Milstein et al. (Kohler, G. and Milstein, C., Methods Enzymol. (1981) 73: 3-46). When the immunogenicity of an antigen is low, immunization may be performed after linking the antigen with a macromolecule having immunogenicity, such as albumin. Antigens used to prepare monoclonal antibodies that have a binding and/or neutralizing activity against human IL31-RA are not particularly limited, as long as they enable preparation of antibodies that have a binding and/or neutralizing activity against human IL31-RA. For example, it is known that there are a number of variants of human IL31-RA, and any variant may be used as an immunogen as long as it enables preparation of antibodies that have a binding and/or neutralizing activity against human IL31-RA. Alternatively, under the same condition, a peptide fragment of IL31-RA or a protein in which artificial mutations have been introduced into the natural IL31-RA sequence may be used as an immunogen. Human IL31-RA.3 is one of preferred immunogens in preparing antibodies that have an activity of binding and/or neutralizing IL31-RA in the present disclosure.

The IL31-RA-binding activity of therapeutic antibodies can be determined by methods known to those skilled in the art. Methods for determining the antigen-binding activity of an antibody include, for example, ELISA (enzyme-linked immunosorbent assay), EIA (enzyme immunoassay), RIA (radioimmunoassay), and fluorescent antibody method. For example, when enzyme immunoassay is used, antibody-containing samples, such as purified antibodies and culture supernatants of antibody-producing cells, are added to antigen-coated plates. A secondary antibody labeled with an enzyme, such as alkaline phosphatase, is added and the plates are incubated. After washing, an enzyme substrate, such as p-nitrophenyl phosphate, is added, and the absorbance is measured to evaluate the antigen-binding activity. The binding and/or neutralizing activity of a therapeutic antibody against IL31-RA can be measured, for example, by observing the effect of suppressing the growth of the IL-31-dependent cell line. For example, the activity of a purified mouse IL-31 antibody can be assayed by assessing the IL-31-dependent growth of Ba/F3 cells transfected with mouse IL-31 receptor α and mouse OSMR genes.

Any of the anti-IL31RA antibodies (i.e. "therapeutic antibodies") disclosed herein, including nemolizumab and fragments or variants thereof, can be used for treating and/or preventing PN and achieving the disclosed therapeutic endpoints. Optimal doses and routes of administration may vary.

IV. Pharmaceutical Compositions

Provided herein are pharmaceutical compositions for use in the treatment or prevention of prurigo nodularis (PN), including skin lesions or nodules or pruritus caused by PN. The pharmaceutical compositions comprise an anti-IL31RA antibody (i.e. "therapeutic antibody"), such as nemolizumab or a fragment or variant thereof, as an active ingredient.

The phrase "comprise(s) nemolizumab or a fragment or variant thereof as an active ingredient" means comprising nemolizumab or a fragment or variant thereof as at least one of the active ingredients, and does not limit the proportion of the antibody. In addition, the therapeutic agents for PN in the present disclosure may also comprise, in combination with nemolizumab or a fragment or variant thereof, other ingredients that enhance the treatment or prevention of PN. For example, the composition may comprise one or more topical corticosteroid creams or injections, ointments with menthol or phenol to cool and soothe itchy skin, capsaicin cream, oral corticosteroids, selective serotonin reuptake inhibitors (SSRIs), and oral antihistamines.

Pharmaceutical compositions of nemolizumab or a fragment or variant thereof of the present disclosure can be prepared as formulations according to standard methods (see, for example, Remington's Pharmaceutical Science, Mark Publishing Company, Easton, USA). The pharmaceutical compositions generally comprise a carrier and/or additive in addition to the antibody. For example, in some embodiments, the pharmaceutical composition comprises one or more surfactants (for example, PEG and Tween), excipients, antioxidants (for example, ascorbic acid), coloring agents, flavoring agents, preservatives, stabilizers, buffering agents (for example, phosphoric acid, citric acid, and other organic acids), chelating agents (for example, EDTA), suspending agents, isotonizing agents, binders, disintegrators, lubricants, fluidity promoters, corrigents, light anhydrous silicic acid, lactose, crystalline cellulose, mannitol, starch, carmelose calcium, carmelose sodium, hydroxypropylcellulose, hydroxypropylmethylcellulose, polyvinylacetaldiethylaminoacetate, polyvinylpyrrolidone, gelatin, medium chain fatty acid triglyceride, polyoxyethylene hydrogenated castor oil 60, sucrose, carboxymethylcellulose, corn starch, and inorganic salt. In some embodiments, the pharmaceutical composition comprises one or more other low-molecular-weight polypeptides, proteins such as serum albumin, gelatin, and immunoglobulin, and amino acids such as glycine, glutamine, asparagine, arginine, and lysine.

When nemolizumab or a fragment or variant thereof may be prepared as an aqueous solution for injection, in which nemolizumab or a fragment or variant thereof may be dissolved in an isotonic solution containing, for example, physiological saline, dextrose, or other excipients or tonifiers (i.e., tonicity agents). The tonifier may include, for example, D-sorbitol, D-mannose, D-mannitol, and sodium chloride. In addition, appropriate solubilizing agents, for example, alcohols (for example, ethanol), polyalcohols (for example, propylene glycols and PEGs), and non-ionic detergents (polysorbate 80 and HCO-50) may be used concomitantly.

In some embodiments, nemolizumab or a fragment or variant thereof may be encapsulated in microcapsules (microcapsules made of hydroxymethylcellulose, gelatin, polymethylmethacrylate, and the like), and made into components of colloidal drug delivery systems (liposomes, albumin microspheres, microemulsions, nano-particles, and nano-capsules) (for example, see "Remington's Pharmaceutical Science 16th edition" &, Oslo Ed. (1980)). Moreover, methods for making sustained-release drugs are known, and these can be applied for nemolizumab or a fragment or variant thereof (Langer et al., J. Biomed. Mater. Res. (1981) 15, 167-277; Langer, Chem. Tech. (1982) 12, 98-105; U.S. Pat. No. 3,773,919; European Patent Application (EP) No. 58,481; Sidman et al., Biopolymers (1983) 22, 547-56; EP 133,988).

The pharmaceutical compositions of the present disclosure can be administered either orally or parenterally, but are preferably administered parenterally. Specifically, the pharmaceutical compositions are administered to patients by injection or percutaneous administration. Injections include, for example, intravenous injections, intramuscular injections, and subcutaneous injections, for systemic or local administration. The pharmaceutical compositions may be given to sites where inflammation and/or itching is to be suppressed, or areas surrounding the sites by local infusion or intramuscular or subcutaneous injection. In some embodiments, the pharmaceutical compositions are administered at the site of one or more skin excoriations, lesions, or nodules, or proximal to the site of one or more skin excoriations, lesions, or nodules.

The administration methods can be properly selected according to the patient's age, weight, and condition. The single-administration dose can be selected, for example, from within the range of 0.0001 to 100 mg of the antibody (e.g., nemolizumab or a fragment or variant thereof) per kg body weight. Alternatively, for example, when the antibody is administered to human patients, the dose of the antibody can be selected from within the range of 0.001 to 1,000 mg/kg body weight. In some embodiments, the composition is formulated to administer a dose containing, for example, about 0.01 to 50 mg/kg, about 0.01 mg/kg to about 0.1 mg/kg, about 0.05 mg/kg to 0.15 mg/kg, about 0.1 mg/kg to about 0.6 mg/kg, about 0.1 mg/kg to about 1 mg/kg, about 0.25 mg/kg to about 0.75 mg/kg, about 0.4 mg/kg to about 0.8 mg/kg, about 0.4 mg/kg to about 1.8 mg/kg, about 0.5 to about 2.5 mg/kg, about 0.8 mg/kg to about 2.2 mg/kg, about 1 mg/kg to about 2.5 mg/kg, about 1 mg/kg to about 3.5 mg/kg, about 1 mg/kg to about 5 mg/kg, about 2 mg/kg to about 4 mg/kg, about 2.5 mg/kg to about 10 mg/kg, about 5 mg/kg to about 10 mg/kg, about 10 mg/kg to about 20 mg/kg, about 10 mg/kg to about 40 mg/kg, about 20 mg/kg to about 50 mg/kg, about 25 mg/kg to about 75 mg/kg, about 50 mg/kg to about 100 mg/kg, or about 100 mg/kg to about 500 mg/kg, or about 100 mg/kg to about 1000 mg/kg body weight of nemolizumab or a fragment or variant thereof. In preferred embodiments, the dose ranges from about 0.01 mg/kg to about 0.1 mg/kg, about 0.1 mg/kg to about 0.5 mg/kg, about 0.5 mg/kg to about 1.5 mg/kg, about 1.5 mg/kg to about 2.5 mg/kg, or about 2.5 mg/kg to about 10 mg/kg. In some embodiments, the dose is about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3 mg/kg, about 3.5 mg/kg, about 4 mg/kg, about 4.5 mg/kg, about 5 mg/kg, about 6 mg/kg, about 7 mg/kg, about 8 mg/kg, about 9 mg/kg, about 10 mg/kg, about 15 mg/kg, about 25 mg/kg, about 50 mg/kg, about 75 mg/kg, about 100 mg/kg, about 500 mg/kg, or about 1,000 mg/kg. In particular embodiments, the effective amount of nemolizumab or a fragment or variant thereof is about 0.1 mg/kg, about 0.5 mg/kg, about 1 mg/kg, about 1.5 mg/kg, about 2 mg/kg, or about 2.5 mg/kg. In a preferred embodiment, the dose is about 0.5 mg/kg.

The present disclosure provides a pharmaceutical composition for use in the treatment or prevention of prurigo nodularis (PN) in a subject, comprising an anti-IL31RA antibody (e.g., nemolizumab or a fragment or variant thereof), as an active ingredient, wherein the subject differentially expresses at least one gene selected from the genes disclosed in Table 1 compared to a reference level of expression for the at least one gene.

The present disclosure provides a pharmaceutical composition for use in the treatment or prevention of prurigo nodularis (PN) in a subject, comprising an anti-IL31RA antibody (e.g., nemolizumab or a fragment or variant thereof), as an active ingredient, wherein the subject differentially expresses at least one gene selected from the genes disclosed in Table 1 compared to a reference level of expression for the at least one gene, and wherein the subject is diagnosed as having prurigo nodularis (PN), by detecting in a sample obtained from a subject suspected of having PN the expression level of at least one, at least two, at least three, at least four, or at least five of the differentially expressed genes (DEGs) in Table 1, and comparing the expression level of the DEGs to a reference level, wherein the reference level is the corresponding level of gene expression for each DEG in a sample from an individual that does not have PN.

Any of the pharmaceutical compositions disclosed herein, including nemolizumab and fragments or variants thereof, can be used for treating and/or preventing PN and achieving the disclosed therapeutic endpoints. Optimal doses and routes of administration may vary.

V. Methods of Treatment/Prevention and Compositions for Treating or Preventing PN The present disclosure provides methods of treating or preventing pruritus in a subject having prurigo nodularis (PN), the method comprising, consisting of, or consisting essentially of administering an anti-IL-31RA antibody (i.e., a "therapeutic antibody"), such as nemolizumab or a fragment or variant thereof to the subject. The disclosed methods may be performed to achieve specific therapeutic endpoints, which are discussed in more detail below. Also disclosed herein are uses of an anti-IL-31RA antibody (i.e., a "therapeutic antibody"), such as nemolizumab or a fragment or variant thereof to the subject for treating or preventing PN and/or achieving the disclosed therapeutic endpoints. Also disclosed herein are anti-IL-31RA antibodies (i.e., a "therapeutic antibodies"), such as nemolizumab or a fragment or variant thereof to the subject for use in treating or preventing PN and/or achieving the disclosed therapeutic endpoints. Additionally, particular subgroups of subjects with PN may be especially suitable for treatment according to the disclosed methods and uses (e.g., patients presenting with any of the DEGs disclosed in Table 1).

The present disclosure is the first to report a transcriptomic signature for PN that is able to not only identify and positively diagnose PN, but also identify subjects with PN that will likely response to treatment with an anti-IL-31RA antibody (e.g., nemolizumab) and track the response of the treatment with an anti-IL-31RA antibody (e.g., nemolizumab).

The present disclosure is also the first to report a plasma proteome signature for PN subjects that were successfully treated with an anti-IL-31RA antibody, such as nemolizumab. This "responder signature" may be used not only as a marker of positive clinical endpoints, but also identify subjects with PN that will likely response to treatment with an anti-IL-31RA antibody (e.g., nemolizumab) and track the response of the treatment with an anti-IL-31RA antibody (e.g., nemolizumab).

A. Subject Being Treated

A subject being treated for PN according to the disclosed methods and uses may exemplify one or more of the underlying gene expression patterns that are disclosed herein. In particular, a subject with PN that is to be treated according to the disclosed methods and uses may differentially express up to or at least 5,943 genes (known as differentially expressed genes or DEGs), which are shown in FIG. 1A and Table 1 below. This differential gene expression may be observed in the skin of the subject and, in particular, in a skin sample comprising or consisting of a nodule or lesion. Of these DEG, 2,060 may be increased (i.e., overexpressed) and 3,874 may be decreased (i.e., under expressed). Genes that may be increased the most include:

- KRT6C, which may be increased at least 100-fold, at least 150 fold, at least 200-fold, at least 250-fold, at least 300-fold, at least 350-fold, at least 400-fold, at least 450-fold, at least 500-fold, at least 550-fold, or 588-fold compared to the expression level in a sample (e.g., a skin sample) from an individual that does not have PN;
- DEFB4A, which may be increased at least 25-fold, at least 50-fold, at least 75-fold, at least 100-fold, at least 125-fold, or at least 150 fold compared to the expression level in a sample (e.g., a skin sample) from an individual that does not have PN; and
- KRT16, which may be increased at least 10-fold, at least 20-fold, at least 30-fold, at least 40-fold, at least 50-fold, at least 60-fold, at least 70-fold, at least 80-fold, or at least 90 fold compared to the expression level in a sample (e.g., a skin sample) from an individual that does not have PN.

Decreased genes include:

- LCE5A, which may be decreased at least 2-fold, at least 3-fold, at least 4-fold, at least 5-fold, at least 6-fold, at least 7-fold, at least 8-fold, at least 9-fold, at least 10-fold, or at least 11 fold compared to the expression level in a sample (e.g., a skin sample) from an individual that does not have PN; and
- AQP7, which may be decreased at least 2-fold, at least 3-fold, at least 4-fold, at least 5-fold, at least 6-fold, at least 7-fold, or at least 7.9 fold compared to the expression level in a sample (e.g., a skin sample) from an individual that does not have PN.

Genes that encode cytokines may also be overexpressed in subjects suffering from PN that can be treated or prevented according to the disclosed methods and uses. For the cytokine genes, the most prominent up-regulated genes are IL-36 family members and IL-20 family members. These upregulated or overexpressed genes may include:

IL36A (e.g., about 6.8-fold, FDR=$1.8\times10^{-4}$);
IL36G (e.g., about 8.4-fold, FDR=$3.9\times10^{-25}$);
IL19 (e.g., about 5.1-fold, FDR=$7.4\times10^{-4}$);
IL20 (e.g., about 3.5-fold, FDR=$1.7\times10^{-3}$);
IL22 (e.g., about 2.7-fold, FDR=$2.9\times10^{-2}$);
IL24 (e.g., about 5.8-fold, FDR=$3.8\times10^{-10}$); and
IL26 (e.g., about 4.9-fold, FDR=$3.3\times10^{-3}$).

Each of these IL-36 and IL-20 family member cytokine genes may be overexpressed by at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, or at least about 8-5-fold compared to the expression level in a sample (e.g., a skin sample) from an individual that does not have PN.

Other factors that may be upregulated or overexpressed in a sample (e.g., a skin sample) obtained from a subject with PN that is to be treated may include IL1A (e.g., about 4.7-fold, FDR=$1.0\times10^{-12}$), IL1B (e.g., about 4.1-fold, FDR=$3.7\times10^{-6}$, and IL4R (e.g., about 2.6-fold (FDR=$6.3\times10^{-19}$). Table 1 at the end of the examples section of the specification provides a more exhaustive list of the DEGs.

Certain gene ontology (GO) categories also may be evident in the skin of subjects with PN that are treated according to the disclosed methods and uses. These GO categories are:

"cornified envelope" (FDR=$1.5\times10^{-12}$),
"epidermal cell differentiation" (FDR=$6.4\times10^{-10}$),
"keratinization" (FDR=$1.6\times10^{-12}$),
"peptidase regulator activity" (FDR=$1.1\times10^{-4}$),
"interleukin-4 and 13 signaling" (FDR=$6.8\times10^{-7}$),
"interferon alpha/beta signaling" and "response to interferon gamma" (FDR=$4.1\times10^{-7}$, and FDR=$4.1\times10^{-6}$, respectively),
"IL23 pathway" (FDR=$2\times10^{-5}$), and
"mitotic metaphase and anaphase" (FDR=$3.8\times10^{-10}$).

These categories reflect the hyperproliferative nature of PN, which was discovered to be associated with altered epidermal differentiation and inflammatory components. In some embodiments, a subject with PN that is treated according to the disclosed methods and uses may overexpress the proliferative marker Ki67 (MKI67), the cell cycle gene CDKN1A, and/or inflammatory networks involving IL-1 and IL-36.

A subject with PN that is treated according to the disclosed methods or uses may additionally or alternatively present with one or more of the co-expression modules or clusters shown in FIG. 1D and Table 3 at the end of the examples section of the specification. Distinct functions are defined for these co-expressing gene modules, as noted herein.

The present disclosure also provides specific cell-type signatures for non-lesional and lesional PN skin that can be present in subjects with PN that are treated according to the disclosed methods and uses. For example, a subject with PN may possess the transcriptomic signature associated with epithelial cells and keratinocytes was observed in FIG. 2A and/or may possess a Th2 associated signature, as described herein. Other inflammatory signatures, such as macrophages, may also be prominent in PN lesions and the skin of subjects with PN.

In general, the disclosed methods and uses can treat or prevent PN in subjects that suffer from mild, moderate, or severe pruritus. In some embodiments, the PN may be categorized as moderate to severe. In some embodiments, the PN may be categorized as moderate, while in other embodiments, the PN may be categorized as severe. In some embodiments, pruritus can be scored as none, mild, moderate, or severe. "None," "mild," "moderate," and "severe" are terms of art in describing the presence, extent, and/or intensity of excoriations. Those of skill in the art know the metes and bounds of these terms. For example, pruritus can be characterized according to one or more of the following methods known by those skilled in the art. The intensity can be quickly measured with monodimensional scales that are routinely used in clinical care. See Pereira et al., Allergology International (2017) 66:3-78. Additionally or alternatively, patients can be asked to rate their itch intensity from 0 ("no itch") to 10 ("worst imaginable itch") with the numerical rating scale (NRS). Another monodimensional scale, the visual analogue scale (VAS), provides patients with the opportunity to indicate the intensity of their itch by marking on a 10 cm long, ruler-shaped scale. Both endpoints are marked with a number corresponding to the intensity, with 0 representing "no itch" and 10 the "worst imaginable itch." Scores below 3.0 VAS/NRS points are generally associated with mild itch, whereas scores higher than 6.9 illustrate severe itch. Scores above 9.0 represent a very severe itch. The verbal rating scale (VRS) is a further monodimensional scale that allows patients to describe their itch intensity by means of gradually rising adjectives (0—no itch, 4—worst imaginable itch). The NRS, VAS and VRS have been validated in large-scale studies consisting of chronic pruritus patients with pruritic dermatoses or pruritus of various origins. These instruments have high reproducibility and there was a high correlation between scales 6, 7, 8. Chronic pruritus can greatly reduce patient quality of life. For this reason, Dermatology Life Quality Index (DLQI) is widely used and has been validated. DLQI scores range from 0 to 30, with higher scores indicating a lower quality of life. Investigators' Global Assessment (IGA) scores range from 0 (clear) to 5 (very severe disease) and are presented as a percentage of patients in the indicated population. In the present study, IGA scores range from 0 to 4.

A subject being treated for PN according to the disclosed methods and uses may exemplify one or more of the disclosed plasma protein signature alterations that are disclosed herein. In particular, a subject with PN that is to be treated according to the disclosed methods and uses may exhibit (a) a decrease in migration and cell movement of leukocytes; (b) an inhibition of STAT3 and STAT5b pathways; (c) a downregulation in IL-6 and VEGF pathways; (d) a decrease in TGFB1 pathway, or (e) a combination thereof. The foregoing decreases or inhibitions may be observed at a specified time point after the commencement of treatment, such as 2 weeks, 4 weeks, 6 weeks, 8 weeks, 10 weeks, or 12 weeks. The decreases or inhibitions may be determined relative to (i) a control sample obtained from an individual or individuals without PN or (ii) a biological sample obtained from the subject prior to administration of the anti-IL-31RA antibody. Additionally or alternatively, the subject may exhibit an upregulation in a neuronal ontology terms including CREB signaling in neurons, Synaptogenesis signaling pathway, Cell death of neuroglia and Apoptosis of neuroglia and a combination thereof following administration of the anti-IL-31RA antibody.

A subject with PN that is suitable for treatment according to the disclosed methods and uses may exhibit high levels of leukocyte migration or leukocyte cell movement relative to an individual or population without PN or in the subject prior to commencing treatment with an anti-IL-31RA antibody, such as nemolizumab. Additionally or alternatively, a suitable subject may exhibit STAT3 pathway activity or expression that is comparatively high relative to an individual or population without PN or in the subject prior to commencing treatment with an anti-IL-31RA antibody, such as nemolizumab. Additionally or alternatively, a suitable subject may exhibit TGFB1 pathway activity or expression that is comparatively high relative to an individual or population without PN or in the subject prior to commencing treatment with an anti-IL-31RA antibody, such as nemolizumab. Additionally or alternatively, a suitable subject may exhibit amounts of circulating cytokine signature that are comparatively high in a subject with PN relative to an individual or population without PN or in the subject prior to commencing treatment with an anti-IL-31RA antibody, such as nemolizumab. Such cytokine pathways can include, but are not limited to IL-6, and VEGF pathways.

Prior to treatment with an anti-IL-31Ra antibody, such as nemolizumab, the amount of the disclosed protein markers in the plasma of a subject with PN may be at least 2-fold, at least 3-fold, at least 4-fold, at least 5-fold, at least 6-fold, at least 7-fold, at least 8-fold, at least 9-fold, at least 10-fold, at least 15-fold, at least 20-fold, at least 25-fold, at least 30-fold, at least 35-fold, at least 40-fold, at least 45-fold, or at least 50-fold higher than a baseline level. The baseline level may be determined relative to (i) a control sample obtained from an individual or individuals (i.e., a population) without PN or (ii) a biological sample obtained from the subject prior to administration of the anti-IL-31RA antibody.

In some embodiments, the subject has been diagnosed of PN for at least about 6 months. In particular embodiments, the subject has at least about 20 nodules on his/her body with a bilateral distribution. In particular embodiments, the subject has prurigo lesions on upper limbs, with or without lesions on the trunk or lower limbs. In some embodiments, the pruritus has been assigned a score of at least 7 on the Numerical Rating Scale (NRS). In some embodiments, the mean of the worst daily intensity of the NRS score is at least 7 over the previous 3 days. In some embodiments, the mean of the worst daily intensity of the NRS score is at least 7 over the previous week.

In some embodiments, the subject does not have atopic dermatitis (AD). In some embodiments, the subject does not have chronic pruritus resulting from a condition other than PN, such as scabies, insect bite, lichen simplex chronicus, psoriasis, acne, folliculitis, habitual picking, lymphomatoid papulosis, chronic actinic dermatitis, dermatitis herpetiformis, sporotrichosis, or bullous disease. In some embodiments, the subject does not have neuropathic or psychogenic pruritus, such as notalgia paresthetica, brachioradial pruritus, dilutional parasitosis, or pathomimia.

B. Therapeutic Endpoints for Treatment

Based on the data provided herein, it is believed that IL-31 signaling is upstream of IL-17 and IL-4 signaling, at least in subjects with PN, as treatment with the anti-IL-31RA antibody nemolizumab was able to alter the transcriptome expression signature of IL-17 and IL-4. Accordingly, the disclosure provides methods of normalizing differentially expressed genes (DEGs) in subjects with PN, comprising administering to a subject with PN an anti-IL-31RA antibody, such as nemolizumab or a fragment or variant thereof. As shown in the Examples section below, treatment or prevention with nemolizumab leads to normalization of a number of PN associated DEGs for both increased (e.g., about 969 genes), and decreased genes (e.g., about 1,268 genes). See FIG. 4A. In some embodiments, about 5, about 10, about 15, about 20, about 25, about 50, about 75, about 100, about 150, about 200, about 250, about 300, about 350, about 400, about 450, about 500, about 550, about 600, about 650, about 700, about 750, about 800, about 850, about 900, about 950, about 1000, about 1100, about 1200, about 1300, about 1400, about 1500, about 1600, about 1700, about 1800, about 1900, about 2000, about 2100, about 2200, about 2300, about 2400, or about 2500 DEGs may be normalized in a subject with PN after treatment with an anti-IL-31RA antibody, such as nemolizumab or a fragment or variant thereof. In some embodiments, at least 5, at least 10, at least 15, at least 20, at least 25, at least 50, at least 75, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, at least 1000, at least 1100, at least 1200, at least 1300, at least 1400, at least 1500, at least 1600, at least 1700, at least 1800, at least 1900, at least 2000, at least 2100, at least 2200, at least 2300, at least 2400, or at least 2500 DEGs and up to 2500, 3000, 3500, 4000, 4500, 5000, 5500, or about 6000 DEGs may be normalized in a subject with PN after treatment with an anti-IL-31RA antibody, such as nemolizumab or a fragment or variant thereof. In some embodiments, treatment or prevention may comprise administration of the anti-IL-31RA antibody (e.g., nemolizumab) once a week, once every 2 weeks, once every 3 week, once every 4 weeks, once every 5 weeks, once every 6 week, once every 7 week, or once every 8 weeks. Administration about once every 4 weeks may be preferred. Administration may be perform via injection, such as subcutaneous injection. The timeframe for determining/comparing the normalization of the DEGs may be 4 week, 5 weeks, 6 weeks, 7 weeks, 8 week, 9 weeks, 10 weeks, 11 weeks, or 12 weeks or more. For example, a baseline (i.e., at or before treatment commences) a sample (e.g., a skin sample) may be obtained from the subject to detect the level of expression of some or all of the putative DEGs disclosed in Table 1 (e.g., KRT6C, DEFB4A, KRT16, LCE5A, AQP7, IL-36 family members, IL-20 family members, etc.), and another sample can be taken and assessed at 4 week, 5 weeks, 6 weeks, 7 weeks, 8 week, 9 weeks, 10 weeks, 11 weeks, or 12 weeks or more weeks after treatment has commenced in order to determine whether the expression level of the DEGs has changed and in more in line (i.e., "normalized") with reference expression levels of the DEGs that are associated with normal, healthy skin (e.g., expression levels obtained from a skin sample from a subject without PN). Such methods can be used to track treatment and assess whether a subject is responsive to the treatment with the anti-IL-31RA antibody (e.g., nemolizumab).

GO categories enriched amongst DEGs may also be decreased or altered as a result of treatment with an anti-IL-31RA antibody (e.g., nemolizumab). For example, after 12 weeks of treatment, the following GO categories were observed to decrease: "cell cycle" (FDR=$5.6\times10^{-14}$), "keratinocyte differentiation" (FDR=$1.8\times10^{-4}$), and "interleukin-4 and 13 signaling" (FDR=$1.5\times10^{-2}$). Indeed, the data provided in the Examples section demonstrates that nemolizumab treatment (and treatment with other anti-IL-31RA antibodies) normalizes epidermal hyperproliferation, normalizes differentiation, and decreases inflammatory responses, particularly related to Th2 responses. Accordingly, the present disclosure provides methods of normalizing epidermal hyperproliferation, normalizing epidermal differentiation, and/or decreasing inflammatory responses in the skin, comprising administering to a subject with PN an anti-IL-31RA antibody (e.g., nemolizumab). In some embodiments, the inflammatory response may be a Th2 response. In some embodiments, administration of the anti-IL-31RA antibody (e.g., nemolizumab) may be once a week, once every 2 weeks, once every 3 week, once every 4 weeks, once every 5 weeks, once every 6 week, once every 7 week, or once every 8 weeks. Administration about once every 4 weeks may be preferred. Administration may be perform via injection, such as subcutaneous injection.

Figure 5A:
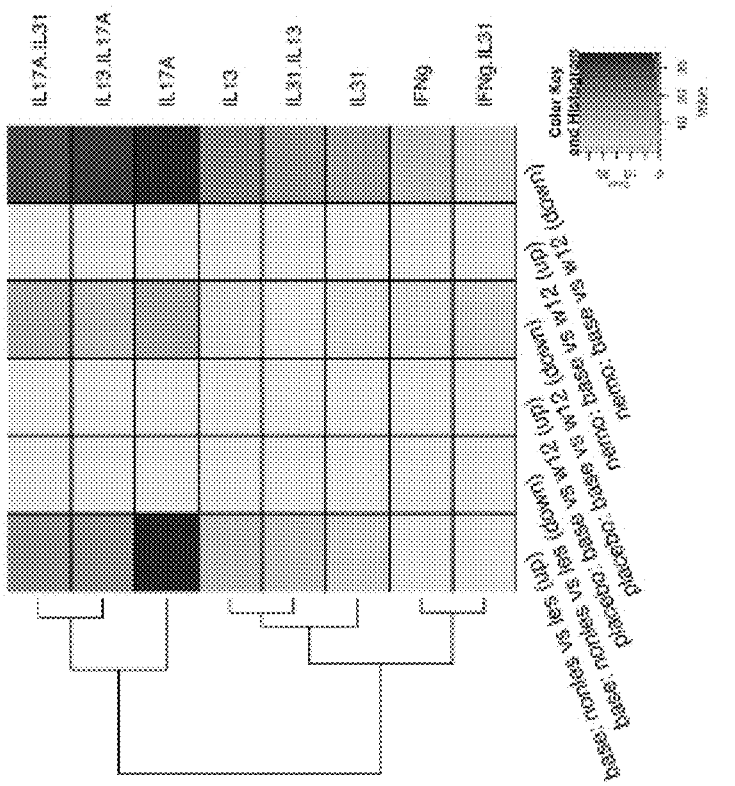
FIGS. 5A-5D shows nemolizumab treatment leads to normalized epidermal differentiation and decreased IL-31/Th2 responses in PN skin. Nemolizumab treatment led to decrease in IL-31 and IL-13 responses in PN skin compared to placebo, along with decreased expression of IL-17A response genes (A). Nemolizumab treatment was accompanied by decreases in transcriptomic signatures for Th1, Th17 and Th2 cells (B). Cross comparing transcriptomic responses in PN skin against cellular signatures obtained from single-cell data of healthy epidermis demonstrated that nemolizumab treatment led to normalization of epidermal gene expression related to the differentiated layer (KRT10+) of the epidermis, corresponding to normalization of epidermal differentiation. The different nomenclatures correspond to the different layers of the epidermis with "basal" corresponding to KRT5$^+$ basal cells, KRT1 "differentiated" corresponding to the spinous layer, and "keratinized" corresponding to the granular layers (FLG$^+$) (C). Transcription Factor Binding Site (TFBS) of PN associated DEGs that greater normalization amongst nemolizumab down-regulated genes compared to placebo (5D).
Figure 5B:
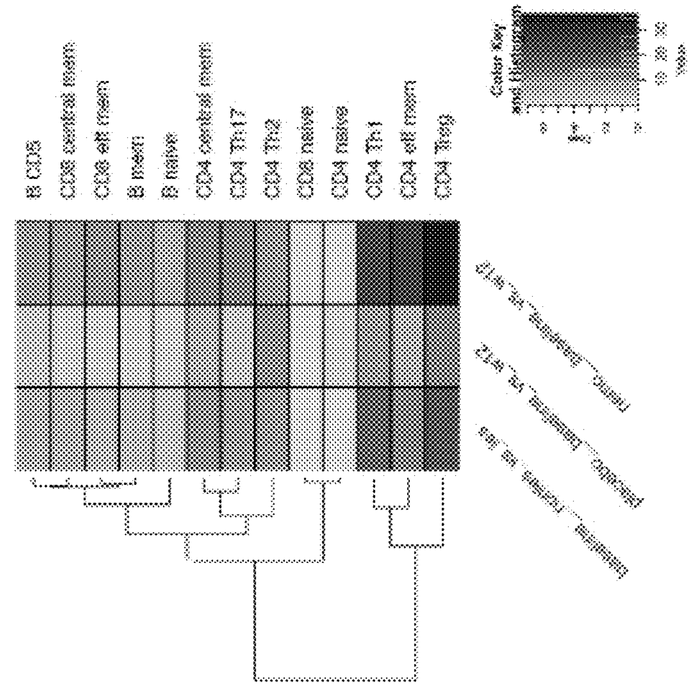

With respect to the disclosed methods of decreasing inflammatory responses in the skin of a subject with PN, in some embodiments, the cytokine response signatures generated in human epidermal rafts of the subject's skin may be altered. For example, IL17A mRNA expression was not significantly different in non-lesional vs lesional skin, nor was it different after a 12 week treatment with nemolizumab. A consistent decrease in IL-31 responses, either solitary, or in combination with other inflammatory cytokines, including the Th2 cytokine IL-13 or IL-17A can be seen in FIG. 5A, thus providing evidence of blockade of the IL-31 pathway by nemolizumab. However, IL-17A response genes are shown herein to be enriched in PN skin and are down-regulated by nemolizumab. This suggests that while IL-17A itself is not a dominant cytokine in PN, it is down-stream of IL-31 signaling. Indeed, a consistent decrease in IL-31 responses, either solitary or in combination with other inflammatory cytokines (including the Th2 cytokine IL-13, or IL-17A), was observed with treatment with nemolizumab (FIG. 5A), and more robust decreases were observed in Th1, Th17, and Th2 markers (FIG. 5B). Accordingly, IL-31 signaling is likely upstream of IL-17 and IL-4 signaling.

Figure 5C:
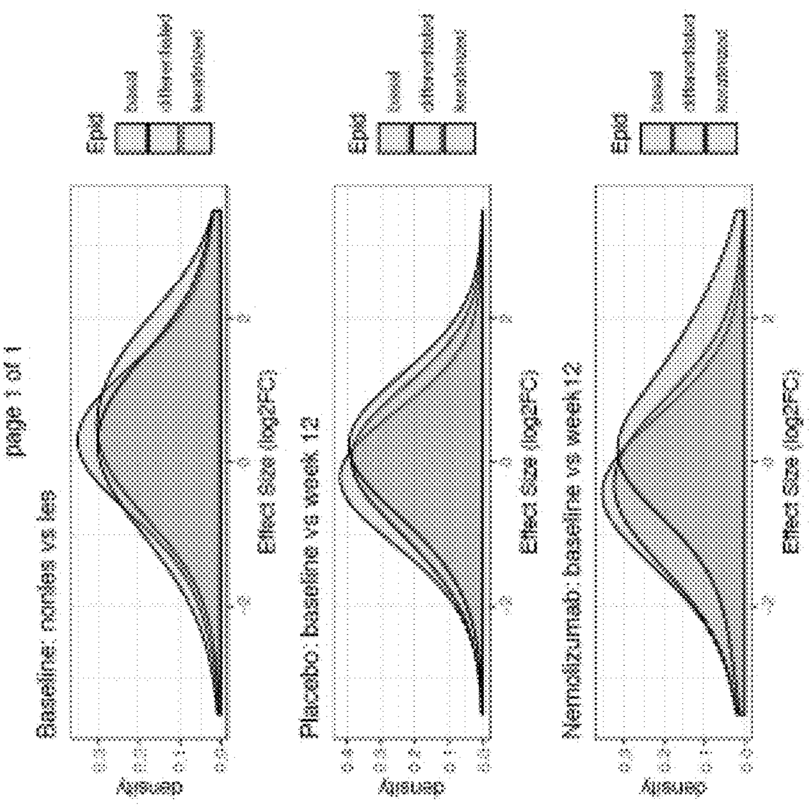

In some embodiment, a basal keratinocyte (KRT14+) signature may be elevated in the lesional skin of PN, and this signature may be restored to normal (i.e., non-PN) when treated according to the disclosed methods and uses. In some embodiments, a spinous layer (KRT10+) signature may be elevated in the PN lesional skin, and this signature may be restored to normal (i.e., non-PN) when treated according to the disclosed methods and uses (FIG. 5C).

Figure 5D:
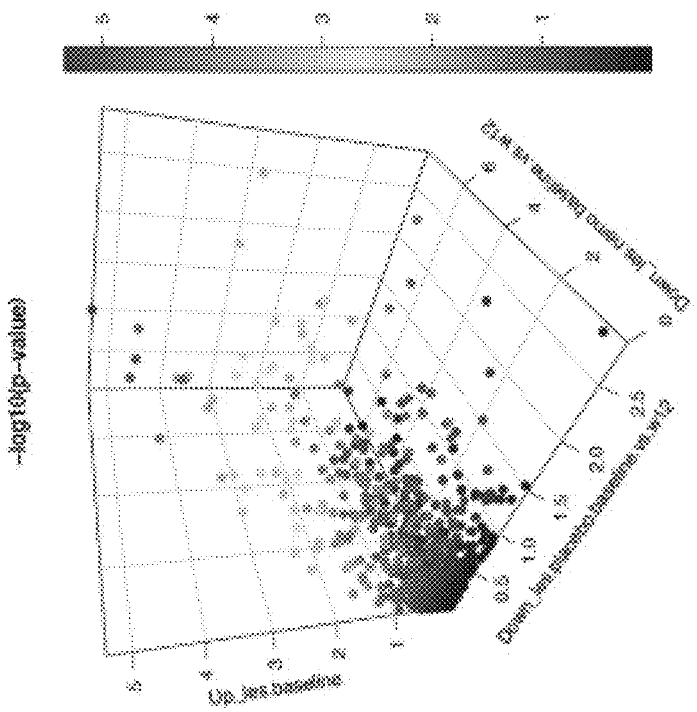
Figure 7:
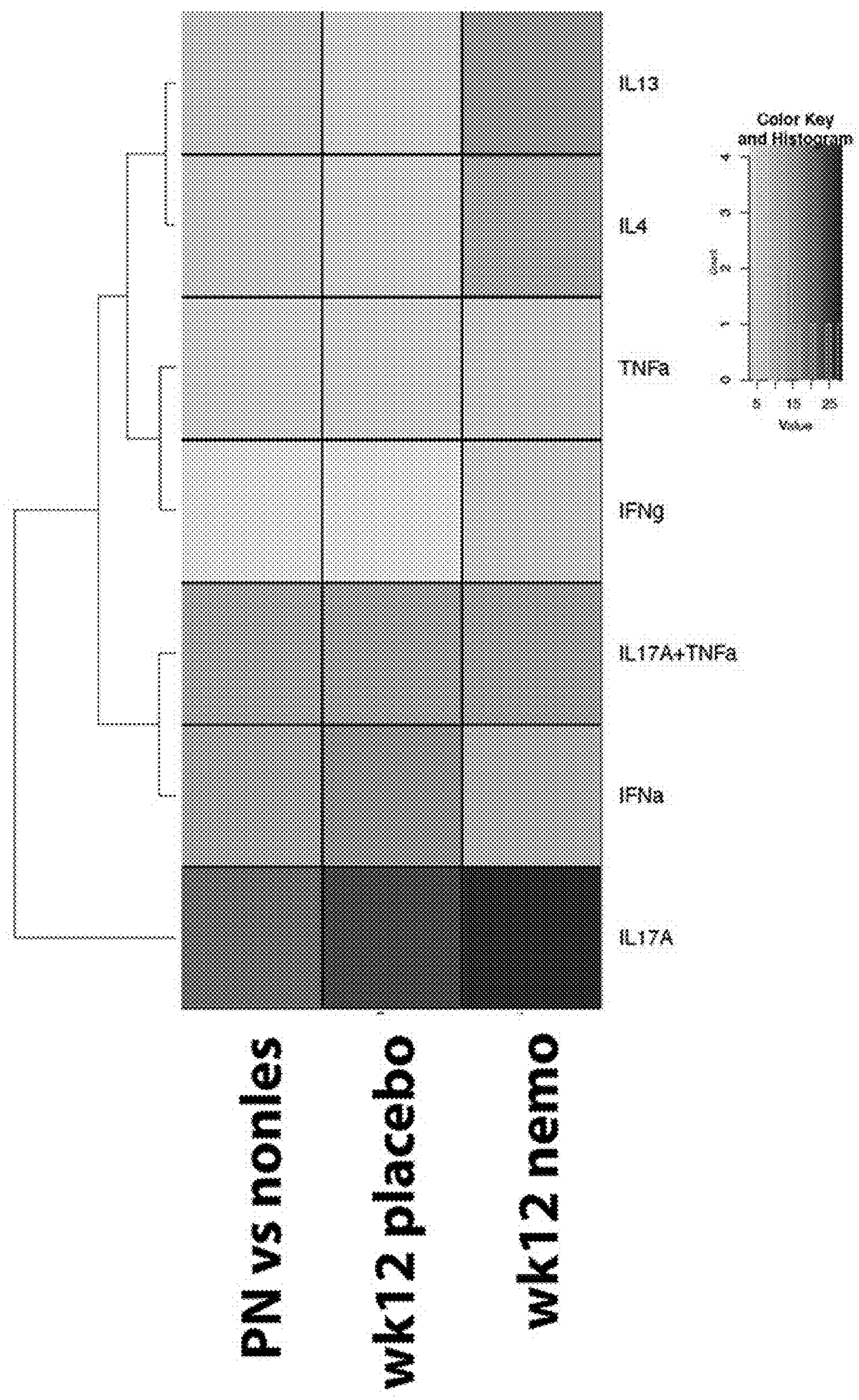
FIG. 7 shows cytokine signatures in PN in placebo vs. nemolizumab treated skin. Literature-based network generated using Genomatix Pathway System (GePS, genomatix.de), using the function-word co-citation filter and showing key cytokines as main nodes in PN skin.
Figure 8:
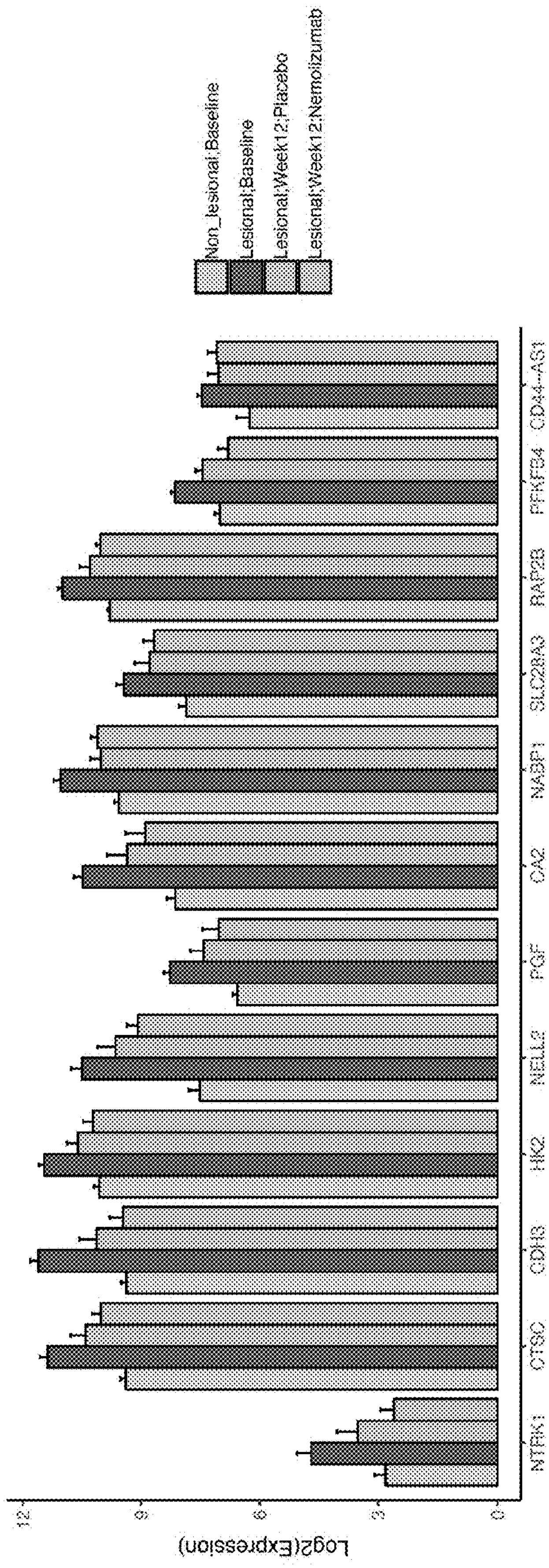
FIG. 8 shows expression of selected TFs in PN skin pre- and post-nemolizumab treatment.
Figure 9:
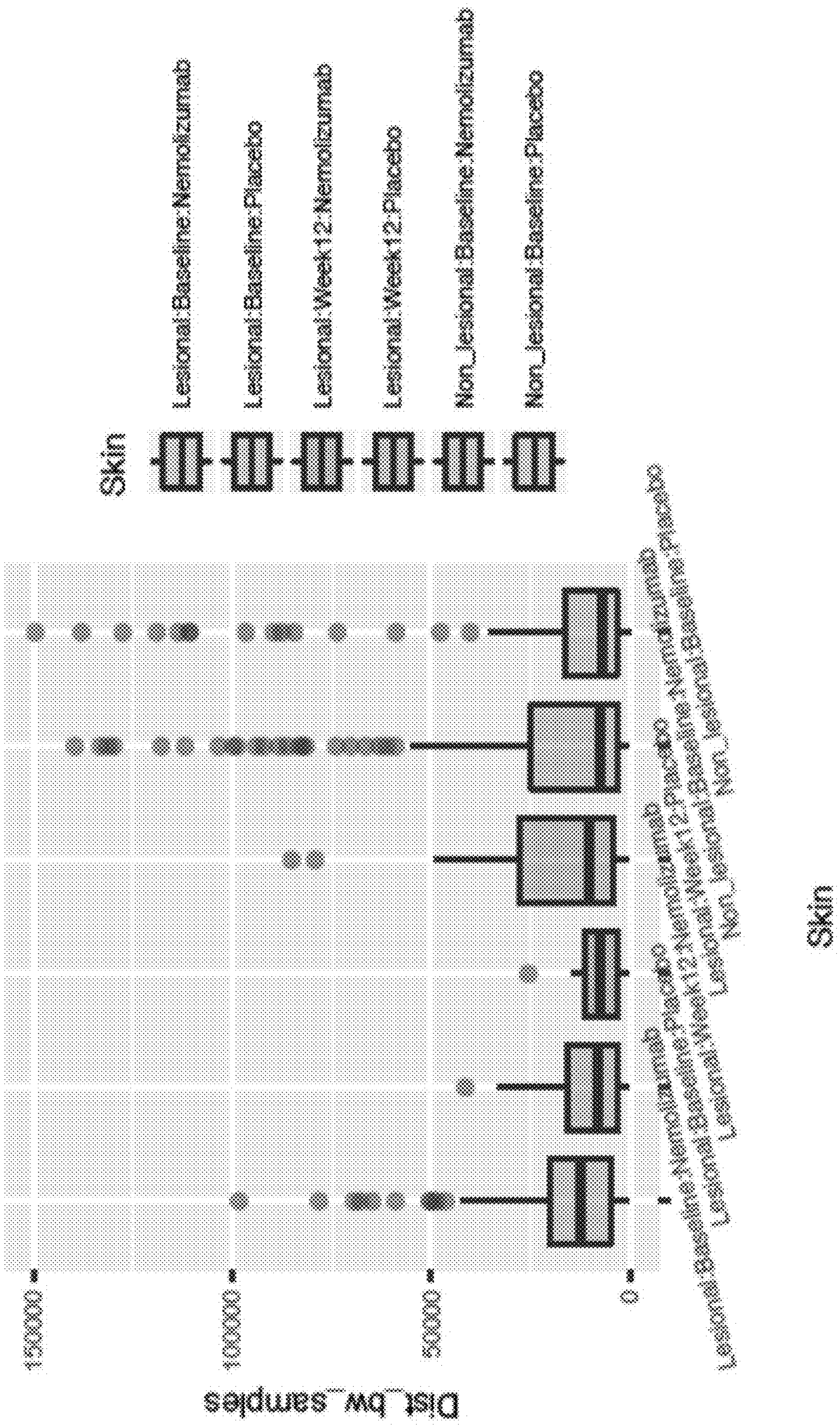
FIG. 9 shows the distance between PCA components in PN, pre- and post-nemolizumab treatment.

In some embodiments, transcription factor binding site (TFBS) that are enriched among genes up-regulated in baseline lesional skin are more likely to be enriched among the nemolizumab down-regulated genes following treatment with an anti-IL-31RA antibody, such as nemolizumab (e.g., by week 12 post-treatment, as shown in FIG. 5D). In some embodiments, the transcription factor that is down regulated by treatment can be EGR4 (which is a member of the EGF family of zinc finger transcription factors), STAT3, and/or KLF16.

The present disclosure additionally provides plasma protein markers that have been identified in subjects that were successfully treated with nemolizumab, and therefore the resulting alteration in biomarkers can be considered a "responder signature" for establishing success, as well as a means of tracking responsiveness. Thus, disclosed herein are methods of treating or preventing prurigo nodularis (PN) in a subject, comprising administering to a subject with PN an anti-IL-31RA antibody, wherein treatment with the anti-IL-31RA antibody results in: (a) a decrease in leukocyte migration and cell movement, (b) a decrease in IL-6 or a decrease in IL-6 pathway signaling, (c) a decrease in VEGF or a decrease in VEGF pathway signaling, (d) a decrease in STAT3 or a decrease in STAT3 pathway signaling, (e) a decrease in STAT5b or a decrease in STAT5b pathway signaling, (f) a decrease in TGFB1 or a decrease in TGFB1 pathway signaling, or (g) a combination thereof. In some embodiments, the subject may also exhibit an increase in the disclosed neuronal ontologies. Additionally, disclosed here are methods of altering an immune response in a subject with PN, comprising administering to a subject with PN an anti-IL-31RA antibody, wherein treatment with the anti-IL-31RA antibody results in: (a) a decrease in leukocyte migration and cell movement, (b) a decrease in IL-6 or a decrease in IL-6 pathway signaling, (c) a decrease in VEGF or a decrease in VEGF pathway signaling, (d) a decrease in STAT3 or a decrease in STAT3 pathway signaling, (e) a decrease in STAT5b or a decrease in STAT5b pathway signaling, (f) a decrease in TGFB1 or a decrease in TGFB1 pathway signaling, or (g) a combination thereof. In some embodiments, the subject may also exhibit an increase in the disclosed neuronal ontologies. The disclosed plasma protein markers are detectable by, for example, mass spectrometry and other methods of protein assessment (e.g., ELISA, Western blot, etc.).

In particular, when a subject with PN is treated with an anti-IL-31RA antibody, such as nemolizumab, the immune cells (e.g., leukocytes) may experience a decrease migration or cell movement or both.

STAT3 pathway activity, may decrease in a subject with PN that is treated with an anti-IL-31RA antibody, such as nemolizumab, relative to an individual or population without PN or to the subject prior to commencing treatment with an anti-IL-31RA antibody, such as nemolizumab.

The amount of cytokine activity may also be comparatively high in a subject with PN relative to an individual or population without PN or in the subject prior to commencing treatment with an anti-IL-31RA antibody, such as nemolizumab. Such cytokine pathways can include, but are not limited to IL-6 and VEGF pathways. In a PN subject that receives treatment with an anti-IL-31RA antibody, such as nemolizumab, the treatment may result in a decrease in IL-6 or VEGF signatures or both relative to a baseline level. The baseline level may be determined relative to (i) a control sample obtained from an individual or individuals (i.e., a population) without PN or (ii) a biological sample obtained from the subject prior to administration of the anti-IL-31RA antibody.

TGFB1 pathway activity may decrease in a subject with PN that is treated with an anti-IL-31RA antibody, such as nemolizumab, relative to an individual or population without PN or the subject prior to commencing treatment with an anti-IL-31RA antibody, such as nemolizumab.

For the purposes of the disclosed plasma protein markers, the amount of the disclosed protein markers in the plasma of a subject with PN may be at least 2-fold, at least 3-fold, at least 4-fold, at least 5-fold, at least 6-fold, at least 7-fold, at least 8-fold, at least 9-fold, at least 10-fold, at least 15-fold, at least 20-fold, at least 25-fold, at least 30-fold, at least 35-fold, at least 40-fold, at least 45-fold, or at least 50-fold higher than a baseline level. The baseline level may be determined relative to (i) a control sample obtained from an individual or individuals (i.e., a population) without PN or (ii) a biological sample obtained from the subject prior to administration of the anti-IL-31RA antibody. Similarly, after a subject with PN is treated with an anti-IL-31RA antibody, such as nemolizumab (e.g., 2 weeks, 4 weeks, 6 weeks, 8 weeks, 10 weeks, or 12 weeks after administration of the antibody), the amount of the disclosed plasma protein markers in the subject may decrease at least 2-fold, at least 3-fold, at least 4-fold, at least 5-fold, at least 6-fold, at least 7-fold, at least 8-fold, at least 9-fold, at least 10-fold, at least 15-fold, at least 20-fold, at least 25-fold, at least 30-fold, at least 35-fold, at least 40-fold, at least 45-fold, or at least 50-fold relative to a baseline level. The baseline level may be determined relative to (i) a control sample obtained from an individual or individuals (i.e., a population) without PN or (ii) a biological sample obtained from the subject prior to administration of the anti-IL-31RA antibody.

Additionally, neuronal ontologies (e.g., CREB signaling in neurons, Synaptogenesis signaling pathway, Cell death of neuroglia and Apoptosis of neuroglia) may be upregulated in subject with PN, and subsequently downregulated in nemolizumab responders subjects.

In some embodiments of the disclosed methods and uses, treatment or prevention with an anti-IL-31RA antibody, such as nemolizumab or a fragment or variant thereof, leads to decrease in pruritus scoring. The decrease in scoring may be measured by, for example, the peak pruritus numeric rating scale (PP-NRS). See, e.g., FIG. 6A. Indeed, the data provided herein show that all subject with PN that were treated with nemolizumab showed improvement in pruritus scoring. In some embodiments, the measured distance between the principle component 1 and principle component 2 (i.e., PC1/PC2 components) may be less than that of a placebo group that was not treated with nemolizumab or another anti-IL-31RA antibody. More specifically, at Week 12 (i.e., 12 weeks after commencing treatment) the proportion of patients achieving 4-point reduction of weekly average of the PP NRS was significantly higher in the nemolizumab group compared to placebo (52.9% versus 8.3%, $p<0.001$). At Week 12 the proportion of subjects achieving IGA Success (Defined as IGA 0 [Clear] or 1 [Almost Clear]) was significantly higher in the nemolizumab group compared to placebo (20.6% versus 2.8%, $p=0.02$).

C. Doses and Dosing Regimen for the Disclosed Methods and Uses

An effective amount of an anti-IL-31RA antibody, such as nemolizumab or a fragment or variant thereof, is an amount sufficient to effect beneficial or desired results such as alleviating at least one or more symptom of PN. An effective amount as used herein would also include an amount sufficient to delay or prevent the development pruritus, alter the course of a PN symptom, or reverse a symptom of PN. Thus, it is not possible to specify the exact "effective amount." However, for any given case, an appropriate "effective amount" can be determined by one of ordinary skill in the art using only routine experimentation.

An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents of the present disclosure for any particular subject depends upon a variety of factors including the activity of the specific compound employed, the age, body weight, general health, sex, and diet of the subject, the time of administration, the rate of excretion, the drug combination, and the severity of the particular disorder being treated and form of administration. Treatment and prevention dosages generally may be titrated to optimize safety and efficacy. The dosage can be determined by a physician and adjusted, as necessary, to suit observed effects of the treatment. Typically, dosage-effect relationships from in vitro and/or in vivo tests initially can provide useful guidance on the proper doses for patient administration. In general, one will desire to administer an amount of the compound that is effective to achieve a serum level commensurate with the concentrations found to be effective in vitro. Determination of these parameters is well within the skill of the art. These considerations, as well as effective formulations and administration procedures are well known in the art and are described in standard textbooks.

Dosage regimens for treating or preventing PN may comprise flat dosing (i.e., administering the same dose repeatedly at pre-determined intervals) or comprise a loading dose (i.e., administrating an initial dose that is higher or different than subsequent, serial doses). For the purposes of either type of dosing regimen an effective dose may be administered topically, parenterally, subcutaneously, subdermally, intradermally, or intramuscularly. In preferred embodiments, administration comprises subcutaneous injection.

In some embodiments, a loading dose and the subsequent serial doses may be administered via the same route (e.g., subcutaneously), while in some embodiments, a loading dose and the subsequent serial doses may be administered via different routes (e.g., parenterally and subcutaneously, respectively). In some embodiments, the loading dose may be about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, or higher. In some embodiments, the loading dose may be 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, or higher. In some embodiments, the loading dose may be about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3 mg/kg, about 3.5 mg/kg, about 4 mg/kg, about 4.5 mg/kg, about 5 mg/kg, about 6 mg/kg, about 7 mg/kg, about 8 mg/kg, about 9 mg/kg, about 10 mg/kg, about 15 mg/kg, about 25 mg/kg, about 50 mg/kg, about 75 mg/kg, about 100 mg/kg, about 500 mg/kg, or about 1,000 mg/kg. In some embodiments, the loading dose may be 0.01 mg/kg, 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3 mg/kg, 3.5 mg/kg, 4 mg/kg, 4.5 mg/kg, 5 mg/kg, 6 mg/kg, 7 mg/kg, 8 mg/kg, 9 mg/kg, 10 mg/kg, 15 mg/kg, 25 mg/kg, 50 mg/kg, 75 mg/kg, 100 mg/kg, 500 mg/kg, or 1,000 mg/kg. In some embodiments, the loading dose is administered as a single injection. In some embodiments, the loading dose is administered as multiple injections, which may be administered at the same time or spaced apart at defined intervals.

The subsequent serial doses of a loading dose regimen are generally lower than the loading dose. For examples, in some embodiments, the dosing regimen may comprise a loading dose of 60 mg and a serial dose of 30 mg, which may be administered a defined interval of, for example, every 4 weeks. In some embodiments, the serial dose of a dosing regimen may be about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, or higher. In some embodiments, the serial dose may be 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, or higher. In some embodiments, the serial dose may be about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3 mg/kg, about 3.5 mg/kg, about 4 mg/kg, about 4.5 mg/kg, about 5 mg/kg, about 6 mg/kg, about 7 mg/kg, about 8 mg/kg, about 9 mg/kg, about 10 mg/kg, about 15 mg/kg, about 25 mg/kg, about 50 mg/kg, about 75 mg/kg, about 100 mg/kg, about 500 mg/kg, or about 1,000 mg/kg. In some embodiments, the serial dose may be 0.01 mg/kg, 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3 mg/kg, 3.5 mg/kg, 4 mg/kg, 4.5 mg/kg, 5 mg/kg, 6 mg/kg, 7 mg/kg, 8 mg/kg, 9 mg/kg, 10 mg/kg, 15 mg/kg, 25 mg/kg, 50 mg/kg, 75 mg/kg, 100 mg/kg, 500 mg/kg, or 1,000 mg/kg.

For the purposes of a loading dose regimen, the first serial dose may be administered 1 day, 2 days, 3 days, 4 days, 5 days, 6 days, 7 days, 8 days, 9 days, 10 days, 11 days, 12 days, 13 days, 1 week, 2 weeks, 3 weeks, 4 weeks, 5 weeks, 6 weeks, 7 weeks, 8 weeks, 9 weeks, or 10 weeks after the initial loading dose. In some embodiments, the first serial dose is administered 4 weeks after the initial loading dose. In some embodiments, the subsequent serial doses are administered once every 1 day, 2 days, 3 days, 4 days, 5 days, 6 days, 7 days, 8 days, 9 days, 10 days, 11 days, 12 days, 13 days, 1 week, 2 weeks, 3 weeks, 4 weeks, 5 weeks, 6 weeks, 7 weeks, 8 weeks, 9 weeks, or 10 weeks. In some embodiments, the serial doses are spaced 4 weeks apart (i.e., nemolizumab or a fragment or variant thereof is administered once every 4 weeks).

In some embodiments, the dose of nemolizumab or a fragment or variant thereof administered to the subject can be within the range of 0.001 to 1,000 mg/kg body weight of the subject. In some embodiments, the dose ranges from about 0.01 to 50 mg/kg, about 0.01 mg/kg to about 0.1 mg/kg, about 0.05 mg/kg to 0.15 mg/kg, about 0.1 mg/kg to about 0.6 mg/kg, about 0.1 mg/kg to about 1 mg/kg, about 0.25 mg/kg to about 0.75 mg/kg, about 0.4 mg/kg to about 0.8 mg/kg, about 0.4 mg/kg to about 1.8 mg/kg, about 0.5 to about 2.5 mg/kg, about 0.8 mg/kg to about 2.2 mg/kg, about 1 mg/kg to about 2.5 mg/kg, about 1 mg/kg to about 3.5 mg/kg, about 1 mg/kg to about 5 mg/kg, about 2 mg/kg to about 4 mg/kg, about 2.5 mg/kg to about 10 mg/kg, about 5 mg/kg to about 10 mg/kg, about 10 mg/kg to about 20 mg/kg, about 10 mg/kg to about 40 mg/kg, about 20 mg/kg to about 50 mg/kg, about 25 mg/kg to about 75 mg/kg, about 50 mg/kg to about 100 mg/kg, or about 100 mg/kg to about 500 mg/kg, or about 100 mg/kg to about 1000 mg/kg body weight of nemolizumab or a fragment or variant thereof. In preferred embodiments, the dose ranges from about 0.01 mg/kg to about 0.1 mg/kg, about 0.1 mg/kg to about 0.5 mg/kg, about 0.5 mg/kg to about 1.5 mg/kg, about 1.5 mg/kg to about 2.5 mg/kg, or about 2.5 mg/kg to about 10 mg/kg. In some embodiments, the dose is about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3 mg/kg, about 3.5 mg/kg, about 4 mg/kg, about 4.5 mg/kg, about 5 mg/kg, about 6 mg/kg, about 7 mg/kg, about 8 mg/kg, about 9 mg/kg, about 10 mg/kg, about 15 mg/kg, about 25 mg/kg, about 50 mg/kg, about 75 mg/kg, about 100 mg/kg, about 500 mg/kg, or about 1,000 mg/kg. In particular embodiments, the dose of nemolizumab or a fragment or variant thereof is about 0.1 mg/kg, about 0.5 mg/kg, about 1 mg/kg, about 1.5 mg/kg, about 2 mg/kg, or about 2.5 mg/kg. In a preferred embodiment, the dose is about 0.5 mg/kg.

In some embodiments, the dose of nemolizumab or a fragment or variant thereof administered to the subject is within the range of 1 to 100 mg, 25 to 75 mg, 30 to 60 mg, 40 to 80 mg, 20 to 80 mg, 1 to 25 mg, 1 to 50 mg, 10 to 90 mg, 15 to 85 mg, or ranges there between. In some embodiments, the dose may be about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, or higher. In some embodiments, the dose may be 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, or higher.

In some embodiments of the disclosed methods and uses, a loading dose of about 60 mg of nemolizumab or a fragment or variant thereof may be administered to a subject with PN, followed by subsequent serial doses of nemolizumab of a fragment or variant thereof at about 30 mg once every 4 weeks. In some embodiments of the disclosed methods and uses a first dose of about 60 mg of nemolizumab or a fragment or variant thereof may be administered to a subject with PN, followed by subsequent serial doses of nemolizumab of a fragment or variant thereof at about 60 mg once every 4 weeks (i.e., the dose remains constant or is a "flat" dosing regimen). In some embodiments of the disclosed methods and uses a first dose of about 30 mg of nemolizumab or a fragment or variant thereof may be administered to a subject with PN, followed by subsequent serial doses of nemolizumab of a fragment or variant thereof at about 30 mg once every 4 weeks In some embodiments of the disclosed methods and uses, nemolizumab or a fragment or variant thereof is administered by a topical or parenteral route. In some embodiments, nemolizumab or a fragment or variant thereof is administered subcutaneously. In some embodiments, the dose is administered subcutaneously at or proximal to a site of one or more nodules, lesions, or excoriations.

In some embodiments of the disclosed methods and uses, nemolizumab or a fragment or variant thereof is administered daily, every other day, twice per week, three times per week, four times per week, five times per week, six times per week, once per week, once every two weeks, once every three weeks, once every four weeks, once every five weeks, once every six weeks, once every seven weeks, once every eight weeks, once every nine weeks, once every 10 weeks, once every 11 weeks, once every 12 weeks, twice per year, once per year, and/or as needed based on the appearance of symptoms of PN. In preferred embodiments, nemolizumab or a fragment or variant thereof is administered every four weeks or every eight weeks.

In some embodiments of the disclosed methods and uses, the duration of treatment or prevention is about one day, about one week, about two weeks, about three weeks, about four weeks, about five weeks, about six weeks, about seven weeks, about eight weeks, about nine weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 24 weeks, about 30 weeks, about 36 weeks, about 40 weeks, about 48 weeks, about 50 weeks, about one year, about two years, about three years, about four years, about five years, or as needed based on the appearance of symptoms of PN. In preferred embodiments, duration of treatment or prevention is about 12 weeks to about 24 weeks, about 12 to about 36 weeks, about 12 to about 48 weeks, or about 24 to about 36 weeks.

The present disclosure provides uses of nemolizumab or a fragment or variant thereof in the manufacture of a medicament for the treatment or prevention of PN, for normalizing differentially expressed genes (DEGs) in subjects with PN, for normalizing epidermal hyperproliferation, for normalizing epidermal differentiation, and/or for decreasing inflammatory responses in the skin. All of the disclosed doses, dosing regimens, routes of administrations, biomarkers, and therapeutic endpoints are applicable to these uses as well.

The following examples are given to illustrate the present disclosure. It should be understood that the invention is not to be limited to the specific conditions or details described in these examples.

EXAMPLES

Example 1—Treatment of Prurigo Nodularis with Nemolizumab

Methods

Patient Cohort

The current study was performed in patients with moderate to severe PN. Briefly, 70 patients were randomized 1:1 to placebo (36 patients) or nemolizumab (34 patients), the latter at a dose of 0.5 mg/kg body weight administered at baseline, week 4 and week 8. Peak pruritus score on the numerical rating scale (PP-NRS) was recorded: severity of pruritus on the numerical rating scale ranged from 0 (no itch) to 10 (worst itch imaginable) and the peak pruritus was estimated using the worst scores every 24 hours in a 7-day period, with the highest score recorded as peak score. Primary outcome of the study was percent change from baseline in the PP-NRS at week 4.

Reconstructed Human Epidermis (RHE) Model

Three-dimensional RHE models were generated. Briefly, RHE cultures were generated using Normal Human Dermal Fibroblasts (NHDF) and Normal Human Epidermal Keratinocytes (NHEK). RHE cultures used were full thickness, with a dermis and an epidermis, and composed of autologous Fibroblasts and Keratinocytes. They were scaffold-free (no exogenous matrix) allowing self-assembly of the different layers of the skin by the cells and avoiding some potential inhibitors contained in collagen matrix for the RNA extractions. The RHE were cultivated in 12 well plates with insert (1.2 $cm^2$) for 42 days to obtain a minimum of two layers of dermis and six layers of epidermis. RHE cultures from 6 different donors were left unstimulated or stimulated with 7 different cytokines or cytokine combinations (3 replicates per donor per condition): IL-31, IL-13, IL-17A, IFNg, IL-31+IL-13, IL-31+IL-17A, IL-31+IFNg and IL-13+IL-17A. Concentrations for each of the cytokines used were: IL-31 (500 ng/mL), IL-13 (100 ng/mL), IL-17A (200 ng/mL), IFNg (50 ng/mL). RHE cultures were lysed 72 hours after stimulation, and RNA extraction was performed using MagMAX mirVana Total RNA isolation from Tissue Kit (ThermoFisher Scientific). RNA was purified and concentrated using RNA Clean & Concentrator-5 kit (Zymo Research), according to the protocol, and RNA concentrations ranged from 3 to 380 ng/μL. Total RNA was quantified using the QuantiFluor One RNA kit (Promega) on the GloMax-Multi+ Detection System (Promega). Library preparation was performed using the Illumina® Stranded mRNA Prep Ligation kit (Illumina), according to manufacturer's recommendations.

Skin Biopsy Processing and RNA Isolation

Skin biopsies were collected from 16 placebo and 15 nemolizumab-treated subjects. Samples included lesional and non lesional biopsies at baseline as well as lesional samples after 12 weeks of treatment (placebo or nemolizumab). RNA was extracted from skin biopsies using Tripure Isolation Reagent (Sigma-Aldrich) according to manufacturer's instructions. From these RNA samples, a DNase treatment was applied using the RNase-Free DNase kit (Cat No. 79254, Qiagen), followed by the RNeasy® MinElute® Cleanup Kit (Cat No. 74204, Qiagen).

Total RNA was quantified using the QuantiFluor One RNA kit (Promega). RNA concentration obtained ranging from 4 to 20 ng/μl. Total RNA was qualified using Fragment Analyzer 5300 (Agilent) with the Agilent HS RNA Fragment kit (Agilent). The RNA Quality Number (RQN) obtained ranging from 1 to 6. Library preparation was performed using the SMARTer Stranded Total RNA-Seq Kit V2—Pico Input Mammalian kit (TaKaRa).

RNA-Seq

Libraries were quantified using the QuantiFluor One dsDNA kit (Promega) and library analysis was performed using Fragment Analyzer 5300 (Agilent) with the Agilent HS NGS Fragment kit (Agilent). Following size selection with AMPure XP beads, shotgun libraries were sequenced using NextSeq (Illumina) on an Illumina NextSeq500 sequencer, in 2×75 bp (High Output Kit v2, 150 cycles).

RNA-Seq Data Processing

Following adapter trimming, sequence reads for 83 unique samples were aligned to human genome (GRCh37) using STAR. Gene (GENCODE v29) expression levels were then quantified with HTSeq using reads uniquely mapped to one genome location. Two RNA-seq samples were identified as outliers and 81 samples were used in subsequent analysis. Only genes with an average of at least one read per sample were retained. DESeq2 was used for expression normalization, and the negative binomial distribution was used to model the expression level for differential expression analysis. For non-lesional vs lesional and the baseline vs week 12 comparison, individual effect was included as covariate; for the placebo vs nemolizumab comparison, age and gender were controlled. False Discovery Rate (FDR)≤5% and $|\log_2$ Fold Change$|$>=1 were used as criteria to declare significant differentially expressed genes (DEGs).

Cytokine, Cell Signature, and Functional Inference Analysis

The most significant DEGs were compared against the transcripts induced by cytokines in keratinocytes (defined by FDR<=10% and 1.5-Fold Change (FC)). The top 1,000 most significant DEGs from the PN data were used for fair comparison. For the comparison against epidermal compartments gene signature, we conducted scRNA-seq on the epidermal layer of skin biopsy, and identified the top 50 marker genes for the basal, differentiated, and keratinized layers, respectively. The effect size (in $\log_2$ FC) was then investigated for each marker gene in each differential expression comparison. For transcription analysis, promoter region was defined as 5,000 base pairs upstream of the transcription start site, and the MEME suite was used to compute the enrichment statistics for the transcription factor binging.

Weighted Gene Correlation Network Analysis (WGCNA)

Gene that were expressed in at least 20% of the samples were used in the dataset for the WGCNA. The "softPower" parameter was picked as the smallest value that achieve at least r2>=0.75. Spearman correlation was used to compute the correlation, and minimum module size was set as 100. Upon the module merging, a height cut of 0.2 was used.

Results

Prurigo Nodularis is Characterized by Abnormal Keratinocyte Differentiation and Immune Activation After quality control, RNA-sequencing data analysis of biopsy tissue from patients with prurigo nodularis (PN) was performed. There were 31 PN patients with the transcriptomic data in both lesional and non-lesional skin samples. Using false-discovery rate (FDR) of ≤10% and $|\log_2|\geq 1$ as criteria, 5,943 differentially expressed genes (DEGs) were identified when comparing the uninvolved and lesional skin at baseline, of which 2,060 genes were increased and 3,874 were decreased (FIG. 1A). Genes that showed the most robust increase included KRT6C (588-fold, FDR=$8.2\times10^{-80}$), DEFB4A (150-fold, FDR=$1.1\times10^{-12}$), and KRT16 (90-fold, FDR=$1.9\times10^{-52}$). Decreased genes included LCE5A (11-fold decrease, FDR=$8.1\times10^{-18}$) and AQP7 (7.9-fold decrease, FDR=$2.6\times10^{-17}$). For the cytokines, the most prominent up-regulated genes included the IL36-family members: IL36A (6.8-fold, FDR=$1.8\times10^{-4}$) and IL36G (8.4-fold, FDR=$3.9\times10^{-25}$); IL-20 family members: IL19 (5.1-fold, FDR=$7.4\times10^{-4}$), IL20 (3.5-fold, FDR=$1.7\times10^{-3}$), IL22 (2.7-fold, FDR=$2.9\times10^{-2}$), IL24 (5.8-fold, FDR=$3.8\times10^{-10}$), and IL26 (4.9-fold, FDR=$3.3\times10^{-3}$). Other factors included IL1A (4.7-fold, FDR=$1.0\times10^{-12}$), and IL1B (4.1-fold, FDR=$3.7\times10^{-6}$). The Th2 cytokines IL4 and IL13 did not reach significance but the IL4R was increased by 2.6-fold (FDR=$6.3\times10^{-19}$) (see Table 1 at the end of the examples section of the specification).

Functional enrichment analysis was then performed on the DEGs to define the biological processes associated with PN skin. The most prominent gene ontology (GO) terms included: "cornified envelope" (FDR=$1.5\times10^{-12}$), "epidermal cell differentiation" (FDR=$6.4\times10^{-10}$), "keratinization" (FDR=$1.6\times10^{-12}$), "peptidase regulator activity" (FDR=$1.1\times10^{-4}$), "interleukin-4 and 13 signaling" (FDR=$6.8\times10^{-7}$), "interferon alpha/beta signaling" and "response to interferon gamma" (FDR=$4.1\times10^{-7}$, and FDR=$4.1\times10^{-6}$, respectively), "IL23 pathway" (FDR=$2\times10^{-5}$), and "mitotic metaphase and anaphase" (FDR=$3.8\times10^{-10}$) (FIG. 1B)(see also Table 2 at the end of the examples section of the specification). These reflect the hyperproliferative nature of PN, associated with altered epidermal differentiation and the inflammatory components; by focusing on the key expression modules in the lesional skin transcriptome, the proliferative marker Ki67 (MKI67), the cell cycle gene CDKN1A, and inflammatory networks involving IL-1 and IL-36 were revealed (FIG. 1C).

To gain a better understanding of the disease regulatory networks involved in PN skin weighted gene co-expression network analysis (WGCNA) was performed. 20 co-expression modules were identified in non-lesional skin and 10 clusters in lesional PN skin (FIG. 1D) (see Table 3 at the end of the examples section of the specification). This analysis allowed the inventors to assign distinct functions for these co-expressing gene modules, especially for the co-expression modules in PN lesional skin, with the most prominent involved immunological processes (module #8) including "immune-response" (FDR=$1.8\times10^{-47}$), "defense response" (FDR=$1.2\times10^{-39}$); cell proliferation (module #6) including "cell cycle" (FDR=$2.9\times10^{-94}$), "DNA metabolic process" (FDR=$8.7\times10^{-67}$); and epidermal processes (module #5), such as "epidermis development" (FDR $3.5\times10^{-10}$), "keratinization" (FDR=$1.7\times10^{-6}$). (FIG. 1E). Other notable findings were changes in "extracellular matrix" (FDR=$1.16\times10^{-59}$; module #2) and included genes such as MMP14, MMP16, COL1A1, COL1A2, and COL3A1, which were modestly elevated (FC≥1.4; FDR≤$6\times10^{-2}$) in the lesional skin, consistent with the association of PN with skin fibrosis.

Transcriptomic Changes in PN Lesion are Enriched for Keratinocyte and T-Cell Signatures An in silico approach (xCell) was used to infer specific cell-type signatures for each non-lesional and lesional PN skin sample. Enrichment for transcriptomic signatures associated with epithelial cells and keratinocytes was observed (p<0.001 and p<0.0001, respectively) (FIG. 2A). There was also increased prominence of Th2 associated signature (p<0.0001), consistent with the enriched GO categories for IL-4/IL-13 (FIG. 1B). Other inflammatory signatures, such as macrophages (p<0.01), were more variable (FIG. 2A). To address the relationship of PN with other hyperproliferative skin diseases that also have strong inflammatory signatures, the PN transcriptome was compared against that of atopic dermatitis (AD) and psoriasis. In a 3-way comparison there was a large number of genes that were shared between all three diseases for both up-regulated and down-regulated genes (FIG. 2B). The correlation of the effect sizes in the lesional skin was more pronounced between PN and psoriasis (Spearman correlation p=0.64) than between PN and AD (p=0.55). Genes that are commonly up-regulated in both psoriasis and PN include those participating in cytokine activity (CCL3, CXCL10, IFNG, IL12B, IL19, IL1B, IL20, etc.) and keratinization (KRT16, KRT17, LCE3A, LCE3E, etc.). See Table 4 at the end of the examples section of the specification.

Transcriptomic Changes in PN Skin with the IL31 Receptor Inhibitor Nemolizumab

Clinical results in patients with PN showed that nemolizumab resulted in a higher percentage of improvement of pruritus and skin lesions with overall good safety profile. At Week 12 the proportion of patients achieving 4-point reduction of weekly average of the PP-NRS was significantly higher in the nemolizumab group compared to placebo (52.9% versus 8.3%, p<0.001). At Week 12 the proportion of subjects achieving IGA Success (Defined as IGA 0 [Clear] or 1 [Almost Clear]) was significantly higher in the nemolizumab group compared to placebo (20.6% versus 2.8%, p=0.02).

Figure 3B:
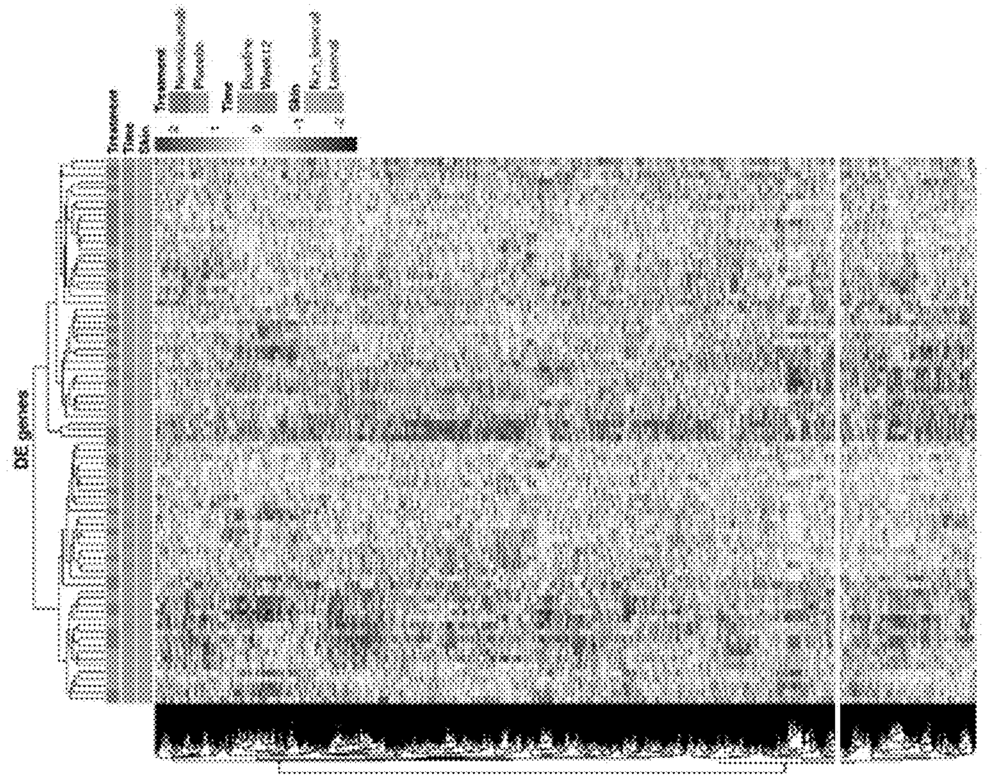
FIGS. 3A-3B shows transcriptomic changes associated with the anti-IL31R inhibitor nemolizumab. Principal component analyses (PCA) of the transcriptomic data from PN biopsies prior to and after 12-weeks of prospective placebo controlled, double blinded clinical trial with the anti-IL-31R inhibitor nemolizumab. Different colors represent different treatment groups, with lesional samples shown as triangles, and non-lesional skin shown as circles (A). Heatmap showing 2-way clustering (using genes differentially expressed between non-lesional vs lesional skin at baseline) for all samples (B).
Figure 3A:
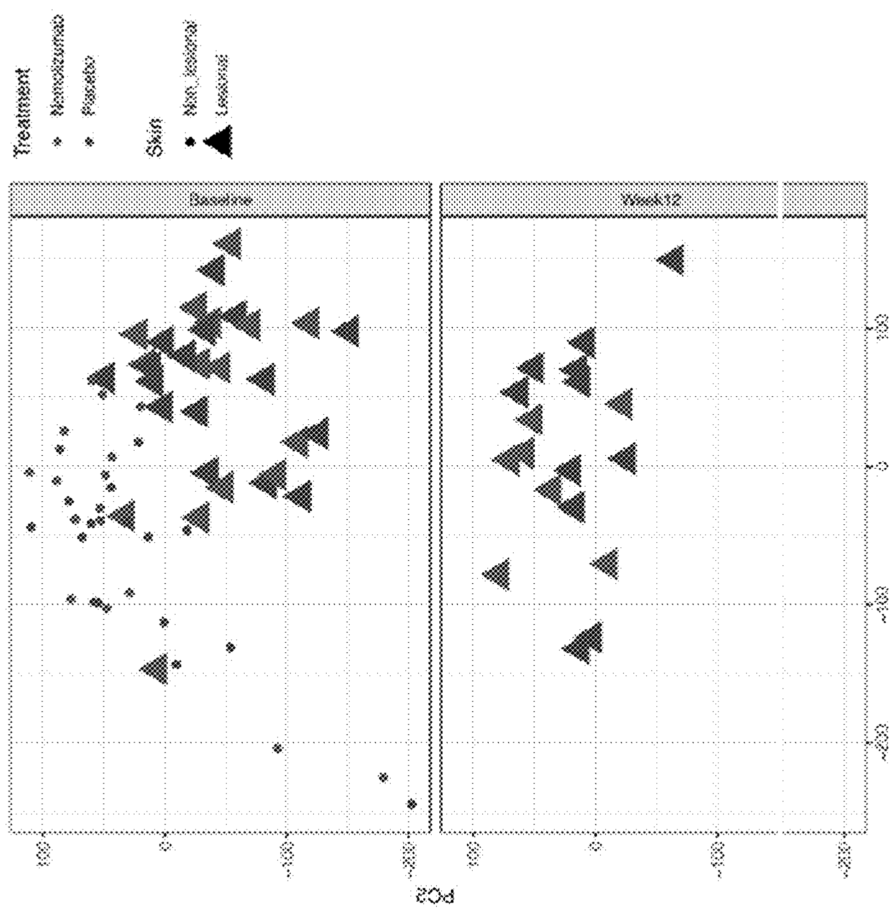
Figures 4A, 4B, 4C:
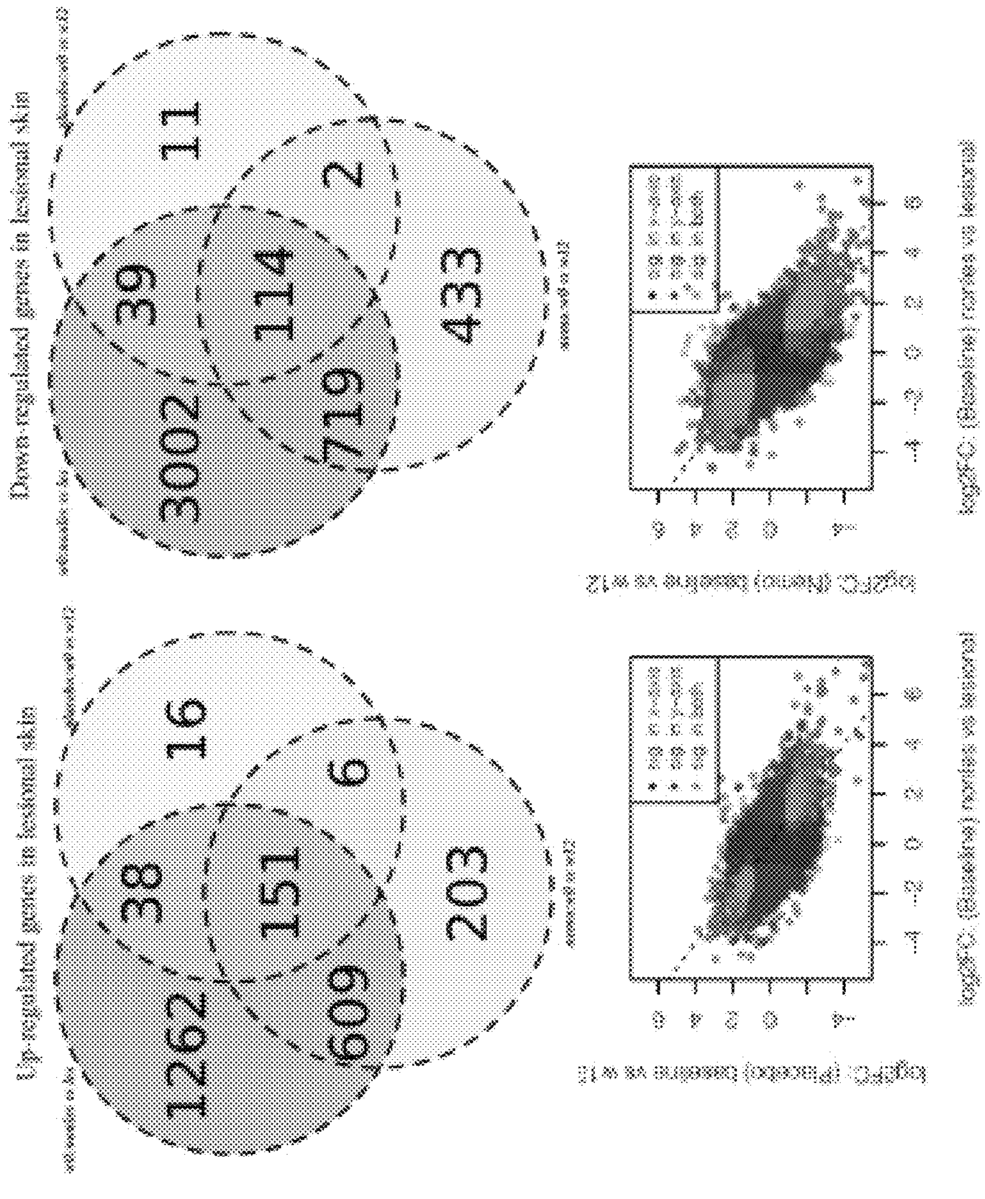
FIGS. 4A-4C shows the effect of nemolizumab on PN associated transcriptomic changes. 3-way Venn diagram of increased and decreased DEGs in PN skin and overlap with DEGs (compared to baseline) in the nemolizumab and placebo cohorts (A). Correlation analyses between different groups (PN baseline vs. placebo and nemolizumab DEGs) (Spearman's rank-order correlation) (B).

To address the therapeutic effect of the IL-31 receptor (IL-31R) inhibitor nemolizumab, RNA-seq data was performed from PN biopsies prior to and after 12-weeks of treatment, and used placebo controlled in a double-blinded study. At baseline, there were 16 and 15 individuals in the placebo and nemolizumab groups, respectively, and at week 12 lesional samples were obtained from 18 of the patients (11 placebo and 7 nemolizumab). Using principal component analysis (PCA) admixing of samples was observed from patients with PN at baseline between the two treatments groups (placebo vs nemolizumab). After 12 weeks of treatment, there was a trend towards grouping of the nemolizumab, but not the placebo cohort (FIG. 3A). This was accompanied by sample clustering using genes that were identified to be differentially expressed in the non-lesional vs lesional skin comparison, with 6 out of the 7 nemolizumab samples (86%) in week 12 grouping with the baseline non-lesional skin samples, versus 57% (4 out of 7) of the placebo group (FIG. 3B). Notably, nemolizumab treatment led to normalization of greater number of PN associated DEGs compared to placebo for both genes upregulated in PN lesional skin (969 nemolizumab vs. 211 placebo) and genes downregulated in PN lesional skin (1,268 genes nemolizumab vs. 166 for placebo) (FIG. 4A). This was also reflected in the correlation between placebo and nemolizumab treated DEGs with much greater overlap between nemolizumab treated group and PN, when compared to placebo vs. PN for both increased and decreased DEGs (FIG. 4B). GO categories enriched amongst DEGs decreased only in the nemolizumab treated group by week 12 included "cell cycle" (FDR=$5.6\times10^{-14}$), "keratinocyte differentiation" (FDR=$1.8\times10^{-4}$), and "interleukin-4 and 13 signaling" (FDR=$1.5\times10^{-2}$), whereas none of these GO categories were found in the placebo controlled group (see Table 2 at the end of the examples section of the specification). These data demonstrate that nemolizumab treatment normalized both epidermal hyperproliferation and differentiation, in addition to decreasing inflammatory responses, particularly related to Th2 responses.

Nemolizumab Response is Accompanied by Decreased IL-31/Th2 Responses in PN Skin

To address the effect of nemolizumab treatment on inflammatory responses in PN skin, nemolizumab and placebo treatment response was interrogated against cytokine response signatures generated in RHE cultures as well as human epidermal rafts. A consistent decrease in IL-31 responses was observed, either solitary, or in combination with other inflammatory cytokines, including the Th2 cytokine IL-13 or IL-17A (FIG. 5A), providing clear evidence of blockade of the IL-31 pathway by nemolizumab. Notably, IL-17A response genes were enriched in PN skin, likely corresponding to the specific downstream immunological cascade overlapping between psoriasis and PN (Table 4). The IL17A mRNA expression was itself not significantly different in the non-lesional vs lesional skin, or in the nemolizumab treatment by week 12 (see Table 1 at the end of the examples section of the specification), suggesting that while IL-17A is not a dominant cytokine in PN IL-17A signatures are downstream of IL-31 signaling. In terms of cellular transcriptomic changes, more robust decrease was observed in the nemolizumab group including Th1 and Th17 (FIG. 5B).

To determine the tissue compartment that has the largest contribution to cellular response to anti-IL-31R blockade, the transcriptomic data from placebo and nemolizumab groups was compared against gene signatures for epidermal compartments obtained from single-cell RNA-seq data. The results indicate the basal keratinocyte (KRT14+) signature was elevated in the lesional skin of PN, while this latter was restored in similar degree in both the placebo and the treatment groups, whereas the induction of the spinous layer (KRT10+) signature in the PN lesional skin was only restored by the treatment but not the placebo group (FIG. 5C). Transcription factor binding site (TFBS) analyses was then performed to further understand the transcriptional regulators of the transcriptomic changes in PN and following placebo or nemolizumab treatment. The results demonstrated that binding sites that are enriched among genes up-regulated in the baseline lesional skin are more likely to be enriched among the nemolizumab down-regulated genes by week 12 (FIG. 5D). The most significantly regulated transcription factors included EGR4 (p=$4.5\times10^{-6}$ and p=$1.2\times10^{-8}$ for enrichment in the promoters of up-regulated genes and for nemolizumab down-regulated genes, respectively), a member of the EGF family of zinc finger transcription factors; STAT3 (p=$2.2\times10^{-4}$ and p=$2.5\times10^{-5}$, respectively); and KLF16 (p=$4.5\times10^{-5}$ and p=$2\times10^{-5}$, respectively) (see Table 5 at the end of the examples section of the specification).

Nemolizumab Leads to Decrease in Pruritus Scoring

Peak pruritus numeric rating scale (PP-NRS), PP-NRS was associated with the transcriptome data (FIG. 6A). While PP-NRS was similar at baseline in both groups, there was consistent decrease in pruritus in the nemolizumab group only, whereas there was wide range of responses in the placebo group. Also, whereas all patients in the nemolizumab group showed improvement, only a subset of patients exhibited significant changes in the placebo group. Notably, the measured distance between the principle component 1 and principle component 2 (PC1/PC2) components for the nemolizumab treated group was much less than that of the placebo group (FIG. 6B), consistent with a therapeutic response.

Discussion

The data presented here are the first to provide a comprehensive view of the global transcriptomic changes in PN skin, and to reveal novel and important insights into the mechanism of action and efficacy of the anti-IL-31 receptor inhibitor nemolizumab. Notably, these data reflect on the transcriptomic level many of the hallmark histologic changes observed in PN, including epidermal alteration, inflammatory response (FIGS. 2A-2C), fibrosis, and pruritus (FIGS. 6A-6B), and how these normalize with nemolizumab treatment.

Many of changes in gene expression in PN skin are related to abnormal keratinocyte proliferation and differentiation (FIGS. 1A-1E). These epidermal alterations accounted for most of the overlap of PN with both AD and psoriasis (FIGS. 2A-2C; Table 4), both of which are also characterized by marked epidermal hyperplasia and altered epidermal differentiation. Notably, these changes demonstrated significant improvement in the nemolizumab treated group by week 12 of treatment, but not in the placebo group (Table 2). Furthermore, consistent with the therapeutic effect of nemolizumab, the greatest effect of normalization was observed on the differentiated layer of the epidermis (FIG. 5C), which may be reflective of decreased keratinocyte proliferation and restoration of normal epidermal differentiation.

Figure 2C:
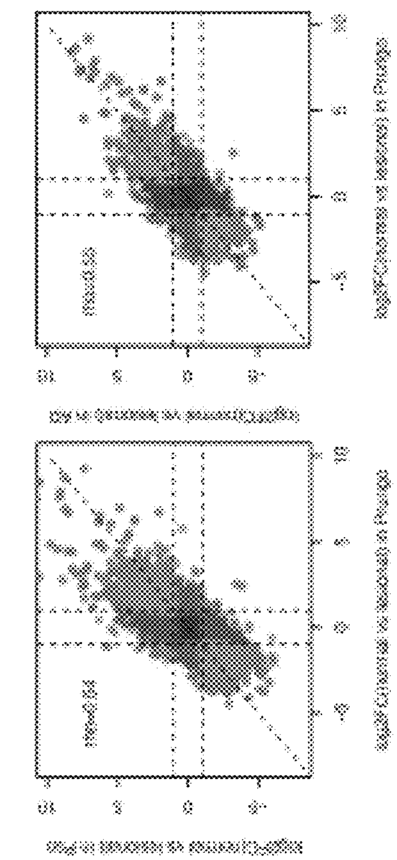

Consistent with PN being a disease process driven by inflammation, immune responses such as Th2 (IL-4/IL-13) response and type I and type II IFN responses were prominent (FIGS. 1A-1E). Th2 responses closely correlate with itch in diseases such as atopic dermatitis, a common predisposing disease to PN development. Interestingly, anti-IL-31 receptor inhibition significantly decreased not only IL-31 responses in keratinocytes in PN skin (FIG. 5A) but also led to decrease in Th2 responses, as well as decreased Th17 (FIG. 5B), corresponding to decreased IL-13 and IL-17 responses in keratinocytes (FIG. 5A). The enriched IL-17 responses in PN skin, as well as contribution from IL-36, likely account for the greater overlap of PN skin with plaque psoriasis, in contrast to AD (FIGS. 2B and 2C). No significant changes were observed in IL17A mRNA expression in the PN data, suggesting that IL-17A is not a dominant cytokine in PN. In addition, the changes in both Th2 and Th17 responses with nemolizumab treatment, and to a lesser extent changes in type II IFN responses, suggest that these cytokines act downstream of IL-31 in PN.

Fibrosis is a feature of PN, most prominent in the papillary dermis, and less commonly in the reticular dermis. Fibrosis in PN is characterized by deposition of vertically oriented collagen fibrils. Modules of genes were found that are involved in extracellular matrix biology to be enriched in PN skin (Table 3), involving both collagen 1 and collagen 3 genes. COL1A1, COL1A2, and COL1A3 mRNA were increased in PN skin at baseline (1.7-, 1.44-, and 1.52-fold respectively, see Table 1) but did not show significant changes with nemolizumab treatment at week 12.

This data also demonstrates how nemolizumab driven transcriptomic changes in PN correlate with improvement in pruritus. Chronic pruritus is a debilitating symptom of PN and has a profound impact on quality of life. The etiology of pruritus in PN still remains unclear but possible factors include the Th2 cytokines, IL-4 and IL-13, major pruritogens in atopic dermatitis, versus changes in cutaneous innervation, with decreased density of intraepidermal nerve fibers being shown to be reduced in both lesional and non-lesional skin. The data from the nemolizumab treatment is consistent with both of these scenarios contributing to itch. Thus, nemolizumab treatment leads to suppression of Th2 and IL-4/IL-13 responses in PN skin and also leads to decrease in expression of factors such as KLF16, which has been shown to inhibit neurite growth. In addition, nerve growth factor (NGF), which was confirmed to increase in PN skin, is also normalized with nemolizumab treatment at week 12 to a larger extent than in the placebo group (Table 1). No changes were seen for the expression of CGRP or substance P (TAC1). These data are highly suggestive of a broad effect of nemolizumab on pruritus and may account for the long duration of pruritus improvement seen beyond the last dose of nemolizumab (>2 months).

In summary, PN is a debilitating and a difficult condition to treat, and no therapies are currently approved for its treatment. This work in-depth characterization of the transcriptomic changes in PN skin and demonstrate the broad mechanisms of action of nemolizumab, an anti-IL-31 receptor inhibitor. These data demonstrate the broad therapeutic effect of anti-IL-31 receptor inhibition with nemolizumab on multiple aspects of PN pathogenesis, including epidermal differentiation, inflammatory responses, pruritus and extracellular remodeling, and confirms the upstream role of IL-31 in PN pathogenesis.

Example 2—Plasma Proteomic Analysis of Nemolizumab Treated Moderate-to-Severe Prurigo Nodularis Patients This example details a randomized, double-blind, phase 2 trial of the anti-human IL31Ra blocking antibody nemolizumab at a dose of 0.5 mg per kilogram of body weight, administered subcutaneously at baseline, week 4 and week 8, as compared with placebo, in patients with moderate to severe prurigo nodularis. The goal of this study was to characterize the effect of nemolizumab on the entire plasma proteome by using mass spectrometry.

Materials and Methods

Patient Dataset

Figure 10:
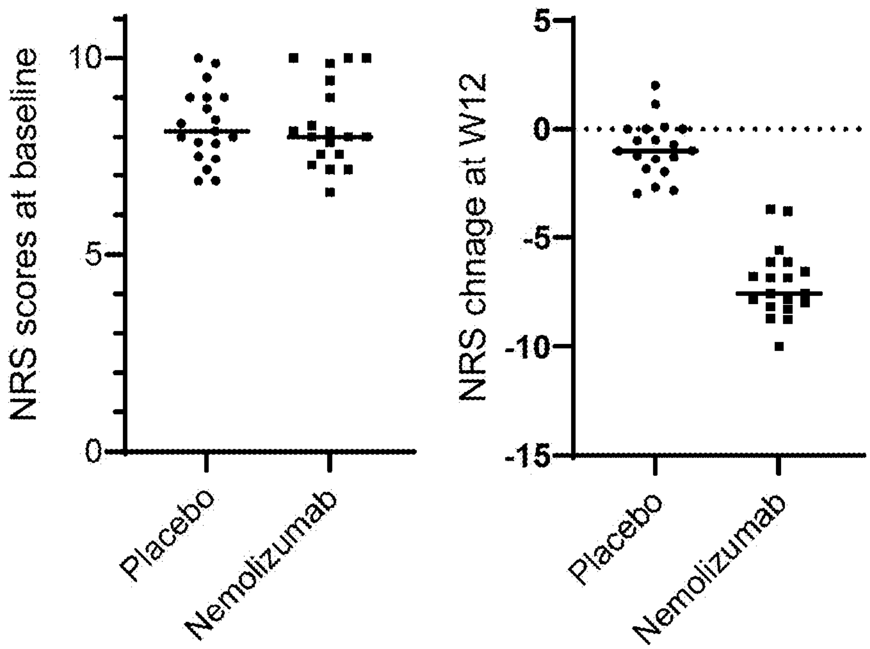
FIG. 10 shows the clinical scores of the patients selected for mass spectrometry analysis. Left panel: PNR scores at baseline. Right panel: NRS change at week 12.

Nineteen (19) placebo non-responders and nineteen (19) nemolizumab responders were selected on the basis of their change in PP-NRS (Peak Pruritus scores on the Numerical Rating Scale) clinical scores at week 12 (19 placebo patients with PP-NRS change ≥−1.4, 19 and nemolizumab patients with PP-NRS change <−5.4). PP-NRS scores at baseline and PP-NRS after 12 weeks of nemolizumab treatment are shown in FIG. 10.

Protocol

After plasma gY14-super-depletion, samples were analyzed using the TMT calibrator MS2 workflow at Proteome Science. A pool of heathy skin biopsies was used in order to 1) allow batch correction between each plex, 2) trigger the mass spectrometer to detect skin related peptide in the blood.

Statistics

Only peptides which corresponded to a unique protein were used for the statistical analysis. Both baseline corrected, and baseline non-corrected values were used to compute differentially expressed proteins. Three statistical tests were used to compute the list of differentially expressed proteins: 1) least square regression method (with and without including patient ID), 2) robust regression method, 3) generalized regression method. 193 proteins were found differentially expressed (adjusted p-value <0.05). No additional (e.g. log FC filters) filters were applied on this protein list. Enrichment analysis was performed using the 193 proteins found differentially expressed with the use of QIAGEN IPA (QIAGEN Inc., digitalinsights.qiagen.com/IPA)).

Results

The list of 193 differentially expressed proteins was then analyzed with the enrichment software IPA. While the p-values indicate the significance of the pathways impacted in the dataset, the z-scores provide insights into the directionality, i.e., how "activated" or "inhibited" are the pathways in the dataset.

Figure 11:
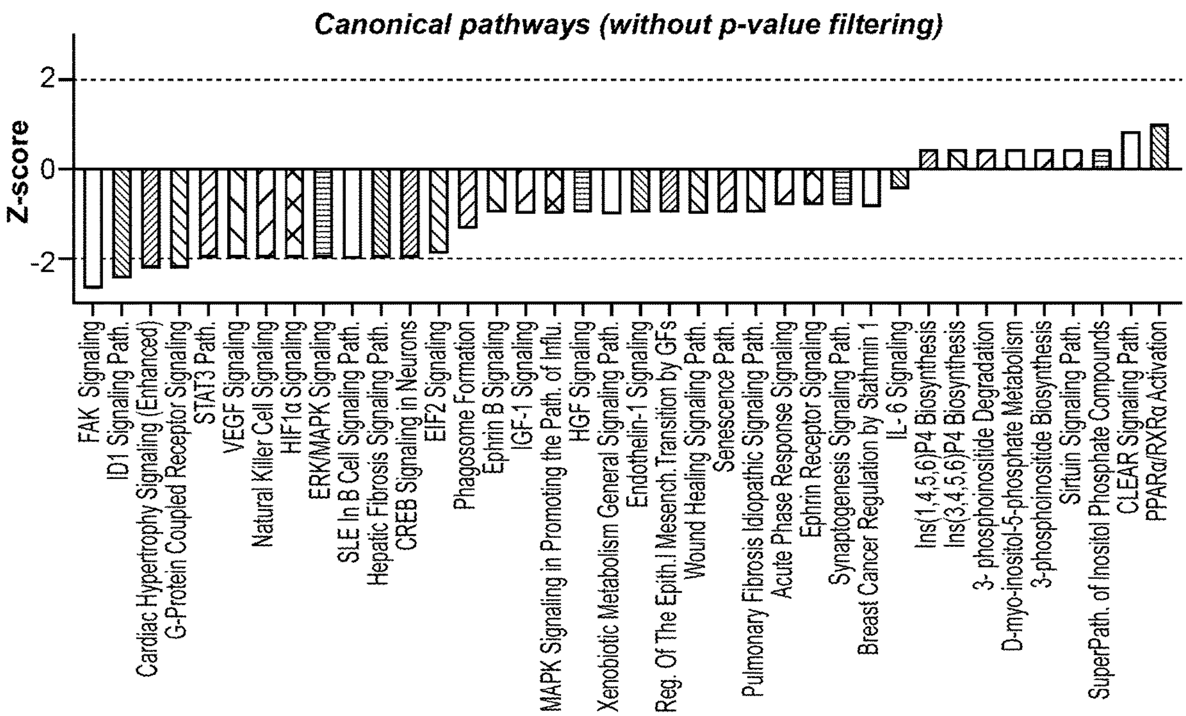
FIG. 11 shows enriched canonical pathways from mass spectrometry. Enriched canonical pathways were sorted according to: right) z-scores only, left) z-scores and p-value ($p<0.05$).
Figure 11:
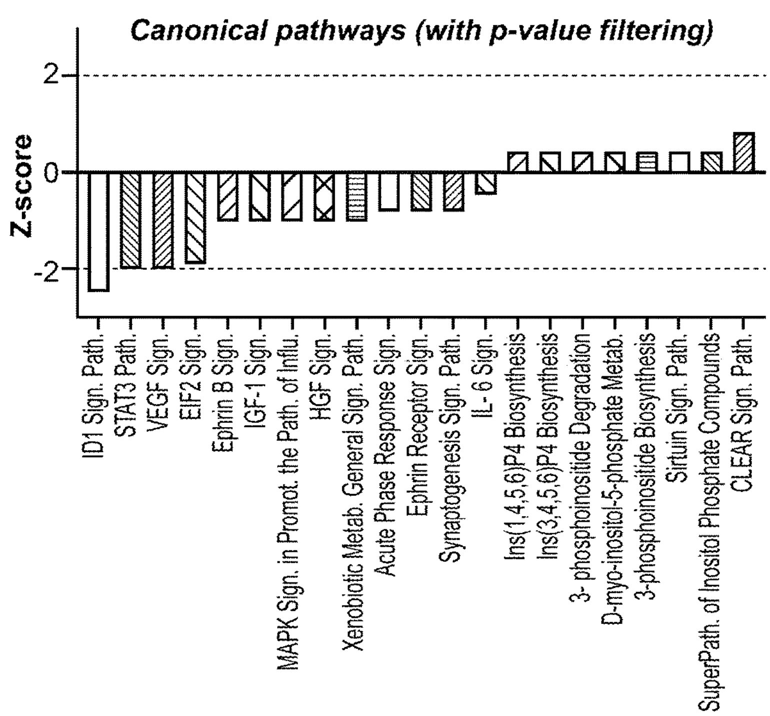

Canonical pathways were either sorted according to z-scores only (FIG. 11 right), or sorted by z-scores and filtered by p-value (FIG. 11 left; −log(p-value)>1.3 corresponding to p-value<0.05). IL-31 has been shown to induce STAT3 activation. Though STAT3 activation is not specific to IL-31, the downregulation of this pathway in nemolizumab responders suggests target engagement by nemolizumab. Further, as compared to placebo non responders, nemolizumab responder signature was characterized by the downregulation the IL-6 pathway. Additionally, the Vascular Endothelium Growth Factor (VEGF) pathway, which has been showed to correlate with PN severity, was downregulated in nemolizumab responders, possibly reflecting clinical improvement. Finally, two neuronal ontologies ("CREB signaling in neurons" and "Synaptogenesis signaling pathway") were identified as downregulated in nemolizumab responders subjects, emphasizing the impact of IL-31 as a neuro-inflammatory cytokine in PN.

Figure 12:
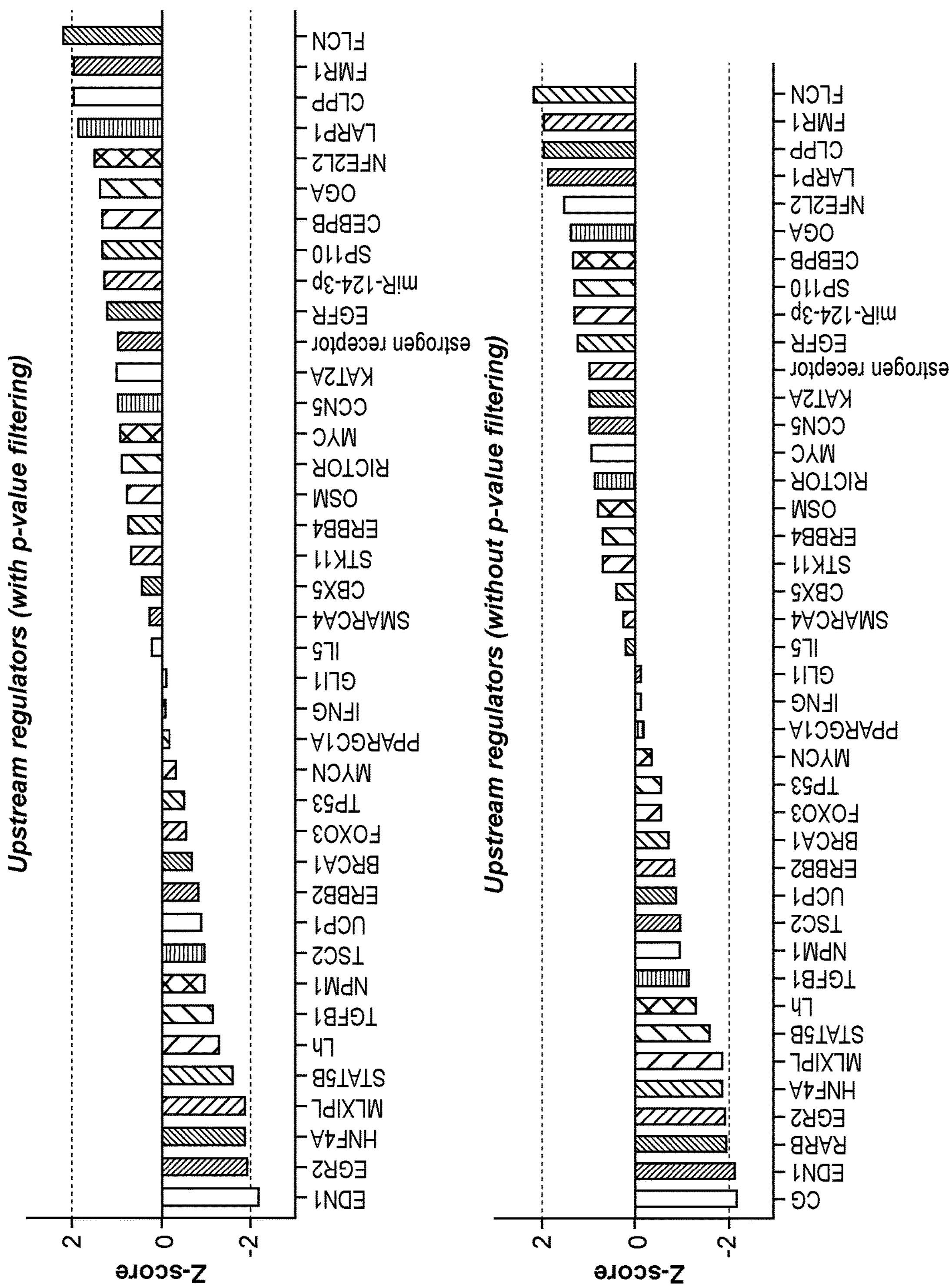
FIG. 12 shows upstream regulator analysis from mass spectrometry. Above: Upstream regulators were sorted according to: right) z-scores only, left) z-scores and p-value ($p<0.05$).

Upstream regulator analysis allowed for the identification of transcription factors and small molecules whose functions are impacted by disease or treatment depending in the dataset analyzed. Though proteins identified in this analysis may not themselves be differentially expressed in the studied dataset, their activation/inhibition status could explain the expression changes in the dataset. Canonical pathways were either sorted according to z-scores only (FIG. 12 right), or sorted by z-scores and filtered by p-value (FIG. 12 left; p-value<0.05). The pro-fibrotic Transforming Growth Factor Beta 1 (TGFβ1) was found as a potential regulator of nemolizumab responder signature, possibly indicating resolution of fibrotic nodules. Another potential regulator was Signal Transducer And Activator Of Transcription 5b (STAT5b), which may reflect target engagement by Nemolizumab. These data clearly suggest that nemolizumab strongly impacts inflammation and tissue remodeling processes in PN.

Figure 13:
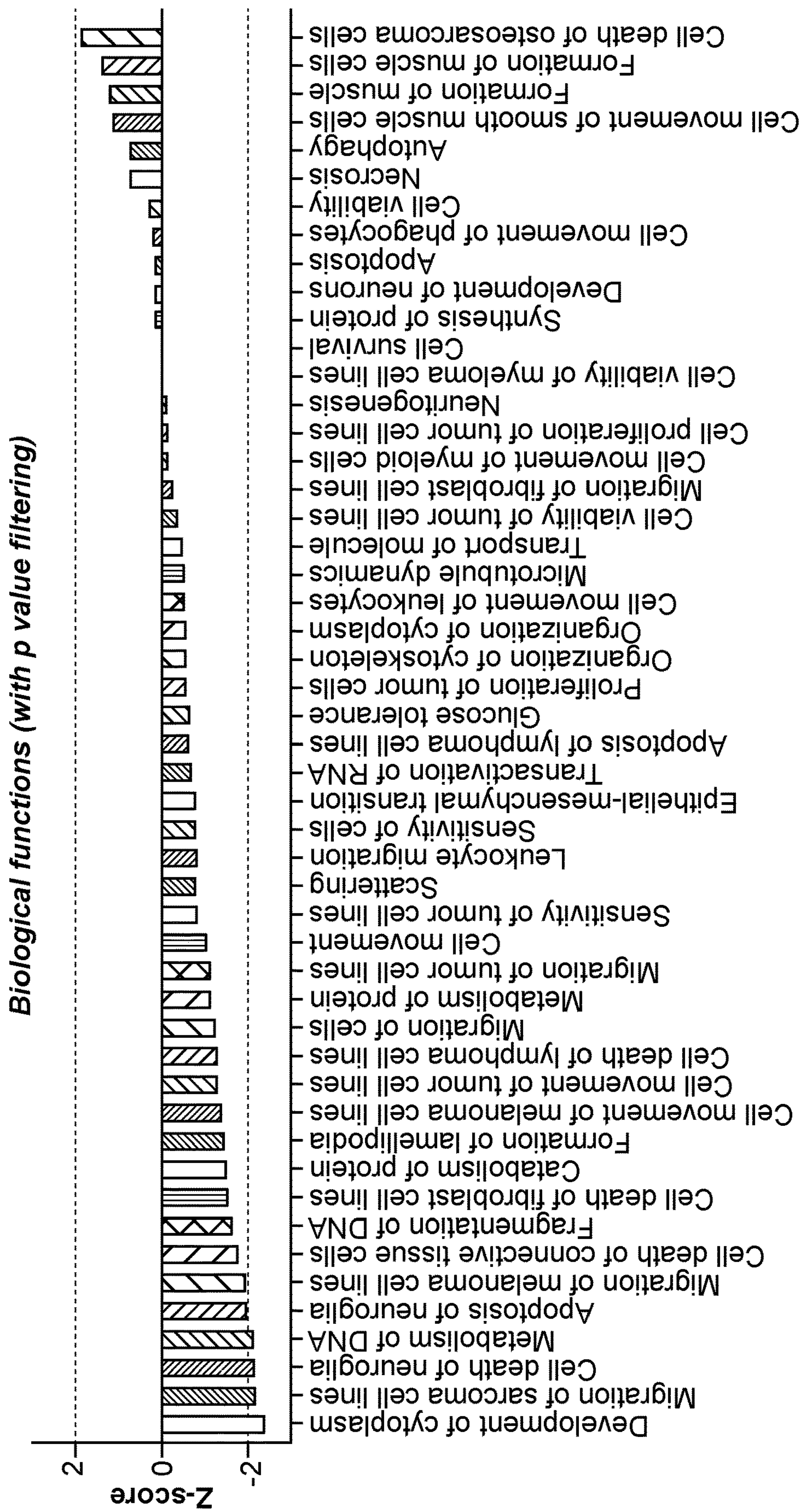
FIG. 13 shows enriched biological functions as identified by mass spectrometry. Enriched biological function ontologies were sorted according to z-scores and p-values ($p<0.05$).

Biological function analysis of nemolizumab responders revealed downregulated "leukocyte migration" and downregulated "cell movement of leukocytes". In addition, two terms associated with the neuronal axis were downregulated: "Cell death of neuroglia", "Apoptosis of neuroglia", possibly reflecting an improvement pruritus (FIG. 13).

Discussion

The present Example aimed to perform a broad and exploratory analysis to identify plasma protein biomarkers that could also explain the mechanism of action of nemolizumab treatment.

To characterize the entire gamut of plasma proteomic changes, pre-selected groups of nemolizumab responders and placebo non-responders were assessed. Due to this pre-selection of patients, the signature described in this Example may not only reflect the changes induced by nemolizumab but also the change due to decreasing PP-NRS.

The dataset analyzed in this study reveals that nemolizumab responder signature was characterized by an improvement of various aspects of PN pathophysiology including inflammation, neuroimmune function, and tissue remodeling.

Enrichment analysis reveals that the nemolizumab responder signature was characterized by a decrease of migration and cell movement of leukocytes. The STAT3 pathway, a direct target of IL-31 signaling was also inhibited in nemolizumab responder subjects suggesting target engagement. Nemolizumab responders also displayed downregulation of other pro-inflammatory cytokine pathways including IL-6 and VEGF pathways.

Pathway analysis also revealed the impact of nemolizumab treatment on neuron-associated processes including "("CREB signaling in neurons" and "Synaptogenesis signaling pathway", "Cell death of neuroglia", "Apoptosis of neuroglia", in line with the observed clinical impact of nemolizumab on pruritus.

Finally, the data set showed a decrease in TGFB1 pathway activation suggesting an impact of nemolizumab treatment on tissue remodeling.

These observations reinforce the understanding that plasma proteomics can effectively capture, at least in part, tissue specific (i.e., skin) effects of nemolizumab in PN.

TABLE 1

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| KRT6C | 9.20 | −3.51 | −7.48 | −0.45 | −5.44 | RNA5SP264 | −1.49 | −0.19 | 0.57 | 1.81 | 0.76 | AC135012.3 | −0.44 | −0.27 | −1.82 | −0.11 | −1.15 |
| KRT6B | 6.24 | −2.76 | −5.81 | −0.34 | −4.47 | CYP2T1P | −0.43 | 0.71 | 0.01 | 0.49 | −0.20 | AC120036.1 | −0.45 | 0.62 | 0.56 | −0.25 | −0.68 |
| S100A7 | 6.91 | −3.55 | −4.72 | −0.99 | −2.57 | SEMA4C | −0.26 | 0.12 | −0.17 | 0.30 | −0.05 | AL355306.2 | −0.37 | −0.26 | −0.48 | 0.32 | 0.30 |
| S100A9 | 7.56 | −3.78 | −6.63 | −0.43 | −4.23 | RNU6-44P | −0.99 | 0.64 | 1.30 | 0.22 | −0.17 | PSMA6P4 | 0.66 | −0.61 | 0.07 | 0.44 | −0.31 |
| PI3 | 6.68 | −5.07 | −7.10 | −0.44 | −3.99 | KIRREL2 | 1.29 | −1.71 | −1.83 | −0.70 | −0.93 | MORN5 | 0.73 | −0.56 | 0.11 | −1.17 | −1.86 |
| KRT16 | 6.49 | −2.81 | −5.85 | −0.28 | −4.18 | AC079880.1 | 0.66 | −0.26 | −0.41 | −0.56 | −0.15 | MIR411 | −0.53 | 1.03 | 0.59 | −0.86 | −0.56 |
| SERPINB4 | 8.43 | −4.09 | −6.23 | −0.51 | −4.01 | AC011476.2 | 1.11 | 0.54 | −0.02 | 0.24 | −0.41 | AC104117.1 | 0.35 | 0.07 | 0.14 | 0.17 | 0.43 |
| S100A8 | 7.89 | −3.98 | −6.16 | −0.61 | −3.83 | GFM2 | 0.18 | −0.11 | −0.14 | −0.06 | −0.10 | PANX3 | 0.42 | −2.85 | −0.61 | 0.54 | 0.07 |
| SPRRIA | 5.51 | −2.05 | −3.71 | −0.10 | −3.22 | PDCL3P6 | −0.46 | −0.31 | −0.12 | 0.10 | 0.19 | AC107294.3 | −0.50 | 0.73 | 2.07 | −1.66 | 1.45 |
| SERPINB3 | 6.15 | −2.90 | −5.01 | −0.63 | −3.74 | EVPL | −0.32 | 0.29 | −0.22 | 0.46 | 0.10 | AC016894.1 | 0.20 | −0.57 | 0.18 | 0.07 | 0.52 |
| KRT16P1 | 3.88 | −1.87 | −3.94 | 0.24 | −1.96 | BATF2 | 0.84 | −1.53 | −1.07 | −1.30 | 0.29 | AC211486.1 | −0.21 | 0.05 | 0.42 | −0.14 | 0.04 |
| AKRIB10 | 4.60 | −1.89 | −3.36 | 0.08 | −1.42 | RNASEH1-AS1 | 0.49 | −0.35 | 0.18 | −0.18 | 0.08 | AIRN | 0.10 | −0.21 | −0.29 | −0.15 | 0.06 |
| FABP5 | 4.21 | −1.09 | −2.95 | 0.18 | −2.43 | MIR32 | 0.92 | −0.30 | −0.55 | 0.08 | −0.07 | DNAJC5G | −0.50 | −1.51 | 0.53 | −0.50 | 0.61 |
| SPRR1B | 5.30 | −2.05 | −3.32 | −0.34 | −2.47 | ST7-OT4 | 0.35 | −0.16 | −0.14 | −0.27 | −0.19 | AC108359.1 | 0.89 | 0.03 | −0.45 | 0.45 | −2.43 |
| KRT6A | 6.04 | −2.72 | −5.22 | −0.33 | −3.37 | SIAH2-AS1 | 0.56 | −0.86 | −0.86 | −0.49 | 0.07 | ACER1 | −0.18 | 0.63 | 1.15 | 1.00 | 0.05 |
| CERNA2 | 5.57 | −1.35 | −3.33 | 0.09 | −1.94 | PJVK | −0.35 | 0.22 | 0.31 | 0.14 | 0.12 | CCNI2 | −0.16 | 0.39 | 0.45 | −0.20 | 0.11 |
| EPGN | 4.98 | −2.85 | −3.51 | −0.88 | −3.04 | DOCK9-DT | 0.66 | 0.29 | 0.18 | 0.35 | −0.17 | AL512594.1 | −0.89 | 0.41 | −0.67 | −0.26 | −2.85 |
| HTR7 | 3.58 | −1.41 | −3.42 | −0.13 | −2.30 | AC023481.1 | −0.63 | 0.27 | 0.29 | 0.43 | 0.01 | RNFT1 | 0.08 | −0.16 | −0.16 | −0.03 | −0.06 |
| DSC2 | 3.87 | −1.90 | −3.73 | −0.48 | −2.52 | PET117 | −0.71 | 0.08 | −0.18 | 0.78 | 0.13 | SUB1P1 | 0.22 | 0.84 | 0.08 | 1.36 | −0.18 |
| C10orf99 | 4.40 | −1.06 | −2.10 | −0.15 | −1.91 | RNU7-113P | 0.89 | −0.35 | 0.40 | −0.45 | 0.35 | AC079238.1 | 0.59 | −0.66 | 0.39 | 0.03 | 0.84 |
| MIR31HG | 6.23 | −2.03 | −2.82 | −0.60 | −1.98 | EIF3L | 0.28 | 0.09 | 0.06 | −0.01 | −0.33 | RNU6-143P | 0.62 | 0.70 | −1.12 | 0.28 | 0.33 |
| CDK5R1 | 2.10 | −0.84 | −1.52 | −0.32 | −1.15 | AVPRIA | −0.56 | 0.25 | 0.79 | 0.08 | −0.11 | AC010307.2 | 0.24 | −0.15 | −0.25 | 0.23 | −0.06 |
| KRT16P6 | 3.19 | −1.35 | −3.73 | 0.67 | −1.29 | CDC42EP3P1 | −0.41 | 0.23 | 0.26 | 0.45 | 0.60 | G35570 | 0.77 | 0.36 | −2.53 | 0.43 | −2.80 |
| KRT16P3 | 3.36 | −2.05 | −3.86 | 0.49 | −1.92 | SPINT5P | −1.80 | 2.24 | 1.96 | 1.28 | 0.71 | PTENP1 | 0.16 | −0.02 | −0.70 | 0.13 | −0.46 |
| SPRR2A | 7.48 | −5.56 | −7.62 | −0.45 | −5.18 | CCDC172 | −1.16 | −0.06 | 0.90 | 0.18 | 1.18 | AC019278.1 | −0.23 | −0.18 | −0.10 | −0.24 | 0.46 |
| PHYHIP | −3.57 | 1.75 | 3.66 | 1.32 | 0.61 | G4440 | −0.87 | 1.27 | 0.93 | 1.07 | −0.22 | AC240565.1 | −0.26 | 0.04 | −0.07 | −0.58 | −0.10 |
| FABP5P7 | 4.43 | −1.05 | −2.78 | −0.28 | −2.26 | AC006001.2 | −0.35 | −0.01 | 0.31 | 0.05 | 0.38 | NOS1 | −0.12 | 0.60 | −0.23 | 0.65 | −0.18 |
| SLC16A1 | 2.35 | −1.44 | −2.40 | −0.23 | −1.29 | CT62 | 0.66 | −0.75 | −1.01 | −0.05 | 0.07 | AC068254.1 | −0.48 | 0.28 | 2.15 | −0.35 | 0.66 |
| PAMR1 | −2.88 | 1.38 | 1.51 | 0.58 | −0.36 | AC078880.5 | −1.70 | 0.14 | 0.56 | −1.15 | 0.35 | COX6B1P5 | 0.32 | 0.53 | 0.21 | 0.87 | 0.20 |
| IVL | 2.99 | −1.66 | −2.40 | −0.45 | −1.45 | MIR3118-3 | −2.42 | −0.54 | 2.89 | −1.45 | 2.98 | AC023905.1 | −0.32 | −1.00 | 0.70 | 0.73 | 1.79 |
| KRT16P2 | 3.80 | −2.75 | −3.99 | −0.19 | −2.24 | DNAJA1P3 | 0.71 | −0.67 | −0.40 | −0.17 | 0.06 | FMR1 | 0.05 | 0.07 | −0.11 | −0.02 | −0.21 |
| LCE3A | 8.68 | −2.72 | −4.91 | −0.24 | −4.14 | C8orf34-AS1 | −1.12 | 0.08 | 0.24 | 0.47 | −0.80 | MMAA | −0.08 | −0.04 | 0.12 | −0.16 | 0.05 |
| GJB2 | 4.33 | −2.19 | −4.17 | −0.40 | −2.71 | AC025271.3 | −1.37 | 1.21 | 2.11 | −0.93 | 0.24 | ELAVL4 | −0.23 | −0.05 | −0.70 | −0.22 | −1.02 |
| DPP6 | −2.85 | 1.43 | 1.23 | 0.96 | −0.14 | ACTG1P3 | −0.41 | 0.17 | −0.03 | 0.27 | −0.01 | LNCARSR | 0.38 | −1.15 | −1.08 | 0.69 | 0.27 |
| SLC7A11 | 2.88 | −1.03 | −2.01 | 0.19 | −1.31 | AK3 | 0.24 | 0.04 | −0.19 | 0.14 | −0.25 | IRF2BP2 | −0.06 | 0.19 | 0.02 | 0.05 | −0.15 |
| SOX5 | −2.16 | 1.36 | 1.72 | 0.84 | 0.34 | AL121580.1 | −0.78 | 0.07 | 0.36 | −0.09 | −0.16 | CEP41 | −0.10 | −0.17 | 0.21 | −0.34 | 0.01 |
| GALNT6 | 2.65 | −1.09 | −1.94 | −0.16 | −1.07 | DUTP7 | −0.41 | −0.09 | 0.88 | −0.26 | 0.65 | AC012322.1 | 0.72 | −0.77 | −1.42 | 0.82 | −1.82 |
| MPZL2 | 2.55 | −1.00 | −2.04 | −0.05 | −1.33 | RN7SKP180 | −0.47 | 0.50 | 0.13 | 0.31 | −0.02 | AC079584.1 | −0.84 | 1.35 | 1.02 | 1.45 | −1.00 |
| S100A7A | 7.21 | −5.15 | −5.65 | −0.48 | −3.44 | DBF4P1 | 1.18 | −0.08 | −1.72 | 0.22 | −1.82 | NDUFA5P2 | 0.24 | −0.25 | 0.23 | −0.61 | 0.10 |
| SNORD39 | 4.23 | −1.59 | −2.34 | −0.15 | −1.94 | RAD1P2 | −1.33 | −0.92 | 1.23 | −0.39 | 1.31 | C4orf51 | 0.47 | 0.19 | 0.40 | 0.14 | −1.55 |
| HS3ST3A1 | 2.55 | −1.27 | −2.64 | 0.09 | −1.04 | EBI3 | 1.18 | −0.89 | −1.09 | −0.26 | −1.23 | AC023781.1 | −0.66 | −0.22 | 0.06 | −0.36 | −0.04 |
| PROB1 | 2.22 | −0.91 | −1.98 | 0.02 | −0.81 | DNAL1 | −0.37 | 0.00 | 0.25 | −0.27 | 0.05 | APOOP5 | −0.67 | −1.07 | 0.71 | −0.67 | 0.23 |
| SLPI | 2.67 | −1.51 | −1.68 | −0.45 | −0.78 | MIRLET7F2 | 0.96 | −0.52 | −0.33 | −0.44 | 0.17 | AL031595.1 | 0.40 | 0.16 | −0.57 | 0.90 | 0.50 |
| AKR1B15 | 3.19 | −1.47 | −2.95 | 0.07 | −1.75 | AC002064.2 | −0.59 | −0.03 | 1.06 | −0.41 | 0.41 | AC004014.1 | 0.65 | −1.37 | −1.54 | −0.43 | −1.38 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| FAM95C | −4.47 | 1.53 | 1.07 | 1.71 | −0.53 | G6426 | 0.84 | 0.27 | 0.26 | −0.45 | 0.12 | DNAJA1P2 | 0.40 | −0.80 | −1.59 | −0.12 | −1.23 |
| KCNJ15 | 2.49 | −1.33 | −2.23 | −0.13 | −0.89 | MZF1 | −0.33 | 0.26 | 0.31 | 0.17 | 0.17 | APOBEC3D | −0.20 | −0.04 | 0.86 | −0.53 | −0.18 |
| LCE3D | 4.88 | −1.81 | −3.08 | 0.00 | −2.57 | AC108751.4 | −1.66 | 1.14 | 1.17 | 0.16 | 0.34 | AP001005.3 | 0.44 | −0.80 | −0.67 | −0.38 | −2.13 |
| LINC01605 | 2.77 | −0.95 | −2.27 | 0.09 | −1.21 | AC008667.1 | −0.87 | 0.16 | 1.00 | −0.21 | 0.10 | AC010619.2 | 0.54 | −0.05 | 0.84 | 0.54 | 0.88 |
| IFI16 | 1.43 | −0.84 | −1.19 | −0.23 | −0.56 | AL136116.1 | 0.79 | −0.38 | −0.35 | −0.12 | 0.03 | S100G | 0.31 | −1.30 | 0.53 | −0.93 | 0.69 |
| ARHGEF26 | −1.48 | 0.85 | 1.39 | 0.43 | 0.44 | AC003957.1 | 0.75 | −0.74 | 0.81 | −0.26 | 0.94 | OR4E1 | −0.37 | 0.29 | −0.88 | 0.24 | −0.28 |
| APOE | −2.13 | 1.36 | 1.47 | 0.65 | 0.38 | AC018620.1 | −0.50 | 0.56 | 1.14 | −0.32 | 0.47 | ESYT3 | 0.10 | 0.10 | −0.03 | 0.11 | −0.18 |
| DSG3 | 2.73 | −1.24 | −2.64 | −0.27 | −1.71 | AC015660.3 | −1.45 | 0.98 | 1.05 | 0.86 | 0.82 | ELOCP32 | 0.42 | −0.75 | −0.55 | −0.26 | −0.71 |
| PITX1 | 3.18 | −1.03 | −2.27 | 0.15 | −1.28 | RFXAP | −0.30 | −0.08 | 0.41 | −0.15 | 0.39 | HOPX | 0.15 | 0.35 | 0.62 | 0.32 | −0.22 |
| IL34 | −2.51 | 1.56 | 2.64 | 0.41 | 0.55 | CCDC188 | −0.62 | 0.27 | 0.40 | 0.43 | 0.16 | FAM19A1 | −0.31 | −0.32 | −2.37 | 0.98 | −0.50 |
| NETO2 | 2.59 | −1.45 | −2.46 | −0.15 | −1.35 | GTPBP8 | 0.33 | −0.16 | −0.05 | 0.02 | −0.05 | AC006205.1 | 0.43 | −0.52 | −2.26 | −0.51 | −0.67 |
| POLR3G | 1.96 | −0.94 | −1.73 | −0.14 | −0.73 | PCBP3 | 0.57 | −0.92 | −1.00 | 0.10 | 0.18 | AL390726.6 | 0.51 | −0.32 | −1.01 | 1.31 | 0.40 |
| IFNE | 6.72 | −1.55 | −1.58 | −0.70 | −1.21 | AC011899.3 | 1.16 | −1.22 | −0.34 | −0.55 | 0.53 | CKS1BP3 | 0.42 | −0.65 | −1.50 | 0.70 | −0.67 |
| OAS2 | 2.43 | −1.37 | −1.83 | −0.66 | −1.21 | AQP9 | 0.79 | −1.28 | 1.57 | −0.10 | −0.01 | AL449363.1 | −0.45 | 0.44 | 0.35 | 1.65 | 0.57 |
| MYH14 | −2.40 | 1.92 | 2.32 | 1.04 | 0.31 | G32993 | 0.72 | 0.57 | 0.34 | −0.04 | −0.74 | AC009060.1 | 0.44 | −1.11 | −2.16 | −0.35 | −0.11 |
| ADAM23 | 2.81 | −1.14 | −2.61 | 0.31 | −1.61 | AC009237.3 | −0.38 | 0.13 | 0.52 | 0.26 | 0.36 | APOBEC2 | −0.15 | 0.27 | 1.04 | −0.13 | 0.59 |
| BCL2 | −1.38 | 0.51 | 1.02 | 0.04 | 0.43 | FXYD1 | −0.99 | 0.79 | 1.08 | 0.42 | −0.54 | RPL34P31 | 0.63 | −0.93 | −0.02 | 0.01 | 0.98 |
| CMYA5 | −1.58 | 1.17 | 1.31 | 0.55 | −0.02 | ADM | 0.44 | −0.63 | −0.71 | −0.36 | −0.36 | RN7SL434P | −0.18 | 0.45 | 0.21 | −0.07 | −0.12 |
| PGAM1 | 1.53 | −0.78 | −1.45 | −0.12 | −0.69 | AC011379.1 | −0.53 | −0.06 | −0.01 | −0.16 | −0.28 | CRYBA4 | 0.71 | −1.01 | −0.57 | 1.61 | 1.71 |
| SH2D5 | 4.32 | −4.89 | −4.79 | −0.20 | −2.71 | PRG4 | −0.88 | 0.41 | 0.93 | 0.39 | −0.74 | LINC02184 | −0.42 | −0.03 | 0.86 | 0.36 | 0.14 |
| PAK3 | −2.18 | 0.95 | 1.85 | 0.65 | 0.85 | GTF3C2 | 0.17 | −0.05 | −0.18 | 0.06 | −0.09 | FKBP11 | 0.09 | −0.15 | 0.07 | −0.29 | 0.12 |
| PPP4R1 | 1.27 | −0.72 | −1.30 | −0.16 | −0.63 | AC008663.2 | −0.83 | 0.07 | −0.25 | 0.05 | −0.41 | CDC37 | 0.10 | −0.25 | −0.71 | 0.07 | −0.06 |
| PNPLA7 | −2.21 | 1.54 | 2.16 | 0.94 | 0.41 | H2AFVP1 | −0.79 | −0.67 | 0.88 | −0.38 | 0.77 | RPS3AP47 | 0.21 | −0.15 | −0.37 | −0.23 | −0.35 |
| CSTA | 3.51 | −1.27 | −1.70 | −0.42 | −2.04 | RNA5SP466 | −1.27 | 0.14 | −0.81 | −0.41 | −0.30 | LINC01658 | −0.51 | 0.08 | −0.94 | −0.46 | −1.85 |
| G30412 | −2.84 | 1.20 | 1.79 | 0.64 | 0.40 | CPD | 0.28 | −0.11 | 0.02 | −0.09 | −0.03 | FTLP2 | −0.66 | −0.32 | 1.61 | −0.07 | 0.20 |
| CD24P4 | 2.40 | −0.90 | −1.88 | −0.57 | −1.52 | AC090607.1 | −0.56 | 0.55 | 0.30 | 0.66 | 0.37 | DLSTP1 | −0.12 | 0.25 | 0.25 | 0.43 | 0.36 |
| RSPH1 | −1.99 | 1.19 | 1.74 | 0.25 | 0.08 | CNTN6 | −0.98 | 0.96 | 1.03 | 0.34 | −0.90 | RNF17 | −0.30 | −0.60 | 0.63 | −0.25 | 0.25 |
| BTC | −2.75 | 1.57 | 3.50 | 0.20 | 0.46 | RSPO4 | −0.56 | 0.01 | 0.49 | −0.32 | 0.36 | RNFT1-DT | 0.32 | 0.07 | −0.23 | −0.64 | −1.59 |
| ATP1A2 | −2.69 | 1.82 | 1.55 | 1.01 | −0.14 | AC007435.1 | 1.26 | −0.19 | −0.90 | −0.52 | −0.71 | FAM171A1 | −0.10 | 0.27 | 0.58 | −0.16 | 0.05 |
| GSTM2 | −2.17 | 1.26 | 1.51 | 1.13 | 0.27 | FAM3D | −0.87 | 0.45 | 0.97 | −0.50 | 0.29 | LINC02435 | −0.82 | 0.27 | −0.94 | 0.05 | −1.77 |
| AL161431.1 | 3.12 | −1.31 | −2.34 | −0.68 | −1.13 | SSBP4 | −0.37 | −0.20 | 0.02 | −0.03 | 0.36 | AC099560.1 | −0.32 | −0.80 | −1.42 | 0.18 | 0.06 |
| S100A2 | 3.25 | −1.84 | −3.19 | −0.30 | −2.21 | AC008443.5 | −0.66 | −0.20 | 0.71 | −0.66 | −0.05 | GHSR | 0.40 | −0.21 | −0.02 | 0.79 | −0.02 |
| STON2 | 1.41 | −0.63 | −1.17 | −0.14 | −0.46 | FIGNL2 | −0.78 | −0.16 | 0.05 | −0.10 | −0.14 | G41235 | −0.21 | −0.25 | 0.34 | 0.09 | 0.41 |
| CNFN | 2.69 | −1.10 | −1.87 | −0.28 | −1.67 | PPP4R1L | −0.19 | 0.06 | 0.06 | 0.00 | −0.01 | AC091114.1 | 0.49 | −0.01 | −1.17 | 0.83 | −1.78 |
| IL36G | 3.07 | −1.36 | −2.21 | −0.37 | −2.35 | CAHM | −0.43 | 0.13 | 0.04 | 0.39 | 0.52 | RNU6-697P | 0.50 | 0.16 | −1.39 | 0.73 | 0.00 |
| CFAP70 | −1.50 | 1.08 | 1.29 | 0.40 | 0.07 | LIPI | −0.84 | −0.18 | −0.15 | −0.17 | −0.71 | C22orf23 | 0.11 | 0.10 | 0.03 | 0.03 | −0.15 |
| C1QTNF7 | −2.29 | 0.90 | 1.27 | 0.98 | 0.24 | INO80 | 0.13 | −0.07 | −0.21 | 0.02 | −0.08 | RNUSE-3P | 0.39 | 0.07 | 0.55 | −0.44 | 0.19 |
| OASL | 3.31 | −2.14 | −3.11 | −0.47 | −2.33 | NEK5 | −0.34 | 0.04 | 0.64 | −0.19 | 0.18 | AC005540.1 | 0.12 | 0.13 | −0.11 | −0.01 | 0.00 |
| ADAP2 | 1.70 | −0.76 | −1.60 | −0.28 | −1.28 | NUB1 | 0.24 | −0.17 | −0.20 | −0.14 | −0.16 | PCEDIA | 0.09 | −0.07 | −0.24 | 0.08 | −0.06 |
| ARNTL2 | 2.32 | −1.16 | −1.96 | −0.43 | −1.34 | AP000908.1 | −1.72 | 1.59 | 0.01 | 0.78 | −1.85 | SETP10 | 0.18 | −0.39 | −0.67 | −0.36 | 0.01 |
| MYEOV | −2.90 | 1.67 | 2.42 | 1.52 | 0.65 | SLC1A4 | 0.34 | −0.26 | −0.57 | −0.02 | −0.30 | AC104779.1 | 0.19 | −0.31 | −0.14 | −0.13 | 0.18 |
| MMP1 | 6.96 | −5.96 | −5.84 | −1.67 | −2.08 | RNU6-711P | 0.73 | −0.58 | −0.52 | 0.34 | 0.30 | C16orf46 | 0.46 | −0.27 | 0.78 | 0.70 | 1.70 |
| PRKN | −1.53 | 0.95 | 1.40 | 0.30 | 0.23 | AC091812.2 | −1.84 | −0.03 | 2.21 | 0.55 | 1.59 | OR5R1 | 0.94 | 0.34 | 0.00 | 0.69 | 0.20 |
| MXD1 | 1.61 | −0.78 | −1.66 | −0.36 | −1.44 | LATS1 | 0.17 | 0.04 | −0.08 | −0.08 | −0.13 | AC093648.1 | −0.88 | 0.77 | 1.16 | 1.27 | 1.29 |
| KPNA2 | 2.13 | −1.39 | −1.71 | −0.47 | −0.70 | AC022679.1 | −1.02 | −0.33 | 0.64 | 0.54 | 1.32 | AC092131.1 | −0.44 | −0.36 | −1.62 | −0.25 | −0.67 |
| PGF | 1.72 | −1.13 | −1.53 | −0.49 | −1.07 | AC136604.2 | −0.36 | 0.28 | 0.43 | 0.20 | 0.22 | LIPT2 | −0.18 | 0.04 | 0.13 | 0.18 | 0.32 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| FAM110C | 2.38 | −0.70 | −1.66 | 0.08 | −1.06 | AL109659.3 | −1.27 | 0.47 | 2.92 | −1.21 | −0.07 | LINC01180 | −0.46 | −1.34 | −0.70 | −0.92 | 0.70 |
| RORC | −1.96 | 1.46 | 2.17 | 0.70 | 0.21 | PCDHB7 | −0.62 | 0.20 | 1.02 | 0.03 | 0.74 | AC108449.2 | 0.14 | 0.11 | 0.30 | −0.01 | 0.14 |
| S100A11 | 1.78 | −1.07 | −1.36 | −0.46 | −0.49 | KRT19 | −0.74 | 0.89 | 1.10 | 0.40 | 0.42 | SPESP1 | 0.17 | −0.68 | −0.44 | −0.07 | −0.09 |
| ELL2 | 1.53 | −0.59 | −1.23 | −0.06 | −0.75 | AL359715.4 | −1.02 | 0.25 | 2.72 | −0.51 | 0.76 | AC013549.2 | 0.16 | −0.35 | −0.21 | −0.15 | 0.12 |
| IL36RN | 3.15 | −1.28 | −1.28 | −0.05 | −1.57 | AMN | −0.50 | 0.15 | −0.54 | 0.34 | −0.29 | RN7SL582P | −0.79 | 0.21 | 1.13 | 1.38 | −0.19 |
| CKAP4 | 1.48 | −0.74 | −1.21 | −0.25 | −0.55 | AC026355.2 | −1.10 | 0.87 | −0.25 | −0.09 | −0.84 | AC107241.1 | 0.23 | 0.50 | 0.85 | 0.19 | −0.09 |
| CDH3 | 2.29 | −1.79 | −2.73 | −0.37 | −1.42 | AC092140.2 | 0.69 | −0.07 | −0.31 | 0.09 | −0.48 | OR52A4P | 0.64 | −1.99 | −1.00 | −0.51 | −0.19 |
| APBA1 | −1.42 | 0.95 | 1.15 | 0.31 | 0.18 | AL512625.1 | −0.45 | 0.19 | 0.58 | −0.01 | 0.09 | AGO3 | −0.04 | 0.06 | 0.21 | −0.06 | 0.09 |
| MACROD2 | −1.51 | 0.94 | 1.23 | 0.46 | 0.30 | H2AFZP3 | 0.72 | −0.14 | −0.31 | −0.07 | −0.35 | AKRID1 | −0.39 | 0.85 | −1.51 | 0.06 | −1.76 |
| MAPK6 | 1.91 | −0.71 | −1.47 | −0.18 | −1.08 | POM121L14P | −0.91 | 0.90 | 2.23 | −0.34 | 0.22 | RN7SL212P | −0.26 | −0.74 | 1.07 | −0.67 | 1.09 |
| IQCN | −1.90 | 1.04 | 1.66 | 0.73 | 0.74 | PPEF1 | −0.60 | −0.29 | −0.15 | 0.06 | 0.09 | AC127024.8 | 0.10 | 0.06 | 0.01 | 0.22 | 0.17 |
| SCIN | −1.80 | 0.97 | 1.81 | 0.32 | 0.12 | RPL23AP48 | 1.85 | 0.27 | −0.57 | 0.87 | 0.07 | AL139288.1 | −0.33 | −0.98 | −0.77 | −0.39 | 0.21 |
| STXBP6 | −1.47 | 0.77 | 1.12 | 0.14 | 0.22 | ARSH | 1.18 | −0.27 | −2.72 | 0.65 | 0.16 | NME1P1 | 0.67 | −1.50 | −0.51 | −1.83 | 1.64 |
| PPIF | 1.74 | −1.17 | −1.53 | −0.32 | −1.15 | AC003682.1 | −0.82 | 0.42 | 0.69 | −0.16 | −0.76 | AC136618.2 | 0.37 | 0.68 | 0.70 | 0.47 | −0.05 |
| CYP4B1 | −2.30 | 0.82 | 1.69 | 0.76 | 0.99 | AC010326.3 | −0.43 | 0.02 | 0.04 | 0.25 | 0.16 | OR56B3P | −0.64 | 1.87 | −0.30 | −0.91 | −1.07 |
| GSDME | 1.56 | −0.95 | −1.22 | −0.24 | −0.19 | HEATR5A | 0.22 | −0.11 | −0.02 | −0.04 | −0.04 | RGPD6 | −0.26 | 0.40 | 0.59 | 0.25 | 0.07 |
| SULF2 | 1.13 | −0.46 | −0.87 | −0.08 | −0.42 | ANKRD18CP | −0.57 | 0.42 | 0.34 | 0.16 | −0.08 | CFHR5 | 0.53 | −1.62 | −0.56 | 0.47 | 0.81 |
| CYP4A11 | −2.59 | 1.34 | 1.99 | 0.58 | 0.88 | AC090825.1 | −0.62 | 0.31 | 0.94 | −0.04 | 0.36 | AC113410.3 | 0.17 | −0.31 | −0.01 | −0.40 | −0.27 |
| CNDP2 | 1.03 | −0.62 | −0.97 | −0.07 | −0.31 | SERTAD3 | 0.21 | 0.23 | −0.14 | 0.07 | −0.37 | EIF4EP3 | −0.43 | −0.74 | −0.33 | −0.11 | 0.00 |
| MYD88 | 1.13 | −0.65 | −1.02 | −0.30 | −0.52 | AL138789.1 | 1.20 | −1.02 | −2.13 | −0.38 | −1.24 | RN7SL296P | −0.48 | 0.03 | −1.76 | 0.91 | −2.02 |
| SGSM1 | −2.17 | 0.93 | 1.26 | 1.02 | 0.66 | ACKR3 | −0.46 | −0.02 | 0.37 | −0.31 | −0.54 | E2F3P1 | 0.25 | −0.48 | 0.27 | −0.71 | 0.47 |
| LCE3E | 4.85 | −1.76 | −2.84 | 0.10 | −2.81 | ADGRF3 | −0.37 | −0.27 | −0.11 | −0.35 | 0.01 | MIR573 | 0.21 | −0.13 | 0.05 | −0.17 | 0.24 |
| GSTO1 | 1.08 | −0.71 | −0.75 | −0.30 | −0.42 | ESRRB | −0.73 | 0.17 | 0.12 | 0.02 | 0.40 | FAM90A11P | −0.96 | 0.75 | 0.32 | 0.53 | 0.36 |
| MTCL1 | 1.35 | −0.35 | −0.89 | 0.00 | −0.30 | PLA2G4E | 0.39 | −0.33 | −0.50 | −0.12 | −0.08 | AC012306.2 | 0.19 | 0.64 | −0.61 | 0.15 | −1.09 |
| CHST12 | −1.53 | 0.84 | 1.44 | 0.22 | 0.26 | AP000344.1 | −1.49 | 1.20 | 1.48 | 0.77 | 0.87 | NAT14 | −0.12 | 0.31 | −0.07 | 0.14 | −0.24 |
| IGFL1 | 4.24 | −0.82 | −2.59 | 0.06 | −2.32 | SALRNA2 | −0.52 | 0.28 | 0.22 | 0.15 | 0.34 | NCK1-DT | −0.11 | −0.23 | 0.01 | −0.02 | 0.13 |
| FBLIM1 | 1.56 | −0.76 | −1.72 | −0.37 | −0.92 | JKAMP | 0.29 | −0.06 | −0.02 | −0.08 | −0.11 | AC018442.3 | −0.30 | 0.68 | 0.52 | 0.77 | 0.14 |
| S100A16 | 1.87 | −0.71 | −1.61 | −0.01 | −1.20 | HERC2P5 | −0.58 | 0.70 | 0.33 | 0.41 | 1.20 | KLF18 | 0.63 | −1.09 | −2.55 | 0.70 | −0.54 |
| CEP55 | 2.28 | −1.41 | −2.33 | −0.39 | −0.75 | CETN4P | −0.64 | 0.25 | 0.67 | 0.69 | 1.04 | DLGAP1-AS4 | −0.43 | −0.04 | 0.46 | −0.57 | 0.43 |
| ITGA6 | 1.79 | −0.76 | −1.69 | −0.20 | −0.82 | AP000487.1 | −0.36 | 0.09 | 0.44 | −0.24 | 0.13 | HMGB3P12 | 1.19 | 0.06 | 0.43 | −0.12 | −1.71 |
| HSPH1 | 1.70 | −0.95 | −1.42 | −0.49 | −0.65 | FTCD | −0.67 | 0.04 | 0.12 | −0.22 | 0.27 | AL021877.2 | −0.25 | 0.09 | −0.41 | −0.69 | −1.22 |
| GARS | 1.39 | −0.59 | −0.98 | −0.27 | −0.68 | MED19 | 0.20 | −0.14 | −0.26 | −0.01 | −0.10 | AC022217.2 | 0.56 | −0.28 | −1.17 | −0.46 | −2.10 |
| SFN | 2.05 | −1.02 | −2.04 | −0.07 | −1.37 | AL161669.3 | −1.06 | 0.25 | 1.39 | −0.25 | −0.43 | AL590560.2 | −0.33 | −0.05 | −1.56 | 0.38 | −0.26 |
| BAK1 | 1.31 | −0.74 | −1.13 | −0.17 | −0.57 | CNPPD1 | 0.18 | 0.09 | −0.17 | 0.16 | −0.11 | OR7E108P | 0.61 | 0.50 | 0.28 | 0.93 | 0.89 |
| AL513303.1 | −3.81 | 1.25 | 2.36 | 1.80 | 0.75 | SEPT14P12 | 0.61 | −0.58 | −2.09 | −0.03 | −0.30 | AC021237.1 | 0.14 | −0.44 | −0.37 | −0.19 | −0.16 |
| LGALS9C | 3.60 | −1.01 | −3.39 | 0.22 | −1.70 | KLHL21 | 0.25 | −0.03 | −0.60 | 0.23 | −0.42 | AC137810.1 | −0.57 | −1.50 | 1.34 | −0.26 | 1.93 |
| DDX25 | −2.13 | 0.75 | 1.47 | 0.28 | 0.72 | ASNS | 0.31 | −0.04 | −0.08 | 0.10 | 0.12 | OTUD4P1 | −0.13 | −0.48 | −0.06 | −0.24 | −0.05 |
| PHF2P2 | −3.44 | 1.64 | 2.93 | 1.52 | 1.07 | SCN11A | −0.57 | 0.09 | −0.15 | 0.53 | 0.53 | AC107959.2 | 0.23 | −0.33 | −0.39 | −0.06 | 0.02 |
| FSCN1 | 1.81 | −1.06 | −1.81 | −0.02 | −0.60 | AL136361.1 | 2.02 | −0.93 | −2.03 | −0.02 | −0.31 | PRKACB | −0.09 | 0.04 | 0.27 | 0.00 | 0.19 |
| G33755 | 3.57 | −1.80 | −3.56 | −0.43 | −2.11 | RNU4-85P | 1.71 | −0.71 | 1.97 | −0.45 | 0.67 | RNY4P2 | −0.66 | 0.63 | 0.90 | 0.14 | −1.08 |
| JPT1 | 1.62 | −0.87 | −1.50 | −0.08 | −0.57 | AC008543.3 | −0.74 | 0.21 | 0.19 | −0.30 | −0.70 | AL390860.1 | −0.37 | 0.51 | −0.44 | 1.01 | 0.52 |
| CACNA2D2 | −1.82 | 1.07 | 1.38 | 0.68 | 0.53 | ELF5 | −0.67 | 0.46 | 0.98 | 0.23 | 0.92 | AC116552.1 | −0.17 | 0.65 | −0.68 | 0.59 | −0.46 |
| KCNK10 | 2.87 | −1.15 | −2.80 | 0.12 | −0.82 | RPS15AP27 | −1.26 | −0.20 | 0.26 | 0.04 | 0.75 | GSTTP2 | −0.47 | −0.53 | 0.17 | 1.31 | −0.12 |
| CACNB1 | −1.51 | 0.75 | 1.55 | 0.22 | 0.58 | AC034229.4 | −1.56 | −0.48 | 1.59 | −2.28 | 0.13 | AL118508.2 | 0.46 | −0.34 | −2.04 | 0.54 | −1.69 |
| AC123777.1 | −3.95 | 2.02 | 4.92 | 0.62 | 2.14 | INF2 | −0.29 | 0.05 | −0.45 | 0.33 | −0.02 | FAM240A | 0.80 | −1.35 | 0.23 | −0.78 | 0.55 |
| ANKRD18A | −2.48 | 1.09 | 1.53 | 0.48 | 0.39 | PRKX-AS1 | 0.56 | −0.07 | 0.16 | 0.21 | 0.26 | AC026991.2 | −0.66 | −0.10 | −1.11 | −0.55 | −2.15 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| MELK | 1.86 | −1.38 | −2.07 | −0.40 | −0.83 | AC024884.2 | 0.93 | −1.25 | −1.26 | −0.44 | −0.84 | RN7SL247P | 0.33 | −0.94 | −0.45 | 0.11 | 1.30 |
| ADCY2 | −2.01 | 1.00 | 1.00 | 0.57 | 0.55 | AL513165.1 | 0.50 | −0.28 | −0.25 | 0.00 | 0.09 | MIR365A | 0.27 | −0.45 | −0.57 | 0.10 | 0.36 |
| PKM | 1.42 | −0.86 | −1.37 | −0.17 | −0.57 | HIST3H2A | 0.45 | −0.63 | −0.73 | −0.03 | 0.18 | CRYBB1 | −0.42 | 0.33 | 2.42 | 0.10 | 1.01 |
| PFN1 | 1.18 | −0.66 | −1.01 | −0.29 | −0.48 | EVI2B | 0.36 | −0.22 | 0.05 | −0.21 | 0.16 | AC079779.1 | 0.49 | −2.14 | −0.06 | −0.21 | −0.13 |
| LTBP1 | 1.47 | −0.78 | −0.98 | −0.35 | −0.16 | RNU1-32P | −1.27 | −0.35 | −0.84 | 1.59 | −0.06 | AC099566.1 | −0.41 | −1.88 | −0.73 | 0.59 | −0.38 |
| CRABP2 | 1.74 | −0.71 | −1.28 | −0.16 | −0.61 | DCLK3 | −0.54 | −0.25 | 1.42 | −0.72 | 0.17 | AC010480.1 | −0.18 | 0.05 | 0.73 | −0.41 | 0.21 |
| AMMECR1 | 1.53 | −0.70 | −1.13 | −0.04 | −0.66 | AL662890.3 | 1.75 | −0.76 | −2.70 | −0.05 | −3.05 | MEIOC | −0.12 | −0.09 | −0.42 | 0.28 | −0.12 |
| LGI3 | −2.96 | 2.02 | 2.19 | 0.44 | 0.38 | SEC31A | 0.14 | −0.08 | −0.07 | −0.23 | −0.22 | AL356235.1 | −0.22 | −0.07 | 0.68 | −0.51 | 0.02 |
| ADGRB1 | −2.03 | 1.23 | 1.52 | 0.82 | 0.00 | AC007285.1 | 0.49 | −0.20 | −0.56 | 0.23 | −0.09 | AC068768.1 | 0.10 | −0.35 | −0.20 | −0.08 | 0.09 |
| IFI27 | 2.22 | −0.87 | −1.80 | 0.02 | −1.34 | AC004540.1 | −0.57 | 0.92 | 0.25 | 0.60 | −0.05 | CEACAMP8 | −0.56 | −0.08 | −0.82 | −0.45 | −1.90 |
| LINC00342 | −1.24 | 0.55 | 0.51 | 0.33 | 0.09 | RRAS | −0.35 | 0.24 | 0.29 | 0.01 | 0.03 | LINC02365 | −0.26 | −0.89 | −0.37 | 0.11 | 0.30 |
| PHYHD1 | −1.65 | 0.94 | 0.96 | 0.66 | 0.17 | RNU6-975P | 1.48 | −1.05 | 0.16 | −0.43 | 1.58 | RPL12P29 | 0.20 | −0.12 | −0.26 | −0.04 | −0.46 |
| LDHA | 1.64 | −0.98 | −1.57 | −0.13 | −0.63 | AC119427.1 | 0.56 | −0.22 | −0.59 | −0.01 | 0.08 | GGN | −0.15 | −0.51 | −0.01 | −0.07 | 0.15 |
| SERPINB13 | 2.85 | −1.30 | −2.39 | 0.08 | −1.83 | KHDC4 | −0.17 | −0.02 | 0.15 | −0.05 | 0.14 | MIR4663 | 0.54 | −0.16 | 0.27 | 0.95 | 0.63 |
| AC007663.1 | −3.12 | 1.51 | 2.67 | 1.84 | 0.64 | AC020658.3 | 0.63 | −0.39 | 0.32 | −0.03 | −0.03 | GPR158 | −0.21 | 0.62 | 0.03 | 0.71 | 0.27 |
| FAM189A2 | −1.81 | 0.84 | 1.15 | 0.67 | 0.42 | CBFA2T3 | −0.49 | 0.12 | 0.33 | −0.10 | 0.04 | P2RX5-TAX1BP. | −0.14 | −0.21 | −0.11 | 0.37 | 0.18 |
| SIRPA | 0.85 | −0.58 | −0.71 | −0.20 | −0.17 | SLC9A3P2 | −1.24 | −0.78 | 0.81 | −1.10 | 2.33 | SDR16C6P | 0.39 | −0.72 | −1.48 | −0.87 | −0.99 |
| CA2 | 2.42 | −1.25 | −2.15 | −0.45 | −1.46 | AC119396.1 | −0.43 | −0.14 | 0.13 | −0.64 | −0.11 | RPL35AP19 | −0.62 | 0.51 | 2.27 | −0.15 | 0.48 |
| AP002800.1 | 2.13 | −0.61 | −2.04 | 0.20 | −0.86 | AC008079.1 | −0.33 | −0.26 | 0.10 | 0.00 | 0.42 | AL138974.1 | −0.68 | −0.02 | −0.08 | 0.75 | −2.73 |
| GPRIN1 | 2.71 | −1.34 | −1.92 | −0.11 | −1.28 | ACKR4 | 0.35 | −0.57 | −0.05 | −0.13 | 0.15 | KRTAP13-4 | −0.87 | −0.47 | 0.21 | −0.42 | 0.22 |
| GSTP1 | 1.47 | −0.67 | −1.30 | −0.24 | −0.76 | GRIP1 | −0.27 | 0.39 | −0.04 | 0.44 | −0.15 | SLC35G2 | 0.12 | −0.02 | −0.08 | −0.15 | 0.03 |
| MCF2L | −1.42 | 0.70 | 0.87 | 0.57 | 0.33 | AC139491.7 | −1.40 | −0.63 | 3.64 | −0.52 | 0.51 | AC004994.1 | −0.29 | 0.93 | 1.08 | −0.10 | 0.20 |
| ENO1 | 1.75 | −0.98 | −1.56 | −0.31 | −0.66 | HJV | −1.07 | 0.31 | 0.97 | 1.40 | −0.58 | CTSLP1 | −0.99 | 0.55 | 0.19 | 0.83 | 0.42 |
| CAP1 | 1.25 | −0.72 | −1.04 | −0.41 | −0.63 | SLC47A2 | 0.54 | −0.13 | −0.63 | 0.57 | −0.16 | NDUFA5P11 | −0.21 | −0.41 | −0.67 | −0.21 | −0.12 |
| AC068587.4 | −1.79 | 1.09 | 1.47 | 0.38 | 0.35 | AC091544.5 | −1.05 | −0.07 | 2.67 | −0.93 | 1.19 | NGF-AS1 | −0.38 | −1.04 | −0.82 | 0.93 | 0.57 |
| KRT16P4 | 2.66 | −1.24 | −3.28 | 0.24 | −1.42 | RBP7 | −0.56 | 0.70 | 0.96 | 0.45 | −0.15 | RPS27P25 | −0.68 | 0.21 | −0.49 | −1.03 | −2.67 |
| INA | 3.18 | −0.72 | −2.08 | 0.21 | −1.55 | AL034417.3 | −0.71 | −0.37 | 0.81 | 0.50 | 1.31 | AC010894.2 | −0.47 | −0.33 | 2.79 | −0.34 | 1.49 |
| RGS20 | 1.81 | −0.88 | −1.51 | −0.33 | −1.25 | HNRNPA1P66 | −0.77 | 0.56 | 0.12 | 0.89 | 0.19 | PLCB1-IT1 | 0.26 | 0.28 | −0.25 | 0.16 | 0.32 |
| ID4 | −1.59 | 1.22 | 1.70 | 0.42 | 0.35 | AL139161.2 | 1.01 | −0.96 | −0.84 | 0.50 | 0.29 | AL450263.1 | −0.16 | 0.53 | 0.58 | 0.60 | 0.07 |
| CDC25B | 1.34 | −0.90 | −1.47 | −0.06 | −0.39 | CXCR3 | 0.63 | −0.08 | 0.39 | −0.81 | −0.22 | MEPE | −0.40 | 0.36 | −2.33 | −0.58 | −2.83 |
| STUM | −2.06 | 1.23 | 1.74 | 0.86 | 0.31 | AL049697.1 | 0.37 | 0.07 | 0.01 | −0.04 | −0.18 | HNRNPH3 | 0.05 | −0.13 | 0.05 | −0.16 | −0.01 |
| MANF | 1.09 | −0.34 | −0.95 | −0.20 | −0.57 | RNA5-8SP3 | −0.86 | 0.72 | −1.00 | 1.31 | −1.31 | RN7SKP281 | 0.55 | −0.22 | 0.06 | 0.37 | −0.55 |
| CRY2 | −1.20 | 0.69 | 1.22 | 0.10 | 0.12 | KRT79 | −0.97 | 1.53 | 0.99 | 1.87 | 0.54 | EPPIN | −0.40 | −0.42 | −0.51 | −0.46 | −0.83 |
| ENAH | 1.16 | −0.58 | −1.24 | −0.19 | −0.61 | OR2A2 | −0.80 | −0.19 | 0.51 | 0.02 | 0.48 | AP003717.3 | −0.32 | −0.22 | 0.34 | −0.12 | 0.11 |
| GSDMB | −1.29 | 0.51 | 1.06 | 0.20 | 0.37 | AC124312.6 | −0.85 | 0.91 | 1.10 | −0.55 | 0.07 | AC073172.1 | 1.32 | 0.22 | 0.07 | 0.13 | −0.11 |
| RAP2B | 1.23 | −0.74 | −1.20 | −0.36 | −0.49 | AL117209.1 | 0.62 | 0.17 | 0.06 | −0.22 | −0.70 | RUNX3 | −0.13 | −0.09 | −0.11 | −0.35 | −0.27 |
| MRPL23-AS1 | −3.16 | 2.20 | 2.35 | 1.97 | 0.93 | AC010894.4 | 0.92 | −0.38 | −0.41 | −0.06 | −0.21 | AP001372.4 | 0.67 | −0.08 | 0.81 | 1.21 | 0.07 |
| CEP126 | −1.44 | 0.90 | 1.35 | 0.21 | 0.14 | FAM172A | −0.18 | 0.22 | 0.26 | 0.08 | 0.00 | AL139405.1 | 0.34 | −0.49 | −0.73 | −0.38 | 0.59 |
| G26976 | −2.41 | 0.71 | 1.77 | 0.10 | 0.67 | AC019193.2 | −1.01 | −0.36 | 0.07 | −0.09 | 0.33 | AC010624.4 | 0.65 | −2.02 | −0.83 | 0.04 | 0.93 |
| OAS3 | 1.55 | −1.04 | −1.58 | −0.36 | −0.74 | AC005230.1 | 0.54 | −0.22 | −1.01 | −0.15 | −0.59 | AC133485.2 | 0.52 | 0.05 | −1.23 | 0.18 | −0.70 |
| MATIA | −2.63 | 1.11 | 1.19 | 0.30 | 0.26 | AL008582.1 | −0.83 | 1.07 | 1.36 | 0.13 | −0.41 | FSTL5 | 0.31 | −0.15 | −0.79 | 0.73 | 0.57 |
| INSYN1 | −2.41 | 0.91 | 2.18 | 0.45 | 0.65 | AL354993.1 | −0.27 | 0.13 | 0.47 | 0.13 | 0.23 | POT1 | −0.06 | −0.08 | 0.29 | −0.10 | 0.14 |
| CLEC7A | 2.24 | −0.98 | −1.39 | 0.27 | −0.42 | SLC27A3 | −0.26 | −0.14 | −0.27 | 0.07 | 0.17 | NACA4P | 0.18 | 0.06 | −0.61 | −0.11 | −0.49 |
| PNP | 1.77 | −0.98 | −2.20 | −0.11 | −1.38 | MTRNR2L1 | −0.72 | 0.36 | −0.48 | 2.28 | 0.02 | AC090337.1 | −0.25 | 0.14 | 0.57 | 0.05 | 0.41 |
| ARMCX4 | −0.87 | 0.38 | 0.87 | 0.07 | 0.40 | RN7SL38P | −1.03 | −0.78 | −0.37 | −0.63 | −0.09 | FAM223A | −1.06 | 1.32 | −0.19 | 1.11 | −0.59 |
| CTSC | 2.05 | −1.26 | −1.85 | −0.15 | −0.98 | G14995 | 0.66 | −0.28 | −0.19 | −0.25 | 0.31 | AC009220.1 | −0.69 | 1.45 | 1.06 | 0.03 | −1.16 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC091182.2 | 3.84 | −1.25 | −2.62 | −0.21 | −1.46 | ELOVL2-AS1 | −1.68 | 0.98 | −0.38 | 0.25 | −0.52 | AC072022.1 | 0.19 | −0.43 | 0.17 | 0.02 | 0.63 |
| SLC1A2 | −1.75 | 0.57 | 0.44 | 0.05 | −0.49 | MTRNR2L4 | −0.81 | −0.37 | −0.27 | 0.01 | 0.20 | AC104316.1 | 0.18 | 0.35 | −0.16 | 0.00 | −0.54 |
| SLC26A5 | −1.75 | 1.17 | 1.34 | 0.79 | 0.54 | CDH18 | −0.76 | −0.30 | −0.43 | 0.05 | −0.11 | MPPE1P1 | −0.63 | 0.66 | 1.96 | 0.70 | −0.36 |
| CFL1 | 1.12 | −0.65 | −1.04 | −0.18 | −0.50 | SIRT2 | −0.21 | 0.22 | 0.13 | 0.23 | 0.08 | DDX47 | −0.12 | 0.05 | −0.29 | 0.07 | −0.17 |
| OPHN1 | −0.84 | 0.67 | 0.99 | 0.25 | 0.20 | RN7SL126P | −1.94 | 0.39 | −0.48 | 1.29 | −0.16 | AC007423.1 | −0.90 | 0.62 | −0.19 | 0.88 | 0.52 |
| CLCA2 | 2.61 | −0.99 | −1.67 | −0.40 | −1.03 | OR7A19P | −0.77 | −0.21 | 1.15 | −0.02 | 0.73 | AC114760.1 | −0.69 | 0.66 | 3.65 | −1.32 | 1.13 |
| MALL | 1.95 | −0.70 | −1.36 | −0.32 | −0.77 | MARK4 | −0.18 | 0.20 | −0.01 | 0.14 | −0.09 | LINC01209 | −0.28 | −0.55 | 0.09 | −0.32 | −0.57 |
| SCGB3A2 | −2.61 | 1.29 | 1.91 | 0.92 | −0.05 | G28051 | 0.66 | −0.25 | −0.34 | 0.26 | −0.16 | AC131097.4 | −0.42 | 0.98 | −0.25 | 0.47 | −0.63 |
| CNKSR2 | −2.15 | 0.97 | 1.52 | 0.74 | 0.41 | ABLIM2 | −0.39 | 0.13 | −0.17 | −0.01 | −0.05 | AC079160.1 | −0.41 | −0.27 | −1.70 | −0.34 | −1.35 |
| EREG | 2.68 | −0.84 | −1.48 | −0.66 | −2.82 | KMT2E | −0.15 | 0.21 | 0.18 | 0.04 | −0.11 | MIR544B | 0.27 | 0.12 | 0.27 | −0.37 | −0.79 |
| PTGFRN | 1.27 | −0.64 | −1.10 | −0.17 | −0.47 | BLID | −0.93 | 0.65 | 1.87 | −0.99 | −0.72 | SNORD56 | −0.14 | −0.39 | −0.36 | −0.10 | 0.23 |
| AC009902.2 | 2.83 | −0.44 | −1.60 | −0.24 | −1.38 | AC084018.2 | −0.75 | 0.94 | 0.83 | 0.26 | −0.33 | AC108102.1 | 0.13 | −0.21 | 0.45 | −0.20 | 0.59 |
| HSPB7 | −2.70 | 1.53 | 1.96 | 0.71 | 0.35 | AJ003147.3 | −0.46 | 0.61 | 1.11 | 0.34 | 0.28 | SAMD10 | 0.11 | 0.12 | 0.03 | 0.01 | 0.07 |
| EMX2 | −1.89 | 0.92 | 1.64 | 0.34 | −0.09 | PRKXP1 | −0.42 | −0.23 | 0.02 | 0.18 | 0.75 | AC005695.3 | −0.38 | 0.85 | 1.05 | 0.09 | 0.26 |
| FRG2HP | −2.85 | 2.49 | 3.67 | 1.72 | 1.14 | AC104574.2 | −1.22 | 1.75 | 1.42 | −0.07 | 0.33 | AL499627.1 | −0.54 | −0.32 | −1.90 | 1.16 | −1.30 |
| MN1 | 1.26 | −0.47 | −1.16 | −0.05 | −0.67 | CNTNAP4 | −0.88 | 0.17 | 0.31 | 0.28 | −0.76 | LINC01820 | 0.48 | −0.56 | 1.04 | −1.15 | −0.25 |
| FAM83A | 2.78 | −1.65 | −2.26 | −0.49 | −1.11 | CYP20A1 | −0.15 | 0.08 | 0.21 | 0.03 | 0.03 | GTF2H2B | −0.12 | −0.15 | 0.26 | 0.46 | 0.66 |
| AC010329.1 | −1.87 | 1.06 | 2.01 | 0.68 | 0.64 | SNORD113-3 | 0.84 | 0.39 | −0.82 | −0.17 | −0.50 | AL450263.2 | 0.25 | −0.95 | −0.48 | −0.40 | 0.56 |
| FAM221A | −1.56 | 0.55 | 1.23 | 0.36 | 0.52 | FBXO25 | −0.16 | 0.30 | 0.21 | 0.12 | −0.19 | MIR141 | −0.64 | 1.32 | 0.77 | 0.44 | −0.55 |
| COQ8A | −1.20 | 0.68 | 0.78 | 0.58 | 0.32 | OR2F1 | −0.93 | −0.23 | −0.62 | 0.78 | −0.08 | KIN | −0.06 | −0.02 | 0.04 | −0.15 | −0.07 |
| CAPZA1 | 1.18 | −0.64 | −0.96 | −0.15 | −0.49 | AC087164.2 | −0.50 | 0.06 | 0.11 | −0.04 | 0.40 | PSAT1P3 | −0.27 | −0.66 | 1.72 | −0.85 | 1.33 |
| GJB6 | 3.02 | −1.49 | −2.76 | −0.50 | −1.86 | FRMD5 | 0.33 | −0.54 | −0.64 | −0.22 | −0.02 | ELOCP20 | −0.96 | 1.12 | −0.51 | 1.79 | −1.19 |
| DLEC1 | −1.10 | 0.48 | 0.24 | 0.24 | 0.13 | AC004678.2 | −0.60 | −0.56 | 0.27 | 0.29 | 0.63 | BISPR | 0.21 | −0.08 | −0.06 | −0.08 | 0.15 |
| BDKRB2 | 1.37 | −0.91 | −1.09 | −0.33 | −0.71 | AL008636.1 | −0.49 | −0.16 | 0.63 | −0.57 | 0.35 | OR8S1 | −0.63 | 0.25 | 1.05 | −1.04 | −0.24 |
| MYOC | −3.84 | 1.82 | 2.60 | 1.97 | 0.61 | AC096637.2 | −1.28 | 1.09 | −0.28 | 0.25 | −2.21 | AL133262.1 | 0.16 | −0.62 | −0.01 | −0.27 | 0.29 |
| DZIP1L | −1.54 | 0.23 | 0.98 | 0.27 | 0.18 | RNA5SP325 | −1.40 | 0.27 | −0.35 | 0.93 | −0.12 | AC021739.3 | −0.18 | 1.11 | 0.68 | 0.23 | −0.05 |
| NELL2 | 3.20 | −0.97 | −1.80 | −0.21 | −1.25 | CD247 | 0.63 | −0.72 | −0.13 | −0.64 | 0.20 | MLIP-IT1 | −0.17 | 0.08 | 0.34 | 0.08 | 0.19 |
| C12orf56 | 2.26 | −0.54 | −0.93 | −0.35 | −0.52 | AC022075.2 | −1.43 | 1.04 | 0.01 | 0.61 | −0.72 | G38640 | −0.61 | 1.48 | 1.52 | 1.63 | −0.20 |
| MSN | 1.11 | −0.82 | −1.11 | −0.35 | −0.47 | MYRF | −0.37 | −0.04 | 0.02 | 0.06 | 0.11 | OR9G3P | 0.83 | −1.03 | −0.41 | −0.95 | 0.06 |
| AMY2B | −1.25 | 0.84 | 1.34 | 0.35 | 0.51 | AC091849.1 | −0.97 | 0.38 | 1.20 | 0.21 | 0.61 | FBRS | −0.06 | 0.14 | −0.21 | 0.15 | −0.04 |
| MYOM2 | −2.39 | 0.85 | 1.44 | 0.72 | −0.12 | RPL5P30 | −0.56 | 0.52 | 0.78 | 0.19 | 0.26 | AC104212.2 | 0.35 | −0.07 | −0.15 | 0.32 | 0.39 |
| AC140479.7 | 3.12 | −0.51 | −0.90 | 0.08 | −0.23 | AC002553.1 | −0.48 | 0.33 | 0.83 | 0.03 | 0.71 | C2orf48 | −0.17 | −0.41 | −1.00 | 0.03 | −0.55 |
| FAM13A | −1.12 | 0.77 | 0.75 | 0.33 | −0.02 | RBPMS-AS1 | −0.87 | 0.57 | −0.08 | 0.81 | −0.92 | AL049610.1 | −0.54 | −1.39 | 0.06 | −0.52 | 0.61 |
| KIF4A | 1.82 | −1.21 | −1.95 | −0.34 | −0.69 | RN7SL258P | 0.70 | −0.66 | −0.03 | 0.15 | 0.72 | AC048346.1 | −1.11 | 1.27 | 1.01 | 0.66 | −0.78 |
| MAPT | −1.41 | 1.10 | 1.53 | 0.52 | 0.38 | ALK | −0.36 | 0.33 | 0.54 | 0.16 | 0.04 | AP000238.1 | 0.38 | 0.85 | −0.63 | 0.42 | −0.62 |
| NR3C2 | −1.56 | 1.00 | 1.38 | 0.36 | 0.26 | RN7SL696P | 0.91 | 0.23 | −0.48 | 0.08 | −0.65 | OR3A2 | 0.43 | 0.26 | −1.71 | 0.62 | −0.97 |
| KIF23 | 1.66 | −1.13 | −1.97 | −0.32 | −0.73 | NPR3 | 0.40 | 0.37 | −0.50 | 0.27 | −0.89 | AL078645.2 | 0.12 | 0.29 | −0.55 | 0.37 | −0.32 |
| IL4R | 1.38 | −1.10 | −1.29 | −0.20 | 0.11 | MIR5096 | 1.32 | −0.12 | −1.39 | −0.32 | −0.50 | AP001922.2 | −0.70 | 0.99 | 1.60 | 0.40 | 1.12 |
| NOCT | 1.26 | −0.82 | −1.36 | −0.25 | −0.61 | RNU6-414P | 0.84 | −0.24 | 0.00 | 0.12 | 0.14 | AL160274.1 | 0.14 | 0.13 | 0.75 | 0.00 | 0.32 |
| PRELID1 | 1.58 | −0.84 | −1.30 | −0.36 | −1.01 | AL158040.1 | −1.04 | −0.60 | 0.68 | −0.25 | 0.77 | NRBF2P2 | 0.62 | −0.86 | 0.60 | −1.28 | 0.98 |
| PDZD2 | −1.31 | 0.86 | 1.15 | 0.56 | 0.17 | AC011337.1 | 0.46 | −0.07 | −0.12 | 0.05 | 0.00 | PLEKHA3P1 | 0.41 | −0.65 | −0.23 | −0.38 | 1.12 |
| JAKMIP3 | −1.74 | 0.76 | 1.20 | 0.83 | 0.68 | OR1Q1 | −0.68 | −0.08 | 0.17 | −0.57 | −0.26 | ELFN1-AS1 | 0.28 | −0.95 | −1.13 | −0.22 | −0.18 |
| G30347 | 3.15 | −0.63 | −1.17 | 0.22 | 0.00 | C6orf48 | 0.36 | −0.34 | 0.17 | −0.23 | 0.28 | AC020558.2 | −0.22 | 0.57 | −0.93 | 0.28 | −0.47 |
| GNA15 | 1.54 | −0.80 | −1.69 | 0.02 | −1.04 | SCFD2 | 0.19 | −0.28 | −0.29 | −0.04 | 0.04 | AL122001.1 | 0.18 | 0.28 | −0.34 | 0.60 | −0.14 |
| CNTFR | −2.57 | 1.39 | 1.36 | 1.29 | 0.60 | AC096564.2 | −0.61 | 0.14 | 0.86 | 0.38 | 0.63 | HNRNPA3P7 | 0.16 | −0.31 | −0.02 | −0.42 | −0.12 |
| MMP10 | 5.79 | −4.53 | −2.85 | −0.44 | −0.15 | STK36 | −0.21 | 0.03 | 0.25 | −0.01 | 0.27 | AC063919.1 | −1.02 | −0.61 | −0.68 | 0.34 | 0.58 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| CCT5 | 1.41 | −0.81 | −1.11 | −0.38 | −0.58 | NTNG2 | −0.59 | −0.65 | −0.34 | −0.11 | 0.52 | RASGRF2 | −0.15 | 0.03 | 0.68 | −0.27 | −0.13 |
| LRRC59 | 1.62 | −1.09 | −1.68 | −0.25 | −0.69 | SLC15A5 | −1.18 | 0.34 | 0.82 | 0.16 | 0.36 | FOCAD- AS1 | −0.26 | −0.37 | 0.65 | −0.31 | 0.52 |
| ACADL | −2.35 | 1.43 | 1.34 | 1.01 | −0.02 | AC005730.3 | 0.59 | −0.48 | 0.13 | −0.32 | 0.45 | HDHD5 | 0.07 | −0.15 | −0.29 | 0.07 | 0.03 |
| CCT3 | 1.30 | −0.64 | −0.92 | −0.32 | −0.65 | NECAB3 | −0.30 | 0.06 | 0.27 | 0.07 | 0.25 | KIR2DL3 | −0.64 | −0.63 | 0.11 | 0.27 | 0.42 |
| KLK6 | 3.90 | −2.46 | −2.96 | −1.29 | −0.57 | PCDHA3 | −0.95 | 1.25 | 0.91 | 1.75 | 0.32 | MYORG | 0.09 | 0.10 | 0.09 | −0.06 | −0.09 |
| LRP4 | −1.96 | 1.35 | 1.78 | 0.76 | 0.63 | AC137894.1 | −0.79 | 0.24 | 0.57 | 0.21 | 0.66 | NUDT16P1 | −0.15 | 0.15 | −0.38 | 0.34 | −0.09 |
| CENPE | 1.71 | −1.22 | −1.89 | −0.42 | −0.55 | RPSAP61 | 1.17 | −0.60 | −1.10 | 0.36 | −0.16 | ASH1L | 0.04 | 0.09 | −0.01 | 0.00 | −0.06 |
| RAN | 1.57 | −0.86 | −1.28 | −0.22 | −0.79 | INSM1 | −0.82 | 0.11 | 0.41 | 0.92 | 1.07 | AC012170.3 | 0.26 | −0.10 | 0.06 | 0.40 | 0.04 |
| PLAU | 1.76 | −1.30 | −1.93 | −0.32 | −1.13 | ST20-AS1 | −0.41 | 0.25 | 0.33 | 0.11 | −0.06 | AC009951.2 | 0.24 | −0.42 | 0.55 | −0.39 | 0.53 |
| LINC01091 | −1.64 | 0.80 | 1.80 | 0.34 | 0.34 | CR545473.1 | 0.84 | −0.14 | −0.10 | 0.15 | 0.10 | HCFC1-AS1 | −0.23 | −0.05 | 0.17 | 0.14 | 0.07 |
| PLEKHH1 | −1.43 | 0.91 | 1.06 | 0.57 | 0.53 | AL132765.1 | 0.53 | −0.09 | −0.45 | −0.24 | −0.51 | GTF3AP6 | −0.87 | 0.17 | 1.59 | 1.08 | 0.78 |
| LGALS9B | 3.31 | −1.17 | −2.49 | 0.22 | −0.75 | CD28 | 0.71 | −0.57 | 0.72 | −0.30 | 0.38 | ETNPPL | 0.47 | −1.34 | 0.49 | −0.18 | 0.56 |
| GBP6 | 2.26 | −1.02 | −1.57 | −0.17 | −1.03 | DRAM1 | 0.35 | −0.26 | 0.00 | −0.31 | −0.17 | AC120024.1 | −0.20 | −0.32 | 0.40 | −0.23 | 0.14 |
| ECT2 | 1.35 | −0.90 | −1.38 | −0.30 | −0.63 | AL139384.1 | −0.52 | −0.53 | 0.43 | −0.17 | 0.85 | LINC01699 | 0.52 | −1.06 | −1.26 | 0.51 | −0.64 |
| HEPHL1 | 3.24 | −2.54 | −3.35 | −0.09 | −2.65 | RXYLT1 | 0.21 | −0.24 | −0.10 | −0.17 | 0.03 | MAPK12 | 0.15 | −0.54 | −0.26 | −0.08 | −0.21 |
| CCNA2 | 1.55 | −1.11 | −1.46 | −0.36 | −0.32 | CCL7 | 1.75 | −1.22 | −1.23 | −0.30 | −1.59 | AC136489.1 | −0.25 | 0.88 | 0.48 | 0.18 | −0.55 |
| AFF3 | −1.80 | 0.78 | 1.32 | 0.47 | 0.18 | AL356320.1 | 0.50 | −0.22 | −0.37 | 0.24 | 0.12 | G4025 | 0.82 | −1.29 | −2.75 | 0.21 | −1.12 |
| PRDM4 | 0.78 | −0.38 | −0.61 | −0.17 | −0.33 | AP000842.3 | −0.76 | −0.62 | 0.38 | −0.81 | 0.63 | C19orf38 | 0.23 | −0.76 | −0.24 | −0.38 | 0.67 |
| HPSE2 | −2.40 | 1.01 | 1.54 | 0.81 | 0.76 | AC026801.1 | −1.52 | 1.53 | 1.23 | 2.24 | 0.95 | CHRNE | 0.16 | −0.16 | −0.38 | 0.08 | 0.21 |
| CAB39L | −1.30 | 0.91 | 0.98 | 0.48 | 0.02 | AC099791.1 | −1.79 | 2.05 | 0.70 | 0.37 | −0.36 | COX6CP14 | 0.28 | −0.12 | 0.69 | 0.22 | 0.48 |
| HAS3 | 2.22 | −1.66 | −2.54 | −0.21 | −2.24 | RNA5SP55 | 0.90 | 0.13 | 0.13 | −0.08 | 0.04 | LINC01856 | −0.38 | −0.91 | 0.16 | −1.18 | −0.03 |
| CYP24A1 | 2.93 | −1.97 | −3.39 | −0.08 | −1.70 | AC108861.1 | 0.62 | −0.41 | −0.06 | 0.40 | 1.18 | AC010323.2 | −0.26 | −0.62 | 0.45 | −0.56 | 0.08 |
| CCNB1 | 2.10 | −1.22 | −1.93 | −0.37 | −0.78 | GPR15 | 1.14 | −0.80 | −1.08 | 0.06 | 0.34 | C19orf25 | −0.05 | −0.05 | 0.07 | 0.07 | 0.20 |
| NHLH1 | −2.53 | 1.56 | 2.49 | 0.75 | 0.87 | AC011893.1 | 1.50 | −1.90 | −1.85 | −0.10 | 0.38 | LHX2 | −0.28 | −0.11 | 0.61 | −0.60 | −0.57 |
| FAM129B | 1.10 | −0.47 | −1.10 | 0.01 | −0.54 | PBX3 | 0.16 | −0.11 | −0.06 | −0.11 | 0.00 | LYRM1 | −0.09 | 0.12 | 0.22 | −0.12 | −0.20 |
| BMP2K | 0.91 | −0.49 | −0.85 | −0.24 | −0.36 | LINC00993 | −1.36 | 1.83 | 0.93 | 1.22 | −0.18 | AC010729.1 | −0.71 | 0.25 | −0.41 | −0.93 | −2.07 |
| CDYL2 | 1.26 | −0.67 | −1.03 | −0.27 | −0.51 | AC010240.2 | 0.49 | −0.11 | −0.18 | 0.14 | −0.01 | RNU6-379P | 0.43 | 0.61 | −1.54 | 0.60 | −0.06 |
| KLF15 | −2.43 | 1.37 | 1.49 | 1.14 | 0.51 | APTR | −0.21 | 0.13 | 0.39 | −0.20 | 0.08 | EEF1A1P16 | 0.26 | 0.43 | −0.76 | 0.99 | −0.86 |
| SSPO | −1.59 | 0.48 | 1.16 | 0.26 | 0.31 | RN7SKP269 | 0.60 | −1.13 | −0.66 | −0.07 | 0.30 | AC023509.2 | −0.34 | 0.67 | 1.56 | −0.49 | −0.44 |
| SMOX | 1.59 | −0.81 | −1.65 | 0.02 | −1.43 | SNORA28 | −0.48 | 0.42 | 0.47 | 0.28 | −0.45 | RNA5SP29 | −0.64 | −0.86 | 1.04 | 0.17 | −1.19 |
| CDKN3 | 1.81 | −0.84 | −1.38 | −0.44 | −0.68 | G16541 | −0.87 | 0.85 | 1.26 | 0.66 | 0.93 | DOTIL | −0.09 | −0.08 | −0.47 | 0.19 | 0.10 |
| EPHX2 | −1.49 | 1.06 | 1.47 | 0.74 | 0.50 | ARHGEF38 | −0.51 | 0.40 | 0.54 | 0.33 | 0.43 | KCNJ6 | 0.22 | −1.36 | −0.97 | −0.60 | −0.69 |
| KRT77 | −2.57 | 0.95 | 2.61 | 0.62 | 0.13 | AC066616.2 | 1.16 | −0.69 | 0.28 | 0.03 | 0.58 | RPL36AP26 | −0.59 | −0.87 | −0.85 | 0.79 | 0.14 |
| MTHFD2 | 1.14 | −0.58 | −0.58 | −0.38 | −0.40 | SSUH2 | 0.77 | −0.36 | −0.24 | 0.06 | −0.08 | MYH15 | −0.14 | 0.38 | 0.58 | −0.14 | −0.29 |
| CSTB | 1.85 | −1.21 | −1.82 | −0.54 | −0.93 | DDX3P2 | −0.61 | 0.17 | 1.59 | −0.31 | 0.56 | RPL7P50 | −0.53 | 0.56 | −2.46 | −0.24 | −1.48 |
| BLACAT1 | 2.77 | −1.49 | −1.99 | −0.16 | −0.58 | COQ4 | −0.21 | 0.11 | 0.16 | 0.13 | 0.19 | AC087762.2 | 0.25 | −0.36 | −0.34 | 0.46 | 0.32 |
| IL11RA | −1.79 | 0.70 | 1.42 | 0.54 | 0.75 | COMT | 0.25 | 0.05 | −0.28 | 0.12 | −0.01 | LGR6 | 0.12 | 0.33 | 0.14 | 0.73 | 0.26 |
| EIF4A3 | 1.26 | −0.69 | −1.42 | −0.19 | −0.68 | RNU6-856P | 0.90 | −0.29 | 0.82 | 0.29 | 0.76 | AC123784.1 | −0.67 | 0.13 | 1.25 | 0.91 | −1.40 |
| GPC2 | −1.89 | 0.68 | 1.57 | 0.86 | 0.70 | AC021723.2 | −0.97 | 0.09 | −0.36 | −0.17 | −0.29 | RUVBL1-AS1 | −0.19 | −0.14 | 0.01 | −0.31 | 0.34 |
| SAMD9 | 1.72 | −0.96 | −1.19 | −0.36 | −0.89 | AL049781.1 | −0.91 | −0.70 | −0.17 | −0.67 | 0.35 | ST6GALNAC6 | −0.14 | −0.22 | 0.73 | −0.36 | 0.52 |
| SPRR2B | 4.53 | −3.70 | −4.36 | −0.55 | −1.36 | AP001458.1 | 1.23 | −0.03 | −0.40 | −0.21 | −1.13 | NAT16 | −0.35 | −0.03 | −1.14 | 0.00 | −3.13 |
| MLXIPL | −2.38 | 1.36 | 1.38 | 1.47 | −0.05 | SIRPG | 1.03 | −0.55 | −0.15 | −0.57 | 0.57 | C12orf42 | −0.29 | −0.08 | −0.33 | −0.08 | −0.65 |
| DLGAP5 | 2.01 | −1.39 | −1.74 | −0.45 | −0.61 | AC002059.1 | 0.85 | −0.40 | −1.50 | 0.38 | −0.09 | G16052 | 0.52 | −1.08 | −1.93 | −0.05 | 0.87 |
| LINC01422 | −1.47 | 0.91 | 1.25 | 0.40 | 0.43 | GEMIN7 | 0.46 | −0.23 | −0.01 | −0.29 | 0.05 | AC010632.1 | −0.30 | 2.04 | 0.19 | −0.22 | −1.20 |
| PRODH | −1.97 | 1.04 | 1.22 | 0.96 | 0.50 | AC009135.2 | −1.49 | −0.28 | 0.00 | −0.11 | 0.58 | AC104078.1 | 0.50 | −0.37 | −2.28 | 1.08 | −2.41 |
| HSPA8 | 1.49 | −0.98 | −1.30 | −0.42 | −0.81 | RNU6-1145P | −0.91 | 0.19 | −0.82 | 1.10 | −0.72 | DRAIC | 0.21 | −0.59 | −0.92 | 0.04 | 0.26 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AHCY | 1.11 | −0.63 | −0.85 | −0.22 | −0.34 | AC006369.1 | 1.27 | −0.02 | −0.12 | −0.37 | 1.46 | AP001043.2 | −0.63 | −1.14 | −1.15 | −0.73 | 0.38 |
| CSNK1A1 | 1.10 | −0.41 | −0.86 | −0.04 | −0.52 | AL359844.1 | −0.62 | −0.70 | −0.20 | −0.21 | 1.00 | LINC00678 | −0.21 | 0.94 | 0.87 | −0.03 | 0.02 |
| LCE5A | −3.50 | 2.44 | 3.85 | 1.78 | 0.63 | MIR3134 | −1.64 | 0.66 | 1.72 | −0.41 | 0.18 | RN7SL846P | 0.29 | 0.19 | 0.35 | 0.34 | −0.04 |
| RPS3AP34 | −1.81 | 0.96 | 1.93 | 0.25 | 0.45 | G27569 | −1.08 | −0.20 | 1.61 | −0.13 | 1.32 | RN7SKP191 | −0.89 | −0.25 | 0.50 | −0.85 | −0.51 |
| PTTG1 | 1.92 | −1.01 | −2.07 | −0.33 | −1.09 | SHOC2 | 0.20 | 0.00 | −0.08 | −0.18 | −0.27 | CRLF1 | 0.12 | 0.06 | −0.45 | 0.28 | −0.41 |
| AC011369.2 | 1.96 | −1.03 | −2.09 | −0.18 | −0.48 | GOLGA6A | −1.17 | 2.10 | −0.01 | 2.00 | −0.40 | AC015967.2 | −0.32 | 1.11 | 0.09 | −0.22 | −0.44 |
| ACP6 | −1.03 | 0.65 | 1.04 | 0.30 | 0.41 | HAUS4 | −0.22 | 0.04 | −0.02 | 0.13 | 0.07 | AC060834.1 | −1.21 | 1.01 | −0.74 | 2.05 | −1.20 |
| EGF | −2.04 | 0.76 | 1.70 | 0.66 | 0.68 | OGN | 0.31 | −0.08 | 0.19 | −0.09 | −0.12 | CSNKA2IP | −0.37 | −0.72 | −0.73 | −0.19 | 0.00 |
| CNOT6 | 0.74 | −0.32 | −0.57 | −0.03 | −0.26 | AC122134.1 | 1.53 | −1.00 | 0.34 | −0.13 | 1.43 | AC114812.2 | 0.31 | 0.41 | 1.01 | 0.68 | 1.09 |
| NSUN7 | −1.44 | 1.19 | 0.77 | 0.61 | 0.23 | ACTC1 | −0.76 | −0.08 | 0.12 | −1.13 | −0.39 | ERICH6B | 0.33 | −0.55 | −0.36 | −0.21 | −0.25 |
| RAB10 | 1.24 | −0.54 | −0.89 | −0.23 | −0.54 | ERICH3 | −0.73 | −0.04 | −0.31 | 0.11 | 0.19 | AC003070.1 | −0.15 | −0.02 | −0.46 | 0.12 | −0.20 |
| FGFBP1 | 2.59 | −1.50 | −2.11 | 0.00 | −1.80 | AC002480.2 | 1.27 | −1.67 | 0.75 | −0.67 | 0.41 | AC141557.2 | −0.21 | −0.77 | −0.87 | 0.31 | 1.25 |
| GPRASP1 | −1.21 | 0.55 | 1.07 | 0.26 | 0.31 | AC093535.1 | −0.39 | 0.42 | 0.60 | −0.18 | −0.30 | CSF2RBP1 | 0.65 | −2.49 | −0.79 | −0.56 | 2.13 |
| SLC7A5 | 2.27 | −1.10 | −2.03 | −0.14 | −0.87 | AC114939.1 | 0.55 | −0.37 | 0.12 | −0.22 | 0.28 | AC003006.1 | −0.62 | 0.50 | 0.72 | −0.15 | −0.45 |
| GAPDH | 1.39 | −0.76 | −1.33 | −0.15 | −0.76 | PPIAP9 | 1.02 | −0.70 | −1.10 | 0.16 | 0.21 | CELA2A | −0.47 | −1.10 | 0.21 | 0.23 | 1.65 |
| OCA2 | −2.16 | 1.22 | 1.08 | 0.90 | 0.42 | R3HCC1 | −0.14 | 0.07 | 0.10 | −0.01 | −0.07 | ASCL4 | 0.39 | −0.25 | 0.09 | 0.55 | 0.34 |
| NOVA1 | −2.19 | 1.34 | 2.13 | 0.69 | 0.26 | PSD4 | 0.26 | −0.05 | −0.24 | 0.04 | 0.00 | AP000844.2 | −0.78 | 0.06 | 0.77 | 0.98 | −0.99 |
| EIF4EBP1 | 1.58 | −0.98 | −1.32 | −0.43 | −0.66 | INTS4P1 | −0.58 | 0.16 | 0.43 | 0.15 | 0.25 | PIEZO1P2 | −0.50 | −0.36 | −0.55 | 0.13 | −0.22 |
| AC092691.1 | −2.72 | 1.25 | 2.90 | 1.67 | 0.80 | AGBL5-AS1 | 1.78 | −1.58 | 0.25 | −0.40 | 1.54 | AC127459.2 | −0.53 | −0.61 | −1.90 | 1.43 | −1.82 |
| EMX2OS | −1.54 | 0.90 | 1.34 | 0.37 | 0.02 | AL096701.3 | −0.50 | −0.07 | −0.10 | −0.22 | −0.40 | AC106739.1 | 0.85 | −1.58 | −0.07 | 0.12 | 0.34 |
| STRIP2 | 1.80 | −1.35 | −1.70 | −0.62 | −0.67 | LINC01558 | −0.65 | 0.90 | 0.92 | 0.50 | −0.05 | RNU6-1026P | 0.37 | −0.20 | 0.11 | 0.31 | −0.40 |
| PARD3B | −0.93 | 0.66 | 0.65 | 0.25 | 0.00 | MIR301A | 1.41 | −1.71 | 0.97 | 0.03 | 0.74 | FAM205A | −0.18 | 0.17 | −0.74 | 0.39 | −0.40 |
| FAM117A | −1.20 | 0.61 | 1.08 | 0.11 | 0.29 | KDM4E | −0.68 | −0.04 | 1.13 | 0.54 | 0.97 | AC006206.1 | 0.22 | −0.21 | −0.22 | 0.09 | −1.10 |
| MUC5B | −1.79 | 0.82 | 1.21 | 0.90 | 0.14 | NANOGP11 | −1.64 | 2.01 | 2.74 | 1.00 | −1.23 | RNA5SP77 | −0.84 | −0.56 | −0.30 | 0.45 | −0.72 |
| PALM | −1.93 | 1.10 | 1.63 | 0.69 | 0.25 | AC020891.2 | 0.89 | −0.53 | −0.21 | 0.28 | −0.20 | AC021755.2 | −0.56 | 1.10 | 1.83 | 0.36 | 0.53 |
| ACTR3 | 1.14 | −0.71 | −0.80 | −0.41 | −0.45 | RNF182 | −0.72 | 0.27 | −0.66 | 0.25 | −0.88 | AC139769.3 | −0.47 | 0.25 | 1.14 | −0.01 | 0.38 |
| MAST1 | −1.70 | 0.84 | 0.79 | 0.62 | 0.15 | EIF4HP1 | 0.47 | 0.20 | −0.17 | 0.12 | −0.47 | AL590132.1 | 0.45 | 0.05 | −1.58 | 0.31 | −0.42 |
| PSMD1 | 1.10 | −0.59 | −0.83 | −0.28 | −0.49 | AC082651.3 | 0.68 | −0.40 | 0.93 | 0.33 | 0.39 | PCAT19 | 0.13 | −0.13 | 0.90 | −0.29 | 0.12 |
| ADAMTSL3 | −1.90 | 0.90 | 1.25 | 0.50 | 0.15 | FLNB-AS1 | 0.33 | −0.08 | −0.28 | −0.30 | −0.24 | AP005901.3 | −0.92 | −0.18 | 0.61 | −0.70 | 0.88 |
| AC008969.1 | −0.98 | 0.56 | 0.97 | 0.15 | 0.23 | SPRY4-AS1 | −0.54 | −0.15 | 0.03 | −0.17 | −0.12 | LINC01602 | −0.61 | −0.40 | −0.27 | 1.02 | 0.59 |
| HIF3A | −2.03 | 1.21 | 1.62 | 1.15 | 0.46 | AC012360.3 | 0.37 | −0.28 | −0.41 | 0.08 | 0.06 | AC093890.1 | −0.22 | 0.10 | 0.48 | −0.12 | 0.15 |
| NDC80 | 1.64 | −1.24 | −1.56 | −0.34 | −0.39 | KRTAP10-9 | −1.63 | 0.03 | 0.08 | 1.90 | −0.81 | NUDT19P5 | −0.26 | 0.30 | 1.26 | −0.01 | 0.14 |
| CORO2B | −1.77 | 0.91 | 1.61 | 0.13 | 0.21 | RN7SL825P | −0.95 | −0.76 | −0.91 | 0.51 | −0.18 | AC103974.1 | 0.17 | 0.66 | 0.56 | 0.30 | −0.13 |
| PA2G4 | 1.02 | −0.57 | −1.01 | −0.05 | −0.41 | RNU4-82P | −0.78 | 1.89 | 0.86 | −0.50 | −1.36 | AC011008.1 | 0.90 | −0.65 | −1.07 | 0.09 | −1.27 |
| IL12RB2 | 1.52 | −0.97 | −1.56 | −0.22 | −0.87 | LETMD1 | −0.16 | −0.06 | 0.13 | 0.12 | 0.34 | ANKRD10-IT1 | 0.12 | −0.18 | 0.08 | −0.32 | 0.13 |
| AQP7 | −2.98 | 2.26 | 2.10 | 1.58 | −0.19 | AC007128.1 | −1.73 | 1.16 | 0.06 | 0.14 | −1.14 | AC137767.1 | −0.14 | −0.24 | 0.13 | 0.05 | 0.36 |
| PLEKHA6 | −1.83 | 0.76 | 1.27 | 0.49 | 0.65 | SNX10 | 0.67 | −0.70 | −1.15 | −0.03 | −0.67 | AC022336.3 | 0.14 | 0.37 | 0.37 | 0.14 | −0.29 |
| SPTBN4 | −1.87 | 0.94 | 1.19 | 0.67 | 0.29 | 5-Sep | −0.59 | 0.85 | 1.21 | 0.22 | −0.28 | RBM39 | −0.06 | −0.01 | −0.17 | −0.05 | −0.12 |
| PPIL1 | 1.53 | −0.79 | −1.16 | −0.45 | −0.63 | SEMG1 | 1.31 | −1.95 | −3.65 | −0.23 | −2.73 | AL161742.1 | −0.18 | 0.14 | 0.85 | −0.27 | 0.81 |
| MFHAS1 | 1.41 | −0.39 | −1.12 | 0.05 | −0.72 | AC084757.2 | 0.94 | −1.60 | −1.74 | −0.03 | −0.70 | CISTR | −0.58 | 0.40 | −0.87 | 1.39 | 0.03 |
| EIF4E | 0.99 | −0.55 | −0.75 | −0.19 | −0.40 | OGFR-AS1 | −0.86 | 0.80 | −0.80 | 0.51 | −0.45 | AC048380.2 | −0.12 | 0.02 | 0.29 | −0.02 | 0.07 |
| LRIG1 | −0.97 | 0.48 | 0.89 | 0.23 | 0.35 | AC100793.3 | −0.95 | −0.78 | 0.74 | 0.08 | −0.32 | SAP18P3 | 0.71 | 0.16 | 1.38 | 0.25 | 0.09 |
| ASCC3 | 0.89 | −0.46 | −0.66 | −0.09 | −0.23 | AC137590.1 | 0.84 | −0.63 | 0.10 | −0.15 | 0.52 | MIR1267 | 1.00 | −0.23 | −1.53 | 1.88 | −0.45 |
| GGH | 2.05 | −0.55 | −0.95 | −0.05 | −1.41 | COLCA2 | −0.87 | 0.04 | 0.86 | −0.47 | 0.36 | AC092042.2 | −0.30 | 0.05 | 1.33 | −0.15 | 1.29 |
| CLSPN | 1.76 | −1.44 | −1.80 | −0.52 | −0.41 | RPL34 | 0.30 | −0.22 | 0.06 | −0.41 | −0.20 | CYCSP39 | 0.88 | −1.17 | 1.22 | −0.11 | 0.21 |
| PPIB | 1.15 | −0.75 | −0.93 | −0.41 | −0.42 | AC126773.4 | −0.60 | −0.10 | 0.66 | 0.28 | 0.99 | AL138895.1 | −0.44 | 0.46 | −0.18 | −0.13 | −0.07 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| KIAA1328 | −0.71 | 0.39 | 0.69 | 0.09 | 0.11 | AL132777.1 | 0.46 | −0.14 | −0.29 | 0.24 | −0.06 | AC004817.3 | −0.28 | −1.44 | −0.59 | −0.86 | −0.94 |
| SLC5A9 | −1.27 | 0.90 | 1.53 | 0.30 | 0.37 | RB1-DT | −0.75 | 0.47 | −0.06 | −0.09 | −0.22 | AC068647.1 | −0.29 | 1.18 | 1.48 | 1.09 | −0.38 |
| MARS | 0.75 | −0.42 | −0.58 | −0.18 | −0.26 | AL138713.1 | −0.69 | 0.78 | 0.75 | −0.16 | −0.18 | LINC00525 | −0.28 | 0.06 | −0.72 | −0.53 | −0.28 |
| ERVMER34-1 | 2.29 | −0.89 | −1.42 | −0.18 | −0.42 | AC020900.2 | 0.87 | −0.35 | −1.34 | 0.27 | −0.85 | AP003168.1 | 0.26 | −1.13 | −0.50 | −0.95 | −0.09 |
| MYO1B | 1.39 | −0.74 | −1.16 | −0.64 | −0.86 | AC004067.1 | −0.31 | 0.10 | −0.25 | 0.33 | −0.02 | GBP7 | −0.28 | 0.80 | 0.30 | 0.19 | 0.35 |
| DPP3 | 1.03 | −0.70 | −0.98 | −0.18 | −0.13 | GK-IT1 | 1.05 | −0.99 | −1.78 | −0.87 | −1.73 | PTMAP8 | −0.17 | 0.47 | −0.64 | 0.29 | −0.85 |
| ABCA2 | −1.25 | 0.54 | 0.98 | 0.20 | 0.36 | AL139807.1 | −0.66 | 0.23 | −0.07 | −0.29 | 0.06 | ANKRD45 | −0.55 | −1.08 | −1.15 | 0.36 | 0.19 |
| SERBP1 | 1.09 | −0.50 | −0.86 | −0.11 | −0.44 | GAPDHP47 | −0.52 | 0.11 | 1.16 | −0.14 | 0.30 | BX255925.1 | 0.24 | −0.54 | −1.21 | −0.27 | −2.11 |
| HMOX2 | 1.08 | −0.69 | −1.18 | −0.28 | −0.43 | KANK4 | −0.62 | 0.08 | 0.64 | −0.26 | 0.40 | AL359633.1 | −0.44 | −0.58 | 1.62 | −0.61 | 1.62 |
| PSMC1P9 | −2.00 | 1.58 | 1.82 | 1.37 | 0.17 | DNAI1 | −0.77 | 0.05 | −0.25 | 0.13 | 0.09 | OR2AG2 | 0.26 | −0.83 | −1.56 | −0.36 | −1.13 |
| NEFM | 2.93 | −1.27 | −2.12 | −1.25 | −2.47 | SHD | 1.12 | −2.65 | −1.30 | −0.80 | 0.20 | AP001099.1 | 0.32 | 0.06 | 1.30 | −0.48 | 0.24 |
| CYP2W1 | −2.69 | 1.48 | 1.61 | 1.58 | 0.86 | AP000654.2 | 1.18 | 0.65 | −0.66 | −0.17 | −0.05 | AC009686.1 | 0.20 | −0.06 | 0.31 | 0.09 | 0.36 |
| AC007262.2 | −1.54 | 1.15 | 1.34 | 0.13 | −0.15 | FBXW10 | 0.82 | −0.28 | −0.65 | 0.14 | −0.94 | AL138830.2 | 0.63 | −1.66 | −1.04 | 0.57 | 2.01 |
| CRYZL2P | −1.00 | 0.37 | 0.97 | 0.07 | 0.40 | AC060780.2 | −0.96 | 0.82 | 0.75 | −0.65 | −0.51 | CLCP1 | −0.54 | 1.41 | −0.94 | 1.70 | −1.81 |
| CNN2 | 1.00 | −0.73 | −0.93 | −0.34 | −0.29 | COX5B | 0.28 | 0.20 | −0.27 | 0.33 | −0.48 | RNU6-1263P | −0.77 | −1.19 | 1.35 | −0.57 | 1.65 |
| ANKRD29 | 1.00 | −0.32 | −0.75 | 0.06 | −0.24 | RNASEK | −0.40 | −0.09 | −0.06 | 0.16 | 0.07 | AC074029.3 | −0.27 | 0.25 | 0.39 | 0.36 | −0.34 |
| GOT2 | 1.28 | −0.64 | −1.13 | −0.18 | −0.52 | AC019330.1 | −1.34 | −0.74 | −0.12 | −0.10 | −0.01 | OR2A01P | −0.28 | 0.31 | 2.40 | 0.23 | 0.32 |
| HDGF | 0.78 | −0.40 | −0.82 | −0.07 | −0.31 | CAMK4 | 0.54 | −0.46 | −0.45 | −0.13 | −0.02 | AC016766.1 | −0.41 | −0.53 | −1.13 | 0.65 | −0.46 |
| MX1 | 1.80 | −1.07 | −1.82 | −0.81 | −1.27 | GLDC | 0.89 | −0.84 | −2.35 | 1.06 | 0.17 | SERPINA6 | 0.78 | −0.42 | −2.43 | 1.96 | −1.32 |
| FGFBP2 | −2.85 | 1.71 | 1.98 | 1.17 | −0.20 | HMGB3P31 | −0.66 | 0.98 | −0.07 | 0.42 | −0.06 | CFAP161 | −0.13 | −0.20 | 0.11 | −0.37 | −0.11 |
| ENTPD7 | 1.04 | −0.78 | −1.00 | −0.41 | −0.47 | AP000779.1 | 0.59 | −0.26 | 0.31 | −0.41 | −0.14 | AC012603.1 | 0.77 | −1.26 | −0.77 | 0.60 | −0.78 |
| LINC01451 | −2.16 | 0.88 | 0.75 | 0.92 | 0.39 | ERN2 | −0.81 | 0.36 | −1.07 | 0.68 | −0.09 | AC244093.4 | −0.11 | −0.05 | 0.23 | −0.28 | 0.20 |
| AC022784.1 | −2.06 | 0.76 | 1.18 | 0.38 | 0.20 | KDF1 | 0.40 | 0.03 | −0.41 | 0.08 | −0.24 | ITGAD | 0.30 | −1.45 | −1.45 | 0.10 | 0.76 |
| EIF4G2 | 1.08 | −0.45 | −0.92 | −0.13 | −0.59 | AP003063.1 | −0.85 | 0.52 | 0.17 | 0.24 | −0.07 | AC079340.2 | −0.51 | 0.51 | −1.70 | −0.88 | −2.71 |
| MKI67 | 1.86 | −1.29 | −1.89 | −0.50 | −0.63 | RCN3 | −0.42 | 0.07 | 0.91 | −0.53 | 0.08 | RN7SL31P | −0.49 | −0.53 | 0.45 | 0.18 | 1.41 |
| PSME3 | 1.19 | −0.52 | −0.84 | −0.19 | −0.37 | NFU1 | 0.35 | −0.03 | −0.29 | −0.06 | −0.21 | SLC24A4 | −0.15 | −0.38 | 0.39 | −0.05 | 0.33 |
| CNGB1 | 3.31 | −1.71 | −3.30 | −0.26 | −1.65 | AC005086.1 | −0.66 | −0.11 | 0.15 | −0.14 | 0.72 | AC073569.1 | −0.12 | 0.18 | 0.25 | −0.12 | −0.10 |
| CCT6A | 1.15 | −0.60 | −0.82 | −0.28 | −0.45 | ANKRD30B | −1.08 | −0.03 | 1.21 | 0.97 | 0.63 | IFNW1 | −0.80 | 0.12 | −0.40 | 1.04 | −0.17 |
| ADAM10 | 0.79 | −0.39 | −0.65 | −0.17 | −0.32 | AL450163.1 | −0.95 | 0.60 | 1.74 | 0.05 | 1.17 | PANO1 | −0.26 | 0.05 | −0.56 | 0.12 | −0.86 |
| DMD | −1.52 | 1.02 | 0.91 | 0.56 | 0.20 | AP001442.1 | 0.23 | −0.22 | −0.40 | 0.05 | 0.04 | CHIA | −0.43 | −1.11 | −0.76 | −0.11 | −1.35 |
| PGBD5 | 2.52 | −1.27 | −2.69 | −0.12 | −2.05 | CPA3 | 0.64 | −0.02 | 0.81 | −0.22 | −0.14 | DUSP13 | −0.43 | −0.39 | 0.38 | 1.25 | 0.38 |
| PER1 | −1.40 | 1.17 | 1.33 | 0.66 | −0.07 | SIL1 | −0.15 | 0.04 | 0.04 | −0.01 | −0.02 | IGBP1P3 | 0.71 | −0.30 | −2.67 | 1.08 | −2.46 |
| AGFG2 | −1.09 | 0.93 | 1.22 | 0.28 | 0.18 | KMT2A | −0.14 | 0.13 | 0.18 | 0.00 | 0.00 | RPL5P15 | 1.12 | −0.86 | −1.31 | −1.35 | −0.90 |
| SPRR2D | 3.00 | −2.23 | −2.44 | −0.62 | −2.13 | STK16 | 0.20 | 0.01 | −0.18 | 0.18 | −0.12 | AL021807.1 | 0.43 | −0.69 | −3.12 | −0.26 | −2.64 |
| CENPF | 1.63 | −0.96 | −1.48 | −0.30 | −0.45 | CCDC116 | −0.70 | 0.47 | 0.44 | 0.35 | −0.70 | GLMP | −0.07 | −0.02 | 0.22 | 0.01 | −0.04 |
| PTPRE | 1.01 | −0.58 | −1.04 | −0.20 | −0.70 | PANK4 | −0.22 | −0.04 | −0.22 | 0.23 | 0.13 | AL136309.1 | −0.31 | 0.14 | 0.76 | 0.87 | 0.56 |
| AC010731.2 | 3.77 | −1.43 | −3.53 | 0.32 | −1.46 | SNORD88A | −0.97 | 1.43 | 0.88 | 0.86 | 0.30 | CEACAMP2 | −0.39 | −0.96 | −1.57 | 0.34 | −0.34 |
| ABCC3 | −1.38 | 0.64 | 0.68 | 0.39 | 0.30 | AKR1B1P3 | −0.78 | 0.07 | −0.38 | 0.37 | −0.06 | MAP3K11 | 0.06 | 0.05 | −0.34 | 0.23 | −0.10 |
| KCNMB4 | −1.59 | 0.82 | 1.00 | 0.61 | 0.10 | AC063965.1 | 0.37 | −0.38 | −0.74 | 0.08 | −0.04 | RPL12P49 | −0.38 | −0.79 | 1.00 | 0.06 | 1.59 |
| P4HTM | −1.22 | 0.77 | 1.20 | 0.14 | 0.06 | AC010491.1 | −0.35 | −0.06 | 0.59 | 0.20 | 0.22 | KBTBD11-OT1 | 0.90 | −1.15 | 0.69 | −0.88 | 1.09 |
| SLC6A11 | 1.96 | −0.54 | −1.23 | −0.21 | −0.71 | ALDH1A2 | −0.49 | 0.14 | −0.15 | 0.29 | −0.07 | MINOS1P2 | −0.29 | −0.49 | 0.90 | −1.04 | 0.41 |
| SEMA3E | −1.85 | 0.93 | 1.29 | 0.17 | 0.04 | AC069528.2 | 0.76 | −0.21 | −0.41 | 0.00 | −0.18 | AC018629.1 | −0.14 | 0.26 | −0.31 | 0.29 | 0.06 |
| ATOH8 | −1.99 | 0.81 | 1.58 | 0.93 | 0.54 | RNU6ATAC27P | 0.65 | −0.04 | −0.58 | 0.18 | 0.08 | AC239802.1 | −0.37 | 0.04 | 1.14 | −0.17 | −0.99 |
| AL135818.2 | 2.81 | −1.70 | −2.25 | −0.11 | −1.19 | AC100827.5 | −0.90 | 0.40 | 0.03 | 0.81 | 0.55 | AC127502.3 | −0.30 | −0.96 | 0.38 | 0.36 | −0.18 |
| CDH22 | −2.59 | 1.34 | 1.48 | 1.81 | 0.80 | RBM17P4 | −0.30 | 0.19 | −0.05 | 0.32 | 0.05 | COL5A1-AS1 | −0.27 | −0.77 | 0.18 | −0.73 | 0.04 |
| PKNOX2 | −1.44 | 0.51 | 0.61 | 0.33 | 0.26 | RHBDL1 | −0.57 | 0.16 | −0.27 | 0.22 | 0.08 | AC245452.5 | 0.66 | −0.59 | −2.37 | 2.09 | −0.86 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| DCST2 | −1.77 | 1.12 | 1.08 | 0.65 | 0.57 | SCAMP2 | 0.21 | 0.08 | −0.09 | −0.01 | −0.31 | DUX4L47 | −0.91 | 0.04 | 0.33 | 0.53 | −0.54 |
| PRSS3 | 2.11 | −0.99 | −1.41 | −0.25 | 0.97 | CBX8 | −0.33 | 0.26 | 0.06 | 0.26 | 0.03 | AF013593.1 | −0.52 | 0.51 | 0.41 | −0.39 | 0.23 |
| L3MBTL4 | −1.06 | 0.69 | 0.79 | 0.22 | 0.34 | AP000942.3 | −1.75 | 0.01 | 1.26 | −0.78 | 0.25 | AC026765.1 | −0.56 | −0.55 | −1.92 | −0.66 | −1.88 |
| SEMA3B | −1.67 | 1.17 | 1.83 | 0.34 | 0.67 | AL355075.1 | −0.78 | 0.70 | 0.17 | 0.53 | 0.51 | FOXJ3 | −0.04 | 0.17 | 0.08 | 0.00 | −0.12 |
| PGK1 | 1.04 | −0.65 | −1.05 | −0.09 | −0.54 | AC090970.1 | −0.44 | −0.27 | −0.02 | −0.26 | 0.51 | PPIAP13 | 0.57 | −1.62 | −0.23 | −0.51 | 0.39 |
| HSF4 | −1.91 | 0.98 | 1.02 | 0.97 | 0.46 | LINC02031 | 0.96 | −0.34 | −1.23 | 1.01 | −0.14 | IMPG2 | −0.14 | −0.01 | 0.36 | 0.05 | 0.08 |
| PLCH2 | −1.64 | 0.63 | 1.00 | 0.37 | 0.65 | FST | −0.46 | −0.27 | 0.12 | −0.60 | 0.20 | RNY3P6 | −0.30 | 0.42 | 0.82 | 0.27 | 0.13 |
| ESPN | −2.15 | 1.36 | 1.56 | 1.08 | 0.82 | ADD2 | −0.61 | 0.12 | 0.26 | 0.02 | 0.24 | AC090953.1 | 0.20 | −0.02 | −0.12 | −0.11 | −0.35 |
| SNX18P3 | −2.71 | 1.12 | 2.32 | 0.65 | 0.49 | SMLR1 | −0.75 | −0.40 | 0.40 | −0.14 | 0.09 | RASSF8 | −0.12 | −0.06 | 0.30 | −0.42 | −0.09 |
| FAHD2B | −1.18 | 0.89 | 1.04 | 0.52 | 0.40 | HPS4 | −0.22 | 0.20 | 0.20 | 0.29 | 0.25 | AL079307.1 | −0.25 | −0.61 | −0.80 | 0.61 | 0.02 |
| AC068587.2 | −1.95 | 1.14 | 2.10 | −0.05 | 0.40 | SH3TC2 | −0.44 | 0.15 | −0.28 | −0.03 | −0.12 | MIR3611 | 0.26 | 0.86 | −0.16 | 0.40 | −0.86 |
| IL1RAP | 1.19 | −0.67 | −1.00 | −0.21 | −0.37 | AC007292.2 | −0.44 | 0.27 | 0.64 | −0.47 | −0.39 | RNU4ATAC11P | 0.20 | 0.11 | 0.33 | −0.36 | −0.32 |
| RNU5F-1 | 2.21 | −1.24 | −2.81 | 0.34 | −1.78 | RSF1 | −0.19 | 0.11 | 0.20 | −0.05 | −0.08 | RP11-497H16.2 | −0.22 | −0.88 | 0.54 | −0.10 | 0.63 |
| SERPINB5 | 1.84 | −0.37 | −1.34 | −0.04 | −1.44 | GTF2I | 0.13 | 0.07 | −0.10 | 0.11 | −0.09 | AC092687.3 | 0.20 | −0.50 | 0.43 | −0.22 | −0.17 |
| SLC16A9 | 2.69 | −1.55 | −2.09 | −0.60 | −0.82 | AC138392.1 | 0.63 | −0.05 | −0.60 | 0.03 | −0.65 | DRD5P2 | −0.77 | 0.11 | 1.00 | 0.37 | −1.02 |
| RRM2 | 2.22 | −1.86 | −1.80 | −0.28 | −0.68 | GLRA2 | −0.94 | 0.58 | −0.28 | 1.19 | 0.12 | MC5R | 0.49 | −0.29 | 0.92 | −0.69 | 0.40 |
| MAMDC2-AS1 | −1.62 | 0.76 | 1.42 | 0.55 | 0.22 | ARL6IP4 | −1.04 | −0.29 | 0.87 | −0.17 | 1.19 | LINC02023 | −0.68 | −0.30 | 1.18 | −0.44 | 0.63 |
| SLC7A11-AS1 | 2.18 | −1.27 | −1.27 | −0.11 | −0.27 | AC023790.2 | −0.68 | 0.03 | −0.29 | 0.96 | 0.47 | AL663074.2 | 1.12 | 0.37 | −1.59 | −1.44 | −2.05 |
| FBXO45 | 1.58 | −0.40 | −1.06 | 0.06 | −1.02 | ICE2 | 0.18 | −0.04 | 0.13 | −0.04 | 0.04 | LINC02490 | 0.62 | −0.46 | −2.05 | −0.02 | −1.59 |
| LMNB1 | 1.38 | −1.20 | −1.30 | −0.37 | −0.22 | AC008250.2 | −1.12 | 0.19 | 2.52 | −1.82 | −0.10 | AL358072.1 | 0.34 | −0.47 | 0.56 | −0.51 | 0.08 |
| MYBL2 | 1.81 | −1.52 | −2.23 | −0.40 | −0.92 | CYCSP2 | 0.76 | −1.09 | 0.06 | −0.66 | 0.17 | AL049637.2 | −0.78 | −0.30 | 0.04 | −1.97 | 1.05 |
| MUC20 | −1.79 | 0.69 | 1.54 | 0.77 | 0.66 | GGTAIP | −0.47 | 0.40 | 0.77 | 0.08 | 0.26 | AC020663.4 | 0.91 | 0.68 | −0.94 | 1.19 | −0.86 |
| CATSPERG | −1.46 | 0.65 | 1.37 | 0.04 | 0.39 | GRK3 | −0.37 | −0.01 | −0.37 | 0.19 | −0.08 | RPL26P29 | 0.33 | 0.54 | −0.13 | −0.97 | −0.68 |
| JADE1 | −0.80 | 0.57 | 0.65 | 0.27 | 0.16 | C17orf58 | 0.30 | −0.23 | −0.24 | 0.19 | −0.05 | LY6K | 0.14 | 0.30 | −0.76 | 0.42 | −0.52 |
| ACP7 | 2.41 | −1.30 | −2.09 | −0.26 | −1.17 | RNF40 | −0.21 | 0.04 | −0.08 | 0.02 | 0.00 | RPE65 | 0.29 | −1.80 | −0.82 | −0.78 | 0.17 |
| HOMER1 | 1.39 | −0.63 | −1.22 | −0.19 | −0.73 | AC104964.2 | −0.32 | 0.29 | 0.28 | −0.07 | −0.11 | PTPRA | 0.04 | 0.03 | 0.07 | −0.06 | −0.05 |
| SERPINB1 | 1.88 | −1.80 | −2.07 | −0.65 | −0.94 | RNF139 | 0.31 | 0.15 | 0.06 | 0.01 | −0.42 | ABCF3 | −0.05 | −0.03 | −0.20 | 0.10 | 0.05 |
| CACNA1H | −2.75 | 0.54 | 1.49 | 1.29 | 0.37 | AC093414.1 | 0.55 | −0.10 | −0.45 | 0.29 | −0.45 | AL079305.1 | −0.52 | 0.13 | −1.66 | 0.95 | −1.47 |
| RARS | 0.82 | −0.48 | −0.50 | −0.21 | −0.17 | ATF4P3 | 0.43 | −0.43 | −0.67 | −0.13 | −0.27 | SNORD113 | 0.23 | 0.06 | 0.35 | −0.04 | 0.17 |
| SERPINE1 | 1.87 | −1.63 | −1.89 | −1.22 | −1.14 | CSNK1G2 | 0.20 | −0.17 | −0.55 | 0.13 | 0.00 | AC104461.1 | 0.30 | −0.32 | 0.75 | −0.25 | 0.65 |
| CES1 | −2.35 | 1.30 | 2.08 | 1.03 | 0.80 | FBXL2 | 0.17 | −0.10 | −0.06 | −0.01 | 0.02 | AC126474.2 | −0.09 | 0.02 | −0.29 | 0.12 | −0.04 |
| MALT1 | 1.00 | −0.47 | −0.73 | −0.17 | −0.47 | PRORSD1P | 0.32 | −0.69 | −0.09 | 0.11 | 0.44 | KLRC3 | 0.70 | −1.76 | 0.68 | −0.12 | 3.23 |
| BCAR3 | −1.16 | 0.43 | 1.05 | 0.08 | 0.32 | AC020911.1 | −1.19 | −0.38 | 0.79 | −0.57 | 0.51 | MIR4639 | 0.37 | −0.07 | 1.52 | 0.16 | 0.06 |
| PLLP | −1.28 | 0.88 | 1.58 | 0.30 | 0.29 | SLC51A | 0.29 | −0.14 | −0.17 | −0.17 | −0.23 | AC074141.1 | −0.12 | 0.15 | 0.16 | 0.13 | −0.09 |
| IFITM3 | 1.33 | −1.11 | −0.89 | −0.47 | −0.14 | LINC00992 | −0.67 | 0.47 | 1.43 | 0.78 | 0.76 | AC124947.2 | −0.31 | 0.90 | −0.06 | 0.50 | −0.34 |
| PRAG1 | 1.32 | −0.67 | −1.53 | 0.11 | −0.59 | PLPP7 | −0.74 | 1.01 | 0.33 | 0.27 | −0.54 | BPIFA1 | 0.96 | −0.93 | 0.31 | −0.57 | 0.59 |
| PRKCQ | 1.56 | −0.98 | −1.65 | 0.07 | −0.52 | AL078645.1 | 0.51 | −0.34 | −0.25 | 0.02 | 0.09 | LINC00919 | 0.63 | −0.99 | 1.66 | 1.29 | 1.19 |
| HMCN2 | −2.24 | 1.19 | 1.74 | 1.22 | 0.30 | RHOC | 0.19 | −0.18 | −0.12 | −0.01 | 0.08 | CENPM | 0.13 | −0.75 | −0.47 | −0.23 | 0.17 |
| CASP4 | 0.99 | −0.49 | −0.73 | −0.27 | −0.42 | PPP1R2B | 1.06 | −0.49 | −0.58 | 0.09 | 0.09 | C8orf86 | −0.33 | −0.47 | 0.73 | 0.00 | 2.06 |
| AC018716.2 | 4.02 | −1.62 | −2.21 | 0.35 | 0.89 | MKKS | 0.24 | −0.24 | −0.24 | 0.02 | −0.03 | AC002347.1 | 0.40 | 0.45 | −0.52 | 1.06 | −0.37 |
| AC046168.2 | −3.35 | −0.26 | 1.63 | 1.62 | 1.40 | COL1A2 | 0.53 | 0.30 | 1.56 | −0.94 | −0.32 | AC006014.10 | −0.42 | −0.09 | −0.44 | 1.00 | 1.26 |
| SLC39A6 | 1.52 | −0.37 | −0.84 | −0.08 | −0.58 | AC079336.4 | 0.78 | −0.45 | −0.25 | −0.28 | 0.68 | C2orf50 | −0.31 | 0.15 | 0.06 | 0.15 | −0.32 |
| NAALADL2 | −1.20 | 0.87 | 1.17 | 0.26 | 0.23 | PIK3R3 | 0.39 | −0.16 | −0.11 | 0.03 | 0.16 | RPL21P9 | −0.96 | −0.36 | 0.25 | −1.73 | −0.48 |
| CALCOCO1 | −1.03 | 0.79 | 0.75 | 0.46 | 0.07 | AC127002.1 | 1.28 | −0.61 | −3.36 | 0.66 | −1.56 | HNRNPA1P32 | 0.95 | −1.86 | −1.94 | 0.73 | 0.93 |
| AC016582.3 | −1.86 | 1.14 | 1.39 | 0.32 | 0.11 | ERBB2 | −0.27 | 0.50 | 0.36 | 0.32 | −0.05 | RNU6-1194P | −0.75 | 0.54 | 2.52 | −0.92 | 1.06 |
| CHADL | −1.74 | 1.12 | 1.21 | 0.99 | 0.37 | MTND5P16 | −0.99 | −1.34 | −0.80 | −0.50 | −0.09 | AC090912.2 | −0.20 | 0.14 | −0.71 | −0.10 | −0.18 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC005089.1 | −2.35 | 1.10 | 1.09 | 0.99 | 0.73 | MAP2K7 | −0.18 | 0.14 | −0.21 | 0.16 | −0.11 | AC006017.1 | −0.12 | 0.11 | 0.30 | −0.08 | 0.35 |
| EBNA1BP2 | 1.18 | −0.76 | −1.02 | −0.30 | −0.34 | CHRM3-AS1 | −1.43 | −0.69 | 1.15 | −0.26 | 2.31 | FOXI1 | −0.28 | 0.87 | 0.55 | 0.47 | 0.48 |
| CRIP1 | −1.80 | 0.39 | 1.63 | 0.58 | 1.50 | RNF215 | −0.22 | 0.05 | 0.23 | 0.01 | 0.15 | AL451064.1 | −0.27 | 0.37 | 1.21 | −0.17 | 0.55 |
| FN3K | −1.45 | 0.76 | 1.07 | 0.51 | 0.42 | CCT6P1 | −0.23 | −0.05 | 0.18 | 0.10 | 0.26 | CCT6P2 | 0.56 | −0.13 | −1.60 | 0.20 | −1.38 |
| PAQR5 | 1.67 | −0.83 | −1.26 | −0.28 | −0.92 | FUCA1 | −0.27 | 0.25 | 0.39 | −0.02 | −0.04 | HNRNPA3P1 | 0.22 | −0.17 | −0.14 | 0.12 | −0.41 |
| AC018716.1 | 4.09 | −2.04 | −1.90 | 0.20 | 1.16 | CATSPER1 | −0.56 | 0.43 | 0.32 | 0.17 | −0.30 | LINC00487 | −0.37 | −0.62 | −1.15 | 0.40 | −1.21 |
| ACACB | −1.83 | 1.12 | 1.31 | 0.91 | 0.24 | NHSL2 | −0.37 | 0.24 | 0.75 | −0.21 | −0.05 | AC024581.1 | 0.46 | −0.04 | 1.43 | 1.17 | 1.10 |
| CPSF3 | 0.71 | −0.43 | −0.55 | −0.19 | −0.28 | AC092038.1 | 1.02 | −0.63 | 0.06 | −0.59 | 0.78 | AC093524.1 | 0.32 | −1.31 | 0.31 | −0.81 | 1.60 |
| AP1B1 | 0.83 | −0.37 | −0.80 | −0.10 | −0.37 | RN7SL732P | −1.00 | 0.42 | −0.03 | 0.97 | 0.10 | AC016245.1 | −0.10 | 0.22 | 0.10 | 0.01 | −0.05 |
| H2AFZ | 1.23 | −0.67 | −1.13 | −0.11 | −0.63 | RNA5SP382 | −1.30 | 0.10 | 1.07 | −0.35 | −0.03 | RNU2-10P | 0.61 | −1.24 | 0.19 | −1.58 | 1.37 |
| NMI | 1.20 | −0.67 | −1.04 | −0.15 | −0.61 | SNORD100 | −0.65 | 0.33 | −0.43 | 0.58 | −0.45 | AC126763.1 | −0.54 | 0.31 | −2.44 | 0.34 | −2.62 |
| RAB31 | 1.48 | −0.98 | −1.38 | −0.38 | −0.96 | PWAR1 | −0.84 | 0.53 | 0.26 | 0.53 | 0.22 | STMN2 | −0.21 | 0.04 | 1.16 | −1.04 | 0.43 |
| AHSA2P | −1.09 | 0.35 | 0.71 | 0.42 | 0.40 | MAPK9 | 0.15 | −0.07 | −0.13 | −0.07 | −0.07 | RNU6-934P | 0.42 | −1.19 | −0.89 | −0.79 | 0.34 |
| PGM2 | 1.20 | −0.45 | −0.83 | −0.01 | −0.46 | ATP2B3 | −0.80 | −0.92 | −1.18 | 0.06 | −0.09 | RNF166 | −0.08 | −0.23 | −0.01 | −0.06 | 0.21 |
| DDX21 | 1.40 | −0.90 | −1.24 | −0.24 | −0.72 | LINC02388 | −1.04 | −0.64 | 0.37 | 0.23 | 0.22 | AC016757.1 | −0.25 | −0.79 | −0.01 | 0.71 | 1.34 |
| EIF5A | 1.20 | −0.64 | −0.94 | −0.14 | −0.37 | AL513548.4 | −0.67 | 0.75 | 1.14 | 0.46 | 0.20 | G33743 | 0.51 | −0.82 | −1.08 | 0.19 | −0.08 |
| AMD1 | 1.25 | −0.50 | −0.97 | −0.15 | −0.66 | AL662795.2 | −0.23 | 0.08 | 0.39 | −0.19 | 0.17 | LINC01835 | −0.25 | 0.31 | 1.20 | 0.51 | 0.72 |
| PSMA5 | 1.05 | −0.54 | −0.84 | −0.15 | −0.44 | EID2B | −0.47 | −0.25 | 0.63 | 0.15 | 0.88 | AL359317.1 | −0.32 | 0.52 | 0.05 | −0.07 | 0.79 |
| PRR11 | 1.45 | −1.18 | −1.56 | −0.43 | −0.41 | CYP7A1 | −0.90 | 0.73 | −0.98 | 0.51 | −0.66 | AL139022.2 | 0.17 | 0.11 | 0.34 | −0.11 | 0.06 |
| HDAC1 | 0.77 | −0.37 | −0.78 | −0.11 | −0.38 | FBXW9 | 0.34 | 0.01 | −0.66 | 0.48 | −0.13 | AC020904.2 | −0.19 | −0.20 | 0.85 | −0.23 | −0.15 |
| EPRS | 1.11 | −0.47 | −0.76 | −0.20 | −0.56 | RDM1 | −1.04 | 0.25 | −1.19 | −0.53 | −0.80 | AC096537.2 | −0.52 | −0.15 | −0.03 | −0.87 | −0.04 |
| KYNU | 1.93 | −1.20 | −1.88 | 0.08 | −1.20 | GIMAP8 | −0.37 | 0.29 | 0.90 | 0.06 | 0.27 | MAB21L2 | 0.16 | 0.05 | 0.46 | 0.20 | 0.27 |
| GNAI3 | 1.11 | −0.44 | −0.72 | −0.20 | −0.55 | AC244034.1 | −0.50 | 0.86 | 0.40 | 0.06 | 0.10 | KRT27 | −0.42 | −1.38 | 2.93 | 0.13 | 4.00 |
| DIO3OS | −2.04 | 0.97 | 1.52 | 0.59 | 0.56 | AL831711.1 | −0.89 | 0.57 | 1.72 | 0.36 | 0.60 | AC083899.2 | 0.84 | −0.40 | −2.44 | 0.94 | −2.34 |
| LINC00632 | −2.03 | 1.23 | 2.07 | 0.27 | 0.34 | CDC20P1 | −0.82 | 0.38 | −0.01 | −0.05 | −0.13 | DPPA2P1 | 0.49 | −0.76 | −1.49 | 0.01 | 0.05 |
| DEPDC7 | 1.29 | −0.47 | −0.86 | −0.16 | −0.44 | PTPN2P2 | −0.82 | 0.15 | 0.19 | 0.02 | −0.19 | SPACA4 | 0.28 | 1.93 | 0.06 | −0.33 | −1.59 |
| LINC00894 | −1.08 | 0.58 | 1.01 | 0.20 | 0.25 | SPART | −0.24 | 0.18 | 0.37 | −0.05 | 0.00 | G5756 | 0.38 | 0.31 | −1.03 | 0.35 | −1.67 |
| CDC20 | 1.91 | −1.17 | −1.82 | −0.41 | −0.65 | AL109920.1 | 1.43 | −0.42 | −0.86 | −0.37 | −0.69 | PCDH9-AS3 | −1.23 | 1.30 | 0.83 | 0.30 | −1.33 |
| CDH12 | −2.30 | 0.90 | 1.12 | 0.52 | 0.29 | RN7SL349P | −0.69 | −0.30 | −0.88 | −0.41 | −0.60 | F9 | −0.39 | 0.83 | −0.19 | 0.70 | −0.94 |
| SHC2 | −1.67 | 0.50 | 1.03 | 0.64 | 0.51 | AL160254.1 | −1.44 | −0.15 | 2.30 | −1.34 | 0.86 | PGAM1P11 | −0.15 | 0.37 | 0.28 | 0.19 | 0.08 |
| ADAR | 0.60 | −0.37 | −0.60 | −0.16 | −0.36 | AC110998.1 | −0.89 | −0.26 | −1.04 | 0.43 | −0.07 | CTSK | 0.14 | 0.33 | 1.02 | −0.50 | −0.09 |
| KLK1 | −1.62 | 1.04 | 1.56 | 0.58 | 0.24 | AC007529.1 | −0.71 | 0.22 | −0.02 | 0.78 | −0.51 | AC108120.3 | −0.83 | 0.53 | −0.63 | 2.06 | 0.26 |
| NACC1 | 0.93 | −0.41 | −0.91 | −0.03 | −0.40 | AC135776.4 | −0.86 | −0.39 | 0.37 | 0.06 | 0.19 | AL590032.1 | −0.92 | 1.16 | 2.00 | −0.25 | 0.02 |
| FAXDC2 | −0.71 | 0.56 | 0.66 | 0.26 | 0.22 | AC090607.2 | 0.25 | 0.08 | 0.13 | 0.00 | −0.03 | AC123567.1 | −0.42 | 0.78 | −1.26 | 1.84 | −0.65 |
| KRT16P5 | 2.99 | −1.38 | −2.85 | 0.03 | −1.03 | CHRNB3 | 1.53 | −0.82 | −1.39 | −0.04 | −0.02 | AC114741.1 | −0.83 | 0.95 | −2.05 | 2.90 | 0.16 |
| NPM3 | 1.38 | −0.75 | −0.77 | −0.38 | −0.16 | G1580 | 0.78 | −0.94 | −2.72 | −0.29 | −1.64 | AC015983.2 | 0.61 | 0.15 | −0.15 | 0.55 | −1.35 |
| CLTA | 0.78 | −0.41 | −0.65 | −0.13 | −0.26 | AC103760.1 | −0.46 | 0.09 | 0.53 | 0.18 | 0.67 | NDUFB9P1 | 0.34 | −0.84 | 0.21 | 0.21 | 0.22 |
| APOD | −2.43 | 2.04 | 2.43 | 0.99 | 0.27 | OR51Q1 | −0.89 | 0.86 | 1.19 | 0.15 | 0.54 | RNY4P3 | 0.69 | −0.29 | −0.07 | 0.75 | −0.63 |
| ACSF2 | −1.25 | 0.53 | 0.63 | 0.59 | 0.25 | AL118506.1 | 0.34 | −0.29 | −0.83 | −0.20 | −0.37 | STUB1 | −0.07 | 0.09 | −0.13 | 0.17 | 0.03 |
| CCT2 | 1.18 | −0.70 | −1.03 | −0.19 | −0.57 | FCAR | 0.99 | −1.76 | −2.16 | −0.75 | −1.36 | AP001496.4 | 0.63 | −1.22 | 1.10 | 0.95 | 1.33 |
| SNRPG | 1.29 | −0.67 | −0.92 | −0.26 | −0.45 | AC021087.1 | 0.50 | −0.23 | −0.31 | 0.04 | −0.22 | LINC01901 | −0.97 | −0.43 | −0.36 | −0.72 | 1.71 |
| CBX7 | −1.26 | 0.86 | 1.15 | 0.46 | 0.45 | AC083864.1 | −1.15 | 0.44 | 0.45 | 1.26 | 0.15 | PABPC1P3 | 0.16 | −0.25 | −0.56 | −0.08 | −0.03 |
| SGCG | −1.81 | 1.38 | 1.16 | 0.61 | −0.03 | HOXC8 | −0.38 | −0.06 | −0.33 | 0.32 | −0.34 | G480 | 0.24 | −0.22 | −0.51 | −0.34 | −0.59 |
| PLXNA3 | −1.17 | 0.50 | 0.73 | 0.36 | 0.29 | AC096751.1 | −0.83 | −0.16 | 2.24 | 0.27 | 1.42 | EXOC3 | −0.06 | 0.09 | −0.29 | 0.15 | −0.05 |
| OR2T11 | −3.77 | 1.17 | 2.35 | 0.70 | 1.83 | G18962 | 0.71 | −0.83 | −1.18 | −0.37 | −0.08 | AC006254.2 | 0.34 | 0.64 | 1.40 | −0.13 | 1.37 |
| KRT32 | −3.22 | 1.90 | 0.98 | 0.60 | 1.40 | SNHG25 | −0.45 | 0.56 | 0.09 | 0.54 | −0.19 | ATF4P4 | −0.22 | −0.11 | −0.66 | 0.33 | −0.66 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| PSMB3 | 0.80 | −0.47 | −0.74 | −0.20 | −0.50 | AC080013.1 | −0.41 | 0.29 | 0.83 | −0.03 | 0.18 | AL132709.1 | −0.56 | −1.33 | 1.16 | −0.58 | 1.65 |
| KNL1 | 1.53 | −1.21 | −1.73 | −0.38 | −0.47 | AC009075.1 | 0.65 | −0.48 | −0.32 | 0.18 | 0.83 | AC009063.2 | −0.14 | 0.35 | −0.21 | 0.32 | 0.25 |
| CDCA2 | 1.56 | −1.27 | −1.62 | −0.44 | −0.30 | AL133368.1 | 0.74 | −0.23 | 0.03 | 0.35 | 0.11 | RNU6-422P | −0.40 | 0.35 | 0.58 | −0.27 | −1.00 |
| EZH1 | −0.80 | 0.53 | 0.79 | 0.19 | 0.17 | COPS5 | 0.13 | 0.02 | −0.03 | 0.00 | −0.03 | AC098936.1 | −0.43 | 0.75 | −0.86 | 1.26 | −1.22 |
| FAM49B | 0.91 | −0.74 | −0.95 | −0.25 | −0.30 | RPL13P12 | 0.34 | −0.05 | 0.25 | −0.72 | −0.66 | CDKL5 | −0.07 | 0.07 | 0.15 | −0.13 | −0.05 |
| RHCG | 3.38 | −2.15 | −3.66 | −0.99 | −2.77 | AC127496.2 | −1.55 | 0.86 | 1.69 | 0.77 | −0.54 | FRG2 | 0.76 | −0.78 | −1.24 | 1.24 | 0.20 |
| CCDC18-AS1 | −1.06 | 0.50 | 1.18 | 0.07 | 0.46 | RASSF8-AS1 | −0.34 | −0.15 | 0.37 | −0.32 | 0.12 | LINC01763 | −0.36 | −1.09 | −0.01 | −0.63 | −0.28 |
| BZW1 | 1.41 | −0.82 | −1.44 | −0.19 | −0.96 | SFMBT1 | −0.17 | 0.05 | 0.11 | 0.01 | 0.10 | AC243967.3 | 0.54 | −1.00 | −0.71 | −0.70 | −0.19 |
| MTURN | −1.04 | 0.86 | 0.87 | 0.41 | 0.15 | PGM5P4-AS1 | −0.98 | 0.44 | −0.01 | 1.15 | −0.18 | AL118556.1 | 0.23 | 0.28 | −0.54 | 0.60 | −0.24 |
| GREM2 | −2.19 | 0.35 | 2.08 | 0.46 | 0.61 | PEBP1P3 | 1.12 | −1.35 | −0.92 | −0.54 | 0.05 | AL929288.1 | −0.85 | 0.98 | 2.37 | 1.00 | 0.67 |
| RN7SL358P | −4.64 | 2.94 | 3.08 | 2.44 | 0.49 | LINC01298 | 1.03 | 0.30 | 0.23 | −0.12 | −0.47 | LDHBP2 | 0.49 | −1.61 | −2.24 | 0.18 | −0.69 |
| IRX6 | −2.02 | 1.50 | 1.36 | 0.98 | 0.37 | AC098617.1 | −0.58 | −0.01 | 0.43 | 0.80 | 0.42 | ELF3 | 0.18 | −0.17 | −1.12 | −0.05 | −0.21 |
| HPSE | 1.55 | −0.88 | −1.29 | −0.35 | −0.95 | RPL7P15 | −0.94 | 0.22 | 0.61 | −0.35 | 0.76 | RNU6-1200P | −1.03 | 0.02 | 0.15 | 0.12 | 1.35 |
| PLK2 | 1.33 | −0.67 | −1.26 | −0.32 | −0.42 | AC092674.1 | 1.37 | −0.98 | −1.57 | 0.06 | 0.34 | AC092978.1 | 0.37 | −1.23 | 0.26 | −0.91 | 0.16 |
| PCDHGA7 | −1.28 | 0.75 | 1.14 | 0.54 | 0.18 | GRAMD1B | 0.44 | −0.55 | −0.47 | −0.34 | 0.02 | AC108474.1 | −0.40 | 0.88 | −0.13 | 0.87 | 0.52 |
| G40351 | −3.10 | 1.39 | 2.44 | 0.96 | 0.67 | AC124069.1 | 0.44 | −0.07 | −0.45 | 0.08 | 0.10 | AL590422.1 | −0.41 | −1.45 | 0.35 | −0.60 | −0.01 |
| SLAMF7 | 2.11 | −1.10 | −1.18 | −0.50 | −0.46 | SEMASA | −0.33 | 0.25 | 0.62 | −0.38 | −0.12 | MYO5B | 0.08 | 0.17 | 0.01 | 0.00 | −0.27 |
| MEGF6 | −1.53 | 0.62 | 1.07 | 0.56 | 0.38 | RNU6-1089P | −1.22 | 1.01 | −0.36 | 0.92 | −2.55 | AC090616.3 | 0.77 | −1.54 | −0.46 | −1.14 | 0.42 |
| FGF14-IT1 | −1.80 | 0.68 | 1.59 | 0.30 | 0.25 | AC093677.2 | 0.82 | −0.31 | −1.13 | 0.09 | 0.11 | AP003419.2 | −0.21 | −0.04 | 0.21 | 0.02 | 0.03 |
| CCDC114 | −2.21 | 0.86 | 1.47 | 0.37 | 0.20 | NDUFB5 | 0.25 | −0.14 | 0.05 | −0.03 | −0.01 | OVAAL | 0.40 | −1.31 | −0.86 | 0.04 | 0.51 |
| NPM1 | 1.23 | −0.84 | −1.00 | −0.39 | −0.44 | AC091185.2 | 0.68 | −0.11 | −0.71 | 0.33 | −0.43 | AC009654.1 | −0.54 | −0.72 | 0.02 | 0.59 | 2.33 |
| ABCE1 | 1.16 | −0.71 | −0.77 | −0.27 | −0.34 | AC067750.1 | −0.36 | 0.05 | 0.55 | 0.02 | 0.39 | OR9M1P | −0.45 | 0.11 | −0.25 | 0.06 | −1.66 |
| C1QBP | 1.33 | −0.72 | −0.93 | −0.34 | −0.30 | AL139147.1 | 0.75 | −0.67 | −0.11 | −0.46 | 0.04 | AC011603.1 | 0.77 | −0.28 | −0.32 | −0.39 | 0.35 |
| CALML3 | 2.42 | −0.23 | −1.08 | 0.75 | −1.47 | COQ10B | 0.26 | 0.09 | 0.01 | −0.16 | −0.42 | AC253536.3 | −0.12 | 0.15 | 0.02 | 0.15 | −0.16 |
| PIWIL2 | −1.72 | 0.77 | 1.01 | 0.31 | 0.05 | NAT10 | 0.22 | −0.29 | −0.26 | −0.08 | 0.14 | COX20P2 | 1.00 | −0.86 | −2.21 | 0.79 | −1.34 |
| HMGB3 | 1.34 | −0.76 | −1.30 | −0.23 | −0.52 | CDYLP1 | 1.76 | −0.85 | −0.36 | −0.40 | −0.68 | MYO5BP3 | −0.47 | 1.03 | −2.19 | −0.49 | −3.59 |
| FABP5P1 | 3.77 | −0.85 | −2.96 | 0.15 | −2.08 | DENND5B-AS1 | −0.89 | −0.73 | 0.93 | −0.36 | 0.12 | AC104653.2 | 0.64 | −0.75 | 0.17 | −1.03 | −1.28 |
| GPT | −1.68 | 1.04 | 1.18 | 0.94 | 0.67 | RHOU | −0.42 | 0.46 | 1.03 | −0.07 | 0.15 | AL031315.1 | −0.46 | −1.37 | 1.71 | 0.36 | 2.02 |
| KRT43P | −3.79 | 1.81 | 1.78 | −0.42 | 0.04 | PHKA2-AS1 | −0.76 | 0.62 | −0.44 | 0.11 | −0.41 | LINC01596 | −0.26 | −0.16 | −0.13 | 0.62 | 0.75 |
| HSPA4 | 1.08 | −0.57 | −0.81 | −0.33 | −0.47 | AC023024.1 | 0.72 | −0.25 | −0.80 | 0.19 | −0.62 | LINC00909 | −0.08 | 0.08 | 0.28 | 0.04 | 0.16 |
| SNHG26 | 1.37 | −0.89 | −1.10 | −0.28 | −0.34 | AC007405.1 | −0.86 | 0.73 | −0.41 | 0.69 | −0.04 | FOXD4 | −0.30 | 0.19 | 0.69 | 0.33 | 0.38 |
| DCST1 | −1.59 | 0.86 | 1.25 | 0.72 | 0.66 | AC006387.1 | −0.76 | −0.29 | 0.78 | 0.07 | 0.57 | AC004771.2 | 0.23 | 0.05 | −2.04 | 0.39 | −0.71 |
| NRAS | 1.05 | −0.38 | −0.81 | −0.10 | −0.69 | AC005522.1 | 0.78 | −0.20 | −0.13 | 0.12 | 0.20 | AC137055.1 | 0.14 | −0.18 | 0.40 | −0.13 | 0.00 |
| PSMA4 | 1.10 | −0.61 | −0.88 | −0.22 | −0.50 | KCTD15 | 0.37 | −0.06 | −0.25 | 0.11 | −0.13 | KLKP1 | 0.28 | −0.07 | 0.63 | −0.70 | −0.47 |
| ST6GALNAC1 | 1.56 | −0.32 | −1.86 | 0.13 | −0.79 | AC104115.1 | −0.48 | 0.12 | 1.11 | −0.29 | 0.49 | AP003730.2 | −0.49 | −1.95 | −1.66 | −0.18 | 0.86 |
| OR1S2 | −3.47 | 1.28 | 1.64 | 1.19 | 0.39 | INGX | −0.76 | 0.00 | −0.07 | 0.33 | −0.13 | AC025048.6 | −0.18 | 0.63 | −0.60 | 0.44 | −0.89 |
| SMC6 | 0.61 | −0.37 | −0.35 | −0.23 | −0.14 | MCM3AP-AS1 | 0.21 | −0.07 | −0.21 | 0.16 | 0.18 | ANKRD10 | −0.06 | −0.06 | 0.04 | −0.11 | −0.02 |
| BCAN | −2.18 | 1.35 | 1.52 | 0.92 | 0.61 | AC103876.1 | −0.50 | 0.19 | 1.00 | −0.64 | 0.00 | AL353586.1 | −0.16 | 0.44 | 0.07 | 0.19 | −0.14 |
| GNL3 | 0.97 | −0.50 | −0.79 | −0.19 | −0.45 | RNU6-302P | 2.01 | −1.44 | −2.07 | −0.14 | −0.71 | AC108941.2 | −0.41 | 0.98 | 1.70 | 1.40 | 1.06 |
| AMOT | −1.72 | 1.20 | 1.69 | 0.39 | 0.10 | ASIC4 | −0.72 | 0.00 | −0.48 | 0.70 | 0.57 | PCDHGC5 | 0.15 | −0.09 | −0.20 | −0.18 | −0.17 |
| ACTRIA | 0.67 | −0.23 | −0.55 | −0.13 | −0.42 | NDUFA11 | −0.34 | 0.27 | 0.15 | 0.34 | 0.22 | MIR3613 | −0.42 | −0.33 | −0.09 | −0.87 | −0.59 |
| AL357078.1 | −2.19 | 1.29 | 2.02 | 0.97 | 0.43 | RPSAP13 | 0.63 | −0.59 | −1.41 | −0.01 | −0.27 | KIAA0319L | −0.05 | 0.04 | 0.08 | 0.05 | 0.12 |
| SCEL | −1.41 | 0.91 | 2.04 | 0.43 | 0.40 | LINC01645 | −1.23 | 1.04 | 1.26 | 1.48 | 0.20 | PPIAP77 | 0.53 | −1.49 | −0.04 | −0.18 | 1.86 |
| MTF1 | 0.88 | −0.34 | −0.70 | −0.21 | −0.47 | AL592293.1 | −1.21 | 0.71 | 1.83 | 0.14 | 0.67 | AC245100.4 | 0.27 | −1.20 | −0.02 | −0.29 | 0.03 |
| RB1 | 0.78 | −0.44 | −0.64 | −0.27 | −0.39 | G36779 | 0.57 | −0.03 | −0.82 | 0.43 | 0.13 | AC008649.1 | 0.58 | −0.60 | −0.28 | −0.63 | 1.15 |
| RALB | 1.03 | −0.58 | −0.99 | −0.26 | −0.39 | G31132 | 0.69 | −1.22 | −0.68 | 0.31 | −0.48 | AC096992.2 | −0.12 | 0.09 | 0.60 | −0.15 | 0.32 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AL031599.1 | -2.96 | 0.91 | 2.16 | 0.44 | 0.98 | EIF2S3B | 0.46 | 0.04 | -0.39 | -0.70 | -0.53 | FAM83C-AS1 | -0.23 | 0.78 | 0.06 | 0.12 | -0.36 |
| SERPINE2 | 1.56 | -0.76 | -1.39 | -0.51 | -1.10 | MIR1302-5 | 2.36 | -0.24 | -2.82 | -0.44 | -3.01 | AC092811.2 | -0.44 | -0.33 | 0.46 | 0.50 | 1.03 |
| GSTM5 | -1.96 | 1.05 | 2.32 | 0.62 | 0.53 | FAM200A | 0.23 | -0.07 | 0.20 | -0.17 | 0.00 | MIR320C2 | 0.38 | -0.28 | 0.01 | 0.31 | 0.96 |
| LINC00893 | -1.18 | 0.52 | 1.12 | 0.27 | 0.40 | G10617 | -1.35 | 1.17 | 0.54 | 0.15 | -0.17 | GALC | -0.07 | 0.00 | 0.44 | 0.02 | 0.14 |
| SPTSSA | 1.30 | -0.67 | -0.84 | -0.14 | -0.31 | LGI1 | -0.89 | 0.17 | 0.72 | 0.27 | 0.09 | SNORD82 | -0.22 | 0.29 | -0.44 | -0.12 | -0.57 |
| PRRG4 | 1.60 | -0.50 | -1.18 | 0.00 | -0.66 | MIR4653 | 0.86 | -0.26 | 0.96 | -0.59 | 0.55 | RN7SL378P | -0.20 | 0.45 | 0.87 | -0.03 | 0.25 |
| FREM1 | -1.55 | 0.99 | 1.73 | 0.73 | 0.48 | FAM110D | -0.54 | 0.11 | 0.69 | -0.13 | -0.07 | AL359073.1 | -0.33 | -0.10 | 0.90 | 0.32 | 0.63 |
| MTAP | 0.53 | -0.35 | -0.59 | 0.20 | 0.09 | AC006539.1 | -0.69 | -0.03 | 0.74 | -0.38 | -0.42 | FTH1P2 | -0.23 | -0.07 | -0.16 | 0.46 | -0.39 |
| LUCAT1 | 2.03 | -1.87 | -2.82 | -0.51 | -1.45 | SLC22A20P | -0.45 | 0.01 | -0.11 | -0.15 | 0.28 | MRPS31P4 | -0.15 | -0.18 | -0.02 | 0.12 | -0.19 |
| PRMT3 | 0.85 | -0.50 | -0.68 | -0.18 | -0.11 | MIR4713HG | 0.76 | -0.53 | -0.52 | -0.08 | 0.44 | AC073065.1 | -0.37 | -1.11 | -1.31 | -0.70 | -0.98 |
| APOBEC3A | 3.68 | -3.22 | -4.80 | -0.22 | -5.45 | LLGL1 | 0.21 | -0.08 | -0.33 | 0.12 | -0.13 | KLF4 | -0.09 | 0.61 | 0.17 | 0.13 | -0.24 |
| ISG15 | 1.84 | -1.39 | -1.24 | -1.18 | -0.50 | CIAO1 | 0.19 | -0.10 | -0.08 | -0.03 | 0.13 | ADRB3 | 0.39 | -0.95 | -1.32 | 0.36 | -1.16 |
| CASC1 | -1.70 | 1.07 | 1.61 | 0.81 | 0.14 | ANK1 | 0.52 | -0.34 | -0.70 | -0.24 | -0.50 | AC011524.2 | -0.43 | 0.26 | -0.35 | 1.99 | 0.50 |
| KIF18A | 1.43 | -1.10 | -1.93 | -0.25 | -0.64 | G3899 | -0.81 | 0.09 | 1.09 | 0.36 | 0.71 | LINC02532 | 0.32 | -0.45 | -1.12 | 0.13 | -0.82 |
| AGPAT5 | 1.08 | -0.53 | -0.84 | -0.22 | -0.39 | EPM2A | -0.21 | 0.10 | 0.20 | 0.17 | 0.06 | POTEH | -0.58 | -0.01 | -0.85 | 0.20 | -0.03 |
| ATIC | 0.81 | -0.62 | -0.74 | -0.15 | -0.33 | ATRAID | 0.28 | -0.04 | 0.09 | -0.11 | -0.07 | AC009276.1 | -0.53 | 0.56 | -1.83 | 1.02 | -2.64 |
| HOOK1 | 1.22 | -0.17 | -0.74 | 0.18 | -0.51 | DPEP1 | -1.17 | 0.17 | 1.47 | -0.95 | 0.16 | AC073342.1 | -0.66 | -1.17 | 0.57 | -1.24 | 0.34 |
| ADH1B | -3.40 | 3.11 | 3.18 | 1.81 | -0.02 | CRLF3 | 0.13 | -0.02 | -0.07 | -0.07 | 0.05 | PXT1 | 0.31 | -1.06 | -1.13 | 0.30 | 0.71 |
| SUB1 | 1.26 | -0.82 | -1.16 | -0.22 | -0.45 | SH3GLB1 | 0.26 | -0.01 | -0.13 | -0.10 | -0.25 | RNA5SP39 | -0.32 | -1.46 | -0.29 | -1.29 | 0.17 |
| ARL14 | 3.87 | -1.40 | -2.97 | 0.28 | -1.42 | AC005332.4 | -0.35 | 0.20 | 0.29 | 0.35 | 0.14 | RN7SKP193 | 0.43 | -2.10 | 0.07 | -0.98 | 0.64 |
| AC004982.2 | -1.30 | 0.98 | 0.64 | 0.65 | 0.11 | LINC01762 | -0.68 | 0.25 | 0.46 | -0.26 | 0.27 | AC023908.3 | 0.16 | -0.18 | -0.18 | 0.07 | -0.12 |
| ADAM22 | -1.34 | 0.59 | 1.16 | 0.22 | 0.39 | EGR3 | -0.34 | 0.49 | 0.63 | 0.21 | -0.11 | RASA4DP | -0.27 | 0.08 | 0.59 | 0.72 | 0.64 |
| CSE1L | 0.93 | -0.47 | -0.60 | -0.23 | -0.25 | MRPL35P3 | 1.20 | -0.68 | -1.84 | -0.01 | -0.91 | AP001994.1 | -0.89 | -0.25 | 0.61 | 0.65 | 0.81 |
| LRRC37A7P | -1.86 | 0.93 | 2.09 | -0.05 | 0.06 | PLBD1-AS1 | 0.54 | 0.33 | -0.10 | 0.30 | 0.05 | AC105940.1 | -0.45 | 0.04 | 1.28 | 0.24 | 0.73 |
| PCDHGA6 | -1.04 | 0.61 | 1.06 | 0.34 | 0.26 | RPS2P7 | 0.57 | -0.04 | -0.09 | -0.12 | -0.16 | SCML4 | -0.19 | -0.05 | 0.29 | -0.32 | 0.61 |
| FUT1 | 1.39 | -0.31 | -1.17 | 0.02 | -1.03 | GTF2IP23 | -0.49 | 0.32 | 0.16 | 0.11 | 0.54 | SH2D6 | -0.27 | -0.71 | -0.26 | -0.39 | 0.12 |
| SLC16A6 | 1.36 | -0.60 | -1.07 | -0.08 | -0.37 | AC010883.1 | -0.63 | -0.05 | 0.50 | 0.37 | 0.48 | LMF1-AS1 | -0.18 | 0.20 | 0.27 | 0.26 | 0.66 |
| KRT17 | 3.87 | -2.84 | -4.11 | -0.79 | -3.01 | AC006063.2 | -1.34 | 0.48 | 0.44 | 0.38 | -0.99 | AL355001.2 | -0.14 | -0.07 | -0.51 | -0.09 | -0.63 |
| SALL2 | -1.48 | 0.76 | 1.56 | 0.17 | 0.43 | AC098850.3 | -0.93 | 0.44 | 1.23 | 0.39 | 1.06 | NPIPB8 | 0.26 | -0.55 | -0.09 | -0.18 | 0.50 |
| CXCL1 | 3.01 | -3.24 | -4.29 | 0.51 | 0.28 | AL354726.1 | 0.56 | -0.78 | -0.22 | -0.34 | 0.01 | G1920 | -0.73 | -0.15 | 2.29 | 0.64 | 1.38 |
| EEF2K | -1.19 | 0.80 | 0.94 | 0.51 | 0.15 | GPR161 | 0.23 | -0.03 | 0.32 | -0.33 | -0.09 | AC024475.1 | 0.19 | -0.52 | 0.27 | -0.07 | 0.48 |
| ACTB | 1.08 | -0.82 | -1.05 | -0.37 | -0.50 | AC007182.2 | 0.77 | -0.78 | -1.32 | 0.19 | -0.37 | LRP1-AS | 0.21 | 0.22 | -0.57 | -0.29 | -1.12 |
| FABP5P11 | 3.97 | -0.66 | -3.26 | 0.27 | -2.52 | G30504 | 0.96 | 0.51 | -0.29 | 0.24 | -0.98 | AC114550.2 | 0.88 | 1.46 | 0.03 | 2.01 | -0.93 |
| POC1B-AS1 | -0.75 | 0.45 | 0.91 | -0.02 | 0.23 | AC096664.1 | -0.98 | -0.53 | 0.23 | 0.02 | 0.27 | AL096712.1 | 0.22 | 0.50 | 0.14 | 0.39 | -0.08 |
| CD27-AS1 | -1.45 | 0.59 | 1.17 | 0.26 | 0.16 | GLIDR | -0.47 | -0.25 | 0.11 | -0.20 | 0.29 | AC091060.1 | 0.25 | -0.33 | -0.58 | -0.06 | -0.69 |
| PDZK1IP1 | 1.90 | -0.94 | -2.06 | -0.10 | -1.35 | RP1 | -0.56 | 0.06 | -0.14 | 0.13 | -0.27 | RPS4XP19 | -0.67 | -1.81 | -0.65 | -1.11 | 0.69 |
| SELENBP1 | -1.43 | 1.13 | 0.94 | 0.54 | -0.01 | KCND3-IT1 | 0.81 | -1.15 | -0.73 | -0.60 | 0.12 | HOXA2 | -0.11 | -0.23 | 0.40 | 0.45 | 0.44 |
| RNF149 | 0.87 | -0.27 | -0.62 | -0.05 | -0.31 | AL360219.1 | 0.88 | -0.89 | 1.46 | -0.89 | 0.75 | SPP1 | 0.28 | -0.63 | 0.25 | -0.59 | 1.64 |
| AL133367.1 | -1.60 | 1.34 | 1.66 | 0.68 | 0.54 | KLRC1 | 1.05 | -1.19 | 0.17 | -0.96 | 1.02 | ATP6VOA2 | 0.06 | -0.01 | 0.15 | -0.12 | 0.10 |
| AC011477.1 | -1.28 | 0.37 | 0.71 | 0.22 | 0.44 | AC008731.1 | -0.44 | 0.11 | 0.21 | 0.15 | 0.44 | G38985 | 0.89 | -0.70 | -0.15 | -0.85 | 0.64 |
| IMMP2L | -0.74 | 0.52 | 0.50 | 0.22 | 0.14 | AC008121.1 | -0.83 | -0.82 | 1.52 | -0.28 | 0.96 | LINC02492 | 0.79 | -0.09 | -0.76 | 0.26 | 0.21 |
| FLOT2 | 0.80 | -0.63 | -0.82 | -0.07 | -0.11 | GRINA | -0.20 | -0.03 | 0.17 | -0.15 | 0.01 | MIR605 | 0.43 | -0.03 | 2.00 | 0.20 | 0.53 |
| CHPT1 | -1.04 | 0.53 | 0.89 | -0.03 | 0.22 | RAMP3 | 0.37 | -0.12 | 0.72 | -0.07 | 0.14 | AC008743.1 | -0.81 | -0.92 | -0.34 | -0.36 | 0.77 |
| IL1RN | 1.67 | -1.28 | -1.26 | -0.07 | -0.69 | PURG | -0.87 | -0.27 | 1.98 | -0.06 | 0.95 | NFYAP1 | -0.50 | -0.66 | -1.29 | 0.12 | -0.78 |
| BTF3 | 1.01 | -0.26 | -0.68 | -0.12 | -0.55 | CTD-2328D6.1 | -1.47 | 0.30 | 0.79 | 0.34 | 0.50 | MTATP6P4 | 0.56 | -1.32 | -1.59 | 1.26 | 2.64 |
| SOX7 | 1.39 | -0.27 | -1.11 | 0.01 | -0.88 | MARK2P13 | -0.94 | 1.49 | 3.15 | 1.21 | 0.34 | AC090888.3 | -0.97 | 0.34 | 2.38 | -1.62 | -0.19 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| NEK2 | 1.78 | −1.23 | −1.58 | −0.18 | −0.15 | AF228730.1 | −1.09 | −0.08 | 2.00 | 0.20 | 0.89 | HCG25 | 0.15 | 0.05 | 0.12 | 0.06 | −0.07 |
| PPIA | 1.01 | −0.44 | −0.93 | −0.03 | −0.60 | RNF220 | −0.15 | 0.15 | 0.10 | 0.15 | 0.03 | NANOGNBP3 | 0.12 | −0.03 | 0.08 | 0.19 | 0.22 |
| PDPN | 1.50 | −1.25 | −1.49 | −0.49 | −0.31 | OR5AZ1P | −0.96 | 0.11 | 0.39 | 0.85 | 0.96 | RNU6-1208P | 0.40 | −1.85 | −1.65 | 0.08 | 1.18 |
| MATN4 | −2.22 | 2.02 | 2.48 | 1.15 | 0.69 | INKA1 | 0.35 | −0.12 | −0.09 | 0.15 | 0.19 | OSMR-AS1 | −0.09 | 0.03 | −0.15 | 0.03 | −0.22 |
| DDX52 | 0.70 | −0.23 | −0.68 | 0.04 | −0.50 | AL031674.1 | 1.57 | −1.09 | −1.75 | −0.92 | −0.47 | MTND1P11 | 0.12 | −0.30 | 0.16 | −0.25 | 0.28 |
| SDK2 | 1.40 | −0.21 | −1.02 | 0.08 | −0.33 | RPL12P24 | −1.01 | −0.39 | 1.97 | −0.92 | −0.20 | AC010601.2 | 0.68 | 0.17 | −0.95 | 0.69 | −2.22 |
| ILF2 | 0.94 | −0.48 | −0.76 | −0.23 | −0.43 | EEF1A1P3 | −0.25 | −0.01 | 0.45 | 0.08 | 0.30 | AANAT | 0.22 | −0.38 | 0.89 | −1.43 | −0.08 |
| ITGA9-AS1 | −1.27 | 0.54 | 1.30 | 0.22 | 0.45 | AP006219.1 | 1.13 | −0.74 | 0.47 | −0.02 | 0.99 | AC141002.1 | 0.23 | −0.24 | 0.69 | −0.04 | 0.91 |
| PKD1L2 | −1.93 | 1.29 | 1.59 | 0.74 | 0.32 | LINC01270 | 0.91 | −0.58 | −2.45 | 0.57 | −0.93 | RNU7-158P | 0.46 | 0.40 | −0.41 | −0.68 | −1.29 |
| ARHGAP40 | −1.71 | 1.17 | 2.13 | 0.26 | 0.67 | ANXA6 | −0.43 | 0.06 | 0.60 | −0.21 | 0.15 | AC087045.2 | −0.93 | 0.27 | 0.28 | −0.39 | −0.28 |
| ANKRD31 | 2.26 | −1.56 | −2.60 | −0.48 | −1.10 | ADGRE5 | −0.34 | −0.22 | −0.26 | −0.15 | −0.29 | AL445483.1 | −0.38 | −1.52 | −1.22 | −0.61 | 0.46 |
| PLP1 | −1.31 | 0.89 | 1.17 | 0.28 | 0.79 | FAM25C | 0.70 | −0.25 | −0.17 | −0.46 | 0.19 | CYP2C18 | −0.18 | 0.93 | 0.08 | 0.70 | −0.22 |
| GFRA1 | −1.74 | 1.42 | 1.81 | 0.26 | 0.41 | ARL2BP | 0.48 | −0.10 | −0.57 | 0.55 | 0.01 | AC115621.1 | 0.13 | −0.49 | −0.10 | −0.06 | 0.16 |
| AC092802.1 | −2.00 | 1.49 | 1.52 | 1.35 | 0.23 | AC096921.2 | 0.50 | −0.01 | 0.22 | −0.07 | −0.22 | AL137781.1 | −0.31 | −0.04 | 0.44 | 0.13 | −0.25 |
| G32308 | 3.51 | −0.92 | −3.49 | 0.04 | −3.04 | AC009502.2 | 1.66 | −1.18 | −2.69 | −0.38 | −1.09 | AL049835.1 | 0.18 | 0.25 | 0.22 | 0.19 | 0.26 |
| NUPR1 | −1.24 | 0.54 | 0.82 | 0.37 | 0.05 | BEX1 | −1.01 | 1.04 | 2.12 | −0.30 | 1.12 | FDXR | −0.09 | 0.06 | 0.00 | 0.17 | 0.23 |
| AC110285.1 | −2.10 | 0.97 | 0.01 | 1.33 | 0.41 | AC005274.1 | −1.32 | −0.61 | 1.16 | 0.71 | 1.50 | AC009102.2 | −0.36 | −0.36 | −1.46 | −0.04 | −1.52 |
| CKAP2L | 1.84 | −1.38 | −1.97 | −0.49 | −0.52 | LINC00240 | −0.52 | −0.02 | 0.00 | 0.11 | 0.26 | AP002991.1 | −0.66 | −0.37 | 0.83 | −0.68 | 0.81 |
| SQLE | 1.66 | −0.71 | −1.21 | −0.12 | −0.89 | AC021683.3 | −1.00 | 1.32 | 0.00 | −0.28 | −0.12 | PTGES3P3 | 0.48 | 0.39 | −0.48 | 1.24 | −0.38 |
| SACS | 0.87 | −0.53 | −0.87 | −0.20 | −0.31 | G5134 | 1.35 | 0.08 | −0.31 | 0.37 | −0.60 | NDUFAF6 | 0.04 | −0.09 | −0.10 | −0.01 | 0.08 |
| AEN | 1.20 | −0.82 | −1.00 | −0.01 | −0.36 | NPM1P46 | 1.00 | −1.00 | −0.76 | −0.21 | 0.15 | DHX34 | −0.07 | −0.12 | −0.16 | −0.04 | 0.30 |
| BNC1 | 2.01 | −0.98 | −2.08 | −0.21 | −1.49 | AC004847.1 | 0.83 | −0.80 | −0.53 | −0.83 | −0.05 | ATP6V1G3 | −0.52 | −1.32 | −2.17 | 0.52 | −1.58 |
| G39634 | 3.70 | −1.67 | −4.21 | −0.12 | −2.00 | GPR37 | 0.49 | −0.17 | −0.75 | 0.38 | 0.21 | AP000859.1 | 0.84 | 0.75 | −2.12 | 1.30 | −2.35 |
| KIF11 | 1.47 | −0.97 | −1.29 | −0.22 | −0.48 | AC019072.1 | −0.34 | 0.41 | 0.04 | 0.19 | −0.18 | SEPT14P21 | −0.43 | −0.18 | −1.43 | 0.03 | −0.72 |
| LY6D | 2.00 | −0.76 | −1.53 | 0.00 | −1.12 | SLC22A7 | −0.70 | 0.07 | 0.52 | 0.14 | 0.79 | AIFM1P1 | 0.50 | 0.36 | −0.89 | 0.34 | −0.52 |
| CMTR2 | 0.98 | −0.55 | −0.76 | −0.20 | −0.24 | AC004974.1 | 0.88 | −0.29 | −0.64 | 0.36 | −0.49 | AC137932.1 | −0.12 | 0.12 | 0.31 | 0.05 | 0.26 |
| G11188 | −1.45 | 1.08 | 1.03 | 0.48 | −0.15 | AC010638.1 | −0.63 | 0.09 | 0.45 | −0.11 | 0.16 | AC006195.1 | −0.26 | 0.13 | −0.79 | 0.32 | −0.26 |
| CROCC | −1.41 | 0.44 | 0.52 | 0.63 | 0.56 | KAZALD1 | −0.40 | 0.43 | 0.50 | 0.21 | 0.09 | AL031733.2 | 0.24 | −0.62 | 0.38 | 0.12 | 0.56 |
| KIF2C | 1.45 | −1.09 | −1.62 | −0.38 | −0.33 | SSX6P | 1.49 | −0.75 | −1.54 | −0.06 | −2.80 | AC097359.1 | −0.29 | 0.25 | 1.24 | 0.55 | −0.06 |
| MAMDC2 | −1.61 | 1.06 | 1.14 | 0.63 | −0.14 | HSPA8P3 | 0.53 | −0.78 | −1.04 | −0.24 | −0.17 | EI24P3 | −0.75 | 0.52 | 0.05 | 1.52 | 0.25 |
| ATP2A2 | 0.75 | −0.47 | −0.86 | −0.24 | −0.41 | AL359095.1 | 0.80 | −0.19 | 0.08 | −0.57 | −0.02 | AP1M1 | 0.05 | −0.07 | −0.28 | −0.10 | −0.16 |
| FURIN | 0.89 | −0.42 | −0.93 | −0.15 | −0.46 | MIR548AA1 | 1.11 | −0.45 | −1.65 | 0.46 | −0.45 | AF127936.2 | 0.42 | −0.53 | −0.35 | 0.60 | −1.06 |
| SRM | 1.08 | −0.74 | −0.80 | −0.39 | −0.25 | SHISAL2B | −0.93 | −0.05 | −0.88 | 0.72 | 0.23 | AL133247.1 | 0.74 | 0.30 | −1.68 | −0.32 | −2.51 |
| MDFI | 1.70 | −1.02 | −2.38 | −0.04 | −1.02 | AC079331.2 | 0.50 | −0.73 | −0.37 | −0.68 | −0.01 | COMMD6 | 0.11 | 0.06 | 0.49 | −0.12 | −0.04 |
| G1047 | 2.49 | −1.45 | −2.62 | 0.00 | −0.79 | LANCL2 | 0.20 | −0.04 | −0.40 | 0.12 | −0.34 | MAPKAPK5-AS: | 0.16 | −0.08 | 0.83 | −0.09 | 0.32 |
| MRNIP | −0.88 | 0.35 | 0.66 | 0.17 | 0.31 | AL589674.1 | 1.17 | −0.67 | −1.53 | −0.67 | −0.88 | SRCAP | −0.08 | 0.08 | −0.20 | 0.05 | −0.12 |
| HS3ST6 | −2.46 | 1.83 | 2.59 | 1.33 | 0.20 | LIX1 | −0.75 | −0.32 | −0.38 | −0.34 | −0.15 | RNU2-46P | −0.29 | 0.26 | 0.36 | 0.14 | −0.23 |
| EDA | −1.13 | 0.82 | 0.86 | 0.42 | −0.03 | AC091078.3 | −1.34 | 1.13 | −1.65 | 1.64 | −1.85 | AC106782.6 | 0.16 | −0.21 | −0.48 | 0.01 | 0.24 |
| HMGCS2 | −2.38 | 1.61 | 2.66 | 0.93 | 0.58 | RAB1C | 1.48 | 1.41 | 0.07 | 0.92 | −1.27 | CYTH4 | 0.16 | −0.54 | −0.36 | −0.26 | −0.05 |
| CADM2 | −2.05 | 1.07 | 1.23 | 0.53 | 0.51 | SFTPD-AS1 | 0.61 | 0.62 | 0.19 | 0.21 | −0.73 | LINC00411 | 0.86 | −1.54 | 1.03 | −0.01 | 0.88 |
| CLDN8 | −2.01 | 1.19 | 2.20 | 0.25 | 0.18 | LINC00266-1 | −1.11 | 0.86 | 1.99 | 0.33 | −0.13 | CDK19 | 0.05 | 0.15 | −0.04 | 0.18 | −0.18 |
| NFIX | −0.89 | 0.71 | 0.76 | 0.37 | 0.16 | RBM26-AS1 | −0.38 | 0.01 | 0.47 | −0.20 | 0.14 | BCRP3 | −0.80 | −0.13 | 0.24 | 0.75 | 1.27 |
| PRKCQ-AS1 | 2.21 | −1.34 | −1.55 | 0.01 | 0.14 | HOMER3-AS1 | 0.96 | −1.87 | −1.45 | −0.41 | −0.97 | NPAP1P6 | 0.44 | −0.05 | −1.68 | 0.50 | −0.78 |
| FAM111B | 1.63 | −1.44 | −1.64 | −0.38 | −0.33 | LPGAT1 | 0.31 | −0.25 | −0.42 | −0.17 | −0.14 | SEC62-AS1 | 0.20 | 0.31 | −0.13 | −0.05 | −0.57 |
| LINC02345 | −1.95 | 0.38 | 0.59 | 0.48 | 0.56 | RNU6-166P | −1.06 | −0.04 | 0.95 | −0.36 | −0.12 | AC093724.1 | 0.18 | −0.73 | 0.08 | −0.18 | 0.77 |
| FAM83D | 1.89 | −1.48 | −1.92 | −0.26 | 0.04 | AC097263.1 | 0.63 | −0.30 | −0.40 | −0.28 | −0.39 | RN7SL334P | 0.41 | −1.09 | −0.04 | −2.35 | −0.75 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| PAK1IP1 | 1.07 | −0.68 | −0.81 | −0.28 | −0.40 | AC008813.1 | −0.83 | 0.39 | 0.37 | 0.35 | 0.77 | G31252 | 0.21 | 0.31 | −0.42 | 0.48 | 0.38 |
| ANP32BP3 | −2.91 | 0.90 | 2.63 | 1.69 | 0.24 | PGM5P3-AS1 | −1.72 | 0.25 | 1.06 | −0.36 | 0.41 | MTRNR2L2 | −0.23 | −0.32 | −0.93 | 0.90 | −0.48 |
| G41001 | 2.12 | −1.13 | −2.18 | 0.09 | −1.26 | BTN2A1 | −0.16 | −0.08 | 0.03 | −0.04 | 0.03 | AC013553.1 | −0.23 | 0.38 | −0.67 | 0.79 | −0.78 |
| SHISA5 | 0.77 | −0.58 | −0.73 | −0.08 | −0.09 | RNU4-40P | 0.58 | 0.30 | −0.44 | 0.10 | −0.50 | RNY4P19 | 0.66 | −0.86 | −0.60 | 0.22 | −0.69 |
| PLBD1 | 1.38 | −0.39 | −0.94 | 0.06 | −0.98 | NCOA2 | −0.15 | 0.28 | 0.22 | 0.18 | −0.10 | AL162412.1 | −0.64 | 1.02 | −1.78 | 1.08 | −1.28 |
| CNTNAP3B | −1.63 | 0.43 | 1.49 | 0.09 | 0.65 | AC006213.2 | −0.79 | 0.82 | 0.76 | 0.58 | 0.05 | CTHRC1 | 0.16 | 0.29 | 1.16 | −0.82 | −0.31 |
| GLI2 | −1.64 | 0.95 | 1.51 | 0.46 | 0.24 | LSMEM2 | 0.62 | −0.07 | −0.06 | 0.39 | 0.53 | AC106864.1 | 0.37 | −0.59 | 3.38 | −0.49 | −0.08 |
| CIRBP | −0.71 | 0.40 | 0.54 | 0.29 | 0.26 | AC062037.1 | 1.53 | −1.13 | 0.08 | −0.05 | 0.39 | RPL15P14 | −0.25 | 0.64 | 0.07 | 0.18 | −0.18 |
| MARK3 | 0.65 | −0.36 | −0.66 | −0.22 | −0.23 | HKDC1 | 0.52 | −1.06 | −0.83 | −0.63 | −0.07 | C8G | −0.24 | 0.20 | 0.03 | 0.33 | −0.15 |
| MYO3A | −2.33 | 0.58 | 0.62 | 1.42 | 0.02 | AL627309.1 | 0.57 | 0.11 | −0.87 | 0.42 | −0.03 | AC008268.1 | −0.66 | −0.63 | −0.33 | −1.13 | −0.01 |
| NABP1 | 1.51 | −1.37 | −1.42 | −0.30 | −0.14 | LINC02155 | −1.30 | 0.30 | −0.02 | 0.73 | 0.14 | DEXI | 0.09 | −0.36 | 0.17 | −0.18 | 0.49 |
| FPGT-TNNI3K | −1.14 | 0.93 | 1.05 | 0.24 | 0.10 | G7527 | −0.41 | 0.08 | 0.60 | 0.17 | 0.18 | AC239600.2 | −0.74 | −0.23 | −0.08 | 2.47 | 1.52 |
| SEMA3D | −1.71 | 1.19 | 1.68 | 0.40 | 0.27 | FOX01 | −0.21 | 0.42 | 0.35 | 0.07 | −0.04 | RN7SL738P | 0.34 | 1.18 | −0.66 | 0.11 | −1.80 |
| ANLN | 1.47 | −0.96 | −1.67 | −0.30 | −0.85 | NSMF | −0.27 | 0.00 | −0.24 | 0.08 | −0.02 | OR8J2 | 0.59 | 0.69 | −0.60 | 0.12 | −2.11 |
| SRP72 | 0.88 | −0.43 | −0.69 | −0.24 | −0.45 | ERGIC2 | 0.19 | −0.05 | 0.02 | −0.06 | 0.07 | AC007349.4 | 0.45 | −1.24 | −0.82 | −0.01 | 0.68 |
| GSN | −1.36 | 0.99 | 0.85 | 0.36 | −0.18 | AL353597.3 | 1.58 | −0.99 | −0.82 | −0.10 | 0.23 | MIRLET7I | −0.76 | 0.55 | 0.30 | 0.38 | 0.88 |
| AP1S3 | 1.23 | −0.43 | −1.32 | 0.07 | −0.52 | ATP5PBP7 | −1.29 | 0.63 | 2.46 | 0.39 | 0.19 | AC025287.2 | 0.53 | 0.18 | −0.59 | 0.82 | −0.82 |
| KIF14 | 1.50 | −1.16 | −1.97 | −0.36 | −0.49 | CYP4A44P | −1.91 | −0.87 | 1.22 | −0.51 | 1.84 | HSPD1P16 | −0.27 | 0.85 | −0.73 | 0.29 | −1.28 |
| ABCB11 | −1.94 | 1.06 | 0.58 | 0.81 | 0.44 | BRI3BPP1 | −1.30 | 1.38 | 1.78 | 0.45 | 0.39 | PGM1 | 0.07 | −0.15 | −0.31 | 0.07 | −0.01 |
| BEX4 | −0.84 | 0.66 | 1.10 | −0.13 | −0.02 | RNA5SP494 | −0.73 | −0.01 | 0.24 | 0.19 | 0.04 | AC092755.1 | 0.26 | −0.99 | −0.67 | −0.72 | −0.24 |
| AC090673.2 | 3.30 | −2.03 | −2.26 | −0.17 | −1.01 | RNU2-50P | −0.70 | 0.11 | −0.60 | 0.81 | −1.36 | HNRNPA1P50 | 0.12 | 0.21 | 0.30 | −0.19 | −0.11 |
| LINC00963 | −0.72 | 0.17 | 0.79 | −0.07 | 0.44 | OR6V1 | −0.71 | 0.09 | 1.24 | −0.57 | 0.35 | AP001993.1 | 0.38 | 0.29 | −0.03 | 0.30 | −0.11 |
| KRT31 | −2.25 | 1.22 | 0.65 | 0.19 | 0.35 | AL023806.1 | −1.33 | −0.44 | 1.52 | 0.17 | 0.95 | AC010326.4 | −0.16 | −0.02 | 0.36 | −0.06 | 0.13 |
| SAE1 | 0.69 | −0.46 | −0.59 | −0.20 | −0.34 | GET4 | −0.38 | −0.02 | 0.21 | 0.00 | 0.19 | SLC9B1P1 | 0.84 | 0.10 | −0.28 | 0.28 | −1.38 |
| RPS6KA6 | −1.25 | 0.88 | 1.62 | 0.31 | 0.40 | AL445253.1 | −0.55 | 0.18 | 0.12 | 0.54 | 0.31 | AC092681.1 | −0.46 | 0.73 | −0.88 | 0.25 | 0.27 |
| LINC01725 | −1.25 | 0.66 | 1.49 | 0.35 | 0.76 | GPR176 | 0.43 | −0.25 | 0.70 | −0.84 | −0.06 | BICD1 | −0.10 | 0.09 | 0.32 | −0.37 | −0.37 |
| ABCA9 | −1.73 | 1.30 | 1.93 | 0.94 | 0.18 | KRT8P3 | −0.64 | 0.44 | 0.38 | 0.46 | 0.74 | AL356966.1 | −0.09 | −0.24 | 0.04 | 0.17 | 0.45 |
| SET | 0.90 | −0.53 | −0.71 | −0.11 | −0.18 | CD55 | 0.27 | 0.07 | −0.14 | −0.29 | −0.40 | RNU6-773P | 0.40 | −0.51 | −0.82 | 0.11 | 0.06 |
| IFT172 | −0.69 | 0.34 | 0.58 | 0.18 | 0.19 | AGBL4-IT1 | −1.88 | 0.75 | 0.71 | 0.39 | −0.32 | AC104135.1 | −0.29 | 0.05 | 0.53 | 0.42 | 1.11 |
| CHD6 | −0.65 | 0.44 | 0.58 | 0.18 | 0.04 | RN7SL698P | 0.64 | −0.46 | −1.28 | −0.38 | −0.75 | KCTD9P6 | 0.41 | 0.10 | −2.16 | 0.07 | −2.73 |
| FBXO46 | 1.05 | −0.49 | −1.15 | −0.05 | −0.37 | AC103853.2 | −0.67 | 0.30 | 0.37 | −0.35 | −0.47 | AC025437.1 | 0.75 | −0.79 | 0.46 | −0.36 | −0.65 |
| PITPNB | 0.70 | −0.37 | −0.71 | −0.14 | −0.36 | RBM8B | 1.04 | 0.43 | −1.12 | 0.39 | −1.16 | PSKH1 | −0.05 | 0.26 | 0.05 | 0.18 | −0.12 |
| PSMD11 | 0.90 | −0.43 | −0.73 | −0.15 | −0.40 | AC012186.1 | −0.84 | 0.29 | −0.52 | −0.54 | −1.27 | AC104109.2 | 0.17 | 0.03 | −0.85 | 0.00 | −0.52 |
| CABLES1 | −0.77 | 0.49 | 0.24 | 0.44 | 0.18 | OCIAD1-AS1 | 0.78 | 0.41 | −0.40 | 0.78 | 0.29 | FAM131B | −0.20 | −0.19 | −0.41 | −0.08 | −0.07 |
| MPZL1 | 0.87 | −0.35 | −0.60 | −0.12 | −0.25 | MRPS18C | 0.24 | −0.02 | −0.08 | 0.09 | −0.08 | ST6GAL1 | −0.11 | 0.15 | −0.12 | 0.13 | 0.14 |
| GLTP | 1.46 | −0.38 | −0.65 | 0.03 | −0.63 | EIF4B | 0.18 | 0.05 | −0.18 | 0.19 | −0.13 | NDUFAF5 | −0.04 | 0.10 | −0.03 | 0.05 | −0.10 |
| PLS3 | 1.03 | −0.25 | −0.82 | −0.11 | −0.78 | RNA5SP91 | 1.20 | −1.52 | −1.41 | −0.91 | −1.13 | CCNHP1 | −0.52 | 0.40 | −1.78 | −0.23 | −1.03 |
| CTSL | 1.75 | −1.49 | −1.72 | −0.46 | −1.08 | ARPIN | −0.21 | −0.01 | 0.14 | 0.01 | 0.08 | AC026391.1 | 0.26 | −0.80 | −1.33 | 0.34 | 0.13 |
| ERO1A | 1.31 | −0.75 | −1.22 | 0.10 | −0.54 | CDC42P1 | 0.84 | −0.83 | 0.69 | −0.44 | 0.05 | AL135791.1 | −0.20 | 0.21 | 0.85 | 0.19 | 0.67 |
| FAM201A | −2.37 | 0.51 | 1.43 | 0.16 | 0.52 | AC020658.7 | 0.58 | −0.28 | −0.48 | 0.04 | −0.23 | AC145141.2 | 0.75 | 1.34 | −0.50 | 1.11 | −2.24 |
| ACTG1 | 0.84 | −0.58 | −0.90 | −0.34 | −0.50 | PSMB10 | 0.31 | −0.46 | −0.21 | −0.18 | 0.03 | LINC00488 | 0.44 | −0.67 | 1.09 | −0.35 | 0.02 |
| IFT122 | −0.70 | 0.32 | 0.54 | 0.17 | 0.22 | FANCM | 0.17 | −0.09 | −0.01 | −0.01 | 0.04 | AC022022.1 | 0.21 | −0.01 | −0.16 | −0.04 | 0.45 |
| PCDH11X | −1.81 | 0.30 | 0.61 | 0.15 | 0.20 | GRAMDIC | −0.26 | 0.47 | 0.69 | 0.49 | 0.07 | AP000907.1 | −0.43 | −0.89 | 1.81 | −0.80 | 1.72 |
| BUB1 | 1.53 | −1.12 | −1.56 | −0.42 | −0.74 | PEX1 | −0.18 | 0.23 | 0.33 | 0.15 | 0.15 | AC005050.1 | −0.27 | 0.12 | 0.89 | 0.71 | −0.02 |
| HAND2 | −2.42 | 0.74 | 2.14 | 0.46 | 0.47 | AC087280.1 | 0.88 | −1.40 | −1.02 | 0.14 | −0.82 | OR10A7 | 0.87 | 0.16 | −1.33 | 1.04 | 0.17 |
| PYGL | 1.22 | −1.06 | −1.43 | −0.17 | −0.20 | ADGRF2 | −0.53 | 0.43 | 1.56 | 0.49 | 0.30 | RN7SL466P | 0.70 | −0.80 | −1.67 | −0.06 | −0.73 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| PCDHGB6 | −0.86 | 0.50 | 0.89 | 0.24 | 0.23 | OR51H1 | 2.04 | −0.97 | −1.60 | 0.16 | 0.29 | PTPN6 | 0.07 | −0.28 | −0.02 | −0.12 | 0.18 |
| C21orf62-AS1 | −1.81 | 0.73 | 1.98 | −0.08 | 0.72 | SNORD119 | −0.58 | 0.08 | −0.12 | 0.43 | −0.76 | SNRNP27 | −0.07 | −0.02 | −0.07 | −0.17 | −0.13 |
| MRPL51 | 1.17 | −0.46 | −0.61 | −0.19 | −0.36 | PRKCA-AS1 | 0.44 | −0.37 | −0.33 | −0.58 | −0.16 | AC007786.2 | −0.79 | 0.12 | 0.95 | −0.69 | 0.08 |
| MYO1E | 0.66 | −0.24 | −0.60 | −0.28 | −0.50 | AC008080.3 | −1.09 | 0.10 | 1.69 | 0.23 | 0.46 | AP000866.6 | 0.10 | −0.12 | 0.00 | −0.02 | 0.11 |
| SMC4 | 1.08 | −0.72 | −1.02 | −0.28 | −0.37 | AP000365.1 | −0.90 | 0.05 | −0.13 | −0.37 | 0.91 | AL031121.2 | −1.06 | 1.57 | 0.63 | −0.75 | −1.63 |
| CDK1 | 1.69 | −1.23 | −1.55 | −0.32 | −0.58 | MIR627 | −0.81 | 0.62 | 0.85 | 0.35 | 0.19 | AC024230.1 | −0.46 | −0.71 | −0.41 | −0.29 | −0.04 |
| IFNWP19 | 4.78 | −1.70 | −3.47 | 0.16 | −1.14 | NFATC1 | −0.28 | 0.46 | −0.04 | 0.32 | −0.31 | FAM220CP | −0.51 | 1.59 | −0.69 | 0.01 | −1.64 |
| KCTD5 | 0.89 | −0.37 | −0.62 | −0.19 | −0.38 | SNX30 | 0.15 | −0.03 | −0.20 | 0.05 | −0.16 | GSX2 | −0.65 | 0.95 | −1.72 | 0.52 | −0.87 |
| BHLHE41 | −1.49 | 1.00 | 1.19 | 0.29 | 0.15 | RN7SL459P | 0.71 | 0.07 | −0.60 | −0.01 | −0.12 | AL138767.1 | 0.81 | 0.65 | −2.62 | 1.47 | −1.59 |
| GPR153 | 0.82 | −0.50 | −1.01 | −0.12 | −0.37 | ACAT1 | −0.20 | 0.28 | 0.25 | 0.07 | −0.11 | RN7SKP98 | 0.65 | −1.73 | 2.03 | −0.19 | 2.46 |
| CCT7 | 1.00 | −0.55 | −0.72 | −0.21 | −0.36 | PAIP2B | −0.36 | 0.69 | 0.76 | 0.48 | −0.12 | AKTIP | 0.06 | 0.26 | 0.13 | 0.09 | −0.22 |
| CENPN | 1.35 | −0.76 | −0.88 | −0.25 | −0.32 | RIPOR1 | −0.28 | 0.07 | 0.06 | 0.01 | −0.01 | LINC01983 | 0.51 | −0.23 | −1.74 | 1.37 | −0.70 |
| PTAFR | 1.18 | −0.67 | −1.28 | −0.26 | −0.81 | AL031985.3 | 0.52 | −0.24 | −0.21 | −0.42 | −0.39 | NCSTN | 0.05 | 0.00 | −0.01 | 0.02 | −0.06 |
| MTPN | 0.73 | −0.38 | −0.64 | −0.17 | −0.35 | MAGED2 | −0.17 | 0.15 | 0.25 | −0.14 | −0.17 | CLUHP3 | −0.08 | −0.05 | 0.02 | 0.10 | 0.28 |
| EIF3D | 0.62 | −0.27 | −0.55 | −0.10 | −0.38 | AC103874.1 | −1.26 | 1.15 | −0.41 | −0.29 | −0.94 | LINC01529 | −0.22 | −0.03 | 0.24 | 0.43 | 0.59 |
| AL139383.1 | −1.49 | 0.32 | 1.51 | 0.00 | 0.36 | GNA12 | 0.22 | −0.24 | −0.62 | −0.16 | −0.22 | PRKY | −0.13 | −0.10 | 0.34 | −0.23 | 0.34 |
| KIF20A | 1.65 | −1.25 | −1.99 | −0.39 | −0.63 | LINC02035 | 0.35 | 0.16 | −0.15 | 0.30 | −0.17 | CTSG | 0.17 | 0.44 | 1.54 | −0.04 | 0.00 |
| AAGAB | 0.73 | −0.43 | −0.56 | −0.16 | −0.20 | ALOX12-AS1 | −0.26 | 0.14 | 0.51 | −0.12 | 0.18 | ADAM21P1 | −0.34 | −1.53 | 0.08 | −0.52 | 0.49 |
| PI15 | 2.18 | −1.75 | −1.77 | −0.81 | −1.15 | G2591 | −0.71 | 1.06 | 1.63 | 0.15 | −0.13 | AC082651.4 | −0.61 | 1.38 | −1.62 | 0.49 | −1.63 |
| CALR | 1.08 | −0.66 | −0.90 | −0.35 | −0.45 | AC012618.3 | −0.47 | 0.30 | 0.86 | 0.15 | 0.07 | AC021739.1 | 0.32 | −0.07 | −0.11 | 0.05 | 0.32 |
| RAB38 | 1.49 | −0.67 | −1.13 | −0.26 | −0.76 | AL078621.3 | −0.53 | 0.20 | 0.63 | −0.11 | 0.55 | AC053481.2 | 0.49 | −1.86 | −1.27 | 0.13 | 0.26 |
| FAM136A | 0.88 | −0.48 | −0.88 | −0.14 | −0.31 | OR5C1 | −0.63 | 0.25 | 0.13 | 0.54 | 0.16 | AL442128.2 | −0.18 | 0.00 | −0.03 | 0.16 | −0.05 |
| MAN2A2 | −0.97 | 0.32 | 0.37 | 0.37 | 0.36 | SMIM31 | −1.23 | −0.34 | 0.52 | 0.38 | 0.42 | AC123768.2 | −0.16 | −0.21 | −0.19 | −0.21 | −0.34 |
| DKK2 | −2.01 | 1.26 | 3.73 | 0.17 | 0.69 | AC114812.1 | 1.10 | −0.14 | −0.55 | 0.03 | −0.02 | RPL5P17 | 0.26 | 0.29 | 0.59 | 0.36 | 0.49 |
| CCT8 | 0.86 | −0.46 | −0.67 | −0.15 | −0.39 | GTF3C5 | −0.16 | 0.08 | −0.04 | 0.10 | 0.12 | CAV2 | 0.10 | 0.19 | −0.24 | −0.23 | −0.47 |
| AC100801.1 | 3.46 | −1.33 | −2.93 | −0.76 | −0.60 | RPL10P16 | 0.44 | 0.17 | 0.26 | −0.04 | −0.51 | AC021006.2 | −0.55 | −0.13 | −2.04 | −0.33 | −2.04 |
| PTPRT | −1.68 | 1.14 | 1.50 | 0.48 | 0.06 | LRRC70 | 0.70 | −0.40 | 0.20 | −0.26 | 0.05 | GAPDHP20 | −0.74 | 0.95 | −0.28 | 0.49 | −1.62 |
| LRP8 | 1.52 | −1.18 | −1.78 | 0.00 | −0.43 | NCF4 | −0.44 | −0.03 | 0.25 | −0.11 | 0.13 | RPL23AP93 | 0.81 | −0.34 | −3.76 | 0.33 | −1.60 |
| IFI6 | 2.09 | −1.37 | −1.97 | −1.12 | −1.10 | AL023583.1 | −0.68 | −0.50 | 0.15 | 0.16 | 1.40 | PAQR7 | 0.11 | 0.08 | 0.52 | 0.22 | 0.19 |
| HDAC5 | −1.10 | 0.76 | 0.76 | 0.44 | −0.06 | AC008687.4 | 0.61 | −0.54 | 0.32 | −0.28 | 0.65 | AC007336.3 | −0.20 | −0.10 | 1.65 | −1.29 | −0.03 |
| EIF2S2 | 0.92 | −0.49 | −0.75 | −0.20 | −0.49 | AC010197.2 | −1.09 | 0.87 | 0.16 | 0.77 | −0.04 | LENEP | −0.28 | −0.60 | 0.95 | 0.05 | 0.87 |
| GPD1 | −3.14 | 3.08 | 1.84 | 1.65 | −0.20 | PPFIA2-AS1 | −0.93 | −0.16 | 0.65 | −0.14 | 0.59 | AC093267.1 | 0.43 | −0.02 | 1.20 | 0.13 | −0.67 |
| PCDHGA8 | −1.50 | 0.90 | 1.17 | 0.73 | 0.42 | NPIPB5 | −0.29 | 0.18 | 0.28 | 0.18 | 0.43 | AC004987.3 | −0.53 | −0.09 | −2.24 | 1.58 | −1.02 |
| RHOXF1-AS1 | −1.48 | 0.78 | 1.69 | 0.13 | 0.05 | AC012236.1 | −0.69 | −0.06 | 0.21 | 0.65 | 0.32 | OR51A3P | 0.77 | −1.10 | −1.06 | 0.04 | 0.26 |
| AL513321.2 | −3.83 | 1.08 | 2.16 | 0.52 | 0.39 | AC084855.2 | −0.54 | 0.15 | −0.07 | 0.35 | −0.07 | AC127035.1 | −0.10 | 0.08 | −0.13 | 0.20 | 0.17 |
| ESPNP | −2.65 | 0.72 | 1.42 | 0.41 | 0.66 | AP001790.1 | −1.31 | 2.13 | 1.73 | 1.92 | −0.19 | BARD1 | 0.07 | −0.16 | −0.17 | 0.07 | −0.05 |
| PLIN1 | −3.80 | 3.32 | 2.75 | 1.56 | −0.12 | AC010261.1 | −0.41 | 0.37 | 0.16 | 0.21 | −0.06 | ATP23 | −0.08 | 0.13 | 0.15 | 0.32 | 0.09 |
| CRCT1 | 2.29 | −0.60 | −1.24 | 0.01 | −1.22 | GUCY2D | 0.75 | −1.08 | −0.63 | 0.49 | 0.15 | AL138799.1 | −0.60 | 1.55 | −0.60 | 0.89 | −0.05 |
| PTBP3 | 1.26 | −0.53 | −0.90 | −0.10 | −0.60 | DPP8 | 0.16 | −0.02 | −0.07 | −0.03 | −0.13 | CCDC60 | −0.23 | −0.49 | −0.40 | 0.46 | 0.29 |
| FSIP2 | −1.25 | 0.90 | 1.72 | 0.26 | 0.59 | AC134669.1 | 0.96 | −0.54 | −1.14 | −0.12 | −1.26 | AC112198.2 | −0.31 | −2.61 | −0.03 | −0.30 | 2.33 |
| ADRA1A | −1.81 | 0.92 | 1.05 | 0.61 | −0.33 | HNRNPUL2 | 0.23 | 0.02 | −0.01 | −0.02 | −0.10 | KCNV1 | −0.32 | −1.69 | 0.22 | 0.56 | 0.63 |
| NRBP2 | −1.43 | 0.57 | 0.48 | 0.86 | 0.33 | AL606517.2 | 0.66 | −0.20 | −0.22 | −0.10 | −0.35 | AC011416.1 | −0.72 | 1.95 | −1.57 | 0.74 | −3.23 |
| NBPF1 | −0.76 | 0.39 | 0.76 | 0.19 | 0.39 | BAZ2B | −0.16 | 0.22 | 0.10 | 0.12 | −0.12 | G41968 | −0.67 | 0.15 | 0.75 | 1.95 | 0.78 |
| PLA2G4D | 1.56 | −0.64 | −1.25 | −0.26 | −0.69 | AC104819.3 | −0.46 | 0.39 | 0.52 | 0.28 | −0.16 | AC009754.1 | 0.20 | −0.36 | −0.01 | 0.14 | 0.10 |
| NEFL | 3.14 | −0.72 | −1.34 | −0.52 | −1.04 | AL357055.3 | −0.41 | −0.41 | −0.05 | −0.25 | 0.31 | POLA1 | 0.05 | −0.14 | −0.13 | −0.05 | 0.01 |
| LIPG | 2.66 | −2.30 | −2.72 | −0.57 | −2.03 | BLK | −0.77 | −0.53 | 0.72 | −0.47 | 0.57 | AC010255.3 | 0.23 | −0.54 | −0.38 | −0.12 | 0.05 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| ARPC2 | 0.64 | −0.35 | −0.71 | −0.07 | −0.41 | AQP6 | −0.63 | 0.29 | −0.25 | 0.13 | −0.08 | PGAM1P6 | −0.13 | 0.20 | 0.10 | 0.12 | 0.12 |
| CRYZL1 | −0.47 | 0.22 | 0.43 | 0.05 | 0.11 | AC017048.1 | −0.79 | 0.27 | 0.73 | 0.95 | 0.40 | RNA5SP235 | −0.71 | −0.45 | 0.52 | 0.49 | −0.08 |
| PRELP | −1.90 | 1.45 | 1.42 | 0.54 | −0.10 | RANBP10 | 0.15 | 0.02 | −0.09 | −0.01 | −0.06 | FAAH2 | 0.11 | 0.15 | −0.04 | 0.16 | 0.23 |
| SORBS1 | −1.85 | 1.26 | 1.39 | 0.56 | −0.06 | AC124804.1 | 0.77 | −0.63 | −1.06 | −0.70 | −0.21 | AC093536.2 | 0.80 | −1.94 | 0.33 | −0.21 | −0.14 |
| MYH3 | −1.29 | 0.11 | 0.21 | 0.14 | 0.14 | ANKRD20A17P | −0.82 | 0.84 | 0.88 | 0.70 | 1.16 | CYP2G2P | 0.45 | −0.72 | −1.08 | 0.04 | 0.20 |
| GPLD1 | −1.48 | 0.61 | 1.98 | 0.51 | 0.61 | MIR155HG | 0.45 | −0.83 | −0.30 | −0.62 | −0.21 | MGME1 | 0.08 | 0.09 | −0.03 | 0.17 | −0.07 |
| GTF2IRD2B | −1.13 | 0.63 | 1.13 | 0.24 | 0.35 | AC092718.7 | 0.46 | −0.72 | 0.38 | −0.33 | 0.47 | LINC01816 | 0.20 | −0.14 | 0.18 | 0.29 | 0.49 |
| HUNK | −1.04 | 0.26 | 0.77 | −0.10 | 0.00 | EARS2 | 0.16 | −0.07 | −0.12 | 0.08 | 0.10 | AC245505.2 | −0.75 | 0.73 | 0.52 | 1.88 | 0.82 |
| ENDOV | −0.93 | 0.31 | 0.63 | 0.17 | 0.26 | BBS1 | −0.35 | 0.23 | 0.11 | 0.30 | −0.02 | OR3A3 | 1.09 | −1.25 | 0.76 | −0.90 | −1.13 |
| AL663070.1 | −1.85 | 0.50 | 0.79 | 0.92 | 1.03 | FKBP1AP1 | 0.67 | −0.05 | −0.22 | −0.05 | −0.33 | SNORD114-16 | 0.52 | −0.06 | −1.55 | 0.71 | −1.70 |
| CCDC146 | −1.02 | 0.83 | 0.89 | 0.46 | 0.38 | SLC2A5 | 0.36 | −0.38 | −0.15 | 0.10 | −0.24 | AC024023.1 | −0.60 | −0.63 | −0.93 | −0.29 | −0.79 |
| PSMD13 | 0.63 | −0.38 | −0.47 | −0.21 | −0.20 | LINC02511 | −0.86 | 0.86 | 0.42 | 0.22 | −0.51 | MAN1B1-DT | 0.13 | −0.05 | −0.28 | 0.32 | −0.20 |
| FAM83B | 1.49 | −0.34 | −0.92 | −0.17 | −0.70 | AC092042.4 | −0.74 | 1.11 | −0.15 | 0.36 | −1.40 | LINC02006 | −0.46 | 0.85 | −1.40 | 1.51 | −0.58 |
| SIDT2 | −0.71 | 0.47 | 0.66 | 0.25 | 0.03 | GYPA | −1.11 | 0.27 | −0.39 | −0.33 | −1.11 | LINC02579 | 0.29 | 0.07 | −0.61 | 0.67 | −0.15 |
| MYH9 | 0.76 | −0.57 | −0.93 | −0.26 | −0.31 | NPM1P52 | −0.97 | 0.59 | 2.27 | 0.66 | 1.27 | AL353662.1 | −0.10 | −0.15 | −0.63 | −0.01 | −0.15 |
| ARPC5L | 1.12 | −0.48 | −0.78 | −0.26 | −0.45 | AC091132.4 | −0.59 | 0.27 | 1.08 | −0.13 | −0.02 | AC104850.1 | −1.08 | 1.54 | 2.54 | −0.04 | 0.45 |
| CDC123 | 0.72 | −0.30 | −0.57 | −0.11 | −0.37 | ME1 | 0.46 | −0.46 | −0.35 | −0.02 | 0.21 | AL592293.2 | −0.30 | 0.09 | 0.11 | −0.32 | −0.46 |
| PNCK | −2.11 | 0.92 | 0.20 | 0.45 | −0.07 | LINC01166 | −1.27 | −0.58 | −0.03 | 1.27 | 2.11 | HMGA1P1 | 0.49 | −1.16 | −1.03 | 0.57 | −0.09 |
| ATP6V1B2 | 0.70 | −0.26 | −0.66 | −0.05 | −0.56 | GTF3AP2 | 0.86 | 0.33 | −1.65 | −0.20 | −1.16 | LASP1 | 0.05 | −0.20 | −0.30 | −0.18 | −0.09 |
| SLC22A17 | −1.37 | 0.92 | 1.23 | 0.38 | 0.32 | AP003721.2 | −1.06 | 0.36 | 2.01 | −0.40 | 0.88 | AC092718.8 | 0.25 | −0.19 | −0.52 | 0.23 | −0.24 |
| HIST1H2AB | 1.94 | −1.74 | −1.85 | −0.47 | −0.83 | AL590235.1 | −0.97 | 0.53 | −1.00 | 0.96 | 0.18 | RASSF7 | −0.10 | 0.24 | 0.07 | 0.22 | 0.21 |
| LAD1 | 1.52 | −0.55 | −1.17 | −0.07 | −0.59 | AC068790.2 | 0.59 | −0.23 | 0.10 | −0.31 | 0.45 | HSPE1P22 | 1.08 | 1.23 | 1.03 | −0.03 | −1.10 |
| KRT15 | −1.74 | 1.24 | 1.64 | 0.70 | 0.22 | AC098829.1 | 0.42 | 0.06 | −0.51 | −0.54 | −0.42 | HSPE1P27 | 0.18 | −0.39 | −0.38 | 0.04 | 0.07 |
| FAM27E2 | −2.78 | 0.29 | 0.73 | 1.60 | 1.28 | AL162394.1 | −1.23 | 0.21 | 0.94 | −0.17 | 0.52 | DEFB118 | −0.75 | −0.45 | −0.92 | −0.62 | −0.36 |
| POU6F1 | −1.23 | 0.60 | 1.00 | 0.34 | 0.26 | RUNDC3A | 0.35 | −0.17 | −0.37 | 0.13 | −0.41 | SMYD5 | 0.07 | −0.19 | −0.28 | −0.02 | 0.08 |
| GPRASP2 | −0.81 | 0.40 | 0.93 | 0.05 | 0.26 | PA2G4P6 | 0.57 | −0.29 | −0.08 | 0.20 | −0.30 | LINC02226 | 0.58 | −1.61 | −1.01 | 0.90 | −0.42 |
| FOSL1 | 2.52 | −2.15 | −3.68 | −0.16 | −3.30 | LRRC3 | −0.31 | −0.40 | −0.13 | 0.04 | 0.39 | AC104009.1 | −1.21 | 1.02 | 2.10 | −0.25 | −0.57 |
| CAPZB | 0.56 | −0.28 | −0.52 | −0.14 | −0.32 | ARHGAP22-IT1 | 1.04 | −1.68 | −0.21 | −0.45 | 1.21 | AL133372.2 | −0.58 | 1.40 | −0.16 | 0.24 | −1.75 |
| MAGI1 | −0.60 | 0.59 | 0.60 | 0.27 | 0.13 | AC138207.2 | −0.91 | 1.10 | 0.80 | 0.19 | −0.10 | KRT8P43 | −0.37 | 0.15 | 1.74 | 0.08 | 0.42 |
| PYCARD | 1.54 | −0.27 | −0.99 | 0.12 | −0.88 | KLHDC2 | −0.18 | 0.27 | 0.21 | 0.10 | −0.08 | AC078922.1 | −0.62 | 0.52 | 2.15 | −0.78 | 0.44 |
| KRT14 | 2.39 | −1.38 | −2.69 | −0.10 | −1.44 | PYY2 | 1.22 | 0.21 | −0.01 | −0.29 | −0.11 | HOXB13 | −0.26 | −0.49 | −0.55 | −0.14 | 0.33 |
| PCNA | 1.28 | −0.77 | −0.92 | −0.26 | −0.48 | AC005514.1 | −0.81 | −0.13 | 0.01 | 1.05 | 1.39 | AL161725.1 | 0.11 | −0.23 | 0.06 | −0.07 | 0.16 |
| OVCH2 | −1.90 | 1.57 | 2.75 | 1.02 | 0.97 | AC021086.1 | −0.70 | 0.08 | 1.61 | 0.03 | 0.50 | SNORA2B | −0.19 | 0.40 | 0.68 | 0.16 | −0.07 |
| SNRPN | −1.07 | 0.51 | 1.13 | 0.19 | 0.26 | LHFPL4 | −0.46 | 0.31 | 0.33 | 0.19 | 0.34 | HAVCR1 | −0.23 | −0.46 | −1.23 | 0.08 | −1.29 |
| MYO5A | 0.76 | −0.28 | −0.87 | −0.06 | −0.56 | AL162615.1 | −0.38 | −0.08 | −0.05 | 0.36 | 0.25 | RN7SKP283 | −0.18 | −0.13 | −0.78 | −0.13 | −0.83 |
| ABCA10 | −1.48 | 1.19 | 1.48 | 1.06 | 0.49 | ROCK1 | 0.24 | −0.14 | −0.19 | −0.16 | −0.18 | BNIP3P29 | −0.39 | 0.14 | −1.15 | −0.10 | −0.90 |
| RDM1P3 | −1.63 | 1.20 | 1.86 | 0.26 | 0.71 | AC005077.2 | 0.91 | −0.34 | −1.62 | 0.26 | −1.07 | OR5D15P | 0.68 | −0.04 | −1.80 | 0.49 | −0.73 |
| EFCAB6 | −1.11 | 0.54 | 0.86 | 0.16 | 0.20 | AC103563.2 | −1.42 | −0.60 | 1.34 | −0.73 | 0.38 | MIR3129 | 0.34 | 0.51 | 0.38 | −0.08 | 0.48 |
| PPOX | −1.28 | 0.73 | 1.31 | 0.44 | 0.53 | AL157786.1 | −0.51 | −0.15 | 0.13 | 0.03 | 0.38 | AC023154.1 | 0.12 | 0.05 | −0.18 | 0.21 | 0.23 |
| KIFC2 | −1.59 | 0.83 | 0.80 | 0.93 | 0.46 | AL121935.2 | −0.83 | −1.06 | 0.97 | −0.60 | 1.60 | AC092944.2 | −0.56 | 0.45 | −0.01 | −0.16 | 0.25 |
| ABCG4 | 2.68 | −1.61 | −2.24 | −0.28 | −1.19 | AC093503.1 | −0.61 | −0.03 | 0.33 | 0.51 | 0.93 | OLIG3 | −0.68 | −1.06 | −0.03 | 0.78 | 2.51 |
| HSPA5 | 1.14 | −0.66 | −1.11 | −0.24 | −0.42 | AP000894.2 | 0.80 | 0.61 | −1.86 | 0.18 | −2.91 | SEPT7P1 | 0.15 | −0.17 | −0.31 | −0.21 | 0.14 |
| MRPL36 | 1.18 | −0.45 | −1.22 | −0.33 | −0.79 | SEZ6L2 | 0.44 | −0.40 | −0.94 | −0.19 | −0.65 | CLIC1P1 | −0.41 | −0.05 | 0.87 | −0.70 | −0.51 |
| AC006329.1 | 2.05 | −1.46 | −2.15 | −0.04 | −0.64 | SPRYD4 | −0.18 | −0.08 | −0.19 | 0.20 | 0.05 | NBPF8 | −0.20 | −0.37 | −0.24 | 0.00 | 0.42 |
| DMGDH | −1.32 | 0.71 | 1.02 | 0.18 | −0.01 | IL2RG | 0.73 | −1.22 | −0.25 | −0.32 | 0.79 | AC002075.2 | 0.38 | 1.15 | −0.64 | 0.67 | −1.19 |
| FAM234B | −0.85 | 0.53 | 0.95 | 0.23 | 0.28 | AL121748.1 | 1.17 | −0.71 | −0.56 | −1.00 | −0.39 | RAB11FIP1P1 | −0.11 | 0.12 | 0.13 | 0.06 | 0.12 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| DENND1B | 0.91 | −0.53 | −0.91 | −0.07 | −0.29 | AL449423.1 | 1.26 | −2.32 | −0.09 | −0.63 | 0.07 | MIR4307HG | −0.71 | 0.70 | −0.13 | 0.69 | −1.58 |
| IRAK1 | 0.72 | −0.38 | −0.82 | −0.08 | −0.39 | LINC02169 | −1.08 | 1.50 | 0.75 | 2.42 | −0.19 | ADGRA1-AS1 | 0.90 | −0.73 | −0.07 | 0.31 | 1.49 |
| RRP36 | 0.81 | −0.43 | −0.70 | −0.18 | −0.38 | IQCC | −0.25 | 0.28 | 0.30 | 0.11 | 0.17 | AC034111.1 | −0.21 | −1.14 | 0.67 | −0.09 | 1.14 |
| CDC6 | 1.40 | −1.31 | −1.37 | −0.37 | −0.22 | SPDYE22P | 0.66 | −1.16 | −0.94 | −0.48 | 0.73 | AC091906.1 | −0.26 | −0.29 | 0.33 | −0.32 | −0.14 |
| CGN | −1.41 | 1.06 | 1.23 | 0.61 | 0.16 | GCSH | −0.44 | 0.50 | 0.39 | 0.26 | −0.07 | KIAA0232 | 0.05 | 0.07 | 0.10 | −0.06 | −0.04 |
| ABCC1 | 0.63 | −0.40 | −0.76 | −0.07 | −0.22 | AC104986.1 | −0.52 | 0.32 | 1.07 | 0.11 | 0.56 | SSBP3-AS1 | 0.11 | 0.06 | 0.24 | −0.16 | 0.05 |
| GVQW3 | −1.09 | 0.42 | 0.72 | 0.07 | 0.26 | AGPAT4 | 0.20 | −0.07 | −0.40 | −0.12 | −0.42 | AC009800.1 | −0.78 | −0.43 | −0.04 | 0.25 | 0.40 |
| GFOD1 | 0.73 | −0.02 | −0.52 | 0.02 | −0.76 | GJA3 | 0.83 | −0.01 | −0.94 | 0.11 | −0.80 | EIF4A2P3 | −0.31 | 0.68 | 0.47 | −0.28 | 0.19 |
| BBS9 | −0.69 | 0.48 | 0.75 | 0.17 | 0.05 | GPRC5A | 0.59 | −0.21 | −1.13 | −0.73 | −1.01 | AC008391.1 | 0.26 | 0.77 | −0.98 | 0.69 | −1.08 |
| AP002884.1 | −0.83 | 0.59 | 0.67 | 0.24 | 0.31 | AP003119.1 | −1.00 | 0.42 | 1.03 | 0.40 | 1.03 | GAPDHP52 | 0.30 | −0.31 | −1.08 | 0.28 | 0.57 |
| CCSER1 | −1.08 | 0.40 | 0.54 | 0.21 | 0.39 | GAPDHP70 | 0.90 | −0.42 | −0.63 | −0.33 | −0.31 | NTF3 | 0.16 | 0.17 | −0.67 | 0.16 | −0.60 |
| NFKB1 | 0.78 | −0.45 | −0.69 | −0.14 | −0.31 | AC093607.1 | −1.21 | −0.32 | 0.90 | −0.50 | −0.08 | SNHG1 | −0.12 | 0.04 | −0.04 | 0.31 | −0.20 |
| ACTR2 | 0.96 | −0.48 | −0.62 | −0.24 | −0.42 | LINC01937 | 1.90 | −3.38 | −1.78 | −1.25 | 0.28 | AC096533.1 | −0.16 | −0.15 | 0.03 | 0.05 | 0.17 |
| PSMD2 | 0.77 | −0.37 | −0.77 | −0.06 | −0.44 | AC009955.2 | 1.58 | −0.11 | −1.51 | 0.18 | −0.44 | RN7SL514P | −0.60 | −0.78 | 0.84 | −0.13 | 1.32 |
| SNX21 | −1.11 | 0.72 | 0.73 | 0.50 | 0.09 | SFXN4 | 0.23 | −0.34 | −0.40 | −0.16 | 0.13 | RNU6-1002P | 0.27 | −0.26 | −0.10 | −0.23 | −1.12 |
| KPNA3 | 0.73 | −0.29 | −0.58 | −0.11 | −0.47 | AC145098.2 | −0.50 | 0.16 | 0.56 | −0.12 | 0.34 | AC026719.2 | 0.97 | −1.83 | 0.10 | −0.92 | 1.09 |
| CTSB | 1.09 | −0.64 | −0.82 | −0.26 | −0.47 | AC107464.2 | −0.46 | −0.41 | 0.20 | −0.22 | 0.68 | HIGD1AP18 | −0.55 | −0.83 | 1.99 | −1.21 | 3.51 |
| OLA1 | 0.84 | −0.40 | −0.67 | −0.10 | −0.34 | CENPB | 0.24 | −0.17 | −0.17 | 0.00 | 0.11 | AC110813.1 | −0.13 | 0.19 | 0.38 | 0.27 | 0.66 |
| PDIA4 | 0.90 | −0.63 | −0.58 | −0.42 | −0.15 | LRIT3 | −0.46 | 0.11 | 0.51 | 0.11 | −0.02 | RPS15AP11 | −0.19 | −0.08 | 0.59 | −0.33 | −0.04 |
| GLO1 | 1.19 | −0.49 | −0.85 | −0.14 | −0.63 | AC060234.3 | 1.07 | −1.02 | −1.10 | −1.09 | 0.55 | ILF2P2 | −0.78 | 0.14 | −0.23 | −0.25 | 0.75 |
| ACOT7 | 1.10 | −0.87 | −1.10 | −0.46 | −0.50 | MRPL37P1 | 0.39 | −0.54 | −0.87 | −0.18 | −0.50 | AC018512.1 | −0.72 | 0.85 | 0.26 | 0.27 | −1.58 |
| NPTX1 | 2.41 | −0.83 | −1.61 | −0.29 | −1.66 | OR7E100P | 0.80 | 0.21 | −0.22 | −0.07 | −0.14 | AP002383.1 | −0.62 | 0.28 | 2.39 | −0.84 | 1.23 |
| NAP1L2 | −1.41 | 0.72 | 1.31 | 0.25 | 0.34 | SEC23A | 0.27 | −0.07 | −0.06 | −0.28 | −0.26 | PRR22 | −0.18 | −0.30 | −0.67 | 0.45 | 0.62 |
| PDZD4 | −1.44 | 0.71 | 0.71 | 0.62 | 0.62 | AC027031.2 | 0.38 | −0.47 | 0.38 | −0.35 | 0.14 | AL133464.1 | 0.37 | −1.11 | −0.12 | 0.02 | −0.71 |
| PFKFB2 | 0.99 | −0.21 | −0.92 | 0.10 | −0.79 | RALGAPA1 | −0.13 | 0.27 | 0.23 | 0.11 | −0.04 | LINC01394 | 0.85 | −1.09 | −1.52 | −0.34 | 0.12 |
| LEMD1 | 2.79 | −0.95 | −1.12 | −0.55 | −0.30 | AC005481.1 | 0.69 | −0.76 | −0.92 | 0.60 | 0.74 | AC099518.3 | −0.80 | −0.19 | 0.69 | −0.12 | 1.03 |
| RPN2 | 0.88 | −0.42 | −0.63 | −0.16 | −0.35 | DGKB | −0.69 | 0.14 | 0.36 | 0.01 | −0.23 | CFAP65 | −0.32 | −0.38 | −1.56 | 0.27 | −0.78 |
| B3GNT5 | 1.35 | −0.54 | −1.26 | −0.35 | −1.25 | AL590428.1 | −0.50 | 0.41 | 0.85 | −0.01 | 0.10 | AL844170.1 | 0.36 | 0.32 | −0.26 | 0.75 | −0.90 |
| CAPRIN1 | 0.78 | −0.38 | −0.70 | −0.15 | −0.36 | AC068254.2 | −0.98 | 0.33 | 1.77 | 0.12 | 0.39 | RNU2-64P | 0.22 | −0.40 | −0.35 | −0.10 | −0.74 |
| SHISAL1 | 1.66 | −0.84 | −1.64 | −0.70 | −1.26 | IFITM10 | −0.46 | 1.12 | 0.57 | 0.68 | −0.18 | C17orf51 | −0.10 | −0.13 | 0.13 | −0.29 | 0.05 |
| ARHGEF19 | −1.01 | 0.62 | 0.79 | 0.45 | 0.23 | NR1H4 | 1.35 | 0.00 | −0.67 | 0.28 | −2.32 | EFCAB8 | −0.14 | −0.30 | 0.56 | −0.37 | 0.19 |
| AC068020.1 | −2.42 | 0.72 | 2.51 | 0.66 | 1.00 | IGFBP7-AS1 | −0.67 | −0.09 | 0.66 | −0.64 | 0.14 | AC020978.6 | −0.85 | −0.72 | 0.85 | 0.19 | 2.02 |
| PLK1 | 1.36 | −1.14 | −1.54 | −0.33 | −0.18 | HNRNPLP2 | −0.62 | 0.59 | −0.24 | 0.14 | −0.76 | AC243830.2 | −0.74 | 0.84 | 1.75 | −0.85 | −0.51 |
| MST1P2 | −1.64 | 1.43 | 1.31 | 1.09 | 0.47 | OR51E1 | 0.91 | −0.60 | −0.69 | 0.13 | −0.55 | NIN | 0.04 | −0.13 | 0.09 | −0.14 | 0.02 |
| PRPF40A | 0.74 | −0.41 | −0.69 | −0.15 | −0.38 | MAP3K6 | −0.29 | 0.09 | −0.16 | 0.25 | 0.03 | AC005291.2 | −0.55 | −0.21 | 0.92 | −1.34 | −0.96 |
| NDNF | −1.62 | 0.97 | 1.07 | 0.57 | 0.24 | EIF5AP2 | 1.19 | −0.98 | −0.26 | −1.42 | 0.03 | AL049840.5 | 0.14 | 0.39 | −0.15 | 0.31 | −0.37 |
| S100A12 | 4.38 | −2.49 | −4.09 | −0.26 | −3.46 | AC008406.1 | 2.16 | −0.21 | −1.98 | 0.59 | −1.21 | AL139316.1 | 0.93 | −1.44 | 0.52 | 0.19 | 1.73 |
| MUC20-OT1 | −0.72 | 0.41 | 0.68 | 0.32 | 0.26 | LINC01761 | −0.99 | 0.22 | −0.45 | 0.09 | −0.64 | PRELID3A | 0.10 | −0.22 | 0.20 | −0.08 | 0.09 |
| ANGPTL5 | −2.20 | 0.80 | 2.19 | 0.29 | 0.69 | LINC00032 | −0.47 | 0.23 | −0.39 | 0.05 | −0.80 | AC048380.1 | −0.15 | −0.37 | −0.27 | −0.44 | 0.29 |
| DHX32 | 0.85 | −0.23 | −0.65 | −0.13 | −0.46 | ECSIT | −0.19 | 0.15 | −0.11 | 0.27 | 0.02 | AC091564.5 | −0.40 | 1.19 | −0.08 | 0.30 | −1.26 |
| CAB39 | 0.83 | −0.37 | −0.87 | −0.16 | −0.54 | AP000350.6 | −0.36 | −0.30 | 0.56 | 0.09 | 0.44 | GPX3 | 0.17 | −0.39 | −0.56 | 0.31 | −0.55 |
| ASPM | 1.70 | −0.98 | −1.62 | −0.22 | −0.52 | PLEKHG2 | 0.41 | −0.60 | −0.96 | −0.27 | −0.32 | G17702 | 0.24 | −0.33 | −1.04 | 0.25 | −0.41 |
| GSE1 | −0.64 | 0.43 | 0.46 | 0.26 | 0.07 | FAM86HP | −0.36 | 0.19 | 0.05 | 0.17 | 0.42 | ABCG1 | 0.09 | 0.06 | 0.00 | 0.18 | −0.18 |
| PHKG1 | −1.27 | 0.50 | 1.30 | 0.33 | 0.55 | NAGA | 0.19 | −0.35 | −0.11 | −0.21 | 0.03 | EEF1AKMT1 | −0.09 | 0.01 | 0.50 | −0.30 | 0.25 |
| KTN1 | 1.07 | −0.62 | −1.28 | −0.07 | −0.53 | BTNL2 | −0.80 | 0.74 | 0.54 | −0.42 | −0.69 | AL731547.1 | −0.94 | 0.92 | 1.39 | 0.25 | 1.42 |
| PBK | 1.77 | −1.38 | −1.58 | −0.37 | −0.58 | PTP4A2 | 0.28 | −0.37 | −0.31 | −0.24 | −0.05 | AC099511.1 | −0.56 | −0.19 | −0.32 | −0.18 | −1.03 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC068587.1 | −2.93 | 1.44 | 3.34 | 0.18 | 1.29 | G16363 | 1.15 | −1.79 | −0.47 | −0.30 | 0.89 | ADAM3B | −0.29 | −0.59 | 1.53 | −0.20 | 0.75 |
| SREK1IP1 | 0.82 | −0.36 | −0.60 | −0.20 | −0.50 | AC063952.1 | −0.53 | 0.17 | 1.13 | −0.17 | 0.66 | SOD1 | 0.06 | 0.13 | 0.04 | 0.05 | −0.31 |
| AC090625.2 | −4.00 | 0.39 | 0.91 | −0.28 | −0.76 | AF228730.4 | −1.30 | 1.26 | 0.42 | 1.63 | 0.28 | AC099786.2 | 0.73 | −0.16 | −0.74 | −1.86 | −1.29 |
| NEIL1 | −1.12 | 0.54 | 0.70 | 0.52 | 0.45 | AC020571.1 | 0.68 | −0.39 | −0.43 | −0.37 | −0.01 | AL121906.1 | 0.35 | −0.21 | −0.73 | −0.07 | −0.09 |
| AC127526.2 | −2.34 | 1.24 | 1.86 | −0.08 | 0.19 | AC091153.2 | 0.76 | −1.44 | −0.65 | −0.23 | 0.67 | AC084026.3 | −0.69 | 0.16 | 0.30 | 0.48 | 0.70 |
| FAM69C | −2.06 | 0.58 | 1.33 | 0.07 | 0.15 | DNAJB4 | −0.25 | 0.10 | 0.51 | −0.24 | −0.14 | ANGPTL8 | −0.17 | −0.21 | 0.54 | −0.23 | −0.13 |
| IPO13 | 0.59 | −0.48 | −0.34 | −0.27 | 0.08 | OPCML | −0.78 | −0.34 | −0.17 | 0.57 | 0.15 | IL23R | 0.27 | −0.16 | −0.46 | −0.06 | 0.00 |
| EIF3I | 0.94 | −0.45 | −0.66 | −0.15 | −0.41 | FAM91A3P | −0.67 | 0.38 | 0.43 | 0.76 | 0.22 | AC018638.5 | −0.13 | 0.16 | −0.05 | 0.22 | 0.02 |
| LYPLA1 | 1.19 | −0.44 | −0.63 | −0.16 | −0.56 | NELL1 | −0.66 | 0.87 | 0.79 | 0.55 | 0.66 | NMRK1 | −0.06 | 0.06 | 0.23 | 0.16 | 0.23 |
| SLC52A2 | 1.17 | −0.42 | −1.13 | 0.02 | −0.45 | CSRP3 | 0.73 | −0.98 | −0.29 | −0.16 | 0.07 | AC078817.1 | 0.24 | −1.04 | 0.04 | −0.54 | 0.33 |
| AC107884.1 | −1.20 | 0.58 | 1.01 | 0.24 | 0.43 | AC073551.1 | −0.84 | 0.47 | 0.30 | 1.11 | 0.64 | AL161420.1 | 0.21 | 0.57 | 0.02 | −0.03 | −0.42 |
| LPCAT1 | 0.99 | −0.70 | −1.12 | −0.04 | −0.29 | LRTOMT | −0.29 | 0.12 | 0.20 | 0.34 | 0.32 | AL450326.1 | 0.23 | −0.66 | 0.33 | 0.00 | 0.79 |
| ARHGEF9 | −0.43 | 0.36 | 0.33 | 0.14 | −0.03 | AC079793.1 | −0.73 | 0.20 | 2.20 | −0.59 | 1.07 | AC005832.3 | 0.54 | −1.68 | −1.81 | −0.82 | −1.03 |
| PLSCR1 | 0.90 | −0.85 | −0.84 | −0.43 | −0.35 | AC026124.1 | −0.46 | 0.33 | 1.07 | −0.08 | −0.16 | AC102797.2 | 0.66 | −0.47 | −2.20 | 1.04 | −0.50 |
| ANKRD36C | −0.74 | 0.42 | 0.58 | 0.07 | 0.10 | EMC6 | 1.10 | 0.18 | −1.59 | 0.76 | −1.93 | PPP2R2D | −0.04 | 0.04 | −0.05 | −0.03 | −0.03 |
| EEF1B2 | 1.18 | −0.43 | −0.64 | −0.26 | −0.60 | NPIPB11 | −0.34 | −0.05 | 0.22 | −0.22 | −0.19 | AC020915.1 | 0.16 | −0.14 | 0.71 | −0.17 | 0.15 |
| LINC00707 | 2.69 | −1.61 | −3.36 | −0.67 | −2.16 | AC004922.1 | 0.46 | −1.09 | −0.81 | −0.33 | −0.14 | AC087516.1 | −0.44 | −0.62 | −1.25 | 0.77 | 0.78 |
| G26897 | −1.70 | 0.70 | 0.86 | 0.56 | 0.39 | OR51H2P | 1.19 | −2.01 | −1.53 | 1.08 | 0.68 | INHBC | 0.37 | 0.34 | −2.12 | 0.43 | −0.59 |
| ANKRD33B | −1.63 | 1.20 | 1.21 | 0.10 | 0.01 | AC020891.3 | 0.87 | −0.69 | −0.71 | 0.24 | 0.89 | RN7SKP100 | −0.62 | −0.22 | −0.09 | 1.67 | 1.95 |
| CCNB2 | 1.60 | −0.80 | −1.34 | −0.35 | −0.58 | AC104809.1 | −1.20 | −0.45 | 1.56 | 0.19 | 1.28 | AC013643.2 | −0.21 | 0.15 | 0.14 | 0.11 | −0.04 |
| CLTC | 0.89 | −0.35 | −0.65 | −0.19 | −0.55 | DCHS1 | −0.39 | 0.23 | 0.64 | −0.21 | −0.11 | MTND3P25 | 0.21 | −0.11 | −1.42 | 0.39 | 0.12 |
| C14orf132 | −1.31 | 1.07 | 1.68 | 0.35 | 0.01 | CCL20 | 1.25 | −0.92 | −2.87 | −0.55 | −3.30 | RNU6ATAC34P | 0.39 | 0.85 | −0.33 | 0.11 | −0.50 |
| OSMR | 0.92 | −0.76 | −0.90 | −0.25 | −0.37 | AC127540.1 | −0.74 | 0.24 | 1.33 | −0.34 | −0.18 | OR6M2P | −0.37 | 0.11 | −1.27 | 0.78 | −0.67 |
| CHPF | 0.89 | −0.31 | −0.59 | −0.31 | −0.44 | RPL17P51 | −1.50 | 0.78 | 0.54 | 0.51 | −1.42 | OR9K2 | 0.55 | −1.15 | −2.36 | 0.17 | −1.98 |
| LPAR3 | 1.38 | −0.65 | −0.94 | 0.00 | −0.09 | SORD2P | 0.72 | −0.17 | −1.00 | 0.41 | −0.62 | DEFA4 | 0.84 | −1.38 | −1.90 | 0.35 | −0.52 |
| ITGB6 | 1.69 | −1.17 | −2.14 | −0.11 | −0.86 | RP11-391M20.1 | −0.34 | 0.05 | 0.82 | 0.03 | 0.67 | RNF175 | −0.19 | −0.06 | −0.37 | 0.24 | −0.10 |
| SPTLC2 | 0.86 | −0.37 | −0.50 | −0.11 | −0.32 | AP001007.2 | 1.51 | −0.70 | −2.27 | 0.26 | −1.29 | DLL1 | −0.11 | 0.10 | −0.60 | 0.16 | −0.04 |
| KIF20B | 1.00 | −0.70 | −0.91 | −0.12 | −0.15 | CEACAMP11 | −1.41 | 1.03 | 0.86 | 0.35 | −0.70 | MIR4322 | −0.80 | −0.08 | 0.94 | −0.57 | 1.76 |
| KLC4 | −0.74 | 0.49 | 0.61 | 0.27 | 0.13 | AL441992.1 | 0.55 | 0.01 | −0.30 | −0.06 | −0.59 | G2580 | 0.88 | 0.30 | 0.06 | −1.74 | −2.14 |
| CYP7B1 | 0.98 | −0.42 | −0.54 | −0.23 | −0.54 | ITPR3 | −0.26 | 0.11 | −0.17 | 0.05 | 0.02 | AC025175.1 | −0.24 | 0.67 | −0.04 | 0.89 | 0.23 |
| GALNT10 | 0.49 | −0.34 | −0.32 | −0.21 | 0.08 | ALKBH8 | 0.18 | 0.02 | −0.22 | 0.03 | −0.12 | AC019205.2 | −0.48 | 1.67 | −1.45 | 1.18 | 0.01 |
| SPATA6 | −0.97 | 0.72 | 1.05 | 0.22 | 0.16 | BX293535.1 | −0.84 | 0.54 | 0.52 | 0.46 | 0.54 | AC109309.1 | −0.90 | 0.10 | 0.61 | −0.06 | −0.83 |
| PPP1CA | 0.81 | −0.24 | −0.72 | 0.01 | −0.57 | RNU6-1215P | 1.22 | −0.98 | −0.49 | −0.33 | −0.42 | AC091564.1 | 0.27 | −0.46 | 0.32 | −0.85 | −0.07 |
| ELFN2 | −2.19 | 0.39 | 0.94 | 0.40 | 0.78 | AC092038.2 | 0.83 | −0.52 | 0.76 | −0.36 | 0.43 | MGAT4A | −0.09 | 0.03 | 0.58 | −0.25 | 0.07 |
| IMPDH1 | 0.81 | −0.52 | −0.83 | 0.05 | −0.14 | DHRS4L2 | 0.27 | 0.08 | 0.00 | 0.20 | −0.14 | AP006248.3 | −0.28 | −1.00 | 0.09 | −0.31 | 0.67 |
| DDIAS | 1.46 | −1.42 | −1.54 | −0.31 | −0.34 | MAP3K2 | 0.21 | 0.03 | −0.09 | 0.02 | −0.30 | AC060766.6 | −0.20 | −0.06 | 0.89 | 0.06 | 0.01 |
| EAF1 | 0.80 | −0.23 | −0.52 | −0.09 | −0.61 | AC023301.1 | −1.40 | −0.64 | 1.39 | −0.86 | 1.64 | AC137932.2 | 0.14 | −0.14 | −0.15 | −0.14 | −0.07 |
| PARP9 | 1.21 | −0.94 | −1.16 | −0.42 | −0.48 | SNORA11B | −0.50 | −0.12 | −0.33 | 0.08 | 0.15 | GUCY2GP | 0.49 | −1.81 | −0.55 | −0.32 | 1.69 |
| SOX9-AS1 | −1.61 | 0.80 | 1.49 | 0.32 | 0.52 | CHD8 | 0.10 | 0.05 | −0.04 | −0.02 | −0.14 | EGFL7 | −0.14 | −0.03 | 0.42 | 0.03 | 0.06 |
| CKAP5 | 0.67 | −0.40 | −0.64 | −0.17 | −0.26 | AC010776.3 | −1.60 | −0.51 | 1.78 | −0.69 | 1.43 | PTGES3P2 | 0.17 | −0.16 | 0.91 | −0.27 | 0.82 |
| LRFN5 | −1.86 | 0.79 | 1.79 | 0.13 | 0.22 | ELFN1 | 0.49 | −0.33 | −0.87 | −0.44 | −1.15 | MTND5P26 | −0.15 | 0.48 | 0.10 | −0.22 | −0.37 |
| PSMB2 | 0.81 | −0.44 | −0.72 | −0.19 | −0.40 | AC093304.1 | 2.09 | −1.07 | −3.21 | −0.16 | −2.86 | SLITRK1 | −0.43 | −1.00 | −0.97 | 0.03 | −1.29 |
| SQOR | 1.25 | −0.79 | −1.28 | −0.24 | −1.00 | SCG5 | 0.53 | −0.55 | −0.45 | −0.60 | −0.15 | NAPSB | 0.16 | −0.69 | 0.27 | −0.49 | 0.36 |
| IL16 | −1.20 | 0.58 | 0.84 | 0.27 | 0.26 | AC137932.3 | −0.34 | −0.07 | 0.27 | −0.09 | 0.26 | AL031727.1 | 0.10 | −0.24 | −0.20 | −0.04 | 0.27 |
| RCC1 | 1.06 | −0.67 | −0.98 | −0.19 | −0.23 | MT-TV | −0.68 | 0.37 | 0.28 | 0.66 | −0.55 | DYNLT3P2 | 0.66 | −0.90 | −1.57 | −0.42 | −1.99 |
| RNF165 | −1.41 | 0.76 | 0.55 | 0.70 | 0.49 | AC140061.7 | −1.07 | −0.73 | 0.54 | −0.17 | −0.18 | AC123767.1 | −0.58 | 0.64 | −1.12 | 0.06 | −1.72 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| HIF1A | 1.34 | −0.78 | −1.16 | −0.49 | −0.53 | AC008897.3 | 0.82 | 0.45 | −0.37 | 0.32 | −0.52 | GJA4 | 0.16 | −0.65 | 0.21 | −0.07 | 0.26 |
| SRPK1 | 0.83 | −0.13 | −0.51 | 0.00 | −0.50 | RHEX | −0.55 | 0.70 | 2.04 | 0.01 | 0.65 | AC131392.2 | 0.40 | −0.59 | −0.23 | 0.55 | −0.09 |
| LCLAT1 | 0.71 | −0.24 | −0.53 | −0.12 | −0.31 | OXTR | 0.67 | −0.29 | −1.43 | −0.02 | −0.64 | SPIRE1 | 0.07 | 0.25 | −0.07 | −0.04 | −0.35 |
| PDIA3 | 1.05 | −0.64 | −0.82 | −0.24 | −0.35 | CPZ | −0.90 | 0.37 | 2.12 | −1.09 | 0.49 | RN7SKP139 | −0.52 | 0.01 | −1.25 | 0.61 | −0.85 |
| CENPW | 1.56 | −1.14 | −1.12 | −0.62 | −0.55 | AC022080.1 | −0.86 | −0.58 | 1.02 | −0.11 | 1.26 | AL157688.1 | 0.70 | −0.93 | −2.81 | 1.59 | −1.88 |
| HNRNPC | 0.70 | −0.49 | −0.72 | −0.09 | −0.24 | MFAP3L | −0.37 | 0.62 | 0.92 | 0.66 | 0.11 | RNU6-1046P | −0.50 | 0.20 | 2.60 | 0.12 | 2.21 |
| PRNP | 1.07 | −0.60 | −0.87 | −0.28 | −0.45 | AC004656.1 | −0.46 | 0.76 | 1.25 | 0.33 | 0.67 | SNURF | −0.24 | 0.44 | 0.44 | 0.63 | 0.21 |
| GART | 0.83 | −0.60 | −0.91 | −0.21 | −0.31 | HSD17B7P2 | −0.36 | −0.06 | 0.49 | 0.31 | 0.55 | AL139354.1 | −0.32 | −0.81 | 0.55 | 0.08 | 1.72 |
| MTERF2 | −0.76 | 0.30 | 0.53 | 0.29 | 0.29 | DIO1 | −0.42 | −0.56 | −0.02 | −0.42 | −0.17 | IL7 | 0.11 | −0.03 | 0.28 | −0.02 | 0.19 |
| RPH3AL | −1.27 | 0.40 | 0.26 | 0.28 | 0.38 | AC004453.2 | −0.94 | −0.13 | 0.66 | 0.35 | 0.79 | AL445218.1 | −0.53 | −0.97 | −2.20 | 0.92 | 0.02 |
| GLCCI1 | −0.81 | 0.85 | 1.06 | 0.24 | 0.13 | G32346 | −1.04 | −0.30 | −0.06 | 0.36 | 0.68 | MTCO3P22 | 0.58 | −1.63 | −1.18 | 0.34 | 0.09 |
| SLC7A1 | 1.54 | −0.58 | −1.28 | 0.06 | −0.60 | MIR103A2 | 0.54 | −0.02 | −0.04 | 0.10 | −0.13 | FAM84B | −0.08 | 0.47 | 0.30 | 0.18 | 0.11 |
| CAMK2B | −2.16 | 0.73 | 0.47 | 1.70 | −0.23 | 11-Mar | −1.19 | −0.32 | 0.72 | 0.40 | 0.78 | AC008871.1 | 0.15 | −0.20 | −0.72 | 0.10 | −0.11 |
| PSMC1P10 | 3.51 | −1.31 | −2.61 | 0.47 | −0.81 | AC018766.1 | 0.70 | 0.32 | −0.75 | 0.04 | −0.54 | MEIS3P1 | −0.13 | 0.14 | 0.63 | 0.02 | 0.37 |
| PSMD14 | 0.96 | −0.53 | −0.72 | −0.17 | −0.50 | AC091053.2 | 0.53 | −0.23 | −0.25 | −0.06 | −0.45 | MED26 | 0.06 | 0.01 | −0.29 | 0.17 | −0.22 |
| ARF6 | 0.83 | −0.25 | −0.52 | −0.13 | −0.41 | AC009065.3 | −0.93 | 0.45 | −0.42 | 0.19 | 0.84 | LINC02243 | 0.23 | 0.13 | 0.54 | 0.02 | 0.36 |
| SLC38A5 | 1.14 | −0.58 | −1.13 | −0.20 | −0.51 | MVB12A | 0.21 | −0.02 | −0.28 | 0.13 | −0.10 | AC018867.2 | 0.97 | 0.92 | −0.37 | −0.15 | −2.92 |
| GADD45GIP1 | 1.05 | −0.65 | −0.89 | −0.32 | −0.43 | AP000870.1 | 1.19 | −0.02 | −1.75 | 0.24 | −1.93 | GDF3 | −0.48 | 0.14 | −1.87 | 2.00 | −0.76 |
| AC092111.1 | −1.77 | 0.78 | 1.24 | 0.47 | 0.34 | AC017028.1 | −0.57 | −0.12 | 0.41 | 0.15 | 0.68 | AL080285.2 | 0.70 | −1.06 | −0.39 | −1.00 | −0.64 |
| GABBR1 | −0.95 | 0.31 | 0.61 | 0.16 | 0.23 | DNM3OS | −0.37 | 0.10 | 1.23 | −0.45 | 0.25 | DPCD | 0.06 | 0.16 | −0.25 | 0.15 | −0.39 |
| ADCY6 | −1.05 | 0.49 | 0.89 | 0.38 | 0.21 | KIAA1211 | −0.43 | 0.13 | 0.33 | −0.06 | 0.20 | RARRES2P10 | −1.25 | 0.49 | −0.12 | 0.07 | −0.72 |
| AR | −1.49 | 1.10 | 1.19 | 0.72 | 0.32 | AC007382.1 | 0.40 | 0.21 | −0.15 | −0.04 | −0.41 | AC009054.2 | 0.19 | −0.09 | 0.19 | −0.42 | 0.10 |
| BTBD10 | 0.65 | −0.34 | −0.51 | −0.23 | −0.30 | ATP8B4 | −0.40 | −0.09 | 0.29 | −0.21 | −0.10 | FARP2 | −0.06 | 0.14 | 0.14 | 0.04 | 0.01 |
| PTPRQ | −2.53 | 0.99 | 1.25 | 0.94 | 1.05 | AC132186.1 | −0.88 | 0.65 | 0.46 | −0.50 | −0.89 | RPS23P2 | −0.51 | 1.57 | −0.65 | 2.36 | −0.40 |
| RGS6 | −2.04 | 1.15 | 1.09 | 0.99 | 0.03 | AP3D1 | 0.22 | −0.20 | −0.55 | −0.07 | −0.11 | SLC25A11 | −0.06 | 0.09 | 0.04 | 0.17 | 0.02 |
| PRDM1 | 1.36 | −0.54 | −0.86 | −0.48 | −0.90 | AP000776.1 | −1.22 | 0.19 | 0.79 | 0.54 | 0.20 | AC008073.1 | 0.17 | −0.29 | −1.08 | −0.30 | −0.69 |
| PIGW | 1.29 | −0.81 | −1.04 | −0.20 | −0.52 | AC004233.3 | −1.29 | −0.92 | −1.10 | 0.68 | −0.64 | ABHD4 | 0.07 | 0.01 | −0.10 | 0.18 | −0.06 |
| GIGYF1 | −0.98 | 0.35 | 0.38 | 0.44 | 0.28 | GCSAM | −0.48 | 0.59 | 1.28 | −0.03 | 0.26 | AC010325.3 | 0.46 | −0.14 | 1.18 | −0.07 | 0.84 |
| ABCA3 | −1.27 | 0.88 | 1.28 | 0.30 | 0.32 | ELOVL5 | −0.53 | 0.04 | 0.41 | 0.22 | 0.72 | DRG2 | 0.05 | −0.14 | −0.26 | −0.02 | 0.04 |
| ACBD4 | −1.24 | 0.46 | 1.02 | 0.36 | 0.36 | AICDA | −0.84 | 0.22 | −0.98 | 0.76 | −0.74 | AC078962.1 | −0.18 | −0.92 | 0.42 | −0.43 | 1.12 |
| RAB7A | 0.79 | −0.32 | −0.75 | −0.12 | −0.49 | PHGDH | 0.36 | 0.25 | −0.29 | 0.47 | −0.20 | SNRPGP14 | 0.27 | 0.00 | 0.17 | 0.57 | 1.00 |
| IL13RA1 | 1.19 | −0.87 | −1.00 | −0.36 | −0.33 | SART1 | −0.23 | 0.00 | −0.19 | 0.09 | 0.05 | AL356515.1 | 0.33 | −0.81 | −1.98 | 0.14 | −0.01 |
| LYPD5 | 1.51 | −0.63 | −1.05 | 0.07 | −0.70 | AL596094.1 | 1.03 | 0.93 | −0.79 | 0.49 | −1.05 | MTCP1 | 0.16 | −0.04 | 0.24 | −0.01 | 0.16 |
| AC011473.4 | 4.14 | −1.59 | −1.70 | −0.20 | −1.12 | GJA9-MYCBP | 1.43 | −0.35 | 0.40 | 0.11 | 0.57 | AP001469.2 | −0.16 | −0.10 | −0.17 | −0.21 | 0.17 |
| STIP1 | 0.84 | −0.45 | −0.72 | −0.30 | −0.36 | AC093821.1 | −1.50 | 1.08 | 1.96 | 0.77 | −0.70 | E2F5 | −0.07 | −0.07 | 0.27 | −0.05 | 0.00 |
| NLGN1 | −1.44 | 0.46 | 0.66 | 0.46 | 0.44 | KEL | −0.67 | 0.30 | 0.66 | 0.35 | −0.54 | AC012047.1 | 0.72 | −1.14 | −1.28 | 0.50 | −0.87 |
| G33207 | −2.18 | 1.17 | 1.65 | 0.63 | −0.34 | AC068987.5 | −1.13 | 0.58 | 0.05 | −0.27 | −1.36 | OR13C6P | −0.96 | 0.34 | 1.17 | −0.17 | −0.16 |
| AFMID | −0.82 | 0.21 | 0.54 | 0.27 | 0.34 | PHTF1 | 0.27 | −0.18 | −0.12 | −0.19 | −0.08 | AP000708.1 | −0.45 | 0.07 | −0.73 | 0.37 | −0.96 |
| DET1 | −1.07 | 0.46 | 0.95 | 0.27 | 0.45 | LINC02225 | −0.78 | −0.03 | 0.28 | −0.40 | −0.11 | RPL12P20 | −0.12 | −0.28 | 0.07 | −0.12 | 0.02 |
| CLOCK | 0.85 | −0.38 | −0.61 | −0.10 | −0.22 | RNA5SP113 | −1.39 | 0.10 | −0.07 | 0.60 | 0.14 | MIR4799 | 0.22 | −0.73 | −0.54 | 0.26 | 0.48 |
| AMZ2P1 | −0.99 | 0.59 | 0.95 | 0.13 | 0.05 | BRINP1 | 0.74 | −0.53 | −1.96 | −0.32 | −1.11 | HSPD1P10 | −0.35 | −0.19 | −1.81 | 0.68 | 0.27 |
| CCM2 | 0.55 | −0.48 | −0.69 | −0.06 | −0.09 | CLEC4D | 1.21 | −1.25 | 0.04 | −0.94 | −0.55 | MTND4P31 | 0.57 | 0.70 | 1.11 | 0.38 | 0.05 |
| SGO2 | 1.22 | −0.99 | −1.15 | −0.45 | −0.33 | ALS2 | −0.10 | 0.05 | 0.16 | −0.05 | 0.06 | CDC42P3 | 0.53 | −0.45 | −0.84 | 0.48 | −1.33 |
| HIST1H1A | 2.09 | −1.38 | −1.06 | −0.72 | −0.41 | PASK | −0.29 | −0.12 | −0.19 | 0.15 | 0.27 | KDM5C | −0.06 | 0.07 | −0.21 | 0.17 | 0.01 |
| SERINC2 | 1.14 | −0.47 | −1.00 | −0.06 | −0.39 | AL691432.2 | 0.36 | −0.15 | 0.11 | 0.13 | −0.09 | LINC00484 | −0.16 | 0.33 | 0.83 | −0.19 | 0.40 |
| SEC61A1 | 0.68 | −0.36 | −0.43 | −0.23 | −0.21 | RER1 | 0.17 | −0.11 | −0.13 | −0.04 | 0.03 | G36957 | −0.30 | 0.10 | −0.10 | −0.64 | −0.07 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| ALG3 | 0.86 | −0.48 | −0.51 | −0.22 | −0.11 | NEPNP | −0.78 | −0.14 | 0.62 | −0.46 | −0.49 | AL390728.1 | −0.25 | 0.75 | −1.29 | 0.21 | −1.36 |
| IGSF3 | 1.28 | −0.27 | −1.00 | 0.13 | −0.54 | PLCL1 | −0.42 | 0.43 | 0.39 | 0.16 | −0.09 | ACSM2B | −0.28 | 0.26 | −0.17 | 0.41 | −0.61 |
| PPP1R32 | −1.45 | 0.80 | 1.50 | 0.49 | 0.47 | AC087683.2 | 0.71 | −0.29 | 0.55 | −0.15 | 0.20 | RPL17P25 | 0.25 | 1.02 | 0.46 | 0.60 | 0.07 |
| MAL2 | 1.67 | −0.28 | −0.74 | −0.06 | −1.01 | AC104162.2 | −0.20 | −0.04 | 0.24 | −0.11 | 0.19 | MRPL35P2 | −0.34 | −0.93 | −0.97 | 0.03 | −0.81 |
| PTPRS | −0.89 | 0.46 | 0.61 | 0.25 | 0.07 | AL591479.1 | −0.49 | 0.31 | 0.75 | 0.25 | 0.24 | LINC02003 | −0.18 | 0.39 | −0.24 | 0.43 | 0.05 |
| AL109809.1 | −1.55 | 0.78 | 1.47 | 0.22 | 0.72 | AC114489.1 | 1.42 | −0.26 | −1.62 | 0.82 | 0.00 | RN7SL635P | −0.51 | −2.20 | 1.87 | −1.13 | 2.54 |
| HIST1H2BB | 1.76 | −1.18 | −1.59 | −0.24 | −1.08 | S100A3 | 0.37 | −0.40 | −0.98 | −0.14 | 0.04 | LINC01972 | −0.62 | −1.01 | 0.27 | 0.20 | 1.42 |
| AC087473.1 | −2.29 | 0.93 | 1.05 | 1.05 | 0.90 | ELP1 | −0.15 | −0.01 | 0.09 | −0.13 | 0.00 | LINC01450 | 0.31 | −0.22 | 0.07 | 0.14 | −0.01 |
| MINDY1 | −0.77 | 0.60 | 0.81 | 0.23 | 0.03 | AC105339.1 | −1.40 | 1.47 | 0.45 | 0.56 | −0.71 | RN7SKP239 | −0.19 | −0.17 | 0.15 | 0.12 | 0.79 |
| RNF145 | 0.87 | −0.51 | −0.65 | −0.18 | −0.24 | AC091133.5 | −0.82 | −0.04 | 0.37 | 0.66 | 1.52 | DHX37 | −0.08 | −0.21 | −0.37 | 0.05 | 0.14 |
| AP2S1 | 0.86 | −0.38 | −0.47 | −0.05 | −0.35 | AC007570.1 | 1.36 | 0.47 | 0.73 | −0.09 | 0.37 | ARL16 | −0.06 | 0.17 | −0.29 | 0.27 | −0.10 |
| HBEGF | 1.91 | −1.43 | −1.94 | −0.80 | −1.78 | AC113146.1 | 0.85 | −0.47 | −1.47 | 0.08 | −0.77 | AC136759.1 | −0.68 | 0.88 | −0.82 | 0.01 | −0.56 |
| CFAP300 | −1.18 | 0.51 | 1.01 | 0.12 | 0.62 | AC064799.1 | 0.51 | −0.40 | −0.28 | −0.38 | −0.07 | MRPL30P1 | 0.43 | −0.33 | −0.48 | −0.42 | −1.26 |
| CCDC88C | 0.85 | −0.42 | −0.72 | 0.01 | 0.11 | AC016722.1 | −1.41 | −0.33 | 1.51 | 0.35 | 0.53 | FAM174A | 0.07 | 0.02 | 0.32 | 0.02 | 0.18 |
| SNRPF | 1.19 | −0.66 | −0.73 | −0.39 | −0.42 | AC034245.1 | 1.03 | −0.25 | −0.10 | −0.18 | −1.05 | LMNB1-DT | 0.71 | −0.71 | −0.73 | −0.28 | −1.67 |
| HSBP1 | 0.80 | −0.35 | −0.51 | −0.27 | −0.42 | RRP7A | 0.23 | −0.34 | −0.45 | 0.09 | 0.05 | RPL29P33 | 0.21 | −0.20 | −0.19 | −0.26 | −0.62 |
| L3MBTL1 | −0.91 | 0.32 | 0.22 | 0.45 | 0.34 | RNU6-487P | −0.75 | 0.24 | −0.44 | 0.93 | −0.72 | EEF1A1P31 | −0.35 | −0.58 | −0.49 | 0.25 | 0.79 |
| AJAP1 | 1.74 | −1.50 | −2.26 | −0.45 | −2.47 | KRTAP12-1 | −1.44 | −0.22 | 1.11 | 0.62 | 0.15 | OR1D2 | −0.41 | −0.08 | −0.72 | 0.65 | −0.40 |
| NKAPP1 | −0.97 | 0.65 | 1.01 | 0.19 | 0.22 | G17366 | 0.48 | −0.15 | −0.32 | −0.26 | −0.04 | SIGLEC17P | −0.24 | 0.55 | 1.30 | 0.24 | −0.12 |
| KARS | 0.85 | −0.42 | −0.64 | −0.28 | −0.50 | FBN2 | 0.55 | −0.86 | −0.23 | −0.75 | −0.36 | CHRNB4 | −0.22 | −0.38 | −0.36 | −0.05 | 0.12 |
| MIR3936HG | −1.23 | 0.46 | 1.21 | 0.02 | 0.43 | RP11-31207.2 | −0.48 | 0.53 | 0.56 | 0.07 | −0.03 | AC010200.1 | 0.15 | −0.32 | −0.16 | 0.02 | 0.30 |
| MAST4-IT1 | 2.22 | −1.37 | −2.50 | −0.27 | −1.25 | MIPEPP3 | −0.38 | 0.33 | 0.87 | 0.20 | 0.34 | AL356289.1 | −0.31 | −0.14 | 0.61 | −0.05 | 0.97 |
| GDNF | 2.02 | −1.17 | −2.46 | 0.10 | −0.88 | SLAMF6 | 0.59 | −0.83 | 0.43 | −0.20 | 1.63 | AC091965.1 | −0.76 | 1.42 | −0.19 | 0.03 | −0.06 |
| NLGN4X | 1.46 | −0.52 | −1.27 | 0.15 | −0.47 | MYL6P4 | −0.89 | 0.03 | 0.77 | −0.20 | 0.86 | CICP11 | −0.72 | 0.20 | 0.44 | 0.06 | −1.67 |
| LSP1 | −1.39 | 0.51 | 0.61 | 0.44 | 0.17 | CORT | 0.78 | −0.56 | 0.38 | −0.18 | 0.35 | AL008729.1 | −0.09 | 0.18 | −0.08 | 0.19 | 0.04 |
| IL1A | 2.24 | −2.37 | −2.74 | −1.22 | −1.40 | RP5-886K2.1 | −0.50 | 0.21 | 0.56 | 0.21 | 0.18 | LINC01205 | −0.48 | −0.73 | 0.01 | 0.48 | 1.32 |
| PCCA | −0.52 | 0.30 | 0.47 | 0.12 | 0.05 | AL022238.3 | −0.44 | −0.02 | 0.12 | −0.46 | 0.14 | NAGPA-AS1 | −0.31 | 0.17 | 0.32 | 0.27 | 0.22 |
| EIF6 | 1.05 | −0.32 | −1.05 | 0.08 | −0.79 | OVOL1 | 0.44 | 0.31 | −0.79 | 0.18 | −1.02 | AC073332.1 | 0.13 | −0.48 | 0.08 | 0.08 | 0.61 |
| AC244033.2 | −1.28 | 0.48 | 1.27 | 0.10 | 0.52 | AP003086.1 | −0.28 | −0.29 | 0.02 | 0.08 | 0.61 | AL049833.3 | −0.24 | −1.19 | −1.66 | −0.05 | 0.04 |
| NCAPH | 1.47 | −1.30 | −1.72 | −0.41 | −0.62 | G35821 | 0.68 | −0.09 | −0.50 | 0.10 | −0.31 | HBBP1 | −0.70 | 1.96 | −1.59 | 2.84 | −0.76 |
| CDH20 | −1.60 | 0.73 | 1.42 | 0.36 | 0.90 | LYL1 | −0.35 | −0.23 | 0.36 | 0.03 | 0.16 | LINC01427 | −0.33 | −1.43 | 0.73 | −0.23 | 0.31 |
| PSPH | 0.94 | −0.45 | −0.57 | −0.11 | −0.23 | AL109840.2 | −0.71 | 0.42 | −1.00 | 0.32 | 0.16 | CALCOCO2 | −0.06 | 0.09 | 0.02 | −0.06 | −0.12 |
| MAP4 | 0.64 | −0.22 | −0.68 | −0.12 | −0.51 | IGHV5-51 | 2.00 | −0.50 | −1.83 | 0.70 | −1.27 | IFNL2 | −0.92 | −0.24 | −0.57 | −1.13 | −0.63 |
| PELI2 | −1.41 | 0.88 | 1.36 | 0.09 | 0.18 | SERP2 | −0.68 | −0.04 | 1.04 | −0.03 | 1.28 | LINC00642 | −0.48 | −0.57 | −0.25 | 0.79 | −0.32 |
| LIFR | −1.47 | 1.12 | 1.67 | 0.42 | 0.53 | AL138781.2 | −0.84 | 0.03 | 0.53 | −0.36 | −0.01 | ACOT13 | 0.07 | −0.02 | 0.25 | −0.13 | 0.17 |
| DEFB4A | 7.26 | −5.42 | −6.51 | −2.46 | −5.43 | IGBP1 | 0.22 | 0.00 | −0.02 | −0.01 | −0.33 | C16orf54 | −0.18 | −0.69 | 0.75 | −0.30 | 0.52 |
| NAV1 | 0.69 | −0.53 | −1.08 | −0.11 | −0.42 | AC099518.6 | −0.63 | 0.48 | 0.44 | 0.40 | 0.27 | CACTIN-AS1 | 0.30 | 0.12 | −0.70 | 0.49 | 0.04 |
| MACROD1 | −1.05 | 0.61 | 0.61 | 0.39 | 0.33 | OR51K1P | −1.29 | 0.32 | 0.60 | −1.08 | −0.44 | RTP5 | 0.71 | 0.14 | −0.36 | 0.08 | −0.49 |
| AL390783.1 | −2.48 | 0.17 | 0.74 | 0.13 | −0.54 | KRT18P37 | −0.61 | 0.11 | 0.41 | 0.54 | 0.35 | LINC02238 | 0.51 | −1.50 | −0.65 | 0.81 | −0.20 |
| KPNB1 | 0.79 | −0.50 | −0.77 | −0.12 | −0.28 | BIN2P1 | −1.12 | −0.30 | −0.14 | 0.19 | −0.62 | BTF3P1 | 0.91 | 0.00 | −0.29 | 0.04 | 0.25 |
| NCAPG | 1.42 | −1.25 | −1.59 | −0.35 | −0.45 | AC007207.2 | −2.14 | 1.00 | 0.30 | 1.60 | −0.78 | AL392046.2 | 0.10 | 0.29 | −0.08 | 0.30 | −0.10 |
| CXCL8 | 4.43 | −4.72 | −5.23 | 0.20 | −2.26 | AC135050.3 | −0.61 | −0.27 | 0.18 | 0.11 | 0.16 | AC099654.2 | 0.44 | −1.49 | −0.61 | −0.14 | −1.64 |
| CCND1 | −0.74 | 0.29 | 0.61 | −0.02 | 0.18 | PSAP | 0.24 | 0.06 | −0.01 | −0.10 | −0.29 | AC018755.1 | 0.24 | −0.24 | 0.83 | 0.17 | 1.17 |
| RNPC3 | −0.70 | 0.48 | 0.68 | 0.19 | 0.25 | RBBP7 | 0.15 | 0.02 | −0.05 | 0.00 | −0.07 | DDX31 | 0.07 | 0.01 | −0.20 | 0.10 | −0.10 |
| ACCS | −0.96 | 0.47 | 0.54 | 0.35 | 0.30 | ARPP21 | −0.85 | 0.62 | 0.24 | 0.09 | −0.30 | AC113340.1 | 0.62 | −1.19 | 0.16 | −1.50 | −2.12 |
| AC104819.2 | −2.10 | 0.70 | 0.75 | 0.78 | 0.42 | AC109587.1 | −0.33 | 0.23 | 0.36 | −0.09 | −0.06 | CNOT4P1 | −0.91 | 0.89 | 1.12 | 0.31 | −1.00 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| FAM98A | 0.79 | −0.46 | −0.44 | −0.32 | −0.23 | AC108159.1 | 0.77 | 0.34 | 0.45 | 0.30 | −0.52 | AF228730.6 | −0.82 | 0.25 | 0.06 | 0.39 | −0.29 |
| SPRY1 | −0.83 | 0.46 | 1.01 | −0.02 | 0.28 | AL162431.2 | 0.71 | −0.71 | −0.28 | 0.18 | 0.00 | CXXC1P1 | −0.47 | −0.34 | −0.81 | −0.79 | −0.24 |
| PCSK2 | −1.81 | 1.20 | 0.97 | 0.68 | 1.01 | AC122714.1 | 0.67 | −0.52 | −0.72 | 0.16 | 0.05 | MT-TR | −0.49 | 0.62 | −0.34 | 0.95 | −0.65 |
| C7 | −2.17 | 1.42 | 1.73 | 1.67 | 0.25 | IQCA1 | 0.50 | −0.22 | −0.74 | −0.19 | −0.43 | GRK1 | 0.39 | −0.65 | −2.17 | 1.80 | −0.59 |
| ATP13A5 | −1.99 | 0.81 | 1.36 | 1.10 | 0.25 | CISD2 | 0.29 | −0.16 | −0.17 | −0.03 | −0.13 | RPS17P2 | 0.46 | 1.08 | −0.31 | 1.76 | 0.00 |
| EFL1 | 0.78 | −0.31 | −0.68 | −0.23 | −0.50 | AP001107.8 | −1.07 | 0.77 | 0.49 | 0.49 | −0.10 | AL445933.2 | −0.19 | −0.10 | −0.01 | 0.18 | 0.20 |
| RUVBL1 | 1.01 | −0.63 | −0.82 | −0.27 | −0.19 | AC017084.1 | 1.68 | −0.15 | −1.27 | −1.36 | −1.86 | SPPL2A | −0.06 | −0.08 | −0.14 | 0.10 | 0.01 |
| PLAC9 | −1.37 | 0.92 | 1.45 | 0.20 | 0.23 | KRT8P34 | 1.34 | −2.20 | −0.41 | −0.78 | 1.49 | SP6 | 0.13 | 0.63 | 0.96 | −0.08 | −0.16 |
| AC005154.2 | −1.19 | 0.85 | 1.14 | 0.32 | 0.16 | PDE4D | −0.20 | −0.11 | −0.05 | −0.10 | −0.07 | AC104564.4 | −0.54 | −1.21 | 0.38 | 0.32 | −0.20 |
| BCL3 | 0.98 | −0.81 | −1.00 | −0.22 | −0.37 | RPL7L1P3 | 0.50 | −0.54 | −0.35 | −0.62 | −0.39 | G32126 | −0.56 | 0.48 | 1.19 | −0.31 | −1.06 |
| C1orf74 | 1.62 | −1.03 | −1.72 | −0.48 | −1.43 | LRRN4 | −0.57 | 0.42 | 0.67 | 0.00 | 0.05 | LILRP1 | 0.70 | −0.97 | −0.45 | 0.26 | −0.24 |
| RAB3B | −1.76 | 1.05 | 1.64 | −0.27 | 0.20 | AGAP10P | −0.65 | 1.16 | 0.69 | 0.62 | −0.22 | NKX6-2 | 0.28 | 0.81 | −1.16 | 0.52 | −0.88 |
| CGNL1 | −1.68 | 0.88 | 1.82 | 0.34 | 0.36 | AP002852.1 | 1.27 | −0.35 | −0.75 | 0.53 | 1.05 | AC022121.1 | 0.28 | 0.46 | 0.44 | −0.24 | −1.12 |
| SRA1 | 0.56 | −0.26 | −0.71 | −0.05 | −0.25 | SRD5A1 | 0.36 | −0.05 | −0.19 | 0.15 | 0.18 | AL353807.2 | −0.39 | 0.99 | −0.26 | 0.64 | −0.72 |
| ASPA | −1.32 | 0.60 | 1.19 | 0.14 | 0.37 | AL160011.1 | 0.80 | −0.15 | −0.22 | −0.51 | −0.27 | AC073174.1 | −0.64 | 0.69 | −1.95 | 0.15 | −3.89 |
| C10orf90 | −1.40 | 0.59 | 0.98 | 0.11 | 0.46 | DPM3 | 0.33 | −0.18 | −0.19 | −0.16 | −0.03 | AC109361.1 | 0.23 | 0.04 | 0.37 | 0.04 | 0.25 |
| CDA | 2.05 | −0.70 | −1.57 | −0.79 | −1.86 | SNORA12 | −0.29 | 0.28 | 0.07 | 0.07 | −0.43 | RNA5SP491 | −0.31 | −0.09 | 1.11 | −0.45 | 0.41 |
| AP001000.1 | 1.00 | −0.21 | −0.74 | −0.26 | −0.63 | AC020928.2 | −1.05 | −2.05 | −0.48 | 0.35 | 2.99 | AC110296.1 | −0.92 | −0.73 | −0.25 | −2.15 | −0.80 |
| KRT17P3 | 2.59 | −2.50 | −3.83 | −1.60 | −1.23 | CDK13 | −0.10 | 0.06 | 0.09 | −0.01 | 0.03 | HMGB1P16 | −0.52 | 0.61 | −0.84 | 0.54 | 0.58 |
| PCDH9 | −1.81 | 1.07 | 1.64 | 0.38 | 0.22 | GHET1 | 0.67 | 0.13 | −1.89 | 0.00 | −1.27 | LINC00857 | −0.36 | −0.12 | 1.19 | −0.88 | 0.40 |
| AC009065.5 | −1.65 | 0.80 | 1.91 | 0.49 | 0.88 | RPL36AP29 | 1.26 | 0.14 | 1.54 | −0.15 | 0.25 | AL355574.1 | −0.10 | 0.02 | 0.27 | −0.45 | −0.01 |
| COPS3 | 0.88 | −0.42 | −0.68 | −0.18 | −0.48 | AL590762.2 | 1.18 | −0.60 | −1.38 | −0.02 | 0.40 | STARD7-AS1 | −0.08 | −0.08 | −0.05 | 0.04 | 0.05 |
| PANX1 | 1.39 | −0.91 | −1.61 | −0.28 | −1.03 | AC087071.2 | 1.00 | −1.00 | 0.38 | −0.61 | 0.99 | HRK | 0.20 | 0.03 | −0.40 | −0.18 | −0.75 |
| COL21A1 | −1.42 | 0.71 | 1.12 | 0.36 | 0.28 | AC010542.5 | 0.83 | −0.61 | −0.08 | −0.21 | −0.55 | AL590729.1 | 0.18 | −0.48 | 0.36 | −0.18 | 0.57 |
| PITPNA | 0.71 | −0.28 | −0.64 | 0.04 | −0.29 | AC008735.5 | −1.17 | −0.15 | 0.20 | 1.12 | −0.41 | RP11-1407015.3 | −0.59 | 0.69 | −1.71 | 0.49 | −1.72 |
| H2AFX | 1.34 | −1.05 | −1.37 | −0.14 | −0.43 | AC233280.1 | 0.96 | −0.42 | 0.19 | −0.38 | 0.06 | AL512506.1 | −0.17 | −0.55 | 0.86 | −0.32 | 0.67 |
| HNRNPF | 0.90 | −0.53 | −0.60 | −0.22 | −0.27 | HNRNPA1P68 | 0.30 | −0.16 | 0.09 | −0.17 | 0.08 | AL162726.3 | −0.26 | −0.23 | −0.69 | 0.22 | −0.55 |
| NRXN3 | −1.60 | 0.38 | 0.74 | 0.34 | 0.47 | RN7SL559P | 0.58 | −0.45 | 0.87 | −0.34 | 0.59 | AL513218.1 | 0.24 | −0.35 | 0.94 | −0.61 | 0.35 |
| FASTKD1 | 0.79 | −0.39 | −0.38 | −0.20 | −0.07 | KDELC1P1 | −0.52 | 0.46 | 1.02 | 0.40 | 0.78 | FOXO3 | −0.06 | 0.16 | 0.21 | 0.01 | −0.10 |
| PHLDA2 | 1.88 | −1.09 | −2.25 | −0.14 | −2.49 | HSD52 | −0.55 | 0.17 | 0.10 | 0.47 | 0.65 | RN7SKP115 | 0.33 | −0.65 | 0.37 | −1.23 | −0.25 |
| CGAS | 1.18 | −1.25 | −1.05 | −0.27 | 0.04 | NES | 0.38 | −0.64 | −0.35 | −0.35 | 0.01 | AC026401.1 | 0.22 | 0.61 | 0.07 | 0.22 | 0.31 |
| GULP1 | −0.95 | 0.52 | 1.12 | 0.29 | 0.36 | SMAD3 | −0.21 | 0.23 | 0.04 | 0.13 | −0.13 | SNORA36 | −0.25 | 0.73 | 0.01 | 0.23 | −0.36 |
| CHRM1 | −2.09 | 1.33 | 1.77 | 0.72 | 0.15 | AL021408.1 | −0.91 | 0.76 | 1.82 | −0.11 | −0.35 | FAM9A | 0.33 | −0.97 | −1.28 | 1.11 | 0.14 |
| STK31 | −1.84 | 0.41 | 1.64 | 0.31 | 0.87 | APOO | 0.26 | −0.04 | −0.05 | −0.19 | −0.02 | CR391992.1 | −0.11 | 0.23 | 0.31 | −0.14 | 0.11 |
| DYNLL1 | 1.21 | −0.27 | −0.77 | −0.02 | −0.93 | MAP3K15 | −0.72 | −0.48 | 0.38 | 0.01 | 0.18 | RAB19 | −0.22 | −0.05 | 0.76 | 0.22 | 1.55 |
| GRIA4 | −1.73 | 1.29 | 1.19 | 0.68 | 0.07 | KRTAP12-2 | −1.97 | −0.41 | 1.36 | −1.49 | 1.17 | RPL18P10 | −0.19 | 0.43 | 0.00 | 0.39 | −0.10 |
| PHACTR3 | −1.69 | 0.43 | 1.07 | 0.34 | 0.54 | RPL34P6 | 0.84 | −0.35 | 0.42 | −0.51 | −0.31 | AL117351.1 | −0.87 | −0.03 | 0.59 | −0.88 | −0.34 |
| OSR1 | −1.96 | 0.86 | 1.66 | 0.93 | 0.32 | AC092364.2 | 0.36 | 0.16 | 0.08 | 0.33 | 0.17 | ERGIC3 | 0.04 | 0.06 | −0.04 | 0.05 | −0.20 |
| CA3 | −1.60 | 0.95 | 1.34 | 0.75 | 0.30 | AL024474.1 | −0.74 | 0.68 | 0.48 | 0.40 | 0.28 | KRT18P20 | −0.89 | −0.34 | 1.09 | −1.89 | 1.30 |
| KRT8P38 | −1.51 | 0.82 | 1.37 | 0.46 | 0.34 | AC004594.1 | −0.42 | 0.30 | 0.33 | 0.09 | 0.18 | ATG7 | 0.04 | −0.07 | −0.12 | −0.04 | −0.05 |
| DTX3L | 1.04 | −0.72 | −0.80 | −0.30 | −0.35 | AC074212.1 | −1.12 | 1.26 | 0.64 | 1.14 | −0.02 | EFCAB3 | −0.36 | 0.38 | −2.40 | 1.55 | −2.18 |
| AL121769.1 | 1.94 | −0.89 | −1.77 | −0.34 | −0.67 | GTF2IRD2P1 | −0.84 | 0.35 | 1.33 | −0.18 | 0.03 | AC090983.1 | −0.36 | −1.08 | −0.43 | 0.36 | −0.81 |
| HSD17B13 | −2.02 | 1.19 | 1.30 | 0.83 | 0.02 | NKX3-2 | −1.03 | 0.01 | 2.63 | −0.41 | 0.58 | AC005915.1 | −0.40 | −0.26 | −0.39 | 0.40 | 0.39 |
| GAS1RR | −1.41 | 0.87 | 1.04 | 0.68 | 0.08 | AK6 | 0.30 | −0.30 | −0.30 | −0.13 | −0.26 | ITGB8 | −0.08 | 0.24 | −0.23 | 0.21 | −0.19 |
| LMAN1 | 0.70 | −0.40 | −0.53 | −0.29 | −0.29 | AC005534.2 | 0.87 | −0.86 | −0.10 | 0.10 | 1.27 | LINC01973 | −0.43 | −0.98 | −0.93 | −0.42 | 0.55 |
| RANBP1 | 1.00 | −0.75 | −0.80 | −0.44 | −0.24 | RPL7P38 | −2.14 | −0.39 | 1.91 | −1.39 | 0.54 | AC113382.2 | −0.58 | 0.42 | −0.09 | −0.20 | −1.92 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| IARS | 0.79 | −0.47 | −0.59 | −0.12 | −0.17 | AL139095.2 | 0.58 | 0.03 | −0.89 | 0.26 | −0.75 | AC092354.2 | −0.34 | 0.59 | 1.49 | 0.51 | 0.04 |
| ATL1 | −0.75 | 0.65 | 1.27 | 0.00 | 0.16 | SAMD9L | 0.40 | −0.50 | −0.31 | −0.53 | −0.19 | OOSP1P2 | 0.43 | −0.70 | −1.18 | 0.23 | −0.48 |
| D2HGDH | −1.35 | 0.49 | 0.48 | 0.70 | 0.56 | MIR3139 | 0.51 | −0.34 | 0.28 | 0.18 | 0.44 | FAM238B | −0.38 | 0.48 | −1.38 | 1.07 | −0.50 |
| DNAH11 | −1.35 | 0.30 | 0.56 | −0.10 | 0.08 | AP000907.3 | 1.23 | −0.11 | −0.20 | 0.76 | 0.57 | LINC01843 | −0.92 | 1.68 | −0.50 | 1.70 | −0.74 |
| ATP10D | 0.94 | −0.33 | −0.58 | −0.12 | −0.27 | SOCS5P2 | −0.94 | 0.90 | −0.01 | 0.83 | −0.64 | AC083841.2 | −0.24 | −1.00 | 0.38 | 0.61 | 2.14 |
| AL590822.1 | −1.77 | 0.43 | 1.34 | 0.27 | 0.90 | CIR1 | 0.16 | 0.02 | −0.19 | 0.03 | −0.27 | LINC00604 | 0.97 | −1.98 | −1.30 | 0.11 | 1.51 |
| H2AFY | 0.71 | −0.33 | −0.58 | −0.07 | −0.24 | GSTM5P1 | −1.27 | −0.40 | 1.21 | −0.30 | 1.10 | AC005277.2 | −0.61 | 0.22 | 1.08 | 0.16 | 0.67 |
| CDCA5 | 1.52 | −1.20 | −1.38 | −0.23 | −0.31 | AC093525.8 | −0.41 | 0.17 | 0.02 | −0.20 | −0.65 | ILDR2 | 0.20 | −0.09 | −1.12 | 0.32 | −0.86 |
| PALLD | 0.70 | −0.07 | −0.60 | 0.04 | −0.53 | ENPP7P2 | −0.87 | 0.43 | 1.17 | 0.71 | 1.20 | AC005863.1 | −0.52 | 1.50 | 0.82 | 0.06 | 0.33 |
| STT3B | 0.79 | −0.25 | −0.59 | 0.00 | −0.24 | AL121900.1 | 0.45 | 0.24 | −0.19 | 0.49 | −0.06 | AC026185.1 | −0.29 | 0.40 | 1.43 | −0.20 | −0.45 |
| MRTO4 | 0.93 | −0.72 | −0.96 | −0.14 | −0.33 | LINC00960 | −0.46 | 0.09 | 0.20 | 0.02 | 0.53 | OR6C66P | −0.44 | −0.24 | −1.79 | 0.88 | −2.47 |
| SLC25A5 | 1.10 | −0.36 | −0.91 | 0.00 | −0.71 | GBGT1 | −0.42 | −0.13 | 0.73 | −0.24 | 0.21 | AC005592.1 | −0.44 | 0.07 | 0.63 | −1.11 | −0.81 |
| CA11 | −1.25 | 0.87 | 1.31 | 0.50 | 0.29 | ATP1B4 | −0.87 | −1.48 | −0.63 | −0.49 | 0.20 | BX546450.2 | 0.60 | −0.54 | −1.73 | −0.69 | −1.11 |
| CLIC1 | 0.75 | −0.40 | −0.56 | −0.20 | −0.43 | POC1B | 0.18 | −0.11 | −0.06 | 0.00 | −0.03 | RNU6-28P | −0.24 | −0.25 | 0.43 | −0.76 | 0.03 |
| PPP1R14B | 0.82 | −0.50 | −0.86 | −0.05 | −0.34 | KCCAT198 | 1.14 | −0.80 | −1.50 | −0.10 | 0.04 | ATP1B3P1 | 0.38 | 0.13 | −0.94 | −0.48 | −0.58 |
| FKBP1A | 0.88 | −0.47 | −0.63 | −0.13 | −0.35 | SHE | −0.36 | 0.13 | 0.75 | 0.11 | 0.15 | AC008385.1 | −0.55 | −0.05 | 1.76 | 0.30 | −0.62 |
| NAA50 | 0.91 | −0.53 | −0.73 | −0.21 | −0.36 | SPATA41 | −0.49 | −0.15 | 0.47 | −0.60 | 0.36 | AMDHD1 | −0.13 | −0.15 | 0.79 | 0.13 | 0.59 |
| CSRP2 | 1.27 | −0.95 | −1.19 | −0.38 | −0.19 | FUT7 | 1.05 | −1.38 | 0.03 | −1.11 | −0.20 | GGACT | 0.09 | −0.10 | 0.17 | 0.18 | 0.43 |
| AL009031.1 | −1.74 | 1.02 | −0.01 | 0.92 | 0.11 | MMP14 | 0.23 | −0.22 | −0.10 | −0.46 | −0.27 | MRPS36P4 | 0.39 | 0.10 | 1.70 | −0.86 | −0.32 |
| AL354761.1 | −3.26 | 2.41 | 3.70 | 1.87 | 1.22 | G5109 | 0.73 | 0.10 | −0.65 | −0.28 | −0.41 | AL162727.1 | 0.32 | −1.58 | −1.45 | −0.93 | −0.34 |
| PAN2 | −0.86 | 0.41 | 0.61 | 0.30 | 0.27 | LINC00482 | −0.73 | 0.01 | 0.67 | 0.11 | −0.22 | LIPE-AS1 | −0.17 | −0.09 | −0.34 | −0.17 | −0.30 |
| KCNK1 | 1.36 | −0.32 | −1.10 | 0.04 | −0.78 | LINC02474 | 1.34 | −1.01 | 0.22 | −0.54 | −0.79 | AC093277.1 | 0.64 | −0.94 | −1.68 | −0.21 | −2.35 |
| SLITRK2 | −1.42 | 0.65 | 0.84 | 0.30 | 0.42 | SETD4 | −0.17 | 0.03 | 0.14 | 0.13 | 0.14 | RP11-417J8.1 | 0.56 | −0.56 | −1.07 | 0.44 | −0.72 |
| SPINK6 | 3.92 | −2.22 | −5.79 | −0.88 | −4.39 | CCDC26 | 0.51 | −0.89 | −0.58 | −0.76 | −0.04 | DNM3-IT1 | 0.28 | −0.07 | 1.31 | −0.42 | 1.29 |
| GRB2 | 0.55 | −0.33 | −0.47 | −0.11 | −0.17 | HMSD | 0.61 | −0.58 | −0.55 | 0.03 | −0.17 | GDI2P2 | −0.21 | 0.13 | 0.87 | −0.41 | 0.24 |
| MROH8 | −1.08 | 0.53 | 0.56 | 0.25 | 0.15 | AC008592.4 | −0.77 | 0.33 | 1.38 | 0.25 | −0.02 | HAGLR | −0.13 | 0.24 | 0.53 | −0.06 | 0.06 |
| HTATIP2 | 1.22 | −0.30 | −0.84 | 0.02 | −0.70 | CNDP1 | −0.66 | −0.29 | −0.18 | 0.12 | 0.10 | LINC02214 | −0.71 | −0.74 | 1.09 | −0.37 | 1.64 |
| ITGA3 | 1.14 | −0.76 | −1.56 | −0.02 | −0.30 | AC137800.1 | −1.23 | −0.85 | 0.86 | 1.37 | 1.56 | RBMX2P5 | −0.43 | −0.13 | −1.52 | 1.21 | −2.25 |
| STEAP3 | 0.88 | −0.53 | −0.44 | 0.02 | 0.09 | AC011477.5 | −1.09 | −0.55 | 1.37 | 0.18 | 0.26 | DUX4L16 | 0.65 | −1.01 | −1.49 | −0.02 | −1.36 |
| GSPT1 | 0.90 | −0.43 | −0.77 | −0.20 | −0.44 | AC007666.1 | −0.69 | 0.26 | −0.38 | −0.16 | −0.19 | AL133355.1 | −0.14 | 0.29 | 0.71 | 0.09 | 0.30 |
| CIAPIN1 | 0.73 | −0.38 | −0.70 | −0.09 | −0.39 | AL133260.1 | 0.50 | −0.90 | −0.33 | −0.46 | 0.40 | DCSTAMP | 0.40 | −0.28 | −0.82 | −0.19 | −0.19 |
| ANKRD36 | −0.58 | 0.23 | 0.45 | 0.11 | 0.21 | KCTD9P4 | −0.39 | 0.36 | 0.77 | 0.15 | −0.12 | AK4P1 | 0.17 | 0.03 | −0.45 | 0.53 | −0.23 |
| MCUB | 0.88 | −0.31 | −0.55 | −0.27 | −0.27 | DEPP1 | −0.58 | 0.66 | 0.74 | 0.45 | 0.18 | AC021876.1 | 0.90 | −0.34 | −0.53 | 0.77 | −1.45 |
| CROCCP3 | −1.21 | 0.35 | 0.64 | 0.40 | 0.35 | AC239804.1 | −0.74 | −0.62 | −0.14 | −0.28 | −0.24 | FOXL2NB | −0.29 | −0.40 | 1.59 | 0.19 | 1.01 |
| ACSS3 | −1.63 | 0.93 | 1.37 | 0.59 | 0.33 | CFAP52 | −0.56 | −1.03 | −0.13 | 0.35 | 0.53 | NT5DC3 | −0.07 | 0.01 | −0.20 | 0.01 | −0.17 |
| DBF4 | 1.06 | −0.70 | −0.99 | −0.21 | −0.50 | NPIPA1 | −0.30 | 0.18 | 0.30 | 0.13 | 0.10 | AC104073.1 | −0.73 | 0.07 | 1.64 | 0.22 | 1.23 |
| G2450 | −1.38 | 0.64 | 0.93 | 0.27 | 0.52 | AC008250.1 | −0.64 | 0.34 | 1.37 | 0.10 | −0.09 | NF1 | 0.04 | 0.00 | −0.08 | −0.01 | −0.04 |
| BFSP1 | 1.10 | −0.48 | −1.23 | −0.15 | −0.63 | AC136601.2 | 1.42 | −1.13 | −0.88 | −1.20 | 0.14 | SPANXN5 | 0.51 | −1.34 | −3.04 | 0.63 | −0.34 |
| ABCA8 | −1.84 | 1.45 | 1.89 | 1.12 | 0.36 | RAB15 | −0.18 | 0.20 | −0.09 | 0.33 | 0.21 | AC011726.1 | −0.19 | 0.44 | 1.05 | 0.11 | −0.20 |
| PRDX1 | 1.04 | −0.38 | −0.80 | −0.19 | −0.76 | DCAF12L2 | −1.05 | 0.90 | 1.77 | −0.06 | −0.15 | AL356289.2 | 0.64 | −0.90 | 0.12 | −0.58 | 0.83 |
| MST1L | −1.40 | 0.49 | 0.62 | 0.91 | 1.16 | MTND1P3 | −0.79 | −0.15 | 1.97 | −0.33 | 0.93 | RN7SL477P | −0.45 | −0.74 | −0.89 | −0.14 | −0.29 |
| IRX1 | −1.43 | 0.86 | 0.75 | 0.53 | 0.08 | AC104066.1 | 1.57 | 0.52 | 1.38 | −0.39 | −0.11 | COX20 | −0.08 | 0.13 | −0.10 | 0.02 | −0.06 |
| RBP4 | −3.48 | 2.81 | 2.74 | 0.58 | −0.02 | G31689 | −0.52 | 0.64 | 0.48 | 0.47 | 0.03 | RN7SKP162 | −0.93 | −0.19 | −0.49 | −0.53 | −0.61 |
| IFI44 | 1.45 | −0.99 | −1.05 | −0.50 | −0.47 | AC020604.1 | −0.72 | −0.48 | 1.02 | −0.20 | 0.63 | RNU6-226P | 0.91 | −1.07 | −2.20 | −0.04 | −0.88 |
| AZIN1-AS1 | −0.95 | 0.36 | 1.02 | 0.26 | 0.42 | RPL12P19 | −1.08 | −0.35 | 1.08 | 1.14 | 0.60 | ARL9 | 0.14 | 0.08 | −0.10 | 0.16 | −0.15 |
| G1562 | −1.29 | 1.06 | 1.27 | 0.28 | 0.18 | S1PR5 | 0.45 | −0.17 | −0.15 | 0.03 | 0.18 | AC012653.1 | −0.40 | −0.74 | −1.04 | 1.54 | 0.00 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| RN7SL486P | −3.82 | 0.01 | 2.85 | 2.02 | 2.17 | GPR149 | −0.95 | 0.89 | −0.12 | 1.03 | 0.10 | RPS4XP18 | −0.58 | −1.62 | 0.25 | −0.45 | 1.30 |
| OSM | 3.36 | −2.75 | −3.03 | −0.41 | −2.22 | AC012157.1 | 0.57 | 0.27 | −0.41 | 0.50 | 0.00 | NLRP12 | −0.22 | −0.68 | −0.22 | 0.05 | −0.02 |
| CHAC2 | 1.27 | −1.04 | −0.63 | −0.35 | 0.08 | AC010255.1 | 1.44 | −1.03 | −1.50 | 0.19 | −0.79 | G40988 | −0.15 | 0.23 | 0.01 | 0.40 | 0.25 |
| MKRN5P | −0.93 | 0.46 | 0.77 | 0.15 | 0.17 | COX14 | −0.28 | 0.10 | −0.14 | 0.37 | −0.16 | AL353132.1 | 0.65 | −0.29 | −0.39 | −0.74 | −2.97 |
| CENPH | 0.89 | −0.44 | −0.69 | −0.18 | −0.34 | AL096869.2 | 0.45 | −0.32 | −1.30 | 0.15 | −0.19 | CBLB | −0.07 | −0.06 | 0.05 | −0.25 | −0.03 |
| AL591485.1 | −0.97 | 0.49 | 0.45 | 0.24 | −0.03 | AC090559.1 | −0.35 | −0.33 | 0.01 | −0.20 | 0.39 | FERMT3 | 0.12 | −0.46 | −0.17 | −0.26 | −0.05 |
| RALGPS1 | −0.74 | 0.68 | 0.63 | 0.35 | 0.18 | STMN1P1 | −0.42 | 0.09 | 0.34 | 0.36 | 0.11 | LINC00167 | −0.22 | −0.37 | 0.80 | −0.33 | 0.93 |
| IDH3A | 0.77 | −0.55 | −0.94 | −0.18 | −0.46 | AP003392.6 | 0.83 | −0.44 | −0.18 | −0.31 | −0.49 | RNU6-823P | 0.96 | −1.44 | 0.16 | −0.12 | 2.02 |
| CLEC3B | −2.08 | 1.38 | 2.23 | 0.65 | −0.27 | LNP1 | −0.38 | 0.13 | 0.50 | −0.17 | −0.13 | HSPE1P26 | 0.16 | 0.08 | −0.32 | −0.06 | −0.31 |
| CLEC2A | −1.93 | 1.62 | 1.94 | 1.03 | 0.13 | AC127502.2 | −0.30 | −0.09 | 0.07 | 0.43 | 0.01 | LINC01318 | −0.26 | −0.56 | −0.33 | −0.33 | 0.04 |
| APBB1 | −1.11 | 0.72 | 0.96 | 0.21 | −0.03 | CALB1 | −0.44 | 0.08 | 0.12 | 0.40 | 0.06 | EGR4 | −0.33 | 0.33 | −0.50 | 0.68 | −0.97 |
| CACNA1D | −0.99 | 0.39 | 0.40 | 0.51 | 0.25 | AP001330.2 | −1.54 | −0.27 | 3.19 | 0.66 | 1.08 | AL354890.1 | −0.16 | −0.09 | 0.13 | −0.25 | 0.11 |
| KRT5 | 1.65 | −0.76 | −1.92 | 0.06 | −1.00 | NCMAP | −0.76 | 0.70 | 1.03 | 0.17 | 0.48 | OR6Q1 | −0.41 | 0.23 | −0.49 | −0.18 | −0.84 |
| N4BP2L1 | −1.23 | 0.60 | 1.12 | 0.07 | 0.22 | KRT17P8 | −0.81 | 0.29 | 2.19 | 0.03 | 0.49 | RPL17P17 | −0.13 | −0.09 | 0.11 | −0.33 | 0.11 |
| DNAJB6 | 0.85 | −0.22 | −0.98 | −0.04 | −0.65 | SSU72 | 0.18 | −0.06 | −0.07 | −0.13 | −0.03 | JPH1 | 0.13 | 0.14 | −0.44 | −0.15 | 0.04 |
| SOWAHC | 1.10 | −0.22 | −1.02 | −0.10 | −0.98 | CLEC2L | −0.94 | 0.03 | 0.68 | −0.54 | 1.17 | AL513128.2 | 0.89 | 0.20 | −1.42 | −0.03 | −1.86 |
| AC139795.1 | −0.83 | 0.42 | 0.66 | 0.20 | 0.11 | FOS | −0.34 | 0.01 | 0.66 | −0.67 | 0.82 | HMGB1P9 | 0.37 | −0.85 | −2.75 | 0.71 | −1.60 |
| FAM149A | −1.52 | 0.75 | 0.98 | 0.23 | 0.43 | AC011447.6 | −0.78 | 0.51 | 1.13 | 0.34 | −0.24 | AC015802.3 | −0.22 | −0.01 | 0.43 | 0.66 | 0.09 |
| OAS1 | 1.33 | −0.70 | −1.10 | −0.27 | −0.33 | AL136369.1 | −0.91 | 0.58 | 1.95 | 0.94 | 0.67 | CLEC1B | 0.23 | −0.75 | −0.70 | 0.33 | 0.00 |
| GNL2 | 0.82 | −0.47 | −0.80 | −0.26 | −0.47 | AC009196.1 | 1.65 | −0.20 | 0.07 | −0.17 | 0.41 | PCMTD1P1 | 0.86 | −0.67 | −1.11 | −0.51 | −1.59 |
| SLC28A3 | 1.63 | −0.83 | −1.35 | −0.27 | −0.60 | AL731569.1 | −0.30 | 0.17 | 0.73 | 0.09 | 0.27 | OR8D4 | −0.33 | 0.91 | 0.70 | −0.21 | −0.81 |
| REELD1 | −1.99 | 0.39 | 1.54 | 0.34 | 0.66 | GPAA1 | 0.18 | −0.04 | −0.24 | 0.17 | −0.04 | AL449212.1 | −0.10 | 0.23 | 0.46 | 0.03 | 0.16 |
| LMNB2 | 1.10 | −0.88 | −1.39 | −0.23 | −0.30 | MT-RNR1 | −0.65 | 0.34 | −0.04 | 0.99 | 0.11 | RARRES2P1 | −0.39 | 1.59 | −1.05 | 2.28 | 0.30 |
| STAU1 | 0.51 | −0.24 | −0.40 | −0.14 | −0.31 | RNU6-1043P | 0.88 | −0.10 | −0.61 | 0.07 | −0.57 | AC079203.2 | 1.17 | −0.79 | 1.52 | 0.44 | 1.62 |
| RAD18 | 0.66 | −0.40 | −0.63 | −0.10 | −0.26 | BIRC3 | 0.51 | −0.80 | −0.02 | −0.65 | 0.21 | RPTOR | 0.06 | 0.10 | −0.13 | 0.16 | −0.14 |
| PLA2G6 | −1.07 | 0.65 | 0.56 | 0.57 | 0.23 | CEP70 | −0.30 | 0.21 | 0.37 | 0.14 | 0.10 | IMP3P2 | −0.81 | −0.16 | 0.60 | −0.66 | 1.00 |
| COA7 | 0.85 | −0.37 | −0.67 | −0.11 | −0.40 | AC078962.2 | −0.98 | 0.26 | 2.47 | 0.45 | 0.66 | SNORD117 | −0.17 | 0.60 | −0.03 | 0.23 | −0.59 |
| EIF2S1 | 1.01 | −0.57 | −0.75 | −0.27 | −0.50 | LINC02363 | −0.64 | 0.23 | 0.06 | 0.13 | 0.08 | RTL8B | 0.06 | 0.11 | −0.04 | 0.15 | −0.05 |
| PSMB6 | 1.05 | −0.45 | −0.74 | −0.30 | −0.53 | MT-TE | −0.90 | 0.18 | −0.52 | 1.05 | −0.05 | HCCAT5 | 0.46 | −0.02 | −0.63 | 1.55 | −2.73 |
| SRCIN1 | −1.39 | 1.02 | 0.85 | 0.79 | 0.52 | AC104805.1 | −1.42 | 0.78 | 2.48 | 0.44 | 1.60 | PDXK | 0.07 | −0.14 | −0.45 | 0.09 | 0.05 |
| DYNLT1 | 0.75 | −0.40 | −0.37 | −0.21 | −0.24 | KRT20 | −0.71 | 0.20 | 1.79 | −0.49 | 0.13 | AC022784.3 | −1.13 | −0.21 | 2.48 | 0.30 | 2.01 |
| AREG | 3.08 | −1.13 | −4.18 | −0.59 | −3.36 | LDAH | 0.20 | −0.18 | −0.08 | −0.12 | −0.01 | AP4S1 | 0.04 | −0.02 | 0.08 | 0.02 | 0.03 |
| PLEKHG5 | −1.27 | 0.39 | 0.16 | 0.61 | 0.49 | INO80D | 0.16 | 0.11 | −0.16 | 0.06 | −0.22 | PHBP12 | 0.15 | 0.34 | −0.41 | 0.19 | −0.27 |
| LINC00377 | −2.85 | 1.60 | 1.26 | 1.98 | 0.20 | C11orf96 | −0.72 | 0.61 | 0.64 | 0.29 | −0.21 | CBWD6 | −0.06 | 0.16 | 0.16 | 0.03 | −0.03 |
| RRAGB | −0.72 | 0.36 | 0.66 | 0.22 | 0.26 | AC090625.1 | −1.93 | −0.25 | 1.41 | −0.51 | 0.75 | DHRS13 | 0.11 | −0.23 | −0.23 | 0.18 | 0.26 |
| LYRM9 | −1.18 | 0.42 | 1.39 | 0.15 | 0.46 | OR7E85P | −1.56 | 1.24 | 3.01 | −0.75 | 0.05 | NRGN | 0.18 | −0.04 | −0.17 | −0.11 | −0.97 |
| NIP7 | 1.05 | −0.60 | −0.85 | −0.03 | −0.35 | AC098483.2 | −2.12 | 0.17 | 2.42 | 1.56 | 3.48 | AC069410.1 | 0.54 | 0.19 | −1.25 | 0.13 | 0.30 |
| GKAP1 | −1.23 | 0.80 | 0.93 | 0.25 | −0.07 | AC079630.1 | −0.57 | −0.11 | 0.63 | −0.15 | 0.13 | AC022167.3 | 0.20 | −0.66 | −0.43 | −0.16 | 0.40 |
| SMARCA2 | −0.45 | 0.35 | 0.51 | 0.07 | 0.06 | AC092171.3 | −0.44 | 0.28 | 0.30 | 0.65 | 0.16 | ACTBP2 | 0.21 | −0.04 | −1.30 | 0.56 | −0.75 |
| LINC01550 | −0.99 | 0.35 | 1.30 | 0.01 | 0.37 | AC092964.2 | 0.67 | −1.17 | −1.38 | 0.05 | 0.36 | AL132709.2 | 0.86 | −0.49 | −0.96 | −0.55 | −0.61 |
| HNRNPM | 0.64 | −0.46 | −0.56 | −0.18 | −0.11 | AL354718.1 | −0.72 | −0.13 | 1.01 | −0.14 | 0.51 | AL080285.1 | 0.55 | 0.18 | −2.84 | 1.48 | −2.25 |
| ARPC3 | 1.05 | −0.63 | −0.92 | −0.37 | −0.69 | AC009226.1 | −0.45 | −0.27 | −0.27 | −0.25 | 0.03 | RNA5SP450 | −0.13 | −0.08 | −1.27 | 0.34 | −0.90 |
| ANXA7 | 0.73 | −0.32 | −0.69 | −0.02 | −0.42 | AC092168.2 | 0.56 | 0.25 | −0.07 | −0.10 | −0.25 | RAB43 | −0.14 | −0.47 | −0.12 | −0.40 | 0.10 |
| COMMD8 | 1.37 | −0.46 | −0.79 | −0.10 | −0.54 | AC092042.1 | −0.88 | 0.24 | −0.51 | −0.24 | −1.98 | SLC7A7 | −0.08 | −0.11 | 0.24 | −0.22 | −0.11 |
| ADAMTS9-AS2 | −1.55 | 1.24 | 1.50 | 0.48 | 0.11 | AL008723.1 | 1.05 | −1.28 | 0.17 | −0.56 | 0.87 | RN7SL36P | 0.27 | −0.34 | 0.07 | 0.02 | 1.08 |
| ANKS1B | −1.26 | 0.64 | 0.76 | 0.48 | 0.20 | AC090515.2 | 0.56 | −0.64 | −0.79 | 0.28 | −0.08 | AC005962.1 | −0.23 | 0.61 | −0.03 | 0.41 | 0.16 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| EXD3 | −1.26 | 0.51 | 1.08 | 0.63 | 0.56 | AC095050.1 | −1.58 | −0.90 | −0.12 | 2.41 | 0.45 | LINC00954 | −0.10 | −0.18 | 0.40 | −0.27 | 0.11 |
| SMC2 | 0.91 | −0.61 | −0.89 | −0.17 | −0.41 | AC022706.1 | 1.00 | 0.59 | 0.23 | −0.26 | −0.30 | KRT33A | 0.53 | −1.93 | 1.01 | 0.34 | 2.18 |
| GTF3C6 | 1.20 | −0.63 | −0.95 | −0.19 | −0.51 | IP6K2 | −0.15 | 0.34 | 0.23 | 0.22 | 0.02 | MIR2052HG | −0.29 | −0.84 | −0.41 | 0.27 | 2.74 |
| AC092070.2 | −1.07 | 0.52 | 1.26 | −0.04 | −0.06 | RN7SL239P | 0.70 | −0.99 | −0.38 | 0.02 | 0.83 | AC126915.2 | −0.43 | 0.78 | 2.55 | 0.14 | 0.71 |
| HAND2-AS1 | −1.65 | 0.29 | 0.95 | 0.11 | 0.06 | AC009171.2 | −0.83 | 0.21 | 0.70 | −0.05 | 0.29 | SIX6 | −0.52 | −0.79 | −1.11 | 1.39 | −0.19 |
| HK2 | 1.40 | −0.94 | −1.37 | −0.32 | −0.53 | G14803 | −0.67 | −0.30 | 1.23 | 0.42 | 1.15 | AC002407.1 | −0.40 | −0.94 | −1.83 | 0.01 | −0.55 |
| IER5 | 0.95 | −0.41 | −1.16 | 0.00 | −0.53 | PRAP1 | −0.96 | −0.70 | −0.39 | 0.43 | 1.14 | AC103702.2 | −0.56 | −1.14 | −1.34 | −0.61 | 1.18 |
| PSMA7 | 0.68 | −0.39 | −0.63 | −0.15 | −0.29 | PTTG3P | 0.68 | −0.67 | 0.12 | 0.07 | 0.84 | AC012506.4 | −0.77 | −0.05 | 0.87 | −1.00 | 0.59 |
| SEC61G | 1.29 | −0.72 | −0.71 | −0.65 | −0.41 | AC009283.1 | −0.49 | 0.50 | 1.31 | −0.14 | 0.52 | AP000619.3 | 0.45 | −1.31 | −1.58 | 0.72 | 1.53 |
| RND3 | 1.12 | −0.84 | −1.26 | −0.44 | −0.43 | STX10 | −0.24 | −0.02 | −0.16 | 0.18 | 0.15 | ERHP2 | 0.46 | 0.84 | 0.54 | −0.25 | −0.32 |
| GRIFIN | −2.82 | 1.32 | 2.35 | 0.99 | 0.33 | MYPOP | 0.21 | −0.05 | −0.42 | 0.05 | −0.24 | LINC00999 | 0.61 | −0.75 | −0.92 | 1.24 | 0.21 |
| SLC9A2 | −1.84 | 1.14 | 1.16 | 1.01 | 0.09 | SLURP2 | 1.14 | 0.19 | 1.09 | 0.16 | −0.52 | FLVCR1 | 0.07 | −0.11 | −0.01 | 0.13 | 0.29 |
| HERC6 | 1.56 | −0.93 | −1.53 | −0.58 | −0.86 | GOLGA2P5 | −0.27 | 0.23 | −0.09 | 0.41 | 0.45 | SNORD114-1 | −0.17 | 0.83 | 0.75 | −0.07 | −0.85 |
| RAP1GDS1 | 0.71 | −0.28 | −0.52 | −0.04 | −0.26 | PPP6R3 | 0.10 | 0.00 | −0.23 | 0.02 | −0.16 | CSPP1 | −0.06 | −0.07 | −0.11 | −0.05 | −0.08 |
| OR2G6 | −3.25 | −0.11 | 1.26 | 1.27 | 1.19 | AGGF1P2 | −0.55 | 0.20 | 0.58 | 0.39 | 0.84 | LINC01685 | −0.59 | 0.44 | 1.37 | 0.33 | −0.45 |
| PDZRN3 | −1.47 | 0.79 | 1.55 | −0.31 | −0.11 | MAGEF1 | 0.22 | 0.08 | 0.04 | 0.01 | −0.02 | ANKRD61 | −0.12 | 0.01 | 0.15 | 0.22 | 0.00 |
| PVT1 | 1.19 | −0.68 | −0.50 | −0.12 | 0.22 | SELPLG | 0.52 | −0.56 | −0.18 | −0.48 | 0.11 | AL035467.1 | −0.69 | −0.94 | −0.35 | −0.36 | −0.05 |
| ETF1 | 0.78 | −0.23 | −0.74 | −0.06 | −0.53 | AP003170.5 | 0.82 | −0.09 | −0.10 | 0.08 | −0.42 | LINC00528 | −0.26 | −1.64 | 0.45 | 0.23 | 1.62 |
| SFXN1 | 0.72 | −0.52 | −0.89 | −0.14 | −0.23 | MYO7A | −0.47 | −0.13 | −0.38 | 0.32 | 0.08 | AC140125.2 | −0.96 | 0.20 | −1.12 | 1.44 | −0.06 |
| SH3BGRL3 | 1.15 | −0.66 | −1.00 | −0.30 | −0.42 | HLA-DPB1 | 0.43 | −0.55 | 0.05 | −0.54 | 0.19 | AC073052.2 | 0.38 | −0.40 | 0.02 | 0.90 | −0.48 |
| LMOD1 | −1.55 | 0.98 | 1.07 | 0.69 | −0.38 | JADE3 | 0.20 | −0.04 | −0.32 | 0.07 | −0.17 | AC067863.1 | −0.45 | −1.09 | 1.40 | −0.16 | 2.33 |
| ANK2 | −1.40 | 1.02 | 1.37 | 0.33 | 0.04 | AP001172.1 | −0.54 | 0.54 | 0.91 | 0.40 | 0.00 | NPM1P34 | 0.35 | −2.13 | −1.01 | −0.58 | −0.43 |
| RNF112 | −1.84 | 0.64 | 1.72 | 0.57 | 0.74 | MIR553 | 0.53 | −0.29 | −0.09 | −0.10 | −0.20 | AC027698.1 | −0.19 | −0.29 | 0.55 | −0.74 | 0.53 |
| CARD6 | 1.26 | −0.59 | −0.92 | −0.08 | −0.35 | DNAH17 | 0.34 | −0.39 | −0.85 | 0.23 | 0.29 | BRCC3P1 | −0.11 | 0.18 | 0.11 | 0.10 | 0.09 |
| AC079781.4 | −2.23 | 0.88 | 1.47 | 1.50 | 0.82 | AC099506.2 | 0.57 | 0.08 | −0.64 | 0.09 | −0.22 | ARSEP1 | −0.71 | 0.49 | −0.50 | −0.08 | −0.75 |
| LRRN3 | −0.79 | 0.60 | 0.63 | 0.39 | 0.23 | AL138781.1 | −0.66 | 0.26 | 0.57 | −0.05 | 0.03 | RNA5SP42 | −0.70 | −0.40 | −0.87 | −0.11 | −0.60 |
| CYCS | 1.13 | −0.68 | −1.15 | −0.41 | −0.58 | PRKD2 | −0.21 | 0.18 | 0.02 | 0.17 | 0.12 | NDUFB2-AS1 | 0.21 | 0.15 | −0.04 | 0.12 | −0.36 |
| MTDH | 0.65 | −0.34 | −0.52 | −0.19 | −0.24 | OR1J4 | 1.09 | −0.30 | −0.38 | 0.00 | 0.54 | AC126323.2 | 0.76 | 0.36 | −0.41 | 1.14 | −0.30 |
| KHDRBS1 | 0.49 | −0.22 | −0.46 | −0.09 | −0.15 | AL133342.1 | 1.01 | −0.81 | −2.31 | −0.64 | −1.53 | MIR27B | −0.13 | 0.29 | 0.29 | 0.19 | −0.14 |
| AC093879.2 | −1.80 | 0.51 | 0.98 | 0.51 | 0.65 | AL022319.1 | −0.70 | 1.04 | 1.08 | 0.40 | 0.42 | AC003984.1 | −0.40 | 0.74 | −0.48 | 0.26 | −1.37 |
| CBX3 | 0.79 | −0.49 | −0.54 | −0.21 | −0.21 | RNU6-1016P | 0.41 | −0.04 | −0.41 | 0.28 | −0.06 | MTERF1 | 0.04 | 0.06 | −0.01 | 0.04 | 0.06 |
| ICA1 | −1.01 | 0.54 | 1.00 | 0.35 | 0.54 | ALKBH2 | 0.21 | −0.20 | −0.21 | 0.02 | 0.21 | AL731533.2 | 0.84 | 0.16 | −0.11 | −0.07 | 1.26 |
| LINC01290 | −1.39 | 0.64 | 1.03 | 0.40 | 0.48 | OR6B1 | −0.84 | 0.79 | 0.64 | 0.77 | −0.13 | ARRDC5 | 0.22 | −0.78 | −0.61 | −0.29 | 0.29 |
| SLC25A27 | −0.96 | 0.75 | 0.92 | 0.60 | 0.27 | IGHA2 | 1.33 | 2.43 | 1.00 | −0.55 | 0.60 | MIR5689HG | 0.30 | −0.27 | 0.15 | −0.31 | −0.22 |
| SNHG14 | −0.83 | 0.48 | 0.77 | 0.25 | 0.17 | GAU1 | −0.43 | 0.00 | 0.05 | 0.09 | 0.17 | MAPRE1P3 | 0.57 | 0.75 | 0.00 | 0.88 | 0.58 |
| MAST4 | 0.72 | −0.15 | −0.68 | −0.07 | −0.50 | AC013468.1 | −0.57 | −0.05 | 0.23 | −0.14 | 0.01 | GCG | 0.45 | −0.36 | 1.96 | 0.31 | 0.81 |
| GGA2 | −0.50 | 0.21 | 0.29 | 0.14 | 0.15 | AC106820.2 | −0.72 | −1.06 | 0.32 | −0.39 | 0.12 | DMKN | 0.14 | 0.40 | 0.71 | 0.17 | −0.21 |
| DCTN5 | 0.62 | −0.28 | −0.42 | −0.20 | −0.33 | STX11 | 0.41 | −0.61 | −0.33 | −0.38 | −0.59 | LINC01030 | 0.27 | −0.17 | −1.00 | 0.63 | −0.09 |
| NOLC1 | 1.07 | −0.73 | −0.92 | −0.28 | −0.30 | LRRC38 | −0.79 | −0.19 | −1.01 | −0.16 | −0.06 | PILRA | −0.14 | −0.35 | −0.07 | −0.23 | 0.35 |
| PKD1 | −1.15 | 0.39 | 0.53 | 0.42 | 0.41 | AL358934.1 | −1.74 | −0.72 | 3.87 | −0.07 | 2.45 | AC025283.1 | −0.35 | −1.40 | 0.12 | 0.61 | 0.03 |
| BLNK | 0.93 | −0.11 | −0.43 | 0.03 | −0.46 | AC002429.2 | −0.95 | −0.08 | 0.46 | 0.59 | 0.76 | GOLGA3 | 0.04 | −0.10 | −0.20 | −0.10 | −0.11 |
| BRCA2 | 1.05 | −0.90 | −1.03 | −0.34 | −0.29 | CDH2 | −0.66 | 0.36 | 1.07 | −0.85 | 0.44 | AC087392.5 | 0.22 | −0.28 | −0.05 | −0.41 | 0.34 |
| RBM3 | 0.62 | −0.33 | −0.65 | −0.04 | −0.39 | AP001922.3 | −0.66 | 0.69 | 0.98 | 0.55 | 0.13 | AC023043.1 | 0.59 | 1.52 | −1.03 | 1.16 | −0.79 |
| GNAZ | −1.29 | 0.60 | 0.71 | 0.16 | −0.03 | AL392023.2 | −0.93 | −0.08 | −0.15 | −0.07 | 0.11 | AL354692.1 | −0.34 | −0.44 | −0.32 | −1.18 | −1.56 |
| FOXM1 | 1.31 | −0.97 | −1.36 | −0.27 | −0.41 | AL031432.5 | −0.61 | −0.25 | 0.69 | −0.35 | 0.11 | AC022164.1 | −0.39 | 0.93 | −3.05 | 0.00 | −1.63 |
| NUP88 | 0.65 | −0.27 | −0.64 | −0.14 | −0.31 | AC119150.1 | −0.88 | 0.38 | 1.89 | −1.02 | 0.08 | ASCL3 | 0.27 | −0.28 | −0.54 | 0.50 | 0.71 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| NTRK3 | −1.82 | 0.69 | 0.65 | 1.10 | 0.23 | AC091948.2 | −0.94 | −0.40 | 1.16 | −0.91 | 0.40 | ATP7A | 0.07 | 0.28 | 0.41 | 0.19 | −0.14 |
| DENND2A | −1.54 | 0.63 | 1.43 | 0.71 | 0.36 | AL022476.1 | −0.61 | 0.69 | −0.79 | 0.36 | −0.45 | MORF4L2P1 | 0.56 | −0.84 | 0.07 | −0.32 | 1.59 |
| NUTF2 | 0.78 | −0.47 | −0.52 | −0.25 | −0.26 | LINC02587 | −1.08 | 0.79 | 2.30 | 0.26 | 0.18 | ODAPH | −0.30 | 0.00 | −2.04 | −0.01 | −1.51 |
| NIPAL4 | 1.56 | −0.62 | −1.21 | −0.13 | −0.96 | PSORS1C1 | 0.39 | −0.12 | 0.06 | −0.22 | −0.27 | NEBL | −0.07 | 0.21 | 0.13 | 0.30 | 0.00 |
| GEN1 | 1.02 | −0.66 | −0.80 | −0.09 | −0.16 | CPNE2 | 0.18 | −0.07 | 0.00 | −0.06 | −0.04 | RNA5SP344 | 0.21 | 0.45 | 0.83 | −0.19 | 0.42 |
| H2AFY2 | 0.88 | −0.26 | −0.70 | −0.13 | −0.39 | MSC-AS1 | −0.41 | −0.02 | 0.52 | −0.31 | 0.15 | ATP5PDP2 | 0.36 | −1.80 | −0.34 | 0.59 | 1.57 |
| SEC61B | 0.74 | −0.50 | −0.52 | −0.29 | −0.29 | LINC02060 | −1.07 | 0.22 | −0.91 | −0.21 | −0.54 | AC108477.1 | −0.38 | 0.95 | 0.26 | 0.56 | −0.72 |
| HIST1H3I | 1.50 | −1.09 | −1.30 | −0.35 | −0.87 | MACC1 | −0.29 | 0.44 | 0.83 | 0.16 | 0.05 | LMO2 | −0.11 | 0.29 | 0.49 | 0.36 | 0.16 |
| C12orf75 | 1.01 | −0.35 | −1.12 | 0.09 | −0.42 | LINC00222 | −0.75 | −0.85 | 0.26 | 0.61 | 0.12 | ASB10 | −0.57 | −0.54 | −2.36 | 2.20 | −0.31 |
| ATP11B | 0.89 | −0.25 | −0.68 | 0.00 | −0.43 | AP001107.1 | −0.37 | −0.07 | 0.27 | 0.04 | 0.36 | FBXW7 | −0.06 | 0.15 | 0.00 | 0.12 | 0.02 |
| OSTC | 0.89 | −0.54 | −0.50 | −0.36 | −0.30 | SEPT10P1 | −0.68 | 0.52 | −0.65 | 0.66 | −0.87 | AC104241.1 | −0.60 | 0.54 | 2.53 | −0.75 | −1.25 |
| JPT2 | 0.95 | −0.37 | −0.66 | −0.20 | −0.25 | AC021491.2 | 0.64 | −0.69 | −0.65 | 0.01 | 0.16 | AC005394.1 | 0.81 | −1.09 | −2.01 | 0.43 | −0.76 |
| ARHGEF10 | −0.91 | 0.37 | 0.52 | 0.19 | 0.10 | DDX50P1 | −0.24 | 0.07 | 0.26 | 0.15 | 0.25 | AC091429.1 | 0.27 | 0.82 | −1.18 | 0.81 | −1.32 |
| LINC01239 | −2.24 | 1.71 | 1.61 | 0.71 | 0.07 | PHGR1 | −1.08 | 2.10 | 2.03 | −0.82 | −1.44 | AC090371.1 | 0.48 | 0.37 | −0.51 | −0.10 | −1.07 |
| ARAP2 | 1.13 | −0.21 | −0.82 | 0.11 | −0.56 | SORD | 0.35 | −0.24 | −0.22 | 0.25 | 0.29 | AC006254.3 | −0.22 | −0.11 | 1.58 | −0.17 | 0.67 |
| CCDC47 | 0.60 | −0.27 | −0.46 | −0.06 | −0.13 | AL390719.1 | 0.44 | −0.43 | −0.73 | −0.30 | −0.38 | RPL21P32 | −0.18 | 1.05 | 0.70 | 0.53 | 0.12 |
| DEPDC1B | 1.43 | −1.00 | −1.19 | −0.46 | −0.40 | AF250324.1 | −0.98 | 0.18 | 0.63 | 0.61 | 1.08 | LINC01277 | −0.17 | −0.17 | −0.24 | 0.39 | −0.08 |
| PIP4K2C | 0.71 | −0.23 | −0.53 | −0.12 | −0.35 | PTMAP3 | −0.54 | −0.16 | 0.66 | −0.27 | 0.79 | C19orf81 | 0.40 | 0.63 | 0.37 | 0.07 | 0.29 |
| GHR | −1.59 | 1.15 | 0.97 | 0.69 | 0.02 | RPS15AP38 | 1.54 | 0.73 | −0.99 | 0.41 | −1.11 | AF001550.2 | 0.20 | −0.53 | −2.10 | 0.25 | −1.40 |
| SPEF2 | −1.13 | 0.55 | 1.11 | 0.21 | 0.35 | AC092145.1 | 0.50 | −1.09 | −1.21 | −0.63 | −0.24 | RNU6-981P | 0.44 | −0.62 | −0.80 | −0.46 | −0.35 |
| PIP | −2.94 | 2.50 | 2.92 | 0.11 | 0.62 | CD3G | 0.60 | −0.73 | −0.28 | −0.29 | 0.14 | LINC01247 | −0.44 | −1.12 | −0.78 | 0.63 | 1.92 |
| OBSCN | −1.04 | 0.55 | 0.36 | 0.44 | 0.12 | CEP128 | −0.21 | −0.14 | 0.10 | −0.26 | 0.09 | SNORD14E | 0.16 | −0.18 | 0.20 | −0.33 | −0.41 |
| SCN7A | −1.95 | 0.82 | 1.47 | 0.77 | 1.34 | AC025183.1 | 0.57 | 0.20 | −1.36 | 0.22 | −0.64 | PCGEM1 | 0.51 | −1.39 | −1.04 | 0.08 | −1.98 |
| STAT1 | 1.21 | −0.94 | −0.95 | −0.62 | −0.45 | RP11-282E4.1 | −0.74 | 0.40 | 0.96 | −0.32 | 0.54 | OR4H12P | 0.51 | −0.19 | 0.31 | 0.08 | −1.45 |
| GGT7 | −1.05 | 0.20 | 0.46 | 0.44 | 0.42 | AC018752.1 | 0.51 | −0.46 | −0.08 | −0.02 | 0.42 | PTDSS2 | 0.06 | −0.30 | −0.19 | 0.01 | 0.20 |
| CKAP2 | 1.05 | −0.59 | −0.90 | −0.27 | −0.31 | C11orf52 | −1.19 | 0.97 | 2.65 | 0.48 | 0.59 | AP004608.1 | −0.31 | −0.42 | −1.33 | 0.73 | −0.01 |
| COL28A1 | −1.46 | 1.02 | 1.37 | 0.35 | 0.74 | AC018523.1 | −1.18 | 0.44 | 3.78 | −1.83 | −0.07 | SNX15 | −0.10 | 0.39 | −0.09 | 0.27 | −0.06 |
| RAB8A | 0.76 | −0.28 | −0.71 | −0.14 | −0.45 | AC011406.1 | 0.80 | −0.56 | −0.71 | −0.10 | −0.83 | OR6C4 | 0.41 | −0.84 | 0.40 | 0.09 | 0.30 |
| ASAP3 | −0.92 | 0.53 | 0.95 | 0.24 | 0.18 | CRYM | −0.48 | 0.19 | 0.16 | 0.36 | 0.09 | LINC01476 | −0.24 | −0.30 | −0.70 | 0.27 | −0.08 |
| PPP1R1A | −3.11 | 2.94 | 1.62 | 1.52 | 0.07 | ITGAE | 0.23 | −0.58 | −0.21 | −0.13 | 0.21 | AC090720.1 | −0.37 | −0.70 | −0.91 | −0.81 | −1.12 |
| CPSF2 | 0.69 | −0.40 | −0.52 | −0.20 | −0.28 | AC010967.2 | −0.95 | 0.45 | −1.66 | 0.83 | −0.34 | MINOS1P3 | −0.48 | −0.91 | 0.85 | −0.27 | 1.34 |
| NMU | 1.83 | −0.29 | −1.01 | −0.01 | −1.12 | MIR548C | 1.24 | −1.44 | −1.29 | −0.41 | −0.31 | MIR4419A | 0.24 | 0.10 | −1.35 | 0.25 | −0.96 |
| OGA | −0.39 | 0.25 | 0.23 | 0.18 | 0.02 | ASCC1 | 0.15 | −0.20 | −0.36 | −0.03 | −0.22 | AL590490.1 | −0.61 | 0.09 | −0.32 | 0.49 | 0.37 |
| KMT5C | −1.19 | 0.43 | 0.53 | 0.57 | 0.56 | GATA2 | −0.31 | 0.37 | 0.80 | 0.01 | 0.03 | AL136100.1 | −0.54 | −0.10 | −0.02 | −0.30 | 0.12 |
| NPAS3 | −1.26 | 0.31 | 0.66 | −0.26 | 0.00 | PLD4 | −0.44 | 0.34 | 0.72 | 0.16 | 0.57 | AC099494.3 | 0.16 | 0.23 | 0.13 | 0.26 | 0.07 |
| LEPR | −1.32 | 0.59 | 0.93 | 0.76 | 0.14 | AC005832.1 | −0.98 | −0.62 | 1.43 | −0.01 | 1.52 | AL357515.1 | −0.19 | −0.07 | −0.30 | 0.52 | 0.00 |
| ANKEF1 | 1.00 | −0.49 | −0.95 | −0.18 | −0.29 | MRM3 | 0.26 | −0.14 | −0.32 | −0.10 | −0.25 | AC068880.1 | 0.43 | −0.77 | −1.27 | 0.46 | −0.47 |
| GLRX3 | 0.83 | −0.44 | −0.65 | −0.20 | −0.23 | RINL | −0.34 | −0.24 | 0.52 | −0.25 | 0.65 | AC092851.1 | −0.18 | 0.74 | 0.57 | 0.62 | −0.06 |
| FTSJ1 | 0.60 | −0.44 | −0.57 | −0.20 | −0.05 | MGAT1 | 0.15 | −0.08 | −0.22 | −0.03 | −0.17 | C2orf42 | 0.05 | −0.01 | 0.03 | −0.11 | −0.05 |
| G18287 | −1.86 | 0.95 | 2.40 | 0.03 | 0.35 | RN7SL548P | −0.89 | 0.38 | 0.06 | −0.30 | 0.30 | KCNT1 | −0.15 | −0.25 | 0.41 | 0.23 | 0.56 |
| ELOVL4 | 1.82 | −0.21 | −0.35 | 0.19 | −0.30 | SIRT7 | 0.23 | −0.03 | −0.30 | 0.03 | −0.18 | AC020892.2 | 0.52 | −1.14 | −2.32 | 0.57 | −1.92 |
| AC008440.3 | −2.25 | 1.54 | 1.83 | 0.06 | 0.01 | RN7SL403P | −0.63 | 0.12 | 0.64 | −0.11 | 0.41 | AL009178.2 | 0.36 | 0.31 | 0.80 | 0.14 | −0.08 |
| PSMC4 | 0.70 | −0.39 | −0.77 | −0.16 | −0.39 | AC022022.2 | 0.57 | −0.88 | −0.64 | −0.31 | 0.34 | EEF1A1P14 | −0.18 | 0.81 | −0.40 | 0.35 | −0.40 |
| MRPL17 | 0.87 | −0.53 | −0.67 | −0.10 | −0.33 | AC097537.1 | −1.29 | 0.12 | −0.18 | 0.86 | −1.45 | IGHV3-7 | 0.63 | −0.24 | 1.40 | −0.40 | −0.35 |
| STX6 | 0.64 | −0.26 | −0.57 | −0.04 | −0.29 | AC007326.1 | −1.51 | 1.11 | −2.09 | 0.13 | −1.49 | AC100784.1 | 0.57 | 0.70 | −0.74 | 0.64 | −0.11 |
| LINC01473 | −1.11 | 0.84 | 1.22 | 0.47 | 0.29 | AC079193.1 | −1.60 | 1.31 | 1.25 | 1.23 | 0.08 | FGFR3P5 | −1.06 | −0.58 | 0.90 | −1.93 | 2.79 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| LINC00273 | 1.36 | −0.97 | −1.72 | −0.35 | −0.47 | AC010175.1 | −0.89 | 0.27 | 1.22 | 0.24 | −0.02 | MIR3677 | −0.39 | 1.04 | −0.20 | 0.16 | −1.17 |
| RCOR1 | 0.80 | −0.37 | −0.74 | −0.12 | −0.51 | CHST3 | 0.26 | −0.02 | −0.41 | 0.07 | −0.23 | RN7SL154P | −0.23 | −0.34 | −0.05 | 0.16 | 0.62 |
| G10489 | −4.10 | 0.68 | −0.11 | 3.25 | −0.23 | G17690 | −0.49 | −0.04 | −0.71 | −0.18 | −0.04 | AC074033.1 | −0.28 | 0.30 | −0.11 | −0.15 | 0.44 |
| SLC25A42 | −0.87 | 0.54 | 0.68 | 0.42 | 0.60 | RPL17P19 | −0.79 | 1.08 | 0.34 | 0.05 | 0.09 | KRTAP16-1 | −0.37 | −0.98 | 2.90 | −0.20 | 2.27 |
| PYROXD2 | −1.06 | 0.60 | 0.92 | 0.22 | 0.16 | AC135721.1 | −0.88 | 0.21 | −0.19 | 0.09 | −1.71 | MAP1LC3BP1 | −0.49 | 0.07 | 1.22 | 0.10 | 0.86 |
| KLK10 | 1.35 | −1.03 | −1.13 | −0.40 | −0.38 | ACSL3 | 0.28 | −0.11 | −0.08 | −0.17 | 0.01 | PIN1P1 | −0.58 | 0.47 | −1.12 | 0.59 | −0.95 |
| ARL4C | 1.06 | −0.38 | −0.68 | −0.10 | −0.40 | AL031721.1 | −1.56 | 0.61 | 1.21 | −1.02 | 0.00 | CERK | 0.05 | 0.05 | 0.12 | −0.13 | 0.09 |
| RPS6KA4 | 0.99 | −0.68 | −1.38 | 0.10 | −0.42 | SLC12A9-AS1 | 0.59 | 0.05 | −0.27 | 0.43 | 0.30 | C12orf65 | −0.04 | −0.10 | 0.29 | −0.14 | 0.21 |
| FAM131A | −0.92 | 0.66 | 1.03 | 0.35 | 0.33 | PIM2 | 0.39 | −0.20 | −0.06 | −0.39 | −0.09 | PTER | −0.06 | 0.11 | −0.19 | 0.13 | −0.09 |
| AP4E1 | 0.56 | −0.16 | −0.35 | −0.02 | −0.24 | AC027811.1 | −0.97 | −0.11 | 1.48 | 0.27 | 1.48 | AC141424.1 | 0.31 | −0.69 | −0.54 | −1.33 | −0.87 |
| COL25A1 | −1.67 | 0.98 | 0.99 | 0.70 | −0.11 | C10orf82 | −0.82 | 0.22 | 0.59 | 0.57 | 0.27 | AC011383.1 | 0.48 | −0.46 | −0.33 | 0.63 | 0.52 |
| NBPF12 | −0.62 | 0.26 | 0.40 | 0.07 | −0.05 | KC6 | −0.85 | 0.93 | −0.26 | 0.79 | −0.92 | AP002360.3 | −0.36 | 1.25 | −0.03 | 0.39 | −0.43 |
| FAM156B | −1.39 | 0.82 | 1.09 | 0.85 | 0.68 | ADAMTS3 | −0.40 | −0.01 | 0.36 | −0.11 | 0.12 | SALL4 | 0.16 | −0.13 | −0.91 | 0.43 | −0.37 |
| 7-Mar | 0.71 | −0.20 | −0.46 | −0.14 | −0.37 | AC021517.2 | −1.18 | −0.04 | −0.24 | −1.07 | −0.14 | AC100860.1 | 1.11 | 0.00 | −1.16 | 0.58 | −0.20 |
| HIST1H2BF | 1.67 | −0.94 | −1.56 | −0.36 | −0.75 | AC005588.1 | −1.78 | 0.90 | 1.67 | 0.08 | 0.80 | RNU6-817P | 0.33 | −0.96 | 0.00 | 0.14 | 0.96 |
| BLM | 1.26 | −1.03 | −1.30 | −0.18 | −0.23 | AC010157.2 | −0.99 | 0.48 | −0.28 | 0.09 | 0.56 | AL160191.3 | 0.40 | −0.33 | −2.22 | 0.17 | −1.40 |
| AL353743.1 | −0.88 | 0.71 | 0.81 | 0.21 | −0.02 | RNU6-401P | −1.61 | −0.47 | 1.03 | −1.31 | 0.35 | LINC01411 | 0.27 | 0.00 | −1.50 | −0.55 | −0.87 |
| P4HB | 0.73 | −0.29 | −0.69 | −0.06 | −0.48 | DNAJC15 | 0.25 | −0.12 | 0.07 | −0.26 | −0.21 | CCR6 | 0.32 | 0.37 | −0.03 | −0.11 | −0.10 |
| BBS2 | −0.81 | 0.47 | 0.86 | 0.38 | 0.41 | AP001363.2 | −0.56 | 0.70 | 0.39 | 0.58 | 0.28 | DEFB109B | −0.33 | 0.36 | 1.96 | 0.59 | 0.63 |
| DKC1 | 0.86 | −0.53 | −0.75 | −0.11 | −0.27 | AL136304.1 | 0.90 | −0.38 | −0.03 | 0.62 | 0.27 | RNU6-1100P | 1.11 | 1.45 | −2.41 | 0.92 | −1.30 |
| RADIL | −1.30 | 0.76 | 1.02 | 0.55 | −0.11 | AL442067.2 | 0.84 | −0.32 | −0.41 | 0.26 | 0.02 | AC005042.3 | −0.84 | 0.94 | 1.16 | 0.74 | 0.72 |
| SNCG | −1.34 | 0.62 | 0.99 | 0.37 | 0.15 | SPINK2 | 1.13 | −0.19 | −0.56 | 0.29 | 0.12 | AC023796.2 | 0.84 | −1.37 | 0.37 | −1.66 | 0.82 |
| PARP12 | 0.91 | −0.63 | −0.77 | −0.34 | −0.21 | AP000251.1 | −0.82 | −0.02 | 0.52 | −0.02 | 0.97 | LINC02033 | 0.20 | −0.30 | −0.25 | −0.07 | −0.17 |
| OR1S1 | −2.78 | 1.26 | 2.35 | 1.37 | −0.44 | AL079352.1 | −2.12 | −0.19 | −0.92 | 1.28 | −0.56 | AL157791.2 | 0.15 | −0.13 | −0.46 | −0.12 | 0.03 |
| HAT1 | 0.87 | −0.40 | −0.61 | −0.21 | −0.51 | AC011524.1 | −1.40 | 0.65 | −1.87 | 1.97 | −0.85 | RXFP2 | −0.38 | −0.21 | −2.06 | 0.23 | −2.90 |
| STK32A | −1.41 | 0.82 | 1.22 | 0.37 | 0.97 | CFDP1 | −0.12 | 0.11 | 0.11 | −0.09 | −0.06 | AC007377.1 | −0.43 | −0.63 | 1.48 | −0.99 | 1.49 |
| COBL | −1.10 | 1.07 | 1.07 | 0.41 | 0.15 | PLAT | 0.44 | −0.54 | −1.54 | 0.59 | −0.21 | AC017083.3 | 0.60 | 0.47 | −0.04 | 0.85 | −0.07 |
| PABPC1 | 0.85 | −0.34 | −0.60 | −0.06 | −0.29 | AC009305.1 | 1.31 | −2.57 | −0.95 | −0.39 | 2.01 | PDE4C | −0.90 | 0.53 | 0.61 | 1.09 | 1.09 |
| FOX06 | −1.55 | 1.05 | 1.32 | 0.60 | 0.46 | RN7SKP26 | 1.01 | −0.54 | −1.52 | 0.25 | 0.50 | AC023310.4 | −0.93 | 1.23 | 0.48 | 2.03 | −1.73 |
| MRPL58 | 0.83 | −0.39 | −0.63 | −0.06 | −0.34 | POU2F2 | −0.36 | −0.27 | 0.13 | −0.29 | 0.11 | AC025171.3 | 0.25 | −0.91 | −0.79 | −0.24 | −0.20 |
| PLIN3 | 0.88 | −0.41 | −1.00 | 0.00 | −0.66 | ENTPD2 | −0.32 | 0.27 | −0.03 | 0.37 | 0.09 | SLC37A4 | 0.08 | −0.14 | −0.29 | 0.15 | 0.09 |
| HAAO | −1.01 | 0.22 | 0.85 | 0.33 | 0.66 | AC091046.2 | 0.79 | −0.68 | −0.17 | 0.04 | 0.86 | LINC00445 | −0.53 | −0.80 | −0.42 | 0.74 | −0.35 |
| PNPT1 | 0.62 | −0.43 | −0.49 | −0.21 | −0.20 | FUCA2 | 0.27 | −0.27 | −0.04 | −0.17 | −0.09 | AC026167.1 | −0.62 | −1.28 | 1.08 | −1.54 | −0.37 |
| AC006019.1 | −2.31 | 0.91 | 2.01 | 0.37 | 0.46 | FBXW7-AS1 | 0.96 | 0.06 | −0.16 | 0.26 | −0.38 | LINC02222 | 0.56 | −0.79 | −1.81 | 0.46 | 0.06 |
| AC126773.3 | 2.28 | −1.80 | −3.42 | −0.51 | −1.93 | PIGS | 0.15 | 0.05 | −0.22 | 0.05 | −0.27 | AC012313.4 | 0.14 | −0.29 | 0.42 | 0.17 | 0.63 |
| OR7E47P | −1.60 | 1.13 | 1.97 | 0.67 | 0.90 | RNF144A | 0.29 | −0.21 | −0.36 | −0.34 | −0.37 | IL10RB | 0.12 | 0.12 | 0.19 | −0.04 | −0.05 |
| KLK7 | 1.62 | −0.42 | −0.58 | 0.16 | −0.68 | AL032819.2 | −1.12 | 1.78 | 0.22 | 1.42 | −0.16 | RRAD | 0.18 | −0.41 | −1.09 | 0.08 | −0.36 |
| LIFR-AS1 | −1.72 | 1.01 | 1.67 | 0.64 | 0.90 | PTP4A1 | 0.53 | −0.25 | −1.37 | 0.32 | −0.50 | AC073487.1 | −0.12 | −0.21 | 0.24 | −0.17 | 0.31 |
| RPS26 | 1.01 | −0.68 | −0.78 | −0.04 | −0.03 | AC018697.1 | −1.07 | −0.48 | −0.18 | 0.85 | 1.15 | AC090415.1 | −0.88 | −0.05 | 1.30 | 0.12 | 0.62 |
| SCARNA6 | −0.84 | 0.62 | 0.87 | 0.13 | −0.02 | HADHAP1 | −0.52 | 0.54 | 1.14 | 0.10 | −0.13 | ADGRG7 | −0.30 | 2.20 | 0.43 | 0.78 | −1.00 |
| DCTN2 | 0.54 | −0.13 | −0.46 | −0.07 | −0.42 | MIR4644 | 0.65 | −0.34 | 0.22 | −0.76 | −0.29 | RPL3L | 0.23 | −1.48 | −1.07 | 0.30 | 0.59 |
| G8412 | 1.11 | −0.63 | −0.58 | −0.19 | −0.08 | COL6A5 | 0.77 | −0.65 | 0.31 | −0.40 | 0.56 | ERVV-1 | 0.80 | −0.67 | −2.35 | −0.43 | −1.15 |
| DIAPH1 | 0.68 | −0.36 | −0.80 | −0.09 | −0.38 | RN7SL745P | 0.80 | −0.47 | 0.42 | −0.07 | 1.01 | SSTR1 | −0.22 | 0.36 | 0.28 | 1.00 | 0.59 |
| HNRNPAB | 0.79 | −0.57 | −0.65 | −0.19 | −0.06 | ATP5MF-PTCD] | 1.09 | 0.08 | 0.45 | −0.16 | 0.90 | AC093422.2 | −0.23 | −0.64 | 1.64 | −0.26 | 1.38 |
| CMAHP | −1.04 | 0.61 | 1.17 | 0.00 | 0.21 | RP11-640M9.2 | −0.19 | −0.17 | 0.18 | −0.10 | 0.32 | MIA | −0.45 | −0.72 | −0.06 | −0.08 | 0.24 |
| GULOP | −2.27 | 1.61 | 2.69 | 0.87 | 1.36 | SMARCE1P2 | −0.97 | −0.42 | 0.61 | 0.52 | 1.54 | RNU5F-3P | −0.39 | 0.79 | 1.37 | −0.41 | 0.65 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| ORMDL3 | −0.82 | 0.55 | 0.74 | 0.25 | 0.25 | AC012414.7 | 1.19 | −1.05 | −1.29 | 1.21 | 1.76 | AC012442.1 | −0.18 | 0.39 | 0.02 | −0.15 | −0.51 |
| PRKAA2 | −1.54 | 0.82 | 1.33 | 0.38 | 0.22 | AC025271.2 | −0.83 | 0.99 | 1.55 | 0.01 | 0.93 | AC089999.2 | −0.18 | −0.10 | 1.06 | −0.25 | 0.13 |
| NDRG4 | 1.21 | 0.26 | −0.66 | 0.56 | −0.60 | AL354861.3 | −1.07 | −0.45 | 1.75 | 0.78 | 1.31 | AL357153.1 | 0.42 | −0.87 | −1.88 | 1.03 | −0.71 |
| GINS3 | 1.27 | −0.35 | −1.52 | 0.04 | −0.90 | SPART-AS1 | −0.67 | 0.52 | 0.23 | 0.54 | −0.37 | ATP5F1AP2 | 0.56 | −0.96 | 0.61 | 0.25 | −0.88 |
| HEATR4 | −1.25 | 0.59 | 0.85 | 0.44 | 0.42 | AL139396.1 | −0.42 | 0.01 | 0.86 | 0.22 | 0.51 | MEIS1-AS3 | 0.35 | −0.80 | 0.10 | 0.79 | 0.10 |
| GHITM | 0.89 | −0.24 | −0.72 | −0.11 | −0.52 | EHMT2-AS1 | −0.79 | 0.48 | −0.03 | −0.29 | −0.45 | CSN1S2AP | 0.70 | −0.09 | −2.23 | 0.25 | −2.46 |
| AURKA | 1.45 | −1.09 | −1.68 | −0.30 | −0.25 | [MJD7-PLA2G4] | −0.44 | 0.50 | 0.15 | 0.44 | 0.24 | RNU6-1309P | 0.26 | 0.64 | 1.58 | −0.30 | −0.52 |
| CDK7 | 0.94 | −0.32 | −0.66 | −0.20 | −0.50 | BCKDHA | −0.36 | −0.14 | 0.37 | −0.21 | 0.27 | AP001469.3 | 0.09 | −0.10 | 0.23 | −0.02 | 0.26 |
| CBX2 | 1.40 | −0.62 | −1.24 | 0.25 | −0.24 | G4361 | 1.21 | −0.09 | 1.03 | −0.09 | −0.77 | CLC | 0.73 | −1.63 | −2.01 | −0.80 | −1.37 |
| LRRC8A | 0.82 | −0.20 | −0.89 | −0.29 | −0.69 | KCNJ11 | −0.70 | 0.84 | 0.13 | 1.16 | −0.44 | AC087318.1 | −0.34 | −0.10 | 1.11 | −0.03 | 0.05 |
| AL109613.1 | −1.22 | 0.92 | 1.33 | 0.43 | 0.44 | RNU6-479P | 0.63 | −0.70 | −0.21 | −0.51 | 0.09 | NRBF2P1 | 0.74 | −0.19 | −2.01 | 1.18 | −1.08 |
| NBPF14 | −0.55 | 0.47 | 0.48 | 0.10 | 0.36 | AC079089.2 | −0.75 | 0.19 | −0.10 | 0.41 | 0.58 | AL135908.1 | 0.73 | 0.84 | −2.01 | 0.11 | −2.84 |
| BAZIA | 0.84 | −0.54 | −0.84 | −0.19 | −0.41 | RPL9P29 | −0.54 | 0.30 | 1.13 | 0.45 | 0.81 | AL583804.1 | 0.91 | −0.06 | −1.62 | −0.33 | −2.20 |
| NABP2 | 0.76 | −0.34 | −0.65 | −0.06 | −0.43 | MIR4482-1 | 0.67 | −0.16 | 0.02 | 0.00 | −0.49 | AC011773.2 | −0.61 | −0.22 | 1.54 | −0.23 | 1.70 |
| CHCHD4 | 0.86 | −0.42 | −0.71 | −0.20 | −0.49 | PDPK2P | −0.42 | 0.11 | 0.53 | −0.12 | 0.40 | AC007528.1 | 0.43 | 0.02 | 0.26 | 0.77 | −0.99 |
| SNRPC | 0.85 | −0.46 | −0.70 | −0.24 | −0.51 | PCDHGA1 | −0.57 | 0.17 | 0.73 | −0.02 | 0.13 | RPL3P10 | 0.38 | −1.01 | −0.04 | −0.07 | −1.05 |
| G3BP1 | 0.74 | −0.41 | −0.55 | −0.09 | −0.16 | PCDHB13 | −0.28 | 0.50 | 0.55 | 0.04 | −0.35 | ACTBP14 | −0.46 | −0.14 | 1.70 | −0.33 | 0.95 |
| MIEF2 | −0.85 | 0.55 | 0.60 | 0.51 | 0.28 | FTLP3 | −0.69 | 0.04 | 1.03 | −0.40 | 0.64 | BEND2 | 0.36 | 0.78 | −1.59 | 0.81 | −2.25 |
| MCM3 | 0.87 | −0.75 | −0.81 | −0.28 | −0.17 | GAPDHP1 | 0.55 | −0.15 | −0.72 | −0.18 | −0.50 | AC087588.1 | −0.65 | −0.36 | 0.18 | −1.13 | 1.96 |
| AP000439.2 | −3.40 | 2.13 | 2.22 | 1.91 | 0.37 | AC105118.1 | −1.32 | 0.98 | 0.09 | 0.25 | 0.32 | CR392039.2 | 0.26 | 0.69 | 0.16 | 0.80 | −0.03 |
| PCDHGB3 | −1.12 | 0.52 | 1.00 | 0.38 | 0.49 | BRS3 | −1.13 | −0.58 | −0.50 | −0.14 | −0.83 | AC011005.1 | −0.42 | 0.72 | −0.89 | 1.53 | −0.49 |
| AL513477.1 | −1.70 | 0.35 | 1.44 | 0.21 | 0.27 | AC140061.1 | −1.86 | 0.27 | 1.45 | 0.44 | 1.52 | AL035425.4 | −0.77 | −0.74 | 1.40 | −1.07 | 0.32 |
| RIN2 | 0.52 | −0.24 | −0.44 | −0.02 | −0.22 | SLC10A5 | −0.48 | 0.43 | 0.09 | 0.20 | 0.02 | LINC02186 | −0.56 | −0.72 | 0.55 | 0.88 | 0.62 |
| NAT8L | −2.13 | 1.76 | 1.55 | 1.07 | 0.04 | RNA5SP197 | 1.10 | −0.88 | −0.19 | −0.01 | −0.07 | LINC00865 | −0.24 | −0.44 | 0.44 | 0.25 | 0.61 |
| LINC01252 | −1.14 | 0.32 | 0.84 | 0.16 | 0.35 | ST8SIA1 | −0.34 | 0.07 | 0.05 | 0.18 | 0.23 | ACTG1P9 | −0.24 | −0.41 | −0.19 | 0.61 | 0.20 |
| G29699 | −1.55 | 0.28 | 1.79 | −0.37 | 0.43 | AL117341.1 | 0.63 | 0.22 | −0.03 | 0.10 | −0.04 | AC003070.2 | −0.49 | −1.24 | −0.26 | −0.61 | −0.21 |
| KRT17P2 | 3.37 | −2.14 | −2.88 | −0.85 | −1.81 | CRAMP1 | −0.17 | 0.10 | −0.05 | 0.12 | 0.01 | AC130689.1 | 0.19 | −0.29 | −0.01 | 0.06 | 0.59 |
| RN7SL85P | −3.23 | 1.79 | 0.69 | 2.17 | 1.13 | MIR5188 | 1.31 | −1.51 | −1.91 | −0.57 | −1.26 | FKBP8 | 0.07 | 0.10 | 0.00 | 0.02 | −0.11 |
| MOK | −0.71 | 0.48 | 0.57 | 0.20 | 0.10 | C16orf95 | −0.42 | −0.06 | 0.01 | −0.32 | 0.29 | AL365194.1 | −0.46 | −0.88 | 2.30 | 0.11 | 1.81 |
| AIMP1 | 0.65 | −0.33 | −0.53 | −0.14 | −0.29 | SNORA16B | 0.74 | −0.20 | 0.06 | 0.25 | 0.60 | LINC01487 | −0.53 | −0.63 | −0.59 | 1.55 | 0.52 |
| FAM89A | 1.11 | −0.50 | −0.90 | −0.23 | −0.83 | AC109597.1 | 0.49 | −0.73 | 0.28 | −0.21 | 0.52 | AC005084.1 | 0.71 | −0.18 | −1.84 | 0.53 | −1.41 |
| CTB-178M22.2 | 2.21 | −0.97 | −1.97 | −0.35 | −0.58 | MRPL55 | 0.17 | −0.01 | −0.19 | 0.01 | −0.32 | AP002807.1 | −0.13 | −0.71 | −0.47 | −0.11 | 0.34 |
| SLC2A4 | −1.67 | 0.92 | 1.06 | 0.40 | 0.22 | LRRC4B | −0.60 | 0.68 | −0.06 | 0.76 | −0.01 | AC090424.1 | −0.46 | −0.30 | 2.74 | −0.21 | 1.40 |
| PRKDC | 0.85 | −0.56 | −0.62 | −0.19 | −0.19 | AL807757.1 | 0.65 | −0.09 | −0.61 | 0.25 | −0.32 | AC145285.6 | 0.12 | −0.31 | −0.02 | −0.14 | 0.13 |
| DLG2 | −1.12 | 0.82 | 1.57 | 0.40 | 0.45 | FPR2 | 1.02 | −1.36 | −3.84 | −0.33 | −2.73 | OR4C14P | −1.00 | −0.45 | −0.05 | −0.30 | −0.37 |
| SMIM12 | 0.63 | −0.34 | −0.53 | −0.13 | −0.27 | AC005479.2 | −0.50 | −0.10 | 0.91 | 0.11 | 0.40 | MRGPRX1 | −0.76 | −0.26 | −1.51 | 1.50 | −2.21 |
| LIPH | −1.33 | 0.47 | 1.40 | 0.19 | 0.70 | AC073130.1 | −0.65 | −0.06 | 0.29 | −0.26 | −0.04 | AC011491.3 | −0.36 | −1.93 | 0.22 | −0.39 | 1.01 |
| KAT8 | −0.53 | 0.23 | 0.35 | 0.18 | 0.31 | SLC25A6P3 | 0.74 | −0.66 | −2.33 | −0.16 | −0.90 | RN7SKP208 | −1.13 | 0.75 | 0.80 | −0.49 | −0.68 |
| MAN2A1 | 0.61 | −0.21 | −0.25 | −0.16 | −0.25 | AC012568.1 | 0.52 | −0.67 | −0.41 | −0.30 | 0.07 | ERVV-2 | 0.82 | −0.63 | −0.52 | 1.59 | −0.65 |
| PLIN4 | −3.11 | 3.12 | 1.89 | 1.75 | −0.01 | GK-AS1 | 0.60 | −1.54 | 0.25 | −0.65 | 0.09 | AC017071.1 | −0.12 | 0.44 | 0.21 | 0.07 | 0.09 |
| P2RY2 | 1.45 | −0.81 | −1.17 | −0.11 | −0.10 | SLC12A3 | 0.88 | −1.52 | −0.69 | −0.36 | 0.39 | NEIL2 | −0.05 | 0.00 | 0.05 | 0.08 | 0.08 |
| FAM210A | 0.73 | −0.48 | −0.67 | −0.19 | −0.19 | CSMD2-AS1 | 1.02 | −0.62 | −0.32 | −0.68 | −0.23 | AC106865.1 | 0.30 | 0.01 | −1.93 | −0.13 | −1.70 |
| SMIM15 | 0.90 | −0.40 | −0.71 | −0.13 | −0.34 | AC006063.1 | −1.32 | 1.28 | 0.78 | 0.35 | −0.66 | AC119751.3 | −0.34 | −0.99 | 2.33 | −0.56 | 2.58 |
| SCGB2B2 | −1.33 | 0.53 | 1.15 | −0.04 | 0.55 | RN7SL409P | −0.53 | 0.04 | −0.22 | −0.17 | −0.04 | STX8P1 | −0.40 | 0.69 | 1.36 | −0.55 | −0.10 |
| SEMA4B | 1.18 | −0.40 | −1.06 | 0.00 | −0.46 | NIP7P2 | −1.80 | −0.57 | 1.78 | −1.32 | −0.54 | RPL7AP53 | 1.14 | −0.45 | −1.55 | −0.62 | 2.42 |
| CDKN1A | 1.05 | −0.55 | −1.29 | −0.38 | −1.13 | DIO2-AS1 | −0.77 | −0.91 | −0.12 | 0.34 | 0.55 | MANEAL | −0.15 | 0.15 | −0.25 | 0.26 | −0.23 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| HNRNPCP6 | −1.78 | 0.77 | 1.36 | 0.76 | 0.48 | PRR34 | −0.39 | 0.63 | −0.12 | 0.54 | −0.04 | AP000866.4 | −0.35 | 0.44 | 2.62 | 0.17 | 1.08 |
| RHOD | 1.45 | −0.45 | −1.18 | 0.00 | −1.00 | CTAGE12P | −1.12 | −0.59 | −0.02 | −0.10 | −0.95 | AL592490.1 | 0.68 | −0.31 | −0.94 | −0.73 | −1.26 |
| AK9 | −0.82 | 0.56 | 0.91 | 0.17 | 0.21 | ATP2B1 | 0.21 | −0.25 | −0.34 | −0.07 | −0.21 | AC110799.1 | 0.92 | −0.52 | −1.72 | 1.97 | −2.32 |
| IRS2 | −1.14 | 0.82 | 0.66 | 0.32 | 0.05 | AC002428.1 | −1.66 | −1.55 | 2.01 | −0.65 | 2.02 | AP006287.1 | −0.44 | 0.32 | 0.95 | −0.13 | −1.32 |
| STAG3 | −1.04 | 0.70 | 0.70 | 0.49 | 0.08 | AC025423.3 | −1.14 | 1.40 | 1.04 | 0.98 | 0.05 | RNU6-5P | −0.19 | −0.21 | 0.15 | −0.04 | −0.01 |
| ITFG2-AS1 | −1.54 | 0.74 | 1.11 | 0.20 | 0.37 | NR2F1-AS1 | −0.43 | 0.08 | 0.87 | 0.07 | 0.06 | LINC02407 | −0.40 | −0.27 | −1.49 | −0.42 | −0.40 |
| CD47 | 1.00 | −0.48 | −0.87 | −0.11 | −0.46 | AC012513.3 | 0.31 | −0.16 | 0.03 | −0.16 | 0.07 | RNF157-AS1 | −0.36 | 0.89 | −0.68 | 0.16 | −0.71 |
| MRPL47 | 0.91 | −0.58 | −0.54 | −0.32 | −0.36 | LINGO3 | −0.54 | −0.54 | 0.28 | 0.16 | 0.34 | C14orf177 | 0.46 | −0.89 | −2.43 | −0.18 | −0.56 |
| MY05C | −1.06 | 0.82 | 1.02 | 0.42 | 0.14 | Clorf21 | 0.26 | 0.07 | −0.11 | 0.13 | −0.08 | AC006237.1 | −0.31 | −0.38 | −0.23 | −0.54 | 0.02 |
| PCLO | −1.25 | 0.69 | 1.32 | −0.09 | −0.05 | CEBPA-DT | −0.82 | 0.72 | −0.39 | 1.21 | −0.46 | AC009318.3 | −0.10 | −0.04 | 0.43 | 0.09 | 0.53 |
| CCND2 | 1.05 | −0.77 | −1.15 | −0.07 | −0.64 | AC105760.2 | −0.57 | 0.44 | 1.31 | 0.12 | 0.76 | NR1D2 | −0.07 | 0.34 | 0.46 | 0.07 | −0.32 |
| ADHFE1 | −1.16 | 0.47 | 0.98 | 0.51 | 0.44 | POPDC3 | 0.77 | −0.80 | −0.86 | −0.26 | 0.17 | AL365199.1 | 0.54 | −0.12 | −0.96 | 0.70 | −0.95 |
| DDX60L | 1.02 | −0.76 | −0.68 | −0.53 | −0.31 | AP4M1 | −0.18 | 0.14 | −0.15 | 0.31 | 0.10 | G11279 | 0.33 | −0.73 | −0.54 | −0.10 | 0.47 |
| NUMA1 | −0.45 | 0.35 | 0.28 | 0.21 | 0.07 | AC099506.1 | 0.42 | −0.05 | −0.36 | 0.01 | −0.13 | AP001604.1 | −0.26 | −0.40 | −0.63 | 1.29 | 0.91 |
| LRRC8D | 1.00 | −0.34 | −0.64 | −0.09 | −0.31 | RN7SL220P | 0.40 | −0.62 | −0.56 | 0.00 | 0.09 | AC100771.1 | 0.38 | −1.17 | −0.06 | −0.31 | 0.11 |
| POP1 | 0.95 | −0.62 | −0.86 | −0.30 | −0.21 | ATP6VOE1P1 | 0.56 | −0.23 | 0.14 | 0.03 | −0.16 | LINC01505 | −0.20 | −0.54 | −0.48 | 0.20 | 0.15 |
| OSR2 | −1.68 | 1.59 | 2.09 | 0.21 | 0.21 | AC128714.1 | −0.77 | 0.82 | 1.90 | 0.40 | 1.07 | AC008680.1 | −0.32 | −2.00 | −1.76 | −0.06 | 0.10 |
| HIST1H2BM | 1.95 | −1.16 | −1.66 | −0.51 | −0.92 | ENPP7P7 | −0.68 | 0.65 | 1.28 | 0.13 | 0.15 | AC004637.1 | 0.22 | 0.74 | −0.21 | 0.50 | −0.49 |
| PTCH1 | −1.01 | 0.72 | 1.02 | 0.48 | 0.32 | MRPL2P1 | −1.20 | −0.33 | −0.57 | 0.42 | 0.66 | DNTTIP1 | −0.04 | 0.06 | −0.06 | −0.04 | −0.07 |
| DSP | 1.28 | −0.17 | −0.91 | 0.04 | −0.82 | RPL21P50 | −1.75 | −0.27 | 0.43 | 0.72 | 0.45 | AC023090.2 | −0.09 | 0.12 | 0.30 | 0.13 | 0.18 |
| H6PD | −0.70 | 0.39 | 0.66 | 0.22 | 0.21 | CHRDL2 | 0.77 | −0.76 | −1.19 | −1.05 | −1.29 | AC107886.1 | −0.73 | −0.69 | −0.17 | 0.40 | 1.16 |
| ATP6V1D | 0.75 | −0.25 | −0.60 | −0.11 | −0.44 | AC114811.2 | −0.47 | 0.38 | 0.76 | 0.21 | 0.05 | KLHL17 | −0.11 | −0.18 | −0.26 | 0.05 | 0.36 |
| COX5A | 0.83 | −0.25 | −0.43 | −0.15 | −0.27 | CCT4P2 | −0.90 | −0.58 | 1.69 | −0.89 | 1.47 | AC091932.3 | −0.64 | −0.08 | −0.49 | 1.59 | 1.35 |
| AGBL4 | −1.96 | 0.33 | 0.30 | 0.07 | −0.29 | AC005871.1 | −1.25 | 0.50 | 1.40 | −0.26 | −0.17 | AC069368.1 | 0.61 | 0.01 | −1.71 | 0.13 | −1.27 |
| BACH2 | −1.14 | 0.76 | 1.24 | −0.02 | 0.15 | DICER1-AS1 | −0.32 | 0.00 | 0.45 | 0.24 | 0.46 | AC005703.2 | 1.14 | −1.47 | −1.86 | 0.04 | −0.37 |
| AKT1S1 | 0.48 | −0.19 | −0.41 | −0.05 | −0.18 | FBXO33 | 0.23 | 0.11 | −0.18 | −0.15 | −0.44 | LINC02539 | 0.64 | −0.72 | −0.31 | −0.59 | −0.85 |
| RPL26L1 | 1.37 | −0.82 | −0.60 | −0.83 | −0.49 | AL049812.1 | −1.11 | 1.58 | 1.33 | 0.68 | −0.26 | PCBP2-OT1 | 0.16 | 0.28 | 0.23 | 0.23 | 0.00 |
| BOC | −1.23 | 1.06 | 1.09 | 0.71 | 0.02 | SMIM34B | 0.66 | −0.25 | −1.29 | 0.11 | −1.58 | CFLAR-AS1 | −0.06 | −0.16 | −0.07 | −0.05 | 0.09 |
| SND1 | 0.55 | −0.34 | −0.47 | −0.15 | −0.17 | AC025627.3 | −0.79 | 0.67 | −0.23 | 0.71 | −0.45 | KCNK5 | −0.14 | 0.66 | −0.20 | 0.48 | 0.09 |
| MATN2 | −0.95 | 0.86 | 0.74 | 0.40 | 0.00 | AL445523.1 | −0.73 | 0.20 | 1.18 | −0.26 | 0.48 | G6PC3 | 0.07 | 0.00 | 0.08 | −0.21 | 0.02 |
| ARPC1A | 1.17 | −0.51 | −1.17 | −0.25 | −0.84 | CACNG4 | −0.79 | 0.31 | 0.23 | 0.40 | −0.60 | LINC01690 | −0.68 | 0.19 | 0.58 | 1.04 | 1.35 |
| AL049555.1 | 1.90 | −0.50 | −0.98 | −0.09 | −0.70 | AC006128.1 | −0.57 | 0.34 | 0.68 | 0.34 | 0.02 | RASGRP2 | −0.14 | −0.39 | 0.20 | −0.40 | 0.20 |
| CIAO2A | 0.73 | −0.40 | −0.49 | −0.21 | −0.21 | OR51A10P | −1.20 | 1.34 | 0.75 | 1.12 | 0.64 | AL627230.3 | −0.80 | −1.53 | 0.23 | −0.96 | 0.17 |
| FMO5 | −1.14 | 0.86 | 1.70 | 0.26 | 0.53 | DDX54 | 0.18 | −0.20 | −0.28 | −0.03 | −0.01 | AL035045.1 | −0.45 | −0.89 | 0.70 | 1.16 | −0.05 |
| CTPS1 | 0.92 | −0.78 | −1.01 | −0.20 | −0.12 | RPL3 | 0.26 | 0.11 | 0.12 | −0.08 | −0.19 | LPIN2 | −0.08 | −0.23 | −0.11 | −0.07 | −0.03 |
| DENR | 0.69 | −0.38 | −0.49 | −0.24 | −0.20 | AF131215.1 | 0.42 | −0.08 | −0.29 | 0.17 | 0.04 | AC113607.1 | 0.67 | 0.37 | 0.76 | 1.07 | 1.50 |
| DNAJC5 | 0.80 | −0.39 | −0.80 | −0.02 | −0.33 | GID4 | 0.28 | 0.12 | 0.01 | −0.01 | −0.30 | DWORF | −0.83 | −0.27 | 0.22 | 0.44 | 0.90 |
| RNF222 | 1.62 | −0.39 | −1.11 | −0.40 | −1.10 | AC079209.1 | 1.61 | −1.72 | −0.83 | −0.52 | −0.73 | C2orf83 | −0.26 | −0.72 | −0.76 | −0.18 | −0.63 |
| LONRF2 | −1.55 | 0.92 | 1.28 | 0.63 | 0.53 | AL359853.2 | 1.24 | −0.49 | −1.40 | 0.67 | 0.00 | AC016954.1 | 0.27 | 0.17 | 0.29 | −0.18 | −0.85 |
| S100A14 | 1.90 | −0.70 | −1.23 | −0.22 | −0.84 | AC104996.2 | −0.79 | 0.97 | −0.31 | 1.17 | −0.19 | KRT8P35 | 0.43 | −0.25 | −0.09 | 0.81 | −0.49 |
| ABHD17C | 1.18 | −0.43 | −0.88 | −0.09 | −0.51 | CENPS | 1.11 | −0.88 | −1.88 | 0.06 | −1.75 | DNAAF4 | −0.22 | −0.07 | 1.28 | 0.15 | 0.59 |
| PCDHGA4 | −1.39 | 0.66 | 1.08 | 0.61 | 0.32 | AC114878.2 | 0.74 | −0.62 | −1.25 | −0.03 | −0.39 | KIFC3 | 0.07 | −0.09 | −0.17 | −0.09 | −0.09 |
| SLC35A4 | 0.83 | −0.32 | −0.75 | −0.04 | −0.32 | CDKN2B | 0.29 | 0.26 | −0.22 | 0.21 | −0.45 | AC010203.2 | −0.32 | 0.10 | −0.26 | −0.06 | −0.61 |
| SH3PXD2A-AS1 | 1.47 | −0.57 | −1.28 | 0.10 | −0.54 | AL355472.3 | −0.66 | 0.33 | 0.99 | 0.28 | 0.74 | KIF18BP1 | 0.34 | 0.17 | −0.38 | −0.24 | −0.88 |
| HIST1H2AL | 1.88 | −1.19 | −1.48 | −0.61 | −0.75 | RNU6-123P | 0.65 | −0.34 | 0.13 | −0.08 | 0.42 | LINC01262 | 0.38 | −0.70 | −1.56 | 0.42 | −0.80 |
| MYL12B | 0.99 | −0.41 | −0.79 | −0.22 | −0.62 | RNU6-769P | 0.74 | 0.07 | −0.23 | 0.16 | 0.05 | LHFPL2 | 0.09 | −0.07 | −0.08 | −0.36 | −0.19 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| ADCY5 | −1.40 | 0.64 | 0.64 | 0.55 | 0.06 | PET100 | −0.47 | 0.35 | −0.16 | 0.69 | 0.15 | AL109755.1 | −0.44 | 0.53 | 0.68 | −0.80 | −0.34 |
| DSC3 | 1.76 | −0.34 | −1.09 | 0.13 | −0.72 | BX324167.1 | −1.98 | −0.19 | 4.82 | 2.15 | 4.89 | LINC00658 | 0.37 | −0.45 | −0.95 | 0.87 | −0.22 |
| AC134684.6 | −3.68 | 1.46 | 0.87 | 3.17 | 0.07 | AP000902.2 | 1.55 | −1.50 | −2.20 | −0.03 | −0.92 | AC021231.1 | −0.13 | 0.11 | 0.71 | −0.08 | 0.29 |
| SKA1 | 1.71 | −1.13 | −2.21 | −0.39 | −1.16 | AC245060.4 | −0.24 | −0.06 | 0.03 | −0.10 | 0.10 | AL445248.1 | −0.09 | −0.12 | −0.07 | −0.01 | −0.03 |
| B3GLCT | 0.83 | −0.47 | −0.78 | −0.25 | −0.35 | CHRM3-AS2 | −0.57 | 0.43 | 0.87 | 0.18 | 0.76 | PARP4P1 | −0.36 | 0.35 | 0.48 | 0.10 | 0.45 |
| BTG3 | 1.14 | −0.28 | −0.82 | 0.11 | −0.36 | ARL10 | −0.17 | 0.11 | 0.26 | 0.03 | 0.27 | AC096543.1 | −0.74 | −1.04 | 0.40 | 0.35 | 1.58 |
| G41367 | −1.63 | 0.89 | 1.73 | 0.78 | 0.38 | RPL13P4 | 0.60 | 0.01 | −0.58 | 0.35 | −0.14 | DBIL5P2 | 0.13 | −0.18 | −0.42 | 0.23 | −0.07 |
| GTF2F2 | 0.74 | −0.14 | −0.46 | −0.14 | −0.55 | CCDC71L | 0.41 | −0.49 | 0.01 | −0.52 | −0.31 | HELLPAR | 0.13 | −0.50 | −0.57 | −0.09 | −0.17 |
| C5 | −0.73 | 0.22 | 0.71 | 0.11 | 0.29 | CHIC2 | 0.22 | 0.00 | −0.06 | −0.18 | −0.30 | KDM4A-AS1 | −0.11 | 0.27 | 0.45 | 0.07 | 0.19 |
| PDIA6 | 0.90 | −0.55 | −0.64 | −0.46 | −0.39 | OTOP2 | 0.57 | 0.78 | 0.23 | 0.19 | −0.70 | RN7SL170P | −0.21 | 0.95 | 0.14 | 1.61 | 0.11 |
| DNM1 | −1.09 | 0.59 | 0.92 | 0.13 | 0.03 | AC018475.1 | 0.54 | 0.20 | −0.17 | −0.13 | −0.57 | RPS3AP54 | −0.37 | 0.30 | −2.70 | 1.59 | −1.07 |
| CADM3 | −1.44 | 0.59 | 1.39 | 0.16 | 0.23 | MAP3K10 | −0.29 | 0.16 | −0.16 | 0.21 | 0.12 | AL021937.1 | −0.21 | 0.60 | 0.21 | −0.07 | −0.59 |
| R3HCC1L | 0.61 | −0.29 | −0.72 | −0.12 | −0.37 | HOXB8 | −0.85 | −0.22 | 0.23 | 0.47 | 0.41 | ARL6IP6 | 0.08 | 0.05 | 0.02 | −0.03 | −0.05 |
| GABPB2 | −0.45 | 0.25 | 0.44 | 0.03 | 0.07 | IDH3G | −0.10 | −0.04 | −0.18 | 0.00 | 0.00 | RPL34P22 | −0.25 | 0.26 | 0.67 | −0.22 | −0.08 |
| PRMT1 | 0.70 | −0.35 | −0.74 | −0.21 | −0.29 | AL365181.3 | −0.75 | −0.14 | −0.26 | 0.16 | 0.61 | RPS7P9 | −0.67 | −0.63 | −0.61 | 1.57 | 0.65 |
| ADAM11 | −1.45 | 0.97 | 0.61 | 0.92 | 0.23 | COX5BP1 | 1.33 | 0.11 | −2.41 | 0.44 | −1.76 | AL445223.1 | −0.19 | −0.09 | 1.28 | −0.84 | 0.32 |
| KLF3-AS1 | −1.09 | 0.88 | 0.90 | 0.52 | 0.52 | AC107031.1 | 1.15 | −0.37 | −1.26 | −0.86 | −0.89 | LINC01648 | 0.73 | −1.93 | −2.30 | 0.43 | −1.29 |
| DCAF13 | 0.91 | −0.32 | −0.57 | −0.14 | −0.36 | C9 | 0.72 | −0.52 | 0.08 | 0.31 | 0.43 | AC008761.2 | −0.43 | 0.23 | 1.72 | −0.43 | 0.33 |
| RIMS1 | −1.98 | 1.08 | 1.90 | 0.55 | 1.11 | ARHGAP30 | −0.31 | 0.05 | 0.19 | −0.21 | 0.10 | AOC2 | 0.13 | 0.40 | −0.54 | 0.30 | −0.29 |
| MCL1 | 0.70 | −0.43 | −0.73 | −0.25 | −0.56 | AL356750.1 | −0.49 | −0.29 | 0.57 | −0.11 | 0.89 | MTND5P5 | −0.44 | −0.96 | 1.56 | 0.45 | 1.34 |
| LINC01094 | 1.72 | −0.52 | −0.41 | −0.07 | −0.25 | AL137002.1 | −1.04 | −0.62 | 1.31 | −0.40 | 0.50 | AL355864.2 | −0.29 | 0.25 | 0.68 | −0.33 | 0.69 |
| RACGAP1 | 1.01 | −0.75 | −0.99 | −0.22 | −0.37 | AC025180.1 | 0.84 | 0.24 | −0.26 | 0.02 | 0.06 | AC079328.1 | 0.28 | −1.31 | −1.08 | −0.85 | −1.32 |
| ABO | −1.26 | 0.79 | 1.02 | 0.54 | 0.08 | MIR4449 | −0.60 | 0.59 | −0.29 | 0.68 | −0.63 | G23125 | −0.47 | 0.81 | 3.54 | 0.45 | −0.26 |
| SEC13 | 0.61 | −0.38 | −0.48 | −0.28 | −0.25 | AC083829.1 | 1.33 | −1.17 | −1.00 | −0.95 | −0.74 | AL132796.3 | 0.34 | −0.60 | −0.78 | 0.27 | −0.71 |
| AP001046.1 | −3.01 | 1.14 | 2.14 | 0.16 | 1.16 | GCAT | 0.31 | −0.02 | −0.47 | 0.21 | −0.40 | SNORD28 | −1.12 | 1.53 | −0.45 | 0.66 | −0.85 |
| NIFK | 1.00 | −0.63 | −0.65 | −0.51 | −0.31 | ARL11 | 0.34 | −0.72 | −0.41 | −0.14 | 0.24 | RNU6-43P | 0.23 | −0.01 | 0.72 | −0.58 | −0.24 |
| LRP1B | −1.48 | 1.19 | 1.22 | 0.21 | 0.06 | ANKRD52 | 0.19 | −0.20 | −0.38 | 0.00 | 0.01 | AC023194.2 | 1.11 | −1.07 | −0.23 | 0.40 | 1.64 |
| AC091013.1 | −2.07 | 1.33 | 1.14 | 0.48 | 0.26 | PRED60 | 1.15 | −1.92 | −0.52 | −0.22 | 0.12 | PHF20 | −0.04 | −0.02 | −0.11 | −0.09 | −0.14 |
| HIST1H3C | 1.63 | −1.27 | −1.19 | −0.61 | −0.68 | AC092620.2 | 0.50 | −0.04 | −0.40 | 0.01 | −0.40 | LINC01734 | −0.44 | 0.28 | −0.37 | 0.06 | −0.49 |
| SDF2L1 | 1.13 | −0.73 | −1.06 | −0.27 | −0.23 | SLC43A3 | 0.26 | −0.23 | −0.26 | −0.12 | −0.14 | AL451081.2 | 0.56 | −1.66 | −0.01 | −0.24 | −0.65 |
| PCDH19 | −1.37 | 0.82 | 1.93 | 0.18 | 0.50 | DIP2A | −0.18 | 0.02 | −0.03 | 0.06 | 0.17 | SNORD41 | −0.15 | 0.10 | 0.27 | 0.30 | −0.56 |
| FABP5P2 | 2.64 | −0.59 | −1.93 | −0.06 | −1.40 | HM13-IT1 | −0.43 | −0.44 | 0.17 | −0.02 | 0.64 | AL356234.2 | 0.39 | −0.72 | −0.40 | −0.67 | −1.19 |
| AC004022.2 | −2.92 | 0.62 | 2.59 | 1.29 | 0.18 | MTND6P4 | −0.37 | 0.08 | 0.19 | 0.11 | 0.17 | AL033519.1 | −0.36 | 1.06 | 0.64 | 1.27 | 0.10 |
| BSDC1 | −0.51 | 0.41 | 0.28 | 0.19 | −0.10 | ST18 | 0.63 | −0.46 | −0.62 | 0.17 | −0.13 | LCN15 | −0.63 | −0.37 | 0.15 | −0.09 | −0.61 |
| FAM66C | −1.32 | 0.87 | 1.34 | 0.44 | 0.40 | NPHP3 | −0.23 | 0.10 | 0.38 | 0.14 | 0.24 | AC002558.3 | 0.06 | −0.20 | −0.05 | −0.06 | 0.06 |
| CHAD | −1.50 | 0.56 | 1.47 | 0.39 | 0.47 | MEF2C | −0.35 | 0.09 | 0.58 | 0.04 | 0.07 | AL627309.6 | 0.67 | −1.93 | −0.98 | 0.30 | 3.63 |
| MRPL32 | 0.85 | −0.37 | −0.73 | −0.11 | −0.39 | CLEC2B | 0.34 | −0.04 | −0.02 | 0.07 | −0.34 | NPM1P11 | −0.30 | 0.40 | 0.51 | −0.24 | −0.44 |
| CIP2A | 0.81 | −0.72 | −0.84 | −0.25 | −0.13 | MNAT1 | 0.20 | −0.12 | −0.14 | −0.19 | −0.01 | DUTP6 | −0.14 | −0.11 | 0.27 | 0.21 | 0.36 |
| LINC01534 | −1.22 | 0.57 | 1.08 | 0.27 | 0.46 | HSP90AA6P | 0.92 | −1.41 | −0.24 | −0.29 | 0.12 | PTTG1IP | −0.04 | 0.09 | 0.02 | −0.08 | −0.11 |
| LINC00842 | −1.37 | 0.60 | 0.93 | 0.52 | 0.48 | AC006030.1 | −0.81 | 0.36 | −0.45 | 0.25 | 0.03 | OR7A10 | −0.53 | −1.42 | −1.51 | −0.45 | −0.81 |
| LARP1 | 0.54 | −0.31 | −0.61 | −0.07 | −0.16 | HNRNPA1P29 | −0.91 | −0.56 | 2.01 | −1.26 | 0.45 | PLSCR5 | 0.91 | −0.76 | −1.31 | 0.65 | −2.89 |
| AURKAIP1 | 0.64 | −0.34 | −0.55 | −0.24 | −0.26 | AP001107.9 | −0.31 | 0.16 | 0.38 | 0.12 | 0.30 | AC008985.1 | −0.10 | −0.04 | 0.32 | −0.06 | 0.13 |
| CYB561A3 | −0.95 | 0.30 | 0.25 | 0.24 | 0.07 | PCDHA12 | −1.16 | 0.16 | −0.61 | 0.55 | −1.21 | AC091305.1 | 0.48 | 0.67 | −1.37 | 0.61 | −1.19 |
| KAT2A | −1.04 | 0.35 | 0.43 | 0.43 | 0.32 | METRN | −0.32 | 0.09 | 0.14 | −0.17 | 0.28 | AC026336.3 | 0.49 | −0.20 | −2.47 | 0.52 | −1.45 |
| ACYP2 | −0.60 | 0.29 | 0.54 | 0.16 | 0.33 | EIF5AP3 | −0.45 | 0.20 | 0.37 | 0.27 | 0.14 | AL096700.1 | −0.44 | −1.19 | −1.76 | −0.54 | 1.12 |
| STK26 | 0.86 | −0.23 | −0.80 | −0.17 | −0.84 | AC233723.1 | −0.60 | −0.21 | 0.68 | −0.27 | 0.33 | AC078899.1 | 0.29 | 0.35 | −1.15 | 1.00 | −1.42 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC113383.1 | −1.82 | 1.63 | 1.69 | 0.86 | −0.27 | AL356299.2 | 0.88 | −0.47 | −0.87 | 0.01 | 0.43 | RAB6D | 0.33 | 0.21 | −0.93 | −0.19 | −1.63 |
| CELF4 | −1.23 | 0.18 | 0.91 | 0.00 | 0.50 | SNORD70 | 0.68 | −0.61 | −0.15 | −0.16 | −0.12 | RNA5SP36 | −0.89 | 1.38 | −0.03 | 0.21 | −1.21 |
| CHEK1 | 1.08 | −0.98 | −1.30 | −0.22 | −0.39 | CIAPIN1P | −1.04 | −0.25 | 0.38 | 1.31 | 1.03 | MIR4252 | −0.85 | 0.87 | 2.05 | 0.49 | 1.10 |
| HM13 | 0.53 | −0.30 | −0.46 | −0.22 | −0.32 | AC004877.2 | −0.74 | 0.89 | 0.92 | −0.34 | 0.35 | AC095056.1 | 0.80 | 0.64 | −1.81 | 1.97 | −0.57 |
| AC040160.2 | −1.20 | 0.36 | 0.52 | 0.09 | 0.24 | CACNA1I | −0.67 | −0.69 | −0.40 | −0.08 | 0.02 | ERICH6-AS1 | −0.19 | −0.40 | −0.63 | 0.34 | −0.38 |
| PLK4 | 1.00 | −0.69 | −1.32 | −0.12 | −0.65 | CD5 | −0.34 | −0.09 | 0.69 | −0.19 | 0.51 | AC090515.3 | 0.95 | −2.08 | −1.05 | −0.98 | 1.01 |
| IPO7 | 0.81 | −0.43 | −0.60 | −0.24 | −0.37 | DUSP19 | −0.35 | 0.09 | 0.44 | −0.01 | 0.23 | AC005999.2 | 0.80 | 0.54 | −0.02 | 1.23 | −0.38 |
| RPN1 | 0.83 | −0.42 | −0.52 | −0.32 | −0.32 | SAG | −0.82 | −0.47 | −0.90 | 0.42 | −0.21 | MT-TG | −0.33 | 1.60 | −0.74 | 1.57 | −1.15 |
| G14609 | −3.26 | 2.66 | 2.96 | 1.30 | −0.66 | AC010525.2 | 1.95 | −1.07 | 0.37 | 0.06 | 1.05 | PLOD3 | −0.09 | −0.27 | −0.21 | −0.18 | −0.13 |
| PSMB1 | 0.77 | −0.34 | −0.55 | −0.12 | −0.41 | GPR157 | 0.29 | 0.05 | −0.04 | 0.09 | −0.16 | PAPSS2 | 0.11 | −0.18 | −0.18 | −0.20 | −0.29 |
| RGS9 | −1.31 | 0.28 | 0.83 | 0.28 | 0.63 | AL590006.1 | −0.42 | 0.42 | 0.20 | −0.01 | −0.15 | OSTCP5 | −0.34 | 1.29 | −0.51 | −0.09 | −0.35 |
| C19orf18 | −1.25 | 0.90 | 1.08 | 0.67 | 0.15 | AC120498.2 | −0.90 | 0.78 | 0.90 | 1.25 | −0.23 | MIR122HG | 0.41 | −0.99 | −0.69 | −0.11 | −0.80 |
| CCT4 | 0.82 | −0.41 | −0.44 | −0.23 | −0.21 | AL513523.2 | −0.46 | 0.67 | 0.87 | 0.17 | 0.23 | OR5H6 | 0.57 | −0.68 | −1.30 | 0.96 | 0.11 |
| SRGAP3 | −0.87 | 0.25 | 0.67 | 0.26 | 0.49 | C1QBPP2 | −0.64 | 0.08 | 1.23 | −0.02 | 1.01 | AC073592.7 | 0.16 | 0.20 | −0.79 | 0.00 | −0.74 |
| CXCR1 | 2.57 | −1.32 | −2.75 | −0.28 | −2.47 | G10846 | −0.72 | 0.82 | −0.78 | 0.74 | −0.97 | AC106799.2 | −0.52 | 0.38 | 0.15 | 1.22 | −1.77 |
| KRT13 | 3.32 | −1.65 | −5.08 | 1.48 | −1.94 | SMUG1 | −0.24 | 0.01 | 0.30 | 0.12 | 0.43 | AC104581.3 | −0.40 | −0.64 | −1.84 | 1.53 | 0.84 |
| CES4A | −1.37 | 0.92 | 1.50 | 0.66 | 0.55 | AC010157.1 | −1.40 | 0.57 | 1.89 | −1.16 | 1.20 | AC120338.1 | −0.47 | −1.14 | 0.66 | −0.42 | −0.50 |
| EEF1A1P30 | −1.09 | 0.66 | 0.97 | 0.22 | 0.15 | CHST7 | −0.37 | 0.02 | −0.03 | −0.16 | −0.28 | SNHG18 | 0.13 | −0.13 | 0.50 | −0.46 | 0.01 |
| RIOK1 | 0.70 | −0.42 | −0.56 | −0.31 | −0.28 | PAPOLB | −0.64 | 0.51 | 0.05 | 0.14 | −0.64 | AC022182.3 | 0.21 | 0.26 | −0.39 | 0.23 | −0.25 |
| G6732 | 3.59 | −2.34 | −1.65 | 0.40 | 2.09 | AC095033.1 | 0.57 | −0.65 | −0.26 | 0.26 | 0.05 | AL357094.1 | −0.61 | 0.64 | −0.26 | −0.61 | −0.82 |
| MYH7B | −1.07 | 0.56 | 0.71 | 0.37 | 0.19 | HVCN1 | −0.39 | 0.20 | 0.29 | 0.10 | −0.03 | GUSB | −0.03 | 0.05 | 0.00 | −0.05 | −0.13 |
| MACROD2-AS1 | −1.41 | 0.46 | 1.28 | 0.34 | 1.05 | FTOP1 | −0.47 | 0.01 | 0.92 | 0.27 | 0.56 | AFF2-IT1 | 0.55 | −1.20 | 1.45 | −0.78 | 0.47 |
| PHF1 | −0.89 | 0.33 | 0.50 | 0.32 | 0.25 | AC017083.4 | −1.73 | 1.66 | 2.42 | 0.93 | 1.57 | GPS1 | 0.04 | −0.06 | −0.24 | −0.04 | −0.08 |
| MIR29B2CHG | −0.87 | 0.60 | 0.92 | 0.37 | 0.37 | CRYZ | 0.27 | 0.02 | −0.19 | 0.29 | 0.40 | AC006326.1 | 0.53 | −0.84 | −1.36 | 1.36 | −0.09 |
| NOL3 | −1.07 | 0.62 | 0.87 | 0.43 | 0.44 | SIPA1L1 | 0.16 | −0.17 | −0.20 | −0.15 | −0.15 | RN7SL801P | 0.16 | 0.52 | 0.20 | 0.40 | 0.19 |
| BORA | 0.84 | −0.73 | −0.54 | −0.23 | 0.13 | DCP1B | −0.20 | 0.15 | 0.53 | −0.09 | 0.10 | EPHA1 | 0.09 | 0.04 | −0.15 | 0.13 | 0.17 |
| G31401 | 2.62 | −0.75 | −1.28 | −0.63 | −0.37 | HERC2P8 | −1.10 | 1.68 | −1.56 | 2.20 | 1.30 | MMP26 | 0.47 | −0.16 | −0.36 | 0.48 | −0.72 |
| CD44 | 0.86 | −0.33 | −0.89 | −0.01 | −0.42 | NIM1K | −0.40 | −0.16 | 0.63 | −0.51 | 0.40 | AC092384.1 | 0.17 | −0.49 | 0.42 | −0.06 | 0.64 |
| PATL1 | 0.49 | −0.39 | −0.57 | −0.14 | −0.10 | RPIA | −0.22 | 0.24 | 0.04 | 0.05 | −0.28 | CEP104 | 0.03 | −0.04 | −0.20 | −0.04 | −0.05 |
| AC026470.2 | 1.33 | −0.66 | −0.75 | −0.33 | −0.31 | AC027097.2 | −0.29 | 0.16 | 0.51 | −0.05 | −0.12 | AC025048.2 | −0.16 | −0.42 | 0.07 | 0.50 | −0.11 |
| INTS13 | 0.70 | −0.40 | −0.48 | −0.17 | −0.18 | DPYSL5 | −0.91 | 0.48 | −0.12 | −0.01 | −0.49 | OVCH1 | −0.18 | 0.39 | 0.48 | 0.24 | −0.06 |
| LINP1 | 2.60 | −1.32 | −2.74 | 0.03 | −0.89 | MELTF | −0.46 | 0.51 | 0.58 | 0.19 | 0.48 | G33807 | −0.29 | 0.02 | 0.61 | −0.49 | −0.88 |
| NEDD4 | 0.62 | −0.44 | −0.67 | −0.17 | −0.39 | AC087164.1 | −0.88 | −0.22 | −0.64 | −0.38 | 0.13 | AL669831.3 | 0.20 | −0.23 | 0.04 | −0.23 | 0.42 |
| LARS | 0.44 | −0.22 | −0.31 | −0.16 | −0.11 | NT5DC2 | 0.19 | 0.02 | −0.03 | −0.08 | −0.10 | AL132712.2 | −0.33 | 0.37 | −0.34 | 0.54 | −0.65 |
| CASTOR3 | −1.10 | 0.72 | 0.93 | 0.52 | 0.28 | AC026316.3 | −0.99 | 0.24 | 1.30 | 0.23 | −1.02 | KRT25 | −0.42 | −0.67 | 1.75 | 0.24 | 3.15 |
| SCGB1D2 | −2.59 | 1.96 | 3.07 | −0.18 | −0.06 | LINC01798 | −1.00 | −0.63 | −0.66 | 0.26 | −0.11 | AL355677.1 | 0.52 | −0.12 | −1.94 | 0.13 | −1.58 |
| LINC00906 | −1.86 | 1.03 | 0.84 | 0.22 | 0.23 | MTND5P32 | 0.80 | −0.51 | 0.40 | 0.40 | −0.78 | AC018362.1 | 0.37 | −2.05 | 0.01 | 0.28 | 1.04 |
| NAA15 | 0.73 | −0.40 | −0.63 | −0.17 | −0.31 | SETD3 | 0.17 | −0.02 | 0.02 | −0.02 | −0.01 | OR4C4P | −0.63 | −0.07 | −0.96 | −0.54 | −2.51 |
| AP002518.2 | −2.57 | 1.14 | 2.91 | 0.84 | 0.93 | JPX | −0.18 | 0.04 | 0.19 | 0.16 | 0.13 | AC005005.4 | −0.21 | −0.05 | −0.59 | −0.15 | −0.77 |
| MRPS12 | 0.92 | −0.51 | −0.65 | −0.15 | −0.30 | CTD-3232M19.2 | 1.11 | −0.42 | −1.68 | 0.83 | −0.55 | AC073176.2 | 0.50 | −1.63 | −0.25 | 0.45 | 0.05 |
| IRS4 | −2.73 | 0.22 | 1.43 | 1.53 | 1.60 | MGC27382 | −0.74 | −0.14 | −0.14 | −0.20 | −0.29 | AC027601.3 | 0.28 | −1.15 | −1.61 | −0.93 | −0.69 |
| DTL | 1.17 | −1.01 | −1.08 | −0.24 | −0.30 | AC021739.5 | −0.51 | 0.72 | 0.60 | 0.14 | −0.26 | EEFSEC | 0.06 | −0.19 | −0.23 | 0.09 | 0.09 |
| RIT1 | 0.69 | −0.38 | −0.53 | −0.22 | −0.37 | EEF1GP4 | −0.93 | 1.67 | 1.85 | 0.35 | 0.17 | EGFR | 0.07 | 0.22 | −0.11 | 0.19 | −0.19 |
| EIF4G1 | 0.64 | −0.30 | −0.55 | −0.10 | −0.28 | AC018695.7 | −1.04 | 1.13 | −0.14 | 0.53 | 0.32 | AC124303.2 | 0.58 | 0.46 | −0.46 | 2.21 | −0.34 |
| JADE2 | −0.66 | 0.35 | 0.58 | 0.16 | 0.23 | AC007879.3 | −0.65 | −0.17 | 1.31 | −0.27 | 0.80 | AC132154.1 | −0.37 | −0.30 | −1.42 | 0.80 | −1.29 |
| LIF | −1.15 | −0.33 | 0.15 | −0.43 | 0.20 | KCNQ5-IT1 | 0.79 | −0.58 | 0.23 | 0.03 | 1.33 | AL627171.2 | −0.12 | 0.00 | −0.03 | 0.12 | −0.20 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| CCDC7 | −0.65 | 0.42 | 0.70 | 0.09 | 0.12 | PAXX | −0.29 | 0.03 | −0.09 | 0.27 | 0.32 | AP000432.1 | 0.47 | −2.07 | 0.08 | −0.04 | 2.17 |
| FHL1 | −2.02 | 1.59 | 1.42 | 0.96 | −0.48 | AC092943.1 | −1.14 | 0.96 | −0.78 | 0.79 | −2.50 | SFR1P2 | 0.47 | −0.14 | −2.02 | −0.45 | −1.87 |
| MIR31 | 4.59 | −1.68 | −2.60 | −0.33 | −2.76 | PDIA3P2 | −0.92 | 0.98 | 0.75 | 1.04 | 0.74 | RNU1-16P | 0.15 | −0.01 | −0.73 | 0.53 | −0.42 |
| SNAI2 | 0.97 | −0.49 | −1.02 | −0.24 | −0.54 | POLR2D | 0.16 | −0.19 | 0.00 | −0.14 | 0.01 | RNU7-23P | 0.49 | 0.29 | −1.52 | −0.62 | −1.27 |
| PIP4K2B | −0.42 | 0.16 | 0.30 | 0.07 | 0.19 | SLC2A7 | 1.65 | −0.92 | −2.87 | −0.08 | −2.22 | AC130650.1 | 0.14 | 0.51 | 0.04 | 0.31 | −0.23 |
| SLC30A7 | 0.66 | −0.40 | −0.41 | −0.16 | −0.22 | HIC2 | −0.30 | −0.07 | 0.22 | −0.06 | 0.42 | AC090236.2 | 0.23 | −0.31 | −0.96 | −0.11 | 0.38 |
| CYP4X1 | −1.14 | 0.75 | 0.39 | 0.34 | 0.22 | CTSS | 0.42 | −0.47 | −0.17 | −0.33 | −0.14 | LINC01903 | −0.33 | −0.57 | −2.13 | 1.04 | −0.94 |
| AC011365.1 | −1.55 | 0.81 | 1.07 | 0.30 | −0.05 | SULT1C2P1 | −0.85 | 0.57 | 0.19 | 0.08 | 0.04 | RNF39 | 0.11 | 0.48 | −0.19 | 0.64 | −0.29 |
| QSOX1 | 0.80 | −0.22 | −0.61 | −0.18 | −0.51 | AC068580.1 | 0.72 | −0.06 | 0.64 | −0.15 | −0.16 | SEMA4D | 0.07 | 0.28 | 0.29 | 0.11 | −0.18 |
| SEC14L5 | −1.42 | 0.69 | 1.31 | 0.25 | 0.86 | AL035681.1 | −0.34 | −0.13 | 0.18 | 0.06 | 0.40 | AL731566.2 | −0.30 | 0.30 | 1.59 | −0.25 | 0.61 |
| KRT73 | −2.29 | 2.02 | 2.05 | 1.31 | 0.28 | AC012470.1 | −1.05 | −1.24 | 1.82 | −0.20 | 1.39 | MYCBP2-AS1 | 0.13 | 0.27 | 0.67 | 0.03 | 0.16 |
| COPB2 | 0.68 | −0.37 | −0.48 | −0.18 | −0.28 | HCG2040054 | −0.95 | 0.05 | 1.98 | −0.85 | 0.40 | AC008264.2 | 0.10 | 0.17 | 0.05 | 0.43 | 0.12 |
| ELOA | 0.61 | −0.28 | −0.42 | −0.24 | −0.25 | HSD11B1L | −0.38 | 0.54 | 0.31 | 0.41 | 0.44 | AC007029.1 | −0.32 | −1.13 | 0.86 | −0.91 | 0.72 |
| CDCA8 | 1.29 | −0.97 | −1.48 | −0.31 | −0.24 | AP002381.1 | 0.69 | −0.31 | −0.09 | −0.53 | −0.15 | AL391421.1 | 0.13 | 0.09 | −0.06 | −0.16 | 0.08 |
| CFAP73 | −2.44 | 1.59 | 1.80 | 0.87 | 0.16 | AL359921.1 | 0.85 | −0.13 | 0.62 | 0.71 | 1.23 | AL358473.1 | −0.41 | −1.83 | −1.52 | −0.64 | −1.77 |
| CECR7 | −0.86 | 0.42 | 0.65 | 0.34 | 0.43 | GTF2H2 | −0.36 | −0.06 | −0.01 | 0.33 | 0.34 | PNMA1 | −0.07 | −0.07 | 0.15 | −0.27 | −0.07 |
| CRYBG1 | 0.99 | −0.29 | −0.69 | 0.13 | −0.21 | OR7E94P | −1.00 | 0.54 | 1.69 | 0.70 | 0.62 | CCR8 | −0.25 | −0.50 | 0.55 | −0.65 | 1.27 |
| SIPA1L2 | 0.78 | −0.26 | −0.76 | −0.20 | −0.41 | AC090616.6 | −0.38 | −0.36 | 0.00 | 0.22 | 0.36 | RPSAP44 | 1.09 | −0.48 | −1.23 | 1.39 | 0.29 |
| PSME4 | 0.58 | −0.21 | −0.59 | −0.07 | −0.35 | AP002478.1 | −0.85 | −1.02 | 0.02 | −0.17 | 0.27 | OR1L8 | −0.22 | −0.79 | 1.31 | −0.89 | 0.72 |
| PNO1 | 0.86 | −0.44 | −0.83 | −0.19 | −0.51 | SNORD67 | −0.52 | 0.27 | −0.15 | 0.17 | −0.26 | AC099671.1 | −0.57 | 0.68 | 1.00 | −0.09 | −2.29 |
| NDRG2 | −0.85 | 0.73 | 0.96 | 0.16 | 0.13 | RIPOR3 | 0.33 | −0.25 | −0.11 | −0.47 | −0.15 | RNA5SP152 | 0.22 | 0.57 | 0.75 | 0.26 | 0.43 |
| DOK3 | 1.14 | −0.64 | −1.06 | −0.26 | −0.16 | PISD | −0.18 | 0.08 | −0.07 | 0.10 | −0.03 | MTCO2P1 | −0.52 | −0.48 | 0.78 | −0.94 | 1.20 |
| ARHGAP12 | −0.44 | 0.45 | 0.35 | 0.17 | 0.00 | MRPS18CP6 | −0.91 | −1.12 | 2.32 | −0.68 | 1.43 | C1orf127 | −0.26 | 0.37 | 1.33 | −0.20 | 0.56 |
| FAHD2A | −0.73 | 0.48 | 0.83 | 0.25 | 0.22 | MRGPRE | −1.27 | 0.58 | 1.94 | 1.99 | 0.51 | ECH1 | −0.08 | 0.02 | −0.07 | 0.02 | 0.07 |
| ACVR2B-AS1 | −1.38 | 0.77 | 1.57 | 0.34 | 0.26 | AC010761.6 | −1.39 | −1.34 | 1.88 | −1.44 | 1.93 | AC016739.1 | 0.11 | 0.32 | −0.08 | 0.28 | −0.46 |
| KBTBD12 | −1.53 | 0.80 | 0.90 | 0.76 | 0.47 | AGPAT4-IT1 | 0.41 | −0.03 | −0.53 | 0.08 | −0.20 | RNU4-28P | −0.72 | 0.93 | 0.69 | 0.99 | 0.90 |
| NPM2 | −1.63 | 0.64 | 0.86 | 0.53 | 0.24 | LINC02217 | 1.49 | −1.84 | −3.61 | 0.44 | −1.57 | G13690 | −0.22 | −0.06 | 0.81 | 0.58 | 1.97 |
| MCCC1 | −0.49 | 0.34 | 0.43 | 0.26 | 0.18 | RNU6-1091P | 1.41 | −1.52 | −0.75 | 0.53 | 0.82 | HNRNPA3P13 | −0.28 | 0.00 | −1.35 | −0.15 | −1.54 |
| DUSP14 | 1.39 | −0.13 | −0.89 | −0.11 | −1.48 | AC004803.1 | −0.29 | 0.12 | 0.33 | 0.18 | 0.33 | AL162293.1 | −0.37 | −0.50 | −1.41 | 0.30 | −0.26 |
| MARK1 | 0.77 | −0.21 | −1.10 | 0.03 | −0.52 | AC005154.1 | −0.31 | 0.06 | 0.28 | −0.01 | 0.08 | ALDH16A1 | 0.07 | −0.14 | −0.41 | 0.27 | 0.11 |
| PLXNA4 | −1.35 | 0.50 | 1.09 | 0.12 | 0.17 | RAI1 | −0.21 | 0.06 | −0.05 | 0.10 | 0.16 | AC027088.4 | 0.31 | −1.46 | −0.09 | −0.25 | 0.47 |
| PUDP | 0.73 | −0.28 | −0.76 | 0.07 | −0.25 | NUTM2B | −0.48 | 0.45 | 0.73 | 0.09 | 0.40 | HNRNPA3P10 | −0.17 | −0.06 | −0.58 | 0.34 | −0.06 |
| IFT140 | −0.80 | 0.31 | 0.23 | 0.36 | 0.21 | AC007613.1 | −0.55 | −0.24 | −0.47 | −0.36 | −0.40 | PF4V1 | −0.67 | 0.95 | −0.48 | −1.11 | −0.80 |
| CA1 | −1.26 | 0.97 | 1.35 | −0.13 | 0.03 | AL354733.1 | −0.75 | −0.83 | 0.56 | −0.58 | 0.49 | AC128677.1 | 0.68 | 0.03 | −1.57 | 1.86 | −0.88 |
| EPHB1 | −1.19 | 0.67 | 0.80 | 0.03 | 0.01 | FAM204A | 0.13 | −0.02 | −0.23 | 0.05 | −0.18 | RFLNB | 0.10 | −0.20 | 0.21 | −0.57 | −0.23 |
| AMOTL1 | 0.61 | −0.31 | −0.49 | −0.13 | −0.13 | AC020916.2 | 0.74 | 0.57 | 0.02 | −0.20 | −0.72 | AC126177.8 | −0.41 | −1.10 | −0.20 | −0.12 | −0.29 |
| MAFB | 0.87 | −0.26 | −0.81 | −0.31 | −0.77 | AC006111.1 | −0.84 | 0.32 | 1.05 | −0.84 | 0.07 | FDX1P2 | 0.35 | 0.09 | 1.13 | 0.64 | 0.90 |
| ST8SIA2 | 2.20 | −1.36 | −4.05 | −0.01 | −3.54 | MIR5191 | 1.39 | −0.45 | −0.42 | −0.07 | −1.00 | RNA5SP277 | −0.34 | −0.30 | 0.55 | −0.99 | 0.19 |
| SNX18P9 | −2.03 | 1.51 | 0.51 | 1.26 | 0.33 | LINC01634 | −0.96 | 0.08 | 0.02 | 0.10 | −0.26 | OR4X2 | −0.87 | 1.08 | −2.15 | −0.10 | −2.98 |
| NRXN1 | −1.75 | 0.78 | 1.46 | 0.48 | 0.97 | AL356776.1 | 0.37 | −0.07 | 0.15 | 0.18 | 0.22 | AC096632.2 | 0.36 | −0.73 | 0.81 | 0.29 | 1.46 |
| LEP | −3.40 | 2.97 | 2.76 | 1.13 | 0.03 | PLEKHG3 | 0.25 | −0.09 | −0.66 | 0.13 | −0.02 | SNHG7 | −0.08 | 0.03 | −0.20 | 0.32 | −0.38 |
| SKA2 | 0.90 | −0.60 | −0.78 | −0.30 | −0.37 | C21orf91-OT1 | 0.66 | −0.73 | −0.05 | 0.37 | 0.91 | AC005261.3 | 0.08 | 0.20 | 0.39 | −0.20 | −0.24 |
| AC125807.2 | 1.09 | −0.56 | −0.62 | −0.14 | −0.31 | AC087793.1 | 0.88 | −0.66 | −0.59 | −0.16 | −0.17 | AL137058.3 | 0.50 | −0.37 | −1.29 | −0.28 | 0.08 |
| PEG3 | −1.25 | 0.75 | 1.17 | 0.25 | 0.11 | AL033527.4 | −1.30 | −1.02 | 2.05 | −0.70 | 2.17 | RNU7-193P | −0.31 | 0.65 | −0.54 | 0.78 | 0.07 |
| RRM1 | 0.92 | −0.50 | −0.65 | −0.23 | −0.41 | IL10RA | 0.41 | −0.55 | −0.67 | −0.11 | −0.24 | AC005746.3 | −0.24 | 0.85 | −0.33 | 0.09 | −0.71 |
| FAM162A | 1.04 | −0.25 | −0.73 | 0.03 | −0.69 | GTF2E2 | 0.19 | −0.18 | −0.17 | −0.28 | −0.10 | SRP72P2 | 0.11 | 0.17 | 0.44 | 0.02 | 0.07 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| PDS5A | 0.43 | −0.23 | −0.29 | −0.12 | −0.20 | GTF3C2-AS1 | −0.33 | 0.05 | 0.33 | 0.11 | 0.01 | AL136961.1 | −0.70 | −1.69 | −0.16 | 1.29 | 1.39 |
| POLE2 | 0.96 | −0.49 | −0.61 | −0.07 | −0.24 | AL606834.2 | 0.55 | −0.10 | 0.04 | 0.06 | 0.06 | C5orf60 | −0.41 | 1.95 | 0.76 | −0.11 | −0.78 |
| SLC27A1 | −0.86 | 0.35 | 0.68 | 0.28 | 0.30 | AL359633.2 | −1.76 | 0.73 | 3.18 | 0.39 | 0.96 | AC068647.2 | −0.28 | 0.67 | −1.69 | 0.80 | −1.26 |
| RAB27A | 0.69 | −0.39 | −0.58 | −0.05 | −0.13 | AC092104.2 | −1.90 | 0.34 | 2.84 | 1.29 | 0.86 | AL132780.1 | 0.13 | −0.36 | 0.80 | −0.16 | 0.79 |
| HIST1H2BJ | 1.43 | −0.83 | −1.34 | −0.31 | −0.87 | AC120036.4 | −0.90 | 0.05 | 2.50 | −0.64 | 1.03 | AL391597.1 | 0.86 | −1.70 | −0.78 | −0.90 | 0.49 |
| MED8 | 0.77 | −0.30 | −0.51 | −0.16 | −0.52 | AC034236.2 | −0.37 | 0.09 | 0.35 | 0.01 | −0.05 | LINC00337 | 0.23 | −1.06 | −0.02 | −0.26 | 0.41 |
| KCNA2 | −1.33 | 0.59 | −0.02 | 0.30 | −0.10 | AP000438.1 | −1.78 | 1.41 | 2.69 | 0.41 | 2.00 | GABRG1 | −0.34 | 0.09 | −0.08 | 1.31 | 0.25 |
| KIF15 | 1.07 | −0.91 | −1.21 | −0.28 | −0.38 | DLGAP1-AS3 | −1.32 | −0.36 | −1.37 | −0.57 | 0.74 | AL606489.2 | 0.30 | −0.19 | −0.90 | −0.01 | 0.35 |
| CASQ2 | −1.81 | 0.57 | 0.64 | 0.85 | −0.10 | LINC00839 | −0.53 | −0.13 | −0.26 | 0.14 | 0.23 | RPL23AP57 | 0.40 | 0.01 | 0.21 | 0.20 | −0.39 |
| EHD4 | 0.81 | −0.42 | −0.82 | −0.23 | −0.74 | SERPINI1 | −0.30 | 0.23 | 0.87 | 0.13 | 0.24 | AC068769.1 | 0.60 | −1.65 | −0.53 | −0.60 | 0.81 |
| FGF14 | −1.20 | 1.14 | 1.11 | 0.00 | −0.09 | SNX4 | 0.20 | −0.20 | −0.24 | −0.22 | 0.02 | LCT | −0.16 | −0.60 | 0.24 | −0.34 | 0.22 |
| FUT3 | 1.81 | −1.01 | −1.86 | −0.65 | −1.20 | RNU6-15P | −1.36 | 0.51 | 1.45 | −0.30 | −0.72 | MPC1L | 0.64 | 0.43 | 3.12 | 0.92 | 1.35 |
| FCF1 | 0.55 | −0.33 | −0.46 | −0.07 | −0.13 | ANKRD1 | −0.79 | 0.12 | 0.09 | −0.26 | −0.23 | AC110792.2 | 0.13 | 0.01 | −0.11 | −0.14 | −0.28 |
| RPL22L1 | 1.45 | −0.82 | −0.71 | −0.89 | −0.38 | SMURF2 | −0.15 | 0.11 | 0.12 | −0.08 | −0.06 | CDC16 | −0.04 | 0.03 | 0.07 | 0.14 | 0.11 |
| FAM166B | −1.35 | 0.51 | 1.02 | −0.02 | 0.53 | AP001432.1 | 0.40 | −0.07 | 0.16 | 0.10 | 0.33 | ITPKB-AS1 | 0.14 | −0.56 | 0.69 | −0.45 | 0.34 |
| IL17D | −1.51 | 0.61 | 1.33 | 0.57 | 0.28 | QRICH1 | −0.09 | 0.05 | −0.14 | 0.04 | −0.12 | KDM5DP1 | −0.52 | 0.91 | 0.25 | −0.35 | −0.95 |
| MCM10 | 1.46 | −1.38 | −1.79 | −0.42 | −0.71 | RPL7P14 | −0.29 | 0.29 | 0.04 | 0.22 | −0.10 | SPINK8 | −0.40 | 0.49 | 1.72 | −1.88 | −0.86 |
| FBXO5 | 1.13 | −0.72 | −0.98 | −0.38 | −0.36 | AC092902.3 | −1.24 | 1.04 | 2.95 | 1.02 | 0.48 | AC126177.1 | −0.77 | −0.23 | −0.31 | 1.37 | 0.00 |
| NUDT5 | 0.69 | −0.28 | −0.40 | −0.04 | −0.08 | AL360270.3 | −0.48 | −0.41 | 0.52 | −0.06 | 0.81 | RNU6-828P | 0.22 | 0.12 | 0.44 | 0.37 | 0.91 |
| AC051619.1 | −2.94 | 0.85 | 0.74 | 0.39 | 0.31 | CLTCL1 | 0.24 | −0.31 | −0.60 | 0.12 | −0.08 | AC209007.1 | 0.51 | −0.96 | −0.16 | −0.53 | 1.13 |
| ATP6VOD1 | 0.63 | −0.18 | −0.61 | 0.07 | −0.36 | MRPL33 | 0.26 | −0.14 | 0.15 | −0.35 | 0.04 | LILRA1 | 0.26 | −0.92 | −2.79 | −0.09 | −2.26 |
| PIK3CD | 0.84 | −0.52 | −0.90 | 0.07 | −0.12 | CHCHD4P5 | −0.45 | 0.06 | 0.30 | 0.11 | 0.19 | RHOT1P3 | −0.58 | 1.28 | −0.64 | 1.43 | 0.54 |
| RBBP6 | 0.55 | −0.24 | −0.56 | −0.11 | −0.37 | AC011416.3 | −0.74 | 0.48 | 0.35 | 0.46 | 0.18 | AC104563.1 | −0.20 | 0.78 | 1.05 | 0.44 | 0.09 |
| FAT3 | −1.70 | 0.86 | 1.21 | −0.03 | −0.21 | BSN-DT | −1.04 | 0.47 | 0.74 | 0.18 | 1.31 | OLFM2 | −0.10 | 0.39 | 0.35 | 0.25 | −0.16 |
| PSMC1 | 0.72 | −0.46 | −0.67 | −0.24 | −0.35 | CTBP2P7 | −0.83 | 0.84 | 2.08 | −0.28 | −0.49 | MROH9 | 0.13 | −0.17 | −0.22 | 0.51 | 0.31 |
| EHF | 1.38 | −0.46 | −1.06 | 0.14 | −0.37 | ALG8 | 0.16 | −0.26 | 0.09 | −0.13 | 0.24 | AL772337.1 | −0.44 | −0.99 | −2.19 | 1.97 | 1.56 |
| PRKAR2A | 0.67 | −0.22 | −0.48 | −0.06 | −0.28 | AC005746.1 | −0.58 | 0.28 | 1.49 | −0.20 | 0.16 | SEC14L3 | −0.34 | −0.11 | −2.41 | 0.71 | −0.42 |
| RN7SL138P | 2.10 | −0.57 | −0.96 | −0.18 | −0.50 | DUX4L26 | −0.79 | 0.16 | −0.83 | 0.86 | 0.12 | RP11-467N20.5 | 0.28 | 0.25 | −0.44 | 0.14 | −0.78 |
| PERP | 1.65 | −0.24 | −0.81 | −0.14 | −0.84 | CXADRP3 | 1.67 | −0.93 | −0.01 | −0.59 | 1.11 | SLFNL1 | 0.11 | −0.15 | −0.26 | 0.05 | 0.20 |
| SDR9C7 | 1.67 | −0.43 | −1.01 | −0.28 | −1.02 | RBM38 | 0.36 | −0.38 | −0.62 | 0.15 | −0.09 | AL359881.1 | 0.30 | −0.90 | −1.92 | 0.50 | 0.78 |
| EIF4H | 0.72 | −0.12 | −0.56 | −0.02 | −0.50 | AC008555.5 | −0.90 | −0.17 | 1.91 | −0.75 | 0.25 | AGPAT2 | −0.12 | 0.19 | −0.39 | 0.10 | −0.20 |
| DPAGT1 | 0.83 | −0.54 | −0.48 | −0.23 | −0.03 | AL136981.1 | −1.16 | −0.07 | 0.44 | −1.00 | −0.15 | AL137779.1 | −0.13 | −0.46 | −0.22 | −0.12 | 0.27 |
| INTS6 | 0.56 | −0.35 | −0.25 | −0.23 | −0.10 | IGFBP6 | −0.48 | 0.24 | 0.15 | 0.02 | −0.64 | RNU6-1195P | 0.37 | 0.46 | 0.06 | −0.93 | −1.18 |
| PPARD | 0.78 | −0.37 | −1.02 | −0.16 | −0.62 | PKIB | −0.36 | 0.22 | −0.30 | 0.13 | −0.03 | LINC01807 | −0.72 | −0.17 | 0.28 | −0.08 | −2.13 |
| KRT39 | −2.08 | 2.20 | 2.78 | 0.05 | 0.68 | AL356289.3 | −0.98 | −1.64 | 0.25 | 0.64 | 1.05 | LINC00703 | −0.52 | −0.08 | −1.84 | 0.68 | −2.59 |
| AC019127.1 | 1.65 | −0.69 | −1.60 | −0.05 | −0.90 | AC069499.1 | 0.43 | −0.81 | −0.25 | −0.44 | 0.10 | AL162724.2 | 0.14 | −0.38 | −0.32 | −0.35 | 0.06 |
| LGR5 | −2.24 | 0.72 | 2.45 | −0.70 | 0.08 | PP2D1 | 0.51 | −0.13 | −0.21 | −0.10 | −0.30 | AC012613.1 | −0.35 | 0.12 | 1.13 | −0.07 | 0.33 |
| DHX9 | 0.66 | −0.46 | −0.64 | −0.19 | −0.25 | AC083875.1 | 0.43 | 0.05 | −0.20 | −0.06 | −0.15 | AC008269.2 | 0.19 | −0.69 | 0.50 | −0.04 | 0.45 |
| AHSA1 | 0.72 | −0.33 | −0.30 | −0.24 | −0.24 | AL161645.1 | 0.89 | −0.45 | −1.02 | 0.02 | −0.13 | RUNDC3B | −0.09 | 0.04 | 0.64 | −0.07 | −0.10 |
| CCBE1 | −1.36 | 0.36 | 1.44 | −0.21 | 0.55 | RPL13AP25 | 0.38 | 0.12 | −0.28 | 0.03 | −0.34 | GPA33 | −0.29 | 0.35 | −1.90 | 0.11 | −2.16 |
| SSRP1 | 0.69 | −0.41 | −0.69 | −0.09 | −0.27 | HMGN1P28 | −0.73 | 0.51 | 0.18 | −0.43 | 0.03 | RPL27AP | −0.52 | 0.12 | −0.64 | 0.31 | 0.05 |
| SLC29A1 | −0.92 | 0.54 | 1.04 | 0.09 | 0.13 | FEM1A | −0.28 | −0.12 | −0.35 | 0.14 | 0.02 | AP000676.2 | 0.30 | −1.03 | 0.69 | 0.44 | 0.48 |
| NCAM1 | −1.56 | 0.34 | 1.08 | 0.08 | 0.76 | RFTN1 | 0.28 | −0.43 | −0.39 | −0.22 | 0.08 | HS6ST2 | −0.24 | 0.35 | −0.96 | 0.74 | −0.85 |
| MFSD14C | −0.61 | 0.34 | 0.76 | −0.01 | 0.26 | RN7SKP57 | 1.10 | −0.70 | 0.14 | −0.79 | −0.06 | AL359853.3 | 0.66 | 0.70 | −1.37 | −0.56 | −1.40 |
| DDX28 | 1.01 | −0.48 | −1.00 | 0.08 | −0.60 | AC107956.2 | 0.75 | −0.51 | −0.25 | 0.19 | 0.85 | AC099339.1 | 0.58 | −0.03 | −0.21 | 0.90 | 0.37 |
| FERMT1 | 1.53 | −0.77 | −1.22 | −0.36 | −0.35 | EGR2 | −0.48 | 0.57 | −0.11 | −0.07 | −0.27 | AC108752.1 | 0.64 | 0.22 | −1.61 | 1.02 | −0.55 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| DUXB | −1.53 | 0.82 | 0.67 | 0.23 | −0.18 | AC004223.1 | 0.99 | 0.82 | −0.20 | −0.06 | −0.67 | IPMK | 0.06 | −0.03 | −0.08 | 0.06 | −0.15 |
| KCTD11 | 0.99 | −0.25 | −0.48 | −0.18 | −0.40 | RNU6-402P | 0.74 | −0.57 | −0.16 | −0.20 | 0.18 | AC016405.3 | −0.35 | 0.60 | −1.18 | 0.34 | −0.41 |
| CTR9 | 0.65 | −0.29 | −0.58 | −0.20 | −0.31 | RNA5SP454 | −0.95 | −0.34 | −1.99 | −0.02 | −0.64 | ATG12P2 | 0.20 | 0.00 | −0.76 | 0.29 | 0.45 |
| CHTF8 | 0.66 | −0.31 | −0.40 | −0.11 | −0.29 | RNU6-377P | 0.78 | −0.67 | 0.18 | −0.15 | 0.73 | SLC9A3P4 | −0.50 | 0.44 | 0.75 | 1.41 | −0.83 |
| SLC26A1 | −1.19 | 0.14 | 0.64 | 0.27 | 0.74 | PTGER3 | −0.50 | 0.32 | 1.18 | 0.41 | −0.11 | RNU6ATAC39P | 0.23 | 0.23 | 0.02 | 0.21 | −0.48 |
| CLSTN2 | −2.12 | 1.67 | 1.61 | 1.11 | −0.49 | AL353147.1 | −0.49 | 0.31 | 0.87 | −0.41 | −0.05 | AC023824.1 | 0.41 | −0.62 | 0.55 | 1.35 | −0.79 |
| AP3B1 | 0.42 | −0.24 | −0.41 | −0.14 | −0.24 | LINC01946 | −1.05 | 0.04 | 0.82 | −0.80 | −0.30 | HMGB1P18 | −0.67 | 0.02 | −0.84 | 1.01 | −0.65 |
| PDZD7 | −1.63 | 1.10 | 1.59 | 1.15 | 0.54 | AC138904.3 | −1.41 | 0.05 | −0.89 | 0.04 | 0.11 | LRRC72 | −0.85 | −1.33 | 1.87 | −0.60 | 2.21 |
| AL512643.1 | −2.37 | 0.86 | 1.97 | 1.29 | 0.73 | HOXD8 | −0.40 | 0.19 | 1.04 | 0.10 | 0.20 | NAA40 | −0.06 | −0.15 | −0.07 | −0.03 | 0.31 |
| DCUN1D5 | 0.69 | −0.49 | −0.62 | −0.16 | −0.19 | PITRM1-AS1 | 0.30 | −0.24 | −0.68 | −0.15 | −0.57 | MOSMO | −0.07 | 0.01 | 0.38 | −0.19 | 0.12 |
| HSPA6 | 1.50 | −1.09 | −1.33 | 0.03 | −0.62 | LINC01640 | −1.19 | 0.74 | 0.86 | 0.28 | −0.02 | SPACA7 | −0.45 | 0.85 | −0.75 | −0.08 | −0.91 |
| SSC5D | −1.28 | 0.88 | 1.26 | 0.16 | −0.31 | EYA1 | −0.67 | −0.08 | −0.50 | −0.02 | −0.31 | RN7SL69P | −0.44 | 0.40 | −0.45 | 0.26 | 0.90 |
| MMP9 | 1.89 | −1.69 | −1.46 | −0.43 | −0.34 | BLOC1S1-RDHS | −0.73 | 0.70 | 0.46 | 0.26 | −0.39 | MIR320C1 | 0.43 | −0.75 | −0.54 | −0.36 | −1.23 |
| DYNC1I2 | 0.67 | −0.20 | −0.50 | −0.19 | −0.43 | HMGB3P21 | 0.88 | −0.31 | −0.43 | −0.27 | 0.12 | AC011773.3 | −0.25 | 0.23 | 1.06 | 0.32 | 0.18 |
| PLEKHN1 | −1.27 | 0.53 | 0.59 | 0.60 | 0.49 | P1-UPK3BP1-PM | −0.55 | 0.36 | 0.32 | 0.19 | 0.06 | RPS3AP40 | −0.25 | 1.67 | −0.15 | 0.82 | −0.17 |
| MACO1 | 0.57 | −0.10 | −0.53 | −0.07 | −0.38 | LRRC2-AS1 | −0.73 | 0.85 | 0.13 | 0.08 | −0.05 | AC008622.2 | 0.57 | −0.70 | −0.99 | −0.07 | 1.13 |
| AL513548.1 | −1.07 | 0.37 | 0.95 | 0.13 | 0.20 | CFL1P1 | −0.45 | 0.37 | 0.41 | 0.01 | 0.17 | DMBX1 | 0.28 | 0.00 | −0.99 | 0.95 | −0.02 |
| PRKAG1 | 0.60 | −0.27 | −0.38 | −0.10 | −0.17 | KRT18P59 | 0.68 | −0.90 | −0.24 | 0.00 | −0.49 | DNAI2 | −0.26 | −1.13 | −0.47 | −0.04 | 0.39 |
| SSBP1 | 0.78 | −0.46 | −0.62 | −0.30 | −0.29 | G1033 | −0.94 | 0.18 | 1.15 | −0.48 | −0.16 | RNF2P1 | −0.50 | −0.95 | −1.22 | 0.70 | 0.50 |
| MDM4 | −0.46 | 0.13 | 0.21 | 0.10 | 0.16 | BCAP31P1 | −0.67 | 0.70 | −0.36 | 1.09 | −0.48 | AL512378.1 | −0.34 | −0.24 | 0.18 | 0.54 | −0.54 |
| SNRPGP10 | 1.63 | −0.73 | −1.29 | −0.04 | −0.68 | AC012485.1 | −0.46 | 0.44 | 0.97 | −0.15 | 0.13 | AL390755.1 | 0.65 | 0.17 | 0.85 | 0.85 | 0.08 |
| PRAM1 | −1.66 | 0.13 | 0.96 | 0.45 | 0.42 | ATP5ME | 0.28 | −0.23 | −0.39 | 0.17 | −0.25 | MIR7-3HG | −0.35 | −1.61 | −0.34 | −0.38 | −0.10 |
| MLPH | −1.27 | 0.64 | 0.53 | 0.68 | 0.32 | AL122058.1 | −0.94 | −0.14 | 0.22 | 0.72 | 0.61 | AL022097.1 | 0.11 | −0.28 | 0.20 | −0.15 | 0.39 |
| SERPINB2 | 1.39 | −0.75 | −1.52 | −0.19 | −1.43 | AC025569.1 | −0.43 | 0.17 | 0.64 | −0.09 | −0.20 | AL157395.1 | 0.25 | 0.20 | −0.61 | −0.31 | −0.86 |
| RNU2-63P | 2.61 | −1.57 | −2.22 | −1.49 | −1.46 | ART4 | −0.56 | 0.16 | 0.42 | 0.09 | 0.44 | AC005740.2 | −0.40 | −0.25 | 1.04 | 0.60 | 0.63 |
| G15375 | −1.29 | 0.85 | 1.23 | 0.37 | 0.20 | KIAA1191 | 0.22 | 0.03 | −0.16 | −0.07 | −0.22 | RNU6-1197P | −0.52 | 0.80 | −0.61 | −0.57 | −0.53 |
| STAM | 0.71 | −0.37 | −0.48 | −0.24 | −0.29 | AC005692.3 | −0.87 | −0.57 | −0.84 | 0.03 | 0.53 | ATOH1 | −0.41 | 1.07 | −0.90 | 0.07 | −0.27 |
| GTPBP4 | 0.78 | −0.62 | −0.83 | −0.16 | −0.38 | AL354993.2 | −0.55 | 0.00 | 0.81 | 0.50 | 0.86 | C22orf24 | −0.24 | −0.20 | −0.95 | −0.26 | −0.52 |
| AC027373.1 | 1.61 | −0.58 | −1.48 | −0.27 | −0.68 | AL033504.1 | −0.70 | 0.25 | 1.56 | −0.43 | 0.45 | SRP68P1 | 0.42 | −0.58 | 1.17 | 0.66 | 2.18 |
| BAG3 | 0.74 | −0.32 | −0.87 | 0.03 | −0.33 | AC243773.2 | 0.66 | −0.60 | −0.67 | −0.42 | −0.52 | AL358232.1 | 0.43 | −1.13 | −1.39 | −1.25 | −0.87 |
| AC135506.1 | −1.37 | 0.48 | 0.96 | 0.47 | 0.05 | G20080 | 0.93 | −2.34 | 0.09 | −0.41 | 1.61 | AC079766.1 | 0.47 | −0.12 | −0.32 | −2.00 | −0.91 |
| ERI1 | 0.87 | −0.61 | −0.82 | −0.20 | −0.29 | CLDN9 | −1.33 | 0.28 | 1.20 | −0.17 | −0.25 | GOLGA2 | −0.03 | 0.15 | −0.03 | −0.04 | −0.18 |
| FH | 0.96 | −0.46 | −0.71 | −0.22 | −0.43 | HCG20 | −0.81 | 0.98 | 0.65 | −0.13 | −0.24 | AL590684.1 | −0.38 | −1.29 | 0.82 | −0.69 | 0.40 |
| R3HDM4 | 0.73 | −0.36 | −0.79 | 0.07 | −0.33 | AF131215.2 | 0.40 | −0.12 | −0.22 | 0.17 | 0.43 | IGLV3-19 | 1.33 | 2.50 | 1.19 | −0.39 | −2.97 |
| ARHGAP33 | −1.19 | 0.50 | 0.32 | 0.60 | 0.14 | CRIM1 | −0.26 | 0.21 | 0.20 | 0.01 | 0.11 | ST13P12 | 0.35 | 1.11 | 0.96 | 0.63 | 0.03 |
| PTGES3 | 0.70 | −0.39 | −0.48 | −0.15 | −0.17 | AL583844.1 | 1.74 | −1.84 | −1.70 | −0.10 | −0.87 | POLA2 | −0.06 | −0.37 | −0.20 | −0.05 | 0.28 |
| ANKDD1B | −1.23 | 0.72 | 0.92 | 0.24 | 0.27 | AC006141.1 | −0.21 | 0.14 | 0.56 | 0.08 | 0.21 | AC073575.2 | 0.45 | −2.15 | 1.06 | −0.26 | 0.09 |
| MYOM1 | −1.56 | 0.83 | 1.05 | 1.00 | 0.14 | PRSS3P2 | −1.06 | −0.29 | −0.15 | −0.23 | 2.20 | RNA5SP155 | 0.20 | −0.32 | −0.41 | −0.39 | 0.43 |
| MECP2 | −0.43 | 0.26 | 0.31 | 0.12 | 0.10 | FCRL6 | −0.68 | −0.47 | 0.58 | −0.31 | 0.42 | RBBP4P5 | 0.64 | −1.25 | −1.37 | −1.41 | −0.38 |
| OLMALINC | −0.88 | 0.44 | 0.88 | −0.11 | 0.34 | SRGAP3-AS3 | −0.59 | −0.67 | −0.34 | 0.34 | −0.13 | AC132938.3 | −0.21 | −0.39 | 0.37 | 0.00 | 0.58 |
| AC024075.1 | −0.73 | 0.35 | 0.38 | 0.40 | 0.33 | RNU7-180P | 0.86 | −0.08 | −1.95 | 0.01 | 0.18 | CHID1 | −0.05 | −0.05 | −0.23 | 0.19 | 0.08 |
| STIL | 1.18 | −1.08 | −1.30 | −0.30 | −0.21 | RN7SKP110 | −0.75 | 1.07 | 0.71 | −0.85 | −1.13 | SNAP47-AS1 | 0.21 | −0.35 | −0.36 | 0.12 | 0.54 |
| LRRN4CL | −1.55 | 0.48 | 1.06 | 0.39 | 0.42 | MT-ND5 | −0.34 | 0.05 | 0.24 | −0.02 | 0.14 | DEGS1 | −0.11 | 0.31 | 0.42 | 0.41 | −0.01 |
| AC110048.2 | −1.18 | 0.55 | 0.95 | 0.22 | 0.13 | RGP1 | 0.13 | 0.05 | −0.02 | −0.04 | −0.07 | ADAP1 | −0.16 | −0.76 | −0.21 | −0.46 | 0.26 |
| RABL2A | −0.93 | 0.40 | 1.06 | −0.07 | 0.12 | MIR1284 | −0.87 | 0.68 | 1.77 | −0.29 | −0.16 | AL355102.4 | 0.35 | −0.29 | −1.95 | 0.37 | −0.35 |
| AC092338.2 | −1.43 | 0.17 | 0.90 | −0.45 | 0.57 | PCGF6 | 0.20 | −0.26 | −0.18 | −0.03 | 0.09 | HTR2C | −0.33 | −0.45 | −0.06 | 0.05 | 1.17 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| RGS22 | −1.74 | 1.48 | 2.35 | 0.54 | 0.61 | AC010754.1 | 0.56 | 0.22 | −0.58 | 0.15 | −0.26 | ELAC1 | −0.08 | 0.02 | 0.14 | 0.11 | 0.00 |
| DNAJC9 | 0.79 | −0.46 | −0.45 | −0.29 | −0.31 | FILNC1 | −1.48 | 0.18 | −0.41 | 0.64 | −1.82 | CCNG1 | 0.09 | −0.05 | −0.01 | 0.06 | −0.01 |
| HNRNPA2B1 | 0.56 | −0.43 | −0.52 | −0.25 | −0.06 | G26658 | 0.47 | −0.19 | −0.70 | −0.39 | −0.55 | AL031593.1 | −0.18 | 0.06 | 0.82 | −0.53 | 0.23 |
| ACP5 | 1.17 | −0.49 | −1.11 | 0.00 | −0.63 | AC006272.1 | 0.98 | −0.99 | −1.05 | −1.08 | −0.31 | AC018953.1 | −0.66 | −0.01 | −0.52 | 0.37 | 0.01 |
| AC068152.1 | −0.82 | 0.42 | 0.48 | 0.17 | 0.08 | LINC01931 | −0.68 | 0.44 | 0.45 | 0.22 | 0.66 | AC102945.1 | −0.09 | −0.07 | −0.15 | −0.16 | −0.12 |
| GINS1 | 1.04 | −0.98 | −1.11 | −0.32 | −0.09 | AC128688.1 | −0.93 | 0.63 | 0.65 | −0.09 | 0.21 | PTPRN | 0.30 | −1.03 | −0.22 | −0.26 | 0.78 |
| ATP8B1 | 0.37 | −0.14 | −0.22 | −0.13 | −0.17 | AC011330.2 | 0.89 | −0.78 | −0.48 | −0.52 | 0.25 | G37296 | 0.11 | −0.18 | 0.15 | −0.20 | 0.20 |
| SPCS3 | 0.90 | −0.35 | −0.52 | −0.14 | −0.37 | FAM205C | −0.69 | 0.29 | 0.72 | 0.24 | 0.63 | AC005550.1 | −0.64 | 0.23 | 1.94 | −0.33 | 1.00 |
| DNASE1L3 | 1.20 | −0.50 | −1.04 | −0.14 | −0.43 | G18966 | 1.34 | −1.96 | −1.66 | −1.60 | −0.56 | RP13-996F3.4 | −0.19 | −0.02 | −0.35 | 0.07 | −0.59 |
| CFD | −1.95 | 1.68 | 1.98 | 0.73 | −0.05 | AL358333.2 | −0.76 | −0.19 | 0.16 | 0.05 | 0.27 | AP002759.1 | 0.56 | −0.26 | 1.75 | 0.19 | 0.48 |
| HIST1H4I | 1.68 | −0.98 | −1.18 | −0.42 | −0.35 | AL627308.2 | 0.61 | −0.66 | −0.61 | 0.16 | 0.32 | EIF3IP1 | −0.87 | −0.34 | 0.12 | −0.68 | −0.86 |
| PREP | 0.61 | −0.26 | −0.34 | −0.16 | −0.22 | GPR141 | 0.60 | −0.50 | 0.00 | −0.16 | 0.30 | AC011491.1 | 0.48 | −0.20 | −0.36 | −1.01 | −1.25 |
| RNU6-1291P | 2.60 | −0.82 | −1.35 | 0.09 | −0.25 | AC012050.1 | −0.87 | 0.59 | −0.47 | 0.37 | −1.22 | ELAVL3 | −0.23 | −1.59 | −0.23 | 0.14 | 0.78 |
| GORASP2 | 0.73 | −0.18 | −0.48 | −0.18 | −0.41 | AC105224.1 | 0.86 | −0.21 | −0.13 | −0.78 | −0.41 | AC009318.2 | 0.16 | 0.03 | 0.30 | 0.19 | 0.22 |
| DNAH1 | −0.92 | 0.21 | 0.37 | 0.29 | 0.21 | CREG1 | 0.33 | −0.09 | 0.15 | −0.12 | −0.21 | AL451165.2 | −0.12 | −0.29 | 0.57 | 0.13 | 0.44 |
| STARD9 | −0.91 | 0.60 | 0.88 | 0.28 | 0.23 | ANOS2P | −0.52 | 0.79 | 1.00 | 0.34 | 0.47 | CLN8 | 0.06 | 0.33 | 0.18 | 0.09 | −0.24 |
| NRG2 | −1.00 | 0.99 | 0.97 | 0.72 | 0.22 | PLCG1-AS1 | 0.28 | 0.01 | −0.36 | −0.10 | −0.33 | FOXD4L3 | −0.56 | 0.54 | 1.33 | 1.02 | 0.13 |
| CBL | 0.56 | −0.28 | −0.41 | −0.21 | −0.33 | CTD-2194D22.4 | 0.90 | −0.36 | −3.02 | 0.12 | −1.75 | AL512506.3 | −0.84 | 0.43 | −2.01 | 0.61 | −0.48 |
| MAGI2 | −1.17 | 0.58 | 0.90 | 0.14 | −0.10 | AC124016.2 | 0.47 | 0.11 | −0.17 | 0.22 | −0.11 | RPF2P1 | 0.56 | 0.46 | 1.79 | −0.93 | −0.81 |
| PLEKHH2 | −0.73 | 0.56 | 0.60 | 0.26 | −0.02 | FGF10 | −0.71 | 0.43 | 0.93 | −0.19 | 0.08 | RNU6-1190P | 0.25 | 0.31 | −0.03 | 0.17 | −0.07 |
| HIGDIA | 1.05 | −0.49 | −0.74 | −0.10 | −0.40 | PCDH9-AS2 | −1.09 | 0.55 | −0.52 | 0.46 | −0.29 | AP000346.2 | 0.21 | −0.55 | 0.39 | −0.42 | 1.04 |
| CPED1 | −1.29 | 0.87 | 1.26 | 0.34 | −0.02 | DBNL | 0.15 | −0.09 | −0.34 | 0.05 | −0.03 | PGRMC1 | 0.08 | −0.03 | 0.05 | −0.13 | 0.03 |
| SPRR3 | 3.49 | −3.26 | −4.40 | −0.13 | −4.25 | PABPC1P13 | −1.66 | −0.41 | −0.37 | −0.42 | 0.41 | HSD17B7P1 | −0.51 | −0.96 | −0.41 | 0.64 | 0.01 |
| BUB3 | 0.63 | −0.33 | −0.38 | −0.19 | −0.20 | AC092279.2 | −0.35 | 0.20 | 0.43 | 0.18 | 0.39 | SNRPCP13 | −0.27 | −0.97 | 0.58 | 0.39 | 0.51 |
| PBXIP1 | −0.71 | 0.57 | 0.53 | 0.16 | −0.02 | IFNA1 | 1.95 | −2.41 | −0.40 | −0.14 | 2.10 | G9256 | −0.33 | −1.20 | −0.67 | −0.83 | −0.49 |
| MRPL3 | 0.92 | −0.46 | −0.75 | −0.13 | −0.30 | AL159169.3 | 0.84 | −0.39 | −0.37 | 0.10 | −0.90 | ATP11A-AS1 | −0.11 | −0.02 | −0.02 | −0.35 | −0.11 |
| G35510 | 1.64 | −0.50 | −0.69 | 0.04 | −0.33 | SARAF | 0.23 | 0.05 | −0.02 | 0.04 | −0.20 | MIR23B | 0.16 | 0.18 | 0.35 | 0.24 | 0.02 |
| PPIEL | −0.83 | 0.33 | 0.70 | 0.15 | −0.18 | KIAA0408 | −0.80 | 1.11 | 0.68 | 0.25 | −0.61 | CHTOP | 0.04 | −0.06 | −0.10 | 0.11 | 0.11 |
| NYAP1 | −1.44 | 0.50 | 1.27 | 0.02 | 0.28 | RNU6-579P | 0.90 | −0.71 | −0.43 | −0.14 | 0.08 | AC112715.1 | 0.91 | −0.47 | 1.22 | −1.00 | −1.17 |
| P2RX7 | −1.01 | 0.49 | 0.38 | 0.52 | 0.47 | NOL4 | −0.96 | 0.68 | −0.67 | −0.03 | −0.20 | SLC23A1 | 0.10 | 0.23 | 0.17 | 0.24 | 0.06 |
| NUP37 | 0.68 | −0.43 | −0.59 | −0.01 | −0.17 | AC008840.1 | −1.04 | 1.25 | −0.28 | 0.42 | −0.79 | AL354983.1 | 0.96 | 0.24 | −1.24 | 0.94 | −2.08 |
| F2RL1 | 1.63 | −0.54 | −0.89 | −0.19 | −0.63 | RP11-292F22.7 | −0.77 | −0.16 | 1.23 | −0.40 | 1.32 | MTND4LP7 | 0.30 | 0.77 | −0.24 | 0.51 | −0.13 |
| LINC01852 | −1.29 | 0.04 | 0.51 | 0.09 | 0.36 | HNRNPKP2 | 0.66 | −0.80 | −0.34 | 0.09 | 0.40 | NGEF | −0.10 | 0.28 | −0.62 | 0.45 | −0.34 |
| MRPS16 | 0.72 | −0.43 | −0.51 | −0.10 | −0.19 | AC090921.1 | −1.09 | 0.13 | 0.27 | 0.90 | 0.26 | AC015908.1 | −0.36 | 0.20 | −0.12 | 0.34 | 0.20 |
| SGMS1-AS1 | −0.92 | 0.60 | 0.61 | 0.27 | 0.19 | CCDC107 | −0.49 | 0.34 | 0.52 | −0.30 | −0.09 | AC025576.2 | 0.24 | −0.88 | 0.52 | −0.29 | 0.89 |
| ANKRD35 | −1.45 | 1.21 | 1.61 | 1.13 | 0.70 | AC073862.4 | −0.88 | 0.16 | 1.83 | −0.44 | 1.27 | RN7SKP143 | −0.81 | −0.12 | 1.11 | 0.50 | 2.39 |
| PDSS1 | 0.91 | −0.84 | −1.23 | −0.12 | −0.24 | CELF3 | −0.62 | −0.67 | −0.17 | −0.24 | 0.77 | SERPINA11 | 0.39 | −0.59 | −1.39 | −1.24 | 1.04 |
| CNTN3 | −1.28 | 0.71 | 1.63 | −0.07 | 0.34 | AL356261.1 | 1.49 | −1.21 | −1.26 | 0.16 | −0.30 | AC116609.2 | −0.52 | 0.99 | 2.12 | 1.59 | 2.53 |
| NUF2 | 1.07 | −0.89 | −1.42 | −0.26 | −0.47 | CDCA4P2 | −1.07 | −0.26 | 2.57 | 0.99 | 2.32 | KLK4 | 0.29 | −0.62 | 0.78 | 0.09 | 0.07 |
| DBX2 | −2.48 | 0.79 | 1.63 | 0.57 | 0.32 | CDKN2C | −0.34 | 0.11 | 0.30 | 0.12 | 0.03 | RPL36AP48 | 0.22 | −0.26 | −0.87 | −0.11 | −0.79 |
| MST1 | −1.18 | 0.62 | 0.76 | 0.44 | 0.23 | AC003035.1 | −1.16 | 0.51 | 1.56 | 0.75 | 1.43 | AC093010.2 | 0.31 | −1.39 | 0.76 | −0.91 | 0.11 |
| PDE7A | 0.67 | −0.32 | −0.39 | −0.20 | 0.01 | AC130324.1 | −0.47 | 0.24 | 0.69 | −0.08 | 0.34 | GNS | 0.08 | −0.07 | 0.13 | −0.12 | −0.14 |
| PDE4DIP | −0.76 | 0.23 | 0.63 | −0.05 | 0.16 | KIF3A | −0.19 | 0.11 | 0.31 | −0.07 | 0.06 | MTCO1P39 | −0.82 | 0.75 | −0.62 | 0.73 | −0.84 |
| MRPS7 | 0.73 | −0.37 | −0.58 | −0.01 | −0.21 | AL391994.1 | −0.35 | 0.22 | 0.33 | 0.17 | 0.00 | RNU6-255P | 0.62 | −0.77 | −1.10 | 0.17 | 0.04 |
| CNNM3 | −0.91 | 0.53 | 0.68 | 0.30 | 0.19 | PLEKHO2 | 0.32 | −0.24 | −0.46 | −0.11 | −0.52 | RNU6-719P | 0.76 | −1.39 | 0.16 | −0.65 | 2.93 |
| PSMC5 | 0.51 | −0.24 | −0.50 | −0.05 | −0.30 | ARHGAP26 | −0.27 | −0.02 | 0.42 | −0.09 | 0.27 | MYO9A | −0.03 | 0.12 | 0.14 | −0.03 | −0.02 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| BIRC5 | 1.55 | −1.07 | −2.09 | 0.03 | −0.90 | AC111186.1 | 1.01 | −0.23 | −1.16 | 0.11 | −1.30 | C3orf67 | 0.13 | −0.52 | −0.41 | −0.48 | −0.40 |
| DPP4 | 1.63 | −0.63 | −1.76 | 0.00 | −0.85 | DGKA | −0.26 | 0.12 | −0.03 | 0.16 | 0.08 | RNA5SP204 | −0.69 | 0.38 | −1.05 | 0.56 | −1.47 |
| ALYREF | 0.78 | −0.58 | −1.03 | −0.03 | −0.42 | PARP11 | 0.22 | −0.27 | −0.11 | −0.13 | 0.04 | AC007161.2 | −0.17 | −0.46 | −0.22 | 0.37 | −0.36 |
| HMMR | 1.50 | −1.18 | −1.36 | −0.47 | −0.03 | AC064836.1 | −0.91 | 0.16 | 1.21 | 0.11 | 0.77 | HLA-DQA2 | 0.15 | −0.63 | 0.47 | −1.00 | 0.46 |
| RPL9P16 | 1.60 | −0.32 | −0.68 | 0.26 | −0.35 | AL450998.1 | −0.62 | 0.06 | 0.27 | 0.29 | 1.06 | AL591428.1 | −0.43 | −0.20 | −0.82 | 0.54 | 0.41 |
| AC093908.1 | 1.19 | −0.64 | −1.23 | −0.01 | −0.57 | G32314 | 0.54 | −0.76 | −0.77 | −0.24 | 0.00 | RN7SL563P | −0.52 | 1.01 | −1.32 | 1.71 | −1.72 |
| LTBP4 | −0.96 | 0.69 | 0.59 | 0.74 | 0.35 | BNIP3P38 | 0.77 | −0.92 | −0.75 | −0.25 | −0.21 | CCDC166 | −0.60 | 1.87 | 0.46 | 0.42 | −0.69 |
| PCDHGAS | −1.25 | 0.68 | 1.71 | 0.39 | 0.36 | AL096817.1 | −0.35 | 0.14 | 0.36 | −0.06 | 0.13 | NECAP1P2 | 0.24 | 0.69 | −0.27 | 0.85 | −0.59 |
| CYSRT1 | 1.54 | −0.34 | −1.32 | 0.34 | −1.32 | GPR83 | −0.80 | 0.40 | −0.11 | 1.08 | 0.26 | ASL | 0.09 | −0.01 | −0.51 | −0.01 | −0.19 |
| CNBP | 0.85 | −0.29 | −0.68 | −0.03 | −0.52 | G22722 | −0.46 | −0.25 | −1.13 | 0.17 | −0.74 | AC016987.1 | −0.59 | −0.72 | 1.28 | −0.45 | 0.49 |
| CCNYL1 | 0.84 | −0.52 | −0.71 | −0.22 | −0.28 | HEATR6 | 0.14 | −0.14 | −0.12 | 0.10 | 0.05 | MED25 | −0.05 | 0.00 | −0.26 | 0.10 | −0.01 |
| IFNGR2 | 0.65 | −0.33 | −0.85 | −0.07 | −0.50 | AC015819.1 | 1.00 | −1.10 | −0.87 | 0.28 | 1.46 | AL391058.1 | 0.08 | −0.04 | −0.06 | 0.07 | 0.19 |
| LONRF1 | −0.99 | 0.97 | 1.64 | 0.39 | 0.43 | AC008946.1 | −0.67 | −0.38 | 0.08 | −0.47 | 0.09 | AP005203.1 | −0.58 | −0.48 | 0.80 | −1.09 | 0.31 |
| ANXA2 | 0.75 | −0.38 | −0.97 | −0.08 | −0.69 | AC005828.6 | 0.72 | −0.23 | −0.06 | 0.11 | 0.41 | DUSP2 | 0.15 | −0.10 | −0.40 | −0.07 | −0.35 |
| GRIK4 | −1.62 | 0.39 | 0.12 | 1.47 | 0.26 | SPPL3 | 0.26 | 0.02 | −0.08 | 0.13 | −0.01 | DRD3 | −0.46 | 0.29 | −0.98 | −0.35 | 0.36 |
| MAP6 | −1.47 | 0.81 | 0.79 | 0.49 | −0.24 | G10661 | 1.63 | −1.16 | −3.10 | −1.25 | −2.32 | KIR2DS4 | 0.46 | −0.25 | −0.74 | 0.02 | −1.84 |
| FHOD3 | −1.03 | 0.61 | 0.81 | 0.01 | 0.02 | NKX6-1 | −0.85 | −0.41 | 0.44 | −0.42 | −0.25 | AL109615.2 | −0.26 | −0.24 | 0.80 | −0.18 | 0.52 |
| CCDC6 | 0.70 | −0.11 | −0.55 | 0.11 | −0.49 | AL136419.2 | −0.97 | 1.00 | −1.08 | −0.41 | −1.03 | AL160275.1 | −0.50 | 1.11 | 1.44 | 0.14 | 0.44 |
| PSMB5 | 0.87 | −0.36 | −0.99 | 0.10 | −0.57 | AC012085.2 | −0.25 | 0.20 | 0.57 | −0.10 | 0.37 | AC027601.1 | −0.13 | 0.05 | −1.16 | 0.18 | −0.33 |
| EPHB6 | −1.42 | 1.22 | 1.38 | 0.88 | 0.09 | AC105339.2 | 0.46 | −0.33 | 0.15 | −0.04 | 0.25 | AC007493.2 | 0.60 | 0.73 | −0.52 | 1.48 | −0.11 |
| PNMA8B | −1.32 | 0.82 | 1.01 | 0.33 | 0.31 | RPP25L | 0.33 | −0.19 | −0.35 | 0.27 | 0.31 | LINC02141 | 0.30 | −0.21 | −0.91 | 0.30 | −0.07 |
| G16985 | −3.30 | 0.99 | 1.48 | −0.47 | −0.97 | GLB1 | 0.11 | −0.17 | −0.03 | −0.07 | 0.03 | GPS2P1 | 0.20 | −0.14 | −0.59 | 0.97 | 0.68 |
| OSER1-DT | −1.17 | 0.98 | 1.14 | 0.24 | 0.10 | HNRNPCP7 | −0.41 | 0.40 | 0.47 | 0.08 | −0.21 | AC021491.1 | 0.51 | −1.03 | 0.10 | 0.63 | 0.77 |
| GALNT16 | −1.58 | 1.00 | 1.67 | 0.40 | 0.19 | AF129075.1 | 0.39 | −0.21 | −0.03 | −0.39 | −0.13 | RPL6P24 | 0.19 | −0.35 | −0.66 | −0.11 | −0.34 |
| SMAP1 | 0.65 | −0.16 | −0.52 | −0.14 | −0.40 | ATP1B1 | −0.42 | 0.44 | 0.78 | 0.11 | 0.28 | AC007599.1 | −0.13 | −0.46 | −0.09 | −0.05 | 0.38 |
| N4BP1 | 0.73 | −0.26 | −0.67 | 0.01 | −0.33 | STK38L | 0.20 | −0.02 | −0.15 | −0.18 | −0.40 | ARGFX | 0.51 | −0.49 | 0.31 | 0.12 | −1.23 |
| SEMA4F | −0.79 | 0.13 | 0.23 | 0.11 | 0.18 | B3GAT2 | 0.49 | −0.49 | −0.41 | −0.12 | −0.28 | AC104117.5 | −0.55 | −0.52 | 0.10 | 0.61 | −0.30 |
| SOD3 | −1.52 | 0.99 | 1.77 | 0.03 | 0.26 | NDUFV1 | −0.15 | 0.11 | −0.07 | 0.16 | 0.05 | RNA5SP315 | −0.71 | 0.24 | 0.84 | 1.14 | 2.20 |
| ATG3 | 0.82 | −0.50 | −0.63 | −0.20 | −0.38 | RCHY1 | 0.19 | −0.12 | −0.13 | 0.03 | −0.05 | AC074085.1 | −0.73 | 0.00 | −0.64 | −0.19 | −2.02 |
| ARL8B | 0.73 | −0.14 | −0.59 | 0.02 | −0.52 | AC124947.1 | −0.79 | 0.92 | 0.35 | 0.71 | −0.65 | LINC02380 | 0.42 | −1.38 | 0.50 | −0.82 | 0.63 |
| SCRG1 | −0.98 | 0.40 | 0.78 | 0.09 | 0.44 | AC068669.1 | −0.46 | −0.36 | −0.59 | −0.19 | 0.04 | DSCAM-AS1 | 0.52 | −1.20 | −0.24 | 0.31 | 0.21 |
| PPP2R2C | 1.17 | −0.56 | −1.14 | 0.07 | −0.45 | RP11-61J19.4 | −0.43 | 0.06 | 0.32 | −0.09 | 0.65 | AC092032.1 | −0.23 | −0.56 | 0.44 | 0.00 | 0.81 |
| PSMB7 | 0.69 | −0.23 | −0.62 | −0.16 | −0.54 | NSUN5 | 0.23 | −0.07 | −0.26 | 0.11 | 0.15 | EPYC | 0.74 | −1.73 | 0.21 | −0.13 | −0.89 |
| SLC2A9 | 1.06 | −0.94 | −1.23 | −0.43 | −0.26 | G40352 | −1.13 | −0.43 | 1.00 | −0.17 | 0.54 | AC009185.1 | 0.72 | −0.59 | 0.80 | 0.08 | 1.38 |
| ABCA12 | 1.44 | −0.46 | −0.75 | −0.10 | −0.71 | RNU7-109P | 1.22 | −0.60 | 0.69 | −0.41 | 1.02 | AC073486.1 | 0.60 | −0.74 | −1.34 | −0.87 | −0.93 |
| FAT1 | 0.92 | −0.22 | −0.69 | −0.14 | −0.59 | HAUS6P1 | 0.98 | −0.38 | −0.88 | −0.33 | −1.16 | ATP5MC1P4 | −0.40 | −1.13 | −0.49 | −1.51 | 0.30 |
| STOML2 | 0.69 | −0.38 | −0.65 | −0.22 | −0.38 | MICU1 | −0.14 | 0.32 | 0.34 | −0.10 | −0.25 | MIR3186 | −0.56 | 0.26 | 0.30 | −0.45 | −0.13 |
| POP4 | 0.58 | −0.32 | −0.49 | −0.17 | −0.36 | AL356756.1 | −0.92 | −0.39 | 0.42 | 0.08 | 1.10 | LINC01539 | −0.24 | −0.62 | −1.39 | 0.03 | 0.39 |
| RHOXF1 | −2.18 | 1.04 | 2.55 | 0.80 | −0.18 | EIF4A1P1 | −0.92 | 0.19 | 0.43 | 0.01 | 0.62 | OR2L2 | −0.21 | −0.70 | 0.35 | 0.78 | 0.86 |
| HIST1H2BI | 1.43 | −0.84 | −1.59 | 0.02 | −1.12 | PANK1 | −0.30 | 0.33 | 0.91 | 0.45 | 0.47 | LINC02277 | −0.61 | −1.04 | −0.25 | −2.16 | −1.67 |
| HSPB6 | −2.29 | 1.22 | 1.65 | 0.87 | 0.25 | G4016 | −1.71 | 0.38 | 0.44 | 0.78 | 0.72 | AC009053.3 | −0.48 | −1.00 | −0.39 | −0.46 | 0.46 |
| HIST1H1B | 1.50 | −1.16 | −1.55 | −0.35 | −0.84 | AC007738.1 | 0.76 | −0.32 | −0.24 | −0.08 | 0.15 | OR51B8P | −0.92 | 0.82 | −0.83 | 1.79 | 0.33 |
| AKAP12 | −1.66 | 0.73 | 1.60 | 0.43 | 0.16 | SMIM36 | −0.84 | 0.27 | −0.52 | 1.25 | 0.61 | SLC9B1P4 | −0.51 | 0.16 | 0.27 | −0.33 | −0.21 |
| IL1R2 | 1.64 | −1.54 | −1.75 | −0.26 | −0.01 | LINC00460 | 1.17 | −1.62 | −2.59 | 0.02 | −1.33 | AC040970.1 | −0.17 | −0.03 | −0.63 | −0.04 | −1.34 |
| HNRNPK | 0.79 | −0.34 | −0.58 | −0.14 | −0.41 | ADAMTS14 | 0.42 | −1.10 | −1.30 | −0.87 | −0.24 | MMAB | −0.06 | −0.02 | 0.25 | 0.10 | 0.06 |
| POMP | 1.10 | −0.61 | −0.74 | −0.39 | −0.54 | AC092902.1 | −0.86 | 0.37 | 2.16 | −0.26 | 0.43 | MED28P3 | −0.13 | 0.02 | 0.69 | −0.28 | 0.33 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| SFTPC | −2.93 | 1.25 | 1.56 | 0.56 | 0.21 | MKRN4P | 1.48 | −2.14 | −0.47 | −1.56 | −0.65 | AL035258.1 | −0.32 | 1.23 | −0.37 | 1.13 | 0.58 |
| SNORD94 | −1.19 | 0.86 | 0.96 | 0.23 | 0.00 | AC006461.1 | 0.69 | 0.55 | −0.05 | 0.56 | −0.50 | SNORA70F | 0.50 | 0.14 | 0.28 | 0.64 | −0.37 |
| B4GALT1 | 0.92 | −0.41 | −0.71 | −0.35 | −0.44 | CNEP1R1 | 0.19 | −0.18 | 0.16 | −0.09 | 0.00 | AC097347.1 | 0.33 | −1.19 | 0.93 | −0.11 | 0.03 |
| RAC2 | 1.23 | −1.18 | −0.79 | −0.49 | 0.19 | AC094085.1 | 0.66 | 0.09 | −1.26 | 0.47 | −0.46 | AL137072.1 | 0.32 | −0.04 | 0.35 | −0.94 | −0.98 |
| ECM1 | 0.99 | −0.12 | −0.66 | −0.15 | −0.77 | G3383 | −0.18 | 0.19 | 0.16 | −0.01 | −0.03 | AC092053.2 | 0.22 | −0.22 | 0.39 | −0.74 | −0.15 |
| BRSK2 | −1.50 | 1.08 | 1.55 | 0.63 | 0.31 | KLHL11 | 0.23 | −0.08 | −0.03 | −0.11 | −0.13 | AC138028.1 | 0.11 | −0.07 | −0.59 | −0.10 | −0.34 |
| PRSS27 | 1.45 | −0.94 | −1.91 | −0.04 | −0.78 | AATK | −0.47 | −0.18 | −0.56 | 0.27 | 0.08 | AC138150.1 | −0.18 | 0.07 | 0.43 | 0.38 | 0.41 |
| AC090517.5 | −1.01 | 0.43 | 0.91 | 0.08 | 0.41 | BRSK1 | −0.54 | −0.15 | 0.09 | 0.01 | 0.14 | ADGRG3 | 0.24 | −1.35 | −0.60 | −0.65 | −0.59 |
| MITF | −1.01 | 0.82 | 1.14 | 0.22 | 0.10 | G7528 | 1.58 | −3.19 | −1.15 | −0.94 | 0.69 | BGLAP | −0.21 | 0.62 | 0.14 | 0.23 | 0.05 |
| ISG20 | 1.06 | −0.93 | −0.92 | −0.61 | −0.53 | G28011 | −1.53 | 0.20 | 0.48 | −0.08 | 0.21 | KCNA5 | 0.26 | −0.04 | −0.41 | 0.48 | −0.19 |
| ERBB4 | −1.79 | 0.50 | 1.62 | 0.63 | 0.82 | DLX2 | −0.58 | 0.64 | 0.23 | 0.46 | −0.48 | RN7SL675P | 0.37 | −0.24 | −0.26 | 0.60 | 0.33 |
| ANO9 | −1.31 | 0.73 | 1.28 | 0.40 | 0.60 | LINC01493 | −1.24 | 0.13 | −1.00 | 0.39 | 1.04 | HIST3H2BB | 0.12 | 0.04 | −0.13 | 0.53 | −0.07 |
| BCL10 | 0.73 | −0.33 | −0.69 | −0.12 | −0.45 | SCAF1 | −0.21 | 0.03 | −0.14 | 0.14 | 0.12 | AL158209.1 | 0.41 | −1.10 | −0.92 | 0.28 | 0.23 |
| DCLK1 | −1.47 | 0.74 | 1.89 | 0.14 | 0.47 | AC026523.2 | −0.79 | −0.06 | 0.04 | 0.26 | 0.44 | AC139099.3 | 0.43 | 1.39 | −1.04 | 0.62 | −0.56 |
| LDB1 | −0.90 | 0.47 | 0.29 | 0.47 | 0.09 | LINC02280 | −0.59 | −0.17 | 0.99 | −0.57 | −0.02 | LIME1 | 0.19 | −0.13 | −0.77 | 0.16 | 0.00 |
| HIST1H2BO | 1.69 | −1.01 | −1.60 | −0.32 | −1.05 | LIMCH1 | −0.27 | 0.14 | 0.03 | 0.18 | −0.24 | AC103796.1 | 0.51 | −0.23 | −0.36 | −1.30 | −0.70 |
| FHL3 | 0.65 | −0.35 | −0.90 | 0.08 | −0.25 | AC015987.1 | 0.58 | 0.00 | −0.16 | −0.28 | −0.10 | AC092301.1 | 0.13 | 0.11 | 0.21 | −0.14 | −0.18 |
| PLAA | 0.63 | −0.20 | −0.57 | −0.05 | −0.41 | FBXL13 | −0.21 | 0.28 | 0.31 | 0.20 | 0.20 | LINC00163 | −0.23 | 0.22 | −0.85 | 0.50 | 0.03 |
| RIC8A | 0.51 | −0.31 | −0.66 | −0.03 | −0.33 | AC008429.1 | −0.44 | 0.10 | −0.11 | −0.14 | 0.12 | AC092941.2 | 0.48 | −1.27 | −2.94 | 1.22 | −1.29 |
| ELN | −1.57 | 1.37 | 1.71 | 0.27 | −0.51 | AC020741.1 | −0.60 | 0.24 | −0.15 | 0.30 | 0.38 | OR7E115P | −0.63 | −0.42 | −0.11 | 0.33 | 0.70 |
| GDI2 | 0.85 | −0.45 | −0.61 | −0.25 | −0.49 | AC015908.3 | −0.82 | −0.76 | 0.04 | 0.42 | 0.12 | RPS3AP53 | −0.49 | 0.22 | 2.35 | −1.04 | 0.24 |
| EPN1 | 0.58 | −0.27 | −0.76 | −0.07 | −0.29 | RHBG | −0.49 | 0.49 | 1.37 | 0.71 | 0.22 | APCS | −0.94 | 0.41 | 0.34 | −0.29 | −0.45 |
| CAPS2 | −1.00 | 0.90 | 0.88 | 0.41 | 0.32 | RN7SL520P | −1.30 | −0.42 | 2.86 | −1.36 | 0.89 | G28632 | −0.24 | 0.82 | 1.74 | 0.04 | −0.32 |
| CLPP | 0.64 | −0.27 | −0.56 | −0.01 | −0.16 | AC118553.2 | 0.41 | −0.51 | −0.48 | −0.23 | −0.18 | AL353708.1 | −0.21 | 0.16 | −1.25 | 0.22 | −0.43 |
| RPSA | 0.88 | −0.35 | −0.58 | −0.19 | −0.70 | AC092117.2 | −0.35 | 0.04 | −0.24 | −0.21 | 0.05 | G28650 | 0.16 | −0.09 | −0.12 | 0.14 | 0.23 |
| RBL1 | 0.74 | −0.48 | −0.90 | 0.02 | −0.17 | AC105150.1 | 0.83 | −0.44 | −0.05 | 0.08 | 0.24 | AC003043.2 | −0.29 | −0.87 | 0.27 | −0.40 | 0.89 |
| LINC02457 | 2.54 | −2.07 | −1.64 | −0.29 | 0.35 | AC016257.1 | 1.05 | −1.18 | 0.51 | −1.36 | 0.21 | BX546450.1 | −0.73 | 0.82 | 1.41 | 0.61 | −0.42 |
| GSTM3 | −1.06 | 0.64 | 0.85 | 0.34 | −0.03 | LRRC55 | 0.59 | −0.36 | −0.99 | 0.02 | −0.66 | AC007342.6 | 0.14 | 0.18 | 0.52 | 0.14 | −0.03 |
| SLC2A3P2 | −1.50 | 0.74 | 0.84 | 0.22 | 0.19 | FAM71E1 | −0.58 | −0.04 | 0.39 | 0.02 | 0.34 | CCT5P2 | 0.71 | 0.32 | −0.46 | 0.99 | −0.83 |
| LINC02159 | 2.44 | −0.66 | −0.62 | 0.10 | −0.49 | HSD17B7 | −0.20 | 0.07 | 0.46 | 0.16 | 0.45 | MIR1827 | 0.55 | −1.10 | −0.19 | −1.14 | −0.20 |
| CCHCR1 | −0.71 | 0.07 | 0.30 | 0.05 | 0.35 | PCDH10 | −0.75 | −0.46 | −0.16 | 1.33 | 0.56 | AC024614.4 | 0.59 | −2.21 | −0.63 | −0.01 | 1.90 |
| RALA | 0.96 | −0.46 | −0.75 | −0.35 | −0.59 | PTMAP5 | 0.28 | −0.25 | −0.41 | 0.01 | 0.12 | AC005821.1 | 0.30 | −0.07 | −0.20 | 0.32 | −0.85 |
| FAM120A | 0.51 | −0.33 | −0.39 | −0.14 | −0.08 | PLXNB1 | −0.30 | 0.16 | −0.45 | 0.43 | 0.17 | AC117500.1 | −0.70 | −0.45 | 2.12 | 0.99 | 1.72 |
| MTFR1 | 0.53 | −0.16 | −0.22 | −0.11 | −0.24 | H2BFS | 0.72 | −0.17 | −0.63 | −0.15 | −0.52 | EIF4A1P6 | 0.63 | −1.00 | −0.24 | −0.62 | 0.02 |
| ARPC5 | 0.55 | −0.28 | −0.38 | −0.16 | −0.31 | AC009313.1 | 1.17 | −0.32 | 1.08 | −1.05 | 0.36 | SLC25A31 | 0.53 | −0.05 | 2.45 | 0.59 | 0.96 |
| SRPRB | 0.98 | −0.64 | −0.30 | −0.24 | −0.05 | ENO1P2 | 2.03 | 0.52 | −0.37 | −0.23 | −1.67 | KLHL13 | −0.12 | 0.05 | 0.28 | 0.07 | 0.27 |
| CYP2S1 | 1.06 | −0.44 | −1.40 | 0.15 | −0.32 | AC073583.1 | 0.93 | −0.83 | −0.62 | 0.12 | 0.42 | RNU4-14P | 0.43 | −0.01 | −0.50 | 0.34 | −0.79 |
| PHB | 0.91 | −0.45 | −0.76 | −0.06 | −0.38 | AL353803.1 | −1.16 | −1.52 | 1.54 | −0.23 | 1.28 | AC003973.1 | −0.87 | −1.53 | 0.29 | −1.54 | −0.52 |
| SNORA47 | −1.18 | 0.96 | 1.22 | 0.13 | −0.42 | G4615 | −1.34 | −0.58 | −1.72 | 0.92 | 1.66 | AP000812.1 | −0.51 | −0.16 | −0.17 | 0.78 | −0.12 |
| EIF3M | 0.68 | −0.27 | −0.49 | −0.12 | −0.35 | LINC01637 | −0.75 | −0.35 | 0.52 | −0.01 | 1.47 | NME7 | −0.08 | 0.11 | 0.05 | 0.00 | −0.09 |
| SLK | 0.68 | −0.21 | −0.68 | −0.07 | −0.43 | PPIAP28 | 1.89 | −0.88 | −2.68 | −1.03 | −0.94 | AL356056.1 | 0.29 | −0.76 | −1.73 | −0.41 | −1.05 |
| ARHGEF7 | −0.36 | 0.22 | 0.29 | 0.01 | 0.00 | CUZD1 | −0.44 | −0.33 | 0.30 | −0.35 | −0.05 | AC007279.1 | 0.14 | −0.32 | 0.41 | −0.12 | 0.44 |
| SNU13 | 0.58 | −0.29 | −0.45 | −0.11 | −0.31 | ALOX5AP | 0.64 | −0.83 | −0.45 | −0.11 | −0.30 | MIR548AQ | −0.37 | −0.78 | 1.10 | −0.45 | 1.51 |
| CSK | 0.55 | −0.17 | −0.36 | −0.08 | −0.23 | MGMT | −0.14 | 0.08 | 0.05 | 0.17 | 0.05 | GLYR1 | 0.04 | −0.03 | −0.31 | 0.07 | −0.17 |
| ITIH5 | −1.57 | 1.25 | 1.46 | 0.67 | −0.02 | GRIK1 | 0.24 | −0.08 | −0.20 | −0.33 | −0.21 | AL451050.1 | 0.71 | 0.02 | −1.56 | 1.14 | −0.30 |
| BTBD8 | −0.81 | 0.42 | 0.52 | 0.29 | 0.23 | FAM210B | 0.30 | 0.17 | 0.00 | 0.02 | −0.34 | PRH1 | 0.10 | −0.14 | 0.23 | −0.02 | 0.33 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| HYOU1 | 0.86 | −0.69 | −0.90 | −0.35 | −0.15 | AP003064.1 | −0.65 | 0.84 | 0.65 | 0.44 | 0.35 | AC080038.3 | −0.18 | −0.12 | 0.74 | −0.34 | 0.03 |
| PITPNM1 | 1.00 | −0.63 | −1.46 | 0.06 | −0.37 | AC016831.2 | −0.59 | 0.36 | 0.17 | 0.49 | 0.38 | H2BFM | 0.77 | −0.34 | −1.52 | 1.12 | −1.02 |
| PRXL2B | 0.73 | −0.45 | −0.68 | 0.17 | −0.02 | AC011611.5 | 0.96 | −1.24 | 0.17 | −0.31 | 1.14 | PNLIP | −0.38 | 0.20 | −0.41 | 0.85 | −0.44 |
| SNCB | 2.72 | −1.64 | −3.49 | 0.28 | −2.21 | MCEE | 0.22 | 0.19 | 0.21 | 0.12 | −0.05 | SDHCP2 | −0.20 | 0.61 | −0.05 | 0.20 | 0.09 |
| GFOD2 | 0.72 | −0.14 | −0.51 | −0.10 | −0.48 | NMNAT1P1 | −1.06 | 1.13 | 2.33 | −0.50 | −0.67 | AC003009.1 | 0.56 | −0.39 | −0.75 | 0.00 | 0.98 |
| PGR | −1.57 | 0.89 | 1.19 | 0.47 | 0.31 | C1GALT1 | 0.18 | −0.23 | −0.04 | −0.25 | −0.02 | LACTB2-AS1 | −0.09 | −0.18 | 0.50 | 0.02 | 0.28 |
| PTPN21 | −0.40 | 0.39 | 0.43 | 0.12 | −0.02 | AC027796.4 | −0.44 | −0.10 | −0.15 | 0.10 | −0.08 | DDX18P6 | 0.59 | −2.11 | −1.36 | 0.62 | 1.88 |
| AFAP1L2 | 0.81 | −0.42 | −1.10 | 0.10 | −0.19 | IQCJ | −1.05 | −0.51 | −1.06 | 0.44 | 1.06 | SIGLEC22P | 0.25 | −0.15 | 0.63 | 0.61 | 0.40 |
| BZW1P2 | 1.72 | −0.66 | −2.08 | 0.06 | −1.20 | PTGER4 | −0.33 | −0.07 | 0.02 | −0.06 | 0.18 | AC022167.4 | 0.79 | −0.79 | 0.15 | −0.77 | −0.40 |
| FAM83A-AS1 | 2.48 | −1.79 | −1.89 | −1.02 | −0.43 | AL359504.2 | −0.77 | −0.03 | 0.17 | −0.14 | 0.28 | DUSP16 | 0.06 | 0.19 | 0.28 | −0.01 | 0.04 |
| OXER1 | −1.29 | 0.49 | 0.86 | 0.71 | 0.83 | RPS27P1 | 1.45 | −2.42 | −2.40 | 0.30 | 1.43 | AC009314.1 | 0.38 | −0.56 | −1.67 | 1.03 | −0.48 |
| ANKRD20A3 | −2.30 | 0.76 | 0.87 | 0.27 | 0.33 | DGCR5 | −0.52 | 0.25 | −0.24 | 0.36 | −0.17 | CFAP47 | −0.25 | −0.73 | −0.54 | 0.56 | 0.00 |
| PPP2R5E | 0.60 | −0.28 | −0.50 | −0.04 | −0.20 | AC008474.1 | 0.76 | −0.37 | −0.36 | −0.48 | −0.29 | FLJ33534 | −0.56 | −0.12 | −0.78 | 0.59 | −1.42 |
| SLC38A1 | 1.17 | −0.45 | −0.63 | −0.14 | −0.35 | RNU1-91P | 0.71 | −0.56 | −0.06 | −0.51 | 0.01 | SMG6 | 0.04 | −0.02 | −0.01 | −0.04 | 0.07 |
| SH3BP2 | −0.86 | 0.36 | 0.40 | 0.12 | 0.07 | AC022710.1 | −0.62 | 0.45 | −0.18 | 0.49 | −0.26 | AL355433.1 | −0.30 | 0.22 | −1.20 | −0.33 | −1.78 |
| PSMA3 | 0.68 | −0.43 | −0.47 | −0.22 | −0.14 | AC011632.1 | −0.85 | 0.00 | −0.62 | −0.02 | −0.39 | LINC01483 | −0.31 | −0.68 | −1.16 | −0.47 | −1.08 |
| CRYBB2P1 | −0.53 | 0.25 | 0.21 | −0.01 | −0.09 | RMRPP4 | 0.98 | −0.69 | 0.88 | 0.70 | 1.61 | SRSF4 | −0.05 | −0.14 | −0.27 | −0.03 | −0.07 |
| BRD9P2 | −2.61 | 1.45 | 2.18 | 0.92 | −0.53 | AC140479.1 | 2.30 | 1.68 | −2.15 | 1.11 | −2.53 | ARF4P1 | 0.86 | −0.37 | −1.30 | −0.17 | 0.12 |
| HCG23 | −1.35 | 0.48 | 0.43 | 0.64 | 0.23 | FAM177B | −0.62 | −0.02 | −0.69 | 0.05 | −0.33 | AC008067.1 | −0.37 | −1.13 | −0.53 | −0.22 | −0.62 |
| MYL12A | 0.75 | −0.28 | −0.55 | −0.32 | −0.59 | MYT1 | 0.77 | −0.02 | −1.57 | 0.39 | −0.58 | AC139495.3 | 0.09 | −0.46 | −0.40 | 0.02 | 0.52 |
| NUP153 | 0.63 | −0.29 | −0.51 | −0.16 | −0.39 | AC008764.9 | −0.51 | 0.79 | 0.26 | 0.36 | −0.19 | AL513302.1 | −0.34 | 0.33 | 0.43 | 2.12 | 1.48 |
| FLRT3 | 1.52 | −0.54 | −1.14 | −0.59 | −1.10 | MLIP-AS1 | 0.50 | −0.18 | −0.03 | −0.22 | −0.27 | BIK | 0.15 | 0.25 | −0.10 | −0.05 | −0.04 |
| PUM3 | 0.81 | −0.54 | −0.73 | −0.23 | −0.16 | AL121839.1 | 1.00 | −0.07 | −0.70 | 0.23 | 0.54 | KRTAP5-5 | −0.97 | 0.59 | 0.16 | −0.05 | 0.34 |
| PWAR5 | −1.03 | 0.71 | 1.32 | 0.19 | 0.30 | CD300LG | −0.62 | 0.62 | 0.80 | 0.71 | −0.03 | OR2T6 | 0.37 | −0.62 | −2.21 | 0.68 | −0.29 |
| ATXN3 | −0.43 | 0.28 | 0.47 | 0.09 | 0.07 | AF279873.1 | 1.04 | 0.16 | −2.58 | 0.05 | −1.51 | AC009478.1 | 0.49 | −1.49 | 0.64 | 0.38 | 1.37 |
| OXSR1 | 0.63 | −0.44 | −0.61 | −0.34 | −0.30 | ARFGAP1 | −0.23 | −0.19 | −0.16 | −0.03 | 0.13 | AC016747.4 | 0.27 | −1.31 | 1.37 | −0.67 | 1.14 |
| CDON | −1.16 | 0.73 | 1.26 | 0.37 | 0.13 | OR13G1 | −0.81 | 0.11 | 1.20 | −0.31 | 0.54 | MLLT10P2 | 0.27 | −0.32 | −2.32 | 0.97 | −0.70 |
| RNF6 | 0.79 | −0.24 | −0.51 | −0.17 | −0.42 | G10551 | −1.14 | 0.74 | 1.41 | 0.82 | 1.43 | IPO7P2 | 0.20 | −0.59 | −0.63 | −0.66 | −1.00 |
| OR10Q2P | −2.57 | 1.80 | 2.50 | 0.20 | −0.36 | AC008708.2 | −1.35 | 0.93 | 1.48 | −0.36 | 0.75 | AC008115.1 | −0.44 | −0.36 | 0.50 | −0.87 | −0.25 |
| AC011481.3 | −1.88 | 0.53 | 1.34 | 0.45 | 0.48 | QARS | 0.13 | 0.09 | −0.27 | 0.13 | −0.27 | AC139426.3 | −0.63 | −0.38 | 0.26 | 1.36 | 0.72 |
| BIRC7 | −2.41 | 0.71 | 0.35 | 1.90 | 0.45 | CERS4 | −0.24 | 0.33 | 0.04 | 0.28 | −0.03 | RP11-475I24.8 | −0.52 | −0.61 | 0.94 | −0.42 | 0.23 |
| PRELID3B | 1.06 | −0.27 | −0.64 | −0.21 | −0.78 | AF230666.2 | 0.64 | 0.09 | −0.03 | 0.22 | 0.36 | RPL7AP14 | 0.49 | 0.34 | 1.03 | 0.71 | 0.09 |
| SNRNP40 | 0.53 | −0.31 | −0.51 | −0.06 | −0.15 | AC091825.1 | −0.41 | 0.14 | 0.43 | −0.44 | −0.32 | AC093655.1 | −0.70 | −1.05 | 1.41 | 1.20 | 1.41 |
| AP2M1 | 0.68 | −0.36 | −0.38 | −0.31 | −0.27 | SPATA31C2 | 1.29 | −1.16 | −1.69 | −0.12 | 0.27 | AC006077.1 | 0.28 | −1.19 | −0.61 | 0.04 | 0.79 |
| LMAN2 | 0.48 | −0.21 | −0.41 | −0.03 | −0.13 | AC008770.3 | −0.44 | 0.35 | 1.04 | −0.19 | 0.15 | AL117339.1 | −0.40 | −2.09 | −1.19 | 0.70 | −0.31 |
| RAE1 | 0.61 | −0.38 | −0.72 | −0.05 | −0.26 | AC008481.2 | −0.65 | 0.14 | −0.04 | 0.17 | −0.17 | CR2 | −0.31 | −0.38 | −0.79 | −0.18 | −1.12 |
| GTF2H1 | 0.52 | −0.26 | −0.35 | −0.06 | −0.08 | SEC22A | 0.19 | −0.02 | 0.13 | −0.05 | 0.02 | AC079336.3 | 0.19 | −0.05 | 0.13 | −0.35 | −0.31 |
| ATP6VOE2 | −1.08 | 0.85 | 1.02 | 0.38 | 0.32 | G32329 | −0.58 | −0.28 | 0.76 | 0.36 | 1.50 | AC087672.2 | −0.19 | −0.42 | 0.20 | 0.18 | 1.32 |
| PECR | −1.14 | 0.53 | 0.79 | 0.52 | 0.56 | PGGHG | −0.39 | −0.19 | −0.03 | 0.14 | 0.26 | KRTAP10-5 | −0.58 | −0.94 | 0.40 | −0.47 | 1.04 |
| GUSBP2 | −0.86 | 0.28 | 0.30 | 0.21 | −0.11 | AC112236.1 | 1.20 | 0.15 | 1.09 | 0.70 | −1.22 | LINC02495 | 0.27 | 0.41 | −1.15 | 0.02 | −1.19 |
| ST13P20 | 1.49 | −0.30 | −0.65 | −0.27 | −0.17 | AL356134.1 | 1.83 | −0.10 | −2.10 | −0.22 | −2.19 | AC008154.2 | −0.37 | −0.55 | 0.25 | −0.80 | 1.55 |
| EIF1AX | 0.74 | −0.26 | −0.57 | −0.09 | −0.38 | RNA5SP210 | −0.62 | 0.76 | 1.20 | 0.20 | 0.70 | PALM2-AKAP2 | 0.31 | −0.56 | 1.68 | −1.03 | 0.22 |
| LRRC4 | 1.02 | −0.56 | −1.26 | −0.15 | −0.29 | EDA2R | −0.39 | 0.11 | 0.78 | −0.07 | 0.39 | AC126124.1 | −0.24 | 0.27 | 0.16 | 0.07 | 0.05 |
| MAPRE3 | −0.70 | 0.62 | 0.47 | 0.34 | 0.07 | REXO5 | 0.31 | −0.63 | −0.99 | 0.01 | −0.13 | RNA5SP379 | −0.30 | 0.77 | 0.23 | 0.50 | −0.39 |
| AC080188.1 | 1.66 | −0.18 | −0.55 | 0.05 | −0.55 | RN7SL642P | −0.84 | 0.22 | 0.14 | 0.60 | 0.34 | AL353152.1 | −0.36 | −0.64 | −0.22 | −0.47 | −0.56 |
| HIST1H2BK | 1.16 | −0.70 | −1.21 | −0.31 | −0.72 | PARD3-AS1 | −1.00 | 1.55 | 0.97 | 0.82 | 0.33 | KIR3DX1 | −0.32 | −0.27 | −0.95 | −0.01 | −0.44 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| ATP2B2 | −1.34 | 0.00 | 1.00 | 0.35 | 0.65 | KIRREL3-AS1 | −1.64 | 0.02 | −0.43 | 1.56 | 1.40 | AC025181.2 | −0.11 | 0.10 | 0.20 | 0.08 | −0.18 |
| AP001528.3 | −1.69 | 1.08 | 1.58 | 0.58 | 0.19 | CCRL2 | 0.80 | −0.76 | −0.30 | 0.13 | −0.77 | MTND2P6 | 0.58 | −2.29 | −0.69 | −0.27 | −0.01 |
| SGO1 | 1.17 | −0.70 | −0.98 | −0.24 | −0.38 | APOL6 | 0.47 | −0.67 | −0.70 | −0.51 | −0.37 | DHCR24 | 0.10 | 0.07 | 0.05 | 0.25 | −0.01 |
| CPA6 | 3.10 | −0.07 | −2.05 | 0.27 | −1.06 | B4GALT2 | 0.19 | −0.13 | −0.40 | −0.04 | −0.26 | AC129492.2 | −0.59 | −0.36 | 2.15 | 1.63 | 0.85 |
| KCTD10 | 0.55 | −0.31 | −0.41 | −0.21 | −0.28 | AP000904.1 | 1.26 | −0.58 | −2.83 | 1.20 | −1.20 | PMS2P5 | −0.10 | −0.07 | 0.00 | −0.42 | 0.01 |
| KCNT2 | −1.51 | 0.60 | 1.59 | 0.41 | 0.16 | AC024405.2 | −1.08 | −0.30 | −1.74 | 1.21 | −0.67 | CACYBPP3 | 0.29 | 0.54 | 0.51 | 0.08 | −0.49 |
| CCDC154 | −1.75 | 0.63 | −0.01 | 0.73 | 0.29 | ARAF | −0.14 | 0.03 | −0.13 | 0.12 | 0.01 | G10252 | −0.12 | −0.07 | −0.35 | 0.58 | 0.12 |
| AC018638.1 | −2.06 | 0.26 | 0.39 | 0.78 | 0.39 | RN7SKP274 | −0.40 | 0.48 | 0.35 | 0.16 | −0.36 | AP003065.1 | 0.78 | −0.62 | −0.41 | 0.01 | −0.07 |
| IL24 | 2.53 | −2.19 | −2.17 | −1.92 | −0.95 | CCZ1B | 0.18 | −0.08 | −0.09 | −0.01 | −0.11 | ARHGAP26-AS1 | 0.23 | 0.25 | −0.34 | 0.21 | −0.11 |
| SNHG16 | 0.64 | −0.43 | −0.39 | −0.16 | −0.11 | AC009041.4 | 0.65 | −0.19 | −0.68 | −0.26 | −0.66 | MAGI1-IT1 | 0.11 | 0.18 | 0.23 | −0.13 | 0.13 |
| ASAP2 | −0.65 | 0.22 | 0.24 | −0.01 | −0.09 | C1orf116 | 0.31 | 0.35 | 0.02 | 0.07 | −0.35 | G23691 | −0.37 | 1.52 | −0.44 | 1.27 | 0.08 |
| MRPL13 | 1.01 | −0.56 | −0.88 | −0.27 | −0.54 | GOLGA8T | −1.10 | 0.56 | −1.43 | 1.52 | −1.80 | NELFB | −0.05 | 0.02 | −0.24 | 0.17 | −0.08 |
| CMAS | 0.76 | −0.28 | −0.64 | −0.14 | −0.47 | AC036103.1 | 0.43 | −0.08 | −0.23 | 0.21 | 0.21 | AL354936.1 | −0.32 | −0.40 | −0.91 | 0.46 | −0.04 |
| HMGB1P41 | −0.95 | 0.57 | 0.91 | 0.40 | 0.09 | SH3BP1 | 0.23 | −0.20 | −0.47 | 0.17 | 0.00 | SERTM2 | 0.34 | −0.79 | 0.44 | −0.29 | −0.08 |
| LCN2 | 2.07 | −1.37 | −2.60 | −1.49 | −2.01 | MIR583HG | −0.84 | 0.75 | 1.32 | −0.41 | 0.27 | RPS5P2 | 0.18 | −1.02 | −0.38 | 0.10 | −0.14 |
| C2orf40 | −1.85 | 1.58 | 0.87 | 0.68 | −0.73 | C1orf122 | 0.32 | −0.30 | −0.19 | −0.15 | 0.04 | RN7SKP119 | −0.58 | −0.49 | 0.95 | −1.83 | −0.23 |
| MYH11 | −1.34 | 0.76 | 0.77 | 0.50 | −0.18 | RPL21P132 | 0.94 | −1.61 | −0.40 | 0.13 | 1.37 | SAMD12-AS1 | −0.29 | −0.10 | 0.84 | −0.08 | 0.50 |
| MCM6 | 0.92 | −0.78 | −0.90 | −0.14 | −0.31 | APBB3 | −0.25 | 0.13 | −0.07 | 0.28 | 0.35 | HTR3C | −0.43 | 0.20 | −2.03 | 1.29 | −1.96 |
| EIF2S3 | 0.70 | −0.29 | −0.60 | −0.06 | −0.32 | C9orf24 | −0.66 | −0.36 | 1.86 | −0.59 | 0.72 | AC008817.1 | −0.67 | −0.22 | 0.77 | 1.04 | −0.87 |
| RAB18 | 0.65 | −0.21 | −0.54 | −0.04 | −0.31 | ADAD1P2 | 1.19 | −0.57 | 0.27 | −0.61 | −0.28 | G30962 | −0.26 | 0.37 | 0.28 | 0.48 | −0.83 |
| BEND7 | −1.18 | 0.61 | 0.82 | 0.05 | 0.14 | AC055733.2 | 0.50 | −0.16 | 0.49 | −0.04 | 0.45 | EEF1A1P38 | −0.33 | −0.29 | −0.07 | −1.02 | −0.01 |
| CROCCP2 | −1.02 | 0.20 | 0.26 | 0.42 | 0.18 | LINC02207 | 1.06 | 0.10 | −1.23 | 0.18 | −0.75 | ACTG1P15 | 0.24 | 0.06 | 0.64 | −0.03 | 0.65 |
| CYP2J2 | −1.48 | 1.50 | 1.76 | 0.48 | 0.24 | RPS3P1 | −0.57 | 0.80 | 1.25 | 0.07 | −0.22 | AC017079.1 | 0.77 | −2.54 | 1.35 | −2.08 | 1.65 |
| PSMD12 | 0.65 | −0.38 | −0.63 | −0.24 | −0.30 | RABGAP1L-IT1 | −0.43 | −0.34 | 0.64 | −0.33 | 0.29 | KIF2B | −0.47 | −1.36 | −0.24 | 1.05 | 0.36 |
| MAPRE1 | 0.68 | −0.36 | −0.63 | −0.16 | −0.40 | LINC02050 | −1.00 | −0.28 | −1.45 | 0.21 | −1.34 | CR382287.2 | 0.44 | −0.61 | −1.00 | 0.47 | 0.17 |
| AC109635.5 | −3.01 | 2.12 | −0.18 | 1.70 | 0.06 | MPG | 0.21 | 0.05 | −0.22 | 0.07 | −0.14 | RNA5SP114 | −0.91 | 1.52 | 0.75 | 1.51 | −1.46 |
| SLC7A8 | 1.03 | −0.07 | −0.74 | 0.10 | −0.99 | GEM | −0.32 | 0.38 | 0.77 | −0.28 | −0.10 | AC006020.1 | −0.28 | −0.09 | 0.49 | −0.16 | 0.76 |
| CYP4F12 | −1.45 | 1.06 | 1.05 | 0.80 | 0.31 | SLC25A20 | −0.30 | 0.19 | 0.14 | −0.02 | 0.18 | AC020915.5 | 0.21 | −0.93 | 1.09 | 0.02 | 1.07 |
| KDM1A | 0.49 | −0.25 | −0.49 | −0.14 | −0.20 | AC018467.1 | −1.08 | 0.07 | 0.08 | 1.04 | 0.20 | RPS12P27 | 0.16 | −0.08 | 0.27 | −0.01 | 0.45 |
| DCLRE1B | 0.74 | −0.40 | −0.11 | −0.25 | −0.08 | G42645 | −0.48 | −0.21 | −0.07 | 0.17 | −0.32 | LINC01002 | 0.09 | −0.41 | −0.20 | 0.23 | 0.68 |
| HSPA1L | −1.35 | 0.24 | 0.62 | 0.35 | 0.35 | APCDD1L-DT | −0.41 | 0.52 | 0.26 | −0.51 | −0.42 | KRTAP1-1 | −0.72 | 0.18 | 0.27 | −0.53 | −0.96 |
| SNX5 | 0.65 | −0.56 | −0.66 | −0.14 | −0.11 | COG7 | −0.14 | −0.12 | 0.03 | 0.02 | 0.25 | AL365366.1 | 0.34 | −1.48 | −0.95 | −0.62 | 0.14 |
| ACOX2 | −1.42 | 0.82 | 1.19 | 0.46 | 0.37 | AC005482.1 | −1.40 | −0.17 | −0.70 | −0.93 | −1.08 | AC093827.1 | −0.28 | 0.34 | 1.36 | 0.32 | 0.91 |
| HIST1H2BH | 1.53 | −1.02 | −0.98 | −0.59 | −0.46 | SLC25A5-AS1 | −0.29 | 0.47 | 0.54 | 0.26 | −0.01 | FAM234A | −0.05 | 0.16 | 0.29 | 0.05 | −0.02 |
| AP1S1 | 0.91 | −0.32 | −0.62 | −0.06 | −0.39 | OR7E14P | −0.56 | −0.14 | 0.26 | −0.06 | 0.56 | ATP13A4-AS1 | 0.29 | 0.11 | 0.65 | 0.12 | −0.03 |
| LYPD3 | 1.46 | −0.11 | −1.06 | 0.15 | −0.94 | FDPS | 0.24 | −0.06 | −0.53 | 0.34 | −0.27 | LPA | −0.28 | 0.27 | −1.64 | 0.29 | −1.60 |
| M6PR | 0.66 | −0.41 | −0.50 | −0.19 | −0.07 | AC020891.1 | −0.67 | −0.38 | 0.37 | 0.26 | 0.98 | OR5W1P | −0.61 | −1.08 | 0.12 | 1.27 | 0.39 |
| SLC13A3 | −0.90 | 0.23 | 0.58 | −0.06 | 0.48 | RNA5SP515 | −1.38 | 2.09 | −1.19 | 2.36 | −0.75 | SEMASA-AS1 | −0.12 | −0.21 | 0.25 | −0.30 | −0.01 |
| LINC01219 | −2.99 | 0.69 | 1.34 | 0.76 | 1.07 | ACTL6B | −0.83 | 0.19 | 0.91 | 0.02 | 0.93 | AL606534.4 | −0.23 | −0.99 | −1.56 | −0.20 | −0.13 |
| G25248 | 3.54 | −0.66 | −1.62 | −0.20 | −2.16 | SCOC | 0.27 | −0.20 | −0.03 | −0.07 | −0.02 | OR7D4 | 0.29 | −0.44 | 0.59 | 0.40 | 0.82 |
| COX7B | 1.03 | −0.43 | −0.78 | −0.13 | −0.42 | AC090772.1 | −0.38 | 0.28 | 0.33 | 0.33 | 0.19 | MIR3978 | 0.33 | −0.03 | 1.47 | −1.51 | −0.20 |
| AC133435.1 | −1.47 | 0.87 | 0.68 | 0.84 | 0.22 | AL137803.1 | −0.97 | 0.14 | −0.76 | −0.29 | 0.24 | AL391262.1 | 0.64 | 0.10 | 1.22 | −0.25 | −0.26 |
| LTBR | 0.65 | −0.45 | −0.77 | 0.06 | −0.03 | PRDX2P3 | −0.42 | 0.43 | 0.57 | 0.08 | 0.14 | HS3ST4 | −0.19 | 0.18 | 0.63 | −0.36 | 0.59 |
| SF3B6 | 0.93 | −0.32 | −0.58 | −0.32 | −0.57 | AC007014.2 | 0.83 | 0.29 | 0.76 | −0.55 | 0.13 | AC016588.2 | −0.14 | −0.25 | 0.09 | 0.24 | 0.61 |
| G26894 | −1.76 | 0.86 | 1.31 | 0.44 | 0.45 | G39379 | −0.64 | 0.26 | 0.51 | 0.64 | 0.65 | RNA5SP341 | −0.50 | 0.57 | −0.74 | −0.09 | −0.91 |
| PDCD5 | 0.66 | −0.42 | −0.42 | −0.36 | −0.16 | AL132838.2 | 0.98 | −1.12 | −0.48 | −0.20 | −1.32 | KU-MEL-3 | −0.21 | 0.05 | 0.29 | 0.44 | 0.62 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| CSPG4P11 | −1.06 | 0.58 | 0.91 | 0.38 | 0.22 | AC244517.1 | −0.83 | 1.34 | 0.68 | 0.17 | −0.91 | AC009078.2 | −0.23 | −0.34 | 1.28 | −0.56 | 0.71 |
| PSMC6 | 0.56 | −0.25 | −0.45 | −0.14 | −0.25 | HNRNPA1P37 | 0.72 | 0.18 | −0.52 | 0.61 | 0.30 | AC133106.1 | −0.19 | −0.18 | 0.34 | −1.12 | −0.32 |
| ANXA1 | 1.52 | −1.53 | −2.03 | −0.65 | −1.28 | DEFB108B | −0.81 | −0.23 | 0.24 | 0.45 | 0.80 | AC021072.1 | −0.69 | −0.31 | 0.28 | −0.56 | 0.18 |
| NALCN | −1.47 | 0.55 | 1.40 | 0.52 | 0.80 | AC231657.2 | −1.48 | −1.00 | 2.45 | −2.06 | 1.92 | FOXG1 | −0.45 | 0.15 | 0.52 | −0.27 | 0.40 |
| DBP | −1.07 | 1.00 | 0.98 | 0.69 | −0.05 | RNU6-671P | −1.02 | 0.66 | 0.30 | 0.39 | −0.59 | AC109439.2 | −0.34 | 0.16 | 0.53 | 0.05 | 0.36 |
| CNTNAP3 | −1.44 | 0.81 | 1.30 | 0.55 | 0.29 | RNU1-124P | 0.78 | −0.01 | 0.74 | −0.67 | −0.24 | AC092119.1 | −0.31 | −0.74 | −1.76 | −0.25 | −0.29 |
| PRRT3 | −0.83 | 0.34 | 0.23 | 0.44 | 0.15 | RN7SL494P | −0.69 | 0.22 | −0.34 | 0.82 | 0.11 | C10orf95 | 0.27 | 1.11 | 0.33 | 0.93 | −0.38 |
| CD274 | 1.59 | −1.66 | −1.60 | −0.75 | −0.48 | PPP1R26P1 | 0.29 | −0.10 | −0.49 | 0.08 | −0.30 | LINC01655 | −0.37 | −0.57 | 1.23 | −0.65 | 0.99 |
| SNRPGP2 | 2.35 | −0.47 | −1.76 | −0.12 | −1.24 | GATD3B | −0.38 | −0.09 | 0.14 | 0.18 | 0.39 | MIR4284 | 0.94 | −0.34 | −0.56 | 0.06 | −0.37 |
| AC008991.1 | −1.91 | 1.24 | 0.49 | 0.80 | 0.18 | LCN6 | 1.46 | −0.22 | 0.36 | 0.57 | 0.27 | AC004941.2 | −0.67 | 0.92 | −1.11 | 0.06 | −1.69 |
| IPO5P1 | −0.84 | 0.32 | 0.88 | 0.18 | 0.51 | GACAT2 | 1.08 | −0.90 | −0.65 | 0.11 | −0.21 | AL583832.1 | 0.14 | −0.11 | −0.53 | −0.26 | −0.39 |
| PUS7 | 0.78 | −0.40 | −0.59 | −0.17 | −0.29 | ERICH6 | −0.57 | −0.28 | 1.02 | −0.21 | 0.13 | AC090197.1 | −0.13 | −0.18 | −0.12 | −0.70 | −0.65 |
| PALB2 | 0.60 | −0.26 | −0.44 | −0.02 | −0.19 | DNAJC18 | −0.32 | 0.36 | 0.51 | 0.15 | 0.14 | PKP4-AS1 | −0.06 | −0.01 | 0.03 | 0.06 | 0.25 |
| AC068888.1 | −0.92 | 0.53 | 0.76 | 0.29 | 0.19 | RNU4-31P | 0.83 | −0.68 | −0.75 | −0.59 | −0.61 | GCOM2 | −0.16 | −0.81 | 0.81 | −0.10 | 0.85 |
| HOMER3 | 0.80 | −0.39 | −0.94 | −0.14 | −0.38 | AC092071.1 | −1.06 | −0.80 | 0.89 | −1.71 | 0.38 | SUCLG2 | 0.05 | 0.01 | −0.02 | −0.06 | −0.19 |
| LAMP3 | 1.66 | −1.31 | −0.99 | −1.03 | −0.66 | 3L5P-PVRIG2P- | −0.74 | 0.62 | 0.43 | 0.55 | 0.07 | NAP1L4P3 | 0.23 | 0.17 | −1.28 | 0.59 | −1.68 |
| PGM5 | −1.32 | 0.87 | 1.42 | 0.29 | 0.07 | GNA14-AS1 | 0.97 | −1.83 | 0.16 | −0.25 | 0.85 | CLEC14A | 0.10 | 0.01 | 0.84 | 0.00 | 0.02 |
| MRPS34 | 0.79 | −0.38 | −0.70 | −0.14 | −0.19 | KCNJ8 | −0.59 | 0.51 | 1.13 | −0.13 | −0.30 | AC103810.3 | 0.14 | 0.35 | −0.22 | 0.31 | −0.10 |
| HIF1A-AS2 | 1.36 | −0.62 | −1.09 | −0.45 | −0.28 | ANKS6 | −0.25 | −0.08 | 0.23 | −0.22 | −0.03 | AC078850.2 | −0.25 | 0.41 | 1.15 | 0.27 | 0.30 |
| G18355 | −3.14 | 0.64 | 2.73 | 0.17 | 0.45 | CALML4 | −0.61 | −0.19 | 0.12 | −0.31 | 0.11 | FLG | −0.25 | 0.45 | 0.80 | 1.31 | −0.53 |
| BTNL9 | −1.61 | 1.36 | 1.14 | 1.35 | 0.38 | AC087516.2 | −0.74 | −0.23 | 0.37 | 0.14 | 0.30 | PIGUP1 | −1.38 | −0.31 | 0.27 | 0.07 | 0.55 |
| HIST1H2BC | 1.03 | −0.36 | −1.15 | −0.21 | −0.88 | NARF-AS1 | −0.63 | 0.32 | −0.63 | 0.28 | −0.32 | CHCHD7 | 0.07 | −0.06 | 0.04 | −0.03 | 0.03 |
| CCDC85A | −1.55 | 1.53 | 0.86 | 0.94 | −0.06 | AC023593.1 | 1.07 | −1.35 | −0.62 | −0.45 | 0.11 | AC022400.4 | 0.22 | −0.46 | 0.19 | −0.09 | 0.42 |
| HSPE1P5 | 2.34 | −1.92 | −1.74 | −0.41 | −0.60 | ERVH48-1 | −0.39 | −0.22 | 0.53 | −0.45 | 0.40 | RNU2-35P | 0.82 | −1.38 | −1.29 | −1.00 | −0.15 |
| MED14 | 0.53 | −0.22 | −0.49 | −0.08 | −0.19 | SLC44A3 | −0.39 | 0.15 | 0.80 | 0.07 | 0.19 | AL035413.2 | −0.12 | 0.47 | 0.75 | 0.21 | 0.00 |
| SRRM1P3 | −1.03 | 0.32 | 0.54 | 0.12 | 0.47 | AC092119.2 | −0.39 | 0.11 | 1.11 | 0.17 | 0.44 | MRPL48P1 | 0.76 | −0.67 | −1.34 | 0.84 | −0.69 |
| CLIP4 | −0.59 | 0.45 | 0.47 | 0.30 | 0.03 | SNORD73 | 0.93 | 0.08 | −0.75 | 0.74 | 1.10 | PKN2 | 0.03 | 0.03 | −0.18 | 0.11 | −0.14 |
| HS3ST1 | 1.54 | −1.16 | −1.99 | 0.12 | −1.32 | AC114781.1 | 0.83 | 0.34 | 0.10 | −0.12 | −0.13 | CTC-338M12.4 | 0.14 | −0.15 | −0.04 | 0.47 | 0.49 |
| ELK3 | 0.77 | −0.25 | −0.46 | −0.19 | −0.39 | PSMA2P1 | −0.70 | 0.66 | 0.34 | 0.28 | −0.15 | OR2AK2 | −0.38 | 0.80 | 0.64 | 0.80 | 1.04 |
| PPP2CA | 0.82 | −0.29 | −0.65 | −0.17 | −0.57 | OR2B2 | 1.41 | −1.63 | −1.22 | −0.06 | 0.42 | AP002748.2 | −0.41 | −1.24 | −0.76 | −0.22 | −1.38 |
| GGCT | 1.34 | −0.26 | −0.50 | 0.35 | −0.54 | PLAC8 | 0.64 | −0.91 | 0.38 | −0.46 | 0.38 | MFSD4B | −0.05 | −0.16 | −0.09 | 0.01 | 0.26 |
| LONP2 | −0.35 | 0.15 | 0.22 | 0.12 | 0.12 | AC093732.1 | −0.37 | 0.41 | 0.46 | −0.30 | −0.09 | AC073539.1 | −0.60 | −0.26 | −0.16 | 0.51 | −0.84 |
| CDCP1 | 1.28 | −0.78 | −1.18 | −0.16 | −0.63 | CEACAM3 | 1.00 | −0.75 | −1.21 | −0.61 | −1.20 | RNU1-101P | −0.42 | −0.16 | −1.30 | 0.74 | −0.07 |
| LMF1 | −0.89 | 0.39 | 0.59 | 0.41 | 0.47 | SNORD56B | 1.18 | −0.54 | −1.35 | 0.19 | 0.47 | PNLIPRP2 | −0.41 | −0.66 | −0.59 | 0.07 | 1.85 |
| ENO2 | −0.89 | 0.29 | 0.49 | 0.03 | 0.04 | AL356653.1 | 0.61 | −0.10 | −0.50 | 0.28 | −0.30 | A2M-AS1 | −0.16 | 0.34 | 1.21 | 0.12 | 0.38 |
| PSME2 | 0.83 | −0.70 | −0.80 | −0.41 | −0.31 | RASL10A | −0.43 | 0.65 | −0.08 | 0.16 | 0.21 | GNA01 | −0.09 | −0.22 | −0.68 | 0.03 | −0.19 |
| SDHAP3 | −1.01 | 0.28 | 0.58 | 0.20 | 0.30 | AF124730.1 | 1.15 | −1.36 | −1.52 | −0.60 | −0.92 | PRDX2P1 | −0.24 | −0.65 | 0.91 | 0.50 | 2.09 |
| SOX10 | −1.33 | 0.89 | 0.72 | 0.54 | 0.53 | CCDC85B | 0.25 | 0.12 | −0.26 | −0.03 | −0.54 | NECAP2 | 0.04 | 0.05 | −0.01 | −0.01 | −0.11 |
| NMNAT3 | −0.92 | 0.77 | 1.19 | 0.47 | 0.14 | GDF5OS | −0.89 | −0.78 | 0.28 | −0.03 | 1.49 | LURAP1L-AS1 | 0.15 | −0.27 | −1.11 | −0.10 | −0.52 |
| EXO1 | 1.25 | −1.16 | −1.59 | −0.31 | −0.36 | GGTA2P | −0.63 | −0.23 | 0.70 | 0.30 | 1.22 | PSMD12P | 0.70 | −1.09 | −1.91 | −0.79 | −0.78 |
| HASPIN | 1.59 | −0.85 | −1.52 | −0.19 | −0.61 | RPL13AP7 | 0.38 | 0.06 | −0.33 | 0.08 | −0.49 | PRSS3P4 | −0.71 | −0.25 | 1.44 | −0.34 | −0.37 |
| NOP10 | 1.09 | −0.55 | −0.89 | −0.19 | −0.71 | RNU6-1004P | −1.42 | 1.05 | 0.85 | 0.48 | 0.31 | C1QTNF6 | 0.11 | −0.27 | 0.38 | −0.73 | −0.04 |
| G15458 | −2.23 | 0.85 | −0.08 | 0.88 | 0.55 | G38128 | −1.56 | 0.38 | −1.70 | 1.52 | −0.21 | G31307 | 0.27 | −0.54 | 0.04 | −0.92 | −0.70 |
| MBOAT2 | 1.15 | −0.18 | −0.40 | −0.16 | −0.52 | LCE1D | −0.69 | 0.76 | 1.16 | 1.30 | −0.26 | LINC02224 | −0.34 | −0.27 | −0.48 | 0.04 | −0.09 |
| SEMA6C | −0.99 | 0.67 | 0.60 | 0.53 | 0.14 | AC090519.1 | −0.36 | 0.15 | −0.21 | 0.36 | 0.17 | AL035461.2 | 0.22 | −0.52 | −0.90 | −0.67 | −0.67 |
| NIPA2 | 0.77 | −0.46 | −0.41 | −0.27 | −0.12 | OR9Q1 | −0.74 | −0.21 | −0.07 | −0.34 | −0.17 | AC018695.6 | 0.20 | −0.03 | −0.80 | −0.33 | −0.13 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AL662844.4 | −1.21 | 0.19 | 1.07 | 0.03 | 0.26 | LINC02245 | −0.68 | −0.16 | −0.16 | −0.70 | −0.89 | AC012349.1 | −0.21 | 0.33 | −0.06 | 0.09 | −0.44 |
| KRT8P36 | −1.53 | 0.36 | 0.92 | 0.43 | 0.63 | RORA | −0.33 | 0.67 | 0.91 | 0.48 | −0.13 | MIR3121 | −0.27 | −0.69 | 0.56 | −0.29 | 1.27 |
| HIST1H2AE | 1.41 | −0.74 | −1.45 | −0.14 | −0.96 | FBXO21 | 0.17 | 0.00 | −0.07 | 0.02 | −0.11 | AC024601.1 | −0.84 | 0.26 | 1.92 | −0.23 | 1.38 |
| SSPN | −1.38 | 0.60 | 1.29 | 0.12 | 0.51 | CREBL2 | −0.25 | 0.32 | 0.36 | −0.04 | −0.06 | PCAT4 | 0.38 | −1.36 | −3.03 | 0.13 | −0.45 |
| ARPC4 | 0.72 | −0.49 | −0.65 | −0.09 | −0.37 | AP003072.3 | −1.35 | 1.09 | 1.57 | −1.11 | 0.03 | AL663074.1 | 0.50 | −0.27 | −1.72 | −0.58 | −1.37 |
| RN7SL463P | −1.58 | 0.11 | 0.91 | 0.46 | 1.13 | RN7SL208P | 1.11 | −0.18 | −0.25 | −0.54 | −0.48 | MTCO1P22 | −0.27 | −0.63 | −1.21 | 0.52 | −0.57 |
| C12orf4 | 0.72 | −0.46 | −0.49 | −0.28 | −0.19 | RN7SL526P | −1.41 | 0.77 | 0.18 | 2.50 | 0.33 | RPL17P20 | 0.48 | −0.13 | −0.16 | 0.84 | −0.96 |
| LAMB3 | 1.14 | −0.61 | −1.63 | −0.17 | −0.68 | AL034555.1 | 0.69 | −0.82 | −1.63 | 0.43 | 0.20 | AC023302.1 | 0.25 | 1.52 | −0.57 | 0.24 | −0.74 |
| AC073349.1 | −2.08 | 1.25 | 2.59 | 0.50 | 0.74 | AC025176.1 | 1.53 | −1.41 | −1.13 | −0.13 | −0.12 | PIH1D2 | 0.10 | 0.50 | 0.32 | 0.30 | −0.26 |
| FBXO44 | −1.02 | 0.42 | 0.57 | 0.49 | 0.39 | SMPD2 | −0.24 | 0.13 | 0.03 | 0.33 | 0.02 | AGBL2 | −0.12 | −0.36 | 0.27 | −0.20 | 0.58 |
| ARFGEF3 | −1.31 | 0.90 | 1.68 | 0.20 | 0.56 | G8261 | 0.54 | 0.11 | −0.79 | −0.43 | −0.69 | CYCSP10 | −0.13 | 0.03 | −0.26 | 0.46 | −0.06 |
| POU3F3 | −1.83 | 0.83 | 1.46 | 0.73 | 0.58 | B3GAT1 | −0.49 | 0.40 | −0.60 | 0.69 | 0.16 | PFN1P11 | 0.47 | −1.31 | −2.27 | 0.83 | 0.76 |
| PTBP1 | 0.59 | −0.33 | −0.71 | −0.02 | −0.22 | BANK1 | −0.41 | −0.14 | 0.53 | −0.20 | 0.14 | KCNQ2 | −0.31 | −1.17 | −0.96 | 0.45 | 0.99 |
| ARHGAP11A | 0.99 | −0.94 | −1.15 | −0.44 | −0.02 | MTCYBP23 | 0.92 | −0.56 | −2.31 | 0.62 | −1.24 | LYPD8 | −0.55 | −1.53 | −0.07 | −0.04 | 0.89 |
| CYP27C1 | 1.13 | −0.34 | −1.02 | 0.00 | −0.52 | CCL1 | 1.81 | −1.43 | −1.71 | −0.17 | −0.49 | OR2G2 | 0.69 | −1.03 | −1.24 | 0.69 | −0.31 |
| PPM1G | 0.74 | −0.55 | −0.66 | −0.27 | −0.13 | AC090425.1 | −0.56 | −0.06 | 0.64 | 0.39 | 0.65 | AL359541.1 | 0.53 | −0.55 | 0.29 | −0.07 | −0.48 |
| HOOK2 | −0.86 | 0.42 | 0.42 | 0.37 | 0.26 | CIAO2B | 0.19 | 0.00 | −0.23 | −0.08 | −0.27 | MIR331 | −0.16 | 0.02 | 0.28 | −0.09 | 0.56 |
| SGCA | −1.91 | 0.73 | 0.45 | 0.21 | −0.38 | RAPGEF2 | −0.16 | 0.29 | 0.30 | −0.01 | −0.04 | SSXP10 | −0.22 | −0.13 | 0.73 | −0.58 | 0.60 |
| NUDT15 | 1.28 | −0.51 | −1.31 | −0.19 | −0.77 | ALDHIL1-AS2 | −1.45 | −0.17 | 0.82 | −0.48 | −0.01 | AC097534.1 | −0.18 | 0.46 | 0.41 | −0.04 | −0.25 |
| CPHXL | −2.15 | 0.68 | 0.88 | 1.38 | 0.23 | 3CL2L2-PABPN | 0.58 | −0.39 | −0.15 | −0.28 | 0.12 | LINC00687 | −0.43 | 0.38 | −2.71 | −1.06 | −3.31 |
| CDH26 | 1.02 | −0.57 | −1.18 | −0.16 | −1.11 | DSG4 | 0.54 | −0.46 | −1.14 | 0.25 | 0.00 | AC092368.3 | −0.19 | 0.73 | −0.62 | 0.53 | −0.37 |
| GM2A | 0.95 | −0.45 | −0.68 | −0.06 | −0.30 | G19546 | 0.81 | −0.13 | −0.65 | 0.29 | 0.06 | GDF15 | 0.24 | 0.46 | 0.32 | 0.60 | −0.76 |
| ALX4 | −1.45 | 0.99 | 1.71 | 0.49 | 0.42 | NCLP1 | −0.32 | 0.08 | 0.16 | 0.17 | 0.17 | LINC00668 | −0.28 | −0.07 | 1.50 | −0.34 | 0.56 |
| DCTD | 0.63 | −0.35 | −0.52 | −0.06 | −0.26 | DHFRP1 | 1.09 | −0.45 | −1.29 | −0.13 | −1.54 | AC124017.1 | 0.28 | 0.22 | −0.22 | −0.11 | −0.27 |
| SPRR2E | 2.39 | −1.04 | −1.78 | −0.71 | −1.12 | AL353648.1 | −0.75 | 0.17 | 0.85 | 0.41 | 0.59 | NCOA1 | −0.05 | 0.20 | 0.23 | 0.06 | −0.01 |
| MON1A | 0.67 | −0.30 | −0.59 | −0.01 | −0.15 | AP002847.1 | 0.44 | −0.31 | 0.09 | 0.23 | 0.55 | CCZ1 | −0.06 | 0.05 | 0.15 | 0.06 | 0.24 |
| COPB1 | 0.64 | −0.33 | −0.40 | −0.18 | −0.33 | AL392046.1 | −0.89 | 0.28 | −1.31 | 0.66 | −0.61 | AC003985.2 | 0.59 | −0.15 | −1.14 | 0.28 | −0.63 |
| SDHAF4 | −0.64 | 0.26 | 0.49 | −0.10 | 0.05 | RNU6-227P | −1.74 | 1.07 | 0.29 | 0.75 | −1.45 | IQCM | −0.31 | −1.04 | 0.05 | 0.02 | 1.11 |
| POLQ | 1.04 | −1.08 | −1.36 | −0.32 | −0.27 | GGNBP2 | 0.11 | −0.06 | −0.27 | 0.01 | −0.21 | NPM1P37 | −0.10 | 0.27 | 0.40 | −0.02 | 0.08 |
| CYP2D6 | −1.16 | 0.86 | 0.78 | 0.58 | 0.36 | LIN37 | −0.43 | 0.04 | 0.74 | −0.06 | 0.03 | HRAT17 | −0.67 | 0.86 | −0.53 | 1.09 | −0.10 |
| ING2 | 0.79 | −0.24 | −0.44 | −0.13 | −0.31 | GAPDHP76 | −0.74 | −0.20 | 0.35 | −0.07 | 0.05 | MIR5692A1 | 0.35 | 0.83 | 0.27 | 0.31 | −0.06 |
| CDK17 | 0.49 | −0.17 | −0.30 | −0.19 | −0.26 | C4A | −0.53 | 0.15 | 0.58 | 0.39 | 0.38 | AGK | 0.03 | 0.09 | 0.11 | 0.02 | 0.02 |
| LPAR6 | 0.62 | −0.35 | −0.36 | −0.08 | −0.22 | G35948 | −0.70 | 0.29 | 0.23 | 0.23 | −0.06 | MIR3976HG | −0.64 | 0.82 | −0.98 | 1.18 | −1.57 |
| ARF1 | 0.65 | −0.27 | −0.61 | −0.11 | −0.42 | MIR3676 | 0.73 | 0.15 | −0.15 | −0.02 | −0.75 | PNKD | 0.06 | −0.14 | −0.09 | −0.12 | −0.03 |
| LINC02175 | −1.07 | 0.75 | 0.88 | 0.26 | 0.48 | LINC01480 | 0.75 | −0.25 | −1.46 | −0.43 | −0.55 | ARHGAP19 | 0.06 | −0.04 | 0.06 | −0.02 | −0.05 |
| GPR12 | −2.04 | 0.78 | 2.05 | 0.67 | −0.09 | GPKOW | −0.14 | 0.20 | 0.10 | 0.04 | −0.11 | LINC02017 | −0.31 | 0.66 | 1.52 | −0.44 | 0.69 |
| AC008556.1 | 1.42 | −0.54 | −0.78 | 0.02 | −0.34 | PICSAR | 0.48 | −0.01 | −0.29 | 0.18 | −0.06 | HSPA8P18 | −0.17 | −0.08 | 0.11 | 0.76 | 0.42 |
| BRCA1 | 0.90 | −0.79 | −0.89 | −0.38 | −0.15 | JAML | 0.44 | −0.50 | −0.16 | −0.21 | 0.26 | MUC15 | 0.12 | 0.31 | 0.78 | 0.50 | −0.16 |
| PRX | −1.11 | 0.39 | 0.87 | 0.12 | 0.42 | KLHL5 | 0.28 | −0.31 | −0.27 | −0.17 | −0.05 | AL391516.1 | 0.40 | −1.25 | 0.15 | −0.91 | 0.51 |
| MAMDC4 | −1.11 | 0.66 | 0.45 | 0.56 | 0.28 | G555 | −1.06 | 0.53 | 0.87 | −0.31 | 0.11 | AC091806.1 | 0.32 | −0.64 | 0.82 | −0.46 | 1.00 |
| SERPINB9 | 1.38 | −1.63 | −1.23 | −0.75 | −0.59 | G895 | 0.76 | −0.14 | −0.68 | −0.20 | 0.06 | AC013553.4 | −0.55 | −0.11 | 0.72 | 0.28 | 1.99 |
| CCNQ | 0.76 | −0.26 | −0.64 | −0.35 | −0.46 | AC004540.2 | 1.04 | −0.53 | 1.05 | −0.01 | 2.17 | AC097372.1 | −0.48 | −0.81 | −1.23 | 0.84 | 0.72 |
| CDC25A | 1.35 | −1.17 | −1.88 | −0.28 | −0.60 | AL135934.1 | −0.96 | −0.18 | 0.65 | 0.93 | 0.49 | ITPR2 | −0.06 | 0.25 | −0.01 | 0.26 | −0.07 |
| RAB22A | 0.80 | −0.32 | −0.61 | −0.16 | −0.45 | SLC16A4 | −0.21 | 0.02 | 0.34 | −0.15 | −0.11 | AL035461.1 | 0.34 | −1.10 | 0.48 | −1.10 | −0.66 |
| FAM180B | −1.53 | 1.52 | 2.39 | 0.46 | 0.15 | AL138785.1 | 0.62 | −0.67 | −0.99 | −0.39 | −0.67 | AC084026.2 | −0.59 | −0.09 | 0.45 | 0.35 | 1.45 |
| SMARCC2 | −0.60 | 0.23 | 0.29 | 0.14 | 0.07 | AL662797.1 | 0.57 | −0.39 | −0.54 | 0.36 | 0.11 | AC234771.4 | −0.37 | −0.47 | 0.29 | −0.48 | 0.18 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| PCP2 | −1.61 | 0.70 | 1.06 | 0.61 | 0.94 | ING1 | −0.19 | 0.08 | 0.31 | −0.21 | 0.08 | AC004461.2 | −0.14 | 0.10 | 0.03 | 0.36 | −0.07 |
| FNBP1L | −0.73 | 0.61 | 0.86 | 0.07 | 0.16 | AC007879.1 | −0.82 | −0.64 | 1.09 | −0.51 | 0.97 | SOWAHB | −0.20 | 0.16 | 0.28 | 0.21 | −0.04 |
| ASB11 | −2.14 | 0.31 | 1.13 | 0.68 | 0.30 | AC027329.1 | −0.87 | −0.24 | −0.11 | 0.11 | 0.21 | NECTIN4 | 0.09 | 0.36 | 0.10 | 0.12 | −0.19 |
| FRY | −0.81 | 0.49 | 1.04 | −0.07 | −0.01 | SNORA43 | −0.55 | −0.03 | 0.06 | 0.27 | 0.29 | AL359641.1 | −0.79 | −1.21 | 0.10 | −1.07 | 0.11 |
| DDX1 | 0.74 | −0.29 | −0.39 | −0.21 | −0.22 | AL139384.2 | −0.60 | −0.17 | 0.34 | −0.21 | 0.48 | AC087289.1 | −0.18 | 0.51 | −0.08 | −0.02 | 0.07 |
| LINC00174 | −0.76 | 0.26 | 0.80 | 0.26 | 0.53 | SRP14P4 | −0.97 | −0.69 | 2.18 | −0.44 | 1.18 | AC007221.2 | −0.58 | 0.08 | −0.37 | −1.12 | −0.60 |
| RNVU1-9 | −1.53 | 0.36 | 0.12 | 0.48 | 0.26 | CGGBP1 | 0.20 | 0.04 | 0.14 | −0.12 | −0.14 | PRR32 | 0.80 | 0.60 | −1.66 | 1.70 | −0.42 |
| RUSC2 | −0.78 | 0.41 | 0.79 | 0.09 | 0.14 | KLHL7-DT | −0.60 | −0.35 | 0.85 | −0.81 | 0.22 | RPS3AP49 | −0.20 | −0.16 | 0.30 | −0.03 | 1.00 |
| MPHOSPH10 | 0.67 | −0.29 | −0.50 | −0.22 | −0.31 | AL035701.1 | −1.06 | 0.62 | 0.02 | −0.03 | 0.03 | CEP290 | 0.06 | −0.04 | −0.15 | −0.02 | 0.00 |
| DSCAML1 | −1.56 | 0.54 | 0.64 | 1.51 | 0.78 | HNRNPA1L2 | −0.20 | 0.27 | −0.01 | 0.31 | −0.18 | G32279 | 0.55 | −0.76 | 1.30 | 0.61 | 1.73 |
| NTN5 | −2.14 | 1.33 | 3.01 | 1.08 | 0.54 | MEIS3P2 | −0.90 | 0.45 | −0.05 | 0.68 | 1.35 | AC093515.1 | 0.89 | 0.38 | −0.15 | −1.06 | 0.34 |
| PCP4 | −2.11 | 0.72 | 1.24 | 0.00 | −0.43 | KRTAP10-10 | −1.68 | 0.11 | 0.01 | −0.61 | −0.09 | AC090527.3 | −0.53 | −1.96 | 1.03 | −1.48 | 0.57 |
| ACSS1 | −0.92 | 0.49 | 0.74 | 0.25 | 0.27 | AC009387.1 | −1.32 | −0.13 | 2.40 | −0.43 | 1.05 | AC092896.2 | 0.15 | −0.42 | −0.65 | 0.18 | 0.21 |
| EBP | 1.04 | −0.24 | −0.91 | 0.14 | −0.59 | AC098934.3 | 0.76 | −0.91 | 0.77 | −0.67 | 0.72 | QTRT1P1 | 0.66 | 0.84 | −0.80 | 0.36 | 0.15 |
| AC026740.2 | −3.08 | 1.63 | 3.12 | 0.55 | 0.48 | FEN1P1 | −0.92 | 0.93 | 0.57 | 0.92 | 0.37 | DAZAP2P1 | 0.22 | −0.72 | −2.58 | 0.81 | −0.96 |
| EPHX1 | −0.97 | 0.64 | 0.95 | 0.17 | 0.22 | C9orf57 | −0.79 | 0.79 | 0.56 | −0.02 | −0.55 | AC114755.5 | 0.47 | −1.62 | −1.09 | −0.01 | 0.38 |
| HECTD4 | −0.55 | 0.26 | 0.39 | 0.12 | 0.26 | RNU6-653P | 1.24 | −0.94 | −1.31 | 0.20 | −0.46 | AC005392.3 | 0.60 | −2.70 | −2.33 | −0.83 | −1.34 |
| AC004816.1 | 1.55 | −0.54 | −1.03 | −0.01 | −0.79 | ASAP1-IT2 | 0.25 | −0.31 | −0.14 | −0.03 | 0.01 | AC008676.1 | 0.18 | −0.48 | 0.07 | −0.50 | 0.24 |
| RPF2 | 0.73 | −0.45 | −0.99 | −0.14 | −0.55 | AL360268.1 | 0.78 | 0.12 | 0.65 | −0.08 | 0.00 | GABRB1 | 0.28 | 0.24 | −0.33 | 0.30 | −1.34 |
| C5orf66 | 1.41 | −0.57 | −0.95 | −0.01 | −0.09 | FXR1 | 0.16 | −0.08 | −0.15 | −0.12 | −0.11 | AL109924.5 | 0.36 | −0.16 | 4.46 | −0.95 | 0.96 |
| CDRT1 | 1.46 | −0.83 | −1.12 | −0.38 | −0.08 | AC108488.1 | −0.41 | −0.18 | 0.11 | −0.21 | −0.11 | AL360294.1 | 0.47 | −0.97 | 0.45 | 0.35 | 0.18 |
| NME1 | 1.09 | −0.79 | −0.90 | −0.01 | −0.14 | PM20D1 | −0.79 | 0.73 | 0.35 | 2.30 | 1.91 | FO393418.1 | −0.32 | −0.19 | 0.76 | −0.21 | 1.13 |
| RXRG | −1.45 | 0.63 | 1.09 | 0.09 | 0.34 | IPPK | 0.24 | −0.04 | −0.29 | 0.05 | −0.15 | G42437 | −0.65 | −0.15 | 1.60 | −1.09 | −0.78 |
| NPEPPS | 0.61 | −0.32 | −0.70 | −0.09 | −0.28 | RNU6-21P | −1.47 | 1.41 | −0.57 | 2.00 | −0.39 | AC025048.5 | 0.63 | −0.55 | −0.11 | −0.72 | 0.68 |
| DIP2C | −0.71 | 0.37 | 0.59 | 0.11 | 0.06 | AL352979.3 | 0.72 | −0.25 | −0.50 | 0.21 | −0.60 | AL138760.1 | 0.29 | 0.00 | −1.06 | −0.08 | −0.32 |
| FBXO32 | −0.98 | 0.77 | 0.91 | 0.30 | 0.00 | AC018738.1 | 0.51 | −0.16 | 0.56 | −0.69 | 0.02 | LILRP2 | 0.68 | −1.22 | −2.29 | 0.44 | −0.91 |
| MRPS23 | 0.63 | −0.32 | −0.48 | −0.24 | −0.38 | AC022398.1 | −0.84 | −0.30 | −1.15 | −0.52 | −0.73 | AC024158.1 | −0.30 | 0.67 | 1.65 | −0.47 | 0.55 |
| DEPDC1 | 1.40 | −1.00 | −1.61 | −0.29 | −0.66 | NDUFB4P10 | 0.80 | 0.07 | −0.52 | 0.67 | −0.06 | RN7SL764P | 0.30 | −1.06 | 2.03 | −0.50 | 2.62 |
| PPARGCIA | −1.44 | 0.92 | 1.51 | 0.41 | 0.48 | SLC9C1 | −0.47 | 0.60 | 1.55 | −0.06 | 0.34 | RP11-435B5.2 | −0.88 | −0.73 | 1.07 | 0.01 | 1.97 |
| AC005899.6 | −1.51 | 0.78 | 1.12 | 0.56 | 0.87 | FASTKD3 | 0.26 | −0.26 | −0.05 | 0.08 | 0.19 | AC044839.1 | 0.39 | 0.19 | −0.50 | −0.26 | −0.72 |
| PPP2R2A | 0.55 | −0.18 | −0.47 | −0.03 | −0.27 | LDB2 | −0.37 | 0.41 | 1.13 | 0.08 | 0.20 | HSFY1P1 | 0.58 | −0.45 | −0.44 | 0.52 | 0.10 |
| GSTT2 | −2.03 | 1.24 | 1.15 | 1.11 | 0.45 | AC007036.1 | −0.60 | 0.69 | 0.42 | −0.06 | −0.51 | RPL23AP70 | 0.23 | −0.68 | 0.68 | −0.42 | 0.69 |
| FHIT | −0.78 | 0.60 | 0.80 | 0.23 | 0.19 | RN7SL749P | 0.59 | −0.62 | −0.35 | −0.72 | 0.09 | AC072061.1 | −0.13 | −0.03 | −0.65 | 0.30 | 0.06 |
| SHB | 1.14 | −0.45 | −1.25 | 0.12 | −0.47 | AC015712.2 | 0.36 | −0.64 | −0.22 | −0.63 | −0.20 | AL355472.4 | −0.26 | 0.69 | 1.85 | 0.32 | 0.63 |
| GTF2IRD2 | −1.13 | 0.72 | 1.09 | 0.43 | 0.45 | SLC9A9-AS2 | 0.60 | −0.11 | −0.02 | 0.49 | 0.21 | KATNB1 | −0.06 | −0.03 | −0.18 | 0.25 | 0.10 |
| ITM2A | −1.09 | 0.82 | 1.09 | 0.25 | 0.01 | HLA-W | −0.60 | 0.64 | 0.97 | 0.01 | −0.16 | AC007686.2 | 0.60 | 0.33 | −2.31 | 0.12 | −2.85 |
| POLR3B | 0.73 | −0.32 | −0.60 | 0.00 | −0.21 | AL353898.2 | −0.37 | 0.14 | 0.75 | −0.21 | 0.08 | MIR3133 | 0.60 | −0.84 | 1.69 | −0.93 | 1.86 |
| DNM1L | 0.57 | −0.34 | −0.44 | −0.12 | −0.14 | RNU6-6P | −0.59 | 0.31 | 0.42 | 0.71 | −0.54 | ENTPD1-AS1 | 0.04 | −0.32 | 0.05 | −0.05 | 0.32 |
| HSPA9 | 0.80 | −0.49 | −0.70 | −0.23 | −0.28 | OR5B15P | −1.47 | 0.27 | −1.27 | 0.00 | −1.90 | AC022858.1 | −0.63 | −0.97 | 0.70 | −1.55 | −0.13 |
| G12854 | 1.95 | −1.39 | −2.56 | 0.03 | −1.79 | FBRSL1 | −0.25 | 0.02 | −0.31 | 0.16 | 0.13 | DDX10P2 | −0.37 | −0.96 | 1.80 | −0.27 | 1.32 |
| PARK7 | 0.74 | −0.46 | −0.57 | −0.09 | −0.24 | AC010531.4 | 0.56 | −0.81 | −0.13 | −0.58 | 0.38 | HTRA4 | 0.21 | 0.13 | −1.44 | −0.14 | −1.90 |
| DESI2 | 0.75 | −0.30 | −0.45 | −0.10 | −0.32 | PRR16 | −0.46 | −0.12 | 1.05 | −0.74 | 0.48 | NPM1P12 | 0.40 | −0.58 | −0.81 | 0.63 | 0.17 |
| HNRNPH2 | 0.73 | −0.29 | −0.74 | 0.06 | −0.40 | SIX2 | 0.81 | −0.23 | −0.76 | −0.04 | −0.86 | AC073648.6 | −0.16 | 0.53 | 0.83 | 0.22 | −0.11 |
| METAP1 | 0.81 | −0.25 | −0.45 | −0.06 | −0.27 | CSE1L-AS1 | 1.54 | −0.26 | −0.34 | 0.74 | 0.41 | SCARNA22 | 0.12 | −0.31 | −0.71 | 0.17 | −0.81 |
| ICOSLG | −0.83 | 0.49 | 0.37 | 0.10 | −0.24 | AC129492.5 | 0.84 | −0.72 | 0.52 | −0.20 | 0.40 | RNU6-1140P | −1.00 | 0.81 | 0.86 | −0.05 | −0.62 |
| H3F3AP4 | 1.16 | −0.41 | −0.59 | −0.29 | −0.55 | PIAS2 | −0.13 | 0.05 | 0.12 | 0.14 | 0.09 | RNU6-1084P | −1.19 | 0.70 | 0.67 | 0.48 | 0.92 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| CDC42SE1 | 0.76 | −0.34 | −0.59 | −0.16 | −0.28 | CLDN7 | −0.40 | 0.43 | 0.54 | 0.25 | 0.29 | G31829 | −0.24 | 0.24 | 0.48 | −0.03 | −0.21 |
| HIST1H2AJ | 1.75 | −1.02 | −1.38 | −0.30 | −0.84 | HCFC1R1 | −0.25 | 0.23 | −0.01 | 0.10 | −0.22 | AL355877.2 | 0.32 | 0.17 | −0.01 | −0.24 | −0.98 |
| LINC00598 | −1.22 | 0.40 | 0.74 | 0.21 | 0.16 | AC011431.1 | −0.73 | 0.52 | 1.10 | 0.31 | 0.66 | AL117337.1 | −0.29 | −0.93 | 0.07 | 0.08 | 0.24 |
| HIST1H3H | 1.41 | −1.00 | −1.38 | −0.27 | −0.81 | RPL7AP60 | −0.38 | 0.27 | 0.28 | 0.58 | 0.41 | AC018635.1 | −0.58 | −0.28 | −1.08 | 0.40 | 1.21 |
| MIR99AHG | −0.86 | 0.82 | 1.00 | 0.34 | 0.00 | AC138028.2 | 0.34 | −0.20 | −0.71 | 0.17 | −0.23 | RPL27P12 | 0.28 | 0.10 | −0.86 | 1.08 | −0.02 |
| G41064 | −3.17 | 0.33 | 3.73 | 1.47 | 1.45 | DEFB124 | −1.27 | 1.52 | 0.37 | 0.23 | −0.43 | HMGN2P20 | 0.24 | 0.87 | −0.04 | 0.35 | −0.07 |
| G13086 | −2.02 | 1.51 | 2.25 | 1.01 | 0.97 | AC040904.1 | 0.70 | −0.51 | −0.01 | −0.20 | 0.35 | LNCAROD | −0.21 | −0.51 | 0.06 | −0.09 | −0.42 |
| SCUBE3 | −0.78 | 0.22 | 0.62 | 0.04 | 0.10 | AC024243.1 | −0.85 | 0.06 | −0.88 | 0.00 | −0.09 | AL603965.1 | 0.18 | 0.24 | −0.37 | 0.18 | −0.16 |
| BCR | 0.62 | −0.21 | −0.75 | 0.15 | −0.12 | OSER1 | 0.15 | 0.15 | −0.13 | 0.16 | −0.25 | G43442 | 1.00 | −0.59 | −0.14 | −2.22 | −1.88 |
| PLCB4 | −1.30 | 0.88 | 1.38 | 0.33 | 0.47 | MAP6D1 | 0.70 | −0.29 | 0.94 | −0.03 | 0.43 | RP11-327I22.5 | 0.75 | −0.72 | −2.26 | −0.52 | −2.33 |
| LAMC3 | −1.45 | 0.39 | 1.12 | −0.12 | 0.29 | HOXB-AS1 | −0.44 | 0.03 | 0.95 | −0.15 | −0.03 | C4orf50 | −0.25 | −0.23 | −0.14 | −0.07 | 0.26 |
| MIATNB | −0.75 | 0.20 | 0.48 | 0.06 | 0.51 | RN7SL730P | −0.39 | −0.04 | 0.15 | −0.10 | 0.09 | RPSAP38 | 0.39 | −1.63 | −0.91 | 0.22 | 0.57 |
| ARHGAP1 | 0.43 | −0.22 | −0.45 | −0.17 | −0.31 | AC005160.1 | 1.06 | −0.10 | −0.34 | −0.60 | 0.32 | AC009292.1 | −0.60 | 1.45 | 1.73 | 2.51 | 0.52 |
| SCARA5 | −2.14 | 1.31 | 2.22 | 0.70 | 0.26 | AL353625.1 | 0.35 | 0.10 | −0.19 | 0.25 | −0.07 | RN7SL577P | −0.21 | 0.04 | −0.36 | 0.60 | −0.51 |
| CALM1 | 0.89 | −0.58 | −0.91 | −0.30 | −0.41 | RPL35P1 | 1.46 | 0.39 | −1.46 | 0.65 | −0.81 | AC002456.1 | −0.27 | 0.37 | 0.59 | 0.34 | 0.43 |
| AC112777.1 | 1.43 | −1.21 | −2.05 | 0.12 | −0.04 | RABAC1 | 0.26 | −0.03 | −0.33 | −0.25 | −0.34 | AC011471.2 | −0.15 | 0.20 | −0.26 | 0.07 | −0.04 |
| MAPKAP1 | 0.50 | −0.32 | −0.40 | −0.24 | −0.05 | SLC3A1 | −0.49 | −0.03 | 0.41 | 0.11 | 0.53 | AC244258.1 | 0.14 | −0.73 | 0.06 | −0.40 | 0.03 |
| SLC27A6 | −1.87 | 1.55 | 1.17 | 0.11 | −0.14 | AL139393.1 | −0.88 | 0.54 | 1.32 | −0.60 | 0.08 | AC093668.2 | −0.20 | −0.31 | 0.38 | −0.37 | 0.38 |
| ADAM33 | −1.27 | 0.63 | 1.18 | 0.38 | 0.13 | NPPC | −1.35 | 1.93 | 0.79 | 1.03 | 0.52 | AC027348.1 | −0.26 | −1.16 | −0.22 | 0.22 | −0.05 |
| CENPK | 0.86 | −1.02 | −0.86 | −0.46 | 0.07 | AC109454.4 | −0.42 | 0.06 | 0.76 | 0.31 | 0.62 | AL691403.2 | 0.42 | −1.12 | −0.56 | 0.45 | 0.16 |
| AKR1E2 | −0.96 | 0.26 | 1.13 | −0.03 | 0.59 | OR10A6 | −0.75 | 0.78 | 0.41 | 0.03 | −0.49 | SRGAP3-AS1 | 0.24 | −1.07 | 0.15 | −0.15 | 0.82 |
| MCM4 | 0.96 | −0.63 | −0.93 | −0.11 | −0.50 | B4GALNT4 | −0.36 | 0.17 | −0.07 | 0.26 | 0.11 | RNU6-733P | 0.54 | 0.66 | −0.48 | 1.40 | −1.40 |
| ARHGDIB | 0.77 | −0.56 | −0.48 | −0.24 | −0.19 | AC092120.2 | 0.35 | −0.16 | −0.55 | −0.06 | 0.09 | AL365209.1 | −0.16 | −0.36 | −0.41 | −0.65 | −0.63 |
| IL7R | 1.76 | −1.87 | −0.71 | −1.05 | −0.10 | PCDH8 | −1.17 | 1.01 | 1.30 | −0.03 | −0.36 | SUGT1P2 | −0.11 | 0.30 | −0.01 | 0.32 | −0.28 |
| COX6B1 | 0.64 | −0.21 | −0.56 | −0.03 | −0.55 | SETP6 | −0.42 | 0.36 | −0.05 | 0.13 | −0.49 | AC104823.1 | 0.31 | 0.26 | −2.57 | 0.40 | −1.66 |
| LINC01359 | −1.20 | 0.46 | 1.34 | 0.15 | 0.61 | DCUN1D4 | −0.18 | 0.03 | 0.16 | −0.06 | 0.06 | AL442163.2 | 0.47 | −0.67 | −0.21 | 0.17 | 1.51 |
| G12890 | −1.52 | 0.64 | 0.84 | 0.82 | 0.39 | GNAI1 | 0.24 | 0.04 | −0.11 | 0.03 | −0.20 | AL157414.3 | −0.38 | 0.99 | −0.30 | −0.66 | −1.39 |
| RPL27A | 0.72 | −0.21 | −0.41 | −0.11 | −0.45 | AC004024.1 | −0.66 | 1.09 | 1.24 | 0.50 | 0.11 | AC099548.2 | 0.10 | −0.24 | −0.12 | 0.04 | 0.26 |
| RNF150 | −1.62 | 0.97 | 1.22 | 0.54 | −0.01 | DAGLA | −0.40 | 0.16 | 0.01 | 0.34 | 0.03 | AC093627.2 | −0.84 | −1.27 | −0.51 | −0.45 | 1.07 |
| ADGRD1 | −1.69 | 0.95 | 1.90 | 0.30 | −0.06 | AC099753.1 | −1.17 | 0.10 | 1.41 | 0.44 | 0.70 | AC136469.2 | 0.16 | 0.24 | −0.70 | 0.26 | −0.28 |
| HIST1H3A | 1.40 | −1.05 | −1.25 | −0.40 | −0.84 | C10orf25 | −0.48 | −0.06 | 0.46 | 0.02 | −0.11 | RPL7P27 | −0.73 | −0.83 | 0.25 | −1.54 | −2.34 |
| GLIPRIL2 | −1.59 | 1.11 | 1.34 | 0.19 | −0.21 | RNU2-14P | −0.75 | 0.30 | 0.60 | 0.88 | −0.14 | MIR581 | −0.18 | 0.30 | 0.66 | −0.08 | 0.45 |
| HMGA2 | 1.70 | −1.31 | −2.10 | −0.17 | −0.52 | HNRNPA1P49 | 0.45 | 0.05 | −0.09 | 0.01 | −0.15 | AC093014.1 | −0.26 | 0.54 | 0.12 | −0.05 | −0.20 |
| FRMD4B | 0.45 | −0.07 | −0.49 | −0.04 | −0.23 | ENPP7P4 | −0.43 | −0.32 | 1.04 | −0.67 | 0.24 | MYL12AP1 | 0.49 | 0.33 | 0.03 | 0.82 | −0.94 |
| PLAUR | 1.57 | −1.72 | −1.67 | −0.55 | −1.00 | CELF6 | −1.16 | −0.39 | 0.15 | −0.81 | −0.99 | SMAD5 | 0.06 | 0.10 | 0.16 | 0.11 | 0.02 |
| GYG2 | −1.92 | 1.53 | 1.44 | 1.10 | 0.20 | AC007001.1 | −0.82 | 0.45 | 1.12 | −0.31 | 0.96 | AL355512.2 | −1.02 | −0.36 | 1.03 | −1.41 | −0.26 |
| STRAP | 0.85 | −0.44 | −0.76 | −0.23 | −0.52 | AC099788.1 | −1.62 | −0.65 | 1.04 | −1.28 | 0.78 | ANTXRL | 0.31 | −1.30 | 0.02 | −0.19 | 0.65 |
| CYB5R4 | 0.59 | −0.31 | −0.42 | −0.10 | −0.19 | AL353671.1 | −0.68 | −0.86 | 0.53 | −0.40 | 0.86 | LINC01193 | −0.38 | −1.20 | −1.14 | 0.13 | 0.37 |
| SGK1 | 0.98 | −0.29 | −1.38 | −0.03 | −0.76 | AL445187.1 | 0.58 | −0.43 | −0.65 | −0.28 | −0.46 | AC110774.1 | −0.37 | 0.42 | −0.84 | 0.74 | 0.56 |
| CACNB2 | −0.60 | 0.06 | 0.52 | 0.03 | 0.35 | PCDHA9 | −0.71 | 0.04 | 0.65 | 0.26 | −0.02 | PXN-AS1 | −0.11 | −0.10 | −0.23 | 0.30 | 0.06 |
| KLHDC1 | −0.89 | 0.49 | 1.01 | 0.17 | 0.32 | MRPL30 | 0.16 | −0.11 | −0.19 | −0.01 | −0.05 | AC012170.2 | 0.13 | 0.15 | −0.01 | 0.04 | −0.56 |
| COX7A1 | −1.29 | 0.79 | 1.22 | −0.15 | 0.00 | FILIP1L | −0.27 | 0.20 | 0.54 | −0.30 | −0.30 | AC015468.4 | −0.57 | −0.54 | −0.85 | 0.68 | −0.53 |
| MRPL20 | 0.59 | −0.35 | −0.51 | −0.08 | −0.14 | MTND2P31 | −1.04 | −0.57 | 0.79 | −1.07 | −0.09 | AC027277.2 | −0.16 | 0.26 | 0.14 | 0.31 | −0.26 |
| AL592211.1 | −1.43 | 0.59 | 0.78 | 0.28 | 0.43 | AL357033.4 | 0.47 | −0.35 | −1.23 | −0.31 | −0.37 | MIR625 | 0.76 | −0.56 | 1.89 | −0.97 | 1.32 |
| GYG1 | 0.88 | −0.45 | −0.76 | −0.30 | −0.63 | MST1R | −0.40 | −0.04 | −0.48 | 0.43 | 0.42 | AC093864.1 | 0.15 | −0.40 | 0.12 | 0.11 | 0.63 |
| FAM153C | −2.07 | 0.34 | 0.85 | 0.72 | 1.26 | FHOD1 | 0.26 | −0.18 | −0.84 | 0.14 | −0.28 | LINC02011 | 0.34 | 0.26 | −1.58 | 0.05 | −1.99 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| CCDC191 | −0.63 | 0.25 | 0.43 | 0.16 | 0.20 | EIF3EP1 | 0.43 | −0.06 | 0.19 | −0.26 | 0.04 | AC092953.2 | 0.18 | 0.37 | 0.79 | −0.19 | −0.04 |
| PAICS | 0.91 | −0.64 | −0.77 | −0.15 | −0.12 | AL050341.1 | 1.38 | 0.65 | 0.37 | −0.99 | 0.01 | BNIP3P5 | 0.17 | −0.18 | −0.38 | −0.16 | 0.16 |
| AC006019.2 | −2.21 | 0.69 | 1.08 | 0.48 | 0.45 | GABRA6 | −1.29 | −0.60 | 0.07 | −0.40 | −1.28 | LINC02374 | 0.55 | −0.74 | −1.84 | 0.21 | −0.97 |
| SMYD2 | 0.68 | −0.48 | −0.80 | −0.05 | −0.17 | AL512343.2 | −0.63 | 0.34 | 0.05 | −0.04 | −0.14 | LINC01613 | 0.38 | 0.44 | −1.84 | 1.06 | −0.48 |
| CFTR | −1.65 | 0.79 | 0.62 | 0.44 | −0.46 | ORAI3 | −0.49 | 0.46 | 0.21 | 0.51 | −0.05 | NDUFA3P2 | −0.18 | 0.27 | −0.04 | −0.08 | −0.04 |
| KCNK12 | −1.38 | 0.52 | 1.17 | −0.12 | 0.61 | PDGFRA | −0.39 | 0.09 | 1.13 | −0.53 | 0.05 | G9217 | 0.24 | 1.31 | 2.15 | 0.69 | −0.33 |
| LINC00710 | −1.28 | 0.71 | 1.62 | 0.10 | 0.54 | RP11-193H22.2 | 0.51 | −0.90 | −0.61 | −0.21 | −0.11 | G35542 | 0.26 | −0.01 | −0.78 | 0.65 | 0.16 |
| AL356753.1 | −1.54 | 1.02 | 0.57 | 0.74 | 0.25 | NR2F2 | −0.37 | 0.36 | 0.99 | 0.17 | 0.08 | AC025265.1 | 0.33 | −1.43 | 0.37 | −0.15 | 0.50 |
| ADAM9 | 0.89 | −0.49 | −0.88 | −0.31 | −0.56 | AC115618.3 | 0.66 | −0.12 | −0.87 | −0.22 | −0.34 | AL391669.1 | 0.13 | −0.03 | −0.43 | −0.01 | −0.29 |
| CPQ | −0.88 | 0.48 | 0.85 | −0.11 | 0.08 | RNU2-20P | −1.04 | 0.09 | −0.58 | 0.55 | −0.23 | AC132872.2 | 0.09 | −0.32 | −0.27 | −0.23 | 0.12 |
| STARD4 | 1.18 | −0.58 | −0.77 | 0.10 | −0.27 | AC104534.1 | −0.42 | −0.07 | 0.17 | 0.00 | 0.36 | AL583805.1 | −0.28 | 0.02 | 0.38 | 0.21 | 0.02 |
| PHBP7 | −2.44 | 1.07 | 2.71 | 1.30 | 0.50 | PROX2 | −0.45 | 0.19 | 0.79 | 0.14 | 0.29 | RNU6-1297P | 0.39 | −0.12 | 0.83 | −1.33 | −1.01 |
| NPY6R | −1.43 | 0.72 | 1.19 | 0.46 | 0.47 | C9orf66 | −0.50 | 0.11 | −0.01 | 0.04 | −0.12 | MTCO1P18 | 0.57 | −1.84 | 0.78 | −0.45 | −0.03 |
| LONRF3 | −1.25 | 0.40 | 1.09 | 0.16 | 0.64 | PAFAH2 | −0.17 | 0.17 | 0.29 | 0.04 | 0.21 | G35671 | 0.27 | 0.40 | 0.38 | 0.16 | −0.56 |
| PBDC1 | 0.82 | −0.50 | −0.82 | −0.18 | −0.56 | KIAA1143 | 0.21 | 0.05 | −0.16 | −0.11 | −0.34 | AC084116.1 | −0.46 | −0.73 | −2.71 | 1.30 | −2.03 |
| AC253536.6 | −1.34 | 0.23 | 0.29 | 0.31 | 0.24 | RNU6-1214P | 1.07 | −0.39 | 0.61 | 0.02 | 0.25 | G28250 | −0.14 | 0.14 | 0.15 | 0.01 | −0.13 |
| MTHFD1L | 0.82 | −1.08 | −1.07 | −0.44 | −0.35 | MAP2K1 | 0.18 | −0.15 | −0.42 | −0.01 | −0.13 | OR7E15P | −0.54 | −0.12 | 0.44 | 1.43 | 1.97 |
| FAM169A | 1.29 | −0.77 | −1.15 | −0.23 | −0.43 | AL139246.4 | −0.66 | 0.44 | 1.26 | −0.14 | 0.60 | AC009159.3 | −0.33 | 0.71 | 0.08 | −0.54 | −1.37 |
| G12891 | −1.29 | 0.47 | 0.86 | 0.46 | 0.57 | AC016772.1 | −1.39 | 1.80 | −1.55 | 1.29 | −3.07 | RFPL4AP6 | 0.53 | −1.47 | 0.12 | −0.89 | 0.41 |
| HMGA1 | 1.00 | −0.46 | −0.82 | −0.05 | −0.34 | PRXL2C | 0.27 | −0.36 | −0.32 | −0.42 | −0.47 | AC025470.1 | −0.48 | −1.18 | −1.16 | −0.32 | −1.87 |
| GCNT4 | 1.42 | −0.49 | −1.00 | −0.05 | −0.96 | IFITM2 | 0.42 | −0.68 | 0.63 | −0.47 | −0.01 | RP11-289H16.1 | −0.27 | 0.05 | −0.04 | −0.67 | −1.01 |
| SLC2A11 | −1.00 | 0.38 | 0.87 | 0.13 | 0.29 | AP002336.1 | 0.43 | −0.20 | −0.19 | −0.06 | 0.06 | FOXC2 | −0.19 | 0.23 | 0.29 | 0.63 | 0.36 |
| GUSBP1 | −0.52 | 0.23 | 0.48 | 0.17 | 0.36 | AC091544.2 | −0.82 | 0.43 | 0.12 | 0.63 | 0.31 | GSR | −0.07 | −0.16 | 0.23 | −0.16 | 0.18 |
| NHP2 | 0.82 | −0.42 | −0.47 | −0.15 | −0.35 | CNOT8 | 0.19 | −0.12 | −0.05 | −0.08 | −0.18 | AP001793.1 | 0.19 | −0.05 | −0.35 | −0.01 | −0.29 |
| NUS1 | 0.86 | −0.39 | −0.55 | −0.17 | −0.25 | NPIPA5 | −0.40 | 0.24 | 0.05 | −0.10 | 0.05 | MTND5P18 | 0.65 | −0.86 | 0.38 | −0.57 | −1.65 |
| KCNIP2 | −1.47 | 0.82 | 1.24 | 0.22 | 0.16 | AC007038.1 | −0.19 | 0.10 | 0.41 | −0.08 | 0.12 | AL021026.1 | 0.36 | −0.47 | −0.71 | 0.07 | −0.49 |
| MFN1 | 0.70 | −0.13 | −0.39 | −0.09 | −0.38 | AL158801.2 | 0.70 | −0.24 | −1.05 | 0.40 | −0.52 | MIR566 | 0.24 | 0.38 | −0.17 | 0.66 | −0.13 |
| AGTR1 | −2.11 | 1.57 | 2.84 | 0.48 | 0.41 | AC010280.1 | −1.59 | 1.87 | 1.24 | 1.50 | −0.19 | LY75 | −0.10 | −0.19 | 0.30 | −0.24 | 0.14 |
| ABAT | −0.96 | 0.48 | 0.94 | 0.10 | 0.31 | HMGN2P5 | 0.29 | −0.07 | −0.45 | −0.13 | −0.48 | AL049873.1 | 0.16 | 0.30 | −0.15 | −0.23 | −0.77 |
| GALT | −1.05 | 0.38 | 0.67 | 0.58 | 0.56 | ANO1 | −0.29 | 0.38 | −0.39 | 0.33 | −0.21 | HMGB3P6 | 0.32 | −1.57 | −0.80 | −0.61 | 0.42 |
| OTUD4 | 0.45 | −0.19 | −0.34 | −0.12 | −0.13 | LY6E-DT | −0.39 | 0.05 | 0.66 | −0.30 | 0.13 | AC090692.3 | −0.36 | −0.31 | −0.07 | 0.04 | −0.70 |
| BX470102.2 | 1.09 | −0.64 | −1.20 | 0.09 | 0.00 | NOP14-AS1 | 0.19 | −0.13 | −0.55 | 0.00 | −0.16 | RNU12-2P | −0.27 | −0.40 | −0.40 | −0.18 | −0.17 |
| ATMIN | 0.78 | −0.16 | −0.51 | −0.03 | −0.54 | AC027612.1 | 0.93 | 0.25 | −2.11 | 0.11 | −1.49 | AC103706.2 | 0.25 | −0.74 | −1.15 | −0.48 | −0.47 |
| ANKRD36B | −0.52 | 0.22 | 0.27 | 0.11 | −0.02 | AC024270.4 | −0.26 | −0.05 | 0.38 | 0.06 | 0.48 | AC018714.1 | −0.49 | 0.05 | 0.10 | 1.04 | 0.89 |
| SRGAP2 | −0.67 | 0.50 | 0.78 | 0.18 | 0.09 | SFXN5 | 0.22 | −0.32 | −0.54 | 0.01 | 0.14 | AL121718.1 | 0.83 | −0.32 | −2.58 | 0.14 | −2.02 |
| EEF1DP4 | −1.80 | 0.02 | 2.10 | −0.10 | 0.36 | FAM92A | −0.28 | 0.00 | 0.44 | −0.17 | 0.14 | AL162390.1 | 0.11 | −0.15 | −0.06 | −0.08 | 0.29 |
| DDX3X | 0.75 | −0.25 | −0.57 | −0.01 | −0.40 | SLIT1 | −0.47 | −0.20 | −0.29 | −0.16 | −0.31 | BAIAP2L1 | 0.06 | 0.07 | −0.24 | −0.01 | −0.01 |
| DDX58 | 0.81 | −0.48 | −0.78 | −0.23 | −0.35 | PHOX2A | −0.93 | 0.76 | 0.59 | 1.61 | 0.17 | OR7D2 | −0.26 | −0.17 | −0.20 | 0.10 | −0.34 |
| GRPEL2 | 1.02 | −0.65 | −1.08 | −0.15 | −0.67 | LCN12 | −1.19 | 0.57 | 0.39 | 0.00 | −0.03 | OR52P1P | −0.36 | 0.05 | 1.86 | 0.13 | 0.57 |
| RNU6-33P | −1.45 | 0.57 | 0.66 | 0.27 | 0.28 | AC126474.1 | 0.47 | −0.29 | −0.26 | 0.02 | 0.17 | AC066615.1 | −0.53 | 1.43 | 0.63 | 0.52 | 0.27 |
| RPL6 | 0.84 | −0.30 | −0.48 | −0.12 | −0.40 | EXOC1L | −1.20 | 1.29 | −1.77 | 1.14 | −2.17 | AL845321.1 | −0.16 | 0.15 | 0.01 | 0.22 | 0.29 |
| HCG27 | −1.05 | 0.08 | 0.78 | 0.18 | 0.67 | AC087639.2 | −1.29 | −0.13 | −0.55 | −0.57 | −1.19 | BCS1L | 0.07 | −0.03 | −0.11 | 0.01 | 0.18 |
| PAK2 | 0.67 | −0.38 | −0.60 | −0.15 | −0.24 | AL138759.1 | 0.97 | 0.41 | −1.53 | 0.94 | 0.15 | AL353611.2 | 0.75 | −1.67 | 0.87 | −0.74 | 1.44 |
| CLCN3 | 0.83 | −0.20 | −0.41 | 0.04 | −0.28 | AL353763.2 | −0.43 | 0.18 | 0.54 | 0.05 | 0.41 | AC009977.1 | −0.18 | −0.18 | 0.06 | 0.14 | 0.78 |
| ARVCF | −0.92 | 0.42 | 0.44 | 0.34 | 0.18 | MAMSTR | −0.42 | −0.03 | 0.67 | −0.26 | −0.02 | FGD2 | 0.10 | −0.34 | −0.22 | −0.24 | 0.04 |
| MUC6 | −1.19 | 0.39 | 0.43 | 0.27 | 0.30 | CFAP44-AS1 | −0.58 | −0.18 | 0.77 | −0.16 | 0.27 | AL365318.1 | 0.13 | 0.13 | 0.64 | 0.14 | 0.21 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| SH2D2A | 1.82 | −1.60 | −1.91 | −0.99 | −0.78 | AL353706.1 | 0.64 | −0.10 | −0.38 | −0.48 | −0.49 | OTUD3 | −0.03 | 0.02 | −0.14 | 0.02 | 0.05 |
| CFAP44 | −0.57 | 0.44 | 0.62 | 0.09 | 0.25 | SPTLC3 | 0.26 | 0.21 | 0.28 | 0.22 | −0.14 | AL355512.1 | −0.25 | −0.66 | 0.68 | −0.81 | 0.79 |
| RPP40 | 1.22 | −0.68 | −0.81 | −0.36 | −0.70 | RNA5SP513 | −1.14 | 1.82 | −1.03 | −0.23 | −1.99 | AC007431.1 | −0.15 | 0.42 | −0.17 | 0.44 | 0.08 |
| FAM96AP2 | 1.42 | −1.34 | −1.89 | −0.61 | −0.72 | RNASE6 | 0.54 | −0.46 | 0.04 | −0.20 | 0.14 | AC079922.1 | 0.22 | −0.19 | −0.34 | −0.41 | −0.18 |
| ARNTL2-AS1 | 2.24 | −0.79 | −1.73 | −0.47 | −1.23 | HMGN2P8 | 0.79 | 0.04 | −1.28 | −0.03 | −1.20 | MIR501 | 0.54 | −1.10 | 0.05 | −0.34 | 0.45 |
| AC055716.3 | −3.10 | 2.33 | 3.66 | 0.10 | −0.35 | NKAIN1 | 0.58 | 0.11 | −0.17 | 0.14 | −0.35 | OLA1P3 | 0.17 | −0.28 | −0.41 | 0.31 | 0.29 |
| G32307 | −1.59 | 0.75 | 0.53 | 0.13 | −0.21 | RAD51 | 0.65 | −0.73 | −1.88 | −0.39 | −1.34 | CTBP2P3 | 0.84 | −0.39 | −0.26 | −1.02 | −0.38 |
| SP5 | −1.91 | 1.51 | 1.89 | 1.21 | 0.45 | AL023755.1 | −0.77 | −0.23 | 0.11 | 0.38 | 0.30 | B4GALNT3 | −0.09 | 0.25 | −0.16 | 0.14 | −0.03 |
| HEATR3 | 0.50 | −0.47 | −0.34 | −0.03 | 0.19 | DDX55P1 | −0.51 | 0.11 | −0.06 | 0.07 | −0.44 | AC016866.2 | 0.16 | 0.23 | −0.06 | 0.17 | −0.48 |
| 'RYZL2P-SEC16 | −1.35 | 0.34 | 1.32 | 0.01 | 0.25 | PKIG | −0.26 | 0.22 | 0.54 | −0.25 | −0.04 | AL645944.2 | 0.72 | −1.94 | −0.38 | 0.37 | 3.05 |
| CAPS | −0.90 | 0.42 | 0.52 | 0.37 | 0.54 | ETF1P2 | 0.47 | 0.07 | 0.05 | −0.09 | −0.22 | AL590632.1 | 0.15 | −1.19 | 0.09 | −0.55 | 0.41 |
| PON3 | −1.03 | 0.71 | 1.24 | 0.09 | 0.30 | PSIP1 | −0.18 | −0.03 | 0.32 | −0.02 | 0.17 | AC024619.2 | −0.86 | 1.04 | −0.02 | 1.58 | 1.29 |
| CCDC159 | −1.16 | 0.49 | 0.52 | 0.61 | 0.23 | LINC00858 | −1.33 | 0.84 | −1.77 | −0.60 | −1.99 | PRMT1P1 | 0.16 | −0.01 | −0.81 | 0.30 | −0.63 |
| LIMS1 | 0.69 | −0.38 | −0.58 | −0.16 | −0.36 | AL137026.1 | −0.80 | −0.05 | 0.30 | 0.60 | 0.15 | LINC02357 | 0.37 | −1.23 | −2.00 | −0.43 | −1.27 |
| AP002762.1 | 1.67 | −0.67 | −1.48 | −0.09 | −0.94 | CALHM2 | −0.26 | 0.15 | 0.36 | −0.11 | −0.13 | LINC02047 | 0.53 | −1.33 | −2.06 | −0.70 | −1.34 |
| FAM126A | 0.63 | −0.40 | −0.44 | −0.19 | −0.09 | NCR1 | 0.94 | −0.91 | −1.37 | −0.06 | −0.60 | LINC00474 | 0.80 | −0.42 | −2.10 | 1.24 | −0.72 |
| SMIM8 | −0.50 | 0.29 | 0.48 | 0.18 | 0.17 | QSOX2 | −0.22 | −0.12 | −0.14 | −0.01 | 0.10 | MYT1L | −0.21 | −0.43 | −0.25 | 0.12 | −0.51 |
| G6PD | 0.58 | −0.14 | −0.82 | 0.26 | −0.43 | AC006270.1 | 0.42 | −0.33 | −0.25 | −0.34 | −0.20 | LINC01689 | 0.41 | 0.07 | −1.84 | 0.85 | −1.96 |
| NFIB | −0.59 | 0.54 | 0.45 | 0.27 | 0.09 | AL157932.1 | 0.78 | −0.52 | −0.60 | −0.54 | −0.25 | HMGB3P16 | −0.61 | 0.64 | −0.70 | 1.44 | −2.14 |
| ADRB1 | −1.93 | 1.71 | 0.78 | 1.23 | 0.78 | KIAA0391 | 0.21 | −0.37 | −0.36 | −0.28 | 0.10 | AL109658.1 | 0.58 | −1.27 | −0.46 | −1.31 | −0.35 |
| RGL3 | −1.60 | 0.60 | 0.13 | 0.90 | 0.10 | AC092628.2 | −0.99 | −0.39 | 0.14 | 0.85 | 0.90 | AC117422.1 | 0.28 | 0.02 | 0.88 | 0.07 | 0.88 |
| IGSF10 | −1.56 | 1.45 | 2.18 | 0.40 | 0.27 | AC005083.1 | −0.69 | 0.28 | 1.28 | 0.47 | 1.37 | RPS15AP36 | −0.68 | −0.34 | 1.42 | −0.74 | −1.28 |
| MAD2L1 | 1.21 | −0.99 | −1.27 | −0.36 | −0.61 | NLRC5 | −0.30 | −0.33 | 0.04 | −0.28 | 0.43 | AL512310.7 | 0.41 | 0.35 | −1.24 | 1.22 | −0.47 |
| MAGI2-AS3 | −1.38 | 0.52 | 1.76 | −0.33 | 0.25 | FOXP2 | −0.29 | 0.29 | −0.02 | 0.28 | −0.45 | KCNS2 | 0.09 | −0.18 | 0.30 | 0.01 | 0.21 |
| FGGY | −0.53 | 0.18 | 0.49 | 0.01 | 0.18 | NDUFV3 | −0.14 | 0.00 | 0.15 | −0.03 | 0.16 | AC097641.2 | −0.16 | 0.66 | 0.70 | 0.16 | −0.41 |
| ING4 | −0.68 | 0.47 | 0.68 | 0.20 | 0.09 | AP001625.2 | −0.46 | −0.15 | 0.80 | 0.15 | 0.60 | AL049833.2 | 0.49 | 0.37 | −1.77 | 1.28 | −0.54 |
| PPIAP29 | 1.36 | −0.53 | −0.99 | −0.30 | −0.86 | AC068860.1 | −0.72 | 0.44 | 0.21 | 0.19 | 0.01 | AC023347.1 | −0.60 | −0.14 | −1.07 | 0.21 | −0.34 |
| CACUL1 | 0.51 | −0.20 | −0.40 | −0.08 | −0.23 | AC021224.1 | 1.01 | −0.88 | 0.26 | 1.02 | 0.92 | KCNK7 | 0.12 | 0.52 | 0.33 | 0.53 | −0.19 |
| CTBP2 | 0.39 | −0.21 | −0.53 | −0.06 | −0.18 | RNU6-836P | 1.21 | −0.45 | −0.95 | 0.02 | −0.27 | AP003031.1 | −0.25 | 1.04 | 1.01 | 0.99 | −0.98 |
| PURB | 0.78 | −0.20 | −0.58 | −0.07 | −0.59 | AL136982.1 | −0.67 | 0.87 | 0.29 | −0.18 | −0.53 | LINC00927 | 0.44 | −0.85 | −0.74 | 0.62 | −0.97 |
| DNTTIP2 | 0.79 | −0.40 | −0.65 | −0.26 | −0.56 | AC009716.2 | 0.36 | −0.16 | 0.00 | −0.19 | 0.05 | AC007389.4 | −0.69 | 1.13 | −0.32 | −0.81 | −2.13 |
| RIOK3 | 0.51 | −0.10 | −0.51 | 0.08 | −0.38 | AL158847.1 | −1.12 | 1.25 | 1.70 | 1.03 | 0.65 | NELFE | −0.06 | −0.05 | −0.18 | −0.10 | −0.06 |
| QRFPR | 3.02 | −0.34 | −2.50 | −0.02 | −2.40 | ERP27 | 0.42 | −0.60 | 0.20 | −0.16 | 0.45 | AC105129.3 | 0.14 | −0.21 | −0.24 | 0.00 | 0.17 |
| PDAP1 | 0.69 | −0.33 | −0.63 | −0.20 | −0.28 | AC012073.1 | 0.40 | −0.50 | −0.49 | −0.15 | −0.09 | AC063976.1 | −0.32 | 0.97 | 0.02 | 0.44 | 0.54 |
| RAC1 | 0.67 | −0.32 | −0.47 | −0.19 | −0.29 | AL023581.1 | 0.63 | −0.64 | −0.03 | −0.15 | −0.04 | CAV1 | 0.09 | 0.16 | −0.24 | −0.07 | −0.50 |
| PRRC2C | 0.59 | −0.38 | −0.67 | −0.19 | −0.25 | SFMBT2 | 0.29 | −0.26 | −0.39 | 0.01 | 0.13 | MSLNL | −0.51 | 1.40 | 0.12 | 0.69 | 0.79 |
| CSRNP3 | −0.91 | 0.62 | 0.99 | 0.08 | −0.05 | AC104170.2 | −0.57 | 0.30 | 0.56 | −0.24 | 0.48 | FOXN3P1 | 0.42 | −0.31 | −1.22 | 0.47 | −1.34 |
| PCDHGB2 | −1.13 | 0.69 | 1.41 | 0.37 | 0.54 | AL139398.1 | −0.63 | 0.46 | −0.19 | 0.64 | 0.18 | AC008948.1 | 0.33 | −0.84 | −2.23 | 1.40 | −0.55 |
| ARTN | 2.03 | −1.59 | −2.11 | −0.24 | 0.17 | LIMD1-AS1 | −0.91 | 0.02 | 1.18 | −0.07 | 1.06 | CEACAM16 | 0.30 | −0.19 | 0.16 | −0.48 | 0.43 |
| AL645608.2 | −2.10 | 0.50 | 1.01 | 0.77 | 0.66 | HLA-DRB9 | −0.87 | 1.10 | 0.12 | 1.03 | 0.76 | RASSF9 | −0.08 | 0.47 | 0.69 | 0.33 | −0.03 |
| NOP53 | −0.70 | 0.60 | 0.68 | 0.33 | 0.20 | ETV3 | 0.20 | 0.07 | −0.14 | 0.03 | −0.32 | HPS3 | 0.05 | −0.05 | 0.12 | −0.01 | 0.07 |
| AC016229.1 | −1.58 | 0.61 | 1.73 | −0.34 | −0.26 | PRKAA1 | 0.14 | 0.02 | −0.01 | −0.12 | −0.16 | CERS2 | 0.06 | −0.06 | −0.33 | −0.18 | −0.22 |
| HS6ST3 | −1.81 | 0.11 | 0.66 | 0.87 | 1.01 | ITPKB | −0.17 | 0.15 | −0.01 | 0.10 | −0.11 | RNU6-1093P | 0.77 | 1.59 | 0.48 | 1.68 | 0.81 |
| A2ML1 | 1.32 | −0.26 | −0.58 | −0.10 | −0.54 | NPR2 | −0.29 | 0.18 | 0.10 | 0.10 | 0.09 | AC010320.5 | −0.29 | −0.15 | −0.80 | −0.70 | −0.23 |
| NUFIP2 | 0.57 | −0.27 | −0.48 | −0.20 | −0.32 | SLC01C1 | −0.50 | 0.25 | 1.00 | −0.23 | 0.15 | AC104472.2 | 0.42 | −1.41 | 0.38 | −0.63 | 1.03 |
| IER5L | 0.83 | −0.17 | −0.33 | −0.38 | −0.70 | OR55B1P | 0.43 | −0.36 | −0.86 | −0.20 | −0.47 | G35131 | −0.19 | 0.92 | −0.02 | 0.21 | −0.37 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| ANKRD20A7P | −1.65 | 0.80 | 1.45 | 0.50 | 0.64 | ASB9 | −0.51 | 0.67 | 0.19 | −0.06 | −0.60 | NME8 | −0.19 | 0.18 | 0.37 | 0.01 | 0.13 |
| SNORD116-8 | −1.66 | 1.02 | 1.48 | 0.76 | −0.26 | MYO19 | 0.23 | −0.16 | −0.50 | 0.06 | −0.05 | KRTAP15-1 | −0.79 | −0.38 | −0.24 | −0.51 | −0.44 |
| ADD3 | −0.92 | 0.54 | 1.08 | 0.23 | 0.23 | HNRNPCL1 | 1.29 | −1.48 | −1.36 | −0.11 | 0.48 | AC026310.2 | 0.44 | −0.69 | −2.67 | −0.21 | −1.33 |
| MTIF2 | 0.63 | −0.40 | −0.50 | −0.16 | −0.06 | RNU6-194P | 0.79 | −0.18 | −1.95 | −0.05 | −1.30 | AC005921.3 | −0.10 | −0.07 | −0.26 | 0.17 | 0.03 |
| HCCS | 0.72 | −0.27 | −0.42 | −0.25 | −0.40 | AC097488.1 | −1.45 | 1.47 | 0.42 | 0.30 | 0.66 | AL117338.1 | 0.52 | −0.40 | −1.88 | 1.46 | −0.97 |
| CEBPB-AS1 | −1.49 | 1.02 | 0.96 | 0.65 | −0.11 | RNU6-1024P | 0.89 | −0.67 | 0.15 | −0.37 | −0.04 | AC007278.1 | 0.16 | −0.66 | −0.62 | −0.25 | −0.12 |
| CAMSAP2 | 0.53 | −0.16 | −0.36 | −0.15 | −0.33 | JMJD1C | 0.17 | 0.07 | −0.07 | −0.04 | −0.22 | RPSAP57 | 0.40 | 0.20 | 0.60 | −0.08 | 0.63 |
| BUD31 | 0.73 | −0.31 | −0.53 | −0.24 | −0.38 | SAAL1 | 0.16 | −0.31 | −0.15 | 0.05 | 0.24 | SRGAP1 | −0.09 | 0.11 | −0.02 | −0.26 | −0.05 |
| CNOT11 | 0.65 | −0.18 | −0.32 | −0.12 | −0.20 | RAPGEF4 | 0.23 | 0.11 | −0.09 | 0.25 | −0.18 | LINC01276 | 0.70 | −0.31 | −0.97 | −0.26 | −1.32 |
| PWAR6 | −1.02 | 0.72 | 1.11 | 0.25 | 0.58 | ALKBH1 | 0.18 | −0.08 | −0.18 | −0.01 | −0.22 | AL512328.1 | −0.38 | 0.25 | 0.62 | 1.51 | 0.47 |
| POLE3 | 0.74 | −0.51 | −0.82 | −0.12 | −0.41 | AC107871.1 | −0.22 | 0.16 | 0.16 | 0.01 | 0.03 | ARMC10P1 | 0.41 | −1.16 | −0.81 | −0.96 | −0.57 |
| SCARB1 | −0.73 | 0.60 | 0.33 | 0.33 | 0.08 | DENND6A-AS1 | 0.69 | −0.48 | 0.04 | −0.11 | 0.36 | AC004000.1 | −0.08 | −0.07 | 0.39 | −0.11 | 0.22 |
| PSMD8 | 0.72 | −0.38 | −0.49 | −0.22 | −0.42 | HNRNPA1P15 | 0.44 | −0.44 | −0.40 | 0.01 | 0.14 | AC009435.1 | 0.67 | −0.96 | −1.62 | −1.16 | −1.41 |
| AL662800.2 | −1.91 | 0.61 | 1.08 | 1.08 | 1.07 | OR1L4 | −0.55 | 0.51 | 0.12 | 0.26 | 0.23 | AC097468.1 | −0.67 | 0.74 | −1.18 | 2.45 | −2.24 |
| FARSB | 0.69 | −0.55 | −0.69 | −0.20 | −0.08 | RPS10P14 | 0.90 | −1.69 | −0.38 | 0.66 | 1.28 | AC104984.4 | 0.36 | 0.35 | −1.70 | 1.40 | −1.71 |
| DPH2 | 0.84 | −0.53 | −0.98 | −0.14 | −0.44 | AC010332.2 | −1.22 | −0.64 | 0.35 | −0.49 | 0.11 | AC068189.1 | 0.14 | −0.32 | −0.79 | 0.52 | 0.01 |
| CDC45 | 1.19 | −1.14 | −1.96 | −0.13 | −0.66 | STOML3 | −0.97 | −0.26 | 0.70 | 0.19 | 0.64 | LEXM | 0.13 | 0.22 | 0.58 | 0.38 | 0.09 |
| AC026150.1 | −1.36 | 0.46 | 1.01 | 0.49 | 0.24 | DDX11L8 | −0.64 | 1.23 | 0.67 | 0.44 | 0.32 | LINC00343 | 0.27 | −0.79 | −2.38 | 0.55 | −2.20 |
| ASIC3 | −1.20 | 0.58 | 0.67 | 0.45 | 0.28 | RPS20P31 | 0.45 | 0.09 | −1.46 | 0.13 | −1.12 | AP001257.1 | 0.34 | −1.40 | −1.09 | 0.16 | 0.06 |
| CNTN4 | −1.68 | 1.02 | 0.98 | 0.67 | −0.46 | AC091170.1 | −1.61 | 1.67 | 0.08 | 1.56 | −0.92 | OR2L6P | −0.49 | −0.30 | 0.14 | −0.92 | −0.61 |
| PIM1 | 0.87 | −0.15 | −0.78 | 0.09 | −0.80 | AL137161.1 | −0.69 | −0.29 | 0.18 | −0.72 | −0.43 | AL662820.1 | 0.56 | −0.11 | −0.49 | −0.46 | −1.02 |
| CPNE9 | −1.91 | 0.86 | 0.71 | 1.33 | 0.65 | SNORD78 | 0.55 | −0.63 | −0.41 | −0.09 | 0.22 | AC138781.1 | −0.55 | −0.43 | −0.26 | 1.17 | −0.56 |
| AKIRIN2 | 0.65 | −0.35 | −0.55 | −0.16 | −0.26 | RTTN | −0.13 | −0.04 | 0.12 | −0.09 | 0.04 | AL445228.2 | −0.19 | −0.24 | −0.89 | 0.72 | −0.62 |
| OR52B6 | −1.19 | 0.56 | 0.66 | −0.27 | −0.45 | AL357146.1 | −1.17 | −0.20 | 0.12 | −0.13 | −1.06 | KATNBL1P6 | 0.29 | 0.75 | 1.22 | 0.20 | −1.67 |
| AC005332.5 | −1.20 | 0.63 | 1.22 | 0.16 | 0.40 | RPL17P26 | 1.12 | −0.23 | −2.13 | 0.90 | −0.81 | ENY2 | −0.05 | 0.02 | −0.09 | 0.00 | −0.12 |
| ING5 | −0.72 | 0.26 | 0.14 | 0.30 | 0.19 | CLDN1 | −0.36 | 0.58 | 0.89 | 0.05 | 0.04 | OR5K4 | −0.54 | −0.58 | −1.15 | −0.24 | −0.95 |
| COQ2 | 1.03 | −0.59 | −0.39 | −0.38 | −0.37 | DNM2 | −0.18 | 0.03 | −0.10 | 0.07 | 0.01 | AC234644.1 | −0.16 | 0.46 | 0.11 | 0.30 | 0.12 |
| G36288 | −1.57 | 0.84 | 2.17 | 0.17 | 0.55 | PMP22 | −0.32 | 0.29 | 0.00 | −0.05 | −0.29 | RN7SL75P | 0.27 | −1.08 | 0.10 | −0.65 | 1.53 |
| CENPU | 0.74 | −0.40 | −0.67 | −0.25 | −0.39 | MIR4513 | 0.80 | 0.21 | −0.04 | −0.17 | −0.74 | AC009027.1 | 0.40 | 0.74 | −1.23 | −1.31 | −1.66 |
| HSPD1P11 | −1.34 | 0.48 | 1.66 | −0.13 | 0.38 | HMGCS1 | 0.43 | −0.08 | −0.37 | 0.38 | 0.11 | DISC1 | 0.08 | −0.30 | −0.02 | 0.12 | 0.39 |
| KLRF2 | −2.20 | 2.05 | 2.35 | 0.85 | −0.02 | HMGB1P17 | 1.15 | −1.65 | −2.01 | −0.63 | 0.50 | RTP1 | 0.71 | −0.20 | −0.87 | −0.83 | −0.52 |
| MPP2 | −1.54 | 0.15 | 1.67 | 0.09 | 0.90 | AC084824.2 | 0.72 | 0.34 | −1.15 | −0.51 | −1.44 | AC234781.2 | 0.15 | 0.19 | 0.50 | −0.39 | −0.01 |
| LUZP1 | 0.49 | −0.24 | −0.44 | −0.21 | −0.32 | PARGP1 | −0.39 | 0.45 | 0.26 | 0.35 | 0.08 | SERPINA13P | 0.69 | −0.75 | −0.46 | 0.94 | 0.26 |
| LTBP3 | −0.83 | 0.50 | 0.73 | 0.27 | 0.22 | AL591379.1 | −1.31 | 0.01 | 1.66 | 0.21 | 0.90 | LINC02479 | −0.45 | −1.92 | −1.19 | 0.94 | 0.95 |
| GPR87 | 1.47 | −0.40 | −0.77 | −0.01 | −0.75 | C1orf146 | 0.85 | −0.69 | 0.24 | −0.28 | 0.63 | PACERR | −0.22 | 0.08 | 0.70 | −0.35 | −0.11 |
| ARMC2 | −0.67 | 0.33 | 0.83 | 0.03 | 0.24 | FAR1-IT1 | −0.43 | −0.19 | −0.12 | −0.22 | 0.17 | FAM78A | 0.11 | −0.31 | −0.04 | −0.18 | 0.33 |
| KDM1B | 0.51 | −0.25 | −0.52 | −0.02 | −0.15 | AC024257.4 | −0.88 | 0.78 | −0.89 | 0.18 | −0.59 | MIR4529 | 0.25 | 0.33 | 0.94 | −1.04 | −0.30 |
| PRRG3 | −1.32 | 0.63 | 1.67 | −0.33 | 0.10 | DGUOK | 0.19 | −0.08 | 0.09 | −0.13 | 0.05 | RNU6-615P | 0.41 | 0.30 | 0.99 | 0.03 | 0.05 |
| PTDSS1 | 0.65 | −0.13 | −0.35 | −0.07 | −0.40 | AC011933.1 | 0.73 | −0.53 | −0.26 | −0.03 | 0.55 | AC013470.3 | 0.36 | −1.03 | −1.86 | 0.48 | 0.94 |
| SELE | 1.87 | −2.12 | −0.81 | −0.98 | −2.24 | AC017067.1 | −1.62 | 2.85 | 1.82 | 1.02 | 0.29 | AC106827.1 | 0.13 | −0.09 | −0.03 | −0.18 | 0.53 |
| MYOM3 | 1.15 | −0.91 | −1.27 | −0.03 | −0.58 | AC108457.1 | −0.70 | 0.33 | −0.40 | 0.31 | −1.21 | SEPT7P7 | −0.66 | 0.58 | 1.60 | −0.34 | 0.65 |
| PLP2 | 1.01 | −0.24 | −0.73 | −0.16 | −0.61 | BACH1-AS1 | 0.35 | −0.09 | −0.57 | −0.21 | −0.42 | OLFML2B | 0.13 | 0.10 | 0.85 | −0.68 | −0.39 |
| F10 | −1.51 | 1.14 | 1.73 | 0.18 | 0.14 | AP003486.1 | 0.24 | −0.04 | 0.06 | 0.20 | 0.16 | AC073346.1 | 0.50 | 0.30 | 1.18 | −0.63 | 0.01 |
| POLR1B | 0.81 | −0.38 | −0.42 | −0.20 | −0.17 | AC012170.1 | 0.50 | −0.26 | 0.12 | −0.12 | 0.17 | LINC01897 | −0.49 | −1.55 | −0.19 | −1.14 | 1.30 |
| PCSK9 | 1.52 | −0.46 | −1.33 | 0.73 | −0.44 | AP006248.4 | −0.76 | −0.09 | 1.10 | 0.27 | 0.03 | MRPS17 | 0.10 | −0.05 | −0.27 | 0.16 | −0.11 |
| FABP5P3 | 2.02 | −0.97 | −1.37 | 0.33 | −0.89 | AC120498.6 | −1.35 | −0.32 | 2.17 | −0.99 | 1.13 | CTRB1 | −0.21 | 0.43 | −0.06 | 0.62 | −0.30 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| MFSD4A | −1.03 | 0.63 | 0.69 | 0.34 | 0.18 | KIAA1958 | 0.16 | 0.01 | −0.01 | 0.11 | 0.09 | MIR137HG | 0.25 | −1.16 | −1.39 | 0.69 | 1.05 |
| PARP14 | 0.98 | −0.86 | −0.81 | −0.61 | −0.38 | AL022345.4 | −0.98 | 0.08 | 1.24 | −0.51 | −0.11 | AC012363.2 | 0.29 | −0.16 | −0.31 | 0.56 | −1.28 |
| INTS7 | 0.67 | −0.31 | −0.40 | −0.13 | −0.19 | PRB4 | −0.49 | −0.22 | −0.42 | 0.14 | 0.19 | AC116096.1 | −0.14 | 0.13 | 0.12 | −0.16 | −0.25 |
| ARHGEF40 | −0.91 | 0.33 | 0.56 | 0.19 | 0.12 | CARD16 | 0.39 | −0.33 | 0.19 | −0.50 | −0.13 | AL670729.1 | −0.24 | −0.27 | −1.17 | −0.28 | −0.92 |
| MIR222HG | 0.98 | −0.59 | −0.99 | −0.04 | −0.24 | AL392089.1 | 0.47 | −0.63 | −0.40 | −0.15 | 0.29 | AP000844.1 | −0.23 | 0.58 | 0.94 | −0.39 | −0.34 |
| GASAL1 | 1.17 | −1.06 | −1.16 | −0.05 | −0.41 | G33515 | −0.96 | 1.33 | 1.17 | 1.00 | 1.09 | AC007998.5 | 0.24 | −0.72 | −0.04 | −0.36 | 0.64 |
| PES1 | 0.69 | −0.48 | −0.69 | −0.22 | −0.21 | RNA5SP507 | −0.73 | 1.27 | 1.58 | 0.80 | 0.61 | AC067838.1 | −0.19 | 0.72 | 0.64 | 0.53 | 0.19 |
| SENP1 | 0.50 | −0.20 | −0.33 | −0.11 | −0.24 | AL139300.1 | −0.69 | 0.41 | 1.00 | −0.16 | 0.19 | AC008427.1 | 0.64 | −0.73 | −0.77 | 0.73 | −1.27 |
| FLJ42969 | 2.94 | −1.03 | −2.70 | 0.30 | −1.62 | LINC00974 | 1.26 | −1.67 | −0.82 | −0.63 | 0.92 | AC026427.1 | 0.50 | −0.72 | 0.08 | −0.19 | 0.92 |
| OR51M1 | −1.79 | 0.71 | −0.06 | 0.29 | −0.83 | COL6A4P2 | −0.62 | 0.81 | −0.50 | 0.41 | −0.78 | AC010931.3 | 0.55 | −1.76 | −0.52 | −1.23 | 2.79 |
| NAP1L4 | 0.43 | −0.24 | −0.43 | −0.08 | −0.17 | AC109454.2 | −0.44 | −0.01 | 0.21 | −0.11 | 0.28 | RPS6P16 | −0.13 | 0.10 | −1.13 | 0.13 | −0.35 |
| RAB9B | −1.41 | 0.63 | 0.95 | −0.08 | −0.41 | AC026436.1 | 0.61 | −0.31 | 0.97 | −0.61 | 0.52 | PADI4 | 0.27 | −0.06 | −0.94 | −0.40 | −1.02 |
| P2RY1 | 1.35 | −0.59 | −1.05 | −0.07 | −0.75 | AC132942.1 | 0.60 | 0.21 | −0.16 | −0.10 | −0.20 | AC009093.4 | −0.23 | −0.20 | −0.68 | 0.52 | 0.29 |
| LAMA3 | 0.91 | −0.36 | −0.94 | −0.06 | −0.38 | MIR550A1 | 1.07 | 0.19 | 0.81 | −0.39 | −0.28 | AL596442.2 | 0.48 | 0.50 | −2.00 | 2.28 | −1.78 |
| GREB1L | −0.78 | 0.33 | 0.40 | 0.29 | 0.07 | PPP1R12A | −0.17 | 0.09 | 0.05 | −0.08 | −0.19 | AC098872.1 | −0.34 | −0.75 | 1.31 | −0.16 | 0.03 |
| LINC00885 | −1.28 | 1.17 | 1.35 | 0.90 | 0.28 | SLC25A1P1 | 0.97 | −2.68 | −2.87 | −0.14 | 0.09 | AC116447.1 | 0.32 | −1.05 | 0.39 | −0.13 | 0.06 |
| AL031716.1 | −1.22 | 0.38 | 0.67 | 0.22 | 0.30 | RPL21P75 | 0.64 | −0.09 | 0.54 | −1.07 | −0.32 | CNOT3 | −0.05 | −0.04 | −0.23 | −0.06 | −0.06 |
| LRP2BP | −0.57 | 0.53 | 0.36 | 0.04 | −0.18 | RNASE4 | −0.74 | 0.97 | 0.37 | 0.89 | −0.55 | MSL3 | 0.03 | −0.14 | −0.09 | −0.11 | 0.02 |
| C6orf62 | 0.59 | −0.30 | −0.35 | −0.06 | −0.20 | RGS12 | 0.23 | 0.02 | −0.40 | 0.16 | −0.10 | AL591122.1 | 0.87 | −0.23 | −0.26 | 1.01 | 0.88 |
| IFNGR1 | 0.85 | −0.47 | −0.52 | −0.17 | −0.17 | HPCAL4 | 0.90 | −0.43 | −0.53 | −0.20 | −0.58 | RNU6-1255P | 0.26 | 1.16 | −2.22 | 0.29 | −0.89 |
| AQP3 | 1.72 | −0.72 | −1.57 | 0.09 | −0.71 | SDAD1P1 | −0.34 | 0.33 | 0.27 | 0.09 | −0.36 | AP000786.1 | −0.11 | 0.11 | 0.56 | 0.38 | 0.62 |
| FAM208B | 0.51 | −0.29 | −0.31 | −0.14 | −0.11 | ROR1-AS1 | −0.44 | −0.11 | 0.14 | −0.47 | 0.02 | BCL2L2 | −0.04 | −0.01 | −0.13 | 0.02 | 0.03 |
| MCM2 | 0.98 | −0.96 | −1.07 | −0.12 | −0.10 | AC024451.4 | 0.36 | −0.50 | −0.43 | −0.29 | 0.15 | RHPN1-AS1 | −0.24 | −0.52 | −0.19 | −0.60 | −0.66 |
| AC087284.1 | 1.21 | −0.66 | −0.64 | −0.48 | −0.36 | GAPDHP65 | 0.82 | 0.20 | −1.43 | 0.58 | −0.41 | IFNL1 | 0.40 | −0.71 | −1.03 | 0.12 | 0.15 |
| AAMDC | −1.50 | 0.65 | 0.94 | 0.93 | 0.33 | SNORD85 | 0.53 | −0.59 | 0.27 | −0.27 | 0.09 | LINC01093 | −0.51 | −0.45 | 0.17 | 0.54 | 0.53 |
| IQGAP1 | 0.53 | −0.14 | −0.45 | −0.10 | −0.37 | RBM5-AS1 | −0.24 | −0.22 | −0.48 | 0.03 | 0.00 | SCARNA1 | −0.14 | 0.60 | 0.75 | 0.25 | −0.88 |
| COL11A2 | −1.18 | 0.51 | 0.44 | 0.67 | 0.19 | C7orf26 | −0.17 | 0.03 | 0.02 | 0.01 | 0.13 | AC107021.2 | −0.22 | −0.52 | 0.27 | −0.03 | 0.70 |
| RP11-7G23.4 | −3.14 | 1.72 | 1.96 | 2.45 | 1.99 | AC112484.4 | 1.09 | 0.65 | −0.71 | 0.94 | −0.18 | MTCO1P53 | −0.40 | 0.70 | 1.06 | 0.99 | 0.24 |
| EPOP | 1.53 | −0.97 | −2.28 | 0.24 | −1.37 | AC000111.2 | −1.49 | 0.24 | 0.10 | 1.88 | 1.36 | AC087439.1 | 0.41 | −0.94 | 2.51 | −0.31 | 1.66 |
| PHBP16 | 3.10 | −2.19 | −3.52 | −0.34 | −2.52 | CCNYL2 | −1.14 | 1.02 | 0.22 | 0.83 | −0.13 | NAIP | 0.09 | −0.20 | −0.04 | −0.01 | −0.05 |
| LRRFIP1 | 0.56 | −0.32 | −0.78 | −0.19 | −0.36 | AL158207.1 | 0.69 | −0.19 | −0.09 | 0.51 | 0.49 | FLJ20306 | −0.15 | −0.31 | 0.13 | −0.27 | 0.34 |
| MMP3 | 3.11 | −2.83 | −3.24 | −1.10 | −4.67 | CATIP-AS2 | 1.38 | −1.69 | −1.28 | −0.11 | −0.47 | AC005341.1 | 0.56 | −0.55 | −1.60 | −0.06 | −1.76 |
| CHD1 | 0.63 | −0.36 | −0.63 | −0.16 | −0.40 | AC009065.8 | −0.36 | 0.17 | 0.37 | −0.09 | 0.10 | AC002558.2 | −0.10 | −0.37 | 0.06 | −0.10 | 0.50 |
| HNRNPA1P2 | −1.38 | 0.78 | 0.92 | 0.67 | 0.35 | ANKRD12 | 0.16 | 0.13 | −0.10 | 0.06 | −0.27 | AC019201.1 | 0.50 | 0.16 | −1.01 | −0.77 | −1.09 |
| PSMC2 | 0.70 | −0.30 | −0.53 | −0.16 | −0.45 | BX322650.1 | −0.59 | 0.51 | 0.45 | −0.28 | −0.10 | FGF5 | 0.33 | 0.34 | −0.50 | −0.46 | −1.26 |
| DDTL | −1.36 | 0.01 | 0.30 | 0.55 | 0.78 | AC130895.1 | 0.27 | −0.57 | −0.09 | −0.03 | 0.54 | SDC4P | −0.72 | 0.72 | −1.20 | 0.86 | 1.04 |
| AC016705.1 | −1.65 | 0.50 | 0.74 | −0.06 | −0.13 | G38011 | −0.45 | 0.05 | −0.25 | −0.02 | −0.32 | AC106734.1 | −0.55 | −2.46 | 1.36 | −2.38 | 0.64 |
| ST6GAL2 | −1.74 | 0.75 | 0.55 | 0.29 | 0.27 | AF274858.1 | −0.58 | −0.10 | −0.06 | −0.21 | −0.42 | BPIFB2 | −0.51 | −0.75 | 0.38 | −2.11 | −0.57 |
| ACSM5 | −1.75 | 1.19 | 0.74 | 0.86 | −0.05 | GFPT2 | −0.43 | −0.06 | 0.36 | −0.28 | −0.14 | C9orf85 | −0.04 | −0.01 | 0.05 | −0.02 | 0.05 |
| GYS1 | 0.58 | −0.44 | −0.90 | 0.02 | −0.08 | AC012557.1 | 0.58 | 0.18 | 0.03 | 0.09 | −0.15 | AC092435.3 | −0.38 | −0.05 | −1.27 | 0.38 | −1.25 |
| MCMBP | 0.62 | −0.30 | −0.33 | −0.17 | −0.21 | CPSF1P1 | 0.53 | −0.58 | −0.51 | 0.08 | 0.04 | AL121758.1 | 0.60 | 0.24 | −2.04 | 1.17 | 0.35 |
| CREBRF | −0.71 | 0.69 | 0.88 | 0.25 | 0.00 | LINC02446 | 1.16 | −0.10 | −0.94 | −0.54 | 0.00 | MTCO3P16 | −0.73 | −0.12 | 0.72 | −0.26 | −1.42 |
| AC108062.1 | −0.89 | 0.63 | 1.04 | 0.68 | 0.42 | FAAP24 | 0.35 | −0.36 | −0.34 | −0.01 | −0.01 | CCRLIP1 | −0.37 | −0.03 | 1.36 | 0.12 | 0.71 |
| MSANTD3 | 0.79 | −0.38 | −0.70 | −0.35 | −0.41 | RASAL3 | 0.45 | −0.65 | 0.06 | −0.60 | 0.32 | HEXIM1 | −0.03 | 0.05 | −0.06 | 0.13 | −0.04 |
| PFKFB1 | −1.45 | 0.35 | 1.15 | 0.27 | 0.46 | AC027279.2 | −0.42 | 0.42 | 0.17 | 0.40 | 0.10 | LINC02417 | −0.87 | −0.69 | 0.39 | 0.26 | 1.04 |
| PHB2 | 0.59 | −0.25 | −0.52 | −0.10 | −0.33 | RNU6-429P | −1.18 | −0.16 | 0.34 | 1.42 | 0.93 | AC002464.1 | 0.66 | 0.20 | −0.55 | −0.40 | −0.85 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| INSR | −0.52 | 0.36 | 0.36 | 0.16 | −0.04 | AC090103.1 | −0.77 | 0.15 | −0.72 | 0.30 | −0.85 | AL359753.1 | 0.41 | −1.20 | −1.22 | −1.06 | −0.34 |
| FAHD1 | 0.64 | −0.15 | −0.66 | 0.10 | −0.35 | POU2F1 | 0.12 | −0.04 | −0.18 | 0.03 | −0.22 | AL442125.1 | 0.08 | −0.17 | 0.28 | −0.17 | 0.11 |
| RHOG | 0.69 | −0.52 | −0.60 | −0.34 | −0.27 | AP000892.1 | −0.64 | 0.71 | 1.81 | −0.45 | 0.02 | AL139039.3 | −0.49 | −0.58 | −1.89 | 0.48 | −1.43 |
| NARS | 0.60 | −0.31 | −0.63 | −0.17 | −0.31 | RN7SL336P | −0.83 | −0.25 | 1.78 | 0.10 | 0.60 | AC079070.1 | −0.78 | −0.04 | −2.35 | 2.21 | −0.39 |
| SLC1A6 | −1.42 | 0.60 | 1.78 | 0.40 | 0.43 | GJA1P1 | −0.22 | 0.30 | −0.18 | 0.07 | −0.14 | AC008937.3 | 0.07 | −0.08 | 0.23 | −0.31 | 0.04 |
| DPM1 | 0.69 | −0.32 | −0.53 | −0.16 | −0.36 | AC022018.1 | 0.73 | −0.53 | 0.16 | −0.44 | 0.24 | AL356270.1 | −0.15 | 0.06 | 0.20 | 0.25 | 0.35 |
| ERP44 | 0.58 | −0.24 | −0.48 | −0.18 | −0.32 | LMAN2L | −0.18 | 0.12 | 0.40 | −0.01 | 0.20 | GPATCH11 | −0.07 | 0.00 | 0.11 | −0.19 | −0.07 |
| SLC4A7 | 0.84 | −0.50 | −1.12 | −0.13 | −0.24 | AC002366.1 | −0.64 | 0.36 | 0.56 | 0.31 | −0.11 | CABCOCO1 | −0.18 | −0.01 | 0.45 | −1.05 | −1.04 |
| RAETIL | 1.85 | −0.49 | −1.76 | −0.33 | −1.26 | MTTP | −0.86 | 0.50 | 0.39 | 0.28 | 0.01 | MTF2 | −0.03 | 0.01 | 0.07 | 0.04 | 0.05 |
| RALGPS2 | 1.09 | −0.15 | −0.62 | 0.19 | −0.51 | GPSM3 | 0.34 | −0.48 | −0.29 | −0.24 | 0.06 | AP3S2 | 0.04 | 0.00 | 0.04 | −0.03 | 0.03 |
| MRPL37 | 0.63 | −0.22 | −0.58 | −0.06 | −0.41 | LINC02063 | −1.22 | −0.46 | 0.53 | 0.38 | 1.45 | AC002044.2 | −0.16 | −0.06 | 0.49 | −0.27 | 0.01 |
| SEM1 | 0.71 | −0.24 | −0.61 | −0.05 | −0.49 | SMARCA5-AS1 | −0.81 | 0.14 | 0.67 | −0.02 | 0.46 | ST3GAL6-AS1 | 0.16 | 0.22 | −0.32 | −0.15 | −0.45 |
| COL24A1 | −1.48 | 0.03 | 1.16 | −0.25 | 0.50 | AC108002.2 | −1.08 | 0.71 | 0.62 | 1.03 | −0.24 | AC098798.1 | 0.23 | −0.75 | −1.56 | −0.58 | −0.58 |
| FAM227A | −1.00 | 0.17 | 0.26 | 0.21 | 0.00 | RPS20P4 | 0.56 | 0.34 | −0.20 | 0.13 | −0.11 | LINC00923 | −0.16 | 0.34 | −0.47 | 0.25 | −0.13 |
| PDCD10 | 0.56 | −0.12 | −0.45 | −0.16 | −0.49 | LINC02082 | −1.34 | −0.41 | 1.10 | −0.20 | 1.57 | AL662884.3 | −0.33 | 1.45 | 0.60 | −0.45 | −2.65 |
| SP8 | −1.79 | 0.38 | 0.65 | 0.57 | −0.38 | NRBF2P5 | 0.51 | −0.18 | 0.00 | 0.04 | 0.32 | AP001979.2 | 0.70 | −0.31 | −1.43 | 1.12 | −0.18 |
| SSR1 | 0.67 | −0.33 | −0.51 | −0.16 | −0.27 | AC239799.2 | −0.73 | 0.81 | −0.19 | 0.68 | −0.54 | SAFB | −0.04 | −0.11 | −0.08 | −0.10 | 0.11 |
| CNOT1 | 0.49 | −0.19 | −0.34 | −0.07 | −0.24 | FANCE | −0.26 | 0.14 | −0.18 | 0.10 | −0.18 | G4633 | −0.30 | −0.26 | 2.06 | −0.95 | 0.42 |
| SLC4A4 | −1.59 | 0.72 | 1.27 | 0.29 | 0.10 | LSM3P5 | −0.56 | 0.51 | 0.41 | 0.69 | −0.03 | GSTA2 | 0.52 | −1.43 | −2.67 | 1.08 | −0.99 |
| AL021707.2 | −0.90 | 0.12 | 0.89 | 0.36 | 0.42 | BFAR | 0.17 | −0.10 | −0.13 | −0.11 | 0.00 | G20595 | −0.32 | −0.35 | −1.60 | −0.96 | −1.97 |
| EPSTI1 | 1.36 | −1.28 | −1.24 | −0.84 | −0.40 | PCYOX1L | 0.23 | 0.01 | 0.07 | 0.03 | 0.03 | LINC01001 | 0.18 | −0.37 | −0.41 | 0.37 | 1.05 |
| CNIH3 | −0.72 | 0.32 | 1.09 | −0.15 | 0.43 | RP11-343N15.5 | 0.33 | 0.17 | 0.34 | 0.05 | −0.34 | CR392039.1 | 0.13 | −0.28 | −0.46 | 0.57 | 0.79 |
| CNNM1 | −1.11 | 0.35 | 0.83 | 0.37 | 0.37 | SPIN1 | 0.17 | 0.09 | 0.02 | 0.08 | −0.09 | 14-Sep | 0.29 | −0.77 | −0.98 | 0.64 | 0.47 |
| KIAA0100 | 0.46 | −0.24 | −0.35 | −0.07 | −0.11 | LINC02412 | −0.68 | 0.94 | 0.03 | 0.99 | 0.08 | LINC01920 | −0.36 | 0.34 | −0.68 | 0.41 | −2.12 |
| APEX2 | 0.65 | −0.40 | −0.68 | −0.01 | −0.16 | ABI3 | 0.38 | −0.60 | −0.19 | −0.38 | 0.05 | AC023509.5 | 0.15 | −0.27 | −0.57 | −0.13 | −0.18 |
| ATG14 | −0.38 | 0.26 | 0.21 | 0.22 | −0.03 | AC010969.2 | 0.34 | −0.09 | −0.18 | −0.17 | −0.35 | AL009028.1 | 0.40 | −0.82 | −1.29 | 0.14 | −0.62 |
| ELF4 | 0.49 | −0.37 | −0.77 | −0.17 | −0.48 | AC037198.1 | 0.65 | −0.65 | −1.21 | −1.52 | −1.13 | C17orf97 | −0.12 | 0.30 | 0.17 | 0.00 | −0.25 |
| ANGPT4 | −1.53 | 0.94 | 1.73 | 0.43 | 0.32 | PPDPFL | −1.39 | 1.32 | 1.83 | 0.28 | 0.20 | DPPA2P4 | 0.35 | 0.47 | 0.34 | −0.77 | 0.06 |
| AC005225.4 | −1.81 | 1.10 | 2.02 | 0.13 | 0.28 | STAC2 | −0.67 | 0.54 | 1.32 | 0.48 | 0.65 | HSPD1P12 | 0.61 | 0.26 | −2.68 | −0.16 | −1.60 |
| MPPED1 | −2.23 | 0.84 | 0.60 | 0.54 | 0.10 | MALRD1 | −0.51 | 0.58 | 0.52 | −0.13 | −0.72 | SEC11B | 0.51 | −0.56 | −0.71 | 0.73 | 0.56 |
| KCNH8 | −1.47 | 0.78 | 0.57 | 0.61 | −0.13 | CELSR1 | 0.28 | −0.21 | −0.68 | 0.24 | 0.17 | AC087289.5 | −0.14 | 0.15 | −0.11 | 0.35 | −0.38 |
| PSMD6 | 0.61 | −0.25 | −0.53 | −0.12 | −0.36 | IQCA1L | −0.68 | −0.93 | −0.76 | 0.81 | 0.32 | AC099681.1 | −0.92 | 0.19 | −0.01 | 0.60 | −0.81 |
| ROPN1B | −1.38 | 0.75 | 1.70 | 0.19 | 1.31 | PTCD2 | 0.16 | −0.07 | −0.02 | −0.02 | 0.09 | EIF4A1P9 | −0.64 | −0.13 | 0.32 | 0.08 | −0.11 |
| ITGAV | 0.85 | −0.41 | −1.00 | 0.00 | −0.65 | AC022540.1 | 0.40 | −0.19 | 0.07 | −0.08 | 0.10 | SNORD113-7 | 0.61 | −0.25 | 0.95 | 0.01 | 0.37 |
| AC090673.1 | 1.39 | −0.74 | −1.48 | −0.11 | −0.82 | AL138847.1 | −0.36 | 0.21 | 0.16 | 0.23 | 0.05 | MED6 | −0.03 | 0.16 | 0.17 | 0.07 | −0.01 |
| RRP7BP | −1.09 | 0.29 | 0.48 | 0.44 | 0.41 | AC097501.1 | −1.78 | 1.13 | 1.27 | 2.76 | 1.17 | LINC02173 | −0.60 | 1.12 | −1.57 | 1.81 | −0.05 |
| BLOC1S2 | 0.95 | −0.30 | −0.63 | −0.29 | −0.47 | MAPT-IT1 | −0.77 | 0.67 | 1.45 | 0.06 | −0.35 | AQP2 | −0.26 | 0.11 | −1.27 | 0.57 | 0.93 |
| CADPS | −1.58 | 0.59 | 0.85 | 0.64 | 0.58 | CSPG5 | −0.40 | −0.27 | 0.35 | 0.02 | 0.75 | RNU2-23P | −0.42 | −0.24 | −0.46 | 0.59 | −1.48 |
| EDEM3 | 0.61 | −0.27 | −0.26 | −0.29 | −0.12 | AC013391.2 | 0.70 | −1.47 | −1.81 | 1.00 | 1.48 | ADH4 | 0.10 | −0.40 | 0.51 | −0.24 | 0.41 |
| COG1 | −0.37 | 0.16 | 0.21 | 0.05 | 0.01 | AL132639.3 | 0.60 | −0.35 | −0.97 | 0.37 | −0.36 | AP000547.1 | −0.87 | −0.92 | 0.00 | −1.56 | 0.31 |
| RAB11A | 0.89 | −0.18 | −0.58 | −0.05 | −0.51 | INTS9-AS1 | −0.31 | −0.24 | 0.17 | 0.07 | 0.44 | MRPL2 | 0.05 | −0.01 | −0.25 | 0.21 | −0.03 |
| CNOT2 | 0.49 | −0.16 | −0.32 | −0.02 | −0.14 | LINC01756 | −0.99 | 1.39 | 1.31 | 0.18 | −0.82 | PLA2G2A | −0.26 | −0.40 | 0.81 | 0.21 | 1.19 |
| PSMD7 | 0.62 | −0.26 | −0.41 | −0.16 | −0.28 | RNA5SP109 | −1.55 | 0.71 | 0.51 | −0.27 | −0.24 | AL132875.1 | 0.36 | −1.24 | −0.82 | 0.43 | 1.32 |
| LINC00674 | −0.70 | 0.43 | 0.81 | 0.20 | 0.29 | AC105918.1 | −1.36 | 1.97 | 0.08 | 1.05 | −0.89 | AC133134.1 | 0.27 | −0.21 | 0.58 | 0.12 | −0.39 |
| ACOT1 | −1.55 | 0.71 | 0.61 | 1.07 | 0.89 | CAT | −0.33 | 0.45 | 0.26 | 0.26 | −0.23 | RNU2-30P | −0.41 | 0.12 | 0.39 | 0.50 | 1.19 |
| AC092127.2 | −1.17 | 0.37 | 0.32 | 0.07 | 0.07 | MTND4P35 | −0.70 | 0.07 | 0.09 | −0.07 | −0.47 | AC092364.1 | −0.50 | −0.64 | 1.63 | 1.07 | 0.65 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| PRSS22 | 1.74 | −1.42 | −2.60 | 0.07 | −0.62 | PMS2CL | −0.20 | 0.03 | 0.11 | 0.07 | 0.21 | AL138815.1 | 0.81 | 0.40 | 0.33 | 0.82 | −1.42 |
| ANAPC16 | −0.66 | 0.20 | 0.37 | 0.30 | 0.26 | AL359253.1 | −1.17 | 0.21 | 1.38 | −1.22 | 0.24 | OR5K2 | 0.36 | 0.57 | 1.33 | −0.29 | −0.71 |
| DNAJB11 | 0.75 | −0.40 | −0.68 | −0.23 | −0.20 | CD177P1 | −1.45 | −0.31 | 0.80 | 0.36 | −0.62 | CPNE6 | −0.14 | −0.15 | −1.06 | 0.45 | −0.09 |
| SCD5 | −1.06 | 0.43 | 0.82 | 0.25 | 0.11 | MTCO3P43 | 0.54 | −0.15 | −0.93 | 0.12 | −0.41 | AP001048.1 | −0.36 | 2.54 | 0.15 | 1.03 | −1.45 |
| AC133540.1 | −1.42 | 0.32 | 0.54 | 0.66 | 0.80 | G34216 | 0.79 | −0.57 | −1.25 | −0.49 | −0.73 | AL031663.1 | −0.77 | −1.36 | 1.08 | −1.12 | 1.22 |
| SNORD116-1 | −1.68 | 1.17 | 2.01 | 0.74 | −0.52 | RN7SKP287 | 0.52 | 0.20 | 0.86 | 0.16 | 0.43 | AC110011.1 | 0.90 | −1.87 | −0.98 | −0.40 | 0.00 |
| G5264 | −2.10 | 1.51 | 3.17 | 0.26 | 1.10 | BIRC2 | 0.19 | −0.01 | −0.09 | −0.15 | −0.27 | MTMR12 | −0.05 | 0.33 | 0.20 | −0.01 | −0.21 |
| MPHOSPH6 | 0.85 | −0.54 | −0.90 | −0.04 | −0.18 | SLC16A1-AS1 | −0.21 | −0.37 | −0.13 | −0.21 | 0.19 | AC007679.1 | −0.30 | −0.53 | −0.21 | 0.26 | 0.67 |
| AC099398.1 | −2.18 | 0.64 | 0.56 | 0.14 | 0.01 | AC023043.4 | 0.85 | −0.55 | −0.72 | −0.05 | −0.19 | AC025741.1 | 0.24 | 0.05 | 0.28 | 0.25 | 1.37 |
| KRT36 | −2.73 | 1.64 | 0.80 | 1.57 | 0.09 | KRTAP21-4P | −0.78 | −0.19 | −1.34 | 0.24 | −0.92 | LYZL2 | −0.88 | −0.45 | −0.13 | 1.23 | −0.17 |
| CREBZF | −0.65 | 0.19 | 0.25 | 0.24 | 0.21 | MMP17 | −0.35 | 0.06 | −0.17 | 0.23 | 0.41 | OTOL1 | 0.43 | −0.94 | −1.97 | 0.75 | −1.49 |
| ATAD3A | 0.84 | −0.62 | −0.93 | −0.17 | −0.05 | RNU6-335P | 0.96 | −1.63 | 0.02 | −0.18 | 1.84 | AC016877.3 | −0.80 | 1.92 | 3.58 | 0.38 | −0.14 |
| SNORD116-2 | −1.71 | 1.14 | 1.50 | 0.83 | −0.28 | HOXD10 | −0.45 | 0.00 | 0.33 | −0.01 | 0.57 | CX3CR1 | −0.14 | −0.01 | 0.55 | −0.49 | 0.39 |
| SNCA | −1.17 | 0.67 | 1.08 | 0.22 | −0.10 | RNU6-1095P | 1.66 | −1.02 | 1.30 | −0.57 | 1.33 | AC098969.1 | −0.45 | 0.07 | 0.47 | −0.17 | 0.54 |
| SLC39A7 | 0.50 | −0.34 | −0.43 | −0.28 | −0.19 | SNORD92 | 0.62 | −1.05 | −0.14 | −0.04 | 0.12 | AC008915.2 | −0.24 | 0.08 | −0.48 | −0.03 | −0.15 |
| HNRNPR | 0.41 | −0.25 | −0.33 | −0.05 | −0.07 | RNU6-407P | 0.74 | −0.04 | −0.04 | −0.21 | 0.06 | MEG3 | −0.09 | 0.48 | 0.35 | −0.47 | −0.44 |
| HDAC2 | 0.60 | −0.33 | −0.42 | −0.21 | −0.27 | AC096947.1 | 0.48 | −0.31 | −0.35 | 0.32 | 0.43 | CFAP46 | 0.11 | 0.07 | −0.34 | 0.44 | −0.08 |
| EFHD1 | −1.41 | 1.09 | 1.69 | 0.85 | 0.13 | SHLD2 | 0.16 | −0.06 | −0.11 | −0.09 | −0.11 | AL353770.4 | −0.67 | 0.38 | 2.32 | −1.35 | 1.98 |
| DDX18 | 0.67 | −0.28 | −0.51 | −0.11 | −0.25 | HGS | 0.17 | −0.18 | −0.59 | 0.07 | −0.11 | RPS6KA2-IT1 | −0.14 | 0.11 | 0.79 | −0.09 | 0.09 |
| ENPP5 | −1.29 | 0.48 | 0.82 | 0.02 | 0.12 | IGSF22 | 0.38 | 0.15 | 0.14 | 0.13 | −0.87 | AKR1C4 | −0.26 | −2.45 | −0.02 | −0.18 | 1.84 |
| SSR4 | 0.62 | −0.13 | −0.49 | −0.02 | −0.44 | AC090644.1 | −0.37 | 0.40 | 0.88 | −0.16 | 0.17 | STXBP4 | −0.04 | 0.10 | 0.17 | 0.03 | −0.03 |
| DIMT1 | 0.52 | −0.22 | −0.30 | −0.17 | −0.20 | MAGOHB | 0.15 | −0.18 | −0.01 | −0.19 | 0.05 | ANO6 | 0.07 | −0.01 | −0.16 | −0.08 | −0.20 |
| ATP1B3 | 1.02 | −0.13 | −0.85 | 0.16 | −0.60 | SETD1A | −0.19 | 0.03 | −0.26 | 0.23 | 0.02 | AC007620.3 | 0.17 | 0.64 | 0.99 | 0.13 | 0.18 |
| SNRPD3 | 0.57 | −0.34 | −0.59 | −0.11 | −0.36 | RNU6-866P | −1.12 | −0.27 | 2.11 | −0.74 | 0.92 | LINC01748 | −0.18 | −0.77 | 0.09 | −0.22 | 0.14 |
| PRR33 | −1.67 | 0.93 | 1.05 | 0.52 | 0.02 | RNA5SP338 | −1.33 | 1.15 | −1.86 | 1.25 | −1.23 | AC009271.1 | 0.28 | 1.14 | 0.27 | 1.57 | 0.03 |
| BUB1B | 1.09 | −1.10 | −1.45 | −0.42 | −0.29 | GK3P | 0.35 | −0.02 | −0.23 | −0.32 | 0.00 | MIR491 | −0.15 | 0.08 | 0.15 | 0.39 | −0.26 |
| JUP | 1.15 | −0.19 | −0.98 | 0.08 | −0.77 | AL049548.1 | −1.09 | 0.37 | 0.78 | −0.63 | 0.14 | AC012254.4 | 0.14 | 0.13 | −0.04 | 0.07 | −0.29 |
| KIF1A | −1.85 | 0.95 | −0.19 | 0.75 | −0.50 | KCTD20 | 0.18 | −0.07 | −0.02 | −0.09 | −0.18 | RPS10P18 | −0.19 | 0.04 | −0.48 | −0.54 | −0.14 |
| AC011483.3 | 3.10 | −3.44 | −2.67 | −2.79 | 0.16 | AC008736.2 | 1.01 | −0.32 | −0.46 | −0.26 | 0.11 | MXRA5 | −0.11 | 0.33 | 0.81 | −0.21 | 0.18 |
| CEP68 | −0.46 | 0.39 | 0.51 | 0.19 | 0.07 | LINC00399 | −1.66 | −0.22 | 0.11 | 1.17 | −1.46 | MIR629 | 0.31 | −0.28 | −0.02 | −1.65 | −0.53 |
| HADHA | 0.57 | −0.25 | −0.58 | −0.06 | −0.32 | MTND5P11 | −0.19 | −0.19 | −0.12 | 0.06 | 0.44 | MIR378E | 0.46 | −0.56 | 0.93 | 0.83 | 2.96 |
| CTTN | 0.48 | −0.21 | −0.58 | −0.15 | −0.34 | RNU1-72P | 1.34 | −1.76 | −3.23 | −0.44 | −2.37 | AC090692.1 | −0.58 | −1.57 | −1.63 | −0.29 | −0.15 |
| SSBP2 | −0.66 | 0.52 | 0.59 | 0.25 | 0.01 | AC073655.2 | −0.34 | 0.25 | 0.31 | −0.11 | 0.13 | OR4L1 | 0.93 | −0.64 | −1.78 | 1.04 | −0.73 |
| ORC1 | 1.17 | −1.26 | −1.58 | −0.34 | −0.56 | POU5F1P5 | −0.31 | 0.05 | −0.08 | 0.13 | 0.23 | MIR378G | 0.60 | 0.67 | 1.74 | −0.12 | 0.27 |
| HECTD1 | 0.51 | −0.07 | −0.33 | 0.01 | −0.34 | NPW | 0.78 | −0.19 | −0.09 | −0.02 | 0.24 | C6orf89 | −0.04 | 0.07 | 0.16 | −0.06 | −0.13 |
| RIMS3 | 1.27 | −0.15 | −0.72 | −0.07 | −0.80 | SNORA75 | −0.39 | 0.26 | 0.17 | 0.38 | −0.23 | AL133372.3 | −0.76 | 0.70 | −0.22 | 0.80 | −0.21 |
| RABGGTB | 0.66 | −0.37 | −0.65 | 0.00 | −0.20 | MIR326 | 0.67 | −0.32 | 0.18 | −0.12 | 0.99 | AL354984.1 | 0.38 | −1.18 | −1.74 | 0.15 | −1.16 |
| SRGAP2B | −0.82 | 0.39 | 0.69 | 0.20 | 0.12 | HACL1 | −0.20 | 0.10 | 0.34 | 0.05 | 0.23 | MTCYBP43 | 0.16 | −0.11 | −0.60 | 0.17 | −0.01 |
| PDCD6IP | 0.60 | −0.19 | −0.51 | −0.09 | −0.35 | AC127070.4 | 0.32 | −0.12 | 0.02 | −0.15 | −0.01 | PTP4A2P2 | 0.17 | 0.06 | 0.46 | −0.40 | −0.26 |
| CLDN16 | −1.53 | 1.03 | 0.85 | 0.79 | −0.01 | INHBA-AS1 | 0.68 | −0.46 | −0.94 | −0.03 | −1.02 | AL080313.2 | 0.38 | 0.18 | −0.28 | −0.76 | −0.40 |
| AC006262.1 | −1.14 | 0.90 | 0.91 | 0.35 | 0.27 | NAALADL2-AS3 | −0.76 | 0.78 | −0.30 | 0.36 | −0.98 | ARX | −0.31 | −0.99 | −0.11 | 0.41 | 0.28 |
| AL031846.2 | −1.06 | 1.09 | 0.54 | 0.64 | 0.00 | RPL12P31 | 0.63 | −0.24 | −0.47 | −0.14 | −0.46 | KRT18P67 | −0.56 | −0.49 | −1.52 | −0.65 | −0.77 |
| DHX29 | 0.51 | −0.19 | −0.31 | −0.10 | −0.24 | HNF1B | 0.94 | −0.70 | −2.34 | 0.52 | −1.77 | AP003097.1 | 0.66 | −0.80 | −2.11 | −0.52 | −2.27 |
| C12orf29 | 0.72 | −0.07 | −0.26 | 0.05 | −0.26 | C5orf38 | −0.32 | 0.40 | 0.27 | 0.18 | 0.04 | ADSL | 0.05 | −0.38 | −0.24 | −0.04 | 0.05 |
| ATXN7L3 | 0.50 | −0.21 | −0.64 | 0.02 | −0.23 | MED22 | −0.16 | 0.16 | 0.16 | 0.14 | 0.22 | RNU7-107P | 0.61 | −0.06 | 1.56 | −0.26 | 0.47 |
| CCDC180 | −0.96 | 0.51 | 0.63 | 0.21 | 0.03 | GRM6 | −0.51 | 0.29 | 0.91 | −0.06 | −0.12 | RXFP3 | 0.47 | −0.86 | −0.86 | −1.20 | −1.19 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| CENPJ | 0.58 | −0.51 | −0.52 | −0.31 | −0.14 | AC008629.1 | −0.83 | 0.81 | 0.27 | −0.30 | −0.08 | CYP51A1P3 | 0.09 | 0.21 | −0.07 | 0.16 | −0.22 |
| AC008464.1 | 1.67 | −1.35 | −1.52 | −0.68 | 0.42 | RAB11B | −0.15 | 0.21 | −0.11 | 0.24 | 0.01 | LUARIS | −0.20 | 0.16 | −0.59 | 0.25 | −1.02 |
| C16orf58 | −0.70 | 0.40 | 0.58 | 0.27 | 0.27 | CNN2P9 | −0.63 | 0.52 | −0.84 | 0.45 | −0.31 | LINC01038 | −0.73 | 1.37 | −1.36 | 0.84 | −1.38 |
| PCDHA10 | −1.64 | 0.78 | 0.25 | 0.95 | −0.30 | AC019117.1 | 0.44 | −0.90 | −0.83 | −0.66 | 0.26 | AC012494.1 | −0.57 | −1.20 | −1.87 | 0.29 | −1.21 |
| CMTM6 | 0.99 | −0.49 | −0.33 | −0.23 | −0.45 | IGHEP2 | −0.36 | −0.47 | −0.05 | 0.24 | 0.54 | RN7SL871P | −0.68 | 0.15 | 0.81 | −0.72 | 0.16 |
| E2F3 | 1.02 | −0.73 | −0.58 | −0.26 | −0.16 | COL13A1 | 0.34 | −0.46 | −0.69 | −0.09 | −0.16 | AC120024.4 | −0.28 | −0.86 | −1.72 | −0.25 | 0.57 |
| RN7SL622P | −1.78 | −0.06 | 0.98 | 0.41 | 0.93 | C12orf45 | 0.15 | −0.17 | 0.00 | −0.08 | 0.19 | SPATA31E1 | 0.43 | −1.52 | −1.60 | −0.35 | −0.95 |
| APEH | 0.66 | −0.39 | −0.64 | −0.06 | −0.20 | CLEC4M | −0.98 | −0.74 | −1.11 | 0.29 | −0.48 | RPL23AP20 | 0.25 | −1.05 | −0.08 | −0.89 | 0.24 |
| AIMP2 | 0.75 | −0.50 | −0.67 | −0.37 | −0.23 | CELP | −0.74 | −0.92 | 0.42 | 0.01 | 0.59 | CCR3 | 0.21 | −0.67 | 0.08 | −0.72 | 0.27 |
| ELF3-AS1 | −0.81 | 0.31 | −0.15 | 0.42 | −0.01 | SNORA77 | −0.36 | 0.52 | 0.53 | 0.14 | 0.11 | FAM27C | −1.17 | 0.36 | −0.76 | 0.72 | −1.22 |
| AL359542.1 | −1.99 | 0.16 | 0.87 | 0.79 | 0.83 | BST2 | 0.46 | −0.68 | −0.09 | −0.40 | −0.07 | C10orf53 | −0.34 | −1.93 | −0.96 | −0.08 | −0.89 |
| AC013444.2 | 2.65 | −0.83 | −1.32 | −0.02 | −0.80 | AC004824.2 | −1.10 | −1.28 | −0.24 | −0.14 | −0.28 | AC091962.1 | 0.46 | 0.07 | −1.04 | 0.31 | −1.49 |
| GRID2IP | −1.19 | 0.70 | 1.55 | 0.36 | 0.60 | AC009704.2 | 0.62 | −1.22 | −0.65 | −0.50 | −0.24 | AL157902.2 | −0.12 | 0.40 | 0.13 | −0.08 | −0.28 |
| KY | −1.37 | 1.02 | 0.85 | 0.44 | 0.21 | APMAP | −0.35 | 0.08 | 0.15 | 0.17 | 0.49 | DPRX | −0.54 | 0.81 | 1.56 | −0.93 | 0.26 |
| NOL8 | 0.50 | −0.27 | −0.35 | −0.06 | −0.07 | AC113430.1 | 1.56 | −1.29 | −0.76 | 0.29 | 0.10 | AC020763.5 | 0.23 | −0.55 | −0.76 | 0.08 | 0.37 |
| CYFIP1 | 0.39 | −0.14 | −0.45 | −0.13 | −0.28 | AL049780.2 | 0.66 | −0.75 | 0.08 | −0.05 | 0.82 | AL662789.1 | 0.76 | −0.98 | −1.38 | 1.15 | 0.15 |
| PDLIM5 | 0.59 | −0.26 | −0.61 | −0.23 | −0.57 | AC017104.1 | −0.62 | 0.62 | −0.34 | 0.35 | −0.18 | DUSP8 | −0.10 | 0.16 | −0.53 | 0.01 | −0.61 |
| PRR15L | −1.25 | 0.73 | 0.72 | 0.43 | 0.31 | AL512413.1 | −0.66 | 1.04 | 1.10 | 0.09 | −0.14 | FAM71B | 0.46 | −1.31 | −1.62 | 0.36 | 0.85 |
| DGCR6 | −1.32 | 1.00 | 1.12 | 0.55 | 0.17 | AC020634.1 | −0.83 | 0.19 | −0.05 | −0.05 | 0.58 | SNRPCP3 | −0.21 | −0.31 | 0.54 | 0.41 | −0.94 |
| SLC16A8 | −1.22 | 0.52 | 0.71 | 0.57 | 0.31 | CCDC85C | 0.23 | 0.06 | −0.27 | 0.15 | −0.05 | AC069277.1 | 0.25 | −0.36 | −0.49 | 0.02 | −1.64 |
| SLC25A3 | 0.56 | −0.24 | −0.56 | 0.01 | −0.33 | AL353997.4 | 2.33 | −1.23 | −1.29 | −0.71 | −1.70 | AC010735.2 | −0.27 | 0.28 | −0.10 | 1.38 | 0.98 |
| PTPN2 | 0.51 | −0.29 | −0.39 | −0.18 | −0.19 | AC093151.3 | −1.08 | 0.35 | 0.56 | −0.80 | −0.14 | KLHL30-AS1 | −0.28 | −0.95 | −0.15 | −0.97 | −1.03 |
| PRKG2 | −1.27 | 0.95 | 1.82 | 0.11 | 0.35 | RNU6-437P | 0.99 | 0.00 | −1.96 | −0.51 | −1.01 | AC079354.2 | −0.32 | 1.00 | −0.32 | −0.31 | −1.15 |
| PNPO | 0.63 | −0.37 | −0.39 | 0.00 | 0.23 | AC097478.4 | −0.72 | −0.21 | 0.05 | 0.19 | 0.38 | AL122017.1 | −0.18 | 0.29 | 0.67 | 0.42 | −0.01 |
| SERHL2 | −1.05 | 0.86 | 0.72 | 0.61 | 0.29 | CDKAL1 | −0.11 | 0.10 | 0.04 | 0.02 | −0.09 | AL365214.3 | 0.90 | −1.17 | −0.35 | 0.43 | 0.57 |
| NGF | 1.96 | −0.98 | −1.88 | −0.18 | −1.48 | AL357315.1 | 0.75 | −0.24 | 0.60 | −0.14 | 0.34 | AC007686.1 | 0.70 | 0.28 | −2.94 | 0.05 | −2.46 |
| KBTBD8 | 1.27 | −0.84 | −0.94 | −0.36 | −0.69 | CTD-2270F17.1 | −0.69 | 0.12 | 1.32 | 1.02 | 0.70 | APOOL | 0.04 | 0.18 | 0.08 | 0.14 | −0.16 |
| MTR | −0.52 | 0.13 | 0.38 | 0.12 | 0.30 | LINC01942 | −1.65 | −0.48 | −0.15 | 0.18 | −0.47 | GPR19 | −0.16 | −0.42 | 0.10 | −0.56 | 0.29 |
| LAP3 | 0.74 | −0.48 | −0.48 | −0.33 | −0.33 | AC069222.1 | −0.68 | −0.47 | 0.06 | −0.19 | −0.24 | OR1E2 | 1.00 | −1.58 | −0.64 | −0.31 | 0.65 |
| ABCA6 | −1.23 | 1.09 | 1.25 | 0.59 | 0.05 | RBM22P5 | −0.96 | −1.46 | 0.18 | 0.14 | −0.23 | OR8R1P | 0.28 | −0.30 | −0.23 | −0.10 | 0.09 |
| EEF1DP7 | −0.85 | 0.13 | 0.73 | −0.28 | −0.04 | AC016727.1 | −0.22 | −0.14 | 0.20 | 0.08 | 0.13 | EHD2 | −0.07 | 0.01 | −0.26 | −0.02 | −0.19 |
| EEF1DP1 | −1.34 | 0.92 | 1.34 | 0.24 | 0.40 | AC126182.1 | 0.92 | −0.50 | −0.06 | −0.58 | 0.21 | AC012615.1 | −0.16 | 0.16 | 0.53 | 0.20 | 0.62 |
| MICALL1 | 0.65 | −0.19 | −0.67 | 0.01 | −0.32 | G27953 | −1.36 | 0.29 | −0.35 | 2.70 | 3.23 | LINC00243 | 0.16 | −0.62 | 0.17 | −0.66 | −0.21 |
| IPO11 | 0.50 | −0.19 | −0.23 | −0.17 | −0.18 | MYCNOS | −0.84 | −1.09 | −0.47 | 0.26 | 0.18 | AC067942.2 | 0.24 | −0.30 | −0.17 | 0.58 | 0.41 |
| EDEM1 | 0.57 | −0.26 | −0.56 | −0.05 | −0.35 | AC008591.1 | −0.95 | 1.34 | −0.65 | 1.49 | −0.37 | AL513008.1 | −0.21 | 0.50 | 0.72 | 0.10 | −0.30 |
| CRYAB | −1.48 | 1.08 | 0.92 | 0.55 | −0.21 | ARHGAP31 | −0.25 | 0.11 | 0.25 | −0.14 | −0.15 | MC4R | −0.50 | 1.66 | −1.30 | 2.04 | −1.49 |
| LEO1 | 0.71 | −0.39 | −0.53 | −0.27 | −0.20 | PARD6G-AS1 | −0.34 | 0.31 | 0.53 | 0.33 | 0.28 | RPL12P11 | −0.15 | 0.05 | 0.53 | −0.06 | 0.36 |
| OR2T10 | −3.21 | 1.42 | 2.28 | 0.96 | 1.42 | OR2A13P | −0.56 | 0.35 | −0.09 | 0.90 | −0.49 | AC090192.2 | 0.45 | −0.32 | 1.42 | −1.36 | 1.78 |
| FITM2 | −1.05 | 0.32 | 0.45 | 0.28 | 0.25 | PRKCSH | −0.18 | −0.02 | −0.25 | 0.17 | 0.02 | AL391422.1 | −0.20 | 0.10 | 0.94 | 0.37 | 1.09 |
| PTHLH | 2.24 | −1.91 | −1.93 | −1.35 | −1.93 | GABRA3 | −0.49 | 0.64 | 0.12 | 0.10 | −0.56 | EXOGP1 | −0.65 | 0.92 | −0.36 | 0.63 | −1.74 |
| SNRPD2 | 0.67 | −0.31 | −0.50 | 0.15 | −0.42 | RNA5SP237 | 0.74 | −0.71 | 0.77 | −0.09 | 0.14 | AC018641.1 | 0.70 | −1.51 | −0.46 | −0.39 | 1.05 |
| ASTN2 | −1.26 | 0.44 | 0.98 | 0.25 | 0.14 | C1orf226 | −0.36 | 0.26 | 0.29 | 0.23 | 0.36 | AC009227.2 | −0.54 | −0.23 | 1.20 | −0.13 | 0.08 |
| CCNE1 | 1.24 | −1.06 | −1.49 | −0.19 | −0.31 | RN7SL767P | −0.54 | 0.26 | −0.41 | 0.83 | −0.57 | FAM240B | −0.48 | −0.59 | 0.69 | −0.71 | 0.16 |
| KCNA4 | −2.27 | 0.68 | 0.10 | 0.84 | 0.10 | PAXBP1 | −0.14 | 0.02 | 0.11 | 0.03 | 0.15 | MRFAP1L1 | −0.03 | 0.08 | 0.08 | 0.00 | −0.07 |
| GJA1 | 1.33 | −0.27 | −0.74 | 0.23 | −0.61 | G3616 | −0.66 | 0.82 | 0.49 | −0.63 | −0.30 | RN7SL90P | −0.40 | 0.20 | −0.76 | 1.92 | 0.08 |
| AL359922.3 | 0.96 | −0.28 | −0.59 | 0.05 | 0.08 | AF121897.1 | −0.70 | −0.29 | −0.44 | 0.32 | −0.35 | CR589904.1 | −0.58 | 0.20 | 0.43 | 1.94 | −1.78 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| ECHDC2 | −0.71 | 0.48 | 0.56 | 0.47 | 0.26 | CDH13 | 0.24 | 0.17 | −0.55 | 0.08 | −0.40 | AC018861.2 | −0.87 | 0.24 | −0.42 | 0.25 | −0.45 |
| ETHE1 | 1.00 | −0.51 | −1.07 | −0.20 | −0.36 | MOAP1 | −0.22 | 0.31 | 0.26 | 0.13 | −0.18 | APCDD1 | −0.11 | 0.17 | 0.37 | 0.19 | −0.01 |
| INHBB | −1.24 | 0.79 | 0.82 | 0.32 | 0.08 | PRMT8 | 0.64 | −0.95 | −0.68 | −0.52 | 0.24 | LINC02541 | −0.11 | −0.18 | 0.20 | 0.45 | 0.67 |
| SNORD116-15 | −1.61 | 1.07 | 1.46 | 0.59 | −0.61 | RPL3P13 | −1.02 | 1.25 | 2.02 | 0.61 | −1.13 | AC034236.3 | 0.38 | −0.18 | 1.07 | 1.44 | 0.54 |
| MKRN9P | −1.83 | 0.57 | 0.76 | 1.12 | 0.96 | AL357874.1 | −1.21 | 1.08 | −1.87 | 0.18 | −2.17 | SLC9A3-AS1 | 0.12 | −0.06 | −0.33 | 0.34 | 0.47 |
| LINC02256 | −1.24 | 0.24 | 0.91 | 0.49 | 0.51 | LINC01448 | 1.64 | −0.53 | −0.63 | 0.94 | 1.46 | HLA-DQB1-AS1 | 0.17 | −1.19 | −0.09 | −0.95 | −0.36 |
| CWH43 | 1.21 | −0.29 | −0.70 | 0.00 | −0.38 | MLANA | −0.33 | 0.43 | −0.05 | 0.41 | −0.04 | SEBOX | −0.90 | 0.05 | 1.43 | −0.41 | 0.94 |
| CTC1 | −0.52 | 0.22 | 0.35 | 0.23 | 0.34 | AL357507.1 | −0.76 | 0.11 | −0.43 | −0.34 | −1.12 | ANTXR1 | 0.07 | 0.12 | 0.19 | 0.02 | −0.10 |
| ST14 | 0.96 | −0.35 | −0.95 | 0.07 | −0.41 | DIAPH2-AS1 | −0.24 | 0.34 | 0.46 | 0.08 | −0.17 | REV3L | −0.05 | 0.16 | 0.30 | 0.03 | 0.00 |
| SLC4A5 | −0.91 | 0.53 | 0.56 | 0.12 | 0.24 | AC007091.1 | −0.95 | 0.44 | 0.88 | −0.28 | −0.37 | LINC00301 | −0.47 | 0.32 | −0.21 | −1.68 | −2.17 |
| FBXW4 | −0.79 | 0.41 | 0.59 | 0.36 | 0.38 | CTBS | 0.28 | −0.19 | −0.36 | 0.04 | −0.16 | HLA-DMA | 0.09 | −0.24 | 0.00 | −0.16 | 0.07 |
| DENND2C | 0.89 | −0.20 | −0.65 | −0.06 | −0.68 | AC110285.7 | 0.56 | −0.09 | −0.70 | 0.54 | −0.01 | LLCFC1 | −0.36 | 0.99 | −1.10 | 1.11 | −0.65 |
| G22771 | −1.23 | 0.27 | 0.75 | 0.46 | 0.96 | RNU6-344P | 1.25 | 0.50 | −0.93 | 0.28 | −1.10 | LINC01267 | −0.34 | −0.21 | −0.32 | −0.56 | −0.23 |
| NOP16 | 0.92 | −0.45 | −0.74 | −0.08 | −0.41 | AC023794.2 | −0.81 | 0.82 | −0.52 | 0.38 | −0.11 | SLC6A19 | 0.57 | −0.17 | −2.62 | −0.26 | −2.28 |
| IMMT | 0.46 | −0.28 | −0.44 | −0.10 | −0.14 | AP001636.1 | −0.63 | 0.15 | 0.65 | 0.13 | 0.33 | AC109588.1 | 0.52 | 1.69 | −1.61 | 0.89 | −1.21 |
| ARL5B | 0.92 | −0.28 | −0.68 | −0.16 | −0.81 | NCOA5 | 0.14 | −0.06 | −0.21 | 0.03 | 0.03 | RPL9P32 | 0.14 | 0.35 | 0.54 | 0.15 | 0.22 |
| MYEF2 | −1.01 | 0.45 | 0.68 | 0.21 | 0.46 | PRKCZ | −0.27 | 0.21 | 0.04 | 0.26 | 0.26 | IZUMO3 | 0.43 | −1.02 | −1.67 | −1.11 | −1.68 |
| NOB1 | 0.50 | −0.28 | −0.42 | −0.11 | −0.27 | SLC25A21 | −0.52 | 0.31 | −0.54 | 0.37 | −0.50 | GNG4 | 0.21 | −0.96 | −0.65 | 0.08 | 0.18 |
| SNORD116-16 | −1.63 | 1.14 | 1.47 | 0.66 | −0.40 | AL121820.2 | −0.78 | 0.43 | 2.57 | −0.57 | 0.39 | OR6A2 | 0.19 | −0.67 | −1.65 | 0.18 | −1.05 |
| GRHL3 | 1.17 | −0.26 | −0.64 | −0.26 | −0.75 | DPF3 | −0.29 | 0.07 | 0.05 | 0.04 | 0.08 | RBBP4P2 | 0.17 | 0.45 | 0.10 | 0.20 | −0.91 |
| GTF2H3 | 0.65 | −0.53 | −0.41 | −0.18 | −0.04 | AC090971.5 | 0.81 | −0.73 | 1.53 | −0.49 | 0.88 | RNU6-994P | −0.41 | 0.52 | −0.71 | 1.47 | 0.35 |
| CNOT9 | 0.55 | −0.37 | −0.52 | −0.10 | −0.22 | AC097467.3 | −0.63 | 0.14 | 0.12 | −0.45 | −0.24 | AC016550.2 | 0.86 | 0.28 | −1.56 | 0.71 | −0.32 |
| AC007388.1 | −0.67 | 0.31 | 0.60 | 0.07 | 0.11 | G2E3 | 0.14 | −0.19 | −0.10 | −0.11 | −0.01 | BMP8A | 0.17 | −0.12 | −1.06 | −0.32 | −0.86 |
| NLN | 0.71 | −0.39 | −0.45 | −0.02 | −0.20 | RN7SL665P | −0.71 | 0.51 | −0.94 | 1.09 | −0.47 | AP001021.1 | −0.33 | −0.28 | 0.80 | −0.15 | 1.19 |
| CDHR1 | −1.37 | 0.84 | 0.95 | 0.93 | 0.63 | RPL13 | 0.20 | 0.18 | 0.07 | 0.10 | −0.22 | PPP4R3C | 0.74 | −0.94 | −1.44 | 0.25 | −0.10 |
| NBEA | −0.96 | 0.74 | 1.24 | 0.14 | 0.48 | AL358472.5 | 0.58 | −0.31 | −0.03 | −0.08 | 0.26 | NOD1 | 0.05 | −0.08 | 0.24 | −0.11 | 0.05 |
| SHC1 | 0.51 | −0.44 | −0.68 | −0.24 | −0.27 | C1orf147 | 0.62 | 0.14 | −0.21 | 0.12 | −0.21 | DEGS2 | 0.11 | 0.70 | 0.53 | 0.43 | −0.22 |
| OCIAD2 | 0.94 | −0.24 | −0.72 | −0.04 | −0.57 | RPS13P2 | 0.45 | −0.09 | −0.39 | −0.12 | −0.49 | C20orf144 | −0.11 | −0.31 | 0.00 | −0.02 | 0.45 |
| ASXL2 | 0.36 | −0.12 | −0.26 | −0.13 | −0.19 | CCDC190 | −1.03 | −1.05 | −0.06 | 0.15 | 0.40 | METTL26 | −0.05 | 0.12 | 0.01 | 0.01 | −0.20 |
| RN7SL721P | −1.44 | 0.20 | −0.09 | 0.53 | 0.16 | SLAMF9 | 1.38 | −1.07 | −0.66 | −0.21 | 1.22 | AC015853.2 | −0.46 | −0.35 | 0.71 | 0.27 | 0.32 |
| NISCH | −0.77 | 0.39 | 0.53 | 0.33 | 0.31 | KF455155.1 | 0.62 | 0.54 | −0.91 | 0.20 | −0.81 | LEMD2 | 0.04 | −0.06 | −0.11 | 0.02 | 0.10 |
| ELOVL1 | 0.65 | −0.31 | −0.49 | −0.11 | −0.28 | PKP4 | −0.10 | 0.08 | 0.06 | 0.16 | 0.14 | LINC00449 | −0.27 | −0.09 | −0.20 | −0.64 | −0.72 |
| LARP4 | 0.54 | −0.32 | −0.35 | −0.18 | −0.08 | DNAAF5 | 0.21 | −0.25 | −0.56 | 0.06 | −0.12 | RPL21P106 | 0.35 | −0.75 | −0.41 | 0.52 | 1.42 |
| AC135352.1 | −1.15 | 0.38 | 1.02 | 0.29 | 0.53 | OR2M2 | 1.65 | −0.48 | −1.33 | 0.53 | −1.28 | BX322234.2 | −0.33 | 0.59 | 0.87 | 0.08 | 0.61 |
| AC006600.2 | −1.79 | 0.75 | 2.32 | 0.17 | 1.31 | AC034102.8 | 0.83 | −0.54 | 1.29 | 0.19 | 0.82 | NDUFB4P9 | −0.85 | −0.08 | 1.38 | 1.11 | 2.29 |
| LINC00957 | −1.36 | 0.68 | 0.84 | 0.59 | 0.26 | HCLS1 | 0.38 | −0.62 | 0.00 | −0.48 | 0.17 | RN7SL391P | −0.25 | 0.40 | 1.77 | 0.01 | −0.04 |
| DSE | 0.65 | −0.61 | −0.74 | −0.13 | −0.29 | RNF224 | 0.54 | −0.18 | −0.48 | −0.45 | −0.48 | LILRA2 | −0.19 | −0.59 | −0.45 | 0.00 | 0.08 |
| RHOA | 0.57 | −0.33 | −0.52 | −0.10 | −0.31 | AC008691.1 | 0.49 | −0.53 | −0.89 | −0.15 | −0.70 | AL121612.2 | 0.33 | −1.60 | −2.02 | −1.85 | −1.10 |
| PFKFB4 | 1.13 | −0.64 | −1.47 | −0.21 | −0.54 | NMRAL1 | 0.15 | −0.11 | −0.28 | 0.01 | 0.04 | C20orf187 | −0.62 | 0.99 | 0.85 | 1.14 | 0.09 |
| MAPK1IP1L | 0.61 | −0.30 | −0.47 | −0.18 | −0.37 | SNX29 | 0.13 | −0.11 | −0.29 | 0.00 | −0.09 | OR6J1 | −0.25 | −0.10 | −0.72 | 1.53 | 1.14 |
| CDHR5 | −1.42 | 0.61 | 0.63 | 0.62 | 0.18 | AC007151.1 | 0.50 | −0.47 | 0.06 | −0.30 | 0.04 | AC087499.2 | −0.35 | −0.24 | −2.85 | 0.41 | −1.70 |
| NRG1 | 1.37 | −0.88 | −1.75 | −0.29 | −0.91 | LINC02259 | −1.15 | 0.06 | 1.23 | −0.53 | 0.47 | SNORD74 | 0.14 | 0.05 | −0.14 | −0.33 | 0.14 |
| DIS3 | 0.54 | −0.29 | −0.52 | −0.07 | −0.25 | AC008127.1 | −1.67 | −1.40 | 1.77 | 0.44 | 2.36 | AC005162.1 | 0.26 | −1.02 | 1.06 | −0.33 | 1.64 |
| NUP98 | 0.48 | −0.29 | −0.46 | −0.17 | −0.26 | ATF7IP2 | −0.26 | 0.29 | 0.50 | −0.06 | 0.10 | JAZF1-AS1 | −0.29 | −0.84 | 1.34 | −0.36 | 0.46 |
| SLC36A1 | 0.48 | −0.39 | −0.26 | −0.23 | −0.18 | DLGAP2 | 0.45 | −0.52 | −1.40 | 0.42 | −0.49 | STXBP5L | 0.14 | −0.32 | −0.63 | 0.03 | −0.44 |
| MCOLN3 | −1.04 | 0.38 | 0.37 | 0.20 | 0.54 | C2CD4C | −0.70 | 0.37 | −0.85 | 1.42 | 0.85 | AL021920.1 | −0.61 | −1.24 | 0.01 | −1.04 | 1.14 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| MRE11 | −0.34 | 0.14 | 0.25 | 0.12 | 0.04 | FTX | −0.14 | 0.11 | 0.21 | 0.16 | 0.15 | ASIC2 | −0.21 | 0.33 | −0.77 | 0.87 | 0.06 |
| NUP205 | 0.61 | −0.38 | −0.59 | −0.06 | −0.20 | RNA5SP282 | 0.84 | −0.73 | 0.31 | −0.65 | 1.23 | LINC02347 | −0.35 | −0.44 | −1.05 | −0.38 | −0.91 |
| DNA2 | 0.87 | −0.71 | −0.86 | −0.11 | −0.15 | AL034347.1 | 0.79 | 0.00 | −1.60 | 0.49 | −0.93 | KCNK3 | −0.17 | 0.28 | 0.11 | 0.42 | −0.28 |
| RPS13 | 0.79 | −0.28 | −0.51 | −0.12 | −0.59 | FAU | 0.17 | 0.06 | −0.38 | 0.24 | −0.30 | AC012629.4 | −0.43 | 1.69 | 2.93 | −0.81 | −0.46 |
| ISM1-AS1 | −1.37 | 0.95 | 0.88 | 0.45 | −0.22 | NCAPGP1 | −0.53 | 0.33 | 0.71 | 0.07 | −0.12 | RNA5SP431 | 0.50 | −0.34 | −0.60 | −1.07 | −2.19 |
| FAM20A | 0.78 | −0.52 | −0.34 | −0.24 | 0.13 | SFTPA1 | −0.74 | 0.33 | −0.78 | 0.97 | −0.98 | AC096644.1 | −0.57 | −0.53 | 0.28 | −1.46 | −0.94 |
| IDUA | −1.15 | 0.35 | 0.42 | 0.38 | 0.32 | RPL32P1 | 0.57 | −0.63 | −0.57 | −0.47 | −0.31 | AC010333.1 | 0.13 | 0.30 | −0.56 | −0.04 | −0.50 |
| PLCD4 | 0.90 | −0.49 | −1.55 | 0.09 | −0.52 | AC016885.2 | −1.54 | 0.80 | 2.22 | 2.10 | 1.01 | AC096667.1 | 0.42 | −1.49 | −1.78 | −0.63 | −1.05 |
| CPEB1 | −1.47 | 0.70 | 1.45 | −0.01 | 0.54 | MTND4P12 | −0.27 | 0.09 | −0.09 | 0.19 | 0.01 | AC005702.4 | 0.30 | −0.03 | −0.25 | −0.02 | 0.31 |
| OSGEP | −0.51 | 0.16 | 0.24 | 0.30 | 0.27 | AC092437.1 | −1.00 | 0.15 | 2.03 | −0.75 | 0.72 | SMAD9-IT1 | −0.16 | −0.31 | 0.74 | −0.14 | 0.29 |
| RBBP8 | 0.70 | −0.37 | −0.73 | −0.12 | −0.19 | AC037441.1 | −0.82 | 0.06 | −0.12 | 0.43 | 0.03 | CDK11A | 0.10 | 0.12 | 0.55 | −0.33 | −0.11 |
| CKS2 | 1.76 | −0.86 | −1.37 | −0.28 | −0.96 | AOAH | 0.50 | −0.67 | 0.13 | −0.60 | 0.24 | AL031770.1 | −0.10 | 0.09 | −0.12 | −0.20 | −0.05 |
| DGKG | −1.20 | 0.64 | 0.77 | 0.54 | 0.14 | RNU6-647P | 0.94 | −0.76 | −0.45 | 0.38 | 0.72 | RN7SL153P | 0.28 | −0.86 | 0.10 | 0.75 | 1.10 |
| IGDCC4 | −1.19 | 0.62 | 1.51 | −0.23 | 0.16 | AL669841.1 | −0.61 | 0.22 | 0.99 | 0.19 | 0.55 | AC011742.1 | 0.39 | −0.42 | −0.28 | −0.84 | 0.21 |
| RENBP | −1.19 | 0.26 | 0.76 | 0.15 | 0.24 | RMRPP2 | 0.60 | 0.05 | −0.95 | 0.32 | −0.48 | AP003469.1 | −0.22 | −0.18 | −1.50 | −0.10 | −0.98 |
| G656 | −1.36 | 0.37 | 0.75 | 0.30 | 0.36 | SCN1A | −0.61 | 0.15 | −0.03 | −0.18 | −0.70 | AL442663.1 | 0.30 | −0.49 | 0.27 | 0.04 | 0.55 |
| MORN3 | −0.95 | 0.44 | 0.35 | 0.38 | 0.17 | AC091868.1 | 0.67 | −0.37 | −0.99 | −0.33 | 0.03 | PSKH2 | −0.33 | 0.64 | −1.92 | 0.87 | −1.79 |
| PRPS1 | 0.55 | −0.25 | −0.14 | −0.19 | −0.06 | G40907 | −0.29 | 0.16 | 0.62 | 0.22 | 0.53 | BPIFB3 | 1.04 | −1.02 | −0.62 | 0.60 | −0.52 |
| IRX5 | −0.75 | 0.82 | 0.41 | 0.53 | −0.07 | GRHL2 | 0.24 | 0.01 | −0.17 | 0.10 | 0.08 | CYP2AB1P | 0.67 | −0.17 | −1.52 | 0.29 | −1.82 |
| G42176 | −1.90 | 1.31 | 2.81 | 0.09 | 0.55 | AC025154.2 | −0.78 | 0.26 | 0.91 | 0.86 | 0.84 | AL139132.1 | 0.17 | −0.34 | −0.27 | 0.13 | −0.27 |
| MRPS30-DT | −1.33 | 0.54 | 2.73 | −0.28 | 0.81 | AC020913.2 | −0.59 | −0.89 | −0.58 | 0.12 | 0.67 | AL157938.3 | 0.09 | 0.04 | 0.08 | 0.06 | −0.11 |
| HIST1H3G | 1.61 | −0.92 | −1.08 | −0.40 | −0.63 | ALPK3 | −0.41 | 0.07 | −0.48 | 0.18 | −0.45 | LINC02514 | −0.68 | −1.19 | 0.53 | −1.04 | 2.51 |
| AC112504.1 | −1.49 | 0.12 | 1.05 | 0.79 | 1.02 | SEC14L1 | 0.19 | −0.03 | −0.21 | −0.05 | −0.26 | AL445488.1 | −0.61 | 0.51 | −0.19 | −0.07 | −2.50 |
| PPP1R15B | 0.59 | −0.29 | −0.63 | −0.12 | −0.45 | AC007683.2 | −0.64 | −0.08 | −0.13 | 0.80 | 0.39 | AC092053.3 | 0.10 | −0.05 | −0.75 | −0.33 | −0.72 |
| COX10 | 0.62 | −0.29 | −0.64 | −0.07 | −0.12 | RBM42 | 0.17 | −0.08 | −0.37 | 0.02 | −0.21 | RP1-169K13.3 | 0.36 | −0.78 | −0.84 | 0.24 | 1.11 |
| AC010615.2 | −1.20 | 0.29 | 1.32 | 0.30 | 0.96 | AC060226.1 | 0.80 | −0.59 | −0.58 | 0.76 | 0.16 | RN7SKP160 | 0.18 | −0.44 | 1.17 | −0.09 | 0.32 |
| PWP1 | 0.62 | −0.30 | −0.70 | −0.08 | −0.38 | CASK-AS1 | 1.90 | 0.16 | −1.00 | 0.18 | 0.19 | MIR1277 | 0.48 | 1.32 | 0.96 | −1.17 | −0.71 |
| SELENOT | 0.69 | −0.26 | −0.43 | −0.09 | −0.36 | AL117334.1 | 0.93 | −0.77 | −0.36 | −0.20 | 0.56 | SRR | 0.07 | −0.15 | 0.29 | −0.11 | 0.25 |
| CDC42EP1 | 0.91 | −0.34 | −1.03 | 0.20 | −0.34 | AP000345.2 | −0.73 | 0.12 | 0.74 | 0.07 | 0.58 | GIMAP1 | −0.12 | −0.04 | 0.48 | −0.01 | 0.14 |
| SLMAP | 0.49 | −0.18 | −0.75 | −0.10 | −0.45 | AL136097.2 | 0.55 | −0.60 | −0.57 | −0.43 | −0.35 | HSPA8P5 | −0.17 | −0.20 | −0.70 | −0.39 | −0.92 |
| MAST4-AS1 | 1.34 | −0.56 | −1.11 | −0.12 | −0.60 | AC127496.4 | 1.12 | 0.49 | 0.18 | −0.01 | −0.33 | GGTLC4P | 0.29 | 0.31 | 0.92 | 0.24 | −0.35 |
| MRPL18 | 0.85 | −0.43 | −0.46 | −0.26 | −0.24 | AC005972.2 | 0.84 | −1.23 | 0.17 | −0.13 | 1.05 | SCN4B | −0.07 | 0.06 | −0.39 | 0.07 | −0.03 |
| LINC01287 | −2.08 | 0.59 | −0.02 | 0.49 | −0.54 | MLLT1 | −0.17 | 0.13 | −0.07 | 0.12 | −0.03 | HK2P1 | 0.24 | −0.79 | −1.15 | 0.04 | −1.11 |
| RN7SL562P | −1.94 | −0.16 | 1.48 | 0.49 | 1.44 | AC051649.1 | −0.98 | −1.51 | 1.18 | −1.32 | 1.73 | AC114810.1 | −0.19 | −0.62 | 0.42 | −0.17 | 0.65 |
| ADAM17 | 0.43 | −0.22 | −0.38 | −0.06 | −0.15 | NLRP14 | −0.66 | −1.48 | 0.17 | 0.11 | 0.62 | AC022395.1 | 0.11 | −0.40 | −0.05 | −0.06 | 0.09 |
| RPS29 | 0.62 | −0.24 | −0.64 | 0.14 | −0.68 | LINC00515 | −0.47 | 0.22 | 0.28 | 0.21 | 0.41 | AC094108.1 | −0.62 | −0.55 | 0.11 | −0.41 | −0.15 |
| AC011586.2 | −1.96 | 1.66 | 0.95 | 0.47 | −0.61 | AC009533.1 | −0.31 | −0.18 | −0.55 | 0.14 | 0.02 | LINC02316 | −0.20 | −0.48 | −0.49 | −0.27 | −0.64 |
| SMARCD1 | 0.38 | −0.23 | −0.57 | −0.13 | −0.25 | AK3P3 | −0.30 | 0.26 | 0.59 | −0.09 | −0.02 | AC131935.2 | −0.37 | 0.25 | −1.24 | −0.17 | −3.03 |
| NOMO1 | 0.46 | −0.26 | −0.38 | −0.14 | −0.22 | G28347 | 0.37 | −0.46 | −0.36 | −0.18 | 0.11 | HAP1 | 0.10 | −0.06 | −0.26 | 0.34 | 0.35 |
| C14orf119 | 0.77 | −0.42 | −0.84 | −0.14 | −0.62 | ATRNL1 | −0.55 | −0.41 | −1.00 | 0.59 | 0.20 | AC137630.3 | 0.38 | −0.48 | 0.74 | −0.36 | −0.05 |
| RHOBTB3 | −1.15 | 0.62 | 1.49 | 0.05 | 0.25 | LINC01579 | −0.73 | −0.11 | −0.34 | 0.18 | −0.21 | EPS15L1 | 0.04 | 0.02 | −0.18 | 0.07 | −0.10 |
| PPP1R12B | −0.57 | 0.36 | 0.31 | 0.24 | −0.09 | AL157823.2 | −1.02 | 0.14 | 0.19 | −0.23 | −0.60 | AP001020.3 | −0.12 | 0.27 | 0.41 | 0.09 | 0.45 |
| C2orf92 | −0.86 | 0.33 | 1.02 | 0.28 | 0.46 | AC012486.1 | −0.53 | 0.00 | −0.11 | 0.55 | 0.56 | LINC02485 | 0.56 | −2.42 | −0.99 | 0.19 | 2.03 |
| ERC1 | 0.48 | −0.19 | −0.61 | −0.07 | −0.21 | AC092821.3 | −0.42 | −0.08 | −0.19 | 0.17 | 0.14 | AL591518.1 | 0.32 | −0.41 | −0.27 | 0.05 | −0.74 |
| MND1 | 1.28 | −0.80 | −1.27 | −0.43 | −0.86 | AC138965.3 | 1.34 | −0.81 | −0.30 | −0.29 | 0.82 | INVS | 0.04 | −0.08 | 0.01 | −0.15 | 0.05 |
| HJURP | 1.22 | −1.25 | −1.61 | −0.37 | −0.35 | SPDEF | −0.69 | 1.19 | 1.34 | 0.59 | 0.50 | LINC00973 | 0.40 | 0.05 | −1.02 | 0.13 | −0.98 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| CRK | 0.44 | −0.20 | −0.46 | −0.09 | −0.30 | RN7SL490P | −0.68 | −0.50 | 0.82 | 0.50 | 1.35 | PTPRB | −0.09 | 0.09 | 0.51 | 0.07 | −0.06 |
| DCBLD1 | 0.84 | −0.60 | −0.91 | −0.18 | −0.22 | LINC01767 | 0.49 | −0.12 | −0.46 | −0.47 | −0.70 | AC016821.1 | −0.19 | 0.08 | −0.31 | 0.39 | 0.19 |
| ANKRD20A1 | −1.66 | −0.01 | 1.07 | 0.58 | 1.23 | RNASE1 | −0.55 | 0.62 | 0.49 | 0.20 | −0.24 | RAX2 | −0.26 | 0.32 | −0.95 | 0.29 | 0.33 |
| MRPS35 | 0.80 | −0.52 | −0.49 | −0.15 | −0.27 | AC010476.1 | 1.78 | −1.15 | −2.93 | −0.67 | −2.44 | AL009050.1 | −0.42 | 1.23 | 1.05 | 1.62 | 0.29 |
| ITPA | 0.52 | −0.23 | −0.51 | 0.03 | −0.19 | AC079380.1 | −1.01 | −0.05 | −0.14 | 0.53 | −0.28 | MIR3664 | 0.97 | −0.76 | 0.31 | −1.81 | 1.45 |
| HEATR1 | 0.60 | −0.35 | −0.47 | −0.11 | −0.14 | LINC00900 | 0.61 | −0.48 | −0.34 | 0.07 | 0.34 | AC068721.1 | 0.49 | −1.27 | −1.18 | 0.86 | −0.29 |
| EEPD1 | −0.78 | 0.54 | 0.65 | 0.31 | 0.12 | RNU6-826P | −0.98 | 0.42 | −0.05 | 0.14 | 0.12 | MAP7D3 | −0.09 | −0.06 | −0.06 | −0.05 | −0.22 |
| HPX | −0.94 | 0.75 | 0.12 | 0.41 | −0.56 | RNA5SP336 | −1.12 | 1.01 | 0.85 | 1.11 | 0.70 | AC002075.1 | −0.96 | 1.13 | −0.06 | 0.26 | −1.85 |
| ANXA2P2 | 0.83 | −0.30 | −1.18 | 0.03 | −0.79 | RIMBP3 | 0.89 | 0.10 | −1.50 | 1.05 | 0.61 | PRDM14 | 0.32 | −0.13 | −0.29 | 0.33 | −0.88 |
| NCL | 0.78 | −0.68 | −0.74 | −0.33 | −0.18 | AC211485.1 | −1.53 | −0.70 | 1.06 | 0.31 | 2.72 | ACTL7B | −0.23 | −0.59 | −1.78 | 0.74 | −0.71 |
| KCTD21 | 0.82 | −0.37 | −0.44 | −0.28 | −0.45 | ANKRD18EP | 0.33 | −0.15 | −0.64 | 0.09 | −0.18 | AL136126.1 | −0.29 | 1.05 | −1.02 | −0.02 | −1.74 |
| KANTR | −0.83 | 0.53 | 0.92 | 0.37 | 0.37 | LIPC | −0.50 | 0.57 | 0.46 | −0.04 | 0.21 | RN7SL195P | −0.20 | 0.62 | 0.57 | 0.45 | −0.17 |
| PCDHGA2 | −1.05 | 0.63 | 1.02 | 0.43 | 0.37 | ADAT3 | 0.37 | −0.03 | −0.43 | 0.17 | −0.01 | AC106800.1 | −0.27 | −0.54 | −0.84 | 0.44 | 0.77 |
| PSMC3 | 0.69 | −0.32 | −0.61 | −0.22 | −0.54 | BRI3 | −0.16 | 0.12 | 0.29 | 0.03 | 0.15 | ARL6 | −0.08 | −0.07 | 0.29 | −0.05 | −0.03 |
| DIAPH3 | 1.04 | −0.98 | −1.13 | −0.39 | −0.28 | CCDC32 | −0.17 | 0.08 | 0.18 | 0.03 | 0.04 | AC124283.4 | 0.13 | −0.11 | −0.25 | 0.23 | 0.30 |
| BCAS2 | 0.76 | −0.29 | −0.57 | −0.13 | −0.31 | AL022238.1 | 0.49 | −0.59 | −0.35 | −0.55 | −0.38 | ENO4 | −0.11 | 0.42 | 0.58 | 0.24 | 0.38 |
| C16orf96 | −1.67 | 0.94 | 1.17 | 0.86 | 0.60 | SPATA6L | −0.20 | 0.28 | 0.83 | 0.06 | 0.37 | AL357833.2 | −0.92 | −0.55 | 0.61 | 0.37 | 1.69 |
| PSMB8 | 0.86 | −0.59 | −0.58 | −0.31 | −0.39 | DEDD2 | 0.18 | −0.10 | 0.00 | 0.00 | −0.06 | OFD1P17 | −0.10 | −0.14 | −0.05 | −0.10 | 0.32 |
| ORC5 | 0.56 | −0.38 | −0.20 | −0.19 | 0.03 | ATF1 | 0.15 | 0.00 | 0.03 | −0.13 | 0.00 | AC027607.1 | −0.15 | 0.45 | 0.49 | 0.26 | 0.44 |
| FRMD4A | −0.54 | 0.01 | 0.10 | 0.06 | 0.13 | KRTAP5-9 | −0.85 | 0.51 | 0.27 | −0.38 | −0.31 | FBXO27 | −0.08 | 0.18 | −0.06 | 0.42 | −0.07 |
| AP001528.2 | −1.48 | 1.22 | 1.28 | 0.51 | −0.17 | NCF2 | 0.26 | −0.25 | −0.42 | −0.12 | −0.39 | AC092078.2 | 0.56 | −1.17 | −0.72 | 0.04 | −0.37 |
| CANX | 0.72 | −0.38 | −0.50 | −0.24 | −0.24 | CRELD2 | 0.23 | −0.19 | −0.64 | −0.15 | −0.19 | IGLV6-57 | 0.90 | 0.38 | −0.44 | 0.23 | −0.82 |
| FP325330.3 | −1.39 | 0.98 | 1.24 | 0.44 | 0.08 | AL137784.3 | −1.16 | 0.23 | −0.81 | 0.07 | 1.06 | AC092447.5 | −0.79 | −1.21 | 1.50 | −2.70 | 1.54 |
| AC068533.2 | −2.47 | 0.97 | 1.73 | 1.26 | 1.59 | G18316 | 0.76 | −1.55 | −0.27 | −0.21 | 0.59 | AC076966.1 | 0.44 | 0.76 | 1.36 | 0.51 | 0.90 |
| RABIA | 0.72 | −0.28 | −0.53 | −0.15 | −0.46 | AC005954.1 | −0.88 | −0.18 | 0.18 | 1.19 | 1.18 | AC092296.1 | −0.23 | 0.28 | 1.09 | 0.76 | 0.64 |
| MIA2 | 0.50 | −0.22 | −0.40 | −0.04 | −0.10 | PIK3CD-AS1 | 0.65 | −0.58 | −0.05 | −0.42 | 0.12 | NME9 | −0.05 | 0.05 | 0.11 | 0.12 | 0.18 |
| SLC27A4 | 0.75 | −0.13 | −0.39 | −0.05 | −0.30 | ARMH1 | −0.46 | 0.09 | 0.21 | 0.35 | 0.48 | AC063944.2 | −0.37 | −0.27 | 2.01 | 0.19 | 1.18 |
| CKB | −0.92 | 0.86 | 0.40 | 0.28 | −0.46 | LINGO2 | −0.82 | 0.66 | 0.51 | 0.64 | 0.03 | SMPX | −0.43 | 0.40 | −2.84 | 1.19 | −0.88 |
| AC003958.2 | −1.71 | 0.02 | −0.05 | 0.02 | 0.07 | FAM24B | −0.38 | −0.23 | 0.61 | 0.09 | 0.42 | AC092849.1 | 0.21 | 0.19 | −0.03 | 0.13 | 0.10 |
| C6orf163 | −0.50 | 0.25 | 0.61 | −0.07 | 0.16 | SPACA6P-AS | −0.53 | 0.40 | −0.02 | −0.34 | 0.27 | C1orf143 | −0.60 | −0.61 | −0.07 | −1.44 | −1.47 |
| GPD1L | −0.67 | 0.50 | 0.59 | 0.42 | 0.16 | AC110079.1 | −0.24 | 0.02 | 0.25 | −0.27 | −0.03 | KCNMB3P1 | 0.42 | −0.47 | −0.47 | 0.56 | −0.66 |
| DSG1 | 1.90 | −0.17 | −0.81 | 0.26 | −0.91 | AC013762.1 | 0.79 | −0.25 | 0.52 | 0.35 | 0.58 | CCNL1 | 0.05 | −0.01 | −0.45 | −0.07 | −0.22 |
| SLC4A8 | 1.07 | −1.08 | −1.53 | −0.37 | −0.47 | MCM7 | 0.17 | −0.27 | −0.43 | 0.00 | −0.03 | NMNAT1P5 | −0.67 | −0.28 | −2.53 | 0.85 | −0.76 |
| AF117829.1 | −0.40 | 0.14 | 0.53 | −0.20 | 0.08 | LINC01654 | 1.31 | −0.32 | −1.76 | −0.16 | −3.11 | RN7SL367P | −0.43 | 0.73 | 1.98 | 0.45 | 1.53 |
| PGM5P4 | −2.57 | 1.82 | 2.37 | 0.97 | 0.66 | REEP5 | 0.20 | 0.03 | −0.08 | −0.06 | −0.17 | AC018553.1 | −0.12 | 0.19 | 0.18 | 0.28 | 0.02 |
| CHST1 | 1.79 | −0.55 | −2.63 | 0.82 | −0.85 | NHS | −0.24 | −0.03 | 0.15 | 0.02 | −0.04 | PNRC2P1 | 0.21 | −0.77 | 0.07 | −0.96 | −0.47 |
| DPT | −1.64 | 0.80 | 2.09 | −0.13 | 0.21 | EEF1A1P6 | 0.28 | 0.02 | 0.07 | −0.09 | −0.16 | ISY1 | 0.05 | 0.11 | −0.28 | 0.09 | −0.38 |
| AKR7A2P1 | 2.28 | −0.68 | −1.47 | 0.07 | −0.89 | AC244502.1 | 0.80 | −0.58 | −0.62 | 0.10 | 0.25 | SPDYE2B | 0.19 | 0.68 | −0.21 | 0.37 | 0.42 |
| DRC3 | −0.58 | 0.29 | 0.37 | 0.18 | 0.06 | CEACAMP6 | −1.50 | −0.48 | 1.37 | −0.59 | 0.63 | RN7SL810P | −0.67 | 0.20 | −0.51 | 1.17 | −0.24 |
| FAM27E3 | −2.21 | 0.68 | 1.44 | −0.01 | 1.00 | CYP51A1-AS1 | −0.64 | −0.10 | −0.66 | 0.78 | −0.08 | AC104024.2 | 0.33 | −0.07 | −1.09 | −0.39 | −0.66 |
| ELOVL7 | 1.18 | 0.05 | −0.11 | 0.24 | −0.82 | Metazoa_SRP | −0.27 | −0.18 | −0.19 | 0.03 | 0.09 | AC022497.1 | 0.12 | 0.34 | 0.14 | 0.19 | −0.32 |
| EIF5 | 0.71 | −0.27 | −0.66 | −0.01 | −0.57 | PAX8 | −0.26 | 0.23 | 0.47 | 0.12 | 0.26 | ARHGAP27P2 | −0.26 | 0.35 | 0.60 | 1.09 | −0.06 |
| PPA1 | 0.83 | −0.44 | −0.62 | −0.26 | −0.42 | RNA5SP294 | 0.60 | −1.03 | −0.55 | −0.26 | 0.45 | DDX18P4 | −0.48 | −2.29 | 1.00 | −0.70 | 0.13 |
| CLYBL | −0.71 | 0.38 | 0.43 | 0.46 | 0.44 | AC078785.1 | −0.61 | 0.21 | −0.16 | 0.58 | −0.16 | AP000679.1 | 0.13 | 0.21 | −0.39 | 0.20 | −0.59 |
| CFAP69 | −0.84 | 0.37 | 0.82 | −0.44 | −0.09 | RNF144A-AS1 | 0.63 | −0.24 | −1.04 | −0.84 | −1.12 | CYR61 | −0.09 | −0.41 | 0.36 | −0.91 | −0.23 |
| ASB16 | −1.05 | 0.01 | 0.32 | 0.22 | 0.60 | HNRNPABP1 | 1.53 | −0.19 | −2.37 | 0.50 | −0.58 | RN7SL528P | −0.52 | 0.55 | −0.10 | 2.49 | 0.96 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| DTD2 | 0.83 | −0.46 | −0.81 | −0.21 | −0.33 | AC107884.2 | 0.46 | −0.37 | −0.77 | −0.07 | 0.01 | AC005162.3 | −0.10 | −0.51 | 0.29 | 0.09 | 0.56 |
| C7orf43 | −0.81 | 0.32 | 0.28 | 0.51 | 0.38 | AC020612.3 | −0.31 | 0.03 | 0.27 | 0.07 | 0.28 | MTCYBP42 | 0.61 | −1.32 | 0.44 | 1.14 | 0.01 |
| ERH | 0.75 | −0.49 | −0.68 | 0.00 | −0.37 | AC022778.1 | 0.47 | −0.43 | −0.01 | −0.18 | 0.16 | MIR4635 | −0.34 | −1.79 | −0.01 | 0.23 | 0.49 |
| AC080188.2 | 1.29 | −0.30 | −0.98 | −0.06 | −0.61 | AHCYL1 | 0.13 | −0.08 | −0.13 | 0.04 | −0.02 | RPL32P34 | −0.23 | −0.36 | −0.74 | 0.51 | −0.62 |
| PSD3 | −0.51 | 0.30 | 0.65 | −0.07 | 0.04 | PIGFP1 | −0.87 | −0.34 | 1.32 | −0.25 | 0.15 | RPS26P45 | 0.35 | −0.32 | −0.57 | −0.46 | −0.84 |
| SSX2IP | 0.69 | −0.34 | −0.66 | 0.01 | −0.25 | AC012038.2 | −1.30 | −0.80 | 0.39 | −0.85 | 0.86 | C12orf40 | −0.14 | 0.50 | 0.38 | −0.04 | −0.42 |
| HRH1 | 0.81 | −0.57 | −1.10 | −0.13 | −0.84 | SLC28A2 | −0.49 | −0.26 | 0.23 | −0.23 | 0.11 | NANOGPS | 0.10 | −0.14 | 0.27 | −0.26 | 0.24 |
| CACNA2D1 | −1.13 | 0.62 | 1.08 | 0.16 | 0.16 | FBXL6 | 0.30 | −0.44 | −0.76 | 0.12 | 0.26 | MDH1B | −0.11 | 0.64 | −0.28 | 0.67 | −0.16 |
| IGSF11 | −1.34 | 0.64 | 0.67 | 0.32 | 0.30 | AC018868.2 | 0.58 | −0.51 | −0.37 | 0.57 | 0.83 | MAEL | −0.22 | 0.40 | −1.30 | 0.89 | −0.84 |
| PSMG1 | 0.74 | −0.30 | −0.67 | 0.07 | −0.14 | AL355499.1 | −0.82 | 1.14 | 0.13 | 0.61 | −0.55 | AC092718.1 | −0.25 | 0.40 | −0.83 | 0.11 | −1.23 |
| G5909 | −1.08 | 0.74 | 0.66 | 0.68 | −0.05 | MAP2K6 | −0.28 | 0.26 | 0.54 | 0.32 | 0.23 | AC002310.2 | −0.36 | 0.72 | −1.92 | 0.46 | −0.49 |
| EEF1A1P32 | 1.46 | −0.53 | −1.42 | 0.16 | −0.66 | F5 | −0.48 | 0.37 | 0.94 | 0.09 | 1.27 | LLfos-48D6.1 | 0.37 | −1.10 | −2.36 | −0.02 | 0.04 |
| LINC01805 | −1.63 | 0.94 | 2.29 | 0.87 | 0.47 | RN7SL374P | −1.24 | −1.79 | 0.59 | −0.58 | 0.45 | SLC25A12 | 0.04 | 0.16 | −0.02 | 0.05 | −0.20 |
| SMARCD3 | −0.91 | 0.47 | 0.89 | 0.22 | 0.33 | MTG1 | 0.40 | 0.08 | −0.30 | 0.04 | −0.10 | AL096711.2 | −0.24 | 0.02 | 1.08 | 0.59 | 0.72 |
| LARP6 | −1.23 | 0.73 | 1.24 | 0.09 | 0.02 | GDI2P1 | −1.45 | −0.94 | −0.16 | −1.09 | −0.13 | HMGN1P36 | 0.17 | −0.11 | −0.70 | 0.23 | −0.26 |
| SEC24B-AS1 | −0.95 | 0.52 | 1.01 | 0.25 | 0.36 | AREGB | 1.55 | −0.86 | −2.27 | −1.06 | −1.26 | AF228730.2 | −0.27 | 0.42 | 2.36 | 0.36 | 0.99 |
| NDUFAF2 | 0.70 | −0.51 | −0.58 | −0.25 | −0.11 | BTBD19 | 0.25 | −0.32 | −0.17 | −0.30 | −0.23 | FOXN3-AS2 | −0.12 | 0.10 | −0.13 | 0.18 | −0.11 |
| LYPLA2 | 0.60 | −0.35 | −0.70 | −0.02 | −0.23 | RPS3AP32 | 0.56 | −0.83 | −0.69 | 0.32 | 0.25 | C1orf174 | 0.04 | −0.08 | −0.23 | 0.04 | −0.07 |
| ATG16L2 | −0.91 | 0.30 | 0.45 | 0.41 | 0.48 | AC095057.3 | −0.25 | 0.28 | 0.28 | 0.05 | −0.27 | AC048351.1 | 0.34 | 0.15 | −1.08 | −0.70 | −2.69 |
| NCCRP1 | 1.65 | −0.36 | −0.42 | 0.11 | −0.92 | PRB3 | −0.35 | −0.01 | 0.14 | 0.06 | −0.34 | CAPSL | 0.58 | −0.60 | −1.51 | 1.03 | −1.32 |
| AL137182.1 | −1.71 | 1.31 | 1.64 | 0.91 | 0.10 | AC124319.1 | 0.41 | −0.52 | −0.18 | −0.45 | 0.36 | LINC01913 | −0.24 | −0.29 | −0.19 | −0.33 | −0.58 |
| GPSM2 | 0.85 | −0.27 | −0.59 | −0.05 | −0.24 | PCAT18 | −0.85 | 0.38 | 0.90 | 1.03 | 0.68 | OR4N5 | −0.40 | −1.92 | −0.17 | −0.36 | 0.36 |
| RCAN1 | 0.89 | −0.10 | −0.39 | −0.71 | −1.12 | RAB34 | 0.19 | −0.23 | −0.50 | −0.15 | −0.13 | RPL6P9 | 0.49 | −1.41 | 0.09 | 1.70 | 0.01 |
| CLK3 | −0.52 | 0.15 | 0.20 | 0.09 | 0.17 | CHAF1B | 0.22 | −0.58 | −0.97 | −0.06 | −0.13 | GLYATL3 | 0.57 | −1.31 | −0.42 | 0.48 | 1.32 |
| KDM4B | −0.63 | 0.37 | 0.38 | 0.26 | 0.16 | CERS1 | −0.85 | −0.37 | 1.56 | −0.26 | 1.36 | SERPIND1 | 0.07 | −0.24 | 0.36 | −0.21 | 0.17 |
| RBPMS2 | −1.41 | 0.67 | 0.98 | 0.16 | −0.02 | AC069209.1 | −0.91 | 0.75 | 0.05 | 0.76 | −1.14 | RNA5SP465 | −0.27 | −0.22 | 0.40 | 0.37 | 1.68 |
| G14548 | −1.37 | 0.42 | 0.96 | 0.01 | 0.03 | MIR4453HG | 0.17 | −0.29 | −0.03 | 0.00 | 0.25 | FANCG | 0.05 | −0.26 | −0.46 | −0.08 | −0.01 |
| MMADHC | 0.98 | −0.30 | −0.58 | −0.03 | −0.53 | SRSF11 | −0.16 | 0.02 | −0.14 | 0.05 | −0.05 | AC087752.4 | 0.15 | −1.04 | −0.38 | −0.21 | 0.47 |
| AL008707.1 | −2.15 | 1.84 | 2.03 | 1.35 | 0.24 | AP000942.1 | 0.78 | 0.09 | 0.36 | −0.20 | −0.34 | CLDN20 | 0.10 | −0.13 | 0.31 | −0.21 | 0.04 |
| GNPNAT1 | 0.97 | −0.75 | −0.70 | −0.58 | −0.18 | CNIH2 | −0.38 | 0.11 | 0.30 | −0.13 | −0.17 | HSPD1P8 | −0.45 | −0.80 | −2.17 | 0.60 | −1.70 |
| ASF1B | 1.28 | −1.14 | −1.12 | −0.28 | −0.03 | BX005132.1 | 1.39 | −0.73 | −2.68 | −0.30 | −0.65 | AC018628.2 | 0.12 | −0.22 | 0.33 | 0.03 | 0.25 |
| EXT2 | 0.43 | −0.17 | −0.33 | −0.15 | −0.20 | PRICKLE2-AS1 | 0.49 | −0.69 | −0.38 | −0.38 | −0.05 | AC009487.3 | 0.39 | −0.22 | 0.05 | 0.45 | 1.78 |
| IFITM1 | 1.13 | −0.39 | −1.05 | −0.04 | −1.05 | KLC2 | 0.22 | −0.07 | −0.29 | 0.04 | −0.01 | AC096887.2 | −0.28 | −0.13 | 0.10 | 0.17 | 0.74 |
| LRRC37A3 | −0.57 | 0.27 | 0.67 | 0.00 | 0.41 | FAM86C2P | 0.27 | −0.04 | −0.29 | 0.06 | −0.01 | PIH1D3 | −0.49 | −0.48 | −0.20 | −0.09 | −1.00 |
| LGI4 | −1.26 | 1.09 | 1.05 | 0.57 | −0.31 | AC002074.2 | −0.84 | 1.41 | 0.41 | −0.38 | −0.60 | AC140847.2 | −0.37 | −1.02 | −0.06 | 0.17 | −0.20 |
| HELLS | 0.93 | −0.75 | −0.98 | −0.17 | −0.19 | AC096540.1 | −0.83 | 0.16 | 1.23 | 0.04 | −0.02 | MTCO1P49 | 0.77 | −1.72 | −0.84 | −0.69 | −0.88 |
| MGP | −1.46 | 1.18 | 1.23 | 0.45 | −0.27 | RPL11P3 | 0.38 | −0.31 | −0.45 | −0.23 | 0.07 | AC008799.2 | −0.79 | −0.14 | −0.66 | 1.09 | −0.07 |
| FAM98C | −0.59 | 0.23 | 0.25 | 0.15 | 0.20 | LINC00092 | −0.45 | −0.07 | 0.34 | 0.47 | 0.17 | OR5T2 | 0.58 | −1.26 | −0.44 | 0.50 | 0.82 |
| PDZRN4 | −1.59 | 1.12 | 1.51 | −0.10 | −0.30 | STOX2 | −0.19 | 0.42 | 0.23 | 0.27 | 0.30 | AP002530.1 | 0.67 | −0.74 | −2.01 | 0.40 | −0.72 |
| RPS7 | 0.75 | −0.25 | −0.40 | −0.09 | −0.57 | LINC02352 | −0.65 | 0.69 | 1.26 | 0.43 | −0.27 | AC087235.1 | −0.49 | 0.67 | −1.25 | 1.85 | 0.70 |
| ALDHIL1 | −1.83 | 1.53 | 0.80 | 1.45 | −0.18 | SELENOK | 0.21 | 0.14 | −0.23 | −0.08 | −0.52 | LINC01235 | −0.19 | −0.05 | −0.04 | 0.29 | 0.25 |
| CLDN18 | −1.02 | 0.41 | 1.23 | −0.18 | 0.18 | STRA8 | −1.20 | 1.34 | 0.49 | 0.52 | −0.46 | BTNL10 | −0.40 | −0.50 | 0.72 | 1.32 | 0.33 |
| MUC20P1 | −1.73 | 0.35 | 0.90 | 1.52 | −0.46 | EGLN1 | 0.24 | 0.04 | 0.07 | −0.02 | −0.04 | RPL18AP14 | −0.52 | −0.42 | 1.08 | 0.07 | 0.65 |
| HRASLS5 | −2.32 | 2.10 | 1.28 | 1.25 | 0.19 | AC011389.2 | −0.73 | 0.91 | 0.58 | −0.21 | −0.49 | PARD6A | −0.15 | 0.55 | −0.20 | 0.58 | 0.25 |
| POU2F3 | −1.11 | 0.73 | 0.95 | 0.51 | 0.48 | LINC01465 | −0.28 | −0.04 | −0.03 | 0.02 | 0.22 | RN7SKP266 | −0.61 | 0.84 | −1.02 | 2.23 | 0.65 |
| C10orf55 | 1.74 | −0.90 | −2.17 | 0.13 | −1.23 | GSTO2 | −0.28 | 0.38 | 0.47 | 0.31 | 0.29 | AL355365.1 | 0.81 | 0.43 | −2.29 | 0.30 | −3.06 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| FGFR1 | −1.03 | 0.72 | 1.07 | −0.10 | −0.04 | RNU7-18P | 0.80 | −1.21 | −0.50 | −0.80 | −0.18 | HOXB9 | 0.28 | −0.32 | −0.10 | 0.59 | −0.38 |
| SLIT2 | −1.06 | 0.72 | 1.47 | 0.08 | 0.13 | ETV6 | 0.17 | 0.05 | −0.06 | −0.03 | −0.07 | DUXAP5 | 0.65 | −0.81 | −0.98 | 1.26 | 0.22 |
| FABP7 | −2.35 | 1.32 | 1.15 | 1.64 | −0.08 | AL139300.2 | −0.54 | 0.38 | 0.55 | −0.11 | −0.02 | SNORA36C | −0.18 | −0.47 | −0.33 | 0.52 | −0.62 |
| ADAM1B | −1.31 | 0.90 | 2.00 | 0.00 | 0.37 | PUS1 | 0.26 | −0.35 | −0.50 | 0.07 | 0.22 | G26215 | −0.26 | −0.78 | −0.23 | 0.46 | 0.32 |
| GATB | 0.76 | −0.34 | −0.72 | 0.05 | −0.21 | AC027338.1 | 1.03 | 0.19 | 0.05 | 0.06 | −0.87 | AC126178.1 | −0.33 | −0.29 | 0.10 | 0.05 | −1.27 |
| LSS | −0.66 | 0.22 | 0.19 | 0.24 | 0.05 | AC027288.3 | −0.55 | 1.10 | 0.73 | 0.65 | −0.10 | PTGER4P2 | −0.56 | 1.49 | 0.94 | 2.77 | 1.31 |
| MAP2K4 | 0.62 | −0.17 | −0.49 | −0.06 | −0.38 | ARSE | −0.74 | 1.12 | 1.11 | 0.36 | 0.18 | OR6K1P | −0.69 | −1.12 | −0.48 | −0.62 | −0.86 |
| FAM84A | 1.02 | −0.29 | −0.35 | −0.07 | −0.12 | HSPA8P15 | 0.38 | 0.09 | −0.39 | 0.21 | 0.13 | DUX4L45 | 0.40 | −0.39 | −0.73 | 0.87 | −0.14 |
| ATP5PB | 0.75 | −0.32 | −0.55 | −0.22 | −0.44 | ST13P10 | −0.39 | 0.51 | 0.96 | 0.37 | 0.33 | NUDT4B | 0.30 | −1.02 | 0.61 | −0.33 | 0.27 |
| SLC3A2 | 0.70 | −0.31 | −0.81 | −0.07 | −0.48 | MIR766 | 0.82 | −0.40 | −1.02 | −0.47 | −0.57 | OR13C8 | −0.59 | −2.00 | −1.35 | −0.73 | −0.09 |
| MISP3 | −1.05 | 1.39 | 1.09 | 0.78 | −0.11 | AC017048.3 | −0.69 | −0.11 | 1.10 | −0.57 | 0.46 | AC010460.3 | 0.50 | −0.43 | −1.01 | 0.87 | 0.50 |
| GOLGA8M | −1.53 | 0.84 | 1.26 | 0.71 | 0.05 | RALYL | −0.91 | 0.04 | −0.35 | −0.30 | −1.12 | G3928 | −0.42 | 0.32 | 0.79 | −0.65 | 0.54 |
| SCRN1 | 0.79 | −0.24 | −0.47 | −0.04 | −0.29 | AL355490.2 | 0.86 | 0.40 | −0.23 | 0.25 | −0.95 | PLCH1-AS1 | −0.34 | 0.18 | −0.47 | −0.15 | −0.10 |
| MRM2 | 0.65 | −0.40 | −0.44 | −0.11 | 0.04 | CCDC144A | −0.43 | 0.03 | 0.78 | 0.35 | 1.38 | GPR32 | −0.76 | 1.12 | 0.34 | −0.09 | −2.20 |
| SPIN4 | 0.85 | −0.50 | −1.12 | −0.08 | −1.00 | RN7SL792P | −1.34 | 1.66 | 0.53 | 0.60 | −0.70 | AL023693.1 | −0.52 | −0.87 | −0.14 | 0.16 | −0.99 |
| PLEK2 | 1.08 | −0.70 | −1.20 | −0.11 | −0.36 | MRPS36P2 | −0.81 | 0.38 | 1.14 | 0.39 | 0.71 | AC105020.6 | −0.19 | −0.04 | −0.29 | −0.35 | −0.11 |
| AC016735.1 | −2.20 | 0.06 | 0.94 | 1.15 | 0.94 | CA4 | −0.67 | −0.26 | 0.12 | 0.28 | −0.27 | FGFR4 | −0.12 | 0.06 | −0.99 | 0.54 | 0.05 |
| NEO1 | −0.70 | 0.65 | 0.98 | 0.37 | 0.25 | SIGLEC9 | 0.62 | −0.90 | −0.71 | −0.42 | −0.25 | OR51F2 | 0.42 | −0.13 | 0.26 | 0.15 | −1.46 |
| KIF5B | 0.75 | −0.31 | −0.61 | −0.29 | −0.56 | BTNL8 | −0.78 | 0.55 | −0.90 | 0.16 | −1.16 | COLEC10 | −0.30 | 0.12 | −0.80 | 0.23 | −0.12 |
| DDX3P1 | −0.93 | 0.62 | 1.00 | 0.06 | 0.23 | AP003064.2 | −1.15 | 0.08 | 2.19 | −0.09 | 0.30 | LINC01684 | −0.15 | −0.34 | 0.84 | 0.00 | 0.75 |
| AGPS | 0.72 | −0.41 | −0.37 | −0.26 | −0.19 | ANKRD18DP | 0.65 | −0.96 | −1.63 | 0.16 | −0.62 | KRCC1 | −0.06 | 0.04 | 0.04 | −0.13 | −0.06 |
| MIR100HG | −0.95 | 0.53 | 1.34 | 0.04 | 0.35 | AL021155.2 | 0.79 | 0.74 | −2.19 | −0.99 | −1.64 | AC005280.1 | −0.33 | −1.01 | 1.57 | −0.05 | 2.64 |
| SUCLG1 | 0.64 | −0.16 | −0.51 | 0.03 | −0.38 | NKAIN2 | −0.38 | 0.30 | −0.06 | 0.12 | −0.16 | BLOC1S5 | 0.05 | 0.01 | 0.32 | 0.01 | 0.30 |
| PCLAF | 1.26 | −1.33 | −1.34 | −0.39 | −0.30 | AC069154.1 | −0.80 | 0.30 | −0.29 | 0.53 | −0.07 | AC009053.2 | 0.18 | −0.69 | −0.30 | 0.41 | 0.26 |
| ABI1 | 0.50 | −0.05 | −0.55 | 0.00 | −0.44 | AL390774.1 | 0.88 | −1.10 | −1.54 | 0.40 | 1.09 | AL356432.3 | −0.97 | 1.44 | 0.94 | 1.12 | 0.39 |
| LINC01819 | −1.17 | 0.30 | 0.70 | 0.79 | 0.84 | CC2D2A | −0.17 | 0.12 | 0.09 | 0.03 | −0.05 | AC087636.1 | 0.76 | −0.65 | −0.56 | −0.33 | −0.55 |
| NAMPT | 1.24 | −1.00 | −1.33 | −0.39 | −0.77 | MYCBP2-AS2 | 0.59 | 0.59 | 1.11 | 0.25 | −0.21 | OR56B2P | −0.34 | −0.47 | 2.40 | 0.16 | 1.62 |
| MTMR2 | 0.58 | −0.34 | −0.45 | −0.21 | −0.24 | RN7SKP36 | −0.65 | −0.43 | 0.97 | −0.74 | 0.49 | AC138028.4 | −0.15 | −0.37 | −0.99 | 0.26 | −0.34 |
| ISM1 | −1.01 | 0.60 | 1.00 | 0.10 | 0.05 | AL157813.1 | 0.61 | −0.59 | −0.65 | 0.31 | −0.02 | FOLR3 | 0.28 | −0.61 | −1.30 | 0.11 | −0.88 |
| GSTA3 | −1.44 | 1.91 | 2.23 | 0.44 | 0.59 | RN7SKP95 | 0.60 | −0.91 | −0.72 | −0.24 | 0.54 | DUSP10 | −0.07 | 0.10 | 0.00 | 0.17 | −0.04 |
| RPL5P14 | −2.16 | 1.03 | 1.37 | 0.41 | −0.31 | ING3 | 0.18 | 0.04 | −0.09 | 0.09 | −0.14 | AL033527.6 | 0.24 | −2.09 | −1.22 | 0.44 | 1.70 |
| CUBN | −0.83 | 0.40 | 0.76 | −0.10 | 0.21 | CD96 | 0.52 | −0.75 | −0.24 | −0.45 | 0.30 | SMIM11B | −0.27 | −1.00 | −0.94 | −0.55 | −0.57 |
| PFDN2 | 0.79 | −0.56 | −0.60 | −0.32 | −0.31 | AL109659.1 | −1.10 | 0.38 | 2.35 | 0.18 | 1.74 | FLJ40194 | −0.19 | −0.81 | −0.08 | 0.50 | 0.76 |
| CIDEC | −3.04 | 3.06 | 2.63 | 1.57 | −0.03 | HECTD2 | 0.16 | −0.04 | −0.05 | −0.12 | −0.08 | AC020937.1 | −0.62 | −0.68 | 0.83 | −1.98 | 0.72 |
| GK | 1.01 | −0.82 | −0.44 | −0.16 | −0.09 | NUTM2HP | −0.87 | 0.21 | 1.32 | 0.21 | 1.21 | DMXL1 | −0.04 | 0.16 | 0.21 | 0.02 | −0.05 |
| RRNAD1 | −0.72 | 0.31 | 0.42 | 0.33 | 0.32 | AC121761.2 | −0.67 | 0.76 | 1.02 | 0.24 | 0.28 | DUSP4 | −0.12 | 0.00 | −0.51 | −0.02 | −0.52 |
| ADGRG2 | −0.70 | 0.24 | 0.57 | 0.18 | 0.07 | OR5B10P | −1.23 | −0.15 | 2.14 | 0.33 | 1.07 | IHH | −0.35 | −0.06 | 0.57 | −0.27 | −0.25 |
| AC006441.4 | −2.59 | 0.87 | 1.00 | 0.47 | −0.50 | TORD53_SNORD | −0.74 | 0.16 | 0.20 | 1.04 | 0.12 | AL031284.1 | −0.33 | −1.13 | −0.66 | −0.13 | 0.73 |
| MRPS15 | 0.74 | −0.50 | −0.60 | −0.35 | −0.28 | LY86 | 0.71 | −0.83 | 0.58 | −0.47 | 0.82 | LINC01502 | −0.48 | 0.77 | 0.05 | 0.87 | −0.12 |
| KRT35 | −3.39 | 0.95 | 3.28 | −1.51 | 2.02 | HCN4 | −0.77 | −0.13 | −0.60 | 0.44 | −0.01 | SNX18P4 | −0.42 | 0.07 | 0.71 | −0.79 | 0.50 |
| GLRB | −1.53 | 0.57 | 1.56 | 0.28 | 0.72 | AC106892.1 | −0.92 | 0.17 | 0.21 | 0.19 | −0.12 | PLAC1 | 0.35 | −0.67 | −0.02 | 0.15 | −0.83 |
| RUNX1T1 | −1.19 | 0.74 | 1.74 | 0.17 | 0.35 | OR14L1P | 1.40 | −0.63 | −2.12 | 0.20 | −0.73 | RN7SKP272 | −0.31 | 0.76 | −0.06 | 0.81 | 1.24 |
| CP | −1.25 | 0.44 | 1.34 | 0.11 | 0.21 | LINC00881 | 1.17 | −1.40 | −1.24 | 0.32 | 0.66 | NNT | −0.04 | −0.06 | −0.02 | 0.02 | −0.13 |
| RPL36 | 0.67 | −0.18 | −0.41 | −0.01 | −0.48 | AC012378.2 | −1.07 | 1.70 | 0.59 | 0.96 | 0.10 | G21031 | −0.21 | 0.56 | 0.76 | 0.29 | 0.66 |
| AL162274.3 | −1.09 | 0.32 | 0.96 | 0.21 | 0.21 | AL136360.2 | 1.08 | 0.51 | −0.55 | 0.25 | 0.49 | AC008750.3 | 0.24 | 1.02 | 0.02 | 1.19 | −0.26 |
| RPL23AP32 | −1.19 | 0.66 | 0.96 | 0.45 | 0.09 | AGAP1-IT1 | 0.35 | −0.14 | −0.21 | −0.07 | −0.15 | RNU7-101P | 0.20 | −0.04 | −0.25 | 0.27 | 0.19 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| DYNC1I1 | −1.07 | 0.60 | 0.55 | 0.55 | 0.27 | AC130709.1 | −0.49 | 0.82 | −0.05 | 0.85 | −0.01 | RNA5SP103 | −0.66 | −0.18 | 0.90 | −1.01 | 1.25 |
| MAPK14 | 0.59 | −0.21 | −0.49 | 0.11 | −0.24 | AL590822.2 | −0.31 | 0.13 | −0.04 | 0.30 | 0.27 | LINC01510 | 0.70 | 0.47 | 0.13 | 1.03 | −2.45 |
| PPP1R3F | −0.65 | 0.25 | 0.41 | 0.09 | 0.21 | AC011592.1 | −0.84 | −0.14 | −0.51 | 0.29 | 0.37 | CFAP298 | 0.07 | 0.07 | 0.22 | −0.07 | 0.06 |
| C3orf35 | −0.74 | 0.56 | 0.50 | 0.43 | 0.18 | AC063926.3 | −0.61 | 0.23 | 0.42 | 0.84 | 0.43 | KPRP | 0.17 | 0.16 | 0.11 | 0.90 | −0.66 |
| ALDH6A1 | −0.79 | 0.70 | 0.79 | 0.48 | 0.17 | ACO1 | −0.28 | −0.05 | 0.27 | −0.06 | 0.30 | ATP5MFP1 | 0.37 | −0.93 | −1.53 | 0.13 | −0.67 |
| HIST1H2AH | 1.39 | −1.18 | −1.40 | −0.30 | −0.60 | MIR548J | 1.37 | −1.41 | 0.29 | 0.39 | 1.46 | AC011124.1 | −0.30 | −0.64 | 0.42 | 0.36 | −0.34 |
| PDLIM1 | 0.71 | −0.36 | −0.60 | −0.09 | −0.31 | SDIM1 | 0.67 | −0.49 | −1.77 | −0.49 | −1.06 | AC005548.1 | 0.69 | 0.77 | −1.05 | 1.17 | −2.35 |
| NDST1 | 0.54 | 0.00 | −0.22 | −0.02 | −0.29 | RPS27AP9 | 0.88 | −0.83 | −0.46 | 0.27 | 0.38 | C6orf118 | 0.42 | 0.64 | 0.16 | −0.97 | −2.08 |
| ENPP1 | −1.28 | 0.81 | 0.90 | 0.26 | 0.13 | AC137723.2 | −1.21 | 0.08 | 2.39 | −0.67 | 0.75 | CYP2C23P | −0.57 | 0.25 | −0.08 | 1.26 | 0.29 |
| DAAM2 | −1.10 | 0.35 | 0.93 | 0.08 | 0.10 | LINC01666 | 0.63 | 0.35 | −0.13 | 0.13 | −0.16 | HMGB3P19 | −0.55 | −0.53 | 0.30 | −0.36 | −1.85 |
| BPHL | −0.50 | 0.34 | 0.40 | 0.38 | 0.35 | AC108058.1 | 0.33 | −0.03 | −0.54 | −0.16 | −0.55 | AC018735.1 | −0.67 | 0.35 | −1.78 | 1.41 | −1.73 |
| ISOC2 | 0.76 | −0.46 | −0.59 | −0.11 | −0.06 | RN7SKP268 | −1.17 | 0.13 | 1.45 | −0.82 | −0.41 | AC008868.1 | 0.29 | −0.23 | −1.05 | −0.19 | −0.84 |
| AP003025.1 | −1.62 | 0.58 | 0.90 | 0.63 | 0.43 | BTG3-AS1 | 0.35 | 0.17 | 0.12 | 0.09 | −0.17 | BFSP2 | 0.38 | −0.71 | −1.83 | −0.24 | −1.37 |
| LARP4B | 0.47 | −0.23 | −0.37 | −0.11 | −0.15 | LINC00461 | −0.84 | −0.27 | 1.08 | −0.77 | 0.07 | LINC01532 | −0.39 | −1.66 | 1.13 | −0.26 | 1.75 |
| FAM107A | −1.31 | 0.45 | 1.79 | 0.13 | 0.78 | AC068228.1 | 1.44 | −1.47 | −1.45 | 0.97 | 1.26 | RNU7-179P | −1.25 | 0.44 | 0.80 | −1.11 | −0.01 |
| PLAG1 | −0.97 | 0.61 | 0.71 | 0.18 | 0.19 | AP005436.1 | 0.78 | −0.36 | 0.20 | −0.03 | −0.10 | AC099344.1 | 0.49 | −0.83 | −2.64 | −0.27 | −2.54 |
| STPG2-AS1 | −2.33 | 0.98 | 0.30 | 0.86 | −0.19 | LINC00683 | −0.74 | −0.17 | 0.17 | 0.22 | 0.46 | RNU6-551P | −0.45 | 0.00 | 1.12 | −0.67 | 0.56 |
| AP006623.1 | −1.13 | 0.53 | 0.54 | 0.17 | 0.10 | AC087752.3 | −0.52 | 0.80 | 0.57 | 0.71 | 0.07 | MYL2 | 0.55 | 0.04 | −2.50 | 0.90 | −2.52 |
| ARMT1 | 0.67 | −0.32 | −0.48 | −0.17 | −0.17 | CHCHD10 | −0.26 | 0.26 | 0.13 | 0.17 | 0.10 | AC025038.1 | −0.16 | 0.75 | 0.70 | −0.20 | 0.17 |
| IL1RL1 | 1.41 | −0.98 | −0.53 | −0.04 | 0.06 | OR51S1 | 1.18 | −1.04 | −1.46 | −0.46 | −0.17 | AC096733.1 | 0.30 | 0.10 | −0.92 | −0.37 | −0.44 |
| STX1B | −0.89 | 0.54 | 0.56 | 0.35 | 0.19 | G31329 | −0.73 | 0.60 | 0.94 | −0.09 | −0.19 | LINC01268 | −0.14 | −0.21 | −0.21 | −0.23 | 0.08 |
| MRPL52 | 0.61 | −0.41 | −0.61 | −0.09 | −0.12 | DNAJA3 | 0.18 | −0.22 | −0.27 | −0.12 | 0.06 | OR5AP2 | −0.92 | 0.49 | 0.99 | −0.10 | −0.11 |
| AC112220.2 | 0.97 | −0.41 | −0.60 | −0.05 | −0.40 | SNORA73 | 0.60 | −0.42 | −0.52 | −0.53 | −0.37 | AL096701.1 | −0.16 | 0.34 | 0.09 | 0.14 | −0.28 |
| PPP1R8 | 0.50 | −0.12 | −0.35 | −0.06 | −0.31 | AC104472.1 | −1.13 | −0.47 | −0.73 | −0.03 | 0.48 | AC080013.6 | 0.19 | −0.22 | 0.06 | 0.02 | 0.59 |
| DAD1 | 0.64 | −0.34 | −0.59 | −0.26 | −0.51 | AL035071.2 | 0.53 | −0.30 | −0.63 | −0.21 | −0.30 | BORCS8-MEF21 | −0.26 | −0.99 | 0.16 | 0.39 | 0.72 |
| SMIM10L2A | −1.37 | 0.78 | 1.83 | 0.86 | 0.84 | G1159 | −0.61 | 0.31 | −1.18 | 0.37 | −0.68 | ANAPC1P1 | −0.17 | −0.20 | −0.82 | −0.15 | −0.85 |
| GSTM4 | −0.45 | 0.26 | 0.24 | −0.02 | −0.17 | AC015563.1 | −0.53 | 0.98 | 0.53 | 0.62 | −0.05 | AGAP4 | −0.10 | 0.05 | 0.28 | −0.08 | 0.26 |
| PAX3 | −1.07 | 0.62 | 0.45 | 0.44 | 0.32 | HSD17B2 | 0.44 | −0.19 | −0.57 | 0.30 | 0.23 | FAM92B | 0.36 | −0.58 | −0.59 | −0.10 | −0.86 |
| SLC27A5 | −0.72 | 0.15 | 0.68 | −0.03 | 0.45 | AC025588.1 | −0.43 | 0.46 | 1.12 | 0.46 | 0.48 | AL390039.1 | 0.20 | −0.78 | −0.15 | 0.19 | 0.65 |
| CBFB | 0.38 | −0.26 | −0.40 | −0.12 | −0.12 | SMAD7 | 0.21 | −0.15 | −0.52 | −0.18 | −0.33 | CSKMT | −0.10 | −0.25 | 0.01 | 0.26 | 0.16 |
| SPRR2F | 2.93 | −3.67 | −4.28 | 0.11 | −1.40 | C9orf38 | 0.21 | −0.18 | −0.30 | −0.18 | −0.06 | LGSN | −0.28 | −0.61 | −0.89 | 0.57 | −0.16 |
| CANT1 | 0.64 | −0.30 | −0.85 | −0.10 | −0.44 | AL354794.2 | −0.63 | 1.11 | 0.40 | 0.71 | 0.10 | G40462 | 0.26 | −0.14 | −0.12 | 0.92 | 0.78 |
| SNRNP70 | −0.79 | 0.25 | 0.24 | 0.29 | 0.24 | RNU6ATAC7P | 0.95 | −0.44 | 0.45 | −0.38 | 0.10 | FAM102B | 0.07 | −0.02 | 0.09 | −0.16 | −0.22 |
| CDKN2AIP | 0.67 | −0.36 | −0.43 | −0.05 | −0.21 | NUP133 | 0.13 | −0.08 | −0.08 | 0.01 | −0.09 | SHANK2 | −0.12 | 0.23 | −0.14 | 0.09 | 0.03 |
| SNORASA | −1.12 | 0.67 | 0.63 | 0.41 | −0.13 | BCL2L15 | 0.32 | −0.30 | −0.23 | 0.34 | −0.13 | AL136298.3 | 0.21 | −0.67 | −1.20 | −0.70 | −0.28 |
| COPS2 | 0.72 | −0.30 | −0.46 | −0.14 | −0.32 | GAS6-DT | −0.39 | 0.04 | 0.20 | −0.09 | −0.35 | AL035660.2 | 0.86 | −1.43 | 1.37 | −0.78 | 1.64 |
| AL162741.1 | −1.44 | 0.25 | −0.30 | 0.70 | 0.08 | AC090617.7 | 0.67 | −0.16 | 0.20 | −0.49 | −0.11 | HELZ | 0.04 | 0.00 | −0.17 | −0.04 | −0.08 |
| NUMBL | −0.70 | 0.38 | 0.56 | −0.02 | −0.08 | AP000358.1 | −1.89 | −0.08 | 1.49 | 1.35 | 2.50 | RNU6-859P | 0.24 | −1.12 | 1.29 | −0.55 | −0.53 |
| FRMD6 | 0.63 | −0.21 | −0.17 | −0.21 | −0.26 | AC093520.2 | 1.10 | −1.34 | −1.46 | 0.00 | −1.19 | AL359976.1 | 0.30 | −0.97 | −0.67 | −0.65 | −0.92 |
| AGAP1 | −0.39 | 0.36 | 0.29 | 0.21 | 0.06 | AL110118.2 | 0.95 | −0.37 | 0.96 | −0.21 | 0.16 | LINC01793 | −0.49 | 0.32 | 0.00 | 1.21 | 0.66 |
| NBPF24 | −0.91 | 0.60 | 0.49 | 0.01 | 0.03 | AL133338.1 | −0.33 | 0.00 | 0.35 | 0.10 | 0.21 | OR2G1P | −0.64 | 0.49 | −0.74 | 0.99 | −0.32 |
| SHANK1 | −1.34 | 0.68 | 0.80 | 1.18 | 0.45 | CDH16 | 0.93 | −1.69 | −1.75 | 0.43 | 1.62 | AC121161.2 | 0.62 | −1.87 | −1.09 | 0.64 | −0.53 |
| EEF1B2P3 | 0.95 | −0.60 | −0.32 | −0.31 | −0.15 | AC091614.2 | −0.66 | 0.42 | 0.05 | 0.33 | −0.73 | G5707 | −0.18 | −0.61 | 0.12 | −0.39 | 0.23 |
| PARD3 | −0.45 | 0.49 | 0.42 | 0.27 | −0.05 | SMDT1 | −0.23 | 0.57 | 0.44 | 0.19 | −0.09 | PDRG1 | 0.05 | −0.06 | −0.08 | −0.08 | 0.06 |
| AL357078.3 | −1.56 | 0.32 | 1.69 | 0.18 | 0.36 | RNA5SP144 | −1.28 | 1.57 | 1.93 | 0.98 | 1.13 | POTEG | −0.50 | 0.35 | −0.01 | 1.63 | −0.50 |
| SNW1 | 0.43 | −0.16 | −0.42 | −0.13 | −0.34 | AL138916.2 | −0.69 | 0.17 | 0.94 | 0.30 | 1.02 | RRH | −0.13 | −0.08 | 0.67 | 0.27 | 0.47 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| MSH6 | 0.49 | −0.34 | −0.47 | −0.20 | −0.20 | B4GALNT1 | −0.50 | −0.61 | 0.34 | −0.10 | 1.08 | LINC01016 | 0.23 | −0.30 | −2.04 | 0.63 | −1.19 |
| FUT2 | 1.05 | −0.56 | −1.35 | −0.41 | −0.52 | RPS29P22 | 0.80 | 0.32 | −0.49 | 0.45 | −0.64 | G34929 | 0.20 | −1.44 | 0.41 | −0.57 | 1.06 |
| AP006621.3 | −0.97 | 0.51 | 0.73 | 0.52 | 0.59 | STX4 | −0.21 | −0.02 | −0.24 | 0.15 | 0.03 | AP001596.1 | 0.14 | −0.20 | 0.04 | 0.19 | 0.02 |
| NPRL2 | −0.70 | 0.49 | 0.32 | 0.47 | 0.14 | AC006372.3 | 0.57 | −1.02 | −0.80 | −0.76 | −0.34 | CTD-3080P12.3 | −0.35 | 0.40 | −0.85 | 0.66 | −0.61 |
| FOXN2 | 0.77 | −0.41 | −0.69 | −0.36 | −0.66 | BHMG1 | −1.17 | −1.54 | −0.74 | −1.54 | 0.35 | AL354919.1 | −0.24 | −0.08 | −1.66 | 0.54 | 0.18 |
| KRT18P4 | −1.17 | 0.27 | 0.62 | 0.29 | 0.03 | AC007785.2 | −0.39 | −0.05 | 0.70 | −0.22 | 0.50 | MTND2P16 | −0.42 | −0.18 | 0.76 | −0.31 | 0.90 |
| PLRG1 | 0.57 | −0.28 | −0.53 | −0.11 | −0.30 | GRM1 | −0.75 | 0.53 | −0.57 | 0.09 | −0.94 | RPS4XP21 | 0.82 | −0.76 | −1.24 | 0.06 | −0.31 |
| CYP27A1 | −0.96 | 0.66 | 0.81 | 0.40 | 0.37 | AC079466.1 | −0.76 | −1.41 | −0.98 | −1.35 | −1.24 | CNN3 | −0.08 | 0.23 | 0.53 | −0.09 | 0.09 |
| ORC6 | 1.12 | −1.17 | −1.44 | −0.26 | −0.31 | AC008760.2 | −0.71 | −0.60 | 0.33 | 0.64 | 0.49 | LINC02375 | 0.44 | −0.06 | −1.32 | 0.45 | −2.03 |
| MORN1 | −0.89 | 0.15 | 0.26 | 0.42 | 0.43 | AC138473.1 | −0.81 | 0.83 | 0.01 | 0.11 | −0.48 | OR4N1P | 0.70 | 0.23 | −1.09 | 0.49 | −1.21 |
| RN7SL274P | −2.87 | 0.13 | 1.38 | 2.18 | 1.74 | CCDC140 | −0.81 | −0.78 | −0.56 | −0.31 | −0.09 | AL035419.1 | −0.42 | 1.71 | 0.47 | 1.05 | −0.91 |
| PUS7L | 0.67 | −0.37 | −0.34 | −0.19 | −0.10 | BALAP2-DT | −0.23 | 0.20 | 0.16 | 0.13 | 0.05 | MIR495 | 0.84 | −0.66 | 1.86 | −1.95 | 0.18 |
| HSP90AB1 | 0.76 | −0.52 | −0.62 | −0.28 | −0.31 | AP001094.2 | −0.66 | 0.01 | 0.70 | −0.37 | −0.23 | CD163 | −0.16 | −0.22 | 0.61 | −0.24 | 0.11 |
| NSF | 0.49 | −0.15 | −0.44 | 0.01 | −0.31 | MT-TT | −0.76 | −0.12 | 0.11 | 0.37 | −0.36 | AL031846.1 | −0.41 | −0.65 | 0.50 | 0.34 | −0.09 |
| MAP2K2 | 0.36 | −0.02 | −0.38 | 0.03 | −0.29 | AC005498.3 | −0.60 | 0.18 | 0.39 | 0.76 | 0.14 | AL031864.1 | 0.35 | 0.06 | −0.34 | 0.11 | 0.33 |
| FIGNL1 | 0.76 | −0.34 | −0.40 | 0.01 | −0.13 | ARPC1B | 0.32 | −0.49 | −0.69 | −0.26 | −0.31 | AL731566.1 | 0.10 | 0.09 | 0.30 | 0.13 | 0.02 |
| DEK | 0.52 | −0.40 | −0.35 | −0.18 | −0.08 | AC105450.1 | −0.78 | 0.22 | 0.74 | 0.10 | 0.69 | PHKB | 0.03 | 0.03 | 0.01 | −0.02 | −0.01 |
| KLHL31 | −1.35 | 0.65 | 1.17 | 0.26 | 0.37 | AL596137.1 | 1.00 | −0.69 | 0.54 | −0.24 | 0.31 | AC006252.1 | −0.15 | 0.00 | 0.16 | 0.50 | 0.18 |
| ARV1 | 0.79 | −0.40 | −0.47 | −0.25 | −0.23 | AC073850.1 | 0.71 | 0.36 | −0.35 | 0.36 | −0.61 | AL139424.2 | −0.09 | 0.49 | 0.05 | 0.44 | −0.06 |
| KRT17P6 | 3.16 | −1.82 | −2.65 | −0.07 | −0.34 | ATG2A | −0.19 | 0.25 | −0.15 | 0.30 | −0.14 | RNU6-10P | 0.22 | −0.10 | −0.84 | 0.44 | 0.63 |
| AC008443.3 | −1.87 | 1.27 | 1.00 | 1.09 | 0.51 | AC090541.1 | 0.46 | −0.33 | 0.05 | −0.36 | 0.26 | AC012254.1 | −0.22 | −0.51 | 0.25 | 0.02 | 0.65 |
| RRM2B | 0.76 | −0.28 | −0.66 | −0.10 | −0.61 | CALCB | −0.67 | 0.43 | 0.93 | −0.49 | −0.12 | LCN10 | 0.30 | −0.21 | −0.64 | −0.06 | −0.26 |
| AC022898.2 | −1.33 | 0.68 | 1.90 | 0.10 | 0.41 | AC108693.1 | 0.59 | −0.33 | 0.08 | 0.30 | 0.48 | CNOT10-AS1 | 0.18 | −0.26 | −0.01 | −0.09 | −0.55 |
| LIG4 | 0.95 | −0.42 | −0.69 | −0.29 | −0.58 | PTCD1 | −0.34 | 0.26 | 0.29 | 0.17 | 0.23 | PFN1P2 | 0.10 | −0.29 | 0.36 | −0.11 | 0.50 |
| POCIA | 1.15 | −1.09 | −1.56 | −0.25 | −0.36 | HLA-E | 0.17 | −0.08 | −0.18 | −0.05 | −0.20 | MIR582 | −0.43 | −2.03 | 0.43 | −1.61 | 2.33 |
| AC116565.1 | −1.86 | 1.30 | 1.57 | 0.83 | 0.47 | NECAP1 | −0.16 | 0.13 | 0.21 | −0.01 | −0.03 | FAM92A1P2 | −0.33 | −0.15 | 0.35 | 0.29 | 0.65 |
| RAD51AP1 | 0.87 | −0.81 | −1.19 | −0.25 | −0.55 | IMPDH1P8 | −0.50 | −0.04 | −0.24 | −0.10 | 0.14 | OR52B2 | 0.46 | −0.99 | −1.71 | 0.63 | −1.20 |
| AL359710.1 | −1.03 | 0.88 | 1.17 | −0.01 | −0.23 | HDHD5-AS1 | −0.65 | −0.06 | 1.08 | 0.05 | 0.51 | OR6C7P | 0.99 | −1.86 | 0.63 | −1.05 | 2.33 |
| GRN | 0.72 | −0.28 | −0.63 | 0.10 | −0.46 | HLA-F | −0.32 | −0.27 | 0.15 | −0.32 | 0.24 | FRG2GP | 0.90 | 0.24 | 2.11 | −0.58 | −0.25 |
| IQSEC3P1 | −2.58 | 0.59 | 2.43 | −0.53 | −0.16 | AL035106.1 | 0.87 | −0.84 | −1.67 | −0.37 | −0.74 | AC090337.2 | 0.19 | −0.53 | 1.18 | −0.17 | 0.34 |
| PTEN | 0.58 | −0.22 | −0.59 | 0.01 | −0.36 | CAMK2N1 | −0.41 | 0.29 | 0.74 | 0.14 | 0.58 | LINC01965 | −0.37 | −0.15 | −1.22 | 0.72 | 0.25 |
| MAGIX | −0.82 | 0.44 | 0.55 | 0.21 | 0.22 | AC007611.1 | 0.67 | −0.10 | −0.38 | 0.28 | −0.29 | G6277 | 0.17 | −0.64 | 0.93 | −0.29 | 0.40 |
| EYS | −0.79 | 0.24 | 0.86 | 0.20 | 0.34 | MTCO2P11 | 0.39 | −0.01 | −0.02 | 0.02 | 0.28 | OR5AC2 | −0.83 | −0.53 | −1.43 | −0.85 | −1.30 |
| AC130352.1 | −1.15 | 0.65 | 0.88 | −0.28 | 0.15 | AC090912.1 | 0.48 | −0.27 | −0.61 | −0.01 | −0.30 | AC018797.2 | −0.13 | 0.10 | 0.84 | 0.17 | 0.08 |
| LDLRAD2 | −1.21 | 0.22 | 1.34 | −0.06 | 0.10 | NAIF1 | 0.17 | −0.13 | −0.43 | 0.00 | −0.27 | AC139149.1 | −0.16 | 0.44 | 0.52 | 0.04 | 0.24 |
| PHLDB1 | −1.05 | 0.30 | 0.49 | 0.29 | 0.10 | AK1 | 0.42 | 0.09 | −0.72 | −0.05 | −0.66 | LINC01621 | 0.42 | −0.60 | 2.17 | −1.44 | −0.73 |
| AC124312.2 | −1.23 | 0.56 | 1.77 | 0.27 | 0.76 | GDAP2 | 0.17 | 0.03 | −0.01 | −0.01 | −0.12 | G43621 | −0.89 | 0.14 | 1.65 | 0.54 | 3.29 |
| NCLN | 0.73 | −0.54 | −0.82 | 0.02 | 0.02 | KCNRG | −0.24 | −0.28 | 0.16 | −0.42 | 0.20 | GPS2 | 0.14 | 0.00 | 0.25 | 0.04 | 0.57 |
| MYO15A | −1.07 | 0.48 | 0.72 | 0.60 | 0.61 | CUTC | −0.15 | 0.04 | 0.07 | 0.11 | 0.09 | AC005786.4 | −0.59 | −0.97 | 1.47 | 0.00 | 1.64 |
| LRCH4 | −0.89 | 0.26 | 0.33 | 0.19 | 0.21 | PTPRN2 | −0.32 | 0.21 | 0.17 | 0.07 | −0.05 | AL607028.1 | 0.22 | −0.46 | 0.28 | 0.40 | 0.33 |
| RN7SL488P | −2.32 | 1.24 | 0.68 | 1.37 | 1.30 | AC106753.1 | −0.55 | 0.61 | −0.14 | 0.54 | −0.46 | AL008638.5 | −0.41 | −0.83 | 1.85 | −0.70 | −0.34 |
| G15649 | −2.25 | 1.31 | 3.33 | −0.10 | 0.93 | AL590762.4 | −0.70 | 0.55 | 1.45 | −0.08 | −0.25 | BEND7P1 | 0.21 | 0.69 | 0.79 | 0.60 | −0.12 |
| SMU1 | 0.55 | −0.16 | −0.39 | −0.13 | −0.37 | PRTG | −0.47 | 0.03 | 0.37 | 0.46 | 0.11 | AC034238.1 | −0.31 | −0.74 | −1.07 | 0.20 | −0.62 |
| LDB3 | −1.16 | 0.39 | 0.67 | 0.59 | −0.09 | MLLT11 | 0.27 | −0.16 | −0.05 | −0.11 | 0.07 | CIR1P2 | −0.29 | −0.66 | 1.23 | 0.23 | 1.21 |
| ACACA | 0.55 | −0.20 | −0.41 | 0.10 | −0.13 | ASB2 | −0.45 | 0.29 | 0.15 | 0.46 | −0.35 | SLFNL1-AS1 | 0.07 | −0.17 | −0.20 | −0.02 | 0.34 |
| RNF7 | 0.78 | −0.38 | −0.53 | −0.03 | −0.33 | AC009135.1 | −1.40 | −0.68 | 1.13 | −0.79 | 0.91 | OR2AJ1 | −0.35 | −0.92 | −0.18 | −1.14 | −1.11 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| LINC01254 | −1.63 | −0.45 | −0.30 | −0.16 | 0.03 | AC008687.3 | −0.74 | −0.10 | −0.14 | 0.08 | 1.04 | BX276092.7 | 0.15 | −0.76 | −1.72 | −0.38 | −0.77 |
| CATSPER2P1 | −0.76 | 0.21 | 0.59 | −0.06 | 0.42 | AC004908.2 | −0.44 | 0.29 | 0.30 | −0.07 | 0.07 | HBD | 0.38 | −0.84 | −0.89 | 0.40 | −2.02 |
| AL353149.1 | 2.37 | −0.87 | −1.97 | 0.33 | −0.55 | MIRLET7A1 | 0.50 | −0.26 | −0.14 | 0.06 | −0.03 | MCAM | −0.12 | −0.16 | −0.09 | −0.11 | −0.39 |
| NEXMIF | −1.07 | 0.15 | 0.72 | 0.17 | 0.23 | HEPH | −0.33 | 0.37 | 0.86 | −0.32 | −0.11 | SOST | 0.39 | −0.30 | −0.29 | −0.24 | 1.41 |
| ISG20L2 | 0.60 | −0.41 | −0.79 | −0.13 | −0.22 | AC012645.4 | 0.70 | −0.43 | −1.19 | −0.53 | −1.21 | RNU2-37P | 0.23 | −0.61 | 0.39 | −0.10 | 0.53 |
| RUVBL2 | 0.62 | −0.29 | −0.50 | −0.13 | −0.19 | CBWD3 | −0.25 | 0.24 | 0.42 | 0.35 | 0.35 | KCNJ4 | −0.34 | 0.64 | 1.06 | 0.21 | −0.36 |
| CYP4F24P | −2.07 | 0.21 | 0.75 | 0.89 | −0.88 | AC009123.1 | −0.82 | 0.93 | 1.78 | 0.56 | 0.37 | AC024132.1 | −0.41 | −0.75 | 1.21 | 0.03 | 0.20 |
| PCDHB15 | −1.04 | 0.83 | 0.67 | 0.45 | 0.16 | AC012467.2 | 0.34 | −0.03 | −0.36 | 0.06 | −0.11 | BOLA1 | 0.09 | −0.14 | −0.22 | 0.12 | −0.01 |
| RASIP1 | 0.68 | −0.10 | −0.72 | −0.07 | −0.33 | AC025594.2 | 0.57 | 0.08 | 0.04 | −0.44 | −0.10 | CACNA1C-IT1 | −0.70 | 0.10 | −0.47 | 0.17 | 0.83 |
| SRD5A3 | 0.78 | −0.36 | −0.37 | −0.15 | −0.13 | LINC00612 | −0.57 | 0.13 | 0.80 | −0.23 | 0.34 | AL355390.1 | 0.51 | −1.26 | −0.82 | 0.63 | −2.44 |
| SNORA63 | −0.97 | 0.54 | 0.98 | 0.16 | −0.06 | SLITRK3 | −0.88 | −0.76 | −1.03 | 0.08 | −0.53 | LINC01423 | 0.36 | −0.46 | −1.62 | −0.77 | −1.71 |
| NCKAP5-IT1 | 1.61 | −0.42 | −0.86 | −0.25 | −0.51 | LINC01347 | −0.36 | 0.24 | 0.40 | −0.11 | −0.30 | OR7E99P | 0.59 | −1.05 | 1.32 | −0.88 | 0.10 |
| KIF13A | 0.42 | −0.18 | −0.60 | −0.07 | −0.31 | AC010776.2 | −0.72 | −0.64 | 1.45 | 0.16 | 0.83 | MTND4LP13 | 0.35 | −0.53 | 1.50 | −0.65 | 1.18 |
| G14339 | 1.55 | −0.44 | −0.56 | −0.14 | −0.13 | CHFR | 0.16 | −0.21 | −0.33 | −0.07 | −0.04 | AP003072.1 | −0.70 | 0.29 | 0.97 | −0.63 | 1.57 |
| SNORA54 | −1.32 | 0.84 | 0.93 | 0.42 | −0.14 | AP001029.1 | −0.79 | 0.10 | 0.10 | 0.17 | 0.37 | AC009237.5 | −0.37 | −0.03 | 1.67 | −0.79 | 0.51 |
| ANKRD22 | 1.35 | −0.50 | −0.70 | −0.12 | −0.36 | ETFB | −0.18 | 0.28 | 0.00 | 0.17 | −0.15 | CHD4 | −0.05 | 0.07 | −0.19 | 0.24 | 0.12 |
| SARM1 | −0.98 | 0.35 | 0.82 | 0.22 | 0.25 | LINC00452 | 0.99 | −0.82 | −1.78 | −0.32 | −0.75 | AC097506.1 | −1.60 | −0.41 | 0.70 | 1.44 | 1.08 |
| MOBIA | 0.72 | −0.28 | −0.42 | −0.12 | −0.38 | MTND4P32 | −0.39 | −0.24 | 0.89 | −0.10 | 0.31 | CCDC74BP1 | −0.23 | 0.60 | 0.38 | 0.56 | 0.39 |
| SAMD4A | −1.06 | 0.17 | 0.99 | −0.33 | 0.22 | IL27RA | 0.45 | −0.62 | −0.14 | −0.43 | 0.20 | SAT2 | −0.05 | 0.14 | 0.07 | 0.03 | −0.04 |
| ARF4 | 0.80 | −0.39 | −0.43 | −0.32 | −0.38 | H2AFV | 0.15 | −0.05 | −0.04 | −0.01 | −0.06 | AF279873.3 | −0.38 | −0.93 | −0.09 | −0.32 | −0.23 |
| HINT1 | 0.73 | −0.22 | −0.49 | −0.07 | −0.36 | SLC26A4 | 0.65 | −0.71 | −0.95 | −0.08 | −0.39 | DISP3 | 0.29 | −1.46 | 0.23 | −0.34 | 1.07 |
| ATP5S | −0.42 | 0.16 | 0.42 | 0.17 | 0.24 | MT1P1 | −0.83 | −0.54 | 0.97 | −0.51 | 0.80 | AC132807.2 | −0.53 | 0.67 | 0.17 | 1.29 | 0.70 |
| AC006262.2 | −1.41 | 1.03 | 2.05 | 0.55 | 0.43 | AL162457.2 | −0.69 | 0.37 | 0.49 | 0.24 | 0.10 | RN7SL754P | 0.19 | 0.24 | −1.04 | 0.03 | −0.74 |
| CAMSAP3 | −1.06 | 0.83 | 0.49 | 0.51 | −0.18 | AC013275.1 | −1.06 | 0.15 | 0.55 | 0.72 | 0.20 | AC005393.1 | −0.34 | −0.44 | 1.06 | −0.64 | 0.71 |
| DNAJA4 | −0.53 | 0.43 | 0.39 | 0.07 | −0.07 | CTAGE11P | −0.61 | 0.81 | 0.01 | 0.62 | −0.96 | AC091738.2 | 0.33 | −1.01 | 0.01 | −1.64 | 0.62 |
| AC022098.1 | −0.81 | 0.33 | 0.78 | 0.13 | 0.40 | IPO8P1 | 1.23 | −0.05 | −0.66 | 0.02 | 0.29 | AL590434.1 | 0.32 | 0.00 | −1.69 | 0.60 | −0.17 |
| AC092902.5 | −1.07 | −0.02 | 1.44 | −0.41 | 0.50 | AL139156.3 | 0.73 | 0.65 | −1.07 | 0.66 | −0.54 | AL160287.1 | 0.22 | −1.54 | −1.67 | 0.71 | 0.48 |
| SORBS2 | −1.09 | 0.82 | 1.06 | 0.56 | 0.28 | AP000943.2 | −0.60 | 0.70 | −0.29 | 0.97 | −0.63 | RNU6-372P | 0.54 | −0.54 | 2.04 | 0.57 | 0.27 |
| RBM41 | 0.34 | −0.16 | −0.28 | 0.00 | 0.03 | FBXL15 | 0.26 | −0.12 | −0.20 | 0.14 | −0.03 | MYF5 | 0.67 | −0.96 | −0.07 | −0.77 | −1.01 |
| HIST1H3J | 2.00 | −1.41 | −1.57 | −0.31 | −0.89 | AL009174.1 | 0.42 | 0.10 | −0.38 | 0.47 | −0.71 | AC138932.5 | 0.10 | −0.06 | −0.19 | 0.19 | 0.18 |
| GSKIP | 0.81 | −0.37 | −0.54 | −0.11 | −0.59 | AC020928.1 | −0.85 | 0.33 | −0.13 | 0.54 | −0.41 | AL162730.1 | 0.50 | −0.82 | 0.68 | −0.78 | 1.03 |
| CYP4F11 | 1.58 | −1.21 | −1.31 | −0.39 | −0.66 | ASH2L | −0.11 | 0.02 | 0.03 | 0.02 | −0.05 | FAM222B | 0.03 | 0.07 | 0.17 | −0.04 | 0.06 |
| FANCI | 0.77 | −0.81 | −1.10 | −0.23 | −0.32 | HCG9 | −0.66 | −0.45 | −0.38 | 0.12 | 0.61 | C1orf141 | −0.31 | 0.04 | −1.66 | 0.91 | −0.41 |
| GRIK5 | −1.27 | 0.59 | 0.18 | −0.01 | −0.59 | AC132153.1 | −0.87 | 0.22 | 0.98 | 0.94 | 0.46 | AC107021.1 | 0.15 | −0.42 | −0.09 | −0.38 | 0.44 |
| MROH7 | −1.25 | 0.85 | 1.05 | 0.29 | 0.28 | FBXO16 | −0.60 | −0.13 | 1.11 | 0.55 | 0.87 | AC006449.6 | 0.09 | 0.00 | −0.85 | −0.01 | −0.52 |
| PCSK5 | −1.11 | 0.41 | 0.98 | 0.05 | 0.10 | RMND1 | 0.15 | −0.20 | 0.00 | −0.02 | 0.25 | IGF1 | −0.16 | 0.07 | 0.59 | 0.08 | −0.08 |
| CAND1 | 0.44 | −0.17 | −0.24 | −0.05 | −0.14 | AC110285.3 | −1.04 | 0.48 | −0.18 | 0.02 | 0.05 | AC087379.1 | 0.50 | −0.37 | −1.19 | 0.52 | −0.97 |
| RAMP2- AS1 | −1.48 | 1.08 | 1.75 | 0.74 | 0.31 | LINC01554 | −0.44 | 0.84 | 0.84 | 0.94 | 0.04 | PRDM13 | −0.44 | −0.28 | −1.09 | −1.22 | −1.65 |
| PHF8 | −0.47 | 0.17 | 0.15 | 0.09 | 0.09 | AL356414.1 | 1.67 | −1.44 | −1.57 | −1.26 | −1.36 | AC011551.1 | −0.44 | −1.77 | −0.19 | −0.08 | 2.02 |
| LINC01786 | −1.59 | 0.26 | 0.76 | 0.63 | 0.44 | BATF | 0.53 | −0.89 | −0.72 | −0.45 | −0.32 | HIST2H4B | 0.26 | −0.10 | −0.57 | −0.03 | −0.61 |
| RBAK | 0.60 | −0.19 | −0.23 | −0.04 | 0.01 | CSF3R | 0.56 | −1.01 | −0.72 | −0.42 | −1.04 | BRD3OS | −0.07 | 0.19 | −0.13 | 0.01 | −0.26 |
| OIP5 | 1.24 | −0.93 | −0.48 | −0.33 | 0.54 | RNU6-38P | −0.87 | 0.39 | 0.63 | 0.44 | −0.34 | AL135925.1 | −0.14 | 0.06 | 0.42 | 0.39 | 0.17 |
| FAM229A | −0.98 | 1.07 | 0.88 | 0.51 | −0.26 | FMC1 | −0.59 | −0.26 | 0.34 | 0.33 | 0.62 | MOBP | −0.19 | −0.23 | −0.09 | 0.30 | 0.07 |
| SHMT2 | 0.72 | −0.51 | −0.81 | −0.04 | −0.16 | MRPS31P5 | −0.36 | 0.06 | 0.48 | −0.04 | 0.15 | NDP-AS1 | 0.58 | −2.42 | 0.04 | −0.64 | 1.62 |
| SNORD116-14 | −1.64 | 1.09 | 1.60 | 0.77 | −0.11 | BRI3P1 | −0.67 | 0.61 | 1.25 | 0.48 | 0.20 | AC007537.2 | −0.24 | −0.81 | 0.38 | 0.01 | 1.25 |
| OBSL1 | −0.71 | 0.41 | 0.34 | 0.30 | 0.14 | SNORA3 | −0.57 | 0.34 | 1.00 | −0.21 | 0.97 | AC008592.5 | −0.18 | 0.77 | −0.12 | 1.12 | −0.69 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| SH3GLB2 | −0.82 | 0.64 | 0.59 | 0.45 | 0.23 | FAM181B | −0.52 | 0.31 | −0.08 | 0.47 | −0.08 | AJ011932.1 | −0.52 | 0.49 | 0.81 | −0.51 | −1.67 |
| STAT3 | 0.54 | −0.38 | −0.53 | −0.03 | −0.15 | AL450345.1 | −0.83 | 0.56 | 0.97 | 0.64 | 0.63 | RPL31P60 | 0.32 | −0.96 | −0.09 | −0.13 | −1.24 |
| DARS | 0.60 | −0.31 | −0.38 | −0.21 | −0.19 | SLC18B1 | 0.21 | −0.04 | 0.02 | 0.06 | 0.12 | CROCC2 | −0.16 | −0.05 | −0.57 | −0.02 | 0.07 |
| CRELD1 | −0.63 | 0.31 | 0.74 | 0.19 | 0.35 | AC004895.1 | −0.64 | 1.03 | 0.03 | 0.36 | 0.41 | MSL3P1 | 0.28 | 0.09 | −0.97 | 0.17 | −0.57 |
| NIPSNAP3B | −1.03 | 0.48 | 1.07 | 0.19 | 0.32 | INSIG1 | −0.39 | 0.23 | 0.34 | 0.29 | 0.53 | MIR4659B | 0.37 | 0.05 | −0.16 | −0.39 | 0.40 |
| RC3H2 | 0.45 | −0.15 | −0.17 | −0.13 | −0.18 | HSPA9P1 | −0.74 | 0.56 | 0.04 | −0.30 | −0.32 | CT55 | 0.38 | −0.35 | −0.13 | −0.82 | −0.18 |
| PDLIM3 | −1.07 | 0.53 | 0.56 | 0.06 | −0.37 | AC007563.3 | −0.89 | 0.40 | 1.50 | −0.24 | 0.74 | OR11K2P | −0.47 | 0.24 | 0.84 | 0.21 | −0.05 |
| CNTN2 | −0.93 | 0.23 | 0.60 | 0.09 | 0.37 | AL023284.3 | 0.73 | 0.36 | 0.89 | −0.36 | −0.17 | AC015908.5 | −0.46 | −0.73 | 1.52 | −0.97 | 1.31 |
| SH3BGRL2 | −1.09 | 0.94 | 1.52 | 0.34 | 0.46 | AC004233.1 | −0.95 | 0.66 | 0.09 | 1.02 | −0.23 | G14986 | 0.29 | −0.48 | 0.30 | 0.12 | −0.53 |
| INO80E | −0.81 | 0.20 | 0.38 | 0.19 | 0.19 | AC021205.3 | −0.51 | 0.11 | 1.06 | 0.14 | 0.52 | AC093850.1 | −1.14 | 0.76 | 0.57 | 0.78 | −1.01 |
| AC135626.1 | 2.23 | −0.43 | −1.57 | −0.10 | −0.85 | CFAP58-DT | 0.52 | −0.15 | −0.80 | 0.07 | −1.04 | AL590326.1 | −0.14 | −0.61 | 0.37 | 0.06 | 0.84 |
| RAB40B | −0.58 | 0.57 | 0.43 | 0.45 | 0.18 | RNU6-496P | −0.95 | 0.41 | 0.31 | 0.76 | −0.44 | DPPA3 | 0.76 | −0.54 | −0.54 | 1.61 | 1.02 |
| MIEF1 | 0.53 | −0.35 | −0.47 | −0.11 | −0.20 | CDYL | 0.15 | 0.01 | −0.33 | 0.00 | −0.30 | AC010761.4 | 0.28 | 0.24 | −1.60 | 0.37 | −0.38 |
| CYS1 | −1.29 | 0.55 | 1.76 | 0.31 | 0.81 | MTATP8P2 | −0.53 | 0.06 | 0.50 | −0.12 | 0.54 | LOX | 0.10 | 0.14 | 0.78 | −0.35 | 0.21 |
| SECISBP2 | −0.40 | 0.14 | 0.21 | 0.19 | 0.16 | ATE1-AS1 | −0.55 | 0.14 | 1.34 | −0.58 | 0.32 | SUGCT | 0.09 | −0.01 | −0.32 | −0.25 | −0.22 |
| HMGN1 | 0.56 | −0.30 | −0.34 | −0.20 | −0.15 | CCDC82 | −0.17 | −0.04 | 0.18 | −0.03 | 0.15 | MYL12BP1 | 0.16 | −0.57 | −0.66 | 0.61 | −0.04 |
| LINC01159 | −2.60 | 0.40 | 1.03 | 0.78 | 1.15 | SH2D1A | 0.69 | −0.69 | 0.74 | −0.51 | 1.21 | AL591163.1 | −0.48 | 1.56 | −1.08 | 1.59 | 0.37 |
| SEC31B | −0.87 | 0.26 | 0.61 | 0.26 | 0.26 | SLC9A3 | −0.43 | 0.31 | −0.40 | 0.66 | 0.38 | RPL21P40 | 0.52 | −0.87 | −1.32 | −0.34 | −2.38 |
| AQR | 0.44 | −0.16 | −0.33 | −0.13 | −0.29 | IQSEC1 | −0.18 | 0.05 | 0.05 | 0.01 | −0.04 | H19 | −0.11 | 0.56 | 0.24 | 0.15 | −0.46 |
| AC021752.1 | −1.56 | 0.66 | 1.26 | 0.40 | 0.24 | MCCD1 | −0.78 | 0.08 | 1.05 | 0.26 | 1.08 | RPL39P38 | 0.24 | 0.61 | −1.42 | 0.62 | −1.45 |
| AC099850.3 | 2.50 | −1.55 | −1.45 | −0.71 | −0.14 | AL157714.2 | −1.04 | −0.34 | −0.68 | −0.52 | −0.02 | RN7SL236P | −0.39 | 1.25 | 0.47 | −0.14 | −0.46 |
| RAB5A | 0.55 | −0.05 | −0.35 | 0.05 | −0.43 | ILF3-DT | −0.13 | 0.14 | 0.05 | 0.19 | 0.06 | AC006116.5 | 0.15 | −0.69 | 1.05 | −0.53 | 0.81 |
| CD300E | 1.82 | −1.58 | −1.51 | −0.78 | −1.02 | G1863 | −0.45 | 0.08 | 0.17 | −0.18 | 0.07 | OR7E59P | 0.54 | −0.90 | −1.69 | 0.38 | 1.20 |
| AL356275.1 | −1.05 | 0.33 | 1.16 | 0.13 | 0.10 | AC103591.2 | −0.69 | −0.04 | 1.29 | 0.06 | 0.65 | LINC02443 | 0.22 | −0.20 | 0.29 | −0.57 | 0.50 |
| CDC42BPG | −0.93 | 0.65 | 0.34 | 0.58 | 0.22 | AL353699.1 | −1.20 | 0.34 | −0.16 | 0.17 | −1.32 | AC093484.2 | −0.18 | −0.44 | −2.49 | −0.06 | −1.38 |
| SLC2A1 | 1.15 | −0.35 | −1.15 | 0.02 | −0.48 | STXBP1 | −0.15 | 0.18 | −0.11 | 0.10 | −0.23 | AC007346.2 | −0.26 | 0.46 | −0.57 | −0.38 | −0.16 |
| KATNBL1 | 0.33 | −0.24 | −0.18 | −0.20 | −0.12 | OR52N1 | −0.99 | 0.25 | 0.82 | −0.15 | −0.23 | ADAM30 | 0.31 | −0.63 | 0.00 | 0.03 | −0.15 |
| EIF1B-AS1 | −0.81 | 0.75 | 0.96 | 0.16 | 0.23 | AL157935.1 | −0.41 | 0.56 | 0.24 | 0.46 | 0.13 | MTMR14 | −0.03 | 0.04 | 0.04 | −0.05 | −0.07 |
| PDK4 | −1.91 | 1.50 | 1.42 | 1.18 | 0.17 | NXF3 | −0.78 | −0.46 | −0.77 | 0.75 | −0.21 | ASS1P9 | −0.62 | 0.18 | −2.26 | 0.78 | −1.62 |
| ATP6V1A | 0.69 | −0.21 | −0.54 | 0.04 | −0.44 | C7orf61 | −1.00 | 0.98 | 1.09 | −0.44 | −0.48 | LINC02456 | −0.21 | 0.09 | 1.11 | −0.02 | 0.24 |
| RP11-20312.1 | −1.39 | 0.60 | 0.73 | 0.50 | 0.09 | PTPDC1 | −0.12 | −0.01 | 0.08 | −0.01 | 0.16 | MIR4514 | 0.40 | −0.30 | −0.36 | −0.40 | −0.35 |
| ERLIN1 | 0.51 | −0.21 | −0.22 | −0.16 | −0.09 | SMAD4 | −0.14 | 0.08 | 0.26 | 0.06 | 0.13 | CCDC92 | −0.08 | 0.01 | −0.08 | −0.11 | 0.03 |
| MPV17L2 | 0.81 | −0.54 | −1.35 | 0.09 | −0.45 | AC079944.2 | 0.74 | −0.46 | −0.08 | 0.01 | −0.74 | DNER | −0.14 | 0.43 | 0.47 | 0.15 | 0.36 |
| SCYL2 | 0.59 | −0.20 | −0.46 | −0.10 | −0.32 | RCN1 | 0.24 | −0.20 | −0.07 | −0.18 | −0.24 | MAMLD1 | −0.07 | −0.06 | −0.36 | 0.15 | −0.05 |
| ITPRID1 | −1.68 | 0.57 | 1.44 | 0.65 | 0.78 | RPS10P3 | 0.85 | −0.19 | 0.15 | −0.09 | −0.38 | IFITM4P | −0.24 | 0.26 | −0.03 | 0.63 | 0.82 |
| SPTAN1 | −0.39 | 0.20 | 0.31 | −0.03 | −0.05 | RNU4-4P | 1.57 | −1.25 | −1.89 | −0.50 | −0.83 | AC245452.1 | −0.05 | −0.16 | −0.23 | 0.09 | −0.03 |
| MAOA | −1.25 | 0.66 | 0.65 | 0.55 | −0.04 | AL158212.2 | −0.75 | 1.00 | −0.14 | 0.91 | −0.32 | RN7SL254P | 0.25 | −0.75 | −0.56 | 0.23 | 0.57 |
| SKINTIL | −1.49 | 0.61 | 1.28 | 0.07 | 0.38 | EMD | 0.16 | 0.12 | −0.21 | 0.13 | −0.04 | AC010900.2 | 0.59 | −0.43 | 0.36 | −1.16 | −1.15 |
| EFHC2 | −0.96 | 0.79 | 0.90 | 0.58 | −0.03 | DTHD1 | 0.41 | 0.06 | 0.44 | −0.01 | 0.68 | NDUFB4P3 | 0.19 | −0.30 | −0.45 | −0.41 | −0.13 |
| CLUAP1 | −0.56 | 0.32 | 0.55 | 0.02 | 0.06 | NIPAL2 | 0.29 | 0.12 | 0.37 | 0.15 | −0.01 | COL9A1 | −0.23 | −0.40 | −0.55 | 0.14 | −0.17 |
| G27376 | 2.55 | −1.61 | −3.10 | −0.98 | −2.31 | G39837 | −1.04 | 0.68 | 2.09 | 0.36 | 0.44 | KRTAP4-12 | −0.73 | −0.36 | 0.30 | 0.37 | −1.32 |
| HYKK | −0.82 | 0.42 | 0.73 | 0.27 | 0.37 | KAT6A | −0.10 | 0.24 | 0.32 | −0.06 | −0.07 | AC021483.1 | −0.20 | 0.38 | 0.19 | 0.12 | 0.69 |
| LRRC17 | −1.11 | 0.77 | 1.45 | 0.13 | −0.01 | RNU6-141P | 1.49 | −1.24 | −2.06 | −0.44 | 0.12 | AF235103.1 | 0.27 | 0.58 | 0.51 | −0.20 | −0.34 |
| SERPINA9 | −1.69 | 0.20 | 1.21 | −0.35 | 0.75 | AC009549.1 | −0.69 | 0.54 | 0.77 | 0.16 | 0.04 | MIR4484 | 0.28 | −0.26 | −0.14 | 0.93 | 0.70 |
| GPCPD1 | 0.44 | −0.31 | −0.32 | −0.16 | −0.12 | ECHS1 | 0.22 | 0.01 | −0.33 | 0.06 | −0.30 | RPL3P8 | −0.55 | 0.99 | −1.85 | 1.12 | −2.31 |
| SGSM2 | −0.77 | 0.31 | 0.34 | 0.32 | 0.39 | HNRNPA1P65 | −1.54 | 0.96 | −0.90 | 1.80 | −0.38 | AC018563.1 | 0.30 | −0.38 | −2.17 | −0.01 | −1.93 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC087491.1 | -2.61 | 1.40 | 3.27 | 0.93 | 1.28 | AC106712.1 | 1.64 | -1.78 | -0.94 | -0.22 | -0.26 | RPL10P6 | 0.17 | -0.33 | 0.12 | 0.09 | -0.13 |
| ACSBG1 | -1.43 | 1.10 | 0.64 | 1.26 | 0.20 | IBA57 | -0.15 | 0.09 | -0.19 | 0.12 | -0.15 | MTCO1P7 | 0.88 | 0.84 | -2.84 | 2.09 | -1.93 |
| KIAA1217 | 0.59 | -0.23 | -0.83 | -0.02 | -0.23 | LENG9 | 0.32 | -0.42 | -0.49 | 0.19 | 0.62 | RHOQP2 | 0.19 | -0.56 | -0.41 | 0.01 | -0.25 |
| FLNB | 0.58 | -0.35 | -0.84 | -0.19 | -0.25 | STEAP2-AS1 | -0.78 | 0.04 | 0.08 | 0.25 | 0.43 | LINC01109 | -0.48 | 1.20 | -0.11 | 1.41 | -0.67 |
| OR2T29 | -4.56 | 1.03 | 3.19 | 1.97 | 1.27 | HYPK | -0.30 | 0.08 | 0.22 | 0.15 | 0.26 | AC124283.5 | 0.20 | -1.65 | -0.79 | 0.41 | 1.83 |
| GRM7 | -1.48 | 0.30 | 0.63 | 0.18 | 0.23 | FTL | -0.44 | -0.12 | 0.75 | -0.35 | 0.21 | AC025171.1 | -0.06 | -0.10 | 0.30 | -0.18 | 0.13 |
| PTK7 | 0.64 | -0.38 | -0.51 | -0.17 | -0.12 | BTBD10P2 | 0.40 | -0.12 | -0.12 | 0.04 | 0.30 | AC009120.4 | -0.29 | -1.20 | -0.17 | 0.29 | 1.19 |
| CCDC30 | -0.81 | 0.43 | 0.76 | 0.04 | 0.11 | EDNRB | -0.29 | 0.23 | 0.28 | 0.00 | 0.20 | RNU6-822P | -0.49 | 1.72 | -1.46 | 1.03 | -1.09 |
| PGM5P2 | -1.02 | 0.42 | 0.33 | -0.23 | -0.48 | MRPL34 | 0.22 | -0.13 | -0.08 | -0.09 | 0.00 | PKMP2 | 0.54 | -1.62 | -1.00 | 0.27 | -0.02 |
| DICER1 | 0.44 | -0.19 | -0.38 | -0.04 | -0.16 | PLBD2 | 0.21 | -0.16 | -0.01 | -0.29 | -0.24 | PRSS44 | -0.69 | -0.59 | 1.95 | -1.44 | 0.83 |
| PSG8 | -2.12 | 0.93 | 0.94 | -0.13 | 0.40 | CAB39P1 | 0.85 | -1.10 | -1.32 | -0.60 | -0.41 | AC005042.2 | -0.22 | 0.45 | 1.20 | 0.12 | 0.03 |
| SPATA20 | -0.72 | 0.20 | 0.39 | 0.16 | 0.19 | AP001527.2 | 0.41 | -0.28 | -0.71 | -0.09 | 0.00 | AC100836.1 | 0.45 | -0.77 | -1.85 | 1.45 | -1.93 |
| NAPG | 0.46 | -0.14 | -0.61 | -0.01 | -0.41 | HSPA8P20 | -1.29 | -0.14 | 0.65 | -0.64 | 1.08 | AC017053.1 | 0.30 | -1.64 | -3.12 | 0.71 | -1.33 |
| GMPR2 | 0.43 | -0.22 | -0.41 | -0.18 | -0.11 | DPEP2 | -0.41 | -0.08 | -0.20 | -0.15 | -0.32 | ANKRD30BP3 | -0.34 | 0.04 | -0.02 | -0.22 | -0.01 |
| SCO2 | 1.75 | -1.12 | -1.85 | -0.23 | -0.71 | C1orf50 | -0.17 | 0.07 | 0.37 | 0.06 | 0.21 | G7468 | -0.37 | 0.48 | 1.02 | 0.23 | 1.11 |
| MBOAT7 | 0.53 | -0.38 | -0.30 | -0.23 | -0.05 | INO80C | 0.21 | -0.28 | -0.44 | 0.05 | -0.14 | AC084357.2 | -0.22 | -1.07 | -0.95 | -0.34 | -0.06 |
| LINC01703 | -1.18 | 0.48 | 0.79 | 0.05 | 0.68 | IRF4 | -0.39 | -0.37 | -0.51 | -0.21 | -0.08 | BMPR1AP2 | -0.27 | 1.08 | 0.05 | 0.70 | -0.20 |
| EIF3J-DT | -0.67 | 0.37 | 0.81 | 0.18 | 0.31 | POU5F1P6 | -0.93 | 0.04 | 2.36 | -0.18 | -0.16 | CD46P1 | 0.76 | -1.34 | -0.64 | -0.62 | 1.09 |
| APRT | 0.64 | -0.16 | -0.58 | 0.04 | -0.41 | MRGPRF | -0.46 | 0.21 | 0.45 | 0.09 | -0.02 | RP11-395P13.3 | 0.61 | -0.62 | 0.07 | 1.47 | 1.96 |
| SAMSN1 | 1.76 | -1.60 | -1.14 | -0.36 | -0.36 | AC020728.1 | 0.52 | 0.43 | -0.98 | -0.02 | -1.08 | AL136442.1 | 0.24 | 0.10 | 1.13 | -0.73 | 0.17 |
| RXRB | -0.60 | 0.26 | 0.27 | 0.25 | 0.11 | DLK1 | -0.97 | 0.28 | -2.03 | 1.75 | -0.73 | AC007685.1 | 0.54 | 1.06 | 0.06 | 2.38 | -1.81 |
| RDH16 | 1.51 | -0.46 | -1.12 | 0.06 | -0.40 | LETM2 | -0.25 | 0.02 | 0.04 | -0.31 | -0.02 | CYP11B1 | 0.32 | -0.86 | 0.09 | -0.45 | -0.38 |
| AC079316.2 | 1.22 | -1.13 | -1.08 | -0.78 | -0.19 | RPS26P42 | 0.48 | 0.57 | -0.13 | 0.22 | -0.15 | AL591848.2 | 0.30 | 1.01 | 1.09 | 0.92 | 0.69 |
| MPPED2 | -1.31 | 0.41 | 0.55 | 0.45 | -0.03 | LDLRAD3 | 0.19 | -0.02 | -0.35 | 0.10 | 0.00 | AC124319.3 | 0.31 | -1.42 | 0.24 | -1.11 | 0.70 |
| AK7 | -0.94 | 0.96 | 1.28 | 0.44 | -0.11 | KCCAT333 | 0.55 | -0.49 | -0.02 | -0.34 | 0.91 | LDHAP1 | 0.42 | -1.43 | -0.32 | 0.19 | 1.06 |
| AC138123.1 | -1.70 | 1.46 | -0.09 | 0.82 | -0.30 | DNMT3A | -0.18 | -0.01 | -0.12 | -0.09 | -0.15 | AC008760.1 | -0.11 | 0.28 | -0.75 | 0.16 | -0.32 |
| ATF4 | 0.46 | -0.25 | -0.70 | -0.14 | -0.37 | G24237 | -0.44 | 0.32 | 1.18 | 0.29 | 0.49 | RNU6-1077P | -0.82 | -0.52 | 0.08 | -0.45 | -0.41 |
| CYP2C9 | -1.88 | 0.34 | 1.15 | 0.21 | 0.38 | HIST4H4 | 0.24 | -0.20 | -0.37 | 0.02 | -0.18 | AC034154.1 | -0.27 | 1.75 | -0.58 | 1.17 | -1.43 |
| AC097103.2 | -0.83 | 0.21 | 1.05 | 0.06 | 0.56 | CFAP157 | -0.37 | 0.23 | 0.14 | 0.21 | 0.50 | PRELID3BP7 | 0.93 | -0.99 | 0.93 | -0.90 | -0.45 |
| SF3B4 | 0.56 | -0.20 | -0.51 | -0.11 | -0.32 | AC011999.1 | -0.55 | 0.28 | 1.27 | 0.03 | 0.31 | KLK15 | -0.24 | -0.30 | 0.94 | 0.17 | 1.41 |
| PITPNC1 | 0.97 | -0.77 | -0.87 | -0.38 | -0.13 | AC131212.4 | -0.81 | 0.08 | -0.84 | -0.41 | -1.40 | CCNB3P1 | -0.54 | 1.07 | 0.20 | 0.34 | -1.31 |
| PABPC4 | 0.57 | -0.44 | -0.42 | -0.20 | -0.06 | AL591516.1 | -0.57 | -0.17 | 1.22 | -0.46 | 1.40 | AC012361.1 | -0.67 | -0.35 | -0.11 | 0.19 | -1.21 |
| AC007728.3 | 1.69 | -0.70 | -0.32 | -0.20 | 0.00 | FYB1 | 0.44 | -0.69 | -0.15 | -0.46 | 0.25 | GPR151 | 0.14 | -0.26 | -1.31 | -0.14 | -0.69 |
| GPATCH2 | 0.40 | -0.15 | -0.38 | -0.09 | -0.30 | KRTAP10-6 | -1.96 | 0.40 | 0.60 | -0.46 | -1.08 | ATP5A1P5 | -0.62 | -0.89 | 0.20 | 0.81 | 0.08 |
| ADAMTS10 | -1.20 | 0.37 | 1.16 | 0.23 | 0.39 | AC102945.2 | -0.34 | 0.17 | -0.01 | 0.17 | -0.18 | AL132780.4 | 0.12 | -0.16 | -0.28 | -0.50 | -0.33 |
| CSNK2A1 | 0.37 | -0.12 | -0.24 | -0.07 | -0.12 | AC133555.1 | -1.25 | -0.08 | 0.85 | -0.97 | -0.24 | AP001554.1 | -0.41 | -0.23 | 0.90 | 1.02 | 1.05 |
| SOGA1 | -0.44 | 0.03 | 0.20 | 0.01 | 0.27 | CHCHD5 | 0.24 | -0.21 | -0.42 | -0.06 | -0.33 | AKAP4 | 0.42 | -1.63 | -1.59 | 0.15 | -0.78 |
| MAPK8IP1 | -1.14 | 0.75 | 0.81 | -0.08 | 0.09 | AC006427.1 | -0.76 | -0.26 | -0.11 | 0.67 | 0.20 | AC015871.1 | 0.55 | -0.40 | -1.69 | 1.23 | -2.01 |
| PATZ1 | -0.58 | 0.44 | 0.42 | 0.11 | 0.13 | NEU4 | -0.93 | -0.70 | 0.55 | -0.08 | 0.20 | LINC02585 | 0.23 | -0.13 | 1.41 | -0.87 | 0.38 |
| AC074032.1 | -0.68 | 0.10 | 0.41 | -0.01 | 0.15 | AC011342.1 | 0.56 | -0.69 | 0.12 | -0.06 | 0.59 | ISCU | -0.05 | 0.07 | 0.29 | -0.12 | -0.03 |
| PARP1 | 0.57 | -0.37 | -0.49 | -0.15 | -0.15 | RN7SKP185 | -0.70 | 0.57 | 0.34 | 0.58 | 0.05 | AL021707.1 | -0.25 | -0.62 | 0.18 | -0.35 | 0.52 |
| AC087242.1 | -2.08 | 1.73 | 1.11 | 0.80 | 0.18 | GOLGA6L7 | -0.83 | -1.63 | 0.24 | -0.68 | 0.32 | AP000593.3 | 0.12 | 0.06 | -0.09 | -0.34 | -0.06 |
| PCK1 | -2.64 | 2.50 | 2.13 | 1.02 | -0.27 | EDEM2 | 0.14 | 0.04 | 0.23 | -0.08 | 0.06 | RRN3P2 | -0.18 | -0.50 | 0.10 | -0.54 | -0.07 |
| DNAJA2 | 0.65 | -0.27 | -0.47 | -0.14 | -0.35 | HNRNPU | 0.12 | -0.23 | -0.15 | -0.09 | 0.16 | RELL1 | 0.06 | -0.05 | 0.03 | -0.09 | -0.11 |
| CTSF | -1.13 | 0.87 | 0.96 | 0.29 | 0.09 | NOMO3 | 0.29 | -0.19 | -0.06 | -0.28 | 0.14 | AC099568.1 | -0.30 | -0.51 | 0.00 | -0.60 | 0.89 |
| PPP4C | 0.58 | -0.23 | -0.57 | -0.01 | -0.25 | FNDC8 | 0.67 | 0.72 | -2.27 | 0.59 | -2.40 | IGFN1 | -0.15 | -0.57 | -0.10 | -0.33 | 0.15 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| HIST1H2BN | 0.96 | −0.51 | −0.85 | −0.29 | −0.52 | RNU1-120P | 0.56 | −0.66 | 0.14 | −0.94 | −0.27 | AC105383.1 | −0.26 | −0.31 | −0.68 | 0.51 | −0.89 |
| RRAGA | 0.60 | −0.17 | −0.46 | −0.06 | −0.39 | MFAP2 | 0.42 | −0.01 | 0.33 | −0.78 | −0.47 | OR2AT1P | −0.28 | 0.18 | 0.52 | −0.75 | 0.21 |
| KANSL3 | −0.32 | 0.17 | 0.25 | 0.10 | 0.10 | ADAM29 | −1.11 | −0.78 | −0.69 | −0.53 | −1.29 | PRAF2 | −0.09 | 0.01 | 0.66 | −0.29 | 0.00 |
| G34277 | −1.34 | 1.01 | 1.19 | 0.30 | 0.37 | AC010082.1 | −0.91 | 0.05 | 0.51 | 0.01 | 0.05 | AL356020.1 | −0.20 | −0.81 | 0.51 | −0.96 | −0.08 |
| HNRNPA1 | 0.56 | −0.31 | −0.56 | −0.01 | −0.21 | LINC01638 | 1.13 | −0.75 | −0.54 | −0.50 | 0.91 | AC067930.5 | 0.15 | −0.25 | −1.22 | 0.01 | −0.24 |
| CRACR2B | −1.50 | 0.82 | 1.17 | 1.14 | 0.56 | AC025165.5 | 0.44 | −0.29 | −0.11 | −0.16 | −0.29 | G32125 | 0.24 | 0.02 | 0.09 | 0.88 | 0.12 |
| NDUFA6 | 0.80 | −0.36 | −0.48 | −0.34 | −0.46 | RN7SL664P | −0.48 | −0.23 | −0.61 | 0.02 | −0.38 | AC034232.2 | 0.38 | −1.31 | −0.76 | 0.22 | 0.65 |
| FAM90A2P | −2.01 | 0.66 | 1.13 | 0.15 | 0.08 | G6PC | 1.08 | −1.99 | −0.59 | −0.40 | 0.76 | AC093909.5 | −0.41 | −1.06 | −0.80 | −0.38 | 1.14 |
| E2F7 | 1.04 | −0.92 | −1.26 | −0.13 | −0.27 | AC093591.3 | −0.30 | 0.58 | 0.33 | 0.52 | 0.24 | AC090061.1 | −0.17 | −0.07 | 0.80 | 0.03 | 0.59 |
| NEGR1 | −1.25 | 0.67 | 1.65 | −0.14 | 0.40 | PGRMC2 | −0.22 | 0.34 | 0.47 | 0.27 | −0.02 | DAOA-AS1 | 0.47 | −0.35 | −0.39 | 0.52 | −0.74 |
| SLC17A7 | −1.40 | 0.77 | 1.05 | 0.70 | 0.13 | STAMBP | 0.11 | −0.08 | −0.12 | −0.03 | 0.03 | AC103706.1 | −0.15 | −0.08 | 0.09 | 0.23 | 0.43 |
| MFSD14B | 0.74 | −0.34 | −0.46 | −0.12 | −0.34 | ABCG5 | −0.52 | 0.37 | 1.11 | 0.42 | 0.38 | FAUP1 | 0.09 | 0.18 | −0.15 | 0.26 | −0.13 |
| MSRB1 | 0.94 | −0.60 | −0.86 | −0.09 | −0.48 | AC105114.2 | −0.43 | 0.11 | 0.64 | 0.13 | −0.08 | MTCYBP20 | −0.77 | 0.30 | 0.64 | −1.18 | −1.62 |
| ARF4P4 | −3.37 | 1.08 | 2.48 | 0.21 | 0.76 | AC026904.3 | −0.76 | −0.81 | 0.19 | −0.79 | 0.83 | MMP21 | −0.16 | −0.57 | −0.40 | 0.03 | 0.04 |
| CALML6 | −1.49 | 0.60 | 0.79 | 1.41 | 0.78 | AC002310.6 | −0.43 | 0.16 | 0.35 | 0.46 | 0.39 | RN7SKP258 | 0.31 | 0.14 | 0.55 | −0.26 | 0.63 |
| SF3A3 | 0.43 | −0.30 | −0.43 | −0.13 | −0.15 | AC021744.1 | −0.50 | −0.90 | −0.18 | 0.29 | 0.79 | AC097105.1 | 0.63 | −0.51 | −0.89 | 1.76 | 1.03 |
| FNTA | 0.35 | 0.00 | −0.31 | 0.09 | −0.30 | AC009152.3 | 0.31 | −0.29 | −0.06 | −0.40 | −0.19 | AC073636.1 | −0.67 | −0.46 | 2.17 | −0.28 | 2.18 |
| APP | 0.52 | −0.12 | −0.29 | −0.22 | −0.24 | CHST9 | −0.54 | −0.27 | 0.81 | 0.25 | 0.74 | AC003002.3 | 0.39 | 0.00 | 2.30 | −0.22 | 1.46 |
| G13883 | 1.97 | −1.03 | −2.37 | 0.29 | −0.62 | AC074194.1 | −0.35 | 0.09 | −0.15 | 0.17 | 0.12 | AC068760.1 | 0.27 | −0.84 | 0.12 | 0.16 | 0.71 |
| AL035563.1 | −1.00 | 0.70 | 0.32 | 0.31 | −0.04 | AC061992.1 | 0.73 | −1.67 | −1.74 | −0.73 | −0.74 | RPL23AP72 | −0.15 | −0.63 | −0.66 | 0.41 | 0.45 |
| RIC3 | −0.79 | 0.50 | 0.64 | 0.19 | 0.21 | HSPA7 | −0.34 | 0.16 | 0.58 | 0.12 | 0.27 | SNORD62 | −0.19 | −0.14 | −0.73 | −0.15 | −0.37 |
| DYSF | 1.09 | −0.84 | −0.91 | −0.49 | −0.39 | AC108059.1 | 0.67 | −0.02 | −0.41 | 0.36 | 0.33 | PROX1 | 0.11 | 0.31 | 0.37 | 0.06 | −0.13 |
| RSL24D1 | 0.69 | −0.26 | −0.46 | −0.13 | −0.33 | AC008581.2 | −1.93 | 1.23 | 0.98 | −0.37 | 0.17 | AL162632.3 | −0.23 | −0.24 | 0.20 | −0.04 | 0.07 |
| RNA5SP398 | 2.69 | −1.85 | −2.20 | −0.17 | −1.65 | AC103592.1 | −0.87 | −0.55 | 0.42 | −0.32 | −0.20 | MIR4748 | 0.54 | −0.25 | −1.78 | 0.81 | −2.45 |
| AC008127.2 | −3.19 | 0.88 | 2.78 | 1.36 | 1.34 | AL163541.1 | −0.85 | 0.86 | −1.37 | 0.96 | −1.01 | HMGB3P30 | 0.55 | −1.22 | −1.03 | 0.66 | −0.27 |
| LINC00886 | −1.10 | 0.32 | 1.29 | −0.27 | 0.24 | PRDX3P1 | 0.47 | −0.08 | −0.19 | −0.42 | −0.73 | AC112503.2 | −0.12 | −0.11 | 0.95 | 0.01 | 0.69 |
| PPP4R3A | 0.37 | −0.03 | −0.29 | −0.01 | −0.21 | AC004264.2 | 0.53 | −0.84 | 0.03 | 0.10 | 0.29 | AC254633.1 | 0.16 | 0.26 | −0.10 | 0.51 | −0.41 |
| HELZ2 | 0.88 | −0.89 | −1.54 | −0.22 | −0.65 | AC009041.2 | −0.59 | 0.44 | 0.26 | 0.45 | 0.56 | AC016597.1 | 0.14 | −0.08 | 0.37 | −0.60 | −0.37 |
| KLHDC7B | 2.23 | −1.97 | −1.85 | −0.64 | −0.53 | FAM120B | −0.11 | 0.03 | 0.13 | −0.08 | 0.12 | AL139005.1 | 0.38 | −0.70 | 1.55 | 0.03 | 0.23 |
| AL512658.2 | −2.03 | 0.97 | 0.30 | 0.65 | 0.28 | BATF3 | 0.54 | −0.73 | −0.33 | −0.37 | 0.38 | LINC01415 | −0.14 | −0.03 | −0.31 | −0.61 | −0.40 |
| BEST4 | −1.42 | 0.54 | 1.11 | 0.08 | 0.60 | CEACAMP3 | 1.64 | −0.93 | −1.26 | 0.88 | 1.19 | AC020978.2 | −0.24 | 0.17 | 0.84 | −0.12 | 0.42 |
| FAM25BP | 2.17 | −0.63 | −1.55 | −0.83 | −1.84 | DCC | −0.57 | 0.00 | −0.66 | 0.10 | −0.70 | RNU7-4P | −0.32 | −0.16 | 0.51 | 0.84 | 0.79 |
| AXIN2 | −0.78 | 0.61 | 0.71 | 0.48 | 0.36 | G15373 | −0.80 | 1.06 | 0.70 | 0.99 | −0.11 | CTXN1 | −0.13 | 0.39 | 0.35 | 0.29 | −0.68 |
| SIPA1L3 | −0.54 | 0.36 | 0.25 | 0.18 | 0.17 | MIR4782 | −0.66 | −0.23 | 0.46 | 0.01 | 0.62 | AC091917.2 | −0.72 | −1.24 | 0.51 | −1.00 | 0.99 |
| AC010605.1 | −1.32 | 1.20 | 1.04 | 0.88 | 0.32 | R3HDM2P1 | −1.28 | −0.25 | −0.23 | 0.52 | −0.23 | KRTAP5-8 | −0.30 | 1.15 | 0.19 | 0.52 | 0.45 |
| FLNA | 0.52 | −0.48 | −0.87 | −0.20 | −0.46 | LINC01165 | −0.86 | −0.94 | −0.07 | 0.75 | 1.35 | C4B | −0.20 | 0.15 | −0.14 | 0.16 | −0.10 |
| AC116345.1 | −1.52 | 1.08 | 1.67 | 0.21 | 0.30 | AP003396.3 | 0.79 | −0.24 | −0.39 | −0.51 | −0.54 | AHSG | −0.36 | 1.19 | −0.09 | 1.22 | −1.25 |
| FAM189B | 0.59 | −0.22 | −0.57 | 0.14 | −0.19 | RPUSD1 | 0.34 | −0.18 | −0.67 | 0.24 | 0.03 | ACA59 | 0.17 | −0.26 | 0.19 | −0.45 | −0.21 |
| DNM1P46 | −1.24 | 0.48 | 0.95 | −0.05 | 0.45 | FOXH1 | −0.64 | 0.07 | 0.01 | 0.89 | 1.04 | AL158210.1 | 0.31 | −1.26 | −1.48 | −0.24 | 0.21 |
| LINC01836 | −1.52 | 0.47 | 0.32 | 0.88 | −0.02 | AC099804.1 | 0.32 | −0.39 | −0.28 | −0.17 | 0.13 | METTL25 | −0.05 | 0.09 | 0.08 | 0.13 | 0.10 |
| SNORD116-24 | −1.55 | 1.23 | 1.44 | 0.86 | −0.39 | AC016737.1 | 0.42 | −0.62 | −0.41 | 0.09 | 0.65 | BNC2-AS1 | −0.15 | 0.25 | 0.60 | 0.23 | 0.80 |
| GRIA1 | −1.76 | 0.86 | 1.66 | 0.04 | −0.08 | ABCD1 | −0.29 | −0.05 | −0.03 | 0.03 | 0.25 | AC024937.1 | −0.29 | −1.10 | 0.22 | 0.63 | 2.09 |
| NUDCD1 | 0.71 | −0.43 | −0.43 | −0.33 | −0.14 | BOLA2B | 1.10 | 0.13 | −0.44 | −0.69 | −0.27 | RPL23AP71 | −0.86 | −0.48 | −0.08 | −0.29 | −0.07 |
| SEC24D | 0.52 | −0.32 | −0.20 | −0.45 | −0.17 | AP001646.2 | 1.13 | −2.35 | −0.08 | 1.38 | 1.64 | AC021755.1 | 0.55 | 0.17 | −1.52 | 2.61 | −1.11 |
| P2RX6 | −1.63 | 1.04 | −0.30 | 0.64 | −0.36 | LINC01344 | −0.56 | −0.29 | −0.42 | 0.65 | 0.78 | GNPAT | −0.04 | 0.03 | 0.20 | 0.05 | 0.18 |
| DHRS1 | 0.72 | −0.11 | −0.65 | 0.12 | −0.49 | FRYL | 0.11 | 0.05 | 0.02 | 0.00 | −0.06 | G40005 | 0.93 | 0.21 | 0.61 | 2.21 | 0.17 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| G10803 | 3.22 | −0.95 | −1.06 | −0.17 | −0.13 | RN7SKP103 | 1.42 | −0.95 | −0.57 | −0.28 | 0.37 | AFM | −0.27 | 0.08 | −1.39 | 0.31 | −1.21 |
| AC092431.2 | 1.62 | −0.94 | −0.43 | −0.18 | 0.71 | AC090971.3 | 0.37 | −0.06 | −0.36 | −0.11 | −0.26 | C7orf71 | 0.18 | −0.17 | −0.56 | −0.19 | −0.05 |
| CHST11 | 0.96 | −0.91 | −0.73 | −0.55 | −0.24 | LINC00322 | −1.78 | −0.26 | 0.07 | 0.09 | −0.10 | AL358234.1 | −0.53 | −0.61 | 0.04 | 0.57 | −0.32 |
| MTFR2 | 0.86 | −1.12 | −0.76 | −0.29 | 0.12 | CMTM2 | −0.54 | 0.30 | −0.44 | 0.36 | −0.56 | RPS6KL1 | −0.07 | 0.22 | −0.10 | 0.25 | 0.02 |
| HSPD1 | 0.77 | −0.62 | −0.63 | −0.25 | −0.05 | NKAPL | −0.40 | 0.40 | 0.80 | −0.13 | 0.05 | FAM167A | 0.12 | 0.56 | 0.01 | 0.54 | −0.34 |
| AC011444.4 | −1.49 | −0.21 | 0.77 | −0.76 | 0.40 | AC009879.1 | −1.13 | 1.10 | 0.17 | 0.36 | −0.32 | AC024224.2 | 0.57 | −1.00 | 1.04 | 0.00 | 2.62 |
| AL137145.1 | −0.99 | 0.51 | 0.39 | 0.12 | −0.08 | CYP4A27P | −1.38 | 0.10 | 3.04 | −0.01 | −0.08 | CCNO | −0.12 | 0.20 | 0.04 | 0.86 | 0.55 |
| AC104232.2 | 0.94 | −0.49 | −0.47 | −0.23 | −0.04 | CASP10 | 0.17 | −0.21 | −0.13 | 0.10 | 0.07 | KRT18P41 | 0.63 | −0.91 | 0.08 | 0.46 | 2.16 |
| ATP5F1D | 0.58 | −0.24 | −0.32 | −0.17 | −0.20 | SNORD96B | 1.01 | 0.20 | −0.26 | 0.39 | −0.06 | MTRNR2L6 | −0.21 | −0.50 | −0.83 | 0.85 | 0.02 |
| DNAJC7 | 0.48 | −0.21 | −0.59 | −0.09 | −0.34 | AC011632.2 | −1.28 | 1.30 | 0.12 | 0.60 | −0.38 | AL391069.3 | −0.51 | −0.17 | −0.85 | −1.49 | −2.12 |
| KRTAP3-3 | −3.52 | 2.44 | 3.05 | 0.40 | −0.93 | LINC01353 | 0.84 | −0.98 | 0.30 | −0.25 | 0.83 | RPL23AP59 | 0.42 | −0.83 | −1.82 | −0.50 | −2.52 |
| DTX1 | −1.27 | 0.89 | 0.95 | 0.59 | 0.01 | G31075 | −0.73 | −0.18 | 1.73 | −0.18 | 0.99 | HLX | −0.09 | −0.51 | 0.17 | −0.14 | 0.54 |
| ENGASE | −0.88 | 0.35 | 0.24 | 0.34 | 0.13 | RNA5SP481 | −0.91 | −0.26 | −0.61 | 1.28 | −0.49 | AL358334.2 | 0.19 | −0.31 | −0.61 | −0.31 | −0.10 |
| RELN | −1.23 | 0.78 | 1.20 | 0.48 | 0.26 | AC021678.3 | 1.37 | −0.67 | 0.59 | −0.31 | 1.00 | AL513190.1 | −0.15 | 0.19 | 0.77 | −0.15 | 0.21 |
| ARPP19 | 0.68 | −0.21 | −0.60 | −0.07 | −0.48 | AC087239.1 | 0.60 | −0.39 | −1.11 | 0.10 | 0.13 | MTATP6P16 | 0.39 | −0.17 | −0.55 | −0.48 | −0.05 |
| LYZ | 1.50 | −1.15 | −0.46 | −0.31 | 0.25 | ADNP2 | 0.16 | −0.08 | −0.21 | 0.13 | −0.03 | PCTP | −0.08 | 0.02 | 0.20 | 0.03 | 0.39 |
| LINC02018 | −1.27 | 0.59 | 1.57 | 0.56 | 0.68 | AC073215.1 | 0.59 | 0.05 | −0.60 | 0.45 | 0.67 | LINC00427 | −0.20 | −0.37 | 1.01 | 0.34 | 0.95 |
| MICU3 | −0.99 | 0.45 | 0.93 | 0.02 | 0.09 | ADCK5 | −0.26 | −0.02 | −0.17 | 0.36 | 0.29 | SLC25A14P1 | 0.13 | 0.22 | −0.12 | 0.41 | −0.20 |
| SNHG28 | −0.92 | 0.53 | 0.62 | 0.28 | 0.35 | AC021205.1 | −0.83 | 0.29 | 0.46 | −0.09 | 0.98 | BNIP3P11 | −0.12 | 0.16 | 0.45 | −0.17 | 0.45 |
| DTNA | −1.06 | 0.49 | 0.80 | 0.22 | 0.32 | EPHA5-AS1 | −0.79 | 0.36 | −0.36 | 0.59 | −0.12 | AC002395.1 | 0.38 | −0.09 | 1.49 | −0.88 | −0.44 |
| MINPP1 | 0.67 | −0.19 | −0.08 | −0.10 | −0.19 | CHST10 | 0.33 | −0.13 | −0.34 | −0.06 | −0.03 | AC118282.3 | 0.38 | −0.65 | 0.08 | 0.87 | 0.97 |
| AC022165.1 | 1.85 | −1.13 | −1.08 | −0.17 | 0.19 | ANAPC10 | 0.24 | −0.22 | −0.15 | −0.04 | 0.00 | PRR23B | −0.48 | −1.01 | −0.17 | −0.38 | 1.54 |
| LINC02323 | 1.82 | −0.99 | −2.63 | −0.42 | −1.27 | LTO1 | −0.17 | 0.09 | 0.40 | 0.08 | 0.32 | AC104667.2 | −0.27 | 0.52 | −0.96 | 0.76 | −0.67 |
| AC108734.4 | −1.47 | 1.05 | 1.74 | −0.36 | −0.55 | AC138305.3 | 1.01 | −1.94 | 0.67 | −0.34 | 1.35 | SAP18 | 0.05 | 0.03 | 0.09 | −0.01 | −0.10 |
| PHF2 | −0.44 | 0.22 | 0.17 | 0.17 | 0.13 | GLS | 0.26 | −0.10 | −0.04 | −0.23 | 0.03 | AC048347.1 | 0.67 | 0.38 | −0.80 | 1.67 | −0.41 |
| SKA3 | 1.28 | −1.04 | −1.53 | −0.67 | −0.80 | RPS4XP17 | −0.34 | −0.18 | 0.14 | 0.09 | 0.36 | AC004951.4 | −0.19 | −0.39 | 1.89 | −0.43 | 1.17 |
| SDC1 | 1.22 | −0.27 | −0.82 | −0.13 | −0.48 | PCDHA7 | −1.24 | 0.62 | −0.18 | 1.92 | −0.69 | NKX2-4 | −0.62 | −0.83 | −0.98 | 0.94 | −1.49 |
| RAB40C | −0.84 | 0.77 | 0.90 | 0.35 | 0.08 | AC011853.1 | 0.85 | 0.82 | 0.74 | 0.02 | −0.83 | LINC01163 | 0.33 | −0.89 | −1.14 | −0.12 | −0.27 |
| PRKCI | 0.69 | −0.04 | −0.33 | 0.01 | −0.27 | ACTG1P18 | −0.71 | −0.19 | −0.45 | 0.76 | −0.08 | RNU7-138P | 1.17 | −1.11 | −0.71 | 0.03 | 2.21 |
| PAFAH1B2 | 0.57 | −0.25 | −0.32 | −0.23 | −0.12 | AC012313.10 | 1.02 | −0.79 | 0.31 | 0.01 | 1.60 | AC130456.7 | −0.75 | −0.38 | 0.86 | −0.74 | 1.29 |
| RWDD4P2 | 1.46 | −0.47 | −0.67 | −0.62 | −0.19 | AL354811.1 | −1.30 | −0.62 | 0.82 | −1.20 | 0.09 | SPDYE2 | 0.13 | 0.09 | 0.28 | 0.10 | 0.26 |
| LINC01695 | −1.35 | 0.63 | 0.93 | 0.27 | 0.24 | RAB13 | 0.33 | −0.44 | −0.17 | −0.28 | −0.02 | FAM13B | −0.04 | 0.08 | 0.01 | 0.07 | 0.04 |
| LDLR | 1.10 | −0.75 | −1.51 | 0.10 | −0.80 | AC024337.2 | −0.68 | 0.62 | 1.18 | −0.13 | −0.02 | AC073089.1 | 0.19 | −0.98 | 0.27 | −0.54 | 0.81 |
| LSM4 | 0.60 | −0.20 | −0.42 | −0.08 | −0.28 | RNU6-911P | −1.57 | 1.15 | −0.27 | 0.26 | −1.13 | AC093581.1 | 0.75 | 0.70 | −1.50 | 1.47 | −0.54 |
| G22770 | −2.07 | 0.87 | 1.86 | 0.66 | 1.57 | SATL1 | −0.55 | −0.53 | −0.43 | 0.08 | −0.07 | AP000802.1 | 0.46 | −0.44 | 1.25 | −1.04 | 1.10 |
| PUS3 | 0.73 | −0.37 | −0.33 | −0.36 | −0.26 | RAD50 | 0.26 | −0.06 | 0.08 | −0.07 | 0.05 | AC104590.1 | −0.17 | 0.26 | 0.30 | 0.40 | 0.15 |
| DHRS7 | 0.71 | −0.40 | −0.76 | −0.22 | −0.45 | LINC00165 | 1.11 | −2.01 | −0.98 | −0.24 | 1.20 | AC090286.2 | 0.08 | −0.26 | −0.33 | 0.05 | 0.20 |
| SPAG16 | −0.66 | 0.39 | 0.84 | 0.13 | 0.12 | AL161652.1 | −0.67 | 0.79 | −1.30 | 0.04 | −1.17 | AF038458.3 | −0.44 | 1.57 | 0.14 | −0.20 | −0.97 |
| EIF2B2 | 0.48 | −0.20 | −0.43 | −0.03 | −0.14 | EPHA2 | 0.34 | −0.12 | −1.06 | 0.09 | −0.62 | AL034418.1 | −0.15 | 0.06 | −0.08 | 0.02 | −0.68 |
| HSD17B10 | 0.77 | −0.27 | −0.23 | −0.18 | −0.13 | G10272 | −0.43 | 0.41 | 0.42 | 0.91 | 0.69 | G34112 | 0.27 | 0.21 | −0.02 | 0.24 | 1.09 |
| RFWD3 | 0.65 | −0.39 | −0.64 | −0.11 | −0.24 | HMGB1P20 | 0.31 | −0.21 | −0.21 | −0.17 | −0.24 | AC079336.2 | 0.11 | 0.07 | 0.76 | −0.23 | 0.42 |
| NEXN | −0.99 | 0.37 | 0.75 | 0.04 | −0.29 | AC126323.6 | −1.22 | 0.46 | −0.96 | 0.85 | −0.52 | AC061975.9 | −0.38 | −0.67 | −1.10 | 0.10 | 0.55 |
| DAPK1 | −0.95 | 0.36 | 0.66 | −0.06 | 0.15 | MIRLET7C | −0.85 | 0.91 | 0.53 | 0.51 | 0.02 | AC009145.3 | 0.17 | 0.42 | −0.01 | 0.47 | 0.28 |
| CHCHD1 | 0.58 | −0.30 | −0.35 | −0.11 | −0.08 | MIR5706 | 0.57 | −0.07 | −0.38 | −0.21 | −0.49 | GEMIN8P4 | 0.16 | 0.11 | −1.10 | 0.38 | −0.17 |
| SKOR1 | −1.36 | 0.87 | 0.84 | 0.97 | 0.62 | AC005828.2 | 0.52 | −0.34 | −0.31 | −0.27 | 0.12 | AL512593.1 | 0.12 | 0.05 | −0.45 | 0.11 | −0.01 |
| DNAJC27-AS1 | −1.08 | 0.27 | 0.74 | 0.13 | 0.19 | MAN1B1 | −0.12 | 0.09 | 0.17 | 0.06 | 0.17 | A2M | 0.10 | 0.14 | 0.63 | −0.22 | −0.21 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| RTCB | 0.58 | −0.15 | −0.54 | 0.04 | −0.41 | AL365226.2 | −0.85 | 1.72 | 0.82 | 0.87 | −0.51 | AL158211.5 | −0.32 | 0.49 | 0.18 | −0.40 | −0.43 |
| FGD1 | 0.46 | −0.24 | −0.70 | 0.06 | −0.20 | C12orf80 | 0.61 | 0.75 | −0.91 | −0.05 | −1.33 | PPIAP73 | 0.29 | 0.04 | −1.97 | 0.60 | −3.16 |
| DENND6A | 0.34 | −0.21 | −0.14 | −0.07 | −0.02 | MIR1273F | −0.70 | 0.21 | 0.25 | 0.36 | 0.21 | AC078842.2 | −0.17 | 0.12 | 0.56 | 0.23 | 0.13 |
| AC011752.1 | −2.51 | 0.92 | 1.04 | 1.34 | 0.59 | AL356390.1 | −0.77 | −0.81 | 0.17 | −0.27 | 0.40 | PPIAP54 | −0.28 | −0.37 | −1.17 | 0.79 | 0.51 |
| MAPK6P3 | 0.73 | −0.60 | −0.83 | −0.10 | −0.08 | KLHL3 | −0.20 | 0.22 | 0.39 | 0.21 | 0.10 | AP001619.1 | 0.15 | −0.94 | −0.46 | 0.31 | 0.78 |
| API5 | 0.61 | −0.30 | −0.31 | −0.18 | −0.18 | MIR5692C2 | 1.11 | 0.24 | 0.86 | −0.14 | 0.51 | RP11-782C8.3 | 0.27 | −0.12 | 0.24 | −0.41 | −0.18 |
| FMN1 | −0.72 | 0.47 | 0.27 | 0.33 | 0.13 | FOXCUT | −0.84 | 1.03 | 0.51 | 1.07 | 0.25 | OR5AU1 | −0.23 | −0.77 | −1.67 | 0.13 | −1.13 |
| CLPX | 0.52 | −0.21 | −0.33 | −0.05 | −0.23 | EGOT | −0.46 | −0.03 | −0.63 | −0.10 | 0.12 | AL592424.1 | 0.19 | −0.88 | −0.57 | 0.42 | 0.28 |
| MORF4L2 | 0.50 | −0.33 | −0.52 | −0.20 | −0.37 | AL022323.1 | 0.33 | −0.03 | 0.01 | −0.16 | 0.00 | OTOG | −0.28 | −0.58 | −1.09 | 0.14 | −0.64 |
| IDNK | −0.51 | 0.25 | 0.50 | 0.04 | 0.22 | RNU2-18P | −1.07 | 0.54 | 1.10 | 0.43 | 1.45 | RN7SL278P | −0.44 | 0.03 | −0.11 | 0.11 | 0.84 |
| SLC25A29 | −0.98 | 0.62 | 1.09 | 0.44 | 0.54 | SNX19 | 0.09 | −0.09 | −0.17 | 0.03 | 0.01 | DCP1A | 0.03 | 0.05 | 0.04 | −0.11 | −0.13 |
| IFRD2 | 0.74 | −0.62 | −1.07 | −0.04 | −0.13 | AL583834.1 | −1.17 | 0.78 | 1.94 | 0.21 | 1.92 | C17orf102 | −0.36 | 0.26 | −1.39 | −0.10 | −0.49 |
| PCGF3 | −0.49 | 0.24 | 0.21 | 0.11 | 0.08 | FABP7P2 | −1.01 | 0.40 | 1.11 | −0.34 | −1.08 | AC079298.2 | −0.47 | 2.36 | −0.53 | 1.32 | −1.98 |
| PLGRKT | 0.76 | −0.37 | −0.48 | −0.28 | −0.25 | AC035139.1 | 0.88 | −2.00 | −0.83 | −0.61 | 0.63 | SLC2A2 | −0.25 | −0.77 | 0.96 | 0.47 | 0.62 |
| MFAP4 | −1.40 | 1.30 | 2.45 | −0.01 | 0.08 | AC012613.2 | −0.58 | 0.56 | 0.46 | −0.15 | −0.20 | KRIT1 | −0.05 | 0.09 | 0.13 | 0.08 | 0.12 |
| NUP58 | 0.54 | −0.36 | −0.36 | −0.18 | −0.08 | HM13-AS1 | −0.70 | 0.28 | 0.44 | −0.62 | −0.32 | AC084128.1 | 0.37 | −0.92 | −0.58 | −0.29 | 1.47 |
| EPN2 | −0.73 | 0.59 | 0.67 | 0.38 | 0.23 | RPLP1 | 0.25 | 0.13 | 0.12 | 0.05 | −0.36 | AL157400.4 | −0.14 | −0.20 | 1.38 | 0.00 | 0.32 |
| PINX1 | 0.69 | −0.51 | −0.69 | −0.22 | −0.09 | GPR108 | −0.13 | 0.21 | −0.04 | 0.16 | −0.12 | RNU7-163P | 0.41 | 0.62 | 0.44 | 0.10 | 0.30 |
| ICA1L | −0.62 | 0.54 | 0.33 | 0.38 | −0.16 | AC008406.2 | 1.75 | −0.32 | −2.20 | −0.37 | −2.26 | RASGRF1 | 0.15 | −0.60 | −0.50 | −0.04 | 0.15 |
| HAL | 1.42 | −0.48 | −0.34 | 0.20 | −0.37 | N4BP2L2-IT2 | −0.22 | 0.42 | 0.47 | 0.14 | −0.03 | GALP | 0.91 | −1.16 | −1.65 | −0.62 | 0.20 |
| CYP4Z2P | −1.49 | 0.42 | 0.78 | 0.51 | 1.16 | AC018730.1 | −2.06 | −0.58 | 1.42 | 0.93 | 1.03 | AC008875.1 | 0.29 | −0.83 | −0.77 | 0.33 | −0.09 |
| AL603750.1 | −1.50 | 0.51 | 1.70 | −0.14 | 0.68 | MEMO1P1 | 0.44 | 0.12 | −0.24 | 0.18 | −0.39 | KRTAP2-4 | −1.56 | 1.06 | 3.36 | −0.37 | −2.01 |
| ALAD | −0.49 | 0.37 | 0.37 | 0.29 | 0.05 | PPP1R13L | −0.25 | 0.37 | −0.02 | 0.35 | 0.04 | SPDYE17 | −0.16 | 0.02 | 0.26 | −0.40 | 0.22 |
| AL078581.1 | −1.80 | 0.32 | 1.82 | −0.32 | 0.55 | AC018643.1 | −1.01 | 0.54 | −0.22 | −0.58 | −0.87 | PPM1B | −0.05 | 0.03 | 0.09 | 0.36 | 0.26 |
| AL157996.1 | −1.63 | 0.83 | 0.88 | 0.34 | −0.19 | GNAT1 | −0.74 | 0.84 | −1.88 | 0.68 | −0.13 | CHMP4A | −0.10 | −0.05 | 0.65 | −0.11 | 0.35 |
| CISD1 | 0.92 | −0.53 | −0.41 | −0.27 | −0.04 | RN7SL798P | 0.90 | −0.41 | −0.77 | −0.19 | −0.62 | AC008738.1 | −0.51 | −0.12 | −0.20 | 0.41 | 1.30 |
| CTNNA1 | 0.42 | −0.13 | −0.48 | −0.02 | −0.34 | AC002094.5 | −0.63 | 0.28 | −0.13 | 0.06 | 0.14 | CTBP2P1 | 0.36 | −1.70 | −0.50 | −0.37 | −0.30 |
| NCOA3 | 0.39 | −0.06 | −0.29 | 0.03 | −0.19 | AC005229.1 | 0.48 | −0.02 | 0.41 | −0.35 | −0.41 | LDHAL6CP | 0.34 | −1.23 | 0.25 | 1.04 | −1.10 |
| SPINT4 | −1.99 | 2.00 | 1.83 | 1.31 | −0.67 | AL357140.4 | 0.54 | −0.26 | −0.51 | −0.22 | −0.29 | IGKV1-12 | 0.79 | −0.22 | −1.23 | 0.98 | −2.38 |
| SNORD116-6 | −1.63 | 1.17 | 1.70 | 0.62 | −0.36 | AL138688.2 | 0.62 | −0.82 | 0.27 | 0.26 | 1.20 | RHCE | 0.12 | −0.60 | 0.40 | −0.10 | 0.66 |
| CRMP1 | −0.51 | 0.26 | 0.12 | 0.06 | 0.01 | C19orf67 | −0.53 | 0.78 | 0.26 | 0.54 | 0.10 | BRWD3 | 0.03 | 0.11 | 0.18 | 0.08 | 0.05 |
| RNVU1-7 | −1.57 | 0.37 | 0.92 | 0.28 | −0.04 | AC024475.4 | 0.90 | −1.53 | −1.78 | 1.13 | 1.13 | RN7SL830P | −0.63 | −0.14 | 1.32 | 1.72 | 1.09 |
| SLC2A4RG | −0.61 | 0.35 | 0.30 | 0.24 | 0.11 | LYG2 | −0.40 | 0.54 | 0.31 | 0.05 | 0.36 | DNAJC19 | 0.06 | −0.06 | 0.23 | −0.20 | 0.07 |
| MFAP1P1 | −1.31 | 0.04 | 0.93 | 0.40 | 0.54 | MRPL46 | 0.26 | −0.01 | −0.02 | 0.18 | −0.05 | ARHGEF7-AS1 | −0.24 | −1.17 | 1.77 | 0.96 | 1.64 |
| ITGBL1 | −1.18 | 1.21 | 1.63 | −0.01 | −0.11 | AP001825.1 | −1.45 | 0.60 | 1.59 | −1.25 | 0.92 | HNRNPH1P1 | 0.06 | −0.20 | 0.11 | 0.03 | −0.08 |
| AC104781.1 | 2.40 | −0.20 | −1.06 | −0.04 | −1.37 | AC011458.1 | −0.68 | 0.04 | −0.11 | −0.41 | 0.50 | G35308 | −0.63 | −0.34 | −1.50 | −0.29 | −0.85 |
| MPDZ | −0.79 | 0.37 | 0.93 | 0.10 | 0.05 | KBTBD11 | 0.38 | −0.35 | −0.36 | −0.15 | −0.31 | AC025171.4 | 0.13 | −0.08 | 0.57 | −0.28 | 0.13 |
| S100A10 | 0.96 | −0.65 | −1.04 | −0.38 | −0.50 | RNU6-8 | 0.76 | −0.42 | 0.47 | −0.57 | −0.39 | AC233728.1 | −0.23 | 0.79 | 1.69 | −0.17 | 0.39 |
| SDR42E2 | −1.35 | 0.77 | 0.60 | 0.84 | 0.65 | AC032011.1 | −0.77 | 1.59 | −0.95 | 0.24 | −1.48 | AC079600.3 | −0.16 | −0.34 | 0.29 | −0.63 | 0.17 |
| LINC01697 | −1.35 | 0.56 | 0.98 | 0.56 | 0.64 | CSPG4P13 | −0.69 | −0.22 | 0.95 | −0.08 | 0.11 | AC005519.1 | −0.12 | −0.06 | 0.35 | −0.10 | 0.02 |
| MYO15B | −1.04 | 0.26 | 0.74 | 0.19 | 0.38 | SBK3 | 1.19 | −0.83 | −1.67 | 0.42 | −0.95 | SHLD1 | 0.08 | −0.13 | −0.24 | 0.17 | −0.08 |
| RPL35 | 0.74 | −0.34 | −0.42 | −0.28 | −0.51 | AC104058.1 | −0.52 | 0.57 | 1.25 | −0.04 | 0.77 | AC003101.2 | 0.16 | −0.57 | 0.27 | −0.16 | 0.86 |
| NHLRC3 | −0.51 | 0.24 | 0.55 | 0.08 | 0.23 | SLC25A26 | −0.16 | 0.07 | −0.03 | 0.20 | −0.10 | GOLGA8UP | −0.18 | 0.33 | −0.35 | −0.36 | −0.38 |
| HIST1H1D | 1.04 | −0.86 | −1.36 | −0.04 | −0.39 | RPS3P2 | 0.41 | −0.32 | −0.04 | −0.35 | 0.12 | CYP2R1 | 0.06 | 0.06 | 0.32 | 0.12 | 0.18 |
| OGG1 | −0.51 | 0.16 | 0.47 | −0.05 | 0.21 | CAPNS2 | 0.42 | 0.43 | 0.09 | 0.42 | −0.38 | AC074029.4 | 0.48 | 0.04 | −1.13 | 0.28 | −1.66 |
| AC006001.3 | −0.60 | 0.23 | 0.32 | 0.07 | 0.22 | PIGT | −0.11 | 0.08 | 0.16 | −0.20 | −0.11 | AL109804.1 | −0.29 | −0.93 | 0.60 | −0.57 | 0.82 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC003973.3 | −1.27 | 0.74 | 1.16 | 0.10 | 0.45 | BRDT | −0.72 | −0.01 | −0.03 | 0.10 | 0.85 | LINC02530 | −0.48 | −0.41 | −0.92 | 1.48 | 0.55 |
| KRT8P26 | −1.90 | 0.81 | 1.79 | 1.10 | 0.56 | FAM213AP1 | 0.68 | −0.84 | −0.98 | −0.14 | −0.02 | ETV3L | 0.37 | −0.35 | −1.88 | −0.90 | −1.21 |
| CDK4 | 0.60 | −0.33 | −0.14 | −0.09 | −0.05 | MFSD6 | 0.24 | 0.19 | 0.07 | 0.05 | −0.26 | AC087623.2 | −0.12 | −0.02 | −0.02 | 0.04 | 0.10 |
| SAMD12 | −0.71 | 0.29 | 0.85 | 0.07 | 0.45 | MYCL | 0.39 | −0.05 | 0.20 | 0.24 | 0.13 | RPS11P1 | 0.43 | −0.48 | −0.19 | 0.40 | −0.59 |
| ADAD2 | −1.38 | 0.89 | 1.14 | 0.77 | 0.26 | LCAT | −0.28 | −0.02 | −0.31 | 0.29 | 0.24 | HNRNPA1P56 | 0.42 | −0.53 | −1.60 | 0.45 | −1.27 |
| AC022898.1 | −1.07 | 0.23 | 1.64 | −0.07 | 0.33 | G30345 | −0.91 | 0.89 | 3.48 | −0.53 | −0.12 | RPL10AP2 | 0.21 | −1.61 | 0.48 | −0.72 | 0.47 |
| NUTM2D | −1.13 | 0.44 | 0.44 | 0.03 | 0.01 | HNRNPLL | 0.17 | −0.08 | −0.11 | −0.16 | −0.04 | AC078889.1 | −0.17 | −0.40 | −0.47 | 0.84 | −0.56 |
| ACTL6A | 0.54 | −0.22 | −0.34 | −0.16 | −0.22 | AC040977.1 | −0.47 | 0.65 | 0.74 | 0.42 | 0.31 | RNU6-415P | 0.16 | −0.40 | −0.13 | 0.02 | 0.19 |
| GID8 | 0.73 | −0.13 | −0.39 | −0.01 | −0.38 | CCDC59 | 0.18 | −0.13 | −0.25 | −0.06 | −0.22 | AMH | −0.14 | −0.19 | −1.08 | −0.01 | −0.19 |
| C2orf68 | −0.60 | 0.29 | 0.40 | 0.30 | 0.06 | LINC01963 | 0.27 | 0.04 | 0.33 | −0.15 | −0.17 | ETV5-AS1 | −0.17 | 0.15 | 0.06 | 0.50 | 0.20 |
| RABSIF | 0.83 | −0.41 | −0.76 | −0.12 | −0.43 | AC004924.1 | −0.75 | 1.05 | 2.56 | −0.83 | 0.35 | ADORA3 | 0.21 | −0.92 | −0.74 | 0.10 | −0.07 |
| AC007389.3 | −1.64 | 0.47 | 0.55 | 0.62 | 0.44 | SEPT4-AS1 | −0.96 | −0.73 | 1.47 | −0.36 | 2.19 | AL139806.1 | −0.53 | −0.53 | −1.12 | 0.60 | 1.28 |
| RALBP1 | 0.56 | −0.15 | −0.37 | −0.03 | −0.35 | SNX16 | 0.25 | 0.13 | −0.09 | 0.23 | −0.10 | PLOD2 | 0.10 | −0.32 | −0.20 | −0.27 | −0.12 |
| POLD3 | 0.53 | −0.40 | −0.49 | −0.24 | −0.22 | CTAGE14P | −0.94 | −0.82 | −0.38 | 0.11 | −0.82 | AC091874.1 | −0.92 | 1.34 | −1.42 | 3.34 | −1.56 |
| PCDHGA3 | −1.37 | 0.72 | 1.09 | 1.16 | 0.16 | AC068620.2 | 0.68 | −0.88 | 0.49 | −0.59 | −0.15 | GRM5 | −0.23 | −0.18 | −1.38 | 0.02 | −0.17 |
| CRIP2 | −0.83 | 0.54 | 0.62 | 0.35 | 0.07 | AQP1 | −0.34 | 0.47 | 0.84 | 0.17 | −0.16 | CASC8 | 0.13 | −0.29 | −0.33 | −0.44 | −0.06 |
| G10911 | −0.77 | 0.84 | 0.42 | 0.30 | −0.09 | AC005692.1 | −0.84 | −0.82 | −0.20 | 0.20 | −0.07 | SPNS3 | −0.16 | 0.32 | −0.13 | 0.28 | 0.10 |
| CHSY1 | 0.53 | −0.32 | −0.51 | −0.25 | −0.36 | AC009244.1 | 0.52 | −0.55 | 0.16 | −0.36 | 0.17 | RNA5SP469 | −0.18 | −0.46 | 0.59 | 0.06 | 0.66 |
| RTCA | 0.51 | −0.36 | −0.46 | −0.25 | −0.11 | RN7SL418P | −0.78 | 0.80 | 1.59 | −0.80 | −0.55 | MAGEB10 | 0.34 | −1.29 | −2.10 | −0.77 | −1.15 |
| MFSD2A | −0.94 | 0.21 | 0.36 | 0.31 | 0.59 | AL356124.2 | 0.90 | 0.25 | 0.19 | −0.52 | 0.04 | GAPDHP2 | −0.11 | −0.39 | −0.05 | −0.12 | 0.50 |
| MTX2 | 0.72 | −0.35 | −0.53 | −0.03 | −0.17 | MMP19 | 0.42 | −0.61 | −1.04 | −0.30 | −0.38 | AC013565.1 | 0.22 | 0.45 | −0.32 | 1.38 | 0.56 |
| AC012317.2 | −2.30 | 1.80 | 2.85 | 0.80 | 0.59 | RPL17P50 | −0.39 | −0.13 | 0.86 | 0.03 | 0.52 | FABP12 | −0.39 | −1.83 | 1.43 | −0.69 | 1.39 |
| LINC01133 | −0.71 | 0.18 | 0.71 | 0.05 | 0.17 | REV3L-IT1 | −0.42 | −0.02 | 0.43 | −0.05 | 0.03 | RNU6-899P | −1.35 | −0.13 | 0.78 | −0.04 | 0.55 |
| PEBP4 | −2.20 | 0.78 | 1.68 | 0.43 | 0.47 | RUNDC1 | −0.18 | 0.03 | −0.09 | 0.16 | 0.15 | CER1 | −0.27 | −0.76 | 1.84 | −0.22 | 0.81 |
| PRPF4 | 0.55 | −0.37 | −0.52 | −0.21 | −0.24 | ENDOG | 0.40 | −0.50 | 0.07 | −0.36 | 0.48 | AC022390.1 | 0.32 | 1.28 | −1.26 | 0.30 | −1.03 |
| SMG7 | 0.24 | −0.04 | −0.21 | 0.01 | −0.14 | LARGE-AS1 | 0.23 | −0.19 | −0.41 | −0.43 | −0.38 | HAPLN1 | −0.24 | −0.77 | −0.49 | 0.29 | 0.38 |
| PCDHGB9P | −0.87 | 0.16 | 0.81 | 0.09 | 0.48 | RN7SL189P | −0.93 | 0.99 | 2.05 | −0.79 | −0.77 | ALOX5 | −0.10 | −0.34 | 0.01 | −0.44 | −0.16 |
| CARNS1 | −1.18 | 0.86 | 0.88 | 0.50 | 0.29 | AC016526.3 | 0.63 | 0.06 | −1.03 | −0.28 | −1.30 | AC004973.1 | −0.56 | −0.34 | −1.10 | −0.21 | −2.58 |
| PRR36 | −1.30 | 1.41 | 1.26 | 1.15 | 0.57 | AC013452.1 | 0.68 | −1.00 | −0.31 | 0.03 | 0.11 | FOXD4L1 | −0.25 | −0.59 | 0.93 | 0.37 | 1.83 |
| NGLY1 | 0.32 | −0.11 | −0.21 | −0.04 | 0.00 | AL390037.1 | −0.94 | −0.75 | 0.88 | −0.18 | −0.14 | PINCR | 0.43 | −1.29 | −1.12 | −0.59 | −0.12 |
| PRUNE2 | −0.83 | 0.56 | 0.62 | −0.28 | −0.33 | MGST1 | −0.47 | 0.08 | −0.29 | 0.09 | 0.52 | OR10G3 | −0.28 | 0.65 | −1.06 | 1.26 | −1.45 |
| G26828 | −1.70 | 0.76 | 0.07 | 0.97 | −0.22 | ODR4 | 0.12 | −0.03 | −0.03 | −0.04 | −0.01 | AC090907.2 | −0.25 | −0.61 | 0.67 | 1.08 | 2.11 |
| CAMK1 | −1.06 | 0.24 | 1.60 | −0.15 | 0.57 | AL008723.3 | 0.72 | 0.44 | −0.37 | 0.38 | −0.09 | LIN28B | −0.30 | −0.61 | −1.09 | −0.46 | −1.62 |
| BX324167.2 | −2.52 | 0.97 | 3.35 | 0.95 | 0.82 | RERG-IT1 | −1.08 | 1.35 | 1.39 | 0.64 | −0.09 | KRT42P | −0.12 | −0.56 | −1.94 | −0.15 | −1.16 |
| PCOLCE2 | −1.95 | 1.26 | 1.72 | 0.59 | 0.00 | G8456 | −0.53 | 0.38 | 1.19 | −0.07 | 0.69 | EFCAB10 | 0.13 | −0.70 | 0.01 | −0.40 | 0.20 |
| CYP4F22 | 1.18 | −0.33 | −0.55 | −0.07 | −0.56 | SEMA6B | 0.41 | −0.66 | −1.01 | −0.25 | −0.48 | PIK3AP1 | −0.13 | −0.41 | 0.43 | −0.40 | 0.33 |
| CYP3A5 | −1.05 | 1.07 | 1.25 | 0.52 | 0.28 | SOX21-AS1 | 0.41 | 0.17 | −0.19 | 0.47 | −0.24 | RPL26P20 | −0.66 | 0.39 | −0.50 | −0.12 | −1.21 |
| OR2T2 | −3.15 | 0.56 | 1.30 | 0.63 | 0.65 | CNBD2 | −0.49 | 0.74 | −0.54 | 0.62 | −0.19 | CRYBG2 | −0.08 | −0.01 | −0.15 | 0.14 | 0.27 |
| ADGRD2 | −1.36 | 0.32 | 0.10 | 0.76 | 0.55 | AC087280.2 | 0.67 | −0.19 | −1.65 | 0.61 | −1.13 | MANBA | 0.05 | −0.08 | 0.23 | −0.01 | 0.11 |
| ANKFN1 | −1.34 | 1.20 | 1.63 | 0.43 | 0.41 | MAP4K2 | −0.18 | 0.22 | −0.22 | 0.29 | −0.08 | LST1 | −0.12 | −0.42 | 0.46 | −0.24 | 0.47 |
| KCNK6 | 0.79 | −0.59 | −0.88 | −0.19 | −0.27 | AL606537.1 | 0.90 | −0.32 | 0.49 | −0.08 | 0.16 | FNBP4 | 0.04 | −0.04 | −0.01 | 0.00 | 0.05 |
| EXOSC9 | 0.43 | −0.42 | −0.42 | −0.20 | −0.09 | AP003071.2 | −0.97 | −0.29 | 0.61 | −0.04 | 0.13 | EIF4BP8 | −0.24 | −0.14 | −1.42 | 0.90 | −1.09 |
| ADK | 0.60 | −0.36 | −0.63 | −0.07 | −0.30 | NLRP10 | 0.50 | 0.07 | 0.74 | 0.59 | −0.62 | AL590079.1 | −0.30 | 0.56 | 0.39 | 1.50 | −0.50 |
| NEK3 | −0.44 | 0.20 | 0.50 | 0.01 | −0.08 | PTPN20CP | −0.86 | −0.32 | 3.04 | −1.60 | 0.62 | LINC02077 | 0.76 | 0.64 | −2.28 | −0.11 | −1.16 |
| AC122129.1 | −0.96 | 0.41 | 0.81 | 0.25 | 0.54 | RNA5SP502 | −1.25 | 1.06 | −0.31 | 1.84 | −0.50 | AC004988.1 | 0.10 | −0.01 | 0.54 | −0.20 | −0.34 |
| ABI3BP | −1.26 | 0.80 | 1.42 | −0.38 | −0.02 | ENOX1-AS1 | −0.55 | −0.92 | 0.31 | −0.33 | 0.72 | LINC01490 | 0.35 | −1.23 | −0.85 | 0.96 | 1.41 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| DMAP1 | −0.44 | 0.30 | 0.37 | 0.18 | 0.13 | RN7SL395P | −0.70 | 0.01 | 0.13 | −0.47 | 0.62 | AL513122.2 | −0.12 | −0.01 | −0.07 | −0.33 | −0.24 |
| LRRC36 | −1.43 | 0.14 | 0.42 | 0.52 | 0.36 | SHC4 | −0.36 | 0.17 | 0.89 | 0.13 | 0.79 | GTF2H2C | 0.05 | −0.24 | −0.16 | −0.26 | 0.20 |
| RPL36AL | 0.82 | −0.42 | −0.65 | −0.25 | −0.43 | ARG2 | 0.34 | 0.05 | −0.02 | 0.13 | −0.30 | HNRNPA1P25 | 0.20 | −0.44 | −0.72 | 0.32 | 0.34 |
| COPG1 | 0.41 | −0.24 | −0.41 | −0.20 | −0.28 | IZUMO2 | −0.99 | −0.46 | 0.04 | 0.46 | 1.21 | KIF25-AS1 | 0.37 | −1.13 | −0.72 | −1.70 | −1.91 |
| GSG1 | −1.11 | 0.30 | 0.82 | 0.00 | 0.22 | AC104984.2 | 0.62 | 0.14 | −0.25 | 0.24 | −0.37 | AC092933.1 | 0.24 | 0.13 | −1.37 | 0.22 | −0.85 |
| DYRK1B | −0.72 | 0.46 | 0.54 | 0.42 | 0.19 | AL139156.2 | 0.54 | 0.23 | −0.86 | 0.50 | −0.66 | AC010336.2 | −0.57 | 0.25 | 0.78 | 0.02 | 0.18 |
| KRT40 | −2.13 | 1.17 | 2.75 | 0.39 | 1.07 | RPS27AP11 | 0.59 | −0.50 | −0.27 | 0.28 | −0.44 | RNA5SP425 | 0.26 | −1.47 | −1.09 | 0.43 | 0.80 |
| LINC01881 | −0.46 | 0.40 | 0.34 | 0.07 | 0.19 | AC099509.1 | −0.89 | 0.70 | 0.87 | 0.17 | −0.33 | AC064874.1 | 0.08 | −0.08 | −0.10 | 0.13 | 0.11 |
| AP002761.4 | 1.37 | −0.71 | −0.89 | −0.04 | 0.24 | AC009495.3 | −0.48 | −0.01 | 0.54 | 0.27 | 0.62 | AC098484.4 | −0.11 | −0.20 | −0.26 | 0.02 | −0.18 |
| HERC4 | 0.47 | −0.22 | −0.33 | −0.06 | −0.10 | AL121992.1 | −0.58 | 0.11 | −0.66 | −0.24 | −0.62 | EIF4EP4 | 0.51 | 0.91 | −2.12 | 0.07 | −2.19 |
| PPT1 | 0.48 | −0.24 | −0.43 | −0.10 | −0.28 | CCDC90B | 0.21 | −0.08 | 0.22 | −0.18 | 0.02 | CHST4 | −0.24 | 0.13 | −0.40 | −0.35 | 0.23 |
| NFE2L2 | 0.63 | −0.22 | −0.35 | −0.02 | −0.27 | AC027309.2 | 0.41 | 0.25 | −0.56 | 0.12 | −0.46 | SDCBP2P1 | 0.45 | −0.51 | −0.12 | 0.64 | 0.52 |
| RANBP2 | 0.56 | −0.19 | −0.32 | −0.14 | −0.23 | AC097638.1 | −0.47 | 0.09 | 1.56 | −0.56 | 0.86 | AP001065.1 | −0.12 | 0.15 | 0.21 | 0.12 | 0.02 |
| CCDC110 | −1.53 | 1.41 | 1.10 | 0.52 | −0.04 | OR52N4 | −0.94 | −0.90 | 2.00 | −1.14 | 1.96 | AC131281.1 | 0.26 | 0.60 | 0.47 | 0.29 | 0.18 |
| INTU | −0.45 | 0.41 | 0.59 | 0.10 | 0.14 | RPL22P16 | −0.56 | 0.81 | 0.68 | 0.24 | −0.35 | LINC01222 | −0.35 | −0.18 | −0.93 | −0.20 | −0.58 |
| PSMC1P1 | 0.95 | −0.68 | −0.98 | −0.19 | −0.68 | MRPS14 | −0.18 | 0.18 | 0.51 | 0.01 | 0.23 | BTNL3 | −0.28 | −0.57 | −0.74 | 0.84 | −0.21 |
| GPN1 | 0.50 | −0.34 | −0.34 | −0.24 | −0.21 | AC092794.2 | 0.69 | −0.43 | 0.07 | −0.45 | 0.37 | AC068987.3 | −0.16 | −0.08 | 1.49 | −0.22 | 0.91 |
| SEMA4G | −0.99 | 0.96 | 1.30 | 0.60 | 0.12 | SNORD3C | −0.51 | 0.20 | −0.01 | 0.96 | 0.53 | AL139237.2 | −0.28 | −0.77 | 0.68 | −0.10 | 0.71 |
| SARS | 0.47 | −0.10 | −0.53 | −0.02 | −0.45 | LINC00562 | 0.30 | −0.32 | −0.66 | −0.16 | −0.45 | AC073283.2 | 0.48 | −1.02 | 2.52 | −0.42 | 2.83 |
| NOP58 | 0.62 | −0.57 | −0.60 | −0.18 | −0.08 | BNIP3P25 | 0.50 | −0.12 | −0.43 | −0.03 | −0.12 | AC122713.2 | −0.24 | 1.15 | −0.37 | 0.59 | −0.59 |
| AC005387.1 | −1.36 | 0.09 | 1.15 | 0.67 | 0.48 | AL049830.4 | 0.41 | −0.03 | −0.55 | 0.07 | −0.36 | CTNNBIP1 | 0.08 | 0.27 | 0.13 | 0.25 | −0.19 |
| AP002495.1 | −0.55 | 0.10 | 0.50 | −0.13 | 0.17 | BICC1 | −0.34 | 0.03 | 0.78 | −0.58 | 0.16 | DHRS4L1 | −0.14 | 0.12 | 0.18 | 0.29 | 0.33 |
| RNU1-27P | −1.42 | 0.51 | 0.01 | 0.51 | 0.23 | OR10A5 | 0.68 | −2.30 | −0.17 | 0.15 | 1.67 | AP006295.1 | 0.52 | −0.38 | −0.91 | −0.19 | −0.78 |
| COA3 | 0.79 | −0.35 | −0.23 | −0.23 | −0.16 | FAM157C | 0.33 | −0.74 | −0.48 | 0.24 | 0.74 | PPIAP66 | −0.53 | −0.06 | −1.44 | 1.28 | 0.32 |
| AMOTL2 | −0.76 | 0.36 | 0.19 | 0.10 | −0.10 | RPL10P3 | 0.69 | −0.63 | −0.90 | 0.42 | −1.06 | AL121894.2 | 0.19 | 0.19 | −0.73 | −0.05 | −0.56 |
| PSG5 | −1.65 | 0.56 | 0.72 | 0.38 | 0.38 | AC022306.3 | 0.98 | 0.51 | 0.83 | −0.67 | −0.75 | RNU6-124P | −0.89 | −0.79 | −0.63 | −0.43 | −1.16 |
| ATP5MD | 0.91 | −0.31 | −0.62 | −0.19 | −0.58 | FAM219A | −0.15 | 0.02 | 0.28 | −0.20 | 0.03 | AC067747.1 | −0.24 | 1.21 | −0.14 | 1.08 | −0.38 |
| HNRNPA3 | 0.38 | −0.28 | −0.33 | −0.03 | −0.02 | SPIC | 1.14 | −1.29 | −1.71 | 1.09 | 0.84 | ATP5F1BP1 | −0.74 | 0.76 | 0.04 | 1.39 | −0.91 |
| SGK2 | −1.49 | 0.91 | 1.00 | 0.93 | 0.86 | MTND2P2 | −0.40 | 0.16 | 1.03 | −0.21 | 0.48 | NKX1-2 | −0.17 | 0.73 | −0.46 | 0.34 | −0.01 |
| MLKL | 0.66 | −0.57 | −0.82 | −0.28 | −0.25 | OIT3 | 0.83 | −0.47 | −0.23 | 0.55 | −0.20 | AP000889.1 | −0.28 | 1.20 | 0.94 | 0.42 | −0.12 |
| 6-Mar | −0.30 | 0.26 | 0.19 | 0.12 | −0.07 | HSPE1P11 | 0.39 | 0.20 | −0.41 | 0.38 | −0.23 | AC131025.1 | 0.40 | −0.46 | −1.47 | −0.64 | −0.62 |
| MLLT6 | −0.58 | 0.28 | 0.27 | 0.28 | 0.24 | MIF4GD | −0.18 | 0.38 | 0.42 | 0.20 | 0.00 | EBLN2 | 0.07 | 0.03 | −0.17 | 0.13 | −0.15 |
| MORN4 | −0.83 | 0.66 | 0.99 | 0.17 | 0.18 | RNU7-50P | 0.73 | −0.19 | −0.34 | −0.20 | −0.38 | AL035460.1 | −0.39 | −1.45 | 1.99 | −2.05 | 1.35 |
| KCNB1 | −1.32 | 1.02 | 0.88 | 0.62 | −0.21 | MAP3K1 | 0.18 | 0.21 | 0.02 | 0.06 | −0.03 | AC104463.2 | −0.21 | 0.98 | −0.01 | 0.24 | −0.34 |
| SDAD1 | 0.52 | −0.33 | −0.28 | −0.30 | −0.16 | AC022467.1 | −0.46 | 0.19 | 1.48 | −0.26 | 0.15 | FO393408.1 | −0.66 | −0.50 | 0.74 | 0.83 | −0.20 |
| HCAR2 | 1.27 | −1.26 | −1.11 | −0.20 | −0.58 | AC009362.1 | −1.07 | 0.00 | 1.07 | −0.92 | 0.21 | AL442067.1 | 0.14 | −0.19 | 0.28 | 0.26 | 0.51 |
| HSPA4L | 0.81 | −0.17 | −0.70 | −0.18 | −0.60 | SCN2B | −0.48 | −0.09 | −0.13 | −0.29 | −0.06 | AC129510.1 | 0.20 | 0.54 | −0.18 | 0.59 | 0.33 |
| AL022322.2 | −0.95 | 0.23 | 0.54 | 0.40 | 0.60 | AC107072.1 | −1.83 | −0.25 | 2.61 | −1.85 | 0.74 | LINC00348 | −0.64 | −1.50 | 0.02 | −1.63 | −0.02 |
| AC123912.1 | −1.26 | 0.31 | 1.46 | −0.19 | 0.69 | CPVL | 0.42 | −0.29 | 0.11 | −0.33 | 0.07 | AC004224.1 | −0.89 | 0.29 | −0.04 | 0.84 | 0.17 |
| MDH2 | 0.62 | −0.25 | −0.49 | −0.09 | −0.24 | AC023137.1 | −0.92 | 0.42 | 0.53 | −0.05 | 0.92 | PPBPP1 | 0.82 | −1.38 | −1.16 | 0.60 | −0.50 |
| ALDH3A2 | −0.82 | 0.64 | 1.14 | 0.40 | 0.47 | AC022826.1 | 0.44 | −0.62 | −0.55 | −0.18 | 0.17 | AC015989.1 | 0.39 | 0.32 | 0.05 | 1.37 | 2.06 |
| SERPINA12 | −1.58 | 0.60 | 2.81 | 0.78 | 0.35 | AL358176.4 | −1.29 | 0.44 | 1.09 | −0.40 | 0.29 | AL359555.4 | 0.52 | −0.63 | −2.81 | 0.32 | −1.43 |
| AC079781.3 | −1.04 | 0.80 | 0.90 | 0.57 | 0.12 | MKLN1 | −0.11 | 0.06 | 0.15 | −0.01 | 0.04 | IL17C | 0.61 | −0.54 | −0.83 | 1.11 | −0.14 |
| DPP10 | −1.78 | 0.79 | −0.02 | −0.11 | −1.51 | RUFY1 | −0.11 | 0.08 | −0.07 | 0.08 | −0.07 | AC079200.1 | −0.15 | −0.27 | −0.28 | 0.00 | −0.41 |
| NFKBIL1 | −0.66 | 0.12 | 0.20 | 0.28 | 0.28 | SAFB2 | −0.20 | −0.06 | −0.06 | −0.04 | 0.11 | RNU6-670P | 0.57 | −0.45 | 0.67 | −0.56 | 0.94 |
| NUP50 | 0.44 | −0.42 | −0.59 | −0.12 | −0.08 | AC007919.2 | −0.59 | 0.49 | 0.29 | −0.26 | 0.28 | LINC01858 | 0.32 | 0.12 | −0.95 | 0.25 | −1.53 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| MYL5 | −0.78 | 0.10 | 0.04 | 0.30 | 0.18 | AC015563.2 | 0.96 | −0.09 | −0.94 | −0.22 | −0.19 | NAP1L4P1 | −0.07 | −0.31 | −0.37 | 0.06 | 0.10 |
| CAPN11 | −1.21 | 0.33 | 1.49 | 0.19 | 0.30 | AC095032.1 | −1.06 | 1.04 | 1.87 | −0.47 | 0.77 | AC007349.3 | −0.28 | −0.97 | −0.85 | 0.23 | 0.63 |
| CFH | −1.25 | 0.73 | 1.74 | 0.03 | 0.13 | AC091230.1 | 0.98 | 0.01 | 0.36 | −0.26 | −0.84 | AC022405.1 | 0.19 | −1.38 | −1.74 | −0.16 | 0.20 |
| STYX | 0.55 | −0.24 | −0.38 | −0.06 | −0.22 | AL354893.1 | −0.49 | 0.67 | 1.05 | 0.46 | 0.52 | MIR548N | 0.76 | 0.53 | −1.53 | 0.73 | −1.18 |
| AL008727.1 | −1.10 | 0.47 | −0.15 | 0.68 | 0.11 | FKBP6 | −0.78 | −1.07 | −1.31 | −0.89 | −0.72 | BBS12 | −0.09 | −0.18 | 0.40 | −0.26 | 0.09 |
| HMBS | 0.81 | −0.65 | −0.85 | 0.01 | 0.02 | SNHG10 | 0.30 | −0.21 | 0.04 | 0.22 | 0.11 | IGLL5 | 0.79 | −0.68 | −0.66 | 0.55 | 0.07 |
| NXN | 0.52 | −0.38 | −0.60 | −0.03 | −0.07 | SPNS1 | −0.35 | 0.32 | −0.41 | 0.27 | −0.03 | AC025539.1 | −0.20 | 0.32 | −1.02 | 0.29 | −0.53 |
| ATP8A1 | −0.84 | 0.62 | 0.96 | 0.24 | 0.11 | AC078842.1 | −1.02 | −0.70 | −0.49 | −0.75 | −0.19 | G12115 | −0.93 | −1.14 | −0.52 | 0.60 | 1.07 |
| RNF223 | 1.92 | −0.64 | −2.10 | −0.27 | −1.88 | AC005052.1 | −0.93 | 1.25 | −0.91 | 1.41 | −1.50 | AC078778.1 | 0.12 | −0.41 | 0.02 | −0.17 | 0.19 |
| EFR3B | 0.99 | −0.42 | −1.05 | −0.01 | −0.49 | AC108134.2 | 0.32 | −0.21 | −0.60 | 0.14 | −0.14 | ERMP1 | 0.05 | 0.04 | 0.19 | 0.08 | 0.02 |
| CDH4 | −1.54 | 0.37 | −0.69 | 0.75 | 0.25 | ADAMTS12 | 0.42 | −0.47 | 0.02 | −0.79 | −0.19 | RNA5SP501 | −1.42 | 0.07 | 2.79 | −0.30 | 3.38 |
| FIBIN | −1.33 | 0.83 | 1.99 | −0.24 | −0.04 | LINC00847 | −0.37 | 0.22 | 0.65 | 0.23 | 0.26 | GNAT3 | −0.28 | −1.76 | −1.46 | −0.44 | 0.97 |
| STK17A | 0.74 | −0.37 | −0.39 | −0.47 | −0.29 | AL136038.4 | −0.39 | −0.12 | 0.11 | 0.29 | 0.43 | AL133279.1 | 0.76 | −0.76 | −0.30 | −0.08 | 0.18 |
| CCDC149 | −0.65 | 0.31 | 0.63 | 0.08 | 0.11 | RPL3P7 | −0.52 | −0.08 | 0.59 | 0.24 | 0.43 | DECR2 | 0.07 | −0.12 | −0.37 | 0.06 | −0.07 |
| AL358394.2 | −1.67 | 0.15 | 0.02 | −0.01 | 0.54 | RN7SL48P | −0.80 | −1.02 | 0.54 | −0.75 | 0.58 | LINC02195 | 0.64 | −1.46 | −0.97 | −0.49 | 0.41 |
| SLC22A23 | 0.72 | −0.15 | −0.59 | 0.12 | −0.30 | RPS23P1 | −0.98 | −0.56 | 0.41 | −1.44 | 0.26 | AC023090.1 | 0.14 | −0.20 | −0.21 | 0.09 | −0.28 |
| AC011473.3 | −2.06 | −0.01 | 2.89 | −1.48 | 0.42 | AC004900.1 | 0.59 | −0.14 | 0.23 | −0.01 | −0.02 | SLC12A9 | −0.05 | −0.14 | −0.03 | 0.14 | 0.41 |
| C5orf46 | −1.43 | 1.42 | 2.19 | 0.84 | −0.23 | AC103853.1 | −0.58 | 0.04 | 1.01 | 0.25 | 0.39 | KMT5B | 0.03 | 0.11 | 0.12 | 0.00 | 0.02 |
| ANAPC1 | 0.47 | −0.37 | −0.49 | −0.07 | 0.02 | CEND1 | −0.62 | 0.36 | 0.00 | 0.18 | −0.14 | AL606834.1 | −0.08 | 0.20 | 0.25 | 0.05 | −0.05 |
| RILPL1 | −0.71 | 0.19 | 0.37 | 0.12 | 0.28 | AF213884.3 | 0.62 | −0.18 | −1.05 | 0.39 | 0.12 | AC011239.1 | −0.14 | 0.23 | −0.64 | 0.01 | −0.46 |
| AC040174.1 | −1.25 | 0.57 | 1.28 | 0.25 | 0.16 | AC009269.5 | 0.53 | 0.25 | −0.46 | 0.08 | −0.20 | RGS18 | 0.17 | −0.31 | 0.07 | −0.36 | 0.02 |
| ATP6V1F | 0.96 | 0.07 | −0.36 | −0.03 | −0.69 | AC093495.1 | −0.33 | −0.14 | 0.42 | 0.13 | 0.45 | AL022329.2 | −0.13 | −0.46 | −0.66 | −0.01 | 0.14 |
| CSAD | −0.70 | 0.41 | 0.43 | 0.35 | 0.29 | AC233992.3 | −1.02 | −0.49 | −0.40 | −0.72 | −0.37 | KRT28 | −0.42 | −1.03 | 3.94 | −0.05 | 2.78 |
| GPR4 | 1.46 | −0.89 | −0.76 | −0.46 | −0.35 | MYL6P3 | −1.88 | 0.48 | −1.00 | 1.32 | −0.74 | RN7SKP227 | −0.15 | 0.54 | 0.86 | 0.03 | −0.81 |
| LINC01659 | −3.12 | 2.48 | 1.97 | 2.78 | 1.48 | AL139353.3 | −1.00 | 0.93 | 2.82 | −0.47 | 0.21 | CD160 | −0.07 | −0.28 | 0.41 | −0.36 | 0.21 |
| PCDHGB5 | −0.65 | 0.22 | 0.70 | 0.04 | 0.18 | AC009803.1 | −1.02 | 0.86 | 0.51 | 0.32 | −1.43 | PJA2 | 0.05 | 0.13 | 0.04 | −0.06 | −0.17 |
| KIAA1549 | −0.94 | 0.67 | 0.91 | 0.13 | 0.10 | RNY4P10 | 0.60 | 0.68 | −0.47 | 0.40 | −0.67 | AC068643.2 | 0.48 | −0.33 | −0.74 | 0.33 | −0.50 |
| CD58 | 0.70 | −0.32 | −0.29 | −0.20 | −0.15 | RN7SL375P | 1.04 | −0.96 | −1.47 | −0.39 | −0.78 | EP300-AS1 | 0.13 | −0.04 | −0.10 | −0.01 | 0.04 |
| IFIT3 | 1.23 | −1.06 | −1.23 | −0.81 | −0.64 | AC012146.2 | −1.19 | 0.23 | 0.95 | 1.07 | 0.84 | GPR89B | −0.09 | 0.35 | −0.10 | 0.19 | −0.18 |
| RNA5SP92 | 1.98 | −1.11 | −1.01 | −0.24 | −0.05 | MMP28 | −0.40 | 0.09 | −0.29 | 0.24 | 0.21 | G40865 | 0.10 | 0.28 | 0.62 | 0.36 | 0.29 |
| PSME1 | 0.65 | −0.34 | −0.41 | −0.21 | −0.44 | AC138915.3 | 1.29 | −0.46 | −0.87 | 0.08 | −0.50 | AC096711.2 | −0.21 | −0.41 | 1.15 | −0.33 | −0.14 |
| DNAJC8 | 0.69 | −0.41 | −0.50 | −0.21 | −0.34 | SPATA13-AS1 | −0.48 | 0.25 | 0.98 | 0.13 | 0.53 | RNU6-245P | 0.25 | −0.21 | −0.58 | 0.11 | 0.06 |
| AC106795.1 | 0.83 | −0.21 | −0.40 | 0.17 | 0.12 | ARF1P2 | −0.36 | −0.11 | 0.21 | 0.25 | 0.52 | RINT1 | 0.03 | −0.08 | 0.06 | −0.16 | 0.00 |
| AC073336.1 | −2.90 | −0.61 | 1.23 | 1.38 | −0.45 | OVOL2 | −0.30 | 0.44 | −0.33 | 0.31 | −0.18 | RASEF | 0.08 | 0.35 | −0.46 | 0.31 | −0.29 |
| PTK2B | −0.73 | 0.28 | 0.45 | 0.03 | 0.17 | CA8 | −0.47 | 0.28 | 0.42 | 0.19 | −0.12 | RPL7P13 | −0.50 | 1.30 | −1.38 | 0.93 | −1.94 |
| HIST1H2AG | 1.34 | −0.90 | −1.05 | −0.62 | −0.68 | G18713 | −0.72 | 1.14 | 0.59 | 1.01 | 0.71 | AC090409.1 | 0.14 | −0.76 | −1.37 | −0.14 | 0.32 |
| KAT6B | −0.47 | 0.37 | 0.44 | 0.15 | −0.01 | AC107032.1 | 0.71 | −0.12 | 0.03 | 0.16 | −0.33 | CDC27P2 | 0.22 | −0.76 | −1.44 | 0.02 | −0.70 |
| AC114546.1 | −1.73 | 0.61 | −0.52 | 0.31 | −0.69 | AC009656.1 | 0.86 | −0.64 | 0.18 | 0.19 | 0.79 | PTGDS | −0.15 | −0.38 | 1.14 | −0.37 | 1.62 |
| AC105345.1 | −1.55 | 0.90 | 1.01 | 0.43 | 0.44 | RPS7P10 | 0.62 | 0.00 | −0.68 | 0.00 | −1.01 | GNB4 | −0.05 | −0.02 | 0.28 | −0.11 | 0.03 |
| ABCF2 | 0.71 | −0.51 | −0.55 | −0.22 | −0.13 | AC099795.1 | −0.50 | 0.00 | 0.68 | 0.10 | 0.90 | ITIH1 | 0.24 | −0.56 | −1.18 | 0.35 | −0.85 |
| SMARCC1 | 0.43 | −0.20 | −0.34 | −0.07 | −0.17 | OR7E11P | −1.59 | −0.45 | 0.37 | −0.90 | 1.85 | RPS17P15 | −0.74 | −0.01 | −0.95 | 0.13 | −1.21 |
| AL031705.1 | −1.73 | 0.68 | −0.04 | 0.72 | 0.50 | AC090954.1 | −1.10 | 1.08 | 3.42 | 0.73 | 1.57 | AL354896.1 | 0.62 | −1.14 | 1.12 | 0.15 | 1.80 |
| DNAJC4 | −0.62 | 0.37 | 0.43 | 0.28 | 0.14 | DKK3 | −0.21 | 0.17 | 0.17 | −0.15 | −0.11 | MC3R | 0.45 | −0.72 | −0.67 | 0.36 | −1.27 |
| FRMD6-AS2 | 1.59 | −0.63 | −0.79 | −0.19 | −0.08 | GVINP1 | 0.38 | −0.60 | 0.12 | −0.52 | 0.26 | AL355073.2 | −0.34 | 0.67 | 0.46 | 0.82 | 0.16 |
| LRRN1 | −1.26 | 0.92 | 1.29 | 0.12 | −0.30 | HMGB1P44 | −0.87 | 0.73 | 2.03 | 0.38 | 0.15 | AC114550.1 | 0.32 | −1.70 | −1.60 | −0.21 | −0.19 |
| CCDC158 | −1.47 | 0.57 | 1.01 | 0.61 | 0.04 | SNORA70G | 0.36 | −0.36 | −0.09 | −0.16 | −0.04 | AL132655.3 | 0.80 | −0.52 | −0.06 | −0.51 | −0.57 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| ADAT1 | 0.35 | −0.37 | −0.24 | −0.20 | 0.05 | HMGB1P51 | 0.53 | −0.11 | −0.76 | −0.11 | −0.63 | RNU4-39P | −0.29 | −1.48 | −0.60 | −0.48 | 0.70 |
| HIST1H2AI | 1.33 | −0.86 | −1.06 | −0.29 | −0.81 | RWDD4P1 | 0.39 | −0.39 | −0.05 | −0.20 | 0.30 | AL034417.1 | 0.77 | −0.19 | 0.19 | 0.48 | −0.17 |
| POLDIP2 | 0.56 | −0.28 | −0.39 | −0.08 | −0.14 | RP11-141C7.4 | 0.80 | −0.38 | −0.55 | 0.21 | 0.40 | AC008676.3 | 0.20 | −0.52 | 0.45 | −0.31 | 0.48 |
| AL445309.1 | 1.23 | −0.37 | −0.75 | 0.06 | −0.28 | AL353704.1 | −0.59 | 0.55 | 1.00 | −0.08 | −0.09 | SOX11 | −0.16 | −0.61 | −0.07 | 0.40 | 0.21 |
| RMI1 | 0.72 | −0.49 | −0.41 | −0.16 | −0.06 | BAG1 | 0.19 | 0.14 | −0.33 | 0.14 | −0.28 | AL391361.3 | −0.63 | 0.84 | 1.10 | 1.56 | 0.73 |
| ATP5F1C | 0.65 | −0.20 | −0.49 | −0.12 | −0.40 | SMAD9 | −0.32 | 0.38 | 0.86 | 0.08 | −0.02 | FKSG63 | 0.43 | −0.57 | 0.86 | −0.53 | 0.15 |
| LAMTOR2 | 0.69 | −0.17 | −0.34 | −0.04 | −0.29 | IGFBP4 | 0.39 | −0.15 | 0.48 | −0.37 | −0.14 | AL731567.1 | 0.15 | 0.03 | 0.60 | −0.47 | 0.58 |
| EXOC3L2 | 1.10 | −0.84 | −0.68 | −0.15 | −0.24 | SPDYE7P | −0.75 | −0.98 | 0.46 | 0.62 | 0.94 | RN7SL638P | −0.36 | −0.67 | 0.27 | −0.53 | 1.66 |
| POR | 0.43 | −0.24 | −0.36 | −0.04 | −0.18 | ACOT6 | −1.03 | 0.30 | 0.16 | 0.16 | −0.24 | EGFLAM-AS4 | 0.15 | −0.67 | −0.09 | 0.29 | 0.53 |
| AC018742.1 | −1.82 | 0.82 | 0.98 | 0.75 | 0.63 | AC023908.1 | 0.92 | −0.53 | −1.45 | −1.04 | −1.54 | ASB5 | −0.26 | −0.45 | −1.24 | 0.53 | −0.79 |
| PURA | −0.39 | 0.25 | 0.44 | 0.02 | 0.15 | AC058823.1 | 0.47 | −0.13 | 0.13 | 0.00 | −0.03 | ADCY10 | −0.12 | −0.39 | 0.06 | 0.04 | 0.59 |
| SNORD12B | 1.11 | −0.79 | −1.23 | 0.14 | −0.19 | PIPSL | −0.43 | 0.35 | 0.12 | 0.48 | −0.30 | AC093157.1 | 0.06 | −0.16 | 0.21 | −0.29 | 0.13 |
| AC011369.1 | 1.49 | −0.65 | −1.75 | −0.11 | −0.46 | AC090181.3 | 0.30 | −0.43 | −0.21 | 0.20 | 0.22 | AL161756.1 | 0.13 | −0.54 | 0.19 | −0.26 | 0.78 |
| ASNA1 | 0.53 | −0.13 | −0.36 | −0.04 | −0.40 | AL357552.2 | −0.36 | 0.00 | 0.26 | −0.09 | 0.41 | DGCR2 | −0.06 | 0.25 | 0.05 | 0.24 | 0.03 |
| HMOX1 | 1.19 | −0.57 | −1.06 | −0.70 | −1.10 | AC027290.2 | 0.23 | −0.33 | −0.80 | −0.13 | −0.07 | AC006566.1 | 0.21 | 0.06 | 0.90 | −1.01 | −0.59 |
| CHD5 | −1.48 | 0.37 | 0.32 | 0.26 | 0.11 | ESF1 | 0.20 | −0.19 | −0.10 | −0.14 | −0.01 | LINC02260 | 0.48 | −1.59 | −1.03 | −0.32 | 0.54 |
| SLC9A3R1 | 0.66 | −0.11 | −0.67 | 0.15 | −0.21 | SIN3A | 0.10 | 0.06 | 0.02 | 0.04 | −0.09 | AC087241.4 | 0.14 | −0.39 | −0.57 | 0.16 | 0.19 |
| AC122718.2 | 0.77 | −0.30 | −0.44 | −0.23 | −0.16 | SETP9 | 1.43 | −0.70 | −1.22 | 0.72 | 0.51 | MRGPRX3 | 0.26 | −0.36 | −1.18 | −0.54 | −0.94 |
| RWDD4 | 0.78 | −0.29 | −0.43 | −0.32 | −0.18 | SDR42E1 | 0.37 | 0.27 | 0.15 | 0.25 | −0.09 | RPL12P21 | −0.16 | 0.35 | −0.48 | 1.04 | 0.14 |
| KATNA1 | 0.41 | −0.17 | −0.33 | −0.07 | −0.14 | PCDHB17P | −0.93 | 0.38 | 0.95 | 0.61 | −0.21 | INO80B | −0.22 | 1.35 | 0.05 | 0.63 | −0.62 |
| NLRX1 | 0.84 | −0.32 | −0.59 | 0.00 | −0.12 | AC008738.2 | −0.57 | −0.51 | 0.46 | 0.22 | 1.17 | SMTN | 0.07 | −0.13 | −0.38 | −0.32 | −0.14 |
| CXXC4 | −1.54 | 0.76 | 1.11 | 0.62 | 0.46 | DRD2 | −0.58 | 1.26 | 0.40 | 0.60 | −0.43 | LINC02257 | 0.30 | −0.83 | −0.12 | −0.05 | 0.65 |
| AC105020.1 | −1.00 | 0.80 | 0.68 | 0.28 | 0.03 | AC078880.3 | −0.97 | −0.95 | 0.90 | 0.23 | 0.60 | EBAG9P1 | 0.09 | −0.19 | 0.49 | −0.25 | 0.25 |
| EPHX3 | 1.29 | −0.10 | −0.55 | 0.09 | −0.64 | AP001362.2 | −0.40 | 0.11 | 0.42 | 0.02 | 0.12 | AC108210.2 | 0.47 | −1.85 | −1.19 | −0.01 | 0.08 |
| AL357093.1 | −1.16 | 0.63 | 0.22 | 0.61 | −0.25 | RP11-187C18.3 | −1.25 | 1.23 | 2.04 | 1.44 | 0.53 | KNCN | 0.44 | −0.73 | −1.74 | 1.32 | 0.27 |
| PWWP2AP1 | −2.28 | 1.60 | 1.63 | 0.22 | 0.22 | G35698 | −0.41 | 0.29 | 0.44 | 0.13 | −0.01 | AC040169.4 | −0.29 | −0.51 | −0.65 | −0.15 | −0.34 |
| DCTPP1 | 0.93 | −0.60 | −0.58 | −0.25 | −0.36 | RNU6-862P | 1.13 | −0.31 | −1.35 | 0.18 | 0.80 | HMGB3P4 | −0.09 | 0.16 | 0.14 | 0.05 | 0.28 |
| SLC2A1-AS1 | −1.16 | 0.35 | 0.92 | 0.20 | 0.51 | AL513412.1 | 0.37 | 0.20 | −0.10 | −0.15 | −0.22 | MEGF11 | −0.07 | 0.18 | 0.46 | 0.08 | 0.20 |
| RP11-680G24.5 | −0.72 | 0.18 | 0.43 | 0.26 | 0.48 | KRT7 | −0.66 | 0.80 | 0.79 | 0.66 | 0.32 | P2RX5 | −0.28 | 0.07 | 0.59 | −0.30 | 1.01 |
| SLC1A5 | 0.90 | −0.56 | −0.95 | −0.10 | −0.05 | PLCXD2-AS1 | 1.28 | 0.02 | −1.29 | −0.60 | −1.61 | LINC01551 | −0.29 | −0.79 | −0.53 | 0.37 | −0.88 |
| SDR16C5 | 1.30 | 0.15 | −0.55 | 0.20 | −0.81 | FRRS1 | 0.24 | 0.06 | −0.06 | 0.17 | 0.03 | AL353754.1 | 0.25 | −0.80 | 0.88 | −0.78 | 0.80 |
| SNTB1 | −0.86 | 0.58 | 1.15 | −0.10 | −0.03 | COL12A1 | 0.36 | −0.24 | 0.03 | −0.96 | −0.48 | PARAL1 | −0.65 | −0.53 | −0.99 | 0.87 | −0.46 |
| GATAD2A | 0.37 | −0.17 | −0.44 | 0.02 | −0.14 | AC027288.1 | 0.26 | 0.22 | 0.29 | 0.42 | 0.03 | RNU6-1053P | 0.17 | −0.18 | 0.06 | −0.49 | −0.08 |
| LINC01238 | −0.91 | 0.34 | 0.95 | 0.40 | 0.73 | MIR4432HG | −0.51 | −0.56 | 0.20 | −0.55 | 0.02 | G26223 | −0.23 | −0.12 | 0.66 | −0.55 | 0.22 |
| ILDR1 | −1.27 | 1.00 | 1.94 | 0.26 | 0.13 | AL353572.2 | 1.22 | −0.93 | −1.14 | 0.89 | 0.72 | AL445433.2 | 0.37 | −0.78 | −0.41 | −0.16 | 0.32 |
| LRRC23 | −0.74 | 0.21 | 0.48 | 0.11 | 0.12 | AL133215.2 | 0.56 | −0.47 | 0.03 | 0.00 | −0.14 | HMGB1P15 | −0.89 | −1.11 | 1.52 | −1.03 | 0.90 |
| BHMT2 | −1.46 | 1.12 | 1.32 | 0.38 | 0.22 | AC020978.1 | −0.45 | 0.08 | 0.47 | 0.03 | 0.38 | NHLRC2 | 0.04 | 0.04 | −0.03 | 0.05 | −0.01 |
| AC096642.1 | −0.88 | 0.17 | 1.11 | −0.15 | 0.44 | PMCHL2 | −0.93 | −0.35 | 1.18 | −0.66 | 1.58 | AP001267.3 | −0.25 | −0.10 | 0.95 | 0.89 | 0.42 |
| AL445524.1 | 1.11 | −0.68 | −0.53 | −0.28 | −0.20 | AC025287.3 | −0.37 | 0.03 | 0.49 | 0.10 | 0.50 | HPGD | 0.12 | 0.30 | 0.60 | 0.33 | −0.38 |
| AC016885.3 | −2.65 | 2.96 | 3.07 | 1.22 | 0.23 | NPM1P19 | 0.64 | 0.78 | −0.62 | 0.47 | −1.42 | AL451137.1 | 0.34 | −0.48 | 0.80 | 0.07 | −0.64 |
| MLYCD | −0.56 | 0.28 | 0.19 | 0.32 | 0.11 | GNA13 | 0.16 | −0.11 | −0.01 | −0.15 | −0.19 | MIR30C1 | 0.21 | 0.65 | −0.56 | 0.51 | −0.75 |
| DOC2GP | −1.26 | 0.34 | 0.67 | 0.34 | 0.33 | KCNG1 | 0.49 | −0.14 | −0.71 | −0.10 | −0.68 | LINC02039 | −0.33 | −1.58 | 1.13 | −0.88 | 1.22 |
| NDUFB9 | 0.69 | −0.22 | −0.47 | −0.14 | −0.40 | RNU6-57P | 0.91 | 0.00 | 0.74 | 0.65 | 0.01 | ADAM28 | −0.10 | −0.13 | 0.74 | −0.39 | 0.58 |
| ATP6V1E1 | 0.56 | −0.19 | −0.57 | −0.05 | −0.53 | AL589745.2 | −1.28 | −1.22 | 0.12 | −2.05 | −0.62 | AL079301.1 | 0.24 | −0.67 | −3.04 | −0.05 | −1.96 |
| LINC00265 | −0.94 | 0.39 | 0.59 | 0.47 | 0.16 | KIAA1024L | −0.97 | 0.32 | 0.22 | 0.27 | 0.69 | LINC00269 | 0.26 | 0.30 | −1.73 | −0.01 | −1.80 |
| FEM1C | 0.45 | −0.11 | −0.47 | −0.04 | −0.38 | HLA-DRB5 | 0.36 | −0.48 | −0.07 | 0.05 | 0.73 | AC211476.2 | 0.10 | −0.21 | 0.43 | −0.20 | 0.20 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| EXTL3 | 0.61 | −0.28 | −0.56 | −0.05 | −0.27 | AC015971.1 | −0.28 | −0.01 | 0.28 | −0.04 | 0.23 | BEND3P2 | 0.63 | −0.26 | 0.38 | 1.05 | −1.13 |
| OGFOD1 | 0.52 | −0.37 | −0.40 | −0.19 | −0.17 | GIF | 0.66 | −0.71 | −0.19 | −0.28 | −0.19 | AC096659.1 | −0.74 | −0.22 | 0.76 | 0.71 | 0.96 |
| PMS2P4 | −0.60 | 0.31 | 0.21 | 0.27 | −0.04 | ADGRE4P | −0.48 | −0.12 | 0.40 | 0.31 | 0.59 | MPL | 0.12 | 0.08 | 0.38 | 0.25 | −0.27 |
| HERC1 | −0.19 | 0.15 | 0.19 | 0.04 | −0.04 | AC005730.2 | −1.00 | −0.81 | 1.97 | −1.98 | −0.91 | LINC02575 | −0.26 | 0.10 | 0.90 | −0.25 | −0.13 |
| FAM174B | −0.75 | 0.49 | 0.33 | −0.01 | 0.01 | LINC01126 | −0.43 | 0.13 | 0.20 | 0.50 | 0.33 | AL445205.1 | −0.26 | 1.11 | 1.17 | −0.07 | −0.89 |
| DNAJC6 | −0.94 | 0.38 | 0.25 | 0.18 | 0.00 | BICRAL | −0.15 | 0.21 | 0.32 | 0.02 | −0.02 | MAGEC1 | 0.34 | −1.13 | −1.92 | 0.34 | −0.09 |
| CDNF | −0.86 | 0.59 | 1.09 | 0.08 | 0.40 | AADACP1 | −0.49 | 0.36 | −0.57 | 0.93 | −0.76 | CTNNA2 | 0.21 | −0.18 | −1.03 | 0.49 | −0.40 |
| SF3B5 | 0.74 | −0.28 | −0.89 | 0.11 | −0.67 | CSF1R | −0.34 | 0.01 | 0.31 | −0.14 | 0.08 | AC136475.3 | 0.18 | −1.18 | −0.32 | −0.55 | 0.20 |
| KRT18P61 | −1.07 | 0.73 | 0.66 | 0.19 | −0.44 | LRFN2 | −1.07 | 0.35 | 0.93 | −0.75 | −0.45 | LINC02127 | 0.71 | −1.30 | −1.25 | 1.15 | −0.85 |
| AC022007.1 | −0.84 | 0.40 | 0.66 | 0.08 | 0.33 | RN7SL108P | 1.29 | −0.13 | −1.26 | 0.75 | 0.56 | EVPLL | 0.19 | −0.38 | 0.11 | 0.42 | 0.34 |
| AC009053.1 | −0.62 | 0.08 | 0.18 | 0.06 | 0.20 | KATNBL1P3 | 1.67 | −0.80 | −2.33 | 0.97 | −0.67 | AL590730.1 | 0.30 | 0.06 | −1.27 | 0.61 | −1.28 |
| HAVCRIP1 | −1.42 | 0.53 | 0.99 | 0.74 | 0.14 | KLHDC7A | −0.89 | 0.49 | −0.09 | 0.90 | 0.49 | RPL7P22 | 0.43 | 0.51 | −0.27 | 1.64 | 0.77 |
| HYDIN | −1.07 | 0.17 | 0.70 | −0.01 | 0.43 | RNU6-425P | 1.06 | −0.64 | 1.20 | 0.16 | 0.38 | AL391832.2 | 0.21 | −1.56 | 0.01 | 0.38 | 1.47 |
| PCIF1 | −0.47 | 0.33 | 0.20 | 0.26 | 0.09 | LINC00052 | 1.46 | −1.95 | −0.46 | 0.45 | 1.26 | CCDC71 | 0.05 | −0.08 | −0.07 | −0.06 | 0.10 |
| KRT9 | 2.06 | −0.15 | −1.29 | 1.88 | −2.17 | LRRC53 | −0.97 | 0.69 | 1.51 | 0.97 | 1.36 | LINC01776 | −0.35 | −1.26 | 0.02 | −0.15 | −1.80 |
| ADCY10P1 | −0.63 | 0.11 | 0.25 | −0.04 | 0.11 | PODXL2 | −0.28 | 0.13 | 0.25 | 0.11 | 0.25 | GPR160 | −0.07 | 0.05 | −0.19 | 0.04 | 0.08 |
| FGFR3 | −1.03 | 0.46 | 0.04 | 0.63 | 0.24 | AC114982.2 | 0.70 | −0.91 | 0.35 | −0.40 | −0.32 | GOLGA6C | 0.49 | 0.25 | −2.70 | 1.43 | −2.21 |
| AREL1 | 0.39 | −0.24 | −0.29 | −0.09 | −0.06 | PLPP1 | −0.33 | 0.47 | 0.80 | −0.07 | 0.03 | AC105429.1 | −0.06 | 0.14 | −0.11 | 0.20 | −0.05 |
| LNX1 | −0.83 | 0.77 | 1.01 | 0.07 | −0.27 | G32324 | −0.75 | −0.76 | 1.53 | −0.26 | 0.99 | RNU6-824P | −0.28 | 0.14 | 1.75 | −0.10 | 0.44 |
| CHRNA2 | −1.29 | 0.19 | 0.59 | −0.44 | 0.35 | AC027279.4 | −0.29 | 0.03 | 0.09 | 0.19 | 0.18 | AC027613.1 | −0.39 | 0.08 | 0.24 | 0.66 | 0.53 |
| EIF5B | 0.66 | −0.47 | −0.58 | −0.27 | −0.25 | CSTF2T | 0.14 | −0.22 | −0.16 | −0.17 | −0.11 | G353 | 0.26 | 0.27 | 0.91 | −0.17 | 1.02 |
| SNX1 | −0.35 | 0.23 | 0.34 | 0.04 | 0.11 | APLP1 | 0.49 | −0.90 | −0.11 | −0.43 | −0.07 | AL645728.1 | −0.10 | −0.32 | −0.56 | −0.04 | −0.03 |
| AC005477.1 | −2.09 | 0.32 | 1.40 | 0.23 | 0.33 | RPSAP17 | 0.94 | −1.04 | −1.83 | 0.74 | −1.31 | KLHL32 | −0.14 | −0.66 | −0.41 | −0.07 | −0.19 |
| CCDC124 | 0.66 | −0.30 | −0.93 | 0.03 | −0.53 | SH3KBP1 | −0.32 | 0.06 | 0.62 | −0.23 | 0.09 | AC006116.6 | 0.45 | −0.36 | −1.14 | 0.90 | −0.37 |
| FXYD5 | 0.77 | −0.68 | −1.00 | −0.33 | −0.10 | AL606760.1 | 0.60 | −0.38 | −0.21 | −0.22 | 0.16 | SHROOM1 | −0.10 | −0.04 | −0.34 | 0.33 | 0.10 |
| ATG4A | 0.73 | −0.19 | −0.44 | −0.13 | −0.35 | CFAP299 | −0.86 | 0.17 | −0.13 | 0.06 | −0.59 | MIR3939 | −0.20 | 0.40 | 0.63 | −0.33 | 0.23 |
| PGAP3 | −0.67 | 0.60 | 0.47 | 0.33 | 0.11 | RGS5 | −0.36 | 0.68 | 0.88 | 0.10 | −0.26 | AC009133.3 | −0.30 | 1.20 | −0.22 | 0.09 | 0.04 |
| CCDC171 | −0.58 | 0.34 | 0.71 | 0.18 | 0.19 | AC004865.1 | 0.40 | −0.21 | −0.35 | 0.01 | −0.08 | SNORD114-3 | −0.18 | 0.41 | 1.29 | −0.69 | −0.32 |
| PHC2 | 0.49 | −0.39 | −0.34 | −0.35 | −0.20 | AC093426.1 | −1.03 | −0.98 | −2.52 | 0.77 | −0.19 | AC009090.3 | −0.15 | −0.43 | 1.09 | −0.10 | 1.00 |
| G1561 | −1.35 | 0.75 | 1.66 | 0.28 | 0.59 | AC009032.1 | 0.33 | −0.27 | 0.12 | −0.15 | −0.08 | RN7SKP24 | −0.64 | 1.47 | −2.22 | 0.12 | −2.88 |
| ITGA6-AS1 | 1.21 | −0.44 | −1.29 | 0.00 | −0.28 | ANXA2P1 | −0.40 | 0.58 | 0.48 | 0.32 | −0.22 | ELMO1-AS1 | 0.14 | −0.25 | 0.09 | −0.08 | 0.37 |
| MYRIP | −0.96 | 0.71 | 1.02 | 0.45 | 0.61 | AL137793.1 | −1.28 | 1.64 | 0.30 | 1.86 | −0.13 | AC091885.2 | −0.38 | 1.34 | −0.02 | 0.47 | −0.34 |
| ANKRD24 | −1.42 | 0.07 | 0.92 | 0.19 | 0.47 | HMGB1P10 | 0.33 | −0.26 | −0.79 | 0.04 | −0.19 | RASGEF1B | −0.06 | 0.14 | 0.34 | 0.11 | 0.20 |
| JPH2 | −1.14 | 0.65 | 0.20 | 0.44 | −0.37 | KLLN | 0.39 | 0.01 | −0.05 | −0.08 | −0.26 | AC004832.1 | −0.35 | −0.17 | −0.92 | −0.10 | 1.10 |
| RGS11 | −1.17 | 1.18 | 0.98 | 0.28 | −0.06 | APOB | −0.53 | 0.56 | 0.63 | 1.45 | −0.18 | RPL22P23 | −0.19 | 0.41 | −0.02 | 0.39 | −0.14 |
| PACS2 | −0.69 | 0.37 | 0.30 | 0.34 | 0.23 | SMC5-AS1 | −0.29 | 0.19 | 0.50 | −0.17 | 0.14 | PAICSP2 | 0.47 | −0.60 | −1.18 | 0.08 | −1.40 |
| ACSBG2 | −0.95 | −0.04 | 0.94 | 0.06 | 0.87 | MIR561 | −1.10 | 1.37 | 1.26 | 0.05 | 0.09 | FAM209B | 0.22 | 0.28 | −0.61 | −0.05 | −1.13 |
| LFNG | −0.84 | 0.41 | 0.03 | 0.46 | 0.06 | FGF7 | −0.49 | 0.19 | 1.11 | −0.79 | −0.04 | KRI1 | −0.06 | −0.15 | −0.23 | 0.06 | 0.18 |
| FGF22 | −1.36 | 1.64 | 2.48 | 0.20 | 0.16 | FRMD6-AS1 | 0.38 | −0.09 | −0.20 | 0.26 | 0.29 | AL591424.3 | 0.42 | −1.46 | −0.55 | 1.06 | 1.71 |
| PKD1P6 | −0.83 | 0.15 | 0.24 | 0.34 | 0.29 | C19orf57 | −0.22 | 0.23 | 0.19 | 0.24 | 0.08 | AL583842.1 | −0.81 | 1.06 | 1.24 | 0.49 | 0.08 |
| HMGCR | 1.01 | −0.29 | −0.71 | 0.06 | −0.50 | AL662907.1 | −0.40 | 0.74 | 0.71 | −0.04 | −0.30 | MLIP | −0.10 | 0.16 | −0.22 | 0.11 | −0.42 |
| RAB25 | 1.16 | −0.09 | −0.53 | 0.09 | −0.65 | RNU6-1322P | 0.92 | −0.14 | −1.34 | 0.00 | −1.06 | DBX1 | 0.52 | −0.26 | −0.19 | −0.12 | 1.90 |
| LEPROTL1 | 0.65 | −0.17 | −0.06 | −0.14 | −0.20 | HSD17B6 | −0.45 | 0.27 | −0.68 | 0.09 | −1.24 | AP001208.1 | 0.85 | −1.67 | 1.55 | −0.41 | 1.42 |
| AL627402.1 | 0.79 | −0.12 | −0.72 | 0.08 | −0.27 | AP001273.1 | 0.27 | −0.30 | −0.04 | −0.11 | 0.28 | NPBWR1 | 0.18 | 0.29 | −0.09 | 0.66 | −0.85 |
| NCAPG2 | 0.75 | −0.63 | −0.86 | −0.19 | −0.32 | AC004986.1 | −0.68 | 0.29 | 1.15 | −0.49 | 0.31 | LY6G6C | 0.11 | 0.21 | 0.20 | 0.54 | −0.22 |
| AC093583.1 | −1.22 | 0.67 | 0.86 | −0.14 | 0.33 | DNM3 | −0.15 | 0.23 | 0.20 | 0.10 | 0.00 | MIR548AM | 0.27 | −1.49 | −1.16 | 0.41 | 0.84 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| NSA2 | 0.70 | −0.47 | −0.44 | −0.35 | −0.33 | PRR13P2 | 0.41 | 0.15 | −1.26 | 0.26 | −0.75 | CUBNP1 | −0.81 | −0.39 | 0.27 | −1.18 | 0.27 |
| KCMF1 | 0.60 | −0.25 | −0.53 | −0.14 | −0.45 | CERS6-AS1 | −0.65 | 0.13 | 1.22 | −0.22 | 1.12 | AC103957.1 | −0.35 | −0.32 | 0.13 | 0.04 | 0.43 |
| OSCP1 | −0.63 | 0.36 | 0.55 | −0.08 | 0.06 | AC109635.6 | −1.39 | 0.10 | 1.06 | −0.14 | 0.83 | MUCL3 | −0.20 | 0.01 | −0.63 | 0.24 | −0.71 |
| LIMS2 | −0.97 | 0.42 | 0.86 | 0.30 | 0.23 | AC024451.1 | 0.39 | −0.44 | 0.23 | −0.02 | 0.47 | LINC02133 | 0.19 | −0.46 | −2.29 | 0.49 | −1.41 |
| FNDC5 | −0.92 | 0.66 | 0.52 | 0.44 | −0.05 | RNU6-537P | 0.97 | −0.97 | −0.98 | −0.56 | −1.02 | AL121992.2 | −0.22 | −0.17 | 0.35 | −0.90 | 0.47 |
| CUBNP3 | −2.11 | 0.72 | −0.27 | 0.26 | 0.10 | EFCAB11 | −0.20 | −0.12 | 0.18 | −0.16 | 0.22 | GPR139 | 0.38 | −0.41 | −2.73 | 0.84 | −1.57 |
| ATP12A | 2.49 | −1.76 | −2.29 | −1.29 | −0.07 | MORC2-AS1 | −0.47 | −0.17 | 0.15 | −0.83 | −0.51 | C20orf202 | −0.21 | 0.41 | 0.43 | −0.01 | −0.03 |
| DDX20 | 0.50 | −0.37 | −0.29 | −0.22 | −0.08 | MGRN1 | −0.11 | −0.01 | 0.01 | −0.11 | 0.02 | CBX3P3 | 0.16 | −0.28 | −0.14 | −0.04 | 0.09 |
| NUP62 | 0.64 | −0.46 | −0.73 | −0.13 | −0.17 | AC102941.1 | 1.45 | −1.51 | −2.01 | 0.40 | 1.34 | CCDC22 | −0.06 | 0.08 | −0.18 | 0.19 | 0.07 |
| AC012085.1 | 1.76 | −0.29 | −1.90 | 0.17 | −0.95 | HLA-L | −0.23 | −0.42 | 0.11 | −0.25 | 0.14 | MTCO1P24 | −0.43 | −0.68 | −0.23 | 0.56 | −0.69 |
| RNU6-1159P | −2.45 | −0.16 | 3.30 | 0.12 | 1.09 | KCTD7 | −0.21 | 0.25 | 0.29 | 0.13 | −0.08 | CFB | 0.08 | −0.26 | −0.14 | −0.32 | −0.38 |
| KRT72 | −1.81 | 1.66 | 1.80 | 1.50 | 0.09 | RNU2-65P | −0.44 | −0.39 | 0.48 | 0.23 | 0.88 | MOGS | 0.05 | 0.03 | −0.14 | 0.11 | 0.08 |
| DMTN | −0.93 | 0.59 | 0.37 | 0.17 | −0.19 | CCND2-AS1 | −0.45 | −0.25 | −0.09 | −0.02 | −0.21 | AC105362.1 | −0.80 | −1.00 | −0.49 | 0.04 | −0.97 |
| PIF1 | 1.21 | −1.40 | −1.85 | −0.51 | −0.25 | RNA5SP364 | 1.00 | −1.11 | −0.06 | 0.16 | 1.08 | PRAMEF1 | 0.58 | 0.24 | −1.01 | −0.11 | −1.70 |
| DRD4 | −1.75 | 0.84 | 1.40 | 0.59 | 0.79 | MS4A4A | −0.54 | 0.10 | 0.71 | −0.02 | 0.12 | G2112 | 0.23 | −0.27 | 0.23 | 0.72 | 1.01 |
| AC093879.1 | −1.65 | 1.26 | 1.30 | 0.24 | 0.58 | AL355355.1 | −0.49 | 0.44 | 0.22 | 0.38 | 0.03 | FGF8 | −0.29 | −0.93 | −0.41 | −0.47 | 0.27 |
| LINC01266 | −1.71 | 0.71 | 0.37 | −0.04 | −1.19 | ALG9 | −0.15 | −0.08 | 0.19 | 0.06 | 0.19 | AC106895.1 | 0.42 | −1.44 | −2.39 | 0.68 | −0.68 |
| CARNMT1 | 0.45 | −0.27 | −0.27 | −0.16 | 0.08 | AC087294.1 | −0.29 | −0.17 | 0.30 | −0.19 | 0.02 | AC026412.3 | −0.08 | 0.10 | −0.33 | 0.20 | −0.12 |
| MYO1D | 0.51 | −0.18 | −0.31 | −0.18 | −0.33 | AC105036.1 | 0.44 | −0.24 | 0.12 | −0.30 | 0.03 | NANOGNBP1 | 0.57 | −0.76 | −1.06 | −0.46 | −1.29 |
| IFI44L | 1.22 | −1.19 | −0.98 | −0.98 | −0.28 | AL136115.2 | 0.44 | −0.24 | 0.02 | −0.14 | 0.25 | EEF1A1P29 | 0.22 | 0.47 | 0.16 | −0.19 | −0.31 |
| NPM1P41 | 1.59 | −0.27 | −0.97 | −0.08 | −0.17 | ADGRF4 | 0.33 | 0.17 | 0.20 | 0.28 | 0.02 | CCDC70 | 0.63 | −1.18 | −1.03 | 1.07 | 0.00 |
| KANK2 | −1.01 | 0.46 | 0.67 | 0.23 | −0.09 | MS4A1 | 0.74 | −0.62 | 0.63 | −0.58 | 0.28 | LINC00567 | −0.39 | −0.52 | 0.62 | −1.78 | −0.27 |
| MFAP3 | 0.49 | −0.37 | −0.21 | −0.30 | −0.13 | AC106782.2 | −0.42 | 0.30 | −0.08 | 0.27 | −0.27 | L22NC01-81G9. | 0.49 | −1.61 | 1.48 | −0.84 | 1.72 |
| EPN2-AS1 | −0.89 | 0.49 | 0.82 | 0.17 | 0.18 | NMD3P1 | −0.99 | 0.94 | 2.30 | 0.23 | 0.29 | AP000459.1 | −0.50 | 0.30 | −1.50 | 0.19 | −0.74 |
| AC060780.1 | −0.47 | 0.07 | 0.76 | −0.07 | 0.29 | LINC01361 | −0.90 | 0.60 | 1.26 | −0.20 | −0.02 | MAPK8IP1P1 | −0.49 | −0.04 | 1.81 | 0.35 | 4.09 |
| GPATCH4 | 0.75 | −0.78 | −0.78 | −0.31 | 0.09 | AC066613.1 | 0.39 | −0.41 | 0.57 | −0.43 | 0.09 | RNU2-33P | −0.18 | −0.12 | 0.66 | −0.33 | −0.90 |
| GDPD1 | −0.91 | 0.43 | 0.86 | 0.43 | 0.30 | CDK5RAP2 | −0.14 | 0.01 | −0.14 | −0.04 | 0.01 | SLC35D2 | −0.06 | −0.05 | −0.36 | 0.01 | 0.16 |
| SPTBN1 | −0.83 | 0.49 | 0.58 | 0.18 | 0.08 | AL354928.1 | −0.66 | 0.31 | −1.07 | 0.30 | −0.13 | AL133279.3 | 0.38 | −0.48 | 0.22 | −0.55 | −1.17 |
| RAI2 | −1.40 | 0.91 | 2.03 | 0.40 | 0.42 | RNU6-262P | 1.40 | −0.90 | −0.06 | 0.06 | 0.20 | AC233699.1 | 0.46 | −0.17 | −0.85 | −1.08 | −0.80 |
| KIAA1755 | −1.25 | 0.25 | 0.79 | 0.37 | 0.34 | AC068473.3 | −0.58 | 0.74 | 1.11 | −0.36 | −0.50 | LINC01111 | −0.65 | 0.47 | −0.48 | 1.20 | −0.78 |
| HSD17B12 | 0.66 | −0.27 | −0.54 | −0.02 | −0.29 | AL161626.1 | −0.52 | 0.33 | 0.61 | 0.65 | −0.51 | AL133485.1 | 0.17 | 0.17 | −0.48 | −0.02 | −0.26 |
| NDUFS6 | 0.59 | −0.35 | −0.34 | −0.18 | −0.08 | AC110609.1 | −1.27 | 1.29 | 2.29 | 0.25 | 0.69 | F3 | 0.09 | 0.18 | 0.18 | −0.26 | −0.07 |
| LNX2 | 0.62 | −0.06 | −0.39 | −0.01 | −0.24 | EXOSC3 | 0.20 | −0.14 | −0.15 | −0.05 | 0.12 | HAND1 | −0.41 | 0.25 | −0.07 | 0.15 | −1.87 |
| CHMP4B | 0.62 | −0.10 | −0.42 | −0.10 | −0.41 | NFKBIZ | 0.23 | −0.15 | −0.67 | 0.05 | −0.11 | AC012048.1 | −0.19 | 0.59 | −1.01 | −0.20 | −1.25 |
| EI24 | 0.74 | −0.29 | −0.47 | −0.14 | −0.29 | AC090498.1 | 0.29 | 0.19 | 0.25 | 0.18 | −0.40 | AL109811.1 | −0.17 | −0.80 | 0.64 | −0.38 | 0.59 |
| MIR663B | 1.01 | −0.45 | −0.40 | −0.11 | 0.30 | AC126177.2 | −1.34 | 1.09 | 1.13 | 1.08 | −0.36 | ALOXE3 | 0.11 | 0.12 | 0.25 | −0.08 | −0.20 |
| DSTN | 0.73 | −0.09 | −0.39 | −0.14 | −0.59 | AC011815.1 | 0.25 | −0.05 | −0.15 | 0.12 | −0.11 | AC096741.1 | 0.08 | −0.26 | −0.10 | −0.37 | −0.02 |
| AC092718.4 | 1.35 | −0.94 | −1.39 | −0.28 | −0.77 | RPL11P4 | 1.29 | −0.66 | −1.24 | 0.41 | −0.38 | DNAJC19P7 | −0.19 | 0.19 | 0.16 | 0.21 | −0.51 |
| PRSS51 | −0.71 | 0.43 | 0.84 | −0.01 | 0.13 | AL109935.1 | 0.84 | −1.91 | −0.11 | −0.94 | 1.08 | AP001189.6 | 0.81 | −0.63 | −1.71 | −1.14 | −2.13 |
| INTS3 | −0.50 | 0.10 | 0.48 | −0.02 | 0.24 | RPL21P135 | −0.72 | 0.89 | 0.73 | 0.38 | 0.33 | MIR548H1 | −0.17 | 0.78 | 0.83 | 0.40 | −0.62 |
| STRN3 | 0.40 | −0.14 | −0.44 | −0.06 | −0.22 | CD86 | 0.46 | −0.46 | −0.31 | −0.53 | −0.26 | LINC00534 | −0.41 | 0.49 | −0.49 | 0.52 | −0.44 |
| FBLN5 | −1.25 | 0.64 | 1.49 | 0.01 | 0.12 | AC243654.2 | 0.43 | −0.13 | 0.02 | 0.13 | 0.31 | AL392183.1 | −0.19 | 0.14 | 0.12 | 0.43 | 0.28 |
| SHISA6 | −1.02 | 0.16 | 0.24 | 0.69 | 0.21 | AC015712.6 | −0.61 | −0.11 | 0.52 | −0.27 | 0.68 | AC079089.3 | 0.32 | −1.62 | 0.71 | −0.18 | 0.74 |
| KCNJ1 | −1.16 | 0.27 | 0.25 | 0.22 | −0.20 | RPL3P1 | −0.46 | 1.00 | 0.98 | 0.15 | −0.33 | AC106871.1 | 0.46 | −1.13 | −1.59 | 0.07 | 0.19 |
| MIPOL1 | −0.51 | 0.25 | 0.41 | 0.07 | 0.09 | AL049637.1 | 0.31 | −0.06 | 0.20 | 0.03 | 0.29 | OR7E41P | 0.36 | −2.24 | −1.01 | −0.07 | 1.41 |
| MTMR6 | 0.53 | −0.19 | −0.34 | −0.11 | −0.40 | AL390036.1 | −0.47 | 0.17 | 0.47 | 0.03 | −0.40 | 12-Sep | −0.47 | 0.29 | −0.62 | 1.27 | 0.51 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| ARHGAP24 | −0.59 | 0.43 | 0.42 | −0.04 | −0.19 | AL031281.1 | 0.50 | 0.07 | 0.15 | 0.04 | 0.20 | AC009041.1 | 0.52 | 0.53 | −1.85 | −1.17 | −1.18 |
| LIN9 | 0.75 | −0.46 | −0.42 | −0.15 | −0.13 | FAM87B | −0.27 | 0.19 | 0.34 | 0.08 | 0.13 | AC026798.1 | 0.92 | −0.67 | −1.51 | 0.46 | 1.17 |
| LTA4H | 0.52 | −0.22 | −0.44 | 0.06 | −0.14 | NR2E3 | −0.36 | 0.53 | −0.80 | 0.62 | −0.04 | AL365440.2 | 0.54 | −0.79 | −2.48 | 0.67 | 2.55 |
| EIF4G3 | 0.35 | −0.20 | −0.37 | −0.07 | −0.20 | HMGB1P19 | 0.33 | −0.17 | −0.82 | 0.07 | −0.43 | MEGF9 | 0.06 | 0.34 | 0.35 | 0.25 | −0.11 |
| POLR2B | 0.42 | −0.14 | −0.29 | −0.03 | −0.19 | JAZF1 | −0.24 | 0.25 | 0.53 | 0.06 | −0.06 | AC019226.1 | 0.12 | −0.31 | 0.54 | 0.09 | 0.93 |
| PPP1R9A | −1.54 | 0.94 | 0.92 | 0.79 | 0.31 | MTND6P22 | −0.55 | −0.58 | 0.38 | −0.44 | −0.02 | COL18A1 | −0.07 | −0.13 | −0.40 | 0.11 | −0.12 |
| C16orf72 | 0.41 | −0.20 | −0.54 | −0.03 | −0.38 | RNA5SP217 | 0.51 | −0.06 | −0.25 | 0.30 | 0.16 | CACNG1 | −0.26 | −1.55 | 0.11 | 0.53 | 2.55 |
| ECPAS | 0.39 | −0.20 | −0.34 | −0.13 | −0.17 | AC093602.1 | −0.79 | −0.40 | −0.79 | −0.13 | 1.15 | LINC02125 | −0.40 | −0.85 | 0.63 | −0.97 | 0.92 |
| FRA10AC1 | −0.34 | 0.10 | 0.42 | 0.04 | 0.25 | PPFIBP1 | −0.15 | 0.02 | 0.01 | −0.15 | −0.05 | OR5B3 | −0.64 | 0.51 | 0.19 | 1.93 | −1.46 |
| PSMD3 | 0.48 | −0.14 | −0.57 | −0.06 | −0.34 | PRSS16 | −0.27 | 0.01 | −0.15 | −0.08 | −0.08 | NEK2P4 | −0.66 | 0.29 | 0.05 | −1.84 | −0.70 |
| PSMF1 | 0.43 | −0.11 | −0.31 | −0.07 | −0.14 | RPL7P25 | 0.44 | −0.16 | −0.44 | −0.25 | −0.48 | PTGIR | −0.11 | −0.71 | −0.20 | −0.46 | 0.32 |
| SDCBP2 | 0.93 | −0.25 | −1.33 | 0.24 | −0.94 | AC130324.2 | −0.57 | −0.27 | 0.89 | −0.04 | 1.01 | RNU4-30P | 0.71 | −0.87 | 0.32 | −0.95 | 0.77 |
| PDP1 | 0.56 | −0.21 | −0.46 | −0.23 | −0.31 | ACTBP7 | −0.69 | −0.59 | −0.31 | 0.02 | 0.39 | GLYCTK-AS1 | 0.08 | 0.01 | −0.07 | 0.05 | 0.21 |
| GPC4 | −0.93 | 0.50 | 0.61 | 0.36 | 0.04 | ITGB2 | 0.37 | −0.61 | −0.01 | −0.29 | 0.01 | LARGE-IT1 | 0.17 | −0.90 | 1.34 | −0.87 | 1.02 |
| PPIL6 | −1.04 | 0.48 | 1.26 | 0.19 | 0.43 | SNORD14A | 0.42 | 0.20 | −0.12 | −0.10 | −1.01 | ABCC2 | −0.08 | 0.19 | −0.84 | 0.36 | −0.64 |
| SCAF11 | 0.34 | −0.16 | −0.15 | −0.13 | −0.08 | RN7SL568P | 1.18 | −1.55 | 0.11 | 0.62 | 1.47 | OR10J8P | −0.65 | −0.19 | −0.90 | −0.91 | −1.85 |
| NAE1 | 0.55 | −0.23 | −0.52 | −0.07 | −0.34 | AC025188.1 | −0.70 | −0.48 | 0.78 | 0.34 | 1.12 | ORC2 | 0.03 | −0.03 | −0.10 | 0.07 | 0.05 |
| G34301 | −2.51 | 1.06 | 2.32 | 0.38 | 0.17 | AP000266.1 | 0.44 | −0.36 | 0.30 | 0.15 | 0.48 | FAM129C | −0.13 | −0.53 | 0.47 | −0.61 | 0.13 |
| RNU1-28P | −1.39 | 0.44 | 0.10 | 0.55 | −0.12 | AL034417.4 | 0.31 | −0.21 | 0.24 | −0.39 | 0.07 | AP000894.4 | −0.27 | 0.00 | 1.28 | −0.48 | 0.29 |
| POLD4 | −0.91 | 0.44 | 0.40 | 0.31 | 0.22 | AC105137.2 | −0.36 | 0.22 | 0.53 | 0.15 | 0.30 | MINK1 | 0.06 | −0.05 | −0.54 | 0.20 | 0.06 |
| AC092747.4 | 0.96 | −0.09 | −0.52 | 0.11 | −0.31 | RPL35AP | −1.99 | −0.39 | 0.52 | −0.13 | 1.66 | LINC01847 | −0.26 | 0.34 | −0.42 | 0.64 | −0.54 |
| SRGAP2C | −0.66 | 0.44 | 0.72 | 0.21 | −0.04 | SNORD77 | 0.96 | −2.52 | −0.06 | −0.06 | 1.18 | AC011287.1 | −0.16 | −0.01 | −0.41 | 0.51 | −0.58 |
| MLXIP | −0.57 | 0.13 | 0.28 | 0.01 | 0.12 | AC002059.2 | 0.54 | −0.31 | 0.07 | −0.13 | 0.02 | AP000867.1 | 0.36 | −1.75 | 0.57 | −0.67 | 1.39 |
| ANKRD17 | 0.30 | −0.13 | −0.22 | −0.09 | −0.11 | AL354714.1 | −0.87 | 0.75 | −0.29 | 0.25 | −0.46 | AL592295.4 | −0.11 | 0.04 | 0.98 | −0.03 | 0.64 |
| SPATA24 | 1.31 | −0.40 | −1.17 | −0.07 | −0.60 | RNU6-861P | −1.13 | 1.41 | 0.99 | −0.98 | −0.34 | AC007376.2 | −0.26 | 0.67 | 0.93 | 0.09 | −0.32 |
| AC010368.1 | −2.07 | −0.30 | 0.50 | −0.23 | 0.46 | G34428 | −0.41 | 0.11 | −0.64 | 0.50 | −0.06 | RBM45 | −0.04 | −0.01 | 0.14 | 0.05 | 0.09 |
| NDUFS5 | 0.68 | −0.22 | −0.38 | −0.18 | −0.44 | HSD17B1 | −0.19 | 0.12 | 0.37 | 0.21 | 0.43 | SNORA81 | −0.14 | 0.19 | 0.86 | 0.46 | 0.72 |
| PPM1J | −0.97 | 0.51 | 0.55 | 0.56 | 0.53 | LPP | −0.18 | 0.06 | 0.08 | −0.05 | −0.17 | GPRC6A | 0.34 | −0.92 | −0.66 | 0.29 | 0.09 |
| SEC23B | 0.59 | −0.34 | −0.48 | −0.23 | −0.25 | AC087632.1 | 0.44 | −0.04 | 0.08 | −0.29 | 0.28 | RPL12P33 | −0.28 | −1.18 | −1.21 | −0.02 | −0.05 |
| MPHOSPH8 | −0.43 | 0.18 | 0.33 | −0.02 | 0.06 | AC008894.3 | 0.35 | −0.53 | −1.21 | −0.69 | −0.43 | PTCHD4 | 0.12 | −0.37 | −0.06 | 0.21 | 0.31 |
| AL391005.1 | −2.43 | 1.09 | 1.70 | 0.99 | 0.27 | BDH2P1 | −1.01 | 0.86 | 2.46 | −0.65 | −0.41 | IGKV1-27 | 1.14 | −0.55 | −0.81 | 1.99 | −0.46 |
| SELENOI | 1.09 | −0.31 | −0.46 | −0.01 | −0.32 | AP000676.4 | 0.67 | 0.25 | −0.76 | 0.37 | 0.08 | PRSS36 | 0.09 | −0.01 | −0.58 | 0.72 | −0.02 |
| AC078883.2 | 1.65 | −0.51 | −2.46 | −0.04 | −0.89 | LRRC14 | −0.22 | 0.21 | 0.20 | 0.18 | 0.17 | CT83 | 0.39 | −0.70 | −0.85 | −1.12 | −0.25 |
| L3MBTL4-AS1 | −0.99 | 0.58 | 1.06 | −0.36 | 0.18 | RAD54L2 | −0.10 | 0.06 | −0.13 | 0.05 | −0.05 | OR2AE1 | −0.20 | 0.61 | 0.64 | −0.75 | −0.89 |
| REPS2 | −0.71 | 0.67 | 0.45 | 0.23 | 0.07 | ANKRD13B | −0.22 | 0.34 | 0.10 | 0.40 | 0.32 | MIR2909 | 0.19 | 0.24 | 0.51 | −0.35 | 0.53 |
| PPAT | 0.69 | −0.45 | −0.46 | −0.15 | −0.02 | LINC02004 | −0.86 | 0.97 | 0.46 | 1.10 | −0.28 | AC118555.1 | 0.16 | −0.27 | 0.10 | 0.03 | 0.27 |
| RFC4 | 0.70 | −0.50 | −0.63 | −0.23 | −0.06 | GOLGA2P4 | −0.65 | −0.15 | 1.27 | −0.99 | 0.50 | C10orf120 | 1.01 | 0.21 | −0.98 | −0.23 | −1.95 |
| SH3GL1P2 | −1.14 | 0.49 | 0.43 | 0.52 | −0.02 | GMDS | 0.20 | −0.10 | −0.38 | 0.02 | 0.02 | AL353726.1 | 0.44 | 0.22 | −1.59 | −0.37 | −1.66 |
| PTPRVP | −1.67 | 0.27 | 1.15 | 0.40 | 0.50 | DNAJB14 | 0.14 | −0.01 | −0.01 | 0.04 | −0.06 | A2MP1 | −0.14 | 0.23 | 0.88 | −0.03 | 0.69 |
| ECT2L | −0.75 | 0.44 | 0.59 | 0.40 | 0.32 | RNU6-288P | 1.11 | −0.82 | −0.49 | 0.44 | 1.36 | AL592431.1 | −0.52 | 0.55 | 0.65 | −0.47 | −1.22 |
| RNU6-103P | 2.33 | 0.39 | −1.27 | 0.51 | −0.75 | AC006014.1 | −0.82 | 0.38 | 0.95 | 0.02 | 0.31 | LINC01082 | −0.48 | −1.58 | −0.59 | 0.81 | −0.29 |
| FFAR4 | −1.41 | 0.48 | 0.92 | −0.08 | 0.33 | AP005131.3 | −0.37 | 0.36 | 0.01 | −0.14 | 0.08 | RNY4P24 | −0.19 | −0.54 | −0.72 | 0.06 | −0.18 |
| FGD3 | 0.78 | −0.40 | −0.39 | −0.44 | −0.20 | RNA5SP218 | −1.08 | 0.40 | −0.43 | 1.24 | 0.13 | FAM19A3 | 0.26 | −0.39 | −0.37 | 0.26 | 0.18 |
| DCAF16 | −0.36 | 0.10 | 0.21 | 0.12 | 0.23 | AC120049.1 | 0.28 | 0.18 | −0.08 | −0.19 | −0.42 | AL162274.1 | 0.12 | −0.21 | −0.43 | −0.17 | −0.19 |
| CKS1BP1 | 1.63 | −0.41 | −1.06 | 0.22 | −0.67 | LOXL2 | 0.31 | −0.59 | −0.36 | −0.69 | −0.49 | AP002992.1 | −0.42 | −0.88 | −0.86 | 0.36 | −0.16 |
| DBI | 0.96 | −0.02 | −0.30 | 0.12 | −0.61 | BANF1P2 | −0.82 | 0.63 | −0.27 | 0.93 | 1.07 | SLC35G6 | −0.12 | −0.06 | −0.12 | 0.21 | 0.14 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| NEURL4 | −0.72 | 0.16 | 0.19 | 0.18 | 0.28 | ARMS2 | −0.78 | 0.90 | 0.92 | −0.10 | −0.70 | LCORL | 0.04 | 0.13 | 0.08 | 0.01 | −0.11 |
| MPZ | −1.21 | 0.40 | 1.38 | −0.14 | 0.63 | OR10AD1 | −0.43 | −0.24 | 0.64 | −0.26 | 0.17 | SOX2 | −0.13 | 0.21 | 0.15 | 0.31 | 0.46 |
| SLC10A6 | 1.01 | −0.18 | −0.53 | −0.27 | −0.37 | AC027644.3 | 0.83 | −0.05 | 0.83 | −0.52 | 0.00 | OR8D1 | 0.27 | 0.12 | −0.14 | 0.21 | 1.08 |
| PCDH7 | 0.93 | −0.37 | −1.02 | 0.08 | −0.50 | G28021 | −0.66 | 0.58 | 0.40 | 0.40 | −0.38 | CEACAM20 | 0.33 | −1.16 | 0.39 | −0.30 | 1.04 |
| AL359999.1 | 3.52 | −2.18 | −4.29 | 0.25 | −2.97 | NME5 | −0.59 | 0.93 | −0.35 | 0.49 | −0.61 | AC006065.1 | 0.95 | 1.00 | −1.60 | 0.76 | −2.83 |
| PKP3 | 0.93 | −0.19 | −1.12 | 0.27 | −0.68 | RNU6-580P | 0.79 | −0.63 | −0.79 | −0.14 | −0.05 | RNU6-433P | −0.14 | 0.13 | 0.70 | 0.02 | 0.45 |
| AC018730.2 | −2.85 | 0.67 | 2.43 | 0.55 | 1.50 | AC010260.1 | 0.53 | −0.31 | 0.36 | 0.12 | 0.32 | LINC01770 | 0.15 | −0.19 | −0.32 | 0.64 | 0.99 |
| LENG8 | −0.77 | 0.24 | 0.20 | 0.27 | 0.25 | BIN3 | −0.20 | 0.12 | −0.25 | 0.18 | −0.19 | AC025437.4 | −0.55 | −0.18 | 1.94 | −0.74 | 1.47 |
| SPTLC1 | 0.55 | −0.20 | −0.37 | −0.24 | −0.38 | CHAT | 0.87 | −1.74 | −1.65 | −0.68 | 0.93 | MIR3126 | 0.24 | −0.14 | −0.04 | 0.53 | 0.37 |
| ALDH5A1 | −0.89 | 0.53 | 1.20 | 0.57 | 0.65 | AC021092.1 | 0.92 | −0.02 | 0.83 | 0.67 | 0.38 | RPL39P5 | −0.19 | 0.82 | −0.56 | 0.70 | −0.41 |
| PICALM | 0.46 | −0.20 | −0.38 | 0.01 | −0.20 | RNA5SP85 | −1.26 | 2.15 | −1.10 | 1.98 | −1.92 | BET1L | −0.04 | 0.05 | −0.06 | 0.01 | −0.05 |
| SLC20A1 | 0.93 | −0.78 | −1.42 | −0.31 | −0.75 | AC005072.1 | 0.35 | −0.58 | −0.40 | −0.17 | 0.44 | AC092159.1 | −0.41 | 0.80 | 1.25 | 1.39 | 1.95 |
| EBPL | 0.91 | −0.47 | −0.32 | −0.15 | 0.00 | AC112694.2 | 0.54 | −0.40 | 0.29 | −0.08 | 0.30 | G38557 | −0.61 | −0.05 | 0.61 | 0.24 | −1.08 |
| KLHL18 | 0.49 | −0.14 | −0.33 | −0.04 | −0.33 | AC009078.3 | 0.40 | −0.40 | −0.85 | 0.01 | −0.21 | IGHV1-46 | 0.62 | 0.56 | 0.28 | −0.15 | −2.10 |
| AL513164.1 | 1.84 | −0.44 | −0.31 | 0.05 | 0.03 | PIP5K1A | 0.12 | −0.12 | −0.04 | −0.06 | 0.01 | SPATA48 | 0.41 | −1.70 | −1.45 | 1.00 | 1.13 |
| DUSP6 | 1.08 | −0.68 | −1.24 | −0.38 | −0.73 | AL354808.2 | 0.32 | −0.26 | −0.16 | −0.06 | 0.27 | AC062032.1 | 0.27 | −0.81 | −0.43 | 0.43 | −0.08 |
| KRT8P48 | −1.64 | 1.04 | 0.38 | 1.39 | −0.04 | RNU7-48P | 1.02 | 0.26 | −0.64 | 0.07 | −0.70 | ITPRID2 | −0.04 | 0.38 | 0.27 | 0.08 | −0.11 |
| GABARAPL1 | −0.95 | 0.76 | 0.65 | 0.24 | −0.09 | AC005329.1 | −0.77 | 0.83 | 0.22 | 1.36 | 0.44 | RFX6 | 0.24 | −1.30 | −0.78 | 0.85 | 0.52 |
| DST | 0.53 | 0.00 | −0.62 | 0.00 | −0.31 | RNU6-1011P | 1.00 | −0.97 | 0.04 | 0.02 | 0.54 | SNRPD2P1 | −0.32 | 1.30 | 0.27 | 1.79 | −0.63 |
| N6AMT1 | −0.65 | 0.35 | 0.99 | −0.16 | 0.39 | MAPRE2 | 0.21 | 0.33 | 0.11 | 0.14 | −0.59 | AL590240.3 | −0.65 | −0.90 | 1.39 | −1.53 | 1.90 |
| FAM86C1 | 0.72 | −0.20 | −0.44 | −0.05 | −0.13 | ALKAL2 | −0.44 | 0.56 | 1.63 | 0.55 | 1.20 | OXCT2P1 | −0.27 | 0.06 | −0.49 | −0.49 | −0.12 |
| ACVR2B | −0.54 | 0.39 | 0.52 | 0.28 | 0.31 | AC046158.4 | −0.32 | 0.00 | 0.33 | 0.32 | 0.30 | AC007848.2 | −0.34 | 0.17 | −0.21 | −0.26 | −1.02 |
| RPS6KC1 | 0.35 | −0.15 | −0.07 | −0.18 | −0.12 | AC002128.2 | −0.35 | −0.57 | 0.51 | 0.01 | 0.98 | AL359547.1 | −0.38 | −1.14 | −1.30 | −1.72 | −0.83 |
| G4024 | 2.19 | −1.13 | −3.18 | 0.15 | −1.63 | BX842568.2 | −0.81 | −0.35 | −0.22 | −0.33 | 0.00 | KNOP1P5 | 0.81 | −0.19 | −0.90 | −1.10 | −1.58 |
| AP001021.2 | −1.17 | 0.29 | 0.69 | 0.08 | 0.53 | DYNLL1P2 | 0.96 | 0.40 | −1.62 | −0.07 | −0.41 | AF123462.1 | 0.93 | −1.26 | 0.59 | 1.22 | 0.49 |
| DNAH6 | −1.16 | 0.65 | 0.47 | 0.29 | −0.19 | MKNK1 | 0.13 | −0.22 | −0.13 | −0.16 | 0.08 | FRG2B | −0.58 | −0.77 | −0.01 | −1.81 | −1.56 |
| FADD | 0.74 | −0.39 | −0.74 | −0.07 | −0.29 | SNORD83A | 0.41 | −0.52 | −0.29 | −0.16 | −0.13 | LBX1-AS1 | −0.26 | −0.59 | −1.56 | 1.06 | −0.63 |
| CDH1 | 0.99 | −0.16 | −0.63 | −0.01 | −0.47 | LINC02285 | 1.18 | −1.92 | 0.54 | −0.30 | 1.65 | AC103982.1 | 0.51 | −0.38 | 0.74 | 0.30 | 0.51 |
| G26269 | −2.56 | 2.52 | 1.81 | 1.27 | −0.29 | SNORD63 | −0.64 | 0.53 | 0.37 | 0.00 | 0.00 | MARVELD1 | −0.06 | 0.11 | −0.05 | −0.09 | −0.19 |
| SLC14A2 | −1.48 | 0.59 | 0.55 | 0.64 | 0.15 | AC098679.2 | −0.38 | 0.27 | 0.30 | 0.06 | −0.14 | RNU6-645P | 0.24 | −0.91 | 0.80 | −0.06 | 0.74 |
| LINC01515 | −0.80 | 0.17 | 0.58 | 0.08 | 0.06 | ATP5PDP4 | 0.36 | −0.27 | −0.16 | −0.35 | −0.22 | AC005549.1 | −0.40 | −1.07 | −0.54 | −0.11 | −0.16 |
| PSCA | −1.77 | 1.16 | 2.66 | −0.30 | 0.30 | PIH1D1 | −0.15 | 0.10 | −0.09 | 0.19 | 0.02 | AC008264.1 | 0.30 | −0.87 | 0.55 | −0.21 | 1.13 |
| LTB4R | 1.13 | −0.57 | −0.77 | −0.07 | 0.11 | AL031594.1 | 1.06 | −0.27 | −0.37 | 0.16 | −0.17 | AC131235.3 | −0.22 | 0.05 | −0.24 | −0.23 | 0.16 |
| RNU7-67P | −3.10 | 0.57 | 2.16 | 0.58 | −0.12 | AC120057.3 | −0.50 | 0.36 | 0.37 | 0.24 | 0.55 | HSPD1P1 | 0.18 | −0.49 | 0.24 | −0.33 | 0.04 |
| PHF5A | 0.65 | −0.34 | −0.44 | −0.23 | −0.47 | AC016583.1 | −0.72 | 0.00 | −0.36 | −0.01 | −0.14 | AC009961.2 | −0.16 | 0.15 | 0.25 | −0.50 | 0.11 |
| AP000757.1 | −1.93 | 1.77 | 0.99 | 1.10 | −0.16 | AL392172.1 | −0.29 | 0.30 | 0.17 | 0.10 | −0.07 | AP002353.1 | 0.42 | −0.94 | −0.64 | 1.92 | 0.26 |
| F12 | 1.38 | −0.78 | −1.20 | 0.17 | 0.10 | DDX18P5 | 0.48 | −0.01 | −0.08 | 0.17 | 0.06 | AP000676.3 | 0.57 | 0.20 | −0.03 | −1.18 | −1.65 |
| LINC02437 | −1.25 | 1.44 | 2.21 | 0.70 | −0.43 | KIAA1841 | −0.10 | −0.05 | 0.02 | −0.06 | 0.02 | AC108749.1 | 0.15 | −0.28 | −0.30 | 0.07 | −0.34 |
| CERS3 | 1.05 | −0.20 | −0.54 | 0.07 | −0.46 | SMTNL1 | 0.52 | 0.01 | −0.85 | −0.20 | −0.10 | BMS1P6 | −0.27 | 0.60 | 0.98 | 0.80 | 1.65 |
| LYAR | 1.03 | −0.83 | −0.92 | −0.36 | −0.29 | MNT | −0.20 | 0.28 | −0.33 | 0.28 | −0.33 | MED28P7 | −0.37 | 0.17 | 1.78 | 0.11 | −0.53 |
| SFR1P1 | −1.08 | 0.72 | 1.33 | 0.64 | 0.23 | ATP13A1 | 0.17 | −0.26 | −0.39 | 0.03 | 0.14 | AL031119.1 | −0.31 | −0.04 | −0.16 | 1.35 | −0.92 |
| ALG1L9P | −0.91 | 0.25 | 1.09 | 0.07 | 0.47 | AC130454.1 | −1.25 | 1.04 | 2.03 | 0.60 | −0.28 | AC068286.1 | 0.30 | 0.16 | −1.17 | 1.35 | 0.36 |
| PCDHB3 | −1.32 | 0.62 | 1.34 | −0.13 | 0.76 | GPR137B | 0.19 | −0.03 | −0.07 | −0.07 | −0.10 | AC008026.1 | 0.14 | 0.44 | −0.17 | 0.30 | −0.20 |
| AC008705.1 | 1.69 | −0.90 | −2.26 | −0.18 | −0.68 | OR51A7 | 1.15 | −0.83 | −2.48 | 0.95 | −1.91 | CTDSP2 | −0.04 | 0.21 | 0.13 | 0.09 | −0.19 |
| MRPS11 | 0.36 | −0.23 | −0.23 | −0.13 | −0.09 | SNORD38 | 0.62 | −0.11 | −0.67 | −0.32 | −0.38 | AC011479.2 | −0.17 | 0.49 | 0.27 | 0.13 | 0.43 |
| KRT18P58 | −2.54 | 1.69 | 0.47 | 0.20 | −0.27 | AC116351.1 | −0.69 | 0.07 | −0.21 | −0.50 | −0.36 | CCL3L1 | 0.83 | −0.29 | −1.09 | 1.93 | 0.57 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| G29271 | 1.29 | −1.22 | −1.00 | −0.42 | −0.36 | LGALS3 | −0.20 | 0.53 | 0.04 | 0.21 | −0.55 | AC093663.2 | 0.11 | 0.17 | −0.31 | −0.10 | −0.62 |
| RABIF | 0.72 | −0.35 | −0.62 | −0.23 | −0.53 | ANKRD26P3 | −0.86 | −0.78 | 1.63 | 0.14 | 1.24 | RAPIA | 0.06 | −0.05 | 0.06 | −0.03 | −0.07 |
| STMN1 | 0.68 | −0.53 | −0.72 | −0.16 | −0.39 | ST3GAL3 | −0.22 | −0.26 | 0.09 | −0.17 | 0.24 | AL591742.2 | 0.34 | −0.42 | −1.31 | 1.51 | −0.81 |
| PDK2 | −0.75 | 0.55 | 0.88 | 0.30 | 0.03 | AL162464.1 | −1.11 | −2.36 | 0.35 | −0.18 | 2.50 | GLIS1 | −0.10 | −0.02 | 0.56 | 0.22 | −0.20 |
| RN7SL471P | 1.06 | −0.65 | −0.48 | −0.64 | −0.31 | DEUP1 | −0.56 | 0.17 | 0.39 | 0.32 | 0.10 | MIR941-3 | 0.14 | −0.25 | −0.78 | −0.32 | −0.46 |
| AC007563.2 | −1.63 | 1.30 | 1.25 | 0.69 | −0.02 | AC005498.2 | −1.12 | −0.73 | 0.95 | −1.13 | 0.14 | AC022210.1 | 0.16 | −0.41 | −0.20 | −0.07 | −0.14 |
| NRP2 | 0.96 | −0.79 | −0.76 | −0.38 | −0.26 | AF015720.1 | −1.17 | 0.97 | 1.82 | −1.63 | 0.68 | AL391704.1 | 0.27 | 0.14 | −1.83 | 1.26 | 0.33 |
| 1-Mar | −1.52 | 0.71 | 0.96 | 0.76 | 0.12 | LINC01597 | −0.85 | 0.72 | −1.14 | 1.08 | −0.84 | RN7SL419P | 0.51 | −0.50 | −1.00 | 0.18 | −1.64 |
| SPCS1 | 0.60 | −0.13 | −0.39 | −0.18 | −0.44 | AL807757.2 | 0.42 | −0.13 | −0.62 | 0.21 | −0.57 | PATE1 | −0.25 | −0.26 | −0.27 | 0.08 | 0.09 |
| CMPK2 | 1.27 | −1.14 | −1.47 | −0.66 | −0.86 | SLCO1A2 | −0.76 | −0.14 | −1.06 | −0.01 | −0.92 | LINC00242 | 0.16 | 0.06 | −0.49 | −0.16 | −0.72 |
| MRPL1 | 0.61 | −0.41 | −0.32 | −0.20 | 0.07 | RPL13AP20 | 0.31 | −0.10 | 0.06 | −0.17 | 0.26 | AC073869.3 | −0.42 | 0.19 | 0.91 | −0.64 | 0.64 |
| FAM83C | 1.20 | −0.13 | −0.60 | 0.08 | −0.56 | AC107081.3 | −0.75 | −0.54 | −0.86 | 0.58 | 0.77 | LARP7P2 | −0.31 | 0.46 | 0.31 | 1.24 | −0.22 |
| CICP14 | −0.72 | 0.20 | 0.49 | 0.06 | 0.34 | G16357 | 0.32 | −0.26 | −0.52 | −0.29 | −0.49 | AC025754.2 | −0.34 | 0.13 | 0.01 | −0.67 | −0.89 |
| FAM19A5 | −1.21 | 0.16 | 1.33 | −0.35 | 0.30 | PAXBP1-AS1 | −0.33 | 0.24 | 0.44 | −0.05 | 0.05 | MB21D2 | −0.06 | 0.04 | 0.10 | −0.08 | −0.28 |
| ALAS1 | 0.69 | −0.33 | −0.73 | −0.13 | −0.60 | LNX1-AS2 | −0.93 | 0.30 | 1.05 | 0.32 | 0.34 | LINC01398 | 0.29 | −0.79 | −0.84 | −0.17 | −0.36 |
| PHKA2 | −0.43 | 0.21 | 0.17 | 0.20 | 0.19 | FSTL1 | −0.42 | 0.34 | 0.93 | −0.16 | −0.15 | AL589666.2 | −0.19 | −0.39 | 0.86 | −0.37 | −0.57 |
| SNRPE | 0.68 | −0.48 | −0.31 | −0.36 | −0.17 | AL161630.1 | −0.92 | −0.46 | 0.13 | −0.04 | 0.61 | NBPF7 | −0.32 | 1.36 | 0.19 | 1.06 | −0.49 |
| RPL39 | 0.72 | −0.32 | −0.32 | −0.19 | −0.43 | C1QTNF3 | −0.45 | 0.37 | 0.45 | −0.05 | −0.07 | AC011247.2 | −0.12 | −0.06 | 0.57 | −0.23 | 0.29 |
| AC104170.1 | −1.17 | 0.77 | 1.01 | 0.32 | 0.22 | RNA5SP511 | −1.38 | 0.96 | 0.83 | 0.89 | 0.84 | C14orf144 | 0.27 | −0.56 | −1.07 | 0.29 | 0.27 |
| MAP4K4 | 0.72 | −0.49 | −0.60 | −0.41 | −0.25 | AC010271.1 | −0.44 | 0.11 | −0.47 | 0.31 | −0.13 | AC011005.4 | 0.16 | 0.26 | 0.40 | 0.58 | −0.09 |
| CYB561 | 0.56 | 0.03 | −0.18 | −0.04 | −0.28 | SNRPEP2 | 0.99 | −1.21 | −0.90 | 0.22 | −1.28 | MCF2L2 | −0.09 | −0.33 | −0.10 | −0.12 | 0.22 |
| RPS3AP35 | −2.11 | 1.74 | 1.81 | 1.08 | 0.79 | RHOXF2 | −0.67 | 0.30 | 0.42 | −0.51 | −0.54 | AC022809.1 | −1.01 | −0.89 | −0.48 | 0.48 | −0.19 |
| HIST1H2BE | 1.17 | −0.92 | −1.37 | −0.23 | −0.61 | AC108112.1 | 1.36 | −0.15 | 0.76 | −0.02 | −0.09 | RPL21P112 | −0.59 | 0.04 | 0.15 | 0.71 | −0.62 |
| EDN3 | −1.82 | 0.48 | 1.50 | 0.41 | 0.30 | SNORA64 | −0.64 | 0.52 | 0.41 | 0.48 | −0.17 | CYCSP40 | 0.15 | −0.26 | −0.24 | −0.50 | −0.52 |
| CASZ1 | −0.69 | 0.66 | 0.47 | 0.34 | 0.03 | RPL12P6 | 1.21 | −1.04 | −1.39 | −0.42 | −0.66 | AC116634.1 | 0.53 | −0.37 | −3.72 | 1.45 | −3.32 |
| SETP21 | −1.28 | 0.53 | 0.58 | 1.10 | 0.30 | AC018693.1 | 0.88 | −0.73 | −1.02 | −0.30 | −0.29 | AC023424.1 | −0.14 | 0.26 | 0.56 | 0.02 | 0.10 |
| RBP1 | 0.99 | −0.65 | −0.61 | −0.28 | −0.26 | PLA2G4F | −0.35 | 0.39 | 0.26 | 0.52 | 0.36 | BMS1P7 | 0.13 | 0.24 | 0.28 | −0.15 | 0.54 |
| RACK1 | 0.58 | −0.15 | −0.30 | −0.13 | −0.42 | AC012501.1 | 0.68 | 0.03 | −0.22 | 0.49 | −0.86 | AC104063.1 | −0.43 | −1.54 | −0.08 | −0.58 | 1.35 |
| OSTF1 | 0.50 | −0.05 | −0.25 | −0.01 | −0.22 | AC079313.2 | −0.83 | −0.79 | 0.31 | 0.02 | 0.55 | B3GNT6 | −0.29 | −0.16 | −3.44 | 0.63 | −1.54 |
| AC078883.1 | 0.81 | −0.47 | −1.00 | 0.07 | −0.33 | RTL1 | −0.44 | 0.21 | 0.78 | −0.41 | −0.29 | EEF1B2P5 | −0.45 | −0.53 | −2.17 | 0.89 | −0.43 |
| CSNK2A2 | 0.73 | 0.03 | −0.30 | 0.04 | −0.51 | LINC01936 | −0.66 | −0.21 | 1.05 | −0.41 | 0.20 | PSPHP1 | 0.27 | −0.33 | −0.06 | −0.42 | −1.88 |
| NOL11 | 0.60 | −0.34 | −0.42 | −0.26 | −0.27 | RPL12P13 | −0.59 | 0.63 | 0.67 | 0.32 | 0.86 | AC009090.2 | 0.19 | −0.31 | 0.58 | 0.65 | 0.81 |
| MCTP2 | 0.58 | −0.14 | −0.27 | −0.11 | −0.19 | CSRP1 | −0.20 | 0.12 | 0.02 | −0.01 | 0.05 | DKFZP434H168 | −0.27 | −1.66 | −0.15 | −0.95 | 2.35 |
| G43480 | −1.62 | 0.16 | 0.07 | 0.77 | 0.38 | LINC01191 | 1.06 | −0.27 | −3.52 | −0.60 | −3.26 | PQLC2 | −0.08 | −0.05 | −0.20 | 0.30 | 0.02 |
| CHORDC1 | 0.55 | −0.24 | −0.28 | −0.30 | −0.14 | LINC00967 | −1.07 | −0.35 | −0.72 | 1.17 | 2.33 | G33879 | 0.60 | −0.32 | 0.03 | 1.30 | −0.22 |
| ERG | 0.67 | −0.33 | −0.26 | −0.20 | −0.18 | KCNJ14 | −0.32 | 0.33 | 0.24 | −0.06 | −0.13 | AL355531.1 | 0.53 | 1.22 | −0.26 | −0.22 | −0.44 |
| PIFO | −1.29 | −0.32 | 0.85 | −0.16 | 0.59 | AC117465.1 | −1.20 | −0.30 | 2.76 | −0.30 | −0.28 | MTND1P21 | −0.20 | 1.12 | 0.76 | 0.59 | 0.02 |
| DES | −1.87 | −0.19 | 0.64 | −0.29 | −0.38 | FOXA1 | −0.57 | 0.47 | 1.55 | 0.52 | 0.83 | SERTAD4-AS1 | −0.07 | 0.40 | 0.47 | −0.01 | 0.15 |
| HIST1H3B | 1.35 | −1.03 | −1.06 | −0.66 | −0.64 | LRRC45 | −0.24 | −0.10 | −0.31 | 0.23 | 0.16 | ADCK2 | 0.06 | 0.09 | 0.14 | 0.04 | 0.06 |
| CUL3 | 0.54 | −0.12 | −0.39 | 0.00 | −0.37 | AC078925.1 | −0.80 | 1.47 | 0.65 | 0.89 | −0.48 | AC060773.1 | 0.22 | −0.29 | 0.19 | −0.74 | −0.32 |
| HIST1H4B | 0.85 | −0.67 | −0.61 | −0.46 | −0.65 | AC100810.1 | −0.24 | 0.20 | 0.07 | −0.08 | −0.13 | AC007406.5 | −0.08 | 0.05 | 0.44 | 0.02 | −0.05 |
| PHF23 | 0.48 | −0.36 | −0.35 | −0.17 | 0.01 | GLRX3P2 | −0.67 | 0.78 | −0.06 | 0.65 | −0.02 | AP003398.2 | −0.36 | −0.94 | −3.37 | 0.76 | −2.07 |
| C1orf115 | −1.13 | 0.87 | 1.19 | 0.22 | 0.46 | EIF3C | 0.20 | −0.28 | −0.09 | −0.20 | 0.21 | OR7E35P | 0.52 | −0.33 | −0.52 | 0.07 | −0.57 |
| AL139805.1 | −1.63 | 0.91 | 1.38 | 0.14 | −0.28 | FDXACB1 | 0.41 | −0.50 | −0.34 | −0.26 | −0.17 | ABCD3 | 0.04 | 0.10 | 0.09 | 0.17 | 0.03 |
| ARHGAP10 | −0.44 | 0.14 | 0.25 | 0.11 | 0.08 | RPL7AP65 | 0.53 | −0.10 | −0.43 | −0.21 | −0.34 | AC023906.1 | 0.21 | −0.36 | −1.78 | 0.11 | −0.29 |
| R3HDM1 | 0.44 | −0.32 | −0.53 | −0.10 | −0.15 | AL355990.2 | −1.06 | 1.50 | −1.33 | −0.11 | −2.04 | GCM1 | −0.25 | −1.12 | 0.29 | 0.50 | 0.11 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| LDOC1 | −0.79 | 0.92 | 0.60 | 0.22 | −0.26 | AC118282.2 | −1.02 | −0.66 | 0.92 | −1.11 | 1.08 | RPL5P6 | 0.29 | 0.22 | −0.63 | 0.01 | −0.16 |
| CASP3 | 0.77 | −0.58 | −0.54 | −0.31 | −0.07 | MTATP6P26 | 0.54 | −0.79 | −0.23 | −0.28 | 0.42 | AC022905.1 | 0.17 | −0.23 | 0.50 | −0.31 | −0.38 |
| AMIGO1 | −0.83 | 0.75 | 0.33 | 0.19 | 0.12 | STAP2 | 0.26 | 0.20 | −0.50 | 0.30 | −0.41 | AP002001.2 | 0.47 | −1.05 | −1.32 | −1.22 | −2.15 |
| AL590666.2 | −2.30 | 0.03 | −0.23 | 0.40 | 0.52 | HCP5B | −0.75 | −1.21 | 1.29 | −0.53 | 2.02 | LINC02448 | 0.74 | −1.98 | 0.55 | 0.56 | 0.72 |
| FBXO38 | 0.24 | −0.09 | −0.27 | 0.01 | −0.17 | RABL6 | 0.15 | −0.12 | −0.35 | 0.05 | −0.07 | AL583808.2 | −0.23 | 0.71 | −0.87 | 1.00 | −0.85 |
| EIF2A | 0.56 | −0.11 | −0.46 | 0.07 | −0.31 | G5880 | −1.37 | −1.58 | 0.66 | 0.01 | 3.32 | RN7SKP161 | −0.30 | −0.93 | 0.69 | −0.92 | 1.03 |
| MRPS22 | 0.61 | −0.20 | −0.43 | −0.26 | −0.45 | RPSAP72 | −1.25 | 0.73 | 1.98 | −1.16 | 1.16 | AL590867.3 | −0.85 | 0.52 | −0.33 | 0.80 | 0.24 |
| AC119751.6 | −2.99 | 1.19 | 1.54 | 0.38 | 0.49 | CDS2 | −0.15 | 0.18 | 0.08 | 0.11 | −0.12 | AC068768.2 | 0.12 | −0.39 | 0.00 | −0.39 | 0.12 |
| CEP295NL | −1.26 | 0.21 | 0.98 | 0.52 | 0.20 | AC006946.1 | 0.63 | 0.59 | −0.36 | 0.39 | 0.13 | DDX11L5 | −0.39 | 0.52 | −0.35 | −0.38 | 0.21 |
| AC092155.1 | −1.78 | 1.54 | 1.26 | 1.32 | 0.35 | RP11-242024.5 | −0.37 | 0.01 | −0.43 | 0.33 | −0.04 | AC084819.1 | −0.59 | −1.40 | −0.74 | 0.02 | 0.37 |
| RPL39L | 0.78 | −0.67 | −0.50 | −0.37 | −0.08 | MTFMT | 0.14 | 0.01 | −0.11 | −0.02 | −0.01 | AC130448.2 | 0.31 | −0.52 | 0.89 | 0.00 | 0.63 |
| AL359915.2 | −0.67 | 0.15 | 0.43 | 0.33 | 0.41 | AL359265.2 | −1.25 | −1.83 | 0.55 | −1.61 | 2.43 | MAGI3 | −0.04 | 0.20 | 0.05 | 0.01 | 0.02 |
| EYA3 | 0.41 | −0.20 | −0.12 | −0.20 | 0.02 | MYH2 | −0.68 | 0.57 | −0.69 | 0.46 | −0.34 | AC092653.2 | 0.12 | 0.32 | 0.33 | 0.14 | −0.22 |
| SLC38A2 | 0.68 | −0.17 | −0.61 | −0.12 | −0.50 | AL031686.1 | −0.86 | −0.10 | −1.10 | 0.53 | 0.40 | AC135782.3 | 0.10 | −0.13 | 0.28 | −0.16 | 0.19 |
| OSBPL5 | −0.60 | 0.19 | −0.02 | 0.18 | 0.00 | LEPROT | 0.22 | −0.04 | −0.02 | 0.04 | −0.11 | SLC16A2 | −0.08 | 0.09 | 0.09 | −0.30 | −0.01 |
| NXPH3 | −1.14 | 0.69 | 0.94 | 0.20 | 0.17 | KCNQ5-AS1 | 0.89 | −1.38 | −0.94 | 0.48 | 1.21 | AC246817.1 | 0.19 | 0.41 | −0.14 | 0.44 | −0.02 |
| FRMD1 | −2.23 | 0.69 | 1.09 | 0.71 | 0.24 | MIR708 | 0.52 | −1.08 | −0.35 | −0.27 | 0.89 | CLK3P2 | −0.37 | 0.20 | 3.04 | −0.12 | 1.65 |
| AC093158.1 | −1.76 | 0.89 | 1.57 | 0.63 | 0.74 | AC104564.2 | 0.52 | −0.35 | −1.60 | 0.43 | −0.27 | AC013489.1 | 0.28 | 0.55 | 1.46 | 1.64 | 0.80 |
| GCNT2 | −0.73 | 0.25 | 0.03 | 0.36 | 0.29 | AC068790.9 | −0.79 | 0.24 | 0.90 | −0.23 | −0.18 | AC106748.1 | −0.35 | 0.84 | 1.61 | −0.67 | −0.66 |
| SBSN | 1.24 | −0.40 | −0.48 | −0.31 | −0.47 | PCP4L1 | 0.50 | 0.34 | −0.36 | 0.33 | −0.06 | AC093599.1 | 0.53 | −0.77 | −0.78 | −0.56 | 0.31 |
| AC091196.1 | −1.07 | 0.82 | 0.91 | 0.46 | 0.09 | MIR3160-2 | 0.69 | −0.59 | 0.22 | 0.07 | 0.34 | PRR20G | 0.82 | −1.54 | −0.67 | −2.33 | −1.55 |
| CDK20 | −0.66 | 0.22 | 0.33 | 0.08 | 0.46 | SNORD115 | 0.70 | −0.95 | 0.24 | −0.12 | 1.21 | AP003110.1 | 0.13 | −0.42 | −0.37 | −0.20 | 0.32 |
| AC021078.1 | 1.03 | −0.38 | −0.61 | −0.03 | −0.18 | AC005086.3 | 0.66 | −1.39 | −1.01 | −0.85 | −0.12 | AL158212.4 | −0.12 | 0.37 | 0.22 | 0.11 | −0.25 |
| AUP1 | 0.42 | −0.27 | −0.48 | −0.04 | −0.05 | AKAP8 | −0.17 | −0.06 | −0.26 | 0.17 | 0.02 | SRGAP3-AS4 | −0.70 | 0.49 | −0.29 | −0.41 | −0.08 |
| LRR1 | 1.01 | −0.47 | −1.05 | −0.03 | −0.55 | SNORA30 | 0.48 | −0.11 | −0.21 | 0.44 | −0.34 | NAPB | 0.04 | −0.02 | 0.12 | 0.00 | 0.09 |
| JRK | −0.64 | 0.31 | 0.56 | 0.14 | 0.29 | RNU1-139P | −0.85 | 0.09 | −0.15 | 0.97 | −0.56 | RN7SL83P | 0.57 | −1.18 | −0.39 | −0.01 | 1.10 |
| NDUFAF8 | 0.73 | −0.33 | −0.37 | −0.32 | −0.14 | MED31 | 0.35 | 0.01 | −0.13 | 0.20 | −0.14 | REG4 | 0.29 | −0.54 | −3.04 | 0.51 | −1.27 |
| SRSF5 | −0.32 | 0.33 | 0.25 | 0.18 | 0.08 | GPR39 | 0.44 | −0.15 | −1.19 | 0.36 | −0.40 | COQ5 | −0.04 | −0.01 | 0.02 | −0.03 | −0.06 |
| STEAP4 | 1.09 | −0.50 | −0.44 | −0.24 | −1.10 | AL445928.2 | −0.58 | −0.06 | 1.01 | 0.37 | 0.58 | AL354897.1 | 0.19 | −0.28 | −1.66 | 0.14 | 0.72 |
| AP006284.1 | −1.64 | 1.31 | 1.33 | 0.97 | −0.16 | DLEU1 | 0.18 | −0.12 | −0.16 | 0.10 | 0.01 | LINC02368 | 0.67 | −1.35 | −1.09 | 1.58 | 0.95 |
| AC026401.2 | −1.21 | 0.01 | −0.01 | 0.26 | 0.27 | C8orf48 | −0.46 | 0.04 | 1.53 | −0.20 | 0.84 | CREB3L3 | 0.33 | −0.22 | −1.99 | 0.51 | −0.80 |
| RPF1 | 0.57 | −0.30 | −0.29 | −0.21 | −0.26 | AC114947.2 | 0.59 | −0.25 | −0.01 | 0.35 | 0.33 | AL450384.1 | −0.11 | −0.10 | 0.77 | −0.17 | 0.39 |
| SERBP1P3 | −1.79 | 0.65 | 0.95 | 1.08 | 0.06 | EEF1AKMT3 | −0.21 | 0.12 | 0.14 | 0.10 | 0.23 | AL022163.1 | 0.67 | −0.37 | 0.30 | 1.33 | 0.10 |
| MPDU1 | 0.49 | −0.35 | −0.63 | −0.10 | −0.27 | AC087481.2 | 0.81 | −0.34 | −0.51 | 0.72 | 0.22 | AL357835.1 | 0.38 | −0.66 | −1.21 | 0.65 | 0.98 |
| AC008267.2 | −1.13 | 0.51 | 0.66 | −0.16 | 0.31 | RN7SKP210 | −0.67 | 0.74 | 1.60 | −0.31 | −0.61 | AC118278.1 | 0.18 | −0.02 | 0.53 | 0.67 | 0.42 |
| MED10 | 0.46 | −0.30 | −0.50 | −0.17 | −0.17 | RPS26P15 | 0.68 | −0.95 | −0.42 | 0.03 | 1.07 | OR2AG1 | 0.14 | −0.45 | −1.02 | 0.31 | −0.10 |
| AC087500.2 | −1.57 | 0.25 | 0.91 | −0.83 | −0.42 | LNPK | 0.21 | −0.11 | −0.04 | −0.03 | −0.06 | AL136162.1 | 0.18 | −0.54 | −1.10 | 0.16 | 0.14 |
| ATXN10 | 0.48 | −0.22 | −0.27 | −0.17 | −0.23 | ESRRAP2 | −0.70 | −1.47 | 0.06 | −0.89 | −0.10 | AC142293.3 | 0.35 | −0.34 | −2.33 | 0.93 | −0.70 |
| BACH1 | 0.69 | −0.11 | −0.36 | −0.10 | −0.50 | ERBB3 | −0.23 | 0.53 | 0.39 | 0.43 | 0.06 | AC092687.2 | 0.41 | −0.36 | 0.42 | −0.84 | 0.79 |
| CLP1 | 0.66 | −0.28 | −0.51 | −0.05 | −0.52 | AL121821.1 | −0.82 | 1.10 | 0.53 | 0.63 | 0.18 | AC018712.1 | −0.37 | 0.47 | −0.44 | −0.63 | −1.05 |
| AL139081.1 | −1.25 | 0.86 | 0.77 | 0.36 | −0.29 | AC105339.3 | −0.39 | 0.10 | 0.36 | −0.11 | 0.55 | PMS2P11 | −0.24 | 1.33 | 0.26 | 0.42 | −0.43 |
| GOLGA8R | −1.00 | 0.67 | 0.91 | 0.31 | −0.03 | AL160314.2 | −0.70 | −0.40 | 0.57 | −0.07 | −0.05 | HSPBAP1 | 0.05 | 0.13 | 0.01 | 0.15 | −0.05 |
| LAMP2 | 0.81 | −0.26 | −0.48 | −0.06 | −0.29 | RNU6-857P | 2.15 | −1.29 | −1.51 | 0.27 | 0.78 | BANCR | −0.28 | −0.46 | −1.39 | 0.74 | −0.36 |
| STMP1 | 0.64 | −0.23 | −0.22 | −0.17 | −0.22 | RN7SL595P | −0.74 | 0.88 | −0.07 | −0.06 | −1.09 | GDPD4 | −0.23 | −0.38 | 0.04 | −0.83 | −1.23 |
| ANKRD20A4 | −1.44 | 0.47 | 1.36 | 0.40 | 0.66 | AP000302.1 | −0.87 | 0.60 | 2.64 | −0.52 | 0.06 | EGFLAM | 0.09 | −0.26 | −0.11 | 0.07 | −0.02 |
| ANKZF1 | −0.60 | 0.32 | 0.25 | 0.41 | 0.22 | CR786580.1 | −0.65 | −0.04 | −0.20 | 0.51 | −0.21 | ABHD17AP6 | −0.35 | −0.12 | −1.19 | −0.30 | −1.53 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| G35531 | −0.88 | 0.91 | 0.51 | 0.47 | −0.10 | PALM2 | −0.53 | −0.17 | 0.22 | −0.08 | −0.11 | IFNA22P | −0.59 | −0.76 | 1.63 | −0.19 | 0.92 |
| CCDC9B | −0.84 | 0.65 | 0.94 | 0.12 | −0.08 | DPYD | 0.21 | −0.23 | −0.20 | −0.02 | 0.05 | SNORD123 | −0.23 | −0.97 | 0.78 | −1.00 | 0.27 |
| KRT38 | −2.04 | −0.76 | 0.78 | −0.12 | 1.14 | MIR500A | 1.60 | −0.27 | 0.20 | 0.43 | −0.14 | G36605 | −0.11 | 0.51 | 0.28 | 0.08 | −0.54 |
| MYLK | −0.93 | 0.37 | 0.70 | −0.03 | −0.04 | ATP6VOD2 | 0.97 | −0.42 | −0.94 | −0.76 | −0.84 | AC090409.2 | 0.20 | −0.56 | −1.35 | 0.38 | −0.33 |
| AL136982.5 | 1.68 | −0.40 | −0.27 | −0.43 | −0.16 | IQSEC3 | −0.58 | 0.73 | −0.12 | 0.34 | 0.54 | RP11-38M15.11 | 0.86 | −0.18 | −0.68 | 0.90 | 1.98 |
| RAB6A | 0.63 | −0.22 | −0.37 | −0.14 | −0.39 | AC090286.1 | −0.74 | 0.07 | 0.29 | −1.02 | −0.69 | SMG1P7 | −0.05 | −0.13 | −0.11 | 0.19 | 0.03 |
| G3BP2 | 0.52 | −0.23 | −0.33 | −0.17 | −0.23 | AC016027.5 | −0.56 | −0.11 | 0.41 | −0.14 | −0.14 | AL136309.3 | 0.31 | −0.11 | −0.56 | 0.13 | −0.02 |
| SERPINB10 | 1.79 | −0.22 | −1.09 | 0.12 | −1.53 | AL135937.1 | −0.63 | 0.78 | 0.52 | 0.54 | −0.15 | SPATA4 | −0.34 | −0.91 | −1.30 | −0.94 | −1.34 |
| ABCD4 | −0.51 | 0.17 | 0.31 | 0.18 | 0.18 | LEMD1-AS1 | 0.71 | −1.52 | −0.54 | 0.22 | 1.20 | RNA5SP101 | −0.59 | −0.36 | 0.97 | 0.97 | −0.30 |
| HID1 | −1.06 | 0.83 | 0.90 | 0.51 | 0.35 | ASRGL1 | −0.51 | −0.24 | 1.40 | −0.69 | 0.38 | S100P | 0.13 | −0.02 | −1.67 | 0.47 | −0.98 |
| RSAD2 | 1.38 | −1.29 | −1.66 | −1.02 | −1.02 | AC099066.1 | −0.72 | −0.58 | 0.19 | −0.97 | 0.41 | G30917 | −0.54 | −0.61 | −0.71 | 0.69 | −0.17 |
| FAM27E1 | −2.60 | 1.69 | 1.94 | 0.62 | 0.88 | P2RX6P | −1.04 | −0.28 | 1.63 | −0.91 | 0.42 | AC099329.2 | −0.13 | −0.12 | 0.06 | 0.11 | −0.19 |
| HIBADH | −0.75 | 0.42 | 0.97 | 0.10 | 0.31 | EIF4BP3 | 0.34 | 0.15 | −0.26 | 0.32 | −0.20 | LINC01280 | 0.43 | −0.35 | −1.81 | 0.55 | −1.12 |
| AL356479.1 | −1.60 | 0.97 | 0.93 | −0.09 | 0.19 | AC016712.1 | −0.89 | −0.13 | 1.11 | 1.39 | 1.14 | PCDH8P1 | −0.50 | −0.76 | 1.70 | 1.50 | 1.31 |
| SLC22A3 | 0.66 | −0.47 | −0.62 | 0.16 | 0.16 | MTCO3P12 | −0.30 | 0.27 | 0.18 | 0.13 | 0.10 | HA01 | −0.34 | 0.24 | 0.02 | 1.32 | 0.27 |
| AL023754.1 | 1.74 | −1.09 | −0.72 | −0.08 | 0.33 | LAMTOR5P1 | 0.73 | 1.30 | −0.99 | 0.95 | −0.59 | SLC22A15 | −0.07 | 0.00 | 0.49 | −0.06 | 0.03 |
| AC134312.1 | −1.28 | 0.82 | 1.38 | 0.03 | 0.36 | AC004980.4 | −1.68 | 1.77 | 1.69 | 1.23 | 0.56 | BTF3P11 | −0.67 | −0.10 | −0.70 | −0.75 | −0.81 |
| LYN | 0.88 | −0.72 | −0.40 | −0.15 | −0.31 | CYP21A1P | −0.91 | −0.67 | 0.61 | 0.02 | 1.86 | PLCB2 | −0.11 | −0.47 | −0.01 | −0.20 | 0.26 |
| AC068733.3 | −1.39 | 0.06 | 0.67 | 0.14 | 0.46 | PLPP4 | 0.68 | 0.67 | 0.49 | −0.33 | −0.34 | GPR119 | 0.62 | −0.80 | −1.34 | −0.23 | −0.25 |
| AC131392.1 | −1.10 | 0.59 | 0.34 | 0.79 | −0.34 | RNU6-198P | 0.64 | −0.09 | −0.95 | 0.03 | −0.12 | AC140061.11 | −0.51 | 0.50 | 0.58 | −1.13 | −1.75 |
| AL138751.1 | −1.29 | −0.01 | 0.87 | 0.53 | 1.17 | LINC01135 | −0.51 | 0.09 | 0.67 | 0.47 | 0.79 | AC064836.2 | 0.27 | −1.01 | 1.56 | −1.05 | 0.55 |
| AC010325.1 | −1.62 | 0.12 | 0.81 | −0.27 | 0.40 | AC010642.1 | 0.68 | −0.50 | −0.25 | −0.32 | −0.11 | AC018442.2 | 0.10 | 0.24 | 0.67 | 0.05 | −0.04 |
| NDRG1 | 0.87 | −0.31 | −1.02 | −0.36 | −0.60 | RPL12P4 | 0.34 | −0.13 | 0.05 | −0.18 | −0.66 | AL355103.1 | 0.44 | −0.87 | −2.85 | 1.11 | −1.70 |
| RAD23B | 0.58 | −0.22 | −0.56 | −0.10 | −0.39 | RN7SL617P | −0.98 | −0.08 | −0.60 | 0.08 | −0.71 | AC012055.1 | −0.71 | 0.74 | −0.09 | 0.87 | −1.38 |
| NKRF | 0.63 | −0.22 | −0.58 | 0.01 | −0.16 | AC005911.1 | 0.61 | −0.70 | −1.15 | −0.04 | −0.51 | KRT18P16 | 0.75 | 0.64 | −1.47 | −0.79 | −2.56 |
| COA4 | 0.55 | −0.42 | −0.26 | −0.33 | −0.02 | PIGN | 0.12 | 0.02 | 0.00 | 0.14 | 0.07 | BLOC1S1 | −0.08 | 0.14 | 0.03 | 0.23 | −0.34 |
| IFITM9P | −3.51 | 3.83 | 3.15 | 1.53 | 0.93 | IFNL3P1 | −0.76 | −0.11 | 1.51 | 0.26 | 0.15 | MRPS6P2 | 0.18 | 0.01 | −0.66 | 0.23 | −0.36 |
| AC009126.1 | −0.83 | 0.18 | 0.80 | −0.09 | 0.18 | FES | −0.31 | 0.09 | 0.16 | 0.05 | 0.08 | AL162253.1 | −0.12 | −0.10 | −0.51 | 0.08 | −0.32 |
| CKMT2 | −0.56 | 0.34 | 0.76 | −0.03 | 0.39 | RNA5SP30 | −1.17 | 0.54 | −0.03 | 1.98 | 0.10 | RN7SL130P | 0.13 | −0.02 | 0.60 | −0.40 | 0.12 |
| KIF2A | 0.49 | −0.33 | −0.27 | −0.16 | −0.14 | AC018931.1 | −0.54 | 0.13 | 0.53 | 0.44 | 0.44 | SNORD114-29 | 1.15 | −0.16 | 0.95 | 0.24 | 1.77 |
| PPP2R2B | −1.12 | 0.86 | 0.60 | 0.30 | −0.13 | ODF2-AS1 | 1.07 | −0.41 | −1.05 | −0.53 | −0.19 | CHSY3 | −0.09 | 0.02 | 0.51 | −0.42 | −0.11 |
| RPS27AP13 | 2.47 | −1.21 | −2.64 | −0.69 | −2.03 | EXOC1 | 0.09 | 0.05 | −0.06 | 0.05 | −0.04 | AP002008.2 | −0.27 | −1.04 | 0.21 | −0.53 | −0.01 |
| EIF3B | 0.50 | −0.37 | −0.61 | −0.10 | −0.11 | ONECUT1 | −0.66 | −0.29 | −1.17 | −0.11 | −0.10 | RNU2-17P | −0.35 | −0.62 | 0.86 | 0.66 | 0.52 |
| SNRK-AS1 | −0.72 | 0.67 | 1.01 | −0.02 | 0.11 | PEX16 | −0.15 | 0.04 | −0.22 | 0.27 | 0.06 | CEP83-DT | −0.15 | −1.13 | −0.87 | −0.22 | 0.02 |
| LDHD | −1.13 | 0.87 | 0.61 | 0.87 | 0.38 | AL512598.1 | −0.76 | 0.10 | −0.72 | 0.19 | −0.09 | AC007016.1 | 0.16 | −0.82 | −1.20 | 0.48 | 1.14 |
| SLBP | 0.62 | −0.50 | −0.55 | −0.28 | −0.25 | RNU6-126P | 0.62 | −0.25 | −0.99 | 0.12 | −0.06 | AC016026.1 | −0.11 | −0.47 | 0.20 | 0.04 | 0.83 |
| MTCYBP44 | 1.68 | −0.15 | −1.43 | 0.07 | −0.70 | AL359643.2 | −0.39 | 0.19 | 0.79 | −0.38 | −0.10 | AC024560.1 | −0.55 | 0.18 | 0.27 | 0.67 | −0.20 |
| LRPPRC | 0.59 | −0.29 | −0.46 | −0.10 | −0.19 | AP003170.4 | −0.50 | 0.95 | 0.24 | 0.37 | −0.16 | AC013476.1 | 0.18 | −0.68 | 0.38 | −0.08 | 1.21 |
| KDM5B | 0.51 | −0.17 | −0.44 | −0.14 | −0.25 | HDC | −0.30 | 0.48 | 1.53 | −0.01 | 0.40 | CCDC87 | 0.18 | 0.23 | −0.61 | 0.22 | −0.08 |
| SERBP1P1 | 1.32 | −0.56 | −0.97 | 0.14 | −0.56 | GRB10 | 0.21 | −0.19 | −0.11 | −0.08 | −0.02 | AC010680.2 | 0.22 | −0.31 | 1.05 | 0.20 | 0.32 |
| SLC35F4 | −1.31 | 0.85 | 0.21 | 0.38 | −0.04 | PRTFDC1 | 0.32 | −0.03 | 0.17 | −0.19 | −0.22 | LLPH | 0.07 | −0.07 | −0.33 | 0.12 | −0.14 |
| AP000842.2 | −2.91 | 1.10 | 4.28 | 0.03 | 1.13 | CNPY2 | −0.21 | −0.29 | −0.13 | 0.11 | 0.30 | MIR374B | −0.11 | −0.49 | 0.55 | 0.20 | 0.49 |
| G4388 | −1.67 | 1.04 | 1.25 | 1.17 | −0.01 | CBWD5 | 0.22 | −0.24 | −0.25 | −0.28 | −0.11 | CRISP1 | 0.36 | −0.84 | −2.39 | 0.07 | −0.64 |
| GTF2IP13 | −0.95 | 0.26 | 0.61 | 0.20 | 0.54 | G30008 | −0.74 | 0.77 | −0.02 | 1.69 | 0.31 | EXOC3L1 | −0.08 | −0.08 | 0.30 | −0.13 | −0.06 |
| B3GNTL1 | −0.67 | 0.13 | 0.47 | 0.03 | 0.00 | GABRD | −0.71 | −0.58 | −1.02 | 0.38 | −0.62 | NTS | −0.29 | 0.00 | −1.17 | 1.91 | 0.16 |
| EP300 | 0.24 | 0.04 | −0.24 | −0.03 | −0.27 | MCC | −0.14 | 0.17 | 0.27 | 0.11 | 0.13 | OR11H13P | −0.53 | −1.35 | 0.83 | −0.93 | 0.64 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| ADIPOQ | −2.89 | 2.65 | 2.18 | 1.63 | −0.12 | KMT2E-AS1 | −0.26 | 0.00 | 0.22 | 0.18 | 0.11 | MTND2P4 | −0.38 | −0.34 | 0.20 | −0.86 | −0.19 |
| ENDOD1 | 0.87 | −0.01 | −0.55 | −0.08 | −0.66 | SLC1A1 | −0.24 | 0.10 | 0.78 | −0.33 | 0.29 | CYP2C8 | 0.16 | −0.48 | −0.85 | −0.23 | −0.68 |
| SNORA60 | −1.17 | 0.73 | 1.03 | 0.33 | −0.22 | LINC01122 | −0.83 | −0.60 | −0.74 | 0.34 | 0.22 | AC025674.2 | −0.54 | −0.72 | 0.98 | −2.09 | −0.09 |
| SLC35B1 | 0.45 | −0.32 | −0.50 | −0.02 | −0.14 | ANKH | −0.18 | 0.33 | 0.41 | 0.18 | 0.04 | DOCK8 | 0.07 | −0.16 | −0.11 | −0.11 | −0.11 |
| AC107068.1 | 0.70 | −0.31 | −0.37 | −0.20 | −0.12 | ACO2 | 0.14 | −0.10 | −0.31 | 0.08 | −0.04 | RPL4P6 | −0.08 | −0.06 | −0.56 | −0.02 | −0.11 |
| FAM47E | −0.95 | 0.42 | 0.38 | 0.52 | 0.18 | AC129492.1 | 0.47 | −0.07 | −0.94 | −0.03 | −0.37 | MIMT1 | 0.39 | −0.85 | −0.51 | −0.59 | −1.09 |
| PRCC | 0.35 | −0.16 | −0.44 | 0.03 | −0.19 | SNORA55 | −0.47 | 0.00 | −0.27 | 0.49 | −0.60 | MIR4645 | 0.27 | 0.12 | 0.65 | −0.70 | −0.63 |
| CUL2 | 0.51 | −0.20 | −0.38 | −0.14 | −0.33 | CDPF1 | −0.22 | 0.08 | 0.25 | −0.04 | 0.22 | AP002812.5 | −0.12 | 0.39 | 0.30 | 0.09 | 0.00 |
| ANKRD20A19P | −1.64 | 0.79 | 1.07 | 0.74 | 0.90 | LINC01722 | −0.98 | −0.23 | 0.15 | 1.27 | 1.57 | RNU6-1157P | −0.17 | −0.56 | 0.79 | −0.53 | 0.41 |
| CA15P1 | −1.36 | 0.79 | 1.04 | 0.62 | 0.34 | G40216 | −0.65 | 0.83 | 1.45 | 0.24 | −0.18 | OR2H5P | −0.66 | 0.45 | −0.49 | −1.38 | −2.24 |
| AC004022.1 | −1.66 | 0.46 | 1.28 | 0.33 | 0.85 | AL355312.3 | 1.01 | 0.28 | −0.46 | 0.06 | −0.41 | IRX4 | 0.08 | 0.26 | −1.08 | 0.58 | −0.31 |
| BZW2 | 0.48 | −0.18 | −0.38 | 0.02 | −0.09 | NHLRC1 | 0.29 | −0.39 | −0.06 | 0.14 | 0.24 | BMT2 | −0.06 | 0.16 | 0.39 | 0.12 | 0.20 |
| SLC20A2 | 0.55 | −0.26 | −0.39 | −0.11 | −0.17 | AC087241.3 | −1.10 | 1.68 | −0.43 | 0.47 | −2.79 | RNU6-541P | −0.43 | 1.00 | 0.11 | 0.40 | −2.52 |
| CENPA | 1.11 | −0.86 | −1.21 | −0.17 | −0.46 | RPS26P28 | 0.59 | −0.36 | −0.47 | −0.25 | 0.06 | G39251 | −0.63 | 2.38 | 1.96 | −0.10 | −0.87 |
| PLEKHA8 | 0.49 | −0.15 | −0.30 | −0.10 | −0.19 | GTSF1 | −0.65 | 0.81 | 0.60 | −0.22 | −0.71 | REGIA | 0.51 | −0.76 | −1.16 | 0.86 | 1.91 |
| OTOGL | −1.40 | −0.01 | 0.66 | 0.03 | 0.48 | AP001425.1 | 1.22 | −2.49 | −3.53 | 0.83 | 0.29 | AL049557.2 | 0.18 | −0.30 | −1.05 | 0.99 | −0.21 |
| REEP2 | −1.26 | 0.67 | 0.42 | 0.33 | −0.24 | AL512634.1 | −0.98 | 0.28 | 0.39 | −0.89 | 0.45 | GFY | 0.28 | −1.02 | −1.31 | 0.80 | 0.80 |
| AC025430.1 | −1.03 | 0.00 | 0.59 | 0.04 | 0.20 | AC009107.2 | 0.57 | 0.10 | 0.91 | −0.39 | −0.02 | LINC01878 | 0.20 | −0.24 | −0.99 | 0.24 | −0.72 |
| RRP15 | 0.56 | −0.39 | −0.46 | −0.17 | −0.17 | CXXC5 | −0.23 | 0.36 | 0.48 | 0.12 | −0.13 | LINC02338 | −0.35 | −0.18 | −2.19 | −0.39 | −1.36 |
| CEBPZ | 0.48 | −0.25 | −0.34 | −0.11 | −0.09 | AC004771.1 | 0.47 | −0.15 | 0.03 | −0.42 | −0.01 | GNPTAB | −0.03 | 0.15 | 0.02 | 0.09 | −0.05 |
| RNF168 | 0.44 | −0.10 | −0.50 | −0.04 | −0.31 | AC092017.1 | 1.57 | 0.09 | −0.82 | 0.91 | 0.65 | ADH6 | −0.08 | 0.18 | 0.38 | −0.30 | −0.30 |
| CCDC40 | −1.02 | 0.42 | 0.76 | 0.62 | 0.47 | RNA5SP141 | −0.63 | 0.11 | −1.12 | 0.87 | −0.95 | FAM86FP | −0.13 | 0.37 | −0.20 | 0.37 | 0.11 |
| RFX2 | −0.86 | 0.33 | 0.43 | 0.37 | −0.12 | KCNJ13 | −0.21 | 0.21 | 0.20 | 0.43 | 0.08 | AP001803.2 | −0.27 | 0.62 | −0.07 | 0.71 | 0.36 |
| PDZD8 | 0.58 | −0.19 | −0.33 | −0.20 | −0.33 | NFASC | −0.29 | 0.50 | 0.28 | 0.44 | −0.10 | AC122685.1 | 0.50 | −1.61 | −0.78 | −0.41 | −2.09 |
| COA5 | −0.45 | 0.12 | 0.48 | 0.08 | 0.13 | AC073911.1 | −1.03 | −0.61 | −1.44 | 0.31 | 0.23 | CHRNB1 | −0.05 | 0.16 | −0.14 | 0.10 | −0.10 |
| INTS2 | 0.40 | −0.27 | −0.21 | −0.02 | 0.07 | ACD | 0.17 | −0.15 | −0.28 | −0.17 | −0.06 | AC110760.3 | −0.31 | 2.03 | 1.14 | 1.31 | −0.16 |
| CBWD1 | 0.47 | −0.11 | −0.26 | 0.04 | −0.14 | SIKE1 | 0.15 | 0.08 | −0.03 | −0.12 | −0.21 | AC019294.1 | −0.20 | −0.57 | −0.80 | 0.21 | 0.36 |
| G28274 | 1.40 | −1.02 | −1.97 | −0.36 | −0.96 | LIX1L | −0.25 | 0.04 | 0.26 | −0.09 | −0.10 | MIR421 | 0.08 | 0.02 | 0.48 | −0.07 | 0.10 |
| PDCD11 | 0.55 | −0.46 | −0.57 | −0.14 | 0.00 | RIPK2 | 0.22 | −0.10 | −0.03 | −0.12 | −0.32 | AL451140.1 | 0.78 | −1.14 | −2.36 | 0.25 | −0.63 |
| MTCH1 | −0.40 | 0.15 | 0.23 | 0.08 | 0.09 | AC007314.1 | 0.45 | −0.22 | −0.29 | 0.05 | −0.88 | AC011921.1 | 0.15 | −0.61 | −0.84 | 0.36 | 0.00 |
| STT3A | 0.47 | −0.38 | −0.31 | −0.27 | −0.07 | AC073320.1 | −0.57 | −0.26 | 0.42 | −0.06 | 0.17 | AC109446.3 | 0.16 | −0.07 | −0.13 | −0.04 | −0.07 |
| SOX5-AS1 | −1.75 | 1.04 | 1.59 | 0.27 | 0.51 | GPR101 | −0.87 | −2.25 | 0.55 | −0.78 | 1.55 | ECSCR | 0.09 | 0.20 | 1.04 | −0.41 | −0.03 |
| MAPK8IP3 | −0.78 | 0.29 | 0.29 | 0.28 | 0.16 | LINC00968 | −0.55 | −0.33 | −0.03 | −0.53 | −0.13 | FTH1P11 | −0.19 | −0.39 | 0.71 | −0.55 | 0.08 |
| SOCS3 | 1.58 | −1.75 | −2.54 | −0.34 | −1.55 | AC137630.2 | 0.65 | 1.08 | −0.60 | 0.20 | −1.09 | MTCYBP18 | 0.08 | −0.45 | −0.43 | −0.08 | 0.43 |
| SPDL1 | 0.71 | −0.63 | −0.84 | −0.25 | −0.24 | AC007998.4 | 0.71 | −0.42 | −0.59 | 0.19 | −0.36 | RNU6-1064P | −0.22 | −0.11 | 0.51 | −0.26 | 0.77 |
| SKIL | 0.76 | −0.13 | −0.56 | −0.25 | −0.76 | SCARNA9 | −0.27 | 0.55 | 0.86 | 0.11 | 0.01 | AL591212.1 | 0.22 | −0.04 | −0.34 | 0.45 | −0.51 |
| ELAC2 | 0.45 | −0.27 | −0.52 | −0.06 | −0.18 | DCST1-AS1 | −0.45 | 0.29 | 0.94 | 0.12 | 0.71 | HOMER2P1 | 0.74 | −1.29 | −0.60 | 1.39 | 1.09 |
| MRPL57 | 0.56 | −0.31 | −0.16 | −0.21 | −0.14 | EWSAT1 | −0.63 | −0.23 | 1.35 | 0.35 | 0.39 | OR8H1 | 0.44 | −1.03 | 0.80 | −0.59 | 0.28 |
| KPNA6 | 0.48 | −0.09 | −0.45 | 0.01 | −0.39 | AC104964.1 | −0.55 | 0.68 | 0.78 | 0.50 | 0.21 | ILKAP | −0.03 | −0.08 | −0.08 | 0.04 | 0.07 |
| CEMIP | 1.20 | −0.87 | −0.66 | −0.86 | −0.02 | AC121334.3 | −0.80 | −0.07 | 0.80 | −1.07 | −1.50 | NUDT19P4 | −0.27 | −0.83 | −0.63 | 0.94 | 0.15 |
| AC012291.2 | −0.95 | 0.26 | 1.14 | −0.02 | 0.56 | AL391095.3 | 0.53 | −0.75 | −0.53 | 0.00 | 0.30 | G8154 | −0.19 | −0.37 | −0.40 | 0.13 | 0.41 |
| SPIN2A | −0.74 | 0.54 | 1.14 | −0.01 | 0.37 | RAD23A | 0.13 | −0.01 | −0.14 | 0.09 | −0.13 | AL355297.4 | −0.27 | −0.38 | 0.06 | −0.20 | −0.18 |
| ABRACL | 0.79 | −0.44 | −0.38 | −0.36 | −0.38 | RN7SL326P | −1.31 | 0.71 | 0.59 | 1.42 | 0.37 | ARHGEF7-IT1 | −0.25 | 0.80 | 0.37 | −0.17 | −0.53 |
| MESTP1 | −1.44 | 0.72 | 1.11 | 0.98 | 0.42 | SDC4 | −0.28 | 0.59 | 0.22 | 0.19 | −0.28 | SPATA31D1 | −0.32 | −1.35 | 0.49 | −0.25 | −0.71 |
| ENPP4 | −1.05 | 0.62 | 1.07 | −0.10 | 0.36 | LINC01482 | 0.47 | −0.29 | 0.07 | 0.03 | 0.34 | AL358335.2 | −0.65 | −0.68 | 0.33 | 0.47 | 1.96 |
| ITFG2 | −0.54 | 0.27 | 0.30 | 0.26 | 0.26 | HMGN5 | 0.23 | −0.17 | −0.19 | 0.11 | −0.11 | SCAF8 | −0.02 | 0.07 | 0.07 | −0.01 | −0.04 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| HSD11B1 | −1.43 | 0.80 | 1.00 | 0.59 | 0.28 | AMY2A | −1.11 | 0.61 | −0.07 | −0.27 | −1.04 | RP11-7G23.8 | −1.33 | 0.25 | −0.09 | 1.94 | 1.30 |
| ODC1 | 1.64 | −1.69 | −1.50 | −1.11 | −1.94 | AC015912.2 | 0.84 | −0.26 | −0.23 | −0.67 | −0.65 | FLT1P1 | 0.24 | 0.03 | −1.48 | 0.17 | −0.10 |
| HIST1H3F | 1.36 | −0.92 | −1.10 | −0.34 | −0.69 | MIR4473 | −0.66 | 0.60 | −0.17 | 0.10 | −0.25 | LINC01888 | 0.70 | −1.46 | −1.18 | −1.55 | −0.46 |
| ADCYAP1 | 2.31 | 0.22 | 0.18 | −0.73 | −2.28 | KCNJ10 | −0.38 | −0.42 | −0.08 | 0.10 | 0.36 | MRPS36P5 | −0.56 | −0.11 | 0.32 | −0.06 | 1.35 |
| GPC1 | −0.84 | 0.48 | 0.31 | 0.39 | 0.26 | OR7E91P | 0.51 | −0.50 | −0.34 | −0.57 | −0.19 | AC009118.3 | 0.11 | 0.22 | 0.09 | 0.19 | 0.35 |
| STRN | 0.46 | −0.10 | −0.35 | −0.10 | −0.28 | RPL26P9 | 0.78 | −0.45 | −0.48 | 0.83 | 0.41 | IMPDH1P10 | 0.39 | −1.35 | −0.46 | −1.99 | −0.17 |
| SRRM2-AS1 | −0.76 | 0.23 | 0.38 | −0.04 | 0.40 | AL162171.3 | −0.24 | −0.22 | 0.26 | −0.15 | 0.34 | RIMKLBP1 | 0.08 | 0.11 | 0.34 | 0.01 | 0.12 |
| AC027801.4 | −0.79 | 0.32 | 0.24 | 0.34 | 0.17 | AC092431.1 | −1.15 | 0.70 | 1.86 | −0.68 | 0.93 | AC016747.2 | 0.13 | −0.51 | −0.36 | 0.68 | 0.88 |
| NSUN2 | 0.46 | −0.32 | −0.54 | −0.10 | −0.11 | PCSK4 | −0.39 | −0.17 | −0.01 | 0.28 | 0.24 | AC245100.7 | −0.15 | 0.22 | 1.13 | −0.09 | −0.31 |
| PDZD11 | 0.53 | −0.30 | −0.64 | −0.12 | −0.38 | AL121929.2 | 0.36 | −0.07 | −0.64 | 0.11 | −0.24 | LHX1 | −0.40 | 0.48 | 1.22 | 0.95 | 0.09 |
| MTRF1LP2 | 1.45 | −1.03 | −1.14 | −0.27 | −0.62 | ATG101 | 0.23 | 0.09 | −0.15 | −0.08 | −0.25 | AP003355.2 | −0.12 | 0.33 | 0.72 | 0.06 | −0.05 |
| RABEP2 | −0.69 | 0.38 | 0.16 | 0.40 | 0.22 | KRT83 | −1.32 | 1.58 | 2.89 | 0.03 | 1.70 | AC073592.1 | −0.13 | 0.12 | 0.64 | 0.07 | 0.26 |
| AC012501.2 | 1.56 | −0.27 | −0.59 | 0.04 | −0.54 | RPL23AP35 | −0.33 | 0.26 | 0.87 | 0.02 | 0.80 | LINC01864 | 0.30 | −0.55 | 0.25 | −0.17 | −0.26 |
| P3H2 | 0.90 | −0.64 | −1.42 | −0.05 | −0.60 | LRG1 | 0.51 | −0.94 | −1.57 | 0.66 | 0.02 | AL133215.1 | −0.34 | 0.89 | 1.42 | 0.00 | −1.01 |
| G1862 | −1.35 | 0.22 | 0.61 | 0.21 | 0.53 | AC073916.1 | −0.46 | 0.08 | 0.34 | −0.06 | −0.26 | PSPC1P1 | −0.17 | 0.32 | −0.75 | 0.96 | 0.44 |
| DLGAP1 | −1.15 | 0.36 | −0.36 | 0.28 | −0.20 | AC022440.1 | −0.99 | 0.55 | 0.40 | 0.72 | −0.52 | HNRNPA1P14 | 0.10 | 0.04 | −0.12 | −0.13 | 0.02 |
| NRBF2 | 0.78 | −0.25 | −0.56 | −0.28 | −0.60 | SREBF2 | 0.19 | 0.17 | −0.17 | 0.33 | −0.12 | AC006483.2 | −0.39 | −0.12 | −0.64 | 1.99 | 0.94 |
| SLC47A1P1 | −2.33 | 1.11 | 2.55 | 0.54 | 0.99 | AC109630.1 | −0.99 | −0.10 | −0.69 | 0.10 | −0.98 | FAM90A12P | 0.42 | −0.54 | −2.49 | 1.66 | −0.51 |
| AL162231.2 | −1.23 | 0.14 | 0.56 | 0.02 | −0.14 | AC020978.4 | 0.51 | −0.55 | −0.70 | 0.08 | 0.54 | RNU7-160P | −0.30 | 0.18 | 1.03 | 0.55 | 0.67 |
| CCL18 | 2.07 | −1.00 | −0.96 | 0.05 | 0.67 | AC004461.1 | −0.56 | 0.47 | 1.04 | 0.10 | 0.63 | AC005005.2 | −0.63 | −1.06 | −0.68 | −0.99 | −0.26 |
| RAD21 | 0.55 | −0.25 | −0.37 | −0.11 | −0.23 | EXOC4 | 0.09 | 0.07 | −0.17 | 0.07 | −0.15 | RNU6-854P | 0.57 | 0.62 | −0.50 | 0.27 | −1.35 |
| SIK2 | −0.68 | 0.53 | 0.46 | 0.19 | 0.03 | AC044784.2 | 1.09 | −0.81 | −0.93 | −0.35 | −0.53 | CFL1P7 | −0.62 | 1.25 | 0.43 | 1.84 | 0.05 |
| MYL9 | −1.15 | 0.65 | 0.76 | −0.01 | −0.39 | KLHL38 | −0.85 | 0.60 | −1.46 | 0.77 | −1.87 | CNN3P1 | −1.15 | 0.29 | 1.43 | −1.87 | 0.75 |
| FAM218A | −1.03 | 0.13 | 1.06 | −0.03 | 0.42 | RNU6-515P | −1.22 | 1.22 | 0.81 | 1.09 | −0.78 | RC3H1 | 0.02 | 0.19 | 0.00 | 0.06 | −0.23 |
| PDCL3 | 0.70 | −0.17 | −0.47 | −0.06 | −0.56 | LINC00616 | 1.14 | 1.09 | −1.10 | 1.44 | −1.15 | MYF6 | 0.54 | −0.35 | −2.24 | 0.99 | −1.54 |
| PRMT6 | 0.53 | −0.17 | −0.21 | 0.11 | −0.08 | AL355796.1 | −0.76 | −0.97 | −0.38 | −0.42 | 0.93 | AL137077.2 | −0.14 | 0.37 | 0.49 | 0.23 | 0.22 |
| NFKBIB | 0.56 | −0.18 | −0.70 | 0.00 | −0.47 | GATC | 0.11 | −0.01 | −0.06 | −0.04 | −0.10 | AC099673.1 | −0.33 | −1.79 | −0.92 | −0.34 | −1.79 |
| AL034399.1 | 2.00 | −0.27 | −2.43 | 0.11 | −1.52 | AC104763.1 | 0.34 | −0.31 | −0.86 | −0.17 | −0.57 | AC245047.1 | −0.52 | 0.05 | −0.51 | 0.35 | 0.07 |
| AC011379.2 | −0.77 | 0.46 | 0.69 | 0.49 | 0.48 | CAMK2N2 | 0.85 | 0.18 | −0.39 | 0.42 | 0.10 | AC008438.2 | 0.41 | 0.99 | −0.45 | 0.19 | −1.45 |
| ESCO2 | 1.02 | −1.16 | −1.16 | −0.50 | −0.28 | AC015911.8 | 0.44 | −0.45 | −0.11 | −0.62 | 0.49 | OR4A8 | −0.40 | −0.74 | −0.94 | 0.75 | −0.11 |
| PTRH2 | 0.55 | −0.33 | −0.36 | −0.12 | −0.11 | ABT1 | 0.15 | −0.02 | −0.38 | 0.14 | −0.40 | LINC01842 | 0.34 | −1.23 | −0.59 | 1.40 | −1.21 |
| SLIT3 | −1.27 | 1.00 | 1.47 | 0.15 | −0.11 | AL035411.1 | −0.38 | −0.12 | −0.28 | −0.28 | 0.10 | AC073133.1 | −0.39 | −0.76 | −0.53 | 1.71 | 1.17 |
| IDE | 0.89 | 0.01 | −0.26 | 0.25 | −0.49 | ITPR1-DT | −0.89 | −0.85 | 0.77 | 0.94 | 2.28 | JAK2 | 0.04 | −0.11 | −0.03 | −0.06 | −0.03 |
| MAP3K9 | 0.88 | −0.23 | −0.67 | −0.07 | −0.55 | CPLANE1 | −0.10 | 0.08 | 0.18 | −0.06 | 0.03 | LINC02137 | 0.17 | 1.00 | 0.43 | 0.55 | −0.32 |
| DTX2P1 | −1.12 | 0.48 | 0.92 | 0.08 | 0.15 | AP004289.1 | 0.43 | −0.18 | −0.93 | 0.07 | −0.48 | LINC02531 | −0.43 | 0.44 | −2.16 | −0.41 | −3.85 |
| LIMA1 | 0.67 | −0.46 | −0.99 | −0.26 | −0.52 | AC105384.2 | −1.02 | 1.18 | 2.08 | 1.32 | 0.75 | NME4 | −0.06 | −0.17 | 0.08 | 0.00 | 0.17 |
| GPC3 | −1.93 | 1.58 | 1.46 | 0.54 | −0.40 | NDUFS7 | −0.21 | −0.06 | −0.28 | 0.13 | −0.12 | RNU6-242P | −0.26 | −0.29 | 0.11 | 0.38 | 1.58 |
| ACTG1P1 | −1.38 | 0.16 | 1.11 | −0.18 | 0.44 | KLHDC10 | 0.17 | 0.05 | −0.07 | 0.00 | −0.24 | NCR3 | 0.26 | −0.52 | 1.10 | −0.94 | 0.66 |
| SETX | 0.39 | −0.15 | −0.14 | −0.18 | −0.06 | LINC01467 | −1.37 | 0.68 | 1.18 | 0.27 | −1.13 | SCARNA15 | 0.28 | −0.19 | 0.04 | −0.13 | −0.18 |
| CXCL13 | 2.68 | −2.46 | −1.76 | −1.54 | 0.09 | SP2-AS1 | −0.23 | −0.39 | 0.05 | −0.25 | 0.32 | AC137579.1 | −0.62 | −0.53 | 0.08 | 0.22 | −0.65 |
| CARHSP1 | 0.62 | −0.48 | −0.64 | −0.18 | −0.13 | SMIM19 | −0.22 | 0.25 | 0.24 | 0.13 | −0.02 | MSLN | −0.21 | 1.52 | −1.18 | 0.28 | −1.24 |
| SLC6A17 | −1.19 | 0.17 | 0.44 | 0.09 | 0.87 | ACHE | −0.45 | −0.19 | 0.24 | −0.22 | 0.27 | OR4C2P | 0.60 | −0.82 | −2.83 | 0.03 | −3.91 |
| AL132657.1 | −0.86 | 0.28 | 0.67 | −0.07 | −0.12 | CHMP3 | 0.22 | 0.07 | −0.07 | 0.19 | −0.25 | OR4K14 | 0.66 | −0.03 | −2.26 | 0.43 | −2.33 |
| OSBPL10 | 0.45 | −0.12 | −0.55 | −0.13 | −0.37 | SNAP23P1 | 1.16 | 0.30 | 0.63 | 0.23 | −0.97 | RNA5SP143 | −0.32 | −0.10 | −1.58 | 0.81 | −0.74 |
| GUCA1B | −1.19 | 0.60 | 0.79 | −0.01 | 0.25 | DNASE1L1 | 0.21 | −0.22 | −0.34 | 0.07 | 0.10 | KRT18P32 | −0.63 | −0.54 | −1.00 | 1.41 | −1.75 |
| SERPINA1 | 1.80 | −1.15 | −1.07 | −0.16 | −1.23 | GAP43 | −0.60 | −0.34 | 0.46 | −0.69 | 0.19 | AC099552.1 | 0.40 | −1.21 | −0.86 | −0.58 | −1.74 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| PTHIR | −1.42 | 0.26 | 2.25 | −0.10 | 0.46 | SLA2 | 0.30 | −0.39 | −0.42 | −0.18 | −0.03 | ABCC12 | −0.23 | −1.03 | 0.42 | −0.51 | −0.33 |
| IGKC | 2.30 | 1.66 | 2.28 | 1.20 | −1.39 | RBL2 | −0.14 | 0.14 | 0.39 | 0.10 | 0.17 | LINC02101 | −0.44 | −0.87 | 0.35 | −0.83 | 0.72 |
| ATP6AP1L | −0.61 | 0.12 | 0.85 | 0.09 | 1.01 | AL356968.2 | −0.59 | 0.01 | 0.32 | −0.49 | −0.72 | AL357052.1 | −0.52 | −0.40 | −0.07 | 0.32 | 0.61 |
| FXYD6 | −1.55 | 0.89 | 1.91 | 0.58 | 0.44 | C5orf30 | −0.21 | 0.06 | 0.23 | 0.03 | 0.01 | AL158196.1 | 0.14 | −0.26 | −1.16 | −0.05 | −1.09 |
| AL021368.2 | −0.81 | 0.49 | 1.18 | 0.02 | 0.35 | PLEKHA2 | 0.21 | −0.07 | −0.17 | −0.26 | −0.33 | OCM2 | 0.76 | −0.06 | −0.73 | −0.43 | −3.52 |
| NCAPD2 | 0.59 | −0.34 | −0.47 | −0.17 | −0.18 | AC009090.6 | 0.30 | −0.19 | −0.06 | −0.07 | 0.09 | AC026888.1 | −0.45 | 1.64 | −0.78 | 0.72 | −0.63 |
| PSMD4 | 0.47 | −0.17 | −0.33 | −0.12 | −0.24 | RPL17P40 | 0.95 | −0.57 | −2.17 | 0.42 | −1.73 | G22284 | −0.30 | −1.67 | −1.10 | 0.20 | 1.21 |
| AP000902.1 | 1.85 | −1.33 | −2.63 | −0.62 | −1.96 | MICD | −0.46 | 0.42 | 0.45 | −0.26 | −0.07 | MIR107 | 0.27 | −0.52 | 0.64 | 0.60 | 0.25 |
| STAG3L3 | −0.60 | −0.07 | 0.36 | −0.12 | 0.25 | ABCG2 | 0.31 | 0.17 | −0.27 | 0.47 | −0.27 | RN7SL182P | −0.15 | −0.12 | −0.34 | 0.15 | 0.07 |
| CARTPT | −1.67 | 0.41 | 0.58 | 0.68 | 0.58 | RARRES1 | 0.29 | −0.05 | −0.14 | 0.35 | 0.15 | DNAJA1P1 | 0.42 | 0.00 | 1.35 | 0.38 | 0.12 |
| PALM3 | −1.61 | 0.65 | 1.97 | −0.11 | 0.50 | LINC01116 | −0.45 | 0.16 | 0.62 | 0.16 | −0.13 | AC012488.1 | 0.58 | −1.46 | −1.18 | 1.34 | 0.01 |
| RECQL | 0.58 | −0.35 | −0.30 | −0.36 | −0.29 | SPSB1 | 0.19 | 0.09 | −0.13 | 0.00 | −0.26 | AC008892.1 | 0.17 | 0.11 | −0.86 | −0.46 | −0.64 |
| G34083 | 2.53 | −0.39 | −1.96 | 0.29 | −0.66 | GBP2 | 0.24 | −0.14 | −0.14 | −0.34 | −0.45 | AC073167.1 | 0.46 | −0.30 | 1.36 | −0.01 | 0.17 |
| H3F3B | 0.63 | −0.22 | −0.73 | −0.13 | −0.51 | AL662889.1 | −0.63 | 0.02 | 0.86 | 0.46 | 0.32 | PPIAP47 | 0.87 | −0.84 | −1.69 | 0.11 | −1.33 |
| AKIRIN1 | 0.51 | −0.34 | −0.37 | −0.19 | −0.30 | AL451047.1 | 0.42 | 0.09 | −0.32 | −0.21 | −0.52 | SCG3 | −0.13 | 0.45 | −0.53 | 0.27 | −0.48 |
| ANO8 | −0.82 | 0.64 | 0.55 | 0.43 | 0.18 | RNMT | 0.14 | 0.05 | 0.03 | 0.00 | −0.14 | AC090751.1 | −0.71 | 0.74 | 1.12 | 1.76 | 0.46 |
| LAMA2 | −1.04 | 0.73 | 1.36 | −0.10 | −0.05 | AC016876.1 | −0.41 | 0.54 | 0.49 | −0.13 | −0.01 | INTS4 | −0.03 | 0.05 | 0.04 | 0.03 | 0.04 |
| FBXO11 | 0.41 | −0.17 | −0.39 | −0.17 | −0.30 | AC105036.3 | 0.43 | −0.65 | −0.91 | 0.20 | 0.04 | BBS10 | 0.08 | 0.23 | 0.18 | −0.11 | −0.09 |
| G34276 | −0.86 | 0.50 | 0.75 | 0.06 | 0.14 | AC022080.3 | −1.19 | −0.88 | 0.50 | 0.11 | 0.62 | C3orf22 | 0.32 | −0.21 | 1.14 | −0.86 | 0.79 |
| HIST1H4L | 1.44 | −0.85 | −1.41 | 0.19 | −1.18 | RNA5SP119 | −1.52 | 0.13 | −0.26 | −0.09 | −0.43 | RNU4-48P | −0.21 | 0.45 | −0.80 | 0.22 | −0.50 |
| C5orf24 | 0.46 | −0.18 | −0.44 | 0.02 | −0.30 | ITGB2-AS1 | −0.41 | −0.48 | 0.63 | −0.26 | 0.74 | RAB17 | −0.08 | 0.37 | −0.43 | 0.96 | 0.36 |
| KIZ | −0.46 | 0.45 | 0.37 | 0.22 | −0.07 | AC113155.1 | 0.48 | −0.09 | −0.64 | 0.16 | 0.14 | KIAA1614-AS1 | −0.20 | 0.48 | 0.14 | 0.04 | −0.08 |
| ATP10A | −0.92 | 0.47 | 0.86 | −0.01 | 0.05 | CYP2F1 | −0.65 | 0.28 | −0.71 | 0.62 | 0.15 | SH3RF3 | −0.06 | −0.03 | 0.05 | 0.18 | 0.23 |
| GRPEL1 | 0.63 | −0.33 | −0.63 | −0.19 | −0.46 | PSTPIP1 | 0.30 | −0.69 | −0.70 | −0.21 | 0.24 | RPS7P7 | 0.36 | 0.29 | −0.15 | −0.29 | 0.17 |
| ATP5MPL | 0.82 | −0.47 | −0.49 | −0.46 | −0.42 | RNU1-103P | 1.01 | −0.22 | 2.65 | −1.36 | 1.18 | AC104297.1 | −0.54 | −0.29 | 0.26 | −0.86 | −1.11 |
| DCT | −1.33 | 1.21 | 0.51 | 0.75 | 0.23 | CST3 | 0.28 | 0.06 | −0.24 | 0.03 | −0.37 | AC012593.1 | −0.23 | 0.77 | −0.06 | 0.11 | −0.72 |
| COPE | 0.47 | −0.35 | −0.46 | −0.11 | −0.29 | AC009133.1 | 0.30 | −0.36 | −0.02 | −0.20 | 0.34 | CCDC39-AS1 | −0.65 | 1.18 | 1.30 | −0.34 | 0.13 |
| AC087783.2 | 2.58 | −1.91 | −1.68 | −0.53 | −0.50 | SINHCAFP1 | −0.50 | 0.19 | 0.50 | −0.13 | 0.72 | LINC02206 | −0.53 | −0.30 | 1.35 | 0.50 | 1.43 |
| ADAMDEC1 | 2.27 | −0.38 | 0.35 | −0.74 | 0.62 | MRPL24 | 0.17 | −0.08 | 0.08 | −0.03 | 0.00 | RSL24D1P2 | −0.46 | 1.56 | 0.91 | 1.49 | 1.36 |
| KHSRP | 0.38 | −0.25 | −0.49 | 0.02 | −0.11 | LAMTOR4 | −0.25 | 0.47 | 0.60 | 0.24 | 0.02 | AC108727.2 | −0.35 | 0.91 | −0.88 | 0.65 | −1.48 |
| GTF2F2P1 | 1.22 | −0.68 | −1.44 | −0.09 | −0.69 | MIR4786 | 0.89 | −0.66 | 0.05 | −0.32 | 1.08 | MTND5P17 | 0.43 | 0.69 | 0.10 | 1.18 | −0.15 |
| AL356488.2 | −0.68 | 0.23 | 0.30 | 0.26 | 0.38 | CEBPE | 1.42 | −1.00 | 0.69 | −1.06 | −0.57 | SNORD114-7 | 0.21 | 1.14 | 1.35 | −0.36 | 0.03 |
| CDK2AP1 | 0.61 | −0.33 | −0.55 | 0.10 | −0.19 | AP001775.2 | 0.65 | −0.73 | −0.52 | 0.05 | 0.03 | CYP2A7P2 | 0.34 | 1.89 | 1.24 | 0.48 | 0.38 |
| BRD7 | 0.36 | −0.06 | −0.37 | 0.03 | −0.21 | LINC02289 | −0.48 | 0.89 | −0.32 | 0.68 | −1.21 | AC114912.1 | 0.51 | 0.89 | −1.81 | 0.75 | −2.62 |
| MRPL15 | 0.67 | −0.29 | −0.23 | −0.29 | −0.40 | G38688 | 0.59 | −1.12 | −1.03 | −0.75 | −0.34 | RNA5SP519 | −0.59 | 2.14 | 0.23 | 1.10 | −0.94 |
| G38775 | 2.78 | −0.41 | −1.80 | 0.45 | 0.04 | CBWD4P | 0.62 | 0.09 | −0.50 | 0.43 | −0.51 | AC120057.1 | 0.63 | 0.52 | −1.45 | 2.40 | −2.16 |
| CEP250 | −0.46 | 0.13 | 0.14 | 0.15 | 0.19 | AC104695.3 | 0.49 | −0.33 | −0.56 | −0.46 | −0.39 | ARL6IP5 | −0.07 | 0.03 | 0.13 | −0.09 | −0.07 |
| DAPP1 | 0.80 | −0.48 | −0.46 | −0.34 | −0.34 | AC099314.1 | 0.59 | −0.03 | 0.51 | −0.08 | 0.45 | CTU1 | 0.07 | −0.07 | −0.03 | −0.16 | 0.15 |
| MPP5 | 0.46 | −0.18 | −0.42 | −0.01 | −0.18 | ARHGAP31-AS1 | −0.37 | 0.15 | 0.23 | 0.28 | 0.25 | DAO | 0.31 | −1.18 | −0.77 | −0.28 | −0.65 |
| PBX4 | −0.71 | 0.40 | 0.25 | 0.32 | 0.12 | RDH14 | 0.21 | −0.13 | 0.06 | −0.09 | 0.04 | AC136932.2 | 0.26 | 0.77 | −0.63 | 0.75 | −0.63 |
| DYNC2LI1 | −0.41 | 0.32 | 0.47 | 0.16 | 0.05 | RNU6-936P | 0.63 | −0.12 | 0.15 | −0.35 | 0.47 | AC009137.1 | 0.60 | −1.48 | 0.56 | −0.78 | 1.26 |
| HSPA12A | −0.52 | 0.29 | 0.18 | 0.18 | −0.01 | SMG1 | −0.15 | 0.04 | 0.16 | −0.01 | 0.14 | AGAP2-AS1 | 0.16 | −0.61 | 0.00 | −0.76 | −0.34 |
| PNPLA3 | −1.09 | 0.76 | 1.34 | 0.89 | 0.60 | BHLHE22 | −0.42 | 0.20 | 1.09 | −0.51 | 0.08 | SNRPFP2 | −0.54 | −0.41 | 0.54 | −0.65 | −0.17 |
| ATP2A1 | −1.04 | 0.57 | 0.65 | 0.26 | 0.34 | STX18 | −0.13 | 0.00 | 0.06 | 0.03 | 0.09 | RNU4-53P | −0.37 | 0.79 | 0.67 | 0.38 | 0.10 |
| GSTT2B | −1.80 | 0.77 | 1.32 | 0.53 | −0.05 | G39827 | 1.41 | −0.02 | 0.23 | −1.33 | −0.64 | SOAT1 | 0.10 | −0.20 | −0.24 | 0.16 | 0.98 |
| HDAC6 | −0.38 | 0.12 | 0.15 | 0.09 | 0.12 | RN7SL280P | −1.06 | −0.72 | −1.06 | −0.03 | −0.34 | AL445471.2 | 0.35 | −0.25 | −2.73 | 0.76 | −0.87 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| SHCBP1 | 0.72 | −0.60 | −1.02 | −0.21 | −0.15 | LCA5L | −0.32 | 0.06 | 0.50 | −0.35 | −0.02 | CDHR2 | −0.10 | −0.13 | 0.18 | −0.28 | 0.19 |
| NEK9 | −0.28 | −0.02 | 0.15 | 0.03 | 0.24 | AC099518.1 | −0.59 | 0.14 | 1.04 | 0.09 | 0.51 | AC244015.2 | −0.27 | −1.32 | −1.26 | −0.29 | −0.15 |
| MACF1 | 0.37 | −0.07 | −0.36 | −0.09 | −0.22 | CLIC4 | 0.27 | −0.03 | 0.00 | −0.28 | −0.43 | RNA5SP339 | −0.24 | −0.33 | 1.10 | 0.02 | 0.55 |
| HEXDC | −0.84 | 0.29 | 0.34 | 0.33 | 0.35 | IQCJ–SCHIP1 | −0.40 | −0.15 | 0.08 | −0.49 | −0.28 | RNU6-986P | −0.42 | −0.54 | −0.51 | 0.05 | −1.12 |
| DDX6 | 0.54 | −0.13 | −0.31 | −0.04 | −0.31 | RPL26P27 | 0.50 | 0.00 | 0.15 | −0.18 | −0.13 | RPL22P14 | −0.34 | −1.14 | 0.35 | −0.31 | 1.48 |
| PPFIA3 | −0.86 | 0.60 | 0.30 | 0.50 | 0.21 | KLHL10 | −0.48 | −0.56 | −0.23 | 0.06 | 0.28 | PGGT1BP2 | 0.47 | 0.37 | 1.53 | 0.90 | 0.52 |
| AC034199.1 | 2.78 | −3.37 | −2.11 | 0.47 | −0.90 | AC106786.1 | −0.67 | −1.10 | 0.97 | −0.62 | 0.70 | AC022196.1 | −0.31 | 1.57 | 0.37 | 0.32 | −0.86 |
| SCUBE1 | −1.53 | 0.73 | 1.12 | 0.62 | 0.87 | ARAP1-AS2 | 0.39 | −0.11 | −0.33 | 0.05 | −0.20 | CNGA2 | 0.59 | −1.18 | −0.56 | −0.78 | 1.59 |
| CETN2 | 0.72 | −0.39 | −0.51 | −0.17 | −0.25 | ADGRG4 | −0.69 | 0.30 | −0.47 | 0.82 | −0.48 | FAAHP1 | 0.15 | 0.27 | −0.68 | −0.22 | −0.59 |
| AC103718.1 | 1.17 | −0.81 | −0.71 | −0.65 | −0.39 | RPL17P10 | −0.86 | −1.14 | 0.01 | −0.35 | 0.96 | PAX4 | 0.42 | −1.42 | −0.53 | −0.14 | 0.22 |
| ARHGAP6 | −1.12 | 0.63 | 0.98 | 0.23 | 0.03 | MMGT1 | 0.25 | −0.09 | −0.07 | −0.18 | −0.36 | AC004052.1 | −0.36 | −0.82 | 1.45 | −0.01 | 1.52 |
| GALNT1 | 0.71 | −0.17 | −0.24 | −0.18 | −0.32 | CREM | 0.24 | −0.41 | −0.10 | −0.36 | −0.07 | NRROS | −0.10 | 0.02 | 0.38 | 0.12 | 0.05 |
| ITGA7 | −1.29 | 0.37 | 0.69 | 0.35 | −0.17 | HES7 | −0.67 | 1.24 | 1.12 | 0.58 | 0.47 | KFZp779M065. | 0.21 | −0.33 | −1.26 | 1.50 | 0.20 |
| BOP1 | 0.81 | −0.57 | −0.77 | −0.16 | 0.01 | CUEDC1 | −0.20 | −0.01 | −0.17 | 0.08 | 0.04 | AL022326.1 | −0.35 | −0.59 | −0.02 | −0.44 | 1.05 |
| AC010332.1 | −1.52 | 0.57 | 2.05 | −0.33 | 0.25 | AC022447.7 | −1.45 | −1.26 | 1.10 | −1.52 | −0.33 | AC074325.1 | −0.60 | −0.20 | −0.67 | 2.04 | −1.07 |
| MAGOH | 0.79 | −0.41 | −0.54 | −0.28 | −0.31 | LINC00514 | −0.70 | 0.12 | −1.74 | 0.65 | −1.77 | MIR4458HG | −0.09 | 0.43 | 0.22 | 0.13 | −0.41 |
| NEUROD2 | −1.50 | 0.51 | 0.75 | 0.22 | 0.04 | AC114284.1 | 0.97 | 0.31 | 0.32 | −0.05 | 0.62 | HR | −0.07 | 0.53 | −0.33 | 0.53 | −0.32 |
| ELF1 | 0.44 | −0.08 | −0.26 | −0.04 | −0.27 | RN7SKP245 | −1.46 | 0.58 | 0.59 | 1.27 | −0.38 | AC068898.2 | −0.26 | −1.53 | 0.77 | −1.73 | 0.13 |
| ABCC4 | 0.68 | −0.49 | −0.60 | −0.22 | −0.37 | RNA5SP305 | 0.81 | −0.98 | −1.12 | −0.15 | −1.12 | RANBP20P | −0.27 | 0.19 | −1.11 | 0.67 | −0.71 |
| PPP1R8P1 | −0.97 | 0.39 | 0.58 | 0.41 | −0.16 | AC004878.7 | −1.28 | 0.91 | 2.00 | −0.45 | 0.25 | AC019080.1 | −0.07 | −0.23 | 0.80 | −0.09 | 0.34 |
| GSC | −1.61 | 1.21 | 1.01 | 0.38 | −0.32 | AP004782.1 | −0.87 | 0.13 | −0.09 | 0.73 | −0.61 | DSCR4 | 0.36 | −1.37 | −0.48 | 0.29 | 1.17 |
| RNVU1-6 | 1.81 | −1.95 | −2.83 | −1.31 | −1.44 | LBHD1 | −0.28 | −0.17 | 0.27 | −0.22 | 0.12 | REG1B | 0.36 | −0.11 | −0.69 | 0.76 | 0.95 |
| EXOC5 | 0.54 | −0.24 | −0.34 | −0.11 | −0.21 | HAS2 | −0.37 | −0.29 | 0.56 | −0.24 | −0.06 | AL109918.1 | −0.08 | −0.02 | 0.15 | −0.01 | 0.25 |
| GFM1 | 0.48 | −0.28 | −0.41 | −0.21 | −0.21 | FSHR | −1.08 | −0.23 | −1.24 | 0.99 | 0.47 | AL133279.2 | 0.48 | −1.33 | −1.96 | 0.86 | −0.21 |
| KLF16 | 0.72 | −0.20 | −1.05 | 0.12 | −0.64 | CADM2-AS1 | −1.23 | 0.82 | 0.15 | 0.65 | −0.52 | MTCO1P23 | 0.56 | −0.20 | −1.63 | −0.34 | −2.47 |
| HMGCLL1 | −1.88 | 0.05 | 0.87 | 0.40 | 0.51 | SRXN1 | 0.43 | −0.24 | −0.43 | 0.20 | −0.68 | AC112206.2 | −0.15 | −0.28 | 0.32 | 0.57 | 1.78 |
| KLK13 | 1.42 | −1.50 | −0.82 | −0.68 | −0.05 | CXorf21 | 0.46 | −1.01 | 0.30 | −0.40 | 0.67 | AL162151.2 | −0.19 | 0.66 | −0.92 | 0.75 | −0.58 |
| CCKBR | −1.90 | 1.13 | −0.02 | 1.16 | 0.14 | CARD17 | 0.54 | −0.32 | −0.50 | 0.19 | 0.38 | AC104581.4 | −0.05 | −0.20 | −0.19 | 0.16 | 0.22 |
| SLITRK5 | −1.53 | 0.38 | 0.60 | 0.23 | 0.85 | G4402 | −0.90 | −1.20 | −0.29 | 0.67 | 1.04 | HAUS6P3 | 0.27 | −0.47 | −0.71 | 0.87 | −0.77 |
| CFAP43 | −0.91 | 0.57 | 0.43 | 0.35 | 0.26 | AC128709.2 | −0.98 | 0.94 | 0.76 | −1.24 | −0.55 | AC104332.1 | −0.14 | 0.24 | −0.09 | 0.16 | −0.45 |
| GRWD1 | 0.54 | −0.42 | −0.72 | −0.15 | −0.18 | BNIP3P24 | 0.50 | −0.51 | −0.27 | −0.12 | −0.21 | AL442644.1 | −0.42 | −1.15 | 0.66 | −1.21 | −0.93 |
| AC090877.1 | −1.22 | 0.83 | 0.70 | 0.47 | 0.13 | AC080112.1 | 0.32 | 0.06 | 0.03 | −0.09 | −0.53 | AC004678.1 | 0.12 | 0.08 | −0.06 | 0.19 | 0.01 |
| RRAS2 | 0.63 | −0.39 | −0.88 | −0.16 | −0.35 | AC002091.2 | 0.99 | −1.34 | 0.77 | 0.29 | 0.71 | AP001999.1 | −0.27 | −0.40 | −1.99 | 0.62 | −0.15 |
| MOCS3 | 0.67 | −0.39 | −0.43 | −0.17 | −0.15 | LINC02334 | −0.35 | 0.37 | 0.00 | 0.09 | −0.21 | CHIAP2 | 0.33 | −1.60 | −1.42 | −1.01 | −1.36 |
| AC012020.1 | 1.36 | −0.97 | −1.18 | −0.44 | −0.39 | FAM216A | −0.24 | −0.01 | 0.43 | −0.16 | 0.22 | GTF2IP2 | 1.42 | −1.08 | −1.45 | −1.22 | 0.43 |
| SNRPB2 | 0.72 | −0.49 | −0.53 | −0.37 | −0.26 | ARRDC3-AS1 | 0.28 | −0.21 | −0.15 | 0.09 | 0.00 | AP005062.1 | 0.44 | −1.07 | −0.38 | 0.32 | 0.21 |
| RPS12P26 | 1.27 | −0.51 | −0.88 | −0.08 | −0.17 | LMBRIL | −0.18 | 0.23 | 0.39 | 0.05 | 0.10 | AL139339.1 | 0.26 | 0.00 | 1.55 | −0.74 | 1.00 |
| ACER3 | 0.55 | −0.33 | −0.67 | −0.09 | −0.20 | HNRNPCP2 | 0.28 | −0.53 | −0.18 | −0.20 | −0.09 | RNY4P31 | −0.38 | −2.00 | −0.34 | −2.40 | −2.10 |
| CXCL16 | 0.80 | −0.52 | −0.76 | −0.21 | −0.49 | HSBP1P1 | 0.70 | −0.36 | 0.15 | 0.14 | 1.41 | RNU6-703P | 0.20 | −0.36 | 1.22 | −1.23 | 0.56 |
| CENPC | −0.35 | 0.24 | 0.32 | 0.12 | 0.01 | PPDPF | 0.23 | 0.29 | 0.11 | −0.12 | −0.54 | CDC14C | −0.25 | −0.47 | −2.11 | 0.45 | −1.97 |
| CYGB | −1.00 | 0.38 | 0.85 | −0.02 | −0.06 | HOXC12 | −0.37 | 0.34 | 0.58 | 0.18 | 0.46 | AC093755.1 | 0.38 | 0.52 | −1.34 | −0.91 | −3.29 |
| MRPS10 | 0.71 | −0.35 | −0.58 | −0.26 | −0.37 | SGO1-AS1 | −0.40 | −0.07 | −0.12 | 0.05 | −0.24 | LINC01289 | −0.25 | 1.16 | −3.66 | 0.65 | −3.52 |
| AC064836.3 | −0.84 | 0.70 | 0.91 | 0.41 | 0.48 | CLDN17 | 1.54 | −1.91 | −0.33 | −0.78 | −0.78 | AP002414.2 | −0.18 | 0.16 | 0.19 | −0.10 | −0.19 |
| DYNLT3 | 0.97 | −0.24 | −0.80 | −0.18 | −0.80 | AC010768.2 | 0.41 | −0.01 | −0.54 | 0.05 | −0.01 | RNU1-100P | −0.18 | 0.44 | 0.37 | 0.32 | 0.10 |
| AL356055.1 | 1.65 | −0.81 | −0.73 | −0.45 | −0.28 | AC113410.1 | 0.58 | −0.70 | −1.27 | 0.19 | 0.01 | AC145138.1 | −0.13 | 0.25 | 0.49 | −0.03 | 0.61 |
| PITHD1 | 0.66 | −0.07 | −0.46 | 0.09 | −0.38 | G25345 | 0.43 | −0.43 | 0.62 | −0.76 | 0.03 | RPL21P7 | 0.65 | −1.62 | −0.58 | −0.92 | −0.62 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| HMBOX1 | −0.26 | 0.22 | 0.27 | 0.05 | 0.01 | AF130359.1 | −0.68 | 0.81 | 1.91 | −0.40 | −0.18 | AL049840.4 | 0.08 | 0.03 | −0.12 | −0.14 | −0.16 |
| DHPS | −1.00 | 0.53 | 0.92 | 0.37 | 0.25 | AC115284.3 | 0.59 | 0.20 | −0.27 | −0.01 | −0.22 | AP006287.2 | −0.22 | 0.05 | −0.30 | 0.42 | −0.44 |
| GABPB1 | 0.62 | −0.44 | −0.51 | −0.28 | −0.42 | AC040975.1 | 0.64 | −0.64 | 0.48 | 0.20 | 1.10 | AC008429.4 | −0.10 | 0.04 | 0.01 | 0.16 | 0.03 |
| LINC01237 | −1.02 | 0.14 | 0.54 | 0.00 | 0.77 | AC007920.2 | 0.50 | −0.04 | 0.55 | −0.39 | −0.20 | LINC02199 | −0.30 | 0.63 | −1.12 | 0.58 | −1.68 |
| SNX29P2 | −0.90 | 0.21 | 0.55 | −0.08 | 0.03 | LINC01141 | 0.97 | −1.44 | −1.54 | 0.52 | 0.52 | GABRR2 | −0.12 | −0.14 | 0.40 | −0.10 | −0.17 |
| SNORA11 | −1.43 | 0.93 | 0.82 | 0.82 | −0.08 | AC098818.2 | 0.76 | −0.04 | −0.27 | −0.10 | 0.27 | AC090525.2 | 0.42 | −1.13 | −1.16 | 0.47 | 1.84 |
| GUSBP9 | −0.75 | 0.34 | 0.34 | 0.25 | 0.89 | AKAP9 | −0.12 | 0.33 | 0.17 | 0.16 | −0.11 | CD1A | −0.15 | −0.19 | 0.35 | 0.18 | 0.11 |
| AL022068.1 | −1.25 | 0.63 | 1.47 | 0.20 | 0.26 | SLFN14 | −0.91 | 0.47 | 1.01 | −0.37 | 1.12 | LINC02319 | −0.61 | 0.21 | 1.07 | 0.40 | 0.75 |
| ENTR1 | 0.46 | −0.37 | −0.72 | 0.01 | 0.02 | QPCT | −0.25 | 0.41 | 0.40 | 0.19 | −0.05 | AC024257.2 | −0.40 | 0.42 | 0.27 | −0.02 | 1.09 |
| METAP2 | 0.54 | −0.30 | −0.44 | −0.17 | −0.30 | AC007494.2 | 0.40 | −0.49 | 0.03 | −0.03 | 0.73 | PPP1R42 | 0.25 | 0.10 | −1.08 | 1.14 | 0.35 |
| ATP5F1B | 0.64 | −0.25 | −0.55 | −0.14 | −0.35 | NTMT1 | 0.20 | −0.29 | −0.38 | 0.08 | 0.09 | OR7E38P | 0.12 | 0.15 | 0.09 | 0.11 | −0.01 |
| ATP5IF1 | 0.51 | −0.07 | −0.22 | 0.06 | −0.11 | SMKR1 | 0.63 | −0.25 | −1.05 | −0.04 | 0.04 | ONECUT2 | −0.17 | −0.24 | −0.16 | 0.07 | −0.26 |
| RAB12 | 0.37 | −0.05 | −0.31 | 0.12 | −0.17 | LRRTM1 | −0.86 | 0.26 | 1.44 | −0.18 | 0.70 | AC006942.1 | −0.40 | 0.01 | 0.03 | 0.87 | 0.37 |
| AUNIP | 1.24 | −1.02 | −1.88 | −0.35 | −1.00 | CDC26 | 0.28 | −0.18 | 0.00 | −0.24 | −0.14 | SAA4 | 0.31 | −0.28 | −1.96 | 0.55 | −1.09 |
| GNL1 | −0.41 | 0.28 | 0.13 | 0.16 | 0.05 | AF287957.1 | 0.45 | −0.46 | −0.18 | −0.27 | 0.08 | AC027808.2 | 0.11 | −0.21 | −0.17 | −0.85 | −0.04 |
| BCAP31 | 0.58 | −0.28 | −0.59 | 0.01 | −0.28 | AC068389.3 | 0.41 | −0.14 | −0.13 | −0.09 | −0.03 | AL132642.1 | 0.24 | −1.11 | −0.98 | 0.37 | 1.69 |
| EDNRA | 0.84 | −0.35 | −0.72 | −0.09 | −0.44 | AC079777.1 | −0.53 | 0.01 | 0.26 | 0.32 | 0.59 | MIXL1 | 0.20 | −1.11 | 0.59 | 0.26 | 0.43 |
| LINC01278 | −0.39 | 0.35 | 0.44 | 0.06 | 0.15 | HCG22 | 0.88 | 1.07 | −0.55 | 0.11 | −0.52 | AC011944.1 | −0.31 | −0.98 | −2.09 | 0.34 | 0.87 |
| EFHC1 | −0.45 | 0.35 | 0.43 | 0.09 | −0.10 | AC092535.2 | 0.79 | −0.25 | 0.24 | −0.10 | 0.73 | LMO7-AS1 | −0.10 | 0.08 | 1.17 | 0.03 | 1.02 |
| MTA2 | 0.48 | −0.29 | −0.44 | −0.03 | −0.11 | C11orf65 | −0.23 | 0.19 | 0.34 | −0.16 | −0.16 | AC009533.2 | 0.15 | 0.42 | −0.91 | 0.61 | −0.72 |
| NPM1P8 | −1.85 | 1.42 | −0.51 | 1.56 | 0.47 | AC084024.2 | −0.45 | −0.35 | 1.03 | −0.33 | 0.72 | AC108865.2 | −0.26 | −0.55 | −0.03 | −0.31 | 0.77 |
| AGGF1 | 0.51 | −0.28 | −0.35 | −0.08 | −0.06 | MIR4766 | 1.08 | −0.60 | 1.61 | −0.98 | −0.28 | PRELID1P3 | −0.12 | −0.23 | −0.35 | −0.08 | 0.13 |
| KANSLIL | −0.50 | 0.42 | 0.68 | 0.10 | 0.12 | HOXD13 | −0.91 | −0.10 | −0.18 | 0.58 | 0.60 | SLC12A5 | 0.12 | −0.23 | −0.20 | 0.00 | −0.07 |
| AC087500.1 | −1.12 | 0.28 | 0.45 | 0.42 | 0.16 | RAB28 | 0.18 | −0.08 | 0.21 | −0.16 | 0.10 | GLE1 | 0.03 | −0.05 | −0.26 | 0.06 | −0.06 |
| JUNB | 0.85 | −0.49 | −1.18 | −0.16 | −0.60 | MY06 | −0.20 | 0.29 | 0.14 | 0.11 | −0.21 | ELDR | −0.31 | −0.58 | −2.50 | 0.57 | −1.40 |
| SHROOM2 | 0.62 | −0.13 | −0.84 | 0.22 | −0.23 | RNU6-298P | 0.92 | 0.80 | −0.57 | 0.71 | 0.24 | MIR191 | 0.45 | 0.13 | −0.53 | −0.06 | −0.63 |
| SERBP1P5 | 1.01 | −0.28 | −1.05 | 0.20 | −0.54 | AC005682.1 | 0.33 | −0.15 | −0.32 | −0.03 | −0.09 | COL27A1 | 0.07 | −0.47 | −0.73 | 0.13 | 0.25 |
| SLC24A2 | −1.39 | 0.54 | 0.30 | 0.63 | 0.49 | SLC12A1 | −0.52 | 0.20 | 0.48 | −0.04 | 0.03 | GLI3 | 0.03 | 0.12 | −0.12 | 0.14 | −0.08 |
| LYSMD2 | 0.79 | −0.48 | −0.08 | −0.33 | −0.14 | AC132008.1 | −1.14 | 2.59 | 0.86 | 0.51 | −1.25 | LINC02384 | −0.15 | −0.51 | 0.47 | −0.20 | 0.86 |
| INPP5J | −0.87 | 0.79 | 0.80 | 0.21 | −0.17 | MYO1H | 0.30 | −0.11 | −0.06 | −0.18 | −0.22 | AC097376.1 | −0.06 | 0.10 | 0.09 | 0.09 | 0.19 |
| EIF2S2P4 | 1.09 | −0.51 | −1.04 | 0.17 | −0.65 | KLHL6-AS1 | 1.56 | −1.93 | −1.76 | −0.13 | −0.39 | AL645924.2 | 0.10 | −0.34 | −0.22 | −0.16 | 0.24 |
| GARS-DT | −0.40 | 0.14 | 0.56 | −0.01 | 0.25 | RN7SKP43 | −1.36 | 0.31 | 0.52 | 0.27 | −0.45 | KRT8P32 | −0.58 | −0.20 | −2.04 | 1.73 | −1.71 |
| AL357497.1 | −2.04 | −0.61 | 2.01 | −1.81 | 1.24 | RNU6-1275P | −0.71 | 0.01 | 1.05 | −0.06 | 0.75 | AC011487.1 | −0.22 | −0.47 | 1.71 | −0.60 | 0.76 |
| AC138207.6 | −1.09 | 0.94 | 0.94 | 0.59 | −0.28 | SPATA12 | 0.36 | 0.01 | −0.24 | 0.25 | −0.13 | AC092650.2 | 0.42 | 0.19 | −0.63 | 1.16 | −0.64 |
| G16276 | −2.16 | −0.89 | 0.56 | 0.25 | 1.11 | DDX43P1 | −0.71 | 0.27 | 0.54 | 1.41 | 0.30 | AL391834.2 | 0.11 | −0.24 | −0.36 | 0.10 | −0.32 |
| NDUFB3 | 0.80 | −0.49 | −0.62 | −0.22 | −0.45 | NQ01 | 0.27 | −0.21 | −0.20 | −0.19 | −0.17 | AL121936.1 | −0.25 | −0.53 | 0.39 | −1.07 | 0.02 |
| RN7SL470P | −1.64 | 0.37 | −0.38 | 0.76 | 0.42 | ARIH2 | 0.10 | −0.08 | −0.17 | −0.06 | 0.01 | AP000944.2 | 0.18 | 0.15 | 0.63 | 0.38 | 0.36 |
| RPA1 | 0.47 | −0.18 | −0.31 | 0.03 | −0.23 | AC009495.1 | −0.75 | 0.17 | 0.57 | −0.20 | 0.25 | ACOXL-AS1 | −0.21 | 1.01 | 0.10 | 1.35 | 0.64 |
| AC023157.3 | 1.24 | −1.19 | −0.77 | −0.09 | −0.31 | AC021351.1 | −0.80 | 0.20 | −0.93 | −0.13 | −1.15 | NPHS2 | 0.30 | 0.76 | −2.10 | 1.71 | 0.99 |
| FAM184B | −0.81 | 0.20 | 0.40 | 0.13 | 0.18 | MIR5009 | 0.62 | −0.77 | 0.29 | −0.58 | 0.43 | AC092139.3 | 0.06 | −0.28 | −0.21 | −0.34 | 0.06 |
| C6orf106 | 0.53 | −0.25 | −0.48 | −0.05 | −0.36 | RNA5SP399 | −0.88 | 0.02 | −1.81 | 0.42 | −1.33 | LINC02445 | −0.71 | −1.11 | 0.41 | 0.03 | 0.11 |
| GALNT18 | 0.57 | −0.28 | −0.62 | 0.02 | −0.16 | AL139041.1 | 0.69 | −0.31 | 0.40 | −0.01 | −0.63 | AC068389.2 | 0.25 | 0.41 | −0.44 | −0.48 | −0.32 |
| CCDC125 | −0.38 | 0.07 | 0.18 | 0.07 | 0.15 | AL035658.1 | 0.63 | −0.79 | 0.22 | −0.26 | −0.01 | G41963 | −0.16 | −0.01 | 0.30 | −0.21 | 0.43 |
| SNORA7B | −1.13 | 0.92 | 0.72 | 0.37 | −0.27 | RN7SL694P | −0.69 | −0.22 | 0.10 | 0.45 | 1.25 | GAPDHP23 | −0.56 | 0.64 | 0.17 | −1.08 | −0.11 |
| GALNT3 | 0.83 | −0.26 | −0.51 | −0.34 | −0.37 | CDRT4 | −0.24 | 0.14 | 0.03 | 0.33 | −0.01 | RNU6-523P | 0.12 | −0.15 | 0.50 | −0.34 | 0.28 |
| HAUS7 | −0.83 | 0.24 | 0.19 | 0.22 | −0.16 | NTF4 | −0.43 | 0.55 | −0.21 | 0.41 | 0.53 | AC073909.1 | 0.32 | 0.63 | 0.57 | −1.03 | 0.58 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| RBMS1 | 0.47 | −0.14 | −0.26 | −0.18 | −0.35 | RNU6-800P | 1.15 | −0.57 | −1.32 | 0.55 | −1.36 | BMP1 | 0.06 | −0.16 | −0.14 | −0.23 | −0.04 |
| SCFD1 | 0.48 | −0.14 | −0.42 | −0.08 | −0.33 | RNUSD-2P | −1.22 | 0.13 | −1.41 | 0.85 | −0.76 | AC079598.1 | −1.10 | −0.12 | −0.56 | −0.70 | −0.54 |
| SNHG22 | −0.88 | 0.77 | 0.93 | 0.19 | −0.34 | ANXA2R | −0.44 | 0.22 | 0.39 | −0.08 | 0.05 | AC010320.1 | −0.22 | 0.79 | 0.09 | 0.08 | −0.03 |
| PPP1R11 | 0.45 | −0.18 | −0.45 | −0.09 | −0.24 | SLC5A10 | −0.41 | 0.10 | −0.35 | 0.15 | −0.29 | LDHAP2 | 0.13 | 0.03 | −0.07 | 0.06 | −0.03 |
| PYM1 | 0.52 | −0.11 | −0.57 | 0.06 | −0.31 | AC141557.1 | −0.46 | 0.07 | −0.01 | 0.31 | 0.58 | AC040978.1 | −0.10 | 0.03 | −0.52 | −0.11 | −0.18 |
| NPY1R | −1.46 | 0.63 | 1.40 | 0.40 | 0.60 | AC015959.1 | −0.55 | 0.28 | −0.22 | 0.56 | 0.03 | PRICKLE2-AS3 | −0.13 | −0.55 | −0.33 | −0.54 | −0.11 |
| OR2A1 | −1.16 | 0.50 | 1.17 | 0.60 | 0.58 | LINC01208 | −0.96 | 0.66 | 2.12 | 0.91 | 0.04 | RN7SL124P | −0.35 | −0.43 | −2.00 | 0.29 | −1.02 |
| G2449 | −1.30 | 0.92 | 1.06 | 0.28 | 0.55 | SPCS2P4 | 0.52 | −0.36 | −0.35 | 0.12 | −0.13 | HMGB1P13 | 0.45 | 1.14 | −1.07 | 1.88 | −1.91 |
| AC090696.1 | −2.26 | 1.27 | 2.78 | 0.41 | 0.79 | RPS20 | 0.27 | −0.03 | 0.14 | −0.29 | −0.19 | AC091151.1 | −0.20 | −0.48 | 1.20 | −0.28 | 0.80 |
| AC044810.2 | −1.18 | 0.91 | 1.77 | 0.84 | 0.29 | MIR936 | 0.54 | −0.02 | −1.00 | 0.30 | −0.18 | AC016687.3 | 0.37 | −2.54 | −0.32 | 0.66 | 1.49 |
| BCAS3 | −0.40 | 0.44 | 0.46 | 0.16 | 0.02 | IPO9-AS1 | −0.34 | −0.62 | −0.51 | −0.18 | 0.10 | FGF12-AS2 | 0.34 | −1.19 | −1.97 | −0.51 | −0.90 |
| ITGA11 | −0.88 | 0.70 | 1.04 | −0.36 | −0.28 | AC018529.3 | 0.40 | −0.50 | −0.40 | 0.08 | 0.18 | SNORA70B | 0.59 | 0.32 | −0.09 | −0.44 | −1.18 |
| RAB14 | 0.56 | −0.15 | −0.40 | −0.11 | −0.38 | PLEKHJ1 | 0.12 | −0.31 | −0.29 | −0.05 | 0.13 | RGS17P1 | −0.08 | −0.19 | −0.55 | −0.01 | 0.05 |
| KLF7 | 0.66 | −0.43 | −0.84 | −0.35 | −0.43 | AL033384.2 | 0.70 | −0.63 | −0.17 | 0.29 | 1.02 | AC078878.2 | 0.64 | 1.51 | 0.89 | 0.62 | 0.27 |
| SKP2 | 0.52 | −0.45 | −0.39 | −0.19 | −0.01 | RNU6-195P | 0.64 | 0.18 | −0.04 | 0.44 | −0.59 | MTND4LP9 | −0.21 | −1.00 | −1.24 | −0.06 | 0.14 |
| HHIP | −1.24 | 0.30 | 0.08 | 1.09 | −0.24 | AC103746.1 | −0.55 | −0.29 | 0.84 | −0.49 | 0.28 | AC026316.5 | −1.34 | 0.76 | 2.82 | 0.16 | 0.73 |
| SLC35D1 | 0.75 | −0.35 | −0.56 | −0.07 | −0.20 | MCPH1 | 0.10 | −0.10 | −0.24 | −0.01 | −0.05 | AC010904.1 | −0.38 | 0.74 | −0.23 | 0.08 | −0.99 |
| MIR663AHG | 0.75 | −0.46 | −1.02 | 0.03 | −0.11 | MAP3K4 | −0.10 | 0.14 | 0.04 | −0.01 | −0.15 | RNA5SP441 | −1.28 | 0.47 | 0.11 | 0.30 | 0.59 |
| SNAP29 | 0.59 | −0.09 | −0.38 | −0.08 | −0.51 | DMXL2 | 0.20 | −0.23 | −0.04 | −0.22 | −0.06 | RPL21P10 | 0.13 | −0.17 | 0.28 | 0.02 | 0.29 |
| PRRC2B | −0.42 | 0.22 | 0.21 | 0.20 | 0.13 | AC015802.6 | −0.42 | 0.30 | 0.30 | 0.48 | 0.19 | AC108721.1 | 0.65 | −0.41 | −0.67 | 1.27 | −0.73 |
| LINC01484 | −2.39 | 1.61 | 1.24 | 0.21 | 0.06 | AC118463.1 | −1.82 | 0.41 | 1.68 | 0.95 | 1.21 | EXOC7P1 | 0.36 | −1.89 | −0.87 | −0.23 | −1.01 |
| CLIP3 | −0.79 | 0.31 | 0.82 | −0.26 | 0.30 | G5553 | −1.36 | 1.09 | 0.68 | 0.38 | −1.30 | AC002310.3 | 0.20 | −0.52 | 0.60 | −0.88 | 0.80 |
| AARS | 0.45 | −0.33 | −0.48 | −0.11 | −0.14 | RNU6-59P | 0.52 | −0.28 | −0.39 | −0.01 | 0.31 | LINC01282 | −0.53 | 0.52 | 0.95 | −0.17 | −0.12 |
| LINC01136 | −1.28 | 0.71 | 1.35 | −0.08 | 0.47 | AC004584.1 | −0.56 | −0.24 | 1.33 | −0.10 | 0.25 | AC010267.1 | 0.71 | −1.94 | −0.35 | −0.13 | 0.75 |
| C1orf131 | 0.52 | −0.37 | −0.43 | −0.12 | −0.10 | HLA-T | −0.75 | −0.38 | 2.38 | −0.62 | 0.71 | OR6C2 | −0.65 | −0.21 | −0.27 | 1.35 | 1.07 |
| SLC25A45 | −0.66 | 0.34 | 0.56 | 0.20 | 0.36 | CSF3 | 0.92 | −2.31 | −0.74 | −3.02 | −1.90 | KRT18P17 | −0.68 | −0.16 | −0.45 | −0.08 | −0.70 |
| SNX18P13 | −1.99 | 0.22 | 1.17 | 0.41 | 1.29 | DCAF6 | 0.15 | 0.02 | −0.27 | 0.05 | −0.22 | RNU6-602P | −0.52 | −0.36 | −0.50 | −0.88 | 1.58 |
| LINC01449 | −2.09 | 1.38 | 1.04 | −0.62 | −0.04 | AIF1L | −0.19 | 0.25 | 0.60 | 0.10 | 0.32 | BASP1-AS1 | −0.16 | −0.79 | 0.33 | −1.05 | −0.17 |
| SLC50A1 | 0.47 | −0.20 | −0.39 | 0.01 | −0.27 | LINC01114 | −1.00 | 0.42 | −0.28 | 0.93 | −1.07 | CALHM1 | −0.19 | 0.52 | −1.25 | 0.68 | −1.23 |
| NCALD | −1.02 | 0.96 | 1.57 | 0.11 | 0.71 | SNORA74A | 0.39 | 0.67 | 0.03 | 0.57 | −1.24 | AC067904.2 | −0.34 | −0.87 | −0.99 | 1.68 | −2.01 |
| PEX11A | −1.01 | 0.49 | 0.37 | 0.55 | 0.47 | AC009087.1 | 0.56 | −0.73 | 0.39 | −0.08 | 0.82 | CYP2A13 | −0.42 | −2.12 | −0.69 | −0.99 | 1.19 |
| ESR1 | −0.97 | 0.62 | 1.22 | 0.11 | 0.23 | COBLL1 | 0.20 | −0.09 | −0.43 | 0.11 | −0.20 | LINC01789 | 0.58 | −1.98 | −0.03 | −0.57 | 1.79 |
| LINC00339 | −0.78 | 0.08 | 0.46 | 0.18 | 0.55 | AKAP7 | −0.21 | −0.04 | −0.07 | 0.04 | −0.09 | RNU6-106P | 0.18 | −0.37 | −0.75 | −0.24 | 0.30 |
| GRSF1 | 0.42 | −0.23 | −0.34 | −0.03 | −0.10 | RGS17 | −0.28 | 0.06 | 0.42 | 0.07 | 0.18 | ARL5AP3 | −0.22 | 0.05 | −0.52 | 0.32 | 0.29 |
| FKBPL | 1.03 | −0.34 | −0.54 | −0.05 | −0.30 | KDM8 | −0.26 | −0.15 | −0.01 | 0.01 | 0.43 | SLC22A31 | −0.23 | 0.12 | −0.45 | 1.03 | 0.09 |
| AC135279.2 | 2.07 | −0.14 | −0.99 | −0.21 | −0.49 | AL135786.1 | −0.87 | −1.61 | 0.42 | −0.66 | 1.67 | AP001341.1 | −0.40 | 0.00 | −0.58 | −0.80 | −0.96 |
| PGPEP1 | −0.94 | 0.38 | 0.73 | 0.24 | 0.18 | LINC01250 | −0.95 | −1.00 | −0.68 | 0.04 | 0.32 | PDHA2 | −0.43 | 0.53 | 1.10 | 0.44 | −0.23 |
| FLYWCH1P1 | −2.36 | 2.22 | 3.36 | 0.32 | 0.26 | AP003043.1 | −1.28 | 1.70 | 2.65 | 0.47 | 0.56 | AC097714.1 | −0.29 | −1.27 | −0.20 | 0.91 | 1.44 |
| RSL1D1 | 0.59 | −0.30 | −0.40 | −0.19 | −0.28 | DIRAS1 | 0.27 | 0.10 | −0.13 | −0.18 | −0.44 | AC009831.3 | −0.21 | 0.10 | 1.01 | 0.32 | 1.83 |
| AC010422.8 | −1.02 | −0.11 | 0.48 | 0.05 | 0.58 | BLMH | 0.30 | 0.29 | 0.34 | 0.53 | −0.23 | AC130360.1 | −0.33 | 0.45 | 0.62 | 0.37 | −0.11 |
| LGALSL-DT | −0.98 | 0.47 | 0.55 | 0.28 | 0.27 | RNA5SP479 | 1.08 | −1.05 | 0.39 | −0.23 | 0.15 | RNU6-606P | 0.16 | 0.24 | 0.97 | −0.46 | 0.22 |
| AP000785.1 | −2.52 | 0.54 | 0.37 | −1.63 | −0.25 | AL590233.1 | 0.69 | −0.24 | 0.08 | −0.30 | −0.72 | AL731575.1 | 0.42 | 0.63 | −0.54 | 0.53 | 0.11 |
| SRFBP1 | 0.63 | −0.28 | −0.42 | −0.15 | −0.22 | BCDIN3D-AS1 | −0.39 | −0.46 | 0.29 | 0.06 | 1.08 | ARHGEF18 | 0.07 | −0.28 | 0.12 | −0.01 | 0.22 |
| CASP16P | −1.07 | 0.52 | 0.86 | 0.81 | 0.95 | DSCAM | 0.79 | −0.70 | −1.16 | −0.42 | −0.34 | OR5AR1 | 0.83 | −0.42 | −2.36 | 1.43 | −0.99 |
| SPC25 | 1.08 | −0.68 | −1.07 | −0.44 | −0.50 | AL365338.1 | −0.36 | −0.06 | −0.03 | −0.10 | 0.28 | SKA2P1 | 0.21 | −1.01 | 0.38 | −0.06 | 0.34 |
| SEMA3A | −1.09 | 0.53 | 1.21 | 0.10 | 0.14 | ABHD5 | 0.25 | 0.20 | 0.13 | 0.25 | −0.01 | AC017074.2 | −0.41 | −0.18 | −0.92 | 1.58 | −0.13 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| CTNNA3 | −1.45 | 0.63 | 0.55 | 0.97 | −0.15 | RNF146 | −0.15 | 0.12 | 0.23 | 0.01 | 0.05 | NBEAL1 | 0.03 | 0.08 | −0.01 | 0.01 | −0.11 |
| SPAG1 | 0.48 | −0.04 | −0.07 | −0.08 | −0.20 | AC011978.2 | 0.34 | −0.63 | −0.29 | −0.04 | 0.09 | AC099667.1 | 0.18 | −0.12 | 0.52 | −0.38 | −0.18 |
| AC004585.1 | 1.78 | −1.09 | −1.97 | −0.44 | −1.02 | PM20D2 | 0.16 | −0.04 | 0.13 | 0.00 | 0.16 | MIR380 | 0.52 | 0.29 | 1.74 | −0.85 | 0.12 |
| MRPL27 | 0.49 | −0.25 | −0.43 | −0.03 | −0.19 | CHCHD3P1 | −1.73 | 1.86 | 0.46 | 0.62 | −1.02 | AL160237.2 | −0.63 | 0.11 | −0.25 | −0.58 | −1.49 |
| BMS1P10 | −0.99 | 0.30 | 0.52 | 0.25 | 0.67 | AL031658.1 | −0.46 | −0.06 | 1.18 | −0.08 | −0.04 | NPM1P26 | 0.06 | −0.08 | −0.07 | 0.00 | −0.21 |
| DGLUCY | −0.51 | 0.20 | 0.40 | 0.18 | 0.18 | MIR429 | −0.75 | −0.17 | −0.28 | 1.24 | 0.24 | NT5DC4 | 0.30 | −0.11 | −1.74 | 0.17 | −0.90 |
| ANO3 | −1.48 | 0.77 | 0.94 | 0.37 | −0.07 | MMD | −0.44 | 0.13 | 0.14 | 0.19 | 0.11 | SNRPCP4 | 0.16 | 0.06 | −0.53 | −0.04 | −0.60 |
| RNU6-115P | −2.18 | 0.32 | 0.26 | −0.12 | −0.18 | AC002056.1 | 0.64 | −0.53 | 0.23 | 0.55 | 0.54 | ATP5MGP4 | −0.81 | −0.65 | 0.79 | −0.95 | 1.55 |
| CHUK | 0.49 | −0.20 | −0.39 | −0.12 | −0.32 | AC096638.2 | 0.99 | −1.35 | −1.80 | 0.17 | 0.17 | EIF4BP7 | 0.08 | 0.20 | −0.10 | 0.20 | −0.19 |
| MOB3B | 0.47 | −0.38 | −0.59 | −0.04 | −0.27 | AC010618.2 | −0.45 | 0.10 | −0.18 | −0.19 | 0.05 | AMPD2 | −0.05 | −0.22 | −0.22 | −0.01 | 0.04 |
| POLR2G | 0.48 | −0.28 | −0.30 | −0.07 | −0.35 | AC026316.2 | −1.42 | −1.78 | 1.03 | −1.68 | −0.38 | RPS8P3 | −0.53 | −0.75 | 0.89 | −1.69 | 0.76 |
| SPTY2D1 | 0.54 | −0.21 | −0.45 | −0.21 | −0.46 | AL031320.1 | 0.37 | −0.67 | −0.66 | −0.09 | 0.46 | MTCO1P47 | 0.41 | −0.67 | −0.71 | 0.33 | 0.33 |
| RNF8 | 0.40 | −0.23 | −0.30 | −0.12 | −0.06 | C4orf47 | −0.37 | 0.14 | 0.56 | 0.22 | 0.51 | C19orf85 | −0.22 | −0.83 | −0.13 | −0.40 | 1.08 |
| LURAP1 | −1.06 | 0.81 | 0.15 | 0.81 | 0.15 | AL138885.3 | 0.94 | −0.26 | −2.65 | −0.45 | −1.92 | IFNA17 | 0.81 | −1.34 | −1.12 | 0.16 | 1.03 |
| PMM2 | 0.51 | −0.43 | −0.40 | −0.19 | 0.07 | BALAP2L2 | −0.31 | −0.02 | 0.00 | 0.14 | 0.41 | LINC02322 | −1.31 | −0.45 | 1.25 | −0.51 | 1.59 |
| NNT-AS1 | −0.61 | 0.24 | 0.44 | 0.05 | 0.13 | AL391987.5 | −0.98 | 0.25 | 0.44 | 0.78 | 1.60 | RN7SKP291 | 0.26 | −0.88 | 0.35 | −0.85 | 0.51 |
| AC004890.2 | −1.10 | 0.62 | 0.50 | 0.65 | 0.15 | CDKL4 | −0.49 | 0.24 | 0.31 | 0.35 | 0.00 | AC111000.4 | 0.52 | −1.08 | 0.04 | 0.52 | 0.15 |
| PCDHGC3 | 0.48 | −0.17 | −0.31 | −0.09 | −0.08 | AC005288.1 | 0.23 | 0.02 | 0.09 | −0.02 | −0.08 | MIR101-2 | 0.35 | −0.29 | 0.44 | −0.48 | 1.94 |
| MLF2 | 0.43 | −0.16 | −0.35 | 0.05 | −0.18 | AC004801.6 | 0.68 | −0.52 | −0.28 | −0.29 | −0.38 | AL118523.1 | 0.68 | −1.31 | 1.03 | 0.04 | 1.96 |
| CCDC162P | −0.79 | 0.10 | 0.82 | 0.16 | 0.30 | FCGRIB | 0.82 | −1.68 | −0.59 | −0.64 | 0.14 | AC017037.4 | 0.64 | −0.16 | 0.95 | 0.18 | −0.57 |
| AL133245.1 | −0.95 | 0.25 | 0.81 | 0.19 | 0.46 | AC115102.1 | −0.30 | −0.10 | 0.03 | −0.10 | 0.17 | C1orf189 | −0.15 | 0.11 | 0.31 | −0.28 | 0.04 |
| SEMA3G | −1.24 | 1.08 | 1.06 | 0.76 | 0.27 | AL360169.1 | 1.04 | 0.11 | −0.46 | 0.25 | −0.75 | AC009831.4 | −0.28 | −0.31 | −2.53 | 1.34 | −1.41 |
| SLC14A1 | −1.54 | 0.63 | 2.15 | 0.53 | 1.96 | AC023794.1 | −0.45 | 0.40 | 0.79 | 0.27 | 0.64 | MIR3127 | 0.40 | 0.64 | −0.58 | −0.69 | −2.85 |
| IL17RE | −0.75 | 0.54 | 0.37 | 0.37 | 0.13 | SIGLEC11 | −0.85 | 0.18 | 0.06 | 1.05 | −0.40 | AC002091.1 | −0.27 | −1.19 | −0.03 | −0.63 | 0.05 |
| CEBPB | 0.71 | −0.24 | −0.57 | −0.27 | −0.68 | AL355102.3 | 1.13 | 0.33 | −0.05 | 0.24 | 0.05 | AC092614.1 | −0.11 | −0.21 | −0.30 | −0.34 | −0.09 |
| KSR1 | −0.57 | 0.17 | 0.33 | 0.20 | 0.35 | AC120498.3 | −1.20 | −0.44 | 0.02 | −0.04 | 0.61 | LCE1E | 0.15 | 0.26 | 0.62 | 0.97 | −0.31 |
| CEP152 | 0.54 | −0.42 | −0.66 | −0.24 | −0.18 | LINC02510 | −1.10 | −0.62 | 1.33 | −0.41 | −0.05 | FAM138B | −0.51 | 0.71 | 0.70 | 1.90 | 0.32 |
| NPHP1 | −0.89 | 0.59 | 0.82 | 0.07 | −0.23 | SPECC1L | 0.17 | 0.00 | −0.13 | −0.07 | −0.06 | AC061961.1 | 0.63 | −1.01 | −1.12 | 0.16 | 0.12 |
| FAM156A | −1.14 | 0.00 | 0.97 | −0.41 | −0.19 | MBD1 | 0.13 | −0.01 | −0.30 | −0.02 | −0.13 | ABHD16A | 0.08 | 0.24 | 0.02 | 0.19 | −0.16 |
| PRKAG2 | −0.71 | 0.36 | 0.55 | 0.01 | 0.09 | AC138951.1 | −0.34 | 0.12 | 0.61 | 0.38 | 0.25 | AL137220.1 | −0.35 | 0.69 | 0.70 | 0.31 | 0.61 |
| RBM20 | −0.97 | 0.51 | 1.30 | −0.13 | 0.20 | FP325330.2 | −0.75 | −0.24 | 0.83 | 0.32 | 1.04 | AL390835.1 | −0.34 | −1.35 | −2.19 | 1.18 | 1.63 |
| NAMPTP1 | 1.65 | −1.16 | −1.64 | 0.00 | −1.38 | AL035078.1 | −0.80 | −0.39 | 1.02 | −1.13 | 0.69 | PXDNL | 0.12 | −0.19 | −0.24 | 0.59 | 0.21 |
| AL133216.2 | −1.06 | 0.15 | 0.60 | 0.61 | 0.36 | AL355304.1 | 0.97 | −0.70 | −2.01 | −0.07 | −1.13 | KLF17 | 0.33 | −1.51 | −2.24 | 0.49 | −0.94 |
| BYSL | 0.63 | −0.50 | −0.35 | −0.23 | −0.06 | OPN3 | 0.39 | −0.05 | −0.24 | −0.03 | −0.61 | NCEH1 | 0.07 | −0.07 | −0.25 | −0.06 | −0.22 |
| RAB11FIP3 | −0.62 | 0.19 | 0.26 | 0.20 | 0.22 | CLIC4P1 | −1.05 | 1.01 | 1.37 | 0.88 | 1.15 | AL513523.1 | −0.06 | 0.06 | −0.17 | 0.11 | 0.14 |
| AL162385.1 | −1.86 | 1.12 | 0.77 | 1.49 | 0.84 | NUP210 | −0.27 | −0.22 | 0.08 | −0.01 | 0.62 | OR2W3 | 0.22 | −0.08 | −0.07 | −0.02 | −0.84 |
| POMT1 | −0.52 | 0.27 | 0.43 | 0.03 | 0.20 | BTG1P1 | −0.74 | 0.25 | 2.39 | 0.06 | 1.14 | GJB7 | −0.10 | 0.36 | −0.09 | 0.50 | −0.27 |
| GOLGA8N | −0.84 | 0.70 | 1.14 | 0.10 | 0.23 | LINC02477 | 0.54 | 0.02 | −0.72 | 0.04 | −0.20 | HTR3D | 0.32 | −0.69 | −1.36 | 0.57 | −0.71 |
| BTBD1 | 0.58 | −0.21 | −0.40 | −0.05 | −0.26 | AC008972.2 | 0.74 | −0.28 | 0.60 | 0.40 | 0.17 | MYOZ3 | −0.14 | 0.00 | −0.59 | 0.44 | 0.28 |
| SLC25A15 | 0.62 | −0.16 | −0.47 | −0.01 | −0.12 | IDS | −0.20 | 0.23 | 0.19 | −0.01 | −0.21 | AC010609.1 | 0.30 | −0.98 | −0.70 | −0.68 | −1.34 |
| C17orf113 | −1.23 | 1.04 | 0.60 | 0.67 | 0.20 | IGFL4 | 0.45 | −0.46 | −0.34 | −0.22 | 0.17 | G27536 | 0.30 | 0.09 | 1.96 | −0.68 | 0.03 |
| NUAK1 | −0.76 | 0.65 | 1.00 | 0.17 | 0.18 | HOXC-AS1 | −0.42 | 0.72 | 0.47 | 0.11 | −0.25 | AP003066.1 | −0.76 | 0.45 | −0.38 | 1.58 | −1.85 |
| NT5C2 | 0.46 | −0.23 | −0.36 | −0.14 | −0.15 | C9orf50 | −0.73 | 0.83 | −0.15 | 0.25 | −0.04 | LINC01104 | −0.31 | −1.40 | −2.24 | 1.09 | −0.12 |
| AC103591.4 | −0.97 | 0.17 | 0.70 | −0.41 | 0.25 | ATP6V1E2 | −0.18 | −0.10 | 0.41 | −0.04 | 0.22 | RNU4-38P | 0.55 | −0.51 | −2.00 | −0.63 | −1.04 |
| CREB5 | −0.96 | 0.66 | 0.38 | −0.13 | −0.68 | POU6F2 | −0.63 | 0.45 | −0.63 | 0.34 | −0.76 | AC063943.1 | 0.22 | −0.34 | −0.15 | 0.22 | 1.05 |
| SLC35E3 | −0.38 | 0.28 | 0.27 | 0.16 | 0.14 | AC118758.3 | −0.68 | 0.32 | 0.03 | −0.02 | −0.82 | AC093117.1 | −0.25 | −0.26 | −0.19 | −0.14 | 0.42 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC127496.5 | −1.58 | 0.20 | 0.36 | 0.04 | 0.36 | RNU6-135P | 0.61 | −0.69 | −0.63 | −0.81 | −0.29 | AL512658.1 | 0.74 | −0.97 | −1.63 | −1.43 | −1.40 |
| COL9A2 | −1.33 | 0.78 | 0.46 | 0.39 | −0.10 | LINC01516 | −1.40 | 0.01 | −0.61 | 0.46 | −0.91 | OGFOD1P1 | 0.18 | −0.69 | −0.76 | 0.31 | −0.04 |
| REN | −1.54 | −0.53 | 0.77 | −0.11 | 0.35 | P4HA3-AS1 | 1.11 | −0.86 | −2.81 | 0.04 | −0.31 | GAPDHP72 | 0.26 | −0.35 | −1.33 | −0.13 | −1.23 |
| ARHGEF33 | −0.89 | 0.40 | 1.03 | −0.44 | 0.08 | HNRNPRP1 | 0.27 | −0.05 | −0.10 | −0.08 | 0.13 | EGFL6 | 0.17 | −0.62 | −0.24 | −0.42 | −0.27 |
| SNORD116-23 | −1.55 | 0.94 | 1.46 | 0.85 | −0.52 | AL391650.1 | −0.60 | −0.02 | 0.01 | 0.32 | −0.32 | AL080251.1 | −0.16 | 0.75 | −0.29 | 0.55 | −0.61 |
| MT2A | 1.30 | −1.39 | −0.83 | −1.00 | −0.22 | HMGN1P7 | −0.48 | −0.18 | 0.14 | 0.39 | 0.62 | AC012379.1 | 0.57 | −2.07 | −0.92 | −1.92 | 0.03 |
| COX7A2 | 0.60 | −0.26 | −0.59 | 0.00 | −0.49 | PZP | −0.37 | 0.14 | 1.33 | −0.16 | 0.41 | RNU6-890P | 0.18 | 0.37 | −0.22 | −0.21 | −0.75 |
| LVRN | −1.57 | 0.80 | 1.29 | 0.54 | 0.25 | SACMIL | 0.13 | −0.08 | −0.02 | −0.06 | 0.01 | CEP170B | −0.06 | 0.05 | −0.56 | 0.30 | −0.10 |
| RPS15A | 0.65 | −0.18 | −0.69 | 0.24 | −0.63 | AKR1B1 | 0.22 | −0.16 | −0.04 | 0.04 | 0.04 | FO704657.1 | 0.22 | 0.24 | 0.69 | −0.39 | 1.18 |
| GBA | 0.60 | −0.31 | −0.49 | −0.11 | −0.40 | RN7SL750P | −0.60 | 0.24 | −0.21 | 0.66 | 0.20 | AC025284.1 | −0.34 | 0.03 | 0.55 | −1.74 | 0.67 |
| SGPP2 | 1.09 | −0.18 | −0.38 | −0.02 | −0.13 | AL731571.1 | −0.25 | 0.34 | −0.26 | 0.48 | −0.02 | AC090377.1 | 0.22 | −0.37 | −0.83 | 0.44 | 0.06 |
| ADCY8 | −1.79 | 1.85 | 1.75 | 0.31 | 0.73 | AC103831.1 | 1.50 | −2.30 | −2.11 | 0.37 | 0.38 | AC105213.1 | 0.35 | −0.83 | −0.38 | 0.79 | −0.45 |
| SUCO | 0.63 | −0.21 | −0.55 | −0.04 | −0.39 | AC009166.2 | 0.86 | −0.63 | −0.52 | −0.32 | −0.99 | AC090589.2 | 0.18 | −0.38 | 0.20 | 0.31 | 0.25 |
| FAM21FP | −1.10 | 0.32 | 0.81 | 0.08 | 0.22 | G10021 | −0.76 | 0.44 | 1.25 | 1.01 | 0.74 | AL603865.2 | −0.55 | 0.84 | 1.00 | 0.49 | 1.73 |
| RN7SL613P | −1.75 | −0.01 | 1.22 | 0.41 | 0.63 | RN7SL521P | 0.51 | −0.46 | 0.04 | −0.29 | 0.49 | AC114684.1 | 0.54 | −0.82 | 0.15 | −1.24 | −0.51 |
| KRT75 | 2.44 | −0.60 | −1.30 | −0.30 | −1.96 | MTCYBP11 | 1.15 | −2.21 | −1.64 | −0.73 | −1.73 | AC004899.1 | 0.83 | −0.87 | −1.27 | 0.52 | 0.10 |
| ACSL4 | 0.75 | −0.56 | −0.44 | −0.35 | −0.29 | AC025459.1 | −0.54 | 0.13 | −0.77 | 0.86 | 0.20 | RNA5SP284 | 0.43 | −0.39 | −1.69 | 0.62 | −0.90 |
| AC093028.1 | −2.12 | 0.96 | 0.45 | 0.62 | −0.14 | AC005920.2 | 0.51 | 0.09 | −0.71 | −0.44 | −0.66 | LINC01953 | 0.75 | −2.23 | 0.42 | −1.38 | 0.51 |
| RAD52 | −0.57 | 0.27 | 0.56 | 0.01 | 0.22 | LINC02268 | −0.67 | −0.59 | 0.05 | 0.12 | 0.10 | NIFKP1 | 0.57 | −0.83 | −2.01 | 0.19 | −0.73 |
| CACNAIF | −1.43 | 0.54 | 0.58 | 0.59 | 0.50 | AC092375.1 | −0.94 | 0.94 | 0.81 | −0.24 | −1.61 | RPS29P20 | 0.28 | 0.48 | −1.86 | −0.54 | −0.74 |
| GJB4 | −1.31 | 0.95 | 2.41 | −0.41 | 0.62 | AL035693.1 | 0.54 | −0.62 | −0.52 | −0.40 | 0.60 | PEX14 | −0.05 | 0.05 | −0.21 | 0.14 | −0.01 |
| ALDH18A1 | 0.46 | −0.25 | −0.22 | −0.25 | −0.16 | CPSF6 | −0.09 | 0.05 | −0.04 | 0.14 | 0.00 | AC079584.2 | −0.27 | −0.39 | −2.02 | 0.81 | −0.48 |
| LSM7 | 0.52 | −0.28 | −0.39 | −0.11 | −0.03 | AC090515.1 | 0.97 | −0.70 | −0.79 | 0.90 | 0.56 | AL137025.1 | −0.14 | −0.07 | −0.14 | −0.14 | 0.01 |
| HRNR | 1.41 | −0.91 | −0.35 | 0.56 | −0.61 | AC015802.2 | −1.18 | −0.64 | −1.12 | 0.53 | 1.56 | PIN4P1 | 0.13 | −0.66 | −0.12 | −0.62 | 0.10 |
| RAD51-AS1 | −0.67 | 0.39 | 0.74 | 0.22 | 0.37 | EIF4A2P2 | −0.29 | 0.25 | 0.61 | 0.08 | 0.15 | AC027541.1 | −0.76 | −0.59 | −0.02 | 0.69 | −0.62 |
| INTS4P2 | −0.90 | 0.39 | 0.62 | 0.50 | 0.06 | POLD1 | 0.21 | −0.42 | −0.65 | 0.06 | 0.06 | LINC01996 | −0.35 | −0.45 | −1.92 | 0.94 | −0.57 |
| LPL | −1.97 | 1.82 | 1.54 | 0.91 | −0.14 | MARCKSL1P1 | 0.52 | −0.32 | 0.70 | −0.30 | 0.97 | AC009396.1 | 0.73 | −0.70 | −1.33 | −0.01 | −1.33 |
| BRF1 | −0.62 | 0.30 | 0.13 | 0.42 | 0.22 | EDDM13 | −0.24 | 0.04 | 0.41 | 0.01 | 0.38 | AL356489.1 | 1.12 | −0.01 | 0.24 | 0.62 | 0.73 |
| NSFLIC | 0.42 | −0.15 | −0.46 | −0.05 | −0.27 | AC025627.1 | −0.59 | 0.47 | 0.47 | 0.55 | 0.44 | GMCL2 | −0.45 | −0.92 | −0.14 | 0.42 | 0.93 |
| BRCC3 | 0.67 | −0.37 | −0.39 | −0.07 | −0.10 | AC097375.2 | −0.78 | 0.13 | 1.54 | −0.38 | 0.61 | LINC01879 | −0.32 | −1.31 | −1.24 | 1.19 | 1.60 |
| DNAJC16 | 0.29 | −0.10 | −0.09 | −0.10 | −0.04 | LINC01989 | 0.98 | −0.47 | −0.03 | −0.09 | −0.11 | AC108218.1 | 0.13 | −0.67 | −0.52 | 0.30 | 0.00 |
| AC079848.1 | −1.22 | 0.26 | 1.07 | 0.19 | 0.93 | LINC01544 | −0.64 | 0.32 | −0.07 | 0.41 | 0.15 | AP000477.1 | −0.54 | 0.23 | 0.29 | 0.24 | 0.58 |
| HLF | −0.96 | 1.11 | 1.19 | 0.56 | 0.02 | AC073343.1 | −0.62 | 0.37 | 0.80 | −0.56 | −0.36 | EIF4E1B | 0.33 | −0.25 | −2.09 | −0.05 | −2.79 |
| RECQL5 | −0.64 | 0.25 | 0.21 | 0.27 | 0.19 | ATP1B3-AS1 | 0.44 | −0.20 | −0.38 | 0.23 | −0.11 | LRFN1 | −0.09 | −0.18 | 0.05 | 0.05 | 0.69 |
| G7779 | 2.33 | −2.42 | −3.58 | −0.46 | −1.91 | RPP21 | −0.31 | −0.35 | 0.37 | −0.05 | 0.50 | RNU6ATAC38P | −0.43 | −0.71 | 0.62 | 0.25 | 1.76 |
| LINC02233 | 2.01 | −0.66 | −1.82 | −0.27 | −0.36 | CYCSP23 | −0.99 | 0.68 | 0.61 | 0.03 | 0.91 | MIR3941 | 0.17 | −0.05 | 0.48 | −0.05 | 0.13 |
| HSP90B1 | 0.76 | −0.59 | −0.60 | −0.36 | −0.19 | PRRT3-AS1 | −0.38 | 0.32 | 0.77 | 0.29 | 0.33 | AL157385.2 | −0.14 | −0.69 | −0.54 | −0.59 | −0.48 |
| ENTHD1 | −1.32 | 0.54 | 1.70 | 0.16 | 0.82 | AL158071.2 | −0.82 | 0.84 | 1.18 | −0.31 | 0.24 | AC073657.2 | 0.22 | −0.57 | 0.67 | −0.15 | 0.02 |
| PTPRZ1 | 0.97 | −0.21 | −0.34 | −0.09 | −0.13 | AL357054.1 | 0.38 | −0.47 | −0.31 | −0.23 | −0.23 | AC093915.1 | 0.38 | −1.92 | −1.28 | −1.54 | 1.45 |
| SPAG8 | −1.23 | 0.74 | 1.18 | 0.34 | 0.39 | GRTP1-AS1 | −0.48 | 0.29 | 0.35 | 0.28 | 0.33 | KRTAP4-1 | −0.45 | 0.49 | 1.93 | −2.25 | −0.72 |
| SGPP1 | 0.66 | −0.44 | −0.35 | −0.21 | −0.42 | AC022068.1 | −1.16 | 0.08 | −0.99 | −0.15 | −0.38 | GABARAPL2 | −0.05 | 0.16 | 0.33 | 0.03 | −0.21 |
| MRPS6 | 0.61 | −0.33 | −0.70 | 0.05 | −0.31 | RNA5SP129 | 0.58 | 0.53 | 0.24 | −0.35 | −0.43 | AC005363.2 | 0.23 | −0.75 | 0.49 | 0.06 | 1.22 |
| MARCKS | 0.47 | −0.44 | −0.60 | −0.03 | −0.08 | AL591025.1 | 0.48 | −0.25 | −0.33 | −0.13 | 0.05 | RAD21L1 | 0.24 | −1.26 | −0.79 | 0.70 | 0.08 |
| C11orf80 | −0.55 | 0.36 | 0.45 | 0.19 | 0.31 | IDI2-AS1 | −0.71 | −0.39 | −0.15 | −0.25 | −0.13 | AL139819.1 | 0.68 | 0.39 | −1.26 | −0.53 | −1.70 |
| DPH1 | −0.66 | 0.40 | 0.22 | 0.43 | 0.14 | FBXL5 | 0.18 | −0.04 | −0.08 | −0.10 | −0.13 | MIR135A1 | 0.20 | −1.17 | −0.69 | −0.30 | 0.70 |
| PYGM | −1.13 | 0.35 | 0.79 | 0.38 | 0.25 | PLXNA1 | 0.16 | −0.18 | −0.46 | −0.01 | 0.00 | HAR1B | 0.50 | −1.35 | −0.25 | −0.48 | −0.76 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| PACS1 | 0.39 | −0.20 | −0.45 | −0.03 | −0.02 | RN7SL672P | 0.58 | −0.74 | −0.89 | −0.15 | 0.07 | RNU4-23P | −0.26 | 1.28 | 1.22 | 0.00 | 0.33 |
| HMGB1P6 | 0.81 | −0.55 | −0.37 | −0.37 | −0.17 | MIR4525 | −0.99 | −1.55 | 1.14 | 0.42 | 1.53 | AC025125.1 | 0.57 | −0.57 | −1.27 | −0.08 | 0.92 |
| LEKR1 | −0.85 | 0.27 | 0.83 | −0.05 | 0.29 | LINC01497 | −1.03 | −0.68 | −0.26 | 0.60 | −0.14 | AL356108.1 | −0.22 | −0.14 | −0.17 | 0.07 | −0.70 |
| RNF19B | 0.75 | −0.57 | −1.22 | −0.25 | −0.81 | AC005702.1 | 0.64 | −0.12 | 0.06 | 0.49 | 0.40 | RPL22P11 | −0.63 | 0.32 | 1.91 | −0.58 | 1.53 |
| C8orf34 | −1.48 | 0.95 | 1.11 | 0.75 | −0.06 | OVOL3 | 0.64 | 0.05 | −0.21 | 0.08 | 0.14 | AC090519.6 | 0.22 | 0.25 | 0.31 | −0.17 | 0.12 |
| LINC01322 | 2.79 | −1.56 | −3.15 | 0.27 | −0.93 | AC005759.1 | −1.14 | 1.14 | 0.59 | 0.02 | −0.59 | AL929472.1 | −0.31 | −1.25 | 1.64 | −0.60 | 1.63 |
| CEACAM19 | 0.62 | −0.07 | −0.72 | 0.01 | −0.52 | RPS3AP22 | −0.71 | 0.24 | 1.25 | 1.21 | 1.71 | RN7SL245P | −0.34 | −0.41 | 0.65 | 0.14 | 1.93 |
| COTL1 | 1.05 | −1.08 | −0.65 | −0.38 | 0.04 | AP001596.2 | 1.29 | −1.06 | 0.10 | 0.73 | 1.09 | AC006484.1 | −0.50 | −0.20 | −1.60 | −0.31 | 0.08 |
| ALG2 | 0.53 | −0.28 | −0.32 | −0.23 | −0.14 | OPRK1 | −0.81 | −0.46 | −0.17 | 0.58 | 0.42 | AF127577.4 | −0.14 | 0.22 | −0.50 | −0.22 | −0.73 |
| AHDC1 | −0.67 | 0.45 | 0.30 | 0.35 | 0.05 | AC016493.1 | −0.38 | −0.19 | 0.26 | 0.06 | 0.31 | MIR602 | −0.63 | −0.20 | −0.06 | 0.44 | 0.49 |
| CCDC43 | 0.51 | −0.26 | −0.57 | 0.03 | −0.24 | C2CD3 | −0.11 | −0.07 | −0.10 | −0.09 | 0.00 | AC008780.1 | −0.97 | −0.12 | 0.70 | −0.93 | 0.96 |
| AC113208.1 | −1.70 | 1.49 | 1.38 | 0.74 | 1.32 | AP005435.1 | 0.81 | 0.64 | 0.03 | 0.86 | −0.42 | MGAT3-AS1 | −0.28 | 0.57 | −1.42 | 0.44 | 0.42 |
| AC092349.1 | 2.05 | −0.95 | −4.35 | −0.05 | −2.51 | DNMT3B | 0.22 | −0.26 | −0.17 | −0.05 | −0.29 | POLR3H | 0.04 | 0.03 | −0.19 | 0.16 | 0.02 |
| AC008147.2 | 0.55 | −0.68 | −0.81 | −0.11 | −0.05 | PTK2 | −0.12 | 0.07 | 0.08 | −0.07 | −0.08 | MIR4744 | 0.24 | −0.16 | −0.85 | −0.39 | −0.43 |
| EIF4A1P10 | 1.27 | −0.66 | −1.58 | −0.05 | −0.80 | CYYR1 | 0.25 | 0.12 | 0.36 | −0.14 | −0.24 | PLGLB2 | −0.18 | 0.17 | 0.32 | 0.13 | 0.55 |
| FOXD2 | −1.23 | 0.66 | 0.27 | 0.55 | 0.09 | AC093278.2 | 0.50 | −0.50 | −0.41 | −0.26 | −0.07 | MIR3151 | −0.37 | 0.34 | 1.95 | 0.51 | 0.36 |
| DDX10 | 0.53 | −0.47 | −0.41 | −0.20 | 0.06 | AC019257.2 | 1.60 | −1.02 | −2.28 | 0.24 | −1.52 | BAMBI | −0.10 | 0.44 | −0.14 | 0.08 | 0.14 |
| AWAT1 | −1.28 | 0.86 | 0.97 | 0.71 | 1.03 | NT5M | −0.37 | 0.34 | 0.24 | −0.04 | 0.18 | PPATP1 | 0.55 | −1.57 | −0.10 | −0.08 | 0.70 |
| SON | 0.39 | −0.13 | −0.32 | −0.14 | −0.26 | HDAC10 | −0.44 | 0.24 | 1.00 | 0.21 | 0.79 | KRT37 | 0.15 | −0.42 | −1.27 | −0.22 | −1.04 |
| AL590452.1 | −0.74 | 0.08 | 0.59 | −0.27 | 0.00 | ERG28 | 0.20 | −0.01 | −0.07 | 0.13 | 0.03 | HMGB1P28 | 0.47 | −1.15 | −0.36 | 0.15 | −0.08 |
| RN7SL862P | 1.44 | −1.13 | −1.98 | −0.69 | −1.74 | RAB30 | −0.19 | 0.08 | 0.29 | 0.14 | 0.18 | AC100773.1 | −0.59 | 0.93 | 1.75 | −0.28 | 0.94 |
| KDM4A | −0.43 | 0.30 | 0.26 | 0.22 | 0.12 | AL109936.1 | 0.88 | −0.13 | −0.49 | −0.42 | −1.21 | AC104042.1 | 0.59 | −0.69 | −0.23 | 1.33 | 1.91 |
| BANF1 | 0.51 | −0.26 | −0.31 | −0.14 | −0.15 | AL033527.5 | −0.61 | 0.51 | 0.13 | 1.32 | 0.42 | AGAP14P | −0.17 | 0.28 | 0.50 | 0.39 | 1.17 |
| CPSF1 | −0.66 | 0.23 | 0.22 | 0.33 | 0.33 | LINC00705 | 0.98 | −0.36 | −0.78 | −1.40 | −0.51 | SPATA19 | 0.29 | −0.73 | −1.59 | −0.34 | −1.36 |
| LINS1 | 0.43 | −0.36 | −0.25 | −0.06 | 0.18 | COL5A3 | −0.23 | −0.19 | 0.05 | −0.25 | −0.03 | AP006621.5 | −0.16 | 0.21 | 0.57 | 0.17 | 0.43 |
| SRPK3 | −1.17 | 0.02 | 0.77 | 0.42 | 1.05 | AC133919.2 | 0.73 | −0.03 | 0.67 | 0.44 | 1.86 | C17orf67 | −0.07 | −0.08 | 0.20 | 0.04 | 0.42 |
| CDO1 | −1.95 | 1.89 | 1.61 | 0.99 | −0.30 | FAM170A | 1.00 | −1.45 | −0.09 | 0.24 | 0.90 | FAM8A1 | 0.06 | 0.25 | 0.26 | 0.08 | −0.24 |
| MBD2 | 0.55 | −0.28 | −0.50 | −0.22 | −0.30 | CLEC12A | −0.52 | 0.08 | 1.60 | −0.13 | −0.35 | LINC00565 | 0.22 | −0.87 | −0.24 | 0.22 | −0.53 |
| G39286 | −1.54 | 0.51 | 1.08 | 0.39 | 0.17 | SPAG9 | 0.14 | 0.06 | −0.20 | −0.02 | −0.31 | CYTH1 | 0.04 | −0.03 | −0.07 | −0.14 | −0.07 |
| AC093827.3 | −0.85 | 0.14 | 0.53 | 0.35 | 0.58 | AC004910.1 | −1.61 | 0.02 | 0.96 | 1.64 | 0.82 | RPL5P16 | 0.32 | −1.14 | −0.06 | −1.03 | 0.10 |
| NDUFB10 | 0.58 | −0.10 | −0.36 | −0.19 | −0.40 | HIGD1AP17 | 1.00 | 0.13 | −0.13 | 0.12 | 0.50 | AC018809.1 | 0.10 | −0.13 | 0.10 | −0.09 | 0.22 |
| SPOCK1 | −1.14 | 0.30 | 1.21 | −0.42 | −0.16 | ACSM4 | −0.56 | −0.47 | 0.48 | 0.01 | 0.46 | AP005242.1 | 0.63 | −0.41 | −1.79 | 1.32 | −2.01 |
| BACH1-IT1 | 0.75 | −0.42 | −0.34 | −0.30 | −0.30 | MIR4435-2 | 1.46 | −2.66 | 0.08 | −1.60 | 1.38 | FKBP1B | 0.09 | 0.11 | −0.12 | 0.16 | −0.23 |
| EMID1 | −1.01 | 0.34 | 0.52 | 0.04 | 0.38 | PINK1 | −0.19 | 0.22 | 0.12 | 0.10 | −0.05 | OR4F14P | 0.46 | −0.33 | −1.67 | 0.46 | −1.87 |
| ELMOD3 | −0.50 | 0.22 | 0.41 | 0.07 | 0.20 | KRT18P9 | −1.74 | −0.45 | −0.71 | 1.42 | 0.80 | LINC01479 | −0.46 | 1.62 | 0.73 | 1.38 | 0.82 |
| ARL13A | −0.67 | 0.41 | 0.46 | 0.31 | 0.24 | DNAJC1 | 0.12 | −0.03 | 0.01 | −0.15 | −0.03 | AC006116.10 | −0.75 | −0.09 | 2.55 | −1.84 | 0.29 |
| AC073869.1 | −0.69 | 0.21 | 0.37 | 0.28 | 0.31 | AC022784.6 | −1.28 | 0.98 | 1.32 | −1.23 | −1.63 | LINC01900 | 0.39 | −0.89 | −0.49 | −0.34 | 1.25 |
| AL713852.1 | −1.28 | 1.33 | 1.06 | 0.65 | 0.41 | RNU1-34P | −1.02 | −0.84 | 0.81 | 0.09 | 1.86 | MMRN1 | 0.12 | 0.27 | 1.34 | 0.01 | −0.07 |
| DNAH7 | −0.89 | 0.53 | 0.54 | 0.05 | −0.08 | AL139246.1 | −0.65 | −0.02 | 0.01 | 0.16 | 0.43 | SMIM2-AS1 | −0.18 | −0.66 | −0.75 | 0.07 | 0.77 |
| NPAS1 | −1.07 | 1.06 | 1.10 | 0.70 | 0.10 | AC095350.1 | −0.44 | 0.36 | −0.69 | 0.91 | −0.17 | ABI1P1 | 0.14 | −0.88 | 0.51 | 0.26 | 0.87 |
| AC115989.1 | −1.34 | 1.21 | 1.48 | 0.98 | 0.68 | 10-Sep | 0.13 | 0.09 | −0.02 | 0.01 | −0.21 | STK32C | −0.06 | −0.15 | −0.17 | 0.05 | 0.22 |
| AC006372.1 | 1.69 | −0.84 | −1.03 | −0.52 | −0.85 | AL049776.1 | −0.31 | 0.00 | 0.30 | −0.19 | 0.36 | AC104596.1 | −0.13 | 0.29 | 0.78 | −0.09 | 0.01 |
| RNF26 | 0.70 | −0.37 | −0.59 | 0.05 | −0.24 | C1orf216 | 0.15 | −0.08 | −0.29 | −0.06 | −0.19 | CRYBB3 | 0.15 | −0.39 | −0.07 | −0.40 | 0.72 |
| CAMSAP1 | 0.44 | −0.05 | −0.52 | 0.11 | −0.31 | AL136320.1 | −0.33 | −0.16 | 0.00 | −0.45 | −0.20 | LINC02549 | −0.51 | −1.60 | −0.03 | −0.41 | −0.19 |
| AP000864.1 | 2.06 | −0.59 | −0.86 | −0.29 | −0.71 | AC091534.1 | −1.00 | −0.32 | 0.41 | −0.37 | −0.48 | AC104046.1 | 0.05 | 0.00 | 0.05 | −0.02 | −0.02 |
| AC139769.1 | −0.80 | 0.68 | 1.37 | 0.33 | 0.46 | AP000317.1 | −0.98 | −0.53 | −0.25 | −0.18 | −0.94 | KRT18P44 | −0.82 | 0.66 | −0.66 | −0.63 | −2.53 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC008870.2 | −1.31 | 0.08 | 0.49 | 0.76 | 0.53 | AL122013.1 | −0.63 | 0.59 | 0.63 | 0.14 | 0.06 | AC068641.1 | −0.17 | −0.61 | 0.30 | −0.62 | 0.07 |
| HSP90AA1 | 0.82 | −0.57 | −0.75 | −0.32 | −0.46 | AL450124.1 | −0.60 | 0.16 | 0.84 | 0.61 | 0.07 | G5552 | −0.18 | 1.25 | 1.82 | 0.83 | −0.42 |
| C14orf180 | −2.69 | 1.81 | 2.26 | 1.72 | 0.11 | LMBRD2 | 0.15 | 0.01 | 0.03 | 0.00 | −0.04 | AC099786.1 | 0.47 | 0.06 | −1.89 | 0.47 | −2.07 |
| CHMP2B | 0.60 | −0.07 | −0.34 | −0.10 | −0.49 | RN7SKP235 | 0.55 | 0.23 | −0.13 | −0.18 | −0.40 | MIR2276 | 0.31 | −0.16 | 1.32 | 0.10 | 0.94 |
| NDUFA1 | 0.64 | −0.28 | −0.52 | −0.11 | −0.26 | RNU6-874P | 1.01 | −0.54 | −2.14 | 0.78 | −0.17 | C3orf85 | 0.49 | 0.75 | −2.74 | 1.09 | −0.70 |
| FLNC | −0.93 | 0.51 | 0.33 | 0.22 | −0.45 | HNRNPMP1 | −0.34 | 0.09 | 0.42 | −0.41 | 0.20 | CYP4F23P | 0.14 | 0.83 | 0.05 | 0.08 | −0.94 |
| AC009119.2 | −1.12 | −0.02 | 0.55 | 0.34 | 0.60 | AC023632.6 | 0.29 | −0.29 | 0.09 | −0.03 | 0.16 | LINC02229 | 0.60 | −0.50 | −1.03 | −0.61 | −0.92 |
| AC234582.1 | −1.03 | 0.28 | 0.50 | 0.43 | 0.22 | HOTAIRM1 | 0.22 | −0.17 | 0.13 | 0.01 | 0.33 | RPS20P10 | −0.36 | −0.37 | 0.63 | −0.38 | 0.14 |
| AC092377.1 | −1.93 | 0.60 | 0.04 | 0.11 | 0.03 | CDC42EP2 | −0.96 | −0.19 | 0.53 | −0.72 | 0.16 | RASSF4 | −0.09 | −0.31 | 0.24 | −0.24 | 0.33 |
| PLEKHG6 | −0.69 | 0.48 | 0.18 | 0.33 | 0.00 | SNRPCP16 | −0.94 | 1.07 | 1.03 | −0.63 | −0.35 | AC023513.1 | 0.35 | −0.39 | 0.89 | −0.21 | 0.24 |
| DCAF17 | 0.48 | −0.16 | −0.22 | −0.02 | −0.11 | AC100823.1 | −1.03 | −1.03 | 1.86 | 0.47 | 2.74 | HIST1H2BPS2 | −0.69 | −0.10 | 0.73 | 0.43 | −0.36 |
| GMDS-DT | −0.69 | 0.22 | 0.87 | 0.02 | 0.36 | KLHDC3 | 0.16 | 0.10 | 0.14 | 0.07 | −0.13 | CCDC34 | 0.06 | −0.12 | −0.08 | −0.11 | −0.27 |
| RNF4 | 0.39 | −0.26 | −0.30 | −0.21 | −0.12 | AL355922.2 | −0.50 | 1.26 | 0.61 | 0.25 | −0.16 | AL161722.3 | −0.28 | −1.32 | −1.87 | 0.04 | −1.04 |
| PIGZ | −0.53 | 0.49 | 0.20 | 0.33 | 0.03 | INPP5B | −0.09 | 0.01 | 0.14 | 0.16 | 0.15 | CNST | −0.03 | 0.18 | 0.16 | 0.06 | −0.22 |
| CTNND2 | −1.61 | 1.00 | 1.03 | −0.09 | −1.12 | MIR644A | 0.67 | −0.26 | −0.24 | 0.27 | 0.22 | KCNG4 | −0.22 | −0.83 | −1.19 | −0.69 | −0.64 |
| NATD1 | −0.64 | 0.40 | 0.26 | 0.29 | 0.02 | CYP1B1 | −0.44 | 0.18 | 0.40 | 0.17 | 0.29 | AC093155.3 | 0.28 | 0.07 | −0.16 | 0.01 | 0.91 |
| BPNT1 | 0.52 | −0.23 | −0.47 | 0.02 | −0.19 | AL020997.1 | −0.62 | 0.49 | −1.18 | 0.50 | −0.57 | PFN2 | 0.06 | 0.22 | 0.17 | 0.07 | −0.11 |
| ATP5MC1 | 0.74 | −0.22 | −0.56 | 0.06 | −0.34 | AC025580.2 | 0.50 | −1.14 | −0.31 | −0.47 | 0.47 | AC004687.2 | 0.18 | −0.11 | −0.28 | −0.36 | −0.61 |
| S100A5 | −1.41 | 1.18 | 0.62 | 1.27 | 0.25 | CCDC192 | −0.37 | 0.13 | 0.75 | 0.02 | 0.34 | AC026117.1 | −0.12 | 0.29 | 0.17 | −0.27 | −0.45 |
| PKD1P1 | −0.87 | 0.25 | 0.45 | 0.42 | 0.50 | AC012618.1 | −0.80 | 0.56 | −2.37 | 0.47 | −2.17 | LINC01863 | −0.48 | 0.01 | −1.42 | 1.78 | 0.30 |
| DNAJC25 | 0.57 | −0.25 | −0.46 | −0.20 | −0.36 | OR52K2 | −1.22 | −0.83 | 1.74 | 0.60 | 0.78 | AC018495.1 | 0.81 | −1.02 | −1.80 | −0.50 | −1.49 |
| SLC34A3 | −1.24 | 0.70 | 0.50 | 0.83 | 0.23 | AC008569.2 | −0.41 | −0.33 | 0.74 | −0.02 | 0.64 | COL18A1-AS1 | −0.13 | 0.03 | −0.75 | 0.22 | −0.44 |
| CCNE2 | 0.76 | −0.56 | −0.62 | −0.15 | −0.29 | RPGRIP1L | −0.15 | 0.06 | 0.39 | −0.21 | 0.05 | RN7SL538P | −0.45 | −0.30 | 1.54 | 0.23 | 1.29 |
| C6 | −1.80 | 0.86 | 0.61 | 2.11 | −0.78 | PCSK7 | −0.17 | −0.04 | 0.03 | 0.07 | 0.27 | RARG | −0.05 | 0.26 | 0.05 | 0.18 | −0.06 |
| SEPHS2 | 0.65 | −0.27 | −0.64 | −0.11 | −0.46 | LINC01607 | −1.07 | 0.46 | 2.34 | −0.26 | 0.40 | B4GALT4-AS1 | 0.21 | −0.30 | −0.54 | 0.63 | 0.26 |
| RN7SKP80 | −0.72 | 0.50 | 0.66 | 0.25 | 0.06 | SNRPGP4 | −0.42 | 0.50 | 0.46 | 0.32 | 0.14 | DUOXA2 | −0.09 | 0.47 | 0.21 | 0.64 | 0.46 |
| MUC16 | −1.23 | 0.27 | 0.17 | 0.00 | 0.34 | AC007161.1 | −0.36 | 0.21 | 0.77 | −0.54 | 0.14 | AC011504.1 | −0.23 | 0.39 | 0.13 | 0.35 | −0.16 |
| LBR | 0.57 | −0.33 | −0.37 | −0.10 | −0.07 | OR52V1P | −0.95 | −0.01 | 0.10 | 0.05 | 0.32 | ARHGAP42P1 | −0.41 | −0.22 | −0.78 | 1.37 | −1.00 |
| PCDHB11 | −0.92 | 0.06 | 1.40 | −0.24 | 0.57 | ODF2 | 0.18 | −0.28 | −0.36 | −0.20 | −0.06 | JRKL-AS1 | −0.54 | −1.35 | −0.51 | −0.02 | 1.17 |
| NDUFAB1 | 0.67 | −0.44 | −0.30 | −0.35 | −0.24 | LINC00838 | 1.28 | −1.45 | −0.75 | 0.04 | 0.24 | SPINK4 | 0.20 | −0.03 | −0.19 | −0.03 | 0.80 |
| SCCPDH | −0.73 | 0.53 | 1.19 | −0.13 | −0.02 | GNG11 | −0.32 | 0.33 | 1.21 | −0.22 | −0.02 | NPHP3-AS1 | 0.17 | −0.16 | −1.11 | 0.11 | −0.69 |
| MRPL44 | 0.45 | −0.27 | −0.46 | −0.10 | −0.25 | MARK2P6 | 0.98 | −0.51 | −1.90 | 0.66 | −1.50 | MKI67P1 | −0.26 | −0.94 | −0.02 | −0.85 | −0.06 |
| SLC9B2 | 0.53 | −0.41 | −0.39 | −0.14 | −0.21 | LINC01013 | −0.54 | −0.43 | 1.08 | −0.69 | 0.29 | C18orf63 | −0.24 | 0.15 | −0.86 | 0.75 | −0.65 |
| CIAO3 | −0.59 | 0.17 | −0.08 | 0.29 | 0.14 | AC087457.1 | −1.29 | −0.90 | 0.35 | −0.98 | −0.30 | LINC00971 | −0.21 | −0.31 | −0.94 | 0.76 | 0.04 |
| SPINK1 | −1.86 | 0.09 | 2.35 | −0.35 | −0.27 | AL583856.2 | −0.54 | −0.07 | 1.61 | 0.30 | 1.05 | AL442125.2 | −0.06 | −0.02 | 0.70 | −0.15 | 0.36 |
| AL031587.5 | −1.03 | 0.44 | 0.04 | 0.82 | 0.14 | SENP5 | 0.10 | −0.10 | −0.11 | −0.11 | −0.05 | AC006213.3 | 0.14 | −0.70 | 0.17 | −0.02 | 0.31 |
| AC092809.4 | −1.15 | 0.87 | 1.84 | 0.29 | −0.17 | RN7SKP30 | 0.49 | −0.32 | −0.19 | −0.20 | −0.10 | KRBOX1 | 0.20 | −0.28 | −0.95 | 0.59 | 0.16 |
| HES2 | 0.97 | −0.36 | −0.99 | 0.22 | −0.32 | GPC6-AS2 | −0.87 | −0.35 | 1.09 | −0.21 | −0.43 | AKR1C5P | −0.37 | −0.38 | −0.67 | 1.57 | 0.47 |
| SMOC1 | −1.44 | 1.07 | 0.97 | 0.02 | −0.33 | MIR576 | 1.13 | 0.38 | −1.29 | 0.35 | −1.00 | RIPPLY1 | −0.35 | −1.85 | −0.58 | −0.77 | 0.14 |
| MCM5 | 0.66 | −0.66 | −0.95 | −0.03 | −0.20 | RN7SKP273 | −0.83 | 0.92 | 0.58 | 0.25 | −0.70 | NCOA4P3 | 0.12 | −0.17 | 0.44 | −0.28 | −0.02 |
| NPY5R | −1.77 | 0.55 | 1.61 | 0.33 | 0.24 | AC243585.1 | 1.60 | −0.19 | −1.46 | 0.64 | −1.36 | AL606763.1 | −0.25 | −0.12 | 0.10 | −0.45 | 0.13 |
| RXRA | −0.56 | 0.32 | 0.27 | 0.39 | 0.15 | MIR4439 | 0.88 | −1.83 | −0.67 | −0.40 | 1.10 | AL512271.1 | 0.63 | −1.29 | −1.07 | 1.18 | 1.91 |
| EIF2B1 | 0.28 | −0.14 | −0.31 | −0.02 | −0.12 | AC098828.3 | −0.99 | 1.46 | 1.60 | 1.28 | 0.07 | AC004965.1 | 0.54 | −2.06 | −1.49 | 0.66 | 1.39 |
| AC093484.4 | 1.68 | −1.08 | −1.67 | 0.06 | −0.53 | C5orf58 | 0.58 | −1.16 | −1.17 | 0.30 | −0.20 | AC110994.2 | −0.11 | −0.01 | 0.57 | −0.21 | 0.24 |
| G25515 | 1.47 | −1.00 | −1.10 | −0.15 | 0.10 | AL035706.1 | −0.63 | 0.83 | 1.38 | 0.28 | 0.55 | AL353751.1 | 0.33 | 1.25 | 0.08 | 0.99 | 0.08 |
| C20orf203 | −1.72 | 0.47 | 1.41 | 0.27 | 0.82 | AKR1B10P1 | 0.95 | −0.33 | −1.87 | 1.31 | −0.35 | AC099518.2 | 0.26 | −0.94 | −2.65 | −0.19 | −0.97 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| GNB5 | 0.43 | −0.10 | −0.60 | 0.00 | −0.41 | G23640 | −1.34 | 0.28 | 0.49 | −0.32 | −0.33 | OR11H5P | −0.43 | −0.73 | −1.58 | −0.61 | −2.25 |
| AL162231.1 | −1.79 | 0.53 | 1.02 | −0.09 | 0.90 | AC092490.1 | −0.60 | 1.20 | −0.33 | 2.24 | 0.41 | FGFR1OP2P1 | 0.65 | −2.01 | −1.66 | −0.64 | 0.45 |
| HOGA1 | −1.10 | 0.50 | 0.34 | 0.47 | −0.03 | AL589935.2 | −1.05 | −0.60 | 1.85 | 0.22 | 2.42 | AL163051.2 | 0.09 | −0.01 | 0.47 | 0.01 | 0.13 |
| SFT2D2 | 0.59 | −0.07 | −0.13 | −0.10 | −0.34 | AC004466.2 | 0.47 | −0.07 | −0.16 | −0.14 | −0.34 | AC097381.2 | 0.21 | 0.68 | 0.20 | 0.34 | −0.20 |
| LMNTD2 | −1.21 | 0.67 | 0.85 | 0.55 | 0.34 | AC112196.1 | −0.51 | 0.60 | 1.48 | −0.27 | 0.26 | AP000892.2 | −0.15 | 0.01 | −0.02 | 0.35 | −0.05 |
| CHMP1B2P | −0.77 | 0.97 | 0.75 | 0.54 | 0.31 | RN7SL417P | −1.17 | 0.34 | 2.13 | −0.55 | 0.57 | RBPMS2P1 | −0.47 | 1.09 | −1.37 | 2.37 | −1.16 |
| IFIT5 | 0.65 | −0.31 | −0.68 | −0.13 | −0.44 | C9orf116 | 0.54 | −0.41 | −0.37 | 0.23 | −0.03 | MPC2 | 0.06 | 0.09 | −0.19 | 0.19 | −0.09 |
| Clorf229 | −1.77 | 0.79 | 0.32 | 0.71 | 0.41 | AC097460.1 | −0.66 | 0.61 | 1.05 | 0.89 | 0.36 | PRKCG | −0.25 | 0.52 | −0.73 | 0.46 | −0.47 |
| AC092894.1 | −1.81 | 0.05 | 2.48 | 0.22 | 0.62 | AL137790.1 | −0.61 | 0.51 | 1.30 | 0.34 | 0.54 | AC009803.3 | 0.39 | −1.71 | 0.61 | −0.47 | 1.36 |
| ADRM1 | 0.48 | −0.29 | −0.78 | 0.15 | −0.38 | AL096869.1 | 0.49 | −0.60 | −0.07 | 0.00 | 0.51 | PHBP19 | −0.07 | −0.32 | 0.50 | −0.27 | 0.27 |
| CD34 | −1.03 | 0.72 | 1.45 | 0.24 | 0.07 | AC092135.1 | 0.24 | −0.41 | −0.65 | −0.38 | −0.46 | RNU6-251P | 0.28 | −0.90 | −1.14 | 0.40 | 0.40 |
| MAP3K5 | 0.37 | −0.27 | −0.38 | 0.02 | 0.00 | F8A1 | 0.37 | −0.04 | −0.12 | −0.34 | −0.08 | RAB5CP2 | −0.19 | −0.93 | 0.61 | −0.71 | 0.65 |
| FZD7 | −0.91 | 0.66 | 1.19 | −0.01 | −0.12 | IGKV1-5 | 1.42 | 1.18 | 1.37 | −0.58 | −0.57 | RUBCN | 0.04 | −0.10 | −0.23 | −0.06 | −0.01 |
| AC011444.3 | −1.57 | 1.03 | 2.35 | 0.08 | 0.95 | AC105219.3 | −0.35 | 0.14 | −0.34 | 0.34 | 0.05 | AC096537.1 | 0.26 | 1.10 | −0.63 | 0.13 | −1.32 |
| FBLN7 | −0.87 | 0.33 | 0.99 | −0.04 | 0.21 | RAB37 | −0.56 | 0.39 | 0.81 | 0.28 | 0.52 | HNRNPA1P39 | −0.23 | 0.78 | −1.09 | 0.45 | −0.07 |
| ACVR2A | −0.55 | 0.37 | 0.76 | 0.11 | 0.30 | AC243562.1 | −0.68 | 0.54 | 1.02 | 0.02 | −0.15 | LINC02521 | 0.22 | −0.45 | −0.57 | −0.81 | −0.29 |
| GALNT13 | −1.14 | 0.54 | 0.50 | −0.09 | −0.14 | CD74 | 0.32 | −0.35 | 0.10 | −0.39 | 0.14 | RAB42P1 | 0.25 | −0.68 | −0.53 | 0.02 | 0.01 |
| SDHB | 0.57 | −0.29 | −0.60 | −0.15 | −0.36 | GGT5 | −0.36 | 0.15 | 0.75 | 0.02 | 0.23 | OR2H1 | −0.30 | −0.11 | 0.03 | 1.28 | −0.74 |
| DNAH9 | −0.91 | 0.10 | 0.45 | 0.15 | 0.34 | NXPE4 | −0.55 | 0.16 | −0.27 | 0.57 | −0.17 | AL390115.1 | −0.83 | 0.17 | 0.68 | −0.81 | −0.86 |
| RBM4B | −0.57 | 0.11 | 0.25 | 0.18 | 0.20 | AL353807.4 | 0.67 | −0.81 | 0.43 | −0.07 | 0.79 | LAIR1 | −0.12 | −0.44 | 0.37 | −0.43 | 0.41 |
| AL355312.1 | −1.44 | 0.63 | 0.38 | 1.06 | 0.60 | AC090948.1 | 0.37 | −0.49 | −0.07 | −0.42 | 0.06 | AL355355.2 | 0.18 | −0.59 | −0.35 | 0.05 | −0.12 |
| RRM2P3 | −1.14 | 0.75 | 0.62 | 0.65 | 0.23 | AL355075.5 | 0.79 | −0.44 | −0.19 | 0.49 | −0.06 | AC068790.7 | −0.10 | −0.02 | −0.28 | −0.33 | −0.59 |
| KCND3 | 0.64 | −0.42 | −0.62 | −0.03 | 0.01 | EPB41L5 | 0.14 | 0.16 | −0.12 | 0.05 | −0.17 | RPS15P5 | 0.13 | 0.19 | −0.57 | 1.04 | −0.53 |
| ERAL1 | 0.42 | −0.19 | −0.29 | −0.08 | −0.12 | AC068792.1 | −1.14 | 0.55 | 1.16 | −1.14 | 0.28 | LINC01442 | −0.41 | −0.41 | −0.47 | −0.62 | −1.42 |
| AC091100.1 | −1.46 | 0.75 | 1.22 | 0.20 | 0.49 | AL589669.1 | −0.90 | 1.46 | −0.43 | 0.82 | −0.65 | AC007780.1 | −0.08 | 0.23 | 0.53 | −0.26 | 0.01 |
| OR52B5P | −1.11 | 0.97 | 0.86 | 0.41 | −0.24 | SLC51B | −0.67 | 0.21 | 0.85 | 0.50 | 0.33 | AL359771.1 | 0.55 | −1.50 | −1.40 | 0.25 | 0.17 |
| AC027237.3 | 1.61 | −1.30 | −1.01 | −0.36 | −0.70 | RNU6-750P | 0.89 | 0.52 | −1.07 | 1.08 | −0.29 | OMP | −0.29 | −0.61 | 0.30 | 0.44 | 0.98 |
| AP1AR | 0.44 | −0.08 | −0.24 | 0.06 | −0.10 | FANCL | 0.15 | −0.13 | −0.25 | −0.11 | −0.11 | AL353681.1 | 0.46 | −1.57 | −1.59 | 0.58 | 0.21 |
| PARPBP | 0.84 | −0.77 | −1.04 | −0.29 | −0.52 | PRSS21 | 0.67 | 0.08 | −1.85 | 0.46 | −0.35 | LINC01231 | −0.39 | −0.36 | −0.20 | 1.04 | −1.29 |
| AP005060.1 | −0.83 | 0.46 | 0.70 | −0.08 | 0.52 | MT-TL2 | −0.97 | −0.12 | 0.01 | 0.65 | 0.03 | AP001485.1 | −0.81 | −0.32 | −0.24 | −0.91 | −1.80 |
| MTDHP1 | −1.47 | 0.64 | 1.64 | 0.25 | 0.60 | SPINT1 | 0.20 | 0.19 | −0.25 | 0.14 | −0.26 | LINC02372 | 0.17 | −0.01 | −1.52 | 0.47 | −0.83 |
| CNIH1 | 0.73 | −0.42 | −0.60 | −0.21 | −0.46 | KLC3 | −0.29 | 0.55 | 0.13 | 0.55 | 0.04 | KRT8P45 | −0.25 | −0.19 | 0.69 | 0.18 | 0.78 |
| BRD3 | −0.33 | 0.36 | 0.21 | 0.19 | −0.09 | DNAJB2 | −0.18 | 0.48 | 0.22 | 0.26 | −0.16 | AL133481.1 | 0.14 | −0.01 | 0.09 | −0.41 | −0.42 |
| PDCL3P4 | −1.32 | 0.60 | 1.09 | 0.24 | 0.26 | RNU6-589P | −0.76 | 0.22 | 1.35 | −0.28 | 0.36 | AL353768.1 | 0.15 | −0.07 | −0.01 | 0.19 | 0.04 |
| EIF4E2 | 0.53 | −0.29 | −0.61 | −0.04 | −0.45 | AP001094.1 | −0.65 | −0.70 | 0.15 | −0.63 | 0.28 | AC000078.1 | 0.13 | −0.04 | −0.34 | 0.18 | −0.20 |
| ANKRD30A | −2.36 | 0.87 | 2.07 | 1.05 | 0.75 | POU4F1 | −0.65 | 0.77 | 0.37 | 0.49 | −0.65 | AL157400.3 | −0.18 | 0.03 | 2.13 | −0.58 | 0.45 |
| GRIN2A | −1.26 | 0.45 | 0.72 | 0.60 | 0.14 | AP003392.4 | −0.30 | −0.36 | 0.57 | −0.12 | 0.56 | ECEL1P1 | −0.44 | −0.17 | 1.34 | −2.20 | −0.06 |
| AC069272.1 | −1.79 | 1.14 | 1.71 | 0.42 | 0.30 | MIR505 | 1.18 | 1.10 | −1.51 | 0.80 | −1.21 | RPL37P3 | 0.36 | 0.50 | −0.78 | 1.13 | −1.23 |
| FRZB | −1.07 | 1.19 | 1.23 | 0.42 | 0.00 | AL035413.1 | −0.37 | 0.40 | 0.58 | 0.16 | 0.02 | STXBP3 | 0.03 | 0.13 | 0.14 | 0.05 | −0.14 |
| CA3-AS1 | 1.49 | −1.18 | −0.48 | −0.46 | 0.19 | CHST8 | −0.72 | 0.71 | 0.18 | 0.83 | −0.15 | AC138649.2 | −1.08 | 1.08 | −0.64 | 0.13 | −3.61 |
| AC012404.1 | −1.20 | 0.68 | 1.72 | 0.05 | 0.51 | AL451069.2 | −0.80 | 1.66 | −0.56 | 0.86 | −0.78 | F2RL3 | 0.12 | 0.04 | −0.41 | −0.36 | −0.34 |
| AC026877.1 | −0.72 | 0.48 | 0.60 | −0.12 | −0.05 | LAP3P1 | 0.69 | −0.85 | −1.08 | −0.71 | −0.42 | AC024559.2 | 0.53 | 0.41 | 0.02 | −1.02 | −0.96 |
| MSANTD1 | −1.05 | 1.09 | 0.16 | 0.92 | 0.22 | OR4D1 | −0.77 | −0.36 | −0.39 | 0.15 | 1.14 | AL356417.3 | 0.17 | −0.99 | −0.06 | 0.06 | −0.38 |
| LAMP1 | 0.56 | 0.01 | −0.29 | 0.11 | −0.39 | AC093766.1 | −0.80 | 1.76 | 0.55 | 0.56 | −0.55 | CTBP2P4 | −0.20 | 0.23 | −2.10 | 0.98 | −1.18 |
| HIST1H2BG | 1.07 | −0.54 | −1.65 | −0.20 | −1.03 | AC021218.1 | 1.06 | −1.53 | −0.94 | −0.68 | −0.79 | COPS8 | 0.04 | −0.03 | 0.00 | −0.16 | −0.08 |
| DDX60 | 0.92 | −0.64 | −0.51 | −0.62 | −0.37 | AC008443.6 | −0.72 | 0.13 | 0.74 | −0.10 | 0.41 | BBOX1-AS1 | −0.11 | 0.19 | 0.65 | −0.08 | 0.09 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| RBMXP4 | −1.43 | 0.98 | 1.15 | 0.36 | 0.14 | HEBP1 | −0.15 | 0.09 | 0.24 | 0.14 | −0.03 | SETP2 | −0.13 | −0.43 | −0.50 | −0.11 | 0.64 |
| AC012651.1 | −0.79 | 0.24 | 0.48 | 0.17 | 0.36 | SLX4 | 0.18 | −0.30 | −0.40 | −0.12 | 0.08 | AC003975.1 | 0.33 | −1.49 | −1.92 | −0.02 | −1.53 |
| PI4K2B | 0.82 | −0.21 | −0.40 | −0.08 | −0.37 | AC079140.2 | 0.56 | −0.69 | −0.03 | −0.45 | −0.01 | DPYD-AS1 | 0.11 | −0.28 | −0.27 | 0.06 | 0.00 |
| RALGAPA2 | −0.30 | 0.25 | 0.53 | 0.07 | 0.24 | AL035410.2 | 1.54 | −1.88 | −2.56 | 0.03 | −1.82 | RNU2-56P | 0.30 | 0.66 | −1.04 | 1.05 | −2.10 |
| AC002066.1 | −1.46 | 0.31 | 1.64 | −0.81 | 0.58 | AC027176.3 | −1.20 | −1.01 | 0.29 | −0.34 | 0.93 | AL161912.2 | 0.39 | −1.06 | −1.82 | 0.97 | 0.23 |
| AC012181.2 | −1.02 | −0.06 | 0.64 | −0.41 | 0.65 | RNU6-74P | 1.15 | −0.17 | −1.10 | 1.71 | 0.32 | LINC02019 | −0.09 | 0.37 | 0.60 | −0.01 | 0.18 |
| SMIM7 | −0.36 | 0.20 | 0.13 | 0.26 | 0.18 | AC019206.1 | −0.47 | −0.32 | −0.35 | 0.43 | 0.37 | AL118511.2 | −0.19 | −0.38 | −1.24 | −0.14 | −1.37 |
| NEK11 | −0.48 | 0.28 | 0.34 | 0.15 | 0.17 | IL18 | 0.37 | 0.25 | 0.28 | 0.46 | −0.08 | ESAM | 0.10 | 0.00 | 0.30 | −0.05 | −0.18 |
| FASTKD2 | 0.49 | −0.24 | −0.35 | −0.10 | −0.19 | CPNE7 | −0.43 | 0.05 | −0.64 | 0.61 | 0.05 | BX255923.3 | 0.43 | −0.14 | −0.57 | 0.85 | 2.17 |
| SLIRP | 0.70 | −0.45 | −0.28 | −0.42 | −0.11 | AC018450.1 | −0.84 | −0.62 | 1.51 | −1.52 | 0.00 | AC006277.1 | −0.09 | −0.43 | 0.20 | −0.10 | 0.37 |
| MARVELD2 | 0.63 | −0.10 | −0.37 | 0.00 | −0.05 | AC246787.1 | 0.55 | 0.19 | −0.61 | 0.14 | −0.50 | RRP1 | 0.05 | −0.23 | −0.47 | 0.10 | 0.14 |
| HPRT1 | 0.76 | −0.75 | −0.69 | −0.23 | −0.06 | MTCO3P24 | 0.98 | −1.12 | −1.83 | 0.39 | −0.59 | AC017074.1 | −0.11 | 0.06 | 0.32 | −0.49 | −0.14 |
| LINC02273 | 2.37 | −1.75 | −2.28 | −1.09 | −0.22 | ARFRP1 | 0.17 | −0.18 | −0.62 | 0.13 | 0.00 | STARD6 | 0.22 | 0.31 | 0.14 | −0.32 | −0.32 |
| KRT8P15 | −1.24 | 0.54 | 0.27 | 0.52 | −0.54 | PCGF1 | 0.15 | −0.10 | −0.16 | −0.12 | 0.01 | AL591034.2 | −0.71 | −0.25 | NA | −0.61 | −2.31 |
| CSNK1G1 | 0.52 | −0.23 | −0.20 | −0.19 | −0.08 | SPATS2L | 0.16 | −0.18 | −0.11 | −0.34 | −0.26 | AL022069.2 | −0.20 | 0.04 | 0.46 | −0.53 | 0.46 |
| LRRC4C | −1.63 | 0.23 | 2.07 | 0.22 | 0.76 | SNORD69 | −0.63 | −0.33 | 0.41 | 0.19 | 0.29 | AC103769.1 | −0.10 | 0.36 | 0.52 | −0.12 | 0.00 |
| FAM13C | −0.81 | 0.79 | 1.28 | 0.26 | 0.11 | RNU6-1005P | 0.52 | −0.58 | −0.04 | −0.49 | −0.24 | MIR4715 | −0.45 | 0.21 | 0.66 | −1.02 | −0.87 |
| AL034376.1 | 2.84 | −1.34 | −1.38 | 0.70 | −1.63 | MIR1537 | 0.54 | −0.29 | 0.43 | −0.12 | 0.22 | AP003355.1 | −0.17 | 0.29 | 0.82 | 0.01 | 0.50 |
| NEDD1 | 0.49 | −0.28 | −0.43 | −0.14 | −0.31 | AC015911.3 | 0.68 | −1.46 | −0.28 | −0.41 | 1.32 | G36985 | 0.19 | 0.70 | −0.21 | 0.31 | −0.58 |
| ENHO | −2.76 | 1.34 | 1.82 | 0.23 | 0.73 | MIR148B | 0.92 | −0.09 | 0.83 | 0.15 | 0.87 | RPL7AP2 | 0.15 | −0.09 | 0.75 | 0.25 | 0.52 |
| AC092745.1 | −1.30 | 0.29 | 1.21 | 0.64 | 1.03 | AL138916.1 | 0.92 | −1.16 | −2.72 | 0.44 | −1.94 | LINC00161 | 0.25 | −0.14 | −0.97 | −0.87 | −0.98 |
| PHYH | −0.82 | 0.56 | 0.91 | 0.20 | 0.09 | MFSD11 | −0.14 | 0.10 | −0.08 | 0.06 | −0.14 | EPB41L4A | 0.04 | 0.24 | 0.04 | 0.27 | −0.16 |
| CLASRP | −0.84 | 0.28 | 0.01 | 0.52 | 0.16 | RNU6V | 0.71 | −0.32 | −0.37 | −0.71 | 0.23 | AL365204.1 | 0.35 | −0.02 | −2.39 | −0.20 | −1.84 |
| HEXDC-IT1 | −1.01 | 0.17 | 0.16 | 0.50 | 0.47 | C2orf49 | −0.10 | 0.06 | 0.23 | 0.03 | 0.10 | AC079467.1 | 0.25 | 0.29 | 1.52 | 0.60 | 1.11 |
| MC1R | −0.91 | 0.26 | 0.20 | 0.48 | 0.06 | LINC01117 | −0.49 | 0.45 | 0.89 | −0.41 | −0.13 | MTND1P5 | −0.53 | −0.85 | 0.84 | −1.61 | 1.16 |
| AL132656.1 | −0.98 | 0.31 | 0.90 | 0.29 | 0.76 | AC021739.2 | 0.43 | 0.21 | −0.89 | −0.04 | −1.20 | NCKIPSD | −0.04 | 0.02 | −0.11 | 0.13 | 0.11 |
| MIR1-1HG−AS1 | −2.38 | 0.81 | 1.51 | −1.01 | 0.37 | MIR655 | 1.42 | 0.20 | −1.76 | 0.30 | −1.03 | AL024493.1 | 0.52 | −0.40 | −1.11 | 0.45 | −0.17 |
| BX664727.3 | −2.11 | 1.01 | 2.43 | 0.07 | 0.49 | AC144530.1 | 0.30 | −0.34 | −0.28 | −0.16 | 0.14 | AC018680.1 | −0.51 | 0.12 | 0.71 | 0.50 | 0.25 |
| MANBAL | 0.42 | −0.22 | −0.37 | −0.12 | −0.21 | KCNJ16 | −0.67 | −0.21 | −0.59 | 0.81 | 0.43 | MTND4P29 | −0.39 | 0.05 | 1.14 | −0.60 | −0.68 |
| RP11-640M9.1 | −1.07 | 0.37 | 0.58 | −0.07 | 0.68 | CCDC13-AS1 | 0.95 | 0.64 | −0.39 | 0.55 | 0.06 | MIR647 | 0.15 | 0.26 | 0.13 | −0.16 | −0.18 |
| CTPS2 | −0.43 | 0.34 | 0.45 | 0.11 | 0.09 | RPS23P6 | 0.42 | −0.75 | −0.08 | −0.49 | 0.36 | EEF1A1P34 | 0.82 | 0.25 | 0.62 | −0.61 | 0.52 |
| RRS1 | 0.68 | −0.62 | −0.67 | −0.02 | 0.09 | RNU6-430P | 0.53 | −0.56 | 0.32 | −0.36 | 1.06 | METTL15P3 | −0.54 | 1.63 | 1.52 | −0.34 | −0.60 |
| PIK3IP1 | −0.62 | 0.56 | 0.49 | 0.49 | 0.09 | AC025750.2 | 0.60 | −0.41 | −1.94 | 0.30 | −0.87 | NECTIN3-AS1 | −0.24 | −0.78 | 1.53 | 0.03 | 0.72 |
| SRP54 | 0.47 | −0.18 | −0.35 | −0.09 | −0.18 | RNU2-51P | −0.71 | 0.59 | 0.84 | −0.49 | −0.57 | AC073548.1 | −0.09 | 0.12 | 0.12 | 0.19 | 0.22 |
| BTBD16 | −1.01 | 0.99 | 1.14 | 0.55 | 0.20 | AC118658.1 | 0.45 | 0.21 | −0.56 | 0.90 | −0.22 | AC073878.1 | −0.29 | 1.21 | 3.01 | −0.46 | −0.29 |
| IFT27 | −0.45 | 0.22 | 0.53 | −0.14 | 0.14 | RANGAP1 | 0.21 | −0.14 | −0.31 | −0.04 | −0.01 | LINC01070 | −0.36 | −0.35 | −0.04 | 0.04 | −1.76 |
| CFAP410 | −0.95 | 0.53 | 0.59 | 0.53 | 0.29 | RP6-206I17.1 | −0.28 | 0.03 | 0.04 | 0.17 | 0.15 | AC005041.3 | −0.19 | −0.22 | −0.66 | −0.52 | −0.55 |
| PTGR2 | −0.75 | 0.05 | 0.46 | 0.27 | 0.57 | RNU7-96P | 0.71 | 0.19 | −0.38 | 0.79 | 0.01 | LINC02460 | 0.71 | −1.71 | −0.20 | −0.17 | −0.72 |
| LIN54 | 0.61 | −0.20 | −0.36 | −0.10 | −0.49 | AC012409.2 | −0.60 | 0.07 | 0.13 | 0.22 | 0.19 | AC019193.3 | −0.27 | 0.45 | −1.03 | −0.12 | 0.24 |
| AC244033.1 | −1.56 | −0.34 | 1.04 | 0.14 | 1.05 | SMPD5 | −0.53 | 0.64 | −0.41 | 0.59 | 0.39 | AL136084.3 | −0.35 | −0.54 | −0.07 | −0.68 | −0.05 |
| HMGB1 | 0.47 | −0.33 | −0.35 | −0.19 | −0.21 | RNVU1-20 | 0.66 | −1.79 | −0.58 | −1.39 | −0.47 | LRRC37A5P | 0.20 | −0.82 | −0.55 | 0.48 | −0.07 |
| OR2A42 | −1.10 | 0.22 | 0.90 | −0.04 | 0.68 | AC145285.3 | −0.34 | −0.36 | 0.82 | −0.28 | 1.07 | AP000477.2 | −0.92 | 0.50 | −1.40 | 0.79 | −0.93 |
| DIXDC1 | −0.81 | 0.40 | 0.80 | 0.12 | 0.15 | AL354977.1 | −0.57 | 0.13 | 0.35 | 0.21 | −0.09 | SLC5A4 | 0.11 | −0.18 | 0.09 | 0.15 | −0.44 |
| AC005324.3 | 1.47 | −0.90 | −0.64 | −0.43 | 0.12 | HOXD11 | −0.89 | 1.39 | 0.64 | 1.21 | −0.81 | LINC00352 | −0.59 | 1.06 | 0.80 | 0.72 | −0.21 |
| CCDC51 | 0.64 | −0.47 | −0.88 | −0.14 | −0.35 | PGC | −0.94 | −0.63 | 0.55 | 0.13 | 0.18 | FAM167B | −0.16 | 0.11 | −0.75 | 0.05 | 0.27 |
| SEC24A | 0.63 | −0.38 | −0.38 | −0.36 | −0.25 | AC007639.1 | 0.62 | −0.30 | −0.85 | −0.31 | −0.26 | AC005013.1 | 0.23 | 0.60 | −0.34 | 1.58 | 0.14 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| GAL3ST4 | −0.85 | 0.86 | 1.04 | 0.47 | 0.21 | AL137013.1 | −0.43 | 0.55 | 0.49 | 0.73 | 0.19 | AC006238.1 | −0.30 | −0.23 | −1.33 | 0.73 | −0.04 |
| ACAP3 | −0.83 | 0.35 | 0.04 | 0.59 | 0.29 | MGAT5B | −0.41 | 0.51 | 0.21 | 0.34 | 0.05 | H2AFZP1 | 0.15 | −0.34 | −0.20 | 0.05 | 0.55 |
| SERINC5 | 0.79 | −0.16 | −0.45 | 0.05 | −0.30 | CEP164P1 | −0.57 | 0.73 | −0.31 | 0.40 | 0.10 | LINC01747 | 0.28 | −0.16 | −1.22 | 0.32 | −0.78 |
| IMPDH2 | 0.58 | −0.19 | −0.18 | −0.17 | −0.22 | CD300LF | 0.76 | −1.18 | −0.53 | −0.83 | −0.52 | RNU6-727P | −0.62 | −1.27 | 0.08 | 1.69 | 1.78 |
| LGALS12 | −2.37 | 1.35 | 1.84 | 0.88 | 0.32 | RPL13AP5 | 0.26 | 0.08 | 0.09 | −0.19 | −0.19 | MTND4LP14 | 0.40 | −0.20 | −0.94 | 0.23 | −0.19 |
| SEC23IP | 0.41 | −0.26 | −0.27 | −0.16 | 0.00 | HLA-DOB | 0.46 | −0.46 | −0.52 | −0.12 | 0.03 | AC025946.1 | −0.50 | −0.30 | −0.77 | −0.46 | −0.34 |
| MIGA2 | −0.56 | 0.21 | 0.24 | 0.14 | 0.25 | AC091152.4 | −0.59 | −0.77 | −0.43 | −0.51 | 0.22 | RNY3P7 | −0.45 | 0.43 | 2.91 | −0.01 | 1.12 |
| MAN2C1 | −0.72 | 0.28 | 0.14 | 0.41 | 0.19 | APOC1P1 | −1.07 | 0.39 | 0.36 | 0.31 | −0.05 | LINC02422 | 0.29 | 0.21 | 0.31 | −0.85 | −0.64 |
| CEP350 | 0.32 | −0.06 | −0.13 | −0.08 | −0.19 | AC017101.1 | 0.54 | 0.19 | −0.64 | −0.22 | −0.61 | AC023813.3 | 0.28 | 1.11 | 0.18 | 0.86 | 0.33 |
| ARL4D | 0.87 | −0.31 | −0.81 | 0.06 | −0.60 | MAPK8 | 0.15 | 0.17 | −0.02 | 0.04 | −0.20 | EEF1GP5 | 0.22 | −0.64 | 0.31 | −0.11 | 0.70 |
| EMC10 | −0.66 | 0.31 | 0.29 | 0.23 | 0.31 | AC084032.1 | −0.89 | 0.11 | 1.13 | −0.41 | 0.85 | AC016074.1 | 0.85 | −1.18 | −2.09 | −0.38 | −1.53 |
| AC080038.1 | −1.28 | 0.82 | 1.19 | −0.28 | −0.09 | AC011352.1 | −0.71 | 0.53 | 1.94 | −0.38 | −0.36 | LINC02548 | 0.28 | 1.11 | −2.24 | 1.10 | −1.74 |
| DDOST | 0.50 | −0.14 | −0.30 | −0.11 | −0.38 | RPS26P39 | 0.74 | 0.60 | −0.17 | 0.51 | −1.24 | ACTG1P24 | 0.20 | −1.03 | −0.95 | −0.12 | 1.26 |
| AF064858.1 | −1.09 | 0.29 | 0.59 | 0.30 | 0.01 | RNU6-216P | −0.78 | −0.03 | 0.70 | −1.13 | 0.04 | RPS14P8 | 0.13 | 0.77 | 0.07 | 0.34 | −0.02 |
| AC099550.1 | −1.23 | 0.53 | 1.23 | 0.37 | 0.76 | RPGR | −0.18 | −0.03 | 0.16 | −0.02 | 0.09 | AL135926.1 | 0.29 | −1.21 | −0.56 | −0.69 | 0.62 |
| B3GAT3 | −0.73 | 0.20 | 0.39 | 0.43 | 0.40 | SH3PXD2B | 0.15 | −0.10 | 0.01 | −0.37 | −0.25 | LINC01204 | 0.21 | −0.47 | 0.07 | 0.35 | 1.23 |
| FAM41C | −2.72 | −0.13 | 2.14 | −0.58 | −0.09 | ATP6V1G1P4 | −0.49 | −0.42 | 0.59 | 0.61 | 0.58 | AC009093.6 | 0.15 | −0.40 | 0.62 | −0.11 | 0.63 |
| AC100788.2 | −0.84 | 0.05 | 0.66 | −0.29 | 0.02 | H1FOO | 1.65 | −2.44 | −0.58 | −0.70 | 0.14 | RNU6-313P | 0.35 | 1.51 | −0.61 | −0.70 | −0.87 |
| NKAIN4 | −2.03 | 0.40 | 0.64 | 1.33 | 0.43 | RNU6-396P | 1.32 | −0.91 | −1.55 | 0.22 | 0.97 | RPL23AP43 | 0.20 | −0.36 | −0.42 | 0.38 | 0.32 |
| ATAD5 | 0.59 | −0.51 | −0.57 | −0.13 | −0.08 | RUSC1-AS1 | 0.32 | −0.31 | −0.22 | 0.01 | 0.17 | NDP | 0.18 | −0.60 | −0.37 | −0.34 | 0.33 |
| G10488 | −2.79 | −1.46 | −1.59 | 1.57 | −0.51 | CPA4 | 0.36 | −0.16 | −0.22 | 0.39 | −0.25 | MDK | 0.09 | 0.08 | 1.09 | −0.71 | 0.22 |
| RIOX2 | 0.43 | −0.28 | −0.33 | −0.18 | −0.03 | LRRC47 | −0.16 | 0.02 | −0.12 | 0.21 | 0.15 | AL445471.1 | 0.18 | −0.53 | 0.22 | −0.41 | −0.03 |
| AC007040.2 | −1.44 | 1.06 | 0.57 | 1.26 | 0.51 | RNU4ATAC12P | −0.60 | −0.18 | 1.30 | 0.12 | 0.81 | CTD-2173L22.4 | −0.16 | 0.08 | 0.90 | −0.88 | 0.00 |
| FYTTD1 | 0.60 | −0.16 | −0.21 | −0.20 | −0.33 | AC104772.1 | −1.21 | 0.70 | −1.38 | 1.21 | −0.74 | RRS1-AS1 | −0.09 | −0.21 | 0.27 | 0.20 | 0.49 |
| BCAS1 | −1.25 | 0.54 | 1.07 | 0.10 | 0.30 | CLEC4G | 0.64 | −0.63 | −0.52 | 0.15 | 0.30 | AC231981.1 | −0.18 | 0.14 | −0.28 | 0.48 | −0.57 |
| EFCAB2 | −0.66 | 0.29 | 0.74 | −0.07 | 0.07 | RNF31 | −0.18 | 0.07 | −0.16 | 0.19 | −0.01 | MIR4797 | 0.51 | 0.08 | −0.27 | −0.06 | −0.87 |
| AL591848.4 | −0.99 | 0.57 | 1.40 | 0.06 | 0.20 | PLAC8L1 | 0.44 | −0.15 | 0.32 | −0.13 | 0.09 | AC010099.4 | −0.53 | 0.78 | −0.29 | −1.13 | −1.39 |
| JOSD1 | 0.52 | −0.19 | −0.50 | −0.04 | −0.34 | AC064852.1 | 0.55 | 0.10 | −0.09 | 0.36 | −0.06 | AL805961.2 | −0.24 | −0.93 | −2.13 | 0.61 | −1.12 |
| CHAC1 | 1.88 | −2.12 | −2.63 | 0.18 | −1.46 | RNU6-321P | −0.82 | −0.08 | 0.65 | 0.12 | 0.62 | SOCS5P5 | −0.48 | 0.86 | −2.06 | 1.51 | −1.46 |
| IL6R | 0.44 | −0.39 | −0.68 | 0.02 | −0.47 | AP003108.4 | −0.23 | −0.24 | 0.00 | −0.21 | 0.25 | AC009396.2 | 0.41 | −0.39 | −3.11 | 2.27 | −0.91 |
| NSD2 | 0.51 | −0.49 | −0.70 | −0.19 | −0.11 | AP001646.1 | 0.47 | 0.42 | 0.57 | 0.42 | 0.09 | F2R | −0.07 | 0.21 | 0.69 | −0.17 | −0.09 |
| SCGB1B2P | −1.92 | 2.18 | 2.69 | 0.28 | 0.68 | ACTBL2 | −0.85 | 0.48 | 0.23 | −0.28 | 0.29 | AC004890.1 | −0.21 | −0.30 | −0.31 | −0.12 | −0.23 |
| AL049767.1 | 2.26 | −2.29 | −1.26 | −0.54 | −1.31 | AC104667.1 | −0.86 | 0.01 | 0.00 | −0.45 | −0.63 | AC243312.2 | 0.53 | −1.58 | −0.39 | −0.49 | 0.92 |
| AC103740.1 | −1.07 | 0.37 | 0.05 | 0.49 | 0.27 | AL049712.1 | −0.81 | 0.67 | 0.43 | 0.73 | −0.53 | AC005180.1 | 0.16 | −0.64 | 0.82 | −0.07 | 0.34 |
| GALNT14 | 1.05 | −0.78 | −1.23 | −0.09 | 0.09 | HNRNPA1P21 | 0.63 | −0.65 | −1.15 | −0.47 | −0.46 | IL15 | 0.08 | −0.49 | −0.01 | −0.52 | −0.13 |
| JAG1 | 0.46 | −0.15 | −0.54 | 0.03 | −0.26 | AL669818.1 | −0.38 | 0.20 | −0.05 | −0.08 | −0.04 | HSP90AA5P | −0.23 | −1.84 | 0.65 | −0.57 | 0.73 |
| MYDGF | 0.53 | −0.33 | −0.44 | −0.17 | −0.30 | RNU1-148P | −0.90 | −0.22 | −0.11 | −0.18 | −0.13 | LXN | 0.05 | 0.15 | 0.03 | 0.04 | −0.09 |
| SLC5A1 | 1.16 | −0.12 | −0.26 | −0.08 | −0.85 | PCNX2 | 0.13 | −0.09 | −0.22 | 0.21 | 0.08 | GCKR | 0.15 | −0.25 | −0.10 | 0.26 | 0.32 |
| LINC00667 | −0.47 | 0.25 | 0.68 | 0.05 | 0.14 | AC073896.4 | −0.28 | −0.17 | 0.27 | −0.31 | 0.21 | G8455 | 0.16 | 0.62 | −0.44 | 0.35 | 0.23 |
| MED4 | 0.46 | −0.24 | −0.17 | −0.14 | −0.02 | GLRA3 | −0.70 | 0.27 | 0.90 | −0.04 | 0.28 | AC140725.1 | 0.53 | −0.20 | −1.83 | 0.71 | −0.18 |
| LRRC2 | −1.13 | 0.71 | 1.26 | 0.12 | 0.13 | AC108463.2 | 1.10 | −1.73 | −0.58 | −1.77 | 0.70 | PROC | −0.12 | 0.30 | −0.38 | 0.13 | −0.28 |
| SLC35E2B | −0.43 | 0.25 | 0.29 | 0.27 | 0.37 | AC110772.1 | −1.16 | −0.22 | 2.71 | −0.92 | 0.35 | G12163 | −0.10 | 0.02 | 0.11 | 0.09 | 0.34 |
| CPTP | 0.56 | 0.11 | −0.30 | 0.23 | −0.16 | AC144833.1 | −0.56 | 0.09 | 0.00 | 0.92 | 0.25 | AC021820.1 | 0.45 | −0.64 | 1.22 | 0.18 | 1.46 |
| AL445426.1 | −1.85 | 1.74 | 1.70 | 0.58 | −0.27 | GTF2IP1 | 0.26 | 0.23 | 0.02 | 0.17 | −0.11 | RPS4Y1 | 0.11 | −0.32 | −0.17 | −0.04 | 0.55 |
| MIR548AC | 2.87 | −0.95 | −1.36 | −0.02 | −1.25 | APOBEC3F | −0.25 | 0.09 | 0.22 | −0.21 | 0.02 | AL390728.5 | 0.42 | 0.27 | 1.13 | 1.11 | 0.08 |
| LINC00702 | −1.09 | 0.58 | 0.61 | 0.25 | −0.44 | ARL1 | 0.16 | 0.06 | 0.11 | −0.12 | −0.09 | AL139811.2 | 0.41 | −0.09 | −1.94 | 2.17 | −1.70 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| OXNAD1 | 0.36 | −0.31 | −0.19 | −0.27 | 0.03 | PMEPA1 | 0.27 | −0.05 | −0.30 | −0.29 | −0.17 | AC126283.1 | −0.41 | 0.61 | 0.39 | 1.53 | 0.80 |
| SSSCA1 | 0.49 | −0.27 | −0.44 | −0.10 | −0.18 | RTL8A | 0.16 | 0.02 | −0.36 | 0.06 | −0.24 | AL355870.1 | −0.66 | −0.64 | 1.01 | 0.06 | 1.30 |
| NOP14 | 0.52 | −0.36 | −0.65 | −0.07 | −0.12 | ABHD14A | −0.28 | 0.23 | 0.19 | 0.29 | 0.10 | PRDX3 | 0.05 | −0.18 | −0.19 | −0.28 | −0.11 |
| RIOK2 | 0.58 | −0.22 | −0.20 | −0.20 | −0.24 | LINC01227 | 1.06 | −1.15 | −4.41 | 0.40 | −2.10 | AC080080.1 | −0.10 | −0.06 | 0.57 | 0.08 | 0.53 |
| PAPOLA | 0.49 | −0.14 | −0.23 | −0.08 | −0.12 | LINC01311 | −0.40 | 0.03 | 0.17 | 0.10 | 0.19 | AC007240.2 | 0.20 | −0.34 | −0.70 | 0.34 | 0.10 |
| BRMS1L | 0.48 | −0.23 | −0.30 | −0.08 | −0.26 | G3878 | −0.69 | 0.58 | 0.80 | −0.52 | −1.12 | LINC02057 | −0.28 | 1.08 | 0.35 | −0.49 | −0.33 |
| OR2T3 | −3.95 | 0.43 | 0.83 | −0.94 | −0.02 | NUTF2P3 | 1.35 | −0.86 | −0.30 | −0.09 | −0.02 | BNIP3P31 | −0.63 | −0.11 | −0.96 | 0.94 | −1.13 |
| CENPX | 0.60 | −0.44 | −0.48 | −0.16 | 0.05 | LMX1B | −0.29 | 0.31 | 0.25 | 0.08 | 0.09 | AL353718.1 | 0.36 | −0.51 | −1.48 | 1.98 | −0.82 |
| AL513320.1 | −1.31 | 1.01 | 1.61 | 0.59 | 0.16 | SNORD18 | 1.74 | −1.35 | −1.18 | 0.51 | 0.71 | PABPC1P1 | 0.10 | −0.53 | −0.01 | −0.20 | 0.02 |
| G40864 | −0.66 | 0.30 | 0.49 | 0.19 | 0.26 | AC055731.1 | 0.83 | 0.09 | −0.04 | 1.18 | 0.88 | MIR3188 | −0.29 | 0.12 | −1.18 | −1.04 | −0.06 |
| CYP46A1 | −0.82 | 0.35 | 0.92 | 0.15 | 0.35 | RNU6-254P | 0.67 | −0.24 | −0.05 | −0.02 | −0.37 | ACAD11 | −0.15 | 0.19 | 0.48 | −0.34 | −0.05 |
| ESRRG | −1.39 | 0.67 | 1.29 | 0.23 | 0.50 | HAGLROS | 0.90 | −0.07 | −0.16 | −0.04 | −0.81 | AL354824.2 | 0.43 | 0.31 | −0.36 | −0.33 | −1.31 |
| COPA | 0.29 | −0.21 | −0.28 | −0.17 | −0.21 | ALS2CR12 | −0.29 | −0.09 | −0.24 | 0.11 | −0.01 | AC239600.1 | −0.82 | −0.25 | 0.95 | 0.64 | 0.35 |
| PRPSAP2 | 0.34 | −0.13 | −0.06 | 0.02 | 0.12 | 7SK | 0.34 | −0.21 | −0.42 | −0.01 | −0.01 | STAG3L4 | −0.03 | −0.08 | −0.14 | 0.04 | 0.07 |
| PRKAR2B | −1.55 | 1.27 | 0.95 | 0.56 | −0.09 | RNU6-142P | 0.67 | −0.43 | 0.54 | −0.27 | 0.37 | PLUT | 0.49 | 1.08 | −0.26 | 0.68 | −1.76 |
| COPS6 | 0.37 | −0.15 | −0.31 | −0.14 | −0.21 | AC011481.2 | 1.38 | −1.80 | −1.78 | −0.28 | −0.45 | ISOC1 | −0.08 | 0.15 | 0.06 | 0.18 | 0.21 |
| MASTL | 0.45 | −0.41 | −0.41 | −0.12 | −0.11 | HGFAC | −0.95 | 0.86 | 0.40 | −0.29 | −0.58 | LINC02528 | −0.72 | 0.95 | 1.34 | −0.37 | −0.37 |
| NLRP3P1 | 1.14 | −0.93 | −1.55 | −0.17 | −0.31 | AL355994.4 | 0.42 | −0.47 | −0.03 | −0.68 | −0.10 | DDX4 | 0.20 | −0.43 | −0.68 | −0.03 | −0.56 |
| AC083799.1 | 0.82 | −0.07 | −0.85 | 0.21 | −0.66 | AC003965.2 | 2.16 | −2.50 | −2.76 | 0.62 | 1.35 | LDHAL6A | −0.10 | 0.13 | 0.24 | −0.08 | −0.25 |
| RCAN2 | −1.01 | 0.65 | 1.42 | 0.43 | 0.72 | AC006055.1 | −0.89 | −0.41 | 0.55 | 0.06 | −1.34 | LINC00489 | 0.50 | −1.49 | −0.23 | −0.75 | 0.99 |
| ATP2C2 | −0.85 | 0.29 | 1.04 | −0.06 | 0.44 | AC002542.1 | 1.03 | −0.09 | −0.77 | 0.07 | −1.15 | AC110056.1 | 0.52 | −0.82 | −0.91 | 0.34 | −0.93 |
| KIF27 | −0.41 | 0.32 | 0.40 | 0.18 | 0.02 | AC025165.4 | −0.34 | 0.15 | 0.50 | −0.14 | 0.17 | HNF4GP1 | −0.49 | 0.43 | −0.82 | 0.94 | −0.61 |
| SBNO1 | 0.44 | −0.05 | −0.25 | −0.08 | −0.26 | AC079140.5 | −0.80 | 0.65 | 1.44 | 0.76 | 0.10 | KLHL28 | 0.05 | 0.13 | 0.25 | −0.18 | −0.11 |
| CDKN1B | −0.46 | 0.42 | 0.36 | 0.18 | −0.02 | AC005070.3 | −0.22 | 0.03 | 0.19 | 0.08 | 0.17 | GOLGA8G | 0.51 | 0.23 | −0.51 | 0.84 | −0.45 |
| AL117336.3 | −0.76 | 0.34 | 0.55 | 0.05 | 0.22 | RPL10P15 | 0.79 | −1.42 | −0.91 | −0.35 | 0.20 | RPSAP18 | −0.16 | −0.05 | 2.06 | 0.05 | 1.22 |
| GRIK2 | −0.91 | 0.22 | 0.87 | 0.29 | 0.61 | AL109924.1 | −0.82 | 0.80 | 1.59 | 0.48 | 0.55 | AP001330.1 | −0.63 | 0.90 | 1.44 | 0.66 | 0.47 |
| AL049796.1 | −1.31 | 0.65 | 0.68 | 0.85 | 0.36 | G39214 | 0.45 | −0.06 | 0.28 | 0.22 | 0.14 | SLC39A10 | −0.07 | 0.00 | 0.27 | −0.19 | 0.02 |
| MTMR11 | −0.63 | 0.47 | 0.47 | 0.24 | −0.01 | MIGA1 | −0.13 | 0.16 | 0.11 | −0.05 | −0.05 | AL158155.1 | 0.20 | 0.34 | −0.34 | 0.36 | 1.61 |
| CCDC167 | 0.99 | −0.43 | −0.21 | −0.32 | −0.32 | APBA3 | −0.23 | −0.20 | −0.05 | 0.12 | 0.32 | AL035530.2 | −0.07 | 0.13 | −0.20 | 0.14 | −0.15 |
| HSD11B2 | −0.95 | 1.24 | 0.65 | 0.73 | −0.17 | KRT33B | 1.31 | −0.83 | 0.87 | 0.25 | 0.68 | AC156455.1 | −0.11 | 0.02 | −0.14 | −0.23 | −0.67 |
| RBM12 | 0.42 | −0.18 | −0.28 | 0.08 | −0.01 | AL391001.1 | 0.47 | −0.10 | 0.10 | −0.14 | 0.07 | PTPRD | −0.07 | 0.02 | −0.71 | −0.08 | −0.78 |
| CCDC127 | −0.46 | 0.28 | 0.26 | 0.09 | −0.10 | AL031123.3 | −0.31 | −0.12 | 0.18 | −0.24 | 0.42 | DCAF1 | −0.03 | −0.10 | −0.19 | −0.04 | −0.03 |
| POLR3E | −0.49 | 0.20 | 0.17 | 0.18 | 0.15 | GOLGA1 | −0.12 | −0.01 | 0.13 | 0.02 | 0.11 | ANKRD44-IT1 | −0.09 | −0.43 | 0.24 | −0.47 | 0.11 |
| RRP1B | 0.45 | −0.36 | −0.55 | −0.08 | −0.07 | RPL6P2 | −0.42 | 0.21 | 0.67 | −0.24 | 0.34 | AC090519.5 | −0.18 | −0.29 | 0.64 | −0.23 | 0.20 |
| PLCE1 | −0.67 | 0.28 | 0.58 | 0.31 | 0.31 | SFTPB | −0.43 | 0.12 | −0.02 | −0.19 | −0.08 | AC116533.2 | −0.66 | 1.64 | 0.67 | 0.22 | −0.43 |
| SERPINB8 | 0.75 | 0.03 | −0.17 | 0.08 | −0.60 | AC063923.1 | 1.38 | −1.92 | −0.77 | 0.37 | 0.30 | AC015853.3 | 0.12 | −0.08 | −0.17 | 0.36 | −0.12 |
| ARMC6 | 0.47 | −0.44 | −0.78 | 0.02 | −0.04 | PCED1B | 0.30 | −0.41 | −0.16 | −0.08 | 0.37 | AC093582.1 | 0.17 | 0.13 | −0.17 | 0.05 | 0.11 |
| HIST1H2BD | 0.91 | −0.26 | −1.12 | −0.13 | −0.98 | SATB2-AS1 | −0.73 | 0.11 | 0.72 | 0.05 | 0.02 | MIR4300HG | −0.20 | 0.24 | −1.45 | 0.38 | −0.43 |
| SLC25A24 | 0.52 | −0.43 | −0.55 | −0.18 | −0.28 | SOX17 | 0.48 | −0.30 | −0.03 | 0.14 | 0.05 | PYY | −0.26 | −1.78 | −2.00 | −0.13 | 0.82 |
| PEAK3 | −1.07 | 0.10 | −0.20 | 0.54 | −0.06 | C1orf52 | −0.10 | 0.07 | 0.11 | −0.08 | −0.06 | DHCR24-DT | 0.22 | 1.36 | 0.32 | 0.56 | 0.34 |
| SNHG15 | 0.74 | −0.52 | −1.06 | −0.04 | −0.57 | DPRXP5 | 0.92 | 0.23 | −0.28 | 0.20 | −1.03 | RNU6-79P | −0.25 | −0.44 | 1.55 | −0.72 | 1.08 |
| DAP3 | 0.32 | −0.14 | −0.26 | −0.10 | −0.09 | MIR660 | 1.42 | −0.78 | −0.11 | −0.27 | 1.75 | RNU6-1189P | 0.36 | −0.70 | 1.43 | 1.54 | 2.52 |
| RLIM | 0.40 | −0.19 | −0.44 | −0.12 | −0.33 | PPIP5K2 | 0.15 | −0.01 | −0.03 | −0.01 | −0.16 | PDHA1 | 0.05 | −0.08 | −0.12 | −0.08 | 0.09 |
| FAM43A | 0.91 | −0.30 | −0.76 | 0.03 | −0.55 | MTMR9LP | −0.30 | 0.16 | 0.73 | 0.12 | 0.22 | AP001198.1 | 0.41 | 0.20 | −0.60 | −0.49 | 0.29 |
| ANKRD53 | −1.02 | 0.25 | 0.81 | −0.10 | 0.05 | AC113382.1 | −0.84 | 0.39 | 0.62 | 0.62 | 0.18 | AC118942.1 | −0.36 | −0.26 | −1.26 | 0.82 | −1.47 |
| FGF17 | −2.22 | 0.10 | 2.98 | 1.07 | 0.67 | AC069281.1 | −0.91 | −0.38 | 2.20 | 0.07 | 1.19 | AL161757.1 | 0.33 | −0.53 | 0.37 | 0.52 | 0.21 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| B3GNT3 | 1.52 | −0.90 | −0.27 | −1.23 | −0.96 | AL844908.2 | −0.85 | 0.89 | 0.43 | 0.91 | −0.02 | SLC15A3 | 0.08 | −0.50 | −0.31 | −0.41 | −0.23 |
| AC006042.3 | −0.65 | 0.88 | 1.41 | 0.34 | 0.24 | AC093799.1 | −0.32 | −0.02 | 0.47 | −0.37 | 0.56 | AC245128.3 | 0.95 | −0.67 | −1.00 | 0.02 | −2.97 |
| BSN | −0.71 | 0.01 | 0.24 | −0.16 | 0.09 | AL110292.1 | −1.09 | −0.60 | 1.00 | −0.97 | 0.53 | APOA1 | 0.26 | −0.32 | 0.52 | −0.26 | 1.21 |
| PLA2G4C | −0.91 | 0.37 | 0.67 | 0.35 | 0.06 | KCNE5 | 1.45 | −0.90 | −0.09 | −0.94 | −0.07 | LINC01251 | 1.10 | −0.75 | 0.66 | 0.58 | −0.66 |
| BACH1-IT2 | 1.07 | −0.58 | −0.36 | −0.28 | −0.15 | RNU6-1141P | 0.80 | −0.80 | −1.06 | 0.51 | 0.21 | F10-AS1 | −0.42 | −0.61 | 2.06 | −0.13 | 2.71 |
| CCL21 | 1.36 | −0.62 | 0.30 | −0.36 | −0.75 | PEX5L-AS2 | −1.66 | 0.01 | 0.18 | 0.96 | −0.49 | DDX18P3 | 0.19 | 0.31 | 1.09 | 0.98 | 0.64 |
| HIST1H1C | 0.60 | −0.49 | −0.83 | −0.16 | −0.48 | AC021382.1 | −1.06 | −1.20 | −1.49 | −0.28 | −1.09 | LINC02584 | −0.84 | −0.15 | −0.11 | 0.49 | 0.12 |
| NAXE | 0.55 | −0.27 | −0.12 | −0.18 | −0.04 | OR10V2P | −0.49 | −0.03 | 0.62 | 0.56 | 0.87 | AC073508.1 | 0.29 | −1.41 | −1.06 | 0.94 | 1.58 |
| AC007637.1 | −1.07 | 0.39 | 0.64 | 0.46 | 0.20 | ARFIP1 | 0.12 | −0.06 | 0.22 | −0.12 | 0.11 | ATP5F1AP3 | −0.19 | 0.20 | 0.38 | 0.14 | 0.38 |
| G16268 | −1.37 | 0.13 | 1.40 | 0.55 | 0.79 | LINC00670 | −0.54 | −0.07 | 0.19 | 0.22 | −0.93 | FAF1 | 0.02 | 0.04 | −0.08 | 0.08 | −0.07 |
| SAR1B | 0.48 | −0.11 | −0.27 | 0.03 | −0.14 | SLC5A8 | 0.77 | −0.77 | 0.78 | −0.07 | 1.01 | AC103764.1 | −0.37 | −0.79 | −0.11 | 0.39 | 0.19 |
| GSTT1 | −0.59 | 0.30 | 0.80 | 0.30 | 0.02 | POLR3C | 0.10 | 0.02 | −0.15 | 0.01 | −0.21 | CTRC | −0.16 | −0.26 | −0.36 | −0.04 | −0.32 |
| G8227 | −2.27 | 1.36 | 2.57 | 0.85 | 0.63 | AC055733.4 | −0.44 | −0.19 | −0.25 | −0.06 | 0.50 | AL158070.2 | 0.50 | −1.11 | −0.30 | −0.85 | 0.60 |
| ATP6VOE1 | 0.60 | −0.30 | −0.13 | −0.23 | −0.20 | MIR640 | 0.66 | −0.51 | 0.06 | −0.62 | 0.33 | C2orf27A | −0.08 | −0.15 | 0.26 | −0.36 | 0.06 |
| KLF9 | −0.72 | 0.65 | 0.82 | −0.06 | −0.10 | SPAG5-AS1 | −0.33 | −0.26 | 0.24 | −0.30 | 0.65 | CCDC11P1 | −0.40 | −1.33 | −0.64 | 1.08 | −0.72 |
| NPTN | 0.46 | −0.15 | −0.42 | −0.12 | −0.37 | RPS29P5 | 0.62 | −0.06 | −0.35 | 0.08 | −0.13 | STK19 | −0.04 | 0.08 | −0.05 | 0.14 | −0.05 |
| QTRT2 | 0.37 | −0.25 | −0.28 | −0.02 | −0.01 | RNA5SP283 | −0.56 | 0.02 | 0.19 | −0.13 | −0.13 | AC022146.1 | 0.46 | −0.74 | −3.67 | 0.63 | −0.94 |
| FRMPD3 | −1.58 | 0.91 | 0.77 | −0.17 | −0.23 | SLC22A10 | −0.81 | 0.14 | −1.23 | 0.90 | 0.52 | AC068472.1 | 0.95 | −0.97 | −0.49 | 0.12 | −4.10 |
| ARHGEF3 | 0.38 | 0.03 | −0.14 | 0.16 | −0.05 | CCNG2 | −0.21 | 0.22 | 0.33 | 0.01 | 0.20 | LINC01828 | 0.12 | 0.07 | −1.05 | −0.08 | −0.87 |
| PRDM8 | −1.12 | −0.09 | 0.89 | 0.23 | 0.68 | AC002351.1 | −0.96 | 0.81 | 0.43 | 0.45 | 0.11 | PDCL3P3 | 0.41 | 0.22 | −0.98 | 0.70 | −0.82 |
| BX322639.1 | −0.92 | 0.42 | 1.05 | −0.24 | 0.67 | NUDCD3 | 0.11 | −0.06 | −0.09 | −0.01 | 0.05 | OR11N1P | −1.04 | −0.50 | NA | −0.43 | −1.95 |
| CIB1 | 0.54 | −0.22 | −0.98 | 0.20 | −0.30 | SH3D21 | −0.30 | 0.36 | −0.48 | 0.16 | −0.33 | FARSA-AS1 | 0.12 | −0.32 | −0.36 | −0.06 | 0.26 |
| SLC6A2 | −1.12 | 0.13 | 0.39 | 0.76 | 0.85 | PLEKHM1 | 0.14 | 0.04 | −0.20 | −0.10 | −0.24 | AC008012.1 | 0.48 | −0.66 | −0.62 | −0.04 | −2.10 |
| CHCHD2 | 0.59 | −0.36 | −0.40 | −0.22 | −0.34 | AC092115.1 | 0.35 | −0.99 | −0.94 | −0.30 | 0.07 | AP001271.2 | −0.21 | 0.99 | −0.05 | −0.08 | 0.69 |
| MZT1 | 0.74 | −0.20 | −0.52 | −0.16 | −0.50 | MAX | 0.10 | 0.08 | 0.18 | −0.03 | 0.02 | SNRPGP12 | −0.30 | 0.37 | 0.68 | −0.87 | −0.07 |
| IQCD | −0.81 | 0.65 | 1.01 | 0.03 | −0.12 | NCR3LG1 | 0.26 | −0.16 | −0.29 | 0.15 | −0.16 | AC100778.1 | 0.15 | −0.76 | 0.48 | −0.73 | 0.59 |
| APTX | 0.34 | −0.15 | −0.16 | −0.18 | −0.04 | AL512656.1 | 0.67 | 0.44 | 0.00 | −0.29 | −0.55 | AC012558.1 | 0.28 | 0.21 | −0.83 | −0.57 | −0.59 |
| AL031714.1 | −0.83 | 0.25 | 0.21 | 0.30 | 0.24 | AC108676.1 | −0.65 | −0.66 | 0.27 | 1.15 | 0.91 | AL031056.1 | 0.26 | −0.72 | −0.28 | −0.18 | 0.39 |
| MOV10 | −0.55 | 0.11 | 0.20 | 0.06 | 0.16 | MTND5P8 | 1.09 | 0.11 | −1.76 | −0.50 | −1.72 | AC011266.1 | −0.29 | 1.51 | −0.40 | 0.32 | −2.53 |
| CAVIN2 | −1.16 | 0.80 | 1.24 | 0.33 | 0.08 | AC234782.1 | 1.81 | −1.08 | 1.73 | −1.34 | 1.42 | AC022469.1 | 0.41 | −0.03 | 0.01 | −0.36 | −1.42 |
| RACGAP1P | −2.55 | 1.37 | 2.36 | −0.56 | 0.41 | AC005304.3 | 0.49 | −0.26 | −0.02 | 0.22 | 0.22 | AC138057.1 | 0.63 | −1.12 | −1.96 | −0.78 | −0.66 |
| SLC31A1 | 0.71 | −0.17 | −0.32 | −0.01 | −0.40 | AC024933.1 | 0.54 | −0.04 | −0.95 | −0.11 | −1.08 | AC117430.1 | −0.48 | 0.25 | 0.96 | 0.03 | −0.28 |
| PRMT7 | −0.41 | 0.04 | 0.26 | 0.04 | 0.24 | G39803 | 1.22 | 0.73 | −1.50 | −0.13 | −1.81 | AC145625.1 | −0.20 | 0.31 | 1.44 | −0.40 | 0.99 |
| PEX3 | 0.52 | −0.34 | −0.20 | −0.06 | 0.02 | STON1 | −0.27 | 0.23 | 0.83 | −0.26 | 0.15 | AC013290.1 | −0.34 | −1.63 | 2.02 | −1.43 | 2.42 |
| RDM1P5 | −1.01 | 0.15 | 0.27 | 0.24 | 0.36 | C12orf60 | −0.35 | 0.31 | 0.32 | 0.22 | 0.44 | AP005205.3 | −0.37 | −0.25 | 2.56 | 0.00 | 0.75 |
| HADH | −0.45 | 0.06 | 0.13 | 0.23 | 0.13 | KRTAP10-3 | −1.68 | −0.44 | 2.21 | −0.46 | 0.69 | DNAJB9 | −0.06 | 0.21 | 0.20 | −0.29 | −0.19 |
| RPS3 | 0.60 | −0.10 | −0.26 | 0.10 | −0.43 | AC027796.5 | −0.79 | 0.35 | 1.23 | −0.87 | 0.27 | CLEC2D | −0.05 | −0.13 | 0.30 | −0.16 | 0.25 |
| HDAC11 | −0.67 | 0.64 | 0.53 | 0.32 | 0.10 | SFT2D1 | 0.18 | −0.01 | −0.20 | 0.07 | 0.00 | MIR4677 | 0.13 | −0.20 | 0.86 | −0.73 | 0.23 |
| AL031281.3 | −0.99 | 0.10 | 0.60 | 0.09 | 0.32 | NODAL | −0.52 | 0.26 | 0.37 | 0.07 | −0.34 | RTBDN | −0.25 | −1.15 | −2.72 | −0.13 | −2.10 |
| POFUT2 | −0.76 | −0.01 | 0.37 | 0.04 | 0.25 | AL139128.1 | 0.45 | −0.05 | −0.20 | 0.39 | −0.31 | DDX39BP2 | −0.19 | 0.41 | 0.75 | −0.21 | 0.45 |
| DACT2 | −1.18 | 0.78 | 0.22 | 1.01 | 0.50 | RPS24P17 | 1.29 | −0.14 | −0.64 | 0.10 | 0.27 | AC080125.1 | −0.21 | 0.83 | 0.52 | 0.73 | 0.25 |
| GBAP1 | 0.83 | −0.66 | −1.01 | −0.05 | −0.28 | HIST1H1T | 0.98 | −1.47 | −1.36 | −0.81 | 0.52 | PLS1-AS1 | 0.32 | −0.01 | −0.63 | 0.38 | −0.96 |
| AF111167.1 | −1.46 | 1.28 | 1.99 | 0.26 | 0.60 | GAB4 | −0.82 | 0.45 | −0.92 | 0.08 | −0.75 | AC020550.1 | 0.17 | 0.19 | 0.59 | −0.11 | 0.17 |
| G38642 | −2.63 | 1.72 | 1.81 | 1.77 | 0.16 | AL118508.3 | 1.13 | −0.70 | −2.12 | 0.70 | −1.25 | SETP17 | 0.12 | −0.30 | 0.23 | 0.21 | 0.05 |
| ARMCX3 | −0.75 | 0.35 | 1.13 | −0.22 | 0.31 | RNY4P4 | 0.43 | −0.50 | 0.20 | −0.46 | 0.39 | FAAP100 | 0.04 | −0.11 | −0.26 | 0.19 | 0.25 |
| E2F4 | 0.48 | −0.37 | −0.56 | −0.01 | 0.05 | PADI6 | 1.21 | −1.74 | −0.54 | 0.11 | 1.48 | RNU6-1320P | −0.44 | −2.25 | 0.26 | −0.87 | 1.19 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| CXADR | 1.40 | −0.07 | −0.51 | 0.24 | −0.32 | AC010333.2 | 0.49 | −0.51 | −0.17 | −0.28 | 0.37 | MIR4740 | 0.29 | 0.03 | −1.55 | 0.19 | −1.42 |
| SLC39A9 | 0.61 | −0.20 | −0.38 | −0.12 | −0.28 | AL359094.1 | −0.24 | 0.21 | 0.07 | 0.09 | −0.03 | GATA4 | 0.35 | −0.11 | −0.76 | 0.87 | −2.27 |
| MYOCD | −1.36 | 0.46 | 1.04 | 0.31 | 0.01 | LINC02201 | −0.75 | 0.15 | −1.01 | 0.76 | 0.08 | KCTD9P1 | −0.14 | 0.20 | 1.24 | −0.07 | 0.27 |
| SLC38A7 | 0.51 | −0.45 | −0.38 | −0.30 | −0.16 | DCPS | 0.16 | 0.01 | −0.08 | 0.14 | 0.13 | AP005136.1 | 0.73 | −0.52 | 0.17 | −1.16 | −0.65 |
| AC097470.1 | 3.62 | −1.75 | −1.83 | 0.27 | −3.23 | SCRN3 | 0.14 | −0.08 | 0.05 | 0.05 | 0.10 | ARHGAP18 | 0.06 | −0.03 | −0.06 | −0.08 | −0.04 |
| H1FX-AS1 | −1.19 | 0.44 | 0.82 | 0.74 | 0.45 | RPL26P35 | 0.50 | 0.07 | −0.68 | 0.19 | −0.80 | AC015845.2 | 0.34 | 0.16 | 0.77 | 0.75 | 0.13 |
| FAM184A | −0.79 | 0.49 | 0.74 | 0.07 | 0.23 | AC010974.1 | 1.79 | −0.58 | 0.32 | −0.76 | 0.62 | LINC01941 | 0.56 | −1.77 | −0.13 | 0.20 | 0.63 |
| RN7SL407P | −1.51 | −0.23 | 0.12 | 0.23 | 0.94 | AC069366.2 | 0.49 | −0.11 | −0.38 | 0.95 | 0.38 | KRT223P | −0.28 | −0.41 | −0.43 | −0.52 | −1.39 |
| RCC2 | 0.50 | −0.25 | −0.33 | −0.03 | −0.13 | PPP1R3B | −0.25 | 0.08 | 0.41 | −0.30 | −0.07 | AC097173.2 | 0.71 | −1.27 | −0.72 | −2.01 | 0.37 |
| DNAJC22 | −1.03 | −0.27 | 0.48 | 0.26 | 0.85 | AC114495.2 | 0.47 | −0.36 | 0.09 | −0.33 | −0.12 | KLF1 | −0.30 | −0.29 | −0.72 | 0.67 | −0.45 |
| RPS6KA5 | −0.48 | 0.35 | 0.33 | 0.28 | 0.00 | AC011899.2 | 0.53 | −0.42 | −0.35 | −0.12 | 0.31 | AL356807.1 | −0.44 | −0.78 | 1.34 | −0.78 | 1.31 |
| NSD1 | 0.36 | −0.15 | −0.26 | −0.03 | −0.06 | AC092598.1 | −1.00 | −0.07 | 1.23 | −1.55 | 0.59 | MIR376A1 | 0.66 | 1.32 | 0.61 | 0.23 | −1.15 |
| AC027237.4 | 1.54 | −0.76 | −1.57 | 0.06 | −1.06 | AC019254.1 | 0.89 | −1.78 | −2.64 | −0.15 | −0.89 | AC087501.4 | −0.08 | −0.30 | −0.36 | 0.07 | 0.01 |
| CAPN1 | 0.50 | −0.25 | −0.80 | 0.15 | −0.33 | RNU6-766P | −0.63 | 0.62 | −0.36 | 0.20 | 0.08 | GCNT3 | 0.14 | 0.17 | −0.67 | 0.81 | −0.07 |
| MUSK | −0.89 | 0.49 | 1.03 | −0.03 | 0.38 | AC092755.2 | 0.83 | −0.55 | −0.17 | −0.75 | 0.02 | RGS21 | −0.27 | −1.19 | 0.55 | −0.93 | 1.60 |
| MIR101-1 | −1.63 | 0.59 | 2.42 | −0.18 | 0.31 | AC092291.2 | −0.64 | −0.61 | −0.56 | −0.10 | 0.40 | FRAT1 | 0.10 | 0.74 | 0.46 | 0.38 | −0.13 |
| PPIAP22 | 0.91 | −0.32 | −1.09 | 0.09 | −0.76 | RPSAP36 | 0.23 | −0.10 | 0.01 | −0.14 | 0.05 | DHRS2 | 0.20 | −1.04 | −2.59 | 1.12 | 0.42 |
| LSINCT5 | −1.56 | 0.65 | 1.47 | 0.27 | 0.47 | FLVCR2 | 0.23 | −0.43 | 0.06 | −0.09 | 0.23 | SIGLEC18P | 0.30 | 0.46 | −0.55 | 0.75 | −1.11 |
| RAP2C | 0.54 | −0.38 | −0.35 | −0.18 | −0.15 | HMX3 | −1.57 | 0.21 | −0.01 | 0.55 | −0.47 | SMG1P6 | 0.06 | −0.24 | −0.21 | 0.01 | −0.04 |
| DUSP7 | 0.85 | −0.44 | −0.80 | −0.21 | −0.42 | PI4KB | 0.10 | 0.06 | −0.09 | 0.02 | −0.11 | AC107220.1 | 0.66 | −1.82 | 1.56 | −1.18 | 1.50 |
| OR2A7 | −0.94 | −0.05 | 0.57 | 0.44 | 0.80 | LCE2D | −0.52 | 0.33 | 1.10 | 0.28 | −0.28 | G19262 | −0.31 | −0.07 | 1.04 | 0.37 | 0.24 |
| SIAH2 | 0.87 | −0.16 | −0.47 | −0.17 | −0.62 | ABHD11-AS1 | −0.64 | 0.73 | 1.06 | 0.20 | 0.12 | AC105177.1 | −0.64 | −0.34 | −0.41 | 1.72 | −0.05 |
| MTCH2 | 0.64 | −0.30 | −0.54 | −0.15 | −0.42 | BPTF | −0.08 | 0.14 | 0.02 | 0.03 | −0.07 | HOXB7 | 0.08 | 0.06 | 0.68 | 0.12 | 0.11 |
| FAM66B | −0.98 | 0.46 | 1.50 | −0.32 | 0.33 | AL031432.2 | −0.47 | 0.09 | 0.62 | 0.06 | −0.33 | LINC02424 | 0.40 | 0.33 | 0.01 | 0.72 | −2.45 |
| ERVW-1 | −0.52 | 0.08 | 0.73 | −0.21 | 0.25 | SRL | −0.37 | 0.08 | −0.20 | 0.32 | 0.14 | AC011352.2 | −0.27 | 1.01 | 1.96 | 0.30 | −0.19 |
| HTR2B | 0.82 | −0.27 | −0.40 | 0.00 | −0.16 | AC108704.2 | 0.23 | −0.18 | 0.17 | −0.29 | −0.09 | HACD4 | 0.03 | 0.06 | 0.20 | 0.15 | 0.08 |
| MYOF | 0.37 | −0.16 | −0.42 | 0.02 | −0.17 | MIR646HG | −0.30 | −0.04 | 0.22 | 0.41 | 0.41 | CTSZ | 0.07 | −0.22 | −0.03 | −0.21 | −0.04 |
| G42897 | 2.42 | 0.01 | −0.63 | −0.21 | −0.68 | ATP5MC1P3 | −0.92 | 0.09 | 0.81 | 0.91 | −1.11 | NDUFS5P5 | −0.32 | −1.77 | 0.58 | −1.34 | 0.85 |
| NDUFAF1 | 0.48 | −0.50 | −0.30 | −0.13 | 0.01 | AL139317.4 | −0.51 | 0.50 | 0.18 | −0.15 | −0.56 | KRT18P46 | −0.54 | −0.94 | −0.11 | −0.71 | 0.58 |
| AFF2 | −1.04 | 0.14 | 0.91 | −0.24 | 0.30 | CCDC186 | 0.15 | 0.12 | −0.11 | 0.07 | −0.23 | NGFR | −0.10 | 0.30 | 0.43 | 0.11 | 0.19 |
| MBD4 | 0.29 | −0.13 | −0.28 | −0.04 | −0.12 | PPP2R5A | 0.19 | 0.04 | −0.03 | 0.12 | 0.11 | AL354674.1 | −0.31 | −1.33 | −0.96 | 0.81 | −1.25 |
| SPG7 | −0.51 | 0.12 | 0.25 | 0.16 | 0.32 | RNA5SP490 | −0.83 | −0.31 | 0.77 | −0.52 | 0.95 | RP11-7G23.5 | −0.70 | 0.04 | 0.37 | −2.14 | 1.00 |
| ATOX1 | 0.51 | −0.03 | −0.08 | 0.00 | −0.31 | MT1F | 0.36 | −0.12 | 0.01 | −0.35 | −0.27 | ADPGK-AS1 | −0.09 | −0.15 | −0.65 | 0.06 | −0.39 |
| AC021491.4 | −1.34 | −0.03 | 0.75 | 0.09 | 0.52 | AC008915.1 | −0.44 | −0.22 | 0.46 | 0.22 | 0.80 | HMGB1P25 | −0.59 | 0.05 | −0.50 | 0.20 | 0.70 |
| MIR221 | 1.79 | −1.10 | −0.45 | −0.47 | 0.14 | BIRC6-AS2 | 0.38 | −0.08 | −0.72 | 0.13 | −0.44 | AGXT2 | −0.20 | −0.62 | −0.15 | 0.78 | 0.22 |
| AL034553.1 | −1.61 | −0.15 | 0.27 | 0.55 | 1.16 | CFP | −0.30 | −0.41 | 0.03 | 0.21 | 0.31 | AC027281.2 | 0.11 | −0.41 | −0.45 | −0.12 | −0.02 |
| SH3BP5-AS1 | −0.48 | 0.41 | 0.60 | 0.08 | 0.19 | LCN1P1 | −1.56 | 1.10 | 1.57 | 0.75 | −0.42 | LINC01825 | −0.45 | −0.57 | −1.01 | 0.54 | 1.08 |
| LINC02024 | −2.04 | 1.32 | 2.64 | 0.39 | 0.48 | RNU6-446P | 0.88 | −0.46 | −0.72 | −0.25 | 0.02 | RNU6-625P | 0.53 | −1.09 | −0.58 | 0.01 | −1.07 |
| COG8 | −0.50 | 0.14 | 0.17 | 0.32 | 0.32 | AC015967.1 | −0.89 | 0.15 | 0.44 | −0.25 | −0.56 | AC104090.1 | 0.17 | 0.46 | −0.14 | 0.71 | −0.05 |
| NRG3 | −1.40 | 0.67 | 0.78 | 0.10 | 0.45 | RNA5SP366 | −0.86 | 0.13 | −0.05 | 0.83 | 0.29 | AL133297.1 | −0.13 | 0.56 | 0.12 | 0.60 | −0.24 |
| SRSF1 | 0.82 | −0.48 | −0.49 | −0.13 | −0.09 | ARL4AP1 | 0.48 | 0.04 | −0.10 | 0.36 | 0.19 | AC010424.3 | −0.33 | −0.48 | −1.57 | −0.49 | −1.03 |
| IER3 | 0.98 | −0.52 | −1.46 | −0.65 | −1.14 | ELMO2 | −0.10 | −0.04 | 0.18 | −0.05 | 0.21 | AC106872.1 | −0.46 | 0.68 | 0.20 | 1.10 | 0.06 |
| NR2F2-AS1 | −1.12 | 0.63 | 1.24 | 0.66 | 0.49 | RNU4-29P | 1.27 | 0.58 | 0.23 | −0.40 | −0.32 | PRSS38 | 0.31 | 0.24 | −2.54 | 1.33 | −2.50 |
| AC092376.2 | −0.73 | 0.40 | 0.30 | 0.28 | 0.12 | AC008147.3 | −0.29 | −0.32 | −0.60 | −0.03 | 0.13 | AC137627.1 | −0.41 | 0.26 | −1.04 | 1.38 | −0.44 |
| C5orf22 | 0.48 | −0.28 | −0.29 | −0.04 | −0.09 | AC046185.2 | 0.84 | −0.26 | 0.69 | 0.00 | −0.11 | CA7 | 0.50 | −1.06 | −0.79 | 0.52 | −1.28 |
| AL031587.1 | −1.77 | 0.71 | 1.81 | 0.85 | 0.77 | NKAP | −0.23 | −0.01 | 0.08 | −0.06 | −0.05 | AF129075.2 | 0.20 | −0.68 | 1.19 | −0.18 | 0.60 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| PDE11A | −1.56 | 0.87 | 0.81 | 0.72 | 0.50 | AC010265.1 | 0.47 | −0.32 | 0.43 | 0.27 | 0.40 | AP000593.1 | 0.27 | 0.15 | −0.01 | −0.27 | −0.91 |
| AC073062.1 | −2.57 | −0.20 | 1.51 | 1.48 | 0.41 | PUDPP2 | 1.16 | −0.75 | −0.73 | 0.29 | 0.21 | AC090282.1 | 0.40 | −1.12 | −1.12 | −0.50 | −0.08 |
| NDC1 | 0.76 | −0.51 | −0.41 | −0.25 | −0.14 | AC007683.1 | −0.35 | 0.05 | 0.25 | 0.17 | 0.35 | AC007598.3 | 0.07 | −0.05 | −0.13 | 0.18 | 0.17 |
| HNRNPA1P53 | −1.06 | 0.46 | 0.64 | 0.52 | 0.00 | PCID2 | −0.10 | −0.09 | 0.09 | −0.10 | 0.11 | RN7SL574P | −0.14 | −0.42 | −0.51 | 0.06 | −0.24 |
| HIST1H2AC | 0.69 | −0.25 | −0.79 | −0.30 | −0.58 | AL357079.2 | −0.54 | 0.50 | −0.48 | 0.06 | −0.68 | BSNDP1 | −0.39 | −1.29 | −1.28 | −0.81 | −1.42 |
| SQSTM1 | −0.41 | 0.21 | 0.22 | 0.10 | −0.08 | AC091132.1 | −0.54 | 0.01 | 0.41 | −0.19 | −0.03 | LINC00605 | 0.34 | −2.00 | 1.03 | 0.56 | 1.90 |
| AC009120.2 | −0.59 | 0.25 | 0.52 | 0.09 | 0.10 | HSP90AB2P | 0.31 | −0.55 | −0.96 | 0.09 | −0.16 | MTHFS | −0.08 | −0.23 | 0.43 | −0.11 | 0.69 |
| DCDC1 | −1.41 | 0.23 | 0.38 | 0.31 | 0.16 | AC068305.1 | −1.08 | 0.78 | 2.30 | 0.01 | −0.02 | AC114752.2 | −0.55 | 0.79 | −0.70 | −1.02 | −3.81 |
| RNF227 | −0.88 | 0.87 | 1.15 | 0.47 | 0.13 | MGAT4C | −0.66 | 0.45 | −0.41 | 0.67 | −0.73 | IGLV4-69 | 0.76 | 0.25 | −1.15 | 0.02 | −0.78 |
| PKMYT1 | 1.12 | −1.11 | −1.96 | −0.16 | −0.52 | AC004987.2 | 0.58 | −0.06 | −0.18 | 0.08 | −0.32 | MIR3920 | −0.32 | 0.07 | 0.95 | 1.57 | 0.39 |
| AC104389.4 | −1.03 | 0.08 | 0.42 | 0.21 | 0.33 | HDHD3 | 0.21 | 0.07 | −0.10 | 0.09 | −0.09 | PRPH2 | −0.09 | 0.00 | 0.18 | −0.25 | −0.12 |
| MEOX2 | −1.01 | 0.67 | 1.29 | 0.34 | 0.29 | CCL19 | 0.50 | −0.84 | 1.20 | −0.39 | −0.33 | C1orf61 | 0.12 | −0.62 | −0.76 | −0.20 | 0.02 |
| DTX4 | −0.81 | 0.38 | 0.51 | 0.20 | 0.37 | QDPR | −0.23 | 0.12 | 0.14 | 0.17 | 0.21 | ADAM18 | −0.30 | 0.09 | −0.81 | −0.17 | −1.14 |
| EML1 | 0.56 | −0.06 | −0.30 | −0.08 | −0.67 | AL138706.1 | 0.89 | −0.49 | −0.31 | −0.22 | −0.70 | RNU6-50P | −0.29 | 0.09 | 0.91 | −0.62 | 0.29 |
| RFX7 | 0.50 | −0.25 | −0.52 | 0.24 | −0.06 | G9978 | 0.21 | 0.15 | 0.05 | −0.14 | −0.20 | AL391666.1 | 0.41 | −1.08 | −0.72 | 0.34 | −0.03 |
| DNM1P47 | −0.98 | 0.21 | 0.55 | 0.00 | 0.41 | HACD2 | 0.24 | −0.06 | −0.24 | 0.08 | −0.14 | KIF9-AS1 | 0.09 | 0.18 | −0.06 | 0.06 | −0.10 |
| CDHR3 | −0.63 | 0.01 | 0.27 | 0.11 | 0.33 | FLJ46906 | 0.35 | 0.16 | 0.58 | 0.10 | 0.34 | AC092979.1 | −0.20 | 0.37 | 1.38 | 0.51 | 1.40 |
| ARHGEF10L | −0.53 | 0.34 | 0.27 | 0.19 | 0.07 | AC015908.4 | −0.99 | −0.80 | −0.77 | −0.23 | 0.10 | AC002069.1 | −0.66 | 0.69 | −0.35 | 0.34 | −0.62 |
| RERG | −0.87 | 0.68 | 0.89 | 0.39 | −0.02 | PLPP6 | 0.21 | 0.12 | −0.21 | 0.16 | −0.24 | AC096775.1 | 0.18 | −0.91 | −1.18 | −0.26 | 0.08 |
| CCDC136 | −0.74 | 0.14 | 0.55 | 0.19 | 0.14 | AC005414.1 | 0.38 | 0.08 | −0.89 | −0.61 | −1.02 | RNA5SP90 | 0.39 | −0.25 | 0.10 | 0.29 | 0.54 |
| AC211476.6 | −1.43 | 0.13 | 1.37 | 0.15 | 0.97 | AC015815.1 | −0.88 | −0.42 | 1.16 | −0.11 | 1.27 | LINC01335 | 0.69 | −1.58 | −1.81 | −0.25 | −1.78 |
| GDPD3 | 0.70 | −0.20 | −0.87 | −0.08 | −0.65 | SLC46A2 | −0.40 | 0.68 | 1.60 | 0.77 | 0.00 | METTL21C | 0.25 | 0.83 | −0.89 | 0.51 | −0.20 |
| ARMH4 | −0.86 | 0.71 | 0.93 | 0.16 | −0.06 | RNU6-490P | 0.97 | −0.67 | 0.04 | 0.62 | 0.01 | AC099521.1 | −0.34 | −1.49 | −1.35 | −0.59 | 0.37 |
| OR2T35 | −3.50 | −0.23 | 3.56 | 0.69 | 3.36 | RNU6-1313P | −1.57 | 1.00 | 1.69 | −0.43 | 0.43 | AL162254.1 | −0.18 | 0.15 | 1.01 | −0.26 | −0.87 |
| FOXI2 | −1.69 | 0.46 | 1.09 | 0.63 | 0.68 | MIR4742 | 0.69 | −0.40 | −0.45 | −0.48 | −0.51 | SENP3-EIF4A1 | 0.12 | −0.09 | −0.82 | 0.27 | −0.51 |
| AL590999.1 | −1.02 | 0.23 | 0.48 | 0.15 | 0.18 | AL121601.1 | −0.68 | 0.77 | 0.89 | 0.27 | −0.60 | AC073072.1 | 0.64 | −1.46 | 0.24 | −0.02 | 0.95 |
| AC005225.1 | −1.45 | 0.56 | 1.46 | 0.71 | 0.70 | CLIC6 | −0.40 | 0.27 | 0.94 | 0.03 | 0.33 | RNA5SP23 | −0.42 | −0.45 | 0.35 | 0.33 | 0.04 |
| FUK | −0.64 | 0.38 | 0.39 | 0.44 | 0.27 | RNU6-1025P | −1.27 | 0.72 | 1.36 | −0.86 | −0.33 | AC130469.1 | −0.16 | −0.22 | 1.03 | −0.29 | 0.71 |
| GABPB1-AS1 | −0.48 | 0.12 | 0.48 | −0.25 | −0.01 | MTRNR2L10 | −0.63 | 0.08 | −0.21 | 0.78 | 0.50 | AC053503.2 | 0.50 | 1.18 | −0.31 | 1.95 | 0.41 |
| RN7SL119P | −0.78 | −0.12 | 0.89 | −0.32 | 0.71 | HNRNPA1P26 | −0.76 | −0.25 | −0.19 | 0.19 | −0.08 | RP6-206I17.4 | 0.28 | −1.32 | 2.05 | −0.66 | 1.77 |
| COG2 | 0.34 | −0.12 | −0.18 | −0.05 | −0.10 | AL390760.1 | −0.61 | 0.09 | 0.72 | −0.24 | 1.06 | AC026316.4 | −0.17 | 0.25 | 0.45 | 0.85 | 0.25 |
| SORCS1 | −1.13 | 0.44 | 0.81 | 0.18 | 0.63 | LINC00907 | −0.43 | 0.20 | −0.38 | 0.77 | −0.16 | NRCAM | 0.09 | −0.15 | 0.00 | −0.43 | −0.13 |
| AC140658.1 | −1.68 | 0.96 | 0.53 | 1.22 | −0.02 | AC007000.1 | −0.43 | 0.68 | 0.35 | 0.44 | 0.28 | AC141586.1 | 0.05 | −0.13 | −0.13 | −0.10 | 0.05 |
| CLINT1 | 0.36 | −0.04 | −0.12 | −0.11 | −0.17 | LINC01679 | −0.34 | 0.54 | −0.21 | 0.24 | −0.36 | AC073387.1 | −0.47 | 0.72 | −1.12 | 2.55 | 1.61 |
| MTOR | 0.34 | −0.30 | −0.44 | −0.10 | −0.05 | AC010343.1 | 0.35 | −0.03 | −0.21 | −0.08 | −0.15 | DUXAP9 | −0.18 | −0.38 | 0.43 | −0.08 | 0.70 |
| PCDHGA9 | −0.63 | 0.49 | 0.77 | 0.04 | 0.15 | MRPS17P1 | −0.71 | −0.10 | 0.35 | 0.35 | 1.07 | AF015262.1 | −0.59 | −0.17 | 0.77 | −0.99 | 0.57 |
| FKBP15 | 0.24 | −0.09 | −0.22 | −0.11 | −0.21 | AC100756.2 | −1.08 | −0.18 | 1.34 | −1.11 | 1.96 | C5orf64-AS1 | 0.35 | −0.50 | −1.60 | 1.24 | −1.22 |
| FBXO31 | −0.42 | 0.27 | 0.11 | 0.18 | −0.02 | OR8J3 | −1.06 | −0.40 | −0.78 | 0.09 | −0.50 | CLCA1 | −0.25 | −0.22 | −1.31 | 0.97 | 0.25 |
| G41319 | 1.21 | −0.65 | −1.10 | −0.06 | −0.58 | FAM13A-AS1 | −0.21 | 0.18 | 0.38 | 0.11 | 0.26 | AC092798.1 | −0.11 | 0.30 | 0.51 | 0.14 | 0.44 |
| C15orf41 | 0.61 | −0.11 | −0.38 | 0.07 | −0.31 | LINC01990 | −0.99 | 0.95 | 0.18 | 0.04 | −1.86 | AC067752.1 | 0.22 | −0.84 | −0.58 | 0.43 | 0.40 |
| AP005233.2 | −1.97 | 2.27 | 1.86 | 1.52 | 0.78 | PFN1P4 | −1.29 | 0.98 | 1.25 | 0.62 | 0.14 | MTATP8P1 | −0.16 | −0.06 | −0.30 | 0.02 | −0.48 |
| CYP27B1 | 1.46 | −1.24 | −2.53 | 0.01 | −1.06 | AC025300.1 | 0.57 | −0.40 | 0.38 | −0.03 | 0.29 | MED28P6 | −0.30 | −1.79 | 0.46 | −0.40 | 0.24 |
| PITRM1 | 0.39 | −0.28 | −0.65 | 0.03 | −0.16 | AC093620.1 | −0.35 | 0.34 | 0.04 | 0.67 | 0.48 | ADGRL3-AS1 | −0.57 | −1.00 | −0.79 | 0.06 | −0.66 |
| MRPL35 | 0.56 | −0.44 | −0.37 | −0.26 | −0.19 | HCN2 | −0.39 | 0.29 | −0.42 | 0.42 | −0.49 | CRH | −0.50 | 0.28 | −1.94 | 1.92 | −1.94 |
| RPLPO | 0.77 | −0.10 | −0.20 | −0.16 | −0.65 | C11orf74 | −0.27 | 0.25 | 0.39 | −0.33 | −0.09 | COMMD10 | −0.03 | −0.05 | −0.12 | 0.10 | −0.03 |
| ERCC1 | −0.48 | 0.15 | 0.15 | 0.03 | 0.10 | NCBP2L | −1.01 | 0.26 | 0.82 | 0.21 | −0.68 | IGHV3-74 | 0.48 | 1.68 | −0.39 | 0.21 | −0.68 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| MPHOSPH9 | 0.37 | −0.43 | −0.37 | −0.14 | 0.06 | HMGN2P38 | 0.59 | −0.04 | −1.25 | −0.23 | −0.58 | AC010967.1 | −0.17 | −0.80 | −0.53 | −0.04 | −0.05 |
| HA02 | −2.07 | 1.20 | 0.93 | 0.37 | 1.32 | AC019186.1 | 0.45 | −0.21 | −0.31 | −0.11 | −0.29 | AC055733.1 | 0.10 | 0.19 | 0.15 | −0.04 | −0.04 |
| AL138756.1 | 0.74 | −0.46 | −0.83 | 0.01 | −0.15 | HOXD9 | −0.32 | 0.22 | 0.38 | 0.51 | 0.14 | RNU1-65P | −0.62 | −0.61 | −1.41 | 0.70 | 1.16 |
| CILP | −1.90 | 2.17 | 1.96 | 0.90 | −0.84 | AL137005.1 | −0.91 | −1.00 | 0.47 | 0.55 | 0.10 | ACTBP8 | 0.49 | −0.91 | −1.29 | −0.16 | 0.57 |
| IL2RA | 1.59 | −1.63 | −1.38 | −0.68 | −0.54 | SLC30A3 | −0.79 | −0.51 | 0.28 | 0.22 | 0.51 | RAP1AP | 0.20 | −0.46 | −0.83 | 0.01 | −0.80 |
| PLEKHD1 | −1.12 | 0.46 | 1.32 | 0.33 | 0.57 | SNX14 | 0.11 | −0.01 | 0.11 | −0.06 | 0.04 | AL133215.3 | 0.25 | −0.72 | 0.28 | −0.36 | 0.27 |
| FOXE1 | 1.01 | −0.41 | −1.23 | 0.08 | −0.40 | ADAMTS15 | 0.42 | 0.00 | −0.92 | 0.23 | −0.66 | AC112484.3 | −0.17 | −0.14 | 0.50 | −0.30 | 0.49 |
| LINC01806 | 1.09 | −0.35 | −1.32 | 0.06 | −1.11 | AC007485.1 | 1.17 | −0.22 | −1.41 | 0.62 | −1.25 | EMC3-AS1 | 0.05 | −0.31 | −0.08 | −0.11 | 0.14 |
| AC025884.1 | 1.64 | −0.73 | −1.02 | 0.89 | 1.36 | RN7SL499P | −1.22 | 0.19 | 2.17 | 0.17 | 0.66 | AC111188.2 | 0.16 | 0.32 | 0.97 | 0.09 | 0.34 |
| RAET1E | 1.23 | −0.07 | −0.21 | 0.25 | −0.38 | FOXR1 | −0.99 | −0.01 | −0.25 | 0.33 | 0.23 | KLHL20 | 0.03 | 0.06 | 0.02 | −0.05 | −0.09 |
| ERCC6L | 0.84 | −0.62 | −0.73 | −0.32 | −0.21 | LINC01908 | −1.35 | 1.79 | −0.03 | 1.00 | 0.84 | AC068039.1 | −0.19 | 0.84 | 0.04 | 0.07 | −1.18 |
| AL354893.2 | −1.22 | 0.54 | 1.04 | 0.18 | 0.48 | IL11 | 0.44 | −0.77 | −1.11 | −0.77 | −0.32 | AC009404.1 | 0.05 | −0.11 | 0.25 | −0.12 | 0.10 |
| AL359715.2 | −1.10 | 0.95 | 1.42 | 0.36 | 0.25 | AC020913.3 | −0.28 | −0.34 | −0.08 | −0.29 | 0.24 | G7666 | −0.13 | 0.21 | −0.45 | 0.58 | 0.72 |
| AL121753.2 | −0.77 | 0.57 | 0.84 | 0.11 | 0.16 | AP001178.3 | 0.52 | −0.88 | −0.39 | −0.36 | −0.19 | AC104561.1 | 0.37 | −0.84 | −2.04 | 1.46 | −0.04 |
| MED27 | 0.48 | −0.31 | −0.49 | −0.05 | −0.11 | AC027796.2 | −0.27 | 0.02 | −0.04 | −0.07 | 0.07 | FAM138D | 0.37 | −0.32 | −2.25 | 2.02 | −1.13 |
| DLG1 | 0.35 | −0.10 | −0.33 | −0.06 | −0.19 | LYNX1-SLURP2 | 1.03 | 0.01 | −2.25 | 0.95 | −1.72 | RNU6-510P | −0.17 | 0.12 | 0.49 | 0.37 | 0.35 |
| SNORD89 | −1.40 | 0.76 | 0.70 | 0.58 | −0.22 | RNU4-51P | 0.70 | 0.44 | −0.76 | −0.13 | −0.58 | RNA5SP435 | 0.12 | −0.81 | 0.04 | −0.14 | 0.01 |
| NUTM2A | −0.88 | 0.29 | 0.74 | −0.17 | 0.11 | AJ011931.1 | 0.65 | −0.76 | −1.48 | 0.06 | −0.41 | AC005090.1 | −0.65 | −0.66 | 0.39 | 2.73 | 1.53 |
| MDGA2 | −1.15 | 0.20 | 0.19 | 0.30 | 0.20 | AL450996.1 | −0.88 | 0.55 | 0.37 | 1.47 | 0.89 | AC005912.2 | −0.08 | −0.09 | −0.19 | 0.15 | 0.05 |
| FIGN | −0.84 | 0.38 | 0.83 | 0.12 | 0.54 | AC019205.1 | −0.24 | −0.11 | −0.05 | −0.01 | 0.20 | MTCO2P20 | 0.42 | −0.62 | −0.84 | 0.20 | −1.19 |
| LSM1 | 0.68 | −0.26 | −0.45 | −0.05 | −0.33 | AC020907.4 | 0.84 | −1.05 | 0.51 | −0.68 | 0.77 | AL031905.1 | 0.22 | −0.47 | 0.38 | 0.21 | 0.94 |
| CASKIN1 | −0.97 | 0.68 | 0.89 | 0.41 | 0.52 | AC027104.1 | −0.36 | 0.15 | −1.01 | 0.82 | −0.40 | IGLV1-40 | 1.02 | 0.98 | 1.01 | 1.59 | 0.59 |
| AKT2 | −0.33 | 0.17 | −0.02 | 0.18 | 0.03 | AC026725.1 | −0.56 | −0.84 | 0.82 | −0.02 | 1.45 | AC004023.1 | 0.31 | −0.03 | −1.95 | −0.05 | −2.71 |
| SMC3 | 0.55 | −0.28 | −0.36 | −0.21 | −0.22 | AC242426.2 | −0.70 | 0.21 | 0.51 | 0.20 | 0.16 | AP002439.1 | 0.12 | −0.35 | −0.24 | −0.23 | 0.37 |
| RPS27A | 0.68 | −0.12 | −0.27 | −0.07 | −0.58 | HNRNPA3P11 | −0.25 | 0.22 | 0.02 | −0.06 | −0.04 | RN7SKP231 | −0.75 | −0.58 | 0.08 | 0.54 | 0.30 |
| LRSAM1 | −0.60 | 0.40 | 0.34 | 0.29 | 0.09 | AC000003.2 | −0.39 | −0.27 | 0.32 | −0.19 | −0.26 | NUDT13 | −0.06 | 0.00 | 0.25 | −0.04 | 0.20 |
| CDC42SE2 | 0.48 | −0.18 | −0.25 | −0.03 | −0.21 | AC087854.1 | −0.36 | −0.31 | 0.23 | −0.28 | 0.13 | RNA5SP402 | 0.31 | 0.46 | −1.20 | 1.38 | −1.40 |
| RPL32P3 | −0.56 | 0.31 | 0.47 | 0.14 | 0.18 | RPL36AP15 | 0.43 | −0.14 | −0.51 | −0.48 | −0.37 | RPL12P12 | 0.12 | −0.63 | 0.95 | 0.14 | 1.46 |
| PSME2P2 | 1.58 | −1.01 | −0.82 | −0.46 | −0.56 | AC093591.1 | 0.72 | 0.23 | −0.29 | 0.33 | −0.13 | SNX19P1 | −0.51 | −0.30 | −0.88 | 0.23 | 0.33 |
| MPZL3 | 0.82 | 0.02 | −0.23 | 0.18 | −0.69 | RPL7P33 | 1.65 | −1.08 | −1.73 | 1.41 | 1.80 | AL450468.2 | 0.25 | −1.15 | −1.98 | 0.52 | 0.10 |
| AC093270.1 | 1.75 | −0.51 | −1.15 | −0.11 | −0.94 | RNU2-59P | 0.28 | 0.16 | −0.82 | 0.45 | −0.67 | AL109628.1 | −0.16 | −0.02 | −0.80 | 0.04 | −0.99 |
| DANCR | 0.79 | −0.13 | −0.41 | −0.11 | −0.34 | MTND1P34 | 1.09 | −0.73 | −0.17 | −0.41 | −1.05 | AC007448.2 | −0.13 | 0.66 | 0.06 | 0.53 | −0.03 |
| AC104825.1 | −0.84 | 0.92 | 1.16 | 0.46 | 0.30 | NDUFB8 | 0.22 | 0.04 | −0.06 | 0.20 | 0.03 | AC073621.1 | 0.16 | −0.43 | −1.22 | 0.13 | 0.10 |
| CMSS1 | 0.58 | −0.47 | −0.39 | −0.28 | −0.11 | AC124067.2 | 0.79 | −0.96 | −1.03 | −0.42 | −1.29 | AL135999.3 | −0.55 | 0.61 | 1.25 | −0.57 | 0.23 |
| LOXL4 | −0.56 | 0.29 | 0.18 | 0.17 | 0.11 | KRT8P9 | −1.15 | 0.82 | 1.18 | −0.62 | −1.72 | LTV1P1 | 0.19 | −0.64 | 0.47 | −0.01 | 0.82 |
| PPP1R3E | −0.66 | 0.27 | 0.73 | 0.13 | 0.37 | AC132825.3 | −1.32 | 0.80 | 1.01 | 0.33 | 0.41 | AC100830.2 | 0.13 | 0.27 | 0.28 | 0.02 | −0.25 |
| LTN1 | 0.48 | −0.14 | −0.26 | −0.11 | −0.19 | AC008759.2 | −1.00 | 0.54 | 1.32 | 0.49 | −1.18 | AC105316.1 | 0.18 | −0.62 | −0.08 | 0.16 | 0.72 |
| GDAP1 | 0.72 | −0.52 | −0.34 | −0.49 | −0.10 | CALB2 | −0.65 | 0.35 | −0.03 | 0.02 | −0.16 | AP002336.2 | 0.13 | 0.17 | 0.15 | 0.09 | 0.43 |
| PAK1 | 0.44 | −0.31 | −0.46 | −0.22 | −0.21 | AC004825.2 | −0.43 | −0.35 | 0.61 | 0.06 | 0.63 | KCNK9 | −0.18 | −0.23 | 0.53 | −0.26 | 0.33 |
| SLC9A1 | 0.52 | −0.20 | −0.55 | −0.11 | −0.09 | AC110792.3 | 0.60 | 0.25 | 0.52 | 0.43 | 0.15 | FO680682.1 | 0.18 | −0.56 | 0.73 | −1.00 | −0.22 |
| NTSR1 | 1.98 | −1.07 | −2.69 | −0.08 | −2.05 | RNU1-63P | −0.74 | 0.58 | 0.60 | 0.86 | 0.70 | SLC16A14P1 | −0.68 | 0.00 | −0.14 | 1.19 | −0.97 |
| LRAT | 1.51 | −1.42 | −2.22 | −1.18 | −1.15 | AC093297.2 | −0.19 | 0.15 | 0.65 | 0.04 | 0.25 | EBLN3P | −0.04 | 0.10 | 0.40 | 0.03 | 0.09 |
| AL359715.1 | −0.90 | 0.45 | 1.04 | 0.12 | −0.02 | AC092634.4 | −0.70 | −0.40 | 0.84 | −0.29 | 1.33 | AC103719.1 | −0.69 | 0.18 | −0.32 | 1.92 | −0.51 |
| AL928654.3 | −1.78 | 0.49 | 0.50 | 0.52 | 1.13 | KBTBD4 | 0.22 | −0.16 | −0.17 | 0.00 | −0.19 | AC007370.2 | −0.12 | 0.30 | 0.58 | −0.23 | −0.01 |
| MARF1 | −0.30 | 0.26 | 0.31 | 0.12 | 0.06 | P2RY10 | 0.68 | −0.75 | −0.04 | −0.55 | 0.13 | LINC00345 | −0.12 | −0.66 | −1.19 | −0.23 | −0.13 |
| PSMG3 | 0.65 | −0.23 | −0.45 | −0.09 | −0.29 | AC133565.1 | −1.02 | −0.43 | −0.60 | 0.17 | 1.06 | NAB1 | 0.05 | −0.01 | 0.19 | −0.04 | 0.00 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AL356599.1 | −0.51 | 0.38 | 0.63 | 0.16 | 0.29 | IRF8 | 0.36 | −0.69 | 0.15 | −0.57 | 0.74 | AC106872.13 | −0.23 | −0.91 | 0.57 | −0.14 | 0.11 |
| AC005840.3 | −1.65 | 1.67 | 0.60 | 1.13 | 0.18 | C15ORF31 | 0.51 | −0.11 | −0.93 | −0.05 | −1.06 | AC005303.1 | −0.48 | −1.58 | −0.54 | −1.20 | −0.51 |
| MORC4 | 0.36 | −0.23 | −0.27 | −0.03 | −0.12 | DDX11L9 | −0.93 | 1.44 | 1.14 | 1.53 | 0.64 | LINC01692 | −0.29 | 0.40 | −2.16 | 1.20 | −1.56 |
| RASGEF1C | −1.35 | 0.23 | 0.62 | 0.65 | 0.52 | PCM1 | −0.12 | 0.12 | 0.17 | 0.00 | −0.02 | LINC02037 | −0.41 | 0.41 | −1.64 | 1.28 | −0.47 |
| STAG3L5P | −0.74 | 0.26 | 0.40 | 0.24 | 0.64 | AC004817.1 | −0.58 | 0.69 | 0.74 | 0.12 | −0.16 | LINC01733 | 0.26 | −0.36 | −1.37 | 0.56 | −0.07 |
| MRPL54 | 0.73 | −0.07 | −0.57 | 0.23 | −0.32 | INTS1 | −0.16 | −0.03 | −0.22 | 0.18 | 0.10 | AL355834.1 | 0.28 | 0.19 | −0.77 | 0.59 | −1.45 |
| BBIP1 | −0.52 | 0.52 | 0.92 | 0.09 | 0.32 | OR2B8P | −1.28 | −1.30 | 1.07 | 0.45 | 1.29 | AC114763.2 | −0.12 | 0.07 | 0.24 | −0.47 | 0.28 |
| AC019322.4 | −2.23 | 1.62 | 1.66 | −0.66 | 0.59 | LANCL3 | 0.31 | −0.47 | −0.26 | 0.05 | 0.20 | AL021707.8 | 0.17 | −0.57 | −0.76 | −0.21 | −0.88 |
| FABP4 | −2.30 | 2.19 | 2.73 | 0.77 | −0.09 | MIR4266 | 1.12 | −0.26 | 0.42 | −0.42 | 1.32 | IGHV3-64 | 1.31 | −1.28 | −0.19 | −0.12 | −0.04 |
| CD276 | 0.64 | −0.39 | −0.69 | −0.24 | −0.42 | CERCAM | −0.34 | 0.27 | 0.68 | −0.48 | −0.18 | AL049820.1 | 0.11 | 0.00 | 0.03 | −0.12 | −0.01 |
| EFTUD2 | 0.36 | −0.35 | −0.58 | −0.05 | −0.12 | SMYD3-IT1 | −0.40 | −0.21 | 0.62 | −0.23 | 0.73 | PRR15 | −0.13 | 0.63 | −1.30 | 0.71 | −0.59 |
| KCTD1 | 0.62 | −0.01 | −0.24 | 0.12 | −0.11 | CHD3 | −0.12 | 0.03 | −0.05 | 0.02 | 0.04 | AL445647.1 | −0.26 | −1.20 | −2.51 | 0.29 | −1.98 |
| NIPAL1 | 1.10 | −0.11 | −0.22 | −0.10 | −0.56 | ESPL1 | 0.26 | −0.41 | −0.75 | −0.03 | −0.11 | AC103563.7 | 0.41 | −0.88 | 0.09 | 0.45 | 0.64 |
| GGT8P | 2.68 | −0.95 | −2.78 | 0.06 | −1.94 | AJ239328.1 | 0.45 | −0.99 | −0.99 | −0.07 | 0.13 | AL357054.2 | −0.16 | 0.32 | −0.14 | 0.16 | −0.56 |
| CXCL11 | 2.55 | −2.55 | −3.50 | −1.75 | −3.46 | AL355581.1 | 0.59 | −0.54 | −0.03 | 0.03 | 0.17 | AC006333.1 | 0.19 | −0.23 | −1.17 | −0.14 | −0.98 |
| ARNT | −0.32 | 0.22 | 0.54 | 0.04 | 0.18 | AC096733.2 | 0.53 | −0.10 | −0.55 | −0.16 | −0.35 | DDX53 | −0.25 | −2.09 | −1.10 | 0.99 | 0.81 |
| AC012020.2 | 1.08 | −0.94 | −1.16 | −0.16 | −0.02 | LINC01375 | −0.73 | 0.69 | −0.16 | −0.25 | −0.17 | RTN4RL1 | −0.09 | 0.38 | 0.08 | 0.25 | 0.21 |
| PRKD1 | −0.82 | 0.36 | 0.72 | −0.14 | −0.12 | RN7SL744P | −1.09 | 0.04 | 0.50 | −0.10 | 0.32 | HPD | −0.13 | −0.53 | 0.67 | −0.14 | 0.65 |
| DGCR9 | −1.14 | −0.10 | 0.55 | −0.50 | −0.05 | EVA1A | −0.32 | 0.11 | 0.12 | 0.06 | 0.35 | LINC01907 | −0.20 | 0.30 | −0.23 | −0.29 | −0.33 |
| KIAA1551 | 0.56 | 0.00 | −0.04 | −0.16 | −0.24 | MTRNR2L5 | −1.22 | −0.78 | 1.03 | −0.11 | 1.09 | MGAT4EP | −0.24 | −0.09 | 1.67 | −0.47 | 0.74 |
| PLA2G5 | −1.73 | −0.01 | 1.53 | 0.09 | 0.93 | DNAJC19P6 | 0.68 | −0.30 | 0.55 | 0.18 | 0.46 | LINC00624 | 0.07 | −0.34 | −0.03 | −0.25 | −0.16 |
| RPL6P27 | 0.77 | −0.42 | −0.34 | −0.22 | −0.10 | AC012078.1 | −1.28 | −0.24 | 0.39 | 0.31 | −0.96 | HSPE1P2 | −0.15 | −0.87 | 0.38 | −0.35 | 0.69 |
| ARL5AP2 | −2.48 | 1.08 | 2.18 | 0.59 | −0.92 | ALDH7A1P2 | 0.59 | 0.32 | 0.25 | 0.59 | −0.37 | RN7SL556P | −0.48 | −0.15 | 0.34 | −0.24 | 1.21 |
| SLC35E1 | 0.41 | −0.18 | −0.41 | −0.10 | −0.28 | C3orf14 | 0.27 | 0.03 | 0.31 | −0.25 | −0.12 | AC004386.1 | −0.32 | −1.10 | 2.06 | −0.95 | 2.20 |
| APOC1 | −1.64 | 0.70 | 0.94 | 1.00 | 0.84 | AC004241.3 | 0.63 | −1.22 | −1.55 | −0.12 | −0.68 | OR52M2P | 0.76 | −0.40 | −0.74 | 1.52 | −0.69 |
| DRG1 | 0.39 | −0.17 | −0.34 | −0.17 | −0.24 | NT5CP1 | −1.15 | 0.79 | 2.48 | −0.48 | 1.39 | AC007879.4 | −0.29 | −0.30 | 0.75 | −0.12 | −0.29 |
| MGC12916 | 1.22 | −0.87 | −1.23 | −0.04 | −0.20 | LRRK2 | −0.19 | 0.25 | 0.28 | 0.07 | 0.10 | MKRN1 | −0.04 | 0.17 | 0.12 | 0.07 | −0.15 |
| RGMA | −0.88 | 0.65 | 0.47 | 0.34 | −0.12 | AC009142.1 | 0.51 | 0.03 | −0.70 | 0.45 | −0.18 | AC079174.2 | 0.08 | 0.46 | 0.03 | 0.34 | −0.10 |
| AC009120.1 | −0.82 | 0.11 | 0.69 | 0.21 | 0.30 | BTN2A3P | −0.21 | −0.26 | 0.15 | −0.02 | 0.24 | SPARC | −0.09 | 0.27 | 1.03 | −0.52 | −0.25 |
| MAFTRR | −0.97 | 0.88 | 0.81 | 0.32 | −0.11 | SF3A3P2 | 0.76 | −0.46 | −0.59 | −0.01 | −0.57 | SPATA2P1 | 0.47 | −2.26 | −1.69 | −0.33 | −0.36 |
| HAGH | −0.58 | 0.43 | 0.21 | 0.38 | −0.01 | AC008555.8 | 0.51 | −0.38 | −0.37 | −0.25 | −0.44 | AC007663.3 | 0.17 | −0.44 | 1.25 | 0.02 | 1.17 |
| RPL22P1 | 0.72 | −0.39 | −0.21 | −0.28 | −0.22 | AC010201.1 | −0.66 | 0.47 | 1.74 | 0.21 | 0.57 | DPYSL4 | 0.10 | −0.54 | −0.47 | −0.67 | −0.71 |
| SIGLEC16 | −0.96 | −0.09 | 1.16 | 0.22 | 1.02 | AL022324.3 | 1.14 | −1.41 | −0.71 | −1.92 | 0.65 | RN7SKP240 | −0.30 | 1.17 | 0.78 | −0.74 | 0.39 |
| FCHO1 | −0.90 | 0.67 | 1.03 | 0.23 | 0.15 | CCT8L1P | −0.83 | 0.73 | −0.28 | 1.22 | −0.58 | AC012146.3 | −0.27 | 0.99 | 0.41 | 1.51 | 0.82 |
| SFI1 | −0.58 | 0.17 | 0.17 | 0.21 | 0.11 | LINCR-0001 | −0.32 | 0.19 | 0.15 | 0.11 | −0.02 | AC019070.1 | 0.14 | 0.08 | −0.10 | 0.27 | 0.52 |
| LINC01915 | −1.31 | 0.75 | 0.45 | 0.61 | −0.43 | HNRNPA1P1 | −1.00 | 0.73 | 1.39 | 1.46 | 0.69 | MIR5093 | 0.27 | −2.01 | −0.07 | 0.42 | 1.56 |
| AC072062.1 | 1.19 | −0.19 | −0.50 | −0.21 | −0.59 | RNA5SP289 | −0.79 | 0.15 | 0.09 | 0.10 | −0.13 | AC116655.1 | 0.34 | −0.63 | −2.46 | 0.29 | −1.04 |
| MRPL14 | 0.71 | −0.10 | −0.45 | 0.01 | −0.32 | ANGPT2 | 0.21 | −0.22 | 0.20 | −0.30 | −0.14 | GPX1P1 | 0.15 | −0.67 | 0.11 | −0.30 | 0.32 |
| PPP4R2 | 0.48 | −0.23 | −0.35 | −0.16 | −0.19 | AL500527.2 | 0.88 | −0.83 | −0.49 | −0.06 | 0.55 | MTRNR2L13 | −0.30 | 0.44 | −1.37 | 1.27 | −1.65 |
| HBB | −2.07 | 1.28 | 2.22 | 1.45 | −1.60 | SPECC1 | 0.24 | −0.22 | −0.49 | −0.13 | −0.30 | MIR4423 | −0.21 | −1.61 | −0.33 | 0.92 | 2.50 |
| IL1B | 2.02 | −3.07 | −2.07 | −0.47 | −0.71 | MIR4774 | 0.74 | −0.63 | −0.03 | −0.32 | 0.14 | MIR3663HG | 0.34 | −1.17 | −0.10 | −0.69 | 1.67 |
| NLGN1-AS1 | −1.42 | 0.02 | 0.19 | 0.13 | 0.63 | PSG10P | −0.70 | 0.50 | 0.10 | 1.06 | −0.56 | RNU6-1154P | −0.33 | 0.93 | 1.69 | −0.71 | 0.31 |
| FLJ37035 | −0.93 | 0.53 | 1.07 | 0.23 | 0.45 | AC133965.1 | 0.80 | −0.64 | −1.07 | −0.45 | −0.36 | AL020993.1 | 0.18 | −1.14 | 0.79 | 0.29 | 2.03 |
| EPB41L2 | −0.84 | 0.34 | 0.86 | −0.04 | −0.01 | ATP6VOC | −0.46 | 0.03 | 0.31 | 0.09 | 0.11 | SNORD112 | −0.05 | 0.00 | −0.04 | −0.22 | −0.34 |
| AL627230.4 | −1.45 | 0.36 | −0.04 | 0.75 | 0.06 | CTAGE7P | 0.41 | −0.23 | 0.39 | −0.01 | 0.68 | AC087878.1 | 0.16 | 0.74 | −0.59 | 0.78 | −0.71 |
| APOBEC3B | 1.22 | −0.80 | −1.79 | −0.31 | −1.62 | LINC01873 | −0.49 | 0.16 | 0.45 | −0.11 | −0.31 | RNU6-1245P | −0.31 | −0.30 | −1.33 | 0.00 | 0.40 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| SLC35F1 | −1.17 | 0.46 | 1.25 | 0.14 | 0.91 | AC009159.2 | 0.59 | −0.66 | −0.44 | 0.31 | 0.22 | RNU6-971P | 0.41 | −0.36 | 0.68 | −0.28 | 0.07 |
| ADSSL1 | −0.64 | 0.55 | 0.62 | 0.19 | −0.21 | SOX18 | 0.34 | −0.28 | 0.12 | 0.03 | −0.46 | AC108039.1 | −0.48 | 1.60 | −1.05 | 1.27 | −2.72 |
| CR769775.4 | −2.18 | 0.47 | 0.84 | 0.82 | 1.47 | AP001007.3 | −0.71 | 0.27 | 0.03 | 0.34 | 0.72 | AC131210.1 | −0.12 | 0.32 | 0.71 | 0.11 | −0.21 |
| AC004551.1 | 2.35 | −0.64 | −1.58 | −0.12 | −0.36 | RNU6-235P | −0.92 | −0.47 | 1.22 | 0.34 | 0.07 | AL354702.1 | −0.17 | 1.02 | 1.58 | 0.10 | −0.68 |
| AC245884.9 | −1.02 | 0.40 | 1.05 | 0.00 | 0.37 | LSMEM1 | 0.32 | −0.31 | −0.65 | 0.15 | −0.60 | HIGD1AP13 | 0.59 | −1.42 | −0.09 | −0.47 | 0.35 |
| G37087 | 2.32 | 0.78 | −2.05 | 0.80 | −1.58 | HMGN2P6 | −1.16 | 0.11 | 0.71 | −1.07 | −0.03 | AC098657.2 | 0.52 | −0.37 | −1.04 | 1.01 | 0.60 |
| AC007318.1 | 1.12 | −0.11 | −0.59 | −0.01 | −0.16 | NFE2 | 0.42 | 0.02 | −0.22 | −0.05 | −0.53 | MCHR2-AS1 | 0.33 | −2.04 | −0.77 | −0.09 | 0.60 |
| AC018647.1 | −1.37 | 1.08 | 1.75 | 0.44 | −0.02 | RTKN2 | 0.34 | −0.36 | −0.15 | −0.20 | 0.13 | MYH6 | −0.26 | −0.41 | −1.26 | −0.09 | −0.04 |
| SLC6A6 | 0.50 | −0.22 | −0.66 | −0.01 | −0.50 | AC009245.1 | 0.43 | −0.35 | −0.25 | −0.07 | 0.18 | AL353807.1 | 0.16 | −0.02 | 0.08 | −0.56 | 0.16 |
| RPL41 | 0.54 | −0.14 | −0.40 | 0.09 | −0.48 | AL079341.1 | −0.53 | 0.84 | 0.71 | 0.37 | −0.06 | NANOGP3 | −0.77 | −0.49 | 0.51 | −0.74 | −0.32 |
| AC004834.1 | −1.29 | 0.50 | 0.93 | 0.47 | 0.75 | AC019257.1 | −0.67 | 0.15 | −0.60 | 0.98 | −0.35 | AL158825.2 | 0.10 | 0.02 | 0.28 | 0.02 | 0.15 |
| FAHD2CP | −0.99 | 0.80 | 1.05 | 0.71 | 0.33 | NHLH2 | −0.50 | 0.89 | 0.37 | 0.64 | −0.62 | HTR1E | −0.37 | −1.79 | −1.08 | −0.94 | 0.93 |
| CCDC106 | −0.58 | 0.26 | 0.39 | 0.07 | 0.12 | AC004148.2 | −0.24 | 0.37 | 0.40 | 0.44 | 0.22 | AL136968.2 | −0.44 | 0.11 | 1.19 | 0.34 | 1.40 |
| MFSD8 | −0.34 | 0.25 | 0.43 | 0.24 | 0.16 | AL354943.1 | 0.41 | −0.24 | 0.05 | −0.16 | 0.08 | LINC00290 | −0.68 | 0.85 | −0.03 | −0.97 | −1.20 |
| CAPG | 0.61 | −0.32 | −0.97 | 0.00 | −0.64 | FOXJ1 | −0.49 | −0.55 | −0.60 | −0.16 | 0.21 | LINC02117 | 0.31 | −0.54 | −1.27 | −0.02 | −0.56 |
| AP005212.4 | −2.15 | 0.34 | 1.65 | −0.18 | 0.68 | GK5 | −0.18 | 0.20 | 0.18 | 0.19 | 0.17 | AC010524.1 | 0.19 | −0.38 | 0.53 | −0.47 | 0.46 |
| RBM17P1 | −1.51 | 1.20 | 1.04 | 0.65 | 0.02 | NIPSNAP1 | 0.17 | 0.02 | −0.22 | 0.10 | −0.12 | G3632 | −0.09 | 0.18 | 0.34 | 0.09 | 0.18 |
| RPS21 | 0.75 | −0.21 | −0.13 | −0.31 | −0.41 | AP001351.1 | −0.60 | 0.15 | 0.44 | 0.96 | 0.71 | DCAF12L1 | −0.35 | −0.22 | 1.67 | −0.75 | 1.76 |
| ARFGEF1 | 0.32 | −0.01 | −0.25 | 0.04 | −0.17 | KIF1C | 0.16 | 0.03 | −0.35 | 0.01 | −0.36 | AC133552.4 | −0.16 | 0.89 | 1.01 | 0.48 | 0.73 |
| MLC1 | −1.61 | 1.25 | 1.33 | −0.25 | −0.50 | RN7SL373P | −0.56 | −0.04 | −1.72 | 0.03 | −0.38 | NLGN4Y-AS1 | −0.25 | 0.05 | 0.84 | −0.48 | 0.44 |
| LETM1 | 0.52 | −0.41 | −0.71 | −0.07 | −0.09 | ABCC6 | −0.34 | 0.31 | −0.20 | −0.04 | −0.21 | DEFA3 | 1.29 | −2.62 | −0.72 | −2.38 | −1.15 |
| SPATA7 | −0.48 | 0.26 | 0.63 | −0.02 | 0.10 | AC005776.1 | 0.51 | −0.31 | −0.16 | −0.17 | 0.07 | GPAT4 | 0.03 | −0.08 | −0.18 | −0.03 | −0.06 |
| GINS4 | 0.70 | −0.78 | −1.03 | −0.21 | −0.11 | AL355916.1 | 0.45 | 0.01 | −0.25 | 0.07 | 0.15 | DIMT1P1 | −0.47 | −0.58 | 1.15 | 0.10 | 2.24 |
| MRGBP | 0.43 | −0.37 | −0.62 | −0.16 | −0.06 | AL121835.2 | −1.26 | −0.78 | −0.79 | 0.14 | 1.32 | INSL4 | −0.34 | −0.26 | 2.43 | 0.82 | 0.81 |
| SAT1 | 0.71 | −0.72 | −0.84 | −0.43 | −0.40 | AC080128.1 | −0.73 | −0.41 | 1.34 | −0.52 | −1.13 | LBP | −0.23 | −0.73 | −0.63 | 1.33 | −0.36 |
| ADIRF-AS1 | −0.84 | 0.49 | 0.13 | 0.26 | −0.12 | AC069234.5 | 0.60 | −1.01 | −1.17 | −0.63 | −0.69 | AC026348.1 | 0.10 | −0.06 | −0.74 | 0.45 | 0.14 |
| NKIRAS2 | 0.39 | −0.10 | −0.30 | −0.06 | −0.21 | AC131571.2 | −0.23 | −0.15 | −0.31 | 0.17 | 0.44 | IBSP | 0.26 | −2.02 | −0.14 | −0.94 | 0.75 |
| ANKRD20A5P | −1.15 | 0.40 | 0.71 | −0.32 | 0.18 | A1BG-AS1 | −0.53 | 0.15 | 0.98 | 0.42 | 0.41 | LINC02266 | 0.64 | −0.08 | 0.03 | −0.95 | −0.21 |
| AC010300.1 | −0.75 | 0.61 | 1.28 | 0.29 | 0.30 | MBLAC2 | 0.25 | 0.09 | −0.12 | 0.19 | −0.08 | RNU7-140P | 0.17 | 0.68 | 0.03 | 0.37 | −0.23 |
| RIMBP2 | −0.83 | 0.69 | 0.29 | 0.75 | 0.10 | MCUR1P1 | 0.22 | −0.14 | −0.11 | −0.05 | −0.03 | RAB32 | 0.08 | −0.04 | 0.03 | −0.33 | −0.43 |
| AL023775.1 | 1.11 | −0.80 | −1.36 | −0.22 | −0.29 | AC009065.6 | −1.31 | 0.53 | 0.77 | 0.84 | 1.12 | AGGF1P8 | −0.28 | −1.21 | 0.48 | −0.30 | 2.27 |
| CARM1 | 0.33 | −0.28 | −0.73 | 0.10 | −0.18 | RPS2P39 | 0.84 | −0.30 | 0.08 | −0.03 | 0.17 | HCG17 | 0.27 | −0.06 | −0.44 | 0.45 | −1.22 |
| AC016590.2 | −0.87 | 0.23 | 0.86 | 0.02 | 0.22 | PPP1R12A-AS1 | −0.30 | −0.29 | 0.68 | −0.44 | 0.01 | CPS1-IT1 | −0.30 | −2.07 | −1.12 | 0.15 | 1.25 |
| RP11-111G23.1 | −0.90 | 0.37 | 0.87 | 0.29 | 0.56 | LINC01780 | −1.01 | −0.15 | 1.87 | 0.96 | 1.10 | AC009318.4 | 0.14 | 0.77 | 0.17 | 0.25 | 0.18 |
| MTCO1P28 | −1.29 | 0.55 | 0.36 | −0.32 | −0.50 | RPS20P1 | −0.76 | 0.02 | 0.00 | −0.23 | 0.57 | AL451069.3 | −0.25 | 0.23 | 0.18 | 0.85 | 0.07 |
| PLA2G16 | −1.71 | 1.60 | 0.90 | 0.86 | −0.08 | AL353608.4 | 0.75 | 0.09 | −0.09 | 1.30 | 0.52 | IGBP1-AS1 | −0.12 | 0.60 | 0.03 | 0.47 | −0.27 |
| EMC8 | 0.65 | −0.37 | −0.63 | −0.11 | −0.17 | AC092436.4 | 0.44 | −0.17 | −0.49 | 0.23 | −0.43 | AP003071.4 | 0.14 | 0.01 | −0.52 | 0.16 | −0.80 |
| PLA2G3 | 1.03 | −0.49 | −1.54 | 0.23 | −0.76 | SH3GL3 | 0.44 | 0.07 | −1.04 | 0.76 | −0.94 | MTMR10 | 0.04 | 0.13 | 0.06 | 0.13 | 0.00 |
| EFCAB13 | −0.58 | 0.34 | 1.02 | −0.17 | 0.23 | HSP90AA2P | 0.35 | −0.22 | −0.30 | −0.20 | −0.03 | SNHG9 | −0.08 | 0.27 | 0.19 | 0.08 | −0.16 |
| PPP1CB | 0.53 | −0.11 | −0.39 | −0.04 | −0.34 | PCCA-AS1 | −0.28 | 0.25 | 0.35 | 0.31 | 0.27 | AC025277.1 | −0.36 | −0.26 | −0.25 | 0.63 | −0.33 |
| EIF3A | 0.51 | −0.33 | −0.55 | −0.17 | −0.23 | AF213884.1 | 0.98 | −1.12 | 0.12 | −0.36 | 0.74 | AC007394.1 | −0.32 | 0.69 | 0.25 | 0.51 | −0.37 |
| COL16A1 | −0.69 | −0.02 | 0.22 | −0.09 | −0.05 | EIF2B3 | 0.15 | −0.23 | 0.04 | −0.17 | 0.21 | RGL4 | −0.06 | −0.08 | 0.06 | −0.11 | 0.17 |
| ENPP3 | −0.85 | 0.44 | 1.10 | 0.32 | 0.52 | KDELR3 | 0.27 | −0.27 | 0.17 | −0.59 | −0.25 | LINC00466 | −0.19 | −0.44 | −0.81 | 0.38 | −0.93 |
| LGALS4 | −1.19 | 0.25 | 0.73 | −0.02 | 0.05 | RPL35P5 | 0.45 | 0.06 | 0.67 | −0.07 | 0.09 | KRTAP26-1 | −0.40 | −0.43 | 0.82 | −0.87 | 1.22 |
| RGS19 | 0.60 | −0.48 | −0.57 | −0.05 | 0.09 | G27940 | −1.33 | 0.70 | −1.70 | 1.15 | −1.38 | RPL22P12 | 0.22 | −1.82 | −0.77 | −1.09 | 0.39 |
| CNN1 | −1.35 | 0.38 | 0.77 | −0.06 | −0.15 | MXRA8 | −0.25 | 0.26 | 0.39 | −0.10 | −0.03 | SNORD64 | −0.59 | 0.73 | 1.96 | 1.69 | 2.42 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| RP11-435B5.5 | −1.19 | 1.18 | 1.03 | 0.78 | 0.40 | AKR1B1P6 | −1.68 | 0.39 | 1.12 | 1.53 | 0.76 | AC022558.2 | −0.11 | 0.28 | 0.56 | −0.29 | 0.16 |
| SNX18P12 | −1.80 | 0.50 | 1.96 | 1.53 | 2.14 | G36170 | 0.43 | −0.87 | −0.92 | 0.23 | 0.47 | SPDYE5 | −0.06 | −0.04 | 0.21 | −0.08 | 0.28 |
| LINC00921 | −0.85 | 0.40 | 0.83 | 0.33 | 0.41 | AL161751.1 | −0.92 | 0.07 | 0.26 | −0.35 | 0.48 | G31133 | 0.13 | −0.57 | −0.73 | 0.32 | −0.21 |
| RPS27P16 | −1.13 | 0.50 | 1.16 | 0.83 | 0.71 | AC109826.1 | 0.59 | −0.42 | −0.08 | −0.55 | −0.43 | MCM9 | 0.03 | 0.11 | −0.07 | 0.13 | −0.06 |
| AC232323.2 | 2.16 | −1.21 | −3.71 | −0.68 | −1.51 | AC008074.1 | −0.54 | −0.05 | 0.50 | 0.07 | 0.76 | AC018618.1 | −0.37 | 0.46 | −1.09 | 0.98 | −0.35 |
| RPL21 | 0.65 | −0.16 | −0.41 | −0.07 | −0.50 | PTPN5 | −0.51 | 0.07 | 0.38 | −0.20 | 0.35 | LINC00507 | 0.38 | −1.34 | 0.12 | −0.50 | 0.20 |
| OSBPL11 | 0.48 | −0.05 | −0.32 | −0.02 | −0.31 | MBNL1-AS1 | −0.24 | −0.07 | 0.29 | −0.02 | 0.12 | AC100774.1 | 0.11 | −0.02 | 0.24 | 0.11 | 0.18 |
| GAS6 | −0.53 | 0.42 | 0.37 | 0.31 | 0.09 | PNPLA4 | 0.22 | 0.03 | −0.09 | 0.11 | −0.10 | AC013429.2 | 0.18 | −0.41 | 0.59 | −0.30 | 0.18 |
| EIF3H | 0.54 | −0.11 | −0.23 | −0.08 | −0.29 | AL139095.4 | 0.62 | 0.01 | 0.88 | −0.24 | 1.19 | AC005632.1 | 0.34 | −0.57 | −1.56 | −0.43 | −1.48 |
| RASAL2-AS1 | −1.19 | 0.29 | 0.43 | 0.01 | −0.08 | KRT8P39 | −0.31 | −0.17 | −0.39 | 0.33 | 0.11 | OSBPL9P1 | 0.81 | 0.97 | −1.25 | 0.58 | −2.63 |
| ATP5F1A | 0.58 | −0.20 | −0.34 | −0.08 | −0.25 | RTL3 | −0.66 | −0.24 | 0.91 | −0.03 | 1.04 | AP003557.2 | 0.21 | −0.71 | −0.80 | −0.40 | −0.41 |
| AC005332.2 | −1.26 | 0.63 | 0.81 | −0.28 | −0.36 | SHLD2P1 | −0.62 | −0.63 | 0.86 | −0.18 | 1.09 | SIX5 | −0.08 | 0.18 | −0.17 | 0.17 | 0.05 |
| METTL7A | −0.70 | 0.46 | 0.80 | 0.15 | 0.21 | AC012184.3 | −0.40 | 0.31 | 0.24 | 0.47 | −0.14 | AL353691.1 | 0.19 | −0.20 | −0.73 | 0.01 | 0.26 |
| IFIH1 | 0.74 | −0.54 | −0.79 | −0.42 | −0.44 | PLEKHS1 | 0.44 | −0.03 | −1.06 | −0.20 | −0.75 | AL162734.1 | 0.19 | −0.42 | −0.06 | −0.78 | −0.08 |
| SPAG17 | −0.97 | 0.59 | 0.65 | 0.08 | 0.16 | HFM1 | −0.44 | −0.27 | 1.27 | −0.76 | 0.47 | NSD3 | 0.02 | 0.06 | 0.04 | 0.01 | −0.06 |
| AC134407.2 | −1.21 | 0.03 | −0.03 | 0.08 | 0.51 | C7orf69 | 0.96 | −2.79 | −0.91 | −0.26 | 0.74 | MIR563 | 0.39 | −1.70 | 0.06 | −0.88 | 1.43 |
| OR52D1 | −1.69 | 0.80 | 0.78 | 1.05 | 0.16 | AC079949.2 | 0.49 | −0.03 | −0.04 | 0.64 | 0.06 | AC090099.1 | −0.28 | 0.14 | −1.05 | 0.91 | −0.67 |
| AC083855.2 | 0.79 | −0.82 | −0.73 | −0.45 | −0.29 | RPL7P19 | 0.83 | −3.10 | −1.60 | −0.39 | 0.01 | AC016908.1 | 0.64 | −0.30 | −1.76 | −0.59 | −1.68 |
| NOD2 | 0.89 | −0.43 | −0.70 | 0.02 | −0.10 | CICP4 | −1.08 | 1.29 | 2.50 | 1.14 | 1.05 | RPL23AP61 | −0.37 | 0.53 | 0.58 | −0.44 | −0.56 |
| PER2 | −0.57 | 0.43 | 0.45 | 0.21 | −0.21 | BAG6 | 0.11 | 0.07 | −0.28 | 0.16 | −0.21 | FP565260.1 | −0.12 | 0.11 | 0.23 | 0.10 | 0.33 |
| CNR1 | −1.07 | 0.60 | 0.77 | 0.30 | −0.36 | AC010468.2 | 0.75 | −2.09 | −0.11 | −0.61 | 1.06 | HSD17B3-AS1 | 0.65 | −0.85 | −0.76 | 1.51 | −0.30 |
| FOXRED2 | 0.48 | −0.07 | −0.26 | −0.04 | −0.29 | AC103810.1 | −0.36 | 0.11 | 1.04 | 0.27 | 1.19 | SRRM1P2 | −0.70 | −0.42 | −0.08 | 0.22 | 0.62 |
| FCGBP | −1.56 | 0.33 | 2.16 | −0.15 | 0.87 | AL513123.1 | 0.68 | −0.94 | −1.11 | 0.21 | −0.43 | LINC01397 | −0.19 | −0.42 | −0.54 | 0.01 | −0.77 |
| CDC5L | 0.37 | −0.19 | −0.31 | −0.19 | −0.24 | RNA5SP397 | −0.70 | 1.10 | 1.52 | 0.53 | 0.24 | AC002375.1 | 0.35 | −0.04 | −0.28 | 0.69 | −1.35 |
| NIFK-AS1 | −0.58 | 0.36 | 0.65 | 0.15 | 0.19 | AC092910.3 | −0.28 | −0.26 | 0.25 | −0.23 | 0.16 | C2orf91 | 0.22 | −0.47 | −0.02 | 0.44 | 0.02 |
| FAM228B | −0.66 | 0.38 | 0.40 | 0.28 | 0.01 | DNLZ | −0.44 | 0.20 | −0.05 | −0.01 | 0.03 | AC090643.1 | 0.22 | 0.11 | −1.29 | 0.75 | −0.90 |
| PRCD | −1.09 | 0.36 | 0.75 | 0.45 | 0.33 | LGR4 | −0.20 | 0.33 | 0.14 | 0.21 | −0.07 | DYM | 0.02 | 0.06 | 0.04 | 0.01 | −0.04 |
| RNF10 | 0.29 | −0.11 | −0.40 | −0.01 | −0.32 | MIR381HG | 0.76 | 0.79 | 0.15 | 0.51 | −0.91 | PCDHA1 | −0.33 | 0.15 | −1.66 | 1.38 | 0.48 |
| STN1 | 0.51 | −0.13 | −0.09 | −0.10 | −0.07 | RNU6-264P | 1.67 | −0.12 | −1.35 | −0.11 | −1.80 | AL390728.2 | −0.09 | −0.13 | 0.25 | −0.05 | 0.03 |
| PHTF2 | 0.49 | −0.23 | −0.44 | −0.13 | −0.29 | AL513550.1 | −0.24 | 0.10 | 0.28 | 0.04 | 0.08 | FBXO3 | 0.03 | 0.14 | 0.11 | −0.02 | −0.11 |
| MAP1A | −1.06 | 0.55 | 0.99 | −0.11 | −0.10 | AC022447.1 | −1.57 | 2.10 | 0.84 | 0.24 | −1.10 | AL035401.1 | −0.26 | −2.07 | 0.29 | 0.05 | 2.52 |
| BAIAP3 | −1.00 | 0.39 | 0.44 | 0.31 | 0.30 | RBM48 | 0.11 | 0.08 | 0.04 | 0.18 | 0.00 | AC023237.1 | −1.21 | 0.13 | 0.03 | −0.56 | −1.36 |
| PYCR1 | 0.97 | −0.45 | −0.40 | −0.50 | −0.32 | AC011477.3 | −0.60 | 0.24 | 0.61 | −0.08 | 0.11 | AC079791.1 | −0.66 | −0.15 | 2.16 | −0.06 | −0.85 |
| NOL6 | 0.61 | −0.52 | −0.82 | 0.03 | −0.12 | HPR | 0.34 | −0.23 | −0.05 | 0.07 | −0.13 | AC004908.3 | 0.13 | 0.08 | 0.74 | 0.41 | −0.07 |
| SMO | −0.69 | 0.52 | 0.56 | 0.37 | 0.11 | AC009145.2 | 0.60 | 0.11 | −1.05 | −0.12 | −1.01 | AP003498.2 | 0.07 | 0.31 | −0.31 | 0.06 | −0.56 |
| ALPL | 1.46 | −0.54 | −0.86 | 0.41 | −0.48 | NUDC | 0.15 | −0.18 | −0.17 | −0.12 | 0.00 | AC090312.1 | −0.56 | 0.27 | 0.10 | 1.85 | −1.49 |
| GJB3 | 1.05 | −0.12 | −0.56 | −0.02 | −0.73 | SLC15A1 | 0.41 | −0.10 | 0.28 | 0.39 | 0.22 | OR2M5 | −0.31 | −0.28 | 0.27 | 0.56 | 2.07 |
| ETS2 | 0.65 | −0.47 | −0.69 | −0.06 | −0.20 | FOXP4-AS1 | −0.44 | −0.36 | −0.14 | 0.11 | 0.69 | AC138749.1 | −0.23 | 0.08 | −0.27 | 0.00 | −0.67 |
| SH2B1 | −0.57 | 0.23 | 0.24 | 0.25 | 0.20 | FNIP2 | 0.13 | 0.09 | −0.05 | −0.04 | −0.32 | AC009319.1 | −0.18 | 0.01 | −0.06 | 1.00 | 0.39 |
| AC010616.1 | −1.34 | 0.41 | 0.75 | 0.40 | 0.47 | AC006355.2 | −1.18 | 1.14 | 2.91 | 0.22 | −0.13 | AL513493.1 | 0.36 | −1.67 | −1.50 | 0.21 | −0.89 |
| EXOSC8 | 0.36 | −0.36 | −0.27 | −0.17 | −0.03 | LRP2 | −0.61 | 0.11 | −0.78 | 0.10 | −0.91 | DNAH8 | −0.15 | 0.47 | −0.47 | 0.41 | −0.72 |
| PPP3CB-AS1 | −0.50 | 0.17 | 0.46 | −0.03 | 0.21 | AC090772.4 | 0.89 | 0.45 | −1.84 | 0.79 | −1.82 | MARK2P11 | −0.53 | 0.22 | −0.02 | 1.75 | 0.62 |
| AC008267.1 | −1.78 | 1.62 | 1.69 | 0.59 | 0.42 | MT-ND4 | −0.28 | 0.11 | 0.18 | 0.00 | 0.06 | HIGD2B | −0.56 | 0.36 | −0.30 | −0.63 | 0.48 |
| SELENOF | 0.59 | −0.19 | −0.27 | −0.13 | −0.21 | AL049779.2 | 0.63 | 0.35 | −0.83 | 0.22 | −0.69 | GPR137 | 0.05 | 0.03 | −0.18 | −0.01 | −0.12 |
| AC006994.1 | −1.12 | 0.66 | 1.61 | 0.04 | 0.38 | AC022613.1 | 1.04 | −1.91 | −2.59 | −0.21 | −0.79 | AC242426.1 | −0.46 | 0.20 | −0.37 | 1.33 | −0.02 |
| SLC19A2 | 0.66 | −0.03 | −0.35 | 0.01 | −0.73 | PLD6 | −0.29 | 0.14 | 0.25 | 0.15 | 0.21 | AC022893.2 | −0.25 | −0.99 | −1.52 | 0.19 | 0.77 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| CLU | −1.18 | 1.03 | 1.17 | 0.39 | 0.13 | PCGF5 | −0.20 | 0.33 | 0.48 | 0.10 | 0.03 | PPIAP90 | 0.11 | 0.31 | 0.83 | 0.33 | 0.50 |
| RIBC1 | −0.70 | 0.44 | 0.46 | 0.21 | 0.15 | AC080100.1 | −0.64 | −0.50 | −0.96 | 0.35 | −0.33 | AC068672.3 | −0.48 | −0.94 | −1.77 | 0.31 | 1.00 |
| SIGMAR1 | 0.79 | −0.43 | −0.60 | −0.09 | −0.06 | AC100861.1 | 0.53 | −0.80 | −0.75 | −0.31 | 0.03 | LINC01643 | 0.45 | −1.50 | 1.16 | 0.37 | 2.21 |
| RCOR3 | −0.37 | 0.34 | 0.24 | 0.32 | 0.04 | CD226 | 0.45 | −0.62 | −0.15 | −0.20 | 0.20 | SLC25A30-AS1 | 0.29 | −1.05 | 1.53 | 1.00 | 1.94 |
| MIR503HG | 1.21 | −0.90 | −1.05 | −0.37 | −0.04 | RN7SL71P | −1.10 | 0.67 | 0.24 | 1.03 | 0.07 | AC025682.1 | 0.07 | −0.32 | 0.27 | 0.11 | 0.83 |
| DCD | −2.27 | 1.80 | 2.70 | 0.35 | 1.95 | AP001462.1 | −0.35 | 0.06 | 0.31 | 0.55 | 0.76 | AC108727.1 | −0.13 | 0.05 | −0.05 | 0.17 | −0.18 |
| DDAH1 | −0.57 | 0.17 | 0.96 | −0.35 | 0.17 | KRT84 | 0.79 | −0.26 | −2.11 | 0.05 | −1.61 | RNU6-877P | −0.13 | −0.24 | −0.14 | −0.31 | 0.23 |
| AC067945.1 | 1.07 | −0.71 | −0.56 | −0.46 | 0.08 | AL359881.3 | −0.73 | −0.71 | 0.23 | 0.62 | 0.52 | C16orf78 | −0.32 | −0.09 | −0.66 | 0.21 | −0.80 |
| DCTN4 | 0.35 | −0.08 | −0.30 | −0.02 | −0.21 | AC091152.2 | 0.86 | 0.21 | −0.56 | −0.17 | −1.36 | AC006538.3 | −0.26 | −0.08 | 1.28 | −0.13 | 0.78 |
| HERC2P9 | −0.50 | 0.20 | 0.32 | 0.34 | 0.37 | AC079075.1 | −1.04 | −0.13 | 0.11 | 0.66 | −0.26 | AC087499.5 | 0.45 | −1.45 | 1.81 | −0.70 | 1.30 |
| ANAPC2 | −0.56 | 0.34 | 0.18 | 0.38 | 0.13 | AL591888.1 | −1.43 | 0.61 | −1.18 | 1.80 | −0.11 | AC006026.1 | 0.39 | −1.32 | 0.48 | −1.55 | 1.49 |
| SCG2 | 1.88 | −1.26 | −1.41 | −0.49 | −1.54 | AC027020.2 | 0.29 | −0.46 | −0.21 | 0.17 | 0.88 | CCND2P1 | −0.69 | −0.44 | 0.38 | −0.06 | 0.77 |
| RN7SKP154 | 1.20 | −0.40 | −0.95 | 0.02 | −0.19 | ARHGEF37 | −0.23 | 0.23 | 0.19 | 0.23 | 0.29 | GPR141BP | −0.25 | −0.19 | 1.13 | 0.03 | 0.34 |
| FCGRT | −0.76 | 0.51 | 0.64 | 0.33 | 0.16 | DNAAF3 | −0.56 | 0.30 | 0.69 | −0.18 | 0.18 | AC096570.2 | 0.43 | 0.32 | −1.92 | 0.30 | −1.08 |
| MTM1 | 0.38 | 0.03 | −0.19 | 0.03 | −0.27 | HLA-C | 0.18 | −0.35 | −0.05 | −0.40 | −0.26 | AZIN2 | −0.05 | 0.09 | −0.11 | −0.01 | −0.17 |
| ASXL3 | −1.22 | 0.70 | 0.38 | 0.51 | 0.06 | NPIPB13 | −0.36 | 0.28 | 0.38 | 0.28 | 0.52 | AC010809.2 | 0.08 | −0.27 | −0.93 | 0.08 | −0.17 |
| ARSG | −0.54 | 0.37 | 0.72 | 0.13 | 0.39 | AL390754.1 | −0.36 | 0.10 | −0.08 | −0.05 | 0.18 | AL035555.1 | −0.43 | −0.87 | −0.53 | 1.15 | 1.38 |
| SORCS2 | 0.70 | −0.43 | −1.09 | −0.22 | −0.41 | AL121950.1 | −0.97 | 0.52 | −0.25 | −0.25 | −1.79 | AF254983.2 | −0.32 | −0.34 | −1.09 | 0.77 | −1.34 |
| AC126177.4 | −1.69 | 1.35 | −0.01 | 1.48 | −0.07 | MPPED2-AS1 | −0.95 | 0.66 | 0.80 | 0.61 | 0.20 | HNRNPA1P20 | −0.49 | 0.39 | 0.13 | 0.22 | −0.31 |
| AC145124.1 | −1.05 | 0.55 | 1.10 | 0.32 | −0.23 | HERC2P7 | −1.06 | 0.25 | −1.03 | −1.46 | −0.90 | RXFP1 | 0.17 | −0.15 | 0.43 | −0.53 | 0.27 |
| HMGN2 | 0.41 | −0.34 | −0.38 | −0.19 | −0.14 | AL589740.1 | −0.59 | −0.41 | −1.21 | −0.07 | −0.74 | AL132655.1 | −0.17 | −0.09 | 0.12 | −0.41 | 0.03 |
| AL359922.2 | 0.61 | −0.13 | −0.51 | 0.07 | −0.06 | KLHL22-IT1 | 0.45 | 0.45 | 0.37 | −0.31 | −0.44 | ANXA4 | −0.03 | 0.13 | −0.10 | 0.16 | −0.07 |
| FAM27A | −2.01 | 0.70 | 1.03 | 1.94 | 2.06 | AC073863.1 | 0.81 | −1.18 | −0.16 | −0.04 | 1.07 | SNORA4 | 0.20 | −0.02 | 1.21 | −0.12 | 0.96 |
| ATP5MC3 | 0.63 | −0.31 | −0.75 | −0.04 | −0.54 | LRRC74B | −0.61 | −0.76 | 0.64 | −0.69 | −0.33 | MDFIC | 0.06 | 0.09 | 0.19 | −0.25 | −0.29 |
| BHLHE40 | 0.64 | −0.07 | −0.83 | −0.01 | −0.57 | SIRT6 | 0.21 | −0.25 | −0.43 | 0.09 | 0.13 | ABCB10P1 | −0.35 | −0.91 | −0.52 | 0.78 | 1.00 |
| SCYL1 | 0.30 | −0.16 | −0.36 | −0.11 | −0.24 | CEP131 | −0.26 | −0.26 | −0.49 | 0.13 | 0.22 | AL035412.1 | −0.26 | 0.17 | −0.89 | 0.24 | −0.72 |
| G37465 | −1.31 | 0.01 | 0.48 | 0.11 | 0.96 | LAH1 | −0.14 | −0.10 | 0.05 | 0.01 | 0.08 | DNAJC5B | 0.26 | 0.07 | −0.06 | 0.97 | 0.44 |
| 1-Dec | 1.17 | −1.37 | −1.36 | −0.97 | −0.30 | OR5BD1P | −0.61 | −0.58 | 1.09 | −0.23 | 0.42 | SLC34A1 | 0.11 | −0.13 | −0.45 | 0.08 | 0.08 |
| LSM12 | 0.68 | −0.47 | −0.49 | −0.34 | −0.14 | ODF3B | 0.33 | −0.65 | −0.46 | −0.19 | 0.22 | AC021915.1 | 0.38 | −1.28 | −2.28 | −0.29 | −0.55 |
| BTBD7 | 0.43 | −0.08 | −0.13 | −0.11 | −0.17 | LINC00271 | −0.40 | 0.47 | 0.87 | 0.25 | 0.26 | AL353748.2 | −0.07 | 0.05 | 0.22 | −0.04 | 0.09 |
| ADAMTS17 | −0.73 | 0.47 | 0.10 | 0.18 | −0.29 | AC006499.3 | 1.24 | −0.73 | −0.44 | −0.82 | −0.51 | HSPA8P19 | −0.12 | −0.04 | 0.53 | 0.04 | 0.35 |
| KLHL33 | −1.41 | 0.47 | 0.56 | 0.56 | 0.03 | AC012485.3 | −0.58 | 0.52 | 1.54 | −0.57 | 0.11 | AC004522.1 | 0.63 | 0.19 | −1.20 | 0.02 | −1.51 |
| FAM160A2 | −0.49 | 0.23 | 0.45 | 0.16 | 0.26 | AC020661.2 | 0.56 | −0.47 | 0.01 | −0.32 | 0.71 | AL161908.2 | 0.43 | 0.27 | 1.53 | −0.45 | 1.27 |
| QRICH2 | −0.76 | 0.19 | 0.77 | −0.30 | 0.17 | RPS3AP46 | −0.82 | −0.10 | 1.30 | −0.50 | −1.44 | RN7SL51P | 0.49 | −0.24 | −2.10 | 0.09 | −0.57 |
| RN7SL9P | −1.38 | −0.08 | −0.07 | 1.29 | 0.75 | AP001267.2 | −0.66 | −0.70 | 0.75 | −0.12 | 0.92 | AC117569.1 | −0.40 | −0.76 | −0.27 | −0.43 | −0.58 |
| ARHGAP44 | −0.90 | 0.27 | 0.67 | 0.39 | 0.30 | AC018754.1 | −0.83 | −0.50 | 1.34 | −0.41 | 0.33 | SLC8B1 | −0.03 | 0.05 | −0.17 | 0.04 | −0.10 |
| C19orf53 | 0.60 | −0.23 | −0.56 | −0.07 | −0.57 | HSPD1P5 | −0.79 | 0.10 | −1.10 | 0.32 | 0.57 | RNU6-1294P | 0.18 | −0.35 | −0.21 | −0.02 | 0.22 |
| HIST1H4F | 0.95 | −0.48 | −0.39 | −0.14 | −0.15 | MICE | −0.40 | 0.20 | 0.25 | −0.03 | −0.38 | HTR1A | 0.35 | −0.64 | −1.39 | −0.11 | −1.60 |
| ASNSD1 | 0.51 | −0.08 | −0.31 | −0.04 | −0.31 | SNORA74 | 0.31 | 0.03 | −0.41 | −0.06 | −0.46 | ACOXL | 0.13 | −0.41 | −0.41 | −0.01 | −0.54 |
| SNX6 | 0.51 | −0.23 | −0.42 | −0.14 | −0.30 | AC138028.6 | −0.41 | 0.35 | −0.58 | 0.04 | −0.71 | AC069287.3 | −0.70 | −0.15 | 0.59 | −0.46 | 0.42 |
| CROT | 0.68 | −0.05 | −0.71 | 0.39 | −0.21 | RBSN | −0.08 | 0.15 | 0.03 | 0.10 | −0.04 | AL592156.1 | −0.50 | 0.44 | 0.20 | −0.29 | −0.93 |
| AC243562.2 | −1.12 | 0.82 | 0.79 | 0.30 | 0.04 | AL157791.1 | 0.38 | −0.42 | 0.13 | −0.03 | −0.26 | AC007256.1 | −0.09 | −0.04 | −0.02 | 0.03 | −0.18 |
| MRI1 | −0.58 | 0.12 | 0.20 | 0.32 | 0.30 | CASTOR2 | −1.39 | 1.68 | −1.79 | 1.80 | −0.57 | AP000560.1 | 0.06 | 0.31 | −0.17 | 0.15 | −0.19 |
| BCL2A1 | 1.87 | −2.35 | −2.40 | −0.46 | −0.44 | CASC4 | −0.21 | 0.13 | 0.37 | −0.17 | 0.00 | AC009264.1 | −0.23 | −0.21 | 0.54 | −0.26 | −0.43 |
| AMT | −0.96 | −0.04 | 0.67 | 0.24 | 0.42 | RABGEF1 | 0.17 | 0.20 | 0.07 | −0.05 | −0.13 | SLC35A5 | 0.05 | −0.03 | 0.05 | −0.04 | 0.00 |
| ADM2 | 1.26 | −0.11 | −1.85 | 0.18 | −1.21 | G10908 | −0.84 | 1.27 | 0.46 | 0.94 | −0.37 | BOLL | 0.12 | 0.07 | 0.04 | 0.27 | −0.14 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| SMCO2 | 1.27 | −0.86 | −1.40 | −0.22 | −0.32 | GABRG3-AS1 | −1.07 | 0.51 | −0.70 | 1.23 | −0.23 | HNRNPA1P62 | −0.12 | 0.51 | −0.12 | −0.02 | −0.47 |
| AC145423.2 | −1.35 | 0.18 | −0.12 | 0.58 | 0.08 | AL603839.3 | −0.40 | 0.17 | 0.61 | −0.14 | 0.01 | AP005059.1 | −0.16 | 0.43 | 0.78 | 0.93 | 0.47 |
| CEBPG | 0.42 | −0.06 | −0.37 | 0.00 | −0.28 | SLC25A30 | 0.13 | 0.09 | −0.22 | 0.06 | −0.15 | AC013553.2 | −0.15 | 0.30 | −0.55 | −0.05 | −0.49 |
| RPS6KB1 | 0.34 | −0.15 | −0.21 | −0.08 | −0.14 | AL034374.1 | −1.34 | 0.24 | −0.19 | 1.71 | −0.05 | RPS2P24 | −0.49 | −1.25 | 0.84 | 0.04 | 1.98 |
| ETNK2 | −0.91 | 0.56 | 0.50 | −0.01 | −0.23 | AC137056.1 | −1.18 | −0.81 | −0.85 | 0.18 | 0.76 | MIR377 | 0.55 | 1.15 | −0.15 | −0.27 | −0.75 |
| BTBD11 | 0.81 | −0.44 | −0.87 | −0.18 | −0.24 | RNU1-21P | −0.77 | −1.84 | −2.00 | 0.08 | −0.88 | MIR554 | −0.15 | 0.16 | 0.46 | 0.37 | 0.06 |
| GNB2 | 0.35 | −0.06 | −0.45 | 0.04 | −0.36 | RNU6-1226P | −0.54 | −0.17 | 0.80 | −0.15 | 0.64 | OARD1 | −0.04 | 0.18 | 0.14 | 0.24 | 0.14 |
| PRXL2A | 0.76 | −0.29 | −0.90 | 0.16 | −0.51 | MIR4762 | 0.76 | −1.03 | −0.13 | −0.44 | 1.16 | AL589765.7 | 0.33 | −0.43 | −0.96 | 0.06 | 0.44 |
| RPL27 | 0.63 | −0.26 | −0.14 | −0.30 | −0.32 | AC104304.2 | −1.01 | 1.20 | −0.68 | 2.03 | 1.48 | RASSF1 | 0.03 | −0.16 | −0.26 | −0.04 | −0.01 |
| GLA | 0.60 | −0.40 | −0.69 | 0.15 | −0.19 | AC007216.4 | −0.35 | 0.19 | 0.99 | −0.04 | 0.46 | AC022730.2 | −0.47 | −0.19 | 0.56 | −0.38 | 1.18 |
| RN7SL308P | −1.74 | 1.43 | −0.03 | 0.20 | 0.05 | RNU6-1318P | −0.47 | 0.23 | 0.19 | −0.52 | −0.82 | OR4A10P | 0.38 | 0.85 | −0.70 | −1.00 | −2.20 |
| DBN1 | −0.91 | 0.36 | 0.98 | 0.13 | 0.18 | AC023794.4 | −0.44 | −0.16 | 0.79 | −0.01 | 0.55 | LAMC1 | −0.06 | 0.07 | 0.21 | −0.26 | −0.27 |
| MAATS1 | −1.38 | 0.60 | 1.70 | −0.23 | 0.23 | LAIR2 | 1.09 | −0.83 | −2.11 | 0.40 | −0.30 | C12orf54 | −0.13 | −0.38 | −1.11 | −0.14 | 0.71 |
| RNU1-24P | −2.16 | 1.30 | 1.21 | 1.50 | 0.86 | CTSL3P | 1.29 | −2.12 | −2.55 | 0.50 | −0.30 | AC015660.1 | −0.17 | −0.01 | −0.40 | 0.36 | 0.10 |
| CCDC89 | −0.83 | 0.55 | 0.95 | 0.29 | −0.10 | ARMC4P1 | −0.66 | 0.31 | 1.83 | 0.93 | 1.03 | AC119403.1 | 0.16 | −0.17 | −1.11 | 0.02 | −0.72 |
| POLR2K | 0.64 | −0.29 | −0.30 | −0.12 | −0.23 | AC104435.2 | −0.95 | −0.47 | 2.70 | −0.78 | 2.02 | ARSK | 0.05 | 0.18 | 0.12 | −0.01 | −0.20 |
| GALR1 | −1.58 | 0.92 | 1.12 | 0.26 | 0.64 | RP11-417J8.3 | −0.47 | 0.98 | 0.17 | 1.03 | 0.94 | REEP6 | 0.08 | 0.58 | −0.01 | 0.94 | 0.22 |
| DCAF4 | −0.42 | 0.18 | 0.20 | 0.19 | 0.30 | AC006445.2 | −0.78 | 0.32 | 0.52 | 0.85 | 0.14 | AC012555.2 | 0.19 | −0.35 | −1.31 | 0.46 | −0.96 |
| NCBP2-AS2 | 0.59 | −0.16 | −0.28 | 0.07 | −0.28 | AC104237.3 | −0.83 | 1.60 | 2.07 | −0.13 | −0.66 | LINC00423 | 0.46 | −0.15 | −2.06 | 0.27 | −1.41 |
| EFNB1 | 0.64 | −0.26 | −0.97 | 0.06 | −0.56 | HLCS | −0.19 | −0.02 | 0.05 | 0.01 | 0.24 | NRXN2 | −0.09 | 0.19 | −0.08 | −0.05 | −0.28 |
| NUP107 | 0.33 | −0.28 | −0.45 | 0.03 | 0.03 | CDC42BPB | 0.09 | −0.09 | −0.20 | −0.03 | −0.04 | RNU1-146P | −0.20 | −0.41 | −0.85 | 0.75 | 0.10 |
| SMIM35 | 1.78 | −1.38 | −1.46 | −0.42 | −0.49 | COL15A1 | 0.32 | −0.32 | 0.53 | −0.64 | −0.08 | FGF20 | −0.37 | −0.42 | 0.78 | −0.36 | −0.60 |
| BEND5 | −1.14 | 0.90 | 1.05 | 0.39 | 0.16 | AL583842.3 | −1.08 | 0.19 | 1.29 | 0.60 | 0.76 | AC113618.1 | 0.66 | −1.50 | −1.56 | −0.63 | −1.75 |
| MYADML | −1.39 | 0.46 | −0.66 | 0.60 | −0.40 | AC100847.1 | 0.67 | −0.54 | −0.07 | 0.03 | 0.12 | AC064847.1 | −0.10 | 0.10 | 0.24 | 0.47 | 0.81 |
| BAALC-AS1 | −1.08 | 0.61 | 0.69 | 0.56 | 0.18 | AP003071.1 | −0.57 | 0.81 | −0.72 | 0.92 | −0.24 | AC069234.1 | 0.10 | −0.32 | −0.34 | 0.17 | 0.55 |
| AC005392.2 | 2.33 | −3.43 | −3.97 | −0.28 | −1.01 | RAC1P7 | 1.66 | −2.25 | −2.07 | −0.28 | −1.24 | LINC01324 | −0.58 | 0.43 | 0.14 | −1.03 | 0.36 |
| PRDX5 | 0.49 | −0.13 | −0.40 | −0.10 | −0.30 | ROR2 | −0.28 | −0.06 | −0.08 | −0.21 | −0.10 | SNORD1B | 0.19 | 0.30 | −1.10 | 0.68 | −1.01 |
| LAMA5 | −0.79 | 0.31 | −0.14 | 0.57 | 0.34 | AL008635.1 | 0.72 | −0.36 | −1.34 | 0.81 | −1.13 | CPT1B | 0.10 | −0.65 | −0.79 | −0.19 | 0.74 |
| HEXA | −0.41 | 0.20 | 0.19 | 0.10 | −0.03 | BX284668.5 | −0.56 | −0.69 | −0.64 | 0.81 | 0.95 | IFI27L1 | −0.05 | −0.09 | 0.17 | −0.20 | 0.01 |
| INAFM2 | 0.71 | −0.36 | −0.33 | −0.18 | −0.38 | FGFR1OP2 | 0.14 | 0.00 | 0.07 | −0.12 | −0.09 | LINC01039 | −0.61 | −0.80 | 0.88 | −1.02 | −1.18 |
| BPGM | 0.63 | −0.13 | −0.29 | −0.23 | −0.57 | DOCK11P1 | −0.69 | −0.22 | −0.36 | −0.58 | −0.87 | AC048341.2 | 0.09 | 0.10 | −0.14 | 0.17 | −0.08 |
| MID1 | 0.59 | −0.19 | −0.77 | 0.15 | −0.21 | RP11-353N4.4 | −0.43 | 0.04 | −0.09 | 0.84 | 0.36 | MTND3P5 | 0.47 | −1.40 | 0.06 | 1.14 | 2.42 |
| SESN2 | 0.63 | −0.34 | −0.64 | −0.37 | −0.47 | AL353748.1 | 1.28 | −1.78 | 0.75 | −1.08 | 0.34 | AIMP1P2 | −0.61 | −0.47 | 1.94 | −0.53 | 0.68 |
| HIST1H4K | 1.30 | −0.40 | −0.67 | −0.24 | −1.01 | CYP4A26P | −1.81 | 0.11 | 2.49 | −0.49 | 0.28 | AL121578.2 | 0.61 | −1.57 | 0.38 | 0.70 | 2.78 |
| LPAR1 | −0.92 | 0.31 | 1.33 | −0.34 | 0.51 | AC012370.2 | −0.62 | 0.41 | −0.42 | 0.74 | −0.15 | LINC01234 | −0.20 | −0.08 | −1.37 | 0.63 | −0.55 |
| FAM110A | 0.79 | −0.08 | −0.35 | 0.04 | −0.35 | CEP19 | 0.35 | −0.50 | −1.09 | −0.10 | −0.31 | RN7SL422P | 0.36 | −0.87 | −0.26 | 1.29 | 0.22 |
| MRPL28 | 0.47 | −0.42 | −0.81 | −0.08 | −0.18 | C1orf198 | −0.20 | 0.21 | 0.32 | −0.13 | −0.23 | ANKRD26P2 | 0.38 | −0.76 | −1.29 | 0.05 | −1.04 |
| KLF3 | 0.51 | 0.17 | −0.20 | 0.05 | −0.50 | RNU6-37P | 0.31 | −0.26 | −0.15 | −0.36 | −0.36 | FITM1 | −0.16 | 0.34 | −0.08 | 1.10 | −0.10 |
| BRIX1 | 0.63 | −0.46 | −0.50 | −0.14 | −0.26 | STC2 | −0.35 | −0.32 | −0.51 | −0.06 | −0.34 | HMGB1P8 | 0.07 | −0.25 | −0.46 | 0.20 | −0.04 |
| MAP2K5 | −0.33 | 0.29 | 0.31 | 0.21 | 0.17 | GAK | −0.15 | −0.04 | −0.24 | 0.09 | 0.06 | CYP2B6 | −0.18 | 0.12 | −0.18 | 0.02 | −0.34 |
| KYAT1 | −0.77 | 0.20 | 0.40 | 0.34 | 0.25 | SNX24 | 0.17 | 0.05 | −0.16 | 0.14 | −0.19 | OR5M2P | 0.24 | −1.20 | −0.26 | 0.76 | −1.14 |
| LINC01088 | −1.31 | 0.51 | 0.83 | 1.14 | 0.09 | SLC10A4 | −0.59 | 0.17 | −0.32 | 0.15 | −0.80 | LINC02002 | 0.52 | −1.97 | 0.09 | −1.84 | 0.09 |
| ROBO1 | 0.52 | −0.23 | −0.47 | 0.09 | −0.20 | RPL9P30 | 0.51 | −0.46 | −0.16 | −0.06 | 0.23 | AL138826.1 | 0.32 | 0.66 | −1.61 | 1.00 | −0.74 |
| AC092809.2 | −1.23 | 1.06 | 1.16 | 0.72 | 0.54 | RPL3P4 | 0.24 | 0.22 | 0.23 | −0.08 | −0.18 | NOS2P3 | 0.44 | −0.80 | −0.78 | −0.34 | −0.52 |
| RPL23AP77 | 2.23 | −0.49 | −2.32 | 1.17 | −0.55 | LINC01226 | 0.73 | −0.71 | −0.39 | −0.36 | −0.64 | RPL19P21 | −0.28 | −0.28 | −2.11 | 0.98 | −1.04 |
| MTHFD1 | 0.55 | −0.49 | −0.49 | −0.17 | −0.07 | AC104819.1 | 0.38 | 0.00 | −0.08 | 0.18 | −0.12 | RNU2-11P | −0.16 | −0.72 | −1.02 | −0.22 | 0.17 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| SRSF2 | 0.51 | −0.24 | −0.34 | 0.02 | −0.12 | DUSP5P1 | −0.67 | −0.89 | 0.52 | 0.60 | 2.67 | AC010401.1 | 0.13 | −0.29 | 0.05 | 0.47 | 0.36 |
| DNAJB1 | 0.52 | −0.01 | −0.68 | 0.01 | −0.69 | AC005828.5 | −1.07 | 0.12 | 1.14 | −0.02 | −0.28 | CDC42EP3 | 0.05 | 0.01 | −0.09 | −0.13 | −0.08 |
| AC087477.2 | −1.10 | 0.45 | 0.99 | 0.72 | 0.25 | CASC17 | −1.11 | −1.17 | −0.20 | 0.66 | 0.00 | PRKCD | −0.03 | −0.06 | −0.25 | 0.04 | −0.20 |
| CD80 | 1.58 | −1.16 | −1.52 | −0.80 | −1.03 | AC027018.1 | 0.40 | 0.19 | 0.37 | 0.08 | 0.03 | NEURL1-AS1 | 0.47 | −1.29 | −0.20 | 1.50 | 0.72 |
| SPINT2 | 0.84 | −0.16 | −0.75 | 0.21 | −0.33 | AC092828.1 | 0.23 | −0.04 | 0.06 | −0.09 | 0.08 | FXN | 0.05 | −0.09 | −0.11 | 0.16 | 0.21 |
| HERC2P2 | −0.60 | 0.24 | 0.44 | 0.10 | 0.23 | MKX | −0.47 | 0.90 | 0.30 | −0.66 | −1.08 | AL589946.1 | 0.72 | −1.21 | −0.91 | 0.02 | 1.17 |
| HYAL3 | 1.09 | −0.46 | −0.85 | 0.23 | −0.21 | OR6F1 | −0.61 | −0.13 | −1.06 | 0.20 | 0.57 | CYP4F9P | 0.52 | −1.31 | −0.81 | 0.97 | 1.73 |
| PTOV1-AS1 | −0.70 | 0.26 | 0.76 | 0.50 | 0.59 | AC011477.6 | −0.90 | 1.29 | 0.62 | 0.44 | −0.56 | AC008277.2 | −0.11 | −0.04 | 0.26 | −0.49 | −0.15 |
| AL592429.2 | −1.28 | 0.43 | 0.82 | 0.17 | 0.54 | AC012443.1 | 1.20 | −0.33 | −1.21 | −1.18 | −1.93 | AC012254.5 | −0.15 | 0.29 | 0.82 | 0.33 | 0.71 |
| PDLIM4 | −0.69 | 0.51 | 0.76 | 0.13 | 0.20 | DAND5 | −0.62 | −0.28 | 0.42 | −0.35 | 0.67 | DNAJB12 | −0.02 | 0.15 | −0.01 | 0.09 | −0.10 |
| MTERF4 | −0.58 | 0.15 | 0.44 | 0.14 | 0.18 | RN7SL396P | −0.44 | 0.09 | −0.46 | 0.38 | −0.65 | AC027176.2 | 0.13 | −0.06 | −0.53 | 0.34 | 0.33 |
| MED12 | −0.30 | 0.19 | 0.07 | 0.14 | 0.01 | CHMP4C | 0.27 | 0.33 | 0.18 | 0.16 | −0.62 | AL512604.2 | 0.67 | 1.53 | −1.75 | 0.24 | −3.43 |
| GPIHBP1 | −1.38 | 1.57 | 1.55 | 0.76 | 0.04 | SLC4A11 | 0.24 | 0.28 | −0.51 | 0.32 | −0.17 | NCOA4P4 | −0.33 | 1.14 | −1.15 | 1.40 | −1.75 |
| HMGXB4 | 0.32 | −0.25 | −0.43 | −0.12 | −0.25 | AL353768.2 | 0.38 | −0.03 | −0.18 | 0.06 | −0.43 | RNY4P8 | −0.11 | −0.38 | −0.06 | −0.72 | −0.69 |
| DZIP3 | −0.50 | 0.18 | 0.66 | −0.03 | 0.14 | G35422 | 0.73 | −0.08 | 0.22 | 0.45 | 0.68 | CCL26 | −0.22 | −0.47 | 0.09 | 0.12 | −0.18 |
| AC005264.1 | 0.95 | −0.51 | −1.28 | −0.30 | −0.48 | ANKRD54 | −0.14 | −0.08 | −0.32 | 0.12 | 0.05 | AC093642.1 | −0.39 | −0.91 | 0.24 | −0.85 | −0.28 |
| RNU6-942P | 1.41 | −0.88 | −0.78 | −0.26 | 0.12 | RGS3 | 0.22 | −0.44 | −0.58 | −0.30 | −0.15 | NOP56P1 | 0.23 | −1.26 | −1.63 | 0.51 | −1.20 |
| RBBP9 | 0.64 | −0.02 | −0.29 | 0.05 | −0.41 | AC015922.3 | −0.45 | −0.34 | 1.49 | −0.10 | 0.33 | AC009336.2 | −0.30 | 0.73 | 0.24 | 1.09 | −0.30 |
| ALG5 | 0.44 | −0.06 | −0.35 | −0.04 | −0.27 | HMGA1P2 | 0.41 | 0.65 | 0.17 | 0.19 | −0.45 | SLC6A6P1 | −0.37 | −0.30 | −1.28 | 0.97 | −0.33 |
| RNF180 | −0.60 | 0.47 | 0.89 | 0.18 | 0.26 | RNU6-62P | 1.54 | 0.65 | −1.49 | 0.87 | −1.00 | PSMC1P6 | −0.49 | −1.95 | 0.95 | −0.30 | 1.53 |
| AC092611.1 | 1.06 | −0.33 | −1.03 | 0.24 | −0.35 | G17177 | 0.81 | −1.10 | −2.35 | −0.20 | −1.59 | KIF4B | −0.15 | 0.38 | −0.62 | 0.45 | −0.05 |
| STAU2-AS1 | −0.71 | 0.09 | 0.53 | −0.05 | 0.48 | CACNA1B | −0.46 | 0.57 | 0.84 | −0.30 | −0.28 | AP000542.3 | −0.32 | −0.54 | 0.21 | −0.41 | −0.39 |
| JAK3 | 1.04 | −1.16 | −0.80 | −0.67 | −0.04 | AC091812.3 | −1.60 | −0.50 | 0.83 | 1.57 | 0.76 | KANSL1 | −0.03 | 0.06 | 0.09 | −0.02 | 0.21 |
| PKHD1 | −1.24 | 0.44 | 0.51 | 0.24 | 0.26 | CLCA4 | 0.42 | 0.25 | 0.62 | 0.45 | 0.60 | AL049749.1 | 0.66 | −0.40 | −0.85 | 0.02 | −1.74 |
| MIS18A | 0.68 | −0.42 | −0.37 | −0.10 | −0.04 | AC017007.5 | −1.23 | −0.21 | −0.29 | 0.24 | 1.32 | AC104123.1 | 0.11 | 0.47 | 0.27 | 0.04 | −0.05 |
| AC129915.3 | 2.67 | −1.23 | −3.11 | −0.02 | −2.39 | AC005154.4 | −0.39 | 0.48 | 0.38 | 0.04 | 0.17 | MAJIN | 0.14 | −0.80 | −0.74 | −0.34 | 0.49 |
| PRKG1 | −0.90 | 0.36 | 1.03 | 0.03 | −0.02 | RPL12P35 | 1.05 | −0.87 | 0.16 | −0.49 | −0.63 | AL162233.1 | −0.10 | 0.11 | −0.07 | 0.40 | −0.24 |
| AC107398.2 | 1.33 | −0.23 | −0.83 | 0.18 | −0.42 | RPS18P1 | 0.85 | −0.68 | −0.23 | −0.39 | −0.56 | AL592494.1 | −0.64 | −0.33 | −0.79 | 0.84 | −0.58 |
| LSM5 | 0.69 | −0.22 | −0.34 | −0.22 | −0.27 | AC073569.2 | 0.63 | −0.12 | −0.74 | −0.43 | −0.62 | REC8 | 0.07 | −0.27 | −0.53 | 0.03 | 0.27 |
| EIF4EP2 | 1.32 | −0.73 | −1.28 | −0.25 | −0.69 | SH3RF1 | −0.17 | 0.16 | −0.17 | −0.08 | −0.33 | OSBP2 | −0.05 | 0.17 | −0.22 | −0.19 | −0.44 |
| FOXD3-AS1 | −2.18 | 0.13 | 0.92 | 0.36 | 2.21 | CCNB3 | −0.42 | 0.11 | −0.22 | 0.34 | −0.48 | OR8C1P | −0.69 | 0.26 | 0.02 | −0.39 | 0.35 |
| AC006946.2 | −0.86 | 0.64 | 1.07 | −0.03 | 0.26 | KCTD18 | 0.16 | −0.03 | −0.07 | 0.16 | 0.02 | ASH1L-AS1 | 0.08 | −0.30 | 0.20 | −0.09 | 0.26 |
| KLF7-IT1 | 1.05 | −0.78 | −1.15 | −0.50 | −0.36 | AL162274.2 | −0.26 | −0.17 | 0.68 | −0.13 | 0.49 | RPL7P53 | −0.48 | 0.06 | 0.39 | 1.81 | 1.89 |
| AXL | −0.75 | 0.47 | 0.58 | −0.09 | −0.10 | AP000892.3 | −0.80 | −0.02 | 0.91 | −0.78 | −0.97 | LINC01778 | 0.23 | −0.20 | −1.04 | 0.47 | 0.65 |
| HIST1H2BL | 1.16 | −0.71 | −1.31 | −0.23 | −0.90 | MTCO3P29 | 0.42 | 0.12 | −0.19 | −0.20 | 0.07 | IGLV3-1 | 0.48 | 0.03 | 1.61 | 0.25 | −0.07 |
| RSPRY1 | 0.24 | −0.04 | −0.22 | 0.05 | −0.10 | OSBP | 0.10 | 0.04 | −0.06 | 0.00 | −0.12 | G3524 | −0.11 | 0.07 | −0.51 | −0.01 | 0.19 |
| AL590094.1 | −1.18 | 0.45 | 0.76 | −0.23 | 0.27 | DBET | −0.66 | −1.25 | 0.78 | 0.32 | 1.28 | AC003956.1 | −0.16 | 0.45 | 0.37 | 0.13 | 0.65 |
| SASS6 | 0.67 | −0.34 | −0.67 | −0.22 | −0.31 | AL031274.1 | −0.29 | 0.23 | 0.46 | −0.01 | −0.03 | COQ10A | 0.05 | −0.10 | 0.14 | −0.02 | 0.26 |
| AL158212.1 | −1.59 | 0.08 | 0.38 | 0.63 | −0.10 | PTPN23 | −0.14 | 0.11 | −0.20 | 0.20 | −0.03 | AL137230.1 | −0.30 | −0.68 | −1.23 | 0.22 | −0.33 |
| NLRP1 | −0.62 | 0.24 | 0.28 | 0.29 | 0.34 | RNASSP223 | −1.21 | 0.74 | 1.71 | 0.87 | 1.29 | AC139497.1 | −0.95 | 1.18 | 0.68 | 1.33 | −0.90 |
| ID1 | 0.73 | −0.34 | −0.99 | −0.10 | −0.58 | SPATA31C1 | 1.20 | −0.52 | −0.99 | 0.74 | 0.07 | RN7SL789P | −0.13 | −0.05 | 0.15 | 0.18 | 0.19 |
| LINC02145 | −1.47 | 0.18 | 0.80 | 0.77 | 0.81 | AL021368.1 | −1.30 | 2.11 | 1.99 | 0.80 | 0.53 | LHFPL3-AS1 | −0.13 | −0.06 | −0.63 | 0.26 | 0.13 |
| MAPK15 | −1.16 | 1.02 | 0.41 | 0.70 | 0.31 | AC018861.1 | −1.20 | 0.35 | 0.41 | 0.84 | 0.64 | RNA5SP201 | 0.13 | 0.38 | −0.70 | 0.26 | −0.86 |
| GOLGA7B | 0.80 | −0.42 | −1.16 | −0.05 | −0.31 | AP000688.1 | −0.39 | −0.08 | 0.41 | 0.37 | 0.45 | AC099567.1 | −0.52 | −0.35 | −1.86 | 2.04 | 0.53 |
| OSBPL3 | 0.45 | −0.26 | −0.57 | −0.11 | −0.20 | FCRL5 | 0.66 | −0.12 | 0.27 | −0.08 | −0.46 | AC122710.3 | −0.17 | −0.76 | 0.57 | −0.23 | 0.56 |
| EBF1 | −1.10 | 0.71 | 1.50 | 0.18 | 0.08 | AC092835.1 | −0.23 | 0.19 | 0.84 | −0.48 | −0.03 | AL157392.2 | 0.13 | −0.21 | −0.29 | −0.18 | 0.72 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| GMPS | 0.36 | −0.24 | −0.23 | −0.09 | −0.05 | CBX3P9 | 0.64 | −0.88 | −0.89 | −0.47 | −0.18 | DYNLRB1 | −0.04 | 0.24 | 0.14 | −0.08 | −0.30 |
| HARS | 0.36 | −0.11 | −0.43 | 0.02 | −0.23 | MIR4306 | 0.85 | −1.44 | −0.55 | −0.03 | 0.34 | AL158070.1 | −0.15 | −0.06 | −0.27 | 0.05 | −0.58 |
| GPR17 | −0.97 | 0.56 | 1.07 | 0.25 | 0.24 | RNU7-128P | 1.58 | −0.24 | −1.17 | −0.50 | −2.11 | LINC01724 | 0.40 | 0.54 | −0.53 | −0.21 | −0.72 |
| AC009542.1 | 0.92 | −0.58 | −1.17 | −0.09 | −0.29 | RNU6-1048P | 0.70 | 0.27 | −0.81 | 0.85 | −0.15 | RNU6-306P | −0.20 | −0.23 | −0.43 | 0.06 | 0.62 |
| NECTIN1 | 1.02 | −0.23 | −0.54 | 0.02 | −0.23 | SLC45A1 | −0.58 | 0.90 | 0.15 | 0.62 | −0.13 | AL121603.2 | −0.10 | 0.12 | −0.78 | 0.13 | −0.73 |
| RRAGC | 0.81 | −0.32 | −0.91 | −0.12 | −0.94 | SH2B3 | 0.18 | −0.29 | −0.19 | −0.25 | −0.08 | RN7SL398P | −0.10 | −0.39 | 0.36 | 0.23 | 0.51 |
| G22769 | −1.62 | 0.60 | 1.38 | 0.73 | 0.14 | OR7E89P | −1.13 | 1.31 | 2.02 | −1.02 | 0.40 | RPL21P4 | 0.28 | −0.67 | 0.34 | −0.39 | 0.37 |
| PIK3R1 | −0.57 | 0.39 | 0.69 | 0.22 | 0.30 | AL122035.2 | −0.29 | 0.59 | 0.07 | 0.85 | 0.31 | CICP8 | −0.84 | 0.10 | 0.76 | −0.40 | 1.61 |
| SGCE | −0.86 | 0.44 | 0.71 | 0.13 | 0.07 | MIR5194 | 0.47 | −1.49 | −1.33 | −0.14 | 0.00 | LINC01097 | −0.40 | −0.22 | −0.31 | 1.33 | −0.47 |
| RAB3D | 0.82 | −0.05 | −0.39 | 0.19 | −0.30 | AC034229.1 | −0.81 | −0.48 | 0.16 | 0.15 | 0.18 | NLRC3 | 0.09 | −0.60 | 0.39 | −0.36 | 0.70 |
| PCDHGB7 | −0.59 | 0.44 | 0.72 | 0.18 | 0.10 | PFN4 | −0.32 | −0.03 | 0.09 | −0.19 | −0.12 | AC005008.2 | −0.30 | −0.90 | 0.24 | −0.42 | 1.03 |
| ERICH1 | −0.55 | 0.15 | 0.33 | 0.18 | 0.17 | C17orf49 | −0.48 | 0.59 | −0.04 | −0.07 | −0.25 | AL365330.1 | −0.07 | 0.03 | 0.41 | 0.04 | 0.44 |
| KCNA1 | −1.49 | 0.35 | 0.16 | 0.74 | −0.51 | C18orf15 | −0.42 | −0.14 | 0.49 | 0.17 | 0.33 | ABRA | −0.10 | 0.22 | 0.08 | 0.51 | −0.41 |
| NRIP2 | −0.69 | 0.34 | 0.57 | 0.24 | 0.38 | AC007952.6 | 0.73 | −0.70 | 0.35 | −0.59 | −1.06 | LINC02561 | 0.27 | −0.48 | −2.46 | 0.05 | −1.45 |
| SGCD | −0.77 | 0.35 | 0.80 | −0.21 | −0.06 | C5orf34 | −0.17 | −0.25 | 0.05 | −0.26 | −0.03 | FAM167A-AS1 | −0.11 | 0.28 | 0.37 | 0.45 | 0.08 |
| ECC1L-ADORA | −2.21 | 0.18 | 0.68 | −0.10 | 0.71 | AL592528.1 | 0.65 | −2.21 | −0.58 | −0.45 | 0.16 | LINC00879 | 0.36 | −0.87 | −0.86 | −0.56 | −1.42 |
| AC021106.1 | 1.16 | −0.27 | −0.23 | 0.10 | −0.18 | AL034369.1 | 0.96 | 0.07 | −0.05 | 0.73 | 0.45 | GAPDHP45 | −0.39 | 1.47 | 1.74 | 0.93 | 0.96 |
| ABTB1 | −0.60 | 0.17 | −0.15 | 0.34 | −0.07 | MROH2A | −0.46 | −0.20 | −0.84 | 0.72 | −0.30 | PRPF38AP2 | −0.26 | −0.21 | −0.42 | 0.77 | −0.21 |
| AC132938.5 | −0.86 | 0.19 | 0.70 | 0.07 | 0.41 | AL512329.1 | −0.62 | −0.02 | −0.27 | 0.87 | −0.04 | AL160290.2 | −0.27 | 0.93 | 1.39 | 1.72 | 1.24 |
| PGM5P1 | −0.79 | 0.63 | 0.46 | 0.47 | 0.15 | DACH2 | −0.74 | 0.98 | 0.06 | 1.13 | 0.47 | MIS18A-AS1 | 0.11 | −0.59 | 0.04 | −0.19 | 0.57 |
| C21orf91 | 0.92 | −0.04 | −0.35 | 0.25 | −0.31 | CCAR2 | −0.16 | −0.01 | −0.17 | 0.12 | 0.01 | RNA5SP187 | 0.14 | 0.19 | 0.43 | 0.04 | 0.30 |
| AC018442.1 | −0.86 | 0.19 | 0.50 | 0.62 | 0.41 | FLJ20021 | −0.32 | 0.45 | 0.25 | 0.40 | 0.12 | AC100793.4 | −1.25 | −0.18 | 0.11 | −0.43 | 1.35 |
| BMP3 | −1.80 | 0.31 | 1.32 | 0.09 | 0.57 | RNA5SP160 | −0.52 | 1.12 | 1.48 | −0.17 | −0.04 | PPIAP87 | 0.28 | 1.30 | −1.43 | 1.05 | −2.21 |
| HIVEP2 | 0.50 | −0.27 | −0.59 | −0.05 | −0.41 | ISCA2 | −0.18 | −0.05 | 0.11 | 0.19 | 0.19 | MEG9 | 0.17 | 0.20 | 1.36 | −0.57 | −1.79 |
| GOLGA8H | −0.94 | 0.49 | 0.70 | 0.20 | 0.23 | AC104260.2 | −0.50 | 0.38 | 1.60 | −0.52 | −0.53 | AL161646.1 | 0.51 | 0.77 | 0.24 | −0.44 | −0.99 |
| G25251 | 2.71 | −1.12 | −2.85 | −0.65 | −0.12 | AP000346.1 | −0.51 | 0.78 | 1.05 | −0.02 | −0.11 | RP1-12G14.6 | −0.11 | 0.30 | 0.28 | 0.25 | 0.05 |
| ARHGAP20 | −1.33 | 0.97 | 1.23 | 0.37 | −0.15 | MIR760 | −1.14 | 1.52 | 1.99 | 1.34 | −0.88 | CTAGE6 | −0.08 | 0.00 | 0.51 | 0.06 | 0.29 |
| CD72 | −0.95 | 0.02 | 0.86 | −0.07 | 0.67 | AL646090.2 | −0.79 | 0.49 | −0.60 | 0.90 | −0.39 | OR10H5 | 0.19 | −0.54 | −1.09 | −0.04 | 0.05 |
| CENPQ | 0.66 | −0.38 | −0.52 | −0.35 | −0.40 | ASB8 | 0.21 | 0.14 | −0.07 | 0.06 | −0.21 | AC104073.2 | −0.28 | −0.53 | 1.95 | 0.70 | 1.78 |
| RABL2B | −0.48 | 0.16 | 0.47 | 0.11 | 0.34 | MICB | 0.36 | −0.77 | −0.31 | −0.14 | −0.45 | BNIP3P32 | −1.24 | −0.44 | −0.14 | −0.49 | −0.13 |
| LINC01866 | 2.93 | −0.68 | −1.20 | 0.12 | −0.34 | PPT2 | 0.29 | 0.35 | 0.29 | 0.07 | −0.32 | QCJ–SCHIP1-AS | −0.10 | −0.73 | −0.13 | −0.60 | 0.11 |
| CCL14 | −1.44 | 1.03 | 1.65 | 0.81 | 0.64 | RHOV | 0.29 | 0.11 | −0.11 | 0.15 | −0.08 | AC124944.2 | −0.08 | −0.64 | 0.51 | 0.01 | 0.84 |
| RN7SKP71 | −0.62 | 0.54 | 0.44 | 0.36 | −0.31 | BVES-AS1 | −0.61 | −0.36 | −0.76 | 0.35 | −0.75 | CYSLTR1 | −0.10 | −0.15 | 0.64 | −0.15 | 0.24 |
| RPL24 | 0.68 | −0.27 | −0.32 | −0.35 | −0.33 | RNU6-474P | −1.12 | 1.64 | −0.99 | 2.89 | −0.60 | PDCD7 | −0.03 | 0.00 | −0.07 | 0.12 | 0.19 |
| AC009242.1 | −0.83 | 0.51 | 0.12 | 0.48 | 0.17 | ANXA10 | 0.57 | −0.97 | −0.16 | −0.30 | 0.60 | AL451085.2 | −0.27 | 0.96 | 0.14 | 0.92 | 0.48 |
| AL022323.3 | 0.66 | −0.27 | −1.01 | −0.23 | −0.85 | ATP11C | 0.17 | −0.19 | 0.06 | −0.20 | 0.02 | AC244505.1 | 0.58 | −1.27 | −1.50 | −0.07 | −2.35 |
| RPL7A | 0.58 | −0.05 | −0.30 | −0.03 | −0.58 | HLA-DRB1 | 0.32 | −0.45 | −0.07 | −0.35 | 0.03 | SPEF1 | −0.21 | 1.11 | 0.20 | 0.26 | −0.46 |
| CSTF1 | 0.44 | −0.15 | −0.44 | −0.02 | −0.30 | IL9RP3 | −0.54 | −0.60 | 0.32 | −0.10 | 1.10 | RNU7-43P | 0.23 | 0.95 | 1.84 | −0.78 | −1.16 |
| NUP54 | 0.40 | −0.28 | −0.33 | −0.13 | −0.18 | CBX3P5 | 0.71 | −0.35 | 0.29 | −0.58 | −0.03 | MIR4698 | 0.29 | 0.80 | 0.29 | 0.05 | −0.39 |
| PCDHB4 | −0.99 | 0.71 | 0.90 | 0.00 | 0.21 | IL21R-AS1 | 0.89 | −1.25 | 1.04 | −1.04 | 1.30 | AC000111.1 | −0.60 | 0.16 | −1.22 | −0.67 | −1.08 |
| SCN9A | −0.98 | 0.36 | 0.46 | 0.31 | 0.25 | OR2M4 | −0.79 | −0.43 | −1.89 | 1.07 | −0.98 | C7orf50 | 0.03 | −0.05 | −0.10 | −0.14 | −0.05 |
| ATR | 0.38 | −0.23 | −0.37 | −0.05 | −0.04 | RN7SL181P | −0.46 | 0.33 | 0.31 | 0.40 | −0.07 | PPP3CB | 0.03 | −0.03 | 0.05 | −0.02 | 0.02 |
| CASK | 0.55 | −0.21 | −0.25 | −0.23 | −0.08 | LSM14B | −0.09 | 0.07 | −0.04 | 0.08 | 0.04 | RPL4P2 | 0.22 | 0.58 | −0.70 | 1.78 | −0.38 |
| LRRC56 | −0.95 | 0.39 | 0.31 | 0.53 | 0.23 | AL135786.2 | 0.77 | 0.38 | −0.11 | 0.77 | −0.72 | AC123912.3 | −0.26 | 0.21 | −1.22 | 0.61 | −0.96 |
| BCORL1 | −0.51 | 0.32 | 0.65 | −0.05 | 0.24 | AC092463.1 | −0.84 | −0.59 | 1.35 | −0.83 | 1.14 | RNU2-61P | −0.10 | 0.42 | −0.45 | 0.68 | −0.54 |
| SNORA42 | −1.26 | 0.40 | 0.38 | 0.54 | −0.31 | LSM3P2 | 0.58 | −0.59 | −0.59 | −0.52 | 0.33 | MRM1 | −0.06 | −0.33 | 0.14 | −0.23 | 0.27 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| FAF2 | 0.33 | −0.08 | −0.35 | −0.10 | −0.29 | ASB16-AS1 | −0.21 | −0.26 | 0.22 | 0.05 | 0.49 | AP000436.1 | 0.27 | −0.65 | 1.66 | −0.59 | 1.23 |
| SOAT2 | −1.46 | 0.63 | 1.62 | −0.16 | 0.16 | ANKRD34C | 0.83 | −1.65 | −2.07 | 0.08 | −1.37 | EEF1GP6 | −0.80 | 1.60 | 0.09 | 2.13 | −0.96 |
| G18534 | −0.72 | 0.52 | 0.83 | 0.17 | 0.46 | EVX1 | 1.46 | −0.53 | −1.28 | −0.74 | −1.95 | CACFD1 | 0.06 | 0.14 | −0.04 | 0.13 | 0.09 |
| NDUFB4 | 0.59 | −0.10 | −0.29 | −0.04 | −0.32 | PGBD4P3 | −0.85 | 0.66 | 0.17 | −0.20 | 0.22 | AL449214.1 | −0.10 | −0.13 | −0.27 | 0.25 | 0.32 |
| SNX18P15 | −1.11 | 0.40 | 0.67 | 0.53 | 1.06 | RNA5SP179 | 0.45 | −0.95 | −0.65 | −0.27 | 0.76 | AC010973.2 | −0.30 | 0.48 | 1.06 | 0.74 | 0.92 |
| CCDC25 | 0.49 | −0.23 | −0.35 | −0.11 | −0.25 | AC130650.2 | 0.30 | 0.05 | 0.06 | 0.08 | −0.11 | RNU4-36P | 0.22 | 0.92 | 0.91 | 0.40 | 0.17 |
| SLC25A25-AS1 | −0.67 | 0.16 | 0.21 | 0.22 | 0.52 | MBNL2 | 0.12 | 0.17 | −0.11 | 0.04 | −0.29 | MCAT | 0.04 | 0.04 | 0.28 | −0.13 | −0.04 |
| BX005266.2 | −1.38 | 1.12 | 1.27 | 0.44 | 0.22 | AC110926.1 | −0.53 | −0.56 | 0.13 | 0.32 | 0.28 | AL020994.2 | 1.24 | −0.05 | −1.22 | 0.17 | 0.05 |
| AC011472.5 | −1.34 | −0.02 | 0.50 | 0.59 | 1.05 | SCARB2 | 0.18 | 0.02 | 0.06 | −0.12 | −0.07 | LCE1F | −0.12 | 0.16 | 0.43 | 0.32 | −0.26 |
| CDH19 | −1.01 | 0.79 | 0.91 | 0.24 | 0.76 | CASP5 | 0.71 | −0.07 | −0.03 | −0.03 | −0.42 | AC093155.2 | 0.13 | 0.06 | 0.17 | 0.08 | 0.00 |
| G35614 | −1.88 | 1.53 | 2.21 | 1.72 | −0.25 | GDA | 0.44 | −0.32 | 0.27 | −0.11 | −0.11 | AC013410.2 | 0.29 | 0.67 | 0.40 | 0.37 | 0.84 |
| FER1L4 | −0.95 | 0.52 | 0.77 | 0.27 | 0.27 | SLC25A17 | 0.14 | −0.17 | −0.18 | 0.08 | 0.09 | SLA | 0.08 | −0.43 | 0.24 | −0.44 | 0.06 |
| AL355102.1 | 1.42 | −0.91 | −0.60 | −0.14 | 0.08 | RNU6-1177P | 0.60 | −0.35 | −0.44 | 0.05 | −0.34 | AL031726.1 | 0.42 | −0.49 | 0.22 | 0.39 | 0.90 |
| AC093110.1 | −0.89 | 0.72 | 0.90 | 0.46 | 0.29 | PARD6B | 0.21 | 0.21 | 0.02 | 0.05 | −0.37 | G36323 | 0.30 | 0.99 | 0.84 | 0.98 | 0.14 |
| GNRHR | 0.81 | −0.58 | −0.72 | −0.39 | −0.03 | AC093827.5 | −0.45 | 0.54 | 1.42 | −0.05 | 0.34 | AP005264.7 | −0.16 | −0.51 | −1.18 | 0.98 | 0.07 |
| LSAMP | −0.71 | 0.65 | 1.06 | 0.37 | 0.29 | AL645504.1 | 0.31 | −0.38 | −0.27 | −0.17 | 0.15 | AC079907.1 | −0.24 | −1.38 | −1.12 | −0.18 | 0.32 |
| NRBP1 | 0.33 | −0.07 | −0.20 | −0.18 | −0.30 | AL162311.3 | −0.31 | −0.05 | 0.16 | 0.91 | 0.92 | G31357 | 0.11 | −0.47 | 0.29 | 0.03 | 0.69 |
| G38643 | −2.86 | 0.93 | 2.05 | 2.02 | 1.64 | AP000233.2 | −1.06 | 1.24 | −1.20 | 1.54 | −1.52 | SFTAIP | −0.26 | −0.14 | 1.70 | −1.08 | −0.88 |
| AL356740.2 | −1.40 | 1.43 | 1.20 | 0.79 | 0.20 | BDNF | −0.34 | 0.47 | 0.62 | −0.01 | −0.34 | AC027328.1 | 0.37 | −0.91 | 0.39 | −0.26 | 0.05 |
| SP4 | −0.47 | 0.23 | 0.59 | −0.15 | 0.15 | AC113414.1 | −0.53 | 0.04 | −0.74 | 0.66 | −0.51 | HSDL1 | −0.03 | 0.00 | 0.14 | 0.00 | 0.04 |
| SNORD66 | −1.82 | 0.35 | 0.76 | 0.81 | −0.32 | AP002840.1 | −0.93 | 0.89 | 0.76 | 1.13 | −0.61 | MAGEB2 | 1.19 | −0.33 | 0.51 | −0.65 | 0.97 |
| AC011444.1 | −1.29 | 0.05 | 0.97 | 0.18 | 0.23 | RNU6-620P | −1.15 | 0.35 | 0.78 | 1.23 | 0.63 | SIRLNT | −0.39 | 0.45 | −0.78 | 0.60 | −0.94 |
| Clorf109 | 0.49 | −0.21 | −0.31 | 0.02 | 0.07 | AP000879.2 | −0.54 | 0.42 | −0.28 | 0.11 | −0.39 | AC017100.1 | 0.15 | −0.06 | −0.06 | −0.06 | 0.12 |
| OR9I1 | −1.31 | 0.83 | 0.54 | 0.43 | −0.57 | C2orf80 | −0.94 | 0.55 | −1.39 | 0.51 | −0.70 | LINC00588 | −1.24 | 0.76 | 0.96 | 0.07 | −0.65 |
| LYRM2 | 0.48 | −0.21 | −0.23 | −0.03 | −0.08 | GJA5 | 0.54 | −0.34 | −0.57 | 0.27 | −0.53 | AC114977.2 | 0.24 | −0.03 | 0.23 | −0.89 | −0.68 |
| STK24 | 0.45 | −0.05 | −0.48 | −0.02 | −0.30 | RPS4XP7 | −0.92 | −0.07 | 0.56 | 1.00 | 1.50 | AC112173.1 | −0.25 | 0.10 | 0.47 | 0.58 | 0.16 |
| G30851 | 1.57 | −0.70 | −2.63 | −0.27 | −0.94 | SNRPFP4 | 1.10 | −2.40 | −0.80 | −1.10 | 0.59 | MIR548AT | 0.22 | 0.33 | 0.53 | 0.41 | 0.06 |
| KRT12 | −1.54 | 1.28 | 1.97 | 0.15 | 0.12 | AC010999.2 | −0.65 | 1.16 | 0.17 | 0.94 | 0.04 | AC009965.2 | −0.49 | −1.28 | −1.16 | −1.69 | −0.76 |
| PTCH2 | −1.06 | 0.71 | 1.21 | 0.33 | 0.42 | RN7SL297P | −1.14 | −0.33 | −0.50 | 0.04 | −1.62 | AC074351.1 | 0.58 | −0.57 | −0.63 | −0.78 | 1.07 |
| LZTS2 | −0.51 | 0.23 | 0.17 | 0.30 | 0.16 | RNU6-1301P | 0.50 | −0.09 | 0.90 | −0.45 | 0.17 | AL445669.1 | 0.54 | −0.82 | −0.04 | 0.90 | 0.51 |
| AFF4 | 0.37 | −0.05 | −0.32 | −0.11 | −0.38 | BREA2 | −0.41 | 0.49 | −0.16 | 0.59 | 0.09 | KCNMA1-AS2 | −0.23 | −2.15 | −1.39 | −0.30 | 0.16 |
| B3GALT5 | −1.42 | −0.01 | 0.68 | 0.47 | 0.20 | CFL1P6 | −1.06 | 1.46 | 0.60 | 1.53 | 0.99 | AC019055.1 | 0.28 | 0.11 | −2.57 | 0.77 | −1.59 |
| OR1K1 | −1.34 | 0.44 | 1.02 | 0.88 | 0.08 | SALRNA3 | −0.72 | 0.30 | 1.19 | −0.29 | 0.48 | AL359885.1 | −0.11 | −0.10 | −0.53 | 0.26 | 0.04 |
| BLOC1S6 | 0.46 | −0.23 | −0.45 | −0.02 | −0.30 | ADGRF5P1 | 0.61 | 0.72 | −0.35 | −0.67 | −0.97 | AC074132.1 | −0.19 | 0.08 | −1.04 | 0.28 | −0.91 |
| RBFA | −0.34 | 0.25 | 0.02 | 0.20 | 0.03 | AC026992.2 | −0.60 | 0.50 | 0.33 | −0.20 | 0.34 | GCSHP5 | 0.11 | −0.18 | 0.23 | −0.23 | 0.23 |
| ACTN1 | 0.93 | −0.73 | −1.19 | −0.41 | −0.43 | AP006621.4 | 0.84 | 0.32 | −0.23 | 0.18 | 0.48 | PDILT | 0.31 | −0.92 | −1.68 | 0.87 | −2.24 |
| FKBP4 | 0.62 | −0.21 | −0.52 | −0.10 | −0.25 | PDLIM1P4 | −0.38 | 0.35 | 0.83 | −0.06 | 0.48 | AC245033.2 | 0.26 | −0.30 | −0.35 | −0.44 | −0.38 |
| CDCA3 | 0.77 | −0.77 | −1.02 | −0.51 | −0.14 | AC008738.4 | −0.98 | −0.54 | 0.41 | 0.53 | 0.69 | RNU6-228P | −0.43 | −0.87 | 0.53 | −0.63 | 1.29 |
| AC079781.1 | −1.14 | 1.18 | 1.44 | 0.25 | 0.66 | PDE1B | −0.24 | −0.23 | −0.29 | −0.09 | −0.02 | AC136604.3 | −0.13 | −1.17 | 0.63 | −0.29 | 1.55 |
| MYC | 0.67 | −0.22 | −0.99 | 0.11 | −0.34 | ABHD15 | 0.19 | −0.22 | −0.51 | 0.05 | −0.15 | GFER | −0.05 | 0.12 | −0.14 | 0.18 | −0.07 |
| AC012186.2 | −1.35 | −0.02 | 0.08 | 0.19 | 0.78 | MT-TP | −0.30 | −0.05 | 0.59 | −0.19 | 0.25 | AC116049.2 | 0.53 | −1.07 | −0.62 | 0.84 | −0.83 |
| AC007012.2 | −2.47 | 0.03 | 1.17 | −0.29 | 0.34 | LINC02560 | 0.49 | 0.22 | −0.58 | 0.14 | −1.08 | SAP30L-AS1 | −0.04 | −0.02 | 0.04 | 0.12 | 0.03 |
| NUDT8 | 0.87 | 0.07 | −0.59 | 0.29 | −0.52 | RNU6-1096P | −1.29 | 0.73 | 3.19 | −0.36 | 0.20 | C5orf17 | −0.18 | 1.60 | −0.40 | 1.69 | −0.46 |
| DRAP1 | 0.69 | −0.33 | −0.99 | −0.12 | −0.53 | AC131254.1 | 0.83 | −0.62 | −0.74 | −0.24 | −0.31 | MTHFD2P1 | −0.25 | −0.34 | 0.28 | 0.55 | 0.31 |
| C9orf106 | −1.25 | 0.05 | 0.60 | 0.19 | 0.20 | PTPRG-AS1 | −0.32 | −0.21 | 0.98 | −0.29 | 0.45 | POM121B | 0.06 | 0.11 | −0.30 | −0.02 | −0.26 |
| SLC35E1P1 | −1.02 | 0.27 | 0.46 | −0.36 | 0.51 | LINC00538 | −0.98 | −0.27 | −0.63 | 0.51 | −0.32 | AC016769.2 | 0.34 | −1.72 | −1.67 | 0.52 | 3.05 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| SPDYE18 | −0.97 | 0.63 | 0.62 | 0.25 | 0.36 | HES6 | 0.47 | −0.12 | −0.99 | 0.38 | −0.48 | AL022345.2 | −0.40 | 1.11 | 1.98 | −1.04 | 0.18 |
| AC027307.2 | −1.16 | 0.80 | 0.56 | 0.75 | 0.11 | AC015920.1 | −0.31 | 0.13 | 0.43 | 0.30 | 0.55 | SNORD111B | −0.13 | 0.02 | 0.80 | −0.22 | 0.14 |
| DUSP12 | 0.49 | 0.05 | −0.37 | −0.01 | −0.43 | PITPNA-AS1 | −0.79 | 1.08 | 0.30 | 0.66 | 0.43 | AL031656.1 | 0.28 | −0.16 | −0.90 | 0.11 | 0.02 |
| MRPS27 | 0.42 | −0.19 | −0.30 | −0.06 | −0.09 | G1730 | −0.60 | 0.42 | 0.43 | 0.15 | −0.54 | AL356804.1 | −0.29 | −0.95 | 0.34 | 0.75 | 0.15 |
| AC100854.1 | −0.89 | 0.60 | 0.55 | 0.67 | 0.45 | RN7SL517P | −0.40 | −0.11 | −0.57 | 0.31 | 0.12 | OSTM1-AS1 | 0.18 | −0.78 | −1.19 | −0.22 | −0.61 |
| SLC12A7 | −0.83 | 0.23 | 0.34 | 0.21 | 0.06 | RNF20 | 0.15 | −0.04 | 0.01 | −0.08 | −0.12 | LINC01173 | 0.64 | −0.69 | 0.73 | −0.66 | −0.22 |
| IRAK2 | 0.77 | −0.51 | −0.80 | −0.12 | −0.48 | LINC01993 | −0.64 | −0.93 | −0.76 | 0.43 | 0.72 | LINC01914 | 0.22 | −0.63 | 0.48 | −0.74 | −1.28 |
| KEAP1 | 0.41 | −0.20 | −0.41 | 0.05 | −0.12 | HTT | −0.11 | 0.09 | 0.02 | 0.20 | 0.08 | PCF11 | −0.02 | 0.08 | −0.04 | 0.00 | −0.05 |
| CD81-AS1 | −0.98 | 0.65 | 0.85 | 0.19 | −0.14 | AC022784.2 | −1.28 | −0.51 | 0.87 | −1.24 | −1.63 | LINC00856 | −0.11 | −1.12 | −0.02 | −0.38 | 0.47 |
| AC022726.1 | −1.25 | 0.07 | 0.45 | 0.04 | 0.59 | AL354710.1 | 0.50 | 0.45 | −0.03 | 0.29 | −0.32 | COX7BP2 | −0.14 | −0.53 | 0.41 | 0.09 | 0.49 |
| PLAGL1 | −0.61 | 0.25 | 0.93 | −0.04 | 0.21 | PTGES2 | 0.17 | −0.19 | −0.46 | 0.15 | 0.18 | AP001318.2 | 0.17 | −0.13 | 0.79 | −0.28 | 0.26 |
| GAB1 | 0.43 | −0.11 | −0.35 | 0.06 | −0.15 | ERVK9-11 | −0.34 | −0.06 | 0.61 | 0.57 | 0.64 | MIR93 | −0.36 | 0.86 | 0.98 | 0.11 | −0.08 |
| GPR79 | −0.88 | 0.59 | 0.71 | 0.26 | 0.29 | NPM1P42 | −1.06 | −0.11 | 0.79 | 0.27 | −0.72 | AC009093.2 | −0.08 | 0.04 | −0.10 | 0.24 | 0.38 |
| FGFRL1 | −0.74 | 0.46 | −0.02 | 0.00 | −0.18 | RNA5SP104 | 1.12 | −1.03 | −1.97 | 0.52 | 0.09 | AC131571.1 | 0.05 | −0.20 | 0.13 | −0.25 | 0.16 |
| GRAMD4 | −0.58 | 0.10 | 0.15 | 0.23 | 0.45 | RN7SL608P | −0.35 | 0.00 | −0.04 | −0.15 | −0.25 | LINC01498 | 0.25 | −1.42 | −0.52 | 0.05 | 0.39 |
| GALNT12 | −0.96 | 0.22 | 1.04 | −0.08 | 0.21 | SNX18P25 | −1.42 | 0.39 | 1.86 | −0.22 | 0.23 | AC079988.1 | −0.53 | −0.22 | 1.32 | 0.02 | 1.10 |
| ATE1 | 0.44 | −0.21 | −0.13 | −0.19 | −0.05 | RNU6-60P | 0.50 | 0.42 | −1.12 | 0.28 | −1.09 | RPL5P27 | −0.69 | 0.74 | 1.29 | 1.37 | 1.21 |
| RAD51B | −0.42 | 0.26 | 0.49 | 0.05 | 0.13 | AP003086.2 | 0.77 | 0.23 | 0.19 | 0.71 | 0.18 | AL117350.1 | 0.11 | 0.49 | 0.05 | 0.41 | 0.16 |
| C18orf21 | 0.56 | −0.33 | −0.78 | 0.04 | −0.26 | RESP18 | 1.41 | −1.98 | −1.18 | 0.12 | 0.92 | RNA5SP383 | 0.12 | 0.24 | −1.34 | −0.12 | −1.07 |
| CPPED1 | 0.50 | −0.16 | −0.44 | −0.13 | −0.31 | COX10-AS1 | 0.16 | −0.14 | −0.23 | −0.01 | 0.09 | AC243830.1 | −0.42 | −0.13 | 1.18 | −0.14 | 1.93 |
| EDIL3 | −1.01 | 0.94 | 1.30 | 0.12 | −0.15 | AC016542.2 | 0.37 | −0.37 | −0.18 | −0.49 | −0.15 | NLRP5 | 0.27 | 0.48 | −0.40 | 0.80 | −0.46 |
| ALDH1A1 | −1.01 | 0.58 | 0.55 | 0.50 | 0.20 | RPL23AP64 | 0.32 | −0.03 | −0.19 | 0.01 | 0.17 | NBR1 | −0.03 | 0.16 | 0.32 | 0.05 | −0.03 |
| AP000301.1 | −2.09 | 0.86 | 1.65 | 1.11 | 1.75 | CC2D1A | −0.17 | 0.18 | −0.13 | 0.26 | 0.04 | IGHV5-78 | −0.60 | 0.30 | 0.75 | 0.70 | 2.03 |
| HHAT | −0.54 | 0.54 | 0.89 | 0.15 | 0.13 | FAM118A | −0.17 | −0.01 | 0.29 | −0.19 | −0.17 | AC113404.1 | −0.39 | −0.31 | 0.63 | −0.05 | 0.76 |
| MAK | −0.54 | 0.40 | 1.02 | −0.28 | 0.19 | AC113349.1 | −0.55 | −0.16 | 0.97 | −0.31 | 0.33 | MOCS2 | −0.05 | 0.02 | 0.07 | −0.06 | 0.09 |
| AC016909.2 | 0.73 | −0.30 | −0.49 | 0.05 | 0.07 | SCDP1 | −1.03 | 0.43 | 0.85 | 0.83 | −0.48 | RP11-395P13.6 | −1.23 | 0.97 | 0.62 | 0.34 | −0.28 |
| POLD2 | 0.56 | −0.32 | −0.43 | −0.03 | −0.04 | RN7SKP29 | 0.66 | 0.05 | −0.18 | −0.07 | −1.16 | OR4C46 | 0.65 | −0.69 | −1.97 | 2.41 | −0.39 |
| AL807742.1 | −1.83 | −0.42 | −0.02 | 0.62 | 0.65 | AP001468.1 | −0.33 | 0.45 | 0.87 | 0.03 | 0.05 | AC010789.1 | 0.34 | −1.31 | 0.46 | −0.31 | 0.12 |
| AL162632.1 | −1.61 | 0.69 | 0.78 | 0.47 | 0.91 | MTND4P7 | −0.87 | 0.81 | −0.97 | 0.21 | −0.58 | LINC00603 | 0.25 | 0.18 | 0.34 | 1.13 | 1.02 |
| RYR1 | −0.74 | 0.36 | 0.39 | 0.55 | 0.17 | AL603914.1 | −0.49 | −0.01 | −0.32 | 0.12 | −0.05 | AC125616.1 | −0.36 | −1.15 | 0.74 | 0.03 | 1.38 |
| DNASE1 | −0.62 | 0.35 | 0.63 | −0.15 | 0.16 | AC005387.2 | 0.46 | −0.23 | 0.44 | −0.11 | 0.25 | CHD1L | −0.03 | −0.11 | −0.10 | 0.07 | 0.08 |
| CDS1 | 0.58 | 0.02 | −0.37 | 0.15 | −0.32 | EXTL2 | 0.18 | −0.09 | −0.12 | −0.05 | 0.12 | AC027544.3 | −0.46 | −1.84 | 0.35 | −1.35 | 1.26 |
| AC093225.1 | −1.05 | 0.57 | 0.84 | 0.58 | 0.62 | ETFA | 0.13 | 0.01 | −0.01 | −0.04 | −0.09 | DCAF5 | 0.02 | 0.08 | 0.07 | −0.02 | −0.03 |
| SS18 | 0.33 | −0.06 | −0.27 | −0.01 | −0.22 | AC109927.1 | −0.63 | −0.01 | 1.42 | −0.16 | 0.23 | ALG3P1 | −0.16 | −0.04 | 1.09 | −0.66 | 0.94 |
| SCHLAP1 | −2.16 | 2.13 | 2.71 | 2.13 | 0.20 | RPS20P33 | −0.42 | 0.13 | 1.04 | 0.29 | 0.22 | AC093433.1 | 0.13 | −0.49 | 0.16 | −0.24 | −0.39 |
| LINC01181 | 2.38 | −2.28 | −1.02 | −0.38 | 1.29 | AL359836.1 | 0.79 | −0.29 | −0.84 | −0.39 | −0.25 | AC138783.11 | −0.18 | −0.27 | 0.37 | −0.86 | 0.50 |
| PAAF1 | −0.37 | 0.03 | 0.06 | 0.02 | 0.17 | NT5C1B | 0.38 | −0.14 | 0.36 | −0.02 | 0.41 | AP000487.2 | 0.14 | 0.37 | −0.76 | 0.34 | −0.07 |
| AC013643.3 | −1.47 | 1.17 | 0.94 | 0.81 | 0.26 | GUK1 | 0.14 | −0.10 | −0.32 | −0.05 | −0.33 | AL365181.4 | −0.39 | −0.98 | 0.77 | −0.64 | 0.10 |
| PPM1K | −0.71 | 0.24 | 0.97 | −0.15 | 0.35 | AL365222.1 | 1.49 | 0.11 | 0.24 | 0.43 | −1.43 | FAM200B | −0.04 | 0.04 | 0.20 | 0.04 | 0.06 |
| BCLAF3 | −0.32 | 0.27 | 0.28 | 0.06 | 0.01 | RPL12P25 | −0.64 | −0.06 | 1.42 | 0.30 | 0.71 | NROB1 | −0.23 | −0.82 | 0.17 | 0.29 | 0.82 |
| RERE | −0.40 | 0.25 | 0.22 | 0.15 | 0.07 | G41275 | −0.34 | −0.22 | 1.14 | −0.06 | 0.71 | AC008125.1 | −0.38 | 0.45 | −0.43 | 1.80 | 0.42 |
| NEU2 | 1.62 | −0.58 | −1.17 | 0.14 | −0.98 | LTBP2 | 0.22 | 0.04 | −0.47 | −0.14 | −0.44 | RNA5SP190 | 0.23 | −0.86 | −0.72 | 0.06 | 0.63 |
| LINC02568 | −1.42 | 0.45 | 1.29 | 0.72 | 1.12 | CDKN2D | 0.22 | −0.22 | −0.25 | −0.20 | −0.28 | MS4A5 | −0.32 | −0.37 | 0.72 | −0.79 | 0.39 |
| C1orf43 | 0.46 | −0.17 | −0.36 | −0.15 | −0.42 | G36172 | 0.24 | −0.48 | −0.02 | −0.22 | 0.04 | AC017078.1 | 0.33 | −0.52 | −0.41 | 0.65 | −0.57 |
| G25302 | −1.83 | −0.16 | −0.01 | −0.03 | 0.55 | FANCF | 0.26 | −0.15 | 0.22 | 0.16 | 0.48 | AL358813.2 | 0.11 | 0.07 | 0.12 | 0.27 | 0.12 |
| CECR2 | −1.09 | 0.62 | 0.49 | 0.77 | 0.13 | SLC27A2 | −0.55 | −0.56 | 0.18 | 0.50 | 1.78 | AC005845.1 | −0.32 | −1.35 | −1.91 | −0.09 | 1.12 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC017007.2 | −1.39 | 0.51 | 1.41 | 0.47 | 0.26 | OR9K1P | −0.95 | 0.29 | −1.27 | 1.04 | −0.21 | ARFGAP3 | 0.04 | −0.02 | 0.08 | −0.15 | 0.07 |
| AP3M2 | 0.32 | −0.31 | −0.28 | −0.04 | 0.00 | SIAE | 0.11 | −0.19 | −0.04 | 0.03 | 0.09 | COG5 | 0.02 | 0.06 | 0.05 | −0.08 | −0.03 |
| CCDC50 | −0.47 | 0.28 | 0.42 | 0.08 | 0.12 | DUTP1 | 0.43 | −0.45 | −0.18 | −0.13 | −0.01 | AL161722.1 | 0.68 | −1.31 | −0.08 | −0.53 | −0.38 |
| MET | 0.67 | −0.28 | −0.77 | −0.17 | −0.58 | GAPLINC | −0.53 | 0.17 | −1.61 | 0.46 | −0.35 | FMNL1 | −0.07 | −0.55 | −0.17 | −0.36 | 0.18 |
| FZD8 | −1.06 | 0.65 | 0.87 | −0.26 | −0.09 | B3GALNT2P1 | −1.56 | 0.50 | 0.38 | 0.06 | −0.67 | NPIPA7 | −0.53 | 0.06 | −1.29 | 0.95 | −0.37 |
| RBFOX1 | −1.46 | −0.01 | −0.03 | 0.62 | 0.19 | AC026458.1 | −0.84 | −0.55 | −0.12 | 0.36 | 0.67 | RPL7P34 | 0.37 | −1.85 | 2.13 | −0.35 | 1.98 |
| ARF3 | 0.65 | −0.07 | −0.22 | −0.01 | −0.20 | MICAL2 | 0.17 | 0.05 | −0.03 | −0.04 | −0.15 | AC078962.4 | 0.37 | −2.37 | 0.13 | 1.21 | 1.01 |
| CCT8P1 | −0.87 | 0.99 | 1.49 | 0.52 | 0.54 | C12orf10 | 0.10 | −0.01 | 0.01 | 0.05 | −0.02 | MIR4765 | 0.56 | −0.27 | −0.91 | −0.56 | −0.83 |
| LRP5 | −0.47 | 0.22 | 0.05 | 0.31 | 0.17 | AL591368.1 | −0.69 | −0.31 | −0.20 | 1.00 | 0.43 | CTSH | −0.04 | 0.17 | 0.71 | −0.05 | 0.04 |
| ACTBP13 | −1.44 | 0.50 | −0.28 | 0.75 | 0.50 | FHL2 | 0.16 | −0.03 | −0.49 | −0.10 | −0.50 | AL122035.1 | 0.14 | −0.46 | 0.85 | −0.44 | 0.96 |
| GDI1 | −0.42 | 0.10 | 0.13 | −0.01 | 0.04 | PDK1 | 0.22 | 0.18 | 0.01 | 0.22 | −0.12 | HMGN2P7 | −0.41 | 0.22 | 0.33 | 0.32 | 1.06 |
| ACTRT3 | 1.22 | −0.85 | −1.22 | −0.64 | −0.65 | SPATA31B1P | −1.18 | −0.03 | 0.21 | −0.56 | 0.78 | AC006065.6 | 0.65 | 0.15 | 0.15 | −1.14 | −1.60 |
| SBF2-AS1 | −0.52 | 0.30 | 0.25 | 0.18 | 0.02 | CLEC4C | 0.84 | −0.44 | −1.16 | −0.51 | −0.30 | OR2AT4 | −0.19 | −2.32 | −0.61 | −1.02 | 0.09 |
| AC011595.1 | −0.85 | 0.56 | 0.90 | 0.12 | 0.16 | AC024075.3 | −0.35 | 0.43 | 0.27 | 0.32 | 0.13 | CD1C | 0.12 | −0.21 | 0.82 | 0.08 | 0.72 |
| FAS | 0.55 | −0.44 | −0.36 | −0.11 | −0.02 | AC007728.1 | 0.54 | −0.21 | −0.57 | 0.59 | −0.47 | GSTA10P | 0.43 | −1.00 | −2.17 | 1.25 | −0.63 |
| DPY30 | 0.49 | −0.09 | −0.05 | −0.14 | −0.25 | AP001476.2 | −1.21 | 1.02 | 1.25 | 0.01 | −1.55 | AC009021.2 | −0.23 | −1.80 | 1.26 | 0.01 | 3.90 |
| SLC44A1 | 0.70 | −0.01 | −0.26 | −0.01 | −0.52 | BOLA3P4 | −1.01 | 0.39 | 0.78 | 1.04 | 0.64 | CD40 | 0.05 | −0.25 | −0.33 | −0.12 | −0.19 |
| SCPEP1 | −0.61 | 0.47 | 0.88 | 0.28 | 0.12 | RNU6-272P | 0.45 | −0.12 | 0.08 | 0.25 | 0.28 | REG3A | 0.35 | −2.71 | −0.75 | 1.13 | 1.03 |
| NOS1AP | −0.93 | 0.47 | 0.72 | 0.51 | 0.28 | OR7E62P | 0.53 | −0.15 | −0.38 | −0.25 | −0.04 | RPS3AP9 | −0.43 | −0.76 | −1.21 | −0.21 | −0.59 |
| COMTD1 | 0.67 | −0.20 | −0.87 | 0.26 | −0.17 | MIR325HG | −0.79 | 0.56 | −0.86 | −0.20 | −1.00 | AC148476.1 | 0.27 | −0.10 | −1.09 | −0.32 | −1.27 |
| KRT8P13 | −2.11 | 0.55 | 1.14 | 1.77 | 0.81 | AL353662.3 | −0.67 | −0.17 | 0.83 | 0.22 | 0.19 | SPATA31D5P | −0.26 | −1.62 | −0.01 | 0.08 | 0.56 |
| MSS51 | −0.48 | 0.10 | 0.28 | 0.28 | 0.22 | AL158064.1 | −0.41 | 0.28 | −0.18 | 0.48 | −0.12 | DFFB | 0.06 | 0.20 | 0.01 | 0.01 | 0.06 |
| MIR4435-2HG | 0.84 | −0.79 | −0.83 | −0.55 | −0.42 | G18696 | 0.38 | 0.23 | 0.40 | 0.13 | −0.11 | AC090772.2 | 0.11 | −0.14 | 0.19 | −0.07 | 0.10 |
| LRCH2 | −1.13 | 0.58 | 1.50 | 0.21 | 0.10 | GOLGA7 | 0.19 | 0.15 | 0.19 | −0.06 | −0.31 | AC114956.3 | −0.09 | −0.33 | 0.29 | −0.26 | 0.19 |
| AC005524.1 | −2.10 | −0.21 | 1.90 | −0.41 | 0.19 | C17orf80 | 0.14 | −0.23 | 0.19 | −0.27 | 0.15 | AP001269.1 | 0.11 | −0.08 | 0.14 | 0.18 | 0.48 |
| SEL1L3 | 0.62 | −0.59 | −0.34 | −0.31 | 0.00 | DYNLL1P4 | −0.76 | 1.01 | 1.92 | 0.85 | 0.46 | AC079779.3 | −0.29 | −1.94 | −1.63 | −1.39 | 1.02 |
| NUP93 | 0.42 | −0.35 | −0.37 | −0.12 | −0.08 | IRS1 | 0.22 | 0.03 | −0.51 | 0.20 | −0.20 | HMGB1P48 | 0.70 | −1.63 | −0.35 | −0.08 | 1.17 |
| AC124068.2 | −1.41 | 0.66 | 0.33 | 0.88 | −0.22 | OSBPL9P5 | −0.89 | 1.45 | 0.68 | 1.87 | 0.42 | AC092474.1 | −0.53 | −0.20 | 1.06 | 0.60 | 0.35 |
| NTRK1 | 2.05 | −1.97 | −3.60 | −0.27 | −2.54 | AL390205.1 | −1.01 | 0.83 | −1.75 | 1.30 | −2.58 | LINC01541 | 0.26 | −1.18 | −1.50 | −0.83 | −2.59 |
| RPL7L1P2 | −1.07 | 0.96 | 1.02 | 0.10 | 0.19 | RPL5P5 | 0.59 | 0.38 | −0.51 | −0.24 | −0.57 | AC011471.3 | −0.17 | 1.22 | −0.88 | 0.17 | −0.95 |
| AL355483.3 | 1.83 | −1.76 | −1.59 | 0.08 | −0.40 | AC027644.4 | 0.53 | −0.58 | −0.56 | −0.58 | −0.02 | MTCO3P2 | −0.13 | 0.15 | 0.39 | 0.02 | 0.27 |
| RNF212 | −0.86 | 0.85 | 0.81 | 0.67 | −0.12 | AC104407.1 | −1.25 | 0.39 | 1.20 | 0.31 | 0.59 | AL596220.1 | −0.07 | −0.47 | 0.13 | 0.09 | 0.51 |
| EPDR1 | −1.09 | 0.75 | 0.56 | 0.49 | −0.29 | KRT8P42 | −0.49 | 0.39 | −0.47 | 0.85 | −0.01 | DKFZP434K028 | −0.27 | −0.81 | −0.56 | 1.99 | −0.54 |
| HIST2H2BF | 0.82 | −0.45 | −0.71 | −0.31 | −0.51 | SLC36A2 | −0.52 | −0.50 | 0.73 | 0.26 | 0.34 | SNORA25 | 0.08 | −0.51 | −0.12 | −0.23 | 0.34 |
| DENND5B | −0.77 | 0.49 | 0.65 | 0.19 | 0.14 | RPL7P56 | −1.01 | −2.61 | −0.09 | −1.34 | 1.36 | GOSR2 | −0.03 | 0.14 | 0.23 | 0.00 | 0.09 |
| SCAND1 | 0.58 | −0.12 | −0.73 | 0.24 | −0.45 | AP002444.1 | −0.82 | −0.58 | −0.43 | −0.19 | 0.16 | AC242376.2 | −0.20 | −1.92 | 1.61 | −0.69 | 0.80 |
| INTS6-AS1 | −0.73 | 0.02 | 0.64 | −0.03 | 0.18 | RPL37P6 | 0.70 | −0.61 | 1.11 | −0.52 | 0.94 | EEF1A1P27 | −0.36 | 0.39 | −0.47 | 0.36 | −1.69 |
| AL356121.2 | 1.59 | −0.85 | −0.95 | 0.08 | 0.28 | PCAT1 | −0.19 | 0.26 | 0.16 | 0.25 | 0.19 | EIF4A2 | 0.03 | −0.05 | −0.02 | 0.02 | 0.06 |
| HS3ST3B1 | 1.09 | −0.71 | −0.53 | −0.35 | 0.09 | OR10AC1 | −0.43 | −0.33 | 0.23 | −0.27 | 0.52 | AL031666.3 | 0.10 | −0.40 | 0.69 | −0.14 | 0.69 |
| NUAK2 | 0.67 | 0.03 | −0.76 | −0.03 | −0.74 | AC132219.1 | −0.95 | 1.62 | 1.94 | 0.37 | 0.49 | SNORD114-17 | 0.44 | 0.22 | 2.10 | 0.12 | 1.20 |
| POP7 | 0.55 | −0.11 | −0.38 | 0.05 | −0.36 | AC091697.1 | −1.13 | −0.03 | 0.31 | −0.14 | −0.75 | LINC01121 | 0.17 | −0.81 | −0.25 | −0.61 | −0.46 |
| RPRML | −2.00 | 0.65 | 2.36 | 0.01 | 0.68 | AC112693.1 | −1.21 | 0.65 | −1.16 | 0.81 | −1.17 | AP001542.3 | −0.10 | −0.05 | 0.28 | 0.23 | 0.47 |
| HNMT | −0.87 | 0.68 | 1.00 | 0.00 | 0.03 | AC022916.1 | −0.27 | −0.36 | 0.31 | −0.10 | 0.84 | HSPA8P9 | −0.26 | −1.00 | −0.58 | −0.56 | −0.76 |
| MIR205HG | 0.84 | −0.33 | −0.68 | 0.17 | 0.02 | AL121790.2 | −0.67 | 0.55 | 1.72 | −0.46 | 0.47 | AP001925.1 | −0.17 | 0.66 | −0.47 | 0.18 | 0.19 |
| LIPA | 0.70 | −0.47 | −0.61 | −0.07 | −0.26 | RN7SL487P | 0.62 | −1.12 | 0.24 | 0.16 | 1.11 | AP003027.1 | 0.21 | −0.72 | −3.35 | 0.27 | −2.40 |
| CYP1A1 | −2.01 | 0.38 | 0.88 | −0.14 | 0.01 | AL162457.1 | −0.78 | −1.22 | −0.41 | −0.51 | −0.37 | SNORA32 | −0.38 | 1.44 | 0.66 | 0.37 | −0.19 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| SPEG | −0.98 | 0.24 | −0.09 | 0.57 | −0.08 | G15152 | −0.79 | 0.69 | 1.45 | −1.31 | −0.41 | AL662791.1 | 0.41 | −0.79 | −0.19 | −0.67 | 0.08 |
| CD82 | 0.60 | −0.52 | −0.67 | −0.19 | 0.03 | AL158212.5 | −0.30 | 0.24 | −0.03 | 0.28 | 0.05 | G3262 | −0.35 | −0.05 | −0.16 | −1.75 | −2.62 |
| AC092903.2 | −0.75 | 0.05 | 0.36 | −0.52 | 0.03 | AC006504.8 | 0.54 | −0.44 | 0.47 | −0.83 | −0.05 | OR4F15 | 0.32 | 0.33 | 0.22 | 0.95 | −1.91 |
| HPCAL1 | 0.56 | −0.35 | −0.84 | 0.04 | −0.23 | CCDC39 | −0.21 | 0.12 | 0.18 | −0.09 | 0.04 | AC021146.10 | 0.53 | −1.29 | −2.20 | −0.31 | 0.21 |
| KITLG | 0.71 | −0.26 | −0.09 | 0.06 | 0.23 | CXXC5-AS1 | −0.53 | 0.55 | 0.77 | 0.58 | 0.21 | RN7SL449P | −0.18 | 0.15 | −0.65 | −0.47 | −1.41 |
| AL359091.1 | −1.22 | 0.47 | −0.20 | 0.82 | 0.00 | AC008758.4 | −0.81 | −0.93 | −0.93 | 1.75 | 1.08 | GPD2 | −0.04 | −0.09 | 0.18 | −0.24 | 0.13 |
| P3H3 | −0.81 | 0.43 | 1.01 | −0.42 | 0.12 | AC138965.1 | 0.89 | 0.91 | −1.53 | 0.40 | −1.05 | AC015813.3 | 0.20 | −0.65 | −1.63 | 0.20 | −0.12 |
| AC006273.1 | −1.43 | −0.45 | 0.63 | −0.03 | 1.06 | AP003721.1 | 0.77 | −0.18 | 0.10 | 0.24 | 0.42 | MTND5P29 | 0.37 | −1.25 | −2.21 | 0.61 | −0.35 |
| SLC22A5 | −0.60 | 0.39 | 0.54 | 0.29 | 0.36 | HMGB1P3 | 0.38 | −0.38 | 0.05 | −0.58 | −0.04 | AC005280.2 | 0.39 | −1.41 | −0.68 | −0.51 | 0.75 |
| PRPS2 | 0.51 | −0.38 | −0.38 | −0.24 | −0.13 | C3orf84 | −0.80 | 0.49 | 2.48 | 0.40 | 0.37 | POTEI | −0.30 | −1.98 | 0.40 | 0.38 | 2.04 |
| KYAT3 | 0.55 | −0.18 | −0.24 | −0.19 | −0.26 | AC090427.1 | −0.79 | 0.29 | −0.93 | 0.25 | −0.84 | AF146191.1 | 0.49 | −0.67 | −0.17 | 0.78 | −0.53 |
| KLF12 | −0.74 | 0.48 | 0.97 | 0.04 | −0.01 | ARID3A | −0.19 | −0.25 | −0.09 | −0.08 | 0.19 | OOSP1 | 0.27 | −2.11 | 0.38 | −0.84 | 0.37 |
| ARHGDIA | 0.54 | −0.47 | −0.95 | 0.05 | −0.28 | SLC35F5 | 0.18 | 0.02 | 0.16 | 0.05 | −0.03 | AP000977.1 | −0.16 | −0.64 | 0.30 | −0.84 | −0.09 |
| AC015961.2 | −1.45 | 0.97 | 0.97 | 0.71 | −0.14 | DDX3Y | 0.22 | −0.10 | −0.47 | 0.10 | −0.31 | LINC01103 | 0.37 | 0.55 | −0.23 | 0.20 | 0.06 |
| G5901 | −1.42 | 1.41 | 1.31 | −0.30 | 0.06 | MIR1245A | 0.49 | 0.09 | 1.41 | −0.63 | −0.02 | OR52N5 | −0.19 | −0.16 | 1.23 | 0.44 | 0.10 |
| SLC10A3 | 0.56 | −0.07 | −0.30 | −0.05 | −0.39 | RNU6-883P | −0.85 | 1.08 | 0.57 | 0.67 | −2.17 | SNORA48 | 0.09 | −0.13 | 0.35 | 0.12 | 0.32 |
| ATP5PD | 0.62 | −0.36 | −0.32 | −0.36 | −0.22 | AL024474.2 | −0.41 | 0.15 | 0.31 | 0.00 | 0.14 | SDHAF2 | 0.07 | 0.16 | 0.29 | −0.10 | −0.01 |
| HMGB3P7 | −1.49 | 0.79 | 2.16 | 0.75 | 0.53 | RNF214 | −0.14 | −0.01 | 0.17 | −0.11 | 0.04 | FAM57A | 0.07 | 0.26 | 0.24 | 0.15 | −0.12 |
| RFX3-AS1 | −0.63 | 0.19 | 0.58 | 0.28 | 0.81 | BRWD1-IT2 | −0.36 | 0.04 | 0.01 | 0.30 | −0.27 | CD209 | −0.11 | 0.23 | −0.04 | 0.23 | −0.24 |
| LINC02381 | −0.70 | 0.47 | 0.77 | 0.14 | 0.57 | SNAI1 | 0.49 | −0.28 | −0.30 | −0.63 | −0.80 | LINC01040 | 0.36 | −0.69 | −0.81 | 0.36 | −2.47 |
| POLRIA | 0.42 | −0.48 | −0.48 | −0.06 | 0.13 | PRMT2 | −0.10 | 0.10 | 0.18 | 0.10 | 0.04 | KLRD1 | −0.11 | −0.27 | 0.16 | −0.08 | 0.54 |
| SSNA1 | 0.49 | −0.02 | −0.64 | 0.21 | −0.36 | HOXC5 | −0.32 | 0.17 | 0.48 | 0.65 | 0.12 | AL158207.2 | −0.10 | 0.04 | −0.12 | −0.01 | −0.79 |
| GNB3 | −0.95 | 0.07 | 0.63 | −0.24 | 0.13 | JOSD2 | 0.17 | −0.08 | −0.19 | 0.01 | 0.01 | CACNAIE | 0.13 | −0.61 | −0.42 | −0.17 | −0.30 |
| HCFC1 | 0.46 | −0.28 | −0.51 | −0.02 | −0.08 | AC008592.2 | 0.57 | −0.02 | 0.16 | 0.06 | 0.67 | AC021818.1 | 0.44 | 1.31 | −1.52 | 0.90 | −2.44 |
| SLC16A11 | −1.12 | 0.49 | 0.69 | 0.30 | 0.37 | MIR4798 | 1.68 | −0.25 | −2.14 | −0.92 | −1.75 | CACNAIS | −0.19 | 0.41 | 0.44 | 0.72 | −0.38 |
| RDH5 | −0.88 | 0.77 | 1.02 | 0.57 | 0.54 | PPIAP72 | −0.37 | 0.43 | 0.28 | 0.40 | 0.20 | PLEKHA5 | 0.03 | −0.01 | −0.06 | −0.08 | −0.06 |
| ASAH2B | 0.60 | −0.46 | −0.49 | 0.17 | −0.03 | IGF2BP3 | −0.40 | −0.82 | 0.00 | −0.15 | 0.35 | LINC02509 | 0.58 | 0.12 | 0.25 | −0.50 | −2.30 |
| CTIF | −0.67 | 0.45 | 0.48 | 0.14 | 0.00 | SCNN1A | −0.24 | 0.70 | 0.53 | 0.49 | −0.06 | RNU1-87P | 0.12 | −0.61 | −0.36 | 0.23 | −0.03 |
| GRIN3A | −0.67 | 0.37 | 0.38 | 0.20 | −0.05 | RNF212B | −0.42 | 0.09 | 0.39 | 0.07 | 0.35 | CCDC63 | 0.12 | −0.17 | −0.96 | 0.27 | −0.65 |
| GNPTG | −0.44 | 0.19 | 0.39 | 0.20 | 0.30 | ELL3 | −0.57 | 0.09 | 0.67 | −0.30 | −0.36 | MUC22 | 0.27 | −0.31 | −0.56 | 0.41 | −0.60 |
| ITGA9 | −0.65 | 0.14 | 0.59 | 0.12 | 0.18 | GUSBP3 | −0.63 | 1.77 | 1.36 | 0.16 | −0.32 | OR2J2 | −0.24 | −0.68 | −1.08 | 0.90 | 0.02 |
| AL603840.1 | −0.95 | 0.45 | 1.29 | −0.09 | 0.53 | AC020978.7 | −0.32 | 0.00 | −0.50 | 0.09 | −0.35 | AC003991.2 | 0.15 | −0.54 | −0.30 | −0.46 | 0.27 |
| SUCLA2 | 0.46 | −0.29 | −0.50 | −0.17 | −0.21 | MYMX | −0.96 | 1.34 | 0.29 | 1.93 | 0.42 | LINC02044 | −0.14 | 0.20 | −0.21 | 0.04 | −0.08 |
| PPP2R3A | 0.75 | −0.10 | −0.38 | 0.14 | −0.20 | SNAP25 | 0.45 | −0.13 | 0.08 | −0.33 | −0.40 | AF279873.2 | 0.25 | 0.62 | −0.46 | −0.32 | −1.36 |
| CBFA2T2 | −0.42 | 0.30 | 0.38 | 0.15 | 0.09 | RN7SL787P | −1.33 | −1.39 | 2.20 | 0.24 | 1.69 | AC004846.1 | −0.08 | 0.33 | −0.46 | 0.22 | −0.63 |
| RANBP6 | 0.56 | −0.24 | −0.46 | −0.03 | −0.30 | AC002064.1 | −0.57 | −0.91 | 0.94 | −0.56 | 0.03 | MS4A18 | −0.31 | 0.20 | 0.56 | 1.24 | 0.09 |
| PPP5D1 | −0.57 | 0.49 | 0.54 | 0.14 | 0.19 | HMGA1P3 | 0.62 | 0.57 | −1.03 | 0.18 | −0.05 | AC005189.1 | −0.14 | −0.75 | −0.02 | 0.07 | 0.39 |
| BRIP1 | 0.76 | −0.77 | −1.21 | −0.10 | −0.34 | ITFG1 | 0.12 | 0.01 | 0.00 | −0.11 | −0.19 | AL355994.5 | 0.76 | −1.64 | −1.01 | −1.65 | −1.54 |
| AL354813.1 | 0.98 | −0.16 | −0.64 | 0.07 | −0.20 | AL359851.1 | −0.63 | −0.49 | −0.04 | −0.16 | −0.26 | SAGE1 | 0.31 | 1.43 | −1.71 | −0.45 | −2.36 |
| ASAP1 | 0.31 | −0.14 | −0.40 | −0.10 | −0.29 | NCSTNP1 | −1.40 | −0.78 | 1.97 | −0.26 | −0.15 | AC062017.1 | 0.12 | −0.19 | −0.22 | −0.10 | 0.13 |
| CCNL2 | −0.48 | 0.15 | 0.10 | 0.27 | 0.27 | CYCSP29 | 0.68 | −0.64 | 0.12 | −0.09 | 0.63 | BX649601.1 | −0.20 | −1.71 | 2.10 | 0.19 | 2.88 |
| GJB5 | 1.04 | −0.21 | −0.47 | −0.27 | −0.74 | NTSR2 | 1.45 | −0.34 | −1.94 | 0.68 | −0.62 | ADGRA3 | −0.05 | 0.06 | 0.02 | 0.04 | 0.08 |
| MAP7 | 0.55 | 0.02 | −0.46 | 0.00 | −0.40 | RN7SKP40 | −0.78 | 1.60 | 0.66 | −0.34 | −0.20 | AC111006.1 | −0.24 | −0.10 | −0.55 | 0.47 | −0.93 |
| LINC01845 | 1.12 | −0.69 | −1.86 | 0.01 | −0.62 | KCNMB2-AS1 | −0.58 | −0.57 | −0.12 | 0.07 | 0.04 | AC013652.1 | −0.08 | −0.02 | −0.04 | −0.19 | 0.03 |
| RPSAP69 | −1.80 | 1.06 | 1.67 | −0.03 | 0.68 | AC022126.1 | −1.16 | 0.79 | −0.59 | 1.06 | −0.73 | RNU7-37P | 0.21 | 0.43 | 0.81 | −0.59 | 0.23 |
| CAPZA2 | 0.51 | −0.23 | −0.36 | −0.13 | −0.45 | LRRC73 | −0.51 | 0.20 | 0.20 | 0.01 | 0.38 | AC078899.4 | −0.64 | −0.46 | 0.61 | −1.15 | 1.40 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC099509.2 | 1.75 | −0.15 | −0.74 | −0.50 | −0.74 | SLC24A3 | −0.19 | 0.10 | 0.12 | 0.14 | 0.11 | SLC35A3 | −0.03 | 0.00 | 0.18 | −0.01 | 0.09 |
| SNX18P23 | −1.93 | −0.08 | 0.28 | 0.71 | 0.32 | HTT-AS | −0.56 | 0.64 | 0.46 | 0.49 | 0.79 | AC004840.1 | 0.18 | 0.71 | −0.16 | −0.01 | 0.21 |
| ABCB9 | −0.53 | 0.25 | 0.31 | 0.18 | 0.38 | AL034546.1 | −0.80 | −1.01 | −0.80 | 0.45 | 0.50 | KRR1P1 | −0.08 | 0.12 | 0.80 | 0.03 | 0.46 |
| CSF2RB | 0.91 | −1.04 | −0.80 | −0.61 | −0.37 | AC116312.1 | −1.25 | 0.69 | 3.01 | −0.83 | 0.75 | RNA5SP78 | 0.12 | −0.07 | 0.21 | −0.02 | −0.31 |
| HIBCH | 0.45 | −0.33 | −0.33 | 0.05 | 0.10 | RNU6-865P | −1.07 | 0.01 | 2.03 | −1.43 | 0.01 | AC023055.1 | 0.23 | 0.37 | 0.31 | 0.14 | 0.08 |
| IL31RA | −0.82 | 0.43 | 0.10 | −0.04 | −0.87 | SENP3 | 0.14 | −0.14 | −0.18 | −0.04 | 0.25 | RPL7P39 | 0.27 | −0.45 | −1.23 | 0.13 | −0.72 |
| RFX3 | −0.45 | 0.48 | 0.58 | 0.24 | 0.01 | AF117829.2 | −0.71 | 0.63 | 0.07 | 0.31 | −0.43 | MTND5P19 | 0.44 | −0.23 | −1.44 | 0.22 | −1.44 |
| KRT3 | 1.45 | 0.44 | −1.46 | 1.62 | −1.39 | PRPF38AP1 | −0.94 | 0.91 | −0.85 | 0.11 | −2.26 | AC091959.1 | 0.16 | −0.55 | −0.03 | −0.26 | −0.40 |
| CAND2 | −0.76 | 0.17 | 0.48 | 0.35 | 0.33 | C15orf53 | 0.45 | −0.03 | 0.72 | −0.29 | 0.12 | LINC02274 | −0.20 | −1.27 | 0.86 | −0.71 | 0.49 |
| PDE9A | −1.09 | 0.91 | 1.53 | 0.36 | 0.35 | MIR1288 | 0.92 | −0.48 | −1.85 | −0.75 | −1.53 | AP003062.3 | 0.47 | −1.27 | −2.62 | 0.32 | −2.59 |
| NCOA4 | 0.52 | −0.11 | −0.36 | −0.01 | −0.44 | AC090771.2 | 1.13 | −0.88 | 0.10 | 0.47 | 1.02 | ENPP7 | 0.37 | −0.38 | −1.90 | 0.43 | −1.78 |
| RTL5 | −0.96 | 0.13 | 1.07 | 0.21 | 0.48 | OR7K1P | −1.51 | −1.78 | −0.97 | 0.10 | −0.63 | RN7SL312P | −0.15 | −0.67 | −0.24 | −0.02 | 0.65 |
| DOK6 | −0.98 | 0.51 | 1.34 | −0.23 | 0.73 | GRAP | 0.67 | −1.14 | 0.31 | −0.22 | 0.12 | AL031673.1 | −0.11 | −0.33 | −0.13 | −0.24 | 0.17 |
| CUL9 | −0.57 | 0.28 | 0.49 | 0.24 | 0.26 | COL14A1 | −0.38 | 0.71 | 1.26 | −0.21 | −0.51 | AC126603.1 | 0.17 | −0.72 | −0.93 | 0.82 | −0.91 |
| AC027514.2 | 0.81 | −0.22 | −0.31 | −0.28 | −0.10 | PKD1P6-NPIPP1 | −0.51 | −0.31 | 0.67 | 0.24 | 1.03 | LINC00365 | −0.18 | 0.24 | −0.23 | 0.53 | −0.28 |
| DNM1P51 | −1.06 | 0.40 | 0.87 | 0.01 | −0.11 | HMGB1P11 | −0.67 | −0.45 | −0.43 | −0.13 | 0.43 | RNU6-842P | 0.93 | −0.49 | −1.48 | 0.28 | −1.94 |
| CHRDL1 | −1.74 | 1.58 | 2.15 | 0.32 | −0.33 | AL138899.1 | −0.62 | −0.04 | 0.14 | −0.48 | −0.14 | CTHRC1P1 | 0.48 | −1.28 | 1.18 | 1.54 | 1.77 |
| COA6 | 0.80 | −0.83 | −0.57 | −0.39 | −0.17 | AL359962.2 | 0.65 | −0.91 | 0.47 | −0.76 | 0.25 | RAB28P5 | −0.26 | −0.46 | 0.81 | −0.38 | 0.96 |
| CUL1 | 0.38 | −0.14 | −0.45 | −0.14 | −0.33 | AKIRIN1P2 | −1.11 | −0.08 | 1.41 | −1.70 | −0.16 | RPL10P9 | 0.10 | 0.25 | 0.05 | 0.12 | −0.22 |
| AC138207.4 | 0.75 | −0.21 | −0.63 | 0.03 | −0.38 | AL356133.2 | 1.07 | −1.39 | −1.70 | 1.09 | 1.09 | LINC02267 | 0.24 | −1.25 | −1.41 | 0.97 | −0.89 |
| SOX13 | −0.84 | 0.42 | 0.83 | 0.38 | 0.23 | SENP2 | −0.10 | 0.18 | 0.16 | 0.06 | 0.01 | HMGB3P26 | 0.45 | −1.01 | −2.53 | 1.01 | −1.25 |
| ELANE | −1.53 | 0.35 | 1.85 | 0.09 | 0.81 | CSNK1G2-AS1 | 0.43 | −0.06 | −0.34 | −0.04 | −0.18 | LMAN1L | 0.40 | −0.64 | −0.73 | −0.67 | −1.03 |
| RN7SL834P | 1.13 | −0.57 | −0.32 | −0.40 | −0.20 | QRSLIP3 | 0.39 | 0.17 | 0.20 | −0.08 | −0.27 | AL133384.2 | 0.10 | 0.18 | −0.24 | 0.00 | −0.40 |
| RANP1 | 1.49 | −0.91 | −2.22 | 0.35 | −0.64 | HERPUD2 | 0.11 | 0.10 | 0.04 | 0.02 | −0.18 | PSMD9 | −0.04 | 0.04 | −0.09 | 0.11 | −0.16 |
| ANKRD20A11P | −1.22 | 0.51 | 1.07 | −0.03 | 0.88 | AC005726.1 | −0.29 | −0.08 | −0.01 | 0.24 | 0.57 | AL590556.1 | −0.11 | −0.48 | 0.25 | −0.59 | 0.31 |
| PELI3 | −0.55 | 0.09 | 0.18 | 0.31 | 0.44 | SUCLA2P3 | −0.85 | −0.01 | 1.24 | −0.86 | 0.48 | AC109466.1 | −0.18 | 0.04 | −0.61 | 0.62 | −0.22 |
| BEX2 | −0.86 | 0.92 | 1.56 | 0.10 | 0.05 | FDCSP | 1.05 | −1.91 | −2.33 | −0.57 | 0.69 | HNRNPA1P23 | 0.22 | −1.50 | −1.77 | 0.99 | −2.13 |
| AL031058.1 | 0.97 | 0.19 | −1.04 | 0.22 | −0.67 | MTATP6P19 | −0.44 | 0.04 | −1.33 | 0.19 | −0.34 | AC125618.1 | 0.24 | −0.63 | 0.09 | 0.67 | 0.28 |
| C19orf71 | −1.29 | 0.59 | 0.44 | 0.63 | −0.09 | RNU6-466P | 0.46 | 0.17 | 0.43 | −0.14 | 0.06 | PPP1R26-AS1 | −0.07 | 0.21 | −0.38 | −0.19 | −0.37 |
| ATP6V1B1 | −1.47 | 0.79 | 1.25 | 0.40 | 0.36 | ABCC5-AS1 | 0.41 | −0.08 | 0.43 | 0.02 | −0.07 | AC104521.1 | −0.28 | −0.63 | −0.28 | −0.71 | −1.24 |
| RPS24 | 0.54 | −0.16 | −0.18 | −0.11 | −0.21 | SPEM3 | −0.65 | −0.75 | 0.04 | −0.27 | −0.16 | AC103987.2 | 0.29 | −0.54 | −0.95 | 1.85 | −1.24 |
| DGKH | 0.39 | −0.24 | −0.56 | 0.00 | −0.17 | AC025262.1 | −1.02 | −0.26 | 2.25 | −0.94 | 1.27 | KRT18P13 | 0.47 | −1.59 | 0.09 | −1.35 | 0.31 |
| CDV3 | 0.51 | −0.39 | −0.52 | −0.21 | −0.25 | PDCL2 | 0.44 | 0.10 | −0.69 | 0.06 | −0.67 | MUT | −0.04 | 0.19 | 0.14 | 0.22 | −0.06 |
| RBM33 | −0.26 | 0.21 | 0.16 | 0.13 | 0.11 | OR2A12 | −0.64 | 0.29 | −0.12 | 0.88 | −0.27 | GUCY1A1 | 0.08 | −0.07 | 0.78 | −0.03 | 0.06 |
| AC079316.1 | 1.88 | −1.03 | −1.84 | −0.34 | −0.64 | AC092814.1 | 1.17 | 0.59 | 0.31 | −0.17 | −0.68 | AC044781.1 | −0.14 | −0.29 | 0.30 | −0.49 | −0.17 |
| AC027796.3 | −1.46 | 0.31 | −0.02 | 0.25 | −0.10 | CA5BP1 | 0.19 | −0.04 | −0.08 | 0.09 | 0.16 | AL136526.1 | 0.18 | 0.35 | 1.17 | 0.26 | 0.56 |
| DACT1 | −1.32 | 0.50 | 1.52 | −0.60 | −0.43 | PSMC1P11 | 1.08 | 0.03 | 2.15 | −1.47 | −0.19 | KRTAP4-4 | −1.21 | 0.32 | 0.09 | 0.40 | 0.94 |
| RN7SL774P | −1.34 | −0.55 | 0.48 | 0.42 | 1.58 | OR5B19P | −1.21 | −1.04 | 1.61 | −0.39 | 1.53 | SLC5A5 | 0.19 | −0.94 | −1.91 | −0.68 | −0.36 |
| PGD | 0.59 | −0.35 | −0.51 | −0.07 | −0.32 | AC004898.1 | 0.28 | −0.16 | −0.55 | 0.04 | −0.09 | RNU6-375P | 0.29 | −0.49 | −0.12 | −0.71 | 0.13 |
| SEC24AP1 | −1.47 | 1.24 | 1.70 | 0.63 | 0.20 | MRPS18A | 0.15 | 0.02 | −0.24 | −0.05 | −0.31 | RN7SL43P | 0.28 | −0.74 | −2.40 | 2.03 | −1.19 |
| AP001453.2 | 1.63 | −0.95 | −1.71 | 0.13 | −0.57 | LY6G5B | −0.27 | 0.34 | 0.38 | 0.37 | 0.11 | OR4B1 | 0.42 | 0.19 | −0.79 | −0.74 | −1.17 |
| AC099684.1 | −1.12 | 0.48 | 0.49 | 0.47 | 0.82 | RWDD2B | 0.18 | −0.21 | 0.17 | −0.02 | 0.23 | AC044839.4 | 0.37 | −0.63 | −1.26 | 1.04 | 0.39 |
| IL17RC | −0.44 | 0.41 | 0.09 | 0.43 | 0.02 | AP005118.1 | −0.92 | −0.12 | 2.63 | −0.98 | −0.04 | MARK2P9 | −0.12 | −0.35 | 0.00 | 0.05 | −0.07 |
| LRRC37A11P | −1.14 | 0.26 | 1.16 | 0.44 | 0.55 | MTND3P10 | 0.63 | −0.57 | −0.46 | 0.02 | −0.66 | AC010615.1 | −0.08 | 0.00 | 0.82 | −0.37 | 0.17 |
| GSDMA | 0.93 | −0.30 | −0.56 | 0.08 | −0.27 | MT-ND4L | −0.26 | 0.15 | 0.10 | 0.12 | −0.15 | C8orf76 | −0.06 | −0.18 | −0.19 | 0.05 | −0.19 |
| COPZ1 | 0.42 | −0.16 | −0.31 | 0.01 | −0.19 | AC211469.1 | 0.64 | −1.05 | −0.35 | −0.74 | −0.28 | AC129507.3 | 0.20 | −0.40 | 0.16 | 1.24 | 1.16 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| LSM3 | 0.81 | −0.40 | −0.38 | −0.12 | −0.32 | RWDD3 | −0.18 | 0.00 | 0.22 | 0.23 | 0.27 | AC096887.1 | −0.12 | 0.00 | 0.09 | 0.17 | 0.53 |
| CRISPLD1 | −0.94 | 0.65 | 1.01 | 0.29 | 0.27 | DRAXIN | −0.45 | −0.66 | 0.08 | −0.12 | 0.46 | AC046195.2 | 0.57 | 1.04 | −0.36 | 1.49 | −2.57 |
| CYP4Z1 | −1.08 | −0.50 | 0.12 | 0.15 | 0.83 | AC116562.4 | −0.53 | 0.64 | 0.58 | 0.98 | 0.39 | AC095030.1 | 0.24 | 0.03 | −1.51 | −0.04 | −1.35 |
| AP000897.2 | −1.16 | 0.01 | 0.87 | −0.62 | 0.17 | RP11-39704.1 | −0.45 | 0.62 | 1.21 | −0.45 | 0.50 | DISC1-IT1 | 0.12 | −0.06 | −1.09 | −0.08 | −0.80 |
| C4orf19 | −0.70 | 0.29 | 0.07 | −0.05 | −0.10 | NDUFA5 | 0.19 | −0.03 | −0.05 | −0.11 | −0.22 | AC106037.1 | −0.17 | −0.11 | −0.54 | −0.31 | −0.75 |
| SEPT5-GP1BB | −1.10 | 1.07 | 1.34 | 0.41 | 0.12 | SDCBPP2 | −0.56 | 0.00 | −0.09 | 0.22 | 0.38 | GALNTL5 | −0.21 | −0.49 | −1.49 | 0.89 | 0.00 |
| SKI | −0.35 | 0.25 | 0.20 | 0.12 | −0.07 | AC103778.1 | 1.14 | −0.24 | −0.42 | 0.02 | 0.22 | LINC01067 | −0.82 | 0.41 | 0.42 | −1.32 | −0.19 |
| CENPO | 0.64 | −0.49 | −0.71 | −0.22 | −0.28 | AL133260.2 | 0.53 | −0.93 | −0.64 | −0.26 | 0.77 | AC002511.1 | −0.12 | −0.05 | −0.57 | 0.34 | 0.53 |
| CIT | 0.64 | −0.54 | −0.75 | −0.41 | −0.25 | RHOF | −0.33 | 0.02 | 0.44 | −0.03 | 0.38 | CLK2P1 | 0.26 | −0.08 | −1.91 | −0.05 | −1.19 |
| AP2A1 | 0.29 | −0.17 | −0.39 | −0.01 | −0.22 | LRRFIP2 | 0.12 | −0.07 | −0.28 | −0.09 | −0.21 | C8orf49 | −0.26 | −0.17 | 0.63 | −0.21 | 0.35 |
| AC106886.5 | 1.05 | −0.17 | −1.08 | 0.12 | −1.03 | AC087620.1 | −0.25 | −0.57 | −0.26 | −0.19 | 0.50 | AC009309.1 | 0.34 | −0.36 | −0.18 | 0.45 | −1.21 |
| PNPLA2 | −0.88 | 0.73 | 0.53 | 0.49 | −0.05 | CLEC19A | −1.04 | 0.74 | 0.22 | 0.24 | −0.33 | AC006450.1 | −0.36 | 0.54 | 0.78 | −0.43 | −1.01 |
| GTF2B | 0.48 | −0.26 | −0.30 | −0.13 | −0.26 | G6708 | 0.45 | 0.04 | −0.36 | 0.06 | −0.04 | CCDC189 | 0.15 | 0.72 | −1.03 | 1.00 | 0.09 |
| PACSIN2 | −0.41 | 0.17 | 0.14 | 0.00 | 0.01 | NLRP9 | −0.44 | 0.16 | −0.34 | 0.09 | 0.03 | RNA5SP474 | 0.16 | 0.02 | 0.22 | 0.07 | 0.01 |
| EIF4A1P2 | 1.65 | −0.64 | −0.72 | −0.16 | −0.37 | AC005229.4 | 0.37 | 0.24 | −0.74 | −0.05 | −0.79 | AC005921.4 | −0.32 | −1.95 | 0.96 | −0.01 | 0.06 |
| AC009145.4 | −0.83 | 0.12 | 0.22 | 0.24 | 0.48 | CMA1 | −0.44 | 1.01 | 0.83 | 0.45 | −0.19 | LMO4 | −0.05 | 0.29 | 0.44 | −0.06 | 0.03 |
| APOBEC3C | 0.52 | −0.35 | −0.24 | −0.10 | 0.07 | PRED62 | 0.89 | −1.08 | 0.44 | −0.33 | 1.43 | C1RL | 0.04 | −0.19 | −0.14 | 0.02 | 0.16 |
| PEX13 | 0.53 | −0.27 | −0.47 | −0.06 | −0.17 | CCP110 | 0.14 | −0.01 | 0.21 | −0.03 | 0.06 | INPP4A | 0.03 | −0.12 | −0.01 | −0.07 | 0.07 |
| FPR1 | 1.83 | −1.81 | −1.91 | −0.25 | −1.42 | AC007991.2 | 1.35 | −1.90 | −1.29 | −0.96 | −0.39 | RPL24P7 | −0.63 | 0.21 | 0.01 | −0.90 | 0.61 |
| PLEKHF2 | 0.70 | −0.12 | −0.49 | 0.10 | −0.48 | AC011475.1 | −0.39 | 0.12 | 0.46 | −0.35 | 0.05 | AC239798.2 | 0.23 | −0.29 | 0.07 | −0.80 | −0.37 |
| RTRAF | 0.53 | −0.15 | −0.24 | −0.17 | −0.42 | AC091393.1 | 0.66 | −1.05 | −1.18 | −0.04 | 0.02 | CELSR3 | −0.06 | −0.19 | −0.53 | 0.16 | 0.13 |
| RETREG1 | −0.66 | 0.39 | 0.92 | −0.04 | 0.23 | NTAN1 | −0.19 | 0.13 | 0.10 | 0.16 | 0.06 | KIF1B | 0.02 | 0.13 | −0.06 | 0.00 | −0.28 |
| SOCS4 | 0.43 | −0.06 | −0.06 | −0.10 | −0.20 | GNRHR2 | −0.39 | −0.03 | 0.01 | 0.63 | 0.59 | BPI | −0.27 | −0.77 | 0.29 | −0.38 | −0.90 |
| JUND | −0.57 | 0.64 | 0.20 | 0.38 | −0.28 | G35488 | −0.41 | 0.35 | 0.81 | 0.22 | 0.55 | G34413 | −0.16 | 0.47 | −0.15 | −0.20 | −1.37 |
| KARSP2 | −2.09 | 1.53 | 4.08 | 0.79 | 0.00 | SPATA22 | 0.68 | −1.08 | −1.06 | −0.09 | −0.42 | PGDP1 | −0.29 | −1.18 | −0.87 | 0.20 | 0.77 |
| CLEC4F | −1.20 | 0.76 | 0.51 | 0.88 | 0.94 | PPEF2 | −0.58 | −0.37 | 0.37 | 0.07 | 0.93 | AL136455.1 | 0.62 | −1.94 | −2.13 | −0.44 | 0.68 |
| SPINK5 | 0.88 | 0.05 | 0.12 | −0.05 | −0.20 | HGC6.3 | 1.11 | 0.26 | −0.19 | −0.17 | −0.77 | AP000676.5 | 0.09 | −0.27 | −0.73 | −0.13 | −0.52 |
| BCL2L12 | 0.61 | −0.55 | −0.29 | −0.20 | 0.21 | LINC01460 | −0.70 | −0.34 | −0.30 | −1.07 | −0.15 | RPL9P2 | 0.18 | −0.17 | 0.36 | −0.04 | 0.22 |
| NOL10 | 0.47 | −0.31 | −0.41 | −0.11 | −0.17 | AP001350.1 | 0.37 | 0.31 | 0.04 | 0.23 | −0.21 | S100Z | −0.17 | −0.21 | −0.03 | −0.24 | 0.09 |
| FAM90A20P | −1.44 | 0.35 | 1.10 | 0.57 | 0.36 | MSC | 0.37 | −0.22 | −0.07 | −0.57 | −0.50 | AC016831.4 | −0.06 | −0.16 | −0.18 | −0.12 | 0.19 |
| REX02 | 0.44 | −0.07 | −0.08 | −0.04 | −0.18 | AC006978.1 | 0.19 | 0.15 | −0.13 | 0.14 | −0.05 | LINC01595 | 0.47 | −2.30 | −1.03 | −0.49 | −0.46 |
| NSDHL | 0.69 | −0.26 | −0.77 | 0.14 | −0.34 | LTA | 0.67 | −0.64 | 0.16 | −0.77 | 0.09 | AL121723.1 | −0.28 | −0.83 | −0.27 | −0.82 | −0.60 |
| CDK2AP2 | 0.58 | −0.14 | −0.65 | 0.02 | −0.34 | AC009927.1 | −0.37 | 0.06 | 0.23 | −0.02 | −0.07 | AL139353.1 | −0.16 | 1.01 | 0.14 | 0.57 | 0.12 |
| FAM106A | −0.87 | 0.60 | 0.98 | 0.34 | −0.65 | NDST1-AS1 | 0.72 | 0.43 | −0.04 | 0.14 | −0.37 | AC107058.1 | −0.41 | −1.13 | −0.26 | −1.32 | −2.46 |
| ARL8A | −0.38 | 0.41 | 0.19 | 0.09 | −0.21 | AL024507.2 | 0.38 | −1.08 | −0.33 | −0.23 | 0.77 | ANKRD55 | −0.15 | −0.83 | 0.88 | −0.21 | 2.11 |
| RN7SL347P | −1.39 | 0.21 | 0.40 | 0.07 | 0.71 | AL359092.1 | 0.83 | −0.60 | 0.84 | −0.19 | 0.64 | AC234781.5 | −0.19 | 0.50 | 1.81 | −0.72 | −0.11 |
| ABCA17P | −0.90 | 0.37 | 0.19 | 0.68 | 0.58 | AC098850.1 | −0.94 | −0.23 | −0.60 | 1.27 | 1.75 | FO393414.1 | −0.47 | 1.20 | −0.94 | 1.82 | −0.67 |
| RNU1-11P | −1.10 | 0.34 | 0.13 | 0.07 | −0.14 | RN7SL809P | 0.49 | −0.12 | 0.31 | 0.03 | 0.20 | AP001094.3 | −0.13 | −0.51 | −0.87 | −0.16 | −0.26 |
| SLC30A1 | 0.81 | −0.28 | −0.36 | −0.02 | −0.40 | NPR1 | −0.34 | −0.01 | 0.09 | 0.14 | 0.00 | AC104695.2 | −0.12 | −0.14 | 0.13 | −0.28 | 0.24 |
| RNASEHI | 0.44 | −0.38 | −0.38 | −0.26 | −0.18 | AL136980.1 | 0.48 | −0.02 | −0.07 | 0.11 | 0.38 | AC012317.1 | −0.76 | 0.07 | 0.90 | 0.04 | 0.61 |
| NACAD | −1.00 | 0.14 | 0.59 | 0.01 | 0.39 | AL450326.2 | −0.39 | 0.45 | 0.93 | 0.33 | 0.15 | MIR548L | −0.18 | 0.02 | 1.99 | 0.24 | 0.99 |
| ATP1B2 | −0.89 | 0.52 | 1.37 | 0.45 | 0.43 | AL035696.1 | 1.20 | −1.79 | −1.95 | 0.38 | 0.08 | ASS1P1 | 0.16 | −1.00 | 0.98 | −0.75 | 0.83 |
| OR2A14 | −1.44 | 0.09 | 0.79 | 1.28 | 1.47 | HOXB-AS2 | −0.50 | 0.17 | 1.99 | −0.23 | 0.58 | C3orf79 | −0.20 | 1.44 | −1.68 | 1.03 | −1.49 |
| BNC2 | −0.92 | 0.62 | 1.03 | −0.19 | −0.11 | G26856 | −0.65 | 1.09 | −0.47 | 0.52 | −0.93 | AP002770.2 | −0.13 | 0.07 | 0.29 | −0.64 | −0.16 |
| SLC6A16 | −0.90 | 0.43 | 0.78 | 0.22 | 0.20 | AC068725.1 | −1.25 | 0.14 | 1.83 | 0.61 | 1.47 | MTND2P13 | 0.24 | −0.39 | −1.51 | 0.80 | −1.36 |
| DNMT1 | 0.58 | −0.70 | −0.80 | −0.25 | −0.08 | RPL39P26 | 0.38 | −0.06 | −0.28 | −0.04 | −0.21 | AC104012.1 | 0.37 | −1.23 | −0.58 | 0.01 | 0.86 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| LGALSL | 0.85 | −0.25 | −0.04 | −0.17 | −0.45 | AC007621.1 | −0.84 | −0.06 | 1.11 | −0.19 | −0.44 | AL441943.2 | 0.61 | −0.14 | −1.55 | −0.06 | −1.22 |
| MOGAT1 | −2.51 | 1.89 | 0.86 | 2.80 | 1.25 | RNU6-47P | −0.71 | 0.83 | −1.40 | 0.90 | −0.71 | G16904 | −0.16 | 0.49 | 0.58 | 0.27 | −0.23 |
| AC118344.2 | −0.69 | 0.25 | 0.88 | −0.01 | 0.52 | FGFR2 | −0.21 | 0.21 | −0.14 | 0.49 | 0.20 | RHOXF1P1 | −0.21 | −0.69 | −0.61 | 0.07 | −0.38 |
| MED21 | 0.52 | −0.10 | −0.55 | −0.01 | −0.49 | DSG2 | −0.30 | 0.26 | 0.40 | −0.21 | 0.29 | HMGB3P20 | 0.28 | −1.30 | −1.17 | 0.05 | 0.10 |
| PIK3R6 | −0.94 | 0.32 | 1.49 | 0.37 | 0.73 | RPL30 | 0.20 | 0.11 | 0.13 | −0.03 | −0.39 | AL133346.1 | −0.41 | 0.27 | 1.82 | −0.94 | 1.41 |
| AC133041.1 | −1.98 | 0.26 | 1.78 | 1.00 | 1.29 | CDSN | 0.38 | 0.20 | 0.38 | 0.15 | −0.35 | DSCR10 | 0.52 | −1.07 | −0.93 | −0.47 | −0.32 |
| SCARA3 | −0.81 | 0.56 | 0.54 | 0.28 | −0.17 | AL391427.1 | −0.49 | −0.09 | 1.43 | −0.42 | 0.73 | MRGPRX4 | −0.47 | −0.34 | −0.71 | −0.14 | −2.94 |
| NLRP2 | 1.18 | −0.69 | −1.44 | −0.36 | −1.90 | SNORA51 | −0.35 | −0.19 | −0.36 | −0.10 | 0.14 | AC087612.1 | −0.22 | −0.63 | 0.71 | −0.63 | 0.08 |
| MAPKAPK2 | 0.50 | −0.25 | −0.71 | −0.06 | −0.40 | COX6B1P3 | 0.58 | −1.14 | −1.16 | −0.38 | 0.15 | AL353804.1 | 0.09 | 0.12 | 0.25 | 0.03 | 0.30 |
| PIGA | 0.54 | −0.10 | −0.88 | 0.04 | −0.67 | AC007494.1 | −0.32 | 0.60 | −0.27 | 0.31 | −0.20 | AC108868.2 | 0.42 | −0.81 | −0.49 | 1.41 | 1.50 |
| NUP155 | 0.32 | −0.29 | −0.35 | −0.09 | −0.13 | OMA1 | −0.19 | 0.22 | 0.59 | −0.06 | 0.18 | AL357033.1 | −0.13 | −0.01 | 0.07 | −0.14 | −0.04 |
| SLC25A53 | −0.54 | 0.15 | 0.58 | −0.03 | 0.31 | G30001 | 0.46 | −0.22 | −0.13 | −0.30 | −0.10 | KLF8P1 | 0.24 | −1.08 | −0.67 | 1.10 | −0.26 |
| PNISR | −0.46 | 0.21 | 0.28 | 0.14 | 0.03 | RNU6-199P | 0.42 | −0.14 | 0.48 | −0.28 | 0.26 | AP000781.2 | 0.15 | −0.04 | −0.14 | 0.94 | 0.20 |
| ADAMTS13 | −0.86 | 0.59 | 0.29 | 0.47 | 0.22 | MIR454 | 0.62 | −0.47 | −0.44 | −0.01 | −0.53 | AP001783.1 | 0.28 | −0.96 | −0.75 | 0.93 | −0.16 |
| ACOT11 | −0.60 | 0.33 | −0.21 | 0.34 | −0.26 | MTCYBP3 | 0.35 | −0.60 | −0.10 | −0.28 | 0.89 | RNU6-378P | 0.22 | −0.06 | 0.56 | −0.49 | 0.09 |
| ABCB10 | 0.36 | −0.25 | −0.28 | −0.08 | 0.07 | AC096586.2 | 0.52 | 0.29 | 0.04 | 0.09 | −0.21 | MTND5P25 | −0.10 | 0.01 | 0.17 | 0.25 | −0.09 |
| MUTYH | −0.52 | 0.17 | 0.17 | 0.18 | 0.14 | DPY19L2P4 | −0.66 | 0.30 | 0.63 | −0.27 | −0.05 | AL137071.1 | 0.28 | 0.27 | −0.59 | −1.04 | −0.97 |
| MIR149 | −2.39 | 0.67 | 1.25 | 0.71 | 0.77 | PGAP2 | −0.21 | 0.22 | 0.43 | 0.15 | 0.24 | AC011195.2 | 0.28 | −1.18 | 1.34 | −0.86 | 1.70 |
| PARG | 0.46 | −0.04 | −0.34 | −0.03 | −0.35 | NDST4 | −0.88 | 1.39 | −1.21 | 0.72 | −0.28 | NRADDP | 0.09 | 0.08 | 0.33 | −0.54 | −0.28 |
| BROX | 0.47 | −0.09 | −0.29 | −0.06 | −0.34 | ALOX12P2 | −0.24 | 0.05 | 0.01 | −0.01 | 0.26 | AL451042.2 | 0.10 | −0.07 | −0.37 | 0.20 | −0.35 |
| DEPTOR | −0.63 | 0.77 | 0.77 | 0.45 | 0.17 | AC084876.2 | 0.75 | −0.21 | −1.11 | 0.04 | −0.42 | AC004801.2 | 0.07 | −0.22 | −0.21 | −0.11 | 0.09 |
| AP005212.2 | −2.03 | −0.01 | 0.69 | −0.02 | 0.56 | AC106820.4 | −0.39 | 0.10 | 0.09 | −0.16 | 0.37 | MS4A13 | 0.47 | −1.48 | 0.57 | −0.33 | 0.46 |
| MBD5 | −0.30 | 0.27 | 0.38 | 0.02 | 0.01 | AL354793.1 | 0.33 | −0.01 | −1.07 | 0.50 | −0.50 | LINC00517 | −0.14 | −0.12 | −0.03 | −0.04 | 0.38 |
| OPA1 | 0.31 | −0.16 | −0.34 | −0.04 | −0.14 | NUCB2 | 0.22 | −0.11 | 0.03 | −0.26 | −0.07 | AC008852.1 | −0.70 | 0.21 | −1.09 | 1.00 | −1.10 |
| ACRV1 | 1.14 | −1.06 | −1.41 | −0.29 | −0.18 | KRT17P5 | 1.04 | −0.98 | −0.46 | −0.17 | 0.25 | AL807752.5 | −0.13 | 0.82 | −0.95 | −0.11 | −1.15 |
| G8320 | −1.27 | 0.41 | 0.22 | −0.25 | −0.13 | AC026367.1 | 0.91 | −0.32 | 0.63 | 0.25 | 0.83 | DNASE2 | 0.05 | −0.01 | 0.13 | −0.01 | −0.06 |
| CLCN6 | −0.31 | 0.11 | 0.17 | 0.14 | 0.14 | HMGN2P30 | 0.62 | 0.21 | 0.08 | 0.52 | 0.05 | CCDC178 | −0.14 | 0.22 | −1.23 | 0.38 | −0.90 |
| NOS3 | 0.85 | −0.29 | −0.37 | −0.23 | −0.41 | MIR3117 | 0.83 | −1.72 | −1.36 | −0.36 | −1.37 | AP000289.1 | 0.45 | −0.78 | −0.21 | 0.86 | 1.59 |
| MIR938 | 1.85 | −0.83 | −0.27 | −0.34 | 0.17 | RAB6C | −0.83 | −0.32 | 0.45 | 0.92 | 0.33 | AL359458.1 | −0.28 | 0.02 | −1.05 | −0.83 | −2.01 |
| AC142384.1 | −1.53 | 0.26 | 0.14 | 0.76 | −1.40 | BTF3P12 | 0.39 | 0.09 | −0.30 | 0.06 | −0.31 | CORIN | 0.08 | 0.66 | 1.19 | 0.20 | 0.24 |
| NOP56 | 0.73 | −0.72 | −1.03 | −0.08 | −0.17 | RAB11FIP1 | 0.19 | 0.11 | −0.34 | 0.03 | −0.54 | OR51A1P | −0.55 | −0.53 | 1.00 | −1.72 | 1.15 |
| RGCC | −0.78 | 0.16 | 0.61 | −0.39 | 0.09 | DNMBP-AS1 | 0.42 | −0.04 | −0.51 | −0.02 | −0.40 | AL583803.1 | 0.60 | −0.29 | −3.36 | 1.79 | −0.61 |
| GPAT2 | −0.84 | 0.06 | 1.20 | −0.35 | 0.61 | MSANTD4 | −0.17 | 0.01 | 0.49 | −0.03 | 0.39 | ATP1A3 | −0.21 | −0.46 | −0.12 | 0.36 | 0.60 |
| G23688 | −1.92 | 0.50 | 2.28 | −0.92 | −0.79 | RNU6-1010P | −0.63 | 0.44 | 0.67 | −0.68 | 0.15 | RNU6-891P | 0.99 | −1.92 | 1.14 | −1.45 | −0.44 |
| FIBP | 0.48 | −0.31 | −0.09 | −0.07 | −0.04 | RNA5SP215 | −1.33 | 1.17 | −0.54 | 0.99 | −2.01 | STX17 | −0.03 | 0.12 | 0.13 | 0.11 | 0.03 |
| ACOT2 | −0.68 | 0.33 | 0.19 | 0.26 | 0.52 | EIF2AK3 | −0.13 | 0.13 | 0.19 | −0.12 | 0.13 | SLC25A1P3 | −0.31 | 0.04 | −1.07 | 0.66 | −0.50 |
| CDT1 | 0.77 | −0.57 | −0.90 | 0.00 | −0.14 | SDSL | −0.45 | −0.06 | 0.03 | −0.36 | −0.19 | BPESC1 | −0.34 | −0.03 | −2.35 | 1.86 | −0.95 |
| PRMT5 | 0.60 | −0.41 | −0.41 | −0.12 | −0.01 | AC007387.1 | 0.82 | 0.42 | 1.18 | 0.37 | 0.81 | PPIAP1 | 0.71 | 0.02 | 0.45 | 0.13 | −0.72 |
| MED1 | 0.33 | −0.10 | −0.20 | −0.08 | −0.13 | AC135983.3 | −0.61 | 0.04 | 0.89 | −1.32 | −0.97 | NAV3 | 0.06 | −0.39 | −0.55 | −0.15 | −0.10 |
| KRT41P | −1.88 | 0.49 | −0.79 | −0.27 | −0.65 | DINOL | 0.75 | −0.82 | −2.61 | 0.49 | −2.31 | RIT2 | −0.29 | −0.53 | −0.35 | −0.38 | −0.89 |
| SNORA35 | −1.07 | 1.17 | 1.01 | 0.55 | −0.04 | AC044840.1 | 0.44 | −0.23 | −0.08 | −0.43 | 0.04 | AC006487.2 | 0.24 | −0.09 | −1.00 | 0.00 | −0.10 |
| COQ3 | 0.65 | −0.34 | −0.51 | −0.03 | −0.23 | PDGFC | 0.20 | −0.27 | −0.63 | 0.10 | −0.13 | SERPINA7 | 0.33 | −0.79 | −0.48 | 0.22 | 0.51 |
| BLVRA | 0.52 | −0.33 | −0.42 | −0.12 | −0.20 | LINC00840 | −0.44 | 0.57 | 0.57 | 0.54 | 0.22 | MTCYBP2 | 0.35 | 0.42 | 0.46 | −0.24 | 0.37 |
| CCER2 | −1.47 | 2.00 | 1.62 | 0.64 | 0.14 | RPL23AP23 | 0.45 | −0.80 | 0.08 | −0.20 | 0.54 | HMGB1P26 | 0.50 | −0.63 | −0.01 | −0.96 | −2.21 |
| LINC01336 | 1.17 | −0.66 | −0.56 | −0.25 | −0.22 | AC007563.1 | −1.01 | −0.91 | 3.14 | −0.48 | 0.53 | AC011451.2 | −0.18 | 0.85 | 1.41 | 0.41 | 0.41 |
| MORC3 | 0.37 | −0.13 | −0.29 | −0.08 | −0.15 | RN7SL324P | −0.84 | −0.09 | 0.92 | −0.07 | −0.58 | RPL5P3 | 0.17 | 0.29 | −0.43 | −0.13 | −0.56 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| DLAT | 0.56 | −0.27 | −0.49 | −0.19 | −0.28 | HOXD-AS2 | −0.45 | 0.41 | 1.13 | 0.33 | 0.80 | MIR193BHG | 0.04 | −0.21 | −0.50 | 0.18 | −0.03 |
| ENOX2 | 0.46 | −0.28 | −0.42 | −0.16 | −0.17 | GOLGB1 | 0.12 | 0.15 | −0.03 | 0.00 | −0.22 | RNU6-1099P | 0.13 | 0.37 | 0.24 | −0.15 | −0.40 |
| CUX1 | 0.44 | −0.33 | −0.47 | −0.02 | −0.10 | AP000221.1 | 1.00 | −0.87 | −0.22 | −0.40 | −0.47 | AC005329.3 | −0.16 | 0.78 | 0.98 | −0.12 | 0.21 |
| OR7C1 | −1.23 | 0.59 | 0.72 | 0.67 | 0.48 | AL031676.1 | −1.09 | 0.37 | −0.98 | 0.46 | −0.80 | AC069114.2 | −0.58 | −0.13 | −0.26 | 0.52 | −1.28 |
| CRKL | 0.48 | −0.12 | −0.30 | −0.14 | −0.29 | LINC01194 | −1.22 | −0.12 | −1.53 | 1.76 | 1.54 | AL450426.1 | −0.51 | −0.20 | −0.47 | −0.74 | −1.51 |
| AL353731.1 | −1.85 | 0.67 | 0.85 | 0.78 | 0.43 | CNNM4 | 0.21 | 0.10 | −0.33 | 0.37 | −0.22 | AL158147.2 | −0.16 | −0.92 | −0.87 | 0.00 | 0.09 |
| RPS16 | 0.54 | −0.14 | −0.19 | −0.22 | −0.36 | AC106798.1 | −0.59 | 0.32 | 1.02 | 0.55 | 1.43 | CLEC16A | −0.03 | 0.01 | 0.11 | −0.04 | 0.10 |
| HMGB1P5 | 0.60 | −0.38 | −0.46 | −0.41 | −0.38 | LINC02156 | −0.72 | 0.38 | 0.54 | −0.03 | 0.20 | AC136604.1 | −0.61 | 0.66 | 1.39 | 1.60 | 0.21 |
| METTL24 | −1.00 | 0.43 | 1.86 | −0.49 | 0.47 | AC016542.1 | 0.62 | −0.13 | −1.01 | −0.36 | −1.18 | G39215 | −0.09 | −0.09 | 0.19 | 0.48 | 0.55 |
| CCDC183 | −0.71 | 0.32 | 0.82 | 0.35 | 0.79 | RTL9 | −0.66 | 0.18 | −0.41 | 0.32 | −0.03 | FAM207BP | 0.32 | −0.66 | −0.84 | 0.89 | −1.43 |
| RSU1 | 0.43 | −0.15 | −0.29 | −0.19 | −0.35 | RNU6-516P | −0.45 | −0.09 | 1.33 | −0.38 | 0.77 | GSX1 | −0.63 | −0.60 | −0.87 | −0.89 | −0.27 |
| NDUFB11 | 0.49 | −0.11 | −0.13 | −0.10 | −0.30 | AL109947.2 | −1.52 | −0.73 | 1.50 | 0.24 | 1.91 | PDE8B | −0.05 | 0.10 | 0.31 | 0.30 | −0.06 |
| SLC47A1 | −0.78 | 0.34 | 0.86 | 0.32 | 0.76 | ALKBH4 | −0.19 | −0.01 | −0.30 | 0.20 | 0.03 | AC026703.2 | −0.41 | 0.76 | −1.55 | 2.40 | −1.06 |
| ELOC | 0.51 | −0.32 | −0.36 | −0.22 | −0.14 | RAB11B-AS1 | 0.31 | −0.06 | −0.63 | 0.35 | 0.02 | AC019080.5 | 0.13 | −0.27 | 0.80 | −0.47 | −0.01 |
| SLC18A2 | −0.94 | 0.32 | 1.77 | −0.04 | 0.75 | MUC12 | −0.40 | −0.57 | −0.31 | −0.28 | −0.54 | RNF7P1 | −0.76 | 1.65 | 1.15 | 2.47 | −0.04 |
| AC112496.1 | 1.03 | −1.28 | −0.27 | −0.32 | 0.50 | AC140061.12 | −0.70 | −0.14 | −0.19 | 0.08 | −0.44 | LDHBP1 | 0.20 | −0.90 | −0.95 | −0.44 | −0.36 |
| SPC24 | 0.83 | −1.03 | −1.24 | −0.31 | −0.33 | AC112247.1 | −1.20 | 1.48 | −0.51 | 1.37 | −1.36 | MIR455 | −0.18 | 0.34 | 1.24 | 0.38 | 0.88 |
| IL18BP | −0.65 | 0.03 | 0.35 | −0.07 | 0.15 | AL441963.1 | −0.29 | 0.50 | −0.08 | 0.21 | 0.04 | CHRNB2 | −0.05 | −0.23 | −0.08 | −0.19 | 0.12 |
| MIR3936 | −1.76 | 0.69 | 1.27 | 0.78 | −0.13 | RPS26P11 | −0.47 | −0.08 | 0.59 | −0.92 | −0.04 | AC005837.1 | 0.19 | −1.30 | 0.13 | −0.85 | −0.61 |
| CCDC9 | −0.50 | 0.21 | 0.28 | 0.08 | 0.08 | LINC01998 | 0.92 | −0.38 | 0.19 | 0.87 | −0.07 | AC008533.1 | −0.10 | −0.22 | 0.88 | −0.09 | 0.48 |
| RARRES2 | −1.35 | 0.79 | 1.72 | −0.71 | −0.08 | MAN1A2 | 0.15 | 0.00 | 0.05 | −0.07 | −0.10 | LINC01952 | −0.21 | 0.57 | −0.17 | 0.66 | −0.74 |
| GREB1 | −0.84 | 0.42 | 0.55 | 0.36 | 0.05 | PAX7 | −0.83 | −0.01 | 0.28 | 0.20 | 0.93 | MUC21 | 0.27 | 0.40 | −0.18 | 0.64 | −0.57 |
| AC055713.1 | −0.54 | −0.08 | 0.35 | 0.18 | 0.53 | CREB1 | 0.10 | −0.02 | 0.11 | −0.13 | −0.05 | MIR4295 | 0.33 | −0.26 | 0.13 | −0.26 | −0.12 |
| KDM7A-DT | 0.74 | −0.41 | −0.82 | −0.52 | −0.44 | AL513318.2 | −0.47 | 0.52 | 0.72 | 0.31 | 0.39 | AL360181.4 | 0.54 | 0.79 | −1.34 | 2.50 | 0.81 |
| FGF14-AS1 | −2.00 | 1.25 | 0.95 | 1.10 | 0.26 | PHPT1 | −0.17 | 0.12 | 0.04 | 0.17 | 0.12 | AC022469.2 | 0.35 | −0.49 | 0.83 | −1.05 | −1.22 |
| KIF7 | −0.94 | 0.19 | 0.70 | 0.23 | 0.34 | CICP26 | −0.83 | −0.76 | −0.49 | 2.34 | 0.01 | OACYLP | 0.15 | −0.94 | −1.01 | −0.26 | 0.13 |
| AL445673.1 | −1.03 | 0.21 | 1.21 | −0.18 | 0.02 | G28648 | 0.30 | 0.23 | 0.11 | 0.25 | 0.17 | CLPS | 0.71 | −0.87 | −0.10 | −0.98 | −1.92 |
| LINC00910 | −0.50 | −0.19 | 0.30 | −0.20 | 0.30 | AC131182.1 | −0.33 | 0.51 | 1.06 | 0.36 | 0.68 | G7822 | 0.11 | 0.01 | −0.14 | 0.04 | 0.49 |
| LINC00681 | −2.52 | 1.88 | 2.12 | 0.28 | 0.10 | AC022168.1 | −1.26 | −0.55 | 2.83 | −2.47 | 0.77 | OR1J2 | 0.23 | −1.24 | −0.10 | −0.44 | 1.09 |
| SNORA20 | −1.16 | 0.78 | 0.64 | 0.58 | −0.42 | AL117329.2 | −0.42 | −0.23 | −0.29 | 0.54 | 0.53 | AC073585.1 | −0.12 | 0.28 | −0.01 | −0.25 | −0.02 |
| AP000711.1 | −2.04 | 1.17 | 1.21 | 1.26 | 0.62 | MIR217HG | 1.04 | 0.50 | −1.38 | −0.51 | −0.42 | GTSCR1 | −0.36 | −1.14 | −1.60 | −0.35 | −2.10 |
| RCN2 | 0.39 | −0.18 | −0.14 | −0.07 | −0.07 | AC006480.2 | −0.55 | 0.70 | −0.44 | 1.09 | −0.30 | METTL11B | −0.33 | −1.07 | −2.06 | −0.03 | −1.22 |
| ASB3 | −0.50 | 0.37 | 0.34 | 0.13 | −0.12 | GAD1 | −0.50 | −0.05 | −0.36 | 0.13 | −0.19 | IDH2-DT | −0.23 | −0.38 | 0.31 | −0.22 | −0.74 |
| SNRPD1 | 0.62 | −0.70 | −0.34 | −0.54 | −0.03 | AL591806.3 | −0.38 | 0.12 | 0.50 | −0.03 | 0.83 | AP002001.1 | 0.24 | −0.20 | 1.50 | −0.58 | −0.16 |
| RSPH14 | −1.58 | 0.81 | 0.51 | 0.40 | 0.39 | AL033527.3 | −1.08 | 1.05 | 2.45 | 0.65 | 1.24 | AC009169.1 | −0.56 | 0.09 | −1.00 | 1.19 | −1.92 |
| OR6L2P | −0.90 | 0.62 | 0.54 | 0.17 | 0.06 | GIPR | 0.29 | −0.05 | −0.79 | 0.03 | −0.01 | AC005225.3 | −0.94 | 2.05 | 1.75 | −0.16 | −0.92 |
| AC009163.6 | −0.80 | 0.59 | 0.75 | 0.39 | 0.15 | RN7SL287P | −0.86 | −0.35 | 0.36 | −0.60 | 0.48 | ARRDC1-AS1 | −0.06 | −0.03 | −0.11 | 0.02 | 0.05 |
| RNA5SP74 | −1.81 | 0.67 | 0.53 | 1.42 | 0.02 | AC084880.1 | −0.31 | 0.24 | 0.28 | 0.32 | 0.21 | AL137784.2 | −0.08 | 0.68 | 0.25 | 0.14 | −0.30 |
| DTYMK | 0.62 | −0.43 | −0.52 | −0.12 | 0.07 | FOXF2 | −0.37 | 0.06 | −0.30 | 0.42 | −0.41 | AC021646.1 | 0.35 | −0.06 | −1.27 | −0.03 | 0.11 |
| FGD6 | 0.50 | −0.19 | −0.60 | 0.03 | −0.15 | HSD17B4 | 0.12 | 0.08 | 0.10 | 0.02 | 0.02 | AL391097.2 | −0.09 | 0.24 | −0.62 | 0.22 | −0.26 |
| RBM43P1 | 1.09 | −0.60 | −1.26 | 0.10 | 0.12 | AC115522.1 | 0.40 | −0.05 | −0.87 | −0.11 | −0.36 | LINC02271 | 0.45 | 1.10 | −0.42 | 2.02 | 0.30 |
| AC098591.2 | 1.45 | −0.39 | −0.31 | −0.29 | −0.10 | PKD2L1 | 0.86 | −0.56 | −0.74 | −0.40 | −0.36 | PC | 0.07 | −0.16 | −0.65 | 0.03 | −0.01 |
| CDR2 | −0.53 | −0.04 | 0.44 | −0.22 | 0.24 | AC097532.2 | −0.46 | 0.26 | −0.18 | 1.07 | 0.35 | AL022099.1 | 0.35 | −1.25 | 1.35 | 0.76 | 1.21 |
| AC106882.1 | 1.44 | −0.28 | −0.11 | 0.17 | 0.22 | AP000866.2 | 0.32 | −0.29 | 0.18 | −0.01 | 0.14 | AC068714.1 | −0.50 | −0.90 | 1.50 | 0.86 | 0.10 |
| AC131212.3 | −0.99 | 0.33 | −0.25 | 0.80 | 0.01 | CD7 | 0.47 | −1.29 | −0.77 | −0.90 | 0.13 | AP005262.1 | 0.45 | −0.81 | −0.80 | 1.29 | 0.25 |
| GDAP1L1 | −1.00 | 0.79 | 1.12 | 0.05 | 0.09 | MIR1180 | −0.87 | 1.52 | 0.61 | 0.49 | −0.55 | ASS1P6 | −0.53 | −0.65 | 2.18 | −1.10 | 1.31 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| GLUD1P2 | −1.59 | 0.81 | 1.34 | 0.08 | 0.43 | OR5B1P | −1.06 | −0.93 | 2.13 | −0.62 | 0.86 | PPIAP55 | 0.30 | −0.79 | −0.60 | −1.76 | −1.39 |
| EPB42 | −1.73 | 1.25 | 0.31 | 1.30 | −0.82 | FOXJ2 | −0.10 | 0.13 | 0.12 | 0.03 | −0.07 | AC006499.1 | −0.36 | −0.61 | −2.15 | 0.11 | −0.96 |
| RPL11 | 0.59 | −0.14 | −0.21 | −0.14 | −0.39 | BMS1P8 | −0.43 | −0.28 | 0.04 | 0.23 | 0.19 | GRAMD4P4 | −0.51 | −0.16 | 0.11 | 0.97 | 0.10 |
| CSNK1G3 | 0.48 | −0.05 | −0.27 | −0.05 | −0.20 | NR2C2 | 0.10 | 0.09 | −0.20 | 0.10 | −0.19 | OR5H14 | 0.20 | −0.92 | −1.84 | 1.55 | 0.80 |
| MCFD2 | 0.59 | −0.26 | −0.26 | −0.22 | −0.15 | LINC01366 | 1.08 | 0.58 | −0.60 | 0.40 | −1.00 | CR381653.2 | 0.17 | −1.70 | −0.20 | 0.89 | 3.01 |
| DLC1 | −0.90 | 0.30 | 1.26 | −0.10 | 0.14 | BX255925.3 | 0.22 | 0.05 | −0.54 | 0.32 | −0.11 | EXO5 | −0.04 | −0.21 | 0.15 | −0.06 | 0.36 |
| GPAM | −1.43 | 1.15 | 0.84 | 0.53 | −0.06 | LINC01611 | −0.86 | −0.31 | 0.88 | 0.34 | 0.73 | AL391361.2 | −0.52 | 1.16 | 0.27 | −0.37 | −0.25 |
| PBLD | −0.48 | 0.13 | 0.07 | 0.14 | −0.05 | MIR4459 | −0.36 | 0.17 | 0.18 | 0.22 | 0.31 | CYP26B1 | 0.05 | −0.07 | −0.54 | −0.08 | −0.38 |
| GAS2 | −1.24 | 0.55 | 1.24 | −0.02 | 0.27 | AC020916.1 | −0.21 | −0.33 | −0.30 | −0.10 | 0.18 | RN7SL709P | −0.25 | −0.59 | −0.58 | 0.04 | 0.06 |
| DLK2 | −0.78 | 0.19 | 0.40 | 0.20 | 0.53 | AC135050.6 | −0.16 | −0.13 | 0.34 | 0.08 | 0.55 | JAKMIP2 | −0.12 | −0.33 | 0.01 | −0.26 | 0.21 |
| PPP1R14A | −1.15 | −0.03 | −0.02 | −0.08 | −0.41 | RN7SL439P | −0.85 | −0.35 | 0.44 | −0.85 | −0.31 | AL358214.1 | 0.56 | −1.42 | −0.43 | 0.17 | 0.67 |
| GALNT17 | −1.14 | 0.72 | 0.78 | 0.56 | 0.24 | PPIP5K1 | 0.20 | 0.05 | −0.20 | 0.03 | −0.05 | IGSF21-AS1 | 0.28 | −1.63 | −0.57 | −0.32 | 0.44 |
| PTGR1 | 0.47 | −0.35 | −0.29 | 0.04 | 0.15 | RP6-206I17.2 | −1.33 | 0.19 | 1.11 | −0.98 | 0.45 | CAP1P2 | 0.22 | −0.75 | −0.16 | 0.08 | 0.17 |
| FILIP1 | −0.95 | 0.74 | 1.21 | 0.07 | −0.24 | ARL4AP4 | 0.37 | −0.30 | 0.28 | −0.39 | 0.19 | SALL1P1 | −0.36 | −1.72 | 0.89 | −1.29 | −0.68 |
| AC092127.1 | −0.84 | 0.14 | 0.42 | 0.08 | 0.20 | AC104982.1 | 0.44 | −0.06 | 0.07 | 0.15 | 0.48 | AL096803.1 | −0.28 | −1.12 | 2.35 | −0.97 | 0.82 |
| NUDT19 | 0.48 | −0.24 | −0.40 | −0.03 | −0.11 | AC104809.2 | −1.17 | −0.51 | 0.72 | −0.56 | −0.74 | AC009812.4 | 0.15 | −0.75 | −0.38 | 0.13 | 0.70 |
| AC138331.1 | −1.25 | 0.79 | 1.71 | −0.11 | −0.02 | CARD8 | −0.15 | −0.08 | 0.52 | −0.24 | 0.25 | RP4-604K5.2 | −0.15 | −0.01 | 1.03 | −0.30 | 0.86 |
| FUZ | −0.79 | 0.34 | 0.67 | 0.20 | 0.55 | NARSP2 | −0.93 | 0.57 | −0.15 | 0.44 | 0.35 | AC007216.3 | 0.07 | −0.13 | 0.01 | 0.15 | 0.19 |
| PRKRIP1 | −0.50 | 0.26 | 0.20 | 0.17 | 0.11 | AC010980.2 | 0.95 | 0.30 | −0.74 | 0.64 | −0.66 | RAD1 | 0.03 | −0.08 | 0.05 | −0.02 | 0.02 |
| MMP12 | 2.12 | −2.39 | −2.54 | −1.14 | −2.99 | OR7A5 | −0.50 | 0.37 | −0.52 | 1.17 | 0.39 | RNU1-78P | −1.18 | 0.47 | 0.97 | −0.62 | −0.51 |
| CCNC | 0.55 | −0.16 | −0.35 | −0.07 | −0.18 | AC069200.1 | −0.23 | −0.13 | −0.16 | 0.13 | 0.15 | AC121332.1 | −0.58 | 0.76 | −0.49 | 0.28 | −1.36 |
| GABRQ | 1.23 | −0.26 | −1.09 | 0.40 | −0.81 | PADI2 | −0.46 | 0.28 | 0.82 | 0.16 | 0.71 | AC114763.1 | 0.07 | −0.06 | 0.02 | −0.23 | 0.06 |
| PHF21A | −0.33 | 0.12 | 0.33 | 0.05 | 0.09 | HACE1 | −0.10 | 0.09 | 0.26 | 0.05 | 0.07 | AP003500.1 | 0.17 | −0.11 | −1.04 | −0.60 | −2.58 |
| LINC01118 | −0.98 | 0.08 | 0.21 | −0.08 | −0.42 | GPR63 | −0.36 | 0.14 | −0.35 | 0.07 | −0.34 | ELP2 | −0.03 | 0.10 | 0.34 | 0.01 | 0.14 |
| AL365356.5 | 2.32 | −0.56 | −1.39 | −0.53 | −0.98 | GAPDHP61 | 0.30 | −0.13 | −0.35 | 0.23 | −0.07 | AC063926.2 | −0.15 | 0.24 | 0.49 | 0.04 | 0.12 |
| PSMD10 | 0.61 | −0.28 | −0.33 | −0.13 | −0.37 | AGAP3 | −0.16 | 0.08 | −0.26 | 0.26 | 0.10 | AC087894.2 | −0.41 | 0.15 | 0.86 | −0.86 | −0.34 |
| B4GALNT2 | −1.50 | 0.75 | 1.14 | 0.23 | 0.23 | MIR5003 | 0.60 | −0.14 | 0.12 | −0.50 | −0.63 | IPCEF1 | 0.08 | −0.17 | 0.36 | −0.04 | 0.44 |
| PLA2G4A | 0.59 | −0.35 | −0.45 | −0.18 | −0.24 | NENF | −0.23 | 0.16 | 0.55 | −0.27 | −0.01 | RPL12P5 | 0.61 | −0.34 | −1.05 | 0.78 | 0.42 |
| G2582 | 2.46 | 0.02 | −0.20 | −0.37 | −0.49 | OR2A5 | −0.51 | −0.05 | −0.22 | 0.74 | 0.27 | DCUN1D2 | −0.03 | 0.01 | −0.14 | 0.23 | 0.01 |
| CYP4V2 | −0.74 | 0.35 | 0.81 | −0.03 | 0.50 | AC004672.1 | 0.21 | −0.07 | −0.21 | 0.18 | −0.01 | AL136172.1 | 0.30 | 0.26 | −0.19 | 1.15 | −0.36 |
| RAP2C-AS1 | −0.55 | 0.22 | 0.31 | 0.15 | 0.02 | NIPAL3 | −0.19 | 0.43 | 0.47 | 0.13 | 0.03 | SMR3B | 0.37 | −1.28 | −0.47 | −0.48 | −1.24 |
| BEX5 | −1.11 | 0.42 | 0.57 | 0.45 | 0.36 | EIF4A1P8 | −0.49 | 0.21 | 1.06 | −0.02 | 0.65 | DEFB136 | 0.32 | −0.28 | −1.67 | 0.24 | −1.69 |
| BCL6 | −0.42 | 0.22 | 0.32 | 0.16 | 0.11 | LINC02433 | −0.89 | 0.43 | 0.44 | 1.30 | 1.83 | LINC02022 | −0.67 | 1.35 | 0.61 | 1.71 | −0.23 |
| C11orf68 | −0.47 | 0.12 | 0.20 | −0.02 | 0.12 | IGKV1OR2-108 | −0.65 | −0.50 | 1.41 | 0.40 | 1.45 | LINC01787 | −0.25 | 0.25 | −1.58 | 0.62 | −0.62 |
| RPL28 | 0.54 | −0.17 | −0.22 | −0.28 | −0.50 | AL691449.1 | 1.05 | −1.06 | 0.50 | −0.84 | −0.49 | NUTF2P7 | −0.22 | 0.91 | −0.05 | 0.11 | −1.36 |
| CISD3 | 0.55 | −0.37 | −0.42 | 0.06 | −0.05 | LINC01098 | 0.92 | −1.11 | −0.63 | −0.39 | 0.09 | RN7SKP144 | 0.64 | −0.73 | −1.51 | 0.38 | −1.33 |
| MXRA7 | −0.72 | 0.36 | 0.67 | −0.12 | −0.05 | FO393401.1 | −0.53 | −0.45 | 0.32 | −0.36 | 0.49 | OR13F1 | −0.43 | 0.11 | 1.56 | 0.68 | 0.29 |
| NBPF13P | −1.17 | −0.17 | 0.50 | 0.02 | 0.32 | AP002957.1 | 0.40 | −0.26 | −0.65 | 0.11 | 0.46 | AL606804.1 | −0.26 | −0.27 | −1.49 | 1.50 | 0.12 |
| DIP2B | 0.43 | 0.00 | −0.47 | 0.10 | −0.33 | G10734 | −0.36 | 0.02 | 0.44 | 0.32 | 0.06 | AC005772.1 | 0.47 | −0.58 | −0.47 | 1.37 | −0.12 |
| KDELR2 | 0.57 | −0.32 | −0.06 | −0.33 | −0.14 | AP000437.1 | −0.26 | 0.10 | 0.77 | 0.28 | 0.62 | RTP2 | 1.18 | −0.32 | −2.50 | 1.61 | −1.90 |
| C12orf49 | 0.50 | −0.06 | −0.25 | −0.08 | −0.20 | RN7SL859P | 0.49 | −1.42 | −0.92 | −0.58 | 0.68 | AC022166.1 | 0.31 | 0.34 | 0.92 | −1.21 | 0.24 |
| FRS3 | −0.68 | 0.26 | 0.12 | 0.30 | 0.02 | AOC1 | −0.39 | −0.07 | 0.39 | −0.16 | 0.05 | AC138783.12 | −0.20 | 0.33 | 1.25 | 1.38 | 1.37 |
| RPS2P5 | 0.71 | −0.20 | −0.30 | 0.11 | −0.45 | AGAP5 | −0.45 | 0.29 | 1.04 | −0.42 | 0.45 | LINC02183 | −0.22 | −2.31 | 0.71 | −0.10 | 1.41 |
| LUC7L | −0.45 | 0.15 | 0.28 | 0.04 | 0.19 | HSD3BP2 | −1.06 | −0.54 | 1.18 | 1.03 | 1.24 | AC010291.1 | 0.35 | −1.29 | 0.26 | 0.44 | 0.98 |
| PLEKHB2 | 0.37 | −0.23 | −0.37 | −0.13 | −0.34 | LINC01058 | −0.53 | 0.71 | 0.54 | 0.28 | 0.37 | KRT8P10 | −0.55 | −0.42 | 0.79 | 0.97 | 2.34 |
| AIMP1P1 | −0.86 | 0.82 | 1.12 | 0.38 | 0.06 | FBXL3 | 0.20 | 0.13 | 0.06 | 0.00 | −0.28 | KRT18P66 | −0.64 | −0.42 | 0.99 | −0.77 | 0.57 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| BID | 0.54 | −0.64 | −0.63 | −0.03 | −0.14 | AL360093.1 | −0.39 | 0.00 | 0.57 | −0.21 | 0.26 | RPL4P1 | 0.26 | −1.00 | 0.98 | 0.16 | 0.09 |
| ADORA2BP1 | 2.53 | −2.23 | −2.07 | −0.58 | −2.42 | FLG2 | −0.56 | 0.54 | 1.74 | 1.63 | −0.17 | AC091163.1 | −0.54 | 0.24 | 2.30 | 2.05 | 2.51 |
| C11orf91 | 1.83 | −0.75 | −0.69 | −0.60 | −0.38 | AC018868.1 | 0.37 | −0.19 | −0.63 | 0.01 | 0.00 | AL157770.1 | −0.17 | 0.85 | 1.64 | −0.26 | 0.14 |
| ACTRIB | −0.50 | 0.23 | 0.10 | 0.49 | 0.18 | AL662800.1 | 0.43 | −0.33 | 0.29 | −0.17 | 0.15 | AL353148.1 | −0.24 | −0.22 | −0.95 | −0.17 | −1.00 |
| ARHGEF25 | −1.11 | 0.38 | 1.58 | 0.12 | −0.04 | RNU6-444P | 0.44 | −0.28 | 0.40 | −0.36 | −0.04 | AL583808.1 | −0.17 | 0.91 | 0.41 | 0.82 | −0.11 |
| KPNA4 | 0.51 | −0.19 | −0.41 | −0.10 | −0.32 | MTND2P29 | −1.50 | −0.31 | 1.18 | −1.31 | −0.79 | AC022639.1 | −0.20 | −0.20 | −1.73 | 0.83 | −1.31 |
| MVB12B | −0.38 | 0.28 | 0.23 | 0.33 | 0.18 | AC004477.3 | 0.33 | 0.09 | −0.30 | 0.09 | −0.08 | OR7E24 | 0.37 | −1.95 | −0.59 | 0.63 | 0.28 |
| ARCN1 | 0.52 | −0.27 | −0.29 | −0.32 | −0.26 | OLIG2 | −0.76 | −0.76 | −1.23 | 0.36 | 0.74 | AL356583.3 | 0.66 | −2.22 | −1.07 | −1.28 | −2.81 |
| EOGT | 0.47 | −0.28 | −0.45 | −0.09 | −0.08 | C1S | 0.29 | −0.12 | 0.43 | −0.31 | −0.11 | PHBP9 | −0.08 | 0.11 | 0.21 | 0.26 | 0.31 |
| SRGN | 1.37 | −1.25 | −0.40 | −0.16 | −0.41 | AC015815.8 | −0.72 | −0.02 | 2.88 | −0.96 | 0.78 | RN7SL614P | 0.15 | −0.70 | −0.07 | −1.08 | −0.23 |
| PABPC5-AS1 | −2.08 | 0.44 | 2.68 | 0.72 | 0.89 | ARL17A | −0.20 | −0.18 | 0.58 | −0.26 | 0.57 | AC024909.1 | −0.20 | −0.53 | −1.91 | 1.13 | −0.71 |
| FABP5P10 | 3.05 | −0.75 | −1.86 | 0.04 | −1.35 | MTA3 | −0.09 | 0.20 | 0.10 | 0.15 | −0.04 | CA10 | −0.18 | −0.64 | −0.61 | −0.16 | −0.92 |
| PTPRU | −0.60 | 0.34 | 0.74 | 0.07 | 0.09 | AC097634.3 | −0.63 | −0.62 | 0.31 | 0.35 | 0.67 | ATXN2L | 0.03 | −0.12 | −0.32 | 0.04 | 0.05 |
| AL139330.1 | 1.88 | −1.24 | −2.00 | 0.49 | −0.21 | ARHGEF4 | 0.25 | −0.02 | −0.44 | 0.34 | −0.01 | RN7SL480P | −0.28 | 0.97 | −0.10 | 0.99 | −0.75 |
| RNGTT | 0.31 | −0.19 | −0.32 | −0.05 | 0.06 | AHCYP1 | 1.43 | −0.30 | 0.12 | 0.27 | −1.23 | MTND1P30 | −0.35 | −0.34 | −2.63 | 0.37 | −1.60 |
| AC120042.2 | 2.27 | −0.03 | −0.97 | 0.14 | −1.42 | BCL2L13 | 0.12 | 0.05 | −0.12 | 0.06 | −0.14 | NTPCR | 0.03 | 0.03 | 0.08 | 0.19 | 0.18 |
| DR1 | 0.49 | −0.15 | −0.26 | 0.09 | −0.18 | AC009119.1 | −0.41 | 0.75 | −0.71 | 0.17 | −0.34 | LINC01630 | −0.19 | −0.11 | −2.44 | 0.49 | −1.13 |
| DDAH2 | −0.66 | 0.36 | 0.41 | 0.00 | −0.15 | AL139010.1 | −0.80 | −0.09 | 0.74 | 0.41 | 0.21 | G33057 | 0.40 | 1.04 | −0.09 | −0.28 | −1.57 |
| MRPL39 | 0.45 | −0.04 | −0.23 | −0.12 | −0.30 | AC105046.1 | 0.33 | −0.08 | −0.19 | 0.13 | −0.43 | RPS6P14 | −0.74 | 0.67 | −0.63 | −0.31 | −1.84 |
| AL391280.1 | 0.79 | −0.57 | −0.67 | −0.05 | 0.05 | AC024884.1 | 1.15 | −2.13 | 0.12 | −0.18 | −0.26 | OR51C4P | 0.40 | −1.26 | −1.00 | 0.39 | 1.38 |
| DERA | 0.39 | −0.13 | −0.27 | −0.12 | −0.35 | AC134312.6 | 1.09 | −2.04 | 1.07 | 0.17 | 2.62 | RNU6-1136P | 0.16 | 0.66 | 0.16 | 0.98 | 0.27 |
| DCDC2C | −1.92 | −0.08 | 1.95 | 1.21 | 1.79 | AC109631.1 | 0.41 | −0.07 | −0.29 | 0.10 | 0.05 | AC110014.1 | −0.34 | 0.63 | −1.00 | 0.19 | −0.53 |
| HSPBP1 | 0.59 | −0.33 | −0.88 | 0.16 | −0.33 | ST6GALNAC4 | 0.25 | −0.36 | −0.23 | −0.22 | 0.01 | AC131212.1 | 0.39 | −2.27 | 0.86 | −0.10 | 1.13 |
| NXT1 | 0.68 | −0.56 | −0.57 | −0.26 | −0.32 | AL392086.1 | 2.15 | 0.06 | −1.82 | 0.46 | −0.76 | GM2AP1 | −0.59 | −0.02 | −0.09 | 0.59 | −0.43 |
| FAM32A | 0.33 | −0.07 | −0.33 | −0.01 | −0.39 | AP003419.3 | −0.48 | 0.61 | 0.58 | −0.07 | −0.16 | AC020595.1 | 0.56 | −0.32 | −3.38 | 0.73 | −2.76 |
| ACADSB | −0.60 | 0.79 | 0.96 | 0.44 | 0.42 | INPP5K | −0.13 | 0.19 | −0.16 | 0.21 | −0.17 | RPL22P3 | −0.13 | −0.17 | 0.05 | 0.34 | 0.64 |
| PCSK1 | 0.77 | −0.38 | −0.28 | −0.29 | −0.29 | DALRD3 | −0.19 | 0.12 | 0.05 | 0.18 | 0.15 | MON2 | 0.03 | 0.03 | 0.14 | −0.01 | 0.06 |
| EIF3E | 0.54 | −0.13 | −0.28 | −0.08 | −0.29 | NPFFR2 | −0.79 | −0.76 | 0.15 | −0.41 | 0.27 | CYP2C19 | 0.23 | −1.59 | 0.02 | −0.60 | 0.10 |
| SSR2 | 0.39 | −0.20 | −0.13 | −0.13 | −0.01 | GCC1 | 0.09 | 0.05 | −0.22 | 0.03 | −0.23 | AC084398.2 | −0.14 | −0.30 | 0.22 | −0.17 | −0.31 |
| RPS14 | 0.45 | −0.05 | −0.15 | 0.00 | −0.41 | AC012676.4 | −0.35 | −0.40 | 0.15 | −0.04 | 0.67 | LINC01142 | −0.15 | −0.78 | 1.47 | −0.91 | 0.25 |
| MEIS2 | −0.36 | 0.34 | 0.11 | 0.13 | −0.12 | RNA5SP390 | −1.05 | 1.39 | −1.14 | 1.47 | −2.04 | RPS2P45 | −0.08 | −0.47 | −0.35 | −0.27 | 0.44 |
| G12464 | −1.39 | 0.92 | 1.38 | 0.17 | −0.55 | NR6A1 | −0.19 | 0.23 | 0.13 | 0.01 | 0.01 | LRRIQ4 | 0.25 | −1.01 | 0.13 | −0.46 | −0.63 |
| FAAH | −0.70 | 0.13 | 0.10 | 0.57 | 0.60 | CYP39A1 | −0.30 | 0.51 | 0.80 | 0.49 | 0.13 | AP001024.1 | 0.16 | −0.45 | −2.12 | 1.04 | −0.41 |
| AC138207.5 | 1.11 | −0.72 | −0.86 | −0.43 | −0.33 | LILRB1 | 0.59 | −1.01 | −0.38 | −0.53 | −0.72 | AL136131.2 | 0.27 | −0.57 | −0.82 | −0.73 | −1.84 |
| PARP6 | −0.28 | 0.13 | 0.10 | 0.13 | 0.08 | AC016737.2 | −0.57 | −0.07 | 0.01 | 0.31 | 0.41 | DYNAP | −0.24 | −0.29 | −0.60 | 0.15 | −0.56 |
| SERP1 | 0.46 | −0.35 | −0.34 | −0.27 | −0.01 | AP005018.1 | 1.10 | −1.61 | −1.77 | −0.09 | 0.01 | G3148 | −0.15 | −0.06 | −0.10 | −0.83 | −0.21 |
| DYNC1H1 | 0.25 | −0.04 | −0.16 | −0.10 | −0.21 | HMGN2P41 | 0.99 | −0.21 | 0.36 | −1.05 | 0.16 | AL121672.3 | 0.11 | 0.56 | 0.28 | 0.33 | −0.19 |
| FHDC1 | 0.62 | 0.08 | −0.31 | 0.06 | −0.37 | AC079209.2 | 0.56 | −1.22 | 0.06 | −0.52 | 0.53 | CARS-AS1 | −0.08 | −0.26 | −0.25 | −0.04 | −0.52 |
| AC245297.2 | −1.03 | 0.06 | 1.08 | −0.29 | 0.62 | LINC01715 | 0.43 | −0.25 | 1.01 | −0.42 | 0.52 | FER1L6-AS1 | 0.28 | −0.71 | −0.87 | −0.24 | −0.51 |
| GTF2A2 | 0.71 | −0.27 | −0.39 | −0.28 | −0.25 | DBNDD1 | 0.31 | 0.42 | −0.23 | 0.31 | −0.04 | ALG1L3P | −0.84 | 0.85 | −0.72 | 0.78 | −0.93 |
| COLEC12 | −1.08 | 0.75 | 1.05 | 0.21 | 0.15 | AL450442.1 | −1.22 | 0.60 | 1.24 | 1.32 | 0.51 | NPM1P9 | 0.10 | −0.62 | −0.62 | 0.02 | 0.65 |
| METTL4 | 0.47 | −0.16 | −0.03 | −0.23 | −0.03 | CFHR1 | 1.00 | −1.47 | −2.11 | −0.14 | −0.21 | AC007536.1 | 1.17 | −1.64 | −1.00 | −2.04 | −0.06 |
| CLVS1 | −1.02 | 0.53 | 0.59 | 0.39 | −0.13 | HMGB1P21 | 0.31 | −0.04 | −0.43 | −0.15 | −0.40 | AC005757.1 | −0.10 | −0.38 | 0.25 | −0.37 | 0.59 |
| DUSP5 | 0.78 | −0.61 | −0.96 | −0.35 | −0.76 | AC108673.1 | −1.42 | −0.90 | 1.24 | 0.53 | 0.66 | AC022400.2 | 0.07 | −0.30 | 0.31 | −0.11 | 0.52 |
| ESRP1 | 0.63 | −0.03 | −0.46 | 0.18 | −0.28 | AC004917.1 | 0.55 | −0.41 | −0.27 | 0.06 | −0.28 | AL360091.3 | −0.12 | 0.20 | 0.49 | 0.14 | 0.42 |
| AASDHPPT | 0.53 | −0.28 | −0.19 | −0.10 | 0.08 | AL391863.2 | 0.53 | 0.53 | −0.26 | −0.41 | −0.51 | GAS2L3 | −0.03 | −0.22 | 0.28 | −0.27 | 0.23 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| SMUG1-AS1 | −1.19 | 1.15 | 1.38 | 0.80 | 0.56 | MEX3A | 0.26 | −0.06 | 0.31 | −0.45 | 0.04 | LINC00692 | 0.43 | −0.18 | 0.65 | 0.78 | 2.42 |
| NUSAP1 | 0.81 | −0.68 | −0.86 | −0.01 | −0.07 | G18244 | 0.37 | −0.48 | −1.06 | 0.04 | −0.25 | AC010998.1 | −0.76 | 0.56 | 1.03 | −0.02 | 0.76 |
| SDHAF3 | 0.62 | −0.19 | −0.24 | −0.10 | −0.25 | AC005358.1 | −0.80 | −0.82 | −0.70 | 0.74 | 1.20 | RPSAP22 | 0.32 | 0.24 | −1.44 | −0.29 | −1.62 |
| MERTK | −1.02 | 0.20 | 0.78 | 0.37 | 0.15 | AL591242.1 | −0.67 | −0.13 | 0.07 | 0.13 | −0.15 | MORF4L1P3 | −0.17 | 0.29 | −1.39 | 0.36 | −0.35 |
| PLCB3 | 0.53 | −0.39 | −0.99 | 0.10 | −0.21 | RNA5SP82 | 0.49 | −0.04 | −0.30 | −0.11 | −0.21 | AL138787.1 | 0.18 | 1.40 | −2.06 | 0.53 | −2.10 |
| AMELX | −1.56 | 0.38 | 1.50 | −0.63 | 0.10 | SRRM2 | −0.15 | 0.07 | −0.12 | 0.12 | 0.13 | LCMT1-AS2 | 0.06 | 0.28 | 0.43 | −0.03 | −0.10 |
| ELAVL1 | 0.31 | −0.22 | −0.47 | −0.07 | −0.18 | CAPN13 | −0.55 | 0.34 | 0.43 | 0.73 | 0.92 | OR9H1P | −0.13 | −0.37 | −0.13 | 0.49 | 0.53 |
| AC132938.2 | −1.44 | 0.49 | 0.27 | 0.67 | 0.41 | AC010998.2 | −0.45 | 0.40 | −0.27 | 0.73 | −0.59 | LINC01949 | −0.23 | 0.11 | −0.99 | 0.77 | −0.71 |
| CDAN1 | −0.53 | 0.15 | 0.10 | 0.24 | 0.15 | HEIH | 0.34 | −0.09 | 0.31 | −0.20 | −0.11 | AC009055.2 | −0.32 | 0.59 | −0.64 | −0.30 | −1.06 |
| AC011742.3 | 1.03 | −0.59 | −0.76 | −0.13 | −0.24 | ANKRD7 | −0.64 | 0.47 | −0.75 | −0.10 | −1.45 | AC106794.2 | −0.54 | 0.59 | −1.05 | 2.16 | −1.09 |
| FAM91A1 | 0.36 | −0.14 | −0.30 | −0.07 | −0.26 | RN7SK | −0.21 | 0.41 | 0.59 | −0.10 | −0.16 | RPL17P34 | 0.19 | −0.88 | −0.60 | 0.10 | −0.30 |
| IPO5 | 0.57 | −0.34 | −0.46 | −0.24 | −0.29 | CEP164 | −0.16 | −0.05 | −0.15 | 0.04 | 0.07 | AL133338.2 | −0.16 | 0.71 | 0.90 | 0.94 | 1.16 |
| CXCL10 | 2.18 | −2.46 | −1.95 | −3.04 | −1.86 | HOXC-AS3 | −0.31 | −0.10 | −0.71 | 0.06 | −0.37 | AC114689.1 | 0.38 | −1.86 | −0.06 | 0.82 | −0.19 |
| STARD10 | 0.52 | 0.09 | −0.64 | 0.27 | −0.47 | LINC01011 | −0.29 | −0.02 | 0.83 | 0.15 | 0.57 | GAGE10 | 0.27 | −0.19 | 0.67 | −0.07 | −0.35 |
| NPNT | 0.52 | −0.40 | −0.51 | −0.13 | −0.17 | RPL31P63 | 1.04 | −1.05 | 0.27 | −0.84 | 0.89 | KRTAP4-2 | −1.10 | 0.57 | 0.81 | −1.33 | −2.89 |
| GAS2L2 | −1.47 | 0.06 | −0.44 | 0.78 | 0.46 | RNU6-1305P | 0.51 | −0.35 | 0.20 | 0.22 | 0.75 | SLC9A3P3 | 0.28 | 0.15 | −0.49 | −1.46 | −1.59 |
| DCK | 0.63 | −0.06 | −0.08 | 0.01 | −0.21 | OR8B8 | 1.12 | −1.32 | −1.20 | 0.23 | 1.59 | NPM1P49 | 0.18 | 0.93 | 0.65 | 0.21 | −0.38 |
| CNOT7 | 0.52 | −0.13 | −0.41 | 0.02 | −0.27 | AP001092.1 | 0.97 | −2.11 | 0.08 | −0.21 | 0.36 | SMIM18 | 0.08 | −0.36 | 0.69 | −0.49 | 0.48 |
| NYNRIN | −0.68 | 0.58 | 0.87 | 0.12 | −0.08 | G40079 | 1.35 | −1.08 | −0.45 | 0.26 | −0.39 | AC091167.5 | 0.70 | −0.20 | −0.76 | 0.35 | −0.68 |
| ASCL2 | 0.98 | −0.38 | −1.21 | 0.32 | −0.24 | AC068418.2 | −0.87 | 0.18 | −0.33 | −0.08 | −1.06 | AC092691.3 | −0.62 | −0.74 | 1.56 | 0.68 | 1.79 |
| LINC02249 | −1.50 | 1.73 | 0.07 | 0.93 | −0.12 | HNRNPA1P57 | −1.01 | 0.53 | 2.78 | 0.28 | 1.49 | AC091987.1 | −0.33 | −1.06 | −0.61 | −0.05 | −1.40 |
| G10958 | −0.54 | 0.43 | 0.70 | 0.35 | 0.33 | AC013356.3 | −0.51 | 0.40 | 0.30 | −0.20 | −0.54 | ERLIN2 | 0.03 | −0.01 | −0.03 | −0.04 | 0.05 |
| COCH | −1.30 | 0.48 | 1.37 | 0.16 | 0.50 | AC018638.2 | −0.27 | 0.28 | −0.08 | 0.10 | −0.11 | CNGB3 | −0.09 | 0.42 | −0.83 | 0.45 | −0.68 |
| PSG3 | −1.56 | 0.13 | 0.49 | 0.28 | −0.39 | AL121972.1 | −0.66 | −0.47 | 1.65 | −0.77 | 0.75 | KRTAP17-1 | −1.08 | 0.07 | 0.87 | −0.01 | 2.31 |
| RP11-353N4.8 | −1.85 | 1.69 | 1.39 | 0.54 | −0.45 | AL137058.2 | 1.34 | −0.02 | 0.87 | −0.55 | −0.90 | AC005014.2 | 0.33 | 0.61 | 1.09 | −0.56 | −1.19 |
| FAM228A | −1.31 | 0.46 | 1.70 | −0.24 | 0.03 | AC004828.1 | −0.83 | −0.36 | 0.27 | −0.14 | 1.26 | AC090950.2 | 0.18 | −0.26 | 0.09 | −0.45 | −0.49 |
| SFXN3 | −0.46 | 0.39 | 0.43 | 0.18 | 0.16 | MIR378H | −0.54 | 0.59 | 0.40 | 0.63 | 0.15 | HLA-Z | 0.28 | −0.66 | −0.36 | 1.62 | 0.53 |
| MYBPC1 | −1.58 | 0.94 | 1.01 | 1.15 | 0.47 | POTEC | −0.74 | 0.12 | 0.29 | −0.08 | −0.57 | OR5L2 | 0.56 | −1.32 | −0.88 | 1.57 | 1.32 |
| P2RX1 | −1.10 | 0.23 | 0.92 | −0.14 | 0.11 | AL356413.1 | −1.00 | 0.49 | −0.33 | −0.59 | 0.02 | LINC00430 | −0.52 | 0.59 | −0.63 | 1.21 | −0.32 |
| AC018521.7 | −1.17 | 0.62 | 1.29 | 0.33 | 0.70 | CCDC126 | −0.25 | 0.15 | 0.34 | −0.22 | −0.15 | AC011726.3 | 0.12 | 0.52 | 0.95 | −0.32 | −0.55 |
| NT5C | 0.47 | −0.32 | −0.74 | 0.15 | −0.03 | AC124798.1 | 0.41 | −0.45 | −0.62 | 0.22 | 0.03 | RPS3AP15 | −0.42 | 0.35 | 0.96 | −0.44 | 0.77 |
| DHRS3 | −0.54 | 0.53 | 0.08 | 0.48 | −0.15 | LINC02306 | −0.92 | 0.04 | 0.98 | 1.09 | 0.35 | AL161891.1 | 0.04 | 0.14 | −0.22 | 0.10 | −0.17 |
| MYLIP | −0.55 | 0.31 | 0.43 | 0.37 | 0.23 | PTPRD-AS2 | 1.19 | −0.18 | −1.26 | 0.19 | −0.96 | DLG4 | −0.06 | 0.02 | 0.26 | −0.05 | 0.16 |
| LPP-AS2 | −0.72 | 0.13 | 0.46 | 0.28 | 0.27 | LIG1 | −0.17 | −0.13 | −0.12 | 0.02 | 0.20 | NF1P6 | 0.34 | −0.05 | −0.90 | −0.49 | −0.29 |
| MRAS | −1.08 | 0.68 | 1.11 | 0.07 | 0.34 | LINC01883 | −0.73 | 0.30 | 1.80 | 0.37 | 0.93 | PATE3 | −0.20 | −0.42 | 0.65 | −1.62 | −0.61 |
| METTL9 | 0.57 | −0.25 | −0.16 | −0.17 | −0.14 | G12578 | −0.66 | −0.51 | −0.67 | 0.78 | −1.35 | PPM1AP1 | 0.18 | −0.74 | 0.11 | 0.95 | 1.32 |
| BRAFP1 | −1.37 | 0.81 | 1.11 | 0.32 | 0.57 | AC013394.1 | 0.20 | −0.05 | −0.25 | 0.06 | −0.03 | LINC01134 | −0.11 | −0.39 | −0.99 | −0.08 | −0.47 |
| NOL9 | 0.35 | −0.30 | −0.44 | −0.01 | −0.03 | AC019080.2 | 1.05 | −2.13 | −0.17 | 0.00 | 0.28 | FGFR1OP | 0.03 | −0.18 | 0.11 | −0.07 | 0.13 |
| IL5 | −1.20 | 0.19 | 0.30 | 0.00 | −0.05 | AC091563.1 | −0.38 | 0.37 | 1.21 | 0.09 | 0.49 | PGBD2 | −0.05 | −0.10 | 0.15 | 0.15 | 0.30 |
| ECM2 | −0.77 | 0.54 | 0.93 | 0.10 | −0.06 | MYLK4 | −0.23 | 0.12 | 0.23 | 0.29 | 0.34 | BX284668.3 | −0.42 | 0.21 | 0.14 | 0.85 | 1.55 |
| PER3 | −0.51 | 0.39 | 0.60 | 0.19 | −0.11 | AC092608.1 | 0.50 | −0.73 | −1.13 | −0.01 | −0.22 | KRTAP19-5 | 0.52 | 1.77 | −0.60 | 1.02 | −2.06 |
| NBPF10 | −0.35 | 0.15 | 0.29 | −0.02 | 0.28 | ARSF | 0.41 | 0.09 | −0.19 | 0.78 | 0.41 | AL080273.1 | 0.40 | −0.18 | 1.84 | 1.11 | 1.66 |
| AC023794.5 | −1.05 | 0.66 | 1.27 | 0.59 | 0.51 | AL133330.2 | −0.92 | −0.18 | −1.39 | 1.05 | −2.22 | GRK5-IT1 | −0.09 | −0.50 | 0.90 | −0.46 | 0.05 |
| MXD3 | −0.67 | 0.09 | −0.18 | 0.40 | 0.19 | ACTG1P20 | −0.35 | 0.25 | 0.54 | 0.48 | 0.12 | AL357060.1 | 0.08 | −0.03 | −0.01 | −0.12 | −0.28 |
| SERPINA5 | −1.47 | 1.21 | 1.87 | 0.61 | 0.96 | AC009994.1 | 0.62 | 0.10 | 0.27 | −0.40 | −0.68 | AC062028.1 | 0.45 | −0.31 | −1.58 | 0.70 | −0.98 |
| FGF1 | −1.17 | 0.56 | 0.09 | 0.29 | −0.36 | AL355075.2 | −0.33 | 0.55 | 0.14 | 0.63 | −0.44 | CD5L | 0.17 | −0.42 | −0.01 | 0.67 | 0.64 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| LINC02202 | −1.25 | 0.52 | 0.97 | 0.09 | 0.19 | RN7SKP173 | −0.28 | −0.19 | −0.04 | 0.20 | 0.44 | AC136475.9 | 0.49 | −1.29 | 0.00 | −0.59 | −1.24 |
| FKBP3 | 0.51 | −0.27 | −0.15 | −0.16 | −0.11 | AC025766.1 | 0.45 | 0.03 | 0.34 | 0.10 | 0.44 | AP001469.1 | −0.09 | 0.07 | 0.61 | 0.14 | 0.30 |
| LHFPL6 | −0.77 | 0.43 | 1.20 | 0.14 | 0.02 | CMTM7 | −0.28 | −0.02 | 0.36 | −0.26 | −0.15 | AC011257.1 | 0.46 | −1.57 | 0.00 | −0.19 | 1.48 |
| ELOF1 | 0.45 | −0.15 | −0.46 | −0.07 | −0.55 | AC009716.1 | 0.60 | −0.60 | −0.41 | −0.12 | −0.40 | LINC02099 | 0.12 | −0.43 | −0.58 | 0.34 | 0.01 |
| PLEKHG4 | −0.55 | 0.34 | 0.00 | 0.34 | 0.19 | AC018682.1 | 0.24 | −0.38 | 0.28 | −0.25 | 0.17 | FTLP5 | −0.74 | −0.17 | 0.48 | −0.65 | 1.39 |
| PPIC | 0.60 | −0.07 | 0.08 | 0.07 | −0.10 | AC097382.1 | 0.37 | −0.05 | −0.61 | 0.11 | −0.22 | CHD9 | −0.02 | 0.13 | 0.02 | 0.03 | −0.05 |
| DOCK3 | −0.80 | 0.61 | 0.88 | 0.37 | 0.14 | LRMDA | −0.25 | 0.00 | 0.29 | −0.01 | 0.07 | CST6 | −0.10 | 0.81 | 0.56 | 0.56 | −0.25 |
| SLC4A1 | −1.65 | 0.64 | 0.47 | 0.46 | −2.13 | ERICH3-AS1 | −0.81 | 0.58 | 0.09 | 0.15 | −0.79 | LINC02294 | 0.53 | −0.78 | −0.66 | 1.17 | 1.71 |
| AC009318.1 | −0.47 | 0.17 | 0.61 | −0.03 | 0.31 | AC104984.3 | −0.35 | −0.14 | 0.20 | −0.38 | 0.26 | RPL7AP3 | −0.13 | −0.29 | 0.38 | 0.14 | 0.76 |
| AC009974.1 | −1.19 | 1.00 | 1.39 | 0.34 | 0.36 | AC090286.3 | 0.43 | −0.16 | −0.56 | −0.25 | −0.56 | AL442003.1 | 0.06 | −0.35 | −0.11 | −0.25 | −0.05 |
| PDCD2L | 0.83 | −0.31 | −0.84 | −0.18 | −0.61 | PSORS1C3 | −0.43 | 0.36 | −0.50 | 0.35 | −0.41 | ATP6V1B1-AS1 | −0.36 | 0.56 | −0.31 | 2.30 | 0.32 |
| CAMK2A | −1.20 | 0.27 | 0.07 | −0.05 | 0.03 | FBXO39 | 0.34 | −0.69 | −1.01 | 0.34 | −0.12 | LINC02251 | 0.28 | 1.22 | −0.81 | 0.40 | −2.20 |
| RTEL1P1 | −0.75 | 0.02 | 0.13 | 0.15 | 0.19 | OR10A2 | 0.44 | −1.00 | −1.48 | 0.34 | −0.09 | AC005100.1 | 0.24 | −0.93 | −1.47 | −0.19 | −1.43 |
| RPSAP52 | 2.09 | −1.36 | −1.82 | −0.26 | −1.68 | AC095040.1 | −0.65 | 0.50 | 1.31 | 0.58 | 0.04 | MAGEB5 | 0.67 | −0.01 | 0.70 | −0.05 | 0.30 |
| G23195 | −1.21 | 0.73 | 0.32 | 0.78 | 0.22 | G6795 | −0.45 | 0.00 | −0.33 | −0.03 | −0.19 | RHO | −0.29 | −0.92 | 0.75 | −0.65 | −0.15 |
| AC024075.2 | −0.44 | 0.32 | 0.54 | 0.10 | 0.21 | AC006504.4 | −1.02 | −0.39 | −1.96 | 1.41 | −0.84 | AC025431.1 | 0.44 | −0.76 | −1.26 | 0.79 | 0.92 |
| POU5F2 | −0.44 | 0.03 | 0.52 | 0.07 | 0.44 | AHRR | −0.28 | −0.31 | −0.09 | −0.16 | 0.40 | AC118138.2 | −0.23 | −1.22 | 0.21 | −0.87 | 0.42 |
| BX842242.1 | −1.35 | 1.13 | 0.07 | 0.77 | −0.08 | AC010536.1 | −0.38 | 0.35 | −0.05 | 0.48 | 0.12 | HSPA8P7 | −0.30 | −0.60 | 0.11 | −0.26 | −0.47 |
| ATP13A3 | 0.69 | −0.67 | −0.82 | −0.32 | −0.35 | RNU6-69P | 0.87 | −0.18 | 0.33 | −0.21 | −0.25 | AL031667.3 | 0.11 | 0.95 | −0.32 | 1.03 | −0.10 |
| RN7SL127P | 0.95 | −0.56 | −0.17 | −0.57 | 0.05 | SCML2P2 | −0.53 | 0.69 | 0.74 | 0.67 | 0.76 | SUCLG2P2 | 0.14 | −0.07 | 0.56 | −0.72 | 0.14 |
| CTDNEP1 | 0.41 | −0.18 | −0.27 | 0.06 | −0.05 | AC087501.2 | −0.43 | −0.40 | 0.16 | −0.28 | 0.12 | AL450063.1 | −0.20 | 0.88 | −0.64 | 1.03 | −0.06 |
| AL353789.1 | −1.83 | 1.31 | 2.13 | −0.45 | 0.61 | RNU6-603P | −0.96 | 1.28 | 1.81 | −0.06 | −0.71 | AP000781.1 | 0.20 | 1.56 | −1.09 | 0.74 | −0.23 |
| DLEU7 | −1.25 | 0.35 | 0.92 | 0.72 | 0.70 | AL596087.2 | −0.53 | −0.15 | 0.42 | −0.01 | 0.90 | AC079753.1 | 0.13 | −1.26 | −0.37 | −0.51 | 0.09 |
| AL138920.1 | 0.79 | −0.53 | −0.55 | 0.12 | 0.51 | PTPN7 | 0.31 | −0.87 | −0.34 | −0.30 | 0.18 | CLNS1AP1 | 0.51 | −1.28 | 1.14 | −1.35 | 0.04 |
| MFSD1 | 0.52 | −0.24 | −0.23 | −0.05 | −0.06 | GZMM | −0.72 | 1.07 | −0.48 | 0.61 | −1.48 | NONOP2 | 0.05 | 0.10 | −0.09 | 0.11 | −0.15 |
| SLC1A7 | −1.27 | 0.75 | 1.70 | 0.55 | 0.16 | CAPN7 | −0.12 | 0.15 | 0.16 | 0.11 | 0.05 | SCARNA18 | −0.10 | 0.36 | −0.39 | 0.15 | −0.99 |
| LPIN3 | −0.70 | 0.54 | 0.39 | 0.50 | 0.12 | AC005476.2 | −0.39 | 0.15 | −0.37 | 0.31 | −0.11 | AL606516.1 | 0.33 | −0.89 | −0.09 | −0.21 | −0.80 |
| HMCES | 0.41 | −0.09 | −0.35 | −0.03 | −0.24 | AL078612.2 | 0.99 | −0.77 | −1.77 | −0.38 | −0.80 | AC020983.1 | −0.33 | −0.20 | 0.77 | 0.89 | 1.08 |
| PRSS23 | 0.92 | −0.24 | −0.09 | −0.51 | −0.34 | IGBP1P1 | −0.45 | −0.10 | 1.23 | −0.56 | −0.02 | AL357793.1 | 0.31 | −0.45 | −1.32 | 0.03 | −1.50 |
| MCTS1 | 0.62 | −0.47 | −0.17 | −0.21 | 0.05 | RPRD1B | 0.08 | −0.09 | −0.17 | 0.03 | −0.07 | STAU2 | 0.03 | 0.07 | 0.08 | 0.04 | 0.02 |
| PTGS2 | 1.57 | −1.74 | −2.22 | −0.71 | −1.75 | LINC01410 | −0.22 | −0.06 | 0.08 | −0.15 | −0.19 | AP002856.3 | 0.64 | −1.68 | 1.53 | −1.04 | 2.67 |
| AC027575.1 | 0.71 | −0.24 | −0.47 | 0.00 | −0.13 | PRRC2A | 0.10 | −0.01 | −0.22 | 0.07 | −0.02 | AC243964.2 | 0.17 | −1.27 | 0.64 | −0.34 | 0.92 |
| PGAM5 | 0.63 | −0.52 | −0.74 | 0.02 | −0.10 | F11-AS1 | −0.80 | −0.78 | 0.54 | 0.22 | 0.55 | LALBA | 0.30 | −1.38 | −1.26 | 0.12 | −0.39 |
| C2orf69 | 0.61 | −0.27 | −0.36 | −0.14 | −0.36 | AP002433.1 | 0.88 | 0.14 | 1.73 | −0.19 | 1.20 | AC007878.1 | 0.06 | −0.05 | 0.04 | 0.08 | 0.21 |
| FTCDNL1 | −0.57 | 0.30 | 0.37 | 0.27 | 0.27 | AC244090.2 | 0.82 | −0.34 | 1.30 | 0.59 | −0.41 | LINC01815 | 0.42 | 0.93 | −1.95 | 1.75 | −1.82 |
| CYP2A6 | −1.03 | 0.92 | 0.65 | 0.02 | 0.08 | HOOK3 | 0.14 | 0.03 | 0.08 | −0.16 | −0.23 | MYO9B | −0.04 | −0.29 | −0.38 | −0.16 | 0.02 |
| SPATA5L1 | 0.46 | −0.34 | −0.41 | −0.04 | −0.05 | AADACL2-AS1 | −0.57 | 1.03 | 0.62 | 1.49 | 0.25 | NEURL3 | −0.20 | −1.09 | 0.61 | −0.54 | 1.14 |
| AC112243.1 | −2.00 | 1.46 | 0.33 | 1.14 | 0.42 | PLG | −0.77 | −0.96 | −0.42 | −0.02 | −0.49 | AC009498.1 | −0.33 | −1.52 | 1.03 | 0.08 | 1.12 |
| STXBP5 | 0.46 | −0.03 | −0.35 | 0.11 | −0.25 | AL121594.1 | −0.66 | 0.03 | −1.46 | −0.57 | −1.19 | AL390778.1 | 0.39 | −1.31 | −1.52 | −1.11 | −1.83 |
| SHKBP1 | 0.34 | −0.25 | −0.46 | −0.12 | −0.35 | LINC01614 | 0.95 | −1.50 | −0.56 | −1.60 | 0.79 | AC007375.2 | −0.58 | 0.26 | −0.47 | 1.22 | −0.01 |
| ACAP2 | 0.37 | −0.05 | −0.13 | −0.07 | −0.25 | PDIA2 | −0.53 | 1.06 | −0.27 | 0.42 | −0.66 | RASSF3 | 0.06 | 0.05 | 0.15 | −0.13 | −0.01 |
| AC100797.1 | −0.95 | −0.08 | 0.60 | 0.04 | 0.67 | C6orf203 | −0.15 | −0.07 | 0.14 | −0.06 | 0.31 | AC138207.7 | −0.09 | −0.05 | −0.27 | 0.10 | 0.27 |
| NRIP1 | 0.82 | −0.50 | −0.93 | −0.45 | −0.86 | AC128707.1 | −1.35 | 0.90 | −1.20 | 0.06 | −1.44 | RPSAP2 | 0.16 | 0.33 | 0.01 | −0.11 | −1.54 |
| RPL18A | 0.58 | −0.03 | −0.33 | 0.05 | −0.53 | FAM27D1 | −1.24 | 0.42 | 0.14 | 0.67 | −1.20 | RPL30P2 | 0.19 | −0.30 | 0.08 | 0.73 | 0.72 |
| PPID | 0.53 | −0.30 | −0.10 | −0.25 | 0.00 | AP001207.2 | 0.49 | −0.92 | 0.05 | 0.12 | 1.09 | AC005534.1 | −0.14 | −0.22 | 1.83 | 0.05 | 1.32 |
| SMG8 | 0.49 | −0.19 | −0.14 | 0.00 | −0.19 | LINC00924 | −0.50 | −0.07 | 0.37 | 0.30 | −0.02 | AC025822.2 | −0.18 | −0.43 | −0.68 | 1.38 | 0.15 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| NBPF3 | −0.46 | 0.08 | 0.34 | 0.17 | 0.24 | RPL21P1 | 0.51 | −0.78 | −0.51 | −0.28 | 0.18 | AC234917.1 | 0.20 | −0.30 | 0.71 | 0.39 | 0.20 |
| AC009414.2 | −1.08 | 0.48 | 1.65 | 0.59 | 0.96 | RPLP1P6 | −0.64 | 0.56 | 0.58 | 0.83 | 0.92 | AC090502.4 | −0.47 | −1.12 | 1.55 | −1.03 | 1.00 |
| AP003035.1 | −1.24 | 0.38 | 1.06 | 0.03 | −0.24 | FSTL4 | −0.34 | 0.59 | 0.18 | 0.42 | −0.25 | RPS7P3 | 0.14 | 0.30 | −0.64 | 0.41 | −0.71 |
| RNF34 | 0.29 | −0.27 | −0.26 | −0.17 | −0.04 | AL583835.2 | −1.35 | 0.74 | −0.35 | 2.07 | 1.64 | AL450423.1 | −0.41 | −0.63 | −1.85 | −1.22 | −1.19 |
| GCM2 | −1.43 | 0.78 | 1.49 | 0.04 | 0.10 | SNORD19 | 0.51 | −0.44 | −0.02 | −0.29 | −0.43 | OR51B3P | −0.24 | 0.33 | −0.16 | −0.11 | −1.86 |
| AC010168.1 | −1.13 | 0.51 | 0.49 | 0.29 | 0.25 | HSD3BP4 | −0.58 | 0.20 | −0.59 | 0.28 | 0.26 | AL158834.1 | −0.12 | 0.31 | 1.04 | −0.14 | 0.38 |
| RNA5SP156 | 3.37 | −2.44 | −2.44 | −0.08 | −1.66 | AC068888.2 | 0.35 | −0.17 | −0.55 | 0.07 | −0.26 | MTND2P9 | 0.31 | −1.10 | 0.05 | 0.00 | 0.82 |
| GMPR | −0.83 | 0.46 | 0.60 | 0.24 | 0.12 | FTH1P7 | −0.75 | 0.10 | 0.99 | −0.55 | 0.12 | AC022150.4 | 0.04 | −0.15 | 0.24 | −0.36 | −0.11 |
| AC068491.4 | 0.92 | −1.27 | −0.61 | −1.02 | −0.19 | AL035446.1 | −1.45 | 2.17 | 3.03 | −0.26 | −0.58 | RFXANK | −0.04 | −0.10 | −0.34 | 0.07 | −0.08 |
| PAIP1 | 0.50 | −0.20 | −0.28 | −0.15 | −0.23 | AL031597.1 | 0.52 | −0.43 | −0.73 | 0.03 | 0.38 | CD24P2 | 0.22 | −0.41 | 0.12 | −1.01 | 0.19 |
| GAPDHP59 | 1.17 | −0.27 | −1.41 | −0.01 | −0.65 | AC073857.1 | 0.48 | −0.52 | 0.05 | −0.23 | 0.69 | LHX4 | 0.06 | −0.08 | 0.00 | −0.07 | 0.18 |
| RNU6-212P | 1.30 | −0.36 | −1.08 | −0.37 | −0.57 | AC141930.1 | 0.93 | −1.13 | −2.30 | −0.56 | 0.20 | AP001062.2 | 0.33 | −0.07 | −1.04 | −1.23 | −2.49 |
| PTPA | 0.45 | −0.13 | −0.19 | −0.03 | −0.08 | AC016526.2 | 0.66 | −0.91 | −0.78 | −0.76 | −0.45 | MIR4694 | −0.38 | 0.43 | 0.88 | 0.32 | −0.16 |
| SLITRK4 | −1.19 | 0.99 | 1.39 | 0.51 | 0.33 | AC127070.1 | −0.65 | 0.54 | 0.81 | 0.82 | 0.41 | SNCA-AS1 | 0.20 | −1.10 | −0.68 | 0.48 | −0.16 |
| RN7SL624P | −1.79 | −0.28 | 0.88 | 0.25 | 1.06 | HOMEZ | −0.16 | −0.04 | 0.29 | −0.07 | 0.28 | MS4A10 | −0.23 | −1.14 | 0.43 | 0.04 | −0.51 |
| HIPK2 | 0.52 | −0.14 | −0.58 | −0.01 | −0.20 | GRM7-AS3 | 0.98 | −0.94 | −0.79 | −0.56 | 0.78 | AL021407.3 | 0.16 | −1.29 | −0.57 | 0.39 | 1.40 |
| MIR1305 | 3.15 | −1.46 | −1.20 | −0.59 | −2.13 | PXMP4 | −0.24 | 0.29 | 0.43 | 0.38 | 0.12 | SMC2-AS1 | −0.15 | −0.08 | −0.88 | 0.46 | 0.06 |
| SPATA18 | −0.62 | 0.62 | 0.88 | 0.37 | 0.13 | MIR5579 | 0.53 | −0.80 | −0.38 | 0.29 | 0.37 | IGHV3-9 | 0.87 | −0.25 | 1.26 | −2.16 | −4.50 |
| CD9 | 0.66 | −0.07 | −0.66 | 0.04 | −0.59 | CETP | −0.22 | −0.46 | 0.25 | −0.11 | 0.61 | KIRREL3-AS2 | −0.17 | 0.33 | −1.27 | 0.43 | −0.01 |
| MAPK4 | −1.14 | 0.94 | 0.53 | 0.31 | 0.29 | AL160272.1 | −0.45 | −0.04 | −0.01 | 0.00 | −0.17 | AL358334.1 | −0.48 | −1.83 | 0.84 | −1.06 | 0.75 |
| AMER1 | −0.41 | 0.38 | 0.33 | 0.29 | 0.09 | AL139139.1 | −1.68 | −0.68 | 0.09 | 1.52 | −0.12 | AL138498.1 | −0.70 | 0.35 | 2.01 | −0.46 | 1.78 |
| CCDC148 | −0.94 | 0.38 | 0.64 | 0.18 | 0.47 | AL390334.1 | −0.89 | 0.20 | −0.12 | 0.17 | −0.78 | FAXC | 0.09 | −0.06 | 0.08 | −0.27 | −0.10 |
| PPP4R4 | 1.12 | −1.30 | −1.49 | −0.28 | −0.54 | AC009153.1 | 0.46 | −0.56 | −1.06 | −0.36 | −0.85 | AL163193.1 | 0.11 | −0.45 | 0.63 | −0.06 | 0.62 |
| STKLD1 | −0.67 | 0.63 | 0.36 | 0.43 | 0.06 | GUCY2EP | −0.85 | −0.01 | 0.27 | 0.10 | 0.36 | AC010608.1 | 0.19 | 0.88 | −1.63 | 0.61 | −0.81 |
| AL080317.3 | −0.44 | 0.22 | 0.35 | 0.25 | 0.31 | AL121949.2 | −1.17 | 0.51 | −0.36 | −1.14 | −1.87 | AC022294.1 | −0.18 | 0.29 | 1.46 | −0.10 | 0.01 |
| CSMD1 | −1.31 | 0.44 | 0.31 | −0.20 | −0.69 | AL445363.1 | −0.96 | −0.55 | −0.18 | 0.54 | 0.47 | ALLC | −0.21 | −0.93 | −2.06 | −0.61 | −0.97 |
| MYO1A | −1.02 | 0.11 | 0.34 | −0.13 | 0.00 | AC022903.2 | −0.82 | 0.97 | 0.18 | 1.05 | 0.33 | G26250 | −0.19 | −0.09 | 0.44 | 1.18 | 0.82 |
| OGDHL | 1.77 | −1.40 | −3.60 | 0.04 | −0.80 | AC117500.2 | −0.28 | 0.10 | 0.08 | 0.06 | 0.18 | AC026469.1 | 0.22 | 1.06 | −0.50 | 0.98 | −1.59 |
| RPL10A | 0.51 | −0.06 | −0.26 | −0.06 | −0.44 | RNU6-1302P | 1.13 | −0.20 | −0.48 | 0.86 | 0.08 | AC104619.3 | 0.11 | −0.06 | 0.10 | 0.40 | 0.07 |
| KHK | −0.66 | 0.06 | 0.51 | −0.09 | 0.14 | AL591212.2 | −0.66 | 0.88 | 0.10 | 1.09 | −0.06 | ARSA | −0.04 | −0.10 | −0.29 | 0.17 | 0.01 |
| CYBRD1 | −1.00 | 0.94 | 1.33 | 0.07 | 0.00 | ARID1B | −0.11 | 0.24 | 0.18 | 0.17 | −0.03 | AC013727.1 | 0.52 | −1.41 | −1.74 | −0.03 | −0.58 |
| AC006539.2 | −1.02 | 0.30 | 1.64 | −0.25 | 0.26 | RNU6-979P | 0.59 | 0.19 | −0.73 | 0.42 | −0.18 | AL365356.3 | 0.13 | −0.52 | −0.45 | −0.41 | 0.40 |
| ALCAM | −0.64 | 0.22 | 0.52 | −0.12 | 0.28 | MTCO1P55 | −0.65 | 0.59 | 2.05 | 0.05 | 0.22 | HMGN1P37 | 0.17 | −0.82 | 0.02 | −0.35 | −0.54 |
| ATXN1 | 0.42 | −0.18 | −0.50 | −0.05 | −0.16 | AC003101.1 | −0.31 | −0.22 | 0.15 | 0.20 | 0.68 | C1QTNF1 | 0.08 | −0.06 | −0.81 | 0.17 | −0.49 |
| AC009061.1 | −1.00 | 1.29 | 1.08 | 0.40 | −0.20 | CICP9 | −1.05 | 1.20 | 1.49 | 0.86 | 1.15 | RN7SL748P | 0.18 | −0.71 | −1.25 | 0.08 | −0.08 |
| HAUS2 | 0.57 | −0.26 | −0.41 | −0.22 | −0.20 | LINC00944 | 0.64 | −0.35 | 0.34 | −0.12 | 0.44 | DLGAP1-AS2 | −0.06 | −0.36 | 0.11 | −0.18 | 0.40 |
| RPL7 | 0.55 | −0.10 | −0.16 | −0.09 | −0.33 | AL355922.1 | −0.62 | 0.61 | 1.19 | −0.01 | 0.47 | AL078459.1 | −0.07 | −0.28 | 0.53 | −0.74 | 0.10 |
| SDC2 | −1.01 | 0.53 | 0.95 | −0.29 | −0.17 | ABT1P1 | 0.62 | −0.83 | −1.08 | −0.89 | −0.35 | AC092964.1 | −0.12 | −0.19 | −0.31 | −0.35 | −0.43 |
| DNAJB5 | 0.51 | −0.25 | −0.41 | −0.39 | −0.39 | AC010280.3 | −1.04 | 1.39 | −0.34 | 0.38 | −0.64 | ITGA1 | −0.08 | −0.02 | 0.32 | −0.33 | −0.33 |
| G33445 | 0.75 | −0.57 | −0.46 | −0.10 | −0.02 | RAPH1 | 0.12 | −0.04 | −0.15 | −0.11 | −0.06 | MANSC1 | 0.04 | 0.13 | −0.01 | 0.16 | −0.19 |
| SLC25A46 | 0.52 | −0.19 | −0.27 | −0.11 | −0.26 | PGLYRP3 | 0.26 | 0.09 | 0.13 | 0.09 | 0.04 | AL161793.1 | −0.38 | −1.92 | 1.26 | −0.95 | 1.37 |
| 2-Mar | −0.92 | 0.55 | 1.22 | 0.17 | 0.67 | RNF152 | −0.24 | 0.46 | 0.56 | 0.00 | 0.06 | FOXR2 | −0.45 | 0.14 | 0.04 | 0.07 | 0.43 |
| CDC23 | 0.43 | −0.18 | −0.21 | −0.10 | −0.19 | POLR2KP1 | 0.49 | −0.84 | −0.29 | −0.35 | 0.13 | AC068831.7 | 0.06 | −0.05 | 0.24 | 0.13 | 0.39 |
| APOPT1 | −0.49 | 0.09 | −0.09 | 0.13 | −0.01 | AL080243.2 | −0.49 | −0.54 | 0.13 | −0.25 | 0.21 | FXR2 | −0.02 | 0.01 | −0.09 | −0.02 | −0.02 |
| G26573 | −1.44 | 0.90 | 0.83 | 0.56 | 0.15 | AF131215.3 | −0.42 | 0.93 | 0.12 | 0.84 | 0.75 | FLII | 0.03 | −0.12 | −0.30 | −0.01 | −0.05 |
| PRKCE | −0.46 | 0.07 | 0.37 | 0.02 | 0.28 | G29700 | −0.83 | 0.29 | 0.93 | 0.24 | 0.28 | MIR5010 | 0.52 | 1.50 | 0.43 | 0.79 | 0.33 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| CBR1 | 0.63 | −0.17 | −0.41 | 0.07 | −0.25 | ERVK3-1 | 0.21 | 0.08 | −0.10 | 0.00 | −0.09 | LHX6 | 0.09 | 0.14 | 0.80 | 0.09 | 0.25 |
| AL592114.3 | −2.00 | 0.13 | 0.64 | 1.65 | 0.91 | DNAJC28 | −0.19 | 0.26 | 0.28 | 0.12 | 0.00 | AL031666.2 | −0.09 | −0.33 | 0.44 | −0.41 | 0.07 |
| DENND2D | 0.44 | −0.20 | 0.01 | −0.12 | 0.15 | AL590133.1 | 0.70 | −0.99 | −2.07 | 0.56 | 0.09 | RPL12P37 | 0.36 | −0.56 | 0.01 | −0.34 | −1.41 |
| DNASE1L2 | −1.11 | 0.71 | 0.94 | 0.71 | −0.10 | ARHGAP21 | 0.18 | 0.02 | −0.31 | −0.16 | −0.36 | AC079907.2 | 0.46 | 1.76 | −1.06 | 0.24 | −0.83 |
| AC103705.1 | 2.95 | 0.18 | −0.54 | 0.99 | 0.22 | AC034236.1 | 0.50 | −0.17 | 0.34 | 0.03 | −0.51 | AC239798.4 | −0.23 | −0.96 | 0.49 | −0.73 | −0.21 |
| ITGAX | 1.24 | −1.47 | −1.38 | −0.49 | −0.46 | COMMD7 | 0.16 | 0.11 | 0.17 | 0.14 | −0.07 | PIWIL3 | −0.18 | −0.91 | −0.38 | 0.19 | 0.14 |
| KLK8 | 0.91 | −0.43 | −0.21 | −0.07 | −0.19 | GAPDHP21 | −1.32 | −0.90 | 2.30 | −1.23 | 1.23 | AL358394.3 | −0.45 | −0.71 | 1.00 | −0.65 | 0.30 |
| AK2 | 0.33 | −0.27 | −0.33 | −0.10 | 0.01 | SNRPGP9 | 0.70 | −0.92 | −1.48 | −0.26 | 0.00 | ATP5MGP2 | 0.55 | −1.21 | −1.63 | 0.29 | −1.13 |
| RPL29 | 0.60 | −0.14 | −0.37 | −0.13 | −0.58 | ACSM2A | 0.70 | −1.02 | −1.58 | −0.29 | −1.40 | AL163953.1 | −0.29 | 1.14 | 0.09 | 0.62 | −0.98 |
| CAPN10 | −0.57 | 0.28 | 0.40 | 0.23 | 0.30 | RNU6-872P | −1.07 | 0.62 | 0.40 | −0.19 | 1.54 | LINC02517 | −0.39 | 0.10 | −0.92 | 2.22 | −0.41 |
| AL353583.1 | 0.80 | −0.27 | −0.92 | 0.00 | −0.25 | MBTPS2 | 0.16 | −0.12 | −0.13 | −0.09 | −0.14 | AC078899.5 | −0.72 | 0.92 | 1.47 | 0.40 | 1.60 |
| MFSD5 | 0.66 | 0.06 | −0.19 | 0.10 | −0.50 | KIAA2012 | −0.49 | −0.22 | −0.12 | 0.13 | 0.08 | AC005537.1 | −0.09 | 0.09 | 0.40 | 0.78 | 0.49 |
| RBM6 | −0.46 | 0.09 | 0.26 | 0.01 | 0.14 | AC124312.4 | −0.68 | −0.88 | 0.67 | −0.58 | 0.86 | C6orf15 | −0.16 | 0.95 | −0.26 | 0.03 | −2.00 |
| FAM222A | −0.74 | 0.63 | 0.62 | 0.38 | 0.19 | AC092782.1 | 0.63 | −0.39 | 0.68 | −0.55 | 0.48 | OR8F1P | −0.68 | 1.41 | 0.07 | −0.07 | −1.47 |
| CCDC134 | −0.53 | 0.19 | 0.31 | 0.04 | 0.23 | AL604028.2 | 0.22 | 0.04 | 0.33 | −0.04 | 0.01 | AC004690.2 | 0.28 | 0.47 | −1.17 | 0.50 | −0.63 |
| PCDHB16 | −1.10 | 0.40 | 0.89 | 0.10 | 0.25 | RNU6-1231P | 0.88 | −0.63 | 0.73 | −1.34 | −0.35 | AC010307.4 | −0.18 | −0.54 | −0.93 | −0.27 | −1.11 |
| SPAG5 | 0.61 | −0.78 | −1.13 | −0.26 | −0.12 | CUL1P1 | −0.96 | 0.63 | 0.54 | −0.18 | −0.33 | DNAJC30 | −0.05 | 0.14 | 0.16 | 0.30 | 0.14 |
| RN7SL512P | −1.45 | −0.05 | 2.01 | −0.04 | 0.43 | MID2 | 0.16 | 0.23 | 0.25 | 0.12 | −0.25 | AL512353.3 | 0.27 | 0.10 | −0.45 | −0.23 | −0.28 |
| GON7 | 0.51 | −0.21 | −0.34 | −0.16 | −0.30 | LINC00662 | −0.12 | 0.04 | 0.24 | −0.02 | 0.15 | BX255923.1 | 0.20 | 0.91 | 0.94 | −0.02 | −0.04 |
| CACYBP | 0.55 | −0.39 | −0.22 | −0.38 | −0.05 | KCNN4 | −0.32 | 0.27 | 0.09 | 0.16 | 0.30 | RNU6-388P | −0.29 | 1.31 | 0.91 | 0.70 | −0.55 |
| SLC25A39 | 0.51 | −0.29 | −0.52 | −0.03 | −0.16 | AC091891.1 | −0.37 | 0.31 | −0.86 | 0.71 | −0.54 | AC243591.1 | 0.65 | −0.36 | −1.50 | −1.02 | −1.51 |
| SBSPON | −0.78 | 0.31 | 0.75 | 0.45 | 0.35 | AL391988.1 | 0.34 | −0.31 | −0.33 | −0.05 | −0.36 | AL138885.1 | 0.26 | −0.89 | −1.13 | 0.39 | −1.58 |
| RN7SL4P | −1.45 | 0.48 | −0.69 | 1.19 | −0.59 | KIF17 | 0.33 | −0.30 | −0.71 | −0.20 | −0.37 | C12orf77 | −0.20 | 0.25 | −2.75 | 0.06 | −2.36 |
| SRSF6 | 0.47 | −0.18 | −0.39 | −0.09 | −0.25 | CBLL1 | 0.12 | 0.00 | 0.02 | −0.16 | −0.11 | SSX9P | 1.08 | −1.79 | −1.46 | 0.11 | 0.09 |
| FAM149B1 | −0.25 | 0.12 | 0.29 | 0.00 | 0.09 | OVCH1-AS1 | −0.36 | 0.20 | 0.30 | 0.09 | 0.06 | DCDC2 | 0.11 | −0.14 | −0.26 | −0.23 | −0.39 |
| AC010207.1 | −0.94 | 0.91 | 0.56 | −0.10 | −0.53 | G18793 | 1.10 | 1.22 | 0.10 | 0.40 | −0.67 | ASNSP5 | −0.14 | 0.18 | 1.24 | 0.48 | 0.47 |
| IL4I1 | 1.50 | −1.67 | −1.57 | −1.00 | −0.74 | CABYR | −0.19 | 0.25 | 0.41 | 0.23 | 0.06 | AC021483.2 | 0.15 | −0.28 | −0.03 | 0.35 | 0.25 |
| CASP1 | 0.52 | −0.31 | −0.49 | −0.22 | −0.36 | FAM133CP | −0.32 | −0.07 | 0.53 | −0.58 | −0.10 | RPL26P31 | 0.57 | 0.38 | −1.86 | −0.10 | −3.43 |
| AC092802.3 | −2.05 | 2.17 | −0.53 | 2.42 | 0.52 | AC131159.1 | 0.88 | −1.12 | −0.18 | 0.22 | 0.35 | AC010636.1 | −0.25 | −0.77 | 2.30 | −0.65 | −0.26 |
| G26246 | −1.44 | 1.01 | 1.62 | 0.76 | 0.86 | FAM220A | 0.19 | 0.00 | −0.24 | 0.08 | −0.44 | GPR84 | −0.10 | −0.42 | −0.03 | −0.80 | −0.34 |
| CLVS2 | −1.65 | 0.53 | 0.35 | 0.49 | −0.23 | AC073957.1 | 0.52 | −0.74 | −0.21 | 0.15 | 0.82 | AC097372.4 | −0.71 | −0.27 | −0.63 | −0.47 | −2.70 |
| OR7E128P | −0.59 | 0.29 | 0.65 | −0.01 | 0.27 | AL049840.6 | 0.43 | 0.70 | −0.22 | 0.35 | −0.40 | GCNA | −0.05 | 0.09 | −0.05 | 0.01 | −0.16 |
| BBS5 | −0.76 | 0.40 | 0.30 | 0.44 | 0.32 | RNU6-767P | 0.47 | −0.49 | 0.09 | 0.03 | 0.25 | LINC02148 | −0.23 | −0.40 | 0.72 | 0.69 | 0.27 |
| ASPDH | −1.07 | 0.31 | 1.07 | 0.25 | 0.60 | MIR130A | 0.74 | −1.23 | 1.40 | −1.62 | 0.77 | AC005842.1 | 0.07 | −0.16 | 0.05 | 0.24 | 0.57 |
| ETFBKMT | −0.51 | 0.42 | 0.34 | 0.15 | −0.08 | EGFR-AS1 | −0.29 | 0.20 | 0.24 | 0.17 | 0.21 | CEP170 | 0.03 | −0.02 | 0.23 | −0.17 | 0.00 |
| DHX33 | 0.38 | −0.40 | −0.46 | −0.04 | 0.04 | AC093767.1 | −1.05 | 0.58 | 0.33 | 1.33 | 0.29 | GAPDHP60 | −0.06 | −0.28 | 0.50 | −0.30 | 0.42 |
| FAM120AOS | −0.25 | 0.23 | 0.18 | 0.08 | 0.01 | AC008277.1 | 0.31 | 0.04 | 0.23 | 0.26 | 0.23 | AL031055.1 | 0.49 | 0.41 | −0.86 | 0.84 | −1.04 |
| AP001610.1 | 1.67 | −0.96 | −2.20 | −0.42 | −1.16 | NLRP8 | −0.59 | −0.31 | −0.17 | 0.07 | 0.23 | MIR30A | −0.31 | 0.15 | 0.68 | 0.11 | −0.03 |
| PFDN4 | 0.56 | −0.21 | −0.55 | 0.01 | −0.28 | HNRNPA3P12 | 0.35 | −0.53 | −1.29 | 0.22 | −0.37 | IGHD | 0.23 | −0.24 | 0.89 | −0.52 | −2.67 |
| PRKCH | 0.34 | −0.06 | −0.22 | −0.08 | −0.11 | AC108676.2 | 0.70 | −0.95 | −2.12 | 0.06 | −1.33 | AL606490.2 | −0.18 | 0.87 | −1.53 | 0.10 | −1.38 |
| AC015912.3 | 1.56 | −0.63 | −1.74 | 0.20 | −0.80 | AC007938.2 | −0.61 | 0.59 | 0.06 | 0.93 | −0.42 | RNU6-341P | 0.15 | −0.38 | 0.01 | −0.06 | −0.49 |
| AL109917.1 | −1.32 | 0.55 | 1.35 | 0.22 | −0.17 | RNU6-155P | 0.92 | 0.42 | 2.03 | −0.21 | −0.44 | AC011008.2 | −0.15 | 0.54 | 0.48 | 0.89 | −0.34 |
| BTF3L4P2 | 0.89 | −0.18 | −0.86 | −0.14 | −0.66 | RNA5SP37 | 0.32 | −0.10 | −0.30 | −0.02 | 0.17 | AL354863.1 | −1.14 | −0.09 | 1.53 | −0.75 | −0.54 |
| HDAC1P1 | −1.67 | 1.85 | 1.71 | 1.58 | 0.72 | HNRNPA1P35 | 0.29 | −0.09 | 0.15 | 0.12 | −0.23 | GAPDHP15 | 0.21 | −0.57 | 2.51 | −0.84 | 0.94 |
| ROMO1 | 0.53 | −0.16 | −0.15 | −0.22 | −0.35 | G31400 | 0.80 | −0.24 | −1.63 | −0.34 | −0.02 | AC011284.1 | 0.12 | −0.21 | 0.41 | −0.91 | −0.33 |
| AL591069.1 | 0.78 | −0.44 | −0.54 | −0.04 | 0.04 | PRKCA | −0.13 | 0.04 | 0.02 | 0.03 | −0.01 | CASR | 0.18 | −0.29 | −0.96 | 0.08 | −0.59 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| PCBP1-AS1 | −0.33 | 0.22 | 0.36 | 0.06 | 0.10 | LINC00661 | −0.98 | 1.26 | −2.10 | 1.25 | −1.05 | AL035414.1 | 0.48 | −0.18 | −0.20 | −0.14 | 0.25 |
| IGFLIP1 | −1.29 | 1.26 | 1.60 | 1.00 | −0.24 | LINC01794 | −0.85 | −0.22 | 2.07 | −0.23 | −0.28 | GOLGA6B | −0.23 | 1.11 | 0.14 | 0.83 | 1.37 |
| DEFB103B | 3.59 | −3.41 | −4.22 | 0.21 | −4.00 | AL022344.1 | 1.05 | −1.40 | −1.37 | −0.13 | −0.56 | AP001360.2 | −0.20 | 1.48 | −0.51 | 0.04 | −2.34 |
| CA5B | −0.46 | 0.28 | 0.52 | 0.12 | 0.08 | ACSM6 | −0.24 | 0.03 | −0.08 | −0.06 | 0.02 | FAM242A | −0.23 | 0.22 | 0.21 | 0.44 | −0.60 |
| AC020907.1 | −1.07 | 0.12 | 0.99 | −0.01 | 0.19 | IRF2 | 0.12 | −0.03 | 0.01 | −0.21 | 0.01 | AC106900.2 | −0.41 | −0.05 | 0.33 | 0.21 | 0.44 |
| FRMD7 | −1.27 | 0.66 | 0.92 | −0.30 | −0.38 | AC090373.1 | 0.47 | −0.46 | 0.20 | −0.11 | 0.55 | SDR42E1P5 | −0.32 | 0.20 | −1.89 | −0.36 | −2.80 |
| RPL38 | 0.57 | −0.20 | −0.17 | −0.17 | −0.31 | RN7SL306P | 0.57 | −0.78 | 0.55 | −0.50 | −0.04 | AL136141.1 | 0.20 | −0.92 | 0.01 | 0.69 | 1.05 |
| RNU6-495P | −2.03 | 0.69 | 3.35 | −0.05 | 0.58 | AC233723.2 | 0.23 | −0.27 | −0.50 | 0.12 | −0.11 | HPAT5 | −0.32 | 1.30 | 0.18 | 0.38 | −0.70 |
| MED13 | 0.32 | −0.02 | −0.27 | −0.05 | −0.34 | GPR135 | 0.24 | −0.25 | −0.03 | 0.01 | 0.16 | IL20RB | 0.07 | 0.31 | 0.18 | 0.25 | 0.16 |
| SPTBN2 | −0.65 | 0.56 | 0.35 | 0.43 | 0.09 | AL139118.1 | −0.67 | 0.04 | 0.85 | −0.08 | −0.74 | KRTAP4-8 | −0.41 | −0.36 | 1.43 | −0.79 | −2.35 |
| SLC49A3 | −0.67 | 0.36 | 0.26 | 0.25 | −0.10 | LINC02073 | 0.70 | −0.15 | −1.55 | 0.36 | −0.80 | CCKAR | −0.27 | −1.20 | −0.79 | 0.14 | 0.94 |
| AC007308.6 | −0.77 | 0.32 | 0.43 | 0.27 | 0.04 | AP001178.1 | 0.64 | −0.79 | −0.02 | −0.05 | −0.12 | AC025574.1 | −0.45 | 0.16 | −0.33 | −0.42 | −2.25 |
| MOB4 | 0.70 | −0.12 | −0.42 | 0.09 | −0.55 | FTH1P25 | 0.45 | −0.03 | −0.40 | 0.08 | 0.12 | RNU7-91P | 0.14 | −0.25 | −0.81 | −0.32 | −0.59 |
| FAR1 | 0.45 | −0.22 | −0.35 | −0.13 | −0.12 | SLC12A2 | −0.38 | 0.63 | 1.03 | 0.11 | 0.74 | ANKRD62 | 0.14 | −0.28 | 0.15 | 0.56 | −0.18 |
| OR56A1 | −1.29 | 0.52 | 0.64 | 0.21 | 0.25 | AC105415.1 | −0.97 | −0.20 | 0.15 | −0.03 | −0.04 | EIF4BP9 | −0.21 | −0.38 | −3.00 | 0.50 | −2.84 |
| AC105101.1 | −0.78 | 0.14 | 0.79 | 0.22 | 0.48 | FKBP2 | 0.16 | −0.04 | 0.18 | −0.29 | 0.06 | AC079203.1 | −0.10 | 0.12 | −0.10 | −0.07 | 0.21 |
| ACSF3 | −0.46 | 0.01 | 0.19 | 0.23 | 0.36 | SRGAP3-AS2 | −0.43 | −0.07 | 0.20 | −0.03 | −0.04 | CCT6P4 | 0.44 | −0.76 | −0.44 | −0.17 | −0.65 |
| AC097493.4 | −1.43 | 0.86 | 0.88 | 0.58 | 0.10 | RBM28 | −0.12 | −0.14 | −0.05 | −0.01 | 0.16 | LINC02392 | −0.26 | −0.19 | 0.15 | 0.20 | 1.64 |
| ADAM8 | 0.98 | −1.48 | −1.73 | −0.58 | −0.62 | RN7SL464P | 0.71 | 0.53 | −0.01 | 0.17 | −0.63 | AC010997.5 | 0.09 | −0.30 | −0.17 | −0.11 | 0.03 |
| ALDH1A3 | 1.21 | −0.90 | −0.91 | −0.33 | −0.79 | AC009229.3 | −0.80 | 1.24 | 2.69 | −0.72 | −0.16 | AC002511.2 | 0.28 | −0.47 | −2.51 | −0.37 | −2.57 |
| F11R | 0.69 | −0.12 | −0.51 | 0.19 | −0.21 | LINC02551 | 0.47 | −0.16 | −1.15 | −0.13 | −0.79 | LINC01755 | −0.18 | −1.10 | 0.10 | 0.31 | 0.47 |
| SLC26A7 | −1.13 | 0.66 | 0.84 | 0.68 | 0.62 | ANGEL2 | −0.09 | 0.03 | 0.14 | 0.11 | 0.15 | OR8A1 | 0.22 | −0.75 | −0.47 | 0.27 | −0.16 |
| PRDX4 | 0.58 | −0.17 | −0.29 | −0.41 | −0.32 | NMRAL2P | 0.36 | 0.00 | 0.44 | 0.23 | 0.26 | FAM3C2 | 0.08 | −0.35 | 0.48 | −0.49 | 0.09 |
| GALK1 | 0.56 | −0.40 | −0.48 | 0.00 | −0.14 | GNG3 | 0.56 | 0.37 | −0.19 | −0.12 | −0.61 | RNA5SP437 | 0.20 | −0.79 | −2.04 | 0.44 | −0.62 |
| AL390957.1 | −0.71 | 0.09 | 0.38 | 0.29 | 0.37 | DUSP3 | 0.14 | −0.10 | −0.09 | −0.13 | −0.21 | AC019176.1 | 0.20 | 0.21 | −1.12 | 0.78 | 0.15 |
| AC104794.2 | −0.75 | 0.26 | 1.05 | 0.31 | 0.29 | RNU6-80P | −0.57 | −0.34 | 0.45 | 0.32 | 0.21 | RPL7P35 | 0.54 | 0.52 | 0.95 | 0.58 | 0.81 |
| MCU | 0.36 | −0.04 | −0.16 | −0.15 | −0.33 | CACNA1G−AS1 | −0.54 | −0.19 | 0.91 | −0.54 | 0.28 | SLC7A13 | −0.18 | −0.69 | 0.57 | −0.14 | 0.94 |
| HIST1H1E | 0.48 | −0.16 | −0.63 | −0.24 | −0.52 | AC022215.1 | −0.85 | 0.99 | 1.28 | 0.47 | 0.02 | SORCS3-AS1 | −0.30 | −1.85 | 0.10 | −0.16 | −0.05 |
| LRGUK | −0.59 | 0.27 | 0.32 | 0.30 | 0.43 | HYI-AS1 | −0.68 | −0.24 | 0.16 | −0.13 | −0.22 | ITCH | 0.02 | 0.01 | −0.03 | −0.12 | −0.17 |
| AC105233.5 | −0.80 | 0.35 | 0.33 | 0.20 | 0.20 | AC063952.2 | −0.65 | 0.36 | −0.50 | 0.47 | −0.01 | MT-TD | −0.15 | −0.02 | 0.03 | 0.57 | −0.18 |
| AP000240.1 | 1.36 | −0.61 | −0.87 | −0.65 | −0.56 | RN7SL125P | −1.15 | 1.34 | −0.06 | 0.97 | 0.80 | C9orf147 | 0.08 | −0.01 | 0.22 | −0.12 | 0.09 |
| ANXA11 | −0.42 | 0.30 | 0.34 | 0.04 | −0.04 | GYG2P1 | −1.06 | 0.17 | 0.35 | 0.27 | −0.31 | AP001372.1 | −0.24 | 0.47 | −0.35 | −0.06 | −0.46 |
| FP325332.1 | −0.91 | 0.02 | 0.39 | 0.46 | 0.90 | RNU6-450P | 0.85 | −1.29 | −0.31 | −0.75 | 1.19 | MIR100 | −0.33 | 0.69 | 0.84 | 0.12 | −0.54 |
| C2orf72 | −1.62 | 0.56 | 1.31 | 0.33 | 1.03 | LINC01470 | −0.79 | 0.21 | 0.17 | 0.64 | −0.24 | CPHLIP | −0.17 | −0.49 | −0.25 | 0.45 | 0.08 |
| ELN-AS1 | −2.02 | 2.24 | 3.16 | 0.25 | 0.01 | AL365217.1 | −0.90 | 0.40 | 0.26 | −0.13 | −0.35 | AL138762.1 | 0.17 | −0.01 | −1.52 | 0.31 | −1.67 |
| RBMS3 | −0.83 | 0.50 | 1.17 | 0.12 | 0.14 | DDX12P | −0.27 | −0.27 | −0.42 | 0.15 | 0.20 | CLEC20A | 0.19 | −0.79 | −2.22 | 0.65 | −0.49 |
| NR5A1 | −1.57 | 0.77 | 0.82 | 0.49 | 0.18 | AL157756.1 | −0.42 | 0.15 | 0.18 | 0.10 | 0.03 | RNA5SP457 | 0.31 | 0.99 | 1.43 | −0.14 | 0.15 |
| SHOX2 | −0.86 | 0.48 | 1.11 | −0.29 | −0.08 | AC079296.1 | 0.64 | −0.47 | −0.79 | 0.36 | 0.20 | AC002350.1 | 0.09 | 0.11 | −0.61 | 0.03 | −0.27 |
| AC013474.1 | −1.28 | 0.69 | 1.24 | −0.06 | −0.10 | SMARCE1P5 | −0.53 | 0.92 | 0.79 | 0.05 | −0.82 | ITGA5 | −0.06 | −0.20 | 0.22 | −0.51 | −0.25 |
| AL031282.2 | −0.76 | 0.31 | 0.29 | 0.69 | 0.63 | AC244034.2 | 0.50 | 0.49 | −0.87 | 0.53 | −0.58 | LINC00303 | 0.27 | −0.67 | −0.17 | 0.69 | 1.69 |
| RREB1 | 0.36 | −0.21 | −0.52 | −0.01 | −0.09 | AC006111.3 | −0.43 | −0.24 | −0.68 | 0.24 | −0.29 | AC087752.2 | 0.13 | −0.58 | −0.42 | −0.12 | −0.25 |
| G40303 | −0.88 | −0.09 | 0.41 | −0.01 | 0.42 | PSG4 | −0.33 | −0.34 | −0.52 | 0.14 | −0.71 | LINC02537 | 0.34 | −2.05 | −1.18 | 1.13 | 1.70 |
| SCAI | −0.31 | 0.18 | 0.49 | 0.03 | 0.19 | AL122023.1 | 0.76 | −0.46 | −0.60 | −0.41 | −0.38 | AC023051.2 | −0.13 | −0.26 | 0.60 | −0.06 | 0.77 |
| AL353743.3 | −1.42 | 0.46 | 1.76 | −0.52 | 0.18 | CCDC65 | 0.24 | −0.04 | 0.21 | −0.11 | 0.03 | AC007364.1 | −0.17 | −0.29 | −0.37 | 0.25 | −0.65 |
| ACOT8 | −0.44 | 0.39 | 0.53 | 0.21 | 0.20 | AC010280.2 | −1.10 | 1.58 | 0.48 | 0.91 | 0.70 | MIR30E | 0.12 | 0.52 | 0.32 | 0.35 | 0.21 |
| MESP1 | −1.50 | 0.02 | 1.74 | 0.08 | 1.14 | AP000842.1 | −1.20 | −0.11 | 0.57 | −0.75 | 0.46 | AC012175.1 | −0.34 | −0.73 | 0.81 | −0.42 | −0.48 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| JTB | 0.72 | −0.31 | −0.16 | −0.19 | −0.05 | LINC02122 | −0.99 | 0.33 | −0.88 | 0.98 | −2.01 | OR1H1P | 0.12 | −0.14 | 1.32 | 0.03 | 0.45 |
| AC018647.2 | 0.68 | −0.32 | −0.41 | 0.01 | −0.36 | AL021918.3 | −0.82 | 0.76 | 0.37 | 0.40 | −1.50 | AL139397.2 | 0.20 | −0.79 | −1.14 | −0.11 | −1.72 |
| FBF1 | −0.68 | 0.21 | 0.41 | 0.22 | 0.47 | MMP11 | 0.49 | −0.23 | 0.21 | −0.50 | −0.37 | AFAP1 | −0.04 | 0.01 | 0.14 | −0.25 | −0.03 |
| AC005703.6 | −1.21 | 0.41 | 0.00 | 0.29 | −0.37 | AC004134.1 | −0.29 | 0.07 | −0.36 | 0.29 | 0.44 | AC109347.2 | 0.18 | 0.24 | 0.44 | −0.58 | −1.61 |
| SPINT1-AS1 | −0.67 | 0.60 | 0.23 | 0.63 | −0.10 | AL050343.2 | 0.61 | 0.47 | 0.16 | −0.15 | −0.09 | AC003986.3 | −0.18 | 0.00 | 0.33 | −0.78 | 0.39 |
| CLCN5 | 0.40 | −0.22 | −0.16 | −0.03 | −0.03 | AL137783.1 | −1.04 | −0.08 | 0.54 | −0.06 | 1.53 | G35261 | 0.08 | 0.32 | 0.32 | 0.10 | 0.19 |
| SIRT5 | −0.35 | 0.20 | 0.34 | 0.03 | 0.16 | AC093726.2 | −0.32 | 0.28 | 0.17 | 0.30 | 0.13 | AL157831.2 | 0.26 | −0.29 | −1.76 | −0.38 | −2.94 |
| AC008114.1 | 1.53 | −0.47 | −0.44 | 0.15 | −0.60 | AC010457.1 | −0.61 | −1.63 | 1.09 | −0.04 | 1.50 | LIN52 | 0.03 | −0.04 | −0.11 | 0.15 | −0.09 |
| LAMC2 | 0.95 | −1.13 | −1.16 | −0.56 | −0.34 | CETN3 | 0.19 | −0.06 | 0.02 | 0.04 | 0.10 | AL008638.6 | −0.20 | −0.81 | −1.68 | 0.06 | 0.17 |
| CDADC1 | −0.39 | 0.07 | 0.28 | 0.04 | 0.11 | RNU6-1295P | −1.27 | 0.93 | 0.39 | 0.86 | −1.98 | LINC01777 | 0.37 | −2.16 | −1.25 | −0.28 | 0.51 |
| SLC7A14 | −1.24 | 0.57 | 1.50 | 0.38 | 0.75 | AC021698.1 | −1.18 | −1.23 | −2.90 | 0.35 | −1.31 | AC087045.3 | 0.35 | 0.17 | 0.65 | −0.76 | 0.59 |
| FEN1 | 0.86 | −0.81 | −1.01 | −0.36 | −0.29 | GNG13 | −0.76 | −0.78 | 0.05 | 0.30 | 1.00 | AC092637.1 | 0.32 | −1.50 | −2.16 | −0.16 | −1.08 |
| ANKMY1 | −0.58 | 0.36 | 0.67 | 0.13 | 0.12 | ST13P2 | −1.13 | 0.47 | −0.61 | 1.20 | −0.42 | MED13L | 0.02 | 0.17 | −0.10 | 0.16 | −0.13 |
| AC074138.1 | −0.75 | 0.61 | 0.55 | −0.08 | −0.05 | ABHD2 | 0.15 | −0.05 | −0.09 | −0.17 | −0.11 | AC005161.1 | −0.34 | 0.30 | 1.75 | 0.84 | 0.91 |
| SMIM10L2B | −0.84 | 0.76 | 0.26 | 0.49 | 0.01 | GSTM3P2 | 0.49 | −0.21 | −0.18 | 0.18 | −0.08 | GRM3 | −0.13 | −0.51 | −1.06 | −0.01 | −0.65 |
| MIR3687 | 0.81 | −0.76 | −1.13 | −0.37 | −0.03 | AC116021.1 | 1.18 | −2.03 | −2.21 | 0.09 | −0.03 | AC026979.1 | −0.13 | 0.21 | −0.91 | −0.01 | −0.33 |
| G28013 | −2.02 | 1.05 | 0.14 | 0.58 | 0.36 | AC010173.1 | −0.53 | −0.17 | 0.62 | −0.76 | 0.44 | BTF3L4P4 | 0.22 | −0.68 | 0.07 | −0.81 | 0.14 |
| CXCL5 | 2.01 | −3.05 | −1.28 | −0.13 | 0.29 | LCK | 0.50 | −0.94 | 0.23 | −0.77 | 0.72 | LINC01744 | 0.23 | −1.27 | −1.31 | 1.06 | 0.73 |
| AC108199.1 | 1.77 | −1.21 | −2.56 | −0.78 | −0.56 | DDTP1 | 0.93 | 0.33 | 0.42 | 0.15 | 0.38 | AC245052.3 | 0.14 | −1.07 | −0.65 | −0.06 | 0.21 |
| RRN3P3 | −0.63 | 0.23 | 0.47 | 0.05 | 0.30 | SHANK2-AS3 | 0.64 | 0.60 | −1.16 | −0.55 | −0.24 | RPS3P7 | 0.08 | 0.18 | −0.16 | 0.37 | −0.14 |
| PA2G4P4 | −0.92 | 0.42 | 0.85 | 0.26 | 0.28 | ERVMER61-1 | −0.52 | 0.34 | −0.45 | 0.16 | −0.37 | RN7SL302P | 0.17 | 1.68 | −0.51 | 1.12 | −0.65 |
| FAM83H | 0.78 | −0.25 | −0.87 | 0.19 | −0.31 | RNU6-905P | 1.68 | −1.64 | −0.65 | 0.04 | −0.29 | RARA-AS1 | 0.09 | −0.06 | 0.22 | −0.11 | −0.12 |
| CMIP | 0.38 | −0.15 | −0.46 | −0.13 | −0.33 | FAM72B | 0.36 | −0.19 | −0.27 | −0.36 | −0.22 | C8orf87 | −0.31 | −1.30 | 0.21 | −1.01 | −0.78 |
| AL158154.2 | −1.52 | −0.14 | −0.43 | 0.31 | 0.35 | ADAMTSL4-AS1 | 0.17 | −0.47 | −0.59 | −0.24 | −0.05 | CHCHD3P3 | 0.15 | −0.23 | −0.52 | −0.11 | −0.26 |
| DPM2 | 0.51 | −0.23 | −0.30 | −0.13 | −0.09 | NF1P8 | 1.22 | −1.42 | −1.49 | 0.74 | 0.85 | LINC02244 | 0.20 | 0.73 | 0.08 | 0.30 | −1.11 |
| ENKUR | 1.51 | −1.55 | −2.35 | −0.28 | −0.89 | MTG2 | 0.12 | −0.11 | −0.27 | −0.05 | −0.04 | AC079917.1 | −0.35 | −0.92 | 0.86 | −1.56 | −0.31 |
| LSM14A | 0.25 | −0.01 | −0.15 | −0.01 | −0.13 | RNA5SP317 | 0.54 | 0.55 | 0.54 | −0.30 | 0.38 | LINC00572 | −0.36 | −0.32 | 0.05 | −0.63 | −1.01 |
| PTCSC2 | −1.14 | 1.22 | −0.03 | 0.92 | −1.26 | AL583810.1 | −0.37 | −0.25 | −0.48 | 0.29 | 0.22 | AC007221.1 | 0.59 | −2.01 | 0.04 | −0.70 | 0.68 |
| GREM1 | 1.02 | −0.79 | 0.08 | −0.89 | −0.17 | AC009779.1 | −0.84 | 0.58 | 2.10 | −1.23 | 1.29 | RNU6-1340P | 0.26 | −1.07 | −0.66 | −0.02 | −1.97 |
| AC138305.1 | −1.18 | 0.95 | 1.02 | 0.47 | 0.03 | AC011466.2 | −0.56 | −0.12 | −0.98 | 0.62 | −0.14 | AC006971.1 | −0.13 | 0.28 | 0.04 | 0.17 | −0.28 |
| NAT1 | 0.71 | −0.37 | −0.87 | −0.14 | −0.66 | CYP4F10P | 0.90 | −0.24 | −1.43 | −0.18 | −1.79 | AC007562.1 | −0.34 | 1.62 | −0.16 | 1.44 | −1.08 |
| GAS6-AS1 | −0.71 | 0.52 | 0.41 | 0.40 | −0.02 | AC097527.1 | 1.32 | −1.28 | −1.01 | 0.26 | −0.44 | ST8SIA5 | −0.13 | −0.44 | −0.57 | 0.47 | 0.33 |
| SH3BP5 | −0.80 | 0.51 | 0.92 | −0.11 | 0.06 | CARD18 | 0.43 | 0.22 | 0.29 | −0.14 | 0.06 | SALL4P2 | 0.42 | −0.84 | −0.26 | −0.40 | 0.22 |
| LINC02487 | 1.75 | −1.26 | −1.80 | 0.37 | −0.27 | FBXL22 | −0.27 | 0.07 | 0.15 | 0.31 | 0.19 | AC234781.1 | 0.12 | 0.40 | −0.71 | 0.08 | 0.10 |
| AC079089.1 | −1.59 | 0.51 | −0.23 | 1.28 | 0.38 | ITK | 0.44 | −0.84 | 0.36 | −0.75 | 0.03 | OR8A2P | 0.44 | −1.66 | −0.64 | −1.14 | 0.95 |
| AC090044.1 | −2.08 | 1.94 | 0.62 | 1.89 | −1.69 | BNIP3P41 | 0.92 | −0.75 | −1.05 | 0.84 | −0.74 | AP003467.2 | −0.09 | −0.08 | 0.78 | −0.29 | 0.44 |
| HDDC2 | 0.43 | −0.19 | −0.23 | −0.13 | −0.19 | MYCN | −0.51 | −0.08 | 1.94 | −0.72 | 0.89 | RPL29P24 | −0.13 | 0.44 | 0.71 | 0.38 | 0.40 |
| RBM15B | 0.45 | −0.04 | −0.50 | 0.11 | −0.33 | AC108673.3 | 0.38 | −0.19 | −0.50 | −0.05 | −0.19 | ITPK1 | 0.04 | −0.20 | −0.70 | 0.11 | −0.15 |
| FNDC10 | 1.15 | −0.25 | −1.03 | 0.11 | −0.38 | SETP3 | 0.58 | −0.70 | −0.51 | −0.18 | 0.03 | AC032027.1 | 0.16 | 0.30 | 0.24 | 0.74 | 0.62 |
| CARD10 | 0.75 | −0.31 | −1.30 | 0.11 | −0.24 | ERCC6 | −0.08 | 0.13 | 0.18 | −0.01 | 0.03 | AC079779.2 | −0.19 | 0.07 | 0.94 | 0.74 | −0.42 |
| LINC01698 | −1.65 | 0.80 | 0.79 | 1.11 | 0.43 | AC131568.1 | 0.64 | −0.28 | 0.61 | −0.77 | −0.07 | AC009275.1 | 0.17 | −0.41 | −0.67 | −0.75 | −0.98 |
| NTM | −0.66 | 0.15 | 0.19 | 0.05 | 0.10 | AL513485.1 | −0.54 | 0.11 | 0.81 | −0.02 | −0.04 | ST7L | 0.03 | −0.02 | −0.03 | 0.08 | 0.14 |
| ASPSCR1 | −0.54 | 0.20 | 0.09 | 0.31 | 0.17 | SETBP1 | −0.12 | 0.30 | 0.05 | 0.02 | −0.23 | AC139491.2 | −0.43 | −1.34 | −1.03 | 0.22 | −0.17 |
| C2CD6 | −0.97 | 0.19 | 0.41 | 0.06 | 0.08 | AC002094.4 | −0.65 | 0.64 | −0.05 | 0.49 | −0.66 | AL137222.1 | −0.14 | −0.62 | 0.84 | −0.42 | 0.71 |
| PYROXD1 | 0.40 | −0.05 | −0.28 | −0.09 | −0.22 | AL157815.1 | −0.80 | 0.04 | −1.14 | 0.12 | 0.36 | MIP | −0.17 | −0.91 | −0.73 | −0.17 | −0.46 |
| FPR3 | 1.26 | −1.03 | −0.74 | −0.52 | −0.35 | NBPF15 | −0.11 | 0.01 | 0.27 | −0.15 | 0.23 | OR7E39P | −0.32 | 0.17 | −0.01 | 0.59 | −1.60 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| NOXA1 | −0.86 | 0.34 | 0.33 | 0.78 | 0.36 | MIR3688-2 | 0.88 | −0.74 | 0.55 | −0.28 | 1.07 | AC138356.3 | −0.23 | −0.81 | −1.50 | 0.31 | −0.59 |
| AC087203.2 | −1.66 | 0.95 | 0.65 | 0.42 | −0.87 | AP000857.1 | −0.73 | 0.69 | 1.28 | 0.35 | 0.25 | AC004908.1 | 0.09 | −0.10 | −0.11 | 0.14 | 0.15 |
| AC093330.2 | −0.65 | −0.02 | −0.09 | 0.25 | 0.04 | AC073046.1 | −0.25 | 0.19 | 0.03 | 0.07 | 0.06 | AL513331.1 | −0.47 | 0.38 | 1.87 | −0.06 | 1.76 |
| C3 | −1.48 | 1.38 | 2.48 | 0.62 | 0.33 | RNU6-807P | 0.84 | 0.13 | −0.60 | −0.54 | −0.48 | RN7SL653P | 0.12 | −0.31 | 1.02 | −0.28 | 0.66 |
| MIR920 | −1.60 | 1.44 | 0.89 | 0.89 | −0.15 | PDGFRB | −0.29 | 0.22 | 0.82 | −0.35 | −0.27 | FAR2P1 | −0.20 | −0.47 | −0.56 | 0.35 | 0.32 |
| AC090114.2 | −0.52 | 0.32 | 0.02 | 0.37 | 0.06 | AL731568.1 | 0.45 | 0.04 | −0.13 | −0.13 | −0.07 | LINC00628 | −0.29 | −1.80 | −1.49 | −0.25 | −0.94 |
| OVGP1 | −0.79 | 0.68 | 0.57 | 0.55 | 0.11 | AC024619.3 | −0.33 | −0.15 | −0.65 | −0.02 | −0.03 | COL4A3BP | 0.03 | 0.06 | −0.01 | 0.01 | −0.17 |
| ATP5PF | 0.70 | −0.23 | −0.40 | −0.14 | −0.54 | CNOT4 | −0.08 | 0.12 | 0.15 | −0.05 | −0.05 | AC011498.6 | −0.15 | −0.02 | 0.87 | −0.44 | −0.73 |
| AC104763.2 | 1.65 | −0.30 | −0.72 | −0.30 | −0.65 | LINC01615 | 0.42 | −0.09 | 1.26 | −0.20 | 0.35 | MT-ATP8 | −0.08 | 0.28 | −0.02 | 0.17 | −0.47 |
| ODF3 | −1.26 | 0.80 | 1.30 | 0.10 | 0.29 | LRTM1 | 0.40 | 0.12 | −0.26 | 0.30 | −0.16 | AL391422.2 | −0.34 | 0.00 | 0.37 | 1.05 | −0.86 |
| CTSA | 0.42 | −0.28 | −0.28 | 0.10 | −0.12 | PRR5 | 0.20 | 0.01 | −0.31 | 0.05 | 0.07 | AL139281.1 | −0.50 | 0.18 | −0.91 | 1.25 | −0.37 |
| SDF2 | 0.43 | −0.21 | −0.30 | −0.06 | −0.25 | RAB33B | −0.16 | 0.27 | 0.57 | −0.06 | 0.03 | OR2Y1 | 0.38 | 0.01 | −0.12 | 0.86 | −0.74 |
| AP1G1 | 0.33 | −0.13 | −0.25 | −0.05 | −0.09 | AC022494.1 | −0.86 | 0.86 | −1.04 | 0.97 | −1.67 | G20694 | 0.32 | 0.58 | −1.63 | 1.40 | −0.93 |
| AC017091.1 | −1.79 | −0.41 | 0.83 | −0.34 | 0.51 | ABCC13 | −0.67 | 0.33 | −1.48 | 0.80 | −0.47 | AL139099.2 | −0.14 | 0.49 | −0.21 | −0.21 | −0.55 |
| H3F3A | 0.53 | −0.10 | −0.46 | 0.15 | −0.24 | NPY2R | −1.05 | −0.51 | 0.49 | 1.19 | 2.20 | MTNR1A | −0.31 | −0.09 | −1.76 | 0.79 | 0.42 |
| BACE1-AS | −0.52 | 0.30 | 0.39 | 0.05 | 0.08 | IFNL4 | −1.10 | −1.23 | 0.85 | −0.46 | −0.21 | RN7SL836P | 0.33 | −1.21 | −1.16 | 1.29 | 0.72 |
| G34082 | 2.47 | −0.50 | −1.88 | 0.46 | −1.12 | AC115284.2 | −0.46 | −1.03 | −0.50 | 0.80 | 1.81 | AC015540.1 | 0.31 | −0.46 | −0.71 | 0.69 | 0.99 |
| SNORA14B | −0.87 | 0.69 | 0.46 | 0.40 | −0.24 | DAXX | 0.18 | −0.26 | −0.31 | −0.13 | 0.02 | AC107952.2 | −0.57 | 0.23 | 0.95 | −0.59 | −1.08 |
| ARL6IP1 | 0.72 | −0.33 | −0.47 | −0.05 | −0.21 | SFTPA2 | 1.18 | 0.52 | −3.67 | 1.30 | −2.46 | AC096582.3 | −0.31 | −0.53 | −1.02 | 0.54 | −0.92 |
| LRRC27 | −0.60 | 0.16 | 0.24 | 0.12 | 0.02 | B4GALT5 | 0.18 | −0.26 | −0.23 | −0.16 | −0.03 | LINC00613 | 0.69 | 0.82 | −1.61 | 0.62 | −1.82 |
| RMND5B | −0.38 | 0.26 | 0.39 | 0.19 | 0.15 | MSRA | −0.12 | 0.10 | −0.24 | 0.09 | −0.03 | AL008638.2 | −0.29 | 0.03 | −0.92 | −1.09 | −0.08 |
| ACSL1 | −0.69 | 0.38 | 0.48 | 0.33 | 0.21 | NANOGP1 | 0.83 | −2.32 | −1.18 | −0.63 | −0.29 | AC007559.1 | 0.26 | 1.41 | −0.71 | 0.19 | −0.17 |
| AC007557.4 | −1.72 | 2.05 | 0.32 | 0.02 | 0.39 | STPG3 | −0.72 | 0.72 | 1.01 | 0.11 | −0.55 | AL049634.1 | −0.22 | −1.15 | 0.77 | −0.69 | 0.85 |
| DYRK2 | 0.37 | −0.07 | −0.05 | −0.04 | −0.12 | ARHGAP27 | −0.16 | 0.09 | −0.11 | 0.03 | −0.05 | AC022535.1 | 0.61 | −0.54 | −0.92 | −0.66 | 0.32 |
| DDX50 | 0.27 | −0.12 | −0.13 | −0.06 | −0.04 | AL591846.1 | 0.42 | −0.11 | −0.59 | −0.70 | −0.70 | OR11I1P | −0.26 | −1.28 | −2.53 | 0.53 | −1.41 |
| AC009554.2 | −0.98 | −0.08 | 0.38 | 0.02 | 0.84 | ADRA2B | −0.52 | 0.52 | 0.32 | 0.18 | 0.70 | OR52A1 | 0.23 | 0.36 | −0.46 | 0.94 | −0.52 |
| CCDC84 | −0.42 | 0.08 | 0.12 | 0.15 | 0.22 | G14419 | 0.59 | −0.40 | −0.43 | 0.10 | −0.65 | AL160408.1 | −0.09 | 0.19 | −0.36 | −0.72 | −0.71 |
| LINC02210 | −0.58 | 0.44 | 0.52 | 0.16 | 0.09 | LEF1-AS1 | −0.48 | −0.18 | 0.00 | −0.14 | 0.24 | AC007262.1 | 0.27 | 0.70 | 0.04 | −0.16 | −0.49 |
| BEND3 | 0.77 | −0.71 | −1.23 | −0.04 | −0.37 | AC006460.1 | 0.41 | −0.29 | 0.43 | 0.02 | 0.65 | RPL41P2 | 0.07 | −0.38 | −0.26 | 0.09 | 0.58 |
| ATP7B | −0.47 | 0.17 | 0.40 | −0.01 | 0.17 | RNU6-1003P | 0.79 | −0.74 | −0.33 | −0.72 | 1.06 | AL159978.1 | −0.44 | −0.78 | 0.22 | 1.47 | −0.46 |
| GALNT15 | −1.19 | 0.68 | 0.62 | 0.56 | −0.45 | AC104849.1 | −0.90 | 0.13 | 0.71 | −1.19 | 0.15 | AC005252.3 | −0.40 | 0.95 | −0.79 | 0.47 | −1.50 |
| POMK | 0.35 | −0.23 | −0.41 | 0.05 | −0.12 | FAM30A | 0.65 | −0.88 | 0.36 | −0.68 | −0.19 | MTND4P8 | −0.58 | −1.37 | −0.50 | −0.74 | −0.53 |
| NTN4 | −0.79 | 0.55 | 1.03 | 0.24 | 0.40 | NRG1-IT1 | −0.89 | −0.53 | −1.26 | 0.07 | −0.53 | AC021736.1 | −0.56 | −0.64 | −0.72 | 0.73 | −1.40 |
| CRTAP | −0.57 | 0.35 | 0.47 | 0.05 | 0.02 | AC010931.2 | −0.66 | 1.16 | 0.06 | 1.00 | −0.64 | AC090987.1 | 0.27 | −1.41 | −0.18 | −1.49 | 0.10 |
| KRT18P15 | −0.89 | 0.56 | 0.82 | 0.38 | 0.08 | AC090617.4 | 0.49 | −0.60 | −0.37 | −0.43 | −0.52 | GCNT1 | 0.08 | 0.10 | 0.65 | −0.11 | −0.02 |
| NAPSA | −1.03 | 0.53 | 0.08 | 0.56 | 0.19 | ASB18 | −0.67 | −0.60 | −0.45 | −0.09 | 0.10 | AL023773.2 | 0.36 | −0.45 | −1.55 | 1.30 | 0.51 |
| AC068446.1 | −0.66 | 0.28 | 1.13 | 0.73 | 1.02 | CNTNAP3P1 | −1.14 | −0.23 | 2.21 | −1.61 | −0.15 | RAF1P1 | 0.16 | −0.28 | −1.86 | 0.72 | −0.56 |
| LINC01127 | 1.56 | −1.39 | −1.97 | −0.13 | 0.08 | G32319 | −0.87 | 0.48 | 0.63 | 0.54 | −0.13 | AC078993.1 | 0.22 | −1.79 | −0.32 | 0.48 | 1.18 |
| PUS10 | 0.58 | −0.10 | 0.03 | 0.03 | −0.14 | GLP2R | −0.58 | −0.82 | −0.38 | 0.00 | 0.37 | GAS8-AS1 | 0.09 | −0.43 | −0.24 | 0.38 | 0.83 |
| RNF181 | 0.36 | −0.30 | −0.19 | −0.18 | −0.29 | LINC00184 | −0.56 | −0.28 | −0.49 | −0.94 | −1.06 | SNORA15 | −0.15 | −0.06 | −0.33 | 0.54 | −0.67 |
| SRP68 | 0.36 | −0.15 | −0.34 | −0.09 | −0.16 | POU4F3 | 0.64 | −1.22 | −0.02 | −0.17 | −0.03 | AC009988.1 | 0.63 | 0.68 | 0.45 | −1.06 | −1.17 |
| RPS18 | 0.65 | −0.07 | −0.06 | −0.16 | −0.48 | AC090531.1 | −0.74 | 0.55 | 0.13 | −0.59 | 0.17 | AL713866.1 | 0.55 | −1.70 | −2.10 | 0.28 | −0.44 |
| OTOP3 | 1.34 | 0.62 | −0.93 | 0.16 | −1.42 | HSDL2 | 0.23 | 0.07 | 0.28 | 0.11 | −0.04 | GEMIN8P3 | −0.46 | 1.23 | −0.02 | 1.77 | −0.97 |
| SPOPL | 0.46 | 0.00 | −0.33 | 0.09 | −0.22 | COX7A2P1 | 0.59 | 0.37 | 0.51 | −0.07 | −0.31 | LINC02331 | −0.31 | −0.62 | 0.39 | −0.57 | −1.43 |
| AC108734.3 | −1.49 | 0.88 | 1.27 | 0.46 | −0.23 | PABPN1 | −0.16 | 0.07 | 0.14 | 0.01 | 0.05 | ANKHD1 | −0.04 | 0.11 | 0.22 | 0.10 | 0.09 |
| PPP1R7 | 0.40 | −0.11 | −0.12 | 0.07 | −0.13 | G4303 | −0.45 | −0.22 | 0.86 | −0.56 | 0.61 | AC131274.3 | 0.41 | 1.21 | −1.55 | 1.33 | −2.09 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| DMRT2 | −1.60 | 1.33 | 1.76 | 1.32 | −0.33 | BDP1 | 0.12 | −0.04 | −0.11 | −0.11 | −0.01 | AC126696.1 | 0.50 | 0.48 | −0.86 | 1.03 | −1.12 |
| EIF3K | 0.39 | −0.19 | −0.26 | −0.14 | −0.21 | AC083864.2 | −1.08 | 0.05 | 1.00 | 0.32 | 1.00 | RNU6-204P | 0.34 | −0.11 | 0.01 | 2.44 | 1.54 |
| G14382 | −2.50 | 1.81 | 2.27 | 1.41 | 0.51 | AL031600.1 | −0.41 | 0.67 | 0.10 | 0.62 | −0.03 | RSU1P1 | −0.69 | 0.03 | −0.64 | 0.34 | 0.96 |
| PRDM6 | −0.92 | 0.06 | 1.19 | 0.24 | 0.46 | MIR4500HG | −0.71 | −0.42 | 0.35 | −0.65 | 0.00 | AC019155.3 | −0.39 | −1.02 | 0.68 | 1.49 | 0.80 |
| RASGRP4 | −0.65 | 0.03 | 0.33 | 0.08 | 0.23 | RN7SKP79 | −0.58 | 0.82 | −0.17 | 0.71 | −0.50 | PIGV | −0.04 | −0.03 | −0.09 | 0.05 | −0.14 |
| SDHAP1 | −0.42 | 0.14 | 0.41 | 0.17 | 0.12 | DUS3L | −0.21 | −0.04 | −0.39 | 0.20 | 0.15 | PHF24 | 0.07 | −0.24 | −0.55 | −0.57 | −0.53 |
| AL356481.2 | −1.01 | 0.17 | 0.54 | −0.01 | 0.22 | NBL1 | 0.18 | 0.01 | 0.00 | −0.15 | −0.14 | NPHS1 | 0.18 | −0.53 | −0.80 | 0.09 | 0.17 |
| MAB21L1 | −1.18 | 0.80 | 1.24 | 0.44 | 0.23 | SLC22A25 | −0.63 | 0.04 | −0.22 | 1.01 | 1.53 | OR4A44P | 0.59 | −1.92 | 1.04 | 0.31 | 1.58 |
| NTN1 | −0.63 | 0.12 | 0.32 | −0.23 | 0.03 | RPS20P14 | 0.62 | 0.11 | 0.54 | −0.52 | −0.17 | RNU6-399P | 0.24 | −0.08 | −0.23 | −0.72 | −2.53 |
| HECW2 | 0.47 | 0.06 | −0.43 | −0.09 | −0.43 | AP001150.1 | −0.44 | 0.49 | 0.32 | 0.29 | 0.20 | MTND2P20 | −0.29 | 1.12 | −1.31 | 1.07 | −2.15 |
| BMS1 | 0.41 | −0.32 | −0.41 | −0.15 | −0.04 | RPS6P25 | 0.26 | 0.10 | −0.28 | 0.44 | 0.15 | AC016397.2 | −0.14 | −0.23 | 0.42 | −0.47 | 0.28 |
| SMC1A | 0.41 | −0.37 | −0.45 | −0.20 | −0.13 | FCGR2B | −0.31 | 0.00 | 0.09 | 0.29 | 0.20 | AC023824.4 | 0.45 | 0.20 | −0.24 | −0.14 | −2.38 |
| RPS3AP29 | −1.17 | 0.89 | 1.57 | 0.41 | 0.87 | AC010999.1 | 0.45 | −0.14 | 0.04 | 0.06 | −0.29 | AL731661.1 | −0.44 | −0.49 | 2.38 | 0.11 | 0.80 |
| AC092691.2 | −2.52 | 1.74 | 2.22 | 0.78 | 0.47 | G37757 | 0.26 | −0.23 | 0.12 | −0.23 | 0.39 | AC008434.1 | 0.12 | −1.33 | −0.29 | −0.29 | 0.87 |
| SLC8A1 | −0.70 | 0.07 | 0.83 | −0.07 | 0.30 | OR2AS2P | −2.18 | −0.39 | 1.01 | −0.34 | 0.95 | RN7SKP56 | 0.16 | −0.80 | −0.89 | 0.41 | −0.17 |
| AC110285.2 | −1.01 | 0.65 | 0.67 | 0.61 | 0.36 | AC009562.1 | −0.62 | 0.49 | 0.15 | 0.53 | 0.42 | APIP | −0.05 | 0.14 | −0.06 | 0.40 | 0.32 |
| GTSE1 | 0.89 | −1.10 | −1.74 | −0.32 | −0.39 | KLHL36 | −0.13 | 0.11 | 0.10 | 0.12 | 0.05 | RFC1 | 0.03 | −0.07 | −0.07 | −0.07 | −0.03 |
| RIMKLA | −1.13 | 0.03 | 0.70 | 0.40 | 0.69 | PHOSPHO2 | −0.26 | 0.26 | 0.43 | 0.09 | 0.36 | AC009097.1 | 0.21 | 0.44 | −0.63 | 1.58 | 1.22 |
| LTV1 | 0.47 | −0.28 | −0.40 | −0.09 | −0.18 | PAN3-AS1 | 0.24 | −0.13 | −0.13 | 0.09 | −0.02 | OPRPN | −0.23 | −0.96 | 0.90 | −0.06 | 1.07 |
| SESN1 | −0.45 | 0.36 | 0.75 | 0.13 | 0.22 | AKAP10 | 0.07 | −0.11 | −0.02 | −0.07 | 0.09 | SFTA3 | −0.27 | −0.16 | −0.75 | −0.03 | −0.39 |
| ATF3 | −0.69 | 0.08 | 0.53 | −0.02 | 0.22 | AC125437.1 | 0.42 | 0.45 | 0.15 | 0.01 | −0.30 | AC020549.2 | −0.46 | 0.27 | 0.51 | −0.09 | 1.25 |
| SMAP2 | 0.38 | −0.30 | −0.27 | −0.23 | −0.19 | MIR199A1 | 0.64 | −0.08 | −1.03 | 0.11 | −1.23 | AP000350.2 | −0.08 | −0.43 | 0.13 | −0.07 | 0.24 |
| GFRA3 | −1.42 | 0.46 | 1.29 | 0.40 | 1.41 | PHLDA3 | −0.16 | 0.06 | −0.22 | 0.07 | −0.09 | AC084754.1 | 0.19 | 0.96 | 0.14 | 0.90 | 0.59 |
| LINC00640 | −0.82 | 0.50 | 0.77 | 0.73 | 0.48 | AC021860.1 | −1.05 | 1.00 | 2.17 | −0.12 | 0.34 | AC114550.3 | −0.71 | 0.55 | 1.18 | 1.03 | 2.04 |
| EIF3J | 0.43 | −0.30 | −0.38 | −0.19 | −0.14 | AC069503.2 | 0.75 | −0.19 | −1.35 | 0.29 | −0.99 | C8orf17 | 0.09 | −0.03 | −0.22 | 0.08 | 0.25 |
| NUDT1 | 0.51 | −0.24 | −0.34 | −0.01 | −0.20 | KRTAP10-4 | −1.55 | 0.87 | 0.31 | −0.67 | −2.68 | FLI1 | −0.06 | 0.02 | 0.65 | −0.13 | 0.12 |
| NPHP4 | −0.61 | 0.10 | −0.02 | 0.13 | 0.07 | AL160286.3 | −0.76 | 1.29 | −0.64 | 1.12 | 0.71 | EIF1P7 | 0.11 | −0.25 | 0.43 | −0.33 | 0.67 |
| SRP14 | 0.53 | −0.17 | −0.17 | −0.23 | −0.28 | B4GALT6 | 0.20 | 0.03 | −0.29 | 0.07 | 0.08 | HMHB1 | 0.37 | −2.28 | −0.59 | −0.82 | 0.96 |
| SLC35C1 | 0.51 | −0.45 | −0.55 | −0.28 | −0.23 | DLX6 | −0.39 | 0.47 | 0.56 | 0.67 | 0.26 | KIDINS220 | 0.02 | 0.11 | 0.05 | 0.01 | −0.11 |
| KCNMB1 | −0.82 | 0.42 | 0.28 | 0.06 | −0.28 | LINC00304 | −0.65 | 0.13 | −0.52 | 0.13 | −0.30 | RNU6-707P | −0.46 | 0.43 | −0.70 | 1.51 | −0.80 |
| SIM1 | −1.06 | 0.58 | 1.40 | 0.01 | 0.00 | MIR1273C | 0.71 | −0.30 | −0.08 | −0.71 | 0.11 | AL009178.1 | −0.70 | 1.02 | 1.28 | 0.08 | −1.08 |
| GCH1 | 0.81 | −0.65 | −0.57 | −0.22 | −0.23 | AC005520.3 | 0.37 | 0.19 | −0.92 | 0.06 | −0.50 | LINC02168 | 0.50 | 0.19 | −1.50 | 0.96 | −1.41 |
| FRMD8 | 0.47 | −0.24 | −0.71 | 0.15 | −0.30 | AC092745.2 | −0.64 | 0.28 | 0.74 | −0.16 | 0.80 | RN7SKP264 | −0.47 | 0.06 | −0.32 | −0.84 | −1.60 |
| IGHG1 | 2.62 | 2.63 | 4.41 | 0.39 | −0.69 | RP11-231C14.4 | −0.33 | 0.16 | 0.14 | 0.45 | 0.78 | OR10R3P | 0.50 | −1.10 | −0.22 | 1.23 | −0.40 |
| HEPACAM | −2.07 | 0.96 | 1.47 | 0.66 | 0.25 | AL391803.1 | 0.89 | 0.06 | −1.19 | 0.60 | −0.62 | AC022413.1 | −0.16 | −1.82 | 1.02 | −0.84 | 1.29 |
| LINC02447 | −1.13 | 1.36 | 0.51 | 1.11 | −0.05 | RPL5P22 | 0.80 | −0.46 | −0.21 | −0.43 | −0.34 | RPL21P90 | −0.20 | −0.46 | 0.17 | −0.01 | 1.18 |
| SNRPB | 0.59 | −0.41 | −0.91 | 0.02 | −0.48 | AC108472.1 | −0.40 | 0.44 | 1.05 | 0.18 | 0.71 | AC011377.1 | 0.18 | −1.44 | −0.39 | −0.14 | 0.55 |
| AL138688.1 | 2.29 | −0.72 | −2.12 | 0.03 | −0.21 | CRCP | 0.09 | −0.10 | 0.00 | 0.02 | 0.17 | AL451065.1 | 0.39 | −1.24 | −0.44 | −0.38 | 2.88 |
| NRN1 | −0.86 | 0.46 | 1.28 | 0.07 | 0.32 | OTUD1 | −0.17 | 0.37 | 0.05 | 0.22 | −0.15 | AC007238.1 | 0.09 | −0.24 | −0.41 | 0.40 | −0.30 |
| EVC2 | −0.44 | 0.22 | 0.10 | 0.14 | 0.02 | LDLRAD1 | 0.96 | −0.75 | 2.04 | −0.25 | 1.20 | AC074029.1 | 0.48 | −1.23 | −2.43 | 0.22 | −0.31 |
| PCDHA13 | −1.67 | 0.35 | 1.12 | 1.09 | 0.71 | PEX2 | 0.14 | 0.07 | −0.18 | 0.08 | −0.25 | AL358781.2 | −0.22 | −0.92 | −1.28 | −0.66 | −1.05 |
| AP000662.1 | −0.88 | 0.10 | 0.62 | 0.25 | 0.51 | RGR | −0.80 | 0.96 | −0.24 | 1.34 | −0.18 | KIR3DL1 | 0.27 | 0.00 | −2.50 | −0.02 | −1.84 |
| RNF167 | 0.36 | 0.02 | −0.29 | 0.09 | −0.23 | AP4B1 | −0.10 | −0.06 | 0.24 | 0.00 | 0.29 | HMGB3P14 | −0.07 | −0.04 | −0.88 | 0.15 | −0.35 |
| DND1P1 | −0.98 | 0.16 | 1.03 | 0.52 | 0.97 | HIST2H2BD | 0.34 | −0.53 | −0.07 | −0.23 | 0.49 | CABYRP1 | 0.50 | −1.17 | −1.99 | 0.64 | −0.53 |
| AC092162.2 | −0.78 | 0.52 | 1.29 | 0.03 | 0.43 | MIR762HG | −0.37 | −0.11 | 0.57 | −0.39 | 0.14 | AC063976.2 | −0.08 | 0.23 | 0.53 | −0.18 | 0.14 |
| SINHCAF | 0.62 | −0.22 | −0.50 | −0.05 | −0.24 | AC109133.1 | 1.34 | −0.04 | −0.16 | 0.23 | −0.66 | AL160286.2 | 0.46 | −0.65 | −1.53 | 0.84 | 1.56 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| PCBP1 | 0.42 | −0.06 | −0.61 | 0.07 | −0.46 | MRPL23 | 0.15 | 0.08 | −0.05 | −0.11 | −0.18 | SCARNA21 | 0.08 | 0.38 | 0.81 | −0.50 | −0.02 |
| CORO6 | 0.72 | −0.25 | −1.76 | 0.69 | −0.28 | SLC22A6 | −0.83 | 0.77 | 0.18 | −0.58 | −0.25 | MTND5P6 | −0.48 | 0.38 | 0.52 | 1.86 | −1.58 |
| PPARA | −0.41 | 0.24 | 0.48 | 0.19 | 0.46 | AC006435.2 | −0.28 | 0.29 | 0.57 | −0.05 | 0.22 | LINC01811 | −0.28 | −0.25 | 0.00 | 0.35 | 0.92 |
| AP003969.2 | −0.98 | 0.38 | 0.52 | −0.31 | 0.23 | B4GALT7 | −0.14 | 0.09 | −0.04 | 0.12 | 0.05 | MYO16-AS1 | 0.27 | −0.12 | 1.18 | 0.73 | 2.33 |
| DYNC1LI1 | 0.35 | −0.05 | −0.12 | −0.21 | −0.17 | CLDN4 | 0.26 | 0.59 | 0.18 | 0.00 | −0.67 | CR381572.2 | 0.24 | −1.24 | −1.08 | 0.07 | 0.50 |
| MRPL4 | 0.42 | −0.25 | −0.59 | 0.07 | −0.19 | BODIL1 | 0.10 | −0.01 | −0.09 | −0.08 | −0.09 | PLK3 | −0.05 | −0.13 | −0.34 | 0.08 | 0.00 |
| CRAT | −1.11 | 0.53 | 0.48 | 1.05 | 1.03 | KRT80 | 0.31 | 0.40 | 0.08 | 0.23 | −0.58 | NHS-AS1 | −0.08 | −0.74 | −0.59 | −0.26 | 0.20 |
| AVEN | 0.42 | −0.42 | −0.75 | −0.21 | −0.01 | LACRT | −1.08 | 1.41 | 1.57 | 0.83 | 0.33 | AC114776.1 | 0.24 | −1.01 | −0.53 | 0.20 | 0.12 |
| AL031429.1 | −1.41 | 1.14 | 1.73 | 0.25 | −0.01 | DERL3 | −0.45 | 0.46 | 1.01 | 0.41 | 0.97 | MT1X | −0.08 | 0.29 | −0.09 | 0.34 | −0.10 |
| AC005520.2 | −1.17 | 0.19 | 0.61 | 0.09 | 0.26 | NRP1 | −0.23 | 0.04 | 0.52 | −0.06 | −0.05 | RPSAP55 | 0.63 | −0.59 | 0.91 | −0.43 | −0.33 |
| GPRC5C | −0.82 | 0.66 | 0.44 | 0.51 | 0.01 | MTATP6P1 | −0.29 | 0.02 | 0.28 | 0.46 | 0.12 | AL590068.1 | 0.29 | −0.65 | −1.73 | 0.47 | 0.26 |
| CENPL | 0.50 | −0.45 | −0.48 | −0.06 | −0.24 | LINC00412 | −0.75 | −0.52 | −0.27 | 0.57 | 0.72 | LINC01435 | −0.16 | −0.34 | 0.14 | 0.24 | 0.19 |
| AC136632.1 | −0.77 | 0.06 | 0.72 | −0.05 | 0.83 | AL158850.1 | −0.84 | 0.16 | 1.00 | 0.24 | 0.96 | RGS16 | 0.10 | −0.67 | −0.21 | −0.98 | −0.32 |
| AC005674.1 | 1.61 | −1.85 | −2.03 | −0.54 | −0.08 | POU3F2 | −0.60 | 0.95 | 0.29 | 0.25 | −0.80 | AL022069.1 | −0.11 | −0.64 | −0.24 | −0.04 | 0.61 |
| AC098483.1 | −3.93 | 0.35 | 1.95 | −0.89 | −0.77 | GPC5-IT1 | −1.14 | −0.17 | 1.04 | −0.36 | 0.37 | AL138725.1 | 0.14 | 0.21 | 1.05 | 0.39 | −0.08 |
| DNAJB8 | −1.59 | −0.22 | −0.33 | 0.15 | −0.27 | RN7SKP249 | −0.93 | −0.06 | 0.54 | −1.00 | −0.91 | AL591770.1 | 0.22 | −0.32 | −0.20 | −0.29 | 0.43 |
| SRSF3 | 0.41 | −0.25 | −0.50 | −0.03 | −0.25 | PPP3R2 | −0.78 | 1.34 | −1.15 | 0.72 | −1.38 | OR4D11 | −0.60 | 0.52 | 0.71 | 0.63 | −1.09 |
| LRP3 | −0.67 | 0.26 | 0.25 | 0.11 | 0.21 | RPS26P41 | −0.50 | −0.18 | 1.22 | −0.01 | 1.00 | AL133243.3 | −0.04 | 0.26 | 0.04 | 0.06 | −0.08 |
| PDE12 | 0.44 | −0.21 | −0.37 | −0.07 | −0.24 | AL358933.1 | −0.64 | 0.36 | 0.49 | 0.79 | 0.27 | AC006499.5 | −0.40 | 0.17 | −0.21 | −0.59 | −0.25 |
| LRRC58 | 0.48 | −0.16 | −0.25 | −0.06 | −0.22 | LINC01447 | −0.58 | −0.35 | −0.68 | 0.50 | −0.18 | MFSD3 | −0.05 | 0.21 | −0.05 | 0.32 | 0.15 |
| ATP6AP2 | 0.48 | −0.08 | −0.11 | −0.15 | −0.40 | RPS2P35 | 0.52 | −0.19 | −0.45 | 0.27 | 0.29 | MTCO3P17 | 0.29 | −0.84 | −0.56 | 0.10 | 0.41 |
| ACTA1 | −1.48 | −0.28 | 0.31 | −0.38 | −0.69 | CYP4F26P | −0.44 | 0.12 | 0.23 | 0.14 | 0.25 | AC005730.1 | 0.23 | −0.99 | 1.72 | −0.05 | 1.66 |
| PSG1 | −1.07 | 0.36 | 1.41 | −0.20 | 0.38 | AC092574.1 | −0.53 | −0.33 | 0.89 | −0.92 | −0.17 | LINC00934 | −0.29 | −0.57 | 0.23 | 0.27 | 0.49 |
| SOX15 | 0.87 | −0.51 | −1.07 | −0.05 | −0.61 | EMP3 | −0.24 | −0.10 | −0.23 | −0.12 | −0.26 | AC090116.1 | −0.62 | 2.22 | 0.21 | −0.87 | −1.54 |
| GAS7 | −0.57 | 0.37 | 0.66 | 0.04 | −0.21 | AP001001.1 | 0.33 | 0.33 | −0.06 | 0.28 | −0.21 | LINC01591 | 0.40 | −0.08 | 0.27 | 0.54 | 0.15 |
| LINC01343 | 1.41 | −1.32 | −1.20 | −0.08 | 0.05 | H3F3AP6 | 0.40 | −0.10 | −0.02 | 0.08 | 0.14 | RN7SL741P | −0.89 | −0.15 | 0.59 | 0.16 | 1.40 |
| PCDHGB1 | −1.09 | 0.59 | 1.48 | 0.11 | 0.40 | PREB | 0.16 | −0.19 | −0.27 | −0.05 | 0.00 | LINC02107 | 0.88 | −0.94 | 0.55 | 0.61 | 2.87 |
| ST5 | 0.51 | −0.46 | −1.15 | 0.05 | −0.31 | C2CD4A | 0.54 | −1.23 | −1.26 | −0.23 | 0.01 | SCGN | 0.21 | −0.88 | 0.82 | −0.25 | 1.03 |
| SATB2 | −0.71 | 0.04 | 0.55 | −0.06 | 0.22 | AL589993.1 | −0.33 | 0.22 | −0.04 | 0.06 | −0.18 | C17orf77 | 0.20 | −2.30 | −2.10 | 0.53 | −0.77 |
| GTF2E1 | 0.42 | −0.29 | −0.30 | −0.09 | −0.06 | AC021549.1 | 0.68 | −0.51 | −3.91 | −0.36 | −3.21 | LINC02130 | −0.26 | −0.98 | −0.03 | −1.18 | −0.27 |
| DCTN6 | 0.43 | −0.11 | −0.55 | −0.04 | −0.34 | AC144521.1 | 0.71 | 0.10 | 0.39 | 0.46 | 0.68 | DPY19L4 | −0.02 | 0.00 | 0.08 | −0.01 | 0.02 |
| AC010311.1 | −1.97 | 1.09 | 0.92 | 0.29 | −0.96 | AL022724.1 | 0.52 | −0.51 | −0.82 | 0.06 | −0.22 | LINC01751 | −0.28 | −0.60 | −0.90 | 1.83 | 1.04 |
| AC142472.1 | −0.78 | 0.44 | 0.80 | 0.36 | 0.32 | ADAM32 | −0.29 | −0.09 | 0.27 | −0.19 | 0.05 | G39722 | −0.52 | 0.35 | 1.10 | 0.68 | −0.48 |
| AL022067.1 | 1.79 | −0.53 | −1.37 | −0.82 | −1.06 | RNU6-181P | 0.61 | −1.66 | 0.71 | −0.96 | 0.68 | RPL3P9 | −0.23 | −0.38 | 0.12 | −0.81 | −0.39 |
| ABHD18 | −0.38 | 0.11 | 0.11 | 0.09 | −0.07 | CASKIN2 | 0.15 | 0.06 | −0.22 | 0.13 | −0.08 | AC120057.4 | 0.23 | −0.13 | −1.38 | 0.50 | −0.54 |
| SLCO3A1 | −0.51 | 0.20 | 0.58 | 0.01 | 0.02 | PFAS | −0.18 | −0.35 | −0.17 | 0.13 | 0.41 | FKBP9 | −0.03 | 0.10 | 0.35 | −0.15 | −0.03 |
| SLC25A4 | −0.52 | 0.36 | 0.35 | 0.13 | 0.02 | FYTTD1P1 | 0.88 | −0.46 | −0.71 | −0.29 | 0.29 | CALHM3 | −0.35 | −0.85 | −0.35 | 0.30 | −1.03 |
| GPC6 | −1.24 | 0.68 | 0.92 | −0.33 | −0.25 | MGAM2 | −0.58 | 0.15 | 0.52 | −0.10 | 0.24 | CXorf66 | 0.64 | −0.05 | −1.29 | 1.92 | 1.06 |
| COQ8B | −0.47 | 0.20 | 0.44 | 0.14 | 0.38 | CCDC27 | −0.84 | −0.22 | 0.65 | 0.21 | 0.88 | AC104260.1 | −0.28 | −0.36 | 0.17 | −0.19 | 1.20 |
| FAM182B | −0.74 | −0.05 | 0.12 | 0.57 | 0.77 | AC117402.1 | −0.71 | −0.17 | 0.70 | −0.20 | 0.44 | AC027045.3 | 0.28 | −1.09 | −3.06 | 0.32 | −1.25 |
| RAB3IL1 | −1.02 | 0.53 | 1.13 | 0.15 | 0.27 | RNA5SP134 | −1.04 | 0.89 | −1.00 | 1.37 | −1.08 | RN7SL234P | 0.43 | −1.08 | −0.64 | 1.42 | −0.39 |
| CTLA4 | 2.02 | −1.44 | −1.17 | −1.07 | −0.50 | IDH1-AS1 | −0.82 | 0.40 | −0.90 | 0.07 | −0.47 | OR5V1 | 0.27 | −0.04 | −0.17 | 0.38 | −0.27 |
| AL117339.4 | −0.82 | 0.28 | 0.19 | 0.23 | 0.28 | AC132872.3 | 0.37 | −0.89 | −0.82 | −0.39 | −0.13 | G23132 | 0.11 | −0.41 | −1.00 | −0.25 | −0.67 |
| FKBP5 | −0.39 | 0.22 | 0.22 | 0.31 | 0.04 | PXDN | 0.39 | −0.27 | −0.32 | −0.66 | −0.53 | MTND1P18 | 0.56 | −1.08 | −0.43 | 0.71 | 0.58 |
| RP11-417J8.6 | −1.00 | 1.02 | 0.42 | 0.82 | 0.25 | AL445649.1 | 0.78 | 0.12 | 0.48 | 0.69 | 0.52 | G28242 | −0.08 | −0.10 | −0.64 | 0.20 | −0.74 |
| DNAJC17 | −0.62 | 0.28 | 0.12 | 0.23 | −0.02 | AL136366.1 | −0.44 | 0.94 | 0.71 | 0.40 | −0.11 | AC006249.1 | −1.10 | −0.67 | −0.05 | 0.60 | 0.43 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| ANAPC7 | 0.44 | −0.28 | −0.46 | −0.04 | −0.02 | CFL1P5 | −0.45 | 0.79 | 0.13 | 0.23 | 0.05 | RAD23BP1 | 0.27 | 0.10 | 0.82 | −0.16 | 0.64 |
| IKBKB | −0.41 | 0.13 | 0.19 | 0.16 | 0.21 | AC092807.1 | 0.91 | 0.90 | 1.79 | 0.24 | −0.20 | BBS4 | −0.02 | 0.06 | −0.09 | 0.07 | −0.02 |
| RPL34-AS1 | −0.83 | 0.31 | 1.26 | 0.09 | 0.63 | AC016949.1 | −0.14 | −0.09 | 0.18 | −0.13 | 0.15 | CD79B | 0.14 | −0.79 | 0.29 | −0.38 | 0.72 |
| PIGX | 0.53 | −0.37 | −0.38 | −0.10 | 0.09 | AL121761.1 | −0.51 | −0.06 | 0.41 | −0.40 | 0.21 | AC006924.1 | −0.43 | 0.03 | 1.72 | −1.01 | 0.08 |
| DNAJC3 | 0.50 | −0.21 | −0.24 | −0.24 | −0.16 | AC008937.2 | 0.31 | 0.02 | 0.22 | 0.01 | 0.25 | AC026904.1 | 0.65 | −1.27 | −0.51 | −0.34 | −0.38 |
| AP001627.1 | −1.43 | 1.11 | 1.72 | 0.86 | 0.20 | SPAG7 | 0.14 | 0.02 | −0.41 | 0.11 | −0.34 | KRT18P48 | 0.40 | −0.20 | −0.75 | 0.05 | −1.57 |
| DNAAF1 | −1.15 | 0.21 | 0.64 | −0.14 | 0.37 | AC025434.1 | −0.55 | −0.14 | 0.22 | 0.46 | 0.27 | FER1L6-AS2 | 0.31 | −0.17 | −2.31 | 0.16 | −0.24 |
| CYP1A2 | −2.11 | −0.13 | 0.45 | −1.27 | 0.09 | ABHD6 | −0.18 | 0.38 | 0.35 | 0.05 | 0.00 | AC139493.2 | −0.27 | −0.84 | −0.86 | −1.09 | −1.42 |
| LINC01485 | −1.66 | 0.74 | 0.99 | 0.52 | 0.76 | AC004522.2 | −0.77 | 0.76 | 0.60 | 0.83 | 0.12 | LINC02442 | 0.66 | −0.93 | 0.12 | −1.69 | 0.18 |
| GOLGA4 | 0.42 | −0.04 | −0.32 | −0.04 | −0.24 | AC055811.4 | −0.24 | 0.11 | 0.13 | −0.10 | 0.12 | CYBB | 0.10 | −0.50 | 0.14 | −0.18 | −0.34 |
| G20736 | 1.57 | −0.08 | −0.31 | 0.51 | −0.14 | RMND5A | 0.19 | 0.32 | 0.18 | 0.23 | −0.29 | AC008397.1 | 0.39 | −0.51 | −0.89 | 1.34 | 0.30 |
| KCNJ5 | −0.80 | 0.60 | 0.24 | 0.19 | −0.30 | LINC02181 | −0.57 | −0.05 | −2.01 | 0.49 | −0.77 | SNX25P1 | 0.11 | −0.21 | 0.20 | 0.06 | −0.04 |
| LRRC75A-AS1 | 0.49 | −0.10 | −0.25 | 0.03 | −0.31 | KRTAP1-3 | −1.55 | 1.07 | 0.87 | 0.64 | −1.59 | RPS6P4 | 0.34 | −0.28 | −2.53 | 0.92 | −1.34 |
| LINC00665 | −0.64 | 0.11 | 0.75 | −0.25 | 0.20 | MIR378A | 0.75 | −1.51 | −1.44 | 0.49 | 0.76 | RN7SKP97 | −0.07 | −0.38 | 0.12 | 0.01 | 0.68 |
| HDDC3 | −0.53 | 0.20 | 0.67 | 0.07 | 0.49 | AC010422.2 | −0.51 | −0.45 | −1.37 | 0.28 | 0.33 | AL353596.1 | 0.32 | −0.14 | 0.20 | 0.08 | 1.72 |
| RECK | −0.82 | 0.56 | 1.49 | −0.08 | 0.26 | RNA5SP295 | 0.49 | −0.58 | 0.60 | −0.08 | 0.83 | AL158071.1 | −0.25 | 0.29 | 1.11 | 0.50 | −0.20 |
| AC018809.2 | −0.51 | 0.29 | 0.48 | 0.38 | 0.39 | N4BP2 | 0.14 | 0.04 | −0.14 | 0.03 | −0.20 | BX119904.3 | −0.59 | −0.04 | −1.29 | 0.64 | −1.23 |
| EFR3A | 0.38 | −0.16 | −0.17 | −0.09 | −0.18 | LINC00861 | 0.48 | −0.58 | 1.46 | −0.85 | 1.06 | AC005785.1 | 0.07 | −0.42 | 0.33 | −0.21 | 0.39 |
| RGS7BP | −1.46 | 0.76 | 0.92 | 0.84 | 0.31 | AL136038.5 | 0.38 | −0.05 | 0.01 | 0.70 | 0.30 | AD001527.1 | −0.09 | −0.64 | 0.00 | −0.67 | 0.24 |
| RN7SL784P | −1.03 | 0.03 | 0.34 | 0.25 | 0.84 | AC073571.1 | 0.58 | −1.23 | −1.30 | −0.56 | −0.18 | BMS1P17 | 0.36 | −0.38 | −0.16 | −0.60 | 0.53 |
| MRPL42 | 0.41 | −0.19 | −0.03 | −0.24 | −0.13 | ARHGEF3-AS1 | 0.38 | −0.34 | −0.03 | 0.07 | 0.33 | AC012313.1 | −0.04 | −0.10 | 0.17 | −0.13 | 0.10 |
| AC011363.1 | 1.23 | 0.14 | 0.15 | 0.16 | −0.14 | AL592435.1 | −0.56 | −0.43 | −0.96 | −1.29 | −0.55 | AC237221.2 | −0.45 | 0.86 | −0.06 | 0.93 | −1.34 |
| AL049629.2 | 1.61 | 0.26 | −1.00 | −0.11 | −0.77 | MTCO2P30 | −0.84 | 0.53 | −0.62 | −0.18 | −1.87 | LINC00922 | 0.19 | −0.67 | −0.55 | −0.55 | 0.45 |
| ATP5MGL | −0.88 | 0.81 | 0.49 | 0.43 | −0.09 | LINC00320 | 1.10 | −1.30 | −1.03 | 0.56 | −0.63 | AL161937.1 | 0.43 | −0.78 | 0.33 | 0.30 | 0.51 |
| AP001528.1 | −1.46 | 0.68 | −0.04 | 0.24 | 0.01 | RN7SL359P | −0.61 | 0.17 | −0.51 | −0.85 | −0.89 | AC078852.1 | 0.11 | −0.05 | −0.50 | 0.08 | −0.06 |
| FZD4 | −1.13 | 0.91 | 1.08 | 0.40 | −0.05 | DDX23 | 0.14 | −0.19 | −0.25 | −0.17 | −0.07 | AC020899.1 | 0.15 | 0.14 | −0.54 | 0.00 | −0.38 |
| AC007036.2 | −0.87 | 0.55 | 1.35 | 0.13 | 0.46 | AL353807.3 | −0.24 | −0.15 | −0.09 | −0.33 | 0.13 | GPHA2 | 0.16 | 0.79 | −0.53 | 0.51 | −0.68 |
| DEFB103A | 3.39 | −2.81 | −4.44 | −0.07 | −3.52 | C3orf62 | 0.14 | 0.03 | 0.09 | −0.08 | −0.04 | C8B | 0.22 | −1.87 | −2.67 | 0.25 | −0.88 |
| MIR2467 | 1.72 | −0.78 | −0.73 | −0.28 | −0.43 | RLN1 | −0.89 | 0.11 | 0.14 | 0.57 | 1.35 | AC034205.3 | −0.34 | −0.06 | 1.14 | −0.22 | −0.43 |
| G29706 | −1.17 | 0.28 | 0.99 | 0.33 | 0.10 | AL358176.2 | −1.02 | −0.54 | 0.71 | −0.45 | −0.06 | AC138207.3 | 0.13 | −0.28 | 0.41 | 0.55 | 0.62 |
| BCL2L11 | 0.52 | −0.09 | −0.66 | −0.10 | −0.42 | AL133406.1 | 0.43 | −0.27 | −0.08 | −0.24 | −0.26 | NADK2 | 0.03 | −0.08 | −0.18 | 0.11 | 0.10 |
| ADAM19 | 0.99 | −1.10 | −1.18 | −0.47 | −0.55 | PSMC1P5 | −0.79 | −0.12 | 0.15 | −0.32 | −0.18 | G4640 | −0.20 | −0.88 | −0.17 | −1.03 | −0.65 |
| CERS3-AS1 | 0.97 | −0.22 | −0.23 | 0.10 | −0.09 | AC090739.1 | 0.38 | −0.39 | −0.11 | −0.14 | 0.28 | AC098859.1 | −0.21 | 0.46 | −0.84 | 0.06 | −0.92 |
| AC125612.1 | 0.62 | −0.49 | −0.15 | −0.37 | 0.22 | MTCO1P51 | 1.65 | −0.21 | −1.38 | 0.79 | −1.30 | AC023796.1 | −0.42 | −0.46 | −0.97 | 1.19 | −0.16 |
| SEPSECS-AS1 | −0.61 | 0.29 | 0.88 | 0.38 | 0.71 | G32325 | −0.63 | 0.91 | −0.04 | 0.08 | 0.01 | KCTD2 | 0.03 | 0.24 | −0.07 | 0.15 | −0.32 |
| FAIM | 0.56 | −0.11 | −0.28 | −0.01 | −0.27 | RPS4XP14 | 0.34 | −0.29 | −0.22 | −0.18 | −0.15 | KRTAP24-1 | −0.47 | −0.72 | 1.24 | −1.18 | 0.08 |
| SPATA13 | −0.51 | 0.31 | 0.54 | −0.15 | 0.15 | AC005972.1 | 0.60 | −0.18 | −0.39 | −0.84 | −0.81 | AC079310.1 | −0.40 | −0.08 | 0.69 | 0.32 | 0.57 |
| RNPS1 | 0.37 | −0.24 | −0.42 | −0.12 | −0.18 | AC008440.1 | −0.69 | −0.22 | −0.42 | −0.43 | 0.45 | RPS26P47 | −0.08 | −0.52 | 0.46 | 0.03 | 0.86 |
| SGMS2 | 0.50 | −0.17 | −0.36 | −0.17 | −0.70 | AL499627.2 | −1.25 | −0.55 | 0.82 | 0.63 | −0.06 | DUSP26 | −0.21 | 0.78 | −1.14 | −0.52 | −1.10 |
| AC008056.1 | −2.04 | 1.01 | 1.75 | −1.06 | 0.54 | EWSR1 | 0.12 | −0.20 | −0.42 | 0.00 | −0.01 | PGAM1P10 | 0.34 | −0.39 | −1.19 | 0.54 | 1.07 |
| NMUR1 | −1.62 | 0.28 | 0.46 | 0.03 | −0.21 | ARID3B | −0.15 | −0.12 | 0.14 | −0.33 | 0.10 | LINC01859 | −0.48 | −0.50 | −1.54 | 1.01 | −0.36 |
| BICDL1 | −0.71 | 0.56 | 0.32 | 0.49 | 0.09 | AC092159.2 | −0.55 | −0.32 | −0.31 | 0.32 | 1.09 | AC022031.2 | 0.24 | −1.75 | −0.59 | 0.06 | −0.38 |
| IER3IP1 | 0.74 | −0.24 | −0.22 | −0.06 | −0.39 | RNU6-128P | −0.60 | 0.03 | −0.59 | 0.55 | −0.61 | DEFB133 | −0.56 | 0.79 | −0.70 | −0.67 | −2.76 |
| CREB3L4 | −0.51 | 0.58 | 0.77 | 0.14 | 0.32 | G6PC2 | −0.78 | 0.58 | 0.08 | 0.31 | −0.04 | RP11-436G20.1 | −0.79 | 0.56 | 2.20 | −0.54 | 2.22 |
| LRFN3 | 0.45 | −0.19 | −0.29 | −0.09 | 0.04 | AC008638.2 | 1.05 | −0.92 | −2.78 | 0.12 | −1.15 | LINC00544 | −0.24 | −1.38 | −0.44 | −1.08 | −0.55 |
| ABI2 | −0.28 | 0.14 | 0.47 | −0.03 | 0.24 | IQCA1-AS1 | 1.93 | −1.44 | −3.04 | 1.66 | 0.63 | PSMD10P3 | −0.28 | −0.36 | −0.80 | 0.10 | 0.45 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| KRAS | 0.40 | −0.14 | −0.40 | −0.10 | −0.40 | CFTR-AS1 | −1.61 | 0.48 | 1.48 | 0.48 | −0.13 | LINC02361 | 0.08 | −0.09 | −0.67 | 0.06 | −0.59 |
| AL118508.1 | −1.13 | 0.85 | 0.76 | 0.70 | 0.16 | APOA2 | 0.93 | −0.94 | 0.22 | −1.49 | −0.23 | MIR124-2HG | 0.39 | 0.79 | −2.40 | 1.51 | −2.50 |
| DACH1 | −1.03 | 0.78 | 1.67 | −0.52 | 0.21 | FETUB | 0.48 | 0.04 | 0.48 | 0.20 | −0.54 | G5142 | 0.14 | −0.03 | 0.45 | 0.02 | 0.48 |
| MAEA | 0.31 | −0.05 | −0.33 | −0.14 | −0.26 | METTL21EP | −0.40 | 0.00 | 1.32 | −0.15 | 0.51 | AC007547.1 | 0.37 | −0.27 | −0.95 | −1.76 | −2.60 |
| SLC30A4 | 0.59 | −0.13 | −0.40 | −0.14 | −0.60 | CLASP1 | −0.07 | 0.17 | 0.07 | 0.01 | −0.13 | AC092306.1 | 0.09 | 0.00 | −0.02 | 0.09 | −0.08 |
| LINC00346 | 0.94 | −0.55 | −1.03 | −0.19 | −0.69 | CBLN3 | −0.30 | −0.33 | 0.47 | 0.01 | 0.37 | G1997 | −0.10 | 0.35 | 0.12 | −0.14 | −0.55 |
| BICD2 | 0.54 | 0.10 | −0.42 | 0.06 | −0.55 | AP001525.1 | −0.50 | −0.11 | −0.74 | −0.20 | −0.74 | RPL12P39 | −0.59 | 1.27 | −0.59 | 1.65 | −0.55 |
| BSG | 0.44 | −0.41 | −0.64 | −0.18 | −0.29 | CCDC33 | 0.77 | −2.11 | −1.47 | −0.16 | −1.04 | AC026462.5 | −0.34 | 1.20 | −2.75 | 1.65 | −1.63 |
| ACSS2 | −0.51 | 0.28 | 0.13 | 0.30 | 0.16 | AL590666.1 | 0.38 | −0.06 | −0.61 | 0.19 | −0.05 | AC129507.4 | −0.17 | −0.15 | −0.22 | 0.75 | 1.17 |
| LINGO4 | −1.48 | 1.51 | 2.08 | 1.09 | 0.69 | AC026120.1 | −1.01 | 0.23 | 1.76 | −0.95 | 0.98 | MIR562 | 0.27 | 0.45 | 1.27 | −0.33 | −0.80 |
| KAT14 | −0.34 | 0.22 | 0.35 | 0.06 | 0.17 | EIF2D | −0.10 | 0.06 | 0.15 | 0.07 | 0.10 | AC091544.7 | −0.49 | 0.17 | 0.52 | 0.64 | 1.22 |
| NDEL1 | 0.53 | −0.13 | −0.48 | −0.17 | −0.40 | SUGT1P1 | −0.37 | −0.23 | −0.08 | 0.45 | 0.62 | AC008739.3 | 0.17 | −0.23 | −0.27 | −0.08 | −0.77 |
| AP003354.1 | −1.19 | 0.33 | 1.25 | −0.08 | 0.83 | EEF1A1P11 | 0.27 | 0.14 | −0.13 | 0.26 | −0.03 | AC017035.1 | −0.08 | −0.28 | 0.39 | 0.00 | 0.40 |
| AC023157.2 | 3.08 | −3.00 | −2.33 | −0.71 | −0.01 | MIR320D1 | 0.38 | −0.08 | −0.05 | 0.30 | −0.03 | OR1X5P | 0.28 | −1.56 | −1.14 | −0.85 | −1.26 |
| C15orf40 | −0.39 | 0.11 | 0.66 | −0.03 | 0.21 | AAMP | 0.13 | 0.02 | −0.13 | 0.04 | −0.08 | AC087664.1 | −0.67 | 0.71 | −0.98 | 1.44 | −0.57 |
| CFAP97 | 0.47 | −0.20 | −0.35 | −0.06 | −0.14 | FAM186B | −0.21 | −0.02 | 0.22 | −0.18 | 0.01 | FBXO2 | −0.05 | 0.36 | −0.25 | 0.33 | −0.31 |
| SLC31A2 | −0.49 | 0.51 | 0.55 | 0.29 | −0.02 | HYMAI | −0.26 | 0.18 | 0.45 | 0.17 | 0.10 | OR4C11 | 0.31 | −1.70 | −0.38 | −0.67 | 1.81 |
| SAMM50 | 0.35 | −0.08 | −0.35 | 0.05 | −0.17 | AC068870.2 | 0.34 | −0.28 | −0.10 | −0.25 | −0.18 | LINC01720 | −0.35 | 0.17 | −0.67 | −0.51 | −0.12 |
| AC019069.1 | 1.47 | −1.30 | −1.70 | −0.43 | −0.42 | MAGEA8 | −0.87 | −0.41 | 1.20 | 0.02 | 0.18 | AC245052.2 | −0.13 | −0.07 | −1.08 | 0.00 | 0.15 |
| SNORD11 | 1.06 | −0.26 | −0.09 | 0.15 | 0.35 | FBXO36-IT1 | 0.49 | −0.28 | −0.02 | −0.18 | −0.03 | AL512785.1 | 0.26 | 2.28 | 0.39 | 1.38 | 0.16 |
| AC139713.2 | −0.92 | 0.11 | 0.77 | 0.11 | 0.45 | RPL30P14 | −1.20 | 0.21 | 1.05 | −0.42 | −0.11 | SLC41A3 | −0.03 | 0.12 | −0.07 | 0.20 | −0.15 |
| FAM19A2 | −0.56 | 0.01 | 0.38 | −0.03 | 0.31 | AVPI1 | −0.22 | 0.62 | −0.06 | 0.30 | −0.81 | PSMD10P2 | −0.23 | −0.27 | −0.91 | 0.79 | −1.11 |
| AL365475.1 | −1.20 | −0.09 | 1.11 | 0.22 | 0.55 | MEIOB | −0.51 | −0.45 | 0.93 | −0.34 | 0.68 | C10orf111 | 0.13 | −0.03 | 0.14 | 0.46 | 0.31 |
| AC074124.1 | −1.76 | 0.72 | 0.29 | 0.09 | 0.27 | AC243960.1 | 0.61 | −1.47 | 0.16 | −0.86 | 1.36 | RNU6-1233P | −1.09 | 0.50 | 1.21 | −0.45 | 0.53 |
| AC005697.2 | −1.65 | 0.36 | 0.83 | 0.84 | 0.84 | RNA5SP165 | 0.64 | 0.10 | −0.49 | 0.05 | 0.32 | HIST1H2BPS3 | 0.23 | −1.34 | −1.64 | −0.56 | −0.62 |
| HABP4 | −0.73 | 0.27 | 0.52 | −0.14 | 0.13 | AC005183.1 | 0.25 | −0.29 | −0.25 | −0.18 | −0.22 | AC093520.1 | 0.40 | 1.29 | −0.60 | 0.64 | −1.01 |
| AC021231.2 | −1.08 | 0.75 | 1.22 | 0.34 | 0.95 | RGL1 | −0.19 | 0.10 | 0.26 | 0.03 | 0.09 | CCDC42 | 0.29 | −1.36 | −1.78 | 0.33 | −1.70 |
| AC004233.2 | −1.31 | −0.12 | 0.56 | −0.21 | 0.25 | LINC01291 | 0.34 | −0.59 | −0.28 | 0.24 | 1.08 | AC010327.3 | −0.36 | −0.17 | 0.97 | −1.36 | −0.41 |
| DGAT2 | −0.96 | 0.89 | 1.27 | 0.72 | 0.37 | OR11H7 | −0.66 | 0.68 | 0.80 | 1.21 | 0.80 | AC013244.1 | 0.35 | −1.54 | 0.00 | −2.09 | 1.03 |
| RPAP3 | 0.38 | −0.18 | −0.35 | −0.09 | −0.15 | AL136376.1 | −0.98 | 1.21 | −0.39 | 0.88 | 0.53 | LINC01520 | −0.26 | 0.41 | −1.46 | 1.29 | −2.46 |
| DCAF7 | 0.30 | −0.20 | −0.28 | −0.10 | −0.07 | AC002090.1 | 1.49 | −0.40 | −3.52 | 0.99 | −1.84 | AC007956.1 | −0.12 | 0.40 | −0.07 | −0.29 | −0.60 |
| ANXA9 | −0.73 | 0.75 | 1.27 | 0.51 | −0.10 | AC104836.1 | −0.77 | 0.04 | 1.87 | 1.02 | 0.88 | AL132639.2 | −0.15 | 0.41 | −0.78 | 0.08 | −1.20 |
| ST8SIA6 | −0.90 | 0.49 | 0.02 | 0.22 | −0.06 | LINC01562 | 0.56 | −0.56 | −1.09 | −0.27 | 0.13 | BX571846.1 | 0.40 | 0.18 | 0.96 | 3.03 | 2.67 |
| AL512363.1 | 1.60 | −0.53 | 0.66 | −0.88 | −1.17 | MIB1 | 0.09 | 0.02 | 0.03 | 0.02 | −0.02 | AC022400.8 | 0.18 | −0.29 | 0.13 | −0.50 | −0.35 |
| DAZAP1 | 0.34 | −0.24 | −0.53 | 0.05 | −0.08 | AC139712.3 | −1.06 | −0.29 | −0.29 | 1.14 | 0.61 | RNU2-25P | −0.09 | 0.10 | 0.60 | −0.05 | −0.01 |
| PKD1P5 | −0.96 | 0.38 | 0.59 | 0.95 | 0.79 | MNS1 | −0.22 | 0.02 | 0.30 | −0.12 | −0.02 | AC007496.3 | −0.05 | 0.16 | 0.38 | 0.03 | 0.11 |
| MED28 | −0.27 | 0.21 | 0.33 | 0.10 | 0.15 | LY6H | 1.12 | −0.52 | −0.18 | −0.90 | −2.11 | ADCY4 | −0.07 | 0.01 | 0.19 | 0.05 | −0.03 |
| KLK5 | 1.01 | −0.42 | −0.43 | 0.39 | −0.56 | AC135731.1 | −1.00 | 0.77 | −1.06 | 2.11 | −0.54 | AL591468.1 | 0.23 | −1.67 | −2.45 | −1.13 | −1.21 |
| AC118282.4 | −1.49 | −0.47 | 0.12 | 0.41 | −0.78 | C1QTNF9 | −0.60 | 1.25 | 0.78 | 0.73 | −0.13 | AL513314.2 | −0.10 | 0.39 | −0.25 | 0.45 | −0.10 |
| AL132656.4 | −0.74 | 0.43 | 0.73 | −0.14 | 0.30 | AC012074.1 | −0.37 | 0.36 | −0.05 | 0.34 | 0.08 | RAD9B | −0.05 | −0.16 | 0.14 | −0.09 | 0.18 |
| GLDN | −0.89 | 0.23 | 1.22 | −0.13 | 0.61 | AP003059.2 | −0.66 | 0.21 | 0.91 | −0.09 | 0.30 | BCL2L10 | 0.07 | 0.05 | −0.22 | 0.28 | −0.14 |
| CDK10 | −0.55 | 0.03 | 0.02 | 0.27 | 0.36 | LINC02478 | 0.54 | −0.75 | −0.05 | −0.33 | 0.78 | RNU7-135P | 0.19 | −0.34 | −0.20 | −0.13 | −0.09 |
| AL160163.1 | −0.87 | 0.07 | −0.43 | 0.05 | 0.15 | AC098820.1 | −0.57 | −0.06 | 0.62 | −0.47 | 1.05 | LINC01922 | −0.29 | 1.10 | −1.48 | 0.10 | −2.18 |
| BEST2 | −1.51 | 1.25 | 0.97 | 0.56 | 0.10 | LILRB3 | 0.40 | −0.84 | −0.57 | −0.63 | −0.07 | RN7SKP257 | 0.48 | −0.56 | −0.40 | −0.28 | 0.22 |
| C11orf24 | 0.49 | −0.34 | −0.30 | −0.36 | −0.23 | DBIL5P | −0.40 | 0.03 | 0.22 | 0.61 | 0.45 | AC099654.8 | −0.31 | −0.81 | −0.57 | 0.55 | 1.17 |
| HIRA | 0.51 | −0.16 | −0.41 | −0.13 | −0.18 | FBXO34 | 0.13 | 0.14 | −0.04 | 0.12 | −0.15 | RNU6-32P | 0.10 | −0.46 | 0.32 | −0.04 | 0.96 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| RNASEH2CP1 | −1.02 | 0.32 | 1.06 | 0.59 | 0.51 | OMG | 0.19 | −0.13 | −0.09 | −0.12 | 0.00 | AC036111.2 | 0.71 | 0.37 | −1.36 | 1.63 | 0.77 |
| RSPO1 | −0.79 | 0.49 | 0.20 | 0.21 | −0.03 | CEACAM22P | 0.58 | −1.01 | −0.70 | 0.30 | 0.04 | FOXD1 | −0.49 | −0.31 | −0.69 | −0.50 | −0.21 |
| AIFM2 | −0.89 | 0.45 | 0.57 | 0.18 | 0.17 | RHOT1 | −0.14 | 0.13 | 0.46 | 0.08 | 0.13 | AL596275.1 | −0.37 | 1.07 | 0.09 | −0.38 | −1.91 |
| FO393400.1 | −2.11 | 1.55 | 1.34 | 0.71 | 0.33 | AF067845.1 | 0.72 | −1.28 | −2.17 | 0.26 | −0.54 | SPANXD | −1.08 | 0.07 | −0.13 | −1.20 | −2.51 |
| RELL2 | 0.73 | −0.51 | −0.77 | −0.11 | −0.10 | AC090204.1 | −0.49 | −0.22 | 0.88 | −0.45 | 0.46 | MIR548XHG | −0.31 | −1.46 | 1.78 | −0.03 | 2.49 |
| AC008056.2 | −1.93 | −0.25 | 0.03 | 1.10 | 1.04 | PRICKLE2-AS2 | 0.52 | −0.69 | −0.23 | −0.29 | 0.18 | RNU6-540P | −0.23 | 1.24 | 1.84 | 0.14 | −0.26 |
| ARHGAP5 | 0.47 | −0.03 | −0.36 | 0.06 | −0.21 | RPL12P42 | 0.82 | −0.47 | −0.22 | −0.91 | −0.01 | LINC01865 | −0.20 | −0.36 | −0.98 | 0.45 | −0.62 |
| PPRC1 | 0.59 | −0.45 | −0.80 | −0.07 | −0.22 | PCDHGA10 | −0.15 | 0.32 | −0.05 | 0.13 | −0.19 | AL772363.1 | 0.24 | −0.45 | −1.13 | 1.11 | −1.50 |
| PSENEN | 1.20 | −0.20 | −0.98 | 0.06 | −0.86 | RNU6-893P | 0.59 | −0.90 | −0.57 | −0.12 | −0.15 | ALKBH3-AS1 | 0.06 | 0.19 | −0.02 | 0.41 | 0.12 |
| OR2A20P | −0.70 | 0.32 | 0.47 | 0.78 | 0.87 | AC087477.1 | −0.69 | 1.44 | 1.24 | 1.54 | 0.03 | MIR185 | 0.30 | −0.12 | −0.12 | −1.17 | −1.40 |
| AC005899.8 | −0.66 | 0.24 | 0.42 | 0.16 | 0.39 | CLLUIOS | 0.85 | −1.30 | −1.55 | −0.16 | 0.47 | AL591643.1 | 0.32 | −1.59 | −0.73 | 0.62 | 0.12 |
| RIC1 | 0.34 | −0.10 | −0.24 | 0.00 | −0.08 | KIAA1658 | 0.51 | 0.06 | 0.51 | −0.12 | 0.15 | OLA1P1 | 0.10 | 0.60 | −0.12 | 0.43 | −0.29 |
| CSNK2A3 | 1.16 | −0.48 | −0.80 | 0.37 | −0.33 | KRT7-AS | −0.69 | 0.63 | 1.08 | 0.12 | −0.24 | MTND4P22 | −0.38 | 0.02 | 0.74 | −0.57 | −1.49 |
| CENPT | −0.66 | 0.45 | 0.36 | 0.27 | 0.06 | CMTM3 | −0.22 | 0.10 | 0.37 | −0.18 | 0.04 | LINC01582 | −0.63 | 0.69 | 0.11 | 1.23 | 1.21 |
| ACLY | 0.52 | −0.40 | −0.47 | −0.10 | 0.02 | SNORD113-1 | 0.85 | 0.34 | 0.73 | −0.24 | 0.16 | AC087588.2 | 0.43 | 0.80 | −1.20 | 0.00 | −2.50 |
| CHRNA3 | 1.23 | −0.18 | −0.22 | 0.07 | −0.21 | NGB | 0.95 | −0.72 | −1.64 | −0.31 | −1.20 | LINC00364 | −0.60 | −0.10 | 0.35 | −2.14 | −1.39 |
| AOC4P | −1.55 | 0.43 | 1.52 | 0.45 | 0.42 | AC096558.2 | 0.64 | −0.57 | −0.43 | −0.42 | 0.44 | FBXL12 | −0.03 | 0.02 | 0.10 | −0.09 | 0.01 |
| CASP17P | −0.95 | 0.17 | 1.25 | −0.21 | 0.22 | AC087639.1 | −0.71 | −0.18 | −0.20 | 0.84 | 0.43 | AL157834.1 | −0.12 | 0.07 | 0.05 | −0.20 | 0.12 |
| OGDH | 0.31 | −0.05 | −0.31 | −0.01 | −0.29 | RNU6-633P | −0.57 | 0.29 | 1.29 | −0.02 | 0.17 | AL138899.2 | −0.19 | 0.32 | 1.14 | 0.61 | 0.91 |
| NASP | 0.38 | −0.46 | −0.34 | −0.21 | 0.12 | SLC26A8 | −0.43 | −0.16 | 0.11 | −0.17 | −0.24 | AC069294.1 | −0.35 | −1.31 | 0.83 | −1.56 | 1.03 |
| DHFR | 0.74 | −0.74 | −0.54 | −0.28 | −0.08 | NCOA6 | 0.11 | 0.08 | −0.08 | 0.00 | −0.08 | AC099811.4 | 0.08 | 0.05 | 0.05 | −0.48 | −0.27 |
| AL031848.1 | −1.57 | 0.81 | 1.66 | 0.15 | 0.71 | AC011742.2 | 0.37 | 0.08 | −0.42 | 0.52 | 0.11 | SNORD113-9 | 0.49 | 1.04 | 1.19 | 0.50 | 2.06 |
| EXT1 | 0.39 | −0.26 | −0.64 | 0.12 | −0.09 | GNA14 | 0.27 | −0.40 | 0.43 | −0.18 | 0.39 | GYG1P1 | −0.34 | −0.01 | −1.46 | 1.15 | −1.67 |
| EID2 | 0.48 | −0.10 | −0.38 | 0.04 | −0.20 | LINC02544 | 0.38 | 0.37 | 0.44 | −0.25 | 0.08 | AC016885.1 | −0.50 | 0.65 | 2.84 | −0.53 | 0.68 |
| CACNA1G | −0.80 | 0.42 | 1.06 | −0.22 | 0.07 | ASICS | 1.43 | −1.04 | −1.36 | −0.27 | −1.09 | AC116666.1 | −0.40 | 0.73 | −1.96 | 1.26 | −0.25 |
| FAM114A2 | 0.37 | −0.28 | −0.18 | −0.21 | −0.08 | RNU6-595P | 0.44 | −0.08 | 0.14 | −0.07 | −0.07 | GLRX | −0.06 | 0.17 | 1.08 | 0.00 | 0.11 |
| LINC01585 | −1.15 | 0.12 | 0.42 | 0.31 | 0.32 | AC244021.1 | −0.55 | −0.03 | 1.18 | 0.44 | 0.06 | ARHGAP36 | 0.24 | 0.15 | −2.03 | 0.24 | −2.62 |
| MAGEE1 | −0.61 | 0.28 | 0.71 | 0.08 | 0.04 | G20593 | −1.18 | 1.26 | 0.64 | 0.81 | −0.39 | AC006581.2 | −0.13 | 0.21 | −0.26 | −0.38 | −0.55 |
| ACAD9 | −0.41 | 0.29 | 0.37 | 0.15 | 0.09 | AC007000.3 | −0.45 | 0.37 | 0.30 | 0.00 | −0.45 | AC046158.1 | −0.08 | −0.16 | 0.22 | 0.15 | 0.15 |
| IPO8 | 0.31 | −0.12 | −0.17 | −0.07 | −0.19 | LACTB2 | 0.20 | −0.38 | 0.37 | −0.12 | 0.12 | AL033397.1 | −0.19 | −1.28 | −1.08 | −0.19 | 0.13 |
| AC007292.3 | −1.30 | 0.57 | 1.19 | −0.03 | 0.32 | PMF1 | −0.13 | 0.15 | −0.16 | 0.27 | 0.01 | AC112178.1 | 0.19 | −0.95 | −0.09 | −0.34 | 1.24 |
| IFI30 | 1.48 | −1.21 | −1.21 | −0.32 | −0.74 | ARFGEF2 | 0.08 | 0.05 | −0.13 | 0.15 | −0.01 | AC104083.1 | 0.07 | 0.02 | 0.68 | −0.05 | 0.06 |
| AC068491.2 | 2.02 | −2.51 | −1.81 | −1.27 | −0.24 | AC021683.2 | −0.44 | 0.02 | 0.48 | −0.02 | 0.57 | LINC00708 | −0.42 | −0.30 | 1.76 | −1.84 | 0.87 |
| AC008514.1 | −1.65 | 1.21 | 2.04 | 0.21 | −0.04 | HOXA11-AS | −0.83 | −0.98 | 1.43 | −0.61 | 0.13 | OR6K3 | −0.31 | 0.09 | 1.17 | −0.99 | −1.69 |
| FJX1 | 1.06 | −0.77 | −0.94 | 0.07 | −0.16 | RNU6-529P | 0.63 | 1.17 | −0.20 | 0.42 | −0.88 | AC099654.7 | −0.26 | −0.27 | −0.31 | 1.81 | 0.66 |
| ST3GAL5-AS1 | −1.08 | 0.51 | 1.09 | 0.45 | 0.67 | RPS12P31 | 0.60 | 0.16 | 0.74 | 0.68 | 0.96 | PMM2P1 | 0.57 | −1.21 | 0.07 | 0.03 | 1.72 |
| SPRY4 | 0.87 | −0.66 | −1.25 | −0.44 | −0.62 | DPRXP4 | 0.24 | 0.23 | −0.25 | 0.22 | −0.32 | AP002892.2 | 0.11 | −0.76 | 0.24 | −0.74 | −0.03 |
| EXOSC4 | 0.67 | −0.25 | −0.59 | 0.08 | −0.05 | OTULINL | 0.28 | −0.41 | −0.10 | −0.03 | 0.19 | AC009220.3 | −0.23 | −0.82 | 0.56 | −0.70 | 0.67 |
| GPR20 | −1.59 | 0.41 | 2.78 | 0.28 | 0.99 | MTATP6P15 | −0.46 | 0.68 | 0.80 | 0.33 | 0.47 | FABP5P5 | 0.14 | −0.01 | 0.32 | −0.06 | −0.03 |
| C6orf10 | −0.90 | −0.16 | 0.60 | 0.12 | 0.26 | LINC00636 | 0.59 | −0.87 | 0.01 | −0.46 | 0.66 | IRAK4 | −0.03 | −0.07 | 0.13 | −0.04 | 0.12 |
| GSTA4 | 0.52 | 0.04 | −0.14 | 0.19 | 0.01 | CIC | −0.14 | 0.10 | −0.21 | 0.27 | 0.06 | G31837 | 0.14 | −0.69 | −0.48 | −0.54 | 0.25 |
| G39546 | −2.13 | 2.84 | 0.67 | 2.41 | −1.96 | RNU6-1284P | 0.39 | −0.47 | −0.31 | −0.56 | 0.00 | RDM1P2 | −0.25 | 0.63 | −0.57 | 0.22 | 0.79 |
| GIMAP3P | −1.83 | −0.56 | 0.75 | −0.60 | 1.27 | AP004372.1 | −1.08 | 1.60 | 0.89 | −0.55 | −0.54 | MTND2P33 | −0.41 | 1.06 | 0.42 | −1.96 | −1.96 |
| HIST1H4J | 1.08 | −0.65 | −0.61 | 0.14 | −0.18 | RPSAP21 | −0.30 | 0.11 | 0.01 | 0.77 | 0.16 | RPL7P42 | 0.36 | −1.02 | −0.95 | 1.28 | −0.87 |
| LINC02580 | −0.72 | 0.06 | 0.00 | 0.14 | 0.49 | SH3TC2-DT | 0.39 | −0.10 | −1.13 | 0.22 | −0.56 | KC877392.1 | 0.30 | −1.35 | −0.66 | 0.31 | 2.38 |
| SLC35A2 | 0.64 | −0.46 | −0.42 | −0.24 | −0.10 | AL353803.5 | −1.45 | 0.72 | 1.33 | −0.18 | 0.27 | AL592049.1 | −0.48 | −1.00 | −1.59 | 0.31 | −0.32 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| NPC1 | 0.33 | −0.06 | −0.15 | −0.06 | −0.12 | EPHA7 | −0.43 | 0.36 | 0.36 | 0.59 | 0.58 | AP003028.1 | −0.56 | 1.62 | −1.04 | −0.40 | −2.86 |
| SLC9A6 | 0.40 | −0.22 | −0.25 | 0.00 | −0.07 | AC007041.1 | 0.58 | −0.77 | −0.22 | 0.04 | 0.49 | PSMC1P2 | −0.37 | −0.17 | 0.80 | −1.80 | 0.20 |
| ATG9A | 0.38 | −0.01 | −0.40 | 0.03 | −0.35 | AL157938.2 | 0.26 | −0.28 | −0.02 | −0.15 | 0.13 | AP005264.2 | −0.42 | 0.89 | −1.31 | 1.44 | −0.76 |
| MTREX | 0.36 | −0.11 | −0.25 | −0.04 | −0.15 | AC007283.2 | 0.42 | 0.03 | 0.40 | −0.12 | −0.15 | AC135048.4 | −0.10 | 0.32 | 0.36 | 0.36 | 0.08 |
| MAK16 | 0.53 | −0.49 | −0.43 | −0.28 | −0.24 | PDZD9 | 0.39 | 0.06 | −0.03 | −0.07 | −0.33 | G13451 | 0.10 | 0.16 | −1.72 | 0.54 | −0.67 |
| AURKB | 0.81 | −1.00 | −1.58 | −0.20 | −0.10 | RNPEPL1 | −0.12 | 0.01 | −0.23 | 0.18 | −0.03 | AC092653.1 | 0.09 | 0.12 | 0.01 | 0.14 | −0.11 |
| DEPDC5 | −0.32 | −0.09 | 0.05 | −0.10 | 0.13 | AC092573.2 | 0.72 | −0.38 | −0.20 | −0.08 | 0.02 | G25097 | 0.17 | 1.11 | −1.65 | 0.73 | −1.26 |
| NUDT11 | −1.03 | 0.27 | 0.28 | −0.23 | 0.46 | BAAT | 0.73 | 0.15 | 0.16 | −0.04 | −0.73 | RPGRIP1 | 0.08 | 0.09 | 0.32 | −0.09 | −0.07 |
| HEMK1 | −0.42 | 0.04 | 0.19 | 0.12 | 0.33 | AC013553.3 | −0.81 | 0.11 | −0.26 | 0.07 | 0.08 | AC109460.2 | −0.06 | −0.26 | −0.29 | 0.27 | 0.42 |
| ERI2 | 0.57 | −0.26 | −0.20 | −0.12 | −0.01 | AC104964.4 | −0.82 | 0.82 | 0.41 | −0.18 | −0.32 | AC011825.4 | −0.18 | −0.22 | −2.00 | 1.17 | 0.13 |
| MIR4516 | −1.56 | 0.74 | 0.07 | 0.67 | −0.04 | EEF1A2 | −0.34 | 0.50 | −0.46 | 0.46 | −0.98 | AC016751.1 | 0.59 | −0.38 | −1.65 | 0.47 | −1.82 |
| HEXB | 0.48 | −0.20 | −0.14 | −0.31 | −0.21 | CLDN5 | −0.32 | 0.64 | 0.60 | 0.74 | 0.00 | AL590369.1 | −0.15 | 0.42 | −0.85 | 0.73 | −0.28 |
| LARS2 | 0.51 | −0.22 | −0.25 | −0.19 | −0.16 | AKAP3 | −0.27 | 0.49 | 0.03 | 0.07 | −0.31 | HIST2H4A | 0.14 | −0.35 | −1.25 | 0.92 | −0.65 |
| PCDHGB8P | −0.69 | 0.15 | 1.08 | −0.11 | 0.37 | AC073413.2 | −0.74 | −0.68 | −0.25 | −0.70 | 0.96 | RP1L1 | −0.06 | 0.47 | −0.08 | 0.19 | −0.92 |
| CRBN | −0.32 | 0.31 | 0.49 | 0.12 | −0.01 | AC126124.2 | −0.45 | 0.08 | 1.04 | −0.04 | 0.27 | SRP72P1 | 0.36 | −0.61 | −1.84 | −0.21 | 0.85 |
| RHPN1 | −0.89 | 0.38 | 0.02 | 0.45 | 0.24 | AC144548.1 | 0.72 | −0.56 | −1.23 | −0.53 | −0.67 | AL589990.1 | −0.20 | −1.18 | 0.71 | −0.16 | 0.88 |
| RHBDL2 | 0.64 | −0.18 | −0.48 | −0.03 | −0.40 | MIR941-2 | 0.70 | −1.14 | 0.14 | −0.13 | 0.69 | AC125611.2 | 0.05 | −0.11 | −0.08 | 0.10 | 0.22 |
| AKIP1 | 0.55 | −0.36 | −0.49 | −0.35 | −0.23 | BEAN1-AS1 | −0.65 | 0.65 | −0.12 | 0.29 | 1.34 | HMGB3P8 | −0.12 | −0.22 | 1.07 | −0.89 | −0.16 |
| AL683813.1 | −0.80 | 0.04 | 0.65 | 0.00 | 0.28 | LOH12CR2 | −0.43 | 0.28 | −0.26 | 0.65 | −0.20 | SLC10A5P1 | 0.22 | −0.93 | −0.60 | 0.07 | 0.97 |
| SNRNP25 | 0.55 | −0.48 | −0.44 | −0.22 | −0.12 | AC113386.1 | −1.56 | 0.60 | −0.17 | 1.12 | −0.66 | AC093083.1 | 0.17 | 0.80 | −0.74 | −0.32 | −0.89 |
| ATP6V1H | 0.32 | −0.12 | −0.23 | 0.00 | −0.15 | C11orf71 | −0.25 | 0.31 | 0.44 | 0.10 | −0.17 | AC097512.1 | −0.22 | −0.36 | −1.40 | −0.09 | −0.64 |
| SNORA49 | −0.71 | 0.59 | 0.75 | 0.19 | −0.33 | AL645568.1 | −0.17 | 0.06 | 0.37 | −0.15 | 0.05 | AC142381.4 | −0.77 | 1.07 | −0.39 | 1.09 | −2.29 |
| AP2B1 | 0.36 | −0.23 | −0.28 | −0.17 | −0.23 | RPL23AP55 | 0.51 | −0.06 | −1.25 | 0.50 | −0.74 | PRICKLE3 | 0.04 | −0.01 | −0.28 | 0.10 | 0.00 |
| AC084824.1 | −0.55 | 0.30 | 0.40 | 0.25 | 0.15 | EMC2 | 0.13 | 0.03 | 0.01 | 0.03 | −0.12 | MTHFR | −0.04 | −0.03 | −0.34 | 0.19 | 0.06 |
| AC022893.1 | −0.64 | 0.36 | 0.56 | 0.22 | 0.10 | RNU6-14P | −0.56 | 0.06 | −0.10 | 0.72 | −0.09 | EXTL3-AS1 | 0.06 | −0.28 | 0.00 | −0.04 | 0.30 |
| G14979 | 1.61 | −0.23 | −2.05 | 0.48 | −0.92 | AP001172.2 | −0.59 | 0.45 | 2.81 | −0.17 | 0.48 | AC084125.1 | 0.14 | −0.83 | 0.68 | 0.00 | 0.81 |
| EEF1AKMT4 | 1.29 | −0.70 | −1.03 | −0.51 | −0.61 | SCAANT1 | 0.56 | −0.06 | 0.33 | 0.12 | 0.77 | LINC01432 | 0.43 | −1.54 | −1.77 | −0.01 | −0.17 |
| KDM5D | −0.58 | 0.33 | 0.55 | 0.23 | 0.18 | AC003992.1 | 0.62 | 0.57 | −1.07 | 0.46 | −1.03 | BNIP3P33 | −1.07 | 0.97 | −0.11 | 0.86 | −1.59 |
| AC007114.1 | −0.84 | 0.64 | 0.93 | 0.72 | 0.41 | CHST6 | 0.42 | −0.05 | −0.47 | −0.56 | −0.63 | RP11-439L8.3 | 1.03 | −1.26 | −0.88 | 0.65 | −0.45 |
| CES5AP1 | −1.69 | 0.49 | 0.70 | −0.49 | −0.52 | LY6G6F | −0.81 | 0.81 | 1.54 | 0.46 | 0.13 | AC092641.1 | 0.09 | 0.32 | 0.23 | 0.14 | −0.04 |
| FAM122C | −0.52 | −0.12 | 0.40 | −0.02 | 0.27 | HIST1H4PS1 | 1.37 | 0.00 | −1.83 | 1.21 | −2.05 | RBKS | 0.07 | −0.10 | 0.16 | −0.14 | 0.13 |
| SPX | −1.85 | 0.24 | 0.54 | 1.36 | −0.06 | AL449106.1 | 0.34 | 0.01 | 0.10 | 0.05 | −0.13 | RP11-395P13.4 | −0.38 | 0.56 | −0.08 | 1.52 | 1.38 |
| RBM22 | 0.26 | −0.11 | −0.31 | −0.12 | −0.25 | AC026369.2 | 1.10 | −2.13 | −1.46 | −0.13 | −0.52 | BOK-AS1 | −1.06 | 0.79 | 0.97 | 1.05 | −0.28 |
| CR848007.1 | −2.06 | 0.40 | 1.21 | 0.35 | 0.50 | AL450003.1 | −0.76 | 0.44 | 0.37 | 0.17 | 0.15 | AL450992.2 | 0.07 | 0.02 | 0.04 | 0.60 | 0.49 |
| MRPS36 | 0.67 | −0.06 | −0.42 | 0.00 | −0.66 | CUTA | 0.18 | 0.17 | −0.06 | 0.00 | −0.29 | C17orf53 | 0.06 | −0.50 | −1.11 | 0.09 | −0.30 |
| RPL10AP6 | 0.80 | −0.38 | −0.55 | −0.29 | −0.36 | G10020 | 0.48 | −1.09 | −1.56 | −0.54 | 0.34 | GAB3 | −0.06 | −0.21 | 0.22 | −0.10 | 0.16 |
| HIC1 | −0.87 | 0.50 | 0.76 | 0.19 | −0.26 | AC139256.1 | −0.30 | 0.16 | −0.12 | 0.65 | 0.31 | SDCCAG3P2 | −0.71 | −0.48 | 0.15 | −0.93 | 0.41 |
| GCLC | 0.60 | −0.13 | −0.56 | 0.30 | −0.32 | AC022538.1 | −1.15 | −0.73 | 1.64 | −0.45 | 1.57 | AC103974.2 | −0.51 | −0.65 | −0.49 | 1.79 | −0.02 |
| ALDH4A1 | 1.01 | −0.09 | −0.76 | 0.29 | −0.24 | AC093388.1 | −0.36 | 0.22 | 0.25 | −0.14 | −0.11 | HNRNPA1P55 | −0.25 | 0.07 | −0.89 | 0.31 | −0.48 |
| NPM1P43 | −1.06 | 0.56 | 1.67 | 0.11 | 0.56 | RPL7AP34 | 1.08 | −1.69 | −2.11 | −0.23 | −1.21 | NSMCE3 | 0.03 | 0.00 | −0.17 | −0.04 | −0.16 |
| AL158071.4 | −0.97 | 0.52 | 0.89 | 0.25 | 0.51 | RNU6-1209P | 0.72 | 0.80 | −1.58 | −0.03 | −0.97 | AEBP2 | −0.03 | 0.03 | 0.12 | −0.02 | 0.17 |
| LINC00472 | −0.87 | 0.36 | 1.31 | −0.07 | 0.50 | RPS27P15 | 0.88 | 0.66 | −0.84 | 1.05 | 0.59 | P27P1-BPTFP1-P | −0.07 | −0.20 | 0.14 | −0.30 | 0.19 |
| SASH3 | 1.01 | −0.92 | −0.41 | −0.43 | −0.04 | RGS7 | 0.58 | −0.58 | 0.86 | −0.77 | 0.95 | GPBP1 | 0.03 | 0.10 | −0.02 | 0.02 | −0.08 |
| FAM69B | −0.70 | 0.46 | 0.55 | 0.24 | 0.31 | IL1R1 | 0.19 | −0.18 | 0.30 | −0.25 | −0.02 | OR7E121P | −0.38 | 0.04 | 2.12 | 1.31 | 1.52 |
| GOLT1B | 0.62 | −0.36 | −0.37 | −0.19 | −0.22 | KRTCAP2 | −0.22 | −0.18 | 0.16 | 0.03 | 0.28 | OR52P2P | 0.23 | −0.58 | −0.17 | −0.99 | −0.57 |
| SPRR2C | 3.09 | −2.78 | −3.92 | 0.18 | −3.28 | PAWRP1 | −0.79 | 0.28 | −0.88 | 1.17 | −0.12 | EIF4A2P4 | −0.12 | −0.96 | −0.29 | −0.19 | 0.00 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| MINCR | −0.72 | 0.52 | 0.39 | 0.59 | 0.26 | LINC02104 | −1.01 | 0.95 | 2.06 | 0.72 | 1.40 | AC003001.1 | 0.72 | −0.18 | −1.87 | 0.88 | −1.47 |
| HILS1 | −1.40 | 0.43 | 0.67 | −0.74 | −0.24 | STRA6LP | −0.90 | 1.44 | 0.36 | 0.13 | −0.96 | AC068057.1 | −0.53 | −0.51 | 2.06 | 0.02 | 2.99 |
| MRPS21 | 0.36 | −0.19 | −0.48 | 0.07 | −0.26 | GRM4 | 0.52 | −0.09 | −0.81 | 0.11 | −0.52 | APOC2 | 0.29 | −0.35 | 1.13 | −0.04 | 0.01 |
| NANOGP8 | −1.17 | 0.60 | 0.72 | 0.77 | 0.42 | REXO1L1 | 0.84 | −0.78 | −2.16 | 0.66 | −1.01 | GSTK1 | −0.02 | 0.04 | −0.08 | 0.01 | −0.09 |
| AL162231.4 | −1.41 | 0.67 | 1.17 | 0.50 | 0.66 | AC092910.2 | 0.40 | 0.28 | 0.01 | −0.21 | −0.13 | AC107982.2 | 0.10 | −0.46 | −0.16 | −0.13 | −0.12 |
| CCDC74A | −0.67 | 0.49 | 0.38 | 0.21 | −0.05 | CFAP57 | −0.43 | 0.56 | 0.36 | 0.21 | −0.03 | HIF1AP1 | 0.15 | −0.33 | −0.84 | −0.18 | −0.51 |
| KCNJ9 | −0.95 | 0.56 | 0.20 | 0.54 | 0.02 | AC018695.3 | 0.51 | −0.18 | −1.17 | −0.07 | −0.84 | AC025521.1 | −0.87 | 0.94 | 0.41 | −0.52 | −0.68 |
| RPL7AP6 | 0.72 | −0.33 | −0.27 | −0.08 | −0.09 | AC013562.1 | −1.22 | −0.02 | 0.50 | 0.03 | −0.20 | CDX2 | −0.18 | −0.32 | −1.30 | −0.31 | −1.13 |
| DPYSL3 | −0.85 | 0.28 | 1.27 | −0.27 | 0.19 | AC096570.1 | −0.78 | −1.07 | −1.13 | 0.86 | −0.27 | BX005132.2 | −0.73 | −0.03 | −0.60 | −0.83 | −0.15 |
| CLIC5 | −1.02 | 0.35 | 1.10 | 0.02 | 0.48 | LCE1C | −0.51 | 0.72 | 0.91 | 0.74 | −0.37 | RNU6-1170P | −0.23 | −0.65 | 1.95 | −0.08 | 1.58 |
| LINC00663 | −0.97 | 0.48 | 0.76 | 0.26 | −0.01 | ANKRD49 | 0.15 | −0.02 | 0.05 | 0.02 | −0.02 | GPR34 | 0.07 | 0.05 | −0.16 | −0.06 | −0.26 |
| LY6E | 0.49 | −0.53 | −0.25 | −0.42 | −0.07 | FNDC4 | −0.31 | 0.26 | 0.54 | −0.01 | 0.21 | AL357568.1 | 0.06 | 0.37 | −0.17 | 0.34 | −0.18 |
| HNRNPA1P3 | −1.74 | 1.28 | 2.45 | 0.58 | −0.63 | POLK | −0.12 | 0.03 | 0.23 | −0.12 | 0.07 | HSPE1P13 | 0.11 | 0.11 | −0.07 | 0.10 | 0.04 |
| AL033384.1 | 1.05 | −0.11 | −0.44 | 0.03 | −0.55 | AL606489.1 | −0.31 | 0.18 | 0.16 | 0.17 | 0.10 | AC003092.2 | −1.06 | −0.01 | 1.48 | 0.09 | 0.51 |
| KNTC1 | 0.47 | −0.49 | −0.59 | −0.14 | −0.09 | C3orf20 | −0.36 | 0.16 | −0.02 | 0.03 | 0.15 | FDPSP7 | −0.12 | −0.46 | 0.36 | 1.15 | 1.70 |
| FTO | −0.24 | 0.23 | 0.25 | 0.13 | 0.06 | KCNK15 | −0.55 | −0.19 | 0.09 | −0.08 | −0.09 | OR7E31P | −0.48 | −0.84 | 0.98 | −0.10 | −0.26 |
| DCLRE1C | 0.35 | −0.26 | −0.20 | −0.19 | −0.07 | AC010198.1 | −0.56 | −0.74 | 1.64 | 0.23 | 1.29 | RNU6-731P | −0.18 | −1.62 | 0.49 | 0.19 | 1.96 |
| FABP6 | 2.19 | −0.53 | −2.06 | 0.14 | −1.86 | AL590399.5 | −0.55 | 0.26 | 1.39 | −0.61 | 0.10 | MIR4777 | −0.50 | −0.39 | −0.98 | −0.38 | −1.03 |
| LINC01303 | 0.98 | −0.79 | −1.65 | −0.30 | −0.98 | AC089983.1 | 0.78 | −0.46 | −0.42 | 0.44 | −0.70 | AC092343.1 | −0.10 | 0.13 | 0.67 | −0.12 | 0.69 |
| G33960 | −2.18 | 0.75 | 2.12 | 0.27 | 0.84 | PDE4A | −0.26 | −0.09 | 0.18 | −0.10 | 0.10 | IPO4 | 0.09 | −0.21 | −0.27 | 0.26 | −0.21 |
| RFK | 0.73 | −0.03 | −0.38 | −0.02 | −0.51 | MIR3175 | −1.12 | −0.72 | 0.31 | −0.76 | −0.42 | LINC02402 | 0.37 | 1.77 | −2.17 | 0.83 | −1.76 |
| SLC4A1AP | 0.31 | −0.18 | −0.28 | −0.24 | −0.21 | AL353622.2 | −0.59 | 0.50 | −0.34 | 0.64 | 0.18 | KRT8P5 | −0.29 | −0.13 | 1.17 | −1.13 | 1.88 |
| AL050403.2 | −1.20 | 0.49 | 0.30 | 0.44 | −0.53 | AC016065.1 | 0.31 | −0.80 | −0.29 | −0.35 | 0.31 | F13B | 0.26 | −0.85 | −0.68 | −1.47 | 0.11 |
| RPL3P6 | 0.78 | −0.20 | −0.39 | −0.14 | −0.11 | RBM46 | 0.74 | 0.43 | −1.93 | 0.27 | −2.13 | AC005838.2 | 0.09 | 0.16 | 0.78 | −0.04 | 0.27 |
| ENOPH1 | 0.37 | −0.15 | −0.25 | −0.08 | −0.17 | AC022762.1 | −1.11 | −0.08 | 0.31 | 0.67 | 0.37 | HNRNPRP2 | −0.57 | 0.28 | −0.48 | 0.21 | −1.98 |
| FREM2 | −0.87 | 1.36 | 1.08 | 0.45 | −0.43 | PDCD4-AS1 | −0.37 | 0.31 | 0.37 | −0.01 | −0.08 | AP003108.1 | −0.94 | 0.34 | 0.26 | 0.29 | −1.73 |
| AC005336.1 | 1.82 | −1.32 | −1.64 | −0.16 | −0.90 | AC006011.2 | −0.48 | −0.34 | 0.37 | −0.21 | 0.01 | RNU6-784P | −0.32 | −0.12 | 0.92 | 0.85 | 0.20 |
| SLC7A10 | −1.82 | 0.70 | 1.24 | 1.03 | −0.31 | AC135050.7 | 0.43 | −0.27 | −0.83 | −0.26 | −0.54 | SPOP | −0.03 | 0.01 | 0.26 | −0.06 | 0.04 |
| CTSD | 0.55 | 0.02 | −0.58 | 0.28 | −0.58 | AC012498.2 | 1.35 | −0.01 | 1.13 | 0.06 | 0.45 | AP000442.2 | −0.10 | −0.13 | 0.58 | −0.08 | 0.35 |
| MAML3 | −0.48 | 0.56 | 0.62 | 0.33 | 0.10 | AL356423.1 | 0.28 | −0.27 | −0.39 | −0.03 | −0.19 | AL158058.1 | −0.60 | −0.30 | 1.33 | −1.56 | 1.50 |
| FMNL2 | 0.65 | −0.43 | −0.70 | −0.19 | 0.05 | KIAA0513 | 0.16 | 0.13 | −0.02 | 0.16 | −0.25 | PGA3 | 0.23 | −1.40 | −0.01 | −0.03 | −0.08 |
| DEFB1 | 0.92 | −0.48 | −0.91 | −0.45 | −0.52 | RHEBP3 | −0.45 | 0.29 | −0.87 | 0.50 | 0.14 | AC105105.3 | 0.51 | −0.81 | −1.50 | −1.74 | −2.58 |
| RPL7L1P9 | −1.19 | 0.31 | 0.77 | 0.07 | −0.12 | AP003550.1 | −0.55 | −0.04 | 1.08 | 0.69 | 0.86 | AC037487.3 | −0.25 | −0.49 | 0.26 | 0.46 | 1.05 |
| BTRC | 0.33 | −0.13 | −0.26 | −0.20 | −0.15 | AC091057.2 | −0.51 | 0.78 | 1.55 | −0.24 | −0.09 | AC092652.1 | −0.13 | −0.63 | 1.49 | −0.22 | 1.65 |
| SLITRK6 | −0.86 | 0.90 | 1.27 | 0.54 | 0.30 | G8687 | 0.41 | 0.26 | −0.23 | 0.57 | 0.21 | LINC00324 | −0.05 | −0.04 | 0.04 | −0.07 | −0.17 |
| AC011243.1 | 1.50 | −0.78 | −0.53 | −0.18 | 0.58 | AC004593.1 | −0.37 | −0.14 | −0.08 | −0.10 | 0.40 | BNIP3P3 | 1.06 | −0.47 | −1.68 | 1.79 | 0.78 |
| STBD1 | −1.13 | 0.04 | 0.60 | −0.05 | 0.44 | FGF12 | −0.41 | 0.34 | 0.74 | −0.02 | −0.16 | AC079447.1 | −0.10 | 0.11 | −0.06 | −0.09 | −0.21 |
| LINC01800 | −1.31 | 0.62 | 0.95 | −0.01 | 0.31 | BGN | −0.27 | −0.05 | 0.58 | −0.61 | −0.34 | NCBP1 | 0.02 | −0.06 | 0.02 | −0.06 | 0.08 |
| IGFL2 | −1.02 | 0.68 | 1.87 | 0.40 | 0.51 | KIAA0895LP1 | −0.43 | 0.18 | 0.73 | 0.66 | 0.44 | CFHR3 | −0.19 | 0.13 | −1.51 | 0.37 | −2.40 |
| AC139491.5 | −2.41 | 1.48 | 1.95 | 0.39 | −0.84 | GPR31 | 1.16 | −0.22 | −0.81 | 0.93 | −0.79 | RN7SL812P | 0.18 | 0.59 | −0.90 | 0.59 | −0.11 |
| ALDH7A1 | 0.42 | −0.12 | −0.49 | 0.11 | −0.20 | AC245452.2 | −0.57 | 1.14 | −0.03 | 1.09 | −0.10 | RN7SL625P | 0.26 | 0.33 | −1.45 | 0.99 | −1.73 |
| SPACA6 | −0.70 | −0.01 | 0.03 | −0.17 | −0.08 | RFPL3S | −0.56 | −0.57 | −0.07 | 0.30 | 0.19 | AL354892.1 | 0.16 | 0.12 | 1.50 | −0.39 | 0.13 |
| CARF | −0.39 | 0.28 | 0.54 | 0.07 | 0.10 | SNORA26 | −0.32 | 0.54 | −0.38 | 0.62 | −0.64 | AL359880.1 | 0.11 | 0.09 | −0.24 | −0.32 | −0.98 |
| AL132656.3 | −0.94 | 0.33 | 1.18 | −0.26 | 0.48 | ENSAP1 | −1.78 | 1.13 | 1.51 | −0.17 | 0.66 | RPS4XP20 | 0.28 | 0.76 | −0.98 | −0.06 | −0.80 |
| CACNB4 | 0.98 | −0.01 | −0.62 | 0.51 | −0.22 | OR52L1 | −1.13 | 0.37 | 0.16 | 1.39 | 0.01 | ASS1P5 | 0.26 | −0.41 | 2.02 | −0.07 | 0.12 |
| LCMT1 | 0.41 | 0.09 | −0.11 | 0.00 | −0.51 | CPB2 | 0.48 | −0.56 | −0.46 | 0.22 | 0.16 | AC092436.2 | −1.06 | 0.52 | NA | 0.32 | −0.85 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AP000351.10 | −1.30 | 0.50 | 0.88 | 0.36 | 0.04 | IRF2BP1 | −0.15 | 0.24 | 0.05 | 0.18 | −0.05 | LINC02520 | 0.42 | −0.84 | 0.47 | −0.56 | 1.32 |
| NPLOC4 | 0.29 | −0.14 | −0.44 | 0.03 | −0.18 | IGHG3 | 1.00 | 0.72 | 3.65 | −1.16 | −0.52 | RN7SL444P | −0.13 | −0.10 | 0.58 | −0.89 | −0.44 |
| RASL12 | −1.00 | 0.30 | 0.82 | 0.09 | 0.02 | BX537318.2 | −0.33 | 0.42 | 0.64 | 0.08 | 0.22 | EIF3LP3 | 0.35 | −1.09 | −1.03 | −0.52 | −1.15 |
| CLIP2 | −0.50 | 0.07 | 0.17 | 0.04 | 0.02 | GPR3 | 0.35 | −0.09 | −1.07 | −0.46 | −1.66 | RP11-417J8.2 | −0.31 | −1.05 | −1.35 | 0.35 | 0.73 |
| CENPI | 0.69 | −0.76 | −0.98 | −0.14 | −0.22 | LINC01719 | −0.25 | 0.28 | 0.21 | −0.15 | −0.08 | GYS2 | −0.51 | −0.18 | −0.05 | −0.22 | −0.04 |
| AC012404.2 | −1.18 | 0.97 | 2.09 | −0.07 | 0.23 | AC087286.1 | 0.33 | −0.29 | −0.17 | −0.40 | 0.10 | AC083855.1 | −0.14 | 0.63 | −0.41 | −0.02 | −1.87 |
| GAB2 | −0.57 | 0.60 | 0.56 | 0.03 | −0.27 | AC127526.3 | −0.53 | 0.61 | 0.75 | −0.49 | 0.36 | AL049875.1 | 0.08 | −0.06 | −0.51 | −0.10 | −0.19 |
| GMEB1 | 0.34 | −0.12 | −0.36 | 0.00 | −0.31 | RNU6-1153P | 0.61 | −0.45 | 0.60 | −0.01 | 0.71 | G31554 | 0.14 | 0.44 | 0.46 | 0.76 | −0.05 |
| DPF1 | 0.94 | −0.44 | −2.15 | −0.04 | −0.98 | DAW1 | −0.72 | 0.07 | −0.57 | −0.37 | −2.49 | DUXAP1 | −0.40 | −0.25 | −0.59 | −0.79 | −0.82 |
| RNA5SP19 | −1.80 | 0.48 | 0.44 | 0.61 | 0.33 | FAM227B | −0.24 | 0.10 | 0.49 | 0.10 | 0.32 | AL603839.4 | −0.17 | 0.09 | 0.39 | −0.20 | −0.10 |
| G29048 | −1.50 | 1.73 | 1.27 | 0.83 | 0.42 | GCN1 | 0.12 | −0.16 | −0.28 | 0.02 | 0.05 | AC245517.1 | 0.55 | −1.73 | −1.19 | −0.14 | 0.82 |
| LINC02240 | −1.75 | 0.71 | 0.77 | 1.67 | 1.17 | AC138474.1 | −0.42 | 0.48 | 0.43 | 0.69 | 0.23 | AL136964.1 | 0.26 | −1.36 | 0.26 | −0.66 | 1.82 |
| AC087260.1 | −1.88 | 1.50 | 1.98 | 1.08 | −0.12 | FRY-AS1 | −0.34 | −0.20 | 0.67 | 0.21 | 0.14 | OR3A1 | 0.42 | −1.56 | 0.09 | −0.72 | 0.85 |
| ALKBH5 | 0.44 | −0.12 | −0.30 | −0.05 | −0.21 | FEZ2 | 0.13 | −0.11 | −0.25 | −0.09 | −0.09 | AC020980.1 | 0.45 | −0.89 | −2.49 | −0.48 | −0.85 |
| FRG1JP | −0.46 | 0.10 | 0.76 | −0.14 | 0.54 | SP140 | −0.34 | −0.64 | 0.72 | −0.68 | 0.59 | AC005381.1 | −0.45 | −2.19 | 0.01 | −1.34 | 1.20 |
| KDM5C-IT1 | −1.01 | 0.00 | 0.16 | 0.30 | 0.48 | NGDN | 0.12 | −0.09 | −0.12 | −0.17 | −0.22 | NUDT3 | −0.04 | −0.05 | −0.03 | 0.05 | 0.29 |
| HSPA14 | 0.40 | −0.23 | −0.16 | −0.10 | −0.09 | MTCYBP35 | −0.31 | 0.02 | 0.36 | −0.17 | 0.14 | G30960 | −0.14 | −0.15 | 0.94 | −0.38 | 0.87 |
| LIN7C | 0.54 | −0.15 | −0.26 | −0.08 | −0.22 | MIR4669 | 0.77 | 0.29 | −0.31 | 0.49 | 0.10 | RUSC1 | 0.03 | 0.08 | −0.33 | 0.16 | −0.21 |
| SPRR2G | 1.81 | −0.80 | −0.30 | −0.99 | 0.53 | LINC02599 | −0.44 | −0.77 | 1.40 | −0.68 | 0.40 | KCP | 0.07 | −0.48 | −0.89 | −0.10 | −0.17 |
| METTL8 | 0.51 | −0.14 | −0.39 | 0.17 | −0.08 | RPL36AP21 | −0.62 | 0.18 | −0.97 | −0.10 | −0.33 | FGG | −0.26 | −0.56 | 0.01 | 0.03 | −2.14 |
| GNG12-AS1 | −0.56 | 0.20 | 0.21 | 0.39 | 0.09 | DUTP2 | 0.46 | −0.56 | −0.70 | 0.09 | 0.08 | PRLHR | −0.23 | −0.24 | −0.67 | 0.75 | −1.49 |
| INMT | −1.16 | 0.56 | 1.07 | 0.95 | 0.53 | GPX1 | 0.22 | −0.14 | −0.03 | −0.21 | −0.14 | AL441988.1 | −0.10 | −0.27 | −0.17 | −0.19 | 0.24 |
| PPP1R12C | −0.64 | 0.16 | 0.00 | 0.28 | 0.13 | AC104076.1 | −1.12 | 0.43 | −0.55 | −0.22 | −2.17 | AC099681.3 | −0.53 | −1.13 | −0.23 | −0.95 | −0.29 |
| REEP3 | 0.52 | −0.26 | −0.32 | −0.13 | −0.43 | AP001880.2 | −1.25 | 0.18 | −0.60 | 0.08 | −0.77 | MRTFA | −0.03 | −0.06 | −0.15 | −0.06 | −0.04 |
| AC011498.1 | −0.77 | 0.02 | 0.55 | 0.43 | 0.50 | RPL34P27 | 0.51 | −0.57 | −0.27 | −0.41 | −0.04 | AL355578.1 | 0.35 | −0.15 | −2.12 | 1.33 | −1.40 |
| AC084759.3 | −1.82 | 1.36 | 2.64 | 1.19 | 0.29 | RNU6-920P | 0.66 | 0.05 | 0.75 | −0.97 | −0.22 | AC087481.1 | −0.17 | −0.87 | 0.09 | 0.31 | 0.42 |
| AC022726.2 | −1.15 | 0.43 | 0.73 | −0.04 | 0.23 | AL445991.1 | 0.41 | −0.90 | 0.57 | −0.64 | 0.78 | DHX 40 | 0.03 | 0.15 | 0.17 | 0.09 | −0.15 |
| FRG1-DT | −0.98 | 0.19 | 0.52 | 0.35 | 0.60 | AL590302.1 | 1.07 | −0.27 | −1.25 | −0.41 | −2.21 | AC011472.4 | −0.08 | 0.33 | 0.21 | 0.18 | −0.07 |
| MUL1 | 0.47 | 0.03 | −0.20 | −0.07 | −0.28 | AC005828.7 | 0.46 | −0.05 | −0.77 | −0.01 | 0.05 | AC087664.2 | −0.31 | −0.75 | −2.04 | 1.23 | 0.21 |
| SHC3 | −1.25 | 0.32 | 0.43 | 0.47 | 0.21 | AC100800.1 | −0.25 | 0.09 | 0.29 | 0.01 | 0.30 | CTD-2297D10.2 | −0.43 | −0.44 | −1.28 | 1.11 | −1.63 |
| KIAA1324L | −0.79 | 0.35 | 0.71 | −0.03 | 0.35 | AC106038.1 | −0.27 | 0.64 | 0.48 | 0.43 | 0.32 | AC027369.3 | −0.74 | 0.24 | −0.46 | 1.09 | −0.26 |
| NOC3L | 0.40 | −0.43 | −0.22 | −0.26 | 0.17 | AC114728.1 | 0.78 | −0.32 | 1.23 | −0.26 | −0.22 | EEF1A1P9 | 0.07 | 0.01 | −0.42 | 0.04 | −0.54 |
| CRIP3 | −1.72 | 0.16 | 2.08 | 0.14 | 1.71 | ME3 | −0.24 | 0.06 | 0.44 | −0.14 | 0.31 | OR7E33P | −0.57 | −0.68 | −0.86 | 1.24 | 3.90 |
| AC123912.4 | −2.02 | 0.80 | 0.68 | 0.22 | 0.70 | RAB39A | 0.56 | −0.28 | 0.22 | −0.38 | 0.07 | OR5BE1P | 0.32 | 0.44 | −1.34 | 0.17 | −1.65 |
| AC008080.1 | −1.11 | 0.84 | 1.35 | 0.14 | 0.03 | GPR6 | −1.60 | 0.33 | 1.37 | 1.20 | 1.59 | GAPDHP67 | 0.67 | −0.50 | −2.38 | 0.93 | −1.02 |
| NEIL3 | 0.93 | −0.82 | −1.40 | −0.13 | −0.44 | RETREG2 | −0.10 | 0.21 | −0.10 | 0.32 | −0.09 | APLF | −0.03 | 0.21 | 0.30 | 0.02 | 0.00 |
| MIR210 | −1.72 | 1.71 | 1.73 | 0.90 | −0.43 | RPS4XP11 | 0.62 | 0.09 | 0.04 | 0.24 | 0.36 | CCR12P | −0.14 | −1.37 | −0.41 | 0.25 | 0.22 |
| DSC1 | 1.32 | 0.16 | 0.15 | 0.85 | −0.83 | AC022973.1 | 0.36 | −0.53 | −0.57 | −0.36 | −0.31 | LINC00964 | −0.06 | 0.37 | 0.53 | 0.25 | 0.21 |
| PROCA1 | −0.53 | 0.06 | 0.11 | −0.06 | 0.03 | SNORD116-13 | −0.70 | 0.96 | 0.42 | 0.53 | 0.83 | PSRC1 | 0.05 | −0.50 | −0.83 | −0.25 | −0.11 |
| ITM2B | 0.59 | −0.05 | −0.22 | 0.06 | −0.30 | RPL21P54 | −0.86 | −0.18 | 1.15 | −0.25 | 0.29 | AC073283.1 | 0.10 | 0.44 | 0.39 | 0.25 | 0.32 |
| KIT | −0.73 | 0.47 | 0.85 | 0.12 | 0.29 | CHD2 | 0.08 | 0.04 | −0.24 | 0.09 | −0.17 | AC138035.1 | 0.08 | −0.12 | −0.17 | 0.22 | 0.46 |
| ARID3C | −1.40 | 0.40 | 1.74 | −0.15 | 0.38 | G42644 | −0.63 | 0.21 | −0.46 | 0.82 | −0.25 | AC104758.2 | −0.12 | 0.38 | 0.45 | 0.57 | 0.45 |
| AHCTF1 | 0.32 | −0.12 | −0.14 | −0.14 | −0.11 | GPR152 | −0.73 | 0.56 | −0.74 | 0.57 | −0.54 | AC091932.1 | −0.12 | −0.24 | 0.22 | −0.57 | 0.76 |
| MTMR9 | 0.46 | −0.32 | −0.30 | −0.18 | −0.18 | AC138623.1 | −0.84 | −0.07 | 1.03 | 0.98 | 0.14 | AC087897.2 | −0.37 | 0.73 | −0.61 | 0.57 | −0.86 |
| G40766 | 1.66 | −0.90 | −2.21 | −0.11 | −1.16 | ENAM | 0.71 | −1.08 | −1.02 | 0.42 | −0.01 | AC026887.1 | −0.26 | −1.46 | −2.87 | 0.40 | −0.97 |
| PTMAP1 | −0.79 | 0.02 | 0.27 | 0.28 | 0.48 | RPS2P1 | −0.79 | 0.76 | 0.20 | 0.75 | −0.14 | AC110491.2 | −0.08 | 0.13 | 0.28 | −0.10 | −0.14 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| PEG10 | −0.90 | 0.76 | 0.30 | 0.44 | 0.07 | AP001107.5 | −0.78 | −1.51 | −0.27 | −0.37 | −0.74 | HSP90AB6P | 0.18 | −1.50 | −2.25 | 0.30 | −0.78 |
| GPAT2P2 | −2.06 | 2.26 | 2.29 | 0.70 | 0.64 | RP6-42F4.1 | −0.19 | 0.05 | 0.42 | −0.24 | 0.23 | AC108025.1 | −0.34 | −0.42 | 0.31 | 0.42 | 1.04 |
| DPY19L1 | 0.51 | −0.40 | −0.41 | −0.12 | −0.24 | PADI1 | 0.42 | 0.77 | 1.12 | 0.16 | −0.12 | LINC01358 | 0.11 | −0.22 | −0.68 | −0.20 | −0.13 |
| LZTS3 | −0.75 | 0.68 | 0.44 | 0.48 | 0.07 | C1GALT1C1L | −0.41 | 0.14 | 0.08 | −0.07 | −0.41 | DNAJB8-AS1 | −0.24 | −0.12 | 1.57 | 0.16 | 1.07 |
| AC011498.7 | −0.66 | −0.01 | 0.22 | 0.23 | 0.28 | SLC34A2 | 0.61 | −0.15 | 0.14 | 0.34 | 0.14 | AC004846.2 | 0.10 | −0.09 | 0.82 | −0.40 | −0.12 |
| KRTAP10-11 | −2.11 | 0.71 | −0.74 | 0.56 | −0.79 | AC093311.1 | −0.38 | 0.49 | 1.07 | 0.05 | −0.11 | CLDND1 | 0.05 | 0.11 | 0.21 | 0.04 | −0.13 |
| PSMA6 | 0.34 | −0.23 | −0.33 | −0.04 | −0.08 | LINC01168 | 0.66 | −1.84 | −0.67 | −0.09 | 0.19 | LINC02444 | 0.24 | −0.30 | −0.11 | 0.47 | 0.16 |
| RPS2P46 | 0.75 | −0.33 | 0.30 | −0.19 | −0.07 | MIR3138 | 0.45 | −0.42 | −0.61 | 0.18 | 0.21 | STRADBP1 | −0.36 | −0.09 | −0.66 | 0.22 | −0.53 |
| GRHL1 | 0.60 | −0.08 | −0.42 | −0.02 | −0.19 | PRSS37 | −0.46 | 0.43 | 0.83 | 0.03 | 0.17 | MIR339 | 0.17 | 0.14 | −0.48 | 0.03 | −0.32 |
| AOC3 | −1.37 | 1.04 | 1.11 | 0.47 | −0.24 | CKLF | 0.35 | −0.66 | 0.06 | −0.54 | 0.26 | RNF208 | −0.06 | 0.41 | −0.14 | 0.29 | −0.07 |
| AC139426.1 | −2.58 | 1.46 | 0.16 | 1.08 | −1.31 | ALG1L | −0.46 | −0.34 | 0.52 | 0.21 | 0.82 | MIPEPP1 | −0.15 | 0.62 | −0.86 | 0.51 | −0.18 |
| CH25H | 1.42 | −1.37 | −0.96 | −0.21 | −0.10 | AC013403.2 | −0.29 | −0.38 | 0.46 | −0.25 | 0.47 | CEP76 | −0.04 | 0.08 | 0.33 | 0.12 | 0.00 |
| GYPC | −0.97 | 0.59 | 0.90 | −0.05 | −0.17 | CLEC4E | 0.64 | −0.89 | −1.22 | −0.57 | −1.86 | AC109322.1 | −0.09 | 0.30 | −0.01 | 0.21 | −0.06 |
| PPP1R2 | 0.52 | −0.17 | −0.36 | −0.10 | −0.46 | NYAP2 | −0.58 | 0.23 | 0.49 | −0.05 | 0.06 | AC021683.4 | −0.32 | −2.07 | 0.65 | 0.14 | 1.19 |
| CYP1B1-AS1 | −0.79 | 0.38 | 0.45 | 0.08 | 0.19 | AC006064.2 | 0.53 | −0.23 | −0.30 | 0.40 | 0.23 | AC243967.2 | 0.69 | −0.05 | −0.13 | −0.21 | 0.48 |
| GPR82 | 0.69 | −0.38 | −0.40 | −0.07 | 0.02 | MIR4804 | 0.71 | −0.16 | −0.26 | 0.08 | 1.33 | AP003501.3 | 0.15 | −0.48 | 0.07 | −0.50 | −0.26 |
| AC073349.2 | −0.93 | 0.62 | 1.34 | 0.31 | 0.51 | AC087481.3 | −0.22 | 0.12 | 0.34 | 0.12 | 0.36 | MTCO3P44 | −0.40 | −1.51 | −1.19 | −0.21 | −0.06 |
| PDCD2 | 0.48 | −0.27 | −0.16 | −0.29 | −0.01 | LINC01708 | −0.80 | −0.61 | 0.97 | −0.37 | 0.34 | RPSAP33 | 0.39 | 0.42 | −0.18 | 1.37 | −0.40 |
| PLPP3 | −0.63 | 0.30 | 1.20 | −0.14 | 0.36 | BUD23 | 0.12 | −0.02 | −0.25 | 0.08 | −0.07 | AP002478.2 | −0.24 | −0.67 | −1.08 | 1.91 | −0.28 |
| AL109628.2 | −0.91 | −0.04 | 0.39 | 0.15 | 0.80 | AC087749.2 | −0.28 | 0.06 | −0.40 | −0.11 | −0.21 | AC010745.2 | 0.28 | 0.09 | −1.22 | 1.24 | −1.75 |
| POLR2E | 0.33 | −0.13 | −0.52 | 0.11 | −0.19 | GPAT2P1 | −0.83 | 0.48 | 0.97 | 0.60 | 0.09 | AC245100.3 | −0.71 | 0.18 | −0.73 | 0.92 | 2.29 |
| ASB7 | 0.39 | −0.17 | −0.20 | −0.06 | −0.13 | AC079416.2 | 0.26 | −0.28 | −0.11 | 0.10 | 0.24 | AC062022.1 | 0.43 | 1.02 | −1.42 | 1.27 | 0.73 |
| MXRASY | −0.89 | 0.99 | 1.11 | 0.51 | 0.64 | GNE | −0.14 | 0.14 | 0.21 | −0.01 | 0.04 | BNIP3P20 | 0.33 | −0.81 | −0.63 | 1.53 | 1.37 |
| C20orf204 | −0.77 | 0.34 | −0.03 | 0.40 | 0.24 | GXYLT1P4 | −1.26 | 0.41 | −0.42 | 1.54 | −1.75 | SALL1 | 0.10 | −0.67 | −0.51 | −0.71 | −0.39 |
| PPIAP16 | 1.08 | −0.89 | −1.01 | −0.11 | −0.28 | AP000722.1 | −1.28 | −1.28 | 1.98 | −1.67 | 0.56 | RPL31P7 | 0.11 | −0.96 | 1.35 | −0.46 | 1.42 |
| AC006238.2 | 0.98 | −1.04 | −1.19 | −0.48 | −0.50 | GAN | −0.28 | 0.77 | 1.35 | 0.36 | 0.06 | DMC1 | 0.07 | −0.10 | −0.09 | −0.17 | 0.07 |
| RAB2A | 0.47 | −0.06 | −0.28 | −0.06 | −0.36 | ATP5MG | 0.20 | −0.04 | −0.07 | −0.02 | −0.23 | AC005181.1 | −0.41 | −1.21 | 0.25 | 0.09 | 0.73 |
| RFX1 | −0.55 | 0.48 | 0.39 | 0.24 | 0.02 | OR52W1 | −0.48 | 0.67 | 0.07 | 0.09 | −0.95 | AL357552.1 | −0.10 | 0.00 | 0.36 | 0.22 | 0.66 |
| DNAAF2 | 0.46 | −0.12 | −0.06 | −0.20 | 0.07 | GRPR | −0.65 | −0.41 | 0.49 | −0.06 | −0.67 | KRTAP9-3 | −1.05 | −0.48 | 1.25 | −2.45 | −2.62 |
| SMNDC1 | 0.37 | −0.26 | −0.31 | −0.07 | −0.05 | RPL9P8 | 0.67 | −0.14 | 0.05 | −1.51 | −0.82 | AC007240.1 | −0.08 | −0.50 | −0.78 | −0.17 | −0.53 |
| DOP1B | −0.30 | 0.29 | 0.37 | 0.07 | 0.03 | AC005899.7 | −0.55 | 0.32 | 0.64 | 0.34 | 0.43 | AC108456.1 | 0.25 | 0.15 | 0.02 | 0.54 | 0.81 |
| RAB2B | −0.40 | 0.15 | −0.04 | 0.21 | −0.01 | PABPC4L | −0.28 | 0.09 | 0.23 | 0.41 | 0.02 | AC093635.1 | 0.19 | −2.21 | 1.77 | −0.19 | 0.40 |
| MED16 | −0.40 | 0.23 | 0.08 | 0.21 | 0.07 | PLEKHG1 | −0.17 | 0.21 | 0.83 | −0.34 | 0.00 | GANC | −0.02 | −0.02 | −0.11 | 0.01 | 0.11 |
| OR10Q1 | −1.54 | −0.36 | −0.20 | 0.79 | −0.52 | SEPHS1P6 | −0.99 | 0.24 | 1.07 | −0.28 | −0.25 | G18243 | 0.11 | −0.08 | 0.99 | 0.10 | 0.34 |
| NTM-AS1 | −2.35 | 0.74 | 1.77 | −0.31 | 0.92 | IGF2BP2 | 0.22 | −0.26 | −0.10 | 0.17 | 0.16 | AP001831.1 | 0.11 | 0.36 | −0.30 | −0.08 | −0.36 |
| PRIMPOL | −0.33 | 0.06 | 0.29 | 0.00 | 0.07 | AL357140.5 | −0.33 | 0.28 | 0.61 | 0.12 | 0.22 | AC003965.1 | 0.37 | 0.62 | −0.60 | 0.43 | −1.36 |
| AC010834.3 | −0.73 | 0.00 | 0.65 | 0.06 | 0.52 | OR6X1 | −1.18 | −0.23 | 0.14 | 0.94 | 0.13 | NDUFB4P11 | −0.17 | −0.45 | −0.44 | 0.62 | −0.90 |
| LINC01705 | 1.91 | −1.99 | −3.97 | −1.08 | −1.52 | G38115 | −0.66 | 1.47 | −0.91 | 0.88 | −0.99 | C5orf63 | −0.04 | 0.08 | 0.27 | −0.11 | 0.34 |
| RPL4 | 0.57 | −0.07 | −0.25 | −0.13 | −0.49 | AP000695.2 | 0.53 | −0.69 | −1.34 | −0.68 | −0.70 | AC103691.1 | 0.09 | −1.32 | −0.71 | −0.67 | 0.71 |
| SMAGP | 0.55 | 0.06 | −0.36 | 0.20 | −0.33 | CDKN2B-AS1 | 0.37 | −0.15 | −0.02 | 0.24 | 0.20 | AC005703.1 | −0.38 | −0.35 | 0.82 | −0.24 | 1.60 |
| AC019270.1 | −1.02 | 0.57 | 1.87 | −0.10 | 0.10 | RPS2P55 | 0.34 | −0.66 | −0.50 | −0.03 | 0.03 | RNU6-1013P | −0.40 | 0.46 | 0.80 | −0.08 | −2.00 |
| PODN | −1.32 | 1.05 | 2.29 | −0.08 | 0.10 | MIR3192 | −0.57 | 0.35 | 0.26 | 0.59 | −0.27 | HDGFP1 | 0.16 | −0.15 | −1.18 | 0.64 | −0.03 |
| AC005495.1 | −1.19 | 0.32 | 0.33 | 0.89 | 0.49 | ASB15 | 0.51 | −0.53 | −2.00 | 0.14 | −1.26 | AC010531.8 | 0.29 | −0.45 | 0.48 | 0.13 | −0.06 |
| CARS | 0.31 | −0.09 | −0.39 | 0.00 | −0.20 | RN7SKP253 | 0.39 | 0.17 | 0.36 | 0.27 | 0.27 | BCDIN3D | 0.05 | 0.03 | −0.18 | 0.28 | 0.03 |
| IREB2 | 0.38 | −0.19 | −0.24 | −0.02 | −0.13 | AC013564.1 | 0.88 | 0.26 | 2.91 | −0.37 | 0.03 | MTCO2P9 | −1.01 | −1.51 | 0.82 | −1.17 | 0.76 |
| BDKRB1 | 1.14 | −0.45 | −1.04 | −0.16 | −0.84 | AC139887.1 | −0.50 | 0.42 | 0.50 | 0.84 | 1.14 | PDC | −0.09 | 0.16 | 0.28 | 0.10 | −0.03 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AL133458.1 | −0.80 | 0.46 | 0.56 | 0.18 | 0.34 | HDAC2-AS2 | −0.35 | 0.27 | −0.26 | 0.14 | −0.42 | HMGB1P27 | −0.20 | 0.65 | 1.01 | 0.36 | 0.53 |
| RFTN2 | −0.71 | 0.50 | 1.18 | −0.16 | 0.28 | AL132656.2 | −0.43 | 0.47 | 1.04 | 0.04 | 0.44 | AL391244.3 | −0.05 | −0.40 | −0.10 | −0.17 | 0.31 |
| RNU6-638P | 1.14 | −0.41 | 0.02 | −0.44 | −0.06 | SOGA3 | −0.97 | 1.23 | 1.69 | 0.98 | −0.59 | RNU6-423P | 0.60 | −1.14 | −1.25 | −1.09 | −0.63 |
| AC067930.3 | −1.25 | 0.56 | 0.59 | 0.28 | 0.34 | CCNJ | 0.14 | −0.09 | 0.15 | −0.02 | 0.12 | AC124283.2 | 0.10 | −0.05 | 0.34 | −0.34 | 0.27 |
| RNU1-136P | −1.76 | −0.26 | −1.00 | 0.32 | 0.25 | NOTCH4 | −0.27 | −0.09 | 0.30 | 0.29 | 0.25 | OR2A25 | −0.18 | −0.21 | −0.74 | 1.02 | −0.47 |
| BX088645.3 | −1.98 | 1.82 | 1.89 | 0.86 | 1.09 | PAICSP3 | −0.94 | 0.50 | 1.56 | −0.84 | −0.53 | OR10Y1P | −0.18 | 0.47 | 0.86 | 1.15 | 0.95 |
| LGALS3BP | 0.74 | −0.51 | −1.15 | −0.18 | −0.55 | AC011448.1 | −0.54 | 0.47 | 0.76 | −0.21 | 0.44 | AL390719.2 | −0.09 | 0.30 | −0.58 | 0.45 | 0.05 |
| LINC01255 | −1.74 | 0.62 | 0.33 | 0.99 | −0.08 | AC109326.1 | 0.23 | −0.18 | −0.41 | 0.02 | 0.06 | MARK2P12 | −0.28 | 1.85 | −0.54 | 3.69 | −1.66 |
| CTNND1 | 0.44 | −0.10 | −0.28 | −0.04 | −0.09 | FUBP1 | 0.12 | −0.17 | −0.25 | −0.08 | 0.01 | PPP1R10 | 0.03 | −0.16 | −0.12 | −0.24 | 0.03 |
| RPS7P11 | 0.75 | −0.23 | −0.87 | −0.22 | −0.77 | MCRS1 | 0.11 | −0.13 | −0.44 | 0.04 | −0.14 | PCBD1 | 0.04 | 0.29 | 0.03 | 0.06 | −0.07 |
| COLGALT1 | 0.34 | −0.40 | −0.50 | −0.10 | −0.04 | AC004906.1 | 1.28 | −1.04 | 0.50 | −1.23 | 1.09 | AC132938.1 | 0.60 | −0.53 | 0.55 | 0.18 | −1.97 |
| NANOGP2 | 1.05 | −0.34 | −0.34 | 0.08 | 0.20 | LINC01080 | −0.80 | 0.68 | −0.91 | 0.02 | −0.82 | AC099522.2 | −0.13 | −0.25 | 0.11 | −0.60 | −0.48 |
| AC012409.1 | −1.34 | 1.12 | 1.83 | 0.86 | 0.71 | AC012400.1 | −1.32 | −0.09 | 1.31 | 0.31 | 1.03 | AC079465.1 | −0.08 | 0.26 | 0.51 | 0.38 | 0.13 |
| MESD | 0.27 | −0.11 | −0.21 | −0.11 | −0.13 | MIR1299 | −0.61 | 0.05 | 0.30 | −0.40 | 0.58 | C19orf66 | 0.05 | −0.29 | −0.32 | −0.16 | 0.15 |
| AL390023.1 | −2.15 | 0.83 | −1.18 | 0.92 | −0.61 | L1TD1 | −0.37 | −0.17 | 0.38 | 0.07 | 0.24 | GMPPB | 0.04 | −0.14 | −0.33 | −0.03 | 0.06 |
| COPS4 | 0.42 | −0.14 | −0.25 | −0.14 | −0.30 | FAM178B | −0.36 | 0.78 | −0.19 | 0.72 | −1.19 | NIPBL-DT | −0.06 | 0.09 | 0.31 | 0.05 | −0.09 |
| AC007622.2 | 0.63 | −0.28 | −0.50 | −0.07 | −0.34 | CHM | 0.13 | −0.07 | −0.16 | −0.13 | −0.13 | AC009630.1 | −0.21 | 0.02 | 0.25 | 0.60 | 0.38 |
| AJM1 | −0.78 | 0.16 | 0.65 | 0.39 | 0.92 | AL512637.1 | 0.46 | 0.19 | −0.77 | −0.58 | −1.62 | OR11A1 | 0.23 | 0.32 | −1.80 | −0.20 | −2.93 |
| LHCGR | −1.37 | 1.48 | 1.11 | 1.01 | 0.05 | PHC1 | −0.16 | 0.05 | 0.09 | −0.05 | −0.10 | AL138927.1 | 0.22 | −1.14 | −1.12 | 0.35 | −1.17 |
| RNU7-124P | 1.90 | −0.88 | −0.34 | −0.81 | 0.31 | G38113 | −0.47 | 0.60 | 0.46 | 0.52 | −0.29 | OR5D18 | −0.46 | −1.11 | −1.36 | 0.30 | 0.41 |
| G12735 | −1.25 | 0.68 | 1.62 | 0.11 | 1.06 | LCMT1-AS1 | −0.50 | 0.60 | 0.69 | 0.04 | 0.41 | AL137159.1 | 0.20 | 0.78 | 0.78 | 0.17 | 0.73 |
| C3orf70 | −0.59 | 0.09 | 0.59 | −0.08 | 0.40 | RSPH4A | −0.20 | −0.01 | 0.24 | 0.01 | 0.21 | AC083843.1 | −0.14 | −0.93 | 0.34 | 0.25 | 0.00 |
| ITGA8 | −1.02 | 0.54 | 0.64 | 0.30 | −0.12 | ST8SIA3 | −0.84 | 0.52 | −0.51 | 0.70 | −0.14 | AC112495.1 | 0.65 | −1.50 | −1.09 | 0.31 | 0.10 |
| MRRF | 0.31 | −0.08 | −0.13 | −0.04 | −0.05 | G25996 | 1.00 | 0.89 | −0.25 | −0.42 | −0.71 | LINC02087 | −0.30 | 0.60 | −2.15 | 1.24 | −1.44 |
| RAB3GAP1 | 0.29 | −0.06 | −0.18 | −0.05 | −0.20 | ACTR8 | 0.11 | 0.04 | −0.01 | −0.09 | −0.25 | GAPDHP73 | 0.20 | −0.29 | 0.36 | 1.46 | 0.46 |
| ADHIC | −1.88 | 0.76 | 0.92 | 0.49 | −0.59 | AL137060.1 | −0.34 | 0.18 | −0.74 | 0.28 | −0.46 | RPL36AP45 | −0.13 | −0.23 | −1.15 | 0.68 | −0.55 |
| AC005165.1 | −1.84 | 1.19 | 2.93 | 0.40 | 1.37 | SESN3 | 0.20 | −0.03 | −0.12 | −0.08 | −0.25 | PRR14 | 0.03 | 0.02 | −0.15 | 0.04 | 0.03 |
| DOCK1 | −0.21 | 0.29 | 0.09 | 0.14 | −0.04 | AP002364.1 | −0.52 | 0.68 | 0.71 | 0.19 | 0.17 | AL122019.1 | 0.35 | 0.39 | 0.69 | 0.98 | −3.01 |
| IFIT1 | 0.88 | −0.52 | −0.60 | −0.52 | −0.47 | PTH2R | −0.51 | −0.13 | 0.15 | −0.16 | −0.06 | POTEA | −0.24 | −0.52 | 0.34 | −0.03 | 0.33 |
| LTK | −1.13 | −0.25 | −0.09 | 0.36 | 0.66 | G41823 | 0.38 | 0.00 | 0.08 | −0.16 | 0.19 | RNU1-105P | −0.30 | −1.56 | −1.57 | 0.77 | 0.70 |
| GJC2 | −0.92 | −0.03 | 0.20 | −0.04 | 0.08 | OR9L1P | −0.76 | 0.57 | 0.66 | 1.18 | 0.52 | ATP5MC2P3 | 0.08 | −0.36 | −0.17 | −0.84 | −0.22 |
| PRCP | 0.57 | −0.19 | 0.14 | −0.15 | −0.14 | AC119868.2 | −0.76 | 1.52 | 1.06 | −0.86 | −0.03 | AC012668.3 | −0.18 | −0.28 | −0.13 | 0.06 | 0.17 |
| NANS | 0.41 | −0.28 | −0.33 | −0.21 | −0.12 | PKIA | 0.33 | −0.01 | −0.30 | 0.49 | −0.01 | FTLP15 | 0.38 | −0.65 | −1.41 | −0.51 | −0.27 |
| AC068491.3 | 1.53 | −1.78 | −0.57 | −1.02 | −0.23 | AL357140.3 | −0.46 | 0.27 | 0.48 | −0.03 | −0.18 | AC073389.3 | −0.12 | 0.39 | 0.07 | 0.13 | −0.08 |
| LINC02594 | −2.75 | 0.53 | −0.06 | 1.20 | 0.84 | AC093627.3 | 0.74 | −1.22 | −2.05 | −0.61 | −0.91 | RAC1P5 | −0.31 | −0.26 | 2.06 | 0.65 | 0.52 |
| CYP2B7P | −1.27 | 0.28 | 0.74 | 0.34 | 1.04 | AC007601.2 | 0.43 | −0.30 | −0.82 | −0.20 | 0.04 | RN7SL12P | −0.12 | 0.60 | 1.07 | 0.04 | 0.22 |
| POLR2A | 0.35 | −0.08 | −0.33 | 0.02 | −0.21 | RBM22P4 | 0.55 | −0.23 | −0.49 | −0.79 | −0.61 | AL157827.2 | −0.06 | 0.01 | 0.17 | 0.09 | 0.15 |
| HSPA8P16 | −1.92 | 0.23 | 0.51 | 0.44 | 0.10 | ROCK2 | 0.15 | −0.04 | −0.16 | −0.10 | −0.23 | IGHV3-11 | 1.04 | −0.49 | 0.17 | −2.24 | −0.08 |
| KLF10 | 0.49 | −0.13 | −0.60 | −0.23 | −0.66 | AC108693.2 | 0.69 | 0.03 | −0.12 | 0.49 | −0.65 | PTBP1P | 0.27 | −0.12 | 1.13 | 0.00 | 0.02 |
| G26051 | 2.05 | −2.10 | −1.96 | −1.25 | −1.41 | AP004290.1 | 0.34 | 0.05 | −0.66 | −0.22 | −0.49 | AC004655.1 | −0.40 | 0.72 | 0.41 | 1.36 | −0.54 |
| EPS15 | −0.31 | 0.21 | 0.21 | 0.01 | −0.10 | AL359547.2 | −1.51 | 0.08 | −0.23 | 0.59 | −0.36 | AC239367.3 | −0.59 | −0.67 | 0.13 | 1.22 | 1.73 |
| AL356266.1 | −2.35 | 0.77 | 2.00 | 0.90 | 0.74 | AL138820.1 | −0.28 | 0.15 | −0.12 | 0.19 | 0.07 | RBM12B-AS1 | −0.06 | −0.20 | −0.15 | 0.15 | −0.13 |
| AQP7P1 | −1.59 | 1.49 | 1.80 | 1.44 | −0.41 | FTLP8 | 0.62 | −0.60 | −1.24 | 0.05 | −0.26 | PPIAP8 | 0.40 | 0.67 | 0.58 | 0.32 | 0.22 |
| LINC01285 | −1.36 | 0.57 | 0.78 | 0.75 | 0.88 | AL512506.2 | 0.94 | −0.17 | −1.88 | 0.29 | −0.63 | CLDN34 | −0.10 | −0.14 | 0.40 | 0.25 | 0.70 |
| KRBA1 | 0.51 | −0.15 | −0.68 | 0.14 | −0.05 | G10910 | −0.49 | 1.25 | 0.65 | 0.76 | 0.55 | KCNS1 | 0.08 | −0.31 | −0.06 | −0.61 | 0.06 |
| BACH1-IT3 | 1.24 | −0.38 | −0.40 | −0.57 | −0.45 | CRNKL1 | 0.11 | 0.12 | 0.03 | −0.11 | −0.19 | RNU6-463P | −0.70 | 0.23 | −0.87 | 0.39 | −1.31 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AP001381.1 | 1.17 | −0.47 | −0.95 | −0.21 | −0.34 | SMUG1P1 | −0.93 | 0.26 | −0.21 | 1.49 | −0.10 | LINC02403 | 0.39 | −1.15 | −0.71 | −1.30 | −1.60 |
| CD99L2 | −0.47 | 0.33 | 0.33 | 0.22 | 0.05 | KCNA10 | −0.74 | −0.98 | −0.43 | 0.35 | −0.54 | CRIPT | −0.04 | 0.31 | 0.43 | 0.17 | 0.12 |
| CMBL | −0.91 | 0.43 | 0.85 | 0.06 | 0.15 | BX322234.1 | 0.28 | −0.01 | −0.35 | −0.27 | −0.30 | KCNK16 | 0.29 | −1.05 | 0.49 | 0.06 | 0.72 |
| AC093305.1 | −1.77 | −0.01 | 1.48 | 0.11 | 0.67 | ECEL1 | 0.80 | −0.61 | −0.46 | −0.22 | −0.68 | SPATC1 | 0.12 | −0.08 | −1.26 | −0.35 | −0.22 |
| HABP2 | 2.43 | −0.85 | −2.50 | −0.29 | −1.97 | AXIN1 | −0.13 | 0.07 | −0.23 | 0.15 | −0.05 | RPL31P12 | 0.37 | −0.98 | −0.69 | 0.04 | 0.97 |
| LMX1A | −1.51 | 0.07 | 1.29 | 0.26 | 0.44 | LINC00511 | 0.30 | −0.20 | −0.58 | −0.09 | −0.29 | PRRG2 | 0.05 | 0.23 | 0.12 | 0.28 | 0.01 |
| AC005899.1 | −1.29 | 1.24 | 1.42 | 0.45 | 0.19 | RN7SL775P | −0.44 | 0.28 | 0.44 | −0.66 | −0.70 | AC091180.4 | −0.20 | 0.74 | 2.04 | −0.35 | 1.31 |
| AL356801.1 | −0.60 | 0.25 | 0.39 | 0.17 | −0.09 | AC009248.1 | 0.90 | −1.69 | −0.55 | 0.17 | 1.92 | AC020594.1 | 0.15 | 0.43 | 0.30 | 0.37 | 0.20 |
| PTPRF | −0.45 | 0.40 | 0.18 | 0.30 | 0.07 | BX322784.1 | 1.27 | −1.51 | −0.93 | 0.49 | 0.13 | AC093510.2 | 0.26 | 0.78 | 0.01 | 1.57 | −0.36 |
| ATP6VOA4 | −1.19 | 1.04 | 1.29 | 0.35 | 0.39 | AP003392.1 | −0.24 | −0.10 | −0.35 | −0.11 | 0.08 | AC008549.1 | 0.34 | −0.97 | −1.25 | 0.22 | 0.27 |
| CAP2P1 | −0.63 | 0.35 | 0.23 | 0.20 | −0.07 | AC069257.1 | 0.33 | 0.13 | 0.09 | −0.35 | −0.14 | AL133329.1 | −0.41 | −0.53 | 0.25 | 1.21 | −1.42 |
| CRTC1 | −0.47 | 0.28 | 0.28 | 0.30 | 0.21 | AL049629.1 | 0.37 | 0.15 | 0.57 | −0.26 | 0.13 | AC023043.3 | 0.42 | −0.05 | 0.07 | 0.37 | 0.31 |
| HMGB1P33 | −1.25 | 0.13 | 1.33 | −0.30 | 0.54 | AL031316.1 | −0.67 | 0.35 | −0.45 | 0.09 | −0.31 | AC005479.1 | −0.14 | −0.62 | 1.20 | −0.01 | 0.92 |
| AC051619.3 | −1.94 | −0.42 | 1.19 | 0.20 | 0.62 | C1orf54 | 0.19 | −0.06 | 0.69 | −0.33 | 0.06 | LINC01681 | −0.41 | 0.29 | 1.55 | −0.14 | 0.68 |
| MIR944 | 1.74 | −0.48 | −0.73 | −0.30 | −0.43 | ATPAF2 | 0.12 | −0.02 | −0.14 | 0.15 | 0.02 | IGKV1-6 | 0.54 | 2.06 | 0.33 | 0.71 | −1.65 |
| SNX33 | −0.42 | 0.34 | 0.14 | 0.20 | −0.01 | AL158835.2 | −0.65 | 0.52 | 0.36 | 0.50 | −0.73 | AC091304.1 | −0.25 | −0.64 | −1.39 | 0.15 | −1.69 |
| PGGT1B | 0.44 | −0.18 | −0.17 | −0.07 | −0.10 | MID1IP1-AS1 | 0.43 | −0.48 | −1.10 | −0.26 | −0.19 | AL096869.3 | −0.40 | −0.43 | −2.01 | 0.59 | −0.63 |
| CR392039.4 | −0.88 | −0.03 | 0.22 | 1.00 | 1.26 | MIR3176 | 0.54 | −0.02 | −1.43 | −0.23 | −1.01 | AC005342.2 | 0.46 | 0.61 | 1.65 | −0.41 | 0.36 |
| AL354872.2 | −2.50 | −0.33 | 1.25 | 0.95 | 1.07 | MAPK6P1 | 1.09 | −0.84 | −1.66 | −0.08 | −0.64 | MYHAS | −0.15 | −0.59 | −0.92 | 0.87 | 0.43 |
| CES3 | −0.80 | 0.81 | 0.41 | 0.73 | 0.24 | AC074286.1 | 0.81 | −1.85 | −1.91 | 0.06 | −0.10 | C15orf61 | 0.05 | 0.17 | 0.20 | 0.14 | 0.17 |
| AL133410.1 | −0.90 | 0.30 | 0.49 | 0.38 | 0.14 | RSU1P3 | −0.45 | 0.01 | 0.94 | −0.10 | 0.50 | FAM122B | −0.02 | −0.01 | −0.09 | 0.01 | −0.04 |
| IGHG4 | 2.69 | 0.88 | 2.91 | 0.28 | 0.72 | RNA5SP297 | 0.65 | 0.32 | 0.40 | 0.33 | −0.23 | IGKV3-15 | 1.03 | −0.14 | 0.65 | 2.78 | −1.69 |
| SLC35E2A | −0.54 | 0.35 | 0.50 | 0.29 | 0.31 | A1BG | −0.54 | 0.55 | 1.09 | 0.23 | 0.84 | SERPINA4 | −0.29 | −0.73 | 1.46 | 0.08 | 0.71 |
| INTS8 | 0.32 | −0.09 | 0.01 | −0.11 | −0.03 | IFT80 | −0.14 | 0.08 | 0.40 | −0.05 | 0.07 | AC097625.1 | −0.11 | −0.20 | 1.08 | −0.33 | 0.58 |
| CDHR4 | −1.16 | 0.43 | 1.81 | 0.19 | 0.65 | HMGN1P15 | −0.44 | 0.54 | −0.13 | 0.69 | 0.10 | MLN | 0.42 | −0.66 | 1.25 | −1.17 | 1.50 |
| C2CD2L | −0.48 | 0.19 | 0.20 | 0.11 | 0.01 | AC116563.1 | −1.01 | 0.54 | 0.50 | −0.54 | −0.79 | HSPD1P9 | −0.08 | −0.49 | −0.52 | 0.03 | −0.37 |
| RAP1B | 0.40 | −0.29 | −0.38 | −0.20 | −0.26 | RAB3IP | −0.16 | 0.25 | 0.19 | 0.02 | −0.13 | AC002070.1 | −0.14 | −0.28 | 0.80 | 0.48 | 0.46 |
| CDK3 | −1.70 | 1.90 | 0.59 | 0.67 | −1.02 | AC003681.1 | −0.13 | 0.14 | 0.17 | 0.02 | 0.01 | AC096638.1 | 0.40 | −0.55 | 2.85 | −2.13 | 1.25 |
| CKS1B | 0.67 | −0.33 | −0.67 | −0.16 | −0.32 | AP006621.2 | −0.42 | 0.22 | 0.40 | 0.02 | 0.17 | AL391069.2 | 0.46 | −0.37 | 0.13 | 0.18 | −0.13 |
| RFC2 | 0.46 | −0.36 | −0.64 | −0.07 | −0.33 | SERPINF1 | −0.34 | 0.36 | 0.63 | −0.25 | −0.15 | AC007569.1 | 0.09 | −0.91 | 1.13 | −0.91 | 0.90 |
| INCA1 | −0.72 | 0.11 | 0.59 | −0.03 | 0.27 | AC025031.4 | −0.25 | −0.01 | 0.10 | 0.21 | 0.25 | AL359711.2 | −0.21 | 1.13 | 1.49 | 0.42 | −0.26 |
| AC092612.1 | −0.85 | 0.79 | 0.53 | 0.22 | 0.05 | AC000120.1 | −0.22 | −0.02 | −0.09 | 0.02 | 0.22 | G32202 | −0.46 | 1.22 | 0.34 | 1.03 | −1.11 |
| MFSD12 | −0.71 | 0.18 | −0.11 | 0.04 | −0.03 | CACHD1 | −0.15 | 0.22 | 0.07 | 0.32 | 0.14 | LINC01499 | 0.19 | −0.68 | −0.96 | 0.38 | 0.41 |
| MAP3K3 | −0.34 | 0.19 | 0.32 | 0.02 | 0.05 | AC125232.2 | −0.33 | 0.50 | 0.63 | 0.67 | 0.26 | RN7SKP37 | −0.16 | 0.77 | 0.58 | −0.29 | 0.44 |
| AC104781.2 | 1.51 | −0.20 | −0.18 | 0.06 | 0.16 | AL132989.1 | −0.26 | 0.23 | 0.06 | 0.09 | 0.05 | NCOA4P2 | 0.16 | −1.72 | −0.80 | 0.38 | 0.34 |
| AC073578.3 | 1.88 | −0.35 | −0.97 | 0.08 | −0.74 | AL360270.1 | 0.37 | −0.67 | −0.51 | 0.10 | 0.16 | LINC02390 | −0.18 | −0.20 | 0.52 | −0.29 | 0.86 |
| STPG2 | −1.03 | 0.49 | 0.96 | 0.00 | −0.01 | MIR3116-1 | 1.17 | −0.94 | −1.01 | −0.92 | 0.16 | AL391261.1 | −1.03 | −1.43 | 0.29 | −0.71 | −0.38 |
| INTS14 | 0.35 | −0.12 | −0.20 | −0.11 | −0.09 | LEF1 | −0.25 | −0.03 | 0.36 | 0.01 | 0.36 | IL22RA1 | 0.05 | 0.11 | 0.29 | 0.17 | 0.03 |
| L3MBTL2 | −0.44 | 0.05 | −0.01 | 0.19 | 0.25 | AC092597.1 | −0.43 | 0.56 | 1.55 | −0.70 | 0.23 | FOXL1 | 0.11 | −0.04 | −1.24 | 0.87 | −0.60 |
| RNU1-4 | −1.20 | −0.09 | 0.00 | −0.40 | 0.23 | AL136115.1 | 0.22 | −0.39 | −0.20 | −0.11 | 0.21 | MIR181B2 | 0.16 | 1.35 | 0.39 | 0.58 | −0.50 |
| G36510 | 1.01 | −0.48 | −0.52 | 0.08 | 0.09 | JMJD4 | −0.26 | 0.10 | 0.61 | −0.08 | 0.49 | CUL4A | 0.02 | −0.04 | −0.11 | 0.04 | 0.03 |
| AC106738.1 | −1.18 | 0.64 | 1.13 | 0.18 | 0.21 | AC026412.2 | −0.38 | 0.21 | 0.66 | 0.15 | 0.46 | AC023078.6 | 0.34 | −1.18 | 0.04 | −0.99 | −0.81 |
| NPM1P39 | 1.19 | −0.55 | −1.03 | 0.12 | −0.26 | KCNQ1 | −0.32 | 0.27 | −0.03 | 0.20 | −0.06 | AC092868.1 | 0.52 | −0.52 | 0.91 | −0.87 | −1.03 |
| NINL | −0.66 | 0.03 | 0.36 | 0.15 | 0.29 | AC016027.3 | −0.35 | −0.48 | −0.64 | −0.13 | 0.23 | AC068759.1 | −1.03 | 0.16 | 0.21 | −0.77 | 0.23 |
| SETMAR | −0.32 | 0.30 | 0.37 | 0.19 | 0.11 | AL590286.2 | −0.70 | 0.18 | 1.42 | −0.84 | −0.01 | SHROOM2P1 | −0.40 | 0.02 | −0.33 | 0.24 | −0.40 |
| PTS | 0.48 | −0.25 | −0.41 | −0.15 | −0.14 | RPSAP32 | −1.58 | 1.47 | 2.18 | 0.28 | 0.86 | AC100849.2 | 0.47 | 0.70 | −1.72 | 0.80 | −3.07 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| LACTB | 0.49 | −0.24 | −0.45 | −0.21 | −0.41 | GPN3 | 0.20 | −0.16 | −0.17 | −0.15 | −0.20 | LINC01399 | 0.50 | −0.59 | 0.61 | −1.22 | −0.46 |
| CCDC153 | −0.81 | 0.27 | 0.35 | 0.07 | 0.15 | AL133163.2 | 1.49 | −0.51 | −1.70 | 0.56 | −0.31 | AL590002.1 | 0.38 | −0.76 | 0.46 | −1.60 | 1.49 |
| PICART1 | −0.89 | 0.65 | 0.25 | 0.53 | 0.52 | RN7SL351P | 0.53 | −0.53 | 0.53 | −0.54 | 0.41 | PABPC1P4 | 0.08 | −0.32 | 0.73 | −0.25 | 0.42 |
| EHD4-AS1 | 1.08 | −0.50 | −1.63 | −0.60 | −1.21 | AP001042.1 | 1.42 | −1.15 | −1.38 | 0.22 | 0.16 | AC004884.1 | −0.14 | 0.52 | 0.03 | 0.02 | −0.16 |
| AL139317.5 | −0.92 | 0.21 | 0.91 | −0.14 | 0.11 | FOCAD | 0.09 | −0.03 | 0.05 | 0.01 | 0.05 | EPHB3 | 0.05 | 0.42 | −0.04 | 0.17 | −0.07 |
| CEPT1 | 0.43 | −0.14 | −0.28 | 0.06 | −0.09 | AL133384.1 | 0.47 | 0.68 | −0.11 | −0.10 | −0.27 | SLC13A1 | 0.19 | 0.38 | −0.88 | 0.83 | −0.60 |
| RN7SL603P | −2.22 | 2.99 | 1.28 | 2.07 | 0.20 | AC022079.2 | −0.53 | −0.39 | 0.52 | −0.06 | 0.78 | BX890604.2 | 0.05 | 0.06 | 0.18 | 0.28 | 0.34 |
| AC008543.1 | −0.73 | 0.40 | 1.02 | 0.32 | 0.45 | AP001767.3 | −0.65 | 0.05 | 1.31 | 0.85 | 0.82 | RNU6-672P | 0.34 | −0.82 | −0.39 | −0.04 | −0.04 |
| ADPRHL2 | 0.48 | −0.28 | −0.59 | −0.08 | −0.31 | FAM102A | −0.18 | 0.38 | 0.37 | 0.25 | 0.04 | AC116562.1 | −0.13 | 0.11 | 1.55 | 0.29 | 1.08 |
| AC138089.1 | −3.16 | −1.07 | 0.99 | −1.84 | 0.33 | IRGC | −1.29 | −0.97 | 0.27 | −0.33 | 0.34 | AC005544.1 | 0.45 | −0.71 | −0.92 | 0.00 | −0.03 |
| SHROOM3 | −0.92 | 0.60 | 1.14 | 0.05 | 0.32 | NDUFS2 | 0.09 | −0.04 | −0.10 | 0.00 | 0.01 | AL627309.2 | 0.23 | −0.21 | −1.06 | 1.04 | 0.19 |
| AC002401.2 | −1.27 | 1.24 | 0.78 | 0.74 | −0.03 | MIR3142HG | −0.34 | −0.28 | 0.47 | −0.24 | 0.47 | DUXAP2 | 0.45 | −1.35 | −0.45 | −0.19 | 0.57 |
| CES1P1 | −1.57 | 1.39 | 0.98 | 0.83 | −0.02 | AL132875.2 | 1.07 | 0.28 | −2.38 | 0.00 | −2.00 | AC006205.2 | −0.16 | 1.32 | 0.39 | −0.05 | −1.95 |
| RNU4-25P | 2.06 | −1.13 | −1.15 | −0.14 | 0.25 | LINC02234 | −0.91 | −0.88 | 0.35 | −0.20 | 1.38 | AC104689.1 | 0.37 | −1.42 | −1.20 | 0.18 | 0.21 |
| EZH2 | 0.45 | −0.28 | −0.38 | −0.03 | −0.08 | PAQR6 | −0.35 | 0.32 | −0.01 | 0.44 | 0.16 | FAM96AP1 | −0.32 | −0.39 | 0.54 | −0.46 | 0.63 |
| AC007362.1 | 1.10 | −1.03 | −0.57 | −0.16 | 0.03 | RN7SL18P | −1.05 | 0.02 | −1.31 | 2.06 | −0.08 | RPS3AP36 | −0.18 | −0.73 | −0.41 | 0.07 | 0.66 |
| OR7E13P | 1.07 | −0.47 | −0.18 | −0.62 | 0.02 | CYP4F25P | −1.18 | 2.25 | −0.90 | 1.90 | −0.30 | MRPL50P4 | −0.31 | −2.14 | 0.64 | −0.21 | 3.65 |
| DUSP9 | 1.66 | −0.63 | −0.96 | 0.15 | −1.03 | CD200 | −0.29 | −0.06 | 0.59 | −0.53 | 0.32 | AC007998.1 | 0.81 | −1.31 | −1.08 | 0.56 | 0.80 |
| FARP1 | −0.60 | 0.38 | 0.59 | −0.19 | 0.04 | RNU6-665P | 0.76 | 0.14 | −1.02 | 0.40 | −0.09 | AC011997.1 | −0.24 | −0.11 | 1.80 | −0.43 | 1.42 |
| NR1D1 | −0.74 | 0.89 | 0.65 | 0.45 | −0.48 | AL022328.2 | −0.39 | 0.92 | −0.15 | 0.37 | −0.28 | AC108748.1 | −0.36 | −1.91 | 0.16 | −0.81 | 0.88 |
| NR1H3 | −0.72 | 0.22 | 0.28 | 0.38 | 0.23 | AC083964.2 | −0.26 | 0.24 | 0.27 | 0.05 | 0.35 | AP000229.1 | 0.17 | −0.75 | −0.49 | 0.24 | −0.06 |
| SPRYD7 | 0.38 | −0.06 | −0.36 | −0.02 | −0.08 | AL035417.2 | −1.32 | −0.03 | 1.53 | −0.57 | 1.89 | AL139349.1 | 0.12 | 0.41 | 0.11 | 0.36 | 0.07 |
| RARS2 | 0.29 | −0.15 | −0.16 | −0.11 | −0.09 | PAN3 | −0.10 | 0.19 | 0.04 | 0.17 | −0.08 | MS4A6E | 0.26 | −2.52 | −1.83 | −0.72 | −0.02 |
| LRP12 | 0.43 | −0.15 | −0.24 | −0.17 | −0.17 | RN7SL246P | 0.46 | −0.26 | −0.18 | −0.48 | −0.07 | AC243829.2 | 0.52 | −0.56 | 0.24 | 0.66 | 0.29 |
| AACS | −0.50 | 0.30 | 0.29 | 0.34 | 0.15 | AC074050.4 | 0.96 | 0.28 | 0.38 | 0.19 | 0.53 | AGAP7P | 0.13 | −0.97 | −0.16 | 0.85 | 1.67 |
| AC099521.2 | 1.70 | −0.94 | −0.63 | −0.10 | −0.25 | AL137003.2 | 0.30 | −0.48 | 0.14 | −0.28 | 0.33 | SDHCP1 | 0.34 | −0.91 | 1.20 | −0.95 | 2.53 |
| SRBD1 | 0.40 | −0.35 | −0.21 | −0.29 | 0.03 | EIF5P1 | 0.53 | −0.87 | −1.05 | 0.22 | 0.07 | LINC01176 | −0.04 | 0.17 | 0.20 | 0.25 | 0.26 |
| AKT3 | −0.66 | 0.33 | 0.88 | −0.10 | 0.08 | RNU6-968P | 1.68 | −0.55 | −1.33 | −0.64 | −0.87 | AC011840.2 | −0.23 | −0.83 | 0.32 | 0.99 | 2.17 |
| ENKD1 | −0.50 | 0.19 | −0.12 | 0.29 | 0.12 | AC087203.3 | −1.07 | 0.01 | 0.33 | 0.45 | 0.03 | AC084768.1 | 0.35 | −0.28 | 0.72 | 0.66 | 0.66 |
| FAM155B | 1.84 | −0.56 | −2.08 | −0.22 | −0.86 | RNU7-170P | 1.31 | 0.03 | 0.79 | 0.96 | 1.89 | MTRNR2L11 | −0.30 | −0.15 | −0.11 | 1.07 | −0.04 |
| PRR14L | 0.32 | −0.13 | −0.15 | −0.25 | −0.13 | PTPRD-AS1 | −0.48 | −0.19 | −2.19 | −0.03 | −2.02 | AL132780.5 | −0.08 | −0.16 | 0.26 | −0.16 | 0.12 |
| LYSMD3 | 0.53 | −0.12 | −0.07 | −0.09 | −0.20 | ASHIL-IT1 | 0.32 | −0.43 | −0.46 | −0.30 | −0.22 | PDCL | 0.03 | 0.05 | 0.14 | −0.14 | −0.07 |
| MRPL50 | 0.56 | −0.32 | −0.44 | −0.38 | −0.38 | FAM204BP | 0.28 | −0.54 | −0.44 | −0.04 | 0.37 | CPS1 | −0.04 | 0.00 | 0.13 | −0.13 | −0.18 |
| SGPL1 | 0.47 | 0.00 | −0.22 | −0.08 | −0.34 | PRG2 | −0.46 | 0.58 | −0.89 | 0.36 | −1.09 | SAPCD2P3 | 0.12 | −0.54 | 0.11 | 0.16 | 0.85 |
| KLHDC4 | −0.57 | 0.12 | 0.04 | 0.20 | 0.17 | AC023595.1 | −1.54 | −1.20 | 1.93 | −1.82 | 1.87 | AL136115.3 | 0.27 | −0.16 | −0.02 | 0.08 | −1.01 |
| BTAF1 | −0.32 | 0.21 | 0.28 | 0.11 | 0.24 | AL512625.2 | −0.51 | 0.70 | 0.15 | 0.58 | −0.04 | D21S2088E | 0.29 | −1.46 | −0.66 | 0.10 | −0.18 |
| GSDMC | 0.79 | −0.56 | −0.84 | −0.03 | −0.01 | CCDC155 | −0.65 | −0.61 | 0.50 | −0.17 | 0.89 | RBMXP1 | −0.28 | −0.01 | −1.13 | 0.75 | −0.95 |
| QRSL1 | 0.44 | −0.25 | −0.21 | −0.09 | 0.02 | AL121574.1 | 0.79 | −1.73 | −1.42 | −0.01 | −0.23 | SNAP47 | 0.02 | 0.06 | −0.08 | −0.04 | −0.06 |
| FAM229B | −0.78 | 0.44 | 1.14 | −0.06 | 0.40 | AJ239322.1 | −0.57 | 0.56 | −0.12 | 0.83 | −0.19 | AC112203.1 | 0.19 | −0.93 | 0.67 | −0.27 | 0.63 |
| AL590666.4 | 1.37 | −0.66 | −0.57 | 0.17 | −0.12 | AL122016.1 | −1.64 | 0.40 | 1.41 | −0.38 | −0.72 | KRT8P11 | −0.20 | −1.12 | 0.94 | −0.87 | 1.68 |
| B9D1 | −0.63 | 0.67 | 1.02 | 0.13 | 0.15 | G2927 | −0.66 | 0.90 | 2.48 | 0.59 | 0.95 | RNU6-656P | −0.49 | 0.62 | 0.91 | 0.89 | 0.40 |
| AC010201.2 | −0.96 | 0.72 | 1.72 | −0.01 | 0.34 | LINC00112 | 0.79 | −0.27 | −0.49 | 0.40 | −0.64 | HOTTIP | −0.15 | −0.92 | −1.31 | −0.07 | −0.03 |
| LCOR | 0.28 | −0.08 | −0.15 | −0.08 | −0.14 | SNTN | −0.72 | 0.14 | 1.38 | 0.31 | 0.60 | AC073544.1 | −0.32 | −0.84 | −1.05 | 1.17 | 0.07 |
| LGALS7B | 1.03 | 0.11 | −0.78 | 0.56 | −0.93 | AL450322.1 | 1.09 | −0.25 | 0.55 | −0.82 | 0.20 | AC091614.1 | −0.21 | 0.10 | 1.46 | 1.18 | 0.18 |
| GOLGA5 | 0.41 | −0.19 | −0.32 | −0.13 | −0.21 | AC037479.1 | 0.39 | −0.49 | 0.15 | −0.06 | 0.61 | SIGLEC6 | −0.11 | −0.26 | 1.66 | −0.48 | 0.15 |
| ADIPOR1 | 0.38 | 0.00 | −0.50 | 0.02 | −0.56 | AF127577.3 | 0.68 | −1.19 | −0.18 | 0.11 | −0.18 | LINC01455 | −0.80 | 0.36 | 0.99 | −0.36 | −1.21 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| PIP5K1B | −1.00 | 0.67 | 0.72 | 0.47 | 0.37 | GJD3 | 0.84 | −0.34 | 0.97 | 0.04 | 0.64 | EEF1A1P26 | −0.25 | 0.15 | −1.99 | 0.78 | −2.05 |
| SCGB2A2 | −1.69 | 1.50 | 3.16 | −0.53 | 0.17 | AMD1P4 | 1.20 | −0.30 | −0.38 | −0.25 | 0.46 | LINC01594 | −0.20 | −0.14 | −0.38 | −0.33 | −0.57 |
| SLC35E4 | 0.48 | −0.12 | −0.58 | −0.18 | −0.43 | STARD3NL | 0.20 | −0.20 | −0.15 | −0.26 | −0.23 | AL137847.1 | −0.13 | −0.29 | 1.00 | −0.59 | −0.23 |
| CASC15 | −0.75 | 0.26 | 1.06 | −0.21 | 0.33 | AC084855.1 | −1.75 | 0.60 | 1.33 | 1.67 | −0.61 | AC006329.2 | 0.82 | 0.24 | −2.44 | 0.79 | 0.96 |
| AC007919.1 | 1.88 | −0.94 | −0.98 | 0.07 | −0.39 | AL035696.3 | 1.54 | −0.95 | −1.79 | 0.74 | −1.98 | AGTR2 | −0.28 | −0.76 | −0.39 | 1.31 | −0.25 |
| DUSP23 | 0.49 | −0.04 | −0.17 | 0.11 | −0.26 | AC010136.1 | −0.46 | −0.21 | −1.26 | 0.45 | −0.03 | SIRPB2 | −0.07 | −0.48 | 0.05 | −0.33 | −0.27 |
| MFAP5 | −1.48 | 0.96 | 1.89 | 0.21 | −0.25 | RNU6-494P | 0.54 | 0.13 | −0.95 | 0.12 | −0.92 | AC018765.1 | −0.25 | −0.79 | 0.10 | 0.00 | 0.50 |
| DDX49 | 0.32 | −0.15 | −0.23 | 0.07 | −0.11 | HIST1H2APS5 | 0.89 | −0.68 | −0.76 | −0.42 | −0.55 | EIF4EBP1P1 | 0.12 | −0.04 | 0.38 | −0.29 | 0.27 |
| SEC11C | 0.62 | −0.25 | −0.02 | −0.33 | −0.05 | SNORD114-28 | 1.64 | −0.45 | 0.61 | −1.09 | −0.59 | MIR765 | 0.26 | −1.04 | −0.05 | −0.97 | −1.07 |
| GMFB | 0.60 | −0.40 | −0.55 | −0.31 | −0.38 | SCAPER | 0.13 | 0.00 | −0.28 | 0.14 | 0.04 | C13orf42 | 0.21 | −0.93 | −0.05 | −0.05 | 0.76 |
| PCDHGA11 | −0.57 | 0.26 | 0.46 | 0.25 | 0.25 | AC022166.2 | 1.00 | −0.98 | −0.40 | 0.46 | 0.72 | RN7SL454P | 0.25 | −0.67 | −1.16 | 0.78 | −1.71 |
| FXYD2 | −1.24 | 0.62 | 0.33 | 1.10 | 0.21 | DAPL1 | 0.36 | 0.79 | 0.91 | 0.46 | −0.59 | AC011767.1 | 0.25 | −1.14 | 1.18 | 0.28 | 0.81 |
| SETP14 | 0.77 | −0.54 | −0.70 | −0.05 | −0.09 | AKR1A1 | 0.11 | −0.14 | −0.02 | −0.03 | 0.06 | AC099535.1 | −0.25 | −0.84 | 0.85 | −1.27 | −0.08 |
| FASTKD5 | 0.38 | −0.20 | −0.13 | −0.10 | −0.16 | MIR3140 | 0.46 | −0.53 | −0.39 | −0.18 | −0.12 | RNU7-40P | 0.11 | 0.39 | 0.73 | −0.34 | 1.12 |
| RPL23AP7 | −0.53 | 0.30 | 0.65 | −0.14 | 0.10 | AL390726.3 | −1.61 | −0.29 | 0.58 | −0.41 | 1.85 | AL592309.2 | −0.28 | −0.99 | −1.76 | 0.34 | −0.55 |
| SLC5A2 | −1.18 | 0.28 | 1.58 | −0.03 | 0.64 | ALG1L13P | 0.34 | −0.31 | −0.54 | 0.24 | 0.19 | AKRID1P1 | −0.23 | −0.08 | −0.24 | −0.28 | −1.09 |
| PCDH11Y | −1.72 | 0.58 | 1.03 | 0.66 | 0.28 | LINC02461 | −0.94 | −0.73 | 0.85 | −0.58 | 0.20 | AL136298.2 | −0.13 | 0.51 | 0.40 | 0.21 | 0.84 |
| DGAT2L6 | −1.53 | 1.41 | 0.95 | 1.74 | 1.40 | AL135902.1 | −0.68 | 0.03 | 2.22 | 0.52 | 1.39 | AP001107.3 | 0.30 | −0.92 | −0.31 | −0.79 | 0.71 |
| R3HDM2 | −0.22 | 0.12 | 0.32 | −0.02 | 0.13 | AL589843.1 | −0.39 | −0.28 | 0.18 | 0.38 | 0.50 | IQCK | −0.04 | 0.08 | 0.04 | −0.04 | −0.14 |
| ABTB2 | −0.51 | 0.19 | 0.27 | −0.02 | 0.09 | AC007336.1 | 0.25 | −0.07 | 0.18 | −0.07 | 0.08 | ADH5P4 | −0.15 | −0.31 | −1.71 | 0.10 | −0.19 |
| PLCXD3 | −1.23 | 0.29 | 0.46 | 0.83 | −0.55 | OR52I1 | −0.45 | 0.10 | 1.00 | 0.10 | −0.26 | AC242022.1 | −0.34 | 0.24 | −0.86 | 1.41 | 0.33 |
| CREBBP | −0.16 | 0.22 | −0.03 | 0.08 | −0.16 | ADAMTS7P3 | 0.43 | 0.80 | −0.33 | 0.50 | −0.82 | LINC02401 | −0.20 | −0.22 | −1.34 | 0.21 | −0.97 |
| RND2 | −0.76 | 0.61 | 1.04 | 0.32 | 0.30 | CNTD1 | 0.28 | −0.06 | −0.03 | 0.11 | −0.01 | GAS2L1P2 | 0.32 | −0.94 | −0.66 | 0.59 | 1.19 |
| AC105398.1 | −2.08 | 2.16 | 1.00 | 1.34 | 0.40 | AC138696.2 | 0.72 | −0.22 | −0.44 | 0.32 | 0.27 | AC024149.1 | 0.33 | −1.98 | −0.92 | −1.45 | 0.97 |
| AL121890.4 | −1.65 | 0.05 | 0.61 | 0.97 | 0.32 | AC087623.1 | −0.53 | 0.61 | 1.50 | −0.32 | 0.54 | SORT1 | −0.06 | 0.33 | 0.25 | −0.03 | −0.43 |
| EHBP1L1 | 0.45 | −0.49 | −0.78 | −0.18 | 0.01 | RSL24D1P1 | 0.87 | 0.81 | −0.68 | 1.26 | −0.66 | AC104841.1 | −0.10 | 0.35 | 0.44 | 0.01 | −0.06 |
| SRP14-AS1 | −0.74 | 0.22 | 0.93 | −0.30 | 0.07 | NDUFAF3 | −0.18 | 0.22 | 0.07 | 0.10 | −0.02 | BMS1P15 | −0.15 | −0.13 | 0.87 | 0.15 | 1.10 |
| PDGFRL | −1.00 | 1.21 | 2.40 | −0.41 | −0.34 | FAM81A | −0.26 | 0.07 | 0.00 | 0.11 | 0.13 | AL138881.1 | −0.36 | −0.33 | 1.22 | −0.34 | −0.83 |
| BAKIP1 | −1.30 | 0.85 | 1.48 | 0.42 | 0.74 | IL4 | −0.73 | −0.15 | −0.87 | −0.72 | −0.72 | SAMM50P1 | −0.10 | −0.08 | 0.57 | −0.04 | 0.55 |
| PKP1 | 0.85 | −0.02 | −0.63 | 0.18 | −0.52 | RNU7-59P | 0.83 | −0.01 | −0.80 | −0.18 | −1.39 | KLK3 | 0.21 | −0.44 | −0.07 | −0.28 | −1.11 |
| AC009061.2 | −0.79 | 0.17 | 0.96 | −0.10 | 0.41 | CRYBA1 | 0.38 | −0.27 | −0.35 | 0.10 | −0.12 | AP001574.1 | −0.13 | −0.05 | 0.94 | 0.26 | 0.30 |
| AL031722.1 | −1.21 | 0.59 | 0.86 | −0.25 | 0.39 | AC016397.1 | 1.07 | −0.95 | 1.62 | −1.37 | 1.83 | HBM | −0.81 | 1.53 | 0.37 | 0.05 | −3.06 |
| RPS12 | 0.59 | −0.01 | −0.10 | −0.01 | −0.41 | LINC01184 | −0.11 | 0.18 | 0.27 | 0.28 | 0.32 | G7038 | −0.12 | −0.01 | −0.32 | 0.10 | 0.23 |
| IMPDH1P5 | −0.79 | 0.31 | −0.25 | 0.54 | 0.29 | OR2L3 | 0.78 | −2.80 | −2.14 | 0.37 | 0.48 | RPL23AP67 | 0.16 | 0.29 | −0.75 | −0.30 | −1.30 |
| MS4A4E | −0.86 | 0.28 | 1.30 | 0.48 | 0.52 | RN7SL414P | 0.55 | −0.05 | −0.38 | −0.19 | −0.61 | OR11H2 | −1.02 | 0.36 | −1.00 | 0.40 | −1.33 |
| SLTM | 0.32 | −0.15 | −0.32 | −0.09 | −0.11 | AL606534.2 | 0.55 | −0.65 | 0.14 | −0.12 | 0.31 | AL391152.1 | −0.19 | 0.25 | −1.65 | 0.72 | −1.48 |
| GLMN | 0.53 | −0.18 | −0.43 | −0.01 | −0.23 | AC091212.1 | −1.01 | 0.97 | 0.24 | −0.11 | −0.60 | MYL7 | 0.36 | −0.61 | 0.24 | −0.63 | 0.03 |
| AP002453.1 | 1.49 | −0.83 | −0.67 | −0.33 | −0.72 | MPLKIP | 0.13 | −0.12 | 0.01 | −0.23 | −0.10 | AC016868.1 | −0.66 | 1.14 | −0.40 | 0.77 | 0.74 |
| RNU6-522P | 0.99 | −0.29 | −0.71 | 0.15 | −0.20 | SATB1-AS1 | 0.46 | −0.89 | −0.99 | 0.04 | −0.09 | AC009097.4 | 0.12 | −0.13 | 0.64 | −0.21 | 0.28 |
| HYLS1 | 0.62 | −0.41 | −0.92 | 0.01 | −0.33 | MPST | −0.14 | 0.16 | 0.06 | 0.14 | −0.03 | AL161631.1 | −0.55 | 0.53 | −2.04 | −0.77 | −1.80 |
| AL079343.1 | −1.55 | 1.39 | 1.22 | 0.90 | −0.06 | AC006116.8 | −0.69 | −0.38 | −0.09 | −0.52 | 1.08 | AL121832.1 | 0.42 | −0.51 | 2.05 | −0.87 | 0.45 |
| SP110 | 0.44 | −0.44 | −0.52 | −0.26 | −0.09 | ITIH6 | −0.46 | −0.23 | 0.74 | −0.42 | −0.13 | AL078604.3 | 0.40 | 1.04 | −1.43 | 1.08 | −1.88 |
| RNF111 | 0.22 | 0.02 | −0.19 | 0.00 | −0.16 | HDAC8 | 0.11 | −0.10 | −0.04 | 0.00 | 0.06 | HMGB1P45 | 0.41 | −1.68 | 0.19 | −1.19 | 0.11 |
| CASP7 | 0.50 | −0.45 | −0.58 | −0.27 | −0.22 | AC093107.2 | −0.54 | −0.68 | 0.05 | 0.15 | −0.30 | AC114737.1 | 0.10 | −0.31 | 0.46 | −0.08 | 0.56 |
| RNF11 | 0.63 | −0.07 | −0.62 | 0.12 | −0.57 | AC253576.2 | −0.53 | 0.40 | 1.29 | −0.37 | −0.09 | LINC02349 | 0.30 | −0.96 | −1.05 | −0.02 | −1.05 |
| GUF1 | 0.48 | −0.24 | −0.27 | −0.07 | −0.05 | ACOX1 | −0.15 | 0.16 | 0.13 | 0.10 | −0.07 | AC004593.2 | 0.12 | −0.08 | 0.37 | −0.44 | 0.03 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| PIK3R4 | 0.35 | −0.02 | −0.22 | 0.06 | −0.14 | GLYCTK | 0.24 | −0.31 | −0.39 | 0.41 | 0.39 | IGHV3-23 | 0.28 | 1.78 | 2.94 | −0.40 | −2.08 |
| RNY5 | −1.22 | 0.72 | 0.60 | 0.57 | −0.28 | ACTL10 | 0.21 | −0.04 | −0.46 | 0.25 | 0.02 | AC233280.2 | 0.13 | 0.37 | −0.71 | 0.18 | −0.26 |
| LINC00641 | 0.56 | −0.14 | −0.32 | −0.08 | −0.21 | AC008494.3 | 0.65 | −0.55 | 0.55 | −0.33 | 0.24 | MIR4292 | −0.12 | 0.44 | 0.74 | 0.29 | 0.56 |
| AC015878.2 | −2.66 | 1.09 | 1.57 | 1.34 | −0.64 | C2orf76 | −0.20 | 0.36 | 0.44 | −0.01 | 0.03 | MIR5697 | −0.13 | −0.06 | 0.79 | −0.36 | 0.01 |
| AC011389.1 | −0.82 | 0.61 | 0.85 | 0.11 | −0.02 | RBMXP2 | −0.44 | 0.92 | −1.25 | 0.43 | −1.11 | AC005908.2 | 0.53 | −0.74 | −0.55 | 1.22 | −0.16 |
| ATP1A1 | 0.68 | −0.25 | −0.50 | −0.15 | −0.03 | FGL2 | −0.27 | 0.21 | 0.56 | −0.02 | 0.31 | HLA-H | −0.05 | −0.28 | −0.15 | −0.10 | 0.04 |
| DISP2 | −1.10 | 0.47 | 0.49 | 0.35 | −0.62 | MAP3K8 | 0.18 | −0.15 | −0.29 | −0.13 | −0.56 | AC106707.1 | 0.27 | −1.35 | −0.35 | −0.69 | −0.92 |
| CPAMD8 | −0.99 | 0.35 | −0.16 | 0.37 | −0.23 | LRRC75A | 0.19 | −0.18 | −0.09 | −0.11 | 0.14 | GML | 0.57 | −1.49 | −0.86 | 0.62 | 0.09 |
| LINC02067 | −1.36 | 1.18 | 1.48 | 0.71 | −0.33 | GPR88 | −1.00 | 0.17 | −0.67 | 0.97 | −1.68 | AC110768.2 | −0.33 | −0.06 | 0.85 | 0.09 | 1.01 |
| RN7SL80P | −1.28 | −0.01 | −0.43 | 1.18 | 0.91 | RTEL1 | −0.22 | −0.16 | 0.33 | −0.07 | 0.31 | PLXNC1 | 0.05 | −0.26 | 0.02 | −0.42 | −0.04 |
| AC007638.2 | −1.07 | 0.89 | 0.92 | 0.55 | 0.01 | LIPT1P1 | −0.81 | −0.68 | 1.30 | −0.29 | 1.58 | FALEC | 0.09 | 0.65 | 0.43 | 0.07 | −0.18 |
| COLQ | −0.65 | 0.10 | 0.43 | 0.06 | 0.47 | LRIG2 | −0.11 | 0.10 | 0.12 | 0.06 | 0.07 | PTCRA | 0.30 | −0.55 | −1.21 | −0.22 | 0.50 |
| SPR | 0.84 | −0.56 | −0.72 | 0.09 | 0.01 | AL031651.2 | −0.68 | −0.66 | −0.19 | −0.02 | 0.47 | RGPD4 | −0.12 | −0.75 | 0.77 | −0.27 | 0.56 |
| SERPINB6 | 0.40 | −0.32 | −0.35 | −0.14 | −0.06 | RCOR2 | −0.26 | 0.20 | 0.05 | −0.03 | −0.06 | AC005224.2 | 0.28 | −1.49 | −0.24 | 0.35 | 1.18 |
| AP001642.1 | 1.19 | −0.84 | −0.46 | −0.39 | −0.15 | RN7SL188P | −0.62 | 0.31 | −0.53 | 0.69 | −0.05 | ANKRD30BP1 | 0.34 | −0.28 | −0.06 | 0.48 | 1.47 |
| MGC15885 | −1.48 | 0.72 | 0.63 | 0.58 | 0.23 | DUSP28 | −0.19 | 0.18 | 0.34 | 0.38 | 0.07 | AP000924.1 | −0.16 | −1.21 | −1.56 | 0.10 | 0.01 |
| SEL1L | 0.38 | 0.01 | −0.13 | −0.08 | −0.28 | AC007014.1 | 0.34 | 0.00 | 0.19 | −0.41 | 0.08 | NCRNA00250 | −0.47 | −0.17 | 0.68 | 0.73 | −1.82 |
| PSG9 | −1.40 | 0.23 | 0.84 | 0.22 | 0.90 | AC000089.1 | −0.34 | 0.68 | 0.31 | 0.65 | 0.18 | FDX1 | −0.04 | 0.00 | 0.31 | −0.08 | 0.25 |
| CEP295 | 0.36 | −0.36 | −0.33 | −0.20 | −0.02 | GTPBP1 | −0.14 | −0.02 | −0.40 | 0.10 | −0.12 | G42804 | −0.19 | −0.96 | 0.87 | −1.14 | 1.53 |
| GGT1 | −0.68 | 0.16 | 0.15 | 0.00 | 0.39 | DLG3 | 0.16 | 0.24 | 0.16 | 0.11 | −0.05 | PPIAP67 | −0.09 | −0.22 | −0.25 | −0.06 | 0.12 |
| RELT | 0.72 | −0.85 | −1.29 | −0.26 | −0.35 | CCDC173 | −0.28 | 0.10 | 0.12 | −0.07 | −0.30 | LINC00626 | −0.25 | −0.79 | −0.12 | 0.45 | 1.10 |
| AC005064.1 | −1.51 | 0.71 | 0.69 | 0.28 | 0.10 | AC008895.1 | 0.18 | 0.12 | −0.07 | 0.15 | −0.10 | ERICH4 | 0.12 | 0.86 | −0.71 | 0.30 | −0.80 |
| LUZP2 | −1.06 | 1.13 | 0.45 | 0.21 | −0.49 | AC013652.2 | 0.45 | 0.57 | −0.60 | 0.06 | −0.78 | AP005482.2 | −0.44 | 0.28 | 0.28 | 1.75 | 0.47 |
| CHD7 | 0.42 | −0.16 | −0.55 | 0.01 | −0.17 | REEP1 | 0.20 | 0.30 | −0.40 | 0.40 | −0.40 | RNU6-476P | 0.30 | 0.10 | 1.20 | −1.00 | −0.46 |
| HOXA10-AS | −1.05 | 0.52 | 0.64 | 0.08 | −0.06 | AC007952.2 | −0.52 | 0.41 | 1.32 | −0.16 | 0.51 | RN7SL648P | −0.06 | 0.00 | 0.39 | −0.01 | 0.17 |
| AP000866.1 | −0.77 | 0.45 | 0.39 | 0.08 | −0.07 | AC139722.1 | −0.87 | 1.20 | 0.67 | 0.46 | −0.82 | BNIP3P34 | −0.41 | −0.05 | −1.35 | 0.93 | −1.41 |
| CAPN6 | −1.21 | 1.35 | 1.33 | 0.18 | −0.15 | AL137005.2 | 1.65 | −0.66 | 0.34 | 0.70 | 1.26 | AL590085.1 | 0.14 | −0.58 | −0.29 | −0.36 | 1.47 |
| MRPL11 | 0.45 | −0.34 | −0.40 | −0.13 | −0.21 | AC092667.1 | −1.09 | −0.95 | 0.66 | −0.54 | −0.02 | AC098590.1 | 0.30 | −0.60 | −0.34 | 2.03 | −0.53 |
| AP000547.3 | −0.98 | 0.14 | 0.05 | 0.54 | 0.18 | RN7SL229P | −1.13 | −0.52 | −0.91 | 1.59 | 1.63 | AC009403.1 | −0.07 | −0.32 | 0.73 | −0.05 | 0.62 |
| AC091729.1 | −0.93 | 0.19 | 0.14 | −0.29 | 0.17 | RPS8P6 | −0.79 | −1.43 | −0.12 | −0.38 | 2.60 | AC105935.2 | 0.24 | 0.28 | −2.80 | −0.04 | −1.32 |
| AC074051.1 | −2.39 | 0.61 | 2.88 | −1.63 | 0.27 | KIR3DL2 | 1.02 | −1.09 | −0.28 | −0.34 | −0.09 | EEF1A1P21 | 0.42 | −0.01 | −2.26 | 2.03 | −1.03 |
| HRCT1 | −1.42 | 0.73 | 1.30 | 0.26 | −0.04 | AIPL1 | 0.93 | −0.54 | −1.38 | 0.70 | 0.56 | RNU1-69P | 0.31 | −0.98 | 0.21 | −0.01 | 0.55 |
| G6134 | −2.63 | 0.83 | 1.84 | 0.81 | 1.06 | APBB1IP | −0.39 | −0.10 | 0.38 | −0.26 | 0.22 | SEPHS2P1 | −0.45 | −0.72 | −0.61 | 0.94 | 0.17 |
| HBS1L | 0.30 | −0.05 | −0.09 | −0.11 | −0.08 | AC090695.1 | 0.33 | −0.09 | 0.11 | −0.27 | −0.48 | AC084030.1 | 0.37 | −0.56 | −0.87 | 0.20 | −0.90 |
| SMIM24 | −1.78 | 0.86 | 0.94 | 0.19 | −0.39 | FAM107B | −0.22 | −0.02 | 0.34 | −0.12 | −0.27 | SERF1AP1 | −0.38 | 0.10 | 0.75 | −0.05 | −0.74 |
| STK17B | 0.61 | −0.43 | −0.33 | −0.26 | −0.42 | INPP5E | −0.17 | −0.05 | −0.29 | 0.11 | 0.07 | AP001486.1 | −0.37 | −0.34 | −0.89 | 0.01 | −0.79 |
| AC115115.1 | −1.62 | 0.51 | 0.45 | 0.01 | −0.28 | LCE1A | −0.47 | 0.71 | 1.00 | 0.80 | −0.45 | HES1 | 0.04 | 0.21 | −0.05 | −0.15 | −0.32 |
| AC135983.4 | −1.41 | 0.23 | 0.77 | 0.11 | 0.18 | AC011753.4 | 0.43 | −0.14 | 0.58 | 0.06 | 0.38 | AL035078.2 | −0.36 | −0.36 | −2.28 | 0.72 | −2.80 |
| PDXDC1 | −0.19 | 0.13 | 0.12 | 0.10 | 0.09 | DOCK6 | −0.15 | 0.05 | −0.16 | 0.16 | 0.01 | NPSR1-AS1 | 0.17 | −0.45 | −1.19 | 0.08 | −0.12 |
| OTUB2 | 0.70 | −0.03 | −0.52 | 0.33 | −0.55 | AC007191.1 | 0.24 | −0.25 | −0.33 | −0.36 | −0.26 | AC010976.2 | 0.11 | −0.31 | −0.23 | −0.42 | −0.17 |
| AC068050.1 | −1.34 | 1.35 | 1.96 | 0.60 | 0.67 | RNASEL | −0.11 | −0.01 | 0.26 | −0.17 | 0.21 | AC009884.2 | 0.14 | −0.23 | 0.54 | −0.46 | 0.05 |
| MSI2 | −0.29 | 0.29 | −0.05 | 0.28 | 0.07 | AC007318.2 | −0.41 | 0.03 | 0.22 | −0.35 | −0.15 | KRT10 | 0.14 | 0.96 | 0.77 | 1.44 | −0.47 |
| SORBS3 | −0.54 | 0.33 | 0.31 | 0.19 | 0.00 | AL109955.1 | −0.62 | −0.14 | 0.03 | 0.03 | −0.14 | AC092811.1 | −0.07 | 0.19 | 0.02 | 0.30 | −0.31 |
| FOPNL | 0.51 | −0.16 | −0.25 | −0.08 | −0.28 | OR9A2 | −0.85 | 0.27 | −0.08 | 1.11 | 0.85 | MIR181A2HG | 0.06 | −0.05 | 0.41 | −0.05 | 0.14 |
| AP000755.2 | −1.82 | 0.56 | 2.07 | 0.21 | 0.53 | AC015909.5 | −0.31 | 0.09 | 0.26 | 0.34 | 0.45 | CDRT7 | −0.39 | −1.12 | 0.41 | −0.20 | 1.49 |
| STARD7 | 0.47 | −0.20 | −0.25 | −0.06 | −0.11 | NEMP1 | −0.19 | −0.03 | 0.16 | 0.03 | 0.23 | AP002008.3 | 0.24 | 0.94 | −0.52 | −0.39 | −0.79 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AL669831.1 | −0.78 | 0.01 | 0.19 | −0.02 | 0.35 | RN7SKP11 | 1.53 | 0.78 | −0.16 | 0.09 | 0.61 | SREBF2-AS1 | 0.06 | 0.33 | 0.03 | 0.53 | 0.19 |
| MPP7 | 0.71 | −0.07 | −0.42 | 0.21 | −0.43 | AC007614.1 | −0.60 | 0.57 | 0.14 | 0.39 | −0.47 | SDCCAG3P1 | 0.46 | 0.04 | −0.69 | −0.67 | −1.20 |
| GOLGA6L5P | −0.79 | 0.23 | 0.38 | 0.31 | 0.28 | AC084033.3 | −0.37 | 0.62 | 1.31 | 0.01 | 0.20 | RPSAP45 | 0.23 | −1.12 | −0.53 | −1.34 | −0.59 |
| AL513283.1 | −0.81 | 0.46 | 0.48 | 0.15 | 0.00 | AL031291.1 | −0.71 | 0.94 | 0.63 | 0.59 | 0.16 | AL353753.1 | −0.20 | 0.76 | −0.92 | 0.38 | −0.80 |
| PRRT2 | −0.77 | 0.20 | 0.75 | 0.12 | 0.52 | AP000785.2 | −1.06 | 1.05 | 1.38 | 0.24 | 0.27 | GGT3P | −0.16 | 1.12 | −0.07 | 0.56 | −0.11 |
| SMARCAD1 | 0.42 | −0.06 | −0.24 | 0.10 | −0.15 | LINC00457 | −0.86 | 0.38 | 0.45 | 0.77 | 1.16 | AL137792.1 | 0.18 | −1.15 | −1.71 | 0.53 | −0.18 |
| IBTK | 0.37 | −0.24 | −0.20 | −0.16 | 0.05 | AC012301.1 | 0.67 | −1.84 | −0.63 | −0.12 | 0.11 | CDH15 | −0.15 | −0.92 | −0.46 | −0.47 | −0.33 |
| MRPL9 | 0.38 | −0.11 | −0.47 | 0.06 | −0.32 | AMIGO2 | 0.28 | −0.59 | −0.29 | −0.02 | 0.12 | RN7SL404P | −0.34 | 0.18 | 1.05 | 0.92 | 1.98 |
| AL158201.1 | −1.06 | 0.76 | 1.55 | 0.38 | 0.46 | RNU6-1058P | −0.65 | 0.07 | −0.18 | 0.10 | −0.13 | OR4P4 | 0.37 | 0.86 | −1.90 | 0.73 | −1.98 |
| SNORD9 | −1.23 | 0.17 | 1.69 | −0.42 | 0.63 | SNORD113-2 | 0.61 | −0.07 | −0.37 | −0.41 | −0.26 | AP003072.5 | 0.07 | 0.17 | −0.32 | 0.01 | −0.46 |
| RNU6-1222P | 2.28 | −0.18 | −0.78 | −0.07 | −0.62 | B3GALT2 | 0.29 | 0.00 | 0.10 | −0.25 | −0.14 | AC010203.1 | −0.06 | −0.41 | 0.55 | 0.16 | 1.43 |
| MLF1 | −0.59 | 0.36 | 0.46 | −0.11 | −0.33 | RN7SL118P | −0.24 | 0.16 | 0.46 | −0.16 | 0.23 | GOLGA2P8 | −0.15 | 0.33 | 1.39 | −0.86 | 0.30 |
| AL589935.1 | −0.81 | 0.36 | 0.59 | −0.25 | 0.24 | GPR156 | −0.28 | 0.53 | −0.15 | 0.29 | −0.62 | AC098614.4 | 0.14 | −0.97 | −1.23 | 0.79 | 0.65 |
| RSF1-IT1 | −1.47 | −0.01 | 0.64 | 0.40 | 0.41 | ANKRD28 | 0.10 | 0.04 | −0.15 | −0.05 | −0.22 | DUX4L52 | 0.37 | −0.80 | −1.58 | 0.71 | 0.24 |
| RGMB-AS1 | −0.98 | 0.45 | 1.52 | 0.25 | 0.99 | G23966 | −0.64 | 0.77 | 1.02 | 0.14 | 0.02 | LINC02263 | 0.53 | −0.54 | −0.18 | −1.27 | −1.36 |
| RN7SL315P | −1.49 | 0.03 | 1.50 | −0.81 | 0.63 | AC008957.1 | 0.32 | −0.98 | 0.20 | 0.00 | 0.65 | AC007881.3 | −0.15 | 0.54 | 0.87 | 0.21 | −0.33 |
| COX4I1 | 0.43 | −0.06 | −0.32 | 0.02 | −0.31 | FMOD | −0.34 | 0.20 | 0.56 | −0.25 | −0.09 | RPL7P40 | 0.34 | −0.21 | −0.69 | 1.09 | −1.46 |
| MACROD2-IT1 | −1.19 | 0.81 | 0.91 | 0.54 | 0.39 | DNAJB3 | 0.54 | 0.31 | −0.09 | 0.89 | 0.97 | AL590639.1 | 0.11 | 0.67 | 0.26 | 0.25 | −0.48 |
| IQCH-AS1 | −0.41 | 0.16 | 0.51 | 0.11 | 0.48 | HLA-DOA | 0.34 | −0.35 | 0.09 | −0.30 | −0.10 | IFNA6 | 0.42 | −1.57 | −0.42 | 0.71 | 1.69 |
| BEND3P1 | −1.28 | 0.04 | 1.24 | 0.50 | 0.27 | RNA5SP60 | −0.90 | −0.36 | 0.68 | 1.26 | 0.24 | GAPDHP14 | −0.18 | 0.76 | 0.59 | −0.56 | −0.76 |
| MRFAP1 | 0.30 | −0.19 | −0.42 | −0.04 | −0.08 | G25498 | −0.56 | 0.91 | 0.63 | 0.09 | 0.61 | HNRNPA3P3 | 0.11 | −0.43 | −0.39 | −0.03 | −0.09 |
| POLR2L | 0.50 | −0.16 | −0.69 | −0.01 | −0.53 | LINC02198 | −0.61 | 1.17 | 0.20 | 0.21 | −0.82 | OR5P1P | −0.15 | 1.24 | 2.74 | 0.43 | 0.28 |
| PDHA1P1 | 1.11 | −0.58 | −0.90 | −0.39 | −0.53 | AC005699.1 | 0.71 | −0.35 | −2.01 | 0.58 | −0.15 | CTAGE10P | 0.24 | −1.48 | −2.17 | 0.50 | 0.41 |
| BRMS1 | 0.44 | −0.23 | −0.77 | 0.03 | −0.29 | AC009248.2 | 0.51 | 0.14 | −0.10 | −0.40 | −0.22 | RNU6-780P | −0.12 | −0.34 | 0.21 | −0.27 | 0.03 |
| KATNAL2 | −0.36 | 0.24 | 0.41 | −0.10 | 0.18 | RNU6-808P | 0.66 | −0.22 | 1.59 | −0.60 | 0.54 | HOXD1 | −0.19 | 0.14 | −0.50 | 0.09 | −1.36 |
| RN7SL524P | −1.70 | 0.50 | −0.53 | 0.37 | 0.28 | AL031667.2 | −0.40 | 0.10 | 0.02 | 0.24 | 0.16 | SLC6A5 | −0.17 | −0.21 | −1.99 | 0.65 | −1.47 |
| AC097375.1 | −1.34 | 0.48 | 2.15 | −0.06 | 1.04 | DHX16 | −0.13 | −0.05 | −0.11 | −0.10 | 0.08 | LINC02176 | −0.58 | 0.18 | −0.63 | −0.63 | −1.17 |
| LINC01712 | −2.11 | 0.81 | 1.61 | −0.05 | −0.50 | NUP35P1 | −0.93 | −0.96 | −0.49 | 0.87 | 0.57 | AL023283.1 | 0.20 | −0.04 | −1.24 | −0.21 | −1.06 |
| PVR | 0.55 | −0.36 | −0.73 | −0.19 | −0.16 | DDHD1 | 0.11 | 0.03 | 0.00 | 0.07 | −0.07 | MEI1 | 0.10 | −0.52 | −0.12 | −1.20 | −0.14 |
| G42257 | −2.30 | 1.13 | 1.33 | 1.12 | −0.33 | OR10N1P | −1.25 | 0.45 | −1.91 | 1.01 | −3.18 | AL354733.3 | 0.12 | 0.25 | 0.23 | −0.14 | −0.03 |
| CD101 | 0.61 | −0.55 | −0.87 | 0.03 | −0.32 | AL133227.1 | 0.31 | −0.30 | 0.49 | 0.01 | 0.45 | IGBP1-AS2 | −0.11 | 0.03 | 0.09 | −0.22 | −0.48 |
| SLC24A1 | −0.34 | 0.03 | 0.28 | 0.00 | 0.24 | SH2D7 | 0.56 | −1.51 | −0.73 | −0.93 | 0.58 | FP700111.2 | −0.19 | 1.02 | −0.28 | −0.11 | 0.27 |
| SLC22A18 | −0.60 | 0.40 | 0.64 | 0.30 | 0.21 | AL353692.1 | −0.35 | 0.01 | −0.89 | 0.25 | −0.88 | KRT18P42 | 0.46 | 0.29 | 0.21 | −0.20 | −1.99 |
| AL355483.2 | 2.01 | −0.99 | −2.05 | −0.24 | 0.18 | AC139495.1 | −0.53 | 0.02 | −0.60 | 0.50 | 0.16 | LPXN | −0.05 | −0.30 | −0.16 | −0.36 | −0.09 |
| KIF18B | 0.79 | −0.99 | −1.68 | −0.34 | −0.21 | AC005410.2 | −0.46 | 0.59 | 0.86 | 0.66 | 0.86 | CRP | 0.22 | −0.59 | −0.14 | 0.33 | 0.83 |
| RNF187 | 0.43 | 0.01 | −0.51 | 0.21 | −0.20 | RAB36 | 0.23 | 0.09 | −0.12 | 0.12 | −0.08 | AC009088.1 | 0.07 | −0.37 | 0.10 | −0.02 | 0.61 |
| ARID1A | 0.31 | −0.17 | −0.27 | −0.03 | −0.06 | AC020910.1 | −0.58 | −0.13 | −0.40 | 0.70 | 0.21 | RBCK1 | 0.02 | −0.07 | −0.20 | −0.03 | 0.02 |
| PRELID2 | −0.54 | 0.11 | 0.36 | 0.04 | 0.19 | LINC02166 | 0.52 | −0.81 | −0.29 | −0.71 | 0.37 | AC025419.1 | 0.14 | 0.16 | −0.19 | 0.00 | 0.39 |
| C11orf58 | 0.36 | −0.18 | −0.16 | −0.15 | −0.15 | ASPHD1 | 0.49 | −0.84 | −0.49 | −0.99 | 0.32 | RNU6-34P | −0.43 | −0.26 | 0.63 | 0.11 | 1.06 |
| AC092881.1 | 0.55 | −0.23 | −0.17 | −0.13 | 0.04 | RNA5SP246 | −0.53 | −0.36 | 0.47 | 0.04 | 0.74 | AC114786.1 | 0.55 | −0.87 | 0.65 | −0.72 | −0.53 |
| EXTL1 | −1.29 | 0.90 | 0.82 | 0.74 | 0.45 | KRT81 | −0.70 | 0.25 | 1.12 | −0.05 | 1.18 | LINC01799 | 0.30 | −1.17 | −1.14 | 1.38 | −0.08 |
| MIR3118-1 | −2.22 | 1.23 | 0.81 | 1.86 | 1.91 | G26738 | 0.48 | 0.25 | −0.82 | 0.27 | −0.58 | GUSBP4 | −0.15 | −0.86 | 0.56 | 0.22 | 1.36 |
| RNASEH2C | −0.35 | 0.11 | 0.28 | 0.02 | 0.03 | AC073415.1 | −0.57 | 0.15 | 0.75 | 0.15 | 0.32 | NAA30 | 0.03 | 0.14 | 0.23 | −0.03 | −0.06 |
| LINC00854 | −0.83 | −0.10 | 0.16 | 0.06 | 0.24 | RPS24P12 | −0.47 | 0.07 | 0.18 | −0.52 | 0.05 | CXorf36 | 0.06 | −0.03 | 0.83 | −0.23 | 0.11 |
| PLA2R1 | −0.67 | 0.53 | 0.79 | 0.20 | 0.48 | IKZF2 | −0.19 | 0.07 | 0.10 | 0.23 | 0.09 | ROPN1L | 0.13 | −0.36 | 0.05 | −0.26 | −0.01 |
| EXOC8 | 0.31 | 0.04 | −0.18 | 0.02 | −0.34 | AC097468.2 | −1.03 | −0.11 | −1.22 | −0.26 | −0.14 | OR5G1P | 0.43 | −1.62 | −0.18 | −0.68 | 1.50 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC108010.1 | −0.48 | 0.19 | 0.25 | 0.10 | 0.01 | AL359845.1 | −1.04 | −1.49 | 1.70 | 1.45 | 2.20 | MAGEA4-AS1 | 0.42 | −0.43 | −1.21 | −0.29 | −0.82 |
| GAMT | −0.84 | 0.79 | 1.03 | 0.73 | 0.28 | MT-CO3 | −0.22 | 0.17 | 0.19 | 0.05 | 0.08 | AC046158.2 | 0.07 | −0.21 | 0.33 | 0.01 | 0.12 |
| RN7SL134P | −1.80 | −0.04 | 2.06 | 0.05 | 0.41 | C6orf47 | 0.16 | 0.02 | −0.08 | −0.03 | −0.09 | AL645465.1 | 0.41 | −0.07 | 0.71 | 1.32 | 0.72 |
| C16orf87 | 0.54 | −0.43 | −0.32 | −0.08 | 0.00 | NR2C2AP | 0.18 | −0.24 | −0.37 | −0.01 | −0.07 | EDRF1-AS1 | 0.05 | −0.16 | −0.07 | −0.06 | 0.08 |
| ADORA1 | −1.08 | 0.46 | 0.96 | 0.09 | 0.39 | MIR3683 | −1.92 | 1.37 | 1.52 | 0.27 | −0.04 | ICE2P2 | 0.40 | −0.10 | −2.02 | 0.70 | 0.09 |
| AC012158.1 | 1.19 | −0.34 | −0.37 | 0.22 | −0.35 | GRK2 | −0.13 | −0.08 | −0.23 | −0.01 | 0.02 | SLC2A3P4 | −0.06 | −0.22 | 0.07 | 0.01 | 0.20 |
| AC104986.2 | −0.73 | 0.34 | 1.12 | −0.04 | 0.51 | MIR4999 | 0.91 | −0.18 | −0.81 | 0.30 | 0.45 | MIR125B2 | 0.09 | 0.98 | 0.15 | 0.24 | −0.71 |
| MT1E | 0.88 | −0.80 | −0.13 | −0.53 | −0.10 | AC007278.2 | 0.60 | −0.07 | 0.52 | −0.27 | −0.10 | OR8X1P | 0.53 | −0.86 | −0.58 | 2.21 | 1.60 |
| AL136982.3 | −0.57 | −0.20 | 0.27 | 0.06 | 0.64 | RRM1-AS1 | 0.84 | −0.60 | −0.83 | 0.31 | 0.23 | CD99 | −0.22 | −0.32 | 0.99 | −0.04 | −1.27 |
| LINC02232 | −1.46 | 0.71 | 2.11 | −0.17 | 0.31 | SHCBP1L | −0.68 | −0.26 | 0.39 | 0.10 | −1.58 | ATP5F1AP4 | 0.27 | −0.97 | −2.49 | 0.64 | −1.31 |
| RN7SL430P | 1.17 | −0.56 | −0.34 | −0.35 | 0.14 | CHODL-AS1 | −0.45 | 0.09 | −0.11 | 0.32 | 0.39 | AC022509.1 | 0.17 | −0.48 | 0.05 | −0.20 | 0.12 |
| OR5BK1P | −0.66 | 0.32 | 0.88 | 0.26 | 0.67 | AC136475.5 | −0.71 | −0.11 | 0.58 | −1.00 | 0.92 | SOCS2-AS1 | −0.10 | −0.08 | 0.51 | −0.49 | 0.41 |
| AL078590.2 | 1.65 | −0.62 | −0.89 | −0.04 | 0.03 | RNU6-998P | 0.49 | −0.18 | −0.59 | 0.27 | −0.26 | AL356309.3 | −0.25 | −0.42 | −1.11 | 0.71 | 0.08 |
| AF067845.2 | 1.34 | −0.78 | −2.00 | 0.17 | −0.55 | AP002793.1 | 1.27 | −0.66 | −1.55 | 1.02 | −1.25 | LINC02484 | 0.41 | −1.20 | 0.02 | −1.29 | 0.48 |
| LINC02284 | −1.15 | 0.12 | 0.81 | 0.53 | −0.52 | BASP1P1 | −1.04 | −0.81 | 1.58 | −1.89 | −0.04 | AC133919.3 | 0.23 | −1.28 | 0.28 | 0.26 | 1.41 |
| CSRNP2 | −0.32 | 0.03 | 0.35 | −0.06 | 0.21 | FCGR1CP | 1.16 | −1.48 | 1.62 | −0.50 | 1.41 | AC009784.1 | 0.47 | −0.88 | 0.56 | −1.14 | −0.09 |
| P3H2-AS1 | −1.49 | 0.00 | −0.16 | 0.17 | 0.26 | METTL14 | 0.09 | 0.01 | 0.05 | −0.05 | −0.06 | AC084116.2 | 0.25 | −1.19 | −0.37 | 0.90 | −0.54 |
| AKAP5 | −0.56 | −0.12 | 0.40 | 0.04 | 0.41 | SNORA38 | −0.43 | 0.19 | −0.33 | 0.98 | 0.29 | DCAF8L1 | −0.24 | 0.31 | −0.95 | −0.16 | −1.77 |
| LINC01839 | −1.45 | 1.34 | 1.96 | 1.05 | 0.48 | RNU6-658P | 0.73 | 0.20 | −0.94 | 0.05 | −0.56 | AC007861.1 | 0.50 | −0.70 | 1.02 | −1.58 | −0.31 |
| KIRREL3 | −0.69 | 0.00 | −0.12 | 0.15 | −0.02 | AL513475.2 | 0.46 | −0.13 | −0.01 | 0.01 | −0.07 | C1DP5 | 0.43 | −1.32 | 1.14 | −0.13 | 1.48 |
| C20orf96 | −0.69 | 0.37 | 0.55 | 0.02 | 0.04 | DCUN1D2-AS | −0.32 | 0.10 | −0.65 | 0.48 | −0.02 | AL121895.2 | 0.19 | −0.55 | −1.06 | 0.32 | −0.26 |
| ADRA1B | −1.64 | 0.95 | 0.89 | 0.33 | −0.23 | FAM187B2P | 1.04 | −0.49 | 1.79 | −0.09 | 1.82 | AL132712.1 | −0.15 | 1.19 | −1.17 | 0.09 | −2.14 |
| RPS6KA1 | 0.49 | −0.37 | −0.80 | 0.04 | −0.07 | IL27 | 0.65 | −0.56 | 0.15 | −0.42 | 0.15 | AP000787.2 | 0.11 | 0.31 | 0.43 | −0.17 | −0.19 |
| COG3 | 0.27 | −0.11 | −0.23 | −0.14 | −0.10 | AL512791.1 | 0.25 | −0.50 | −0.23 | −0.14 | 0.24 | AL359233.1 | −0.60 | −0.47 | 1.75 | −0.81 | 1.17 |
| AC092332.1 | 1.42 | −0.79 | −1.50 | 0.00 | −0.65 | AL157392.1 | −0.55 | 0.42 | −0.08 | −0.21 | −0.13 | AC008735.4 | −0.07 | −0.06 | −0.33 | −0.14 | −0.11 |
| CNTN4-AS2 | −2.29 | 1.98 | 2.63 | −0.54 | 0.27 | MUC1 | −0.34 | 0.02 | −0.38 | 0.28 | 0.45 | AL138807.1 | 0.18 | 0.13 | −0.27 | −0.26 | −1.36 |
| LSR | 0.49 | 0.02 | −0.63 | 0.20 | −0.26 | ALG1L6P | −0.37 | 0.23 | 0.39 | 0.27 | 0.55 | AL354676.1 | −1.00 | 0.77 | 0.27 | 1.50 | −0.35 |
| DNHD1 | −0.38 | 0.10 | 0.22 | 0.07 | 0.13 | A2ML1-AS2 | −0.46 | 0.20 | 0.73 | −0.17 | 0.27 | RN7SL298P | 0.17 | −1.56 | −1.35 | −0.97 | −0.94 |
| RN7SL227P | −1.07 | 0.06 | 0.84 | −0.24 | 0.37 | AL441964.1 | −0.95 | −0.81 | 2.05 | 1.24 | 0.86 | LINC00284 | −0.18 | −0.35 | −0.61 | 0.91 | 1.00 |
| ARMC1 | 0.41 | −0.22 | −0.29 | −0.09 | −0.11 | AC106785.2 | −0.88 | −0.92 | 0.81 | −0.39 | 0.84 | LCE2A | −0.11 | 0.32 | 0.86 | 0.07 | −0.73 |
| AC073389.1 | −0.70 | −0.36 | 0.16 | 0.21 | 0.69 | LINC00501 | −0.75 | 0.11 | 1.05 | 1.18 | 1.19 | KRT18P55 | −0.29 | −0.49 | −0.12 | −0.81 | −2.13 |
| KCNU1 | −1.54 | 0.56 | 0.92 | 0.29 | 0.09 | EIF3FP3 | 0.37 | −0.18 | −0.08 | −0.20 | −0.49 | AC025917.1 | 0.07 | 0.10 | 0.41 | 0.26 | −0.07 |
| AC011586.1 | −2.29 | 1.56 | 1.39 | −0.14 | −0.52 | AC007370.1 | −0.65 | 0.55 | −1.03 | 0.15 | −0.97 | PSMC1P8 | −0.31 | −0.07 | −0.97 | 0.14 | −2.25 |
| MEGF8 | −0.35 | 0.11 | 0.14 | 0.20 | 0.25 | ATG10-IT1 | −0.50 | −0.56 | 0.28 | 0.03 | 1.09 | RAD17P2 | 0.06 | −0.34 | −0.22 | 0.07 | 0.31 |
| OR5BA1P | 0.88 | −0.61 | −1.07 | −0.17 | −0.10 | GJC1 | 0.29 | −0.16 | −0.20 | −0.01 | −0.43 | CRADD | 0.03 | 0.11 | 0.05 | 0.14 | 0.08 |
| MRTFB | −0.26 | 0.19 | 0.40 | 0.08 | 0.07 | AC018644.1 | 0.29 | −0.28 | −0.72 | −0.36 | −0.38 | AL513185.2 | 0.21 | −1.04 | 0.94 | −0.63 | −0.41 |
| HMGN2P23 | 3.12 | −0.19 | −1.53 | −1.04 | −1.42 | LINC01182 | −0.82 | 0.47 | −1.36 | 0.65 | 0.20 | AC099782.1 | −0.23 | 1.10 | −0.69 | 0.83 | −1.97 |
| AL008718.3 | 1.71 | −0.92 | −1.60 | 0.10 | −0.77 | FOXB2 | −0.78 | 0.30 | −1.07 | 0.68 | 0.33 | AC016773.1 | 0.10 | 0.56 | 0.31 | 0.64 | 0.12 |
| HSD17B14 | −1.09 | 0.28 | 1.05 | −0.14 | 0.39 | IGLC3 | 1.32 | 0.38 | 0.89 | −0.20 | −1.68 | AC092132.2 | 0.39 | −0.60 | −0.65 | 0.24 | −0.20 |
| NDUFA12 | 0.57 | −0.03 | −0.32 | 0.09 | −0.44 | RTN4R | 0.33 | 0.30 | −0.46 | 0.16 | −0.61 | AL033381.1 | −0.11 | 0.10 | −1.14 | 0.09 | −1.01 |
| LINC02237 | −2.13 | 1.18 | 0.34 | 0.72 | −0.29 | AC055764.2 | 0.51 | −0.18 | −0.74 | 0.03 | −0.46 | MIR3163 | 0.15 | −1.23 | 0.68 | −1.68 | 0.30 |
| ARL5A | 0.52 | −0.03 | 0.22 | 0.10 | −0.08 | AC007677.1 | −1.15 | −0.35 | 1.30 | −0.52 | 0.27 | AC025678.3 | 0.07 | −0.24 | −0.80 | −0.28 | −0.21 |
| AC024361.3 | −1.30 | 1.20 | −0.59 | 1.25 | −0.08 | PIGF | 0.18 | −0.16 | 0.28 | −0.13 | 0.15 | AL138921.1 | 0.09 | −0.27 | −0.55 | −0.41 | −0.22 |
| FBX09 | 0.28 | −0.18 | −0.36 | 0.09 | 0.05 | RBM15 | −0.14 | −0.09 | 0.00 | −0.02 | 0.20 | SLC9B1P2 | −0.26 | −0.75 | −0.48 | 0.11 | 0.90 |
| RHOT1P1 | −1.85 | 0.25 | 1.26 | −0.82 | 0.15 | RPA4 | −0.28 | −0.09 | 0.21 | 0.13 | 0.13 | CDK2AP2P2 | −0.35 | 1.80 | 2.47 | 1.20 | −0.53 |
| FLCN | −0.36 | 0.17 | 0.22 | 0.10 | 0.01 | AC007619.1 | 0.41 | −0.67 | 0.11 | 0.05 | 0.47 | AC087667.1 | 0.33 | −1.52 | −0.30 | −0.13 | 1.42 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| HMGCL | −0.38 | 0.08 | 0.44 | −0.10 | 0.20 | MAG | −0.71 | 0.37 | 0.18 | 0.88 | −0.08 | AC112694.1 | −0.08 | 0.02 | 0.57 | −0.02 | 0.43 |
| RTCA-AS1 | −0.77 | 0.41 | 1.13 | −0.01 | 0.34 | RYKP1 | 0.25 | −0.09 | −0.46 | 0.04 | −0.13 | FO393409.1 | 0.60 | 0.15 | −0.81 | 0.87 | −0.02 |
| LAMB2 | −0.55 | 0.52 | 0.52 | 0.17 | −0.02 | G34553 | 0.39 | −0.63 | 0.15 | −0.11 | 0.84 | AC036222.2 | 0.46 | 0.84 | 1.07 | −2.12 | −0.18 |
| FANCD2 | 0.55 | −0.58 | −0.85 | −0.23 | −0.29 | PHF19 | 0.13 | −0.36 | −0.36 | −0.17 | −0.01 | KLK12 | 0.14 | −1.02 | −0.86 | −1.04 | −0.52 |
| KIAA0895 | −0.59 | 0.34 | 0.23 | 0.33 | 0.10 | AC006499.7 | 0.75 | −1.18 | 0.02 | −0.59 | 0.34 | RN7SL610P | −0.11 | −1.19 | −0.55 | −0.55 | 0.51 |
| RNF207 | −0.77 | 0.32 | 0.18 | 0.14 | −0.03 | CRYL1 | 0.18 | −0.13 | −0.21 | −0.16 | −0.12 | NIPA2P5 | 0.80 | −0.68 | −1.67 | −1.50 | −1.00 |
| AL109659.2 | −1.26 | 0.75 | 1.02 | 0.52 | 0.14 | SRP14P2 | 0.38 | −0.71 | −0.69 | −0.38 | −0.36 | GTDC1 | −0.03 | 0.01 | 0.12 | −0.04 | −0.02 |
| G38700 | 1.21 | −0.28 | −2.10 | 0.32 | −0.88 | APOM | −0.21 | 0.08 | 0.27 | −0.09 | 0.14 | SNORD114-4 | 0.29 | −0.12 | 1.54 | −0.93 | −0.21 |
| LZIC | 0.45 | −0.10 | 0.00 | −0.14 | −0.06 | AC007285.2 | 0.43 | −0.02 | 0.35 | 0.02 | 0.07 | PGBD4P2 | 0.81 | −0.41 | −0.03 | −1.12 | −0.86 |
| G26248 | −1.26 | 0.26 | 2.03 | 0.01 | 0.88 | RNF152P1 | 0.33 | 0.08 | 0.09 | 0.41 | 0.55 | KRT18P34 | −0.11 | 0.06 | −1.24 | 0.81 | −0.03 |
| AC004951.1 | −0.74 | 0.21 | 0.64 | 0.14 | 0.63 | NEU1 | −0.14 | 0.05 | 0.27 | −0.21 | −0.01 | AC243654.1 | −0.15 | 0.30 | 0.53 | −0.15 | 0.12 |
| PSAT1 | 0.96 | −0.05 | −0.44 | 0.20 | −0.28 | LINC01307 | 1.16 | −0.89 | −1.60 | 0.47 | −0.82 | OR4A5 | −0.43 | 0.42 | 0.61 | 0.74 | 0.19 |
| AGFG1 | 0.39 | −0.15 | −0.47 | 0.01 | −0.34 | RPS6P22 | −0.41 | 0.36 | 0.53 | 0.48 | 0.41 | AC012181.1 | −0.14 | −0.16 | 0.89 | −0.69 | −0.27 |
| RAB1B | 0.39 | 0.04 | −0.54 | 0.10 | −0.58 | AC009152.1 | 0.39 | −0.59 | −0.49 | −0.39 | −0.31 | FAR2P3 | −0.88 | −0.41 | 0.25 | −2.42 | −0.84 |
| RNF115 | −0.30 | 0.10 | 0.32 | −0.04 | 0.16 | ERMN | 0.43 | −0.70 | −0.29 | −0.31 | 0.32 | AL136140.2 | 0.47 | 0.33 | −0.72 | 0.22 | −1.36 |
| MAP3K13 | −0.30 | 0.17 | 0.23 | 0.07 | 0.21 | MIR4718 | 0.85 | −1.32 | −0.12 | −0.74 | 0.18 | RNU7-52P | 0.61 | −1.09 | −1.47 | 2.36 | 1.82 |
| AC021979.2 | −2.16 | 0.03 | 0.89 | −0.54 | 0.21 | AC114491.1 | −0.84 | 0.42 | −1.10 | 2.55 | 0.05 | LINC02360 | 0.29 | −0.01 | −2.22 | −0.18 | −1.51 |
| DRICH1 | −0.85 | 0.41 | 0.31 | 0.24 | 0.40 | AL021408.2 | −1.12 | 1.45 | 1.38 | 0.79 | −1.03 | OR7A8P | 0.96 | −0.60 | −1.98 | 0.09 | −1.79 |
| CALHM6 | 2.11 | −1.08 | −1.37 | −0.45 | −0.05 | RNU6-895P | 0.64 | 0.09 | −1.02 | 0.04 | 0.27 | AL358075.3 | 0.19 | −0.68 | −1.86 | −0.18 | −0.39 |
| LMCD1-AS1 | −0.75 | 0.61 | 0.66 | 0.24 | −0.01 | SOSTDC1 | −0.38 | 0.71 | 1.08 | 0.25 | −0.02 | SNORA44 | −0.43 | 0.94 | 1.76 | −0.53 | −0.37 |
| C10orf143 | −0.72 | 0.18 | 1.15 | −0.24 | 0.33 | G26459 | −0.51 | 0.92 | 1.70 | −0.19 | −0.38 | C20orf78 | 0.39 | −0.15 | −0.21 | −0.12 | 0.55 |
| CHL1 | −0.80 | 0.97 | 1.02 | 0.14 | 0.18 | AC044860.1 | 0.45 | −0.40 | 0.55 | 0.22 | 0.44 | AC138907.10 | −0.61 | 0.06 | −0.10 | 0.31 | −2.06 |
| PIGP | −0.44 | 0.11 | 0.42 | 0.05 | 0.01 | DDX11L1 | −0.61 | 0.32 | 1.40 | 0.86 | 0.69 | AL591438.2 | −0.25 | −0.69 | 1.19 | −0.52 | 2.25 |
| AC243960.2 | 1.16 | −0.93 | −0.87 | −0.45 | −0.35 | RN7SL674P | −0.32 | 0.26 | −0.31 | 0.42 | −0.67 | AC092868.3 | 0.33 | 0.71 | −0.05 | 1.42 | −1.58 |
| GOT1 | 0.58 | −0.27 | −0.62 | −0.09 | −0.08 | RNVU1-10 | −0.95 | 0.74 | 1.02 | −0.21 | −1.12 | OR6N2 | 0.20 | −1.16 | −0.45 | −0.80 | −1.52 |
| SLC30A9 | 0.40 | −0.14 | −0.20 | −0.13 | −0.16 | P4HA3 | 0.26 | −0.34 | −0.13 | −0.56 | −0.33 | SCARNA16 | −0.10 | −0.32 | −0.70 | 0.14 | 0.07 |
| AC026150.2 | −1.33 | −0.27 | 0.89 | −0.34 | 0.48 | AL157712.2 | −0.78 | −0.46 | 0.12 | 0.12 | 1.40 | AL358613.1 | 0.21 | −0.57 | 1.54 | −0.89 | −0.37 |
| FZD5 | 0.74 | −0.65 | −0.89 | −0.09 | −0.43 | RPL10P1 | −1.15 | 0.20 | 1.75 | 0.73 | 1.21 | GLRA1 | 0.08 | 0.30 | −1.23 | 0.25 | −0.57 |
| GEMIN6 | 0.48 | −0.45 | −0.25 | −0.34 | 0.12 | AL133500.1 | −0.77 | −1.00 | 1.37 | −0.27 | 1.32 | AC098859.2 | −0.35 | −0.13 | 1.98 | −0.76 | −0.34 |
| AADAT | −0.79 | 0.21 | 0.38 | −0.17 | −0.15 | AL365361.1 | 0.48 | −0.75 | 0.17 | −0.84 | 0.55 | AP003469.3 | 0.37 | −1.80 | −0.86 | 1.04 | 0.04 |
| PRSS42 | −1.65 | 1.86 | 0.27 | 0.96 | 0.60 | FBXO15 | −0.44 | −0.25 | 0.19 | 0.30 | −0.31 | AC008278.2 | 0.47 | −0.83 | −0.74 | −1.09 | −2.32 |
| PIDD1 | −0.71 | 0.23 | 0.09 | 0.58 | 0.26 | AC011944.2 | 0.34 | −0.16 | 0.25 | −0.07 | −0.03 | LINC01831 | 0.59 | −1.24 | −1.88 | 1.28 | −0.90 |
| MRPL19 | 0.53 | −0.23 | −0.38 | −0.09 | −0.17 | AVPR2 | −0.37 | −0.38 | 0.57 | −0.35 | 0.51 | RNU4-86P | −0.17 | 0.79 | −0.44 | 1.66 | 0.54 |
| SOCS6 | 0.48 | 0.03 | −0.12 | −0.18 | −0.26 | CARD14 | −0.24 | 0.22 | −0.03 | 0.19 | 0.15 | AC235097.1 | −0.49 | 0.68 | −0.87 | 0.42 | 0.97 |
| SRPRA | 0.26 | −0.18 | −0.29 | −0.06 | −0.05 | AC105052.4 | −0.32 | 0.46 | −0.12 | 0.77 | 0.22 | MTAPP1 | 0.32 | −0.64 | −0.08 | 0.63 | 0.97 |
| AL596244.1 | −0.65 | −0.09 | 0.51 | −0.15 | 0.34 | AC009975.2 | 0.92 | −1.59 | −1.40 | 0.15 | 0.21 | AC005833.2 | 0.56 | −0.74 | −0.01 | 0.46 | −2.44 |
| MAGOH2P | −0.79 | 0.28 | 0.54 | 0.67 | 0.63 | SP7 | −0.39 | −0.97 | 0.33 | −0.01 | 0.34 | LINC02378 | 0.23 | −1.63 | −0.44 | −0.35 | 1.50 |
| AP002812.2 | −1.37 | 1.66 | 2.15 | 0.52 | −0.01 | NAT8B | −0.76 | −0.21 | 0.69 | −0.53 | 0.52 | BRWD1-AS1 | −0.10 | 0.01 | −0.65 | −0.03 | −0.52 |
| AC023813.2 | 1.29 | −0.65 | −0.53 | 0.00 | 0.05 | PAX5 | 0.50 | −0.71 | 0.18 | −0.16 | 0.14 | RNASEH1P2 | −0.28 | −0.05 | 1.18 | −0.68 | 1.69 |
| FAM83G | 0.80 | 0.05 | −0.79 | 0.13 | −0.71 | AC084018.1 | −0.40 | −0.02 | 0.67 | −0.07 | 0.39 | AL355482.2 | 0.20 | 0.00 | 0.74 | 0.74 | 0.29 |
| AC124067.1 | 2.99 | −0.44 | −4.11 | 0.26 | −2.76 | CTNNA1P1 | 0.97 | 0.34 | −0.22 | −0.75 | −1.59 | RHOQ | 0.05 | −0.13 | −0.11 | −0.18 | −0.20 |
| FN3KRP | −0.38 | 0.11 | 0.05 | 0.15 | −0.01 | AC079140.4 | −0.74 | 1.52 | 0.33 | 0.70 | 0.31 | AC092813.1 | −0.28 | 0.45 | −0.38 | 0.22 | −1.48 |
| AL355516.1 | −2.75 | 0.92 | 2.74 | 0.32 | 1.72 | AC106900.1 | −0.38 | −0.32 | −0.33 | −0.08 | 0.02 | OR4C7P | 0.50 | −2.27 | −0.47 | −1.77 | −0.84 |
| OLFML1 | −0.85 | 0.61 | 1.41 | −0.15 | 0.22 | AC040169.2 | −0.49 | −0.04 | 1.27 | 0.08 | 0.38 | AP004245.1 | −0.19 | 0.28 | 1.13 | 0.58 | 0.24 |
| AC023855.1 | −1.09 | 0.78 | 1.03 | 0.66 | 0.42 | G7242 | 0.38 | −0.19 | −0.27 | −0.13 | −0.09 | AC015914.1 | 0.07 | −0.01 | −0.28 | −0.17 | −0.03 |
| BMP8B | −0.52 | 0.06 | 0.45 | −0.23 | 0.35 | AP001207.1 | 0.44 | −0.26 | −0.06 | −0.24 | 0.13 | AL109615.1 | 0.15 | 0.06 | 1.77 | −0.40 | 0.45 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| SRC | 0.37 | −0.32 | −0.67 | −0.10 | −0.17 | RNU4-78P | 0.66 | −0.30 | −0.36 | 0.05 | −0.02 | CYP2E1 | −0.06 | 0.21 | −0.41 | 0.37 | −0.09 |
| AC073591.1 | −1.13 | 0.68 | 1.15 | 0.34 | 0.07 | CFAP54 | 0.39 | −0.42 | 0.20 | 0.06 | 0.42 | MIR4778 | −0.34 | −0.66 | 0.71 | 0.31 | 0.11 |
| KIF24 | 0.56 | −0.55 | −0.67 | −0.30 | −0.07 | GIPC2 | −0.21 | 0.21 | 0.53 | −0.03 | 0.04 | AC108063.1 | 0.10 | −0.19 | 0.74 | −0.15 | 0.89 |
| KRD62P1-PARP | −1.57 | 0.26 | 1.12 | −0.46 | 0.19 | P2RX3 | 0.89 | −1.71 | −1.89 | 0.16 | 0.09 | AC124854.1 | −0.40 | −1.29 | 0.29 | −0.85 | −0.83 |
| MSMB | −1.55 | 0.08 | 4.13 | −0.61 | 1.19 | AC138951.2 | −0.43 | 0.79 | −0.22 | 0.86 | 0.21 | SPN | −0.08 | −0.73 | 0.30 | −0.58 | 0.42 |
| MYL6 | 0.39 | −0.11 | −0.79 | 0.11 | −0.74 | AL157385.1 | 0.58 | −0.45 | −1.08 | −0.59 | −0.19 | RN7SL328P | −0.09 | −0.23 | −0.61 | 0.04 | 0.07 |
| RP11-435B5.3 | −1.39 | 0.82 | 1.45 | 0.74 | 1.07 | DHRS7B | −0.11 | 0.05 | 0.09 | 0.04 | 0.02 | SNORD114-25 | −0.26 | 0.36 | 1.50 | 0.64 | 0.21 |
| HECA | 0.50 | −0.11 | −0.33 | 0.08 | −0.42 | ST3GALIP1 | 0.37 | −0.22 | −0.95 | 0.14 | −0.26 | IDH1 | 0.05 | −0.12 | −0.37 | 0.08 | −0.04 |
| AC012409.3 | −1.24 | 0.85 | 1.15 | 0.70 | −0.12 | AC022400.1 | 0.39 | −0.10 | −0.02 | −0.05 | −0.21 | AC112493.1 | −0.25 | −1.35 | 0.40 | −0.14 | 0.98 |
| GPR182 | −0.71 | 0.17 | 0.47 | 0.24 | 0.10 | AC074389.3 | 1.30 | −1.38 | −1.74 | −0.18 | −0.08 | OR52B1P | −0.32 | 0.49 | −0.37 | 0.99 | 1.07 |
| SEPT7-AS1 | −0.74 | 0.38 | 1.03 | 0.02 | 0.45 | CDCA7L | −0.19 | 0.09 | 0.19 | 0.07 | −0.02 | HNRNPA1P46 | 0.32 | −0.04 | −1.01 | 1.01 | −0.34 |
| ETS1 | 0.49 | −0.41 | −0.12 | −0.40 | −0.04 | NFKBID | 0.20 | −0.58 | −0.78 | −0.15 | −0.17 | AC233266.2 | 0.22 | −0.69 | 1.77 | −0.10 | 1.06 |
| SNORA37 | −0.81 | 0.66 | 0.43 | 0.18 | −0.35 | CAMLG | −0.16 | 0.21 | 0.40 | 0.01 | −0.01 | AC091038.1 | −0.13 | −0.18 | −0.36 | 1.32 | 1.04 |
| PRR3 | −0.39 | 0.21 | 0.66 | 0.21 | 0.53 | AC091042.1 | 1.11 | −1.82 | 0.45 | 0.85 | 0.29 | RPL36AP13 | 0.09 | 0.25 | 0.48 | −0.69 | −0.56 |
| SLC25A13 | 0.40 | −0.26 | −0.39 | −0.03 | −0.16 | GPATCH2L | 0.09 | 0.04 | −0.02 | −0.07 | −0.16 | MLLT10 | 0.02 | 0.10 | −0.07 | 0.11 | 0.01 |
| RN7SL94P | −1.25 | −0.04 | 1.18 | 0.47 | 0.63 | AC016586.1 | −0.27 | 0.28 | 0.16 | 0.31 | 0.06 | PLA2G2D | 0.22 | −0.62 | −2.32 | −0.34 | −1.28 |
| SLC16A3 | 0.72 | −1.02 | −0.87 | −0.76 | −0.13 | ATXNIL | 0.10 | 0.04 | −0.23 | 0.04 | −0.24 | AC025884.2 | 0.99 | 0.13 | −1.52 | −0.25 | 0.86 |
| RAB6B | −0.68 | 0.39 | 0.56 | 0.12 | −0.05 | AC005104.2 | −0.37 | 0.41 | 0.57 | 0.06 | −0.08 | F2 | 0.12 | −0.04 | 0.20 | −0.52 | −0.52 |
| C1orf35 | −0.60 | 0.10 | −0.11 | 0.27 | 0.09 | AP001981.1 | −1.03 | 0.51 | 1.32 | 0.57 | 0.44 | AC100863.1 | 0.36 | −0.60 | −0.20 | 0.11 | −0.67 |
| AC090589.3 | −0.69 | 0.27 | 0.18 | 0.41 | 0.57 | AC027117.2 | −0.54 | 0.90 | 1.45 | 0.22 | 0.28 | RNU6-571P | 0.13 | 0.32 | −0.70 | 0.00 | −0.78 |
| HINFP | −0.39 | 0.24 | 0.30 | 0.17 | −0.01 | AL365271.1 | −0.74 | 0.68 | 0.78 | −0.75 | −0.80 | G35852 | −0.36 | −1.24 | −0.84 | 0.62 | 1.95 |
| AGTRAP | 0.45 | −0.48 | −0.40 | −0.25 | −0.01 | AC079336.1 | 0.65 | −0.15 | −0.02 | −0.13 | −0.25 | AC020663.3 | −0.05 | −0.20 | −0.20 | −0.09 | −0.06 |
| GALNT2 | 0.36 | −0.38 | −0.41 | −0.19 | −0.19 | LINC01305 | −0.42 | 0.23 | 0.32 | 0.59 | 0.12 | AC091887.1 | −0.08 | −0.13 | 0.05 | 0.44 | 0.91 |
| PHLDA1 | 0.81 | −0.48 | −0.70 | −0.73 | −0.15 | RNPEP | 0.12 | −0.08 | −0.13 | 0.09 | −0.01 | PADI3 | −0.11 | −0.57 | 0.78 | 0.19 | 1.52 |
| OR5P4P | −1.19 | 1.38 | 1.81 | 0.63 | 0.46 | RPS7P6 | −1.26 | −0.13 | 1.24 | 1.49 | −0.32 | AC073409.1 | 0.99 | 0.19 | −1.23 | 0.27 | 0.88 |
| KRT8P33 | −0.68 | 0.03 | 0.33 | 0.37 | 0.40 | PDSS1P2 | 1.29 | −0.50 | −3.02 | 1.03 | −0.87 | AC007064.2 | −0.24 | 0.13 | −0.78 | 0.05 | 0.64 |
| HBA2 | −2.16 | 1.02 | 2.05 | 0.59 | −1.38 | AC020917.2 | 0.44 | 0.40 | −0.26 | 0.76 | 0.05 | G10989 | 0.31 | 0.18 | 0.01 | −0.81 | −1.83 |
| AAK1 | 0.23 | −0.15 | −0.20 | −0.14 | −0.14 | AC112484.1 | −0.29 | −0.35 | 0.10 | −0.15 | 0.30 | AL354989.2 | 0.37 | 0.58 | 0.12 | 0.79 | 0.38 |
| AC110769.1 | 1.15 | −1.25 | −1.63 | −0.61 | −0.36 | AC090952.1 | 0.81 | 0.63 | −0.27 | 0.98 | −0.14 | AC027801.1 | −0.10 | 0.24 | 0.18 | 0.40 | 0.19 |
| N4BP3 | −0.50 | 0.63 | 0.24 | 0.45 | −0.03 | PSMB9 | 0.19 | −0.63 | 0.10 | −0.47 | 0.20 | AL596325.2 | −0.06 | −0.47 | −0.30 | −0.10 | 0.39 |
| LINC01230 | −2.09 | 1.93 | 1.66 | 1.82 | −0.35 | LINC02068 | 0.46 | −0.43 | 0.05 | −0.45 | 0.23 | ATP5F1EP2 | 0.26 | −1.12 | −0.36 | 0.25 | 0.51 |
| FBXO28 | 0.49 | 0.12 | −0.15 | 0.01 | −0.40 | AC012498.1 | 1.39 | −1.05 | −2.24 | 0.89 | −1.54 | PROSER2-AS1 | −0.07 | −0.02 | −0.50 | −0.21 | 0.23 |
| PPP1CC | 0.42 | −0.09 | −0.23 | −0.01 | −0.29 | RNA5SP319 | 0.96 | −2.58 | −0.35 | −0.88 | 0.45 | IGHA1 | −0.14 | 1.33 | 2.26 | −0.40 | 0.73 |
| BCKDK | 0.34 | 0.00 | −0.10 | 0.04 | −0.22 | AC026782.2 | 0.98 | −2.02 | −0.95 | 0.04 | 0.74 | AL049871.1 | −0.12 | −0.15 | −0.16 | 0.17 | 0.42 |
| AC064807.1 | −0.44 | 0.07 | 0.54 | 0.00 | 0.64 | AC007066.1 | 0.44 | 0.22 | 0.00 | −0.16 | −0.12 | AC010468.1 | −0.11 | −0.18 | 0.39 | 0.63 | −0.01 |
| AC131649.2 | −0.76 | 0.57 | 0.85 | 0.02 | 0.26 | PAWR | 0.08 | 0.28 | 0.02 | 0.17 | −0.10 | AC084759.2 | −0.25 | −1.38 | 0.45 | −0.21 | 1.25 |
| AC113385.3 | −1.65 | 0.02 | 1.47 | 0.29 | 1.45 | NPIPP1 | −0.30 | 0.39 | 0.37 | 0.44 | 0.28 | AP003400.2 | 0.55 | −2.15 | 1.15 | −1.33 | 1.44 |
| AP003352.1 | −0.81 | 0.03 | 0.12 | 0.36 | 0.21 | ANKRD66 | −0.80 | −0.75 | −0.36 | 0.10 | −0.57 | POU6F2-AS2 | −0.42 | −1.00 | 0.16 | 0.01 | 0.87 |
| DDX46 | 0.30 | −0.18 | −0.34 | −0.13 | −0.14 | AL645608.6 | −1.44 | 1.80 | −0.56 | 2.04 | −1.03 | CFAP20 | −0.04 | 0.04 | 0.09 | −0.20 | −0.09 |
| COMMD2 | 0.41 | −0.09 | −0.32 | −0.20 | −0.41 | AC092608.3 | 0.73 | −2.02 | −0.74 | −0.78 | 0.05 | RPL21P109 | 0.36 | −0.49 | 1.36 | −0.92 | 0.50 |
| CFAP74 | −1.38 | 0.08 | −0.10 | 0.45 | −0.08 | AC099687.1 | −1.02 | −0.06 | −1.34 | 0.91 | 1.37 | MIR548AH | −0.37 | 0.52 | 2.16 | −0.01 | 1.27 |
| AC006994.2 | −1.70 | 0.61 | 0.24 | 0.51 | −0.99 | HEYL | −0.23 | 0.01 | 0.76 | −0.09 | 0.18 | AC001226.1 | 0.14 | 0.86 | −0.08 | 1.26 | −0.49 |
| AC113143.1 | 1.37 | −0.01 | −0.67 | 0.30 | −0.49 | BANP | −0.12 | −0.13 | −0.11 | −0.27 | 0.11 | RN7SL348P | −0.15 | −0.79 | −1.05 | 0.97 | 0.38 |
| GCNT1P3 | 1.38 | −0.21 | −0.37 | 0.34 | −0.22 | ALG1L8P | −0.75 | 2.04 | 1.14 | 1.17 | 0.00 | AL139158.1 | −0.12 | 0.62 | 0.72 | 0.50 | 0.10 |
| NEAT1 | 0.72 | −0.05 | −0.54 | 0.15 | −0.50 | EPHB2 | 0.32 | −0.33 | −0.34 | −0.14 | −0.16 | NPM1P6 | 0.07 | 0.13 | −0.01 | −0.01 | −0.29 |
| GSG1L | −1.27 | 0.25 | 0.60 | 0.44 | −0.12 | AC015911.4 | −0.46 | 0.08 | 0.08 | 0.54 | 0.20 | AC104843.1 | −0.17 | −0.02 | −1.38 | −0.07 | −0.86 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC126755.1 | −0.97 | 0.21 | 0.21 | 0.75 | 0.58 | AC012254.3 | −0.26 | 0.26 | 0.19 | 0.25 | 0.28 | MTND1P28 | −0.34 | −0.58 | −1.82 | 0.44 | 1.14 |
| AL031587.3 | −1.16 | −0.25 | 1.42 | 0.33 | 1.23 | AC138123.2 | −0.82 | 0.32 | 0.33 | 0.15 | 0.04 | AC006463.1 | 0.69 | 0.96 | 0.02 | 0.69 | −1.32 |
| GABRP | −1.21 | 0.70 | 0.71 | 0.45 | −0.36 | RPL29P11 | −0.26 | −0.08 | 0.53 | −0.21 | 0.46 | AC012507.2 | −0.16 | −0.39 | −0.50 | −0.63 | 0.26 |
| DNALI1 | −0.63 | 0.26 | 0.49 | 0.30 | 0.16 | G25988 | 0.36 | −0.03 | −0.17 | −0.04 | −0.44 | HES5 | 0.07 | 0.55 | −0.23 | −0.14 | −0.70 |
| CHI3L2 | 1.11 | −0.91 | −0.93 | 0.03 | −1.11 | AL358075.1 | 0.50 | −0.31 | −0.26 | −0.05 | 0.70 | IL2 | 0.36 | −0.65 | 0.89 | −1.63 | 0.26 |
| SLC25A19 | 0.61 | −0.46 | −0.51 | −0.20 | −0.18 | CCDC97 | 0.08 | −0.05 | −0.29 | 0.01 | −0.07 | CALHM4 | −0.19 | 0.13 | −0.17 | −0.18 | 0.79 |
| NCAM2 | −0.88 | 0.54 | 0.88 | 0.02 | 0.50 | HCRTR2 | −0.99 | −1.07 | 0.30 | −0.04 | 0.19 | LRRIQ3 | −0.10 | 0.15 | −0.03 | 0.11 | −0.39 |
| APC2 | −0.77 | 0.36 | 0.56 | 0.50 | 0.45 | RNA5SP97 | 1.20 | 0.35 | −0.56 | 0.67 | −0.36 | AL645949.2 | 0.12 | −0.10 | −0.46 | −0.67 | −0.01 |
| PDGFD | −1.22 | 1.27 | 2.24 | −0.04 | −0.09 | AC023509.3 | −0.45 | −0.40 | 0.85 | −0.25 | 1.46 | AC026770.1 | 0.08 | −0.15 | 0.64 | −0.32 | −0.11 |
| PCDH17 | 1.04 | −0.92 | −0.26 | −0.58 | −0.09 | SNORD79 | 1.30 | −0.35 | 1.31 | −1.14 | 0.02 | ALG1L10P | −0.13 | −0.50 | −0.12 | 0.08 | 0.42 |
| ATP6V1C2 | −0.80 | 0.65 | 0.99 | 0.26 | 0.27 | FSCN1P1 | −0.66 | 0.27 | −0.88 | 0.51 | −0.21 | AC018511.5 | −0.19 | −0.80 | −0.67 | −1.10 | −1.08 |
| AC004972.1 | −1.71 | −1.90 | 0.56 | −0.49 | 0.48 | MUC3A | −0.44 | −0.20 | 0.95 | −0.28 | 0.40 | AL450992.3 | 0.07 | −0.36 | −0.06 | 0.07 | 0.45 |
| ATP6V1G1 | 0.45 | −0.16 | −0.40 | −0.24 | −0.43 | PIR | −0.18 | 0.32 | 0.28 | 0.20 | 0.16 | CNN2P3 | −0.98 | −0.07 | −1.14 | 2.95 | −0.88 |
| AC107308.1 | 2.63 | −0.13 | −2.48 | −1.19 | −3.36 | PPFIA1 | 0.11 | −0.05 | −0.40 | 0.00 | −0.11 | ATOH7 | −0.30 | −0.25 | −0.52 | 0.73 | 1.08 |
| MAF | 0.52 | −0.02 | −0.56 | 0.37 | −0.20 | AL137074.1 | 0.43 | 0.17 | 0.67 | −0.34 | −0.23 | AL136307.1 | −0.32 | −1.17 | 0.55 | −0.01 | 2.08 |
| SF3B3 | 0.33 | −0.27 | −0.19 | −0.08 | 0.04 | GIT1 | 0.12 | 0.06 | −0.33 | 0.21 | −0.08 | AC090505.2 | 0.43 | −0.86 | −0.49 | −0.36 | −0.10 |
| PID1 | −0.72 | 0.26 | 0.65 | 0.06 | 0.05 | CCDC175 | −0.54 | −0.01 | 0.42 | 0.34 | 0.53 | AP003721.4 | 0.17 | 0.07 | 0.11 | 0.42 | −0.49 |
| CASC3 | −0.27 | 0.13 | 0.16 | −0.02 | 0.08 | MIR620 | 0.66 | −0.33 | 0.09 | −1.05 | −0.03 | GHDC | 0.04 | −0.15 | −0.05 | 0.06 | 0.12 |
| ACTR3B | −0.41 | 0.14 | 0.23 | 0.00 | 0.26 | AL603865.1 | 0.83 | 0.14 | −0.35 | −0.91 | −0.65 | LIPK | 0.07 | 0.28 | 1.06 | 0.13 | 0.13 |
| ANKRD30BL | −1.03 | 0.08 | −0.35 | 0.70 | 0.48 | SAMD8 | 0.13 | −0.04 | −0.01 | −0.12 | −0.19 | ACTR5 | 0.03 | −0.04 | −0.24 | 0.11 | 0.01 |
| RRN3P1 | −0.60 | 0.14 | 0.58 | 0.02 | 0.13 | MIR320A | −0.80 | 0.27 | 1.61 | −0.19 | 0.28 | AC011900.1 | 0.25 | 0.09 | −2.03 | 0.47 | −1.58 |
| BDH2 | −0.44 | 0.32 | 0.58 | 0.16 | 0.10 | AC138356.1 | −0.51 | 0.62 | −0.44 | 0.64 | −0.45 | MAP2K4P1 | 0.09 | −0.16 | −0.29 | −0.47 | −0.31 |
| LENG8-AS1 | −0.56 | 0.34 | 0.56 | 0.06 | 0.18 | RNU4-35P | 1.06 | −0.59 | 1.86 | −2.37 | 0.18 | HMGN2P47 | −0.98 | −0.67 | 1.36 | 0.91 | 2.08 |
| GPR162 | −0.94 | −0.05 | 1.28 | −0.08 | 0.59 | RN7SL669P | −0.97 | −0.34 | 0.31 | 0.79 | 1.12 | POM121L9P | −0.12 | 0.22 | 0.78 | 0.02 | −0.39 |
| IDH2 | 0.41 | −0.05 | −0.30 | 0.04 | −0.27 | BMP10 | −0.87 | 1.02 | −1.64 | 0.51 | −1.46 | NANOS3 | −0.11 | 0.24 | −0.64 | 0.10 | −0.64 |
| AC234775.3 | −0.68 | 0.06 | 0.60 | −0.01 | 0.27 | C9orf153 | −0.31 | −0.24 | 0.55 | −0.12 | 0.15 | IGHV4-31 | 0.98 | 0.39 | 2.08 | −0.10 | −0.77 |
| KRTDAP | 0.94 | 0.18 | −0.29 | 0.32 | −0.80 | AC093512.2 | −0.31 | 0.04 | 0.22 | −0.18 | 0.26 | AC136475.7 | −0.17 | −1.29 | −0.10 | −0.04 | −0.95 |
| CD2 | 1.28 | −0.83 | 0.18 | −0.49 | 0.63 | LMNA | 0.13 | −0.09 | −0.65 | 0.11 | −0.30 | BTLA | −0.10 | −0.49 | −0.01 | −0.83 | 0.61 |
| POLR2J4 | −0.47 | 0.23 | 0.36 | 0.13 | 0.21 | AC090692.2 | −0.58 | −1.06 | −1.19 | −0.32 | −0.04 | AC008429.2 | 0.15 | 0.89 | −1.14 | 0.22 | −0.12 |
| IFI27L2 | 0.52 | −0.35 | −0.43 | −0.40 | −0.40 | NECAB2 | 0.63 | −1.44 | −1.62 | 0.66 | 0.24 | AC100850.1 | 0.11 | 0.21 | −1.09 | −0.60 | −0.97 |
| CHRNA9 | 1.65 | −0.53 | −0.32 | 0.42 | −0.26 | AC104438.1 | −0.33 | −0.64 | 0.38 | −0.06 | 0.68 | AC025947.1 | 0.29 | −0.91 | 0.41 | −0.92 | 1.09 |
| BCAT2 | −0.46 | 0.32 | 0.42 | 0.26 | 0.39 | AC104653.1 | −0.46 | −0.03 | 0.99 | −0.43 | 0.19 | AL158042.1 | 0.34 | −0.87 | 1.26 | −2.73 | −0.79 |
| CAPZA3 | −1.37 | 1.29 | 2.34 | 0.17 | 0.07 | AC011373.1 | −1.04 | 0.83 | −0.19 | −1.07 | −1.75 | SAMHD1 | −0.06 | −0.63 | 0.20 | −0.35 | 0.43 |
| PYURF | 0.55 | −0.18 | −0.20 | −0.31 | −0.24 | SNORA57 | −0.30 | −0.26 | −1.02 | 0.02 | −0.37 | AC016582.2 | −0.14 | 0.30 | −0.78 | 0.53 | −0.63 |
| CCDC115 | −0.34 | 0.32 | 0.15 | 0.21 | −0.14 | ICMT | 0.15 | −0.26 | −0.34 | −0.05 | −0.11 | MIR4520A | 0.13 | −0.42 | 0.49 | −0.15 | 1.36 |
| SMARCB1 | 0.31 | −0.22 | −0.30 | −0.16 | −0.16 | OR10D3 | 1.13 | 0.46 | −1.01 | 1.23 | −1.16 | AC087699.1 | 0.38 | −1.19 | −0.96 | 0.27 | 1.19 |
| PABPC1L | −0.53 | 0.08 | −0.15 | 0.26 | 0.11 | MZT2B | 0.19 | −0.11 | −0.64 | 0.10 | −0.36 | CD164L2 | 0.06 | 0.23 | 0.07 | 0.45 | −0.11 |
| MTND2P12 | −1.94 | −0.63 | 2.69 | 0.07 | 1.90 | LINC01791 | 1.02 | −0.94 | −1.55 | 0.56 | −0.48 | AL023875.1 | 0.22 | −0.69 | −0.11 | 0.07 | 0.86 |
| PLD2 | 0.38 | −0.31 | −0.69 | −0.04 | −0.17 | RCSD1 | −0.30 | −0.19 | 0.44 | −0.18 | 0.43 | OR6R1P | −0.23 | −1.35 | −0.82 | 1.69 | 2.33 |
| BLOC1S3 | 0.50 | 0.07 | −0.26 | 0.12 | −0.38 | AC021231.3 | −0.49 | −0.39 | 0.92 | −0.11 | 0.97 | AC090589.1 | −0.12 | −0.36 | 0.28 | −0.23 | 0.35 |
| C14orf39 | −1.95 | 1.26 | 0.54 | 1.21 | 0.08 | AL590489.1 | −0.68 | −1.19 | 1.13 | −0.42 | 0.21 | AC073195.1 | −0.12 | 0.22 | −1.13 | 0.39 | −1.19 |
| KB-226F1.1 | −1.21 | 0.27 | 0.14 | −0.04 | −0.28 | AC074117.2 | −0.54 | 0.53 | 0.20 | 0.20 | −0.23 | LINC01781 | −0.97 | 0.67 | 0.92 | 0.31 | 0.90 |
| KRT24 | 1.92 | −1.04 | −3.35 | −0.37 | −3.50 | ANKRD13D | −0.15 | 0.01 | −0.04 | 0.16 | 0.19 | AC010240.1 | 0.19 | −0.80 | −0.01 | −0.05 | −0.01 |
| ALDOA | 0.65 | −0.14 | −0.66 | 0.03 | −0.70 | AP000997.2 | 0.79 | −0.65 | −0.92 | −0.20 | −0.30 | RNF103-CHMP3 | 0.11 | −1.01 | 0.47 | −0.19 | 0.24 |
| FBLN2 | −0.94 | 1.01 | 1.81 | −0.08 | −0.13 | AC105389.2 | 0.54 | −0.44 | −0.14 | −0.07 | 0.52 | OR7E53P | −0.37 | 0.11 | −0.29 | 0.24 | −0.35 |
| C8orf44 | −0.46 | 0.08 | 0.76 | 0.05 | 0.49 | NXPH1 | −0.87 | −0.76 | −1.16 | 0.53 | −0.37 | AC083836.1 | −0.15 | 0.56 | −0.47 | 1.08 | −1.18 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC005261.1 | 0.41 | −0.20 | −0.16 | −0.15 | −0.10 | BAALC | −0.26 | 0.20 | 0.99 | −0.10 | 0.24 | PGGT1BP1 | 0.25 | −0.28 | −0.83 | 0.03 | −0.78 |
| LINC01589 | −1.52 | 0.93 | 1.42 | 1.00 | 0.16 | AC090517.2 | 0.57 | −0.01 | −0.22 | 0.03 | −0.23 | PRDX3P4 | −0.09 | 0.08 | −0.24 | −0.21 | 0.18 |
| FAM104B | 0.57 | −0.03 | −0.27 | −0.11 | −0.50 | RPARP-AS1 | −0.21 | 0.03 | 0.58 | 0.00 | 0.38 | 8-Sep | 0.03 | 0.14 | −0.13 | 0.06 | −0.22 |
| LEMD3 | 0.28 | −0.11 | −0.13 | −0.08 | −0.04 | AL161672.1 | 0.41 | −0.60 | −0.71 | −0.12 | −0.50 | LRRC28 | 0.03 | −0.05 | 0.03 | 0.11 | 0.09 |
| AC104447.1 | 0.68 | −0.48 | −0.31 | −0.37 | −0.28 | AC019294.2 | −0.86 | −0.73 | −0.28 | 0.21 | 0.85 | AC234771.2 | −0.31 | −1.93 | 0.81 | −0.24 | 2.48 |
| OR10AB1P | −1.10 | 1.08 | 1.85 | 0.90 | 0.75 | ACVR1B | −0.18 | 0.46 | 0.46 | 0.22 | 0.02 | AC103881.1 | −0.42 | −0.84 | 0.63 | −1.87 | 2.07 |
| PBRM1 | 0.27 | −0.06 | −0.21 | −0.04 | −0.15 | EIF4EBP2P2 | −0.67 | 0.46 | 2.03 | 0.23 | 1.25 | AC090888.1 | −0.35 | 0.55 | 0.18 | 0.68 | 0.38 |
| GRB14 | −1.13 | 0.72 | 1.29 | 0.14 | 0.55 | SNORD11B | 0.80 | −1.01 | −1.08 | −0.56 | −0.48 | NDUFC2 | −0.04 | −0.03 | −0.15 | 0.03 | −0.17 |
| EGFL8 | −0.74 | 0.44 | 0.34 | −0.06 | 0.05 | AC022816.1 | 0.81 | −1.51 | −0.71 | −0.77 | 0.57 | MT1HL1 | −0.69 | 0.57 | −0.66 | 2.27 | 0.47 |
| AC061709.2 | −2.10 | 0.23 | 1.08 | 0.72 | 0.00 | FNTB | 0.20 | 0.13 | −0.11 | 0.05 | −0.07 | HNRNPA1P31 | −0.30 | −1.54 | 1.62 | 0.07 | 2.11 |
| AC026740.1 | −0.70 | −0.36 | −0.17 | 0.08 | 0.29 | AL161449.2 | −0.45 | 0.71 | 0.67 | 0.46 | 0.09 | AL118522.1 | 0.22 | −0.86 | 0.59 | 1.24 | 0.92 |
| CALML5 | 1.21 | 0.36 | −0.23 | 1.09 | −0.64 | AL358813.1 | 0.67 | −0.05 | 0.18 | 0.46 | −0.42 | DAPK3 | 0.04 | −0.06 | −0.44 | −0.11 | −0.35 |
| CITED2 | −0.54 | 0.71 | 0.43 | 0.41 | −0.23 | KDELC2 | 0.18 | −0.21 | −0.11 | −0.14 | −0.15 | CHRNA10 | −0.07 | −0.49 | −0.06 | 0.04 | 0.52 |
| EDC4 | −0.37 | 0.11 | −0.08 | 0.16 | 0.04 | AC058791.1 | −0.16 | −0.24 | −0.07 | −0.24 | 0.31 | OR5L1 | −0.43 | 0.22 | −0.41 | −0.93 | 0.28 |
| SELL | 1.34 | −1.26 | −0.09 | −0.79 | −1.01 | AC012358.2 | −0.27 | −0.02 | 0.46 | 0.25 | 0.32 | AC114982.1 | 0.16 | 0.62 | 0.28 | 0.79 | −0.32 |
| LINC02185 | −1.12 | 1.24 | 1.70 | −0.12 | −0.19 | AP002505.2 | −0.39 | 0.17 | −0.22 | 0.20 | 0.24 | NORAD | 0.04 | 0.18 | 0.27 | −0.07 | −0.13 |
| EPHB4 | 0.51 | −0.15 | −0.61 | 0.23 | −0.04 | AC002540.1 | −0.47 | 0.70 | 0.13 | 0.71 | −0.46 | AL136537.1 | −0.37 | −0.76 | −0.06 | −0.37 | 1.46 |
| RRAGD | −0.75 | 0.80 | 0.56 | 0.31 | −0.10 | G37023 | 1.09 | −1.36 | −0.98 | −1.44 | −0.92 | OR5AK1P | −0.61 | −0.63 | 0.88 | −0.57 | 0.83 |
| LINC01315 | −1.21 | 0.98 | 1.17 | 0.24 | 0.21 | LINC01899 | −1.09 | 1.49 | −0.41 | −0.64 | −1.02 | HNRNPA3P8 | −0.27 | −1.88 | 0.96 | 0.82 | 2.73 |
| SELENON | 0.35 | −0.31 | −0.26 | −0.08 | 0.09 | DHX38 | −0.12 | 0.01 | −0.13 | −0.03 | −0.03 | RN7SL387P | −0.24 | −0.69 | −0.88 | 1.26 | 2.01 |
| BTG1 | 0.62 | 0.02 | −0.42 | 0.30 | −0.57 | LINC02343 | −0.70 | 0.92 | 0.37 | 0.92 | 1.11 | AP001330.3 | −0.56 | 0.89 | 3.87 | 0.16 | 2.10 |
| AC073964.1 | 1.51 | −1.36 | −0.26 | −0.50 | 0.51 | LINC01043 | −1.11 | 0.16 | 0.29 | 0.70 | 0.46 | MIR4787 | −0.34 | 0.06 | 1.46 | 0.91 | 0.10 |
| GXYLT2 | −1.04 | 0.64 | 2.09 | −0.43 | 0.28 | DOCK7 | −0.08 | 0.11 | −0.05 | −0.07 | −0.08 | AC092757.2 | 0.08 | 0.17 | 0.58 | −0.23 | −0.03 |
| RORB | −1.15 | 0.57 | 0.42 | 0.72 | 0.07 | STK11 | 0.11 | −0.12 | −0.47 | 0.15 | 0.00 | SPIN4-AS1 | 0.13 | 0.11 | 0.61 | 0.19 | −0.05 |
| NSUN5P1 | −0.58 | 0.21 | 0.25 | 0.32 | 0.16 | HNRNPA1P30 | −0.86 | 0.76 | 0.01 | −0.13 | −0.89 | AL355340.1 | 0.13 | 0.58 | 0.22 | 0.33 | −0.61 |
| MTSS1 | 0.40 | −0.31 | −0.86 | 0.07 | −0.12 | MRGPRD | −0.67 | −0.85 | −0.76 | 0.59 | 0.84 | MIR606 | 0.14 | 0.44 | −0.20 | −0.03 | −0.01 |
| AC139712.1 | −1.65 | −0.15 | −0.96 | 1.09 | 0.82 | RNF183 | −0.61 | 0.27 | −0.03 | 0.71 | −0.18 | AL391811.1 | 0.69 | 0.97 | −0.77 | 1.01 | −0.51 |
| CITED4 | 0.79 | 0.06 | −0.97 | 0.10 | −0.55 | LINC-PINT | −0.15 | −0.07 | −0.07 | −0.19 | 0.18 | ARF4P3 | 0.49 | −0.33 | −0.79 | −0.01 | −0.41 |
| PLCZ1 | −0.90 | 1.07 | 1.32 | 0.69 | 0.16 | NRSN2-AS1 | −0.19 | 0.29 | 0.42 | 0.35 | 0.14 | AC005323.1 | 0.24 | 0.25 | 1.14 | −0.55 | −0.18 |
| AL110115.1 | 1.45 | −0.39 | −0.89 | −0.15 | −0.47 | MIR370 | 1.10 | −0.33 | 0.71 | −0.39 | −0.52 | AC090193.1 | 0.21 | 0.28 | −1.07 | 0.75 | −0.40 |
| ATAD2 | 0.45 | −0.62 | −0.73 | −0.16 | −0.14 | ANKRD19P | 0.35 | −0.93 | 0.59 | −0.01 | 1.23 | BX547991.1 | −0.23 | −0.36 | 1.19 | 1.35 | 3.98 |
| RFESD | −0.85 | 0.75 | 0.87 | 0.75 | 0.18 | AL049651.1 | 1.34 | −3.29 | −2.55 | 0.81 | −0.86 | KATNBL1P1 | 0.37 | −1.07 | 1.37 | −1.23 | 1.05 |
| LIMK1 | 0.43 | −0.31 | −0.43 | −0.20 | 0.00 | KCNH6 | −0.69 | 0.77 | 0.65 | 0.04 | −0.30 | RNU6-1290P | 0.23 | −0.45 | 0.17 | 0.04 | 0.01 |
| AC116533.1 | 0.72 | −0.08 | −0.05 | −0.14 | −0.25 | AC093503.3 | −0.56 | −0.42 | 0.60 | 0.20 | 0.39 | LINC01693 | 0.48 | −0.77 | −0.85 | −1.47 | −1.26 |
| MALAT1 | 0.53 | −0.10 | −0.19 | −0.15 | −0.19 | CLECL1 | 0.47 | −0.72 | −0.35 | 0.09 | 0.63 | AC116025.1 | −0.14 | 0.72 | 0.47 | 0.72 | −0.40 |
| AP003548.1 | −1.59 | −0.18 | 0.66 | −0.22 | −0.38 | LINC01006 | −0.22 | 0.06 | 0.47 | −0.09 | 0.72 | RNU6-611P | −0.08 | −0.55 | 0.50 | −0.41 | 1.19 |
| G20559 | −1.33 | 0.29 | 1.37 | −0.17 | −0.29 | FOLH1 | 0.30 | −0.13 | 0.15 | 0.37 | 0.61 | CACNG3 | −0.17 | 0.35 | −0.55 | 0.29 | −0.38 |
| KRBOX4 | −0.41 | −0.01 | 0.36 | −0.06 | 0.34 | AC244131.1 | 0.23 | −0.15 | −0.48 | 0.17 | −0.38 | FUT8-AS1 | 0.13 | 0.14 | 0.78 | −0.75 | 0.14 |
| PHACTR2-AS1 | 0.94 | −0.43 | −0.17 | −0.08 | 0.48 | LINC00571 | −0.19 | 0.36 | 0.14 | 0.35 | 0.09 | AC091799.1 | −0.23 | −0.36 | 1.23 | 0.26 | 0.24 |
| ALOX12B | 0.84 | −0.18 | −0.06 | −0.22 | −0.25 | AL392024.1 | −0.62 | −0.27 | −1.70 | 0.18 | 0.26 | AL391261.2 | 0.14 | −0.71 | −0.05 | −0.35 | 0.60 |
| AC023590.1 | −0.60 | 0.00 | 0.81 | 0.06 | 0.85 | PNKP | −0.18 | −0.22 | −0.38 | 0.05 | 0.19 | AL049872.1 | 0.06 | 0.02 | −0.04 | −0.06 | 0.01 |
| JAM3 | −0.46 | 0.12 | 0.75 | −0.22 | 0.14 | OR52N3P | −0.91 | −0.77 | −2.52 | 0.80 | −2.44 | AC007406.2 | −0.56 | −0.49 | 0.53 | −0.95 | 0.86 |
| CALCRL | 0.78 | −0.31 | −0.71 | −0.03 | −0.41 | AC036214.2 | 0.19 | 0.05 | −0.06 | −0.05 | −0.02 | AL356022.1 | −0.22 | −0.98 | 0.20 | 0.43 | 0.65 |
| ARHGAP42 | −0.35 | 0.32 | 0.44 | 0.00 | −0.01 | FAIM2 | 0.46 | 0.40 | 0.72 | 0.73 | −0.85 | AC139100.2 | 0.08 | 0.19 | 0.15 | 0.37 | 0.06 |
| EIF5AL1 | 1.17 | −0.65 | −0.99 | −0.32 | −1.50 | RNASSP452 | −1.09 | 1.55 | −0.72 | 1.01 | −0.99 | LINC01189 | −0.24 | −0.22 | 1.45 | −0.50 | −0.39 |
| HAS2-AS1 | −1.04 | −0.47 | −0.04 | −0.17 | 0.29 | DDX18P1 | 0.24 | −0.09 | −0.13 | −0.07 | 0.01 | OR52J1P | −0.42 | −0.01 | −2.78 | 1.85 | −1.02 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| EPB41 | −0.32 | 0.28 | 0.28 | 0.12 | 0.03 | SLC6A10P | −0.59 | 0.18 | 0.10 | 1.10 | 0.04 | AL591416.1 | 0.36 | −0.11 | 0.37 | 1.70 | −0.18 |
| CX3CL1 | −0.70 | 0.73 | 0.87 | 0.37 | 0.14 | AC004835.2 | 0.72 | −0.18 | −2.16 | 0.03 | −1.13 | AC012146.1 | −0.09 | −0.40 | −0.70 | 0.26 | −0.25 |
| ANO5 | −1.01 | 0.50 | 0.40 | 0.16 | 0.18 | AC093787.1 | −0.89 | 1.14 | 1.22 | 0.30 | 0.39 | ADAM20P2 | −0.39 | −0.52 | −1.18 | 0.04 | 1.09 |
| EPS8 | −0.74 | 0.50 | 0.92 | −0.04 | −0.12 | MIR3162 | 0.64 | −0.06 | 0.40 | 0.25 | 0.08 | PLEKHA8P1 | −0.05 | −0.11 | 0.33 | −0.27 | 0.19 |
| DOCK4-AS1 | 0.62 | −0.23 | −0.55 | −0.26 | −0.32 | AL355864.1 | 0.85 | −1.20 | −2.04 | 0.13 | −0.16 | PRR18 | −0.22 | −0.30 | −0.65 | 0.86 | 0.81 |
| LSM10 | 0.34 | −0.30 | −0.25 | −0.06 | 0.03 | AKAP6 | −0.18 | 0.14 | −0.13 | 0.25 | −0.08 | AL445465.1 | −0.15 | 0.17 | 0.50 | 0.54 | −0.66 |
| CEBPA | −0.89 | 0.77 | −0.17 | 0.45 | −0.99 | AC092435.4 | −0.69 | 0.58 | 0.53 | 0.31 | 0.29 | OR7E130P | −0.33 | 0.59 | 0.33 | −0.08 | 0.02 |
| PGLYRP4 | 0.85 | −0.42 | −0.10 | −0.40 | −0.29 | NDFIP1 | −0.17 | 0.19 | 0.34 | −0.07 | −0.02 | AC018692.1 | 0.21 | −1.12 | −2.71 | 0.11 | −1.31 |
| SULT1A1 | −0.81 | 0.14 | 0.71 | 0.07 | 0.39 | AC060809.1 | −0.74 | −0.04 | −0.18 | −0.07 | −0.37 | STK39 | 0.05 | 0.12 | 0.03 | −0.19 | 0.08 |
| AC104852.1 | −2.25 | 2.50 | 1.01 | 2.06 | −0.10 | PRR13P5 | 0.35 | −0.48 | −0.81 | 0.00 | 0.29 | PCMTD1P2 | −0.49 | 0.16 | −0.61 | 0.12 | −1.98 |
| SLC9B1 | −0.79 | 0.15 | 0.82 | 0.18 | 0.46 | AC022028.2 | −0.69 | 0.04 | 0.15 | 0.44 | −0.15 | FABP1 | 0.23 | −0.22 | −0.87 | −0.04 | −0.26 |
| MTERF3 | 0.37 | −0.30 | −0.21 | −0.14 | 0.02 | AL160408.3 | −0.39 | −0.16 | 0.54 | −0.43 | −0.20 | RN7SL532P | 0.10 | −0.39 | −0.15 | −0.35 | −0.27 |
| ELMOD2 | 0.45 | −0.24 | −0.17 | −0.12 | −0.09 | AC068594.2 | 0.74 | −1.02 | −0.23 | −0.72 | −0.50 | CSNK1A1L | 0.22 | 0.13 | −0.29 | 0.03 | −0.50 |
| GRIN2C | −0.73 | 0.66 | 0.04 | 0.54 | −0.09 | AC051619.8 | 0.47 | 0.15 | −0.31 | −0.05 | −0.96 | LINC00448 | −0.37 | 1.27 | −2.67 | 1.76 | −0.78 |
| AC091231.1 | −0.74 | −0.13 | −0.29 | −0.02 | 0.28 | PRPF38A | 0.09 | −0.04 | −0.12 | −0.02 | −0.02 | KREMEN1 | −0.03 | 0.15 | 0.19 | 0.12 | −0.13 |
| NECAB1 | −0.98 | 0.51 | 0.93 | 0.28 | 0.42 | NOP56P2 | 0.75 | −0.67 | 0.33 | −0.68 | −0.24 | AC125238.2 | 0.29 | −1.05 | 0.29 | −1.92 | 0.29 |
| HERC2P3 | −0.50 | −0.10 | 0.15 | 0.59 | 1.18 | AL356133.1 | 0.42 | 0.16 | 0.18 | 0.11 | 0.00 | AC092723.1 | 0.52 | −0.12 | 1.09 | 0.85 | −1.82 |
| GPATCH1 | −0.23 | 0.16 | 0.19 | 0.07 | 0.00 | FOXO3B | −0.26 | 0.23 | 0.50 | −0.05 | 0.45 | AL157902.1 | −0.31 | 1.00 | −1.07 | 1.28 | −0.18 |
| AC018445.4 | −0.71 | 0.08 | 0.46 | 0.22 | −0.12 | SDHD | 0.16 | −0.17 | −0.23 | 0.07 | −0.03 | AC008883.1 | 0.08 | −0.55 | −0.24 | −0.15 | 0.12 |
| G42895 | 1.70 | −1.02 | −1.05 | −0.28 | −0.26 | AC107075.1 | 0.55 | −0.25 | −0.49 | −0.24 | −0.39 | PGAM1P4 | −0.25 | −0.34 | 0.79 | 0.45 | 1.44 |
| SNHG3 | 0.65 | −0.14 | −0.82 | 0.34 | −0.99 | AF067845.4 | 1.23 | −0.23 | −2.89 | 0.31 | −2.98 | HHEX | 0.06 | −0.10 | 0.45 | −0.13 | 0.01 |
| AC092634.3 | −1.87 | 1.16 | 0.85 | 1.33 | −0.12 | DROSHA | 0.08 | −0.17 | −0.22 | −0.08 | 0.01 | G31990 | −0.24 | 0.43 | 1.05 | −0.27 | 0.04 |
| FABP3 | −0.64 | 0.19 | 0.47 | 0.08 | 0.03 | AC019118.1 | 0.52 | −0.25 | −0.82 | 0.13 | −0.59 | DRC7 | −0.15 | −1.16 | −0.16 | −0.62 | −0.17 |
| FBLN1 | −0.90 | 0.80 | 2.03 | −0.01 | 0.29 | C7orf25 | 0.31 | −0.17 | −0.12 | 0.05 | 0.18 | LINC02250 | −0.07 | −0.03 | −0.22 | 0.20 | −0.27 |
| PPIAP31 | 1.22 | −0.17 | −1.39 | 0.40 | −0.81 | SPAM1 | 0.86 | −1.47 | −2.44 | −0.10 | −1.99 | AL590240.2 | −0.34 | −1.71 | 0.72 | −0.58 | 0.13 |
| EFS | −0.48 | 0.45 | 0.33 | 0.36 | 0.16 | AC020718.1 | −1.24 | −0.18 | −0.06 | 1.61 | −0.53 | RECQL4 | 0.05 | −0.33 | −0.58 | 0.11 | 0.29 |
| RBM23 | −0.19 | 0.07 | −0.02 | 0.07 | −0.08 | AP000435.1 | −0.99 | −0.17 | −0.55 | 1.28 | 0.14 | MAGED1 | 0.03 | 0.05 | 0.10 | −0.38 | −0.33 |
| RPL23 | 0.54 | −0.25 | −0.23 | −0.15 | −0.21 | PRMT9 | 0.08 | −0.22 | 0.02 | −0.11 | 0.21 | AC073611.1 | 0.09 | −0.25 | 0.11 | −0.28 | 0.37 |
| AC013448.1 | −2.38 | 1.29 | 0.72 | −0.07 | 0.31 | AC012360.1 | 0.45 | 0.02 | −0.24 | 0.22 | −0.11 | RNY4P6 | −0.11 | −0.28 | −1.11 | −0.11 | −0.51 |
| AL161457.2 | −0.95 | 0.71 | 1.47 | 0.46 | 0.32 | OR52N2 | −0.97 | −0.04 | 0.08 | 0.19 | −0.15 | MTND5P7 | 0.26 | −2.24 | 0.19 | −0.87 | 0.22 |
| GPR183 | 0.81 | −0.53 | −0.57 | −0.30 | −0.38 | AC095055.1 | −0.22 | 0.50 | 0.00 | 0.44 | −0.36 | AC112176.1 | −0.29 | −0.95 | −0.21 | −0.73 | 0.58 |
| AGR3 | −2.41 | −0.03 | 2.22 | −0.58 | 1.32 | AL161912.4 | 1.02 | −0.83 | −1.14 | −0.01 | −0.73 | AC012370.1 | −0.10 | −0.71 | 0.26 | −0.68 | 0.03 |
| MYCBP | 0.65 | −0.18 | −0.55 | −0.11 | −0.47 | FIRRE | −0.41 | −0.28 | 0.04 | 0.21 | 0.09 | RNU6-343P | 0.10 | 0.11 | 0.45 | 0.17 | 0.31 |
| CLN3 | −0.65 | 0.36 | 0.60 | 0.36 | 0.44 | LILRA6 | 0.39 | −0.88 | −0.09 | −0.34 | −0.32 | NMRK2 | −0.41 | 0.72 | 1.46 | −0.20 | 0.59 |
| AC096745.2 | −1.11 | 0.52 | 0.93 | 0.43 | 0.10 | RN7SL318P | 0.71 | −0.78 | −1.68 | 0.11 | 0.34 | NCKAPIL | 0.06 | −0.41 | −0.06 | −0.27 | 0.03 |
| AC026583.1 | 2.06 | −1.69 | −1.30 | 0.06 | 0.30 | OR4K13 | −0.74 | 0.63 | 0.01 | 0.18 | −0.72 | KLHL15 | 0.03 | 0.07 | −0.03 | −0.06 | −0.15 |
| RHBDD1 | 0.31 | −0.08 | −0.26 | −0.03 | −0.25 | OR9A3P | −1.07 | −0.76 | −0.69 | −0.47 | 0.51 | BUB1B-PAK6 | 0.13 | −0.18 | −1.15 | −0.23 | −0.67 |
| COMMD1 | 0.41 | 0.08 | 0.12 | 0.02 | −0.15 | AP002340.1 | −0.53 | 0.14 | −0.14 | 0.49 | 0.42 | LINC02542 | −0.12 | 0.61 | 0.22 | −0.36 | −0.53 |
| PLK5 | −1.92 | 0.08 | 1.91 | 0.45 | −0.64 | CPB2-AS1 | −0.43 | −0.06 | −0.01 | 0.26 | −0.12 | RNA5SP52 | −0.61 | 1.47 | −1.29 | 2.07 | −2.00 |
| NUDT6 | −0.44 | 0.06 | 0.65 | 0.10 | 0.49 | FMO10P | 1.05 | −2.52 | −0.57 | 0.79 | 1.82 | AC004893.1 | 0.07 | 0.31 | 0.31 | 0.07 | −0.09 |
| RPS4X | 0.54 | −0.09 | −0.08 | −0.20 | −0.38 | MUC13 | −0.68 | −0.06 | −0.99 | 0.20 | −0.72 | AC007552.2 | 0.14 | −0.50 | −2.02 | 0.53 | −1.15 |
| MTSS1L | −0.51 | 0.17 | 0.17 | 0.13 | 0.12 | AC093523.1 | −1.45 | 0.78 | 1.76 | 0.11 | −0.34 | GARSP1 | −0.75 | 0.22 | 0.23 | −0.74 | −1.12 |
| GNPDA1 | 0.37 | −0.08 | −0.26 | −0.07 | −0.23 | AL583842.2 | −0.70 | 0.68 | 0.30 | 0.95 | 0.57 | AC034268.2 | −0.25 | 0.05 | −1.63 | 0.14 | −0.35 |
| PMAIP1 | 0.84 | −0.26 | −0.71 | −0.04 | −0.26 | CD302 | −0.21 | 0.29 | 0.34 | 0.08 | −0.09 | PGAP1 | 0.05 | 0.07 | −0.05 | 0.28 | −0.07 |
| G11672 | −1.21 | −0.20 | −0.19 | 0.36 | 0.54 | MORF4L1P5 | −0.75 | 0.20 | 0.12 | −0.15 | −1.06 | FO082842.1 | 0.49 | −0.68 | −1.31 | 0.37 | −1.92 |
| FAM222A-AS1 | −1.38 | 0.35 | 1.72 | −0.69 | 0.24 | AL513547.1 | 0.83 | −0.85 | 0.26 | −0.54 | −0.14 | ATP6V1FNB | 0.06 | −0.08 | −0.17 | −0.04 | −0.09 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AL158839.1 | −1.91 | 0.25 | 2.70 | −0.65 | −0.24 | LINC02588 | −1.06 | 0.82 | −1.65 | 0.83 | −1.35 | LINC01609 | −0.21 | −0.47 | 1.03 | −0.38 | 0.45 |
| AC005392.1 | −1.57 | 0.48 | −0.24 | 0.50 | 0.66 | AL450992.1 | −0.32 | −0.13 | −0.65 | 0.01 | −0.41 | AC068135.2 | 0.96 | 0.25 | 0.04 | 0.71 | −0.54 |
| AL008721.2 | −0.47 | 0.24 | 0.76 | −0.35 | 0.03 | AL022344.2 | −0.56 | 0.90 | 2.43 | 0.86 | 0.69 | AC245041.1 | 0.06 | −0.15 | −0.08 | 0.22 | 0.40 |
| BTBD3 | 0.53 | −0.18 | −0.46 | 0.14 | −0.19 | AL390195.1 | 0.33 | 0.07 | 0.16 | −0.04 | −0.14 | ATF1P1 | 0.52 | −0.76 | 1.33 | −1.95 | −0.27 |
| HAUS1 | 0.38 | −0.25 | −0.21 | 0.00 | −0.02 | AC007906.2 | −0.46 | 0.14 | −0.69 | 0.51 | 0.33 | AC004888.1 | −0.52 | 0.64 | 2.01 | −1.50 | 0.07 |
| PARP4 | 0.25 | −0.16 | −0.31 | −0.03 | −0.15 | RPS6P15 | −0.87 | −1.15 | 0.50 | −0.77 | 0.31 | AC100832.2 | 0.47 | −1.48 | −0.98 | −0.12 | −0.05 |
| AC090198.1 | −0.52 | 0.06 | 0.57 | −0.02 | 0.27 | AP003117.2 | −0.78 | 0.13 | 3.21 | −0.82 | 1.05 | AC074198.1 | 0.34 | −2.55 | −0.88 | −0.62 | NA |
| AP002812.3 | −0.83 | 0.44 | 0.77 | 0.20 | 0.35 | AC012454.1 | −1.03 | −0.05 | 1.37 | 0.20 | 0.11 | AC092171.2 | −0.03 | 0.11 | 0.01 | −0.02 | −0.20 |
| GMNN | 0.55 | −0.61 | −0.29 | −0.34 | 0.17 | CXCL17 | 0.38 | −0.38 | −0.72 | −0.01 | −0.67 | SNORA53 | 0.06 | 0.34 | 0.89 | −0.12 | −0.35 |
| HMGB3P22 | −0.89 | 0.45 | 1.27 | 0.32 | 0.34 | AC004801.1 | 0.42 | −0.41 | −0.12 | 0.06 | 0.30 | AC092042.3 | −0.22 | −0.07 | 0.20 | −0.55 | −0.87 |
| DDX41 | 0.40 | −0.25 | −0.72 | −0.04 | −0.19 | AC008280.1 | −0.44 | 0.34 | 0.43 | 0.54 | 0.08 | RN7SL804P | 0.38 | 0.96 | −0.92 | 1.96 | −1.57 |
| AC116099.1 | −1.64 | 1.01 | 1.79 | −0.09 | 0.59 | AC096558.1 | 0.51 | −0.74 | −0.26 | −0.11 | 0.37 | AC092118.2 | 0.16 | 0.62 | −1.12 | 0.42 | −0.59 |
| ELK1 | 0.30 | −0.13 | −0.23 | −0.03 | −0.13 | AL591885.1 | −0.83 | 0.17 | 0.75 | 0.58 | −0.49 | AC108729.1 | −0.38 | 1.48 | −0.83 | 0.83 | −1.06 |
| MIB2 | −0.55 | 0.25 | 0.17 | 0.30 | 0.29 | HMGB3P5 | 1.24 | −1.25 | 0.66 | 1.32 | 0.85 | RNA5SP514 | −0.32 | −0.58 | −0.86 | −1.04 | −0.57 |
| SLC16A12 | −1.24 | −0.18 | 0.33 | 0.56 | 0.57 | RPL5P34 | 0.33 | 0.00 | −0.36 | −0.17 | −0.25 | LINC01220 | 0.13 | −0.56 | 0.32 | −0.60 | 0.41 |
| AIFM1 | 0.39 | −0.22 | −0.52 | −0.14 | −0.18 | AC010608.2 | 0.95 | −1.21 | −1.85 | 0.92 | −0.65 | AC016746.1 | −0.21 | 0.48 | 1.32 | −0.96 | 1.06 |
| EFHD2 | 0.44 | −0.57 | −0.89 | −0.15 | −0.25 | MIR874 | −0.80 | 0.97 | 0.09 | 0.12 | −1.48 | RPL6P30 | 0.39 | −1.35 | −1.83 | 1.13 | −0.38 |
| SAC3D1 | 0.57 | −0.21 | −0.54 | 0.04 | −0.08 | PPP2R5B | 0.18 | −0.05 | −0.54 | −0.02 | −0.11 | AL137798.1 | 0.09 | −0.10 | 0.21 | −0.11 | 0.19 |
| AL139158.3 | 1.29 | −0.96 | −1.51 | −0.13 | −0.40 | RPL21P93 | 0.89 | −0.09 | −0.64 | −0.56 | −0.72 | DUX4L19 | −0.22 | −1.76 | −0.05 | 0.46 | 0.35 |
| NCKAP1 | 0.42 | −0.08 | −0.26 | −0.12 | −0.33 | AC024270.1 | 0.43 | −0.32 | 0.15 | −0.52 | −0.17 | AC091820.1 | −0.56 | 0.74 | 1.45 | 0.28 | 1.31 |
| KCNAB3 | −0.50 | −0.09 | −0.42 | 0.06 | 0.12 | RN7SL384P | 1.45 | 1.05 | 0.17 | 0.06 | 0.80 | RNU4-68P | −0.17 | −0.15 | 1.90 | −0.26 | 0.79 |
| AC254562.1 | −1.20 | 0.45 | 1.14 | 0.10 | 0.30 | AL360181.2 | −0.30 | 0.42 | −0.14 | 0.69 | −0.15 | HMGN1P9 | 0.44 | 0.65 | −1.94 | 0.44 | −0.58 |
| AGER | −0.65 | −0.03 | −0.27 | 0.16 | 0.15 | AC004771.5 | 0.48 | 0.06 | 0.15 | −0.31 | −0.04 | AP000553.3 | −0.29 | −0.05 | −0.99 | 0.34 | −0.31 |
| CAAP1 | 0.30 | −0.05 | −0.13 | −0.01 | −0.06 | AC022080.2 | −0.50 | 0.46 | −0.58 | 0.58 | −0.39 | MIR1200 | 0.28 | −0.39 | 0.25 | 0.38 | −0.12 |
| ANKRD20A2 | −2.29 | −0.47 | 2.74 | −0.04 | 2.11 | AC123769.1 | 0.73 | 0.43 | −1.40 | −0.27 | −1.16 | AL353795.1 | 0.21 | −0.73 | 0.37 | −0.80 | −0.03 |
| RNF138 | 0.45 | −0.16 | −0.42 | 0.01 | −0.27 | AC019197.1 | −0.36 | 0.24 | 0.15 | 0.50 | −0.15 | AP005901.2 | −0.39 | −0.99 | −1.61 | 1.63 | −1.15 |
| AC004448.2 | −1.28 | 0.55 | 0.38 | 1.06 | 0.68 | AC135012.1 | −0.71 | −2.08 | 0.38 | −0.46 | 1.72 | BNIP3P35 | 0.91 | −1.47 | 0.96 | −1.49 | −0.27 |
| DSG1-AS1 | 1.19 | 0.05 | −0.07 | 0.15 | −0.18 | FNDC1-IT1 | 1.17 | −1.27 | −2.29 | −2.17 | −1.29 | AL352984.1 | −0.30 | 0.23 | −0.13 | 0.06 | −0.82 |
| PSG8-AS1 | −1.57 | 0.43 | 0.22 | 1.14 | 0.00 | G34066 | 0.51 | −0.25 | 0.88 | −0.62 | −0.19 | MIR4319 | 0.11 | 0.05 | 0.60 | 0.26 | 0.18 |
| ST6GALNAC5 | −1.13 | 1.02 | 1.33 | 0.26 | 0.55 | BPIFA2 | 1.21 | −2.33 | −2.27 | 0.18 | −1.91 | AC073176.3 | 0.33 | −1.25 | −0.74 | 0.24 | −1.36 |
| CSTF3 | 0.34 | −0.36 | −0.20 | −0.19 | 0.06 | AC103810.2 | −0.22 | 0.02 | 0.32 | 0.07 | 0.38 | GTF2H4 | −0.13 | 0.60 | −0.83 | 0.45 | −1.26 |
| HEMGN | −1.70 | 0.73 | 1.04 | 0.74 | −1.05 | SLC25A6P5 | −0.82 | 0.97 | −1.22 | 1.98 | −1.06 | SCRT2 | 0.18 | −1.29 | −1.65 | 0.14 | −0.58 |
| NDUFA6-DT | −0.56 | 0.12 | 0.59 | 0.17 | 0.52 | ADORA2A | −0.54 | −0.05 | 0.03 | −0.37 | −0.55 | CYP2AC1P | 0.21 | 0.64 | −1.61 | −0.48 | −2.88 |
| SNORA40 | −0.63 | 0.48 | 0.41 | 0.24 | −0.23 | AC019227.1 | −0.20 | −0.21 | 0.15 | −0.04 | 0.33 | AC023141.6 | −0.61 | −0.67 | −0.11 | −0.16 | 0.27 |
| MEX3B | −0.70 | 0.75 | 0.88 | −0.10 | 0.09 | RALY-AS1 | −0.20 | −0.16 | 0.13 | −0.01 | 0.35 | AC074051.3 | −0.95 | NA | 1.21 | 0.92 | 2.80 |
| G3793 | −3.20 | −0.11 | 2.49 | 1.21 | 1.98 | FUNDC2P2 | 1.24 | −0.76 | −2.01 | 1.38 | −0.49 | IGHV4-59 | 0.95 | 0.19 | 0.45 | 0.03 | −0.06 |
| FERMT2 | −0.88 | 0.50 | 1.05 | −0.28 | −0.11 | CACNA1C-AS3 | 0.57 | −0.43 | −1.37 | −0.74 | −2.23 | AC078851.1 | 0.95 | −1.47 | −1.24 | −1.24 | −0.26 |
| FYCO1 | −0.24 | 0.31 | 0.19 | 0.14 | −0.06 | AC004223.3 | 0.59 | 0.19 | −0.17 | −0.34 | 0.11 | RN7SL45P | −0.14 | 0.00 | 0.12 | 0.47 | 1.18 |
| SLCO2A1 | 0.71 | −0.55 | −0.53 | −0.43 | −0.22 | AC005972.3 | 0.23 | −0.37 | −0.49 | −0.14 | 0.16 | HORMAD2-AS1 | −0.12 | 0.27 | −0.54 | −0.50 | −1.73 |
| AP3M1 | 0.34 | −0.12 | −0.26 | −0.04 | −0.17 | AC017006.1 | −0.78 | −0.14 | −1.06 | 0.08 | 0.22 | ALPP | −0.43 | 0.31 | 1.41 | −0.27 | 0.39 |
| MYH16 | −0.69 | 0.22 | 0.49 | 0.29 | 0.29 | AL513185.1 | 0.61 | −0.59 | 0.34 | −0.55 | 0.40 | AC018529.2 | 0.04 | −0.33 | −0.52 | 0.00 | 0.07 |
| AC079880.2 | 1.00 | −0.67 | −0.56 | −0.46 | −0.02 | AC084082.1 | −0.40 | −0.04 | 0.19 | −0.24 | −0.12 | AC027688.1 | −0.42 | −1.39 | −1.08 | 0.44 | 0.35 |
| SPRTN | 0.38 | −0.14 | −0.28 | −0.06 | −0.11 | AC020910.4 | −0.47 | −0.11 | 0.48 | −0.14 | 0.40 | AC053481.3 | 0.16 | −1.65 | −0.94 | 0.05 | 1.23 |
| AC009084.2 | −0.92 | 0.81 | 1.44 | 0.33 | 0.23 | GJA9 | 0.73 | −0.83 | 0.38 | 0.20 | 0.78 | AC079612.1 | 0.42 | −0.13 | −2.07 | 0.30 | −0.98 |
| G43233 | −1.55 | 0.45 | 1.87 | −0.75 | 0.55 | IL17A | 1.16 | −0.64 | −2.61 | −0.59 | −1.64 | AC021066.1 | 0.49 | −0.38 | −0.59 | −1.59 | −0.44 |
| OR5E1P | −1.09 | 1.08 | 2.23 | 0.38 | 0.82 | SKIV2L | −0.14 | −0.17 | −0.26 | 0.12 | 0.13 | AC000099.1 | 0.23 | −1.40 | −1.26 | 0.90 | 0.91 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| SERTAD1 | 0.86 | −0.51 | −0.76 | −0.12 | −0.98 | C15orf39 | 0.13 | −0.06 | −0.47 | −0.02 | −0.24 | SLC25A40 | 0.03 | −0.08 | −0.16 | 0.12 | 0.02 |
| AC093525.10 | −0.89 | 0.15 | 0.09 | 0.28 | 0.41 | AL929236.1 | 0.48 | −0.10 | −0.31 | 0.31 | 0.12 | AC245291.2 | 0.95 | −1.90 | −2.00 | −0.43 | −0.58 |
| POLB | 0.44 | −0.33 | −0.57 | −0.02 | −0.18 | CMTM5 | −0.63 | 0.81 | −0.95 | 0.49 | −0.82 | AC026410.1 | −0.34 | 1.71 | −1.68 | 2.60 | −2.05 |
| RNU4-2 | −0.84 | 0.33 | 0.32 | 0.37 | −0.02 | RNF121 | 0.12 | −0.06 | −0.14 | −0.02 | 0.07 | AL035454.1 | 0.30 | −0.57 | 0.31 | 0.02 | 0.49 |
| SLC48A1 | −0.29 | 0.23 | 0.27 | 0.03 | 0.03 | AL512288.2 | 0.36 | −0.21 | −0.15 | −0.13 | 0.24 | AC004112.1 | 0.09 | 0.10 | −0.79 | −0.05 | −0.30 |
| PIEZO2 | −0.70 | 0.54 | 1.30 | −0.14 | −0.42 | CTSLP8 | 1.02 | −1.81 | −1.96 | 0.85 | 0.62 | OR1D5 | 0.67 | −0.38 | 0.59 | −0.46 | −0.95 |
| NPM1P27 | 0.51 | −0.37 | −0.48 | −0.18 | −0.12 | AC092620.3 | 0.29 | −0.06 | −0.05 | −0.02 | 0.09 | MRC1L1 | −0.08 | 0.09 | −0.24 | 0.02 | −0.18 |
| KLHL42 | 0.37 | −0.21 | −0.26 | −0.15 | −0.12 | AC126615.2 | 0.38 | −0.16 | −0.51 | 0.00 | −0.19 | AC090502.1 | 0.21 | −1.77 | −1.77 | 0.72 | 1.59 |
| AC091078.1 | −1.59 | 0.46 | 0.81 | 0.28 | 0.16 | FAM149B1P1 | −1.07 | −0.44 | 0.29 | 0.63 | 0.13 | LINC02454 | 0.17 | −0.04 | 0.80 | −0.46 | −0.06 |
| AC138932.3 | −0.75 | 0.23 | 0.39 | 0.62 | 0.34 | SSBP3 | −0.11 | 0.13 | 0.12 | 0.10 | −0.06 | INPP5D | −0.05 | −0.06 | 0.44 | −0.28 | 0.05 |
| PPP1R3G | −0.79 | 0.56 | 0.47 | 0.17 | 0.65 | AP000577.1 | −0.31 | −0.01 | 1.06 | 0.12 | 0.51 | CR383658.1 | 0.29 | −1.37 | −0.98 | −0.69 | −0.99 |
| PUM1 | 0.20 | −0.04 | −0.20 | −0.03 | −0.14 | PQBP1 | 0.12 | −0.04 | −0.07 | 0.01 | −0.05 | OR7E129P | 0.47 | −1.09 | −1.31 | 0.89 | −0.63 |
| KMT2B | −0.57 | 0.18 | −0.03 | 0.33 | 0.20 | DOK4 | 0.20 | 0.23 | 0.21 | 0.08 | −0.16 | NSUN6 | −0.02 | 0.02 | 0.23 | −0.12 | 0.15 |
| B2M | 0.61 | −0.50 | −0.31 | −0.27 | −0.35 | AL157712.1 | 0.63 | −0.37 | 0.88 | −0.06 | 0.80 | SERF1B | −0.11 | −0.85 | 0.24 | 0.13 | 0.83 |
| AC011405.1 | −0.48 | 0.13 | 0.21 | 0.01 | 0.30 | EEF1GP3 | −0.98 | 0.26 | −0.11 | 0.63 | 0.51 | AL591516.4 | −0.18 | −1.16 | 1.51 | −0.10 | 1.78 |
| MKS1 | −0.41 | 0.22 | 0.19 | 0.28 | 0.20 | MAP4K5 | 0.09 | 0.14 | 0.09 | 0.00 | −0.10 | AL031587.4 | −0.33 | 0.23 | 0.05 | −0.93 | −1.75 |
| RNU2-5P | −1.29 | 0.88 | 0.86 | 0.25 | −0.68 | NEB | −0.19 | −0.11 | 0.50 | −0.13 | 0.26 | AL049833.1 | 0.63 | −0.45 | 0.77 | −0.20 | −0.78 |
| RDH12 | 0.84 | 0.13 | −0.14 | 0.28 | −0.26 | RNASE9 | 0.88 | −1.11 | −1.74 | 0.03 | −0.60 | AL035696.4 | 0.61 | 0.03 | −1.51 | 1.01 | −1.11 |
| RN7SL137P | −1.21 | 0.60 | 1.72 | −0.04 | 1.19 | LINC01426 | 0.51 | −0.97 | −0.48 | −1.06 | 0.16 | RNU6-738P | −0.33 | 0.14 | −0.22 | 0.81 | −0.63 |
| KIFC1 | 0.69 | −0.77 | −1.29 | −0.34 | −0.18 | SDHA | 0.12 | −0.08 | −0.22 | −0.07 | −0.06 | RSRC2 | −0.03 | −0.03 | −0.17 | −0.12 | −0.21 |
| AKR7L | −0.69 | 0.53 | 0.48 | 0.62 | 0.24 | RNU2-52P | −0.84 | 0.13 | 1.48 | −0.27 | 0.36 | AC243830.3 | 0.29 | −1.42 | −0.27 | −0.42 | 1.56 |
| NCKAP5L | −0.62 | 0.09 | 0.28 | 0.17 | 0.19 | CPLX2 | −0.35 | −0.05 | 0.01 | −0.22 | −0.28 | AL731557.1 | −0.18 | 0.31 | 2.88 | −0.65 | 0.61 |
| PRKAG2-AS1 | −1.05 | 0.45 | 0.84 | 0.00 | −0.27 | CENPUP2 | −0.73 | 0.32 | 3.64 | −0.80 | 0.84 | HMGB3P1 | −0.24 | −1.74 | −1.07 | −0.50 | 0.33 |
| CARS2 | −0.34 | 0.03 | 0.17 | 0.13 | 0.19 | EIPR1-IT1 | 0.25 | −0.17 | −0.20 | −0.14 | 0.09 | PPBPP2 | −0.32 | 0.29 | −1.03 | −0.30 | −0.01 |
| AC002558.1 | −0.81 | 0.06 | 0.28 | 0.18 | 0.17 | C3orf33 | −0.53 | 0.48 | 0.54 | −0.03 | −0.02 | AL162464.2 | 0.19 | −0.74 | −2.14 | −0.39 | −1.99 |
| AC104759.1 | −1.22 | 0.78 | 0.59 | 1.33 | 0.29 | AC013460.1 | 0.50 | 0.01 | −0.96 | −0.10 | −0.56 | AC098476.1 | 0.15 | 0.42 | −0.39 | 0.39 | −0.32 |
| ATP2C1 | 0.32 | −0.03 | −0.17 | 0.06 | −0.13 | G36500 | −0.98 | 1.18 | 0.56 | 0.84 | −1.17 | AC211486.5 | 0.21 | 0.41 | 0.32 | 1.73 | 0.78 |
| RING1 | −0.32 | 0.14 | 0.15 | 0.16 | 0.17 | AC055874.1 | −0.87 | 0.98 | 1.90 | 0.75 | 0.42 | AC133550.2 | −0.07 | 0.07 | 0.52 | −0.21 | −0.06 |
| MICA | −0.49 | 0.02 | 0.20 | 0.16 | 0.04 | AL109983.1 | 0.57 | 0.34 | 0.82 | 0.62 | −0.43 | LINC02180 | 0.35 | −1.01 | −1.00 | 0.55 | 0.05 |
| MARS2 | 0.70 | −0.27 | −0.37 | −0.15 | −0.27 | RNF113B | −0.43 | −0.05 | −0.25 | −0.43 | 0.09 | PSME2P6 | 0.52 | −0.73 | −1.55 | 0.06 | −0.67 |
| JGT1P4-STRA61 | −0.87 | 0.75 | 0.62 | −0.01 | −0.40 | AC026367.3 | 0.52 | 0.59 | −0.43 | 0.60 | −0.36 | FNDC1 | −0.11 | 0.38 | 1.25 | −2.17 | −0.71 |
| STK32A-AS1 | −1.31 | 1.57 | 0.06 | 0.80 | 0.19 | BABAM1 | −0.17 | 0.11 | −0.02 | 0.16 | 0.04 | AC090618.1 | −0.33 | 0.13 | 0.59 | 1.92 | 0.61 |
| FSCN2 | −0.92 | 0.64 | 0.39 | 0.61 | 0.02 | SMYD4 | −0.11 | −0.20 | 0.14 | −0.19 | 0.26 | AC006450.2 | −0.47 | −0.42 | 0.37 | 0.87 | 0.18 |
| CHRM3 | −1.06 | 0.78 | 1.43 | 0.38 | 0.67 | AC055839.1 | −0.29 | 0.14 | 0.40 | −0.03 | −0.06 | RPL23AP87 | 0.13 | 0.06 | −0.50 | 0.40 | −0.03 |
| HPS6 | 0.51 | −0.24 | −0.45 | 0.02 | −0.23 | FAM117B | −0.15 | 0.21 | −0.02 | 0.26 | −0.15 | PDCD6IPP1 | 0.12 | −0.12 | −1.07 | 0.85 | −0.71 |
| ADH7 | 1.38 | −0.04 | 0.12 | 0.00 | −1.34 | LAX1 | 0.32 | −0.29 | 0.26 | −0.35 | 0.07 | AC022325.1 | 0.22 | −0.63 | −0.55 | 0.22 | 0.69 |
| AURKC | −0.64 | 0.49 | 0.16 | 0.19 | −0.30 | KCNH1-IT1 | 0.97 | −0.64 | −2.43 | 0.57 | −0.32 | AL354941.1 | −0.16 | 1.07 | 1.26 | 0.13 | −0.86 |
| DERL1 | 0.45 | −0.11 | −0.22 | −0.03 | −0.31 | RN7SKP78 | −0.46 | −0.73 | −0.61 | −0.21 | 0.39 | AC109361.2 | 0.18 | 0.01 | −1.47 | 0.71 | −0.01 |
| SLC26A6 | 0.56 | −0.45 | −1.20 | 0.04 | −0.17 | NPM1P5 | 0.72 | −0.70 | −1.96 | −0.09 | −0.99 | HMGB1P36 | −0.67 | −0.11 | 0.00 | −0.24 | 0.23 |
| LINC02242 | −1.55 | −0.06 | 1.38 | 1.54 | 2.44 | AC022915.2 | 0.56 | −0.99 | −1.30 | 0.16 | −0.52 | ALG10 | 0.05 | −0.04 | 0.17 | −0.06 | 0.06 |
| MOSPD1 | 0.67 | −0.23 | −0.10 | −0.21 | −0.34 | AC134026.1 | −1.32 | 1.14 | 1.58 | 0.82 | −0.82 | OR4A43P | 0.42 | −2.23 | 0.34 | −1.54 | 0.80 |
| ARG1 | 0.98 | −0.44 | 0.14 | 0.66 | −0.37 | DOCK2 | 0.28 | −0.56 | −0.05 | −0.34 | 0.27 | LINC01549 | 0.12 | −0.85 | −1.53 | −0.37 | 0.07 |
| ALDH8A1 | −0.76 | 0.22 | 0.89 | −0.30 | 0.47 | AC007099.1 | −0.35 | −0.24 | −0.03 | −0.38 | 0.65 | AC079601.1 | −0.13 | 0.32 | 0.60 | 0.43 | 0.13 |
| MAD2L1BP | 0.54 | −0.34 | −0.59 | −0.13 | −0.47 | RNASE8 | −0.80 | −0.34 | 0.70 | −0.55 | 0.64 | RBMX2P2 | −0.32 | 0.22 | 2.66 | −0.28 | 0.21 |
| C1QTNF4 | −1.33 | 1.12 | 2.19 | 0.09 | −0.11 | AC010976.1 | −0.12 | −0.10 | 0.18 | −0.12 | 0.26 | OR7A2P | 0.31 | −0.78 | −1.51 | −0.50 | −2.84 |
| HDLBP | 0.36 | −0.17 | −0.29 | −0.19 | −0.28 | AC009228.1 | 0.52 | −0.81 | 0.46 | −0.62 | 0.29 | PEBP1P2 | −0.15 | −0.55 | −0.90 | 1.29 | 0.09 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC010632.2 | −0.83 | 0.53 | 0.54 | 0.37 | 0.34 | RN7SL47P | 0.63 | −0.05 | 0.53 | −0.40 | −0.17 | C4BPAP1 | −0.13 | 0.08 | −0.66 | 0.32 | 0.11 |
| ATP9B | −0.27 | 0.19 | 0.16 | 0.15 | 0.07 | AC106788.1 | −0.87 | −0.24 | 1.20 | −1.02 | 0.93 | CTC-550B14.8 | −0.19 | −1.55 | −0.80 | −0.56 | 0.63 |
| CTNNAL1 | 0.46 | −0.17 | −0.19 | −0.01 | −0.34 | DLX6-AS1 | −0.31 | 0.23 | 0.23 | −0.11 | −0.29 | AC073614.1 | 0.59 | −0.77 | −0.63 | 0.86 | 0.47 |
| ITGB7 | −0.80 | 0.65 | 0.61 | 0.13 | −0.08 | AC107072.2 | −0.84 | 0.61 | 0.46 | 0.46 | 0.66 | AC004920.1 | 0.84 | −0.69 | −1.81 | 1.10 | −0.66 |
| BUD13 | 0.29 | −0.20 | −0.31 | −0.05 | −0.10 | ATP6AP1 | 0.12 | 0.11 | 0.06 | 0.10 | −0.17 | G16028 | −0.07 | 0.19 | 0.54 | 0.04 | −0.03 |
| SNORD12C | 0.67 | −0.27 | −1.01 | 0.23 | −0.79 | AL353662.2 | 0.22 | −0.38 | −0.26 | −0.22 | 0.14 | AC023934.1 | −0.48 | 0.09 | 0.11 | 0.35 | 0.44 |
| STAC | −0.91 | −0.09 | 0.09 | 0.04 | −0.06 | AC083837.2 | 0.34 | −0.73 | −0.37 | −0.16 | 0.13 | AC128709.3 | 0.36 | 0.98 | 1.53 | 0.54 | 0.25 |
| ALX1 | −1.13 | 0.31 | 0.10 | 0.56 | 0.30 | AL928921.2 | −0.47 | −0.08 | 0.38 | 0.43 | 0.44 | AL391903.2 | 0.94 | −0.87 | −1.10 | 1.72 | −0.60 |
| GATAD1 | −0.31 | −0.01 | 0.39 | 0.02 | 0.31 | AC008735.1 | −0.30 | −0.03 | −0.58 | −0.20 | −0.29 | HMG20A | 0.02 | 0.06 | 0.02 | 0.08 | −0.04 |
| STX3 | 0.28 | 0.02 | −0.37 | 0.03 | −0.19 | AC106738.2 | −0.53 | 1.22 | −0.52 | 1.02 | 0.49 | RPSAP31 | 0.29 | −1.24 | −1.88 | 1.17 | 0.34 |
| CDK14 | −0.74 | 0.37 | 1.22 | −0.19 | 0.33 | LRRC66 | −0.37 | −0.63 | 0.70 | −0.36 | 1.11 | CD8B | −0.11 | −0.16 | 0.27 | −0.19 | 0.75 |
| ST13P11 | 0.77 | −0.80 | −0.85 | −0.06 | 0.13 | LINC00680 | −0.14 | 0.24 | −0.03 | 0.25 | −0.12 | KIAA1522 | 0.05 | 0.25 | −0.16 | 0.32 | 0.01 |
| DDX5 | 0.31 | −0.21 | −0.25 | −0.16 | −0.14 | AC012309.2 | −1.49 | 0.19 | 2.27 | 0.62 | 2.05 | OR8J1 | −0.33 | −0.73 | −1.64 | 0.89 | −0.32 |
| DNMBP | −0.37 | 0.27 | 0.17 | 0.25 | 0.02 | CEP44 | −0.13 | 0.22 | 0.18 | 0.14 | −0.03 | AL365181.2 | 0.15 | −0.38 | −0.05 | 0.28 | 0.10 |
| DPH3 | 0.59 | −0.30 | −0.44 | −0.17 | −0.33 | AC022558.3 | −0.50 | 0.23 | −0.21 | 0.50 | −0.05 | LINC02333 | −0.50 | 0.59 | 0.27 | 0.67 | −1.66 |
| CCT6P3 | −0.39 | 0.17 | 0.32 | 0.05 | 0.25 | PATJ | 0.15 | 0.07 | −0.21 | 0.11 | 0.00 | AC009623.1 | 0.32 | −0.25 | −0.03 | 0.82 | −1.26 |
| AC092542.1 | −1.75 | 0.55 | 1.50 | 0.94 | 0.74 | HNRNPA1P59 | 0.31 | −0.42 | 0.34 | −0.42 | 0.02 | RABEPKP1 | −0.56 | 0.20 | 1.66 | −0.95 | 0.74 |
| PPP1R9B | 0.34 | −0.36 | −0.57 | 0.05 | 0.01 | SERPINC1 | −0.45 | −0.37 | −0.03 | −0.62 | −0.44 | AC005865.1 | −0.09 | −0.50 | −0.75 | 0.10 | 0.08 |
| NACA | 0.64 | −0.16 | −0.31 | −0.23 | −0.59 | SSC4D | −0.29 | 0.33 | 0.45 | 0.37 | 0.34 | AP005018.2 | −0.11 | −0.12 | −0.16 | 0.25 | 0.37 |
| EIPR1 | 0.43 | −0.30 | −0.39 | −0.11 | −0.06 | AC113194.1 | 1.82 | −0.79 | −0.99 | −0.42 | −1.15 | LINC00523 | −0.23 | −0.47 | −2.42 | 0.78 | 0.00 |
| MSNP1 | 0.97 | −0.62 | −0.81 | −0.22 | −0.22 | RNA5SP440 | 0.62 | −1.56 | 0.78 | 0.21 | 2.11 | AL358972.1 | −0.53 | 0.04 | 1.03 | −1.02 | 1.22 |
| ARRDC3 | 0.58 | −0.21 | −0.40 | −0.13 | −0.34 | MIR194-2HG | 0.64 | −1.19 | 0.25 | −0.03 | 0.85 | OR51R1P | 0.22 | −1.19 | 1.97 | 0.26 | 1.96 |
| HSP90B3P | −1.05 | 0.32 | 1.23 | 0.12 | 0.78 | RPS3AP26 | 0.24 | 0.18 | 0.22 | −0.20 | 0.00 | AC024589.2 | −0.48 | −0.11 | −1.98 | 1.32 | −1.75 |
| G4403 | −1.47 | 0.65 | 1.15 | 0.58 | 0.32 | AC073578.2 | 1.01 | −1.11 | −2.66 | 0.60 | 1.26 | AC073346.2 | 0.26 | 0.30 | −1.09 | 0.59 | −0.78 |
| NRAV | 0.42 | −0.19 | −0.52 | −0.07 | −0.13 | C2orf73 | −0.56 | −0.40 | −1.22 | −0.10 | −0.11 | AL049641.1 | −0.76 | 0.11 | 0.86 | 0.35 | −0.09 |
| MRPS2 | 0.46 | −0.19 | −0.46 | −0.13 | −0.19 | G12797 | −1.23 | −0.73 | 1.61 | 0.20 | 2.44 | G22194 | 0.90 | −0.63 | −0.62 | −0.33 | −1.38 |
| NXT2 | 0.79 | −0.39 | −0.25 | −0.13 | −0.30 | RNU5E-10P | 1.05 | −0.68 | 0.49 | −0.09 | 1.78 | AC011481.1 | −0.18 | 0.85 | 0.93 | 2.07 | −0.50 |
| FCHSD1 | 0.58 | −0.54 | −1.07 | −0.18 | −0.29 | AC025280.3 | 0.34 | −0.97 | −0.89 | −0.78 | −0.20 | AL451007.1 | 0.12 | 0.57 | −0.29 | −0.14 | −0.42 |
| ERVFRD-3 | 1.34 | −0.27 | −1.17 | 0.03 | −0.69 | FAT4 | −0.24 | 0.32 | 1.05 | −0.47 | −0.02 | MS4A12 | −0.29 | 0.52 | −0.86 | 1.34 | −1.94 |
| APEX1 | 0.33 | −0.10 | −0.27 | −0.03 | −0.18 | KPTN | 0.22 | −0.18 | −0.48 | −0.09 | 0.18 | MIR30B | −0.07 | −0.04 | 0.87 | −0.44 | 0.19 |
| AL139193.1 | 1.92 | −1.29 | −0.46 | −0.28 | 0.62 | AC131157.1 | −0.96 | 0.54 | −0.14 | 1.14 | −0.64 | AC009090.4 | −0.08 | −0.22 | −0.21 | 0.20 | 0.29 |
| LINC01137 | 0.52 | −0.30 | −0.18 | −0.01 | 0.23 | RNU6-689P | 0.69 | −0.52 | 0.21 | −0.50 | 0.26 | RNU3P3 | −0.27 | 0.46 | −0.67 | 0.82 | −0.83 |
| CPEB3 | −0.51 | 0.56 | 0.59 | 0.24 | 0.29 | GIN1 | 0.20 | −0.15 | −0.12 | 0.01 | 0.12 | L22NC03-63E9. | 0.29 | −0.99 | −2.48 | 0.01 | −1.51 |
| SEPHS1 | 0.26 | −0.11 | −0.28 | −0.04 | −0.15 | DDN-AS1 | 0.42 | −0.48 | −0.48 | −0.15 | 0.11 | AC079140.3 | 0.12 | −0.26 | 0.41 | −0.17 | 0.40 |
| RAB27B | 0.68 | 0.18 | −0.04 | 0.34 | −0.28 | LINC00491 | 0.72 | −0.70 | −0.44 | 0.78 | 0.50 | RPL10P11 | −0.58 | 0.09 | 1.82 | 0.88 | −0.71 |
| NKAIN3-IT1 | −1.20 | 0.53 | 0.60 | 0.67 | 0.52 | C15orf54 | 0.39 | 0.00 | −0.16 | −0.32 | −0.51 | RNVU1-8 | −0.94 | 0.62 | 1.04 | 2.39 | 0.71 |
| SERPINB7 | 1.31 | −0.25 | 0.19 | 0.48 | −1.14 | AC098934.2 | −0.31 | −0.29 | −1.13 | 0.49 | −0.40 | AC090912.3 | 0.19 | −0.29 | 0.97 | −0.40 | 0.67 |
| PPIAP30 | −0.94 | 0.04 | −0.27 | 0.83 | −0.12 | AP001631.1 | −0.96 | −1.02 | 0.70 | −2.25 | −1.40 | MTND4P4 | −0.30 | 0.05 | −0.77 | 1.82 | −1.73 |
| OSTM1 | 0.45 | −0.24 | −0.52 | −0.10 | −0.24 | AC092802.2 | −0.24 | 0.40 | 0.61 | 0.12 | 0.30 | MTCO2P8 | −0.94 | 0.05 | 0.98 | −1.64 | −0.55 |
| 1-Sep | −0.59 | 0.06 | 1.00 | −0.18 | 0.42 | RNU6-601P | 0.90 | −0.88 | 1.87 | −0.10 | 1.04 | AC003071.1 | 0.39 | 0.32 | −1.06 | 2.04 | −0.34 |
| CYB5R3 | −0.41 | 0.28 | 0.34 | −0.05 | −0.03 | AC118754.1 | 0.57 | 0.23 | −0.33 | 0.47 | −0.26 | LINC01413 | 0.49 | −0.47 | −1.20 | 0.77 | −1.36 |
| MIR3945HG | 2.37 | −2.07 | −4.53 | 0.14 | −3.07 | AL118516.1 | 0.22 | −0.09 | −0.05 | 0.04 | −0.07 | AC022092.1 | 0.69 | −1.04 | −1.20 | 0.44 | 0.49 |
| FBXL20 | −0.39 | 0.42 | 0.50 | 0.16 | −0.08 | AF064860.1 | −0.81 | 0.35 | 0.47 | 0.30 | −0.19 | AC073941.1 | −0.56 | −0.24 | 0.13 | −0.70 | −1.65 |
| DDIT4L | −1.26 | 0.85 | 0.89 | 0.11 | 0.19 | DPP10-AS1 | −0.70 | 1.14 | −2.20 | 0.83 | −3.37 | CTAGE8 | −0.10 | 0.13 | −0.27 | 0.59 | 0.46 |
| CYB5RL | −0.47 | −0.17 | 0.79 | −0.28 | 0.29 | AC002553.2 | 0.40 | 0.12 | 0.21 | −0.14 | 0.02 | AC009501.1 | −0.11 | 0.13 | 0.55 | 0.09 | 0.33 |
| KCTD8 | −1.51 | 1.02 | 0.91 | 1.47 | −0.51 | SNORA59A | 0.44 | −0.27 | 0.31 | −0.15 | 0.31 | FP475955.1 | −0.93 | 0.49 | 0.60 | −0.66 | −0.36 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| RBBP4 | 0.21 | −0.12 | −0.21 | 0.01 | −0.08 | RN7SL353P | −0.85 | −0.04 | 1.17 | 0.71 | 0.79 | AC131056.5 | −0.32 | −0.45 | 0.76 | 0.48 | −0.49 |
| CCR5 | 1.14 | −1.07 | 0.06 | −0.72 | 0.67 | IGSF8 | 0.24 | −0.01 | −0.19 | 0.16 | −0.07 | AC005034.4 | −0.93 | 0.17 | 1.15 | 1.03 | 0.26 |
| RPL9 | 0.47 | 0.03 | −0.18 | 0.20 | −0.58 | AP001136.1 | −0.86 | 0.13 | −0.02 | −0.25 | −0.73 | MUC19 | 0.11 | −0.24 | −0.53 | 0.41 | −0.07 |
| F7 | −1.10 | 0.53 | 1.11 | −0.19 | 0.10 | AC006435.5 | 0.45 | −0.17 | 0.18 | 0.15 | 0.49 | AC064875.1 | 0.10 | 0.41 | 0.48 | 0.91 | 0.20 |
| MFSD1P1 | 0.90 | −0.35 | −0.57 | −0.32 | −0.28 | BMS1P4 | −0.22 | −0.11 | −0.13 | 0.23 | 0.54 | AC108206.1 | −0.17 | −0.37 | 0.36 | −0.14 | 0.32 |
| NDUFA8 | 0.40 | −0.10 | −0.06 | −0.28 | −0.17 | FAM177A1P1 | −0.79 | 0.34 | 1.36 | 0.11 | −0.58 | AC087564.1 | −0.13 | −0.14 | −0.14 | −0.15 | −0.20 |
| RPSAP50 | −2.09 | 0.90 | 1.95 | −0.96 | 0.99 | SNORA1 | 0.41 | −0.45 | 0.03 | 0.10 | 0.51 | G39805 | 0.40 | −0.37 | −0.94 | 1.00 | −0.41 |
| DYRK3 | 0.82 | −0.38 | −1.07 | −0.37 | −1.03 | AL109924.4 | −0.91 | 0.53 | 3.28 | −1.52 | −0.35 | MAPK11 | 0.06 | −0.10 | −0.42 | 0.00 | −0.08 |
| ABCD2 | −1.33 | 1.23 | 1.13 | 0.45 | 0.00 | AC005539.1 | −1.35 | 1.85 | 0.39 | 1.63 | −1.50 | PPP4R1-AS1 | −0.13 | −0.87 | −0.59 | 0.92 | 1.56 |
| PPM1H | −0.65 | 0.52 | 0.92 | 0.27 | 0.51 | AC002470.1 | 0.88 | −0.55 | −0.19 | 0.01 | −0.17 | GHRH | 0.24 | −0.03 | −1.66 | 0.24 | −0.82 |
| XDC2P-NPIPB1 | −0.49 | 0.18 | 0.59 | 0.08 | 0.24 | AC006197.1 | 0.83 | −0.21 | −0.22 | 1.03 | 0.53 | KRT90P | 0.33 | −0.13 | 1.55 | 0.02 | 0.78 |
| RPL19P16 | −1.78 | 2.95 | 0.31 | 2.17 | −0.55 | RN7SL32P | −0.78 | −0.56 | −1.11 | 0.48 | −1.40 | LINC02005 | 0.17 | −1.65 | −2.85 | −0.07 | −1.46 |
| AP002784.2 | 1.08 | −0.92 | −0.81 | −0.31 | 0.00 | C4BPAP2 | 0.74 | −0.52 | −1.16 | 0.10 | −0.32 | AP001180.1 | 0.24 | −0.13 | 0.57 | 0.70 | 0.00 |
| MITD1 | 0.31 | −0.19 | −0.11 | −0.19 | −0.05 | AL157884.3 | −0.35 | −0.79 | −0.15 | 0.01 | 0.64 | SLC25A1 | 0.03 | 0.02 | −0.20 | 0.27 | 0.00 |
| DUOXA1 | 0.67 | −0.42 | −0.87 | 0.00 | −0.07 | AC114546.2 | −0.57 | 0.14 | 0.49 | −0.04 | 0.35 | LINC01547 | 0.04 | −0.14 | 0.15 | −0.47 | 0.16 |
| RNU6-1045P | 1.31 | −0.77 | −1.43 | −0.76 | −0.70 | NAPRT | 0.20 | −0.14 | −0.78 | 0.56 | 0.01 | AL391244.1 | −0.04 | −0.07 | 0.18 | 0.05 | 0.19 |
| RP11-782C8.1 | −0.55 | 0.57 | −0.21 | 0.56 | −0.07 | AC105917.1 | −1.38 | 0.45 | −0.46 | 0.29 | 0.07 | MESTP3 | −0.40 | −0.21 | 0.41 | 0.63 | 1.92 |
| AP3S1 | 0.50 | −0.30 | −0.17 | −0.14 | −0.12 | GAL3ST2 | −0.86 | −0.27 | −0.08 | 0.02 | −0.73 | GAPT | −0.10 | −0.26 | 0.99 | −0.26 | 0.50 |
| CXCR2 | 0.97 | −0.61 | −0.93 | −0.24 | −1.14 | AC009093.1 | 0.22 | −0.15 | 0.22 | 0.02 | 0.40 | SNORD121A | 0.09 | −0.67 | 0.48 | 0.31 | 0.96 |
| AL356019.2 | −0.76 | 0.36 | 1.06 | 0.19 | 0.15 | AC012435.2 | −0.34 | 0.33 | −0.53 | −0.23 | −0.26 | AL157938.1 | −0.26 | 0.13 | 0.34 | −0.59 | −0.56 |
| MIR1207 | 1.52 | −0.11 | −0.85 | 0.50 | −0.10 | PAM16 | 0.24 | −0.31 | −0.26 | 0.11 | 0.38 | AD000813.1 | 0.09 | −1.07 | −1.60 | −0.09 | 0.12 |
| SLC25A21-AS1 | −1.38 | 1.76 | 0.40 | 0.87 | −0.37 | AC073862.5 | −0.69 | 1.42 | 0.82 | 0.38 | −0.08 | RN7SL164P | 0.49 | 0.29 | 0.26 | 1.29 | −0.44 |
| RN7SL832P | −0.94 | −0.51 | 0.46 | −0.23 | 0.47 | BAHCC1 | −0.19 | −0.18 | −0.36 | 0.20 | 0.16 | AL139231.1 | −0.54 | −0.94 | −1.43 | 0.10 | 0.77 |
| SLC26A9 | 1.23 | −0.87 | −0.92 | 0.19 | −1.38 | AC093249.6 | −0.29 | 0.18 | −0.04 | −0.06 | −0.01 | MARK3P3 | 0.21 | −0.82 | 2.22 | 0.22 | 0.97 |
| BEGAIN | −0.76 | 0.09 | 0.36 | 0.27 | 0.34 | AL451074.5 | 1.05 | 0.13 | −2.08 | −0.41 | −1.15 | RNU6-517P | −0.22 | −0.47 | 0.00 | −0.60 | 0.14 |
| SH3TC1 | 0.76 | −0.71 | −1.00 | −0.50 | −0.78 | AC007496.2 | −0.29 | −0.01 | −0.15 | 0.31 | 0.23 | AC109780.1 | −0.36 | 0.43 | −0.45 | 0.63 | −2.48 |
| FUNDC1 | 0.56 | −0.17 | −0.34 | −0.06 | −0.22 | PSMA6P2 | 1.05 | 0.04 | 0.16 | −0.58 | −0.68 | G36296 | 0.22 | 1.49 | −1.08 | 1.22 | −0.27 |
| SLAIN1 | −0.93 | 0.22 | 0.54 | 0.39 | 0.51 | SERPINH1P1 | 0.71 | −0.82 | −2.81 | −0.16 | 1.02 | FBXL4 | −0.03 | 0.16 | 0.08 | 0.12 | −0.09 |
| LINC01154 | −2.21 | 1.31 | 1.29 | −0.35 | −0.64 | AC005342.1 | −0.83 | −0.56 | −0.54 | 0.75 | 1.70 | AC093698.1 | 0.57 | −0.48 | −0.33 | 0.63 | −1.17 |
| SPINK7 | 1.73 | −0.60 | −0.91 | 0.77 | −1.57 | KCTD6 | −0.15 | 0.08 | 0.38 | −0.04 | 0.03 | OR4A9P | 0.33 | −0.82 | −1.84 | 1.22 | 1.46 |
| GPRIN2 | −0.81 | 0.92 | 0.66 | 0.91 | 0.41 | LINC02583 | −0.75 | 0.39 | 0.18 | 0.40 | 0.07 | MS4A2 | −0.08 | 0.33 | 1.80 | 0.30 | 0.75 |
| GSTCD | 0.48 | −0.31 | −0.40 | −0.06 | −0.09 | AC008073.2 | −0.44 | 0.62 | 1.14 | 0.10 | 0.32 | AL132822.1 | −0.28 | −1.65 | 0.54 | −0.19 | 0.82 |
| C3orf52 | −0.78 | 0.84 | 1.31 | 0.25 | 0.36 | OR56A7P | −1.16 | −0.05 | 1.58 | 0.35 | 1.13 | AC090001.2 | 0.36 | −0.47 | 0.17 | −0.42 | −1.33 |
| CHEK2 | 0.46 | −0.61 | −0.63 | −0.18 | 0.21 | AC114760.2 | −0.19 | −0.34 | 0.11 | −0.50 | 0.27 | AL109954.1 | 0.51 | −0.57 | −0.29 | −0.64 | 0.43 |
| MESTIT1 | −1.79 | 0.10 | 2.67 | −0.32 | 0.80 | OR6C74 | 1.38 | −1.54 | −1.32 | 0.94 | 0.73 | GPR55 | 0.11 | −0.64 | −0.23 | −0.59 | 0.35 |
| CHP2 | −1.12 | 1.08 | 2.23 | 1.22 | 0.23 | HNRNPA1P42 | 0.91 | 0.12 | −1.23 | 0.72 | −1.24 | RNU1-68P | −0.17 | −0.08 | 0.11 | −0.29 | 1.50 |
| AC062004.1 | −1.54 | 1.81 | 0.97 | 0.15 | −0.93 | AC018638.6 | −0.42 | −0.59 | 0.58 | −0.56 | 0.57 | AP000807.1 | 0.26 | −0.60 | 1.40 | −0.36 | 1.46 |
| CDCA7 | 0.73 | −0.73 | −0.80 | −0.06 | 0.13 | MKRN2OS | 0.22 | −0.03 | −0.15 | 0.24 | 0.09 | AL360157.1 | −0.13 | −0.89 | 0.11 | −1.19 | 1.03 |
| RPL14 | 0.50 | −0.18 | −0.17 | −0.24 | −0.21 | AC110760.1 | −0.50 | 0.63 | 0.70 | 0.09 | −0.50 | AC087276.2 | 0.07 | 0.09 | −0.26 | 0.14 | −0.03 |
| SMYD3 | −0.30 | 0.14 | 0.44 | −0.06 | 0.20 | LINC00298 | −0.71 | −0.10 | 1.03 | 0.73 | 1.02 | AL359918.1 | −0.16 | 0.21 | −0.52 | 0.71 | 0.66 |
| IL36A | 2.76 | −2.43 | −3.92 | 0.78 | −3.04 | AC110285.5 | −0.71 | 0.66 | −1.37 | 1.68 | 0.52 | AL512844.2 | −0.41 | −0.27 | −1.98 | 1.15 | −0.92 |
| RNA5SP202 | −1.37 | 0.61 | −0.29 | 0.93 | −0.67 | HTR1DP1 | 0.21 | 0.12 | −0.63 | 0.02 | −0.35 | G31097 | 0.20 | −0.23 | −0.21 | −0.34 | 0.31 |
| AC018413.1 | 0.86 | −0.21 | −0.66 | 0.29 | 0.18 | MIR3198-1 | 0.71 | −1.43 | −0.68 | −0.19 | 0.11 | KRBOX1-AS1 | 0.16 | −0.32 | −1.18 | 0.03 | −0.77 |
| LINC02288 | −1.06 | 0.09 | 0.21 | 0.31 | −0.04 | SERINC1 | −0.18 | 0.24 | 0.29 | 0.06 | −0.07 | AC012377.1 | −0.15 | −0.50 | −0.03 | 0.10 | 0.11 |
| PKDREJ | −0.71 | 0.21 | 0.41 | 0.22 | 0.15 | NPIPB1P | −0.52 | 0.34 | 1.09 | 0.92 | 0.86 | OR8H2 | −0.27 | 0.11 | −2.12 | 0.26 | −0.53 |
| RNASET2 | −0.49 | 0.19 | 0.22 | 0.01 | 0.36 | HMCN1 | 0.24 | 0.40 | 0.59 | −0.40 | −0.22 | AC124861.1 | −0.31 | −0.23 | 1.04 | 0.97 | 2.18 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| ATP5F1E | 0.58 | −0.24 | −0.16 | −0.25 | −0.15 | AC108156.1 | −1.19 | −0.70 | 1.47 | 0.86 | 1.63 | AC068858.1 | 0.39 | −1.60 | −0.76 | −0.74 | −0.14 |
| FBXW11P1 | −1.40 | 0.54 | 0.95 | −0.33 | 0.53 | FABP5P14 | −1.32 | 0.52 | 3.12 | 1.81 | 1.65 | AC118273.1 | 0.31 | −1.38 | −1.89 | 0.14 | 0.35 |
| NUFIP1 | 0.48 | −0.34 | −0.78 | −0.02 | −0.32 | GFRAL | −0.88 | 0.64 | 1.68 | −0.20 | −0.13 | AC099342.1 | 0.27 | −1.06 | 0.74 | 0.54 | 0.13 |
| FADS2P1 | 2.08 | −0.21 | −2.21 | 1.02 | −1.18 | CLCF1 | 0.20 | −0.18 | −0.26 | −0.40 | −0.18 | AC002519.2 | −0.35 | −0.63 | 0.19 | 0.28 | −1.27 |
| IFFO1 | −0.71 | −0.15 | 0.35 | 0.09 | 0.30 | HIF1AN | −0.11 | 0.15 | 0.28 | 0.02 | 0.10 | AC004808.1 | −0.26 | −1.05 | 0.86 | −0.82 | 1.75 |
| CFAP61 | −1.13 | −0.04 | 0.14 | 0.28 | −0.20 | LINC02475 | 0.85 | 0.11 | −1.84 | −0.39 | −0.39 | AC133473.1 | −0.06 | −0.33 | 0.28 | −0.44 | 0.43 |
| MYL3 | −1.21 | 0.98 | 0.88 | 0.41 | 0.04 | MIR200C | 0.50 | −0.22 | −0.61 | 0.32 | −0.14 | AC109136.1 | 0.40 | −0.72 | −0.80 | 1.04 | 0.06 |
| RP2 | 0.51 | −0.35 | −0.14 | −0.20 | −0.26 | DNAJC19P9 | 0.95 | −0.40 | −2.27 | −0.53 | −1.83 | AL162311.2 | 0.11 | −1.59 | 0.53 | −0.18 | 0.95 |
| RNVU1-15 | 1.26 | −1.31 | −1.54 | −2.31 | −0.66 | KLHL35 | −0.25 | 0.25 | 0.64 | 0.02 | 0.33 | PRICKLE2 | −0.04 | −0.07 | −0.07 | −0.13 | −0.07 |
| IVNS1ABP | 0.52 | −0.29 | −0.45 | −0.04 | −0.08 | DUXAP4 | −0.91 | 0.44 | 1.20 | 1.12 | −0.10 | IGLV1-47 | 0.92 | 0.48 | 0.54 | −1.12 | −1.27 |
| AGRN | 0.52 | −0.47 | −1.10 | 0.14 | −0.07 | MIR9-3HG | 0.44 | −1.48 | −1.12 | 0.02 | 0.56 | AL109945.1 | −0.27 | −1.18 | −0.28 | 0.67 | 0.68 |
| CYTOR | 0.77 | −0.73 | −0.60 | −0.82 | −0.42 | KRT18P57 | 0.26 | −0.19 | 0.13 | −0.13 | 0.19 | AL034397.3 | 0.09 | 0.10 | 0.67 | −0.01 | 0.11 |
| GADD45A | 0.54 | −0.29 | −0.57 | −0.37 | −0.44 | HIST2H2BC | 0.20 | −0.18 | −0.10 | −0.07 | −0.04 | AL139130.1 | −0.11 | −0.27 | −1.68 | 0.25 | −0.38 |
| HMGB3P10 | −0.71 | 0.19 | 0.70 | 0.15 | 0.25 | AC079760.1 | −0.86 | −0.43 | −1.63 | −0.43 | −0.84 | AL512633.1 | −0.09 | −0.50 | −0.73 | 0.04 | 0.12 |
| SLC23A2 | 0.43 | −0.35 | −0.64 | 0.03 | −0.05 | AL450226.1 | 0.35 | −0.04 | 0.00 | 0.34 | 0.12 | GALNT4 | −0.08 | 0.16 | −0.68 | 0.46 | −0.77 |
| AL589843.2 | −1.18 | 0.41 | 0.57 | −0.70 | 0.34 | APAF1 | −0.10 | −0.09 | 0.20 | −0.11 | 0.29 | KRTAP13-2 | 0.45 | −0.56 | 0.16 | −1.04 | −1.24 |
| G25250 | 2.51 | 0.21 | −0.73 | −0.09 | −1.03 | CSNK1G2P1 | −0.35 | 0.10 | −0.36 | 0.23 | −0.25 | FAM76A | −0.02 | 0.12 | 0.16 | 0.11 | −0.03 |
| ARHGAP25 | 0.57 | −0.73 | −0.67 | −0.25 | 0.10 | AL590431.1 | 0.35 | −0.38 | −0.11 | −0.17 | 0.17 | AL121601.2 | 0.12 | −0.12 | 1.12 | −0.45 | 0.65 |
| SNX25 | −0.35 | 0.27 | 0.27 | 0.10 | 0.12 | AL353791.1 | −0.40 | 0.49 | 1.11 | 0.62 | 0.36 | ALG9-IT1 | 0.08 | 0.35 | 0.37 | 0.07 | 0.11 |
| FDFT1 | 0.50 | −0.10 | −0.53 | 0.19 | −0.21 | AC007741.1 | −0.79 | −0.27 | 0.32 | −0.39 | −0.17 | RNU6-354P | −0.37 | −0.32 | 0.14 | 0.97 | 0.04 |
| AL031985.4 | 1.88 | −2.83 | −0.46 | −0.19 | 1.13 | LINC00431 | −0.84 | −0.04 | 0.51 | 0.99 | −0.20 | BMS1P16 | −0.32 | 0.72 | 1.91 | 0.39 | 0.93 |
| CSPG4P12 | −0.54 | 0.19 | 0.46 | 0.11 | 0.35 | AC022417.1 | 0.54 | 0.20 | −0.62 | 0.73 | −0.76 | HA02-IT1 | −0.36 | 0.88 | −1.98 | 0.63 | −1.32 |
| ARHGEF26-AS1 | −1.24 | 0.06 | 0.32 | 0.71 | 0.48 | RNU6-1112P | 0.67 | −0.37 | −0.09 | 0.35 | −0.62 | AL590240.4 | 0.92 | −1.95 | −2.11 | 0.29 | 0.91 |
| AL160286.1 | −1.49 | −0.11 | 0.66 | 0.80 | 0.85 | ELOVL3 | −0.79 | 0.76 | 1.14 | 1.86 | 1.08 | CASC23 | −0.37 | −0.01 | −2.88 | 1.87 | −1.98 |
| CD93 | 0.77 | −0.35 | 0.08 | −0.35 | −0.27 | AC093591.2 | 0.26 | −0.17 | −0.18 | −0.10 | −0.26 | AL162373.1 | 0.31 | −0.53 | −0.94 | 1.73 | 0.16 |
| RPL5 | 0.54 | −0.13 | −0.13 | −0.19 | −0.23 | AC010542.1 | −0.65 | −0.19 | 1.15 | −0.26 | 0.95 | AVPR1B | 0.20 | −0.32 | −0.76 | 0.90 | 0.15 |
| AF127577.6 | 0.74 | −0.71 | −1.21 | −0.65 | −0.67 | STEAP1 | 0.36 | −0.57 | 0.09 | −0.49 | −0.03 | AC008627.1 | −0.20 | 0.44 | 0.13 | 0.69 | 0.75 |
| FBXL7 | −0.70 | 0.27 | 1.02 | −0.28 | −0.02 | CCNH | −0.10 | 0.09 | 0.06 | 0.00 | −0.05 | AP000550.3 | −0.34 | 1.92 | 2.16 | 0.87 | 1.02 |
| PRIM1 | 0.75 | −0.52 | −0.52 | −0.30 | 0.06 | AP002789.1 | −0.44 | −0.13 | 0.52 | 0.23 | 0.76 | RPS7P14 | 0.21 | −0.59 | −0.25 | 0.36 | 0.19 |
| AC245060.6 | −0.48 | 0.25 | 0.52 | 0.06 | 0.29 | ALDH3B1 | −0.20 | −0.17 | 0.04 | −0.07 | 0.08 | AC002378.1 | 0.40 | −0.86 | −1.41 | 0.54 | −0.12 |
| LRRC37A4P | −0.67 | 0.46 | 0.96 | 0.28 | 0.19 | AC016395.1 | −0.67 | −0.05 | −1.26 | 0.79 | −0.48 | MTND4P11 | 0.25 | −1.17 | −0.80 | −0.82 | −1.81 |
| AC079193.2 | −0.94 | 0.55 | 0.92 | −0.06 | 0.22 | ADAM5 | 0.97 | −1.14 | −1.38 | 0.05 | 0.70 | ATP1B1P1 | −0.04 | −0.08 | 0.23 | 0.01 | 0.11 |
| AC020915.2 | −0.78 | 0.27 | 1.14 | 0.07 | 0.49 | AC026461.3 | −0.83 | −0.38 | −0.80 | −0.70 | −0.08 | LINC00244 | −0.24 | −0.38 | 1.70 | −0.04 | 2.15 |
| BLZF1 | 0.36 | −0.17 | −0.38 | −0.18 | −0.34 | RPS27AP12 | 0.19 | −0.06 | −0.52 | 0.26 | −0.08 | IGFLR1 | −0.10 | −0.66 | −0.57 | 0.20 | 0.29 |
| PRO1804 | −0.59 | 0.69 | 0.48 | 0.35 | −0.20 | CTDSPL | −0.18 | 0.24 | 0.34 | 0.12 | 0.07 | AC083795.1 | 0.70 | 0.30 | −0.64 | 2.34 | 1.14 |
| ESYT2 | −0.31 | 0.27 | 0.18 | 0.05 | −0.16 | AC113342.1 | 1.54 | −0.97 | 0.15 | −1.03 | 1.01 | ORAI1 | 0.04 | 0.12 | −0.14 | 0.12 | −0.16 |
| AL021068.2 | 1.75 | −0.39 | −0.20 | −0.19 | −0.54 | RN7SL589P | 0.33 | −0.35 | 0.10 | −0.47 | −0.08 | PTPRG | −0.04 | −0.04 | 0.22 | −0.13 | −0.11 |
| RPL37P18 | −0.68 | 0.59 | 0.97 | 0.06 | 0.27 | CLECIA | 0.26 | −0.13 | 0.33 | −0.16 | 0.08 | IGBP1P5 | 0.27 | −0.17 | −2.08 | 0.35 | −2.22 |
| FARS2 | 0.25 | −0.09 | −0.28 | 0.07 | 0.06 | CYP26C1 | −0.52 | 0.06 | 0.20 | −0.15 | 0.41 | FNDC3CP | 0.24 | 0.69 | −2.28 | −0.02 | −3.96 |
| AP002383.2 | 1.39 | −0.49 | −0.71 | 0.34 | −0.42 | PPL | −0.15 | 0.15 | −0.07 | 0.12 | −0.24 | AP000343.1 | −0.25 | −1.43 | 1.49 | 0.83 | 1.56 |
| DGUOK-AS1 | 0.90 | −0.10 | −0.59 | 0.07 | −0.10 | SH3BGRL | 0.17 | 0.12 | −0.02 | 0.12 | −0.39 | RB1CC1 | −0.03 | 0.30 | 0.29 | 0.12 | −0.16 |
| AC006511.5 | −0.80 | 0.40 | 0.80 | −0.08 | −0.20 | AL161729.3 | −0.46 | 0.05 | −0.03 | 0.14 | 0.21 | CYP11B2 | 0.39 | −0.95 | −1.22 | 0.38 | −0.70 |
| AC020917.3 | −1.02 | 0.78 | 0.68 | 0.57 | 0.25 | AC113398.2 | −0.49 | −0.57 | 1.95 | −1.29 | 0.96 | FAM35DP | −0.07 | −0.53 | −0.30 | 0.39 | 0.39 |
| CTNNB1 | 0.34 | −0.05 | −0.21 | −0.10 | −0.28 | MIR593 | 0.90 | −0.31 | −0.01 | 0.56 | −1.28 | MTCO1P40 | −0.06 | 0.09 | 0.44 | −0.05 | 0.14 |
| MTO1 | 0.24 | −0.18 | −0.37 | 0.04 | −0.05 | AL353759.1 | 0.59 | −0.50 | −0.40 | −0.15 | −1.18 | GLDCP1 | −0.12 | −0.78 | −0.13 | −0.04 | 0.09 |
| GABPB1-IT1 | −0.31 | 0.09 | 0.12 | 0.04 | 0.00 | AQP8 | −0.56 | −0.17 | −0.17 | 0.29 | −0.76 | RANP6 | 0.38 | 0.10 | 0.06 | −0.50 | −1.72 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| PTPRM | −0.60 | 0.28 | 0.69 | −0.12 | 0.16 | AC103724.3 | 1.46 | −1.11 | −0.55 | 0.51 | −0.17 | SPATA17-AS1 | −0.43 | −1.83 | 0.19 | 0.23 | 1.29 |
| CERS5 | −0.30 | 0.05 | 0.32 | −0.01 | 0.25 | DPY19L2P1 | −0.50 | 0.05 | 0.09 | 0.05 | −0.30 | CYCSP26 | −0.26 | −0.12 | 1.34 | −0.29 | 0.64 |
| MTFP1 | 1.75 | −0.93 | −1.71 | −0.23 | −0.65 | AL135905.1 | 0.39 | 0.11 | −0.85 | 0.36 | −0.56 | AC098850.2 | 0.71 | −0.16 | −1.18 | 0.25 | −0.55 |
| FAM118B | 0.41 | −0.16 | −0.19 | −0.18 | −0.18 | FGF11 | 0.26 | −0.09 | 0.23 | 0.06 | 0.08 | AC084291.1 | −0.56 | −0.58 | 0.63 | −0.09 | 1.48 |
| PLEKHG7 | 1.21 | −0.37 | −0.78 | 0.16 | 0.20 | AC092142.1 | −0.54 | 0.65 | 0.45 | 0.20 | 0.08 | LINC02458 | −0.17 | 0.48 | −1.15 | 0.57 | −1.97 |
| DCUN1D3 | 0.46 | −0.31 | −0.60 | −0.16 | −0.57 | STX12 | 0.13 | −0.10 | −0.12 | −0.10 | −0.20 | SENCR | 0.10 | 0.32 | −0.16 | −0.06 | −0.27 |
| LAMB4 | −1.03 | 0.86 | 0.71 | 0.72 | 0.34 | LINC00310 | −0.34 | 0.19 | 0.25 | 0.23 | 0.16 | PRR30 | 0.25 | −1.29 | −1.47 | −0.03 | −1.46 |
| AGO2 | 0.33 | −0.08 | −0.30 | −0.06 | −0.20 | ENPP7P11 | −0.64 | 0.90 | 1.14 | −0.26 | −0.53 | AC005829.1 | −0.11 | −0.23 | 1.07 | 0.49 | 0.86 |
| FAM25A | 1.21 | −0.32 | −0.30 | −1.06 | −0.60 | SKAP2 | 0.15 | −0.07 | 0.06 | −0.11 | −0.13 | AL136139.1 | −0.17 | −0.23 | −0.39 | −0.18 | −0.12 |
| C4orf46 | 0.58 | −0.39 | −0.42 | −0.30 | −0.53 | LINC00887 | −0.38 | 0.31 | 0.03 | 0.58 | 0.20 | SMIM26 | 0.07 | 0.23 | 0.17 | 0.24 | −0.44 |
| EML6 | 0.58 | −0.08 | −0.47 | 0.38 | −0.08 | RNF151 | 0.84 | −0.92 | 0.81 | −0.62 | −0.04 | NEUROG2 | −0.29 | −1.36 | −0.35 | 2.06 | −1.95 |
| PKD2 | −0.41 | 0.21 | 0.10 | 0.14 | −0.10 | SMAD1-AS1 | 0.53 | −0.76 | 0.81 | −0.15 | 0.78 | RNU1-134P | 0.08 | 0.14 | −0.51 | 0.10 | −0.28 |
| HADHAP2 | −1.19 | 0.21 | 1.12 | 0.25 | −0.27 | AC067931.2 | 0.27 | −0.55 | −0.61 | −0.23 | 0.02 | LINC02165 | −0.41 | 0.13 | −2.04 | −0.04 | −1.77 |
| G30725 | −1.93 | −0.62 | 1.65 | −0.17 | 1.57 | RNF225 | 0.33 | −0.15 | −0.43 | 0.04 | −0.71 | OR7A17 | −0.15 | −0.46 | −0.76 | 0.43 | 0.09 |
| EIF2AK2 | 0.41 | −0.44 | −0.47 | −0.28 | −0.14 | G28443 | 0.30 | 0.09 | 0.59 | 0.14 | 0.25 | MTND1P16 | −0.24 | 0.31 | 1.35 | −0.46 | −0.99 |
| AL024508.2 | 1.34 | −0.75 | −1.50 | −0.19 | −1.42 | AL139241.1 | −0.25 | 0.17 | 0.08 | 0.10 | −0.39 | AC068112.1 | 0.27 | −2.49 | −1.50 | 0.37 | 1.57 |
| PQLC2L | −1.39 | 1.11 | 1.21 | 0.44 | 0.50 | LINC02058 | −0.88 | 0.63 | −2.01 | 1.17 | −1.67 | AC002454.1 | 0.17 | −0.34 | −2.19 | 0.92 | −1.12 |
| LMO3 | −0.98 | 0.59 | 0.42 | 0.54 | −0.49 | KRTAP3-1 | −0.92 | −1.96 | 1.43 | −0.63 | 1.39 | AC005091.1 | −0.14 | 0.30 | −0.52 | −0.37 | 0.72 |
| AC244197.2 | −1.62 | 1.04 | 1.38 | 1.27 | 0.56 | AC011385.2 | −0.71 | 0.58 | 2.54 | 0.07 | 0.30 | GTPBP2 | 0.03 | −0.18 | −0.32 | −0.05 | −0.08 |
| MTND5P1 | −1.00 | 0.14 | 0.51 | −0.05 | 0.66 | MLH3 | −0.11 | 0.01 | 0.29 | 0.06 | 0.33 | AP001858.2 | 0.42 | 0.40 | −2.03 | 0.75 | −1.71 |
| ACRBP | −0.87 | 0.24 | 0.95 | −0.02 | 0.15 | LINC02505 | −1.17 | 0.14 | −0.50 | 0.59 | 0.04 | DMWD | −0.03 | −0.02 | −0.18 | 0.14 | 0.12 |
| AL160269.1 | −1.55 | 0.53 | 0.20 | 0.15 | 1.06 | MTCO2P27 | −0.69 | −0.13 | −0.49 | −0.28 | 0.72 | MINDY4 | 0.04 | −0.11 | −0.10 | −0.13 | −0.01 |
| AC008770.2 | −1.32 | 0.05 | 1.31 | 0.38 | 1.02 | AC073896.2 | 0.36 | −0.52 | 0.64 | −0.43 | 0.58 | AC021151.1 | −0.23 | −0.19 | 0.14 | 0.48 | 1.40 |
| RN7SL29P | −1.16 | −0.63 | 0.00 | 0.35 | 1.30 | RN7SL160P | −1.03 | 1.03 | −0.15 | −0.07 | −0.19 | LINC01105 | −0.14 | −0.17 | −1.54 | 0.16 | −1.41 |
| PHF3 | −0.33 | 0.32 | 0.40 | 0.11 | −0.02 | FAM71C | −0.53 | 0.28 | 0.55 | 0.95 | 0.52 | PTGES2-AS1 | −0.08 | 0.09 | 0.14 | 0.26 | −0.35 |
| CTTNBP2 | −0.63 | 0.44 | 0.46 | 0.30 | 0.22 | AC016575.1 | −0.72 | −0.47 | 0.07 | 0.42 | 0.63 | AC109811.2 | −0.62 | −0.84 | −0.61 | 0.28 | 2.17 |
| CYTH2 | −0.41 | 0.37 | 0.14 | 0.24 | 0.07 | AL137224.1 | −0.74 | −0.65 | 1.48 | −0.53 | 1.37 | RPL7P44 | 0.31 | 0.86 | −0.64 | 1.86 | −0.18 |
| DACT3 | −0.84 | 0.38 | 0.96 | 0.06 | 0.25 | MIR1972-1 | −0.36 | −0.55 | −0.05 | −0.24 | 0.36 | AL353705.3 | −0.27 | −1.73 | 0.54 | −1.97 | −0.48 |
| PAX6 | −1.28 | −0.15 | 0.23 | 0.45 | −0.06 | RNU6-1323P | −0.74 | 0.09 | −0.25 | 0.65 | −0.15 | GAL | 0.15 | 0.73 | 0.30 | 1.46 | 0.96 |
| MIER3 | 0.32 | −0.06 | −0.33 | 0.01 | −0.26 | AC104791.1 | 0.32 | −0.99 | −0.10 | −0.36 | 0.62 | RPS5P3 | 0.25 | 0.59 | −0.15 | 0.63 | 0.00 |
| POLR2J | 0.53 | −0.01 | −0.24 | −0.16 | −0.52 | BRWD1P3 | 0.99 | −0.61 | −0.04 | 0.47 | 2.33 | RPP30 | 0.02 | −0.02 | 0.09 | −0.05 | 0.00 |
| SLC25A43 | 0.42 | −0.24 | −0.19 | −0.11 | −0.03 | AL096865.1 | 0.46 | −0.42 | −1.11 | −0.17 | −0.42 | AC090819.1 | −0.30 | −0.59 | 0.36 | −0.87 | −2.59 |
| CIZ1 | −0.33 | 0.18 | 0.02 | 0.17 | −0.07 | CEP57L1 | −0.12 | −0.05 | 0.20 | 0.00 | 0.16 | AL513324.1 | −0.32 | −0.89 | −0.80 | −0.15 | −1.46 |
| LINC00672 | −0.67 | −0.06 | 0.63 | 0.11 | 0.52 | AC009237.14 | −0.49 | 0.20 | 1.23 | −0.39 | 0.44 | AC090888.2 | 0.35 | −1.50 | 0.73 | −1.10 | 0.23 |
| AC098824.1 | −1.17 | 0.63 | 1.42 | 0.19 | 0.71 | ROM1 | −0.25 | 0.33 | −0.41 | 0.48 | −0.33 | NLE1 | −0.04 | −0.07 | −0.22 | 0.73 | −0.05 |
| CST7 | 1.18 | −1.10 | −0.27 | −0.78 | −0.12 | AC145676.1 | 0.32 | −0.48 | −0.45 | −0.38 | −0.10 | LINC01563 | −0.12 | −0.08 | −0.28 | 0.06 | 0.14 |
| CCL17 | 1.92 | −1.95 | −0.85 | −0.04 | −2.36 | AC084757.1 | 0.52 | −0.71 | −1.31 | −0.28 | −0.18 | SMIM22 | 0.11 | 0.32 | 0.36 | 0.07 | −0.61 |
| CEP85L | −0.58 | 0.21 | 0.72 | −0.28 | 0.31 | GPR142 | 1.04 | −0.88 | −1.16 | 0.09 | 0.72 | AC073352.1 | 0.13 | 0.27 | −0.71 | 0.04 | −0.10 |
| PPP6R2 | −0.47 | 0.04 | −0.06 | 0.17 | 0.18 | RN7SL425P | 0.34 | −0.45 | −0.33 | −0.17 | 0.27 | AL356475.1 | 0.06 | −0.23 | 0.24 | −0.20 | 0.62 |
| SLC12A6 | 0.24 | −0.09 | −0.07 | 0.04 | 0.00 | RNU6-762P | 0.63 | 0.14 | −0.66 | 0.26 | −1.14 | AC016292.2 | 0.11 | −1.32 | −2.79 | 0.05 | −1.76 |
| AL008628.1 | −1.11 | 0.50 | −0.06 | 0.44 | 0.09 | RNU11-6P | −0.68 | −0.16 | 0.15 | 0.83 | 0.01 | AL596268.1 | 0.61 | −0.51 | −1.06 | 0.66 | −2.65 |
| KNSTRN | 0.68 | −0.62 | −0.64 | −0.35 | 0.07 | NKAIN3 | −0.56 | 0.19 | 0.56 | 0.54 | −0.16 | AC093807.1 | 0.29 | −0.15 | −0.28 | 0.17 | 0.35 |
| RPL37 | 0.44 | −0.16 | −0.09 | −0.12 | −0.18 | MIR5094 | 0.61 | 0.17 | −0.82 | 0.20 | −0.84 | RTL8C | 0.03 | 0.06 | −0.16 | −0.02 | −0.14 |
| AC095064.1 | −1.89 | 1.26 | 1.60 | 0.15 | 0.50 | AC130462.1 | 0.65 | 0.53 | −1.72 | 0.29 | −0.41 | MINDY2 | 0.02 | 0.01 | −0.03 | −0.13 | −0.02 |
| SSB | 0.51 | −0.39 | −0.38 | −0.18 | −0.19 | AL031432.3 | −0.42 | 0.04 | 1.07 | −0.44 | 0.16 | AC022360.1 | −0.91 | 0.11 | −0.11 | −0.50 | −0.80 |
| CRTC3 | −0.20 | 0.11 | 0.31 | −0.08 | −0.02 | SDCCAG8 | −0.10 | −0.01 | 0.34 | −0.21 | 0.10 | AL162395.1 | −0.91 | −0.16 | 0.23 | −0.55 | −1.46 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| FBL | 0.41 | −0.19 | −0.14 | −0.06 | 0.00 | AC009652.2 | −0.55 | 0.30 | 0.16 | 0.13 | −0.27 | RPS27P20 | −0.30 | 1.31 | −1.35 | 1.38 | −0.92 |
| AP004609.1 | −1.79 | 0.55 | 0.38 | 0.91 | 0.39 | RNA5SP241 | −0.82 | 0.51 | −0.96 | −0.21 | −2.45 | AL139095.3 | 0.25 | 0.27 | 0.56 | −0.63 | 0.17 |
| STAT5B | −0.30 | 0.11 | 0.25 | −0.02 | 0.10 | PDP2 | 0.16 | −0.16 | −0.21 | 0.01 | 0.00 | AC016598.1 | 0.36 | 0.20 | 0.10 | 0.30 | 0.67 |
| BCAR1 | 0.44 | −0.17 | −0.81 | −0.02 | −0.34 | AC092316.2 | −0.57 | −0.68 | −0.91 | −0.05 | 0.27 | G12194 | −0.11 | 0.66 | 0.19 | 0.14 | 0.06 |
| CCL28 | −0.51 | 0.57 | 0.21 | 0.26 | −0.21 | AC090971.2 | 0.31 | 0.25 | −0.17 | −0.20 | −0.43 | IGHV3-21 | 0.91 | −1.26 | −0.49 | 0.40 | 1.41 |
| DDX39B | −0.46 | 0.19 | 0.04 | 0.31 | 0.07 | AL121721.1 | −0.79 | −0.46 | −0.16 | −0.52 | −0.23 | AC016716.1 | 0.21 | −0.52 | −0.95 | 0.22 | −0.18 |
| AL138752.2 | 1.24 | −0.50 | −1.01 | 0.05 | −0.17 | RNA5SP123 | 0.26 | 0.03 | −0.04 | 0.27 | 0.22 | AC055811.3 | −0.07 | 0.13 | 0.01 | 0.26 | −0.30 |
| CAPN3 | −0.61 | 0.28 | 0.37 | 0.02 | 0.46 | JCHAIN | 0.61 | −0.18 | 1.42 | 0.13 | −0.44 | SNORD111 | −0.09 | −0.34 | 0.42 | −0.81 | −0.36 |
| AL353150.1 | −0.67 | 0.60 | 0.49 | 0.33 | 0.29 | ATP9A | −0.19 | 0.19 | −0.11 | 0.18 | −0.26 | CTAGE16P | −0.31 | 1.47 | −0.79 | 0.83 | −0.07 |
| SOCS5P4 | −0.58 | 0.22 | 0.31 | 0.43 | 0.50 | ATP2C2-AS1 | 0.38 | −0.16 | −0.05 | 0.02 | 0.27 | AL359852.1 | 0.25 | −1.60 | −1.61 | 0.83 | 0.54 |
| IQUB | −0.95 | 0.20 | 0.79 | 0.25 | 0.51 | SCEL-AS1 | −0.62 | 0.76 | 3.03 | 0.95 | 0.77 | C11orf97 | 0.54 | −1.15 | −0.48 | −0.26 | −1.47 |
| AC010323.1 | −2.06 | −0.52 | 0.77 | 1.43 | 0.65 | AP001267.4 | 0.42 | 0.25 | −0.43 | 0.33 | −0.27 | CD151 | −0.04 | 0.02 | −0.11 | −0.06 | −0.15 |
| RNU5A-8P | 2.02 | −1.52 | −3.04 | −0.13 | −1.90 | AL158050.1 | 0.79 | −0.45 | −1.74 | 0.47 | −0.39 | AC022098.3 | 0.22 | −0.57 | 2.63 | 0.13 | 1.45 |
| RAC1P1 | −2.24 | 1.62 | 0.14 | 1.45 | −0.45 | FAM153B | −0.74 | −0.48 | 1.30 | 0.37 | −0.03 | LINC02046 | 0.29 | −1.18 | −1.11 | 0.29 | 0.65 |
| AC114730.2 | −1.68 | 0.02 | 1.16 | 1.23 | 1.08 | OR1B1 | −0.54 | 0.09 | 0.47 | −0.16 | 0.81 | OTULIN | 0.02 | 0.03 | −0.10 | 0.10 | 0.02 |
| KBTBD7 | −0.44 | 0.48 | 0.75 | 0.04 | 0.11 | GADD45B | 0.23 | −0.49 | −0.65 | −0.55 | −0.56 | GZMAP1 | −0.44 | −0.90 | −0.91 | −0.56 | −1.31 |
| MOXD1 | 0.74 | −0.23 | −0.48 | 0.03 | −0.25 | PRDM10 | 0.08 | −0.06 | −0.13 | −0.05 | −0.16 | AC002480.1 | 0.16 | −1.13 | −0.50 | −1.02 | −0.67 |
| SLC25A48 | −0.94 | 0.74 | 0.81 | 0.41 | 0.16 | LINC02178 | 0.67 | −0.95 | −0.73 | −0.44 | −0.15 | AP001324.2 | 0.53 | −0.89 | 0.16 | −1.01 | −0.09 |
| AC025178.1 | −0.59 | 0.43 | 0.53 | 0.45 | 0.35 | AC022021.1 | 0.60 | −0.86 | −0.48 | −0.40 | 0.75 | EEF1DP8 | −0.42 | −0.57 | 0.03 | 0.60 | −1.28 |
| AC009994.2 | −1.35 | 0.77 | 0.09 | 0.47 | 0.29 | IKBKGP1 | −0.58 | 0.03 | −0.78 | 0.60 | −0.40 | AC009948.3 | 0.11 | −0.18 | 0.03 | 0.24 | 0.32 |
| FAM66D | −1.32 | 0.05 | 1.94 | −0.39 | 1.01 | SOX5P1 | −1.21 | 0.63 | 0.11 | 0.05 | 1.50 | FAM230B | −0.26 | −0.85 | −0.34 | −0.23 | 0.40 |
| LRRC37A17P | −0.59 | 0.15 | 0.87 | −0.05 | 0.39 | INAVA | 0.23 | 0.15 | −0.20 | 0.10 | −0.25 | LINC01765 | −0.45 | 1.00 | −0.65 | 1.21 | −1.38 |
| AC008080.2 | −1.42 | 0.20 | 2.14 | 0.05 | 0.02 | OR8T1P | −0.92 | 1.12 | −0.79 | 0.73 | −1.14 | GLRA4 | −0.12 | −0.31 | −0.31 | 0.60 | 0.56 |
| ALS2CL | −0.70 | 0.30 | 0.27 | 0.40 | 0.36 | AC129492.4 | −0.93 | 1.18 | 0.32 | −0.41 | −1.35 | AC136285.2 | 0.21 | −1.81 | −0.83 | −0.58 | 0.80 |
| RNUSD-1 | 0.97 | −0.70 | −0.91 | −0.87 | −0.73 | AC068014.1 | 0.42 | −0.56 | −0.18 | 0.19 | 0.56 | RPS26P21 | −0.10 | −0.17 | 0.98 | −0.27 | 0.56 |
| RNU6-1336P | 1.87 | −0.11 | −0.25 | 0.10 | −0.27 | ASPHD2 | 0.28 | 0.07 | 0.11 | 0.19 | −0.12 | AC138907.9 | 0.27 | −0.10 | −1.24 | −0.22 | −0.10 |
| ATP5PO | 0.48 | −0.13 | −0.27 | 0.08 | −0.36 | NFIA-AS1 | 0.28 | −0.15 | −0.35 | 0.27 | 0.03 | AC026407.1 | 0.29 | −1.22 | 0.56 | 0.03 | 0.21 |
| MEST | −1.16 | 0.98 | 0.62 | 0.62 | −0.23 | CYREN | 0.14 | −0.13 | −0.34 | 0.01 | −0.07 | AC108868.1 | 0.28 | −0.95 | 0.29 | −1.43 | −0.84 |
| AC226118.1 | −1.23 | −0.10 | 0.49 | 0.13 | 0.42 | AC004471.2 | −0.65 | 0.39 | 0.80 | 0.43 | 0.23 | LINC01623 | 0.17 | −1.08 | −1.67 | 1.32 | −0.03 |
| ID2-AS1 | −1.03 | 0.79 | 0.94 | 0.43 | −0.10 | EQTN | −0.56 | −0.35 | −1.74 | −0.10 | 0.11 | G2E3-AS1 | 0.10 | −0.46 | 0.12 | −0.74 | −0.27 |
| AC009159.4 | −0.95 | 0.64 | 1.06 | 0.09 | 0.38 | AC123567.2 | 0.71 | 0.10 | 0.00 | 0.15 | 0.56 | NCAPD2P1 | −0.30 | −0.55 | 0.05 | −0.92 | 0.65 |
| AL390879.1 | −0.68 | 0.08 | 0.57 | 0.12 | 0.24 | ATP6VOB | 0.15 | −0.04 | −0.30 | 0.00 | −0.37 | EXOSC10 | −0.02 | 0.00 | −0.26 | 0.02 | −0.17 |
| IFNK | 0.64 | −0.75 | −0.63 | −0.17 | 0.22 | BRI3BP | −0.23 | −0.18 | −0.23 | 0.35 | 0.35 | AC027335.1 | −0.09 | −0.24 | 1.08 | −0.39 | 0.40 |
| ABLIM3 | −0.86 | 0.46 | 0.69 | 0.01 | 0.06 | AP000756.2 | −0.64 | 1.27 | 2.03 | 0.29 | −0.44 | COX6B1P6 | 0.28 | −0.66 | 0.24 | 1.17 | 1.09 |
| CCDC93 | −0.26 | 0.09 | 0.23 | −0.11 | 0.04 | RNY4P7 | −0.37 | 0.02 | 0.34 | −0.12 | 0.01 | AC009093.5 | −0.11 | 0.20 | −0.40 | 0.32 | −0.17 |
| IGFBP3 | 0.79 | −0.36 | −1.20 | 0.23 | −1.10 | AC010343.2 | −1.02 | −0.25 | −0.96 | 0.85 | −0.94 | EID1 | −0.04 | 0.13 | 0.34 | −0.02 | 0.01 |
| AC116407.1 | −0.98 | 0.56 | 0.40 | 0.56 | 0.12 | ERF | 0.18 | −0.07 | −0.62 | 0.29 | −0.08 | NDUFB9P3 | −0.90 | NA | 0.35 | 0.69 | 0.91 |
| 7-Sep | 0.41 | −0.13 | −0.17 | −0.09 | −0.29 | NHP2P1 | −0.41 | 0.87 | 0.03 | 0.10 | −0.50 | NAV2-AS2 | −0.48 | 0.63 | 0.42 | 0.11 | −0.26 |
| HAUS6 | 0.34 | −0.27 | −0.27 | −0.18 | −0.05 | AC022872.1 | 0.33 | 0.09 | 0.18 | 0.14 | 0.01 | AC093857.1 | 0.29 | −0.46 | 0.30 | 0.46 | −1.33 |
| AP003119.2 | −0.79 | −0.02 | −0.21 | 0.72 | 0.32 | MIR4526 | −0.72 | 0.43 | 1.27 | −0.12 | 0.09 | LINC00846 | −0.33 | −0.46 | 0.25 | −2.18 | −0.93 |
| SPATA20P1 | 2.10 | −2.08 | −0.83 | −0.69 | 0.10 | FECH | 0.16 | −0.03 | −0.02 | −0.18 | −0.33 | AC073365.1 | 0.19 | −0.54 | −0.78 | 0.32 | −1.81 |
| GNAL | −0.50 | 0.28 | 0.41 | 0.10 | 0.19 | DNAJC3-DT | −0.20 | −0.19 | 0.65 | −0.26 | 0.49 | AL354719.2 | −0.21 | −0.12 | −1.52 | 1.52 | 0.64 |
| PRR26 | −0.44 | 0.11 | 0.07 | −0.08 | −0.14 | SNRK | 0.13 | 0.17 | 0.03 | 0.01 | −0.29 | AC093107.1 | 0.22 | −0.56 | −0.53 | −0.22 | 0.77 |
| PSMB8-AS1 | 0.81 | −0.43 | 0.08 | −0.12 | −0.07 | MYOCOS | −0.42 | 0.07 | −0.26 | 0.08 | −0.24 | KRTAP19-3 | −0.90 | −0.48 | 1.21 | −1.05 | −0.10 |
| HIGD1AP1 | 2.14 | −0.65 | −2.14 | −0.86 | −1.46 | G30414 | −0.48 | 0.63 | −0.66 | 0.54 | 0.13 | G38630 | 0.30 | −0.34 | 0.77 | −0.59 | −0.78 |
| RETSAT | −0.46 | 0.26 | 0.04 | 0.25 | −0.12 | AL022315.1 | 1.27 | 0.10 | −0.20 | 0.75 | 0.49 | SLC25A38 | −0.02 | −0.10 | −0.20 | 0.07 | 0.00 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| FLYWCH1 | −0.46 | 0.10 | 0.28 | 0.29 | 0.61 | AP005131.4 | −0.32 | 0.32 | 0.31 | 0.16 | 0.07 | AC034206.1 | −0.14 | −0.23 | 1.17 | 0.46 | 0.06 |
| DLGAP1-AS5 | −1.02 | 0.39 | −0.06 | −0.20 | −0.40 | NFRKB | −0.10 | 0.02 | −0.10 | 0.04 | 0.10 | RN7SKP190 | 0.43 | −0.86 | −2.34 | 1.62 | 0.02 |
| NCOR2 | −0.41 | 0.19 | 0.07 | 0.18 | −0.02 | AC099048.1 | −0.50 | 0.72 | 1.10 | 0.45 | 0.06 | EFNA3 | 0.07 | 0.74 | 0.73 | 0.50 | −0.21 |
| MAFG | 0.48 | −0.15 | −0.28 | −0.03 | −0.37 | RNU6-312P | 0.60 | 0.32 | −0.73 | 0.73 | −0.61 | C17orf47 | −0.11 | −0.54 | −0.12 | −0.53 | −0.21 |
| RILP | −0.62 | 0.24 | 0.09 | 0.30 | 0.05 | AC097478.2 | −0.67 | 0.63 | 1.25 | −0.74 | −0.51 | EAF2 | −0.06 | −0.23 | −0.06 | −0.45 | −0.21 |
| RPS3A | 0.46 | 0.06 | 0.02 | 0.15 | −0.25 | LAMTOR3P2 | −0.37 | 0.72 | 0.73 | 0.14 | 0.51 | CD27 | −0.11 | 0.00 | 1.30 | −0.27 | 0.19 |
| LINC01140 | −1.21 | 0.41 | 1.19 | 0.19 | 0.01 | KCNH4 | −0.51 | 0.17 | 0.07 | 0.17 | −0.59 | AC055764.1 | −0.09 | −0.31 | 0.25 | 0.23 | 0.32 |
| AL138720.1 | −1.35 | 0.55 | 0.17 | 0.01 | 0.04 | AC010343.3 | 0.43 | −0.31 | −0.06 | −0.28 | 0.01 | H3F3BP1 | 0.15 | 1.03 | 0.23 | 0.90 | 0.55 |
| RPLP2 | 0.43 | −0.01 | −0.27 | 0.06 | −0.42 | PHF10 | 0.12 | 0.07 | 0.01 | 0.00 | −0.07 | RNU6-1035P | −0.08 | −0.44 | 0.13 | −0.27 | 0.46 |
| MRPS9 | 0.39 | −0.05 | −0.35 | −0.08 | −0.30 | FOLH1B | 0.71 | −0.56 | −0.66 | 0.00 | −0.17 | AC016700.3 | 0.15 | −2.39 | −0.54 | −1.49 | −0.07 |
| LRRC8C-DT | −0.74 | 0.21 | 1.17 | 0.22 | 0.68 | AC007000.2 | −0.34 | 0.40 | 0.91 | −0.19 | 0.29 | AL714022.1 | 0.17 | 0.65 | 0.17 | 1.45 | 0.30 |
| RDH11 | 0.58 | −0.25 | −0.34 | 0.13 | 0.09 | AC092378.1 | 0.58 | −1.66 | −0.64 | 0.36 | 0.43 | RNU7-77P | 0.13 | −0.88 | −1.90 | −0.68 | −1.43 |
| GOLGA8VP | −1.13 | 0.15 | 0.24 | 0.06 | 0.29 | RPL13P5 | 0.31 | −0.50 | −0.79 | −0.22 | −0.05 | RNU6-1329P | −0.27 | −1.60 | 0.04 | −0.71 | 1.62 |
| AC134043.2 | −1.06 | −0.09 | 0.70 | −0.10 | 0.25 | OOEP | −0.81 | −0.82 | −0.86 | 0.93 | 0.00 | AC138466.5 | 0.10 | −0.59 | 0.47 | −0.30 | 0.41 |
| RAB11FIP4 | −0.51 | 0.36 | 0.10 | 0.29 | 0.04 | OR2A3P | −0.46 | 0.75 | −0.01 | 0.55 | −0.34 | LINC01256 | 0.84 | −0.16 | −1.42 | 0.69 | −0.38 |
| MEF2D | −0.36 | 0.28 | 0.20 | 0.02 | −0.11 | AC069155.1 | −0.82 | −0.18 | 2.58 | −0.28 | 1.95 | APOA1-AS | 0.06 | −0.25 | −0.46 | 0.06 | −0.26 |
| AC027514.1 | 0.72 | −0.05 | −0.20 | −0.05 | −0.22 | AC092969.1 | −0.49 | −0.11 | 0.60 | −0.13 | 0.44 | LINC01934 | −0.08 | −0.59 | −0.19 | −0.14 | 0.74 |
| RGL2 | −0.37 | 0.21 | 0.11 | 0.31 | 0.17 | C1orf220 | −0.40 | 0.19 | 1.38 | 0.06 | 0.44 | AL583856.1 | 0.13 | −0.88 | −1.76 | 0.37 | 0.08 |
| AC007100.1 | −1.91 | 0.62 | 0.89 | 0.23 | −0.04 | ERLEC1 | 0.16 | −0.03 | 0.20 | −0.26 | −0.03 | BX005019.1 | −0.29 | 1.71 | −1.54 | 2.54 | −1.21 |
| AL109809.4 | −1.28 | 0.48 | 1.71 | −0.36 | 0.75 | ARL4AP2 | −0.66 | 1.09 | 1.22 | 0.64 | 0.57 | AL512361.1 | −0.41 | −1.84 | 0.92 | −2.31 | 2.27 |
| HAMP | −1.42 | −0.10 | 0.66 | 0.15 | 0.66 | RNF216-IT1 | −0.32 | 0.31 | 0.16 | 0.11 | −0.09 | SKAP1 | 0.09 | −0.33 | 0.85 | −0.67 | 0.46 |
| MAST3 | −0.43 | 0.22 | 0.50 | 0.02 | 0.10 | AC026150.3 | −0.65 | −0.25 | 1.53 | −0.46 | 1.02 | AC126121.2 | −0.31 | −0.82 | −0.38 | 0.08 | −0.14 |
| OR51B6 | −1.80 | 0.37 | −0.15 | 0.21 | −1.02 | AC007906.1 | 0.38 | −0.51 | 0.17 | 0.17 | 0.54 | RCC2P7 | −0.51 | −0.42 | 0.63 | −1.51 | −0.68 |
| COX8A | 0.72 | −0.11 | −0.89 | 0.31 | −0.83 | RAB41 | −0.26 | −0.07 | 0.23 | −0.23 | −0.15 | G39812 | 0.13 | −0.53 | −0.45 | 0.93 | 0.71 |
| DGKQ | −0.54 | 0.14 | −0.12 | 0.44 | 0.39 | FAM3A | −0.11 | 0.13 | −0.03 | 0.16 | −0.01 | AL135936.1 | 0.10 | 0.26 | −0.03 | −0.06 | 0.07 |
| NUDCD2 | 0.37 | −0.19 | −0.21 | 0.01 | −0.07 | AL031281.2 | 0.21 | −0.02 | 0.08 | 0.07 | 0.14 | LINC01405 | −0.20 | −1.16 | −2.05 | 0.07 | −1.94 |
| RFC3 | 0.53 | −0.50 | −0.64 | −0.13 | −0.06 | HCG18 | 0.11 | −0.08 | 0.07 | −0.12 | 0.04 | AC074281.2 | 0.46 | −1.18 | 0.29 | −0.55 | −0.08 |
| EVC | −0.39 | 0.07 | 0.10 | −0.05 | 0.08 | AC090001.1 | −0.80 | −0.57 | −0.67 | 0.19 | 0.87 | FSHB | −0.23 | −1.02 | −0.40 | 0.78 | −0.93 |
| DMTF1 | −0.23 | 0.11 | 0.08 | 0.01 | 0.04 | C1QL2 | −0.59 | 1.18 | 0.19 | 1.11 | 0.15 | FBH1 | −0.02 | −0.06 | 0.13 | −0.09 | 0.09 |
| AC027228.2 | 1.96 | −1.00 | −1.52 | −0.26 | 0.23 | AC022001.2 | 0.37 | −0.65 | 0.55 | 0.06 | 1.71 | C10orf113 | 0.06 | 0.35 | 0.39 | 0.21 | −0.32 |
| CCDC137 | 0.45 | −0.43 | −0.80 | 0.00 | 0.06 | AC242988.2 | −0.57 | 0.04 | −1.71 | 0.40 | 0.20 | AC010422.4 | −0.08 | −0.16 | 0.60 | −0.16 | 0.72 |
| HYAL2 | 0.58 | −0.25 | −0.19 | 0.01 | −0.04 | KCNQ3 | −0.29 | −0.33 | −0.69 | 0.14 | −0.47 | GMIP | −0.04 | −0.15 | −0.35 | −0.01 | 0.05 |
| AC245014.3 | 1.40 | −1.25 | −2.30 | −0.77 | −0.81 | SNORD45 | 0.41 | 0.32 | −0.22 | −0.01 | −0.54 | AC092905.1 | 0.38 | −1.16 | −1.56 | 0.41 | −0.28 |
| SLC35B4 | 0.42 | −0.37 | −0.41 | −0.20 | −0.09 | AL391095.1 | 0.30 | −1.09 | −0.56 | −0.41 | 0.21 | KRTAP2-1 | −0.90 | −0.21 | 0.17 | 0.04 | 0.98 |
| COX6C | 0.64 | −0.32 | −0.21 | −0.36 | −0.37 | RNU6-1098P | 0.63 | 0.41 | −1.30 | −0.31 | −1.17 | AP001888.1 | 0.81 | 0.41 | −0.48 | 0.12 | −0.36 |
| PDLIM7 | 0.57 | −0.49 | −0.86 | −0.38 | −0.46 | AC093673.1 | 0.37 | −0.65 | 0.02 | −0.33 | 0.36 | AC020897.1 | 0.61 | −1.87 | −0.72 | −0.84 | −0.81 |
| RPL5P32 | −1.88 | −0.05 | 3.27 | −0.86 | 1.33 | PLXNA2 | −0.15 | 0.04 | 0.32 | 0.14 | 0.21 | MIR148A | −0.10 | −1.33 | 1.32 | −0.17 | 1.31 |
| AL121584.1 | −2.12 | 0.66 | 2.63 | −0.68 | 0.50 | AL122008.2 | 0.69 | −0.09 | −0.95 | −0.62 | −0.16 | SPP2 | −0.33 | 0.02 | −0.54 | −0.81 | 0.88 |
| KDELR1 | 0.34 | −0.13 | −0.20 | −0.22 | −0.13 | GRASP | −0.22 | 0.05 | −0.26 | 0.08 | −0.49 | DESI1 | 0.04 | −0.20 | −0.29 | 0.03 | 0.14 |
| RAMAC | 0.58 | −0.27 | −0.38 | 0.05 | −0.38 | METTL17 | −0.12 | 0.17 | 0.01 | 0.22 | 0.06 | PHBP3 | −0.18 | −0.01 | −0.65 | −1.38 | −0.72 |
| PTMS | −0.49 | 0.07 | 0.25 | 0.00 | 0.12 | LINC02119 | 0.91 | −0.78 | −3.05 | 0.70 | −2.67 | PRC1-AS1 | 0.06 | −0.38 | −0.08 | −0.28 | 0.14 |
| SNAPIN | 0.46 | −0.15 | −0.30 | −0.11 | −0.30 | RN7SL96P | −1.20 | −0.78 | 0.80 | −0.83 | 1.44 | AC022733.1 | 0.43 | −1.30 | −1.49 | 1.26 | 0.49 |
| MRPL22 | 0.44 | −0.25 | −0.42 | −0.15 | −0.25 | CYCSP38 | 0.56 | 0.19 | 1.72 | −0.05 | 0.24 | CAMK2G | 0.02 | −0.02 | −0.18 | 0.10 | 0.04 |
| AC002398.1 | −1.06 | −0.23 | −0.26 | 0.37 | 0.23 | IL9 | −0.68 | 0.07 | 0.15 | 0.43 | −0.25 | HNRNPCP9 | 0.38 | −0.01 | −1.80 | −0.20 | −1.62 |
| PCDHGB4 | −0.67 | 0.37 | 0.64 | 0.17 | 0.21 | AC091965.4 | −1.27 | 2.12 | −1.87 | 1.82 | −1.59 | SCOCP1 | 0.08 | 0.32 | −0.34 | 0.04 | −0.02 |
| MAST2 | −0.40 | 0.17 | 0.42 | −0.04 | 0.22 | RN7SL651P | −1.03 | 0.08 | 0.15 | 0.94 | 1.02 | AC005486.1 | 0.18 | 0.88 | −0.29 | 0.75 | −0.58 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| IGLON5 | 1.02 | 0.09 | −0.12 | −0.54 | −0.70 | AL356274.2 | −0.62 | −0.12 | −0.04 | 0.04 | −1.19 | AC114485.1 | 0.32 | −0.05 | −1.48 | 0.36 | −1.26 |
| MAFK | −0.63 | 0.49 | −0.30 | 0.34 | −0.35 | AC104393.1 | 0.56 | −0.06 | −1.07 | −0.45 | 0.13 | KLHL25 | −0.04 | 0.39 | 0.15 | 0.10 | −0.10 |
| NDUFS8 | 0.39 | −0.16 | −0.27 | −0.04 | −0.04 | AL356000.1 | −0.51 | 0.26 | 1.20 | −0.25 | 0.61 | PHF5CP | −0.11 | −0.86 | 0.86 | −0.44 | 1.07 |
| FNBP1P1 | −0.40 | 0.18 | 0.34 | −0.13 | 0.04 | AC009019.1 | 0.45 | 0.06 | −0.11 | −0.01 | −0.36 | AC019288.1 | 0.08 | −0.30 | 0.30 | −0.28 | 0.21 |
| ANP32C | −1.43 | 0.21 | −0.36 | 0.29 | −0.40 | AL121652.1 | 0.35 | −0.16 | −0.05 | −0.24 | 0.01 | BOK | 0.04 | 0.13 | −0.30 | 0.18 | −0.10 |
| CATSPER2 | −0.49 | 0.25 | 0.53 | −0.01 | 0.56 | ABCA1 | −0.13 | −0.02 | 0.17 | 0.10 | 0.08 | AC007684.1 | 0.10 | 0.28 | −0.07 | 0.46 | −0.38 |
| EGLN3-AS1 | −1.98 | −0.12 | 2.69 | 0.02 | 1.12 | MIRLET7F1 | −0.74 | −1.08 | 0.28 | 0.25 | 0.61 | HSP90AB7P | −0.29 | −0.15 | 2.08 | 0.59 | −0.42 |
| RPS20P22 | −0.88 | 0.37 | 1.04 | −0.25 | 0.24 | AC013476.2 | −0.54 | 0.47 | −0.32 | 0.03 | −0.97 | AC008659.1 | −0.09 | −1.21 | −0.62 | −0.77 | 1.00 |
| ARF5 | 0.50 | 0.06 | −0.59 | 0.25 | −0.63 | AC093423.1 | 0.35 | −0.69 | −0.53 | −0.38 | −0.21 | AC121758.2 | −0.38 | −0.11 | −1.55 | −0.06 | −2.71 |
| OR2A1-AS1 | −0.93 | 0.11 | 1.22 | 0.26 | 0.16 | RN7SL655P | 0.70 | −1.17 | −0.80 | −0.18 | 0.56 | AC010359.1 | −0.10 | 0.77 | −1.04 | 0.97 | −0.28 |
| PI4K2A | 0.52 | −0.03 | −0.63 | −0.06 | −0.52 | CDH5 | 0.26 | −0.14 | 0.61 | −0.23 | −0.07 | AC092451.3 | −0.51 | −0.31 | 0.42 | −0.49 | −0.89 |
| MEA1 | 0.34 | −0.04 | −0.30 | −0.03 | −0.45 | HELQ | 0.11 | 0.00 | 0.08 | −0.05 | −0.05 | AC007773.1 | −0.10 | 0.23 | 1.02 | 0.12 | 0.67 |
| NDUFB1 | 0.45 | −0.14 | −0.06 | −0.09 | −0.07 | LINC01543 | −0.63 | 0.66 | 0.09 | −0.12 | −1.08 | AC093734.1 | 0.36 | −1.14 | −0.44 | −0.03 | 0.58 |
| BNIP3P37 | −1.78 | 0.13 | 1.20 | −0.33 | 0.59 | OR5AN1 | −0.63 | −0.37 | −0.95 | 0.10 | 0.24 | AC023206.1 | −0.11 | 0.30 | 0.63 | −0.45 | −0.13 |
| AL136531.2 | 0.79 | −0.08 | −0.78 | 0.02 | −0.74 | G113 | −1.09 | 1.33 | −0.19 | 1.58 | 0.94 | RPL27AP5 | 0.21 | 0.90 | 0.38 | −0.28 | −0.01 |
| AC138409.1 | −0.56 | 0.31 | 0.54 | 0.21 | 0.46 | AC011676.2 | −0.43 | −0.12 | 0.23 | −0.60 | 0.12 | DENND4B | −0.03 | −0.28 | −0.20 | 0.03 | 0.24 |
| AC009948.2 | −0.92 | 0.07 | 0.04 | 0.98 | 0.24 | PA2G4P1 | 0.83 | 0.17 | 0.09 | 0.23 | 0.41 | PPIAP88 | 0.73 | 0.65 | −0.66 | 1.66 | −1.21 |
| SNTA1 | −0.51 | 0.22 | 0.22 | 0.10 | 0.00 | ERVFRD-1 | −0.23 | 0.05 | 0.26 | 0.02 | 0.22 | AC099326.1 | 0.19 | 1.09 | 0.06 | 0.20 | −1.39 |
| AC023906.5 | 0.88 | −0.03 | −0.66 | −0.15 | −0.62 | GMNC | −0.64 | −1.43 | −0.26 | 0.27 | −0.52 | AC068413.1 | −0.36 | 0.05 | 0.98 | −0.03 | −1.55 |
| AL592429.1 | −1.47 | 0.27 | 0.94 | 0.31 | 0.44 | NLGN4Y | 0.23 | 0.29 | 0.43 | −0.26 | −0.08 | G39927 | 0.24 | 0.24 | 1.31 | −0.20 | −0.45 |
| AL138999.2 | −0.83 | 0.46 | 0.99 | −0.47 | 0.01 | AP000880.1 | −0.65 | 0.28 | 1.00 | −0.43 | 0.27 | AC105235.1 | −0.07 | −0.34 | −1.11 | −0.20 | −0.20 |
| CBX6 | −0.42 | 0.10 | 0.35 | −0.08 | 0.14 | INO80-AS1 | 0.33 | −0.12 | −0.50 | −0.04 | −0.17 | BX119904.2 | −0.85 | −0.41 | 1.62 | −1.23 | 1.09 |
| GANAB | 0.32 | −0.19 | −0.34 | 0.00 | −0.14 | HAUS3 | 0.13 | −0.05 | 0.08 | −0.12 | 0.04 | DUX4L18 | 0.28 | −0.31 | −1.35 | 0.28 | 0.70 |
| CLIP1 | 0.37 | −0.07 | −0.52 | −0.13 | −0.53 | OR52E4 | −0.73 | 0.32 | −0.88 | 0.04 | −0.99 | RN7SL11P | 0.16 | −0.59 | 0.02 | −0.17 | 0.92 |
| METAP1D | −0.43 | 0.19 | 0.34 | 0.05 | 0.12 | G39423 | −0.75 | 0.53 | 0.12 | 1.32 | 0.41 | AL590705.3 | −0.22 | 0.21 | 0.36 | 0.17 | −1.07 |
| CCDC152 | −0.55 | 0.48 | 0.20 | 0.25 | −0.05 | MIR624 | 0.57 | −0.79 | −0.73 | 0.36 | 1.15 | IQCH | −0.04 | 0.12 | 0.12 | 0.14 | 0.10 |
| CDK8P2 | −2.08 | 1.85 | 2.23 | −0.28 | −0.02 | AC008781.1 | 0.32 | 0.05 | −0.13 | −0.05 | −0.02 | AC095050.2 | −0.22 | −0.43 | −1.61 | 0.21 | −0.81 |
| RP11-42302.1 | −0.60 | 0.72 | 0.42 | 0.83 | 1.12 | AC007114.2 | −0.24 | 0.07 | 0.31 | 0.25 | 0.39 | AP003072.2 | 0.09 | −0.53 | 0.45 | −0.37 | 0.19 |
| AC039056.2 | 0.87 | −0.16 | −1.18 | 0.15 | −0.87 | LINC02255 | 1.61 | −2.11 | −2.15 | −0.83 | −1.03 | AC092435.1 | −0.29 | −1.00 | −0.74 | 1.43 | 0.08 |
| NUDT21 | 0.43 | −0.14 | −0.21 | −0.01 | −0.18 | G6968 | −1.29 | 2.03 | 2.94 | −0.59 | −0.24 | LINC02546 | −0.30 | −2.07 | −0.44 | −0.05 | 1.67 |
| 9-Sep | 0.38 | −0.46 | −0.75 | −0.06 | −0.05 | AL033378.1 | −0.74 | 0.28 | −0.66 | 0.82 | −1.20 | RN7SKP153 | 0.30 | 0.47 | 0.66 | −0.01 | 1.15 |
| RN7SL204P | −1.35 | 0.63 | −0.27 | 0.87 | −0.28 | AC022532.1 | −0.35 | 0.65 | −0.05 | 0.32 | −0.55 | INTS6L | 0.02 | 0.04 | 0.02 | 0.17 | −0.01 |
| PPM1M | −0.47 | 0.04 | 0.04 | 0.07 | 0.11 | ANK3 | −0.16 | 0.45 | 0.30 | 0.21 | −0.06 | FLG−AS1 | 0.07 | 0.38 | 0.81 | 0.51 | 0.16 |
| HMGN2P15 | −1.38 | 1.16 | 0.99 | 1.40 | 0.46 | AC114730.1 | −1.28 | 0.39 | 1.71 | 0.81 | 2.28 | AL353622.1 | 0.07 | 0.10 | 0.37 | 0.24 | 0.13 |
| RHPN2 | −1.03 | 0.92 | 1.38 | 0.24 | 0.55 | AL845552.2 | −0.75 | 0.52 | −0.70 | 1.13 | 1.14 | ARL15 | −0.04 | 0.22 | 0.27 | 0.03 | −0.16 |
| NFKBIE | 0.70 | −0.82 | −0.59 | −0.34 | −0.06 | LINC01588 | 0.20 | −0.20 | −0.37 | −0.18 | −0.22 | AC084290.1 | 0.20 | 0.49 | 0.09 | 0.69 | −0.47 |
| GRM2 | −0.76 | 0.28 | 0.33 | 0.01 | 0.31 | POLR3D | −0.13 | −0.11 | 0.08 | −0.24 | 0.12 | MIR646 | 0.21 | −1.16 | −0.60 | 0.30 | 0.73 |
| LINC00276 | −1.47 | −0.15 | 0.69 | −0.04 | 0.00 | AL022718.1 | 0.68 | 0.37 | −0.86 | 0.43 | −0.90 | AC106800.2 | −0.09 | 0.50 | −0.88 | 0.43 | −0.93 |
| AC099313.1 | 1.79 | −0.67 | −1.03 | −0.87 | −1.42 | RPL5P18 | −0.36 | −0.41 | 0.72 | −0.33 | 0.71 | AC034187.1 | −0.18 | −0.46 | −0.88 | 1.24 | 0.91 |
| G30604 | −1.81 | 0.56 | −0.51 | 0.24 | 0.06 | CTAGE13P | 1.07 | −1.47 | −3.72 | −0.21 | −2.68 | CIR1P1 | −0.23 | 0.26 | −1.43 | −0.55 | −1.89 |
| AL035420.1 | −1.99 | 1.77 | 3.18 | 1.23 | 0.18 | GLRX5 | 0.14 | −0.09 | 0.04 | −0.12 | 0.05 | RNU6-150P | −0.26 | −0.04 | 1.40 | 0.40 | 0.17 |
| AC012358.1 | −0.78 | 0.01 | 1.15 | 0.00 | 0.58 | CBLL2 | −0.99 | 0.24 | 1.17 | −0.25 | 0.93 | SAP18P2 | 0.47 | 0.15 | −2.27 | 0.40 | −1.42 |
| GPR1 | 1.33 | −0.31 | −0.97 | 0.11 | −1.34 | AC018529.1 | 0.46 | −0.69 | 0.00 | −0.59 | −0.27 | AC005034.2 | −0.06 | −0.26 | 0.54 | −0.14 | 0.34 |
| LSG1 | 0.25 | −0.16 | −0.32 | −0.02 | −0.06 | GKN2 | −0.59 | 0.33 | 0.27 | 0.69 | −0.13 | AC019080.4 | 0.09 | −0.21 | 0.94 | −0.15 | 0.58 |
| HSPA8P14 | −1.09 | −0.11 | 0.72 | 0.07 | −0.12 | IZUMO1 | 0.30 | −0.10 | −0.40 | 0.40 | 0.13 | AC073236.1 | −0.44 | 1.37 | 1.81 | 0.61 | 0.40 |
| KSR2 | −1.04 | 0.15 | 0.51 | 0.23 | 0.24 | AP001011.1 | 0.36 | −0.22 | −0.74 | −0.12 | −0.76 | MAN2B1 | 0.03 | −0.04 | −0.17 | 0.03 | −0.23 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| LINC02570 | 1.46 | −0.75 | −1.69 | −0.32 | −0.81 | AC022274.1 | −0.96 | −0.10 | 0.62 | −0.58 | 0.01 | AL590867.1 | −0.32 | 0.26 | 0.65 | 1.19 | −0.09 |
| LINC01772 | −0.60 | 0.03 | 0.35 | −0.14 | 0.16 | MIR5002 | −0.85 | 0.34 | 1.40 | 0.01 | 0.25 | OR4A7P | −0.38 | −1.09 | −0.28 | 0.10 | −0.38 |
| BCAM | −0.54 | 0.64 | 0.38 | 0.55 | −0.05 | AC104564.5 | 0.20 | −0.43 | 0.26 | −0.31 | 0.45 | CNOT7P2 | 0.89 | 1.10 | −0.08 | −0.13 | −2.77 |
| ARR3 | −0.64 | 0.18 | 0.70 | 0.11 | 0.64 | CPNE8 | 0.13 | −0.25 | −0.14 | −0.18 | −0.05 | KRTAP19-8 | −0.89 | 0.32 | −0.49 | 0.10 | −0.72 |
| ATP13A2 | 0.44 | −0.22 | −0.37 | −0.14 | −0.14 | RNU1-106P | 0.52 | 0.42 | −0.18 | 0.71 | −0.47 | RNA5SP428 | −0.35 | −0.88 | −0.74 | 0.59 | 0.29 |
| GRIA2 | −1.25 | 0.84 | 1.35 | 0.98 | 1.29 | LARS2-AS1 | 0.44 | 0.22 | −0.61 | −0.37 | −0.99 | RN7SL146P | −0.10 | −0.99 | −0.05 | 0.28 | 1.13 |
| AC110619.1 | −0.93 | 0.78 | 0.82 | 0.42 | 0.22 | AC005410.1 | −0.47 | −0.60 | 0.10 | −0.90 | 0.08 | CD1D | 0.11 | −0.63 | −0.09 | 0.00 | 0.08 |
| HAS1 | −1.20 | 0.52 | −0.24 | 0.00 | −0.68 | RNF5P1 | −0.89 | 0.22 | 1.32 | 0.12 | −0.47 | AC069079.1 | −0.10 | 0.14 | −0.70 | 0.13 | −0.42 |
| RPAIN | −0.33 | 0.36 | 0.46 | 0.22 | 0.08 | HORMAD2 | 0.81 | −0.76 | −1.26 | 0.01 | −0.17 | RN7SL113P | 0.12 | 0.10 | 0.29 | −0.35 | −0.11 |
| CFAP45 | −0.62 | 0.13 | 0.09 | 0.30 | 0.07 | ARHGAP22 | 0.22 | −0.54 | −0.15 | −0.37 | 0.24 | RNF216 | 0.01 | 0.04 | −0.03 | −0.12 | −0.18 |
| C10orf71 | −1.57 | 0.41 | 0.66 | 0.61 | 0.26 | G31549 | 0.42 | −0.22 | 0.65 | −0.17 | −0.12 | FBXL17 | −0.02 | 0.11 | −0.02 | 0.09 | −0.10 |
| ERAP2 | 0.53 | −0.73 | −0.45 | 0.12 | −0.02 | LINC00606 | 1.06 | −1.52 | −1.22 | 0.50 | 0.22 | RNU6-436P | −0.72 | 0.97 | 0.73 | −0.05 | −0.65 |
| ENTPD3 | 0.56 | −0.08 | −0.10 | −0.44 | −0.18 | ITGA4 | 0.27 | −0.54 | −0.12 | −0.64 | −0.23 | LINC00917 | −0.26 | −1.13 | −1.01 | −0.83 | −1.16 |
| G23133 | −0.82 | 0.79 | 1.27 | 0.28 | 0.26 | BSND | −0.70 | −0.05 | −1.22 | −0.11 | −0.05 | ALG1L12P | 0.26 | 0.88 | −1.06 | 0.49 | −0.11 |
| CPEB2 | 0.44 | 0.17 | −0.54 | 0.19 | −0.50 | AC024267.3 | −0.25 | −0.32 | −0.53 | 0.35 | 0.28 | DRD5 | 0.12 | −0.56 | −1.00 | 0.40 | −0.07 |
| DCAF13P3 | 0.42 | 0.01 | −0.10 | 0.00 | −0.36 | PIEZO1 | 0.16 | −0.25 | −0.58 | 0.10 | −0.06 | CLRN1 | 0.20 | 1.07 | −1.95 | 0.10 | −3.10 |
| CHPF2 | 0.33 | −0.27 | −0.10 | −0.22 | 0.06 | PORCN | 0.18 | −0.01 | 0.00 | −0.06 | −0.03 | CLSTN3 | 0.04 | −0.36 | −0.47 | 0.17 | 0.29 |
| CCS | −0.50 | 0.17 | 0.24 | 0.26 | 0.18 | AQP11 | −0.22 | 0.01 | 0.15 | −0.12 | −0.05 | C9orf139 | 0.07 | 0.08 | −0.13 | −0.01 | −0.07 |
| PPP1R18 | 0.40 | −0.44 | −0.78 | −0.14 | −0.19 | FGR | 0.28 | −0.65 | −0.51 | −0.20 | −0.42 | HMGA1P4 | 0.08 | −0.56 | −0.22 | −0.49 | 0.54 |
| HNRNPUL1 | 0.21 | −0.05 | −0.23 | −0.01 | −0.16 | RNU6-852P | 0.77 | 0.54 | −0.32 | −0.09 | −0.23 | AC243962.1 | 0.45 | 1.43 | −1.80 | 0.96 | −2.59 |
| RBMS3-AS2 | −0.77 | 0.36 | 0.90 | −0.25 | 0.24 | SNHG12 | −0.24 | 0.04 | −0.28 | 0.30 | −0.24 | AC009996.1 | 0.05 | −0.46 | −0.19 | −0.10 | 0.42 |
| AP001605.1 | −1.15 | −0.23 | 0.81 | 0.56 | 0.85 | MTCO1P11 | 0.24 | −0.19 | −0.09 | −0.41 | −0.14 | AC007541.1 | −0.13 | 0.65 | 1.30 | 0.27 | −0.15 |
| SCARNA11 | −0.98 | 0.25 | 0.31 | 0.10 | −0.12 | AC018470.1 | −1.06 | −0.85 | −0.78 | 0.16 | −1.05 | AC092675.1 | −0.21 | −0.65 | −0.34 | −0.18 | 0.86 |
| ADAMTS4 | 1.12 | −1.26 | −1.56 | −0.05 | −0.84 | JUN | 0.23 | 0.06 | −0.76 | −0.38 | −0.53 | AC097637.2 | −0.11 | 0.06 | −0.33 | −0.59 | 0.24 |
| AC010319.4 | −0.83 | −0.21 | 0.54 | 0.27 | 0.85 | MIR3155A | 0.56 | 0.34 | −0.25 | 0.04 | 0.46 | NDUFB9P2 | 0.32 | 0.93 | 0.43 | −0.36 | −1.09 |
| NEDD8 | 0.57 | −0.19 | −0.63 | 0.11 | −0.45 | NBAS | 0.07 | −0.01 | 0.03 | −0.08 | −0.05 | MTND4P5 | −0.26 | −0.71 | −0.84 | −1.57 | −0.04 |
| PHF6 | 0.38 | −0.27 | −0.26 | −0.07 | 0.03 | GALM | −0.17 | −0.03 | 0.06 | −0.03 | 0.15 | LINC02429 | −0.52 | −0.03 | −0.87 | 0.91 | 0.39 |
| G3386 | 2.07 | −0.58 | −3.36 | 0.57 | −2.44 | LCE3C | 2.07 | −0.47 | −3.64 | 0.79 | −3.91 | RNA5SP321 | −0.16 | −0.37 | −0.10 | −0.65 | −0.26 |
| RAF1 | 0.27 | −0.04 | −0.36 | 0.00 | −0.29 | KIF3C | 0.20 | 0.00 | −0.16 | −0.03 | −0.24 | RNU6-136P | −0.18 | −0.35 | 0.09 | 0.07 | 0.69 |
| BAZ2A | −0.37 | 0.13 | 0.06 | 0.11 | 0.00 | LRRC31 | −0.80 | −0.37 | −0.26 | −0.02 | 0.43 | AC004491.1 | −0.06 | 0.17 | 0.27 | −0.30 | −0.06 |
| ANGPT1 | −0.94 | 0.61 | 1.27 | 0.00 | −0.05 | NPM1P24 | 0.69 | 0.37 | −1.42 | 0.29 | −1.27 | ATXN7 | 0.02 | 0.06 | 0.08 | 0.00 | −0.03 |
| AGMO | −1.25 | 0.65 | 1.36 | 0.62 | −0.18 | AC027455.1 | 0.38 | −0.34 | −0.09 | 0.04 | 0.23 | MTCO1P43 | −0.50 | −0.84 | −0.01 | 0.71 | 0.60 |
| FAM189A1 | −1.23 | 0.38 | 0.16 | 0.41 | 0.52 | RAB43P1 | −0.42 | 0.52 | 0.32 | 0.73 | 0.06 | OR10C1 | 0.37 | 0.15 | 0.46 | 1.27 | 0.84 |
| CPE | −0.83 | 0.79 | 1.23 | −0.12 | −0.19 | SLC25A47 | 0.97 | −2.26 | −1.38 | −1.53 | −1.52 | LINC02453 | −0.11 | 0.13 | 0.74 | 0.07 | −0.03 |
| AC044784.1 | 2.12 | 0.24 | −1.70 | 0.15 | −1.23 | RN7SL412P | −0.46 | −0.18 | 0.19 | −0.13 | 0.42 | CD200R1 | −0.07 | 0.11 | 0.16 | 0.32 | 0.54 |
| AL592158.1 | −0.78 | 0.33 | 0.89 | 0.10 | −0.18 | RNU1-93P | 1.09 | 0.02 | −1.76 | 0.56 | −1.43 | SMPD4P2 | −0.34 | 0.30 | −1.03 | −0.24 | −2.50 |
| AP000873.4 | −0.76 | −0.20 | 0.28 | −0.16 | 0.57 | RNU6-1300P | −0.37 | 0.00 | −0.59 | 0.11 | 0.04 | OR13H1 | −0.55 | −0.73 | −0.69 | 0.67 | 0.76 |
| PTN | −0.88 | 1.21 | 1.32 | −0.65 | −0.10 | ACY1 | 0.40 | −0.29 | −0.47 | 0.25 | −0.53 | FGF19 | 0.31 | −0.85 | −0.40 | 0.47 | −0.48 |
| AL359091.2 | −0.84 | 0.36 | 0.89 | 0.29 | 0.26 | AC000068.1 | 0.28 | −0.33 | −0.17 | 0.44 | 0.33 | RNA5SP492 | 0.16 | −0.90 | 1.51 | −1.10 | 0.90 |
| BORCS8 | −0.46 | 0.10 | 0.24 | 0.02 | 0.27 | HK3 | 0.38 | −0.78 | −0.96 | −0.02 | 0.21 | LINC01905 | 0.16 | −0.29 | −0.13 | 1.34 | −0.37 |
| DVL2 | −0.38 | 0.24 | 0.16 | 0.31 | 0.07 | MIR4530 | −0.52 | −0.11 | 0.79 | −0.76 | 0.47 | LINC02307 | 0.46 | −0.82 | −0.54 | 0.10 | −1.18 |
| PSMB4 | 0.32 | −0.10 | −0.41 | 0.06 | −0.33 | LIN28AP2 | −0.85 | 0.16 | 0.07 | −0.78 | −0.30 | CPXM2 | 0.05 | −0.19 | 0.25 | −0.33 | −0.43 |
| ITGB4 | 0.61 | −0.27 | −1.14 | 0.09 | −0.22 | AL079303.1 | −0.76 | 1.28 | 0.53 | 1.02 | −0.14 | AC096736.3 | 0.88 | 1.02 | −0.34 | 1.10 | −2.41 |
| ADCK1 | −0.40 | 0.06 | 0.22 | 0.28 | 0.43 | AC124283.3 | 0.34 | −0.07 | −0.24 | 0.19 | −0.01 | RNA5SP67 | −0.39 | −0.25 | 0.03 | −0.12 | 0.13 |
| CHMP4BP1 | −0.77 | −0.04 | 0.09 | 0.22 | 0.32 | RHOXF1P3 | −0.36 | 0.02 | 0.05 | 0.12 | 0.35 | AC094103.1 | 0.19 | −1.12 | −1.23 | −1.01 | −1.24 |
| FAM214B | 0.36 | 0.03 | −0.13 | −0.12 | −0.33 | CNMD | −0.42 | −0.16 | 0.78 | −0.37 | 0.18 | AC022364.2 | −0.30 | −1.51 | 1.06 | −1.16 | 0.66 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| MPV17L | −0.62 | 0.34 | 0.36 | 0.12 | 0.15 | AC019109.1 | −0.94 | −0.14 | −0.48 | −0.41 | −1.98 | ALOX15 | −0.13 | −0.15 | −0.36 | 0.23 | 0.27 |
| BMP5 | −1.35 | 0.79 | 1.05 | 0.22 | 0.08 | AC100782.1 | −1.24 | 0.93 | 2.29 | 1.12 | 0.52 | AC067930.6 | 0.11 | −0.51 | −0.11 | 0.40 | 0.74 |
| COLEC11 | −1.26 | 0.36 | 0.53 | 0.03 | 0.70 | DMD-AS3 | −1.33 | 1.48 | 1.07 | −1.80 | 0.19 | LINC01214 | −0.11 | −0.41 | 0.91 | −0.58 | 0.15 |
| NFATC2 | −0.69 | 0.32 | 0.41 | −0.01 | −0.24 | AC092952.1 | 1.10 | −1.65 | −1.43 | −0.94 | −0.97 | RNA5SP172 | 0.16 | 0.57 | 0.71 | 1.00 | 0.08 |
| AC025918.1 | 1.61 | 0.26 | −0.38 | 0.41 | −0.81 | AF131215.7 | 0.84 | −0.65 | −2.24 | 0.76 | −0.17 | AC135012.2 | −0.48 | 0.27 | 0.54 | −0.06 | −2.15 |
| MAD2L2 | 0.41 | −0.30 | −0.10 | −0.38 | 0.02 | AC139272.1 | −0.40 | −0.05 | 0.32 | 0.13 | 1.20 | AC012075.1 | −0.71 | −0.50 | 1.54 | −1.47 | −0.29 |
| RNU6-167P | 1.41 | 0.02 | −0.23 | 0.20 | −0.44 | AC006064.1 | −0.46 | −0.76 | 0.10 | 0.09 | 1.42 | IGHV1-58 | 0.88 | −0.96 | −0.28 | 0.28 | −0.01 |
| RASGRP1 | 0.73 | −0.33 | −0.67 | 0.12 | −0.27 | OMD | 0.23 | −0.09 | 0.21 | −0.04 | 0.02 | MIR188 | 0.27 | −0.67 | −0.10 | −0.03 | 0.36 |
| PBOV1 | −1.17 | 0.89 | 1.96 | −0.40 | 0.70 | C22orf34 | −0.27 | −0.03 | 0.22 | 0.08 | 0.13 | RPL17P2 | 0.47 | 0.43 | −1.22 | 0.11 | −1.62 |
| C5orf51 | 0.38 | −0.08 | −0.09 | −0.04 | −0.17 | AC097504.1 | −0.72 | −1.20 | −0.18 | −0.74 | 0.10 | FANK1-AS1 | 0.27 | −0.65 | 0.68 | 0.13 | 2.00 |
| AC093535.2 | −0.72 | 0.46 | 0.70 | 0.01 | −0.07 | RN7SL479P | −1.18 | 1.28 | 0.18 | 1.65 | −1.19 | AC009623.3 | −0.28 | −0.31 | 0.31 | −0.28 | −0.31 |
| AC024940.5 | 1.81 | −0.28 | −1.88 | 0.21 | −0.69 | AC103739.1 | −0.18 | −0.13 | 0.61 | −0.19 | 0.39 | SPATA31D2P | 0.19 | −0.84 | −1.10 | 0.05 | 0.09 |
| SLC7A2 | −0.61 | 0.46 | 0.61 | 0.15 | 0.09 | AGR2 | −0.28 | 0.23 | −0.34 | 0.02 | −0.47 | AC092821.2 | 0.16 | −0.18 | 0.22 | −0.80 | −1.39 |
| FUT9 | −1.35 | 0.22 | 1.36 | 0.51 | 1.28 | GBA2 | 0.10 | −0.02 | −0.23 | 0.10 | 0.08 | AC022796.1 | 0.47 | −0.99 | −1.55 | 0.25 | −0.96 |
| SELENOS | 0.35 | −0.22 | −0.20 | −0.28 | −0.18 | OOSP3 | 0.86 | −1.77 | 0.08 | 0.10 | 1.52 | SLC16A12-AS1 | 0.38 | −0.20 | −1.23 | 0.68 | −0.66 |
| GLCE | 0.45 | −0.01 | −0.27 | −0.02 | −0.26 | AC008417.1 | 0.52 | 0.37 | −0.48 | −0.12 | −1.19 | LINC01069 | −0.34 | −1.12 | −2.72 | 1.55 | 1.05 |
| AP000962.1 | −0.88 | 0.77 | 0.35 | 0.27 | −0.21 | SPANXN2 | −1.05 | 0.12 | −0.46 | 0.36 | −1.45 | LINC02346 | −0.20 | 0.46 | −1.38 | 1.13 | −0.29 |
| AC016734.1 | −0.75 | 0.30 | 0.11 | 0.14 | 0.10 | MCM3AP | −0.09 | −0.07 | −0.13 | 0.02 | 0.11 | KRTAP9-2 | −0.88 | 0.12 | 0.97 | −1.16 | −3.23 |
| EFCC1 | −0.74 | 0.44 | 0.52 | 0.71 | 0.23 | SECTM1 | 0.26 | −0.56 | −0.66 | −0.43 | −0.09 | AC090138.1 | −0.43 | 1.63 | −2.14 | 1.41 | −2.85 |
| CLMN | −0.55 | 0.40 | 0.29 | 0.26 | −0.04 | MT4 | −0.66 | 1.89 | 0.11 | 0.95 | −0.26 | LINC00880 | 0.23 | −0.88 | −0.92 | −1.14 | 0.61 |
| SLC13A2 | −1.29 | 1.19 | 1.57 | −0.01 | 0.36 | RNU6-190P | 0.59 | −0.10 | −1.03 | −0.10 | −0.84 | AL365226.1 | 0.14 | 0.85 | −0.65 | 0.28 | −1.18 |
| NDN | −0.88 | 0.47 | 0.95 | 0.01 | −0.02 | NDUFB2 | 0.11 | 0.02 | −0.27 | 0.16 | −0.11 | EBLN1 | 0.65 | 0.30 | −1.45 | 1.12 | −2.40 |
| PLA2G15 | −0.41 | 0.18 | 0.25 | 0.04 | −0.30 | AL021391.1 | −1.21 | −0.70 | 1.01 | −0.52 | 1.13 | AC006927.1 | −0.46 | −0.33 | −0.66 | −0.76 | −2.15 |
| PTMA | 0.43 | −0.28 | −0.32 | −0.15 | −0.18 | LINC00837 | −0.88 | −0.63 | 1.01 | 0.47 | 0.05 | AL162411.1 | −0.18 | 0.12 | −0.76 | 1.13 | 0.76 |
| FGD5P1 | −0.63 | 0.21 | 0.63 | 0.06 | 0.83 | AC090519.2 | −0.35 | 0.38 | 0.81 | −0.50 | 0.18 | AC092159.3 | −0.68 | 0.43 | −0.02 | −0.41 | 0.03 |
| AL391987.1 | −2.68 | −0.12 | 2.45 | 1.04 | 1.54 | AC080037.1 | 0.36 | −0.17 | −0.40 | 0.36 | 0.04 | AC073316.3 | 0.11 | −0.05 | −1.15 | −0.47 | −1.31 |
| ABLIM1 | 0.45 | 0.16 | −0.13 | 0.03 | −0.47 | AC090420.1 | −0.79 | 0.87 | 2.89 | −0.83 | 0.36 | AL596330.1 | 0.13 | 0.45 | 1.94 | 0.49 | 0.42 |
| AC002383.1 | −1.71 | −0.22 | 0.07 | 0.07 | 1.17 | STARD8 | 0.24 | −0.39 | −0.08 | −0.19 | −0.07 | ENPP7P9 | −0.21 | 0.62 | 0.53 | −0.67 | 0.39 |
| AC026403.1 | 0.74 | −0.03 | −0.66 | 0.33 | −0.75 | CPT2 | 0.18 | −0.21 | 0.13 | −0.22 | 0.05 | CPLX1 | −0.08 | −0.35 | −0.20 | 0.12 | −0.03 |
| CYP2A7 | −0.94 | 0.14 | 0.96 | −0.67 | 0.17 | ATM | −0.11 | 0.01 | 0.37 | −0.06 | 0.23 | AC017000.1 | 0.37 | 0.24 | 2.10 | −1.18 | −0.66 |
| SELENOP | −0.87 | 0.99 | 0.96 | 0.35 | 0.07 | MSX2 | 0.28 | −0.03 | 0.05 | −0.29 | −0.18 | MRC1 | −0.10 | −0.11 | −0.40 | 0.13 | −0.44 |
| CLCN4 | −0.75 | 0.31 | 1.27 | −0.15 | −0.15 | AL353801.3 | −0.68 | 1.52 | −0.83 | 1.11 | 0.52 | AC008379.1 | 0.10 | −0.11 | 0.04 | −0.14 | 0.38 |
| OLFML3 | −0.81 | 0.64 | 1.73 | −0.17 | 0.01 | AC078860.1 | −1.15 | 1.16 | 0.08 | 0.07 | −0.58 | HNRNPUP1 | −0.16 | 0.05 | −0.54 | 0.96 | 0.18 |
| ALG10B | −0.41 | 0.26 | 0.54 | 0.03 | 0.05 | SLC22A14 | 0.50 | −1.70 | −0.92 | −0.13 | 0.59 | RNU7-71P | 0.15 | 0.07 | −0.84 | −0.93 | −0.19 |
| LRRC6 | −0.56 | 0.17 | 0.40 | −0.06 | 0.09 | AC008638.1 | 1.01 | −0.61 | −3.01 | −0.37 | −2.15 | AL359752.1 | −0.05 | 0.65 | 0.07 | 0.48 | −0.05 |
| CYP2F2P | −0.76 | 0.65 | −0.07 | 0.28 | −0.25 | AC005840.1 | 0.43 | −0.13 | −0.66 | −0.64 | −0.61 | SNORA50 | 0.05 | 0.50 | 0.08 | 0.18 | −0.50 |
| AC009879.3 | −1.43 | 1.16 | −0.63 | 1.17 | −0.12 | IGFBP7 | −0.23 | 0.21 | 0.67 | −0.19 | −0.12 | AC027243.2 | 0.46 | −1.67 | −0.52 | −1.54 | −0.32 |
| LYRM4 | 0.32 | −0.22 | −0.30 | −0.07 | −0.22 | IGSF23 | 0.74 | −0.85 | 0.27 | −0.44 | 0.77 | IDI2 | 0.12 | −0.57 | −0.68 | −0.22 | −0.14 |
| AL135999.2 | −1.15 | 0.49 | 0.79 | −0.17 | 0.16 | GGNBP1 | 0.53 | −1.08 | −0.98 | 0.44 | 0.28 | AL354821.1 | −0.32 | −1.10 | −0.36 | 0.08 | 0.74 |
| CXXC1 | −0.61 | 0.24 | −0.02 | 0.37 | 0.15 | AL357153.4 | −0.33 | 0.10 | 0.93 | −0.23 | 0.15 | LINC01561 | −0.15 | 1.17 | 0.84 | −0.12 | 0.28 |
| FCGR3B | 1.18 | −1.04 | −0.44 | −0.56 | −1.02 | AC102953.1 | −0.63 | 1.11 | 0.55 | 0.59 | −1.18 | RNU6-605P | 0.32 | 0.44 | 0.73 | 0.41 | −0.09 |
| OLR1 | 1.79 | −1.75 | −0.74 | −0.12 | −0.51 | AC011445.1 | −0.69 | −0.14 | 0.05 | −0.36 | 0.55 | AL121990.1 | −0.21 | 1.33 | −0.89 | 0.18 | −0.50 |
| PLANP | −0.73 | −0.02 | 0.55 | 0.20 | 0.36 | G5265 | −0.89 | 2.85 | 1.85 | 1.67 | −0.40 | ARHGEF9-IT1 | −0.09 | 0.07 | 1.19 | 0.55 | 1.36 |
| G42642 | −0.85 | 0.25 | 0.76 | 0.47 | 0.48 | PMS2 | −0.10 | 0.04 | 0.11 | 0.08 | 0.22 | RNA5SP118 | 0.13 | 0.83 | 0.90 | 0.46 | −0.10 |
| HS3ST2 | −1.28 | 0.46 | 1.15 | −0.28 | −0.56 | ARHGEF5 | −0.18 | 0.38 | 0.07 | 0.42 | 0.33 | AC112907.1 | 0.25 | −1.33 | −1.50 | 0.31 | −0.39 |
| DNAJA1 | 0.49 | −0.40 | −0.31 | −0.46 | −0.18 | SOCS5P3 | 1.12 | −1.02 | −1.91 | 0.00 | −1.56 | AC003092.1 | 0.20 | 0.25 | 0.17 | 0.52 | −0.39 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| METTL3 | −0.31 | 0.10 | 0.07 | 0.16 | 0.13 | AL031663.3 | −0.37 | 0.32 | 0.75 | −0.43 | −0.11 | EIF2B5 | −0.02 | −0.04 | −0.16 | 0.10 | 0.02 |
| PRKX | 0.32 | −0.13 | −0.16 | 0.08 | 0.22 | PLEKHA3 | −0.16 | 0.15 | 0.22 | −0.04 | −0.08 | HMGN1P10 | −0.17 | 0.12 | −0.85 | 0.25 | −0.96 |
| PMPCA | 0.34 | −0.20 | −0.32 | −0.10 | −0.05 | RPS3AP44 | 0.39 | −0.21 | −0.23 | −0.12 | −0.02 | AC108078.1 | −0.87 | 0.16 | −0.56 | 0.20 | −0.64 |
| MUC4 | −1.00 | 0.02 | 0.26 | 0.81 | 1.11 | AC008764.1 | 0.42 | −0.80 | −0.31 | −0.39 | 0.06 | AC084871.2 | 0.39 | 0.43 | −1.01 | 1.16 | −2.26 |
| C8orf33 | 0.30 | −0.21 | −0.24 | −0.12 | −0.05 | LINC02043 | 0.36 | −0.99 | −0.48 | 0.31 | 0.85 | LINC01711 | 0.19 | −0.64 | −0.30 | −0.77 | −0.28 |
| AC018445.3 | −0.97 | −0.02 | 0.24 | −0.05 | 0.68 | AL137786.1 | −0.56 | −0.97 | −0.99 | −0.16 | −0.24 | AC109830.1 | 0.47 | −0.55 | −0.63 | −0.17 | −2.55 |
| AP000654.1 | 1.09 | −0.28 | −0.11 | −0.43 | −0.36 | LINC01646 | 1.26 | −0.89 | −1.62 | −0.44 | −2.85 | OR2T1 | −0.21 | 0.58 | 1.05 | 0.18 | 0.04 |
| AC022973.2 | 0.99 | −0.75 | −0.71 | −0.52 | −0.12 | PHKG2 | 0.14 | −0.20 | −0.44 | −0.03 | −0.17 | AC011290.1 | 0.48 | −1.16 | 0.99 | −1.16 | −0.64 |
| AC112128.1 | −0.65 | 0.49 | 0.50 | 0.40 | 0.40 | CAP2 | −0.23 | 0.29 | −0.03 | 0.27 | −0.46 | AC004869.2 | 0.87 | −1.26 | −0.96 | 0.53 | 0.33 |
| MAP1B | −0.68 | 0.33 | 0.96 | 0.36 | 0.17 | MPO | 0.71 | −1.01 | −0.20 | −0.10 | 0.48 | OR6M3P | −0.38 | 0.14 | −1.06 | 2.01 | 0.55 |
| SHQ1 | 0.28 | −0.20 | −0.24 | −0.16 | −0.04 | SLC39A1 | 0.35 | −0.51 | −0.61 | −0.18 | −0.16 | FENDRR | −0.13 | −1.38 | 0.45 | −0.12 | 1.13 |
| CLPTM1 | 0.29 | −0.07 | −0.40 | −0.06 | −0.32 | RNU6-482P | 0.81 | −0.64 | 1.08 | −0.80 | 0.53 | LHX1-DT | −0.23 | −1.11 | −1.92 | −0.34 | 0.33 |
| AC123768.1 | 1.48 | −0.61 | −0.77 | 0.40 | −0.06 | AC009961.1 | −0.20 | 0.11 | 1.10 | −0.04 | 0.41 | KRT8P46 | −0.05 | 0.20 | 0.12 | 0.13 | −0.04 |
| KCND2 | −1.22 | 0.71 | 1.72 | 0.49 | 0.23 | AL390730.2 | 1.00 | −1.22 | −0.51 | −0.31 | −0.17 | AC007223.1 | −0.39 | −0.60 | −0.40 | 0.44 | 0.56 |
| KRTAP3-2 | −2.49 | 0.97 | 2.27 | −0.14 | −0.68 | CDC42-IT1 | −0.25 | −0.15 | 0.58 | −0.26 | 0.63 | BICD1P1 | −0.29 | −1.08 | 0.60 | −0.54 | 1.68 |
| NPTXR | −0.89 | −0.19 | 0.53 | 0.03 | 0.19 | AC025186.1 | 0.99 | −0.70 | −0.20 | −0.60 | 0.52 | AC090960.1 | 0.15 | 1.52 | 0.57 | 1.03 | −0.10 |
| ANKS3 | −0.41 | 0.13 | 0.16 | 0.09 | 0.29 | AC006116.1 | −0.49 | −0.48 | −0.76 | −0.18 | 0.23 | CLDN6 | 0.46 | −0.21 | −0.96 | 0.32 | −1.42 |
| GALNT8 | −1.21 | 0.73 | 1.70 | −0.15 | −0.25 | AC022001.3 | 0.31 | 0.20 | −0.12 | 0.03 | −0.35 | AC025265.2 | −0.35 | 0.43 | 2.80 | −1.04 | 0.78 |
| LINC00471 | −0.87 | −0.05 | 0.91 | −0.09 | 0.44 | RPL19P14 | 0.45 | −0.43 | 0.64 | −1.19 | −0.63 | SSX7 | 0.87 | 0.06 | 1.37 | 0.55 | 0.58 |
| AC134312.4 | −1.03 | 0.81 | 1.23 | 0.34 | −0.10 | LZTR1 | −0.16 | −0.12 | 0.00 | −0.08 | 0.13 | AC013436.1 | 0.51 | 0.60 | −0.01 | 1.90 | 0.60 |
| ABCA5 | −0.49 | 0.47 | 0.54 | 0.27 | 0.18 | AC131953.1 | 0.45 | −0.14 | −0.08 | 0.25 | 0.32 | SSH3 | −0.02 | 0.08 | −0.32 | 0.27 | 0.09 |
| AL136018.1 | −1.79 | 1.06 | 0.09 | −0.39 | −0.05 | SPTA1 | −0.52 | −0.03 | 0.04 | 0.38 | −0.16 | BPIFA3 | 0.20 | −0.20 | −1.87 | 0.91 | −0.43 |
| AES | −0.28 | 0.31 | 0.04 | 0.19 | −0.02 | SAMD11P1 | 0.48 | 0.18 | −0.81 | −0.07 | −1.07 | FHAD1 | −0.06 | −0.01 | −0.03 | −0.23 | −0.26 |
| CINP | 0.33 | −0.25 | −0.13 | −0.18 | −0.03 | AC090952.2 | 0.89 | −0.34 | −0.27 | 0.40 | −0.78 | CCDC17 | 0.05 | 0.16 | 0.14 | 0.22 | −0.06 |
| STK11IP | −0.53 | 0.14 | −0.08 | 0.38 | 0.18 | RSPH10B | −0.51 | 0.11 | −0.13 | 0.06 | −0.53 | LINC02394 | −0.22 | 0.43 | −0.83 | 0.53 | 0.73 |
| SIX1 | −1.40 | 1.08 | 1.36 | 0.09 | 0.12 | GABRA5 | −0.67 | 0.79 | −0.14 | 0.52 | −1.55 | FO393401.2 | 0.14 | −1.02 | 0.61 | −0.64 | 0.18 |
| RARB | −0.54 | 0.44 | 0.53 | 0.22 | 0.21 | C16orf70 | 0.14 | 0.07 | 0.17 | 0.15 | −0.02 | POC1B-GALNT< | −0.06 | −0.11 | 0.18 | −0.02 | 0.55 |
| CCDC80 | −1.15 | 0.94 | 2.53 | −0.17 | 0.48 | LAPTM4A | 0.17 | 0.08 | 0.03 | −0.10 | −0.23 | RPRM | 0.08 | 0.90 | 0.07 | 0.43 | −0.33 |
| SLC39A2 | 0.96 | 0.20 | 0.06 | 0.41 | −0.42 | RNU7-119P | −0.75 | −0.26 | 1.05 | −0.42 | 0.54 | OR51B4 | −0.28 | 1.20 | 1.31 | 0.50 | −0.79 |
| CASC18 | −1.49 | −0.09 | −0.42 | 0.80 | 0.63 | NUDT14 | −0.19 | 0.25 | −0.35 | 0.39 | 0.02 | AC016651.1 | −0.20 | 0.06 | −1.00 | −1.42 | −1.84 |
| MIR4524B | −1.29 | 1.03 | 1.10 | 0.00 | 0.45 | G31721 | 1.03 | −1.67 | −2.78 | −1.75 | −1.38 | AC117525.1 | −0.56 | −0.21 | −0.97 | 1.32 | −0.08 |
| MIR570 | −0.62 | 0.24 | 0.85 | −0.04 | 0.18 | LINC01395 | −0.42 | 0.26 | 0.49 | 0.26 | 0.03 | LINC01729 | 0.32 | −0.50 | −1.15 | 1.09 | 0.84 |
| SLC25A16 | −0.35 | 0.04 | 0.06 | 0.02 | 0.12 | CCDC91 | 0.12 | −0.10 | −0.28 | 0.03 | −0.04 | AC007384.1 | 0.06 | −0.62 | −0.15 | −0.06 | −0.05 |
| PHF11 | 0.24 | −0.08 | −0.26 | −0.05 | −0.17 | SLC37A2 | 0.25 | 0.21 | 0.19 | 0.52 | −0.40 | AL512430.2 | 0.13 | 0.22 | −0.13 | 0.64 | 0.01 |
| BTN3A1 | −0.57 | −0.06 | 0.92 | −0.35 | 0.23 | AC097515.1 | −0.59 | −0.73 | 1.32 | 0.00 | 0.86 | CCDC185 | 0.20 | −0.15 | −0.47 | −0.21 | −2.13 |
| CYSTM1 | −0.55 | 0.41 | 0.19 | 0.04 | −0.13 | OR52T1P | −0.51 | 1.01 | −0.16 | 0.19 | −1.09 | LINC01603 | 0.11 | 0.17 | −0.27 | 0.13 | 0.17 |
| C9orf152 | −1.13 | 0.48 | 1.31 | 0.01 | 0.96 | RNU7-13P | 0.88 | −0.69 | −1.57 | 0.47 | −0.98 | PTAR1 | −0.02 | 0.11 | 0.11 | 0.03 | 0.01 |
| SUGT1P3 | −0.78 | 0.62 | 0.98 | 0.04 | 0.16 | LINC01429 | −0.51 | −0.30 | 0.24 | 0.19 | −0.59 | AC092848.1 | 0.32 | −0.48 | −0.67 | −0.73 | −1.13 |
| OR56A3 | −1.70 | 0.19 | 0.87 | −0.36 | 0.38 | HNRNPA1P72 | −0.70 | 1.98 | 2.06 | 0.80 | −0.31 | RN7SKP1 | 0.41 | −1.10 | −0.31 | 0.24 | 2.01 |
| EEA1 | 0.44 | −0.10 | −0.40 | −0.16 | −0.36 | ADAMTSL5 | 0.22 | −0.64 | −0.74 | 0.02 | 0.50 | AL050327.1 | −0.18 | 0.09 | 0.54 | −1.79 | −1.34 |
| ADAMTS16 | −1.16 | 0.50 | −0.07 | 0.41 | 0.51 | SLFN12 | 0.18 | −0.42 | 0.12 | −0.41 | 0.13 | AGXT | −0.12 | 0.50 | −1.50 | 0.63 | −1.10 |
| RN7SL850P | −1.42 | 0.26 | −0.13 | 0.94 | 0.94 | AC011095.1 | −1.07 | −1.04 | −1.37 | 0.24 | 0.32 | AC009093.7 | −0.11 | 0.18 | −1.03 | 0.48 | −0.44 |
| C19orf70 | 0.30 | −0.06 | −0.09 | 0.00 | −0.08 | CEP85 | 0.14 | −0.20 | −0.47 | 0.03 | −0.03 | RBMS2P1 | −0.05 | 0.25 | 0.64 | −0.18 | −0.06 |
| BOLA3 | 0.75 | −0.62 | −0.37 | −0.39 | 0.07 | AC130371.2 | −0.31 | 0.73 | 0.78 | 0.00 | −0.10 | MBTPS1 | 0.02 | 0.11 | 0.18 | −0.03 | −0.06 |
| FZD6 | 0.44 | 0.07 | −0.17 | −0.03 | −0.32 | NLRP4 | 0.72 | −0.38 | −1.38 | 0.30 | −1.25 | AC147651.1 | 0.15 | 0.61 | −0.95 | 0.37 | −0.65 |
| DDIT4 | 0.75 | −1.06 | −1.28 | −0.31 | −0.45 | OR2B11 | 0.51 | −0.76 | −0.49 | 0.10 | 0.16 | C1orf140 | −0.10 | 0.39 | −1.05 | 0.54 | −0.98 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| CCAR1 | 0.33 | −0.26 | −0.48 | −0.08 | −0.17 | AC108718.1 | 0.66 | −0.03 | 0.86 | 1.06 | 0.91 | AL451000.1 | 0.35 | −0.98 | −1.32 | 0.53 | 0.31 |
| AC108097.1 | 1.83 | −0.17 | −0.96 | −0.17 | −0.89 | CBX1P4 | −0.66 | 0.30 | 0.16 | 1.27 | 0.68 | RN7SL851P | −0.15 | 0.92 | −0.19 | 0.81 | −0.09 |
| PICK1 | −0.52 | 0.27 | −0.25 | 0.40 | 0.06 | RN7SKP38 | 0.65 | −0.35 | 0.27 | −1.00 | −0.62 | LINC00368 | −0.26 | −0.93 | −0.12 | −0.04 | 0.24 |
| ELAVL2 | 1.06 | −0.74 | −1.66 | −0.15 | −0.51 | AC005520.1 | 0.39 | 0.27 | −0.51 | 0.48 | −0.14 | RN7SKP75 | −0.45 | −1.11 | −0.16 | 1.19 | 1.82 |
| G25761 | 1.50 | −0.66 | −0.79 | −0.19 | 0.22 | AC023906.4 | 0.35 | −0.28 | −0.22 | −0.06 | 0.11 | LINC02483 | −0.31 | −1.37 | −1.24 | 0.01 | −0.51 |
| MAPK10 | −0.71 | 0.52 | 0.45 | 0.36 | −0.29 | RNU6-1121P | 0.86 | −1.15 | 1.83 | −0.43 | 1.28 | AL138921.2 | −0.09 | 0.16 | −0.01 | 0.61 | 0.07 |
| MSRB3 | −0.79 | 0.40 | 1.06 | −0.07 | 0.03 | FAM131C | −0.50 | −0.09 | 0.16 | 0.02 | −0.08 | AC083964.1 | −0.14 | 0.25 | 1.01 | 0.16 | −0.34 |
| RN7SL133P | −1.13 | −1.03 | 0.19 | 0.04 | 1.16 | AC138894.1 | −0.95 | 0.89 | 1.28 | 0.56 | 1.35 | MOG | 0.13 | −0.28 | −0.03 | 1.05 | 1.59 |
| FLJ16779 | −1.16 | 0.98 | 0.55 | −0.04 | −0.30 | FTH1P23 | −0.38 | 0.44 | 1.14 | 0.04 | 0.11 | AC007992.1 | 0.42 | −0.21 | −1.09 | −0.23 | −0.35 |
| MEF2C-AS1 | −0.98 | 0.37 | 0.89 | 0.06 | −0.25 | AP000919.1 | 0.25 | −0.53 | −0.32 | −0.26 | 0.00 | RP11-318K12.1 | 0.28 | −0.14 | −0.61 | 0.14 | −1.98 |
| AGBL3 | −0.45 | 0.25 | 0.62 | −0.16 | 0.00 | AC022762.2 | −0.27 | 0.28 | 0.43 | −0.02 | −0.03 | AC104073.4 | 0.30 | −0.86 | −2.99 | 0.52 | −2.23 |
| C10orf67 | −0.93 | 0.38 | 0.53 | 0.44 | 0.66 | AC004233.4 | −0.76 | 0.38 | 0.58 | 0.59 | −1.27 | ATP2B4 | 0.03 | 0.16 | 0.04 | 0.14 | −0.17 |
| RN7SL564P | −1.39 | 1.06 | 0.21 | 0.71 | −0.16 | PDXP | 0.47 | −0.09 | 0.02 | 0.13 | 0.32 | KDM4C | 0.02 | 0.01 | 0.05 | 0.01 | 0.09 |
| GDF10 | −1.32 | 1.42 | 1.88 | 0.51 | −0.06 | AC041040.1 | 0.39 | −1.19 | −0.06 | −1.21 | 0.16 | DDX6P2 | −0.24 | −0.92 | −1.96 | −0.10 | −0.94 |
| METTL2B | −0.28 | 0.09 | 0.11 | 0.02 | 0.12 | GNA11 | −0.10 | 0.04 | −0.05 | 0.11 | 0.19 | RNU6-293P | −0.54 | 0.79 | 1.48 | 0.97 | 0.96 |
| G26723 | −1.45 | 0.33 | 1.19 | 0.17 | 0.98 | AC087741.2 | 0.77 | 0.67 | 0.23 | 0.30 | 0.52 | SHMT1P1 | −0.06 | −0.78 | −0.44 | 0.13 | 0.12 |
| AL122125.1 | 1.10 | −0.42 | −0.11 | 0.07 | 0.34 | RPS17P13 | 0.51 | −0.02 | 0.16 | 0.47 | 0.02 | HPRT1P1 | 0.59 | −0.62 | −0.16 | 0.57 | −0.40 |
| COX15 | 0.41 | −0.21 | −0.17 | −0.14 | 0.01 | SNORD53 | −0.36 | 0.48 | −0.09 | −0.07 | −0.16 | HAVCR2 | 0.06 | −0.49 | −0.10 | −0.34 | 0.12 |
| AF064858.3 | −1.34 | −0.94 | 0.94 | 0.09 | 0.61 | NADSYN1 | 0.11 | 0.08 | −0.31 | 0.13 | −0.13 | API5P2 | 0.20 | 0.29 | 1.05 | 0.77 | 0.93 |
| CLEC18A | −1.10 | 0.42 | 0.35 | 0.25 | 0.03 | KBTBD13 | −0.59 | 0.04 | 0.83 | −0.31 | 0.23 | MIR933 | 0.13 | −1.72 | −0.53 | −0.20 | 0.75 |
| AC018557.2 | −0.86 | 0.25 | 0.00 | 0.34 | 0.34 | MT-TL1 | −0.42 | 0.10 | 0.07 | 0.66 | −0.58 | AP000753.2 | −0.06 | 0.00 | 0.13 | −0.10 | 0.21 |
| DUS2 | 0.39 | −0.22 | −0.59 | 0.10 | −0.13 | AC019131.2 | 0.26 | −0.12 | 0.11 | 0.00 | 0.01 | LINC01647 | −0.29 | 0.01 | −1.29 | 0.13 | −0.26 |
| MKRN2 | 0.34 | −0.21 | −0.13 | −0.10 | −0.06 | AC239803.3 | −1.08 | 0.90 | −0.42 | 1.49 | −1.33 | CA9 | −0.10 | −0.38 | −0.33 | −0.33 | −0.45 |
| CASP8 | 0.35 | −0.46 | −0.43 | −0.08 | 0.10 | AC064850.1 | 0.33 | −0.72 | −0.54 | −0.12 | −0.27 | AC091173.1 | −0.15 | −1.44 | 0.32 | −0.41 | −0.22 |
| KMT5A | 0.33 | −0.05 | −0.49 | 0.03 | −0.27 | DEPDC1-AS1 | 0.80 | −0.72 | −3.04 | 0.03 | −1.79 | LINC00351 | 0.44 | −0.93 | −0.85 | 0.37 | 0.12 |
| AC078864.1 | −1.34 | 1.15 | 2.37 | 0.15 | 0.64 | CR381670.1 | −0.44 | 0.15 | 1.21 | 0.52 | 1.50 | RP11-439A17.7 | −0.08 | 0.25 | 0.52 | 0.07 | −0.27 |
| ADGRD1-AS1 | −1.38 | 2.01 | 1.31 | 0.93 | −0.35 | AC068722.2 | 0.58 | −0.54 | 0.65 | −0.26 | 0.72 | AL161644.1 | 0.07 | 0.25 | −0.62 | 0.10 | −0.24 |
| HOXA3 | −0.55 | 0.14 | 0.47 | 0.27 | 0.19 | LINC02052 | 1.11 | −0.90 | −1.39 | 0.14 | −1.13 | PPIAP69 | −0.22 | −0.27 | 1.51 | −0.05 | 0.18 |
| AC106800.4 | 1.74 | −0.10 | 0.06 | −0.02 | 0.21 | ODAM | −0.92 | −0.08 | 0.81 | 0.06 | −0.55 | RPL7P41 | 0.47 | −0.24 | 0.12 | −0.01 | 0.41 |
| CAMTA2 | −0.42 | 0.17 | −0.03 | 0.21 | 0.02 | G33836 | −0.72 | −1.65 | 0.16 | −0.33 | 0.88 | LINC02111 | 0.28 | −2.13 | 0.88 | −0.69 | 0.65 |
| NBPF20 | −0.42 | 0.01 | 0.25 | −0.01 | 0.37 | AC009803.2 | −0.70 | 0.84 | 0.70 | −0.13 | 1.33 | AC069304.1 | −0.36 | −1.61 | −0.68 | 0.37 | 0.69 |
| RPLPOP6 | 0.70 | −0.10 | −0.29 | −0.14 | −0.49 | AC008115.3 | 0.28 | −0.15 | 0.01 | 0.32 | 0.27 | NWD2 | 0.08 | −0.27 | −0.60 | 0.47 | −0.26 |
| ORMDL2 | 0.48 | −0.33 | −0.45 | −0.02 | −0.27 | AL137058.1 | −0.41 | −0.16 | −0.85 | 0.24 | −0.05 | BAGE2 | −0.12 | 0.06 | −1.77 | 0.57 | −1.63 |
| ETV4 | 0.75 | −0.49 | −0.65 | 0.27 | −0.02 | RNU1-75P | −1.27 | 1.79 | −0.26 | 0.43 | −1.79 | AC007686.3 | −0.04 | 0.29 | −0.62 | 0.43 | −0.26 |
| NAA25 | 0.36 | −0.20 | −0.42 | 0.06 | −0.09 | AC092747.1 | 0.45 | −0.85 | −0.15 | −0.19 | 0.12 | AP001282.2 | −0.16 | 0.13 | 1.17 | −0.16 | −0.02 |
| RNF139-AS1 | −0.34 | 0.11 | 0.29 | 0.14 | 0.11 | LINC01504 | −0.36 | −0.16 | 0.67 | −0.22 | 0.56 | AC027026.1 | −0.29 | −0.57 | −1.58 | 0.52 | 1.64 |
| GALE | 0.64 | −0.72 | −0.93 | −0.17 | −0.10 | AC092535.4 | −0.45 | 0.39 | 0.59 | 0.37 | −0.12 | RPL7P7 | 0.04 | −0.33 | −0.17 | −0.23 | 0.53 |
| CXCR4 | 1.02 | −1.12 | −0.92 | −0.37 | −0.18 | AL136988.2 | 0.29 | −0.15 | −0.81 | −0.25 | −0.56 | STX18-IT1 | 0.08 | −0.06 | −0.65 | −0.21 | −0.29 |
| NSMCE1 | 0.43 | −0.04 | −0.03 | −0.17 | −0.30 | AC079414.3 | −0.32 | 0.14 | 0.25 | 0.38 | −0.22 | AC097059.1 | −0.15 | 0.22 | −0.48 | −0.31 | −1.08 |
| AC012100.2 | −1.04 | 0.43 | −0.14 | 0.54 | −0.02 | AC009303.1 | −0.65 | 0.14 | −0.38 | 0.09 | −0.31 | SINHCAFP3 | −0.33 | 0.93 | −0.34 | 0.79 | −0.43 |
| SPIN3 | −0.49 | 0.21 | 0.54 | 0.14 | 0.29 | AC022404.1 | −0.98 | −1.72 | 1.70 | −1.41 | 2.36 | LIG3 | 0.02 | 0.04 | 0.08 | 0.09 | 0.01 |
| RNFT2 | −0.80 | −0.33 | 0.17 | −0.23 | 0.22 | EIF4ENIF1 | −0.08 | 0.03 | 0.10 | 0.01 | 0.05 | RSF1-IT2 | −0.07 | 0.06 | 0.65 | −0.39 | −0.03 |
| EEF1B2P6 | 1.05 | −0.83 | −0.86 | −0.23 | −0.56 | SCN2A | −0.33 | −0.27 | 0.22 | −0.04 | 0.30 | MCOLN1 | −0.02 | 0.07 | −0.09 | 0.17 | −0.15 |
| RGMB | −0.45 | 0.34 | 0.91 | 0.13 | 0.37 | AC009630.2 | 0.96 | −2.28 | −1.44 | 0.36 | 2.80 | MTCO2P16 | −0.50 | −0.96 | −0.77 | −0.18 | −0.27 |
| C9orf131 | −0.57 | 0.28 | 0.50 | −0.20 | 0.37 | EEF1A1P5 | 0.18 | 0.20 | 0.27 | −0.03 | −0.20 | AC004221.1 | 0.20 | −0.43 | −0.13 | 0.89 | −0.09 |
| SNORA80 | −1.08 | 0.33 | −0.41 | 0.94 | 0.03 | ARHGAP28 | −0.22 | 0.08 | 0.64 | −0.42 | 0.07 | EGFLAM-AS2 | 0.12 | 0.16 | 0.06 | −0.02 | −0.57 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| LTF | 1.48 | −0.27 | −2.32 | 0.81 | −1.86 | RNU6-249P | 1.12 | −0.08 | 1.14 | −0.97 | 1.13 | AC146944.3 | 0.14 | −0.94 | −0.24 | −0.72 | 0.80 |
| AC009063.3 | −0.87 | 0.16 | −0.31 | 0.30 | 0.14 | RETNLB | −1.04 | 0.36 | 0.08 | 0.93 | 1.07 | RN7SL253P | −0.36 | −1.95 | 0.58 | −0.63 | 2.28 |
| AL049647.1 | 0.90 | −0.32 | −0.19 | 0.05 | 0.12 | SH3RF2 | 0.22 | 0.41 | −0.04 | 0.27 | −0.09 | AP006216.1 | 0.40 | 0.76 | −1.93 | 0.47 | −1.17 |
| AC005906.2 | −1.46 | 0.54 | 0.43 | 0.79 | −0.46 | HNRNPA1P5 | −0.26 | 0.42 | 0.53 | −0.04 | 0.14 | AP002026.1 | 0.03 | 0.17 | 0.00 | −0.07 | −0.44 |
| LINC00899 | −0.59 | 0.23 | 0.26 | 0.44 | 0.28 | AC109460.3 | −0.56 | 0.34 | 0.55 | 0.63 | 1.04 | AL109935.2 | 0.61 | −0.42 | 1.48 | 0.15 | 2.07 |
| GPR107 | 0.35 | −0.13 | −0.11 | −0.11 | −0.10 | SRARP | −0.84 | −1.30 | 0.60 | −1.74 | 0.90 | AC063980.1 | 0.79 | 1.64 | −0.25 | 1.27 | −1.86 |
| AC104031.1 | 0.96 | −0.11 | −0.53 | −0.19 | −0.32 | AC090115.1 | −0.50 | 0.15 | −0.31 | 0.32 | −0.13 | CDH8 | −0.09 | 0.09 | 0.27 | 0.00 | 0.04 |
| AC004982.1 | −0.75 | 0.94 | 0.86 | 0.41 | −0.06 | AL161636.2 | −0.86 | 1.59 | 1.62 | −0.05 | −0.13 | NUP58P1 | −0.34 | −0.70 | 0.93 | −0.50 | 1.65 |
| PRSS8 | 0.60 | −0.07 | −0.46 | −0.01 | −0.33 | LINC01508 | −0.95 | 0.64 | −0.69 | 0.88 | 0.17 | AC013286.1 | 0.10 | −0.48 | 0.17 | −0.55 | 0.62 |
| EBF3 | −0.85 | 0.45 | 1.20 | 0.28 | 0.13 | AC009065.4 | −0.32 | 0.16 | 0.62 | 0.03 | 0.24 | PPIAP33 | 0.39 | −0.27 | −0.62 | 1.20 | −1.18 |
| GRIN1 | −1.21 | 0.54 | 0.50 | 0.84 | 0.57 | EEF1D | 0.15 | −0.13 | −0.48 | 0.12 | −0.09 | FAM106B | −0.35 | −0.05 | 1.03 | −0.52 | 1.47 |
| AL163192.1 | 0.97 | −0.74 | −0.56 | 0.03 | −0.04 | IGF2BP1 | 0.69 | −0.12 | −1.40 | 0.29 | −0.10 | ASCL5 | −0.12 | −1.31 | −1.09 | 0.45 | 0.68 |
| RPL29P14 | 0.75 | −0.48 | −0.62 | −0.20 | −0.06 | AL450344.3 | −0.43 | 0.80 | 0.59 | −0.20 | 0.31 | HMGB1P14 | −0.06 | 0.05 | 0.20 | 0.04 | 0.17 |
| AC097478.3 | −1.20 | 0.49 | 1.94 | −0.09 | 1.00 | AC006077.2 | 0.37 | 0.34 | −0.55 | 0.72 | −0.31 | AC004882.1 | −0.49 | −0.04 | 1.73 | 0.93 | 1.70 |
| LINC02235 | −0.92 | 1.08 | 0.69 | 0.60 | 0.02 | AL359473.1 | −1.20 | −0.07 | −0.86 | 1.07 | 0.90 | C2orf69P3 | 0.59 | −1.06 | −1.94 | 0.17 | −0.11 |
| NQO2 | 0.29 | −0.16 | −0.19 | −0.06 | −0.08 | MTCO3P11 | 0.27 | 0.30 | −0.05 | 0.17 | −0.08 | GLUD2 | 0.07 | 0.56 | −0.12 | −0.05 | −0.21 |
| RN7SL368P | 2.00 | −1.19 | −0.60 | −1.33 | −1.13 | IGHV1-2 | 1.64 | 2.81 | 0.30 | 1.24 | −0.93 | AC009078.1 | 0.40 | −1.41 | −0.44 | 1.45 | 1.96 |
| C19orf24 | 0.52 | −0.28 | −0.49 | 0.09 | 0.00 | RBFOX2 | 0.09 | 0.04 | −0.07 | −0.02 | −0.12 | AC004241.2 | 0.10 | 0.08 | −0.70 | 0.16 | −0.17 |
| AC012368.1 | −0.73 | 0.48 | 0.25 | 0.40 | 0.02 | AC106801.1 | 0.41 | −0.66 | −0.93 | −0.81 | −0.46 | C19orf54 | 0.03 | −0.03 | −0.27 | 0.01 | −0.11 |
| MAPT-AS1 | −1.34 | 0.16 | 0.62 | 0.01 | −0.17 | BMP6 | 0.29 | 0.05 | −0.52 | −0.09 | −0.39 | SRSF10 | 0.02 | −0.12 | −0.15 | −0.13 | −0.03 |
| CXCL3 | 1.55 | −0.91 | −1.21 | −1.07 | −1.02 | AC098869.2 | 0.38 | −0.35 | 0.33 | −0.45 | −0.02 | LINC01339 | −0.36 | −0.48 | −0.82 | −0.53 | 0.66 |
| LGALS7 | 1.00 | 0.03 | −0.56 | 1.03 | −1.04 | AC090971.4 | 0.29 | −0.21 | −0.54 | −0.29 | −0.29 | MT-CO2 | 0.04 | −0.05 | 0.08 | −0.13 | 0.00 |
| NDUFA4L2 | 0.84 | 0.03 | −0.43 | 0.20 | −0.91 | KIAA1210 | −0.55 | 0.05 | −0.04 | 0.29 | 0.13 | ADAM6 | 0.42 | −0.80 | −0.69 | −0.39 | −1.59 |
| PPP1R1B | −1.19 | 0.87 | 1.00 | 0.46 | 0.54 | AC004253.1 | 0.34 | −0.03 | 0.32 | 0.32 | 0.44 | AC109446.2 | 0.39 | −0.87 | −1.83 | 0.11 | −0.24 |
| SNX12 | 0.34 | 0.05 | −0.27 | 0.06 | −0.25 | RGS9BP | −0.50 | 0.63 | 0.95 | −0.08 | 1.15 | AC092106.1 | 0.35 | −0.48 | −0.89 | −0.58 | −1.05 |
| CA13 | −0.50 | 0.52 | 0.95 | 0.03 | 0.35 | IFIT6P | 1.12 | −1.05 | −2.33 | 0.10 | −2.04 | PPIAP36 | 0.12 | 0.31 | 0.49 | 0.20 | −0.48 |
| AC079804.1 | −2.44 | 0.54 | 3.42 | −0.45 | 1.70 | AC104958.2 | −0.87 | 0.58 | −1.45 | 1.56 | −1.34 | SOCS5P1 | −0.46 | −0.71 | 1.01 | −1.23 | −0.04 |
| LDHAL6B | 0.63 | −0.15 | −0.54 | −0.08 | −0.57 | LGMN | 0.22 | 0.06 | −0.16 | 0.00 | −0.32 | AC069528.1 | −0.39 | −0.08 | −0.10 | 0.79 | −0.06 |
| MIR26B | −1.09 | 0.20 | 0.18 | 0.48 | 0.18 | PDCD1 | 0.46 | −0.56 | −0.83 | −0.45 | 0.69 | OR4A40P | −0.28 | 0.72 | −1.80 | 0.68 | −1.73 |
| AC004923.1 | −0.93 | 0.87 | 0.72 | 0.73 | −0.25 | RAP2CP1 | −1.70 | 1.06 | 0.05 | 0.62 | −0.70 | LINC00634 | −0.19 | 0.03 | 0.60 | −0.37 | 1.09 |
| RAB11FIP5 | 0.36 | −0.03 | −0.59 | 0.06 | −0.32 | PRRX1 | −0.28 | 0.13 | 1.19 | −0.48 | 0.00 | HLA-DMB | 0.05 | −0.41 | 0.00 | −0.24 | 0.32 |
| KCND3-AS1 | 1.17 | −0.64 | −0.23 | −0.27 | 0.43 | RNU6-1266P | 0.47 | 0.19 | 0.62 | −0.23 | 0.18 | PIM3 | −0.03 | −0.06 | −0.22 | 0.03 | −0.06 |
| CRACR2A | −0.81 | 0.15 | 0.90 | 0.09 | 0.72 | OTUD6B-AS1 | 0.15 | 0.17 | 0.13 | 0.04 | −0.04 | AL049792.1 | −0.58 | 0.54 | 0.34 | 0.45 | −0.87 |
| EBF4 | −0.71 | 0.06 | 0.13 | 0.21 | 0.34 | AC008700.1 | −0.40 | −0.04 | −0.44 | 0.68 | −0.12 | AL133406.3 | −0.10 | −0.42 | 0.43 | −0.68 | 0.25 |
| AC004943.2 | −0.54 | 0.13 | 0.27 | −0.18 | −0.09 | HAUS4P1 | 0.96 | −1.35 | −1.11 | −0.88 | 0.51 | CORO7 | 0.04 | −0.27 | −0.21 | −0.18 | −0.05 |
| AC026894.1 | 0.70 | −0.93 | −1.56 | −0.06 | −0.49 | AL590648.3 | 0.89 | 0.23 | −2.11 | 0.42 | −3.24 | GGT6 | 0.05 | 0.64 | 0.29 | 0.48 | −0.24 |
| AC103858.1 | −1.04 | 0.38 | 0.99 | 0.20 | 0.06 | AC005000.1 | 0.51 | −0.18 | 0.26 | −0.47 | 0.05 | AP005482.3 | −0.10 | −0.39 | 1.43 | −0.40 | 0.13 |
| G26815 | −0.99 | 0.48 | 0.35 | 0.34 | 0.00 | DPH6-DT | −0.38 | −0.24 | 1.27 | −0.32 | 0.75 | PPFIBP2 | 0.03 | 0.04 | −0.37 | 0.07 | −0.10 |
| PLCH1 | −0.89 | 0.29 | 0.51 | 0.21 | 0.35 | PTGDR2 | −0.28 | 0.13 | 0.49 | −0.03 | −0.15 | MTCYBP31 | −0.33 | −2.17 | −0.87 | −0.47 | 0.23 |
| AP001205.1 | 1.01 | −0.23 | −1.37 | 0.09 | −0.95 | AC068473.1 | −0.77 | −0.01 | −0.22 | 1.07 | 1.36 | POLDIP3 | 0.02 | 0.06 | −0.02 | −0.07 | −0.10 |
| LSM2 | 0.54 | −0.28 | −0.12 | −0.16 | −0.04 | MRPL3P1 | 0.97 | −2.67 | −0.29 | 0.03 | 2.27 | AC111152.3 | −0.23 | 0.38 | −1.55 | 0.58 | −0.74 |
| CEACAM4 | 2.16 | −0.31 | −0.13 | −0.96 | −1.71 | OR10W1 | −0.57 | −0.35 | 0.17 | 0.82 | 0.82 | RPL23AP58 | −0.07 | −0.25 | 0.21 | 0.06 | 0.45 |
| B3GNT9 | 0.60 | −0.17 | −0.14 | −0.23 | −0.19 | NUDT16L1 | 0.14 | 0.06 | −0.25 | 0.29 | −0.05 | HMGB1P7 | −0.12 | 0.71 | 0.18 | 0.42 | −0.46 |
| MIDN | 0.46 | −0.13 | −0.93 | 0.06 | −0.67 | PIAS1 | 0.10 | 0.04 | 0.14 | −0.04 | −0.11 | AC046130.1 | 0.41 | −0.80 | −0.42 | −1.01 | 1.57 |
| SLC4A3 | 0.76 | −0.33 | −1.08 | 0.20 | 0.05 | PPP1R15A | −0.19 | −0.10 | −0.33 | −0.07 | −0.29 | AC008738.6 | −0.46 | 0.60 | −0.43 | 0.56 | −1.02 |
| C9orf41-AS1 | −0.51 | −0.18 | −0.06 | 0.08 | 0.36 | AL691403.1 | −0.81 | 0.41 | 1.93 | 0.01 | 0.24 | LINC00210 | 0.45 | −0.23 | 0.43 | 0.29 | 0.79 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| DCAF15 | −0.48 | 0.10 | −0.06 | 0.17 | 0.03 | SLC12A4 | −0.15 | −0.11 | −0.30 | 0.22 | 0.12 | AC024361.2 | 0.19 | −1.96 | −0.01 | 0.42 | 1.71 |
| AL845472.2 | −0.83 | 0.41 | 1.42 | 0.35 | 0.46 | MAP3K21 | −0.15 | 0.10 | 0.26 | 0.30 | 0.32 | MIR4472-2 | −0.85 | 1.41 | 0.29 | 0.91 | −1.17 |
| PPWD1 | −0.31 | 0.21 | 0.17 | 0.09 | −0.12 | AL136295.2 | 0.35 | −0.68 | 0.45 | −0.29 | 0.64 | AC036108.2 | −0.11 | 0.36 | 0.54 | 0.98 | 0.59 |
| FIG4 | −0.25 | 0.18 | 0.30 | 0.02 | 0.03 | LINC02109 | −0.71 | −0.31 | −1.63 | −0.31 | −1.76 | AC060766.5 | −0.09 | −0.44 | 0.45 | −0.17 | 0.31 |
| FAM217B | 0.35 | −0.29 | −0.38 | 0.13 | −0.02 | SEMA3F | 0.21 | 0.02 | −0.18 | 0.14 | −0.04 | ASCL1 | 0.26 | −0.98 | −1.70 | −0.21 | 0.43 |
| AC012313.8 | −0.79 | −0.13 | 0.90 | −0.41 | 0.44 | DCAF4L2 | −0.70 | 0.20 | 0.12 | −0.04 | −0.19 | AC013268.3 | 0.15 | −1.78 | −1.80 | −0.45 | −0.26 |
| G8260 | 2.37 | −0.08 | −2.89 | 0.36 | −2.73 | GVQW2 | −0.47 | −0.02 | 1.24 | −0.40 | 0.21 | AC073316.2 | 0.80 | 0.50 | 0.11 | −2.88 | −1.47 |
| NR4A3 | 1.18 | −1.30 | −1.67 | −0.42 | −1.20 | RPL23AP81 | 0.63 | 0.12 | 1.37 | 0.11 | −0.48 | OR5D16 | 0.41 | −0.30 | −0.94 | −1.90 | −1.94 |
| GPR171 | 1.43 | −1.29 | −0.68 | −0.43 | −0.35 | AL445931.1 | −0.32 | 0.16 | 0.00 | 0.39 | 0.43 | RN7SL376P | −0.14 | −0.89 | −3.74 | 1.05 | 0.08 |
| AC134878.2 | −1.10 | 0.51 | 0.64 | 0.86 | 0.96 | SLC6A1-AS1 | −0.58 | 0.38 | −0.76 | −0.11 | 0.48 | GPR89P | −0.18 | −0.44 | −2.28 | 0.77 | 1.15 |
| GTF3C3 | 0.22 | −0.15 | −0.15 | −0.07 | −0.05 | RN7SL458P | −1.02 | 0.83 | 1.39 | 0.91 | 0.86 | AL122126.1 | 0.30 | −0.64 | −2.23 | 1.00 | −0.61 |
| PPP1R14BP3 | −0.82 | 0.18 | 0.39 | 0.24 | 0.22 | AC004765.1 | −0.14 | 0.16 | 0.02 | 0.11 | 0.15 | AL392083.1 | 0.17 | −0.61 | 0.01 | 0.08 | 0.48 |
| MAVS | −0.23 | 0.03 | 0.02 | 0.13 | 0.16 | SNORD114-2 | 0.93 | −0.20 | 0.89 | −1.27 | 0.17 | GOLGA6L2 | 0.11 | −0.20 | −0.48 | 0.00 | 0.25 |
| NAMA | −1.26 | −0.03 | 0.29 | 0.05 | 0.42 | RPS27AP1 | 0.78 | 0.08 | −0.90 | 0.28 | 0.11 | RTL4 | −0.15 | −1.31 | −0.33 | 0.89 | 1.48 |
| LINC01301 | −1.17 | 0.03 | 0.40 | 0.38 | 0.29 | AC034231.1 | −0.28 | −0.13 | 0.22 | −0.28 | 0.25 | POLR2H | 0.03 | −0.11 | −0.13 | 0.03 | 0.25 |
| RDH10 | 0.36 | −0.05 | −0.52 | 0.16 | −0.31 | NOC2L | 0.15 | −0.25 | −0.52 | 0.05 | 0.14 | AC004980.2 | −0.06 | 0.14 | −0.17 | 0.52 | 0.79 |
| CENPV | −0.65 | 0.63 | 1.08 | 0.25 | 0.34 | AC004076.2 | −0.22 | 0.01 | 0.35 | 0.11 | 0.44 | DDX11L10 | 0.10 | 0.18 | −0.86 | 0.39 | −0.26 |
| G11629 | −1.22 | 0.65 | 0.76 | 0.14 | 0.59 | AL136084.2 | −0.50 | 0.09 | −1.30 | 0.34 | −0.31 | OR5B12 | −0.17 | 0.68 | −2.35 | 1.03 | −1.03 |
| KDM3B | −0.19 | 0.18 | 0.07 | 0.15 | −0.02 | HTR2A-AS1 | 0.67 | 0.06 | −0.80 | −0.39 | 0.00 | AL683842.1 | −0.11 | 0.34 | −0.86 | 0.99 | 0.28 |
| AC099684.2 | −1.01 | 0.43 | 0.19 | 0.19 | 0.33 | NKPD1 | −0.26 | 0.52 | 0.35 | 0.54 | 0.15 | SNORD42 | 0.12 | −0.12 | 0.30 | 0.86 | 0.28 |
| SNORD105B | −1.18 | 0.23 | 1.10 | 0.40 | −0.28 | AL592148.3 | 0.26 | 0.10 | −0.29 | 0.08 | −0.44 | CMC1 | 0.03 | −0.04 | 0.04 | −0.10 | −0.04 |
| AF186192.2 | −1.32 | −0.35 | 1.12 | 0.78 | 0.96 | SNAI3-AS1 | −0.32 | −0.55 | 0.25 | −0.41 | 0.80 | PCYOX1 | 0.04 | 0.21 | 0.14 | 0.07 | −0.18 |
| MRVI1 | −0.76 | 0.24 | 0.59 | 0.17 | −0.14 | RPS27AP6 | 0.77 | −0.19 | 0.49 | −0.44 | 0.53 | SDHCP3 | −0.09 | −0.33 | 0.06 | 0.45 | 0.52 |
| AL353804.2 | −0.75 | −0.06 | 0.62 | 0.13 | 0.76 | SERPINI2 | −0.54 | 0.93 | −1.34 | 1.19 | −1.14 | AC024341.1 | 0.27 | −1.49 | −1.61 | 0.15 | −0.95 |
| RAP2A | 0.52 | −0.24 | −0.26 | −0.26 | −0.33 | RPL12P44 | −0.42 | 0.74 | 0.59 | 0.19 | −0.10 | AC079799.1 | −0.43 | 0.12 | −0.84 | 1.79 | 0.00 |
| RN7SL179P | −1.03 | −0.51 | 0.26 | 0.12 | 0.83 | GTF2H5 | 0.20 | −0.09 | −0.14 | −0.25 | −0.18 | AL049870.4 | −0.80 | −0.16 | 0.80 | 1.94 | 0.70 |
| FAM83E | −0.77 | 0.42 | 0.06 | −0.18 | −0.16 | PPP6R1 | 0.15 | −0.21 | −0.62 | 0.10 | −0.10 | AC092953.1 | −0.05 | 0.17 | 0.31 | 0.15 | 0.43 |
| AL135818.1 | 0.71 | −0.60 | −0.55 | −0.08 | −0.01 | AC005736.1 | −0.38 | 0.16 | 0.22 | 0.20 | −0.09 | PON2 | 0.03 | 0.28 | 0.38 | 0.15 | −0.02 |
| PALMD | −0.39 | 0.49 | 0.41 | 0.18 | −0.16 | MIRLET7A2 | −0.80 | −0.57 | 2.40 | 0.00 | 0.71 | AL365496.1 | −0.84 | 0.47 | −0.46 | 2.04 | −1.37 |
| NAP1L3 | −0.99 | 0.43 | 0.62 | −0.06 | −0.25 | RNU6-353P | 0.85 | −0.22 | −0.01 | −1.13 | 1.04 | AC013558.1 | −0.42 | −0.43 | 0.80 | 0.15 | −0.47 |
| OTUD7B | −0.22 | 0.23 | 0.33 | 0.08 | 0.15 | MTHFSD | −0.09 | −0.08 | 0.03 | −0.02 | 0.15 | LINC02358 | −0.20 | −0.56 | −1.29 | 1.04 | 1.16 |
| AC126323.1 | −1.50 | −0.33 | 0.94 | 0.00 | 1.25 | AL954705.1 | 0.45 | −0.33 | −0.08 | −0.34 | 0.11 | RMRPP3 | 0.06 | −0.78 | 0.31 | −0.38 | 0.82 |
| AC011453.1 | −1.38 | 0.00 | −0.37 | 0.22 | 0.60 | IBA57-DT | −0.35 | −0.22 | −0.27 | 0.16 | −0.05 | G35954 | −0.24 | 0.29 | −2.46 | 1.26 | −2.10 |
| CTCF | 0.24 | −0.10 | −0.20 | −0.11 | −0.10 | RNU7-115P | 0.66 | −0.48 | −0.44 | −0.44 | −0.68 | AP000797.1 | 0.22 | −0.86 | −1.26 | 0.43 | −0.40 |
| KIAA1211L | −0.56 | 0.79 | 0.94 | 0.52 | 0.16 | AC011509.2 | −1.04 | −0.91 | −0.22 | 0.22 | 1.50 | AP000866.5 | 0.10 | −0.09 | 0.41 | −0.48 | −0.06 |
| AL645929.1 | −1.45 | 0.32 | 0.59 | −0.42 | 0.08 | AC011465.1 | 0.51 | −0.11 | 0.76 | −0.33 | 0.74 | ALOX15B | 0.09 | 0.09 | −0.62 | 0.64 | 0.51 |
| RPS3AP37 | −1.21 | 1.06 | 2.24 | 0.16 | 0.10 | KNG1 | 0.86 | −1.83 | −1.46 | −0.46 | 0.93 | QKI | −0.02 | −0.02 | −0.04 | −0.05 | −0.03 |
| POLE | −0.43 | 0.01 | −0.10 | 0.17 | 0.20 | AL031687.1 | −1.00 | −1.44 | 0.19 | −0.09 | 1.13 | CCNT2P1 | 0.26 | −1.49 | 0.43 | −0.69 | −0.09 |
| AC010148.1 | −0.96 | 0.12 | 0.23 | 0.51 | 0.53 | CACYBPP1 | 0.35 | 0.19 | −0.37 | −0.02 | −0.29 | RNU2-28P | −0.06 | −0.07 | 0.10 | −0.14 | 0.07 |
| AC037459.2 | −0.48 | −0.03 | 0.32 | −0.12 | 0.08 | AC121338.1 | 0.29 | −0.19 | −0.42 | −0.07 | −0.24 | AC025437.6 | −0.32 | 0.13 | −0.67 | 0.75 | −2.33 |
| SLC35F2 | 0.49 | −0.11 | −0.09 | −0.17 | −0.01 | AC135050.1 | 0.31 | −0.97 | −0.70 | −0.38 | 0.02 | AC090568.1 | −0.54 | 0.22 | 0.58 | 1.25 | 1.17 |
| G26933 | −1.27 | 0.31 | 0.20 | 1.09 | −0.42 | ABCB6 | 0.35 | 0.06 | 0.44 | 0.16 | 0.08 | LINC00911 | −0.50 | −0.37 | 0.39 | −0.94 | 0.76 |
| AC120498.10 | −2.11 | 1.43 | 1.02 | 0.75 | 1.16 | RNU6-531P | 0.44 | −0.50 | −0.15 | −0.56 | 0.09 | AL731537.1 | −0.18 | −1.32 | 0.99 | −0.47 | 1.20 |
| ODF3L1 | −1.41 | 0.81 | 2.10 | 1.31 | 0.54 | AL356652.1 | −0.75 | 0.63 | 1.28 | −0.40 | −0.15 | SLC9A9-AS1 | 0.09 | 0.39 | 0.95 | 0.46 | −0.23 |
| HCAR3 | 1.14 | −2.30 | −1.04 | 0.00 | 0.47 | OR9R1P | 1.36 | −0.90 | −2.48 | −0.72 | −1.86 | AC092138.1 | 0.76 | −0.61 | −1.04 | −0.99 | −0.30 |
| ADO | 0.44 | −0.11 | −0.39 | −0.01 | −0.29 | PBX2 | −0.09 | 0.05 | 0.03 | 0.07 | 0.15 | G33270 | 0.41 | −0.03 | 0.25 | 0.57 | 0.50 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AL158163.1 | −0.54 | 0.53 | 0.88 | 0.11 | 0.18 | HSPA1A | −0.16 | 0.38 | −0.04 | 0.32 | −0.12 | AL356094.1 | −0.84 | 0.15 | 0.24 | 1.38 | 0.83 |
| FOXQ1 | −0.77 | 0.58 | 0.41 | 0.28 | 0.19 | ST13P13 | 0.78 | −0.43 | −2.10 | 0.07 | −2.48 | GNRH2 | 0.09 | 0.25 | 0.59 | −0.15 | 0.58 |
| PPP1R35 | −0.63 | 0.29 | 0.29 | 0.31 | 0.24 | LINC02126 | −1.04 | 0.08 | 2.58 | −0.43 | 1.03 | AL513188.1 | −0.10 | 0.40 | −0.31 | −0.23 | −0.30 |
| MTX1 | 0.39 | −0.31 | −0.37 | −0.10 | −0.02 | GRK7 | −0.49 | 0.48 | 0.02 | 0.05 | −0.35 | AC106706.1 | −0.32 | −1.58 | 0.48 | −0.57 | 0.95 |
| LCP1 | 0.93 | −0.97 | −0.22 | −0.39 | −0.28 | AC010327.2 | −0.68 | −0.67 | 0.02 | −0.18 | −0.53 | COX6CP10 | 0.13 | 0.99 | 0.00 | 0.93 | −0.69 |
| OXCT1 | 0.36 | 0.11 | −0.33 | 0.20 | −0.32 | CD8A | 0.37 | 0.24 | −0.09 | 0.06 | −0.02 | RPL12P17 | −0.17 | −0.09 | −1.06 | 0.07 | −0.86 |
| MREG | 0.57 | −0.46 | −0.90 | −0.06 | −0.37 | AL356473.1 | 0.29 | −0.27 | 0.06 | −0.07 | 0.15 | FBP2P1 | 0.45 | −0.90 | −1.86 | 2.29 | 0.41 |
| HIRIP3 | −0.45 | 0.24 | 0.62 | −0.14 | 0.11 | AC127024.3 | −0.26 | −0.08 | 0.05 | 0.28 | 0.56 | AC008055.1 | −0.84 | 0.29 | 0.17 | 0.72 | 0.50 |
| C19orf48 | 0.75 | −0.64 | −0.87 | 0.04 | −0.11 | PIGB | −0.11 | 0.28 | 0.25 | 0.25 | 0.01 | AL512430.3 | 0.80 | −0.38 | 0.10 | −0.17 | −0.02 |
| AC107375.1 | −0.50 | 0.19 | 0.55 | 0.28 | 0.39 | PSMD10P1 | 0.22 | −0.08 | −0.21 | −0.09 | 0.01 | LINC01783 | −0.12 | −0.14 | −0.62 | 0.43 | −0.37 |
| KLHL2 | 0.35 | −0.16 | −0.19 | −0.13 | −0.08 | AL021918.1 | −1.26 | −0.34 | 1.46 | 0.73 | 1.91 | AC004817.4 | −0.09 | 0.32 | 0.09 | 0.15 | 0.34 |
| AC093585.1 | −0.94 | 0.18 | 1.14 | 0.26 | 0.80 | GFAP | −0.44 | 0.28 | −0.95 | 0.62 | −0.77 | AC096711.1 | 0.29 | 0.64 | −1.86 | 0.24 | −1.22 |
| ARL4AP5 | 1.23 | −0.84 | −0.83 | −0.36 | −0.43 | KIF3B | 0.12 | −0.12 | −0.26 | −0.07 | −0.15 | PIGO | 0.03 | −0.08 | −0.07 | 0.14 | 0.09 |
| SLC25A44 | 0.32 | −0.12 | −0.29 | −0.03 | −0.14 | GOLGA8K | −0.30 | −0.57 | 0.08 | −0.34 | 0.37 | AL160290.3 | −0.37 | 1.57 | −0.38 | 0.00 | −0.81 |
| OR7E2P | 1.06 | −0.32 | −0.04 | −0.45 | 0.24 | AC109462.2 | −0.94 | 0.73 | 0.39 | 0.60 | 1.03 | HNRNPA1P69 | 0.36 | −0.89 | −1.83 | 0.00 | −1.21 |
| AIM2 | 0.96 | −1.13 | −0.23 | −1.13 | −0.05 | CCDC54 | −0.73 | 1.46 | −1.66 | 0.98 | −0.22 | AC107419.1 | 0.16 | −1.85 | −1.95 | 1.14 | 0.64 |
| SEC63 | 0.44 | −0.28 | −0.35 | −0.18 | −0.16 | PLA2G10 | −0.49 | −0.72 | −0.04 | 0.54 | 1.49 | AC104390.1 | 0.32 | −0.86 | −0.45 | −0.59 | −0.57 |
| ADGRL1 | −0.37 | 0.27 | 0.11 | 0.26 | 0.13 | RPL7P16 | −0.53 | 0.63 | 0.72 | 0.25 | −0.11 | RPL7P43 | −0.15 | 0.36 | 0.85 | 0.84 | 0.66 |
| AC022832.1 | −2.24 | 0.29 | −0.85 | 2.45 | −0.58 | AC007998.3 | 0.41 | −0.05 | −1.13 | 0.00 | −1.00 | CDKL3 | 0.05 | −0.28 | 0.31 | −0.10 | 0.53 |
| EEF1E1 | 0.67 | −0.38 | −0.78 | 0.04 | −0.39 | LINC01894 | −0.76 | −0.30 | 0.70 | −0.15 | 1.27 | G5931 | 0.20 | −0.47 | −0.86 | −0.05 | 0.02 |
| KIF28P | −0.80 | 0.82 | 0.72 | 0.03 | −0.20 | RBBP4P1 | −0.18 | 0.22 | 0.52 | 0.12 | 0.31 | ANKUB1 | 0.07 | 0.01 | −0.94 | 0.48 | −0.60 |
| AL132768.1 | −1.75 | 0.70 | 0.03 | 1.15 | −0.25 | AC003002.2 | 0.67 | −0.15 | −1.47 | −0.15 | 0.15 | PPIAP11 | 0.05 | −0.02 | 0.08 | −0.03 | 0.10 |
| RPL10AP1 | 1.10 | −0.44 | −0.42 | −0.06 | 0.20 | AC068726.1 | −1.03 | 1.27 | 2.31 | 1.61 | 2.19 | OR4B2P | 0.80 | −0.61 | −0.83 | −0.24 | 1.08 |
| GAS1 | −0.58 | 0.47 | 0.89 | −0.03 | 0.06 | MTMR4 | −0.09 | 0.03 | 0.09 | 0.10 | 0.20 | MIR651 | 0.76 | −1.48 | 0.34 | 0.10 | −0.10 |
| G37230 | 1.30 | −0.45 | −0.62 | 0.18 | −0.84 | AC105020.2 | −0.50 | 0.42 | −0.45 | 0.26 | −0.39 | LINC01085 | −0.12 | −0.21 | −0.23 | −0.52 | −0.57 |
| MYOZ2 | −1.12 | 0.27 | 0.73 | 0.37 | 0.34 | AC068724.3 | −0.68 | −1.26 | 0.41 | 0.50 | −0.10 | MIR126 | 0.10 | −0.04 | −0.06 | 0.33 | 0.29 |
| CDK15 | −0.83 | 0.54 | 0.65 | 0.15 | 0.14 | AC007098.1 | −0.19 | 0.12 | 0.14 | 0.03 | 0.32 | C9orf135 | −0.25 | −0.42 | −1.75 | 0.30 | −1.55 |
| MLLT3 | −0.46 | 0.56 | 0.69 | 0.18 | 0.09 | EPM2AIP1 | 0.13 | −0.11 | 0.16 | −0.07 | 0.12 | AC007608.2 | −0.08 | 0.23 | −0.47 | 0.50 | 0.22 |
| PHAX | 0.43 | −0.30 | −0.24 | −0.32 | −0.18 | EAPP | 0.15 | 0.17 | −0.10 | 0.06 | −0.43 | ADAM20P3 | 0.35 | −2.06 | −0.81 | −0.35 | 0.88 |
| ATP2B1-AS1 | −0.71 | −0.12 | 0.69 | −0.08 | 0.37 | HSD3BP5 | −0.40 | 0.13 | 1.02 | −0.22 | 0.60 | AL353093.1 | −0.51 | 1.15 | −1.47 | 2.54 | −2.04 |
| AC018737.2 | −1.60 | 0.45 | 0.00 | −0.34 | −0.34 | AC098847.1 | −0.43 | 0.08 | 1.21 | 0.24 | 0.25 | AC090643.2 | −0.16 | 0.03 | 0.65 | −0.17 | −0.21 |
| EPAS1 | 0.51 | −0.27 | −0.24 | −0.23 | −0.35 | SDHDP2 | 0.39 | 0.07 | −0.34 | 0.35 | −0.25 | AC104316.2 | 0.18 | −0.80 | 0.51 | −1.01 | 0.33 |
| HOXA-AS3 | −0.78 | 0.21 | 0.98 | 0.11 | 0.00 | G40986 | −0.36 | 0.45 | 0.64 | 0.09 | 0.52 | AC005186.1 | −0.22 | −0.39 | 0.32 | 0.45 | 1.42 |
| RPL26P30 | −0.82 | 0.33 | 1.34 | 0.20 | 1.02 | AC012184.4 | 0.46 | −0.64 | −0.49 | −0.21 | 0.26 | OR52B3P | −0.25 | −0.02 | 0.33 | −0.54 | 0.59 |
| PRKAR1B | 0.43 | −0.34 | −0.70 | 0.07 | −0.06 | LGMNP1 | −0.63 | 0.77 | −1.08 | −0.05 | −1.48 | AP001972.4 | −0.27 | −0.16 | 0.72 | −1.19 | 0.39 |
| RN7SL533P | −1.24 | −0.20 | −0.88 | 0.14 | 0.62 | AC005041.1 | −0.56 | −0.12 | −0.68 | 0.30 | −0.77 | DCBLD2 | 0.03 | 0.01 | 0.13 | −0.07 | −0.07 |
| INPP5A | −0.29 | 0.23 | 0.34 | 0.05 | −0.02 | AC034223.2 | 0.54 | −0.16 | −0.47 | 0.19 | −0.71 | HSPE1P4 | 0.48 | −0.71 | −1.39 | −0.10 | 0.72 |
| CAMK1G | 1.13 | −0.75 | −1.78 | −0.26 | −0.70 | NR112 | −0.61 | 0.03 | 0.15 | −0.16 | −0.74 | G35130 | 0.07 | 0.43 | −0.97 | 0.46 | −0.74 |
| POLRIE | 0.29 | −0.28 | −0.51 | −0.19 | −0.19 | PWRN3 | −1.12 | −1.28 | −1.46 | 0.76 | 0.54 | AL161670.2 | 0.21 | −0.57 | 0.50 | 0.28 | 0.55 |
| PDCD6 | 0.30 | −0.11 | −0.18 | 0.03 | −0.01 | PHLDB2 | 0.16 | −0.29 | −0.61 | 0.00 | −0.21 | LINC01350 | 0.32 | −1.65 | 1.40 | 0.65 | 2.57 |
| AFG3L2 | 0.36 | −0.11 | −0.22 | −0.11 | −0.15 | AC104462.2 | 0.68 | −0.34 | 1.00 | −0.84 | 0.56 | PSMD7P1 | 0.48 | −0.54 | −1.67 | −0.03 | −0.96 |
| ITSN2 | 0.44 | −0.21 | −0.51 | −0.14 | −0.34 | DECR1 | −0.11 | 0.13 | 0.18 | 0.02 | 0.01 | AC000124.1 | 0.22 | −1.13 | −0.02 | 0.95 | 0.01 |
| SUCLG2-AS1 | −0.89 | −0.05 | 0.79 | −0.03 | 0.30 | CYP4A22 | −0.27 | −0.11 | −0.32 | 0.08 | 0.04 | AC009597.1 | 0.41 | −1.60 | 1.63 | 1.46 | 1.03 |
| HLA-F-AS1 | −0.66 | 0.35 | 0.37 | 0.52 | 0.51 | RNU6ATAC | −0.37 | 0.36 | −0.51 | 0.86 | −0.80 | AC104784.1 | 0.84 | −1.02 | −1.18 | −0.16 | −0.72 |
| AC093827.4 | −0.50 | 0.32 | 0.47 | 0.29 | 0.44 | HPCA | 0.51 | −0.35 | −1.01 | 0.55 | −0.28 | RPL7P45 | 0.19 | −2.00 | −0.86 | 0.70 | −1.49 |
| RPA3 | 0.60 | −0.41 | −0.30 | −0.21 | −0.03 | LINC01987 | 0.93 | −1.06 | −2.53 | 0.43 | −1.63 | AC105313.1 | 0.65 | −0.97 | −0.78 | −0.38 | −1.39 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| LINC01153 | −1.84 | 0.62 | 1.56 | 1.09 | 1.39 | AL596188.1 | −0.76 | 0.27 | 0.75 | 1.06 | 0.57 | FAM221B | −0.11 | −1.11 | −0.25 | 0.15 | 0.24 |
| EPN3 | 0.52 | −0.09 | −0.91 | 0.27 | −0.45 | AC018410.1 | −0.28 | 0.26 | 0.74 | 0.33 | 0.35 | AC010205.1 | −0.48 | 0.51 | 0.42 | 0.61 | −1.96 |
| SOBP | −1.02 | 0.57 | 1.05 | −0.10 | 0.04 | AL121658.1 | 0.43 | −0.46 | −0.42 | −0.04 | −0.12 | FAM198B | 0.06 | 0.10 | 0.61 | −0.38 | −0.02 |
| G39463 | −1.58 | 1.15 | 2.87 | 0.07 | 0.14 | DEFB130C | −0.56 | −0.22 | 0.64 | −0.14 | 0.24 | AL049836.1 | 0.10 | −0.26 | 0.68 | 0.48 | 0.24 |
| MTX3 | 0.46 | −0.07 | −0.14 | 0.03 | −0.06 | LINC00476 | −0.16 | 0.07 | 0.19 | 0.00 | 0.25 | EIF4EBP3 | −0.08 | 0.41 | 1.10 | 0.26 | 0.52 |
| AC005696.4 | −0.95 | 0.28 | 0.43 | 0.71 | 0.70 | AC005740.3 | −0.39 | 0.08 | 1.09 | −0.42 | −0.02 | CYLC1 | 0.28 | −0.21 | −0.89 | −0.88 | −3.42 |
| LINGO1 | −0.80 | 0.00 | 1.06 | 0.09 | 0.70 | AKNAD1 | −0.26 | 0.21 | −0.17 | 0.29 | −0.04 | EPC1 | 0.02 | 0.08 | 0.15 | 0.00 | 0.00 |
| GPX2 | 0.74 | −0.31 | −0.56 | 0.07 | 0.04 | PFDN5 | 0.13 | 0.04 | 0.18 | −0.10 | −0.13 | AL133396.1 | −0.29 | −2.36 | −0.03 | −0.41 | 0.71 |
| ADGRA2 | −0.69 | 0.45 | 1.23 | −0.14 | 0.27 | CAMKID | −0.17 | 0.31 | 0.08 | 0.31 | −0.19 | GGCX | −0.02 | −0.03 | −0.15 | 0.11 | 0.02 |
| AC069148.1 | −1.92 | 2.00 | 1.76 | 0.77 | −0.17 | AL360182.1 | −0.34 | 0.39 | 0.71 | 0.08 | −0.18 | RPL5P21 | −0.44 | −0.93 | −0.95 | −0.27 | 1.18 |
| EEF1B2P8 | −1.52 | −0.23 | −0.25 | −0.45 | 0.23 | LINC02382 | −1.29 | 0.20 | −1.38 | −0.08 | −3.08 | AC104971.3 | 0.47 | 0.08 | −0.91 | 0.85 | −0.02 |
| CEBPD | 0.43 | −0.26 | −0.69 | −0.08 | −0.44 | C11orf21 | −0.36 | −0.73 | 0.59 | −0.37 | 0.96 | AC116667.2 | 0.27 | −0.76 | −0.14 | 0.72 | 0.38 |
| AC008537.3 | −1.21 | 0.93 | 1.10 | −0.45 | −0.27 | CSN1S1 | −0.73 | −1.08 | −0.23 | 0.25 | 1.51 | AC105460.1 | 0.48 | −2.14 | 1.08 | −1.89 | 2.10 |
| CRISP2 | −1.59 | 0.64 | 1.03 | −0.25 | 0.12 | RNU1-22P | −0.55 | 0.55 | 1.08 | −0.13 | 0.28 | MIR4431 | −0.23 | 0.38 | −0.12 | 0.85 | −0.72 |
| STAT6 | −0.33 | 0.10 | 0.00 | 0.15 | 0.09 | MGC32805 | 0.38 | −0.14 | −1.30 | −0.23 | −1.06 | MIR5091 | −0.13 | −0.26 | 1.35 | 0.06 | 1.07 |
| RPS4XP5 | −1.03 | 0.31 | 0.26 | 0.43 | 0.44 | FLJ30679 | −0.69 | 0.45 | −0.82 | −0.05 | −1.76 | AC116036.2 | 0.38 | 0.35 | 0.73 | 1.61 | −0.26 |
| AKAP8L | −0.45 | 0.17 | 0.07 | 0.29 | 0.05 | ADCY7 | 0.16 | −0.26 | −0.30 | −0.15 | −0.14 | CLCP2 | −0.18 | 0.58 | 0.73 | −0.15 | 0.01 |
| NUP188 | 0.29 | −0.21 | −0.33 | 0.00 | −0.02 | STX16-NPEPL1 | −0.28 | 0.26 | 0.12 | 0.24 | −0.16 | AC016994.1 | −0.47 | 0.95 | 0.12 | 2.01 | −0.04 |
| LINC00630 | −0.29 | −0.01 | 0.23 | 0.08 | 0.15 | LINC02405 | 0.67 | −0.48 | −0.60 | −0.11 | −0.65 | KLK2 | −0.14 | −0.12 | −1.52 | 0.06 | −1.01 |
| CLDN24 | 1.25 | −0.80 | −1.23 | −0.30 | −0.10 | STX2 | −0.16 | −0.10 | 0.20 | −0.35 | −0.05 | GRAMD4P3 | −0.81 | 1.29 | 2.21 | 0.31 | 0.92 |
| AC002451.1 | −1.86 | 0.93 | 0.44 | 1.50 | 0.25 | RNU6-25P | −0.45 | 0.68 | 0.06 | 0.53 | 0.35 | EVI5L | −0.03 | 0.13 | −0.39 | 0.34 | −0.05 |
| C11orf49 | −0.49 | 0.43 | 0.53 | 0.22 | 0.09 | AC092757.1 | 0.45 | −0.75 | 0.01 | −0.42 | 0.55 | SNX9 | −0.03 | 0.14 | −0.01 | −0.03 | −0.29 |
| IDH3B | 0.28 | −0.17 | −0.23 | −0.11 | −0.04 | EP400 | −0.08 | −0.02 | −0.06 | 0.05 | 0.08 | AC104117.3 | 0.15 | 0.13 | 1.84 | −0.50 | 0.35 |
| CD109 | 0.57 | 0.00 | −0.23 | −0.08 | −0.37 | AL161752.1 | −1.07 | 1.80 | 0.87 | 0.40 | −2.12 | AC027045.2 | 0.18 | −1.04 | −1.21 | −0.19 | −0.16 |
| ESD | 0.43 | −0.15 | −0.35 | −0.04 | −0.38 | CPT1A | 0.14 | −0.38 | −0.51 | −0.09 | 0.03 | AC021506.1 | 0.39 | −0.59 | 0.27 | −1.21 | −0.53 |
| SNRNP200 | 0.24 | −0.14 | −0.26 | −0.12 | −0.13 | AC093817.1 | −0.65 | 1.46 | −0.12 | 1.06 | 0.06 | RNU6-554P | 0.21 | −0.45 | −0.60 | −0.81 | −0.11 |
| AC093227.1 | −0.70 | 0.11 | 1.17 | −0.07 | 1.00 | C6orf201 | −0.32 | 0.38 | −0.08 | 0.95 | 0.33 | LINC02241 | −0.16 | −0.94 | −0.83 | 0.70 | −0.12 |
| RPL26P19 | 0.71 | −0.25 | −0.23 | −0.44 | −0.25 | MIAT | 0.22 | −0.30 | −0.03 | −0.16 | 0.37 | AP000720.1 | 0.14 | 0.19 | −1.82 | 0.15 | −1.64 |
| KBTBD2 | 0.35 | −0.14 | −0.16 | −0.12 | −0.21 | AC092916.2 | 1.13 | −1.04 | 0.40 | −0.90 | 0.25 | CDK7P1 | −0.20 | −1.40 | −0.46 | −0.36 | −0.11 |
| AL358394.1 | −1.44 | −0.46 | 0.54 | 0.11 | 0.84 | LRFN4 | 0.23 | −0.20 | −1.01 | 0.13 | −0.28 | FCRLA | −0.08 | 0.31 | 0.17 | 0.17 | 0.11 |
| NAPA | 0.33 | −0.08 | −0.26 | −0.11 | −0.33 | SGTB | −0.17 | −0.17 | 0.19 | −0.30 | 0.11 | AC005086.4 | 0.08 | −0.83 | 0.14 | −0.15 | −0.06 |
| HAUS5 | −0.45 | 0.07 | −0.12 | 0.23 | 0.07 | RNU6-879P | 0.62 | −0.03 | −0.34 | −0.34 | −0.43 | PAUPAR | 0.16 | −0.65 | −1.59 | 0.39 | −0.97 |
| ABRAXAS1 | −0.39 | 0.24 | 0.62 | 0.08 | 0.22 | LNCOC1 | −0.35 | −0.22 | −0.27 | 0.11 | 0.07 | AC009262.1 | −0.17 | 1.26 | 1.20 | 0.98 | −0.50 |
| SLC9A4 | −1.27 | 0.38 | 0.32 | 0.88 | 0.17 | PRSS35 | −0.52 | 0.33 | 0.71 | 0.00 | −0.96 | AC138932.2 | −0.19 | −0.41 | −0.30 | 0.95 | 0.14 |
| OR2T34 | −3.05 | −0.32 | 2.38 | −1.42 | 0.98 | SLC2A14 | −0.61 | −0.91 | −0.40 | 0.37 | 0.37 | PA2G4P3 | −0.56 | 0.47 | −1.49 | 0.96 | 0.55 |
| CCDC121 | −0.58 | 0.41 | 0.64 | 0.01 | 0.09 | IFNAR1 | 0.13 | −0.09 | −0.02 | −0.03 | −0.03 | RN7SL515P | 0.11 | −0.31 | 1.67 | 0.08 | 0.71 |
| AC110760.2 | −0.79 | 0.50 | 0.67 | −0.05 | −0.35 | RP11-24B13.2 | −0.32 | 0.23 | −0.26 | −0.01 | −0.60 | AC114969.1 | −0.20 | 0.68 | −0.14 | 0.36 | −0.55 |
| ISLR | −0.83 | 0.76 | 1.53 | −0.09 | −0.17 | AL136317.2 | −1.01 | −0.01 | 1.30 | −0.27 | 1.76 | AL590065.1 | 0.15 | 0.20 | −0.56 | 0.62 | 0.60 |
| AL133444.1 | −0.92 | −0.37 | 1.63 | −0.86 | 0.26 | RN7SL704P | −0.45 | 0.89 | −0.14 | −0.17 | −1.43 | RABEPK | −0.02 | −0.14 | 0.05 | −0.02 | 0.21 |
| MRPL43 | 0.34 | −0.06 | −0.31 | −0.06 | −0.33 | SLC35G1 | −0.18 | 0.04 | 0.35 | 0.03 | 0.24 | SEMA3F-AS1 | −0.05 | 0.13 | −0.15 | 0.14 | −0.30 |
| SLC12A8 | 0.69 | −0.50 | −0.95 | 0.02 | 0.16 | ALG1L11P | −0.98 | 0.85 | 3.27 | 0.35 | 1.42 | AC023510.2 | 0.16 | 0.76 | 1.03 | 0.14 | 0.15 |
| MLH1 | 0.21 | −0.29 | −0.20 | −0.20 | −0.03 | AC068205.2 | −0.31 | 0.08 | 0.52 | 0.42 | 0.38 | AL158206.1 | 0.06 | −0.05 | 0.09 | 0.28 | 0.08 |
| LUC7L3 | −0.44 | 0.07 | 0.25 | 0.00 | 0.12 | AC117454.1 | −1.03 | 0.86 | 0.34 | 1.41 | 0.35 | CEACAM5 | −0.07 | −0.72 | 0.23 | −0.54 | 0.22 |
| AP000763.3 | 1.40 | −0.23 | −0.94 | −0.79 | −0.29 | SPECC1P1 | −0.71 | −2.18 | 0.03 | 0.27 | 1.63 | AC061975.3 | −0.48 | 2.05 | 1.58 | 0.00 | −1.70 |
| OSTCP6 | 1.64 | −0.93 | −1.49 | 0.22 | 0.49 | AL121830.1 | 0.38 | 0.34 | 0.55 | 0.63 | 0.40 | AL121917.2 | 0.17 | 0.53 | −1.25 | 1.45 | −1.87 |
| GBP1 | 0.77 | −1.20 | −0.63 | −1.35 | −0.58 | AC104453.1 | −0.72 | −1.38 | −0.58 | 0.09 | 1.37 | AC013565.3 | −0.20 | 1.10 | −0.72 | 0.30 | −1.04 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| PPFIA2 | −0.82 | −0.11 | 0.15 | 0.04 | −0.05 | SNRPCP19 | 0.34 | −1.07 | −0.86 | −0.24 | 0.15 | IGKV1-9 | 0.58 | 0.21 | 0.68 | −0.13 | −1.96 |
| STPG1 | 0.40 | 0.08 | −0.21 | −0.04 | −0.32 | AC106782.5 | −0.49 | 0.07 | 1.24 | −0.67 | −0.43 | AC106772.1 | −0.17 | −0.95 | −1.33 | 0.67 | 0.78 |
| SLC38A9 | 0.27 | −0.12 | −0.09 | −0.12 | 0.01 | BDP1P | −0.70 | −0.22 | −0.71 | 0.95 | 0.47 | AC011611.2 | 0.52 | −0.97 | −0.51 | 0.36 | 1.43 |
| FAM161A | −0.47 | 0.27 | 0.73 | 0.02 | 0.19 | AC087742.1 | 0.45 | −0.41 | −0.16 | 0.14 | 0.15 | OR5A01P | 0.58 | −0.31 | 0.43 | −0.77 | 0.55 |
| GNL2P1 | −1.50 | 0.30 | 0.65 | 0.02 | 0.37 | AC024995.1 | 0.68 | 0.10 | −3.09 | 0.87 | −1.33 | RAC1P3 | 0.18 | 0.13 | −0.37 | −0.06 | −0.08 |
| AC004967.1 | −0.67 | 0.49 | 0.66 | 0.42 | 0.56 | CCNA1 | 0.55 | −0.85 | −0.51 | −0.32 | −0.71 | AL359385.1 | −0.14 | −0.63 | 0.69 | −1.52 | −0.60 |
| AC102953.2 | −0.70 | 0.70 | 0.58 | 0.59 | 0.46 | CHAF1A | −0.16 | −0.28 | −0.45 | −0.01 | −0.01 | NF1P2 | −0.55 | 0.80 | −0.51 | 1.50 | −1.65 |
| AL023803.2 | 1.84 | −1.17 | −2.20 | 0.33 | −0.13 | APOL4 | 0.30 | −0.66 | −0.11 | −0.14 | 0.79 | FBXL18 | −0.03 | −0.01 | −0.29 | 0.10 | −0.14 |
| MIER1 | 0.30 | −0.09 | −0.18 | −0.09 | −0.23 | ACA64 | 0.39 | 0.09 | 0.65 | −0.44 | −0.03 | AC112492.3 | 0.46 | −1.59 | −1.48 | −0.33 | −0.30 |
| CYP19A1 | 0.91 | −0.67 | −0.62 | 0.28 | −0.01 | RNU6-1306P | 0.60 | −0.41 | −0.62 | −0.03 | −0.84 | G37568 | 0.18 | −0.81 | 1.67 | 0.71 | −0.05 |
| ANKLE2 | 0.28 | −0.27 | −0.54 | 0.00 | −0.13 | MATN3 | −0.30 | 0.50 | −0.04 | 0.38 | 0.15 | MYL1 | −0.19 | −1.30 | −1.72 | 0.33 | −0.46 |
| AP004147.1 | −1.24 | −0.03 | 0.19 | 0.80 | 0.80 | FAM53B | 0.17 | 0.03 | −0.39 | 0.28 | −0.09 | IGHV3-48 | 0.82 | −0.45 | 0.10 | 0.36 | −0.39 |
| POTEKP | −1.59 | 0.74 | 2.17 | −0.26 | 1.15 | RN7SL844P | 0.39 | −0.45 | −0.14 | −0.07 | 0.26 | AC078788.2 | 0.10 | −0.85 | −0.33 | −0.43 | 0.24 |
| AC007834.1 | −1.27 | 0.39 | 0.71 | 0.37 | 0.06 | AL136382.1 | −0.32 | 0.14 | −0.32 | −0.01 | 0.14 | AC099522.1 | −0.27 | 0.55 | 0.18 | 0.15 | 0.80 |
| RPSAP54 | 1.75 | −1.09 | −0.11 | −0.63 | −0.04 | AC015908.2 | −0.70 | −2.35 | 1.21 | 0.06 | 2.43 | SNORD114-14 | −0.08 | 0.59 | 1.08 | −0.56 | −0.53 |
| EIF2AK1 | 0.36 | −0.08 | −0.14 | −0.11 | −0.16 | GATAD2B | −0.09 | 0.23 | 0.19 | 0.17 | 0.04 | LHX5 | −0.16 | −0.60 | −1.64 | 0.79 | 0.53 |
| ARFIP2 | 0.25 | −0.05 | −0.25 | 0.02 | −0.06 | AC016394.1 | 0.34 | −0.32 | 0.43 | −0.43 | 0.42 | BOD1L2 | 0.29 | −0.58 | −2.18 | −0.11 | −1.31 |
| PRRT1 | −0.87 | 0.22 | 0.79 | 0.30 | 0.23 | AC024293.1 | 0.14 | 0.12 | −0.13 | −0.08 | −0.28 | BCL11A | −0.05 | 0.31 | 0.38 | 0.43 | 0.16 |
| AC009495.2 | −0.87 | 0.40 | 0.86 | 0.22 | 0.39 | AC008671.1 | 0.60 | −0.32 | 0.38 | −0.81 | −0.67 | LINC02418 | −0.17 | −0.98 | −0.24 | 0.07 | −0.44 |
| ACAP1 | −0.57 | −0.07 | 0.56 | −0.21 | 0.45 | RPS6P8 | −0.63 | 0.77 | 0.33 | 1.05 | 1.16 | MINOS1P4 | −0.57 | −0.33 | 1.06 | −0.99 | 1.50 |
| AC023157.1 | 1.64 | −0.59 | −0.98 | 0.46 | −0.56 | AC016256.1 | −1.28 | −0.22 | −1.25 | 1.48 | −0.91 | AC090109.1 | −0.20 | 0.04 | −0.63 | −0.36 | −0.74 |
| AL596218.1 | −1.24 | 0.32 | 0.36 | 0.53 | 0.58 | LINC00997 | −0.24 | 0.28 | 0.14 | 0.06 | −0.08 | LINC00221 | −0.19 | −0.30 | −0.42 | 0.65 | 0.52 |
| CARMN | −0.83 | 0.08 | 0.47 | 0.20 | −0.12 | LINC02197 | −1.42 | 0.19 | 1.34 | −0.68 | 1.49 | SCGB1D5P | −0.82 | 0.32 | 1.32 | 2.89 | −1.02 |
| AC032019.1 | 1.77 | −0.59 | −0.94 | −0.13 | −0.02 | AC016182.1 | 1.00 | −2.69 | −1.83 | 0.32 | 1.63 | EML5 | −0.05 | −0.22 | −0.27 | 0.09 | 0.09 |
| POLN | −0.42 | 0.16 | 0.20 | 0.05 | 0.24 | AC093162.1 | −0.60 | 1.47 | 0.09 | 0.12 | −0.58 | AC093323.2 | 0.35 | −0.79 | −0.93 | −0.76 | −0.32 |
| COL4A4 | 0.86 | −0.25 | −0.54 | 0.16 | −0.11 | C6orf52 | −0.39 | 0.56 | 0.52 | 0.45 | 0.64 | SDCBPP3 | −0.40 | −1.08 | −0.11 | −1.61 | −0.40 |
| NHEG1 | −1.70 | 0.47 | 2.14 | −0.10 | 0.44 | NANOGP9 | 0.71 | 0.30 | −2.68 | 0.45 | −2.96 | AC008105.2 | 0.08 | −0.48 | −1.14 | −0.07 | −0.44 |
| PPHLN1 | 0.21 | −0.10 | −0.17 | −0.04 | −0.01 | AC105411.1 | 0.38 | −0.38 | −0.77 | −0.08 | −0.36 | AC093270.2 | 0.26 | −0.39 | −0.58 | −0.58 | −0.99 |
| SP100 | 0.32 | −0.33 | −0.37 | −0.26 | −0.12 | AC005829.2 | −0.65 | 0.41 | 0.36 | 0.04 | 4.92 | RPL23P8 | −0.15 | 0.95 | 0.43 | −0.64 | −0.65 |
| NUDT10 | −1.33 | 0.06 | 1.36 | −0.01 | 0.95 | AP005264.5 | −0.44 | 0.50 | 0.16 | 0.72 | 0.17 | AP001258.1 | 0.12 | −0.12 | 0.18 | 0.83 | −0.04 |
| CYC1 | 0.35 | −0.12 | −0.44 | −0.02 | −0.24 | C5orf64 | −0.53 | −0.35 | −0.37 | 0.40 | 0.37 | AC084262.2 | 0.12 | −0.76 | −1.18 | 0.51 | 0.55 |
| SSR3 | 0.45 | −0.34 | −0.15 | −0.34 | −0.07 | RN7SL103P | −1.22 | −0.66 | −0.13 | 0.56 | 0.53 | AFAP1L1 | 0.04 | −0.13 | −0.13 | −0.16 | −0.19 |
| AL033543.1 | −0.67 | 0.06 | 0.31 | −0.27 | −0.15 | MTND4P16 | −0.83 | −0.10 | −0.04 | 0.20 | 0.04 | AGGF1P1 | −0.11 | −0.75 | 0.17 | −0.27 | 0.53 |
| GABRG3 | −1.12 | 0.32 | −0.18 | 0.32 | 0.15 | AC139099.2 | 0.62 | −0.14 | 1.14 | −0.71 | −0.19 | AL354796.1 | −0.27 | 0.08 | −0.62 | −0.07 | −2.40 |
| AL589655.1 | 1.02 | −0.38 | −0.43 | −0.17 | −0.12 | PIGR | −0.52 | 0.76 | 0.65 | 0.71 | 0.23 | AL590396.4 | 0.28 | −1.81 | −2.60 | 0.62 | −1.05 |
| LIN7B | −0.61 | 0.60 | 0.72 | 0.39 | 0.07 | AC124248.1 | 0.69 | 0.01 | 0.32 | 0.37 | 0.90 | AC011385.1 | −0.06 | −0.34 | 0.30 | −0.73 | 0.08 |
| DOLPP1 | 0.43 | −0.11 | −0.52 | 0.06 | −0.27 | CNNM3-DT | −0.57 | 0.91 | 0.82 | 0.16 | −0.32 | COL4A3 | −0.05 | −0.22 | −0.02 | 0.25 | 0.58 |
| HCAR1 | −1.16 | 0.39 | −0.05 | 0.07 | −0.04 | AC090679.1 | 1.01 | −0.74 | −0.67 | 0.13 | −1.74 | AL133351.1 | −0.20 | 0.02 | −0.40 | −0.47 | −1.11 |
| ARHGAP39 | −0.54 | 0.40 | −0.04 | 0.46 | 0.26 | MIR3164 | 0.63 | −0.26 | −0.32 | −0.24 | −0.43 | AC022217.3 | 0.14 | −0.96 | −0.20 | −0.89 | 0.11 |
| SMPD4P1 | −1.18 | 0.57 | 1.41 | −0.09 | 0.58 | CTAGE15 | −0.38 | −0.26 | 0.09 | 1.36 | 2.12 | RP11-435B5.7 | 0.19 | 0.09 | −2.87 | 0.42 | −2.56 |
| GPER1 | −0.79 | 0.03 | 0.08 | 0.36 | 0.47 | G26744 | −0.43 | 0.75 | 0.07 | 0.35 | −0.25 | RNU6-922P | 0.61 | 1.22 | −0.14 | 0.66 | −1.84 |
| CEACAMP10 | −1.51 | −0.92 | 0.16 | −0.28 | 0.50 | AC131902.1 | −0.87 | 2.11 | 0.75 | 0.55 | −0.56 | LINC02292 | 0.29 | −0.45 | −1.10 | 0.78 | −1.27 |
| ATG5 | 0.31 | −0.14 | −0.14 | −0.07 | −0.07 | CHCHD2P6 | 0.54 | 0.44 | −1.18 | −0.22 | −1.43 | AL359834.1 | −0.24 | −1.56 | 1.56 | −0.87 | 1.48 |
| AC126768.2 | −1.01 | 0.98 | 0.67 | 1.13 | 0.19 | RPL23AP95 | 0.80 | 0.43 | −1.27 | 1.01 | −0.30 | AL121974.1 | −0.82 | 1.32 | −0.48 | 0.94 | −2.87 |
| AL353708.3 | 1.11 | −0.80 | −0.69 | −0.31 | −0.49 | AP003472.1 | 0.63 | 0.42 | −0.72 | 0.87 | −0.61 | AC011700.1 | 0.13 | −0.88 | 0.52 | −0.58 | 0.27 |
| AC009093.3 | −1.10 | −0.78 | 1.36 | 0.14 | 1.55 | SRD5A3P1 | 0.95 | −1.63 | −1.14 | 0.01 | −0.47 | AC146507.1 | −0.08 | 0.15 | 0.05 | 0.28 | 0.10 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| SLC39A3 | 0.45 | −0.47 | −0.33 | 0.11 | 0.28 | MIR5585 | −0.68 | 1.13 | 0.17 | 1.71 | 0.78 | AP003128.1 | −0.15 | −0.34 | −0.84 | −1.56 | −1.79 |
| PDZK1 | −0.85 | 0.53 | 0.82 | 0.76 | 0.92 | JADRR | −0.83 | −0.10 | 1.37 | 0.16 | 0.68 | RPL34P20 | 0.10 | −0.59 | −0.16 | −0.05 | −0.11 |
| RNF19A | 0.44 | 0.02 | −0.26 | −0.05 | −0.36 | CNBD1 | −0.90 | 0.48 | 0.66 | −0.34 | −0.72 | AC018761.1 | −0.16 | 0.51 | 1.43 | −0.65 | 0.39 |
| RHBDF1 | −0.49 | 0.28 | −0.11 | 0.32 | 0.00 | SLC35G5 | −0.41 | −0.12 | −0.50 | −0.24 | −0.64 | RNU6-432P | 0.09 | 0.16 | 1.27 | −0.55 | −0.02 |
| OTUD5 | −0.24 | 0.18 | −0.02 | 0.11 | −0.09 | C15orf48 | 0.52 | −0.77 | 0.09 | −0.09 | 0.85 | RPL36AP39 | 0.35 | 0.47 | −0.81 | 0.57 | −1.58 |
| FAM180A | −0.72 | 0.47 | 0.86 | −0.28 | −0.02 | AC007638.1 | −0.65 | 0.78 | 2.08 | 0.41 | 0.51 | AC093156.1 | −0.66 | −0.13 | 0.05 | 0.26 | 0.42 |
| AL133268.1 | −1.13 | 0.30 | 1.96 | −0.31 | 0.44 | PTPRO | 0.33 | −0.49 | −0.88 | −0.16 | −0.25 | AC121764.3 | −0.82 | 0.50 | 1.25 | −0.20 | 0.94 |
| POFUT1 | 0.29 | −0.16 | −0.09 | −0.07 | 0.00 | AL132857.2 | −0.70 | −0.57 | −0.56 | 0.32 | 0.25 | AC092919.1 | −0.82 | 0.60 | −0.26 | 1.14 | −0.87 |
| SLC30A6 | 0.41 | −0.29 | −0.09 | −0.22 | −0.08 | RNU1-18P | −1.39 | 0.38 | −1.09 | 1.19 | −0.88 | MYBL1 | 0.03 | −0.39 | −0.02 | −0.49 | 0.10 |
| MEX3C | 0.27 | 0.05 | −0.18 | −0.01 | −0.26 | AC083829.2 | 1.25 | −2.43 | −1.47 | −1.13 | 0.62 | AC007495.2 | 0.27 | −1.27 | −0.71 | 1.48 | 3.11 |
| KCTD17 | −0.61 | −0.15 | 0.35 | −0.39 | −0.07 | AC007406.3 | 0.58 | −1.24 | −1.60 | −0.39 | −0.45 | AL161668.4 | −0.30 | −0.49 | −0.45 | 2.08 | 2.45 |
| RNA5SP221 | 1.36 | −0.68 | −1.37 | 0.17 | −0.26 | PIP5KL1 | 0.18 | 0.00 | −0.08 | 0.21 | 0.09 | CGA | −0.16 | −2.97 | −0.91 | −0.48 | −1.41 |
| RN7SKP150 | −1.30 | 1.80 | 0.95 | 1.24 | 0.29 | AC245187.1 | −0.79 | −0.35 | 0.20 | 0.42 | −0.42 | PRR23C | −0.23 | −0.38 | −0.18 | 0.57 | 1.42 |
| GPRC5B | −0.66 | 0.64 | 1.19 | −0.02 | −0.08 | AC010132.4 | 0.38 | −0.23 | −0.27 | −0.38 | 0.05 | RNMTL1P2 | 0.44 | 0.51 | −2.12 | 0.52 | −1.47 |
| RNF126 | 0.45 | −0.13 | −0.75 | 0.19 | −0.29 | CLCN3P1 | −0.39 | 0.15 | 0.21 | 0.12 | −0.32 | BMI1P1 | −0.47 | 0.34 | 0.18 | −1.40 | −1.11 |
| HBA1 | −1.93 | 0.66 | 1.84 | 1.64 | −1.80 | GIMAP7 | −0.25 | 0.17 | 0.93 | −0.23 | 0.00 | HDAC11-AS1 | −0.31 | 1.31 | −0.06 | 1.52 | −1.25 |
| AL137145.2 | −0.69 | 0.35 | 0.33 | 0.08 | 0.17 | AL157777.1 | −0.76 | 0.62 | 0.64 | −0.36 | −0.28 | AC090578.2 | 0.41 | −1.10 | −0.85 | 0.39 | 4.56 |
| FSIP2-AS1 | −1.01 | 1.22 | 1.88 | 0.36 | 0.31 | FXNP2 | −0.41 | 0.31 | 0.56 | −0.34 | 0.03 | LINC00539 | 0.05 | −0.21 | 0.19 | −0.13 | 0.12 |
| AL513477.2 | −1.41 | −0.48 | 1.39 | −0.22 | 1.30 | AC245884.3 | 0.48 | 0.38 | 0.50 | 0.19 | −0.12 | RPS2P28 | 0.17 | 0.57 | 1.27 | 1.15 | −0.20 |
| MPND | −0.36 | 0.20 | 0.17 | 0.00 | 0.04 | AC000123.3 | 0.17 | 0.08 | 0.11 | −0.13 | −0.19 | AC007496.1 | 0.05 | 0.06 | 0.37 | −0.03 | 0.27 |
| RNU6-292P | 2.21 | −0.15 | 0.24 | −0.06 | 0.58 | MIR342 | 0.62 | 0.55 | 0.46 | −0.13 | −0.12 | AC090957.1 | −0.26 | −0.78 | −1.27 | −0.21 | −0.45 |
| SLC5A6 | 0.52 | −0.61 | −0.85 | 0.00 | 0.05 | AC078820.1 | −0.53 | −0.17 | −0.41 | 0.13 | −0.46 | CHIAP1 | −0.27 | 1.01 | −3.34 | 1.66 | −1.02 |
| ELOVL2 | −1.01 | −0.01 | 1.09 | −0.07 | 1.01 | DPY19L2P2 | −0.19 | 0.07 | −0.33 | 0.43 | 0.27 | RNA5SP88 | −0.07 | 0.70 | 0.00 | 0.29 | −0.38 |
| KLHL24 | −0.48 | 0.56 | 0.70 | 0.24 | −0.04 | PLA2G2C | −0.63 | −0.26 | 0.54 | −0.61 | 0.31 | COX4I1P2 | 0.34 | −1.80 | −0.58 | −0.47 | 2.28 |
| AC015910.1 | −1.01 | 0.74 | 1.48 | 0.54 | 0.71 | NPM1P25 | 0.34 | −0.03 | 0.19 | −0.15 | −0.25 | AL133166.1 | 0.17 | −1.11 | −1.37 | 0.56 | −0.32 |
| AL359265.3 | −0.82 | 0.20 | 1.06 | −0.08 | 0.69 | RANP8 | −0.46 | −0.08 | 0.02 | −0.26 | −0.45 | IRF5P1 | −0.28 | −1.11 | 1.01 | 0.02 | 0.88 |
| FAM53A | −0.69 | 0.27 | 0.01 | 0.40 | 0.38 | AC116337.3 | 0.51 | 0.12 | −0.64 | 0.74 | −0.69 | FRG2LP | 0.79 | −0.38 | −0.82 | 1.01 | −0.33 |
| RHOBTB2 | −0.46 | −0.04 | 0.18 | −0.18 | 0.05 | G10656 | 0.65 | −0.22 | 0.66 | −0.21 | −0.80 | AC099568.2 | −0.10 | −0.30 | −0.25 | −0.76 | −0.07 |
| CHST5 | −1.94 | 0.40 | 0.19 | 0.24 | −0.23 | G15537 | −1.16 | −1.22 | 0.62 | −2.16 | 2.24 | SLC26A4-AS1 | −0.08 | 0.34 | −0.86 | 0.17 | −0.10 |
| CFAP53 | −0.74 | 0.26 | 0.67 | 0.12 | 0.26 | AL133243.1 | 0.39 | −0.27 | −0.44 | −0.26 | 0.11 | AC234775.2 | 0.09 | 0.10 | −0.91 | −0.11 | −0.47 |
| AL022322.1 | −0.62 | 0.35 | 0.49 | 0.09 | 0.06 | AGAP2 | 0.19 | −0.27 | 0.10 | −0.22 | 0.18 | AC011525.1 | 0.32 | −0.10 | −2.78 | 1.62 | −1.47 |
| ACTG1P10 | −0.81 | −0.01 | 1.02 | 0.14 | 0.60 | RN7SL438P | 0.57 | 0.03 | 0.79 | −0.28 | 0.61 | AC013472.2 | 0.15 | 0.20 | 0.37 | 0.03 | 0.83 |
| SPATA17 | −0.64 | 0.54 | 0.45 | 0.37 | −0.01 | G25440 | −0.53 | 0.36 | 0.34 | 0.27 | −0.20 | C9orf135-DT | −0.27 | −0.64 | −1.48 | 0.63 | −0.44 |
| FGF9 | −1.31 | −0.03 | 0.35 | 0.08 | 0.31 | AL021878.2 | −0.35 | 0.19 | 0.44 | 0.00 | −0.07 | FLJ42351 | 0.07 | −0.14 | 0.17 | 0.06 | 0.17 |
| PHACTR4 | 0.20 | 0.09 | −0.20 | 0.04 | −0.28 | FOXN1 | 0.24 | 0.28 | −0.15 | 0.26 | −0.10 | ELOCP28 | −0.42 | −0.46 | −0.91 | 0.78 | −0.36 |
| 11-Sep | −0.73 | 0.26 | 0.74 | −0.19 | 0.14 | AKT1 | 0.12 | −0.24 | −0.50 | 0.00 | 0.03 | OR4A16 | −0.27 | −0.28 | −1.17 | 0.62 | 0.04 |
| BST1 | −0.74 | 0.18 | 0.58 | −0.03 | 0.30 | MCFD2P1 | −0.80 | 0.78 | 0.39 | 0.92 | −0.27 | PQLC3 | −0.04 | 0.05 | 0.25 | −0.05 | 0.16 |
| MSL1 | −0.32 | 0.13 | 0.06 | 0.12 | 0.01 | AC011815.2 | −0.31 | −0.05 | 0.91 | 0.03 | 0.31 | MTND4P9 | 0.19 | −1.77 | 0.05 | −0.75 | −0.42 |
| H3F3AP2 | −0.88 | 0.38 | 1.21 | 0.20 | 0.35 | AL157371.2 | 1.43 | −2.27 | −0.57 | 0.01 | 1.59 | AC087762.1 | 0.47 | −1.49 | 0.20 | −1.20 | −0.10 |
| FMO1 | −0.88 | 0.49 | 0.90 | −0.06 | 0.24 | AC063947.2 | −0.56 | 1.23 | −1.51 | 0.86 | −0.81 | AL445305.1 | 0.06 | −0.21 | −0.09 | −0.13 | 0.32 |
| FAM153A | −1.05 | 0.52 | 0.50 | 0.03 | −0.05 | CCL11 | 0.89 | −0.61 | −2.96 | −1.45 | −2.35 | AL096772.1 | −0.14 | −1.44 | 0.19 | 0.23 | 0.75 |
| NMT1 | 0.23 | −0.14 | −0.28 | −0.11 | −0.19 | RNU6-1267P | 1.03 | −0.10 | 0.70 | −0.37 | −1.30 | AL713851.1 | 0.48 | −0.97 | −2.32 | 0.92 | −0.87 |
| SEPT7P2 | −0.32 | 0.16 | 0.32 | 0.08 | −0.01 | GAPDHP39 | −0.28 | 0.12 | 0.05 | 0.35 | 0.36 | CCER1 | −0.14 | −0.64 | −1.50 | 0.19 | −2.05 |
| AC027544.2 | −0.75 | 0.12 | 0.45 | 0.25 | 0.69 | AC005046.1 | −0.27 | −0.14 | −0.25 | −0.03 | 0.17 | RN7SL145P | 0.11 | −0.18 | 0.48 | 0.37 | 1.49 |
| RNA5SP44 | 0.99 | −0.08 | −0.60 | −0.43 | −0.48 | NAP1L1P3 | 0.29 | −0.10 | 0.30 | 0.10 | 0.65 | AC108681.1 | −0.37 | 1.46 | 0.15 | 1.89 | −0.39 |
| ARHGAP32 | 0.38 | −0.02 | −0.32 | 0.10 | −0.12 | ENPP6 | −0.43 | −0.51 | −0.55 | −0.03 | −0.21 | RP11-495P10.8 | 0.34 | −0.88 | −1.26 | 0.03 | −0.70 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC092279.1 | −0.61 | 0.26 | 0.29 | 0.33 | 0.61 | DAPK1-IT1 | −0.44 | −0.10 | 0.60 | −0.10 | 0.51 | LARP1BP2 | 0.81 | 0.41 | −2.88 | 2.18 | −0.96 |
| SNX3 | 0.49 | −0.10 | −0.16 | −0.03 | −0.18 | AP003557.1 | 0.65 | −0.33 | −1.22 | 0.25 | −1.09 | AC096577.1 | 0.15 | −0.48 | −0.33 | −0.79 | −0.50 |
| FOXC1 | −0.82 | 0.37 | 1.11 | −0.06 | 0.19 | MIR219-1 | 0.59 | 0.79 | 1.16 | 0.12 | 0.41 | HNRNPA1P51 | 0.17 | −0.72 | −0.83 | −0.06 | −0.60 |
| AC104763.3 | 1.23 | −0.36 | 0.44 | −0.20 | −0.32 | AC138356.2 | −0.24 | 0.32 | 0.30 | −0.13 | −0.24 | ERC2-IT1 | 0.17 | −1.32 | −0.14 | 0.42 | −0.01 |
| RN7SL206P | −1.07 | 0.16 | −0.13 | 0.49 | 0.06 | AC023538.1 | 0.91 | −1.57 | 0.22 | 0.80 | 1.21 | LINC02212 | −0.37 | −1.74 | 0.38 | −0.95 | 1.88 |
| ARGLU1 | −0.43 | 0.15 | 0.12 | 0.14 | 0.12 | LINC01932 | 0.84 | −0.08 | −0.80 | −0.69 | −0.69 | G22271 | −0.05 | 0.02 | 0.25 | −0.08 | 0.16 |
| DUSP11 | 0.38 | −0.05 | −0.24 | −0.04 | −0.18 | FAM241B | −0.31 | −0.10 | 0.14 | −0.09 | 0.42 | SPATA8 | −0.32 | −0.96 | −0.66 | 0.64 | 0.21 |
| NCK2 | 0.39 | 0.12 | −0.65 | 0.20 | −0.47 | MIR579 | 1.03 | 0.35 | −0.55 | −0.21 | 0.60 | AC011824.2 | −0.17 | −0.25 | −2.81 | 1.03 | −1.72 |
| GALK2 | −0.30 | 0.08 | 0.16 | 0.03 | 0.17 | GRIP2 | −0.21 | 0.35 | 0.20 | 0.04 | 0.23 | EI24P2 | 0.29 | 0.06 | −0.36 | 0.81 | 0.42 |
| SCARNA8 | −1.09 | 0.90 | 0.17 | 0.76 | −0.12 | G39662 | −1.04 | 1.37 | 2.34 | −0.48 | −0.40 | CYP51A1 | −0.05 | 0.08 | −0.08 | 0.18 | −0.49 |
| RN7SL275P | −2.33 | 0.66 | 1.41 | −0.47 | 0.36 | AL109620.1 | 0.90 | −2.69 | −0.96 | 0.04 | −0.20 | AC109583.3 | −0.29 | 0.47 | 1.74 | 0.00 | 0.16 |
| AC068397.1 | −1.28 | 0.42 | 2.58 | −0.24 | 0.52 | AC117529.1 | −0.98 | −1.58 | 0.15 | −1.66 | −0.97 | AC097451.1 | −0.35 | −0.15 | −1.67 | 2.66 | −0.17 |
| EML4 | 0.37 | −0.06 | 0.01 | −0.08 | −0.01 | AL121944.1 | 0.34 | 0.01 | −1.11 | 0.03 | −0.37 | CELA1 | −0.41 | 1.34 | −0.82 | 1.25 | −2.75 |
| CEACAMP5 | −1.31 | 0.75 | 1.15 | 0.51 | 0.65 | CEP170P1 | −0.30 | −0.04 | −0.92 | 0.50 | −0.26 | LINC01195 | −0.43 | −0.12 | −1.00 | 1.10 | −1.35 |
| SHLD3 | 0.48 | −0.01 | −0.49 | 0.10 | −0.41 | AC073115.2 | 1.33 | −1.03 | −1.96 | 1.12 | −0.79 | AC007255.2 | −0.23 | 0.41 | −0.94 | 0.69 | −2.97 |
| ARNT2 | −0.71 | 0.37 | 0.30 | 0.02 | 0.11 | SMYD1 | 0.65 | −1.98 | −2.51 | −0.08 | −0.05 | CLRN3 | 0.47 | −1.34 | −1.68 | −0.19 | 0.27 |
| AHR | 0.40 | −0.23 | −0.30 | −0.08 | −0.04 | G30963 | −0.55 | −0.12 | 0.51 | 0.31 | 0.18 | AL450336.1 | −0.26 | 0.22 | −0.39 | −1.38 | 0.38 |
| RBM24 | −1.06 | −0.02 | 1.25 | −0.08 | 0.11 | RSPH6A | −0.50 | 0.04 | 0.14 | 1.23 | 1.10 | RNU1-140P | −0.20 | −0.42 | −0.18 | −0.50 | −1.97 |
| NAV2-AS5 | −0.97 | 0.17 | 0.36 | 0.70 | −0.21 | LINC01378 | −0.66 | −0.46 | 0.64 | −0.48 | −0.81 | AC099670.2 | 0.50 | −2.27 | −0.49 | −1.35 | −1.43 |
| CICP22 | −1.53 | −0.26 | −0.45 | −0.06 | 0.45 | MTCO1P9 | −0.99 | 1.00 | −0.59 | 1.51 | −2.37 | MTRNR2L7 | −0.20 | −0.32 | 0.69 | 0.41 | 0.42 |
| RNF128 | −0.78 | 0.44 | 0.94 | −0.19 | 0.18 | MIR3612 | −1.18 | 0.07 | 0.59 | 1.31 | 1.24 | AL162384.1 | 0.38 | −0.95 | −1.11 | −0.70 | −0.44 |
| CHMP2A | 0.36 | 0.01 | −0.26 | −0.04 | −0.30 | LINC01665 | −1.18 | 0.98 | −0.95 | −0.70 | −2.24 | CDK5RAP1 | 0.02 | −0.06 | −0.11 | 0.11 | 0.08 |
| RMST | −1.64 | 0.02 | 0.71 | 0.07 | 0.37 | RN7SL585P | −1.27 | 0.15 | −0.05 | 1.92 | 0.06 | LINC00676 | −0.35 | −0.39 | −0.23 | 0.98 | −1.78 |
| AL136164.3 | −0.80 | 0.35 | 1.06 | −0.21 | 0.44 | CACNA1C-AS1 | 0.31 | −0.03 | −0.73 | −0.04 | −0.61 | AL355592.1 | 0.43 | −1.67 | −0.12 | −0.95 | 1.21 |
| DTX3 | −0.51 | 0.46 | 0.37 | 0.27 | −0.01 | AC018904.2 | 0.50 | −1.12 | −2.13 | −0.27 | −0.45 | GAGE1 | −0.35 | −0.52 | −0.04 | 3.01 | 0.62 |
| SOD2 | 0.84 | −0.75 | −0.67 | −0.21 | −0.43 | RPL23AP2 | 0.84 | −0.17 | −1.08 | −0.73 | −1.23 | RFPL4B | 0.33 | −0.83 | 0.26 | 0.89 | 0.29 |
| IL37 | −1.23 | 0.58 | 1.59 | 1.57 | 0.49 | PROSER3 | −0.13 | −0.02 | −0.33 | 0.09 | −0.12 | AC008155.1 | 0.06 | −0.30 | −0.49 | −0.37 | 0.07 |
| PRRC1 | 0.36 | −0.05 | 0.04 | −0.16 | −0.20 | LINC02055 | −0.55 | 0.23 | −0.75 | 0.17 | −1.15 | AC090802.1 | −0.36 | 0.85 | 0.00 | −0.96 | −0.25 |
| STEAP1B | 1.17 | −1.31 | −0.81 | −0.75 | 0.02 | AC084121.3 | −1.30 | 1.96 | 1.14 | 1.28 | 1.09 | AC136428.4 | −0.15 | −1.35 | −1.37 | 0.06 | 0.21 |
| HIST2H2AC | 0.39 | −0.13 | −0.73 | −0.06 | −0.62 | C2orf88 | −0.16 | 0.27 | 0.28 | 0.13 | 0.21 | RWDD2A | −0.04 | 0.20 | 0.26 | 0.01 | −0.21 |
| AC096732.1 | −1.96 | −0.23 | 3.24 | 0.53 | −0.39 | HNRNPA1P8 | 0.39 | −0.62 | −0.43 | −0.06 | 0.04 | AC008551.1 | −0.24 | 1.07 | 0.63 | 0.76 | −0.95 |
| RN7SKP93 | 1.78 | −0.06 | −1.68 | −0.27 | −0.74 | AC106795.3 | 0.90 | 0.13 | −1.46 | 0.03 | −1.51 | AC138956.2 | 0.07 | −0.10 | 0.34 | 0.11 | 0.28 |
| SEC24B | 0.28 | 0.03 | −0.23 | −0.03 | −0.24 | AP001056.1 | −0.53 | −0.67 | −0.08 | −0.47 | 0.14 | AC112206.1 | 0.60 | 0.22 | −0.10 | 0.07 | −1.63 |
| LAGE3 | 0.66 | −0.16 | 0.09 | −0.22 | −0.09 | NR3C1 | 0.13 | 0.10 | 0.00 | −0.01 | −0.20 | OR4A50P | 0.77 | 0.25 | −1.65 | 0.95 | −0.38 |
| CBR3 | 0.63 | 0.13 | −0.54 | −0.06 | −0.46 | AC010285.3 | −0.29 | 0.38 | 0.47 | −0.02 | 0.15 | LINC01081 | −0.22 | −1.53 | 0.00 | 0.98 | −0.23 |
| SLC35D3 | −1.83 | 0.65 | 0.52 | 0.32 | −0.34 | AL080317.2 | 0.27 | −0.19 | 0.11 | −0.02 | 0.33 | AC114774.1 | 0.36 | −0.93 | −1.38 | 1.46 | 0.91 |
| CAPN5 | −0.70 | 0.44 | 0.93 | −0.01 | 0.04 | AL390729.2 | 1.46 | −0.57 | −1.49 | −0.53 | 0.96 | AL078605.1 | 0.27 | 0.05 | −0.03 | 0.34 | 0.11 |
| SERTAD2 | 0.46 | −0.01 | −0.13 | −0.14 | −0.32 | KHSRPP1 | 0.85 | −1.36 | −2.48 | 0.32 | 0.38 | SUCLA2P1 | −0.18 | 0.21 | 0.60 | 0.47 | 1.45 |
| ADRA2A | −1.05 | 0.40 | 1.44 | 0.18 | 0.29 | AC007132.1 | −0.59 | −1.22 | 0.03 | 0.70 | 0.65 | AL110505.1 | −0.37 | −0.72 | −1.57 | −0.07 | 1.14 |
| ESR2 | −0.43 | 0.10 | 0.39 | 0.17 | 0.34 | LINC02512 | −1.43 | −0.35 | 1.12 | 0.89 | 1.73 | CCT7P2 | 0.42 | 0.13 | 0.50 | 0.42 | −0.11 |
| AC091948.1 | −0.90 | 0.84 | 0.85 | 0.21 | 0.24 | OTOP1 | −0.45 | 0.55 | −0.34 | 0.83 | −0.08 | AC015813.8 | −0.18 | −0.87 | 0.34 | 0.36 | −0.37 |
| KLF8 | −0.44 | 0.51 | 0.67 | 0.26 | 0.15 | AC004980.1 | −0.21 | 0.15 | 0.16 | 0.17 | 0.28 | AC103843.2 | −0.51 | 0.11 | −1.07 | −0.12 | −1.73 |
| CYB5B | 0.31 | −0.14 | −0.31 | 0.03 | −0.09 | ELMO3 | −0.19 | 0.12 | −0.47 | 0.41 | 0.02 | AC011933.4 | 0.13 | −0.42 | −0.43 | −1.30 | −0.99 |
| AC068228.2 | 2.76 | −1.11 | −1.50 | −0.67 | −1.50 | RPSAP12 | 0.49 | −0.05 | −1.17 | −0.34 | −1.08 | KRTAP3-4P | −0.74 | 0.72 | −0.65 | 0.26 | −2.30 |
| G36295 | −1.67 | 0.84 | 0.57 | 0.59 | −0.43 | AC010997.3 | 0.31 | −0.31 | −0.38 | −0.04 | −0.05 | AL390730.1 | 0.34 | −0.48 | −2.29 | 0.42 | 0.68 |
| CC2D1B | −0.36 | 0.11 | 0.02 | 0.21 | 0.18 | MED15 | 0.13 | −0.09 | −0.62 | 0.07 | −0.23 | AC022695.3 | 0.42 | −1.04 | 0.12 | −1.00 | 0.52 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AL590084.1 | −1.61 | 0.31 | 1.88 | 0.54 | 0.65 | AC092100.1 | 0.91 | −1.11 | −2.48 | 0.45 | −1.64 | RNU6-795P | 0.18 | −1.70 | 0.28 | −0.50 | 1.98 |
| ADGRL3 | −0.85 | 0.54 | 0.73 | 0.36 | 0.22 | AC124242.2 | −0.56 | −0.52 | −0.04 | −0.50 | 0.40 | BCAP31P2 | −0.15 | 0.43 | 1.02 | 0.27 | −0.82 |
| AC090543.2 | 0.95 | −0.96 | −0.27 | −0.18 | 0.50 | NDOR1 | −0.18 | −0.13 | −0.07 | 0.14 | 0.29 | OSTCP4 | −0.28 | −0.10 | −1.05 | −0.28 | −1.92 |
| AC046168.1 | −1.42 | −0.29 | −0.12 | 0.26 | 0.56 | LINC00315 | −0.77 | 0.98 | −1.27 | 0.62 | −0.01 | MIR499A | −0.19 | 1.49 | 0.83 | 0.63 | 0.04 |
| FAM21EP | −0.87 | 0.19 | 1.35 | 0.00 | 0.73 | STMN4 | −0.72 | 0.56 | 0.57 | −0.12 | −0.28 | AL592430.1 | −0.06 | 0.50 | −0.50 | 0.67 | −0.05 |
| LRP5L | −0.55 | 0.11 | 0.06 | 0.14 | 0.13 | AL022334.1 | −0.71 | −0.19 | −0.07 | 0.47 | −0.27 | AC016405.2 | −0.14 | −0.01 | 0.39 | −0.03 | 0.47 |
| DDX19B | −0.29 | 0.18 | 0.19 | 0.18 | 0.05 | CARD19 | 0.12 | 0.18 | −0.12 | 0.06 | −0.18 | ETF1P1 | −0.08 | −0.18 | 0.26 | 0.69 | 0.86 |
| AC080014.1 | −1.21 | 0.18 | 1.54 | −0.08 | 0.75 | SLC1A3 | 0.17 | −0.58 | −0.06 | −0.06 | 0.11 | LINC00336 | 0.38 | 0.19 | −0.13 | −0.55 | −0.90 |
| AFTPH | 0.45 | −0.02 | −0.06 | 0.04 | −0.18 | GABRG2 | −0.54 | −0.24 | −0.41 | 0.54 | −0.84 | AC090200.1 | −0.28 | 0.09 | 0.49 | 1.20 | 1.33 |
| PLN | −0.95 | 0.74 | 1.02 | 0.83 | −0.09 | AC104837.2 | 0.54 | −0.64 | −0.95 | −1.13 | −0.80 | AC009567.1 | 0.35 | −0.41 | −3.01 | 1.09 | −0.01 |
| ELP6 | 0.38 | −0.28 | −0.18 | −0.23 | 0.12 | OR1L1 | −0.51 | −0.78 | 0.90 | 0.76 | 0.32 | AC090151.1 | 0.27 | −0.53 | −1.40 | 0.10 | −0.07 |
| AF238378.1 | −2.32 | 0.77 | 1.76 | 1.29 | 0.81 | HPYR1 | −0.82 | −1.24 | −0.26 | −0.19 | 0.04 | CCND3P1 | −0.80 | 0.00 | 0.35 | −0.83 | −0.67 |
| CD207 | −1.18 | 0.65 | 1.62 | −0.19 | 0.65 | ACY3 | 0.93 | −1.79 | −0.50 | 0.23 | 1.04 | IL17F | 0.33 | −1.00 | −1.79 | −2.55 | −0.13 |
| LINC01050 | 2.13 | −2.39 | −2.00 | −0.67 | 0.72 | AC097460.3 | 0.45 | −0.21 | 0.54 | 0.04 | 0.43 | RNU6-1174P | 0.49 | −0.36 | −2.29 | −0.22 | −2.42 |
| AC091074.1 | −1.59 | 0.74 | 0.96 | 0.45 | 0.56 | AC004951.3 | −0.44 | 0.75 | 0.68 | 0.64 | 0.51 | C1orf56 | 0.04 | 0.03 | 0.13 | 0.15 | 0.19 |
| DLD | 0.42 | −0.25 | −0.37 | −0.07 | −0.08 | FKBP1BP1 | −1.25 | 1.27 | 2.16 | −1.11 | 0.28 | G2447 | −0.08 | 0.30 | −0.29 | −0.01 | −0.72 |
| PTGIS | −1.16 | 0.44 | 0.79 | 0.38 | −0.25 | AL021917.1 | 0.51 | 0.17 | 0.21 | 0.21 | 0.13 | MTND5P24 | 0.17 | −0.21 | −0.59 | 0.14 | −1.28 |
| ITGA2 | 0.74 | 0.16 | −0.45 | 0.16 | −0.51 | PPP1R17 | −0.77 | 0.04 | 1.77 | −1.13 | −0.03 | AC068446.3 | −0.41 | −1.13 | 0.97 | 1.49 | 2.43 |
| PCDHB12 | −0.93 | 0.18 | 1.19 | −0.25 | 0.16 | AC116616.1 | 0.97 | −1.41 | 0.38 | 0.33 | 1.76 | SLC25A37 | −0.04 | −0.07 | −0.25 | −0.08 | −0.14 |
| AC091057.4 | 1.21 | −0.65 | −0.37 | −0.42 | −0.16 | AL023495.1 | 0.81 | −0.84 | −0.45 | −0.61 | 0.41 | AL162456.1 | −0.15 | −0.59 | −0.33 | −0.71 | −1.14 |
| NFE2L3 | 0.49 | 0.14 | −0.02 | 0.09 | −0.12 | AC022517.1 | −1.03 | 1.13 | −0.50 | 0.37 | −1.93 | AC011431.2 | −0.13 | 0.61 | 0.85 | 0.93 | 0.43 |
| ADAM21 | −0.74 | 0.20 | 0.30 | −0.30 | −0.31 | MUC2 | −0.60 | −0.70 | −0.81 | −0.03 | −0.67 | RNA5SP307 | 0.15 | 0.24 | −1.01 | −0.25 | −0.81 |
| AC092611.2 | 1.18 | 0.01 | −0.35 | 0.09 | −0.46 | AL136146.2 | 0.39 | −0.47 | −1.13 | 0.16 | 0.18 | ATXN8OS | 0.25 | −0.26 | −0.59 | −0.21 | −0.88 |
| ABCA4 | −0.91 | 0.38 | 0.56 | 0.18 | 0.13 | AC021087.3 | −1.36 | 0.32 | 0.94 | 0.81 | 0.94 | ARHGEF1 | −0.03 | −0.25 | −0.40 | 0.03 | 0.11 |
| PGM3 | 0.41 | −0.22 | −0.07 | −0.35 | −0.05 | ATP8B2 | −0.19 | 0.06 | 0.39 | −0.28 | −0.15 | HMGN2P27 | −0.09 | 0.46 | −0.63 | 0.52 | −0.59 |
| BNIPL | −0.63 | 0.64 | 0.58 | 0.40 | 0.09 | G43605 | 1.91 | −1.45 | −1.84 | −0.95 | −1.10 | MIR3178 | 0.15 | 0.87 | −0.66 | −0.02 | −0.98 |
| STX18-AS1 | −0.39 | 0.08 | 0.40 | −0.09 | 0.32 | AP000769.3 | 0.97 | −0.14 | 2.01 | 0.38 | 1.20 | KLRG1 | −0.07 | −0.08 | 0.44 | −0.11 | 0.36 |
| SRP9P1 | 1.05 | −0.12 | −0.26 | −0.16 | −0.32 | CERKL | 0.38 | −0.55 | −0.79 | −0.43 | −0.91 | G28914 | −0.18 | −0.06 | 0.82 | −0.09 | 1.36 |
| EFCAB14 | 0.33 | −0.01 | −0.12 | −0.04 | −0.18 | RN7SL508P | −0.91 | −0.90 | 0.85 | −1.27 | 0.94 | MAS1L | −0.19 | 0.74 | 2.95 | 0.43 | 0.57 |
| NBPF11 | −0.52 | 0.27 | 0.63 | 0.11 | 0.51 | G36482 | 0.27 | −0.20 | 0.10 | −0.02 | 0.12 | S1PR1 | 0.05 | 0.06 | 0.71 | −0.29 | −0.16 |
| ANKRD37 | −0.71 | 0.44 | −0.04 | 0.57 | −0.02 | AC009987.1 | −0.40 | −0.39 | 0.75 | −0.62 | 0.25 | RNU7-73P | 0.18 | 0.40 | −0.49 | −0.07 | −0.83 |
| SLC43A1 | −0.53 | 0.19 | −0.08 | 0.65 | 0.19 | JMJD7 | 0.31 | 0.13 | 0.27 | 0.28 | 0.34 | RASA3-IT1 | −0.08 | −0.16 | 0.24 | −0.50 | 0.15 |
| AL161909.1 | −0.97 | 0.46 | 0.78 | 0.42 | 0.28 | AL354950.1 | −0.62 | −0.12 | 2.49 | −0.51 | 0.92 | AL136460.1 | 0.40 | −0.35 | −0.66 | −0.25 | −3.12 |
| CAMKK1 | −0.49 | 0.46 | 0.41 | 0.53 | 0.09 | SCP2 | 0.11 | 0.07 | 0.11 | 0.09 | −0.06 | PFKM | 0.02 | −0.03 | −0.27 | 0.09 | −0.01 |
| DENND6B | −0.62 | 0.18 | 0.16 | 0.13 | 0.27 | SEMG2 | 0.92 | −0.05 | −1.94 | 0.36 | −1.49 | LINC01015 | −0.36 | −0.14 | −1.73 | −0.17 | −1.21 |
| RNU6-652P | 0.88 | 0.19 | −0.17 | 0.18 | 0.06 | AC093801.1 | 0.66 | −0.88 | −0.78 | 0.22 | 1.34 | B3GALNT1 | −0.04 | −0.04 | 0.01 | −0.05 | −0.11 |
| PALD1 | 0.56 | −0.14 | −0.51 | 0.10 | 0.02 | AP002075.1 | 0.71 | −0.49 | 1.07 | −1.38 | −0.24 | RPL3P12 | −0.39 | 0.90 | 0.19 | −2.12 | −1.13 |
| GABRB3 | −1.03 | 0.62 | 0.29 | 0.85 | 0.19 | AC006296.2 | −0.66 | −0.79 | −2.56 | 0.84 | −0.22 | FAM129A | 0.04 | 0.09 | −0.18 | −0.02 | −0.19 |
| KIAA1671 | 0.41 | 0.09 | −0.31 | 0.12 | −0.10 | AC010531.6 | −0.36 | −0.65 | 0.30 | −0.18 | 0.49 | AC006288.1 | −0.31 | 0.77 | −0.52 | 0.02 | −2.41 |
| FAN1 | −0.30 | 0.20 | 0.30 | 0.15 | 0.24 | NCBP3 | −0.07 | 0.03 | 0.06 | −0.05 | 0.05 | CCDC66 | −0.02 | −0.09 | 0.13 | −0.03 | 0.12 |
| FEZF2 | −1.05 | 0.79 | 0.40 | −0.02 | −2.34 | SRRM5 | −0.21 | 0.12 | −0.21 | 0.13 | −0.02 | RPEP4 | 0.07 | −0.38 | 0.54 | 0.20 | 0.73 |
| AC011503.1 | −1.38 | 0.08 | 2.96 | 0.48 | 1.07 | PPIAP2 | −0.28 | 0.46 | 0.17 | 0.36 | −0.12 | NAP1L4P2 | −0.30 | −0.76 | 0.68 | 2.32 | 1.43 |
| AC013448.2 | −1.85 | −0.39 | 1.73 | −0.69 | 0.94 | AL359182.2 | 0.40 | −0.57 | −0.33 | −0.01 | 0.37 | MIR4646 | −0.33 | −0.80 | 1.04 | −1.42 | 0.77 |
| RNU1-89P | −1.58 | 0.09 | −0.10 | 0.88 | −0.20 | AC131956.2 | −0.53 | −0.19 | −0.90 | 0.42 | −0.16 | AC009145.1 | 0.07 | 0.15 | 0.22 | 0.47 | 0.54 |
| NSG1 | 0.77 | 0.20 | −0.30 | 0.30 | −0.44 | FSCB | −0.89 | 0.34 | 0.67 | −0.15 | 0.34 | AP003041.2 | −0.07 | 0.29 | −0.14 | 0.57 | 0.06 |
| CCR7 | 0.92 | −0.91 | −0.66 | −0.74 | −0.05 | PCNT | −0.11 | −0.12 | −0.28 | 0.02 | 0.04 | MARK2P15 | −0.34 | 1.49 | 0.66 | 0.10 | −1.58 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| BNIP3P28 | −1.91 | 0.97 | 1.64 | 0.33 | 0.01 | RCBTB1 | −0.11 | 0.07 | 0.21 | 0.08 | 0.13 | AC099670.3 | −0.56 | −1.38 | 0.95 | −0.91 | 2.31 |
| AP003469.4 | −0.68 | 0.71 | 1.20 | 0.07 | 0.22 | SMARCE1P6 | 0.30 | −0.01 | −1.75 | 0.14 | −0.87 | GOLGA6D | 0.80 | −0.42 | −1.50 | 1.33 | −0.08 |
| AC009148.1 | −0.71 | 0.65 | 1.17 | 0.60 | 0.34 | RNU6-588P | 0.61 | 0.10 | −0.33 | 0.75 | 0.26 | AC024587.2 | 0.26 | −1.36 | −1.30 | 0.83 | −0.16 |
| A4GALT | −0.63 | 0.38 | 1.01 | −0.21 | 0.13 | CD3EAP | 0.20 | −0.43 | −0.54 | 0.13 | 0.16 | AC105429.2 | −0.08 | −0.08 | 0.25 | −0.06 | 0.41 |
| DDR2 | −0.94 | 0.45 | 1.29 | −0.08 | 0.24 | NR5A2 | −0.27 | 0.35 | 0.79 | 0.02 | 0.15 | AC084121.4 | −0.50 | 0.27 | 1.95 | 0.20 | 1.49 |
| DUSP8P5 | −0.71 | 0.39 | 0.31 | 0.67 | 0.22 | SNORD113-8 | 0.63 | 1.05 | 0.64 | −0.13 | −0.70 | AC090630.1 | −0.19 | −0.60 | 1.34 | 0.17 | 2.60 |
| AL645929.2 | −0.85 | 0.49 | 0.73 | −0.40 | −0.34 | AC245389.1 | −0.79 | 0.10 | 0.74 | 0.53 | 0.52 | AL162377.2 | −0.39 | −1.46 | 1.17 | −0.70 | 1.55 |
| AL133467.1 | −1.36 | 0.27 | 1.38 | 0.74 | 0.48 | L34079.2 | 0.49 | −0.18 | −0.54 | −0.32 | −1.01 | HNRNPA1P17 | 0.40 | 0.15 | −0.57 | −0.63 | −1.87 |
| PARP8 | 0.44 | −0.10 | −0.44 | 0.17 | −0.05 | MIR1290 | 1.15 | −1.63 | −2.25 | −0.67 | −0.56 | DHX40P1 | 0.71 | 0.64 | −1.75 | 1.56 | −2.27 |
| PCARE | −0.76 | 0.39 | 0.66 | 0.16 | 0.19 | AC093729.1 | −0.64 | −0.40 | 1.45 | −0.48 | 1.68 | AL445433.1 | 0.22 | −1.20 | −1.36 | −0.01 | −0.03 |
| AC005865.2 | −0.92 | 0.47 | 0.58 | 0.39 | 0.14 | LINC01896 | −0.87 | 0.63 | −0.24 | 0.38 | −0.57 | KRT18P39 | 0.24 | −0.38 | −0.08 | 0.89 | −0.48 |
| FUBP3 | 0.27 | −0.11 | −0.26 | −0.09 | −0.14 | AC032044.2 | 0.46 | 0.17 | 0.25 | −0.07 | 0.11 | ATP5PBP4 | 0.39 | −0.67 | −1.15 | 0.29 | −1.66 |
| RPL17P42 | 1.68 | −1.03 | −1.24 | −0.47 | −0.45 | G32019 | −0.74 | 0.63 | 0.60 | 0.96 | 0.39 | MED15P9 | −0.22 | −1.17 | −1.86 | 0.72 | −0.71 |
| CALU | 0.54 | −0.44 | −0.26 | −0.57 | −0.33 | AC011242.1 | −0.35 | 0.14 | −0.01 | 0.01 | −0.17 | PRF1 | 0.08 | −0.64 | 0.37 | −0.50 | 0.13 |
| C1QL4 | −1.58 | 0.06 | −0.91 | 0.13 | −1.34 | GS1-600G8.3 | 1.66 | −0.90 | −1.60 | −0.15 | 0.84 | RNFT1P3 | 0.48 | 0.22 | −0.14 | 0.33 | −1.22 |
| AL365295.1 | −0.68 | 0.20 | 0.54 | 0.30 | 0.29 | AL513497.1 | 0.28 | −0.01 | −1.37 | 0.00 | −0.52 | AC020895.2 | 0.20 | −0.67 | −0.98 | 0.08 | −0.12 |
| GAS8 | −0.51 | 0.18 | 0.04 | 0.29 | 0.11 | MIR3165 | 0.83 | −1.06 | −0.33 | −0.71 | −0.68 | AP001059.2 | −0.18 | −1.08 | 1.51 | −0.59 | 1.54 |
| FGF14-AS2 | −1.08 | 0.61 | 0.82 | −0.27 | −0.21 | RN7SL232P | −0.93 | 0.27 | −0.15 | −0.53 | −0.12 | AC069277.2 | 0.34 | −0.73 | −0.24 | 0.48 | −2.35 |
| SULT1A2 | −1.25 | 0.75 | 0.79 | 0.53 | 0.06 | AL512324.1 | −1.26 | 1.66 | 0.87 | −0.64 | −0.26 | DDX43P2 | 0.41 | 0.00 | 0.76 | 1.04 | −1.13 |
| PES1P2 | −1.92 | −0.59 | 1.08 | 0.61 | 1.22 | ERAP1 | 0.14 | −0.17 | −0.12 | −0.04 | −0.16 | AC007731.2 | −0.05 | −0.44 | 0.16 | −0.25 | 0.30 |
| CD2AP | 0.30 | 0.04 | −0.13 | −0.11 | −0.26 | LMNTD1 | 0.70 | −1.64 | −1.38 | 0.19 | 0.19 | MTND6P5 | 0.05 | −0.37 | 0.11 | −0.10 | 0.35 |
| SLC46A1 | −0.66 | 0.87 | 0.76 | 0.19 | −0.25 | KDM5A | −0.07 | 0.10 | 0.14 | 0.04 | 0.02 | PLSCR2 | −0.09 | −0.66 | 0.13 | 0.16 | −0.31 |
| GKN3P | −2.77 | 1.87 | 1.95 | 3.25 | 0.64 | SPOCD1 | 0.53 | −2.20 | −1.74 | −1.72 | −0.80 | AL442639.1 | −0.29 | 0.83 | −1.87 | 0.51 | −1.88 |
| CCDC150 | 0.52 | −0.45 | −0.82 | −0.20 | −0.29 | MIR5581 | 0.57 | 0.07 | 0.03 | −0.30 | −0.78 | AC068535.1 | −0.43 | −0.63 | 0.81 | −0.77 | 1.92 |
| AC010469.1 | −2.08 | 0.86 | 3.20 | 0.90 | 0.83 | AJUBA | 0.23 | −0.07 | −0.36 | 0.08 | 0.00 | AC108734.2 | 0.20 | 0.76 | −0.49 | −0.26 | −1.97 |
| SCGB2A1 | −2.01 | 0.90 | 2.95 | −0.10 | 0.12 | SCNN1G | 0.27 | 0.04 | −0.93 | −0.10 | −0.76 | AC007450.4 | 0.29 | 0.49 | −1.35 | 2.12 | −0.33 |
| RN7SL437P | −1.23 | −0.12 | −0.91 | 0.74 | 0.50 | LNCTAM34A | −0.27 | −0.73 | −0.02 | 0.42 | 1.07 | BRD4 | 0.02 | 0.04 | −0.21 | 0.06 | −0.11 |
| MIR5690 | −0.89 | 0.34 | 1.01 | 0.30 | 0.37 | RMCX5-GPRAS. | −0.11 | 0.22 | 0.04 | 0.18 | 0.02 | CLUHP4 | 0.36 | −0.67 | −0.16 | 2.23 | 1.69 |
| CCNK | 0.37 | −0.15 | −0.40 | −0.09 | −0.12 | SLC25A5P2 | −0.79 | 0.54 | −0.23 | 0.42 | 0.09 | AC064834.1 | 0.80 | 0.09 | 1.18 | 0.47 | 1.44 |
| SRSF8 | 0.34 | 0.05 | −0.26 | 0.13 | −0.20 | AL121772.2 | 0.50 | 0.59 | −0.31 | 0.07 | −1.28 | AL356356.1 | −0.06 | −0.34 | −0.72 | 0.16 | −0.01 |
| SIRT4 | −0.77 | 0.34 | 0.67 | 0.46 | 0.63 | AC107993.1 | 0.32 | 0.19 | 0.47 | 0.32 | 0.48 | PRMT5P1 | 0.31 | −0.19 | −0.85 | 2.10 | −0.72 |
| CATSPERE | −0.52 | 0.22 | 0.43 | 0.09 | 0.13 | AC097716.1 | 0.51 | −0.03 | 0.01 | −0.10 | 0.22 | LINC2194 | 0.23 | −1.67 | −2.10 | −0.35 | −1.32 |
| IL36B | 1.61 | −0.19 | −0.32 | 0.26 | −0.62 | BIVM | 0.13 | −0.06 | 0.35 | −0.08 | 0.35 | AC005614.1 | 0.25 | −1.31 | −1.00 | −0.55 | −1.53 |
| PHF12 | −0.23 | 0.00 | 0.19 | −0.03 | 0.23 | CYLC2 | −0.76 | −0.67 | 0.73 | −0.23 | 0.44 | LINC01657 | 0.11 | −0.38 | 0.38 | −0.37 | 0.38 |
| RAC1P2 | 0.85 | −0.53 | −0.43 | −0.62 | −0.26 | LINC01167 | 0.71 | 0.11 | 0.13 | 0.16 | 1.38 | NT5C3AP1 | −0.15 | −0.33 | −0.47 | 1.19 | 0.57 |
| ALKBH3 | 0.29 | −0.09 | −0.29 | 0.05 | −0.21 | EIF4BP2 | 0.32 | 0.63 | 0.08 | 0.47 | −0.31 | MTCO3P19 | −0.12 | 0.78 | 0.50 | 1.01 | 0.87 |
| FCER2 | −1.17 | 0.63 | −0.20 | 1.48 | 0.01 | AC019130.1 | 0.74 | −1.09 | −0.76 | −0.24 | 0.30 | IGHV3-53 | 0.79 | 0.01 | 2.21 | −1.04 | 0.52 |
| CCDC102A | −0.60 | 0.21 | 0.33 | 0.20 | 0.20 | G43078 | 0.32 | 0.12 | 0.78 | 0.08 | 0.12 | AC091544.1 | −0.21 | −1.86 | 1.02 | −0.15 | 1.94 |
| NAA38 | 0.38 | −0.21 | −0.35 | −0.04 | −0.46 | GACAT1 | −1.05 | −0.57 | −0.80 | 0.56 | −1.88 | AC010969.1 | 0.06 | 0.40 | 0.04 | 0.17 | −0.43 |
| PPP2R1A | 0.29 | −0.07 | −0.42 | 0.06 | −0.20 | LARP1P1 | 1.21 | −0.40 | −1.03 | −0.94 | −1.03 | EDNRB-AS1 | −0.18 | 1.00 | −0.48 | −0.25 | 0.00 |
| EFCAB1 | −0.67 | 0.16 | 0.48 | 0.39 | 0.34 | RNU6-1102P | −0.61 | 0.40 | −0.14 | 0.73 | −0.04 | AL353671.4 | −0.07 | −0.02 | 0.37 | 0.49 | 0.17 |
| SLC9A5 | −0.53 | 0.16 | 0.06 | −0.07 | 0.04 | RASA4 | −0.18 | 0.19 | 0.38 | 0.31 | 0.23 | AC016266.1 | −0.45 | −0.68 | −0.30 | 0.41 | 0.47 |
| GEMIN7-AS1 | 1.04 | −0.40 | 0.12 | −0.06 | 0.26 | AL049775.1 | −0.39 | −0.08 | −0.32 | 0.39 | −0.72 | AL355773.1 | 0.20 | −0.82 | −2.59 | 0.60 | −1.75 |
| AC005476.1 | 0.92 | −0.71 | −0.31 | −0.24 | −0.16 | G31770 | −0.84 | 1.61 | 0.02 | 1.09 | −0.79 | RN7SL522P | 0.43 | −0.93 | −1.69 | −0.79 | 0.41 |
| MFSD10 | 0.45 | −0.27 | −0.79 | 0.04 | −0.11 | AC008758.2 | −0.40 | 0.96 | 0.88 | −0.16 | −0.43 | AC126915.3 | −0.79 | −0.80 | 1.25 | 0.46 | 0.94 |
| AC119800.1 | 1.82 | −0.52 | −1.12 | −0.41 | −1.08 | AC002524.1 | 0.68 | −0.45 | −1.12 | 0.49 | −0.29 | SCARF1 | −0.04 | −0.40 | −0.06 | −0.16 | 0.16 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| LINC02066 | −1.27 | 0.91 | 1.03 | 1.11 | −0.28 | G10695 | 0.65 | 0.59 | −0.47 | 0.96 | −0.60 | AC068014.2 | 0.20 | −0.86 | 0.93 | −0.36 | 1.91 |
| AC073133.2 | −1.46 | 0.87 | 1.16 | 1.76 | 0.83 | FAM215B | −0.30 | 0.10 | 0.68 | 0.26 | 1.18 | G28942 | −0.05 | 0.36 | 0.61 | −0.04 | 0.10 |
| LRRN2 | −0.97 | −0.65 | 0.55 | −0.37 | 0.26 | CDK2 | 0.15 | −0.26 | −0.75 | 0.17 | −0.20 | DLG5-AS1 | 0.05 | −0.43 | −1.03 | 0.23 | −0.26 |
| EPB41L1 | −0.46 | 0.28 | 0.19 | 0.13 | −0.06 | AL513220.1 | −0.60 | 0.01 | −1.29 | −0.40 | −0.98 | LINC02366 | 0.38 | 1.45 | 0.51 | 1.34 | 0.54 |
| AL031731.1 | −1.11 | 0.63 | 0.72 | 0.68 | 0.28 | SLC2A10 | −0.24 | 0.09 | 0.83 | −0.42 | 0.19 | RP11-89F17.5 | 0.07 | −0.56 | −0.44 | 0.12 | 0.05 |
| AL023284.2 | 1.09 | −0.11 | −0.30 | −0.26 | −0.47 | AC112250.2 | 0.52 | −0.48 | −0.60 | −0.53 | −0.87 | RN7SKP105 | −0.41 | 0.11 | 0.13 | 0.33 | 1.03 |
| COASY | 0.36 | −0.17 | −0.52 | 0.11 | −0.12 | PAK6 | 0.28 | −0.09 | −0.36 | 0.23 | −0.05 | OR7E145P | 0.32 | 0.11 | 0.22 | 0.53 | 0.38 |
| AC115618.2 | 0.60 | −0.28 | −0.22 | −0.24 | −0.01 | AL135787.1 | 0.48 | −0.79 | −0.39 | 0.25 | 0.38 | AL772337.4 | 0.79 | −0.59 | −2.11 | 0.81 | 0.63 |
| GNAS-AS1 | −0.86 | −0.48 | 0.78 | −0.55 | 0.58 | AL049874.2 | −0.76 | −0.52 | −0.49 | −0.38 | 0.67 | AC010320.4 | −0.05 | −0.13 | 0.24 | −0.18 | 0.33 |
| HMG20B | −0.56 | 0.32 | −0.24 | 0.29 | −0.20 | SLC39A13 | 0.14 | −0.09 | −0.68 | 0.15 | −0.23 | AL160037.1 | 0.14 | 0.67 | 0.30 | 0.17 | −0.56 |
| AC099336.1 | −1.14 | 1.08 | 0.78 | 0.26 | 0.04 | AL022400.1 | 0.46 | −0.09 | −0.74 | 0.45 | 1.01 | HINT1P1 | 0.33 | 0.22 | −1.54 | 0.96 | −0.75 |
| RN7SKP230 | −0.87 | 0.43 | 0.87 | 0.22 | 0.06 | AC060766.7 | 0.37 | 0.04 | 0.32 | −0.12 | 0.53 | DYDC1 | −0.30 | −1.36 | 1.01 | −0.81 | 1.35 |
| SLC25A18 | −0.90 | 0.70 | 0.53 | 0.05 | −0.03 | KCNMB2 | −0.51 | −0.37 | 0.35 | −1.16 | −0.01 | RNU6-285P | 0.24 | −0.09 | −0.55 | 2.13 | 0.19 |
| SLC16A5 | −0.46 | 0.18 | 0.04 | 0.23 | 0.02 | AC087276.3 | 0.39 | −0.77 | −0.45 | −0.22 | 0.01 | ACTN1-AS1 | 0.13 | 0.81 | 0.11 | −0.05 | 0.12 |
| PLD5 | −1.45 | 0.33 | 0.69 | 0.27 | −0.58 | AC013549.1 | −0.46 | −1.00 | 0.22 | −0.84 | 0.65 | AC018685.2 | 0.47 | −0.45 | −0.46 | −0.52 | 0.98 |
| GAPDHP33 | −1.41 | 0.60 | 1.34 | 0.63 | 0.83 | NPAS4 | −0.51 | −1.28 | 0.07 | −0.53 | 0.32 | EHHADH-AS1 | 0.21 | −0.18 | −0.27 | 0.63 | −0.14 |
| MOCOS | 0.47 | −0.28 | −0.30 | −0.21 | −0.08 | AC135782.1 | −0.56 | −0.45 | −0.53 | 0.30 | 1.73 | AC131160.1 | 0.16 | −0.73 | 1.64 | −0.64 | 1.28 |
| AC012038.1 | −1.75 | 1.28 | 0.98 | 0.69 | 1.16 | BCL6B | 0.20 | −0.05 | 0.60 | −0.53 | −0.21 | MIR4518 | 0.47 | −0.35 | −0.58 | −1.79 | 0.90 |
| AC005224.3 | 1.09 | −1.72 | −0.73 | −1.02 | 0.70 | AL035588.1 | 0.36 | 0.23 | 0.14 | 0.48 | 0.20 | AC083805.2 | −0.06 | 0.11 | 0.60 | 0.10 | 0.26 |
| LACC1 | 0.45 | −0.43 | −0.06 | −0.27 | 0.05 | AL121656.1 | −0.76 | 0.04 | −1.14 | −0.42 | −0.67 | AP001357.1 | −0.35 | 0.44 | 2.44 | 0.22 | 1.27 |
| POLRID | 0.27 | −0.03 | −0.10 | −0.01 | −0.16 | RNF38 | −0.10 | 0.27 | 0.15 | 0.08 | −0.10 | CCDC14 | −0.03 | 0.00 | 0.21 | −0.06 | 0.15 |
| SMIM10 | −0.85 | 0.05 | 1.62 | −0.24 | 0.53 | LDHAP5 | 0.69 | 0.08 | 0.60 | 0.17 | 0.24 | MTATP6P9 | 0.22 | −1.31 | −0.94 | 0.43 | −0.24 |
| 5S_rRNA | −1.08 | 0.59 | −0.30 | 1.15 | −0.19 | AL049542.1 | −0.37 | −0.24 | −0.18 | −0.19 | 0.52 | CADM1 | 0.04 | 0.28 | 0.08 | 0.32 | 0.28 |
| CFL2 | −0.63 | 0.30 | 0.36 | −0.14 | −0.26 | ETV1 | −0.22 | −0.03 | 0.67 | −0.08 | 0.44 | AC009558.2 | 0.30 | −0.04 | 0.72 | 0.79 | 0.16 |
| PCSK6 | 0.61 | −0.26 | −0.11 | −0.18 | −0.35 | AC055855.1 | −0.40 | 0.26 | 0.13 | 1.17 | 0.90 | AL592437.2 | 0.06 | 0.20 | −0.10 | 0.31 | −0.08 |
| MYO10 | 0.40 | −0.36 | −0.81 | −0.08 | −0.12 | PSORS1C2 | −0.34 | 0.32 | 1.28 | 0.65 | −0.32 | AC114689.2 | 0.49 | −0.43 | 0.50 | 1.36 | 0.45 |
| IGSF9B | −0.74 | 0.13 | 0.06 | 0.09 | 0.17 | AC092447.7 | −0.63 | −0.16 | 0.79 | −0.44 | −1.00 | AC055813.1 | −0.08 | −0.14 | −0.88 | 0.82 | −0.45 |
| ADAMTS19 | −1.07 | 0.05 | 0.14 | −0.13 | −0.19 | AL096678.1 | 0.75 | −0.14 | −1.54 | 0.31 | −0.91 | RLN2 | 0.20 | 0.07 | −0.46 | 0.45 | −0.05 |
| GNB1 | 0.32 | −0.14 | −0.18 | −0.23 | −0.14 | PEX19 | −0.16 | 0.21 | 0.14 | 0.07 | −0.08 | CDH23-AS1 | 0.32 | −2.74 | 0.26 | −2.45 | 0.93 |
| FBXL16 | −0.70 | 1.15 | 1.11 | 0.62 | 0.10 | IL12A | −0.66 | −0.75 | 2.19 | −0.39 | 2.99 | CYP2C61P | 0.40 | −0.47 | 0.65 | 0.72 | 0.77 |
| CNNM2 | −0.29 | 0.31 | 0.33 | 0.22 | 0.09 | AC010336.1 | 0.34 | 0.05 | −0.70 | 0.26 | −0.51 | BCAR4 | 0.24 | −0.66 | −1.32 | −0.09 | −1.28 |
| MSTN | −1.04 | −0.03 | 1.02 | −0.31 | 0.19 | HNRNPA1P64 | −0.85 | −0.36 | −0.22 | 1.18 | −0.97 | LINC01148 | −0.79 | 0.15 | −0.08 | −0.20 | −0.26 |
| LRRC57 | −0.38 | 0.16 | 0.16 | 0.12 | 0.02 | RND1 | 0.47 | −1.00 | −2.15 | 0.37 | −1.13 | MTND2P15 | 0.49 | −0.87 | −2.38 | 1.32 | −2.04 |
| RSRP1 | −0.31 | 0.17 | 0.52 | −0.16 | 0.22 | GOT1L1 | 1.24 | −0.26 | −2.41 | 1.30 | −0.85 | AC126773.1 | −0.10 | −0.25 | −0.96 | 0.07 | −0.31 |
| DNAH3 | −0.76 | 0.30 | −0.01 | 0.36 | −0.21 | AC092669.1 | 0.67 | 0.38 | −0.57 | 0.49 | −1.86 | GPR75-ASB3 | −0.08 | −0.89 | 0.42 | 0.01 | 1.25 |
| FADS2 | −1.44 | 1.02 | 0.14 | 2.73 | 0.98 | AC091492.1 | −0.41 | 0.31 | −0.33 | 0.10 | −0.22 | AC087430.1 | 0.18 | −0.38 | −0.70 | −0.22 | −0.33 |
| STIM2 | 0.27 | 0.02 | −0.36 | 0.10 | −0.31 | PPP2R2DP1 | −0.75 | 0.11 | −0.78 | 1.03 | −0.84 | AL592114.1 | 0.11 | −0.18 | 0.18 | 0.18 | −0.67 |
| PARM1 | −0.63 | 0.57 | 0.72 | −0.19 | −0.37 | RNU6-875P | 0.88 | −0.30 | −0.03 | −0.87 | 0.80 | AC005856.1 | 0.05 | 0.10 | 0.83 | 0.11 | 0.62 |
| BEND6 | 0.71 | −0.55 | −0.11 | −0.48 | 0.20 | DAB2IP | 0.09 | 0.18 | 0.01 | 0.03 | −0.16 | OR6K2 | −0.26 | −0.96 | −0.20 | −1.04 | 0.38 |
| SLC19A3 | −1.22 | 0.68 | 1.50 | 1.13 | 0.32 | AL627171.1 | −0.54 | 0.01 | 1.12 | −0.01 | 0.64 | AC108471.2 | −0.06 | −0.34 | 0.17 | −0.18 | 0.57 |
| G31765 | −1.27 | 1.07 | 1.24 | 0.68 | 0.47 | CAPN10-DT | 0.25 | −0.22 | 0.37 | −0.02 | 0.22 | AC121333.1 | 0.20 | −0.72 | −1.15 | −0.32 | −1.28 |
| G25680 | 1.50 | −0.02 | −0.58 | −0.15 | −0.30 | PLEC | 0.16 | −0.16 | −0.63 | 0.09 | −0.08 | HARIA | −0.11 | 0.10 | 1.04 | 0.57 | 0.58 |
| AL731563.3 | −0.61 | 0.30 | 0.31 | −0.12 | 0.26 | CASC4P1 | −0.41 | 0.68 | −0.11 | 0.68 | −0.35 | SLC38A3 | 0.10 | 0.37 | −0.29 | 0.24 | −0.24 |
| NEFH | 0.86 | −0.81 | −0.80 | −0.68 | −0.27 | LRRC37A6P | −0.32 | 0.06 | 0.83 | −0.13 | 0.42 | ANKRD27 | 0.01 | −0.01 | 0.04 | −0.03 | 0.09 |
| HOXA-AS2 | −0.56 | −0.03 | 0.75 | 0.28 | 0.31 | ITGB1BP2 | 0.21 | −0.56 | −0.37 | −0.18 | 0.01 | RN7SL142P | 0.24 | 0.16 | −0.82 | 1.22 | −0.74 |
| ARMH3 | 0.18 | −0.11 | −0.17 | −0.09 | −0.05 | AC139792.1 | −0.29 | 0.17 | 0.66 | −0.04 | 0.44 | AC060234.2 | 0.08 | −1.18 | 0.02 | −0.10 | 1.30 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| CARMIL3 | −0.87 | 0.80 | 0.55 | 0.61 | 0.12 | CLIC3 | 0.24 | 0.35 | −0.05 | 0.19 | −0.82 | PHF13 | 0.03 | −0.03 | 0.10 | 0.06 | −0.07 |
| ST8SIA4 | 0.81 | −0.80 | −0.50 | −0.62 | −0.29 | AMPH | −0.30 | −0.02 | 0.37 | 0.03 | 0.47 | GTSF1L | 0.28 | −0.60 | −1.80 | 0.39 | 2.19 |
| STRIP1 | 0.18 | −0.10 | −0.31 | 0.03 | −0.07 | SDCBP2-AS1 | 0.18 | 0.00 | 0.03 | −0.08 | −0.19 | ANKRD40CL | 0.12 | −1.01 | 0.11 | 0.83 | 1.82 |
| G15105 | −2.59 | 0.93 | 2.61 | 0.11 | 1.20 | AP000857.2 | −0.79 | −0.20 | 2.92 | −0.49 | 0.64 | RPL7AP4 | −0.11 | −0.62 | 0.08 | 0.22 | 0.53 |
| AL645608.1 | −1.46 | 0.24 | 0.27 | 0.83 | 0.02 | ACTR3BP4 | −0.77 | 0.73 | −0.30 | 0.94 | 0.63 | AC009902.3 | −0.11 | −0.13 | 0.71 | −0.12 | 1.01 |
| KLHL41 | −0.71 | 0.28 | 0.40 | 0.11 | 0.01 | AL137127.1 | −0.23 | −0.06 | 0.17 | −0.45 | −0.04 | PCAT6 | −0.06 | 0.71 | −0.04 | 0.58 | −0.21 |
| MTA1 | −0.47 | 0.04 | 0.06 | 0.17 | 0.23 | AL049825.1 | 0.92 | −0.81 | −1.09 | −0.96 | −1.98 | LINC02167 | −0.20 | −0.02 | 0.20 | 0.47 | 1.37 |
| G119 | −2.20 | 2.19 | 1.21 | 1.23 | 0.61 | AC010487.2 | −0.65 | 0.26 | 1.34 | 0.43 | −0.14 | AC090458.1 | −0.23 | 0.34 | −1.16 | 1.26 | −0.51 |
| AC116535.1 | −0.75 | −0.01 | 0.73 | −0.50 | 0.24 | OR5212 | −0.33 | 0.00 | 0.63 | 0.16 | 0.20 | AC112698.1 | 0.34 | −0.16 | −1.41 | −1.21 | −1.88 |
| ISYNA1 | −0.82 | 0.84 | 1.03 | 0.58 | −0.08 | CACNG2 | −0.63 | −0.29 | 0.22 | −0.38 | 0.45 | SULT1B1 | −0.09 | −0.33 | −0.60 | −0.56 | −0.46 |
| AL137186.1 | 2.02 | −1.21 | −1.27 | −0.98 | −0.64 | RN7SL493P | −0.75 | −0.24 | −0.77 | 0.73 | −0.18 | C1orf94 | 0.19 | −0.81 | −0.85 | 0.21 | 0.17 |
| AC091153.1 | 0.90 | −0.25 | −0.01 | 0.51 | 0.33 | AL445190.1 | −0.95 | −0.54 | 1.84 | −1.29 | 1.39 | AL445604.1 | 0.45 | −0.55 | 0.33 | −0.90 | −0.22 |
| ANXA8 | 0.98 | −0.53 | −0.60 | −0.68 | 0.06 | NOL4L | −0.16 | 0.03 | 0.01 | −0.18 | −0.09 | AC005009.1 | −0.32 | −1.03 | −1.02 | −0.26 | 0.22 |
| CKM | −1.16 | 0.00 | 0.78 | 0.44 | −0.53 | HNRNPA1P16 | −0.23 | −0.62 | 0.08 | −0.15 | 0.12 | BPIFB4 | 0.19 | −0.43 | −1.02 | 0.15 | −0.07 |
| AC008267.3 | −0.75 | 0.59 | 1.24 | −0.06 | 0.34 | CASC19 | 0.15 | 0.03 | 0.09 | 0.17 | 0.26 | AC012442.3 | −0.16 | 0.08 | −0.33 | 0.82 | −0.09 |
| DISC1FP1 | −1.24 | −0.03 | 0.92 | 0.24 | 0.20 | LETM1P2 | −0.75 | −0.96 | 0.86 | 0.34 | 0.59 | AC242842.1 | 0.08 | −0.11 | −0.18 | 0.16 | 0.67 |
| E2F8 | 0.61 | −0.76 | −0.67 | −0.19 | −0.01 | AL031708.1 | −0.20 | −0.21 | −0.17 | 0.14 | 0.44 | LRPAP1 | 0.02 | 0.04 | −0.40 | 0.09 | −0.26 |
| FAM206A | 0.33 | −0.07 | −0.13 | 0.05 | 0.00 | AL390208.1 | −0.65 | 0.58 | 2.23 | 0.13 | −0.12 | ALX3 | −0.24 | 0.18 | −0.31 | 0.22 | 1.20 |
| ST8SIA6-AS1 | −1.06 | 0.80 | 0.71 | 0.50 | −0.02 | MCHR1 | 0.40 | −0.57 | −1.12 | 0.18 | 0.14 | BNIP3P9 | −0.28 | −0.60 | 0.90 | 0.11 | 0.13 |
| SMS | 0.54 | −0.56 | −0.57 | −0.29 | 0.02 | ERCC5 | −0.12 | 0.27 | 0.36 | 0.28 | 0.01 | KHNYN | −0.02 | −0.02 | −0.19 | 0.10 | −0.01 |
| IRS3P | −1.29 | 0.53 | 1.22 | 0.49 | 0.68 | CHKB-CPT1B | 0.59 | −0.55 | −0.66 | 0.06 | 0.04 | SRMS | 0.08 | 0.11 | −1.69 | 0.06 | −0.69 |
| PDE8A | 0.23 | −0.05 | −0.24 | 0.03 | −0.16 | AC124276.2 | 0.79 | −0.72 | −0.39 | −1.17 | −1.41 | AC124276.1 | 0.18 | −0.18 | 0.11 | 0.44 | 0.95 |
| GLUD1P3 | −0.44 | 0.37 | 0.22 | 0.39 | 0.15 | AC100778.3 | 0.54 | −0.19 | 0.03 | 0.23 | −0.06 | OR812 | −0.46 | −0.98 | 1.45 | −0.49 | 2.88 |
| APLP2 | 0.44 | −0.20 | −0.19 | −0.18 | −0.06 | AC137834.2 | 1.35 | 0.19 | −1.47 | 0.55 | −2.24 | AC079416.1 | −0.03 | 0.01 | 0.43 | −0.23 | −0.10 |
| AC027763.2 | −0.98 | 0.54 | 2.12 | −0.26 | 0.41 | BTF3P10 | 1.25 | −0.89 | −0.60 | −0.14 | 0.53 | KRT18P45 | 0.45 | −0.58 | 0.16 | −0.66 | 0.41 |
| AP1M2 | 0.53 | −0.03 | −0.38 | 0.03 | −0.22 | AC093281.2 | 1.38 | −2.02 | −0.87 | 0.11 | 0.22 | RPS10P16 | 0.09 | 0.43 | −0.27 | 0.52 | −0.08 |
| PPP1R36 | −0.73 | 0.24 | 0.11 | 0.21 | −0.17 | EMC9 | 0.25 | 0.09 | 0.14 | 0.15 | 0.19 | AC117834.1 | −0.08 | −0.03 | 0.61 | −0.01 | 0.22 |
| NFIC | −0.27 | 0.29 | 0.24 | 0.21 | 0.07 | RN7SL233P | 0.39 | −0.62 | 0.27 | −0.13 | 0.51 | EFNA1 | 0.03 | 0.34 | −0.19 | 0.22 | −0.28 |
| BRICD5 | −0.79 | 0.08 | 0.11 | 0.27 | 0.05 | AHCYL2 | −0.14 | 0.22 | −0.02 | 0.13 | −0.18 | AC037486.1 | −0.20 | 0.08 | 0.39 | 0.20 | −1.68 |
| CYB5R1 | 0.47 | −0.30 | −0.62 | 0.06 | −0.15 | AC087269.1 | 0.73 | −0.14 | −0.73 | 0.28 | −0.26 | AC034102.7 | 0.29 | −1.18 | −0.83 | −0.81 | 0.47 |
| C18orf54 | 0.51 | −0.40 | −0.54 | −0.38 | −0.36 | SNORD60 | −0.29 | 0.08 | 0.36 | 0.53 | −0.41 | LINC02149 | −0.22 | −0.75 | −0.50 | −0.61 | −1.59 |
| PCA3 | −0.61 | 0.15 | 0.13 | 0.02 | −0.34 | AP003467.1 | 0.34 | −0.15 | 0.44 | 0.07 | 0.56 | RPL21P23 | 0.08 | −0.35 | 0.39 | −1.07 | 0.20 |
| AGTPBP1 | 0.26 | −0.19 | −0.32 | −0.01 | −0.15 | AC008982.2 | −0.22 | 0.00 | −0.09 | 0.09 | 0.13 | AL355802.1 | −0.04 | −0.12 | 0.05 | 0.14 | 0.63 |
| AC025030.2 | 1.17 | −0.97 | −0.97 | −0.05 | 0.49 | OR4M1 | −0.69 | 0.59 | 0.37 | 0.32 | 0.77 | AP005271.1 | −0.25 | 1.33 | −0.69 | −0.72 | −2.02 |
| LINC01224 | −1.35 | 1.40 | −0.12 | 0.95 | −0.59 | LINC01389 | 0.35 | −0.57 | 0.47 | −0.32 | 0.59 | AC234782.2 | −0.26 | −1.08 | −1.48 | −0.34 | 0.89 |
| ALMS1P1 | −1.27 | 0.17 | 1.78 | 0.30 | 0.93 | RNU1-77P | 0.75 | −0.71 | −1.63 | 0.16 | −1.22 | AC239859.1 | −0.14 | −1.48 | 0.47 | −0.68 | 1.08 |
| MIS18BP1 | 0.32 | −0.16 | −0.27 | −0.05 | −0.14 | AC091814.1 | 0.51 | 0.46 | 0.28 | 0.24 | 0.41 | PRELID3BP4 | 0.75 | 0.78 | 0.56 | 0.70 | 1.59 |
| DLX4 | −0.84 | 0.93 | 0.77 | 0.71 | −0.02 | B4GAT1 | −0.19 | 0.28 | 0.35 | 0.19 | −0.04 | AC112206.4 | −0.13 | 0.03 | −0.15 | 0.32 | 1.85 |
| STRA6 | 1.37 | −0.97 | −1.35 | −0.20 | −0.53 | AB015752.1 | 0.30 | −0.05 | 0.42 | 0.38 | 0.39 | MRPL41 | −0.02 | 0.04 | −0.19 | 0.11 | −0.08 |
| CCPG1 | −0.39 | 0.36 | 0.44 | 0.08 | 0.03 | AC097103.1 | −0.40 | 0.02 | 0.54 | 0.24 | 0.42 | AL080316.1 | 0.61 | −1.01 | −0.09 | 0.24 | −1.08 |
| SNORA38B | −1.07 | 1.06 | 0.12 | 1.07 | −0.06 | AC013731.1 | −0.47 | 0.22 | 1.33 | −0.35 | 0.26 | AC010273.2 | −0.16 | 1.51 | 1.56 | 0.26 | −1.69 |
| AC103736.1 | 1.67 | −0.90 | −2.23 | 0.25 | −0.06 | RN7SL596P | −1.16 | −1.61 | 3.01 | −1.77 | 2.06 | SNX19P3 | 0.15 | −0.07 | −1.16 | −0.14 | −1.55 |
| SEH1L | 0.34 | −0.16 | −0.33 | −0.04 | −0.10 | BOLA2P2 | 0.39 | −0.74 | −0.16 | −0.33 | 0.84 | IGKV1D-8 | −0.41 | −0.20 | 2.48 | −2.71 | 1.47 |
| PKDCC | −1.08 | 0.66 | 0.88 | 0.32 | −0.18 | LINC02574 | 1.31 | 0.11 | −2.78 | 1.27 | −1.95 | CBY3 | 0.13 | −0.54 | 0.31 | 0.21 | 0.66 |
| NARF | −0.30 | 0.09 | −0.05 | 0.10 | 0.04 | AC015909.2 | −0.68 | −1.69 | −0.83 | 0.12 | 0.79 | OR8K3 | −0.34 | −1.38 | −0.53 | −0.43 | 3.13 |
| NCBP2 | 0.31 | −0.23 | −0.02 | −0.13 | 0.12 | ANPEP | 0.20 | −0.41 | −0.23 | −0.41 | 0.07 | PITPNM2-AS1 | 0.05 | −0.39 | −0.03 | −0.37 | −0.05 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| INSC | −1.19 | 0.50 | −0.07 | 0.53 | 0.14 | AC120193.1 | 0.53 | −0.14 | 0.15 | −0.04 | 0.32 | GTSE1-DT | −0.08 | −0.61 | 0.23 | −0.12 | 1.32 |
| GABPA | 0.40 | −0.15 | −0.25 | −0.07 | −0.25 | AC073508.3 | −0.40 | 0.26 | −0.43 | 0.31 | −0.70 | LINC00440 | 0.30 | 0.13 | 0.29 | 0.89 | −1.43 |
| G22682 | −1.59 | 1.36 | 1.80 | −0.35 | 0.29 | AC113139.1 | 0.73 | −0.94 | 0.66 | 0.64 | 1.38 | LINC02326 | −0.19 | 1.14 | −2.21 | 1.16 | −2.69 |
| PERM1 | −0.78 | 0.62 | 0.25 | 0.48 | −0.11 | RN7SL708P | 0.81 | 0.15 | −2.61 | 0.42 | −0.61 | AC024082.1 | −0.37 | −0.75 | 0.91 | 0.68 | 1.52 |
| AC083973.1 | 1.24 | −0.64 | −1.86 | 0.33 | −0.61 | AL157827.1 | 0.49 | −1.53 | −0.23 | −0.10 | 0.83 | AC018797.3 | 0.05 | 0.25 | 0.38 | −0.02 | −0.14 |
| SCGB1A1 | −1.31 | 0.07 | 0.56 | 0.43 | −0.05 | MYB-AS1 | 1.06 | 0.37 | 0.26 | 0.22 | −0.10 | ASAH2C | −0.10 | −0.14 | −0.61 | 0.20 | 0.58 |
| AL049840.1 | −0.50 | 0.01 | 0.35 | 0.04 | 0.33 | AL359382.1 | −0.62 | 0.90 | 0.83 | −0.05 | −0.64 | AC099786.3 | −0.22 | −1.23 | −0.89 | −1.15 | −0.72 |
| NOP56P3 | 1.34 | −0.17 | −1.20 | 0.67 | −0.82 | AL355531.2 | 0.40 | −0.28 | 0.08 | 0.23 | 0.27 | AP001189.5 | 0.09 | 0.21 | −0.24 | −0.09 | −0.72 |
| G29073 | 2.71 | 0.26 | −2.01 | 0.94 | −1.76 | IL13 | 0.68 | −1.15 | −2.08 | 0.93 | −1.06 | G26457 | −0.16 | 0.55 | −2.64 | −0.15 | −3.03 |
| AL355102.5 | 1.17 | −1.22 | −0.76 | −0.75 | 0.18 | AC012640.1 | 0.99 | −0.54 | 0.83 | −1.28 | 0.99 | RNU4-60P | 0.08 | −0.44 | −0.05 | −0.51 | 0.01 |
| NAP1L1 | 0.38 | −0.22 | −0.08 | −0.19 | −0.03 | RP11-42302.3 | 0.50 | −0.33 | 0.30 | 0.40 | 1.17 | AGAP9 | −0.06 | 0.25 | 0.10 | 0.18 | 0.06 |
| PDSS2 | 0.39 | −0.16 | −0.30 | −0.14 | −0.23 | AC093525.7 | −0.34 | 0.16 | 0.11 | 0.58 | 0.49 | NLGN2 | −0.03 | −0.13 | 0.10 | −0.19 | 0.23 |
| CSPG4 | −0.47 | 0.12 | −0.09 | −0.03 | −0.30 | CCNB2P1 | −0.43 | 0.39 | 0.02 | 0.26 | 0.02 | DLX2-DT | 0.19 | 0.06 | −0.70 | 0.64 | −0.25 |
| ANKAR | −0.39 | 0.24 | 0.39 | 0.10 | −0.02 | PLIN2 | −0.23 | 0.00 | −0.05 | 0.25 | 0.41 | AC139103.1 | 0.12 | 0.60 | 1.30 | −0.10 | 0.69 |
| PTPRC | 0.84 | −0.75 | −0.13 | −0.41 | 0.10 | RNF169 | 0.07 | 0.02 | −0.06 | −0.05 | −0.03 | MT1A | 0.16 | −0.40 | −1.03 | 0.01 | −2.13 |
| KCTD19 | −0.83 | 0.64 | 0.05 | 0.25 | 0.26 | AC027308.1 | −0.69 | −0.51 | 1.82 | −0.67 | −0.79 | MIR1301 | 0.22 | −0.18 | −0.84 | 0.63 | −1.02 |
| AL022323.2 | 0.68 | 0.14 | −0.69 | −0.16 | −0.61 | HTR1B | 0.61 | −0.82 | −0.57 | 0.22 | −0.30 | HMGA1P5 | 0.26 | −0.50 | 0.63 | −0.65 | −0.12 |
| LCA5 | −0.73 | 0.49 | 1.14 | 0.12 | 0.30 | MYLK3 | −0.40 | −0.16 | −0.15 | −0.12 | −0.30 | AC093248.1 | 0.49 | −0.31 | 0.86 | 0.87 | 1.22 |
| AC108860.1 | 0.87 | 0.21 | −0.20 | 0.05 | −0.06 | FAM238A | −0.58 | 0.34 | 0.15 | 0.55 | −0.24 | AC108059.2 | −0.28 | −0.59 | −0.28 | −0.05 | 1.63 |
| MIR3973 | 1.70 | −1.72 | −2.01 | 0.05 | −0.05 | MIR26A2 | −0.70 | 0.70 | 1.52 | 0.33 | −0.96 | AC027088.2 | 0.77 | −0.40 | −1.51 | 0.98 | −0.71 |
| NDST2 | −0.58 | 0.15 | 0.43 | 0.07 | 0.30 | AL133153.2 | 1.34 | −2.85 | 0.76 | −0.89 | 2.32 | AC020703.1 | −0.14 | 0.40 | 0.52 | 0.06 | −0.06 |
| AC022113.1 | −1.48 | 0.24 | 0.88 | −0.25 | −0.13 | RP11-435B5.6 | −0.73 | −0.72 | −2.24 | −0.23 | −1.69 | AL160314.1 | 0.27 | 0.28 | −1.50 | 1.39 | 0.27 |
| GPALPP1 | −0.26 | 0.13 | 0.25 | 0.09 | 0.08 | NPIPB15 | −0.24 | −0.22 | 0.48 | 1.45 | 1.64 | AP000439.3 | 0.22 | −1.60 | 0.88 | −0.39 | 0.24 |
| ELOVL6 | 0.55 | 0.11 | 0.35 | 0.24 | 0.07 | AL445074.1 | −0.79 | 0.62 | −0.53 | 0.46 | −1.65 | CTSW | 0.05 | −0.13 | 0.15 | −0.32 | 0.36 |
| RPS5 | 0.50 | −0.07 | −0.22 | −0.09 | −0.69 | MIR3926-2 | −1.51 | 1.80 | 1.63 | −0.12 | −1.82 | AC136601.1 | −0.11 | −0.13 | −0.24 | 0.21 | −0.62 |
| SNX20 | 1.00 | −1.02 | −0.34 | −0.48 | −0.39 | AC114808.1 | 0.75 | −0.82 | −0.80 | −0.59 | −0.01 | ALG1L5P | −0.77 | −0.13 | 0.54 | 0.21 | −0.38 |
| BNIP2 | 0.38 | −0.04 | −0.26 | −0.04 | −0.34 | AGL | 0.13 | −0.03 | −0.09 | −0.06 | −0.08 | ADH5P3 | −0.24 | −1.16 | −1.12 | 1.03 | 0.22 |
| RN7SKP23 | −0.60 | 0.19 | 0.35 | 0.20 | 0.20 | G25462 | −0.26 | −0.53 | −0.19 | −0.40 | 0.61 | AL031736.1 | 0.45 | −0.42 | 0.37 | 0.59 | −1.40 |
| NREP | 0.61 | −0.20 | −0.10 | −0.25 | −0.42 | NHLRC4 | −1.13 | 0.39 | 2.93 | −0.84 | 1.16 | AC024569.1 | 0.18 | 0.08 | −0.20 | −0.52 | 0.78 |
| LTB4R2 | 0.68 | −0.25 | −0.51 | 0.01 | −0.01 | AL031768.1 | −0.46 | −0.03 | 1.20 | −0.35 | 0.86 | AC093831.2 | 0.19 | −0.50 | −1.42 | −0.36 | −0.35 |
| MUM1 | −0.24 | 0.15 | 0.20 | 0.02 | 0.17 | RPSAP19 | 0.57 | 0.84 | −0.10 | 0.86 | −0.78 | AC007207.1 | −0.26 | −0.13 | 0.80 | −0.04 | 1.16 |
| OR7E12P | −1.04 | 0.15 | 1.03 | 0.01 | 0.02 | APOH | −0.71 | 1.32 | 0.79 | 0.48 | −1.03 | AP006545.2 | −0.28 | −0.37 | 1.18 | −0.91 | 0.05 |
| AC112242.1 | −1.19 | 0.47 | 0.44 | −0.22 | 0.84 | AC005304.2 | 0.41 | −0.62 | −0.08 | −0.89 | −0.34 | AP003774.1 | −0.13 | −0.81 | −1.05 | −0.59 | 0.84 |
| AL132780.2 | −0.64 | 0.18 | 0.32 | 0.21 | 0.42 | AC133961.1 | 0.71 | −1.08 | −1.44 | −0.14 | 0.29 | AP006333.1 | −0.16 | 1.18 | 0.66 | 1.04 | 0.80 |
| SLC37A1 | −0.50 | 0.16 | 0.34 | 0.07 | 0.16 | AC005344.1 | 0.50 | −0.22 | −1.07 | −0.52 | −1.07 | LINC01854 | −0.21 | −1.71 | −3.64 | 0.14 | −1.34 |
| CKMT1A | 0.55 | −0.09 | −0.74 | 0.16 | −0.06 | MYH4 | 0.49 | −0.54 | −0.78 | 0.12 | 0.06 | LINC02093 | 0.37 | −1.00 | −1.27 | −0.22 | −0.50 |
| GINS2 | 0.61 | −0.78 | −0.73 | −0.05 | −0.02 | C12orf66 | −0.12 | 0.14 | −0.08 | 0.18 | −0.11 | PPP1R2P6 | 0.16 | −2.18 | −1.19 | 0.61 | 1.44 |
| AL513327.1 | 0.50 | −0.49 | −0.59 | −0.31 | −0.20 | SEMA5B | −0.38 | −0.29 | 0.10 | −0.39 | −0.17 | AC015853.1 | −0.07 | −0.01 | −0.24 | 0.08 | −0.01 |
| AC027796.1 | −0.76 | 0.21 | 0.58 | 0.15 | 0.44 | AC068631.1 | −0.45 | −0.32 | −0.01 | 0.21 | −0.65 | AC106736.1 | −0.66 | −0.17 | −0.11 | 2.43 | −0.97 |
| LRIF1 | 0.53 | −0.25 | −0.08 | −0.25 | −0.03 | F2RL2 | 0.22 | −0.32 | 0.29 | −0.50 | −0.08 | AL354685.2 | −0.77 | −0.22 | 0.25 | 0.56 | −0.07 |
| RPL14P1 | 0.59 | −0.12 | −0.18 | −0.16 | −0.22 | DPY19L4P1 | −0.77 | 1.67 | −0.85 | 0.81 | −2.80 | MTND5P27 | 0.18 | −0.78 | −0.28 | 0.81 | 0.38 |
| SLC39A4 | 0.56 | −0.45 | −0.47 | −0.32 | −0.36 | SNN | 0.15 | 0.04 | −0.37 | 0.10 | −0.47 | OR8B1P | 0.40 | −1.47 | 0.39 | 0.08 | 3.21 |
| RNA5SP304 | 1.68 | −0.17 | −1.25 | −0.37 | −1.28 | AC126389.1 | 0.26 | 0.24 | 0.17 | 0.07 | −0.06 | AL359921.2 | −0.06 | 0.25 | 0.15 | 0.20 | −0.06 |
| CPNE3 | 0.35 | −0.09 | −0.20 | −0.04 | −0.20 | AL391704.2 | 0.84 | −0.09 | −3.19 | 1.05 | −2.25 | AL391294.1 | 0.12 | −1.82 | −1.06 | 0.58 | 0.14 |
| INPPL1 | −0.49 | 0.05 | 0.05 | 0.20 | 0.25 | HOXC13 | 0.26 | 0.33 | −0.11 | 0.14 | −0.25 | AC023394.2 | −0.29 | −0.79 | 0.85 | 1.06 | 1.35 |
| AC097063.1 | −1.12 | 0.04 | 1.01 | 0.50 | 0.42 | OPN1SW | 0.21 | −0.46 | −0.24 | −0.26 | −0.19 | AC020743.2 | 0.30 | −0.48 | 0.69 | −0.41 | −0.81 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AL360007.1 | −2.05 | 0.48 | −1.38 | 1.19 | −1.19 | GPR52 | 0.32 | −0.10 | −0.01 | −0.19 | 0.18 | RN7SL569P | 0.22 | −0.69 | 0.43 | −0.25 | 0.85 |
| DDHD2 | −0.27 | 0.15 | 0.03 | 0.11 | 0.02 | G6796 | −0.29 | 0.38 | 0.52 | −0.39 | −0.68 | SLC39A12-AS1 | −0.25 | 0.45 | −0.07 | 0.99 | −0.37 |
| LINC01481 | −0.56 | 0.29 | 0.88 | 0.32 | 0.53 | AC103855.3 | 1.34 | −0.70 | −0.44 | 1.02 | 1.75 | MIR608 | −0.53 | 2.19 | 2.65 | 1.12 | −0.37 |
| AC011476.3 | −0.59 | 0.13 | 0.49 | −0.02 | 0.14 | ANKRD62P1 | −0.92 | 0.98 | 0.86 | −0.43 | −0.39 | MIR574 | 0.13 | 0.16 | −0.50 | −0.86 | −1.40 |
| RPL23AP82 | −0.44 | 0.19 | 0.62 | −0.06 | 0.22 | AC090617.6 | 0.67 | −0.06 | 0.39 | −0.21 | −0.54 | LGALS17A | 0.17 | 0.22 | −1.20 | −0.91 | −1.52 |
| INHBA | 0.95 | −0.58 | −0.45 | −0.90 | −0.57 | NPAP1P4 | 0.72 | −1.59 | −1.71 | −0.31 | −1.12 | CTSO | −0.04 | 0.16 | 0.43 | −0.08 | 0.03 |
| AFG1L | 0.40 | −0.20 | −0.11 | −0.21 | −0.09 | AC011912.1 | −0.24 | 0.16 | 0.07 | 0.10 | 0.11 | AC092809.3 | 0.19 | −1.18 | −0.54 | −0.01 | −0.49 |
| AC096720.2 | 0.91 | −0.77 | −1.33 | 0.35 | −0.14 | RPL26P37 | 0.72 | −0.66 | 0.69 | 0.02 | −0.71 | LINC02026 | −0.10 | 0.21 | −0.42 | −0.36 | −0.60 |
| RPS20P15 | 1.16 | 0.12 | −0.70 | 0.12 | 0.00 | MTCO1P19 | 0.38 | −0.02 | 0.07 | 0.17 | −0.06 | AC131097.2 | −0.08 | 0.06 | 0.03 | 0.23 | −0.11 |
| ITSN1 | −0.56 | 0.14 | 0.28 | −0.05 | −0.01 | ALG14 | 0.15 | −0.28 | −0.27 | 0.01 | 0.17 | CENPVL3 | −0.24 | −1.04 | −2.42 | 0.84 | 0.21 |
| DHTKD1 | 0.29 | −0.22 | −0.31 | −0.01 | −0.07 | AC022613.2 | 0.41 | −0.12 | −0.15 | −0.04 | −0.03 | AL645939.5 | −0.11 | 0.58 | 0.04 | 0.59 | 0.47 |
| CPEB1-AS1 | −1.01 | 0.29 | 0.38 | 1.01 | 0.97 | AC073592.2 | 1.28 | −1.51 | −1.69 | 0.42 | −0.18 | AL391069.4 | −0.18 | −0.34 | −1.18 | 0.04 | −0.27 |
| CELF2 | −0.58 | 0.43 | 0.49 | −0.03 | 0.01 | AC010186.2 | −0.24 | 0.40 | 0.16 | 0.20 | 0.08 | LINC01829 | −0.12 | 0.24 | 0.47 | 0.43 | 0.03 |
| PSMD5 | 0.33 | −0.14 | −0.19 | −0.16 | −0.17 | AL049648.1 | −1.48 | −0.81 | 1.49 | 0.34 | 0.91 | AC005180.2 | 0.07 | −0.19 | −0.93 | 0.08 | −0.96 |
| HK1 | 0.32 | −0.12 | −0.39 | −0.02 | −0.18 | DKFZP434A062 | 0.59 | 0.02 | −1.31 | −0.53 | −2.09 | LINC01886 | −0.16 | 0.27 | −1.20 | 0.30 | −0.58 |
| RAET1G | 0.71 | −0.39 | −0.89 | 0.09 | −0.35 | AC005822.1 | −0.23 | 0.08 | −0.19 | −0.08 | −0.15 | DLGAP4-AS1 | −0.04 | 0.02 | 0.43 | −0.31 | 0.04 |
| MIR16-2 | 2.69 | −0.97 | −0.32 | −0.88 | 0.16 | SPZ1 | −0.93 | −0.96 | −0.51 | 0.09 | −1.56 | RPS24P7 | 0.26 | 0.11 | −1.34 | 0.45 | −1.40 |
| CD177 | 1.53 | −2.21 | −2.38 | −0.90 | −0.21 | RNU6-908P | 1.04 | −0.31 | −0.74 | 0.22 | −1.60 | SLC6A8 | 0.04 | −0.06 | −0.40 | 0.23 | 0.11 |
| CNIH4 | 0.41 | −0.11 | −0.12 | −0.07 | −0.28 | AC079610.2 | 0.49 | 0.10 | 1.06 | −0.20 | 0.56 | G30143 | −0.16 | 0.37 | −1.53 | 1.46 | −0.66 |
| SNED1 | −0.68 | 0.48 | 0.63 | 0.22 | 0.22 | GPR26 | −0.49 | −0.26 | 0.44 | −0.29 | 0.22 | AP001160.3 | −0.19 | −0.59 | 2.64 | −0.75 | 1.24 |
| PRELID1P4 | −0.88 | 0.59 | 0.86 | 0.54 | 0.08 | LINC02160 | 0.56 | 0.19 | −0.79 | 0.33 | 0.01 | AC036101.1 | −0.54 | −0.56 | −1.18 | −0.70 | −1.56 |
| C11orf42 | −0.91 | 0.85 | −0.25 | 0.57 | −0.38 | RNU6-693P | 1.05 | −1.10 | −1.60 | −0.76 | −1.23 | SMCR5 | −0.05 | 0.12 | −0.22 | 0.07 | −0.06 |
| DCUN1D1 | 0.40 | −0.08 | −0.24 | 0.00 | −0.22 | EEF1A1P8 | −0.71 | 1.25 | 0.01 | 0.17 | 0.45 | RN7SKP170 | −0.29 | −0.80 | 0.66 | 0.55 | 0.11 |
| NOP53-AS1 | −1.14 | 0.66 | 0.16 | 0.56 | −0.11 | AC096920.1 | 0.67 | −1.40 | −0.05 | −0.21 | 1.35 | FNDC3B | 0.03 | −0.12 | −0.06 | −0.27 | −0.12 |
| RNA5SP371 | 1.75 | −1.09 | −1.58 | −1.30 | −1.54 | CRX | −0.49 | −0.98 | −0.02 | 0.06 | 0.88 | AP000997.3 | 0.15 | −0.67 | −0.94 | 0.66 | −0.77 |
| AP003049.2 | −1.34 | 0.45 | 0.69 | 0.07 | 0.37 | CRISP3 | −0.46 | 1.07 | 1.37 | 0.10 | −0.43 | RPSAP4 | 0.23 | −0.81 | 0.56 | −0.38 | −0.65 |
| MAPK3 | 0.34 | −0.06 | −0.42 | 0.09 | −0.36 | AC012669.1 | −1.12 | −0.21 | 1.01 | −1.13 | 0.24 | G7721 | −0.22 | 1.25 | −1.75 | 2.73 | −1.14 |
| LINC00696 | −0.97 | −0.08 | 0.41 | 0.11 | 0.67 | MRTFA-AS1 | 0.19 | −0.12 | −0.05 | −0.08 | −0.17 | KIF21A | −0.03 | 0.23 | 0.09 | 0.00 | −0.10 |
| AC007557.2 | −1.32 | 0.91 | 0.62 | 0.66 | 0.15 | MIR3177 | 0.72 | −0.45 | −0.68 | −0.86 | −0.17 | AC006509.1 | −0.20 | −2.05 | 0.39 | 0.18 | 0.70 |
| PEG13 | −0.55 | 0.03 | 0.20 | 0.02 | 0.48 | AL354809.1 | −0.54 | −0.02 | −0.26 | 0.73 | 0.54 | AC025871.1 | −0.27 | −0.43 | 1.36 | −0.45 | 2.61 |
| LINC02519 | −1.29 | 0.53 | 2.01 | −0.04 | 0.46 | GRID2 | −0.53 | 0.02 | 0.10 | 0.68 | 0.17 | RNVU1-19 | 0.10 | −0.43 | −0.99 | −1.09 | 0.07 |
| AC022874.1 | 2.26 | −1.31 | −2.13 | 0.49 | −0.12 | ACBD7 | −0.39 | −0.10 | 0.07 | −0.27 | −0.21 | PSMC1P13 | 0.38 | 0.44 | −1.46 | 0.28 | −0.67 |
| DIRC2 | 0.57 | −0.03 | −0.44 | 0.24 | −0.26 | RNU6-319P | 0.61 | −0.57 | 0.49 | −0.33 | 0.81 | AP001267.5 | 0.11 | −0.61 | −0.91 | 0.04 | −0.54 |
| RASL11A | −0.58 | 0.39 | 0.92 | 0.04 | 0.03 | RN7SL758P | −0.45 | −0.77 | 0.14 | −0.56 | 0.68 | RNU7-191P | 0.12 | −0.10 | 0.94 | −0.04 | 0.89 |
| FBXO24 | −0.74 | 0.66 | 0.74 | 0.14 | 0.26 | AL358777.1 | −0.27 | −0.48 | −0.29 | 0.11 | 0.17 | AC005520.5 | −0.11 | 0.72 | 0.38 | 0.83 | 0.97 |
| ALDH1L2 | 0.48 | −0.10 | −0.10 | −0.35 | −0.34 | SPIN2B | −0.18 | 0.07 | 0.55 | −0.07 | 0.16 | CAMKK2 | −0.02 | 0.00 | −0.13 | −0.02 | −0.16 |
| AC074051.4 | −1.80 | −1.38 | −0.22 | −0.54 | 0.61 | AC079684.1 | 0.37 | −0.57 | −0.80 | −0.07 | 0.29 | AC147651.3 | 0.08 | −0.41 | −0.45 | −0.08 | −0.25 |
| HRH3 | 1.57 | 0.12 | −0.72 | −0.29 | −0.77 | AC096644.4 | 0.63 | −1.67 | −1.82 | −0.28 | −0.39 | AC092718.5 | −0.08 | −0.23 | 0.25 | 0.18 | 0.06 |
| STAG2 | 0.34 | 0.05 | −0.22 | 0.05 | −0.31 | AKAP14 | −0.62 | −0.23 | −0.63 | 0.86 | 1.56 | NIFKP3 | −0.24 | −1.14 | 0.86 | −1.08 | 1.83 |
| AL049757.1 | −1.33 | 0.12 | 0.50 | −0.21 | 0.69 | AC010731.3 | 1.29 | −0.03 | −2.75 | 0.66 | −0.48 | AL359552.1 | −0.43 | −0.36 | −0.91 | 0.98 | 1.19 |
| CNP | 0.36 | −0.24 | −0.53 | 0.06 | −0.14 | MAP4K1 | −0.28 | −0.39 | 0.41 | −0.31 | 0.42 | KCNH5 | 0.10 | −0.49 | −0.22 | −0.05 | −0.41 |
| PHC3 | −0.19 | 0.14 | 0.14 | 0.02 | 0.00 | NAA80 | −0.20 | 0.21 | −0.21 | 0.31 | 0.11 | AC010528.1 | −0.32 | −1.74 | −0.02 | −1.11 | −0.86 |
| MUC7 | −1.41 | 1.62 | 2.26 | −0.37 | 0.32 | AP001858.1 | −0.73 | 0.36 | −0.21 | −0.95 | −1.59 | RNU7-154P | 0.18 | −1.15 | −0.19 | −0.39 | 1.43 |
| DNAJC19P8 | 1.64 | −0.35 | −1.50 | −0.44 | −0.66 | CRYBB2 | 0.57 | −0.02 | −0.63 | 0.31 | 0.26 | RAD21-AS1 | −0.11 | −0.46 | 2.12 | −0.49 | 1.19 |
| MMP24OS | −0.33 | 0.34 | 0.18 | 0.18 | −0.17 | RNU6-2 | 0.36 | −0.19 | −0.39 | 0.15 | 0.09 | AC107208.1 | −0.34 | 0.06 | −1.49 | 1.28 | −0.31 |
| AL355001.1 | −1.09 | −0.17 | 0.10 | 0.22 | 0.23 | SLC5A4-AS1 | 0.80 | 0.96 | −1.61 | 1.17 | −2.27 | AC060788.1 | 0.76 | 0.43 | −1.91 | −0.85 | −1.68 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| RNY1 | −0.92 | 1.09 | 1.17 | 0.67 | −0.53 | GEMIN8 | −0.12 | 0.04 | 0.16 | 0.21 | 0.19 | ACTR3BP3 | 0.35 | −0.81 | −0.66 | 2.04 | 2.08 |
| AC008610.1 | −1.04 | 0.04 | 1.31 | 0.21 | 0.85 | ITGB3 | −0.33 | 0.01 | 0.50 | −0.45 | −0.38 | DNAJB1P1 | 0.15 | −1.92 | 1.63 | −0.60 | 1.13 |
| AC064801.2 | −0.59 | 0.31 | 0.52 | −0.01 | 0.42 | MTCYBP28 | 0.48 | −1.32 | −0.57 | −0.62 | 0.31 | OXCT2 | 0.11 | 0.21 | −0.27 | 0.28 | 0.17 |
| AC020900.1 | 1.34 | −0.14 | −0.83 | 0.02 | −0.99 | AC089998.3 | 0.32 | 0.62 | −0.29 | −0.22 | −0.64 | AC104073.3 | −0.60 | 0.16 | −0.23 | 0.96 | 0.88 |
| HS6ST1 | 0.36 | −0.06 | −0.22 | −0.02 | −0.05 | KCNQ5 | 0.42 | −0.09 | −0.62 | −0.12 | −0.01 | AC006518.2 | 0.07 | 0.33 | 0.60 | 0.16 | 0.10 |
| CKMT1B | 0.53 | −0.19 | −0.75 | 0.31 | 0.01 | AP002414.4 | −0.68 | 0.25 | −0.76 | 0.75 | −0.53 | AC008725.1 | 0.08 | 0.08 | −0.55 | 0.27 | −0.52 |
| PRKCZ–AS1 | −0.88 | 0.23 | 0.44 | −0.07 | 0.24 | ANO7L1 | −0.28 | 0.30 | 0.15 | 0.29 | −0.12 | AL606760.4 | 0.36 | −0.53 | 0.12 | −0.27 | 0.57 |
| PTGDR | −0.96 | 0.03 | 1.60 | −0.12 | 0.69 | AP002768.1 | −0.41 | −0.26 | −0.19 | 0.13 | 0.34 | AL133268.3 | −0.39 | −2.35 | −0.07 | −1.52 | 0.51 |
| AC241952.1 | −0.85 | 0.06 | 0.56 | 0.26 | 0.06 | LOXL3 | −0.17 | −0.34 | −0.08 | −0.13 | 0.17 | RRM2P4 | 0.61 | −0.50 | 1.97 | 0.85 | 3.46 |
| LINC02076 | −1.04 | −0.77 | 0.14 | 0.32 | 1.14 | AC084033.1 | −0.93 | 1.62 | 1.14 | 0.05 | −0.21 | AC013733.1 | −0.68 | 0.11 | −0.91 | −0.19 | −0.81 |
| PRKAR1AP1 | −1.04 | 0.84 | 1.00 | 0.06 | 0.46 | AC139453.2 | −0.95 | 0.94 | 1.74 | 0.38 | 1.04 | ITGA10 | −0.04 | 0.04 | 0.20 | −0.07 | −0.01 |
| EXOC2 | 0.24 | −0.22 | −0.40 | −0.11 | −0.22 | RNU6-152P | −0.86 | −1.06 | −0.93 | 0.78 | −0.09 | AC024575.1 | −0.15 | 0.46 | 1.75 | −0.77 | −0.69 |
| AC004584.3 | −0.77 | 0.60 | 1.76 | 0.36 | 0.37 | AL355472.2 | 0.81 | 0.28 | −0.41 | 0.05 | 0.27 | AL355339.1 | −0.46 | 1.46 | 0.03 | 0.42 | −0.06 |
| AC093642.2 | −0.93 | 0.51 | 0.85 | 0.33 | 0.65 | RNU6-1062P | 0.63 | −0.07 | 0.19 | −0.38 | −1.17 | LINC01019 | 0.29 | −0.75 | −0.89 | −0.39 | 0.58 |
| AC092123.1 | −0.65 | −0.10 | 0.78 | 0.12 | 0.76 | LINC01962 | 1.11 | −0.03 | 1.40 | −0.14 | 0.96 | LINC01995 | 0.14 | 0.27 | −1.14 | 0.43 | −1.31 |
| NXPE2 | −1.20 | −0.97 | 0.47 | −0.22 | 0.81 | AC024600.1 | −1.04 | −1.08 | 0.40 | −0.71 | 0.81 | KLF3P1 | −0.05 | 0.11 | −0.36 | 0.23 | −0.29 |
| MID1IP1 | 0.44 | −0.40 | −0.35 | −0.13 | −0.28 | SCN1B | −0.30 | −0.28 | 0.60 | −0.61 | −0.14 | RN7SL619P | −0.12 | −0.83 | 0.89 | −0.28 | 0.87 |
| IKBIP | 0.56 | −0.63 | −0.06 | −0.68 | 0.19 | RNU1-14P | −1.61 | 0.81 | −0.24 | 2.28 | 0.48 | RNU6-9 | −0.09 | 0.54 | 0.52 | 0.09 | 0.43 |
| GDF7 | −0.68 | 0.60 | 1.11 | 0.23 | 0.11 | AC244093.3 | 0.29 | −0.22 | 0.03 | −0.09 | 0.09 | RN7SL270P | −0.13 | −1.80 | 0.28 | −0.33 | −0.03 |
| SNRPA | 0.39 | −0.31 | −0.62 | 0.03 | 0.01 | DYNLRB2 | −0.30 | −0.60 | 0.46 | 0.12 | 0.96 | CACNA1C | 0.04 | −0.15 | 0.11 | −0.50 | −0.33 |
| CDKN2A | 0.86 | −0.31 | −0.31 | −0.04 | 0.17 | AC114801.3 | −0.77 | 1.26 | 0.11 | 1.23 | −1.09 | RNU7-105P | −0.20 | 0.94 | −0.07 | 0.87 | 0.87 |
| MCEMP1 | 2.08 | −1.01 | −2.83 | 0.14 | −1.83 | RN7SL285P | 0.51 | −1.01 | 0.66 | −0.18 | 1.00 | RN7SL172P | 0.19 | −0.79 | 1.09 | 0.12 | 1.74 |
| IMP3 | 0.65 | −0.15 | −0.65 | 0.21 | −0.27 | KCNC2 | −0.72 | 0.09 | −0.58 | −0.31 | 0.00 | AC138627.2 | −0.76 | −0.10 | 0.29 | −0.37 | 0.27 |
| CNTF | 0.88 | −0.46 | −0.91 | 0.04 | −0.55 | NMNAT1P4 | −1.26 | 1.16 | −1.92 | −0.03 | −3.38 | AL390964.1 | −0.18 | −0.57 | −0.69 | 0.19 | −0.67 |
| FMO2 | −1.20 | 0.88 | 0.97 | 0.95 | −0.50 | P4HA2 | 0.12 | 0.06 | −0.02 | −0.17 | −0.19 | BMS1P5 | 0.03 | 0.02 | 0.00 | −0.03 | 0.11 |
| DCP2 | 0.38 | −0.17 | −0.11 | −0.15 | −0.05 | AL596247.1 | 0.34 | −0.55 | −0.51 | −0.32 | 0.71 | OR52E6 | −0.30 | −0.76 | −0.10 | −0.37 | 1.29 |
| PFDN6 | 0.38 | −0.22 | −0.27 | −0.03 | −0.04 | SNHG21 | −0.27 | 0.45 | −0.07 | 0.48 | −0.26 | AC080013.5 | 0.15 | 0.27 | −0.24 | 0.29 | −0.74 |
| AC024940.3 | 0.85 | −0.28 | 0.45 | −0.45 | 0.44 | BCORP1 | −0.48 | 0.50 | 0.61 | −0.15 | 0.00 | AC087071.1 | −0.17 | −0.53 | 1.86 | −1.60 | −0.26 |
| NDUFA4 | 0.46 | −0.24 | −0.13 | −0.31 | −0.32 | AC005546.1 | −0.28 | −0.24 | −0.49 | −0.20 | −0.45 | AC090774.2 | −0.55 | 0.22 | 0.11 | −0.32 | 0.35 |
| AL365356.4 | 1.65 | −1.48 | −1.11 | −1.39 | −0.09 | MIR1289-2 | 1.10 | −0.03 | −2.42 | −0.16 | −2.14 | AC005412.1 | 0.28 | −1.09 | −1.69 | 0.65 | −1.52 |
| PDE6C | −0.60 | 0.33 | −0.05 | 0.23 | −0.04 | G16026 | −0.33 | 0.23 | 0.10 | −0.15 | −0.27 | LINC01396 | 0.32 | −1.28 | 2.40 | 0.54 | 0.74 |
| AC092546.1 | −1.11 | 0.29 | −0.58 | 0.25 | −0.19 | HNRNPA3P14 | 1.03 | 0.43 | −2.47 | 0.28 | −2.02 | ATG16L1 | 0.02 | −0.04 | −0.09 | 0.01 | 0.10 |
| RBMX | 0.29 | −0.20 | −0.16 | −0.08 | 0.06 | AC008686.1 | −0.51 | −0.49 | 0.52 | −0.68 | 0.06 | MIR3944 | 0.18 | −1.12 | 1.64 | 0.43 | 2.61 |
| PPP1R16A | −0.51 | 0.48 | 0.09 | 0.53 | 0.00 | FKRP | 0.13 | −0.10 | −0.19 | 0.01 | 0.11 | RNU6-969P | −0.09 | −0.07 | 0.45 | −0.38 | −0.02 |
| AL136985.3 | −0.71 | 0.07 | −0.39 | 0.06 | −0.22 | NBPF2P | −0.32 | −0.24 | 0.33 | 0.59 | 0.75 | OR2L13 | −0.20 | −1.25 | 1.35 | 0.84 | 0.83 |
| PIP5K1P1 | −1.14 | 0.16 | 1.48 | −0.18 | −0.13 | AC011297.1 | −0.72 | 0.20 | 0.41 | −0.20 | 0.33 | AC068620.3 | 0.04 | −0.16 | 0.10 | 0.03 | 0.21 |
| E4F1 | −0.45 | 0.24 | −0.04 | 0.27 | 0.02 | AL157955.2 | 0.56 | −1.69 | −2.35 | 0.21 | 0.07 | AC004241.4 | −0.09 | 0.21 | 0.18 | −0.14 | 0.39 |
| AL356275.2 | −1.04 | 0.15 | 1.72 | −0.12 | 0.34 | POLL | −0.12 | 0.00 | 0.05 | 0.08 | 0.15 | CHKB | −0.05 | −0.05 | 0.08 | 0.03 | 0.06 |
| CASP12 | −1.10 | 0.79 | 1.84 | 0.57 | 1.42 | AL132994.2 | −1.21 | −0.40 | −0.07 | 0.20 | −0.52 | RNU1-46P | 0.24 | −0.45 | −1.90 | 0.62 | −1.40 |
| RNASE7 | 1.04 | −0.64 | −0.43 | −0.04 | −0.59 | AC104164.2 | −0.48 | 0.80 | 0.59 | −0.19 | 0.59 | AC022217.1 | −0.18 | 0.66 | −0.18 | −0.83 | −0.33 |
| AC023421.2 | −1.20 | 0.04 | 0.57 | 0.15 | 1.47 | LILRB4 | 0.41 | −0.82 | −0.90 | −0.48 | −0.90 | FAR1P1 | −0.31 | −1.08 | −0.60 | −0.02 | 0.31 |
| RPL22 | 0.37 | −0.24 | −0.22 | −0.12 | 0.01 | MIR642A | 0.91 | 1.63 | 0.59 | 0.12 | −0.23 | RNU6-722P | 0.46 | −0.18 | −1.50 | 2.01 | −1.31 |
| RNU7-181P | 1.78 | −1.20 | −1.93 | −0.15 | −0.24 | BANF1P4 | 0.48 | 0.46 | −0.65 | 0.12 | −0.01 | JRKL | 0.02 | −0.09 | 0.15 | −0.28 | 0.11 |
| MARCO | −1.18 | 0.36 | 0.41 | 0.72 | −0.72 | LINC02465 | 0.82 | −0.65 | −1.44 | 0.02 | −1.11 | OAZ3 | 0.07 | −0.18 | −1.12 | 0.07 | −0.33 |
| G35511 | 1.06 | −0.51 | −1.33 | 0.14 | −0.94 | NUDT4 | 0.12 | 0.03 | −0.03 | 0.07 | −0.08 | SHROOM4 | −0.04 | −0.02 | 0.60 | −0.27 | 0.07 |
| CAPNS1 | 0.53 | −0.39 | −0.56 | −0.18 | −0.15 | AL049697.3 | −0.97 | −0.05 | −0.36 | 1.25 | 0.09 | S1PR2 | −0.03 | −0.10 | 0.24 | −0.16 | −0.07 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AL354977.2 | −0.79 | −0.18 | 1.04 | −0.21 | 0.55 | AL121834.1 | 0.43 | −0.30 | −0.50 | −0.04 | −0.03 | RNA5SP183 | −0.23 | −1.50 | 0.99 | 0.72 | −1.34 |
| NDUFS5P1 | 1.31 | −0.03 | −0.85 | −0.09 | −0.31 | RNU6-1027P | 1.02 | 0.50 | −1.37 | 1.89 | −0.53 | RP11-216M21.7 | −0.26 | −0.47 | −0.17 | 0.64 | 0.59 |
| DCAKD | −0.42 | 0.11 | 0.29 | 0.21 | 0.49 | MIR4505 | −0.37 | −0.29 | −0.03 | −0.25 | 0.17 | PABPC1P6 | −0.27 | 0.00 | 1.21 | 1.07 | 0.93 |
| GPR35 | −0.83 | 0.08 | 0.35 | 0.13 | 0.08 | CYP51A1P2 | 0.50 | −0.96 | −0.76 | −0.34 | −0.39 | AL353072.2 | −0.23 | −2.65 | 2.43 | −1.26 | 1.07 |
| PNRC2 | 0.35 | −0.20 | −0.33 | −0.14 | −0.27 | G21027 | −0.26 | 0.28 | 0.75 | −0.01 | 0.67 | AL954650.1 | 0.29 | 0.34 | 0.72 | −0.31 | 0.07 |
| AC092611.3 | 0.91 | 0.13 | −0.60 | 0.18 | −0.79 | MIR3619 | 0.39 | 0.09 | −0.51 | 0.21 | −0.41 | AC025031.1 | 0.10 | −1.86 | −0.73 | −0.09 | 0.23 |
| AC146507.2 | 0.86 | −0.43 | −0.48 | 0.05 | 0.40 | AL109923.1 | 0.45 | −0.06 | 0.07 | 0.01 | −0.25 | AC087501.3 | −0.10 | −0.05 | −0.91 | −0.12 | −0.21 |
| STAT5A | −0.52 | 0.04 | 0.09 | −0.01 | 0.13 | RN7SL689P | −0.39 | −0.05 | 0.33 | −0.07 | 0.04 | AC068299.1 | 0.20 | −0.68 | −0.98 | −0.94 | 0.21 |
| AC139795.2 | −0.53 | 0.44 | 0.62 | 0.24 | 0.17 | AC092125.1 | −0.62 | 0.55 | −0.19 | 0.65 | −0.31 | HNRNPCP4 | 0.10 | −0.59 | 0.11 | −0.67 | 0.66 |
| CHMP1A | 0.31 | −0.18 | −0.44 | 0.05 | −0.14 | LINC02572 | −0.53 | −0.27 | 0.19 | −0.11 | −0.22 | AC115990.1 | −0.16 | 0.61 | −2.07 | 0.36 | −2.03 |
| MMP13 | 0.98 | −0.83 | −0.91 | −1.15 | −0.81 | MEIS1-AS2 | −0.46 | 0.77 | 0.74 | 0.01 | −0.23 | SLC25A6P4 | −0.12 | 0.17 | 1.30 | 0.23 | 1.07 |
| AC090844.2 | −1.50 | 1.34 | 1.92 | 0.35 | 0.53 | HMGN1P14 | 0.77 | 0.39 | 1.19 | −1.05 | −0.06 | AC015600.1 | −0.39 | −0.19 | 1.29 | −0.82 | 0.31 |
| SCN5A | −0.99 | 0.67 | 0.58 | 0.48 | −0.12 | AP005660.1 | 0.86 | 0.21 | −0.24 | 0.48 | −0.54 | AC090572.2 | −0.26 | −0.62 | −1.15 | 0.80 | 0.54 |
| AL355482.1 | −1.67 | 0.36 | 0.73 | 0.29 | 0.65 | AC109460.1 | 0.33 | 0.14 | 0.34 | 0.46 | 0.07 | CTXND2 | −0.26 | 0.15 | 0.20 | 0.41 | −0.01 |
| MRPL21 | 0.38 | −0.09 | −0.55 | −0.04 | −0.43 | IRF5 | −0.14 | −0.03 | 0.05 | −0.05 | −0.05 | RPL31P11 | −0.10 | −0.39 | −0.88 | 0.40 | 0.46 |
| SIRT1 | −0.30 | 0.29 | 0.49 | 0.01 | 0.05 | HOXC-AS2 | −0.22 | 0.26 | −0.01 | 0.12 | 0.11 | AL356596.1 | 0.76 | −0.37 | −1.57 | 0.44 | −1.00 |
| SBNO2 | 0.56 | −0.78 | −1.12 | −0.12 | −0.03 | AC105265.4 | 1.05 | −1.10 | −0.01 | −0.71 | 0.07 | AP002360.1 | −0.05 | −0.19 | 0.41 | −0.32 | 0.45 |
| NUP160 | 0.28 | −0.20 | −0.18 | −0.10 | −0.09 | MIR3130-1 | 1.20 | 1.05 | −0.99 | 0.76 | −0.70 | LINC01741 | −0.22 | −0.78 | −2.78 | 1.56 | 0.28 |
| AC244093.2 | 1.19 | −0.30 | −0.46 | 0.13 | −0.24 | AC005300.1 | −0.92 | −0.91 | 0.95 | −0.32 | 0.33 | HLX−AS1 | −0.20 | −2.11 | −0.31 | 0.03 | 1.29 |
| CCDC24 | −0.89 | 1.00 | 0.76 | 0.56 | 0.07 | SCN8A | −0.25 | −0.45 | −0.11 | 0.14 | 0.39 | AL445487.1 | −0.13 | −0.09 | −1.36 | −0.66 | −0.55 |
| KRTAP11-1 | −2.09 | 1.51 | 1.38 | 0.00 | 1.10 | RNY5P5 | −0.65 | 0.38 | 1.54 | −0.04 | −0.55 | AC074099.1 | 0.23 | −1.96 | −0.80 | −0.51 | 0.37 |
| AL356481.1 | −0.62 | 0.19 | 0.88 | −0.21 | −0.06 | RN7SL331P | 0.78 | −0.51 | 0.84 | −0.46 | 1.23 | AL161645.2 | 0.18 | 0.06 | 0.31 | 0.21 | 0.57 |
| PTPN9 | 0.27 | −0.11 | −0.06 | −0.19 | −0.09 | AL356488.3 | 0.26 | −0.32 | −0.74 | −0.08 | −0.16 | AC131235.4 | 0.26 | −0.89 | 1.38 | −0.64 | −0.05 |
| HECTD3 | −0.30 | 0.15 | 0.01 | 0.25 | 0.07 | RFX8 | 0.29 | −0.66 | −0.32 | −0.54 | 0.10 | RNU6-882P | 0.10 | 0.10 | 1.32 | −0.58 | 0.83 |
| AC007540.1 | 2.09 | −0.27 | −0.54 | −0.47 | −0.03 | MAPRE1P1 | −0.46 | 0.68 | −1.19 | 0.28 | −1.22 | AP005139.1 | 0.39 | 0.19 | −1.64 | 0.11 | −2.20 |
| RPS3AP38 | 0.60 | −0.31 | −0.01 | −0.23 | 0.20 | MIR3685 | 0.60 | −0.08 | −0.20 | 0.03 | 0.35 | LINC02179 | −0.21 | −0.23 | −0.20 | 0.29 | 0.52 |
| ICOS | 1.56 | −1.56 | −0.80 | −0.94 | −0.12 | OR7E28P | −1.08 | 2.37 | 2.61 | −1.07 | 0.20 | OR12D2 | 0.25 | 0.24 | −1.27 | 0.47 | −0.18 |
| DCAF12 | 0.43 | −0.08 | −0.39 | −0.02 | −0.51 | AC109597.2 | 0.33 | 0.30 | −0.23 | 0.12 | −0.24 | AC010149.2 | 0.75 | −0.67 | 0.00 | −1.86 | −0.91 |
| AC011247.1 | −1.14 | 0.56 | 0.97 | 0.89 | 0.96 | AP000936.3 | 0.30 | −0.47 | −0.54 | −0.29 | 0.25 | OR7A15P | −0.75 | −0.40 | −1.22 | 1.65 | −0.35 |
| LCP2 | 0.90 | −1.19 | −0.69 | −0.22 | 0.06 | MRPL50P2 | −0.50 | 0.53 | 0.52 | 0.11 | −0.26 | AC005099.1 | −0.09 | 0.17 | 0.66 | −0.44 | −0.27 |
| AP006222.2 | −0.72 | 0.44 | 0.68 | −0.09 | 0.23 | SLURP1 | 0.40 | 0.55 | 0.35 | 1.55 | −0.97 | AC092580.3 | 0.51 | −1.15 | 0.51 | −0.92 | −1.91 |
| SNAP23 | 0.31 | −0.15 | −0.07 | −0.15 | −0.12 | G16199 | −0.47 | 0.82 | −0.39 | 0.93 | 0.79 | AC106897.1 | −0.25 | 0.27 | 0.74 | −1.11 | −0.70 |
| FAM3B | −1.08 | 0.21 | 0.43 | 0.22 | 0.80 | CORO1A | 0.25 | −0.66 | 0.00 | −0.31 | 0.07 | BRD7P5 | −0.09 | 0.20 | −1.03 | 0.85 | −0.18 |
| AC006064.5 | −0.49 | 0.35 | 0.70 | 0.04 | 0.10 | PCED1CP | −0.99 | −0.77 | 0.44 | 0.32 | 0.23 | AP005264.1 | −0.21 | 1.54 | −0.20 | 0.88 | −1.52 |
| AL356740.1 | −1.60 | 1.49 | 1.84 | −0.93 | 0.88 | FAM66E | −0.76 | −0.15 | 1.87 | −1.54 | 0.53 | LRCH1 | −0.02 | 0.23 | 0.24 | 0.01 | −0.13 |
| COX6B2 | −0.81 | 0.41 | 0.16 | 0.53 | 0.82 | AC115099.1 | 1.15 | 0.23 | −3.08 | 0.16 | −2.30 | OR52E1 | 0.46 | −0.29 | −0.86 | 1.95 | −1.06 |
| JDP2 | −0.46 | 0.19 | 0.49 | 0.14 | 0.24 | GLIS3 | 0.28 | −0.38 | −0.06 | −0.76 | 0.07 | RN7SL46P | −0.52 | 0.82 | 0.90 | −0.02 | −0.16 |
| GTF2IP20 | −0.42 | 0.12 | 0.62 | −0.01 | 0.27 | AL161935.3 | −0.64 | 1.36 | 1.33 | −0.17 | 0.49 | AL160191.1 | 0.16 | −1.05 | 0.41 | −0.05 | 1.14 |
| AL928654.1 | −0.83 | −0.08 | 0.72 | 0.03 | 0.47 | AL359762.3 | 0.25 | −0.24 | −0.20 | −0.05 | 0.04 | IMPDH1P6 | −0.14 | 0.43 | −0.08 | 1.31 | 0.31 |
| CWC27 | 0.38 | −0.16 | −0.32 | −0.04 | −0.19 | AC142086.1 | −0.88 | 1.34 | −0.18 | 0.72 | −1.26 | C3orf30 | −0.16 | −1.46 | −1.40 | −1.25 | −1.56 |
| G19573 | 1.07 | 0.34 | −0.75 | 0.67 | −0.30 | AC107463.1 | 1.06 | −0.94 | −1.52 | −1.12 | −1.68 | IGHV4-4 | 0.75 | 1.17 | 1.57 | 1.58 | 1.10 |
| AC114494.1 | 1.43 | 0.30 | −0.69 | 0.29 | −0.91 | AC093690.1 | −0.17 | −0.03 | 0.57 | −0.01 | 0.26 | LINC01169 | −0.18 | −1.14 | −0.72 | −0.92 | −1.17 |
| KCNIP1 | −1.40 | 0.60 | 0.84 | 1.11 | 0.42 | AC026746.1 | −0.72 | −0.53 | 0.18 | −0.22 | −1.08 | AC020915.4 | 0.41 | −0.35 | 0.30 | −0.46 | −0.63 |
| P2RY4 | −0.81 | 0.65 | 1.44 | 0.41 | 0.70 | GPR1-AS | 0.49 | −0.10 | −1.31 | −0.43 | −2.06 | LINC00970 | −0.22 | 1.37 | 0.09 | 1.17 | −0.60 |
| LINC01570 | −1.66 | −0.12 | 0.19 | 0.34 | 0.68 | MEIG1 | 0.63 | 0.19 | 2.07 | −0.53 | −0.29 | AC026950.2 | 0.48 | −0.91 | −1.17 | 0.09 | 0.15 |
| LINC00486 | −1.02 | 0.38 | 0.45 | 0.26 | −0.14 | RNU6-419P | −0.61 | 0.90 | 0.50 | 0.55 | 0.48 | IGKV3D-15 | 0.75 | 0.38 | 0.15 | 1.64 | 0.19 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AMPD3 | 0.36 | −0.28 | −0.66 | −0.08 | −0.26 | RAB33A | 0.47 | 0.51 | −0.31 | −0.18 | −0.02 | CPXCR1 | −0.37 | 0.69 | −0.90 | 1.34 | −0.12 |
| LRRC61 | 0.67 | −0.36 | −0.58 | −0.10 | −0.23 | NDFIP1P1 | −0.35 | 0.54 | 0.57 | 0.39 | −0.02 | MIR3659 | 0.14 | −0.47 | −0.93 | 1.23 | 0.11 |
| AC073111.5 | −0.50 | −0.08 | 0.18 | 0.16 | 0.45 | AL157713.1 | 0.57 | 0.74 | −0.35 | 0.56 | −0.34 | MYADML2 | −0.28 | 1.01 | 0.78 | 0.52 | −0.37 |
| AMZ2 | 0.32 | 0.07 | −0.11 | 0.01 | −0.34 | RNU6-13P | −0.64 | 0.36 | −0.65 | 0.07 | −0.47 | OR5BS1P | 0.29 | 0.01 | 2.48 | −1.88 | −0.96 |
| RPS10 | 0.73 | −0.76 | −0.49 | −0.14 | 0.17 | SMPD3 | 0.24 | −0.32 | −0.57 | −0.04 | −0.27 | SDAD1P2 | −0.16 | 0.03 | 0.97 | −0.74 | −1.68 |
| C9orf170 | −0.82 | −0.12 | 0.19 | −0.22 | −0.08 | RPL12P14 | 0.73 | −1.25 | −0.55 | −1.34 | −1.31 | LINC02364 | −0.30 | −0.13 | 2.04 | 0.00 | 1.20 |
| BCCIP | 0.44 | −0.26 | −0.47 | −0.03 | 0.33 | LGALS2 | 0.28 | 0.02 | −0.28 | 0.42 | 0.06 | AP000356.1 | −0.08 | −0.06 | 0.24 | −0.28 | 0.12 |
| AC106028.1 | −1.38 | 0.02 | 0.69 | −0.21 | 0.52 | AL049646.1 | 0.29 | −0.42 | −0.14 | −0.15 | 0.03 | SEMA6D | 0.03 | −0.02 | 0.22 | 0.01 | 0.14 |
| LRRC75B | −0.43 | 0.16 | −0.09 | 0.33 | 0.04 | COX5BP3 | 0.26 | −0.08 | −0.28 | 0.31 | 0.24 | OR4S2 | 0.30 | −1.28 | −0.73 | −1.66 | 1.12 |
| PRPF19 | 0.45 | −0.26 | −0.35 | −0.02 | −0.12 | AL121906.2 | −0.46 | 0.23 | 0.37 | −0.30 | 0.05 | G39342 | 0.75 | 0.03 | 0.47 | 1.51 | 0.43 |
| RUFY3 | −0.26 | 0.13 | 0.19 | 0.04 | 0.11 | MFSD6L | −0.47 | 0.15 | 0.70 | −0.26 | 0.48 | AKR7A2 | 0.03 | 0.08 | 0.05 | −0.09 | −0.12 |
| BRK1 | 0.55 | −0.11 | −0.17 | −0.01 | −0.47 | AL773545.3 | 0.66 | 0.06 | −0.64 | 0.58 | 0.78 | CRYZP1 | 0.04 | −0.13 | 0.00 | 0.03 | −0.14 |
| DOK7 | −0.91 | 0.55 | 0.47 | 0.16 | −0.01 | ATF7IP | 0.10 | 0.05 | 0.12 | −0.04 | −0.03 | OR6S1 | 0.36 | −1.64 | −1.01 | −1.92 | −0.59 |
| SCARNA4 | −0.82 | 0.60 | 0.67 | 0.30 | −0.14 | AC099508.2 | −0.92 | −0.14 | 2.39 | −0.87 | 1.47 | AC084083.1 | −0.07 | −0.01 | 0.71 | 0.06 | 0.23 |
| STK33 | −0.90 | 0.13 | 0.97 | 0.17 | 0.49 | AC244517.5 | −0.66 | 0.36 | −0.77 | 0.72 | 0.04 | RNU6-1212P | −0.18 | 0.22 | −0.56 | 0.24 | −0.95 |
| AL356056.2 | −0.85 | 0.38 | 0.54 | 0.35 | 0.04 | IGHGP | 0.93 | 2.42 | 0.79 | 1.17 | −1.32 | CNOT7P1 | −0.24 | 2.19 | 1.49 | 1.22 | −0.41 |
| RYR2 | −0.91 | 0.36 | 0.58 | 0.56 | 0.10 | SERTM1 | −0.66 | 0.62 | 0.31 | 0.48 | −0.17 | KIF26B | 0.05 | −0.16 | 0.11 | −0.49 | −0.01 |
| CLTB | 0.43 | 0.07 | −0.54 | 0.16 | −0.43 | HMGB1P49 | 0.48 | −1.41 | −0.92 | −0.55 | 0.93 | AC104827.1 | 0.12 | 0.04 | 1.24 | 0.46 | 0.68 |
| NCDN | 0.44 | −0.11 | −0.25 | 0.03 | −0.07 | AC243964.3 | 0.23 | −0.27 | −0.22 | −0.20 | 0.00 | PMS2P9 | 0.28 | −0.89 | −0.67 | −0.89 | −1.65 |
| EIF1AX−AS1 | 1.18 | −1.02 | −1.05 | −0.14 | 0.14 | RASSF5 | 0.14 | −0.03 | −0.09 | −0.06 | −0.28 | AC243960.3 | −0.09 | 0.18 | −1.01 | 0.10 | −0.31 |
| MRPL16 | 0.41 | −0.35 | −0.32 | −0.22 | 0.00 | KRT18P63 | −0.30 | −0.31 | 0.50 | −0.27 | 0.21 | EIF3LP2 | 0.15 | 0.32 | −0.57 | 1.12 | −0.30 |
| AC132008.2 | −0.35 | 0.14 | 0.38 | 0.01 | 0.17 | DENND4C | −0.11 | 0.14 | −0.06 | 0.14 | −0.12 | LINC02598 | −0.15 | 0.33 | 1.28 | 0.24 | 1.14 |
| ABCB4 | −0.57 | 0.08 | 0.19 | −0.03 | 0.19 | AC011462.3 | −0.51 | −0.72 | 0.27 | −0.37 | 0.30 | PSMC1P12 | −0.30 | 0.87 | −0.82 | 0.86 | −2.08 |
| SUCLA2-AS1 | 1.32 | −0.36 | −0.59 | −0.36 | 0.61 | AC022415.1 | −0.40 | −0.07 | 1.66 | −0.35 | 0.49 | G28010 | −0.06 | −0.37 | −0.61 | 0.69 | 0.69 |
| SAP30 | −0.40 | 0.18 | 0.29 | 0.05 | 0.25 | RPL23AP53 | −0.16 | 0.08 | 0.16 | 0.04 | 0.23 | AL161638.2 | 0.29 | −1.44 | −0.55 | −0.06 | −0.97 |
| AC079781.2 | −1.91 | 1.51 | 2.90 | −0.20 | 0.12 | AC112249.1 | −1.27 | 1.13 | 0.25 | 1.54 | −0.03 | LINC01419 | 0.24 | 0.97 | 0.08 | 0.42 | −2.77 |
| AC119751.5 | −2.04 | 0.62 | 1.15 | −0.45 | −0.44 | AC073592.9 | −0.44 | −0.45 | −0.72 | −0.66 | 1.15 | AC087369.1 | 0.22 | 0.35 | −0.42 | 1.04 | −0.29 |
| PNMA5 | −1.03 | 0.79 | 0.26 | 0.48 | 0.17 | DAP | 0.13 | 0.00 | 0.01 | −0.24 | −0.11 | CTD-2144E22.7 | −0.37 | −0.54 | 0.45 | 1.57 | 1.23 |
| RBFOX3 | −0.86 | 0.35 | 0.11 | 0.25 | −0.13 | OR51C1P | 0.70 | −0.56 | −1.24 | 0.84 | −0.24 | RNA5SP128 | −0.16 | 0.49 | 0.17 | 1.22 | 0.55 |
| DIO3 | −1.90 | 1.22 | 2.95 | 0.26 | 0.25 | RN7SKP88 | −0.49 | 0.82 | −0.08 | 0.59 | −0.86 | AC074131.1 | −0.75 | 1.07 | 0.51 | −0.40 | −1.47 |
| GXYLT1P6 | −2.10 | −0.31 | 0.35 | 1.96 | 0.75 | BOLA2-SMG1P6 | −0.41 | −0.13 | 0.00 | −0.26 | 0.74 | BSNDP2 | −0.22 | −0.97 | 2.14 | −0.59 | 0.95 |
| AC106028.3 | −0.84 | 0.18 | 1.35 | 0.05 | 0.42 | AL139339.2 | −0.89 | 0.38 | −1.11 | 0.60 | −1.76 | AL357315.2 | −0.30 | −0.95 | −0.62 | −0.13 | 3.58 |
| AL031595.3 | −0.61 | −0.14 | −0.01 | −0.14 | 0.07 | RNA5SP434 | 0.47 | −0.31 | 0.29 | 0.40 | 0.53 | AC018521.6 | −0.07 | 0.45 | 0.48 | 0.32 | 0.33 |
| G30522 | −0.98 | 0.82 | 0.72 | 0.31 | −0.12 | NSUN4 | 0.09 | −0.04 | −0.17 | 0.04 | 0.10 | FIS1 | 0.02 | 0.02 | 0.10 | −0.06 | −0.22 |
| PMS2P3 | −0.48 | 0.10 | 0.22 | 0.13 | 0.26 | AC073389.2 | −0.63 | 0.43 | 0.80 | −0.15 | 0.36 | DPYS | −0.09 | 0.20 | −0.32 | 0.07 | −0.61 |
| OR11H4 | −1.18 | 0.48 | 0.77 | 0.68 | 0.52 | MTCO3P39 | −1.33 | 0.62 | 1.32 | 2.45 | 1.25 | AC006450.3 | 0.13 | 0.14 | 0.20 | 0.33 | −0.70 |
| GDF11 | −0.34 | −0.03 | 0.44 | −0.12 | 0.26 | AC139749.1 | −0.52 | −0.34 | −2.03 | 1.17 | −1.05 | LINC00955 | 0.17 | −1.52 | −0.50 | −0.53 | −0.24 |
| ARHGEF16 | 0.64 | −0.43 | −1.40 | −0.23 | −0.24 | LY9 | 0.39 | −0.43 | 0.64 | −0.46 | 0.79 | AC104306.1 | −0.10 | −0.40 | 0.66 | −0.45 | −0.03 |
| HACD1 | 0.51 | −0.67 | −0.83 | −0.24 | −0.23 | AC092068.2 | −0.66 | −1.18 | 0.44 | −0.85 | 1.04 | AL158151.1 | −0.12 | 0.25 | 2.28 | −0.02 | 0.43 |
| AC103987.1 | 1.55 | −0.79 | 0.66 | −0.20 | 0.02 | AL132800.1 | −0.56 | 0.33 | 1.88 | −0.58 | −0.35 | SLC36A3 | −0.05 | 0.29 | 0.09 | 0.42 | −0.61 |
| AL157832.3 | −0.87 | 0.69 | 0.80 | 0.40 | 0.18 | AL590440.2 | −0.56 | −0.58 | 0.44 | −0.23 | 0.65 | MIR5691 | −0.17 | 0.56 | −1.37 | 1.05 | −1.71 |
| GATA1 | −1.39 | −0.23 | 0.71 | 0.65 | 1.40 | IL12A-AS1 | −0.50 | 0.48 | −0.26 | 0.82 | 0.99 | AC015660.2 | −0.13 | 0.09 | −0.28 | 0.12 | 0.94 |
| AC092839.1 | −0.98 | −0.01 | 0.45 | 0.29 | 0.53 | RPL39P40 | 0.84 | −0.91 | 0.62 | −0.68 | 0.13 | CDC42EP4 | 0.03 | 0.38 | −0.12 | 0.39 | −0.23 |
| DSEL | −0.76 | 0.37 | 1.21 | −0.55 | 0.20 | AC011124.2 | 0.76 | −1.05 | −1.12 | 0.34 | 0.59 | LINC01003 | 0.05 | −0.25 | 0.62 | −0.17 | 0.44 |
| G13213 | 2.01 | 0.14 | −2.04 | 0.40 | −2.68 | AL359792.1 | 0.54 | −0.59 | −0.30 | 1.87 | 2.12 | ADAM15 | 0.03 | 0.17 | 0.06 | 0.14 | −0.08 |
| MCUR1 | 0.47 | −0.11 | −0.24 | −0.01 | −0.31 | APOL5 | 1.00 | −2.01 | −1.85 | −0.24 | −2.00 | AC024267.5 | 0.07 | 0.05 | 0.47 | −0.01 | 0.18 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| FSD1L | 0.42 | −0.25 | −0.69 | −0.19 | −0.43 | DNAH17-AS1 | 0.32 | −0.62 | −1.14 | 0.52 | 0.31 | AL031963.2 | −0.18 | −0.11 | −0.68 | 0.43 | −0.25 |
| AC027644.1 | −0.56 | −0.02 | 0.53 | 0.28 | 0.36 | AC089984.3 | −1.04 | −1.41 | 0.51 | −0.80 | 0.20 | C19orf84 | 0.20 | −1.61 | 0.37 | −0.61 | 1.56 |
| FOXN4 | −1.95 | 0.22 | −0.21 | 1.12 | −0.29 | AL121895.1 | −0.20 | 0.19 | −0.08 | 0.46 | 0.19 | MIR193B | 0.12 | −0.43 | 0.03 | −0.04 | 1.14 |
| AP000446.1 | −0.83 | 0.41 | 1.22 | 0.05 | 0.57 | AC244394.2 | −0.49 | −0.03 | −0.14 | −0.51 | −0.77 | NLRP9P1 | −0.18 | −0.80 | −1.82 | 0.38 | −0.79 |
| G23007 | −1.55 | 2.70 | 0.08 | 1.49 | 0.42 | AC008750.5 | −0.31 | −0.04 | 0.76 | 0.18 | 0.33 | SLC25A20P1 | −0.71 | 0.77 | −0.11 | 1.81 | 1.98 |
| PEF1 | 0.32 | −0.11 | −0.31 | 0.04 | −0.32 | PIGC | 0.14 | 0.04 | 0.20 | 0.05 | −0.17 | MTCO1P27 | −0.17 | 0.31 | 0.81 | 0.51 | −0.89 |
| LURAPIL | 0.74 | −0.26 | −1.15 | 0.11 | −0.84 | MTATP6P11 | 0.38 | 0.30 | 0.40 | 0.12 | −0.11 | SOX1-OT | −0.42 | 0.50 | 2.70 | −0.80 | −0.28 |
| AC011499.1 | −1.28 | 0.06 | 1.10 | 0.25 | 0.68 | RN7SL161P | −0.76 | 0.08 | −0.40 | 0.36 | −1.71 | AQP10 | −0.12 | −0.98 | −0.92 | −0.07 | 1.18 |
| PARP16 | −0.37 | 0.42 | 0.44 | 0.21 | 0.01 | KIRREL1-IT1 | −0.27 | −0.07 | 0.00 | −0.06 | 0.07 | AL161621.1 | 0.15 | 0.02 | 0.32 | 0.32 | −0.37 |
| ATL2 | 0.40 | −0.06 | −0.27 | −0.07 | −0.14 | AC092666.1 | −0.48 | 0.26 | 0.54 | −0.52 | −0.24 | RNA5SP20 | 0.09 | 0.27 | 0.80 | 0.16 | −0.02 |
| PCMT1 | 0.39 | −0.19 | −0.11 | −0.17 | −0.19 | ATF2 | −0.11 | 0.08 | −0.09 | −0.03 | −0.12 | FOXL2 | 0.13 | −1.03 | 0.00 | −0.49 | 1.24 |
| FCHSD2 | 0.32 | −0.35 | −0.27 | −0.17 | 0.01 | DLGAP1-AS1 | −0.20 | −0.33 | −0.03 | −0.12 | 0.22 | LINC00317 | −0.74 | −0.74 | 0.66 | 0.23 | 1.80 |
| LINC00159 | −1.70 | −0.07 | 2.48 | −0.94 | 1.83 | RN7SKP234 | −0.79 | −0.83 | −0.24 | 2.09 | 1.05 | SLC35F3 | −0.06 | 0.68 | −0.55 | 0.34 | −0.59 |
| IL19 | 2.35 | −2.03 | −4.93 | −0.83 | −2.50 | AC016396.2 | −0.82 | −0.94 | 2.76 | 0.45 | 0.59 | AC097636.1 | −0.17 | −0.87 | −0.15 | −0.31 | 0.03 |
| ROCR | −1.22 | 0.97 | 1.67 | 0.64 | 0.77 | AC211476.1 | −0.55 | 1.47 | −0.21 | 0.63 | −0.51 | C10orf105 | 0.11 | −0.53 | −0.98 | −0.04 | −0.13 |
| CLUHP6 | −1.43 | 0.70 | 0.81 | 1.79 | 0.59 | BARX2 | 0.18 | 0.43 | −0.04 | 0.04 | −0.38 | AC018541.1 | 0.18 | −0.80 | −0.96 | −0.03 | −0.73 |
| AL357143.1 | 1.44 | −1.33 | −1.42 | −0.52 | 0.11 | AC138028.5 | −0.78 | 0.10 | 0.02 | −0.62 | −0.40 | RNU6-189P | 0.48 | −0.52 | 0.19 | −1.04 | −0.92 |
| NONO | 0.29 | −0.17 | −0.45 | 0.00 | −0.26 | C8orf58 | −0.17 | 0.11 | 0.01 | 0.28 | 0.15 | HTRA3 | 0.08 | 0.13 | 0.70 | −0.14 | −0.14 |
| STAC3 | −0.54 | −0.21 | 0.38 | −0.29 | 0.25 | AC131009.4 | 0.27 | 0.29 | 0.18 | 0.15 | −0.13 | AC109464.2 | −0.74 | −0.04 | 0.40 | −1.43 | −2.58 |
| RRBP1 | 0.42 | −0.36 | −0.49 | −0.29 | −0.21 | RNU1-83P | −1.09 | 0.47 | 1.00 | −0.42 | −0.14 | AC089987.2 | −0.16 | −0.92 | −0.26 | −1.14 | 0.67 |
| AL442663.4 | −1.18 | 0.32 | 0.30 | 0.37 | 0.18 | AC010181.1 | −0.81 | −0.17 | −0.71 | −0.14 | −0.52 | AC083867.1 | 0.34 | −2.15 | −0.66 | −0.83 | −0.39 |
| AC091982.3 | −0.86 | 0.72 | 0.53 | 0.47 | 0.40 | NKHD1-EIF4EB. | 0.17 | 0.10 | −0.06 | 0.06 | −0.06 | AC113615.1 | −0.14 | −0.15 | 1.16 | 0.08 | 0.50 |
| SLC25A28 | 0.30 | −0.28 | −0.55 | −0.01 | −0.18 | RNU6-1138P | 0.78 | −1.03 | −0.53 | 1.20 | 0.87 | RTL10 | 0.04 | 0.12 | 0.19 | 0.11 | 0.01 |
| EFNB3 | −0.69 | 0.68 | 1.03 | 0.18 | 0.26 | AC009269.2 | 0.23 | 0.36 | 0.22 | 0.01 | −0.29 | RN7SL713P | −0.48 | 0.68 | 1.81 | −0.41 | −0.47 |
| FGF13 | −0.99 | 0.30 | 0.80 | 0.46 | 0.40 | NTRK3-AS1 | −0.88 | −0.18 | 0.46 | 0.11 | −0.27 | GPR158-AS1 | 0.22 | −1.01 | −0.68 | 0.19 | 0.06 |
| CWC25 | −0.42 | 0.12 | 0.01 | 0.07 | 0.07 | CREB3L2 | 0.14 | 0.02 | −0.19 | −0.18 | −0.24 | AL772284.2 | −0.27 | −1.06 | −0.43 | 1.00 | −0.26 |
| LINC02593 | −1.11 | 0.55 | 1.43 | 0.50 | 0.64 | FZD1 | −0.21 | 0.36 | 0.74 | 0.04 | 0.27 | AC117373.1 | 0.74 | −1.05 | −0.98 | 0.75 | −0.70 |
| RNU6-16P | −1.61 | 0.17 | −1.12 | 1.07 | −0.63 | OR11M1P | 0.46 | −0.53 | −0.12 | 0.24 | 0.38 | AC026336.2 | 0.37 | 0.83 | 1.55 | 0.22 | 0.14 |
| RBPMS | −0.50 | 0.10 | 0.34 | 0.14 | 0.01 | AC098484.2 | −0.30 | 0.35 | 0.80 | 0.50 | 0.16 | AL163051.1 | 0.08 | −0.10 | −0.18 | 0.51 | 0.12 |
| AC022568.1 | −1.88 | 0.90 | 2.05 | 0.33 | 0.60 | JAKMIP1 | 1.56 | −1.07 | −0.94 | −0.15 | −1.01 | LINC02279 | −0.74 | 0.71 | 0.66 | −0.59 | −0.43 |
| AC069281.2 | −1.09 | 1.09 | 0.65 | 0.36 | −0.05 | NARF-IT1 | −0.23 | −0.23 | −0.14 | 0.11 | 0.16 | AL109766.1 | 0.15 | −0.10 | −0.27 | −0.31 | −0.78 |
| AC006145.1 | −0.86 | 0.25 | 0.87 | 0.33 | 0.56 | AC098613.1 | 0.68 | −0.87 | −1.93 | −0.89 | −0.44 | DOK2 | 0.06 | −0.65 | −0.48 | −0.22 | −0.04 |
| PRPF4B | 0.26 | −0.08 | −0.37 | −0.05 | −0.20 | DAB1-AS1 | −0.57 | −0.43 | −0.69 | 0.42 | 0.20 | OR4C3 | 0.28 | −0.45 | −1.23 | 0.89 | −0.41 |
| SENP7 | −0.32 | 0.24 | 0.57 | 0.09 | 0.11 | AC022537.1 | −0.33 | 0.16 | 1.36 | −0.26 | 0.33 | PEX12P1 | −0.74 | 0.75 | 0.87 | 0.57 | −0.15 |
| GJC3 | −1.04 | 0.88 | 1.27 | 0.58 | 0.11 | SELENOKP3 | −0.61 | −0.37 | 0.29 | 0.02 | −0.74 | SNORD113-5 | 0.26 | −1.25 | −1.58 | 0.35 | 1.04 |
| AC080023.1 | 1.17 | −0.73 | −1.93 | 0.36 | −0.92 | PTGER2 | −0.28 | −0.28 | 0.69 | −0.02 | 0.29 | AP003357.1 | −0.08 | −0.05 | 0.63 | −0.46 | 0.22 |
| AL109936.6 | −0.51 | −0.18 | 0.66 | −0.16 | 0.75 | RPL21P119 | 0.75 | −0.14 | 0.39 | −0.21 | −0.21 | LINC00690 | 0.25 | −1.93 | −0.29 | −1.00 | 0.18 |
| CD44-AS1 | 1.03 | −0.47 | −0.56 | −0.19 | −0.13 | FCF1P1 | −0.31 | −0.09 | 0.03 | 0.02 | 0.40 | MIR613 | −0.33 | 0.09 | 0.55 | 1.02 | −0.65 |
| METTL16 | −0.25 | 0.09 | 0.26 | 0.03 | 0.14 | AC073575.1 | 0.28 | −0.20 | −0.45 | 0.04 | −0.03 | AC079915.1 | −0.05 | −0.32 | 0.44 | −0.41 | 0.27 |
| PXYLP1 | −0.37 | 0.38 | 0.18 | 0.08 | −0.15 | CBLN2 | −0.61 | 0.53 | −1.15 | −0.54 | −2.44 | AC108025.2 | 0.62 | −0.36 | −0.87 | 1.05 | 0.01 |
| AC069113.3 | −1.83 | 0.44 | 1.89 | 0.17 | 0.77 | AC024568.1 | 0.14 | −0.14 | −0.31 | 0.01 | −0.06 | LDHC | −0.11 | −0.54 | −0.32 | −0.35 | −0.23 |
| SPSB3 | −0.83 | 0.97 | 0.99 | 0.49 | 0.27 | LINC01861 | 1.01 | −1.04 | −0.16 | −1.34 | −0.56 | SGO1P1 | 0.18 | 0.69 | −0.61 | 1.01 | −1.11 |
| LARP1B | 0.31 | −0.12 | −0.27 | −0.18 | −0.17 | AC007954.1 | −0.42 | 0.59 | 0.09 | 0.52 | 0.40 | RNU6-1169P | 0.14 | −1.40 | 0.61 | −0.21 | 0.79 |
| ATP6VOCP4 | 1.20 | −0.40 | −1.04 | −0.89 | −0.34 | BNIP3P10 | −0.36 | 0.53 | 0.64 | 0.02 | 0.11 | AC012673.1 | −0.10 | −1.04 | −2.21 | 0.96 | −0.87 |
| MAIP1 | 0.40 | 0.07 | −0.33 | 0.06 | −0.14 | AL513321.1 | −1.85 | 0.55 | 0.63 | −0.12 | −1.35 | AL160237.1 | −0.35 | −1.28 | −0.50 | 2.56 | 0.42 |
| COL4A1 | 0.86 | −0.85 | −0.56 | −0.68 | −0.51 | AC011979.1 | 0.61 | 0.46 | −0.70 | −0.67 | −1.18 | RNU6-297P | 0.52 | −1.23 | −0.30 | −0.45 | −0.87 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| FAT2 | 0.65 | −0.36 | −0.46 | 0.02 | 0.10 | MIR550A3 | −0.85 | 0.94 | 0.86 | −0.33 | −0.73 | RN7SKP163 | −0.05 | 0.18 | 0.13 | 0.29 | 0.15 |
| ARMCX1 | −0.44 | 0.27 | 0.41 | 0.14 | −0.01 | GMFG | 0.27 | −0.60 | 0.33 | −0.47 | 0.31 | AC079896.1 | 0.74 | −0.38 | 0.46 | 0.38 | 0.75 |
| COIL | 0.33 | −0.08 | −0.13 | −0.06 | −0.07 | HID1-AS1 | −0.52 | −0.37 | 0.96 | 0.98 | −0.19 | CCDC37-DT | −0.40 | −0.04 | −0.68 | 0.25 | −2.87 |
| AC069120.1 | −1.71 | 1.65 | 1.84 | 1.03 | 0.80 | AC008957.3 | 0.27 | −0.62 | 0.10 | −0.16 | 0.28 | LINC00334 | 0.19 | −1.52 | 1.40 | −0.20 | 1.60 |
| AC034195.1 | −1.36 | 0.02 | 1.56 | −0.18 | 0.68 | RBPJL | −0.45 | 0.10 | −0.10 | 0.30 | 0.39 | AC136944.3 | 0.17 | −0.43 | −0.83 | 0.08 | −1.97 |
| RNU6-268P | 1.22 | −0.19 | −1.03 | −0.26 | −1.43 | MPRIPP1 | −0.28 | 0.15 | 0.24 | 0.13 | 0.43 | MCHR2 | −0.22 | −0.20 | −1.25 | −0.37 | −0.03 |
| PABPC1P7 | −1.26 | 0.67 | 1.80 | 0.67 | 0.43 | AP000919.2 | 0.43 | −0.46 | −0.20 | −0.16 | −0.58 | AC020551.1 | −0.21 | 0.82 | 0.68 | −0.40 | −0.61 |
| KPNA1 | 0.24 | −0.10 | −0.34 | −0.04 | −0.12 | OR2T33 | 0.77 | −0.59 | −1.36 | 0.34 | −0.60 | AC097372.3 | 0.07 | −0.70 | −0.33 | −0.48 | −0.27 |
| SHF | −0.41 | 0.29 | 0.03 | 0.11 | −0.20 | RNU2-7P | 0.49 | −1.23 | 0.91 | −0.15 | 0.84 | SLC22A18AS | 0.08 | 0.17 | 0.17 | 0.90 | 0.20 |
| EFEMP1 | −0.72 | 0.23 | 0.58 | 0.10 | 0.06 | AC068389.1 | −0.43 | −0.20 | 0.19 | −0.35 | −0.51 | RNA5SP354 | 0.09 | 0.23 | 0.40 | 0.27 | 0.59 |
| PCDH15 | −1.17 | 0.07 | −0.57 | 0.72 | −0.17 | RNVU1-17 | −1.23 | 1.51 | −0.54 | 2.96 | −0.26 | RNU6-964P | 0.28 | −1.76 | 2.71 | −0.56 | 2.26 |
| C21orf58 | −0.51 | −0.24 | 0.07 | 0.02 | 0.60 | KNDC1 | 0.30 | −0.19 | −0.67 | 0.03 | −0.46 | RPS15AP3 | −0.69 | −0.84 | 0.00 | −0.19 | 1.45 |
| G12287 | −1.48 | 0.25 | 1.88 | −0.01 | 0.80 | AC241584.2 | −0.48 | −0.40 | 0.73 | −0.27 | 1.02 | G4026 | 0.26 | 0.01 | 0.07 | −0.80 | −1.34 |
| GEMIN5 | 0.34 | −0.35 | −0.35 | −0.17 | 0.01 | NR4A2 | −0.31 | 0.47 | −0.20 | −0.34 | −0.65 | AC004943.3 | 0.28 | −0.67 | 0.53 | −0.16 | 0.51 |
| LINC01215 | 1.82 | −1.42 | −1.91 | 0.46 | −0.51 | EIF5A2P1 | −0.35 | −0.15 | 0.48 | 0.45 | 1.11 | EEF1A1P13 | 0.04 | 0.04 | 0.35 | 0.03 | 0.09 |
| GATA6 | −0.98 | 0.63 | 1.16 | 0.06 | 0.21 | AC022733.2 | 1.13 | −1.64 | −1.49 | 0.38 | −2.05 | AC093424.1 | −0.20 | −0.17 | 0.15 | 2.17 | −0.19 |
| PCDHB8 | −1.04 | 0.69 | 1.59 | −0.01 | −0.19 | AC009652.1 | −0.51 | −0.23 | −0.67 | −0.14 | −0.33 | PHB2P1 | 0.29 | −0.56 | −0.33 | −0.90 | −1.27 |
| AC021242.2 | −1.84 | −0.23 | 0.72 | −0.61 | 0.09 | PNLDC1 | −0.51 | 0.32 | −0.26 | 0.73 | 1.10 | AC073429.1 | 0.45 | −0.50 | −2.03 | −1.03 | −2.71 |
| GOLGA6L4 | −0.70 | 0.06 | 0.46 | 0.17 | 0.02 | PCDHA2 | −0.78 | −0.66 | 0.38 | 1.03 | 1.04 | LINC00557 | −0.31 | 0.47 | 0.70 | −0.12 | −0.25 |
| RNU6-1033P | 1.42 | −0.01 | −1.74 | 0.06 | −0.96 | RPL23AP75 | −0.78 | −0.88 | −0.16 | −1.14 | −0.04 | DCAF13P2 | −0.13 | −0.51 | −0.64 | −0.01 | −1.24 |
| AL450322.2 | 1.76 | −0.66 | −2.90 | 0.27 | −3.01 | AC098826.1 | −1.19 | 1.08 | 1.25 | 1.50 | −0.31 | AL355076.2 | −0.14 | −0.93 | 0.04 | −1.05 | −0.63 |
| AC002401.4 | 2.54 | −2.86 | −2.31 | 0.56 | −0.83 | AC023906.2 | 0.42 | 0.31 | 0.05 | 0.01 | −0.20 | MYO18B | 0.08 | 0.13 | −0.80 | 0.11 | −0.34 |
| NEDD9 | −0.47 | 0.29 | 0.45 | −0.04 | −0.09 | GLT8D2 | −0.25 | 0.19 | 0.91 | −0.47 | 0.07 | SLC25A15P4 | −0.44 | −0.11 | −1.24 | 0.34 | −1.01 |
| ARMC8 | 0.27 | −0.06 | −0.09 | −0.02 | −0.06 | SMIM9 | −0.86 | −0.49 | −0.10 | 0.54 | −0.83 | OPCML-IT2 | −0.34 | −0.77 | −0.95 | 0.10 | −0.15 |
| AC108451.1 | −1.13 | 0.06 | −0.65 | −0.43 | −0.71 | LINC02452 | 0.59 | −1.19 | −1.72 | 0.08 | −1.39 | CRNDE | −0.03 | 0.14 | 0.21 | 0.01 | −0.07 |
| RNF157 | −0.79 | 0.20 | 0.78 | 0.04 | 0.72 | AC145146.1 | 0.94 | −0.92 | −1.05 | 0.11 | −2.26 | C20orf85 | 0.16 | −0.26 | 1.80 | −0.32 | 0.53 |
| RPL21P28 | 0.77 | −0.20 | −0.27 | −0.15 | −0.74 | AP005120.1 | −0.87 | −0.99 | 2.93 | −2.44 | 2.66 | LINC02591 | −0.03 | −0.16 | −0.26 | 0.19 | 0.27 |
| PIK3C2G | −0.69 | 0.90 | 0.84 | 0.64 | 0.08 | FANK1 | −0.15 | 0.33 | −0.01 | 0.19 | −0.01 | CABS1 | 0.24 | −0.43 | −0.97 | −0.26 | −0.87 |
| PRH2 | −0.81 | 0.15 | 0.85 | 0.00 | 0.39 | GKN1 | −0.64 | 0.25 | −0.06 | −0.41 | −0.08 | AC012213.1 | −0.15 | −1.44 | −0.24 | −0.92 | 0.47 |
| PACRG | −0.89 | 0.73 | 1.17 | 0.58 | 0.37 | AC104237.1 | −0.47 | 1.07 | 2.38 | 0.10 | 0.51 | COA1 | −0.02 | 0.05 | 0.13 | 0.07 | 0.18 |
| AC018628.1 | −0.54 | −0.02 | −0.33 | 0.21 | 0.09 | AL161935.1 | −0.43 | −0.33 | 1.41 | −0.07 | 1.28 | AP005901.1 | −0.17 | 0.01 | −0.68 | 1.15 | 0.74 |
| SEC1P | −1.28 | 0.80 | 1.31 | 0.77 | 0.37 | AC016747.1 | −0.25 | −0.17 | 0.10 | 0.10 | 0.54 | AC015849.12 | 0.35 | −2.01 | −0.06 | −1.59 | 0.86 |
| AC105001.1 | 0.71 | −0.37 | −0.64 | −0.23 | −0.41 | G21034 | −0.25 | 0.07 | 0.60 | 0.14 | 0.52 | SPRED3 | 0.04 | −0.37 | 0.04 | −0.27 | 0.38 |
| AWAT2 | −1.93 | 1.08 | 1.80 | 0.16 | 1.40 | SHARPIN | −0.10 | 0.07 | −0.11 | 0.03 | 0.04 | OR2B3 | 0.42 | −0.73 | −0.03 | −0.02 | 0.05 |
| AC092171.4 | −0.77 | 0.16 | 0.42 | 0.24 | 0.16 | RN7SL107P | −0.79 | 0.83 | −1.47 | 1.42 | −1.44 | AC090826.1 | 0.10 | −0.47 | 0.30 | 0.06 | 0.03 |
| CYBC1 | 0.31 | −0.45 | −0.36 | −0.20 | −0.02 | MBOAT4 | 0.41 | −0.16 | −0.31 | 0.59 | 0.01 | CBLN4 | −0.21 | −1.04 | 0.57 | 0.46 | −1.50 |
| OR51I2 | −1.03 | 0.52 | 1.49 | 0.16 | 0.31 | PPP2R5C | 0.08 | 0.02 | −0.05 | 0.00 | −0.11 | AC087045.1 | 0.16 | −1.14 | −0.90 | −0.63 | 0.16 |
| PGR-AS1 | −1.40 | 0.29 | 1.28 | 0.52 | 0.82 | LYST | 0.11 | 0.05 | 0.05 | −0.04 | −0.05 | AL357873.1 | −0.07 | 0.06 | 1.34 | −0.32 | 0.14 |
| FAM90A1 | −1.05 | 0.92 | 0.53 | 0.40 | −0.12 | GUCY1B1 | −0.24 | 0.01 | 0.76 | −0.37 | −0.23 | LINC00211 | 0.11 | −0.46 | −1.31 | −0.49 | −1.00 |
| KLRG2 | −0.87 | 0.79 | 0.90 | 0.60 | 0.03 | GAPDHP63 | 0.58 | −0.47 | −0.86 | 0.24 | −0.55 | IGKV1D-16 | 0.73 | −0.45 | −0.40 | 1.54 | −1.07 |
| GNG7 | −0.74 | 0.27 | 1.10 | 0.06 | 0.66 | SASH1 | −0.10 | 0.40 | 0.27 | 0.25 | −0.20 | AC018653.1 | −0.52 | −0.30 | −0.61 | −1.85 | −0.43 |
| CEP83 | 0.33 | −0.27 | −0.27 | −0.17 | −0.03 | RN7SKP226 | 1.22 | −1.98 | −1.69 | 2.21 | 0.58 | MTCYBP41 | −0.08 | 0.13 | 0.85 | −0.13 | 0.34 |
| COP1 | 0.24 | −0.11 | −0.15 | −0.06 | −0.05 | RN7SL8P | −0.85 | 0.01 | −1.01 | 0.45 | −2.00 | LINC01438 | −0.69 | 0.58 | 0.07 | 0.82 | −0.56 |
| FOXO4 | −0.49 | 0.71 | 0.73 | 0.39 | −0.04 | AL645937.1 | −1.28 | −0.76 | 0.82 | 0.92 | −0.52 | IGKV1-8 | 0.55 | −0.11 | −1.54 | 1.70 | −1.67 |
| FBXL8 | −0.66 | 0.33 | 0.56 | 0.30 | 0.46 | RNU6-1246P | 0.67 | 0.70 | 0.09 | 1.47 | −0.23 | AC073648.1 | 0.07 | −0.06 | 0.45 | −0.29 | −0.32 |
| AL353803.2 | −1.87 | −0.68 | −0.32 | 0.97 | 0.62 | COL22A1 | 0.42 | −0.88 | −1.28 | 0.01 | −0.74 | RTN4 | −0.02 | 0.03 | −0.02 | 0.06 | 0.03 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| G12085 | 2.07 | 0.45 | −5.16 | 0.49 | −4.67 | RPL23AP37 | 1.00 | 0.54 | −0.13 | 0.72 | −0.88 | AL450471.1 | −0.20 | −0.62 | 0.29 | −0.17 | 0.17 |
| HIST1H4D | 0.88 | −0.62 | −0.65 | −0.09 | −0.61 | RNU1-2 | −0.38 | −0.25 | 0.29 | −0.81 | 0.08 | AC004801.7 | 0.21 | −0.42 | −0.88 | 0.42 | −0.34 |
| IGSF9 | −0.61 | 0.18 | −0.18 | 0.38 | 0.41 | AC008734.1 | −0.54 | −0.44 | −0.47 | −0.03 | 0.23 | MIR1255A | −0.12 | −0.53 | 1.87 | −1.45 | 0.29 |
| AGBL5 | −0.30 | 0.18 | 0.45 | 0.04 | 0.20 | BTF3P6 | 0.31 | −0.83 | −0.88 | −0.06 | 0.30 | AP000797.2 | −0.31 | 0.45 | −0.31 | 1.72 | 0.24 |
| MYOT | −0.66 | 0.49 | 0.38 | 0.45 | 0.41 | REPS1 | 0.10 | 0.13 | −0.06 | 0.10 | −0.07 | AC092376.1 | 0.21 | 0.10 | −1.53 | 1.19 | −0.76 |
| LMCD1 | −0.70 | 0.25 | 1.11 | −0.53 | 0.16 | RPL13AP17 | −0.49 | −0.77 | −0.20 | −0.56 | 0.21 | OR13C5 | −0.36 | −0.50 | −0.43 | 0.72 | 0.81 |
| AC138230.1 | −0.94 | −0.06 | 0.56 | −0.04 | 0.21 | LINC02252 | −0.87 | −0.75 | 0.09 | −1.03 | −1.05 | LINC01606 | −0.15 | −1.44 | −1.47 | 1.10 | 1.73 |
| BCAS4 | −0.54 | 0.29 | 0.14 | 0.37 | −0.09 | RHOJ | −0.21 | 0.24 | 0.87 | −0.24 | 0.09 | AC096751.2 | −0.18 | 0.19 | 1.03 | 0.69 | 0.48 |
| FAM160A1 | 0.57 | 0.04 | −0.45 | 0.15 | −0.24 | AL021393.1 | −0.34 | 0.63 | −0.05 | 0.60 | −0.17 | OR2F2 | −0.25 | −0.40 | 1.42 | 1.21 | 1.84 |
| ERICH2 | −1.20 | 0.46 | 0.91 | 0.38 | 0.09 | AC074276.1 | 0.48 | −0.60 | 0.62 | 0.17 | 0.37 | RPL7P58 | 0.24 | −0.86 | −0.63 | −0.03 | −0.63 |
| RAB40A | −0.84 | 0.07 | 1.48 | −0.51 | 0.31 | IER3-AS1 | 0.98 | −0.95 | −1.88 | −0.42 | −1.29 | AL356961.1 | 0.47 | −0.53 | 0.57 | 1.34 | 1.96 |
| SERPINH1 | 0.53 | −0.46 | −0.03 | −0.65 | −0.29 | CHI3L1 | −0.34 | 0.11 | 0.71 | 0.59 | 0.35 | MYPN | 0.09 | 0.64 | −0.93 | 0.55 | −0.83 |
| FGD5 | −0.59 | 0.31 | 0.77 | 0.08 | 0.23 | RPL24P2 | 0.49 | 0.09 | −0.64 | −0.39 | −1.30 | AC073115.1 | −0.73 | 0.74 | 0.57 | 0.65 | −0.67 |
| SNAPC1 | 0.37 | −0.22 | −0.43 | −0.02 | −0.09 | EME2 | −0.19 | 0.13 | −0.17 | 0.29 | 0.08 | AL049737.1 | 0.20 | −0.60 | −2.17 | 0.36 | −2.57 |
| FRG2DP | −1.22 | 0.14 | −0.20 | 0.34 | 0.28 | AC016700.2 | 0.65 | −0.91 | −0.30 | −0.56 | 0.09 | LINC01661 | 0.32 | −0.16 | −0.23 | 0.99 | 1.72 |
| MGAT3 | −0.83 | 0.70 | 0.74 | 0.20 | −0.23 | MMP7 | −0.36 | −0.13 | −0.25 | −0.12 | −1.08 | AL020994.1 | 0.73 | −0.64 | 0.54 | −0.43 | 1.39 |
| RPL7P1 | 0.58 | −0.06 | 0.02 | 0.13 | −0.17 | GRK5 | −0.19 | 0.15 | 0.30 | 0.06 | −0.01 | AC007785.3 | −0.10 | −1.59 | −0.21 | −0.77 | 0.85 |
| SNORA45 | −0.81 | 0.88 | 0.82 | 0.51 | 0.28 | LMBRD1 | −0.14 | 0.27 | 0.15 | 0.09 | −0.20 | LINC01716 | −0.18 | 0.13 | −1.63 | 0.16 | −1.80 |
| OR52H1 | −1.10 | 0.08 | 0.99 | 0.25 | 0.46 | ST13P5 | −0.49 | 0.47 | 0.49 | 0.52 | 0.04 | AL157904.1 | 0.17 | −0.87 | −1.27 | 0.33 | −1.31 |
| AC121320.1 | −1.01 | 0.80 | 1.15 | 0.42 | −0.23 | B3GALT6 | 0.13 | −0.05 | 0.01 | 0.04 | 0.29 | OR1M1 | 0.15 | −0.52 | −1.35 | 0.45 | 0.14 |
| RAB3GAP2 | 0.22 | −0.11 | −0.22 | −0.09 | −0.11 | RNU6-31P | −0.46 | 0.56 | −1.26 | 1.00 | −1.11 | RNU1-52P | −0.68 | 0.30 | 0.48 | 1.10 | −0.26 |
| SPIDR | −0.18 | 0.02 | 0.13 | −0.08 | 0.05 | PILRB | −0.21 | 0.09 | 0.06 | 0.33 | 0.74 | AC097535.2 | −0.72 | 0.49 | −1.28 | 2.19 | −2.23 |
| CR381653.1 | −0.79 | 0.62 | 0.89 | 1.27 | 1.16 | AC097639.1 | 0.33 | 0.12 | 0.08 | 0.42 | 0.01 | AL596325.1 | 0.15 | −0.94 | −1.06 | −0.68 | −0.41 |
| ANXA3 | 1.02 | −1.31 | −1.36 | −0.81 | −0.19 | AC023078.1 | −0.80 | 0.54 | 2.09 | 1.40 | 1.51 | LINC02129 | 0.71 | −1.96 | −0.73 | 0.03 | 0.55 |
| OTUB1 | 0.31 | −0.03 | −0.67 | 0.25 | −0.37 | CDC42BPA | −0.11 | 0.07 | 0.05 | −0.04 | −0.07 | AL591135.1 | −0.07 | −0.10 | −0.73 | −0.07 | −0.85 |
| AL137229.1 | −0.98 | −0.01 | −0.73 | −0.05 | −0.29 | G33524 | 0.52 | −0.56 | −0.20 | 0.14 | 0.79 | AC098679.3 | 0.59 | −0.38 | 0.16 | −0.28 | 2.55 |
| FUNDC2P1 | 1.06 | −0.48 | −1.71 | 0.45 | 0.12 | OR2M3 | −0.59 | −0.46 | −1.45 | 0.02 | −1.20 | RNA5SP95 | 0.37 | 0.83 | −0.66 | −0.26 | −2.04 |
| ANKK1 | −0.80 | 0.50 | 0.33 | 0.17 | 0.19 | KCTD21-AS1 | −0.26 | −0.25 | 0.72 | 0.30 | 0.99 | RNA5SP345 | 0.11 | −0.38 | 0.15 | −0.61 | −0.55 |
| LMOD3 | −0.84 | 0.25 | 0.24 | −0.18 | −0.16 | RN7SL147P | 0.70 | 0.46 | −2.17 | 1.22 | −1.64 | SERPINB9P1 | 0.06 | −0.52 | −0.50 | −0.26 | −0.18 |
| EPHA3 | −0.93 | 0.64 | 0.49 | 0.62 | −0.38 | AC026427.2 | 0.61 | −0.29 | 0.29 | −0.15 | 0.61 | HNRNPA1P9 | 0.12 | −0.88 | 1.10 | −0.27 | 0.29 |
| CMTR1 | −0.23 | −0.06 | 0.09 | −0.05 | 0.16 | PREX1 | 0.21 | −0.54 | −0.27 | −0.34 | −0.03 | AC105460.2 | 0.23 | −1.43 | −2.76 | 0.89 | −0.93 |
| ANG | −0.82 | 0.80 | 1.10 | 0.35 | 0.51 | AL158163.2 | −0.50 | 0.55 | 0.32 | 0.02 | −0.19 | AC010425.1 | −0.14 | 1.27 | −0.83 | 0.14 | −1.44 |
| LRRC3B | −1.39 | 1.39 | −1.08 | 0.63 | −2.07 | AC073592.3 | −0.33 | −0.16 | −0.68 | 0.08 | −0.05 | CNTD2 | −0.11 | 0.58 | −0.68 | −0.02 | −0.68 |
| CHRAC1 | 0.53 | −0.19 | −0.31 | −0.19 | −0.36 | AP003969.1 | −0.75 | −0.08 | 1.52 | −0.43 | 0.23 | GADD45G | −0.05 | −0.05 | −0.20 | 0.40 | 0.29 |
| BLZF2P | 0.95 | −0.94 | −1.08 | −0.65 | −0.63 | PDZK1P1 | −1.20 | 1.01 | 1.01 | 1.73 | −0.04 | AC124916.1 | 0.12 | −0.88 | 0.14 | −0.14 | 0.37 |
| PANK3 | 0.44 | 0.01 | −0.13 | −0.09 | −0.33 | RN7SKP130 | 0.80 | −0.84 | 1.10 | −0.48 | 1.42 | AC087721.1 | 0.09 | −1.16 | −1.25 | −0.20 | 0.18 |
| SCLY | 0.50 | −0.29 | −1.15 | 0.14 | −0.47 | CLEC10A | 0.32 | −0.45 | −0.11 | −0.09 | 0.36 | AL513128.1 | −0.72 | −0.11 | 1.32 | −0.22 | 1.14 |
| MTCO1P42 | −1.84 | −0.05 | −0.10 | 0.84 | 0.95 | NRG4 | −0.24 | −0.02 | 0.00 | 0.49 | −0.08 | G42447 | 0.24 | 0.73 | 0.96 | 2.25 | 0.50 |
| SLCO4A1-AS1 | −0.93 | 0.22 | −0.59 | 0.18 | −0.33 | HSPA8P1 | −0.48 | 0.59 | −1.23 | −0.32 | −1.19 | GAMTP2 | −0.45 | 0.54 | 1.50 | 1.31 | 2.28 |
| HRC | −0.99 | 0.93 | 1.52 | 0.78 | 0.22 | FBXO36 | −0.15 | 0.32 | 0.00 | 0.30 | −0.03 | AC099328.2 | −0.23 | −0.06 | −2.63 | 0.36 | −1.87 |
| HDX | −0.65 | 0.42 | 0.69 | 0.03 | 0.03 | AL031719.2 | 0.52 | −0.25 | −0.45 | 0.13 | −0.51 | SHANK2-AS2 | −0.10 | 0.31 | −0.38 | −0.12 | −0.82 |
| STEAP2 | −0.61 | 0.06 | 1.29 | −0.60 | 0.20 | AL049839.1 | 1.46 | −1.02 | −0.62 | 0.93 | −1.17 | LRRC37A12P | 0.16 | −0.81 | −0.93 | −0.16 | −0.11 |
| PODXL | 0.57 | −0.24 | 0.14 | −0.10 | 0.15 | AL355885.1 | −0.47 | −0.84 | 0.87 | −0.68 | 0.83 | EDN1 | 0.03 | −0.13 | 0.04 | −0.02 | −0.03 |
| KLHL29 | −0.37 | 0.16 | −0.06 | 0.20 | 0.09 | GPX7 | 0.25 | −0.17 | 0.32 | −0.53 | −0.26 | GPBAR1 | −0.04 | −0.04 | −0.22 | −0.03 | −0.12 |
| C14orf28 | −0.56 | 0.48 | 0.58 | 0.21 | −0.11 | EIF4A1P4 | 0.72 | −0.73 | −1.25 | −0.34 | −1.17 | RPL5P25 | −0.26 | 1.65 | −0.63 | 2.51 | −0.16 |
| EPHA6 | −1.02 | 0.30 | 0.65 | −0.09 | −0.02 | AC097480.1 | −1.04 | 1.15 | 0.88 | 0.82 | −0.28 | AC097523.1 | 0.11 | −0.26 | −0.14 | 0.33 | 1.00 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| PRDM5 | −0.37 | 0.07 | 0.44 | −0.10 | 0.09 | PHETA2 | 0.14 | −0.26 | −0.10 | −0.30 | 0.04 | RNU6-704P | −0.27 | −0.68 | 1.51 | −0.17 | 0.74 |
| NETO1 | −1.31 | 0.29 | 0.79 | 0.20 | 0.24 | H2AFZP4 | 0.31 | −0.05 | −0.19 | −0.25 | −0.58 | IGKV1-33 | 0.72 | 0.57 | 0.66 | 0.87 | −2.04 |
| KIAA1147 | −0.27 | 0.18 | 0.40 | 0.09 | 0.20 | AL008638.4 | −0.90 | 0.68 | 1.17 | 1.24 | 0.44 | AC027667.1 | −0.24 | −0.58 | 1.85 | −0.03 | 0.40 |
| AC010654.1 | −0.81 | 0.02 | 0.71 | 0.14 | 0.20 | AC135050.4 | 0.40 | −1.63 | −1.46 | −0.96 | −0.56 | AL353052.1 | 0.41 | −1.63 | 0.38 | 0.96 | 1.87 |
| AL158824.1 | 1.47 | −0.45 | −0.85 | −0.20 | −0.04 | PLEKHG4B | −0.27 | 0.39 | 0.18 | 0.43 | 0.34 | AC006033.2 | 0.10 | −0.25 | −0.80 | −0.03 | −0.90 |
| CSF2 | 2.06 | −2.12 | −1.70 | −0.94 | −0.27 | IGKV3-20 | 1.01 | 2.53 | 2.33 | 1.08 | −0.35 | AL161757.3 | 0.19 | −0.63 | −2.54 | 1.41 | −3.55 |
| POLR3GL | −0.58 | 0.29 | 0.62 | 0.19 | 0.21 | AP000852.1 | −0.80 | 0.58 | 0.85 | −0.41 | 0.20 | AC006960.3 | −0.18 | 0.98 | 0.36 | 0.73 | −0.72 |
| RN7SL243P | −1.02 | 0.01 | 0.42 | 0.27 | 0.37 | ARHGAP17 | −0.08 | 0.17 | 0.20 | −0.05 | −0.06 | AC002460.1 | 0.70 | −0.69 | 0.87 | −0.19 | 0.45 |
| HAX1 | 0.32 | −0.13 | −0.20 | −0.17 | −0.24 | CU639417.1 | 0.41 | 0.13 | −0.42 | −0.53 | −0.61 | OR8H3 | −0.34 | −0.63 | −1.90 | −0.45 | −1.31 |
| DDI1 | −0.98 | 0.96 | 1.20 | 0.60 | 0.37 | MYO1C | 0.12 | −0.12 | −0.59 | 0.08 | −0.25 | AL138767.3 | −0.20 | −1.22 | −1.85 | −1.18 | −2.63 |
| ENPP7P1 | −1.38 | −0.04 | 1.17 | 0.36 | 0.40 | AC023051.1 | −0.23 | 0.45 | 0.36 | 0.35 | 0.02 | LINC02538 | −0.11 | −0.68 | −0.18 | 0.32 | 0.20 |
| KPNA5 | −0.28 | 0.26 | 0.47 | 0.14 | 0.21 | AC006028.1 | 0.58 | −0.57 | −2.43 | 0.08 | −0.72 | LINC00583 | −0.72 | 0.33 | 1.55 | −1.13 | 0.40 |
| IGF2R | 0.25 | −0.16 | −0.29 | −0.06 | −0.12 | AC093206.1 | −0.79 | 1.27 | −0.47 | 0.00 | −0.05 | AC084809.2 | 0.15 | −1.02 | 0.87 | −0.08 | 0.84 |
| LINC00648 | −1.24 | 0.27 | −0.34 | 1.21 | 0.12 | G35258 | −0.46 | 0.82 | 0.83 | −0.74 | −0.07 | AC013270.1 | 0.42 | 0.10 | 0.02 | 1.47 | −1.78 |
| AC011477.4 | −1.96 | 0.03 | 1.52 | 0.05 | 0.71 | AL035252.2 | −0.79 | 1.06 | −0.78 | 1.09 | −0.84 | C5AR2 | −0.06 | −0.05 | −0.17 | −0.39 | −0.52 |
| ESCO1 | 0.29 | −0.03 | −0.11 | −0.04 | −0.09 | PWWP2A | 0.11 | −0.03 | 0.12 | −0.08 | 0.06 | GHc-362H12.3 | 0.09 | −0.07 | −0.70 | 0.80 | 0.03 |
| B4GALT3 | −0.36 | 0.21 | 0.34 | 0.11 | 0.23 | EEF1A1P4 | 0.24 | −0.04 | 0.17 | 0.09 | 0.21 | EIF4EP5 | 0.28 | −1.05 | 0.61 | −1.01 | −1.27 |
| RN7SL670P | −1.66 | −0.64 | 0.32 | 2.04 | 2.42 | AC069113.1 | −1.22 | 0.54 | 1.48 | 2.13 | 1.40 | AC023510.1 | 0.15 | −0.98 | −0.25 | −0.18 | −0.10 |
| IGHG2 | 2.22 | 1.73 | 2.63 | −1.64 | −1.48 | AC084036.1 | −0.29 | 0.48 | 0.13 | 0.24 | −0.09 | SEMA3C | 0.04 | 0.12 | 0.04 | −0.45 | −0.50 |
| DDIT3 | −0.74 | 0.23 | 0.24 | 0.24 | −0.05 | RP11-395P13.5 | −1.07 | 0.63 | 0.23 | 0.28 | −0.06 | SLCO6A1 | 0.14 | −0.69 | −0.82 | 0.47 | −1.21 |
| FBXO17 | −0.50 | 0.12 | 0.37 | 0.21 | 0.29 | OR6M1 | −0.96 | −0.89 | −0.06 | −0.36 | 0.16 | HNRNPA1P18 | 0.66 | 0.45 | −0.51 | 0.17 | −0.38 |
| PSMG3-AS1 | −0.53 | 0.16 | 0.54 | −0.02 | 0.16 | SNORD19B | 0.97 | 0.72 | −2.30 | 1.14 | −0.92 | AC114401.1 | −0.06 | −0.34 | −0.72 | 0.28 | −0.18 |
| AC234772.2 | 1.12 | −0.67 | −1.65 | 0.10 | −0.67 | ADAMTS20 | 0.64 | −0.04 | −0.85 | 0.24 | −1.05 | AC100852.2 | 0.23 | −1.97 | 1.17 | −1.21 | 2.15 |
| NPIPB2 | −0.71 | −0.18 | 0.53 | 0.06 | 0.72 | SNORD20 | −0.30 | −0.02 | −0.41 | 0.12 | −0.60 | LINC01991 | −0.17 | −0.66 | −1.10 | 0.55 | −1.09 |
| AC022968.1 | 1.42 | −0.30 | −0.76 | −0.62 | −0.89 | FO393419.3 | −0.36 | 0.39 | 0.61 | 0.28 | 0.23 | AL117378.2 | −0.30 | −1.65 | −0.99 | 0.17 | 0.04 |
| FAM104A | 0.36 | −0.05 | −0.32 | 0.19 | −0.23 | RPSAP51 | 0.45 | −0.41 | −0.01 | −0.59 | 0.72 | COPS8P2 | 0.28 | −2.05 | 0.10 | 0.96 | 1.20 |
| RPS6 | 0.43 | 0.08 | −0.04 | 0.05 | −0.35 | LINC01566 | 0.59 | −1.53 | −0.65 | 0.73 | −0.30 | AC010424.1 | −0.25 | −0.40 | 0.28 | 0.07 | 0.83 |
| SLC25A51 | 0.37 | −0.23 | −0.21 | −0.03 | 0.00 | AL391832.3 | 0.77 | −1.20 | −2.49 | −0.64 | −1.76 | AL137802.3 | 0.33 | −1.44 | −1.30 | 0.13 | 2.63 |
| AC114546.4 | −1.88 | 1.52 | 2.00 | 0.65 | 0.83 | FAM243B | −0.73 | −0.84 | 1.23 | −0.66 | 0.91 | CD8B2 | 0.10 | 0.76 | −1.59 | 0.03 | −1.47 |
| AL356806.1 | 2.12 | −1.87 | −1.34 | −0.43 | −0.70 | CRYM-AS1 | −0.21 | −0.13 | 0.10 | −0.01 | 0.40 | KRTAP2-3 | −0.45 | −0.33 | −0.21 | −0.07 | −2.21 |
| RBM43 | −0.48 | 0.26 | 0.30 | 0.24 | 0.06 | INSM2 | −0.48 | 0.01 | −0.47 | −0.16 | −0.19 | AC132825.4 | −0.18 | 0.83 | −0.53 | 0.44 | −0.52 |
| AC011472.2 | 1.55 | −0.64 | −0.20 | 0.21 | −0.14 | CPNE5 | 0.22 | −0.51 | −0.11 | −0.50 | −0.05 | LINC01754 | 0.29 | −1.93 | −0.76 | −0.86 | 0.71 |
| PMM1 | −0.35 | 0.34 | 0.06 | 0.32 | −0.14 | SCAMP5 | −0.25 | 0.19 | 0.42 | 0.18 | 0.27 | C4orf17 | 0.14 | −0.80 | −0.38 | −0.85 | −1.13 |
| NECTIN2 | 0.32 | −0.12 | −0.30 | −0.13 | −0.27 | LINC02395 | −0.55 | 0.59 | 0.24 | −0.15 | −0.68 | AL356277.1 | 0.18 | −0.50 | 0.99 | −0.89 | −0.76 |
| CD1B | 1.63 | −1.73 | −2.14 | −0.63 | −0.69 | AP001160.1 | 0.83 | −0.39 | −1.41 | −0.11 | −0.61 | AC010240.3 | −0.16 | −0.40 | −0.07 | 0.57 | 1.09 |
| AP3B2 | −0.65 | 0.41 | 0.19 | 0.10 | −0.20 | AC090049.1 | 1.11 | −1.72 | −0.98 | 0.47 | 2.00 | AL391425.1 | −0.09 | −0.68 | 0.17 | 0.45 | 0.38 |
| RNU6-745P | 2.91 | −2.42 | −2.95 | −0.20 | −0.63 | AC091826.1 | −1.38 | 0.83 | 0.58 | 1.53 | 0.64 | OR7G1 | −0.40 | −0.70 | −1.68 | 0.91 | −0.57 |
| AC011676.5 | −0.75 | 0.05 | 1.31 | −0.36 | 0.33 | SRSF12 | −0.21 | −0.10 | 0.17 | −0.21 | 0.14 | STX16 | −0.02 | 0.01 | 0.23 | 0.07 | 0.26 |
| AL031118.1 | −1.00 | −0.19 | 0.70 | 0.32 | 0.82 | OTP | 0.89 | −0.96 | 0.64 | 0.22 | 0.37 | AC008517.1 | 0.72 | −1.63 | −0.39 | 0.43 | 0.76 |
| AC106881.1 | −1.46 | 1.05 | 0.57 | 1.35 | 0.56 | RNU7-198P | 0.82 | −1.55 | −0.16 | −0.53 | −0.10 | LINC00649 | −0.04 | 0.12 | 0.25 | −0.21 | −0.16 |
| AL008638.3 | −1.23 | −0.19 | −0.11 | 0.25 | 0.34 | AL355838.1 | −1.03 | −0.92 | −0.36 | 1.40 | −1.08 | FAM47C | −0.21 | 0.58 | −0.74 | 0.92 | −1.39 |
| FLT3LG | −1.02 | −0.91 | 0.07 | −0.10 | 0.91 | AL158069.1 | 1.26 | −2.24 | −0.68 | −1.00 | 1.21 | AC007899.1 | −0.10 | −0.14 | 0.39 | −0.48 | −0.08 |
| CNTFR-AS1 | −1.30 | 0.62 | −0.63 | 0.63 | −0.15 | LINC02048 | −0.82 | 0.94 | 1.55 | −1.01 | −1.00 | ELP5 | 0.02 | −0.10 | −0.06 | 0.04 | 0.19 |
| CTGF | −0.68 | 0.47 | 1.43 | −1.06 | −0.15 | STIP1P3 | 1.20 | −1.27 | −1.16 | 0.50 | 1.25 | FCF1P6 | 0.55 | −0.19 | −1.53 | 2.13 | −0.76 |
| ABRAXAS2 | 0.32 | −0.29 | −0.33 | −0.12 | −0.20 | MIR4689 | −1.24 | −0.33 | 1.58 | −0.61 | 1.27 | OR52Q1P | −0.38 | −0.79 | 0.86 | 0.02 | 1.92 |
| G40298 | −0.92 | 1.05 | 0.26 | 0.96 | −0.25 | AC007383.2 | −0.27 | 0.33 | 0.31 | 0.09 | 0.27 | AC006960.2 | −0.12 | −1.64 | 0.14 | −0.04 | 0.87 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| CAMP | 2.00 | −1.07 | −2.32 | 0.45 | −3.11 | AF196972.1 | 0.57 | 0.38 | −0.09 | 1.04 | 0.94 | GRAMD2A | 0.05 | −0.05 | −0.17 | 0.38 | 0.35 |
| AL157829.1 | 1.39 | −1.95 | −2.95 | −0.08 | −1.64 | COX7CP1 | 0.35 | −0.06 | −0.67 | 0.03 | 0.13 | MCRIP2 | −0.04 | 0.02 | −0.20 | −0.02 | 0.01 |
| MGC16275 | −0.76 | 0.45 | 0.41 | 0.12 | −0.11 | AC008833.1 | −0.41 | −0.56 | 0.54 | −0.37 | 0.89 | AC005229.2 | −0.65 | −1.40 | 0.20 | −1.66 | 0.99 |
| IQSEC2 | −0.33 | 0.17 | 0.22 | 0.17 | 0.26 | IFNG−AS1 | 0.58 | −1.52 | 0.07 | −0.46 | 0.12 | G26809 | −0.15 | −0.51 | −0.68 | 0.58 | 1.12 |
| DDX59 | −0.25 | 0.34 | 0.29 | 0.16 | −0.11 | AC096708.3 | 0.80 | −0.53 | 1.08 | −1.65 | 0.36 | CLDN23 | −0.18 | 0.86 | 1.60 | 0.56 | −0.52 |
| SEC14L1P1 | −0.55 | 0.16 | 0.23 | 0.30 | 0.23 | NPAS2 | −0.12 | 0.38 | 0.05 | 0.06 | 0.01 | SNRPCP10 | −0.22 | −0.25 | 0.05 | 1.51 | −1.42 |
| MYLK-AS2 | −1.18 | 0.91 | 1.15 | −0.27 | 0.07 | AC037441.2 | −0.72 | 1.42 | 1.22 | 0.61 | −0.72 | AL139275.1 | −0.45 | −0.10 | −0.85 | −0.71 | −0.89 |
| SOX8 | −1.05 | 0.95 | 0.72 | 0.58 | 0.48 | SPDYA | 0.19 | 0.00 | 0.13 | 0.03 | 0.20 | OR1X1P | 0.38 | −2.07 | −0.69 | −1.47 | −0.10 |
| G13084 | −1.48 | 1.02 | 1.10 | 0.02 | 0.33 | AC083806.2 | 0.22 | −0.21 | −0.55 | −0.14 | −0.31 | MIR643 | 0.17 | −0.71 | 3.31 | −0.57 | 2.03 |
| SLC52A1 | −1.07 | 1.11 | 0.85 | 0.93 | 0.32 | RPS27AP7 | 0.22 | −0.15 | −0.37 | −0.31 | −0.25 | JKAMPP1 | 0.31 | −0.02 | −1.31 | −0.07 | −1.99 |
| DYNLL1P1 | 1.14 | −0.31 | −0.69 | 0.21 | −0.77 | AC134043.1 | 0.76 | −0.48 | −1.77 | 0.05 | −1.30 | RNA5SP461 | −0.72 | −0.22 | 0.35 | −0.66 | 0.13 |
| G26344 | −1.80 | 0.16 | 1.69 | 0.54 | 0.76 | NAGLU | 0.14 | −0.24 | −0.02 | 0.06 | 0.20 | ELL2P4 | −0.72 | 0.10 | −0.94 | 1.27 | −1.34 |
| SNUPN | −0.37 | −0.04 | 0.28 | 0.00 | 0.23 | AC002401.1 | 0.38 | 0.07 | −0.36 | 0.24 | −0.46 | SLC25A6P2 | −0.35 | −0.70 | 0.66 | −0.49 | −0.08 |
| AC008147.4 | −0.94 | 0.11 | 1.00 | −0.34 | 0.75 | BMX | −0.27 | 0.20 | 0.70 | −0.04 | 0.25 | MICC | 0.32 | 0.14 | 0.79 | 0.53 | −1.05 |
| MYADM | −0.60 | 0.16 | 0.31 | −0.02 | −0.27 | L2HGDH | 0.14 | −0.04 | 0.13 | 0.06 | 0.09 | PLCG2 | 0.02 | 0.11 | 0.11 | 0.11 | 0.02 |
| CS | 0.39 | −0.18 | −0.42 | 0.00 | −0.23 | LINC02421 | −0.37 | −0.03 | 0.48 | −0.24 | 0.01 | AC092338.1 | −0.08 | −0.25 | 0.88 | −0.24 | −0.43 |
| ANAPC13 | 0.36 | −0.16 | −0.17 | −0.14 | −0.16 | KCTD9P5 | 0.27 | −0.69 | −0.13 | −0.42 | 0.20 | AC112200.2 | −0.44 | 0.22 | −0.19 | 1.91 | −0.24 |
| CES2 | 0.40 | −0.25 | −0.45 | −0.10 | −0.11 | AL603832.1 | 0.38 | −0.03 | −0.95 | −0.19 | −0.54 | CHGA | 0.07 | 0.29 | 0.48 | 0.30 | 0.38 |
| ANKRD36BP2 | −0.71 | 0.67 | 0.78 | 0.19 | −0.43 | SLC39A11 | −0.08 | −0.05 | 0.12 | 0.11 | 0.32 | AL583722.4 | 0.09 | −0.43 | −0.24 | 0.11 | 0.34 |
| AC109462.3 | −2.37 | 0.66 | 1.20 | 1.75 | 0.76 | RNU6-758P | −0.72 | −0.21 | 1.63 | −0.31 | 0.32 | PDYN | −0.19 | −0.21 | −0.46 | −1.07 | 0.49 |
| AC025580.3 | −1.74 | 0.96 | 1.71 | 1.33 | 1.22 | AC079140.1 | −0.32 | 0.13 | −0.36 | 0.04 | 0.00 | AC098614.1 | −0.03 | −0.11 | −0.41 | 0.11 | 0.25 |
| CSTF2 | 0.38 | −0.42 | −0.81 | −0.08 | −0.10 | DOC2B | 0.28 | −0.22 | −0.37 | 0.09 | 0.30 | RNA5SP51 | −0.23 | −1.90 | −0.11 | −0.59 | 1.47 |
| AC025165.1 | −0.93 | −0.07 | 0.23 | 0.30 | 0.44 | AC084117.1 | −0.33 | −0.97 | −0.93 | 0.06 | 0.65 | AC090833.1 | 0.19 | −0.68 | −1.07 | −1.00 | −0.38 |
| AC114296.1 | −1.20 | 0.57 | 1.67 | 0.22 | 0.60 | HMGN2P13 | 1.00 | −1.61 | 0.39 | −0.35 | 1.19 | AL136310.1 | 0.05 | −0.15 | 0.11 | −0.28 | 0.05 |
| RNU1-85P | 1.56 | −1.43 | −2.14 | −1.31 | 1.03 | SNORA84 | 0.31 | 0.21 | −0.28 | 0.55 | −0.82 | ATP5MFP4 | 0.07 | −0.75 | −0.61 | 0.08 | 0.89 |
| AZGP1P1 | 0.86 | −0.17 | −0.63 | 0.39 | −0.24 | RPS3AP2 | −0.62 | −1.67 | −0.22 | −0.86 | 0.56 | KDM4D | −0.05 | −0.21 | 0.52 | −0.45 | 0.32 |
| AC069542.1 | 1.04 | −1.17 | −0.90 | −0.41 | 0.63 | COG4 | 0.08 | −0.05 | −0.14 | 0.01 | −0.01 | MTND4P2 | 0.32 | −0.92 | −1.27 | 1.28 | 0.62 |
| C6orf141 | 0.53 | −0.62 | −1.12 | −0.06 | −0.08 | HESX1 | 0.24 | 0.07 | 0.23 | 0.63 | 0.70 | FGF7P8 | 0.14 | 1.01 | −0.06 | 0.29 | −2.68 |
| LINC02473 | −1.41 | 0.79 | 0.58 | 0.77 | 0.87 | GALNT7 | 0.21 | −0.16 | −0.06 | −0.25 | 0.33 | RPS25P9 | 0.07 | −0.86 | 0.12 | −0.77 | 0.26 |
| AC090953.2 | −1.44 | 0.66 | 1.09 | −0.59 | −1.46 | AC253576.1 | −1.01 | −0.04 | −0.45 | 1.75 | −0.17 | AL607077.1 | −0.34 | −1.24 | −0.92 | −0.89 | −0.61 |
| NUDT18 | −0.38 | −0.19 | 0.10 | −0.03 | 0.29 | AC011503.2 | −0.40 | −0.05 | −0.52 | 0.12 | −0.18 | LINC02264 | 0.23 | −0.34 | −0.62 | 1.01 | −1.10 |
| AC008124.1 | −0.31 | 0.27 | 0.53 | 0.16 | 0.12 | DHRS4 | 0.15 | 0.13 | 0.00 | 0.15 | −0.30 | AC100858.2 | −0.25 | −0.73 | 0.77 | −1.26 | 0.94 |
| NOL8P1 | −1.53 | 0.60 | 0.01 | 0.13 | −0.72 | AL160313.2 | −1.31 | −0.15 | 1.74 | −1.26 | 1.54 | MTCO2P12 | 0.06 | −0.18 | 0.11 | −0.07 | 0.31 |
| AL009176.1 | −1.43 | 1.22 | 1.10 | 1.01 | 0.36 | AC100756.3 | 0.57 | −0.19 | −1.42 | 1.51 | −0.44 | AC073534.1 | 0.07 | 0.54 | 0.38 | 0.81 | 0.16 |
| PCDHB19P | −0.94 | 0.50 | 0.99 | 0.41 | 0.36 | NDE1 | −0.11 | −0.04 | −0.21 | −0.01 | 0.00 | CPN1 | 0.22 | 0.56 | −0.38 | 0.89 | 0.47 |
| MAP1LC3A | −0.55 | 0.81 | 0.60 | 0.52 | −0.31 | AC016144.1 | 0.33 | −0.18 | −0.06 | 0.56 | 1.06 | LINC02215 | 0.25 | −0.48 | −1.78 | 1.52 | 1.10 |
| AL732292.2 | 1.62 | −0.65 | −1.19 | 0.19 | 0.45 | G15372 | −0.51 | −0.34 | 1.60 | 0.79 | 1.37 | AC140658.4 | 0.67 | −1.71 | 0.59 | −0.72 | 1.27 |
| RALGDS | −0.57 | 0.25 | 0.36 | 0.14 | 0.13 | AC022447.5 | −1.59 | 1.53 | 2.23 | −0.80 | −0.70 | AC008735.2 | −0.06 | −0.17 | 0.27 | −0.06 | −0.17 |
| AC016866.3 | 1.00 | −0.46 | −0.96 | 0.13 | 0.11 | AC079834.2 | 0.35 | 0.03 | −0.24 | 0.52 | −0.08 | AL592295.3 | 0.06 | −0.17 | 0.76 | −0.07 | 0.72 |
| SMG7-AS1 | −0.71 | 0.13 | 0.28 | 0.44 | 0.63 | NEK4P1 | 0.59 | 0.40 | −1.72 | −0.41 | −2.00 | RN7SKP219 | 0.09 | 0.14 | 0.19 | −0.51 | −0.54 |
| LINC02298 | −0.93 | 0.04 | 0.22 | 0.40 | 0.60 | PCOLCE | −0.26 | 0.23 | 1.20 | −0.48 | −0.04 | AC083899.3 | 0.40 | 0.38 | −0.26 | 2.34 | −0.82 |
| FAM57B | −0.92 | −0.02 | −0.39 | 0.21 | −0.09 | BCL2L1 | 0.12 | −0.04 | −0.21 | −0.10 | −0.15 | AC124290.1 | 0.35 | −1.63 | −1.92 | 0.00 | −0.47 |
| CYP2D7 | −0.77 | 0.38 | 0.11 | 0.46 | 0.34 | AC139792.2 | 0.56 | 0.32 | −0.17 | 0.23 | −0.06 | AC103563.4 | 0.71 | −1.29 | NA | −0.80 | −1.19 |
| PMP2 | −0.85 | 0.38 | 1.04 | 0.22 | 1.15 | RN7SL264P | −0.41 | −1.42 | 0.17 | 0.61 | 1.44 | LINC02523 | −0.30 | 0.14 | −0.14 | 1.11 | 0.66 |
| SBDS | 0.52 | −0.22 | −0.49 | −0.16 | −0.48 | MTND4LP30 | −0.31 | 0.12 | 0.49 | −0.01 | 0.23 | BMI1 | 0.03 | 0.16 | 0.21 | −0.03 | 0.06 |
| AL031008.1 | −1.42 | 1.14 | 0.66 | 0.31 | 0.55 | CLDN10 | −0.41 | 0.22 | 1.01 | −0.13 | 0.65 | AC004148.1 | −0.21 | 0.11 | −0.54 | −0.08 | −0.91 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC068446.2 | −0.76 | 0.49 | 1.20 | 0.73 | 1.33 | AC096564.1 | 0.24 | −0.27 | −0.62 | −0.05 | −0.25 | AC015936.1 | 0.21 | −1.15 | −2.24 | 2.46 | −0.49 |
| SH3D19 | −0.27 | 0.34 | 0.19 | 0.20 | −0.16 | AC127502.1 | −0.19 | 0.10 | 0.28 | −0.02 | −0.24 | AL662844.2 | −0.63 | 0.20 | 1.17 | 3.51 | 2.07 |
| AL451042.1 | 1.27 | −0.54 | −0.75 | −0.56 | −0.62 | AC008850.1 | 0.36 | −0.05 | 0.45 | 0.31 | 0.34 | AC080128.2 | 0.14 | −0.86 | −0.91 | 0.38 | 0.25 |
| RUBCNL | 0.89 | −0.77 | −0.34 | −0.32 | 0.02 | AC099850.1 | −0.26 | −0.15 | 0.32 | 0.62 | 0.57 | IMPG1 | 0.05 | −0.06 | 0.31 | 0.23 | −0.08 |
| MIR200CHG | 0.70 | −0.05 | 0.14 | −0.06 | −0.08 | AC132872.1 | −0.20 | −0.03 | −0.46 | 0.44 | 0.39 | MTCO3P7 | 0.71 | 0.05 | −1.87 | 0.82 | −2.51 |
| NKX2-5 | −1.32 | −0.10 | 0.73 | −0.38 | 0.82 | AL162171.1 | −0.30 | 0.85 | −0.61 | 0.48 | −0.70 | RPL23AP15 | −0.39 | −1.39 | −0.51 | −0.96 | 1.07 |
| AC007292.1 | −0.98 | −0.22 | 0.17 | −0.29 | −0.27 | AC118344.1 | −0.24 | −0.09 | 0.12 | −0.10 | 0.17 | AL391417.1 | −0.56 | 0.49 | −0.12 | −0.19 | −1.03 |
| KRR1 | 0.31 | −0.07 | −0.23 | −0.06 | −0.26 | AC011816.2 | −0.59 | −0.35 | 0.14 | 0.44 | 0.90 | AC084824.5 | −0.06 | −0.17 | −0.34 | 0.11 | 0.12 |
| PRKG1-AS1 | −1.01 | 0.13 | 1.01 | −0.05 | 0.19 | CASP6 | 0.14 | 0.03 | −0.18 | 0.14 | −0.07 | COX17P1 | 0.19 | 1.09 | 0.02 | 0.98 | −0.46 |
| AHNAK | −0.32 | 0.31 | 0.13 | 0.09 | −0.11 | AC090159.1 | 0.67 | −0.60 | −0.27 | 0.42 | 1.08 | SELENOH | 0.02 | −0.13 | 0.01 | 0.04 | 0.12 |
| RNA5SP206 | −1.71 | 0.98 | 1.62 | 0.60 | 0.29 | CCDC157 | −0.24 | 0.30 | −0.06 | 0.27 | −0.02 | AC103564.2 | 0.32 | 0.55 | −0.89 | −0.11 | −1.97 |
| MLEC | 0.37 | −0.29 | −0.33 | −0.16 | 0.01 | RNA5SP132 | −0.70 | −1.43 | 0.98 | −1.27 | 1.26 | RRM2P2 | −0.16 | −0.85 | 0.57 | −1.21 | 1.26 |
| METTL5 | 0.45 | −0.21 | −0.23 | −0.17 | −0.11 | MTND4P26 | 0.24 | −0.36 | −1.05 | −0.16 | −0.39 | EIF4A2P5 | −0.24 | −0.43 | −1.01 | 1.06 | 1.46 |
| IL1RAPL1 | −1.15 | 0.14 | −0.25 | 0.17 | 0.11 | OR14J1 | −0.73 | 0.50 | −0.59 | 0.41 | −0.59 | SPAG11A | 0.32 | −0.72 | −2.11 | 1.45 | −0.20 |
| PRPF38B | 0.33 | −0.33 | −0.36 | −0.17 | −0.04 | AL133353.1 | 1.24 | 0.00 | −1.47 | −1.40 | −1.49 | AC010445.1 | 0.33 | −0.76 | −0.93 | 0.54 | −0.97 |
| RPL18 | 0.44 | 0.03 | 0.00 | −0.12 | −0.28 | EIF1AD | 0.10 | 0.01 | −0.26 | −0.05 | −0.23 | KCNQ1-AS1 | 0.14 | −1.92 | −0.57 | 0.28 | 1.88 |
| RPS19 | 0.41 | 0.00 | −0.01 | −0.08 | −0.28 | CCDC69 | −0.25 | 0.00 | 0.04 | 0.08 | −0.16 | AL121757.1 | 0.21 | −0.23 | 1.64 | −0.33 | 0.74 |
| SRF | 0.28 | −0.27 | −0.62 | −0.12 | −0.23 | PRDM15 | −0.13 | −0.14 | −0.31 | 0.11 | 0.25 | AL158055.1 | −0.42 | 1.50 | 1.63 | 0.85 | 0.77 |
| AC009411.1 | −1.95 | −0.68 | −1.05 | 0.96 | 0.19 | AL355032.1 | 0.36 | 0.00 | −0.27 | 0.05 | −0.14 | AC010975.1 | −0.33 | −0.37 | 0.37 | 0.99 | 0.01 |
| AK3P5 | 0.81 | −0.25 | −1.29 | −0.09 | −0.50 | AP000354.1 | 1.12 | −2.70 | −1.58 | −0.15 | 0.13 | LINC00972 | 0.29 | 0.73 | −1.99 | 0.94 | −1.29 |
| AL355312.5 | −0.63 | 0.03 | 0.23 | 0.11 | −0.12 | AC021242.3 | −0.85 | −0.53 | 0.05 | 0.40 | 0.89 | AC008957.2 | 0.06 | −1.00 | −1.04 | −0.34 | 0.33 |
| CD69 | 1.14 | −1.46 | −1.00 | −0.28 | −0.52 | SCN3B | 0.20 | 0.17 | −0.23 | −0.24 | −0.30 | SH3PXD2A | 0.02 | 0.02 | 0.02 | −0.04 | −0.07 |
| AL139289.1 | 0.77 | −0.29 | −0.21 | −0.16 | −0.31 | AL583824.1 | 0.26 | 0.15 | 0.03 | −0.43 | −0.52 | RNU6ATAC26P | 0.17 | −1.13 | 0.62 | −0.02 | 0.49 |
| MCCC2 | 0.31 | −0.08 | −0.17 | 0.00 | −0.04 | LINC02359 | 0.77 | 0.24 | −0.38 | 0.42 | −0.97 | AC007431.2 | −0.08 | −0.01 | −0.69 | 0.42 | 0.51 |
| DACT3-AS1 | −0.81 | 0.40 | −0.20 | 0.64 | 0.01 | RPS4XP13 | 0.95 | −0.40 | −0.89 | 0.02 | −0.19 | SERPINB11 | 0.16 | −0.16 | −0.06 | 0.16 | −1.78 |
| RANBP3L | −1.62 | 0.73 | 2.07 | 0.70 | 0.72 | AC002044.1 | 0.96 | −0.21 | 0.48 | −1.28 | −1.90 | SLC4A1APP2 | 0.29 | −1.08 | −0.98 | −0.17 | −1.23 |
| SNORD3B-1 | 0.81 | −1.02 | −0.93 | −0.51 | 0.56 | AC004941.1 | −0.60 | −0.35 | 0.99 | −0.10 | −0.36 | AC078962.3 | 0.06 | 0.27 | −0.58 | −0.43 | −0.59 |
| AC008537.2 | −1.17 | 1.03 | 1.98 | −0.41 | 0.24 | IFT43 | −0.10 | −0.09 | 0.04 | −0.13 | 0.04 | RIMS4 | −0.08 | 0.36 | 0.94 | 0.36 | 0.18 |
| AP000907.2 | −1.35 | −0.08 | 0.83 | 1.09 | 1.07 | AC140134.1 | −0.26 | 0.20 | 0.62 | 0.34 | 0.75 | C11orf53 | 0.36 | −1.36 | −0.36 | 0.36 | −0.17 |
| AC073174.2 | −1.62 | 0.70 | −1.19 | 0.86 | −1.26 | NUP210L | −0.16 | −0.30 | −0.33 | 0.09 | 0.23 | NKILA | −0.09 | −0.96 | −0.93 | −0.46 | −0.34 |
| HIST2H2AA3 | 0.96 | −0.86 | −1.96 | 0.06 | −0.84 | IFNWP2 | 1.16 | 0.42 | −1.70 | −0.13 | −1.11 | AC135999.1 | 0.71 | 0.22 | −1.87 | 0.51 | −0.48 |
| ABHD11 | −0.47 | 0.36 | 0.26 | 0.23 | 0.01 | PXMP2 | −0.26 | 0.02 | 0.34 | 0.13 | 0.18 | PRODH2 | −0.31 | −0.33 | −2.53 | 1.11 | −0.47 |
| AZI2 | 0.39 | −0.18 | −0.34 | 0.06 | −0.21 | AC007690.1 | −0.25 | −0.17 | −0.40 | 0.12 | 0.38 | AC008635.1 | −0.06 | −0.47 | −0.04 | 0.30 | 0.36 |
| SCOC-AS1 | −0.86 | 0.05 | 0.97 | 0.14 | 0.14 | FKTN | 0.11 | −0.12 | −0.17 | −0.07 | −0.16 | QRSL1P2 | 0.30 | 0.13 | −0.69 | 0.02 | −1.49 |
| LAMTOR3 | 0.41 | −0.02 | −0.13 | −0.05 | −0.27 | ATAD3C | −0.31 | −0.80 | 0.37 | −0.95 | 0.23 | RPS18P13 | −0.17 | −0.44 | 2.46 | −1.22 | 1.55 |
| AC231533.2 | −1.05 | 0.47 | 1.04 | 0.10 | 0.70 | KIAA0040 | −0.17 | 0.05 | 0.26 | −0.12 | −0.13 | AC008565.1 | −0.24 | −0.35 | 0.09 | 2.44 | 0.45 |
| AP000811.1 | −0.91 | 0.94 | 1.21 | 0.12 | 0.03 | AC025164.1 | −0.25 | −0.20 | 0.01 | 0.24 | 0.24 | LINC02428 | 0.19 | −0.83 | −1.88 | −0.76 | −1.12 |
| RPL36A | 0.40 | −0.29 | −0.47 | 0.18 | 0.16 | AL356277.2 | 1.49 | 0.20 | −0.49 | 0.22 | −0.10 | RFPL2 | 0.14 | −0.73 | 0.03 | −0.54 | 0.99 |
| AC093772.1 | 1.98 | 0.20 | −1.85 | −0.96 | −1.99 | ANKRD34B | 0.57 | −0.56 | −1.32 | 0.19 | −0.77 | AL365220.1 | −0.70 | −1.42 | 0.76 | −1.11 | 1.39 |
| RNA5SP351 | −2.19 | 1.00 | 0.44 | 0.88 | −1.14 | STK25 | −0.11 | −0.05 | −0.23 | 0.15 | 0.13 | RN7SL482P | 0.10 | −0.35 | 0.70 | −0.16 | 0.33 |
| MCF2L-AS1 | −1.23 | 0.09 | 0.83 | 0.47 | 0.90 | LINC01709 | −0.97 | −0.35 | 0.21 | −0.52 | −1.17 | RN7SL14P | −0.18 | 0.37 | −0.62 | 0.25 | −1.30 |
| AC006547.1 | −0.54 | 0.00 | 0.25 | 0.14 | 0.31 | MYBPC3 | −0.30 | −0.48 | −0.83 | −0.22 | −0.44 | OR10J4 | −0.70 | 0.69 | 0.59 | −0.27 | −1.20 |
| RABGAPIL | −0.19 | 0.18 | 0.26 | 0.05 | −0.01 | GOLT1A | −0.92 | −0.28 | 0.51 | 0.06 | 0.23 | ALG1L7P | −0.10 | −0.10 | 0.28 | −0.40 | 0.11 |
| AL138902.1 | 1.06 | −0.75 | −1.51 | −0.18 | −0.75 | AC012467.1 | −0.84 | −0.75 | 3.31 | −1.27 | 2.10 | PAGE5 | 0.24 | −0.40 | −0.96 | 1.20 | 1.48 |
| CHMP1B | 0.33 | 0.16 | −0.53 | 0.21 | −0.62 | ASB12 | −0.83 | 2.17 | −0.82 | 1.98 | −0.83 | AC097721.1 | −0.04 | −0.34 | 0.03 | −0.36 | 0.20 |
| SLC29A4 | −0.97 | 0.36 | 0.27 | 0.06 | 0.31 | AC023866.2 | 0.83 | −0.77 | 0.58 | 0.41 | 0.12 | AC079362.1 | −0.38 | −0.96 | −1.18 | 0.90 | −0.02 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| PPP1R3D | 0.42 | −0.06 | −0.33 | 0.13 | −0.18 | MCCD1P2 | −0.58 | 0.82 | 0.51 | 0.77 | 0.10 | AC103855.2 | 0.27 | 0.13 | 0.13 | 0.74 | −0.55 |
| AC129507.1 | −0.71 | 0.29 | −0.25 | 0.60 | −0.16 | CELA2B | −0.40 | 0.38 | 0.75 | −0.16 | 0.43 | HOXB1 | −0.14 | −0.98 | −1.19 | 0.11 | 2.20 |
| AL160313.1 | −1.07 | 0.87 | 2.08 | 0.08 | 0.41 | ETS1-AS1 | 0.43 | −1.10 | −1.03 | −0.62 | −0.63 | PTX4 | 0.16 | 0.35 | −1.28 | −0.65 | −0.91 |
| SAXO2 | −0.57 | −0.03 | 0.44 | −0.42 | 0.07 | CPT1C | 0.22 | 0.19 | −0.03 | 0.10 | −0.38 | AC068756.1 | −0.38 | 0.78 | −0.37 | 0.01 | −1.72 |
| AC006122.1 | 1.25 | −0.94 | −0.61 | −0.52 | −0.26 | NOX3 | 0.92 | −0.77 | −2.13 | 0.94 | −0.63 | OR8U1 | 0.25 | 0.09 | −1.76 | 1.07 | 0.05 |
| PKN2-AS1 | −0.65 | −0.18 | −0.31 | 0.01 | 0.18 | SRGAP2-AS1 | 0.42 | −0.03 | 0.24 | −0.29 | −0.67 | IMMP1LP2 | 0.56 | −0.97 | −1.26 | −0.51 | −1.38 |
| MYO3B | −0.82 | 0.54 | 0.25 | −0.27 | −0.80 | SDHAF1 | 0.13 | −0.03 | −0.15 | 0.07 | −0.04 | AC013399.1 | −0.51 | −0.73 | 2.16 | −1.57 | 2.70 |
| PML | 0.40 | −0.49 | −0.73 | −0.13 | 0.01 | LIN28A | −0.43 | −0.57 | 0.79 | −0.06 | 0.09 | AC019163.1 | 0.23 | 0.55 | 0.66 | 0.01 | −1.04 |
| CLEC3A | 2.02 | −2.29 | −2.64 | 1.85 | 0.23 | OR5K1 | −0.48 | 0.43 | 0.03 | 0.55 | −0.45 | LINC02419 | −0.27 | 0.25 | 0.66 | −0.06 | 2.05 |
| GOLPH3 | 0.34 | −0.10 | −0.18 | −0.12 | −0.14 | AL512380.2 | −0.62 | 0.89 | 0.92 | 0.59 | 0.60 | LINC00892 | 0.08 | 0.03 | −0.26 | −0.36 | −0.52 |
| LINC01090 | −1.12 | 0.80 | 0.66 | 0.52 | 0.25 | AC010980.1 | 0.20 | −0.07 | −0.80 | 0.37 | 0.02 | C16orf90 | −0.16 | 0.22 | 0.50 | 0.75 | 0.08 |
| PGM5-AS1 | −1.48 | 0.84 | 1.90 | 0.16 | 0.18 | AC016596.1 | 0.28 | 0.07 | −0.14 | −0.34 | −0.30 | AP001002.1 | −0.24 | −0.67 | −1.82 | 1.84 | −0.62 |
| MBOAT1 | −0.44 | 0.26 | 0.27 | 0.08 | −0.05 | AL445489.1 | 0.26 | −0.54 | 0.07 | −0.09 | 0.68 | OR11L1 | −0.19 | −0.38 | 0.10 | −0.22 | 0.52 |
| SUGT1 | 0.29 | −0.08 | −0.15 | −0.09 | −0.10 | RNA5SP168 | 0.44 | −0.03 | 0.19 | 0.00 | −0.04 | AC009084.1 | −0.23 | 0.24 | 0.62 | 0.46 | 0.19 |
| CHRNA5 | 0.88 | −1.21 | −0.75 | −0.57 | 0.41 | RNU7-84P | −0.42 | 0.19 | 0.26 | 0.50 | 0.32 | AC062020.1 | 0.70 | −1.80 | 0.79 | −0.48 | 1.16 |
| AL161719.1 | −1.33 | 0.50 | 0.99 | 0.14 | 0.51 | PA2G4P2 | −0.49 | 1.10 | −1.05 | 0.96 | −0.44 | AC011447.5 | −0.13 | 0.23 | 0.54 | −0.02 | 0.01 |
| PLSCR4 | −0.56 | 0.59 | 0.73 | 0.29 | 0.07 | MYCBP2 | 0.11 | 0.22 | 0.21 | 0.20 | −0.08 | AL360271.1 | −0.27 | 0.55 | −0.14 | −0.06 | −1.13 |
| CLEC5A | 0.89 | −0.86 | −0.14 | −0.30 | −0.09 | SNX22 | −0.21 | −0.33 | 0.17 | −0.34 | 0.23 | MAGEB4 | 0.56 | −0.79 | 0.67 | −0.12 | −0.76 |
| AC026401.3 | 0.58 | −0.32 | −0.38 | −0.36 | −0.07 | RNU6-1054P | 0.82 | −0.46 | 0.25 | −0.30 | −0.18 | AL139421.1 | 0.08 | −0.33 | 0.37 | −0.19 | 0.05 |
| FGF2 | −0.90 | 0.71 | 1.10 | 0.28 | 0.24 | AL645949.1 | −0.31 | −0.16 | 0.44 | −0.10 | 0.26 | LINC01877 | −0.15 | 0.10 | −0.45 | 0.64 | −0.47 |
| SEZ6L | −1.16 | 0.54 | 1.95 | −0.23 | −0.06 | EFNA2 | −0.92 | −0.01 | 0.10 | −0.02 | 0.64 | LINC01221 | 0.43 | −1.41 | 0.21 | 0.71 | 2.38 |
| PPIL2 | −0.32 | 0.10 | −0.10 | 0.24 | 0.16 | GLS2 | −0.38 | 0.58 | −0.66 | 0.86 | −0.40 | AC018767.1 | −0.49 | 1.31 | −0.18 | 0.78 | −1.62 |
| ARHGEF6 | −0.78 | 0.28 | 0.49 | 0.21 | 0.11 | C10orf91 | −0.39 | −0.26 | −1.37 | 0.35 | −0.17 | MIR3161 | −0.14 | −0.21 | 0.46 | 0.08 | 0.31 |
| PNMA8A | −0.77 | 0.28 | 0.57 | −0.14 | −0.65 | AC136285.3 | −0.36 | −0.19 | 0.06 | −0.05 | 0.01 | AGO1 | −0.02 | 0.19 | 0.21 | 0.19 | 0.05 |
| RBBP8NL | −0.65 | 0.40 | 0.02 | 0.43 | 0.39 | AC016042.1 | −0.41 | −0.16 | −1.05 | 0.64 | −0.97 | AC009643.2 | 0.24 | −1.42 | −1.18 | 0.82 | 1.88 |
| IRAK1BP1 | −0.43 | 0.26 | 0.80 | 0.11 | 0.08 | AC018521.3 | −0.65 | 0.19 | 0.47 | 0.41 | 0.91 | OR1D3P | 0.38 | −0.93 | −1.02 | 0.62 | −0.20 |
| PMS2P1 | −0.28 | 0.13 | 0.29 | 0.06 | 0.07 | AC104078.2 | 0.95 | −0.85 | −2.61 | 0.79 | −2.58 | SBDSP1 | 0.02 | −0.15 | −0.11 | −0.17 | −0.06 |
| G43312 | −2.12 | 0.00 | 1.60 | −0.18 | 1.18 | AC004129.3 | 1.23 | −0.36 | −1.95 | 1.08 | −0.28 | MARK2P4 | −0.15 | −2.24 | −0.35 | −0.16 | 2.02 |
| ETNK1 | 0.39 | −0.19 | −0.25 | 0.02 | −0.07 | GZMK | 0.82 | −1.08 | 1.06 | −0.82 | 1.66 | MTCO2P23 | −0.36 | −0.07 | 0.46 | 0.42 | −1.02 |
| SCMH1 | −0.27 | 0.07 | −0.04 | −0.02 | 0.06 | AC080112.3 | −0.29 | −0.23 | −0.04 | −0.21 | 0.39 | RP11-152F13.7 | −0.08 | −0.24 | 0.10 | −0.06 | 0.30 |
| ADRB2 | −0.66 | 0.61 | 0.38 | 0.13 | −0.11 | LINC00996 | 0.51 | −1.34 | 0.26 | −0.57 | 0.92 | ADGRF5P2 | 0.25 | −1.40 | 0.01 | 0.66 | 1.40 |
| MAFG−DT | 0.94 | −0.26 | −0.91 | 0.08 | 0.08 | AC008747.1 | −0.72 | 0.20 | 1.40 | 0.56 | 1.04 | LINC01808 | −0.09 | 0.48 | 0.02 | 0.15 | −0.34 |
| ENPP2 | −0.79 | 0.39 | 1.02 | −0.18 | 0.03 | FAM53C | 0.09 | −0.02 | −0.12 | 0.07 | −0.01 | AC027288.2 | 0.07 | −0.41 | 1.03 | −0.14 | 0.12 |
| ABL2 | 0.34 | −0.33 | −0.33 | −0.35 | −0.26 | RNU4-58P | −0.97 | −0.70 | −0.38 | −0.65 | 0.16 | HOXA11 | 0.09 | 0.18 | 1.44 | −0.41 | −0.79 |
| SLC35C2 | −0.35 | 0.09 | 0.16 | 0.08 | 0.15 | MTND5P15 | 0.55 | 0.07 | −0.35 | −0.15 | −0.13 | AL031670.1 | −0.05 | 0.08 | −0.22 | 0.28 | 0.24 |
| CEP95 | −0.22 | 0.16 | 0.21 | 0.09 | 0.04 | INSYN2 | 0.18 | −0.05 | −0.24 | 0.03 | −0.04 | LINC02543 | 0.38 | −0.97 | −1.19 | 0.43 | −0.83 |
| ST7 | 0.21 | −0.03 | −0.43 | 0.04 | −0.41 | G36217 | −0.36 | 0.43 | 0.54 | −0.61 | −0.20 | AC110602.1 | −0.12 | 0.71 | 1.21 | 0.15 | 0.24 |
| HPS5 | 0.35 | −0.26 | −0.14 | −0.10 | 0.21 | MIR5480 | 0.51 | 0.79 | −0.17 | 0.24 | 0.03 | NPHP3-ACAD11 | −0.17 | 0.16 | 1.55 | −0.84 | −0.62 |
| OR2A9P | −1.08 | 0.18 | 1.42 | −1.22 | 0.05 | CHST15 | 0.11 | −0.17 | −0.31 | −0.02 | −0.13 | AL354872.1 | 0.33 | −2.14 | 1.54 | −0.81 | 2.20 |
| AC005224.1 | 0.71 | −0.30 | −0.79 | −0.12 | −0.16 | AC096921.1 | −0.24 | −0.21 | 0.57 | −0.08 | 0.67 | MIR3135A | −0.16 | 1.22 | 0.69 | 1.39 | 0.13 |
| LRRC37A2 | −0.34 | 0.14 | 0.23 | 0.01 | 0.16 | C1orf100 | 0.55 | −0.80 | −0.22 | −0.63 | −0.24 | AC007656.2 | −0.15 | −0.81 | −1.07 | 0.07 | 0.88 |
| AC079858.1 | 1.46 | −0.75 | −0.91 | 0.26 | 0.20 | PDS5B | 0.09 | −0.03 | −0.05 | −0.08 | −0.02 | SLC25A24P1 | 0.20 | 0.45 | −0.79 | −0.72 | 0.07 |
| FAM133A | −1.21 | 0.46 | 1.05 | −0.14 | 0.77 | RPSAP53 | 0.83 | −0.71 | −0.45 | 1.24 | 0.30 | AC006530.1 | −0.17 | −1.16 | 2.53 | −1.54 | 0.99 |
| MIR4534 | −1.57 | 0.54 | 2.19 | 1.41 | 1.49 | EIF1AXP1 | 0.26 | −0.21 | −0.44 | 0.05 | −0.25 | DEFB121 | 0.23 | −1.46 | −1.30 | −0.11 | −0.58 |
| AC091057.6 | 0.69 | −0.77 | −1.14 | −0.48 | −0.07 | FBXO8 | −0.12 | 0.19 | 0.12 | 0.04 | −0.24 | AL161911.1 | −0.08 | −0.17 | 0.01 | 0.39 | 0.23 |
| AP000445.1 | −2.04 | 1.56 | 2.65 | 0.61 | 0.68 | KRTAP5-AS1 | 0.48 | −0.34 | −1.07 | 0.15 | 0.80 | PYHIN5P | −0.31 | 0.57 | −2.14 | 0.42 | −1.71 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| MEI4 | −1.37 | 0.28 | 0.58 | −0.78 | −0.32 | RN7SL687P | −0.86 | 0.50 | −0.60 | 1.58 | −0.70 | AC007950.2 | −0.09 | −0.23 | −0.07 | −0.18 | −0.15 |
| BMPR2 | 0.42 | −0.03 | −0.09 | −0.09 | −0.33 | RPL37P23 | 0.62 | −1.04 | −1.95 | 0.11 | −0.30 | LINC01556 | 0.68 | −1.09 | −1.72 | 1.56 | 1.00 |
| OR1F12 | −1.02 | 0.08 | 1.25 | −0.03 | 0.76 | CABLES2 | −0.12 | −0.06 | −0.19 | 0.09 | −0.03 | RPL7P26 | 0.09 | 0.76 | −0.22 | −0.22 | −1.35 |
| ATP5PBP1 | 0.91 | −0.46 | −0.52 | −0.40 | −0.50 | EDDM3CP | 0.41 | −0.08 | 0.43 | −0.29 | −0.01 | OPN1LW | −0.25 | −0.26 | −0.78 | −0.29 | −1.66 |
| MAPKAPK3 | 0.38 | −0.05 | −0.30 | 0.09 | −0.19 | C2 | −0.25 | −0.23 | 0.16 | 0.22 | 0.42 | RAP1GAP | 0.05 | −0.29 | −1.00 | 0.10 | 0.35 |
| PTGFR | −0.98 | 0.67 | 1.83 | −0.69 | 0.01 | MKNK2 | 0.12 | 0.15 | −0.15 | 0.21 | −0.25 | MRPS18BP2 | −0.45 | −0.58 | −1.34 | −0.90 | −0.92 |
| CLPTM1L | 0.23 | −0.13 | −0.42 | −0.01 | −0.17 | RNU6-886P | −1.17 | 0.49 | 0.88 | 0.26 | 1.75 | LGALS14 | 0.32 | 0.28 | −2.66 | 0.34 | −1.82 |
| CCDC130 | −0.48 | 0.11 | 0.05 | 0.16 | 0.12 | KRT8P12 | −0.16 | −0.08 | 0.22 | −0.02 | 0.16 | LINC01928 | −0.22 | −0.17 | −2.28 | 0.06 | −2.68 |
| SP3 | 0.28 | 0.00 | −0.24 | 0.01 | −0.30 | AC121493.1 | −0.69 | 0.24 | 2.18 | −0.59 | 0.09 | AC091951.3 | −0.69 | 0.21 | −0.06 | 0.92 | 0.58 |
| RN7SL13P | −1.46 | 0.55 | −0.99 | 1.45 | −0.62 | AL117379.1 | 0.29 | −0.26 | 0.51 | 0.03 | 0.52 | AC114477.1 | −0.48 | −0.69 | 1.62 | −0.48 | 1.85 |
| RPSAP70 | −2.20 | 3.33 | 0.76 | 1.39 | −0.69 | AC136628.3 | 1.09 | 0.69 | 1.85 | 0.47 | 0.54 | RPS17P11 | −0.69 | 1.60 | 0.64 | −1.13 | −0.90 |
| AC078925.4 | −1.18 | 0.88 | 1.56 | 0.95 | 0.41 | AL160291.1 | 0.59 | −0.73 | 0.57 | −0.64 | −0.51 | AP005229.1 | 0.37 | 0.09 | −0.99 | 0.41 | −0.12 |
| RGN | −0.86 | 0.73 | 1.06 | 0.42 | 0.05 | AC116025.2 | −0.33 | 0.27 | −0.18 | 0.25 | 0.35 | AL031430.1 | 0.27 | 0.21 | 0.36 | 0.04 | 1.02 |
| GALNTL6 | −1.08 | 0.81 | 0.16 | 0.96 | 0.06 | AC104640.1 | 1.10 | −0.71 | −0.10 | −0.53 | −0.65 | IGKV1D-39 | 0.69 | 0.35 | 0.62 | 2.47 | 0.03 |
| AC138932.1 | −0.67 | 0.10 | 0.36 | 0.50 | 0.56 | NRG3-AS1 | −0.86 | −0.70 | −0.22 | 0.39 | 1.46 | LINC01412 | −0.26 | 0.32 | −0.13 | 1.30 | 0.08 |
| AC114488.2 | −0.63 | −0.09 | 0.57 | −0.05 | 0.30 | AC092746.1 | 1.36 | −0.70 | −2.83 | −0.21 | −2.46 | AC012065.3 | 0.15 | −0.80 | 2.48 | −1.60 | 0.12 |
| AF001548.2 | −0.77 | 0.44 | 0.29 | 0.46 | 0.51 | RNA5SP444 | −0.87 | 0.58 | −0.42 | 1.93 | 0.08 | GOLPH3L | −0.02 | 0.01 | 0.09 | 0.11 | 0.04 |
| CEP112 | −0.54 | 0.23 | 0.53 | −0.21 | −0.12 | G11189 | 0.59 | 0.59 | 0.40 | −0.64 | −1.24 | AL662890.1 | −0.11 | −1.07 | −2.37 | 0.15 | −0.02 |
| SNORA79 | −0.57 | 0.40 | 0.42 | 0.15 | −0.38 | AL365502.1 | −0.94 | 0.81 | 0.61 | −0.18 | −0.72 | RBM22P1 | −0.18 | −0.88 | −1.60 | 1.07 | −0.18 |
| ISX | 1.74 | −0.32 | −2.42 | 0.46 | −1.15 | HLA-DPB2 | 0.91 | 0.36 | −2.39 | 0.09 | 0.08 | LINC01891 | 0.15 | −0.53 | −0.62 | −0.31 | −0.04 |
| LINC00323 | −1.55 | 0.62 | 2.11 | 0.48 | 0.41 | AL050316.1 | 0.66 | 0.07 | 0.19 | −0.58 | −0.78 | CCDC148-AS1 | −0.21 | −0.14 | −1.02 | 0.79 | 0.51 |
| SHTN1 | 0.24 | −0.06 | −0.40 | 0.04 | −0.11 | AC003072.1 | 0.30 | 0.31 | −0.51 | 0.01 | −0.49 | CSMD3 | −0.09 | −0.33 | −0.46 | 0.10 | −0.15 |
| EVA1C | −0.41 | 0.30 | 0.07 | 0.26 | 0.16 | ANKRD18B | 0.19 | −0.18 | −0.14 | 0.24 | 0.30 | CSNK2B | 0.03 | 0.34 | −0.10 | 0.32 | −0.20 |
| G17695 | −0.78 | −0.48 | 0.26 | −0.19 | 0.46 | NKIRAS1 | 0.11 | −0.05 | 0.00 | 0.00 | 0.08 | AC090132.1 | −0.69 | −0.42 | −0.20 | −1.01 | 0.57 |
| LDHAP7 | 1.31 | −0.92 | −1.93 | 0.14 | −0.78 | AC140061.6 | −1.05 | −0.50 | 0.92 | −0.65 | −0.40 | AC132807.1 | 0.42 | −0.58 | −0.14 | 0.67 | −0.33 |
| CCNY | 0.28 | −0.06 | −0.16 | −0.05 | −0.14 | AC004947.1 | −0.57 | −0.36 | −0.99 | 0.96 | 0.59 | LINC00251 | −0.22 | −0.89 | 0.29 | 0.76 | −1.35 |
| PACRGL | −0.23 | 0.08 | 0.32 | 0.08 | 0.23 | MB | −0.46 | 0.20 | 0.63 | 0.59 | 0.84 | LINC02371 | −0.17 | 0.26 | 0.20 | 0.28 | 0.39 |
| IMPA1 | 0.34 | −0.25 | −0.32 | −0.18 | 0.05 | OPRD1 | −0.49 | 0.54 | −0.70 | 0.34 | −0.56 | CICP17 | −0.33 | 0.26 | 0.42 | 0.03 | −2.27 |
| AC084024.4 | −0.69 | −0.40 | 0.57 | 0.01 | 0.49 | AC106744.2 | −0.66 | 0.31 | −0.74 | 0.62 | −0.22 | CEACAM1 | −0.04 | 0.10 | 0.28 | −0.01 | 0.31 |
| HMGN2P28 | −1.01 | 0.79 | 0.96 | 0.70 | 0.09 | AC015849.6 | 0.83 | −0.21 | −1.31 | 0.83 | −0.36 | RNU6-350P | −0.20 | 1.68 | −0.97 | 0.59 | −1.41 |
| RALY | 0.16 | −0.08 | −0.16 | −0.08 | −0.10 | AC087821.1 | −0.41 | −0.34 | 0.84 | −0.59 | 0.02 | OR6C6 | −0.42 | 0.40 | −1.96 | 0.49 | −1.76 |
| APC | 0.25 | 0.04 | −0.22 | −0.02 | −0.29 | AL133243.2 | 0.21 | 0.12 | 0.26 | −0.11 | −0.10 | AC073626.1 | −0.09 | −0.13 | −0.83 | 0.21 | −0.09 |
| AC022150.2 | −0.88 | 0.01 | 0.86 | 0.10 | 0.33 | RNA5SP355 | −0.36 | 0.31 | −0.07 | 0.52 | −0.21 | MYOD1 | −0.18 | 0.88 | −0.74 | 2.64 | −0.45 |
| BCLAF1 | 0.25 | −0.03 | −0.20 | 0.00 | −0.18 | PRELID3BP8 | 0.67 | −0.99 | 1.62 | −1.11 | 0.86 | AC106744.1 | −0.41 | −0.17 | −2.13 | 1.63 | −0.37 |
| MIR3174 | 1.68 | −0.38 | −0.52 | −0.40 | 0.09 | G25971 | −0.99 | 1.73 | 1.92 | −0.38 | −1.44 | HNRNPA1P60 | −0.25 | −1.02 | 0.53 | −0.08 | −1.05 |
| AC051619.10 | −1.08 | 0.15 | 1.03 | 0.08 | 0.24 | AC009108.4 | −0.58 | 0.77 | −0.79 | 1.57 | −0.93 | CCDC181 | 0.05 | 0.06 | −0.52 | 0.53 | −0.01 |
| DARS2 | 0.30 | −0.30 | −0.08 | −0.20 | 0.13 | C11orf87 | 0.38 | −0.40 | −0.70 | 0.15 | 0.37 | SLC25A14 | 0.02 | 0.03 | −0.06 | 0.01 | −0.13 |
| PRKAR2A-AS1 | −0.80 | 0.17 | 0.22 | 0.24 | 0.27 | AP000893.2 | −0.59 | −0.24 | 0.36 | −0.07 | −1.08 | AC022167.5 | −0.09 | −0.44 | −2.66 | 0.62 | −2.18 |
| AC092164.1 | −1.02 | 0.75 | 0.56 | 0.78 | 0.85 | PKP2 | 0.27 | −0.36 | −0.69 | −0.41 | −0.15 | DUX4L9 | −0.12 | −0.59 | −0.13 | 0.97 | 0.04 |
| AL035425.1 | −2.46 | 1.18 | 0.45 | 1.05 | −0.21 | SCIMP | −0.24 | −0.09 | 0.25 | 0.00 | −0.16 | AC068506.1 | −0.13 | −0.35 | 0.61 | 0.08 | 0.41 |
| LINC01433 | 2.04 | −2.67 | −2.26 | −0.07 | −2.23 | AC078880.4 | −0.74 | −0.19 | −0.75 | −0.70 | −0.43 | HDAC4 | −0.02 | −0.22 | −0.40 | 0.04 | 0.07 |
| IL1F10 | 1.12 | 0.10 | 0.45 | 0.26 | 0.09 | CREB3 | −0.08 | 0.07 | 0.09 | −0.15 | −0.15 | OR7M1P | −0.08 | 0.66 | 0.33 | 0.05 | −0.32 |
| AC026355.1 | −1.24 | −0.49 | 1.00 | 0.46 | 0.37 | MTCO3P5 | 1.39 | −2.78 | −2.48 | 0.74 | −0.41 | MIR4422HG | −0.10 | −0.45 | −0.31 | −0.33 | −1.18 |
| LHFPL1 | −1.63 | 0.98 | 0.69 | 0.36 | 0.37 | RNU6-1196P | −0.86 | 0.09 | 0.78 | 0.32 | 0.81 | AC079322.1 | −0.08 | −0.38 | −0.01 | 0.23 | 0.67 |
| AC004837.2 | 1.06 | −0.30 | −0.21 | −0.24 | −0.35 | RNU6-107P | 0.33 | 0.49 | −0.17 | 0.21 | −0.54 | HNRNPA1P36 | 0.05 | 0.50 | 0.08 | 0.34 | −0.28 |
| RN7SL864P | −1.50 | 0.56 | 1.91 | −0.26 | 0.34 | ME2P1 | 0.78 | −0.17 | −0.88 | −0.14 | 0.43 | RN7SL23P | 0.12 | 0.26 | 1.36 | −0.27 | −0.26 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| RN7SKP124 | −1.05 | 1.13 | 1.99 | 0.45 | 0.54 | AC007991.3 | 0.77 | −1.20 | −2.42 | 0.33 | −1.79 | GMPPA | −0.02 | −0.31 | 0.03 | −0.25 | 0.18 |
| INTS5 | 0.66 | 0.01 | −0.35 | −0.04 | −0.58 | AC004949.1 | −1.15 | 0.05 | −1.70 | −0.79 | −2.05 | NMS | 0.69 | −1.04 | −0.11 | −1.80 | −0.78 |
| AL359232.1 | −0.88 | 0.04 | 0.46 | −0.10 | 0.18 | RBBP5 | 0.08 | −0.09 | −0.17 | −0.11 | −0.12 | AC008109.1 | −0.34 | −0.38 | 0.25 | −0.62 | 0.10 |
| MOB3A | 0.29 | −0.23 | −0.25 | −0.23 | −0.15 | RN7SL81P | 0.32 | −0.59 | −0.58 | −0.28 | −0.54 | AL161757.4 | −0.14 | 0.01 | −1.56 | 0.15 | −1.55 |
| G5173 | −1.58 | 0.06 | 1.53 | −0.25 | 0.53 | AC093367.1 | 0.30 | −0.59 | 0.28 | −0.06 | 0.62 | APOBR | −0.05 | −0.86 | −0.11 | −0.69 | 0.55 |
| EEF2 | 0.29 | 0.02 | −0.26 | 0.04 | −0.22 | CYP3A7 | −0.38 | −0.20 | 0.44 | 0.17 | 0.20 | SEPT14P1 | 0.23 | −1.72 | −0.80 | −0.21 | 1.92 |
| FAM71F2 | −0.68 | 0.43 | 0.73 | 0.11 | 0.24 | AC092068.3 | −0.41 | −0.13 | −0.52 | 0.36 | 0.12 | FCF1P5 | 0.05 | −0.13 | 0.01 | 0.04 | 0.10 |
| PREPL | −0.27 | 0.28 | 0.39 | 0.03 | 0.00 | RN7SL413P | 0.35 | −0.19 | −1.49 | 0.08 | −0.67 | AP000462.3 | −0.07 | −0.42 | 0.03 | −0.08 | 1.00 |
| IGFL2-AS1 | −0.76 | 0.50 | 0.67 | 0.65 | −0.04 | RNU6-1237P | 0.45 | 0.30 | 0.38 | 0.27 | −0.25 | AL365258.2 | 0.10 | 0.45 | 0.15 | −0.25 | 0.08 |
| ENDOU | 0.60 | −0.22 | −0.82 | 0.24 | −0.39 | ATXN7L2 | −0.15 | 0.10 | −0.24 | 0.05 | −0.15 | ERHP1 | 0.20 | −1.02 | 0.00 | −0.97 | 1.31 |
| EDAR | −0.86 | 0.70 | 0.87 | 0.39 | −0.42 | LUC7L2 | −0.11 | 0.15 | 0.18 | 0.14 | 0.10 | AC092017.2 | 0.48 | 1.03 | −0.21 | 1.34 | −0.39 |
| AC005618.1 | −1.08 | −0.01 | 0.97 | −0.23 | −0.01 | AC006449.3 | 0.86 | −0.45 | −1.16 | −0.43 | −0.38 | AL353572.1 | 0.37 | 1.10 | −2.48 | 2.08 | −1.30 |
| CASP14 | 0.83 | 0.19 | 0.09 | 0.64 | −0.68 | AC005326.1 | 0.46 | −0.20 | 0.65 | −0.30 | 0.12 | MIR4290HG | 0.17 | 0.26 | −2.00 | −0.27 | −3.17 |
| C5orf66-AS2 | 1.34 | −0.18 | −1.45 | 0.29 | −0.99 | AC068880.4 | 0.44 | −0.35 | −0.69 | 0.20 | 0.26 | AL731577.1 | −0.04 | −0.13 | −0.24 | 0.00 | 0.09 |
| BASP1 | 0.64 | −0.47 | −0.07 | −0.49 | −0.01 | CEACAM8 | −0.37 | −0.42 | −1.14 | 0.43 | −0.27 | AC024937.2 | 0.12 | 0.94 | −0.77 | 0.63 | −0.33 |
| PTOV1 | −0.44 | 0.22 | 0.13 | 0.30 | 0.33 | RN7SL7P | −0.73 | 0.63 | −0.14 | 0.45 | −0.72 | EIF4E2P1 | −0.09 | 0.87 | 1.88 | −0.28 | 0.57 |
| GPR65 | 1.15 | −1.05 | −0.29 | −0.04 | 0.14 | OR7E7P | −0.40 | 0.32 | 0.81 | 0.09 | 0.52 | RNU2-39P | 0.08 | −0.06 | −0.45 | −0.08 | 0.45 |
| AC116407.3 | −1.01 | 0.17 | 0.88 | 0.79 | 1.01 | G42509 | −0.57 | 0.12 | 0.66 | 0.24 | 0.20 | PABPC1P8 | −0.19 | −1.26 | −0.58 | 0.67 | 0.76 |
| AL360089.1 | −1.79 | 1.03 | 1.01 | 0.15 | 0.68 | COX20P1 | −0.43 | 0.88 | 0.23 | −0.11 | −0.57 | PKNOX2-AS1 | 0.08 | −0.81 | 0.19 | −0.03 | 0.72 |
| LINGO1-AS1 | −1.79 | 0.47 | 0.55 | 0.71 | 1.10 | ACTG1P14 | −0.20 | −0.05 | 0.45 | 0.03 | 0.41 | AC105206.3 | −0.06 | −0.09 | −0.38 | −0.64 | −0.61 |
| AIG1 | 0.40 | −0.28 | −0.17 | −0.07 | −0.05 | P2RY11 | −0.24 | 0.20 | −0.31 | 0.46 | −0.09 | AC125494.2 | −0.10 | 0.19 | −1.53 | 0.88 | −0.29 |
| RPS8 | 0.48 | 0.05 | −0.04 | 0.00 | −0.37 | AC015878.1 | −1.29 | −0.06 | −0.08 | 0.32 | 0.64 | AL442647.1 | 0.28 | −0.43 | 0.33 | 2.01 | −0.21 |
| CLK2 | −0.37 | −0.01 | 0.08 | 0.10 | 0.23 | FAM110B | −0.23 | −0.13 | 0.57 | −0.33 | 0.24 | AC026362.2 | −0.03 | −0.35 | −0.15 | −0.19 | 0.19 |
| ATF6 | 0.27 | −0.04 | −0.01 | −0.11 | −0.22 | LINC01416 | 0.64 | 0.14 | 0.36 | 0.04 | 0.03 | FREM2-AS1 | −0.19 | −1.01 | 0.87 | 0.59 | 1.12 |
| CDH23 | −0.56 | 0.02 | 0.46 | −0.12 | 0.10 | LIN28B-AS1 | −0.69 | 0.57 | 0.01 | 0.46 | −0.01 | MIR569 | −0.55 | 0.38 | −0.12 | 0.52 | −0.38 |
| LOXL1-AS1 | −0.89 | 0.37 | 0.18 | −0.44 | −0.51 | IL21 | 0.85 | −0.72 | −0.83 | −0.37 | −0.36 | GRAMD4P7 | 0.69 | −1.44 | 0.17 | −0.08 | −0.94 |
| AC063950.1 | −0.58 | 0.22 | −0.15 | 0.46 | 0.08 | MC2R | −0.80 | 0.37 | 1.88 | −0.72 | 0.77 | HTRA1 | 0.04 | 0.16 | 0.42 | −0.60 | −0.30 |
| AC105219.1 | −1.25 | 0.56 | 0.55 | 1.16 | 1.42 | LINC01531 | −0.47 | 0.00 | −0.12 | −0.75 | −1.19 | OR8G1 | 0.15 | −3.67 | −1.45 | 0.36 | 1.94 |
| EFNA4 | −0.52 | 0.60 | 0.35 | 0.46 | −0.03 | RN7SL55P | 0.52 | 0.42 | −1.02 | 0.52 | −0.37 | DAOA | −0.16 | 0.09 | −1.68 | 0.89 | −1.55 |
| KCNIP2-AS1 | −1.20 | 0.54 | 0.42 | 0.61 | 0.35 | NPFFR1 | −0.41 | 0.11 | 1.04 | 0.16 | 0.25 | AC127496.3 | −0.09 | 0.26 | 0.56 | 0.13 | −0.11 |
| RAD17 | 0.30 | −0.11 | 0.00 | −0.10 | 0.00 | KHDRBS2 | −0.49 | −0.96 | −0.41 | 0.40 | 1.26 | MIR599 | 0.46 | −0.80 | −0.80 | −0.20 | 0.04 |
| HDGFL2 | −0.43 | 0.03 | 0.00 | 0.16 | 0.22 | AC127024.6 | 0.45 | 0.07 | −0.71 | −0.34 | −0.28 | AC013480.1 | 0.68 | −0.78 | −0.71 | 0.05 | −0.44 |
| AL133284.1 | −1.05 | −0.19 | 0.82 | −0.04 | −0.05 | SNHG20 | −0.19 | 0.50 | 0.53 | 0.09 | −0.24 | AL024497.2 | 0.44 | −0.12 | −1.96 | 0.54 | −0.55 |
| AC092135.3 | 0.74 | −0.24 | −0.78 | −0.27 | −0.44 | AC104448.1 | −0.45 | −0.54 | −0.47 | 0.56 | 0.29 | MIR4776-2 | −0.68 | −0.17 | 0.25 | −0.68 | −0.41 |
| ADGRB3 | −0.70 | 0.39 | 0.81 | 0.10 | 0.50 | ARID4B | −0.10 | 0.06 | 0.15 | −0.10 | −0.04 | NEK1 | −0.02 | −0.01 | 0.23 | −0.06 | 0.21 |
| LINC00940 | −1.53 | −0.18 | 0.53 | 0.15 | −0.02 | AC127520.1 | −1.14 | −1.20 | 1.89 | −2.50 | 1.16 | AC022493.1 | 0.11 | 0.14 | −0.17 | −0.10 | −0.52 |
| PAFAH1B3 | 0.56 | −0.15 | −0.84 | 0.02 | −0.46 | AC096576.3 | −0.76 | −0.82 | −0.20 | 0.43 | 0.07 | CNTN5 | −0.11 | −0.18 | 0.08 | 0.87 | −0.04 |
| AL589739.1 | −1.41 | −0.10 | −0.13 | −0.51 | 0.00 | GRAP2 | −0.26 | 0.06 | 0.59 | −0.44 | 0.03 | AC103957.2 | −0.12 | 0.46 | 0.83 | −0.96 | −0.73 |
| AC012435.1 | −0.58 | 0.17 | 0.52 | −0.04 | 0.14 | ITGAL | 0.33 | −0.70 | 0.24 | −0.78 | 0.40 | AL138731.1 | −0.35 | 1.01 | −0.48 | 1.80 | 0.06 |
| G5617 | −1.65 | 1.23 | −1.93 | 0.85 | −2.02 | RBP3 | −0.87 | −0.95 | 1.84 | −0.74 | 1.29 | GIMAP5 | −0.05 | −0.01 | 0.93 | −0.08 | 0.40 |
| KCNIP4-IT1 | −1.07 | −0.34 | 0.22 | −0.68 | −0.83 | AC018946.2 | −0.74 | 0.82 | 0.28 | 0.70 | 0.84 | AF001548.1 | 0.17 | 0.08 | −0.17 | 0.01 | −0.23 |
| PCMTD1 | −0.42 | 0.42 | 0.59 | 0.09 | −0.06 | FDPSP3 | 0.40 | −0.61 | −0.57 | −0.21 | 0.04 | AC103996.2 | −0.14 | −0.92 | 0.70 | −0.18 | 0.44 |
| LINC00578 | −1.47 | 0.57 | 2.07 | 0.13 | 0.61 | AC100812.1 | −0.60 | −0.11 | −0.68 | −0.74 | −1.47 | OR5F1 | 0.28 | −0.66 | −2.17 | 1.25 | −1.05 |
| HNF1A-AS1 | −1.40 | 0.15 | −0.87 | 0.47 | −0.57 | MSL2 | 0.10 | 0.08 | 0.06 | −0.03 | −0.07 | AC016383.2 | 0.17 | −0.81 | −1.28 | 1.18 | −1.25 |
| RBMXL1 | 0.25 | −0.17 | −0.27 | −0.06 | −0.09 | CCDC141 | −0.28 | −0.09 | 0.13 | 0.34 | 0.35 | RN7SL165P | −0.19 | −0.79 | 1.87 | −0.65 | −1.09 |
| RNU6-387P | 1.39 | −1.46 | −1.53 | 0.35 | 0.50 | AL365259.1 | −0.54 | −0.42 | 0.15 | −0.22 | −0.09 | SDCBPP1 | −0.08 | −0.42 | −0.33 | 0.30 | 0.13 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AL365258.1 | 1.26 | −0.62 | −0.13 | 0.00 | 0.13 | HMGN2P40 | −0.81 | −0.49 | −1.79 | 0.93 | −2.01 | AK6P1 | −0.29 | 0.29 | −2.04 | 0.18 | −1.04 |
| AC012368.2 | 0.92 | −0.92 | −1.06 | 0.12 | −0.06 | RNA5SP473 | −1.00 | 1.00 | 2.72 | 0.91 | 0.73 | AP003355.3 | −0.09 | 0.30 | 0.18 | 0.11 | −0.45 |
| AL390728.4 | 0.40 | −0.23 | −0.13 | −0.19 | −0.05 | MMEL1 | −0.48 | −0.26 | −0.51 | 0.35 | −0.15 | AC130371.1 | 0.05 | −0.19 | 0.60 | 0.07 | 0.59 |
| AAR2 | 0.31 | −0.10 | −0.18 | 0.00 | −0.25 | AC109635.2 | −1.07 | −0.48 | −1.96 | 0.96 | −1.50 | AL121672.1 | −0.04 | 0.18 | −0.17 | 0.31 | −0.05 |
| AC092574.2 | −0.64 | 0.33 | 0.40 | 0.18 | 0.22 | SERF2 | 0.10 | 0.06 | 0.02 | −0.04 | −0.13 | SMIM2 | 0.32 | 0.26 | −0.28 | −1.16 | −1.23 |
| AC004492.1 | −0.45 | 0.58 | 0.63 | 0.06 | −0.05 | GPR27 | −0.38 | −0.06 | −0.53 | 0.44 | 0.35 | APOF | −0.11 | −2.31 | −0.67 | 0.16 | 2.06 |
| NKD1 | −0.46 | 0.20 | 0.40 | 0.24 | 0.20 | AC004130.1 | 0.47 | 0.34 | −0.93 | 0.62 | −0.71 | PLEKHA1 | 0.02 | 0.26 | 0.27 | 0.11 | −0.05 |
| ATF5 | 0.45 | −0.53 | −0.76 | −0.20 | −0.17 | LINC02069 | −0.53 | −0.16 | 0.86 | −0.52 | 0.34 | OR4K15 | −0.30 | 0.40 | −1.15 | 2.05 | −0.35 |
| KCTD12 | −0.57 | 0.37 | 0.98 | 0.17 | 0.43 | NOC4L | 0.15 | −0.13 | −0.66 | 0.12 | −0.10 | ODF3L2 | −0.19 | −0.26 | −0.33 | 1.27 | 0.62 |
| ATP13A4 | −0.64 | 0.45 | 1.43 | 0.19 | 0.70 | DMRTA2 | −0.86 | −0.32 | −0.47 | −0.86 | −0.74 | LINC01489 | −0.16 | 0.38 | −0.40 | 0.99 | 0.46 |
| PLIN5 | −1.20 | 0.44 | 0.88 | 0.52 | 0.72 | AC125603.4 | −0.41 | −0.69 | −0.88 | 0.59 | 0.44 | AC097173.1 | −0.21 | −0.92 | −2.48 | 0.95 | −0.83 |
| MCM8 | 0.33 | −0.44 | −0.27 | −0.17 | 0.17 | AC093700.1 | 1.23 | −0.94 | −1.93 | 0.31 | −3.49 | AC139720.2 | −0.17 | 1.03 | −2.35 | 0.92 | −2.88 |
| LRRIQ1 | −0.94 | 0.45 | −0.02 | 0.25 | −0.38 | LINC02562 | 0.34 | 0.18 | −0.03 | 0.23 | −0.44 | G3945 | −0.08 | −0.07 | 0.50 | 0.11 | −0.06 |
| DMPK | −0.46 | 0.18 | 0.09 | 0.13 | 0.02 | AC011676.3 | −0.35 | 1.29 | 0.77 | 0.60 | −0.18 | LINC00518 | 0.08 | 0.46 | −0.50 | 0.05 | −0.24 |
| PRPF6 | −0.23 | 0.14 | 0.13 | 0.03 | 0.03 | AC009312.1 | −1.01 | 0.98 | 0.03 | 0.42 | −2.36 | AC140125.3 | 0.53 | −0.99 | 0.87 | −0.61 | 0.39 |
| GLYATL1P2 | 1.06 | −0.72 | −1.04 | 0.12 | 0.39 | ATP8B5P | 0.31 | −0.73 | −0.61 | 0.39 | 0.53 | SREK1 | −0.02 | −0.03 | −0.12 | 0.00 | −0.08 |
| PAF1 | 0.26 | −0.18 | −0.37 | −0.11 | −0.18 | PPIAP40 | 0.26 | 0.01 | −0.19 | 0.35 | 0.11 | AC034102.6 | 0.05 | −0.16 | −0.51 | 0.13 | −0.01 |
| BECN1 | 0.21 | −0.14 | −0.28 | 0.01 | −0.07 | EPC2 | 0.09 | 0.12 | −0.03 | 0.01 | −0.19 | AC004674.1 | 0.29 | 0.58 | −2.20 | 0.85 | −3.00 |
| AL139424.3 | −0.47 | 0.40 | 0.05 | 0.23 | −0.11 | HCST | 0.92 | −0.98 | −0.64 | −0.40 | 0.23 | AL163636.1 | 0.17 | −0.14 | 1.34 | −0.45 | 0.79 |
| AL354733.2 | −0.53 | 0.42 | 0.50 | 0.51 | 0.07 | GPR155 | −0.19 | 0.12 | 0.07 | 0.22 | 0.30 | ADAL | 0.02 | −0.32 | −0.05 | −0.14 | 0.26 |
| HSPE1P28 | 0.87 | −0.52 | −0.07 | 0.09 | −0.11 | OR4K16P | 1.46 | −0.55 | −2.86 | 0.55 | −2.18 | LINC01346 | −0.16 | 0.07 | −1.20 | 0.07 | −1.23 |
| SLC7A6OS | −0.27 | 0.16 | −0.02 | 0.21 | −0.05 | AL109767.1 | 0.36 | 0.09 | −0.01 | 0.10 | −0.08 | AC116359.1 | −0.53 | 0.16 | 0.52 | −0.14 | 0.90 |
| SESTD1 | −0.56 | 0.40 | 0.41 | 0.12 | 0.00 | AC091059.2 | −0.38 | 0.44 | 1.04 | −0.40 | 0.15 | AL158801.1 | 0.06 | −0.63 | 0.12 | −0.27 | 0.35 |
| AL732414.1 | 1.04 | −0.32 | −0.60 | −0.31 | −0.80 | AC011270.2 | 0.63 | −0.60 | −1.74 | 0.45 | −0.26 | CHRM5 | 0.03 | −0.18 | −0.60 | 0.00 | −0.22 |
| C16orf45 | −0.62 | 0.23 | 0.59 | −0.02 | 0.17 | AC010266.2 | 0.81 | −0.93 | −2.30 | 0.60 | −1.92 | AC010186.1 | −0.15 | −0.67 | 0.45 | 0.13 | 0.43 |
| AL136303.1 | 1.90 | −1.66 | −1.19 | −0.69 | 0.28 | AC008494.2 | 1.13 | −0.57 | 1.54 | 1.56 | 1.10 | LINC02315 | −0.13 | −1.52 | −0.06 | −0.36 | 1.09 |
| LINC00607 | −1.04 | −0.14 | 0.42 | 0.33 | 0.48 | AL590704.1 | 0.39 | 0.17 | −0.79 | 0.36 | −0.46 | FIBCD1 | −0.13 | 1.30 | 0.34 | −0.07 | −1.05 |
| HDAC7 | −0.36 | 0.12 | 0.18 | 0.04 | 0.10 | RNA5SP290 | 0.31 | −0.70 | −1.13 | −0.27 | −0.49 | AC010547.2 | 0.39 | −0.76 | −1.85 | −0.63 | 0.79 |
| DMAC2 | 0.30 | −0.09 | −0.31 | 0.09 | −0.02 | MIR3137 | 0.53 | −0.69 | 0.37 | −0.10 | 0.70 | AC126120.1 | 0.18 | 0.84 | −0.89 | 0.73 | −1.58 |
| CCT5P1 | 1.17 | −0.42 | −1.18 | −0.27 | −0.90 | AC093616.1 | 0.30 | −0.53 | −0.14 | −0.42 | −0.30 | RN7SKP94 | −0.17 | −0.78 | 0.34 | 0.03 | 1.56 |
| GOLGA8A | −0.50 | 0.22 | 0.03 | 0.05 | −0.04 | AC099677.1 | −0.37 | 0.49 | 0.57 | 0.30 | 0.22 | AP000357.2 | 0.54 | −1.01 | 0.08 | −1.43 | 0.41 |
| GNB1L | −0.66 | 0.31 | 0.21 | 0.36 | 0.47 | RNU7-166P | −1.05 | −0.25 | 1.26 | 0.31 | 2.39 | RPSAP60 | −0.35 | −0.18 | 0.40 | 0.99 | 2.20 |
| NF2 | 0.25 | −0.26 | −0.31 | −0.09 | −0.07 | BRD8 | −0.10 | −0.03 | 0.02 | −0.05 | 0.01 | LINC00543 | 0.18 | −0.29 | −0.80 | −0.32 | −1.92 |
| SRPX2 | −0.87 | 0.05 | 0.44 | 0.05 | −0.13 | LINC01619 | 0.25 | −0.19 | −0.65 | 0.45 | 0.06 | C16orf82 | 0.21 | −1.62 | −1.49 | 0.77 | 2.06 |
| G41381 | −1.08 | 0.37 | 1.11 | −0.01 | 0.36 | AP001877.1 | 0.28 | −0.21 | 0.19 | −0.23 | −0.01 | POLR2CP1 | −0.26 | −0.07 | −0.96 | 1.32 | −1.54 |
| SNAPC4 | −0.50 | −0.06 | −0.18 | 0.22 | 0.14 | RAB11FIP2 | −0.10 | 0.01 | 0.20 | −0.02 | 0.07 | HSF2 | −0.02 | 0.19 | 0.21 | 0.07 | −0.21 |
| RN7SL711P | −1.15 | 0.57 | 0.54 | 0.78 | −0.27 | AC010608.3 | 0.52 | 0.32 | −0.06 | 0.51 | −0.17 | AF181450.1 | −0.13 | 0.36 | 1.83 | −0.62 | 0.37 |
| LINC02009 | 1.65 | 0.05 | −1.85 | 0.74 | −1.06 | C8orf88 | −0.26 | 0.64 | 0.15 | −0.06 | −0.60 | LINC01048 | 0.25 | −1.05 | −2.29 | −0.26 | −0.96 |
| SCRN2 | −0.42 | 0.26 | 0.15 | 0.36 | 0.23 | AC011933.3 | 0.36 | −0.26 | −0.67 | −0.01 | 0.08 | AC016168.2 | −0.54 | 0.26 | −1.19 | 0.93 | −0.85 |
| NFYA | 0.35 | −0.26 | −0.27 | −0.34 | 0.00 | AC023512.1 | −0.78 | 0.26 | −0.06 | −0.16 | −2.19 | LINC02525 | −0.14 | −0.44 | −0.11 | 0.12 | 0.06 |
| AL022311.1 | −0.51 | −0.05 | −0.09 | 0.08 | 0.10 | RNU6-481P | 0.68 | 0.33 | 0.83 | 0.43 | 0.11 | PTPN20A | −0.09 | 0.86 | 1.06 | −0.06 | −0.10 |
| SPDYE21P | −0.71 | 0.28 | 0.69 | 0.35 | 0.69 | NIFKP4 | −0.84 | −1.18 | −0.31 | 0.34 | 0.69 | ACTG1P21 | 0.24 | −0.76 | 0.63 | −0.73 | −0.81 |
| ARHGEF11 | −0.20 | 0.06 | 0.09 | −0.02 | 0.02 | FRMPD4 | −0.49 | 0.12 | 0.42 | 0.39 | 0.38 | BTF3L4P3 | 0.27 | −0.99 | −0.13 | −0.81 | 0.52 |
| KRT17P1 | 1.55 | −1.16 | −2.10 | 0.52 | 0.17 | AC004381.2 | 0.37 | 0.20 | 0.21 | 0.14 | −0.04 | AC004063.1 | −0.13 | 0.48 | 0.23 | 0.98 | −0.03 |
| RNA5SP298 | −1.35 | 0.89 | −1.12 | 1.85 | −0.78 | RSPO2 | −0.65 | −0.82 | −0.83 | 0.43 | −0.91 | RN7SL128P | −0.06 | 0.05 | −0.12 | 0.44 | −0.44 |
| LMTK3 | 0.56 | −0.24 | −1.01 | 0.08 | −0.06 | NANOGP7 | 0.52 | −1.25 | 0.45 | −0.58 | 1.45 | FAM86MP | −0.27 | −0.15 | 0.87 | 1.86 | 1.29 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC022973.4 | 0.92 | −0.85 | −0.65 | −0.24 | 0.07 | AP001207.3 | 0.37 | 0.19 | 0.50 | 0.02 | −0.35 | AC114316.2 | −0.13 | −0.66 | −0.24 | −1.55 | −1.28 |
| PART1 | −0.49 | 0.52 | 0.03 | 0.30 | −0.33 | PPIAP3 | 0.95 | 0.30 | −0.60 | 0.63 | −0.67 | AF131216.4 | 0.20 | −0.59 | −1.62 | −0.67 | −2.90 |
| MMS22L | 0.34 | −0.32 | −0.28 | 0.03 | 0.03 | AC005884.1 | 0.98 | 0.36 | 0.03 | 0.13 | 0.23 | FAM169B | 0.10 | −0.20 | 0.54 | −0.05 | −0.92 |
| AC008739.5 | −0.57 | −0.22 | 0.33 | 0.22 | 0.49 | OR52K3P | −0.61 | 0.23 | 0.90 | −0.13 | 0.01 | RPL13AP6 | −0.04 | 0.33 | 0.23 | 0.21 | −0.01 |
| CHCHD4P4 | 1.90 | −1.50 | −1.03 | 0.04 | 1.03 | AC005014.3 | 0.86 | −0.19 | −0.70 | 0.14 | 0.72 | AL391361.1 | −0.68 | 0.18 | −1.11 | 3.04 | 0.76 |
| ARID4A | −0.31 | 0.21 | 0.22 | 0.11 | −0.05 | EMILIN1 | −0.24 | 0.11 | 1.26 | −0.62 | 0.17 | MGAM | 0.08 | −0.59 | −0.81 | −0.22 | −1.11 |
| LMBR1 | 0.20 | 0.05 | −0.02 | 0.01 | −0.06 | AL139020.1 | −0.73 | −0.66 | −0.45 | 0.09 | 0.54 | OR7E161P | 0.16 | −1.58 | −0.70 | −0.37 | −0.41 |
| DTD1 | 0.43 | −0.16 | −0.31 | 0.12 | −0.19 | MARCOL | −0.57 | −0.29 | −1.68 | 0.96 | −1.71 | INSL6 | −0.04 | −0.40 | −0.03 | −0.08 | 0.25 |
| CRTAC1 | 0.76 | −0.44 | −0.82 | 0.18 | −0.54 | PSMA3-AS1 | −0.12 | 0.06 | 0.19 | 0.13 | 0.27 | PSAT1P1 | −0.29 | 0.64 | −0.59 | −0.02 | −1.57 |
| RPL8 | 0.39 | −0.01 | −0.08 | −0.09 | −0.36 | BX088651.4 | −0.41 | 0.06 | 0.52 | 0.61 | 0.39 | DEFB130D | 0.66 | −1.17 | −1.06 | −0.22 | −2.46 |
| SLC30A10 | −1.24 | 0.61 | −0.48 | 0.53 | −0.16 | LINC01128 | −0.12 | −0.06 | 0.16 | −0.10 | 0.07 | AC092104.5 | −0.54 | 0.85 | −0.98 | 2.21 | −0.11 |
| CIB2 | 0.68 | −0.72 | −0.89 | −0.18 | −0.69 | AC079145.1 | −0.84 | 0.08 | 1.83 | −0.10 | 0.00 | AL031668.1 | 0.05 | 0.08 | −0.20 | −0.21 | −0.34 |
| RASSF10 | 0.49 | 0.32 | −0.64 | 0.54 | −0.19 | PHKA1-AS1 | 0.77 | 0.04 | −0.54 | 0.72 | 0.17 | AC011498.3 | −0.09 | 0.10 | −1.16 | 0.36 | −0.25 |
| CCR10 | −0.80 | −0.36 | 0.36 | −0.12 | 0.46 | MSTO1 | −0.18 | −0.04 | 0.12 | −0.06 | 0.29 | AL138828.2 | −0.43 | −0.84 | −2.12 | 1.26 | 0.44 |
| LRRC42 | 0.39 | −0.28 | −0.59 | −0.16 | −0.36 | LRRC20 | 0.21 | 0.00 | −0.78 | 0.06 | −0.89 | MTCYBP29 | −0.28 | 0.22 | 1.43 | −0.53 | −0.01 |
| C5orf67 | −1.76 | 1.11 | 0.41 | −0.38 | 0.42 | HHIPL2 | −0.37 | −0.04 | −0.48 | −0.11 | −0.16 | BUB3P1 | −0.40 | 0.53 | −0.75 | −0.53 | 1.21 |
| HNRNPL | 0.33 | −0.16 | −0.31 | −0.04 | −0.08 | AL355490.1 | 0.88 | −1.73 | 0.60 | −0.63 | 2.13 | AL590103.1 | 0.10 | 0.58 | 0.12 | 0.10 | 0.22 |
| FADS6 | −0.78 | 0.66 | 1.20 | 0.58 | −0.10 | G34931 | 0.47 | −1.11 | 0.15 | −0.82 | 0.15 | MIR95 | 0.09 | 0.13 | 0.29 | 0.12 | 0.48 |
| RAB40AL | −1.34 | 0.18 | 0.23 | −0.02 | 0.11 | AL138733.1 | 0.43 | −1.83 | −0.32 | 0.08 | 0.67 | CPN2 | 0.11 | 0.25 | −1.57 | −0.97 | −1.89 |
| DANT2 | −0.63 | 0.91 | 0.79 | 0.23 | 0.18 | AC138655.1 | −0.50 | −0.47 | −0.75 | 0.82 | 1.63 | LINC02261 | −0.09 | 0.52 | −0.58 | 0.24 | −0.56 |
| RMDN2 | 0.39 | −0.36 | −0.46 | 0.04 | 0.02 | RABGAP1 | −0.08 | 0.17 | 0.00 | 0.13 | −0.05 | AC078795.1 | −0.04 | −0.22 | 0.36 | −0.16 | 0.29 |
| BIRC6 | 0.26 | −0.06 | −0.11 | −0.04 | −0.06 | HSP90AA4P | 0.61 | −0.40 | −1.69 | 0.04 | −1.87 | AC100821.1 | 0.04 | −0.13 | −0.09 | 0.04 | 0.09 |
| LINC02062 | −0.80 | 0.08 | 1.71 | −0.05 | 0.31 | B3GNTL1P1 | −0.92 | 0.48 | 0.68 | 0.65 | 0.57 | AL391845.1 | 0.28 | 0.66 | 1.12 | 0.75 | 0.86 |
| LRP10 | 0.30 | 0.10 | −0.21 | 0.05 | −0.38 | SCO1 | −0.10 | −0.24 | −0.07 | −0.09 | 0.22 | AC009509.1 | 0.10 | −0.81 | −0.93 | −0.28 | −0.45 |
| AC008764.8 | −0.62 | 0.11 | 0.20 | 0.10 | 0.05 | APOBEC3H | −0.41 | −0.48 | 0.40 | −0.28 | 0.15 | AC092718.3 | −0.07 | 1.02 | 0.22 | 0.10 | −0.95 |
| G32166 | 0.58 | −0.12 | −0.26 | −0.09 | 0.00 | CYYR1-AS1 | 0.16 | −0.20 | 0.71 | 0.06 | 0.72 | ACTR6P1 | −0.67 | −0.25 | 0.72 | −0.37 | −0.02 |
| AL512770.1 | −0.58 | −0.06 | −0.12 | 0.27 | 0.32 | LINC02499 | −0.81 | 0.92 | −2.12 | 1.16 | −3.33 | ELL2P2 | −0.67 | 0.06 | −0.52 | −0.36 | −2.05 |
| SERBP1P6 | −0.71 | 0.34 | 0.69 | 0.42 | 0.42 | MT1JP | −0.87 | −1.97 | 0.74 | −1.15 | −0.12 | AC007032.1 | 0.26 | −0.27 | −2.03 | 0.00 | −1.87 |
| RPS28 | 0.50 | −0.01 | 0.07 | 0.05 | −0.27 | LINC01342 | −1.04 | −0.80 | −0.77 | 0.66 | 1.00 | AC034205.1 | −0.35 | 0.80 | −2.31 | 0.53 | −2.39 |
| AC093797.1 | −0.99 | 0.53 | 1.96 | −0.18 | 1.27 | CEACAM21 | 0.40 | −0.47 | −0.85 | 0.21 | −0.08 | HMGB1P46 | −0.30 | 0.22 | 0.11 | −0.20 | −2.44 |
| NDUFC1 | 0.55 | −0.22 | −0.02 | −0.36 | −0.29 | IGHV1-18 | 1.10 | 1.92 | 3.05 | −1.08 | −0.36 | OR8K1 | −0.22 | −0.35 | −0.68 | 1.55 | −1.26 |
| AL096677.1 | 1.11 | −0.85 | −0.68 | 0.04 | 0.10 | AP003471.1 | −0.79 | 0.04 | 0.82 | −0.75 | 0.62 | AC010105.1 | 0.48 | −0.60 | −0.51 | −1.22 | 0.47 |
| CDC27 | 0.35 | −0.26 | −0.42 | −0.15 | −0.28 | AC000036.1 | −0.35 | 0.50 | −0.19 | 0.24 | −0.51 | NEUROD1 | 0.17 | −0.29 | 0.11 | −0.41 | −0.35 |
| AC138207.8 | −0.45 | 0.52 | 0.53 | 0.18 | 0.05 | RPS20P20 | 0.40 | −1.03 | −1.54 | −0.07 | 0.24 | RNU6-1182P | 0.12 | −0.27 | −0.47 | −0.05 | −0.41 |
| SLX4IP | 0.29 | −0.20 | −0.19 | −0.10 | −0.01 | CAPN8 | −0.40 | 0.42 | 0.39 | 0.75 | 0.17 | AP003774.4 | 0.14 | 0.32 | −2.60 | 0.88 | −2.84 |
| DOLK | 0.39 | −0.04 | −0.14 | −0.06 | −0.14 | AC027013.1 | −0.65 | 0.17 | 1.71 | −0.54 | 0.94 | LINC01029 | 0.17 | −1.16 | −0.86 | −0.07 | 1.06 |
| SPSB4 | −1.02 | 0.51 | 0.16 | −0.27 | −0.69 | RPL21P134 | 0.70 | 0.66 | 0.50 | −0.51 | −0.57 | AL359693.1 | 0.15 | −0.04 | 2.05 | 0.09 | 0.45 |
| AC023095.1 | −1.53 | 1.08 | −0.95 | 1.68 | −1.04 | AC104066.2 | −0.69 | −0.16 | −0.63 | −0.03 | −1.41 | AL137026.2 | −0.49 | −0.27 | −0.08 | −1.39 | −1.32 |
| MTLN | 0.63 | −0.29 | −0.38 | −0.40 | −0.20 | ID3 | 0.17 | −0.21 | −0.05 | −0.17 | −0.38 | AC013467.1 | 0.65 | −1.02 | −1.84 | 0.91 | 0.69 |
| RP11-292B8.1 | −0.62 | 0.26 | 0.52 | 0.62 | 0.58 | MIR603 | 0.52 | −0.58 | −0.30 | −0.59 | 0.67 | RN7SL314P | −0.27 | 0.13 | −1.21 | 1.89 | −0.35 |
| COL2A1 | −0.86 | −0.06 | 0.32 | 0.64 | 0.30 | AC022748.2 | 1.04 | −0.20 | −1.08 | 0.48 | 0.15 | AC008825.1 | −0.23 | −0.66 | −2.68 | 3.08 | 0.25 |
| NUP62CL | 0.59 | −0.46 | −0.71 | −0.02 | −0.08 | LINC02275 | −0.61 | 0.09 | −0.24 | 0.46 | −0.18 | SAMSN1-AS1 | 0.27 | −1.89 | −0.44 | −1.76 | 0.57 |
| AC017002.1 | 1.41 | −1.37 | −1.94 | −0.80 | −0.99 | PLEKHH3 | −0.18 | 0.28 | 0.04 | 0.38 | 0.05 | AC016933.1 | −0.67 | −0.20 | 0.19 | 2.12 | 0.31 |
| AC108463.3 | 1.04 | −0.84 | −1.33 | −0.72 | −1.22 | AL662907.2 | 0.23 | 0.15 | −0.16 | 0.11 | −0.45 | CCDC194 | −0.09 | −0.83 | 0.69 | −0.79 | 1.10 |
| AL451074.2 | −0.67 | −0.32 | 0.26 | 0.45 | 1.41 | HMGN2P4 | 0.84 | −1.12 | −0.41 | 0.21 | 0.83 | AL731574.1 | 0.24 | −0.81 | 0.78 | −0.29 | 0.40 |
| MPC1 | −0.23 | 0.19 | 0.19 | 0.10 | 0.04 | LINC01584 | 0.77 | 0.06 | −0.20 | 0.93 | −0.09 | MIR641 | −0.25 | 0.12 | 1.82 | −0.40 | 0.94 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AL136116.3 | 0.74 | −0.13 | −0.91 | 0.12 | −0.48 | AXDND1 | −0.46 | 0.26 | −0.60 | 0.82 | 0.76 | AC017037.3 | −0.26 | −0.77 | 0.50 | 1.27 | 2.54 |
| AP1G2 | −0.46 | 0.32 | 0.15 | 0.32 | 0.16 | AC008069.1 | 0.92 | −0.54 | −0.44 | 0.67 | 0.19 | SOWAHD | −0.09 | −0.31 | 0.58 | 0.02 | 0.17 |
| ARMCX6 | −0.39 | 0.37 | 0.58 | 0.08 | 0.02 | RNY4P20 | −0.95 | 0.80 | −0.03 | 0.89 | 0.76 | AC002550.1 | 0.27 | −0.97 | −1.01 | −1.04 | −1.32 |
| AD000090.1 | −1.18 | 0.36 | −0.40 | 1.32 | −0.04 | MAN1A2P1 | −1.00 | −1.40 | −0.48 | −2.17 | −1.13 | MIR4768 | −0.09 | −0.58 | −0.55 | −0.19 | 0.05 |
| REL | 0.48 | −0.10 | −0.33 | 0.10 | −0.33 | AL031602.1 | 0.78 | −0.48 | −0.78 | 0.02 | −0.92 | AC026803.1 | −0.10 | 0.63 | −0.44 | 0.61 | −0.20 |
| NUS1P1 | 0.95 | −0.31 | −1.33 | −0.19 | −0.49 | SIGLEC1 | −0.28 | −0.12 | 0.26 | 0.08 | −0.12 | AC016987.2 | 0.42 | −1.29 | 1.81 | 0.30 | 0.46 |
| SNRPCP9 | −1.12 | 0.96 | 2.34 | 0.42 | 1.21 | CD52 | 0.30 | −0.12 | 0.68 | −0.26 | 0.16 | AP003555.3 | −0.14 | −0.37 | 0.86 | −0.71 | 0.49 |
| MIR2355 | 1.49 | −1.12 | 0.13 | −1.25 | −0.05 | AC005105.1 | −0.59 | 1.42 | −0.79 | 0.92 | −2.07 | AC004923.4 | −0.07 | −0.33 | 0.80 | −0.19 | 0.67 |
| ENOX1 | −0.87 | −0.21 | 1.03 | −0.28 | 0.39 | SF3A2 | −0.12 | 0.08 | −0.20 | 0.19 | −0.01 | MTATP6P14 | 0.27 | −1.01 | −1.21 | 0.41 | 1.13 |
| C19orf44 | −0.47 | 0.11 | 0.48 | −0.08 | 0.23 | SNORD71 | −0.21 | 0.34 | 0.58 | 0.14 | −0.34 | AC027335.2 | 0.09 | 0.70 | 0.40 | −0.58 | −0.61 |
| C3orf18 | −0.75 | 0.33 | 0.39 | −0.04 | 0.10 | SNORD125 | 0.42 | −0.18 | −0.68 | 0.43 | 0.04 | AL049869.3 | −0.04 | −0.04 | 0.00 | −0.17 | −0.18 |
| MLX | 0.30 | −0.23 | −0.36 | −0.12 | −0.12 | G29000 | −0.79 | −0.02 | 2.62 | 0.59 | 1.95 | AL354989.1 | 0.06 | 0.11 | 0.27 | −0.19 | −0.27 |
| CDK5 | 0.45 | −0.07 | −0.17 | 0.06 | −0.12 | NPM1P40 | −0.92 | −0.18 | 0.23 | 0.75 | −0.37 | AC012174.1 | −0.19 | 0.12 | −1.55 | −0.58 | −0.67 |
| LYG1 | −0.83 | 0.15 | 0.93 | 0.20 | 0.59 | H1FX | 0.14 | 0.08 | −0.37 | 0.21 | −0.19 | G27754 | −0.05 | 0.21 | −0.58 | 0.50 | −0.36 |
| AL049597.1 | 1.48 | −0.40 | −1.24 | 0.30 | −0.75 | AC073111.1 | 0.44 | −0.58 | −0.71 | 0.31 | 0.47 | AL160290.1 | −0.43 | −0.07 | 1.46 | −1.01 | 1.21 |
| DDX39A | 0.45 | −0.53 | −1.05 | −0.05 | −0.21 | LINC01360 | 0.87 | 0.54 | −1.14 | 0.94 | −0.66 | OR2M7 | −0.20 | −0.99 | −0.83 | 0.99 | 1.38 |
| GNG2 | −0.67 | 0.31 | 0.52 | 0.09 | 0.16 | INSYN2B | 0.29 | −0.62 | 0.26 | −0.48 | 0.61 | AC097493.2 | 0.08 | 0.84 | −0.23 | 0.39 | −0.87 |
| AC027644.2 | 0.98 | −0.07 | −0.16 | 0.03 | −0.29 | INPP4B | −0.16 | −0.03 | 0.12 | −0.15 | −0.01 | AC025174.1 | −0.64 | 0.33 | −0.27 | −1.75 | −2.86 |
| NUP35 | 0.38 | −0.15 | −0.29 | −0.12 | −0.17 | RNA5SP296 | 0.40 | −0.58 | 0.62 | −0.33 | 0.01 | PAGE2B | −0.17 | −0.11 | −2.05 | 0.80 | −1.03 |
| AC100839.1 | −1.54 | 1.18 | 1.64 | 0.40 | 1.36 | AL138962.1 | 0.44 | −0.97 | −1.06 | −0.56 | −0.41 | SPDYC | −0.13 | 0.33 | −0.33 | 1.04 | 0.71 |
| HMGB1P39 | −1.07 | 0.36 | 0.28 | 0.05 | −0.13 | CACNG7 | −0.88 | −0.88 | −1.67 | −0.54 | −3.61 | IGKV1D-33 | 0.67 | −0.29 | 0.13 | −0.16 | −3.85 |
| C8orf59 | 0.41 | −0.34 | −0.36 | 0.01 | −0.09 | IL1RL2 | 0.16 | −0.16 | −0.13 | −0.09 | 0.03 | AC055720.2 | −0.06 | 0.61 | −0.24 | 0.53 | 0.01 |
| LSM12P1 | 0.81 | −0.42 | −0.27 | −0.38 | −0.29 | AC137761.1 | −0.96 | −0.30 | 0.64 | 0.13 | −0.55 | KRT18P40 | −0.24 | −0.53 | −0.53 | −0.47 | −1.37 |
| BMPR1B | 0.54 | −0.65 | −1.02 | −0.05 | −0.77 | AC127537.1 | −0.41 | 0.83 | 1.22 | 0.71 | 0.73 | AC097059.2 | 0.31 | −0.91 | −1.24 | 0.42 | −0.78 |
| AP5S1 | 0.31 | −0.17 | −0.37 | 0.07 | −0.14 | AC012513.2 | 0.20 | −0.30 | 0.00 | −0.28 | 0.15 | KRT18P38 | −0.34 | 0.86 | −0.07 | 0.50 | −1.32 |
| KMT2C | −0.18 | 0.23 | 0.18 | 0.08 | −0.02 | AC017083.1 | −0.24 | −0.32 | 0.26 | 0.00 | 0.44 | AC006023.1 | −0.09 | −0.52 | 2.08 | −0.62 | 0.40 |
| MTND2P23 | −2.13 | 0.40 | 0.38 | 0.84 | 0.51 | LINC00392 | −0.59 | 0.98 | 0.49 | −0.57 | −0.03 | AL354714.3 | 0.39 | −0.80 | 0.57 | −1.01 | −1.86 |
| RPS15AP29 | 0.58 | −0.15 | 0.18 | −0.08 | 0.04 | AC011939.1 | 0.21 | −0.07 | −0.04 | 0.16 | 0.22 | AC063949.1 | −0.38 | −0.94 | 2.17 | −0.56 | 1.25 |
| AC091132.5 | −1.07 | 0.49 | 1.14 | −0.03 | 0.60 | GAPDHP25 | 1.14 | −0.42 | −1.94 | 0.57 | −2.03 | ARHGEF7-AS2 | −0.33 | 0.20 | 0.56 | −0.10 | 1.39 |
| CUL7 | −0.31 | 0.03 | 0.09 | 0.10 | 0.17 | OR7E136P | −1.26 | 0.57 | −0.09 | −1.20 | 1.00 | PGAM4P2 | −0.33 | −0.29 | −0.66 | 1.75 | −1.40 |
| AC010210.1 | −0.47 | 0.05 | 0.18 | −0.05 | 0.27 | RN7SL110P | −0.81 | −0.15 | −1.46 | 0.31 | −3.19 | MTND5P3 | 0.13 | −2.03 | −0.15 | −0.28 | 2.19 |
| FAM78B | −0.61 | 0.02 | 0.83 | −0.47 | 0.09 | POTEE | 0.62 | 0.09 | −1.31 | 0.20 | −0.90 | RPSAP48 | −0.21 | −0.89 | −0.36 | −0.30 | 0.01 |
| MFNG | 0.61 | −0.76 | −0.36 | −0.18 | 0.17 | SP140L | 0.18 | −0.37 | −0.16 | −0.26 | 0.07 | OR13C4 | −0.28 | −0.08 | −2.12 | 0.58 | −1.43 |
| AC007529.2 | −1.31 | 0.39 | 0.50 | 0.52 | −0.80 | FGF10-AS1 | −0.52 | 0.19 | 0.58 | −0.47 | 0.66 | AC009831.1 | 0.06 | 0.31 | 0.34 | −0.10 | −0.48 |
| LINC01269 | 1.93 | −0.20 | −0.57 | −0.18 | −0.35 | AL162430.1 | 0.30 | −0.06 | 0.14 | 0.25 | 0.33 | AC130464.1 | 0.23 | −0.62 | 0.46 | 0.18 | 0.22 |
| PPA2 | 0.29 | −0.07 | −0.10 | −0.08 | −0.09 | AC022149.1 | 0.40 | −0.14 | 0.11 | −0.27 | −0.42 | AL513478.2 | −0.66 | −0.92 | −0.65 | −0.63 | NA |
| RPS23 | 0.36 | 0.00 | −0.20 | 0.01 | −0.41 | ENPEP | 0.28 | −0.37 | 0.28 | −0.56 | −0.08 | ACE | 0.04 | 0.04 | 0.10 | −0.17 | −0.12 |
| CISH | 0.75 | −0.69 | −1.03 | −0.08 | −0.20 | GMPSP1 | 1.05 | −1.46 | −0.55 | −0.70 | 1.90 | AC113167.1 | −0.15 | −1.88 | −0.39 | 0.95 | 0.95 |
| CCDC18 | 0.37 | −0.47 | −0.51 | −0.20 | −0.02 | SLC35G3 | 0.46 | −0.33 | −0.73 | −0.10 | −0.68 | AP003774.3 | −0.23 | −0.92 | −0.68 | −0.11 | −0.41 |
| AC091390.1 | −0.83 | 0.38 | 0.01 | −0.42 | −0.36 | AC018816.1 | −0.28 | 0.14 | 0.47 | −0.22 | 0.36 | AC027673.1 | 0.45 | −0.54 | −1.27 | 2.12 | −0.94 |
| AFDN-DT | −0.80 | 0.66 | 0.41 | 0.33 | −0.46 | AC017028.8 | 0.59 | −0.48 | 1.43 | −0.01 | 1.55 | AC010745.1 | 0.48 | −0.01 | −1.01 | 0.14 | −0.81 |
| MAP4K3 | −0.16 | 0.21 | 0.22 | 0.06 | −0.07 | AC093844.1 | 0.87 | −1.94 | −1.51 | −0.43 | −0.98 | AC068657.1 | 0.09 | −0.17 | 0.65 | −0.46 | −0.04 |
| CYP17A1 | −1.38 | 0.01 | 2.73 | −1.08 | 0.13 | SLC44A2 | 0.11 | 0.21 | 0.04 | 0.07 | −0.26 | OOSP2 | 0.45 | −0.74 | −0.99 | −0.16 | −1.30 |
| ANP32D | −1.23 | 0.38 | 0.53 | 1.26 | −0.11 | PITPNM2 | −0.14 | −0.02 | −0.13 | 0.08 | 0.12 | OR5K3 | 0.30 | 0.47 | −1.41 | 0.40 | −2.01 |
| PTRHD1 | 0.69 | −0.19 | −0.88 | −0.17 | −0.74 | HSPD1P14 | 0.93 | −0.59 | −0.46 | −1.16 | −1.27 | AC005695.2 | −0.09 | −0.56 | 0.54 | −0.43 | 0.77 |
| PTPN1 | 0.31 | −0.26 | −0.58 | −0.08 | −0.31 | CAPNS1P1 | 0.55 | −0.60 | −1.21 | 0.83 | 0.01 | PQLC1 | −0.02 | 0.09 | −0.33 | 0.13 | −0.25 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC008393.1 | −0.61 | 0.49 | −0.24 | 0.35 | −0.44 | AL356575.1 | 0.75 | 0.52 | 0.65 | 0.52 | −0.16 | AL133465.1 | −0.66 | 0.70 | 0.45 | 1.26 | −1.05 |
| RNU6-83P | 1.14 | −0.18 | −0.09 | −0.21 | −0.04 | NDUFB10P2 | −1.19 | −0.08 | 1.62 | 0.12 | 0.45 | RPL15P20 | 0.17 | 0.14 | −0.11 | −0.26 | −1.42 |
| AC025470.2 | −1.30 | 0.60 | 0.15 | 1.00 | 0.34 | FAM21B | 0.15 | 0.06 | −0.18 | 0.94 | 1.03 | CASP2 | 0.02 | −0.13 | −0.21 | 0.06 | 0.00 |
| RHBDD3 | 0.37 | −0.33 | −0.54 | 0.14 | 0.05 | PCDHA8 | −0.57 | −0.12 | 0.95 | 0.60 | 0.60 | AC017002.4 | 0.28 | −0.71 | −2.81 | 1.80 | −1.95 |
| ACBD6 | 0.23 | −0.16 | −0.20 | −0.09 | 0.06 | AP001630.1 | −0.93 | 0.13 | 2.08 | −0.17 | 0.72 | EFCAB14-AS1 | 0.05 | −0.35 | −0.25 | −0.41 | −0.23 |
| OBP2A | −1.51 | 0.61 | 1.15 | 0.53 | 0.18 | HRAS | 0.15 | −0.12 | −0.65 | 0.19 | −0.04 | AC015815.2 | −0.07 | −0.82 | −0.25 | −0.12 | −0.27 |
| RPS10P7 | −0.49 | 0.27 | 0.26 | 0.31 | 0.38 | AL049844.1 | 0.71 | 0.09 | −0.68 | −0.18 | −1.66 | AP002812.1 | 0.06 | −0.30 | −0.10 | −0.19 | 0.38 |
| SLC22A4 | −0.47 | 0.18 | 0.37 | −0.22 | 0.10 | AC087741.1 | −0.19 | 0.20 | 0.22 | 0.18 | 0.14 | AL139174.1 | 0.06 | −0.53 | 0.76 | −0.27 | 0.62 |
| SIGLEC12 | 1.98 | −1.35 | −1.85 | −0.48 | −2.21 | AL365394.1 | −0.91 | −0.20 | −0.32 | 1.10 | 0.99 | AL357054.3 | 0.06 | 0.20 | −0.63 | 0.59 | 0.05 |
| BEST3 | −1.03 | 0.54 | 1.59 | 0.24 | 0.61 | SUDS3P1 | −0.25 | 0.19 | 0.45 | 0.34 | 0.31 | STON1-GTF2A1 | 0.10 | 0.36 | −1.24 | 0.54 | −0.30 |
| PRKCB | −0.62 | −0.37 | 0.71 | −0.40 | 0.34 | AC046130.2 | −0.52 | −1.45 | −0.14 | 0.12 | 1.30 | AC018926.3 | −0.06 | 0.43 | 0.21 | −0.07 | −0.03 |
| RNF135 | 0.23 | −0.08 | −0.33 | 0.09 | −0.27 | MTND4P15 | 0.19 | −0.07 | −0.31 | −0.06 | −0.28 | AC035140.1 | 0.64 | −0.46 | 0.49 | 0.67 | 0.47 |
| AC092153.1 | 1.45 | −1.08 | −1.48 | 0.06 | 0.02 | AL034351.1 | −0.86 | −0.54 | 1.43 | −0.24 | −0.84 | MTCO1P57 | −0.41 | 0.54 | 0.25 | 0.43 | −0.70 |
| HSPB3 | −1.62 | 0.07 | 1.48 | −0.83 | −0.49 | AC026356.1 | 0.39 | 0.03 | −0.61 | −0.65 | −0.69 | ARID5A | 0.04 | −0.36 | −0.15 | −0.28 | −0.06 |
| AL157871.5 | −0.69 | −0.06 | 0.82 | −0.28 | 0.55 | MYT1L-AS1 | 0.97 | −1.51 | −3.23 | 0.33 | −2.72 | RNU6-1228P | −0.19 | 2.13 | −1.08 | 0.80 | −1.22 |
| NDUFA7 | −0.53 | 0.22 | 0.20 | 0.32 | 0.29 | ETV2 | 0.32 | −0.36 | −0.03 | 0.21 | 0.20 | DCAF8L2 | −0.14 | −0.93 | −0.56 | 1.20 | 1.10 |
| RN7SL550P | −1.95 | 0.25 | 1.96 | 0.38 | 1.63 | CASA | −0.44 | −0.34 | −1.06 | 0.39 | −0.67 | AL033539.1 | 0.21 | 0.05 | −0.29 | 0.80 | −0.90 |
| FLRT1 | −0.85 | 0.82 | 0.92 | 0.19 | 0.44 | RN7SKP8 | −0.61 | −0.21 | −0.34 | 0.05 | 1.13 | AL589702.1 | −0.66 | 0.22 | −0.21 | 0.73 | −1.07 |
| AC092104.1 | −1.40 | 0.19 | 0.95 | −0.34 | 0.06 | AC103681.2 | −0.56 | 0.45 | 0.29 | −0.58 | 0.17 | SPON1-AS1 | −0.09 | −0.42 | 0.33 | −1.07 | 0.20 |
| ADGRB2 | −0.62 | 0.15 | 0.10 | 0.12 | −0.11 | FZD3 | −0.13 | 0.31 | 0.05 | 0.16 | −0.05 | AMMECR1-IT1 | −0.06 | −0.63 | −0.16 | −0.18 | 0.37 |
| AC244153.1 | 0.96 | −0.42 | −0.68 | −0.26 | −0.61 | MDH1 | 0.15 | −0.06 | −0.22 | −0.03 | −0.16 | SNORD91B | 0.05 | 0.28 | 0.06 | 0.22 | −0.34 |
| AL590560.1 | −0.52 | 0.50 | 0.39 | 0.44 | 0.31 | LYZL6 | 1.28 | 0.09 | −1.64 | 1.39 | −2.47 | AC078950.1 | −0.06 | 0.44 | −0.30 | 0.23 | −0.84 |
| SPG21 | 0.33 | −0.26 | −0.17 | −0.17 | −0.04 | DNPEP | −0.11 | 0.02 | −0.19 | 0.25 | 0.05 | AL033523.1 | 0.66 | −0.41 | −0.31 | −0.20 | −0.90 |
| FAM186A | −0.91 | 0.23 | 0.66 | −0.07 | 0.01 | IGKV5-2 | 1.16 | −0.50 | −1.48 | 0.17 | −3.21 | CEP63 | −0.02 | 0.02 | 0.02 | −0.02 | 0.01 |
| C10orf62 | −1.30 | 0.92 | 0.72 | 0.37 | −0.32 | AC019211.1 | −0.43 | −0.04 | 0.19 | 0.13 | 0.58 | AC087565.1 | −0.40 | 0.12 | −0.13 | 0.46 | −0.81 |
| AC090844.3 | −1.46 | 0.23 | 1.82 | −0.14 | 1.11 | LINC00987 | 0.40 | −0.11 | −0.41 | 0.23 | −0.19 | GPR75 | 0.04 | 0.24 | −0.18 | 0.07 | −0.19 |
| SLC2A13 | −0.36 | 0.23 | 0.44 | −0.06 | 0.13 | LGALS8-AS1 | 0.48 | −1.24 | 0.35 | −0.05 | 0.53 | PIKFYVE | −0.01 | 0.06 | 0.07 | 0.01 | −0.04 |
| AC073107.1 | −0.68 | 0.11 | 0.51 | 0.03 | 0.47 | AL137186.2 | −0.15 | 0.06 | 0.00 | 0.08 | −0.01 | GNGT1 | −0.12 | −0.47 | −1.65 | 0.22 | −1.16 |
| CD3E | 1.10 | −0.61 | 0.01 | −0.46 | 0.22 | CNN2P6 | −0.93 | −0.03 | 0.59 | 0.38 | 0.13 | AL591222.2 | 0.26 | −1.72 | −0.35 | −0.04 | 0.10 |
| AC103810.5 | −0.85 | 0.24 | 0.53 | 0.47 | 0.47 | AC126768.3 | −0.45 | −0.49 | −1.19 | 1.31 | 1.16 | LINC00941 | −0.05 | −0.67 | −0.26 | −0.21 | 0.28 |
| ALB | −1.22 | −0.09 | 0.65 | 0.18 | 0.70 | AC007249.1 | −0.66 | 0.51 | 1.33 | −0.66 | −1.25 | AL035665.1 | 0.06 | −0.05 | −0.23 | 0.35 | −0.28 |
| AF064858.2 | −1.02 | 0.47 | 0.73 | 0.17 | 0.46 | SMIM21 | 0.86 | −2.28 | −1.85 | 1.68 | 0.90 | AL118496.2 | 0.23 | −0.40 | −1.51 | −0.76 | −1.11 |
| AL133445.2 | 1.02 | −0.80 | −0.63 | −0.35 | 0.20 | AC008035.1 | −0.36 | −0.17 | −0.06 | 0.79 | 0.48 | AC105275.2 | −0.37 | 0.11 | −0.89 | 0.23 | −2.04 |
| PEX6 | −0.40 | 0.17 | 0.16 | 0.16 | −0.09 | AC027271.1 | 0.69 | 0.35 | −0.54 | 0.17 | −0.49 | AL136528.1 | −0.36 | 0.15 | 0.01 | 0.21 | 1.27 |
| ASIP | −0.81 | 0.04 | 1.30 | 0.10 | 0.81 | RPL21P89 | 0.39 | −0.32 | 0.17 | 0.18 | 0.34 | OR6C70 | −0.32 | −0.32 | −0.66 | −0.81 | 0.37 |
| AC245052.7 | 1.63 | −0.40 | −1.48 | 0.02 | 0.21 | AC009158.1 | 0.82 | −0.78 | −0.29 | −0.02 | 1.48 | RN7SL362P | 0.09 | 0.04 | −2.01 | −0.58 | −1.56 |
| SNORA17 | 1.05 | −0.35 | −0.52 | −0.16 | −0.24 | AC021683.5 | −0.55 | −0.41 | 0.40 | −0.04 | 0.77 | G8112 | 0.04 | −0.29 | −0.36 | 0.25 | 0.22 |
| SNRPGP13 | 2.59 | −2.59 | −2.56 | −1.17 | −0.62 | SP3P | 0.90 | −0.21 | −3.53 | 0.91 | −1.75 | OR7E158P | 0.13 | −1.28 | −1.54 | −0.42 | −1.60 |
| FSD2 | −0.60 | 0.35 | 0.21 | 0.20 | 0.12 | GOSR1 | 0.08 | −0.01 | 0.04 | −0.04 | −0.06 | MTND6P18 | 0.05 | 0.02 | −0.23 | −0.15 | −0.29 |
| BTN2A2 | −0.46 | 0.03 | 0.29 | −0.03 | 0.14 | AL133243.4 | 0.12 | −0.08 | −0.20 | −0.06 | −0.16 | OR5BR1P | 0.14 | −0.80 | −0.02 | −0.24 | 0.19 |
| PSMG4 | 0.35 | −0.15 | −0.17 | −0.10 | −0.04 | ST6GALNAC3 | −0.28 | 0.26 | 0.68 | 0.15 | 0.07 | RNU6-972P | 0.18 | −1.12 | 0.86 | −0.43 | 1.17 |
| C1orf158 | −1.50 | 0.58 | −0.91 | 2.57 | 0.98 | AC073529.1 | −0.21 | 0.11 | 0.15 | 0.31 | 0.09 | AC007450.3 | −0.18 | 0.09 | 0.95 | −0.12 | 0.15 |
| AL513304.1 | 3.10 | −2.37 | −3.53 | −0.02 | −2.05 | SNTG1 | −0.47 | −0.21 | −0.55 | 0.34 | −0.09 | OR4D6 | −0.32 | 1.37 | 0.37 | 1.25 | −1.02 |
| SNORA34 | −0.65 | 0.38 | 0.26 | 0.49 | −0.24 | MARK2P17 | 0.66 | −0.60 | 0.63 | −0.85 | 0.75 | G554 | 0.11 | 0.63 | 1.06 | 0.23 | −0.32 |
| GNG12 | 0.51 | −0.01 | −0.29 | −0.02 | −0.51 | AC108067.1 | 1.17 | 0.91 | −1.00 | 0.71 | −1.26 | HIST1H1PS2 | 0.56 | 0.94 | 1.78 | −0.54 | 0.61 |
| RP11-782C8.6 | −0.98 | 0.93 | 0.70 | 0.53 | −0.16 | RN7SL178P | −1.32 | 0.76 | −0.21 | 0.64 | −1.74 | PRPF40B | −0.02 | 0.07 | −0.06 | 0.12 | 0.13 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| NME3 | −0.55 | 0.29 | 0.04 | 0.43 | 0.23 | ABCG8 | 0.28 | −0.47 | −0.56 | 0.46 | 0.16 | AC092673.1 | 0.66 | −0.91 | −1.98 | −1.59 | −0.20 |
| SOCS1 | 0.90 | −1.04 | −1.09 | −0.38 | −0.53 | AL157832.2 | −0.31 | 0.02 | 0.12 | 0.34 | 0.43 | NPM1P31 | −0.12 | −1.49 | −2.58 | −0.06 | −0.56 |
| MDGA1 | −0.63 | −0.20 | 0.44 | −0.43 | 0.08 | AC006960.1 | −0.62 | −0.82 | 0.03 | −0.22 | −0.10 | AL358074.1 | −0.09 | −1.43 | −0.15 | −0.02 | 0.89 |
| KIAA0556 | −0.31 | 0.22 | 0.12 | 0.16 | 0.00 | PHOX2B | −0.94 | 1.06 | −0.96 | 0.53 | −0.78 | HSPD1P6 | −0.10 | −0.81 | −0.38 | −0.54 | 0.03 |
| BTF3L4 | 0.33 | −0.10 | −0.27 | −0.08 | −0.40 | AC016722.2 | 0.26 | −0.24 | −0.40 | −0.17 | −0.14 | AC013429.1 | −0.66 | 1.05 | 0.08 | 0.81 | −1.92 |
| FYN | −0.51 | 0.08 | 0.70 | −0.22 | 0.07 | STAMBPL1 | 0.12 | −0.30 | −0.10 | −0.09 | 0.15 | AC096576.2 | −0.62 | −0.24 | −0.02 | 1.25 | 0.21 |
| AC133552.2 | −0.81 | 0.26 | 0.95 | 0.08 | 0.78 | AC069431.1 | −0.51 | −0.57 | −0.12 | 0.05 | 0.04 | LDHAL6DP | 0.43 | 0.02 | 0.94 | 0.13 | 0.97 |
| NFIA | −0.37 | 0.34 | 0.30 | 0.27 | 0.09 | RN7SL262P | −0.95 | 0.33 | 2.00 | 0.52 | 0.49 | LINC01506 | −0.19 | 0.49 | 0.69 | 0.05 | −0.67 |
| DVL3 | −0.27 | 0.19 | −0.10 | 0.15 | −0.02 | AC087752.1 | 0.46 | −1.10 | −0.08 | −0.61 | −0.05 | AL122008.3 | 0.12 | 0.53 | −2.09 | 0.73 | −1.13 |
| AC092067.1 | −0.75 | −0.50 | 0.57 | −0.18 | 0.85 | AC090993.1 | −1.15 | −0.47 | −0.39 | 0.41 | 1.61 | GTF2A1L | 0.45 | −0.52 | 0.14 | −1.24 | −0.34 |
| CHKA | −0.45 | 0.06 | 0.23 | −0.12 | 0.10 | LYZL4 | −0.99 | 0.35 | −0.54 | 0.64 | −1.63 | AC025887.2 | 0.08 | −0.02 | −0.43 | 0.06 | −0.26 |
| SIN3B | −0.40 | 0.03 | −0.01 | 0.05 | 0.09 | ANKRD23 | −0.37 | 0.42 | 0.31 | 0.27 | −0.07 | AC011472.1 | −0.04 | 0.60 | 0.27 | 0.07 | −0.40 |
| LOR | −1.27 | 1.30 | 1.73 | 1.84 | −0.03 | AC097641.1 | 0.53 | −1.59 | −0.09 | −0.80 | 0.26 | AC073324.1 | −0.25 | −0.78 | 0.78 | −0.74 | −1.04 |
| AC016738.1 | −0.74 | 0.36 | 0.47 | −0.13 | 0.68 | AC025171.5 | −0.23 | −0.04 | 0.42 | 0.46 | 0.80 | ACTBP6 | 0.27 | −0.44 | 0.91 | −0.05 | −0.38 |
| MBNL1 | 0.32 | −0.06 | −0.18 | −0.07 | −0.29 | AL353588.1 | 0.42 | 0.75 | −0.36 | 0.58 | −0.58 | PACRG−AS2 | 0.12 | 0.34 | −0.35 | 1.13 | −0.38 |
| AC092162.3 | −1.41 | 1.20 | 1.47 | 0.63 | −0.39 | SNORA62 | 0.23 | −0.45 | −0.88 | 0.02 | −0.11 | AC068781.1 | −0.35 | 1.04 | −0.10 | −0.58 | −1.26 |
| ATAD1 | 0.36 | −0.11 | −0.21 | −0.10 | −0.24 | NAALADL2-AS2 | −0.67 | −1.21 | 1.34 | −0.10 | 1.35 | AC003001.2 | 0.38 | −1.50 | 0.18 | −1.16 | −0.43 |
| PSAT1P2 | −2.40 | 1.74 | 1.79 | −0.83 | −0.31 | NKX2-3 | −0.59 | 0.50 | 0.23 | 0.85 | 0.64 | FOXP1-AS1 | −0.05 | 0.19 | 0.46 | 0.39 | 0.27 |
| AC009065.2 | −0.96 | 0.04 | −0.57 | 0.06 | −0.07 | RAD51C | −0.15 | −0.15 | 0.33 | −0.46 | 0.15 | FAM24A | 0.26 | −0.41 | −2.41 | 0.28 | 0.03 |
| DSCAS | 1.07 | 0.18 | 0.76 | 0.48 | 0.05 | RNU6-1079P | 0.54 | 0.28 | −0.75 | 0.37 | −0.23 | ASH2LP2 | 0.27 | −0.45 | −2.17 | 0.02 | −3.35 |
| GLYATL1B | −1.45 | 1.30 | 1.70 | 0.08 | −0.43 | RN7SL769P | −0.70 | −0.63 | −1.66 | 0.90 | 0.04 | PCGF7P | −0.13 | 0.59 | 0.53 | −0.66 | 0.36 |
| AC124312.5 | −1.00 | 0.68 | 1.20 | 0.20 | 0.52 | AC110023.1 | −1.29 | 0.01 | 1.40 | 0.36 | 1.74 | RNA5SP69 | −0.12 | 1.04 | 1.03 | −0.52 | −0.89 |
| POM121 | 0.24 | −0.11 | −0.22 | −0.04 | −0.02 | AL031665.2 | 0.41 | −0.19 | 1.09 | −0.12 | 0.54 | AC112656.1 | −0.21 | 1.02 | 0.22 | 0.26 | 1.01 |
| AC017048.2 | −0.91 | 0.66 | 1.35 | 0.78 | 0.68 | AL137077.1 | 0.31 | −0.42 | −0.21 | 0.09 | 0.30 | LINC02270 | −0.28 | −0.83 | −0.54 | −0.08 | −0.48 |
| AC053513.1 | −0.54 | 0.04 | 0.49 | 0.05 | 0.40 | G35259 | −0.34 | 0.51 | 1.11 | −0.10 | 0.10 | AL031775.2 | −0.05 | 0.01 | 0.21 | 0.12 | −0.02 |
| AC104164.1 | −0.90 | 0.67 | 1.21 | −0.08 | 0.23 | AC006504.1 | −0.17 | −0.04 | −0.03 | −0.10 | −0.21 | AC016903.1 | 0.40 | 0.56 | 0.59 | 0.64 | −0.79 |
| SLC39A5 | −0.89 | 0.18 | −0.03 | 0.21 | −0.14 | AL139317.1 | −1.00 | −0.05 | −0.24 | −1.10 | −1.32 | C8A | 0.18 | 0.31 | −1.51 | 1.44 | −2.52 |
| CD70 | −1.19 | 0.69 | 2.01 | −0.12 | 0.21 | AC104971.1 | 0.73 | −1.04 | −0.19 | −1.02 | −1.06 | NPL | −0.02 | −0.11 | 0.03 | −0.07 | −0.02 |
| SNX18P16 | −1.48 | 0.99 | 0.46 | 0.78 | 0.45 | AC012640.2 | 0.33 | 0.56 | 0.18 | 0.42 | −0.36 | IQCF1 | 0.34 | 0.11 | 1.14 | −1.27 | −0.41 |
| CPXM1 | 1.14 | 0.23 | 1.04 | −0.77 | −0.44 | CALR3 | 0.91 | −2.52 | −1.72 | −0.09 | 0.19 | OR13C1P | −0.12 | −0.03 | −0.14 | −0.21 | −0.63 |
| ANKRD34A | −0.63 | 0.08 | 0.18 | 0.20 | 0.25 | LINC02228 | 0.65 | −1.48 | −2.13 | 0.40 | −0.40 | AC093816.1 | −0.21 | −0.21 | −2.34 | 0.93 | −0.57 |
| MORF4L1 | 0.32 | −0.17 | −0.21 | −0.17 | −0.22 | AC244093.1 | 0.27 | −0.18 | −0.35 | −0.09 | −0.11 | IGHV3-66 | 0.65 | 0.67 | −0.68 | 2.40 | −2.58 |
| AL450405.1 | 0.54 | 0.13 | −0.27 | 0.28 | −0.41 | SCN3A | −0.26 | −0.05 | 0.42 | 0.20 | −0.05 | LINC01713 | −0.20 | −0.26 | −0.15 | 0.18 | −0.26 |
| SH3GL1P1 | −0.59 | 0.44 | 0.63 | 0.56 | 0.38 | FOXN3-AS1 | −0.20 | −0.54 | 0.34 | −0.12 | 0.62 | AC000372.1 | −0.24 | 0.45 | −0.72 | −0.98 | −2.49 |
| GTF3C4 | 0.44 | 0.00 | −0.08 | 0.04 | −0.24 | NDUFA3 | −0.09 | −0.07 | 0.08 | 0.03 | 0.20 | AC243965.1 | −0.17 | −1.44 | −0.24 | −1.09 | −0.98 |
| AL356273.2 | −0.50 | 0.38 | 0.34 | 0.18 | −0.01 | MIR140 | −0.62 | 0.68 | 0.99 | −0.60 | 0.86 | AC079035.1 | 0.04 | 0.25 | 0.49 | 0.00 | 0.12 |
| FAM242C | −1.04 | 0.54 | 1.31 | 0.08 | 0.43 | AL590093.1 | −0.46 | −0.10 | 1.76 | 0.22 | 1.29 | LINC00355 | −0.16 | 0.55 | −0.07 | 0.73 | 0.01 |
| AC036176.3 | 1.27 | 0.23 | −0.72 | −0.22 | −0.59 | AL356535.1 | 0.71 | −0.27 | 0.44 | 0.26 | 0.22 | AC110491.1 | −0.11 | −0.36 | −0.39 | 1.36 | 0.36 |
| AP000769.1 | 0.62 | −0.34 | −0.23 | −0.18 | −0.45 | AC079313.1 | −0.25 | −0.28 | 0.10 | −0.65 | −0.30 | AC020763.3 | −0.04 | −0.10 | 0.00 | −0.03 | 0.11 |
| G3030 | −0.86 | −0.23 | 0.32 | 0.11 | 0.88 | GHRHR | −0.77 | −1.33 | −1.62 | 0.17 | 0.25 | OR4C1P | 0.22 | 1.03 | −0.67 | 1.53 | 0.98 |
| AC004053.1 | −1.61 | 0.88 | 0.13 | 0.43 | −0.12 | RPL23AP90 | 0.43 | 0.51 | −0.47 | 0.29 | −0.59 | DPP3P1 | 0.30 | 0.75 | −0.67 | 0.71 | −2.95 |
| RN7SL637P | −1.13 | 0.53 | 1.43 | 0.71 | 0.44 | AL023802.1 | −0.59 | −0.36 | −0.90 | 0.66 | 0.15 | RNU6-810P | 0.12 | 0.48 | 1.71 | 0.37 | 0.67 |
| AOX1 | −0.90 | 0.34 | 1.47 | 0.01 | 0.31 | EPO | −0.63 | −0.04 | 0.92 | 0.39 | 1.04 | LINC01812 | −0.22 | 0.18 | −1.73 | −0.37 | −1.88 |
| CABP7 | −1.25 | 0.74 | 0.27 | 1.32 | 0.20 | AC078802.1 | 0.68 | −0.65 | 0.77 | −0.09 | 0.05 | LINC02450 | −0.31 | −0.44 | 0.18 | −0.44 | 0.48 |
| ANO2 | −0.72 | 0.27 | 0.57 | 0.10 | 0.60 | MIR194-1 | 0.70 | 0.26 | −0.45 | 0.37 | −0.91 | SH3BP4 | 0.02 | 0.10 | −0.19 | 0.05 | 0.04 |
| AC004241.5 | −0.73 | 0.48 | 0.20 | 0.00 | −0.31 | BRF2 | −0.15 | 0.10 | 0.06 | 0.15 | −0.15 | AC005632.4 | −0.31 | −1.29 | −0.78 | 0.41 | −0.28 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| DENND4A | 0.32 | −0.17 | −0.24 | 0.01 | −0.12 | AP003327.1 | 1.39 | −0.55 | −0.98 | −1.42 | −2.63 | AP000889.2 | 0.21 | 0.14 | 0.84 | 1.26 | 0.24 |
| GRIK3 | −1.19 | 0.60 | 1.39 | 0.38 | 0.83 | AC023403.1 | −0.52 | 0.16 | 1.35 | −0.61 | −0.20 | MIR4298 | 0.21 | −1.70 | 0.38 | −0.58 | 2.89 |
| KAT5 | −0.34 | 0.43 | 0.07 | 0.18 | −0.09 | AL158801.3 | 0.39 | −0.16 | −0.10 | −0.20 | −0.12 | AL021997.3 | −0.15 | 0.29 | 1.01 | −0.33 | 0.60 |
| ANAPC11 | 0.36 | −0.09 | −0.18 | 0.06 | −0.23 | AC024592.1 | −0.57 | 0.39 | 0.74 | 0.14 | 0.18 | PTPN20B | −0.07 | −0.06 | −0.27 | 0.36 | 0.59 |
| STMN3 | −0.50 | 0.03 | 0.43 | −0.18 | 0.18 | AC006499.4 | 1.43 | −1.00 | −1.00 | −1.31 | 0.51 | CHEK2P2 | −0.17 | −1.01 | −0.55 | −0.38 | 0.40 |
| PLCD1 | 0.33 | −0.11 | −0.73 | 0.06 | −0.44 | G8296 | 0.38 | 0.49 | −0.22 | 1.09 | −0.18 | AC012676.5 | 0.04 | −0.42 | −0.30 | −0.04 | 0.48 |
| MTRR | 0.21 | −0.24 | −0.19 | −0.06 | 0.06 | RGS13 | −0.37 | 0.23 | 0.07 | 0.04 | −0.31 | AC090709.1 | 0.34 | −0.40 | −1.53 | 0.08 | −1.88 |
| PLEKHB1 | −0.64 | 0.80 | 0.79 | 0.25 | 0.25 | AC079340.1 | −0.79 | −0.55 | −0.22 | −0.03 | −0.59 | HTR1D | 0.12 | −0.49 | −0.99 | −0.51 | −0.49 |
| ASS1 | −0.51 | 0.18 | 0.00 | 0.27 | −0.65 | MSRB2 | −0.17 | 0.05 | 0.49 | −0.08 | 0.11 | LAMA1 | −0.06 | 0.10 | 0.30 | −0.40 | 0.00 |
| AC010680.5 | −1.12 | 0.45 | 0.94 | −0.77 | −0.24 | AC136469.1 | −0.50 | −0.26 | 1.93 | −1.55 | 0.37 | SNORA18 | 0.07 | −0.26 | −0.64 | −0.12 | 0.13 |
| DCAF10 | 0.35 | −0.09 | −0.04 | −0.11 | −0.16 | GAS5-AS1 | −0.24 | −0.23 | −0.18 | 0.03 | 0.39 | AP002782.1 | −0.65 | 1.18 | −0.01 | −0.17 | −1.89 |
| LINC00937 | −0.71 | −0.58 | 0.75 | −0.36 | 0.80 | G19261 | −0.49 | 0.50 | 0.59 | −0.40 | −0.12 | LINC01939 | −0.32 | 0.96 | −0.46 | 2.02 | 1.19 |
| RPS3AP30 | −1.89 | 0.56 | 3.92 | −1.12 | 1.47 | RN7SL552P | 0.37 | −0.10 | −0.69 | −0.15 | −0.85 | DEFB119 | −0.23 | −0.44 | 0.60 | −0.80 | −1.00 |
| ESS2 | −0.36 | 0.07 | 0.07 | 0.14 | 0.14 | AL512326.1 | 0.25 | −0.33 | −0.49 | −0.10 | −0.21 | AC010834.2 | −0.17 | 0.79 | 1.39 | 0.20 | 0.07 |
| SLC44A3-AS1 | −0.73 | 0.27 | 0.61 | 0.06 | −0.13 | SLC16A7 | 0.22 | −0.26 | −0.01 | −0.15 | −0.03 | EGLN3P1 | −0.05 | 0.35 | −0.41 | 0.54 | −0.21 |
| SPRY2 | −0.37 | 0.40 | −0.01 | 0.29 | −0.14 | AC051642.1 | 1.16 | −2.88 | 1.04 | −0.59 | 2.15 | MIR5683 | −0.12 | −0.49 | −0.25 | −0.26 | 0.76 |
| NUDT16 | −0.38 | 0.20 | 0.35 | 0.03 | 0.10 | OR2V1 | 1.15 | −0.89 | −0.05 | 0.63 | 0.08 | AC011824.3 | 0.65 | 0.69 | −2.04 | −0.39 | −3.19 |
| PAPLN | −0.61 | 0.49 | 0.65 | 0.40 | −0.02 | GOLGA6L9 | −0.29 | 0.28 | 0.06 | 0.15 | −0.44 | CBR4 | −0.02 | 0.01 | 0.14 | 0.01 | 0.17 |
| RDX | 0.38 | −0.19 | −0.31 | −0.17 | −0.25 | RAB5CP1 | 0.29 | −0.37 | −0.08 | −0.20 | 0.29 | AL109806.1 | −0.06 | −0.83 | −0.05 | 0.50 | 0.83 |
| CMKLR1 | −0.81 | 0.21 | 0.61 | 0.06 | 0.11 | RNU6-1165P | 0.76 | −0.02 | 0.19 | 0.52 | −0.03 | KM-PA-2 | −0.19 | −0.40 | −0.16 | 1.03 | 0.44 |
| BTN1A1 | −0.96 | −0.03 | 1.65 | −0.05 | 0.58 | AC008802.1 | 0.94 | 0.42 | −0.55 | 0.62 | −0.61 | IFNA20P | −0.07 | −0.27 | 0.51 | −0.23 | 0.67 |
| POLM | −0.46 | −0.05 | 0.20 | 0.06 | 0.25 | AC093392.1 | −0.75 | −0.93 | 0.41 | −0.01 | 1.38 | LINC01213 | −0.10 | −0.06 | 0.40 | 0.69 | 0.43 |
| CHST2 | 0.86 | −0.16 | 0.13 | −0.89 | −1.03 | GCDH | −0.11 | −0.09 | 0.02 | 0.01 | 0.18 | FAM216B | −0.11 | −0.87 | −1.07 | −0.58 | 0.42 |
| AC027237.1 | 1.38 | −0.99 | −1.25 | −0.59 | −1.08 | AL392023.1 | −0.88 | −0.95 | 0.13 | −0.16 | 0.27 | PRR5L | 0.03 | −0.18 | 0.10 | −0.21 | 0.13 |
| HOXC13-AS | 0.72 | 0.19 | −0.25 | 0.28 | −0.24 | RPL22P2 | 0.51 | −0.51 | 1.74 | −0.44 | −0.01 | OSTCP2 | −0.11 | 1.13 | 2.58 | 1.69 | 0.77 |
| AC009113.1 | −0.55 | 0.34 | 0.76 | 0.23 | 0.59 | AC087441.2 | 0.40 | −0.13 | −0.87 | 0.27 | −0.13 | LINC01927 | −0.16 | −2.11 | 1.55 | 0.37 | 3.73 |
| AC087286.4 | −0.58 | −0.13 | 0.30 | −0.27 | 0.32 | CXCR2P1 | 0.66 | −1.81 | −1.24 | −0.87 | −0.60 | AP003717.2 | −0.13 | 0.79 | 0.19 | 0.27 | 0.54 |
| MOB3C | 0.31 | −0.22 | −0.52 | −0.07 | −0.07 | MIR5684 | 1.29 | −1.47 | −0.40 | −2.43 | 0.21 | AL161740.1 | −0.65 | 0.48 | −0.20 | 0.06 | 0.82 |
| LINC01844 | −1.46 | 0.89 | 0.44 | 0.96 | 0.63 | CDH24 | 0.17 | 0.09 | −0.36 | 0.26 | −0.10 | SMIM15-AS1 | 0.06 | −0.29 | 0.11 | −0.17 | −0.10 |
| ABCF1 | 0.32 | −0.19 | −0.45 | −0.17 | −0.26 | AC097532.1 | −0.63 | 0.13 | 0.10 | 1.21 | 0.54 | AL121902.1 | 0.64 | −0.70 | −0.58 | 0.31 | 0.01 |
| ST6GALNAC2 | −0.56 | 0.26 | 0.09 | 0.34 | 0.04 | AC008536.1 | −0.68 | 0.30 | 0.71 | −0.52 | −0.49 | IGLV3-10 | 0.65 | −0.39 | 1.48 | −2.13 | 0.15 |
| RPS4XP16 | −0.98 | 0.55 | 0.60 | 0.26 | −0.09 | FAM237A | 0.83 | −0.88 | −0.34 | −0.53 | 0.62 | AC091980.2 | −0.14 | −1.71 | −2.06 | −0.03 | −1.09 |
| AL078590.3 | −0.71 | 0.33 | 1.00 | 0.50 | 0.49 | PF4 | −0.72 | 0.47 | 1.05 | 0.55 | −1.30 | MDFIC2 | 0.25 | 0.19 | −0.72 | 1.20 | −1.89 |
| AC138969.1 | −0.99 | 0.01 | −0.10 | 0.83 | 0.37 | AC092650.1 | −0.48 | −0.64 | −0.79 | 0.43 | −0.18 | AC069307.1 | −0.08 | −0.09 | −0.02 | 0.09 | 0.46 |
| RHEBL1 | −0.62 | 0.43 | 0.11 | 0.13 | −0.11 | AC113404.3 | 0.38 | −0.13 | −0.15 | 0.07 | 0.41 | LINC00333 | −0.24 | −0.99 | 0.07 | −1.43 | 0.52 |
| LINC01352 | −1.76 | 1.78 | 0.79 | 0.69 | −0.44 | HSPB1P2 | 0.49 | 0.02 | −0.38 | 0.06 | −0.40 | RANP7 | 0.29 | −0.93 | 0.92 | 0.03 | 0.20 |
| CYTIP | 0.76 | −1.00 | −0.38 | −0.39 | −0.13 | CDC73 | −0.07 | 0.12 | 0.02 | −0.06 | −0.13 | AC087521.3 | −0.06 | 0.19 | −0.64 | 0.09 | −0.49 |
| POGZ | −0.24 | 0.17 | 0.30 | −0.02 | 0.12 | SMPD1 | 0.14 | 0.25 | 0.09 | 0.00 | −0.30 | FCERIA | −0.05 | 0.03 | 0.66 | 0.24 | 0.24 |
| SAPCD1 | −0.90 | 0.26 | 0.64 | 0.26 | 0.28 | RN7SKP67 | 0.94 | −0.41 | −1.49 | −0.15 | −1.71 | CCDC183-AS1 | 0.04 | 0.00 | −0.16 | 0.05 | 0.03 |
| ENG | 0.57 | −0.56 | −0.06 | −0.26 | −0.33 | CRYBA2 | 1.16 | −0.94 | −1.45 | −0.20 | −1.91 | AC011978.1 | −0.17 | −0.99 | −1.34 | 0.13 | 0.51 |
| KCNG3 | 0.76 | −0.25 | −1.02 | 0.49 | −0.31 | MIR549 | 1.24 | −1.76 | −0.91 | −1.05 | −0.28 | GAL3ST3 | −0.13 | −1.01 | −1.28 | 1.18 | −0.24 |
| GATM | −0.68 | 0.50 | 1.02 | 0.39 | 0.52 | AC104332.2 | 0.39 | −0.25 | 0.14 | −0.01 | −0.25 | RPL34P26 | −0.13 | −0.65 | 0.17 | 0.55 | 0.95 |
| SARNP | −0.45 | 0.03 | 0.03 | 0.08 | 0.26 | AC121761.1 | 0.21 | −0.57 | 0.11 | −0.28 | 0.47 | AC004706.1 | −0.06 | 0.05 | 0.58 | −0.23 | 0.15 |
| CD300C | 1.08 | −0.97 | −0.70 | −0.59 | −0.23 | HOXC11 | 0.22 | 0.29 | −0.30 | 0.02 | −0.34 | RN7SKP25 | 0.19 | −0.98 | −0.20 | −0.95 | −1.60 |
| AC007749.1 | −1.29 | 1.66 | 2.29 | 0.64 | −0.16 | ACKR1 | −0.25 | 0.35 | 1.22 | 0.13 | 0.19 | AP002370.1 | 0.17 | −0.60 | 0.93 | 0.43 | −0.53 |
| HSPA13 | 0.50 | −0.34 | 0.07 | −0.48 | −0.31 | RDH8 | 0.89 | −0.46 | −1.28 | −0.41 | −1.51 | OPN5 | −0.10 | −0.57 | −0.68 | 0.07 | −0.19 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| GSAP | −0.35 | 0.12 | 0.45 | −0.14 | 0.31 | AC025161.1 | 1.37 | −0.54 | −2.67 | 0.00 | −2.66 | AC079598.3 | −0.37 | 0.16 | 0.81 | −1.15 | −0.60 |
| NALT1 | −1.11 | 0.50 | −0.08 | 1.03 | 0.99 | AC083798.2 | −0.13 | −0.13 | 0.00 | 0.09 | 0.09 | FAM166A | 0.06 | −0.81 | 0.38 | −0.23 | 0.33 |
| AL020995.1 | 0.92 | −0.22 | −0.62 | 0.19 | 0.03 | G5850 | −1.61 | 1.22 | 0.51 | 0.75 | −0.15 | AC112225.1 | 0.09 | 0.39 | −0.45 | 0.03 | −0.21 |
| AC025030.1 | 0.95 | −1.33 | −1.36 | −0.38 | 0.09 | AL583827.1 | −0.73 | 0.10 | 0.02 | 0.05 | −0.71 | DPH6 | −0.02 | 0.04 | −0.02 | 0.16 | 0.00 |
| PARP10 | −0.50 | −0.09 | 0.23 | −0.11 | 0.27 | LINC01578 | −0.11 | 0.19 | 0.04 | 0.15 | −0.02 | OR4A21P | −0.64 | −0.30 | 1.29 | 1.18 | 1.69 |
| LINC01569 | −0.63 | 0.02 | 0.01 | 0.26 | 0.28 | AC026250.1 | 0.31 | −0.36 | 0.24 | −0.36 | 0.38 | SNORA7 | −0.05 | −0.11 | −0.28 | 0.12 | −0.07 |
| G4558 | −2.48 | −1.36 | 0.00 | −0.68 | 1.18 | AL023803.3 | 0.63 | −0.73 | −1.87 | −0.07 | −0.98 | CCDC8 | 0.04 | −0.06 | −0.19 | 0.21 | 0.24 |
| SMOC2 | −0.54 | 0.72 | 0.45 | 0.01 | −0.42 | MIOX | −0.83 | 0.29 | −0.18 | −0.24 | 0.77 | EDDM3A | 0.26 | −1.28 | −1.98 | −0.15 | −0.87 |
| AC100793.2 | −1.11 | −0.06 | 0.16 | 0.51 | 0.74 | PPP3CC | −0.12 | 0.04 | 0.03 | −0.17 | −0.16 | LINC01340 | 0.17 | −0.60 | 0.44 | −0.11 | 0.99 |
| OLFML2A | −0.55 | 0.50 | 0.60 | 0.19 | −0.02 | AC006058.1 | 0.30 | 0.22 | −0.55 | 0.56 | −0.69 | SLC29A3 | 0.04 | 0.11 | −0.12 | −0.05 | −0.27 |
| AC092756.1 | 0.69 | −0.48 | −0.46 | −0.69 | 0.00 | SDCBP | 0.14 | −0.03 | −0.03 | −0.11 | −0.12 | BLACE | −0.41 | 0.56 | 0.02 | 0.74 | −0.68 |
| NANP | 0.38 | −0.31 | −0.10 | −0.25 | 0.00 | AC016027.1 | 0.27 | 0.12 | −0.08 | 0.29 | −0.48 | AC097493.3 | 0.64 | 1.27 | 0.82 | −0.04 | −1.72 |
| CHCHD2P11 | 1.75 | −0.32 | −1.67 | −0.47 | −1.42 | AC130456.2 | −1.07 | 1.39 | 1.39 | 2.00 | 0.46 | BNIP3P17 | −0.15 | 0.63 | −1.14 | 0.95 | −2.36 |
| AC130366.1 | −1.09 | −0.28 | 1.26 | −0.30 | 1.08 | AL031772.1 | 0.20 | −0.06 | 0.00 | −0.02 | 0.17 | AL365440.1 | −0.09 | 0.20 | −0.77 | 0.16 | −0.08 |
| G10801 | 1.95 | −1.23 | −1.67 | 1.06 | 3.05 | AC005330.1 | −0.54 | 0.30 | −0.18 | 1.11 | 0.04 | NCOR1P2 | 0.28 | 0.12 | −1.12 | 1.57 | 0.50 |
| AC008781.3 | −1.10 | 0.62 | 2.30 | −0.46 | 0.62 | AC131254.2 | −0.55 | −1.01 | −0.88 | 0.14 | 0.43 | GPT2 | −0.03 | −0.23 | −0.11 | 0.15 | 0.33 |
| LHB | −1.43 | 1.06 | −1.19 | 0.09 | −0.77 | H2AFJ | 0.12 | 0.08 | −0.37 | 0.34 | −0.41 | AC022140.1 | −0.27 | 0.29 | 2.45 | −1.16 | −0.51 |
| SMARCA5 | 0.36 | −0.18 | −0.22 | −0.14 | −0.13 | CICP27 | −0.44 | −0.70 | −0.18 | −0.25 | −0.17 | C12orf50 | −0.10 | −0.64 | 0.00 | 0.14 | −0.06 |
| PINK1-AS | −0.37 | 0.48 | 0.34 | 0.06 | −0.17 | PCDH1 | −0.16 | 0.62 | 0.86 | 0.09 | −0.23 | RNU6-598P | 0.60 | 0.46 | 1.36 | −2.25 | 0.62 |
| AKAP1 | −0.33 | 0.29 | 0.16 | 0.31 | 0.18 | PRPS1P2 | −0.19 | 0.10 | −0.15 | 0.06 | −0.35 | PROS2P | −0.11 | 0.90 | −0.91 | 0.40 | 0.29 |
| PRR13 | 0.29 | −0.23 | −0.29 | 0.05 | 0.00 | RNU6-850P | 0.67 | −1.54 | −0.40 | −0.24 | 1.57 | IL17REL | 0.07 | −0.94 | 0.59 | −0.14 | 0.82 |
| LILRA5 | 1.56 | −1.40 | −0.63 | −0.50 | −0.72 | CRHBP | −0.46 | 0.40 | 1.53 | 0.26 | 0.35 | LINC00383 | 0.24 | −1.87 | 0.32 | −0.78 | 1.61 |
| ARHGAP5-AS1 | 0.62 | −0.27 | −0.07 | 0.08 | 0.04 | NIPSNAP2 | −0.12 | 0.20 | 0.17 | 0.05 | 0.05 | AC073911.2 | −0.32 | −0.60 | 0.48 | 0.54 | 0.73 |
| SSR4P1 | −0.66 | 0.55 | 0.54 | 0.22 | 0.02 | AC023818.1 | −0.14 | 0.07 | 0.12 | 0.12 | 0.09 | AC010551.2 | −0.20 | −1.64 | 1.24 | −2.07 | 0.69 |
| RTN1 | −0.78 | 0.04 | 0.82 | −0.17 | 0.60 | ORAOV1P1 | −1.10 | 1.69 | 1.03 | 2.02 | −0.33 | AC011466.4 | 0.07 | −0.77 | −0.91 | 0.29 | 0.88 |
| JHY | −0.40 | 0.39 | 0.48 | 0.16 | 0.01 | OR6W1P | −0.70 | −1.05 | 0.48 | 0.27 | 0.67 | AC091685.2 | 0.15 | 0.17 | −0.47 | 0.24 | −0.71 |
| RPUSD2 | 0.51 | −0.37 | −0.57 | −0.05 | −0.36 | BHLHB9P1 | −0.51 | 0.27 | −0.52 | 0.56 | −0.02 | AC211469.2 | 0.26 | −0.92 | −1.13 | −1.38 | −0.22 |
| AC100788.1 | −0.70 | 0.33 | 0.42 | −0.38 | −0.47 | ORAI2 | 0.16 | −0.20 | 0.09 | −0.29 | −0.06 | AL592291.1 | 0.64 | −1.60 | −0.27 | −0.27 | 1.29 |
| RPL12P41 | −1.44 | 0.57 | 1.64 | 0.23 | 1.10 | LELP1 | −0.86 | −0.33 | 2.18 | −0.72 | 0.73 | RNU6-585P | −0.29 | 0.20 | −0.54 | −0.56 | −1.41 |
| CYP4F8 | −1.88 | 2.00 | 0.92 | 3.96 | 1.02 | AC016831.5 | −1.05 | −1.29 | 0.57 | −1.29 | −0.29 | NPY | −0.24 | 0.60 | 0.35 | 1.48 | 0.25 |
| EEF1GP2 | −1.78 | 1.21 | 3.06 | −0.55 | −0.14 | MIR30C2 | −0.64 | 1.27 | 1.89 | 1.26 | −0.07 | AC008033.1 | −0.31 | 0.10 | −0.25 | −1.41 | −2.28 |
| RN7SL581P | −1.61 | 2.60 | 1.55 | 0.15 | −0.46 | LINC01564 | 0.85 | 1.88 | −1.69 | 0.79 | −0.87 | G39617 | −0.15 | −0.04 | 0.57 | 0.36 | 0.95 |
| AL354707.1 | −0.72 | −0.37 | 0.26 | −0.05 | 0.45 | AP005137.2 | 0.54 | −0.65 | −0.06 | 0.52 | 0.07 | LINC02494 | 0.32 | 0.63 | −2.09 | 0.38 | −1.36 |
| IQGAP2 | −0.64 | 0.29 | 0.93 | −0.18 | 0.53 | G39721 | 0.46 | −0.34 | −0.02 | 0.16 | 0.32 | AC136619.2 | 0.20 | 0.44 | −0.41 | 0.08 | 0.39 |
| AC244517.6 | −1.57 | 0.76 | 2.37 | −1.09 | 0.34 | MS4A15 | −1.08 | 0.29 | −0.54 | −1.03 | −1.89 | AC027458.1 | −0.37 | −0.95 | −0.10 | −0.49 | −0.73 |
| HOXB4 | −0.74 | 0.23 | 0.97 | 0.04 | −0.18 | SRSF9P1 | 0.67 | −0.82 | −0.71 | 0.04 | 0.80 | AC006213.5 | 0.16 | 0.40 | 2.90 | 0.35 | 0.42 |
| ELOB | 0.43 | −0.13 | 0.12 | −0.43 | −0.28 | AL391497.1 | 0.54 | −0.63 | 0.57 | −0.12 | 0.84 | HNRNPA1P58 | 0.64 | −1.81 | −0.20 | 0.03 | 1.00 |
| ICAM1 | 0.78 | −1.18 | −0.80 | −0.48 | −0.29 | AACSP1 | −0.32 | 0.58 | 0.75 | 0.16 | 0.09 | LINC01249 | 0.13 | −0.80 | −0.49 | 2.00 | 0.83 |
| HMGB1P31 | −0.66 | 0.42 | 0.89 | 0.38 | 0.49 | SMC1B | −0.20 | −0.10 | 0.27 | −0.08 | 0.35 | AC092291.1 | 0.10 | −0.76 | −0.30 | 0.12 | 0.29 |
| DSTYK | −0.26 | 0.24 | 0.23 | 0.10 | −0.11 | RN7SL16P | 0.34 | 0.44 | 0.00 | 0.03 | −0.50 | AC017037.1 | −0.17 | −0.75 | −2.63 | 1.73 | −0.69 |
| AC131971.1 | 0.59 | −0.36 | 0.12 | −0.16 | 0.26 | MAN1A1 | 0.19 | −0.14 | −0.01 | −0.22 | −0.18 | AL669831.6 | 0.36 | −1.01 | −0.83 | 0.80 | NA |
| BCL7B | 0.30 | −0.17 | −0.44 | −0.16 | −0.35 | AC011815.3 | −0.23 | −0.45 | 0.63 | −0.34 | 0.76 | RN7SL19P | 0.10 | 0.36 | −0.73 | 0.29 | −0.46 |
| PI4KAP2 | −0.64 | 0.13 | 0.41 | −0.14 | 0.15 | PAPPA-AS2 | 0.45 | 0.60 | −0.52 | −0.47 | 0.04 | AP003392.2 | 0.05 | 0.27 | −0.13 | 0.21 | −0.27 |
| IGFBP2 | 0.75 | −0.01 | −0.48 | −0.03 | −1.22 | AP002512.3 | −0.86 | −1.31 | −0.31 | 0.26 | 0.85 | LINC00554 | 0.20 | −0.56 | −1.99 | 0.32 | −0.85 |
| ADIPOQ-AS1 | −1.87 | 2.04 | 1.32 | 1.54 | −0.50 | AC096649.1 | 0.81 | 0.03 | 0.87 | 0.19 | 0.41 | SHANK2-AS1 | −0.06 | −0.09 | −0.43 | −0.20 | 0.15 |
| SNORD90 | −1.11 | 0.77 | 1.48 | 0.00 | −0.08 | AC091163.2 | −1.32 | −0.57 | 2.63 | −0.75 | 2.14 | LINC01392 | 0.64 | −1.19 | −1.01 | −0.58 | −0.92 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| ELP3 | 0.27 | −0.22 | −0.26 | −0.06 | 0.04 | LINC01494 | −0.49 | 0.17 | 0.18 | 0.61 | −2.00 | LINC00551 | 0.16 | −0.41 | −1.78 | −0.19 | −1.81 |
| HSPE1P18 | 1.47 | −0.76 | −0.67 | −0.20 | 0.43 | RNU2-3P | −0.38 | 0.38 | −0.53 | 0.93 | −0.76 | PGPEP1L | −0.09 | 0.13 | 1.54 | −0.29 | 0.17 |
| FBXW11 | 0.31 | −0.16 | −0.17 | −0.11 | −0.02 | AL080317.1 | 0.20 | −0.10 | −0.28 | −0.18 | −0.04 | LINC00458 | 0.20 | 0.46 | −0.05 | 0.08 | −1.20 |
| RBM7 | 0.36 | −0.11 | −0.27 | −0.02 | −0.25 | AC063960.1 | −0.55 | 0.64 | −0.38 | 0.32 | −1.21 | AL137028.2 | −0.22 | 0.84 | 1.87 | 0.44 | −0.65 |
| PCDHB18P | −0.70 | 0.35 | 1.09 | 0.11 | 0.05 | LINC02526 | −0.88 | 1.94 | 1.18 | 0.38 | −0.49 | GRM5-AS1 | 0.13 | −1.91 | −2.12 | 0.41 | 1.04 |
| PRR12 | −0.44 | 0.19 | −0.01 | 0.33 | 0.15 | RASSF2 | 0.25 | −0.28 | 0.37 | −0.34 | −0.12 | PRAMEF2 | 0.29 | −0.17 | −2.19 | 0.18 | −0.62 |
| AP5M1 | 0.28 | −0.12 | −0.16 | −0.05 | −0.05 | MIR619 | 0.60 | −0.20 | −1.35 | −0.09 | −0.60 | RPL31P35 | 0.31 | −1.20 | −1.08 | −0.13 | 0.55 |
| NRDC | 0.25 | −0.07 | −0.09 | −0.09 | −0.12 | AC024603.1 | −0.39 | 1.06 | 1.45 | −0.34 | −0.48 | OSGEPL1-AS1 | −0.05 | −0.31 | −0.42 | 0.35 | −0.17 |
| AC015802.4 | −0.83 | −0.05 | 0.69 | 0.49 | 0.86 | RUNX2 | 0.17 | −0.42 | −0.31 | −0.47 | −0.10 | RAD23BP3 | −0.31 | 0.07 | −0.33 | −0.30 | −1.38 |
| AL592466.1 | −2.45 | −0.09 | 0.38 | −0.14 | 0.55 | PARP3 | −0.14 | −0.03 | −0.21 | 0.04 | 0.14 | RNU6-878P | −0.24 | −0.12 | 1.14 | −0.77 | −0.70 |
| MIR497HG | −0.89 | 0.66 | 0.66 | 0.19 | 0.21 | GCNT7 | 0.19 | −0.21 | −0.18 | −0.08 | 0.27 | AC092155.2 | 0.15 | −0.43 | −0.52 | −0.15 | −0.36 |
| PSEN2 | −0.43 | 0.36 | 0.16 | 0.11 | −0.09 | OFD1 | −0.08 | 0.10 | 0.17 | −0.03 | 0.06 | AC136428.3 | 0.26 | −1.60 | −0.67 | 0.06 | −0.38 |
| CDX4 | −1.32 | 1.31 | 2.77 | 1.09 | 0.26 | PACSIN1 | 0.40 | −1.23 | 0.28 | 0.88 | 1.30 | BFSP2-AS1 | 0.31 | −1.68 | −0.91 | −1.81 | −0.55 |
| PCDHB9 | −0.98 | 0.40 | 0.58 | 0.33 | −0.10 | AL603832.2 | 0.68 | −0.44 | −0.10 | 0.78 | 0.55 | LINC01555 | −0.18 | 0.03 | 1.26 | −1.41 | −0.76 |
| AC092645.1 | −0.87 | 0.55 | 0.80 | 0.23 | 0.30 | AP005131.1 | −0.22 | 0.22 | 0.33 | −0.02 | 0.24 | RNU6-552P | −0.61 | −0.40 | 0.00 | −0.28 | 0.76 |
| DDI2 | 0.27 | −0.06 | −0.16 | 0.02 | −0.04 | AC003989.1 | −0.28 | 0.08 | 0.46 | 0.13 | 0.49 | AL139021.1 | 0.11 | 0.20 | 0.18 | 0.69 | 0.02 |
| BTBD2 | −0.26 | 0.23 | −0.04 | 0.22 | 0.03 | AC021106.2 | 0.82 | −0.14 | −0.54 | 0.63 | −0.53 | RNU6-930P | −0.14 | 1.16 | 1.27 | 1.67 | 1.76 |
| RN7SL751P | 0.92 | −0.40 | −0.43 | 0.02 | 0.05 | AC002101.1 | 1.27 | −1.18 | −1.35 | 0.05 | −0.53 | LINC01753 | 0.18 | −0.02 | 0.77 | −0.15 | 1.16 |
| KCNAB1 | −0.49 | 0.46 | 0.60 | 0.33 | 0.05 | AL136228.1 | −0.80 | −0.03 | 3.65 | −1.15 | 1.49 | RNA5SP73 | −0.63 | 0.16 | −0.11 | 0.32 | 0.03 |
| APBA2 | −0.66 | −0.09 | 0.05 | −0.06 | 0.13 | AC022916.3 | −0.90 | 1.52 | 0.52 | 1.75 | 0.21 | AC106799.1 | 0.18 | −0.75 | −0.03 | −1.01 | −0.40 |
| KLF17P1 | −1.12 | −0.07 | 0.61 | 0.08 | 0.24 | G4338 | −0.60 | 0.85 | −0.41 | 0.17 | 0.01 | AC011591.1 | 0.21 | −2.07 | 0.59 | −1.31 | 0.91 |
| STARD4-AS1 | 0.56 | −0.10 | −0.19 | −0.13 | −0.46 | RPS29P21 | 0.39 | 0.07 | 0.10 | 0.10 | −0.01 | AC234781.3 | 0.09 | 0.17 | −0.15 | 0.07 | 0.25 |
| BRAT1 | −0.44 | 0.14 | −0.06 | 0.41 | 0.18 | BX248409.1 | −0.37 | 0.32 | 0.67 | −0.16 | 0.17 | LINC01673 | −0.13 | 0.41 | −0.88 | 1.45 | −0.29 |
| ALDH2 | −0.42 | 0.57 | 0.19 | 0.44 | −0.17 | AL157838.1 | −0.14 | −0.25 | −0.23 | −0.14 | −0.12 | AC026774.1 | −0.63 | −0.41 | 0.02 | −0.60 | 0.26 |
| G20113 | −0.71 | 0.36 | 0.55 | 0.10 | 0.30 | EIF4BP6 | 0.19 | −0.10 | −0.10 | −0.25 | −0.22 | FARSBP1 | −0.63 | 0.72 | −1.12 | −0.82 | −1.20 |
| MORF4L1P1 | 0.43 | −0.13 | −0.17 | −0.13 | −0.12 | AP005119.2 | −0.95 | 0.16 | −2.46 | 2.49 | −1.03 | AL392103.1 | −0.13 | 0.62 | −0.24 | −0.96 | −1.28 |
| CLEC4GP1 | −1.05 | 0.18 | 0.46 | 0.80 | 0.11 | AC099811.3 | 0.33 | −1.07 | 0.02 | −0.16 | 0.56 | AP006587.6 | −0.32 | −1.02 | −1.39 | 0.25 | −0.48 |
| MFN2 | 0.26 | −0.13 | −0.43 | 0.02 | −0.16 | G13214 | 0.52 | −0.13 | 0.20 | −0.45 | 0.42 | SNX18P7 | 0.06 | −0.03 | 0.16 | 0.36 | 0.44 |
| RIF1 | 0.27 | −0.07 | −0.24 | −0.03 | −0.12 | AL161909.2 | −0.24 | −0.46 | 0.04 | 0.00 | 0.52 | C17orf99 | −0.09 | 0.12 | −0.30 | −0.01 | −0.46 |
| AL669983.1 | −1.48 | 0.98 | 0.80 | 0.38 | −0.23 | AL023581.2 | 0.39 | −0.15 | −0.55 | 0.16 | −0.02 | NUBP2 | −0.02 | −0.07 | −0.21 | 0.21 | 0.05 |
| AL354696.2 | −0.68 | 0.30 | 0.70 | 0.08 | 0.09 | ASB9P1 | −0.48 | 0.91 | 2.02 | −0.34 | 0.15 | OR14I1 | −0.63 | −0.22 | 1.32 | 0.11 | −0.06 |
| DAAM1 | 0.35 | 0.00 | −0.25 | 0.07 | −0.33 | AC087222.1 | −0.23 | 0.34 | −0.06 | −0.12 | −0.17 | CREB3L1 | −0.04 | 0.20 | 1.18 | −0.62 | 0.01 |
| AC021678.1 | 1.58 | −0.17 | −0.23 | −0.39 | −0.70 | AL161725.2 | −0.55 | 0.65 | 1.95 | −0.25 | 1.12 | LINC01768 | 0.21 | −0.69 | −0.87 | −0.09 | −0.66 |
| GATA3 | −0.66 | 0.81 | 0.72 | 0.60 | 0.21 | AP002961.1 | 0.42 | −0.83 | −0.70 | −0.64 | −0.09 | AF241725.1 | 0.22 | −0.21 | −0.86 | 0.72 | −0.19 |
| CYTH3 | −0.36 | 0.19 | 0.24 | 0.03 | −0.06 | LBH | 0.17 | −0.31 | 0.04 | −0.19 | 0.23 | AC112719.2 | 0.05 | −0.70 | −0.09 | −0.48 | −0.10 |
| GLI1 | −0.82 | 0.58 | 0.98 | 0.26 | 0.41 | G24602 | −0.46 | 1.00 | 0.14 | 0.44 | −1.10 | AC010889.1 | −0.06 | −0.61 | −0.52 | −0.24 | 0.14 |
| RFX5 | 0.25 | −0.34 | −0.29 | 0.01 | 0.09 | AL031775.1 | 0.43 | −0.06 | −0.78 | 0.27 | −0.41 | EIF1B | −0.02 | 0.13 | −0.04 | −0.01 | −0.24 |
| GNRH1 | −0.44 | 0.15 | 0.25 | 0.22 | 0.12 | ADAMTSL1 | −0.27 | 0.24 | 0.88 | −0.24 | −0.09 | C9orf84 | 0.03 | −0.17 | −0.10 | −0.51 | −0.15 |
| CREG2 | 1.16 | −0.40 | −1.71 | −0.20 | −0.74 | HNRNPA1P27 | −0.27 | 0.31 | 0.38 | 0.43 | 0.00 | AL353743.4 | 0.11 | −0.52 | −0.02 | −0.65 | 1.42 |
| AL360169.2 | −0.59 | −0.01 | 0.04 | 0.12 | 0.38 | C6orf223 | 0.50 | −0.71 | −2.45 | 0.12 | −1.33 | SLC6A7 | 0.08 | −0.66 | −1.41 | −0.05 | −0.67 |
| RPL26 | 0.48 | −0.17 | −0.35 | 0.11 | −0.33 | AC008278.1 | −0.65 | −0.65 | 0.74 | −0.66 | 2.12 | RNU6-418P | −0.09 | 0.91 | 0.64 | 0.81 | 0.49 |
| AL162711.1 | −1.29 | 0.01 | 0.29 | −0.01 | 0.58 | FOSB | −0.28 | −0.19 | 0.14 | −0.88 | 0.76 | PLPPR5 | −0.12 | −1.28 | 0.02 | −0.22 | −1.50 |
| AC011473.1 | −2.23 | 0.21 | 1.96 | 0.34 | 1.87 | LINC00526 | −0.34 | 0.45 | 0.34 | 0.24 | 0.00 | IGHV4-61 | 0.63 | 0.89 | −0.61 | 1.32 | 1.30 |
| SLC2A6 | 0.75 | −0.52 | −0.66 | −0.26 | −0.22 | AC080078.2 | 0.42 | −0.36 | −0.18 | −0.48 | −0.07 | LINC00620 | 0.18 | −1.09 | 1.30 | −0.51 | 0.23 |
| NANOG | −1.11 | 0.30 | −0.33 | 0.55 | 0.12 | LY6G6E | −0.73 | 0.26 | 2.29 | −1.43 | −0.19 | AC079178.2 | −0.37 | −0.06 | −0.89 | 1.36 | 0.88 |
| OAZ1 | 0.29 | −0.10 | −0.51 | 0.09 | −0.35 | AL451142.2 | 1.02 | −0.71 | −0.32 | −1.08 | 0.65 | AC016629.2 | 0.14 | −1.43 | −0.64 | −0.64 | −0.31 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| CCDC36 | −0.65 | 0.46 | 0.64 | 0.05 | 0.04 | AC105254.1 | −1.33 | 1.07 | 0.46 | −1.44 | −1.44 | OR10AG1 | 0.18 | −0.07 | −1.63 | 0.59 | −0.29 |
| GTF2A1 | 0.30 | −0.07 | −0.24 | −0.09 | −0.26 | LINC00656 | 0.80 | −0.71 | −2.42 | 0.35 | −0.69 | OR10H4 | 0.16 | −1.57 | −0.89 | 0.47 | 0.65 |
| SPAAR | −0.94 | 0.30 | 0.44 | 0.44 | 0.02 | AC019254.2 | −0.64 | −0.43 | −2.22 | −0.46 | −0.67 | AL353597.2 | 0.21 | 0.19 | −0.60 | −1.70 | −3.55 |
| RAPGEFL1 | −0.66 | 0.59 | 0.75 | 0.40 | 0.23 | EXOSC5 | 0.15 | −0.08 | 0.13 | 0.05 | 0.25 | SLC16A6P1 | 0.06 | 0.18 | −0.02 | 0.27 | 0.26 |
| AL137191.1 | 2.12 | −1.88 | −0.79 | 0.29 | −0.87 | CHODL | −0.28 | 0.28 | 0.07 | 0.45 | −0.28 | LINC02128 | −0.10 | −0.39 | −1.68 | 0.57 | −0.83 |
| CSTL1 | −1.59 | −0.24 | 0.65 | 0.42 | 0.91 | RPP14 | −0.07 | −0.04 | 0.12 | 0.07 | 0.14 | RPL7AP28 | −0.11 | 0.89 | 0.36 | 0.20 | −1.40 |
| KRT8P4 | −1.44 | 1.56 | 1.44 | −0.26 | −0.26 | AC104446.1 | 0.38 | 0.10 | −0.12 | 0.30 | 0.02 | MAPILC3P | 0.28 | −0.35 | 0.50 | −0.96 | 0.14 |
| CAMK2D | 0.30 | −0.14 | −0.19 | −0.04 | −0.14 | SOHLH2 | −0.75 | −0.56 | −0.10 | −0.19 | −0.34 | LINC00547 | 0.13 | −2.55 | −0.38 | −0.31 | −0.53 |
| AL356481.3 | −1.12 | 0.93 | 0.60 | 0.65 | −0.01 | RPS2P32 | −0.27 | 0.01 | 0.60 | 0.08 | 0.64 | LINC01650 | −0.21 | −0.44 | −0.34 | −0.05 | −0.43 |
| MSX1 | −0.79 | 0.19 | 0.95 | −0.13 | −0.02 | ARSJ | 0.23 | −0.26 | 0.13 | −0.53 | 0.16 | AC015687.1 | −0.14 | −0.57 | −0.41 | −0.12 | 0.05 |
| CDCA4 | 0.51 | −0.24 | −0.57 | 0.01 | −0.38 | GOPC | 0.10 | 0.03 | 0.16 | −0.10 | 0.03 | AP001889.1 | −0.16 | −0.24 | −1.17 | 0.35 | 0.32 |
| HHIPL1 | −0.64 | 0.20 | 0.89 | −0.10 | 0.55 | AC105206.1 | 0.36 | −0.22 | −0.33 | −0.27 | −0.03 | CARM1P1 | −0.10 | −0.70 | −1.79 | 1.12 | 0.35 |
| SLC33A1 | −0.36 | 0.08 | 0.42 | −0.05 | 0.25 | AP001623.1 | −0.35 | 0.31 | 1.46 | 0.01 | 0.33 | MTCO1P1 | −0.10 | −1.40 | 0.08 | −0.32 | 0.72 |
| ASB1 | −0.31 | 0.04 | 0.02 | 0.06 | 0.12 | AL032819.3 | −0.93 | −0.36 | 1.33 | −0.96 | 0.10 | SH3GL2 | −0.10 | 0.27 | −0.93 | 0.09 | 0.29 |
| HS1BP3 | −0.31 | 0.27 | 0.30 | 0.22 | 0.09 | AL136520.1 | −0.93 | 0.99 | 1.30 | −0.05 | 0.28 | AC002310.1 | −0.05 | −0.56 | 0.81 | −0.29 | 0.65 |
| MRPS33 | 0.39 | −0.43 | 0.02 | −0.41 | 0.10 | AC084859.1 | −0.22 | 0.07 | −0.29 | 0.32 | 0.15 | LINC01441 | 0.17 | −1.26 | 1.19 | −0.02 | 1.95 |
| OR9I2P | −1.75 | 0.10 | 2.70 | 0.85 | 0.12 | MIR3945 | 1.38 | −1.17 | −1.40 | 0.21 | −1.43 | NAGPA | 0.02 | −0.20 | −0.06 | 0.10 | 0.36 |
| PSMG2 | 0.39 | −0.15 | −0.07 | −0.06 | −0.10 | STYXL1 | 0.12 | −0.19 | 0.01 | −0.36 | −0.29 | MS4A8 | −0.18 | −0.49 | −2.22 | 0.29 | −1.99 |
| AP003168.2 | −0.88 | −0.33 | 0.51 | 0.01 | 0.70 | OSCAR | 0.24 | −0.75 | 0.39 | −0.15 | 1.05 | PAGE4 | 0.15 | 0.42 | −2.40 | 1.55 | −0.36 |
| AQP4 | −1.41 | 1.07 | −0.13 | 0.54 | −0.31 | CCDC3 | 0.22 | 0.46 | 0.13 | 0.22 | −0.48 | AC108751.3 | 0.34 | 0.03 | −1.05 | 0.68 | −1.62 |
| MAL2-AS1 | 0.73 | 0.06 | 0.07 | −0.11 | 0.21 | AC087362.1 | 0.39 | −1.11 | 1.06 | −0.35 | 0.99 | SLC25A3P1 | 0.14 | −1.10 | −0.89 | −0.66 | −0.24 |
| MIOS | 0.34 | −0.02 | −0.04 | 0.08 | 0.06 | RNU6-514P | −0.69 | 0.07 | 1.20 | −1.20 | −0.32 | AC117392.1 | −0.63 | −0.49 | 0.21 | −0.24 | 0.69 |
| NUPL2 | 0.29 | −0.16 | −0.19 | −0.14 | −0.05 | RPS15AP18 | −0.65 | −1.78 | −0.88 | 1.10 | 2.03 | LINC02113 | 0.63 | −1.80 | −0.10 | −1.14 | 0.36 |
| AC010335.1 | −1.34 | 0.45 | 0.70 | 0.16 | 0.22 | METTL15P1 | −0.24 | 0.23 | 0.05 | −0.34 | −0.01 | BNIP3P8 | −0.06 | −0.19 | −0.15 | 0.16 | −0.02 |
| MIR218-2 | −1.53 | 0.50 | 3.04 | 0.08 | 0.42 | SPINDOC | 0.17 | −0.34 | −0.39 | −0.02 | −0.01 | CYCSP17 | −0.63 | −0.14 | −1.62 | 1.54 | −0.39 |
| ANKRD6 | −0.53 | 0.36 | 0.59 | −0.02 | 0.14 | RAD51AP2 | 0.31 | −0.08 | −0.22 | −0.58 | −0.36 | AC006270.2 | 0.04 | −0.78 | −0.13 | −0.17 | 0.94 |
| RALGAPB | 0.22 | 0.01 | −0.04 | 0.01 | −0.12 | KRT4 | −0.53 | 0.66 | 0.12 | 1.24 | 0.58 | MIR151B | −0.09 | 0.80 | 0.29 | −0.72 | −0.36 |
| ERVK13-1 | −0.32 | 0.13 | 0.38 | 0.00 | 0.22 | LINC02147 | −0.61 | 0.39 | 0.29 | 1.38 | 0.49 | FTLP17 | 0.30 | −0.07 | −0.10 | 1.17 | −1.66 |
| LINC01160 | −1.02 | −0.11 | 0.69 | 0.48 | 1.05 | AC009009.1 | −0.55 | −0.03 | 1.42 | 0.53 | 0.10 | IRX1P1 | 0.46 | 0.11 | 0.63 | −1.87 | −1.01 |
| RNU4-24P | 1.33 | −0.08 | −0.37 | 0.19 | −0.53 | RPL21P39 | 0.97 | −1.01 | −1.19 | 0.54 | −0.26 | LINC01445 | 0.56 | −0.33 | −0.23 | 0.15 | −2.35 |
| ADPGK | 0.31 | −0.27 | −0.28 | −0.06 | 0.04 | PPIL4 | 0.09 | −0.09 | −0.01 | −0.11 | −0.01 | MIR4279 | −0.27 | 0.61 | 1.61 | 0.03 | 0.60 |
| CDKL2 | −1.01 | 0.25 | 0.10 | 1.15 | 1.34 | GIT2 | 0.06 | −0.10 | −0.02 | −0.10 | 0.04 | G40866 | 0.04 | 0.16 | 0.37 | 0.38 | 0.40 |
| NKD2 | −0.75 | 0.28 | 0.43 | 0.59 | 0.70 | AC083880.1 | 0.59 | 0.04 | 1.51 | −0.09 | −0.30 | PVALEF | 0.20 | −0.73 | 1.13 | 0.61 | 1.43 |
| AC011510.1 | −1.00 | 0.63 | 1.24 | 0.17 | 0.66 | MTND5P33 | −0.46 | −0.64 | −0.46 | −0.05 | 0.43 | G2589 | −0.13 | 0.44 | 0.45 | −0.37 | −0.95 |
| AL139080.1 | −1.15 | 0.72 | 0.04 | 0.46 | 0.35 | AC025810.1 | 1.47 | −1.33 | −1.53 | 0.35 | −1.43 | AL157834.2 | −0.06 | −0.54 | 0.36 | −0.11 | 0.59 |
| AP000807.2 | 1.93 | −0.57 | −2.01 | 0.38 | −1.31 | OR4D5 | −0.86 | 0.01 | 0.11 | −0.03 | −1.28 | LINC01179 | −0.15 | −1.62 | 1.14 | 1.56 | 1.65 |
| FOXD3 | −1.08 | 0.55 | 1.17 | 0.42 | 1.08 | AC005070.1 | −0.29 | −0.33 | −0.40 | 0.52 | 0.28 | AC090150.1 | 0.26 | −1.02 | 0.27 | −1.75 | 0.47 |
| ALDH3B2 | 0.62 | −0.03 | −0.34 | 0.30 | −0.21 | SNORA9 | 0.32 | −0.12 | −0.65 | 0.14 | −0.44 | AC007497.1 | 0.08 | −0.44 | −0.44 | −0.15 | −0.18 |
| SDAD1P4 | −1.68 | 1.57 | 0.78 | 1.78 | 0.14 | SOCS2 | 0.17 | −0.01 | 0.01 | −0.20 | −0.09 | AC092354.1 | 0.24 | −1.77 | 0.58 | −0.55 | 2.92 |
| AP002370.2 | −0.95 | 0.80 | 1.69 | 0.66 | 0.87 | OCEL1 | −0.23 | 0.00 | 0.12 | 0.14 | 0.16 | AC132803.1 | −0.23 | 2.15 | 0.60 | 0.82 | −0.90 |
| AC005550.2 | −0.71 | 0.37 | 1.20 | 0.17 | 0.57 | C11orf16 | 0.41 | −0.68 | 0.17 | −0.23 | 0.63 | RNY1P5 | 0.32 | −2.13 | −0.65 | 0.54 | 0.15 |
| RMC1 | 0.20 | −0.06 | −0.13 | −0.08 | −0.15 | AL133318.1 | −0.49 | 0.52 | 1.34 | 0.01 | 0.43 | AC004009.1 | 0.29 | −2.05 | 0.08 | −0.72 | −0.59 |
| RPL9P9 | 1.74 | −0.27 | 0.19 | 0.49 | 0.07 | AC010096.1 | −0.65 | −0.49 | −0.39 | 0.80 | 0.43 | RNU7-80P | 0.04 | −0.24 | 0.70 | 0.19 | 0.92 |
| AC009120.3 | −0.53 | 0.25 | 0.39 | −0.06 | 0.10 | AC005077.4 | −0.45 | 0.45 | 0.93 | −0.12 | 0.00 | AL159166.1 | 0.11 | −0.28 | 1.60 | −0.27 | 0.88 |
| RPS6KA3 | 0.33 | −0.18 | −0.17 | −0.13 | −0.21 | EPS15P1 | −0.97 | −1.66 | −1.56 | −0.46 | −0.60 | AC123023.1 | −0.60 | −0.45 | −0.41 | 1.31 | 0.65 |
| AL512274.1 | 0.68 | 0.09 | −0.15 | −0.15 | −0.54 | FAM192BP | −0.26 | 0.06 | 0.49 | 0.00 | 0.11 | ARF4-AS1 | 0.09 | 0.32 | 1.28 | −0.09 | 0.73 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| ANKRD33B-AS1 | −1.78 | 1.05 | 2.13 | 0.18 | −0.06 | AL138689.2 | 0.18 | 0.12 | 0.12 | −0.18 | 0.12 | G15987 | 0.19 | 0.99 | 1.60 | 0.48 | −0.94 |
| AL035425.3 | −1.48 | −0.72 | −0.70 | 0.22 | 0.38 | BX679664.1 | 0.49 | −0.68 | −0.60 | −0.03 | −0.86 | AC023866.1 | 0.15 | 0.85 | 0.65 | 0.33 | −2.12 |
| LRRC37A16P | −0.57 | 0.30 | 0.95 | −0.12 | 0.40 | MED24 | −0.10 | 0.03 | −0.26 | 0.09 | −0.03 | AL645939.2 | −0.10 | 0.49 | −0.70 | 0.51 | 0.77 |
| AC007389.5 | −1.50 | 0.57 | 1.02 | −0.67 | 0.40 | AC068313.1 | −0.85 | 0.89 | 1.09 | 0.96 | 1.87 | MRPS24 | 0.05 | 0.45 | −0.34 | 0.36 | −0.66 |
| SBF1P1 | −1.34 | −0.38 | 1.42 | 0.80 | 1.49 | AHI1 | −0.09 | 0.02 | 0.16 | −0.03 | 0.05 | OPALIN | −0.12 | −0.40 | 0.16 | 1.20 | −0.30 |
| AL603910.1 | −0.86 | 0.03 | 0.23 | 0.25 | 0.55 | MAGI1-AS1 | 0.25 | −0.22 | 0.23 | −0.19 | 0.38 | GUCA1C | 0.26 | −0.29 | −1.18 | 2.11 | 0.36 |
| DGAT1 | −0.41 | 0.09 | −0.11 | 0.27 | 0.24 | AC020898.1 | 0.23 | 0.04 | −0.43 | 0.22 | −0.42 | LINC00328-2P | −0.62 | −0.26 | 0.24 | −0.85 | 1.56 |
| PPM1F | 0.27 | −0.28 | −0.43 | 0.07 | 0.00 | AP000721.2 | −0.60 | 2.00 | 0.41 | 1.07 | −0.15 | APOOP3 | −0.62 | −0.89 | 0.80 | −1.57 | 0.75 |
| AC078909.2 | −1.22 | 0.63 | 1.02 | 0.97 | 0.60 | AC007327.1 | −0.54 | −0.20 | −1.28 | 0.90 | −1.07 | NEMF | 0.02 | −0.06 | −0.16 | 0.01 | −0.05 |
| AC008063.1 | 1.60 | −0.34 | −1.11 | 0.30 | −0.07 | AC007608.4 | −0.23 | −0.16 | 0.38 | 0.22 | 0.46 | RN7SL279P | −0.14 | 0.27 | 0.40 | −0.18 | −1.02 |
| AC092839.2 | −0.78 | 0.48 | 1.05 | −0.01 | 0.27 | CASD1 | −0.13 | 0.04 | 0.43 | −0.06 | 0.28 | FLJ31356 | 0.05 | 0.06 | −0.04 | −0.32 | 0.04 |
| MROH1 | −0.39 | 0.15 | −0.09 | 0.15 | 0.13 | FCRL1 | −0.61 | −0.92 | 0.87 | −0.30 | 0.38 | S100A1 | −0.05 | 0.00 | −0.59 | −0.05 | −0.17 |
| NDUFS3 | 0.32 | −0.08 | −0.23 | −0.04 | −0.22 | AC007679.2 | 0.36 | −0.30 | −0.72 | 0.11 | 0.15 | AC092954.2 | −0.62 | 0.70 | 1.38 | 0.31 | −1.02 |
| RNA5SP150 | −1.34 | 0.73 | −0.96 | 1.68 | −0.81 | PCNPP5 | 0.26 | −0.51 | 0.08 | −0.24 | 0.35 | AL589826.1 | −0.62 | −0.09 | 0.73 | −0.09 | −0.19 |
| PKMP3 | −1.21 | 0.71 | 1.57 | −0.02 | 0.32 | KC877373.1 | 1.04 | 0.59 | −1.29 | 0.60 | −2.43 | AP000919.3 | 0.07 | −0.47 | −0.54 | 0.31 | 0.31 |
| MORF4L1P4 | −1.53 | −1.49 | 0.68 | −1.15 | 1.46 | G28383 | 0.33 | −0.01 | 0.33 | 0.13 | 0.27 | AC117382.2 | 0.06 | −0.08 | 0.28 | −0.53 | −0.90 |
| STK32B | −0.55 | 0.12 | 0.56 | −0.02 | 0.14 | B3GNT8 | 0.22 | 0.24 | −0.22 | 0.00 | −0.31 | SNORD14 | −0.14 | 0.38 | 2.16 | 0.05 | 0.09 |
| AC010504.1 | −0.99 | 0.17 | 0.67 | 0.26 | 0.33 | MIR133A1HG | 0.14 | −0.14 | 0.25 | −0.14 | 0.24 | EIF4BP4 | 0.27 | −0.15 | −1.77 | 0.78 | −2.07 |
| AC007622.1 | 1.04 | −0.94 | −0.87 | 0.06 | 0.30 | CRHR2 | −0.24 | 0.14 | 0.23 | 0.10 | 0.46 | OR2B6 | 0.19 | −1.51 | −2.57 | −0.13 | −1.40 |
| FAM199X | 0.31 | −0.02 | −0.12 | −0.08 | −0.17 | SCARF2 | −0.26 | 0.06 | 0.68 | −0.47 | −0.19 | AC090907.1 | −0.08 | −0.63 | 0.81 | −1.21 | 0.39 |
| GAPDHP49 | 1.07 | −0.74 | 0.14 | −0.16 | 0.59 | AL390776.1 | 1.21 | −0.55 | 0.96 | 0.09 | −0.13 | RNU6-1289P | −0.09 | 0.94 | −0.59 | 0.49 | −0.11 |
| AC015815.7 | −1.42 | 0.12 | −0.21 | −0.31 | 0.20 | AC011466.3 | 0.34 | −0.08 | −0.49 | 0.17 | 0.05 | PLA2G4B | 0.05 | −0.33 | −0.11 | 0.13 | 0.51 |
| CDC25C | 0.72 | −0.91 | −1.04 | −0.50 | −0.29 | MIR3691 | 0.76 | −1.09 | 0.39 | −0.17 | 0.27 | RNU6-678P | −0.16 | −0.86 | 1.26 | 0.81 | 1.37 |
| SSTR5-AS1 | −1.81 | 0.19 | 0.59 | 0.68 | −1.21 | CLK1 | −0.08 | 0.17 | 0.21 | 0.08 | 0.05 | PIGBOS1 | 0.03 | 0.13 | 0.24 | 0.00 | 0.08 |
| NRDE2 | −0.18 | 0.08 | −0.05 | 0.07 | 0.08 | DCTN1 | 0.08 | −0.02 | −0.21 | −0.02 | −0.14 | NDFIP2-AS1 | 0.39 | 1.06 | −0.78 | −0.69 | 0.05 |
| AC244517.7 | −1.95 | 0.70 | 1.60 | 0.95 | 0.69 | AC022079.1 | 0.43 | −0.25 | −0.38 | −0.04 | 0.13 | AC018926.1 | 0.07 | −0.13 | −0.02 | −0.27 | −0.36 |
| RNU6ATAC10P | −1.12 | 0.14 | 0.34 | −1.11 | 0.19 | AC002467.1 | 0.41 | −0.10 | 0.15 | −0.23 | −0.20 | AL161669.1 | 0.46 | −0.74 | −0.05 | −0.41 | 1.82 |
| G41208 | −0.80 | 0.43 | 0.25 | 0.27 | 0.05 | AL049874.3 | −0.87 | 0.54 | −1.48 | 0.22 | −2.99 | AC025809.2 | −0.06 | 0.17 | 0.15 | −0.61 | −0.42 |
| FANCB | 0.52 | −0.43 | −0.60 | −0.10 | −0.16 | AC099782.2 | −0.68 | −1.01 | 1.65 | −0.62 | −0.09 | AC110749.1 | −0.10 | 0.50 | 0.39 | 0.47 | 0.01 |
| NOG | −1.66 | −0.90 | 2.02 | −0.27 | 0.23 | AC006974.2 | 0.70 | −0.28 | −0.48 | −0.04 | −0.63 | FAM86EP | 0.05 | 0.20 | 0.04 | 0.63 | 0.54 |
| LBX2-AS1 | −0.66 | 0.13 | 0.10 | −0.23 | −0.38 | LINC01999 | −1.15 | 1.83 | −2.10 | −0.39 | −2.18 | RN7SL3 | −0.06 | −0.25 | −1.30 | 0.71 | −1.45 |
| LRP6 | −0.28 | 0.33 | 0.38 | 0.11 | 0.15 | AC023983.2 | −0.84 | −0.41 | 1.40 | −0.89 | 0.98 | RNU6-1321P | −0.12 | −0.66 | −0.44 | −1.13 | −0.16 |
| KLHL6 | 0.77 | −0.86 | −0.22 | −0.64 | 0.27 | RN7SKP58 | 0.73 | 0.93 | −0.37 | 0.50 | −0.85 | CFL1P2 | 0.16 | −0.06 | 1.19 | −1.20 | 0.31 |
| AP001527.1 | −1.69 | 0.78 | 0.83 | 0.26 | 0.08 | AC089984.2 | −0.18 | 0.41 | 0.06 | 0.07 | −0.01 | SRMP2 | 0.05 | −0.07 | 0.28 | −0.22 | 0.00 |
| RSL24D1P11 | −1.36 | −0.20 | 0.83 | −0.07 | 0.90 | AL139407.1 | 0.27 | −0.22 | 0.11 | 0.13 | 0.29 | RAG2 | −0.09 | −1.12 | 0.42 | 0.21 | 0.48 |
| NOS2 | −1.12 | −0.74 | −0.61 | 0.82 | 0.70 | LINC01120 | 0.78 | −0.14 | −3.21 | 0.58 | −2.76 | AC104820.1 | −0.55 | −0.33 | 1.53 | 0.33 | 0.95 |
| SLC52A3 | 0.66 | −0.64 | −0.29 | 0.18 | 0.38 | FBXW8 | −0.09 | −0.04 | 0.11 | −0.07 | 0.28 | AL139317.2 | 0.17 | −1.35 | 0.24 | −0.72 | 1.22 |
| KLF11 | −0.37 | 0.35 | 0.14 | 0.24 | −0.07 | G2523 | −0.97 | −0.86 | 0.08 | −0.06 | 2.69 | CXorf56 | −0.01 | −0.03 | −0.02 | −0.14 | −0.08 |
| ST3GAL2 | −0.38 | −0.26 | 0.19 | −0.22 | 0.28 | AL691482.3 | 0.88 | 0.03 | −1.42 | −1.29 | −2.32 | SNORA70 | −0.03 | −0.16 | −0.24 | −0.01 | −0.02 |
| RANBP9 | 0.25 | 0.11 | −0.27 | 0.10 | −0.34 | AC137936.1 | 0.33 | −0.27 | −0.60 | 0.06 | 0.58 | SLC18A1 | 0.10 | −0.28 | −1.45 | 0.15 | −1.43 |
| GAS5 | 0.40 | −0.24 | −0.10 | −0.01 | −0.16 | LRRC37BP1 | −0.15 | 0.14 | 0.32 | −0.15 | 0.15 | AC007950.1 | 0.25 | −0.66 | −2.53 | −0.02 | −1.59 |
| C17orf75 | −0.32 | 0.15 | −0.05 | 0.17 | −0.13 | GOLGA5P1 | 0.52 | −0.48 | 0.32 | −0.96 | 0.49 | BGLT3 | 0.30 | −1.16 | −1.00 | −1.15 | −2.64 |
| AC009229.1 | −1.14 | 0.62 | 1.27 | 0.02 | −0.05 | LINCO2550 | −0.65 | 1.01 | −0.74 | −0.17 | −0.84 | AL078644.1 | −0.06 | −0.54 | −1.20 | 0.13 | −0.30 |
| LINC02351 | −2.25 | 1.19 | 2.61 | 1.91 | 0.12 | DAGLB | −0.10 | −0.01 | 0.18 | 0.05 | 0.19 | AC093714.2 | 0.27 | −0.81 | −1.68 | −0.63 | 0.08 |
| DENND3 | −0.55 | 0.06 | 0.43 | −0.08 | −0.04 | AC093084.1 | −0.93 | −1.34 | 0.82 | 1.47 | 1.99 | OR4V1P | −0.54 | 0.22 | 0.17 | −0.83 | −0.81 |
| PRPF8 | 0.24 | −0.10 | −0.21 | −0.04 | −0.14 | AL359762.1 | 0.43 | −0.61 | 1.37 | −0.41 | 0.11 | NANOGNB | 0.17 | −0.73 | −0.43 | −0.76 | −0.56 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC092295.2 | −0.77 | 0.21 | 0.65 | 0.17 | 0.52 | AP000255.1 | −0.38 | −0.19 | 1.38 | −0.13 | 1.33 | AC021066.2 | −0.18 | −1.04 | −0.80 | −0.82 | 0.29 |
| ANP32E | 0.36 | −0.44 | −0.26 | −0.31 | −0.05 | KRTAP4-6 | −1.30 | −0.54 | 1.67 | −1.37 | 0.34 | AC117395.1 | −0.05 | 0.40 | 0.38 | −0.01 | −0.67 |
| AC078955.1 | −1.21 | 0.02 | 0.96 | −0.44 | 0.95 | PRELID1P1 | 0.67 | 0.04 | −0.01 | 0.22 | −0.22 | SAA1 | −0.09 | 0.41 | −0.23 | 0.11 | −0.14 |
| AL513534.1 | −0.84 | 0.77 | 0.75 | 0.76 | −0.04 | AL359183.1 | −0.52 | −0.14 | −0.98 | 0.41 | 0.14 | AL049839.2 | 0.32 | 1.21 | −1.87 | 2.05 | −2.03 |
| SAPCD2 | 0.63 | −0.03 | −0.87 | −0.08 | −0.29 | KRT18P25 | −0.89 | 1.54 | −2.27 | 1.12 | −2.48 | KRTAP9-9 | −0.62 | −0.21 | 0.66 | −0.80 | −2.99 |
| POGLUT1 | 0.35 | −0.18 | −0.18 | −0.02 | −0.04 | G8329 | −1.83 | 2.54 | 0.37 | 0.56 | −1.78 | RPL7P4 | 0.10 | −0.01 | −1.14 | 0.38 | −0.94 |
| RAB5B | 0.32 | 0.09 | −0.19 | 0.11 | −0.32 | RN7SL333P | 0.27 | 0.00 | −0.09 | −0.07 | 0.14 | AL031963.3 | −0.06 | −0.06 | −0.33 | 0.13 | 0.14 |
| PIP4P2 | −0.49 | 0.41 | 0.66 | 0.27 | 0.11 | AC098487.1 | 0.48 | −0.37 | −1.10 | 0.29 | −0.38 | RNU6-673P | 0.53 | −1.30 | −0.21 | 0.87 | 1.22 |
| AC098650.1 | −0.62 | 0.17 | 1.00 | −0.09 | 0.30 | LRP11 | 0.16 | 0.03 | 0.09 | 0.09 | 0.23 | AC093671.1 | 0.14 | 0.06 | −1.04 | 1.90 | −0.22 |
| IL20 | 1.80 | −0.96 | −3.38 | −0.18 | −2.90 | DAP3P1 | −0.57 | −0.41 | 0.04 | −0.75 | 0.06 | AC116553.2 | −0.17 | −0.26 | 0.67 | 0.36 | 0.04 |
| G36466 | −1.25 | 0.86 | 0.85 | 0.85 | 1.04 | G32522 | 0.75 | 0.17 | 1.46 | 0.95 | −0.03 | LINC01838 | −0.19 | −0.60 | −1.43 | 0.14 | −1.32 |
| AP001056.2 | −0.99 | 0.31 | 0.61 | 0.06 | 0.16 | AC055716.2 | 0.63 | −0.13 | −1.08 | 0.90 | 0.12 | AC104027.1 | −0.49 | 0.90 | 0.02 | 0.94 | −0.72 |
| CALR4P | −1.09 | 1.21 | 0.29 | 1.05 | −0.61 | AC005082.1 | 0.37 | −0.41 | 0.66 | 0.39 | 0.73 | DNM1P33 | 0.26 | −0.40 | −0.35 | 0.49 | 0.76 |
| PAFAH1B1 | 0.29 | −0.04 | −0.19 | −0.03 | −0.25 | RCN1P2 | 0.21 | 0.03 | 0.07 | 0.14 | 0.22 | RNLS | 0.03 | 0.03 | −0.49 | 0.28 | −0.11 |
| ADGRV1 | −0.91 | 0.29 | 0.67 | 0.30 | 0.39 | SLC25A15P3 | −1.00 | −0.73 | 0.22 | 0.21 | 2.09 | AL671883.3 | 0.15 | −1.50 | −1.03 | −0.21 | 0.40 |
| AL592295.1 | −0.70 | 0.19 | 0.06 | 0.33 | 0.00 | ERN1 | 0.09 | −0.10 | 0.01 | 0.04 | 0.09 | AL109954.2 | −0.61 | −1.64 | 0.71 | −1.00 | 2.22 |
| PFN1P1 | 1.38 | −0.73 | −2.92 | 0.30 | −1.41 | OR52U1P | −0.53 | −0.05 | 1.80 | −0.47 | 0.13 | AP000439.4 | −0.61 | −0.37 | NA | −1.18 | −0.57 |
| LDLRAD4 | −0.55 | 0.43 | 0.58 | −0.02 | 0.21 | LINC01687 | 0.79 | −1.19 | −1.91 | 0.53 | −1.37 | OR5P3 | 0.08 | 1.48 | 1.06 | 0.27 | −0.34 |
| ERGIC1 | −0.22 | 0.10 | 0.20 | −0.12 | 0.02 | FAM83F | 0.24 | 0.15 | −0.21 | 0.33 | 0.10 | AC096996.1 | 0.61 | −1.54 | 0.10 | 0.55 | 1.76 |
| POLE4 | 0.36 | −0.38 | −0.33 | −0.16 | 0.29 | FMO3 | −0.23 | 0.06 | 0.87 | −0.21 | −0.07 | IGHV3OR16-13 | 0.61 | 0.71 | −0.01 | 0.99 | −3.30 |
| IGSF1 | −1.19 | 0.20 | 0.52 | 0.44 | 0.49 | LHFPL5 | 0.62 | −0.31 | −1.16 | −0.30 | −1.02 | LINC02411 | −0.15 | −1.53 | −2.04 | 0.46 | −1.63 |
| AC010531.3 | −0.66 | 0.65 | 0.29 | 0.01 | −0.26 | AC093525.4 | −0.50 | 0.16 | 0.33 | −0.38 | −0.42 | SNORA31 | −0.04 | −0.10 | −0.25 | 0.30 | −0.29 |
| INSL3 | 1.85 | −2.54 | 0.07 | 0.33 | 0.54 | AC245060.5 | 0.19 | −0.33 | 0.49 | −0.39 | 0.59 | AC016813.1 | 0.61 | 0.00 | −0.85 | 0.63 | 0.57 |
| AC091808.1 | 1.72 | −0.86 | −2.46 | −0.79 | −1.94 | AL354702.2 | −0.73 | 0.77 | 1.31 | 0.36 | 0.87 | LINC01216 | −0.59 | −0.40 | 1.02 | −0.56 | 0.98 |
| C17orf50 | −1.18 | 0.70 | 0.22 | 0.13 | 0.80 | FTLP6 | −0.24 | 0.29 | 0.87 | −0.10 | 0.17 | RN7SL225P | −0.09 | 0.06 | 0.14 | −0.47 | −0.24 |
| G10181 | −0.76 | 0.23 | 0.40 | −0.01 | −0.39 | KREMEN2 | −0.33 | −0.10 | −0.72 | 0.65 | 0.06 | AC113361.1 | −0.09 | −0.53 | 1.07 | −0.19 | 0.18 |
| FAM71D | −0.68 | 0.19 | 0.29 | 0.24 | 0.37 | HRAT5 | 0.47 | −0.69 | −0.15 | −0.67 | 0.33 | AC091729.3 | 0.03 | −0.19 | 0.02 | −0.22 | 0.25 |
| RAD17P1 | −1.69 | −0.33 | −1.27 | −0.20 | −0.74 | AC015883.1 | −0.17 | −0.20 | 0.27 | 0.15 | 0.64 | AC007493.1 | 0.11 | −0.12 | −0.35 | 0.17 | 0.65 |
| SCARNAS | −0.45 | 0.18 | 0.35 | 0.20 | 0.04 | AP003900.1 | 0.74 | −0.23 | −4.22 | 0.81 | −4.00 | MT3 | −0.19 | 0.14 | 2.39 | 0.63 | 1.50 |
| FAM86GP | −0.94 | 0.55 | 1.22 | 0.13 | −0.19 | STPG3-AS1 | −0.47 | 0.17 | 0.29 | 0.45 | 0.39 | AC099520.1 | −0.09 | −0.07 | 0.19 | 0.17 | 0.10 |
| CLIP1-AS1 | 0.61 | −0.17 | −0.34 | −0.20 | −0.19 | OR2B7P | −0.85 | 0.18 | 1.56 | 0.17 | 0.51 | BIRC8 | −0.24 | −0.70 | −0.25 | −1.40 | −1.00 |
| LINC01521 | −0.65 | −0.22 | 0.27 | −0.16 | 0.41 | LINC01546 | 0.60 | −0.45 | 0.39 | 0.31 | 0.02 | OR51T1 | 0.12 | −0.63 | −0.61 | 0.50 | −1.46 |
| COL23A1 | −0.65 | −0.02 | −0.21 | 0.14 | 0.48 | C16orf86 | −0.35 | 0.18 | 0.09 | −0.13 | 0.24 | SLC37A3 | 0.02 | −0.05 | 0.09 | −0.12 | 0.02 |
| MEFV | 1.08 | −1.61 | −1.69 | −0.62 | −0.71 | HYAL4 | −0.32 | 0.51 | −0.90 | 0.20 | −1.05 | RFPLIS | −0.07 | −0.21 | 0.21 | −0.25 | 0.17 |
| BMPER | −0.93 | 0.38 | 0.32 | −0.01 | −0.39 | C11orf72 | −0.70 | −0.39 | −0.07 | −0.46 | −0.30 | RPL7P11 | 0.04 | −0.25 | 0.21 | 0.08 | 0.48 |
| KLF14 | −1.30 | −0.81 | 0.13 | 0.66 | 0.71 | HMX1 | −0.90 | −1.04 | 2.01 | −0.64 | 0.61 | PROKR2 | −0.25 | −0.95 | 1.92 | 0.46 | 1.04 |
| MEX3D | 0.42 | 0.02 | −0.31 | 0.07 | −0.17 | RIBC2 | −0.23 | −0.42 | −0.35 | −0.32 | −0.03 | BNIP3L | −0.04 | 0.26 | 0.11 | 0.26 | −0.45 |
| ACTN2 | −1.07 | −0.29 | −0.55 | 0.68 | −0.52 | RNUSE-2P | −0.42 | 0.28 | −0.61 | −0.03 | −0.87 | ADAM3A | 0.19 | −0.51 | −0.39 | 0.21 | 1.65 |
| COX6B1P4 | −2.09 | 2.60 | 2.96 | 0.49 | 0.05 | RN7SKP74 | −0.31 | 0.70 | −0.34 | 0.39 | −0.34 | RN7SKP102 | −0.22 | 0.53 | 1.86 | 1.02 | 0.06 |
| ABHD12 | −0.27 | 0.18 | 0.35 | −0.14 | −0.09 | AL049844.2 | 0.28 | −0.41 | −0.26 | 0.10 | 0.27 | RP11-125N22.4 | −0.26 | −1.20 | −0.62 | −0.27 | 0.81 |
| RN7SKP86 | −2.20 | 1.55 | 0.96 | 1.51 | 1.10 | OR1L3 | −0.41 | 0.25 | −0.14 | −0.57 | −0.78 | AC127383.1 | 0.31 | −1.05 | −1.77 | 0.60 | −0.31 |
| FBXO48 | −0.49 | −0.08 | 0.38 | −0.16 | 0.27 | RPL12P27 | −0.97 | −0.41 | 0.57 | −0.43 | 0.51 | RN7SKP243 | 0.06 | 0.83 | −0.39 | 0.60 | −0.33 |
| ABCA7 | −0.49 | 0.10 | −0.15 | 0.41 | 0.43 | AL135744.1 | 0.70 | 0.02 | −0.59 | 0.38 | −1.30 | AC034232.1 | 0.18 | −0.06 | −0.04 | −1.06 | −0.54 |
| CCDC86 | 0.48 | −0.49 | −0.55 | 0.05 | −0.10 | AC104394.1 | −0.83 | 0.27 | −0.97 | 0.48 | 0.34 | LINC01387 | 0.21 | −1.50 | 0.76 | 0.54 | 0.68 |
| LINC01822 | −1.67 | −0.63 | 0.98 | 0.31 | 2.09 | AL590683.1 | 0.70 | −1.80 | −2.81 | −0.18 | −1.76 | GLYATL2 | −0.06 | −0.03 | 0.49 | −0.09 | 0.09 |
| RPL7P24 | 1.25 | −0.23 | −1.39 | 0.04 | −1.17 | AL592148.1 | 0.42 | 0.45 | −1.03 | 0.31 | −0.51 | MS4A6A | 0.05 | −0.17 | 0.23 | −0.15 | −0.02 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| HMBOX1-IT1 | −0.63 | 0.14 | 0.39 | 0.01 | 0.27 | AC007096.1 | 1.31 | −0.66 | 0.33 | −1.05 | −0.14 | CARMIL2 | 0.05 | −0.49 | 0.11 | −0.46 | 0.47 |
| FAM135A | 0.33 | 0.00 | −0.17 | 0.12 | −0.10 | BTBD10P1 | 0.70 | −1.34 | −1.20 | 0.18 | −1.28 | AC015522.1 | −0.16 | −0.73 | −1.27 | 0.35 | 0.15 |
| PABPC3 | 0.66 | −0.34 | −0.41 | 0.11 | −0.31 | GPR85 | −0.38 | 0.35 | −0.05 | 0.17 | −0.39 | G33837 | −0.17 | −0.69 | 1.35 | 0.76 | 1.87 |
| CCDC151 | −0.96 | 0.00 | −0.40 | 0.45 | −0.12 | AC005244.1 | 0.31 | 0.04 | 0.10 | 0.00 | 0.35 | AC025035.1 | 0.13 | −0.40 | −0.06 | −0.27 | 0.42 |
| MAN1C1 | −0.48 | 0.09 | 0.32 | 0.17 | 0.36 | AC069113.2 | −1.32 | 0.71 | 0.82 | 0.03 | 0.70 | LINC01912 | −0.35 | −1.45 | 0.26 | 0.21 | 1.22 |
| BMP2KL | −0.69 | 0.57 | 0.69 | 0.15 | 0.07 | AGKP1 | −0.39 | 0.46 | 1.09 | 0.14 | 0.33 | AL590482.1 | 0.19 | −0.70 | −1.96 | −0.53 | −2.35 |
| HIST1H3E | 0.79 | −0.53 | −0.58 | −0.16 | −0.24 | ARHGEF38-IT1 | −0.64 | −0.56 | −0.22 | 0.13 | 0.11 | AC093853.1 | 0.11 | −0.13 | −0.61 | 0.51 | 0.05 |
| AC009411.2 | −1.74 | 1.17 | 0.83 | 0.31 | −0.42 | MRPL57P3 | 0.41 | 0.11 | −1.13 | −0.27 | −0.09 | KLF4P1 | −0.04 | −0.51 | −0.06 | −0.04 | 0.57 |
| SLC45A4 | −0.42 | 0.15 | 0.89 | −0.18 | 0.39 | MIR3909 | 0.32 | −0.63 | 0.05 | −0.30 | 0.56 | MIR4265 | 0.06 | −0.38 | −0.56 | −0.05 | −0.85 |
| RBM11 | −1.16 | 0.46 | 1.03 | −0.10 | −0.14 | SNORD99 | −0.28 | 0.27 | 0.21 | 0.44 | −0.60 | AL691515.1 | 0.28 | −0.65 | −0.25 | 0.18 | −1.30 |
| DUSP18 | 0.34 | −0.03 | −0.55 | −0.14 | −0.35 | AC040162.1 | −0.18 | 0.07 | 0.09 | 0.13 | 0.15 | AC027312.1 | 0.10 | 0.26 | −0.21 | −0.13 | −0.64 |
| CHDH | −0.63 | 0.50 | 0.38 | 0.43 | 0.39 | ACTG1P12 | −0.48 | 0.81 | −0.73 | 0.54 | −0.91 | AL355377.2 | −0.07 | 0.16 | −0.23 | 0.13 | 0.17 |
| GSK3B | 0.25 | 0.05 | −0.08 | −0.07 | −0.17 | AC021074.1 | −0.61 | 0.04 | 0.95 | 0.54 | 0.55 | AP001599.1 | −0.09 | 0.15 | −0.01 | −0.93 | 0.31 |
| AC005753.1 | −1.27 | 1.13 | −0.33 | 0.87 | −0.44 | DNASE2B | −0.69 | 1.24 | 0.85 | 0.28 | −0.29 | LINC02150 | −0.08 | −0.66 | 0.12 | −0.54 | 0.47 |
| ANKRD11 | −0.30 | 0.02 | −0.02 | 0.01 | 0.06 | AC092171.1 | −0.22 | 0.56 | 0.28 | 0.45 | 0.33 | AC139887.4 | −0.04 | 0.29 | 0.85 | −0.18 | 0.07 |
| RN7SL441P | 1.16 | −0.14 | −0.12 | −0.04 | −0.51 | LAYN | 0.28 | −0.24 | −0.66 | 0.05 | −0.56 | AC003688.2 | 0.32 | 1.36 | 0.00 | 0.86 | 0.15 |
| LYRM7 | −0.25 | 0.15 | 0.36 | 0.01 | 0.02 | SNORA33 | 0.27 | 0.06 | −0.59 | 0.78 | −1.13 | FCF1P7 | 0.05 | −0.02 | 0.32 | −0.10 | 0.19 |
| CIART | −0.52 | 0.45 | 0.62 | 0.20 | −0.23 | C10orf142 | −0.59 | 1.37 | −0.50 | 1.30 | 0.10 | AC002525.1 | −0.04 | 0.17 | 0.96 | −0.07 | −0.01 |
| AP001206.1 | −0.68 | 0.66 | 0.08 | 0.52 | −0.08 | HNRNPKP4 | 0.32 | −0.55 | −0.66 | −0.60 | −0.80 | HSPD1P21 | −0.61 | 0.24 | 0.36 | 0.60 | 1.17 |
| RPL7L1P12 | 0.73 | −0.15 | 0.08 | −0.11 | −0.09 | AL034375.1 | 0.72 | −0.91 | 0.63 | −0.62 | 0.89 | COMP | 0.05 | 0.04 | −0.49 | −0.45 | −1.40 |
| MIS12 | 0.28 | −0.32 | −0.22 | −0.26 | 0.09 | SDE2 | 0.09 | −0.04 | −0.02 | −0.13 | −0.21 | RPSAP63 | 0.22 | −0.80 | −0.70 | 0.27 | −2.57 |
| PLS3-AS1 | −0.73 | 0.27 | 1.32 | −0.11 | 0.16 | CLUH | 0.15 | −0.17 | −0.75 | 0.25 | −0.04 | PTP4A1P6 | −0.23 | 0.79 | 0.01 | 1.39 | 0.24 |
| AC011239.2 | −0.65 | −0.05 | −0.18 | −0.08 | −0.02 | GSC2 | 1.13 | −0.16 | −0.57 | 0.42 | 0.12 | AL096803.2 | −0.24 | −1.70 | 0.44 | −0.85 | 1.02 |
| IQGAP3 | 0.55 | −0.66 | −1.40 | −0.31 | −0.48 | AC008507.2 | −0.20 | 0.33 | −0.02 | 0.36 | −0.14 | MTCO1P17 | −0.26 | −0.26 | 0.12 | 0.11 | 0.43 |
| IPP | −0.27 | 0.03 | 0.30 | 0.06 | 0.23 | AL359697.1 | −0.66 | −0.13 | 1.21 | −1.18 | −1.04 | AC006199.1 | 0.38 | −0.12 | −0.62 | −0.51 | −1.16 |
| LINC01678 | −0.86 | 0.34 | 0.29 | 0.12 | 0.15 | AL139246.5 | −0.28 | 0.01 | −0.28 | 0.52 | 0.19 | AL359091.4 | 0.07 | −0.28 | 0.19 | 0.17 | 0.13 |
| NEXN-AS1 | −0.79 | −0.19 | 0.64 | −0.38 | −0.01 | AC243772.2 | 0.59 | −1.45 | 0.73 | −0.76 | 0.09 | AL121899.1 | −0.10 | −0.80 | 0.89 | 0.19 | 0.44 |
| AP001628.1 | −0.91 | 0.55 | 0.26 | 0.86 | 0.01 | AC013452.2 | −0.53 | −1.62 | 2.13 | −0.94 | 1.33 | AC021979.1 | 0.61 | 0.03 | −0.50 | 0.95 | 0.16 |
| AC023886.2 | 1.41 | 0.13 | −0.77 | 0.22 | −0.80 | SLC16A14 | 0.26 | −0.11 | −0.41 | 0.48 | −0.31 | AC105052.2 | −0.06 | 0.02 | 0.14 | 0.78 | 0.74 |
| AC079949.1 | −0.96 | 0.26 | 0.52 | 1.22 | −0.44 | SLC16A13 | −0.21 | 0.13 | 0.63 | 0.10 | 0.38 | AL691447.3 | 0.05 | 0.10 | −0.50 | −0.03 | −0.14 |
| ICAM5 | 0.73 | −0.80 | −1.57 | 0.03 | 0.08 | AC024145.1 | −0.22 | 0.18 | 0.16 | 0.39 | 0.02 | AC234781.4 | −0.09 | 0.26 | −0.60 | −0.20 | −0.62 |
| AC006019.3 | −2.87 | 1.49 | 3.88 | −0.34 | 0.53 | SNORD114-21 | 0.65 | −0.12 | −0.55 | −0.31 | −0.21 | AC073264.3 | 0.11 | −0.16 | 0.80 | −1.30 | 0.28 |
| PPP1R37 | −0.36 | 0.17 | 0.12 | 0.24 | 0.20 | AC048380.3 | 0.32 | 0.27 | 0.56 | −0.73 | −0.58 | KLK11 | 0.04 | 0.14 | 0.36 | 0.02 | −0.07 |
| STX19 | 0.59 | −0.14 | −0.07 | 0.24 | 0.07 | PLET1 | −0.28 | 0.38 | 0.55 | 0.17 | 0.36 | AC079228.1 | 0.14 | −0.36 | −2.47 | 1.21 | 0.46 |
| PSG11 | −0.86 | 0.21 | 0.17 | −0.07 | −0.11 | LINC01100 | −1.02 | 1.27 | 0.94 | −0.31 | 0.71 | AC091812.1 | 0.10 | 0.22 | 0.10 | −0.41 | −0.66 |
| EBF2 | −0.91 | 0.54 | 1.04 | 0.24 | −0.26 | DYDC2 | 0.50 | −1.03 | −0.83 | −0.16 | 0.44 | GDPGP1 | −0.04 | 0.19 | −0.69 | 0.08 | −0.18 |
| AL117342.1 | −1.29 | 1.03 | 1.96 | −0.02 | −0.44 | ARMC4 | −0.42 | 0.25 | 0.26 | 0.18 | −0.57 | OR5M6P | 0.61 | 0.46 | 0.39 | 0.04 | −1.61 |
| CHAMP1 | 0.34 | −0.14 | −0.10 | −0.09 | −0.09 | AP001893.3 | 0.75 | −0.64 | −0.66 | −0.21 | −0.16 | FEM1AP4 | 0.59 | −0.78 | −0.36 | 1.19 | −1.53 |
| AL513325.1 | −1.49 | 0.09 | 0.45 | −0.45 | −0.32 | AL359504.1 | −0.36 | −0.30 | −0.95 | 0.50 | −0.36 | AC027315.1 | 0.61 | −0.17 | 0.30 | 1.04 | 0.92 |
| LIPE | −0.98 | 0.78 | 0.23 | 0.66 | −0.06 | AC080162.1 | 0.25 | −0.22 | −0.08 | −0.15 | 0.08 | AC092435.2 | 0.20 | −0.26 | −1.11 | 0.84 | −1.02 |
| FUT10 | −0.27 | 0.36 | 0.31 | 0.29 | 0.24 | SAMMSON | −0.39 | −0.39 | −0.30 | −0.04 | 0.02 | AL138880.1 | −0.10 | −0.99 | −0.35 | −0.30 | 0.33 |
| EFNB2 | 0.41 | 0.19 | 0.00 | −0.05 | −0.21 | AP003170.3 | 0.48 | 0.00 | −0.87 | 0.22 | 0.30 | LINC01677 | −0.12 | −0.08 | −1.25 | 0.27 | −1.76 |
| AC239800.2 | −0.89 | 0.33 | 0.73 | −0.02 | 0.22 | G34171 | −0.59 | −0.41 | 0.74 | −0.11 | 0.75 | NOXRED1 | 0.04 | 0.13 | 0.20 | 0.08 | 0.25 |
| PAQR4 | 0.60 | −0.44 | −0.87 | 0.15 | −0.15 | AC006967.3 | −0.99 | −0.59 | 0.55 | −0.65 | 0.75 | SEMA6A-AS2 | −0.12 | 0.61 | −1.42 | 0.51 | −1.64 |
| MY01G | 0.71 | −1.10 | −0.79 | −0.53 | 0.08 | STXBP5-AS1 | 0.23 | −0.17 | −0.74 | −0.12 | −0.32 | RN7SL639P | 0.11 | −0.52 | 0.45 | 0.29 | 0.60 |
| C1orf137 | 2.44 | 0.25 | −2.27 | −0.29 | −2.72 | RNU6-26P | −0.36 | −0.47 | 0.11 | 0.07 | 0.76 | SNORD113-6 | 0.18 | 0.50 | 2.25 | −0.25 | −0.88 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| GPX4 | −0.66 | 0.49 | 0.70 | 0.06 | 0.19 | RN7SL557P | −0.69 | 0.09 | −0.63 | 0.83 | 0.58 | C1GALT1P2 | −0.11 | 0.57 | 1.29 | −0.62 | −0.27 |
| ERMAP | −0.23 | 0.12 | −0.06 | 0.29 | 0.02 | AL161669.2 | −0.72 | 0.40 | 0.39 | 0.86 | −1.67 | ASH2LP3 | 0.20 | −1.45 | 0.13 | −1.15 | 1.63 |
| LAMA4 | −0.66 | 0.24 | 0.92 | −0.22 | 0.13 | RPL36AP33 | −0.28 | 0.15 | 0.72 | −0.16 | 0.22 | LINC02108 | −0.25 | 1.56 | −0.79 | −1.20 | −2.16 |
| AC005237.1 | −0.93 | 0.80 | 1.05 | 0.48 | 0.29 | AC007249.2 | −0.46 | 0.26 | 0.41 | −0.66 | 0.29 | SMIM14 | −0.02 | 0.12 | 0.13 | 0.09 | −0.17 |
| IL18RAP | 0.99 | −0.75 | −0.49 | −0.48 | −0.54 | GSTA1 | −0.60 | −0.79 | −0.97 | 0.20 | 0.34 | ALDOAP2 | −0.36 | −0.16 | −0.03 | −1.45 | −1.65 |
| FAM217A | 0.72 | −0.04 | −0.76 | 0.45 | 0.14 | INSYN1-AS1 | −0.91 | −2.19 | 2.15 | −0.97 | 1.74 | IGHV3-72 | 0.60 | 0.94 | 0.02 | 3.24 | −2.75 |
| ATG4D | −0.46 | 0.18 | −0.15 | 0.33 | −0.07 | GCK | 0.47 | −0.30 | −1.20 | 0.86 | 0.09 | ANHX | −0.18 | 0.26 | 0.01 | −0.75 | 0.56 |
| AC108865.1 | −0.85 | −0.12 | 0.78 | 0.40 | 0.59 | SFTPD | 0.25 | 0.39 | −0.15 | 0.68 | −0.14 | G22375 | 0.14 | 0.16 | 1.89 | 1.63 | 0.21 |
| COPS7B | −0.30 | 0.14 | 0.15 | 0.13 | 0.07 | MTMR7 | 0.13 | 0.23 | 0.19 | −0.04 | −0.04 | AP001024.2 | −0.25 | 0.93 | −0.52 | −0.10 | −1.51 |
| AC100821.2 | 1.02 | −0.57 | −0.68 | −0.11 | 0.07 | MIR222 | 0.36 | 0.05 | −0.42 | 0.38 | −1.08 | PPP1R13B | −0.01 | 0.19 | 0.13 | 0.17 | 0.05 |
| GRIN2D | −0.51 | 0.04 | 0.47 | −0.05 | 0.32 | DCXR | −0.15 | 0.36 | 0.20 | 0.09 | −0.14 | AC091544.3 | −0.56 | 1.34 | 2.23 | 0.17 | 0.49 |
| MAGEA10 | −1.39 | −0.42 | 1.88 | 0.09 | 1.10 | RASA1 | 0.07 | −0.03 | 0.07 | −0.11 | 0.05 | OR51E2 | −0.12 | −0.82 | −1.39 | 0.70 | −1.16 |
| AC061975.1 | −1.66 | 0.02 | 0.97 | −0.19 | −0.50 | AL590302.2 | 1.09 | −0.83 | −0.22 | 0.52 | 2.08 | AC112198.3 | 0.30 | −1.43 | −1.82 | −0.56 | −0.81 |
| RPS15AP30 | −0.58 | 0.10 | 0.10 | 0.34 | 0.15 | AC090617.1 | 0.34 | −0.03 | 0.15 | 0.68 | 0.10 | AC008649.2 | −0.05 | −0.04 | 0.16 | −0.10 | 0.12 |
| AL353671.2 | −0.78 | −0.38 | 0.42 | −0.38 | 0.79 | G28649 | 0.16 | −0.03 | −0.43 | −0.08 | −0.47 | DHRS4-AS1 | 0.02 | −0.13 | 0.13 | −0.10 | 0.31 |
| ANXA8L1 | 0.42 | −0.18 | −0.77 | 0.67 | 0.24 | G36839 | −0.51 | 0.36 | 1.12 | −0.01 | 0.15 | ART2BP | 0.60 | −1.54 | 0.38 | 1.87 | 1.91 |
| ACP1 | 0.36 | −0.12 | −0.07 | −0.23 | −0.16 | LINC01732 | 1.01 | −2.27 | −0.34 | 0.10 | 1.18 | RN7SL342P | 0.14 | 0.78 | −0.29 | 1.01 | −0.70 |
| QTRT1 | −0.51 | 0.15 | −0.06 | 0.36 | 0.32 | AC131011.1 | 0.52 | 0.17 | −0.92 | 0.23 | −1.23 | MIR5699 | −0.06 | −0.62 | 0.99 | −1.02 | 0.69 |
| AC011816.1 | 1.06 | −0.08 | −0.64 | 0.03 | 0.12 | AC005281.1 | −1.39 | 0.48 | 0.08 | −0.39 | −0.61 | AL360091.1 | −0.05 | 0.08 | −0.94 | 0.67 | −0.23 |
| AC004057.1 | 1.03 | −0.43 | −0.15 | −0.22 | 0.79 | AC016822.1 | −1.47 | −0.39 | 0.94 | 0.14 | −0.39 | G28386 | −0.23 | −0.21 | −1.36 | −0.17 | 0.59 |
| GTF2IP5 | −0.79 | 0.12 | 0.69 | −0.27 | −0.01 | RNU6-42P | 0.39 | −0.52 | −0.55 | −0.32 | −0.09 | ACTBP11 | −0.09 | −0.48 | −0.84 | 0.09 | −0.10 |
| DIRAS3 | −0.59 | 0.21 | 0.54 | −0.29 | 0.32 | RPL37AP1 | −0.59 | 2.65 | 0.22 | 2.46 | −0.42 | DCTN3 | 0.02 | 0.27 | 0.19 | 0.06 | −0.14 |
| NLRC4 | 0.70 | −0.74 | −0.78 | −0.41 | −0.43 | AL360182.2 | −0.56 | 0.44 | 1.84 | −0.45 | −0.12 | ORM2 | 0.08 | −0.62 | 0.27 | −0.90 | −0.05 |
| AL513548.3 | −0.70 | −0.22 | 0.54 | 0.25 | 0.62 | ABR | −0.11 | −0.06 | −0.46 | 0.08 | −0.11 | AC010947.1 | −0.48 | −0.96 | 1.83 | −1.12 | 0.90 |
| SHPRH | −0.20 | 0.13 | 0.30 | 0.02 | 0.15 | AL359258.3 | 0.53 | −0.64 | −1.86 | −0.22 | −0.58 | RAD23BP2 | 0.24 | −0.22 | 0.24 | −0.52 | −2.21 |
| AL365277.1 | 0.86 | −0.56 | −0.19 | −0.59 | −0.30 | PTGER1 | −0.48 | 0.21 | −0.09 | −0.23 | 0.47 | IL6STP1 | −0.16 | 1.15 | 0.03 | 0.70 | −0.43 |
| AC018804.1 | −0.84 | 0.72 | 0.16 | 0.68 | 0.16 | RPRD2 | 0.08 | 0.10 | 0.07 | 0.03 | −0.01 | AC140481.1 | 0.30 | −1.62 | −1.27 | −0.10 | −0.40 |
| AC104564.3 | −1.05 | −0.22 | 0.32 | 0.74 | 0.86 | AC011407.1 | 0.57 | 0.45 | −0.03 | 0.05 | −0.84 | AP005242.4 | −0.25 | −0.97 | 0.78 | 0.05 | 2.68 |
| ETFDH | −0.30 | 0.36 | 0.39 | 0.26 | 0.03 | SLC31A1P1 | 1.11 | −0.16 | −2.34 | 0.45 | −1.66 | HIGD1B | −0.05 | −0.17 | 0.45 | −0.10 | 0.63 |
| ALPK2 | 0.79 | −0.43 | 0.35 | −1.28 | −0.48 | AC010624.1 | −0.62 | 1.50 | 0.16 | 1.27 | −1.04 | MTND5P30 | −0.15 | −0.31 | −0.92 | 0.14 | 0.24 |
| AC090519.4 | −1.25 | −0.59 | −0.21 | −0.07 | 1.33 | AL022342.1 | −0.72 | 0.96 | 0.51 | 0.23 | −1.53 | EFCAB6-AS1 | 0.08 | −0.61 | −1.45 | 0.18 | −0.80 |
| FAM111A-DT | −0.53 | 0.32 | 0.49 | −0.03 | 0.21 | RPL23AP65 | 0.40 | 0.07 | 0.02 | 0.09 | −0.23 | OR6Y1 | 0.10 | 0.11 | −1.32 | 1.10 | −0.98 |
| FAM171A2 | −0.66 | −0.07 | 1.19 | −0.08 | 0.76 | RNU4-1 | 0.24 | −0.36 | −0.66 | 0.46 | −0.22 | LINC01063 | 0.11 | −0.64 | −0.23 | −0.70 | 0.45 |
| LPCAT2 | 0.39 | 0.07 | 0.13 | −0.12 | −0.29 | AL442663.3 | 0.43 | −0.55 | −0.69 | −0.22 | −0.58 | G36480 | 0.13 | 0.06 | −1.08 | 0.80 | 0.41 |
| RN7SL510P | −1.13 | 0.21 | 0.01 | −0.42 | 0.46 | NCKAP5 | 0.13 | 0.07 | −0.21 | −0.05 | −0.16 | RNU6-258P | −0.27 | 0.38 | −0.09 | −1.07 | −0.76 |
| FZR1 | −0.35 | 0.21 | −0.24 | 0.10 | −0.04 | KLHDC8B | −0.17 | 0.20 | 0.39 | 0.25 | 0.16 | AC018659.2 | −0.60 | 0.82 | −0.54 | −0.87 | −1.67 |
| KDM3A | −0.30 | 0.30 | 0.43 | 0.17 | 0.13 | RN7SL129P | −0.31 | −0.25 | −0.39 | 0.24 | −0.18 | CENPUP1 | 0.60 | −1.05 | −0.12 | −0.38 | 0.99 |
| EIF5AP4 | 1.55 | −0.74 | −0.77 | 0.06 | −0.60 | AP003972.1 | 0.65 | −0.14 | −1.84 | 1.10 | −1.00 | CDRT8 | −0.18 | −0.44 | 0.09 | 0.79 | −0.13 |
| LARGE1 | −0.33 | 0.06 | 0.00 | −0.05 | −0.11 | AC093909.6 | 0.38 | −0.11 | −0.70 | −0.20 | −1.09 | BTG3P1 | 0.23 | −0.50 | −0.95 | −0.15 | −1.47 |
| DHX8 | 0.20 | −0.08 | −0.19 | −0.10 | −0.15 | SEPT7P9 | −0.33 | −0.45 | 0.29 | 0.35 | 0.59 | AC011092.2 | 0.06 | 0.58 | −0.41 | 0.10 | −1.38 |
| ATXN2 | −0.20 | 0.10 | 0.16 | −0.09 | 0.01 | IGLV1-44 | 1.20 | 1.36 | 0.64 | −0.39 | −1.08 | AC027343.1 | 0.59 | −1.62 | 0.44 | −0.79 | −0.12 |
| ENTPD8 | −1.04 | 0.72 | 1.08 | 0.81 | 0.56 | RARRES3 | −0.32 | 0.00 | 0.34 | −0.35 | −0.03 | DNTT | 0.15 | 0.41 | −1.57 | 0.66 | −0.41 |
| AF178030.1 | 0.78 | 0.38 | −0.55 | −0.06 | −0.64 | LRRC8C | 0.14 | −0.20 | 0.22 | −0.22 | 0.07 | PRR29-AS1 | −0.09 | 0.28 | −0.27 | 0.95 | 0.14 |
| AC138866.2 | −1.16 | 0.46 | 0.42 | 1.16 | −0.49 | AL136313.1 | −1.12 | 1.79 | −0.38 | −0.33 | −0.47 | AC006548.1 | −0.20 | −0.68 | 0.64 | −0.03 | −0.42 |
| HNRNPCP8 | −1.61 | 0.73 | 1.09 | 0.17 | 0.53 | B4GALT1-AS1 | 0.43 | −0.33 | −0.56 | −0.14 | 0.72 | BCL9L | −0.02 | 0.14 | −0.28 | 0.20 | −0.09 |
| MATR3 | 0.26 | −0.14 | −0.18 | −0.05 | −0.12 | IGSF6 | 0.19 | −0.65 | −0.37 | −0.34 | 0.30 | SLC39A8 | 0.04 | −0.25 | 0.72 | −0.68 | 0.28 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC027627.1 | 0.98 | −0.99 | −0.86 | 0.01 | 0.00 | DNAJC14 | 0.10 | −0.09 | −0.14 | 0.05 | 0.03 | ERICD | 0.06 | −0.42 | −0.85 | 0.48 | 0.05 |
| COMMD9 | 0.29 | −0.09 | −0.13 | 0.02 | −0.15 | AC008619.1 | −0.58 | 0.03 | 1.24 | 0.87 | 0.61 | AC233702.3 | −0.59 | −0.63 | 0.62 | 0.48 | 0.69 |
| MRPL53P1 | 0.91 | −0.38 | −1.01 | −0.06 | −0.57 | AC104623.1 | 0.40 | 0.10 | −0.63 | 0.16 | 0.25 | AC008505.1 | 0.09 | −0.48 | −0.37 | 0.32 | −0.84 |
| HDAC1P2 | 0.49 | −0.12 | −0.76 | 0.25 | −0.39 | AL109947.1 | 0.99 | −0.51 | 1.32 | 1.25 | 0.85 | FCN1 | 0.06 | −0.26 | 0.73 | 0.04 | −0.44 |
| LINC00898 | −1.13 | 0.56 | 0.60 | 0.11 | −0.06 | DUXAP10 | −0.22 | −0.54 | 0.33 | −0.19 | 1.23 | MTUS2-AS1 | −0.10 | −0.56 | −0.63 | 0.36 | −0.85 |
| HOMER2 | 0.50 | 0.31 | 0.09 | −0.10 | −0.22 | LINC01804 | −0.76 | −0.81 | 0.40 | −0.05 | 0.37 | AC008567.1 | −0.13 | −0.27 | −0.65 | 1.07 | −0.32 |
| AP2A2 | −0.30 | 0.00 | 0.00 | 0.10 | 0.13 | PCBD2 | 0.09 | −0.19 | −0.15 | 0.11 | 0.19 | AP003080.1 | 0.09 | −0.43 | 0.85 | 0.10 | 0.71 |
| CORO2A | 0.45 | −0.03 | −0.38 | 0.16 | −0.09 | RPS17 | 0.84 | −0.89 | 0.67 | −1.24 | 0.09 | AC087286.2 | −0.03 | 0.23 | 0.61 | −0.16 | 0.16 |
| AC009229.2 | −0.97 | 1.13 | 1.01 | 0.50 | 0.54 | AC092920.1 | 0.47 | −0.53 | −0.20 | 0.02 | 0.56 | AL158047.1 | 0.57 | −0.98 | −0.11 | 0.44 | −0.51 |
| ADAT2 | 0.30 | −0.28 | −0.30 | 0.03 | 0.10 | AL117187.1 | −0.64 | −0.57 | −0.66 | 0.25 | −0.87 | SH2D3A | −0.03 | 0.01 | −0.66 | 0.35 | 0.15 |
| CCDC81 | −0.58 | 0.13 | 0.20 | −0.22 | −0.09 | RNU6-1050P | 0.86 | −1.44 | 0.00 | −0.84 | 0.50 | AC091153.3 | 0.26 | −0.54 | −0.42 | −0.32 | 0.92 |
| LRRC37B | −0.34 | 0.26 | 0.37 | 0.30 | 0.08 | AL133406.2 | 0.27 | −0.24 | 0.07 | −0.59 | −0.09 | PFKFB3 | −0.04 | −0.19 | −0.28 | −0.11 | 0.19 |
| LRRD1 | −1.32 | 1.58 | 0.41 | 0.27 | −0.19 | MT-ATP6 | −0.20 | 0.09 | 0.11 | −0.01 | −0.03 | AL359555.2 | 0.21 | −0.61 | −0.66 | 0.05 | −1.27 |
| IRGQ | 0.27 | −0.05 | −0.38 | −0.01 | −0.13 | AC119868.1 | −0.53 | −1.05 | 1.23 | 0.39 | 1.53 | MIR548AX | −0.25 | 0.70 | 0.54 | 0.18 | 0.96 |
| FTH1P16 | −0.54 | −0.09 | 0.50 | −0.02 | 0.21 | OR5AK3P | 0.99 | −1.09 | 0.85 | −0.13 | 0.43 | LYARP1 | −0.20 | −1.13 | −0.26 | −0.08 | 0.54 |
| RASA3 | −0.56 | −0.10 | 0.46 | −0.25 | 0.08 | BHLHE40-AS1 | −0.31 | −0.01 | 0.55 | −0.30 | −0.05 | EEF1B2P7 | 0.03 | 0.02 | 0.28 | 0.03 | −0.05 |
| AC022447.2 | −1.46 | 1.32 | 1.98 | 1.06 | 0.19 | AC067942.1 | −0.27 | −0.11 | 0.51 | −0.09 | 0.48 | STK33P1 | −0.59 | 0.34 | −0.14 | 0.24 | −1.01 |
| AMER2 | −1.42 | 0.73 | 0.95 | 0.21 | 0.55 | PHIP | 0.07 | 0.03 | 0.03 | 0.00 | −0.06 | AC093911.1 | 0.59 | −0.23 | −0.76 | 1.10 | 0.32 |
| PPP4R3B | 0.24 | −0.01 | −0.18 | 0.03 | −0.16 | MTND3P23 | 0.29 | 0.04 | 0.42 | 0.33 | 0.38 | RN7SL240P | −0.59 | −0.10 | −0.44 | −1.19 | −1.57 |
| STAG3L2 | −0.29 | 0.01 | 0.32 | −0.17 | 0.16 | AFG3L1P | −0.12 | −0.10 | −0.27 | 0.09 | 0.06 | AC009102.1 | −0.09 | −1.02 | −1.64 | −0.42 | 0.29 |
| CHRD | −0.69 | 0.40 | 1.15 | 0.23 | 0.33 | AC010761.1 | 0.21 | −0.53 | −0.71 | −0.01 | 0.34 | HIGD1AP16 | 0.06 | 0.55 | 0.35 | −0.33 | −0.11 |
| CBX5 | 0.35 | −0.21 | −0.09 | −0.12 | −0.06 | AC073263.2 | −0.63 | −2.16 | 0.67 | −0.83 | 1.84 | KL | −0.04 | 0.23 | −0.10 | 0.23 | 0.25 |
| CASC2 | −0.53 | −0.01 | 0.07 | 0.07 | 0.23 | CAVIN3 | −0.16 | 0.10 | 0.19 | −0.06 | −0.18 | RPH3A | 0.09 | −0.85 | −1.31 | −0.07 | −1.21 |
| AC145285.2 | −0.62 | 0.12 | 0.99 | 0.06 | 0.71 | AL513013.1 | 0.88 | −0.84 | −2.50 | 0.40 | −2.13 | AP001317.1 | 0.59 | −0.75 | 0.20 | 0.35 | 1.24 |
| AC091607.1 | −1.98 | 0.05 | 1.73 | 0.86 | 0.34 | SLC30A8 | 0.54 | −0.25 | −1.15 | 0.47 | −0.12 | AC034102.1 | 0.05 | 0.40 | −0.25 | 0.19 | −0.37 |
| AC022173.1 | 0.75 | −0.17 | −0.73 | −0.05 | −0.39 | LINC01028 | −1.34 | −0.09 | 1.55 | 1.82 | 0.81 | RPL31P49 | 0.11 | −0.37 | −0.70 | −0.47 | −0.99 |
| AC053527.1 | −0.67 | 0.41 | 0.67 | 0.39 | 0.15 | PSD2-AS1 | −0.75 | −1.33 | 1.01 | 0.29 | 0.69 | RNA5SP180 | 0.25 | −0.29 | 0.58 | −0.55 | −0.21 |
| EMC4 | 0.30 | −0.14 | −0.13 | −0.23 | −0.23 | CXorf67 | −0.80 | −0.18 | 0.59 | 0.65 | 0.49 | LINC01501 | −0.21 | −1.53 | 0.69 | −1.11 | 1.36 |
| AC026124.2 | 0.82 | −0.12 | −0.63 | 0.10 | −0.24 | SLC11A2 | −0.07 | 0.05 | 0.27 | 0.13 | 0.21 | BNIP3P19 | −0.59 | 0.97 | 1.10 | 0.29 | −0.71 |
| MRPL45 | 0.39 | −0.13 | −0.21 | −0.09 | −0.19 | LRRC34 | −0.25 | 0.06 | −0.26 | 0.25 | −0.01 | HMGA1P8 | −0.13 | 0.08 | 2.23 | −0.46 | 0.75 |
| G8228 | −1.19 | 0.97 | 1.03 | 0.69 | 0.05 | AC067805.1 | −0.98 | −0.37 | 0.14 | −0.22 | 1.24 | AC091691.1 | 0.46 | −0.70 | 0.04 | −1.80 | −1.46 |
| PLCL2 | −0.65 | 0.20 | 0.86 | −0.07 | 0.36 | G909 | −0.90 | 0.68 | 1.92 | −1.02 | −0.26 | AC107973.1 | −0.21 | 0.03 | −0.12 | 0.21 | 1.41 |
| SPDYE3 | −0.45 | 0.10 | 0.35 | 0.14 | 0.45 | SIK3-IT1 | 0.17 | −0.13 | −0.17 | 0.07 | −0.20 | CASC16 | 0.17 | −1.77 | −0.40 | 0.05 | 0.59 |
| SLC25A22 | 0.39 | −0.36 | −0.54 | −0.09 | −0.11 | AC007347.1 | 0.30 | 0.37 | 0.25 | −0.09 | −0.20 | AC104457.1 | 0.15 | −2.11 | 1.21 | −0.80 | 0.06 |
| BX248123.1 | −1.16 | 0.39 | 0.56 | −0.31 | −0.19 | AL139156.1 | 0.33 | 0.05 | 0.21 | −0.05 | −0.15 | LINC02045 | −0.20 | −0.04 | −0.28 | −0.42 | −0.90 |
| RAB35 | 0.29 | −0.10 | −0.54 | 0.07 | −0.28 | ADTRP | −0.24 | 0.07 | 0.34 | −0.01 | 0.38 | AC018630.1 | −0.06 | 0.20 | 0.75 | 0.19 | 0.00 |
| RN7SL381P | −0.58 | 0.61 | 0.08 | 0.46 | −0.46 | AMZ2P2 | 0.48 | −0.70 | 0.83 | −0.73 | 1.04 | AL121892.1 | −0.18 | 0.21 | −0.44 | −0.31 | −2.45 |
| RNA5SP442 | −1.54 | 0.72 | −0.62 | 1.13 | −1.17 | AC048344.4 | 0.42 | 0.04 | −0.44 | −0.24 | −1.12 | ARHGAP26-IT1 | 0.07 | 0.11 | 0.27 | 0.43 | −0.13 |
| PRB2 | −0.87 | 0.55 | −0.06 | 0.24 | −0.54 | PCDH12 | −0.17 | 0.35 | 0.26 | 0.05 | −0.20 | AC010374.2 | −0.32 | −0.14 | −0.17 | 0.46 | 0.05 |
| SLCO5A1 | −1.15 | 0.25 | 0.25 | 0.45 | 0.26 | RNU6-404P | 0.76 | 0.74 | −0.02 | 0.19 | −0.53 | AC013472.3 | −0.06 | 0.29 | 1.12 | 0.05 | 0.44 |
| RPL19 | 0.39 | −0.07 | −0.12 | −0.19 | −0.27 | SNX7 | 0.15 | −0.11 | 0.10 | −0.25 | −0.24 | AL096803.3 | 0.17 | −0.26 | 0.57 | 0.45 | 1.68 |
| RN7SL839P | −1.23 | −0.44 | 0.38 | 0.10 | 0.57 | HEY1 | 0.23 | −0.10 | 0.32 | −0.07 | −0.10 | AC073626.2 | −0.09 | 0.37 | 0.01 | −0.20 | 0.46 |
| AL121894.1 | −1.86 | 0.40 | 1.39 | 1.29 | 0.57 | MIR3200 | −0.65 | 0.15 | −0.12 | −0.05 | −0.23 | RN7SKP126 | −0.28 | 0.60 | −0.77 | 2.93 | −0.91 |
| RNU1-88P | −1.51 | 0.15 | −0.23 | 0.52 | −1.03 | FNDC7 | −0.51 | −0.12 | −1.28 | 0.48 | −0.80 | AC100823.2 | 0.28 | −0.57 | −0.65 | −0.16 | −1.32 |
| ACVR1 | 0.27 | −0.04 | −0.25 | 0.01 | −0.19 | AC005488.1 | 0.89 | −1.54 | −1.39 | −0.55 | 0.13 | NANOGNBP2 | 0.16 | −0.67 | 1.76 | 0.52 | 0.40 |
| MISP | 1.14 | −0.16 | −1.69 | 0.33 | −0.84 | G17634 | −0.53 | 0.61 | 0.62 | −0.35 | 0.53 | MRPL50P1 | 0.27 | 1.96 | −0.65 | 1.21 | −1.40 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| CTBP2P8 | −0.68 | 0.01 | 0.41 | 0.40 | 0.29 | ABCB1 | 0.22 | 0.22 | 0.54 | 0.13 | 0.00 | AC007537.1 | 0.04 | −0.37 | 0.06 | −0.18 | 0.49 |
| E2F3-IT1 | 1.00 | −0.84 | −0.74 | −0.42 | 0.43 | AL590682.1 | 0.67 | 0.10 | −0.16 | −0.47 | −0.12 | C1DP1 | 0.30 | −0.81 | −0.12 | −0.02 | 0.30 |
| RNA5SP161 | −1.20 | 0.20 | −0.65 | 1.44 | −0.73 | COL4A6 | −0.17 | 0.08 | −0.85 | 0.26 | −0.19 | SLC17A1 | 0.14 | 0.79 | −0.89 | 0.94 | −0.94 |
| ANKRD16 | −0.39 | 0.29 | 0.21 | 0.11 | −0.03 | G5174 | −1.10 | −0.64 | −0.82 | 0.71 | −0.48 | CPEB2-DT | −0.03 | 0.19 | −0.34 | 0.49 | −0.36 |
| AL353593.3 | −0.75 | 0.80 | 1.11 | 0.35 | −0.14 | PODNL1 | −0.22 | 0.39 | 0.45 | −0.33 | −0.32 | LPCAT2BP | −0.31 | −0.11 | −0.88 | 0.22 | −0.98 |
| NUDT7 | −0.55 | 0.32 | 0.81 | 0.27 | 0.55 | AC004076.1 | 0.80 | −0.74 | 0.59 | −0.83 | 0.22 | AL365181.1 | 0.12 | −0.61 | −1.74 | 1.10 | 0.83 |
| TEL1-TNFRSF6 | −0.64 | 0.31 | 0.09 | 0.50 | 0.31 | CDH6 | −0.23 | 0.28 | 0.42 | 0.10 | −0.50 | AC087190.2 | −0.15 | 1.01 | −2.36 | 0.16 | −1.67 |
| C6orf132 | 0.45 | 0.08 | −0.41 | 0.10 | −0.31 | CHCHD3P2 | −0.78 | 1.02 | 1.33 | 0.54 | −0.58 | AL353795.2 | −0.08 | −0.50 | 0.26 | 0.20 | 0.77 |
| MRPS5 | 0.29 | −0.32 | −0.32 | −0.21 | 0.05 | KLHL9 | 0.09 | −0.06 | 0.04 | −0.09 | −0.07 | RPL30P6 | −0.59 | 1.55 | 0.47 | 0.60 | −0.85 |
| CPSF4L | −1.00 | 0.30 | 0.19 | 0.19 | 0.42 | ETV7 | 0.26 | −0.53 | −0.13 | −0.55 | 0.02 | LINC02476 | 0.17 | −0.84 | −1.54 | 0.84 | −1.66 |
| STAG3L1 | −0.53 | −0.02 | 0.42 | −0.03 | 0.47 | CHRNA4 | −0.61 | −1.05 | −0.86 | 0.34 | 0.21 | LGALS16 | 0.59 | −1.40 | 0.01 | 1.26 | 1.28 |
| PLEKHM1P1 | −0.38 | 0.21 | 0.15 | 0.07 | 0.06 | LINC01151 | 0.97 | 0.49 | 0.77 | −0.44 | −0.20 | CCDC102B | 0.04 | −0.23 | 0.75 | −0.57 | −0.21 |
| AL590666.3 | 1.12 | −0.27 | −0.20 | −0.14 | −0.01 | AC015849.4 | 0.27 | −0.03 | 0.22 | 0.16 | 0.26 | RN7SL192P | −0.06 | −0.10 | −0.25 | 0.18 | −0.14 |
| FAR2 | −0.52 | 0.21 | 0.39 | 0.39 | 0.81 | RPS10P5 | 0.44 | −1.04 | −0.48 | 0.77 | 1.31 | IGHV3-30 | 0.57 | 1.37 | 1.68 | 0.41 | 1.34 |
| IDSP1 | −1.25 | 0.47 | 1.05 | 0.69 | 1.24 | ATG9B | −0.26 | 0.21 | 0.53 | 0.36 | 0.46 | CYCSP41 | 0.59 | −1.26 | 0.58 | −0.60 | 1.16 |
| AC004156.1 | −0.96 | 0.18 | 0.62 | −0.07 | 0.21 | AC092701.1 | 1.02 | −0.99 | −1.81 | 0.53 | 1.91 | AL353732.1 | 0.34 | −1.12 | −0.89 | 0.76 | −1.04 |
| NBDY | 0.41 | −0.04 | −0.07 | −0.14 | −0.40 | AC108475.1 | −0.48 | 0.54 | 0.87 | 0.59 | −0.18 | DUXA | −0.20 | 1.09 | −2.19 | 0.34 | −2.23 |
| AC011773.4 | −1.47 | −0.02 | 1.37 | 1.19 | 1.20 | SERPINA3 | −0.58 | −0.73 | −1.31 | −0.48 | −1.23 | LINC01846 | 0.36 | 0.16 | −0.47 | 0.49 | −1.94 |
| LRRC40 | 0.24 | −0.09 | −0.29 | −0.05 | −0.26 | MTCYBP10 | 1.62 | −2.13 | −2.29 | −1.27 | −0.62 | AL136987.1 | 0.13 | 0.04 | −1.71 | 1.28 | 0.31 |
| CDK12 | 0.18 | −0.08 | −0.25 | −0.03 | −0.09 | AC022790.1 | −0.88 | 0.47 | 0.13 | 1.03 | 0.69 | SALL4P6 | 0.31 | −0.23 | 0.33 | −0.76 | 2.00 |
| APPL1 | 0.30 | 0.01 | 0.00 | 0.03 | −0.20 | HSPB11 | 0.08 | −0.14 | 0.03 | −0.12 | 0.07 | SLFN11 | 0.04 | −0.18 | 0.71 | −0.34 | 0.08 |
| FCHO2 | 0.29 | 0.00 | −0.13 | −0.04 | −0.25 | RNU6ATAC18P | −0.54 | 1.44 | 0.99 | 0.24 | −0.02 | AP001059.3 | −0.08 | −0.01 | 0.60 | −0.16 | −0.02 |
| MOB2 | −0.32 | 0.34 | 0.21 | 0.28 | 0.09 | KRTAP10-13P | −1.06 | −0.18 | 0.51 | 1.07 | −0.20 | AL035404.1 | 0.28 | 0.00 | −1.55 | 0.34 | −3.37 |
| FAM89B | 0.88 | −0.35 | −1.12 | 0.23 | −1.04 | MYO16 | −0.34 | −0.13 | 0.13 | −0.28 | −0.02 | AC016910.1 | −0.06 | 0.48 | 0.73 | 0.11 | −0.40 |
| IGF2 | −0.87 | 1.03 | 1.18 | 0.26 | −0.51 | BAHD1 | 0.11 | 0.14 | 0.00 | 0.05 | −0.06 | AL441989.1 | −0.22 | 0.29 | −0.64 | 1.90 | −0.04 |
| MGST3 | −0.34 | 0.33 | 0.20 | 0.22 | −0.06 | AC004585.2 | 0.71 | −1.53 | −1.32 | −0.21 | −1.01 | HMGN1P33 | 0.38 | 0.07 | −2.85 | 0.41 | −1.26 |
| GDPD5 | −0.64 | 0.10 | 0.41 | 0.06 | 0.22 | PDCD5P1 | 1.28 | −0.33 | 0.45 | −0.86 | −1.07 | DHRS9 | −0.05 | −0.39 | −0.66 | 0.16 | 0.14 |
| SIM2 | −0.63 | −0.19 | 0.53 | 0.31 | 0.42 | AFP | 0.78 | −0.13 | −0.04 | 0.16 | −0.36 | IGLVIVOR22-2 | −0.19 | −0.31 | 0.46 | −0.33 | 2.95 |
| C8orf37 | −0.40 | 0.00 | 0.31 | 0.07 | 0.02 | RPL30P11 | −0.75 | −0.23 | 0.41 | −0.36 | −0.93 | GSTO3P | −0.26 | −0.20 | −0.83 | 0.72 | −1.41 |
| OIP5-AS1 | −0.39 | −0.01 | 0.27 | 0.14 | 0.41 | SNX5P1 | −0.59 | 0.11 | −0.96 | 0.35 | 0.47 | AC011825.1 | −0.09 | −0.19 | −0.67 | −0.51 | −0.87 |
| AL590139.1 | 0.90 | −0.14 | −0.95 | 0.25 | −0.12 | KCNE1 | −0.21 | −0.32 | −0.25 | −0.38 | −0.25 | AC092747.3 | −0.19 | −1.48 | 0.10 | −1.48 | −0.05 |
| AC104118.1 | 0.35 | −0.02 | −0.18 | −0.28 | −0.37 | RPS29P16 | 0.48 | 0.16 | 0.97 | 0.07 | 0.96 | PTGS1 | −0.04 | 0.33 | 0.70 | 0.32 | 0.14 |
| OR7E106P | 1.97 | −0.99 | −1.20 | 0.67 | 1.34 | C1QL3 | −0.20 | 0.15 | −0.06 | 0.16 | −0.14 | PIBF1 | −0.01 | 0.01 | 0.19 | −0.19 | −0.01 |
| SPSB2 | 0.62 | −0.35 | −0.53 | −0.21 | 0.00 | LINC02253 | 0.75 | −1.63 | −1.58 | 1.27 | 1.04 | OCSTAMP | −0.17 | 0.84 | −0.31 | 1.23 | −0.55 |
| SBF1 | −0.37 | 0.24 | −0.04 | 0.27 | 0.04 | AC012213.3 | 0.47 | 0.71 | 0.54 | 0.04 | −0.59 | MIR604 | −0.05 | 0.35 | −0.98 | 0.45 | −0.67 |
| G10546 | −0.82 | 0.18 | 0.18 | −0.24 | −0.34 | AC090186.1 | −0.35 | 0.53 | 0.26 | 0.13 | 0.16 | RPL17P44 | −0.18 | −0.48 | −1.75 | 1.69 | 0.13 |
| DCLRE1A | 0.42 | −0.26 | −0.23 | −0.08 | 0.07 | GINM1 | 0.14 | 0.13 | 0.21 | 0.06 | −0.15 | AC004987.4 | 0.26 | 0.18 | 0.13 | −0.49 | −0.77 |
| CASP9 | −0.49 | 0.28 | 0.57 | −0.10 | −0.07 | MIR4512 | −0.72 | 1.23 | −0.28 | −0.23 | −0.66 | HMGB1P50 | −0.18 | −1.49 | −0.71 | −1.64 | −0.77 |
| CYCSP34 | −0.91 | 1.03 | 1.19 | 0.86 | 0.20 | AL356215.1 | 0.34 | 0.01 | −0.34 | −0.20 | −0.56 | RNA5SP24 | −0.58 | 0.87 | 0.08 | 1.18 | −1.81 |
| SIAH1 | 0.27 | 0.08 | −0.43 | 0.14 | −0.50 | LYRM4-AS1 | 0.19 | −0.20 | −0.28 | 0.17 | 0.10 | KRT18P24 | −0.13 | −1.24 | −1.54 | 0.52 | −0.11 |
| AC012485.2 | −1.92 | 1.10 | 0.66 | 1.99 | 0.47 | C1orf134 | −0.42 | −0.06 | 0.21 | −0.49 | 0.81 | AL391839.2 | −0.12 | 1.03 | 1.56 | −0.14 | 0.15 |
| PSMA6P1 | 0.80 | −0.11 | −0.76 | 0.04 | −0.67 | RN7SL300P | 0.45 | −0.74 | −1.97 | 0.05 | −0.94 | RNU4-72P | 0.14 | 1.24 | 1.76 | −0.05 | −0.37 |
| AC010325.2 | −1.33 | 0.43 | 0.14 | 0.15 | −1.30 | RETREG3 | 0.12 | 0.09 | 0.10 | 0.04 | −0.08 | KERA | 0.15 | 0.78 | −0.23 | 1.33 | −1.01 |
| AC008663.1 | 1.79 | −1.37 | −1.49 | −1.24 | −1.61 | MTAPP2 | 0.27 | −0.37 | −0.63 | 0.15 | −0.41 | C2CD4B | −0.07 | 0.03 | −0.02 | 0.09 | −0.36 |
| ASGR1 | −1.31 | 0.11 | −0.42 | 0.86 | −0.15 | MIR3145 | 0.66 | −0.42 | −0.12 | 0.13 | −0.24 | AC008554.1 | −0.27 | −0.27 | −0.81 | 0.37 | 0.08 |
| BCL9P1 | −1.39 | 1.13 | 0.89 | 1.49 | 1.12 | MTCO1P12 | −0.16 | −0.06 | 0.19 | 0.84 | 0.52 | PTGES3P4 | 0.25 | −0.29 | −1.41 | 0.43 | −0.79 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC019064.1 | −1.19 | 1.12 | 1.77 | 0.54 | 0.42 | NPM1P48 | 0.93 | −0.05 | −2.16 | 0.80 | −1.23 | SLC32A1 | 0.24 | −1.06 | −1.29 | 0.27 | 0.03 |
| PDLIM2 | −0.52 | 0.55 | 0.29 | 0.44 | −0.02 | AL139260.1 | −0.19 | 0.55 | 0.12 | 0.36 | −0.26 | SLC38A8 | −0.19 | −0.68 | 0.85 | −1.21 | 1.30 |
| MRPL40 | 0.41 | −0.07 | −0.29 | −0.09 | −0.50 | AC009967.1 | −0.90 | −0.19 | −0.94 | 0.05 | −0.20 | RP11-498D10.5 | 0.03 | −0.12 | −0.22 | 0.12 | 0.07 |
| DIS3L2 | −0.31 | 0.12 | 0.05 | 0.06 | 0.09 | G41661 | −0.29 | 0.84 | 0.44 | 0.22 | −0.02 | AC022432.1 | −0.20 | 0.70 | −0.03 | −0.49 | −2.00 |
| LINC01341 | −0.97 | 0.76 | 0.69 | 0.21 | −0.61 | EEF1A1P17 | 0.86 | −2.14 | −1.25 | 0.72 | 0.66 | AC097484.2 | 0.20 | −0.52 | 0.02 | 0.37 | 1.73 |
| RPL37A | 0.41 | −0.06 | −0.08 | −0.14 | −0.35 | AL031864.2 | 0.65 | −1.34 | 0.02 | −0.34 | −0.92 | CTSLP3 | −0.19 | −0.93 | −0.23 | −0.14 | 1.71 |
| IFT20 | −0.32 | 0.21 | 0.33 | −0.11 | −0.06 | AL359962.1 | −0.43 | 0.10 | 0.66 | 0.00 | 0.08 | AC009090.5 | −0.08 | −1.02 | 0.55 | −0.37 | 1.32 |
| AC007785.1 | −0.81 | 0.63 | 1.08 | 0.44 | 0.49 | MIR1183 | −0.53 | 0.65 | 0.50 | 0.16 | 0.64 | RN7SKP112 | −0.07 | −0.02 | −0.06 | −0.24 | −0.74 |
| AC011450.1 | −0.89 | 0.17 | 0.81 | 0.13 | 0.21 | AL353771.1 | 0.35 | −0.42 | −0.12 | 0.25 | 0.48 | AC245100.8 | −0.05 | −0.35 | −0.37 | 0.19 | 0.89 |
| AC073367.1 | 0.54 | −0.54 | 0.13 | −0.24 | 0.25 | AC244093.5 | 0.22 | −0.12 | −0.14 | −0.35 | −0.18 | GPR78 | 0.06 | 0.07 | 0.07 | −0.81 | −0.73 |
| DHRS12 | −0.33 | 0.38 | 0.02 | 0.13 | −0.19 | AP001486.2 | 0.12 | 0.18 | −0.15 | 0.19 | −0.17 | AC005156.1 | 0.06 | 0.40 | 0.01 | 0.35 | −0.05 |
| RPS29P14 | 1.48 | −0.46 | −0.37 | −0.16 | 0.38 | AL355607.1 | 0.90 | 0.65 | 1.10 | −1.00 | −0.27 | RN7SKP39 | −0.52 | −0.75 | NA | −1.16 | −2.00 |
| AC009560.1 | −1.20 | 0.36 | 1.02 | 0.40 | 0.38 | AC066692.1 | 0.36 | −0.08 | 0.52 | −0.29 | −0.19 | AL513323.1 | 0.36 | −0.08 | −1.13 | −0.55 | −1.83 |
| DCDC2B | −0.47 | 0.20 | 0.70 | −0.04 | 0.59 | AP001033.2 | 0.22 | 0.06 | 0.25 | 0.13 | 0.05 | AL163642.2 | 0.58 | −0.69 | 0.32 | −1.03 | 1.68 |
| AC078819.1 | 1.18 | −0.37 | −1.12 | −0.48 | −0.81 | AC010287.1 | 0.38 | −0.54 | −0.07 | −0.14 | 0.51 | AC110615.1 | −0.10 | −1.52 | −0.17 | −1.07 | 0.42 |
| AC004918.1 | −0.82 | 0.23 | 0.38 | 0.50 | 0.45 | ELOA2 | 0.35 | −0.22 | 0.09 | −0.64 | 0.49 | AC019183.1 | 0.23 | −0.50 | −2.50 | 2.09 | −0.20 |
| OCIAD1 | 0.26 | −0.10 | −0.06 | −0.08 | −0.08 | AC024580.1 | −0.50 | 0.71 | 0.75 | 0.56 | 0.07 | DFFBP1 | 0.08 | 1.00 | −0.37 | 1.17 | −0.76 |
| HS3ST5 | −1.06 | 0.54 | −0.22 | 0.42 | 0.24 | AC091117.2 | −0.36 | −0.35 | −0.43 | −0.01 | −0.24 | MOB1AP1 | −0.58 | −0.46 | −0.82 | 0.83 | 0.23 |
| HTR3E | −1.42 | 0.50 | −0.40 | 0.92 | 0.83 | AP002884.2 | −0.37 | −0.17 | −0.28 | 0.17 | −0.27 | AL033528.1 | −0.09 | −0.48 | −0.41 | 0.19 | 0.50 |
| FADS3 | −0.73 | 0.11 | 0.38 | −0.06 | −0.02 | AC008147.1 | 0.20 | −0.31 | −0.51 | −0.19 | 0.29 | NAF1 | 0.02 | 0.01 | 0.00 | 0.01 | −0.05 |
| RHOT2 | −0.49 | 0.05 | −0.09 | 0.26 | 0.34 | AC009403.2 | 0.37 | −0.42 | −0.57 | −0.07 | 0.24 | AC009500.1 | 0.35 | 0.18 | 0.21 | 0.14 | −0.36 |
| LMLN | −0.30 | 0.06 | 0.17 | 0.10 | 0.27 | AC108449.1 | 0.45 | −0.24 | −0.14 | −0.27 | −0.06 | CCDC96 | 0.03 | 0.07 | −0.09 | −0.02 | −0.04 |
| AC025166.1 | −1.14 | −0.11 | 1.30 | −0.03 | 0.50 | AL049552.1 | −0.22 | 0.33 | 0.51 | 0.00 | −0.15 | AC106874.1 | 0.58 | 1.07 | −0.47 | 1.01 | −1.19 |
| AC007342.9 | 1.71 | −0.69 | −1.23 | 0.40 | −0.07 | AL390866.1 | 0.46 | −0.61 | −0.70 | 0.41 | 0.08 | FCRL2 | 0.11 | 1.02 | −1.76 | 0.37 | −1.78 |
| RN7SL276P | −1.23 | 0.06 | 0.58 | 0.58 | 0.76 | G5796 | 0.66 | −2.10 | −1.66 | −0.33 | 0.16 | B3GNT2P1 | −0.35 | −0.30 | 0.06 | −0.91 | −1.02 |
| POLR3DP1 | −0.70 | 0.32 | −0.12 | 0.33 | 0.21 | OBSCN-AS1 | −0.31 | 0.46 | −0.03 | 0.38 | −0.02 | FXYD6P3 | −0.58 | −0.16 | 0.80 | 0.62 | 1.46 |
| EYA2 | −0.62 | 0.46 | 0.96 | −0.01 | 0.03 | AL359745.1 | −0.90 | 0.35 | −1.47 | 1.78 | −1.94 | LINC02324 | 0.16 | −2.24 | 1.24 | 0.49 | 1.72 |
| AC007787.1 | −0.97 | 0.55 | 1.14 | 0.75 | 0.57 | LRRC10 | −0.75 | 0.05 | −0.49 | −0.73 | −0.41 | RPS12P20 | 0.05 | 0.12 | −0.34 | −0.22 | −0.45 |
| AP000925.1 | −0.65 | 0.16 | 0.62 | −0.06 | 0.10 | OR6C3 | −1.10 | −0.36 | −0.58 | −1.04 | −0.90 | PIK3R2 | 0.11 | 0.77 | −1.88 | 0.24 | −0.52 |
| MKNK1-AS1 | 0.50 | −0.07 | −0.82 | −0.04 | −0.55 | EIF4EBP2 | 0.13 | 0.06 | −0.09 | 0.00 | −0.20 | SELENOTP1 | 0.18 | 0.15 | −0.92 | 0.94 | −0.71 |
| OR52H2P | −1.28 | 1.27 | 1.29 | 0.25 | 0.04 | AL357115.1 | 0.65 | 1.22 | −0.05 | −0.25 | −0.64 | RNU1-131P | 0.41 | −0.55 | −1.45 | −0.91 | −1.73 |
| SEPHS1P1 | −1.31 | 1.15 | 2.66 | 0.21 | 0.90 | ROBO2 | −0.22 | 0.50 | 0.53 | 0.41 | −0.01 | NAPGP1 | −0.16 | 0.03 | −0.39 | 1.49 | 0.49 |
| RAB30-AS1 | −0.36 | −0.09 | 0.79 | −0.13 | 0.55 | AL021707.3 | 0.34 | −0.23 | −0.43 | 0.34 | −0.12 | RNA5SP232 | 0.35 | 0.77 | −0.88 | 1.87 | −2.93 |
| AL133353.2 | 1.73 | −1.22 | −0.83 | −0.38 | −0.26 | LINC01580 | 1.17 | −0.65 | −1.94 | 0.64 | −0.69 | AC016632.1 | 0.58 | −0.62 | −1.75 | 0.80 | 0.76 |
| SNORA66 | −0.90 | 0.34 | 0.05 | 0.64 | −0.18 | RN7SL743P | −0.41 | 0.79 | −0.31 | 0.00 | −1.50 | PABPC1P9 | −0.26 | −0.46 | −0.70 | −0.45 | −0.36 |
| MRGPRF-AS1 | −1.04 | −0.52 | 1.06 | −0.85 | −0.55 | LINC02480 | 0.95 | −0.05 | −1.60 | 0.47 | −0.37 | AL355472.1 | −0.04 | −0.28 | 0.77 | 0.35 | 0.67 |
| LINC02080 | −0.99 | −0.04 | 0.85 | −0.13 | −0.29 | NELFCD | 0.08 | −0.02 | −0.21 | 0.10 | −0.08 | RN7SKP50 | −0.04 | −0.49 | 0.79 | −0.54 | 0.66 |
| NIPA1 | 0.44 | −0.01 | −0.43 | −0.13 | −0.24 | LINC00426 | −0.21 | −0.11 | 0.27 | −0.19 | 0.33 | AL512590.1 | 0.35 | −0.47 | −1.45 | 0.41 | −0.81 |
| NTNG1 | −0.86 | 0.43 | 0.92 | 0.46 | 0.71 | HTR7P1 | −0.14 | 0.35 | 0.14 | 0.50 | 0.13 | HMMR-AS1 | 0.19 | 0.01 | −1.95 | 0.27 | −1.57 |
| RELA | 0.26 | −0.08 | −0.43 | 0.03 | −0.29 | PP7080 | 0.39 | 0.10 | 0.02 | 0.55 | 0.03 | L29074.1 | −0.14 | 0.79 | 1.03 | 0.86 | 1.39 |
| AC008014.1 | −0.47 | 0.24 | 0.54 | 0.53 | 0.32 | AC011447.2 | −1.51 | −0.34 | 0.24 | −0.72 | 0.38 | RP11-395B7.2 | 0.13 | −0.49 | −0.39 | 1.16 | 0.02 |
| LINC02102 | −0.67 | 0.09 | 0.01 | 0.02 | −0.08 | RNUSE-4P | 0.38 | −1.18 | −0.39 | −0.47 | 0.42 | LINC02182 | −0.15 | −2.21 | 1.02 | 0.50 | 2.18 |
| AP001020.2 | −0.61 | −0.04 | 0.23 | 0.21 | 0.35 | C12orf71 | 0.33 | −0.16 | −0.81 | 0.15 | −0.58 | AC068724.1 | 0.58 | 0.54 | 0.45 | 0.84 | −1.07 |
| LINC01106 | 0.79 | −0.33 | −0.91 | −0.22 | −0.20 | SMIM1 | −0.47 | −0.54 | 0.28 | 0.01 | 0.13 | OR52K1 | −0.09 | −0.98 | −0.39 | 0.06 | 0.56 |
| AL353763.1 | −0.98 | 0.12 | 1.31 | −0.07 | 0.32 | LINC01978 | −0.61 | −0.53 | 1.06 | 0.66 | 0.45 | AC090386.1 | −0.20 | −2.20 | −1.64 | −0.01 | 0.98 |
| RN7SL64P | −1.14 | 0.01 | 1.24 | −0.59 | 0.93 | AC025278.1 | −0.81 | −1.55 | −0.50 | −0.60 | −0.20 | SNAP25-AS1 | −0.08 | 0.18 | −0.57 | 0.42 | −0.24 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| RPL12P7 | −1.44 | 0.29 | 0.49 | 1.22 | 0.23 | MVK | 0.15 | 0.00 | 0.00 | 0.34 | 0.09 | SULT1C2P2 | −0.27 | −1.04 | −0.34 | −0.79 | −0.52 |
| QRFP | −0.80 | 0.24 | 0.35 | 0.33 | 0.34 | AC015871.3 | −0.16 | −0.05 | 0.50 | 0.06 | 0.52 | NDE1P2 | 0.18 | 0.63 | −0.68 | 0.44 | −0.65 |
| PABPC5 | −0.96 | 0.36 | 0.95 | −0.13 | −0.37 | LINC00652 | −0.39 | −0.02 | 0.56 | 0.24 | 0.47 | AL512310.10 | −0.41 | 0.14 | 0.24 | −0.56 | −0.83 |
| CLMAT3 | −0.58 | 0.53 | 0.51 | −0.18 | −0.27 | RIN1 | 0.19 | −0.26 | −0.63 | 0.33 | 0.22 | AC121758.1 | 0.09 | 0.62 | 0.62 | −0.01 | −1.04 |
| POMZP3 | −0.39 | −0.06 | 0.22 | −0.11 | 0.16 | RP11-459016.1 | −1.10 | 2.24 | 2.07 | 1.90 | −0.16 | ANOS1 | −0.03 | 0.26 | −0.74 | 0.29 | −0.55 |
| FAM151B | 0.56 | −0.34 | −0.51 | 0.06 | −0.28 | PHF21B | −0.47 | −0.33 | −1.38 | 0.48 | −1.54 | AL138957.1 | −0.57 | 1.22 | −1.61 | 2.11 | −1.67 |
| AC009268.1 | 1.24 | −0.53 | −0.32 | −0.13 | 0.06 | COL4A2-AS1 | 0.44 | −0.42 | −1.99 | −0.26 | −1.43 | AL589987.2 | 0.54 | −1.96 | −1.39 | −0.29 | 0.23 |
| AL136295.5 | 0.68 | −0.39 | −0.73 | 0.14 | −0.07 | ANTXR2 | −0.20 | −0.03 | −0.02 | −0.34 | −0.18 | RP9 | −0.02 | −0.01 | 0.26 | −0.15 | 0.14 |
| COL11A1 | −1.18 | 1.23 | 1.85 | −1.72 | −0.78 | CCIN | −0.47 | 0.37 | −1.17 | −0.27 | −1.56 | ISPD | −0.02 | 0.22 | 0.39 | 0.22 | 0.19 |
| AL034399.2 | 0.63 | −0.21 | −0.61 | −0.03 | −0.33 | AL390856.1 | 0.68 | −0.85 | −1.03 | 0.25 | 0.19 | AC093730.1 | 0.55 | −1.05 | 0.05 | −0.02 | −0.45 |
| KCTD9 | 0.31 | −0.04 | −0.32 | −0.09 | −0.25 | AC018653.4 | 0.43 | −0.70 | −1.05 | −0.53 | −0.34 | AL158062.1 | −0.06 | 0.04 | −1.02 | −0.14 | −0.60 |
| AC104771.1 | −1.44 | 1.09 | 0.26 | 0.57 | −0.06 | EPB41L4A-DT | 0.94 | −0.40 | 1.04 | 0.33 | −0.62 | PRRT4 | 0.05 | −0.60 | −0.82 | 0.47 | 0.98 |
| RPL13A | 0.41 | 0.02 | −0.13 | −0.08 | −0.42 | LINC01446 | −0.58 | 0.10 | −0.88 | 0.78 | 0.92 | AC007450.1 | 0.17 | −0.19 | −0.15 | 0.04 | −0.94 |
| HIP1R | −0.50 | 0.43 | −0.13 | 0.43 | −0.03 | AC021127.1 | −0.67 | −0.41 | 1.00 | −1.02 | 0.29 | AC091046.1 | 0.09 | 0.64 | 0.15 | −0.42 | −1.56 |
| HLA-DRA | 0.66 | −0.60 | −0.04 | −0.35 | 0.02 | AC004870.2 | 1.01 | −1.81 | 0.15 | −0.49 | 0.80 | AC012464.3 | 0.06 | −0.31 | −0.29 | 0.34 | 0.08 |
| RNA5SP243 | −1.63 | 0.78 | −0.33 | 1.19 | −0.64 | RCE1 | 0.14 | 0.17 | −0.48 | 0.34 | −0.16 | GLB1L | −0.02 | −0.02 | −0.06 | 0.04 | −0.08 |
| SGCZ | −1.31 | 0.88 | 1.86 | −0.09 | 0.18 | MIR4714 | 0.39 | −0.26 | −0.47 | −0.20 | −0.01 | RCN1P1 | −0.57 | −0.14 | 1.04 | −0.25 | 1.56 |
| G8119 | −2.04 | 0.16 | 2.72 | −0.82 | 0.16 | ABHD17AP3 | 0.44 | −1.19 | −1.11 | −0.37 | 0.05 | RN7SL791P | −0.27 | −0.77 | 0.16 | −0.29 | 0.18 |
| RNF185 | 0.39 | 0.11 | −0.19 | −0.09 | −0.34 | AP000944.1 | −1.00 | 0.20 | 1.53 | −0.03 | 1.60 | AC093847.1 | −0.15 | −1.23 | −3.56 | 1.99 | 0.34 |
| PCOTH | −1.11 | 0.42 | 1.27 | 0.12 | 0.36 | GRID1-AS1 | −0.57 | −0.37 | 0.34 | 0.15 | −0.36 | AC073869.4 | 0.57 | −1.56 | −1.23 | −1.25 | NA |
| RNF141 | 0.48 | 0.00 | −0.29 | 0.05 | −0.28 | AL355338.1 | 0.21 | −0.05 | 0.70 | −0.45 | 0.32 | AC015813.7 | −0.12 | 0.33 | 1.29 | −0.56 | 0.33 |
| CD300H | 1.84 | −1.59 | −1.17 | −1.82 | −0.58 | RNU1-19P | −0.43 | −1.21 | 0.11 | 0.22 | 1.30 | PPIAP70 | 0.07 | −0.76 | 0.41 | −0.58 | −0.05 |
| COL17A1 | 0.64 | −0.23 | −1.04 | 0.13 | −0.41 | AC116456.2 | −0.75 | 0.53 | 0.99 | −0.37 | −0.25 | LINC02213 | 0.25 | −2.61 | 0.77 | −2.20 | 0.21 |
| AC055854.1 | −1.18 | 1.42 | 0.95 | 1.84 | 0.57 | AC120114.3 | −0.17 | −0.32 | 0.10 | 0.02 | 0.56 | G16043 | −0.11 | 0.33 | 0.18 | 0.63 | −0.18 |
| CNTNAP2 | 1.06 | −0.45 | −1.29 | −1.29 | −1.11 | AC024451.3 | 0.40 | −0.35 | 0.52 | −0.12 | 0.92 | RPL21P107 | 0.57 | −0.68 | −1.45 | 2.32 | 0.77 |
| AC079760.2 | −0.91 | 0.68 | 0.02 | 0.03 | 0.31 | HNRNPA3P9 | 0.25 | −0.19 | −0.13 | 0.05 | 0.11 | LINC01568 | −0.09 | −0.26 | −0.66 | 1.08 | −0.09 |
| EPHX4 | −0.88 | 0.18 | 0.91 | −0.37 | −0.06 | CD81 | −0.12 | 0.13 | 0.02 | 0.04 | −0.25 | GAPDHP22 | −0.14 | −1.67 | 2.41 | −0.45 | 1.58 |
| GPAT3 | 0.61 | −0.36 | −0.31 | −0.11 | −0.27 | AL391097.1 | 0.23 | −0.01 | −0.27 | −0.10 | −0.61 | AC129807.1 | 0.24 | −0.41 | −0.28 | 0.82 | −0.15 |
| PIGL | −0.35 | 0.24 | 0.36 | 0.11 | 0.17 | MCRIP1 | −0.17 | −0.08 | −0.14 | −0.04 | −0.02 | NPM1P51 | −0.14 | −0.88 | −1.26 | 0.35 | 0.21 |
| AC007495.1 | −1.09 | 0.05 | 0.17 | 0.41 | 0.81 | HGH1 | 0.25 | −0.24 | −0.03 | 0.14 | 0.23 | MTND5P9 | 0.14 | −2.39 | −1.18 | −0.34 | −0.08 |
| SH2D4A | 0.35 | −0.11 | −0.34 | −0.02 | −0.10 | AL390838.1 | −0.63 | 0.61 | −0.34 | 0.44 | −0.42 | HIGD1AP12 | 0.29 | −0.52 | −1.26 | 0.25 | −0.20 |
| AL591516.2 | −1.18 | 0.06 | 1.29 | −0.09 | 0.61 | CNTNAP3P5 | −1.26 | 1.00 | −0.32 | 0.23 | −0.63 | AL591034.1 | −0.26 | −0.94 | −2.22 | 0.16 | 0.00 |
| AC116158.2 | 1.07 | −0.37 | −1.09 | −0.27 | −0.45 | SIDT1 | −0.26 | 0.08 | 0.06 | −0.14 | 0.16 | LINC01872 | 0.33 | −1.30 | −0.23 | −0.64 | 1.73 |
| RN7SL365P | −1.12 | −0.16 | 0.65 | 0.36 | 0.94 | AC093019.2 | 0.73 | −1.74 | −0.53 | 0.31 | 1.21 | AL355602.1 | 0.22 | −0.31 | −1.42 | −1.07 | −1.13 |
| AC073862.2 | −1.46 | 0.26 | 3.05 | 0.28 | 0.89 | ARHGAP4 | −0.24 | −0.20 | 0.06 | −0.07 | 0.21 | FGD5-AS1 | −0.02 | 0.04 | 0.15 | −0.03 | −0.02 |
| FASN | −0.71 | 0.61 | 0.12 | 0.79 | 0.24 | AC012627.1 | 0.48 | −0.71 | −0.53 | 0.35 | 0.28 | NDUFB5P1 | −0.57 | −0.30 | −0.59 | 2.14 | 1.42 |
| SNX17 | 0.26 | −0.15 | −0.10 | −0.05 | 0.02 | AC046158.3 | −0.19 | 0.04 | 0.27 | 0.21 | 0.42 | C1QC | −0.06 | 0.14 | −0.12 | 0.03 | −0.54 |
| ATP10B | 0.70 | 0.11 | 0.15 | 0.24 | −0.17 | PABPN1L | −0.65 | 0.31 | 2.35 | −0.88 | 0.67 | AP000919.4 | 0.06 | −0.55 | −0.04 | −0.24 | −0.07 |
| COQ9 | 0.29 | −0.11 | −0.05 | −0.08 | 0.01 | NOC2LP1 | −0.46 | −0.70 | −0.52 | 0.98 | 0.54 | AC062031.1 | −0.57 | 1.08 | −0.20 | 0.45 | −1.55 |
| CHCHD4P2 | −0.93 | 0.63 | 0.36 | 0.14 | −0.53 | CAMTA1-DT | 0.40 | 0.26 | −0.09 | −0.47 | −0.72 | AC103563.5 | −0.57 | −0.26 | −1.03 | −1.54 | −0.27 |
| AC073335.2 | −0.52 | 0.35 | 0.40 | 0.10 | 0.29 | SLC4A9 | −0.22 | 0.02 | −0.04 | 0.26 | 0.48 | AC092718.6 | −0.08 | −1.81 | 0.39 | −0.38 | 0.57 |
| AADACL3 | −1.98 | 1.34 | 0.60 | 3.52 | 1.27 | G23016 | −0.33 | −0.06 | 0.70 | −0.35 | 0.13 | AC068722.1 | 0.16 | 0.04 | −0.57 | −0.30 | −1.36 |
| AC069431.2 | 0.73 | −0.12 | 0.04 | −0.23 | −0.32 | DVL1 | −0.16 | 0.09 | −0.54 | 0.44 | 0.07 | SHISA2 | 0.06 | 0.07 | −0.73 | −0.61 | −1.74 |
| AL445670.1 | −1.56 | 0.60 | 1.90 | −0.42 | −0.70 | LINC00470 | −0.49 | −0.10 | 0.00 | −0.21 | −0.65 | AL137779.3 | 0.04 | 0.19 | 0.13 | −0.27 | −0.28 |
| KIAA2026 | −0.19 | 0.18 | 0.25 | 0.07 | 0.11 | AC008885.2 | 0.71 | −1.58 | −1.30 | −2.02 | −1.44 | ATP6V0A1 | −0.01 | 0.17 | 0.18 | 0.00 | −0.06 |
| AC005695.1 | −0.76 | 0.07 | 0.22 | −0.05 | −0.08 | AC079298.3 | −0.32 | −0.12 | −0.37 | −0.02 | −0.29 | POU5F1P7 | −0.57 | 0.60 | 0.59 | −0.45 | −1.77 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| CARD8-AS1 | 0.68 | −0.46 | −0.42 | −0.04 | −0.31 | RNU2-49P | −0.72 | −0.30 | −1.22 | −0.25 | −1.88 | ERCC6L2 | 0.01 | 0.04 | 0.11 | −0.07 | −0.08 |
| GRPEL2-AS1 | 2.39 | −1.38 | −1.10 | −1.01 | −1.44 | GSTA8P | 0.64 | −0.28 | 0.29 | −0.14 | 0.20 | AC018511.2 | 0.06 | 0.26 | 0.46 | 0.02 | −0.28 |
| STARD13 | −0.49 | 0.19 | 0.59 | −0.13 | 0.31 | LINC02248 | −1.11 | 0.20 | −0.06 | 2.94 | 1.15 | AL357832.1 | −0.55 | −0.42 | 0.64 | −1.03 | −0.33 |
| NTRK2 | −0.63 | 0.79 | 0.01 | 0.57 | −0.15 | AC097634.1 | 0.26 | 0.47 | 0.31 | −0.03 | −0.41 | AC009063.1 | 0.08 | 0.45 | −0.83 | 0.50 | 0.57 |
| AL136164.4 | −0.85 | 0.01 | 0.95 | −0.18 | 0.74 | AC104692.1 | 0.42 | 0.14 | −0.62 | 0.40 | −0.31 | AL353151.1 | −0.16 | −0.66 | 1.48 | −1.44 | 1.25 |
| SCNN1B | −0.65 | 0.95 | 1.24 | 0.45 | −0.29 | CR382285.1 | −0.61 | −0.54 | −0.69 | 0.39 | 1.06 | AC078816.1 | −0.08 | −0.23 | 1.02 | −0.62 | 0.84 |
| LARP7 | 0.39 | −0.11 | −0.40 | −0.02 | −0.27 | SIX4 | −0.31 | 0.37 | 0.57 | −0.29 | 0.09 | AC093281.1 | −0.13 | −0.16 | −1.65 | 0.54 | −1.80 |
| SCLT1 | 0.29 | −0.29 | −0.28 | −0.18 | −0.06 | ACAA2 | 0.21 | −0.19 | −0.37 | −0.20 | −0.22 | LINC02293 | 0.15 | −0.26 | 0.64 | 0.33 | 0.71 |
| AC084125.2 | −0.63 | 0.35 | −0.57 | 0.51 | −0.23 | MTND5P12 | −0.29 | −0.87 | −0.22 | −0.26 | 0.67 | CLEC4A | −0.07 | −0.36 | −0.42 | 0.03 | 0.44 |
| KIAA0586 | 0.26 | −0.16 | 0.04 | −0.11 | 0.10 | HIST2H2BA | −0.26 | −0.22 | −0.41 | 0.11 | −0.28 | AC012123.1 | 0.26 | −1.60 | −1.20 | −1.21 | −1.44 |
| AC008280.3 | −0.91 | 0.73 | 0.80 | 0.67 | 0.70 | LINC01702 | 0.96 | −0.49 | −1.03 | −0.96 | −1.42 | OR5G5P | 0.16 | −0.46 | −0.66 | 0.04 | −0.33 |
| FAM182A | −0.77 | 0.35 | 0.16 | 0.82 | 0.26 | MAPK6P6 | 0.92 | 0.36 | −2.76 | 0.85 | −1.00 | IL22RA2 | 0.06 | −1.14 | −0.20 | −0.29 | 0.86 |
| SKIDA1 | −0.45 | 0.38 | 0.33 | 0.39 | −0.10 | CLDN2 | −0.22 | 0.21 | −0.34 | 0.56 | 0.11 | OR51I1 | −0.11 | 0.94 | −1.55 | 0.03 | −1.12 |
| ALAS2 | −1.04 | −0.49 | 0.71 | 0.43 | −1.76 | LINC01005 | −0.92 | −0.89 | −0.55 | −1.10 | −0.28 | RNU6-628P | 0.11 | −0.59 | −0.24 | −0.50 | −0.19 |
| PAIP2 | 0.39 | −0.03 | 0.08 | −0.12 | −0.26 | KCNH7 | −0.37 | 0.45 | −1.35 | 0.13 | −1.12 | EIF3KP1 | −0.07 | −0.06 | 0.23 | 0.23 | 0.31 |
| G42780 | −1.41 | 0.22 | 1.64 | −0.36 | 0.97 | CHURC1 | 0.11 | 0.03 | 0.11 | 0.03 | −0.28 | AP002360.2 | 0.13 | 0.78 | 0.23 | 0.56 | −0.46 |
| AC083906.5 | −1.21 | −0.50 | 1.81 | 0.28 | 1.41 | FAM204CP | −0.62 | 1.24 | 0.50 | 0.34 | 0.44 | G38913 | −0.03 | 0.33 | 0.09 | 0.16 | 0.13 |
| AC084816.1 | −1.15 | −0.30 | −0.10 | −0.07 | 0.17 | G2136 | 0.35 | −0.21 | −0.70 | 0.42 | 0.14 | HHLA2 | 0.09 | −0.32 | −1.04 | 0.03 | −1.28 |
| DAG1 | 0.36 | 0.06 | −0.21 | 0.02 | −0.32 | LINC01300 | −1.34 | −1.40 | 2.39 | 0.14 | 2.86 | AC008543.2 | 0.20 | −0.69 | −0.09 | 0.94 | 1.41 |
| SAMD1 | 0.30 | −0.27 | −0.35 | 0.02 | 0.11 | AC092809.1 | 0.41 | −0.44 | 1.03 | −0.55 | 0.68 | LINC02354 | 0.06 | −0.34 | 0.74 | 0.11 | 0.78 |
| CNRIP1 | −0.66 | 0.33 | 1.13 | −0.22 | 0.27 | NMBR | −0.67 | 0.30 | 0.78 | 0.10 | 0.15 | KLHL26 | −0.02 | 0.21 | −0.16 | 0.13 | −0.08 |
| MOGAT2 | −1.50 | 0.36 | 0.50 | 1.36 | 0.56 | AL121989.1 | 0.19 | 0.14 | 0.39 | 0.10 | 0.09 | AC007922.1 | 0.24 | 0.79 | −0.66 | 0.82 | −1.02 |
| RPL31 | 0.39 | −0.04 | −0.07 | −0.10 | −0.33 | LINC02398 | −0.69 | 1.65 | −0.18 | 0.61 | 0.03 | AL031847.1 | 0.26 | 1.06 | 1.19 | −0.75 | −0.50 |
| PSMC1P7 | −1.06 | 0.65 | 1.82 | −0.29 | −0.01 | FBN1 | −0.29 | 0.32 | 1.39 | −0.16 | −0.13 | AC006548.3 | −0.35 | 0.21 | −0.42 | 0.27 | 1.61 |
| CCDC58 | 0.34 | −0.22 | −0.36 | −0.05 | 0.05 | AC015849.5 | −0.38 | −0.35 | −0.72 | −0.44 | −0.43 | AL158823.1 | −0.10 | −0.69 | 0.27 | −1.23 | −0.24 |
| AL022157.1 | −0.75 | 0.71 | 0.82 | 0.44 | 0.25 | AC016590.3 | −0.69 | 0.94 | 1.48 | 0.17 | 1.07 | AC002386.1 | 0.56 | 0.15 | −0.93 | −0.30 | −3.17 |
| BAG5 | 0.32 | 0.01 | −0.17 | −0.03 | −0.33 | AL050343.1 | 0.24 | −0.04 | 0.66 | 0.08 | 0.61 | LINC00552 | −0.20 | 0.09 | 0.50 | 1.65 | 0.29 |
| MPRIP | −0.27 | 0.06 | 0.12 | −0.03 | 0.06 | NPTN-IT1 | 0.16 | −0.11 | 0.04 | −0.20 | −0.12 | AL034548.1 | −0.32 | 0.31 | 1.32 | 0.04 | −1.06 |
| HRH2 | 0.82 | −1.04 | −1.64 | 0.22 | −0.22 | AL136985.1 | −0.60 | −0.12 | 0.10 | −0.41 | −0.95 | AC024651.2 | 0.13 | −0.25 | −1.47 | −0.04 | −2.15 |
| PNPT1P1 | −0.59 | 0.04 | 0.32 | 0.59 | 0.41 | RN7SL105P | 0.67 | −1.13 | 0.59 | −0.04 | 0.59 | KCTD3 | 0.02 | 0.03 | 0.05 | 0.12 | −0.02 |
| SCART1 | −0.52 | 0.49 | 0.49 | 0.25 | 0.29 | RP11-337C18.9 | 0.21 | 0.09 | −0.03 | 0.02 | −0.34 | ADAM24P | −0.30 | 0.48 | −0.61 | −0.63 | −2.39 |
| KIAA1614 | −0.39 | 0.18 | 0.24 | 0.07 | 0.20 | AC100827.4 | −0.30 | 0.08 | 0.38 | 0.28 | −0.11 | AL138885.2 | 0.13 | 0.57 | −0.29 | 1.48 | 0.84 |
| AC007848.1 | −1.14 | 1.38 | 1.69 | 0.09 | −0.45 | SNTB2 | 0.11 | −0.05 | −0.07 | −0.02 | −0.24 | NTN3 | −0.07 | 0.33 | −1.03 | 0.51 | −0.42 |
| MNDA | 0.87 | −0.73 | −0.05 | −0.25 | −0.02 | LRRC10B | −0.53 | 0.29 | 0.20 | −0.16 | −0.01 | AC024587.1 | −0.13 | 0.41 | −0.87 | 0.74 | −0.92 |
| OR51J1 | −1.55 | 0.22 | 1.18 | 0.25 | 0.58 | DCAF4L1 | 0.21 | −0.38 | 0.04 | −0.44 | 0.20 | LINC02554 | −0.09 | 0.26 | −1.69 | 0.93 | −0.39 |
| RN7SL431P | 0.95 | −0.02 | −0.59 | 0.14 | −0.11 | GUSBP5 | 0.53 | 0.03 | 0.41 | −0.40 | −0.60 | AC233976.1 | 0.21 | −1.78 | 1.11 | 0.45 | 2.08 |
| METTL13 | 0.25 | −0.29 | −0.24 | −0.18 | 0.08 | MYL6B | 0.12 | −0.10 | −0.25 | 0.03 | −0.02 | AC243960.7 | −0.18 | −1.59 | 0.23 | −0.51 | 1.10 |
| MIR2116 | 0.95 | −0.71 | −0.29 | 0.04 | −0.23 | LPAL2 | −0.21 | −0.22 | −0.08 | −0.23 | −0.02 | MEMO1P3 | −0.25 | 0.14 | −0.94 | 1.20 | 0.38 |
| AUH | −0.31 | 0.28 | 0.41 | 0.14 | 0.20 | LINC01567 | −0.63 | −0.47 | −0.85 | −0.22 | 0.04 | AC129926.2 | −0.56 | −0.66 | −1.56 | 1.12 | NA |
| AC116366.1 | −0.51 | −0.14 | 0.28 | −0.03 | 0.36 | RPL29P30 | −0.47 | −0.28 | −0.33 | −0.51 | −0.82 | AHCYP2 | −0.13 | 0.45 | −1.50 | −0.05 | −0.51 |
| C19orf33 | 1.02 | −0.81 | −0.71 | 0.09 | 0.01 | RP11-566K19.6 | −0.28 | 0.12 | −0.21 | −0.28 | 0.38 | IGHV3-32 | 0.56 | −0.85 | −1.52 | −0.58 | −2.41 |
| EFEMP2 | −0.57 | 0.14 | 0.79 | −0.28 | 0.14 | AC093763.2 | −0.70 | 1.35 | 0.07 | 0.10 | 0.68 | CACNG6 | −0.15 | −0.73 | −0.42 | −0.35 | 0.53 |
| AC010653.3 | −0.87 | 0.16 | 0.33 | 0.51 | 0.50 | DOK5 | −0.38 | 0.42 | 0.69 | −0.04 | 0.19 | GSEC | −0.03 | −0.20 | 0.20 | −0.24 | 0.21 |
| AC010618.3 | −0.60 | 0.43 | 0.47 | 0.28 | 0.05 | AC112255.1 | −0.90 | −0.82 | 0.56 | −1.95 | −1.60 | AC004004.1 | −0.30 | −0.38 | 0.65 | −0.24 | −0.49 |
| LINC00205 | −0.39 | −0.04 | 0.38 | −0.07 | 0.36 | STARD13-AS | −0.15 | 0.11 | 0.58 | −0.29 | 0.41 | SPINT3 | 0.56 | 0.07 | −0.67 | 1.64 | 0.77 |
| MAP1LC3C | −1.30 | 0.67 | −0.29 | 0.72 | −0.45 | AC007494.3 | 0.26 | −0.07 | −0.01 | −0.09 | −0.01 | RNA5SP47 | 0.14 | 0.05 | −0.78 | −0.30 | −1.04 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| GSK3A | 0.31 | −0.01 | −0.10 | 0.03 | −0.12 | NACAP10 | 1.02 | 0.21 | −0.39 | −0.50 | 0.82 | CYP4F32P | −0.30 | −0.18 | −0.47 | 0.14 | −1.84 |
| C18orf25 | 0.19 | −0.12 | −0.23 | −0.04 | −0.11 | AL355922.3 | −0.54 | 1.32 | 0.11 | 1.43 | −0.79 | DMP1 | 0.13 | −0.26 | −1.59 | 0.73 | −1.62 |
| FBXL19-AS1 | 0.58 | −0.86 | −0.68 | −0.27 | 0.22 | AC007068.2 | −0.63 | −0.21 | −0.77 | 0.34 | 0.48 | AP006289.1 | 0.18 | 0.32 | 1.03 | −0.17 | 0.22 |
| GAR1 | 0.31 | −0.25 | −0.19 | −0.15 | 0.10 | G11316 | −0.82 | 0.14 | 0.12 | 2.32 | 1.69 | AP004247.1 | 0.12 | 0.96 | −1.45 | 1.04 | −0.06 |
| FER | 0.26 | −0.04 | −0.34 | −0.05 | −0.19 | AC020656.2 | −0.45 | −0.65 | −0.44 | 0.23 | −0.74 | AC017099.1 | 0.05 | −0.71 | 0.72 | −0.66 | −1.46 |
| AL022323.5 | 0.71 | −0.61 | −0.84 | 0.12 | 0.02 | AC009159.1 | 0.53 | −0.25 | −1.96 | 1.09 | 0.14 | RNU6-448P | −0.56 | 0.97 | 0.74 | −0.71 | −1.28 |
| AL109811.3 | −1.23 | 1.10 | 1.29 | 0.55 | 0.15 | HLA-J | −0.35 | −0.26 | 0.42 | 0.27 | 0.87 | PIK3C3 | 0.01 | 0.06 | 0.05 | 0.09 | −0.08 |
| HIST1H4H | 0.44 | −0.54 | −0.49 | 0.04 | −0.13 | AC069360.1 | −0.27 | 0.30 | 0.08 | −0.08 | −0.46 | CYB5D1 | −0.14 | −0.54 | 0.02 | −0.20 | −1.38 |
| DGCR8 | −0.32 | 0.02 | −0.15 | 0.15 | 0.06 | EDN2 | 0.40 | 0.18 | −0.86 | 0.11 | −0.65 | MILR1 | −0.06 | −0.54 | 0.42 | −0.65 | 0.45 |
| RBFADN | −0.60 | 0.41 | 0.72 | 0.17 | 0.40 | AL138749.1 | 1.21 | −1.78 | −2.05 | 0.67 | −0.72 | LINC01968 | −0.09 | 0.75 | 0.74 | 0.54 | 0.01 |
| KCNAB1-AS2 | −1.54 | 1.11 | 0.84 | 1.00 | −0.44 | KRTAP10-2 | −0.80 | −0.84 | 0.69 | 1.20 | 0.48 | IGKV2OR22-3 | 0.56 | −0.08 | −1.97 | 1.35 | −0.63 |
| REX1BD | −0.46 | 0.13 | 0.02 | 0.27 | 0.24 | AC000068.2 | −0.56 | 1.38 | −0.27 | −0.53 | −1.09 | ADGRA1 | 0.16 | −0.78 | −1.46 | 0.76 | −1.14 |
| GRK4 | −0.31 | −0.06 | 0.25 | 0.04 | 0.38 | ALG6 | 0.13 | 0.05 | 0.11 | −0.04 | −0.07 | AL121829.2 | −0.15 | −0.58 | 0.87 | −1.36 | 0.12 |
| CD83 | 0.85 | −0.98 | −1.12 | −0.64 | −0.30 | AL035415.1 | −1.00 | −0.69 | −0.67 | 0.84 | −0.93 | AP000590.1 | 0.12 | 0.24 | −0.31 | −0.90 | −0.13 |
| LRRFIP1P1 | −0.42 | 0.13 | 0.49 | −0.10 | 0.24 | DAPK2 | −0.15 | 0.11 | −0.39 | 0.24 | 0.07 | AC007344.1 | −0.12 | 0.04 | −0.88 | −0.25 | −1.27 |
| G18697 | −0.67 | 0.58 | 0.25 | −0.04 | −0.55 | AP5B1 | 0.12 | 0.04 | −0.55 | 0.03 | −0.62 | LRRC8E | 0.03 | −0.06 | −0.10 | 0.08 | −0.04 |
| GABRA2 | −1.04 | 0.04 | 0.71 | 0.15 | 0.56 | PRND | 0.43 | −0.17 | 1.76 | −0.77 | 0.92 | RPSAP71 | −0.56 | −0.53 | 1.10 | −0.74 | 2.02 |
| AC078846.1 | −0.32 | 0.13 | 0.47 | 0.15 | 0.16 | MTND3P12 | 1.48 | −0.70 | −2.06 | 0.89 | −0.95 | OR4K6P | −0.31 | −0.65 | −1.41 | −0.66 | −0.81 |
| AC114812.3 | 1.67 | −0.27 | −0.99 | 0.92 | 0.18 | SFRP1 | 0.23 | 0.10 | −0.21 | −0.03 | 0.07 | SPRED2 | −0.02 | −0.05 | −0.22 | −0.05 | −0.14 |
| RNF24 | −0.26 | 0.18 | 0.27 | −0.06 | −0.12 | NOL12 | 0.22 | 0.17 | −0.05 | −0.05 | −0.22 | CPA5 | 0.08 | 0.04 | −0.43 | 0.45 | 0.18 |
| AL390728.3 | −1.15 | 0.94 | 1.42 | 0.49 | −0.04 | SLC17A9 | 0.23 | −0.51 | −0.09 | −0.67 | −0.03 | ARL2BPP1 | 0.37 | −0.43 | −0.70 | 0.53 | 0.13 |
| CLUHP10 | −1.65 | 0.75 | 2.08 | 0.63 | 0.38 | CAPN14 | −0.27 | −0.19 | 0.02 | −0.04 | 0.04 | AL355877.1 | −0.08 | −0.88 | −1.81 | 0.28 | −1.48 |
| ACTA2 | −0.66 | 0.20 | 0.76 | −0.02 | −0.04 | AP001318.1 | 0.90 | −0.93 | 0.94 | −0.06 | 1.22 | ACTG1P16 | −0.13 | −1.20 | −0.97 | 1.34 | 1.05 |
| MAZ | 0.34 | −0.10 | −0.55 | 0.26 | −0.08 | AC099328.1 | 0.26 | −0.29 | −1.22 | 0.07 | −0.04 | AC016355.1 | −0.04 | −0.11 | 0.21 | 0.04 | 0.40 |
| AGBL5-IT1 | −0.55 | 0.14 | 0.03 | 0.34 | 0.19 | G291 | 0.97 | 0.56 | −0.85 | 0.42 | −0.04 | AC026304.1 | −0.56 | 0.10 | 0.81 | −0.05 | 0.60 |
| MIR22HG | 0.49 | −0.40 | −0.63 | −0.29 | −0.60 | LINC00592 | 0.40 | 0.10 | 1.30 | −0.37 | −0.13 | AL161722.2 | 0.34 | −1.22 | −1.06 | −0.31 | −0.32 |
| LRRC49 | −0.51 | 0.45 | 0.31 | 0.21 | −0.21 | CES1P2 | −0.74 | −0.53 | −0.39 | −0.15 | 0.65 | AC017007.4 | −0.14 | −0.52 | −1.40 | 0.59 | −0.61 |
| FAM86B1 | −0.60 | 0.40 | 0.50 | −0.01 | 0.10 | NAA60 | 0.07 | 0.04 | −0.17 | 0.08 | −0.12 | LINC02015 | −0.15 | −0.39 | −1.36 | −0.52 | −2.01 |
| OR2H2 | −0.97 | 0.55 | 0.78 | 0.14 | 0.29 | AC010275.1 | 0.65 | −2.12 | −0.36 | −0.45 | 0.45 | RNU6-760P | −0.23 | 0.05 | 0.47 | −0.51 | −0.56 |
| NUBP1 | 0.33 | −0.12 | −0.65 | −0.01 | −0.41 | AC107980.1 | −0.56 | −0.80 | 0.46 | −0.41 | 0.61 | AC010145.1 | −0.56 | −0.65 | 0.10 | −0.90 | 0.36 |
| AL138808.1 | −1.20 | 0.37 | 1.88 | −0.06 | 0.77 | ANKRD20A8P | −0.38 | 0.24 | −0.53 | 1.19 | −0.30 | AC026774.2 | 0.28 | −0.19 | −0.59 | −0.04 | −1.16 |
| AL355596.1 | −1.54 | −1.82 | 0.60 | 0.35 | 0.21 | RN7SL702P | −0.98 | 0.03 | −0.28 | 0.90 | −0.53 | AL353698.1 | −0.05 | 0.38 | −0.18 | 0.58 | −0.11 |
| AC137735.2 | −2.49 | 0.20 | 1.80 | −0.68 | 1.09 | AP003119.3 | −0.18 | −0.11 | −0.29 | 0.15 | 0.03 | AC106894.1 | −0.31 | 0.91 | 1.30 | 0.11 | −0.79 |
| FOLR2 | −1.02 | 0.77 | 1.00 | 0.03 | −0.33 | AC245884.11 | 0.68 | −0.22 | −0.54 | −0.54 | −0.66 | ALDH3A1 | −0.05 | 0.68 | 0.41 | 0.72 | −0.03 |
| CUL5 | 0.35 | −0.05 | −0.15 | −0.04 | −0.15 | CLEC12A-AS1 | −0.59 | −0.24 | 0.32 | −0.12 | −0.59 | AP002358.2 | 0.15 | −0.71 | 0.29 | −0.12 | 2.07 |
| RPS27AP2 | 1.66 | −0.68 | −1.02 | −0.01 | −0.23 | G6485 | −0.36 | −0.12 | −0.02 | 0.30 | 0.16 | AC026356.2 | 0.05 | 0.17 | 1.23 | −0.51 | −0.14 |
| LINC01950 | −1.41 | 0.15 | 1.85 | 1.17 | 0.51 | LINC01559 | 0.49 | −0.15 | 0.40 | −0.60 | −0.67 | POLR3GP2 | 0.29 | −0.06 | 0.38 | 0.31 | −0.33 |
| SNHG11 | −0.57 | 0.23 | 0.13 | 0.55 | −0.14 | PAIP1P1 | 0.20 | −0.03 | −0.04 | 0.06 | 0.13 | LINC02192 | 0.13 | −0.83 | 0.97 | −0.74 | 0.96 |
| LINC02367 | −0.69 | 0.39 | 0.05 | 0.26 | −0.14 | AC012615.4 | −0.35 | −0.76 | −1.29 | −0.05 | −0.04 | LINC01813 | −0.24 | −1.18 | 0.56 | −1.26 | 0.24 |
| AL356317.1 | −0.64 | 0.48 | 0.60 | 0.35 | 0.44 | RSBN1L | −0.06 | 0.02 | 0.10 | 0.00 | 0.08 | OR8K5 | 0.56 | −0.04 | −1.89 | 1.33 | −1.57 |
| LINC01376 | −0.47 | 0.25 | 0.72 | 0.15 | 0.25 | HUS1 | 0.09 | −0.11 | 0.10 | −0.18 | 0.09 | LINC02262 | −0.23 | −0.20 | 1.35 | 1.47 | 1.06 |
| AL359220.1 | −0.31 | 0.21 | 0.35 | 0.26 | 0.31 | SNX29P1 | −0.25 | 0.17 | 0.06 | 0.27 | 0.21 | RNU6-406P | 0.17 | −0.70 | 0.47 | −0.88 | −0.37 |
| CLSTN1 | 0.41 | −0.09 | −0.48 | 0.18 | −0.16 | PCBP2P1 | −0.21 | 0.03 | −0.18 | −0.05 | −0.35 | OR2J4P | −0.37 | −0.46 | 0.18 | −0.89 | −1.10 |
| G42332 | −1.26 | 1.08 | 1.67 | 0.66 | 0.24 | AC006305.1 | 0.45 | 0.70 | −0.53 | 0.83 | 0.11 | AL500522.1 | −0.39 | 0.05 | −1.48 | 1.61 | −0.48 |
| HMGB1P24 | 0.54 | −0.36 | −0.13 | −0.02 | 0.24 | AC092104.3 | −1.23 | −0.59 | 0.38 | 0.20 | −1.38 | MIR3942 | 0.08 | 0.28 | 0.05 | 0.74 | −0.28 |
| SLFN5 | 0.51 | −0.46 | −0.10 | −0.49 | −0.14 | AC004875.1 | −0.52 | −0.28 | 1.22 | −0.47 | 0.35 | AC008507.3 | −0.15 | −0.21 | −0.39 | −0.44 | −0.48 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| KHDRBS3 | −0.56 | 0.38 | 0.89 | −0.16 | 0.17 | RAPGEF1 | −0.09 | −0.20 | −0.44 | 0.00 | −0.07 | AL451063.1 | −0.07 | 0.12 | 0.23 | −0.26 | 0.63 |
| HELB | 0.32 | −0.42 | −0.49 | −0.28 | −0.14 | LINC00939 | −0.54 | 0.26 | −0.62 | 0.37 | −0.57 | AL445685.1 | 0.09 | 0.68 | 0.29 | −0.74 | −1.02 |
| LINC02590 | −2.10 | −0.39 | 0.71 | 0.67 | −0.51 | G25046 | −1.04 | −1.35 | −0.25 | −0.26 | 0.42 | AL358075.2 | 0.12 | −0.62 | −1.62 | 0.40 | −1.16 |
| CHIC1 | −0.35 | 0.38 | 0.64 | 0.25 | 0.10 | C1orf123 | 0.09 | −0.04 | 0.26 | −0.06 | 0.15 | PSTK | 0.03 | −0.02 | 0.35 | 0.02 | 0.16 |
| LINC00556 | 2.06 | −1.93 | −2.31 | −1.03 | −1.03 | KRT18P7 | −0.26 | 0.08 | 0.61 | 0.19 | 0.43 | RPL7P59 | 0.12 | −0.14 | −0.06 | −0.11 | −0.29 |
| AC016590.1 | −1.12 | 0.66 | 1.06 | 0.01 | 0.64 | AC069234.4 | 0.83 | 1.23 | −2.09 | 0.66 | −3.28 | AL591893.1 | −0.19 | 0.81 | −1.00 | 0.64 | −0.45 |
| AL117329.1 | −0.63 | 0.37 | 0.39 | 0.26 | 0.13 | AL139246.3 | −0.49 | 0.13 | 1.22 | 0.14 | 1.47 | AC009365.1 | −0.26 | −1.67 | −0.28 | −1.58 | −0.26 |
| AL391416.1 | 0.75 | −0.73 | −0.43 | −0.21 | 0.08 | MIR3158-1 | −0.73 | −0.06 | 1.82 | −0.67 | 0.58 | KRTAP9-8 | −0.56 | 0.47 | 0.80 | −0.80 | −0.83 |
| RPA2 | 0.34 | −0.28 | −0.02 | −0.19 | 0.05 | AC136285.1 | 0.49 | −0.19 | −1.99 | 0.49 | −1.14 | CSNK1A1P3 | 0.15 | −0.23 | −0.38 | −0.14 | 0.85 |
| MTFR1L | −0.32 | 0.13 | 0.16 | 0.18 | 0.31 | AL357556.1 | −0.56 | −1.13 | 1.32 | 0.54 | 2.95 | PABPC1L2B | 0.55 | −1.65 | −0.48 | −1.04 | −0.24 |
| NECTIN3 | −0.65 | 0.27 | 1.00 | −0.18 | 0.13 | ST13P4 | −0.20 | −0.10 | −0.34 | 0.16 | 0.40 | AC079866.2 | 0.06 | −0.17 | −0.02 | −0.67 | −0.23 |
| HIST1H4C | 0.55 | −0.34 | −0.49 | −0.25 | −0.73 | AL512306.2 | −0.52 | −0.58 | −0.94 | −0.12 | 0.33 | SRRM1 | −0.01 | −0.04 | −0.12 | −0.09 | −0.09 |
| REM2 | −0.75 | 0.84 | 0.12 | 0.61 | 0.15 | GABRR3 | −0.53 | 0.48 | −1.02 | 0.66 | −1.13 | AL133553.1 | −0.06 | 0.81 | −0.44 | −0.15 | −0.71 |
| RHNO1 | 0.36 | −0.32 | −0.32 | −0.03 | 0.04 | PMPCB | 0.10 | 0.03 | 0.09 | 0.02 | 0.01 | AC092142.2 | 0.55 | 0.48 | 0.12 | 1.04 | 1.66 |
| FLJ46284 | −0.51 | 0.34 | 0.45 | 0.26 | −0.03 | AC073023.1 | 0.84 | −1.35 | −0.87 | −0.17 | 0.01 | AL121827.1 | 0.24 | −1.26 | −0.13 | −0.89 | −0.32 |
| AL121753.1 | −0.57 | 0.38 | 0.86 | 0.11 | 0.19 | SIK3 | 0.06 | 0.04 | −0.18 | 0.03 | −0.22 | AC096633.1 | −0.11 | −0.63 | 1.11 | −1.07 | 0.15 |
| G39039 | 0.90 | −0.11 | 0.00 | −0.02 | 0.06 | LINC01902 | −0.42 | −0.51 | −0.71 | 0.24 | −0.35 | AL627309.5 | −0.05 | 0.05 | −0.49 | 0.17 | 0.10 |
| ELOCP21 | −1.47 | 1.29 | 1.07 | 0.39 | 0.29 | AC110801.1 | 0.41 | 0.35 | 0.26 | −0.04 | −0.26 | SIGLEC30P | 0.39 | −0.60 | −0.09 | 1.11 | 0.63 |
| AC090617.2 | 1.70 | −0.37 | −1.16 | −0.26 | −0.87 | NUGGC | −0.34 | −0.05 | 0.21 | −0.06 | 0.06 | AC006970.3 | −0.55 | 1.31 | −1.38 | 1.45 | −1.88 |
| EVI2A | 0.72 | −0.34 | −0.37 | −0.19 | −0.15 | LINC00442 | −0.74 | 1.04 | −1.17 | 0.53 | −2.07 | AC103996.1 | 0.32 | −0.11 | −0.70 | −1.29 | 0.81 |
| AL391807.1 | −0.96 | 0.32 | 1.34 | 0.27 | 0.64 | AC005034.3 | 0.15 | 0.05 | −0.12 | −0.06 | −0.03 | ABHD8 | 0.03 | 0.38 | 0.10 | 0.43 | 0.16 |
| AC010886.1 | −0.97 | 0.44 | 1.15 | −0.07 | 0.11 | EIF5A2 | 0.19 | −0.09 | −0.13 | −0.28 | −0.17 | RNU7-72P | −0.20 | −0.82 | −0.08 | −1.32 | −0.66 |
| FAM98B | 0.33 | −0.14 | −0.10 | −0.08 | −0.04 | RN7SL344P | 0.62 | −0.64 | −1.02 | −0.16 | 0.90 | AC084809.1 | 0.07 | −0.67 | 0.62 | −0.34 | 0.40 |
| AC125613.1 | −0.90 | 0.10 | 0.00 | 0.13 | 0.34 | DMRTB1 | −0.79 | −0.56 | −0.77 | −0.69 | −0.18 | AC105031.2 | −0.17 | −0.50 | −2.45 | 2.51 | −0.50 |
| A4GNT | −1.14 | 0.01 | −0.78 | 0.59 | −0.48 | RPL15P3 | 0.23 | 0.06 | 0.22 | −0.24 | −0.55 | PDE7B | −0.03 | 0.05 | 0.25 | −0.34 | −0.18 |
| GPR18 | 0.45 | −0.17 | −0.23 | 0.02 | 0.06 | CLEC9A | 0.35 | −0.59 | −0.10 | −0.33 | 0.38 | AC009263.1 | 0.26 | −1.25 | 0.00 | 0.26 | 0.68 |
| MX2 | 0.52 | −0.66 | −0.68 | −0.48 | −0.22 | LRCOL1 | −0.49 | −0.17 | −0.63 | −0.47 | −0.67 | AC104109.1 | 0.43 | −0.89 | −0.57 | −0.65 | 1.00 |
| KRT86 | −1.02 | 1.46 | 1.71 | 0.11 | 0.46 | G30965 | −0.33 | −0.12 | 0.06 | −0.14 | −0.08 | AC019178.1 | −0.51 | −0.22 | 0.03 | −1.38 | −1.58 |
| AC000123.2 | 1.45 | 0.33 | −0.63 | 0.42 | −0.45 | RNU4-54P | 0.78 | −0.16 | 0.00 | 0.04 | 0.59 | KRT126P | −0.24 | 0.05 | −1.75 | 0.96 | −0.43 |
| AKR1C3 | −0.72 | 0.50 | 1.08 | 0.17 | 0.14 | DKKL1 | −0.46 | 0.12 | −0.86 | −0.62 | −0.70 | RN7SKP133 | −0.29 | 0.05 | −0.39 | 0.43 | −0.38 |
| AC007566.1 | −0.74 | 0.27 | 1.13 | −0.23 | 0.37 | AC093627.5 | 0.33 | −0.74 | 0.06 | −0.41 | 0.30 | AC006130.1 | 0.33 | −0.27 | −0.19 | −0.87 | −1.89 |
| PRED57 | 0.91 | −0.81 | −0.96 | −0.12 | −0.30 | AC117490.2 | 0.56 | −0.04 | −0.16 | −0.16 | −0.44 | FOXG1-AS1 | −0.15 | −1.22 | −1.60 | 1.05 | 0.52 |
| AC090114.3 | −0.40 | 0.03 | −0.01 | 0.11 | 0.11 | GTF2IRD1P1 | 0.37 | −0.30 | 0.04 | −0.14 | 0.16 | AC009505.1 | 0.15 | 0.23 | 0.09 | −0.28 | −0.79 |
| SLC45A3 | 0.57 | 0.03 | −0.03 | 0.27 | 0.24 | PCNP | 0.10 | 0.05 | 0.23 | −0.11 | −0.06 | AC105339.5 | 0.13 | −0.14 | 2.33 | −0.24 | 0.28 |
| CDK9 | −0.32 | 0.18 | 0.01 | 0.16 | 0.00 | LINC01629 | 0.75 | −0.67 | −3.39 | 0.28 | −0.51 | AC105910.1 | −0.12 | −1.49 | 0.32 | −3.06 | −1.98 |
| LTC4S | −0.67 | 0.31 | 0.75 | 0.27 | 0.41 | LINC00863 | −0.14 | 0.07 | 0.19 | 0.18 | 0.04 | AC245884.10 | 0.06 | −0.35 | 0.06 | 0.20 | 0.75 |
| AC023421.1 | −1.46 | 0.14 | 1.69 | −0.01 | 0.51 | ACBD5 | 0.10 | 0.17 | 0.00 | 0.04 | −0.14 | PROM1 | 0.05 | 0.13 | −0.08 | 0.25 | 0.12 |
| CARD9 | −0.81 | −0.18 | −0.02 | 0.28 | 0.39 | AC123905.1 | −0.88 | 1.22 | −0.43 | −0.13 | −0.98 | CCDC179 | −0.13 | −1.37 | 0.64 | −0.59 | 1.30 |
| FLJ22447 | 0.82 | −0.68 | −0.95 | −0.37 | −0.54 | PNMA2 | −0.29 | 0.00 | 0.57 | −0.25 | −0.04 | KLF2P1 | 0.55 | −2.21 | −0.58 | 0.78 | −0.16 |
| GIPC1 | 0.34 | 0.04 | −0.59 | 0.18 | −0.34 | AP002365.1 | −0.90 | −0.84 | 0.95 | −1.16 | 1.89 | ANGPTL2 | −0.04 | 0.37 | 0.60 | −0.47 | −0.47 |
| ADNP | 0.26 | 0.05 | −0.13 | 0.06 | −0.13 | RPL5P12 | 0.44 | 0.18 | −0.15 | 0.47 | −1.00 | MTCO1P14 | 0.18 | −1.92 | 0.57 | −1.04 | 0.33 |
| COPS7A | 0.23 | −0.13 | −0.07 | 0.01 | −0.04 | LINC01054 | −0.43 | −0.07 | 0.20 | 0.61 | 0.25 | RPSAP6 | 0.03 | −0.39 | −0.11 | −0.05 | 0.66 |
| LINC01959 | −0.82 | 0.36 | 0.64 | 0.30 | 0.50 | AL021395.1 | −0.81 | −0.06 | −0.37 | 0.69 | −0.48 | IGHV3-49 | 0.55 | −0.42 | −0.74 | 2.16 | −0.67 |
| ALDH1B1 | −0.69 | 0.10 | 0.56 | −0.48 | −0.39 | RNF133 | 0.30 | −0.17 | 0.65 | −0.46 | 0.83 | AC092059.1 | 0.55 | −1.61 | −0.87 | −0.02 | 0.59 |
| DLEU2L | −0.41 | 0.06 | 0.16 | 0.18 | 0.05 | ATP6V0CP3 | −0.53 | −1.08 | −0.55 | −0.41 | 0.01 | FABP5P15 | 0.14 | −1.16 | −0.64 | 0.05 | 1.07 |
| RP11-210K20.3 | −1.15 | 0.15 | 0.01 | 0.20 | 1.01 | AC007342.7 | −0.17 | −0.08 | 0.36 | −0.01 | 0.35 | AL450043.1 | 0.17 | 2.23 | −1.36 | 1.02 | −3.28 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| GAL3ST1 | −1.48 | 0.45 | 1.14 | −0.10 | 0.81 | PGS1 | 0.11 | −0.44 | −0.40 | −0.09 | 0.34 | RETN | −0.17 | −0.27 | −0.86 | 0.12 | −1.60 |
| IGSF5 | −1.42 | 0.41 | 0.05 | 0.51 | −0.54 | AC005696.3 | 0.32 | −0.12 | −0.16 | 0.32 | 0.07 | PARS2 | −0.03 | 0.02 | −0.26 | 0.04 | −0.16 |
| AC007557.1 | −1.38 | 0.93 | 1.20 | 0.38 | 0.06 | AC079336.6 | 0.40 | 0.49 | −0.55 | 0.01 | −0.66 | AC006557.2 | −0.42 | −0.46 | 0.12 | −1.04 | −0.60 |
| AL359532.1 | −0.81 | 0.08 | 1.57 | −0.30 | 0.92 | LINC00575 | −0.85 | 0.18 | −0.69 | 1.71 | 0.09 | PPIL1P1 | −0.17 | 0.00 | 0.26 | 0.34 | 0.85 |
| AL359649.1 | −1.88 | −0.43 | 0.80 | 0.73 | 0.36 | RNU1-117P | −0.72 | 0.33 | 1.05 | 0.35 | 0.43 | RNA5SP61 | −0.20 | 0.11 | 0.96 | −0.50 | −0.01 |
| AC123768.5 | 1.32 | −0.61 | −1.63 | 0.16 | −0.61 | FUT8 | −0.15 | −0.05 | 0.43 | −0.34 | 0.01 | AC013248.1 | −0.55 | 0.06 | 0.05 | 1.47 | 0.52 |
| AC010320.3 | −0.56 | 0.26 | −0.07 | 0.24 | −0.07 | RAPGEF4-AS1 | −0.28 | 0.48 | 0.35 | −0.05 | −0.50 | AC015922.2 | 0.05 | 0.05 | 0.47 | 0.05 | 0.21 |
| ADAM12 | 0.77 | −0.61 | −0.58 | −1.22 | −0.78 | KCNV2 | −0.16 | 0.03 | 0.18 | −0.05 | 0.45 | RPL7L1P10 | −0.26 | −1.50 | 1.47 | −0.79 | 1.32 |
| MRPL10 | 0.31 | −0.07 | −0.43 | 0.02 | −0.44 | AP001486.3 | 0.74 | −0.42 | −1.75 | −0.74 | −1.24 | RPL21P3 | 0.06 | 0.03 | 0.01 | 0.47 | 0.30 |
| PTTG4P | 1.01 | −0.13 | −0.82 | 0.00 | −0.90 | AC105020.5 | 0.45 | −0.24 | −0.88 | 0.52 | 1.07 | OR4A17P | 0.29 | −0.26 | −2.52 | 0.71 | −0.79 |
| OCRL | −0.21 | 0.01 | 0.19 | −0.02 | 0.20 | RPL23AP36 | 0.51 | 0.01 | 0.03 | 0.46 | 0.45 | RN7SL330P | 0.05 | −0.52 | 0.64 | −0.53 | 0.34 |
| AC012313.6 | −1.26 | 1.01 | 1.76 | 0.05 | 0.32 | AL136298.1 | 0.43 | 0.07 | 0.02 | 0.21 | 0.19 | MTCO1P48 | −0.44 | 0.87 | −0.93 | 1.34 | −1.33 |
| GDPD2 | −0.76 | 0.40 | −0.11 | 0.56 | −0.08 | AC116562.2 | −1.26 | 1.65 | 1.46 | 1.36 | 1.29 | AC005208.1 | 0.13 | 0.45 | −0.68 | 1.44 | −1.36 |
| AC121757.1 | −1.23 | 0.77 | 2.64 | 0.05 | −0.09 | RNU2-31P | 0.49 | −0.61 | −0.08 | −0.01 | 0.38 | AC107023.1 | −0.55 | −1.04 | 0.27 | −1.36 | 0.23 |
| AC021242.1 | −1.53 | 0.49 | 1.51 | −0.27 | 0.57 | LINC01444 | 0.49 | 0.17 | 0.34 | 1.07 | 0.50 | AL450023.1 | −0.37 | −0.66 | −1.03 | 0.83 | 0.40 |
| AC073347.1 | −2.06 | 0.85 | 1.36 | 2.90 | 0.14 | DEFB125 | 1.02 | −0.92 | 0.37 | −0.07 | 0.25 | LINC02118 | −0.17 | −0.68 | −0.98 | 0.36 | −0.80 |
| SELENOW | −0.30 | 0.12 | 0.30 | −0.03 | 0.10 | AP002812.4 | 0.38 | −0.59 | 0.43 | −0.64 | 0.45 | MED28P4 | 0.55 | −1.15 | 0.32 | −0.64 | 1.35 |
| AC026191.1 | −1.34 | 0.36 | 1.01 | −0.63 | 0.75 | RPL15P2 | 0.42 | 0.39 | −0.43 | 0.39 | −0.68 | AC008906.2 | −0.04 | −0.41 | 0.30 | −0.47 | 0.04 |
| DAZAP2 | 0.31 | 0.05 | −0.31 | 0.04 | −0.44 | AC013244.2 | 0.76 | −1.39 | −0.03 | −0.51 | 0.01 | AC093899.1 | 0.30 | −0.54 | 2.22 | −1.27 | 1.39 |
| RPL5P11 | −1.05 | 0.52 | 1.66 | −0.08 | −0.44 | AC090574.1 | −0.87 | 0.51 | 0.24 | 1.47 | 0.02 | AGRP | −0.07 | 0.42 | 0.23 | 0.48 | 0.77 |
| KBTBD3 | −0.52 | 0.41 | 1.01 | 0.02 | 0.33 | PDZPHIP | −0.48 | 0.25 | 0.61 | −0.37 | 0.47 | AL109763.1 | 0.55 | −1.65 | −1.18 | 0.17 | 0.82 |
| AL391987.2 | −2.02 | −0.80 | 1.46 | 1.85 | 1.71 | AL121845.4 | 0.45 | 0.18 | −0.34 | 0.25 | −0.20 | AL451061.1 | 0.55 | −1.46 | −0.91 | 0.25 | 1.31 |
| CCDC198 | −0.91 | 0.13 | 0.39 | 0.02 | −0.12 | AC027020.1 | 0.26 | −0.19 | −0.37 | 0.37 | 0.33 | AC079226.2 | −0.18 | −0.96 | 1.00 | −0.52 | 2.13 |
| AL158210.2 | 1.93 | −1.45 | −3.12 | −1.00 | −1.64 | AC084368.1 | 0.34 | 0.28 | 0.37 | −0.03 | −0.16 | LINC01345 | 0.33 | −0.19 | −1.57 | −1.35 | −2.29 |
| AC008763.1 | −1.35 | 0.98 | 1.24 | −0.51 | −0.13 | RNU6-222P | −0.87 | 0.31 | 0.91 | 0.51 | −0.11 | PNMA6F | 0.33 | −0.45 | −0.05 | −0.87 | −0.40 |
| MPPE1 | −0.29 | 0.09 | 0.43 | 0.11 | 0.14 | AC087477.5 | −0.67 | 0.22 | −0.11 | 0.90 | 0.19 | NRSN1 | 0.10 | −1.35 | 0.80 | 0.76 | 0.67 |
| AC008781.2 | 0.48 | −0.29 | −0.67 | −0.14 | −0.43 | AL139099.3 | 0.40 | −1.24 | −1.90 | 0.14 | −0.80 | AL357079.1 | −0.04 | −0.33 | 0.74 | −0.42 | 1.03 |
| LINC02140 | −1.18 | 0.53 | 0.91 | 1.03 | 1.05 | LZTFL1 | −0.11 | 0.24 | 0.34 | 0.06 | −0.05 | G20695 | 0.46 | −0.80 | 1.06 | −0.85 | 2.32 |
| LPCAT4 | −0.42 | 0.20 | 0.66 | 0.04 | 0.31 | RNGTTP1 | −0.38 | −0.22 | 1.87 | −0.05 | 1.06 | AP003062.1 | 0.54 | −0.40 | −0.25 | −0.24 | −1.21 |
| L1CAM | −0.58 | 0.61 | 0.08 | 0.49 | 0.27 | LINC02493 | −0.86 | −0.60 | −0.30 | 0.96 | 0.79 | CICP13 | 0.14 | −1.00 | 0.69 | 0.13 | 0.03 |
| AL356258.1 | −0.76 | −0.06 | 0.70 | −0.33 | 0.24 | G6793 | 0.54 | 0.60 | 2.12 | 0.16 | 0.74 | LINC00513 | −0.02 | −0.28 | −0.04 | −0.32 | 0.19 |
| AL133163.1 | 2.46 | −2.79 | −2.65 | −0.13 | −0.66 | AL139230.1 | 0.35 | −0.13 | 0.55 | −0.14 | 0.98 | AL137845.1 | −0.17 | 0.31 | 0.10 | −0.50 | −1.16 |
| LINC01960 | 1.25 | −0.62 | −3.28 | −0.11 | −2.07 | SPATA5 | 0.08 | −0.10 | −0.09 | −0.06 | 0.00 | LINC02016 | −0.15 | −1.99 | 0.04 | −1.74 | 0.13 |
| PSG6 | −0.96 | 0.46 | 0.79 | −0.28 | −0.58 | AL023973.1 | −0.64 | 0.62 | 0.50 | 1.08 | −0.54 | OR5M1 | −0.13 | 0.52 | −0.44 | 0.27 | −0.22 |
| G27476 | −1.18 | 0.21 | 1.34 | −0.14 | 0.64 | HMGB3P32 | −0.50 | 0.48 | −0.27 | 0.04 | −0.51 | C1orf162 | −0.04 | −0.23 | 0.26 | −0.46 | 0.10 |
| RNA5-8SP2 | −1.05 | −0.26 | −0.48 | 0.60 | −0.23 | RP11-497H16.4 | −0.37 | 0.02 | 0.11 | 0.37 | 0.87 | AC113347.4 | 0.21 | −0.54 | −1.21 | 0.68 | −0.96 |
| C11orf44 | 1.37 | −0.97 | −0.91 | −0.26 | −0.31 | AC018462.1 | 0.15 | −0.14 | −0.16 | −0.08 | 0.02 | AC005616.1 | −0.52 | −0.29 | −0.28 | −1.55 | −0.49 |
| RNF125 | −0.36 | 0.13 | 0.27 | 0.12 | 0.12 | PIMREG | 0.20 | −0.47 | −0.21 | −0.28 | 0.17 | AP000943.4 | 0.10 | −0.67 | −0.90 | 0.51 | 0.49 |
| AC015923.1 | 0.95 | −0.50 | −0.89 | −0.02 | −0.06 | APOA5 | 1.16 | −1.91 | 0.02 | −0.63 | 0.18 | AL022345.9 | 0.17 | 0.87 | 0.84 | 0.91 | −1.02 |
| SAMD5 | −0.72 | 0.58 | 0.66 | −0.03 | 0.03 | AP000797.3 | −0.82 | 1.29 | −0.50 | 1.07 | −1.09 | AC111000.2 | −0.28 | 0.86 | 1.93 | 0.15 | 1.19 |
| RNA5SP22 | −1.46 | 0.27 | 1.57 | 0.46 | −0.02 | LINC01491 | 0.79 | 0.12 | −0.64 | 0.27 | −0.35 | AC007595.1 | 0.13 | −0.65 | −1.05 | 1.05 | 0.11 |
| AC022154.1 | −0.78 | −0.28 | 0.31 | −0.33 | 0.40 | SINHCAFP2 | 0.44 | −0.28 | −1.88 | −0.85 | −1.14 | ACIN1 | −0.01 | −0.05 | −0.11 | −0.11 | 0.06 |
| G43485 | −2.14 | 2.04 | 2.50 | −0.09 | 0.11 | LYPD2 | −0.56 | 0.78 | 3.03 | −0.43 | 0.22 | AL590068.3 | 0.24 | −0.02 | −1.65 | 0.17 | −1.50 |
| ADCYAP1R1 | −0.89 | 0.27 | 1.46 | −0.20 | 0.39 | RNU2-22P | −0.57 | −0.38 | 0.81 | −0.53 | 0.89 | RNU6-1146P | 0.09 | −0.65 | 0.50 | 0.22 | 0.61 |
| APELA | 1.16 | −0.80 | −0.36 | −1.00 | −0.73 | HRASLS2 | 0.63 | −0.93 | −1.13 | −0.85 | −0.45 | DCAF13P1 | 0.13 | 0.88 | −1.12 | 0.57 | 0.21 |
| HTR3A | 1.48 | −0.18 | −0.41 | 0.66 | −0.49 | DELE1 | −0.06 | −0.04 | −0.05 | 0.05 | 0.01 | AC133065.2 | 0.16 | −1.51 | −1.19 | −0.64 | 1.67 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| MBTD1 | −0.25 | 0.33 | 0.40 | 0.23 | 0.04 | AC008609.1 | 0.56 | −1.10 | 0.79 | −0.04 | 1.93 | LINC01988 | −0.11 | −0.83 | −0.73 | 0.39 | 1.08 |
| FRRS1L | −1.19 | 0.45 | −0.20 | 0.62 | −0.39 | LINC01500 | −0.78 | 0.38 | 0.62 | −0.35 | 0.09 | NECAP1P1 | −0.18 | 1.33 | 0.72 | −0.60 | −1.13 |
| AL136531.1 | −0.38 | −0.10 | 0.26 | −0.02 | 0.36 | OR2C1 | −0.67 | 0.08 | −0.02 | 0.42 | −0.52 | AL137849.1 | −0.31 | 1.73 | 1.05 | 0.60 | −0.15 |
| RPP25 | 0.39 | −0.32 | −0.53 | 0.11 | −0.07 | ASS1P10 | −1.03 | 0.40 | 2.20 | −1.58 | 1.57 | AC068533.3 | 0.05 | 0.13 | 0.19 | −0.04 | 0.13 |
| AC107398.1 | 1.26 | 0.19 | −0.69 | 0.29 | −0.93 | AL117190.1 | 0.31 | 0.00 | 0.42 | −0.18 | −0.08 | AC004832.4 | −0.07 | −0.13 | 0.46 | −0.29 | 0.53 |
| AP000355.1 | −1.39 | −0.30 | 0.45 | 0.38 | 0.80 | ELMO1 | −0.15 | −0.08 | 0.38 | −0.18 | 0.19 | AC106858.1 | 0.23 | 1.19 | −0.94 | 1.12 | 0.37 |
| AP000897.1 | −0.68 | 0.01 | 0.70 | −0.39 | 0.01 | HMGB3P24 | 0.27 | 0.11 | −0.44 | −0.12 | −0.48 | LYPLA2P2 | −0.16 | −0.34 | 1.44 | 0.95 | −0.13 |
| B3GNT2 | 0.53 | −0.21 | −0.24 | −0.54 | −0.19 | AL122010.1 | 0.20 | −0.09 | 0.06 | −0.35 | −0.12 | AC104619.2 | −0.54 | −0.40 | 0.12 | −0.64 | 1.53 |
| RNUSB-1 | −1.07 | 0.56 | −0.33 | 1.07 | −0.50 | ARIH2P1 | 0.57 | −1.07 | −1.17 | −0.23 | −0.57 | ORSAK4P | 0.19 | 0.33 | 1.37 | −0.23 | −0.45 |
| AC000061.1 | −1.76 | 0.32 | 2.08 | 0.26 | 0.83 | RILPL2 | −0.15 | −0.32 | 0.09 | −0.33 | 0.16 | AL353801.1 | 0.06 | −0.45 | −0.57 | −0.07 | 0.47 |
| HES4 | −0.57 | 0.09 | 0.04 | 0.02 | −0.18 | RBM14-RBM4 | 0.34 | −0.19 | 0.36 | 0.21 | 1.03 | HSPE1P10 | −0.24 | −0.53 | −2.02 | 0.31 | −0.12 |
| SAMD15 | 0.50 | −0.19 | −0.31 | −0.05 | −0.16 | PLPPR2 | 0.10 | 0.05 | −0.15 | 0.09 | −0.05 | G38112 | −0.05 | −0.29 | 0.19 | 0.25 | 0.68 |
| RNF2 | 0.40 | −0.09 | −0.34 | −0.11 | −0.41 | AL132796.2 | 0.67 | 0.17 | 0.11 | −0.62 | −2.04 | LINC00446 | 0.20 | 0.28 | −0.60 | 1.25 | −0.99 |
| AC022211.1 | 1.02 | −1.19 | −0.46 | −0.23 | 0.82 | SNORD114-10 | 0.92 | −0.18 | 0.74 | −0.69 | −0.36 | C1QB | 0.06 | −0.12 | −0.42 | −0.12 | −0.55 |
| PDCD1LG2 | 0.64 | −0.35 | −0.48 | −0.31 | −0.22 | AL020997.3 | 0.58 | 0.41 | 1.20 | −0.33 | 0.09 | AP002387.1 | 0.06 | −0.04 | 1.46 | 0.22 | 0.97 |
| ITPRIPL1 | 0.58 | −0.38 | −0.28 | 0.11 | 0.21 | AL512356.3 | −0.63 | −0.46 | 0.61 | −0.05 | 1.07 | PCNAP1 | −0.11 | −0.41 | 0.46 | −0.02 | 0.30 |
| ADRA2C | −0.94 | 0.45 | 0.28 | 0.72 | 0.14 | AC069549.1 | 0.31 | 0.39 | 0.69 | 0.01 | −0.01 | AL805961.1 | −0.24 | −0.86 | −0.33 | −0.64 | −2.49 |
| AC011495.1 | −0.89 | 0.25 | 0.60 | 0.48 | 0.46 | LECT2 | −0.86 | −0.45 | 1.15 | −1.21 | 1.12 | AC009480.1 | −0.06 | −0.69 | 0.66 | −0.48 | 0.44 |
| SMIM13 | 0.32 | −0.07 | −0.04 | −0.12 | −0.21 | AC005252.2 | −1.46 | 0.27 | −0.36 | 1.29 | −0.37 | CAPRIN2 | −0.01 | 0.03 | 0.10 | −0.09 | 0.07 |
| BCHE | −0.79 | 1.09 | 0.57 | 0.57 | −0.04 | AL449403.2 | −0.67 | −1.52 | 0.06 | 0.39 | 1.66 | SNX18 | 0.02 | −0.01 | 0.29 | −0.22 | −0.10 |
| AC005332.3 | −0.54 | 0.35 | 0.44 | 0.25 | 0.36 | DAP3P2 | 0.37 | −0.76 | 0.59 | 0.04 | 1.24 | AC010542.4 | −0.08 | 0.21 | 1.08 | −0.49 | 1.21 |
| RN7SL540P | −1.20 | 0.06 | 0.08 | 0.42 | 0.31 | AC009509.3 | 0.34 | −0.44 | −0.07 | −0.04 | 0.50 | LINC01985 | −0.32 | 1.72 | 0.27 | 0.82 | −0.99 |
| BRD1 | −0.32 | 0.32 | 0.08 | 0.19 | −0.09 | RPL18AP7 | 0.31 | −0.18 | −0.49 | 0.04 | 0.00 | AL591167.1 | −0.09 | −0.80 | −0.74 | 0.47 | 0.01 |
| RABL3 | 0.37 | −0.05 | −0.23 | −0.06 | −0.29 | P2RY13 | 0.32 | −0.62 | 0.08 | 0.04 | 0.36 | AC010631.1 | 0.23 | −0.26 | −2.22 | 1.43 | −1.14 |
| PI4KAP1 | −0.66 | 0.16 | 0.39 | 0.25 | 0.38 | GBX2 | −0.53 | 0.54 | 0.62 | 1.18 | −0.48 | HIF1A-AS1 | −0.18 | 0.25 | 0.15 | 0.07 | −1.12 |
| OXGR1 | −0.96 | 0.46 | 1.48 | 0.16 | 0.77 | RNU6-428P | −1.19 | 0.15 | 0.72 | −0.13 | 0.27 | RN7SKP205 | −0.54 | −0.48 | −0.44 | 1.17 | 0.72 |
| G29376 | −1.36 | −0.32 | 1.07 | 0.15 | 1.51 | POP5 | 0.09 | −0.01 | 0.08 | 0.00 | 0.17 | AC009509.4 | 0.07 | −0.79 | 1.05 | −0.30 | 1.09 |
| QSER1 | 0.35 | −0.09 | −0.18 | −0.07 | −0.10 | C17orf100 | −0.22 | −0.05 | 0.81 | −0.16 | 0.44 | AC068075.1 | 0.11 | −0.81 | −0.28 | −0.16 | 0.59 |
| DDX17 | −0.26 | 0.23 | 0.26 | 0.12 | 0.11 | C8orf37-AS1 | −0.32 | 0.35 | 0.17 | −0.34 | −0.49 | AC231759.1 | 0.30 | −1.14 | −0.73 | −0.55 | 0.91 |
| RP13-608F4.1 | −0.74 | 0.16 | 0.25 | 0.33 | 0.58 | AP001086.1 | 0.72 | 0.23 | −0.50 | −0.79 | −1.10 | ADAMTS7P4 | −0.07 | 0.32 | −0.03 | −0.03 | 0.13 |
| G29144 | 1.09 | −0.34 | −0.85 | −0.17 | −0.16 | PPIAP42 | 0.36 | −0.62 | 0.27 | −0.21 | 0.64 | DDA1 | −0.02 | 0.00 | −0.20 | −0.03 | −0.09 |
| METRNL | 0.32 | 0.25 | −0.15 | −0.06 | −0.64 | G961 | −0.37 | 0.75 | −0.84 | 0.51 | 0.01 | AC026371.1 | −0.54 | 0.27 | −2.48 | 0.97 | 0.34 |
| AL138963.1 | −0.54 | 0.08 | 0.56 | −0.15 | 0.25 | IST1 | −0.06 | 0.11 | −0.02 | 0.08 | −0.09 | AP003478.1 | 0.39 | −1.13 | −0.48 | −0.41 | 0.70 |
| AC118549.1 | 0.21 | 0.01 | −0.06 | 0.03 | −0.01 | C4orf54 | −0.45 | −0.11 | −0.77 | −0.08 | −0.22 | AL512604.3 | 0.42 | −1.03 | 0.23 | 0.94 | −0.30 |
| RPS29P29 | −1.21 | −0.16 | 0.86 | −0.23 | 0.20 | AC024619.4 | −0.61 | 0.70 | −0.68 | −1.05 | −2.00 | AC084880.3 | −0.06 | 0.94 | 0.03 | −0.32 | −0.85 |
| DONSON | 0.33 | −0.43 | −0.37 | −0.01 | 0.02 | AC244517.12 | −1.16 | −0.03 | 1.34 | 0.04 | 1.89 | CIB4 | 0.20 | −1.11 | −1.84 | 1.36 | 1.86 |
| DZANK1 | −0.34 | 0.14 | 0.27 | −0.01 | −0.03 | SCARNA23 | −0.34 | 0.20 | 0.10 | 0.25 | −0.30 | G6224 | 0.30 | −0.53 | 0.46 | 0.24 | 0.81 |
| STK38 | −0.33 | 0.19 | 0.39 | −0.08 | −0.03 | RNU6-701P | −0.30 | −0.19 | 0.36 | 0.18 | 0.20 | AL596223.1 | −0.12 | −0.88 | 0.51 | −0.92 | −0.19 |
| IMPACT | 0.41 | −0.23 | 0.01 | −0.10 | 0.01 | C7orf65 | −1.10 | −0.55 | 0.92 | −0.15 | 1.18 | AL445493.2 | 0.25 | −1.65 | 1.49 | −0.81 | 2.43 |
| FASTK | −0.29 | 0.09 | 0.09 | 0.12 | 0.19 | AC094019.1 | −0.38 | 0.43 | 0.19 | 0.29 | −0.34 | OR2W2P | 0.40 | 0.28 | −0.86 | −0.73 | −1.83 |
| SLC40A1 | −0.70 | 0.89 | 1.07 | 0.06 | −0.04 | AC132192.1 | 0.28 | −0.77 | −0.54 | −0.23 | 0.20 | AC136624.3 | −0.09 | −1.00 | 0.92 | −0.74 | 0.19 |
| RN7SL426P | −0.94 | 0.31 | 0.22 | 0.70 | 0.40 | AC025575.2 | −0.83 | −0.99 | 0.47 | 1.13 | 2.29 | IL15RA | 0.02 | −0.12 | −0.04 | 0.08 | 0.02 |
| DUSP1 | −0.47 | 0.43 | 1.08 | −0.55 | 0.09 | BTBD6P1 | 0.85 | 1.08 | −0.81 | 1.52 | 0.67 | AC244100.3 | 0.20 | 2.13 | 0.65 | −0.99 | −1.80 |
| CSPG4P9 | −0.93 | 0.28 | −0.07 | 0.57 | 0.33 | AC011731.1 | −0.53 | −0.65 | −0.48 | −0.34 | 1.04 | AC020658.2 | −0.13 | −0.25 | −2.39 | 0.40 | −1.49 |
| CD53 | 0.79 | −0.89 | −0.21 | −0.36 | 0.00 | CC2D2B | −0.11 | 0.01 | 0.28 | −0.05 | 0.15 | CTD-2201I18.1 | −0.04 | 0.48 | −0.82 | −0.10 | −1.17 |
| AL121790.1 | −1.19 | 0.64 | 1.80 | 0.61 | 1.34 | LHX9 | 0.44 | −0.59 | −0.53 | 0.10 | −0.62 | AC079741.1 | 0.14 | 0.65 | 0.02 | 0.22 | 0.90 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| ADGRL2 | 0.49 | 0.00 | −0.10 | −0.09 | −0.46 | HARS2 | 0.06 | −0.14 | −0.11 | 0.08 | 0.16 | AL445259.1 | 0.10 | −0.44 | −0.26 | 1.09 | −1.62 |
| CLCC1 | −0.26 | 0.11 | 0.25 | 0.09 | 0.22 | AL606534.1 | 0.55 | 0.16 | −0.25 | −0.40 | −0.82 | G39807 | −0.12 | 0.37 | 1.10 | 0.42 | −0.64 |
| RNVU1-1 | −1.74 | 1.08 | 0.14 | 1.11 | 0.32 | RNU6-501P | 0.40 | −0.85 | −1.36 | −0.97 | −0.46 | FRK | −0.02 | 0.19 | 0.11 | 0.52 | −0.01 |
| ACVRIC | −1.04 | 1.23 | 0.87 | 0.82 | −0.26 | AL359924.1 | −0.59 | −1.57 | 0.67 | −0.24 | 1.37 | AL096711.1 | 0.15 | −1.12 | −0.13 | −0.48 | 1.27 |
| NCK1 | 0.31 | −0.11 | 0.02 | −0.13 | −0.04 | KIF19 | 0.39 | −1.17 | −0.06 | 0.29 | 0.80 | GPATCH3 | −0.01 | −0.02 | −0.12 | −0.03 | −0.06 |
| GLUD1 | 0.34 | 0.16 | −0.21 | 0.00 | −0.50 | AC016738.2 | −0.33 | 0.96 | −0.68 | −0.12 | −1.26 | AC096576.1 | −0.30 | −0.81 | 1.06 | 0.62 | 0.30 |
| ETAA1 | 0.31 | −0.07 | −0.12 | 0.02 | −0.01 | AC011468.4 | 0.58 | −0.41 | 0.76 | −0.37 | 0.30 | AMER3 | −0.12 | −0.37 | 0.50 | 0.16 | −0.84 |
| STRADB | −0.54 | 0.28 | 0.31 | 0.12 | 0.02 | CFAP221 | −0.33 | 0.13 | 0.59 | 0.46 | 0.26 | AC092162.1 | 0.22 | −0.09 | −0.45 | 0.45 | 0.87 |
| C6orf222 | −1.04 | 0.59 | 1.53 | −0.23 | −0.24 | AC138761.3 | −0.94 | −0.83 | 1.55 | 0.59 | 0.35 | AC008752.3 | 0.03 | −0.10 | −0.14 | 0.08 | 0.27 |
| ST3GAL4 | −0.44 | 0.13 | 0.48 | −0.06 | 0.26 | LINC01488 | −0.74 | 0.81 | −1.14 | 0.25 | −0.24 | LINC00437 | 0.49 | 1.41 | −0.55 | −0.53 | −1.23 |
| OR1C1 | −0.95 | 0.85 | 0.26 | 0.76 | −0.06 | AC096541.1 | −0.37 | −0.28 | −0.55 | 0.19 | −0.21 | RNU2-40P | −0.53 | −0.23 | 0.25 | −0.32 | −0.07 |
| AC118282.1 | −1.16 | 0.47 | 0.40 | 0.69 | 0.06 | MAP1LC3B | 0.13 | 0.23 | −0.07 | 0.05 | −0.43 | AC008115.4 | 0.07 | 0.02 | −0.88 | 0.68 | 0.22 |
| C22orf31 | −0.96 | 0.98 | 1.21 | −0.04 | 0.24 | AC011447.7 | −0.42 | −0.77 | 1.21 | −0.54 | 0.42 | RPL15P21 | −0.13 | −0.57 | 0.52 | 0.37 | 1.18 |
| G27789 | 1.57 | −0.20 | −0.27 | −0.10 | −1.29 | AL161452.1 | −0.68 | −1.27 | 1.41 | 0.10 | 1.89 | AC007533.1 | 0.03 | 0.26 | 0.12 | 0.04 | 0.02 |
| ACCSL | −1.37 | −0.11 | −0.79 | 0.50 | −0.19 | AL158212.3 | −0.12 | 0.31 | 0.32 | 0.08 | 0.08 | RNU6-881P | 0.16 | 1.22 | −0.59 | 1.50 | −0.78 |
| AC100830.1 | −0.75 | 0.91 | 0.48 | 0.70 | −0.04 | AL928970.1 | 0.36 | 0.01 | −0.17 | 0.49 | 0.35 | HTR5A-AS1 | 0.14 | −1.11 | −1.40 | 1.86 | 0.40 |
| AC104958.1 | −0.68 | 0.45 | 1.94 | −0.39 | 0.02 | RP11-782C8.7 | −0.54 | 0.32 | 0.64 | 0.13 | 1.22 | AL445213.1 | −0.10 | −0.67 | −0.65 | −0.28 | −0.62 |
| LATS2 | −0.31 | 0.06 | 0.31 | −0.31 | −0.11 | AC009054.1 | −0.23 | −0.11 | 0.52 | −0.17 | 0.21 | FCAMR | −0.11 | −1.15 | −0.86 | −0.71 | −1.26 |
| INTS9 | 0.27 | −0.17 | −0.31 | −0.03 | −0.10 | AC133785.1 | 0.35 | 0.43 | −0.29 | 0.66 | −0.47 | AC009686.2 | 0.06 | −0.28 | 0.78 | −0.27 | 0.51 |
| AC245884.1 | −1.65 | −0.25 | 1.06 | 0.24 | 1.12 | AC109481.1 | 0.32 | −0.17 | 0.00 | 0.05 | −0.15 | MME-AS1 | 0.09 | −0.22 | −0.78 | −0.41 | 0.16 |
| MYOZ1 | −1.25 | −0.19 | 1.10 | −0.66 | −0.02 | ELOA3 | 0.50 | −0.04 | −0.22 | 1.14 | 0.39 | LINC00454 | 0.24 | 0.35 | 0.36 | 0.30 | 0.53 |
| MIR98 | 1.00 | −0.04 | −1.27 | 0.25 | −1.48 | G13670 | −0.67 | −0.19 | 1.90 | −0.54 | 1.66 | MIR215 | −0.10 | −0.65 | 0.15 | −0.68 | 0.69 |
| G5182 | −0.83 | −0.44 | −0.25 | −0.36 | 0.05 | RNU7-169P | 0.66 | −1.19 | −0.15 | 0.36 | 1.31 | PMEL | −0.04 | 0.63 | −0.54 | 0.78 | −0.43 |
| OTOA | −1.03 | 0.12 | 0.31 | 0.31 | 0.32 | RP11-58A12.3 | −1.35 | −0.10 | 2.03 | −0.44 | 3.02 | SLC19A1 | −0.03 | −0.26 | −0.67 | −0.04 | −0.24 |
| PCYT2 | 0.29 | −0.12 | −0.50 | 0.17 | −0.12 | DEFB109A | −0.72 | −0.43 | 1.67 | 0.19 | 0.93 | AC103691.2 | −0.19 | 0.44 | 2.60 | 0.64 | 0.60 |
| LINC02516 | −0.83 | 0.24 | 0.97 | −0.60 | −0.02 | AC026904.2 | 0.52 | −0.59 | −0.31 | −0.77 | −0.83 | AC092994.1 | 0.53 | −0.62 | −2.23 | 1.98 | −2.28 |
| FCN2 | −1.95 | 1.97 | 1.35 | 1.16 | −1.30 | RPS27P29 | 0.81 | −0.71 | −1.89 | 0.02 | −1.04 | RNU6-315P | −0.05 | 0.39 | −0.02 | −0.27 | −0.42 |
| AL035446.2 | −1.67 | 0.87 | 0.67 | 0.45 | −0.09 | AP003785.1 | 0.48 | −0.05 | −0.11 | −0.62 | −0.80 | AC006115.2 | −0.53 | 1.15 | 0.30 | −0.61 | −1.70 |
| MIEN1 | 0.47 | 0.11 | −0.16 | −0.01 | −0.36 | SLC18A3 | 1.41 | −0.77 | −3.29 | 0.47 | −2.12 | MED14P1 | −0.53 | −0.11 | 0.69 | −0.36 | −0.68 |
| GAS2L1 | 0.47 | −0.09 | −0.41 | 0.16 | −0.06 | MIR1-1HG | −0.78 | 0.28 | 0.86 | 0.66 | −1.76 | AC017015.1 | 0.08 | 0.44 | −1.13 | −0.37 | −1.80 |
| AP005436.2 | 1.06 | −0.69 | −0.45 | −0.28 | −0.04 | PPIAP41 | 0.16 | −0.05 | −0.20 | −0.02 | −0.20 | AC024579.1 | −0.53 | 1.09 | 1.13 | −1.68 | −0.26 |
| NPM1P13 | −1.13 | 0.48 | −0.07 | 0.28 | −0.68 | PARVG | −0.26 | −0.56 | −0.16 | −0.09 | 0.27 | AC008628.2 | −0.53 | −0.03 | 0.80 | 0.58 | 0.26 |
| IMPAD1 | 0.41 | −0.13 | −0.24 | −0.13 | −0.23 | AL121983.2 | 0.39 | −0.17 | −0.83 | 0.08 | −0.56 | AC005521.1 | 0.29 | 0.31 | −0.94 | −0.63 | −2.19 |
| AC008395.1 | −0.79 | 0.19 | 0.43 | 0.52 | 1.06 | NLRP11 | 0.56 | 0.45 | −1.00 | 0.70 | −0.32 | AC134878.1 | 0.09 | 0.30 | 0.63 | 0.67 | 1.31 |
| SNORD116-29 | −1.53 | 0.74 | 1.60 | 0.25 | −0.48 | CERNA1 | −0.30 | 0.78 | 1.03 | 0.26 | −0.15 | NCS1 | 0.02 | 0.22 | −0.12 | 0.08 | −0.33 |
| ATP5MC2 | 0.36 | −0.02 | −0.02 | −0.10 | −0.09 | RPS3AP3 | 0.50 | 0.06 | −0.76 | −0.83 | −2.54 | BNIP3P39 | 0.06 | 0.10 | 0.57 | 0.59 | 0.58 |
| CFAP36 | −0.26 | 0.15 | 0.42 | −0.04 | −0.02 | AL357833.1 | 0.63 | −0.41 | −0.24 | −0.58 | −0.64 | RPL8P2 | 0.40 | −1.65 | −1.40 | 0.75 | 1.73 |
| CTH | −0.74 | 0.39 | 0.56 | 0.12 | 0.06 | RN7SL226P | −0.99 | 0.80 | 1.17 | −1.36 | −1.32 | AC009955.3 | −0.10 | −0.43 | −2.13 | 0.88 | 0.12 |
| S1PR4 | 1.14 | −0.47 | −0.95 | −0.03 | −0.69 | BIRC6-AS1 | 0.36 | 0.47 | −0.46 | 0.50 | 0.07 | GRXCR1 | 0.53 | −0.41 | 0.93 | −1.06 | −1.10 |
| KCNK2 | −0.84 | 0.44 | 1.55 | −0.75 | 0.43 | PLXDC1 | −0.17 | −0.16 | 0.49 | −0.43 | 0.22 | KRT34 | 0.07 | −0.20 | 1.82 | −1.27 | −0.07 |
| RNASEH2B-AS1 | −0.78 | −0.40 | 0.13 | −0.10 | 0.43 | AC092794.1 | 0.32 | −0.41 | 0.24 | 0.10 | 0.43 | AC138938.1 | 0.53 | −0.64 | −2.01 | −0.28 | −0.99 |
| FBXL14 | −0.30 | 0.28 | 0.22 | 0.15 | 0.14 | AL139099.4 | 0.17 | −0.45 | −0.63 | −0.21 | −0.58 | AC091138.1 | 0.33 | −1.39 | 0.21 | 0.06 | −1.19 |
| NT5C3A | 0.29 | −0.02 | −0.08 | 0.08 | −0.18 | HNRNPA1P47 | −0.93 | −0.10 | 0.48 | 1.04 | 0.83 | MIR2117HG | −0.05 | −0.25 | −0.48 | −0.37 | 0.29 |
| MGA | 0.21 | −0.02 | 0.00 | −0.10 | 0.08 | HPN | −0.53 | −1.04 | 1.66 | −0.52 | 0.99 | AC133485.5 | 0.53 | −0.13 | 0.02 | −1.49 | −2.56 |
| PRSS48 | −0.58 | 0.26 | 0.17 | 0.20 | 0.02 | RNY4P25 | 0.48 | −0.25 | −0.80 | 0.36 | −0.18 | AL355798.1 | −0.20 | −1.03 | −0.91 | 0.10 | −0.43 |
| NFIL3 | 0.51 | −0.28 | −0.47 | −0.33 | −0.19 | AC011840.3 | −1.06 | −0.40 | 1.47 | 0.27 | 0.73 | OR10J1 | 0.13 | 0.53 | −0.90 | 0.27 | 0.15 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC232271.1 | −0.51 | 0.23 | 0.46 | −0.05 | 0.04 | AC074389.1 | 0.67 | −0.06 | −1.07 | −0.20 | −1.73 | DEFB131A | 0.49 | 0.88 | −0.13 | 1.68 | 0.42 |
| ATF6B | −0.29 | 0.19 | 0.14 | 0.17 | 0.00 | BTBD7P1 | 0.35 | −0.07 | −0.23 | 0.05 | 0.08 | AL355997.1 | 0.12 | −0.57 | −2.26 | −0.35 | −2.37 |
| AL355483.1 | 2.26 | −0.08 | −0.83 | 0.38 | −0.12 | SFRP4 | −0.46 | 0.68 | −0.59 | 0.14 | −2.19 | MIR635 | 0.04 | −0.12 | 0.35 | −0.29 | 0.67 |
| AL442163.1 | −1.17 | 0.02 | 1.55 | 0.11 | 1.02 | AC011396.2 | 0.95 | 0.36 | 0.70 | −0.01 | −0.85 | SEC14L2 | 0.02 | 0.01 | −0.04 | −0.02 | −0.11 |
| AC008953.1 | 0.51 | 0.22 | −0.04 | −0.04 | 0.02 | AL713922.2 | 0.34 | −0.21 | −0.10 | 0.03 | 0.37 | OR4A4P | 0.22 | −0.65 | −0.28 | −0.17 | −0.58 |
| ATXN7L1 | −0.21 | 0.21 | 0.08 | 0.13 | 0.00 | IQCB2P | −0.78 | −1.50 | 0.56 | −0.66 | 0.17 | AC090539.2 | −0.30 | −1.27 | −1.31 | 2.02 | 2.39 |
| CTSV | 0.81 | −0.27 | −0.21 | −0.20 | −0.23 | AC026803.2 | −0.30 | 0.48 | −0.16 | 0.23 | 0.55 | CENPIP1 | −0.26 | −0.12 | −0.68 | 1.53 | −1.86 |
| PTGES3P1 | 0.51 | −0.21 | −0.27 | −0.17 | −0.09 | STK10 | 0.15 | −0.14 | −0.12 | −0.27 | −0.19 | AL607033.1 | 0.53 | −1.11 | −1.23 | 0.71 | 1.29 |
| KLKB1 | −1.04 | −0.02 | 0.17 | 0.30 | 0.12 | AP000943.1 | −1.17 | −1.13 | 1.59 | −1.02 | 1.83 | HCFC2P1 | 0.21 | −0.67 | −0.17 | 0.56 | −0.45 |
| MIR4664 | 1.07 | −0.10 | −1.23 | 0.31 | −0.28 | FUOM | −0.16 | −0.33 | −0.54 | 0.08 | 0.10 | MIR4725 | −0.09 | −0.57 | 0.58 | 0.99 | 1.57 |
| PRDX6 | 0.35 | −0.05 | −0.27 | 0.04 | −0.45 | AC079866.1 | 0.31 | −0.11 | 0.05 | −0.89 | −0.85 | HSCB | −0.02 | −0.26 | 0.16 | −0.14 | 0.38 |
| RN7SKP69 | −0.65 | 0.52 | 0.43 | 0.06 | 0.15 | AC016382.1 | 1.22 | −2.79 | 0.48 | 0.07 | 2.49 | OR6C71P | 0.22 | 1.07 | −3.01 | 1.36 | −2.31 |
| AP002498.1 | 0.78 | −0.16 | −1.76 | −0.15 | −1.11 | MTND5P40 | −0.86 | −0.79 | 0.33 | 1.15 | 1.61 | MIA3 | −0.01 | 0.17 | 0.18 | −0.03 | −0.06 |
| CCDC144B | −0.34 | 0.31 | 0.81 | 0.14 | 0.89 | CMTM8 | −0.21 | 0.50 | 0.56 | 0.10 | 0.04 | AC098479.1 | −0.19 | −0.10 | 0.96 | −0.31 | 0.88 |
| RNU6-36P | −1.28 | 0.78 | −0.76 | 1.26 | −0.18 | AC107983.1 | 0.35 | −0.43 | −0.10 | −0.09 | 0.10 | IGKVID-12 | 0.53 | 0.30 | 0.04 | 2.25 | −0.81 |
| GTPBP3 | −0.44 | 0.19 | −0.22 | 0.46 | 0.06 | C17orf78 | 0.20 | −0.38 | −0.09 | −0.17 | 0.22 | AC074008.2 | −0.14 | −0.55 | −0.96 | 0.86 | −1.90 |
| RAB21 | 0.30 | −0.04 | −0.11 | −0.02 | −0.18 | SMC5 | 0.08 | −0.01 | −0.28 | −0.03 | −0.19 | AC006065.4 | 0.13 | −0.99 | −0.57 | −0.18 | 0.14 |
| KCNC4 | −0.45 | 0.64 | 0.65 | 0.33 | 0.26 | LINC00382 | 0.59 | −0.83 | −3.22 | 0.53 | −2.44 | SLC7A15P | −0.27 | −0.91 | 0.10 | 0.30 | 0.36 |
| IGHMBP2 | −0.33 | 0.18 | 0.13 | 0.15 | 0.08 | NFX1 | 0.06 | −0.01 | 0.00 | −0.02 | 0.00 | AC098799.2 | 0.37 | −1.11 | −0.43 | 0.07 | −0.12 |
| ROBO3 | −0.48 | 0.18 | 0.34 | 0.35 | 0.17 | AC087277.2 | 0.54 | −1.39 | −0.79 | 0.52 | 1.71 | PGM2L1 | −0.03 | 0.05 | 0.30 | −0.19 | −0.01 |
| DPH5 | 0.29 | −0.32 | −0.22 | −0.17 | 0.03 | AL161893.1 | −0.57 | −0.43 | −0.45 | −0.44 | −0.10 | MCTP1 | 0.03 | 0.03 | 0.69 | −0.39 | −0.11 |
| RNU6-177P | 1.32 | −1.22 | −1.27 | 0.07 | −0.04 | ORC3 | 0.09 | −0.05 | 0.00 | −0.12 | −0.06 | CESSA | −0.08 | −0.70 | 0.94 | −0.16 | 0.56 |
| G7635 | 0.68 | −0.51 | −0.48 | 0.18 | 0.12 | AC092958.4 | 0.95 | −2.21 | −0.27 | −0.67 | −1.41 | RPSAP42 | 0.17 | −1.61 | −2.61 | 0.60 | −0.24 |
| KRT76 | 1.65 | −0.65 | −2.74 | 0.14 | −3.50 | FBXO42 | −0.09 | 0.14 | 0.23 | 0.12 | 0.09 | FEM1AP3 | −0.30 | −0.92 | −1.05 | −0.88 | 0.57 |
| FO681548.1 | −1.31 | 0.41 | 1.07 | 1.22 | 0.35 | AMN1 | −0.14 | 0.33 | 0.83 | −0.14 | 0.07 | RPSAP67 | 0.22 | −0.10 | −1.35 | 0.89 | −0.44 |
| CDC14A | −0.31 | 0.37 | 0.61 | 0.11 | 0.04 | PDSS1P1 | 0.22 | −0.14 | 0.11 | −0.06 | −0.06 | AC091180.1 | 0.12 | −1.45 | −1.45 | 0.06 | 0.98 |
| SNORD103B | 1.00 | −0.35 | −0.16 | −0.19 | −0.05 | AP000553.1 | 0.70 | −0.92 | 0.69 | −0.85 | 0.98 | AC233290.1 | −0.22 | −0.10 | −0.70 | −0.45 | −0.76 |
| MIR621 | 1.05 | −0.24 | −0.28 | −0.43 | −0.24 | C1QTNF1-AS1 | 0.44 | −0.95 | −0.98 | 0.11 | −0.56 | OR7G3 | −0.30 | 0.53 | −0.94 | 0.09 | −0.95 |
| AC017116.2 | −0.50 | 0.23 | 0.26 | 0.15 | 0.02 | AC091198.1 | 0.94 | 0.32 | −2.62 | 0.93 | −1.42 | AC022296.3 | −0.52 | 0.89 | 0.36 | 0.48 | 0.06 |
| HKR1 | −0.23 | 0.17 | 0.38 | −0.06 | 0.06 | AC114689.3 | −0.69 | −0.22 | −0.66 | 1.01 | −0.72 | RNU7-110P | −0.09 | −0.22 | 0.86 | 0.41 | 1.23 |
| RNF217-AS1 | −0.37 | −0.02 | 0.23 | 0.14 | 0.13 | AC104938.1 | −0.27 | 0.37 | 0.01 | 0.43 | 0.21 | G29778 | −0.04 | 0.08 | 0.51 | −0.16 | 0.24 |
| RPL37P2 | 1.11 | −0.59 | −0.11 | −0.10 | −0.16 | RPSAP47 | 0.44 | 0.22 | 1.14 | −0.86 | 0.24 | SMC4P1 | −0.26 | 0.00 | −0.04 | 0.88 | −0.84 |
| AC007598.1 | 0.87 | −0.17 | 0.20 | −0.04 | −0.05 | AC068790.6 | 0.49 | −0.48 | −0.55 | −0.15 | −0.23 | SPG11 | 0.01 | −0.06 | 0.07 | 0.01 | 0.11 |
| FGFBP3 | −0.66 | 0.51 | 0.67 | 0.26 | 0.33 | AC090099.5 | 0.94 | −0.70 | −2.16 | 0.29 | −2.31 | AL159158.1 | −0.19 | 1.65 | 1.33 | 0.85 | −1.59 |
| NOA1 | 0.26 | 0.09 | −0.27 | 0.20 | −0.27 | PDE6H | 0.82 | −1.82 | −1.43 | 0.72 | 0.76 | RN7SL109P | 0.09 | −0.71 | 0.33 | −0.16 | 0.43 |
| PRLR | −0.41 | 0.67 | 0.40 | 0.23 | 0.02 | AC116366.3 | 0.66 | −0.42 | 0.41 | −0.52 | 0.10 | RPS12P17 | −0.06 | −0.09 | −0.37 | 0.26 | −0.59 |
| G42720 | −0.85 | 0.32 | 0.77 | 0.45 | 0.09 | AC005840.4 | −0.35 | −0.31 | 0.50 | −0.12 | 0.89 | BORCS6 | 0.02 | 0.19 | 0.04 | 0.20 | −0.22 |
| FAM168B | 0.29 | −0.08 | −0.10 | −0.06 | −0.17 | MIR200A | −0.42 | 0.95 | −1.90 | 1.34 | −1.55 | AC016751.2 | −0.27 | −0.50 | −0.31 | −0.88 | −1.62 |
| ECHDC1 | 0.48 | −0.16 | −0.40 | −0.10 | 0.03 | KRTAP4-7 | −0.81 | −0.23 | −0.75 | −0.08 | −3.10 | AC068672.2 | 0.52 | −0.61 | −0.46 | −0.05 | 2.10 |
| AP001330.5 | 1.14 | −0.30 | −0.10 | 0.15 | −0.46 | RN7SL681P | −0.60 | 0.73 | 0.29 | 1.72 | 0.85 | KIAA1024 | −0.03 | −0.01 | 0.36 | −0.19 | −0.09 |
| ATG10 | −0.26 | 0.21 | 0.17 | 0.07 | 0.08 | RIPPLY2 | −0.58 | −0.70 | −1.53 | −0.10 | −1.86 | AL359854.1 | 0.17 | −0.38 | −1.07 | −0.40 | −0.97 |
| AC104758.3 | −1.07 | 0.34 | 0.24 | 0.15 | 0.02 | AC092134.1 | −0.66 | −0.18 | 1.58 | −0.83 | 0.58 | HTR3B | −0.12 | 2.05 | −0.72 | 1.30 | −0.96 |
| IDI1 | 0.55 | −0.06 | −0.65 | 0.10 | −0.53 | EIF2AP4 | −0.75 | −0.03 | 1.45 | 0.55 | −0.55 | AC005033.1 | −0.18 | −0.28 | −0.38 | 0.10 | 2.43 |
| IFT81 | −0.27 | 0.23 | 0.20 | −0.03 | −0.09 | CRB1 | −0.41 | 0.12 | −0.43 | 0.45 | −0.68 | AC063926.1 | 0.08 | −0.01 | −0.23 | 0.93 | 0.42 |
| AC079921.1 | 1.46 | −0.63 | −0.74 | −0.24 | −0.29 | SGK494 | −0.16 | −0.01 | 0.10 | −0.02 | 0.34 | RNA5SP363 | −0.06 | −0.37 | −0.47 | 0.13 | 0.22 |
| AC007842.1 | −0.60 | 0.08 | 0.44 | 0.35 | 0.20 | AC044849.1 | −0.56 | −1.55 | 0.75 | 0.33 | 2.85 | AC022558.1 | −0.03 | 0.04 | −0.15 | 0.42 | 0.47 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| MADCAM1 | −0.85 | 0.30 | 1.32 | 0.35 | 0.75 | AC016027.2 | −0.20 | −0.25 | −0.61 | 0.27 | 0.33 | AL133163.3 | −0.25 | 1.51 | −0.40 | 1.08 | −1.58 |
| CD2BP2 | 0.22 | −0.24 | −0.34 | −0.11 | −0.04 | COMMD3 | −0.18 | 0.39 | 0.68 | 0.08 | −0.24 | CYMP-AS1 | −0.52 | −0.40 | 0.29 | −1.35 | −0.27 |
| AP003071.5 | −1.01 | 0.91 | 1.13 | 1.22 | 1.06 | ACTBP9 | 0.58 | 0.13 | −0.37 | −0.08 | −0.21 | ARHGAP42P5 | −0.17 | −1.70 | −0.35 | −0.05 | 0.28 |
| FANCA | 0.53 | −0.90 | −0.92 | −0.19 | 0.14 | AC106733.1 | −0.90 | 0.52 | −0.46 | 1.54 | −0.93 | LINC01717 | 0.32 | 0.36 | −0.71 | 0.82 | −1.04 |
| GRIN3B | −0.63 | −0.16 | 0.09 | 0.41 | 0.35 | AL356057.1 | 0.27 | 0.15 | 0.04 | 0.32 | 0.04 | RD3L | 0.20 | −0.46 | −0.48 | −0.38 | 1.23 |
| SNORD104 | −0.87 | 0.21 | 0.52 | 0.49 | −0.11 | AL353595.1 | −0.75 | −0.73 | −1.50 | 2.46 | 0.22 | CCDC168 | 0.05 | 0.07 | −0.28 | 0.27 | −0.51 |
| C16orf89 | −1.32 | 1.19 | 1.65 | 1.50 | 0.71 | ACADM | −0.16 | 0.03 | 0.13 | 0.18 | 0.38 | AC010374.1 | 0.32 | 0.16 | 0.08 | 0.15 | −2.10 |
| RTF2 | 0.22 | −0.06 | −0.35 | −0.07 | −0.36 | AC093422.1 | 0.40 | 0.36 | −0.82 | 0.39 | −0.33 | AC027250.1 | −0.24 | −1.25 | −1.61 | −0.06 | 0.55 |
| AC004017.1 | −0.82 | 0.26 | 0.64 | 0.03 | 0.37 | G18341 | −0.53 | 0.55 | 0.41 | 0.20 | −0.04 | BX640515.1 | −0.09 | −0.65 | −1.16 | 0.47 | 0.80 |
| COLGALT2 | −0.64 | 0.13 | 0.60 | 0.03 | 0.06 | GOLM1 | −0.16 | 0.09 | 0.35 | −0.35 | −0.03 | AL512283.1 | −0.11 | −2.60 | −0.39 | −0.36 | 1.40 |
| AC008991.2 | −1.35 | 0.90 | 0.47 | 0.46 | −0.19 | OPN4 | −0.55 | −0.81 | 1.90 | −1.01 | −0.59 | AC112673.1 | 0.05 | −0.36 | 0.06 | 0.44 | 0.78 |
| SNORA22 | −0.62 | 0.54 | 0.47 | 0.45 | −0.36 | G26249 | 0.98 | −1.40 | 1.29 | 0.31 | 1.27 | AC092608.2 | 0.06 | −0.48 | −0.83 | 0.05 | 0.00 |
| ADAMTS6 | 0.66 | −0.46 | 0.07 | −0.40 | −0.27 | ADAMTSL4 | −0.15 | −0.21 | −0.10 | −0.14 | 0.05 | G913 | 0.05 | −0.99 | −0.18 | −0.12 | 0.78 |
| ACAP2-IT1 | 0.97 | −0.14 | −0.26 | −0.11 | −0.44 | AC073072.2 | 0.99 | −2.10 | −0.80 | 0.33 | 0.68 | RNA5SP170 | −0.34 | 0.42 | 0.53 | 0.39 | −0.78 |
| AC087392.1 | 0.49 | −0.51 | −0.19 | −0.37 | 0.20 | SSTR2 | −0.24 | 0.10 | 0.02 | 0.05 | −0.26 | RPL9P7 | −0.05 | 0.01 | 0.60 | −0.40 | 0.60 |
| RNF44 | −0.39 | 0.36 | 0.15 | 0.41 | 0.14 | RPS26P31 | −0.38 | 0.57 | −0.14 | −0.46 | −0.06 | ADGRL4 | −0.04 | 0.01 | 1.02 | −0.37 | −0.12 |
| AC092681.2 | −0.84 | 0.49 | 0.68 | 0.20 | −0.09 | H3F3AP1 | 0.73 | 0.57 | −0.18 | 0.55 | −1.16 | AL445528.2 | 0.52 | −0.88 | −0.27 | −1.92 | −1.70 |
| ARAP1 | −0.28 | −0.02 | −0.07 | 0.09 | −0.03 | KRT18P68 | −1.32 | 1.33 | 1.59 | 0.11 | 1.36 | LINC01571 | 0.18 | −0.50 | −0.88 | 0.22 | −1.18 |
| ENPP7P8 | −0.81 | 0.55 | 0.96 | 0.03 | 0.47 | ANP32BP1 | 0.45 | −0.22 | −0.75 | 0.22 | −0.24 | IGLC4 | −0.52 | −0.41 | 0.26 | −0.29 | 0.36 |
| STYK1 | 0.55 | −0.25 | −0.54 | −0.10 | −0.23 | FTH1 | −0.26 | −0.16 | 0.45 | −0.50 | −0.22 | AL136528.2 | −0.07 | 0.82 | −0.97 | 0.56 | −0.10 |
| RAI14 | −0.46 | 0.14 | 1.02 | −0.63 | −0.01 | LINC00407 | −0.66 | 0.46 | 0.05 | −0.97 | −0.70 | PDCL3P7 | 0.25 | −1.50 | 0.04 | −2.18 | −0.79 |
| C16orf91 | 0.57 | −0.03 | 0.04 | −0.28 | −0.21 | AC008568.1 | −0.64 | −0.01 | 0.25 | 0.49 | 1.30 | CCT7P1 | −0.04 | 0.45 | 0.86 | 0.21 | −0.06 |
| G34300 | −1.62 | −1.36 | 0.29 | 0.95 | 1.85 | KIF25 | 0.48 | −0.39 | −1.03 | −0.20 | −1.13 | AL359979.1 | 0.14 | 0.07 | −0.54 | 0.88 | −0.85 |
| AL157832.1 | −0.91 | 0.99 | 0.90 | 1.26 | 0.84 | MIR589 | 0.50 | −0.57 | −1.32 | −0.06 | −0.07 | BX510359.3 | 0.34 | −1.79 | −0.18 | −2.07 | −0.38 |
| AC244197.3 | −0.76 | 0.29 | 1.04 | 0.30 | 0.33 | AC004870.3 | 0.91 | −1.09 | −1.35 | 0.06 | −0.16 | RNU4ATAC17P | 0.31 | 0.13 | 1.21 | 0.51 | 0.39 |
| G13548 | −2.08 | 0.74 | 1.08 | 0.67 | 0.49 | AC010422.1 | −0.53 | 0.42 | 1.31 | −0.29 | −0.62 | AL359237.1 | −0.10 | −0.53 | −1.59 | 0.04 | −0.59 |
| HIST2H3D | 0.67 | −0.65 | −1.24 | −0.09 | −1.01 | AFAP1-AS1 | 0.22 | −0.16 | 0.25 | −0.80 | −0.46 | AC233289.1 | −0.49 | −0.08 | 1.10 | −0.77 | 0.90 |
| AL604028.1 | −0.66 | −0.27 | 0.21 | 0.07 | 0.55 | RPL4P5 | 0.28 | 0.01 | −0.28 | −0.09 | −0.64 | CTBP2P6 | −0.24 | −0.31 | 0.66 | −0.34 | −0.77 |
| AC005358.2 | −1.24 | 0.20 | 0.79 | 0.67 | 0.68 | SEZ6 | −0.24 | 0.17 | 0.41 | −0.13 | 0.13 | AP000525.10 | −0.12 | −1.96 | 1.04 | −0.09 | 2.74 |
| AL357874.2 | −0.75 | 0.32 | 0.95 | 0.18 | 0.16 | AC006504.3 | 0.46 | 0.03 | −0.20 | −0.26 | −0.25 | KIF4CP | −0.11 | −0.21 | −0.80 | 0.68 | −0.76 |
| AL133153.1 | 1.92 | −0.88 | −1.24 | 0.10 | −0.28 | AL845552.1 | −0.28 | −0.55 | −1.14 | −0.28 | 0.04 | ITGB1-DT | 0.09 | −0.08 | 0.19 | −0.51 | 0.58 |
| LINC01979 | −1.55 | 0.06 | −0.11 | 0.70 | 0.14 | AC121334.1 | −1.15 | −0.74 | −1.13 | −0.21 | −0.02 | IPMKP1 | 0.25 | 0.93 | −0.94 | −0.33 | −2.41 |
| RNA5SP496 | 1.30 | −0.65 | −1.93 | 0.02 | −1.79 | RNU6-806P | −0.75 | 0.22 | 2.26 | 0.70 | 0.62 | KRTAP19-10P | −0.52 | 0.23 | NA | 1.83 | −1.09 |
| AC087521.2 | 0.57 | −0.24 | −0.51 | 0.20 | −0.11 | RNU1-73P | 0.52 | −0.30 | 0.41 | −0.40 | −0.81 | AOX3P | −0.06 | −0.92 | −0.37 | −0.39 | 0.08 |
| STIM1 | 0.22 | −0.04 | −0.36 | 0.03 | −0.15 | NDUFS1 | 0.05 | 0.03 | 0.00 | 0.04 | −0.04 | IGHV4-55 | 0.52 | −0.06 | −0.71 | 1.64 | −1.16 |
| ERCC3 | −0.18 | 0.11 | 0.03 | 0.03 | −0.04 | AC091862.1 | −0.77 | −0.45 | −0.40 | −0.33 | −1.24 | CFAP97D2 | 0.11 | −0.69 | −0.44 | −0.50 | −0.19 |
| EMILIN3 | −0.80 | 0.88 | 0.57 | 1.01 | 0.35 | RPL5P8 | −0.75 | −0.06 | −1.39 | 1.70 | −0.82 | IFNA4 | 0.52 | −0.69 | −1.23 | 1.51 | −0.72 |
| HOXC6 | −0.48 | 0.25 | 0.19 | 0.31 | −0.07 | AC114490.3 | −0.32 | 0.65 | 0.48 | 0.21 | 0.26 | AC055872.2 | −0.52 | 0.49 | 0.83 | 0.97 | 1.02 |
| CCNDBP1 | −0.32 | 0.17 | 0.32 | 0.04 | 0.10 | AC010285.1 | −0.34 | 0.39 | 0.81 | 0.14 | −0.20 | G25738 | −0.42 | 0.06 | 0.49 | −0.48 | −1.44 |
| AC073107.2 | −1.13 | 0.21 | 0.61 | −0.62 | −0.15 | RNU6ATAC24P | 0.37 | −0.17 | −0.52 | −0.51 | −0.43 | AC007731.3 | −0.52 | −0.75 | 0.29 | −0.56 | 0.08 |
| AC106820.1 | −1.73 | 1.63 | 1.04 | 1.46 | −0.12 | FAM86B2 | 0.39 | −0.53 | 0.48 | −0.13 | 1.39 | AP002906.1 | 0.13 | 1.08 | −1.13 | 1.43 | 0.22 |
| NANOGP4 | −0.82 | −0.31 | 0.52 | 0.09 | 0.28 | AC091973.1 | −0.93 | −0.49 | 2.17 | −1.23 | 0.09 | AL844165.1 | 0.12 | 0.77 | −0.40 | 0.31 | 0.42 |
| DSCC1 | 0.49 | −0.57 | −0.23 | −0.17 | 0.23 | LINC01917 | −0.66 | 0.43 | 0.73 | −0.21 | −0.30 | RPS4XP6 | 0.04 | −0.40 | 0.52 | −0.18 | 0.17 |
| ENTPD6 | −0.48 | 0.14 | −0.02 | 0.25 | 0.15 | RPS16P5 | −0.34 | −0.77 | −0.53 | −0.36 | −0.01 | AL954642.1 | 0.28 | −1.36 | −0.92 | −0.10 | 0.25 |
| FUNDC2 | 0.28 | −0.14 | −0.35 | −0.02 | −0.26 | LCE2C | −0.36 | 0.43 | 1.30 | 0.31 | −0.38 | RPL18P1 | −0.52 | 0.45 | 1.06 | 0.95 | 0.56 |
| PLVAP | 0.56 | −0.30 | 0.26 | −0.27 | −0.26 | PHBP15 | −0.34 | 0.36 | 0.20 | 0.68 | 0.32 | AL845472.1 | −0.12 | −2.14 | 0.53 | −0.59 | 2.88 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| RPL7L1 | 0.25 | −0.31 | −0.25 | −0.11 | 0.13 | OR8B9P | −0.61 | −0.15 | 0.84 | −1.42 | 0.09 | AL449283.1 | 0.03 | −0.30 | 0.41 | −0.20 | 0.04 |
| LRRC29 | −0.66 | 0.14 | 0.52 | 0.07 | 0.40 | AL078582.1 | −0.73 | −0.48 | 1.59 | 1.28 | 0.00 | AC090857.2 | −0.22 | 0.63 | 0.46 | 0.28 | 0.08 |
| AC127526.1 | −1.47 | 0.58 | 1.78 | 0.19 | 1.00 | FAM173B | −0.15 | −0.19 | 0.13 | −0.20 | 0.25 | AC079395.3 | −0.52 | −0.07 | 0.46 | 0.08 | −1.22 |
| PPARG | −0.88 | 0.69 | 0.15 | 0.50 | 0.12 | AC244394.1 | −0.61 | −0.19 | 1.21 | 0.94 | 2.11 | AC121764.2 | 0.19 | −1.41 | −0.41 | −0.04 | −0.91 |
| AF001548.3 | −1.21 | −0.17 | 0.45 | 1.04 | 0.50 | AC006058.4 | 0.45 | −0.26 | −1.06 | −0.19 | −1.51 | AC009468.1 | 0.19 | −1.00 | −0.64 | 1.78 | 2.28 |
| PLPP5 | −0.28 | 0.02 | 0.38 | −0.07 | 0.24 | AL078624.1 | −0.73 | 1.31 | 2.06 | −0.19 | −0.19 | AC125336.1 | −0.16 | 0.99 | −1.13 | 0.89 | −0.38 |
| BOLA3-AS1 | −0.56 | 0.06 | 0.46 | 0.06 | 0.41 | NKTR | −0.08 | 0.09 | 0.11 | 0.04 | 0.12 | IFNWP4 | 0.52 | −0.53 | −0.80 | 1.13 | 0.16 |
| NBN | 0.35 | −0.26 | −0.30 | −0.11 | −0.13 | KRTAP1-5 | −0.79 | 1.07 | 2.21 | −0.15 | 0.06 | AC083900.1 | 0.04 | 0.00 | 0.04 | −0.09 | 0.38 |
| LINC01170 | −1.52 | 1.17 | −0.13 | 0.79 | −0.65 | CYP11A1 | 0.47 | 0.18 | 1.33 | −0.38 | −0.23 | PRR13P3 | 0.09 | 0.07 | −0.17 | 0.51 | 1.05 |
| SNORA71C | 0.74 | −0.48 | −0.84 | 0.25 | −0.51 | AC087258.1 | 0.90 | −1.73 | 0.49 | −0.39 | 1.42 | AC084346.1 | −0.17 | −0.02 | 1.41 | −0.73 | 0.79 |
| SRSF7 | 0.25 | −0.27 | −0.38 | −0.05 | 0.02 | CCDC58P5 | 0.56 | 0.15 | −0.58 | 1.87 | 0.60 | ARLNC1 | 0.10 | −0.41 | 0.08 | −0.29 | 0.66 |
| KMT2D | −0.29 | 0.10 | −0.03 | 0.14 | 0.11 | AC009108.1 | −0.72 | 0.14 | −0.21 | 0.28 | 0.36 | LINC02406 | 0.25 | 0.03 | −0.94 | −0.80 | −0.59 |
| ISLR2 | −0.84 | 0.32 | 1.35 | −0.16 | 0.26 | LZTS1-AS1 | 0.32 | 0.20 | −0.34 | 0.31 | −0.44 | COX6B1P1 | 0.43 | −1.60 | 1.49 | −1.13 | −1.14 |
| NINJ1 | −0.46 | 0.29 | 0.48 | 0.15 | −0.06 | C12orf57 | −0.21 | 0.54 | 0.61 | −0.06 | −0.23 | AC023442.3 | 0.49 | −0.33 | −0.58 | 0.11 | 0.59 |
| OPA3 | 0.25 | −0.22 | −0.56 | −0.12 | −0.17 | PIAS4 | −0.11 | 0.20 | −0.09 | 0.14 | −0.02 | IGKVID-13 | −0.52 | 0.51 | 0.81 | 0.92 | −0.04 |
| AC008555.1 | −1.13 | 0.87 | 1.68 | −0.08 | 0.68 | RNA5SP256 | −0.53 | 0.10 | 0.32 | −0.33 | −1.58 | KRTAP9-4 | −0.52 | 0.22 | 2.36 | −1.44 | −2.90 |
| OR9Q2 | −1.27 | −0.15 | 1.12 | 0.07 | 0.64 | RPL23AP10 | −1.18 | 0.31 | 0.98 | 0.95 | 0.56 | AC243972.2 | 0.19 | −1.07 | 0.91 | −0.81 | 1.11 |
| ALOX12 | −0.52 | 0.48 | 0.79 | 0.37 | 0.19 | SALRNA1 | −0.58 | 0.00 | 0.48 | −0.23 | −0.27 | HOXB5 | 0.06 | 0.10 | 1.58 | 0.47 | 0.20 |
| SLAIN2 | 0.27 | 0.08 | −0.09 | −0.08 | −0.24 | AC005837.3 | −0.42 | 1.22 | 0.26 | −0.30 | −0.62 | AL662860.1 | −0.15 | 0.01 | 0.35 | −0.43 | 0.79 |
| AC106869.1 | −0.95 | 0.48 | 1.47 | −0.58 | 0.70 | AL590426.1 | −0.48 | −0.66 | 0.70 | −0.24 | 0.36 | AC073648.3 | −0.09 | −0.31 | −0.50 | −0.23 | −0.23 |
| AC104365.1 | 0.60 | −0.28 | −0.68 | 0.08 | −0.37 | AC123912.2 | 0.56 | −1.91 | −1.77 | 0.99 | −0.66 | FOXB1 | 0.09 | 0.17 | −0.93 | −0.13 | −0.50 |
| NDUFB1P1 | 1.73 | −1.37 | −1.86 | −0.26 | −0.92 | AC025271.1 | −0.71 | 0.17 | 2.14 | −1.65 | 0.94 | C16orf97 | 0.11 | 1.16 | −1.35 | 1.79 | −0.68 |
| AC004889.1 | −0.70 | −0.11 | 0.80 | 0.32 | 0.98 | SETP12 | −0.27 | −0.16 | −0.31 | −0.06 | −0.17 | RNA5SP395 | 0.04 | 0.15 | 0.64 | −0.25 | −0.12 |
| AC025524.2 | −0.91 | −0.08 | −0.12 | 0.28 | 0.37 | RNF148 | −0.34 | −0.13 | −0.32 | 0.04 | 0.24 | AC005150.1 | −0.51 | −0.41 | −0.75 | 1.53 | 1.68 |
| SCML2 | −0.50 | 0.03 | 0.26 | 0.24 | 0.40 | MAP3K14 | 0.18 | −0.25 | −0.51 | 0.13 | 0.13 | AL117339.3 | −0.25 | −0.37 | −1.23 | 1.70 | −0.02 |
| LINC01143 | −1.69 | 0.96 | 0.80 | 0.81 | 0.99 | RNU6-770P | 0.72 | 0.62 | 1.59 | 0.50 | 0.23 | AC091770.2 | −0.15 | 1.39 | 0.09 | −0.03 | −0.97 |
| AF241728.1 | 1.65 | −1.19 | −0.87 | 0.67 | 0.90 | AP002754.1 | −0.48 | −0.98 | 0.78 | −0.33 | 1.22 | AC008906.1 | −0.03 | −0.09 | 0.12 | 0.02 | −0.10 |
| AC007272.1 | −0.94 | 0.02 | 1.15 | −0.16 | 0.81 | MIR1256 | 0.79 | 0.77 | −1.50 | 0.70 | −0.31 | RNU7-57P | 0.08 | −0.55 | −0.49 | −0.13 | −0.52 |
| AL133523.1 | −1.33 | 1.47 | −0.15 | 0.69 | −1.75 | AL356234.1 | 0.57 | −0.48 | −0.87 | −0.13 | −1.01 | RN7SL268P | −0.12 | 0.80 | 0.86 | 0.35 | −0.16 |
| MORF4L2-AS1 | −0.65 | −0.23 | 1.07 | −0.04 | 0.84 | RNASSP299 | −0.74 | 0.27 | 1.35 | 0.69 | 0.28 | GOLGA6L10 | −0.07 | 0.98 | −1.01 | 1.57 | −0.71 |
| PHACTR2 | 0.40 | −0.21 | −0.23 | −0.26 | −0.22 | MTND5P31 | −0.53 | −0.17 | 0.00 | −0.08 | −0.01 | RPL7L1P7 | 0.51 | −1.00 | −0.23 | 0.40 | 0.23 |
| SAXO1 | −0.74 | 0.52 | 0.59 | −0.07 | −0.11 | KRT18P18 | 0.53 | −0.41 | 0.90 | −0.37 | 0.66 | OR10J5 | 0.51 | −0.87 | −1.25 | −0.24 | −0.23 |
| PACRG−AS3 | −0.81 | 1.06 | 0.97 | 0.19 | −0.14 | HNRNPCP3 | 0.85 | −0.64 | −0.38 | 0.22 | 0.68 | PPIAP91 | −0.05 | 0.12 | 0.54 | 0.05 | −0.14 |
| SLAMF1 | 1.04 | −1.14 | −0.61 | −0.88 | −0.09 | RNA5SP303 | −1.15 | −0.93 | 0.65 | −1.28 | −0.11 | AC015917.1 | 0.51 | −1.08 | −0.71 | −0.38 | −0.68 |
| SETDB2 | −0.21 | 0.20 | 0.46 | 0.02 | 0.19 | RCC2P4 | 0.45 | 0.45 | −0.44 | 0.24 | −0.41 | RN7SL313P | 0.16 | −0.28 | −1.53 | −0.60 | −2.30 |
| PARD6G | −0.48 | 0.24 | −0.02 | 0.36 | 0.01 | DDX39BP1 | −0.63 | 1.36 | 2.14 | −0.38 | −0.67 | PEX12 | −0.02 | 0.04 | 0.27 | −0.04 | 0.06 |
| RRP12 | 0.50 | −0.41 | −0.72 | −0.06 | −0.18 | GIGYF2 | −0.09 | −0.01 | −0.06 | −0.08 | −0.09 | SARS2 | 0.03 | −0.24 | −0.29 | 0.28 | 0.55 |
| DBNDD2 | −0.77 | 0.74 | 0.71 | 0.45 | −0.45 | PIK3R5 | 0.23 | −0.73 | −0.55 | −0.22 | −0.14 | RPL7P31 | 0.27 | 0.46 | −0.08 | −1.41 | −1.42 |
| AL591767.3 | 1.12 | −0.88 | −0.75 | −0.12 | 0.22 | G10060 | 0.68 | −0.56 | 1.04 | 0.32 | −0.16 | AC040918.1 | 0.22 | −0.95 | 0.34 | −0.59 | −0.24 |
| HADHB | 0.31 | −0.14 | −0.33 | −0.01 | −0.18 | AC074367.1 | −0.19 | 0.09 | 0.15 | 0.19 | 0.27 | AC061965.1 | −0.10 | −0.19 | 2.02 | 0.62 | 1.00 |
| KIRREL1 | 0.41 | −0.31 | −0.25 | −0.29 | −0.10 | MROH2B | −0.46 | −0.33 | −0.77 | 0.26 | −0.84 | AC008764.10 | −0.03 | −0.16 | −0.22 | −0.11 | −0.05 |
| METTL1 | 0.45 | −0.48 | −0.59 | 0.02 | −0.03 | AL136501.1 | −0.94 | −0.65 | −2.46 | 0.85 | −1.05 | BARHL2 | −0.18 | −0.57 | −0.25 | −0.07 | −1.08 |
| MFSD2B | −0.64 | 0.19 | 0.15 | 0.18 | 0.26 | MCCD1P1 | −0.69 | 1.75 | 0.52 | 0.16 | −2.17 | AC084879.1 | −0.07 | 0.45 | −0.90 | −0.18 | −0.67 |
| FCN3 | 0.95 | −0.43 | −0.43 | 0.06 | 0.01 | AC007751.2 | 0.90 | 0.06 | −3.77 | 1.07 | −2.06 | AP005119.1 | −0.51 | 0.11 | 0.64 | 2.51 | −0.93 |
| AC004672.2 | 0.65 | 0.05 | −0.96 | 0.11 | −0.33 | MIR3193 | 0.61 | −1.14 | 0.20 | −0.56 | −1.37 | AC025437.2 | −0.10 | −0.30 | −0.33 | −0.09 | 0.56 |
| CELF1 | 0.21 | −0.15 | −0.33 | −0.07 | −0.07 | AL133257.1 | −0.52 | −0.04 | −0.03 | 1.01 | 1.09 | AC023469.1 | −0.12 | 0.07 | −1.23 | 0.95 | −0.85 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| NR1I3 | −0.53 | 0.31 | 0.89 | −0.01 | 0.36 | AL109618.1 | 0.31 | 0.23 | −0.40 | 0.18 | −0.41 | DNAL4 | 0.02 | 0.29 | 0.38 | 0.10 | −0.15 |
| HORMAD1 | 0.76 | −0.21 | −0.71 | 0.63 | −0.08 | SMG1P4 | −0.23 | −0.02 | 0.68 | −1.26 | −0.99 | AC005178.1 | −0.19 | −0.46 | 1.48 | −1.73 | −0.58 |
| AC069224.1 | −0.79 | 0.55 | 0.93 | 0.63 | 0.48 | MLNR | −0.56 | −0.69 | 1.01 | −0.17 | 1.02 | RN7SL529P | −0.08 | 0.37 | 0.44 | 0.08 | 0.20 |
| SNORA5C | −0.69 | 0.29 | −0.12 | 0.36 | −0.22 | LPAR2 | 0.18 | 0.27 | −0.13 | 0.08 | −0.15 | C10orf71-AS1 | −0.51 | −0.01 | 0.26 | −0.56 | 0.34 |
| EOMES | 1.43 | −0.07 | −0.12 | 0.03 | −0.07 | AL359715.3 | −0.31 | 0.20 | 0.57 | 0.05 | 0.21 | MTCO1P2 | −0.06 | 0.20 | 1.23 | −0.15 | 0.88 |
| AC005480.1 | −0.46 | 0.06 | 0.40 | −0.04 | 0.20 | LINC02469 | −0.58 | −0.11 | 0.19 | 0.10 | −1.40 | AL139289.2 | −0.03 | −0.21 | 0.35 | −0.02 | 0.37 |
| PRSS53 | 0.64 | −0.28 | −0.76 | −0.33 | −0.10 | C11orf95 | −0.13 | 0.10 | −0.05 | 0.16 | 0.05 | CBX1P3 | −0.23 | 0.60 | 0.68 | 1.27 | 2.44 |
| AC239809.2 | −0.86 | 0.79 | 0.58 | 0.12 | −0.64 | LINC00622 | −0.60 | 0.80 | −0.04 | 0.71 | −1.25 | AC013439.1 | −0.13 | 1.65 | 1.22 | 0.60 | −1.02 |
| CXorf57 | −0.52 | 0.31 | 0.08 | 0.00 | −0.20 | MYBPC2 | −0.46 | −0.15 | 0.01 | −0.38 | 0.13 | AC055855.2 | −0.40 | −0.46 | 0.03 | −0.03 | −0.42 |
| AC127024.2 | −0.51 | 0.13 | 0.22 | 0.21 | 0.46 | AP000845.1 | 0.24 | 0.25 | −0.69 | 0.34 | −0.48 | MTCO2P5 | 0.26 | −0.81 | −2.00 | 0.08 | 0.12 |
| AC026462.1 | 1.09 | −0.41 | −1.05 | 0.45 | −0.22 | LHX8 | −0.66 | 0.24 | −0.59 | 0.47 | −2.10 | RNU6-1199P | 0.18 | 0.40 | 0.71 | 0.86 | 1.45 |
| LINC02432 | −1.10 | 0.15 | 0.46 | −0.10 | −0.36 | RNU6-790P | 0.76 | −0.99 | −0.04 | 0.20 | 1.03 | RN7SL806P | −0.07 | 0.70 | 0.20 | 0.71 | 0.15 |
| PRR9 | 1.34 | −1.17 | 0.36 | −0.62 | 0.44 | AC099677.4 | 1.34 | −0.89 | 0.17 | 0.05 | −0.56 | AC092418.1 | 0.17 | −0.34 | 1.18 | 0.79 | 0.40 |
| G37372 | −0.65 | −0.21 | 0.61 | −0.43 | 0.39 | GAPDHP51 | −0.27 | 0.08 | 0.46 | −0.07 | −0.09 | KBTBD6 | 0.02 | 0.16 | 0.46 | −0.08 | −0.19 |
| OSBPL9 | −0.23 | 0.23 | 0.28 | 0.06 | 0.03 | MEGF10 | −0.26 | 0.05 | 0.64 | −0.20 | 0.47 | HSP90AB4P | −0.02 | −0.36 | −0.25 | −0.02 | 0.16 |
| FBXW5 | 0.30 | −0.31 | −0.62 | −0.02 | −0.15 | CABP4 | −0.27 | −0.01 | 0.00 | −0.14 | −0.34 | ABHD15-AS1 | 0.07 | −0.14 | −0.40 | −0.51 | −0.73 |
| EEF1A1 | 0.34 | 0.02 | −0.15 | 0.02 | −0.31 | LINC02153 | −0.85 | −0.68 | −0.13 | −0.50 | −0.36 | AL132796.1 | 0.14 | −1.72 | −1.41 | −0.06 | 0.11 |
| CBLN1 | −1.25 | 1.05 | 0.18 | 0.69 | −0.68 | PRNCR1 | 0.16 | −0.04 | 0.28 | 0.15 | 0.35 | AL096800.1 | −0.17 | −1.60 | −1.10 | 1.07 | −1.10 |
| AC103702.1 | −1.08 | 0.35 | 2.12 | −0.59 | 0.60 | DDC | −0.55 | −0.78 | 0.14 | −0.38 | 0.02 | EPB41L3 | −0.03 | −0.28 | −0.26 | −0.22 | −0.23 |
| C4orf48 | 1.17 | −0.34 | −1.18 | −0.37 | −1.13 | MIR1271 | −0.48 | 0.13 | 2.25 | −0.67 | 1.27 | SPACA5 | −0.25 | −0.83 | 2.07 | 0.25 | 1.50 |
| ADAMTS7 | 0.60 | −0.45 | −0.52 | −0.28 | −0.27 | RN7SL114P | −1.11 | 0.44 | −0.28 | 1.08 | 0.70 | NBPF22P | 0.17 | 0.68 | −0.43 | 0.83 | −1.95 |
| CWF19L1 | 0.21 | −0.12 | −0.34 | 0.07 | −0.28 | AL353784.1 | −0.82 | −1.10 | −0.41 | −0.17 | −1.81 | PPIAP79 | 0.24 | 0.81 | −0.46 | 1.03 | −1.07 |
| LINC01149 | −1.61 | −1.08 | 0.30 | 0.25 | 1.67 | LINC01814 | 0.36 | −0.48 | −0.11 | −0.33 | 0.36 | AC142381.3 | −0.05 | 0.10 | −0.85 | 0.39 | −1.20 |
| GLB1L3 | 0.46 | 0.05 | −0.49 | 0.24 | −0.25 | AL121809.2 | 0.74 | −0.88 | −1.27 | −0.04 | −0.09 | RNU6-110P | −0.25 | −1.08 | 0.95 | −1.67 | 1.75 |
| ASF1A | 0.33 | −0.03 | −0.10 | 0.11 | 0.05 | REEP4 | −0.15 | 0.07 | −0.20 | 0.34 | −0.03 | AL357140.2 | −0.08 | −1.10 | −0.75 | −0.81 | 0.65 |
| RFNG | −0.42 | 0.42 | −0.33 | 0.36 | −0.24 | DLL3 | 0.63 | −1.51 | −2.03 | −0.65 | −0.27 | AP1S2 | 0.02 | −0.03 | 0.26 | −0.06 | 0.17 |
| SLC39A14 | 0.45 | −0.53 | −0.27 | −0.51 | −0.31 | AC097652.1 | −0.55 | 0.16 | 1.04 | −0.36 | 0.93 | OR10G7 | −0.18 | −1.58 | 0.44 | −0.20 | −0.06 |
| AC109486.1 | −1.32 | 0.39 | 0.52 | −0.22 | 0.21 | MS4A3 | 0.90 | −0.30 | −1.23 | −0.69 | −0.03 | FAM225A | 0.14 | 0.21 | 0.13 | −0.26 | −1.23 |
| AC079210.1 | 0.46 | −0.32 | −0.16 | −0.15 | 0.19 | AC119044.1 | 0.19 | 0.08 | −0.24 | 0.03 | 0.04 | MMP2 | 0.05 | 0.51 | 1.61 | −0.97 | −0.38 |
| LINC02302 | −1.52 | −0.30 | 0.82 | 0.17 | −0.80 | AL353803.4 | −0.45 | −0.75 | −0.80 | 0.55 | 1.50 | GPS2P2 | −0.09 | −0.55 | −1.59 | 0.62 | −1.68 |
| DNAJC2 | 0.32 | −0.35 | −0.43 | −0.16 | −0.10 | LINC02196 | −0.61 | 1.32 | −0.29 | −0.23 | −0.32 | AC022146.2 | 0.05 | 0.13 | 0.54 | −0.01 | 0.25 |
| AC000123.1 | 0.55 | −0.16 | 0.10 | −0.15 | −0.02 | AL953854.2 | −0.55 | −0.54 | 0.67 | 0.72 | 0.96 | MIR3927 | −0.11 | 1.07 | −0.78 | 1.26 | −0.24 |
| GOLGA8B | −0.33 | 0.16 | −0.08 | 0.52 | 0.33 | AL157762.1 | 0.44 | −0.32 | −0.05 | −0.03 | 0.23 | REG1CP | −0.14 | 0.26 | 0.10 | 0.23 | 0.34 |
| MEIS1 | −0.26 | 0.25 | 0.13 | 0.11 | −0.10 | IGHV4-39 | 1.36 | 0.02 | −1.66 | 1.05 | 0.42 | OR51F4P | −0.15 | −1.44 | −3.01 | 1.51 | −1.68 |
| ABHD3 | 0.37 | −0.47 | −0.49 | −0.04 | −0.11 | AC110285.6 | −0.42 | 0.03 | −0.36 | 1.44 | 0.37 | RP11-206L10.3 | 0.06 | 0.59 | −1.54 | 0.56 | −0.72 |
| AP001439.1 | 0.95 | −0.61 | −1.19 | −0.07 | −0.47 | ENOX1-AS2 | 1.01 | −0.79 | −1.86 | −0.17 | −0.34 | EHHADH | 0.02 | 0.01 | −0.07 | 0.12 | 0.13 |
| SNORD101 | 0.73 | −0.37 | −0.79 | −0.31 | −0.52 | BBS7 | 0.07 | 0.05 | −0.09 | −0.15 | −0.20 | HINT2 | −0.05 | −0.04 | 0.44 | −0.38 | −0.15 |
| IL26 | 2.29 | −0.64 | −1.25 | 0.42 | 0.17 | AL451123.1 | −0.10 | −0.19 | 0.07 | 0.08 | 0.37 | AC007312.1 | −0.06 | 0.33 | 0.44 | 0.41 | 0.00 |
| MIR4668 | 1.46 | −0.53 | −0.41 | −0.83 | −0.04 | AL392048.1 | 0.55 | −0.22 | 0.75 | 0.11 | −0.27 | G13124 | 0.05 | 0.27 | 0.51 | 0.72 | 0.71 |
| AP001347.1 | −0.68 | −0.03 | 0.95 | −0.01 | 0.50 | MYBBPIA | −0.16 | −0.21 | −0.42 | 0.14 | 0.25 | AC109994.1 | 0.11 | −0.47 | −0.74 | 0.01 | −0.65 |
| GDF5 | −1.45 | 1.15 | 0.23 | 0.59 | −0.05 | AC104350.1 | −0.61 | −0.60 | 0.45 | −0.52 | −0.47 | MIR216B | −0.51 | 0.15 | NA | −0.67 | −1.11 |
| AC126696.2 | 2.53 | −0.79 | −0.85 | −0.48 | −1.31 | LINC01323 | −0.67 | −0.09 | −0.25 | 1.33 | 0.36 | AL359195.1 | 0.51 | −1.33 | −0.85 | 0.51 | 0.23 |
| LINC01402 | −1.52 | 0.05 | 1.77 | 0.05 | 1.30 | AL353608.2 | 0.34 | 0.13 | 0.33 | −0.30 | −0.01 | RN7SL144P | 0.05 | −0.09 | −1.28 | 0.04 | −0.18 |
| AC026624.1 | 0.91 | −0.26 | −0.30 | 0.05 | −0.43 | RIOX1 | 0.12 | −0.15 | −0.09 | −0.07 | 0.04 | PPIAP68 | 0.51 | −0.77 | −1.57 | 0.18 | −0.60 |
| AC108142.1 | 2.16 | −1.56 | −1.13 | −0.02 | −1.26 | AC020633.1 | −0.30 | 0.17 | 0.40 | −0.01 | −0.16 | COX6CP11 | −0.51 | 0.38 | 0.43 | NA | −0.49 |
| LRCH3 | −0.18 | 0.02 | 0.08 | −0.17 | −0.01 | GATA2-AS1 | 0.25 | −0.12 | −0.18 | 0.01 | −0.31 | AC025538.1 | 0.49 | −0.96 | 1.03 | −1.62 | −0.34 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| RHOB | −0.41 | 0.59 | 0.29 | 0.18 | −0.32 | HMGB1P37 | 0.26 | −0.01 | −0.03 | 0.04 | −0.01 | AC105402.2 | −0.51 | −0.15 | −0.13 | 0.29 | 0.09 |
| AC026801.2 | −1.08 | 0.78 | 1.52 | 0.12 | −0.06 | SLC13A5 | 0.33 | −0.77 | −1.60 | −0.70 | −0.98 | AC100791.3 | −0.29 | 0.42 | 1.21 | −0.58 | 1.00 |
| RNA5SP149 | −1.34 | 0.56 | −1.53 | 1.73 | −1.06 | G25674 | −0.59 | 0.19 | 1.30 | 0.25 | 0.27 | AC117490.1 | −0.18 | 0.00 | −0.43 | 0.21 | 0.28 |
| ADGRF1 | 1.21 | −0.89 | −2.18 | 0.17 | −0.92 | ARHGEF2 | −0.15 | −0.18 | 0.02 | −0.18 | 0.07 | PIK3CB | 0.02 | 0.17 | 0.11 | 0.13 | −0.12 |
| DDX19A | 0.28 | −0.08 | −0.32 | 0.03 | −0.23 | FAM163A | 0.88 | −1.27 | −3.13 | 1.71 | 0.38 | LINC00463 | −0.23 | −1.34 | 0.60 | −1.93 | 1.32 |
| MUM1L1 | −1.50 | 0.23 | 0.74 | 0.52 | −0.25 | RPL7P57 | 0.41 | −0.09 | 0.51 | −0.03 | 0.52 | AC234772.1 | 0.11 | −0.12 | 0.65 | −0.23 | −0.31 |
| CLSTN2-AS1 | −1.25 | −0.27 | 0.78 | 0.23 | −0.12 | PIK3CD-AS2 | 0.28 | −0.04 | −0.20 | −0.17 | 0.20 | ATXN2-AS | 0.09 | 0.16 | 0.02 | −0.47 | −0.34 |
| NPEPL1 | −0.42 | 0.13 | −0.11 | 0.44 | 0.15 | RPS3AP12 | 0.28 | −0.22 | 0.24 | −0.44 | 0.39 | AP004609.2 | 0.46 | −0.83 | 0.73 | −0.38 | 2.40 |
| C16orf74 | 0.65 | −0.77 | −1.46 | −0.08 | −0.53 | AC104211.2 | 1.26 | −1.67 | −1.20 | −0.27 | −0.94 | LKAAEAR1 | 0.12 | −1.71 | −1.39 | 0.23 | −0.92 |
| SOX1 | −1.06 | −0.27 | 0.40 | 0.03 | 0.84 | RNF114 | 0.07 | −0.11 | −0.07 | −0.13 | 0.04 | AC063947.1 | −0.50 | 0.06 | −0.36 | −0.26 | 0.43 |
| GP1BA | −0.59 | 0.45 | 0.36 | 0.51 | 0.31 | PSEN1 | 0.08 | 0.08 | −0.06 | −0.01 | −0.16 | AL109933.4 | −0.23 | 0.65 | −1.29 | 0.39 | −0.99 |
| IVD | −0.44 | 0.09 | 0.58 | −0.10 | 0.24 | B3GNT10 | 0.13 | −0.26 | 0.11 | −0.12 | 0.29 | AL450344.2 | −0.06 | 0.21 | 0.82 | −0.52 | 0.10 |
| AP005131.5 | −0.63 | 0.28 | 0.85 | 0.04 | 0.05 | AL162386.2 | −0.36 | 0.16 | 0.97 | −0.33 | 0.14 | AC108210.1 | 0.28 | −1.14 | −1.13 | −0.84 | −1.11 |
| MRC2 | −0.48 | 0.30 | 0.47 | −0.08 | −0.09 | IL21-AS1 | 0.66 | −0.19 | −2.24 | 0.34 | −1.33 | AC104687.2 | 0.50 | −0.97 | 0.22 | 0.98 | 1.64 |
| LINC01649 | −1.63 | 0.98 | 0.71 | 0.60 | −0.46 | AC108463.1 | 0.38 | −0.83 | 0.32 | −0.96 | 0.20 | AL359764.1 | 0.28 | −0.52 | 0.81 | −0.54 | −1.29 |
| PFKP | 0.33 | −0.23 | −0.66 | 0.01 | −0.19 | ABCC5 | 0.14 | 0.15 | 0.24 | 0.04 | −0.05 | AC073314.1 | −0.06 | −0.02 | −0.56 | 0.76 | 0.05 |
| ACTR3C | 0.51 | −0.12 | −0.29 | 0.06 | −0.08 | AC011468.3 | −0.71 | 0.09 | 2.41 | −0.22 | 1.10 | AC073310.1 | 0.50 | −1.04 | 1.18 | −0.58 | 2.43 |
| LRRC71 | −0.71 | 0.08 | −0.07 | −0.09 | 0.02 | RN7SKP282 | 0.57 | −0.72 | −0.49 | −0.21 | 0.46 | AC142086.6 | −0.10 | 0.13 | −1.69 | 0.21 | −0.71 |
| SPEM2 | −1.67 | 1.10 | −0.76 | 0.52 | −0.18 | RN7SL794P | −0.92 | −1.04 | −0.68 | −0.29 | −2.52 | EIF1AXP2 | 0.07 | −1.11 | −1.77 | −0.25 | 0.03 |
| SHISA4 | −0.72 | 0.20 | 1.12 | −0.33 | 0.33 | PPMIN | −0.18 | 0.01 | −0.15 | 0.10 | 0.00 | LINC02327 | −0.14 | −0.30 | −2.24 | −0.61 | −1.41 |
| RELCH | 0.27 | −0.12 | −0.17 | 0.02 | 0.08 | AC010591.1 | 0.87 | −2.02 | 0.15 | −0.57 | 1.17 | LINC01911 | −0.10 | −1.05 | 0.51 | −0.99 | 1.20 |
| CSDE1 | 0.38 | −0.06 | −0.20 | −0.07 | −0.30 | AC010877.1 | −0.55 | 0.10 | 0.22 | −0.02 | 0.23 | AC117482.1 | −0.50 | 0.22 | 0.17 | 1.53 | 0.45 |
| MIR3657 | 1.95 | −0.26 | −1.13 | −0.02 | −0.20 | AL117692.1 | 0.70 | −2.43 | −2.68 | −0.46 | −0.48 | AC112518.2 | 0.50 | −1.01 | −0.73 | 0.59 | −0.62 |
| RN7SL838P | −1.17 | 0.80 | 0.32 | −0.05 | −0.21 | G32188 | 0.33 | −0.74 | −0.63 | −0.33 | 0.50 | MRPS18BP1 | −0.50 | 0.13 | −0.05 | 2.35 | 0.81 |
| FAM111A | −0.31 | 0.04 | 0.56 | −0.16 | 0.23 | CXorf58 | 0.52 | −0.88 | −1.39 | −0.69 | 0.18 | RPL23AP14 | −0.14 | 0.23 | 1.27 | 0.73 | 1.05 |
| G7052 | −2.64 | 1.18 | 1.12 | 1.56 | 0.81 | AC018878.1 | 0.35 | 0.03 | 0.02 | −0.31 | 0.09 | RNA5SP311 | 0.15 | −0.42 | 1.00 | 0.78 | 2.30 |
| GRM7-AS1 | −2.16 | 0.45 | 1.27 | 0.22 | 0.48 | MIR4527HG | −0.88 | 1.30 | 0.28 | 1.23 | −1.40 | AL157884.2 | −0.25 | −1.94 | 1.38 | −1.88 | −0.23 |
| CNOT10 | 0.26 | −0.10 | −0.05 | −0.10 | −0.03 | PTCHD3P2 | −0.58 | 0.51 | 0.32 | 0.05 | 0.26 | AL365400.2 | 0.24 | −1.84 | 0.27 | −0.83 | −0.94 |
| LRRC46 | −0.50 | 0.19 | 0.81 | 0.07 | −0.01 | AC124319.4 | 0.19 | −0.69 | −0.27 | −0.55 | 0.11 | NDUFB4P2 | −0.04 | 0.10 | −1.21 | 0.06 | −0.75 |
| G23773 | −1.35 | −0.70 | 1.09 | 0.21 | 1.76 | G23276 | 0.28 | 0.01 | −0.51 | 0.05 | −0.14 | SMAD5-AS1 | 0.03 | 0.15 | 0.38 | 0.15 | 0.04 |
| MAGEH1 | −0.56 | 0.15 | 0.26 | −0.28 | −0.39 | AC104996.1 | −1.13 | 0.46 | −0.16 | 2.43 | −1.20 | AL160004.2 | −0.21 | −1.53 | −1.21 | −1.02 | 2.13 |
| SEC22B | −0.27 | 0.05 | 0.27 | −0.04 | 0.15 | AC079416.3 | 0.48 | −0.99 | 0.02 | −0.16 | 1.31 | RNU1-122P | 0.50 | −0.39 | −0.80 | −1.64 | −1.71 |
| NIPSNAP3A | 0.39 | 0.08 | −0.13 | −0.09 | −0.43 | RNU6-30P | −0.59 | 1.45 | −0.85 | 0.20 | −1.48 | FGF6 | −0.16 | −1.68 | 0.96 | 0.47 | 0.95 |
| FOXP3 | 0.77 | −0.49 | −0.12 | −0.48 | 0.21 | AL033527.2 | 0.59 | −0.18 | 0.36 | 0.12 | −0.19 | MIRLET7G | 0.06 | −0.19 | −1.01 | 0.24 | −0.51 |
| AC022400.7 | −0.37 | 0.22 | 0.17 | 0.25 | 0.11 | AC093274.1 | −0.69 | 1.77 | 0.13 | 1.37 | −0.39 | AC094104.2 | −0.50 | −0.52 | −0.10 | 0.96 | −0.04 |
| EXOSC1 | 0.30 | −0.20 | −0.13 | −0.12 | −0.02 | RNU6-951P | −0.48 | 0.32 | 0.45 | 0.27 | 1.29 | AC133865.1 | −0.26 | −0.46 | −1.35 | 1.05 | −0.58 |
| EIF1 | 0.35 | −0.17 | −0.54 | −0.04 | −0.42 | RNU6-1310P | 0.54 | −0.56 | 1.20 | −0.14 | 0.57 | KRT18P36 | 0.30 | −0.10 | −1.36 | −0.18 | −1.44 |
| HIPK3 | 0.34 | −0.01 | −0.22 | −0.06 | −0.40 | AL445363.2 | −0.74 | −0.58 | 0.11 | −0.20 | 1.05 | AC007225.1 | −0.07 | 0.14 | −0.65 | 0.51 | −0.29 |
| AP001284.1 | −1.42 | −0.67 | −1.82 | 0.03 | −0.94 | HYAL6P | −1.14 | 1.83 | 0.20 | 0.57 | −1.85 | LARP1BP1 | −0.17 | 0.25 | −0.46 | −0.63 | 0.01 |
| OSGIN2 | −0.52 | 0.24 | 0.46 | −0.02 | 0.13 | AC013267.1 | 0.47 | −0.03 | −1.62 | −0.54 | −1.42 | AC093249.4 | −0.08 | 0.05 | 0.43 | −0.57 | −0.08 |
| STARD3 | −0.33 | 0.17 | 0.05 | 0.19 | 0.11 | BAG2 | −0.20 | 0.04 | 0.38 | −0.38 | −0.22 | AC006305.2 | −0.12 | 0.73 | −0.88 | 0.01 | −1.76 |
| SLC46A3 | −0.56 | 0.19 | 0.57 | −0.06 | 0.46 | RANP3 | 0.42 | 0.10 | −0.50 | −0.46 | −0.04 | AC073569.3 | 0.04 | −0.10 | 0.03 | −0.23 | −0.14 |
| PCMTD2 | −0.25 | 0.36 | 0.53 | 0.24 | 0.01 | MIR1254-1 | 0.30 | −0.40 | 0.16 | −0.06 | 0.08 | INKA2-AS1 | −0.06 | −0.59 | 0.11 | 0.58 | 1.10 |
| LINC00520 | 1.05 | −0.64 | −0.88 | −0.08 | −0.56 | LEAP2 | 0.18 | −0.04 | −0.04 | 0.03 | −0.08 | AC073333.2 | −0.25 | −0.67 | −0.88 | −0.34 | 0.79 |
| AC125437.2 | −0.60 | 0.30 | 0.24 | 0.28 | 0.32 | AC099482.1 | 0.42 | −0.85 | −1.98 | −0.45 | −0.72 | AC012409.4 | 0.09 | 0.73 | 0.18 | 0.65 | −0.29 |
| RPS10P2 | −1.11 | 0.36 | 1.88 | −0.17 | 0.82 | HNRNPA1P61 | 0.47 | −1.34 | −0.96 | 0.06 | −0.10 | SFRP2 | 0.04 | 0.37 | 2.19 | −0.76 | −0.16 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC098592.1 | 2.39 | −3.09 | −0.72 | −0.49 | 0.59 | AC113385.1 | −0.42 | 0.73 | −0.35 | 1.30 | 0.37 | RPL21P43 | −0.42 | −0.05 | 1.65 | −1.47 | 2.03 |
| CABIN1 | −0.33 | 0.06 | −0.15 | 0.25 | 0.09 | AL137856.1 | 0.77 | −0.96 | 0.03 | 0.15 | 0.11 | LINC01947 | −0.50 | −0.75 | −1.03 | 0.15 | NA |
| AP001830.1 | −1.08 | 0.54 | 1.93 | 0.42 | 0.65 | AC112722.1 | −0.33 | 0.74 | 0.43 | 0.23 | −0.24 | DPP3P2 | 0.24 | −0.43 | −0.64 | −1.34 | −0.79 |
| AC104791.2 | 0.63 | −0.36 | −0.43 | 0.09 | 0.15 | AL161729.4 | −0.52 | −0.39 | 0.79 | 0.06 | 0.62 | ORM1 | 0.21 | −0.63 | −0.45 | −1.73 | −3.50 |
| SMARCA1 | −0.40 | 0.30 | 0.57 | −0.11 | −0.02 | RNU6-610P | 0.63 | −0.64 | 1.68 | −0.82 | 0.92 | RPL7P32 | 0.03 | 0.53 | −0.09 | −0.12 | −0.16 |
| GLT8D1 | 0.24 | −0.17 | 0.09 | −0.16 | −0.02 | AC241584.1 | −0.46 | −0.78 | −0.60 | −0.02 | 0.94 | RNU6-1304P | 0.20 | −1.68 | 1.85 | −1.89 | 0.95 |
| AC005062.1 | −0.93 | 0.58 | 1.22 | −0.04 | 0.31 | AC004263.1 | 0.36 | 0.10 | −2.24 | 0.50 | −1.87 | AC004383.1 | 0.07 | 0.18 | 0.20 | −0.13 | −0.36 |
| MARCKSL1 | 0.52 | −0.38 | −0.38 | −0.41 | −0.27 | RNU6-884P | −0.57 | 0.10 | 0.83 | −0.58 | 1.14 | AC005399.1 | −0.07 | 0.08 | 0.21 | −0.03 | 0.43 |
| AC004830.1 | −0.97 | 1.15 | 1.80 | 0.49 | 0.30 | AC103801.1 | −0.73 | 0.83 | −0.34 | 0.18 | −1.79 | MTND4P24 | −0.05 | −0.16 | −0.35 | −0.03 | 0.22 |
| ALG1L2 | −0.66 | 0.26 | 1.11 | −0.01 | 0.68 | AC008015.1 | 0.30 | −0.86 | −0.56 | −0.01 | 0.62 | AL009183.1 | 0.50 | −1.77 | −0.61 | 0.81 | 1.68 |
| ADAMTSL2 | 0.83 | −1.31 | −1.19 | 0.11 | −0.53 | SMIM11P1 | −0.87 | 0.22 | 0.46 | −0.50 | −1.10 | NLRP6 | −0.06 | −0.31 | −0.17 | −0.25 | −0.01 |
| SLC43A2 | 0.59 | −0.77 | −0.69 | −0.37 | −0.10 | MAP2K3 | 0.12 | −0.16 | −0.65 | −0.03 | −0.53 | RPS7P8 | 0.24 | 0.46 | −0.13 | −0.24 | −1.03 |
| ILK | −0.40 | 0.17 | 0.29 | −0.15 | 0.04 | G25499 | −0.39 | 0.29 | 0.33 | −0.20 | 0.08 | AC007619.2 | 0.06 | 0.23 | −0.10 | 0.30 | 0.40 |
| EMP1 | 0.42 | −0.03 | −0.60 | 0.02 | −0.65 | RP11-423O2.2 | −0.38 | 0.92 | 1.51 | 0.96 | 0.68 | G26207 | 0.07 | 0.02 | 0.43 | −0.94 | −0.95 |
| C11orf54 | −0.32 | 0.18 | 0.55 | 0.23 | 0.30 | MRPS15P1 | 0.65 | 0.09 | 1.87 | −0.56 | −1.01 | RPS6P7 | 0.18 | 0.46 | −1.69 | 0.84 | 0.39 |
| AC079331.1 | 1.07 | −0.48 | −0.54 | −0.57 | −0.47 | RNU6-680P | 0.81 | −3.03 | −0.68 | −0.91 | 0.18 | MRGPRG−AS1 | 0.48 | −0.31 | −0.13 | 1.47 | 1.61 |
| RORB-AS1 | −1.42 | 0.36 | −0.25 | 0.20 | −1.68 | AC109779.1 | 0.71 | −0.72 | −0.37 | 1.11 | 0.63 | ENSAP2 | −0.05 | 0.37 | −1.05 | 0.17 | −0.19 |
| CYHR1 | −0.33 | 0.26 | 0.13 | 0.25 | 0.10 | MBP | 0.10 | −0.08 | −0.29 | 0.08 | −0.04 | AC110053.1 | 0.16 | 0.00 | −0.02 | 1.40 | 0.36 |
| CTTNBP2NL | 0.24 | 0.10 | 0.00 | −0.07 | −0.19 | LINC02600 | −0.46 | 1.05 | −0.23 | 0.14 | −1.00 | AC010319.1 | −0.04 | −0.82 | −0.06 | −0.53 | 0.99 |
| AC010519.1 | −0.97 | 0.64 | 0.16 | 0.81 | 0.51 | RN7SL382P | −0.32 | 0.12 | 1.24 | −0.03 | 0.60 | HNRNPH1P2 | −0.50 | −0.66 | −1.25 | 0.99 | NA |
| REV1 | 0.15 | −0.06 | −0.12 | 0.02 | 0.00 | SFSWAP | −0.09 | 0.04 | −0.11 | 0.07 | 0.02 | AP000569.1 | 0.20 | 0.81 | 1.39 | −1.55 | −0.21 |
| KIAA1109 | −0.20 | 0.24 | 0.29 | 0.08 | 0.02 | AL445928.1 | −0.39 | −0.52 | 1.36 | −0.52 | 0.69 | AC093516.1 | 0.11 | −1.51 | 0.05 | −0.68 | 1.61 |
| AC243836.1 | −1.66 | 0.96 | 0.75 | 0.62 | −0.11 | AC026368.1 | −0.25 | −0.23 | 0.48 | −0.12 | 0.81 | EIF4HP2 | 0.05 | 0.27 | 0.01 | 0.31 | 0.13 |
| MLST8 | 0.27 | −0.16 | −0.44 | 0.09 | −0.14 | AL080312.2 | −0.65 | −0.95 | 0.26 | 0.27 | 0.65 | RPL12P40 | 0.45 | −1.15 | −0.87 | −0.08 | 0.92 |
| AL391863.1 | 0.62 | 0.12 | −0.74 | −0.23 | −0.84 | AC127024.1 | −1.05 | −0.38 | 1.85 | 0.09 | 1.03 | LINC00540 | −0.07 | −0.08 | 0.38 | −0.36 | 0.00 |
| PLPPR3 | −0.89 | 0.20 | −0.20 | 0.44 | −0.05 | AL445435.1 | 0.27 | 0.01 | −0.03 | −0.21 | −0.13 | DPRXP1 | −0.05 | 0.59 | −0.37 | 0.22 | −0.34 |
| AC022364.1 | −0.50 | 0.15 | 0.45 | 0.06 | 0.38 | LINC01704 | 0.80 | −1.17 | 0.70 | −0.02 | 0.25 | AC007192.1 | 0.21 | −0.97 | 0.88 | 0.06 | 0.67 |
| AC010331.1 | −0.78 | 0.38 | 1.22 | 0.08 | 0.61 | AL390243.1 | 0.79 | −1.65 | −0.41 | −0.83 | 0.39 | CCL8 | 0.07 | −1.14 | 0.46 | −1.24 | 0.76 |
| MZT1P1 | 1.04 | −0.68 | −0.46 | −0.32 | −0.13 | GIMD1 | 0.91 | −1.55 | −2.38 | 0.07 | 0.33 | FFAR1 | −0.40 | 0.36 | −0.89 | −0.05 | −0.27 |
| HOXA10 | −0.79 | 0.68 | 1.35 | −0.18 | −0.01 | IL31 | 0.95 | −1.92 | −1.43 | −1.11 | 1.49 | AC010209.1 | −0.22 | −0.56 | 1.91 | 1.22 | 2.35 |
| CELF2-AS2 | −0.61 | 0.33 | 0.66 | −0.12 | 0.13 | BX649597.1 | −1.15 | 0.25 | 1.95 | −0.65 | 1.14 | AF240627.1 | 0.16 | −0.78 | −1.30 | 0.34 | −1.96 |
| AC018607.1 | 0.81 | −0.56 | −1.09 | 0.07 | −1.10 | NOX4 | 0.27 | −0.49 | 0.26 | −0.43 | −0.23 | AC080129.2 | −0.09 | 0.12 | 1.60 | 0.00 | 1.57 |
| C1orf68 | −0.90 | 0.69 | 1.65 | 0.36 | −0.14 | RNASSP343 | 0.53 | −1.38 | −0.01 | −0.99 | 1.11 | RPS24P14 | −0.21 | −1.01 | 0.48 | 0.46 | 0.47 |
| FBXO30 | 0.35 | −0.03 | −0.04 | −0.11 | −0.25 | AC024267.4 | −0.24 | −0.36 | 0.58 | −0.15 | 0.62 | LINC02193 | −0.05 | −0.01 | 0.88 | −0.39 | 0.61 |
| AC018761.3 | 0.97 | −0.13 | −1.07 | −0.08 | −0.38 | MT1M | −0.31 | −0.19 | 0.53 | −0.18 | 0.12 | OR7E155P | 0.50 | −0.05 | −1.84 | 1.43 | 1.84 |
| AL139158.2 | −0.79 | 0.59 | 1.02 | 0.52 | 0.60 | AL078621.1 | 0.64 | 0.31 | 0.13 | 0.25 | −0.46 | AC004039.1 | −0.04 | −0.17 | −0.04 | −0.06 | −0.01 |
| HMGN3-AS1 | −0.44 | 0.30 | 0.01 | 0.28 | 0.08 | PRRX2-AS1 | 0.48 | 0.28 | −0.59 | −0.20 | −1.24 | AC093775.1 | 0.17 | 0.69 | 0.59 | 0.24 | −1.30 |
| PCYT1A | 0.23 | −0.10 | −0.28 | −0.09 | −0.14 | OR52E5 | −0.64 | −1.02 | −0.37 | 0.28 | 0.68 | MRPS31P2 | −0.11 | 0.85 | −1.20 | 0.56 | −1.82 |
| AC007405.3 | −1.33 | 0.81 | 3.07 | 0.06 | 1.02 | AC011853.2 | 0.52 | −0.54 | 0.77 | −0.04 | 0.62 | LINC01293 | 0.05 | −0.12 | −0.05 | 0.46 | 0.67 |
| AL159169.2 | 0.74 | 0.13 | −0.50 | 0.23 | −0.48 | IDO2 | −0.28 | −0.81 | −0.22 | −0.23 | 0.71 | AL445465.2 | 0.09 | −0.22 | −0.62 | −0.35 | −1.58 |
| GCGR | −1.22 | 0.29 | 0.99 | 0.30 | 0.54 | NPM1P2 | 0.75 | −0.39 | −1.34 | 1.16 | 0.36 | AC016168.3 | −0.08 | −0.45 | −0.79 | 0.38 | 0.14 |
| AC138627.1 | −0.75 | 0.11 | −0.04 | 0.49 | 0.17 | FAM133DP | 0.27 | −0.66 | −0.39 | 0.04 | −0.07 | AL035416.1 | 0.07 | −0.37 | −0.57 | −0.07 | −0.37 |
| AL390955.2 | 1.39 | −0.22 | −1.47 | 0.03 | −1.08 | FAM133B | 0.11 | −0.23 | −0.13 | −0.16 | −0.06 | AC099793.1 | 0.34 | −0.22 | 0.25 | −0.94 | 0.67 |
| BCL7A | −0.29 | 0.30 | 0.24 | 0.10 | 0.05 | AL162424.2 | −0.42 | 0.26 | −0.33 | 0.36 | −0.19 | DDX6P1 | −0.34 | −1.16 | 0.35 | −1.37 | 1.09 |
| ERV3-1 | −0.55 | 0.25 | 0.49 | 0.35 | 0.32 | AC090572.3 | −0.71 | −0.31 | −1.93 | 0.19 | −1.42 | AC090241.3 | 0.05 | −0.15 | 0.99 | −0.39 | 0.56 |
| AC006043.1 | −1.54 | 1.24 | 1.04 | −0.75 | −1.22 | RPL26P26 | 0.42 | 0.14 | −0.35 | −0.45 | −0.07 | AL132671.1 | 0.21 | −1.03 | −0.74 | 0.82 | 0.25 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| NUDT17 | −0.43 | 0.30 | 0.10 | 0.27 | 0.08 | AC120498.4 | 0.63 | 0.78 | 1.76 | 0.97 | 1.08 | AC107954.1 | 0.29 | 0.01 | −0.84 | −0.26 | −1.51 |
| AC027612.3 | 0.62 | −0.23 | −0.90 | −0.03 | −0.48 | C2orf66 | 0.30 | −0.56 | −0.35 | −0.18 | 0.12 | AL589880.1 | 0.05 | 0.35 | −0.17 | 0.37 | −0.25 |
| ARHGEF12 | 0.26 | 0.08 | −0.12 | 0.06 | −0.22 | AL138689.1 | 0.33 | −0.24 | −0.02 | 0.03 | 0.55 | AC011474.1 | −0.10 | −1.59 | −2.11 | 0.42 | −0.06 |
| HP | 0.73 | 0.13 | −0.59 | 0.94 | −0.53 | RAB6C-AS1 | −0.55 | −0.10 | 1.03 | 0.81 | 0.13 | AC092810.1 | −0.24 | 0.30 | −0.33 | 0.66 | 0.58 |
| AP000941.1 | −0.54 | 0.13 | −0.22 | 0.15 | −0.04 | RP4-761J14.8 | −0.25 | 0.03 | 0.33 | 0.15 | 0.15 | AF001550.1 | 0.50 | −0.72 | −0.20 | −0.41 | −1.41 |
| MICU2 | 0.27 | −0.05 | −0.25 | −0.06 | −0.31 | API5P1 | 0.39 | −0.18 | −2.64 | 0.29 | −1.92 | RN7SKP120 | 0.44 | −0.19 | 0.29 | −0.55 | −1.75 |
| COPS9 | 0.42 | −0.17 | −0.15 | −0.36 | −0.38 | AC135586.1 | 0.41 | −0.39 | 0.05 | −0.18 | −0.25 | AC063979.2 | 0.49 | −0.92 | −0.57 | −0.62 | 1.30 |
| GOT2P1 | 1.71 | −0.31 | −1.33 | −0.53 | −0.66 | AC008937.1 | 0.45 | −0.16 | 0.26 | 0.20 | 0.50 | AC009743.1 | −0.32 | 0.68 | 0.27 | 0.16 | −0.27 |
| AC012464.2 | −0.89 | 1.03 | 1.41 | −0.22 | −0.19 | AC022306.2 | 0.32 | −0.24 | 0.71 | −0.76 | 0.16 | OR4C12 | −0.48 | −0.45 | 1.29 | −1.52 | −1.57 |
| DNM1P35 | −0.83 | −0.27 | −0.04 | 0.30 | 0.05 | MDN1 | −0.09 | −0.06 | 0.00 | 0.01 | 0.14 | RN7SL180P | −0.06 | −0.05 | −0.06 | −0.49 | −0.09 |
| PTPN2P1 | 0.92 | 0.09 | −0.41 | 0.08 | −0.69 | FCRL3 | 0.46 | −0.80 | 0.36 | −0.24 | 0.05 | RN7SKP82 | 0.49 | −0.71 | 0.13 | −0.59 | −0.26 |
| RPS24P8 | 1.06 | 0.25 | −0.74 | 0.57 | −0.99 | STPG4 | −0.26 | 0.08 | 0.02 | 0.00 | 0.74 | AL031601.1 | −0.49 | 0.39 | 0.87 | −0.54 | −0.44 |
| FAM72C | 1.72 | 0.45 | −1.86 | −0.05 | −1.37 | AL162578.1 | 0.18 | 0.10 | 0.31 | −0.20 | 0.05 | KIR2DP1 | −0.17 | −0.52 | −0.81 | 1.89 | −1.40 |
| C7orf57 | 1.06 | −0.73 | −1.55 | −0.53 | −1.32 | DYTN | −0.66 | 0.67 | −1.48 | 0.01 | −1.80 | AL034379.1 | −0.09 | −0.24 | −0.96 | −0.60 | −1.24 |
| AC117382.1 | −0.47 | 0.01 | 0.11 | 0.25 | 0.22 | ARHGAP23P1 | 0.30 | 0.11 | −0.08 | 0.77 | −0.01 | STAG1 | 0.01 | 0.11 | −0.06 | 0.06 | −0.10 |
| AATF | 0.28 | −0.20 | −0.31 | −0.19 | −0.11 | AC124319.2 | 0.15 | 0.06 | −0.48 | −0.12 | −0.35 | AC108738.1 | −0.08 | 0.98 | 1.04 | 0.89 | −0.01 |
| RRP9 | 0.48 | −0.64 | −0.74 | −0.06 | 0.03 | MMP25 | 0.27 | −0.95 | −1.56 | −0.63 | −0.66 | NDUFAF4P2 | −0.49 | 0.87 | 0.68 | 1.75 | −0.78 |
| KRT18P5 | −0.81 | −0.03 | 0.65 | 0.38 | 0.16 | LY6G5C | −0.20 | −0.05 | 0.02 | −0.03 | −0.11 | AC020913.1 | −0.07 | −0.17 | 0.10 | −0.16 | −0.47 |
| PRRT1B | −1.06 | −0.18 | 0.32 | 0.21 | 0.28 | AL158175.1 | 0.67 | −1.32 | −0.88 | 0.25 | −0.09 | GNG5P3 | −0.10 | −0.47 | 0.26 | 0.01 | 1.44 |
| LINC01943 | 0.85 | −1.12 | −0.70 | −0.87 | −0.16 | AL365205.1 | −0.26 | 0.34 | −0.05 | 0.40 | 0.35 | OR52J3 | −0.24 | 0.05 | 0.55 | 0.84 | 0.75 |
| BANF1P1 | 1.22 | −0.67 | −1.07 | −0.67 | −0.08 | AC013549.3 | −0.36 | −0.46 | −0.77 | 0.27 | 0.05 | C15orf32 | 0.14 | −1.71 | −0.45 | −0.03 | 0.18 |
| SETP5 | 0.96 | −0.56 | −1.21 | −0.07 | −0.14 | ABHD1 | −0.15 | 0.24 | 0.22 | 0.28 | 0.24 | FAM230A | −0.14 | −0.44 | 1.81 | 1.25 | 1.06 |
| SCML1 | −0.27 | 0.15 | 0.30 | 0.11 | 0.19 | RNU4-76P | −0.76 | −0.91 | −0.64 | 0.06 | −0.96 | PRSS40A | 0.19 | −0.76 | −1.04 | −0.91 | −0.83 |
| PLPPR1 | −1.32 | 0.67 | 0.25 | 0.80 | −0.17 | G15642 | −0.28 | −0.07 | −0.04 | 0.38 | 0.50 | AC139792.3 | 0.07 | 0.78 | 2.72 | 0.84 | 1.32 |
| MIR34AHG | −0.47 | −0.19 | 0.36 | 0.01 | 0.33 | KLHDC9 | −0.33 | 0.49 | 0.35 | 0.41 | −0.15 | RNU6-897P | 0.15 | −0.03 | 0.92 | −1.03 | −0.66 |
| DIRAS2 | −1.19 | 0.46 | 1.14 | 0.27 | −0.60 | RPS24P16 | 0.47 | −0.24 | 0.02 | −0.38 | −0.11 | RTN3P1 | 0.10 | −0.03 | 0.16 | 0.82 | 0.44 |
| AC090571.1 | −0.50 | 0.19 | 0.67 | −0.14 | 0.39 | AC109347.1 | 0.29 | 0.16 | 0.44 | 0.01 | 0.26 | AC138625.2 | 0.14 | −0.93 | 0.79 | −1.09 | −0.66 |
| OTUD7A | −0.41 | 0.37 | 0.47 | 0.38 | 0.14 | AP005059.2 | −0.42 | −0.75 | −0.33 | −0.85 | −0.14 | LINC01970 | 0.06 | −1.41 | −0.79 | −0.29 | −0.12 |
| ELMSAN1 | −0.31 | 0.25 | −0.01 | 0.13 | 0.05 | AL355922.4 | −0.34 | 1.13 | −0.16 | 0.30 | −0.93 | AC012645.3 | 0.12 | 0.46 | 1.20 | −0.86 | −0.40 |
| FAM198A | −0.63 | 0.41 | 1.27 | −0.11 | 0.32 | GPX5 | 0.89 | −0.43 | −1.17 | −0.16 | −2.17 | MIR1276 | −0.10 | 0.63 | 0.68 | −0.08 | −0.26 |
| AC078925.2 | −1.10 | 0.21 | 1.83 | −0.25 | −0.58 | SPTB | −0.15 | 0.15 | −0.30 | 0.08 | −0.31 | LINC00877 | 0.06 | −0.05 | −0.69 | 0.12 | −0.65 |
| DAB1 | −0.88 | 0.08 | 0.59 | 0.14 | 0.41 | PEMT | −0.16 | 0.35 | −0.16 | 0.36 | −0.06 | AC020907.3 | −0.11 | −1.82 | −0.10 | −0.32 | 1.05 |
| RNY3 | −0.85 | 0.64 | 1.23 | 0.06 | −0.60 | SNORA71A | 0.20 | 0.07 | −0.47 | 0.26 | −0.83 | AL592164.1 | 0.31 | −0.87 | −1.53 | −0.14 | 0.30 |
| PRPH | −1.61 | 1.67 | 2.34 | 0.92 | 1.32 | MRPS33P2 | 0.68 | −0.84 | −1.24 | −0.13 | 0.03 | BOLA2P3 | 0.10 | −1.24 | 0.56 | 0.66 | 1.23 |
| SPIRE2 | −0.42 | 0.18 | 0.20 | 0.25 | 0.13 | RNU6-759P | 0.30 | −0.03 | 0.45 | −0.08 | 0.07 | MTND1P32 | 0.04 | 0.07 | 0.50 | −0.03 | 0.06 |
| CCDC28A | −0.29 | 0.33 | 0.56 | 0.00 | −0.08 | G5706 | −0.57 | 0.23 | 0.60 | −0.39 | −0.59 | AC012146.4 | −0.36 | −0.57 | −0.66 | 0.67 | −0.12 |
| AC007681.1 | −0.65 | 0.11 | 1.00 | −0.11 | 0.17 | AC108134.3 | −0.20 | −0.18 | 0.36 | 0.03 | 0.29 | RSPH10B2 | 0.08 | −0.32 | −0.53 | 0.10 | 0.06 |
| RBP5 | 0.45 | −0.69 | −0.53 | −0.08 | 0.49 | AC092652.3 | −0.37 | −0.02 | 1.08 | −0.29 | 0.31 | AC114940.1 | −0.30 | 0.98 | 0.60 | −1.35 | −2.30 |
| OR2D3 | 1.30 | −1.14 | −3.43 | 0.49 | −1.94 | AC026523.1 | −0.92 | −0.46 | 1.07 | −0.02 | 1.58 | AL031575.1 | −0.49 | 0.04 | NA | 0.23 | −0.98 |
| MEF2B | −1.00 | 0.63 | 0.47 | 0.27 | 0.26 | ANKDD1A | −0.12 | −0.34 | 0.24 | −0.10 | 0.20 | DTWD2 | −0.02 | 0.18 | −0.17 | 0.12 | −0.11 |
| GLYAT | −1.27 | 0.93 | 0.54 | 0.52 | 0.18 | G27544 | 0.67 | −0.76 | −0.08 | −0.16 | −2.00 | PEAR1 | 0.03 | 0.13 | −0.02 | 0.16 | −0.16 |
| HIPK4 | −1.11 | 0.44 | 1.13 | 0.33 | 0.23 | AC012186.3 | 0.41 | 0.59 | 0.39 | 0.57 | −0.12 | LINC00587 | −0.49 | 0.40 | −0.25 | 1.34 | −1.85 |
| AL360012.1 | −1.11 | 0.16 | −0.85 | 1.03 | −0.54 | AL513217.1 | −1.17 | −0.59 | 2.15 | −1.52 | 1.40 | LINC01007 | 0.18 | −1.25 | −1.93 | 0.54 | 0.69 |
| AC100771.2 | −0.79 | 0.38 | 1.04 | −0.15 | −0.26 | KRT18P62 | 0.31 | −0.65 | −1.06 | 0.10 | −0.45 | RNU4-42P | −0.11 | 1.30 | 1.82 | −0.18 | 0.30 |
| RNA5SP335 | −1.40 | 1.31 | −1.15 | 2.37 | −0.85 | AL357673.2 | −0.43 | 0.26 | −1.33 | 0.36 | −1.25 | RPL21P8 | 0.07 | −0.72 | −0.03 | 0.27 | 0.66 |
| HNRNPH1P3 | −1.65 | 1.67 | 0.49 | 1.20 | −0.55 | AC022211.3 | −0.29 | −0.07 | −1.17 | −0.05 | −0.03 | RPS6P12 | 0.20 | −0.85 | −2.10 | 1.94 | −0.36 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC124916.2 | 0.96 | −0.20 | −0.28 | −0.37 | −0.66 | AL121983.1 | −0.55 | −0.89 | 0.38 | −0.59 | 1.58 | RBBP4P3 | −0.17 | −0.78 | −0.05 | 0.15 | −2.53 |
| ADD3-AS1 | −0.74 | 0.50 | 0.69 | 0.77 | 0.21 | AP002833.2 | −0.88 | 0.82 | −1.60 | 0.34 | −1.28 | AL022313.4 | 0.20 | −0.98 | −0.85 | −1.73 | −1.21 |
| STRN4 | 0.17 | −0.08 | −0.39 | −0.02 | −0.21 | AL133371.1 | −0.67 | 1.52 | 2.27 | −1.22 | −0.34 | MMP20 | 0.12 | −0.05 | −1.97 | 0.66 | 0.10 |
| LINC00506 | −0.97 | 0.51 | −0.31 | 0.05 | −0.28 | EEF1A1P25 | −0.20 | 0.11 | 0.07 | 0.13 | −0.11 | AL354751.2 | −0.18 | 0.20 | −0.89 | 0.43 | −0.28 |
| PPP1R14C | 0.53 | −0.02 | −0.50 | 0.24 | −0.37 | KLRB1 | 0.29 | −0.01 | 0.10 | 0.17 | 0.35 | SLC10A1 | −0.02 | −0.04 | −0.39 | 0.10 | −0.33 |
| CLEC17A | 1.68 | −1.20 | −0.39 | −0.14 | 0.73 | GATA6-AS1 | −0.59 | −0.94 | −0.17 | −0.19 | 0.82 | AC000067.1 | 0.36 | −0.04 | −0.44 | 0.11 | 0.80 |
| FAM66A | −1.15 | 0.28 | 1.92 | −0.04 | 0.70 | AC019118.2 | 0.84 | −1.14 | 1.08 | −0.47 | 0.35 | RNASEHIP1 | 0.49 | −0.72 | −1.36 | −0.51 | −5.67 |
| RNU6-1176P | −1.11 | 0.16 | 0.94 | −0.81 | 0.02 | CENPBD1P1 | 0.09 | 0.13 | 0.04 | −0.03 | −0.18 | AC011899.4 | 0.11 | −1.18 | −2.40 | 0.35 | −1.80 |
| SNHG4 | 0.45 | −0.37 | −0.18 | 0.13 | 0.47 | SMIM28 | −0.64 | −0.78 | 0.54 | −0.87 | −0.49 | IGHV3-50 | −0.49 | 0.45 | 0.15 | −0.14 | −1.07 |
| DNAJC13 | 0.19 | −0.14 | −0.13 | −0.09 | −0.09 | CXCL14 | 0.20 | 0.19 | 0.23 | 0.20 | −0.21 | AC087518.1 | 0.49 | −0.48 | −2.03 | 0.10 | −1.37 |
| CHRNA6 | 1.47 | −0.49 | −2.43 | 0.67 | −0.84 | COX11 | 0.10 | 0.03 | 0.03 | 0.01 | −0.04 | AC022919.1 | 0.03 | −0.03 | −0.48 | −0.05 | −0.18 |
| AL136369.2 | −1.18 | 0.65 | 1.07 | −0.16 | −0.05 | AL590635.1 | −1.49 | 1.17 | 0.26 | 2.15 | −2.03 | BCAS2P2 | 0.04 | −0.08 | 0.92 | −0.22 | 0.40 |
| DUSP27 | −1.02 | −0.28 | 0.07 | 0.66 | 0.22 | AC073136.1 | 0.57 | −0.20 | −1.88 | −0.24 | −0.48 | AC009852.1 | 0.49 | −0.52 | −3.09 | −0.32 | −1.39 |
| LINC00596 | −1.19 | 1.22 | 0.20 | 0.97 | 0.32 | AC073316.1 | −0.62 | 0.75 | 2.85 | −0.14 | −0.94 | AC092335.1 | 0.26 | 0.41 | −1.01 | −0.17 | −2.77 |
| BTD | −0.35 | 0.30 | 0.05 | 0.46 | 0.12 | MAP10 | 0.19 | 0.20 | −0.26 | 0.28 | −0.23 | FAM76B | 0.01 | 0.05 | 0.02 | 0.00 | −0.09 |
| AL445250.1 | −1.01 | 0.53 | 0.46 | 0.74 | −0.16 | AC091965.5 | 0.51 | 0.18 | −0.40 | 0.57 | −0.42 | BX284656.1 | −0.18 | −1.24 | −2.84 | 0.29 | −0.43 |
| MIR4670 | 1.34 | −0.87 | −0.64 | 0.12 | −0.24 | GRIA3 | 0.21 | −0.15 | 0.69 | −0.76 | −0.03 | RN7SL604P | −0.15 | −0.61 | −0.68 | 1.30 | −0.22 |
| GNGT2 | 1.13 | −0.65 | −0.49 | −0.23 | −0.42 | AC093783.1 | 0.43 | 0.10 | −0.47 | 0.20 | −0.20 | AC091167.4 | −0.08 | −1.08 | 0.29 | −0.56 | −0.47 |
| OR13J1 | −1.89 | 1.35 | 3.11 | −0.01 | 1.14 | AL353662.4 | −0.84 | −0.09 | −0.88 | 0.25 | −0.63 | C22orf42 | −0.11 | −0.81 | −1.43 | −0.13 | −0.24 |
| GP2 | −1.82 | 1.25 | 0.75 | 0.23 | −0.55 | AC021517.1 | −0.39 | 0.20 | 0.51 | 0.34 | 0.01 | RSL24D1P9 | 0.21 | −0.20 | −0.74 | 1.03 | −1.63 |
| AC005831.1 | −0.86 | 0.42 | 1.03 | −0.22 | 0.42 | AC024940.1 | −0.29 | −0.49 | −0.62 | −0.18 | 0.05 | AP000462.2 | −0.04 | −0.25 | 0.15 | −0.02 | 0.54 |
| SULT1C2 | −0.76 | 0.14 | 0.20 | 0.20 | 0.11 | AC087633.2 | −0.41 | 0.38 | 0.38 | 0.38 | 0.22 | AL445235.1 | −0.13 | 0.28 | −0.49 | 0.07 | −2.61 |
| CYP21A2 | −1.38 | 0.85 | 1.55 | 0.76 | 1.16 | AF186192.3 | −0.77 | −0.18 | 0.19 | 0.38 | 0.39 | AC009336.1 | 0.06 | −0.84 | −0.52 | 0.02 | −0.65 |
| AL158166.1 | 1.32 | 0.46 | 0.46 | 0.36 | −0.46 | RNPS1P1 | 0.35 | −0.42 | −0.83 | 0.21 | 0.05 | RNU6-818P | −0.29 | 0.13 | −0.33 | −0.63 | −1.86 |
| G24464 | −1.19 | 1.30 | 1.11 | 0.96 | 0.06 | AL359396.1 | −0.91 | −0.66 | 0.00 | 0.89 | 1.00 | RPL22P20 | −0.20 | −1.16 | −0.98 | −0.68 | 0.66 |
| CADM3-AS1 | −0.56 | 0.15 | 1.37 | −0.12 | 0.42 | SEC16A | 0.09 | −0.10 | −0.19 | −0.04 | −0.05 | NEK10 | 0.04 | −0.25 | −0.56 | −0.20 | 0.09 |
| PON1 | −1.37 | 0.69 | 1.97 | 0.10 | 0.51 | SCRT1 | −0.73 | 0.54 | 2.15 | −0.13 | 0.22 | LINC01087 | 0.09 | −0.94 | 0.95 | −0.01 | 2.10 |
| HLA-DQB2 | −0.86 | 0.03 | 1.25 | −0.26 | 0.66 | RNU6ATAC40P | −1.27 | 1.40 | 0.09 | 0.17 | −1.00 | RN7SL173P | 0.07 | 0.39 | 0.42 | −0.14 | 0.06 |
| AC107068.2 | 1.51 | −0.86 | −0.77 | −0.62 | 0.24 | RNU6-963P | 0.56 | 0.38 | 1.33 | −0.20 | 0.73 | LINC00395 | 0.22 | 0.09 | −0.61 | 0.89 | −1.82 |
| AC025031.3 | 1.05 | −0.72 | −1.16 | −0.41 | −0.58 | AL355974.1 | −0.75 | −0.74 | −0.10 | −0.06 | −1.20 | FOXS1 | 0.06 | −0.19 | −0.05 | 0.21 | −0.48 |
| FAM193B | −0.39 | 0.19 | 0.13 | 0.27 | 0.29 | AC016573.1 | −0.73 | −0.06 | 0.19 | −0.77 | −0.31 | EEF1A1P2 | −0.16 | −1.53 | −1.04 | 0.49 | 0.55 |
| RPL18AP3 | 0.66 | 0.01 | −0.11 | −0.33 | −0.22 | AL353719.1 | 0.36 | −0.32 | −0.33 | 0.20 | 0.54 | AC080023.2 | 0.13 | 0.81 | 0.01 | −0.52 | 1.05 |
| AL354949.1 | −1.11 | 0.15 | 1.53 | −0.36 | −0.36 | DNAJC19P5 | 0.21 | −0.10 | 0.37 | 0.03 | 0.27 | AL445070.1 | 0.47 | −1.98 | −0.88 | −0.78 | −0.59 |
| PCBP2 | 0.38 | −0.14 | −0.32 | 0.11 | −0.10 | LINC01608 | −0.66 | −1.75 | −0.35 | 0.31 | 1.72 | AP003784.1 | −0.23 | 1.33 | 0.32 | 0.28 | −0.53 |
| AL355613.1 | 0.82 | −0.54 | 0.01 | 0.06 | 0.49 | LDLRAD4-AS1 | −0.24 | 0.16 | 0.07 | 0.21 | −0.09 | LINC00866 | −0.07 | 0.87 | −1.03 | 0.57 | −0.71 |
| NEK8 | −0.45 | 0.07 | 0.27 | 0.33 | 0.44 | PRAL | −0.40 | −0.82 | 0.09 | −1.91 | −0.32 | ABHD17AP4 | −0.14 | −0.81 | 1.79 | −0.58 | 1.67 |
| MAP3K12 | −0.39 | 0.22 | 0.14 | 0.22 | −0.12 | AC020912.1 | −0.46 | −1.00 | −0.01 | −0.39 | 0.28 | MTND1P31 | −0.49 | 0.18 | 0.29 | 0.39 | −0.09 |
| PCAT14 | −1.26 | −0.22 | 0.21 | 0.01 | 0.30 | AC024475.3 | −0.62 | −1.71 | −0.99 | −0.46 | −0.34 | AC093835.1 | −0.12 | −1.44 | −1.63 | 0.39 | −0.23 |
| AC073578.1 | 2.07 | −1.79 | −3.79 | 0.08 | −1.30 | MYCBPAP | −0.25 | −0.21 | −0.71 | 0.09 | −0.24 | LINC02430 | −0.20 | −1.16 | −0.25 | −0.66 | 2.26 |
| FRS2 | 0.29 | −0.06 | −0.25 | −0.07 | −0.20 | HEATR9 | 0.25 | 0.03 | 0.22 | −0.03 | 0.10 | GAPDHP68 | −0.18 | 0.55 | 0.10 | −0.26 | −1.77 |
| AC083864.3 | −1.25 | 1.07 | 1.35 | 0.66 | 1.40 | RNU6-534P | −0.59 | 0.44 | 2.56 | −0.54 | 0.58 | FTH1P5 | −0.10 | −0.33 | −1.23 | 1.30 | 1.39 |
| AL117344.1 | −1.91 | 0.05 | 2.91 | 0.82 | 0.82 | SLC22A24 | −0.38 | 0.37 | 0.49 | −0.01 | 0.31 | RNUSA-6P | −0.05 | −0.52 | 0.34 | −0.61 | 0.19 |
| OLFM1 | 0.50 | −0.28 | −0.18 | −0.21 | −0.33 | AC095031.1 | 0.81 | −1.28 | −0.33 | 0.26 | −0.30 | RFESDP1 | −0.26 | −0.41 | 0.95 | −1.56 | 0.59 |
| LINC00871 | −1.98 | 1.30 | 0.11 | 0.81 | −2.78 | DMRT3 | −0.34 | 0.26 | 1.47 | −0.91 | −0.32 | CD163L1 | 0.03 | −0.08 | 0.04 | −0.25 | −0.16 |
| LARS2 | 0.26 | −0.27 | −0.42 | −0.04 | −0.03 | AC099494.2 | 0.29 | 0.13 | 0.19 | −0.19 | −0.15 | BX679664.2 | 0.06 | −0.33 | −0.03 | 0.00 | 0.18 |
| AP001120.1 | −1.44 | 0.39 | −0.66 | 1.16 | −0.34 | ELL | −0.12 | −0.06 | −0.39 | 0.05 | −0.12 | AC095038.2 | 0.48 | −0.83 | −0.02 | −0.17 | −0.38 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AL591895.1 | −0.75 | 0.35 | 1.47 | −0.03 | 0.91 | POLHP1 | 0.21 | −0.11 | 0.19 | −0.41 | −0.12 | AC025754.1 | −0.07 | −1.20 | 2.48 | −1.52 | 0.07 |
| AL450998.2 | 0.64 | −0.17 | −0.54 | −0.09 | −0.59 | ST13P3 | 0.41 | −0.12 | −0.24 | 0.33 | −0.49 | OR2U2P | −0.25 | −1.01 | −1.50 | −0.59 | −0.49 |
| METTL23 | 0.32 | −0.29 | −0.42 | −0.01 | −0.17 | RPL13AP3 | 0.38 | −0.15 | −1.52 | −0.16 | −0.94 | AC010740.1 | −0.18 | −0.52 | −2.30 | 1.67 | −1.56 |
| B3GALT5-AS1 | −1.12 | 1.09 | −0.33 | 0.82 | −0.87 | HEY2 | −0.23 | 0.27 | 0.76 | 0.04 | −0.14 | RPL7AP10 | 0.04 | 0.00 | 0.64 | −0.13 | −0.19 |
| C1QTNF2 | −0.58 | 0.25 | 0.08 | 0.13 | −0.13 | RPSAP75 | 0.84 | −1.87 | 1.35 | −1.03 | 0.99 | RN7SL284P | −0.05 | −0.01 | 0.09 | 0.00 | 0.03 |
| OLFM5P | −1.00 | 0.86 | 0.62 | −0.22 | −0.67 | BABAM2 | −0.07 | 0.07 | 0.08 | −0.04 | −0.12 | AC023078.2 | −0.32 | −1.16 | 0.39 | −0.38 | −0.32 |
| 1-Mar | 0.30 | −0.30 | −0.05 | 0.00 | 0.16 | RPS18P9 | −0.16 | 0.40 | 0.18 | 0.19 | −0.17 | AHCTF1P1 | 0.04 | −0.08 | 0.18 | 0.19 | 0.29 |
| CEP78 | 0.32 | −0.41 | −0.14 | −0.21 | 0.12 | RNA5SP159 | 0.51 | −0.97 | 0.06 | −0.85 | 0.15 | AC099524.1 | 0.09 | −0.37 | −1.44 | −0.13 | −1.17 |
| JAK1 | 0.31 | −0.03 | −0.04 | −0.06 | −0.27 | GAPDHP16 | −1.04 | 0.73 | −2.65 | 1.72 | −1.71 | RNU2-62P | 0.20 | −0.77 | −1.20 | −1.00 | −1.29 |
| AGBL1 | −1.11 | −0.61 | −0.10 | −0.04 | −0.23 | AP003498.1 | −0.63 | −1.02 | 0.97 | −0.37 | 0.89 | AC011474.4 | 0.31 | −0.30 | −0.77 | −0.94 | −3.35 |
| C20orf194 | −0.23 | 0.03 | 0.05 | 0.02 | 0.03 | G34396 | −0.52 | −0.17 | 1.46 | −0.40 | 0.79 | AL031283.3 | −0.15 | −1.04 | 1.10 | −0.99 | −0.31 |
| IK | 0.29 | −0.12 | −0.31 | −0.09 | −0.24 | SLC25A25 | 0.16 | −0.04 | −0.45 | −0.27 | −0.42 | AC021546.1 | −0.16 | −0.12 | 1.24 | −1.20 | −0.72 |
| RPL23AP86 | −0.97 | 0.70 | −0.18 | −0.16 | −1.14 | GAPDHP44 | −0.39 | −0.70 | 0.59 | −0.73 | 1.09 | G11342 | −0.16 | 0.26 | 1.59 | 0.38 | −0.55 |
| MZF1-AS1 | −0.46 | 0.42 | 0.38 | 0.08 | −0.24 | AC005722.2 | 0.23 | 0.07 | −0.49 | 0.44 | −0.37 | AL109924.2 | −0.09 | 0.32 | 0.87 | −0.31 | −0.50 |
| FOLR1 | −1.26 | 1.05 | 2.14 | 0.11 | 0.33 | LINC00158 | −0.38 | −0.23 | 0.07 | −0.58 | −0.71 | AC020626.1 | 0.48 | −0.48 | −0.55 | 0.45 | 0.27 |
| SPCS2 | 0.23 | −0.04 | −0.31 | −0.02 | −0.26 | NCBP2-AS1 | −0.19 | −0.35 | −0.13 | 0.06 | 0.60 | AC021146.5 | 0.46 | −2.08 | 0.61 | −0.02 | 2.35 |
| AP001453.3 | 0.98 | 0.16 | −0.77 | −0.08 | −0.49 | C2orf74 | 0.25 | −0.69 | 0.03 | 0.10 | 0.19 | RPL9P5 | −0.10 | −0.46 | −0.62 | 1.10 | 0.61 |
| COL6A3 | 0.63 | −0.36 | 0.14 | −0.75 | −0.49 | RNU6-1223P | 0.67 | 0.14 | −1.03 | 0.26 | −1.22 | AC026100.1 | −0.16 | −0.67 | 0.12 | 0.44 | 1.83 |
| LRRC7 | −0.56 | 0.03 | 0.20 | 0.13 | 0.25 | RP11-592B15.3 | −0.88 | 0.46 | 0.05 | 0.32 | −2.66 | AC107958.2 | −0.14 | −0.98 | 1.84 | −2.32 | 0.39 |
| RGPD5 | −0.67 | 0.71 | 0.36 | 0.63 | 0.09 | MIER2 | −0.11 | 0.01 | −0.17 | 0.11 | −0.01 | AL450384.2 | −0.02 | 0.31 | −0.03 | 0.29 | 0.03 |
| EXOSC7 | −0.35 | 0.28 | 0.23 | 0.30 | 0.14 | HNRNPA1P41 | 0.44 | −0.24 | −0.57 | −0.19 | −1.22 | COMMD5 | −0.02 | −0.01 | −0.12 | 0.04 | 0.02 |
| RNA5SP387 | −1.27 | 1.12 | −0.36 | 1.60 | −0.08 | RNU7-19P | 0.60 | −1.22 | 0.68 | −0.18 | 1.15 | AC135507.1 | −0.07 | −0.17 | 0.60 | −0.82 | −0.64 |
| HMGB1P29 | −1.55 | 1.04 | 1.96 | 0.85 | 0.12 | AL162311.1 | 0.41 | −0.38 | 0.13 | 0.09 | −0.11 | LINC01509 | 0.22 | −0.36 | −0.86 | 1.09 | −1.63 |
| AC009108.3 | −1.24 | 0.22 | 0.40 | 0.62 | 0.53 | PIGHP1 | −0.17 | 0.26 | −0.13 | −0.04 | −0.27 | LINC01884 | 0.20 | −1.47 | 0.30 | −0.46 | 0.45 |
| AP001062.1 | −0.65 | 0.56 | 0.38 | 0.33 | 0.18 | SOCS5 | 0.10 | 0.15 | 0.13 | −0.10 | −0.12 | E2F4P1 | 0.48 | −0.19 | −0.53 | 0.49 | 0.96 |
| ATRN | 0.33 | −0.03 | −0.04 | −0.08 | −0.11 | ACP2 | 0.09 | −0.16 | −0.45 | 0.09 | −0.03 | MAPK7 | 0.01 | −0.13 | −0.13 | 0.00 | −0.01 |
| AL162596.1 | 1.88 | −0.11 | −2.65 | 0.08 | −2.95 | AL670729.3 | 0.85 | −2.43 | −0.64 | −1.45 | 0.48 | AC106707.2 | −0.04 | 0.17 | 0.15 | 0.35 | −0.04 |
| MED29 | 0.26 | −0.16 | −0.13 | −0.06 | −0.01 | LINC01919 | −0.36 | −0.03 | 0.61 | −0.08 | 0.33 | OR6K5P | 0.45 | −0.79 | 0.44 | −1.02 | 0.78 |
| ACTL7A | −1.28 | 0.14 | 0.97 | 0.13 | −0.05 | C4orf3 | 0.17 | 0.03 | 0.13 | 0.08 | −0.23 | LINC02161 | −0.33 | −0.78 | −0.08 | −0.73 | 0.42 |
| AC116407.4 | −0.61 | 0.40 | 0.75 | 0.19 | 0.28 | AL160171.1 | −0.51 | −0.42 | 0.22 | −1.11 | 0.32 | ATP11AUN | 0.14 | −1.11 | 1.53 | 0.06 | 2.38 |
| AC015726.1 | −0.50 | −0.18 | 0.38 | −0.39 | 0.46 | RNU6-681P | 0.50 | −0.13 | −0.92 | 0.25 | 0.53 | AL359881.2 | 0.11 | −0.90 | −0.72 | 0.17 | 0.43 |
| ROR1 | −0.34 | 0.48 | 0.49 | 0.08 | −0.06 | AC110084.1 | 0.49 | −0.85 | 0.79 | −1.14 | 0.67 | AC015819.3 | 0.13 | −0.83 | −2.71 | 0.49 | −2.19 |
| AC013451.2 | 1.53 | −0.81 | −0.80 | 0.19 | 0.31 | CCL24 | 0.53 | −0.75 | 0.99 | −0.44 | 0.85 | AC108078.3 | −0.21 | −0.39 | −0.82 | 1.86 | 0.16 |
| AL157871.3 | 1.12 | −0.88 | −0.41 | 0.04 | −0.15 | AC027307.3 | −0.26 | −0.04 | 0.06 | −0.07 | 0.26 | AC114402.2 | 0.03 | −0.30 | −0.22 | 0.13 | 0.03 |
| FAM45A | 0.28 | −0.15 | −0.09 | −0.11 | −0.06 | CYP1D1P | 0.97 | −1.51 | −2.58 | 1.74 | 0.90 | LINC00331 | −0.48 | 0.28 | −1.68 | 0.23 | −2.58 |
| AC007728.2 | 0.86 | −0.34 | −0.81 | −0.11 | −0.37 | AL162718.1 | 0.40 | −0.32 | 0.07 | −0.15 | 0.31 | GABARAP | −0.03 | 0.35 | −0.96 | 0.58 | −0.48 |
| MXI1 | −0.40 | 0.51 | 0.52 | 0.34 | −0.20 | RNU6-202P | 0.42 | −1.33 | −0.61 | −0.49 | 0.12 | AL031073.1 | 0.25 | −1.98 | −0.61 | −1.11 | 0.65 |
| CLCNKA | −1.38 | 0.48 | 1.43 | 0.32 | 0.89 | B3GNT7 | −0.24 | 0.25 | 0.08 | 0.07 | 0.08 | G27123 | 0.44 | 2.13 | 0.32 | 0.49 | −1.39 |
| ENTPD3-AS1 | −0.43 | 0.22 | 0.58 | −0.06 | 0.22 | NBEAP1 | −0.42 | −0.29 | 0.18 | 0.67 | −0.08 | APOBEC4 | 0.04 | −0.58 | 0.16 | −0.41 | 0.33 |
| AC007390.2 | −0.38 | 0.38 | 0.21 | 0.33 | 0.05 | ATP8B3 | −0.23 | −0.10 | −0.11 | −0.06 | −0.04 | AC092634.6 | 0.48 | −1.27 | −0.44 | 0.84 | NA |
| RYBP | 0.30 | −0.03 | −0.32 | −0.15 | −0.39 | RP11-380M21.4 | 0.29 | 0.48 | 0.05 | 0.14 | −0.17 | AC023632.1 | 0.02 | −0.07 | 0.09 | −0.05 | 0.08 |
| NUDT9 | 0.19 | 0.01 | 0.05 | −0.03 | −0.09 | RSL24D1P8 | −0.26 | 0.29 | 0.58 | −0.27 | 0.26 | RN7SL615P | −0.07 | 0.50 | −0.86 | −0.08 | −0.81 |
| SPDYE16 | −0.80 | 0.80 | 0.84 | 0.70 | 0.78 | AL831737.1 | 0.36 | −0.24 | 0.23 | −0.09 | −0.01 | AC007333.2 | 0.20 | −1.25 | 0.18 | −1.83 | −0.65 |
| AC048382.5 | −0.91 | 0.29 | 0.72 | 0.28 | 0.71 | GCC2 | −0.09 | 0.07 | 0.20 | −0.07 | −0.01 | AC073127.1 | −0.08 | 0.31 | −0.11 | −0.21 | −0.40 |
| INPP1 | 0.38 | −0.34 | −0.29 | −0.06 | 0.02 | MIR571 | 0.59 | −0.34 | 1.59 | 0.28 | 0.96 | RNU6-646P | −0.11 | 0.42 | 0.47 | 0.17 | 0.14 |
| AC026951.1 | −0.74 | 0.57 | 0.37 | 0.25 | −0.34 | AL807776.1 | −0.70 | 0.09 | −1.53 | 0.15 | −2.54 | AC105049.1 | 0.20 | −0.13 | 1.23 | −0.33 | −0.34 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| PCDH18 | −0.69 | 0.33 | 1.28 | −0.37 | 0.00 | AC040162.3 | −0.33 | 0.58 | −0.13 | 0.73 | −0.66 | AC092638.1 | 0.28 | −1.55 | −1.22 | −0.99 | −0.16 |
| HOXA6 | −0.84 | 0.33 | 0.65 | 0.57 | −0.36 | AC140912.1 | 0.85 | −1.11 | −2.47 | 1.08 | −1.40 | AC103996.3 | −0.27 | 1.07 | −0.17 | 1.26 | 0.00 |
| GRID1 | −0.65 | 0.11 | 0.94 | −0.15 | 0.01 | AC130456.3 | −0.55 | −1.50 | −2.18 | 0.06 | 1.09 | ANKRD33 | 0.11 | −1.49 | −0.17 | −1.31 | 1.75 |
| NDUFB4P6 | −0.87 | 0.61 | 0.22 | 0.47 | 0.09 | CBARP | −0.21 | 0.34 | −0.18 | 0.41 | −0.26 | NDST3 | 0.03 | 0.11 | −0.31 | 0.10 | −0.23 |
| RAB4A | 0.31 | 0.02 | −0.15 | 0.05 | −0.15 | AC093159.2 | 0.82 | −1.12 | −0.43 | −0.78 | −1.39 | AMMECR1L | 0.01 | −0.07 | 0.01 | −0.09 | 0.01 |
| RAB29 | 0.39 | −0.41 | −0.40 | −0.21 | −0.11 | ATXN7L3B | 0.12 | 0.05 | 0.18 | −0.02 | 0.03 | HTR5A | 0.09 | −1.43 | −1.30 | −0.30 | −1.21 |
| AC010503.4 | 0.86 | 0.25 | −0.18 | 0.23 | −0.77 | NOTCH1 | 0.12 | 0.04 | −0.09 | 0.23 | 0.18 | AC021035.1 | 0.48 | 1.06 | −1.15 | −0.23 | −1.30 |
| CHN1 | 0.52 | −0.32 | 0.26 | −0.67 | −0.02 | AC011939.2 | 0.26 | 0.01 | 0.16 | 0.52 | −0.12 | NOTCH3 | −0.02 | 0.22 | 0.10 | 0.23 | −0.01 |
| BEAN1 | −0.58 | 0.61 | 0.36 | 0.38 | 0.25 | STAB2 | −0.28 | 0.31 | 0.71 | −0.01 | 0.03 | AL162717.1 | 0.18 | −0.22 | −0.91 | 0.49 | −0.46 |
| PNMA3 | −0.89 | 0.33 | 0.17 | 0.14 | 0.42 | MASP2 | −0.25 | 0.38 | 0.29 | 0.20 | −0.04 | AC007751.1 | 0.46 | −0.59 | −0.96 | 0.69 | −2.67 |
| SLC25A10 | 0.58 | 0.01 | −0.55 | 0.69 | 0.13 | LINC01796 | −0.71 | 0.06 | −2.43 | 0.33 | −1.59 | AC025588.2 | 0.48 | −1.21 | −0.53 | 0.59 | −0.31 |
| RNA5SP259 | −1.20 | 1.17 | 0.04 | 1.50 | −0.10 | STIMATE | 0.19 | 0.08 | −0.43 | 0.08 | −0.30 | AL356056.3 | 0.16 | 1.65 | 0.30 | 1.35 | −1.50 |
| PIGFP2 | 0.89 | −0.53 | −1.83 | −0.25 | −0.44 | AC110288.1 | 0.46 | −1.90 | −1.63 | 0.13 | 0.66 | AL049651.2 | 0.23 | −0.83 | −0.22 | 0.36 | −0.70 |
| MAN2B2 | −0.21 | 0.18 | 0.08 | 0.03 | −0.12 | AL354751.3 | −0.22 | −0.31 | 0.06 | 0.39 | 0.88 | SRSF10P1 | 0.04 | −0.14 | −0.56 | 0.32 | 0.04 |
| FMNL3 | 0.40 | −0.53 | −0.25 | −0.44 | −0.01 | AC027097.1 | −0.14 | 0.00 | 0.39 | −0.21 | 0.21 | AC023886.1 | 0.12 | −0.81 | 1.46 | 0.26 | 0.11 |
| SLC7A9 | −1.05 | −0.60 | 1.61 | −0.17 | 1.28 | FAM168A | −0.07 | 0.12 | 0.22 | −0.06 | 0.04 | LINC02404 | 0.15 | −1.48 | −0.90 | 0.15 | 0.77 |
| AF107885.2 | 0.59 | −0.34 | −0.45 | −0.24 | −0.07 | G36840 | 0.46 | 0.14 | 0.82 | 0.20 | −0.11 | AL035404.2 | 0.11 | 0.14 | −0.26 | 0.20 | −1.21 |
| LINC02341 | 1.46 | −0.73 | −0.96 | −0.62 | 0.26 | AL158152.2 | −0.23 | 0.04 | 0.77 | −0.36 | 0.27 | MIR4637 | −0.08 | −0.08 | 0.28 | 0.05 | −0.39 |
| NET1 | 0.31 | 0.17 | −0.28 | 0.10 | −0.42 | LARS2P1 | −0.98 | 0.34 | 1.37 | 1.05 | −1.11 | AC110491.3 | 0.19 | 0.02 | 0.81 | −0.14 | 0.28 |
| DOCK9 | 0.22 | 0.18 | 0.05 | 0.08 | −0.17 | KLF13 | 0.15 | 0.19 | −0.04 | 0.12 | −0.28 | AC134508.1 | −0.12 | −0.41 | −1.17 | 0.32 | 1.43 |
| PPFIA4 | −0.56 | 0.21 | 0.29 | 0.14 | 0.18 | AC093166.2 | 0.43 | 0.55 | −0.83 | 0.23 | −0.71 | AL606760.3 | 0.06 | −0.31 | −0.57 | −0.01 | −0.29 |
| AC093323.1 | −0.26 | 0.09 | 0.36 | 0.14 | 0.39 | AC002984.1 | −0.51 | −0.06 | −0.69 | −0.83 | −1.17 | HLA-P | −0.19 | 0.45 | −1.90 | 0.88 | −1.22 |
| SPATA9 | −0.94 | 0.08 | 1.24 | 0.53 | 0.71 | SIGLEC8 | −0.45 | 0.01 | 1.66 | −0.26 | 0.95 | CLEC18B | −0.07 | −0.77 | 0.58 | 0.28 | 0.63 |
| GXYLT1 | 0.25 | 0.03 | 0.08 | 0.06 | −0.08 | POLRMTP1 | −0.31 | 0.54 | −0.19 | 0.85 | −0.57 | HTN1 | −0.12 | 0.41 | −1.09 | 0.93 | −1.60 |
| CCL22 | 1.27 | −1.66 | −1.48 | −1.37 | −0.85 | EMILIN2 | −0.23 | −0.07 | 0.27 | −0.16 | −0.18 | AC008588.1 | 0.19 | −0.57 | −0.51 | −0.53 | 0.08 |
| NXPE1 | −0.80 | 0.17 | 0.61 | 0.00 | 0.50 | ATP2A1-AS1 | 0.68 | 0.82 | −1.85 | 0.51 | −1.66 | IFNA8 | 0.16 | 0.50 | −2.37 | 0.35 | −2.57 |
| LINC01206 | 1.33 | −0.86 | −1.48 | 0.28 | −0.72 | AC026111.1 | 0.17 | −0.14 | 0.12 | −0.20 | −0.13 | G5709 | 0.08 | −0.11 | −1.35 | 0.52 | −0.47 |
| RNU1-55P | −1.91 | 0.00 | −1.49 | −0.08 | −1.42 | SETD1B | −0.09 | 0.11 | −0.24 | 0.21 | −0.07 | RNU2-29P | 0.15 | −0.12 | −0.51 | 1.76 | 0.20 |
| G24514 | −1.12 | 0.58 | 1.31 | 0.78 | 0.10 | ANKS1A | 0.06 | 0.12 | −0.08 | 0.14 | −0.05 | RNA5SP497 | 0.18 | −0.12 | −1.34 | 1.00 | −0.45 |
| LILRB5 | −0.78 | 0.52 | 0.28 | 0.28 | −0.21 | IGHV1-24 | 1.22 | 0.66 | 1.81 | 1.41 | −0.33 | ARHGEF15 | −0.03 | 0.07 | 0.43 | 0.04 | −0.13 |
| ALDOC | −0.52 | 0.92 | 1.04 | 0.39 | −0.12 | PCNX1 | 0.08 | −0.12 | 0.03 | −0.19 | 0.07 | POU4F2 | −0.11 | −1.66 | 0.66 | −0.89 | 1.08 |
| ADORA2A-AS1 | −0.80 | −0.34 | 0.02 | 0.41 | 0.28 | ANGPTL6 | −0.20 | −0.05 | −0.03 | 0.31 | −0.07 | HOXD3 | 0.04 | −0.17 | 0.95 | 0.03 | 0.90 |
| LINC01152 | −1.02 | 1.02 | 0.86 | 0.40 | 0.66 | NCOR1P1 | −0.96 | 0.06 | −0.82 | −0.43 | −1.00 | AC091435.2 | −0.06 | −0.06 | 0.70 | −0.11 | −0.24 |
| AC067852.4 | 0.74 | −0.17 | 0.10 | 0.12 | −0.01 | NIT2 | −0.10 | 0.08 | 0.16 | 0.21 | 0.24 | RN7SL60P | 0.36 | 0.55 | −0.70 | 3.02 | 0.62 |
| IRX3 | −0.34 | 0.53 | 0.23 | 0.48 | 0.10 | AP000915.2 | −0.39 | −0.49 | 0.48 | 0.12 | 0.08 | CDK5R2 | 0.13 | −1.95 | −0.96 | −1.30 | 0.78 |
| GBP3 | 0.38 | −0.49 | −0.21 | −0.51 | −0.13 | AC004854.1 | −0.43 | 0.64 | −1.39 | 1.03 | −1.08 | AC093155.1 | −0.04 | −0.06 | −0.33 | −0.05 | 0.22 |
| AC105760.1 | −0.63 | 0.48 | 0.94 | 0.05 | 0.15 | G42703 | −0.29 | 0.06 | 0.35 | 0.01 | −0.30 | IGLV9-49 | 0.47 | 0.85 | −0.37 | 1.32 | −0.95 |
| AC005899.5 | −0.89 | 0.35 | 1.73 | −0.33 | 0.29 | ARMC5 | 0.19 | −0.07 | −0.37 | 0.12 | 0.02 | HNRNPA1P73 | 0.20 | 0.03 | −0.75 | −0.72 | −2.39 |
| PDHB | 0.27 | −0.01 | −0.19 | 0.09 | −0.28 | AC008752.2 | 0.35 | −0.85 | 0.18 | −0.46 | 0.47 | RNU6-833P | −0.15 | 1.58 | −0.01 | −0.98 | −1.30 |
| AL161729.2 | −1.14 | 0.77 | 1.54 | 0.59 | 0.44 | KLHL40 | −0.58 | 1.77 | −1.28 | 1.28 | −2.08 | LINC01916 | −0.24 | −0.55 | −0.01 | 0.40 | 1.98 |
| GAPVD1 | 0.18 | −0.03 | −0.13 | 0.00 | −0.17 | NPDC1 | −0.18 | 0.18 | 0.29 | 0.13 | 0.35 | RPL7P29 | −0.24 | −0.97 | −0.84 | 1.93 | 0.12 |
| BMF | −0.42 | 0.43 | 0.50 | 0.05 | −0.10 | AL591463.1 | −0.79 | −0.46 | −0.28 | −0.80 | −1.94 | AL021707.6 | 0.03 | −0.52 | −1.06 | 0.32 | 0.11 |
| AC009299.1 | 0.87 | −0.59 | −0.89 | −0.21 | 0.14 | AC123595.1 | 0.52 | −1.32 | −0.88 | −0.93 | 0.60 | AC084024.1 | −0.06 | −0.03 | 1.21 | −0.31 | 0.58 |
| HSPA12B | −0.59 | 0.37 | 1.04 | 0.06 | 0.07 | LINC00189 | 0.59 | 0.62 | 0.34 | 0.96 | 0.74 | NTAN1P3 | −0.16 | −0.23 | −1.58 | 0.03 | −0.33 |
| AL356747.1 | 1.40 | −0.70 | 0.99 | −1.04 | 0.37 | AL080313.1 | 0.66 | 0.07 | −3.84 | 0.65 | −2.24 | AC024060.1 | −0.04 | −0.02 | 0.61 | −0.18 | −0.06 |
| LINC00958 | 0.65 | −0.17 | −1.42 | −0.12 | −0.37 | NPTX2 | −0.29 | −1.02 | −0.41 | −0.28 | −0.07 | AC093909.1 | −0.03 | 0.45 | 0.04 | −0.40 | −0.88 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC027117.1 | −0.83 | 0.73 | 0.60 | 0.31 | 0.08 | AC006023.2 | 0.53 | −0.82 | −0.04 | −0.52 | −0.66 | SRP19 | −0.01 | −0.11 | 0.05 | 0.02 | 0.13 |
| CLMP | −0.85 | 0.35 | 0.57 | −0.03 | 0.54 | AC023161.2 | 0.48 | 1.22 | −0.64 | 0.57 | −0.54 | AC096664.3 | −0.47 | −0.84 | 1.14 | −0.75 | 0.82 |
| RBMX2 | 0.21 | −0.23 | −0.29 | −0.08 | −0.03 | FLT4 | −0.18 | −0.19 | 0.56 | −0.12 | 0.13 | LINC02320 | 0.06 | −0.64 | 0.15 | 0.62 | 0.83 |
| MAPKBP1 | −0.46 | 0.12 | −0.25 | 0.31 | 0.04 | AC010624.3 | 0.45 | −0.08 | −0.45 | 0.01 | 0.18 | AC079763.1 | 0.22 | −0.51 | 2.25 | −1.60 | 0.31 |
| RN7SL163P | −1.83 | 0.41 | 0.47 | −0.89 | 1.08 | GBA3 | −0.54 | −0.19 | 0.63 | −0.90 | 0.30 | BX539320.1 | 0.05 | −0.41 | −0.56 | −0.64 | −0.15 |
| CTNNBL1 | 0.25 | −0.22 | −0.27 | −0.19 | −0.14 | G24512 | −0.70 | −0.60 | 3.18 | −0.40 | 0.32 | OR4A46P | −0.37 | −0.61 | 1.08 | −0.82 | 1.88 |
| MELTF-AS1 | −0.84 | 0.85 | −0.36 | 0.31 | −0.03 | PPEF1-AS1 | −1.14 | −0.37 | −0.51 | −0.62 | 0.91 | MTCO1P20 | 0.38 | −2.33 | 1.22 | −1.58 | 1.64 |
| POLR2J3 | −0.50 | 0.16 | 0.11 | 0.43 | 0.42 | GTPBP10 | −0.07 | −0.16 | 0.23 | −0.08 | 0.19 | AL360091.2 | 0.03 | 0.15 | −0.15 | 0.58 | 0.31 |
| JMJD8 | −0.35 | 0.29 | 0.30 | 0.11 | 0.08 | RNU5A-4P | 0.58 | −0.08 | 0.10 | −0.16 | 0.01 | AC073135.1 | −0.47 | −0.58 | 0.77 | −0.13 | 1.15 |
| AC091271.1 | −0.88 | −0.61 | −0.15 | −0.29 | 0.70 | ADPRM | −0.13 | 0.13 | 0.22 | 0.08 | 0.00 | AC104574.1 | −0.16 | −1.13 | −1.35 | 0.39 | −0.01 |
| AGGF1P3 | −0.98 | 1.01 | 0.33 | 0.91 | 0.26 | AC074051.5 | −0.75 | 1.01 | −1.29 | 2.02 | −0.11 | NOVA2 | 0.03 | −0.20 | 0.72 | −0.12 | 0.16 |
| RPL12 | 0.39 | −0.02 | 0.02 | −0.07 | −0.36 | RNU1-115P | −0.86 | −0.86 | −0.51 | 0.06 | 0.69 | AC012150.2 | −0.05 | −0.65 | −1.07 | 0.01 | 0.00 |
| AC084783.1 | 0.77 | −0.29 | −0.35 | −0.33 | −0.27 | AL021154.1 | 1.48 | 0.24 | 1.29 | 0.64 | −0.94 | LINC01139 | 0.04 | 0.78 | 0.84 | 0.05 | −0.26 |
| AC007743.1 | −0.68 | 0.63 | 0.79 | 0.10 | −0.24 | AC091588.1 | −0.74 | 0.00 | 0.55 | −1.24 | −0.13 | BNIP3P18 | 0.47 | 1.01 | −2.06 | 2.19 | −2.77 |
| ASPRV1 | 1.04 | −0.10 | −0.46 | 0.91 | −0.90 | PPIAL4G | −0.61 | −0.88 | −1.15 | 0.18 | −0.25 | AC004702.1 | 0.09 | 0.09 | −0.84 | −0.55 | −1.18 |
| RN7SKP35 | 1.01 | −1.68 | −0.87 | 0.23 | 0.93 | AL357568.2 | 0.29 | 0.33 | 0.30 | 0.11 | 0.59 | AC084337.1 | 0.02 | −0.03 | 0.28 | −0.10 | 0.19 |
| SSH2 | 0.24 | −0.21 | −0.37 | −0.08 | −0.07 | MIR28 | 0.42 | 0.03 | −0.61 | −0.60 | −0.53 | NUTM2F | −0.12 | 0.02 | 0.42 | −0.10 | 0.07 |
| LAPTM4B | 0.52 | −0.16 | −0.04 | −0.24 | −0.23 | GUSBP11 | 1.08 | 0.78 | −0.62 | 1.44 | −0.61 | AL158050.2 | 0.47 | −0.27 | 0.05 | −0.03 | 0.05 |
| MMP24 | −0.45 | 0.87 | 0.65 | 0.17 | −0.15 | AL121978.1 | 0.43 | −0.64 | 1.17 | −0.53 | 0.89 | RPS4XP3 | −0.12 | 0.89 | 0.41 | −0.16 | −0.98 |
| DPY19L2P3 | −0.50 | 0.17 | 0.88 | −0.04 | 0.30 | AC096719.1 | −0.43 | −1.02 | 0.15 | 0.38 | 1.17 | LINC01400 | 0.27 | −1.05 | −1.51 | −0.66 | −2.01 |
| HOXA13 | −0.96 | 0.44 | 0.77 | 0.05 | −0.63 | DLGAP4 | −0.08 | 0.27 | 0.31 | −0.11 | −0.21 | OPTC | −0.05 | 0.42 | 1.48 | −0.16 | 0.41 |
| CYB5A | −0.49 | 0.41 | 0.54 | 0.30 | 0.18 | AC116913.1 | 0.27 | −0.17 | 0.11 | −0.22 | 0.14 | OR4A19P | −0.47 | −0.28 | 0.59 | −1.09 | 0.47 |
| ANKFY1 | 0.19 | −0.09 | −0.11 | −0.02 | 0.01 | AC004816.2 | −0.84 | 0.70 | −0.01 | 0.50 | 0.87 | AC005176.1 | −0.14 | −0.03 | −0.33 | −0.61 | −1.28 |
| LINC01310 | −1.61 | −0.28 | 1.19 | 1.70 | 1.33 | PPIAP6 | 0.37 | −0.63 | −0.64 | 0.32 | 0.32 | AC093663.1 | −0.33 | 0.19 | −0.16 | −1.33 | −0.40 |
| AC025458.1 | −0.98 | 0.26 | −0.18 | 0.76 | 0.69 | RNU6-253P | −1.35 | −0.28 | 0.03 | −0.78 | −0.70 | ELSPBP1 | 0.16 | 0.02 | −1.10 | 0.62 | −1.95 |
| KCNB2 | −1.08 | 0.99 | 0.34 | 0.57 | 0.01 | RN7SL706P | 0.45 | 0.82 | −0.97 | 0.89 | 0.58 | CR1L | 0.07 | −0.70 | −1.51 | −0.02 | −0.45 |
| HIST2H2BE | 0.44 | −0.20 | −1.14 | −0.14 | −0.76 | AL355112.1 | −0.55 | 0.48 | 0.38 | −0.30 | −0.67 | AL137078.2 | 0.47 | −1.46 | 0.29 | −1.22 | 1.11 |
| NAA20 | 0.29 | −0.26 | −0.62 | −0.03 | −0.22 | LINC02586 | −0.42 | 0.55 | −0.27 | 0.15 | −0.49 | OR4A12P | −0.18 | −0.43 | −1.01 | 0.96 | −0.93 |
| CACNG8 | −0.70 | 0.56 | 0.65 | 0.21 | 0.41 | AL500527.1 | 0.50 | 0.28 | −1.25 | −0.66 | −1.91 | AC090358.1 | −0.37 | −0.26 | −1.10 | 1.27 | −3.21 |
| PLXNB3 | −0.46 | 0.25 | −0.36 | 0.43 | 0.17 | DLX3 | −0.20 | 0.46 | 0.53 | 0.27 | −0.11 | AL121776.1 | 0.25 | −1.34 | 1.49 | −2.50 | 0.25 |
| AC008625.1 | 1.80 | −0.80 | 0.01 | −0.12 | −0.11 | AL049795.1 | −0.74 | −1.55 | 1.55 | −1.25 | 0.76 | AL133412.1 | −0.09 | −0.01 | −0.21 | 0.01 | 0.14 |
| DPY19L3 | 0.22 | −0.19 | 0.04 | −0.17 | 0.16 | KCNN1 | 0.42 | −0.79 | −1.69 | −0.09 | −0.15 | AL391261.4 | −0.47 | −0.52 | −0.02 | 0.07 | −1.10 |
| PARVA | −0.42 | 0.13 | 0.28 | −0.13 | −0.03 | PHLPP1 | −0.08 | 0.27 | 0.01 | 0.23 | −0.05 | HSFY3P | 0.07 | −0.68 | −0.61 | −0.51 | 0.29 |
| GNL3L | 0.26 | −0.39 | −0.38 | −0.14 | 0.02 | FAM87A | −0.27 | −0.37 | −1.07 | −0.08 | −0.64 | AC011921.3 | −0.05 | −0.43 | 0.59 | −1.09 | −0.26 |
| MAPK8IP1P2 | −1.39 | −0.42 | 0.60 | −0.27 | 2.01 | AC010997.2 | 1.00 | −0.61 | −0.03 | −0.66 | −0.83 | RN7SKP171 | −0.11 | 1.75 | 1.85 | 1.03 | −0.77 |
| PIGU | 0.36 | −0.24 | −0.32 | −0.11 | −0.08 | AC074135.1 | 0.42 | −0.65 | −0.36 | −0.24 | 0.39 | AC134312.5 | −0.08 | 1.47 | 1.32 | −0.17 | −1.76 |
| AC012676.3 | 0.92 | −0.86 | −0.59 | 0.21 | 0.62 | AC135050.5 | 0.22 | −0.34 | −0.01 | −0.09 | 0.62 | AC100871.1 | 0.17 | −0.17 | −2.12 | 0.84 | −1.84 |
| LRRC15 | 0.91 | 0.06 | 1.54 | −1.30 | −0.35 | DEFB131E | −0.68 | −1.69 | 0.38 | −1.56 | −0.88 | FDPSP8 | −0.11 | −1.61 | −1.19 | −0.35 | −0.67 |
| SPPL2B | −0.41 | 0.28 | −0.05 | 0.39 | 0.10 | AC005702.2 | 0.26 | 0.24 | 0.56 | 0.09 | 0.12 | LINC01162 | −0.47 | 0.13 | −1.14 | −0.87 | −1.21 |
| AF230666.1 | 0.64 | 0.14 | −0.20 | 0.17 | −0.17 | RP11-497H16.6 | 0.33 | −0.42 | 0.09 | 0.51 | 0.51 | AL451044.1 | 0.06 | 0.32 | 1.09 | −0.79 | 0.36 |
| FANCC | −0.41 | 0.39 | 0.70 | 0.21 | 0.29 | ADI1P2 | −1.00 | −0.08 | 0.73 | −0.70 | 1.18 | AL512635.1 | 0.20 | −1.80 | −0.51 | −0.63 | 1.48 |
| FAM81B | −0.88 | 0.94 | −0.39 | 0.46 | −0.96 | AC012618.2 | −0.24 | 0.28 | −0.06 | 0.09 | −0.09 | AC104688.1 | 0.30 | −1.29 | −1.54 | −0.48 | −0.72 |
| AC004054.1 | −1.10 | 0.07 | 0.43 | 0.10 | 0.20 | RNU6-122P | 0.68 | −0.41 | 0.23 | 0.53 | 1.39 | AC107032.2 | 0.06 | 0.11 | 0.55 | 0.00 | 0.67 |
| RHOA-IT1 | −0.65 | −0.45 | 0.26 | −0.09 | 0.75 | AC021422.1 | −0.89 | −0.13 | 0.16 | −0.03 | 0.02 | MTCO1P25 | 0.11 | −0.90 | −1.29 | −0.56 | −0.68 |
| AL627309.4 | 1.11 | −0.56 | −1.04 | 0.21 | −0.43 | CDCA4P1 | 0.33 | −0.08 | 0.11 | 0.18 | −0.05 | GSTA6P | 0.47 | −0.86 | −1.37 | 1.35 | 1.53 |
| DDX27 | 0.28 | −0.26 | −0.32 | −0.23 | −0.06 | PIK3CA | 0.10 | 0.08 | −0.01 | −0.02 | −0.19 | PPP3CA | −0.01 | 0.12 | 0.09 | 0.02 | −0.03 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| PLTP | 0.49 | −0.26 | −0.61 | 0.27 | −0.29 | PAQR8 | −0.16 | −0.18 | 0.42 | −0.10 | 0.24 | DNAJB13 | −0.10 | −0.32 | −0.61 | −0.90 | −0.44 |
| RNF130 | −0.48 | 0.19 | 0.67 | −0.05 | 0.22 | AL031283.2 | 0.81 | 0.47 | 0.44 | 0.36 | 0.09 | AC092642.1 | −0.47 | 0.06 | −0.16 | 1.32 | 0.88 |
| DPRXP3 | 0.63 | −0.03 | −0.10 | −0.22 | −0.12 | RPEP1 | 0.75 | −1.09 | 0.71 | −0.67 | −1.10 | AC006115.1 | −0.20 | 0.95 | 0.90 | 1.49 | 0.59 |
| PYCR3 | 0.41 | −0.42 | −0.59 | −0.08 | −0.20 | AC097634.2 | −0.48 | 0.15 | 0.57 | 0.13 | 0.37 | OLA1P2 | −0.15 | −0.85 | 0.04 | 1.29 | 1.69 |
| MIR3680-1 | −0.93 | 0.40 | −0.67 | 0.08 | 0.17 | AC068522.1 | 0.25 | −0.84 | 0.51 | −0.29 | 0.84 | NPM1P29 | −0.02 | 0.18 | 0.32 | 0.38 | 0.39 |
| NIF3L1 | 0.26 | −0.18 | −0.18 | −0.11 | −0.01 | MRPS28 | 0.17 | −0.07 | −0.19 | 0.30 | 0.13 | MIR200B | −0.06 | 0.20 | 0.13 | 0.44 | 0.70 |
| AGAP12P | −0.61 | 0.23 | 0.69 | −0.13 | 1.18 | NFS1 | −0.08 | −0.02 | 0.08 | 0.08 | 0.20 | RNU6-1238P | −0.13 | 0.71 | 1.59 | 1.40 | 2.15 |
| AC107918.4 | −0.68 | −0.23 | −0.25 | −0.40 | −0.39 | AC016747.3 | 0.16 | −0.12 | −0.04 | 0.02 | 0.15 | EPHA1-AS1 | 0.03 | 0.15 | −0.35 | 0.11 | −0.64 |
| FTH1P4 | 0.64 | −0.30 | −0.39 | −0.15 | −0.04 | AC123768.3 | −0.39 | 0.51 | 1.81 | −0.44 | 0.53 | AL109897.1 | −0.21 | −1.12 | 0.28 | −1.65 | −0.11 |
| CLN5 | −0.27 | 0.17 | 0.34 | 0.07 | 0.10 | AL731555.1 | −0.62 | −0.25 | −1.18 | −0.48 | −0.17 | AC079906.1 | 0.06 | −2.10 | −0.55 | −0.55 | 1.14 |
| AC107029.2 | −0.99 | −0.76 | −0.58 | 0.03 | 0.20 | AC010680.1 | −0.76 | 0.67 | 1.67 | 0.31 | 1.03 | HEATR5B | 0.01 | 0.07 | −0.02 | 0.08 | −0.03 |
| RPRD1A | 0.23 | −0.03 | −0.12 | −0.01 | −0.06 | AC092119.3 | 0.55 | −0.75 | 0.36 | 0.35 | −0.01 | AC092832.2 | 0.25 | 0.13 | −1.98 | −0.26 | −0.69 |
| CUEDC2 | −0.23 | 0.10 | −0.04 | −0.04 | −0.12 | ERC2 | 0.33 | −0.41 | −0.80 | 0.13 | −0.09 | AC024958.1 | 0.19 | −1.11 | −1.83 | 0.02 | −0.29 |
| AC104695.1 | 1.68 | −1.21 | −2.60 | −0.11 | −2.14 | PCGF2 | −0.11 | 0.05 | 0.05 | 0.22 | 0.32 | CCT4P1 | −0.10 | −0.46 | 0.86 | 0.18 | 0.12 |
| AC040173.1 | −1.09 | −0.02 | 0.64 | −0.96 | 0.21 | AC096554.1 | −1.04 | −0.94 | 0.94 | −0.13 | 0.91 | NXF1 | 0.01 | 0.05 | −0.23 | 0.00 | −0.05 |
| CR392039.5 | −1.59 | 0.56 | 2.99 | 0.28 | 0.90 | SPERT | −0.62 | 0.89 | 0.14 | −0.02 | −0.44 | IFNLR1 | 0.02 | 0.16 | −0.30 | 0.18 | −0.18 |
| E2F3P2 | −1.04 | −0.03 | 0.82 | −0.31 | 0.06 | SLC41A2 | −0.22 | 0.05 | 0.26 | −0.30 | 0.08 | AL161756.2 | 0.18 | 0.37 | −0.10 | −0.26 | −1.58 |
| ABHD17B | 0.39 | −0.06 | −0.40 | 0.11 | −0.41 | AC006378.1 | −0.31 | 0.14 | 0.99 | 0.42 | 0.88 | AC007556.1 | 0.11 | −0.59 | 0.25 | −1.11 | −0.30 |
| RNASEH2B | −0.23 | 0.06 | 0.25 | 0.06 | 0.21 | AC009119.3 | −0.40 | −0.27 | 1.09 | 0.25 | 0.76 | AC019155.1 | −0.24 | −0.80 | 0.20 | −1.24 | −0.58 |
| AC064799.2 | 0.66 | −0.29 | −0.63 | 0.23 | 0.35 | AL590814.1 | −0.65 | −0.10 | −0.21 | −1.28 | −1.25 | AL450332.1 | −0.05 | −0.37 | −0.03 | 0.49 | −0.49 |
| MTPAP | 0.20 | −0.03 | −0.23 | 0.11 | −0.11 | AL162419.1 | 0.75 | −0.76 | −1.09 | 0.15 | −0.48 | NIPA2P2 | −0.27 | 0.07 | −1.83 | 0.43 | −1.46 |
| AC121154.1 | 1.37 | −0.61 | −0.24 | 0.50 | 0.72 | AL391840.1 | −0.38 | 0.23 | 1.00 | 0.43 | 0.22 | AL122003.1 | 0.21 | −0.34 | 1.61 | 1.49 | 1.49 |
| MIR1205 | 1.92 | 0.02 | 1.08 | −0.66 | −0.30 | LINC01592 | 0.65 | −1.16 | 0.61 | −0.58 | −0.28 | KIAA0753 | −0.01 | −0.05 | −0.15 | −0.03 | −0.06 |
| CCL5 | 0.84 | −0.11 | −0.14 | −0.23 | −0.58 | MT-TM | −0.40 | 0.12 | 0.50 | 0.69 | −0.45 | AC004069.2 | 0.23 | −0.22 | −0.42 | 0.57 | 1.11 |
| AL353726.2 | −1.25 | −1.15 | 0.15 | −0.53 | 0.16 | 4-Mar | 0.75 | −2.02 | −0.55 | 0.13 | 0.82 | OR8D2 | 0.16 | −1.47 | −0.21 | 0.94 | −0.17 |
| HMGN4 | 0.29 | −0.13 | −0.32 | −0.07 | −0.36 | GCSHP4 | 0.63 | −2.07 | −1.31 | −1.68 | −0.20 | RN7SKP278 | 0.33 | −0.82 | −1.28 | 0.42 | −1.86 |
| STK4 | 0.25 | −0.15 | −0.16 | −0.19 | −0.15 | LINC02596 | 1.18 | −0.56 | −2.14 | 0.17 | −1.72 | RNU4-56P | −0.16 | −0.60 | −0.37 | 0.03 | 0.16 |
| DGKI | −0.66 | −0.03 | 0.14 | −0.64 | −0.37 | AL731556.2 | −0.33 | −0.02 | −1.15 | 0.32 | −0.35 | AC015802.1 | 0.09 | 0.41 | 0.49 | 0.78 | 0.47 |
| GBP5 | 0.85 | −1.18 | −0.40 | −1.39 | 0.13 | CBLC | 0.16 | −0.27 | −0.44 | −0.03 | 0.07 | LINC02216 | −0.20 | 0.72 | −0.64 | 1.67 | −0.98 |
| AC087482.1 | −0.97 | 0.14 | 0.03 | −0.19 | 0.19 | AC107956.1 | 0.25 | −0.07 | 0.30 | 0.15 | −0.10 | AC020917.1 | 0.04 | −0.29 | 0.33 | −0.27 | 0.34 |
| AL160153.1 | −1.62 | 1.32 | 2.27 | 0.66 | 1.55 | AP003559.1 | 0.36 | 0.16 | 0.21 | 0.32 | 0.00 | AC104777.2 | −0.17 | −1.24 | −0.09 | −1.27 | −0.08 |
| AC005351.1 | 0.71 | 0.30 | −0.77 | 0.24 | −0.50 | CCT6B | −0.18 | 0.13 | 0.05 | 0.30 | 0.01 | PPIAP84 | −0.46 | −0.64 | 0.45 | −0.06 | 0.51 |
| SLC9A8 | −0.20 | −0.11 | −0.07 | −0.04 | 0.13 | RNU6-223P | 1.27 | −0.65 | −1.38 | −0.27 | −1.56 | AL591623.2 | 0.03 | −0.33 | 0.43 | −0.05 | 0.47 |
| SIGLEC15 | −0.56 | 0.18 | 0.44 | −0.10 | 0.22 | KCNK17 | 0.75 | −2.13 | −0.34 | 0.50 | 1.63 | AL020997.2 | 0.06 | 0.06 | 0.37 | −0.27 | 0.20 |
| ARHGEF34P | −0.43 | 0.30 | 0.22 | 0.38 | −0.03 | LCE4A | −0.49 | 0.39 | 0.48 | −0.08 | −0.64 | CRYBG3 | 0.01 | −0.01 | 0.13 | −0.04 | 0.09 |
| AL392111.1 | −1.03 | 1.00 | 1.13 | −0.03 | 0.66 | FRG2JP | −0.82 | −0.15 | −0.16 | 1.19 | 0.88 | AP003730.1 | −0.25 | 0.22 | −0.95 | −0.17 | −1.73 |
| KRT18P11 | −2.18 | 0.23 | 1.34 | 1.20 | 0.60 | SH3BP5L | −0.09 | 0.22 | 0.03 | 0.05 | −0.12 | RN7SKP42 | 0.08 | 0.11 | 1.97 | −0.58 | 0.03 |
| G35484 | 1.83 | −0.54 | −2.09 | 0.01 | −2.14 | ANAPC5 | −0.06 | 0.09 | 0.12 | 0.14 | 0.09 | AL080272.1 | −0.46 | −0.76 | −0.50 | −1.37 | −0.31 |
| LRRC39 | −0.39 | 0.12 | −0.15 | 0.44 | 0.17 | RN7SL329P | −0.23 | −0.22 | −0.29 | 0.05 | −0.08 | KRTAP13-5P | 0.46 | −1.37 | −0.94 | 0.97 | 0.12 |
| CXorf40B | −0.35 | 0.15 | −0.05 | 0.26 | 0.30 | MIR1343 | 0.70 | 0.11 | 1.75 | 0.09 | 0.14 | AC023968.2 | 0.23 | −0.75 | 0.79 | 1.01 | 0.96 |
| AL356273.3 | 0.46 | −0.49 | −0.50 | 0.20 | 0.30 | MTATP6P17 | 0.76 | −0.47 | 0.29 | −0.60 | −0.78 | G23048 | −0.05 | 0.23 | 0.16 | −0.15 | 0.31 |
| OSTCP8 | 0.72 | −0.45 | −0.01 | 0.04 | 0.17 | LINC00901 | −0.57 | −2.22 | 0.50 | −0.19 | 1.37 | AC245054.2 | −0.40 | −0.25 | 0.39 | −0.27 | 3.71 |
| RGS10 | 0.42 | −0.27 | −0.34 | −0.12 | −0.12 | AC090617.8 | 0.46 | −0.06 | −1.06 | −0.09 | −0.05 | OR5T1 | −0.29 | −1.15 | −0.01 | −1.66 | −1.46 |
| RNU6-4P | −0.66 | 0.70 | 0.36 | 0.40 | −0.35 | AC007066.2 | 0.14 | −0.04 | 0.33 | 0.23 | 0.18 | AC068044.1 | −0.17 | 0.47 | 0.72 | 1.10 | −0.35 |
| RNU6-1327P | 0.98 | −0.29 | −0.03 | 0.03 | 0.18 | STAB1 | −0.22 | −0.13 | 0.31 | −0.08 | 0.18 | AC098820.2 | −0.14 | 1.72 | −2.42 | 1.90 | −2.14 |
| CA6 | −1.17 | 1.50 | 1.88 | 0.65 | 1.00 | OR7E122P | 0.53 | −0.62 | −1.32 | 0.27 | −1.04 | AF107885.1 | 0.03 | 0.03 | −0.32 | 0.32 | −0.02 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC020910.6 | −0.90 | 0.29 | 1.00 | −0.21 | 1.05 | ATAD3B | −0.17 | −0.14 | −0.44 | 0.17 | 0.21 | SETD6 | −0.01 | 0.04 | 0.07 | 0.13 | 0.15 |
| RPL15 | 0.37 | 0.06 | −0.08 | −0.04 | −0.37 | G19165 | −0.60 | −0.54 | 1.93 | −0.09 | 0.11 | PGAM1P13 | −0.46 | 0.11 | NA | −0.17 | −0.43 |
| RPL4P4 | 0.49 | −0.23 | −0.24 | −0.21 | −0.19 | RPAP2 | 0.07 | 0.00 | −0.01 | −0.04 | −0.01 | AC007342.3 | 0.07 | −0.26 | 0.29 | −0.43 | −0.44 |
| AC026471.4 | −0.56 | 0.06 | 0.42 | 0.18 | 0.66 | NKX2-8 | −0.77 | −0.40 | 0.04 | 0.31 | 0.63 | AL645608.8 | −0.10 | −0.45 | −1.67 | −0.75 | −0.74 |
| NRARP | 0.63 | −0.34 | −0.87 | 0.28 | −0.27 | SUCNR1 | −0.22 | 0.67 | −0.04 | 0.83 | −0.05 | RPS17P8 | 0.46 | −0.48 | −0.51 | −0.47 | 0.92 |
| CYCSP55 | 1.23 | −0.34 | −1.80 | −0.24 | −2.28 | REP15 | 0.48 | −0.86 | 0.07 | 0.33 | 0.44 | AL592114.2 | −0.46 | 0.29 | 0.90 | −0.30 | 0.22 |
| AC067940.1 | 0.65 | −0.32 | −0.44 | 0.10 | 0.13 | AL121772.3 | −0.19 | 0.32 | 0.01 | 0.41 | 0.15 | BX842559.2 | 0.20 | −0.79 | 2.43 | −0.94 | 1.36 |
| AC005740.4 | −0.63 | 0.75 | 0.38 | 0.07 | −0.22 | AC018371.2 | −1.24 | 1.94 | −0.30 | 1.60 | −2.45 | LINC02209 | 0.10 | −0.25 | −1.64 | 0.64 | −0.98 |
| CICP16 | −0.68 | −0.11 | 0.38 | 0.30 | 0.36 | AC104451.1 | −0.34 | 0.24 | 0.10 | 0.44 | 0.95 | AC012629.2 | −0.17 | 0.29 | −0.59 | −0.07 | −0.28 |
| RIPK1 | 0.15 | −0.05 | −0.16 | −0.08 | −0.20 | AL161787.1 | 0.37 | 0.01 | −0.51 | 0.33 | −0.74 | AL096816.1 | 0.07 | −0.40 | 0.01 | −0.27 | −0.03 |
| AL358178.1 | 0.85 | −0.23 | −0.18 | −0.27 | −0.18 | AC009005.1 | 0.35 | 0.50 | −0.23 | −0.11 | −1.35 | AC013724.1 | 0.46 | 0.07 | 0.09 | 0.49 | −0.08 |
| SLC10A2 | −1.28 | −0.27 | 1.33 | 0.15 | 0.19 | AC024451.2 | 0.21 | −0.06 | −0.06 | −0.18 | −0.06 | AC112492.2 | −0.46 | 0.53 | −0.39 | 0.33 | −1.03 |
| AC108866.1 | −0.67 | 0.80 | 0.42 | −0.05 | 0.01 | AL138733.2 | −0.57 | −0.24 | −1.30 | 1.17 | 0.14 | CXorf40A | −0.02 | −0.13 | −0.11 | −0.04 | 0.09 |
| AC093849.1 | −1.08 | 0.61 | 1.65 | 0.44 | 0.24 | C3AR1 | 0.34 | −0.40 | 0.21 | −0.26 | −0.12 | AL049794.1 | 0.12 | −0.56 | −0.83 | 1.38 | −0.80 |
| AC084866.1 | −1.08 | 1.05 | 1.36 | 0.87 | 0.66 | AC009121.2 | −0.61 | −0.47 | 1.46 | −0.10 | 0.38 | SLC17A8 | −0.08 | −1.10 | −0.32 | 0.05 | 0.29 |
| RDH13 | −0.41 | 0.40 | 0.50 | 0.07 | 0.09 | AC004528.1 | −0.63 | −1.25 | 0.27 | −1.32 | 0.94 | AC126323.3 | −0.35 | 0.70 | −1.32 | 0.12 | −1.51 |
| AP000920.1 | −1.38 | 1.03 | −0.63 | 0.59 | −0.82 | AL359263.1 | −0.86 | 0.50 | 1.05 | 1.77 | −0.36 | SHBG | −0.08 | −0.58 | −0.54 | −0.28 | 0.09 |
| EHMT2 | −0.32 | 0.04 | 0.07 | 0.17 | 0.28 | C5orf49 | −0.64 | 0.35 | −0.45 | 0.77 | −0.25 | RN7SL73P | 0.09 | −0.05 | 1.27 | 0.03 | 0.62 |
| SPATA33 | −0.39 | −0.13 | 0.06 | −0.17 | 0.01 | AC009646.2 | −0.89 | −1.00 | 0.25 | 1.14 | 0.99 | AC084871.1 | −0.04 | −0.49 | −0.79 | 0.29 | 0.28 |
| RNU6-814P | 1.33 | −0.24 | −1.97 | −0.05 | −1.05 | AC027228.1 | 0.38 | −0.30 | −1.51 | 0.09 | −0.92 | AC092447.1 | 0.46 | −0.90 | −0.69 | 0.78 | 1.34 |
| AC022613.3 | 0.48 | 0.22 | −0.27 | −0.13 | −0.54 | AC128709.1 | −1.05 | 1.79 | 1.76 | 1.83 | 0.08 | AC106875.1 | 0.23 | −0.48 | 0.20 | −0.43 | −0.47 |
| BNIP1 | 0.34 | −0.16 | −0.32 | −0.03 | −0.40 | AC097461.1 | 0.16 | −0.21 | −0.07 | 0.12 | 0.38 | RNASEH2A | 0.04 | −0.13 | 0.01 | 0.18 | −0.10 |
| AC010149.1 | 0.54 | −0.64 | −0.92 | −0.18 | −0.13 | KNOP1P4 | 0.46 | −0.20 | −0.68 | 0.48 | 0.69 | AL606490.8 | −0.46 | 0.04 | −0.02 | −0.35 | −2.29 |
| AC023830.2 | −1.37 | −0.35 | 0.01 | −0.67 | 0.31 | RNU7-162P | −0.38 | 0.29 | 0.78 | 0.18 | 0.37 | AL606970.4 | 0.25 | −0.73 | 1.99 | −0.20 | 3.06 |
| LAMP5 | 1.13 | 0.25 | −0.30 | 0.20 | −0.25 | ACTA2-AS1 | −0.20 | 0.14 | −0.01 | 0.16 | −0.23 | RN7SL91P | 0.19 | −0.61 | −1.76 | 0.43 | −1.31 |
| AL691420.1 | 1.54 | −1.05 | −0.95 | −0.10 | −0.18 | PLB1 | −0.14 | 0.12 | 0.08 | 0.14 | −0.03 | RN7SL823P | −0.15 | −1.37 | −0.05 | 0.49 | 0.80 |
| SEC11A | 0.27 | −0.22 | −0.10 | −0.09 | 0.07 | AC107892.1 | −0.65 | −1.02 | −0.52 | 0.00 | −1.32 | RNU6-906P | −0.06 | −1.10 | 0.07 | −0.12 | 0.02 |
| SFXN2 | −0.36 | −0.08 | 0.19 | 0.07 | 0.46 | RN7SL40P | −0.44 | 0.01 | 0.56 | 0.06 | 0.44 | FCF1P9 | −0.46 | 0.15 | NA | 0.16 | −0.37 |
| RPL39P6 | 1.38 | −0.67 | 0.02 | −0.28 | 0.30 | FOXP1-IT1 | −0.24 | 0.11 | 0.43 | 0.03 | 0.14 | LRWD1 | −0.02 | 0.11 | −0.31 | 0.07 | −0.03 |
| CNPY4 | −0.35 | 0.18 | 0.67 | −0.04 | 0.26 | KRT8P41 | 0.54 | −0.06 | 0.13 | 0.77 | 0.55 | RNU6-455P | 0.14 | 1.77 | 2.88 | −1.22 | 0.60 |
| ANO10 | 0.28 | −0.01 | 0.08 | 0.01 | −0.07 | SAA2 | 0.45 | −0.25 | −1.46 | −0.14 | −1.00 | AC008121.2 | −0.10 | −0.77 | 2.40 | 0.24 | 1.57 |
| OTX2-AS1 | −1.18 | −0.17 | 0.33 | −0.04 | −0.06 | AL731532.2 | −0.46 | −0.18 | 0.32 | −0.68 | −0.01 | AC233702.5 | −0.25 | 0.18 | −0.13 | −0.24 | 0.20 |
| SLC30A5 | 0.24 | −0.12 | −0.08 | −0.12 | −0.12 | AC005775.1 | −0.52 | −0.85 | −0.20 | −0.12 | 0.69 | RFPL4A | 0.46 | −0.33 | −0.14 | 1.05 | −1.18 |
| BCKDHB | −0.33 | 0.35 | 0.64 | 0.05 | 0.25 | AC008938.1 | −0.56 | 0.46 | 0.00 | 0.23 | 0.32 | AC068580.4 | −0.04 | 0.98 | 0.63 | 0.48 | −0.22 |
| LINC00113 | −1.08 | 1.08 | 1.34 | 0.38 | 0.39 | AC055736.1 | 1.30 | −0.49 | −1.33 | 0.43 | −2.76 | MIR125B1 | 0.05 | −0.06 | 1.47 | −0.17 | 0.85 |
| RPS26P3 | 1.34 | −1.13 | −0.36 | −0.25 | −0.53 | AL122008.4 | 0.49 | −0.51 | 0.99 | −0.28 | 0.47 | MIR4477B | 0.03 | 0.10 | 0.68 | 0.01 | 0.24 |
| G34382 | −1.51 | 0.86 | 2.57 | 0.36 | 0.36 | AL162151.1 | −0.56 | 0.29 | 0.60 | −0.30 | 0.41 | AC068408.1 | −0.45 | 0.58 | 1.73 | −0.74 | −0.98 |
| SPON2 | −0.50 | 0.55 | 0.15 | 0.21 | −0.49 | SLC4A10 | 0.42 | −0.29 | −0.55 | 0.38 | 0.01 | NYX | 0.18 | −0.23 | −0.80 | 1.28 | 0.27 |
| RAD51D | −0.27 | −0.25 | 0.00 | 0.06 | 0.31 | AC002116.2 | 0.39 | −0.30 | 0.35 | 0.09 | 0.56 | G5146 | −0.04 | 0.45 | −0.10 | 0.26 | −0.06 |
| AC018992.1 | −0.82 | 0.46 | 1.21 | 0.18 | 0.84 | OR51N1P | 1.14 | −1.32 | −2.14 | −0.65 | −1.23 | RPS29P33 | −0.46 | 0.18 | −0.44 | −0.42 | −1.34 |
| CYP2T3P | −1.21 | 0.16 | 0.56 | 0.45 | 1.19 | AL022331.1 | 0.52 | −0.15 | 0.99 | −0.36 | −0.15 | AC090771.1 | −0.08 | 0.03 | 0.16 | 0.22 | 0.16 |
| AC062029.1 | −0.67 | −0.09 | 0.20 | −0.23 | 0.11 | AC010463.3 | 0.44 | −0.31 | −0.31 | 0.08 | 0.27 | HMGN1P24 | −0.04 | −0.13 | 0.34 | −0.16 | 0.18 |
| AC139887.2 | −0.46 | 0.00 | 0.24 | −0.01 | 0.48 | AC090164.2 | −0.57 | 0.44 | 1.36 | 0.90 | 0.68 | CAV3 | 0.07 | 0.76 | −0.63 | 0.08 | −1.96 |
| AL034417.2 | −1.04 | −0.28 | 0.08 | 0.06 | 0.88 | CICP5 | −0.48 | −0.01 | −1.53 | −0.10 | −0.22 | AC007655.1 | 0.18 | −1.53 | −0.94 | −0.87 | −0.73 |
| AC018690.1 | 0.58 | −0.24 | −0.81 | 0.02 | −0.49 | AC127024.5 | 0.35 | −0.18 | 0.59 | −0.27 | 0.36 | OR5AH1P | −0.22 | −0.95 | −1.00 | 0.75 | −0.66 |
| AL109936.2 | −1.06 | 0.86 | 1.60 | 0.44 | 0.57 | AL159163.1 | 0.84 | −1.25 | 0.26 | −0.22 | 0.41 | AJ239318.1 | 0.45 | −0.27 | −2.33 | 1.19 | −1.05 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| PHACTR1 | −0.39 | 0.24 | 0.28 | 0.03 | 0.03 | AC068733.1 | −0.56 | −1.29 | 1.72 | −1.20 | −0.52 | MIRLET7BHG | −0.03 | 0.01 | −0.31 | 0.26 | 0.21 |
| LINC00645 | −1.22 | 0.40 | 0.21 | 0.10 | −0.66 | AK5 | 0.18 | 0.10 | 0.30 | 0.17 | 0.05 | RN7SL356P | −0.21 | −0.76 | 1.58 | −2.38 | 1.57 |
| MIR548K | 1.12 | 0.02 | 0.01 | 0.19 | 0.12 | RPL17P3 | −0.92 | 0.32 | 0.38 | −0.06 | 0.13 | AL672167.1 | −0.11 | −1.17 | −2.11 | 1.54 | 0.23 |
| HSPB1 | 0.45 | 0.18 | −0.24 | 0.33 | −0.57 | IGHV2-5 | 1.79 | 1.43 | 2.03 | 1.16 | 1.53 | AC005394.2 | 0.17 | 1.28 | −1.09 | 1.20 | −3.25 |
| AL135905.2 | 0.64 | −0.05 | −0.70 | 0.16 | −0.40 | CEP162 | −0.10 | 0.11 | 0.17 | 0.01 | −0.03 | LINC01486 | −0.45 | 0.18 | −0.89 | 1.42 | −0.95 |
| AC011483.1 | 1.17 | −1.27 | −0.09 | −0.62 | 0.00 | AC099340.1 | 0.47 | 0.19 | 0.78 | 0.08 | 0.07 | AC069133.1 | 0.45 | −0.71 | 0.59 | 0.18 | −0.32 |
| DISP1 | −0.46 | 0.36 | 0.38 | 0.21 | 0.21 | AC004944.1 | 0.66 | −0.94 | −0.05 | 0.04 | 0.29 | MTCYBP13 | −0.13 | −0.08 | 0.15 | 0.64 | 0.91 |
| RBM17 | 0.21 | −0.24 | −0.45 | −0.01 | −0.07 | MAP3K19 | −0.30 | 0.02 | 0.38 | −0.11 | 0.24 | AC112518.1 | 0.11 | −1.84 | −1.40 | 0.53 | 1.19 |
| MAPK1 | 0.30 | −0.08 | −0.28 | −0.12 | −0.30 | MATN1-AS1 | −0.23 | −0.05 | 0.23 | 0.09 | 0.43 | CDC20B | −0.07 | −0.28 | −0.70 | 0.07 | 0.43 |
| FOXE3 | −1.27 | 0.72 | 0.58 | 0.89 | 0.48 | AL133480.1 | −0.24 | −0.86 | −0.25 | 0.12 | 0.31 | ENTPD4 | 0.01 | −0.06 | −0.08 | −0.06 | 0.02 |
| ATP5MC1P6 | 1.09 | 0.22 | −0.09 | −0.36 | −0.55 | AC087893.1 | 0.19 | 0.00 | −0.46 | −0.27 | −0.30 | PKIA-AS1 | 0.04 | 0.00 | 0.09 | 0.39 | 0.43 |
| RHD | −0.58 | 0.32 | 0.72 | −0.07 | −0.01 | RFTN1P1 | 1.53 | −0.16 | −0.73 | −0.50 | −0.48 | COPS8P3 | −0.45 | −0.59 | −0.34 | 0.49 | 0.36 |
| AC008764.2 | −0.61 | 0.37 | −0.07 | 0.43 | 0.26 | AL034397.2 | 1.01 | −0.39 | 0.31 | −0.19 | −0.24 | SCAMP3 | 0.01 | −0.03 | −0.15 | 0.05 | −0.02 |
| AC011306.1 | −1.10 | 0.94 | −0.37 | 0.43 | −1.09 | AC131009.1 | 0.60 | −0.34 | −0.36 | 0.41 | 1.74 | FEZF1-AS1 | −0.12 | −0.90 | −2.77 | 1.35 | −1.48 |
| RPL7AP11 | 1.12 | 0.01 | −1.47 | 0.06 | −0.83 | AL161665.1 | 0.36 | 0.37 | −1.00 | 0.54 | −1.07 | AC040169.1 | 0.07 | −0.77 | 0.97 | −0.73 | −0.52 |
| DERL2 | 0.32 | −0.11 | 0.01 | −0.13 | −0.05 | AC092384.3 | −0.32 | −0.62 | 0.35 | −0.04 | 0.55 | AC025768.1 | 0.45 | −0.97 | −1.53 | −0.03 | −0.72 |
| AC006978.2 | 1.06 | −0.19 | −0.21 | −0.20 | 0.08 | RN7SL65P | 0.39 | −0.64 | −0.14 | −0.16 | −0.21 | NUP210P1 | 0.37 | 0.01 | −1.43 | 0.56 | −0.69 |
| SRP9 | 0.47 | −0.15 | −0.09 | −0.18 | −0.13 | POU1F1 | 0.54 | 0.37 | 0.13 | −0.27 | −0.73 | GOLGA8S | 0.13 | −0.78 | −1.66 | −0.28 | −1.88 |
| AC007009.2 | −1.88 | 1.25 | 1.83 | 0.52 | 0.71 | AL355309.1 | 0.57 | −0.57 | −0.35 | −0.51 | −0.09 | RPL37AP8 | 0.12 | −0.48 | 0.11 | −0.38 | 0.83 |
| AC068305.2 | −0.87 | 0.90 | 0.57 | 0.33 | −0.16 | LINC02078 | −0.55 | −0.54 | 0.15 | 0.27 | 0.52 | HTATSF1P1 | 0.45 | −1.38 | −1.11 | 0.84 | 0.37 |
| AC112487.1 | −1.02 | −0.11 | 0.93 | −0.46 | −0.10 | AC026688.1 | 0.92 | −0.50 | −0.46 | 0.31 | 1.79 | COG6 | −0.01 | 0.09 | 0.29 | −0.18 | −0.04 |
| AC009506.1 | −0.70 | 0.45 | 0.73 | 0.38 | 0.28 | AC108467.1 | −0.81 | 0.11 | −2.99 | 2.11 | 0.26 | LINC00581 | 0.11 | −0.67 | −1.48 | 0.24 | −1.59 |
| FKBP14 | 0.31 | −0.25 | −0.10 | −0.17 | −0.04 | HCFC2 | 0.08 | 0.03 | 0.11 | −0.08 | −0.08 | AL133370.1 | 0.05 | −0.15 | 0.32 | 0.44 | 0.95 |
| AL445648.1 | −1.39 | 0.51 | 1.34 | 0.53 | −1.18 | PAG1 | 0.12 | −0.34 | −0.09 | −0.15 | 0.08 | FANCD2P2 | 0.08 | −0.40 | −0.04 | −0.51 | −0.36 |
| SRRD | 0.27 | 0.12 | −0.35 | 0.11 | −0.34 | AC021188.1 | 0.41 | −0.50 | −0.55 | 0.02 | 0.55 | RPS2P25 | −0.45 | 0.73 | −0.68 | −0.20 | −2.62 |
| AC115223.1 | 0.57 | −0.48 | −0.43 | −0.12 | −0.22 | ID2 | 0.16 | 0.23 | −0.09 | 0.03 | −0.34 | KRTAP5-4 | −0.07 | −0.24 | −0.18 | 0.59 | 0.37 |
| GDNF-AS1 | 0.61 | −0.06 | −1.12 | 0.42 | −0.61 | AP001318.3 | −0.45 | −0.27 | −0.43 | 0.09 | 0.25 | AC090510.2 | 0.03 | 0.13 | 0.14 | 0.01 | −0.29 |
| PLCG1 | −0.27 | 0.19 | 0.17 | 0.10 | 0.06 | EEF1A1P19 | −0.13 | −0.04 | −0.10 | −0.01 | −0.11 | MINDY4B | −0.17 | 0.84 | −0.27 | 1.37 | 0.83 |
| SNORD91A | 1.12 | −0.83 | −0.39 | 0.18 | 0.48 | LARGE2 | −0.17 | 0.13 | −0.29 | 0.34 | 0.08 | OTC | 0.13 | −0.81 | 0.45 | −0.39 | −0.84 |
| NOX1 | −1.05 | 0.47 | 1.08 | 0.48 | 0.84 | MRS2 | 0.09 | −0.09 | −0.04 | −0.10 | 0.05 | AC069213.3 | 0.19 | 0.50 | −0.60 | 0.70 | 0.28 |
| FCGRIA | 1.40 | −1.66 | 0.46 | −0.78 | 0.08 | BHLHA15 | −0.47 | 1.83 | 2.62 | −0.02 | 0.44 | IGHVIII-13-1 | −0.45 | 0.96 | −0.52 | 0.08 | −1.47 |
| AF186192.1 | −1.45 | 1.78 | 0.94 | 0.72 | −0.13 | CNTRL | −0.09 | −0.12 | −0.05 | −0.05 | −0.01 | G19624 | −0.12 | 0.08 | 1.10 | −0.24 | −0.04 |
| AL391094.1 | 1.14 | −1.00 | −1.26 | −0.13 | 0.09 | NME2 | 0.20 | −0.12 | −0.37 | 0.01 | 0.12 | AL645939.4 | −0.09 | −0.80 | 1.33 | −0.02 | −0.35 |
| MT-TF | −0.98 | 0.26 | −0.25 | 0.35 | −0.28 | AC140479.3 | 0.54 | −0.27 | −0.58 | −0.27 | −1.58 | AC002551.1 | 0.05 | −0.51 | 0.13 | −0.60 | 0.04 |
| AC145207.5 | 0.45 | −0.32 | −0.37 | 0.04 | 0.15 | NDUFAF4P1 | 0.45 | 0.57 | 0.91 | 0.72 | 0.06 | AL772337.3 | 0.15 | −1.70 | −0.03 | −0.16 | 1.20 |
| G30853 | 1.40 | −1.19 | −1.08 | −0.71 | −0.79 | MFSD4BP1 | −0.74 | 1.61 | −1.49 | 0.67 | −1.71 | DHCR7 | 0.03 | 0.39 | 0.01 | 0.38 | −0.25 |
| CDK8 | 0.27 | −0.05 | −0.34 | −0.10 | −0.18 | HSF2BP | −0.22 | 0.32 | 0.21 | −0.10 | 0.06 | IGLV2-23 | 0.45 | 0.04 | 0.60 | −2.31 | 0.15 |
| AQP7P4 | −2.72 | 1.22 | 0.79 | −0.50 | −2.67 | CDY4P | −0.37 | −0.16 | 0.24 | −0.78 | −0.01 | AC079610.3 | −0.43 | −0.51 | −0.14 | −1.69 | −1.53 |
| ASPH | −0.45 | 0.15 | 0.22 | 0.02 | 0.02 | AC107081.2 | 0.34 | −0.33 | 0.38 | 0.00 | 0.30 | LINC01718 | 0.45 | −0.61 | −0.14 | 1.05 | 2.04 |
| PRC1 | 0.62 | −0.32 | −0.97 | −0.11 | −0.52 | CSNK1A1P1 | 0.26 | −0.22 | 0.33 | −0.16 | −0.21 | AC024224.1 | 0.43 | −0.61 | 0.58 | 1.22 | 0.73 |
| A2ML1-AS1 | 1.19 | −0.23 | 0.60 | −0.64 | 0.09 | AC140061.3 | −0.82 | −0.13 | 0.11 | 0.02 | 0.92 | NIPA2P1 | 0.18 | 0.78 | 1.81 | −0.67 | 0.39 |
| AKR1C2 | −0.59 | 0.24 | 0.34 | 0.35 | 0.40 | BCYRN1 | 0.23 | −0.12 | 0.68 | −0.70 | −0.27 | DBH-AS1 | −0.06 | −1.03 | −1.06 | −0.94 | −0.65 |
| SOX12 | −0.40 | 0.28 | 0.16 | 0.48 | 0.31 | DOCK5 | 0.11 | −0.24 | −0.43 | −0.02 | 0.07 | LINC00896 | −0.05 | −0.26 | 0.09 | 0.17 | 0.47 |
| PURPL | −1.02 | 0.13 | 0.99 | 0.53 | 0.36 | RN7SL733P | −0.35 | 0.92 | 0.03 | −0.12 | −0.04 | NDUFA5P6 | 0.35 | −0.42 | −2.55 | 1.89 | −0.84 |
| IRF9 | 0.66 | −0.23 | −0.49 | −0.08 | −0.32 | LINC01668 | −1.06 | −0.47 | 0.71 | 0.43 | 2.08 | SNX18P26 | −0.25 | 0.35 | −0.23 | 1.03 | 1.94 |
| RCAN3 | 0.34 | 0.10 | −0.12 | 0.10 | −0.08 | SERINC3 | 0.11 | 0.12 | 0.14 | −0.01 | −0.15 | FAM173A | 0.03 | −0.01 | −0.21 | 0.11 | −0.06 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| MIR3671 | −1.34 | 1.66 | 0.86 | 0.76 | 0.33 | AC048383.1 | 0.87 | −0.88 | −0.17 | −0.86 | 1.03 | RN7SL303P | −0.26 | −0.76 | 1.12 | −1.25 | −0.10 |
| AC004494.1 | −0.72 | 0.15 | 0.37 | 0.01 | 0.55 | CACNB3 | 0.10 | −0.21 | −0.16 | 0.03 | 0.16 | LINC00560 | −0.13 | 0.64 | 1.15 | −0.44 | −0.28 |
| AC078925.3 | −1.25 | 0.68 | 2.54 | −0.11 | −0.11 | KCTD14 | −0.48 | 0.60 | 0.45 | −0.64 | −0.02 | PRDM9 | −0.08 | 0.13 | −0.30 | −0.28 | −1.06 |
| CTXN3 | 1.85 | 0.01 | −2.10 | 0.46 | −0.66 | AC117394.2 | 0.57 | −0.14 | −0.70 | −1.47 | −1.82 | OR4D8P | 0.35 | −0.02 | −0.36 | 0.42 | −0.45 |
| AP006193.1 | 1.84 | −0.84 | −1.66 | −0.30 | −0.65 | G19654 | 0.26 | 0.18 | 0.05 | −0.09 | −0.09 | AC022784.5 | −0.05 | −0.72 | 0.12 | −0.71 | 0.20 |
| RTP4 | 0.92 | −0.53 | −0.50 | −0.29 | −0.31 | COX6CP18 | 0.81 | −0.82 | −1.19 | 0.31 | 0.09 | AP001464.1 | 0.25 | 0.56 | −0.95 | −0.56 | −1.26 |
| AKR7A3 | −0.61 | 0.51 | 0.58 | 0.51 | 0.14 | OR2J3 | 0.64 | −0.48 | −1.33 | −0.27 | −0.86 | LDHBP3 | 0.45 | −1.17 | −0.55 | 0.66 | −0.49 |
| MARK2P8 | 0.61 | −0.21 | −0.97 | −0.10 | −0.73 | INKA2 | −0.18 | 0.44 | −0.48 | 0.15 | −0.33 | AL160035.1 | −0.45 | 0.17 | 0.14 | −0.09 | 0.16 |
| MALINC1 | −0.49 | −0.11 | 0.29 | −0.15 | 0.19 | RPUSD3 | 0.09 | −0.06 | −0.08 | 0.14 | 0.23 | CSNK1D | 0.01 | −0.16 | −0.40 | 0.03 | −0.03 |
| CCR4 | 1.14 | −1.08 | 0.22 | −0.83 | 0.30 | ARHGAP42P2 | −1.02 | −0.58 | −1.06 | −0.47 | −1.46 | AC079062.1 | 0.06 | −1.11 | −1.67 | 0.48 | −0.91 |
| CCDC73 | 1.01 | −0.68 | −0.98 | −0.31 | −0.57 | RNU6-151P | 0.42 | −0.09 | 1.02 | −0.29 | 0.34 | AC007608.3 | 0.05 | −0.78 | −0.10 | −0.12 | 0.46 |
| GAPDHP32 | −1.42 | −0.50 | −0.44 | 0.11 | −1.12 | LINC02085 | 1.28 | −1.95 | −0.78 | 0.41 | 0.15 | HSPE1P7 | 0.10 | −0.77 | −1.09 | −0.11 | 0.08 |
| COPZ2 | −0.39 | 0.00 | 0.42 | −0.30 | 0.13 | FAM213AP2 | −0.51 | −0.12 | 0.85 | −0.01 | 0.40 | AC068643.1 | 0.13 | −1.75 | −3.05 | 1.29 | 0.07 |
| G34275 | −0.62 | 0.45 | 0.11 | 0.00 | −0.46 | SORL1 | 0.18 | −0.14 | 0.13 | −0.31 | 0.28 | GMEB2 | −0.01 | −0.01 | −0.35 | 0.06 | −0.15 |
| RPS10P28 | −1.59 | 0.83 | 1.24 | −0.79 | 0.56 | OR51A8P | 0.98 | −0.32 | −1.89 | −0.37 | −0.86 | AL672291.1 | 0.06 | −0.63 | −1.08 | 0.63 | −0.11 |
| AL035420.2 | −1.97 | 0.99 | −1.82 | 1.91 | 0.26 | SLC23A3 | −0.22 | 0.60 | 0.71 | −0.20 | 0.15 | AC016696.1 | −0.16 | −0.11 | −0.10 | 0.02 | 0.05 |
| ACAT2 | 0.66 | −0.06 | −0.68 | 0.11 | −0.37 | FLJ42102 | 0.70 | 0.65 | −1.26 | 0.07 | −0.51 | APPBP2 | 0.01 | 0.04 | 0.20 | −0.07 | 0.03 |
| NAALAD2 | −0.55 | 0.23 | 0.29 | −0.11 | 0.12 | AC117409.1 | −0.40 | 0.64 | 0.01 | −0.22 | −0.71 | AC087498.2 | −0.45 | −0.63 | −0.83 | 1.79 | −1.65 |
| PMCHL1 | −1.76 | 0.62 | 1.82 | 1.01 | 1.82 | G38514 | −0.16 | −0.14 | 0.45 | −0.11 | 0.46 | CALM1P1 | −0.26 | 0.39 | 0.53 | −0.02 | −1.12 |
| 4-Sep | −0.51 | 0.09 | 0.30 | 0.16 | 0.08 | AL591644.1 | −1.15 | −0.20 | 1.12 | 0.04 | 0.80 | G4300 | −0.05 | −0.32 | 0.74 | 0.54 | 0.77 |
| AL031432.4 | −0.46 | −0.13 | 0.77 | −0.16 | 0.52 | AC018638.7 | −0.30 | −0.02 | 1.04 | −0.06 | 0.74 | AC092183.1 | −0.28 | −0.59 | −0.93 | 1.38 | 1.68 |
| NPRL3 | −0.24 | 0.06 | 0.02 | 0.03 | 0.09 | AC022819.2 | 0.44 | −0.63 | 0.29 | −0.41 | −0.04 | LINC01192 | 0.09 | −1.37 | −2.32 | 0.80 | −0.91 |
| ASNSP6 | −0.97 | 0.91 | 1.03 | 0.78 | 0.42 | SNAP91 | −0.52 | 0.68 | −0.54 | 1.10 | −0.58 | MED17 | 0.01 | −0.07 | −0.07 | 0.08 | −0.06 |
| GPR37L1 | −0.52 | −0.16 | −0.03 | 0.14 | 0.12 | IMMTP1 | −0.35 | −0.62 | 0.90 | 0.51 | 0.18 | AL110503.1 | 0.45 | −1.18 | −1.37 | 0.14 | −4.56 |
| RN7SL588P | −0.86 | −0.31 | 0.24 | 0.28 | 1.25 | AC092967.1 | −1.18 | −1.27 | −0.46 | −0.36 | 0.05 | AP001282.1 | 0.05 | 0.53 | 0.05 | −0.06 | −0.38 |
| S100A4 | −0.51 | 0.15 | 0.50 | −0.26 | 0.06 | RPL35P6 | −0.33 | 0.30 | −0.95 | 0.00 | −0.83 | AC121338.2 | −0.05 | −0.11 | −0.19 | 0.79 | 1.03 |
| ABCB5 | −0.85 | 0.64 | 1.47 | 0.09 | 0.30 | MTND2P26 | −0.27 | 0.11 | −0.59 | 0.13 | 0.14 | LINC00237 | −0.07 | −0.25 | 0.07 | −0.09 | 0.24 |
| PTPN12 | 0.35 | −0.14 | −0.14 | −0.35 | −0.26 | AC124856.1 | 0.67 | 0.41 | −1.94 | 0.03 | −0.86 | SLC25A5P4 | −0.26 | −0.19 | 0.42 | −1.03 | −1.02 |
| ANP32BP2 | −1.58 | 0.70 | 1.63 | 1.29 | 0.94 | AC079148.1 | −0.48 | 0.83 | −0.51 | 0.81 | −0.17 | EID3 | 0.02 | −0.04 | −0.61 | 0.21 | −0.13 |
| SIMC1 | −0.23 | 0.08 | 0.17 | 0.00 | 0.14 | ITGB5 | 0.10 | 0.20 | 0.21 | −0.04 | −0.15 | AP005121.1 | 0.41 | −0.57 | 0.34 | −0.51 | −0.80 |
| RASD1 | −0.84 | 0.23 | 0.73 | −0.16 | 0.09 | AGAP8 | −0.29 | 0.08 | 0.20 | 0.08 | 0.17 | EXD2 | −0.01 | 0.05 | 0.06 | −0.05 | 0.06 |
| DPP7 | −0.37 | 0.15 | 0.04 | 0.21 | 0.14 | AC005549.2 | −0.86 | 0.77 | −0.20 | 1.73 | −0.19 | KCNJ6-AS1 | 0.44 | 0.68 | 0.21 | −1.37 | −1.52 |
| CERS6 | −0.33 | 0.22 | 0.18 | 0.12 | −0.02 | RNU6-421P | 0.92 | 0.11 | 1.38 | −0.30 | −0.68 | C2orf15 | −0.04 | −0.02 | 1.10 | −0.03 | 0.70 |
| ARHGEF35 | 0.52 | −0.01 | −0.30 | −0.15 | −0.15 | MIIP | 0.13 | −0.45 | −0.44 | −0.14 | 0.17 | GLT6D1 | −0.16 | 0.15 | 1.40 | −1.45 | 0.71 |
| DNAJC9-AS1 | −0.49 | 0.24 | 0.86 | 0.15 | 0.43 | AC007846.1 | 0.51 | −2.38 | −2.18 | 0.04 | 0.51 | RPL12P30 | −0.15 | 1.76 | 0.50 | 1.08 | −0.48 |
| AC006953.1 | 1.62 | −3.23 | −3.64 | −1.28 | −1.14 | CYB5D2 | 0.13 | 0.06 | −0.36 | 0.15 | −0.28 | AC021192.1 | 0.22 | 0.19 | −0.38 | 0.22 | −1.14 |
| LRIT2 | −0.91 | 0.70 | 1.17 | 0.52 | 0.75 | OR14A2 | −0.67 | 1.88 | 1.89 | 0.01 | 0.14 | AC007391.1 | −0.13 | −1.50 | 0.40 | −0.47 | 0.79 |
| DDRGK1 | −0.39 | 0.00 | 0.03 | 0.01 | 0.23 | ELOBP4 | −0.42 | 0.60 | −0.40 | 0.77 | 0.31 | AL596087.1 | −0.05 | −0.34 | −1.08 | 0.39 | −0.49 |
| AC105345.2 | −0.92 | −0.12 | 0.95 | 0.79 | 0.77 | AL590783.1 | −0.49 | 0.02 | 1.41 | −0.24 | 1.46 | AC013402.1 | 0.44 | −1.25 | 0.62 | −2.20 | −0.23 |
| G31519 | 2.13 | −1.21 | −0.42 | −0.15 | 0.22 | AC004951.2 | 0.34 | 0.14 | −0.37 | 0.05 | −0.56 | RPL15P4 | 0.26 | −0.86 | −0.56 | −0.98 | 0.32 |
| STC1 | 0.68 | −0.84 | −1.21 | 0.41 | −0.81 | MIR186 | 0.47 | 0.99 | 0.08 | 0.31 | −0.87 | MIR320B2 | −0.04 | 0.09 | 0.83 | −0.18 | 0.67 |
| AL353689.1 | −1.10 | 1.58 | 0.94 | 1.01 | 0.33 | CHGB | 0.35 | −0.43 | −0.53 | −0.71 | −0.02 | AL034345.2 | 0.15 | −1.43 | −0.41 | −1.68 | 0.22 |
| AC037450.1 | −1.31 | 1.26 | 1.58 | 0.88 | −0.24 | RNU6-310P | 0.48 | −1.11 | 0.11 | −0.56 | 0.57 | AC010731.1 | 0.40 | −0.28 | 0.55 | 0.59 | 0.95 |
| AFF1 | −0.17 | 0.23 | 0.15 | 0.13 | 0.02 | SH2D1B | −0.49 | −0.13 | 0.28 | −0.83 | 0.16 | KRTCAP3 | −0.02 | −0.04 | −0.18 | 0.20 | 0.45 |
| HENMT1 | 0.53 | −0.51 | −0.10 | −0.38 | −0.21 | DEF8 | −0.09 | 0.04 | −0.07 | −0.10 | −0.11 | DNMT3L | 0.18 | −1.74 | −0.81 | −1.92 | −1.61 |
| SSSCA1-AS1 | −0.57 | 0.25 | 0.71 | 0.28 | 0.25 | AC005088.1 | 0.80 | 0.10 | 0.97 | −0.78 | 0.19 | AC025031.2 | 0.05 | −0.08 | −0.82 | −0.13 | −0.98 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| KCNQ4 | −0.65 | 0.28 | −0.02 | 0.09 | −0.05 | AL627422.2 | −0.50 | 0.55 | 1.29 | −0.20 | 0.76 | AC040963.1 | −0.44 | −0.26 | −0.23 | −0.09 | 0.18 |
| ABCA9-AS1 | −1.06 | 1.03 | 2.32 | 0.29 | 0.27 | AL162414.1 | −0.37 | −0.05 | 0.06 | 0.19 | 0.24 | OR5BB1P | 0.24 | 0.10 | −0.27 | −1.28 | −4.15 |
| AL135999.1 | −0.63 | 0.87 | 0.63 | 0.25 | −0.12 | AC079790.1 | 0.56 | −0.70 | 0.40 | 0.14 | 1.43 | C1QBPP1 | 0.27 | 0.66 | −1.93 | 0.82 | −3.36 |
| LINC00643 | −1.41 | 0.29 | 0.42 | 0.17 | 0.71 | IGBP1P4 | −0.79 | 1.07 | −0.98 | 1.44 | −0.94 | RPL7AP31 | 0.06 | −0.65 | −0.37 | −0.12 | 0.17 |
| EXOSC6 | 0.31 | −0.14 | −0.19 | −0.11 | −0.11 | MIR5692C1 | 0.50 | 0.56 | −0.79 | −0.10 | −0.87 | DCAF11 | 0.01 | 0.11 | −0.07 | 0.23 | −0.07 |
| CDK11B | −0.30 | 0.12 | −0.02 | 0.14 | 0.01 | RAB8B | 0.16 | −0.19 | 0.16 | −0.28 | −0.01 | AC139491.1 | −0.44 | −0.51 | 0.19 | −1.02 | 0.58 |
| SPHK1 | 0.59 | −0.53 | −0.79 | −0.53 | −0.41 | AC131934.1 | −0.22 | 0.15 | 0.25 | −0.31 | −0.09 | AC005252.1 | −0.44 | −0.58 | 0.82 | 0.11 | 1.52 |
| LPCAT3 | 0.32 | −0.06 | −0.20 | −0.08 | 0.03 | KRT17P7 | 1.38 | −1.10 | −1.56 | 0.45 | −2.33 | ATP5MC1P5 | 0.40 | 0.37 | −0.86 | −1.70 | −3.70 |
| AC012065.2 | −0.84 | 0.76 | 0.90 | −0.01 | −0.22 | AC092646.2 | 0.90 | −1.05 | −0.43 | −0.92 | 0.03 | AC011228.1 | −0.27 | −0.63 | −0.87 | −0.51 | −1.92 |
| CALD1 | −0.52 | 0.10 | 0.61 | −0.14 | −0.14 | MIR5685 | −0.55 | −0.34 | 0.07 | −0.69 | 0.96 | LINC01671 | −0.08 | −0.12 | −1.56 | 1.11 | −0.24 |
| AL451074.4 | 0.94 | 0.01 | −0.20 | −0.04 | −0.45 | PHKA1P1 | 0.27 | 0.07 | 0.12 | 0.00 | 0.35 | AL512649.2 | −0.20 | −0.32 | 0.13 | 0.68 | 0.39 |
| AC135983.2 | −0.32 | 0.11 | 0.29 | 0.08 | 0.11 | BRINP3 | −0.48 | 0.47 | 0.33 | 0.48 | −0.75 | AP000851.2 | −0.15 | −0.17 | 1.61 | 1.63 | 1.47 |
| CHML | 0.40 | 0.00 | 0.01 | 0.05 | −0.11 | IRF1 | 0.21 | −0.56 | −0.87 | −0.28 | −0.32 | AC010442.2 | 0.08 | −0.59 | −0.56 | −0.77 | −0.02 |
| COL26A1 | −1.20 | 0.52 | 0.97 | 0.37 | 1.03 | AC084757.3 | 0.42 | −0.87 | 0.16 | −0.50 | 0.59 | HNRNPA3P6 | 0.02 | −0.29 | −0.32 | 0.26 | 0.49 |
| MAL | −0.68 | −0.13 | 0.65 | −0.28 | 0.50 | LINC01356 | −0.36 | −0.14 | 0.31 | −0.24 | 0.48 | KCTD9P2 | 0.06 | −0.37 | 0.43 | −0.10 | −0.20 |
| AC097724.1 | 1.47 | 0.15 | 0.81 | −1.06 | −0.17 | HMGN2P21 | −1.34 | 1.78 | 1.06 | 0.36 | 0.17 | AC092801.1 | 0.02 | 0.03 | 0.32 | −0.09 | 0.14 |
| RP11-24B13.1 | −1.35 | 0.76 | 1.52 | 0.65 | 0.29 | ADAMTS1 | 0.22 | −0.71 | −0.49 | −0.34 | −0.31 | AC107029.1 | −0.20 | 0.12 | −0.49 | 1.82 | −2.32 |
| GCHFR | −1.15 | 1.02 | 0.14 | 1.04 | −0.56 | C1orf105 | −0.25 | 0.24 | −0.13 | 0.63 | 0.22 | NDUFA5P7 | −0.44 | 0.49 | −1.28 | 0.77 | −2.32 |
| AC068025.2 | 0.74 | −0.25 | −0.16 | 0.09 | −0.07 | SIRPB3P | −0.76 | −0.07 | 0.39 | 0.01 | −0.36 | MAGEL2 | −0.13 | 0.25 | 1.94 | −1.46 | −2.00 |
| AC016909.1 | 1.36 | −0.18 | −0.83 | −0.16 | −0.82 | SLC25A15P5 | −0.38 | −0.21 | 0.16 | 0.31 | 0.26 | BARX1 | −0.13 | −1.15 | −1.40 | −0.67 | −1.58 |
| AL445490.1 | 1.01 | −0.73 | −1.28 | −0.95 | −0.43 | AC104232.1 | 0.55 | −2.21 | 0.10 | −0.86 | 0.31 | AP000470.1 | 0.11 | −0.38 | −0.30 | 0.14 | −0.35 |
| RN7SL230P | −0.85 | 0.24 | 0.61 | −0.34 | −0.26 | PCDHA11 | −0.47 | 0.07 | 1.11 | 1.31 | 1.00 | AL139824.2 | 0.44 | −0.86 | −0.77 | −0.43 | 0.78 |
| SF3B2 | 0.20 | −0.19 | −0.23 | −0.10 | −0.07 | AKIRIN1P1 | −1.19 | −0.27 | 0.66 | −1.34 | 0.55 | SNORD114-23 | 0.20 | 0.99 | 0.26 | 0.19 | −1.04 |
| RN7SL92P | −1.96 | 1.47 | 3.48 | 0.42 | 1.86 | RNF103 | −0.11 | 0.30 | 0.29 | 0.10 | −0.07 | MTCYBP39 | 0.34 | −0.54 | −0.49 | −0.27 | 0.14 |
| HAPLN2 | −1.32 | 0.50 | 0.62 | 0.02 | 0.86 | MAGT1 | 0.08 | −0.11 | −0.17 | −0.05 | −0.11 | AC007881.2 | −0.08 | 0.23 | 0.52 | 0.81 | 0.39 |
| AOAH-IT1 | 1.16 | −0.85 | −1.28 | −0.11 | −0.15 | AC005006.1 | −0.58 | 0.82 | −0.12 | −0.25 | −0.66 | AC115220.1 | −0.14 | −1.04 | −1.59 | 0.34 | −1.46 |
| AL358332.1 | −0.86 | 0.58 | 0.88 | 0.94 | 0.55 | HIST2H3C | 0.66 | −0.95 | −1.31 | −0.06 | 0.04 | OR10K1 | −0.07 | −1.06 | −1.01 | 0.40 | −0.64 |
| ANKRD26P4 | 0.98 | −0.66 | −0.78 | −0.12 | −0.43 | AL590282.2 | −0.18 | −0.24 | 0.95 | −0.45 | 0.53 | DLG3-AS1 | −0.05 | 0.47 | 0.16 | 0.25 | −0.06 |
| SAP130 | 0.18 | 0.01 | −0.06 | −0.01 | −0.11 | AC012676.2 | 0.46 | −0.45 | 0.62 | −0.29 | 0.51 | GAPDHP58 | 0.14 | −1.64 | −0.02 | −0.04 | 1.62 |
| CCNT1 | 0.21 | −0.01 | −0.09 | −0.06 | −0.16 | AC009884.1 | 0.25 | −0.15 | −0.98 | 0.10 | 0.01 | AC091182.1 | 0.06 | −0.09 | −0.04 | −0.12 | −0.26 |
| FBXO7 | −0.22 | 0.13 | 0.00 | 0.09 | −0.13 | HSPB9 | 0.32 | −0.21 | 0.59 | 0.00 | 0.48 | AL606534.3 | −0.44 | 0.15 | −0.65 | 0.37 | −0.44 |
| COX6CP17 | 1.02 | −0.36 | −0.46 | −0.22 | −0.17 | HSPE1P25 | 0.35 | −0.17 | −0.43 | −0.08 | 0.32 | AC233728.2 | −0.13 | 0.75 | −1.63 | −0.31 | −2.39 |
| SCARNA13 | −0.67 | 0.63 | −0.09 | 0.31 | −0.80 | PCDHB1 | −0.59 | −0.09 | 0.20 | 0.91 | 0.16 | FNDC3A | −0.01 | 0.04 | 0.13 | −0.06 | 0.06 |
| MTND2P40 | −1.03 | 0.32 | 0.97 | −0.08 | 0.49 | LINC01507 | −0.92 | 0.68 | −0.58 | −0.37 | 0.03 | RN7SL717P | −0.10 | −0.91 | −0.82 | 1.25 | −0.41 |
| G17182 | −1.71 | 0.57 | 1.30 | 0.83 | −0.03 | KRTAP5-11 | −1.41 | 0.64 | −0.91 | 1.01 | −1.85 | AL645568.3 | 0.08 | 0.26 | 1.01 | −1.00 | 0.13 |
| APBB2 | −0.23 | 0.16 | 0.27 | 0.02 | 0.09 | ADH1A | −0.25 | −0.12 | 1.09 | 0.26 | 0.72 | AL136234.1 | −0.44 | 0.54 | −0.44 | −0.78 | −2.35 |
| ENPP7P10 | −0.64 | 0.27 | 0.79 | 0.28 | 0.30 | AC090950.1 | −0.24 | 0.37 | 0.83 | −0.36 | 0.03 | LINC01099 | −0.07 | −0.31 | −0.33 | 0.85 | 0.61 |
| FAM86B3P | 0.66 | −1.01 | −0.79 | 0.61 | 0.09 | AL356118.1 | −0.62 | 0.14 | −0.61 | 0.04 | −0.86 | NUS1P3 | 0.20 | −0.07 | −0.36 | −1.16 | −0.55 |
| PRKAG3 | −0.91 | −0.39 | 1.27 | −0.44 | 0.47 | IGFL3 | −0.20 | 0.61 | 0.57 | 0.09 | −0.19 | AC090398.1 | 0.12 | −1.20 | 0.06 | −0.81 | 1.25 |
| OXR1 | −0.24 | 0.33 | 0.44 | 0.14 | 0.00 | RNU6-182P | 0.77 | 0.66 | −2.46 | 0.04 | −0.78 | AC245100.6 | −0.41 | −0.11 | 0.47 | −1.47 | −1.46 |
| AC008026.3 | −0.57 | −0.31 | 0.28 | −0.21 | 0.33 | AC138305.2 | −0.50 | 0.08 | 1.55 | −1.13 | 0.20 | AL691482.1 | −0.44 | 0.18 | NA | −0.01 | −0.54 |
| G37438 | −1.42 | 0.71 | 3.01 | −0.20 | 1.35 | AC114786.2 | −1.00 | 0.69 | −0.54 | 1.97 | −1.75 | AC093423.2 | 0.03 | −0.30 | 0.15 | −0.10 | 0.37 |
| AC005786.2 | −1.59 | 0.04 | 0.20 | −0.33 | 1.15 | AL049869.1 | 0.50 | −1.16 | −1.05 | −0.01 | −0.59 | KRTAP8-1 | −0.25 | 0.62 | −1.41 | 0.33 | −1.71 |
| AC004231.1 | −0.97 | 0.44 | 0.95 | −0.27 | −0.34 | RN7SL815P | −0.56 | −0.96 | 1.25 | 0.95 | 1.68 | CCL15 | 0.20 | −1.37 | −0.26 | −1.21 | 1.88 |
| HMGN2P35 | 0.95 | −1.71 | −1.10 | −0.03 | 0.45 | BMP7-AS1 | 0.51 | 0.57 | 1.03 | 0.21 | 0.37 | NPM1P22 | −0.13 | −0.98 | −1.70 | 0.57 | −0.26 |
| AC107214.2 | 1.89 | −0.78 | −1.02 | −0.31 | −0.35 | AL445531.1 | 0.45 | 0.56 | −2.49 | 0.95 | −1.50 | AP000745.1 | 0.41 | −0.26 | −0.46 | 1.23 | 2.17 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| OR913P | −1.22 | −0.27 | 0.99 | −0.34 | 0.14 | AL590723.1 | 0.17 | 0.25 | 0.20 | 0.12 | −0.20 | EGLN2 | 0.02 | 0.07 | −0.16 | 0.05 | −0.05 |
| RAB3A | −0.56 | 0.32 | 0.29 | −0.01 | 0.11 | RNU7-195P | 0.53 | −0.88 | 0.56 | −0.94 | −0.03 | AC245052.1 | −0.06 | −0.62 | 0.84 | −0.23 | 0.50 |
| AL121908.1 | −1.46 | −1.69 | −1.34 | −0.37 | −0.12 | AL355852.1 | −0.31 | 0.78 | 0.42 | 0.64 | 0.35 | AC083843.2 | −0.02 | −0.04 | 0.42 | 0.12 | 0.39 |
| KDM7A | 0.31 | −0.05 | −0.30 | −0.25 | −0.45 | LINC02086 | 0.54 | −1.01 | −1.42 | 0.19 | 0.25 | MIR3152 | 0.44 | −0.03 | −0.82 | 0.27 | −1.20 |
| CWC22 | 0.28 | −0.09 | −0.19 | −0.10 | −0.21 | AL049539.1 | −0.27 | 0.47 | 0.13 | −0.10 | −0.13 | RNU6-340P | −0.44 | NA | −0.80 | 0.87 | 0.87 |
| AL591623.1 | −0.50 | 0.11 | 0.18 | 0.07 | 0.14 | RNU4ATAC18P | 0.43 | −0.21 | 0.36 | 0.03 | 0.26 | AC040169.3 | −0.04 | −0.16 | 0.29 | 0.32 | 0.79 |
| ATP6V1C1 | 0.31 | −0.24 | −0.18 | −0.14 | −0.07 | AC079015.1 | −0.70 | 0.54 | 0.43 | 0.54 | −0.92 | DOPIA | 0.01 | 0.15 | 0.10 | −0.04 | −0.23 |
| AC007179.1 | −2.13 | −0.58 | 2.17 | 0.02 | 2.40 | LINC02030 | −0.64 | −0.21 | −0.50 | −0.07 | −0.09 | C2orf69P1 | −0.44 | −0.55 | −0.99 | 0.37 | −2.25 |
| AP002986.1 | −1.02 | 0.61 | 0.89 | 0.36 | 0.76 | AL080243.1 | −0.48 | −0.50 | −1.57 | 0.16 | −0.91 | AC016691.1 | 0.26 | 0.79 | −1.60 | 0.16 | −0.49 |
| AC046143.1 | −0.55 | 0.34 | −0.22 | 0.31 | −0.18 | AL023803.1 | 1.38 | −0.80 | 1.34 | 0.61 | 2.39 | AC087392.3 | 0.03 | −0.14 | 0.26 | −0.40 | 0.13 |
| PLA2G12AP1 | 1.11 | −0.43 | −1.06 | −0.51 | −0.77 | SP1 | 0.10 | 0.12 | 0.05 | 0.06 | −0.11 | RN7SKP197 | −0.17 | 0.58 | −0.58 | 1.61 | −1.96 |
| RPL7P36 | −1.72 | −0.30 | 2.39 | −1.43 | 1.60 | SHLD2P2 | −0.25 | 0.06 | −0.22 | 0.00 | 0.19 | AC091769.2 | 0.05 | −0.37 | 0.27 | −0.42 | 0.32 |
| AC051619.5 | −0.91 | 0.76 | −0.21 | 0.06 | −0.45 | MIR659 | 0.79 | −1.12 | −0.48 | 0.60 | 2.11 | AL162726.1 | −0.23 | 0.43 | −0.79 | −0.36 | −1.41 |
| COL19A1 | −1.03 | −0.11 | −0.72 | 0.29 | 0.00 | AC131235.1 | −0.27 | 0.08 | −1.90 | 0.40 | −0.78 | LRRC63 | −0.06 | −0.32 | 0.07 | 0.32 | 0.55 |
| PCDHB6 | −0.89 | 0.21 | 1.43 | −0.06 | 0.52 | RNU6-928P | 0.78 | −0.32 | −1.47 | 0.79 | −0.35 | MRRFP1 | 0.12 | 0.80 | −1.89 | 2.04 | −0.87 |
| PCAT7 | −1.19 | 0.01 | 0.43 | 0.11 | 0.26 | AC004381.1 | −0.53 | −0.63 | 0.38 | −0.77 | −0.07 | AC091705.1 | −0.43 | −1.26 | 0.47 | −0.69 | 0.80 |
| CATSPERD | −1.05 | 0.02 | 0.83 | 0.48 | 0.59 | AC007786.1 | −0.75 | 0.62 | 0.68 | 1.27 | 1.26 | RPL23P10 | −0.30 | −0.44 | −1.30 | 2.24 | −0.70 |
| STRC | −0.56 | 0.05 | −0.13 | 0.18 | 0.13 | L3HYPDH | 0.08 | −0.12 | −0.06 | −0.17 | −0.03 | AL021392.1 | −0.03 | 0.07 | −0.23 | 0.42 | 0.47 |
| NDUFA8P1 | 1.17 | −0.05 | −1.10 | 0.46 | 0.01 | AL589765.3 | 0.73 | 0.70 | −1.66 | 0.49 | −1.47 | ACTP1 | −0.43 | 0.65 | 0.47 | 0.34 | −0.31 |
| DLEU2 | 0.30 | −0.46 | −0.14 | −0.30 | 0.12 | LINC02278 | 1.21 | −1.62 | −0.33 | 0.59 | 1.97 | AC034159.1 | −0.25 | −0.48 | 0.59 | −1.43 | −0.79 |
| DNAJC21 | 0.30 | −0.20 | −0.19 | −0.20 | −0.12 | AC004231.3 | −0.92 | −0.07 | 2.44 | 0.07 | 0.07 | RPS29P7 | −0.08 | 0.60 | 0.88 | −0.35 | −0.25 |
| AP000318.1 | −1.27 | 1.06 | 0.07 | 1.08 | 0.12 | AC104134.1 | 0.56 | −0.55 | 0.71 | 0.12 | 0.51 | OR3D1P | −0.11 | −1.42 | 0.49 | 0.34 | −0.39 |
| AC010867.1 | −1.33 | 0.44 | −0.86 | 0.72 | −1.51 | AL138729.1 | 0.59 | −0.34 | 0.03 | −0.81 | −0.08 | RNA5SP323 | 0.05 | −0.83 | −1.20 | −0.44 | 0.00 |
| AKR1C1 | −0.59 | 0.27 | −0.15 | 0.27 | −0.07 | SLC22A11 | −0.66 | 0.27 | −2.10 | 1.87 | −0.67 | FDPSP2 | −0.06 | −0.13 | 0.39 | −0.04 | 0.11 |
| SNX13 | 0.19 | −0.01 | −0.08 | 0.06 | −0.05 | NIFKP9 | 1.55 | −1.12 | 1.61 | −1.40 | 1.83 | AC016597.2 | 0.08 | 0.08 | −0.57 | −0.71 | −1.03 |
| BBOF1 | −0.43 | 0.30 | 0.61 | 0.10 | −0.05 | EIF3FP1 | 0.77 | −0.22 | −1.47 | −0.04 | −2.03 | DPF2 | −0.01 | 0.00 | −0.16 | 0.03 | −0.09 |
| B3GALNT2 | 0.31 | −0.04 | −0.22 | 0.09 | −0.08 | MIR623 | 0.30 | −0.49 | 0.09 | −0.33 | 0.22 | PRSS58 | −0.17 | 0.52 | −2.51 | 0.10 | −3.23 |
| PIK3C2A | 0.22 | 0.05 | −0.09 | 0.01 | −0.20 | AC009132.1 | −0.71 | 0.07 | −0.24 | 1.22 | 0.56 | NDUFB4P8 | −0.11 | −0.56 | 0.96 | −0.87 | −0.44 |
| SMIM30 | 0.49 | −0.20 | −0.21 | −0.18 | −0.26 | AL139022.1 | 0.13 | −0.17 | 0.13 | 0.06 | 0.30 | BTBD9 | −0.01 | 0.11 | 0.03 | 0.02 | −0.12 |
| RAB5C | 0.33 | −0.25 | −0.23 | −0.18 | −0.19 | AC079336.7 | −0.20 | 0.11 | 0.25 | −0.19 | 0.29 | MTCYBP19 | 0.14 | −0.16 | −1.24 | 0.35 | 0.40 |
| DDX51 | −0.35 | 0.05 | −0.13 | 0.15 | 0.20 | LNPEP | 0.12 | 0.18 | 0.11 | 0.11 | −0.23 | RNU4-50P | 0.25 | 0.99 | −0.50 | 0.97 | −1.45 |
| MT-ND3 | −0.53 | 0.31 | 0.40 | 0.20 | 0.14 | AC034102.5 | −0.50 | −0.05 | 0.13 | 0.27 | 0.67 | AL353613.2 | −0.07 | −0.54 | −0.43 | 0.65 | −0.79 |
| AL355432.1 | −1.42 | 1.35 | 1.58 | 1.80 | 0.70 | GLYATL1P4 | −0.61 | 0.64 | 1.80 | 0.68 | −0.07 | AL356276.2 | −0.22 | 0.16 | −1.17 | 1.91 | −0.58 |
| G36939 | −0.78 | 0.47 | 1.05 | 0.70 | 0.27 | AC016999.1 | 0.44 | 0.00 | −0.94 | 0.46 | −0.35 | AC012229.1 | 0.43 | 1.25 | −2.15 | 1.85 | −2.81 |
| AC032044.1 | −0.70 | 0.05 | 0.28 | 0.19 | 0.35 | AC008752.1 | 0.64 | 0.50 | 1.82 | −0.32 | −0.24 | MTND4LP26 | 0.43 | −0.95 | −1.69 | 0.46 | −0.50 |
| CRISPLD2 | 0.52 | −0.47 | −0.37 | −0.70 | −0.51 | AC133552.5 | −0.39 | 0.50 | 1.00 | 0.55 | −0.30 | AC073284.1 | −0.30 | −0.63 | 0.58 | −0.61 | 0.89 |
| MAP3K20-AS1 | 0.44 | −0.37 | −0.51 | −0.30 | −0.46 | AC105129.1 | 0.38 | −0.09 | −0.01 | 0.15 | 0.05 | RPL18AP2 | −0.05 | 0.09 | −0.25 | 0.57 | 0.29 |
| CKMT2-AS1 | −0.35 | 0.13 | 0.72 | −0.05 | 0.12 | AC083873.1 | 0.37 | −0.27 | 0.10 | −0.25 | −0.18 | RBM11P1 | −0.43 | −0.45 | −0.47 | −0.25 | 0.23 |
| ST6GALNAC4P: | −0.86 | 0.44 | 1.62 | 0.16 | 0.44 | AL356124.1 | −0.28 | −0.52 | 0.02 | −0.13 | 0.60 | ACTR3BP5 | −0.27 | 0.83 | −1.01 | 2.21 | −0.34 |
| AL390719.3 | 0.46 | −0.51 | −0.36 | −0.27 | 0.09 | CLYBL-AS1 | 0.36 | −0.55 | −0.37 | −0.09 | 0.29 | OR5M11 | −0.22 | −0.03 | −0.75 | 0.41 | −1.57 |
| AC010978.1 | 0.61 | −0.23 | −0.42 | −0.14 | −0.02 | AC089987.1 | −0.73 | 0.47 | −0.03 | 1.90 | 0.65 | CUL4AP1 | −0.09 | 0.53 | −0.42 | 0.30 | −1.01 |
| NDUFAF4P3 | −1.04 | 0.85 | 1.85 | 0.24 | 0.67 | AP000442.1 | −0.45 | −1.08 | −0.36 | 0.35 | 1.04 | SHMT1 | −0.02 | 0.11 | −0.09 | 0.35 | 0.00 |
| RET | −0.52 | −0.07 | 0.62 | −0.02 | 0.49 | OR7E26P | 0.82 | −0.31 | −2.73 | 1.44 | −0.96 | AC018554.1 | 0.42 | −0.79 | −0.83 | −0.70 | −0.48 |
| GTF3C1 | −0.24 | 0.19 | 0.19 | 0.11 | 0.01 | AP001357.2 | −1.27 | 0.90 | 0.37 | 1.57 | 0.65 | AC099552.3 | −0.20 | −0.47 | 0.62 | −0.59 | 0.71 |
| ST13P15 | −0.45 | 0.36 | 0.67 | 0.30 | 0.16 | AL022310.1 | −0.53 | 0.25 | 2.53 | −1.04 | 0.86 | C7orf31 | 0.02 | 0.13 | 0.21 | 0.02 | 0.15 |
| COL1A1 | 0.78 | 0.27 | 1.46 | −1.08 | −0.44 | FAM72A | −0.21 | −0.05 | 0.07 | −0.12 | −0.31 | AL121823.1 | −0.23 | −1.14 | −0.25 | 0.40 | −0.06 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| DCX | −1.19 | 1.32 | 0.65 | 1.22 | 0.13 | EDARADD | 0.15 | −0.27 | −0.29 | 0.08 | 0.25 | 10-Mar | −0.05 | −0.84 | −0.51 | −0.33 | 0.22 |
| KATNAL1 | −0.33 | 0.27 | 0.37 | 0.06 | −0.08 | RN7SL498P | 1.04 | −1.76 | −2.21 | 1.22 | −0.18 | MEG8 | −0.03 | 0.22 | 0.35 | −0.37 | −0.40 |
| C1R | 0.55 | −0.26 | 0.25 | −0.33 | −0.14 | KCNJ12 | 0.17 | 0.22 | −0.05 | 0.23 | −0.44 | OR2AP1 | −0.17 | −1.81 | 1.66 | −0.33 | 0.85 |
| GTF2IP12 | −0.43 | 0.26 | 0.78 | 0.12 | 0.14 | CLYBL-AS2 | 0.30 | −0.09 | −0.06 | 0.01 | 0.32 | EZR-AS1 | −0.04 | −0.14 | 0.12 | 0.06 | 0.48 |
| PPP1R26 | 0.41 | −0.17 | −0.43 | −0.18 | 0.10 | OR5BC1P | −0.77 | −1.44 | 1.50 | −1.51 | −0.62 | GTF2IP3 | −0.27 | −0.30 | −0.23 | −0.11 | −0.90 |
| AC005332.7 | −1.22 | 0.66 | 2.20 | −0.35 | 0.24 | MIR1285-1 | 0.39 | 0.64 | −1.03 | 0.75 | −0.05 | NARS2 | −0.01 | −0.13 | −0.19 | −0.09 | 0.14 |
| PDXDC2P | −0.58 | 0.35 | 0.22 | 0.04 | −0.31 | AC103739.2 | 0.28 | 0.77 | −0.19 | 0.44 | −0.61 | AL121885.2 | 0.13 | −2.60 | −2.03 | −0.84 | −0.61 |
| AL157893.1 | −0.72 | 0.30 | 0.42 | 0.26 | 0.46 | AC105342.1 | −0.46 | −0.81 | 0.97 | 0.07 | 0.10 | AC090587.1 | 0.11 | 2.07 | −0.30 | 1.86 | −1.21 |
| FLT1 | 0.51 | −0.43 | 0.23 | −0.18 | 0.00 | KATNBL1P5 | −1.04 | −0.78 | 0.09 | −0.07 | −0.46 | LINC02569 | −0.05 | −0.39 | −0.81 | 0.15 | −0.04 |
| PDZD3 | −0.97 | 0.67 | 0.35 | 0.94 | 0.93 | RBMS3-AS1 | −0.41 | 0.00 | −0.46 | 0.37 | 0.29 | AP000705.2 | 0.43 | −0.46 | −0.08 | −0.55 | −0.89 |
| DEAF1 | −0.26 | 0.14 | 0.24 | 0.25 | 0.18 | AL355493.4 | 0.64 | −0.47 | −0.19 | 0.80 | −0.47 | HNRNPA3P2 | 0.05 | −0.82 | 0.05 | −0.91 | 0.09 |
| BMPR1AP1 | −0.92 | 0.33 | 0.25 | 0.72 | 0.48 | PIK3IP1-AS1 | −0.31 | 0.28 | 0.34 | 0.79 | 0.21 | KLHL7 | 0.01 | 0.10 | 0.29 | −0.05 | 0.04 |
| PPT2-EGFL8 | −0.72 | 0.43 | 1.14 | −0.12 | 0.17 | OR2A4 | −0.63 | 0.95 | 0.10 | 0.79 | −0.51 | RPS4XP15 | 0.40 | 0.03 | −0.61 | −0.89 | −1.34 |
| RNU6-946P | 1.12 | −0.30 | −0.75 | −0.07 | −0.11 | ARHGAP45 | −0.15 | −0.28 | −0.07 | −0.11 | 0.24 | AC091953.1 | −0.25 | −0.36 | 0.38 | −1.52 | −0.49 |
| DSN1 | 0.26 | −0.40 | −0.24 | −0.27 | −0.04 | ANKRD44 | −0.13 | −0.11 | 0.19 | −0.21 | 0.13 | AL606468.1 | −0.09 | −0.62 | 0.15 | −0.12 | 0.75 |
| ILF2P1 | −0.59 | 0.25 | 0.34 | −0.13 | 0.23 | CATIP | 0.41 | −1.74 | −1.29 | −0.51 | −0.28 | RNU6-855P | −0.08 | 0.10 | −0.48 | 0.07 | −0.51 |
| OR4D2 | −1.77 | 0.49 | −0.66 | 0.29 | −1.05 | AL049569.1 | 0.76 | −2.01 | −2.51 | 0.41 | 0.29 | JAKMIP2-AS1 | −0.11 | −0.15 | −0.12 | 0.32 | −0.55 |
| AL035448.1 | 0.69 | −0.29 | −0.63 | 0.09 | −0.25 | LINC00381 | 0.53 | −1.40 | −1.42 | 0.37 | −0.68 | AC138701.1 | 0.38 | −0.96 | −0.52 | −0.41 | 0.14 |
| OGFOD3 | −0.29 | 0.16 | 0.23 | 0.05 | 0.13 | AC016716.2 | 1.08 | −1.80 | 0.29 | −0.69 | 1.59 | RSBN1 | 0.01 | 0.18 | 0.07 | 0.01 | −0.19 |
| CNPY3 | −0.32 | −0.12 | 0.16 | −0.09 | 0.15 | AC011365.2 | −0.52 | 0.14 | 1.07 | −1.44 | −0.25 | PNMA6E | 0.14 | −0.38 | 0.48 | 0.99 | −0.58 |
| AL136418.1 | −0.89 | 0.79 | 1.27 | 0.29 | −0.15 | PGAM1P7 | −0.39 | −0.41 | −0.34 | 0.39 | 0.68 | CDIPTOSP | 0.10 | −1.10 | −2.56 | 0.43 | −0.37 |
| LGALS8 | 0.28 | 0.05 | −0.14 | 0.14 | −0.14 | C5orf47 | −0.85 | −0.96 | 0.17 | 0.46 | 0.16 | AL807740.1 | −0.11 | −1.56 | 1.49 | −0.25 | 0.73 |
| AC005070.2 | 1.11 | −0.48 | −1.27 | 0.26 | −0.41 | AC245100.5 | −0.85 | 0.04 | 0.71 | 0.80 | 0.01 | AC092079.1 | −0.16 | −0.04 | −1.73 | 1.56 | −1.74 |
| NUBPL | −0.26 | 0.02 | 0.10 | −0.06 | 0.01 | OR13D1 | −0.31 | −0.27 | 0.31 | −0.77 | −0.40 | RPLPOP7 | 0.43 | −0.53 | −0.67 | 0.54 | 0.15 |
| DHX57 | 0.16 | −0.04 | −0.14 | 0.04 | −0.04 | AC010320.2 | 0.32 | 0.12 | 0.02 | 0.25 | 0.17 | AL161454.1 | −0.03 | 0.13 | −0.34 | 0.21 | 0.23 |
| AP006477.1 | −1.45 | −0.19 | 0.27 | −0.24 | 1.42 | AP003174.1 | 1.16 | −1.15 | −0.59 | 0.56 | 0.57 | LHX3 | −0.09 | 1.74 | −0.59 | 0.80 | −0.03 |
| AC091144.2 | −0.65 | 0.12 | 0.47 | 0.66 | 0.58 | SNORA23 | 0.17 | 0.36 | −0.01 | 0.09 | −0.65 | KRT18P50 | 0.30 | −0.83 | −1.50 | 0.19 | −1.22 |
| BHLHB9 | −0.36 | 0.48 | 0.30 | 0.33 | −0.06 | AC134407.3 | 0.21 | 0.14 | 0.08 | 0.10 | −0.06 | AC090079.2 | −0.43 | 1.28 | −1.85 | 0.51 | −1.05 |
| RPL7AP50 | 1.02 | −0.32 | 0.60 | −0.12 | −0.11 | RPL31P2 | −0.44 | −0.53 | 0.76 | −0.13 | 1.00 | LINC02533 | −0.05 | −0.31 | −0.24 | 0.12 | 0.02 |
| INCENP | 0.35 | −0.37 | −0.72 | −0.15 | −0.04 | AL391419.1 | −0.18 | 0.16 | 0.17 | 0.28 | 0.15 | AP003499.3 | −0.18 | −0.41 | −0.67 | −1.41 | −0.96 |
| RN7SL49P | −0.61 | −0.06 | 0.21 | −0.03 | 0.15 | MYZAP | 0.36 | 0.16 | −0.09 | 0.45 | −1.07 | CCNI | 0.02 | 0.15 | 0.23 | 0.04 | −0.06 |
| CPEB4 | 0.30 | 0.02 | −0.35 | 0.04 | −0.37 | SETP15 | 1.15 | 0.98 | −0.02 | −0.01 | −1.15 | AC007673.1 | 0.04 | 0.42 | 0.88 | 0.17 | 0.10 |
| LINC00989 | −0.92 | 0.60 | 0.91 | 0.59 | −0.13 | AC017002.6 | −0.60 | −1.59 | 1.44 | −0.77 | 0.98 | AL031667.1 | 0.43 | −1.60 | 0.60 | −2.23 | 0.00 |
| CDCA4P4 | −0.72 | 0.25 | 0.60 | 0.31 | 0.27 | NNAT | −0.15 | −0.09 | −0.22 | −0.03 | 0.13 | ELOCP31 | 0.04 | −0.78 | −0.53 | 0.34 | 0.22 |
| RUFY2 | −0.19 | 0.14 | 0.18 | 0.07 | −0.02 | LPAR4 | −0.35 | 0.09 | 1.01 | −0.62 | 0.61 | AL109809.3 | 0.18 | 0.19 | −0.29 | 0.68 | 0.41 |
| LINC00384 | −0.99 | 0.55 | −0.71 | 0.11 | −1.18 | NPM1P30 | 0.20 | 0.39 | 0.49 | 0.05 | 0.02 | AC004858.1 | 0.06 | −0.19 | 0.48 | −0.46 | 0.65 |
| LINC00908 | −0.98 | −0.09 | −0.51 | 0.12 | 0.07 | AC129507.2 | −0.74 | 0.64 | 0.67 | 0.79 | −0.08 | HNRNPA1P11 | −0.27 | 0.34 | 0.52 | −0.33 | −0.27 |
| CSMD2 | 0.69 | −0.54 | −0.75 | −0.76 | −0.67 | G25496 | 0.39 | 0.25 | 0.11 | 0.12 | −0.34 | AL138878.1 | 0.11 | 1.07 | 0.72 | −0.13 | −0.80 |
| SEC22C | 0.22 | −0.10 | −0.25 | 0.01 | −0.07 | AC064802.1 | 0.91 | −2.19 | −2.15 | −0.29 | −0.32 | GMFBP1 | 0.42 | 0.37 | 0.55 | 1.17 | −1.74 |
| HAGHL | −0.66 | 0.10 | 0.02 | −0.01 | −0.13 | LINC00933 | −0.21 | 0.48 | 0.85 | 0.37 | 0.07 | AC073176.1 | −0.25 | −1.24 | −0.67 | 0.23 | 1.22 |
| EMG1 | 0.31 | −0.16 | −0.31 | 0.02 | −0.14 | AP000974.1 | −0.33 | −0.41 | 1.41 | −0.33 | 1.04 | MTCO1P54 | −0.06 | 0.72 | −0.95 | 0.45 | −0.92 |
| AC006116.9 | −1.57 | −0.73 | 2.50 | −0.75 | 1.31 | AC005920.4 | 0.41 | 0.02 | 0.94 | 0.11 | 0.52 | AC004870.4 | −0.35 | 1.26 | −0.12 | −0.98 | −1.70 |
| NIPBL | 0.20 | 0.05 | −0.06 | 0.00 | −0.16 | RPS4XP8 | 1.02 | −0.14 | 0.28 | −0.24 | −1.35 | AC016405.1 | −0.02 | 0.01 | 0.06 | 0.03 | 0.08 |
| AL512324.3 | −1.55 | 0.31 | −1.08 | 0.32 | −0.04 | AL592437.1 | 0.40 | −0.77 | −0.37 | −0.11 | 0.16 | LINC02105 | −0.12 | −0.57 | −0.02 | 0.09 | 1.74 |
| STX7 | −0.21 | 0.24 | 0.16 | 0.16 | −0.01 | G39254 | 0.56 | −0.98 | −0.53 | −0.53 | 0.24 | AC106818.1 | 0.08 | 0.01 | −0.85 | 0.47 | −0.51 |
| S100B | −0.72 | 0.76 | 0.39 | −0.08 | 0.04 | AC023310.1 | −0.39 | −0.15 | 0.67 | 0.17 | 0.50 | AC114981.1 | 0.42 | −0.91 | −0.49 | −0.60 | NA |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| FBXO40 | −1.03 | −0.36 | −0.16 | −0.74 | −0.24 | AC090246.1 | −0.59 | −1.27 | 3.06 | −0.07 | 3.02 | AL080276.2 | −0.04 | −0.05 | −0.04 | 0.06 | 0.04 |
| AC002128.1 | −0.43 | −0.07 | 0.26 | −0.01 | 0.06 | AC068896.1 | −0.23 | 0.24 | 0.10 | 0.43 | 0.32 | ADIPOR1P1 | −0.13 | −1.72 | −0.04 | 0.18 | 1.10 |
| EVL | −0.37 | 0.26 | 0.32 | 0.06 | 0.21 | AC105206.2 | −0.40 | 0.42 | 0.37 | −0.47 | −0.62 | AC080068.1 | −0.18 | −0.80 | −1.27 | 0.00 | −1.09 |
| MAGEE2 | −1.27 | 0.24 | 0.98 | 0.24 | 0.84 | AL022345.3 | −0.69 | 0.57 | 3.20 | −0.75 | 0.15 | AC060834.2 | 0.42 | −0.92 | −0.15 | −1.18 | 0.99 |
| RN7SKP237 | −0.78 | 0.15 | 1.45 | 0.18 | 1.22 | LINC02124 | −0.65 | 0.94 | 0.72 | 1.49 | 0.51 | AL157387.1 | −0.22 | −0.49 | 1.02 | −0.71 | 0.57 |
| MRPL48 | 0.27 | −0.05 | −0.34 | 0.01 | −0.12 | AC008940.1 | −0.65 | 1.23 | 1.56 | −0.49 | −0.25 | KRTAP6-3 | −0.42 | 0.45 | 0.65 | NA | 0.39 |
| FAH | −0.48 | 0.14 | 0.09 | 0.27 | 0.02 | RNU6-1111P | 0.32 | −0.12 | −0.78 | −0.14 | −1.01 | AC130456.8 | 0.14 | −0.91 | −1.40 | 0.36 | −0.54 |
| CUL4B | 0.30 | 0.01 | −0.12 | 0.02 | −0.16 | STAP1 | 0.32 | −0.43 | −0.02 | 0.04 | 0.18 | AL035467.2 | 0.12 | 0.71 | −1.16 | 0.95 | −1.96 |
| PPP2CB | 0.27 | −0.03 | −0.17 | −0.04 | −0.32 | EML3 | −0.12 | −0.03 | −0.14 | 0.18 | 0.18 | RPS14P7 | −0.42 | 0.16 | −1.83 | 0.61 | −0.51 |
| KDELC1 | 0.42 | −0.19 | 0.20 | −0.30 | 0.06 | EEF1B2P1 | 0.18 | −0.52 | −0.67 | −0.37 | −0.41 | RN7SL320P | 0.25 | −0.55 | 1.07 | −0.54 | 1.75 |
| AC011444.2 | −0.76 | −0.29 | 1.03 | −0.41 | 0.48 | KRTAP10-7 | −1.14 | −0.10 | 0.13 | 0.42 | 0.28 | AL049779.3 | 0.07 | −0.96 | 1.92 | 0.19 | 1.61 |
| HPS1 | −0.22 | 0.12 | −0.09 | 0.24 | 0.03 | AC145285.1 | −0.39 | 0.14 | 0.35 | −0.29 | 0.29 | OSTCP1 | 0.22 | −0.65 | 0.29 | −0.11 | −1.30 |
| AL356512.1 | −1.02 | 0.62 | 0.77 | 0.00 | 0.27 | AL136231.1 | 0.39 | 0.59 | −0.02 | 0.26 | 0.34 | AC022882.1 | 0.40 | −1.57 | −1.10 | −0.83 | −0.58 |
| BDH1 | 0.35 | 0.06 | −0.30 | 0.06 | −0.11 | MEDAG | −0.29 | 0.23 | 0.28 | −0.07 | −0.49 | OR13C2 | 0.42 | −1.31 | 0.04 | 0.02 | −0.28 |
| AL603756.1 | 0.58 | −0.40 | −0.66 | 0.16 | −0.20 | AL589986.2 | 0.30 | −0.41 | 0.91 | −0.17 | 1.24 | RPSAP11 | −0.12 | 0.58 | −0.37 | 0.33 | −0.62 |
| LINC00536 | −1.03 | 0.12 | 0.83 | −0.26 | −0.57 | AL928711.1 | −0.49 | −0.35 | 0.77 | 0.57 | 1.00 | IGHV1-8 | 0.42 | −0.24 | −0.04 | −0.44 | −0.37 |
| AC008438.1 | −0.55 | 0.19 | 0.67 | 0.14 | 0.34 | AC008170.1 | −0.37 | 0.81 | −0.44 | 0.36 | −0.29 | LINC01688 | 0.42 | −0.94 | −1.27 | −0.86 | −0.25 |
| AL627311.1 | 0.95 | −0.03 | −0.33 | −0.35 | −0.99 | PPM1E | 0.26 | −0.19 | −0.18 | 0.41 | 0.07 | ELOBP2 | 0.42 | −0.92 | −0.62 | −0.41 | 0.02 |
| ARL17B | −0.61 | 0.01 | 0.71 | 0.03 | 0.72 | AL136439.1 | 0.69 | −1.84 | −0.80 | −0.07 | 0.75 | OR10P1 | 0.30 | −0.36 | −1.18 | 0.00 | −0.42 |
| AC034234.1 | −1.41 | 1.35 | 1.61 | −0.25 | −0.27 | AP4B1-AS1 | 0.24 | −0.43 | 0.72 | −0.15 | 0.67 | MIR196A2 | 0.10 | 0.50 | 0.48 | −0.12 | −0.40 |
| SMIM25 | 0.97 | −1.11 | −2.11 | −0.11 | −1.70 | LINC02393 | 0.72 | 0.14 | −1.85 | 0.91 | −1.88 | AL139294.1 | 0.07 | 0.07 | 0.19 | 0.48 | 0.33 |
| CD46 | −0.22 | 0.13 | 0.10 | 0.12 | 0.07 | AP000873.2 | −0.13 | −0.02 | 0.26 | 0.04 | 0.14 | AL357054.4 | 0.03 | −0.50 | −0.70 | −0.10 | −0.24 |
| DUBR | −0.35 | 0.14 | 0.36 | 0.21 | 0.16 | LINC01096 | −0.66 | −0.37 | 0.32 | −0.36 | 0.06 | AC135178.3 | −0.03 | 0.16 | −0.07 | 0.10 | 0.22 |
| AC091946.1 | −1.21 | −0.07 | 0.69 | 0.01 | 0.59 | AC006511.3 | 0.41 | −0.16 | −0.20 | −0.12 | −0.28 | AC020910.2 | −0.09 | −0.50 | 2.07 | 0.88 | 2.08 |
| RNA5SP370 | −1.28 | 0.65 | −1.39 | 1.77 | −1.13 | SENP6 | 0.06 | 0.05 | −0.03 | 0.04 | −0.06 | AC104454.2 | −0.16 | −1.18 | 0.85 | −0.54 | 0.77 |
| GARNL3 | −0.27 | 0.13 | 0.04 | 0.26 | 0.25 | AC090666.1 | 0.23 | −0.12 | −0.05 | −0.01 | −0.35 | RNASE2 | 0.04 | 0.04 | 1.30 | −0.21 | 0.08 |
| SNORD93 | 1.21 | −0.75 | −1.36 | −0.82 | −1.91 | AC048341.1 | −0.09 | −0.11 | −0.13 | −0.10 | −0.01 | SEC61A2 | 0.01 | −0.07 | −0.01 | 0.00 | 0.07 |
| RNU1-98P | −1.27 | 0.01 | −0.44 | 0.46 | −0.08 | LINC01108 | 0.30 | −0.67 | −0.71 | −0.36 | −0.10 | PIP5K1C | 0.01 | 0.03 | −0.17 | 0.08 | −0.02 |
| RPS19BP1 | 0.24 | −0.19 | −0.23 | −0.21 | −0.15 | PPP1R16B | 0.19 | −0.25 | 0.08 | −0.21 | 0.07 | MTND3P22 | −0.11 | −0.52 | 0.35 | −0.39 | −0.02 |
| GATD1 | −0.28 | −0.07 | −0.20 | 0.16 | 0.20 | AC009302.1 | 0.67 | 1.08 | −0.21 | 0.73 | −0.79 | RNU2-53P | −0.42 | 1.13 | 0.06 | −0.41 | −0.27 |
| IRX2 | 0.33 | 0.13 | −0.71 | 0.34 | −0.15 | AC007922.2 | 0.31 | −0.36 | −0.22 | 0.10 | 0.53 | AC013470.1 | 0.22 | −1.08 | −0.81 | 1.90 | 1.16 |
| COL8A1 | −0.60 | 0.50 | 0.16 | −0.19 | −0.51 | AC089998.1 | −0.80 | −0.62 | 0.88 | −0.05 | −1.00 | AP000894.3 | −0.42 | 0.78 | −0.19 | 0.82 | −0.96 |
| DUOX1 | 0.48 | −0.24 | −0.73 | 0.09 | −0.08 | SH2D3C | 0.18 | −0.26 | 0.03 | −0.12 | −0.18 | FPGT | 0.02 | 0.17 | 0.46 | 0.19 | 0.24 |
| AL512444.1 | 1.57 | −1.27 | 0.38 | 0.06 | 0.64 | OR14K1 | 0.93 | −0.70 | 0.96 | 1.42 | 1.31 | LINC01185 | 0.06 | −0.54 | −1.09 | −0.14 | −0.71 |
| AC016924.1 | −2.15 | −0.04 | 1.80 | −0.85 | −0.05 | AC007368.1 | 0.51 | 0.21 | −0.88 | 0.19 | −1.18 | AC023161.1 | −0.33 | 0.14 | −1.27 | 1.08 | −0.56 |
| DUS1L | −0.41 | −0.03 | −0.32 | 0.30 | 0.20 | GALNT9 | −0.55 | −0.02 | −1.26 | 0.48 | −0.83 | AC010328.1 | 0.08 | −1.05 | 0.22 | 0.21 | 0.42 |
| AL357752.1 | 2.45 | −1.17 | −1.88 | −0.37 | −1.49 | CBX3P2 | 0.23 | −0.27 | 0.30 | 0.27 | 0.10 | AC026333.1 | 0.19 | 0.11 | 1.23 | −1.34 | −0.04 |
| AC136621.1 | −1.02 | 0.52 | 0.65 | 0.14 | 0.52 | PBX2P1 | −0.36 | 0.46 | 0.71 | 0.18 | 0.15 | AC092685.1 | −0.33 | 0.06 | −0.41 | 1.47 | −0.73 |
| PNPLA8 | 0.39 | 0.07 | −0.36 | −0.07 | −0.62 | SPATA1 | 0.14 | 0.02 | −0.18 | 0.08 | −0.19 | AC118465.1 | −0.04 | 0.19 | 0.70 | −0.02 | 0.02 |
| AL358472.2 | 0.84 | −0.59 | 0.53 | −0.47 | 0.38 | AL031719.1 | −0.33 | 0.37 | −0.25 | 0.54 | −0.06 | LINC01203 | 0.08 | −0.39 | 1.00 | 1.07 | −0.10 |
| PSMC1P4 | 1.82 | −0.99 | −1.98 | −0.27 | −0.92 | AC099335.1 | −0.72 | −0.35 | 1.11 | 0.26 | 0.57 | PRELID2P1 | 0.11 | −0.54 | −1.29 | 1.09 | −1.02 |
| AC005783.1 | −1.77 | −1.46 | 1.18 | 0.57 | 2.73 | KLHL12 | −0.06 | 0.01 | 0.15 | 0.06 | 0.14 | CASC22 | −0.12 | 0.00 | −2.06 | 0.88 | −2.55 |
| KRT8P31 | −0.59 | 0.80 | 0.97 | 0.28 | 0.15 | AC098869.1 | 0.41 | −0.42 | −0.31 | −0.13 | 0.22 | AC140847.1 | 0.14 | −1.09 | −0.18 | 0.67 | 0.39 |
| PRPF39 | 0.28 | 0.06 | 0.00 | 0.08 | −0.07 | AL121970.1 | −0.34 | −0.39 | 1.11 | −0.39 | −0.21 | MRPS21P7 | −0.25 | 0.36 | 1.78 | 0.40 | 0.55 |
| AC097381.3 | −0.82 | −0.13 | 0.15 | 0.29 | 0.96 | AC068700.1 | 0.26 | −0.10 | −0.07 | 0.43 | −0.09 | AC007920.1 | 0.13 | −0.43 | −0.50 | 0.89 | −1.09 |
| EMC7 | 0.30 | 0.11 | −0.10 | −0.02 | −0.32 | AC060780.3 | 0.52 | 0.25 | 0.24 | −0.23 | −0.47 | NUTF2P6 | −0.04 | −0.27 | −0.14 | 0.24 | 0.34 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| RFFL | 0.27 | −0.04 | −0.36 | −0.05 | −0.10 | IGHV1-3 | 1.52 | 2.25 | −0.31 | 0.11 | −1.52 | RMDN1 | 0.01 | −0.05 | 0.05 | −0.14 | −0.01 |
| AC008555.2 | −0.75 | 0.60 | 0.49 | 0.65 | 0.46 | ABHD17A | −0.11 | 0.22 | 0.11 | 0.09 | −0.03 | MTCYBP5 | −0.15 | −0.33 | −0.32 | 0.40 | −2.00 |
| AC004696.1 | −1.11 | 0.54 | 3.50 | −0.51 | −0.01 | RN7SKP90 | −0.26 | 0.44 | −0.03 | 0.22 | −0.10 | AP003481.1 | 0.16 | −0.96 | −1.59 | 1.80 | 0.73 |
| NAT9 | −0.36 | −0.17 | 0.00 | 0.06 | 0.25 | FABP2 | 0.49 | −1.18 | −0.87 | 0.20 | 0.29 | G31094 | 0.20 | −0.21 | −0.35 | −0.60 | 2.11 |
| NUMB | 0.18 | −0.02 | −0.09 | −0.11 | −0.07 | MPP1 | −0.12 | 0.09 | 0.15 | −0.17 | −0.26 | AC090079.1 | −0.42 | 0.49 | −1.13 | 1.28 | 0.24 |
| SAR1AP2 | 1.52 | −1.17 | −0.47 | −0.71 | −0.01 | AC139451.1 | 0.27 | −0.12 | 0.54 | −0.35 | 0.10 | DHFRP6 | 0.42 | −0.80 | 0.99 | 1.30 | 0.41 |
| AC020951.1 | −0.58 | 0.48 | 1.38 | −0.01 | 0.43 | AC073528.1 | −1.13 | 0.45 | 0.97 | 1.01 | 1.02 | IFT22 | −0.01 | −0.07 | −0.15 | −0.07 | −0.14 |
| AC105114.1 | −0.74 | 0.83 | 0.79 | −0.16 | 0.34 | KIF5A | −0.31 | 0.39 | 0.22 | 0.15 | 0.29 | LINC01714 | −0.13 | −1.95 | −0.57 | −0.71 | 0.17 |
| AC090206.1 | −1.13 | −0.09 | 0.56 | 0.28 | 0.76 | G25497 | −0.47 | −0.15 | −0.74 | 0.53 | −0.49 | AC091729.2 | 0.06 | 0.68 | −0.81 | 0.23 | −0.11 |
| LMO1 | −0.82 | 0.22 | 0.43 | 0.49 | 0.06 | AC022182.2 | −0.62 | 0.65 | −0.18 | −0.21 | −0.42 | HNRNPKP3 | 0.11 | −0.72 | −0.55 | 1.51 | 1.37 |
| LRRTM3 | −1.10 | 0.08 | 0.95 | 0.60 | 0.64 | RN7SL307P | 0.73 | −1.87 | −0.70 | −0.31 | 0.86 | RPL34P33 | −0.06 | −0.81 | 0.44 | −0.95 | 0.71 |
| REM1 | −0.81 | 0.57 | 1.09 | 0.02 | −0.31 | ATP11A | −0.07 | 0.01 | −0.10 | 0.02 | −0.04 | RNU6-723P | −0.12 | −0.51 | 1.40 | −0.01 | 1.21 |
| LINC00475 | −0.78 | 0.53 | −0.15 | −0.07 | −0.18 | AL356272.1 | 1.13 | −0.78 | 0.28 | −1.49 | −0.72 | AL358334.3 | 0.03 | −0.43 | −0.91 | −0.27 | −0.16 |
| CDC7 | −0.56 | −0.08 | 0.53 | −0.14 | 0.47 | RFPL3 | 0.43 | −1.37 | 0.25 | −0.45 | −1.10 | AL139008.2 | −0.20 | 0.01 | 0.26 | −0.44 | −0.44 |
| G32185 | 1.44 | −0.49 | −1.25 | 0.35 | −0.37 | NCR2 | 1.12 | −1.11 | −1.87 | −0.13 | −1.54 | AL109810.2 | −0.21 | 0.11 | −0.21 | 0.24 | −1.44 |
| RN7SKP48 | −1.01 | 0.37 | −0.29 | 0.43 | 0.40 | AC096664.2 | −0.53 | −1.80 | 0.86 | −0.48 | 2.46 | IGLV3-25 | 0.23 | 0.30 | 0.28 | 1.19 | 2.54 |
| ABHD14B | −0.37 | 0.47 | 0.52 | 0.24 | −0.10 | LINC01560 | 0.20 | 0.31 | 0.08 | 0.15 | 0.06 | GC | 0.09 | −1.13 | −1.60 | 0.57 | −0.56 |
| NPIPB6 | −1.39 | 0.58 | 2.20 | −0.31 | 0.54 | GJA10 | 0.92 | −0.20 | −0.35 | 0.29 | −1.60 | AL365214.1 | 0.18 | −0.54 | −2.89 | 1.07 | −2.51 |
| AC004467.1 | −1.20 | 0.40 | 0.38 | 0.31 | −0.27 | LINC02436 | −0.64 | −1.42 | 1.38 | 0.58 | 0.33 | AKR1C7P | −0.05 | 0.51 | −0.57 | −0.45 | −0.91 |
| ICE1 | 0.21 | −0.11 | −0.21 | −0.10 | −0.07 | AC010997.1 | 0.91 | −0.27 | −0.11 | −1.19 | −0.78 | FLJ40288 | 0.13 | −0.61 | −1.01 | −0.22 | −0.96 |
| CNTNAP1 | −0.44 | −0.08 | 0.28 | −0.04 | 0.05 | MTCO2P17 | 0.83 | −1.45 | −0.03 | 0.37 | 1.30 | BX322635.1 | 0.06 | −1.36 | 1.71 | 0.24 | 0.36 |
| IRF3 | −0.41 | 0.16 | 0.08 | 0.29 | 0.24 | LINC01241 | −0.68 | 1.02 | 0.47 | −0.29 | −1.48 | AL160162.1 | −0.42 | −0.51 | −0.42 | −0.79 | −0.04 |
| AC011411.1 | −0.76 | −0.59 | 0.34 | −0.24 | 0.80 | AF165147.1 | −0.24 | −0.31 | 0.36 | −0.43 | −0.09 | AL080276.1 | 0.22 | −0.33 | −0.88 | 1.36 | −0.45 |
| CR769775.1 | −1.87 | 0.78 | 1.95 | −0.39 | 0.56 | RNU4-22P | 0.42 | 0.62 | 0.89 | −0.07 | −0.54 | LINC00621 | 0.13 | −0.35 | 2.38 | 0.66 | 1.33 |
| LRRC8B | 0.49 | −0.36 | −0.34 | −0.09 | −0.18 | NCAPD3 | 0.10 | −0.25 | −0.21 | −0.09 | 0.05 | RN7SL15P | 0.03 | −0.19 | −0.39 | 0.12 | −0.07 |
| GLYATL1P1 | −1.09 | 0.15 | 1.70 | −0.64 | 1.14 | RPL19P18 | −1.32 | −0.09 | 1.31 | 0.01 | 1.03 | RN7SL497P | −0.42 | 0.69 | NA | −0.81 | −2.05 |
| PPP6C | 0.36 | −0.06 | −0.28 | −0.07 | −0.34 | RPL31P20 | 0.46 | −0.94 | −0.39 | 0.19 | −0.03 | ITLN1 | −0.13 | −0.94 | −1.38 | 2.63 | −1.07 |
| AC243829.4 | 1.34 | −1.27 | −1.21 | −0.03 | −0.06 | AL137009.1 | 0.24 | −0.15 | −0.10 | −0.20 | −0.32 | AL033530.1 | −0.09 | 1.22 | −1.98 | 1.53 | −2.03 |
| AP000704.1 | −0.77 | −0.16 | −0.01 | 0.05 | 0.44 | LINC00272 | −0.66 | 0.26 | 0.80 | −0.26 | −0.42 | LINC02135 | −0.14 | −1.53 | −1.77 | 0.90 | 0.47 |
| AP000695.1 | 0.89 | −1.03 | −1.21 | −0.68 | −0.32 | AL161421.1 | 0.32 | 0.08 | −0.53 | 0.14 | −0.35 | AC097717.1 | −0.03 | 0.15 | 0.33 | 0.10 | −0.13 |
| IGSF11-AS1 | −1.27 | −1.01 | 0.73 | −0.24 | 0.90 | SLFN13 | −0.13 | 0.04 | −0.05 | −0.05 | 0.11 | DDR1-DT | 0.06 | −1.37 | −0.60 | −0.32 | 0.68 |
| PRADC1P1 | −1.02 | 0.22 | 1.16 | 0.28 | 0.48 | AL591686.2 | −0.84 | −1.23 | 0.02 | −0.24 | −0.21 | LYST-AS1 | 0.02 | −0.11 | 0.13 | −0.11 | 0.34 |
| DNPH1 | 0.28 | −0.01 | −0.38 | 0.09 | −0.30 | AL139333.1 | 0.37 | 0.13 | −0.22 | 0.00 | −0.28 | FAM172BP | 0.23 | −0.32 | −0.47 | 1.04 | 0.52 |
| RFWD2P1 | −0.85 | 0.58 | 0.84 | 0.24 | −0.25 | AC244131.2 | 0.41 | −0.26 | 0.43 | 0.17 | 0.42 | LINC00615 | 0.15 | −0.63 | 2.15 | 0.68 | 0.34 |
| OAT | 0.42 | −0.04 | −0.14 | −0.03 | −0.30 | CRABP1 | −0.52 | −0.03 | −0.55 | −0.17 | 0.46 | IGHV3-79 | −0.41 | −0.47 | 0.69 | 1.94 | 1.17 |
| PKNOX1 | 0.21 | −0.19 | −0.14 | −0.21 | 0.02 | BICRA | −0.12 | 0.04 | −0.04 | 0.20 | 0.10 | PTP4A2P1 | 0.05 | −0.63 | −0.16 | −0.68 | −0.01 |
| DNAH10OS | −0.64 | 0.47 | 0.57 | 0.13 | 0.46 | G28331 | 0.16 | −0.09 | 0.10 | −0.17 | 0.12 | RPL7P30 | −0.41 | 0.21 | −0.16 | −0.50 | −1.09 |
| AC096536.1 | 1.18 | 0.04 | −0.24 | 0.32 | −0.46 | AC004471.1 | −0.37 | 0.56 | 0.47 | 0.35 | 0.12 | AC244035.1 | 0.41 | 0.64 | 0.15 | 0.69 | −0.20 |
| MIR3682 | 1.20 | −0.15 | 0.43 | −0.04 | 0.13 | ANKRD9 | 0.09 | 0.12 | −0.43 | 0.11 | −0.27 | MTND5P21 | 0.15 | −0.53 | −0.77 | 0.57 | 0.84 |
| AC126773.2 | 1.07 | −1.54 | −3.05 | −0.16 | −1.40 | AP000646.1 | 0.55 | −0.02 | 1.01 | 0.25 | 0.00 | AC012506.1 | −0.37 | 0.68 | 0.84 | −0.05 | 0.33 |
| AP000280.1 | −1.47 | 1.17 | 0.53 | 0.13 | 0.04 | AC145285.5 | −1.18 | 0.34 | 0.08 | −1.70 | −2.29 | ACTR3BP6 | −0.40 | −1.06 | 0.77 | −1.43 | −0.87 |
| AC011462.4 | −0.74 | 0.00 | 0.99 | −0.10 | 0.57 | NPM1P21 | 0.48 | 0.10 | −1.61 | 0.37 | −0.74 | AP000356.3 | 0.17 | 0.72 | 1.69 | 1.24 | 1.12 |
| AMBP | −1.12 | −0.11 | 0.51 | 0.13 | 0.38 | AL109930.1 | −0.54 | 0.49 | 2.84 | −1.31 | 0.20 | AL590096.1 | 0.06 | 0.50 | 0.93 | −0.04 | −0.17 |
| SF3B1 | 0.21 | 0.01 | −0.10 | −0.08 | −0.11 | AL121759.1 | −0.22 | 0.18 | 0.35 | −0.12 | −0.13 | RPS2P41 | −0.04 | 0.44 | −0.21 | 0.29 | 0.01 |
| PRPF3 | −0.24 | 0.05 | 0.05 | −0.02 | 0.05 | AC008083.3 | 0.76 | −0.77 | −1.48 | 0.53 | 0.28 | RN7SL21P | 0.05 | −0.09 | −0.52 | 0.56 | −0.45 |
| AC018889.1 | 0.74 | −0.63 | 0.38 | 0.00 | 0.18 | AC018645.2 | 0.25 | −0.05 | −0.21 | 0.60 | 0.25 | RPL6P29 | 0.24 | −0.53 | 0.38 | −2.46 | −0.40 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| BCL11B | 0.50 | −0.03 | −0.38 | 0.09 | −0.12 | AP003385.1 | 1.72 | −1.58 | −3.18 | 0.60 | −1.11 | RN7SL636P | −0.20 | 0.26 | −0.34 | −0.81 | −0.55 |
| LINC01124 | −1.40 | 0.48 | 2.05 | 0.43 | 0.93 | LINC02471 | −0.47 | −0.01 | −0.48 | 0.25 | 0.05 | RN7SKP198 | −0.05 | 0.23 | 1.59 | −0.33 | 0.04 |
| AC008740.1 | −0.56 | 0.17 | 0.29 | −0.09 | 0.25 | AP006545.1 | 0.29 | −0.45 | 0.10 | −0.38 | 0.10 | LINC02441 | 0.41 | −0.96 | −1.11 | −0.22 | −0.75 |
| AC023794.3 | −0.68 | 0.61 | 0.27 | 0.44 | −0.14 | AP001269.2 | 0.68 | −0.86 | 0.85 | 0.99 | 1.47 | ACAA1 | −0.01 | −0.08 | −0.41 | 0.09 | −0.05 |
| CXCL6 | 2.03 | −2.56 | −4.12 | 0.60 | −2.23 | AC004466.1 | 0.61 | 0.36 | −3.31 | 0.03 | −1.90 | AC012512.1 | 0.33 | −0.22 | −0.69 | 1.18 | 0.67 |
| ASIC1 | −0.58 | 0.07 | 0.19 | 0.38 | 0.50 | AL031717.1 | 0.27 | 0.34 | 0.29 | 0.21 | −0.27 | MTND1P10 | −0.10 | −1.07 | 0.72 | −1.43 | 2.35 |
| MICAL3 | −0.30 | −0.09 | −0.14 | 0.08 | 0.29 | RPL3P5 | 0.60 | −0.92 | 0.01 | −0.51 | 0.28 | IGLV7-46 | −0.41 | −0.12 | 0.49 | 0.51 | −0.83 |
| HSPD1P3 | 2.72 | −0.90 | −3.35 | 1.59 | −4.46 | LCNL1 | −0.37 | −0.10 | 0.86 | 0.24 | 0.81 | FLJ13224 | −0.04 | −0.04 | −0.71 | 0.18 | −0.46 |
| G19170 | 0.91 | −0.29 | 0.87 | −0.31 | 0.44 | AC131206.1 | −0.24 | 0.29 | 0.29 | −0.19 | −0.11 | LINC02029 | −0.08 | 0.37 | −0.91 | 0.74 | 0.06 |
| GYPB | −1.12 | −0.75 | 0.12 | 0.24 | −0.09 | KRT128P | −0.38 | 1.73 | 1.69 | 0.35 | −0.19 | RPL5P29 | 0.10 | 0.31 | 0.78 | 0.08 | −0.19 |
| SNRPGP3 | 2.29 | −0.80 | −2.03 | 0.37 | −1.48 | AC005906.3 | 0.76 | −1.07 | −0.78 | −1.72 | −1.04 | AC020923.1 | 0.41 | −0.17 | −1.98 | 1.44 | −1.12 |
| HERC2 | −0.14 | −0.04 | 0.00 | 0.07 | 0.15 | RNY3P2 | 0.66 | −0.69 | −0.22 | 0.59 | 1.39 | PENK | −0.05 | −0.32 | −1.40 | 0.44 | −0.20 |
| ANGPTL1 | −0.54 | 0.72 | 1.01 | 0.14 | −0.08 | MCOLN2 | 0.26 | −0.79 | −0.25 | −0.64 | −0.02 | SCYGR2 | −0.41 | −0.79 | 0.26 | −1.41 | −0.57 |
| SLC10A7 | 0.32 | −0.25 | −0.10 | −0.17 | 0.07 | DSCR9 | −0.25 | 0.31 | 0.48 | 0.01 | 0.03 | PTK6 | −0.02 | 0.18 | −0.13 | 0.23 | −0.01 |
| LINC02001 | 0.41 | −0.60 | −0.29 | −0.13 | 0.17 | RNA5SP248 | −0.70 | −1.67 | 0.87 | −0.96 | 1.05 | AL157398.1 | 0.06 | 1.03 | 0.49 | 0.38 | 0.30 |
| POLRMT | −0.36 | 0.25 | 0.00 | 0.23 | 0.10 | MAP1LC3B2 | −0.23 | 0.34 | −0.80 | 0.40 | −0.45 | AC091193.1 | −0.41 | 0.16 | −0.49 | −0.08 | −0.25 |
| G39663 | −1.88 | 0.40 | 2.78 | −0.31 | 1.00 | CDH11 | −0.19 | 0.06 | 0.85 | −0.89 | −0.08 | AL031432.1 | −0.07 | −0.13 | −0.18 | −0.32 | 0.85 |
| RPS27AP16 | 0.57 | −0.24 | −0.09 | −0.12 | −0.47 | AC140061.9 | −0.75 | −0.21 | 1.91 | −1.16 | 0.82 | SSXP1 | 0.24 | −0.99 | −0.37 | 2.37 | −0.10 |
| G38918 | −0.65 | 0.43 | 0.06 | 0.45 | −0.06 | PDPK1 | 0.07 | 0.16 | −0.02 | 0.00 | −0.20 | RNU7-167P | −0.41 | 0.07 | −0.68 | 0.44 | −0.83 |
| RNU6-748P | 1.07 | −1.01 | −1.01 | −0.27 | −0.10 | AL445423.1 | −1.33 | 0.42 | 0.06 | 1.37 | −1.16 | RN7SL28P | 0.41 | −1.68 | 0.78 | −1.74 | 0.90 |
| AP000808.1 | −0.86 | 0.40 | 0.97 | −0.33 | −0.31 | PRR34-AS1 | 0.21 | 0.12 | −0.16 | 0.16 | −0.12 | AC018552.1 | 0.41 | −1.95 | 0.43 | −1.39 | 0.36 |
| AC078789.1 | −1.60 | −0.98 | 3.09 | −1.84 | 1.89 | RNU6-564P | 0.56 | 1.04 | 0.54 | 0.02 | −1.01 | AC137695.2 | −0.32 | 0.83 | −0.62 | 0.30 | −1.44 |
| AC079177.1 | −1.40 | −0.52 | −0.17 | 0.82 | 0.58 | AC004854.2 | −0.17 | −0.22 | 0.10 | −0.05 | 0.17 | AC125421.2 | 0.23 | −0.71 | 0.01 | 0.31 | 1.80 |
| AL133244.1 | 1.93 | −0.96 | 0.00 | −0.42 | 0.21 | AC016642.1 | 0.72 | −0.06 | −0.03 | 0.69 | 0.67 | OR7E36P | −0.39 | −1.04 | NA | −1.36 | −0.72 |
| ARPC3P2 | −1.23 | 0.15 | 1.41 | 0.06 | −0.17 | KCNK13 | 0.40 | −1.49 | −0.54 | −0.58 | −0.29 | AL022725.1 | 0.14 | 0.11 | 0.82 | −0.14 | 0.06 |
| EED | 0.23 | −0.14 | −0.16 | −0.09 | 0.01 | FAM185A | −0.10 | 0.02 | 0.15 | −0.15 | 0.26 | AC008105.3 | −0.04 | −0.71 | −0.20 | −0.58 | 0.54 |
| FAM162B | −0.99 | 0.39 | 1.28 | 0.27 | −0.11 | AC026355.3 | −1.13 | 1.22 | 2.62 | 0.77 | 0.84 | HYAL1 | 0.02 | 0.30 | −0.04 | 0.24 | −0.16 |
| AL353593.2 | −0.71 | 0.56 | 0.47 | 0.08 | 0.28 | OFCC1 | 0.30 | 0.05 | −0.20 | 0.02 | 0.27 | NNMT | −0.03 | −0.39 | 0.44 | −0.73 | −0.28 |
| ACAD8 | −0.28 | 0.29 | 0.41 | 0.22 | 0.16 | AC092468.1 | −0.61 | −0.45 | 1.43 | −0.29 | −0.28 | AC104051.2 | −0.08 | −1.07 | −0.58 | 0.53 | −1.03 |
| GRIPAP1 | −0.30 | 0.05 | −0.10 | 0.11 | 0.06 | AL008721.1 | −0.54 | −0.77 | −0.22 | −0.31 | −0.86 | SLC6A3 | −0.08 | 0.23 | −1.07 | −0.78 | −1.90 |
| IFT57 | 0.27 | −0.09 | −0.17 | −0.07 | −0.31 | AC027313.1 | −0.77 | 1.51 | 0.73 | 1.43 | −1.33 | LINC01338 | 0.11 | −0.65 | 2.17 | −0.48 | 0.66 |
| EPX | −0.87 | 0.79 | 0.41 | −0.22 | −0.40 | AP003696.1 | −0.17 | −0.45 | −0.01 | −0.37 | 0.04 | OR4A41P | −0.17 | −1.27 | −0.15 | 1.07 | 0.92 |
| SNRPEP4 | 1.00 | −0.20 | −0.44 | 0.41 | 0.01 | AC134682.1 | −0.38 | 0.52 | 0.37 | 1.43 | 0.36 | AL137014.1 | −0.41 | 0.30 | 0.62 | −0.36 | −1.85 |
| RSPH9 | −0.52 | 0.42 | 0.32 | 0.20 | 0.15 | AC103726.1 | −0.51 | −0.44 | 1.13 | 0.61 | 1.48 | CCDC112 | −0.01 | 0.08 | 0.12 | 0.05 | 0.12 |
| PTMAP4 | 0.56 | −0.02 | −0.07 | −0.01 | −0.14 | AL590426.2 | −0.60 | 0.18 | 1.10 | 0.49 | 0.75 | AC002486.2 | −0.18 | −0.94 | 1.47 | 1.19 | 0.90 |
| AC011445.2 | 0.94 | −0.52 | −1.02 | −0.03 | −1.23 | AP000484.1 | −1.10 | 1.18 | −0.44 | 0.26 | −0.99 | G9021 | −0.15 | 0.53 | 2.89 | 0.85 | 0.29 |
| PLCB1 | −0.49 | 0.35 | 0.62 | −0.07 | 0.09 | AL136164.1 | −0.47 | 0.95 | 0.56 | 0.63 | −0.13 | SLC16A1P1 | −0.10 | 0.45 | −0.58 | 0.08 | −0.81 |
| PDE1C | −0.72 | 0.54 | 0.24 | 0.08 | −0.38 | AC116651.1 | 0.30 | −0.33 | −0.36 | −0.05 | −0.02 | AP006587.2 | 0.41 | −0.17 | −1.39 | −0.21 | −1.89 |
| AC138866.1 | −0.81 | 0.37 | 0.92 | 0.09 | 0.78 | MAPK8IP2 | 0.19 | 0.13 | −0.09 | 0.04 | 0.28 | AL031985.2 | 0.08 | −0.28 | −1.04 | −0.36 | −1.67 |
| ADGB | −0.85 | 0.03 | 0.83 | 0.20 | 0.67 | LINC01119 | −0.29 | −0.28 | −0.13 | −0.47 | −0.25 | AC010327.1 | 0.07 | 1.06 | −0.61 | 1.52 | −0.35 |
| C15orf65 | 0.90 | −0.07 | 0.36 | −0.29 | −0.24 | RPL13P6 | 0.29 | 0.07 | −0.14 | −0.04 | −0.82 | AL138709.1 | −0.28 | 1.21 | 0.38 | 1.38 | 0.01 |
| RBX1 | 0.34 | −0.13 | −0.05 | −0.20 | −0.17 | RNU6-1057P | 1.20 | −0.54 | 0.34 | 0.09 | 0.05 | AC020612.1 | 0.03 | 0.00 | 0.03 | 0.26 | 0.40 |
| ACTG2 | −0.82 | 0.06 | 0.31 | −0.26 | −0.45 | C22orf46 | −0.12 | −0.04 | −0.22 | −0.19 | −0.22 | AC004969.1 | −0.07 | −0.84 | 0.26 | −0.39 | 0.42 |
| ARRB1 | −0.29 | 0.22 | 0.22 | 0.19 | 0.17 | RP11-744K17.9 | 1.09 | 0.12 | −3.47 | 0.41 | −3.50 | PDGFA | −0.02 | −0.12 | −0.14 | −0.18 | 0.04 |
| AC006529.1 | 1.15 | −0.94 | −1.03 | −0.28 | −0.04 | AC007342.1 | 0.33 | −0.12 | −0.03 | −0.42 | −0.31 | C3orf56 | −0.41 | −1.13 | −0.24 | −1.48 | 0.00 |
| LINC02507 | 1.11 | −0.69 | −2.01 | 0.44 | −1.31 | DEFB135 | 0.70 | −2.43 | −1.04 | 0.13 | 0.49 | AL158825.1 | −0.41 | −0.34 | NA | −0.48 | −1.71 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| LINC01320 | −0.84 | 0.38 | −0.19 | 0.31 | −0.39 | GOT2P3 | −0.45 | 0.36 | −0.99 | 1.56 | −0.14 | LINC01904 | 0.25 | −0.43 | −0.01 | 0.25 | −0.67 |
| METTL2A | 0.21 | 0.01 | −0.08 | −0.06 | −0.12 | G39246 | −0.58 | −0.24 | 1.53 | −0.17 | −0.35 | ASAH2 | 0.05 | 0.26 | −0.24 | 0.06 | −0.75 |
| AC136443.5 | 1.11 | −0.29 | 0.20 | −0.29 | −0.25 | AC127024.4 | −0.15 | −0.23 | −0.33 | 0.33 | 0.39 | RNA5SP212 | 0.05 | −0.30 | −0.83 | 0.02 | 0.05 |
| G38234 | −0.75 | 0.41 | 0.16 | 0.30 | 0.08 | AC009518.1 | 0.65 | −1.22 | −1.55 | 0.12 | −0.91 | OR7A3P | −0.22 | −0.24 | −2.42 | 0.72 | −1.35 |
| AC008243.1 | 0.45 | −0.23 | −0.69 | 0.02 | −0.33 | RNU1-138P | −0.64 | 0.39 | −2.04 | 0.39 | −2.78 | CAGE1 | 0.04 | −0.81 | −1.11 | 0.14 | −0.46 |
| ADAMTS5 | −0.74 | 0.24 | 1.00 | −0.12 | −0.04 | HSD3B1 | −0.44 | −0.68 | −0.86 | 0.32 | 0.65 | MIR5189 | −0.12 | −0.75 | 0.33 | 0.49 | 2.65 |
| RHAG | −1.14 | 1.04 | 1.02 | 0.35 | 0.00 | AC006003.1 | 0.57 | −0.48 | 0.47 | 0.02 | 0.66 | RNU6-868P | 0.12 | 0.79 | 0.11 | −0.55 | −0.14 |
| MEP1B | −0.59 | 0.70 | 0.10 | 0.58 | −0.25 | PANTR1 | −0.62 | −0.16 | 0.06 | −0.02 | 0.41 | AC104465.1 | 0.41 | −1.09 | −0.89 | 0.07 | 0.30 |
| CCDC57 | −0.42 | −0.03 | −0.02 | 0.12 | 0.20 | AL356417.1 | 0.72 | −0.73 | −2.93 | 0.94 | −1.13 | CDV3P1 | −0.41 | −0.32 | 0.00 | 0.93 | −0.71 |
| SPHK2 | −0.50 | 0.26 | −0.24 | 0.32 | −0.08 | PLCL2-AS1 | −0.39 | 0.12 | 0.61 | −0.39 | 0.80 | AC111198.1 | −0.41 | −1.44 | 0.29 | −1.80 | −0.15 |
| LINC02470 | −1.64 | −0.54 | 0.69 | 0.48 | 1.17 | AC107464.3 | −0.56 | 0.64 | 0.76 | 0.13 | −0.53 | OR5F2P | −0.33 | 0.25 | −0.60 | 1.26 | −2.18 |
| DIABLO | −0.34 | 0.11 | 0.20 | −0.05 | 0.05 | AC145098.1 | 0.37 | −0.45 | −1.53 | −0.14 | −1.31 | C12orf73 | 0.01 | −0.17 | 0.32 | −0.20 | 0.21 |
| G22228 | 0.96 | −0.45 | −0.58 | −0.13 | −0.08 | AC008883.2 | −0.39 | −0.59 | 0.42 | −0.78 | 0.23 | AC003686.1 | 0.26 | −1.90 | −0.63 | −0.84 | 1.06 |
| HNRNPA1P54 | −0.91 | −0.44 | 0.08 | 0.06 | 1.06 | RPS19P3 | 0.21 | 0.07 | −0.07 | 0.01 | −0.17 | RPL7P60 | 0.10 | 1.23 | −0.88 | 0.42 | −1.05 |
| AC093151.2 | −1.14 | 0.51 | 1.14 | 0.35 | 0.68 | DHX36 | 0.05 | 0.00 | 0.02 | 0.00 | 0.08 | ODF1 | 0.41 | 0.42 | 0.39 | 0.24 | −1.64 |
| SDR39U1 | −0.48 | 0.45 | 0.55 | 0.39 | 0.18 | CYCSP52 | 0.35 | −0.01 | 0.25 | −0.52 | −0.35 | AL032821.1 | 0.19 | 0.30 | 0.67 | 0.46 | −1.22 |
| AC022144.1 | 0.62 | −0.98 | −0.53 | 0.08 | 1.00 | AC100793.1 | −0.34 | 0.51 | −0.22 | −0.49 | −0.01 | PPY | −0.38 | −0.05 | −0.21 | 1.14 | −0.55 |
| RN7SKP168 | 2.51 | −1.18 | −1.46 | 0.25 | 0.80 | GNMT | −0.27 | −0.02 | −0.15 | 0.22 | −0.37 | AC092447.6 | 0.41 | 0.66 | −1.10 | −0.63 | −2.28 |
| MUCL1 | −1.02 | 0.48 | 2.07 | 0.25 | 0.22 | AL136360.1 | 0.44 | 0.50 | 0.23 | 0.45 | 0.12 | AC104793.1 | 0.37 | 0.20 | −0.54 | −0.03 | −1.09 |
| ATCAY | −1.20 | −0.34 | −0.23 | 0.42 | 0.33 | AL590399.4 | −0.59 | 0.82 | 0.06 | 0.32 | −0.56 | AC096631.1 | −0.25 | −0.35 | −1.66 | 0.82 | 0.22 |
| CXCL9 | 1.33 | −2.37 | −0.58 | −3.40 | −0.93 | AC063932.1 | 0.38 | −0.42 | 0.43 | −0.22 | 0.68 | POLR2J2 | 0.02 | −0.58 | 0.08 | 0.58 | 1.06 |
| IL17RD | −0.40 | 0.53 | 0.58 | 0.13 | −0.05 | CENPCP1 | 0.27 | −0.10 | 0.15 | −0.15 | −0.49 | MRPS10P2 | −0.04 | −0.10 | 0.80 | 0.26 | 0.90 |
| C4BPA | −1.21 | 1.11 | 0.83 | 0.79 | 0.16 | AC008496.2 | −0.61 | 0.23 | −1.16 | 0.29 | −0.58 | AL133325.2 | 0.40 | −0.11 | −1.49 | 0.92 | −0.47 |
| ALDH9A1 | 0.33 | −0.12 | −0.52 | 0.13 | −0.32 | G16011 | 0.29 | 0.05 | 0.19 | 0.32 | −0.07 | MUSTN1 | 0.09 | −0.02 | 1.37 | −0.37 | 0.83 |
| AP001626.1 | −1.33 | 1.42 | 0.62 | 1.02 | −0.52 | MYO1F | −0.20 | −0.46 | 0.04 | −0.33 | 0.22 | PPP1R3A | −0.09 | 1.00 | −1.92 | 1.24 | −1.15 |
| RNU6-29P | −1.05 | 0.22 | −0.09 | 0.83 | −0.92 | ITIH3 | −0.30 | −0.28 | −0.26 | 0.71 | −0.32 | AC137590.2 | −0.16 | 0.65 | 0.29 | 0.28 | −1.77 |
| G4674 | 1.31 | −0.67 | −0.14 | −0.65 | 0.11 | POTEF | −0.67 | 1.23 | −2.60 | 2.05 | −3.36 | AC073429.2 | 0.23 | 0.33 | 0.10 | 0.37 | −0.85 |
| FAM183A | −0.50 | 0.40 | 0.54 | 0.27 | 0.53 | AC068790.5 | 0.22 | 0.29 | 0.17 | −0.44 | −0.54 | OR2W1 | −0.11 | −1.39 | 0.38 | −0.16 | −1.04 |
| BNIP3 | 0.50 | −0.38 | −0.71 | 0.07 | −0.33 | AC006538.1 | −0.43 | 0.15 | 1.55 | −0.64 | −0.49 | NDUFA5P9 | −0.40 | −0.34 | NA | −1.35 | −1.63 |
| AC027682.4 | −0.51 | 0.04 | 0.13 | 0.13 | 0.49 | POM121L4P | −0.98 | 0.29 | 0.35 | 0.09 | −0.88 | HNRNPFP1 | 0.37 | −1.38 | −0.27 | −1.23 | −1.93 |
| DSTNP2 | 0.50 | −0.33 | −0.61 | −0.25 | −0.06 | NIP7P3 | 0.26 | −0.31 | 0.14 | −0.18 | −0.05 | OR7E109P | −0.21 | −1.23 | −0.42 | −0.32 | 0.24 |
| SNORD6 | 0.75 | −0.38 | −0.59 | −0.27 | −0.66 | LINC02468 | −0.68 | −0.54 | 1.70 | −0.26 | 0.08 | AL162574.3 | −0.40 | 0.32 | −0.49 | 0.23 | −0.72 |
| AC010487.1 | −0.77 | 0.37 | 1.26 | −0.51 | −0.03 | RPL14P3 | −0.32 | −0.22 | 0.62 | 0.33 | 1.00 | AC091588.3 | 0.12 | −0.29 | 1.38 | 1.12 | 1.01 |
| ALDOB | −1.08 | 0.88 | 0.85 | 0.22 | −0.33 | RNU2-69P | 0.59 | 0.45 | 0.55 | −0.26 | −0.84 | AC104233.1 | 0.15 | 0.23 | 0.37 | −0.12 | −0.74 |
| GDE1 | 0.45 | −0.06 | 0.08 | 0.07 | −0.15 | AC103770.1 | −0.64 | 0.35 | −1.14 | 0.15 | −0.17 | FN1 | 0.03 | −0.03 | 0.71 | −0.92 | −0.20 |
| SELENOM | −0.58 | 0.21 | 1.06 | −0.43 | 0.15 | AL022328.3 | 0.29 | −0.32 | −0.14 | −0.12 | 0.54 | AC092296.2 | 0.13 | 0.39 | −0.51 | 0.61 | −0.76 |
| IMPDH1P11 | −1.38 | −0.21 | 1.05 | 0.77 | 1.19 | RPS29P3 | 1.11 | −0.56 | −0.11 | 0.44 | 1.02 | AF111167.2 | 0.03 | −0.08 | −0.04 | 0.48 | −0.54 |
| NPAP1 | −1.29 | −0.40 | −0.03 | 0.32 | −0.17 | ATP8A2P2 | 0.21 | 0.21 | 0.06 | 0.17 | −0.29 | RPL31P13 | −0.40 | −0.33 | 0.37 | −0.57 | 0.93 |
| PCDHAC1 | −1.05 | −0.03 | 0.07 | 0.75 | 0.39 | AC068802.1 | −0.65 | 1.17 | −0.52 | 1.62 | 0.48 | SLC25A52 | −0.09 | 0.40 | 2.51 | −0.41 | 0.36 |
| NBPF9 | −0.19 | 0.04 | 0.22 | −0.11 | 0.10 | AP005671.1 | −0.34 | 0.66 | 0.44 | −0.01 | −0.39 | AC022960.2 | 0.05 | 0.28 | 0.53 | −0.16 | 0.08 |
| RGS14 | 0.35 | −0.33 | −0.55 | 0.12 | 0.03 | CD40LG | 0.32 | −0.06 | 0.25 | −0.38 | 0.13 | AC010458.1 | −0.28 | −0.94 | −0.19 | 0.42 | 1.59 |
| AL596202.1 | −0.46 | −0.09 | 0.74 | −0.09 | 0.65 | AC036164.1 | 0.28 | −0.27 | −0.01 | −0.09 | 0.06 | LINC01923 | 0.08 | −0.14 | −0.81 | 0.01 | −0.27 |
| IGFBP5 | −0.86 | 0.62 | 1.30 | 0.13 | 0.31 | HIST1H2APS3 | 0.95 | −1.05 | −2.50 | −0.62 | −1.25 | AL589743.4 | −0.10 | −1.38 | 0.26 | 0.25 | 2.44 |
| AP001885.1 | 0.69 | −0.14 | −0.22 | −0.09 | −0.08 | RHEBP2 | 0.40 | −0.09 | −0.06 | 0.06 | 0.45 | AC103855.4 | 0.40 | −0.54 | 0.15 | 1.64 | 3.43 |
| SPNS2 | 0.37 | −0.09 | −0.21 | 0.06 | −0.34 | AP005899.1 | −0.14 | −0.30 | −0.31 | 0.24 | 0.41 | LINC00485 | 0.08 | 0.05 | −2.25 | 0.68 | −1.86 |
| RNA5SP145 | −1.22 | 0.61 | −1.29 | 1.72 | −1.06 | MIR4706 | 0.47 | −0.40 | 1.25 | 0.12 | 1.05 | AC092047.1 | 0.40 | −1.23 | −0.59 | −0.44 | 0.87 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| MT-ND2 | −0.53 | 0.22 | 0.55 | −0.09 | 0.22 | AC008534.1 | 0.27 | −0.25 | −0.16 | −0.16 | 0.09 | GFOD1-AS1 | 0.05 | 0.04 | −1.73 | 0.41 | −0.72 |
| PDE6D | 0.28 | −0.03 | −0.13 | −0.09 | −0.32 | RNU4-21P | −0.33 | −0.39 | 0.20 | −0.17 | 0.36 | G10215 | −0.32 | 0.40 | 0.74 | 1.25 | −1.49 |
| PKMP5 | −1.14 | 0.55 | 0.30 | 1.38 | 0.19 | NPM1P14 | 0.64 | −0.73 | −1.43 | 0.03 | −1.60 | AC138811.1 | 0.06 | −0.80 | −0.34 | −0.33 | 0.14 |
| AL390071.1 | −1.35 | 0.79 | 1.80 | −0.49 | 0.70 | HSD3B2 | −0.47 | −0.01 | −0.28 | 0.37 | −0.48 | AC082651.1 | 0.40 | 0.85 | −0.44 | −0.80 | −1.58 |
| AC022960.1 | 0.65 | −0.27 | −0.14 | −0.20 | 0.20 | AL359740.1 | −0.23 | 0.07 | 0.67 | −0.07 | 0.13 | AC100849.1 | −0.06 | −0.03 | −0.88 | 0.16 | −0.76 |
| ADGRE2 | 0.47 | −0.88 | −0.88 | −0.39 | −0.36 | CRY1 | −0.09 | 0.09 | 0.10 | 0.00 | −0.27 | AL449043.1 | 0.40 | −1.22 | 0.05 | −0.12 | 0.74 |
| AL035410.1 | 0.90 | −0.50 | −1.19 | −0.32 | −0.95 | KPNA2P2 | −0.45 | 0.25 | 0.14 | 1.03 | −0.05 | MAGEB1 | 0.15 | −0.93 | 0.79 | −1.86 | 0.26 |
| AC016745.2 | −0.99 | 0.63 | 1.33 | 0.46 | 1.01 | MGST2 | 0.14 | 0.15 | 0.29 | 0.18 | 0.05 | RNA5SP456 | 0.19 | −1.29 | −1.39 | 0.59 | −1.51 |
| CCDC117 | 0.30 | −0.11 | 0.09 | −0.17 | 0.07 | AC106037.2 | 0.26 | −0.22 | 0.04 | −0.10 | 0.11 | AL354810.1 | −0.17 | −0.26 | −1.98 | 0.26 | −0.76 |
| B3GALT1 | −1.25 | 0.32 | 2.32 | 0.05 | 0.74 | AC004812.1 | −0.29 | 0.04 | 0.21 | 0.21 | 0.34 | AC105277.1 | 0.04 | −0.26 | −0.80 | −0.32 | −0.37 |
| NEK7 | 0.43 | −0.27 | −0.62 | −0.25 | −0.31 | AC023034.2 | −0.82 | −0.95 | 1.78 | −0.71 | 1.73 | AL512661.1 | 0.23 | −0.17 | 1.12 | 2.68 | 1.93 |
| HTR4 | −1.28 | 0.73 | 0.26 | 0.78 | 0.50 | AC073657.1 | −0.29 | 0.10 | 0.05 | 0.28 | 0.55 | MIPEP | −0.02 | 0.10 | −0.01 | 0.26 | 0.14 |
| AC080013.4 | 0.71 | −0.03 | 0.02 | 0.14 | 0.13 | AC067742.1 | 0.42 | −0.47 | 0.56 | −0.82 | 0.94 | RN7SL397P | 0.25 | −0.16 | −0.79 | 0.62 | −0.71 |
| GABBR2 | −0.82 | −0.09 | −0.33 | 0.26 | −0.57 | PRG3 | −0.99 | −0.15 | −2.42 | 1.66 | −1.07 | AL031710.2 | 0.04 | −0.25 | 0.25 | −0.41 | 0.37 |
| RN7SL558P | 0.85 | −0.37 | −0.46 | −0.44 | −0.15 | GALR3 | 0.54 | −0.44 | −1.31 | 0.06 | −0.16 | AC097381.1 | 0.04 | −0.12 | 0.51 | −0.31 | −0.60 |
| AC023355.1 | −0.92 | −0.10 | 0.79 | 0.09 | 0.79 | ETF1P3 | 0.59 | −0.06 | −1.74 | 0.53 | −0.85 | PFN5P | −0.21 | −0.85 | −0.39 | −0.65 | 1.46 |
| AQP4-AS1 | −1.19 | 0.42 | 0.29 | 0.36 | 0.35 | EPCAM | 0.24 | 0.02 | 0.13 | 0.15 | 0.43 | HMGB3P17 | 0.21 | −0.62 | −0.75 | 1.52 | 0.08 |
| HLA-A | 0.43 | −0.57 | −0.16 | −0.46 | 0.00 | AP000346.4 | −0.82 | 0.58 | 2.17 | −0.47 | 1.11 | CCDC197 | 0.14 | −0.25 | −2.86 | 1.40 | −3.02 |
| CAVIN1 | −0.39 | 0.11 | 0.06 | 0.02 | 0.01 | RMRP | −0.14 | 0.36 | 0.05 | 0.10 | −0.65 | RN7SL24P | −0.15 | −0.51 | 0.87 | −0.14 | 1.24 |
| OXSM | 0.47 | −0.29 | 0.28 | −0.38 | 0.04 | AC016559.1 | −0.37 | −0.62 | 0.88 | −0.09 | 0.74 | AC099482.2 | −0.13 | 0.17 | 0.28 | 0.54 | 0.04 |
| APH1B | −0.34 | 0.19 | 0.18 | 0.16 | 0.15 | PLXNB2 | −0.08 | −0.10 | −0.36 | 0.03 | −0.08 | AC136932.1 | 0.11 | 0.07 | −1.13 | 0.19 | −0.93 |
| AC003986.1 | −1.52 | −0.07 | 0.23 | −0.34 | −0.25 | DHX30 | 0.07 | −0.12 | −0.14 | −0.06 | 0.06 | AC091819.1 | −0.19 | −1.42 | −0.87 | 0.98 | −1.80 |
| SLCO4C1 | −1.10 | 0.73 | 0.02 | 1.27 | 1.04 | C6orf58 | −0.45 | −0.52 | 1.53 | −1.18 | 0.67 | RNU6-1277P | −0.40 | −0.44 | 1.12 | −0.97 | 1.54 |
| LAPTM5 | 0.69 | −0.72 | −0.35 | −0.32 | −0.09 | AC012464.1 | −0.29 | −0.25 | 0.90 | −0.13 | 0.39 | AC026320.1 | −0.08 | −0.46 | 0.46 | −0.39 | 0.77 |
| AC027237.2 | −1.17 | 0.06 | −0.17 | 0.56 | 0.77 | MAGEA11 | −0.70 | 1.28 | −0.85 | 1.64 | −1.10 | AC022441.1 | 0.18 | 0.18 | −0.46 | 0.65 | −0.46 |
| ACTG1P17 | −0.94 | 0.26 | 0.17 | 0.46 | −0.18 | RNU6-574P | 0.34 | −0.24 | 0.27 | 0.19 | 0.39 | AC126696.3 | 0.37 | 0.26 | −1.23 | 0.76 | −1.23 |
| AL035587.1 | −0.67 | 0.19 | 0.09 | 0.05 | 0.14 | AL353898.1 | −0.47 | 0.51 | 0.98 | 0.10 | −0.57 | AC092447.4 | 0.40 | −0.69 | 0.10 | −0.75 | −0.49 |
| AC120042.1 | 1.08 | −0.62 | 0.56 | −0.36 | 0.11 | HSPD1P4 | −0.29 | −0.21 | 0.12 | −0.57 | 0.11 | MOGAT3 | −0.08 | −1.76 | −0.34 | −0.68 | 0.93 |
| RP11-435B5.4 | −0.40 | 0.16 | 0.42 | 0.52 | 0.70 | AP000926.1 | −0.35 | −0.35 | 0.59 | −0.41 | 0.28 | AC073655.1 | −0.05 | −0.76 | 0.12 | −0.20 | 0.19 |
| AC013437.1 | 1.38 | −0.70 | −1.26 | 0.22 | 0.35 | ATG4C | 0.13 | −0.17 | 0.19 | −0.32 | 0.03 | AC025442.1 | −0.10 | 0.96 | −0.94 | 0.70 | −0.52 |
| MRPL49 | 0.32 | −0.12 | −0.20 | −0.02 | −0.11 | AL590705.2 | −0.80 | −0.51 | −1.04 | −0.75 | −0.55 | AC024559.1 | −0.09 | −0.63 | −1.79 | −0.02 | −1.00 |
| AC093458.2 | −1.56 | 0.20 | 2.58 | −0.77 | 1.72 | PPME1 | 0.08 | −0.08 | −0.06 | −0.01 | 0.12 | RTN3 | −0.01 | 0.19 | 0.25 | 0.09 | −0.04 |
| AL590084.3 | −1.26 | 0.45 | 0.72 | 0.06 | 0.30 | LINC00841 | −0.45 | 0.43 | 0.53 | 1.31 | −0.25 | AP001267.1 | −0.04 | 0.54 | 0.01 | −0.16 | −0.59 |
| FMO4 | −0.49 | 0.24 | 0.90 | 0.09 | 0.60 | AL049758.1 | −0.36 | 0.37 | 0.33 | −0.65 | −0.83 | LIPF | 0.06 | 0.31 | −0.88 | 0.08 | −0.48 |
| PTCD3 | 0.26 | −0.07 | −0.16 | 0.02 | 0.08 | SNORD15B | 0.18 | 0.13 | 0.28 | 0.03 | −0.32 | ERO1B | −0.01 | 0.17 | 0.31 | −0.14 | −0.01 |
| FAM135B | −0.93 | 0.20 | 0.48 | 0.54 | 0.22 | OR51F3P | 1.09 | −2.24 | −1.60 | −0.52 | 1.19 | OR8B3 | −0.11 | 1.24 | −0.35 | 0.21 | 0.22 |
| AF201337.1 | 0.81 | −0.20 | −1.03 | −0.14 | −0.74 | LINC02218 | 0.93 | −1.71 | −1.20 | 0.95 | −1.61 | AC098799.3 | −0.40 | −0.77 | −0.11 | −1.59 | −1.09 |
| NOSIP | 0.23 | −0.04 | −0.30 | −0.08 | −0.30 | REPIN1 | −0.09 | 0.04 | 0.10 | 0.12 | 0.22 | MS4A14 | −0.03 | −0.33 | −0.27 | −0.32 | −0.58 |
| AC009137.2 | 0.92 | −0.40 | −0.32 | −0.37 | 0.00 | AC061975.7 | −0.57 | −0.54 | 0.07 | 0.14 | 1.17 | IGLC2 | 0.22 | 1.16 | −0.07 | −0.14 | −0.16 |
| AC138470.1 | −0.60 | 0.55 | 1.37 | −0.21 | 0.27 | AC009806.1 | 0.41 | −1.33 | −0.51 | 0.31 | 0.55 | AL137789.1 | −0.13 | −0.28 | −1.53 | 0.14 | −0.22 |
| AL713999.1 | 1.31 | −1.14 | −0.75 | −0.34 | −0.34 | AL024498.1 | −0.24 | 0.02 | 1.04 | −0.53 | 0.27 | FOXA3 | −0.13 | 1.26 | −1.36 | 2.38 | −1.05 |
| C9orf40 | 0.52 | −0.31 | −0.54 | 0.06 | −0.05 | NOTUM | −0.36 | 1.00 | −0.21 | 0.76 | −0.79 | DEFB108F | 0.40 | −0.45 | 0.43 | −0.91 | 0.09 |
| ETV5 | −0.36 | 0.17 | 0.31 | 0.32 | 0.12 | RN7SL566P | −0.34 | −0.43 | −0.09 | 0.31 | 0.58 | PTPN18 | 0.01 | 0.01 | 0.01 | 0.01 | 0.04 |
| G24891 | −0.49 | 0.31 | 0.60 | −0.15 | 0.40 | HELT | −0.66 | −0.46 | 0.28 | 0.32 | −1.48 | AC104561.3 | −0.12 | −0.70 | −1.00 | 1.17 | 0.70 |
| NAV2-AS4 | −0.91 | 0.51 | 0.66 | 0.72 | 0.10 | LINC01775 | 0.52 | −1.09 | −0.96 | −0.57 | −1.27 | AC007349.1 | −0.11 | −0.61 | −0.12 | 0.13 | −1.60 |
| CEL | −0.80 | 0.79 | −0.60 | 0.22 | −0.18 | FAM181A-AS1 | −0.60 | −0.99 | −0.80 | 0.35 | −0.11 | DPRXP6 | −0.40 | −0.24 | 0.84 | −0.14 | 0.06 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| ISX–AS1 | 2.11 | −1.18 | −2.93 | −0.35 | −0.80 | AL590432.1 | −0.93 | −1.39 | −1.92 | −0.33 | 0.31 | IGKV2-28 | 0.40 | 1.45 | 0.56 | −0.22 | −1.24 |
| PIGK | 0.36 | −0.17 | 0.01 | −0.19 | −0.29 | CIRBP-AS1 | −0.23 | 0.17 | 0.32 | 0.01 | 0.52 | CCDC83 | −0.05 | −0.21 | −0.69 | 0.14 | −0.43 |
| SAYSD1 | 0.30 | −0.03 | −0.33 | 0.06 | −0.16 | DPPA4 | −0.43 | −0.72 | −0.74 | −0.50 | −0.47 | AC026367.2 | 0.05 | −0.52 | −0.89 | −0.53 | 0.63 |
| AC002381.1 | 1.28 | −0.34 | 0.16 | 0.25 | 0.44 | LINC01788 | 0.55 | −0.71 | −1.36 | 0.35 | −0.26 | AC074276.2 | 0.07 | 0.45 | −0.12 | −0.54 | −0.04 |
| AL591806.1 | −0.52 | 0.15 | 0.20 | 0.10 | 0.06 | AC010273.1 | 0.52 | −0.33 | −0.31 | −0.16 | 0.15 | AL356157.1 | 0.38 | −0.47 | −0.56 | 0.04 | −0.84 |
| ACPP | 0.56 | −0.04 | 0.17 | 0.32 | 0.07 | FAM170B-AS1 | 0.44 | −2.31 | −0.31 | −0.31 | 1.92 | AC091932.2 | −0.39 | 0.68 | −0.47 | −0.46 | −2.18 |
| BACE2 | 0.28 | −0.19 | −0.16 | −0.15 | −0.08 | AC138965.2 | 0.58 | −0.27 | −1.10 | −0.07 | −0.17 | NCOR1P3 | −0.40 | 0.31 | −0.21 | 1.76 | −0.40 |
| MASP1 | 0.69 | −0.23 | 0.10 | −0.42 | 0.04 | AC087623.3 | −0.55 | 0.86 | 0.99 | −0.35 | 0.51 | LANCL1-AS1 | 0.03 | 0.30 | 0.31 | 0.20 | −0.02 |
| RAVER1 | 0.38 | −0.25 | −0.88 | 0.21 | −0.09 | RPL9P3 | 0.38 | −0.38 | 0.30 | −0.36 | 0.34 | H2AFZP2 | −0.09 | 0.14 | −1.78 | 0.38 | 0.88 |
| AL117328.2 | −1.02 | 0.41 | −1.17 | 1.00 | −0.65 | LYPD4 | 0.73 | −2.30 | −1.64 | 0.42 | 0.01 | SPIB | 0.05 | −0.53 | −0.85 | −0.98 | −0.43 |
| AC117489.1 | −1.21 | 0.53 | 0.30 | 0.25 | 0.27 | SNORA65 | −0.25 | 0.35 | −0.36 | 0.50 | −0.30 | AC103993.1 | −0.24 | −0.12 | −0.27 | 1.97 | −0.72 |
| RPS28P7 | 0.53 | −0.18 | 0.37 | −0.97 | −0.63 | MIR548E | 0.56 | −2.06 | −2.09 | 0.04 | −0.50 | AP003465.1 | −0.08 | 1.07 | −1.14 | 1.12 | −2.27 |
| AC005736.2 | −1.05 | 0.12 | −1.43 | 0.19 | −0.23 | RNU6-196P | 0.44 | −0.79 | −0.43 | −0.72 | −0.69 | PTPRJ–AS1 | −0.03 | −0.49 | −0.49 | −0.42 | 0.13 |
| RN7SL158P | −1.75 | −1.44 | 0.98 | −0.50 | 2.40 | FDX1P1 | 0.50 | 0.03 | 0.75 | −0.04 | 0.60 | AC012456.1 | 0.13 | 0.12 | −0.72 | −0.52 | 1.16 |
| PROK2 | 1.72 | −2.58 | −0.34 | −0.63 | −1.98 | KCNMA1-AS3 | −0.42 | 0.47 | −0.50 | 0.01 | −0.40 | AC044839.2 | 0.39 | −1.72 | −0.56 | −1.73 | −0.29 |
| AC016877.1 | −1.34 | 0.13 | 1.02 | 0.26 | 0.68 | PROKR1 | −0.70 | −0.93 | 2.27 | −1.64 | 0.98 | G30301 | 0.10 | −1.48 | −0.34 | 0.37 | 1.80 |
| RNU6-958P | −1.02 | 0.33 | 0.04 | 0.89 | −0.26 | RNU6-504P | −0.75 | −0.70 | 0.03 | 0.97 | 0.82 | 3-Mar | 0.02 | 0.23 | 0.63 | 0.19 | −0.24 |
| KRT23 | −0.59 | 0.45 | 1.23 | 0.43 | −0.01 | MAP9 | −0.22 | 0.02 | 0.46 | −0.13 | −0.04 | PNPLA6 | −0.01 | −0.09 | −0.32 | 0.12 | 0.01 |
| IFNAR2 | 0.69 | −0.70 | −0.44 | −0.27 | −0.08 | AC018634.1 | 0.83 | −0.95 | 0.24 | −1.19 | 0.14 | GABPAP | −0.08 | 1.03 | −1.91 | 0.40 | −2.57 |
| LINC00671 | −1.12 | 0.35 | −0.04 | 1.38 | −0.14 | HERC2P11 | −0.57 | 0.35 | −0.07 | 1.56 | 0.55 | AL121873.1 | −0.39 | 0.04 | −1.65 | 0.77 | −0.18 |
| REXO4 | 0.23 | −0.15 | −0.25 | −0.13 | 0.05 | CIITA | 0.18 | −0.68 | −0.18 | −0.41 | 0.26 | AC074386.1 | 0.06 | −0.32 | 0.65 | 0.83 | 1.43 |
| AC105749.1 | 0.91 | −0.01 | −0.51 | 0.15 | −0.37 | SOX30 | 0.42 | 0.31 | −0.68 | 0.10 | −0.65 | KRT18P22 | 0.08 | −1.33 | −2.17 | 1.34 | −0.48 |
| SPATA21 | −0.50 | 0.12 | 0.22 | 0.11 | 0.27 | OR52B4 | −0.71 | −0.30 | −1.38 | −0.94 | −1.03 | AC006840.1 | −0.39 | 0.07 | 0.74 | 0.92 | 1.85 |
| AC011483.2 | 1.51 | −1.01 | 0.23 | −0.80 | −0.87 | LINC00629 | 1.04 | 0.70 | −1.09 | 1.25 | −0.97 | MSANTD2P1 | −0.39 | 0.42 | −0.13 | 0.71 | −1.19 |
| IQCE | −0.30 | 0.06 | −0.01 | 0.13 | 0.17 | ERLNC1 | −0.87 | 0.72 | −0.07 | 1.03 | 1.03 | OR7E29P | 0.23 | 0.47 | −1.46 | −0.41 | −0.89 |
| AMD1P1 | −1.07 | 1.30 | 0.52 | 0.85 | −0.75 | GLTPD2 | 0.18 | −0.10 | −0.23 | 0.16 | 0.11 | ITPRIPL2 | −0.01 | −0.24 | −0.03 | 0.07 | 0.26 |
| RN7SKP203 | −0.47 | 0.57 | 0.66 | 0.04 | −0.27 | GCA | −0.17 | 0.01 | 0.11 | −0.10 | −0.02 | MCD2 | 0.05 | −0.97 | 0.11 | −0.40 | 0.13 |
| RNA5SP389 | −1.24 | 0.63 | −1.49 | 1.75 | −1.08 | AC127070.2 | −0.48 | 1.05 | 1.47 | 0.89 | 0.46 | RUNDC3A-AS1 | −0.04 | −0.09 | −0.44 | −0.31 | −0.21 |
| AC016730.1 | −2.13 | 0.97 | −0.98 | 0.41 | −0.88 | AC074031.1 | −1.19 | 0.49 | −0.41 | −0.90 | −0.69 | CNR2 | −0.05 | −1.01 | −0.13 | −0.75 | 0.43 |
| RN7SL500P | 1.19 | 0.03 | −0.42 | 0.18 | −0.36 | FAM43B | 0.31 | 0.04 | 0.06 | 0.05 | −0.09 | AL096701.2 | −0.07 | 0.61 | −0.29 | 0.81 | −0.60 |
| AC109583.1 | −1.35 | −0.51 | 2.37 | −0.78 | 0.15 | OR51A4 | 0.58 | −0.65 | −2.17 | −0.02 | −1.15 | AL121977.1 | 0.31 | −0.61 | −0.30 | −0.40 | −0.85 |
| AP001007.1 | −1.00 | 0.76 | −0.91 | 0.50 | −0.42 | RPL29P32 | −0.50 | 0.06 | 1.19 | −0.10 | 0.33 | C12orf43 | −0.01 | −0.13 | −0.28 | 0.17 | −0.03 |
| PTPN13 | 0.36 | 0.06 | −0.21 | 0.28 | −0.20 | MIR597 | 0.68 | −0.94 | 0.29 | 0.55 | 2.15 | LINC00550 | 0.10 | 0.97 | −0.04 | 0.35 | −1.64 |
| PDE4B | 0.66 | −0.49 | −0.36 | −0.09 | −0.06 | AC026771.1 | 0.41 | −0.04 | 0.68 | −0.01 | 0.17 | KRT8P37 | 0.13 | −0.43 | −1.19 | −0.35 | −1.11 |
| RNU4-62P | 1.34 | −0.67 | 0.00 | −0.24 | 0.28 | FAF2P1 | 1.35 | 0.10 | −1.05 | 1.13 | −0.46 | FAM204DP | 0.39 | −0.76 | −0.43 | −0.56 | −1.44 |
| SLC13A4 | −0.31 | 0.10 | 0.59 | −0.42 | 0.03 | C9orf3 | −0.11 | 0.15 | 0.00 | 0.22 | 0.06 | BOD1P2 | −0.39 | 0.76 | 0.40 | −0.16 | −2.16 |
| MYLK2 | 1.14 | −2.19 | −1.45 | −0.17 | 0.83 | HNRNPA1P74 | −0.81 | −1.03 | −0.60 | −0.87 | −0.62 | AC124657.1 | 0.39 | −0.93 | 0.54 | −0.28 | 0.59 |
| AC083801.2 | 0.67 | −0.23 | −0.61 | −0.16 | −0.07 | RN7SKP151 | −0.45 | 1.37 | 0.02 | 0.63 | 0.20 | AC009878.1 | −0.28 | −1.24 | 0.45 | −0.24 | 0.39 |
| FTH1P1 | −0.59 | 0.17 | −0.03 | 0.15 | 0.20 | FSBP | 0.28 | 0.01 | 0.26 | 0.06 | −0.01 | AC093802.1 | −0.09 | −0.69 | −0.30 | −0.57 | 0.27 |
| AAAS | −0.27 | 0.16 | 0.24 | 0.12 | 0.30 | LINC02310 | 0.93 | 0.30 | −0.98 | −1.58 | −2.81 | RPL23AP40 | −0.04 | −0.41 | 0.46 | 0.26 | 1.18 |
| AC021766.1 | 0.59 | 0.06 | −0.42 | −0.07 | −0.36 | RN7SL491P | −0.88 | −1.80 | 1.27 | −2.22 | 1.46 | AL031679.1 | 0.39 | −1.06 | −0.84 | −2.28 | −2.51 |
| ME2 | 0.22 | −0.31 | −0.21 | −0.24 | 0.04 | AL592166.1 | 0.51 | 0.11 | 0.81 | −0.21 | −0.22 | CSN3 | 0.21 | −0.54 | −0.93 | −0.23 | 0.73 |
| EPS8L2 | −0.39 | 0.28 | −0.18 | 0.35 | 0.01 | PSG2 | −0.41 | 0.68 | 0.39 | 0.75 | −1.07 | MIR558 | 0.12 | 1.51 | 2.02 | −0.47 | 1.34 |
| CUTALP | −0.30 | 0.14 | 0.28 | 0.05 | −0.01 | AC018521.5 | 0.17 | 0.03 | 0.00 | 0.16 | −0.11 | AL049636.1 | −0.16 | −0.76 | −0.42 | −0.13 | −0.61 |
| AL365203.2 | 0.61 | −0.77 | −0.49 | −0.40 | 0.11 | AC097374.1 | −0.33 | 0.31 | −0.56 | 0.69 | −0.70 | AC094104.1 | −0.39 | −0.29 | 0.27 | −0.31 | 0.23 |
| LINC02340 | −0.67 | 0.14 | 0.24 | 0.43 | 0.80 | AC007327.2 | −0.54 | 0.11 | 2.54 | −0.25 | 1.20 | OR2BH1P | −0.39 | −0.30 | −0.68 | 0.36 | −1.33 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| RABGGTA | 0.30 | −0.15 | −0.59 | 0.09 | −0.15 | KLRC4-KLRK1 | −0.57 | −1.48 | −0.48 | −0.44 | 1.23 | GPSM1 | −0.02 | −0.19 | −0.28 | −0.18 | −0.14 |
| RNU2-70P | −0.94 | 0.04 | 0.59 | 1.24 | 0.79 | RNU6-590P | −0.92 | 0.15 | 1.85 | 0.06 | −0.17 | LA16c-60G3.7 | 0.39 | −0.17 | −1.22 | 1.53 | −0.62 |
| AC100763.1 | 0.45 | −0.28 | 0.07 | −0.11 | 0.32 | AC131211.1 | 1.05 | −0.60 | 0.68 | 0.47 | 1.18 | FLJ38576 | −0.09 | 0.03 | 1.44 | −1.68 | −0.78 |
| AC073651.1 | −0.68 | 0.26 | 0.42 | −0.44 | −0.33 | SNX18P8 | −1.24 | 0.14 | 0.29 | −0.66 | 0.91 | NOC2LP2 | 0.11 | −1.14 | −0.92 | 1.98 | 1.69 |
| LINC02413 | −1.59 | 0.26 | 0.76 | −0.08 | −0.32 | AC068580.3 | −0.21 | 0.03 | 0.54 | 0.01 | 0.29 | RNU6-22P | 0.13 | −2.57 | −0.52 | −1.05 | 0.88 |
| FCMR | 0.70 | −0.76 | −0.08 | −0.70 | 0.50 | AC007448.4 | −0.34 | 0.49 | 0.52 | 0.37 | −0.05 | GAPDHP41 | −0.16 | −1.30 | −0.98 | −1.39 | −2.00 |
| ANO7 | −0.69 | 0.17 | −0.08 | 0.00 | 0.07 | ELOA-AS1 | −0.24 | 0.41 | 0.10 | 0.50 | −0.11 | OASL2P | −0.39 | 0.20 | 0.59 | −0.09 | −0.13 |
| EGFEM1P | −0.91 | 0.57 | 0.32 | 0.43 | 0.27 | AL450338.1 | −0.53 | 0.09 | 0.53 | 0.05 | 0.82 | LINC02174 | −0.15 | 0.17 | 1.04 | −1.12 | −2.94 |
| AL158166.2 | 0.95 | 0.67 | −0.34 | −0.25 | −0.76 | MIR1910 | 0.68 | −0.09 | −1.88 | −0.25 | −0.80 | PTH | −0.39 | 1.51 | −0.80 | 0.78 | −0.70 |
| MYO18A | −0.32 | 0.02 | −0.22 | 0.09 | 0.04 | AC091805.1 | 0.36 | 0.03 | −0.60 | 0.30 | 0.71 | RPL35AP26 | 0.08 | 0.45 | 1.13 | 0.94 | −0.05 |
| RANBP17 | −0.55 | 0.25 | 0.75 | −0.18 | 0.27 | G16040 | −1.43 | 0.39 | 0.59 | −1.32 | −0.09 | CYP51A1P1 | −0.11 | 0.47 | −0.61 | 0.50 | −0.61 |
| G2592 | −0.97 | 0.73 | 1.53 | −0.14 | 0.22 | KCNC3 | −0.16 | 0.18 | 0.19 | −0.16 | −0.06 | AC012531.1 | −0.02 | 0.07 | 0.19 | 0.02 | −0.08 |
| AL354694.1 | 1.35 | −0.17 | 0.35 | −1.34 | −0.73 | AC016957.1 | 0.39 | −0.62 | 0.09 | −0.30 | −0.58 | AC024619.1 | −0.18 | 0.52 | 0.63 | 0.42 | 0.84 |
| SKOR2 | −1.03 | −0.04 | 0.72 | −0.17 | −0.11 | SOX21 | 0.25 | 0.52 | −0.06 | 0.66 | −0.31 | AC135507.2 | −0.05 | 0.28 | 0.54 | 0.16 | −0.08 |
| HERC2P4 | −0.85 | −0.42 | −0.03 | 1.45 | 2.74 | SUDS3 | −0.08 | 0.16 | 0.03 | 0.06 | −0.05 | CXCR6 | 0.01 | 0.28 | 0.15 | 0.04 | −0.12 |
| RPS15 | 0.33 | −0.06 | −0.04 | −0.25 | −0.27 | BX276092.9 | −0.52 | −0.57 | −0.04 | 0.33 | 1.75 | AC015922.1 | −0.39 | 0.54 | 1.51 | −0.66 | 0.55 |
| G9222 | −1.59 | 1.25 | 2.66 | 0.67 | 0.71 | SHC1P2 | −0.51 | −0.67 | 0.48 | −1.03 | 0.75 | LINC01248 | 0.22 | −1.42 | 0.61 | −0.61 | 0.14 |
| AC096861.1 | 1.10 | −0.33 | −0.50 | 0.03 | −0.95 | LINC01933 | −0.42 | 0.16 | −1.10 | 0.45 | −0.70 | NIFKP7 | −0.15 | 0.29 | −1.46 | −1.02 | −2.70 |
| INAFM1 | −0.51 | 0.44 | 0.28 | 0.47 | 0.12 | AC020601.1 | −0.91 | 0.30 | −0.34 | −0.70 | −0.47 | AC091180.5 | −0.07 | −0.51 | 0.49 | −0.43 | 0.68 |
| CNTROB | −0.26 | 0.07 | −0.09 | 0.12 | 0.02 | SETD9 | 0.23 | −0.06 | 0.34 | −0.23 | −0.14 | AL354766.1 | −0.39 | −0.40 | −0.21 | −0.44 | −1.22 |
| LINC01869 | −1.16 | 1.24 | 1.17 | 1.04 | 0.65 | AC069213.1 | 0.40 | 0.22 | −0.65 | 0.41 | −1.09 | AL049812.3 | 0.12 | −0.36 | 0.30 | 0.28 | 0.85 |
| HPF1 | 0.32 | −0.17 | 0.01 | −0.19 | −0.18 | MTND1P36 | −0.26 | −0.05 | 0.07 | −0.24 | 0.44 | AC068512.1 | −0.11 | −0.98 | −2.41 | −0.24 | −2.47 |
| PPP3R1 | 0.35 | −0.06 | −0.23 | 0.00 | −0.20 | RNY5P8 | 0.43 | −0.15 | −0.20 | −0.02 | −0.64 | AP000688.4 | −0.10 | −1.38 | 0.93 | −0.35 | 1.88 |
| SMN1 | 0.57 | −0.38 | −0.33 | −0.13 | 0.15 | AC110994.1 | −0.23 | 0.37 | 0.22 | −0.22 | −0.34 | AC132812.1 | 0.02 | −0.05 | 0.16 | −0.06 | 0.00 |
| KRT18P52 | −0.82 | 0.28 | 0.88 | 0.06 | 0.90 | CPO | −0.35 | −0.23 | 0.45 | −0.19 | 0.80 | STK3 | −0.01 | −0.12 | 0.10 | −0.16 | 0.08 |
| EMBP1 | −0.71 | 0.02 | 0.03 | 0.09 | 0.22 | MAPK6P4 | 0.53 | −0.57 | 0.19 | 0.24 | −0.33 | LINC01738 | −0.39 | 0.00 | 1.35 | 0.65 | 0.94 |
| RNA5SP385 | 1.10 | −0.35 | −0.86 | 0.05 | −0.30 | AL137796.1 | −0.39 | 0.29 | 1.69 | 0.35 | 0.53 | PHC1P1 | −0.03 | 0.32 | 0.23 | 0.41 | −0.14 |
| FMR1-IT1 | −0.64 | 0.21 | −0.19 | 0.14 | −0.21 | OR2T5 | −1.92 | 1.09 | 1.08 | 0.56 | −0.30 | AC024908.1 | −0.16 | −0.57 | −0.22 | 1.85 | 1.33 |
| RNU6-1143P | 1.36 | −0.90 | −0.67 | −0.59 | 0.18 | AP001999.4 | 0.78 | −1.07 | −1.42 | 0.10 | −1.60 | LINC00347 | −0.11 | −0.05 | −2.03 | −1.03 | −2.85 |
| SNTG2 | −0.60 | 0.12 | 0.26 | −0.19 | 0.09 | AL138815.2 | 1.04 | 0.19 | −0.44 | −0.07 | −1.19 | C1orf185 | −0.06 | −0.39 | −0.77 | 0.66 | 0.95 |
| PCDHB5 | −0.89 | 0.10 | 1.52 | −0.03 | 0.44 | AL117192.1 | 0.87 | −1.06 | −2.26 | 0.52 | −0.62 | RN7SL141P | −0.04 | −0.31 | −0.11 | −0.41 | −0.11 |
| ACOT4 | −0.72 | 0.43 | −0.54 | 0.00 | 0.28 | AL365357.1 | 0.23 | 0.24 | −0.04 | −0.22 | −0.45 | AC117498.2 | 0.19 | −0.94 | −1.62 | −0.13 | −0.03 |
| AC006042.2 | −1.12 | 1.06 | 1.43 | 0.78 | 0.05 | FAM86DP | −0.11 | 0.12 | −0.19 | 0.23 | 0.05 | NEFMP1 | −0.08 | 0.65 | −0.82 | 0.90 | −1.68 |
| LINC00882 | −0.91 | 0.03 | 0.68 | −0.20 | −0.20 | AC005225.2 | −1.18 | 1.69 | 2.02 | 0.56 | 0.77 | PAH | −0.06 | −0.74 | −0.97 | 0.28 | −0.73 |
| ERCC4 | 0.27 | −0.13 | −0.10 | −0.13 | 0.06 | AC091047.1 | 0.54 | −0.45 | −1.51 | 0.04 | 0.25 | AC106729.1 | 0.19 | 1.37 | −1.43 | −0.04 | −3.10 |
| CHRNA7 | −0.85 | 0.25 | −0.38 | 0.28 | −0.03 | AC036176.1 | 0.39 | 0.46 | 0.12 | 0.44 | 0.06 | POSTN | 0.03 | 0.09 | 0.49 | −0.80 | −0.46 |
| PSMA1 | 0.56 | −0.21 | −0.55 | −0.09 | −0.50 | GLIS2-AS1 | −0.46 | 0.35 | −0.61 | 0.11 | −0.81 | NSG2 | −0.08 | −0.46 | −0.99 | 0.39 | 0.59 |
| NOP9 | 0.32 | −0.25 | −0.41 | 0.10 | 0.03 | PRL | 0.67 | 0.08 | −0.50 | 0.57 | −1.92 | DEFB110 | −0.39 | 0.06 | −0.84 | 0.58 | −1.22 |
| AOX2P | 1.18 | −1.03 | −1.29 | −0.25 | −0.19 | AC027279.1 | −0.16 | 0.00 | 0.16 | 0.24 | 0.21 | PVRIG | −0.04 | 0.52 | 0.24 | 0.42 | −0.28 |
| NAT8 | −1.10 | −0.44 | 0.96 | −0.06 | 0.83 | NT5C1A | −0.97 | 0.12 | −0.46 | −1.90 | −2.97 | AC100781.1 | 0.39 | −1.72 | −0.44 | 0.26 | 1.01 |
| C3orf80 | 1.26 | −0.80 | −0.46 | −1.02 | −0.23 | EXD1 | 0.48 | −0.67 | −1.20 | 0.10 | −0.57 | MIR1249 | −0.06 | −0.23 | −0.94 | 0.50 | −0.90 |
| SLC36A4 | 0.22 | −0.19 | −0.16 | −0.12 | −0.16 | POM121L6P | −0.44 | 0.23 | −0.59 | 0.32 | 0.12 | SUCLG2P4 | −0.14 | 0.73 | −0.25 | 0.23 | −1.94 |
| DPY19L2 | −0.60 | 0.36 | 0.78 | 0.02 | −0.16 | HTRA2 | −0.11 | −0.15 | −0.16 | 0.22 | 0.22 | AL022154.1 | 0.39 | −0.34 | −0.65 | 0.60 | 0.46 |
| CCSER2 | 0.28 | 0.05 | 0.09 | −0.10 | −0.25 | LINC02571 | −0.98 | −0.64 | −0.78 | 1.64 | 0.20 | AC106754.1 | 0.16 | −0.41 | −0.68 | 1.07 | −0.50 |
| AC084064.1 | −1.28 | 1.97 | 1.37 | 0.54 | −0.02 | COL6A4P1 | −0.37 | 0.14 | −0.13 | −0.18 | 0.19 | RN7SL465P | 0.39 | 0.20 | 0.16 | 0.06 | −1.73 |
| NT5DC1 | 0.28 | −0.04 | −0.38 | 0.20 | −0.10 | AASS | 0.13 | 0.05 | 0.00 | 0.39 | 0.08 | AC012456.2 | −0.39 | −1.19 | −1.21 | 0.17 | 0.75 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| MT-ND1 | −0.47 | 0.27 | 0.42 | 0.07 | 0.19 | AP002989.1 | 0.43 | −0.63 | 0.11 | −0.77 | 0.01 | AC073358.1 | 0.04 | 0.01 | 0.40 | −0.29 | 0.18 |
| AL355336.1 | 0.48 | −0.43 | −0.47 | −0.20 | −0.08 | AC007346.1 | −0.45 | 0.33 | 0.26 | −0.19 | −0.62 | BX284668.4 | 0.06 | 0.86 | 0.07 | −0.82 | −0.13 |
| AL161756.3 | −0.99 | 1.10 | 0.96 | 0.40 | 0.24 | AC097468.3 | 0.33 | 0.39 | −0.41 | 0.38 | −0.14 | IGHV3-63 | −0.39 | −0.02 | 0.00 | 0.61 | −0.15 |
| PXK | −0.20 | 0.09 | 0.31 | 0.02 | 0.13 | AC009237.15 | −0.40 | −1.15 | 0.46 | −0.45 | −0.06 | G15477 | −0.21 | 0.47 | 0.07 | 1.05 | 0.26 |
| LINC00393 | −0.69 | 0.01 | 1.32 | 0.05 | 1.23 | AC006581.1 | 0.58 | −0.18 | −1.02 | −0.26 | −1.38 | SP9 | 0.09 | −0.04 | 0.20 | −1.55 | −0.51 |
| DGKD | −0.38 | −0.04 | −0.04 | 0.08 | 0.16 | MIR626 | 0.92 | −0.83 | 1.55 | −0.89 | 0.79 | SAGE4P | 0.09 | 0.55 | −2.81 | 0.53 | −2.49 |
| RBM18 | 0.33 | 0.01 | −0.02 | −0.09 | −0.30 | AC139100.1 | 0.23 | 0.24 | 0.15 | 0.25 | 0.03 | AL606760.2 | 0.08 | −0.50 | 2.89 | −0.77 | 0.09 |
| EXOC7 | −0.17 | 0.10 | −0.08 | 0.04 | −0.07 | AC005593.1 | 0.60 | 0.06 | −0.49 | 0.94 | 0.39 | AC022868.1 | −0.03 | 0.26 | −0.28 | 0.47 | −0.04 |
| RNU2-32P | −1.90 | 0.51 | 0.64 | −1.09 | −0.51 | AL121832.3 | −0.23 | 0.17 | −0.12 | −0.05 | −0.38 | AC004918.3 | −0.03 | 0.21 | 0.23 | −0.02 | 0.11 |
| ADGRG6 | 0.41 | −0.13 | −0.41 | 0.13 | −0.03 | AC007485.2 | 0.16 | −0.02 | 0.25 | −0.05 | 0.27 | NUTF2P5 | −0.09 | −0.63 | −0.08 | −0.95 | −0.50 |
| STRADA | −0.22 | −0.13 | 0.30 | −0.14 | 0.19 | AC010653.1 | 0.29 | 0.08 | 0.03 | −0.04 | −0.31 | AC104971.2 | 0.11 | −0.79 | 0.26 | −2.05 | −1.25 |
| AC016582.1 | −1.03 | −0.22 | 0.74 | 0.22 | 0.01 | AL078604.1 | 0.53 | −0.44 | −0.20 | −0.68 | −0.22 | SPACA9 | −0.02 | 0.43 | 0.25 | 0.32 | −0.02 |
| AC006254.1 | −0.70 | 0.73 | 0.50 | 0.47 | −0.12 | RGS8 | −0.43 | −0.29 | −0.47 | 0.47 | −0.24 | AL355379.1 | −0.13 | −0.01 | −1.99 | −0.25 | −1.83 |
| AC002306.1 | −0.70 | 0.00 | −0.41 | 0.19 | 0.22 | MTHFD1P1 | 0.27 | 0.13 | 0.17 | 0.05 | 0.04 | AC008761.3 | −0.24 | −0.95 | −1.16 | −0.81 | −0.77 |
| RARSP1 | 1.04 | −1.09 | −1.27 | −0.79 | −0.61 | MIR5695 | −0.35 | 0.46 | 0.01 | 0.47 | 0.35 | KRT18P27 | −0.39 | 0.14 | −1.11 | 1.08 | −1.69 |
| SPEN | 0.16 | 0.01 | −0.23 | 0.01 | −0.12 | G7758 | −1.18 | −0.14 | 0.42 | 1.85 | 0.40 | RNA5SP504 | −0.39 | 0.15 | 0.30 | 1.28 | 0.11 |
| SNHG19 | 0.46 | −0.18 | −0.16 | 0.01 | −0.13 | C22orf15 | −0.34 | 0.84 | 0.65 | 0.55 | 0.09 | MALSU1 | −0.01 | −0.10 | 0.31 | −0.18 | 0.16 |
| RP11-14N7.2 | −0.89 | 0.40 | 0.74 | −0.32 | 0.07 | AP001107.4 | 0.22 | 0.06 | 0.21 | −0.24 | −0.14 | OCLN | −0.02 | 0.57 | 0.44 | 0.06 | −0.65 |
| PHRF1 | −0.37 | 0.02 | −0.26 | 0.22 | 0.13 | PXN | 0.14 | −0.24 | −0.56 | 0.00 | −0.06 | BNIP3P36 | −0.25 | −0.19 | −0.89 | 0.15 | −0.86 |
| LINC01229 | −0.80 | 0.69 | 0.31 | 0.14 | −0.65 | RFLNA | 0.32 | −0.42 | −0.40 | −0.50 | −0.59 | AP000403.1 | −0.39 | 0.22 | −0.68 | −0.65 | −0.79 |
| RN7SKP255 | −0.45 | 0.65 | 0.70 | 0.13 | −0.24 | AC073326.1 | −0.39 | −0.37 | 0.65 | −0.50 | −0.39 | AC022601.1 | −0.06 | 0.24 | 0.99 | 0.45 | 0.20 |
| MZB1 | 0.97 | 0.27 | 0.64 | −0.29 | −0.12 | COPRS | 0.12 | −0.01 | 0.11 | −0.11 | 0.03 | LINC00375 | 0.24 | −1.16 | −1.53 | −0.17 | −0.94 |
| OSGEPL1 | −0.37 | 0.26 | 0.25 | 0.09 | 0.21 | AC133555.4 | 0.84 | 0.53 | 0.52 | −0.30 | −0.14 | AC004129.1 | 0.39 | 0.14 | 0.23 | −0.31 | −0.49 |
| AC010735.1 | −0.86 | 1.09 | −1.12 | 0.64 | −0.92 | NCOR1 | −0.05 | −0.01 | −0.04 | −0.04 | −0.05 | OTUD6B | −0.01 | −0.15 | −0.13 | −0.11 | 0.03 |
| PHKA1 | 0.24 | −0.03 | −0.22 | 0.14 | −0.02 | OR8B12 | 0.76 | −1.57 | −0.63 | 0.76 | 2.07 | GIP | 0.24 | −1.31 | 0.53 | 0.19 | 0.04 |
| LINC01431 | −0.73 | 0.59 | 0.88 | 0.13 | −0.36 | CDRT15P1 | 0.27 | −0.48 | −0.56 | 0.38 | 0.26 | RBM22P12 | −0.39 | −0.46 | −2.18 | 1.53 | −0.25 |
| SGTA | 0.29 | −0.17 | −0.56 | −0.07 | −0.15 | FAM155A | 0.29 | −0.03 | 0.61 | −0.27 | 0.10 | AC006064.3 | −0.06 | −0.17 | −0.31 | −0.46 | −0.45 |
| AC087289.3 | −1.31 | 0.04 | 1.30 | −0.12 | 0.56 | MDS2 | −0.43 | −0.63 | −0.20 | −0.34 | 0.86 | AL390816.1 | 0.39 | −1.09 | −0.51 | 1.19 | 0.69 |
| ECD | 0.17 | −0.09 | −0.13 | −0.10 | −0.14 | CENPBD1 | 0.11 | 0.04 | 0.10 | −0.03 | 0.05 | RPL23AP8 | 0.14 | 0.29 | −0.30 | 0.61 | 0.84 |
| RNA5SP268 | 1.31 | −0.68 | 0.32 | 0.32 | 1.21 | SLC28A1 | −0.60 | −0.13 | −0.08 | 0.29 | 0.36 | AC022730.4 | 0.06 | −0.35 | −0.77 | 0.20 | −0.71 |
| AC099329.1 | 1.48 | −0.93 | −1.21 | 0.15 | −0.75 | AP002833.1 | −0.58 | −0.23 | 0.73 | −0.09 | 1.22 | LINC01370 | −0.12 | 0.65 | −2.28 | 0.02 | −2.03 |
| AL132875.3 | 1.58 | −0.48 | −1.25 | 0.84 | 0.11 | MTCO2P19 | 0.34 | −0.36 | 1.14 | −0.19 | 0.45 | OR13K1P | −0.37 | −0.50 | −2.22 | 1.02 | 1.60 |
| MAT2B | 0.37 | −0.05 | 0.00 | −0.13 | −0.13 | CYCSP24 | −0.23 | −0.38 | −0.20 | 0.59 | 0.62 | PRR29 | 0.05 | −1.19 | 0.45 | −0.29 | −0.35 |
| RBM47 | 0.37 | −0.36 | −0.46 | −0.06 | 0.00 | AC079944.1 | 1.13 | 0.93 | −1.21 | 0.83 | −1.59 | AC008737.1 | 0.04 | 0.16 | 0.33 | −0.12 | −0.15 |
| RPL35A | 0.42 | −0.07 | 0.03 | −0.25 | −0.36 | ST13P18 | −0.38 | −0.78 | −0.07 | −0.48 | 0.78 | AC067945.3 | 0.10 | −0.70 | 0.73 | −0.33 | 0.75 |
| HLA-DPA1 | 0.58 | −0.59 | −0.07 | −0.34 | 0.11 | KRT1 | 0.36 | 0.64 | 0.25 | 1.37 | −0.67 | AC087463.2 | 0.38 | 0.08 | −1.28 | −0.32 | −2.13 |
| DDN | 0.96 | −0.83 | −1.48 | −0.09 | −0.62 | AL162502.1 | 0.36 | −0.10 | 0.38 | 0.13 | 0.00 | LINC02385 | −0.39 | −0.24 | 1.45 | −1.02 | 0.31 |
| HIKESHI | 0.37 | −0.16 | 0.25 | −0.27 | −0.06 | AC007386.1 | −0.36 | 0.40 | −0.09 | 0.67 | 0.10 | IGKV2-24 | 0.17 | −1.24 | −0.11 | −0.32 | −1.31 |
| CSDC2 | −0.75 | 0.63 | 0.60 | 0.36 | 0.22 | AC006449.5 | −0.35 | −0.15 | 0.05 | 0.14 | 0.23 | RNA5SP360 | 0.25 | −1.20 | −0.47 | −0.08 | 0.77 |
| LINC01474 | −1.23 | 1.57 | 0.42 | 1.24 | 0.15 | MAFA | −0.50 | −1.56 | −1.61 | 0.37 | 0.59 | AP003040.1 | −0.12 | −1.51 | −0.87 | −0.83 | −0.91 |
| HCN3 | −0.46 | 0.32 | 0.38 | 0.41 | 0.24 | DPEP3 | −0.53 | −0.49 | −1.23 | 0.96 | 0.27 | AC018683.1 | −0.38 | −0.25 | −0.49 | 1.00 | −2.55 |
| SLC38A6 | −0.38 | 0.04 | 0.05 | 0.08 | 0.06 | AL022313.2 | 0.98 | −1.46 | −1.34 | −1.32 | −1.51 | MTND6P25 | −0.19 | −1.01 | 0.06 | 0.33 | −0.30 |
| NFE2L3P1 | 1.26 | −1.16 | −1.36 | 0.76 | 1.12 | SULT1A3 | −0.48 | −0.54 | −0.25 | −0.67 | 0.61 | AL359694.2 | 0.21 | −0.26 | −0.06 | 0.73 | −0.61 |
| RNA5S9 | −1.26 | 0.72 | −1.47 | 1.05 | −1.25 | AL662907.3 | −0.43 | −1.37 | −0.14 | 1.23 | 0.74 | IGKV1-16 | 0.38 | 1.46 | 0.46 | 1.26 | −0.80 |
| AL357992.1 | −0.93 | 0.22 | 1.50 | −0.06 | 0.73 | HLA-DRB6 | 0.25 | −0.59 | −0.04 | −0.11 | 0.56 | RNA5SP326 | 0.38 | −0.90 | −0.22 | 1.43 | −0.25 |
| AL050341.2 | −0.35 | 0.06 | 0.25 | 0.22 | 0.23 | AC107214.1 | 0.22 | −0.36 | 0.15 | −0.30 | 0.00 | AC091819.2 | −0.38 | −0.79 | −0.46 | 1.75 | 1.74 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| RIDA | 0.57 | −0.29 | −0.04 | −0.35 | −0.12 | AC097505.1 | −0.78 | 0.72 | 0.54 | 0.99 | −0.11 | LRRC37A15P | −0.03 | −0.58 | 0.64 | 0.25 | 0.32 |
| C9orf43 | −0.56 | 0.02 | −0.51 | 0.30 | −0.28 | RPL26P6 | 0.17 | −0.06 | −0.05 | −0.12 | −0.18 | LINC02038 | 0.30 | −1.38 | −0.44 | −0.20 | 1.39 |
| EIF4A2P1 | 1.67 | −0.88 | −1.28 | 0.05 | −1.11 | MAP7D2 | −0.17 | 0.16 | −0.09 | −0.02 | −0.57 | AC053503.1 | −0.21 | 1.59 | −1.20 | 1.10 | −2.81 |
| PLEKHM3 | −0.20 | 0.12 | 0.25 | −0.02 | 0.07 | MIR425 | 0.77 | −0.89 | −0.42 | −1.23 | −1.77 | NDUFV2-AS1 | −0.02 | 0.06 | 0.06 | 0.02 | −0.16 |
| AL121957.1 | −1.09 | 0.56 | 1.63 | −0.02 | 0.71 | MTCO2P15 | 0.34 | 0.03 | 0.50 | 0.18 | 0.86 | ADNP-AS1 | −0.02 | 0.32 | 0.15 | 0.20 | 0.00 |
| RHEB | 0.24 | −0.15 | −0.36 | 0.01 | −0.20 | OR2L1P | −0.57 | −0.74 | −0.07 | −0.04 | 0.42 | AC015813.5 | −0.03 | −0.19 | −0.27 | 0.00 | 0.42 |
| LRRC1 | 0.27 | 0.05 | −0.29 | 0.18 | −0.08 | LINC01586 | −0.49 | 0.61 | −0.23 | 0.37 | 0.36 | NEFHP1 | 0.08 | −1.95 | −1.42 | −0.33 | −0.36 |
| AL035252.3 | −0.66 | 0.05 | 0.31 | 0.24 | 0.37 | PPP1R1C | 0.33 | −0.04 | 0.01 | −0.13 | −0.16 | AC116914.2 | −0.04 | −0.73 | −0.32 | 0.00 | 0.91 |
| HHATL | −1.33 | −2.21 | −0.15 | −0.26 | 0.78 | AP001541.1 | −0.80 | −0.73 | −0.90 | −1.13 | −0.93 | AC097639.2 | 0.06 | 0.39 | 2.42 | −0.17 | 0.12 |
| AL139193.2 | 0.80 | −0.13 | −1.23 | 0.06 | −0.90 | SLCO4A1 | −0.16 | −0.18 | −0.51 | 0.05 | 0.09 | AC108688.1 | −0.02 | 0.12 | 0.20 | 0.11 | 0.14 |
| RNA5SP53 | −1.53 | 0.29 | 0.82 | −0.08 | −0.09 | SLC6A18 | −0.74 | 0.18 | −0.59 | 1.98 | 0.14 | HECW1-IT1 | 0.08 | 0.41 | −0.51 | −0.20 | −0.92 |
| AL645608.7 | −0.69 | 0.11 | −0.73 | 0.27 | −0.21 | AC004381.3 | 0.51 | −0.56 | 0.16 | −0.05 | 1.53 | HNF4A-AS1 | −0.20 | −0.52 | 0.64 | −1.14 | 0.05 |
| AC099489.1 | −0.72 | −0.37 | 0.11 | 0.00 | 0.00 | OPRL1 | −0.36 | 0.10 | −0.56 | 0.17 | −0.16 | GLB1L2 | −0.02 | 0.29 | 0.08 | 0.50 | 0.06 |
| HSPB8 | −0.51 | 0.69 | 0.68 | 0.13 | −0.70 | AC027801.3 | −0.47 | 0.70 | 2.79 | −0.05 | 0.14 | SPATA16 | −0.09 | −0.33 | −0.89 | 0.79 | 0.54 |
| CPM | −0.50 | 0.28 | 0.60 | −0.10 | −0.14 | RNU6-1262P | −0.27 | −0.63 | −0.08 | 0.00 | 0.22 | AL591767.2 | 0.12 | −0.13 | −1.05 | −0.03 | −0.71 |
| SNORA2A | −0.71 | 0.33 | 0.17 | 0.67 | −0.02 | LSM1P1 | −0.40 | 0.61 | −0.21 | 0.37 | 0.40 | AL512408.1 | 0.03 | −0.05 | −0.71 | 0.29 | −0.12 |
| AC006557.1 | −0.82 | 0.42 | 1.01 | 0.17 | 0.44 | AL512791.2 | −0.24 | −0.41 | −0.11 | 0.00 | 0.13 | FLJ34503 | −0.05 | −0.19 | 1.42 | −0.90 | 0.78 |
| RNF123 | −0.29 | 0.03 | −0.02 | 0.11 | 0.03 | DSCAM-IT1 | 1.37 | −1.50 | −2.41 | −1.87 | −1.68 | AL591501.1 | −0.31 | 0.12 | 1.25 | −0.44 | 1.66 |
| RNF213 | 0.29 | −0.49 | −0.55 | −0.32 | −0.10 | AL121935.1 | 0.43 | −0.75 | −0.59 | −0.18 | 0.52 | RNA5SP28 | −0.16 | 0.55 | −0.06 | 0.67 | 0.02 |
| SLC38A10 | −0.25 | −0.08 | 0.18 | −0.11 | 0.16 | CDK5RAP3 | −0.11 | 0.29 | 0.35 | 0.15 | −0.05 | AC007923.1 | −0.10 | −0.74 | −0.73 | −0.65 | 0.00 |
| RAB4B | −0.62 | −0.17 | 0.55 | 0.02 | 0.47 | LINC00836 | −0.57 | −0.23 | −0.44 | −0.09 | −1.12 | RN7SKP192 | 0.33 | −0.75 | −0.18 | 0.89 | −1.15 |
| GCOM1 | 0.63 | 0.27 | −0.34 | 0.53 | −0.95 | OR51F1 | 1.03 | −0.17 | −1.10 | −0.17 | −1.39 | GALNT11 | −0.01 | 0.10 | 0.08 | 0.04 | −0.10 |
| AC093019.1 | 1.20 | −0.70 | −0.44 | −0.13 | 0.41 | AL049745.1 | 0.54 | −1.04 | −0.64 | 1.01 | 1.07 | AL138889.2 | 0.38 | −0.66 | −0.29 | −1.40 | 0.95 |
| MESP2 | 0.99 | −1.12 | −0.98 | 0.04 | 0.41 | AL360267.2 | −0.58 | −1.10 | 3.75 | −0.75 | 1.94 | RNU6-1019P | −0.04 | 0.02 | 1.34 | 0.54 | 1.71 |
| SEC24C | 0.19 | −0.12 | −0.26 | −0.03 | −0.17 | RNU6-157P | 0.74 | −0.24 | −0.15 | −0.43 | −0.28 | AC006033.1 | −0.29 | −0.61 | 0.52 | 0.21 | 1.05 |
| RPL23AP11 | 0.90 | −0.78 | −1.73 | 0.04 | −0.38 | HIST1H4A | 0.22 | −0.70 | −0.67 | 0.15 | −0.37 | AL138930.1 | −0.06 | −0.08 | 1.44 | 0.24 | 1.11 |
| GOS2 | −1.50 | 0.17 | 1.53 | −0.22 | −0.40 | AP003068.4 | 0.23 | −0.03 | −0.71 | 0.02 | −0.46 | G11194 | −0.17 | −0.63 | 2.56 | 0.53 | 1.36 |
| RAB9A | 0.39 | −0.11 | 0.11 | −0.32 | −0.22 | GAPDHP46 | −0.35 | 1.27 | −0.38 | 1.15 | 0.17 | AC079776.1 | −0.38 | 0.09 | −0.50 | 1.09 | −0.77 |
| POPDC2 | −0.69 | −0.25 | 0.31 | 0.01 | 0.18 | OR4K3 | 0.76 | −0.75 | −2.50 | 0.26 | −0.84 | RNU6-724P | −0.07 | 0.66 | 0.84 | −0.49 | −1.53 |
| RN7SL805P | −0.85 | 0.43 | 0.48 | 0.32 | 0.03 | RNA5SP188 | 0.62 | −0.03 | −2.04 | 0.60 | −1.19 | AC073349.3 | 0.38 | 0.68 | −1.53 | −0.24 | −1.20 |
| AC018926.2 | 0.94 | −0.47 | −1.56 | −0.06 | −0.70 | LINC00051 | −0.45 | −0.47 | 0.72 | 0.18 | 1.10 | CIB3 | −0.10 | −1.58 | −2.17 | −0.66 | −0.49 |
| MPP4 | −0.69 | −0.38 | 0.23 | 0.19 | 0.20 | CD244 | 0.36 | −0.51 | 0.70 | −0.72 | 0.29 | OR9G4 | 0.17 | −0.53 | −0.12 | −0.65 | 0.10 |
| RDH10-AS1 | 0.47 | −0.03 | −0.26 | 0.08 | −0.25 | LINC00982 | −0.41 | 0.24 | −0.38 | 1.45 | 0.70 | AP000911.2 | −0.04 | 0.00 | 0.18 | −0.17 | −0.57 |
| CTXND1 | −0.68 | 1.01 | 0.06 | 0.43 | −0.53 | RPL5P7 | 1.06 | −0.64 | −1.10 | −0.09 | −0.78 | RNU6ATAC31P | −0.38 | −0.40 | 0.37 | 0.81 | 2.19 |
| PAK5 | −1.38 | 0.44 | −0.11 | 0.49 | 0.42 | AC254562.2 | −0.37 | 0.30 | 0.01 | 0.99 | 0.53 | AC097520.1 | 0.31 | −0.40 | −0.57 | 1.16 | −0.43 |
| HIST2H2AA4 | 0.91 | −0.71 | −1.90 | −0.31 | −0.62 | MPP6 | 0.10 | −0.03 | −0.03 | −0.09 | 0.09 | AC092646.1 | −0.19 | 1.29 | 0.37 | 0.61 | 0.14 |
| STH | −1.65 | 0.17 | 1.27 | 0.97 | 2.34 | AL136537.2 | −0.82 | −0.58 | 0.22 | 0.04 | −1.44 | CST1 | −0.25 | 0.25 | −1.10 | 1.16 | 0.27 |
| DNAJC24 | −0.19 | 0.02 | 0.03 | −0.01 | 0.02 | AC122688.4 | −0.48 | −0.14 | −0.18 | 0.30 | 0.19 | AP000766.1 | −0.01 | −0.01 | 0.03 | 0.18 | 0.20 |
| C2CD2 | −0.43 | 0.36 | 0.17 | 0.05 | 0.06 | AC006453.2 | −0.19 | 0.02 | 0.28 | 0.17 | 0.32 | RPS27AP18 | −0.17 | −1.13 | −0.25 | 1.38 | 1.41 |
| G24578 | 1.59 | −1.11 | −1.55 | −0.93 | −1.10 | AGAP10 | −0.30 | −0.33 | 0.28 | 0.09 | 0.73 | AC084878.1 | 0.38 | −0.66 | −1.00 | 0.29 | 0.37 |
| AP002373.1 | 1.77 | −0.26 | −2.13 | 0.02 | −1.59 | KISS1R | 0.74 | −0.45 | −0.73 | −1.27 | 0.15 | RNU7-172P | 0.07 | −0.12 | 0.74 | −0.13 | 0.11 |
| SCAMP1 | 0.33 | −0.02 | −0.10 | 0.00 | −0.15 | OR51A6P | 0.85 | −0.14 | −2.31 | 1.84 | −1.92 | AC121247.2 | −0.15 | −0.06 | −0.15 | −0.18 | −0.46 |
| AC005828.1 | 0.89 | −0.70 | −0.29 | −0.38 | 0.25 | AL590128.1 | −0.39 | −0.56 | −0.60 | −0.66 | −0.03 | ANGPTL3 | 0.02 | 0.12 | −0.22 | 0.07 | −0.05 |
| KTI12 | 0.73 | −0.09 | −1.08 | 0.22 | −0.65 | AC005696.1 | −0.33 | −0.03 | 0.07 | 0.78 | 0.08 | AC073648.2 | 0.16 | 0.08 | −0.85 | 0.75 | 1.07 |
| FMN2 | −0.84 | 0.11 | 0.90 | 0.02 | 0.50 | AC012183.1 | 0.55 | −0.66 | −2.42 | 0.51 | −0.66 | DENND6A-DT | 0.05 | −1.02 | −1.22 | 0.65 | 0.45 |
| OPLAH | −0.46 | 0.61 | −0.34 | 0.65 | 0.20 | LRTM2 | 0.54 | −1.16 | −0.74 | 1.29 | 0.78 | AC008432.1 | 0.23 | −1.07 | −0.85 | 0.06 | −0.10 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC134312.3 | −2.03 | 2.68 | 2.33 | 0.79 | −0.66 | SPDYE1 | 0.18 | 0.28 | 0.30 | −0.05 | −0.13 | AC008870.5 | −0.24 | 0.14 | 0.08 | 0.25 | −0.80 |
| AC007966.1 | −0.99 | 0.76 | 2.25 | −0.64 | −0.19 | CHERP | 0.08 | −0.10 | −0.30 | 0.11 | 0.00 | HMGN2P19 | 0.16 | −0.43 | −0.19 | −1.42 | −2.30 |
| AC072039.1 | 0.85 | −0.15 | −0.72 | 0.27 | −0.23 | AL592071.1 | 0.83 | −1.22 | −2.38 | −0.55 | −1.23 | AC015813.6 | −0.01 | −0.30 | 0.04 | −0.22 | −0.01 |
| KCTD16 | −1.18 | 0.45 | −0.39 | 0.42 | −0.57 | AP003108.5 | 0.41 | 0.40 | 1.29 | −0.41 | 0.78 | DCLRE1CP1 | 0.12 | −0.20 | −0.70 | −1.06 | −1.23 |
| PCOLCE-AS1 | −0.93 | 0.38 | 0.86 | 0.10 | 0.77 | G22255 | −0.53 | 1.32 | 1.63 | 0.01 | 1.36 | AL353740.1 | 0.22 | −2.10 | 0.27 | −1.26 | −0.60 |
| AC144831.1 | −0.38 | 0.58 | 0.75 | −0.29 | 0.00 | IL12RB1 | 0.28 | −0.89 | −0.23 | −0.70 | 0.40 | AL356130.2 | −0.11 | −1.92 | −2.34 | 0.90 | −0.63 |
| G27759 | 1.16 | −1.19 | −1.65 | −0.15 | −0.46 | EXOC5P1 | 0.49 | 0.25 | −1.46 | 0.47 | −2.11 | AC110716.1 | −0.35 | −0.54 | 1.72 | −0.11 | 1.77 |
| AC109992.2 | 0.74 | −0.13 | −0.20 | 0.43 | 0.05 | RNU6-999P | −0.79 | −1.40 | 0.38 | −1.85 | −0.11 | IGKV10R1-1 | −0.21 | −0.20 | −0.34 | 1.04 | −0.67 |
| MTND1P23 | −0.61 | 0.40 | 0.59 | 1.56 | 0.08 | MBLAC1 | −0.19 | 0.14 | −0.43 | 0.37 | −0.23 | SUB1P4 | 0.10 | −0.55 | 0.53 | 0.04 | −0.74 |
| AC093218.1 | −0.88 | 0.46 | 0.63 | 0.33 | 0.08 | AC020893.1 | 0.23 | −0.19 | 0.24 | −0.25 | −0.15 | G4643 | 0.05 | 0.15 | 0.84 | −0.33 | 0.05 |
| GPI | 0.25 | −0.27 | −0.40 | −0.04 | 0.02 | STK24-AS1 | −0.26 | −0.23 | 0.26 | 0.26 | 0.85 | AL137804.1 | −0.38 | 0.49 | −0.72 | 0.69 | −1.29 |
| RELB | 0.56 | −0.79 | −0.84 | −0.21 | −0.22 | AC138430.1 | −0.77 | −0.46 | −0.50 | −0.17 | 0.88 | IQANK1 | 0.02 | 0.11 | −0.01 | 0.24 | 0.20 |
| AC017002.3 | 0.76 | −1.06 | −0.87 | −0.53 | −0.26 | HTATSF1 | 0.11 | −0.11 | −0.03 | −0.11 | −0.01 | AL163195.2 | −0.37 | −0.07 | 1.05 | 0.75 | 1.14 |
| AC022447.3 | −2.22 | 1.54 | 0.36 | 0.35 | −0.91 | PHBP4 | −0.53 | 0.46 | 1.37 | 0.42 | −0.33 | AC006133.1 | 0.37 | 0.09 | −1.84 | 2.22 | −2.02 |
| METTL22 | −0.25 | 0.07 | 0.21 | 0.06 | 0.18 | RXFP4 | 0.28 | −0.22 | −0.44 | 0.15 | −0.02 | OR13D2P | −0.37 | 1.13 | −0.03 | 1.06 | −1.79 |
| AC018638.4 | −0.43 | 0.26 | 0.29 | 0.00 | 0.16 | MYBPHL | −0.37 | 0.34 | 1.21 | −0.07 | 0.15 | LINC00555 | −0.24 | −0.80 | −0.60 | 0.45 | −1.40 |
| DLGAP3 | 0.81 | −1.52 | −0.89 | −0.93 | −0.15 | MGAT4B | 0.08 | −0.07 | −0.31 | 0.10 | −0.04 | AL118558.2 | −0.04 | 0.39 | 0.34 | −0.14 | −0.34 |
| AC106872.2 | 1.63 | −0.44 | −1.68 | 0.59 | −0.73 | AL157373.2 | −0.44 | 0.55 | 0.43 | 0.22 | −0.04 | AC092068.1 | 0.18 | −1.15 | 1.31 | −0.31 | 1.58 |
| AL109914.1 | −1.64 | −0.03 | 1.63 | 0.02 | −0.18 | KCNG2 | −0.22 | −0.14 | −0.41 | 0.25 | 0.10 | AC087257.2 | 0.02 | −0.12 | 0.27 | −0.26 | 0.29 |
| RCCD1 | −0.38 | 0.32 | 0.12 | 0.37 | 0.19 | PAQR3 | 0.13 | 0.04 | 0.19 | −0.11 | −0.08 | AC123788.1 | −0.19 | −0.30 | −0.10 | 1.15 | 0.88 |
| PARVB | −0.44 | 0.05 | 0.28 | −0.07 | 0.01 | AC012510.1 | 0.95 | 0.30 | −1.21 | 0.49 | −2.23 | AC233981.2 | 0.12 | −0.18 | −1.68 | 0.23 | −1.95 |
| HNRNPDL | 0.23 | −0.14 | −0.32 | 0.00 | −0.03 | AP001010.1 | 0.83 | 0.12 | −1.71 | 0.39 | −1.19 | EXOC6B | 0.01 | 0.20 | 0.10 | 0.07 | −0.08 |
| CCDC61 | −0.38 | −0.06 | 0.11 | 0.06 | 0.35 | NME6 | 0.07 | 0.00 | −0.07 | −0.01 | 0.01 | AP002518.1 | 0.04 | −0.90 | 1.23 | −0.42 | 0.66 |
| SCT | −1.70 | −0.56 | 1.34 | 0.12 | 0.72 | BPIFB6 | 1.09 | −0.07 | −1.34 | 0.74 | 0.30 | LINC01553 | −0.06 | −0.01 | −0.19 | 1.23 | −0.35 |
| PSMC3IP | 0.35 | −0.54 | −0.56 | −0.27 | −0.07 | AC099513.1 | 0.46 | −0.41 | −1.06 | −0.45 | −1.21 | AC096588.1 | −0.17 | −1.55 | 1.00 | −0.95 | 1.40 |
| POLI | −0.34 | 0.23 | 0.30 | 0.18 | 0.28 | AC009690.2 | −0.22 | −0.05 | 0.61 | 0.16 | 0.39 | CHST13 | −0.07 | −0.56 | −0.40 | −0.65 | 0.31 |
| PHEX | 0.58 | −0.28 | −0.78 | 0.41 | 0.23 | GSTM1 | −0.28 | 0.43 | −0.20 | 0.21 | −3.99 | AC044810.1 | −0.07 | 1.62 | 2.60 | 0.83 | 0.44 |
| ELK4 | 0.28 | −0.01 | −0.08 | 0.01 | −0.14 | BNIP3P4 | −0.35 | −0.38 | 0.74 | −0.59 | 0.17 | MYL12BP2 | 0.09 | −0.94 | 0.04 | −1.12 | −0.07 |
| KCNAB2 | −0.46 | 0.09 | −0.27 | 0.20 | 0.12 | AC087465.1 | −0.44 | 0.12 | 0.40 | −0.03 | −0.46 | RNU6-218P | −0.07 | 0.63 | 0.37 | 0.21 | 0.86 |
| RNU6-322P | 1.08 | −0.83 | −0.87 | 0.34 | 0.70 | FKSG61 | 0.69 | −1.09 | 0.00 | 0.67 | 1.49 | AGMAT | −0.02 | −0.47 | −1.09 | −0.04 | −0.26 |
| CPSF4 | −0.26 | 0.17 | −0.01 | 0.15 | −0.11 | AC122136.1 | 0.67 | 0.01 | 0.58 | −0.22 | 0.27 | IGHV3OR16-9 | 0.37 | −0.73 | −0.53 | −1.52 | −2.64 |
| AC005532.2 | −1.63 | −1.55 | 1.37 | −0.53 | 1.84 | RCC2P6 | −0.38 | 1.28 | −0.13 | 0.50 | 0.30 | AC005832.2 | −0.10 | −0.68 | −1.81 | 0.89 | −0.34 |
| C21orf62 | −0.98 | −0.36 | 1.42 | −0.34 | 1.12 | AF111169.3 | 0.39 | 0.43 | −0.45 | −0.14 | −1.11 | MTCYBP12 | −0.11 | 0.56 | −2.14 | 1.43 | −1.72 |
| LYVE1 | −0.87 | 0.83 | 0.62 | 0.75 | −0.60 | SRRM3 | −0.16 | 0.16 | 0.44 | −0.03 | 0.07 | PAGE3 | 0.17 | −1.45 | −1.41 | 1.01 | −0.79 |
| MTND1P14 | −1.43 | −1.97 | 0.91 | 0.11 | 2.88 | PPIAP19 | −0.28 | 0.50 | 0.43 | −0.32 | −0.06 | AC104071.1 | 0.26 | −0.74 | −0.97 | 0.18 | 0.30 |
| KCNAB1-AS1 | −2.03 | 1.58 | 1.41 | 0.99 | −0.05 | AF131215.4 | 0.19 | 0.22 | 0.27 | −0.01 | 0.29 | DNAJA1P4 | −0.25 | 0.75 | 0.69 | 0.05 | 0.04 |
| AC093330.1 | 1.08 | −0.96 | −0.34 | −0.20 | 0.48 | OSBPL9P4 | −0.18 | 0.47 | −0.26 | 0.48 | −0.05 | AL136452.1 | −0.37 | 0.46 | −0.45 | −0.73 | −1.28 |
| CCDC122 | −0.34 | 0.16 | 0.51 | 0.10 | 0.34 | LINC01940 | 0.26 | −0.54 | 0.49 | −0.55 | 0.58 | FAM151A | −0.04 | 0.49 | −0.25 | 0.21 | −0.02 |
| AL021707.4 | −0.87 | 0.30 | 1.21 | 0.68 | 0.64 | HSP90B2P | 0.12 | −0.06 | 0.24 | −0.02 | 0.26 | LINC00845 | −0.37 | 0.42 | −0.29 | −1.54 | −0.80 |
| AL133368.2 | −0.63 | −0.23 | −0.16 | 0.36 | 0.22 | AC011825.2 | 0.22 | −0.33 | 0.01 | −0.37 | 0.39 | AC008522.1 | −0.04 | 0.51 | 0.84 | 0.57 | 0.74 |
| ABCA11P | −0.68 | 0.02 | 0.79 | 0.19 | 0.41 | AGGF1P5 | −0.83 | 1.18 | −0.10 | −0.49 | −1.63 | ASS1P7 | 0.12 | −0.08 | −0.33 | 1.56 | 1.73 |
| AC073410.1 | −0.49 | 0.14 | 0.63 | 0.06 | 0.25 | AC005912.1 | 0.20 | 0.21 | 0.19 | −0.15 | −0.45 | AL589765.1 | −0.03 | 0.05 | 0.76 | 0.03 | 0.18 |
| AL355607.2 | 1.49 | −0.50 | −0.17 | 0.18 | −0.63 | AC016644.1 | 0.34 | 0.41 | −0.70 | −0.01 | −0.99 | AC139768.1 | −0.08 | 0.46 | 0.96 | −0.59 | 0.54 |
| AC108134.4 | −1.34 | 1.04 | 0.65 | −0.40 | 0.53 | AC006111.2 | 0.28 | 0.40 | 0.39 | 0.43 | 0.15 | AC243972.1 | 0.18 | −1.34 | −0.39 | −0.40 | −0.78 |
| PPM1L | −0.30 | 0.56 | 0.52 | 0.33 | −0.04 | AC126177.6 | −0.75 | 0.40 | −1.68 | 0.55 | −1.55 | LINC02008 | −0.09 | 0.49 | −0.25 | 0.00 | 0.11 |
| PDE3B | −0.79 | 0.49 | 0.34 | 0.10 | 0.02 | AC104462.1 | −0.40 | 1.02 | 0.72 | −0.47 | 0.16 | AC114956.1 | 0.02 | 0.02 | 0.00 | 0.24 | 0.10 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| KIF26B-AS1 | 0.91 | −0.54 | −0.28 | −0.60 | 0.38 | CCDC184 | 0.28 | 0.40 | −0.93 | 0.50 | −1.11 | AP000770.1 | 0.09 | 0.19 | −1.40 | 1.51 | 1.18 |
| RPL24P8 | −0.58 | 0.65 | 0.42 | 0.48 | −0.32 | AC036108.1 | 0.31 | 0.23 | 0.17 | 0.31 | 0.29 | IL3 | 0.37 | 0.40 | 0.19 | 0.02 | −2.47 |
| COL9A3 | −0.52 | 0.48 | 0.23 | 0.42 | 0.29 | RHOQP3 | 0.49 | −1.97 | 0.32 | −0.22 | 1.14 | AL132642.2 | −0.12 | −0.19 | −0.37 | 0.68 | −0.14 |
| PKD1L3 | −0.48 | 0.25 | 0.20 | 0.07 | 0.04 | ADAM2 | 0.70 | −0.20 | −2.38 | 1.15 | −2.57 | LINC00533 | 0.37 | 0.67 | 0.65 | 0.94 | 0.88 |
| ST3GAL5 | −0.32 | 0.04 | 0.31 | 0.15 | 0.39 | AL844908.1 | 0.29 | −2.09 | 0.57 | −0.70 | 1.72 | HNRNPA1P24 | −0.03 | 0.74 | −0.96 | 0.58 | −0.97 |
| RPS23P8 | 0.71 | −0.32 | −0.03 | −0.18 | −0.35 | RNA5SP330 | 0.53 | −1.11 | 0.06 | −0.60 | 0.49 | KCNA7 | −0.02 | −0.43 | −0.37 | 0.15 | 0.71 |
| HSF1 | −0.31 | 0.02 | −0.09 | 0.16 | 0.08 | SERGEF | 0.08 | 0.15 | −0.30 | 0.15 | −0.19 | SOD2P1 | 0.36 | −1.51 | −0.31 | −0.06 | 1.37 |
| NFXL1 | 0.26 | −0.27 | −0.35 | 0.00 | 0.01 | AF130417.1 | 0.32 | −0.19 | −0.73 | 0.74 | −0.36 | AC020558.1 | 0.09 | −1.55 | −0.42 | 0.27 | 1.60 |
| MRPS31 | 0.34 | −0.14 | −0.11 | −0.21 | −0.09 | AC093912.1 | −0.73 | −0.45 | −1.01 | 0.51 | 0.75 | CELSR2 | −0.02 | 0.20 | 0.00 | 0.17 | −0.04 |
| AP002748.3 | −0.66 | 0.25 | 0.15 | 0.30 | 0.41 | AC098827.1 | −0.24 | 0.94 | −0.55 | 0.89 | −0.52 | MTND1P37 | 0.15 | 1.00 | 1.63 | 1.03 | −0.82 |
| EIF4A1 | 0.63 | −0.41 | −0.79 | −0.02 | −0.12 | OR10Z1 | −0.59 | −0.80 | −0.34 | 0.35 | −0.55 | AL139100.1 | 0.06 | 0.04 | −0.87 | 0.21 | −0.20 |
| AL354855.1 | −0.66 | 0.42 | 0.19 | 0.36 | 0.67 | AC104333.2 | 1.13 | −1.19 | −1.27 | −0.70 | −1.74 | AC078865.1 | −0.37 | 0.95 | 1.25 | −0.39 | 1.21 |
| AC068587.3 | −1.79 | 1.29 | 2.50 | −1.00 | 0.34 | AC116914.1 | −0.68 | −0.89 | −2.04 | 0.65 | −0.92 | AC108099.1 | −0.10 | 0.08 | −1.35 | 0.62 | −1.30 |
| SMCHD1 | 0.25 | −0.21 | −0.05 | −0.15 | −0.02 | AC093865.1 | 0.30 | −0.22 | −0.64 | −0.07 | 0.03 | AC103808.5 | −0.37 | −0.15 | NA | 1.66 | −0.38 |
| PNRC1 | −0.40 | 0.40 | 0.53 | 0.15 | 0.10 | AC110048.1 | −0.41 | 1.03 | 0.91 | 0.41 | 0.21 | AC007603.3 | −0.35 | −0.85 | −1.12 | 0.32 | −0.82 |
| AL157402.2 | 0.82 | −0.79 | −0.03 | −0.23 | 0.02 | C3orf86 | 0.79 | 0.24 | −2.83 | 0.00 | −1.58 | AC091860.2 | −0.37 | 0.18 | 0.19 | −0.03 | −0.56 |
| PANK2 | 0.19 | −0.14 | −0.17 | −0.01 | 0.01 | GNL3LP1 | 0.61 | −0.47 | 2.44 | −0.83 | 0.97 | PSMB11 | 0.15 | −0.13 | −1.09 | 0.23 | −2.42 |
| NXNL2 | −1.22 | 0.73 | 0.41 | 1.09 | 0.21 | GJE1 | −0.85 | −0.79 | 1.08 | −0.11 | −0.22 | AP000561.1 | 0.12 | −0.48 | −1.47 | −0.49 | −1.72 |
| AC016907.2 | −1.12 | 0.92 | 0.21 | 0.55 | 0.12 | HCG14 | 0.56 | −1.97 | −0.65 | −1.23 | −0.31 | LINC02056 | −0.12 | −0.06 | −0.79 | −0.56 | −2.56 |
| SMCO4 | −0.40 | 0.07 | 0.74 | −0.18 | 0.23 | G25045 | 0.49 | −0.59 | −0.69 | 0.14 | 0.54 | AC011626.1 | 0.37 | 0.10 | 1.27 | 0.54 | 0.35 |
| FO393411.1 | 0.97 | −0.31 | −0.53 | 0.30 | −0.71 | DPEP2NB | 1.11 | −1.46 | −1.84 | −0.15 | −0.60 | RNA5SP18 | −0.18 | 0.44 | −1.01 | −0.66 | 0.11 |
| SMCO1 | 1.77 | 0.51 | −2.56 | 0.61 | −2.48 | CDIPT | 0.13 | 0.06 | 0.03 | 0.15 | −0.26 | AC008696.2 | 0.12 | −1.00 | −1.32 | −0.76 | −0.47 |
| AF127577.2 | 0.82 | −0.54 | −1.00 | −0.86 | −0.90 | RAD51AP1P1 | 0.28 | −0.25 | −0.22 | −0.09 | −0.55 | PPIAP46 | 0.05 | 0.70 | −0.35 | −0.25 | −1.01 |
| AC093162.2 | −0.59 | 0.53 | 0.35 | 0.34 | 0.12 | GPR146 | −0.17 | 0.18 | −0.21 | 0.34 | −0.07 | AL050305.1 | 0.37 | −0.35 | 1.00 | 1.59 | 0.16 |
| PYGO1 | −0.42 | 0.55 | 0.64 | 0.06 | 0.05 | AC005531.1 | −0.45 | −0.33 | −1.29 | −0.29 | −0.58 | MEF2C-AS2 | −0.09 | 1.35 | −0.44 | −0.75 | −2.06 |
| AC055822.1 | 0.85 | −0.41 | −0.38 | 0.06 | −0.23 | FTH1P8 | −0.33 | −0.45 | 1.05 | −0.63 | 0.28 | AC107896.1 | 0.05 | 0.15 | −0.68 | −0.25 | −0.13 |
| AC072022.2 | −0.53 | −0.25 | 0.05 | −0.04 | 0.17 | MIR4803 | 0.60 | −0.05 | −0.20 | 0.69 | 0.39 | DHFR2 | −0.02 | −0.18 | 0.06 | −0.02 | 0.49 |
| PGLS | 0.20 | −0.12 | −0.29 | 0.16 | −0.06 | AC084048.1 | 1.13 | −2.01 | −1.21 | −1.30 | 2.58 | AC066613.2 | −0.05 | −0.26 | −0.52 | −0.43 | −0.96 |
| POLR3GP1 | 1.42 | −0.82 | −0.87 | −0.02 | 0.42 | NEFLP1 | 1.51 | −2.17 | −1.99 | −0.56 | −0.28 | AC105029.1 | 0.37 | −1.75 | 0.35 | −0.96 | 1.37 |
| PELO | 0.26 | −0.12 | −0.21 | −0.08 | −0.24 | LINC01150 | −0.55 | −0.66 | 0.59 | 0.03 | 0.05 | AP002990.1 | 0.02 | 0.13 | −0.16 | −0.12 | −0.33 |
| AC024270.2 | −1.30 | −0.43 | −0.36 | −0.04 | 0.52 | LINC01271 | 0.28 | −0.81 | 0.46 | −0.95 | 0.63 | AC105254.2 | 0.37 | −0.48 | −1.90 | 1.14 | −2.52 |
| AC034105.3 | 1.06 | −0.38 | −0.27 | 0.10 | −0.01 | AL359878.1 | −0.18 | −0.29 | 0.19 | −0.21 | 0.08 | HEPACAM2 | 0.07 | 0.05 | 0.28 | −0.37 | 0.04 |
| CMC2 | 0.35 | −0.42 | −0.17 | −0.12 | −0.01 | CGRRF1 | −0.16 | 0.14 | 0.49 | −0.23 | −0.15 | C7orf77 | −0.20 | −1.56 | −0.79 | 0.65 | 1.19 |
| RNF13 | 0.30 | 0.06 | −0.14 | −0.04 | −0.33 | RNU6-1115P | −0.74 | 0.75 | −1.18 | 1.18 | −1.39 | IGKV3D-11 | 0.37 | 0.21 | 1.62 | −0.08 | 1.11 |
| BRD9 | −0.36 | −0.01 | −0.23 | 0.15 | 0.04 | KRT73-AS1 | −0.36 | 0.91 | 1.73 | −0.06 | −0.18 | BCL2L14 | −0.03 | 0.39 | 0.13 | 0.05 | −0.12 |
| LINC01273 | −1.31 | −0.03 | 0.61 | −0.94 | −0.03 | KCNK18 | −0.68 | 0.73 | 0.62 | 1.67 | 1.06 | AC036108.3 | −0.02 | −0.30 | 0.01 | −0.01 | 0.07 |
| AC133552.3 | −0.86 | 0.61 | 1.07 | 0.60 | 0.82 | NEU3 | −0.07 | −0.14 | −0.08 | −0.10 | 0.05 | OR6C1 | 0.17 | −1.20 | −0.93 | 0.89 | −0.49 |
| HMGXB3 | 0.25 | −0.31 | −0.28 | −0.09 | 0.12 | G8822 | 0.29 | −0.41 | −0.55 | −0.60 | −0.78 | SPTLC1P1 | −0.04 | −0.56 | 0.54 | −0.15 | 0.14 |
| POU3F1 | 0.78 | 0.15 | −0.22 | 0.45 | 0.06 | BOD1P1 | 0.86 | 0.02 | −0.98 | 1.17 | 1.00 | RPL10P19 | −0.04 | −0.29 | 0.65 | 0.20 | 0.73 |
| HMGB2 | 0.32 | −0.50 | −0.50 | −0.41 | −0.23 | AL645940.1 | 0.38 | −0.38 | 0.18 | −0.39 | 0.02 | RPS6KB2 | 0.01 | 0.15 | −0.32 | 0.35 | −0.12 |
| AC022973.3 | 0.66 | −0.47 | −0.88 | 0.02 | 0.05 | G12029 | −0.68 | 0.84 | 0.25 | −0.46 | 0.87 | AC099754.1 | −0.37 | −0.18 | 0.55 | −0.06 | 0.17 |
| AC104113.1 | −0.54 | 0.13 | −0.20 | 0.31 | −0.29 | RNU2-34P | 1.06 | −0.62 | −1.38 | 0.60 | 0.07 | AC104119.1 | −0.37 | −0.21 | 0.55 | 1.14 | −0.55 |
| RN7SL116P | 1.51 | −1.06 | −1.07 | −0.32 | 0.25 | RN7SL682P | −1.32 | 0.17 | 0.90 | 0.66 | 0.27 | AC018553.2 | 0.03 | 0.29 | 0.17 | 0.20 | 0.32 |
| AL451064.2 | −0.70 | 0.47 | 0.78 | 0.49 | 0.31 | KLK14 | −0.26 | −0.92 | 0.24 | −0.52 | 0.42 | AC092647.3 | 0.37 | −1.26 | 0.44 | 0.01 | 3.41 |
| HPDL | 0.79 | −0.40 | −1.30 | 0.54 | −0.17 | CPNE1 | −0.08 | −0.09 | −0.34 | 0.13 | −0.03 | AC091905.2 | −0.29 | −0.32 | −0.12 | −0.21 | −1.12 |
| RPS15AP12 | 0.77 | −0.28 | −0.30 | −0.44 | −0.19 | GABRR1 | −0.32 | 0.44 | −1.11 | 1.15 | −1.19 | EPPIN-WFDC6 | −0.37 | −1.26 | 0.78 | 1.65 | 2.06 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| C12orf76 | −0.35 | 0.23 | 0.50 | 0.08 | 0.27 | KRTAP21-2 | −0.91 | −1.77 | 0.55 | −0.51 | 1.03 | RNU6ATAC14P | −0.09 | 0.83 | 0.24 | 1.13 | −0.11 |
| ART3 | −0.81 | 0.30 | 0.23 | −0.01 | 0.00 | AL445193.2 | −0.77 | 0.14 | 0.55 | 0.30 | 0.67 | AC008115.2 | 0.20 | 0.25 | −0.89 | −0.58 | −1.07 |
| SNHG17 | 0.42 | −0.46 | −0.56 | −0.02 | 0.19 | MTND4P1 | −0.63 | 0.01 | 0.06 | 0.68 | −0.44 | AC092337.1 | 0.08 | −1.66 | −0.37 | −0.21 | 0.84 |
| MIR4427 | 1.49 | −0.92 | −0.88 | −0.39 | −0.22 | AC005048.1 | −1.04 | −0.67 | 1.36 | −0.76 | 1.56 | HMGB3P13 | −0.11 | −1.69 | −0.23 | −0.64 | −0.24 |
| SEPSECS | −0.32 | 0.27 | 0.40 | 0.27 | 0.12 | AC027682.1 | 0.38 | −0.01 | 0.57 | 0.42 | 0.68 | AC018845.3 | 0.04 | −0.40 | −0.02 | 0.28 | 0.10 |
| AC069499.2 | 1.72 | −1.46 | −2.04 | −0.67 | −1.26 | RNU6-708P | 0.45 | −0.12 | 0.78 | −0.12 | 0.12 | AP001999.3 | 0.37 | −0.75 | −0.67 | −1.81 | −1.93 |
| BX679664.3 | 0.57 | −0.20 | −0.68 | −0.20 | −0.44 | GATSL2 | 0.27 | 0.48 | 0.28 | −0.18 | 0.05 | AC092120.1 | 0.04 | −0.08 | −0.07 | 0.04 | 0.45 |
| GUCD1 | 0.26 | −0.11 | −0.43 | −0.05 | −0.35 | AC004975.1 | 0.30 | −0.16 | 0.11 | −0.28 | −0.16 | CYFIP2 | 0.02 | −0.21 | 0.53 | −0.44 | 0.27 |
| KCNIP3 | −0.38 | 0.39 | −0.22 | 0.20 | −0.31 | AC010326.1 | −1.00 | −0.73 | −0.60 | −2.05 | −0.26 | AC087312.1 | 0.17 | −2.25 | −0.41 | −0.49 | 0.23 |
| DOCK10 | 0.37 | −0.41 | −0.26 | −0.21 | 0.06 | AC008758.6 | −0.55 | 1.03 | 1.31 | 1.34 | 0.90 | AC080112.2 | 0.30 | 1.07 | −1.56 | 0.04 | −2.35 |
| OR2D2 | 1.41 | −2.48 | −2.19 | 0.53 | −0.61 | CCNB1IP1P1 | 0.62 | −0.33 | −0.47 | −0.07 | 0.10 | AL353678.1 | 0.20 | 0.58 | 0.29 | 0.26 | −1.66 |
| SAMD14 | −0.59 | 0.33 | −0.02 | 0.29 | −0.23 | AP000813.1 | −0.23 | −0.04 | 0.62 | 0.47 | 0.76 | AL049794.2 | −0.35 | −0.65 | −0.09 | −0.24 | 0.84 |
| AL162584.1 | 0.70 | −0.32 | 0.03 | −0.52 | 0.30 | LINC00456 | −0.51 | 0.67 | 0.28 | 0.95 | 1.12 | AC121161.1 | −0.29 | −1.26 | 0.43 | −0.24 | −0.09 |
| AL358115.1 | 0.61 | 0.11 | −0.05 | −0.02 | 0.01 | RPL12P10 | 0.31 | −1.09 | 0.03 | 0.11 | 0.70 | CEACAM18 | 0.15 | −1.96 | −1.52 | −0.60 | 0.30 |
| SMG1P3 | −0.33 | 0.02 | 0.18 | 0.13 | 0.46 | AC023825.2 | 0.25 | −0.49 | 0.32 | −0.36 | 0.72 | AF131216.3 | −0.08 | −1.78 | 1.14 | −0.96 | 0.64 |
| BHMT | −0.83 | 0.06 | 0.01 | −0.68 | −0.40 | AC009501.2 | 0.35 | −0.47 | −0.75 | 0.29 | 0.19 | MRVI1-AS1 | −0.03 | −0.13 | 0.39 | −0.29 | 0.07 |
| AC133552.1 | −1.61 | 0.33 | 2.76 | −0.21 | 1.45 | OR52A5 | −0.67 | −0.89 | −0.75 | −0.19 | 0.59 | SPATA31A6 | −0.36 | −0.19 | 0.68 | −0.36 | 2.98 |
| NAGS | 0.59 | −0.38 | −1.19 | −0.11 | −0.49 | AC109446.4 | 0.59 | −0.58 | −1.28 | −0.02 | 0.47 | AC096579.1 | 0.34 | 0.54 | 0.74 | −0.89 | −0.47 |
| MAML2 | −0.28 | 0.29 | 0.37 | −0.01 | −0.26 | AC005261.2 | −0.28 | 0.66 | −0.09 | 0.53 | −0.11 | OR7E5P | 0.36 | −1.02 | −0.87 | −0.12 | 0.43 |
| HILPDA | −0.53 | −0.29 | −0.02 | 0.40 | 0.32 | ARPC3P5 | −0.61 | 0.55 | 0.92 | 0.69 | 1.42 | AC008060.4 | 0.15 | −1.89 | −0.75 | −1.06 | 0.90 |
| AC103810.4 | −0.97 | 0.07 | 1.35 | 0.52 | 1.53 | RN7SL151P | −0.34 | −0.06 | −0.84 | 0.44 | −0.69 | AC023162.1 | 0.18 | 0.56 | 0.31 | −1.04 | −0.44 |
| LRMP | −0.54 | 0.16 | 0.48 | 0.06 | −0.13 | AC109449.1 | 0.49 | −0.35 | 0.65 | −0.05 | 0.11 | AC020637.1 | −0.07 | −0.20 | −0.21 | 0.40 | 0.58 |
| SLC41A1 | 0.27 | −0.23 | −0.52 | −0.05 | −0.18 | OR10A4 | 0.28 | −1.09 | −1.77 | 0.38 | −1.10 | LINC01327 | 0.36 | −0.55 | −0.14 | 0.95 | −0.81 |
| AC005632.2 | 0.63 | −0.45 | −0.17 | −0.14 | 0.14 | AL583810.3 | 0.85 | 0.65 | 0.70 | −0.15 | −0.88 | AC010745.4 | 0.20 | −0.17 | −1.92 | 0.05 | −2.27 |
| AC025287.4 | −0.68 | 0.50 | 1.07 | −0.01 | 0.03 | AL513475.1 | 0.33 | −0.17 | 1.09 | −0.29 | −0.52 | LINC02152 | 0.36 | −0.05 | 1.60 | 0.24 | 0.11 |
| PHYKPL | −0.28 | −0.01 | 0.16 | −0.01 | 0.22 | KIF22 | 0.11 | −0.23 | −0.36 | 0.07 | 0.08 | CRYGA | −0.36 | 0.15 | −1.01 | 0.91 | −0.51 |
| ATRIP | 0.26 | −0.27 | −0.36 | −0.19 | 0.04 | AC067751.1 | −0.44 | −0.35 | 0.20 | −0.61 | 0.30 | RN7SKP238 | −0.29 | −0.27 | −0.61 | −0.94 | −0.74 |
| EMC1 | 0.21 | −0.15 | −0.25 | −0.04 | −0.10 | LLGL2 | −0.14 | 0.36 | −0.10 | 0.27 | −0.09 | AC005906.1 | −0.36 | −1.08 | 0.50 | −0.30 | 1.28 |
| PPIAP39 | −1.36 | −0.34 | 2.47 | −0.02 | 1.57 | AC131009.2 | 0.76 | 0.17 | −1.92 | 0.10 | −0.13 | AC139530.1 | −0.03 | 0.30 | 0.50 | 0.21 | 0.13 |
| RNU6-834P | 1.09 | 0.29 | 0.51 | −0.05 | −0.55 | RNU6-1282P | 0.55 | −0.29 | −0.26 | 0.08 | −0.04 | PGAM4 | 0.05 | 0.83 | 0.17 | 0.29 | −0.24 |
| ANKRD20A9P | −0.93 | 1.15 | 0.86 | 0.90 | 1.14 | AC068051.1 | −0.43 | −0.36 | −0.63 | 1.46 | 0.63 | NF1P5 | 0.36 | −0.19 | −1.15 | 1.22 | 0.37 |
| AL353801.2 | −1.16 | −0.33 | −0.30 | −0.12 | −0.02 | LINC00635 | −0.47 | 0.36 | −1.45 | 0.44 | −0.98 | CHORDC2P | −0.06 | −0.39 | −0.01 | 0.16 | −0.61 |
| HMGN1P8 | 0.43 | −0.26 | −0.53 | 0.03 | −0.09 | HNRNPA1P6 | −0.38 | −0.14 | 0.36 | −0.07 | 0.64 | RPL9P18 | −0.09 | −0.46 | −0.34 | 0.65 | −0.59 |
| AC135776.1 | −0.98 | 0.65 | 0.28 | 0.94 | 0.10 | OR4F17 | 0.56 | −1.17 | −0.85 | −0.08 | 0.85 | AL451164.1 | 0.08 | −0.93 | −1.09 | 0.27 | −1.35 |
| SMIM27 | −0.30 | 0.08 | 0.21 | 0.14 | 0.25 | AL158832.1 | 0.40 | −1.02 | −0.83 | −0.36 | 0.20 | ANXA2P3 | −0.11 | −0.42 | 0.37 | −1.36 | −1.00 |
| LYSMD1 | −0.28 | 0.19 | 0.39 | 0.01 | 0.18 | AC144522.1 | −0.46 | 0.28 | −0.76 | 0.46 | −1.05 | ART1 | 0.03 | −0.08 | −1.21 | −0.01 | −1.03 |
| AIP | −0.26 | 0.08 | 0.12 | 0.02 | 0.01 | OLFM3 | −0.55 | −0.11 | −0.74 | 0.15 | −0.33 | AC091027.1 | −0.36 | −0.08 | −0.90 | 0.87 | −1.01 |
| MTRF1L | 0.32 | −0.17 | −0.04 | −0.21 | 0.06 | AHSP | −0.89 | 0.72 | −2.35 | 1.47 | −0.92 | LCN9 | −0.34 | 1.08 | −0.86 | 1.01 | −3.42 |
| C14orf93 | −0.28 | 0.07 | 0.14 | 0.26 | 0.44 | RNU2-44P | −0.51 | 0.57 | 0.37 | 1.07 | 0.33 | AC009097.2 | −0.11 | −0.31 | −0.97 | 0.21 | −0.21 |
| GPR180 | 0.36 | −0.26 | −0.33 | −0.24 | 0.04 | NOP2 | 0.18 | −0.59 | −0.33 | −0.05 | 0.31 | AC008592.3 | 0.03 | 0.01 | −0.25 | 0.80 | 0.41 |
| AC105021.1 | −1.80 | 0.71 | 0.91 | 0.42 | −0.64 | G5758 | −0.41 | −0.32 | 0.43 | −0.49 | 0.89 | AP003973.2 | −0.14 | −0.97 | −1.15 | 0.44 | 0.26 |
| BRPF3 | −0.18 | 0.12 | 0.27 | −0.08 | 0.08 | PEX11G | −0.18 | 0.17 | 0.40 | 0.11 | 0.12 | LINC01548 | −0.16 | −0.15 | −1.88 | 0.22 | −0.43 |
| SFR1 | 0.45 | −0.45 | −0.88 | −0.50 | −0.35 | DTNBP1 | 0.06 | −0.15 | −0.15 | 0.04 | 0.19 | PLEKHF1 | 0.02 | −0.11 | −0.40 | −0.05 | −0.13 |
| AC091181.1 | −0.54 | 0.10 | 0.06 | 0.23 | 0.42 | AC009336.3 | 1.06 | −2.19 | 0.28 | 0.37 | 1.36 | AC244100.2 | 0.08 | 0.26 | 0.63 | 0.60 | −0.58 |
| RN7SKP195 | −1.83 | −0.33 | 1.83 | 0.62 | 0.76 | OPCML-IT1 | 1.00 | −0.20 | −1.61 | −0.34 | −1.86 | NKX2-1 | 0.20 | 0.17 | −0.24 | 1.42 | 2.36 |
| PIAS3 | −0.26 | 0.23 | 0.03 | 0.25 | −0.03 | MTRF1LP1 | −0.44 | 0.66 | 0.18 | 0.61 | 0.28 | AC104408.1 | −0.36 | −0.14 | 0.27 | −0.21 | −0.44 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| MRPL45P2 | −0.25 | −0.04 | 0.25 | −0.08 | 0.14 | POC5 | 0.08 | −0.10 | −0.06 | −0.06 | 0.05 | AL451081.1 | −0.19 | −1.16 | −1.41 | −0.18 | −0.07 |
| HECW1 | −0.59 | −0.22 | 0.36 | −0.19 | 0.41 | AP002761.3 | −0.36 | 0.14 | 1.08 | 0.40 | 0.54 | PIP4K2A | −0.01 | −0.15 | 0.09 | −0.16 | −0.02 |
| RASAL1 | −0.46 | 0.23 | 0.26 | 0.25 | 0.29 | AC005096.1 | 0.27 | −0.35 | −0.13 | −0.41 | −0.28 | DUX4L27 | 0.10 | 0.42 | −0.84 | −0.82 | −1.42 |
| AC020978.9 | −0.44 | 0.47 | 0.55 | 0.03 | −0.02 | RN7SKP184 | 0.25 | 0.16 | −0.40 | 0.13 | −0.52 | LINC00239 | −0.04 | −0.12 | −0.42 | −0.58 | −0.37 |
| AC140479.2 | 0.93 | −1.31 | −0.23 | −0.38 | 0.47 | MTCO3P15 | 0.39 | −0.58 | −0.03 | −0.16 | 0.35 | AL109809.2 | −0.35 | −0.13 | 2.15 | −0.46 | 0.74 |
| BAX | 0.29 | −0.42 | −0.34 | −0.10 | 0.11 | ELF2 | −0.06 | 0.14 | 0.18 | 0.02 | −0.02 | AL513423.1 | −0.36 | −0.97 | −0.38 | −0.15 | 0.43 |
| RLBP1 | −0.68 | 0.43 | −0.11 | 0.13 | −0.68 | RNA5SP131 | −0.99 | 0.10 | 0.98 | 2.88 | 1.28 | CNPY1 | 0.11 | 0.01 | 0.06 | 0.35 | −2.22 |
| C1RL-AS1 | 0.39 | −0.57 | −0.74 | 0.12 | 0.25 | RNU6-171P | 0.35 | −0.10 | 0.85 | −0.40 | 0.60 | GYG1P3 | −0.13 | −0.54 | −0.61 | −1.69 | −1.48 |
| AL050320.1 | −0.82 | 1.02 | 0.91 | −0.35 | −0.44 | EEF1DP5 | −0.67 | 0.11 | 1.24 | −1.28 | 0.81 | AC109315.1 | −0.34 | −0.13 | 0.27 | −1.11 | −1.52 |
| NACAP8 | −1.09 | −0.59 | 1.29 | −0.88 | 0.45 | SNORA27 | −0.45 | 0.11 | 1.05 | 0.60 | 1.38 | POLR2F | −0.01 | 0.09 | −0.01 | 0.11 | 0.02 |
| IP6K1 | 0.21 | −0.03 | −0.24 | 0.11 | −0.19 | PNMT | −0.47 | −0.30 | 0.30 | 0.08 | −1.04 | NPVF | −0.16 | −0.62 | −0.68 | −0.50 | −0.09 |
| COX6CP1 | 0.79 | −0.19 | −0.24 | −0.09 | −0.27 | HSPA1B | 0.15 | 0.13 | −0.40 | 0.28 | 0.03 | AC068279.1 | −0.06 | −0.17 | −1.00 | −0.75 | −0.21 |
| AL513327.2 | 1.36 | −0.43 | −1.76 | −0.83 | −1.39 | AC060766.1 | 0.23 | −0.14 | 0.12 | −0.19 | 0.24 | AP001972.5 | −0.02 | 0.09 | 0.25 | 0.12 | −0.11 |
| PYGO2 | 0.25 | −0.05 | −0.16 | −0.01 | −0.05 | ATP1A4 | −0.38 | −0.58 | −0.39 | 0.21 | 0.17 | AC067930.4 | −0.05 | −0.85 | 0.52 | −0.10 | 1.01 |
| FLYWCH2 | 0.29 | 0.00 | −0.21 | −0.03 | −0.03 | BNIP3P42 | −0.22 | 0.03 | 0.19 | 0.09 | 0.55 | AL645474.1 | −0.36 | −0.44 | −0.86 | 1.12 | −0.75 |
| MTCO1P46 | −1.61 | 1.10 | 1.16 | 0.18 | −0.48 | SAGE3P | 0.79 | −0.86 | −1.22 | 0.66 | −0.17 | CECR9 | −0.23 | 1.28 | 0.95 | −0.45 | −1.14 |
| AC105074.1 | 0.53 | −0.06 | −0.31 | 0.10 | −0.27 | RPS26P8 | 0.45 | 0.36 | −0.29 | −0.46 | 0.57 | AL355297.3 | 0.06 | −0.08 | −0.10 | 0.82 | −0.15 |
| AC020658.4 | 1.70 | −1.36 | 1.07 | 0.46 | −0.21 | RNU6-160P | 0.97 | −1.11 | −0.09 | −0.21 | 0.87 | AC018618.2 | −0.17 | −0.74 | −1.14 | 0.07 | 2.17 |
| AC011595.2 | −0.66 | 0.03 | 1.65 | −0.20 | 0.36 | RPL7AP64 | 0.31 | −0.18 | 0.53 | 0.20 | 0.54 | PHOSPHO1 | 0.02 | −0.47 | 0.01 | −0.38 | 0.05 |
| HOXC4 | −0.36 | 0.19 | 0.09 | 0.28 | 0.00 | AC015909.1 | −0.56 | −0.43 | −0.63 | −0.25 | −0.47 | AC019133.1 | −0.36 | 0.13 | NA | 0.03 | −0.32 |
| GYPE | −0.67 | 0.48 | 0.99 | −0.29 | 0.26 | DENNDIC | −0.16 | 0.24 | 0.28 | −0.14 | −0.06 | RPL36P19 | 0.36 | −0.62 | −0.40 | −1.58 | −0.47 |
| NELFA | −0.29 | 0.23 | −0.18 | 0.25 | −0.06 | KANSL1-AS1 | −0.29 | 0.11 | 1.16 | −0.26 | 1.00 | MTCO3P31 | 0.36 | 0.01 | −0.10 | 0.42 | −0.19 |
| PHLPP2 | −0.26 | 0.15 | 0.19 | −0.04 | −0.04 | SOX4 | −0.10 | 0.30 | 0.75 | −0.21 | 0.09 | AL645924.1 | −0.09 | 0.66 | −0.75 | 0.36 | 0.85 |
| AP000787.3 | 0.48 | −0.17 | −0.11 | −0.19 | −0.19 | AC010501.1 | 0.56 | −1.38 | −1.07 | −0.70 | −0.61 | HDGFL3 | −0.01 | −0.05 | 0.16 | −0.14 | −0.05 |
| AC011389.3 | −0.91 | 0.96 | 0.53 | 0.07 | −0.01 | AC096773.1 | 0.66 | −0.73 | 0.02 | −1.60 | 0.83 | AC093390.1 | −0.07 | −0.10 | −1.18 | 0.09 | −0.77 |
| AC067817.2 | −0.97 | 0.26 | 0.70 | −0.04 | 0.39 | AC098935.1 | 0.52 | −0.49 | −1.15 | −0.04 | 0.56 | OR52E2 | −0.11 | −0.27 | −1.06 | 0.46 | 0.09 |
| MTND2P28 | −0.57 | 0.32 | 0.79 | 0.34 | −1.26 | G4330 | −0.23 | 0.21 | 0.19 | −0.57 | −0.59 | AC074194.2 | −0.02 | −0.08 | 0.08 | 0.21 | 0.63 |
| BMPR1A | −0.26 | 0.23 | 0.41 | 0.04 | −0.05 | RN7SKP292 | 0.25 | 0.05 | −1.35 | 0.22 | −1.03 | AC023245.2 | −0.11 | 0.21 | −0.03 | 0.14 | −0.19 |
| APLN | 0.65 | −0.99 | −0.84 | −0.84 | 0.12 | LINC01782 | −0.59 | 0.92 | −0.45 | 0.93 | −0.70 | AC006499.6 | −0.15 | −1.29 | 0.12 | −1.24 | 0.86 |
| PPP5C | 0.18 | −0.14 | −0.15 | −0.14 | −0.02 | AP000281.2 | −1.07 | −0.84 | 0.91 | 1.05 | 3.11 | NEK2P2 | 0.29 | −1.03 | −1.09 | 0.16 | 2.19 |
| DDB1 | 0.23 | −0.07 | −0.16 | −0.04 | −0.19 | AC092919.2 | −0.52 | −0.22 | −0.26 | 0.19 | 0.29 | AC087575.1 | 0.36 | −0.44 | 0.00 | 0.52 | −1.20 |
| IRF7 | 0.42 | −0.51 | −0.73 | −0.20 | −0.06 | AC004862.1 | −0.34 | −1.32 | −1.06 | 0.26 | 0.33 | HP1BP3 | −0.01 | 0.03 | −0.05 | −0.10 | −0.08 |
| AC090617.9 | 1.13 | −0.77 | −0.56 | 0.23 | 0.18 | AC010422.6 | 0.19 | 0.14 | 0.30 | 0.04 | −0.01 | OR13D3P | −0.03 | −0.10 | 1.12 | 0.33 | 0.99 |
| RPL23AP3 | −1.27 | 1.11 | 1.08 | −0.18 | −0.33 | RNU6-1034P | 0.38 | −1.38 | 0.35 | −0.11 | 0.84 | MTND2P19 | −0.10 | −0.82 | −1.28 | −0.65 | −0.64 |
| ENPP7P12 | −0.82 | −0.10 | 0.40 | −0.19 | 0.73 | RNU6-644P | 0.36 | −0.97 | 0.06 | −0.31 | 0.84 | STK25P1 | 0.09 | −0.34 | −0.63 | −0.32 | −0.72 |
| PCDHGA12 | −0.40 | 0.13 | 0.60 | −0.26 | 0.38 | AL158819.1 | 0.96 | −1.82 | −2.10 | 0.55 | 0.87 | AL109805.1 | −0.05 | −0.68 | −0.51 | −0.09 | 0.38 |
| BZW1P1 | 1.74 | −0.65 | −3.58 | 1.69 | −1.14 | CECR3 | −0.62 | −0.72 | 2.25 | −0.59 | −0.12 | OR7E111P | 0.25 | −0.27 | −2.05 | 0.84 | −2.66 |
| AMHR2 | −1.50 | −0.14 | 0.19 | −0.89 | −0.47 | LINC01258 | −0.52 | −1.32 | −0.39 | −0.34 | −0.49 | DPP10-AS2 | −0.36 | −0.42 | −0.83 | 0.16 | −1.64 |
| GLYATL1 | −0.74 | 0.42 | 0.30 | 0.61 | 0.27 | FLJ31104 | −0.26 | −0.08 | 0.10 | 0.18 | −0.05 | ATP4A | −0.03 | 0.20 | −0.64 | 0.34 | −0.83 |
| ARNTL | −0.27 | 0.21 | 0.12 | 0.25 | 0.27 | C5orf15 | 0.11 | 0.05 | 0.02 | −0.05 | −0.05 | MIR3143 | 0.36 | −0.28 | −0.67 | −2.34 | −0.23 |
| ELL2P1 | 1.11 | −0.18 | −0.85 | 0.54 | −0.78 | FOXP4 | −0.10 | 0.09 | −0.23 | 0.21 | 0.11 | ACTR3BP2 | 0.17 | 1.08 | −0.65 | 1.46 | −1.38 |
| AC091982.1 | 1.19 | 0.29 | −0.55 | 0.43 | −0.52 | RPS6P2 | 0.76 | −1.76 | −2.49 | 0.41 | 0.74 | GAPDHP35 | 0.07 | 0.00 | −1.17 | 0.09 | −0.82 |
| AC105053.1 | −1.39 | 0.69 | 1.65 | 0.85 | 0.92 | OR13I1P | 0.64 | −0.30 | −0.29 | 0.28 | −1.58 | OR1A1 | 0.06 | −1.02 | −0.70 | −0.21 | −0.28 |
| MYL4 | −1.31 | 0.27 | 0.45 | −0.16 | −0.50 | ATP6V1G1P6 | 0.37 | −1.21 | 1.08 | −1.07 | 0.76 | MIR4311 | 0.17 | 1.46 | 0.32 | 0.23 | −0.54 |
| LIPT1 | −0.41 | 0.13 | 0.54 | −0.01 | −0.03 | RNU6ATAC23P | 0.51 | −0.50 | 1.26 | −0.03 | 0.36 | IGKV1-13 | −0.36 | 0.89 | −0.67 | 0.65 | −2.53 |
| FUCA1P1 | −1.07 | 1.66 | 0.96 | 0.72 | −0.22 | ADGRG1 | −0.10 | 0.24 | −0.04 | 0.21 | −0.10 | LINC02053 | −0.21 | 1.09 | −0.92 | 1.16 | −0.86 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| RN7SL707P | −0.93 | −0.32 | −0.37 | 0.56 | 0.24 | PLEKHO1 | 0.15 | −0.38 | −0.10 | −0.36 | −0.13 | AC027702.1 | −0.03 | −0.09 | 0.06 | −0.07 | 0.06 |
| ATN1 | −0.32 | 0.16 | −0.22 | 0.30 | 0.02 | PLA1A | 0.37 | −0.51 | −1.23 | 0.38 | −0.68 | BX293995.1 | 0.09 | −1.51 | −1.50 | 0.05 | 0.56 |
| AC016251.1 | −0.73 | 0.42 | 1.07 | 0.41 | 0.29 | AC012508.1 | −0.68 | 0.48 | 0.03 | 1.53 | −0.87 | RPL30P7 | 0.36 | 0.01 | −1.29 | 1.68 | 0.89 |
| FAM91A2P | −0.89 | 0.42 | 1.12 | 0.03 | 0.35 | RPS12P16 | 0.29 | 0.31 | 0.62 | 0.01 | −0.11 | OR6C5P | −0.36 | 1.27 | −0.02 | 1.89 | −1.30 |
| RNF113A | 0.29 | 0.09 | −0.37 | −0.03 | −0.72 | LSP1P4 | 0.13 | 0.22 | 0.15 | 0.28 | 0.05 | FBP2 | 0.11 | −0.04 | 0.23 | 0.36 | 0.30 |
| AC012560.1 | −1.33 | −0.86 | 0.72 | 0.03 | 0.75 | PROM2 | 0.14 | 0.11 | −0.16 | 0.27 | 0.08 | AC026979.4 | −0.02 | −0.06 | 0.28 | −0.08 | 0.32 |
| FBXL19 | 0.42 | −0.10 | −0.66 | 0.18 | −0.04 | AC007228.1 | 0.36 | 0.48 | −0.77 | −0.08 | −1.73 | NUP214 | 0.01 | −0.03 | −0.05 | −0.04 | −0.01 |
| RP11-42302.5 | −0.41 | 0.21 | 0.82 | 0.59 | 1.16 | AC012676.1 | 0.32 | −0.67 | 0.05 | 0.09 | 0.76 | RPL3P3 | 0.10 | −1.11 | 0.04 | −0.22 | 1.15 |
| AC067931.1 | 0.69 | −0.11 | −0.61 | 0.03 | −0.69 | AC007204.1 | −0.55 | −1.25 | 0.84 | 0.35 | 1.20 | CAVIN4 | 0.03 | −0.05 | −0.50 | −0.77 | −0.78 |
| ACSM1 | −0.71 | 0.47 | −0.10 | 0.16 | −0.05 | AL022314.1 | −0.81 | −1.08 | −0.11 | −0.52 | 0.00 | ARMC7 | 0.01 | 0.23 | −0.10 | 0.15 | −0.11 |
| RN7SL405P | −1.09 | −0.41 | 0.15 | −0.42 | 0.06 | FGA | −0.58 | −0.55 | −0.63 | 0.01 | −0.34 | AC108073.1 | −0.35 | 0.49 | −0.14 | 0.28 | −0.26 |
| AC126768.1 | −0.86 | 0.70 | 1.02 | 0.58 | −0.16 | AC084876.1 | 0.44 | −0.32 | −0.21 | −0.04 | −0.32 | PPM1A | −0.01 | 0.22 | 0.13 | 0.11 | −0.18 |
| G3639 | 1.25 | −0.47 | −1.16 | −0.16 | −0.27 | RPL22P21 | −0.32 | 0.53 | 0.47 | −0.04 | −0.29 | RNA5SP251 | 0.11 | −1.04 | −0.75 | −0.17 | −0.64 |
| MIR26A1 | −0.88 | 0.22 | 1.16 | 0.08 | 0.40 | AL354751.1 | −0.76 | −0.49 | −2.05 | −0.75 | −1.97 | OR4S1 | 0.20 | −0.26 | −1.55 | 1.27 | −1.83 |
| ESYT1 | 0.31 | −0.34 | −0.62 | 0.05 | −0.16 | AL138878.2 | −0.52 | 0.87 | 1.25 | 0.09 | −0.58 | AC092892.1 | −0.09 | −0.59 | 0.13 | −0.52 | 0.50 |
| AC011625.1 | −1.67 | 1.03 | 1.48 | −0.52 | 0.36 | AL359313.1 | −0.62 | 0.40 | −0.36 | −0.29 | −1.60 | RN7SL67P | −0.03 | −0.30 | −0.17 | −0.34 | 0.18 |
| PRDM11 | −0.19 | 0.36 | 0.09 | 0.25 | −0.04 | MIR181A2 | 0.31 | −0.38 | 0.05 | −0.41 | 0.48 | AC243829.7 | 0.35 | −0.68 | −1.23 | 1.30 | 0.23 |
| CBX4 | −0.31 | 0.32 | 0.09 | 0.27 | −0.16 | AL354710.2 | −0.47 | −0.49 | 0.20 | −0.05 | 0.19 | PPP1R2P2 | −0.19 | −0.72 | −0.12 | −0.81 | 1.27 |
| RAPGEF5 | 0.29 | −0.11 | −0.29 | 0.14 | 0.03 | ARPC3P1 | 0.22 | −0.56 | 0.35 | −0.79 | 0.19 | AF096876.1 | −0.35 | 1.05 | −0.31 | −0.79 | −1.70 |
| AC136475.2 | −0.85 | 0.21 | 0.07 | 0.21 | −0.05 | AC061975.5 | 0.87 | −0.87 | −1.88 | 0.87 | −0.84 | ASH2LP1 | 0.34 | −0.92 | −0.64 | 1.35 | NA |
| RAD54B | 0.48 | −0.59 | −0.29 | −0.38 | −0.04 | ACTN4P1 | 0.64 | −0.94 | −0.94 | −0.17 | −0.29 | LINC01710 | −0.21 | 0.62 | −2.61 | 1.15 | −2.04 |
| GATA5 | −1.47 | 1.00 | −1.02 | 2.08 | 0.40 | AL499616.1 | 0.28 | −0.37 | 0.12 | −0.28 | −0.21 | EXOSC3P2 | −0.28 | 0.42 | −0.30 | 1.10 | −1.59 |
| AC068658.1 | −1.21 | 1.55 | −0.75 | 1.01 | −0.40 | AC008736.1 | 0.30 | −0.50 | −0.73 | 0.54 | 0.64 | AC107027.3 | 0.02 | −0.20 | −0.20 | 0.14 | −0.01 |
| AC020558.3 | −1.07 | −0.11 | −0.15 | 1.05 | 2.07 | PLXDC2 | 0.10 | 0.27 | 0.26 | 0.04 | −0.31 | AC012445.1 | −0.35 | −0.42 | 0.29 | 0.21 | 1.10 |
| RP11-157L3.5 | −2.38 | 1.31 | 0.42 | 0.70 | 0.04 | AC093895.1 | −0.67 | −0.05 | 0.15 | −0.67 | 1.36 | AC004805.3 | −0.13 | 1.63 | −1.01 | 1.23 | −0.78 |
| RFC5 | 0.30 | −0.18 | −0.47 | −0.07 | −0.30 | RNU6-1272P | −0.52 | 0.68 | 1.00 | −0.57 | 0.62 | MTND6P12 | −0.35 | −0.72 | 1.44 | 1.30 | 2.08 |
| LCMT2 | 0.33 | −0.24 | −0.52 | 0.00 | −0.48 | MIR1280 | 0.60 | −1.68 | 1.06 | −0.71 | 1.42 | ITPK1-AS1 | −0.02 | −0.40 | −0.48 | 0.02 | 0.12 |
| AC159540.1 | −0.58 | −0.02 | 0.52 | −0.76 | −0.11 | CTAGE1 | 0.54 | −0.49 | −1.46 | 0.31 | −1.18 | AC138304.1 | 0.09 | 0.33 | −1.55 | 1.12 | −1.42 |
| FARSA | 0.31 | −0.27 | −0.47 | −0.03 | 0.05 | AC002074.1 | −0.30 | 0.32 | 0.36 | −0.32 | −0.44 | AC020765.4 | −0.35 | 0.13 | 0.67 | −0.89 | 0.01 |
| CYP4F29P | −1.06 | 0.05 | 0.64 | −0.08 | 1.06 | SLC22A1 | −0.16 | 0.12 | 0.40 | −0.12 | 0.28 | RPL39P28 | 0.25 | −0.38 | −0.44 | 0.27 | 1.00 |
| MSMO1 | 0.69 | −0.19 | −0.46 | 0.37 | 0.09 | AC004257.1 | 0.34 | −0.04 | 0.20 | −0.33 | −0.54 | PRKRA | 0.01 | 0.10 | 0.19 | 0.07 | −0.08 |
| ADI1 | 0.29 | −0.12 | −0.36 | 0.02 | −0.15 | RN7SL200P | 0.29 | −0.17 | −0.89 | 0.05 | −0.15 | PDCL3P1 | −0.19 | 1.95 | −1.19 | 2.12 | −2.82 |
| PLCE1-AS1 | −0.98 | 0.48 | 0.47 | 0.66 | 0.65 | AC107918.3 | −1.02 | 0.36 | 1.51 | −0.14 | 0.33 | AC022523.1 | 0.34 | −0.44 | −0.27 | 1.39 | 1.65 |
| KDR | 0.55 | −0.26 | 0.10 | −0.22 | −0.20 | AL391903.1 | 1.22 | −2.47 | −2.10 | 0.14 | 0.09 | AC012103.1 | −0.35 | 0.03 | −0.30 | −1.16 | −1.05 |
| PFKL | −0.26 | 0.05 | −0.19 | 0.25 | 0.09 | KLHL14 | 0.36 | 0.02 | −0.54 | 0.56 | −0.36 | HIRAP1 | −0.35 | 0.59 | 1.00 | 1.82 | 1.33 |
| FBX06 | 0.45 | −0.38 | −0.49 | −0.26 | −0.40 | AL358852.1 | 0.28 | −0.50 | −1.22 | −0.21 | −0.17 | AL512310.2 | −0.35 | −0.17 | −0.13 | −0.45 | 0.07 |
| MMP15 | 0.40 | 0.10 | −0.34 | 0.19 | −0.13 | AL161901.1 | 0.68 | −0.79 | −2.49 | −0.25 | −3.03 | AQP5 | −0.04 | 0.75 | 1.21 | 0.37 | 0.28 |
| PTPN22 | 0.75 | −0.96 | −0.15 | −0.39 | 0.21 | SMN2 | 0.18 | 0.06 | 0.02 | 0.20 | 0.32 | PPP1R14BP2 | 0.06 | −0.42 | −0.93 | −0.69 | −0.07 |
| AC005840.2 | 0.50 | −0.63 | −1.82 | 0.26 | −0.28 | AC018616.1 | −1.02 | 1.09 | 0.28 | −0.27 | 1.24 | SERPINE3 | −0.03 | −0.32 | 0.55 | −0.22 | 0.15 |
| GNAI2 | 0.33 | −0.24 | −0.21 | −0.21 | −0.01 | LINC01750 | −0.22 | −0.87 | 0.03 | −0.21 | 1.02 | RN7SL366P | 0.12 | −1.92 | −0.91 | −0.56 | −0.14 |
| PHYHIPL | −0.77 | 0.56 | 1.01 | 0.22 | 0.03 | OR4P1P | 1.07 | −0.43 | −1.40 | 0.45 | −1.97 | SDS | 0.03 | −0.61 | −0.12 | −0.49 | 0.17 |
| PLSCR3 | 1.32 | −0.07 | −0.17 | 0.15 | −0.63 | AC006207.1 | −0.46 | 0.67 | 1.13 | −0.17 | 1.01 | STS | −0.02 | 0.18 | 0.02 | 0.13 | −0.26 |
| H1FNT | −1.26 | −0.18 | −0.38 | −0.39 | −0.10 | OR4K17 | 0.63 | −0.18 | −0.48 | 0.36 | −2.11 | DPPA5P1 | −0.25 | −0.38 | 0.64 | 0.53 | 0.82 |
| RPL17 | 0.55 | −0.46 | −0.25 | −0.20 | 0.20 | HIGD2A | 0.11 | 0.13 | 0.17 | 0.05 | −0.15 | OR4R2P | −0.35 | 0.19 | 0.20 | 0.28 | 0.53 |
| METTL27 | −0.73 | 0.21 | 0.78 | −0.35 | 0.58 | RNA5SP348 | −1.36 | 1.31 | 0.29 | 2.08 | −0.52 | MTND5P13 | 0.17 | −1.58 | 1.09 | −0.70 | 2.13 |
| HOTAIR | −0.50 | 0.40 | 0.37 | 0.22 | 0.22 | FAM170B | 1.14 | −1.70 | 1.05 | −0.58 | 2.32 | ALKAL1 | −0.12 | 0.92 | 0.08 | 0.50 | −2.01 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| PPCDC | −0.31 | −0.13 | 0.02 | −0.09 | 0.25 | RN7SL34P | −0.29 | −0.55 | −0.26 | −0.11 | −0.42 | SEMA3B-AS1 | 0.07 | 0.47 | −1.12 | 1.01 | −0.22 |
| RPS15AP10 | 0.63 | −0.07 | 0.40 | −0.19 | 0.06 | CLDN10-AS1 | −0.39 | 0.46 | 0.95 | 0.14 | 0.81 | LINC00868 | −0.09 | 2.60 | 0.60 | 0.77 | −0.16 |
| JMY | 0.34 | 0.19 | −0.01 | 0.29 | −0.37 | AL024508.1 | 0.13 | −0.16 | −0.11 | 0.07 | 0.10 | RASGRF2-AS1 | −0.05 | −0.61 | −0.18 | −0.16 | −0.04 |
| LENG1 | −0.34 | 0.18 | 0.23 | 0.13 | 0.11 | CCDC177 | −0.46 | −0.54 | 0.11 | −0.49 | 0.31 | AC073111.2 | −0.13 | 0.10 | −0.55 | 0.66 | −1.05 |
| CCR2 | 0.84 | −0.50 | 0.54 | 0.01 | 0.69 | AC068594.1 | 0.31 | −1.07 | −0.24 | 0.02 | 0.36 | AK4 | 0.02 | 0.00 | 0.20 | 0.08 | 0.23 |
| LINC01503 | −0.54 | −0.09 | 0.55 | 0.03 | 0.63 | GUCY2F | 0.53 | −0.64 | −1.05 | −0.52 | 0.02 | OR5AW1P | −0.32 | 1.93 | −0.65 | 1.42 | −3.23 |
| CLDN12 | 0.36 | −0.17 | −0.23 | −0.22 | −0.17 | AP001547.1 | 0.28 | 0.57 | 0.43 | 0.32 | 0.24 | AC097474.1 | −0.10 | −0.47 | −1.20 | 0.63 | 1.09 |
| RNF217 | 0.29 | −0.12 | −0.24 | 0.13 | −0.14 | AC007389.1 | −0.46 | −1.19 | −0.17 | −0.32 | −0.04 | G17127 | 0.03 | 0.24 | −0.46 | 0.08 | −0.80 |
| MAB21L3 | 0.58 | −0.29 | −0.58 | 0.24 | −0.09 | AL513548.2 | −0.71 | −0.40 | 0.66 | −1.75 | 0.69 | SAMD7 | 0.08 | −0.18 | −1.12 | 0.86 | −0.37 |
| GPR179 | −0.74 | −0.50 | 0.05 | −0.08 | 0.46 | AC097359.3 | −1.46 | 1.36 | 2.45 | −0.55 | 0.88 | OR10G8 | 0.28 | −0.26 | 0.83 | 0.55 | 0.14 |
| KIAA1324 | −0.76 | 0.53 | 0.92 | 0.42 | 0.71 | AC026634.1 | 0.55 | −0.13 | −0.22 | 0.80 | 0.14 | OR8L1P | 0.35 | −1.56 | −0.12 | 0.82 | −0.63 |
| COL4A5 | −0.36 | 0.30 | −0.31 | 0.48 | 0.09 | AC114956.2 | −0.18 | 0.02 | 0.08 | 0.60 | 0.61 | AC087885.1 | −0.35 | −0.37 | 0.20 | −2.18 | 0.16 |
| GOLGA2P7 | −0.57 | 0.23 | 0.08 | 0.49 | 0.74 | HSPE1P3 | −0.25 | 0.15 | −0.12 | −0.06 | −0.31 | AC022634.2 | 0.35 | −0.52 | −0.25 | 0.52 | −1.73 |
| DHDDS | −0.23 | 0.00 | 0.04 | 0.02 | 0.08 | G25699 | 0.26 | −0.02 | 0.90 | −0.34 | 0.55 | RN7SL99P | −0.05 | −0.63 | 0.18 | −0.11 | 0.84 |
| AC005042.1 | 0.57 | 0.07 | −0.43 | 0.31 | −0.20 | LINC02154 | 0.59 | −0.36 | −2.32 | 0.51 | −1.72 | ARL5C | 0.07 | −0.96 | −0.53 | 0.68 | −0.16 |
| POU5F1B | −0.74 | 0.22 | 1.39 | 0.83 | 0.73 | AC006504.2 | −1.02 | 0.22 | 1.38 | 0.57 | 1.55 | AC003985.1 | 0.35 | −1.13 | −1.03 | 0.59 | 0.89 |
| FFAR2 | 0.96 | −1.90 | −0.92 | −0.48 | −1.08 | DUXAP7 | 0.24 | −0.59 | −0.80 | −0.05 | 0.17 | OR6C72P | 0.35 | −1.11 | −0.49 | 0.22 | 0.50 |
| SLC2A12 | −0.62 | 0.40 | 1.33 | 0.23 | 0.28 | RASA4CP | −0.18 | 0.33 | 0.37 | 0.35 | 0.07 | AC055717.3 | −0.35 | −0.16 | −0.69 | 0.06 | −2.30 |
| STEAP3-AS1 | 0.49 | −0.58 | −0.64 | 0.26 | 0.06 | SOS2 | 0.08 | 0.07 | −0.05 | 0.11 | −0.06 | RPS4XP9 | 0.12 | 0.26 | −0.76 | 0.53 | −1.66 |
| SRSF9 | 0.21 | −0.20 | −0.22 | −0.09 | 0.04 | CCNB1IP1P3 | −1.21 | 0.61 | −0.04 | 0.85 | −0.86 | OR5AL1 | −0.35 | 0.24 | −0.68 | 1.19 | −0.16 |
| AC104041.1 | −1.17 | 0.09 | 1.48 | −0.33 | 0.19 | AC099541.1 | 0.97 | −0.20 | 0.50 | −0.65 | −1.92 | BMP2 | −0.02 | 0.31 | 0.02 | −0.01 | −0.38 |
| CBX1 | 0.26 | 0.03 | 0.10 | −0.19 | −0.10 | RNU6-548P | 0.34 | −0.69 | −1.62 | 0.14 | −0.38 | AL157944.1 | −0.05 | −1.84 | −0.71 | 0.83 | 1.84 |
| AC087521.1 | −1.22 | 0.72 | −0.49 | 0.40 | −0.53 | AP001102.1 | 0.27 | 0.17 | −0.48 | 0.08 | −0.52 | BAIAP2 | −0.02 | 0.04 | −0.50 | 0.26 | −0.06 |
| CCDC113 | −0.28 | 0.20 | 0.51 | 0.14 | 0.05 | AC092376.3 | −0.35 | 0.23 | 0.32 | 0.05 | −0.26 | STX17-AS1 | −0.07 | −0.07 | 0.87 | 0.33 | 0.24 |
| FXYD3 | −0.62 | 0.41 | 0.37 | 0.40 | 0.13 | MTND4P10 | 1.04 | −0.66 | −2.27 | 0.87 | −0.97 | OR4D10 | 0.07 | −1.37 | −1.57 | 0.93 | −0.94 |
| CACTIN | −0.37 | 0.12 | −0.16 | 0.28 | 0.16 | AC120036.3 | −0.77 | 1.13 | 3.28 | 0.31 | 0.80 | AL163973.3 | −0.35 | −0.99 | 0.16 | −0.25 | 0.87 |
| LCTL | 0.75 | −0.91 | −1.04 | −0.24 | −0.32 | AL603766.1 | 0.87 | −1.01 | −2.82 | −0.08 | −2.13 | AC074035.1 | −0.14 | 0.23 | −0.65 | 1.22 | −0.23 |
| SMPDL3A | 0.51 | 0.15 | 0.10 | 0.28 | −0.02 | EAF1-AS1 | 0.25 | 0.05 | 0.18 | 0.14 | 0.01 | RNA5SP477 | −0.05 | −0.23 | −0.34 | −0.31 | −1.69 |
| MTMR1 | 0.26 | −0.02 | −0.36 | 0.17 | −0.10 | SIRPAP1 | 0.35 | −0.14 | −0.07 | 0.26 | 0.52 | AGGF1P9 | −0.18 | 0.23 | −0.67 | 1.04 | −1.64 |
| AC012309.1 | −0.96 | −0.29 | 1.41 | −0.95 | 0.79 | PAICSP1 | 0.24 | −0.23 | −0.19 | −0.14 | −0.12 | AC103843.1 | 0.35 | −1.30 | −0.03 | 0.26 | 1.98 |
| RNVU1-13 | 0.66 | −0.19 | −0.74 | −0.20 | 0.13 | RNU6-1180P | −0.40 | 0.09 | −0.26 | 0.64 | −0.33 | OR9N1P | 0.12 | −0.91 | −1.08 | 0.87 | 1.12 |
| AC009502.1 | 1.25 | −1.28 | −2.49 | 0.06 | −1.10 | G19448 | −0.38 | 0.67 | 0.81 | 0.29 | 0.29 | AC114488.3 | −0.06 | −0.85 | −0.75 | 0.48 | 0.87 |
| AC103591.1 | −0.97 | 0.81 | 0.12 | 0.58 | 0.19 | AC004771.3 | −0.43 | −0.37 | 0.21 | 1.30 | 1.26 | AL078623.1 | −0.15 | −1.03 | 0.02 | 0.13 | −0.85 |
| PTRH1 | −0.86 | 0.50 | 0.73 | 0.61 | 0.09 | SETSIP | 0.41 | 0.03 | −0.19 | −0.55 | −0.38 | AC068946.2 | 0.08 | 0.82 | −0.49 | 0.29 | −0.73 |
| CHCHD3 | 0.28 | −0.30 | −0.26 | −0.24 | 0.03 | AC073648.4 | −0.34 | 0.11 | 1.62 | −0.60 | 0.74 | RBMXL3 | 0.11 | 0.59 | 0.27 | 0.26 | −0.74 |
| AC015799.1 | 0.39 | −0.41 | −0.16 | −0.14 | 0.11 | LINC01478 | 0.54 | −0.58 | −1.71 | −0.22 | −2.01 | LINC02177 | 0.06 | −0.19 | 1.19 | 0.95 | 0.25 |
| RP11-592B15.4 | 0.28 | 0.00 | −0.21 | −0.04 | −0.27 | AC073218.2 | −0.48 | 0.69 | −0.61 | 0.17 | −0.96 | MAP2K1P1 | 0.11 | −0.07 | −0.85 | −0.33 | −2.65 |
| CHIT1 | −0.92 | 0.14 | 0.07 | −0.15 | 0.44 | CT45A11P | −0.45 | −0.80 | 0.39 | −0.59 | 0.10 | AL020994.3 | 0.15 | 0.02 | −0.10 | 0.27 | 0.31 |
| HLA-G | 0.72 | −1.29 | −1.50 | −0.14 | 0.46 | AC011468.5 | 0.31 | 0.47 | 0.66 | −0.03 | 0.05 | NF1P1 | 0.09 | −0.24 | −2.03 | −0.22 | −1.95 |
| RC3H1-IT1 | −0.46 | 0.10 | 0.32 | 0.01 | 0.36 | LINC02115 | −0.41 | 0.14 | −0.26 | 0.33 | −0.86 | AL161757.5 | 0.09 | −0.84 | −1.78 | −0.93 | −2.08 |
| AC092747.2 | −0.48 | −0.11 | 0.04 | 0.20 | 0.16 | AC026688.2 | −1.03 | 0.44 | −1.51 | 0.67 | −0.65 | AL391261.3 | −0.16 | −0.52 | 1.33 | 0.98 | 1.83 |
| RHBDD2 | 0.31 | −0.02 | −0.12 | 0.07 | 0.05 | NDUFB1P2 | −0.54 | 1.26 | 1.40 | 1.12 | 0.52 | NDUFA5P5 | 0.35 | −1.01 | 1.46 | −1.46 | 1.58 |
| SGF29 | −0.32 | 0.30 | −0.13 | 0.34 | −0.09 | GRAMD4P8 | 0.72 | 0.29 | −0.79 | 0.64 | −1.05 | RPL36AP43 | 0.04 | 0.21 | 0.14 | 0.23 | −0.17 |
| HNRNPCP1 | −0.51 | −0.06 | 0.10 | 0.31 | 0.41 | BX664718.1 | −0.60 | 0.46 | 0.71 | 0.28 | −0.57 | AC087627.1 | 0.06 | −0.22 | −0.65 | 0.22 | 0.32 |
| ELP4 | 0.28 | −0.20 | −0.12 | −0.10 | 0.03 | NTAN1P2 | −0.13 | −0.06 | 0.23 | 0.00 | 0.33 | RN7SL762P | 0.10 | 0.26 | −0.38 | 0.32 | −1.73 |
| AC084824.4 | 1.06 | 0.08 | −1.10 | −0.03 | −0.71 | AL354714.2 | 0.33 | −0.89 | −0.13 | −0.27 | −0.07 | AC026786.2 | −0.10 | 0.00 | −1.19 | 1.61 | 0.47 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| RPS15AP16 | 0.77 | −0.24 | −0.59 | −0.10 | −0.08 | LINC00307 | −1.35 | −0.47 | 1.27 | 0.48 | −0.13 | RSL24D1P5 | −0.34 | 0.45 | −0.67 | 2.03 | −1.74 |
| MT-TH | −1.03 | 0.47 | 0.91 | 0.83 | −0.26 | MROH5 | −0.53 | −0.69 | −1.17 | 0.39 | 0.58 | OR2W4P | −0.15 | −0.21 | −0.66 | 1.85 | 0.99 |
| RUFY4 | 1.04 | −1.10 | −1.65 | −1.08 | −0.28 | AC023043.2 | 0.41 | −0.78 | −0.55 | −0.05 | 0.33 | PARP4P2 | −0.04 | −0.13 | −0.34 | −0.27 | −1.01 |
| NUDT12 | 0.23 | −0.06 | −0.21 | 0.06 | 0.00 | AC005197.1 | −0.56 | −1.83 | −0.13 | −0.15 | 2.57 | AC018552.3 | 0.03 | 0.27 | 0.09 | 0.03 | −0.15 |
| AC090092.1 | −1.13 | 1.02 | 1.78 | −0.15 | −0.64 | RN7SL460P | −0.92 | −0.79 | 0.59 | −0.70 | −0.17 | AC147055.1 | 0.34 | −0.62 | −0.49 | −0.23 | −0.94 |
| AVIL | −0.26 | 0.10 | 0.33 | −0.12 | 0.14 | LINC01232 | −0.23 | −0.39 | −0.06 | −0.10 | 0.14 | BX537318.1 | 0.04 | 0.46 | 0.73 | −0.08 | 0.17 |
| ASCC2 | 0.18 | −0.11 | −0.30 | −0.01 | −0.03 | SNORA46 | 0.20 | −0.03 | 0.13 | −0.06 | −0.49 | GEMIN2P1 | −0.14 | −2.07 | 1.19 | −2.15 | 0.18 |
| GPANK1 | −0.31 | 0.05 | 0.12 | 0.10 | 0.19 | G42267 | −0.52 | 0.91 | 2.81 | 0.45 | 1.06 | DUX4L17 | 0.16 | −1.10 | −0.61 | 0.57 | 2.52 |
| MEIS3 | −0.57 | −0.09 | 0.46 | −0.27 | 0.10 | SIRPB1 | 0.33 | −0.38 | −1.36 | −0.06 | 0.12 | AC147067.2 | 0.10 | −0.32 | 0.02 | −0.48 | −0.10 |
| CLDN11 | −0.78 | 0.11 | 1.03 | 0.25 | 0.46 | PEPD | 0.10 | −0.04 | −0.14 | 0.01 | −0.23 | RPL35P9 | −0.33 | −0.48 | 1.05 | 0.26 | 2.05 |
| LINC02097 | −1.26 | 0.03 | 1.55 | −0.86 | 0.78 | LINC01627 | 0.62 | −1.46 | −0.75 | 0.89 | 2.18 | OR12D3 | 0.15 | −0.52 | −1.02 | 1.32 | −2.06 |
| AL121839.2 | 0.39 | −0.13 | −0.04 | 0.01 | 0.07 | BX649632.1 | −0.35 | −0.04 | −0.01 | −0.19 | −0.60 | NXPH2 | −0.11 | −0.53 | −1.36 | 0.70 | 0.14 |
| SELENOO | −0.41 | 0.05 | −0.12 | 0.31 | 0.31 | AC097375.3 | −0.55 | −0.41 | 0.85 | −0.04 | 0.08 | AC015574.1 | 0.07 | −1.75 | −2.19 | 0.18 | −1.06 |
| CDC42P6 | 0.76 | −0.10 | −1.15 | −0.12 | −1.49 | AC073861.1 | 0.15 | 0.09 | −0.08 | 0.18 | −0.17 | MIR616 | −0.03 | −0.03 | −0.25 | 0.05 | −0.75 |
| AC092757.3 | 1.19 | −0.35 | −0.65 | −0.26 | −0.66 | CNTLN | −0.11 | 0.02 | 0.12 | 0.00 | −0.07 | RARA | −0.01 | −0.06 | −0.15 | 0.08 | −0.03 |
| GPRC5D-AS1 | 0.41 | −0.15 | −0.09 | −0.06 | 0.45 | DGKK | −0.42 | −0.01 | −0.65 | 0.04 | −0.89 | RIPK3 | −0.01 | −0.03 | −0.24 | 0.08 | −0.13 |
| MIR17HG | 0.52 | −0.58 | −0.30 | 0.01 | 0.03 | SHISA9 | −0.28 | 0.61 | −0.07 | 0.46 | −0.21 | LINC01676 | 0.09 | −0.62 | −1.05 | 0.54 | −0.32 |
| LINC02254 | −1.25 | 0.24 | 1.57 | −0.08 | 1.04 | AC087301.1 | −0.27 | −0.90 | 0.27 | 0.24 | 1.49 | DDX3P3 | 0.09 | −0.16 | −0.51 | 1.02 | −0.67 |
| AC026358.1 | −1.81 | −0.16 | 0.67 | 0.66 | 1.36 | RNU1-108P | −0.69 | −1.90 | −1.60 | −0.75 | −0.63 | AL592043.2 | 0.33 | −0.81 | −0.35 | −0.55 | 0.52 |
| FAM201B | −1.11 | 0.67 | −0.52 | 1.13 | −0.17 | RNA5SP493 | 0.32 | −0.03 | −0.50 | −0.31 | −0.66 | SNORD114-31 | 0.08 | −0.12 | 1.93 | −0.16 | 1.01 |
| AC131025.3 | 0.76 | −0.39 | −1.21 | −0.20 | −0.50 | OR2J1 | −0.64 | −0.77 | 0.33 | 0.09 | −0.09 | PAM | −0.02 | 0.11 | 0.40 | −0.22 | −0.02 |
| G20013 | −1.79 | 1.11 | 1.45 | 0.16 | 0.69 | MTND5P28 | 0.18 | 0.04 | −0.21 | 0.17 | 0.10 | IRAIN | −0.17 | −0.77 | −0.28 | −0.76 | −0.73 |
| NBR2 | −0.37 | 0.18 | 0.36 | 0.25 | 0.25 | DNAJB7 | 0.25 | −0.09 | −0.34 | −0.23 | −0.31 | AL513327.3 | −0.03 | 0.15 | 0.42 | 0.28 | 0.65 |
| ATP1A1-AS1 | −0.30 | 0.16 | −0.18 | 0.19 | −0.02 | AC006004.1 | 0.60 | −1.36 | 0.23 | 0.43 | 0.50 | AL391384.1 | −0.07 | −0.09 | −0.38 | 0.88 | 0.19 |
| RN7SL857P | −1.42 | 0.55 | 1.13 | −0.06 | 0.74 | BTBD9-AS1 | 0.17 | −0.20 | 0.57 | −0.02 | 0.52 | AC113137.1 | 0.18 | −1.16 | −0.21 | −0.69 | −0.66 |
| FRG2C | −1.00 | 1.00 | 1.10 | 0.18 | 0.33 | AC011491.2 | −0.29 | −0.74 | −0.38 | −0.04 | 0.80 | AC013402.2 | 0.34 | −1.76 | −0.46 | −1.47 | −0.67 |
| AC104306.2 | −1.08 | −0.13 | 0.29 | 0.68 | 0.78 | SARDH | −0.33 | −0.02 | −0.25 | 0.31 | 0.27 | CCDC34P1 | −0.34 | 0.80 | −0.44 | −0.15 | −2.03 |
| RNU6-1251P | −1.21 | 0.30 | 1.03 | 0.01 | −0.44 | FAM47A | −0.65 | −0.57 | 0.53 | 0.00 | −0.31 | AC023050.4 | −0.05 | −1.10 | 0.32 | 0.30 | 0.41 |
| ANAPC4 | 0.20 | −0.09 | 0.01 | 0.00 | 0.17 | EFL1P1 | −0.38 | −0.12 | 0.15 | −0.45 | −0.29 | AL031056.2 | 0.16 | −0.33 | −0.77 | −1.25 | −1.67 |
| NPC1L1 | −1.11 | 0.22 | −0.50 | 0.11 | −1.34 | 2-Mar | −0.14 | 0.37 | 0.07 | 0.16 | −0.37 | AC245140.1 | 0.11 | −1.26 | 1.09 | −0.91 | 1.42 |
| SLC35B3 | 0.24 | −0.19 | −0.04 | −0.17 | 0.05 | SNIP1 | 0.07 | −0.01 | −0.13 | −0.03 | −0.18 | RNU4-47P | 0.03 | −0.01 | 0.56 | −0.07 | 0.61 |
| AL391684.1 | −0.43 | 0.07 | 0.61 | 0.37 | 0.50 | AC104772.2 | −0.88 | −1.95 | 0.85 | 1.20 | 3.16 | AC092620.1 | 0.04 | 0.54 | −0.11 | 0.70 | 0.17 |
| G34278 | −0.95 | 0.50 | 1.63 | 0.05 | 0.15 | HIGD1AP8 | −0.45 | −0.18 | 0.00 | 0.43 | 1.15 | RPS4XP10 | 0.06 | −0.39 | −1.38 | −0.13 | −1.59 |
| AC006372.2 | 1.17 | −0.78 | −0.12 | −0.61 | −0.03 | AC109635.1 | −1.24 | −0.79 | −0.51 | 0.18 | −0.48 | AC009101.1 | 0.30 | −0.68 | −0.49 | 0.88 | −0.54 |
| DDX11L2 | −0.88 | 0.21 | 1.30 | 0.40 | 0.96 | AL117332.1 | −0.21 | 0.10 | 0.68 | −0.30 | −0.13 | SETP22 | −0.05 | −0.12 | −1.41 | 0.05 | −0.40 |
| PTCHD1-AS | −1.29 | 1.80 | −1.01 | 1.28 | −2.27 | CHIAP3 | 0.66 | 0.14 | −0.15 | 1.58 | 0.42 | C7orf33 | 0.09 | −0.26 | −0.90 | −0.32 | −2.46 |
| SLC7A6 | −0.30 | 0.24 | 0.19 | 0.11 | 0.07 | MMD2 | −0.72 | −0.38 | −0.94 | 0.29 | −0.64 | AL031133.1 | 0.04 | −0.38 | 0.38 | −0.20 | −0.18 |
| RNA5SP71 | −1.62 | 0.82 | −0.27 | 0.88 | −0.73 | PRDX3P2 | 0.30 | −0.48 | 0.12 | −0.35 | 0.43 | CARSP2 | 0.34 | −0.52 | −0.36 | −1.39 | −2.83 |
| AC010733.1 | 0.54 | −0.07 | −0.71 | 0.15 | −0.45 | G26935 | −0.38 | 0.00 | 0.52 | 1.36 | 0.69 | SPI1 | 0.02 | −0.43 | −0.34 | −0.21 | −0.09 |
| COQ6 | −0.32 | 0.11 | 0.38 | 0.11 | 0.34 | AL022722.1 | 0.19 | −0.49 | −1.12 | −0.19 | −0.48 | AC025048.4 | −0.04 | −0.30 | 0.91 | 0.03 | 1.10 |
| CDKN1C | −0.66 | 1.00 | 0.41 | 0.57 | −0.45 | AL591074.1 | 0.88 | −1.77 | −2.13 | −0.15 | −0.98 | MORF4L1P7 | 0.09 | −0.10 | −0.96 | −0.65 | −2.03 |
| HDAC9 | −0.45 | 0.16 | 0.65 | −0.14 | 0.14 | RP11-187C18.2 | −0.43 | 0.05 | 1.09 | −0.16 | 0.59 | AL590824.1 | −0.19 | −0.74 | 0.48 | −1.33 | 0.29 |
| AP003068.2 | 0.67 | −0.06 | −0.03 | 0.32 | 0.23 | OR6D1P | −0.41 | 0.34 | −0.72 | 0.17 | −0.19 | AC139720.1 | −0.04 | 0.07 | 0.38 | −0.26 | −0.32 |
| AC008065.1 | 0.71 | −0.59 | −0.33 | 0.09 | 0.68 | POU2AF1 | 0.31 | −0.11 | 0.58 | −0.63 | 0.00 | AL355674.1 | 0.13 | 0.63 | −2.67 | 1.25 | −2.98 |
| CLNS1A | 0.26 | −0.20 | −0.14 | −0.14 | 0.02 | PLA2G2F | 0.23 | 0.07 | 0.00 | 0.26 | 0.42 | RN7SL849P | 0.34 | −0.68 | 0.87 | −1.58 | 0.52 |
| RN7SL57P | 0.78 | −0.39 | −0.75 | −0.23 | −0.19 | SCYL3 | 0.07 | −0.11 | 0.18 | 0.02 | 0.16 | HRASLS | 0.03 | 0.93 | 0.32 | 0.74 | −0.50 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC096720.1 | 0.78 | −0.59 | −0.54 | 0.16 | 0.14 | AC009097.3 | −0.39 | −0.25 | −0.22 | 0.18 | 0.31 | OR7E21P | −0.15 | 0.64 | −0.77 | 1.30 | −0.45 |
| POLG2 | −0.24 | −0.01 | 0.15 | 0.09 | 0.36 | RNU6-937P | 0.95 | −0.58 | 0.68 | −1.96 | −0.78 | AC024132.3 | −0.30 | 0.19 | −0.02 | 1.35 | 1.14 |
| SH2B2 | 0.74 | −0.45 | −0.56 | −0.28 | −0.46 | RSRC1 | −0.09 | −0.04 | −0.12 | −0.01 | −0.08 | AC015689.1 | 0.18 | −0.67 | 0.04 | 0.02 | −1.41 |
| G38269 | 0.73 | −0.08 | 0.05 | −0.30 | −0.05 | OR1N2 | −0.45 | 0.48 | 0.00 | −0.50 | −0.57 | OR10K2 | −0.07 | −1.04 | −0.91 | 0.05 | 1.92 |
| CCL2 | 0.71 | −0.87 | −0.73 | −0.27 | −0.39 | CCDC15 | −0.10 | −0.19 | 0.03 | −0.25 | 0.09 | AC124893.1 | 0.16 | 0.30 | 0.87 | −0.32 | 1.37 |
| OSBPL6 | 0.36 | −0.08 | −0.26 | 0.25 | −0.02 | AC134349.1 | 0.20 | −0.10 | −0.08 | 0.13 | 0.14 | SLC5A4P1 | −0.34 | −0.65 | 0.98 | 0.45 | 1.82 |
| AP002784.1 | 1.41 | −0.90 | −1.09 | −0.26 | −0.24 | AL138889.1 | 0.47 | −0.63 | −0.80 | −0.29 | −0.90 | AC008073.3 | −0.04 | −0.05 | 0.20 | 0.28 | 0.33 |
| AC090877.2 | 1.46 | 0.50 | −0.19 | −1.47 | −1.80 | AC004877.1 | −0.43 | 0.64 | 0.20 | 0.10 | −0.67 | ACTBP12 | 0.34 | −0.35 | −0.46 | 1.46 | −0.07 |
| COL8A2 | −0.39 | 0.16 | 0.11 | −0.15 | −0.06 | AC020893.2 | 0.24 | 0.01 | −0.13 | −0.11 | −0.21 | LINC01440 | 0.06 | −0.04 | −1.96 | 0.73 | −1.47 |
| CCDC120 | 0.46 | 0.27 | −0.41 | 0.24 | −0.47 | AC068987.1 | −0.62 | −0.73 | −1.10 | 0.84 | −0.40 | AL133247.2 | −0.32 | 0.21 | −0.73 | −0.26 | −0.93 |
| AL139082.1 | −0.67 | 0.67 | 0.47 | −0.16 | −0.42 | GTF2IP4 | −0.14 | 0.37 | −0.04 | 0.21 | −0.46 | RNU1-143P | −0.05 | −0.17 | 0.58 | 0.53 | 0.67 |
| PRICKLE1 | −0.50 | 0.34 | 1.01 | −0.09 | 0.09 | AC006213.4 | −0.40 | 0.73 | 1.23 | −0.33 | −0.03 | EDDM3B | −0.14 | 1.66 | 0.57 | −0.97 | −0.81 |
| AP003108.2 | −0.42 | −0.10 | 0.30 | −0.29 | −0.03 | AP000688.2 | 0.22 | −0.34 | 0.66 | −0.25 | 0.41 | MBL1P | 0.03 | −0.17 | 0.65 | 0.13 | 0.01 |
| FUT11 | 0.26 | −0.12 | 0.03 | −0.27 | −0.11 | MRPL57P8 | 0.40 | −0.22 | 0.64 | −0.24 | −0.83 | AL354732.1 | 0.02 | −0.33 | −0.21 | −0.21 | 0.04 |
| RN7SL867P | −0.69 | −0.20 | −0.16 | −0.02 | 0.02 | AC244154.1 | 0.17 | −0.11 | −0.26 | 0.03 | 0.10 | CDC27P1 | 0.04 | −0.54 | −1.21 | 0.02 | −0.72 |
| LINC00639 | −0.83 | 0.91 | 0.71 | 0.29 | 0.11 | LINC01288 | −1.00 | −0.17 | 0.76 | −2.01 | −0.48 | AC103879.1 | −0.17 | −0.61 | 0.23 | 0.37 | 0.69 |
| STRCP1 | −0.49 | 0.30 | 0.39 | −0.01 | 0.04 | RABEP1 | 0.09 | −0.07 | −0.07 | −0.14 | 0.07 | NADK2-AS1 | 0.03 | 0.08 | 0.29 | −0.07 | 0.59 |
| HNRNPA1P10 | 0.51 | −0.08 | −0.17 | 0.15 | −0.26 | AL133467.2 | 1.09 | 0.02 | −0.80 | 0.21 | −1.54 | AC018653.2 | −0.34 | 0.56 | −0.66 | 1.47 | −1.34 |
| LRRTM4 | −1.03 | −0.70 | 0.27 | 0.27 | 0.82 | AC119674.1 | −0.20 | 0.03 | −0.01 | 0.07 | 0.19 | SNAI3 | −0.03 | 0.16 | −0.01 | 0.24 | −0.03 |
| AKR1C8P | −1.34 | −0.41 | 1.48 | 0.04 | 0.55 | GS1-124K5.4 | −0.27 | −0.07 | 1.78 | −0.50 | 0.47 | AP000648.2 | 0.34 | 0.19 | −0.26 | 0.17 | 0.57 |
| AL157702.2 | 1.84 | −1.34 | −1.37 | −0.75 | −1.02 | ACER2 | −0.13 | 0.06 | 0.29 | 0.17 | 0.15 | SEPT7P8 | 0.32 | −0.34 | 0.43 | 0.18 | −0.44 |
| AC020917.4 | −0.46 | 0.37 | 0.67 | 0.04 | 0.15 | MT-RNR2 | −0.78 | 0.34 | −0.35 | 0.92 | −0.11 | OR8G7P | −0.34 | 0.96 | −0.43 | 0.85 | −1.63 |
| G29539 | −0.81 | 0.81 | −0.06 | 0.89 | −0.10 | AC078880.2 | −0.88 | 0.60 | −1.06 | 1.21 | −0.60 | IGKV3D-20 | −0.19 | 0.86 | 0.17 | −0.08 | −0.81 |
| PDCD6IPP2 | −0.75 | 0.14 | 0.01 | 0.10 | −0.37 | MIR3125 | 0.31 | −1.44 | −1.01 | −0.57 | 0.14 | SNX6P1 | 0.22 | −0.34 | −0.92 | 2.26 | 1.49 |
| AC004160.1 | −0.71 | 0.13 | 0.49 | −0.26 | 0.03 | AC136944.2 | 0.88 | −0.63 | −1.55 | −0.09 | −0.63 | AC010387.1 | 0.24 | −0.23 | −0.89 | 0.06 | −0.20 |
| HCN1 | −0.88 | 0.24 | 0.66 | 0.46 | 0.36 | G31873 | 0.32 | 0.42 | 0.33 | 0.11 | −0.03 | MTND1P22 | 0.12 | −0.65 | −1.29 | 1.09 | −0.18 |
| CEBPZOS | −0.20 | 0.03 | 0.10 | 0.04 | 0.17 | LINC00294 | −0.14 | 0.09 | 0.30 | −0.11 | −0.28 | AL451054.1 | −0.32 | −1.18 | 1.71 | 0.90 | 2.54 |
| PLPP2 | −0.56 | 0.66 | 0.54 | 0.61 | 0.43 | LINC01443 | 0.32 | 0.11 | 0.21 | 0.84 | 0.65 | FGF12-AS3 | −0.19 | 0.88 | −0.05 | 1.26 | 0.05 |
| CIDECP | −0.34 | 0.04 | −0.13 | 0.02 | 0.20 | AC007608.1 | −0.23 | −0.05 | −0.23 | 0.32 | 0.07 | RNU6-584P | −0.24 | 1.07 | −0.47 | 1.94 | −0.59 |
| RHBDL3 | −0.76 | 0.17 | −0.40 | −0.19 | −0.63 | CIPC | −0.09 | 0.33 | 0.21 | 0.12 | −0.20 | NIP7P1 | −0.34 | −0.44 | −0.32 | 0.41 | 1.01 |
| BAALC-AS2 | 1.72 | −0.53 | −1.07 | −0.21 | 0.07 | RNU6-616P | 0.45 | 0.44 | 1.29 | 0.29 | 0.54 | AC016708.1 | 0.02 | 0.07 | 0.26 | 0.22 | 0.01 |
| HEG1 | 0.36 | −0.09 | 0.15 | −0.25 | −0.36 | RPL12P26 | −1.53 | −0.69 | 0.84 | −0.88 | −0.32 | AP002490.2 | 0.03 | −0.30 | 0.47 | −0.13 | 0.06 |
| MED20 | 0.29 | −0.18 | −0.07 | −0.11 | −0.02 | AP001271.1 | −0.57 | −0.25 | 0.26 | 0.80 | 1.78 | ETFRF1 | 0.02 | 0.23 | 0.46 | −0.13 | 0.00 |
| AL136146.1 | 0.63 | 0.06 | −0.88 | 0.25 | −0.26 | RNU6-524P | 0.91 | 1.68 | −0.62 | 0.49 | −1.22 | LINC00376 | 0.18 | −0.40 | 1.40 | −0.71 | 2.22 |
| RPS2 | 0.36 | −0.06 | −0.16 | 0.06 | −0.10 | AC097358.2 | −0.55 | −0.78 | −0.54 | 1.15 | 0.39 | AC079117.1 | 0.18 | −1.54 | 0.98 | −0.33 | 1.15 |
| NSMCE2 | 0.23 | −0.11 | −0.24 | −0.06 | −0.17 | AC022148.1 | −0.40 | −0.22 | −0.14 | 0.29 | 0.63 | AC099343.1 | 0.26 | 0.06 | −0.68 | −0.72 | −2.17 |
| G13882 | 0.87 | −0.32 | −0.74 | −0.04 | −0.36 | AC022167.2 | 0.16 | −0.22 | −0.38 | −0.09 | 0.20 | AP005597.1 | 0.33 | −0.38 | −0.87 | 1.06 | −0.38 |
| AC012645.1 | 0.61 | −0.51 | 0.03 | −0.43 | −0.13 | RPS7P15 | 0.28 | −0.12 | −0.30 | −0.17 | −0.31 | AL359502.1 | 0.34 | −0.45 | −1.14 | −1.06 | 0.07 |
| P2RY14 | −0.73 | 0.12 | 0.71 | −0.01 | 0.21 | AL451062.2 | −0.27 | −0.50 | −0.03 | −0.11 | 1.26 | RN7SL122P | −0.20 | −0.66 | −1.02 | 0.43 | −1.72 |
| LINC00327 | −0.53 | 0.27 | 0.52 | 0.41 | 0.35 | ATG2B | −0.09 | 0.27 | 0.25 | 0.27 | −0.03 | LINC02074 | −0.16 | −1.20 | −1.59 | −0.20 | −0.56 |
| IDO1 | 1.18 | −1.32 | −0.51 | −1.97 | 0.61 | AC106028.5 | 0.53 | 0.34 | −1.14 | −0.03 | −0.63 | FRMPD4-AS1 | −0.33 | 0.01 | 0.04 | −0.97 | 0.37 |
| CAPN15 | 0.39 | −0.14 | −0.73 | 0.08 | −0.15 | MAGI2-AS2 | −0.89 | 0.69 | 0.89 | 0.73 | −1.10 | OR12D1 | −0.15 | −0.32 | −1.76 | 0.58 | −1.78 |
| GGA3 | −0.23 | 0.04 | 0.02 | 0.03 | 0.09 | CYP4F2 | −0.45 | −0.43 | 0.15 | 0.16 | 0.62 | ATP6VOE1P2 | 0.07 | −0.56 | 0.87 | −0.96 | −0.19 |
| AC007557.3 | −1.10 | 1.27 | 1.26 | 0.90 | 0.07 | AC019068.1 | −0.88 | 1.19 | −0.27 | 0.36 | −0.42 | AP005357.1 | −0.16 | −0.45 | −0.39 | −1.54 | −0.59 |
| INHA | −0.69 | 0.26 | −0.08 | 0.32 | −0.20 | LINC02438 | −0.92 | −2.13 | 1.23 | −1.46 | 0.85 | LINC00462 | 0.05 | −0.44 | −2.10 | 0.39 | 0.26 |
| PDCD4 | −0.36 | 0.56 | 0.89 | 0.22 | 0.25 | FAM32BP | 0.59 | −1.74 | −0.27 | −0.42 | 1.20 | LINC02144 | 0.17 | −1.32 | −2.24 | −0.15 | −0.38 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| SMAD1-AS2 | 0.65 | −0.34 | −0.46 | 0.17 | −0.05 | ATP4B | 0.48 | −0.78 | −0.90 | −0.44 | −0.66 | BTBD6 | 0.01 | 0.02 | −0.10 | 0.02 | −0.16 |
| HS1BP3-IT1 | −1.26 | 0.55 | 1.62 | −0.66 | 0.33 | RN7SL472P | 0.66 | −0.65 | −1.88 | 0.10 | −1.22 | RPL12P23 | 0.18 | −0.30 | −0.44 | −1.48 | −1.98 |
| PAEP | −1.58 | 0.06 | 2.94 | 0.41 | −0.44 | AL133457.1 | −0.81 | −0.03 | −0.55 | 0.06 | −1.56 | AC233702.7 | −0.05 | 0.37 | −0.06 | −0.23 | −0.49 |
| AC004975.2 | 1.09 | −0.46 | −0.52 | 0.05 | −0.04 | LIX1L-AS1 | −0.20 | −0.72 | −0.05 | −0.19 | 0.61 | EEF1A1P1 | 0.09 | −0.46 | 1.95 | −1.48 | −0.72 |
| LINC00618 | −1.03 | 0.25 | 0.36 | 1.07 | 0.72 | FASLG | 0.42 | −0.28 | 0.33 | −0.40 | 0.18 | GRM7-AS2 | −0.19 | 0.21 | 0.30 | −0.99 | −1.72 |
| RNU6-853P | 1.09 | −0.98 | −0.80 | −0.34 | −0.52 | ITPKA | −0.34 | −0.16 | −0.64 | −0.02 | −0.81 | AC036214.1 | 0.05 | 0.23 | −0.90 | 0.70 | −0.26 |
| MAD1L1 | −0.37 | −0.03 | −0.25 | 0.08 | 0.12 | FAR2P4 | 0.76 | −1.85 | 0.77 | −0.40 | 0.70 | LINC01164 | −0.09 | 0.21 | 1.08 | 0.09 | −1.75 |
| AC245052.4 | −0.55 | 0.13 | 0.43 | −0.02 | 0.42 | AC127070.3 | −1.12 | 1.83 | 0.86 | 1.23 | −0.10 | AC007490.1 | 0.20 | −0.33 | −0.32 | 1.37 | −0.16 |
| AL136441.1 | −1.16 | 0.89 | 0.64 | −0.02 | −0.34 | AC124798.2 | 0.68 | −0.85 | −0.46 | 0.81 | −0.69 | RCC2P3 | −0.33 | 0.31 | −0.02 | −0.12 | −1.11 |
| CNOT6L | 0.36 | 0.05 | 0.01 | 0.11 | −0.20 | AC105384.1 | −0.37 | −0.53 | 0.74 | 0.09 | 0.92 | MTND4P13 | 0.13 | −0.10 | −0.46 | −0.24 | 0.72 |
| FAM237B | −0.90 | 0.22 | 1.39 | −0.69 | 0.46 | LINC01115 | −0.47 | 1.20 | 0.49 | 0.54 | 1.96 | AL359682.1 | 0.13 | −1.02 | 0.77 | 0.72 | 1.90 |
| AL158156.1 | 1.02 | −0.63 | 0.88 | −0.63 | −0.15 | MT-CO1 | −0.14 | 0.06 | 0.23 | −0.08 | 0.11 | MIR4754 | −0.08 | −0.44 | −1.80 | 0.48 | −2.47 |
| DDO | −0.82 | 0.15 | 0.88 | 0.79 | 1.40 | AC140061.10 | −1.08 | 0.58 | 0.81 | 0.86 | −0.49 | AL591419.1 | −0.33 | 0.68 | NA | 0.01 | −2.02 |
| AC012615.6 | −0.46 | 0.08 | −0.51 | 0.36 | 0.19 | C2-AS1 | 0.51 | −0.55 | 0.63 | −0.41 | 0.20 | RNU2-24P | −0.07 | 0.99 | −0.38 | 0.80 | 0.08 |
| KRT8P44 | −1.05 | 0.62 | 2.20 | 0.15 | 0.48 | C4orf45 | 0.35 | −0.47 | −0.54 | 0.01 | 0.07 | AC004074.1 | −0.15 | −1.00 | 0.15 | 1.22 | 0.10 |
| G32068 | 1.17 | −0.57 | −0.66 | −0.21 | 0.06 | AL391056.1 | 0.66 | −1.30 | −0.85 | −0.56 | 0.21 | AC067957.1 | 0.09 | 1.31 | −0.94 | 0.38 | −0.74 |
| RNF144B | 0.47 | −0.09 | −0.48 | 0.11 | −0.48 | AC068134.3 | −0.46 | 0.27 | −0.06 | 0.93 | 0.94 | SSX8P | 0.32 | −0.28 | −1.17 | 0.52 | −1.36 |
| ADRAID | 0.88 | −0.47 | −1.47 | 0.59 | −0.80 | STARD13-IT1 | −0.21 | 0.18 | 0.68 | −0.35 | 0.41 | SI | 0.05 | −1.09 | −0.80 | 0.33 | 0.89 |
| ALPK1 | −0.24 | 0.08 | 0.31 | 0.09 | 0.09 | RNY1P2 | −1.11 | 1.15 | 0.16 | 1.11 | −0.43 | OR8A3P | −0.22 | 1.01 | −0.87 | 1.03 | −1.15 |
| RPL7P49 | −0.59 | 0.17 | −0.03 | 0.00 | −0.10 | RN7SKP179 | 0.64 | −0.19 | −1.40 | −0.26 | −0.97 | EFL1P2 | 0.31 | −0.62 | 0.55 | 0.32 | 1.28 |
| ATL3 | 0.33 | −0.09 | −0.25 | −0.06 | −0.36 | GLYCAM1 | −0.75 | −1.13 | −1.14 | 0.94 | 0.45 | RPSAP25 | 0.33 | −0.64 | −1.22 | 0.36 | −0.54 |
| MEMO1 | 0.36 | −0.17 | 0.04 | −0.09 | 0.01 | AC016576.1 | −0.52 | −0.81 | −0.95 | 1.21 | 0.04 | AL355095.1 | 0.33 | −0.98 | −0.86 | −1.51 | −2.75 |
| DKK1 | −1.13 | 0.03 | 0.54 | −0.93 | 0.33 | RN7SL817P | −1.15 | 0.60 | 2.95 | −1.11 | 2.30 | AC103968.1 | −0.33 | 0.00 | 0.13 | −0.62 | −0.08 |
| HSP90AB3P | 0.53 | −0.22 | −0.48 | −0.13 | −0.43 | HYDIN2 | −0.37 | −0.25 | 0.54 | −0.23 | 0.22 | MOB1AP2 | −0.33 | −0.40 | −0.95 | 1.13 | 0.63 |
| AL162258.2 | −1.05 | 0.33 | 0.54 | 0.15 | −0.14 | RN7SL218P | −0.68 | −0.15 | −1.91 | 1.10 | −1.49 | KIF1BP | −0.01 | −0.04 | 0.09 | −0.18 | −0.04 |
| RUNX1 | 0.45 | −0.32 | −0.24 | −0.55 | −0.17 | OR7E83P | 0.79 | −0.47 | −1.20 | 1.38 | −0.94 | HMGN1P17 | −0.31 | 1.26 | −0.81 | −0.10 | −3.02 |
| AL450327.1 | −1.32 | 0.80 | 0.58 | 0.86 | 0.03 | SPDYE8P | −0.39 | −0.22 | 0.33 | −0.24 | 1.41 | AC092634.5 | −0.16 | −0.15 | −0.43 | −1.46 | −2.30 |
| RNASSP199 | −1.31 | 0.87 | −0.66 | 1.36 | −0.79 | AC021074.3 | 0.84 | −1.71 | −0.17 | −0.18 | −0.90 | AL589642.2 | −0.25 | −0.90 | −1.47 | 0.89 | −0.79 |
| FAM155A-IT1 | 0.94 | −0.26 | 0.08 | −0.54 | 0.11 | HMGN1P34 | −1.40 | 2.05 | −0.04 | 2.13 | −0.63 | OR5B21 | 0.09 | 0.34 | −0.32 | −1.07 | −3.39 |
| AC098826.2 | −1.10 | −0.12 | 0.46 | 0.26 | −0.36 | AL021918.4 | −0.28 | 0.33 | 0.25 | 0.56 | −0.28 | RPSAP20 | −0.07 | 0.19 | 1.72 | 0.92 | 0.06 |
| LINC01524 | 1.51 | −0.56 | −1.13 | −1.01 | −0.69 | G7791 | 0.35 | −0.32 | 0.40 | −0.36 | 0.34 | SNORA8 | −0.05 | −0.33 | −0.72 | −0.43 | −0.51 |
| SNX32 | −0.46 | 0.04 | −0.28 | 0.33 | 0.26 | AL161938.1 | −1.37 | 0.35 | 1.27 | −0.64 | −0.88 | AC104770.1 | 0.33 | −0.53 | 0.05 | 2.16 | 0.67 |
| CEMIP2 | 0.41 | −0.40 | −0.39 | −0.48 | −0.46 | AL356488.1 | 0.29 | −0.78 | −0.36 | −0.13 | 0.24 | AC112907.3 | 0.02 | −0.13 | −0.59 | 0.29 | −0.12 |
| PLA2G4E-AS1 | 0.87 | −0.42 | −0.18 | −0.42 | −0.09 | CH17-340M24.3 | −0.24 | 0.16 | 0.51 | 0.25 | 0.52 | AC008652.1 | −0.29 | −0.31 | 0.66 | 1.02 | −1.19 |
| RPS4XP1 | 0.71 | −0.17 | −1.60 | 0.23 | −1.03 | RNU6-736P | 0.42 | 0.35 | −1.37 | 0.29 | −1.39 | AC103703.1 | −0.02 | −0.27 | −0.36 | −0.06 | −0.02 |
| PLEKHA4 | −0.55 | −0.13 | 0.58 | −0.08 | 0.57 | RPLPOP2 | 0.26 | −0.64 | −0.13 | −0.80 | 0.21 | RSL24D1P6 | 0.04 | 0.51 | −0.81 | 0.29 | −0.29 |
| AC078960.1 | 1.34 | 0.96 | −1.25 | 0.76 | −0.85 | AP001652.1 | 0.59 | −0.44 | −1.62 | 0.35 | 0.92 | LSM1P2 | −0.20 | −0.52 | −1.24 | 1.23 | 0.56 |
| RNA5SP263 | −0.99 | −0.02 | −0.50 | 0.42 | −0.65 | CLCN2 | −0.12 | 0.28 | −0.04 | 0.32 | −0.01 | LINC01837 | −0.07 | −1.13 | −0.96 | 0.59 | −0.90 |
| GPBP1L1 | 0.19 | 0.12 | 0.01 | 0.13 | −0.12 | MIR320E | −0.33 | −0.08 | 1.17 | −0.29 | 0.79 | AL078595.2 | −0.32 | −0.77 | −0.32 | −1.33 | −0.14 |
| KLB | −0.59 | 0.39 | 0.23 | 0.22 | 0.00 | AC006213.1 | −0.45 | −0.02 | 1.25 | −0.15 | 0.29 | CYCTP | 0.33 | −0.92 | −0.44 | −0.77 | −0.38 |
| AL359955.1 | −0.82 | 0.77 | 0.45 | 0.25 | 0.57 | DIP2A-IT1 | 0.15 | −0.10 | −0.38 | 0.02 | 0.03 | RN7SL452P | −0.03 | −0.17 | −0.19 | 0.02 | 0.22 |
| LAMTOR5 | 0.32 | −0.21 | −0.79 | 0.03 | −0.57 | AL645937.4 | −0.64 | −0.31 | −1.07 | −0.02 | 0.21 | AC108043.1 | 0.33 | −0.15 | −0.02 | −0.01 | 0.56 |
| HSD17B11 | −0.51 | 0.49 | 0.82 | 0.07 | 0.10 | RNA5SP86 | −1.08 | 0.62 | 0.23 | 0.91 | 0.60 | NAGK | −0.01 | 0.12 | 0.09 | −0.01 | −0.01 |
| RPL5P24 | −0.84 | 0.32 | 1.37 | 0.24 | 0.68 | AL137246.1 | −0.35 | −0.30 | 0.46 | 0.26 | 0.34 | EXPH5 | 0.02 | 0.55 | 0.57 | 0.42 | −0.11 |
| BBOX1 | 0.59 | 0.17 | −0.25 | 0.33 | −0.66 | ACMSD | −0.25 | −0.63 | 0.08 | −0.02 | 0.57 | AL627443.1 | −0.33 | −0.58 | 0.60 | −1.74 | −0.71 |
| BEST1 | −0.56 | −0.53 | −0.05 | −0.02 | 0.18 | DPYD-IT1 | 0.26 | −0.46 | −0.40 | 0.03 | 0.11 | LINC02451 | 0.14 | 0.72 | −0.81 | −1.09 | −1.38 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| IMPA2 | 0.55 | −0.06 | −0.30 | 0.13 | −0.03 | C1orf87 | −0.44 | −0.11 | −0.46 | 0.04 | −0.29 | AC100818.1 | −0.10 | −0.37 | 0.03 | 1.41 | 0.33 |
| SAMD11 | −0.88 | 0.15 | 0.37 | 0.57 | 0.27 | AC107959.4 | −0.58 | −1.41 | −1.46 | −1.00 | −1.40 | SEC13P1 | 0.04 | −0.37 | −0.92 | 0.63 | 0.18 |
| AC011477.2 | −0.40 | 0.35 | 0.71 | −0.17 | 0.13 | RBM17P2 | −0.32 | −0.03 | 0.40 | 0.33 | 0.07 | AC022081.1 | −0.33 | 0.17 | 0.66 | 0.20 | 0.91 |
| AC231657.1 | −0.93 | 0.22 | 1.07 | 0.30 | 0.54 | GNG10 | 0.39 | −0.62 | 0.54 | −0.66 | 0.56 | GRP | −0.10 | 0.87 | −0.36 | 0.26 | −1.77 |
| ACBD3 | 0.32 | −0.24 | −0.28 | −0.31 | −0.21 | AL391704.3 | 1.00 | −0.93 | −0.57 | −0.12 | 0.93 | AP005901.4 | −0.30 | −0.40 | 0.98 | −0.11 | 1.04 |
| KRBA2 | −0.77 | 0.58 | 0.98 | 0.19 | 0.16 | AL355493.1 | −0.67 | −0.77 | 1.03 | 0.30 | 1.12 | ARHGAP15 | −0.02 | −0.31 | 0.59 | −0.48 | 0.39 |
| SIGLEC14 | 1.33 | −0.99 | 0.70 | −0.48 | −0.31 | AL683813.2 | −1.13 | −0.10 | 1.00 | 1.03 | 1.47 | AC013701.1 | −0.33 | 0.80 | 1.41 | −0.11 | −1.23 |
| AC021851.1 | 0.94 | 0.11 | −0.21 | 0.12 | 0.01 | AC108448.2 | −0.36 | 0.49 | −0.01 | 0.04 | −0.03 | AC026991.1 | −0.16 | −0.52 | −1.12 | 1.29 | −0.63 |
| AC087641.1 | −1.03 | 0.27 | 0.83 | 0.53 | 0.09 | RNY1P7 | 1.12 | −1.52 | −1.73 | −0.90 | −0.68 | AC095060.1 | −0.33 | −0.51 | −1.13 | 0.98 | NA |
| LYNX1 | −0.39 | 0.64 | 0.37 | 0.20 | −0.28 | PKLR | 0.32 | 0.36 | −0.37 | 0.60 | 0.35 | AC015936.2 | −0.16 | 0.38 | −0.43 | 1.08 | −0.13 |
| SNORD116-18 | −1.06 | 0.94 | 0.42 | 3.00 | 2.12 | AC012313.5 | −0.14 | −0.22 | 0.56 | −0.20 | 0.43 | HOXD4 | 0.07 | 0.04 | 1.89 | −0.31 | −1.06 |
| RWDD1 | 0.38 | −0.25 | −0.16 | −0.25 | −0.12 | AC000081.1 | 0.52 | −0.45 | −2.15 | 0.94 | −1.10 | BMP7 | 0.02 | 0.42 | 0.41 | 0.32 | −0.06 |
| KIFAP3 | 0.23 | 0.00 | −0.09 | −0.14 | −0.27 | AC103706.3 | −0.23 | −0.34 | −0.10 | −0.57 | 0.17 | AP001180.4 | 0.08 | 1.30 | −0.07 | 1.07 | −1.09 |
| FHL5 | −0.80 | 0.63 | 0.89 | 0.81 | −0.48 | RTN2 | −0.12 | −0.01 | −0.01 | 0.00 | 0.07 | SPATA31D3 | 0.33 | −1.08 | 1.59 | −1.00 | 0.24 |
| PEA15 | 0.31 | −0.09 | −0.19 | −0.15 | −0.39 | AC100852.1 | −0.46 | 0.01 | −1.76 | 0.54 | −1.25 | AC096666.1 | 0.30 | −0.79 | −0.61 | 0.12 | −0.60 |
| AC147067.1 | −0.72 | −0.13 | 1.13 | −0.17 | 0.58 | AC097662.1 | −0.26 | 0.34 | 0.53 | −0.32 | −0.09 | AC112512.1 | −0.02 | −0.10 | 0.23 | −0.09 | 0.16 |
| AL928654.4 | −0.33 | 0.12 | 0.18 | 0.10 | 0.18 | AL137784.1 | −0.47 | 0.55 | 1.80 | −0.48 | 0.45 | AL731532.1 | 0.08 | −0.67 | −2.27 | 0.12 | −3.22 |
| LGALS1 | −0.60 | 0.13 | 0.59 | −0.46 | 0.01 | NREP-AS1 | −0.49 | 0.10 | −0.35 | −1.68 | −1.71 | OSTN-AS1 | 0.12 | 0.13 | −0.66 | 0.41 | −1.39 |
| AL136116.2 | 0.93 | −0.55 | −1.38 | 0.35 | 0.38 | G19167 | 0.81 | −1.59 | 0.88 | 0.57 | −0.22 | AL133481.2 | 0.33 | −1.18 | −1.32 | −0.55 | −0.25 |
| SMIM10L1 | 0.37 | −0.17 | −0.22 | 0.00 | −0.03 | AP003122.5 | 0.70 | 0.09 | −1.21 | −0.25 | −1.85 | AC093001.1 | 0.32 | −1.03 | 0.54 | −1.07 | 0.84 |
| MPIG6B | −0.35 | 0.48 | 0.54 | −0.03 | −0.13 | AL138880.2 | 0.52 | −0.81 | −2.87 | −0.04 | −0.42 | P2RY10BP | −0.33 | 0.06 | 0.04 | −0.58 | 0.04 |
| HNRNPA1P48 | 0.30 | −0.30 | −0.45 | 0.06 | 0.01 | MTCO1P5 | −0.82 | −0.59 | −0.95 | 0.30 | 0.46 | AC078852.2 | 0.04 | −0.05 | 0.15 | 0.30 | 0.83 |
| PCDHA6 | −1.10 | 0.89 | 0.18 | 0.52 | −0.87 | AC116903.2 | −0.24 | 0.03 | 0.92 | −0.12 | 0.63 | AL691426.1 | 0.19 | 0.16 | −1.22 | 0.46 | −1.51 |
| EHD1 | 0.36 | −0.27 | −0.87 | −0.11 | −0.60 | NDUFAF4P4 | 0.39 | −0.34 | −0.02 | −0.40 | −0.53 | ERP29 | 0.01 | 0.11 | 0.22 | 0.00 | −0.04 |
| AL121787.1 | −1.55 | −0.30 | 1.18 | −1.34 | −0.18 | AP003392.5 | 0.33 | 0.11 | 0.29 | 0.14 | −0.13 | AL929302.1 | 0.33 | −0.35 | −1.13 | −0.30 | −0.54 |
| AL133477.1 | 0.89 | −1.25 | −0.20 | −0.35 | 0.51 | AL132657.2 | −0.44 | −1.41 | 1.71 | 0.19 | 1.73 | AC107613.1 | 0.32 | −1.07 | 0.44 | 1.21 | 1.05 |
| RAD54L | 0.45 | −0.59 | −0.91 | −0.24 | −0.19 | AC008694.2 | 0.78 | −0.51 | −1.61 | 0.90 | −1.05 | CCDC13 | −0.04 | −0.37 | 0.47 | −0.29 | −0.13 |
| SLIT2-IT1 | −1.05 | 0.50 | 2.05 | −0.26 | 0.10 | DMBT1P1 | −0.32 | −0.12 | −0.96 | 0.59 | 0.22 | AC016687.2 | 0.18 | 0.70 | 0.51 | −1.20 | −1.22 |
| LINC01730 | 0.80 | −0.64 | −0.60 | −0.36 | −0.47 | CBX5P1 | 0.23 | 0.03 | 0.04 | −0.27 | −0.20 | AC245054.1 | −0.09 | −0.97 | −0.64 | 1.24 | −0.03 |
| AP001922.6 | −1.78 | 1.06 | 1.06 | −1.88 | −0.46 | MIR203 | 0.28 | 0.18 | −0.09 | 0.10 | −0.01 | ECEL1P3 | 0.08 | 1.44 | 1.05 | 0.86 | 0.21 |
| LINC00659 | 2.33 | −1.54 | −1.34 | −0.33 | 0.29 | RNU6-431P | 0.39 | −0.57 | 2.40 | −0.79 | −0.44 | SIAH1P1 | −0.31 | −0.20 | 0.63 | 0.29 | −0.59 |
| AP000787.1 | −0.31 | 0.10 | −0.09 | 0.17 | −0.11 | OR2S2 | −0.71 | −1.14 | 2.91 | −0.96 | 0.92 | LINC01519 | −0.10 | −0.92 | −0.79 | −0.82 | −2.06 |
| CU639417.3 | −0.88 | 0.64 | 0.94 | 0.23 | −0.45 | LINC02239 | −0.94 | 0.62 | −1.67 | 0.82 | −0.41 | RN7SL237P | 0.08 | 0.53 | 0.89 | 1.18 | −0.25 |
| RPS11P5 | 0.54 | −0.25 | 0.27 | −0.30 | 0.05 | AC092167.1 | −0.56 | 0.08 | −0.39 | 0.11 | −1.26 | AC009432.2 | 0.16 | 1.32 | 0.25 | −0.49 | −2.76 |
| MTND2P41 | 1.31 | −0.84 | −0.86 | 0.37 | −0.18 | AC073288.2 | 0.31 | 0.41 | −1.17 | 0.44 | −0.72 | AC138907.8 | −0.32 | −0.09 | 0.15 | −0.72 | −1.68 |
| AC006042.1 | −0.83 | 0.18 | 0.80 | −0.08 | 0.56 | OR51A5P | 0.76 | 0.23 | −1.17 | 1.54 | −0.56 | OR4Q3 | 0.06 | 0.07 | −0.35 | 1.29 | −0.41 |
| PLD1 | 0.34 | 0.01 | 0.07 | 0.13 | 0.08 | AC124014.1 | 0.39 | −1.58 | 0.78 | −1.03 | 0.35 | OR2P1P | 0.33 | −0.66 | −0.51 | −1.35 | −0.50 |
| AC006355.1 | −1.28 | 0.57 | 0.64 | 0.29 | −0.76 | AC067852.3 | 0.14 | 0.22 | 0.42 | 0.00 | −0.03 | AC090772.3 | 0.03 | 0.00 | 0.72 | 0.23 | 0.57 |
| DIAPH3-AS2 | 1.85 | −1.13 | −0.35 | −0.77 | −0.28 | SERAC1 | 0.09 | 0.11 | 0.18 | −0.05 | 0.05 | AC002127.2 | 0.12 | 0.30 | −0.80 | 1.31 | −0.69 |
| G8415 | −0.76 | 0.00 | 0.95 | −0.48 | 0.54 | AC090241.2 | −0.41 | −1.10 | 0.06 | −1.44 | −0.35 | KDM6B | −0.01 | −0.06 | −0.38 | −0.08 | −0.19 |
| RNU6-1161P | 2.14 | −0.92 | −2.25 | −0.24 | −1.88 | MPV17 | −0.07 | 0.00 | 0.23 | −0.07 | 0.06 | OR4A42P | −0.22 | −0.63 | −0.76 | 1.49 | 0.19 |
| MTMR3 | −0.24 | 0.33 | 0.39 | 0.04 | −0.07 | AC091390.3 | −0.22 | 0.43 | 0.55 | 0.37 | 0.21 | MTATP6P7 | −0.13 | −0.21 | −0.54 | 0.85 | 0.54 |
| NOSTRIN | −0.47 | 0.38 | 0.81 | 0.17 | 0.45 | POT1-AS1 | −0.35 | 0.29 | −0.54 | 0.59 | −0.11 | KLHL1 | −0.07 | −0.04 | −1.98 | 1.00 | −1.35 |
| PHF14 | 0.20 | −0.08 | −0.20 | −0.06 | −0.06 | AC104109.4 | 0.30 | −0.41 | −0.45 | −0.01 | 0.29 | RN7SL197P | −0.32 | 0.51 | −0.74 | 0.17 | −1.11 |
| ASB4 | −1.22 | −0.21 | 0.55 | −0.20 | 0.09 | AC010913.1 | 0.36 | −0.17 | −1.01 | 0.29 | −0.43 | LINC02096 | 0.31 | −0.62 | −2.07 | −0.73 | −0.05 |
| PCDHGC4 | −0.37 | 0.09 | 0.17 | 0.12 | 0.19 | FMO8P | 0.66 | −0.83 | 0.27 | −0.13 | −0.08 | AC092114.1 | −0.11 | −1.40 | −0.59 | 0.56 | 1.96 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| STX1A | 0.48 | −0.77 | −0.95 | −0.55 | −0.14 | G38166 | 0.23 | −0.14 | −0.37 | 0.14 | 0.18 | CTNS | −0.01 | 0.01 | −0.30 | −0.01 | −0.15 |
| CCR9 | −0.49 | 0.68 | 0.37 | 0.21 | −0.44 | SNAPC2 | 0.11 | −0.03 | −0.02 | 0.07 | 0.16 | AC097376.2 | −0.01 | 0.01 | 0.17 | 0.02 | 0.19 |
| AC092111.2 | −1.01 | 0.11 | 0.79 | 0.31 | 0.10 | AC025428.2 | 0.68 | −1.76 | −1.59 | 0.38 | 0.51 | GLIPR2 | −0.02 | −0.22 | 0.46 | −0.25 | 0.19 |
| MTBP | 0.30 | −0.45 | −0.24 | −0.19 | 0.16 | CDIP1 | 0.10 | 0.03 | 0.00 | 0.00 | 0.08 | MIR5587 | 0.06 | −0.78 | −0.98 | 0.21 | 0.02 |
| HINT2P1 | −1.82 | 0.80 | 1.70 | 0.36 | 0.22 | AC021148.1 | −0.30 | 0.73 | 0.40 | −0.04 | −0.27 | GPR50 | −0.09 | −0.54 | −1.92 | 1.15 | 0.93 |
| RN7SL166P | 0.87 | −0.40 | −0.51 | −0.15 | 0.12 | CALM2P3 | −0.51 | 0.34 | 0.77 | 0.19 | 0.12 | AC093286.1 | 0.31 | 0.16 | −1.19 | 0.64 | −0.71 |
| INIP | 0.28 | −0.17 | 0.09 | −0.15 | 0.00 | AC131280.1 | −0.37 | −0.55 | −0.81 | 0.62 | 0.54 | COX7B2 | −0.25 | 0.41 | −0.27 | −0.15 | −1.26 |
| AC027763.1 | −0.68 | 0.29 | 0.54 | 0.26 | 0.20 | AC006972.1 | −0.53 | 0.42 | 1.18 | −0.01 | 1.34 | HMGB3P3 | 0.08 | −1.45 | −0.74 | 0.21 | 0.51 |
| LAMTOR1 | 0.21 | −0.04 | −0.04 | 0.01 | −0.03 | RN7SL684P | 0.69 | −0.90 | −3.07 | −0.03 | 0.46 | CCL23 | 0.06 | 0.24 | 0.82 | −0.29 | 0.13 |
| AC104662.1 | −1.43 | 0.95 | 2.47 | 0.15 | 0.91 | AC111152.1 | 0.86 | −1.07 | −2.25 | −0.61 | −2.11 | RORA-AS1 | −0.03 | 0.55 | 1.00 | 0.09 | −0.02 |
| AC005920.3 | 1.69 | −1.25 | −1.99 | 0.49 | −1.48 | MIR3194 | −0.41 | 0.07 | 0.63 | 0.45 | 0.27 | AC087341.1 | −0.31 | −0.69 | 0.13 | 0.38 | 0.47 |
| ANKS4B | −0.97 | 0.24 | 0.53 | −0.39 | −0.59 | AC004014.2 | 0.45 | −1.91 | −1.58 | 0.03 | 0.91 | AC074052.1 | −0.32 | 0.77 | 0.45 | −0.39 | −1.48 |
| AC037487.2 | −0.59 | −0.39 | 0.24 | −0.42 | 0.44 | AL357033.2 | 0.74 | −0.28 | −0.25 | 0.03 | −0.23 | LINC01533 | 0.09 | 0.08 | −1.40 | 0.19 | −1.50 |
| G32306 | −1.06 | 0.86 | 1.16 | 0.69 | 0.24 | AL022316.1 | −0.44 | −0.40 | 0.27 | −0.43 | 0.17 | AC025043.1 | −0.04 | −0.39 | −1.48 | 0.45 | −0.36 |
| REC114 | 0.54 | −0.23 | 0.04 | 0.07 | 0.31 | AC109129.1 | −0.65 | 0.38 | −0.89 | 1.09 | −0.85 | AC021171.1 | 0.03 | −0.89 | 0.26 | 0.22 | 0.79 |
| AL117190.3 | 1.59 | −0.10 | −0.94 | −0.37 | −0.87 | MIR1273G | −1.19 | 1.50 | 1.08 | 1.28 | 1.81 | PYHIN1 | −0.03 | −0.68 | 0.52 | −0.43 | 0.88 |
| AC004967.2 | −0.50 | 0.29 | 0.72 | 0.09 | 0.54 | HLA-V | −0.21 | −0.68 | −1.01 | 0.10 | 0.44 | SMARCA4 | 0.01 | −0.12 | −0.31 | −0.01 | 0.02 |
| LINC02463 | −1.33 | 2.27 | 1.51 | 1.42 | 0.22 | CALML3-AS1 | −0.15 | 0.18 | 0.06 | 0.04 | 0.04 | FUS | 0.01 | −0.16 | −0.12 | −0.01 | 0.11 |
| AC064807.2 | −1.68 | 0.22 | 0.95 | −0.21 | −0.15 | RPL3P2 | 0.23 | 0.20 | −0.14 | 0.28 | −0.29 | AC005377.1 | −0.17 | 0.61 | −0.18 | 2.11 | −1.38 |
| AL139247.1 | 1.66 | −0.17 | −1.14 | 0.32 | −1.70 | AL139274.1 | 0.21 | 0.06 | 0.01 | 0.22 | 0.16 | EIF4E2P2 | −0.06 | 0.67 | 0.35 | 0.62 | −0.47 |
| RTN4RL2 | −0.66 | 0.28 | −0.30 | 0.78 | 0.34 | LRIT1 | −0.78 | −0.69 | 1.72 | 0.09 | 2.49 | RN7SL837P | 0.16 | 0.70 | −0.34 | −1.05 | −2.60 |
| AC137723.1 | −1.55 | 0.45 | 0.77 | −0.63 | 0.86 | FTH1P24 | −0.27 | 0.28 | 0.66 | −0.16 | −0.26 | AC008415.1 | −0.32 | 0.50 | 1.26 | 2.61 | −0.19 |
| IZUMO4 | −0.59 | −0.06 | −0.13 | 0.14 | −0.09 | AL034370.1 | 0.63 | 0.58 | 0.05 | −0.01 | −1.57 | IFNA2 | 0.32 | −1.25 | −0.50 | −0.98 | −0.26 |
| AL121890.5 | −1.29 | 0.60 | 1.38 | −0.61 | −0.10 | HSPB1P1 | 0.21 | 0.55 | −0.32 | 0.30 | −0.80 | LINC01201 | 0.32 | −0.02 | −1.36 | 0.43 | −0.37 |
| MTND1P8 | −0.86 | 0.08 | 1.08 | −0.45 | 0.56 | FOSL2 | 0.08 | −0.02 | −0.11 | −0.10 | −0.27 | SNHG5 | −0.01 | 0.08 | 0.12 | 0.13 | −0.08 |
| G34279 | −1.25 | 0.79 | 2.47 | 0.45 | −0.06 | AC092143.3 | −0.46 | 0.16 | −0.81 | 0.85 | 0.12 | MIR548X | −0.32 | −0.37 | −0.77 | 0.60 | 0.28 |
| CR769776.1 | −1.46 | 0.55 | −1.02 | 1.00 | 1.42 | CTD-2145A24.3 | 0.26 | −0.57 | −0.75 | 0.34 | 0.15 | AKR1B10P2 | 0.15 | −1.19 | −2.56 | 0.34 | −0.42 |
| AC091868.2 | 0.63 | −0.39 | −0.51 | −0.76 | 0.09 | AC009127.2 | −0.70 | −0.55 | 1.11 | 1.02 | 1.71 | MRPS18AP1 | 0.04 | −0.76 | −1.14 | −0.37 | −0.59 |
| AC104162.1 | −0.71 | 0.01 | 0.53 | 0.18 | 0.44 | AC025162.2 | 0.52 | −0.26 | −1.09 | 0.42 | −0.29 | HTR1F | 0.03 | −0.17 | −0.14 | 0.34 | −0.45 |
| SNORD37 | −1.30 | −0.97 | 0.24 | 0.78 | 0.16 | MIR3128 | 0.33 | −0.14 | −1.02 | 0.52 | −0.03 | AC016876.2 | 0.05 | 0.35 | −0.40 | 0.06 | −0.54 |
| ATAT1 | −0.30 | 0.03 | 0.04 | 0.15 | 0.15 | RAMP1 | −0.25 | −0.46 | −0.64 | −0.25 | 0.01 | LINC00434 | −0.32 | −0.19 | 0.63 | 0.62 | 1.22 |
| AC013472.1 | −0.47 | 0.13 | 0.66 | −0.04 | 0.35 | AC007038.2 | 0.16 | −0.01 | 0.07 | −0.07 | −0.11 | KCTD10P1 | 0.32 | 0.61 | −1.63 | 1.22 | −1.80 |
| FAM50A | −0.49 | −0.05 | 0.00 | −0.03 | 0.06 | MIR1255B2 | 0.85 | −0.33 | −2.18 | 0.91 | 0.33 | AC097658.1 | −0.02 | −0.06 | 0.14 | 0.11 | 0.34 |
| AC092422.1 | −1.92 | 2.14 | 2.43 | −0.81 | −1.09 | POM121L2 | −0.54 | −0.13 | −1.39 | 0.58 | −0.99 | GAPDHP38 | −0.03 | −0.70 | −1.02 | 0.49 | 0.58 |
| LOXL1 | −0.46 | 0.29 | 0.43 | 0.00 | −0.03 | DHX35 | 0.06 | −0.23 | −0.19 | 0.03 | 0.23 | AC063962.1 | −0.32 | −0.02 | −0.43 | 0.12 | −0.39 |
| CHKB-DT | 0.38 | −0.68 | −0.16 | −0.04 | 0.72 | RNU6-118P | 0.34 | −0.05 | 0.33 | 0.06 | −0.04 | AC091730.1 | 0.19 | −0.66 | 0.54 | 1.67 | −0.80 |
| AC026691.1 | −0.80 | 0.28 | −0.21 | −0.09 | −0.47 | LINC02299 | −0.70 | −0.93 | −2.01 | −0.10 | −0.13 | AC007879.2 | −0.06 | 0.15 | 1.34 | −0.15 | −0.46 |
| GPR132 | −0.56 | −0.04 | 0.15 | −0.16 | −0.05 | LAS1L | 0.09 | −0.10 | −0.08 | −0.08 | −0.03 | AL513285.1 | −0.32 | −0.02 | −0.93 | 1.74 | −0.57 |
| SMPD4 | 0.27 | −0.16 | −0.40 | 0.00 | −0.11 | RPS19P7 | −0.48 | −0.87 | −0.41 | −0.50 | −0.61 | AP003122.4 | −0.32 | −0.13 | −1.30 | 0.50 | −0.48 |
| SHISA3 | −1.68 | 0.69 | 0.90 | 1.31 | 0.97 | AC113410.2 | −0.38 | −0.16 | 1.43 | 0.86 | 0.20 | LINC01581 | −0.06 | −0.18 | −0.69 | 0.04 | −0.48 |
| AC018832.1 | −1.07 | 0.55 | 0.49 | −0.17 | −0.35 | AL451139.1 | 0.44 | −0.09 | −0.02 | 0.17 | −0.14 | AP003171.1 | 0.26 | −0.19 | 0.19 | 0.57 | −0.76 |
| DOCK4 | 0.34 | −0.35 | −0.46 | −0.25 | −0.03 | CETN1 | −0.93 | 0.62 | −1.14 | 0.39 | −0.96 | PRELID3BP10 | −0.32 | −0.39 | −1.11 | 0.88 | NA |
| RBMS2 | −0.27 | 0.30 | 0.34 | 0.07 | −0.14 | AL513328.1 | −0.54 | 0.02 | 1.20 | −0.88 | −0.82 | LINC02466 | −0.09 | 0.86 | −0.62 | 1.05 | −0.82 |
| CCDC105 | −1.62 | −0.23 | 2.25 | −0.85 | 0.74 | DNAJC27 | −0.08 | 0.10 | 0.08 | 0.06 | 0.16 | OR2G3 | 0.11 | 0.28 | 1.10 | −1.19 | −0.55 |
| RNU6-48P | 1.07 | −0.34 | −0.18 | 0.21 | 0.00 | RN7SL612P | 0.69 | −1.47 | −0.76 | −0.80 | −0.11 | AL356476.1 | 0.32 | −0.04 | −0.14 | −0.07 | −0.97 |
| RN7SL5P | −0.72 | 0.17 | −0.76 | 0.77 | −0.63 | LINC01694 | 0.36 | −0.53 | −1.60 | 0.06 | −0.24 | RAET1E-AS1 | 0.03 | 0.46 | 0.45 | 0.19 | −0.37 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| GRIN2B | −0.74 | 0.05 | 0.30 | 0.08 | −0.44 | OR5AS1 | −0.42 | −0.34 | −1.34 | 0.07 | −0.72 | RP11-439A17.9 | 0.05 | −0.48 | 0.87 | −0.71 | 0.33 |
| G35951 | −0.93 | 0.47 | 0.69 | 0.60 | −0.33 | AL139002.1 | −0.73 | −0.03 | −0.26 | 0.58 | −0.21 | AC074237.1 | 0.32 | 0.54 | −0.06 | −0.31 | −1.00 |
| SNORA14A | −0.59 | 0.79 | 0.30 | 0.19 | −0.71 | AC116003.1 | 0.76 | −0.66 | 0.38 | −0.80 | −0.46 | AC016710.1 | −0.32 | 0.17 | −0.58 | 0.01 | −1.45 |
| CYP3A4 | −0.90 | 0.75 | 1.46 | 0.15 | 0.26 | ATP6V1E1P1 | 0.72 | −1.79 | −1.42 | −0.04 | −0.94 | AC008897.2 | −0.03 | 0.03 | −1.12 | −0.29 | −1.48 |
| DNAH12 | −0.76 | 0.12 | −0.07 | 0.24 | 0.24 | IKBKE | 0.12 | −0.21 | −0.48 | 0.09 | 0.05 | FAM9C | −0.06 | 0.18 | 0.05 | 1.40 | 2.29 |
| RPL34P21 | 1.04 | −0.13 | −0.66 | −0.22 | −0.53 | RNU6-7 | −0.36 | 0.20 | 0.54 | 0.75 | −0.18 | OR5D17P | −0.14 | 0.91 | −2.55 | 1.83 | −2.27 |
| SETDB1 | −0.18 | −0.05 | 0.02 | 0.08 | 0.05 | AL354920.1 | 0.27 | −0.08 | −0.52 | −0.21 | −0.47 | MTCYBP14 | 0.32 | −1.09 | −0.97 | 0.68 | 0.73 |
| ABCC10 | −0.33 | 0.00 | 0.01 | 0.08 | 0.14 | MTCYBP7 | 0.75 | −1.08 | −1.20 | 0.11 | 0.04 | RPEP3 | 0.03 | 0.17 | 0.44 | 0.22 | 0.10 |
| NSMCE4A | −0.15 | 0.12 | 0.09 | 0.05 | 0.01 | AC016957.2 | −0.28 | 0.51 | 0.98 | 0.06 | 0.54 | IGHJ3P | 0.31 | −0.38 | 0.11 | −0.64 | −1.99 |
| AC012313.3 | −0.75 | −0.17 | 0.19 | 0.16 | 0.23 | LRRC26 | −0.57 | 0.49 | 3.10 | 0.12 | 0.64 | AC003958.1 | 0.32 | −1.36 | −0.82 | −1.03 | −0.74 |
| RNA5SP233 | 1.26 | −0.06 | 0.89 | −0.61 | −0.27 | RNU6-957P | 0.47 | −0.22 | −1.76 | 0.39 | −0.80 | AC090425.2 | −0.04 | −0.32 | −0.58 | 0.03 | −0.18 |
| AC005005.3 | 0.89 | −0.11 | −0.06 | −0.85 | −0.59 | NUTM2E | 0.44 | −0.20 | −0.40 | −0.25 | −0.96 | GALR2 | 0.03 | 0.35 | −0.29 | 0.36 | 0.17 |
| RPL39P36 | −0.98 | 0.43 | 0.98 | −0.48 | 0.33 | AC111149.2 | 1.06 | −0.53 | −3.28 | 0.86 | −2.18 | AC142086.5 | 0.32 | −0.64 | −0.20 | −0.19 | −0.26 |
| AC092117.1 | −0.56 | 0.32 | 0.48 | 0.12 | −0.01 | HTN3 | 0.87 | −0.72 | −1.90 | −0.03 | −1.68 | LINC01033 | 0.06 | −0.71 | 1.88 | 0.73 | 0.04 |
| MANEA-DT | −0.47 | 0.44 | 0.59 | 0.22 | 0.12 | G24802 | −0.30 | −0.02 | −0.13 | 0.11 | −0.01 | AC007993.1 | −0.16 | −1.17 | 0.98 | 0.41 | 1.60 |
| RPS7P1 | 0.51 | −0.33 | −0.50 | −0.03 | −0.50 | GPM6B | −0.11 | −0.19 | 0.40 | −0.37 | 0.28 | BLCAP | 0.01 | −0.09 | −0.38 | 0.16 | 0.05 |
| INTS12 | 0.23 | −0.03 | −0.23 | −0.04 | −0.29 | AL451050.2 | 0.43 | 0.07 | −0.38 | −0.30 | −0.61 | PAGE2 | 0.15 | 1.14 | −2.53 | 2.54 | −1.48 |
| LPAR5 | 0.44 | −0.12 | −0.58 | 0.19 | −0.06 | AC016065.2 | 0.33 | −0.37 | −0.30 | −0.15 | 0.01 | RBM22P13 | 0.25 | 0.82 | −0.56 | −0.83 | −0.84 |
| PDGFB | −0.46 | 0.00 | 0.13 | −0.18 | 0.06 | AC100757.3 | −1.23 | −0.01 | 1.01 | 0.40 | 0.08 | AC116553.1 | −0.13 | −2.43 | −1.38 | −2.45 | −2.04 |
| PI16 | −0.97 | 1.36 | 3.23 | −0.09 | −0.30 | ACR | −0.32 | 0.79 | 0.22 | 0.86 | 0.06 | KRT18P2 | 0.19 | −1.19 | −0.09 | 0.30 | 1.51 |
| CYP4F35P | −1.38 | 0.60 | 1.20 | −0.66 | −0.68 | NTHL1 | −0.12 | −0.18 | −0.19 | 0.29 | 0.41 | GIPC3 | 0.03 | −0.24 | 0.00 | 0.03 | −0.09 |
| CNGA4 | −0.92 | −0.09 | 0.37 | −0.36 | −1.01 | RP11-782C8.8 | −0.56 | 1.63 | 1.23 | 1.04 | −0.20 | AC008794.1 | 0.13 | −0.33 | −1.07 | 0.13 | −2.36 |
| AC113191.1 | 0.62 | −0.37 | −0.41 | −0.16 | −0.34 | RAC3 | −0.14 | 0.21 | 0.13 | 0.17 | 0.20 | CYP4F3 | 0.02 | 0.19 | 0.08 | 0.13 | 0.04 |
| DRD1 | −1.10 | 0.34 | −0.60 | 1.03 | −0.58 | AC008972.1 | 0.47 | −0.77 | −0.61 | 0.38 | 0.07 | COX6CP6 | −0.32 | 0.30 | −0.13 | −1.08 | −1.67 |
| G39661 | −1.46 | 0.53 | 2.96 | −0.30 | 0.31 | SPTBN5 | −0.16 | −0.12 | −0.41 | −0.06 | −0.13 | ARL4AP3 | 0.19 | −0.70 | −1.35 | 1.09 | 1.52 |
| MMP16 | −0.62 | 0.57 | 1.12 | 0.23 | 0.20 | AL162742.1 | 0.23 | 0.26 | −0.51 | −0.50 | −0.76 | OR5M14P | −0.31 | 0.99 | 0.02 | 0.25 | −1.19 |
| AC007610.4 | −0.38 | −0.33 | 0.39 | −0.13 | 0.74 | SPICE1 | −0.11 | 0.09 | 0.41 | 0.04 | 0.23 | AC078777.1 | 0.03 | −0.02 | −0.09 | 0.00 | 0.08 |
| AC007216.1 | −0.63 | 0.59 | 0.70 | 0.16 | −0.04 | RPL12P9 | −0.38 | 0.58 | −0.03 | 0.49 | 0.40 | AC073109.1 | −0.02 | −0.22 | 0.59 | 0.01 | 0.27 |
| PIGH | −0.28 | 0.10 | 0.32 | 0.00 | 0.27 | AL591719.1 | 0.22 | 0.00 | 0.52 | −0.04 | 0.42 | RPL6P21 | 0.31 | −1.05 | 0.22 | −1.43 | −0.48 |
| AC091044.1 | 1.22 | 0.24 | 1.23 | −0.44 | −0.45 | POU5F1 | −0.15 | −0.06 | −0.39 | 0.18 | −0.19 | LINC00824 | −0.05 | −0.53 | −0.51 | 0.65 | 0.49 |
| AC020549.1 | −0.89 | 0.45 | 0.57 | −0.03 | 0.56 | BX284668.2 | −0.40 | −0.57 | −1.90 | 0.23 | −0.69 | ADH5P2 | −0.09 | −1.09 | −0.88 | −0.46 | 0.56 |
| CD59 | 0.38 | 0.05 | −0.11 | −0.14 | −0.07 | AC098934.4 | 0.81 | −1.44 | 0.50 | 0.70 | 0.70 | AC019226.2 | 0.07 | 0.14 | 0.70 | −0.15 | 0.68 |
| NPIPB3 | −0.45 | 0.38 | 0.33 | −0.06 | −0.12 | AC004801.4 | 0.93 | −0.39 | −0.28 | 0.20 | −1.74 | AC078785.2 | −0.04 | −0.81 | 0.11 | −0.23 | 1.02 |
| PSMA2 | 0.37 | −0.08 | −0.46 | 0.01 | −0.39 | RN7SKP259 | −0.91 | −0.93 | −0.47 | 0.02 | −0.46 | AC087499.4 | −0.31 | −0.74 | −0.13 | −0.15 | 0.99 |
| CCDC138 | 0.37 | −0.34 | −0.18 | −0.20 | 0.11 | LINC01355 | −0.11 | 0.00 | 0.51 | 0.02 | 0.35 | AL049874.4 | −0.31 | 1.19 | 0.14 | 2.94 | −2.11 |
| PDPR | −0.17 | 0.00 | −0.05 | −0.06 | −0.27 | RPL23AP50 | 0.32 | −0.53 | 0.04 | −0.04 | 0.59 | AC027544.1 | −0.02 | −0.15 | −0.01 | 0.08 | 0.14 |
| AL158151.2 | −1.19 | 0.45 | 0.52 | 1.11 | 1.12 | GTF2IRD1 | −0.11 | 0.20 | −0.06 | 0.00 | −0.16 | RPL23P11 | −0.31 | −0.43 | −0.24 | 0.02 | −1.34 |
| M1AP | −0.80 | 0.23 | 1.08 | −0.30 | 0.09 | GMCL1 | 0.08 | 0.02 | 0.22 | −0.12 | 0.02 | AC008040.3 | −0.19 | −0.21 | −0.60 | 0.43 | 0.43 |
| NFIA-AS2 | −1.20 | 0.32 | 1.28 | 0.03 | 0.50 | H1F0 | −0.10 | 0.09 | −0.15 | 0.05 | −0.14 | AC128685.1 | 0.06 | −0.45 | −2.96 | 1.68 | −1.74 |
| LINC01840 | −1.64 | 0.49 | 0.65 | 0.24 | 0.59 | KLRC2 | 1.20 | 0.17 | 0.99 | −0.97 | 1.15 | DGKZP1 | 0.02 | 0.02 | 0.06 | 0.01 | 0.33 |
| RCBTB2 | 0.33 | −0.23 | −0.22 | −0.16 | −0.02 | AC087761.1 | −0.47 | −1.85 | 0.72 | −0.75 | 2.99 | ARHGAP8 | −0.02 | 0.02 | 0.02 | 0.02 | 0.55 |
| MMP2-AS1 | −0.96 | −0.45 | 0.52 | −0.06 | 0.31 | AC064801.1 | −0.21 | 0.04 | 0.24 | 0.31 | 0.40 | AP005230.1 | 0.04 | −0.47 | −0.21 | −0.19 | 0.26 |
| AL606491.1 | −0.75 | 1.01 | 1.06 | 0.58 | 0.28 | CEP120 | −0.08 | 0.00 | 0.15 | −0.02 | 0.16 | LINC01909 | 0.02 | −0.39 | −0.31 | −0.19 | 0.03 |
| AC011447.3 | −0.58 | −0.11 | 0.45 | 0.04 | 0.34 | AL021394.1 | 0.62 | 0.56 | 0.65 | −0.05 | 0.24 | IZUMO1R | 0.15 | −0.19 | 0.36 | −0.79 | −1.12 |
| AL445933.1 | −0.52 | −0.10 | −0.46 | 0.49 | 0.27 | SAMD13 | −0.26 | 0.04 | 0.77 | −0.05 | 0.39 | OR7E90P | −0.15 | −0.59 | 1.25 | 0.75 | 3.34 |
| AC133065.1 | 0.87 | −1.51 | −0.52 | −0.41 | 0.15 | NCLP2 | 0.87 | −1.64 | 0.10 | −0.18 | 1.27 | AC009554.1 | 0.03 | −0.31 | −0.65 | 0.16 | −0.25 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| MIR3609 | −0.53 | 0.66 | 1.30 | −0.22 | −0.02 | FANCD2OS | 0.37 | −0.61 | −0.26 | −0.58 | 0.00 | CDC42P2 | −0.13 | −1.08 | −0.90 | 0.00 | −0.80 |
| RN7SL288P | 1.12 | −1.53 | −0.77 | −0.57 | 0.69 | AC116348.3 | 0.76 | 0.13 | 0.90 | −0.37 | 0.13 | ITCH-IT1 | 0.03 | −0.61 | 0.11 | −0.22 | 0.59 |
| CXCL12 | −0.81 | 0.67 | 2.15 | 0.02 | 0.26 | AL391422.3 | −0.99 | −0.07 | 0.16 | 1.01 | 1.39 | AL451069.1 | −0.16 | −0.38 | 0.90 | −0.54 | 0.32 |
| NAV2 | −0.35 | 0.09 | −0.01 | 0.14 | −0.09 | CCDC68 | −0.17 | −0.06 | 0.32 | −0.11 | 0.19 | SIGLEC29P | −0.31 | −0.54 | −0.87 | 0.26 | −0.79 |
| RNU6-674P | −0.88 | 0.56 | 0.92 | −0.19 | 0.08 | AL360181.1 | 0.55 | −0.96 | −0.57 | 0.88 | 0.10 | AC015795.1 | 0.06 | 0.73 | 1.16 | 0.25 | −0.05 |
| LINC01060 | 0.93 | −1.01 | −1.39 | −0.63 | −0.54 | SNORA59B | −0.28 | 0.26 | −0.63 | 0.88 | 0.22 | AC082650.1 | −0.31 | NA | 0.65 | −0.53 | 0.91 |
| CYP3A43 | −0.88 | 0.39 | 0.76 | −0.15 | −0.72 | AC093166.3 | 0.41 | −0.86 | −0.87 | 0.09 | 0.31 | AC087399.1 | 0.31 | −0.19 | −0.86 | 1.50 | −0.51 |
| SMURF2P1 | −0.62 | −0.07 | 1.05 | 0.24 | 0.92 | AC025871.2 | 0.60 | 0.38 | 0.56 | −0.64 | 0.06 | LINC02335 | 0.11 | 0.58 | −2.00 | 1.28 | −2.37 |
| OR7E126P | −0.56 | 0.44 | 0.82 | −0.07 | 0.24 | AL354794.1 | −0.73 | −0.67 | −1.46 | 0.71 | 0.70 | AL592164.2 | 0.17 | −1.71 | 0.85 | −0.64 | 1.14 |
| PCSK6-AS1 | 1.32 | −0.57 | −1.19 | 0.53 | −0.79 | AC006557.5 | −0.57 | 1.21 | 0.02 | 1.20 | −0.55 | PRSS30P | −0.05 | 0.05 | −0.49 | 0.49 | 0.99 |
| RN7SL683P | 0.94 | −0.50 | −0.34 | −0.37 | −0.34 | AL583859.1 | 1.16 | 0.18 | −1.69 | 1.20 | −0.18 | SSTR4 | −0.12 | −1.30 | −1.61 | 0.59 | 0.94 |
| SCAMP1-AS1 | −0.32 | −0.08 | −0.09 | 0.26 | −0.01 | AP000640.2 | −0.38 | −0.06 | −0.47 | 0.54 | −0.21 | AC093462.1 | −0.08 | −0.21 | 0.47 | 1.53 | 0.88 |
| AL451085.1 | 1.42 | 0.22 | −2.00 | −0.27 | −2.29 | AC110769.2 | 0.15 | −0.31 | 0.30 | −0.30 | 0.19 | AL034550.2 | −0.05 | −0.27 | 0.22 | −0.25 | 0.59 |
| G28056 | −1.72 | 0.39 | 2.24 | 0.56 | 0.31 | ST13 | 0.11 | −0.05 | 0.02 | −0.15 | −0.14 | AL121956.4 | −0.20 | 0.28 | −0.14 | 1.58 | −1.20 |
| MDM2 | 0.16 | −0.07 | −0.01 | −0.07 | −0.06 | AL121672.2 | 0.21 | 0.13 | 0.01 | 0.07 | 0.00 | MIR4312 | −0.03 | −0.56 | 0.59 | −0.20 | 0.22 |
| AC008669.1 | −0.48 | 0.11 | 0.75 | −0.08 | 0.21 | LINC02498 | −0.60 | −0.67 | −0.77 | −0.33 | 0.41 | AL157373.1 | 0.31 | −0.81 | 0.81 | 0.97 | 2.17 |
| SLC6A21P | −1.12 | 0.91 | 0.54 | 0.13 | 0.41 | AL731559.1 | 0.18 | 0.14 | 0.06 | 0.16 | −0.21 | AL133297.2 | −0.04 | −0.77 | 1.50 | −0.67 | 1.59 |
| DIDO1 | −0.21 | 0.13 | 0.02 | 0.09 | 0.08 | RNU6-1128P | 0.40 | −0.70 | −1.27 | −0.13 | −0.45 | MTCO3P10 | 0.15 | −1.45 | −1.60 | 1.55 | 0.19 |
| RNA5SP429 | −1.04 | 0.62 | −1.39 | 1.45 | −1.12 | AC092652.2 | −0.37 | −0.51 | 0.84 | −0.19 | 0.89 | BTF3P8 | −0.10 | −1.54 | −0.17 | 0.79 | −0.19 |
| LINC01876 | −0.74 | 0.64 | 0.47 | 0.98 | 0.52 | RN7SL485P | −0.52 | −0.25 | 1.16 | 0.53 | 0.85 | GRAMD1A | 0.01 | −0.47 | 0.03 | −0.47 | 0.22 |
| GAREM1 | 0.34 | 0.29 | −0.28 | 0.32 | −0.28 | AC131902.2 | −0.64 | −0.53 | −0.37 | −0.70 | −1.64 | FDPSP5 | 0.13 | 0.37 | −1.75 | 1.65 | −3.25 |
| AC021106.3 | 0.74 | −0.40 | 0.04 | −0.04 | −0.04 | AC010761.3 | −0.15 | −0.38 | −0.21 | 0.16 | 0.27 | AC114400.1 | −0.21 | −1.20 | 0.16 | 1.16 | −0.28 |
| SPARCL1 | −0.57 | 0.60 | 1.05 | 0.17 | 0.00 | KRT87P | −0.41 | 0.72 | −0.89 | 0.18 | −1.04 | AC022272.1 | −0.02 | 0.11 | 0.46 | −0.19 | 0.17 |
| MTCYBP21 | −0.81 | −0.57 | −0.78 | −0.02 | −0.07 | AC090260.1 | −0.31 | 0.17 | 0.36 | 0.64 | 0.02 | AC024560.2 | 0.02 | 0.13 | 0.45 | 0.19 | 0.36 |
| SEC63P1 | 0.56 | −0.38 | 0.01 | −0.33 | 0.07 | AL591516.5 | −0.49 | −0.55 | 0.47 | −0.05 | 0.22 | AC005008.1 | −0.31 | −1.28 | 0.01 | −1.57 | 0.35 |
| AC138625.1 | −1.40 | −0.28 | −0.14 | 0.57 | 0.63 | SLFN12L | 0.21 | −0.62 | −0.09 | −0.44 | 0.36 | AC012462.1 | −0.31 | −0.44 | 0.36 | −0.26 | 0.74 |
| HOXB3 | −0.53 | 0.35 | 0.86 | 0.31 | −0.06 | DNAH2 | −0.21 | −0.29 | −0.07 | 0.12 | −0.09 | MIR648 | −0.03 | −0.16 | −0.47 | −0.09 | 0.49 |
| AL078604.2 | 1.00 | −0.55 | −1.81 | 0.07 | −0.39 | ST20 | 0.24 | −0.30 | 0.03 | −0.09 | 0.03 | IGKV2-30 | 0.31 | 1.47 | 0.49 | 1.57 | −0.83 |
| AL355075.4 | −0.55 | 0.37 | −0.21 | 0.40 | −0.54 | AL137847.2 | −0.21 | 0.02 | 0.18 | 0.01 | 0.54 | DSG2-AS1 | 0.04 | −0.36 | −0.37 | −0.21 | 0.62 |
| AC040934.1 | −0.58 | 0.82 | 0.63 | −0.35 | 0.09 | OR51D1 | 0.81 | 0.37 | −2.74 | 1.68 | −2.15 | AC090617.5 | 0.02 | −0.05 | −0.49 | 0.07 | −0.58 |
| OR5BT1P | −1.15 | −0.13 | 1.47 | 0.85 | 1.21 | AC135048.3 | −0.65 | 1.15 | 0.87 | 0.87 | −0.24 | RN7SKP250 | −0.24 | 0.01 | −0.88 | −0.49 | −0.77 |
| FAM238C | 0.59 | −0.36 | −0.83 | 0.24 | 0.14 | AL050335.1 | −0.70 | 1.05 | 0.95 | −0.44 | 0.24 | RPL12P45 | 0.31 | −1.29 | −0.99 | −1.05 | −0.42 |
| RN7SL716P | −1.00 | −0.21 | 0.78 | −0.24 | 0.51 | PPP1R1AP1 | 0.40 | 0.02 | −0.81 | 0.40 | −0.56 | AC097523.2 | 0.06 | −0.42 | 0.79 | −0.49 | 0.58 |
| PIGQ | −0.34 | 0.13 | −0.06 | 0.33 | 0.19 | ANKIB1 | −0.04 | 0.09 | 0.11 | 0.04 | −0.01 | DUXAP6 | −0.31 | −1.33 | −1.15 | −0.48 | NA |
| FGD4 | −0.26 | 0.30 | 0.36 | 0.11 | 0.01 | AC138393.2 | −0.54 | 0.91 | 2.16 | 0.13 | −0.25 | AC108039.2 | −0.31 | 0.40 | −1.24 | 0.08 | −1.58 |
| PAPPA2 | −0.83 | 0.17 | 0.99 | 0.13 | 0.62 | ARMC3 | −0.43 | −0.52 | −0.43 | 0.80 | −0.19 | AP003351.1 | −0.07 | 1.59 | 3.14 | −0.19 | −0.38 |
| HNRNPA1P4 | 0.50 | −0.44 | −0.53 | −0.01 | 0.11 | CYP2C58P | −0.71 | −1.37 | 1.82 | −0.79 | 0.60 | OR2L9P | −0.10 | 0.07 | 2.70 | −0.19 | 0.89 |
| LYPD1 | 0.99 | −0.54 | −0.68 | 0.39 | 0.54 | AC006512.1 | 0.35 | 0.81 | −0.41 | 0.36 | −0.97 | KRTAP20-2 | −0.31 | 0.30 | 1.11 | −0.11 | 0.94 |
| MTND2P32 | −1.84 | 1.37 | 0.83 | 0.41 | 0.31 | LINC01312 | 1.11 | −0.65 | −1.89 | 0.73 | −2.22 | G5482 | −0.04 | 0.41 | −0.90 | 0.42 | −0.58 |
| AC073333.1 | 0.58 | −0.29 | −0.24 | −0.15 | 0.00 | GOLGA6L6 | −0.47 | −0.90 | −1.11 | 1.12 | 2.25 | IGHVII-30-1 | 0.31 | −0.99 | −1.48 | 0.10 | −1.41 |
| AC009812.3 | −0.66 | −0.37 | 0.23 | −0.01 | 0.52 | RNU6-39P | −0.39 | 0.53 | 1.23 | −0.08 | −0.59 | AL031428.1 | 0.03 | −0.06 | 0.11 | 0.11 | 0.05 |
| CAST | 0.23 | 0.09 | −0.31 | 0.03 | −0.38 | RN7SKP137 | −0.94 | −0.44 | 0.80 | 2.71 | 2.04 | LINC02300 | 0.19 | −0.43 | −0.86 | −0.24 | −3.01 |
| C22orf39 | −0.35 | 0.31 | 0.44 | 0.06 | 0.12 | AC134407.1 | −0.17 | 0.31 | 0.23 | 0.03 | −0.21 | FEZ1 | −0.01 | −0.17 | 0.13 | −0.03 | 0.16 |
| G43235 | −0.89 | 1.04 | 1.07 | 0.21 | 0.17 | G26243 | −0.52 | −0.07 | −0.08 | 2.55 | 2.58 | MIR3202-1 | −0.08 | −0.49 | −0.55 | 1.18 | 0.98 |
| AC007431.3 | −0.62 | 0.24 | −0.12 | 0.23 | 0.06 | HNF4A | −0.40 | −0.46 | 0.23 | 0.51 | 0.54 | RPL21P11 | 0.06 | 0.68 | 2.05 | −0.95 | −0.02 |
| AL590004.3 | −0.87 | 0.27 | −0.73 | 0.44 | −0.41 | AL356489.2 | −0.32 | 0.71 | 0.48 | 0.56 | 0.25 | AL391839.1 | −0.03 | 0.28 | 0.05 | 0.33 | 0.37 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| SCARNA3 | −0.73 | 0.58 | −0.22 | 0.47 | −0.23 | RNU6-549P | 0.48 | −0.02 | −0.24 | 0.09 | −1.00 | AC005921.1 | 0.31 | −1.26 | −0.66 | −0.41 | NA |
| AC008013.1 | −0.53 | 0.54 | 0.18 | 0.28 | 0.19 | AC015727.1 | −0.22 | 0.17 | 0.52 | −0.05 | 0.45 | AL352977.1 | 0.13 | −0.97 | −1.06 | −0.22 | −0.70 |
| PITPNM3 | −0.37 | 0.27 | 0.01 | 0.31 | 0.06 | HSD3BP3 | −0.56 | −0.02 | 0.37 | 0.91 | 0.40 | AL356361.1 | −0.29 | 0.37 | −1.31 | 1.12 | −0.60 |
| AC107959.1 | −1.12 | 0.26 | 1.18 | 0.94 | 0.08 | BX323043.1 | −0.37 | 0.12 | −0.97 | 0.32 | −1.96 | LINC02219 | 0.16 | −1.34 | −2.18 | 1.46 | −1.02 |
| DKFZP451B082 | −1.37 | 0.17 | −0.28 | −0.31 | −1.30 | AP000873.3 | 0.71 | −0.41 | −0.42 | 1.15 | −0.63 | OR5J1P | −0.13 | −1.23 | 0.48 | 0.38 | −1.47 |
| RASA2 | 0.21 | −0.04 | −0.06 | −0.14 | −0.11 | CCDC144NL | −0.48 | −0.55 | −0.92 | 0.57 | 0.53 | AL158151.4 | −0.05 | −1.38 | 1.07 | 0.11 | 0.31 |
| KCNJ3 | −1.15 | 0.05 | 0.00 | −0.12 | 0.18 | AC003973.2 | −1.01 | 0.35 | 1.30 | 1.04 | 2.33 | MIR3667 | −0.31 | 0.15 | −1.59 | 1.61 | −0.51 |
| LRP1 | −0.52 | 0.33 | 0.62 | −0.16 | −0.17 | AL133387.2 | −0.87 | 0.78 | 0.53 | 0.10 | −1.15 | AC105105.4 | −0.09 | 0.24 | 0.95 | −1.03 | −1.13 |
| AC018653.3 | 0.58 | −0.51 | −0.72 | 0.10 | 0.06 | LYPD6B | −0.22 | 0.70 | 0.65 | 0.43 | 0.04 | MED14OS | −0.09 | 1.40 | −0.32 | −0.70 | −1.89 |
| OR2A15P | −1.84 | 0.87 | 0.11 | −0.54 | −0.36 | SETP11 | −0.44 | −0.23 | 0.21 | −0.58 | −0.20 | HMGB1P40 | −0.07 | −0.79 | 0.33 | −0.54 | 0.06 |
| GAREM2 | −0.55 | −0.13 | −0.12 | −0.13 | 0.42 | CASTOR1 | 0.33 | 0.18 | −0.33 | 0.39 | 0.17 | AC099063.2 | −0.20 | 1.04 | −1.39 | 1.71 | −2.73 |
| AC068473.2 | 1.03 | 0.00 | 0.04 | −0.08 | 0.52 | AC119428.2 | 0.42 | −1.17 | 0.99 | 0.08 | 2.30 | AC022730.3 | 0.31 | −1.29 | −0.49 | 1.71 | 0.42 |
| AC005262.1 | 0.88 | −0.94 | −1.34 | −0.03 | 0.11 | RPL23AP18 | 0.25 | 0.14 | 0.54 | −0.07 | 0.31 | CCDC144CP | 0.02 | −0.32 | 0.00 | −0.30 | −0.20 |
| R3HDM2P2 | −1.77 | −0.34 | 1.58 | −0.27 | 1.48 | AC099811.1 | 0.16 | −0.19 | 0.03 | −0.01 | −0.12 | OR8G3P | −0.10 | −0.94 | −1.23 | 0.94 | −0.66 |
| AC130448.1 | −1.18 | 0.78 | 0.15 | 0.14 | −0.73 | CDH7 | −0.38 | −0.23 | 0.08 | 0.33 | 0.17 | AC092098.1 | −0.20 | 0.27 | −0.50 | −0.47 | −1.58 |
| AL136379.1 | −0.63 | 0.19 | 0.55 | −0.12 | 0.38 | MTND4P23 | 0.18 | −0.19 | 0.62 | −0.09 | 0.69 | RNU6-600P | −0.31 | −0.14 | −0.11 | 0.48 | 1.26 |
| AC006330.1 | −0.41 | −0.01 | 0.47 | −0.33 | 0.11 | FGF16 | −0.67 | −1.30 | 2.46 | 0.13 | 0.79 | OS9 | 0.01 | 0.07 | 0.03 | −0.05 | −0.12 |
| RASSF6 | −0.43 | 0.40 | 0.18 | 0.22 | −0.13 | OR2T4 | −1.32 | −0.28 | 0.38 | 0.59 | −1.33 | FECHP1 | −0.29 | 0.80 | −0.51 | −1.24 | −2.25 |
| G12733 | −1.52 | 1.08 | 1.62 | 0.26 | 1.68 | AL669831.2 | 0.62 | −1.95 | −0.55 | −0.32 | 0.30 | MED6P1 | −0.30 | 0.91 | −0.25 | 0.36 | −0.99 |
| AC073842.2 | −0.88 | 0.19 | −0.03 | 0.02 | 0.57 | AC024361.1 | −0.39 | 0.12 | 1.84 | 0.13 | 1.24 | MTCYBP37 | 0.06 | −0.46 | 0.44 | −0.62 | −0.77 |
| PRIM2 | 0.34 | −0.50 | −0.32 | −0.19 | 0.22 | NR1H5P | −0.79 | 0.08 | −2.30 | −0.15 | −2.05 | MGARP | −0.10 | −1.44 | 0.40 | 0.12 | 1.56 |
| AC004884.2 | 0.71 | −0.44 | −0.16 | −0.34 | 0.06 | HCP5 | −0.17 | −0.04 | 0.23 | 0.02 | 0.14 | RIOK3P1 | −0.16 | −0.51 | −1.27 | −1.10 | −3.45 |
| APOL2 | 0.37 | −0.62 | −0.42 | −0.36 | 0.21 | GABRA4 | −0.30 | −0.94 | −0.91 | 0.09 | 0.19 | MMP8 | 0.07 | −0.76 | −0.79 | −0.26 | −1.13 |
| FOXF1 | 1.03 | −0.62 | −0.28 | −0.51 | −0.15 | OR5D3P | 0.81 | −1.04 | −3.10 | 0.52 | −1.73 | RNA5SP38 | −0.12 | 0.47 | −0.80 | 0.27 | −1.23 |
| CCL16 | −0.97 | 0.21 | 1.55 | 0.47 | 1.09 | AP002851.1 | 0.21 | −0.15 | −0.40 | −0.28 | −0.44 | CD63 | −0.02 | 0.00 | 0.47 | −0.44 | −0.04 |
| RIMKLBP2 | −0.49 | 0.24 | 0.64 | 0.22 | 0.37 | SHH | −0.37 | 0.23 | −0.37 | 0.05 | 0.66 | AL121578.3 | 0.23 | 0.18 | 0.78 | 1.37 | −0.72 |
| CHMP7 | 0.16 | −0.08 | 0.02 | −0.15 | 0.08 | G12586 | 0.93 | −0.01 | 0.08 | 0.33 | 0.67 | AC021594.1 | 0.19 | −0.56 | −0.71 | −1.57 | −0.36 |
| CYP2G1P | −1.01 | 0.47 | 1.07 | 0.20 | 0.39 | AC008870.4 | −0.36 | −1.37 | 1.35 | −0.97 | 2.04 | A1CF | 0.04 | −0.25 | −0.48 | 0.23 | −0.39 |
| EYA4 | −0.90 | 0.65 | 0.61 | 0.31 | −0.46 | AC005304.1 | 0.41 | −0.28 | −0.81 | −0.01 | −0.61 | LUZP4P1 | −0.09 | −1.17 | −0.06 | 0.33 | 0.72 |
| PKN1 | −0.49 | 0.00 | 0.56 | −0.10 | 0.22 | AL606495.1 | 0.64 | −1.57 | −0.01 | 0.25 | 1.16 | SNORD5 | −0.30 | 0.42 | 0.31 | −0.48 | −0.24 |
| GRK6P1 | −0.63 | 0.01 | 0.33 | 0.37 | 0.09 | NDUFB8P2 | −0.23 | 0.02 | −0.21 | −0.20 | −0.27 | DEFB129 | 0.12 | 0.90 | −1.31 | 1.09 | −1.28 |
| PHACTR2P1 | −0.40 | 0.28 | 0.11 | 0.18 | −0.06 | ELOCP19 | 0.27 | −0.18 | 0.30 | 0.24 | 0.02 | MIR3183 | 0.05 | −1.00 | −0.73 | −0.33 | 0.08 |
| CCDC144NL-AS | −0.79 | 0.27 | 0.53 | 0.30 | −0.40 | AL139039.2 | −0.49 | 0.15 | 0.00 | −0.49 | 0.78 | MESTP2 | 0.30 | −0.75 | −1.13 | −0.01 | −0.37 |
| AC084200.1 | −1.89 | 1.30 | 3.82 | 0.28 | 0.78 | AC108467.2 | 1.02 | −0.13 | −2.39 | 0.77 | −1.81 | RPL5P9 | 0.04 | 0.14 | −0.62 | −0.19 | −0.48 |
| AC063944.1 | −0.84 | 0.03 | 0.21 | −0.10 | 0.05 | AC068790.3 | 0.13 | −0.31 | 0.26 | −0.22 | 0.45 | EFNA5 | −0.01 | 0.48 | 0.22 | 0.18 | −0.37 |
| MANEA | 0.46 | −0.05 | −0.01 | −0.16 | −0.12 | PRNT | −0.66 | −1.11 | 0.01 | −0.10 | 0.78 | ILF3 | −0.01 | −0.18 | −0.30 | 0.09 | 0.17 |
| CYP2U1 | −0.48 | 0.21 | 0.75 | 0.06 | 0.05 | AP000808.2 | 0.40 | 0.45 | 0.54 | 0.01 | −0.20 | AC091849.2 | −0.09 | −0.98 | −0.69 | 0.47 | 0.36 |
| FKBP1AP2 | −1.07 | 0.58 | 0.92 | 0.54 | 0.69 | CD180 | 0.29 | −0.17 | −0.99 | −0.04 | −0.52 | AC135895.1 | 0.11 | −0.61 | −1.60 | 1.26 | −0.01 |
| AL161931.1 | −1.67 | 2.14 | 0.77 | 0.99 | 0.39 | RPL17P36 | 0.32 | 0.32 | −0.04 | −0.20 | −0.21 | SLC17A2 | 0.06 | −0.13 | −0.74 | −0.17 | −0.78 |
| MFAP1 | 0.31 | −0.30 | −0.24 | −0.32 | −0.11 | AL451074.6 | −0.66 | 0.27 | 0.25 | −1.91 | −1.43 | PRELID3BP6 | 0.11 | −0.51 | −0.77 | 0.22 | 0.10 |
| PPP2R3C | 0.34 | −0.16 | −0.42 | −0.23 | −0.54 | AC099560.2 | 0.29 | −0.08 | 0.34 | −0.14 | −0.12 | AL451062.1 | −0.03 | −0.86 | 0.53 | −0.14 | 0.72 |
| RASAL2 | −0.16 | 0.07 | 0.27 | −0.09 | −0.06 | AC026704.1 | 0.32 | 0.53 | −0.24 | 0.16 | −0.15 | ICAM2 | 0.03 | −0.11 | 0.81 | 0.13 | 0.18 |
| SEC16B | −0.86 | −0.06 | 0.48 | 0.09 | 0.22 | AL133520.1 | 0.27 | 0.16 | 0.39 | −0.31 | −0.20 | AP002856.1 | −0.18 | −0.72 | −0.69 | −0.33 | 0.23 |
| KLF6 | 0.26 | −0.15 | −0.46 | −0.33 | −0.25 | AC004232.3 | −0.37 | 0.50 | 0.91 | 0.26 | 0.55 | AP002967.1 | 0.02 | −0.07 | 0.17 | 0.13 | 0.22 |
| LINC02158 | 1.11 | −0.59 | −0.63 | 0.21 | 0.20 | AC133963.2 | −0.95 | −0.64 | 1.14 | −1.19 | 1.38 | AJ009632.1 | −0.19 | −0.40 | −0.42 | 0.30 | 0.51 |
| SNORD15A | 1.98 | −0.29 | −1.62 | 0.89 | −0.51 | G10706 | 0.62 | −1.05 | −1.64 | −0.51 | −0.74 | AC108451.2 | 0.06 | 0.30 | −1.05 | −0.56 | −1.83 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC073150.1 | −1.23 | 0.00 | 0.57 | −0.73 | 0.34 | RYK | 0.08 | 0.06 | 0.10 | −0.02 | 0.03 | RPSAP59 | −0.30 | −0.19 | −0.55 | −0.10 | −1.35 |
| COL7A1 | −0.54 | −0.22 | −0.76 | 0.45 | 0.06 | AL161449.1 | 0.59 | 0.31 | −0.42 | 0.19 | 0.25 | MTND1P27 | −0.26 | 0.24 | −0.45 | 0.76 | −0.78 |
| AP002490.1 | −0.48 | 0.34 | 0.21 | 0.19 | −0.01 | AC005779.2 | −1.33 | 0.80 | 1.60 | 0.80 | 2.12 | AC092506.1 | −0.06 | 0.49 | −1.39 | −0.32 | −1.22 |
| GPC6-AS1 | −1.18 | 0.30 | 1.50 | −1.22 | −0.08 | AL449403.1 | −0.66 | 0.17 | 2.49 | −1.11 | 0.21 | GAPDHP26 | −0.12 | −0.01 | −0.09 | 1.55 | −0.36 |
| RP11-12A20.7 | −1.23 | 0.23 | −0.18 | 0.59 | −0.23 | LINC01945 | −1.00 | 1.27 | −0.93 | 1.85 | −0.75 | AL122018.1 | −0.09 | 0.30 | −2.24 | 1.71 | −1.27 |
| CACNA1C-IT3 | 0.87 | −0.36 | 0.28 | −1.25 | −0.18 | GIMAP4 | −0.17 | 0.11 | 0.97 | −0.29 | 0.14 | AC022017.1 | 0.30 | −0.32 | 0.60 | 0.49 | 1.52 |
| C6orf120 | 0.28 | −0.07 | −0.14 | 0.03 | −0.09 | B9D2 | 0.20 | −0.11 | −0.81 | 0.14 | −0.38 | MAPK6P5 | 0.05 | −0.10 | −2.08 | 1.22 | −0.99 |
| PRDM16 | −0.82 | 0.32 | 0.32 | 0.83 | 0.39 | AC015813.1 | 0.14 | −0.07 | −0.09 | 0.10 | 0.01 | PPIAP45 | 0.18 | −1.21 | −1.48 | −1.48 | −0.87 |
| AC068473.5 | −0.39 | 0.11 | 0.63 | 0.09 | 0.47 | LINC02139 | −0.54 | 0.55 | 0.41 | 0.83 | −0.26 | GHRLOS | −0.02 | 0.02 | −0.17 | 0.14 | 0.27 |
| IL33 | 0.48 | −0.15 | 0.35 | 0.17 | 0.20 | AC138393.1 | 0.13 | 0.02 | 0.28 | −0.10 | 0.13 | RN7SKP158 | 0.02 | −0.12 | −0.27 | −0.17 | 0.14 |
| AMPD1 | −1.13 | 0.15 | −0.75 | 0.12 | 0.02 | BTN3A3 | −0.13 | −0.24 | 0.59 | −0.31 | 0.38 | NDUFA9 | −0.01 | −0.05 | −0.02 | 0.17 | −0.03 |
| AL133492.1 | 0.89 | −1.22 | −0.82 | 0.01 | 0.49 | AC068790.4 | 0.19 | −0.28 | 0.01 | −0.41 | 0.42 | AC015849.3 | −0.02 | −0.35 | 0.02 | 0.08 | 0.31 |
| NR2F1 | −0.75 | 0.11 | 1.69 | −0.05 | 0.24 | RPL7P47 | 0.53 | 0.48 | −0.82 | −0.34 | −0.33 | AC119751.4 | −0.09 | −0.58 | 0.73 | −0.36 | 0.70 |
| EPS8L1 | −0.53 | 0.33 | 0.71 | 0.00 | 0.35 | AL117335.1 | −0.17 | −0.26 | −0.14 | 0.05 | 0.27 | AC048382.4 | −0.30 | 0.42 | 0.66 | −0.73 | −0.20 |
| AP003072.4 | 0.99 | −0.11 | −0.21 | 0.52 | −0.35 | LMLN2 | 0.33 | −0.35 | −0.52 | 0.05 | −0.24 | AC046144.1 | −0.29 | 0.34 | 1.00 | −1.98 | −1.69 |
| NEURL1 | −0.47 | 0.27 | −0.18 | 0.30 | −0.12 | ATP6V1G2 | −0.32 | 0.12 | −0.57 | 0.81 | 0.11 | ALG13-AS1 | −0.02 | 0.12 | −0.07 | 0.21 | 0.16 |
| PCDHB2 | −0.76 | 0.58 | 1.00 | −0.09 | 0.07 | MIR134 | 1.09 | −0.43 | 1.37 | −0.32 | 1.11 | AC090515.4 | −0.13 | −1.31 | 1.19 | 0.55 | −0.36 |
| AC145422.1 | −0.94 | 0.85 | 0.84 | 0.54 | 0.47 | SRD5A2 | −0.54 | −0.76 | −1.36 | −0.13 | −1.30 | AC017037.2 | −0.11 | −0.86 | −1.03 | 0.69 | −0.65 |
| G6008 | −0.45 | 0.18 | 0.47 | 0.03 | 0.43 | SNORD116-11 | −1.29 | 1.06 | 2.57 | 0.21 | 0.21 | AC093765.1 | −0.30 | 0.05 | −0.72 | 0.01 | −0.71 |
| AC244517.3 | −0.81 | 0.39 | 0.96 | 0.35 | 0.59 | AC004943.1 | −0.20 | 0.16 | −0.27 | 0.20 | −0.03 | G11315 | −0.11 | −0.22 | 0.03 | 1.59 | 2.58 |
| LRRCC1 | −0.28 | 0.07 | 0.34 | −0.01 | 0.16 | AC024896.1 | −0.13 | 0.01 | 0.05 | 0.20 | 0.13 | AC092326.2 | −0.16 | −0.28 | −1.17 | 1.12 | −0.34 |
| BCRP8 | −1.39 | 1.74 | 0.94 | 0.33 | −0.08 | HOXB-AS3 | 0.29 | −0.76 | −0.38 | 0.26 | 0.59 | AC007566.2 | 0.17 | 0.46 | 0.57 | −0.25 | −1.28 |
| MSTO2P | −0.43 | 0.06 | 0.55 | 0.12 | 0.47 | PPP2R5D | 0.06 | 0.04 | −0.06 | −0.08 | −0.04 | AL022393.1 | −0.06 | −0.70 | 1.10 | −0.84 | 0.57 |
| SNORD116-25 | −1.30 | 1.44 | 2.00 | 0.95 | 0.07 | AC004812.2 | 0.15 | 0.06 | 0.28 | 0.22 | −0.06 | AC091941.1 | −0.30 | −0.13 | 0.01 | 1.32 | 0.14 |
| AC015712.7 | 1.51 | −1.80 | −2.44 | −1.33 | −1.47 | MIR4650-1 | 0.70 | −1.17 | 1.88 | −0.35 | 2.16 | PRAMENP | −0.08 | −1.01 | −0.36 | −0.76 | −0.98 |
| PLCE1-AS2 | −0.95 | 0.30 | 1.25 | 0.52 | 0.16 | AC011601.1 | 0.31 | −0.08 | 0.86 | 0.36 | 0.78 | AC005722.1 | 0.30 | −1.10 | −1.22 | 0.56 | 0.47 |
| RNU4ATAC16P | 0.92 | −0.37 | 0.09 | −0.36 | 0.40 | MIR4511 | 1.14 | 0.27 | −0.29 | 1.22 | 1.42 | CYCSP4 | 0.04 | −0.24 | −0.44 | 0.41 | −0.17 |
| AC005332.6 | −0.32 | 0.44 | 0.50 | 0.24 | 0.08 | DYNC1LI2 | −0.04 | 0.09 | 0.02 | 0.01 | −0.03 | PRPS1P1 | 0.21 | 0.59 | 0.00 | 0.98 | −1.09 |
| BBC3 | −0.54 | 0.76 | 0.77 | 0.46 | 0.18 | AC138832.1 | 0.25 | −0.11 | −0.31 | −0.13 | −0.15 | AC007216.2 | −0.02 | −0.72 | 0.13 | 0.21 | 1.14 |
| AL731556.1 | −0.68 | 0.10 | −0.33 | 0.22 | −0.05 | ADCY9 | −0.06 | 0.00 | −0.09 | 0.02 | 0.04 | LINC01362 | −0.03 | 0.08 | −1.34 | 0.14 | −1.36 |
| CELF2-AS1 | −0.46 | 0.09 | 0.68 | 0.03 | 0.25 | SSX3 | −0.71 | 0.99 | −1.63 | 0.30 | −0.81 | DHDH | −0.04 | −1.31 | 0.10 | −1.04 | 0.41 |
| AL033519.3 | −1.82 | 0.63 | 1.72 | −0.68 | 0.53 | AL356741.1 | 0.50 | −0.03 | −0.94 | 0.28 | −0.64 | AC080013.3 | −0.05 | −0.74 | 0.70 | 0.12 | 1.29 |
| AC026333.3 | 1.07 | −2.37 | −1.82 | −1.06 | −0.39 | AC009563.1 | 0.39 | −0.93 | −0.98 | 0.04 | −0.02 | FGB | 0.07 | −0.92 | −0.32 | −0.83 | 1.60 |
| AC069228.1 | −0.95 | −0.45 | −0.44 | −0.45 | −0.17 | NOX5 | −0.19 | −0.03 | −0.18 | 0.11 | −0.02 | AC010738.1 | −0.13 | −1.00 | −1.40 | −0.69 | −1.06 |
| PTCHD1 | −0.63 | −0.19 | −0.15 | −0.27 | −0.30 | CHL1-AS1 | −0.35 | 0.34 | 1.13 | −0.27 | 0.55 | LINC02420 | −0.16 | −0.36 | −1.77 | 0.75 | 0.05 |
| FCGR2A | 0.79 | −0.88 | −0.44 | −0.05 | −0.26 | AC010478.1 | −0.36 | −0.04 | −0.32 | 0.18 | −0.29 | AC010182.1 | 0.06 | −0.65 | 1.66 | 0.11 | 0.62 |
| EIF3CL | 0.40 | −0.19 | −0.49 | 0.06 | −0.21 | AC138915.2 | −0.63 | −0.65 | −0.57 | 0.81 | 1.15 | AC011611.1 | −0.30 | 0.00 | 0.06 | 0.25 | −0.10 |
| LINC01242 | −1.16 | 0.98 | −0.97 | 1.15 | −0.50 | LINC02021 | 0.34 | −0.14 | 0.87 | 0.15 | 0.75 | AC090023.1 | 0.30 | −0.12 | 0.38 | 0.16 | 0.20 |
| KRT18P33 | −2.11 | −0.80 | 2.53 | −0.81 | 0.86 | C9orf163 | 0.32 | −0.63 | −0.71 | −0.29 | −0.51 | AC104010.1 | −0.30 | 0.34 | 0.18 | −0.73 | 0.97 |
| DMRTA1 | −0.66 | −0.26 | −0.04 | −0.18 | 0.97 | AL034428.1 | −0.29 | 0.29 | 1.18 | −0.16 | 0.00 | AL357172.1 | 0.30 | −0.36 | −0.63 | −0.06 | −2.36 |
| MIR54802 | 1.56 | 0.32 | −1.02 | 0.72 | −1.43 | AP000821.1 | −0.57 | −0.62 | 0.47 | 0.42 | 0.10 | AC079363.1 | 0.06 | 0.72 | 1.84 | −0.59 | 0.00 |
| KDSR | 0.23 | −0.04 | −0.22 | −0.06 | −0.27 | AADAC | −0.25 | 0.17 | −0.24 | 1.13 | −0.30 | PRDX2 | 0.01 | 0.20 | −0.15 | 0.43 | −0.21 |
| AC051619.9 | −1.52 | 1.73 | 1.08 | 0.41 | 0.23 | RPS3AP39 | −0.84 | 0.63 | 2.26 | −0.34 | 0.73 | KIF13B | −0.01 | 0.29 | 0.20 | −0.03 | −0.21 |
| AC106872.5 | −0.93 | −0.18 | 1.38 | −0.66 | 0.63 | AC139783.2 | −0.52 | −0.55 | 0.65 | −0.71 | −0.53 | LINC02092 | 0.09 | 0.04 | −1.16 | 0.90 | −0.56 |
| AC104365.2 | 1.10 | −0.49 | −0.30 | −0.64 | −0.73 | KCNC1 | −0.12 | −0.04 | −0.22 | 0.00 | −0.21 | FBXO43 | 0.02 | −0.83 | −0.44 | −0.29 | 0.25 |
| KIF21B | 0.49 | −0.83 | −0.65 | −0.20 | 0.18 | GP6 | −0.18 | 0.31 | 0.72 | −0.29 | 0.04 | RN7SL292P | 0.30 | 0.14 | −0.29 | 1.82 | −1.13 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| CA14 | −0.50 | 0.49 | −0.05 | 0.53 | 0.04 | RNU1-56P | −0.36 | −0.91 | −0.74 | 0.29 | 1.00 | AL359692.1 | 0.14 | −1.03 | 1.04 | −2.40 | 0.60 |
| PSD | −0.53 | 0.00 | −0.20 | −0.02 | 0.24 | IL1R1-AS1 | 0.96 | −0.05 | 0.17 | −0.22 | −0.16 | AP000688.3 | −0.15 | 0.07 | 1.50 | 0.39 | 0.81 |
| SCTR | −0.81 | 0.27 | −0.09 | 0.55 | 0.51 | AC140061.8 | −0.70 | −0.63 | 1.03 | −0.49 | −0.09 | AC040168.1 | −0.21 | 0.06 | 0.29 | 1.30 | 0.55 |
| LINC01537 | −0.63 | 0.12 | 1.11 | 0.00 | 0.20 | MEPCE | 0.10 | 0.05 | −0.01 | −0.01 | 0.01 | MTND1P33 | −0.30 | −0.47 | −0.05 | −0.29 | −0.23 |
| GNPDA2 | 0.34 | 0.19 | 0.03 | 0.09 | −0.12 | AC078788.1 | 0.43 | −1.13 | 0.90 | −0.18 | 1.03 | IGHV3-43 | 0.17 | −0.70 | 0.90 | −0.77 | 1.58 |
| AC021683.1 | −1.09 | −0.79 | 1.88 | 0.16 | 1.14 | MAFF | 0.17 | 0.05 | −0.55 | −0.23 | −0.94 | RPS4XP4 | −0.15 | −0.40 | −1.26 | 1.22 | 0.99 |
| CASQ1 | −0.60 | 0.16 | −0.13 | 0.27 | −0.20 | AC099063.4 | −0.58 | −0.18 | 1.09 | −0.13 | 0.89 | CD38 | 0.03 | −0.66 | −0.71 | 0.24 | 0.29 |
| AP000563.1 | −1.13 | −0.07 | 0.45 | 0.61 | 0.75 | GORASP1 | −0.07 | 0.03 | −0.09 | −0.01 | 0.05 | RN7SL54P | 0.10 | −0.72 | 1.37 | 0.90 | 1.25 |
| AC121247.1 | −0.82 | −0.15 | 1.56 | −0.33 | 0.68 | AC110603.1 | 0.27 | −0.51 | 0.88 | 0.05 | 0.33 | LINC00326 | −0.06 | 0.22 | −1.32 | −0.02 | −1.07 |
| GDF9 | −0.53 | 0.21 | −0.38 | 0.46 | 0.09 | AC244023.1 | 0.83 | 0.51 | 0.89 | 0.04 | −0.09 | AC112191.1 | −0.05 | 0.33 | −3.40 | 0.94 | −3.17 |
| FAM161B | −0.36 | 0.30 | 0.53 | −0.20 | −0.13 | AL162385.2 | −0.23 | 0.14 | 0.06 | 0.10 | −0.18 | RNU6-659P | −0.07 | −0.78 | 1.19 | 1.08 | −0.04 |
| HMGN1P38 | 0.75 | −0.63 | 0.18 | −0.23 | 0.33 | RNU6-539P | −0.30 | 0.13 | 0.19 | −0.20 | 0.04 | NDUFA3P1 | 0.04 | 0.20 | 0.45 | −0.29 | −0.15 |
| GPR62 | −1.05 | 1.18 | 0.66 | 0.21 | 0.23 | MIR10B | −0.22 | −0.47 | 1.08 | −0.32 | 0.96 | AL138721.1 | −0.03 | 0.13 | 1.08 | −0.12 | 0.66 |
| SND1-IT1 | 0.41 | −0.43 | −0.04 | −0.28 | 0.38 | AL513314.1 | −0.55 | −0.17 | 0.18 | −0.15 | −1.49 | PROCR | −0.01 | −0.05 | −0.06 | −0.14 | 0.16 |
| G36581 | 1.24 | 0.20 | −0.70 | 0.10 | −0.09 | ENO1-AS1 | 0.62 | −1.19 | −1.33 | 0.75 | 0.39 | AL512504.2 | 0.09 | −0.99 | −1.37 | −0.03 | −0.94 |
| AL390318.1 | 0.61 | −0.58 | −0.42 | −0.11 | 0.20 | G16424 | −0.50 | 1.08 | 1.76 | 0.08 | −0.25 | EEF1A1P15 | −0.29 | 0.01 | 0.41 | −0.94 | −0.81 |
| RNU5B-3P | −1.42 | 0.89 | 1.69 | 0.35 | 0.07 | AL596275.2 | −0.58 | 0.41 | −0.01 | 0.11 | 0.41 | OR4A15 | 0.29 | −0.89 | −0.35 | −0.12 | −0.11 |
| OR14A16 | −1.25 | −0.44 | 0.42 | 0.15 | 1.40 | OR56B1 | −0.57 | 0.49 | 0.96 | −0.15 | −0.26 | AC093025.1 | −0.29 | −0.47 | 1.10 | −0.15 | 1.23 |
| AC020661.4 | 0.76 | −0.48 | −0.34 | −0.42 | −0.16 | G5143 | 0.43 | −0.18 | −0.66 | 0.55 | 0.16 | G22256 | 0.03 | −0.67 | 1.05 | −0.19 | 0.88 |
| AC015656.1 | −1.03 | 0.46 | 0.92 | 0.32 | 1.31 | PRKD3 | 0.07 | 0.07 | −0.18 | 0.17 | −0.05 | SELENOOLP | −0.10 | 0.44 | −2.09 | −0.08 | −1.02 |
| AC006435.4 | −1.10 | 0.90 | 0.28 | 0.18 | −0.14 | AL031429.2 | −0.45 | 0.25 | 1.71 | −0.60 | 0.30 | OR1AA1P | 0.29 | 0.15 | −1.28 | 1.78 | 0.63 |
| INTS11 | −0.30 | 0.08 | −0.15 | 0.18 | 0.16 | BEX3 | 0.10 | 0.22 | 0.41 | −0.06 | −0.29 | SMG5 | 0.01 | −0.03 | −0.35 | 0.16 | 0.08 |
| AC016542.3 | 0.72 | −0.49 | 0.06 | −0.10 | 0.17 | DGCR6L | −0.11 | 0.10 | 0.24 | −0.07 | −0.11 | AC112230.1 | 0.03 | 0.16 | 0.16 | 0.39 | 0.82 |
| MSH4 | −0.73 | 0.16 | 1.04 | 0.32 | 0.89 | AC092617.1 | 0.41 | 0.08 | −0.49 | 0.63 | 0.19 | AC073257.2 | 0.10 | 0.12 | −1.29 | 0.62 | 0.59 |
| CTBP1 | −0.26 | 0.07 | −0.12 | 0.24 | 0.11 | FIZ1 | −0.11 | 0.11 | 0.25 | 0.15 | 0.13 | DEFA6 | 0.11 | −1.04 | −1.11 | −0.53 | −0.77 |
| ASPG | −0.51 | 0.45 | 0.23 | 0.26 | 0.10 | AC125793.1 | 0.20 | 0.43 | −0.23 | 0.37 | −0.08 | FAM225B | −0.04 | −0.63 | 1.11 | −0.25 | 0.40 |
| AC092999.1 | −0.97 | 0.46 | 0.06 | 0.12 | −0.89 | AC104463.1 | −1.16 | 0.55 | 0.28 | 0.21 | 0.49 | ARF4P2 | −0.11 | −0.32 | 0.22 | −1.10 | −0.80 |
| SNORC | −0.54 | 0.43 | 0.47 | 0.34 | 0.31 | AC004486.1 | 0.93 | 0.45 | −0.63 | 0.29 | 1.12 | AF099810.1 | −0.07 | −1.75 | 0.63 | −0.12 | 0.84 |
| AC009093.10 | −0.60 | −0.52 | −0.29 | −0.12 | −0.19 | LEFTY1 | −0.64 | 0.91 | 0.21 | −0.41 | 0.97 | SNRPD2P2 | −0.25 | −0.70 | 1.95 | −1.23 | −0.07 |
| ADGRE1 | 1.35 | −1.53 | −0.97 | −0.39 | 0.83 | AC004543.1 | −0.53 | −0.20 | −0.21 | −0.72 | 0.53 | AC127894.1 | −0.06 | 0.17 | −2.93 | 0.57 | −2.75 |
| SETP20 | −0.63 | 0.47 | 0.92 | 0.65 | −0.24 | AS3MT | −0.65 | 0.41 | 1.03 | 0.42 | 0.24 | AL356277.3 | 0.03 | −0.06 | 0.39 | −0.34 | −0.25 |
| AL512598.2 | −1.12 | 0.24 | 1.31 | −0.48 | 0.29 | OR2T7 | −0.63 | 0.66 | 0.70 | 0.36 | −0.34 | AL162731.1 | −0.04 | −1.10 | 0.94 | 0.89 | 2.37 |
| RBP2 | −0.81 | 0.73 | 0.56 | 0.52 | 0.55 | EEF1E1P1 | 1.19 | −1.08 | −2.01 | −1.46 | −3.29 | AC068062.1 | −0.29 | −0.21 | 0.52 | −0.90 | −0.19 |
| KCNMA1 | −0.48 | 0.18 | −0.17 | 0.11 | −0.27 | AC068790.1 | 0.59 | 1.18 | 0.03 | 0.45 | 0.91 | AC073465.2 | 0.21 | −0.82 | −0.98 | 0.51 | −0.81 |
| RAB24 | 0.50 | −0.12 | −0.62 | −0.02 | −0.09 | AP001160.4 | 0.38 | −0.41 | −0.34 | 0.27 | −0.18 | RN7SL216P | 0.29 | −0.18 | −0.69 | −0.52 | −0.64 |
| MYLPF | −1.29 | 0.89 | 0.93 | −0.53 | −0.30 | AC211433.1 | 0.17 | 0.04 | 0.12 | 0.10 | 0.10 | FREM3 | −0.02 | −0.33 | 0.40 | −0.22 | 0.06 |
| PRIMA1 | −0.48 | 0.46 | 0.37 | 0.15 | 0.14 | AL031577.2 | 0.47 | 0.54 | −2.13 | 0.16 | −1.93 | AC093331.2 | 0.18 | 0.53 | −1.17 | 0.46 | −1.04 |
| SCGB3A1 | −1.57 | 1.69 | 0.93 | 0.61 | −0.19 | BCL9 | −0.08 | 0.22 | 0.21 | 0.21 | 0.02 | AP001116.1 | 0.09 | −1.96 | 1.16 | −0.27 | 1.04 |
| 3-Sep | −0.46 | −0.10 | 0.17 | 0.14 | 0.49 | AC004839.1 | −0.52 | 0.57 | 0.49 | 0.16 | −0.30 | GAPDHP75 | −0.29 | 0.01 | 0.89 | 0.86 | 0.67 |
| CBX3P4 | −1.00 | 1.20 | −0.41 | 0.82 | −0.36 | MAP1S | −0.13 | −0.10 | 0.12 | −0.29 | 0.10 | PAGE1 | −0.21 | 0.96 | −1.22 | 0.50 | −3.44 |
| AL118505.1 | −0.61 | 0.53 | 0.55 | 0.66 | 0.67 | MIR16-1 | 1.07 | 0.43 | −0.15 | −0.40 | 0.82 | CTBP1-AS | 0.02 | 0.16 | −0.10 | 0.09 | −0.10 |
| SPAST | 0.25 | −0.03 | 0.01 | −0.09 | −0.08 | SFPQ | 0.09 | −0.11 | −0.38 | 0.02 | −0.09 | AL117382.1 | −0.12 | −0.46 | −1.51 | −0.33 | 0.54 |
| KRT74 | −0.94 | −0.37 | 1.33 | 0.29 | 3.30 | SERPINB12 | 0.29 | 0.46 | 1.06 | 0.36 | −0.58 | AC016229.2 | 0.29 | −0.50 | −1.44 | 1.41 | −0.57 |
| AC023389.1 | −0.52 | −0.20 | −0.09 | 0.16 | 0.44 | PCDHAC2 | −0.39 | 0.90 | 0.90 | 0.10 | −0.56 | OR4A47 | 0.10 | −0.23 | −0.16 | 1.90 | 0.55 |
| AC011467.1 | −1.49 | −0.92 | 0.01 | −0.36 | 0.79 | AF131215.5 | −0.10 | 0.01 | 0.21 | −0.03 | 0.28 | OR11Q1P | 0.29 | 1.38 | −0.22 | 0.52 | −2.15 |
| MIR5092 | 1.47 | 0.16 | −1.07 | −0.05 | −1.48 | AC005357.2 | −0.77 | −0.29 | 1.73 | −0.55 | 1.04 | AL139239.1 | 0.10 | 0.24 | −0.29 | 0.56 | 1.69 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| SLC16A10 | −0.60 | 0.38 | 1.39 | 0.05 | 0.09 | AL645937.3 | 0.79 | −1.06 | −1.28 | 0.00 | −0.94 | AL591503.1 | −0.08 | −0.63 | −0.24 | −0.81 | −0.58 |
| PMS1 | 0.22 | −0.20 | −0.03 | −0.21 | 0.18 | SLC35B2 | 0.09 | −0.19 | −0.09 | −0.26 | −0.12 | KRTAP27-1 | 0.29 | −2.01 | −1.59 | 0.62 | NA |
| RNA5SP219 | 0.64 | −0.45 | −0.09 | −0.25 | −0.13 | AL359513.1 | 0.35 | 0.43 | 0.69 | 0.35 | −0.11 | RNA5SP346 | −0.29 | −0.41 | 0.43 | 1.39 | 0.91 |
| AL135901.1 | −0.57 | 0.25 | 0.37 | 0.12 | −0.04 | G34419 | −0.62 | 1.76 | 1.63 | −0.47 | −0.35 | RNF5 | −0.01 | 0.22 | 0.24 | 0.09 | −0.15 |
| AL138724.1 | 1.07 | −1.09 | −1.05 | −0.56 | −0.17 | SLC9A7P1 | −0.31 | −0.15 | −0.22 | 0.30 | −0.14 | SLC20A1P3 | 0.07 | −0.18 | 0.48 | 0.85 | −0.45 |
| AC005144.1 | −1.35 | 0.46 | 0.52 | 0.14 | −0.25 | AP001804.1 | 0.65 | 0.50 | −1.14 | 0.88 | 0.54 | SNORD114-13 | 0.05 | 0.53 | 0.76 | −0.72 | −0.12 |
| KRT18P31 | −0.41 | 0.30 | 0.13 | 0.33 | 0.04 | AP001496.1 | −0.89 | 0.61 | 0.92 | 0.20 | 1.91 | AC019129.2 | −0.13 | −0.99 | −1.52 | 1.20 | −0.09 |
| AC006946.3 | −0.80 | 0.73 | 0.47 | 0.11 | −0.09 | AL021997.2 | 0.52 | 0.32 | 0.60 | 0.69 | 0.49 | LRRC52 | −0.13 | −1.50 | −1.02 | −1.48 | −1.10 |
| AC073913.1 | −1.06 | 0.45 | 1.61 | 1.44 | 0.04 | MIR4729 | −0.52 | 1.47 | 0.78 | 0.26 | −0.58 | BMS1P21 | −0.02 | 0.09 | 0.26 | 0.18 | 0.09 |
| CCDC92B | −1.20 | 0.23 | −0.01 | 0.57 | 0.35 | CPA2 | 0.57 | −1.16 | −2.18 | −0.86 | −1.97 | MTND4P27 | −0.28 | −0.78 | −1.08 | −0.64 | −1.19 |
| MTND4P20 | −1.45 | 0.12 | 1.03 | 1.02 | 2.17 | DAZL | 0.54 | −0.08 | 1.39 | −0.28 | −0.22 | G11405 | 0.03 | 0.18 | 0.00 | 0.48 | −0.02 |
| LINC01625 | −1.10 | 0.23 | 1.11 | 0.01 | 0.50 | AL512646.1 | −0.72 | −1.21 | 0.34 | 1.43 | 2.09 | RNY5P1 | −0.06 | −1.32 | −1.09 | −0.09 | −1.89 |
| PLD3 | −0.25 | 0.22 | 0.28 | −0.03 | −0.10 | C9orf16 | −0.08 | 0.19 | 0.29 | −0.06 | −0.22 | AL109933.1 | 0.28 | −0.73 | −0.23 | 1.18 | 0.11 |
| ST7-AS2 | 0.34 | −0.14 | −0.36 | −0.09 | −0.29 | ANKRD20A6P | −0.41 | 1.08 | −0.45 | 0.57 | −0.08 | RFX4 | −0.04 | −0.83 | −0.69 | 0.33 | 0.44 |
| AL359510.2 | −0.87 | 0.12 | 0.55 | 0.40 | −0.48 | CTU2 | −0.12 | −0.24 | −0.29 | 0.20 | 0.22 | ABALON | 0.03 | −0.10 | −0.42 | 0.23 | −0.09 |
| AC100858.3 | 0.94 | −0.29 | −0.88 | −0.44 | −0.56 | LINC01948 | 0.20 | 0.20 | 0.61 | 0.44 | 0.04 | AL354771.1 | 0.10 | −0.27 | 1.10 | −0.88 | −1.12 |
| RHOH | 0.85 | −1.27 | −0.04 | −0.25 | 0.50 | RPL10P7 | −0.60 | −0.09 | −0.23 | −1.25 | −0.42 | EIF2S2P2 | 0.02 | 0.08 | −0.13 | 0.28 | 0.30 |
| AC103794.1 | −0.71 | −0.17 | −0.76 | 0.79 | −0.49 | CABP5 | −0.68 | −0.53 | −0.46 | 1.08 | 0.92 | EXOC6 | 0.01 | 0.02 | 0.17 | −0.10 | 0.02 |
| POLR2I | 0.60 | −0.19 | 0.12 | −0.48 | −0.11 | RN7SL350P | 0.27 | −0.20 | −0.19 | 0.08 | 0.08 | PRSS3P3 | 0.13 | 0.27 | −1.93 | 0.58 | −0.43 |
| AL035405.1 | 0.77 | −0.20 | −0.26 | −0.03 | 0.10 | RPS29P19 | 0.69 | 0.37 | −0.15 | −0.08 | −0.96 | AP1S2P1 | −0.29 | −0.42 | 0.28 | 0.24 | −0.31 |
| DOCK9-AS1 | 0.64 | 0.10 | −0.15 | 0.02 | −0.06 | OR7E162P | 1.01 | −0.85 | −2.07 | 1.55 | 0.79 | AL132719.1 | −0.29 | −0.12 | −0.96 | 0.06 | −0.71 |
| AC006452.1 | −0.97 | 0.81 | 0.93 | −0.16 | 0.02 | KANSL2 | 0.06 | −0.14 | −0.14 | −0.07 | −0.15 | RPL35AP31 | 0.07 | 0.52 | 2.20 | −0.06 | 0.80 |
| RNH1 | 0.25 | −0.07 | −0.52 | 0.01 | −0.44 | AC134050.1 | 0.28 | 0.25 | −0.43 | −0.62 | −0.74 | AFG3L2P1 | −0.09 | −1.00 | −0.08 | −1.37 | −0.88 |
| GTF2IP14 | −0.44 | 0.18 | 0.24 | 0.07 | 0.38 | AC127522.1 | −0.52 | −1.34 | 1.64 | −0.85 | 2.64 | POLH-AS1 | 0.02 | −0.73 | 0.11 | −0.34 | 0.40 |
| AC092287.1 | −0.76 | −0.41 | −0.33 | −0.20 | 1.03 | AC019080.3 | 0.30 | −0.33 | 1.71 | −0.33 | 0.37 | AC087683.1 | −0.04 | 0.36 | −0.56 | 0.85 | −0.69 |
| G36147 | −1.63 | 0.33 | 2.45 | 1.72 | 1.69 | AMACR | 0.21 | −0.27 | 0.47 | 0.08 | 0.26 | MIR496 | 0.09 | 1.01 | 2.13 | −2.11 | −0.38 |
| SLC7A4 | −0.89 | 0.66 | −0.71 | 0.59 | −0.17 | RASL10B | −0.35 | 0.79 | 0.57 | 0.27 | −0.53 | GAPDHP56 | 0.22 | −1.02 | −0.46 | −0.21 | 1.29 |
| PWRN1 | −1.08 | −0.72 | −1.65 | 0.23 | −0.72 | MIR103A1 | 0.40 | −0.20 | −0.54 | −0.70 | −0.47 | IGLV3-16 | 0.29 | −0.29 | −0.70 | −1.51 | −2.77 |
| AC090515.5 | −0.73 | −0.50 | −0.07 | −0.02 | 0.71 | AP001189.1 | 0.23 | −0.14 | 0.37 | 0.11 | −0.09 | AL133304.2 | 0.15 | −0.80 | 0.27 | 1.30 | 7.08 |
| SERPING1 | −0.65 | 0.50 | 1.01 | −0.09 | 0.02 | CFAP97D1 | −0.36 | −0.05 | −0.46 | −0.38 | −0.23 | AC091043.1 | −0.29 | −0.43 | 0.43 | −1.31 | −0.96 |
| GZMB | 0.87 | −2.12 | −1.04 | −0.72 | −1.00 | AP001122.1 | 0.37 | −1.27 | −0.44 | −0.25 | −0.50 | AP003171.2 | −0.29 | −0.60 | 0.31 | 0.01 | 0.05 |
| PLAC9P1 | −1.24 | 1.14 | 1.01 | 0.98 | −0.23 | BNIP3P27 | −0.28 | 0.22 | 0.01 | 0.66 | 0.39 | AC009541.1 | −0.29 | 0.69 | 0.68 | −0.65 | −0.42 |
| IKZF1 | 0.59 | −0.63 | 0.11 | −0.44 | 0.26 | RN7SL492P | −0.82 | 1.11 | −0.13 | 0.86 | −0.50 | SAR1AP3 | 0.11 | −1.40 | 1.72 | −0.87 | 1.77 |
| HNRNPD | 0.21 | −0.18 | −0.35 | −0.03 | 0.04 | RPL29P12 | −0.36 | 0.19 | −0.11 | 0.09 | −0.71 | AC090150.2 | 0.29 | 0.13 | −0.74 | −0.06 | −2.63 |
| AC011498.4 | −1.03 | 0.08 | 0.87 | 0.58 | 0.21 | MZT2A | 0.07 | −0.13 | −0.02 | 0.07 | 0.24 | AC063948.1 | 0.03 | 0.06 | 0.71 | −0.16 | −0.18 |
| AL365214.2 | −0.65 | 0.13 | 0.58 | −0.21 | 0.04 | AC000058.1 | −0.45 | −0.36 | −2.22 | 0.67 | −1.02 | AC025811.1 | 0.29 | −0.73 | 0.13 | −1.03 | −0.55 |
| RCL1 | −0.20 | 0.00 | 0.12 | −0.04 | 0.13 | SPDYE12P | −0.23 | 0.05 | 0.19 | 0.06 | 0.81 | AC037471.1 | −0.29 | −0.01 | −1.12 | 1.09 | −0.16 |
| BRAF | −0.16 | 0.21 | 0.41 | 0.02 | 0.06 | DPPA2P3 | −0.42 | −0.47 | 1.10 | 0.18 | 0.21 | SLC25A15P2 | 0.24 | 0.14 | 0.18 | −0.04 | −2.18 |
| CR769775.3 | −1.89 | 0.08 | 0.77 | −0.18 | −0.12 | CDC14B | 0.12 | −0.09 | −0.27 | −0.02 | −0.29 | AC007378.1 | −0.03 | −0.32 | 1.01 | 0.60 | 1.04 |
| STRBP | 0.30 | 0.10 | 0.07 | −0.07 | 0.01 | LINC02303 | −0.58 | 0.83 | −1.21 | 0.34 | −2.13 | AC020743.3 | 0.29 | −0.23 | 0.53 | 1.01 | 0.35 |
| AC108136.1 | 1.55 | −0.24 | −1.69 | 1.00 | 0.05 | AC009303.4 | −0.31 | 0.02 | −1.29 | 0.71 | −0.57 | LINC02353 | −0.29 | 0.10 | −0.73 | 0.76 | 0.65 |
| DAB2 | −0.61 | 0.33 | 1.12 | −0.15 | 0.14 | LINC00843 | −0.13 | 0.15 | 0.11 | 0.17 | 0.13 | AL358154.1 | 0.28 | −0.89 | 0.38 | 0.32 | 1.68 |
| RN7SL448P | −1.16 | 0.77 | 0.33 | 0.07 | 0.07 | SNORD3A | −0.19 | −0.07 | 0.04 | 0.25 | −0.19 | AL357375.1 | 0.14 | −2.04 | −1.13 | −0.75 | −0.63 |
| LINC00391 | −1.31 | 1.08 | −1.44 | 1.22 | −1.35 | RNY4 | −0.28 | 0.78 | 0.43 | 0.75 | −0.98 | AC010235.1 | 0.11 | −1.14 | 0.55 | −0.35 | −0.53 |
| AC119396.2 | −0.80 | −0.08 | 1.10 | −0.71 | 0.54 | LINC01967 | 0.39 | 0.05 | −0.32 | 0.25 | 0.38 | GOLGA2P1 | −0.13 | 0.41 | 0.34 | 0.46 | 0.57 |
| AC012594.1 | −0.74 | 0.31 | 0.60 | −0.50 | −0.77 | RPL7P48 | 0.84 | 0.02 | −0.14 | 0.49 | −0.69 | AC007923.4 | 0.02 | −0.59 | −0.73 | 0.11 | 0.26 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| FAM160B2 | −0.30 | 0.09 | −0.16 | 0.20 | 0.15 | IL6R-AS1 | 0.29 | −0.13 | −1.06 | 0.33 | −0.71 | AL390195.2 | 0.01 | 0.30 | 0.40 | 0.03 | −0.09 |
| AC099066.2 | 0.87 | 0.09 | −0.45 | −0.57 | −0.57 | ENC1 | 0.17 | −0.02 | −0.17 | 0.05 | −0.09 | SLC9A7 | 0.02 | −0.15 | −0.02 | −0.20 | 0.11 |
| AC004706.3 | −0.53 | 0.09 | 0.38 | 0.06 | 0.13 | SELENOV | −0.58 | 0.07 | −1.76 | 0.19 | −0.54 | BX323046.1 | −0.05 | −0.05 | −0.82 | −0.40 | −0.77 |
| NSRP1P1 | −0.38 | 0.04 | 0.29 | −0.01 | 0.02 | AL591516.3 | −0.40 | −0.71 | 0.70 | −0.58 | 0.43 | AC112481.1 | 0.17 | 0.51 | 1.49 | 0.03 | 0.02 |
| EIF3G | 0.22 | −0.02 | −0.50 | 0.17 | −0.29 | G32232 | 0.68 | 0.28 | 0.47 | −0.36 | 0.69 | GFPT1 | 0.01 | −0.04 | 0.09 | −0.26 | −0.02 |
| MYOSLID | 0.90 | −0.99 | −1.13 | −0.43 | −0.08 | DOCK11 | 0.17 | −0.09 | −0.42 | −0.06 | −0.30 | AC051618.1 | −0.28 | 0.59 | 0.07 | −0.35 | −0.60 |
| RNU6-97P | 1.19 | −0.50 | −0.34 | −0.29 | 0.54 | RN7SL136P | −0.87 | 1.48 | −1.31 | 0.28 | −3.09 | AC108879.1 | 0.15 | −0.38 | −0.86 | −0.80 | −0.74 |
| HMGN2P3 | 0.95 | −0.37 | −1.06 | 0.27 | −0.23 | AL049536.1 | 0.88 | −0.93 | −2.58 | 0.02 | −0.91 | LINC02146 | −0.28 | −0.80 | −0.84 | −0.74 | −0.50 |
| AC093159.1 | −1.21 | 1.62 | 0.94 | 0.90 | 0.28 | AC100803.1 | −0.44 | −0.85 | −1.15 | 0.58 | 0.04 | AC007922.3 | −0.08 | −1.41 | −0.73 | 1.13 | 0.79 |
| AC079354.1 | −1.21 | 1.40 | 1.16 | 0.92 | 0.05 | RNU6-137P | 0.40 | −0.93 | −0.38 | 0.30 | −0.16 | AC005703.5 | −0.12 | 0.56 | −0.21 | 0.60 | 0.73 |
| GSN-AS1 | −0.37 | 0.09 | 0.08 | −0.08 | 0.01 | DENNDSA | −0.11 | −0.05 | 0.11 | −0.20 | −0.07 | AC079412.1 | 0.28 | 0.24 | −0.66 | −0.57 | −1.72 |
| LINC00601 | −1.09 | −0.69 | 1.67 | −0.34 | 1.27 | MIR3182 | 0.45 | −0.64 | 0.34 | −0.14 | 1.65 | AL121583.1 | 0.04 | 0.60 | 1.17 | −1.16 | −0.99 |
| AL512353.2 | −1.31 | 1.48 | 1.17 | 0.67 | −0.10 | G38146 | 0.52 | 0.10 | −0.29 | 0.31 | −1.43 | AC108114.1 | −0.28 | −0.29 | −1.15 | 1.26 | −1.75 |
| MT-ND6 | −0.47 | 0.23 | 0.35 | 0.07 | 0.09 | AC078878.1 | 0.51 | 0.38 | −0.41 | 0.28 | −0.95 | KIF9 | 0.01 | 0.09 | −0.12 | 0.05 | −0.20 |
| NOV | −0.52 | 0.61 | 0.11 | 0.38 | 0.03 | RNU7-28P | 0.49 | 0.12 | −0.69 | 0.15 | −0.96 | HNRNPA1P22 | 0.03 | −0.41 | 0.26 | −0.60 | 0.58 |
| SF3A1 | 0.15 | −0.02 | −0.18 | 0.03 | −0.11 | RNU6-594P | 0.49 | −1.29 | −0.12 | −0.69 | 1.66 | OR51A9P | 0.10 | −1.34 | 1.77 | −0.51 | 0.82 |
| AC034198.2 | 0.99 | 0.04 | 0.05 | −0.44 | −0.71 | NEK4 | 0.07 | −0.04 | −0.03 | −0.03 | 0.01 | OR9A4 | 0.06 | −0.49 | 1.57 | 0.80 | 0.70 |
| GLULP4 | −1.30 | −0.94 | 0.09 | 0.04 | 0.57 | DEDD | −0.07 | −0.02 | −0.06 | 0.05 | −0.01 | NPAP1P2 | 0.22 | −0.24 | 1.01 | −0.16 | 0.05 |
| MRPL12 | 0.68 | −0.49 | −1.16 | 0.14 | −0.42 | AC093732.2 | −0.28 | 0.14 | −0.25 | −0.24 | −0.35 | ST7-AS1 | 0.04 | 0.57 | 0.06 | 0.53 | 0.03 |
| G34274 | −0.51 | 0.14 | 0.40 | 0.04 | 0.64 | BRIX1P1 | 1.01 | −1.24 | −0.90 | −0.02 | 0.38 | STOML1 | 0.01 | −0.55 | −0.20 | −0.17 | 0.50 |
| AC126544.2 | −0.84 | 0.43 | −0.15 | 0.86 | 1.06 | DNAJC12 | 0.40 | −0.23 | −0.64 | −0.26 | 0.89 | RNU6-1283P | 0.04 | 0.96 | −0.79 | 0.88 | −0.60 |
| AC022211.4 | −0.74 | −0.41 | 0.05 | 0.31 | 0.48 | KLRA1P | −0.09 | −0.12 | 0.25 | −0.16 | 0.43 | AC024267.1 | 0.07 | 1.45 | 1.15 | 0.17 | −0.73 |
| HLA-K | −0.57 | 0.26 | 0.08 | 0.36 | −0.35 | AC115285.1 | 0.66 | 0.81 | −0.30 | −0.44 | −1.15 | AL021918.2 | −0.28 | −0.15 | 0.57 | −1.26 | −0.23 |
| EBAG9 | 0.30 | −0.07 | −0.15 | −0.14 | −0.19 | AC100797.4 | 0.78 | −0.17 | −1.98 | 0.39 | −1.16 | LINC02089 | −0.22 | −0.36 | −1.12 | 1.79 | −0.03 |
| CCDC170 | −0.66 | 0.62 | 0.57 | 0.40 | 0.14 | AL118558.4 | −0.71 | 0.48 | −0.40 | 1.01 | 1.06 | AMTN | 0.07 | −0.78 | 1.21 | −0.80 | −1.66 |
| EXOG | 0.23 | −0.41 | −0.15 | −0.24 | 0.09 | AL117336.2 | 0.89 | −2.62 | −1.54 | −0.55 | 0.27 | AL390961.1 | 0.28 | −0.29 | −1.31 | 2.05 | 2.59 |
| FOXN3 | −0.31 | 0.38 | 0.40 | 0.19 | −0.13 | EPB41L4A-AS1 | −0.10 | 0.10 | 0.29 | 0.09 | 0.05 | KCNJ2-AS1 | 0.03 | −0.28 | −0.35 | 0.25 | 0.54 |
| AP001350.2 | 0.71 | −0.54 | −0.45 | 0.11 | 0.17 | P4HA2-AS1 | 0.48 | 0.81 | −0.06 | 0.05 | −0.77 | BORCS7 | 0.01 | 0.05 | 0.07 | 0.05 | −0.27 |
| FA2H | −1.02 | 0.96 | 0.71 | 1.58 | 0.35 | AC000374.1 | 0.74 | −0.58 | −3.03 | 0.19 | −2.20 | AC092687.1 | 0.25 | −0.91 | −0.22 | 0.85 | 0.75 |
| C1orf53 | 1.35 | −0.64 | −1.33 | −0.46 | −0.98 | KRT85 | −0.66 | 0.66 | 3.20 | −0.79 | 3.14 | AL159987.1 | 0.28 | −1.34 | −0.24 | −0.50 | −0.34 |
| AC004980.3 | −1.22 | 0.01 | 0.26 | 0.23 | 0.41 | AC120053.1 | 0.27 | −0.14 | 0.50 | −0.28 | 0.68 | RNA5SP464 | 0.05 | −1.21 | 0.60 | −0.45 | 0.36 |
| DIO2 | 0.63 | −0.12 | −0.15 | −0.17 | −0.16 | LINC00208 | −0.78 | −0.82 | −1.25 | 0.49 | −1.51 | AC097484.1 | −0.28 | 0.48 | 0.78 | 0.18 | 0.10 |
| ADIPOR2 | 0.34 | 0.02 | −0.20 | 0.09 | −0.26 | RBM44 | 0.13 | 0.16 | −0.30 | 0.17 | −0.22 | OR7E22P | 0.08 | −0.91 | 0.55 | −1.08 | 0.23 |
| PRSS50 | −1.00 | 0.94 | 0.49 | 1.07 | 0.35 | LCE6A | −0.26 | 0.12 | 0.51 | 0.54 | −0.40 | AC090679.2 | −0.28 | −0.08 | 1.48 | −0.81 | 0.48 |
| AL391825.1 | −0.44 | −0.05 | 0.10 | −0.08 | 0.10 | AGEA10-MAGE | −0.56 | 1.34 | 1.60 | 0.95 | 1.35 | PLA2G12B | 0.06 | −1.38 | −1.59 | 0.99 | −0.05 |
| AP000641.1 | −1.80 | 1.13 | 2.12 | −0.11 | 0.82 | FCRL4 | 0.55 | −1.75 | −0.38 | 0.39 | 0.90 | AC106796.1 | −0.28 | −0.91 | 0.72 | −0.41 | 0.49 |
| LINC02208 | −1.34 | 0.68 | 0.51 | 0.10 | 0.35 | AC097658.2 | 1.13 | −2.16 | −0.53 | −0.39 | 1.95 | AL109954.3 | −0.28 | 0.18 | −0.87 | 0.20 | −0.75 |
| RIMKLB | −0.21 | 0.23 | 0.03 | 0.16 | −0.15 | AL022238.2 | 0.19 | −0.02 | 0.09 | 0.30 | 0.09 | ADAM7 | −0.05 | 0.18 | −1.08 | 0.59 | −0.03 |
| OR51F5P | 1.70 | −0.75 | −1.11 | 0.45 | 0.08 | AL356752.1 | 0.43 | −1.33 | 0.55 | 0.27 | 1.25 | AC002044.3 | −0.03 | −0.21 | 0.03 | 0.05 | −0.07 |
| NDUFV2 | 0.44 | −0.18 | −0.18 | −0.01 | −0.05 | FKBP10 | 0.17 | −0.12 | 0.71 | −0.72 | −0.03 | AL118511.1 | 0.13 | −0.35 | −0.62 | 0.88 | 1.02 |
| G34070 | −1.88 | −0.01 | 0.67 | −0.23 | 1.02 | LPO | −0.39 | 0.28 | 0.60 | 0.17 | −0.22 | HOXC9 | −0.01 | 0.05 | −0.12 | 0.23 | −0.20 |
| AC006947.1 | 1.10 | −0.51 | −0.14 | −0.01 | 0.78 | OXLD1 | 0.11 | −0.06 | −0.11 | −0.02 | 0.02 | ANP32AP1 | −0.02 | 0.04 | 0.05 | 0.07 | 0.19 |
| AC012360.2 | 1.91 | −0.16 | −0.09 | −0.27 | 0.12 | AL157912.1 | 0.30 | 0.28 | 0.20 | 0.44 | 0.22 | PDIA3P1 | −0.01 | −0.01 | −0.14 | −0.27 | −0.44 |
| RPL21P121 | 1.17 | −1.07 | −0.06 | −0.05 | 0.30 | COL18A1-AS2 | 0.28 | −0.43 | −1.48 | 0.26 | −0.55 | OR1E1 | 0.15 | 1.16 | −0.36 | 0.09 | −0.99 |
| REXO1 | −0.37 | 0.05 | −0.38 | 0.31 | 0.03 | AK4P4 | −0.49 | −0.19 | 1.00 | −0.53 | 1.30 | AC130415.1 | 0.07 | −0.64 | 0.07 | 0.47 | 1.03 |
| OXT | −0.98 | 0.97 | 0.78 | 0.35 | 0.11 | IFT88 | −0.08 | 0.02 | 0.20 | −0.04 | 0.02 | LINC00469 | 0.17 | −0.38 | −2.56 | 1.35 | −0.26 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC106779.1 | −0.76 | 0.75 | 1.06 | 0.98 | 0.05 | HSPD1P7 | −0.62 | 0.43 | −0.50 | 0.74 | −0.01 | AC062015.1 | 0.11 | −0.57 | 0.82 | 0.12 | 0.67 |
| BCL7C | −0.27 | 0.33 | 0.23 | 0.16 | 0.00 | AP000346.3 | −0.74 | −0.34 | 0.45 | −1.28 | 0.32 | G41882 | 0.07 | 2.12 | −1.19 | 3.05 | −1.54 |
| CCL3 | 1.72 | −1.23 | −1.82 | 0.08 | −0.56 | LRRC19 | −0.14 | 0.08 | 0.00 | 0.38 | −0.10 | AC009975.1 | 0.06 | −0.34 | 0.35 | 0.69 | 0.25 |
| PRR7-AS1 | −0.60 | 0.22 | −0.04 | 0.09 | 0.09 | AC011603.2 | −0.23 | 0.19 | 0.34 | 0.24 | 0.76 | AL513343.1 | −0.03 | −0.15 | 0.09 | 0.56 | 0.29 |
| PCNX4 | 0.20 | −0.15 | −0.02 | −0.07 | 0.09 | AL355297.2 | 0.33 | 0.68 | 1.02 | −0.05 | −0.42 | AC091515.1 | −0.28 | 0.44 | −1.33 | 1.94 | 0.12 |
| ASB13 | 0.33 | −0.07 | −0.08 | 0.17 | −0.07 | AC008739.2 | −0.77 | 0.87 | 0.44 | −0.91 | −0.52 | AC079943.1 | 0.28 | −0.73 | 0.00 | 0.16 | 1.25 |
| AC008638.3 | 1.60 | −2.06 | −2.93 | 0.35 | −0.33 | AC066612.1 | −0.58 | −0.41 | −1.53 | −0.53 | −1.21 | AC006927.5 | −0.14 | 0.49 | −0.94 | −0.34 | −0.99 |
| NBPF16 | −0.34 | 0.43 | 0.41 | 0.20 | 0.32 | EFCAB14P1 | −0.66 | −0.74 | 0.34 | 0.80 | 1.25 | AC109445.1 | −0.28 | −0.41 | 0.27 | 2.53 | 0.23 |
| CDK6 | 0.33 | −0.26 | −0.29 | −0.20 | −0.07 | AC092957.1 | −0.60 | −1.30 | −1.53 | −0.49 | −0.06 | RPL12P32 | 0.07 | 0.86 | 1.06 | 0.42 | 0.24 |
| AL391822.1 | −0.69 | 0.59 | 0.23 | 0.44 | 0.34 | RN7SKP9 | −0.14 | 0.01 | 0.35 | −0.13 | 0.06 | AL109811.2 | −0.05 | −2.26 | −0.65 | 0.03 | 1.20 |
| DIAPH2 | −0.23 | 0.29 | 0.36 | −0.07 | −0.16 | PCCB | 0.08 | 0.10 | −0.03 | 0.19 | 0.02 | PTP4A1P3 | −0.05 | −0.76 | 0.21 | −0.56 | 0.06 |
| AL122020.1 | 0.75 | −0.33 | −0.97 | −0.11 | −0.68 | LDHAP3 | 0.36 | −0.39 | −0.90 | 0.24 | −0.75 | G39184 | −0.11 | −2.25 | 0.45 | −1.82 | 2.45 |
| SLU7 | 0.26 | −0.02 | −0.20 | 0.06 | −0.30 | SEPT7P3 | −0.45 | 0.40 | −1.02 | 0.12 | −0.94 | RNU6-577P | −0.03 | 0.02 | 0.58 | −0.38 | 0.05 |
| NDUFAF4 | 0.37 | −0.25 | −0.29 | −0.23 | −0.28 | RNA5SP262 | −0.90 | 0.51 | 0.64 | −0.70 | −1.17 | AL589745.1 | 0.06 | 0.02 | −0.35 | −0.25 | −0.16 |
| LRIG3 | −0.27 | 0.36 | 0.40 | 0.22 | 0.12 | RNU6-1039P | −1.33 | 0.43 | 1.20 | 0.08 | 1.35 | AC008507.1 | −0.02 | 0.58 | 0.13 | 0.17 | −0.04 |
| KIAA1549L | −0.44 | −0.06 | 0.29 | −0.42 | 0.30 | SLF1 | 0.07 | −0.09 | −0.11 | −0.14 | −0.17 | AC099654.11 | 0.12 | −1.27 | 0.64 | 0.26 | 0.78 |
| OPA1-AS1 | 0.74 | −0.23 | −0.77 | −0.09 | −0.49 | AL162431.4 | −0.22 | 0.02 | −0.32 | 0.31 | 0.01 | C4orf36 | −0.03 | −0.06 | −0.43 | 0.26 | 0.12 |
| MEAF6 | 0.24 | 0.05 | −0.11 | −0.03 | −0.29 | AL132868.1 | 0.35 | −1.04 | −1.77 | −0.13 | −0.87 | LIMD2 | 0.02 | −0.41 | 0.14 | −0.28 | 0.28 |
| LSAMP-AS1 | −0.87 | 0.72 | −0.67 | −0.14 | −1.68 | RN7SL76P | −0.44 | 0.33 | −0.61 | 0.32 | 0.30 | AC087272.1 | −0.28 | −1.15 | −0.34 | 0.28 | 0.98 |
| RNA5SP453 | −1.40 | 1.24 | 1.58 | 0.70 | 1.08 | JRF2P1-LRRC3. | −0.33 | 0.65 | −0.29 | 0.46 | −0.59 | AC103808.2 | 0.17 | −1.32 | −1.06 | 0.58 | −0.86 |
| AC087277.1 | −1.37 | −0.13 | 1.46 | −0.76 | 0.17 | AC125611.4 | 0.55 | −1.15 | −2.29 | 0.34 | −0.82 | HNF1A | 0.04 | −0.63 | −0.43 | 0.18 | 0.83 |
| AC013737.1 | −1.49 | −0.44 | 0.02 | 1.22 | 1.22 | AC020611.1 | 0.42 | 0.02 | −0.95 | −0.61 | −1.35 | HAUS1P1 | 0.05 | 0.76 | 1.38 | 0.05 | 0.56 |
| NR1H2 | −0.22 | 0.20 | −0.18 | 0.12 | −0.24 | AL138828.1 | 0.18 | −0.06 | −0.67 | −0.11 | −0.48 | AC116348.1 | −0.04 | −1.06 | 0.00 | −0.83 | 0.30 |
| PDCL3P5 | −0.58 | 0.11 | 1.21 | −0.28 | 0.40 | SLC6A20 | 0.25 | 0.01 | −0.74 | 0.13 | −1.23 | AL049830.1 | 0.16 | 0.16 | 0.11 | 1.25 | 0.09 |
| PIP4P1 | −0.28 | 0.26 | 0.25 | 0.14 | −0.03 | AC092692.1 | 0.22 | −0.31 | −0.42 | 0.05 | −0.15 | BTF3P2 | 0.23 | 1.10 | −0.09 | 0.60 | −0.57 |
| MYO7B | −0.49 | −0.08 | 0.39 | 0.02 | 0.05 | AL357509.1 | 1.12 | −1.04 | −1.55 | 0.81 | −1.41 | ERMARD | 0.01 | −0.07 | −0.11 | 0.10 | 0.04 |
| AC087343.1 | 0.96 | −0.08 | 0.06 | −0.49 | −0.30 | RBM19 | −0.10 | −0.08 | −0.41 | 0.12 | 0.04 | LINC02291 | −0.06 | −0.49 | −1.23 | 0.17 | −1.51 |
| AP004609.3 | −0.40 | 0.13 | 0.66 | −0.09 | 0.28 | G5664 | −0.92 | −0.63 | 1.00 | 0.74 | 1.11 | SMIM12P1 | −0.17 | −0.80 | 0.85 | −1.07 | −1.14 |
| OR1N1 | −1.04 | −0.10 | −0.34 | 0.57 | 0.30 | PCYT1B | −0.26 | 0.50 | −0.25 | −0.53 | −1.00 | AC125634.1 | −0.28 | 1.66 | −0.84 | 0.72 | −2.86 |
| RN7SL777P | −1.70 | 0.90 | 1.68 | −0.72 | −0.45 | RNU6-1164P | 0.79 | 0.98 | 0.26 | 0.29 | −1.15 | AC096632.1 | 0.22 | −0.15 | −1.18 | −0.19 | −2.40 |
| SLC22A8 | −0.78 | −0.33 | −0.31 | −0.07 | −0.09 | AC068870.1 | 0.38 | −1.31 | −0.87 | −0.20 | −0.27 | AL157414.1 | −0.09 | −1.31 | −0.50 | 0.44 | 1.74 |
| EPHA5 | −0.76 | −0.04 | 0.03 | 0.44 | 0.10 | ASS1P8 | −0.98 | −0.87 | 0.77 | −0.27 | 2.30 | AP003789.1 | 0.15 | 0.71 | −1.13 | 0.14 | −2.60 |
| AC084782.2 | −0.57 | 0.16 | 0.38 | 0.11 | −0.31 | OR5A2 | 0.46 | −0.06 | −1.07 | 0.59 | −1.09 | AP003400.1 | 0.13 | 0.04 | −1.54 | 0.95 | −1.38 |
| HIST1H4E | 0.44 | −0.21 | −0.19 | 0.04 | −0.32 | NPPA | −0.26 | 0.16 | 0.58 | 0.46 | 0.95 | AC124016.1 | −0.03 | −0.25 | −0.68 | −0.27 | −0.45 |
| AP001178.2 | 0.92 | −0.75 | −0.89 | 0.05 | −0.01 | AC009093.8 | −0.42 | −1.27 | −0.66 | −0.38 | 0.17 | AC010395.2 | 0.11 | −0.95 | −0.49 | 0.01 | 1.35 |
| PARL | 0.35 | −0.37 | 0.04 | −0.06 | 0.31 | AC007598.2 | 0.23 | 0.10 | −0.03 | 0.47 | 0.29 | BTBD7P2 | −0.28 | −0.21 | NA | −1.24 | −0.38 |
| ARIH1 | 0.19 | 0.03 | −0.03 | 0.06 | −0.12 | AC073073.2 | 0.15 | −0.38 | −0.37 | 0.08 | −0.15 | AL138752.1 | 0.02 | 0.03 | −0.26 | −0.10 | −0.02 |
| ERCC2 | −0.31 | 0.23 | −0.05 | 0.15 | −0.02 | AP000235.1 | 1.27 | −1.75 | −0.05 | 0.99 | 1.13 | AC021355.1 | −0.08 | −0.28 | −0.98 | 0.62 | 0.48 |
| COX6A1 | 0.58 | −0.32 | 0.21 | −0.62 | 0.06 | LINC01364 | −0.19 | 0.45 | 0.26 | −0.05 | −0.16 | MTND1P26 | 0.28 | −0.68 | −0.02 | −1.10 | 0.35 |
| AC117503.2 | 0.77 | −0.64 | −0.80 | −0.26 | −0.17 | AC090114.1 | 0.28 | 0.33 | −0.51 | 0.28 | −0.39 | AC097110.1 | 0.28 | −1.51 | −0.96 | 1.00 | 1.48 |
| EPPK1 | −0.55 | 0.47 | 0.72 | 0.27 | 0.02 | CYSLTR2 | −0.18 | −0.38 | −0.31 | −0.08 | 0.27 | AP003170.1 | −0.02 | −0.21 | 0.16 | 0.31 | 0.42 |
| DEF6 | −0.40 | −0.10 | −0.25 | 0.22 | 0.25 | ALOX15P2 | 0.65 | 0.09 | −1.19 | 0.26 | −1.30 | AC112219.1 | 0.12 | −1.03 | −1.05 | −0.39 | −0.84 |
| GSS | 0.20 | −0.09 | −0.39 | 0.02 | −0.15 | AC018463.1 | 0.25 | 0.21 | −0.57 | 0.14 | −0.48 | RBBP4P4 | −0.08 | −1.00 | 0.56 | −0.47 | 0.85 |
| AL118556.2 | 0.81 | −0.34 | −0.01 | 0.24 | 0.43 | AC008667.2 | −0.77 | 0.02 | 0.58 | −0.41 | 0.56 | MTCO3P1 | 0.27 | −0.91 | −0.43 | 0.80 | 0.32 |
| MSANTD2 | −0.23 | −0.03 | 0.43 | −0.07 | 0.21 | FCGR2C | −0.18 | −0.10 | 0.54 | −0.12 | 0.19 | MTND3P17 | 0.08 | −0.92 | −0.31 | −0.75 | −1.73 |
| PDE6B | −0.64 | 0.51 | 0.29 | −0.05 | −0.13 | OR11G2 | −0.51 | 0.85 | 0.18 | 0.65 | −0.61 | RGS2 | 0.02 | −0.48 | −0.01 | −0.30 | −0.13 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| G32140 | 0.74 | −0.68 | −0.57 | −0.36 | −0.12 | AC002563.1 | 0.60 | −0.88 | −0.45 | −0.15 | 0.97 | ACTBP1 | −0.09 | −1.02 | 0.05 | −0.01 | 1.07 |
| RTF1 | 0.18 | −0.07 | −0.18 | −0.07 | −0.14 | LINC01514 | −0.31 | 1.15 | 2.12 | 0.64 | 0.30 | FATE1 | 0.08 | 1.19 | −1.11 | 1.22 | −1.09 |
| AC095052.1 | −1.14 | −1.25 | −0.22 | 0.44 | −0.27 | CARMIL1 | 0.04 | −0.03 | −0.12 | 0.13 | −0.05 | RPL32P33 | −0.17 | −0.53 | 0.00 | −1.59 | −0.79 |
| C1orf195 | 0.51 | −0.26 | −0.48 | −0.01 | −0.19 | AC006299.1 | −0.41 | 0.27 | 1.00 | 0.08 | 0.64 | AL356276.1 | 0.27 | 0.75 | −0.82 | 1.59 | −0.32 |
| AC135178.1 | −0.53 | 0.53 | 0.89 | 0.08 | 0.06 | PAICSP5 | 0.64 | 0.11 | 0.70 | 0.43 | 0.04 | AL160408.6 | −0.07 | −0.79 | 0.12 | 0.52 | 0.99 |
| AC023825.1 | 1.02 | −0.55 | −0.27 | −0.58 | −0.24 | BOD1 | 0.07 | −0.02 | 0.05 | −0.04 | −0.02 | AL031710.1 | −0.03 | 0.14 | −0.51 | 0.31 | −0.15 |
| NUCKS1 | 0.24 | −0.11 | −0.14 | −0.04 | −0.13 | MYLKP1 | −0.55 | 0.21 | −0.04 | 0.60 | −0.75 | AC145423.3 | −0.02 | −0.24 | −0.06 | −0.10 | −0.03 |
| RPL32 | 0.39 | −0.05 | −0.12 | −0.20 | −0.48 | G35913 | −0.29 | 0.20 | −0.49 | 0.35 | −0.96 | RN7SL311P | 0.08 | −0.37 | −0.38 | 0.60 | −0.41 |
| AC007342.5 | 1.06 | −0.90 | −0.58 | 0.34 | 0.90 | MTCO2P2 | 0.25 | 0.19 | −0.02 | 0.13 | −0.08 | AC073136.2 | −0.15 | −1.13 | −0.94 | 0.18 | 0.13 |
| RNA5SP93 | −1.37 | 1.00 | 0.93 | 0.46 | 0.23 | RP11-87H9.2 | −0.19 | −0.06 | 0.54 | −0.28 | 0.06 | AC073911.3 | 0.06 | −1.07 | −0.51 | 1.01 | −0.71 |
| RNU6-608P | 0.95 | −0.76 | −0.81 | −0.77 | 0.07 | SLAMF8 | 0.31 | −1.07 | −0.14 | −0.84 | 0.11 | AL672032.1 | 0.08 | −0.69 | −0.38 | 1.06 | 0.97 |
| LRRC43 | −0.70 | −0.54 | 0.19 | −0.15 | 0.98 | SETD5 | 0.04 | −0.01 | −0.11 | −0.01 | −0.05 | LINC00390 | 0.19 | 0.08 | −0.27 | 1.09 | 0.99 |
| FOXD2-AS1 | −0.71 | −0.10 | 0.57 | 0.43 | 1.08 | NDUFAB1P1 | 0.23 | −0.53 | 0.38 | −0.25 | 0.37 | POU3F4 | 0.05 | 0.10 | 1.34 | −0.20 | −0.28 |
| CDC42 | 0.41 | −0.20 | −0.43 | −0.04 | −0.11 | G230 | 0.51 | −0.38 | −0.55 | −0.81 | −0.85 | AL049840.3 | 0.03 | −0.28 | −0.21 | −0.08 | −0.10 |
| RANP4 | −0.87 | 0.86 | 0.58 | 0.11 | 0.21 | AC092718.2 | 0.28 | −0.30 | −1.62 | −0.39 | −1.70 | LINC02369 | −0.12 | 0.54 | −0.62 | −0.44 | −0.69 |
| AC009962.1 | −0.56 | 0.56 | 0.66 | 0.16 | 0.57 | AC023813.1 | 1.69 | −2.68 | −0.72 | −0.19 | 0.49 | NAA10 | −0.01 | 0.02 | −0.31 | 0.23 | −0.01 |
| C2CD5 | −0.18 | 0.07 | 0.00 | 0.13 | 0.04 | RPUSD4 | 0.07 | −0.05 | −0.37 | 0.14 | −0.21 | NUTM2A-AS1 | −0.01 | 0.05 | 0.21 | −0.18 | −0.04 |
| GPATCH8 | −0.12 | 0.11 | 0.08 | −0.01 | −0.04 | AL157899.1 | 0.54 | −1.31 | −2.48 | 0.46 | −0.69 | AL442224.1 | −0.27 | 0.93 | 1.06 | −0.88 | −1.68 |
| AC100803.2 | −1.68 | 0.77 | 1.28 | −0.08 | −0.70 | AL355303.1 | 0.54 | −2.47 | −1.14 | −0.32 | 1.39 | LINC01257 | −0.07 | −0.38 | −0.30 | 0.24 | −1.20 |
| RCVRN | −0.95 | −0.03 | 0.43 | 0.46 | −0.05 | AC099778.1 | −0.14 | 0.06 | 0.17 | −0.10 | −0.13 | AL589684.1 | 0.09 | −0.88 | −1.82 | −0.51 | −0.74 |
| RTL6 | 0.29 | 0.03 | −0.16 | −0.07 | −0.18 | AL391244.2 | 0.50 | 0.60 | 0.86 | 0.16 | 0.47 | GPR143P | 0.09 | −0.07 | −0.65 | 0.52 | −0.56 |
| E2F2 | 0.43 | −0.39 | −0.60 | 0.21 | 0.25 | LINC01299 | −0.59 | −1.61 | −1.23 | −0.19 | −0.18 | LINC01707 | 0.27 | −1.13 | 1.17 | −1.37 | 0.30 |
| IGFALS | −0.97 | −0.09 | 1.19 | 0.30 | 0.77 | LINC02065 | 0.44 | −1.32 | −0.88 | −0.89 | −0.45 | SETP7 | 0.06 | −1.36 | −1.81 | 0.09 | −0.46 |
| ASTN2-AS1 | −0.78 | 0.10 | 0.06 | 0.49 | −0.12 | AC026318.1 | −0.45 | 0.70 | −1.39 | 1.10 | −0.87 | RBPMSLP | −0.03 | −0.32 | 0.11 | 0.36 | 0.87 |
| KRTAP10-8 | −1.82 | 1.09 | −2.24 | 0.92 | −3.24 | AL035409.1 | −0.68 | 0.71 | 0.99 | 2.38 | −1.22 | RNU6-843P | −0.27 | 0.16 | NA | −0.54 | −0.20 |
| NDUFA2 | 0.35 | 0.21 | −0.36 | 0.26 | −0.55 | AC093010.1 | 0.67 | −0.60 | −1.91 | 0.35 | −1.46 | ANKRD65 | 0.02 | 0.14 | 0.07 | 0.41 | 0.66 |
| DIRC3-AS1 | −0.94 | −0.15 | 1.16 | −0.27 | 0.74 | AL157896.1 | −1.15 | −0.17 | −0.29 | 1.44 | 0.44 | AL138694.1 | 0.05 | −0.18 | −1.42 | 0.43 | −0.74 |
| STOM | 0.36 | −0.20 | −0.19 | −0.16 | −0.24 | G22216 | 1.01 | 0.41 | −0.80 | −0.45 | −1.58 | PRR13P1 | 0.02 | −0.83 | −0.71 | −0.53 | 0.76 |
| RNVU1-18 | −0.61 | 0.05 | −0.29 | −0.40 | −0.51 | ADGRG5 | −0.28 | −0.34 | −0.41 | −0.20 | −0.24 | AC110741.1 | −0.27 | 0.49 | −0.21 | 1.26 | −0.41 |
| NRM | 0.35 | −0.24 | −0.54 | −0.13 | −0.42 | AC107294.2 | −0.32 | −0.25 | 1.13 | −0.01 | 1.05 | AC091152.1 | 0.04 | −0.99 | −0.87 | −0.70 | −0.50 |
| PDE5A | −0.45 | 0.59 | 0.82 | 0.34 | 0.05 | AC134772.1 | −0.39 | 0.79 | 0.32 | 0.11 | −0.07 | AC007403.1 | −0.14 | 0.65 | −0.84 | −0.91 | −2.20 |
| AC010307.3 | −0.88 | 1.58 | −0.53 | 0.17 | −0.76 | PRKAB2 | 0.09 | 0.12 | 0.16 | 0.05 | −0.15 | RPS6KA2-AS1 | −0.04 | 0.65 | 0.39 | 0.86 | −0.35 |
| G23907 | −1.88 | 3.10 | 4.45 | 1.98 | 2.09 | ENO1P3 | 0.25 | −0.16 | 0.27 | −0.13 | 0.22 | MIR1193 | 0.06 | −0.36 | 0.28 | −0.90 | 0.59 |
| PXDC1 | −0.29 | 0.15 | 0.11 | −0.15 | −0.16 | OR4F13P | 0.62 | −1.66 | 0.16 | −1.05 | 0.38 | AC026898.1 | −0.27 | 0.74 | −0.87 | 0.47 | −1.38 |
| AC069547.1 | 0.53 | −0.08 | −0.26 | −0.18 | −0.09 | LINC02355 | −0.47 | −2.16 | 0.83 | 0.52 | 0.85 | AC069304.3 | 0.27 | −0.04 | 1.17 | 0.52 | −0.55 |
| OR51B5 | −1.15 | 0.74 | 0.27 | 0.70 | −0.60 | SRRM4 | 0.29 | −0.97 | −1.01 | 0.36 | −0.24 | NDUFS5P4 | −0.27 | −0.29 | 0.01 | 1.65 | 0.78 |
| ABCC8 | −1.10 | −0.08 | 0.11 | −0.17 | 0.42 | LINC01132 | 0.24 | −0.82 | 0.04 | −0.25 | 0.37 | ARRDC2 | −0.01 | −0.16 | −0.03 | −0.08 | 0.18 |
| LINC01600 | −0.97 | −0.27 | 1.96 | −0.23 | 1.02 | NUS1P4 | −1.00 | −0.91 | −0.28 | −0.08 | −1.39 | OR52S1P | −0.27 | 0.90 | −1.73 | 1.68 | −1.49 |
| IL12B | 1.49 | −0.88 | −0.44 | −0.67 | −0.13 | HSF5 | −0.34 | −0.06 | −1.40 | −0.78 | −1.48 | AP003115.1 | −0.27 | −0.33 | 2.18 | −1.37 | 1.15 |
| MTMR8 | −0.40 | 0.43 | 0.68 | 0.14 | 0.35 | GBE1 | 0.12 | −0.07 | −0.21 | −0.07 | −0.21 | Clorf159 | 0.01 | 0.03 | −0.27 | 0.32 | 0.13 |
| SMG1P1 | −0.40 | 0.13 | 0.12 | 0.05 | 0.12 | AC084706.1 | −0.95 | −0.10 | 0.52 | 2.76 | 1.02 | PAQR9 | −0.06 | −0.55 | −0.85 | −0.04 | −2.69 |
| AC122688.3 | −0.50 | 0.17 | 0.48 | 0.12 | 0.30 | AC018638.3 | −0.31 | 0.07 | 0.35 | 0.14 | 0.37 | LINC00677 | 0.07 | −0.84 | 0.16 | −0.22 | 1.61 |
| LINC01197 | −0.65 | 0.27 | 0.94 | −0.08 | 0.04 | AC008074.2 | 0.22 | 0.06 | −0.68 | 0.40 | −0.35 | RPL22P7 | 0.16 | −0.94 | 1.15 | −1.31 | 0.21 |
| MADD | −0.18 | 0.12 | 0.18 | 0.00 | 0.06 | HMGB3P15 | 0.61 | 0.18 | 0.53 | 0.69 | −0.24 | LINC01393 | 0.05 | 0.86 | −0.50 | 0.90 | −1.79 |
| NLGN3 | −0.64 | 0.07 | 0.45 | 0.21 | 0.75 | LAGE3P1 | −0.29 | −0.20 | 0.64 | 0.13 | 0.50 | AL050344.2 | 0.17 | −0.28 | 0.48 | −0.16 | 0.79 |
| DFFA | 0.20 | −0.23 | −0.66 | 0.01 | −0.21 | NLRP7 | 0.55 | −0.33 | −1.22 | −0.78 | −1.41 | AC011460.1 | −0.08 | −0.61 | −1.74 | 0.99 | −0.81 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| C1orf112 | 0.26 | −0.37 | −0.12 | −0.24 | 0.15 | RNF43 | 0.20 | 0.24 | 0.11 | 0.28 | 0.30 | AC087283.1 | −0.22 | −0.52 | −0.58 | 0.93 | 1.81 |
| LRRC77P | −0.78 | 0.54 | 0.24 | 0.71 | −0.49 | CCDC88B | −0.19 | −0.50 | −0.17 | −0.07 | 0.38 | AL136309.4 | 0.11 | 1.76 | 0.07 | 0.15 | 0.66 |
| SIRT3 | −0.27 | 0.08 | 0.09 | 0.29 | 0.23 | MIR4779 | −0.57 | 0.06 | −0.83 | 0.18 | 0.01 | RN7SL586P | 0.18 | −0.46 | −1.52 | 2.64 | 0.01 |
| CD79A | 1.43 | −0.69 | 0.59 | 0.22 | −1.25 | AC092535.3 | −0.24 | −0.06 | −0.41 | 0.17 | −0.29 | ECM1P2 | 0.08 | 0.35 | −2.34 | 0.74 | −0.64 |
| SPRED1 | 0.27 | −0.13 | −0.20 | −0.12 | 0.01 | SLC5A3 | 0.12 | −0.02 | −0.38 | 0.23 | −0.11 | SAP30BP | 0.01 | 0.01 | −0.21 | −0.08 | −0.12 |
| IPO9 | 0.16 | −0.15 | −0.05 | −0.03 | 0.02 | GJD2 | −0.77 | 0.87 | −0.16 | 0.11 | −0.33 | BTG2 | −0.01 | 0.04 | 0.12 | −0.05 | −0.09 |
| DIRC3 | −0.52 | 0.02 | 0.06 | −0.06 | −0.23 | MED7 | 0.09 | −0.22 | −0.13 | −0.12 | −0.02 | AP003086.3 | 0.03 | 0.53 | 0.28 | −0.40 | −0.71 |
| GZMA | 1.01 | −0.98 | 0.22 | −0.06 | 1.06 | NSFP1 | 0.28 | −0.02 | −0.46 | −0.11 | −0.66 | LINC00358 | −0.27 | 0.18 | 0.45 | −0.30 | −0.56 |
| PLEK | 0.89 | −1.45 | −1.02 | −0.39 | −0.13 | NCF1 | −0.24 | −0.17 | −0.37 | −0.23 | −0.78 | AL137246.2 | 0.06 | 1.55 | 0.09 | 1.24 | 0.36 |
| IL13RA2 | 1.15 | −1.42 | −2.12 | −0.35 | −0.65 | RPL12P15 | −0.30 | −0.57 | 0.55 | −0.37 | 0.69 | RP11-782C8.4 | 0.02 | 0.49 | 0.05 | 0.12 | −0.35 |
| CAPN9 | −0.98 | −0.12 | −0.02 | 0.42 | −0.12 | CTDP1 | −0.09 | 0.08 | −0.14 | 0.07 | −0.07 | AC074134.1 | −0.05 | −1.51 | −0.97 | −0.22 | −0.15 |
| G16361 | 1.08 | −1.46 | −0.42 | −0.29 | 0.89 | AC007450.2 | 0.53 | 0.12 | 0.07 | 1.00 | 1.64 | RNU6-1 | −0.04 | 0.08 | −0.62 | −0.90 | −0.76 |
| RN7SL753P | −0.61 | 0.11 | −0.01 | −0.08 | −0.01 | ILVBL | −0.08 | 0.16 | −0.15 | 0.25 | −0.18 | RPS3AP24 | −0.17 | −0.20 | 1.66 | −0.54 | 2.52 |
| AC098591.1 | −0.91 | 0.25 | 0.22 | −0.20 | −0.04 | AC018696.2 | −0.74 | −1.08 | 1.09 | 0.57 | 1.15 | LRRC69 | 0.01 | −0.07 | 0.00 | −0.13 | 0.01 |
| FAM185BP | −0.45 | 0.34 | 1.00 | 0.01 | 0.45 | AC004453.1 | 0.14 | −0.14 | −0.11 | −0.14 | −0.12 | LINC02034 | −0.08 | −0.35 | −1.05 | −0.87 | −3.19 |
| AC090559.2 | −0.47 | −0.52 | −0.01 | −0.36 | 0.58 | CD84 | 0.22 | −0.37 | 0.08 | −0.27 | 0.29 | NR0B2 | −0.10 | −1.47 | 0.98 | −0.31 | 2.69 |
| KRT18P19 | −1.11 | −0.22 | 1.49 | 0.56 | 2.07 | AC129510.2 | 0.77 | −0.91 | −0.06 | 0.40 | 0.70 | GCNT1P1 | 0.03 | 0.41 | 0.19 | −0.08 | −0.54 |
| AL158827.2 | −0.55 | 0.16 | 1.25 | −0.43 | 0.36 | MTND6P32 | 0.31 | 0.20 | −0.12 | −0.33 | −1.09 | RNU6-134P | 0.24 | 0.51 | −0.29 | 2.48 | −0.17 |
| FBXO10 | 0.38 | −0.09 | −0.14 | 0.15 | −0.03 | CD300LD | 0.91 | −0.62 | −1.80 | −0.21 | −1.28 | AP001363.1 | −0.02 | 0.24 | 0.18 | 0.13 | 0.34 |
| SNORA80B | 0.95 | −1.50 | −0.62 | −1.39 | −0.75 | AL354892.3 | −0.17 | −0.01 | 0.13 | 0.21 | 0.14 | AC073521.1 | 0.27 | −0.57 | −0.87 | −0.17 | −0.70 |
| RNU6-1333P | 1.62 | −1.49 | −0.34 | −0.14 | 0.40 | ANKRD26 | 0.07 | −0.05 | −0.02 | −0.07 | 0.07 | AJ239321.1 | 0.27 | −0.08 | −1.29 | −0.81 | −0.69 |
| G26709 | −1.83 | 1.00 | −0.77 | 1.97 | −0.14 | LINC02227 | −0.29 | −0.07 | −0.40 | 0.46 | 0.03 | G25704 | −0.03 | 0.59 | −2.20 | 1.06 | −0.64 |
| AL161785.1 | −0.92 | −0.51 | 0.18 | 0.26 | 0.71 | AC011120.1 | 0.23 | −0.62 | 0.30 | −0.28 | 0.64 | AC099344.2 | 0.10 | −0.15 | −1.28 | 1.72 | −2.11 |
| G31717 | −1.83 | −0.30 | 2.95 | −1.64 | 0.38 | AC111170.2 | 0.83 | 0.62 | −1.30 | 0.19 | −1.01 | AL161733.1 | 0.27 | −0.75 | −0.49 | −0.22 | 0.49 |
| AC003080.1 | 0.55 | −0.76 | 0.09 | −0.34 | 0.33 | GPR61 | −0.19 | 0.04 | −0.41 | 0.29 | −0.07 | RNU6-923P | −0.11 | −0.45 | 1.24 | −0.01 | 1.79 |
| ARC | 0.73 | 0.15 | −2.24 | −0.04 | −2.17 | RN7SKP92 | 0.71 | −1.51 | −0.74 | 0.27 | 0.42 | BTBD17 | −0.07 | −0.73 | 0.38 | −1.86 | 0.76 |
| AC111194.2 | 1.20 | −0.74 | −1.52 | −0.09 | −0.57 | AL627389.1 | −0.36 | 0.54 | 0.64 | 0.10 | 0.05 | AC024941.2 | 0.05 | −0.62 | 0.91 | −0.46 | 0.76 |
| MARK3P1 | −1.29 | −0.18 | 1.75 | 0.78 | 1.57 | RIPOR2 | −0.19 | −0.21 | 0.43 | −0.37 | 0.34 | RNU6-977P | 0.10 | 0.03 | 0.98 | −0.92 | 0.48 |
| MARK2 | 0.25 | 0.05 | −0.24 | 0.06 | −0.11 | CTAGE9 | −0.38 | 0.95 | −0.54 | 0.74 | −0.64 | MOXD2P | 0.06 | −0.27 | −0.99 | 1.05 | −1.09 |
| RPS12P5 | −0.94 | 0.40 | 0.46 | 0.27 | −0.27 | NPM1P38 | −0.49 | −2.60 | −1.11 | −0.21 | 1.00 | OR13A1 | −0.07 | 1.25 | −1.27 | 0.51 | −1.30 |
| HGD | −0.93 | 0.38 | 0.29 | 0.58 | 0.49 | MIR550A2 | 0.69 | −0.66 | −0.61 | 0.59 | 0.72 | LINC01746 | 0.27 | −0.64 | 0.59 | 0.73 | 0.65 |
| ITPR1 | −0.47 | 0.27 | 0.70 | 0.03 | 0.37 | AC126614.1 | −0.24 | −0.03 | −0.63 | 0.28 | −0.02 | AIG1P1 | 0.03 | −0.01 | −0.41 | −0.49 | −0.42 |
| ANXA13 | −1.01 | −0.03 | 0.42 | −0.28 | 0.49 | RHOXF2B | −0.49 | −0.02 | 1.05 | −0.19 | 0.52 | AC022202.1 | 0.27 | 0.93 | −0.32 | −0.25 | −1.86 |
| AP000763.1 | 1.12 | 0.08 | 0.01 | 0.26 | 0.59 | MANCR | 0.45 | 0.55 | −2.59 | 0.15 | −1.85 | AC116424.1 | −0.03 | −0.38 | −0.61 | −0.11 | 0.00 |
| DZIP1 | −0.46 | 0.18 | 0.95 | −0.11 | 0.19 | LINC02098 | 1.08 | −0.56 | −2.51 | −0.19 | −2.32 | OR4A11P | 0.09 | −1.29 | −1.40 | 1.51 | −0.12 |
| AL158152.1 | 0.74 | −0.04 | −0.13 | 0.04 | 0.01 | CDR2L | 0.12 | 0.08 | −0.07 | −0.12 | −0.02 | AC013400.1 | 0.06 | −0.58 | −1.31 | 0.91 | 1.21 |
| MYSM1 | 0.16 | 0.02 | −0.03 | −0.05 | −0.07 | AL135924.2 | 0.78 | 1.01 | 0.67 | 0.40 | 0.72 | DSPP | 0.04 | 0.37 | −0.02 | 0.45 | −0.80 |
| AC136424.2 | −0.73 | 0.64 | 1.25 | −0.22 | −0.02 | AC046195.1 | −0.51 | −0.66 | 0.15 | −0.88 | −0.76 | SEL1L2 | 0.04 | 0.01 | −1.31 | 0.60 | −1.03 |
| SPA17P1 | −0.93 | 0.78 | 0.53 | 0.88 | 0.60 | RN7SL20P | 0.56 | −1.89 | −0.89 | −0.93 | 0.08 | AC010486.1 | −0.26 | 0.07 | 0.59 | −0.27 | −0.31 |
| AC114490.1 | −0.83 | −0.03 | 1.63 | −0.35 | 0.88 | SSMEM1 | 0.90 | −1.90 | −0.28 | 0.03 | 0.53 | AC011990.1 | 0.27 | −0.58 | 0.28 | 0.52 | 1.60 |
| AC025857.2 | 0.84 | −0.45 | −0.62 | −0.05 | 0.04 | RNU6-567P | 1.15 | 0.22 | −0.93 | 0.86 | −0.10 | NINJ2 | 0.02 | 0.33 | 0.53 | −0.46 | −0.39 |
| AC099343.3 | −0.64 | 0.25 | 0.56 | −0.03 | 0.34 | AC122719.1 | 0.86 | −0.87 | −0.71 | −0.49 | 0.72 | AL157384.1 | −0.02 | 0.13 | 0.14 | 0.22 | 0.32 |
| SNORD59A | −0.70 | 0.51 | 0.73 | 0.19 | −0.32 | RNU6-1127P | 0.56 | −1.48 | 0.51 | −0.73 | 1.86 | AL360085.1 | 0.08 | −0.21 | −1.08 | −1.53 | −1.85 |
| G5386 | 0.63 | −0.50 | −0.81 | 0.38 | 0.66 | KALRN | −0.16 | 0.21 | −0.38 | 0.32 | −0.10 | RNASE13 | −0.06 | −0.55 | −0.37 | 0.04 | −0.02 |
| CCDC160 | −1.06 | 1.20 | 2.14 | 0.32 | 0.67 | PTX3 | 0.33 | −0.26 | 0.09 | 0.15 | 0.54 | AL031659.1 | −0.05 | −0.31 | −0.24 | 0.16 | 1.22 |
| PCDHA4 | −1.30 | 1.05 | 0.55 | 0.54 | −0.13 | PIGM | −0.08 | 0.01 | 0.28 | 0.00 | 0.23 | SCYGR8 | 0.15 | −1.02 | −0.24 | 0.84 | −0.14 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AP005131.6 | −0.42 | 0.45 | 0.52 | 0.08 | 0.16 | AC010261.2 | 0.15 | 0.10 | 0.51 | 0.29 | 0.32 | AC121342.1 | −0.26 | −0.38 | −0.69 | −1.32 | −2.40 |
| AL158068.2 | 0.72 | −0.89 | 0.36 | −0.78 | 0.28 | ATP5MDP1 | −0.28 | 0.36 | 1.06 | 0.18 | 0.37 | MTND6P16 | −0.24 | −0.38 | −0.05 | 0.11 | −0.92 |
| NCAPH2 | −0.30 | −0.02 | −0.26 | 0.12 | −0.06 | PPBP | −0.43 | −0.37 | −1.01 | 0.42 | −1.11 | AC027559.1 | 0.03 | −0.56 | −0.24 | 0.01 | 0.44 |
| IFI35 | 0.41 | −0.52 | −0.33 | −0.62 | −0.09 | DPP9-AS1 | −0.22 | 0.47 | −0.92 | 0.41 | −1.07 | LINC02362 | −0.02 | −0.39 | 0.15 | −0.39 | 0.10 |
| AL603882.1 | 1.85 | −1.27 | −1.92 | 0.05 | 0.09 | AL096855.2 | −0.24 | −0.30 | 0.83 | −0.01 | 0.41 | INSL5 | 0.19 | −0.15 | 1.67 | −1.31 | 0.91 |
| IL18R1 | 0.39 | −0.26 | 0.53 | −0.25 | 0.41 | CTF1 | −0.24 | 0.00 | −0.14 | −0.12 | 0.13 | IPO7P1 | 0.05 | 0.16 | −0.96 | 0.56 | −0.47 |
| EEF1B2P2 | 1.34 | −0.25 | −1.37 | 0.05 | −1.23 | AC003102.1 | 0.12 | −0.08 | −0.70 | 0.35 | −0.22 | MINDY3 | 0.01 | 0.02 | 0.07 | −0.07 | −0.08 |
| AC089998.4 | 1.65 | 0.67 | 0.61 | 0.58 | −0.49 | AP003497.1 | −0.72 | 0.68 | −0.09 | 1.37 | −0.01 | ACE2 | −0.05 | −0.23 | 0.28 | −0.59 | −0.38 |
| AC011455.2 | −1.36 | −0.20 | 0.72 | 0.35 | 1.00 | KCNN3 | 0.15 | 0.12 | 0.31 | 0.28 | 0.02 | AC007823.1 | 0.03 | −0.18 | −0.85 | −0.35 | −0.82 |
| LINC01374 | −1.62 | 1.23 | 0.92 | 0.40 | −0.74 | AC114488.1 | −0.55 | 1.94 | 0.92 | 2.08 | 0.78 | RNA5SP194 | −0.03 | −0.86 | −0.30 | −0.13 | 0.91 |
| EIF2B4 | −0.28 | 0.20 | 0.19 | 0.01 | −0.05 | AL137000.1 | −0.64 | 0.44 | −1.90 | −0.22 | −3.01 | OR52M1 | 0.11 | −1.71 | −0.17 | 0.27 | 0.54 |
| AC015743.1 | −1.35 | 0.37 | −0.03 | 1.76 | 0.19 | HMGN2P46 | −0.20 | −0.25 | −0.04 | −0.39 | 0.05 | AL139095.5 | −0.06 | 1.09 | 1.28 | −0.36 | 1.36 |
| AC011676.1 | −0.71 | 0.22 | 0.42 | −0.39 | 0.07 | AC008064.1 | −1.23 | −0.21 | 2.34 | −0.81 | 1.71 | PGK1P2 | −0.06 | 0.13 | −0.90 | 0.67 | 0.92 |
| OTOF | −0.98 | −0.41 | 0.01 | 0.24 | −0.07 | RNU7-171P | 0.70 | 0.12 | 1.25 | −0.11 | 0.23 | LINC02387 | 0.10 | 0.76 | −0.21 | 0.55 | −1.39 |
| HCK | 0.54 | −0.74 | −0.41 | −0.50 | −0.28 | AC000003.1 | −0.43 | −0.74 | 1.32 | −0.22 | 0.15 | AL450311.2 | −0.15 | −1.02 | −0.47 | −0.63 | 1.95 |
| DIS3L | −0.22 | 0.09 | 0.11 | −0.01 | 0.00 | AGBL1-AS1 | 0.48 | −1.22 | −0.78 | −0.14 | −0.06 | AC007663.4 | −0.03 | 0.64 | 1.31 | 0.28 | 0.12 |
| SNX11 | 0.26 | −0.08 | −0.41 | −0.02 | −0.15 | RNUSB-4P | 0.55 | −0.35 | 0.77 | 0.55 | 0.60 | CLTRN | −0.04 | −0.52 | 0.10 | −0.16 | −0.40 |
| LINC02172 | −1.38 | 1.29 | −0.67 | 1.26 | −0.58 | AL160006.1 | 0.15 | 0.39 | −0.25 | 0.36 | −0.36 | MYH10 | 0.01 | −0.09 | 0.03 | −0.23 | −0.13 |
| RNU4-49P | 0.84 | −0.70 | 0.40 | 0.04 | 0.37 | LINC02556 | 0.77 | −0.24 | −0.04 | 1.07 | 1.30 | RP11-1109M24.1 | −0.11 | −1.06 | 0.86 | 0.13 | 0.12 |
| OGFRP1 | 0.53 | −0.48 | −0.86 | −0.09 | 0.01 | AC139099.1 | 0.87 | −0.51 | −0.36 | 0.40 | −0.80 | AC008620.2 | 0.09 | −0.81 | −2.48 | 0.95 | −1.23 |
| CLK4 | −0.21 | 0.29 | 0.35 | 0.17 | 0.07 | BNIP3P26 | −0.28 | −0.04 | 0.37 | 0.17 | 0.42 | RNU6-597P | −0.06 | −2.40 | 0.67 | −0.97 | 2.71 |
| PARN | 0.11 | −0.07 | −0.08 | −0.02 | −0.02 | ANAPC10P1 | 0.21 | −0.08 | −0.37 | −0.27 | −0.67 | CLRN2 | 0.18 | 0.21 | 1.83 | −0.59 | 2.00 |
| AL136295.7 | −0.38 | 0.11 | 0.55 | 0.21 | 0.37 | ORMDL1 | 0.14 | 0.08 | 0.34 | 0.05 | 0.23 | PCMTD1P3 | −0.15 | −0.65 | −1.31 | −0.64 | −0.81 |
| MT-CYB | −0.47 | 0.21 | 0.27 | 0.08 | 0.14 | IGDCC3 | −0.31 | −0.83 | −0.98 | −0.37 | −0.47 | AC079298.1 | 0.09 | −0.61 | 0.97 | 0.12 | 2.00 |
| LINC02391 | −0.95 | 0.01 | 1.65 | −0.15 | 0.75 | AC112907.2 | 0.52 | 0.02 | 0.76 | −0.61 | 1.31 | OR2W6P | −0.10 | −0.77 | 0.22 | 0.04 | 0.54 |
| SELP | 0.61 | −0.45 | 0.66 | −0.23 | −0.25 | INHBE | 0.33 | −0.80 | −0.64 | 0.01 | 0.01 | AC020611.2 | 0.03 | −0.79 | 0.81 | −0.08 | 1.18 |
| AC133528.1 | −0.85 | 0.84 | 1.02 | 0.26 | 0.35 | AC104777.1 | −0.62 | 1.51 | −0.54 | 0.69 | −0.67 | AC006115.3 | −0.26 | 0.28 | 0.58 | −0.08 | −0.61 |
| RN7SL506P | −0.79 | 0.06 | −0.37 | 0.64 | 0.70 | ADAM20P1 | −0.16 | 0.00 | 0.36 | −0.57 | −0.11 | SMIM6 | −0.02 | 0.11 | 0.28 | 0.04 | −0.11 |
| AC010890.1 | 0.61 | −0.31 | −0.52 | −0.02 | 0.67 | AC005324.5 | 0.41 | −1.19 | −0.10 | −0.56 | 0.44 | AC017079.2 | 0.14 | −0.85 | −0.10 | 0.71 | 0.39 |
| CALN1 | −0.67 | 0.58 | 0.25 | 0.88 | −0.10 | AC007969.1 | 0.16 | −0.08 | 0.25 | −0.39 | 0.00 | AL603839.2 | 0.04 | −0.23 | 0.60 | 0.05 | −0.22 |
| MON1B | 0.20 | −0.08 | −0.18 | −0.01 | −0.08 | AL022721.1 | 0.72 | −1.87 | −1.40 | 0.13 | 0.44 | OR5A1 | 0.05 | −0.34 | −1.15 | 0.10 | −0.79 |
| ITPKC | 0.32 | −0.03 | −0.80 | 0.26 | −0.51 | LINC01832 | −0.31 | 0.61 | 0.49 | 0.54 | −0.22 | HSPA8P11 | −0.05 | −0.30 | −0.28 | 1.03 | 0.29 |
| IL32 | 0.69 | −0.64 | 0.17 | −0.48 | 0.16 | LINC00853 | 0.38 | 0.66 | −0.01 | 0.00 | −0.46 | AP002512.1 | 0.26 | −0.34 | −0.54 | −0.15 | −0.17 |
| AC064805.1 | 1.15 | −1.12 | −1.13 | −0.55 | 0.78 | AL109976.1 | 0.17 | 0.19 | 0.39 | 0.13 | 0.27 | AL121852.1 | 0.05 | −0.02 | 0.75 | −0.10 | 0.53 |
| LIX1-AS1 | −0.93 | −0.15 | 0.01 | −0.66 | −0.93 | ERICH5 | −0.26 | 0.55 | 0.34 | −0.08 | 0.02 | RN7SKP77 | −0.26 | 0.32 | −0.09 | −0.08 | −0.32 |
| AC073530.1 | 0.71 | −0.20 | −0.24 | 0.16 | 0.06 | OR2M1P | 1.03 | 0.44 | 0.65 | 1.22 | −1.76 | AF216667.1 | 0.26 | −0.47 | −0.65 | 0.42 | 0.60 |
| AL109761.1 | 0.60 | −0.26 | 0.08 | 0.44 | 0.33 | AC114808.2 | −0.32 | 0.73 | 0.57 | −0.84 | −0.46 | MTCO2P18 | 0.25 | 0.06 | −1.04 | 0.61 | −2.05 |
| IL6 | 1.10 | −1.76 | −1.22 | −2.47 | 0.06 | MTND2P8 | −0.61 | 0.00 | −0.55 | −1.41 | −1.71 | FAM19A4 | 0.05 | 0.43 | −1.25 | 0.08 | −0.88 |
| RN7SL406P | 1.22 | −1.51 | −0.15 | 0.24 | 1.13 | GCFC2 | 0.08 | −0.06 | 0.06 | −0.14 | 0.04 | SNRPEP10 | 0.18 | 0.34 | 0.49 | 0.17 | 0.27 |
| FBXO4 | 0.29 | −0.15 | −0.18 | 0.01 | −0.08 | NEUROD4 | 0.51 | −0.24 | −1.92 | 0.58 | −1.45 | AL358472.4 | −0.03 | −0.13 | 0.02 | −0.16 | −0.45 |
| AC090229.1 | 0.60 | −0.02 | −0.05 | −0.07 | −0.03 | GVINP2 | −0.41 | 0.96 | −0.20 | 0.81 | 0.08 | KIR2DL1 | −0.08 | 1.03 | −1.43 | 1.16 | −0.54 |
| AC005920.1 | −1.55 | 1.54 | 1.50 | 1.70 | 0.22 | SHANK3 | 0.19 | −0.20 | −0.07 | 0.18 | 0.23 | KLF7P1 | −0.17 | 0.14 | 0.41 | 0.21 | −0.77 |
| AC092944.1 | −0.75 | −0.03 | 0.24 | −0.25 | 0.53 | AC005020.1 | −0.22 | 0.10 | 1.03 | −0.41 | 0.34 | RPL34P34 | −0.06 | −0.53 | 1.87 | −1.98 | 0.06 |
| AC068831.1 | 0.70 | −0.12 | −0.85 | −0.05 | −0.76 | RPL7P8 | 0.64 | −1.41 | 0.99 | −1.63 | 0.60 | ST13P21 | −0.11 | −0.61 | 0.97 | −0.09 | −0.25 |
| PGAM1P3 | −1.86 | 1.95 | 1.84 | −0.36 | 1.07 | SNRPGP5 | 0.36 | 0.09 | 0.21 | −0.01 | −0.51 | LINC01892 | 0.26 | −0.49 | −0.44 | −0.03 | −2.40 |
| PPARGC1B | 0.31 | −0.18 | −0.46 | 0.28 | 0.25 | BMS1P19 | −0.68 | 0.73 | 1.02 | 0.98 | 0.72 | AP003097.2 | −0.12 | −1.20 | −0.62 | −0.01 | −1.33 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| RNU6-469P | 1.61 | −1.16 | −1.73 | −0.45 | −0.18 | CCDC62 | −0.14 | −0.23 | 0.04 | 0.10 | 0.28 | AC073254.1 | −0.01 | −0.06 | 0.57 | −0.10 | 0.38 |
| RERGL | −0.71 | 0.49 | 0.96 | 1.66 | 0.05 | MTCYBP40 | −0.45 | −0.30 | 0.40 | −0.95 | 0.28 | AC005040.1 | 0.25 | 0.10 | −1.82 | 0.55 | −1.51 |
| IFIT1P1 | 0.76 | −1.23 | −1.31 | −0.71 | −0.44 | AC004034.1 | 0.28 | −0.27 | −0.62 | −0.07 | −0.24 | AC090791.1 | 0.09 | −0.43 | −1.25 | 1.64 | −1.32 |
| CEP192 | 0.20 | −0.18 | −0.12 | −0.10 | 0.04 | RN7SL79P | −0.95 | 0.01 | −0.26 | 0.96 | −0.65 | RNU6-927P | 0.20 | 0.73 | 0.34 | 0.50 | 0.40 |
| RN7SKP217 | −0.58 | 0.19 | −0.25 | 0.43 | 0.17 | KRT8P19 | −0.80 | 0.80 | −0.54 | 1.19 | −0.33 | CACNA1C-AS2 | −0.02 | 0.20 | 1.29 | −0.31 | 0.24 |
| RLF | 0.24 | 0.00 | −0.02 | −0.12 | −0.27 | SNAPC5 | 0.07 | −0.05 | −0.19 | 0.03 | −0.12 | AL355974.3 | 0.26 | −1.21 | −0.08 | −0.64 | −1.54 |
| PGBD1 | −0.32 | −0.05 | 0.22 | 0.18 | 0.27 | AC021733.1 | −0.72 | −0.42 | −1.82 | 0.86 | 0.55 | AC011290.2 | 0.02 | −0.40 | −0.01 | 0.34 | 0.32 |
| SCARNA7 | −0.35 | 0.69 | 0.51 | 0.22 | −0.09 | RPL7AP26 | 0.34 | −0.33 | −0.08 | 0.67 | 0.94 | AP000820.1 | −0.10 | −1.43 | −0.52 | −0.09 | 0.08 |
| JAM2 | −0.46 | 0.41 | 1.47 | −0.05 | 0.36 | AL390961.2 | −0.30 | −0.86 | −0.29 | 0.66 | 0.52 | RAB20 | −0.02 | −0.07 | −0.45 | −0.16 | −0.28 |
| HAPLN3 | 0.54 | −0.74 | −1.12 | −0.31 | −0.58 | RNU2-42P | 0.41 | −1.32 | −0.61 | 0.03 | −0.69 | AP002761.1 | 0.09 | −0.93 | −0.10 | −0.22 | −0.30 |
| ETDC | 1.06 | −1.23 | −0.98 | −0.34 | −0.36 | AC007298.1 | 0.45 | −0.54 | 0.19 | −0.52 | −0.11 | C17orf107 | 0.02 | −0.22 | −0.87 | 0.13 | 0.00 |
| AC007610.2 | 1.19 | −0.39 | −0.54 | 0.10 | −0.06 | AC107909.1 | 0.30 | 0.41 | −0.14 | −0.26 | 0.06 | AL360295.1 | 0.15 | 0.37 | 0.13 | −0.53 | −1.48 |
| MNX1 | −1.22 | −0.02 | 0.08 | −0.42 | −0.03 | RNU6-188P | 0.52 | −1.77 | 1.55 | −0.58 | 1.08 | AC005021.1 | −0.11 | 0.70 | 1.25 | −1.17 | −0.89 |
| RNU6-144P | −1.24 | 0.53 | −0.02 | 1.77 | −0.34 | SPDYE4 | −0.43 | 0.34 | 0.37 | 0.67 | 1.23 | AP001999.2 | −0.26 | 0.46 | 1.44 | −0.94 | 0.21 |
| KIF26A | −0.58 | 0.41 | 0.71 | 0.47 | 0.24 | AL121782.1 | 0.40 | −1.16 | 0.59 | −0.15 | 0.95 | LINC01683 | 0.26 | −0.67 | 0.02 | −0.41 | −0.83 |
| AC073592.6 | 1.02 | −0.70 | −0.17 | −0.21 | 0.11 | SLC25A5P7 | −0.74 | 0.86 | 1.31 | −1.92 | −1.16 | HNRNPA1P33 | 0.02 | −0.11 | −0.06 | 0.15 | 0.27 |
| SNORD116-19 | −1.62 | 1.26 | 2.53 | −0.43 | 0.82 | RN7SL10P | −0.69 | −0.55 | 0.68 | −0.66 | −0.09 | AC103409.1 | 0.07 | −1.12 | 0.76 | 0.34 | 0.14 |
| AC024597.1 | 2.13 | −0.75 | −0.89 | 0.79 | 0.09 | MIF | −0.34 | 0.40 | −0.25 | 0.36 | −0.77 | HNRNPA1P45 | −0.02 | 0.25 | 0.07 | −0.08 | 0.02 |
| DDX24 | 0.18 | −0.09 | −0.30 | −0.04 | −0.20 | RPL31P58 | 0.29 | −0.50 | −0.12 | −0.19 | 0.42 | AC016820.1 | −0.07 | −0.80 | −1.35 | 0.12 | 0.13 |
| RCC1L | 0.25 | −0.10 | −0.22 | −0.08 | −0.14 | AL928654.2 | 0.26 | −0.35 | −0.20 | −0.10 | 0.81 | RP11-289I10.3 | 0.26 | −0.91 | −0.95 | 1.07 | 0.23 |
| NAALADL2-AS1 | −1.26 | 0.45 | 2.32 | −0.05 | −0.86 | MLLT10P1 | −0.19 | −0.01 | 0.39 | 0.19 | 0.53 | AC063976.3 | 0.26 | 0.30 | 3.11 | −0.43 | 2.00 |
| AL359832.1 | 2.40 | −0.83 | 0.49 | −0.24 | 1.20 | OLAH | −0.45 | −0.97 | 0.83 | −0.34 | 0.44 | AL512383.1 | 0.05 | −0.04 | −0.50 | −0.18 | −0.17 |
| ARHGEF17 | −0.43 | 0.08 | 0.45 | 0.07 | 0.10 | EMSY | 0.06 | 0.01 | −0.04 | −0.20 | −0.15 | RPS4XP12 | −0.09 | 0.04 | 0.54 | 0.80 | 0.32 |
| MYNN | 0.26 | 0.03 | 0.00 | 0.05 | −0.19 | AL157400.2 | −0.96 | −0.58 | 2.28 | −0.80 | 2.53 | AC005909.1 | 0.09 | −0.89 | −1.33 | 0.13 | −1.30 |
| DXO | −0.37 | 0.22 | −0.06 | 0.36 | 0.16 | AC073587.1 | −0.59 | −0.50 | −1.19 | 1.02 | −0.24 | LINC02555 | 0.09 | −0.58 | −2.06 | 1.09 | −1.75 |
| RNU1-59P | 0.80 | −0.31 | −1.75 | −1.84 | −1.01 | LINC01771 | 0.56 | −1.41 | 0.53 | −1.53 | 1.07 | ACYP1 | −0.01 | −0.24 | 0.08 | −0.23 | 0.10 |
| RPL21P123 | 0.65 | −0.59 | −0.04 | −0.42 | 0.56 | GUCY2C | −0.15 | −0.14 | −0.03 | 0.23 | 0.15 | AC106028.2 | 0.04 | 1.11 | −0.08 | −0.01 | −0.27 |
| PASD1 | −1.72 | 0.50 | −1.12 | 0.71 | −0.42 | AC006148.1 | −0.52 | −0.97 | −1.15 | 0.71 | 0.59 | AC104651.2 | 0.10 | −0.06 | 0.78 | 0.04 | −0.27 |
| C20orf197 | −0.63 | −0.45 | 0.29 | −0.02 | 0.61 | G33562 | −0.28 | 0.58 | 0.60 | 0.22 | 0.15 | AC097066.1 | −0.24 | −0.55 | −0.09 | −0.14 | 1.04 |
| EIF3F | 0.26 | 0.02 | −0.05 | −0.01 | −0.21 | RNU7-151P | 0.65 | 0.12 | 0.30 | −0.41 | −0.11 | RNU6-536P | −0.13 | −1.05 | 0.14 | 0.45 | 3.09 |
| FBP1 | −0.89 | 0.23 | 0.33 | 0.90 | 0.97 | IL5RA | −0.29 | 0.22 | 0.28 | 0.24 | −0.20 | LA16c-60G3.6 | 0.26 | −1.14 | −0.61 | −1.49 | 0.23 |
| GPM6A | −0.86 | 0.10 | 0.30 | 0.10 | −0.25 | BX284613.1 | −0.28 | −0.33 | 0.29 | −0.02 | −0.03 | AC112204.3 | 0.18 | −0.44 | −0.70 | 0.57 | −1.12 |
| RN7SKP134 | 1.81 | −0.38 | −2.14 | 0.67 | −1.83 | AC092295.1 | 0.80 | −1.54 | −1.58 | 1.07 | −0.34 | AC093826.1 | −0.25 | −0.12 | −1.47 | 1.32 | −0.96 |
| JAGN1 | 0.34 | −0.08 | −0.39 | 0.03 | −0.44 | AP001043.1 | 0.23 | −0.81 | −1.32 | 0.25 | −0.11 | APOOP4 | 0.16 | −0.88 | 0.16 | 0.06 | 0.05 |
| AC114878.1 | 1.08 | −0.53 | −1.04 | 0.11 | 0.40 | RPL23AP92 | 0.37 | −0.83 | 0.22 | 0.40 | 0.99 | MATN1 | 0.03 | −0.04 | −0.22 | 0.46 | 0.88 |
| AC026402.1 | 1.44 | −0.75 | −1.14 | 0.83 | −0.03 | LGI2 | −0.27 | −0.16 | −0.12 | −0.28 | −0.31 | AC010530.1 | −0.02 | −0.04 | 0.14 | −0.26 | 0.14 |
| FOXP1 | 0.22 | 0.07 | −0.09 | −0.01 | −0.19 | BCO2 | −0.13 | 0.25 | 0.24 | 0.36 | −0.01 | SIGLECL1 | 0.07 | 0.69 | −0.62 | 0.36 | −1.40 |
| AC006042.4 | −1.13 | 1.16 | 2.83 | −0.22 | 0.56 | BICRA-AS1 | 0.26 | −0.01 | 0.67 | −0.11 | 0.35 | BTBD18 | −0.02 | 0.16 | −0.04 | 0.22 | −0.20 |
| FAM183BP | −1.01 | 0.69 | 0.18 | 1.21 | 0.29 | AC016205.1 | 0.19 | −0.29 | −0.38 | −0.34 | −0.28 | EVX2 | −0.06 | 0.54 | −0.58 | −0.17 | −0.12 |
| AL391903.3 | 2.53 | −4.71 | −2.09 | 0.02 | 0.68 | AC022903.1 | −0.57 | −0.21 | 0.99 | −0.68 | −1.07 | NFE4 | −0.03 | −0.50 | −1.50 | 0.69 | −0.04 |
| AC024257.1 | −0.69 | 0.25 | 0.35 | 0.55 | 0.73 | AC079248.1 | −0.53 | −0.65 | −1.19 | 0.50 | −1.33 | AL513479.1 | 0.13 | 0.40 | −0.09 | 2.29 | 0.71 |
| AC004836.1 | −1.59 | 0.54 | 0.26 | 0.30 | −1.01 | ROGDI | 0.15 | 0.10 | −0.04 | 0.30 | 0.10 | AC093904.2 | 0.04 | 0.80 | −0.28 | 0.16 | −1.47 |
| SNORD72 | 2.14 | −1.12 | −0.23 | 0.09 | 0.29 | SLC25A36P1 | −0.73 | 0.76 | 2.05 | −1.26 | −0.44 | AC008555.7 | 0.25 | −0.03 | −0.70 | 0.24 | −0.82 |
| SRRT | −0.40 | 0.04 | −0.22 | 0.22 | 0.11 | GAPDHP54 | −0.48 | −0.49 | 0.82 | 0.45 | 0.50 | LINC00582 | 0.03 | −0.18 | −0.38 | 0.21 | −0.51 |
| AC100858.1 | 1.04 | −0.32 | −0.78 | 0.92 | 1.08 | RIC8B | −0.07 | −0.12 | 0.20 | −0.26 | 0.11 | AC027682.6 | 0.04 | −0.05 | 1.37 | −0.23 | 0.61 |
| RPL5P4 | 0.41 | −0.19 | 0.05 | −0.08 | 0.02 | CD33 | −0.20 | −0.07 | 0.43 | 0.26 | 0.64 | RPS27P26 | −0.25 | 0.26 | −0.11 | −0.84 | −1.94 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| LIPJ | 0.96 | −0.39 | −0.72 | 0.31 | −0.64 | AC107016.1 | 0.88 | −1.44 | −0.37 | −0.80 | −0.51 | AC136777.1 | 0.25 | −0.97 | 0.59 | −1.98 | −0.50 |
| SHISA7 | −0.97 | 0.02 | 0.29 | −0.25 | −0.74 | RASD2 | −0.29 | 0.30 | 1.12 | −0.01 | 0.37 | SRP14P3 | −0.02 | 0.01 | 0.28 | 0.30 | 0.23 |
| RNU6-301P | 1.26 | −0.87 | 0.60 | −0.78 | 0.12 | AC079594.1 | 0.34 | −0.49 | −0.07 | −0.43 | 0.06 | DUX4L31 | −0.15 | −0.48 | −0.73 | 0.44 | −0.76 |
| PREX2 | −0.46 | 0.31 | 1.01 | −0.10 | 0.16 | RPL7AP25 | −0.72 | −0.67 | 1.12 | 1.21 | 0.71 | SAGE2P | 0.07 | −0.48 | −2.03 | −0.60 | −1.73 |
| AC011294.1 | −0.99 | −0.15 | 0.83 | −0.30 | 0.67 | AC104785.1 | −0.42 | 1.28 | 0.78 | 0.78 | 0.35 | AL512310.9 | −0.25 | 0.25 | −0.32 | 0.73 | −0.79 |
| BPIFB9P | −0.68 | 0.03 | 0.07 | 0.40 | 0.24 | MIR4753 | 0.44 | −0.12 | −0.66 | −0.02 | −0.90 | CHST14 | −0.02 | −0.16 | 0.13 | −0.43 | 0.08 |
| AC093334.1 | −1.10 | −0.18 | 1.89 | 0.39 | 0.52 | AC007448.3 | 0.42 | −0.30 | −0.06 | −0.63 | 0.56 | AC068880.5 | −0.14 | −0.68 | 0.72 | 0.29 | 1.32 |
| GAPDHS | −0.72 | 0.99 | 0.42 | 0.50 | −0.21 | FSIP1 | 0.24 | −0.81 | 0.46 | 0.08 | 0.21 | PSMC1P3 | 0.09 | −0.30 | 0.96 | −0.60 | 0.70 |
| AC011451.3 | −1.20 | 0.71 | 1.78 | 0.31 | 0.86 | AC007255.1 | −0.38 | −0.60 | 0.53 | 0.27 | 0.22 | RNU6-1334P | −0.07 | −0.22 | −0.55 | 0.21 | −0.12 |
| ACSM3 | −0.64 | −0.03 | 0.25 | 0.36 | 0.38 | AC007513.1 | 0.89 | −1.57 | −1.34 | −0.96 | −2.40 | AP000916.1 | −0.25 | 1.92 | 1.57 | −0.68 | −1.50 |
| NUDT2 | 0.47 | −0.21 | −0.20 | −0.30 | −0.46 | LINC00114 | 0.62 | −0.59 | −0.82 | −0.81 | −0.92 | SLCO1B3 | −0.09 | 1.78 | 0.37 | 1.43 | −0.19 |
| G2899 | −1.59 | 1.32 | 1.63 | 0.58 | 1.20 | CNN2P1 | 0.35 | −0.16 | −0.52 | 0.19 | −0.56 | POTED | 0.07 | 0.16 | −0.97 | 0.80 | −0.91 |
| ACADVL | −0.28 | −0.02 | −0.20 | 0.05 | 0.02 | AC004584.2 | −0.34 | −1.13 | 1.47 | −0.52 | 1.61 | AC010760.1 | 0.25 | −0.59 | −0.16 | 1.30 | 3.96 |
| NAV2-AS3 | −0.78 | 0.06 | −0.62 | 0.64 | 0.41 | AL139021.2 | 0.44 | 0.35 | 0.48 | −0.12 | −0.41 | AC093809.1 | −0.07 | −1.40 | 1.44 | 0.38 | 1.31 |
| AC009237.8 | −0.69 | 0.33 | 1.10 | −0.34 | 0.47 | RNU6-360P | 0.42 | 0.10 | −0.24 | −0.88 | −0.37 | AC034243.1 | −0.05 | 0.54 | −0.58 | 0.98 | −0.26 |
| RNU2-38P | −1.49 | −0.96 | 1.46 | −0.35 | 1.37 | RN7SL190P | −0.67 | −0.30 | 0.41 | −0.32 | −0.45 | AC010737.1 | −0.10 | 1.86 | −2.59 | 1.48 | −3.08 |
| ACTG1P23 | −2.11 | 1.59 | 0.69 | 1.77 | −0.83 | RPSAP8 | 0.50 | −0.73 | 0.12 | −0.59 | −0.25 | ANKRD60 | 0.10 | −1.15 | −0.43 | −0.86 | −0.18 |
| AC016877.2 | −1.48 | 0.00 | 2.34 | 0.27 | 1.52 | RPS26P52 | 0.48 | −2.34 | −0.18 | −0.41 | 1.26 | RN7SL703P | −0.18 | 0.45 | −0.67 | 0.59 | −2.25 |
| AP004247.2 | −1.06 | −0.04 | 0.65 | −0.04 | 0.23 | MIR4642 | 0.63 | −0.36 | −1.03 | −0.44 | −0.86 | ESPNL | −0.02 | 0.03 | −2.02 | 0.41 | −1.44 |
| G4573 | −0.91 | 1.17 | 0.38 | 0.05 | −0.02 | KHDC3L | −0.82 | −0.93 | 0.79 | −0.08 | 2.00 | AL354719.1 | 0.10 | −1.56 | 0.23 | 1.44 | 1.29 |
| RNA5SP151 | 0.77 | 0.12 | −1.05 | −0.66 | −0.51 | AL158829.1 | −0.63 | 0.01 | 0.73 | −0.02 | 0.52 | MTCO1P8 | −0.08 | −0.45 | −0.74 | 1.05 | 0.75 |
| HSD17B8 | −0.34 | 0.47 | 0.26 | 0.48 | 0.39 | AC117394.1 | −1.03 | 0.18 | −0.71 | 0.75 | −1.52 | OR10D4P | 0.18 | 0.51 | −1.50 | 1.06 | −1.80 |
| AP001434.1 | 2.13 | −0.99 | −2.42 | −0.78 | 0.58 | AC034207.1 | −0.23 | 0.02 | 0.35 | −0.04 | 0.01 | AC090213.1 | −0.03 | −0.66 | 1.01 | −1.31 | 0.38 |
| MROH6 | 0.51 | −0.22 | −0.46 | −0.06 | 0.06 | KNOP1 | 0.09 | −0.16 | −0.36 | 0.02 | −0.03 | AC019084.1 | −0.10 | 0.80 | −0.13 | −0.19 | −2.67 |
| ARID2 | 0.20 | 0.04 | −0.11 | 0.02 | −0.09 | OR2K2 | 0.75 | −1.90 | −0.42 | −0.43 | −0.20 | OR7E1P | 0.10 | 1.05 | −0.96 | −0.09 | −1.65 |
| KCTD4 | 0.48 | −0.12 | −0.03 | 0.02 | −0.11 | SNX8 | −0.10 | 0.04 | −0.30 | −0.04 | −0.21 | ROBO4 | −0.02 | −0.14 | 0.38 | −0.08 | 0.08 |
| LYPLAL1-DT | −0.99 | −0.19 | −0.91 | −0.07 | 0.14 | G2196 | 0.67 | 0.15 | 1.28 | −0.05 | 0.78 | AP005019.1 | −0.04 | −0.53 | 0.19 | −0.40 | 0.30 |
| MARVELD3 | 0.38 | −0.15 | −0.86 | −0.07 | −0.19 | AP000640.1 | −0.18 | 0.27 | 0.36 | 0.04 | −0.35 | AL365400.1 | −0.25 | −0.97 | −0.92 | 0.26 | −0.31 |
| KIF6 | −0.74 | 0.11 | 0.16 | 0.03 | −0.35 | LINC-ROR | −0.43 | −0.25 | −0.12 | 0.68 | −0.98 | LINC01545 | 0.03 | 0.41 | 0.87 | 0.51 | −0.11 |
| AL162724.1 | 0.90 | −0.22 | −1.46 | −0.24 | −0.76 | NCAN | 0.46 | −0.88 | −0.63 | 0.65 | 0.25 | GLRX2 | 0.01 | 0.25 | 0.31 | 0.02 | 0.00 |
| RNU6-331P | 0.74 | −0.20 | −0.57 | 0.03 | 0.19 | AC008163.1 | −0.29 | −0.54 | 0.06 | −0.32 | 0.07 | AC083822.1 | −0.04 | −0.25 | −0.48 | 0.18 | −0.50 |
| AC090578.1 | −0.89 | 0.92 | 1.26 | 0.34 | −0.10 | HMGN2P16 | −0.63 | −0.12 | 1.07 | 0.09 | 0.73 | OR2V2 | −0.05 | −1.90 | −1.52 | −0.12 | −0.77 |
| RN7SL735P | 0.77 | −0.89 | −0.81 | −0.72 | −0.57 | AL159972.1 | −0.56 | −0.22 | 0.55 | −1.69 | −0.73 | AC242988.1 | 0.08 | −1.43 | 0.93 | −0.94 | 0.93 |
| RNU1-3 | −0.92 | 0.72 | 0.12 | 1.02 | −0.11 | AC131888.1 | −0.32 | −0.79 | 0.50 | −0.69 | 0.77 | CTSLP4 | −0.24 | −0.58 | 0.62 | −0.53 | −0.91 |
| E2F6 | 0.24 | −0.23 | −0.06 | −0.09 | −0.04 | IFIT1B | −0.32 | −0.90 | −0.66 | −0.78 | −1.10 | RAP1BP2 | 0.25 | −0.78 | −0.19 | 0.76 | 1.12 |
| DYRK4 | 0.23 | −0.10 | −0.14 | 0.00 | −0.06 | RNU6-846P | 0.29 | −0.10 | −0.05 | −0.20 | −0.60 | MIR4737 | −0.07 | 0.14 | 0.80 | −0.37 | 0.62 |
| NWD1 | −0.83 | −0.15 | 0.64 | 0.53 | 0.36 | LDLRAP1 | 0.09 | −0.04 | −0.35 | 0.15 | 0.02 | AC069280.1 | −0.25 | −0.21 | −0.72 | 2.07 | −0.35 |
| LMO7 | −0.40 | 0.07 | 0.39 | −0.07 | −0.07 | ANXA8L2 | −0.13 | 0.05 | −0.89 | 0.31 | 0.09 | IMMP1L | −0.01 | −0.22 | 0.15 | −0.13 | 0.16 |
| BRD7P2 | 0.66 | 0.09 | −0.60 | −0.07 | −0.55 | SAMD3 | 0.27 | −0.29 | 0.66 | −0.38 | 0.16 | RPL21P99 | −0.03 | 0.11 | −0.38 | −0.21 | −0.31 |
| AC023509.4 | −0.73 | 0.84 | 0.77 | −0.11 | −0.64 | GCLM | 0.15 | −0.19 | −0.29 | −0.28 | 0.05 | AC091965.2 | 0.17 | 0.37 | −0.08 | 0.23 | 1.40 |
| AL591721.1 | −0.89 | 0.84 | 0.84 | 0.26 | −0.03 | AC006504.5 | 0.09 | −0.13 | 0.01 | −0.15 | 0.20 | EI24P4 | 0.10 | −1.11 | 0.59 | −0.32 | 0.27 |
| ISCA1 | 0.32 | −0.09 | −0.24 | −0.15 | −0.52 | AADACL4 | −0.59 | 0.71 | 0.41 | 0.64 | 0.17 | IGKV1OR10-1 | −0.09 | 0.13 | −1.86 | 1.12 | −0.85 |
| S100PBP | −0.16 | −0.08 | 0.09 | 0.01 | 0.18 | AL512422.1 | 0.43 | −0.98 | −1.41 | −0.03 | −0.16 | OR1G1 | −0.25 | 0.49 | −1.62 | 1.82 | 0.40 |
| AARS2 | −0.30 | 0.07 | 0.02 | 0.10 | 0.16 | PRPSAP1 | −0.07 | 0.10 | 0.35 | −0.16 | 0.03 | RBAKDN | 0.25 | 0.14 | −1.35 | 1.88 | 0.69 |
| CYP2D8P | −0.61 | −0.17 | −0.15 | 0.40 | 0.58 | AC119424.1 | −0.43 | 0.43 | 1.29 | 0.40 | −0.29 | ADIG | −0.08 | −0.27 | −1.23 | −0.64 | −2.01 |
| RALGAPA1P1 | 0.25 | −0.15 | −0.40 | 0.03 | 0.00 | RN7SL121P | 0.76 | −0.77 | −0.80 | −0.38 | −2.02 | NANOS2 | 0.24 | −0.76 | −2.11 | −0.13 | −1.04 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| G43427 | −1.23 | 1.28 | −1.73 | 0.86 | −1.54 | OR2T32P | −0.86 | −1.16 | 0.96 | 0.01 | 0.89 | OR13Z1P | −0.15 | −0.75 | 1.16 | 1.50 | 1.95 |
| AC073862.3 | −1.16 | 1.39 | 1.76 | −0.19 | −0.50 | AL137059.1 | 0.26 | 0.10 | 0.23 | 0.46 | 0.33 | AC011443.1 | 0.03 | 0.17 | 0.74 | 0.22 | 0.13 |
| AC079061.1 | −0.78 | 0.60 | 0.50 | 0.20 | 0.14 | AC009464.1 | 0.36 | −0.44 | −0.20 | 0.14 | 0.63 | AC005828.3 | −0.07 | 0.17 | 0.64 | 0.00 | 0.30 |
| RPL31P61 | −1.35 | 0.07 | 1.35 | −0.72 | 0.07 | HOXB6 | −0.23 | −0.67 | 0.87 | 0.36 | 0.82 | AC023469.2 | −0.09 | −0.79 | −0.45 | 0.65 | 0.28 |
| DDX50P2 | −1.45 | 1.88 | 1.58 | 1.41 | 0.14 | MTND5P14 | 0.20 | −0.22 | 0.67 | −0.27 | 0.27 | AC087311.1 | −0.25 | 0.16 | 0.45 | −1.63 | −1.11 |
| RBMXL2 | −1.15 | 0.52 | 0.14 | 0.06 | −0.19 | BLVRB | −0.09 | 0.08 | −0.13 | 0.14 | −0.21 | AC105343.1 | 0.25 | −0.21 | 0.29 | 0.20 | 0.93 |
| MTND2P5 | −0.77 | 0.46 | 0.98 | −0.48 | −0.41 | AC008481.1 | 0.24 | −0.70 | −0.80 | −0.14 | 0.18 | BMS1P3 | 0.07 | 1.33 | 0.42 | 0.80 | −0.43 |
| PTPN11 | 0.33 | −0.10 | −0.25 | −0.07 | −0.26 | COX6A1P2 | 0.26 | 0.57 | −0.36 | 0.00 | −1.73 | ITM2C | 0.01 | −0.10 | 0.09 | −0.10 | 0.04 |
| P2RY12 | −0.89 | 0.41 | −0.14 | 0.15 | 0.01 | JCAD | −0.16 | 0.13 | 0.82 | −0.21 | 0.04 | AL117372.1 | 0.22 | −0.74 | −1.01 | 0.61 | −0.51 |
| MTRNR2L8 | −0.58 | 0.31 | −0.04 | 0.88 | −0.16 | AL021578.1 | −0.29 | 0.66 | −0.07 | −0.01 | −0.88 | GAPDHP36 | 0.08 | 0.59 | 0.32 | −0.50 | −1.45 |
| AC022113.2 | −1.39 | −0.32 | 1.28 | 0.93 | 0.08 | AC004477.1 | −0.19 | −0.06 | −0.17 | 0.00 | −0.08 | AC097487.1 | −0.13 | 0.20 | −1.46 | −0.08 | −1.34 |
| NRON | 1.51 | 0.34 | 0.34 | 1.30 | 1.11 | AC091390.4 | 0.68 | −0.81 | 0.35 | 0.75 | 1.69 | OR9A1P | −0.16 | 1.87 | −0.10 | 0.01 | −1.23 |
| AC106795.2 | −0.57 | 0.02 | 0.43 | 0.41 | 0.92 | IP6K3 | −0.42 | 0.46 | 1.58 | 0.06 | 0.36 | AC084364.2 | 0.25 | −0.38 | −1.14 | 0.55 | −0.72 |
| G22923 | 2.36 | 0.27 | −0.52 | −0.27 | −0.12 | LINC01821 | 0.59 | −0.43 | −1.39 | −0.14 | −1.91 | PTCHD3P3 | −0.10 | 0.86 | 0.80 | 0.46 | 0.10 |
| G11966 | −0.81 | 0.38 | 1.41 | −0.04 | 0.41 | G33852 | −0.27 | −0.17 | 0.45 | −0.58 | 0.15 | KRTAP4-5 | −0.25 | 0.72 | 1.32 | 0.82 | −3.41 |
| PDIA5 | 0.25 | −0.24 | 0.09 | −0.49 | 0.02 | G14802 | 0.32 | −0.16 | −0.48 | −0.30 | 0.04 | RPSAP27 | −0.25 | −0.31 | −0.71 | 1.00 | −1.53 |
| PDK3 | −0.49 | 0.67 | 1.08 | 0.19 | 0.63 | AC104389.2 | −0.90 | −0.28 | −0.62 | 0.48 | −1.17 | LINC01739 | −0.06 | −0.90 | −0.68 | 1.14 | 1.10 |
| MYB | −0.44 | 0.50 | 0.53 | 0.40 | 0.18 | BAG4 | 0.07 | 0.04 | −0.02 | 0.05 | 0.03 | AC087672.1 | −0.07 | 0.85 | −0.34 | 0.51 | −1.79 |
| ARSB | 0.41 | −0.40 | −0.45 | −0.26 | −0.46 | AC104472.3 | −0.59 | 0.15 | 0.90 | −0.84 | −0.47 | AC106791.2 | −0.08 | −1.18 | −0.84 | 0.14 | 0.41 |
| GPC5 | −0.87 | 0.09 | 0.12 | 0.12 | 0.17 | RNU6-267P | 0.37 | −0.54 | 1.54 | −0.11 | 0.52 | CTSLP6 | 0.12 | −1.65 | −2.37 | −0.09 | 3.47 |
| AC074011.1 | −0.84 | −0.29 | 1.28 | 0.04 | 1.38 | SLC44A5 | 0.21 | 0.55 | 0.06 | 0.50 | 0.20 | AL109918.3 | −0.05 | 0.67 | −0.81 | 1.18 | −0.22 |
| AC007179.2 | −1.01 | 0.33 | −0.93 | 1.26 | −0.89 | ITGAM | −0.20 | −0.15 | 0.54 | −0.17 | 0.09 | RNU6-1015P | −0.24 | −0.19 | 0.53 | −1.44 | −0.67 |
| G32150 | 0.59 | −0.09 | −0.25 | 0.14 | −0.33 | RAP1GAP2 | 0.13 | −0.07 | −0.19 | 0.00 | 0.18 | OR7E10P | 0.14 | 1.32 | −2.51 | 1.48 | −1.98 |
| GLI4 | −0.40 | 0.29 | −0.13 | 0.42 | 0.14 | RPL30P13 | −0.41 | −0.24 | −0.33 | −0.11 | 0.00 | EEF1A1P37 | −0.24 | −0.58 | 1.60 | −0.43 | 1.66 |
| CAMKV | −1.00 | −0.02 | 0.21 | 0.19 | −0.90 | AC134349.2 | −0.14 | −0.26 | 0.51 | 0.17 | 0.23 | CHRNA1 | 0.03 | −1.03 | −0.67 | 0.51 | 0.75 |
| BANF1P3 | 0.68 | −0.47 | −0.71 | −0.36 | −0.02 | HSPD1P2 | 1.38 | −1.68 | −2.03 | 0.58 | −2.27 | AC087257.1 | 0.01 | −0.16 | 0.21 | −0.23 | 0.44 |
| PIPOX | −0.49 | 0.30 | 0.25 | 0.32 | 0.08 | AC106047.2 | 0.26 | −0.25 | 0.03 | 0.25 | 0.53 | AP000949.1 | −0.24 | 0.54 | −0.34 | 0.25 | −0.21 |
| AL391117.1 | −1.14 | 0.55 | 0.22 | 0.31 | −0.35 | 6-Sep | −0.15 | −0.24 | 0.32 | −0.24 | 0.31 | KAZN-AS1 | 0.02 | 0.15 | 0.96 | −0.42 | 0.17 |
| STX5 | −0.14 | 0.15 | −0.16 | 0.09 | −0.25 | AL121936.2 | −0.77 | 0.88 | 0.71 | 0.57 | −0.18 | G38698 | 0.03 | −0.57 | −0.14 | −0.22 | 0.06 |
| ANP32A | 0.30 | −0.44 | −0.14 | −0.37 | 0.04 | CFAP206 | 0.55 | 0.31 | −0.45 | 0.76 | −1.45 | RNA5SP448 | −0.09 | −0.35 | 0.35 | −0.35 | 0.35 |
| RNA5SP242 | −1.06 | 0.54 | −0.32 | 0.95 | −0.52 | G28030 | −0.72 | 0.97 | 1.21 | −1.23 | 0.05 | NDUFB4P4 | 0.24 | −0.44 | 0.11 | −0.97 | −1.24 |
| AC007424.1 | −1.32 | 0.49 | −0.86 | 0.95 | −0.20 | AC092670.1 | 0.59 | −0.92 | 0.97 | 0.63 | 1.34 | AL353600.1 | −0.11 | −0.01 | −0.89 | 0.01 | 0.60 |
| DBR1 | 0.30 | −0.09 | −0.29 | −0.10 | −0.23 | LINCO2100 | −0.71 | −1.66 | −1.36 | −0.13 | 0.25 | RPS20P24 | −0.06 | 0.78 | −0.89 | −0.21 | −1.06 |
| AC130651.1 | −0.60 | 0.73 | 0.04 | 0.42 | −0.29 | AC020663.1 | −0.45 | −0.67 | 1.23 | −0.40 | 0.35 | AC021028.1 | 0.04 | −0.31 | −0.71 | 0.10 | −0.49 |
| AL078599.2 | −0.52 | 0.46 | 0.71 | 0.18 | 0.17 | RAG1 | −0.23 | −0.03 | −0.30 | −0.03 | 0.03 | RGPD2 | −0.02 | 0.16 | −0.75 | −0.12 | 0.18 |
| AC087645.2 | 1.06 | −1.81 | −1.92 | −0.23 | 0.17 | CMTM4 | −0.10 | 0.29 | 0.14 | 0.10 | 0.00 | AL590764.1 | 0.03 | −0.27 | −0.23 | −0.35 | 0.06 |
| AC137936.2 | 1.30 | −1.82 | −1.49 | −0.80 | −1.13 | AL139811.1 | −0.12 | −0.15 | −0.07 | −0.05 | 0.15 | RN7SL263P | 0.03 | −0.16 | −0.83 | −0.30 | −0.38 |
| CRB3 | 0.63 | 0.29 | −0.24 | 0.02 | −0.68 | FAM71F1 | −0.36 | 0.36 | −0.66 | 0.49 | −0.39 | GACAT3 | −0.10 | 0.30 | −0.66 | 0.41 | −1.78 |
| AP003680.1 | −1.08 | 0.78 | −0.38 | 1.10 | 0.05 | AC073648.5 | −0.87 | 0.80 | 2.20 | 0.37 | 0.22 | RNU6-726P | −0.08 | −1.50 | 1.47 | −0.11 | 0.93 |
| FXYD7 | −0.71 | −0.02 | −0.31 | 0.34 | 0.10 | SMG1P2 | 0.16 | −0.25 | 0.04 | −0.12 | 0.33 | AP003057.1 | −0.11 | −0.78 | 0.47 | −0.85 | 0.44 |
| AC103726.2 | −1.50 | −0.21 | 2.29 | −0.01 | 2.30 | G24769 | 0.63 | −1.07 | −1.51 | 1.57 | 1.13 | LINC01758 | 0.24 | −0.02 | −0.27 | 2.17 | −0.43 |
| HOXB2 | −0.61 | 0.07 | 0.95 | −0.01 | −0.01 | AC009570.1 | −0.62 | 2.11 | −0.46 | 2.15 | −0.33 | MOSPD3 | −0.01 | 0.38 | 0.17 | 0.11 | −0.16 |
| DHH | 0.93 | 0.05 | −0.22 | 0.51 | 0.05 | AC109992.1 | 0.49 | −0.45 | 0.87 | −0.22 | 0.02 | AC092818.1 | −0.06 | −0.70 | −1.40 | −2.19 | −1.10 |
| ABHD13 | 0.30 | 0.05 | −0.01 | −0.09 | −0.25 | CR1 | −0.33 | −0.14 | −0.58 | 0.15 | −0.39 | DMRT1 | −0.06 | −1.15 | 0.08 | −1.04 | −0.08 |
| CCDC88A | 0.31 | −0.34 | −0.19 | −0.15 | −0.02 | AL158834.2 | 0.27 | 0.08 | −0.29 | 0.45 | 0.00 | AC093813.1 | 0.15 | −0.67 | 0.42 | −0.88 | 2.93 |
| MAP7D1 | 0.37 | −0.15 | −0.73 | −0.10 | −0.60 | AL138999.1 | −0.40 | 0.99 | −0.21 | −0.07 | −1.82 | AL118496.1 | 0.06 | −1.28 | −1.49 | 0.96 | 1.11 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| OST4 | 0.31 | −0.08 | 0.06 | −0.30 | −0.30 | RPL7P18 | 0.19 | −0.15 | 0.67 | −0.25 | 0.12 | AC007881.1 | 0.03 | −0.20 | −0.09 | 0.09 | 0.05 |
| C19orf47 | −0.26 | 0.20 | −0.09 | 0.11 | 0.07 | AL109910.2 | −1.00 | 0.29 | 0.72 | 1.60 | 0.16 | G26757 | −0.05 | 0.27 | −0.64 | −0.58 | −0.88 |
| NUP43 | −0.16 | −0.03 | 0.12 | −0.07 | 0.11 | AC243654.3 | −0.26 | −0.61 | −1.24 | 0.39 | 0.44 | AC243571.1 | 0.24 | −0.17 | −1.82 | 0.14 | −1.75 |
| AL807752.4 | −1.55 | 0.04 | 1.39 | 0.14 | 2.00 | IL23A | 0.22 | −0.67 | −0.62 | −0.25 | −0.09 | AC067968.2 | −0.24 | −0.22 | 0.27 | 0.21 | 0.26 |
| AC011477.7 | −1.20 | 1.46 | 1.90 | −0.08 | 0.25 | SEPT14P4 | 0.34 | 0.03 | −0.29 | −0.32 | −0.37 | AP005233.1 | −0.17 | 1.17 | −0.88 | −1.14 | −2.21 |
| FKBP9P1 | −0.50 | 0.04 | −0.19 | −0.43 | −0.60 | C5orf56 | −0.13 | −0.17 | −0.17 | −0.10 | 0.14 | GOLGA2P9 | 0.06 | −1.33 | −0.43 | −1.07 | −0.51 |
| RPL23AP30 | 0.93 | −0.46 | −0.58 | 0.15 | 0.02 | AL096828.3 | 0.80 | −0.99 | −0.05 | 1.33 | 2.16 | AC010547.3 | −0.13 | −0.01 | −0.36 | −1.04 | 0.22 |
| LGALS9 | 0.44 | −0.56 | −0.10 | −0.40 | −0.03 | LINC00691 | −0.22 | −0.16 | −0.01 | 0.72 | 0.82 | PABPC1P11 | 0.08 | −0.42 | −1.80 | −0.57 | −1.07 |
| AC136603.1 | −0.56 | 0.59 | 0.02 | 0.28 | −0.21 | SMIM2-IT1 | −0.73 | 1.21 | −0.83 | 1.10 | −2.12 | AL583859.2 | −0.24 | 0.74 | 0.91 | −0.22 | 0.57 |
| RNA5SP393 | 1.23 | −1.25 | −1.01 | −0.91 | −0.19 | SMCO3 | −0.35 | 0.02 | 0.53 | 0.49 | 0.01 | AC138466.4 | 0.24 | −1.04 | −0.79 | 0.84 | 0.43 |
| KDM6A | 0.20 | 0.04 | −0.11 | 0.11 | −0.08 | AC112721.1 | 1.20 | −0.59 | −1.63 | −0.30 | −0.18 | AC026462.3 | 0.09 | −1.68 | 2.39 | 1.24 | 4.03 |
| AL031728.1 | −0.60 | −0.02 | 0.65 | 0.01 | 0.26 | ARL14EP | 0.08 | −0.01 | 0.20 | −0.03 | 0.05 | KDM2A | −0.01 | −0.03 | −0.24 | 0.06 | −0.02 |
| AL035071.1 | 0.33 | 0.08 | −0.50 | 0.05 | −0.38 | SNORD3B-2 | −0.28 | −0.26 | −1.03 | 0.23 | −1.11 | SMG9 | −0.01 | −0.22 | −0.45 | −0.08 | 0.08 |
| RNU6-3P | −0.70 | 0.93 | 0.45 | 0.18 | −0.77 | CDK16 | 0.08 | −0.15 | −0.45 | 0.02 | −0.06 | C1orf194 | 0.01 | −0.73 | −0.45 | −0.02 | 0.01 |
| AC092656.1 | −0.76 | 0.41 | 0.69 | 0.12 | 0.30 | AL591222.1 | −0.69 | 0.28 | 1.27 | 0.29 | 0.44 | AC008571.1 | 0.24 | 0.19 | −0.43 | −0.10 | 1.26 |
| AL161908.1 | −0.84 | 0.58 | −0.49 | 0.06 | −0.01 | AP002833.3 | −0.43 | −0.34 | −0.47 | 0.64 | −0.84 | AC100767.2 | 0.17 | −1.23 | −0.15 | −0.36 | 1.52 |
| AL008726.1 | 1.05 | −0.12 | −0.87 | 0.54 | −0.63 | LINC00920 | 0.20 | 0.15 | 0.31 | −0.07 | −0.14 | PTPN3 | −0.01 | 0.22 | 0.16 | 0.21 | 0.03 |
| AC099811.5 | −0.34 | 0.27 | 0.46 | 0.17 | 0.06 | RN7SL210P | −0.63 | −0.76 | −1.26 | −0.32 | −0.62 | OSBPL9P3 | −0.24 | −0.44 | −0.46 | 1.32 | 1.58 |
| G24964 | −1.35 | 0.56 | 1.86 | 0.28 | 0.76 | SMG6-IT1 | 0.27 | 0.00 | −0.23 | −0.37 | −0.21 | LEUTX | −0.24 | −0.02 | −0.26 | −0.32 | −1.38 |
| B3GALT4 | −0.34 | 0.32 | −0.06 | 0.31 | −0.22 | RN7SL821P | −0.30 | 0.19 | −0.63 | 0.13 | −0.91 | G35839 | 0.04 | −1.55 | −1.06 | −0.83 | −1.74 |
| MVP | 0.29 | −0.43 | −0.78 | 0.00 | −0.18 | SNORD127 | −0.23 | −0.06 | 0.43 | −0.03 | −0.31 | AL049748.1 | −0.14 | −1.30 | 0.25 | −1.60 | 0.35 |
| RNA5SP245 | −1.49 | 0.62 | 0.13 | 1.43 | −0.33 | AC016866.1 | 0.19 | 0.24 | −0.20 | 0.12 | 0.19 | AL929410.1 | 0.24 | −0.25 | −0.05 | 0.99 | 0.49 |
| AL136968.1 | −1.18 | 0.89 | 0.47 | 0.14 | 0.03 | FLJ21408 | −0.19 | −0.41 | 0.16 | 0.09 | −0.03 | OR2AD1P | 0.24 | −0.10 | −0.12 | −0.79 | −1.37 |
| AC012066.1 | 0.60 | −0.45 | −1.15 | 0.13 | −0.17 | HNRNPDP1 | −0.48 | −0.05 | 0.11 | 0.60 | 0.92 | CTRB2 | −0.08 | −1.37 | 1.76 | −0.45 | 1.00 |
| RNU6-1188P | 0.59 | −0.23 | 0.13 | −0.13 | 0.31 | RPS15AP1 | 0.27 | 0.11 | −0.19 | 0.19 | −0.19 | AC005066.1 | −0.16 | 0.01 | 0.93 | −1.06 | 0.02 |
| SOWAHA | −1.23 | −0.18 | 0.89 | 0.59 | 1.51 | OR4K5 | −0.74 | −0.05 | 0.09 | −0.30 | −1.43 | AK4P6 | 0.12 | 0.20 | −1.12 | 1.61 | −1.69 |
| AC136475.10 | 0.61 | −0.14 | 0.43 | −0.09 | −0.11 | AP000911.1 | −0.19 | 0.14 | −0.41 | 0.01 | −0.60 | RN7SL393P | 0.05 | −0.11 | −0.41 | −0.04 | −0.43 |
| AL390728.6 | 0.57 | −0.21 | 0.01 | 0.15 | 0.29 | RNU6-314P | 0.43 | 0.43 | 0.30 | 0.14 | −0.27 | AC008759.1 | −0.24 | −0.92 | −0.01 | 0.28 | 0.78 |
| AC105233.1 | −1.48 | 0.25 | 2.69 | 1.25 | 1.04 | PEX5L | −0.27 | −0.17 | 0.38 | 0.28 | 0.76 | SH3BGR | −0.04 | −0.31 | 0.27 | −0.22 | −0.33 |
| CXCR5 | −1.64 | −0.20 | 2.51 | −0.21 | 1.26 | DPPA2 | −0.74 | −0.38 | −1.83 | 0.21 | −2.57 | GAPDHP42 | −0.02 | −0.07 | 0.74 | 0.42 | 0.67 |
| PEX11B | 0.31 | 0.02 | −0.16 | 0.10 | 0.04 | GJB1 | −0.32 | 0.96 | 1.14 | 0.90 | 0.50 | LINC01424 | 0.03 | −0.06 | 0.43 | −0.22 | 0.29 |
| STAM-AS1 | 0.81 | −0.92 | −0.05 | −0.83 | −0.41 | AC025040.1 | −0.37 | −0.02 | −0.64 | −0.63 | −1.01 | AC138024.1 | 0.11 | 0.35 | 0.49 | 0.85 | −0.28 |
| NPC2 | 0.32 | −0.02 | −0.17 | −0.15 | −0.44 | EDC3 | 0.11 | −0.02 | −0.05 | −0.13 | 0.00 | AL121904.1 | 0.08 | −1.60 | −1.20 | 1.41 | −0.15 |
| ALMS1-IT1 | −0.33 | −0.05 | 0.22 | −0.07 | 0.30 | FAM3C | 0.10 | −0.05 | 0.10 | −0.13 | −0.03 | OR4U1P | −0.24 | 0.89 | 0.47 | 1.04 | 1.04 |
| AL137779.2 | −0.71 | 0.63 | 0.14 | 0.18 | −0.54 | AC097358.1 | −0.56 | 0.64 | −0.01 | 0.20 | −0.98 | RPS6P20 | 0.24 | 0.04 | −0.47 | −1.54 | −1.52 |
| RHOT1P2 | −1.30 | 0.45 | 0.27 | −0.23 | −1.57 | G19426 | 0.17 | −0.02 | −0.13 | −0.02 | −0.06 | HNRNPA1P52 | 0.04 | 0.39 | −0.71 | 0.22 | −0.91 |
| CCDC142 | −0.35 | −0.09 | 0.45 | −0.12 | 0.20 | AL049874.1 | −1.07 | −1.10 | −0.17 | −1.40 | −0.52 | AC104237.2 | 0.05 | 0.89 | 2.76 | 0.20 | 0.76 |
| ANKMY2 | −0.25 | 0.33 | 0.13 | 0.30 | 0.01 | PLPBP | 0.12 | −0.11 | 0.25 | −0.23 | 0.05 | AC134698.1 | 0.24 | 0.55 | −0.69 | 0.40 | −1.62 |
| RGS1 | 1.00 | −1.64 | −1.45 | −0.84 | −0.70 | AC137770.1 | −0.52 | −0.37 | 2.93 | 0.27 | 1.60 | AC010333.3 | −0.14 | −0.83 | 0.52 | 1.09 | 0.75 |
| NACA3P | 0.65 | −0.34 | −0.58 | 0.90 | 0.06 | IFT52 | −0.09 | 0.25 | 0.31 | 0.03 | −0.14 | AC092958.3 | −0.24 | −0.74 | −0.28 | 0.78 | 0.55 |
| GNAS | 0.21 | −0.06 | −0.28 | −0.01 | −0.24 | AC115619.1 | −0.66 | −0.39 | 0.70 | 0.82 | −0.05 | BRD7P1 | 0.13 | 1.37 | 1.05 | −0.14 | −1.66 |
| CALHM5 | −0.67 | 0.28 | 1.09 | −0.39 | 0.09 | AC021097.3 | −0.33 | −0.01 | 1.15 | 0.08 | 0.46 | CMTM1 | −0.02 | −0.42 | −0.26 | −0.13 | 0.09 |
| MKRN7P | −1.25 | −0.07 | 0.54 | 0.32 | 0.70 | C3orf58 | 0.12 | 0.15 | 0.26 | 0.03 | −0.06 | AC068276.1 | −0.24 | 1.82 | 1.99 | −0.19 | −1.77 |
| AL138963.2 | 0.92 | 0.36 | −0.62 | −0.07 | −0.68 | SAP30L | −0.08 | 0.18 | 0.13 | 0.10 | −0.01 | AP001476.1 | 0.04 | −0.64 | −1.34 | 0.82 | 0.33 |
| CHMP5 | 0.31 | −0.19 | −0.27 | −0.19 | −0.31 | PEX26 | −0.06 | −0.14 | −0.15 | 0.04 | 0.06 | ALPG | 0.20 | 0.30 | −0.05 | −0.10 | −0.97 |
| AKAP13 | −0.18 | 0.13 | 0.18 | −0.10 | −0.09 | AEBP1 | −0.16 | 0.12 | 0.83 | −0.62 | −0.14 | AP001960.1 | 0.07 | −1.35 | −1.12 | 0.41 | −0.74 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| EXOC3L4 | −0.90 | −0.24 | −0.02 | 0.02 | −0.17 | AL135838.1 | 0.22 | 0.30 | −0.07 | 0.05 | −0.56 | MRPL42P3 | 0.24 | −0.61 | −0.49 | 0.40 | −0.37 |
| EFHB | −0.63 | 0.39 | 1.69 | 0.43 | 0.46 | SRD5A3-AS1 | −0.11 | −0.21 | −0.02 | 0.11 | 0.35 | AC087463.4 | 0.14 | −0.11 | 1.41 | −0.76 | 0.80 |
| AF067845.5 | 1.63 | −1.16 | −0.49 | −0.63 | 1.47 | LBX2 | −0.18 | 0.51 | 0.08 | 0.19 | −0.01 | CAMTA1-IT1 | −0.05 | 0.00 | −0.05 | 0.37 | 0.73 |
| RN7SL450P | −1.47 | 0.44 | 1.85 | 0.76 | 1.77 | MT-TI | −0.34 | −0.07 | −0.02 | 0.72 | −0.50 | AC091951.4 | 0.12 | −1.18 | 0.75 | −0.88 | 1.70 |
| LTB | 0.83 | −1.14 | −0.01 | −0.84 | 0.39 | CPEB3_ribozyme | 0.27 | 0.91 | 1.25 | 0.48 | 0.33 | AL512624.2 | −0.24 | 0.07 | −1.58 | 1.69 | −1.09 |
| HTR6 | −1.13 | 0.33 | 2.12 | −0.88 | 0.52 | RPS4XP2 | 0.69 | −0.41 | −1.52 | −0.66 | −0.96 | AC021171.2 | 0.02 | −0.41 | 0.21 | 0.12 | 0.51 |
| AC008543.4 | −1.08 | 0.24 | 0.59 | 0.74 | 1.33 | NID1 | 0.18 | −0.04 | 0.27 | −0.54 | −0.50 | LINC01068 | −0.05 | 1.10 | 2.26 | 0.07 | 0.97 |
| PROK1 | −2.04 | 0.09 | 2.17 | 0.45 | 2.33 | PPIAP64 | −0.55 | −0.93 | 1.72 | 0.53 | 1.79 | AC090809.1 | −0.14 | 1.55 | −0.33 | −0.58 | 0.07 |
| AL139246.2 | −1.04 | −0.48 | −0.63 | 0.09 | −0.12 | AC091045.1 | −0.29 | 0.04 | 0.42 | 0.00 | 0.22 | RNU6-1292P | 0.06 | 0.27 | 1.05 | 0.54 | 2.15 |
| CSGALNACT2 | 0.31 | −0.20 | 0.05 | −0.33 | −0.14 | RAX | −0.39 | 0.08 | 0.31 | −0.17 | 0.70 | AC012291.1 | −0.02 | −0.25 | −0.11 | −0.27 | 0.27 |
| AC027682.7 | −0.53 | 0.62 | 0.72 | 0.05 | 0.37 | LINC02188 | −0.30 | −0.21 | 0.64 | −0.11 | 0.69 | L47234.1 | −0.24 | 0.15 | 0.30 | 0.61 | 0.62 |
| AC135178.5 | −0.74 | −0.19 | 0.84 | 0.44 | 0.48 | BET1 | −0.13 | 0.05 | 0.29 | −0.21 | 0.17 | AC007991.1 | 0.14 | −0.62 | −0.23 | −0.80 | 0.20 |
| MED12L | −0.39 | 0.07 | −0.08 | 0.05 | −0.12 | ASLP1 | 0.37 | 0.26 | 1.06 | −0.94 | 0.44 | AC084149.1 | −0.24 | −0.15 | −0.71 | 0.20 | −1.02 |
| CCK | 2.07 | −0.66 | −0.53 | 0.41 | −0.80 | CRAT37 | −0.51 | −0.51 | −0.63 | −1.06 | −1.04 | AC140847.3 | −0.21 | −0.71 | −0.41 | 0.06 | 0.06 |
| PSG7 | −0.75 | 0.36 | 0.49 | 0.05 | −0.35 | G43607 | −0.49 | 0.26 | 0.87 | −0.33 | 0.33 | LINC02189 | −0.08 | −0.03 | 2.07 | −0.05 | 2.76 |
| IGIP | −0.38 | 0.20 | 0.79 | −0.12 | 0.28 | ARAP3 | 0.16 | −0.17 | 0.04 | −0.11 | −0.03 | NF1P12 | −0.24 | −0.71 | 0.26 | 0.33 | 0.39 |
| ABCC6P1 | −1.46 | −0.85 | 0.75 | −1.19 | 0.22 | ITGB5-AS1 | 0.26 | 0.48 | −0.35 | 0.44 | −0.35 | OR51V1 | −0.18 | −1.54 | −0.74 | 0.02 | 0.04 |
| COX7A2L | 0.27 | −0.16 | −0.05 | −0.16 | −0.05 | AC016683.1 | 0.24 | −0.42 | 0.11 | −0.32 | 0.52 | POU5F1P3 | 0.02 | −0.66 | −0.43 | −0.22 | 0.03 |
| AL591848.3 | −0.50 | 0.39 | 0.27 | 0.11 | −0.22 | NCF1C | −0.33 | −0.73 | 0.53 | −0.57 | 0.41 | AC068831.5 | −0.24 | 0.04 | 0.11 | 0.26 | 0.01 |
| CHP1 | 0.37 | −0.05 | −0.24 | 0.00 | −0.35 | G38114 | 0.70 | 0.01 | 0.39 | −0.05 | 0.28 | NDUFB5P2 | 0.03 | −0.31 | 1.49 | −0.03 | 0.39 |
| AC018904.1 | 0.99 | −0.83 | −0.56 | −0.41 | 0.49 | AC007938.1 | −0.50 | −1.01 | 0.22 | 0.61 | 2.34 | AC090518.1 | 0.02 | 0.31 | 0.87 | 0.39 | 0.35 |
| DPYSL2 | −0.35 | 0.24 | 0.53 | 0.02 | 0.04 | RBM48P1 | 0.87 | −1.88 | 0.80 | 0.53 | 1.38 | CCDC77 | 0.01 | −0.18 | −0.20 | 0.02 | 0.13 |
| IGKV4-1 | 1.88 | 2.49 | 1.91 | 0.49 | −1.11 | NOM1 | −0.11 | −0.19 | −0.21 | 0.03 | 0.19 | ACNATP | 0.24 | −0.11 | −0.57 | 1.74 | −0.63 |
| CA12 | 0.47 | −0.26 | −0.18 | 0.08 | 0.18 | BAD | −0.12 | 0.14 | −0.18 | 0.23 | −0.22 | RPA2P3 | −0.24 | −0.50 | 0.37 | 1.47 | 2.17 |
| AC073439.1 | −0.97 | 1.06 | 0.84 | 0.38 | −0.91 | AC092865.1 | −0.37 | −0.36 | 1.22 | −0.67 | 0.01 | FRMPD1 | 0.02 | 0.29 | 0.36 | 0.60 | −0.21 |
| C4BPB | −1.00 | −0.54 | −1.11 | 0.97 | −0.08 | G23403 | 0.58 | −0.72 | −0.11 | −0.87 | 0.04 | AL450344.1 | 0.03 | −0.19 | −0.08 | −0.57 | 0.34 |
| AC072052.1 | −1.19 | 1.10 | 0.95 | 0.94 | −0.60 | LINC01031 | 0.37 | 0.00 | −0.56 | 0.41 | −1.29 | RN7SKP224 | −0.11 | −0.10 | −0.52 | −0.21 | −1.01 |
| BDNF-AS | −0.60 | 0.55 | 1.08 | 0.11 | −0.20 | AC004080.4 | 0.59 | −1.07 | 0.25 | 0.37 | 0.57 | AP003063.2 | −0.06 | −0.41 | −0.87 | −0.93 | −1.51 |
| PLEKHM2 | 0.22 | −0.01 | −0.49 | 0.09 | −0.34 | SCARNA14 | −0.33 | 0.47 | −0.92 | 0.78 | −0.58 | AC138853.1 | 0.24 | −0.63 | −0.15 | 0.58 | −0.98 |
| PDE6A | −0.78 | 0.02 | 0.21 | 0.47 | 1.13 | AC008568.2 | 0.57 | −1.56 | −0.78 | −0.51 | 1.55 | AC034114.2 | −0.05 | −0.30 | −0.59 | −0.03 | 0.02 |
| REST | 0.25 | 0.00 | −0.14 | −0.09 | −0.17 | AC073263.1 | −0.34 | 0.22 | 0.73 | 0.20 | 0.60 | MIR340 | 0.04 | −0.36 | 1.93 | −0.74 | 0.15 |
| AL355073.1 | −0.92 | 0.15 | 0.25 | −0.03 | −0.34 | CCNF | 0.18 | −0.65 | −0.92 | −0.11 | −0.10 | AC091489.2 | 0.13 | −0.97 | −0.19 | 0.51 | 1.02 |
| ROPN1 | −0.85 | 0.66 | 1.33 | 0.83 | 0.88 | RAPGEF6 | 0.08 | −0.06 | −0.07 | −0.13 | 0.01 | LINC01259 | −0.14 | −0.22 | 0.49 | 0.26 | −1.01 |
| ARRB2 | 0.41 | −0.58 | −0.74 | −0.18 | −0.12 | AC108462.1 | −0.39 | 1.29 | 0.57 | 0.24 | 0.82 | G12993 | 0.02 | −0.19 | −0.27 | −0.25 | 0.10 |
| ASAH1 | −0.32 | 0.28 | 0.35 | 0.17 | −0.09 | AC007688.2 | −0.23 | 0.19 | −0.07 | −0.09 | 0.27 | DEFB134 | 0.07 | 0.96 | −0.86 | −0.59 | −2.50 |
| FTH1P20 | −0.92 | 0.30 | 1.07 | −0.42 | −0.48 | AC007218.2 | −1.41 | 0.12 | 2.29 | −1.65 | 0.10 | AL121748.2 | −0.03 | 0.37 | 0.65 | 0.36 | 0.67 |
| RPP38 | 0.29 | −0.19 | −0.35 | 0.01 | −0.17 | SETP8 | 0.36 | −0.44 | −1.52 | 0.50 | −0.23 | AL021707.7 | 0.02 | −0.51 | −0.76 | 0.33 | 0.41 |
| SPOUT1 | −0.29 | 0.07 | −0.16 | 0.21 | 0.04 | FAM157A | 0.19 | −0.50 | −0.87 | 0.03 | 0.19 | AL020996.1 | −0.02 | 0.35 | 0.35 | 0.24 | 0.12 |
| G40027 | 1.22 | 0.07 | −0.05 | 0.26 | −0.71 | MAB21L4 | −0.21 | 0.63 | 0.55 | 0.30 | −0.14 | AP001328.1 | −0.23 | 0.57 | 0.62 | 1.46 | 1.16 |
| G5246 | −1.27 | 1.53 | 1.48 | 1.03 | 0.10 | AC091946.2 | −0.43 | 0.05 | −0.43 | 0.75 | −0.18 | AC090124.2 | 0.08 | −1.75 | 0.27 | −0.51 | 1.40 |
| FAAP20 | −0.26 | 0.13 | 0.04 | 0.21 | 0.07 | AC010864.1 | −0.28 | 0.33 | 1.13 | −0.27 | 0.40 | LINC02091 | 0.04 | −0.47 | 0.08 | −0.01 | 0.77 |
| FBN3 | −0.99 | −0.26 | 0.16 | −0.07 | 0.06 | AC069236.1 | −0.20 | 0.10 | 0.04 | −0.19 | −0.49 | SLC4A1APP1 | −0.04 | 0.09 | 0.21 | −0.40 | −1.44 |
| AL032819.1 | −0.85 | 0.50 | 0.06 | 0.19 | 0.02 | AC002486.1 | −0.86 | 0.76 | 0.47 | 0.36 | −0.42 | AL390198.1 | −0.02 | 0.34 | 0.28 | 0.89 | −0.62 |
| ALOX12P1 | −0.80 | 0.03 | 1.13 | 0.43 | 0.90 | RPL23AP25 | −0.57 | −1.78 | 1.70 | −1.15 | 1.60 | AP005229.2 | 0.23 | −0.13 | −1.21 | 2.80 | −0.21 |
| FRG1BP | −0.28 | 0.20 | 0.48 | −0.09 | 0.34 | AC003684.1 | −0.37 | −0.28 | −0.26 | −0.10 | 0.12 | AL358292.1 | 0.23 | −0.18 | −1.53 | 0.15 | −2.63 |
| G32994 | 1.27 | −0.70 | 1.04 | 0.70 | 1.03 | AC135279.3 | 0.28 | −1.02 | −0.43 | −0.86 | 0.13 | G26252 | 0.10 | 0.52 | 2.39 | −0.31 | 0.46 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| LPIN1 | −0.34 | 0.16 | 0.01 | 0.29 | 0.17 | CTDSPL2 | 0.06 | 0.12 | 0.08 | 0.08 | −0.08 | NAA16 | −0.01 | 0.01 | 0.17 | 0.06 | 0.10 |
| LOXHD1 | 0.57 | −0.52 | −0.55 | −0.28 | 0.02 | RN7SL646P | −0.64 | −0.62 | −1.17 | −0.65 | −0.28 | SNORD114-12 | −0.05 | 0.65 | 1.81 | −0.86 | 0.42 |
| SOX2-OT | −0.60 | 0.20 | 0.61 | 0.23 | 0.43 | RNA5SP122 | −0.36 | 0.29 | −0.65 | −0.35 | −0.77 | CTSE | 0.03 | −0.24 | −0.09 | 0.16 | 0.38 |
| AC073052.1 | 0.38 | −0.04 | −0.30 | −0.06 | −0.29 | CGB7 | −0.29 | 0.30 | −0.32 | 0.20 | −0.54 | AC009518.3 | 0.23 | −0.15 | −0.60 | 1.96 | 0.09 |
| AP000253.1 | −0.69 | 0.47 | 0.23 | 0.92 | 0.82 | CICP20 | −0.99 | 0.77 | 0.20 | −0.75 | 1.01 | ERI3 | 0.01 | −0.02 | 0.14 | −0.03 | 0.09 |
| EPB41L4B | −0.38 | 0.29 | 0.14 | 0.16 | 0.06 | RP11-439A17.10 | 0.48 | −0.92 | 0.26 | −0.44 | −0.78 | CLDN25 | 0.11 | −0.52 | −1.82 | 0.09 | −0.03 |
| AC018695.2 | 1.04 | −0.59 | −1.84 | −0.17 | −1.37 | AC090376.1 | −0.55 | −0.13 | −0.80 | −0.07 | −0.51 | EEF1A1P7 | −0.04 | 0.16 | 0.03 | −0.36 | −0.35 |
| MMP27 | −0.64 | 0.37 | 1.99 | −0.55 | 0.12 | AC079905.2 | 0.37 | 0.23 | 0.28 | 0.17 | −0.09 | MTND3P4 | 0.12 | −1.00 | −0.83 | −0.92 | −1.65 |
| KLHL30 | −0.87 | 0.14 | 0.65 | 0.19 | 0.13 | AC116667.1 | −0.19 | 0.07 | −0.34 | 0.01 | −0.28 | AC021654.1 | 0.05 | 0.07 | 1.05 | −1.02 | −1.16 |
| RPSAP24 | 1.52 | −2.38 | −2.74 | −0.27 | −1.04 | RN7SKP85 | −0.90 | −0.30 | 1.46 | −0.20 | 0.41 | AC117529.2 | −0.05 | −0.55 | −1.68 | 1.37 | 0.24 |
| PSMD8P1 | 0.81 | −0.53 | −0.86 | 0.11 | −0.61 | AP000472.1 | −0.84 | 0.55 | −2.71 | 0.51 | −1.98 | AC087884.1 | 0.04 | −0.74 | −0.51 | −0.51 | −0.46 |
| ANGEL1 | 0.21 | −0.12 | −0.11 | −0.01 | 0.02 | AC145343.1 | −0.59 | −0.25 | 0.85 | 0.75 | 0.01 | GTF2IP6 | 0.23 | −0.38 | −0.02 | 0.31 | 1.16 |
| SLC29A2 | −0.39 | 0.32 | 0.29 | 0.29 | 0.41 | LAMC1-AS1 | −0.25 | 0.20 | 0.47 | −0.38 | 0.60 | PAK4 | −0.01 | 0.22 | −0.09 | 0.28 | 0.05 |
| AC092902.2 | −0.34 | −0.21 | 0.67 | −0.43 | 0.27 | AC007349.2 | 0.46 | −0.93 | −0.86 | 0.90 | 0.46 | BTK | −0.01 | −0.13 | 0.39 | −0.19 | 0.06 |
| FAM3D-AS1 | −1.63 | 0.03 | 2.22 | −0.43 | 0.53 | SLC25A35 | −0.15 | 0.13 | −0.19 | 0.41 | 0.37 | CYTL1 | 0.02 | −0.06 | 0.27 | −0.61 | 0.10 |
| RNU7-75P | 0.85 | −0.26 | −0.35 | 0.22 | 0.48 | LINC01095 | 0.56 | −0.72 | 0.51 | 0.46 | 0.38 | MHENCR | −0.01 | −0.07 | −0.08 | 0.20 | 0.23 |
| PYGB | −0.32 | 0.21 | −0.05 | 0.14 | 0.00 | COX6CP13 | −0.97 | −1.34 | 1.45 | −1.46 | 0.22 | RPSAP28 | −0.21 | 1.36 | −0.72 | 0.71 | −2.01 |
| ALG12 | −0.38 | 0.50 | −0.11 | 0.51 | −0.17 | PIK3CG | 0.19 | −0.47 | 0.08 | −0.21 | 0.26 | AC004466.3 | 0.02 | 0.23 | 0.48 | −0.19 | −0.34 |
| STAM2 | 0.22 | −0.02 | 0.00 | −0.08 | −0.13 | AL136097.1 | 0.43 | 0.00 | 0.44 | 0.16 | 0.25 | RN7SL89P | 0.13 | −1.01 | 0.43 | 1.11 | 1.28 |
| AC092139.2 | 0.54 | −0.37 | −0.57 | −0.19 | −0.12 | PRSS33 | −0.73 | −1.19 | −0.12 | −1.28 | −0.15 | LUZP4 | −0.12 | 0.94 | −1.18 | 0.55 | −1.51 |
| AC114341.1 | −0.81 | −0.81 | 2.23 | −0.30 | 1.51 | HIST1H2APS4 | 0.63 | −1.05 | −0.42 | −2.01 | −1.53 | AC139697.1 | −0.21 | 0.02 | −0.94 | 0.73 | −2.08 |
| MIR5095 | −1.11 | −0.74 | 0.88 | 0.18 | 1.25 | LINC01721 | −0.87 | 0.52 | 0.06 | 0.60 | −0.27 | SETP4 | −0.06 | −0.51 | −0.59 | −0.46 | 0.16 |
| ERVE-1 | −0.50 | 0.76 | 0.50 | 0.42 | −0.34 | AC008083.2 | −0.37 | 0.15 | 0.53 | −0.27 | 0.59 | AP005435.3 | −0.14 | 0.40 | −0.86 | 0.23 | −2.52 |
| AC005726.2 | 0.65 | −0.36 | 0.02 | −0.26 | −0.41 | RPL17P43 | −0.38 | 0.53 | 1.75 | 0.03 | 0.13 | RNA5SP203 | −0.04 | −0.18 | −0.58 | 0.53 | −0.28 |
| G22291 | −1.32 | 0.28 | 2.06 | 0.43 | −0.10 | LINC00499 | −0.63 | 1.39 | −1.39 | 0.16 | −2.93 | LIM2 | 0.14 | −0.27 | −0.85 | −1.97 | −1.55 |
| RNU7-79P | 1.03 | −0.53 | −0.09 | 0.30 | 1.02 | AL161798.1 | 0.57 | −0.45 | 0.93 | −0.19 | 0.59 | AC010329.5 | −0.07 | −0.83 | 0.97 | −0.10 | −0.52 |
| AL136981.2 | 0.57 | −0.20 | −0.02 | 0.06 | 0.18 | G9105 | −0.35 | 0.19 | 0.47 | −0.03 | 0.49 | CTAGE3P | −0.02 | 0.50 | −0.32 | 0.57 | −0.53 |
| AC026471.2 | −0.79 | 0.21 | 0.98 | 0.34 | 0.53 | RPS4XP22 | −0.33 | 0.19 | 0.06 | −0.86 | −0.62 | IGHV3-71 | 0.23 | −0.26 | −1.51 | −0.18 | 1.14 |
| AC136424.1 | −0.69 | 0.28 | 1.57 | −0.01 | 0.26 | AP000347.1 | −0.12 | −0.05 | 0.30 | 0.01 | 0.27 | OR10J6P | 0.21 | −0.48 | −1.56 | 1.54 | 0.93 |
| AC015689.2 | −1.88 | 0.20 | 1.76 | −1.08 | 0.56 | AC009729.1 | −0.90 | 0.23 | −0.11 | −1.69 | −1.96 | AC073525.1 | 0.08 | −0.75 | −1.34 | 1.49 | −0.25 |
| GEMIN4 | −0.36 | 0.29 | 0.25 | 0.17 | 0.04 | AC092580.1 | 0.73 | −1.92 | −0.84 | −0.76 | 1.29 | G25291 | 0.04 | −0.79 | −1.03 | 0.01 | 0.35 |
| HLCS-IT1 | −0.59 | −0.06 | 0.44 | −0.26 | 0.37 | SMARCE1 | 0.07 | 0.07 | −0.01 | 0.09 | −0.08 | CASC6 | −0.12 | 0.45 | −0.84 | 1.53 | −1.17 |
| G2608 | 1.73 | −1.61 | −2.28 | −0.07 | 0.17 | ETDA | 0.66 | 0.38 | 0.04 | −0.51 | −1.01 | RPL31P53 | 0.23 | −0.67 | −1.55 | 0.68 | −0.37 |
| AC104806.2 | −0.66 | −0.13 | 0.76 | 0.26 | 0.75 | INSIG2 | 0.10 | 0.08 | 0.37 | 0.01 | −0.01 | AC022039.1 | −0.14 | −0.05 | 0.17 | 0.65 | −2.44 |
| RNU6-786P | 0.77 | −0.29 | −0.54 | −0.25 | −0.77 | AC100810.3 | 0.35 | −0.14 | −1.32 | 0.07 | −1.26 | PRRX2 | −0.01 | −0.03 | 0.07 | −0.19 | −0.21 |
| ANGPTL7 | −0.58 | 0.57 | −0.08 | −0.23 | −0.95 | AC011451.1 | −0.25 | 0.05 | 0.11 | −0.04 | 0.36 | AL355388.1 | −0.05 | −0.77 | 1.71 | 0.45 | 1.08 |
| AL132801.1 | 1.27 | −0.33 | −2.37 | −0.17 | −1.82 | AL049780.3 | 0.26 | −0.46 | 0.39 | −0.09 | 0.09 | ISM2 | 0.04 | 0.04 | −1.48 | −0.45 | −0.61 |
| AKAP2 | −0.48 | −0.01 | 0.11 | −0.27 | 0.05 | SNRPEP9 | 0.34 | 0.05 | −0.22 | 0.29 | 0.73 | AL583852.1 | 0.23 | −1.09 | −0.77 | 0.43 | 1.46 |
| G35278 | −1.08 | 0.27 | 2.04 | −0.18 | 0.97 | AC003988.1 | 0.58 | 0.49 | −2.20 | 0.56 | −2.73 | LINC00945 | −0.06 | −2.15 | 0.06 | 0.14 | 2.16 |
| GABRB2 | −0.91 | 0.50 | −0.75 | 0.19 | −1.16 | AMBN | 0.52 | 0.68 | −2.91 | 1.20 | −2.49 | AL096828.2 | −0.06 | 0.25 | −0.74 | 0.29 | −1.23 |
| AL023653.1 | 1.47 | −1.24 | 0.25 | −0.79 | 0.45 | RN7SL629P | −0.26 | 0.49 | 0.10 | 0.05 | 0.31 | SPANXN1 | 0.07 | −1.16 | −0.85 | 2.25 | −0.82 |
| CLCN7 | −0.30 | 0.13 | −0.07 | 0.25 | 0.10 | AC104257.1 | −0.67 | −1.28 | 2.57 | −0.43 | 0.72 | AL356274.1 | −0.23 | −0.28 | −0.90 | −1.12 | −1.82 |
| HS2ST1 | 0.28 | −0.05 | 0.06 | −0.03 | −0.12 | AC018410.2 | −0.17 | 0.07 | 0.36 | 0.02 | 0.29 | MEF2A | −0.01 | 0.03 | −0.04 | 0.13 | −0.05 |
| CCNL2P1 | −0.71 | 0.60 | 1.39 | −0.62 | 0.39 | AL353597.1 | 0.63 | −1.43 | −0.20 | 0.13 | 0.43 | AL133230.1 | 0.01 | −0.31 | −0.38 | −0.16 | −0.02 |
| AL669831.4 | −0.49 | 0.22 | 1.02 | −0.33 | 0.26 | AC138761.4 | −1.18 | 0.56 | 0.86 | 0.69 | 0.23 | CROCCP1 | −0.09 | −0.46 | −0.14 | −1.27 | −1.34 |
| IMP4 | 0.24 | −0.30 | −0.45 | 0.01 | −0.05 | SLC6A9 | −0.18 | 0.48 | −0.02 | 0.55 | −0.24 | LIF-AS1 | 0.05 | −1.52 | −2.40 | 0.85 | −1.01 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| RNU6-640P | −0.77 | 0.09 | −0.14 | 0.10 | −0.60 | MIR4305 | 0.56 | −1.50 | −1.04 | −1.02 | −0.22 | SSU72P2 | 0.23 | −0.90 | 0.29 | −0.97 | 0.08 |
| MRPL38 | −0.50 | −0.06 | 0.02 | −0.18 | 0.07 | RN7SKP275 | 0.82 | −0.88 | 1.22 | −1.76 | 0.60 | LCN8 | 0.13 | −1.28 | −1.32 | −1.29 | −0.07 |
| C3orf38 | 0.33 | −0.01 | −0.11 | −0.08 | −0.28 | A3GALT2 | 0.32 | −0.95 | −1.25 | −0.13 | −0.41 | OR4G3P | −0.23 | 0.63 | 1.19 | 0.30 | −1.43 |
| SLC25A39P1 | 0.65 | −0.30 | −0.35 | −0.16 | −0.38 | AL450487.1 | 0.72 | 0.09 | 0.19 | −0.79 | −0.15 | AP001922.4 | −0.06 | 1.05 | −0.46 | 0.25 | −1.26 |
| PROSER1 | 0.26 | −0.04 | −0.08 | −0.05 | −0.05 | LDHAL6EP | −1.11 | 0.42 | 2.83 | −1.52 | 1.23 | PER4 | −0.23 | −0.19 | 0.03 | 1.84 | 0.32 |
| MT-TS2 | −0.79 | 0.60 | 0.66 | 0.73 | −0.38 | FUT6 | −0.31 | −0.70 | −1.99 | 0.16 | −0.66 | AL353616.1 | 0.09 | −1.53 | −1.50 | 1.35 | −0.01 |
| GPRIN3 | 0.53 | −0.47 | −0.17 | −0.52 | −0.14 | PPP1R14BP5 | −0.67 | 1.23 | 2.04 | 0.35 | 0.57 | KIRREL3-AS3 | −0.13 | −0.76 | −0.04 | −0.51 | 0.09 |
| PDE1A | −0.67 | 0.53 | 1.44 | 0.07 | 0.02 | CEP57 | 0.06 | −0.07 | 0.04 | −0.03 | 0.02 | PNN | 0.01 | −0.09 | −0.09 | −0.07 | −0.01 |
| SNORA74B | −0.44 | 0.42 | 0.61 | 0.14 | −0.02 | AC091073.1 | 0.76 | −2.22 | 0.63 | −1.08 | 1.38 | MTATP6P18 | 0.08 | −1.41 | 0.11 | −1.89 | −2.04 |
| RPL36AP41 | 0.96 | −0.74 | 0.59 | −0.86 | 0.25 | NIPA2P4 | 1.20 | 0.89 | −2.49 | 0.85 | −2.53 | C6orf226 | 0.02 | 0.24 | 0.07 | 0.07 | −0.17 |
| CEP89 | −0.19 | 0.02 | −0.02 | −0.05 | −0.01 | DDX42 | 0.04 | −0.07 | −0.19 | 0.05 | 0.03 | RNU6-1162P | −0.06 | 0.21 | 0.46 | 0.17 | 1.33 |
| AC073210.1 | −0.87 | 0.93 | 2.73 | −0.11 | 0.23 | AC104212.1 | −1.16 | 1.80 | 1.71 | 0.95 | −1.62 | BX510359.4 | 0.23 | −0.23 | −0.98 | 1.21 | −0.77 |
| AL139274.2 | −0.50 | −0.22 | 0.23 | −0.57 | −0.40 | RNU7-45P | 0.22 | −0.16 | −0.39 | −0.28 | −0.11 | FGF23 | 0.03 | 0.08 | −1.17 | 0.09 | −0.39 |
| SS18L2 | 0.39 | −0.02 | 0.24 | −0.25 | −0.12 | SOHLH1 | −0.94 | −0.61 | −0.82 | 1.00 | 0.09 | NXF5 | −0.05 | −0.66 | −0.21 | 0.12 | −0.62 |
| POMC | −0.68 | 1.08 | 0.09 | 0.66 | −0.60 | LRRC74A | 0.38 | −0.02 | −0.16 | 0.51 | 0.51 | C19orf73 | −0.03 | 0.07 | 0.52 | 0.12 | −0.11 |
| AL391380.1 | 1.36 | −1.63 | −1.16 | 0.12 | 1.34 | PLAC4 | −0.10 | −0.26 | −0.19 | −0.07 | 0.15 | LINC00943 | 0.03 | −0.23 | −0.31 | 0.15 | −0.01 |
| MTND6P3 | −0.57 | −0.05 | 0.50 | −0.25 | 0.16 | AC092053.1 | −0.45 | −1.16 | −0.20 | 0.43 | 1.52 | MTCYBP33 | −0.03 | −0.73 | −1.02 | 0.22 | −0.43 |
| AC112721.2 | 2.08 | −1.90 | −3.17 | −0.53 | −1.53 | RNU6ATAC6P | 0.40 | −1.38 | −0.48 | −0.16 | −0.37 | AGGF1P7 | 0.10 | −0.15 | 0.37 | −0.94 | 0.64 |
| AC092110.1 | −1.89 | 0.38 | 1.06 | 2.42 | −0.36 | AL390066.1 | −0.16 | −0.25 | −0.12 | −0.44 | 0.02 | LINC00589 | −0.03 | −0.29 | −0.98 | −0.26 | −1.54 |
| AC008443.2 | −1.12 | 0.18 | −0.04 | 0.07 | 0.00 | AL353742.1 | 0.37 | −0.27 | 1.15 | −0.38 | 0.52 | AP000304.1 | −0.02 | 0.23 | 0.55 | 0.39 | 0.31 |
| AC002472.1 | −1.00 | 0.20 | 1.42 | 0.36 | 0.48 | ASTL | 0.30 | −0.91 | −0.57 | −0.59 | −0.29 | RPL19P11 | 0.11 | −0.29 | −1.38 | 0.18 | −1.88 |
| PDF | 0.65 | −0.63 | −0.69 | 0.16 | 0.00 | AL355615.1 | −0.33 | −0.17 | 1.09 | 0.14 | 0.29 | MTND6P2 | 0.11 | −1.36 | −0.45 | −1.53 | −0.01 |
| SLC47A1P2 | −0.74 | −0.18 | 0.79 | −0.19 | 0.69 | LINC01612 | −1.20 | 1.16 | 0.41 | 2.52 | −0.13 | MTND6P8 | −0.23 | −0.30 | −0.86 | 0.20 | −1.07 |
| AC113208.2 | −0.83 | 0.13 | −0.22 | 0.21 | −0.48 | AC125611.1 | 0.49 | −0.36 | −0.63 | −0.43 | −0.55 | AL139824.1 | 0.23 | −0.93 | −2.12 | 0.71 | 0.03 |
| AL590282.1 | 0.59 | −0.36 | −0.25 | −0.19 | −0.57 | CICP3 | −0.40 | −0.22 | 0.49 | −0.01 | 0.15 | AC002064.3 | −0.06 | −0.60 | −0.43 | 0.08 | −1.24 |
| RPL10 | 0.26 | 0.04 | −0.31 | 0.17 | −0.44 | AL645728.3 | −0.97 | −1.29 | 0.14 | −0.13 | 0.40 | AC090099.3 | 0.11 | −1.42 | 0.01 | −1.84 | −1.41 |
| AC046143.2 | −0.52 | −0.26 | −0.07 | −0.16 | 0.58 | AC027319.1 | 0.61 | −1.25 | 0.48 | −1.51 | 1.82 | RNU6-45P | 0.04 | −0.14 | −0.35 | −0.78 | −0.58 |
| GLOD5 | −1.46 | −0.77 | 1.22 | −0.50 | 1.48 | SMIM33 | 0.33 | −0.70 | −0.85 | −0.85 | −0.88 | AL935212.1 | 0.09 | −1.23 | −0.37 | 0.46 | 0.06 |
| DRGX | −1.14 | −0.45 | 0.82 | −0.75 | 1.02 | MIR4767 | 0.37 | 0.22 | −0.29 | −0.20 | −0.78 | RPL7AP23 | 0.23 | −1.87 | 1.15 | −0.60 | 0.05 |
| SGCB | −0.42 | 0.27 | 0.60 | −0.38 | −0.15 | ACSL6 | −0.32 | −0.31 | −0.45 | 0.54 | −0.04 | OTOR | 0.06 | −1.45 | −0.36 | −0.98 | 0.48 |
| AL135910.1 | −0.64 | −0.10 | 0.66 | 0.32 | 0.27 | G15688 | 0.55 | −0.97 | 0.42 | 0.04 | 0.84 | RN7SL481P | −0.02 | 0.00 | −0.42 | 0.32 | −0.24 |
| RNA5SP99 | −1.32 | 0.30 | −0.54 | 1.68 | −0.42 | AC005586.2 | −0.60 | −0.15 | −0.64 | 0.60 | 0.55 | OR10H3 | −0.09 | −0.31 | −0.35 | −0.21 | −0.50 |
| NUCB1-AS1 | 1.23 | −1.13 | −1.15 | 0.62 | 0.68 | AC130686.1 | −0.26 | 0.10 | 0.44 | 0.08 | −0.16 | AC109492.1 | −0.06 | 1.18 | 0.83 | 0.35 | −1.05 |
| METTL7B | −1.27 | −0.21 | 0.79 | 0.10 | 0.42 | MYOG | −0.58 | −0.18 | −0.87 | −0.25 | −1.40 | CACNA2D3 | −0.01 | 0.39 | −0.35 | 0.53 | −0.17 |
| ATP5MFP6 | 1.23 | 0.04 | −0.94 | 0.41 | −0.47 | AC027348.2 | 0.77 | −1.43 | 1.09 | −0.53 | −0.89 | LRRC37A9P | 0.02 | −0.42 | −1.28 | −0.28 | −0.20 |
| HDAC3 | 0.17 | −0.06 | −0.27 | −0.03 | −0.14 | OOEP-AS1 | −0.82 | −0.86 | 0.11 | 1.17 | 1.19 | AL731533.1 | −0.09 | −0.89 | 0.04 | 0.18 | −1.09 |
| AC091057.5 | 1.24 | −1.38 | −1.63 | −0.51 | −0.24 | SNX18P24 | −1.34 | 0.16 | 0.98 | 1.17 | 0.63 | AC044798.2 | 0.11 | −0.95 | −0.39 | 0.58 | −0.41 |
| AC138150.2 | −0.50 | −0.70 | −0.02 | −0.03 | 0.58 | AL035458.2 | −0.39 | 0.55 | 0.29 | −0.61 | 0.30 | AC018892.2 | −0.23 | 0.47 | −0.33 | 0.78 | 0.90 |
| HOXA5 | −0.59 | 0.79 | 0.91 | 0.54 | −0.04 | KNOP1P2 | 0.17 | 0.02 | 0.14 | −0.02 | 0.06 | AL356800.1 | −0.06 | −0.42 | 0.67 | 0.14 | −0.26 |
| INSRR | 0.88 | −0.37 | −1.11 | −0.60 | −1.50 | AC009446.1 | −0.85 | −2.37 | 0.53 | −0.92 | 1.96 | AC026616.1 | −0.23 | 0.66 | 0.37 | 1.63 | −0.05 |
| AC010809.1 | 0.50 | −0.37 | −1.01 | 0.21 | −0.06 | CLHC1 | −0.10 | 0.11 | 0.34 | 0.16 | 0.18 | IFT46 | 0.01 | 0.00 | −0.06 | 0.01 | −0.12 |
| ACTR10 | 0.29 | −0.09 | 0.03 | −0.22 | −0.17 | AC026353.1 | −0.76 | 0.02 | 1.02 | 0.75 | −0.39 | FLVCR1-DT | 0.02 | 0.03 | −0.21 | −0.26 | −0.78 |
| CAMKMT | 0.26 | −0.22 | −0.12 | −0.10 | 0.14 | BNIP3P16 | −0.30 | −0.33 | 0.69 | −0.42 | 0.58 | MIR1294 | 0.04 | −0.83 | 1.43 | −1.48 | 0.17 |
| OR56B4 | −1.61 | −0.11 | 0.92 | −0.80 | −0.62 | NRTN | −0.28 | 0.52 | −0.14 | 0.14 | −0.54 | SUCLA2P2 | 0.13 | −2.16 | 1.22 | −1.15 | 1.69 |
| AL590867.2 | 0.53 | −0.02 | 0.05 | −0.27 | −0.47 | AC126407.1 | −0.54 | −0.56 | −0.36 | 1.37 | −0.79 | RASA2-IT1 | −0.01 | −0.29 | −1.15 | 0.24 | −0.24 |
| AC104964.3 | −0.52 | 0.12 | 0.31 | −0.22 | −0.20 | CTCFL | −0.41 | −1.27 | −1.21 | 0.39 | −0.31 | AL136131.1 | −0.19 | 0.71 | −0.02 | 0.34 | 0.05 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| NDUFA13 | −0.54 | 0.11 | 0.20 | 0.24 | 0.11 | MED23 | 0.06 | 0.10 | 0.07 | 0.04 | −0.09 | AC233724.8 | 0.23 | 0.16 | −0.44 | 0.79 | −0.50 |
| PSD2 | −1.08 | 0.05 | −0.01 | 0.39 | −0.61 | GNAQP1 | −0.56 | 2.13 | −2.22 | 0.79 | −2.09 | OR52Z1 | 0.10 | −0.31 | −1.14 | 0.31 | −1.03 |
| MAFA-AS1 | −1.77 | 0.03 | 0.32 | 1.33 | 1.16 | RPL6P25 | −0.57 | −0.19 | −1.98 | 1.55 | −0.13 | AC022784.4 | −0.21 | 0.40 | −0.50 | 1.57 | 0.00 |
| AC004069.1 | −0.99 | 0.57 | 0.75 | 0.01 | 0.17 | AC055733.3 | 0.31 | −0.43 | 0.02 | −0.24 | 0.48 | AC009812.1 | 0.03 | 0.54 | 1.13 | −0.08 | 0.19 |
| C2orf81 | −0.83 | −0.22 | 1.18 | −0.19 | 0.41 | AC087276.1 | −0.16 | −0.33 | 0.43 | −0.09 | 0.93 | AP001269.3 | −0.22 | −0.57 | −0.24 | −0.97 | −0.22 |
| LRRC9 | −0.74 | −0.67 | −0.58 | −0.43 | 0.12 | IFIT2 | 0.22 | −0.64 | −0.23 | −0.96 | 0.09 | RNA5SP400 | −0.22 | −0.17 | NA | −0.32 | −0.26 |
| MTCO2P34 | 1.93 | −1.32 | −0.07 | −1.59 | −0.01 | AC007395.1 | −0.62 | 0.00 | 1.11 | 0.71 | 0.16 | AC011506.1 | 0.06 | −1.24 | −1.61 | 0.77 | 0.40 |
| CILP2 | −1.02 | 1.36 | 0.94 | 0.21 | −0.14 | AC145207.8 | 0.31 | 0.06 | 0.21 | −0.16 | 0.51 | LINC02311 | 0.13 | −0.62 | 0.77 | −0.85 | −0.36 |
| PCED1B-AS1 | 0.37 | −0.60 | −0.76 | −0.02 | 0.16 | OR10S1 | −0.71 | 0.01 | −0.87 | −0.22 | −0.06 | AC017104.3 | 0.02 | −0.65 | 0.26 | 0.29 | 0.51 |
| GLIPR1 | 0.41 | −0.42 | 0.06 | −0.26 | 0.25 | LINC02075 | −0.92 | −0.66 | 0.05 | 1.19 | 1.44 | AL391650.2 | −0.09 | −0.48 | 1.01 | 0.70 | 0.66 |
| AL591806.2 | −0.69 | 0.36 | 0.77 | −0.10 | 0.14 | AC026741.1 | −0.27 | −0.20 | 0.62 | −0.18 | 0.28 | AP003485.1 | −0.22 | 0.18 | −1.82 | 1.30 | 0.72 |
| AC091544.4 | −0.91 | 0.14 | 0.66 | 0.15 | 0.70 | AC092484.1 | −0.78 | 0.30 | 0.31 | 0.07 | −0.81 | CTBP2P5 | 0.09 | −0.35 | −2.31 | 2.45 | 0.52 |
| AP001781.1 | −1.05 | 0.04 | 0.24 | 0.18 | 0.16 | SLC17A5 | −0.12 | 0.13 | 0.28 | −0.29 | −0.20 | KCNS3 | 0.01 | 0.25 | −0.04 | −0.05 | −0.08 |
| AARSD1 | −0.44 | −0.12 | 0.47 | 0.01 | 0.28 | MOV10L1 | −0.20 | −0.38 | −0.43 | 0.38 | −0.15 | AL162595.1 | 0.02 | 0.27 | 0.56 | 0.34 | 0.35 |
| AC018462.2 | −1.06 | 0.13 | 1.46 | −0.04 | 1.02 | AP003555.2 | 0.40 | −0.31 | 0.41 | −0.83 | 0.26 | AL353708.2 | 0.06 | 0.65 | −1.28 | 0.44 | −1.51 |
| LINC01538 | −1.30 | −0.05 | 1.20 | 0.17 | 0.88 | AC009121.1 | −0.24 | −0.40 | −0.77 | 0.02 | −0.18 | AC090136.3 | 0.03 | −0.69 | 1.64 | −1.17 | 0.95 |
| PHLDB3 | −0.37 | 0.18 | −0.16 | 0.17 | 0.02 | AC068481.1 | 0.16 | −0.32 | −0.36 | −0.29 | 0.05 | RNU2-67P | 0.22 | −0.45 | −2.05 | 0.23 | NA |
| AC245140.2 | 0.61 | −0.81 | −0.33 | −0.59 | 0.26 | AL021068.1 | −0.19 | 0.41 | −0.35 | 0.08 | −0.67 | ASNSP3 | 0.06 | −0.65 | −0.62 | 0.40 | −0.81 |
| SNRPCP6 | −1.21 | 1.23 | 0.95 | 0.50 | 0.10 | CKS1BP7 | −0.72 | 1.68 | 0.61 | 0.95 | −1.17 | C8orf59P2 | −0.07 | −0.07 | −0.16 | −0.80 | −0.62 |
| GOT2P2 | −1.19 | 0.05 | 0.20 | 0.30 | 0.38 | JPH3 | −0.26 | −0.23 | −0.13 | 0.22 | 0.68 | AC068134.2 | −0.22 | −0.73 | 0.25 | −0.04 | 0.23 |
| CLDN3 | −0.82 | 0.81 | 0.36 | 0.70 | 0.41 | AL031666.1 | −0.16 | 0.02 | 0.04 | 0.32 | 0.12 | AL354685.1 | −0.05 | 0.14 | −0.66 | 0.30 | −0.82 |
| AC078881.1 | −0.60 | 0.17 | 0.38 | 0.68 | 0.62 | ATRX | −0.06 | 0.10 | 0.04 | 0.02 | −0.06 | LINC02488 | 0.22 | −0.14 | −0.37 | 0.81 | 1.17 |
| HIP1 | −0.22 | 0.09 | −0.01 | 0.20 | 0.01 | MIR4258 | 0.35 | −0.06 | −1.19 | 0.43 | −0.41 | CFL1P3 | 0.02 | 0.66 | 0.43 | −0.09 | −0.19 |
| MFSD13A | −0.33 | 0.18 | 0.50 | −0.04 | 0.05 | AL031777.1 | 0.87 | 0.61 | −3.43 | −1.19 | −2.71 | AC004490.1 | −0.02 | −0.03 | 0.17 | −0.14 | 0.12 |
| CHN2 | −0.47 | 0.03 | 0.23 | −0.21 | 0.12 | OR5B2 | −0.49 | 0.25 | 0.04 | 0.50 | −1.14 | FTH1P9 | 0.22 | −0.29 | −0.98 | 1.67 | −0.72 |
| AC008149.1 | 0.95 | −1.06 | −0.36 | −0.59 | −0.82 | AC004852.2 | 0.58 | −1.11 | −2.34 | 0.29 | −1.13 | LNCPRESS1 | −0.13 | −1.07 | −0.16 | −1.20 | 0.70 |
| ANKRD40 | −0.30 | 0.10 | 0.14 | −0.03 | 0.00 | KRT19P4 | 0.63 | −1.19 | −1.32 | 0.10 | 0.09 | AC010511.1 | 0.22 | −0.86 | −0.60 | 0.09 | 1.18 |
| GNLY | 0.79 | −1.23 | −0.44 | −0.90 | −0.15 | PAGR1 | −0.17 | 0.13 | 0.64 | 0.04 | 0.26 | AC015871.4 | −0.02 | 0.23 | 0.45 | −0.11 | −0.07 |
| MIR4269 | 1.09 | −0.01 | 0.92 | −0.54 | 0.09 | AC002400.1 | −0.19 | 0.20 | −0.62 | 0.15 | −0.61 | AC068042.1 | −0.18 | −0.14 | −0.82 | −0.58 | −1.63 |
| EGFLAM-AS3 | 1.10 | −0.48 | −1.04 | 0.33 | −0.64 | AC139700.1 | −0.73 | 0.08 | 1.33 | 0.36 | 0.30 | AC027216.1 | 0.22 | −1.28 | 0.25 | 0.36 | −0.49 |
| AC133644.2 | 0.90 | −0.62 | −0.56 | −0.67 | −0.40 | HRG | −0.36 | −0.55 | −0.75 | −0.36 | −0.48 | MTUS2-AS2 | −0.07 | −0.62 | −1.63 | 2.07 | −0.47 |
| SLC22A9 | −1.15 | −0.36 | −0.44 | 0.58 | −0.29 | AC024257.5 | −0.76 | −1.31 | −0.28 | 0.57 | 1.39 | AL121901.1 | −0.22 | −0.04 | 1.68 | −0.27 | −1.20 |
| SLC24A5 | −0.77 | 0.53 | −0.36 | 0.84 | 0.24 | PRR19 | 0.35 | −0.37 | −1.12 | −0.25 | −0.17 | AL133517.1 | −0.02 | −0.48 | −0.08 | −0.31 | 0.01 |
| LINC02157 | −0.91 | 1.08 | 1.83 | 1.39 | 0.20 | AL359317.2 | −0.26 | 0.47 | −0.42 | 0.10 | −0.04 | AC122138.1 | 0.14 | −0.25 | −1.54 | −0.31 | −2.14 |
| IWS1 | 0.24 | −0.23 | −0.28 | −0.19 | −0.02 | PSPN | −0.16 | −0.16 | −0.09 | 0.21 | 0.23 | OR4K2 | 0.04 | 0.10 | −0.80 | 1.65 | −0.25 |
| RNF138P1 | −0.59 | 0.43 | 0.88 | 0.43 | −0.13 | AC087749.1 | 0.18 | 0.02 | −0.59 | 0.22 | −0.04 | AC009055.1 | −0.08 | 1.20 | −0.09 | 1.12 | −0.86 |
| C2CD4D | −0.41 | 0.45 | 0.14 | 0.48 | 0.58 | AL121832.2 | 0.19 | −0.15 | −0.30 | −0.05 | 0.33 | AC113367.3 | −0.10 | −0.10 | −0.75 | 2.82 | 1.42 |
| ANKLE1 | −0.67 | −0.30 | −0.50 | 0.89 | 0.59 | AC027601.5 | −0.19 | 0.26 | −0.17 | 0.19 | 0.36 | NRSN2 | −0.01 | 0.04 | 0.24 | −0.11 | 0.09 |
| RITA1 | 0.28 | −0.09 | 0.01 | 0.04 | 0.19 | AL035398.1 | 0.55 | 0.20 | 1.01 | −0.02 | 0.14 | AC140061.4 | −0.13 | −0.15 | 0.30 | −0.01 | 1.20 |
| AL513175.1 | 1.20 | 0.11 | −0.96 | 0.23 | −0.72 | AC040162.2 | 0.59 | −0.27 | 1.39 | −0.62 | 0.95 | AC021393.1 | −0.21 | −0.34 | −2.62 | 1.33 | −1.09 |
| FEM1B | 0.33 | 0.01 | 0.00 | −0.09 | −0.24 | PHETA1 | −0.12 | 0.42 | −0.17 | 0.34 | −0.28 | AC099654.3 | −0.15 | −1.66 | −1.39 | 0.23 | 3.29 |
| RBM12B | −0.21 | 0.09 | 0.32 | 0.07 | 0.23 | RNU6-1201P | −0.29 | −0.23 | 0.11 | 0.29 | −0.08 | RNA5SP169 | 0.22 | −0.58 | 0.33 | −0.33 | 0.86 |
| SETD2 | 0.14 | 0.01 | −0.03 | −0.05 | −0.06 | AC020910.3 | −0.19 | −0.06 | 0.55 | −0.07 | 0.64 | COX5AP2 | −0.16 | 1.37 | −1.40 | 1.55 | −2.60 |
| ACADS | −0.36 | 0.07 | 0.02 | 0.01 | −0.11 | HRH4 | 0.31 | −0.37 | −1.07 | 0.43 | −0.26 | FDPSP4 | −0.04 | −0.48 | −0.43 | −0.01 | 0.13 |
| AC090181.2 | 0.72 | −0.28 | −0.19 | 0.20 | −0.04 | KRTAP4-9 | −1.13 | 0.25 | 1.79 | −0.26 | −2.48 | OR7E102P | −0.06 | −1.01 | −0.31 | −0.52 | −0.67 |
| AL359915.1 | −0.86 | 0.69 | −0.29 | 0.34 | 0.08 | AC046185.3 | 0.20 | −0.57 | 0.10 | −0.31 | 0.36 | GOLGA8DP | −0.13 | −0.77 | −0.02 | −0.05 | 0.99 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| CYCSP11 | 1.63 | −1.17 | −3.03 | 0.17 | −2.36 | RNU6-484P | 0.50 | −0.11 | −1.56 | −0.36 | −0.10 | SCAMP4 | −0.01 | 0.03 | −0.21 | 0.12 | 0.02 |
| RNA5SP267 | −0.95 | 0.54 | −0.58 | 0.88 | −0.62 | PCAT5 | 0.62 | −1.71 | 1.95 | −1.34 | 0.30 | AC008655.2 | 0.04 | 0.11 | 0.40 | 0.13 | −0.94 |
| COQ7 | −0.21 | 0.27 | 0.14 | −0.08 | −0.11 | AL512380.1 | −0.34 | 0.52 | 0.42 | 0.96 | 0.89 | SMR3A | 0.08 | −0.23 | −0.91 | 0.39 | −0.85 |
| DLST | 0.17 | −0.15 | −0.30 | −0.04 | −0.11 | AL358472.3 | 0.30 | 0.46 | −0.77 | 0.75 | 0.38 | LINC01790 | 0.06 | −1.36 | −2.04 | 1.05 | −1.09 |
| AP001922.5 | −1.04 | 0.45 | 1.01 | 0.60 | 0.92 | AL022324.1 | 0.36 | −0.20 | 1.31 | −0.18 | 0.69 | RASA4B | −0.03 | 0.60 | 1.19 | 1.05 | 0.35 |
| HCG15 | −0.69 | −0.19 | 0.03 | 0.25 | 0.40 | LINC00664 | −0.25 | −0.69 | −0.07 | 0.58 | 0.60 | AP005131.7 | −0.02 | 0.31 | 0.54 | −0.42 | −0.02 |
| MIR4713 | 1.29 | −0.05 | −2.24 | 1.01 | −0.99 | FAM8A6P | −0.58 | 0.20 | 2.18 | 0.09 | 0.06 | RPL5P23 | −0.02 | −0.51 | 0.73 | −0.53 | 0.75 |
| RP4-565E6.1 | −1.36 | 1.46 | 0.77 | −0.01 | 0.55 | MTND5P2 | 0.19 | −0.15 | −0.09 | −0.62 | −0.30 | AC026434.2 | 0.21 | 0.43 | −0.66 | 1.16 | −0.20 |
| SPAG4 | −0.52 | 0.42 | 0.10 | 0.22 | −0.13 | FRG2IP | 1.03 | −0.61 | −2.49 | 0.14 | −2.07 | LINC02287 | −0.12 | 0.62 | −0.16 | 1.69 | −1.06 |
| RP9P | −0.33 | 0.01 | 0.47 | −0.11 | 0.25 | MEOX1 | −0.17 | 0.29 | 0.61 | −0.07 | −0.35 | OR9S24P | 0.22 | −0.37 | −0.98 | 0.48 | −1.18 |
| MUS81 | −0.33 | −0.08 | −0.22 | 0.24 | 0.26 | SLC25A34 | −0.15 | 0.26 | −0.05 | 0.10 | −0.02 | GOLIM4 | 0.01 | 0.04 | 0.13 | −0.24 | −0.21 |
| AC010967.3 | −0.97 | 0.59 | −2.45 | 0.67 | −0.88 | RNU6-1280P | 0.33 | 0.11 | −0.07 | −0.22 | −0.73 | RN7SL168P | −0.04 | 0.04 | −0.27 | 0.38 | −0.61 |
| LINC01527 | 1.94 | −0.94 | −1.96 | −0.43 | −1.28 | AC099489.3 | 0.39 | −1.52 | −1.18 | −0.58 | −0.18 | AC013264.1 | −0.03 | −0.41 | 0.52 | −0.15 | 0.26 |
| ANP32B | 0.34 | −0.44 | −0.31 | −0.18 | 0.01 | AC008632.1 | −0.50 | −0.82 | −0.90 | 0.50 | 1.41 | LINC01304 | 0.06 | −1.61 | −1.77 | −0.21 | −0.56 |
| LINC02204 | −0.83 | −0.14 | 0.63 | 0.15 | 0.71 | AP003175.1 | −0.45 | −1.15 | 1.08 | −0.76 | −0.11 | AL513542.1 | 0.13 | −1.03 | −0.87 | −0.19 | 1.75 |
| AC068473.4 | 1.12 | 0.97 | 0.46 | 0.34 | −0.31 | AL596257.1 | 0.84 | −1.87 | −1.36 | 0.99 | 0.18 | NMNAT1 | −0.01 | 0.02 | 0.05 | −0.13 | −0.05 |
| AC009299.2 | −0.55 | 0.18 | 0.17 | −0.03 | 0.00 | AL133320.1 | 0.65 | −0.83 | 1.34 | 0.45 | 0.85 | AC010376.1 | 0.22 | −0.72 | −0.11 | −0.42 | −0.24 |
| DNAH5 | −0.62 | 0.49 | 0.20 | 0.39 | 0.08 | LINC01982 | 0.88 | 0.30 | −1.38 | 0.73 | −2.53 | GS1-256022.1 | 0.22 | −0.74 | −0.71 | 0.39 | −2.22 |
| AC093752.1 | −0.25 | 0.29 | 0.58 | 0.12 | 0.24 | AC011479.3 | −0.19 | 0.25 | 0.18 | −0.08 | −0.02 | OR7E105P | 0.08 | −1.77 | −1.68 | −0.43 | 1.12 |
| AC069547.2 | 0.62 | −0.17 | −0.55 | 0.09 | −0.12 | CD68 | −0.29 | 0.33 | −0.60 | 0.46 | −0.39 | GIMAP2 | −0.01 | −0.03 | 0.46 | −0.08 | 0.14 |
| AP001266.2 | −0.72 | 0.37 | 1.31 | −0.16 | 0.68 | AC068025.1 | 0.47 | −0.56 | 0.64 | −0.58 | 0.93 | AC095059.2 | −0.11 | −1.04 | −1.76 | 0.69 | 0.67 |
| AC023034.1 | −1.23 | 0.09 | 1.62 | −0.07 | 1.09 | AL162718.2 | 0.48 | 0.15 | 0.20 | 0.64 | −0.65 | AL022578.1 | 0.19 | −0.13 | 0.84 | −0.99 | 0.93 |
| FAM72D | 0.94 | −0.11 | −0.29 | 0.07 | −0.48 | G32334 | −0.26 | 0.27 | −0.45 | −0.36 | −0.53 | AC104137.1 | 0.13 | −0.81 | 0.51 | −0.45 | 0.97 |
| MIR181A1HG | 0.57 | −0.36 | −0.33 | −0.36 | −0.34 | G26553 | −1.08 | −0.03 | −1.26 | 0.91 | −1.63 | SENP8 | −0.01 | 0.15 | 0.13 | 0.18 | 0.22 |
| LINC00654 | −0.67 | 0.44 | 0.77 | 0.14 | 0.07 | AC010127.1 | −0.26 | 0.32 | −0.56 | 0.52 | −0.94 | MIR601 | −0.02 | −0.18 | 0.34 | 0.10 | 0.51 |
| RN7SKP16 | 0.63 | −0.38 | −0.89 | −0.24 | −0.32 | MIR1296 | 0.23 | −0.01 | 0.14 | −0.38 | −0.12 | DGCR11 | 0.01 | 0.00 | 0.00 | 0.25 | 0.17 |
| ARFGAP2 | −0.21 | 0.13 | −0.16 | 0.23 | −0.08 | OSBPL10-AS1 | 0.12 | 0.02 | −0.62 | −0.10 | −0.26 | IQCG | −0.01 | −0.08 | −0.23 | 0.15 | 0.17 |
| AMD1P3 | −1.41 | −0.06 | 0.86 | 1.10 | 0.21 | C1orf210 | 0.19 | 0.27 | 0.22 | −0.20 | −0.17 | LINC02502 | 0.22 | 0.17 | −1.19 | 0.32 | −0.33 |
| DEFB132 | −1.85 | 0.76 | 2.09 | 0.14 | 0.61 | AL160408.4 | −0.37 | 0.37 | 1.27 | −0.22 | −0.12 | OR5BL1P | 0.09 | 0.42 | −0.17 | 0.20 | 0.00 |
| AP001471.1 | −1.58 | 0.08 | 1.64 | −0.88 | 0.93 | AL031577.1 | −0.28 | 0.14 | −0.90 | 0.59 | −0.01 | PSMA2P2 | −0.04 | 0.03 | −0.06 | 0.23 | 0.86 |
| AP001453.1 | −1.28 | 0.92 | 1.78 | −1.28 | 0.26 | LINC02449 | −0.23 | 0.12 | 0.22 | 0.32 | 0.39 | RNU6-1198P | 0.05 | −0.35 | 1.47 | −0.32 | 1.14 |
| FAM157B | 0.64 | −0.32 | −1.08 | −0.17 | −0.36 | BIN2 | 0.20 | −0.55 | 0.15 | −0.44 | 0.24 | LINC01653 | 0.05 | −1.37 | −1.71 | 0.56 | 0.15 |
| AC008443.4 | −1.02 | −0.90 | 1.65 | −0.53 | 0.57 | LINC00319 | −0.61 | 0.82 | 0.94 | −1.46 | 0.36 | SHPK | 0.01 | −0.07 | −0.64 | 0.04 | −0.46 |
| BCAP29 | 0.31 | −0.24 | −0.20 | −0.21 | −0.13 | AL136419.1 | −0.33 | 0.33 | −1.36 | 0.33 | −1.13 | OR4A13P | −0.07 | −0.41 | −2.00 | 1.79 | −0.35 |
| LINC01010 | 0.80 | −0.17 | −1.27 | −0.06 | −0.53 | AL034346.1 | −0.74 | 0.14 | 0.84 | −0.45 | 0.01 | INE1 | −0.01 | 0.06 | 0.19 | −0.30 | −0.08 |
| EEF2KMT | 0.35 | 0.02 | −0.24 | 0.21 | −0.05 | DLEU1-AS1 | 0.36 | −0.77 | −2.05 | 0.98 | −0.42 | DBIP2 | 0.08 | −1.14 | −0.18 | −1.90 | −0.91 |
| AC006270.3 | 0.96 | −0.63 | −0.48 | −0.44 | 0.00 | LINC00115 | −0.17 | 0.14 | 0.60 | 0.01 | 0.42 | AL133371.3 | 0.06 | −0.98 | 1.32 | −1.80 | 0.61 |
| CWC15 | 0.28 | −0.18 | −0.35 | −0.14 | −0.32 | AC008105.1 | 0.20 | −0.85 | 0.13 | −0.44 | 0.52 | AC079382.1 | −0.21 | 0.69 | 0.01 | −0.36 | −0.76 |
| G24393 | 1.20 | −1.61 | −1.57 | −0.99 | −0.56 | SNORD88 | 0.35 | 0.07 | 0.31 | −0.61 | 0.21 | AC009963.3 | 0.18 | −0.34 | 0.72 | 0.11 | 0.86 |
| LINC02028 | −0.88 | −0.20 | 0.10 | −0.05 | 0.58 | AP003122.2 | −1.42 | −0.29 | 0.35 | −0.51 | 1.84 | AC009518.2 | −0.21 | −1.47 | −0.68 | −0.36 | 0.22 |
| GATD3A | −0.72 | −0.67 | 0.36 | 0.11 | 1.23 | NOTO | 0.54 | −2.27 | −0.58 | −0.60 | −0.23 | RPL10P2 | 0.21 | −0.35 | 0.43 | −1.45 | −0.24 |
| AURKAP2 | −2.12 | 0.53 | 1.03 | 0.75 | 2.11 | AC104692.2 | 0.31 | −0.20 | 0.18 | 0.33 | 0.38 | AC093323.4 | 0.16 | −0.48 | −0.53 | 2.13 | −0.32 |
| COL4A2 | 0.54 | −0.59 | −0.32 | −0.59 | −0.36 | G39823 | 0.59 | −0.22 | −0.15 | 0.58 | 0.30 | AC087879.1 | −0.21 | −0.44 | NA | 1.28 | NA |
| AC022034.1 | −0.53 | 0.27 | 0.48 | 0.40 | 0.09 | KATNBL1P2 | −0.60 | −0.06 | 1.57 | 0.99 | −0.30 | RP11-115K3.1 | −0.21 | 0.43 | −0.47 | 0.82 | −1.30 |
| C20orf27 | 0.31 | −0.25 | −0.41 | 0.12 | −0.25 | FOXRED1 | −0.07 | −0.13 | 0.04 | −0.15 | 0.15 | LINC01518 | −0.21 | −0.25 | 0.72 | 0.86 | 0.24 |
| LINC00370 | 1.80 | −0.91 | 0.61 | −1.08 | 0.08 | DPY19L1P1 | −0.15 | 0.24 | 0.38 | 0.22 | −0.04 | MIR193A | −0.03 | −0.60 | −0.36 | −0.59 | 0.23 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC022509.2 | −0.56 | 0.43 | 0.46 | 0.59 | 0.42 | S100A13 | −0.12 | 0.05 | −0.03 | 0.04 | −0.36 | AC243732.1 | 0.02 | 0.14 | −0.02 | 0.28 | 0.17 |
| RN7SL30P | 0.87 | −0.52 | −1.42 | −0.17 | −0.86 | KCNMB3 | −0.11 | 0.14 | 0.14 | 0.21 | −0.07 | CST8 | 0.14 | −0.87 | 0.63 | −1.16 | −0.54 |
| GCC2-AS1 | −1.08 | −0.53 | 0.98 | −0.55 | 1.03 | AC099066.3 | −0.62 | −0.19 | 1.42 | −0.20 | 0.53 | AC034102.3 | 0.06 | −1.86 | −0.50 | −1.05 | 1.20 |
| FAM106DP | 1.02 | −0.75 | −1.17 | −0.53 | −0.28 | LSM3P4 | 0.36 | −0.13 | 0.53 | −0.76 | 0.22 | AL451046.1 | 0.14 | −0.29 | 0.38 | −0.13 | −0.62 |
| ABL1 | −0.23 | 0.06 | 0.21 | −0.11 | 0.00 | LSM8 | 0.06 | −0.14 | 0.11 | −0.07 | 0.09 | AC106827.2 | 0.04 | −1.45 | −0.46 | −0.34 | 0.72 |
| SLC5A7 | −0.99 | 0.16 | −1.44 | 0.25 | −1.57 | FTMT | −1.05 | −0.61 | 0.87 | −1.19 | 0.88 | MIR4499 | −0.05 | 0.70 | −0.90 | −0.02 | −0.78 |
| SKP1 | 0.24 | 0.02 | −0.15 | −0.06 | −0.23 | G30340 | 0.76 | −1.43 | −2.33 | 0.20 | −0.98 | DDX55 | −0.01 | −0.19 | −0.14 | −0.10 | 0.15 |
| PDZRN3-AS1 | −0.94 | 0.76 | 0.06 | −0.25 | −0.61 | AC092868.2 | 0.16 | −0.53 | −1.20 | −0.56 | −0.57 | AC084262.1 | 0.08 | −0.65 | −0.47 | 1.95 | 1.55 |
| NUTM2G | −0.52 | 0.19 | 0.46 | −0.07 | 0.24 | AC087855.2 | −1.20 | −0.39 | 1.38 | 0.37 | 1.68 | AC010536.2 | −0.02 | −0.02 | 0.47 | −0.65 | 0.09 |
| DLEU7-AS1 | −0.88 | 0.49 | 1.24 | −0.03 | 0.54 | OLFM4 | 0.39 | −0.19 | −0.44 | −0.09 | −0.83 | AC010904.2 | −0.03 | 0.10 | −0.65 | −0.51 | −0.34 |
| PDE2A | −0.58 | 0.37 | 0.56 | 0.47 | −0.04 | ECE1 | −0.09 | 0.01 | 0.08 | −0.12 | −0.18 | SERPINA7P1 | −0.21 | 0.58 | −0.47 | 1.68 | −1.41 |
| CASP8AP2 | 0.20 | −0.13 | 0.06 | −0.18 | 0.02 | AC008966.1 | −0.27 | 0.46 | 1.03 | −0.18 | 0.01 | AC114744.1 | −0.04 | −0.47 | −0.25 | 0.14 | 0.02 |
| BTF3L4P1 | 0.84 | 0.08 | −0.39 | 0.16 | 0.02 | AL356234.3 | 0.67 | −0.43 | 0.91 | −1.44 | −1.04 | PGAM1P9 | −0.21 | −0.27 | 2.18 | 0.30 | 1.60 |
| AL049870.3 | −0.82 | 0.80 | 0.67 | −0.54 | −0.02 | ARRDC1 | −0.11 | 0.02 | −0.44 | 0.19 | −0.06 | AL353616.2 | 0.06 | −0.80 | 1.60 | 0.07 | 0.24 |
| AL078581.3 | −0.44 | 0.27 | 0.54 | 0.15 | 0.04 | RN7SL695P | 1.40 | 0.01 | 0.02 | −0.80 | −1.22 | RPS3AP42 | 0.21 | −1.23 | −1.13 | 0.59 | 1.29 |
| GBX1 | −0.95 | −0.15 | 0.97 | −0.18 | 1.00 | HNRNPA1P12 | 0.39 | −0.20 | −1.76 | 0.71 | −1.21 | AL035551.1 | −0.02 | −0.42 | 0.21 | 0.06 | 0.05 |
| AC012313.2 | −0.89 | 0.03 | 0.85 | −0.20 | 0.69 | RN7SL861P | 0.73 | −0.32 | 0.15 | −0.37 | 0.66 | RNF6P1 | 0.08 | −0.87 | −1.00 | −0.52 | −2.15 |
| AL049649.1 | −1.04 | 0.33 | 1.14 | 0.02 | 0.46 | G25631 | −0.59 | 0.45 | 0.88 | −0.32 | −0.48 | PATE2 | −0.04 | −0.30 | −0.41 | 0.11 | −0.12 |
| AC090018.1 | 0.86 | −0.30 | −0.64 | −0.11 | −0.70 | LIPC-AS1 | −0.29 | 0.33 | −0.40 | 0.06 | −1.03 | ISCA1P4 | 0.20 | −0.45 | 0.72 | 1.01 | 1.64 |
| GRTP1 | −0.34 | 0.20 | 0.10 | 0.27 | 0.14 | ALKBH6 | −0.14 | 0.09 | 0.49 | 0.11 | 0.14 | AC114814.1 | 0.21 | −0.48 | 0.61 | −0.66 | 0.35 |
| OR5BJ1P | −1.41 | 0.54 | 2.93 | −1.11 | 0.77 | RNU6-470P | 0.46 | −0.15 | 0.45 | −0.45 | 0.26 | AC096888.1 | −0.21 | −0.87 | −0.31 | 0.83 | 0.19 |
| SLC35F6 | 0.38 | −0.16 | −0.24 | 0.10 | −0.15 | KRT71 | −0.59 | −0.27 | 1.94 | 0.38 | 3.39 | OR2L5 | 0.03 | −1.08 | −0.08 | 0.70 | 1.32 |
| AC009086.3 | −0.74 | 0.04 | 0.43 | 0.02 | 0.71 | AP005482.1 | 0.39 | −0.84 | 0.15 | −0.37 | 0.27 | G5385 | −0.04 | −0.64 | 0.50 | −0.97 | 0.52 |
| LCE2B | −0.92 | 0.56 | 1.70 | 0.47 | −0.07 | CRYZP2 | −0.65 | −0.76 | 1.73 | 0.89 | 2.42 | LINC01428 | 0.09 | −1.62 | −2.42 | 0.79 | −0.26 |
| AC011287.2 | −1.81 | 0.39 | −1.13 | 0.05 | −1.11 | PRSS1 | −0.35 | 0.26 | 0.87 | 0.24 | 1.14 | FTH1P3 | 0.01 | −0.46 | 0.03 | 0.08 | 0.38 |
| AL445472.1 | −0.39 | 0.48 | 0.59 | 0.20 | 0.09 | AP000753.1 | −0.60 | −0.80 | 1.18 | −0.08 | −0.23 | AC027419.1 | 0.17 | −0.49 | −0.93 | −0.60 | −0.34 |
| LMF2 | 0.24 | −0.40 | −0.46 | −0.11 | 0.10 | BRWD1 | 0.05 | 0.15 | 0.03 | 0.14 | −0.02 | AL137845.2 | −0.06 | −1.74 | 0.21 | −0.11 | 1.58 |
| PHF7 | −0.22 | 0.18 | 0.10 | 0.26 | 0.23 | AL136982.6 | −0.38 | 1.19 | −0.56 | 0.86 | −1.05 | AC010307.1 | −0.06 | 0.70 | 0.33 | 0.83 | −0.79 |
| AC068282.1 | −0.57 | −0.18 | 0.44 | 0.56 | 1.03 | METTL18 | 0.14 | −0.02 | 0.27 | −0.23 | −0.07 | KRT19P3 | 0.21 | −0.45 | −0.22 | 1.03 | 0.50 |
| AC016251.2 | −0.73 | 0.75 | 0.39 | 0.59 | 0.28 | GFI1 | 0.21 | −0.10 | 0.22 | −0.05 | 0.13 | AC026271.3 | −0.01 | 0.24 | 0.46 | −0.24 | −0.32 |
| C16orf71 | −0.60 | 0.13 | 0.70 | 0.00 | 0.53 | ERVK-28 | −0.86 | 0.99 | −0.08 | −2.04 | −2.13 | LINC00884 | 0.02 | −0.04 | −1.77 | −0.17 | −1.20 |
| ACP4 | −0.75 | 0.37 | 0.04 | 0.68 | 0.19 | AC007551.1 | 0.33 | −0.25 | 0.74 | −0.15 | 0.63 | AC010463.2 | 0.03 | −1.37 | −0.74 | −0.97 | −0.17 |
| GRHPR | −0.16 | 0.06 | 0.02 | 0.03 | −0.03 | CADM4 | 0.10 | 0.21 | 0.05 | 0.17 | −0.07 | AC006059.1 | −0.01 | 0.12 | 0.63 | −0.15 | 0.16 |
| MAT2A | 0.31 | −0.30 | −0.58 | −0.09 | −0.10 | MME | −0.31 | 0.17 | 0.89 | −1.05 | −0.27 | MIR580 | −0.08 | −1.40 | −0.65 | −0.20 | 0.17 |
| AL391335.1 | −0.77 | 0.38 | 0.53 | 0.16 | 0.12 | AC083862.1 | −0.28 | −0.37 | 0.87 | −0.54 | 0.75 | OR10D1P | −0.05 | 0.67 | −0.01 | −0.82 | −0.21 |
| RPS27L | −0.28 | 0.02 | 0.41 | −0.06 | 0.12 | NGRN | −0.08 | −0.04 | −0.02 | −0.07 | 0.06 | AC090506.1 | 0.13 | −1.03 | −1.20 | 0.39 | 1.48 |
| RNA5SP301 | −0.64 | 0.10 | 0.61 | −0.77 | 0.21 | COPG2 | 0.13 | 0.10 | 0.15 | 0.09 | −0.12 | AC100802.1 | −0.08 | 0.33 | −1.81 | −0.12 | −1.06 |
| AC008687.2 | −0.69 | −0.11 | −0.30 | 0.20 | 0.64 | AZU1 | −0.47 | −0.60 | 0.37 | 0.32 | −0.31 | AL365184.1 | −0.07 | 0.09 | 0.65 | −0.39 | 0.61 |
| AC083805.1 | −0.84 | −0.01 | 0.44 | 0.16 | 0.38 | RNU6-838P | 0.59 | −0.57 | 0.14 | 0.64 | 0.48 | AC069544.1 | 0.02 | −0.08 | 0.33 | 0.05 | 0.11 |
| RNUSA-1 | −0.95 | 0.16 | −0.67 | 0.89 | −0.38 | EIF4A1P7 | 0.58 | −0.05 | −2.05 | 1.09 | −1.13 | RNU6-371P | −0.10 | −1.04 | −0.01 | 0.08 | 0.40 |
| FAM160A1-DT | −0.58 | 0.93 | −0.10 | 0.56 | −0.28 | BVES | −0.16 | −0.15 | 0.07 | −0.24 | −0.30 | AC109464.1 | 0.13 | 0.42 | −0.59 | −1.07 | −0.33 |
| QPCTL | −0.44 | −0.28 | −0.28 | 0.20 | 0.39 | AL137918.1 | 0.31 | −0.48 | −0.44 | −0.09 | −0.29 | AL596451.1 | 0.11 | −1.21 | −1.09 | −1.82 | −1.78 |
| AZGP1 | −0.46 | 0.61 | 0.79 | 0.47 | −0.18 | RNU1-51P | −0.61 | 0.32 | 0.75 | 0.82 | 1.53 | G36224 | −0.02 | 0.25 | −0.35 | −0.17 | −0.30 |
| SLC8A3 | −0.64 | 0.31 | 0.75 | 0.44 | 0.08 | LINC01055 | −0.52 | −0.21 | 1.11 | −0.07 | 0.17 | GAPDHP28 | 0.07 | −1.51 | −1.19 | 0.54 | 5.37 |
| C1GALT1P1 | −0.56 | 0.38 | 1.27 | 0.41 | 0.30 | NOTCH2NLA | −0.08 | 0.23 | 0.47 | 0.00 | 0.17 | APOL3 | −0.01 | −0.08 | 0.34 | −0.15 | 0.26 |
| SGK3 | −0.27 | 0.21 | 0.48 | 0.03 | 0.08 | AC108215.1 | −0.21 | 0.38 | 1.45 | 0.02 | 0.24 | G30130 | −0.01 | −0.28 | −0.23 | −0.02 | 0.39 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| EGLN3 | −0.55 | 0.04 | 0.28 | 0.07 | 0.13 | AC006144.1 | −0.69 | 0.02 | −0.22 | −0.71 | −0.77 | AC107222.1 | −0.07 | 0.09 | −1.71 | 1.39 | −2.54 |
| ARMC9 | −0.32 | −0.07 | −0.13 | −0.16 | −0.22 | AC084346.2 | 0.47 | 1.10 | 0.32 | 0.58 | −0.16 | CEACAMP4 | −0.08 | −0.31 | −0.69 | 2.24 | 0.86 |
| RN7SL756P | 2.08 | −0.13 | −1.89 | −0.09 | −1.54 | AC025918.2 | 0.65 | −0.78 | 0.50 | −1.10 | 0.17 | MUC17 | −0.04 | −0.46 | −0.62 | 0.84 | 0.01 |
| GLIS2 | −0.44 | 0.53 | 0.45 | −0.14 | −0.18 | AC016769.1 | −0.62 | 1.45 | 1.00 | 0.60 | −0.31 | OR52E7P | 0.06 | −1.52 | 0.50 | −0.64 | 0.53 |
| AL583785.1 | 0.91 | −0.11 | 0.89 | 0.04 | −0.10 | AC016876.3 | −0.58 | 1.10 | −0.61 | 0.70 | 0.32 | RP11-89F3.2 | −0.07 | 1.00 | 0.92 | 0.55 | 1.95 |
| KLHL23 | −0.51 | 0.53 | 0.15 | 0.31 | −0.18 | AC008543.5 | −0.41 | 0.07 | 1.05 | 0.07 | 1.10 | AC109635.4 | 0.05 | 0.30 | −1.17 | 1.52 | −0.72 |
| SLC5A12 | −0.96 | 0.23 | −0.07 | 0.57 | 0.49 | SLC25A5P3 | 1.01 | 0.45 | −0.94 | 1.17 | −0.14 | AC008992.1 | −0.13 | −1.03 | −1.17 | 0.65 | 0.23 |
| CTD-3222D19.7 | −0.42 | −0.28 | 0.36 | 0.30 | 0.52 | MAGEC2 | 1.10 | −0.93 | 0.21 | 0.14 | −0.01 | RNU6-1171P | −0.02 | −0.22 | 0.57 | −0.25 | −0.14 |
| NDUFB6 | 0.26 | −0.23 | −0.07 | −0.11 | −0.03 | AC063924.1 | −0.26 | −0.56 | −0.03 | −0.35 | 0.23 | AC100832.1 | −0.07 | −0.48 | −0.94 | 1.62 | −0.61 |
| LRRC41 | 0.22 | −0.20 | −0.25 | 0.00 | −0.03 | AL445222.1 | 0.18 | −0.08 | −0.29 | −0.02 | 0.43 | AL358913.2 | −0.21 | −0.28 | 1.16 | −0.58 | 0.94 |
| AC143336.1 | −1.10 | 0.42 | −0.31 | 0.41 | 0.34 | MIR3679 | 0.41 | 0.11 | −1.37 | 0.06 | −0.37 | PLA2G4C-AS1 | 0.11 | −0.30 | 1.01 | 2.16 | 1.03 |
| ANKRD39 | −0.33 | 0.07 | 0.38 | −0.01 | 0.23 | STK24P1 | 0.64 | 0.82 | −2.89 | 1.91 | −1.36 | EEF1AKMT2 | 0.01 | −0.06 | −0.11 | 0.11 | 0.01 |
| LINC00519 | 1.11 | −1.07 | −0.48 | 0.32 | 0.07 | AL080250.1 | −0.17 | 0.09 | 0.42 | −0.26 | −0.11 | MTCO3P35 | −0.08 | −0.01 | −0.90 | 0.73 | −0.12 |
| HSD3B7 | 0.54 | −0.31 | −0.10 | −0.37 | −0.10 | C2orf78 | 0.48 | −0.70 | −3.10 | 0.52 | −2.21 | G26596 | 0.03 | −0.31 | 0.73 | −0.37 | 0.10 |
| DPPA3P3 | −1.85 | 1.15 | 3.14 | 1.61 | 1.19 | MT1XP1 | −0.40 | 0.97 | 1.15 | 0.00 | 0.34 | G10909 | 0.03 | −0.04 | −0.20 | 0.53 | −0.05 |
| FAM177A1 | 0.20 | −0.03 | −0.22 | −0.23 | −0.31 | RNA5SP388 | −1.22 | 0.46 | 0.43 | −0.25 | −0.32 | GTF2IP9 | −0.11 | −0.18 | 1.88 | −0.26 | 1.37 |
| AL023584.2 | 0.74 | −0.25 | −1.12 | 0.33 | −0.31 | AC026495.1 | 0.39 | −1.79 | −0.80 | 0.77 | 2.29 | MIR5190 | −0.02 | 0.66 | −0.03 | 0.72 | 0.01 |
| OSTN | −1.35 | 0.77 | 0.55 | −0.69 | −0.75 | EFCAB9 | 0.45 | 0.33 | −0.26 | −0.59 | −0.40 | DMRTC2 | −0.05 | 0.91 | −1.87 | −0.40 | −1.45 |
| RPS3AP5 | 0.56 | −0.67 | −0.45 | 0.08 | −0.08 | RNA5SP139 | −1.24 | 0.51 | 1.59 | 0.52 | 1.86 | RNU6-561P | −0.21 | −0.04 | 0.63 | 0.05 | 1.01 |
| AL024509.1 | −0.84 | 0.19 | 0.77 | −0.02 | 0.14 | CSN2 | −0.73 | 0.72 | −0.15 | 0.21 | −1.63 | AC005011.1 | 0.09 | 0.95 | 0.22 | 0.91 | 0.80 |
| CCDC74B | −0.66 | 0.40 | 0.33 | 0.39 | −0.05 | AC080038.2 | −0.29 | −0.15 | −0.13 | −0.76 | −0.33 | AC007907.1 | 0.06 | −0.28 | −0.30 | 0.91 | 0.89 |
| CEACAM7 | −0.94 | −1.17 | 0.11 | −1.01 | 0.08 | G9514 | 0.42 | −0.18 | 0.41 | 0.40 | −0.69 | MIPEPP2 | 0.05 | −1.49 | −0.07 | −0.55 | −0.74 |
| RMDN3 | −0.23 | −0.04 | −0.01 | 0.02 | 0.20 | AC090371.2 | −0.79 | 0.63 | −0.22 | 0.52 | 0.56 | AC113423.2 | 0.05 | −1.17 | −2.71 | 1.63 | −1.36 |
| RNU6-1331P | 1.39 | −2.15 | −1.51 | −0.49 | −1.02 | RNU6-213P | 0.33 | −1.05 | 0.99 | −0.41 | 1.08 | NFU1P1 | −0.12 | −0.25 | −0.80 | −1.00 | −2.91 |
| 2-Sep | 0.22 | −0.14 | −0.11 | −0.11 | −0.22 | MIR3648 | −0.17 | 0.06 | −0.54 | 0.03 | −0.05 | DRC1 | 0.03 | 0.48 | −1.41 | 0.35 | −0.88 |
| HLA-DQB1 | 0.50 | −0.51 | −0.14 | −0.09 | 0.13 | CD164 | 0.10 | 0.03 | 0.12 | −0.06 | 0.00 | AC073913.2 | 0.15 | −0.71 | 1.52 | −0.78 | 0.64 |
| AL691432.1 | −0.48 | 0.34 | 0.49 | 0.51 | 0.43 | RN7SL788P | −0.23 | −0.21 | −0.73 | −0.18 | 0.09 | AC139365.1 | −0.20 | −0.87 | −0.44 | −0.49 | 0.23 |
| AC025271.4 | −1.19 | 1.41 | 1.89 | 1.17 | 0.40 | MACC1-AS1 | −0.31 | −0.25 | 1.00 | −0.32 | 0.09 | LINC02269 | −0.11 | −1.29 | −2.03 | 0.46 | −0.53 |
| AL158211.1 | −1.75 | −0.78 | 3.37 | −0.60 | 2.06 | AC084782.3 | −0.45 | 0.80 | −0.41 | 0.94 | −1.05 | HMGN2P31 | 0.20 | −0.06 | −0.36 | 0.06 | 0.21 |
| FAM171B | −0.34 | 0.60 | 1.35 | 0.12 | 0.17 | PWRN2 | −0.56 | −1.18 | −0.59 | 0.66 | 0.78 | PRR13P4 | −0.19 | 0.29 | 1.02 | −0.51 | 0.07 |
| GEMIN2 | 0.19 | 0.06 | −0.18 | −0.07 | −0.18 | CASKP1 | 0.87 | −0.93 | −1.59 | 0.57 | −0.16 | PRKACA | −0.01 | 0.11 | 0.02 | 0.04 | −0.12 |
| AL442071.1 | 0.57 | −0.20 | −0.72 | −0.15 | 0.04 | SMIM20 | 0.16 | −0.24 | 0.08 | −0.24 | −0.05 | PIGCP2 | 0.19 | −0.81 | −1.40 | 0.39 | 0.71 |
| RNU6-1242P | 0.91 | −1.52 | −1.66 | −0.05 | 0.48 | C5AR1 | 0.24 | −0.55 | −0.21 | −0.49 | −0.49 | AP001208.2 | −0.02 | 0.36 | 0.40 | 0.19 | 0.78 |
| PRKARIA | 0.25 | 0.01 | −0.26 | 0.05 | −0.21 | CKAP2P1 | 0.61 | 0.66 | −0.61 | 1.25 | 0.43 | AL138775.1 | 0.07 | 0.52 | −0.89 | 1.74 | −1.62 |
| DMAC1 | 0.30 | −0.11 | 0.07 | −0.19 | −0.10 | AL161729.1 | −0.47 | −0.45 | −0.52 | 1.41 | 0.43 | RNA5SP324 | 0.05 | −1.56 | −0.75 | 0.09 | 1.50 |
| CRTC2 | −0.27 | 0.20 | 0.05 | 0.19 | 0.02 | AL135960.1 | 0.23 | −0.25 | 0.83 | −0.60 | 0.30 | AC022655.2 | 0.09 | −0.39 | 1.18 | 1.17 | 0.67 |
| POLR3K | 0.52 | −0.60 | −0.38 | −0.39 | 0.04 | AL034550.1 | −0.23 | −0.37 | 0.62 | −0.43 | 0.19 | AC063977.6 | 0.06 | −1.78 | 0.42 | −0.44 | 0.82 |
| AL021396.1 | −1.07 | 1.13 | −0.79 | 1.30 | 0.06 | AL162425.1 | 0.60 | −0.32 | −0.94 | 0.10 | −2.12 | AC011591.2 | 0.04 | 1.49 | 0.03 | 0.54 | −0.04 |
| AC036214.4 | 0.52 | −0.16 | 0.12 | 0.22 | 0.06 | RNA5SP166 | −0.80 | 0.81 | −0.27 | −0.31 | −1.57 | CPNE4 | 0.02 | −0.95 | 0.33 | −0.29 | 0.38 |
| AC007220.1 | −0.97 | 0.75 | 1.32 | 0.53 | 0.98 | AC003035.2 | −0.77 | −0.32 | −0.78 | 1.53 | 2.03 | AC138517.1 | 0.19 | −0.54 | −0.42 | 1.63 | −0.40 |
| AL590627.1 | −0.34 | 0.18 | 0.25 | 0.08 | 0.30 | G24438 | 0.61 | −0.05 | −0.64 | −0.03 | −0.31 | AF279873.4 | 0.20 | −0.59 | −1.60 | −1.25 | −2.22 |
| SCN4A | −0.95 | 0.39 | 0.07 | 1.39 | −0.02 | AL590787.1 | −0.41 | 1.02 | 0.27 | 1.25 | −0.83 | RN7SL390P | −0.03 | −0.80 | −0.26 | 0.24 | −0.17 |
| ACTN4 | 0.19 | 0.04 | −0.25 | −0.03 | −0.31 | RNU6-208P | −0.61 | −1.46 | 0.47 | −0.83 | 0.36 | RNU6-248P | −0.20 | −0.18 | 0.65 | −0.40 | 1.00 |
| NPM1P35 | 1.58 | −0.84 | −2.68 | −0.01 | −1.34 | AL365202.1 | 0.28 | −0.39 | 0.72 | 0.05 | 0.71 | AC040896.1 | −0.08 | 1.47 | 0.64 | −0.18 | −0.09 |
| AVL9 | 0.15 | 0.01 | −0.16 | 0.02 | −0.14 | FABP5P12 | 1.03 | 1.36 | −2.12 | 0.42 | −1.09 | AC087362.2 | 0.03 | −0.23 | 0.10 | 0.01 | −0.01 |
| OXCT1-AS1 | −0.87 | 0.00 | 0.44 | −0.15 | 0.01 | AL442663.2 | 0.24 | −0.88 | −1.66 | −0.39 | −0.49 | AC104445.1 | 0.12 | 1.32 | 0.17 | 0.27 | −2.42 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| CSRNP1 | 0.49 | −0.43 | −0.90 | −0.29 | −0.84 | MED4-AS1 | −0.31 | 0.33 | −0.52 | −0.31 | −0.31 | PRSS56 | −0.04 | −0.76 | 0.80 | −0.87 | 0.41 |
| NDUFA9P1 | 0.43 | −0.19 | −0.33 | −0.17 | 0.11 | AC005726.3 | −0.25 | −0.35 | −0.56 | −0.04 | 0.03 | KLRF1 | 0.02 | −0.35 | 0.31 | 0.00 | 0.09 |
| CNKSR3 | 0.24 | −0.05 | −0.38 | 0.11 | −0.08 | RPL34P18 | 0.40 | 0.18 | −2.06 | 0.78 | −0.98 | MAGEB17 | −0.18 | 0.22 | 0.90 | −0.04 | −0.14 |
| MIR4731 | −0.66 | 0.17 | −0.25 | −0.31 | −0.74 | RN7SL277P | 0.21 | −0.17 | 0.25 | 0.07 | 0.50 | LYZL1 | 0.16 | −0.27 | −0.83 | 0.99 | 0.32 |
| FAM219B | −0.22 | 0.24 | 0.23 | 0.22 | −0.04 | SPON1 | 0.18 | −0.06 | 0.61 | −0.55 | 0.01 | AC100768.1 | −0.19 | −0.88 | −1.72 | 0.72 | −0.72 |
| CTDSP1 | −0.20 | 0.09 | 0.01 | 0.20 | 0.11 | ROCK1P1 | −0.36 | 0.05 | −0.70 | 0.36 | −0.39 | OR11J2P | −0.20 | 0.56 | 0.94 | −1.51 | 0.48 |
| AC073957.3 | −0.35 | 0.37 | 0.46 | −0.03 | −0.20 | AC018648.1 | 0.34 | 0.52 | −0.16 | −0.20 | −0.55 | FMO7P | 0.20 | −0.11 | 0.25 | −0.79 | 1.09 |
| RN7SL752P | −0.65 | 0.15 | −0.40 | 0.40 | −0.34 | KIAA0087 | −0.32 | −0.33 | −0.31 | 0.04 | −0.58 | MTCO2P3 | −0.20 | −0.26 | −0.13 | −0.99 | −0.64 |
| JARID2 | 0.24 | −0.01 | −0.35 | 0.04 | −0.24 | G25290 | 0.57 | 0.26 | −1.01 | −0.19 | −0.43 | RPS3AP23 | −0.03 | −1.61 | −1.05 | −0.59 | −0.74 |
| MFSD9 | 0.27 | 0.05 | 0.11 | 0.05 | −0.10 | KIR3DL3 | 0.74 | −0.85 | −0.80 | −0.23 | −2.41 | RPL10P5 | −0.20 | −0.13 | 0.59 | 0.64 | 1.91 |
| CYBA | 0.44 | −0.34 | −0.05 | −0.45 | −0.16 | RPSAP16 | −0.16 | −0.12 | 0.37 | −0.13 | 0.31 | EVX1-AS | 0.20 | 0.70 | −0.24 | 0.84 | −1.46 |
| LINC01624 | −1.14 | −0.32 | −0.72 | 0.75 | 0.34 | CLEC18C | −0.70 | −0.06 | 0.77 | 0.95 | −0.59 | AC055878.1 | −0.20 | 0.15 | 0.04 | 0.83 | −0.16 |
| RN7SL736P | −1.17 | 0.73 | −0.89 | 0.16 | −1.50 | AC127521.1 | −0.37 | −0.28 | 0.87 | −0.75 | 0.70 | AC231760.1 | 0.16 | −0.48 | −0.64 | −1.27 | −1.86 |
| ANKRD2 | −0.99 | 0.82 | 0.77 | 0.15 | −0.02 | RPL7P12 | −0.85 | −1.04 | 0.34 | 0.41 | 1.93 | AC100814.1 | 0.03 | −1.52 | 0.30 | −0.66 | 0.06 |
| AC004552.1 | 1.11 | −1.36 | −0.38 | −0.26 | 1.09 | LINC02396 | 0.72 | −0.36 | −2.78 | 1.21 | −1.75 | COL4A2-AS2 | −0.02 | −0.48 | 0.21 | −0.69 | −0.10 |
| POMGNT1 | −0.23 | 0.09 | 0.03 | 0.01 | 0.14 | AC009949.1 | 0.53 | −0.47 | 0.11 | −0.50 | 0.19 | AL136181.1 | 0.08 | −0.98 | −0.47 | 0.27 | 0.39 |
| FYB2 | −1.14 | 0.79 | 0.62 | −0.10 | −0.17 | NPM1P32 | 0.49 | 0.26 | −0.29 | 0.41 | −0.62 | AC103740.2 | −0.06 | 0.30 | −0.80 | 0.29 | −0.51 |
| FP325331.1 | −0.50 | 0.21 | −0.05 | 0.22 | −0.04 | AL121768.1 | 0.48 | −1.08 | 0.49 | −0.60 | −1.15 | OR10AA1P | 0.17 | −0.28 | 0.39 | 0.09 | 2.02 |
| AC116347.1 | 1.65 | −0.94 | −3.23 | −0.19 | −1.16 | PDE3A | −0.18 | −0.04 | 0.56 | −0.12 | −0.13 | RGPD1 | 0.02 | 0.90 | −0.48 | 0.66 | −0.48 |
| DTWD1 | −0.30 | 0.19 | 0.63 | −0.10 | 0.17 | ABCC11 | −0.16 | −0.36 | −0.15 | 0.13 | 0.30 | AL606469.1 | −0.05 | 1.22 | 1.47 | −0.34 | −0.31 |
| COL20A1 | −1.21 | 0.33 | −0.74 | 0.31 | 0.44 | LINC00299 | −0.30 | −0.34 | 0.34 | −0.64 | 0.43 | AL021937.2 | −0.03 | 0.19 | 1.76 | 0.29 | 0.10 |
| SEMA4A | −0.27 | 0.08 | 0.06 | 0.12 | 0.14 | AC079341.1 | 0.80 | −0.15 | −0.25 | 1.34 | −1.09 | GH2 | −0.20 | −0.29 | −0.26 | 1.31 | −0.43 |
| SNF8 | 0.13 | −0.11 | 0.05 | −0.13 | 0.04 | AC009804.2 | 0.52 | −0.32 | −0.55 | −0.29 | 1.16 | SNRPGP6 | −0.20 | 0.34 | −0.65 | 1.95 | −0.06 |
| GPR137C | 0.60 | −0.10 | −0.76 | 0.43 | −0.45 | NDUFAF7 | 0.08 | −0.10 | 0.03 | −0.02 | 0.13 | AC091860.1 | −0.20 | −0.25 | −1.48 | 0.73 | −2.59 |
| ERBIN | 0.24 | 0.00 | −0.03 | −0.08 | −0.22 | AC005232.1 | 0.37 | −0.72 | −0.10 | −0.67 | −0.42 | BCRP9 | −0.10 | −0.91 | −1.30 | 0.88 | 0.22 |
| EDF1 | 0.22 | 0.03 | −0.23 | 0.03 | −0.29 | PAX9 | 0.21 | −0.24 | −0.21 | 0.12 | −0.19 | AC090099.2 | −0.20 | 0.62 | −0.58 | 1.29 | −2.13 |
| G41779 | −1.24 | −0.31 | 1.08 | −1.14 | −0.84 | AC019131.1 | 0.60 | −0.42 | −1.22 | −0.15 | −2.35 | AL390840.1 | −0.20 | −0.82 | 0.29 | −1.03 | −0.24 |
| NUTM1 | −0.80 | 0.68 | −0.06 | 0.31 | −0.29 | AKR1B1P1 | −0.34 | −0.09 | 0.19 | 0.13 | 0.10 | AP001823.1 | 0.18 | −1.51 | −1.24 | −1.19 | 0.15 |
| RPL39P3 | 0.60 | −0.36 | 0.08 | −0.38 | −0.18 | MPP3 | −0.11 | −0.24 | −0.30 | 0.05 | −0.02 | AL355377.1 | −0.02 | 0.02 | −0.16 | −0.52 | −0.31 |
| HLA-DQA1 | 0.54 | −0.56 | −0.06 | −0.11 | 0.22 | RLIMP1 | −0.12 | 0.18 | 0.22 | −0.20 | −0.07 | AC024022.1 | 0.08 | −0.60 | 0.32 | 0.99 | 0.48 |
| BCAS2P3 | 2.34 | −1.54 | −3.02 | −1.24 | −2.84 | AC018755.3 | 0.42 | 0.09 | 0.83 | −0.32 | −0.26 | MT1H | 0.02 | −0.40 | −0.05 | −0.26 | 0.14 |
| AC006213.6 | −0.59 | 0.32 | 0.93 | −0.10 | 0.19 | AP001148.1 | −0.22 | −0.01 | 0.79 | 0.11 | 0.75 | AL646016.1 | 0.20 | −1.34 | −0.52 | −1.03 | −0.75 |
| GPR68 | 0.39 | −0.41 | −0.70 | 0.02 | 0.01 | AP000357.1 | 0.51 | −0.46 | −0.59 | −0.17 | −1.35 | HNRNPDLP1 | −0.20 | 0.96 | −0.71 | 1.26 | −1.81 |
| HAUS8 | 0.26 | −0.43 | −0.72 | −0.19 | −0.33 | AC084864.1 | −0.63 | 0.60 | −0.85 | −0.77 | −2.31 | AL160175.1 | −0.02 | −0.18 | −0.67 | 0.44 | 0.28 |
| HSH2D | 0.98 | −1.17 | −0.32 | −0.84 | 0.31 | RNU6-729P | −0.42 | 0.78 | 0.49 | −0.77 | −0.87 | RNU6-892P | 0.03 | −0.53 | 0.10 | −0.04 | 0.45 |
| G29811 | −0.81 | 0.21 | 0.93 | 0.24 | 0.74 | AL157778.1 | 0.60 | −0.14 | −1.92 | 0.06 | −1.75 | OR5AC4P | −0.20 | −0.10 | 0.86 | 1.80 | −1.30 |
| RPL7AP30 | 0.59 | −0.06 | −0.23 | 0.26 | −0.03 | DMBT1 | 0.39 | −0.94 | −0.71 | 0.10 | −0.14 | AP005019.2 | −0.07 | −0.12 | −0.28 | 0.73 | −0.87 |
| OR52X1P | −1.24 | −0.20 | 0.45 | 1.06 | 1.41 | EEF1A1P22 | −0.27 | 0.34 | −0.26 | 0.26 | −0.48 | IGLV2-14 | 0.20 | 0.21 | 0.97 | −0.35 | 1.61 |
| RPL15P18 | −0.82 | 0.43 | 0.78 | 0.57 | 1.09 | AL139123.1 | −0.28 | 0.57 | 0.10 | 0.16 | −0.55 | HNRNPLP1 | 0.04 | 0.38 | −0.99 | 0.74 | −0.02 |
| KCNH2 | −0.76 | 0.01 | −0.39 | 0.12 | −0.66 | BSPH1 | −0.55 | −0.62 | −1.62 | −1.24 | −0.96 | G23010 | −0.02 | 0.11 | 0.26 | 0.17 | −0.37 |
| ART5 | −1.22 | −0.43 | 0.80 | −0.02 | 1.46 | CYCSP5 | 0.96 | −1.45 | 0.63 | −0.89 | 1.94 | AL356019.1 | −0.09 | −0.97 | 0.58 | −0.14 | −0.15 |
| AL117340.1 | −0.64 | −0.03 | 0.21 | 0.28 | 0.14 | AC006487.1 | −0.34 | 0.22 | −0.27 | −0.13 | −0.27 | MRLN | −0.02 | −1.00 | −0.20 | −0.30 | 0.61 |
| ITPRIP | 0.39 | 0.07 | −0.57 | 0.06 | −0.63 | DHX9P1 | 0.47 | −1.29 | −1.48 | 0.28 | −0.80 | GRB7 | 0.01 | 0.38 | −0.18 | 0.36 | −0.12 |
| AC098934.1 | −0.71 | −0.05 | 1.47 | 0.15 | 0.22 | IL17RA | 0.05 | −0.17 | −0.18 | −0.07 | −0.03 | KHDC1 | −0.01 | −0.24 | −0.39 | 0.01 | 0.10 |
| AC026412.1 | −0.29 | 0.21 | 0.25 | 0.04 | 0.18 | MTHFD2P7 | −0.76 | −0.36 | −1.43 | 1.69 | −0.60 | GNPATP | −0.12 | −0.32 | −0.82 | −0.50 | 1.03 |
| LINC02408 | 1.13 | −0.95 | −1.65 | −0.15 | 0.70 | AP003390.2 | 0.29 | 0.16 | 0.05 | 0.15 | 0.16 | AL080312.1 | −0.18 | −0.24 | −1.38 | 1.09 | −0.54 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| KLF5 | 0.43 | 0.15 | −0.14 | 0.18 | −0.14 | AC121251.1 | 0.28 | 0.24 | 0.09 | −0.33 | −0.31 | ODF4 | −0.04 | −2.16 | −0.30 | 0.12 | 0.03 |
| OCM | −1.11 | 1.03 | 0.00 | 0.82 | 0.38 | AC012519.1 | −1.00 | 0.68 | 0.81 | 1.75 | 1.10 | PSPC1-AS2 | 0.02 | 0.17 | 0.28 | 0.37 | −0.18 |
| G36656 | 2.17 | −0.28 | −2.39 | −0.81 | −3.69 | IL10RB-DT | −0.28 | −0.74 | 0.94 | −0.38 | 0.51 | ACTG1P13 | −0.20 | −0.40 | −0.77 | 0.04 | 0.34 |
| SIT1 | 1.00 | −1.30 | 0.31 | −0.46 | 0.88 | FAM86JP | −0.16 | 0.02 | −0.29 | −0.03 | −0.26 | LINC02389 | 0.03 | −0.88 | 0.29 | −0.54 | 0.93 |
| AP005131.2 | −0.55 | 0.20 | 0.53 | −0.04 | −0.05 | NXPE3 | 0.11 | −0.06 | 0.32 | −0.17 | 0.22 | AC063977.4 | −0.14 | 0.25 | −0.97 | 0.26 | −1.05 |
| KCNH3 | −0.58 | −0.19 | −0.15 | 0.30 | 0.68 | RP11-589F5.3 | 0.38 | 1.02 | −0.17 | −0.01 | −0.14 | OR5W2 | 0.06 | −0.31 | 0.09 | 0.34 | −1.33 |
| MROH3P | −0.50 | 0.41 | 0.54 | −0.07 | −0.18 | AL079342.1 | −0.67 | 0.45 | 0.27 | 0.45 | 0.08 | AC093627.4 | −0.02 | −0.07 | 0.64 | 0.33 | 0.32 |
| EMCN | −0.50 | 0.19 | 1.47 | −0.38 | 0.13 | IKBKG | −0.10 | −0.03 | −0.37 | 0.25 | 0.13 | AC099791.3 | 0.04 | 0.29 | −0.51 | 0.14 | −0.84 |
| AC099062.1 | −1.00 | −0.54 | −0.28 | −0.38 | −0.21 | IQCB1 | 0.06 | −0.11 | 0.06 | −0.02 | 0.22 | AC025423.1 | −0.02 | −0.12 | −0.79 | 0.36 | −0.03 |
| AP001922.1 | −1.16 | 0.14 | −0.68 | 0.72 | −0.14 | AL627422.1 | 0.75 | 0.00 | −2.12 | 0.32 | −1.57 | AL137003.1 | −0.01 | 0.15 | −0.88 | 0.13 | −0.41 |
| CYP4A22-AS1 | 1.05 | −0.73 | −1.00 | 0.18 | −0.74 | RNA5SP467 | −0.58 | 0.04 | 1.70 | 0.49 | 0.61 | AC108134.1 | 0.02 | 0.62 | 0.46 | 0.12 | 0.04 |
| AC008771.1 | 0.41 | 0.03 | −0.07 | 0.00 | −0.17 | MTNR1B | 0.48 | −1.04 | −0.93 | −0.02 | −0.96 | OR7E66P | −0.12 | −0.76 | −0.03 | 1.93 | 1.12 |
| GFI1B | −0.83 | −0.14 | −1.07 | 0.02 | 0.00 | CD6 | 0.24 | −0.93 | 0.21 | −0.96 | 0.40 | LINC01641 | 0.04 | −0.37 | 0.13 | 2.02 | 1.06 |
| FAM208A | 0.17 | −0.05 | −0.02 | −0.08 | −0.03 | REG3G | 0.65 | −0.33 | −1.74 | 0.41 | −0.81 | MTDHP4 | −0.14 | −0.60 | 2.19 | −1.13 | 2.44 |
| HRAT92 | −0.73 | 0.71 | 0.00 | 0.19 | −0.42 | AC027338.2 | 0.74 | 0.43 | −1.43 | −0.21 | −2.23 | SDHC | 0.00 | −0.05 | −0.03 | 0.02 | 0.02 |
| AZIN1 | 0.28 | −0.06 | 0.08 | −0.09 | −0.17 | AC078906.1 | −0.35 | −0.99 | 0.74 | −0.33 | 0.47 | DSTNP1 | 0.01 | −0.05 | 0.21 | 0.01 | 0.04 |
| NLRP2B | −1.03 | −0.16 | 0.12 | 0.72 | 0.51 | PCBP4 | −0.08 | −0.09 | −0.06 | −0.02 | 0.15 | AL035090.1 | 0.03 | −0.24 | 0.07 | −0.53 | −0.01 |
| AC008456.1 | 0.97 | 0.61 | 0.17 | 0.14 | −0.39 | G31022 | 0.35 | −0.19 | 0.48 | 0.12 | 0.42 | C20orf173 | 0.05 | −0.88 | 0.16 | −0.14 | 1.35 |
| AC010243.1 | 0.75 | −0.23 | 0.16 | −0.12 | −0.01 | SNORA19 | −0.20 | 0.39 | −0.07 | 0.37 | −0.52 | NPIPB9 | 0.04 | −0.96 | 0.85 | 0.08 | 1.25 |
| IKZF3 | 0.67 | −0.67 | 0.39 | −0.52 | 0.60 | SNORD114-15 | 0.74 | −0.74 | 0.02 | −0.52 | −1.14 | PANCR | 0.10 | −0.90 | 1.31 | 1.21 | 2.12 |
| ADORA2B | 0.46 | −0.39 | −0.46 | −0.08 | −0.05 | AL049869.2 | −0.38 | 1.41 | 0.36 | −0.04 | −0.79 | RAB11AP2 | 0.19 | 0.19 | −0.13 | −0.59 | −1.58 |
| GPR89A | 0.30 | −0.09 | 0.08 | −0.05 | −0.03 | AC004217.2 | −0.27 | 0.46 | −0.01 | −0.12 | −0.75 | AC008608.2 | 0.02 | 1.10 | 0.01 | 0.93 | −0.46 |
| AC010301.1 | 1.13 | −0.55 | 0.31 | −0.03 | 0.28 | RPL24P4 | 0.19 | −0.07 | −0.28 | 0.15 | −0.03 | RN7SL273P | 0.10 | 0.20 | −0.37 | 0.11 | −0.84 |
| CASS4 | 0.76 | −1.12 | −0.77 | 0.05 | −0.29 | LMO7DN | −0.39 | −0.24 | 0.08 | −0.52 | 0.40 | RANP2 | −0.19 | 0.15 | −0.88 | −0.33 | −0.94 |
| LINC02503 | −1.11 | 0.89 | 0.85 | 0.07 | −0.12 | AL035422.1 | −0.38 | 0.45 | −0.81 | 0.20 | −1.29 | AC106820.5 | 0.04 | 0.13 | 1.21 | 0.93 | 1.53 |
| CACYBPP2 | 0.80 | −0.70 | −0.68 | −0.47 | −0.80 | AC104984.1 | −0.41 | 0.62 | −0.57 | 0.97 | −0.88 | RNU6-684P | 0.19 | −0.24 | −0.62 | 0.86 | 1.31 |
| AC048382.1 | −0.69 | 0.83 | 0.67 | 0.21 | 0.06 | NEURLIB | 0.13 | 0.12 | 0.20 | 0.05 | −0.13 | AC078850.1 | −0.03 | −0.15 | −2.00 | 0.81 | −0.42 |
| NR4A1 | −0.65 | 0.65 | −0.85 | −0.16 | −0.66 | BCLAF1P1 | 0.35 | −0.02 | −0.48 | 0.44 | −0.57 | AL512306.1 | 0.02 | 0.12 | −0.43 | 0.08 | −0.10 |
| AL445437.1 | −1.12 | 0.43 | 0.29 | 0.34 | −0.26 | LINC01187 | 0.57 | −1.42 | −1.82 | 0.58 | 0.58 | AL133383.2 | 0.14 | 0.75 | −0.68 | −0.02 | −1.59 |
| KIF12 | −0.77 | 0.45 | −0.49 | 0.45 | −0.04 | RPL7AP9 | −0.37 | 0.69 | 0.03 | 0.50 | 0.19 | C11orf40 | −0.19 | 0.79 | −0.51 | 0.06 | −2.97 |
| AC090543.1 | 0.78 | −0.20 | −0.25 | −0.26 | 0.02 | AC108022.1 | 0.72 | 0.68 | −0.64 | −0.59 | −1.91 | AC007326.3 | −0.05 | −1.05 | 1.23 | −0.28 | 0.62 |
| AC246817.2 | −0.76 | −0.42 | 0.33 | 0.03 | 0.31 | NAP1L5 | −0.09 | 0.09 | 0.30 | 0.11 | 0.02 | PPIAP76 | 0.04 | 0.66 | 1.56 | 0.15 | −0.42 |
| AC004784.1 | −1.24 | 0.55 | 2.07 | 0.09 | −0.14 | AC128676.1 | −1.36 | −0.93 | 1.21 | 0.88 | 2.02 | IGKV1D-43 | −0.09 | 0.39 | 0.70 | 1.50 | −2.53 |
| PCNX3 | 0.25 | −0.20 | −0.37 | 0.06 | 0.00 | ADARB2-AS1 | −0.96 | −1.08 | 1.67 | −2.03 | 1.17 | AP000542.2 | 0.05 | −0.32 | −1.32 | 1.69 | −2.29 |
| KRT8 | −0.69 | 0.86 | 0.81 | 0.26 | 0.03 | RBM8A | −0.07 | 0.08 | −0.25 | 0.17 | −0.13 | ESX1 | 0.19 | −0.27 | 0.43 | −0.31 | 0.43 |
| AL022326.2 | −0.90 | 0.97 | 2.48 | 0.16 | 1.24 | AC004878.6 | −0.68 | 0.82 | 1.28 | 1.37 | 0.83 | AC133963.1 | 0.08 | 1.51 | −1.55 | 0.76 | −1.96 |
| AC106791.1 | −0.68 | 0.52 | 0.58 | 0.24 | −0.02 | RNU7-97P | −1.39 | −0.58 | 1.47 | −2.00 | 1.28 | SSXP3 | −0.08 | 0.10 | −0.01 | −1.49 | 0.05 |
| AC100872.1 | −1.45 | 0.17 | 2.10 | 1.52 | −0.12 | DDX43 | 0.17 | 0.39 | −0.62 | 0.82 | −0.70 | AL031595.2 | −0.02 | −0.39 | −0.62 | −0.40 | −0.39 |
| COX7C | 0.49 | −0.24 | 0.02 | −0.54 | −0.07 | RBMX2P1 | −0.34 | −0.25 | 0.45 | −0.37 | −0.07 | AC009035.1 | −0.05 | 0.22 | 0.17 | −0.65 | 0.38 |
| RN7SL501P | −0.63 | 0.48 | 0.90 | 0.45 | 0.20 | AL139328.1 | 0.48 | −0.43 | −2.01 | 0.09 | −2.11 | IGKV2-23 | 0.19 | 1.12 | −0.36 | 0.46 | −1.84 |
| C10orf88 | 0.23 | −0.08 | 0.03 | −0.07 | 0.18 | AP002392.1 | 0.44 | −1.26 | −1.11 | −0.23 | 0.13 | MIR4504 | 0.09 | −0.78 | 0.28 | 1.69 | 1.20 |
| AL353729.2 | −0.76 | 0.39 | 1.21 | 0.21 | −0.08 | AC097504.2 | −0.99 | −0.83 | 0.21 | −0.06 | 0.71 | IGHV3-29 | 0.19 | −2.12 | −1.13 | −0.54 | −0.68 |
| GSPT2 | −0.40 | 0.24 | 0.64 | −0.01 | 0.37 | AC122710.2 | 0.35 | −0.72 | −0.81 | 0.01 | −0.17 | RP11-463P17.3 | −0.08 | −0.32 | 0.83 | 1.47 | 3.29 |
| MAPK13 | 0.40 | 0.05 | −0.28 | 0.08 | −0.32 | AC241520.1 | −0.16 | −0.41 | 0.22 | −0.10 | 0.92 | AL359821.1 | 0.04 | −1.13 | 0.15 | 0.02 | −0.10 |
| AC009268.2 | 0.80 | −0.79 | −1.12 | −0.36 | −0.51 | SPACA1 | −0.83 | −0.67 | −0.93 | −0.65 | −0.35 | SLC20A1P1 | 0.07 | −1.71 | −1.48 | −1.43 | −1.35 |
| RRP8 | −0.21 | −0.02 | 0.11 | 0.08 | 0.26 | AL121890.3 | −0.81 | 0.59 | −0.39 | 1.02 | −2.02 | OR5M7P | 0.19 | 0.16 | 0.03 | 0.41 | −1.01 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AL050403.1 | −1.11 | 0.99 | 0.51 | 0.38 | −0.36 | SPATA46 | −0.26 | −0.04 | 0.54 | 0.34 | 0.77 | G28534 | −0.04 | −0.52 | −0.51 | −0.11 | 0.58 |
| MIR590 | 0.86 | −0.62 | −0.04 | −0.32 | 0.04 | AC093770.1 | 0.26 | −0.07 | 0.66 | 0.21 | 0.78 | HTR2A | 0.02 | 0.18 | 0.02 | −0.16 | −0.61 |
| AP002336.3 | 1.16 | −0.69 | −1.06 | −0.04 | −0.06 | HMGB3P18 | −0.50 | 1.48 | 1.60 | −0.36 | 0.10 | RNA5SP258 | −0.19 | −1.12 | −0.22 | −1.58 | −1.27 |
| ARMC12 | −0.84 | −0.04 | 0.31 | 0.45 | 0.69 | SNORD17 | −0.13 | 0.14 | 0.16 | −0.07 | −0.11 | AC109780.2 | 0.09 | −0.79 | −0.74 | 0.06 | 0.45 |
| CTBP1-DT | −0.18 | 0.18 | 0.14 | 0.12 | 0.13 | AC083809.1 | 0.78 | −1.53 | −1.31 | −0.14 | 1.11 | SLCO1B1 | 0.06 | −0.66 | −0.30 | −0.36 | 0.69 |
| SNORD38A | −1.43 | 0.00 | 1.84 | −0.10 | 0.64 | RN7SL630P | −0.31 | 0.59 | −0.29 | 0.65 | −0.01 | AC125421.1 | 0.19 | 0.07 | −1.39 | 2.21 | 0.58 |
| FCF1P8 | 0.81 | −0.44 | 0.16 | −0.02 | −0.11 | AL135785.1 | −1.00 | −0.04 | 0.87 | 0.04 | 0.22 | MTND6P9 | −0.19 | −0.17 | 0.59 | −1.15 | −0.45 |
| AC138409.2 | −0.25 | 0.17 | 0.25 | 0.19 | 0.21 | AL133371.2 | 0.48 | −0.72 | −0.79 | −0.18 | 0.10 | AC111170.3 | −0.01 | −0.59 | −0.64 | −0.32 | −0.11 |
| AC090948.3 | 0.45 | −0.34 | −0.53 | −0.24 | 0.11 | MYH13 | 0.29 | −0.67 | −0.76 | −0.57 | −0.68 | HSD17B3 | 0.09 | −0.74 | −0.91 | 0.35 | 0.67 |
| PATL2 | −0.42 | −0.22 | 0.09 | 0.03 | 0.50 | AC104002.1 | −1.09 | 0.25 | 1.71 | 0.77 | 1.41 | OR6B2 | −0.06 | −1.50 | 0.05 | −1.13 | 0.52 |
| SPRR4 | 1.14 | −0.01 | −0.69 | −0.61 | −0.56 | LINC00862 | −0.24 | 0.25 | 0.07 | −0.16 | −0.28 | SNPH | −0.01 | 0.12 | −0.41 | 0.08 | −0.08 |
| KIAA0825 | −0.28 | 0.13 | 0.35 | 0.00 | 0.09 | CDC42EP5 | 0.13 | −0.13 | −0.01 | −0.06 | −0.01 | HOXA4 | 0.02 | 0.20 | −1.26 | 1.25 | −0.14 |
| KIF5C | −0.59 | 0.20 | 0.62 | −0.06 | 0.52 | AL512310.6 | −0.89 | −0.76 | −1.23 | −0.48 | 0.75 | AC084017.1 | 0.07 | −0.04 | −0.66 | 0.01 | −1.46 |
| SLC8A1-AS1 | −0.50 | −0.25 | 0.83 | −0.12 | 0.55 | LINC00570 | 0.39 | −0.15 | −0.78 | 0.45 | −0.92 | AC005758.1 | −0.09 | −0.84 | 1.40 | −0.21 | −1.28 |
| RPS25 | 0.28 | −0.03 | −0.11 | −0.05 | −0.34 | RNU6-140P | 0.31 | −0.28 | −0.40 | 0.92 | 0.07 | AL591503.3 | 0.19 | −0.52 | −0.89 | −0.36 | NA |
| PIK3C2B | −0.31 | 0.36 | 0.39 | 0.37 | 0.12 | CLUHP5 | 0.72 | −1.59 | −2.05 | 0.13 | −1.43 | MTATP6P30 | 0.19 | −0.65 | −0.66 | 0.58 | −0.18 |
| MIR181B1 | 2.11 | −1.71 | −1.63 | −0.70 | −1.53 | AC024909.2 | 0.72 | −0.16 | −0.13 | 0.30 | −0.82 | AC016383.1 | 0.11 | 0.44 | −0.50 | 1.17 | −2.09 |
| AL139240.1 | −1.33 | −1.49 | 0.64 | −0.52 | 1.49 | AC134775.1 | −0.24 | −0.25 | −0.12 | 0.04 | 0.02 | AP002371.1 | 0.19 | 1.42 | −0.47 | 0.41 | −2.18 |
| ESRRA | 0.39 | −0.20 | −0.44 | 0.15 | 0.29 | AC090699.1 | 0.33 | −0.87 | −0.39 | 0.83 | −0.02 | PITX3 | 0.04 | −1.65 | 0.64 | −0.61 | 0.95 |
| EPOR | −0.38 | 0.10 | 0.38 | 0.16 | 0.28 | NLRP13 | 0.62 | −0.39 | −2.55 | 0.13 | −1.85 | LINC00558 | 0.05 | −0.50 | −0.34 | 0.39 | 0.30 |
| AC098851.1 | −0.65 | 0.61 | 1.11 | 0.29 | 0.39 | AL161646.2 | 0.67 | −0.84 | −1.54 | 0.21 | −1.94 | EEF1A1P42 | −0.06 | 0.50 | −2.94 | 0.65 | −2.71 |
| AL121749.1 | −1.07 | −1.54 | 0.24 | −0.67 | 1.22 | AC015911.7 | 0.25 | −0.74 | −0.09 | −0.54 | −0.15 | AC007671.1 | 0.03 | 0.32 | 0.91 | −0.12 | 0.74 |
| AC004696.2 | −1.38 | 0.15 | 2.02 | 0.04 | 1.57 | AC025171.2 | −0.12 | −0.13 | 0.65 | −0.11 | 0.45 | SLC25A33 | −0.01 | −0.07 | 0.29 | −0.20 | 0.05 |
| AL513329.1 | 0.58 | −0.70 | −1.00 | 0.27 | 0.34 | AC092724.1 | 0.45 | −0.33 | −1.57 | 0.66 | −1.02 | NUFIP1P | 0.04 | −0.59 | 1.40 | −1.60 | −0.44 |
| CD48 | 0.79 | −1.65 | 0.58 | −0.48 | 0.86 | AC010531.5 | −0.31 | 0.00 | 0.01 | 0.24 | 0.41 | HMX2 | −0.08 | −1.16 | 0.60 | 0.26 | 0.33 |
| MCM8-AS1 | 1.01 | −0.75 | −0.50 | −0.72 | 0.19 | ARGFXP2 | −0.19 | 0.34 | 0.63 | 0.16 | 0.32 | AC105935.1 | 0.02 | −0.07 | 0.23 | −0.49 | −0.37 |
| MROH7-TTC4 | −1.67 | 0.98 | 0.43 | 0.45 | −0.33 | ATF7 | −0.08 | 0.11 | 0.15 | −0.02 | −0.06 | PLGLA | −0.07 | −0.64 | −0.44 | 0.08 | −0.47 |
| AL358216.1 | −0.37 | −0.04 | 0.09 | −0.11 | −0.11 | AC017007.3 | −0.71 | −0.59 | 0.51 | −1.75 | 0.30 | AC118754.2 | −0.19 | −0.98 | −0.87 | −0.68 | NA |
| GLIS3-AS1 | 1.58 | −1.41 | −2.74 | −0.97 | −1.41 | BMS1P18 | 0.65 | −0.10 | 0.40 | −0.62 | −0.53 | LUNAR1 | −0.03 | 0.41 | −1.15 | −0.07 | −2.04 |
| NHSL1 | 0.29 | 0.15 | −0.19 | 0.11 | −0.30 | FBXO47 | 0.65 | −2.10 | −0.83 | 0.21 | −0.05 | LINC01565 | −0.03 | −0.08 | −0.43 | 0.40 | −1.66 |
| AC008011.2 | 1.87 | −1.83 | −3.23 | −1.35 | −2.91 | AC005086.2 | 0.41 | −0.61 | −0.07 | 0.12 | 0.92 | AC087863.1 | −0.18 | 0.44 | −1.11 | −0.11 | −1.96 |
| MAGOH3P | 1.46 | −0.90 | −0.91 | −0.55 | −0.28 | NDUFA10 | −0.05 | 0.05 | 0.09 | −0.04 | 0.03 | AC009303.2 | −0.01 | −0.13 | 0.05 | −0.18 | −0.16 |
| AC092910.1 | 0.52 | −0.37 | −0.03 | −0.20 | 0.09 | AL356121.1 | 0.48 | −0.42 | −1.86 | 0.34 | 0.14 | CACNA2D4 | −0.01 | −0.28 | −0.24 | −0.19 | 0.14 |
| SLC15A4 | 0.24 | −0.23 | −0.13 | −0.21 | −0.07 | ADARB1 | −0.08 | 0.00 | −0.04 | −0.03 | −0.07 | AC092436.1 | 0.15 | −0.22 | −0.06 | −0.12 | 2.07 |
| AC004264.1 | −1.08 | −0.03 | 0.87 | −0.03 | 0.14 | GCNT2P | −0.40 | 0.11 | 0.34 | −0.20 | 0.43 | MAGEA7P | −0.19 | 0.08 | −0.68 | 0.81 | −2.65 |
| PLAGL2 | 0.31 | 0.00 | −0.27 | 0.02 | −0.23 | RANBP3 | −0.05 | 0.01 | −0.16 | 0.03 | −0.06 | AC010271.2 | 0.14 | −1.31 | 0.73 | −0.54 | 2.00 |
| GFRA2 | −0.63 | 0.22 | 0.04 | 0.39 | 0.02 | RPSAP41 | 0.41 | −1.11 | 0.48 | −0.68 | −0.14 | NFU1P2 | 0.19 | −0.41 | 1.25 | −1.50 | 0.64 |
| FKBP7 | −0.44 | 0.24 | 1.05 | −0.50 | 0.24 | AC020687.1 | −0.84 | 0.32 | 0.04 | 0.15 | −0.74 | AC091059.1 | −0.13 | 0.38 | 0.87 | −0.94 | −1.33 |
| AC097455.1 | 1.16 | −0.17 | −1.17 | −0.19 | −0.73 | OR6N1 | 0.59 | −0.62 | −0.58 | 0.72 | −0.16 | AC131532.1 | −0.09 | −0.21 | −0.49 | −1.87 | −3.08 |
| AL731563.2 | −0.75 | −0.25 | −0.62 | −0.06 | 0.32 | RNASE3 | −0.55 | 1.83 | 0.76 | 2.14 | 0.59 | AL161757.2 | 0.02 | 0.06 | 0.09 | −0.26 | −0.47 |
| AL079304.1 | −1.22 | −0.54 | 1.30 | 0.71 | 1.25 | AL592287.1 | −0.69 | 0.29 | −0.29 | 0.86 | 0.28 | GZMH | 0.02 | −0.56 | −0.32 | −0.15 | 0.38 |
| G18345 | −0.58 | −0.14 | −0.40 | −0.22 | 0.18 | MRPL42P2 | 0.73 | −1.19 | −0.35 | 0.66 | 1.43 | AC084851.2 | −0.10 | −0.08 | −0.56 | 0.08 | 1.30 |
| RN7SL525P | −1.27 | 0.71 | 1.26 | 0.79 | 1.27 | AC044787.1 | 0.19 | −0.05 | −0.58 | 0.17 | −0.19 | IGHV6-1 | 0.17 | 0.92 | 0.64 | 0.10 | −0.13 |
| GPHN | −0.19 | 0.08 | 0.22 | 0.15 | 0.17 | AL391845.2 | −0.56 | 0.37 | −1.96 | 0.03 | −1.95 | AL512347.1 | −0.19 | −0.61 | 0.11 | 0.57 | 3.50 |
| EIF4E3 | −0.38 | 0.28 | 0.35 | 0.16 | 0.00 | CLBA1 | −0.10 | −0.02 | 0.18 | −0.05 | 0.23 | MIR7515HG | −0.03 | 0.61 | −0.81 | 0.70 | −0.86 |
| RGS4 | 0.94 | −0.24 | −0.72 | −0.01 | 0.04 | AC093012.1 | 0.16 | 0.19 | 0.16 | 0.10 | −0.03 | AL023881.1 | −0.04 | 0.28 | 1.43 | 1.60 | 0.81 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC013640.1 | 0.93 | −0.06 | −0.39 | −0.44 | −0.66 | AC007365.2 | 0.39 | −0.81 | −0.07 | 0.32 | −0.51 | CEACAM6 | −0.02 | −0.43 | 0.11 | −0.25 | −0.11 |
| AL161910.1 | −1.05 | −0.44 | 1.14 | −0.16 | 1.62 | AL589863.1 | 0.26 | −0.71 | −0.12 | −0.36 | 0.49 | AL365436.2 | −0.02 | 0.31 | 0.53 | 0.17 | −0.04 |
| KCNK15-AS1 | −0.96 | 0.70 | 0.47 | −0.13 | −0.45 | AL807752.1 | −0.24 | 0.01 | 0.10 | −0.11 | 0.36 | RNA5SP327 | 0.19 | −0.23 | 1.04 | −2.14 | −1.11 |
| SECISBP2L | −0.28 | 0.32 | 0.36 | 0.11 | 0.00 | AC010598.1 | 0.38 | 0.04 | 0.55 | 0.47 | 0.84 | AC098592.2 | 0.19 | 0.32 | −1.06 | −0.45 | −1.60 |
| AL157392.3 | −0.28 | 0.27 | 0.39 | 0.05 | 0.19 | AL590762.1 | −0.24 | −0.13 | −0.12 | −0.05 | 0.03 | NALCN-AS1 | 0.02 | −1.29 | −0.17 | 0.55 | 0.78 |
| RNU6-1225P | −1.36 | −0.76 | −0.47 | −0.59 | −1.31 | KARSP3 | −0.56 | −0.64 | −0.88 | 0.08 | −0.47 | AL445430.1 | 0.18 | −0.49 | −0.01 | −0.46 | 0.30 |
| FBXW2 | 0.23 | 0.04 | 0.01 | 0.04 | −0.05 | AP006296.1 | 0.63 | 0.73 | −1.01 | 1.61 | −0.26 | AC003685.1 | 0.05 | −1.77 | 0.19 | 0.36 | 1.46 |
| PLPPR4 | −0.38 | 0.19 | 0.31 | −0.21 | −0.14 | OR51G1 | 0.61 | −0.12 | −0.63 | −0.25 | −0.97 | SLC9A3R2 | −0.01 | −0.02 | 0.56 | −0.02 | 0.17 |
| SPRN | −0.41 | 0.00 | 0.08 | 0.22 | 0.38 | AC026748.1 | −0.41 | 0.74 | 0.66 | −0.48 | 0.00 | HAUS1P3 | −0.18 | −0.84 | −0.89 | −1.29 | −1.79 |
| FAP | 0.62 | −0.18 | 0.28 | −1.13 | −0.52 | AC091576.1 | −0.66 | −0.71 | −0.46 | 0.85 | 0.00 | AC060764.1 | −0.18 | −0.22 | −0.69 | −0.32 | −0.84 |
| ITIH2 | −0.66 | 0.27 | 0.71 | 0.14 | 0.43 | RNA5SP300 | 0.25 | 0.33 | 0.69 | −0.11 | −0.10 | AC090164.3 | −0.05 | −1.35 | −1.67 | 0.02 | −1.41 |
| PNMA8C | −1.27 | −0.59 | −0.22 | −0.06 | −0.04 | OTOAP1 | −0.39 | 0.80 | −0.90 | 0.83 | −0.29 | AC079395.2 | −0.18 | −1.55 | −0.13 | −1.66 | 0.36 |
| METTL21A | 0.32 | −0.34 | 0.01 | −0.22 | 0.10 | AL049597.2 | 0.19 | −0.06 | −0.01 | 0.32 | −0.15 | FAM47B | 0.18 | −0.52 | −0.88 | 0.79 | −0.29 |
| CLPB | 0.23 | −0.33 | −0.29 | −0.17 | 0.04 | CRSP8P | 0.49 | 0.16 | 0.58 | −0.21 | 0.18 | NUP85 | 0.00 | −0.09 | −0.22 | 0.02 | −0.03 |
| LINC01102 | −1.11 | −0.34 | 0.38 | 0.40 | 0.39 | IGHV4-34 | 0.93 | −0.06 | −1.83 | 0.98 | −2.69 | RPP40P2 | 0.18 | 1.79 | −0.43 | −0.48 | −1.94 |
| AC007938.3 | −0.94 | 0.44 | −0.01 | −0.05 | −0.19 | AL513122.1 | −0.33 | 0.82 | 0.10 | −0.05 | −0.46 | PGAM1P8 | 0.01 | −0.41 | −0.03 | −0.08 | 0.24 |
| SOX6 | −0.44 | 0.27 | 0.14 | 0.54 | −0.17 | FBXW12 | 0.17 | 0.11 | 0.05 | 0.03 | 0.07 | AL035443.1 | −0.09 | −1.35 | −0.91 | −0.46 | −0.44 |
| OGFR | −0.35 | −0.07 | −0.29 | 0.13 | 0.15 | MSH5 | −0.12 | −0.04 | 0.05 | 0.00 | 0.24 | HMGB1P47 | 0.18 | 0.91 | 1.28 | 0.85 | 0.89 |
| LRRC3-DT | −1.60 | 0.97 | 0.35 | 0.33 | −0.67 | GPC5-AS2 | −1.61 | 0.68 | 1.70 | 1.07 | 1.24 | G25594 | 0.01 | −0.25 | 0.12 | −0.04 | 0.58 |
| RNU6-757P | 0.97 | −0.22 | −0.53 | 0.38 | −0.10 | AC137630.1 | −0.66 | 1.16 | −0.89 | 0.68 | −0.84 | RNVU1-16 | 0.18 | −0.40 | −0.52 | 0.62 | NA |
| AL158068.1 | 1.09 | −0.59 | 0.51 | −0.45 | −0.26 | NID2 | 0.16 | −0.28 | 0.50 | −0.50 | −0.09 | PHKBP2 | 0.18 | 0.08 | 0.13 | −1.27 | −0.35 |
| AC126615.1 | 0.87 | −0.39 | −0.77 | −0.08 | 0.11 | AC022445.1 | 0.26 | −0.47 | −0.05 | −0.04 | 0.14 | AC007953.1 | −0.09 | 0.39 | −2.84 | 1.77 | −1.43 |
| AL133485.2 | −0.95 | −0.52 | 0.55 | −0.99 | 0.68 | PAICSP4 | −0.53 | 1.19 | −1.35 | 0.16 | −1.03 | DNM1P34 | −0.18 | −0.66 | −0.32 | 0.64 | −0.03 |
| AC010378.1 | 0.93 | −0.59 | −0.54 | −0.23 | 0.06 | SERF1A | −0.56 | −0.61 | −0.43 | −2.25 | −2.36 | AC069282.1 | 0.01 | −0.13 | 0.28 | −0.12 | 0.15 |
| AC114730.3 | −1.15 | 1.51 | 0.62 | 0.90 | −0.18 | STK4-AS1 | 0.46 | 0.20 | −0.21 | 0.09 | −0.56 | SLC9A9 | 0.01 | 0.15 | 0.34 | 0.17 | −0.04 |
| AP001033.1 | 1.23 | −0.41 | −0.94 | 0.30 | 0.47 | AC022075.1 | −0.16 | −0.53 | 0.44 | −0.25 | 0.54 | AC073488.7 | −0.18 | 0.22 | 0.20 | 0.14 | 0.48 |
| FLOT1 | 0.27 | −0.16 | −0.36 | −0.02 | −0.12 | AP000753.3 | 0.26 | −0.19 | −0.51 | 0.04 | −0.09 | RN7SKP244 | 0.05 | −1.98 | 1.08 | 1.71 | 2.13 |
| OR1J1 | 0.90 | 0.15 | −1.17 | 0.06 | −0.59 | RNU6-509P | 0.30 | 0.47 | −1.08 | 0.91 | −0.76 | AC013457.1 | 0.04 | −0.17 | −1.07 | 0.30 | −1.96 |
| CNGA1 | −0.34 | 0.32 | 0.28 | 0.02 | −0.02 | LINC02592 | 0.62 | −1.11 | −1.63 | 0.29 | 1.03 | AL157402.1 | 0.18 | −0.80 | −1.16 | 1.64 | −1.76 |
| COL6A6 | 0.89 | −0.06 | 0.53 | −0.73 | 0.50 | OR2L8 | 0.84 | −0.42 | −0.41 | 1.48 | −0.32 | C16orf92 | 0.06 | −1.36 | −0.63 | −1.38 | 0.09 |
| APHIA | 0.26 | −0.06 | −0.13 | 0.01 | −0.16 | RHBDF2 | 0.10 | −0.02 | −0.09 | −0.06 | 0.00 | G25047 | −0.18 | −0.43 | 1.66 | −0.91 | 0.69 |
| ENTPD5 | 0.22 | −0.16 | −0.26 | −0.07 | −0.07 | SCNN1D | 0.16 | −0.73 | −1.16 | 0.01 | 0.11 | AL022328.1 | −0.02 | 0.39 | 1.02 | 0.39 | 0.21 |
| MIR1972-2 | 1.15 | −1.50 | −0.65 | −0.17 | −0.85 | AC117503.3 | 0.24 | −0.34 | −0.13 | −0.17 | 0.07 | AC022201.1 | −0.06 | −1.91 | −0.89 | 0.60 | 0.64 |
| LRBA | 0.26 | 0.06 | −0.01 | 0.06 | 0.02 | AC020629.1 | −0.28 | −0.15 | 0.21 | −0.17 | 0.04 | RBMS1P1 | 0.01 | −0.05 | 0.63 | −0.16 | 0.55 |
| SMARCE1P1 | −0.42 | 0.07 | 0.18 | 0.09 | 0.19 | AC083841.1 | 0.30 | 0.00 | 1.04 | −0.15 | 0.06 | AL035411.2 | 0.09 | −1.36 | 0.72 | 0.04 | 2.79 |
| MIR3617 | −1.81 | 1.87 | 1.95 | 1.12 | −0.09 | RNF41 | 0.07 | −0.01 | −0.04 | −0.08 | −0.17 | LINC02552 | 0.05 | −0.67 | 0.95 | 0.31 | 1.62 |
| SRP54-AS1 | −0.33 | 0.19 | 0.89 | −0.12 | 0.37 | AL021808.1 | 0.90 | −1.40 | −2.13 | 1.11 | −0.92 | AC245060.3 | 0.07 | −1.41 | −0.88 | −0.49 | −0.73 |
| AC104169.1 | 1.41 | 0.18 | −0.51 | 0.65 | −1.02 | AC106806.2 | −1.07 | −0.53 | 0.41 | 1.45 | 0.41 | AC021713.1 | 0.18 | −0.93 | −0.72 | 1.03 | −0.20 |
| AC011374.1 | 0.66 | 0.03 | 0.04 | 0.57 | 0.03 | AL031186.1 | 0.36 | −0.27 | 0.79 | −0.40 | 0.96 | APOBEC1 | 0.18 | −0.63 | −0.28 | −0.44 | −0.09 |
| AC090241.1 | −0.42 | −0.45 | 0.17 | −0.09 | 0.37 | KTN1-AS1 | 0.10 | −0.33 | 0.12 | 0.00 | 0.54 | ST6GALNAC2P | 0.18 | 0.10 | −0.41 | −0.65 | −1.01 |
| AP001962.1 | 0.75 | −0.34 | −0.24 | 0.53 | −0.02 | AC007182.1 | −0.29 | 0.26 | −1.06 | 0.34 | −1.63 | RBM4 | −0.01 | 0.01 | 0.11 | 0.14 | 0.13 |
| AC009779.2 | −0.49 | 0.17 | 0.58 | −0.05 | 0.55 | AL021937.4 | −0.32 | 0.48 | −0.06 | 0.97 | −0.08 | RPL21P67 | 0.09 | −0.04 | −1.89 | 2.28 | −0.84 |
| KLF2 | −0.48 | 0.27 | 0.34 | 0.02 | −0.43 | AL136380.1 | −0.25 | 0.03 | 0.34 | 0.23 | 0.17 | AC023200.1 | 0.04 | −1.27 | 0.23 | 0.64 | 0.21 |
| EGR1 | −0.45 | 0.26 | 0.30 | −0.37 | 0.27 | SH2D4B | −0.24 | 0.34 | −0.14 | 0.26 | −0.64 | AL162431.1 | 0.01 | −0.42 | 0.08 | −0.13 | 0.61 |
| DDX56 | 0.24 | −0.22 | −0.48 | −0.01 | −0.02 | PAX1 | 0.28 | −0.68 | 0.07 | −0.43 | −0.32 | AC022387.2 | 0.18 | −1.84 | −0.07 | −0.63 | 3.26 |
| AL157886.1 | 1.10 | −0.50 | −1.73 | −0.21 | −1.19 | C8orf89 | −0.47 | −0.81 | 1.77 | 0.32 | 0.60 | G30952 | 0.02 | 0.85 | 0.99 | −0.10 | −0.93 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| EFCAB12 | −0.74 | 0.32 | 0.10 | 0.24 | −0.08 | CYP3A52P | 0.69 | −0.40 | −0.88 | −0.99 | −1.06 | AC013727.2 | 0.18 | −0.81 | 1.43 | −0.07 | 0.80 |
| RNU7-41P | 1.03 | −0.73 | −0.51 | −0.18 | 0.25 | PGK2 | −0.88 | 0.53 | 0.03 | 1.06 | −0.76 | AL645568.2 | −0.01 | −0.52 | 1.33 | −0.53 | 0.69 |
| AL626787.1 | −0.66 | −0.21 | 0.54 | 0.22 | 0.11 | LINC01951 | 0.64 | −1.06 | −1.13 | 0.49 | 0.82 | RNU7-123P | 0.04 | 0.17 | −0.98 | −0.05 | −0.30 |
| AL445189.2 | −1.17 | −0.26 | 0.39 | 0.34 | 0.51 | JTBP1 | 0.23 | 0.32 | 0.16 | −0.05 | −0.55 | LINC00870 | 0.03 | −0.63 | 0.00 | −0.55 | 0.24 |
| AL139400.1 | −0.67 | 0.36 | 0.81 | 0.15 | 0.75 | CFAP99 | −0.33 | 0.10 | 0.37 | −0.16 | 0.00 | RN7SL671P | 0.07 | −0.35 | 0.63 | 0.49 | 1.40 |
| AC012213.2 | −1.04 | −0.63 | 0.43 | −0.88 | 0.62 | AC004687.1 | 0.22 | −0.89 | 0.25 | −0.87 | 0.48 | AC022893.3 | 0.02 | −1.23 | 0.91 | −0.48 | 0.43 |
| G34423 | −1.05 | 0.20 | 0.93 | 0.94 | 0.72 | RPL13AP19 | 0.66 | −1.03 | −1.08 | 0.63 | −0.53 | HNRNPA1P70 | −0.03 | −0.54 | 0.54 | 0.30 | 0.95 |
| AL449983.1 | −0.73 | 0.34 | 0.91 | 0.24 | −0.17 | AC002347.2 | 0.41 | −0.53 | 0.83 | 0.10 | −0.03 | AC007159.1 | −0.03 | −0.34 | −0.46 | 0.48 | −1.10 |
| HEXA-AS1 | 0.62 | −0.56 | −0.11 | −0.13 | 0.15 | AC091982.2 | 0.73 | 0.24 | −0.71 | −0.71 | −2.26 | AC005523.1 | 0.04 | 0.40 | −0.35 | 0.61 | −0.96 |
| AL136985.2 | −1.04 | 0.17 | 2.34 | −1.29 | 0.46 | PDHX | 0.08 | −0.05 | −0.12 | 0.03 | 0.04 | LINC01264 | −0.09 | 0.47 | −3.12 | 1.77 | −1.33 |
| ESM1 | 1.42 | −0.88 | −1.97 | −0.42 | −0.83 | AP001324.3 | 0.63 | −1.77 | −2.06 | −0.96 | 1.53 | NKX6-3 | −0.08 | −0.76 | −0.61 | 1.25 | 0.20 |
| AC092384.2 | −0.67 | 0.13 | 0.38 | 0.34 | 0.58 | HSFX4 | 0.49 | −1.05 | 0.32 | 0.37 | 2.83 | LINC02565 | −0.18 | 0.28 | 0.59 | 2.52 | −0.09 |
| MDM1 | −0.25 | −0.03 | 0.16 | −0.06 | 0.12 | MED9 | −0.05 | −0.02 | 0.10 | −0.01 | 0.13 | LINC00028 | −0.05 | −0.74 | −0.33 | 0.75 | 0.61 |
| ADSS | 0.24 | −0.03 | −0.21 | 0.01 | −0.13 | RPSAP3 | 0.48 | 0.55 | 0.51 | 0.16 | −0.80 | AL132996.1 | −0.05 | −0.77 | 0.85 | 0.03 | −0.50 |
| NAPEPLD | −0.22 | 0.17 | 0.30 | 0.13 | 0.23 | OR6C75 | −0.54 | −0.03 | 0.31 | 0.66 | −0.57 | MIR4791 | −0.18 | −0.19 | 0.31 | −0.15 | 1.56 |
| DOC2A | −0.76 | 0.29 | −0.02 | 0.13 | −0.45 | AL137024.1 | −0.22 | −0.95 | 0.64 | −0.99 | 0.02 | AC105031.3 | −0.18 | −0.84 | 1.32 | −0.36 | 0.80 |
| AC126915.1 | −1.46 | 1.74 | 1.71 | 2.85 | −0.81 | RNU4-87P | 0.43 | −0.44 | −0.60 | −0.74 | −0.39 | EEF1GP1 | 0.02 | 0.44 | −1.18 | 0.68 | −1.45 |
| AC010719.1 | −0.47 | 0.73 | 0.59 | 0.47 | 0.14 | LHFPL3-AS2 | −0.27 | 0.12 | −1.03 | 0.72 | −0.26 | LINC01047 | −0.17 | 0.13 | 1.78 | −1.24 | −0.10 |
| LINC01620 | −1.46 | 0.64 | 1.53 | −0.66 | −0.34 | FOSLIP1 | 0.22 | 0.03 | 0.01 | 0.20 | 0.13 | SLCO1B7 | −0.18 | −0.68 | −0.24 | −0.59 | −1.01 |
| ANKRD42 | −0.19 | 0.08 | 0.19 | −0.02 | 0.00 | AL589765.4 | 0.54 | −0.15 | 0.27 | 0.09 | 1.57 | AC116366.2 | −0.02 | −0.21 | −0.66 | 0.00 | −0.21 |
| AC015819.2 | 1.07 | −0.78 | −2.67 | 0.60 | −1.15 | MR1 | −0.08 | 0.08 | 0.29 | 0.04 | 0.06 | AL049734.2 | 0.18 | −0.66 | 0.51 | 1.19 | 1.11 |
| HTD2 | 1.07 | −0.77 | −1.39 | −0.14 | −0.60 | AC007552.1 | −0.36 | 0.07 | 0.17 | 0.23 | 0.00 | AL451124.1 | 0.17 | 0.73 | −1.65 | 1.18 | −1.17 |
| PCNPP4 | −2.05 | 0.40 | 1.66 | −1.62 | 0.49 | ELOCP33 | 0.25 | −0.35 | −0.14 | −0.45 | 0.21 | CD14 | 0.02 | −0.02 | −0.06 | 0.22 | −0.10 |
| RPS26P6 | 1.12 | −0.37 | −0.31 | −0.10 | −0.04 | RP11-195B21.3 | −0.55 | 0.39 | 1.11 | 1.11 | 0.01 | AC122683.1 | 0.06 | −1.19 | 0.89 | 0.10 | 0.53 |
| AC011726.2 | 0.77 | −0.06 | −0.56 | 0.08 | −1.15 | OR5I1 | 0.94 | −1.42 | −1.92 | −0.29 | −2.72 | AC012355.1 | −0.18 | −0.30 | 1.13 | 0.77 | 1.42 |
| DDB2 | −0.34 | 0.22 | 0.27 | 0.25 | 0.12 | AC020661.1 | 0.23 | −0.28 | 0.41 | −0.17 | 0.39 | AC107398.4 | 0.07 | 1.60 | −1.75 | 0.59 | −3.69 |
| L3MBTL3 | 0.23 | −0.20 | −0.24 | 0.03 | −0.14 | PTPRJ | −0.11 | −0.21 | 0.18 | −0.13 | 0.32 | NPIPB10P | 0.02 | −0.45 | −0.64 | 0.37 | 0.43 |
| G38764 | 1.15 | 0.20 | −0.66 | 0.78 | 0.31 | OR8G5 | 0.71 | −0.67 | −1.59 | 0.33 | −1.04 | IGKV2-18 | −0.18 | 0.03 | 0.12 | 0.32 | −0.02 |
| AMDHD2 | −0.38 | 0.20 | −0.22 | 0.39 | 0.01 | DPP10-AS3 | −1.00 | 0.91 | −0.07 | −1.57 | −1.93 | RAI1-AS1 | 0.02 | 0.26 | 0.49 | −0.25 | 0.45 |
| AC022507.1 | −1.45 | −0.17 | −0.99 | 0.65 | −0.98 | AP005717.1 | −0.27 | 0.05 | 0.48 | 0.29 | 1.07 | KRTAP5-3 | 0.18 | 0.27 | 0.97 | −0.32 | −1.80 |
| INTS10 | 0.16 | −0.14 | 0.03 | −0.18 | −0.07 | RPS7P4 | 0.49 | −0.57 | 0.17 | −0.86 | −1.22 | AL606970.3 | −0.03 | −0.58 | 0.29 | 0.83 | 1.32 |
| AC087650.1 | −1.33 | 0.89 | 1.43 | −0.77 | −0.05 | FMR1NB | −0.84 | −0.57 | −0.65 | −0.27 | −2.46 | RNU6-168P | 0.18 | −0.98 | 0.05 | −0.81 | 0.32 |
| AF121898.1 | −1.47 | −0.44 | 0.58 | 0.02 | 0.15 | AC128687.1 | 0.33 | 0.68 | −0.49 | 0.26 | −0.48 | PTCD2P2 | 0.14 | −0.31 | −0.09 | −2.04 | −0.75 |
| SMILR | 1.41 | −0.81 | 0.65 | 0.39 | 0.30 | CDH9 | 0.50 | −0.06 | −1.91 | 0.29 | −1.87 | CDC42P4 | 0.02 | 0.52 | 0.13 | 0.41 | −0.27 |
| AC092807.3 | −0.45 | −0.16 | 0.75 | −0.85 | −0.08 | AC007546.2 | −0.86 | 0.44 | −0.22 | 2.15 | −0.91 | MBL2 | −0.04 | −1.39 | 0.49 | 0.72 | 1.60 |
| RAVER2 | −0.22 | 0.21 | 0.43 | 0.05 | 0.00 | AL356981.1 | −0.55 | −0.21 | −1.18 | 0.38 | −0.96 | AC008050.1 | −0.03 | 0.72 | −1.03 | −0.34 | −2.64 |
| CIDEA | −0.75 | 0.67 | −0.40 | 1.28 | 0.10 | AC117386.1 | 0.46 | −0.21 | 0.14 | −0.60 | −1.20 | AC010469.2 | −0.07 | 0.47 | −0.95 | 0.64 | −1.18 |
| MAP3K7CL | −0.42 | 0.16 | 0.36 | 0.12 | 0.21 | FSTL3 | −0.14 | 0.05 | −0.14 | 0.05 | −0.16 | ACSL5 | 0.01 | −0.05 | 0.01 | −0.02 | 0.13 |
| AC009690.1 | −0.85 | 0.91 | 1.37 | −0.43 | 0.28 | AC009107.1 | 0.25 | 0.31 | 0.10 | 0.38 | −0.32 | AC073476.1 | −0.03 | 1.24 | 1.14 | −0.28 | −0.96 |
| CCDC28B | −0.42 | 0.08 | 0.49 | −0.21 | 0.20 | NCOA7-AS1 | 0.25 | −0.16 | 0.02 | 0.15 | 0.31 | AC105389.3 | 0.08 | −1.29 | −1.05 | −2.01 | −2.34 |
| AC005261.5 | 0.48 | −0.11 | −0.43 | −0.07 | −0.26 | AL451142.1 | 0.79 | 0.95 | −2.00 | 0.87 | −1.06 | LINC02373 | −0.03 | 0.67 | −0.24 | 0.15 | −0.96 |
| FBLL1 | −0.89 | 0.07 | 1.31 | −0.18 | 0.35 | AL589872.1 | −0.64 | 0.95 | 1.32 | −0.40 | −0.85 | NTM-IT | 0.09 | −1.79 | −1.15 | −0.67 | 1.29 |
| MRPL42P6 | −1.19 | 1.50 | 1.00 | 0.98 | 0.56 | LINC00689 | −0.36 | −0.50 | −0.29 | −0.39 | −0.41 | FAHD2P1 | −0.18 | −0.60 | 0.71 | −0.22 | 0.76 |
| AP003117.1 | −0.65 | 0.88 | 0.61 | 0.31 | −0.09 | RIPPLY3 | 0.28 | −1.17 | −0.87 | −0.10 | 0.02 | AC128713.1 | −0.18 | −0.17 | NA | −0.08 | −0.50 |
| SIGLEC7 | 1.32 | −1.35 | −0.85 | −0.61 | −0.32 | RN7SKP214 | −0.86 | 1.20 | 1.35 | 1.61 | 0.77 | AC105999.1 | 0.14 | −0.43 | 0.82 | −0.10 | 0.32 |
| RNA5SP449 | 0.95 | −0.98 | −0.79 | −0.42 | −0.18 | AP002815.1 | −0.92 | 1.71 | 2.80 | 0.14 | 0.83 | SPANXN4 | −0.08 | −1.05 | −2.31 | −0.03 | −0.54 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| PPP1R27 | −0.87 | −0.21 | −0.08 | 0.17 | 0.07 | SST | 0.91 | 0.35 | 0.23 | −1.19 | −0.06 | AC099799.1 | 0.18 | −0.67 | −0.25 | −0.93 | 0.16 |
| OAZ2 | −0.22 | 0.26 | 0.25 | 0.08 | −0.21 | KRT8P1 | −0.81 | −0.82 | 1.02 | −0.56 | 1.58 | MIR1262 | −0.03 | −0.66 | 1.12 | −0.03 | −0.18 |
| FKSG52 | −1.02 | 0.33 | 0.92 | −0.17 | 0.66 | PINLYP | −0.11 | 0.43 | 0.24 | 0.23 | −0.09 | RNA5SP25 | 0.05 | −1.52 | −0.91 | −0.61 | 0.27 |
| KIAA2013 | 0.25 | 0.00 | 0.04 | −0.04 | −0.19 | SNRPCP20 | −1.01 | 0.49 | 0.78 | 1.32 | 0.91 | AC010620.2 | −0.07 | −0.46 | −0.40 | 1.95 | −0.38 |
| SEC14L4 | −1.08 | 0.87 | −0.42 | 1.32 | 0.40 | AC068620.1 | −0.21 | 0.23 | 0.19 | 0.07 | 0.31 | DARS-AS1 | −0.01 | −0.19 | 0.22 | −0.20 | 0.05 |
| HIST2H2AB | −0.40 | 0.08 | −0.33 | 0.19 | −0.47 | AC006974.1 | 0.85 | −0.21 | −1.45 | 0.43 | 0.57 | KRT18P35 | −0.11 | −0.95 | 0.05 | −1.11 | 1.18 |
| C1QTNF12 | −0.68 | 0.64 | −0.86 | 0.87 | −0.60 | ADD1 | −0.04 | 0.07 | 0.00 | 0.05 | −0.06 | RNU1-150P | −0.08 | 0.24 | −0.09 | 0.31 | −1.63 |
| AC017033.1 | −1.00 | 0.85 | 0.63 | 0.93 | 0.44 | LINC01924 | −0.35 | 0.32 | 0.56 | −0.12 | −0.84 | ITCH-AS1 | 0.02 | −0.36 | −0.42 | 0.51 | 0.36 |
| RNA5SP225 | −1.09 | −0.05 | −0.65 | 0.89 | −0.19 | SF1 | −0.07 | −0.02 | −0.34 | 0.10 | 0.00 | AC095041.1 | −0.08 | −0.80 | −0.98 | 0.29 | −0.14 |
| AL021937.3 | 1.06 | −0.08 | −0.53 | −0.06 | −0.19 | AC010533.1 | −0.25 | −0.01 | 1.39 | −1.15 | 0.39 | LINC02573 | 0.17 | −1.10 | 1.15 | −0.17 | 2.96 |
| AF064860.2 | −1.22 | 0.71 | 1.69 | 0.56 | 0.32 | AC020908.3 | −0.22 | −0.70 | −1.11 | −0.29 | 0.09 | AC117440.1 | 0.17 | −0.83 | 0.88 | 1.59 | 0.61 |
| RPS3AP6 | 0.51 | −0.02 | −0.05 | −0.13 | −0.48 | NOTCH2 | −0.07 | 0.23 | 0.29 | 0.02 | −0.06 | AL596211.1 | −0.07 | −1.15 | −0.88 | −0.64 | −0.11 |
| RPL17P1 | −1.04 | −0.14 | −0.38 | 0.36 | −0.25 | COMMD4 | 0.06 | −0.02 | −0.05 | −0.04 | −0.02 | AL663058.1 | 0.17 | −0.43 | −0.51 | 0.33 | 0.87 |
| AC007834.2 | 0.75 | −0.42 | 0.09 | −0.38 | 0.52 | RNU6-519P | 0.79 | −0.67 | −1.94 | 1.39 | 1.21 | G38513 | 0.02 | 0.53 | −0.11 | 0.42 | −0.16 |
| PPIG | 0.28 | −0.18 | −0.30 | −0.09 | −0.20 | KLHL2P1 | −0.24 | 0.18 | 0.49 | −0.05 | 0.12 | NRL | −0.01 | 0.10 | −0.35 | −0.10 | −0.21 |
| AL023284.4 | 0.64 | 0.03 | 0.15 | −0.13 | −0.19 | AF131216.1 | 0.13 | −0.28 | 0.01 | −0.15 | 0.24 | AP000793.1 | 0.05 | 0.56 | −1.06 | 2.02 | −1.14 |
| AC091925.2 | 0.74 | −0.65 | 0.00 | 0.21 | 0.23 | AC025423.5 | −0.33 | 0.11 | 0.47 | 0.35 | 0.21 | BMP15 | 0.07 | −0.48 | −0.42 | 1.21 | 0.22 |
| AC098826.3 | −1.61 | 0.26 | 2.54 | 1.14 | 0.32 | ATG10-AS1 | −0.20 | 0.51 | 0.13 | 0.01 | −0.15 | AC015722.1 | −0.17 | −1.45 | 0.96 | −1.60 | 0.91 |
| RPAP2P1 | −0.46 | 0.05 | 0.73 | 0.12 | 0.15 | SEPT7P6 | 0.22 | −0.50 | −0.34 | −0.33 | 0.22 | CFAP58 | −0.01 | −0.21 | 0.10 | −0.37 | −0.12 |
| AC005776.2 | −0.48 | −0.31 | 0.00 | −0.07 | 0.32 | SLC9C2 | −0.36 | 0.07 | −1.38 | 0.74 | −1.67 | AP000959.1 | −0.07 | −0.91 | −0.86 | −0.31 | −0.43 |
| AC120114.1 | −0.70 | 0.10 | −0.25 | −0.12 | −0.09 | SP2 | 0.04 | 0.04 | −0.25 | 0.11 | −0.16 | AC116533.3 | 0.08 | 0.04 | 1.12 | −0.36 | 0.63 |
| HIVEP1 | 0.22 | 0.01 | −0.32 | −0.15 | −0.52 | RN7SL408P | −0.69 | −0.03 | 0.10 | 1.65 | 0.70 | AC024941.1 | −0.07 | −1.50 | −0.39 | −1.02 | 0.73 |
| NFAT5 | 0.17 | 0.17 | −0.11 | 0.03 | −0.28 | AC073071.1 | −0.60 | −0.43 | −1.39 | −0.31 | −2.29 | AC090220.1 | −0.01 | 0.15 | 0.16 | −0.01 | 0.16 |
| PCDHB10 | −0.43 | 0.50 | 0.84 | 0.04 | −0.08 | KPNA2P1 | −0.55 | −0.39 | −0.79 | 0.74 | −0.56 | MIR382 | −0.08 | 1.02 | 1.88 | 0.47 | 1.74 |
| NEMP2 | −0.24 | −0.01 | 0.21 | −0.04 | 0.12 | AC007422.1 | 0.69 | −0.05 | −0.82 | −0.94 | −0.88 | AC005383.1 | 0.03 | 0.07 | 0.01 | −0.09 | −0.91 |
| PUF60 | 0.22 | −0.18 | −0.45 | 0.13 | −0.13 | AC079226.1 | 1.33 | −0.94 | −2.10 | −0.01 | −2.46 | ARHGAP42P4 | −0.17 | −0.67 | −0.27 | −0.47 | 0.36 |
| AL162727.2 | 0.86 | −0.36 | −0.27 | 0.30 | 0.21 | GNAQ | −0.09 | −0.06 | 0.03 | −0.04 | 0.08 | AC080079.1 | −0.08 | 0.31 | −0.51 | −1.86 | −1.88 |
| DUX4L50 | −0.53 | 0.35 | 0.71 | 0.37 | 0.56 | SMARCE1P3 | 0.63 | −0.94 | −1.81 | 1.29 | −1.39 | OR11G1P | 0.17 | 0.58 | −0.41 | 2.26 | −0.92 |
| AL391422.4 | −0.41 | 0.36 | 0.42 | 0.24 | 0.25 | AIDA | 0.12 | −0.12 | 0.09 | −0.20 | −0.10 | LZTS1 | −0.01 | −0.19 | −0.42 | 0.06 | 0.16 |
| PTBP2 | 0.20 | −0.12 | −0.30 | 0.13 | −0.06 | AC005674.2 | −0.13 | −0.05 | 0.02 | 0.06 | 0.01 | RPL21P33 | −0.17 | −0.14 | 1.07 | 0.75 | 1.51 |
| ICAM3 | 1.14 | −0.61 | 0.81 | −0.32 | 1.02 | RN7SL644P | −0.38 | 0.30 | −0.60 | 0.79 | 0.36 | AC104651.1 | 0.05 | −0.38 | −0.39 | 0.00 | −1.38 |
| RORA-AS2 | −1.24 | 0.26 | 0.19 | −0.17 | 0.03 | AP000860.1 | 0.76 | 0.09 | −2.89 | 0.94 | −2.21 | RN7SKP76 | −0.07 | −0.84 | 1.02 | 0.03 | −0.69 |
| CEP97 | 0.19 | −0.01 | −0.06 | 0.00 | −0.07 | AC007298.2 | 0.33 | 1.20 | 0.40 | 0.76 | −0.30 | AL121871.1 | 0.03 | 0.99 | 0.08 | 0.77 | −0.90 |
| C2orf70 | −1.12 | 0.91 | 0.62 | 0.35 | 0.26 | AC103739.3 | −0.17 | −0.33 | 0.46 | −0.27 | 0.27 | CD200R1L | −0.03 | −0.66 | −0.56 | 0.66 | 0.28 |
| AC087392.2 | 0.60 | −0.25 | −0.80 | 0.16 | −0.11 | AC006458.1 | −0.51 | 0.68 | 1.06 | 0.52 | 0.72 | MIR378F | 0.17 | 0.92 | −0.11 | 0.09 | −0.90 |
| AC069503.1 | 1.14 | −1.24 | −0.58 | 0.03 | 0.47 | AC125807.1 | 0.21 | 0.04 | −0.12 | 0.34 | −0.41 | ADAMTS9-AS1 | 0.02 | −0.45 | 0.14 | −0.65 | −0.09 |
| ATG4B | −0.20 | 0.09 | −0.06 | 0.11 | −0.02 | CCM2L | −0.23 | −0.14 | 0.47 | 0.13 | 0.46 | RPL5P13 | −0.02 | −0.06 | −0.10 | −0.22 | −0.75 |
| DDX11-AS1 | −0.67 | 0.49 | 0.62 | 0.01 | −0.09 | GDF6 | −0.30 | 0.19 | 0.32 | −0.84 | −0.04 | AC022880.1 | 0.17 | −0.29 | 0.06 | 0.88 | 1.16 |
| AKR1C6P | −0.68 | 0.03 | 0.62 | −0.54 | 0.31 | CALCA | −0.55 | 0.17 | −0.59 | 0.37 | 0.96 | AC093722.1 | −0.17 | −0.51 | −0.95 | −0.44 | −1.35 |
| AC139795.3 | 0.71 | 0.20 | 0.13 | 0.15 | −0.58 | PTENP1-AS | 0.68 | −0.29 | −0.51 | 1.05 | −1.33 | PEBP1 | 0.01 | 0.24 | 0.13 | 0.22 | −0.07 |
| AC087857.1 | −1.91 | 1.62 | 0.98 | 0.12 | −1.07 | CLDND2 | −0.28 | −0.16 | −0.55 | −0.19 | 0.32 | CBWD2 | 0.00 | 0.08 | −0.08 | 0.04 | 0.04 |
| HARBI1 | 0.39 | −0.23 | −0.10 | −0.29 | 0.05 | MIR5687 | −0.28 | 0.38 | −0.33 | −0.28 | −1.07 | AL390882.1 | −0.07 | 0.47 | −1.51 | 1.78 | −0.55 |
| RPL7L1P8 | 1.07 | −0.81 | −1.37 | 0.07 | −0.38 | MTCO1P30 | −0.97 | 0.52 | −0.54 | 1.13 | 0.03 | AC012339.1 | 0.05 | −1.06 | −1.49 | 0.46 | −1.73 |
| RPL31P52 | 1.05 | −0.56 | −0.35 | 0.50 | 0.23 | EIF1P6 | −0.22 | 0.13 | 0.07 | −0.07 | −0.23 | NKX2-1-AS1 | 0.17 | 1.03 | 0.50 | 0.26 | −1.71 |
| NACC2 | 0.26 | −0.10 | −0.32 | −0.20 | −0.24 | SPATA2L | −0.14 | −0.01 | 0.13 | 0.21 | 0.18 | GEMIN2P2 | 0.09 | −0.47 | −0.08 | −1.46 | −0.97 |
| PRR4 | −0.61 | 0.29 | 0.96 | 0.20 | 0.75 | AC118755.1 | 0.54 | −0.85 | −1.21 | −1.65 | −0.60 | AC111182.1 | 0.01 | −0.63 | −0.55 | 0.10 | 0.10 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC004554.2 | −1.20 | 0.30 | 0.48 | 1.10 | 1.43 | AC090192.1 | −0.21 | 0.35 | 0.42 | 0.29 | 0.25 | AC093142.1 | −0.04 | −0.36 | 0.01 | 0.88 | −1.09 |
| BX470102.1 | −0.42 | 0.08 | 0.69 | −0.51 | −0.09 | AL158840.1 | −0.57 | −0.05 | 0.35 | −0.91 | 0.01 | RN7SL580P | 0.17 | 0.39 | −0.18 | 0.41 | −1.04 |
| ELMOD1 | −0.73 | 0.53 | 1.27 | 0.78 | −0.27 | AC083899.1 | 0.19 | −0.52 | −0.90 | 0.19 | −0.06 | DBH | −0.03 | −0.19 | −0.85 | 0.64 | −0.46 |
| MXD4 | −0.27 | 0.37 | 0.11 | 0.22 | −0.20 | RNA5SP372 | −0.42 | 0.11 | −1.36 | 0.61 | −0.93 | RNU2-6P | 0.02 | 0.21 | −0.16 | 0.59 | −0.52 |
| ARMC10 | 0.25 | −0.06 | 0.07 | 0.00 | 0.10 | NBAT1 | −0.26 | 0.36 | 0.10 | 0.10 | −0.15 | AC128687.2 | 0.07 | −0.47 | −1.10 | −0.11 | −1.41 |
| PAPSS1 | 0.20 | 0.02 | 0.01 | −0.02 | −0.10 | AL031729.1 | 0.33 | −0.95 | −0.86 | 0.51 | 0.01 | AC009965.1 | 0.09 | −0.27 | −0.48 | 1.19 | −0.19 |
| QPRT | −0.55 | 0.66 | 0.80 | 0.42 | 0.32 | AL139412.1 | −0.39 | −0.59 | −1.42 | −0.46 | −0.28 | BCO1 | −0.02 | 0.40 | 0.20 | 0.58 | −0.57 |
| RN7SL171P | −0.57 | −0.35 | −0.54 | −0.03 | 0.37 | RPL12P47 | −0.81 | 0.22 | 1.96 | −0.24 | 1.35 | AL121835.1 | −0.17 | −0.11 | −1.35 | 0.53 | −0.95 |
| SNORA58 | 1.25 | −1.67 | −0.01 | −0.18 | 1.59 | AL606517.1 | 0.21 | −0.05 | 0.24 | −0.07 | −0.19 | AP001189.3 | 0.02 | 0.29 | 0.05 | 0.14 | −0.88 |
| BTF3P7 | 1.07 | −0.73 | −0.91 | −0.45 | −0.37 | AC090651.1 | 0.37 | −1.12 | −0.46 | −0.40 | 0.28 | OR52E3P | −0.10 | 0.16 | −1.66 | 1.71 | −1.33 |
| PCSKIN | −0.64 | 0.61 | 1.07 | 0.20 | 0.11 | CPOX | −0.06 | −0.11 | 0.12 | 0.06 | 0.36 | LINC01386 | −0.17 | 0.93 | −0.18 | 0.43 | −1.58 |
| KCNN2 | −0.68 | 0.04 | 0.20 | 0.40 | 0.29 | RPL5P1 | 0.36 | 0.97 | 0.15 | 0.51 | −0.05 | SMURF1 | 0.00 | 0.05 | −0.20 | 0.00 | −0.16 |
| MYH1 | −0.93 | −0.39 | −0.31 | −0.14 | −0.38 | AC027807.1 | −0.60 | 0.41 | 0.43 | 0.44 | 0.31 | AC113192.3 | −0.10 | −1.15 | −0.49 | −0.77 | 0.38 |
| AL592295.2 | −1.02 | −0.09 | −0.14 | −0.25 | 0.39 | PAQR9-AS1 | −0.41 | −0.53 | 0.01 | 0.66 | 0.97 | RAC1P6 | −0.06 | 0.94 | −0.77 | 1.32 | −0.64 |
| AC055748.1 | 1.25 | −1.07 | 0.64 | −0.42 | 1.15 | AP000851.1 | −0.86 | 0.95 | −0.74 | 0.09 | −2.44 | OR8B7P | 0.17 | −0.75 | 1.45 | −0.78 | 1.88 |
| MFSD13B | −0.33 | 0.40 | 0.53 | 0.08 | 0.27 | MCIDAS | 0.38 | −1.61 | −0.24 | −0.43 | 1.78 | IGKV2OR22-4 | −0.17 | −0.12 | 0.27 | −0.14 | −0.60 |
| FZD10-DT | −0.51 | 0.25 | 0.15 | 0.17 | 0.01 | LINC01526 | −0.62 | 0.78 | −0.41 | 0.72 | −2.06 | AC010620.1 | 0.09 | −1.44 | 1.07 | −1.13 | 0.63 |
| SNORD58 | 0.87 | −0.11 | −0.34 | 0.42 | 0.00 | AC007731.4 | 0.16 | −0.45 | −0.75 | −0.35 | 0.10 | COL11A2P1 | −0.17 | 0.29 | 0.42 | −0.53 | 0.28 |
| CAMTA1 | −0.18 | 0.25 | 0.10 | 0.05 | −0.06 | AC087392.4 | 0.24 | −0.07 | −0.09 | −0.60 | 0.18 | MAGEA13P | −0.17 | −0.66 | 0.36 | 1.72 | 1.82 |
| CHRM4 | −1.39 | 1.61 | 2.50 | 0.86 | −0.58 | RN7SL530P | −0.34 | −2.27 | 0.27 | −0.28 | 2.08 | SIGIRR | 0.01 | 0.15 | −0.54 | 0.11 | −0.40 |
| ANKRD20A14P | −0.52 | 0.90 | 1.02 | 0.81 | 1.09 | RPLP1P13 | −0.28 | −0.92 | 0.24 | −0.64 | −0.05 | AC108673.2 | −0.02 | −0.10 | 1.10 | −0.37 | 0.02 |
| AC099792.1 | −0.76 | 0.76 | 0.41 | 0.83 | 0.25 | RNU6-553P | −0.37 | −1.39 | 1.60 | −1.31 | 0.32 | MIR30D | −0.06 | 0.00 | −0.53 | −0.31 | −1.17 |
| RPL7P9 | 0.44 | −0.12 | −0.21 | −0.12 | −0.29 | AC092639.1 | −1.32 | 0.19 | 0.54 | 0.82 | −0.76 | OR2T8 | 0.06 | 0.71 | 0.43 | −0.86 | 0.40 |
| AC104115.2 | 0.77 | −0.44 | −0.39 | 0.02 | 0.27 | AL159152.1 | −0.67 | 0.00 | −0.05 | −0.04 | −0.99 | PLCD3 | 0.01 | 0.20 | −0.23 | 0.23 | −0.31 |
| ARL13B | 0.20 | 0.01 | −0.12 | −0.08 | −0.25 | SREBF1 | 0.11 | 0.20 | −0.25 | 0.48 | 0.09 | HMGN3P1 | −0.17 | 0.43 | 0.00 | 1.53 | 1.02 |
| ARSD | −0.21 | 0.21 | 0.24 | 0.41 | 0.29 | LINC01964 | 0.52 | 0.15 | −0.64 | 0.46 | −1.14 | AC092278.1 | 0.03 | −1.29 | −0.14 | 0.64 | 1.87 |
| AC024337.1 | −1.23 | 0.52 | 0.93 | 0.53 | 0.37 | RNU6-960P | 0.43 | 0.29 | 1.11 | 0.10 | 0.84 | MTCO1P4 | −0.04 | −0.15 | 1.63 | −0.23 | 1.11 |
| RNU6-619P | 0.82 | −0.41 | 0.69 | −0.53 | 0.43 | AP003038.1 | −1.09 | −0.94 | −0.29 | −1.91 | −1.13 | AL355601.1 | −0.06 | −0.61 | −1.67 | −0.55 | −0.26 |
| CDRT15 | 1.15 | −0.95 | 0.26 | −0.49 | −0.29 | IRAK3 | −0.13 | −0.08 | 0.37 | −0.12 | 0.12 | PRSS12 | 0.01 | 0.05 | 0.16 | 0.19 | 0.04 |
| AC097626.1 | 0.55 | −0.25 | −0.39 | 0.29 | 0.24 | ASTE1 | 0.11 | −0.09 | 0.16 | 0.01 | 0.12 | AC016152.1 | −0.08 | −0.31 | −1.57 | −0.47 | −0.25 |
| CHMP6 | −0.28 | 0.16 | −0.35 | 0.16 | −0.22 | AC091185.1 | −0.17 | 0.28 | 0.71 | −0.11 | 0.27 | BRPF1 | 0.00 | −0.02 | −0.27 | −0.03 | −0.20 |
| AC097493.1 | −1.14 | 0.80 | 2.35 | −1.23 | −0.96 | MIR4480 | 0.27 | 0.37 | 0.70 | −0.27 | −0.32 | AC022616.4 | −0.17 | 0.35 | −0.87 | −0.86 | −1.34 |
| AL360178.1 | −1.57 | 0.32 | 1.72 | 0.54 | 3.29 | RN7SL739P | −0.37 | 1.05 | 1.05 | 0.30 | −0.48 | KIF3AP1 | −0.08 | −0.54 | −0.95 | 1.07 | 0.04 |
| CATSPER3 | 0.71 | −0.41 | −0.49 | 0.25 | 0.05 | AC020978.3 | 0.30 | −0.06 | 0.42 | −0.09 | 0.02 | RNU1-61P | −0.12 | −0.06 | 0.61 | −1.72 | 1.40 |
| POLR3A | 0.17 | −0.12 | −0.26 | 0.03 | 0.03 | MTATP6P2 | −0.35 | 0.18 | −0.61 | −0.14 | −0.43 | RBBP8P1 | 0.02 | 0.12 | −0.31 | 0.62 | 0.23 |
| MTHFD2L | 0.25 | −0.16 | −0.23 | 0.12 | −0.10 | LINC02246 | 0.27 | −0.42 | −0.91 | −0.60 | −0.78 | AC026336.4 | −0.17 | −0.24 | −1.27 | 2.18 | −1.08 |
| ATG13 | 0.21 | 0.10 | −0.16 | 0.07 | −0.31 | FMO9P | 0.50 | 0.67 | −2.16 | 0.72 | −1.33 | AP000525.9 | −0.02 | 0.32 | 0.25 | 0.36 | −0.52 |
| AC144450.1 | 1.32 | −0.72 | −2.54 | 0.46 | −1.01 | CRLS1 | 0.09 | −0.20 | −0.01 | −0.06 | 0.11 | AL162632.2 | −0.05 | −1.60 | 0.97 | −0.06 | 0.03 |
| MSH3 | 0.17 | −0.06 | −0.29 | −0.05 | −0.26 | ECHDC3 | −0.10 | 0.07 | −0.40 | 0.26 | −0.15 | AL033528.2 | 0.05 | 0.71 | 2.42 | 0.65 | 0.29 |
| P2RX4 | −0.27 | −0.14 | −0.21 | −0.07 | −0.22 | AL353997.2 | 0.29 | −0.45 | −0.47 | −0.05 | 0.60 | RNA5SP209 | 0.03 | 0.61 | 0.87 | 0.34 | 0.48 |
| GRAMD2B | −0.26 | 0.44 | 0.55 | 0.00 | −0.09 | AC011247.3 | −1.10 | −0.48 | 0.28 | 0.82 | 0.94 | ANKRD26P1 | −0.02 | −0.63 | −0.52 | 0.19 | −0.59 |
| LLPHP2 | 1.23 | 0.28 | 0.11 | 0.21 | −0.33 | LINC02014 | −0.75 | −1.09 | 2.54 | −1.94 | 2.31 | AL356805.1 | −0.02 | −0.13 | 1.21 | −0.21 | 0.56 |
| AL365436.1 | −0.49 | 0.53 | 0.21 | 0.62 | 0.07 | AC243965.2 | −0.24 | 0.12 | −0.39 | 0.74 | −0.47 | LINC01895 | 0.16 | NA | −1.13 | 1.65 | 0.36 |
| FAM198B-AS1 | −0.51 | 0.48 | 1.05 | 0.13 | 0.17 | AC005586.1 | 0.30 | 0.41 | −0.70 | 0.24 | −1.39 | GNAI2P2 | 0.12 | 0.38 | 0.82 | −0.90 | 1.08 |
| POF1B | 0.54 | 0.44 | 0.29 | 0.31 | −0.53 | AL139094.1 | 0.38 | 0.30 | 0.22 | 0.48 | 0.01 | SLC7A5P1 | −0.01 | −0.16 | −0.77 | 0.41 | −0.36 |
| AC019097.1 | −0.82 | −0.15 | 1.20 | −0.51 | 0.36 | AC022509.4 | −0.67 | −0.22 | −0.84 | 0.58 | −1.04 | AC022118.1 | 0.16 | 0.13 | −1.19 | −0.08 | −0.83 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC069437.1 | −1.15 | 0.59 | 1.22 | 0.43 | 0.28 | OR5B17 | −0.60 | −1.20 | 1.67 | 0.29 | 3.08 | AC124067.3 | 0.08 | 0.57 | −0.18 | 0.44 | −1.88 |
| MOB1B | 0.29 | −0.09 | −0.08 | 0.04 | 0.04 | AC104966.1 | 0.21 | −0.12 | 0.12 | −0.22 | −0.01 | AL442638.1 | 0.16 | 0.15 | NA | −1.49 | −1.75 |
| AP005436.3 | 1.06 | −0.65 | −0.35 | 0.09 | −0.41 | MTND4P14 | 0.19 | −0.10 | −0.05 | −0.26 | −0.16 | LINC01706 | −0.16 | 0.82 | −1.33 | 0.39 | −2.39 |
| G39123 | −1.70 | 0.04 | 1.04 | 2.00 | 1.76 | ERP29P1 | −0.29 | −0.17 | 0.54 | 0.34 | 0.38 | AC018506.1 | −0.02 | −0.08 | −0.13 | 0.22 | −0.24 |
| AL354696.1 | 0.71 | −0.67 | −1.19 | 0.45 | 0.19 | AC009320.1 | −0.36 | 1.01 | 0.11 | −0.47 | −0.89 | AC022743.1 | −0.16 | −0.65 | 0.17 | 0.08 | −0.86 |
| PUSL1 | 0.36 | −0.18 | −0.65 | 0.07 | −0.05 | AC012645.2 | 0.21 | 0.15 | −0.69 | −0.06 | −0.72 | LDHAL6FP | −0.01 | 0.07 | −0.23 | 0.17 | −0.19 |
| AC096708.2 | 1.00 | −0.12 | −0.64 | 0.02 | −0.35 | AL031283.1 | 0.31 | −0.49 | −0.98 | 0.28 | 0.04 | G33346 | −0.04 | 0.70 | −0.30 | 0.93 | −0.83 |
| AL139318.1 | −1.20 | 0.13 | 0.07 | −0.08 | 0.23 | LINC02282 | −0.81 | 0.34 | −0.12 | −0.26 | −1.09 | AC105417.1 | −0.10 | 0.37 | −0.85 | 1.30 | −0.85 |
| AC008171.1 | −0.64 | 0.58 | 0.47 | 0.23 | −0.06 | AC125604.1 | −0.74 | −0.13 | −0.23 | 1.09 | 0.92 | AL451054.3 | 0.16 | −0.81 | −1.79 | 0.72 | 0.34 |
| AC091132.2 | −0.49 | −0.27 | 0.24 | −0.33 | 0.32 | AL451060.1 | 0.38 | 0.82 | −1.65 | 1.16 | −2.17 | AC060766.4 | 0.02 | 0.18 | 0.41 | −0.24 | −1.16 |
| ALG11 | −0.20 | −0.08 | 0.11 | 0.04 | 0.21 | PPIAP10 | 0.31 | −0.52 | 0.25 | 0.03 | 0.45 | OR4T1P | 0.09 | −0.49 | −1.82 | 1.40 | −0.67 |
| AP002803.1 | −1.50 | 1.79 | 1.78 | −0.77 | −0.80 | AL157911.1 | 0.32 | 0.10 | 0.27 | −0.77 | −0.85 | AC093810.1 | 0.16 | −0.87 | 0.19 | −1.85 | 0.90 |
| RN7SL693P | −1.48 | −0.74 | 1.76 | 0.98 | 0.95 | ADAMTS9 | 0.17 | −0.62 | 0.09 | −0.72 | 0.02 | SMAD6 | −0.01 | −0.16 | 0.07 | −0.17 | −0.13 |
| LIMD1 | −0.24 | −0.25 | 0.02 | −0.10 | 0.34 | IL17RB | 0.14 | −0.18 | −0.45 | 0.20 | −0.12 | OR5BH1P | −0.13 | −0.07 | 0.40 | −0.06 | −0.03 |
| ITIH4 | −0.78 | 0.78 | 1.07 | −0.29 | −0.29 | CCDC195 | 0.60 | −0.63 | −1.95 | 1.00 | 0.68 | AC006482.1 | 0.08 | −2.07 | 1.40 | −1.15 | 3.52 |
| IFFO2 | 0.54 | 0.19 | −0.36 | −0.06 | −0.69 | AC131935.1 | −1.03 | 0.30 | −0.09 | 0.28 | −0.49 | RNU4-26P | −0.06 | −0.67 | 0.83 | −1.30 | 0.19 |
| EIF3LP1 | −1.71 | 0.71 | −1.02 | −0.92 | −1.42 | AL606970.1 | −0.65 | −0.63 | 0.36 | −0.21 | −0.43 | AC024940.2 | −0.01 | 0.00 | 0.40 | 0.17 | 0.64 |
| CCR1 | 0.85 | −0.79 | −0.56 | −0.25 | −0.51 | AC017015.2 | −0.38 | −1.62 | 0.68 | −0.01 | 1.56 | PHBP8 | 0.16 | −0.75 | −1.02 | 0.32 | −1.53 |
| DLG1-AS1 | 1.42 | −1.52 | −1.48 | 1.15 | 1.52 | AC015804.1 | −0.31 | 0.20 | 0.34 | −0.37 | −0.32 | AC068234.2 | −0.04 | 1.22 | 0.12 | 1.05 | −0.04 |
| AC116351.2 | −0.94 | 0.01 | 0.60 | 0.08 | 0.68 | IFNL3 | −0.70 | 0.74 | 0.60 | 0.56 | −1.98 | OR4C6 | −0.10 | −0.55 | −2.64 | 1.67 | −0.50 |
| RNU4-80P | 1.11 | −0.50 | −0.56 | −0.31 | −0.45 | AC093214.1 | 0.55 | −0.27 | −2.17 | 0.29 | −1.25 | OR4K1 | −0.04 | −1.29 | 0.63 | 0.23 | 0.82 |
| OSBPL1A | −0.25 | 0.26 | 0.36 | 0.12 | 0.04 | LINC00852 | 0.17 | −0.26 | 0.14 | −0.14 | 0.56 | LINC00350 | 0.03 | −1.04 | 0.01 | 0.04 | 0.66 |
| MGAT5 | 0.20 | 0.02 | −0.26 | −0.05 | −0.19 | PRR5-ARHGAPI | −0.61 | −0.33 | −0.48 | 0.63 | 0.66 | AC073517.1 | −0.02 | 0.49 | −0.09 | 0.83 | −0.14 |
| RP11-293G6__A. | −0.84 | 0.67 | −0.56 | 0.18 | −0.30 | G33828 | −0.24 | 0.15 | 0.16 | −0.10 | 0.13 | AC009021.1 | −0.16 | 1.59 | −0.77 | 0.24 | −1.03 |
| AL139011.1 | −0.49 | 0.22 | 0.59 | −0.05 | 0.06 | AC020779.2 | −0.42 | −0.81 | 0.30 | 0.32 | 0.60 | AKNA | 0.01 | −0.37 | −0.07 | −0.26 | 0.15 |
| AC130466.1 | −0.83 | 0.03 | 0.78 | 0.31 | 0.51 | MTIF3 | −0.08 | 0.14 | 0.10 | −0.10 | −0.03 | AL034403.1 | −0.16 | −0.94 | 0.76 | 0.19 | −0.19 |
| ANKRD50 | 0.28 | 0.00 | 0.03 | −0.12 | −0.13 | AL121893.1 | 0.79 | −0.36 | −1.47 | −0.59 | −0.59 | OR5D2P | 0.16 | 0.22 | 0.64 | −0.81 | −1.88 |
| SCAF4 | 0.14 | −0.02 | −0.30 | −0.01 | −0.23 | SMTNL2 | −0.31 | −0.92 | −0.15 | −0.19 | −0.22 | AC105758.1 | 0.16 | −0.49 | −1.41 | 1.03 | NA |
| AC037487.1 | −0.62 | 0.09 | 0.61 | 0.23 | 0.87 | MMRN2 | 0.11 | 0.04 | −0.08 | 0.08 | −0.23 | AC055758.2 | 0.05 | −0.84 | −0.53 | 1.03 | −0.55 |
| DQX1 | −0.50 | 0.40 | 0.72 | 0.36 | 0.23 | AC025259.3 | −0.60 | 1.63 | −0.75 | −0.91 | −2.87 | AL354836.1 | 0.01 | 0.04 | −0.21 | 0.43 | 0.19 |
| CAD | 0.32 | −0.39 | −0.42 | −0.03 | 0.22 | AC078991.1 | −1.17 | 0.43 | −1.19 | 2.01 | −0.71 | OR4K4P | 0.16 | −0.91 | −0.89 | −0.96 | −0.35 |
| LINC01929 | 1.14 | −1.59 | −2.34 | −1.20 | −1.47 | AC078778.2 | 0.22 | −0.04 | −0.07 | 0.08 | −0.19 | G33806 | −0.02 | −0.18 | −0.16 | −0.06 | −0.17 |
| AP002993.1 | 0.69 | −0.40 | −0.08 | −0.07 | 0.10 | AC020892.1 | 0.44 | −0.76 | −0.62 | −0.38 | −1.95 | AL357793.2 | 0.05 | −0.44 | 0.30 | 0.27 | 2.39 |
| MMS19 | −0.22 | 0.15 | 0.07 | 0.10 | 0.09 | AC105402.3 | −0.32 | 0.00 | 0.42 | −0.01 | 0.25 | AC007368.2 | 0.06 | −0.48 | −1.07 | 0.76 | −0.88 |
| PTPN4 | 0.24 | −0.01 | −0.16 | 0.16 | 0.02 | NXPE2P1 | −1.32 | 0.35 | 3.22 | −1.15 | 1.31 | AC099811.6 | 0.01 | −0.07 | 0.28 | 0.10 | 0.21 |
| PACRG-AS1 | −1.46 | 0.71 | 0.33 | 0.88 | 0.47 | RAP1BP1 | 0.52 | −0.32 | 1.22 | −0.46 | 0.13 | LINC00330 | −0.03 | −0.38 | −0.23 | 0.82 | −1.07 |
| AP000322.2 | −1.06 | 0.15 | 0.95 | 0.44 | 0.60 | SNORD114-11 | 0.65 | 0.70 | −0.08 | 0.23 | −0.37 | AC007333.1 | −0.16 | −0.58 | −0.30 | −1.50 | 1.01 |
| PRPF31 | 0.20 | −0.12 | −0.32 | 0.07 | −0.05 | PKN3 | −0.11 | 0.09 | −0.16 | 0.18 | −0.13 | AL928921.1 | −0.16 | −0.05 | −0.02 | 1.88 | 2.53 |
| ERCC8 | 0.24 | −0.18 | 0.09 | −0.12 | 0.17 | EEF1A1P33 | −0.49 | −0.24 | −2.69 | 0.31 | −0.92 | AC087477.3 | −0.16 | −0.85 | 1.03 | −0.31 | 2.15 |
| NRK | −0.77 | 0.75 | 0.57 | 0.44 | −0.68 | AC011461.1 | 0.26 | −0.69 | −0.43 | 0.59 | 1.00 | MIR645 | 0.01 | −0.30 | 0.35 | −0.16 | −0.12 |
| PAXIP1 | 0.20 | −0.21 | −0.34 | −0.01 | −0.02 | MS4A7 | 0.21 | −0.19 | 0.15 | −0.33 | −0.34 | OR4F6 | 0.12 | −0.88 | −1.40 | 1.05 | −0.21 |
| NRIP3 | 0.52 | −0.61 | −0.86 | −0.30 | −0.36 | GIMAP6 | −0.15 | 0.24 | 1.14 | −0.21 | 0.08 | MTCO3P38 | 0.08 | −1.40 | 1.03 | −0.37 | 0.62 |
| AC009227.1 | −0.96 | 0.76 | 0.34 | 0.03 | −1.21 | AP000943.3 | 0.39 | −0.70 | −0.58 | 0.73 | 1.15 | AC140076.1 | 0.02 | 0.43 | 0.27 | −0.11 | 0.71 |
| ALKBH7 | 0.26 | 0.24 | −0.02 | 0.12 | −0.35 | AC006041.1 | −0.52 | 0.36 | 1.60 | −0.56 | −0.25 | GRPEL2P2 | 0.16 | 0.51 | 0.26 | 2.36 | −0.32 |
| AC093788.1 | 0.47 | −0.24 | −0.19 | 0.24 | 0.24 | SLC22A2 | −0.28 | −0.42 | −1.26 | 0.00 | −0.58 | KRTAP5-10 | 0.03 | −1.30 | −0.73 | −0.15 | −0.06 |
| ENTPD1 | 0.29 | −0.39 | −0.07 | −0.09 | 0.08 | FABP9 | −0.60 | 1.55 | 2.65 | 1.03 | 1.95 | AL445675.1 | 0.10 | 0.76 | −0.73 | 0.83 | −0.59 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| MRPS21P9 | −1.21 | 1.26 | 1.47 | 0.00 | 0.57 | MIR4296 | 0.36 | −0.18 | −0.83 | −0.48 | −0.40 | RNA5SP445 | −0.06 | −0.16 | −0.33 | 1.08 | −0.26 |
| C9orf78 | 0.22 | −0.08 | −0.11 | −0.12 | −0.20 | AL356441.1 | −0.88 | 0.22 | 1.80 | −1.63 | −0.57 | IGKV1-39 | 0.16 | 0.31 | 0.81 | 3.01 | 0.21 |
| PDE10A | 0.49 | −0.38 | −0.43 | −0.19 | −0.26 | AP001057.1 | −0.77 | 1.07 | −1.48 | −0.17 | −2.27 | AC082651.2 | 0.06 | 0.10 | −0.82 | −0.36 | 0.20 |
| AC004990.1 | −1.02 | −0.97 | −1.73 | 0.59 | −0.36 | HNRNPA3P15 | −0.22 | −0.37 | −0.36 | −0.19 | 0.14 | CACNA1C-IT2 | 0.09 | −0.46 | 0.28 | 0.90 | −0.13 |
| AC025627.2 | −2.76 | 0.18 | 3.31 | 1.66 | 2.20 | AL139353.2 | −0.14 | 0.10 | 0.34 | −0.07 | 0.14 | PWRN4 | −0.07 | 0.38 | −1.36 | 1.25 | −1.55 |
| RN7SL345P | −1.73 | 0.11 | 0.27 | −0.11 | 0.41 | AC114781.3 | 0.76 | −1.12 | −0.77 | −0.52 | 0.52 | RNU4-19P | 0.08 | 0.31 | 0.06 | 0.56 | −0.43 |
| AC004241.1 | 0.61 | 0.37 | 0.03 | 0.09 | −0.68 | AC073912.1 | 0.42 | −0.17 | −0.27 | −0.37 | 0.48 | RNU6-621P | −0.02 | 0.31 | 0.83 | 0.14 | 0.15 |
| AP001767.4 | −0.48 | −0.71 | 0.53 | −0.40 | 0.81 | EIF2S2P3 | −0.26 | −0.43 | 0.11 | −0.26 | −0.01 | LINC00867 | 0.04 | −1.38 | −0.73 | −0.37 | −0.10 |
| MORN2 | 0.38 | 0.01 | 0.08 | −0.14 | −0.19 | LINC01700 | −0.62 | −1.37 | −0.26 | −0.20 | 0.14 | SEPHS1P7 | 0.16 | −0.65 | 1.36 | −0.50 | 1.19 |
| AL031709.1 | −0.82 | −0.06 | 0.96 | 0.23 | 0.63 | LINC00559 | 0.46 | −0.83 | −0.44 | 0.70 | 0.84 | AC007218.1 | 0.15 | −0.75 | −0.14 | −0.33 | 0.06 |
| AC010970.1 | −0.76 | 0.34 | −0.10 | 1.49 | −0.41 | AC098583.1 | −0.72 | −0.30 | −0.07 | 0.74 | 1.50 | OR4G1P | 0.08 | −1.29 | 0.57 | −0.61 | 1.22 |
| AC124067.4 | −1.05 | 0.21 | −0.29 | 0.94 | 0.76 | AL451070.1 | 0.35 | −0.66 | −0.73 | −0.74 | −1.18 | LINC01889 | −0.09 | 0.23 | −0.02 | 0.45 | −2.03 |
| RP13-996F3.5 | −0.85 | 0.14 | 0.44 | 0.68 | 0.32 | FNBP1 | −0.06 | 0.02 | 0.01 | −0.07 | 0.01 | AC022400.5 | −0.01 | −0.20 | 0.25 | −0.17 | 0.56 |
| RNU1-60P | 0.64 | 0.04 | −0.22 | −1.14 | 0.12 | AC090403.1 | −0.48 | −1.13 | −0.87 | 0.14 | −0.90 | OR10G6 | 0.07 | 0.12 | −0.72 | 0.84 | −0.52 |
| SNRPGP15 | 0.82 | −0.12 | −0.65 | −0.03 | −0.41 | CYP8B1 | −0.20 | −0.06 | 0.68 | −0.40 | 0.17 | AC006305.3 | −0.05 | 0.05 | 0.47 | 1.47 | −0.07 |
| NPAT | 0.21 | 0.04 | 0.09 | −0.10 | −0.15 | MVD | 0.13 | 0.16 | −0.21 | 0.37 | −0.22 | AC012640.4 | 0.03 | 0.26 | −0.12 | 0.46 | −0.50 |
| AC005703.4 | −1.37 | 0.59 | −0.15 | 0.93 | −0.65 | ECI1 | −0.09 | 0.27 | 0.04 | 0.22 | 0.00 | AC239800.3 | 0.03 | 0.36 | −0.81 | −0.10 | 0.13 |
| AL049840.2 | 1.10 | −0.36 | −0.33 | 0.10 | 0.23 | AL139423.1 | −0.19 | 0.73 | 0.55 | 0.23 | −0.13 | AL645820.1 | −0.16 | 0.22 | −1.70 | −0.92 | −2.05 |
| AC092834.1 | −1.29 | 0.95 | 1.72 | 0.23 | 0.19 | AC099778.2 | 0.41 | −0.82 | 0.14 | −0.09 | 0.16 | AC024382.1 | −0.03 | −0.49 | 0.32 | 0.25 | 1.08 |
| DYNC1I2P1 | 0.53 | 0.00 | −0.66 | −0.04 | −0.71 | RPL7P17 | −0.30 | 0.78 | 1.01 | 0.07 | 0.66 | IGHEP1 | −0.16 | −0.76 | −0.07 | 0.70 | 3.71 |
| SC5D | 0.37 | −0.10 | −0.11 | 0.23 | 0.17 | LINC00928 | 0.97 | −0.49 | −1.34 | −0.90 | −0.63 | LINC00398 | 0.03 | −0.21 | −1.08 | 0.13 | −0.97 |
| PEAK1 | −0.26 | 0.21 | 0.51 | −0.24 | −0.10 | KLC1 | 0.09 | 0.03 | 0.04 | −0.10 | −0.04 | AC107373.1 | −0.05 | −0.27 | 0.58 | −1.57 | −0.27 |
| G9812 | −1.06 | −0.30 | 1.74 | −0.34 | 1.55 | RPL23AP49 | −0.77 | −0.33 | 1.20 | 0.76 | 1.64 | AC109925.1 | 0.06 | −0.88 | 0.77 | 0.00 | 1.37 |
| SNRNP48 | 0.19 | −0.04 | −0.08 | −0.01 | −0.09 | AC020763.1 | 0.37 | −0.11 | −0.65 | −0.88 | −0.75 | AP000692.2 | 0.01 | 0.05 | −0.40 | 0.33 | −0.04 |
| AC093297.1 | −1.17 | 1.30 | 2.20 | −0.10 | 0.75 | G2520 | −0.18 | 0.21 | 0.34 | 0.36 | 0.15 | RNU7-34P | −0.16 | −0.09 | 0.61 | −0.41 | 2.00 |
| MIR4451 | −1.26 | 0.15 | 1.39 | 0.22 | 0.80 | MIR1273D | −0.53 | 0.24 | −1.73 | −0.10 | −2.44 | AL035604.1 | −0.03 | 0.18 | −1.17 | 0.31 | −0.30 |
| PIN1 | 0.19 | −0.05 | −0.23 | −0.04 | −0.30 | AL035427.1 | −0.33 | 0.01 | 1.04 | −0.08 | 0.18 | AC010880.1 | 0.16 | −1.00 | 0.00 | −0.84 | −0.62 |
| RN7SKP44 | −1.75 | 1.53 | 2.31 | 1.07 | 1.12 | AC002428.2 | −0.49 | −0.48 | −0.49 | 0.32 | −1.12 | AC239804.2 | −0.13 | 2.10 | 0.85 | −0.18 | −0.25 |
| CHRFAM7A | −0.89 | −0.64 | 1.55 | −0.78 | 1.12 | MIR4316 | 0.70 | −2.33 | −1.52 | −0.89 | −0.44 | OR5M10 | −0.08 | −1.07 | −1.70 | 1.36 | −0.53 |
| RNF11P2 | −1.34 | −0.23 | 1.94 | −0.40 | −0.04 | PLXND1 | −0.14 | −0.13 | 0.39 | −0.17 | 0.00 | AC017104.2 | −0.16 | −0.52 | −0.11 | −1.47 | −0.24 |
| PELI1 | 0.23 | 0.08 | −0.19 | 0.07 | −0.47 | AC007614.2 | −0.47 | 0.88 | −0.08 | 0.60 | −0.33 | AC092601.1 | 0.16 | −0.65 | −0.30 | 0.32 | 0.84 |
| CDK18 | 0.33 | −0.19 | −1.01 | 0.10 | −0.19 | PPIAP71 | −0.35 | −0.61 | 1.62 | 0.44 | 1.75 | IGHV3-42 | −0.16 | −0.13 | 0.25 | −0.92 | −0.12 |
| RPL21P16 | 0.64 | −0.26 | −0.26 | −0.19 | −0.63 | COX5BP6 | −0.19 | −0.17 | −0.07 | 0.34 | 0.30 | AL162431.3 | 0.01 | 0.24 | 0.21 | −0.06 | 0.06 |
| SFRP5 | −0.78 | 0.67 | 0.79 | 0.01 | −0.16 | EP400P1 | −0.08 | −0.22 | −0.14 | −0.07 | −0.01 | GOLGA2P6 | 0.16 | −0.66 | 0.17 | 1.44 | 1.64 |
| KLHL22 | −0.26 | 0.02 | 0.15 | 0.00 | 0.19 | SNORA68 | −0.25 | −0.60 | 1.39 | −0.01 | 0.80 | AL121759.2 | −0.15 | 0.19 | −0.32 | −0.09 | −0.20 |
| LINC01354 | −1.07 | −0.43 | 0.82 | −0.55 | 0.45 | HNRNPA1P63 | 0.70 | −1.25 | −1.43 | −0.04 | −0.06 | SDC3 | 0.01 | 0.09 | −0.09 | −0.05 | −0.14 |
| RNU6-720P | 0.70 | −0.33 | 0.12 | 0.24 | −0.18 | KRT18 | −0.24 | 0.31 | 0.17 | 0.02 | 0.03 | AL353052.2 | 0.05 | −0.43 | −1.44 | −1.15 | −1.29 |
| FAM241A | 0.25 | −0.03 | 0.08 | −0.19 | 0.05 | CD4 | 0.15 | −0.24 | 0.28 | −0.22 | 0.28 | AC093903.1 | −0.15 | 0.30 | −1.06 | 1.21 | −1.94 |
| SLC2A8 | 0.24 | −0.12 | −0.74 | 0.10 | −0.20 | AC004801.5 | −0.76 | 0.37 | −1.56 | 0.04 | −0.85 | MTCO2P7 | −0.06 | −0.19 | −1.88 | −0.27 | −2.37 |
| NMD3 | 0.22 | 0.00 | −0.16 | −0.13 | −0.29 | OTX2 | 0.52 | −2.27 | −2.55 | 0.89 | −0.80 | LINC00410 | −0.04 | −1.09 | −0.89 | −0.05 | −0.58 |
| FAM205BP | −0.77 | 0.39 | 0.18 | 0.16 | 0.42 | PLCXD2 | 0.15 | −0.34 | −0.22 | −0.20 | −0.03 | AC096721.1 | 0.15 | −0.39 | −0.30 | 0.22 | 0.32 |
| AC019181.1 | 0.70 | −0.22 | −0.76 | 0.30 | 0.31 | AC126175.1 | −0.68 | −0.09 | 1.60 | 0.83 | −0.07 | AC012182.1 | 0.07 | 0.24 | −0.55 | 0.05 | −0.83 |
| STK35 | 0.30 | −0.17 | −0.11 | −0.04 | 0.02 | ERVH-1 | −0.62 | −0.23 | 0.83 | −0.89 | 0.20 | AL139220.2 | 0.01 | −0.84 | −0.99 | −0.13 | −0.02 |
| SMAD1 | 0.29 | 0.02 | −0.18 | 0.15 | 0.00 | AC073912.2 | −0.28 | −0.61 | 0.52 | 0.59 | 0.71 | RNA5SP27 | −0.05 | −1.36 | −2.41 | 0.75 | −1.47 |
| AC131009.3 | 0.86 | −0.85 | −0.56 | −0.10 | −0.16 | AL162171.2 | 0.17 | 0.23 | 0.34 | 0.21 | 0.19 | AL391834.3 | −0.03 | −0.83 | 0.11 | 0.38 | −0.30 |
| AC026271.1 | 0.63 | 0.11 | −0.76 | −0.03 | −0.26 | ECM1P1 | −0.91 | −0.36 | 2.35 | 0.21 | 0.99 | AP000445.2 | 0.10 | −1.07 | −0.12 | −0.66 | −1.60 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| DRAM2 | 0.31 | −0.07 | −0.14 | 0.05 | −0.22 | RNU4ATAC | 0.18 | −0.35 | −0.60 | −0.44 | −0.59 | DCAF8 | 0.01 | 0.13 | 0.21 | 0.10 | 0.08 |
| CDC40 | 0.16 | −0.07 | 0.04 | −0.08 | 0.04 | IFT74 | −0.07 | 0.20 | 0.08 | 0.11 | −0.09 | AC113423.1 | −0.15 | −0.10 | −0.14 | 1.11 | −1.49 |
| SPAG6 | −1.11 | 0.28 | 0.61 | −0.14 | 0.24 | MTCO2P29 | 0.29 | −0.35 | 0.23 | −0.03 | 0.59 | FUT4 | −0.01 | 0.08 | 0.20 | 0.12 | 0.04 |
| AC245100.1 | −0.96 | 0.75 | 0.74 | 0.14 | −0.37 | AL132708.1 | 0.66 | −0.34 | −0.83 | 0.09 | −0.02 | LINC00698 | 0.03 | −0.33 | −1.12 | −0.03 | −0.77 |
| KRT2 | −0.84 | 1.68 | 1.86 | 1.45 | −0.37 | AL161450.1 | 0.24 | −0.23 | 1.01 | −0.28 | 0.85 | IFITM8P | −0.15 | −0.39 | −0.81 | −0.05 | 0.63 |
| DYRKIA | 0.15 | 0.05 | −0.05 | 0.00 | −0.09 | PHBP21 | −0.37 | 0.47 | 0.62 | 0.92 | 0.48 | OR7D1P | −0.09 | −1.79 | 0.23 | −1.21 | 0.21 |
| AC099684.3 | −1.44 | 0.77 | 0.27 | 0.78 | 0.14 | SPANXA2-OT1 | −0.73 | 0.57 | −1.09 | 0.13 | −2.13 | AC009154.1 | −0.09 | −0.12 | 0.78 | −0.81 | −0.06 |
| AC091488.1 | −1.27 | 0.32 | 1.61 | 0.10 | 0.98 | AP001619.2 | 0.27 | −0.52 | −0.28 | 0.00 | −0.08 | AC108729.2 | 0.08 | −1.54 | 0.37 | −1.19 | 0.69 |
| AC026471.1 | −0.37 | 0.08 | 0.41 | 0.08 | 0.45 | MTND3P13 | −1.07 | −0.47 | 0.99 | −0.55 | 1.48 | SSX5 | 0.05 | −1.76 | −1.59 | −1.02 | −0.75 |
| LIMK2 | 0.21 | −0.06 | −0.26 | 0.07 | −0.04 | FAM71E2 | 1.01 | −1.03 | −2.37 | −0.13 | −0.86 | QRSL1P1 | −0.03 | −0.47 | 1.16 | 0.01 | 0.72 |
| FABP7P1 | −0.83 | 0.60 | 1.38 | 0.38 | −0.06 | MIR3681HG | 0.34 | −0.26 | −1.26 | 0.29 | −0.40 | AC084357.3 | 0.03 | −0.97 | −0.73 | −0.37 | −0.03 |
| PCK2 | 0.30 | 0.09 | −0.35 | 0.22 | −0.34 | ARRDC4 | −0.13 | 0.03 | 0.40 | 0.18 | 0.05 | RBMY2JP | 0.15 | −0.45 | −0.56 | 0.14 | −1.08 |
| GOLGA8Q | −0.73 | 0.78 | 0.57 | 0.67 | 0.37 | AL512844.1 | −0.38 | 0.50 | −0.69 | 0.66 | −1.09 | AP001961.1 | −0.07 | −0.36 | −0.40 | 0.24 | −1.54 |
| LITAF | 0.44 | −0.42 | −0.14 | −0.28 | −0.23 | MIR3605 | 0.79 | 0.72 | −0.36 | 0.27 | 0.22 | AC004923.2 | −0.04 | 0.52 | 1.30 | 1.09 | −0.24 |
| RNF216P1 | −0.16 | 0.12 | −0.05 | −0.09 | −0.17 | RPL23AP17 | 0.36 | 0.81 | 0.90 | 1.10 | 0.67 | AKAP17BP | 0.02 | −0.55 | −0.23 | −0.07 | 0.93 |
| AC079174.1 | −0.57 | −0.83 | −0.75 | 0.01 | 0.59 | RNU1-47P | 0.88 | 0.31 | −1.14 | 0.93 | −0.57 | LINC00200 | 0.04 | −0.13 | −0.80 | 0.54 | −0.31 |
| RPSAP9 | 0.88 | −0.03 | −0.06 | 0.33 | −0.28 | G38458 | −0.31 | 0.23 | 1.46 | −0.14 | 0.16 | AL390961.3 | −0.02 | −0.41 | −1.18 | 0.49 | 0.48 |
| G43247 | 1.54 | −0.21 | −2.11 | −0.09 | −0.73 | GYG2-AS1 | −1.56 | 0.24 | −0.14 | 1.18 | −0.85 | IPPKP1 | 0.10 | −0.20 | 0.50 | −0.09 | 0.16 |
| LDHAP4 | 0.53 | −0.25 | −1.27 | 0.63 | −0.47 | AC091180.2 | −0.19 | 0.27 | 0.71 | −0.09 | 0.04 | AC107871.2 | −0.02 | 0.24 | 0.32 | 0.26 | 0.32 |
| PAXIP1-AS2 | −0.35 | 0.26 | 0.68 | 0.10 | 0.15 | HMGB2P1 | 0.38 | −1.06 | −2.01 | −0.73 | −0.76 | LRRC25 | 0.02 | −0.39 | −0.16 | −0.31 | −0.24 |
| RPE | 0.23 | −0.10 | −0.04 | −0.10 | −0.01 | AC026369.1 | −0.30 | 0.23 | −0.15 | 0.58 | 0.66 | NRAP | 0.02 | −1.27 | −0.14 | −0.40 | 0.43 |
| RNU4-8P | −1.17 | 0.05 | 2.22 | −0.10 | 1.00 | SLED1 | −0.17 | 0.17 | 0.00 | 0.27 | −0.06 | AC116035.1 | 0.15 | 0.13 | 1.91 | −0.20 | 0.56 |
| AL731892.1 | −1.31 | −0.30 | 0.35 | −0.27 | 0.66 | RASGEF1A | 0.18 | −0.04 | −0.48 | 0.04 | 0.00 | AC005391.1 | −0.02 | −0.59 | −0.24 | 0.31 | 0.41 |
| LINC01801 | −0.76 | 0.03 | 0.64 | 0.20 | 0.04 | DEPDC4 | −0.13 | −0.26 | 0.01 | 0.02 | 0.10 | CCNQP3 | 0.04 | 0.65 | −0.54 | −0.38 | −1.36 |
| CALM2P4 | −1.40 | 1.24 | 0.61 | 0.29 | −0.68 | G27456 | 0.18 | −0.47 | −0.14 | 0.34 | 0.54 | AC091874.3 | 0.04 | −0.30 | −1.16 | 0.26 | −0.29 |
| AC099336.2 | 0.69 | −0.04 | −0.27 | −0.06 | −0.15 | KRT19P2 | 0.74 | −0.96 | −1.43 | 1.03 | 1.16 | FO393414.2 | 0.15 | −0.66 | −1.16 | 1.27 | 0.23 |
| LINC01281 | 1.93 | −1.40 | −3.36 | 0.29 | −1.07 | AC025263.1 | −0.39 | −1.08 | 0.03 | 0.92 | 0.83 | ERI3-IT1 | −0.01 | −0.14 | 0.05 | −0.11 | 0.40 |
| AP001931.1 | 0.57 | 0.01 | −0.11 | −0.20 | −0.06 | AC008269.1 | −0.21 | −0.07 | −0.12 | −0.09 | 0.14 | RN7SL385P | 0.05 | −1.59 | −0.97 | −0.31 | 1.37 |
| AGA | 0.29 | −0.02 | −0.14 | 0.06 | −0.18 | MYL10 | −0.75 | 0.28 | 0.41 | 1.28 | 2.62 | CST9LP1 | 0.15 | −0.69 | −0.41 | −0.86 | −0.18 |
| LCE1B | −0.76 | 0.59 | 1.28 | 0.71 | −0.24 | CR381572.1 | −0.88 | −1.45 | −0.82 | −0.34 | −0.01 | AL161785.2 | 0.08 | −1.23 | −0.02 | −1.69 | 0.22 |
| RPS3P6 | −1.14 | 0.43 | 0.26 | 0.90 | 0.17 | AC006357.1 | 1.27 | −2.23 | 1.11 | −0.02 | 3.35 | AL121992.3 | 0.03 | −1.06 | 0.12 | 0.01 | 1.48 |
| AL356320.2 | 0.74 | −0.59 | −0.64 | −0.31 | −0.18 | AC060234.1 | 0.54 | −0.76 | 0.44 | −0.71 | 0.96 | CKBP1 | 0.11 | −1.38 | −1.22 | 0.05 | 0.23 |
| FLAD1 | 0.21 | −0.21 | −0.42 | 0.02 | −0.15 | AC105137.1 | 0.22 | −0.10 | −0.52 | 0.09 | −0.07 | LINC01757 | −0.15 | −1.03 | −0.72 | 0.50 | −0.07 |
| NKAPD1 | 0.21 | −0.05 | 0.05 | 0.01 | −0.05 | AC004692.2 | 1.29 | −1.96 | −1.66 | −0.09 | 2.32 | AC113368.1 | 0.14 | −1.21 | −0.01 | −0.41 | 0.27 |
| NCOA7 | 0.26 | −0.13 | −0.23 | −0.03 | −0.14 | SPATS2 | −0.06 | −0.04 | 0.00 | 0.07 | 0.08 | FCF1P3 | 0.12 | −0.98 | 0.59 | −1.09 | 2.09 |
| AC011753.3 | −1.77 | 0.97 | 1.71 | −1.49 | −0.69 | AC018695.4 | 0.18 | −0.37 | −0.26 | −0.21 | 0.54 | MIR578 | 0.07 | 1.27 | −0.62 | −0.09 | −2.12 |
| SNRPFP1 | 1.12 | −1.45 | −2.35 | −0.43 | −1.07 | AC000367.1 | 0.55 | −0.23 | −2.38 | 0.90 | −0.39 | PTOV1-AS2 | −0.01 | −0.20 | −0.51 | 0.25 | 0.30 |
| AC005899.2 | −1.48 | −0.09 | 0.89 | −0.06 | −0.10 | AC015815.6 | −0.20 | −0.24 | 0.08 | 0.06 | 0.44 | PPP1R21 | 0.00 | −0.03 | 0.15 | −0.16 | 0.05 |
| AC008592.1 | 1.01 | −0.94 | −1.01 | −0.04 | −0.89 | AP001646.3 | −0.42 | 1.02 | 1.57 | −0.63 | −0.19 | AL138787.2 | 0.01 | −0.21 | 0.35 | −0.18 | −0.14 |
| AC020911.2 | −1.23 | −1.72 | 1.76 | −0.89 | 0.67 | LINC02258 | −0.73 | 1.28 | 1.98 | 0.55 | 0.35 | SNX27 | 0.00 | 0.03 | 0.03 | −0.02 | −0.05 |
| PTP4A3 | −0.58 | −0.30 | −0.24 | 0.20 | 0.48 | AL160281.1 | 0.20 | −0.26 | −0.22 | 0.03 | −0.04 | AC006534.2 | −0.06 | −0.35 | −0.54 | 0.53 | 1.53 |
| EHMT1 | −0.20 | 0.04 | −0.10 | 0.08 | 0.06 | MIR4676 | 0.36 | −0.65 | −0.03 | 0.09 | 0.21 | FTLP10 | −0.04 | −1.18 | 0.28 | 0.59 | −0.09 |
| KDM2B | −0.28 | 0.00 | −0.16 | 0.05 | 0.04 | CASC11 | −0.25 | 0.11 | 0.00 | −0.07 | −0.62 | AL357093.2 | −0.01 | −0.02 | 0.26 | 0.18 | 0.03 |
| KCNMA1-AS1 | −0.64 | 0.25 | 0.20 | 0.12 | −0.05 | AC024901.1 | −0.31 | 0.49 | 0.31 | −0.74 | −1.01 | GAPDHP29 | −0.05 | −0.08 | −0.66 | −0.03 | 1.17 |
| RNU2-36P | −1.14 | 0.16 | −0.22 | 1.20 | 0.26 | SNORD22 | −1.20 | −0.27 | 2.47 | −2.58 | 0.39 | RN7SL446P | −0.05 | −0.57 | 1.50 | −0.75 | 0.22 |
| MIR600HG | −0.32 | 0.47 | 0.52 | 0.35 | 0.17 | AC092134.2 | −0.57 | −0.97 | 1.98 | −0.35 | 3.05 | AC096708.1 | 0.05 | −1.50 | 0.45 | −0.13 | 0.78 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC016292.1 | 0.95 | −0.42 | −0.48 | 0.19 | −0.39 | EPHA10 | −0.26 | −0.43 | 0.06 | 0.33 | 0.54 | LINC01910 | −0.02 | −0.21 | 1.30 | −0.68 | 0.77 |
| LINC01918 | −0.99 | 1.54 | 0.14 | 0.48 | −0.49 | AC006210.2 | −0.42 | −0.48 | −2.56 | −0.09 | −1.24 | ARL2BPP3 | −0.06 | −0.39 | −0.48 | −0.33 | 0.23 |
| AP005209.1 | 1.10 | −1.46 | 0.06 | 0.09 | 1.37 | AC006059.2 | −0.64 | −0.69 | −0.63 | 1.20 | 0.26 | MRPS35P3 | 0.14 | −1.17 | −1.20 | 0.30 | −2.23 |
| LNX1-AS1 | −0.52 | 0.80 | 0.74 | 0.43 | −0.33 | NMUR2 | 0.55 | −0.99 | −1.40 | 1.11 | 0.44 | MEP1AP2 | −0.15 | 0.16 | 0.22 | 0.58 | 2.70 |
| DPH7 | −0.30 | 0.08 | 0.22 | 0.09 | 0.27 | HEBP2 | −0.07 | 0.20 | 0.08 | −0.03 | −0.14 | LINC01202 | 0.06 | −1.07 | −0.81 | 1.13 | 0.68 |
| AL163952.1 | −1.09 | −0.11 | −0.20 | −0.28 | 0.29 | AC012100.3 | −0.14 | −0.32 | −0.08 | 0.11 | 0.43 | POM121L12 | −0.15 | −0.27 | 1.28 | −0.84 | 0.58 |
| PGLYRP2 | 1.22 | −1.09 | −0.19 | −0.15 | 0.43 | RNU6-593P | −0.35 | −0.66 | −0.29 | 0.96 | 0.53 | AC078776.2 | −0.15 | −0.15 | 1.19 | −1.22 | 1.02 |
| DOK1 | −0.58 | −0.05 | 0.23 | −0.10 | 0.17 | GPX6 | 0.60 | 0.47 | −1.52 | 0.61 | −0.09 | MAGEB6 | −0.15 | −0.49 | 0.00 | 1.19 | 0.52 |
| HEXIM2 | −0.41 | 0.44 | 0.68 | 0.36 | 0.32 | LRRC37A | −0.12 | 0.22 | 0.37 | 0.09 | 0.26 | AC098657.1 | −0.04 | −0.74 | −2.51 | 1.50 | −2.43 |
| LYPD6 | −0.77 | 0.59 | −0.17 | −0.38 | −1.34 | PFN1P3 | 0.29 | 0.10 | 0.55 | −0.38 | 0.32 | CD36 | −0.02 | 0.60 | 0.14 | 0.41 | −0.71 |
| KIAA0895L | −0.33 | 0.12 | 0.14 | 0.20 | 0.16 | OR7G2 | −0.44 | −0.21 | −1.27 | 0.17 | −0.58 | CCDC182 | 0.10 | −1.10 | 0.39 | −1.10 | −0.14 |
| HIPK1 | 0.21 | 0.08 | 0.02 | 0.00 | −0.24 | RHGAP19-SLIT | −0.75 | −0.59 | 0.93 | −2.20 | −0.52 | AC005580.1 | 0.04 | −1.43 | −2.61 | −0.33 | −1.90 |
| CBWD7 | −0.97 | 1.34 | 0.72 | 0.93 | 0.21 | LINC00599 | −0.48 | −1.25 | 0.14 | 0.16 | 1.40 | AC108051.1 | −0.15 | 0.20 | 0.05 | −0.20 | 0.13 |
| G10494 | −0.39 | 0.24 | 0.32 | −0.30 | 0.13 | DDX39B-AS1 | 0.50 | 0.36 | −0.94 | 0.79 | −0.78 | AC087360.1 | 0.14 | −0.55 | −1.09 | 0.84 | −1.32 |
| AL157871.2 | 1.05 | −0.55 | −0.98 | −0.40 | −0.66 | HERPUD1 | −0.06 | 0.22 | 0.17 | −0.07 | −0.11 | AL121820.1 | 0.03 | −0.61 | 1.84 | −0.14 | 0.83 |
| RN7SL587P | 0.65 | −0.53 | −0.82 | −0.35 | −0.40 | ASB14 | −0.11 | 0.06 | 0.65 | 0.00 | 0.35 | AL157698.1 | 0.15 | 0.65 | −0.56 | 0.82 | −1.07 |
| AC133561.1 | −0.75 | 0.69 | −0.52 | 1.96 | −0.55 | RBM25 | −0.10 | −0.13 | −0.14 | −0.07 | 0.04 | RPL36AP10 | 0.13 | −0.10 | 0.11 | −0.90 | −0.71 |
| AL731577.2 | −0.55 | 0.47 | 0.22 | 0.29 | −0.19 | PRAMEF11 | −0.77 | 0.30 | −1.73 | 0.96 | 0.72 | AL160396.2 | −0.01 | −0.13 | −0.16 | 0.16 | 0.27 |
| ACAD10 | −0.26 | −0.03 | 0.13 | 0.04 | 0.34 | CFI | 0.23 | 0.15 | −0.09 | 0.37 | −0.53 | AL590617.1 | −0.01 | 0.06 | −0.11 | 0.26 | 0.17 |
| C3orf49 | −0.24 | −0.12 | 0.16 | 0.00 | 0.27 | GPNMB | −0.11 | 0.30 | 0.35 | 0.04 | −0.21 | OR10D5P | 0.05 | −1.11 | −1.56 | 0.07 | −0.14 |
| LIPN | 0.66 | −0.21 | 0.71 | −0.01 | −0.41 | ISL2 | −0.57 | 0.59 | −0.65 | 0.31 | −0.96 | LINC01492 | −0.03 | 0.31 | −0.88 | 1.03 | −1.19 |
| RPS27AP10 | 0.75 | −0.20 | −0.55 | −0.27 | −0.55 | AL355974.2 | −0.74 | −0.28 | 0.02 | −1.04 | −2.93 | AL392003.2 | −0.14 | 1.09 | −2.29 | 1.42 | −2.52 |
| C6orf136 | −0.30 | 0.28 | −0.05 | 0.36 | 0.12 | AL034397.1 | 0.35 | −0.48 | −0.56 | 0.05 | −0.05 | AC005237.2 | −0.03 | −0.79 | 0.73 | −0.02 | 0.96 |
| GOLGA80 | −0.65 | 0.14 | 1.72 | −1.10 | 0.34 | SOS1 | 0.08 | 0.07 | 0.09 | −0.09 | −0.03 | GRK6 | 0.01 | −0.21 | −0.79 | 0.10 | −0.21 |
| AL512306.3 | −0.98 | −0.01 | 0.27 | −0.28 | 0.39 | LINC00888 | −0.22 | −0.05 | 0.06 | −0.04 | 0.31 | PBX1 | 0.01 | 0.33 | 0.25 | 0.21 | 0.00 |
| LEFTY2 | −1.96 | −0.65 | 2.41 | 1.02 | 1.68 | ADPRH | 0.16 | −0.19 | −0.02 | 0.05 | 0.00 | FAT1P1 | −0.05 | −0.90 | 0.13 | −1.91 | −1.18 |
| AL360081.1 | 0.99 | −0.84 | 0.08 | −0.11 | 0.54 | IFT74-AS1 | 1.02 | 0.07 | −1.80 | 1.27 | −2.25 | RPL23AP83 | 0.02 | 0.21 | 0.18 | 0.41 | −0.98 |
| RPL41P5 | 0.42 | 0.05 | −0.14 | 0.12 | −0.43 | AC116036.1 | −0.49 | 0.81 | 2.71 | 0.88 | 1.18 | AL662791.2 | −0.05 | −0.74 | −1.48 | 0.24 | −1.51 |
| ARHGAP29 | −0.29 | 0.40 | 0.74 | 0.05 | 0.00 | AC009139.1 | 0.40 | −0.28 | −0.33 | 0.15 | 0.23 | GGT2 | −0.02 | 1.30 | 0.42 | 0.44 | −0.11 |
| RNA5SP191 | −0.93 | −0.28 | 0.13 | 0.07 | −0.19 | APCDD1L | −0.12 | −0.01 | 0.31 | −0.29 | 0.22 | AL096828.1 | 0.04 | −0.76 | 0.34 | 1.95 | 3.10 |
| PUM2 | 0.19 | 0.14 | 0.05 | 0.09 | −0.11 | CPLX4 | −0.49 | 0.29 | −1.01 | 0.64 | −1.74 | AP001992.1 | 0.00 | −0.16 | 0.00 | −0.04 | 0.16 |
| AC022336.1 | 0.97 | −1.34 | −0.33 | −0.17 | 0.34 | AC104984.6 | 0.23 | −0.42 | 0.13 | 0.15 | 0.49 | MRPS11P1 | −0.14 | −0.31 | −0.71 | −0.64 | −1.80 |
| RRN3 | 0.23 | −0.19 | −0.28 | −0.02 | −0.07 | PAPPA | 0.11 | −0.16 | 0.17 | −0.46 | −0.12 | AL590644.1 | 0.02 | 0.29 | 0.44 | −0.20 | −0.43 |
| FAM114A1 | −0.29 | 0.14 | 0.58 | −0.41 | −0.03 | AL354760.1 | −0.20 | 0.81 | 0.25 | 0.44 | −0.30 | AC107015.1 | 0.06 | −0.15 | −1.80 | 2.14 | −0.61 |
| OVOL1-AS1 | 0.83 | 0.19 | −0.71 | −0.23 | −1.21 | AL591503.2 | 0.87 | −1.38 | −1.66 | −0.87 | 0.00 | SH3RF3-AS1 | 0.01 | 0.11 | −0.49 | 0.33 | −0.06 |
| CSGALNACT1 | 0.39 | −0.16 | 0.32 | −0.51 | −0.05 | MIR25 | −0.42 | −1.09 | −0.23 | −0.17 | 0.89 | RNU6-547P | −0.05 | 0.45 | −0.83 | −0.69 | −1.15 |
| PPP1R14D | −0.95 | 1.32 | 0.38 | −0.18 | −0.65 | RNA5SP68 | 0.32 | −0.18 | 0.42 | 0.20 | 0.91 | SCD | 0.02 | 0.83 | 0.15 | 0.25 | −0.36 |
| AC005336.3 | 1.64 | −2.14 | −0.42 | −1.18 | 1.54 | LINC02330 | 1.17 | −2.43 | 1.39 | −0.45 | 2.56 | AC023644.1 | −0.06 | 0.92 | 1.22 | 0.54 | −0.66 |
| AL360176.1 | 1.18 | −0.22 | −0.32 | 0.22 | −0.18 | SPATC1L | −0.11 | 0.18 | −0.24 | 0.56 | 0.34 | HNRNPCP10 | 0.06 | −0.65 | 0.69 | 1.60 | 2.44 |
| AC126118.1 | −0.67 | −0.12 | 1.61 | −0.25 | 0.51 | RN7SL86P | −0.55 | −0.95 | 0.58 | 0.59 | 1.93 | KRT17P4 | 0.09 | −0.24 | −0.02 | −0.50 | −1.27 |
| CD3D | 0.96 | −0.98 | 0.16 | −0.41 | 0.36 | DHX58 | 0.11 | −0.29 | −0.20 | −0.14 | 0.23 | AC074281.1 | −0.03 | −0.35 | −2.17 | 1.34 | −0.69 |
| AL451074.3 | 0.97 | −0.48 | 0.62 | 0.76 | 0.69 | FTH1P15 | 0.65 | −0.27 | −0.26 | −0.38 | 0.60 | RN7SL714P | 0.09 | 0.43 | −0.88 | 1.64 | −0.89 |
| POLR3F | 0.27 | −0.03 | −0.26 | −0.07 | −0.42 | AC112487.2 | 0.91 | −0.33 | −0.02 | −0.98 | −0.84 | RNU7-196P | 0.02 | −0.13 | 0.14 | −1.45 | 0.74 |
| GLUL | −0.42 | 0.13 | 0.24 | 0.08 | 0.06 | LINC02427 | 0.61 | −0.42 | 0.23 | 0.90 | 0.96 | PEX5L-AS1 | −0.05 | −0.92 | −0.94 | 0.39 | 0.62 |
| MECR | −0.22 | −0.04 | 0.16 | 0.18 | 0.33 | AC026782.1 | −0.78 | −0.43 | 0.66 | −0.20 | 0.84 | SNORD114-19 | −0.14 | −0.08 | 1.04 | −1.46 | −0.24 |
| AC106886.4 | −0.68 | 0.25 | −0.51 | 0.06 | −0.30 | AC084125.3 | 0.38 | −0.25 | −0.57 | −0.70 | −1.56 | GAPDHP74 | −0.04 | 0.48 | −0.93 | 1.16 | −0.70 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| LINC02301 | −1.13 | 1.04 | −0.94 | 0.88 | −1.41 | AC124944.3 | −0.14 | −0.22 | 0.43 | 0.33 | 0.88 | AC010983.1 | 0.14 | 0.65 | −0.20 | 1.05 | −0.80 |
| SIK1 | −0.74 | 0.67 | 0.71 | −0.43 | −0.20 | BX005040.1 | −0.89 | −0.44 | −1.29 | 0.20 | 0.30 | AC092171.5 | −0.01 | 0.44 | −0.19 | 0.64 | −0.17 |
| CEP135 | 0.25 | −0.26 | −0.44 | −0.08 | −0.06 | AC108161.1 | 0.47 | 0.42 | 0.97 | −0.16 | 0.72 | AL080284.1 | 0.14 | −0.20 | −0.69 | −0.27 | 0.12 |
| COX17 | 0.29 | −0.17 | 0.08 | −0.09 | 0.05 | IMP A1P1 | 0.37 | −0.07 | −1.18 | −0.16 | −0.13 | AL133228.1 | −0.12 | −0.19 | 3.08 | −0.17 | 1.72 |
| AC098864.1 | 0.86 | −0.29 | −1.62 | 0.07 | −1.40 | LINC00929 | 0.62 | −0.89 | −1.79 | 0.55 | −0.63 | GAPDHP66 | 0.03 | −0.52 | −0.32 | −0.47 | 0.21 |
| AC116614.1 | −0.92 | 0.57 | 1.16 | 0.28 | 0.30 | G6313 | 0.29 | 0.73 | 1.02 | 0.51 | −0.91 | AL139350.1 | 0.14 | −0.48 | −0.85 | 1.30 | −0.44 |
| ACAN | 0.77 | −0.46 | 0.11 | −0.42 | −0.80 | AC107398.3 | −0.31 | −0.19 | −0.23 | −0.53 | −0.25 | EIF5P2 | 0.14 | −0.54 | −1.09 | −0.45 | −0.38 |
| SRPK2 | 0.15 | −0.05 | −0.34 | 0.06 | −0.23 | AC092118.1 | 0.23 | −0.26 | −0.61 | 0.30 | −0.60 | AL035698.1 | 0.14 | 0.56 | 0.19 | 1.58 | −1.00 |
| FERP1 | 1.13 | −0.11 | 0.26 | 0.49 | 0.21 | AC104699.1 | 0.29 | −0.22 | −0.52 | −0.45 | 0.15 | LINC00309 | 0.02 | −1.28 | −1.34 | −0.20 | 0.21 |
| AP000568.1 | 1.14 | −0.22 | −0.31 | −0.43 | −1.14 | POMT2 | 0.07 | −0.08 | −0.18 | 0.03 | 0.09 | LINC02163 | 0.11 | −0.15 | −0.62 | 1.70 | −0.27 |
| AL031123.2 | −0.49 | 0.16 | 0.73 | 0.29 | 0.49 | RPL21P110 | 0.86 | −0.72 | −1.72 | −0.14 | −1.22 | CCDC163 | −0.01 | −0.24 | 0.30 | 0.34 | 0.41 |
| SNRPA1 | 0.19 | −0.21 | −0.31 | −0.02 | −0.05 | AL353691.2 | 0.65 | −0.47 | −0.59 | −0.43 | −0.16 | AC104389.6 | −0.14 | −0.19 | 0.62 | 0.21 | −0.22 |
| RN7SL819P | −1.38 | 0.52 | −1.47 | 1.15 | −0.12 | PHEX−AS1 | 0.34 | −0.86 | −0.93 | −0.02 | 0.02 | AC087783.1 | −0.07 | −0.43 | −1.77 | −1.20 | −1.92 |
| AL591686.1 | −1.43 | 0.21 | 0.52 | 1.98 | 1.77 | AC005041.2 | 0.85 | −0.47 | −0.95 | 1.02 | −0.23 | NF1P4 | −0.06 | −0.59 | 1.10 | −0.42 | 2.02 |
| AK8 | −0.59 | 0.63 | 0.59 | 0.55 | −0.05 | G8972 | 0.44 | 0.20 | 0.51 | −0.09 | 0.24 | OR5AC1 | 0.14 | −0.81 | 0.44 | 0.18 | 1.31 |
| SLC5A11 | −0.75 | −0.46 | 0.20 | 0.00 | 1.36 | AC008806.1 | −0.49 | 0.30 | −0.10 | 0.16 | −0.54 | RNF170 | 0.00 | 0.07 | 0.35 | 0.04 | 0.05 |
| MTATP6P27 | −0.66 | 0.40 | 0.87 | −0.13 | 0.05 | AL590438.1 | −0.48 | −0.97 | 0.09 | 0.59 | 1.46 | AC069271.1 | −0.03 | −1.38 | 2.45 | −1.63 | 1.49 |
| AMMECR1LP1 | −1.69 | 0.59 | 0.84 | 0.32 | 1.79 | RNU6-101P | −0.44 | −0.19 | 0.85 | −0.31 | 0.86 | LINC01284 | 0.07 | −1.44 | 0.01 | −0.55 | −0.50 |
| OSBPL8 | 0.26 | 0.01 | −0.10 | −0.09 | −0.28 | ITFG1-AS1 | 0.29 | −0.01 | −0.40 | −0.15 | 0.16 | PPP1R10P1 | −0.08 | −0.66 | 0.97 | 0.06 | −1.37 |
| RP11-782C8.5 | −0.51 | 1.00 | 0.56 | 0.69 | −0.11 | IGHV3-15 | 1.19 | 0.31 | 2.14 | 1.16 | 0.95 | AL157392.4 | 0.02 | 0.03 | 0.19 | 0.17 | 0.13 |
| AL590552.1 | 1.55 | −0.58 | −1.10 | 1.03 | 0.08 | AL683887.1 | −0.25 | 0.49 | 0.37 | 0.08 | −0.41 | AC006159.1 | 0.01 | 0.06 | 0.16 | −0.25 | −0.11 |
| MTRNR2L12 | −0.94 | 0.38 | −0.01 | 1.35 | −0.18 | RP11-277L2.3 | −0.55 | −0.57 | −0.81 | 0.48 | 0.48 | AC021785.1 | 0.02 | −0.23 | −2.90 | −0.56 | −1.86 |
| DUT | 0.25 | −0.28 | −0.38 | 0.06 | −0.02 | ANKRD20A10P | 0.62 | −1.37 | −0.23 | 1.12 | 0.91 | COX18 | 0.00 | −0.25 | 0.12 | 0.00 | 0.36 |
| C3orf67-AS1 | 1.16 | −1.25 | −2.08 | 0.11 | −1.88 | AC024651.1 | 0.38 | −1.30 | −1.94 | 0.91 | −0.48 | AC022929.1 | −0.03 | −0.09 | 0.51 | −0.69 | 0.37 |
| AC011466.1 | 0.94 | −0.53 | −0.96 | 0.43 | 0.35 | AC119751.1 | −0.39 | −1.01 | −0.40 | −0.17 | 0.11 | AL359182.1 | −0.02 | −0.14 | −0.79 | 0.38 | 0.17 |
| AL031289.1 | −1.02 | −0.45 | −0.54 | 0.27 | 0.32 | AC011471.4 | 0.39 | 0.15 | 0.99 | 0.66 | 0.43 | AL022324.2 | −0.01 | 0.17 | −0.06 | 0.43 | 0.06 |
| AC007402.1 | −1.22 | −0.32 | −0.22 | −0.10 | −0.33 | AC020659.1 | −0.26 | −0.15 | 0.24 | −0.27 | −0.42 | ATP6V0CP1 | −0.01 | 0.02 | −0.18 | −0.11 | 0.25 |
| DUOX2 | −0.43 | 0.29 | −0.14 | 0.53 | 0.36 | AC105250.1 | −0.30 | 0.36 | −0.11 | 0.70 | −0.39 | SLC25A51P2 | −0.14 | 0.57 | −1.18 | 1.17 | −0.94 |
| FNDC11 | 0.87 | −0.51 | −1.18 | 0.15 | −0.16 | OPRM1 | −0.39 | −1.19 | −0.81 | 0.47 | −0.49 | SNORA5 | 0.13 | −1.51 | 1.17 | 0.13 | 1.33 |
| AC113935.1 | 0.47 | −0.36 | −0.02 | −0.43 | 0.02 | RN7SL242P | −0.29 | 0.60 | −1.03 | 0.81 | −1.26 | GM2AP2 | −0.14 | 1.02 | −0.32 | 0.87 | 1.21 |
| RAB44 | −0.35 | 0.48 | 0.97 | 0.07 | 0.41 | AC006058.3 | 0.63 | −0.37 | −1.52 | −0.27 | −1.22 | KANK1 | 0.00 | 0.15 | −0.13 | −0.09 | −0.25 |
| AC007277.1 | −0.83 | 1.00 | 0.12 | 0.82 | 0.11 | AC011468.1 | −0.18 | −0.14 | 0.87 | −0.49 | 0.29 | PDX1 | 0.02 | −1.25 | −1.75 | 0.45 | 0.25 |
| AC105942.1 | −0.63 | 0.50 | 1.08 | −0.12 | −0.23 | AL591543.1 | −0.43 | 0.77 | −0.98 | 0.83 | −0.79 | LINC00332 | 0.03 | −0.04 | −0.02 | 0.06 | 1.83 |
| CHRNG | −0.50 | 0.14 | 0.54 | 0.32 | 0.55 | LINC00477 | −0.77 | −1.16 | 2.37 | −0.34 | 2.03 | RPS19P1 | 0.01 | −0.02 | 0.24 | −0.21 | −0.12 |
| COX19 | −0.29 | 0.17 | 0.29 | 0.16 | 0.20 | POU5F1P4 | −0.20 | 0.35 | −0.89 | 0.02 | −0.97 | AC240504.1 | −0.07 | −0.78 | −0.97 | −0.39 | −0.44 |
| RERG−AS1 | −1.07 | 0.60 | 0.48 | 0.42 | −0.07 | OR6P1 | 0.58 | 0.06 | −1.66 | 0.48 | −0.47 | SCUBE2 | −0.01 | 0.58 | −0.11 | 0.55 | −0.14 |
| AL356740.3 | −0.96 | 1.43 | 0.52 | 1.13 | 0.50 | FKSG68 | −0.52 | 1.13 | −0.88 | 0.76 | −0.66 | PROP1 | −0.03 | 0.24 | −1.39 | −0.30 | −0.42 |
| HHLA3 | −0.37 | 0.22 | 0.35 | 0.12 | 0.25 | PRKACG | 0.95 | −2.04 | 0.75 | −0.78 | 3.25 | AL136309.2 | 0.02 | −0.67 | −0.44 | −0.78 | 0.01 |
| AC144652.1 | −0.70 | 0.39 | 0.96 | 0.05 | 0.37 | SERPINF2 | −0.17 | −0.04 | 0.03 | 0.29 | 0.26 | LINC02553 | 0.05 | −0.56 | −1.69 | 1.33 | −0.38 |
| ANKRD13C | 0.12 | 0.04 | −0.04 | 0.02 | −0.12 | MIR5000 | −0.42 | 0.22 | 1.71 | 0.11 | 1.40 | AL360175.1 | −0.14 | −0.61 | −0.63 | 1.70 | 1.29 |
| AC012629.3 | −0.99 | 0.33 | 0.80 | 0.09 | 0.81 | AC008894.2 | −0.18 | 0.13 | 0.40 | −0.05 | 0.41 | AC131212.2 | −0.01 | 0.26 | 0.22 | −0.01 | 0.02 |
| AL359922.1 | 1.46 | −1.05 | 0.20 | −0.71 | 0.33 | AL590084.2 | −0.52 | 0.72 | 1.41 | 0.08 | 0.34 | AC019294.3 | −0.06 | 0.03 | −1.94 | 0.23 | −1.55 |
| IGF2BP2-AS1 | 0.57 | −0.21 | 0.02 | −0.04 | 0.02 | LINC02071 | −0.52 | −1.37 | −0.68 | −0.63 | 0.11 | AL135903.1 | −0.04 | 1.19 | −0.39 | −0.50 | −1.63 |
| AC055811.1 | 0.60 | −0.22 | −0.47 | −0.13 | −0.10 | SPO11 | 0.60 | −0.31 | −1.61 | 0.28 | −1.52 | LINC02536 | 0.08 | −1.08 | 0.67 | −2.24 | 1.85 |
| CATSPERB | 0.48 | −0.65 | −0.78 | −0.10 | 0.16 | POLR2M | 0.10 | 0.03 | −0.11 | 0.13 | −0.11 | FOXD4L5 | 0.03 | −0.52 | −1.01 | 0.77 | 0.82 |
| RPL41P1 | 0.80 | −0.14 | 0.93 | 0.06 | 0.37 | C11orf88 | −0.57 | −0.47 | 0.59 | −0.71 | 0.24 | AC007656.1 | 0.14 | 0.14 | −1.42 | −1.07 | −2.48 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AL583810.2 | −0.77 | 0.84 | 0.75 | 0.08 | −0.35 | MTND2P18 | 1.32 | −1.18 | −1.08 | −0.60 | −0.51 | AC026954.1 | −0.03 | −1.07 | 1.16 | −0.64 | 2.07 |
| AC092821.1 | −0.53 | −0.09 | −0.78 | −0.09 | −1.12 | AC092720.1 | −0.21 | 0.18 | −0.02 | 0.01 | 0.00 | AC105924.1 | 0.06 | −0.82 | −1.20 | 0.55 | 0.69 |
| AC104129.1 | −0.43 | 0.03 | 0.03 | 0.43 | 0.29 | AL031320.2 | 0.17 | −0.11 | 0.25 | 0.03 | 0.24 | AC013644.1 | −0.02 | 0.38 | 0.61 | −0.92 | −1.13 |
| AC104685.1 | 1.09 | 0.70 | −0.39 | 0.89 | −0.21 | LRRK1 | −0.07 | −0.17 | −0.09 | −0.03 | 0.16 | IGF1R | 0.00 | 0.20 | −0.15 | 0.14 | −0.13 |
| ANKRA2 | −0.23 | 0.26 | 0.27 | 0.11 | −0.06 | AC000403.1 | −0.20 | −0.47 | −0.32 | −0.30 | 0.06 | MARK2P10 | 0.14 | −0.55 | −1.57 | 0.68 | 0.29 |
| HMGB1P23 | 0.59 | −0.04 | 0.20 | −0.30 | −0.08 | AC138904.1 | −0.40 | −0.51 | −0.55 | 0.47 | 1.19 | AL032822.1 | −0.05 | 0.07 | 0.15 | 0.82 | −1.02 |
| AL139287.1 | −0.39 | −0.02 | −0.12 | 0.17 | 0.16 | SMG1P5 | 0.11 | −0.17 | 0.09 | 0.24 | 0.61 | RPL13AP23 | −0.13 | −0.66 | −0.34 | 1.97 | 0.56 |
| HUWE1 | 0.12 | −0.02 | −0.08 | −0.02 | −0.07 | CCND3 | 0.07 | −0.09 | 0.00 | 0.08 | 0.01 | BRD7P6 | 0.05 | −1.19 | −1.07 | −1.09 | 0.83 |
| AP003469.2 | −0.86 | −0.21 | 0.60 | 0.54 | 0.63 | AC026765.2 | −0.63 | −1.67 | −0.71 | −0.06 | 1.21 | AL590396.2 | −0.05 | −0.07 | 0.33 | 0.44 | 0.21 |
| AC073050.1 | −1.01 | −0.09 | 1.12 | −0.22 | 0.98 | SART3 | 0.05 | −0.10 | −0.14 | −0.08 | −0.05 | CRYGS | −0.01 | −0.18 | 0.36 | −0.20 | 0.44 |
| LINC02535 | 1.31 | −2.26 | −1.48 | −0.06 | 0.16 | MTND1P9 | 0.15 | −0.32 | 0.07 | −0.25 | 0.36 | RN7SL383P | 0.06 | 0.11 | −0.57 | 0.16 | −1.06 |
| AL035458.1 | 0.60 | −0.44 | −0.06 | −0.57 | 0.40 | LINC02356 | −0.53 | −0.03 | 0.95 | 0.81 | 0.63 | RNU6-925P | 0.02 | 0.97 | 1.23 | 0.30 | 1.41 |
| LINC01089 | −0.42 | 0.37 | 0.41 | 0.27 | 0.08 | AL591848.1 | −0.48 | −0.10 | 1.91 | −0.70 | 0.62 | FDPSP1 | 0.04 | −0.99 | 1.15 | 0.66 | 1.48 |
| OR6T1 | −1.98 | 0.56 | 2.47 | −0.95 | 1.38 | AL451074.1 | −0.33 | −0.03 | −0.04 | 0.90 | 0.02 | B4GALT4 | 0.01 | 0.10 | 0.03 | 0.01 | −0.07 |
| NPIPB4 | −0.30 | 0.21 | 0.22 | 0.46 | 0.23 | AC006970.2 | −1.06 | 0.04 | 0.56 | 1.35 | −0.32 | LINC01517 | −0.02 | −0.81 | −2.08 | −0.16 | −1.48 |
| KLHL8 | 0.20 | −0.17 | 0.05 | −0.07 | 0.11 | MTRNR2L3 | −0.14 | −0.32 | −0.60 | −0.03 | −0.25 | KRT18P8 | −0.04 | −0.30 | −0.53 | 0.55 | −0.22 |
| RNU6-82P | 0.94 | −1.15 | −0.25 | 0.04 | 0.50 | LINC01535 | −0.25 | 0.08 | 0.77 | −0.53 | −0.16 | AL109741.2 | −0.04 | −0.64 | 0.87 | −1.39 | 0.07 |
| RBM34 | −0.43 | −0.23 | −0.01 | −0.19 | 0.06 | MCMDC2 | −0.17 | −0.07 | 0.26 | −0.04 | −0.14 | MAPK6P2 | 0.03 | 0.28 | −0.34 | 0.61 | −0.49 |
| AC091959.2 | 0.86 | 0.36 | −0.27 | −0.39 | −0.48 | G11773 | 0.45 | −0.57 | −0.31 | 0.57 | −0.12 | AC109349.1 | 0.14 | −1.52 | 0.87 | −1.13 | 0.41 |
| HOXA7 | 0.69 | 0.70 | −0.59 | 0.75 | −0.83 | AL513365.1 | 0.18 | 0.03 | 0.01 | −0.07 | −0.07 | HMGB3P9 | 0.01 | 0.08 | 0.19 | 0.13 | 0.14 |
| AC068338.2 | 0.76 | −0.24 | −1.45 | −0.35 | −1.12 | AL137846.1 | 0.33 | −0.37 | −0.29 | −0.25 | 0.13 | AC091769.1 | 0.02 | 0.29 | 1.69 | −0.51 | −0.15 |
| MIR661 | 1.83 | −0.18 | −2.55 | −0.43 | −2.42 | DANT1 | −0.70 | 1.10 | 1.60 | −0.96 | −0.25 | RNU2-47P | −0.14 | −0.50 | 0.82 | −0.22 | 1.01 |
| AC125257.1 | 0.41 | 0.09 | 0.00 | −0.15 | −0.35 | IRF2BPL | 0.09 | 0.08 | −0.51 | 0.27 | −0.37 | AC117945.2 | −0.08 | 0.51 | −3.02 | 2.28 | −0.70 |
| LINC01365 | −1.73 | −0.99 | −0.86 | 0.52 | −0.32 | RN7SL634P | 0.61 | −0.34 | 1.10 | 0.56 | 0.12 | AP005902.1 | 0.07 | −0.21 | −1.43 | 0.31 | −1.67 |
| KCNE3 | −0.62 | −0.05 | 0.97 | −0.26 | 0.38 | KRT26 | −0.54 | 0.26 | 1.87 | 0.30 | 1.12 | AL158090.1 | 0.09 | 0.72 | −0.10 | 1.32 | −0.38 |
| FLJ45513 | −0.56 | 0.27 | 0.73 | 0.19 | −0.13 | AC187652.1 | 0.25 | −0.84 | −0.25 | −0.62 | 0.10 | AL162574.2 | −0.13 | 1.81 | 0.38 | 1.81 | −1.65 |
| AC007224.2 | −1.35 | 0.86 | 0.80 | −0.60 | 0.38 | SAV1 | −0.09 | 0.23 | 0.41 | −0.04 | 0.03 | PPIHP1 | 0.01 | −0.48 | 0.00 | −0.21 | 0.22 |
| AC107079.1 | −0.74 | −0.48 | 0.49 | −0.38 | 0.26 | AL033397.2 | 0.21 | −0.29 | −1.25 | 0.37 | −0.32 | AC012499.1 | 0.05 | 0.79 | 1.19 | −0.50 | −0.56 |
| AL023807.1 | 0.57 | −0.37 | −0.85 | 0.02 | −0.09 | SDHDP6 | −0.58 | 0.04 | −0.62 | −0.32 | −0.24 | RNU6ATAC8P | 0.14 | −0.69 | −0.03 | −1.05 | −1.12 |
| ALMS1 | −0.17 | 0.14 | 0.22 | −0.04 | −0.04 | RNASE10 | −0.43 | −0.80 | −1.30 | 0.31 | −0.28 | AL390955.1 | −0.03 | −1.25 | 0.13 | −0.03 | 2.18 |
| RN7SKP296 | 0.70 | −0.72 | −0.09 | −0.03 | 0.27 | AC092375.2 | −0.29 | 0.08 | 0.16 | −0.01 | −0.29 | AL513422.1 | −0.07 | 0.66 | 0.42 | 1.58 | −0.50 |
| BICDL2 | −0.43 | 0.57 | 0.07 | 0.41 | −0.02 | LINC00433 | −0.63 | −0.16 | −1.61 | −0.26 | −0.81 | AC132216.1 | 0.05 | −0.58 | −1.43 | 0.62 | −0.92 |
| GTF3A | 0.31 | −0.22 | 0.14 | −0.23 | 0.11 | RNY4P15 | −0.46 | −0.21 | 0.76 | −0.09 | −0.40 | LINC01935 | −0.05 | 0.47 | 0.33 | 0.38 | −1.04 |
| MICAL1 | −0.30 | −0.12 | −0.17 | −0.08 | 0.05 | AC109583.2 | −0.49 | 0.16 | −1.35 | 0.47 | 0.27 | SSTR3 | 0.02 | −1.16 | −1.85 | −0.18 | 0.73 |
| CR936218.2 | −1.12 | −0.87 | 0.71 | 0.33 | 1.06 | RNU6-880P | 0.50 | −0.51 | −1.05 | 0.67 | −0.19 | AL359551.1 | −0.02 | −0.29 | −0.07 | −0.19 | −0.22 |
| MIR4802 | 0.74 | −0.20 | −1.14 | 0.22 | −0.37 | OR2R1P | 0.27 | −0.36 | 0.20 | −0.16 | 0.68 | IFITM5 | 0.03 | −1.65 | −1.95 | −0.77 | −1.31 |
| PI4KA | −0.15 | 0.09 | −0.02 | 0.12 | 0.05 | BSCL2 | −0.12 | −0.11 | 0.33 | −0.08 | 0.09 | CCAT2 | −0.01 | 0.18 | 0.11 | 0.61 | 0.34 |
| PYDC1 | 0.95 | 0.33 | 0.88 | 0.66 | −0.31 | AL133370.2 | −0.28 | 0.67 | 0.74 | 0.26 | −0.39 | AL121987.2 | 0.01 | 0.03 | 0.11 | 0.01 | 0.16 |
| AL355388.2 | −0.68 | −0.05 | 0.83 | 0.02 | 0.40 | AC073476.3 | 0.18 | 0.01 | 0.08 | 0.25 | −0.09 | OR5D14 | 0.04 | −0.38 | −0.63 | 0.72 | −0.82 |
| NANOS1 | 0.40 | −0.02 | −0.36 | −0.26 | −0.31 | SNORA72 | 0.19 | −0.43 | −0.62 | −0.60 | −0.71 | RNU6-409P | −0.03 | −0.71 | −0.05 | 0.73 | 0.93 |
| AL357134.1 | −0.81 | 0.61 | 1.34 | 0.71 | 0.81 | NUPR2 | −0.48 | 1.76 | 1.57 | 1.78 | 0.74 | AC063923.2 | 0.13 | 1.97 | 0.96 | −0.03 | 0.12 |
| LINC00926 | −0.31 | 0.30 | 0.30 | 0.09 | 0.17 | AC083967.1 | −0.53 | 0.56 | −1.48 | 1.31 | 0.71 | IGLVI-56 | −0.13 | −0.71 | 0.19 | −0.82 | 1.25 |
| RSU1P2 | −1.27 | 0.35 | 0.33 | −0.99 | −0.50 | HNRNPDLP2 | 0.58 | −1.10 | −0.82 | −0.49 | 0.59 | CD22 | 0.01 | −0.84 | −0.30 | −0.23 | −0.27 |
| AC012441.2 | −2.21 | 1.48 | 0.25 | 1.20 | −1.22 | LINC02143 | −0.87 | 1.20 | −1.68 | 1.36 | 0.06 | PRAMEF30P | 0.07 | −1.05 | −1.03 | 0.70 | 0.30 |
| SPRR5 | 0.92 | −1.53 | −1.60 | −0.60 | 0.41 | CDC42P5 | −0.29 | 0.33 | 0.55 | 0.60 | 0.16 | PTF1A | −0.13 | −1.44 | 0.21 | −0.22 | 1.52 |
| DCN | −0.56 | 0.74 | 1.60 | −0.24 | −0.15 | AC027682.5 | −0.20 | −0.29 | 0.73 | −0.29 | 0.56 | AP004550.1 | −0.13 | 0.34 | 0.13 | 1.44 | −0.08 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| SLC25A36 | −0.26 | 0.28 | 0.42 | 0.17 | 0.10 | ST13P19 | 0.39 | −0.64 | −0.99 | 0.63 | 0.08 | AC093843.1 | −0.03 | −0.19 | −0.14 | −0.28 | −1.64 |
| MMP23B | −0.77 | 0.88 | 0.96 | −0.02 | −0.17 | RNY1P4 | −0.15 | −0.24 | −0.24 | −0.18 | 0.18 | AC104389.1 | −0.13 | −1.49 | 0.53 | 0.29 | −0.46 |
| AP006333.2 | −0.75 | 0.81 | 0.66 | 0.58 | 0.63 | AL050321.1 | 0.28 | 0.28 | 0.58 | 0.14 | −0.19 | ATG3P1 | −0.08 | −1.61 | 0.28 | 0.10 | 1.07 |
| AL079307.2 | 2.28 | −1.81 | −2.13 | −0.52 | −0.93 | AC021945.1 | 0.16 | −0.44 | −0.28 | −0.16 | 0.20 | AC006363.1 | 0.13 | −1.56 | −0.64 | −1.40 | −0.64 |
| OLIG1 | −1.44 | 0.34 | 2.32 | 0.35 | 2.58 | ACSM5P1 | 0.67 | −0.08 | −2.29 | 0.60 | −1.72 | BX323845.3 | −0.09 | −0.81 | 0.60 | −1.61 | −0.30 |
| RGSL1 | −0.82 | −0.54 | 0.01 | 0.47 | 0.06 | AC026369.3 | 1.01 | −2.42 | −1.96 | −0.84 | −0.30 | P3H1 | 0.01 | −0.27 | 0.21 | −0.40 | 0.11 |
| AC021087.2 | −0.49 | 0.20 | 0.37 | 0.27 | 0.26 | AC020658.5 | 1.05 | −0.66 | 0.82 | 0.13 | 0.08 | ARSFP1 | −0.13 | 0.77 | −0.40 | −0.58 | 0.06 |
| PHF20L1 | 0.15 | −0.10 | −0.20 | −0.10 | −0.17 | RPL35AP24 | 0.28 | −0.39 | 0.65 | −0.05 | 0.99 | PNLIPRP3 | 0.01 | −0.29 | −0.41 | −0.23 | −0.38 |
| N4BP2L2 | −0.20 | 0.27 | 0.33 | 0.10 | 0.07 | LINC02054 | −0.30 | 0.45 | −0.59 | 0.62 | −0.52 | OCLM | −0.01 | −0.29 | 0.56 | −0.14 | 0.49 |
| CYLD | 0.28 | −0.10 | −0.13 | 0.02 | −0.18 | AL157895.1 | −0.28 | 0.08 | 1.30 | −0.52 | 0.25 | ST3GAL1 | 0.01 | −0.11 | 0.06 | −0.31 | 0.00 |
| CALM2P2 | 0.40 | −0.04 | 0.02 | 0.05 | −0.01 | GSTZ1 | −0.09 | 0.18 | 0.25 | 0.23 | 0.12 | PRAMEF12 | 0.06 | −0.03 | −0.52 | −0.14 | −1.65 |
| RN7SKP64 | −0.67 | 0.02 | 0.60 | 0.10 | 0.34 | MAML1 | 0.06 | 0.01 | −0.10 | 0.03 | −0.07 | AC091096.1 | 0.02 | 0.05 | −1.04 | 0.25 | −0.71 |
| RPS9 | 0.22 | 0.02 | −0.05 | −0.04 | −0.24 | AL354854.1 | −0.66 | 1.03 | −2.10 | 1.16 | −3.49 | SALL4P1 | 0.03 | −0.28 | −0.27 | 0.50 | −0.49 |
| SCAND2P | −0.33 | 0.18 | 0.03 | −0.03 | 0.01 | RPS27P21 | −0.58 | 0.20 | −0.97 | 1.16 | −0.35 | LYPLA1P1 | −0.13 | 0.50 | −0.97 | 0.93 | −2.25 |
| AL359644.1 | −0.57 | −0.14 | 0.37 | 0.21 | 0.13 | DLL4 | 0.17 | −0.44 | 0.14 | 0.07 | 0.11 | AC079150.1 | 0.06 | −0.80 | −1.30 | 1.95 | −0.27 |
| AC020915.3 | −0.34 | 0.26 | 0.71 | −0.11 | 0.42 | AC084824.3 | −0.12 | −0.44 | −0.28 | 0.02 | 0.30 | AC129926.1 | 0.03 | −0.88 | −1.15 | 1.03 | −0.35 |
| SGMS1 | 0.23 | 0.08 | −0.15 | 0.09 | −0.12 | AC026202.1 | 0.50 | −0.19 | −0.66 | 0.48 | −1.41 | AC055717.1 | −0.03 | −0.71 | −2.27 | 0.30 | −0.94 |
| HMGB4 | 1.36 | −1.34 | −2.77 | −0.75 | −2.02 | AC231533.1 | −0.40 | 0.13 | 0.63 | 0.19 | −0.29 | AC097713.1 | −0.04 | −1.61 | −1.47 | 0.58 | 1.22 |
| AC010776.1 | −1.08 | 0.16 | 1.14 | −0.54 | 0.02 | AL133499.1 | 0.25 | 0.13 | −0.78 | −0.36 | −0.55 | AL352979.1 | 0.03 | 1.20 | −1.55 | 0.75 | −2.52 |
| SNX2 | 0.26 | 0.04 | −0.17 | 0.00 | −0.38 | NFYC-AS1 | −0.21 | −0.24 | 0.42 | 0.14 | 0.35 | AC090820.1 | −0.13 | −0.51 | −0.90 | 1.77 | −0.72 |
| AC114402.1 | 0.74 | −0.15 | −1.06 | 0.05 | −0.63 | ORC4 | −0.07 | 0.18 | 0.29 | 0.05 | 0.03 | AC103810.6 | 0.04 | 0.01 | −0.55 | −1.41 | −2.22 |
| B3GALNT1P1 | 0.70 | −0.12 | −0.46 | −0.09 | −0.39 | AC025280.2 | −0.28 | −0.08 | −1.66 | −0.46 | −0.88 | AC010468.3 | −0.13 | −0.12 | 0.20 | −0.21 | −0.18 |
| AL353693.1 | −0.96 | 0.67 | 1.45 | 0.34 | 1.37 | RPS27 | 0.14 | 0.18 | 0.45 | −0.34 | −0.28 | ABCF2P2 | −0.03 | 0.75 | 0.57 | 0.89 | −0.51 |
| MMP25-AS1 | −0.47 | −0.12 | 0.27 | −0.31 | 0.25 | AC117386.2 | 0.61 | 0.37 | 0.68 | −0.77 | −1.39 | EIF1P1 | −0.02 | −0.57 | −1.34 | −0.67 | −0.24 |
| AC135279.1 | 0.60 | −0.34 | −0.56 | −0.07 | −0.13 | OR1I1 | −0.32 | −1.36 | −0.47 | 0.02 | 0.31 | CTXN2 | 0.03 | −1.12 | −0.79 | −0.05 | −0.73 |
| LINC00638 | −0.70 | −0.85 | 0.79 | −0.93 | 0.39 | GBF1 | 0.04 | −0.05 | −0.14 | −0.07 | −0.10 | BX284668.6 | −0.02 | −0.05 | −0.07 | 0.99 | 0.96 |
| AL450990.1 | −2.37 | 1.21 | 2.01 | 2.28 | 0.18 | MTCO1P6 | 0.63 | −1.27 | −0.61 | 0.26 | −0.05 | AC010451.1 | −0.13 | −0.17 | −0.10 | −0.49 | 0.31 |
| FKBP1C | 1.07 | −0.48 | −1.74 | −0.38 | −1.32 | AL358815.1 | −0.41 | 0.19 | 0.21 | 0.53 | 2.03 | BX119321.1 | −0.08 | −0.93 | −0.80 | 0.45 | 0.51 |
| CCSAP | −0.24 | 0.33 | 0.42 | 0.26 | 0.02 | AC068985.1 | −0.63 | −0.96 | −1.63 | 0.19 | −0.55 | AC092593.1 | −0.04 | 0.39 | 0.80 | −0.02 | −0.56 |
| LINC02547 | −1.59 | −0.77 | −0.29 | 0.53 | 1.58 | AL136368.1 | −0.33 | −0.26 | 1.61 | −0.17 | 1.93 | AL512326.3 | 0.04 | −0.98 | −0.32 | −0.08 | −0.46 |
| AC010627.1 | 0.79 | −0.15 | −0.85 | 0.23 | −0.25 | AC009970.1 | −0.26 | 0.12 | 0.61 | 0.21 | 0.31 | AC004147.2 | −0.03 | 0.58 | −3.37 | −0.73 | −1.42 |
| SPA17 | 0.39 | −0.02 | −0.56 | 0.22 | −0.29 | AC095057.1 | 0.65 | −1.10 | −0.82 | 0.16 | 0.07 | AL121952.1 | 0.01 | −0.37 | 0.62 | 0.06 | 0.79 |
| AC104383.1 | 0.92 | 0.35 | −0.45 | 0.19 | −0.45 | GAPDHP40 | 0.60 | 0.20 | −0.62 | 0.98 | 1.19 | AC100844.1 | −0.08 | −1.01 | −0.92 | 0.24 | −1.44 |
| AC087385.1 | 0.61 | −0.22 | −0.41 | 0.03 | −0.15 | AC015818.2 | −0.55 | −1.25 | 0.42 | −0.51 | 0.51 | AP002892.1 | 0.02 | −0.78 | −0.47 | −0.45 | 0.14 |
| C15orf62 | −0.40 | 0.49 | 0.23 | 0.26 | 0.02 | CLUHP8 | 0.80 | −1.85 | −1.06 | 0.52 | 0.28 | AL353764.1 | −0.03 | 0.02 | 0.30 | −0.61 | −0.48 |
| ACOT9 | 0.24 | −0.28 | −0.50 | −0.22 | −0.31 | AC024581.2 | 0.90 | −0.87 | −0.09 | 0.34 | 1.54 | LINC01233 | −0.13 | 0.54 | −1.24 | 1.17 | −1.93 |
| GTF2IP7 | −0.84 | 0.51 | 0.53 | 0.43 | −0.24 | BMP4 | −0.12 | −0.07 | −0.40 | 0.28 | 0.05 | RTKN | −0.01 | 0.03 | −0.36 | 0.03 | −0.01 |
| AC068733.2 | −1.22 | 0.18 | 0.32 | 0.57 | −0.03 | SPATA2 | 0.08 | 0.02 | −0.05 | 0.08 | −0.04 | AGGF1P6 | −0.06 | −1.00 | −0.10 | −0.72 | −0.90 |
| PACSIN3 | 0.34 | −0.25 | −0.87 | 0.30 | −0.08 | AC026333.4 | 0.35 | −0.68 | −1.11 | −0.54 | −0.27 | RPL7AP72 | −0.09 | −0.99 | −0.49 | 1.01 | −0.74 |
| AC011352.3 | −0.80 | 1.19 | 1.46 | 0.71 | −0.05 | AC107953.2 | −0.72 | 0.24 | 1.64 | 0.04 | 1.47 | AC023442.2 | −0.13 | −0.65 | 0.27 | −0.74 | 0.11 |
| DRP2 | −0.64 | −0.05 | −0.13 | −0.21 | −0.09 | AC103923.1 | −0.17 | 0.16 | 0.00 | −0.07 | 0.01 | AC245427.1 | 0.13 | −0.38 | 0.42 | −0.61 | 0.81 |
| G35086 | 0.76 | −0.73 | −0.82 | −0.25 | −0.66 | INTS6P1 | −0.38 | −0.51 | −1.36 | −0.01 | −1.14 | AL357673.1 | 0.05 | 0.91 | 0.18 | 0.46 | −0.22 |
| CBS | −0.92 | −0.39 | 0.43 | 0.48 | 0.22 | AC108047.1 | 0.20 | −0.53 | 0.01 | −0.30 | 0.46 | AC113331.1 | −0.13 | 0.71 | −0.25 | 0.80 | −0.25 |
| ATP6VOE2-AS1 | −0.79 | 0.71 | 1.04 | −0.33 | 0.62 | AC114321.1 | −1.12 | 0.27 | 1.28 | 1.26 | 0.17 | LINC00851 | 0.13 | −0.99 | 0.08 | 1.33 | 0.45 |
| JPH4 | −0.70 | 0.55 | 0.64 | −0.17 | 0.07 | MIR3170 | −0.32 | 0.06 | −0.75 | −0.01 | 0.38 | KAT2B | 0.00 | 0.27 | 0.02 | 0.06 | −0.25 |
| AC009299.3 | 0.55 | −0.63 | −0.35 | −0.19 | 0.03 | AL365223.1 | −0.24 | 0.20 | 0.55 | −0.18 | 0.06 | MIR548I2 | −0.01 | −0.18 | 0.50 | −0.64 | 0.05 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC136475.1 | −0.59 | 0.68 | 0.10 | 0.53 | −0.30 | OR51P1P | −1.06 | −0.71 | −0.88 | −0.70 | −2.30 | AC069545.1 | −0.07 | 0.64 | −0.83 | −0.19 | −1.63 |
| AL512504.1 | 0.90 | −0.90 | 0.78 | −0.07 | 0.50 | G34424 | 0.35 | −0.34 | −0.87 | 0.00 | 0.16 | AC010183.2 | −0.13 | −0.07 | −0.82 | −0.25 | −0.88 |
| DHX15 | 0.22 | −0.16 | −0.32 | −0.06 | −0.13 | CD1E | 0.31 | −0.44 | 0.08 | −0.05 | 0.56 | PHKBP1 | −0.07 | 0.21 | −0.95 | −1.10 | −0.86 |
| AC008063.2 | 1.56 | −0.95 | −1.64 | −0.01 | −2.11 | RNU1-1 | 0.16 | −0.49 | −0.38 | −0.66 | −0.48 | CRTAM | 0.02 | −0.60 | −0.03 | −0.27 | 0.28 |
| CRB2 | −0.61 | 0.35 | −0.47 | 0.49 | 0.04 | RNU7-63P | 0.63 | −1.34 | −0.66 | −0.20 | −0.65 | AC097462.2 | −0.13 | −1.24 | 0.02 | −0.75 | 1.09 |
| NSRP1 | 0.21 | −0.17 | −0.28 | −0.20 | −0.22 | G40536 | −0.20 | 0.46 | 0.65 | −0.23 | −0.01 | APPL2 | 0.00 | 0.27 | −0.09 | 0.21 | −0.27 |
| RNU1-67P | −0.63 | −0.52 | 0.47 | −0.53 | −0.16 | AC006116.2 | −0.44 | 0.91 | 0.23 | 0.56 | −1.38 | BX510359.2 | −0.13 | −0.32 | 0.62 | −0.67 | 0.48 |
| LHFPL3 | −1.12 | 0.50 | −2.26 | 0.80 | −1.88 | SOS1-IT1 | 0.13 | −0.13 | 0.19 | −0.13 | 0.17 | AC104532.2 | 0.05 | 2.07 | 0.84 | −0.03 | −0.55 |
| CCNJP2 | 0.55 | −0.25 | −0.54 | −0.21 | −0.32 | NPM1P10 | −0.55 | −0.53 | −0.99 | 0.14 | 0.60 | AC009127.1 | 0.02 | 0.51 | 0.18 | 0.95 | −0.84 |
| AC040160.1 | −0.42 | 0.24 | 0.31 | −0.05 | −0.22 | LINC01077 | −1.03 | 1.49 | 0.22 | 0.67 | −0.99 | RN7SKP5 | 0.08 | −1.34 | 0.42 | −1.39 | 1.14 |
| RPL6P8 | −1.34 | −0.22 | 1.12 | 0.28 | 0.58 | DPY19L1P2 | −0.24 | −0.09 | 1.31 | −0.24 | 0.58 | AL008720.1 | 0.06 | −0.03 | −0.22 | 1.24 | 1.54 |
| RPS3AP14 | −1.27 | −0.79 | 1.36 | 0.28 | 1.27 | POLRIC | 0.09 | −0.03 | −0.14 | 0.06 | −0.05 | RNA5SP320 | 0.09 | 0.35 | 2.01 | 0.12 | −0.67 |
| SCAND3P1 | −1.57 | 0.81 | 0.24 | 0.43 | 0.93 | KRT8P40 | 0.72 | −1.37 | −0.92 | −1.76 | −1.86 | AC005297.3 | −0.13 | −1.08 | −0.24 | 1.69 | 0.94 |
| AC073413.1 | −1.03 | 0.23 | 0.99 | 0.57 | 0.42 | AC083949.1 | 0.18 | −0.05 | −0.17 | −0.25 | −0.30 | RN7SKP271 | −0.01 | 0.21 | 0.39 | 0.16 | 0.33 |
| AL365273.1 | 0.43 | −0.73 | −0.53 | −0.06 | 0.21 | AC025580.1 | −0.37 | −1.12 | −0.50 | −0.48 | 1.14 | G32333 | −0.02 | 0.42 | 0.66 | −0.04 | −0.50 |
| SERTAD4 | 0.43 | 0.28 | −0.46 | 0.40 | −0.37 | G14007 | −0.79 | −0.71 | −0.07 | 0.40 | −0.17 | AC244517.11 | −0.08 | 1.82 | −0.96 | 1.91 | −1.48 |
| AC110597.1 | −0.82 | −0.04 | 0.84 | −0.17 | 0.17 | AC009407.1 | −0.69 | 0.53 | 2.20 | −0.91 | 1.03 | AL033529.1 | 0.03 | 0.07 | 1.91 | −0.51 | 0.93 |
| AC093278.1 | −1.74 | 1.02 | 2.48 | 1.83 | 1.91 | AP001972.3 | 0.42 | −0.42 | −1.73 | 0.45 | −0.96 | AC080078.1 | −0.02 | 0.08 | −1.60 | 0.47 | −0.12 |
| AC254562.3 | −0.55 | −0.17 | 0.13 | 0.16 | 0.84 | AC007215.1 | 0.69 | −0.64 | 0.29 | −0.30 | 1.25 | AC087501.1 | 0.01 | 0.03 | 0.26 | −0.05 | 0.16 |
| AL162725.2 | −1.20 | −0.23 | 0.78 | −0.13 | 0.03 | AC073063.1 | −0.14 | −0.11 | 0.37 | −0.12 | 0.35 | MTHFD2P4 | −0.05 | 0.92 | −1.38 | −0.50 | −2.08 |
| AC092666.2 | −0.93 | 0.39 | 1.06 | 0.08 | 1.06 | AL022341.1 | −0.29 | −0.56 | 0.38 | −0.26 | 0.64 | SPATA42 | −0.04 | −0.03 | −0.05 | −0.29 | −0.86 |
| NMT2 | −0.28 | 0.16 | 0.11 | 0.24 | 0.11 | CCNB1IP1 | −0.07 | 0.01 | −0.11 | 0.08 | −0.08 | AL450309.1 | 0.07 | −0.23 | 0.10 | −0.17 | 0.93 |
| LINC01018 | −1.40 | 0.87 | 2.02 | 0.10 | 0.18 | AC113378.1 | 0.64 | −2.05 | −1.26 | −0.72 | 0.41 | RN7SL616P | −0.06 | −0.20 | −1.73 | 0.93 | −0.74 |
| MYBPH | −1.12 | 0.51 | 0.67 | 0.95 | 0.11 | PYCR2 | −0.08 | −0.11 | −0.06 | 0.03 | 0.26 | AL390763.1 | −0.09 | −0.80 | −0.82 | −0.09 | 0.61 |
| ARHGEF28 | −0.21 | 0.24 | 0.09 | 0.07 | 0.07 | KRT78 | −0.17 | 0.19 | 0.29 | 0.14 | −0.27 | AC002127.1 | −0.13 | −0.80 | 0.09 | −0.67 | −0.02 |
| HCG11 | −0.30 | 0.29 | 0.38 | 0.22 | 0.02 | AC104333.3 | −0.44 | 0.63 | 0.44 | −0.77 | −0.45 | NAPA-AS1 | 0.01 | −0.17 | −0.16 | 0.12 | −0.12 |
| AL157700.1 | −0.77 | 0.77 | 0.06 | 0.41 | −0.30 | LINC00278 | 0.23 | 0.18 | −0.10 | 0.19 | 0.09 | AC026979.3 | 0.02 | −0.55 | 1.11 | −1.36 | 0.28 |
| MIR210HG | −0.47 | 0.33 | 0.23 | 0.43 | 0.21 | AC023511.1 | −1.24 | −0.56 | −0.32 | 0.45 | 1.37 | RN7SL442P | −0.02 | −0.90 | −0.13 | 0.38 | 0.58 |
| G27121 | −0.93 | 1.11 | 2.07 | −0.21 | 0.22 | AC117947.1 | −0.84 | −0.13 | 1.49 | −0.11 | 0.52 | AC117377.1 | −0.02 | 0.23 | 0.11 | 0.28 | 0.22 |
| AL445645.1 | −0.97 | 0.73 | 1.09 | 0.37 | −0.42 | SLC17A3 | −0.42 | −1.13 | −0.50 | 0.45 | −0.26 | LINC00408 | −0.13 | −0.17 | −0.08 | 0.41 | −0.32 |
| AL161772.1 | −0.70 | 0.19 | 0.34 | 0.11 | −0.20 | LNCSRLR | 0.26 | −0.09 | −1.29 | 0.04 | −0.68 | MTCYBP38 | 0.08 | 0.31 | −0.33 | −0.76 | −1.88 |
| RN7SL411P | −1.17 | 1.16 | 2.39 | 1.16 | 0.44 | AC096745.1 | −0.44 | 0.94 | 0.85 | −1.10 | −0.79 | DEFA11P | −0.13 | 0.36 | NA | −0.05 | −1.26 |
| PRB1 | −0.67 | 0.14 | 0.17 | −0.08 | −0.47 | AC026992.1 | 0.48 | 0.75 | 0.22 | 0.80 | −0.43 | AL807761.4 | 0.01 | 0.10 | −0.72 | 0.07 | −0.15 |
| BX255925.2 | 1.50 | −0.77 | 0.33 | 0.32 | 1.45 | AGPAT3 | 0.09 | −0.05 | −0.16 | 0.11 | 0.04 | AC103681.1 | 0.13 | −0.95 | −1.11 | −1.34 | −0.25 |
| MPTX1 | −1.10 | 0.73 | 1.09 | 1.18 | 0.69 | CCDC38 | −0.17 | 0.34 | 0.29 | 0.47 | 0.10 | AC011712.1 | 0.13 | −0.50 | −0.70 | 0.64 | −0.62 |
| AC097478.1 | −0.66 | −0.16 | 1.23 | 0.48 | 0.31 | HHLA1 | 0.45 | −0.35 | 0.08 | 0.22 | −0.20 | RPS3AP50 | −0.04 | −1.28 | 0.93 | −0.51 | 0.19 |
| EMB | 0.45 | −0.21 | 0.29 | 0.01 | −0.09 | RN7SL835P | −0.74 | −1.56 | 1.96 | −0.81 | 1.93 | AC078785.3 | 0.04 | −0.96 | 0.36 | −1.92 | −1.91 |
| MBD6 | −0.30 | 0.33 | −0.15 | 0.37 | −0.03 | RPS27AP8 | 0.22 | −1.03 | −0.70 | −0.25 | 0.18 | OR7E117P | −0.07 | −0.59 | −0.45 | −0.53 | −1.61 |
| MYLK-AS1 | −0.48 | 0.12 | 0.15 | −0.26 | 0.02 | HNRNPA1P13 | −0.58 | −0.41 | 0.49 | −0.33 | 0.95 | AC108860.2 | 0.01 | 0.35 | −0.57 | −0.17 | −0.45 |
| RNU6-1316P | 1.31 | −0.68 | −0.42 | −0.03 | 0.87 | MIR33A | 0.45 | 0.72 | 0.43 | 0.24 | −0.55 | AC022182.1 | −0.02 | 0.30 | 0.19 | −0.14 | 0.47 |
| AC119674.2 | −0.51 | −0.47 | 0.46 | −0.50 | 0.45 | AC135977.1 | 0.79 | 0.15 | −0.73 | −0.26 | 0.27 | AC034205.2 | 0.02 | −0.02 | −0.51 | 0.47 | −1.57 |
| AC010973.1 | −0.57 | −0.24 | −0.03 | 0.02 | 0.56 | MAGEB3 | 0.94 | −1.24 | −1.03 | −0.71 | −1.38 | AL450306.1 | 0.01 | −0.01 | −0.21 | −0.02 | 0.17 |
| SLC26A11 | −0.36 | 0.21 | −0.01 | 0.25 | 0.13 | AP005242.2 | −0.65 | 0.13 | 0.05 | 0.35 | 0.39 | AC008040.1 | −0.02 | −0.27 | −0.21 | 0.24 | −0.20 |
| AC117473.1 | −1.45 | −0.80 | −0.11 | 0.84 | 1.02 | CPB1 | −0.31 | −0.04 | 0.82 | 0.35 | 0.44 | MTATP6P31 | 0.12 | 0.96 | 1.05 | 1.20 | −1.27 |
| AL121760.1 | −0.87 | 0.89 | 0.31 | 0.22 | −0.28 | NRBF2P3 | 0.57 | −0.68 | −1.66 | 1.09 | 0.69 | SMAD2 | 0.00 | 0.05 | 0.07 | −0.02 | −0.09 |
| AC011458.2 | −1.58 | −0.84 | 2.98 | −1.35 | 1.45 | NT5E | 0.16 | −0.36 | 0.23 | −0.36 | −0.20 | AP002008.1 | −0.07 | −0.53 | −1.27 | 0.35 | −0.16 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC015818.6 | −1.04 | −0.57 | 0.77 | 0.10 | 1.59 | GUSBP8 | −0.44 | −0.43 | 0.96 | 0.14 | 0.92 | G43342 | −0.09 | −1.40 | 0.57 | −1.78 | 0.17 |
| SLC6A4 | −0.48 | 0.91 | 0.58 | 0.60 | −0.14 | GPR174 | 0.23 | −0.83 | 0.64 | −0.50 | 1.10 | SPTY2D1OS | −0.01 | 0.23 | 0.36 | 0.30 | 0.06 |
| AL137793.2 | −1.82 | 0.25 | 1.85 | −0.79 | 0.52 | ARSDP1 | −0.56 | 0.63 | 1.44 | 0.91 | 0.44 | OR2C3 | 0.04 | −1.08 | 0.11 | −0.72 | 1.09 |
| AC010768.1 | 0.97 | −0.44 | −0.47 | 0.10 | 0.85 | AL512631.1 | −0.62 | −0.26 | 1.37 | −0.26 | 0.81 | AC103808.3 | 0.04 | −0.84 | −1.51 | 0.06 | 0.50 |
| G35257 | −0.71 | 0.65 | 1.68 | −0.68 | 0.39 | BX842568.3 | −0.76 | 0.85 | 0.91 | −0.54 | −0.08 | AL845331.1 | −0.12 | −0.02 | 0.82 | 1.14 | 0.04 |
| MSI1 | −0.85 | 0.32 | 0.65 | 0.28 | −0.06 | CNKSR1 | 0.12 | −0.08 | −0.79 | 0.20 | 0.00 | SELENOKP1 | −0.04 | −0.59 | 0.49 | 0.54 | 0.55 |
| G3670 | −1.31 | 0.47 | 2.12 | 0.27 | 0.35 | SCYGR4 | −0.63 | −0.31 | −0.31 | −0.28 | −0.93 | AC021146.1 | 0.12 | −0.13 | 1.11 | −0.86 | 0.03 |
| PHBP13 | −1.33 | 0.35 | 1.35 | −0.08 | 1.41 | AC008406.3 | 0.53 | 0.06 | −1.67 | −0.01 | −1.76 | AF274573.1 | −0.10 | −0.90 | −0.54 | −0.25 | 0.83 |
| FAM50B | −0.35 | −0.04 | 0.12 | 0.17 | 0.48 | AC067817.1 | −0.29 | −0.08 | 0.16 | −0.25 | 0.12 | AC108066.1 | −0.02 | −0.28 | −1.18 | −0.13 | −0.53 |
| AL589685.1 | −1.06 | −0.09 | 1.47 | 0.11 | 1.74 | COX6CP16 | 0.34 | −0.05 | −0.27 | −1.03 | −0.08 | AC111194.1 | −0.07 | −0.25 | −0.01 | 0.99 | 1.53 |
| CRNN | −0.85 | 1.28 | 3.47 | 0.52 | 1.16 | NMNAT1P3 | −0.63 | −0.12 | 0.50 | −0.62 | −0.79 | AL139280.1 | −0.12 | 0.57 | −0.52 | 0.88 | −0.50 |
| RNA5SP226 | −1.17 | 0.43 | −0.26 | 1.46 | −0.57 | AC107074.1 | 0.31 | −0.09 | 0.46 | 0.31 | 0.46 | LINC02348 | 0.05 | −0.54 | −0.75 | −1.66 | −1.36 |
| AL161804.1 | −1.30 | 0.89 | 0.52 | 0.98 | 0.61 | KXD1 | −0.10 | −0.02 | −0.37 | 0.15 | −0.15 | LA16c-83F12.6 | 0.05 | −1.62 | −0.64 | −1.07 | −1.80 |
| AC011755.1 | 0.43 | −0.53 | −0.38 | −0.09 | 0.38 | AL445220.1 | −0.52 | 0.09 | −0.36 | 0.72 | −0.22 | AC097501.2 | −0.05 | −1.65 | −1.28 | −0.39 | −1.62 |
| PTMAP2 | 0.36 | −0.23 | −0.48 | 0.11 | 0.10 | PROSER2 | −0.15 | −0.18 | −0.38 | 0.02 | 0.01 | IL6RP1 | −0.12 | −0.23 | −1.38 | 0.55 | −0.63 |
| STARD5 | −0.38 | 0.30 | −0.02 | 0.35 | 0.08 | CBX1P5 | 0.74 | −0.28 | −0.77 | −0.60 | −1.61 | AL590113.1 | −0.12 | 0.12 | 0.80 | −0.12 | 2.05 |
| SRPX | −0.69 | 0.45 | 1.13 | 0.09 | −0.11 | RNA5SP475 | −0.76 | 0.10 | −0.99 | −0.29 | 1.20 | LINC02112 | −0.02 | 0.12 | −0.94 | 0.15 | −0.64 |
| HDHD2 | −0.30 | 0.11 | 0.20 | 0.34 | 0.36 | AP003555.1 | −0.43 | 0.12 | −0.08 | −0.55 | −0.05 | EVA1B | −0.01 | 0.18 | −0.03 | −0.12 | −0.12 |
| SNORA71D | −0.68 | 0.16 | −0.20 | 0.76 | −0.44 | NRF1 | −0.06 | 0.01 | −0.05 | −0.03 | 0.01 | AC022306.1 | 0.01 | 0.49 | −0.63 | −0.16 | −0.34 |
| ASTN1 | −0.81 | 0.07 | −0.04 | 0.14 | −0.33 | KRT18P14 | −0.49 | 0.91 | −1.51 | 1.61 | −1.02 | MTND1P4 | 0.12 | −0.46 | −0.47 | 0.77 | −0.52 |
| MIR211 | −1.17 | 1.54 | −0.07 | 1.62 | −1.32 | IGLV5-52 | 0.18 | 0.06 | 0.25 | −0.18 | 0.20 | LINC01980 | 0.02 | 0.73 | −0.11 | −0.46 | −1.23 |
| NDUFS4 | 0.28 | −0.08 | −0.26 | −0.14 | −0.23 | RN7SL74P | −0.44 | −1.10 | 0.29 | 0.15 | 1.02 | AC092720.2 | −0.12 | 0.05 | 0.73 | −0.88 | −0.53 |
| AL592494.2 | −1.62 | −0.63 | 0.94 | 1.07 | 1.68 | SDF4 | −0.06 | −0.04 | −0.29 | 0.11 | −0.07 | AL512631.2 | −0.04 | −1.56 | 0.35 | −1.07 | 0.12 |
| HLA-B | 0.34 | −0.49 | −0.20 | −0.32 | −0.07 | AF106564.1 | 0.94 | −0.35 | −0.03 | −0.36 | −0.31 | OR4C9P | 0.12 | −0.92 | −0.40 | −0.18 | 1.67 |
| ANKRD46 | 0.29 | −0.21 | −0.04 | −0.10 | 0.07 | MORF4 | 0.40 | 0.21 | −1.56 | 0.61 | −0.99 | AC005722.3 | 0.06 | 0.19 | 0.69 | 0.73 | 0.43 |
| HERC2P10 | −0.60 | 0.21 | 0.09 | 0.40 | 0.22 | LINC01186 | −0.41 | 0.95 | 1.34 | 0.47 | 0.27 | STK40 | 0.00 | 0.07 | −0.23 | −0.12 | −0.39 |
| SLC25A32 | 0.73 | −0.26 | 0.04 | −0.28 | −0.15 | ARGFXP1 | −0.80 | 0.81 | 1.29 | 2.57 | −0.38 | CSAG4 | 0.12 | −0.31 | −1.62 | −0.05 | −1.11 |
| NOBOX | −1.01 | 1.50 | 1.13 | 0.41 | −0.31 | AL357033.3 | 0.20 | −0.18 | −0.70 | −0.13 | −0.59 | IGLV3-9 | 0.12 | 0.55 | 2.18 | −0.42 | −2.34 |
| NR2F6 | 0.29 | 0.09 | −0.33 | 0.21 | 0.00 | AL583722.1 | −0.20 | 0.35 | −0.63 | −0.40 | −1.56 | DEFB122 | 0.11 | −0.15 | −1.06 | 1.25 | −1.04 |
| PGAM1P5 | −0.69 | 0.16 | 0.59 | 0.50 | 1.10 | AP001360.1 | 0.81 | 0.73 | −1.75 | 0.01 | −2.99 | AL138960.1 | 0.07 | 0.03 | 2.24 | −2.20 | 1.34 |
| PPIAP52 | 0.89 | 0.23 | −0.38 | 0.75 | 0.21 | AP001025.1 | 0.37 | −0.73 | −0.15 | 0.28 | 0.01 | AC022001.1 | 0.01 | 0.38 | 0.44 | −0.20 | −0.09 |
| RTN4IP1 | 0.26 | −0.24 | −0.09 | −0.07 | −0.02 | AP002358.1 | −0.31 | −0.48 | 0.00 | 0.39 | 0.81 | AL031651.1 | −0.02 | −0.19 | −0.02 | −1.08 | 0.27 |
| C11orf45 | −0.53 | 0.32 | −0.26 | 0.53 | −0.17 | AP001107.6 | 0.36 | −0.28 | 0.47 | 0.92 | 0.12 | C17orf112 | −0.04 | −1.04 | −1.79 | 0.83 | −2.32 |
| AIFM3 | −0.64 | 0.00 | −0.14 | 0.23 | −0.43 | ACOX3 | 0.07 | 0.23 | −0.03 | 0.22 | 0.05 | FGF4 | −0.12 | 1.43 | 0.29 | 0.15 | −2.19 |
| ROS1 | −1.07 | 0.57 | −0.07 | 1.59 | 0.96 | SALL4P7 | −0.49 | −0.02 | −0.67 | 0.46 | −0.13 | AP001496.2 | −0.03 | −0.84 | −1.83 | 0.41 | −0.55 |
| COLCA1 | −0.67 | 0.25 | 0.25 | 0.17 | −0.16 | AC026464.5 | −0.30 | −0.28 | −0.97 | −0.24 | −0.15 | AL391646.1 | −0.12 | 0.09 | −1.34 | 0.00 | 1.07 |
| NAA35 | 0.14 | 0.04 | −0.04 | 0.00 | −0.17 | GP5 | −0.40 | −0.40 | −1.13 | −0.58 | −0.02 | AC087888.1 | −0.04 | 0.71 | −0.35 | −0.50 | −0.28 |
| AC087477.6 | −1.05 | 1.48 | 1.50 | 0.83 | −0.06 | AC004870.1 | 0.39 | −0.06 | −1.48 | −0.52 | −0.65 | AC008751.1 | −0.03 | 0.32 | 1.63 | −1.01 | 0.82 |
| AC020931.1 | 1.01 | −1.28 | −1.27 | 0.23 | 0.27 | AC063960.2 | −0.16 | 0.42 | 0.47 | 0.06 | 0.02 | FBXL21 | 0.03 | 0.33 | −1.82 | 0.65 | −1.75 |
| OR2S1P | −1.62 | −0.26 | −0.72 | 0.69 | −0.38 | NEBL-AS1 | −0.30 | 1.05 | 0.97 | 1.29 | 0.76 | KRT82 | −0.02 | −0.31 | −0.26 | 0.26 | 0.38 |
| RPS2P4 | −1.00 | 0.14 | 0.26 | 0.46 | −0.28 | AL591377.1 | −0.44 | −0.06 | 0.96 | 0.57 | 0.71 | AC022023.1 | −0.02 | −0.30 | 0.26 | −0.69 | 0.44 |
| KLHDC8A | −0.89 | 0.61 | 0.46 | 0.49 | 0.21 | AC005529.1 | 0.27 | −0.22 | −0.69 | −0.35 | −0.69 | AC073359.2 | 0.12 | −0.76 | −0.37 | 1.03 | 1.28 |
| AL022328.4 | −0.75 | 0.20 | 0.02 | −0.10 | 0.23 | EEF1A1P10 | −0.24 | 0.41 | −0.16 | 0.77 | −0.08 | AL354707.3 | 0.05 | 1.39 | −0.94 | 1.39 | −1.39 |
| AL445123.1 | −0.82 | 0.35 | 0.70 | −0.06 | 0.31 | G34551 | −0.30 | 0.37 | 0.36 | 0.75 | −0.56 | AL359538.1 | −0.11 | 0.59 | 0.02 | 1.92 | −1.38 |
| SNRPCP11 | −1.07 | −0.14 | 1.09 | 0.63 | 0.84 | OR4D9 | −0.34 | 0.29 | 0.19 | 0.77 | 0.33 | AC005480.2 | −0.02 | 0.84 | −0.09 | 0.71 | −1.71 |
| OR2I1P | 1.02 | −0.91 | −0.38 | −0.71 | −0.21 | OR4Q2 | 0.59 | −0.37 | −0.62 | 0.16 | −1.38 | HUNK-AS1 | 0.07 | −0.20 | 1.07 | −0.33 | −0.39 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| LCA10 | −1.54 | 0.80 | 2.77 | 0.70 | 1.57 | SSX1 | 0.81 | −1.34 | −1.21 | 0.50 | −2.15 | AL157823.1 | 0.12 | −0.17 | −0.08 | −1.04 | −2.64 |
| SPTSSB | −0.46 | 0.67 | 1.13 | 0.40 | −0.07 | AC090592.1 | −0.46 | −1.39 | −1.65 | 0.35 | 0.05 | AC023115.1 | 0.04 | −0.07 | −0.93 | −0.22 | −2.79 |
| RHOBTB1 | −0.35 | 0.05 | 0.34 | −0.07 | −0.14 | RNU6-1285P | 0.32 | 0.21 | −0.47 | −0.04 | −0.74 | AL158013.1 | 0.12 | 0.84 | 0.27 | 0.24 | −2.12 |
| AC007342.4 | 0.98 | −1.22 | −0.18 | −0.12 | 0.77 | CNTN4-AS1 | −0.93 | 1.57 | 1.26 | 0.66 | −1.28 | MIRLET7D | −0.01 | −0.65 | −0.04 | 0.10 | 0.06 |
| AQP7P2 | −2.20 | 2.56 | 1.96 | 2.30 | −0.06 | AC023271.1 | 0.27 | −0.63 | −0.11 | −0.02 | −0.30 | AC010342.1 | 0.02 | −0.22 | −0.83 | 0.52 | −1.07 |
| AL355353.1 | −0.76 | 0.58 | 1.29 | 0.27 | 0.12 | AC011455.1 | −0.99 | −0.05 | −0.11 | 0.50 | 0.19 | LINC02042 | −0.02 | 0.67 | −0.38 | −0.03 | −0.04 |
| RNU7-70P | 1.17 | −2.34 | −1.24 | −0.19 | 1.55 | ARL2 | 0.12 | 0.03 | −0.12 | 0.17 | −0.27 | AL136984.1 | 0.01 | 0.14 | −0.09 | 0.21 | −0.14 |
| AC007792.1 | −0.86 | 0.93 | −0.03 | 0.76 | −0.20 | MIR567 | −0.49 | −0.19 | 0.80 | −0.83 | 0.25 | RN7SL321P | −0.03 | −0.18 | −0.33 | 0.11 | −0.07 |
| MIR942 | 1.07 | −0.42 | −0.51 | −0.05 | −0.17 | KRT89P | −0.63 | −0.81 | −1.23 | 1.38 | 0.34 | BBIP1P1 | 0.01 | 0.51 | −0.17 | 0.25 | −0.03 |
| G5833 | 0.72 | −0.46 | −0.52 | −0.28 | 0.07 | AC004851.1 | 0.38 | −1.60 | 0.16 | −0.80 | 0.18 | OR7E159P | 0.05 | −1.11 | −1.54 | 1.45 | −0.83 |
| FCER1G | 0.58 | −0.65 | −0.27 | −0.23 | −0.21 | AC020658.6 | 0.21 | −0.33 | −0.32 | 0.25 | −0.05 | RBM14 | 0.00 | −0.13 | 0.03 | −0.15 | 0.20 |
| CCL4 | 0.99 | −1.57 | −0.49 | −0.32 | 0.46 | RASL11B | 0.13 | 0.09 | 0.62 | 0.15 | 0.57 | ATAD2B | 0.00 | 0.06 | −0.03 | 0.05 | −0.01 |
| AC007599.2 | 0.82 | −0.69 | −1.06 | 0.18 | −0.19 | CBX1P1 | −0.22 | −0.15 | 0.67 | −0.21 | 0.07 | AP003461.1 | −0.03 | −1.07 | 0.35 | 0.13 | 1.48 |
| RAD9A | −0.36 | 0.13 | 0.00 | 0.30 | 0.16 | CHTF18 | −0.14 | −0.31 | −0.67 | 0.11 | 0.19 | SNHG27 | 0.04 | −1.23 | −0.77 | 0.07 | −0.53 |
| GALNT5 | 0.43 | −0.15 | 0.10 | −0.62 | −0.39 | RPL34P3 | −0.71 | −1.57 | 0.08 | −1.26 | −0.94 | PABPC1P12 | 0.05 | −0.29 | −1.21 | −0.28 | −0.32 |
| ARID5B | 0.29 | −0.04 | −0.14 | −0.15 | −0.37 | AC004160.2 | −0.44 | 0.30 | 0.69 | −0.05 | −0.61 | FO393414.3 | −0.02 | 1.05 | 0.67 | 0.81 | 0.49 |
| AL157394.1 | 0.72 | −0.36 | 0.04 | 0.10 | 0.25 | RPL6P12 | −0.23 | 0.22 | 0.34 | 0.09 | 0.28 | AC022441.2 | 0.12 | −0.94 | −0.48 | −0.35 | −1.89 |
| KANK3 | −0.50 | 0.31 | 0.12 | 0.33 | 0.12 | FAM160B1 | −0.07 | 0.12 | 0.02 | 0.11 | −0.07 | MYL6BP1 | −0.02 | 0.51 | −0.63 | 0.01 | −0.13 |
| SLC25A23 | −0.30 | 0.65 | 0.14 | 0.42 | −0.29 | HNRNPA1P44 | 0.49 | −0.99 | −0.32 | 0.25 | −0.28 | EIF4BP1 | −0.12 | −0.51 | −0.49 | 0.36 | 0.20 |
| EIF2AK4 | 0.15 | −0.09 | −0.05 | −0.15 | −0.10 | HINT3 | 0.09 | 0.07 | 0.23 | 0.04 | 0.04 | G38528 | 0.01 | −0.07 | −0.46 | 0.19 | −0.42 |
| CABP1 | −0.74 | −0.15 | −0.19 | 0.40 | −0.29 | GAPDHP37 | −0.67 | 0.29 | 0.50 | 0.16 | −0.40 | AC105381.1 | −0.02 | −1.05 | −0.04 | −1.00 | −0.68 |
| SNX31 | −0.80 | 0.49 | −0.33 | 0.15 | −0.40 | AL031985.1 | 0.50 | −1.96 | −0.34 | −1.33 | 0.87 | RNA5SP292 | −0.12 | NA | −0.11 | 0.41 | 0.36 |
| RP11-782C8.2 | −0.39 | 0.50 | 0.15 | 0.46 | −0.31 | FTH1P12 | −0.42 | −0.37 | 0.11 | −0.63 | 0.33 | AC068492.1 | −0.11 | 0.14 | −0.98 | −0.13 | −1.62 |
| COL3A1 | 0.61 | 0.28 | 1.39 | −0.86 | −0.32 | CFAP77 | 0.32 | 0.36 | 0.25 | 0.08 | −0.61 | LINC00366 | 0.05 | −0.64 | −1.28 | 0.14 | −0.28 |
| PCDH9-AS4 | −1.80 | 1.29 | 0.03 | 1.62 | −1.04 | SKAP1-AS1 | −0.30 | 0.47 | −0.27 | −0.35 | −1.29 | AC023300.3 | 0.03 | −1.32 | −1.87 | 0.14 | −0.62 |
| AL445231.1 | 0.52 | −0.19 | 0.11 | 0.01 | 0.26 | AC018755.4 | 1.16 | −0.16 | −0.52 | −0.49 | 0.36 | AC004449.1 | 0.03 | −0.32 | 0.92 | −0.37 | −0.58 |
| AC009365.2 | 0.52 | −0.17 | −0.53 | 0.16 | 0.25 | AC110079.2 | 0.32 | −0.68 | 1.16 | −0.61 | 1.63 | MAGEA4 | −0.11 | 0.32 | −1.49 | 1.41 | −1.50 |
| PCDHB14 | −0.37 | 0.40 | 0.53 | 0.15 | 0.03 | CICP10 | −1.11 | 1.72 | 0.14 | 0.15 | −1.70 | AC007486.1 | −0.12 | 1.06 | −0.67 | −0.89 | −1.82 |
| LINC00535 | −0.90 | 0.47 | 0.77 | 0.09 | 0.13 | AL133216.1 | −0.63 | −0.94 | 2.68 | −0.74 | 2.23 | G826 | 0.02 | 0.94 | −1.06 | 0.17 | −0.91 |
| AC106873.1 | 0.52 | −0.49 | −0.10 | −0.11 | 0.26 | AKAP11 | 0.07 | 0.08 | 0.14 | −0.06 | −0.08 | C11orf94 | −0.01 | 1.07 | −0.54 | 0.12 | −0.42 |
| RBM27 | 0.30 | −0.05 | −0.09 | 0.01 | −0.15 | FICD | 0.07 | 0.06 | 0.13 | −0.02 | −0.07 | HSPE1P8 | −0.01 | 0.03 | −0.07 | −0.28 | 0.05 |
| AL022100.1 | −0.73 | −0.13 | 0.07 | 0.18 | −0.23 | DDR1 | −0.12 | 0.33 | −0.31 | 0.38 | −0.11 | AC104211.3 | −0.11 | −0.23 | 0.46 | 0.74 | −1.99 |
| PTMAP6 | −1.21 | 1.64 | −0.08 | 1.06 | −3.20 | AP000619.1 | −0.58 | −1.27 | −0.67 | −1.70 | −1.75 | AL133259.1 | 0.01 | −0.40 | −1.06 | 0.20 | −0.23 |
| AL358942.1 | 1.26 | −0.41 | −0.67 | −0.12 | −0.43 | RNU6-1142P | 0.29 | −0.82 | −1.30 | −0.12 | 0.03 | LINC01740 | −0.12 | 1.57 | −0.47 | −0.02 | −0.88 |
| AC092958.1 | −1.69 | −0.19 | 1.11 | −0.77 | −0.16 | LINC01802 | −0.39 | −0.27 | −0.07 | 0.73 | −0.56 | AC096734.1 | 0.09 | −0.87 | −0.08 | 2.35 | 2.28 |
| AC100835.1 | −1.21 | 0.72 | 1.78 | 0.34 | 0.62 | ADAMTS18 | −0.27 | 0.58 | 0.41 | −0.10 | −0.52 | AC104455.1 | −0.06 | −1.13 | 0.06 | −1.37 | −1.17 |
| SH3YL1 | −0.25 | 0.33 | 0.50 | 0.18 | 0.16 | AC010139.1 | 0.91 | −1.35 | −1.47 | −0.01 | −0.47 | AC068946.1 | −0.01 | 0.52 | 0.24 | 0.58 | 0.11 |
| MTND2P11 | −0.66 | 0.13 | 0.27 | 0.00 | 0.25 | NR2C1 | −0.05 | 0.09 | −0.05 | 0.00 | −0.13 | MTND4P30 | 0.02 | −0.50 | 0.31 | 0.52 | 1.02 |
| AL359273.1 | −1.86 | 1.58 | −0.19 | 2.83 | 1.05 | RPL7P10 | 0.46 | 0.53 | −0.11 | 0.38 | 0.41 | AL356259.1 | −0.10 | 0.81 | −0.13 | −1.47 | −2.64 |
| RN7SL765P | −1.61 | −1.16 | 0.02 | 1.01 | 3.14 | LINC00700 | −0.52 | −0.86 | 0.61 | 0.51 | −0.56 | NEUROD6 | 0.03 | −0.30 | −0.07 | 1.32 | 0.31 |
| DNAJC10 | 0.22 | −0.14 | 0.07 | −0.27 | 0.03 | AC016134.1 | −0.85 | 1.37 | −0.78 | −1.35 | −3.00 | AL162393.1 | −0.08 | −0.88 | −1.72 | −1.45 | −1.73 |
| PLOD1 | 0.23 | −0.20 | −0.29 | −0.26 | −0.20 | AC015712.1 | −0.49 | 0.94 | 0.31 | −0.01 | 0.18 | LINC02051 | −0.11 | 0.89 | −0.69 | 0.37 | −3.72 |
| EPS8L3 | −1.04 | 0.03 | 0.81 | 0.61 | 0.40 | AL512622.1 | −0.67 | 0.81 | 2.87 | 0.41 | 0.78 | AC073257.1 | −0.07 | −1.00 | −1.74 | 0.45 | −0.37 |
| AL355388.3 | 1.01 | −0.04 | −1.50 | −0.36 | −1.35 | AC007993.2 | −0.69 | −0.39 | −0.83 | 0.26 | −0.78 | SDK1 | −0.01 | 0.38 | 0.41 | −0.72 | −0.48 |
| RN7SL546P | −1.03 | 0.24 | −0.90 | −0.08 | −0.01 | RN7SL364P | 0.24 | −0.21 | −0.15 | −0.35 | −0.58 | AC090071.1 | −0.04 | 0.19 | 1.33 | 1.14 | 1.22 |
| OR2Q1P | −1.71 | 0.19 | 0.72 | −0.20 | −0.76 | AC125603.2 | −0.64 | −0.84 | 0.02 | 0.46 | 1.40 | KHDRBS2-OT | 0.03 | −1.62 | −1.95 | 2.30 | 1.15 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| RPL35P3 | −0.56 | 0.03 | −0.14 | 0.25 | 0.15 | LRRC32 | 0.18 | 0.03 | 0.38 | −0.09 | −0.29 | NDUFS5P6 | 0.11 | 0.53 | 0.00 | 0.61 | 1.09 |
| CUX2 | −0.94 | 0.62 | 0.26 | 0.97 | 0.11 | ATP8A2P3 | 0.43 | −0.57 | −1.79 | 0.92 | −0.41 | OR5H1 | 0.03 | −0.37 | −1.28 | −0.51 | −0.05 |
| G19270 | −1.12 | 0.16 | 1.38 | 0.88 | 0.16 | AC022690.2 | 0.89 | −1.84 | 0.95 | −1.21 | 2.15 | AC067956.1 | −0.02 | −0.65 | −0.35 | −0.02 | −0.10 |
| AC025034.1 | −0.50 | 0.42 | 0.10 | −0.10 | −0.06 | AL137782.1 | −0.15 | −0.13 | 0.35 | −0.19 | 0.14 | AC027343.2 | −0.11 | −0.40 | −0.50 | 0.13 | 0.11 |
| CADPS2 | −0.34 | 0.18 | 0.46 | −0.09 | 0.13 | AP002884.4 | −0.17 | 0.69 | 0.55 | 0.66 | 0.39 | AC015818.3 | −0.02 | −1.06 | 0.36 | 0.73 | 2.95 |
| RNA5SP211 | −1.09 | 1.20 | −0.24 | 1.16 | −0.67 | RNU6-545P | 0.93 | −0.63 | 1.21 | 1.97 | 0.74 | SIVA1 | 0.00 | 0.00 | −0.14 | 0.05 | −0.15 |
| AP001636.3 | −0.65 | 0.25 | 1.28 | 0.19 | 0.50 | CRTC3-AS1 | 0.17 | −0.70 | 0.06 | 0.08 | 0.49 | LINC01425 | 0.04 | 0.58 | −2.20 | 1.96 | 0.29 |
| MSH2 | 0.23 | −0.14 | −0.12 | −0.14 | 0.05 | AC115618.1 | 0.26 | −0.53 | −0.68 | 0.49 | 1.08 | OR5G4P | −0.11 | −0.78 | −0.87 | −0.26 | −2.38 |
| PROS1 | 0.37 | 0.09 | 0.28 | 0.05 | −0.14 | CLPSL1 | 0.84 | −1.43 | −1.18 | 0.84 | 0.57 | KRT222 | 0.02 | −0.03 | 1.03 | 0.05 | 0.53 |
| KRTAP5-7 | −1.20 | 0.66 | 1.21 | 0.13 | −0.49 | IL20RB-AS1 | 0.18 | 0.30 | 0.42 | −0.02 | 0.02 | IL17B | 0.01 | −0.02 | −0.77 | 1.34 | −0.20 |
| CASP1P2 | 0.69 | −0.43 | −0.66 | −0.17 | −0.19 | AC006349.1 | 0.47 | −0.46 | −1.12 | 0.55 | 1.22 | MTCO2P6 | 0.11 | −0.93 | −0.78 | 0.55 | 0.55 |
| COQ10BP2 | 0.96 | −0.29 | −0.43 | −0.09 | −0.21 | AC069257.2 | 0.41 | 0.07 | −1.40 | −0.90 | −1.61 | AC068298.1 | 0.11 | −0.40 | 0.64 | 1.02 | 0.22 |
| LINC01871 | 1.77 | −0.46 | −1.60 | 0.41 | −0.49 | RNU6-929P | −1.00 | 0.81 | 1.40 | 0.00 | 0.26 | MCCC1-AS1 | 0.01 | 0.00 | 0.00 | 0.21 | −0.08 |
| AL360227.1 | −0.88 | 0.87 | 0.17 | 0.69 | −0.35 | CDH17 | 0.33 | −0.33 | −0.40 | 0.16 | −0.41 | SIDT1-AS1 | −0.02 | 0.49 | 0.11 | −0.92 | −0.89 |
| AL121655.1 | −0.55 | −0.45 | 0.46 | 0.13 | 0.63 | KCNE2 | 0.50 | −1.07 | −1.19 | 1.02 | 0.31 | MIR4673 | 0.04 | 0.63 | −1.53 | 0.88 | −1.40 |
| FRAT2 | 0.33 | 0.20 | −0.25 | 0.24 | −0.33 | AL160394.1 | −0.69 | −1.28 | 0.55 | 0.50 | 0.75 | BANF2 | 0.03 | −0.86 | 1.48 | −1.21 | −0.41 |
| KIAA0319 | −0.50 | 0.45 | 0.96 | 0.38 | 0.31 | AC093829.1 | −0.81 | 1.40 | 2.25 | 1.04 | 0.23 | AL392112.1 | −0.10 | −0.57 | −0.05 | 0.23 | 1.07 |
| ALG1 | 0.32 | −0.20 | −0.39 | 0.07 | 0.16 | RN7SL663P | −0.19 | 0.54 | 0.70 | −0.15 | 0.08 | AC092474.2 | −0.09 | −1.51 | 0.47 | −2.57 | 0.56 |
| AL139008.1 | −0.98 | −0.50 | 0.97 | −0.80 | 0.78 | SNORD81 | −0.47 | −1.36 | −0.32 | 0.22 | 1.81 | PMFBP1 | 0.01 | 0.04 | −0.14 | 0.45 | 0.67 |
| AIRE | −0.75 | −0.30 | −0.02 | −0.26 | −0.20 | RAPSN | 0.18 | 0.08 | −0.11 | 0.21 | −0.08 | NSL1 | 0.00 | 0.01 | 0.23 | −0.15 | 0.13 |
| AGT | −1.04 | −0.18 | −0.87 | −0.12 | −1.38 | RAB39B | −0.34 | −0.23 | 0.29 | −0.45 | 0.66 | SMIM23 | 0.02 | 0.61 | −0.33 | 0.40 | 0.08 |
| AC012312.1 | 1.24 | −0.62 | −0.33 | −0.08 | −0.31 | AC092745.3 | 0.49 | 0.17 | 0.97 | −0.16 | 0.49 | AC093292.1 | −0.11 | 0.01 | 0.54 | −0.75 | −0.89 |
| DYNC2H1 | −0.28 | 0.25 | 0.59 | −0.02 | 0.03 | AC091057.3 | −0.43 | −0.63 | 0.98 | 0.26 | 2.39 | RP11-327I22.6 | −0.11 | −1.22 | 0.03 | 1.75 | 1.09 |
| FCGR3A | 0.84 | −1.19 | −1.10 | −0.45 | −0.64 | SETP1 | 0.97 | −0.54 | 0.60 | 0.06 | −0.93 | AC005019.1 | −0.02 | 0.36 | −0.83 | 1.48 | −1.18 |
| AL353653.1 | 1.13 | −0.76 | −0.20 | −0.39 | −0.18 | LINC02223 | 0.36 | 0.42 | 0.11 | −0.34 | −0.13 | RN7SL214P | −0.11 | −0.27 | 0.53 | −0.48 | −0.34 |
| PPIAP51 | 0.53 | −0.37 | −0.38 | −0.20 | −0.05 | RPS6KA2 | −0.07 | 0.12 | −0.03 | −0.08 | −0.20 | AC002543.1 | 0.01 | 0.38 | −0.16 | 0.11 | 0.02 |
| CWF19L2 | −0.18 | 0.12 | 0.09 | 0.04 | 0.01 | FPGS | 0.10 | −0.18 | −0.56 | 0.18 | −0.01 | AC073387.2 | 0.06 | 0.28 | −2.82 | 1.97 | −1.67 |
| CAPN12 | −0.42 | 0.34 | −0.24 | 0.65 | 0.21 | MED11 | 0.09 | 0.00 | −0.23 | 0.25 | −0.12 | AC022145.2 | −0.04 | 0.65 | 0.03 | 0.02 | −1.13 |
| G31356 | −0.45 | −0.04 | 0.29 | 0.03 | 0.25 | RPL23AP66 | 0.45 | −0.02 | 0.93 | 0.57 | 0.85 | AP001893.2 | −0.04 | −0.31 | 0.79 | 0.17 | 1.54 |
| PDIK1L | 0.36 | −0.07 | 0.20 | 0.08 | −0.07 | AC012557.2 | 0.25 | −0.01 | −0.54 | −0.20 | −0.34 | LINC02440 | 0.11 | 0.94 | −0.57 | 0.32 | −1.68 |
| GOLGA8I | −0.75 | −0.03 | 0.41 | 1.21 | 0.25 | IGFBPL1 | 0.48 | −0.42 | 0.63 | −0.47 | 1.51 | GS1-594A7.3 | 0.11 | −1.16 | −0.23 | 0.30 | −0.42 |
| RNA5SP337 | −1.65 | −0.30 | 0.46 | 0.26 | −0.40 | RP11-87H9.3 | −0.22 | −0.13 | 0.77 | −0.23 | −0.05 | AC016550.3 | −0.09 | 0.00 | −0.50 | −1.28 | −2.05 |
| S100A6 | 0.43 | −0.39 | −0.67 | 0.06 | −0.43 | AP000254.1 | 0.26 | 0.67 | 0.56 | 0.12 | −0.70 | MEP1A | 0.02 | −1.91 | 0.02 | 0.62 | 1.77 |
| RAMACL | 0.45 | −0.28 | −0.66 | −0.32 | −0.42 | AC004699.1 | 0.41 | 0.39 | 1.16 | 0.30 | 0.58 | AP005057.1 | −0.11 | 0.17 | −0.12 | 0.01 | −2.34 |
| COL6A1 | −0.39 | 0.00 | 0.74 | −0.70 | −0.03 | AC023385.1 | 0.18 | −0.59 | −0.76 | −0.07 | 0.24 | AC008742.1 | −0.01 | 0.12 | −0.83 | −0.27 | −0.57 |
| EVI5 | 0.16 | −0.02 | −0.09 | −0.10 | −0.13 | CUBNP2 | 0.81 | −0.86 | −0.49 | 0.93 | 1.41 | AC013733.2 | 0.04 | −0.06 | −0.50 | 1.42 | −0.62 |
| BORCS5 | −0.18 | 0.17 | 0.26 | 0.06 | 0.16 | G29816 | −0.27 | 0.97 | −0.29 | 0.59 | −0.78 | FAM49A | 0.01 | −0.04 | 0.13 | −0.37 | −0.23 |
| CMPK1 | 0.34 | −0.17 | −0.22 | −0.08 | −0.14 | FAM181A | −1.10 | −0.13 | 0.65 | 2.34 | −0.66 | ELOCP4 | −0.11 | 0.51 | −0.12 | 0.16 | −1.81 |
| AKT3-IT1 | −0.70 | 0.48 | 0.71 | 0.01 | −0.13 | GS1-279B7.1 | 0.23 | −0.31 | −0.90 | 0.60 | −0.06 | AC087741.3 | −0.01 | −0.40 | −0.17 | −0.11 | 0.46 |
| KCNJ2 | 0.52 | −0.38 | −0.83 | 0.36 | −0.19 | PDYN-AS1 | 0.81 | −1.73 | −1.61 | 0.37 | −0.40 | AC073311.1 | −0.04 | −1.14 | −0.09 | −0.89 | −0.75 |
| AHNAK2 | −0.33 | 0.38 | 0.27 | 0.19 | −0.05 | ARHGAP23 | 0.08 | 0.10 | −0.36 | 0.16 | −0.14 | AC084880.2 | 0.05 | −0.58 | −1.31 | 0.17 | 0.85 |
| IMMP1LP1 | 0.65 | −0.19 | −0.58 | −0.37 | −0.56 | AC093459.1 | −0.77 | −0.10 | 0.00 | 0.19 | −1.00 | AC016723.1 | −0.03 | −0.49 | −0.68 | 1.45 | 1.05 |
| AC087163.2 | −0.52 | 0.49 | 0.77 | 0.32 | 0.58 | HBQ1 | −0.75 | 0.75 | −0.13 | 0.55 | −2.04 | AC007601.1 | −0.01 | −0.13 | −0.79 | 0.02 | −0.32 |
| AC105430.1 | −1.72 | −1.16 | −0.54 | 0.08 | 1.58 | RPL3P11 | −0.57 | 0.89 | 0.93 | 0.14 | −0.61 | AC011410.1 | −0.10 | −0.74 | 0.87 | −1.65 | −0.01 |
| RNU1-20P | −1.61 | 0.42 | −1.10 | 1.20 | −1.28 | AL512430.4 | 0.63 | −2.57 | 0.15 | −0.84 | 2.17 | AL365500.1 | 0.11 | 0.21 | −0.21 | 0.53 | −0.61 |
| LIN7A | −0.62 | 0.00 | 0.59 | −0.03 | 0.00 | LINC02376 | 0.36 | −0.30 | −0.70 | 0.73 | 0.01 | AL109749.1 | 0.11 | −0.52 | −1.16 | −0.84 | NA |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| SEMA7A | 0.47 | −0.42 | −0.85 | −0.26 | −0.63 | AC241585.1 | 0.30 | −0.81 | −0.88 | −0.69 | −0.06 | RN7SL724P | −0.01 | −0.15 | 0.87 | 0.52 | 0.96 |
| AC093627.6 | −1.05 | 0.30 | −0.08 | −0.09 | −2.32 | RNA5SP273 | −0.97 | 0.10 | −0.67 | 1.49 | −1.37 | RN7SKP81 | 0.11 | −0.67 | −1.36 | 0.92 | 0.05 |
| OGFRL1 | −0.30 | 0.37 | 0.49 | 0.04 | 0.08 | NFKB2 | −0.14 | −0.35 | −0.57 | −0.20 | −0.07 | AC022634.1 | −0.11 | −0.75 | −0.67 | −0.59 | 0.69 |
| COL10A1 | 0.40 | −0.26 | 0.01 | −0.01 | 0.15 | AC022915.3 | 0.56 | −0.99 | 0.05 | −0.98 | −1.21 | AC008072.1 | −0.06 | −0.77 | 1.63 | 1.40 | 1.93 |
| RN7SL606P | −1.30 | −0.11 | 1.40 | 0.01 | −0.09 | GHRL | −0.16 | 0.14 | 0.23 | 0.07 | 0.30 | AC130472.1 | −0.01 | −0.09 | 0.03 | 0.36 | 0.95 |
| GRIK1-AS1 | −1.14 | −0.09 | 1.21 | −0.93 | −0.84 | MRPS25 | 0.08 | −0.11 | −0.12 | 0.12 | 0.24 | AC026726.1 | −0.04 | −0.98 | 0.58 | −1.03 | 0.81 |
| BMS1P9 | −0.91 | 0.39 | 0.64 | 0.27 | 0.33 | SLF2 | 0.06 | 0.00 | 0.18 | −0.10 | 0.11 | BTF3P14 | 0.11 | 0.11 | −0.45 | −0.15 | −1.51 |
| AC027801.2 | −1.18 | 0.84 | 2.21 | 0.47 | 0.67 | AC115837.2 | 0.95 | −2.54 | −0.02 | 0.06 | 3.71 | HNF4G | −0.02 | −1.45 | −1.25 | −0.16 | −0.62 |
| OR1L6 | −0.65 | 0.64 | 0.24 | 0.04 | −0.59 | DGKE | 0.08 | 0.09 | 0.05 | 0.19 | 0.13 | AC097521.1 | 0.05 | −0.71 | −1.94 | 0.55 | −1.92 |
| FAM90A25P | −1.31 | 1.07 | 2.28 | 0.57 | 0.59 | G40985 | −0.20 | 0.22 | 0.59 | −0.20 | −0.05 | RN7SL53P | −0.11 | −0.34 | 0.11 | 1.27 | −0.24 |
| LINC02504 | −1.53 | 0.70 | 0.61 | 1.29 | −0.13 | OR7E25P | −0.34 | −0.14 | −0.17 | −0.21 | 0.53 | LINC00443 | −0.04 | −2.63 | 1.89 | −1.89 | 2.69 |
| RAPGEF3 | −0.55 | 0.18 | 0.33 | 0.25 | 0.04 | SMIM32 | 0.20 | −0.35 | 0.63 | −0.30 | 0.26 | AC016571.1 | 0.01 | −0.25 | 0.04 | −0.02 | 0.51 |
| G37033 | −0.68 | −0.03 | 0.60 | −0.67 | −0.16 | AC017006.2 | 0.25 | −0.33 | 0.41 | 0.49 | 0.83 | RNU6-570P | −0.02 | −1.81 | 0.98 | −1.20 | 1.25 |
| MRO | −0.94 | 0.17 | 1.09 | 0.09 | 0.34 | CRYGN | −0.44 | −0.69 | −0.55 | 0.20 | −0.49 | MYH7 | −0.02 | −0.70 | −0.60 | 0.96 | −0.39 |
| SERHL | −0.75 | 0.28 | 0.27 | 0.38 | 0.13 | AL359636.1 | −0.36 | 0.44 | 1.12 | −0.68 | 0.76 | AC139769.2 | −0.01 | 0.37 | 0.60 | −0.22 | 0.14 |
| AL513366.1 | −0.37 | 0.01 | 0.32 | −0.22 | −0.05 | AL929472.4 | 0.31 | −0.94 | −0.98 | −0.23 | −0.55 | C17orf64 | −0.02 | −1.01 | 0.87 | −0.06 | 0.54 |
| PKMP1 | 1.17 | −1.47 | −3.14 | 0.31 | −1.78 | PELP1 | −0.11 | −0.18 | −0.24 | 0.18 | 0.20 | LINC02426 | −0.02 | −0.50 | −2.45 | 0.74 | −1.88 |
| DM1-AS | −0.51 | −0.18 | 0.19 | −0.20 | 0.06 | AC006518.1 | 0.30 | 0.33 | 0.51 | 0.34 | 0.65 | AP002433.2 | −0.01 | −0.26 | 0.48 | −0.07 | 0.39 |
| DHODH | −0.25 | −0.20 | 0.01 | 0.10 | 0.40 | AC069235.1 | −0.70 | 0.78 | −0.42 | 0.65 | 0.62 | AC145285.4 | −0.03 | 0.51 | 0.68 | −1.18 | 0.21 |
| GZF1 | 0.23 | −0.16 | −0.20 | −0.08 | 0.01 | SUGP1 | −0.08 | 0.08 | −0.09 | 0.12 | 0.04 | AC068707.1 | 0.11 | 0.02 | −0.41 | 2.07 | −1.23 |
| AC137630.5 | −0.73 | 0.37 | 1.60 | −0.09 | 0.23 | GOLGA8J | −0.70 | 0.04 | 2.02 | −0.93 | 1.29 | AC091691.2 | −0.09 | −0.13 | −0.87 | −0.75 | −3.01 |
| AL162586.1 | −0.45 | 0.19 | 0.48 | −0.08 | −0.12 | AC016769.3 | −0.76 | −0.49 | 0.45 | −0.21 | 1.11 | AC005828.4 | −0.01 | −0.10 | 0.21 | −0.10 | 0.27 |
| AC024257.3 | −0.41 | −0.09 | 0.45 | 0.01 | 0.36 | S1PR3 | −0.13 | −0.10 | 0.23 | −0.30 | 0.09 | PGAM1P12 | 0.10 | −0.38 | −1.51 | 1.74 | −0.11 |
| AC083837.1 | 0.64 | −1.10 | −0.30 | −0.02 | 0.23 | AL139348.1 | 0.62 | −1.84 | −1.68 | 0.95 | 1.98 | NANOGP10 | 0.10 | −0.19 | −0.32 | −0.04 | −1.69 |
| AP003096.1 | −0.40 | 0.06 | 0.10 | −0.15 | 0.06 | RNU6-943P | 0.64 | 1.16 | 4.36 | 0.01 | 1.22 | OR6U2P | −0.02 | −0.07 | 0.44 | 0.54 | 0.63 |
| RNA5SP350 | −1.30 | 0.24 | 0.00 | 0.47 | −0.22 | BX004987.1 | 0.32 | −0.88 | −0.79 | 0.41 | 0.59 | AL731537.2 | 0.07 | −0.83 | 1.21 | 0.29 | 1.42 |
| MCPH1-AS1 | −0.35 | 0.08 | 0.49 | 0.00 | 0.09 | AL589647.1 | −0.95 | 0.02 | 0.58 | 0.11 | 1.04 | PRR27 | 0.02 | −0.09 | −0.68 | 0.30 | −1.18 |
| PLEKHA7 | −0.25 | 0.29 | 0.03 | 0.20 | 0.22 | AC078923.1 | 0.29 | −0.18 | 0.40 | 0.24 | 0.88 | RN7SKP19 | −0.10 | 0.45 | −0.02 | 1.83 | −0.26 |
| AP5Z1 | −0.32 | −0.10 | −0.16 | 0.06 | 0.04 | AP001117.1 | −0.87 | −0.40 | 0.39 | −0.89 | −1.98 | RSPH3 | 0.00 | 0.10 | −0.12 | 0.18 | −0.13 |
| NDUFB7 | 0.21 | −0.02 | −0.21 | 0.01 | −0.27 | SPDYE6 | −0.14 | 0.15 | 0.07 | 0.50 | 0.58 | KRTAP13-1 | −0.07 | 0.09 | −0.53 | 0.32 | −0.84 |
| AC097518.1 | −1.64 | −0.52 | 1.57 | −0.29 | 2.05 | OR5AM1P | 0.64 | −0.56 | −1.63 | 1.34 | −0.15 | AC234782.4 | 0.02 | −0.21 | −0.89 | −1.16 | −1.83 |
| AC012617.1 | −0.89 | 1.13 | 0.79 | 0.56 | −0.30 | MAGEB16 | −0.72 | −0.13 | −1.87 | 1.61 | −0.43 | AC018685.1 | 0.10 | −1.03 | −0.52 | −0.29 | −1.30 |
| ANTXRLP1 | −0.89 | −0.82 | 0.24 | −0.49 | 0.98 | RN7SL505P | 0.27 | −0.15 | 0.26 | 0.14 | 0.83 | AP003100.2 | 0.03 | −0.70 | 0.03 | −0.71 | −0.53 |
| AC005253.1 | −0.62 | 0.08 | 0.01 | 0.72 | 0.49 | AC104260.3 | −0.29 | 0.21 | 0.06 | 0.34 | −0.41 | AL161640.1 | −0.10 | 0.05 | 0.38 | 1.15 | −0.92 |
| AC103988.1 | −0.46 | 0.16 | 0.25 | 0.44 | 0.37 | AC127496.1 | 0.19 | 0.31 | −0.16 | 0.23 | −0.26 | AJ009632.2 | −0.01 | −0.28 | 0.13 | 0.35 | 0.27 |
| AL078590.1 | −0.96 | 0.27 | 0.30 | 0.11 | −0.42 | HSPA2 | 0.12 | 0.60 | 0.31 | 0.29 | −0.57 | RN7SL535P | −0.01 | −0.31 | −0.12 | −0.10 | 0.20 |
| AC006449.2 | −0.53 | 0.34 | 0.60 | 0.17 | 0.32 | AC011899.1 | −0.37 | 0.03 | −0.77 | 0.35 | −1.32 | RNU4-90P | 0.10 | −0.44 | −0.15 | 0.19 | 1.05 |
| AL031009.1 | 0.53 | −0.14 | −0.27 | 0.10 | 0.17 | RNU6-623P | −0.38 | −1.04 | −1.13 | −0.54 | −0.51 | AL445623.2 | −0.01 | −0.27 | −2.10 | 0.36 | −0.69 |
| IL21R | 0.77 | −1.43 | −0.68 | −0.88 | 0.08 | AC007126.1 | −0.36 | −0.26 | −1.08 | 0.59 | −0.45 | OR4A48P | −0.10 | 0.19 | NA | −1.04 | −0.85 |
| AC131391.1 | 0.50 | −0.37 | 0.03 | −0.04 | 0.37 | AC138956.1 | 0.22 | −0.09 | 0.23 | −0.06 | −0.09 | AC114322.1 | 0.10 | 0.15 | 1.09 | 1.77 | 1.81 |
| G6339 | −1.41 | 1.80 | 1.00 | 1.29 | −0.63 | LINC02506 | −0.59 | 0.84 | −0.68 | −0.30 | −0.78 | AL138900.3 | −0.06 | −0.21 | −0.02 | −1.31 | −0.29 |
| AC124784.1 | 1.13 | −0.67 | −1.06 | 0.01 | −0.48 | AC104126.1 | 0.19 | −0.16 | −0.15 | −0.05 | −0.21 | AC245128.1 | 0.10 | −1.13 | −0.47 | −0.10 | −0.10 |
| CXCL2 | 0.83 | −1.05 | −2.36 | −0.74 | −0.98 | OPTN | −0.08 | 0.11 | −0.09 | 0.04 | −0.16 | AL606500.1 | 0.03 | 0.47 | 0.84 | −0.42 | 0.36 |
| AC006160.1 | 0.70 | −0.37 | 0.81 | −0.24 | 0.58 | RN7SKP285 | −0.27 | 0.28 | 0.98 | 0.30 | −0.06 | AP000402.1 | 0.10 | −0.69 | −0.43 | 0.37 | 1.67 |
| AC079305.1 | −0.61 | 0.38 | −0.40 | 0.33 | −0.64 | AC131235.2 | −0.73 | −1.48 | 1.01 | −0.86 | 2.33 | MAP2 | 0.00 | 0.39 | 0.06 | 0.18 | −0.41 |
| FAM193A | −0.20 | −0.03 | 0.01 | 0.00 | 0.12 | SNX19P2 | −0.63 | −0.51 | 0.19 | 0.18 | −0.10 | AC112482.1 | 0.10 | −0.21 | −1.09 | 0.03 | −0.60 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC090948.2 | 0.46 | −0.57 | −0.43 | −0.58 | −0.14 | SMPDL3B | −0.21 | −0.07 | 0.13 | 0.02 | 0.17 | AC073987.1 | 0.10 | −0.16 | 0.21 | −1.20 | −2.02 |
| AC112236.2 | −0.88 | 0.55 | 1.36 | 0.49 | 0.80 | PLA2G1B | 0.65 | −2.07 | −0.10 | −0.68 | 1.77 | AC012362.1 | −0.04 | 0.61 | −1.82 | −0.17 | −1.91 |
| SAMD4B | 0.11 | 0.00 | −0.11 | −0.10 | −0.18 | SNORD114-9 | 0.86 | −0.61 | 0.58 | −1.54 | 0.36 | AC005746.2 | −0.01 | 0.81 | 0.54 | 0.23 | 0.00 |
| AL034349.1 | 0.58 | −0.60 | −0.67 | 0.13 | 0.02 | AL136979.1 | 0.21 | −0.12 | 0.22 | −0.03 | 0.21 | AC018865.1 | 0.10 | 0.12 | −0.93 | −0.10 | −2.27 |
| ASGR2 | −0.51 | 0.29 | 0.84 | 0.26 | 0.56 | RGPD8 | 0.08 | −0.12 | 0.00 | 0.11 | 0.55 | AL669914.1 | 0.03 | −0.05 | −0.57 | 0.89 | −0.63 |
| APOL1 | 0.66 | −1.24 | −1.13 | −0.67 | 0.10 | AC011840.5 | −0.77 | 0.00 | 0.23 | 1.24 | 1.26 | MED30 | 0.00 | 0.06 | 0.30 | −0.21 | 0.03 |
| ITGA2B | −0.62 | 0.05 | −1.10 | 0.14 | −1.00 | RNU6-125P | −0.16 | 0.70 | −0.08 | 0.43 | −0.24 | AL135938.1 | −0.10 | −0.40 | −1.09 | −0.42 | NA |
| CHRND | −0.72 | 0.59 | 0.60 | 0.60 | 0.55 | AC012447.1 | −0.30 | 0.33 | 0.46 | −0.04 | −0.59 | PPP2R1B | 0.00 | 0.08 | −0.21 | −0.01 | −0.15 |
| RPL17P11 | 1.03 | 0.00 | −0.32 | 0.84 | 0.37 | AL445669.2 | −0.62 | 0.95 | −0.13 | −0.84 | 0.44 | AC012354.1 | −0.03 | −2.45 | −0.03 | −0.77 | 0.28 |
| LAMA5-AS1 | −0.73 | 0.18 | −0.13 | 0.44 | 0.21 | AL109741.1 | −0.28 | −0.55 | 1.06 | −0.54 | 0.09 | AC048344.1 | −0.07 | −1.03 | −0.34 | 1.72 | 0.84 |
| RNU6-1156P | 1.82 | −1.70 | 0.42 | −0.23 | 2.83 | NPM1P33 | 0.68 | −0.87 | −0.63 | −0.12 | 0.29 | AC024610.2 | −0.01 | 0.10 | −1.74 | 0.37 | −0.62 |
| AC005343.1 | 0.32 | −0.29 | −0.23 | −0.05 | −0.05 | AC084882.1 | −0.39 | 0.77 | 0.41 | 1.79 | 1.24 | AC124045.1 | −0.01 | 0.20 | 0.04 | 0.09 | 0.00 |
| IL22 | 1.44 | −0.84 | −4.62 | 0.07 | −3.81 | PAX2 | −0.40 | 0.43 | −0.45 | 0.45 | −0.84 | SRY | 0.01 | −0.17 | 0.23 | 0.22 | −0.10 |
| AL031777.3 | 1.20 | −1.50 | −2.36 | −1.13 | −2.27 | CASC20 | −0.71 | 1.27 | 1.47 | 0.84 | 0.23 | AC003687.1 | 0.10 | 0.19 | −0.55 | 0.74 | 1.07 |
| LARP4P | 0.46 | 0.02 | −0.19 | 0.09 | −0.07 | G33789 | 0.19 | 0.13 | −0.96 | 0.76 | −0.40 | IGLV3-30 | −0.10 | −0.59 | NA | −0.42 | −0.62 |
| CCNJL | 0.54 | −0.42 | −1.15 | 0.08 | −0.24 | SCARNA24 | 0.23 | −0.32 | 0.09 | 0.28 | 0.06 | AC108082.1 | 0.10 | −0.11 | −0.90 | 1.97 | −0.09 |
| ASPN | 0.41 | −0.13 | −0.10 | −0.15 | −0.44 | AC003989.2 | −0.26 | 0.34 | 0.55 | 0.18 | 0.09 | AL117378.1 | 0.03 | 1.08 | −0.83 | 0.26 | −1.33 |
| AC245187.2 | −1.83 | −0.46 | 2.38 | −1.88 | 1.10 | CLLU1 | 0.37 | −0.02 | −0.61 | 0.39 | −1.14 | CERNA3 | 0.03 | 0.31 | −0.04 | −0.06 | 0.06 |
| G24400 | −0.63 | 0.05 | 0.55 | −0.09 | 0.08 | OR51L1 | −0.41 | −0.12 | −0.35 | −0.21 | −0.84 | AC104564.1 | −0.01 | −0.67 | 0.33 | −0.13 | 0.75 |
| OR52R1 | 1.83 | −0.68 | −3.34 | 0.33 | −2.66 | LAT | 0.17 | −0.27 | −0.12 | 0.16 | −0.04 | LINC02312 | 0.02 | 0.16 | 0.17 | 0.76 | 0.35 |
| AFDN | −0.28 | 0.23 | −0.01 | 0.06 | −0.13 | PROZ | 0.21 | −0.01 | 0.01 | 0.06 | 0.10 | AC016769.4 | −0.10 | 0.36 | −1.86 | 0.83 | 1.08 |
| FBXO41 | −0.35 | −0.16 | 0.02 | 0.14 | 0.37 | BEND4 | −0.32 | −0.75 | −0.21 | 0.78 | 0.79 | FAM209A | −0.01 | 0.03 | 0.03 | 0.56 | −0.61 |
| AC135584.1 | −1.00 | −0.49 | 1.75 | −0.73 | −0.83 | OR11H6 | 0.82 | −0.51 | −0.16 | 1.46 | 0.58 | RAET1K | 0.03 | −0.21 | −0.62 | 0.25 | −1.51 |
| AC074043.1 | −0.84 | 0.23 | 1.35 | −0.17 | 0.25 | AL669831.5 | −0.09 | −0.05 | 0.13 | −0.20 | −0.13 | IGSF21 | 0.01 | −0.19 | −0.52 | −0.38 | 0.17 |
| AC025219.1 | −1.21 | 0.04 | 0.40 | 0.82 | 2.24 | AC068870.3 | 0.22 | 0.23 | 0.01 | 0.06 | −0.63 | AC078886.1 | −0.02 | 0.22 | 1.17 | −0.08 | 0.80 |
| HOXA1 | 0.47 | −0.19 | −0.61 | 0.31 | −0.06 | LINC02455 | −0.52 | 0.38 | −1.04 | 0.03 | −2.27 | AL512637.2 | −0.10 | −0.45 | −0.30 | 0.24 | 0.92 |
| RNU6-98P | −1.70 | 0.42 | −0.45 | 1.23 | −1.46 | BX640514.2 | −0.28 | −0.75 | 1.21 | 0.19 | 0.32 | AP000936.2 | −0.01 | −0.65 | −0.76 | −0.26 | 0.02 |
| SPINK9 | 0.85 | 0.14 | −0.21 | 0.12 | −1.12 | AL513365.2 | −0.10 | −0.05 | −0.19 | 0.12 | −0.03 | AC018845.1 | −0.09 | 0.50 | −0.77 | 2.66 | −0.17 |
| PPIL3 | 0.22 | −0.05 | 0.07 | −0.08 | 0.07 | G4736 | −0.61 | −0.17 | −0.37 | −0.48 | −1.74 | C18orf65 | −0.01 | −0.69 | −0.29 | −0.51 | −0.52 |
| CLASP2 | 0.16 | 0.00 | −0.21 | 0.05 | −0.08 | AC093909.3 | 0.60 | −1.53 | −1.82 | 0.99 | −0.94 | NEURL2 | 0.01 | −0.07 | 0.08 | 0.19 | 0.42 |
| PRKAB1 | 0.15 | 0.04 | −0.18 | −0.02 | −0.17 | AL590677.1 | −0.86 | 0.71 | 0.84 | 0.40 | −0.06 | LINC02032 | −0.10 | −0.17 | −1.66 | 1.29 | −1.91 |
| FAM214A | −0.25 | 0.37 | 0.37 | 0.30 | −0.02 | NPM1P4 | 0.74 | −1.32 | −1.11 | −0.66 | −1.03 | RNU7-20P | 0.04 | 0.15 | −1.91 | 0.46 | −1.80 |
| CBR3-AS1 | −0.34 | 0.30 | 0.26 | 0.25 | 0.13 | ITM2BP1 | 0.31 | 0.05 | −0.38 | −0.13 | −0.56 | RPL22P8 | 0.02 | −0.75 | −1.79 | −0.83 | −0.78 |
| GAA | −0.30 | 0.21 | 0.04 | 0.24 | −0.01 | G356 | −0.13 | 0.21 | 0.59 | −0.23 | −0.07 | RN7SKP254 | 0.06 | 1.56 | −1.04 | 1.62 | −1.49 |
| RN7SL389P | −1.10 | 0.05 | 0.39 | 0.88 | 0.56 | AC095038.1 | −0.55 | −0.26 | 0.40 | 1.09 | 0.03 | SLC25A5P8 | −0.10 | 0.28 | −0.04 | −0.74 | −1.01 |
| RPS17P1 | −1.10 | 0.84 | 2.76 | 1.05 | 0.79 | GPR45 | −0.37 | −0.50 | −0.70 | 0.53 | 0.92 | AC116003.3 | 0.10 | −0.12 | 0.14 | 0.46 | 0.88 |
| EPHA4 | 0.31 | 0.14 | −0.11 | 0.08 | 0.07 | AC120349.2 | 0.28 | −0.62 | 0.42 | −0.33 | −0.07 | ASB17 | −0.06 | 0.36 | −1.71 | 0.62 | −0.92 |
| AC133644.1 | 1.53 | −1.20 | −0.36 | −0.49 | −0.39 | AC141586.4 | −0.20 | −0.64 | 0.24 | −0.34 | 0.32 | RNU6-909P | 0.10 | −0.75 | 0.23 | −0.30 | 0.87 |
| IL1RAPL2 | −0.85 | 0.78 | 0.76 | 0.60 | 0.56 | AC110794.1 | −1.22 | 0.11 | −0.36 | 0.80 | 0.39 | RPS27AP3 | −0.01 | 0.00 | −1.17 | 0.11 | −0.54 |
| AL353795.3 | −0.30 | 0.22 | 0.49 | −0.16 | 0.47 | ACTG1P22 | −0.44 | 1.06 | −0.98 | −0.36 | −1.15 | AL008719.1 | 0.10 | 0.30 | −0.03 | −1.31 | −3.05 |
| AL356218.1 | −1.42 | −0.61 | 2.70 | 0.32 | 0.97 | SNRPEP8 | −0.76 | −0.19 | −1.97 | 1.06 | −1.02 | MT1L | −0.01 | −0.19 | 0.51 | −0.42 | 0.26 |
| AC020910.5 | −0.63 | 0.30 | 0.96 | −0.52 | −0.11 | CYCSP28 | 0.36 | −0.74 | −0.40 | 0.20 | 0.09 | AP001970.1 | 0.01 | −0.51 | 0.47 | −0.20 | 0.30 |
| OSBPL7 | −0.46 | −0.16 | 0.04 | 0.02 | 0.05 | AC109335.1 | −0.60 | −0.62 | −0.47 | 0.15 | −0.57 | AC022239.1 | −0.02 | −1.35 | −0.04 | 0.23 | 1.78 |
| NAP1L6 | −1.11 | 0.77 | −0.57 | 0.56 | −0.37 | AL357153.2 | −0.37 | 0.17 | −0.14 | −0.64 | −0.59 | AMBRA1 | 0.00 | −0.05 | −0.10 | 0.02 | 0.07 |
| PIN4 | 0.24 | −0.19 | 0.18 | −0.41 | −0.02 | APOLD1 | −0.13 | −0.38 | 0.17 | −0.46 | −0.28 | RPL17P22 | −0.02 | −0.15 | −0.23 | 0.12 | 0.11 |
| LINC00173 | −0.60 | 0.27 | 0.27 | 0.52 | 0.60 | KCTD9P3 | −0.58 | 0.68 | −1.22 | 0.39 | −0.36 | AC004066.2 | −0.02 | −0.56 | −0.13 | −0.17 | 0.11 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| EDRF1 | 0.21 | −0.18 | −0.10 | −0.01 | 0.09 | PEX10 | 0.08 | 0.08 | −0.17 | 0.18 | 0.09 | IQCF5-AS1 | −0.05 | 0.08 | 0.51 | −0.79 | −0.57 |
| SNORD105 | −0.72 | 0.23 | 0.22 | 0.05 | −0.69 | AC083864.4 | −0.44 | −0.34 | 0.87 | −1.50 | −0.24 | GPR33 | 0.04 | −0.60 | 0.76 | 0.70 | 0.75 |
| LINC01004 | 0.37 | −0.15 | −0.14 | 0.06 | −0.13 | AC239799.1 | 0.16 | 0.19 | 0.62 | −0.09 | 0.11 | AC130456.1 | −0.10 | −0.93 | −0.99 | −1.26 | −0.76 |
| RPL27AP8 | 1.61 | −1.41 | −1.28 | 0.24 | 0.21 | BAP1 | 0.06 | −0.21 | −0.55 | 0.03 | −0.04 | AC009313.2 | 0.03 | −1.64 | −1.10 | −0.24 | 1.01 |
| ERRFI1 | 0.37 | −0.06 | −0.40 | −0.17 | −0.61 | AL136099.1 | −0.63 | −0.40 | −0.84 | −0.26 | 0.04 | AC120036.5 | −0.06 | 0.30 | −0.84 | −0.47 | −1.20 |
| HGSNAT | −0.19 | 0.23 | 0.18 | 0.07 | −0.04 | LINC01823 | 0.49 | −0.03 | −1.36 | 0.14 | −1.66 | RN7SL169P | 0.02 | −0.19 | −1.12 | 0.43 | −0.79 |
| RN7SL377P | −1.05 | −0.22 | 1.46 | 0.33 | 0.87 | MTCYBP32 | 0.17 | 0.03 | 0.41 | −0.18 | −0.06 | PVALB | −0.05 | −0.79 | −0.51 | −0.72 | −1.08 |
| PAX8-AS1 | −0.29 | 0.13 | 0.63 | 0.13 | 0.49 | MIR548Q | 0.51 | −0.88 | 1.07 | −0.20 | 0.03 | IGF2-AS | −0.04 | 1.31 | −1.02 | 0.14 | −2.95 |
| AL356608.1 | −1.03 | 0.70 | 0.11 | 0.32 | 0.61 | RN7SL605P | −0.80 | −0.57 | 0.58 | −0.47 | 0.49 | OR5J7P | 0.10 | −0.43 | −0.32 | 0.72 | 0.91 |
| FAM126B | 0.18 | −0.03 | 0.06 | 0.01 | −0.02 | NSUN5P2 | −0.19 | −0.11 | 0.88 | −0.12 | 0.95 | MYO16-AS2 | 0.06 | 0.42 | 0.76 | −1.65 | −2.01 |
| DEFB109D | −1.16 | 1.29 | 0.78 | 0.20 | 0.93 | AP002856.2 | 1.02 | 1.02 | 0.59 | −1.37 | −0.92 | RNU7-134P | 0.04 | −0.87 | 0.83 | 0.17 | 0.80 |
| AC008013.3 | −0.97 | 0.09 | −0.73 | 0.10 | −0.05 | PABPC1P2 | −0.44 | −1.30 | −1.09 | −0.27 | 0.19 | AP000720.2 | 0.02 | −0.45 | 0.25 | −0.30 | 0.27 |
| ADPRHL1 | −0.35 | 0.00 | −0.18 | −0.15 | −0.07 | C14orf178 | −0.73 | −0.43 | 1.02 | 0.21 | −0.58 | GAPDHP64 | 0.04 | 0.22 | −2.41 | 1.13 | −1.19 |
| DCLK2 | −0.41 | 0.06 | 0.83 | −0.26 | 0.44 | AL359878.2 | 0.28 | −0.16 | −1.40 | −0.46 | −0.37 | G10019 | −0.02 | 0.19 | 4.60 | −0.45 | 0.68 |
| AC023830.3 | −0.42 | 0.13 | 0.46 | −0.04 | 0.22 | HUS1B | 0.15 | 0.20 | −0.50 | 0.30 | −0.42 | AC022106.1 | 0.10 | −1.34 | 1.40 | −0.36 | 1.76 |
| AL355987.4 | −0.30 | −0.37 | 0.36 | 0.11 | 0.61 | MIR4796 | −0.37 | 0.78 | −0.10 | 0.35 | −1.11 | MTHFD2P6 | −0.01 | −0.13 | −0.64 | −0.55 | −1.15 |
| AL022329.1 | −1.46 | 0.94 | 3.23 | 0.57 | 0.82 | RNU6-1086P | −0.65 | 0.93 | −0.19 | 1.37 | 0.37 | IGKV3-11 | 0.03 | 0.26 | 3.13 | 1.74 | 1.19 |
| AC099343.2 | 0.52 | 0.00 | −0.52 | −0.08 | −0.70 | LINC01198 | −0.34 | 0.38 | −1.29 | 0.97 | −0.57 | AC003005.2 | 0.02 | 0.18 | 0.06 | 0.63 | 0.70 |
| AP000322.1 | −1.50 | 0.91 | 1.85 | 0.03 | −0.05 | AC026700.1 | −0.42 | 0.23 | −0.93 | −0.22 | −0.70 | LINC00313 | 0.02 | 1.52 | −0.45 | 0.54 | −1.25 |
| MIR4705 | −1.52 | 0.96 | 1.87 | −1.27 | 0.76 | SETD7 | −0.09 | 0.12 | 0.34 | −0.05 | −0.08 | AL772337.2 | −0.10 | −0.81 | 0.29 | 0.00 | 1.34 |
| MYRFL | −0.62 | 0.16 | 0.35 | 0.31 | 0.11 | LINC02601 | −0.94 | 0.36 | 0.81 | 1.38 | 0.76 | ACTG1P19 | 0.05 | −0.34 | −0.88 | 1.28 | −0.34 |
| ITGB1 | 0.42 | −0.39 | −0.35 | −0.45 | −0.24 | AL024497.1 | −0.61 | −0.03 | −2.12 | 0.82 | −3.12 | AC093430.1 | 0.02 | 0.18 | −0.77 | 0.90 | −0.36 |
| AC112206.3 | −1.11 | −0.53 | 0.86 | 1.57 | 2.14 | PRPF18 | 0.06 | 0.12 | 0.14 | −0.09 | −0.02 | RN7SL660P | 0.02 | −0.48 | 0.68 | 0.07 | 0.89 |
| KIR2DL4 | 1.70 | −1.43 | −3.79 | 0.22 | −2.37 | AL360270.2 | 0.20 | −0.46 | −0.79 | −0.28 | −0.45 | AC132825.1 | −0.03 | −2.40 | 1.44 | 0.17 | 1.99 |
| SLC25A2 | −0.74 | −0.36 | 0.83 | 0.27 | 0.94 | RNA5SP247 | 0.31 | −0.32 | −0.08 | −0.39 | −0.20 | AL137002.2 | 0.01 | 0.05 | −0.58 | 1.68 | 0.50 |
| AC104211.1 | −1.69 | 1.00 | 1.80 | 1.64 | 0.04 | AL591845.1 | −0.15 | 0.58 | −0.32 | −0.14 | −0.72 | AC104777.3 | −0.04 | 0.28 | −0.12 | 0.79 | −0.84 |
| G41741 | 0.69 | −0.07 | 1.00 | −0.69 | −0.12 | AC022069.1 | 0.25 | −0.08 | 0.25 | −0.50 | −0.49 | AC239727.1 | −0.04 | 0.65 | −0.10 | 0.24 | −1.76 |
| FBXW4P1 | −0.46 | 0.05 | 0.12 | 0.26 | 0.41 | RPS20P2 | −0.49 | −1.18 | 0.57 | −0.80 | 0.23 | BPIFB5P | −0.03 | 0.31 | 0.43 | 0.84 | 0.29 |
| RNF219 | 0.25 | −0.17 | −0.18 | −0.16 | −0.24 | C17orf82 | −0.46 | −0.14 | 0.09 | −0.09 | −0.89 | BOLA2P1 | 0.10 | −0.22 | −0.14 | −0.31 | −0.67 |
| AC239800.1 | −0.88 | 0.36 | 1.35 | 0.21 | 0.90 | G10667 | −0.86 | 0.02 | 0.98 | 0.82 | 1.15 | DUTP5 | 0.10 | −0.43 | −0.43 | 0.18 | −0.22 |
| SNRPGP18 | 0.74 | −1.04 | 0.17 | −0.24 | 0.56 | CPNE8-AS1 | −0.31 | −0.65 | −0.06 | −0.79 | 0.00 | AC108174.1 | 0.03 | 0.20 | −0.26 | 0.18 | −0.44 |
| CLUL1 | −0.77 | −0.43 | 1.09 | −0.30 | 1.00 | RIN3 | 0.08 | −0.11 | −0.06 | −0.01 | −0.09 | LINC00502 | −0.03 | −1.33 | −0.40 | −0.27 | 1.30 |
| KIF16B | −0.16 | 0.12 | −0.06 | 0.06 | −0.08 | AC008126.1 | 0.41 | −0.44 | 0.44 | −0.25 | −0.87 | KRT19P1 | −0.09 | 0.28 | −0.41 | 0.31 | −0.99 |
| HIPK1-AS1 | −0.47 | −0.29 | 0.02 | −0.06 | 0.46 | AP000265.1 | −0.37 | 1.03 | 0.00 | 0.06 | −0.51 | BRD7P4 | −0.01 | 0.05 | 0.31 | 0.18 | 0.25 |
| AC022493.2 | 0.66 | −0.45 | 0.01 | −0.25 | −0.03 | OR51G2 | 0.42 | −0.56 | −1.13 | 0.43 | −0.30 | AC091893.1 | −0.09 | −0.59 | 0.18 | −0.73 | 3.35 |
| CBY1 | −0.32 | 0.41 | 0.23 | 0.47 | 0.12 | CLRN1-AS1 | −0.64 | −1.81 | 0.62 | 0.18 | 0.94 | AL390237.1 | −0.02 | 0.32 | −0.60 | −0.20 | −1.67 |
| RPS14P4 | 0.83 | −0.61 | −1.59 | −0.79 | −1.03 | SPOCK3 | −0.28 | 0.43 | −0.16 | 0.43 | −0.81 | AC021439.1 | 0.04 | −0.29 | −1.37 | 0.66 | −1.21 |
| AC025031.5 | −0.35 | 0.11 | 0.35 | 0.24 | 0.30 | SNORD46 | −0.16 | 0.37 | 0.53 | 0.32 | −0.47 | AC069218.2 | −0.09 | −0.39 | −0.05 | −1.31 | 0.59 |
| BRD2 | 0.15 | −0.14 | −0.35 | −0.06 | −0.10 | OSBPL2 | −0.07 | 0.23 | −0.08 | 0.16 | −0.09 | AC130710.1 | 0.07 | −0.41 | −0.91 | 1.85 | 1.06 |
| AL121772.1 | −0.65 | 0.33 | 0.68 | 0.58 | 0.78 | AC010884.1 | −0.31 | −0.32 | −1.08 | 0.12 | 0.30 | LINC00415 | 0.06 | −0.50 | −0.13 | 0.64 | −1.83 |
| APLNR | 0.59 | −0.18 | 1.00 | −0.28 | 0.06 | AC010285.2 | −0.31 | 0.14 | −1.16 | −0.23 | −0.51 | RNU1-133P | −0.09 | 0.35 | 0.27 | 1.07 | −1.06 |
| G8321 | −1.22 | 1.21 | 1.41 | −0.06 | −0.33 | METTL15 | 0.07 | −0.02 | 0.02 | −0.13 | −0.10 | G40091 | −0.02 | −0.47 | 0.21 | 0.73 | 0.28 |
| CXorf38 | 0.20 | −0.15 | −0.38 | 0.05 | −0.09 | NUP50-DT | 0.09 | −0.17 | −0.27 | 0.09 | 0.23 | AL359535.1 | −0.05 | 0.95 | −2.32 | 1.35 | −2.43 |
| SBK1 | −0.52 | 0.29 | 0.58 | −0.07 | −0.02 | BPIFA4P | −0.62 | −0.18 | −0.90 | 0.44 | −0.94 | AP001767.1 | −0.01 | −0.40 | −0.40 | 0.28 | 0.35 |
| IL20RA | −0.44 | 0.70 | 0.69 | 0.75 | 0.17 | RNA5SP84 | −0.69 | −0.46 | 0.39 | 1.68 | 2.49 | LINC02123 | 0.09 | −0.25 | 0.47 | 1.09 | 0.04 |
| FLJ37453 | −0.35 | 0.15 | 0.42 | 0.22 | 0.37 | BTG4 | −0.73 | −0.28 | 0.04 | −0.60 | 1.25 | AL138693.1 | −0.02 | −0.96 | −1.05 | −0.37 | 0.86 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| PTPRK | 0.20 | 0.14 | 0.09 | 0.03 | −0.17 | HNRNPA1P67 | 0.64 | −0.73 | −1.73 | −0.26 | 0.22 | EN2 | −0.01 | 0.28 | −0.71 | 0.31 | 0.14 |
| AP001893.1 | 0.95 | −0.50 | −1.04 | 0.24 | −0.25 | RPS29P17 | −0.51 | −1.21 | 2.47 | −1.56 | 0.91 | LRRC30 | 0.09 | −0.55 | −1.16 | 1.11 | −0.38 |
| AL035634.1 | 0.71 | 0.06 | −0.94 | −0.30 | −0.81 | SNX18P1Y | 0.27 | −0.94 | 0.78 | 0.38 | 1.87 | AL353692.2 | 0.09 | −0.60 | −0.25 | 0.05 | 0.37 |
| AL136531.3 | 0.58 | 0.30 | −0.82 | −0.02 | −0.69 | FAM47DP | −0.73 | 0.51 | 0.87 | 0.20 | −0.05 | MYCNUT | −0.04 | −1.16 | 1.23 | −0.83 | 1.44 |
| AC005779.1 | −0.54 | −0.14 | 0.58 | −0.22 | 0.53 | CSNK1E | 0.08 | 0.27 | −0.12 | 0.16 | −0.26 | AC016180.1 | −0.09 | −0.34 | NA | −0.36 | −0.62 |
| E2F1 | 0.37 | −0.43 | −1.07 | 0.04 | −0.32 | AC022431.1 | −0.52 | −1.02 | 0.43 | 0.06 | −0.21 | AP003715.1 | −0.09 | 0.12 | −0.72 | 0.14 | −0.86 |
| POM121C | 0.19 | 0.01 | −0.24 | 0.02 | −0.11 | AC007790.1 | 0.18 | −0.16 | −0.08 | −0.02 | 0.37 | AP001372.2 | 0.00 | 0.17 | 0.55 | −0.17 | 0.24 |
| RN7SL560P | −1.19 | 0.14 | 0.13 | 0.69 | 0.48 | SPINK13 | −0.37 | 0.03 | 0.19 | 0.63 | −0.01 | RCC2P5 | 0.09 | 0.62 | −0.43 | −1.39 | −3.18 |
| AC021054.1 | −0.33 | 0.04 | 0.31 | 0.06 | 0.29 | CYB561D1 | −0.09 | 0.18 | 0.18 | 0.07 | −0.20 | AC106872.10 | −0.07 | −0.15 | −0.23 | −0.45 | −2.60 |
| AC012414.5 | −0.82 | 0.57 | 1.44 | 0.71 | 0.83 | PP12613 | −0.95 | 0.07 | 0.65 | −0.27 | −0.75 | AC234778.1 | 0.05 | −0.84 | 1.53 | 0.60 | 1.86 |
| GALNS | −0.29 | 0.04 | −0.02 | 0.12 | 0.18 | AC004853.1 | −1.08 | −1.21 | 2.51 | −0.88 | 3.18 | ABCF2P1 | −0.02 | −0.37 | −1.94 | 1.34 | −1.76 |
| LAMTOR5-AS1 | −0.24 | −0.20 | 0.26 | 0.13 | 0.44 | AC010442.1 | 0.35 | −1.02 | 0.03 | −0.36 | 0.03 | AC099539.1 | −0.09 | 0.17 | 0.50 | 0.37 | −1.02 |
| PFDN1 | 0.29 | −0.11 | −0.33 | −0.09 | −0.41 | CBX1P2 | −0.55 | −0.04 | 0.26 | −0.46 | −0.40 | LINC00994 | 0.01 | 0.30 | −0.23 | 0.12 | −0.28 |
| FAM120C | −0.18 | 0.04 | 0.12 | 0.08 | 0.10 | AC009301.1 | −0.34 | 0.05 | −0.10 | 0.04 | 1.20 | AC011139.1 | −0.01 | −0.19 | −0.30 | −0.27 | −0.39 |
| CLEC11A | −0.45 | 0.29 | 0.67 | −0.11 | 0.27 | MAOB | −0.17 | 0.01 | −0.62 | 0.22 | −0.19 | AL359704.1 | −0.02 | 0.55 | 0.58 | 0.44 | −1.60 |
| GGA1 | −0.25 | 0.06 | 0.00 | 0.13 | 0.10 | NUCKS1P1 | −0.63 | −2.01 | 1.37 | −0.13 | 1.53 | AL390774.2 | −0.01 | −0.19 | −0.05 | −0.44 | 0.22 |
| RNU6-238P | 0.77 | −0.19 | −1.16 | 0.23 | −0.58 | ASZ1 | −0.48 | −1.92 | −2.48 | −0.04 | −0.63 | AC002519.1 | −0.01 | −1.30 | 0.92 | −0.73 | 1.00 |
| MFF | 0.18 | −0.07 | 0.01 | −0.15 | −0.05 | AC090517.4 | −0.22 | 0.67 | 0.70 | 0.53 | 0.28 | AC005185.1 | −0.09 | 0.65 | −1.11 | 1.46 | −1.96 |
| AC111170.1 | 0.70 | −0.57 | −0.79 | −0.66 | −0.25 | PANX2 | 0.20 | −0.38 | −0.75 | −0.15 | 0.37 | AL592486.1 | 0.04 | −0.51 | 0.74 | 0.22 | 1.89 |
| AP002383.3 | −0.99 | −0.83 | 0.29 | 0.19 | 1.31 | MMACHC | −0.08 | −0.20 | −0.23 | −0.04 | −0.01 | SCN10A | −0.02 | −0.21 | −0.15 | 0.15 | 0.69 |
| RCBTB2P1 | 1.16 | 0.62 | 0.28 | −0.28 | −0.60 | ICK | 0.08 | 0.23 | 0.00 | 0.18 | −0.12 | AC061999.1 | −0.05 | 0.63 | 1.36 | −1.32 | 0.53 |
| RNU6-51P | −0.82 | −0.91 | 0.96 | −0.09 | 1.79 | CACNA2D3-AS1 | 0.24 | −0.75 | −0.15 | −0.56 | 0.07 | LINC01857 | 0.05 | 0.42 | −1.72 | 0.27 | −0.43 |
| OR56A5 | −1.75 | −1.47 | 0.52 | 0.84 | 1.86 | AC021739.4 | 0.28 | 0.05 | −0.06 | 0.33 | −0.08 | AC104117.4 | 0.09 | −0.39 | 0.76 | 0.16 | 0.96 |
| KAT7 | −0.18 | 0.19 | 0.16 | 0.11 | −0.02 | AP005136.2 | 0.25 | 0.09 | 0.49 | 0.11 | −0.19 | NBPF21P | −0.04 | 1.06 | 1.08 | 0.44 | −1.37 |
| AC027088.3 | 1.69 | −0.59 | −2.67 | 0.62 | −1.27 | PAOX | 0.11 | −0.06 | −0.54 | 0.22 | 0.13 | LUADT1 | 0.03 | −0.16 | 0.56 | 0.42 | 0.76 |
| NMNAT2 | −0.44 | 0.01 | −0.07 | −0.08 | −0.23 | RPS15AP34 | −0.58 | 1.23 | 0.29 | 0.35 | −0.09 | SLC7A3 | −0.03 | 0.83 | −1.10 | 1.57 | −1.51 |
| C8orf31 | −0.66 | −0.77 | 0.97 | −0.37 | 0.50 | AC126544.1 | −0.25 | −0.38 | 0.63 | 0.18 | 4.07 | OR6K6 | −0.09 | 0.47 | 0.86 | 1.01 | 0.84 |
| AC093249.2 | −0.66 | 0.01 | 0.07 | −0.05 | 0.26 | AC006557.6 | 0.29 | −0.87 | −1.02 | −0.04 | −0.40 | AC012358.3 | 0.00 | −0.14 | 0.23 | 0.14 | 0.23 |
| LINC02344 | −0.72 | 0.25 | 1.48 | −0.33 | 0.34 | MIR218-1 | −0.63 | 0.15 | 0.58 | −1.53 | −0.68 | MECOM | −0.01 | −0.13 | 0.48 | 0.00 | 0.26 |
| PARP2 | −0.16 | 0.04 | −0.02 | 0.06 | 0.04 | AP005328.1 | −0.51 | −0.44 | −1.68 | 2.21 | −1.37 | AC009220.2 | −0.01 | −0.71 | 0.75 | −0.08 | 0.67 |
| ACTR6 | 0.24 | 0.00 | 0.08 | 0.11 | 0.04 | IKZF4 | −0.06 | 0.07 | 0.14 | −0.01 | 0.09 | AC104806.1 | −0.01 | 0.74 | 1.72 | 0.30 | 0.99 |
| HIVEP3 | −0.42 | −0.05 | −0.19 | 0.28 | 0.35 | G36254 | 0.19 | −0.20 | −0.63 | 0.30 | −0.11 | AL355149.1 | −0.09 | −0.21 | −0.10 | −0.56 | −1.06 |
| AC009486.1 | 0.75 | −1.44 | −0.35 | −0.08 | 1.06 | JMJD1C-AS1 | 0.21 | 0.24 | −0.41 | 0.25 | 0.10 | LINC02567 | −0.09 | 0.57 | −1.27 | 0.49 | −2.62 |
| AC093157.2 | 0.74 | −0.69 | −0.32 | −0.31 | 0.42 | AC104024.1 | −0.48 | −0.94 | −1.39 | 0.65 | −0.67 | BX248415.1 | −0.04 | −0.36 | −1.74 | 1.33 | −0.85 |
| AC007686.4 | 0.99 | −1.87 | −3.19 | 0.36 | −0.75 | AC073410.2 | 0.25 | −0.17 | 0.40 | −0.55 | −0.09 | AP001029.2 | 0.00 | −0.20 | −0.32 | −0.05 | 0.07 |
| AC234778.2 | −1.05 | −0.16 | 1.55 | −0.89 | 0.14 | HNRNPKP1 | 0.31 | −0.56 | 0.36 | 0.29 | 0.21 | AL354984.2 | −0.02 | −0.37 | 0.78 | −0.98 | 1.20 |
| AC008038.1 | 0.24 | 0.20 | −0.36 | 0.09 | −0.36 | HNRNPA1P40 | 0.30 | −0.23 | −0.52 | 0.01 | 0.06 | AC137549.1 | 0.09 | −0.24 | −0.02 | −0.42 | −0.75 |
| FLJ12825 | −0.47 | 0.26 | 0.40 | 0.21 | 0.16 | DLX1 | −0.22 | 0.40 | 0.01 | 0.31 | −0.15 | AC107081.1 | 0.09 | −0.16 | 1.01 | −1.30 | −0.08 |
| AC016831.6 | −0.28 | −0.13 | −0.53 | 0.05 | 0.04 | AP005432.1 | 0.13 | 0.12 | 0.11 | 0.16 | −0.07 | AP001595.1 | −0.07 | −0.64 | 0.63 | −0.22 | −1.73 |
| CAPN2 | 0.32 | −0.18 | −0.76 | −0.08 | −0.27 | LATS2-AS1 | 0.20 | 0.10 | 0.17 | −0.43 | −0.68 | G12855 | 0.02 | 1.25 | −0.35 | 1.32 | −0.73 |
| AC008498.2 | 0.47 | −0.16 | −0.04 | 0.07 | 0.20 | AC097382.2 | −0.22 | −0.08 | −0.15 | 0.11 | −0.18 | RNU6-1147P | 0.01 | 0.20 | −1.75 | 0.86 | −0.98 |
| AC005306.1 | −2.00 | 1.50 | 1.31 | 0.76 | 1.06 | LINC00504 | −0.15 | 0.28 | 0.60 | 0.26 | 0.02 | AC091939.1 | 0.02 | −1.14 | −1.91 | −0.15 | −1.23 |
| GSTP1P1 | 1.44 | −0.24 | −0.43 | 0.05 | 0.07 | LINC00467 | −0.10 | −0.12 | 0.00 | −0.13 | 0.07 | G26311 | 0.02 | −0.69 | 1.90 | 0.14 | 0.71 |
| ANO4 | −0.73 | 0.62 | 0.22 | 0.08 | −0.26 | AC007688.1 | 0.33 | −0.53 | 0.28 | −0.24 | 0.54 | AC074044.1 | −0.04 | −1.09 | 2.03 | −0.91 | 2.45 |
| HIGD1AP14 | 0.78 | −0.29 | −0.71 | −0.03 | −0.53 | AL355802.2 | 0.17 | 0.04 | −0.70 | 0.17 | −0.32 | RGPD3 | −0.01 | −0.28 | −0.42 | 0.27 | 0.01 |
| AC046176.1 | 0.64 | −0.53 | −0.19 | −0.03 | −0.05 | RBM10 | −0.07 | 0.01 | −0.16 | 0.05 | −0.01 | LINC01674 | 0.09 | −0.70 | −1.58 | −0.22 | −1.51 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| POLR2C | 0.20 | −0.03 | −0.21 | −0.11 | −0.44 | AC018867.1 | 0.29 | 0.21 | 0.43 | −0.28 | −0.35 | RARRES2P6 | 0.04 | −0.28 | −0.87 | 1.31 | 2.72 |
| RPL7P23 | 0.58 | 0.09 | 0.02 | 0.01 | −0.25 | GPX8 | 0.13 | −0.32 | 0.43 | −0.48 | 0.07 | AC011718.2 | 0.06 | −0.60 | −1.28 | 0.83 | 1.06 |
| MIR548V | 0.77 | 0.18 | 0.09 | 0.32 | 0.23 | RPL7AP52 | −0.55 | −1.02 | 0.45 | −0.30 | −0.22 | CHEK2P3 | 0.09 | −1.42 | −0.13 | 1.50 | 0.64 |
| AL096855.1 | −0.41 | 0.08 | 0.75 | 0.03 | 0.30 | LINC02377 | −0.94 | 0.00 | 1.54 | −0.06 | 1.18 | OR5D13 | 0.09 | −1.06 | −0.59 | −0.27 | −1.46 |
| NOMO2 | 0.19 | −0.16 | −0.06 | −0.20 | −0.11 | AC018552.2 | 0.78 | −1.65 | −1.57 | −1.04 | −1.20 | HMGB1P38 | −0.09 | 0.10 | 1.24 | −0.04 | 1.24 |
| RPAP1 | −0.21 | −0.07 | −0.03 | −0.03 | 0.12 | AC092135.2 | 0.14 | −0.33 | −1.13 | −0.04 | −0.47 | AC099689.1 | −0.01 | 0.27 | 0.06 | 0.16 | −0.15 |
| AC083862.2 | 0.88 | −0.08 | −0.17 | −0.23 | 0.38 | AC068196.1 | 0.38 | −0.17 | 0.13 | −0.80 | −0.79 | AL021879.1 | 0.09 | −0.68 | −0.89 | −0.84 | −2.94 |
| AC025518.1 | 0.92 | −1.14 | −0.33 | −0.57 | −0.06 | AC010247.2 | −0.25 | 0.47 | 0.50 | −0.05 | −0.04 | SPATA32 | −0.01 | −0.55 | −0.65 | −0.31 | 0.11 |
| BX571818.1 | 1.13 | −0.62 | 0.61 | −0.28 | 0.85 | LINC01994 | −0.33 | −0.61 | 0.66 | −0.01 | 1.06 | AC093725.1 | 0.02 | −0.18 | −0.82 | 0.02 | −1.76 |
| MT1G | 0.79 | −0.56 | −0.26 | −0.38 | −0.30 | HNRNPA1P76 | 0.16 | 0.04 | −0.11 | −0.02 | 0.24 | SIPA1 | 0.00 | −0.18 | 0.12 | −0.13 | 0.03 |
| AC017104.5 | −0.66 | −0.60 | 0.37 | −0.39 | 1.19 | LRRC37A14P | −0.42 | −0.18 | 0.65 | −0.39 | 0.11 | PCNAP4 | 0.03 | −1.92 | −0.21 | 0.02 | 0.89 |
| LINC02577 | 1.27 | −1.35 | −1.23 | −0.89 | 0.22 | HNRNPA3P16 | −0.62 | 0.81 | −1.18 | 1.49 | −2.30 | AP003497.2 | −0.03 | −0.23 | 1.19 | −0.04 | 2.14 |
| G19302 | −1.36 | 0.78 | 2.89 | −1.60 | −0.14 | ARL4A | 0.13 | 0.13 | 0.40 | 0.05 | 0.17 | AC051619.7 | −0.01 | 0.27 | 0.21 | 0.44 | −0.56 |
| AP005329.2 | −0.77 | 0.55 | 1.05 | 0.69 | 0.67 | CDX1 | −0.38 | −0.43 | 0.72 | −0.04 | −0.08 | AC011487.2 | 0.01 | −1.60 | 0.73 | 0.08 | 0.46 |
| C9orf64 | 0.31 | −0.12 | −0.13 | −0.27 | −0.03 | EEF1A1P12 | 0.15 | 0.28 | −0.33 | 0.20 | −0.52 | KRT18P1 | −0.03 | −0.60 | −1.47 | 1.41 | 0.13 |
| G36324 | 1.24 | −0.49 | −0.86 | −0.17 | −1.22 | NAT2 | −0.55 | −0.67 | −0.69 | 0.13 | −0.75 | AC046134.1 | 0.02 | 0.32 | 0.33 | −0.67 | −0.29 |
| LINC01616 | −1.86 | −0.91 | −0.26 | −1.33 | 2.04 | AC025062.2 | −0.97 | −1.39 | 0.72 | −0.22 | 1.04 | MPEG1 | −0.01 | −0.06 | 0.58 | −0.34 | 0.02 |
| AC008080.4 | −0.56 | 0.17 | 1.35 | −0.28 | 0.18 | RBMX2P3 | −0.17 | 0.07 | −0.22 | −0.11 | −0.51 | NUTM2B-AS1 | 0.00 | 0.09 | 0.25 | −0.08 | 0.28 |
| AC004016.1 | 1.72 | −1.16 | −2.08 | −0.36 | −0.22 | OGFOD2 | 0.20 | 0.15 | −0.55 | 0.27 | 0.09 | SPATA3 | 0.02 | −0.81 | −1.42 | 0.39 | 0.15 |
| AC008132.13 | −1.29 | −0.86 | 0.75 | −0.49 | 1.85 | ENPP7P5 | −0.32 | 0.87 | 1.50 | 0.62 | 0.51 | AC009166.1 | −0.09 | −0.72 | −0.14 | −1.01 | −1.33 |
| RHBDF1P1 | 1.63 | 0.02 | −1.06 | 0.28 | 0.01 | KLHL4 | −0.24 | 0.29 | 0.35 | 0.09 | −0.12 | EIF4A1P5 | 0.01 | −0.23 | 0.05 | 0.25 | −0.01 |
| AC007750.1 | 1.06 | −0.76 | 0.09 | −0.97 | −0.03 | PFN1P8 | 0.30 | 0.19 | 0.27 | 0.50 | 0.48 | CFHR4 | 0.02 | 0.01 | 0.74 | −1.03 | −1.04 |
| LRRTM2 | 0.32 | −0.12 | −0.08 | −0.15 | −0.01 | AC013451.1 | 0.32 | −0.27 | −0.83 | −0.38 | −0.42 | FAM90A27P | −0.08 | −0.91 | −0.02 | −0.45 | 0.26 |
| MT-TY | −0.52 | 0.32 | 0.16 | −0.01 | 0.05 | AL451105.2 | −1.03 | −0.31 | 1.09 | 0.09 | 0.94 | RPL7P61 | 0.05 | 0.30 | −0.10 | 0.51 | −1.18 |
| FRG1 | 0.17 | 0.00 | −0.16 | −0.04 | −0.15 | CD300LB | 0.28 | −0.22 | −0.41 | 0.43 | −0.97 | AC069114.1 | 0.08 | −1.03 | −1.55 | −0.26 | NA |
| AL160411.1 | −1.46 | 0.40 | 1.32 | −0.53 | 0.62 | AC087359.1 | −0.16 | −0.29 | 0.17 | −0.27 | 0.15 | AC113554.1 | −0.07 | −0.07 | −0.95 | 0.82 | −1.05 |
| PRSS55 | −1.12 | −0.27 | 0.04 | 0.53 | 0.69 | AC023824.6 | 0.69 | −0.95 | −1.95 | −0.39 | 0.42 | AC099520.2 | 0.08 | 1.13 | −0.41 | 1.40 | −1.28 |
| HNRNPH1 | 0.15 | −0.18 | −0.33 | 0.04 | −0.02 | AC074366.1 | 0.28 | 0.12 | −0.50 | 0.33 | −0.36 | MIR365B | −0.02 | 0.83 | 1.45 | 0.63 | 0.33 |
| DDX11 | −0.30 | −0.11 | −0.20 | 0.00 | 0.33 | SLC39A12 | −0.52 | −0.36 | −0.64 | −0.20 | −0.24 | KRT8P25 | 0.07 | −0.92 | 0.02 | −0.31 | 0.00 |
| GUCY1B2 | −0.84 | 0.84 | 0.22 | 0.04 | −1.13 | PRAME | −0.30 | 0.15 | −0.20 | −0.50 | −0.50 | AC092568.1 | 0.03 | −1.28 | −0.86 | 2.33 | 0.67 |
| PTGES | 0.43 | −0.06 | −0.67 | 0.20 | −0.51 | RNU6-676P | 0.39 | −1.51 | 0.23 | −0.74 | −0.31 | AL354741.1 | −0.03 | −0.88 | −0.65 | −0.48 | 2.17 |
| AL162727.3 | 1.22 | −0.68 | −1.72 | −0.89 | −1.28 | B3GNT4 | −0.14 | 0.10 | 0.00 | 0.07 | 0.35 | AP003386.1 | −0.08 | −0.04 | 0.86 | −1.65 | 0.31 |
| AC096746.1 | 1.86 | −0.24 | 0.35 | −0.26 | −0.73 | AC025040.2 | 0.34 | −0.79 | −1.49 | 0.24 | −0.03 | AC096669.1 | 0.03 | −0.19 | 0.33 | −0.25 | 0.38 |
| AC009269.4 | −1.26 | −0.94 | 1.46 | 0.86 | 1.20 | RN7SL688P | −0.37 | 0.71 | 1.17 | 0.60 | −0.20 | AC105036.2 | −0.01 | −0.13 | 1.84 | −0.10 | 0.61 |
| NBPF17P | −0.56 | −0.31 | 0.63 | −0.08 | 0.85 | RN7SL503P | 0.22 | −0.44 | −0.66 | −0.40 | 0.38 | AC079601.2 | 0.01 | 0.01 | −0.27 | 0.16 | −0.04 |
| CLDN15 | −0.33 | 0.11 | 0.43 | −0.04 | 0.35 | LINC02518 | −0.47 | −0.12 | 0.69 | 0.73 | 0.51 | AC010230.1 | −0.03 | 0.06 | −1.19 | 2.24 | −1.49 |
| CBX3P7 | −0.96 | 0.84 | 0.21 | 0.72 | 0.12 | RPS3AP4 | −0.64 | 0.33 | −1.10 | 1.39 | −2.01 | OOSP4B | 0.03 | −1.52 | 0.37 | −0.64 | −0.89 |
| MRGPRX2 | −0.97 | 0.19 | 1.03 | 0.76 | 0.94 | MORC1 | −0.37 | 0.53 | −0.61 | 0.38 | −0.16 | AL445189.1 | −0.08 | −0.08 | 0.70 | 0.39 | −0.48 |
| SLC26A3 | −0.81 | −0.06 | −0.81 | 0.16 | −0.35 | AC013714.1 | −0.36 | 0.27 | 1.05 | 0.42 | 0.77 | AC016396.1 | −0.03 | 0.28 | 0.03 | 0.56 | 0.97 |
| RBM5 | −0.17 | 0.10 | 0.14 | 0.00 | 0.09 | PSMA3P | 0.72 | −1.96 | 0.29 | −1.06 | 0.70 | LINC01210 | −0.03 | 0.41 | 1.16 | −0.11 | −0.17 |
| SUFU | 0.24 | 0.07 | 0.03 | −0.02 | −0.14 | RN7SL652P | −0.37 | 0.83 | −0.88 | 0.36 | 0.36 | RNA5SP401 | 0.08 | 0.46 | 0.66 | 1.50 | −2.10 |
| AC093510.1 | 0.90 | 0.05 | −0.35 | 0.43 | 0.16 | AP003059.1 | −0.33 | 0.51 | 0.58 | −0.61 | 0.09 | AL139275.2 | 0.08 | 1.34 | 0.55 | 1.88 | −0.69 |
| AP002505.1 | −1.01 | −1.17 | 0.09 | 0.10 | 0.52 | FSD1 | −0.26 | 0.44 | −1.82 | 0.19 | −1.00 | CTGLF8P | −0.05 | 0.18 | 0.28 | 0.70 | −0.52 |
| RPSAP15 | 0.86 | −0.85 | −0.55 | −0.18 | −0.32 | AC118345.1 | −0.80 | 0.61 | −0.95 | 0.84 | −1.89 | STAT4 | 0.01 | −0.33 | 0.21 | −0.57 | −0.03 |
| CEACAMP7 | −1.34 | 0.34 | 0.76 | −0.48 | 0.07 | FAM192A | 0.06 | −0.06 | −0.11 | 0.03 | 0.00 | AL136040.1 | 0.01 | −0.19 | 0.77 | −0.24 | 0.57 |
| AL033519.2 | 0.93 | −1.01 | −1.51 | 0.34 | −0.62 | AC117434.1 | 1.38 | −2.09 | −1.34 | −1.15 | 1.38 | AC106895.2 | 0.02 | 0.10 | −0.60 | 0.30 | −2.19 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| SPOCK2 | 0.57 | −0.80 | −0.29 | −0.60 | 0.38 | KF456110.1 | −0.48 | 1.22 | 0.74 | −0.32 | −0.53 | AL589678.1 | 0.04 | 0.27 | −1.22 | 0.96 | −1.40 |
| AL133241.1 | 0.54 | 0.02 | 0.34 | −0.28 | 0.11 | PRSS54 | 0.54 | −0.94 | −0.99 | 1.56 | 0.76 | AL357500.1 | −0.01 | −0.51 | 0.56 | −0.16 | 0.42 |
| CHRM2 | −1.04 | 0.11 | 0.21 | −0.32 | −0.53 | AC103792.1 | −0.46 | 0.50 | 1.32 | 0.63 | 0.63 | AC080075.1 | −0.01 | 0.02 | 0.59 | −0.24 | 0.24 |
| NSMAF | 0.15 | −0.04 | −0.14 | 0.08 | −0.03 | GGPS1 | −0.11 | 0.07 | 0.05 | 0.15 | −0.12 | AL133240.1 | 0.08 | 0.18 | 0.05 | 1.64 | 0.56 |
| EFCAB7 | −0.26 | 0.38 | 0.22 | 0.12 | −0.12 | PSMD6-AS2 | −0.06 | 0.12 | −0.07 | 0.20 | 0.03 | ATP5PDP3 | 0.06 | 0.18 | 0.34 | −1.06 | −1.47 |
| PRRG1 | 0.32 | −0.20 | −0.12 | −0.13 | −0.09 | RPL5P35 | 0.50 | −1.01 | −0.57 | −1.58 | −0.60 | NXF4 | 0.02 | −0.07 | −1.64 | 0.45 | −0.95 |
| ECI2 | −0.32 | 0.10 | 0.64 | 0.30 | 0.34 | AC105265.3 | 0.64 | −1.42 | −1.34 | −0.26 | −0.01 | LINC00564 | 0.03 | −1.52 | −0.82 | −0.31 | 0.81 |
| RP11-1212A22.4 | −0.94 | −0.44 | 0.28 | 0.07 | −0.46 | H2AFZP6 | 0.49 | −1.21 | 0.04 | 1.01 | 1.42 | PNLIPRP1 | 0.01 | −1.04 | −1.31 | −0.06 | −1.40 |
| SATB1 | −0.22 | 0.33 | 0.21 | 0.24 | 0.04 | AC009971.1 | −0.83 | 0.14 | 0.49 | 0.24 | 0.06 | CKS1BP2 | −0.02 | 0.03 | −1.39 | −0.32 | −1.50 |
| AC093567.1 | 0.74 | −0.07 | −0.57 | 0.26 | −0.27 | RAD1P1 | 0.49 | −0.63 | −1.28 | 0.43 | 0.77 | LINC02020 | −0.04 | −0.44 | 1.12 | −0.66 | 0.36 |
| AC010525.1 | 0.82 | −0.70 | −0.71 | −0.04 | 0.59 | AP000759.1 | 0.17 | 0.10 | −0.55 | 0.20 | 0.05 | 1QTNF3-AMAC | −0.01 | 0.84 | −0.19 | 0.75 | −1.59 |
| AC002550.2 | 0.60 | −0.09 | −0.48 | −0.05 | −0.30 | ITLN2 | −0.42 | 0.24 | 2.11 | −0.83 | 0.47 | G4754 | 0.00 | 0.13 | 0.20 | 0.21 | 0.17 |
| AL137100.1 | −1.41 | 0.40 | 0.30 | −0.50 | −0.12 | AC068633.1 | 1.04 | −0.91 | −2.29 | −0.08 | 0.04 | AC104131.1 | −0.07 | −0.90 | 0.79 | 0.35 | 1.38 |
| LINC02290 | −1.32 | 0.65 | 0.08 | −0.15 | −0.28 | AC074375.1 | 0.33 | 0.37 | 0.09 | 0.40 | 0.82 | AC007376.1 | −0.03 | 0.13 | 1.26 | 0.48 | 0.43 |
| SACS-AS1 | −1.09 | 1.13 | 0.39 | 0.90 | −0.10 | MIR4650-2 | 1.01 | 0.45 | 0.67 | −2.24 | −1.80 | CNTNAP5 | −0.01 | −0.22 | −0.81 | 0.96 | −0.05 |
| PTPN14 | −0.23 | 0.21 | 0.22 | 0.09 | 0.02 | AC013356.2 | 0.74 | −1.79 | −0.35 | −0.23 | 0.75 | OR10J7P | 0.08 | −0.21 | 0.57 | −0.35 | −1.28 |
| AC007193.2 | −1.38 | 1.34 | 1.37 | 0.79 | 0.73 | AC012493.1 | 0.67 | 0.02 | −1.45 | 1.08 | −1.47 | SHISAL2A | 0.01 | −0.50 | −0.42 | −0.13 | −0.21 |
| AC022211.2 | −0.47 | 0.31 | 0.30 | 0.07 | 0.40 | CCDC169 | −0.29 | −0.11 | −0.75 | −0.01 | −0.37 | RN7SKP3 | 0.08 | −0.50 | −0.10 | −0.68 | 0.73 |
| MIR199B | −1.38 | 1.15 | 2.11 | −0.16 | −0.18 | MIR3680-2 | 0.33 | −1.73 | −1.19 | 0.24 | 1.60 | ONECUT3 | −0.01 | −0.64 | 0.41 | −0.09 | 0.00 |
| SERPINA10 | 0.84 | −1.20 | −1.68 | 0.14 | −0.22 | AL160412.1 | 0.54 | −0.89 | −1.96 | 0.32 | −3.57 | PHBP18 | −0.04 | −0.93 | −0.37 | −1.16 | 0.73 |
| CCDC12 | −0.31 | 0.16 | −0.23 | 0.31 | −0.07 | MAGEC3 | −0.60 | −1.81 | −0.31 | −1.27 | 0.68 | AL353613.1 | 0.03 | −1.13 | 0.79 | −0.02 | 1.30 |
| AC019257.7 | −0.94 | 0.64 | −0.12 | −1.00 | −1.06 | NHEJ1 | −0.19 | −0.12 | 0.72 | −0.47 | 0.52 | AC005162.2 | −0.01 | −0.59 | 1.35 | 0.03 | 1.21 |
| AMZ1 | 0.31 | −0.34 | −0.46 | −0.19 | 0.08 | RPL22P17 | −0.80 | 0.47 | 0.69 | −0.70 | −0.68 | F11 | −0.02 | −0.18 | 0.01 | 0.24 | −0.70 |
| MBNL3 | 0.34 | −0.13 | −0.39 | 0.19 | −0.26 | AL139042.1 | −0.66 | −0.04 | −1.23 | −0.40 | −0.79 | RFT1 | 0.00 | −0.15 | 0.08 | −0.15 | 0.10 |
| RPL23P2 | −0.61 | 0.46 | 0.08 | 0.27 | −0.17 | FRMPD2 | −0.35 | 0.24 | −1.11 | 0.71 | 0.33 | AL590396.3 | −0.08 | 0.13 | −0.15 | 1.59 | −0.68 |
| AC016705.2 | −0.76 | 0.61 | −0.32 | 0.90 | 0.18 | HAUS6P2 | −1.04 | −0.20 | −0.65 | 1.19 | 0.29 | AC011467.5 | 0.08 | −0.51 | −0.39 | 0.48 | 2.69 |
| MTND2P14 | −1.83 | 0.80 | 1.74 | 0.19 | −0.56 | ESRG | −0.22 | −0.56 | 0.57 | −0.05 | 1.26 | GABRE | 0.00 | −0.08 | −0.19 | 0.10 | 0.07 |
| PTPMT1 | 0.62 | 0.12 | 0.00 | 0.31 | −0.17 | FAM20C | 0.11 | −0.21 | −0.24 | −0.16 | −0.11 | AC069366.1 | −0.01 | −0.11 | −0.40 | 0.25 | −0.25 |
| RN7SL68P | 0.75 | 0.04 | −0.06 | −0.28 | −0.08 | HMGB1P4 | 0.31 | 0.24 | −0.78 | 0.97 | 0.02 | ARL14EPL | −0.02 | 0.11 | −0.14 | 1.20 | −1.31 |
| GLIPRIL1 | −0.55 | 0.37 | 0.82 | 0.24 | 0.34 | AC087441.1 | 0.34 | −0.43 | −0.68 | 0.30 | 0.13 | FUNDC2P4 | 0.01 | −1.74 | 0.44 | −1.21 | 1.11 |
| MRPL40P1 | 1.53 | −1.34 | −1.18 | −0.26 | 0.95 | AC074101.1 | −1.06 | 0.33 | 0.90 | −1.51 | −0.22 | AC098868.1 | −0.07 | −1.02 | −1.60 | −0.39 | 0.29 |
| PSAPL1 | −0.61 | 0.89 | 1.42 | 0.52 | 0.35 | IGKJ4 | 1.38 | −1.08 | 0.46 | −0.44 | −0.02 | SLC25A5P5 | 0.03 | −0.60 | −0.16 | −0.28 | 1.43 |
| OR56A4 | −1.06 | −0.21 | 0.26 | 0.49 | 1.29 | PITX2 | −0.19 | 0.34 | 0.18 | 0.02 | 0.28 | HHATL-AS1 | −0.08 | −0.33 | −0.49 | 0.41 | 0.65 |
| NKG7 | 0.83 | −0.77 | 0.89 | −0.39 | 0.98 | RNFT1P2 | −0.42 | 1.06 | 0.25 | 0.58 | −0.31 | AC026785.3 | −0.08 | −0.60 | −0.52 | 0.65 | −0.98 |
| CHCHD6 | −0.32 | 0.09 | 0.05 | 0.17 | 0.32 | FEZF1 | 0.77 | −1.27 | −1.23 | 0.89 | 0.49 | AC093720.1 | 0.08 | −0.41 | −0.10 | −0.41 | −1.69 |
| SALL3 | 1.25 | 0.42 | −0.77 | −0.72 | −2.68 | AL133343.2 | 0.42 | −0.96 | −1.95 | −0.03 | 0.40 | FP236240.2 | 0.02 | −1.58 | 1.07 | −0.41 | 0.74 |
| AC108471.1 | 0.49 | −0.38 | −0.20 | 0.22 | 0.24 | AL353811.1 | −0.63 | 0.38 | −0.92 | 0.17 | −2.81 | AC008641.1 | −0.05 | −0.01 | 1.15 | −0.30 | −0.04 |
| AC084198.1 | −0.90 | −0.40 | 0.84 | 0.07 | 0.44 | AC100778.2 | −0.22 | −0.23 | −0.19 | −0.16 | −0.02 | LIAS | 0.00 | −0.13 | 0.08 | −0.07 | 0.20 |
| AC068448.1 | −1.01 | −1.08 | 0.19 | −0.29 | −0.93 | AL391834.1 | 0.27 | 0.26 | 0.20 | 0.37 | −0.25 | LINC01826 | −0.04 | −0.18 | −1.94 | 0.64 | −1.36 |
| LIMS1-AS1 | 0.60 | −0.02 | −0.54 | −0.19 | −0.53 | OR10J3 | 1.15 | −0.98 | −0.75 | −0.12 | 1.59 | AC026797.1 | 0.02 | −0.29 | 0.46 | −0.58 | −0.02 |
| ALG13 | −0.17 | 0.08 | 0.30 | −0.04 | 0.20 | AC011374.2 | 0.37 | 0.03 | 0.88 | 0.12 | −0.28 | KRT18P6 | 0.02 | 0.07 | −1.62 | 1.29 | −1.39 |
| AL355990.1 | −1.36 | 0.15 | 0.19 | −0.87 | −0.10 | MFSD14A | −0.12 | 0.38 | −0.09 | 0.56 | −0.27 | RAMP2 | −0.01 | 0.22 | 0.95 | −0.19 | −0.02 |
| RBM22P2 | −0.53 | −0.11 | 0.06 | 0.04 | 0.10 | MSR1 | −0.23 | 0.26 | 0.42 | −0.33 | −0.07 | OR10G1P | 0.08 | −0.36 | 0.33 | −0.65 | −0.08 |
| MIR4697HG | −0.41 | 0.21 | 0.27 | −0.23 | 0.07 | RN7SKP70 | −0.20 | 0.77 | −0.16 | 0.70 | −0.07 | PNPT1P2 | −0.02 | 0.31 | 0.09 | 1.24 | −0.96 |
| KCTD13 | −0.29 | 0.08 | 0.16 | 0.20 | 0.20 | HLA-U | 0.31 | −0.06 | 0.55 | 0.11 | −0.34 | OR8B6P | −0.08 | −0.13 | 0.73 | 0.44 | 1.19 |
| LRP4-AS1 | −0.75 | 0.11 | 1.59 | 0.14 | 0.82 | RNA5SP342 | 0.61 | −0.38 | 0.52 | −0.70 | −0.72 | RPL29P25 | 0.02 | 2.00 | 0.89 | 0.66 | −0.83 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| RSPO3 | −0.66 | 0.45 | 0.96 | 0.06 | 0.02 | AL121987.1 | −0.42 | 0.59 | −0.59 | −0.09 | −1.10 | MYCT1 | −0.01 | 0.27 | 0.74 | 0.15 | −0.02 |
| RNU5F-7P | −1.26 | 0.48 | 0.31 | 0.99 | 0.02 | AC027130.1 | 0.23 | 0.71 | −0.18 | 0.68 | −0.61 | RPL7P6 | −0.01 | 1.19 | 0.71 | 0.25 | 0.03 |
| MAP3K14-AS1 | 0.43 | −0.31 | −0.48 | 0.00 | −0.01 | AC011773.1 | −0.56 | −0.43 | 1.72 | −1.17 | 0.74 | AC005102.1 | −0.03 | −0.11 | 0.14 | −1.04 | 0.09 |
| SLC15A2 | −0.43 | 0.46 | 0.50 | −0.08 | 0.12 | POGK | −0.05 | 0.11 | 0.11 | 0.04 | 0.01 | OR2AF1P | 0.07 | −0.03 | −1.46 | −0.67 | −2.00 |
| AC010186.3 | −0.35 | −0.04 | 0.39 | −0.07 | 0.33 | RPS15AP24 | 0.32 | 0.64 | 0.27 | 0.20 | −0.97 | AL158063.1 | 0.01 | −0.28 | 1.02 | −0.05 | 0.36 |
| AC015961.1 | −0.65 | 0.59 | 1.18 | 0.18 | 0.47 | MTUS2 | 0.14 | −0.32 | −0.47 | −0.05 | −0.05 | FEV | −0.03 | 0.13 | −1.42 | 2.40 | 1.40 |
| ENPP7P6 | −0.90 | 0.82 | 0.33 | 0.02 | −0.34 | AC079943.2 | −0.71 | −0.06 | −0.25 | 0.89 | −1.07 | RPEL1 | 0.01 | 0.05 | −0.29 | 0.09 | −1.24 |
| NUDT9P1 | −1.05 | −0.33 | 1.92 | 0.12 | 0.99 | PCDHA5 | −0.32 | 1.04 | −0.34 | 1.43 | −0.36 | AP000790.1 | −0.06 | −0.29 | −0.46 | −0.95 | 1.57 |
| GAPDHP71 | −1.24 | 0.48 | −0.25 | 0.20 | 0.20 | AL354766.2 | −0.36 | −0.46 | 0.42 | 0.92 | 0.63 | AC103724.4 | −0.03 | −0.67 | −0.50 | 0.57 | 0.39 |
| C1D | 0.28 | −0.14 | −0.11 | −0.26 | −0.16 | AL512430.1 | 0.28 | 0.24 | −0.25 | −0.15 | −0.59 | AP003472.2 | 0.02 | −1.46 | 0.20 | −0.35 | 0.08 |
| AC022679.2 | −1.17 | −0.33 | 1.74 | 0.15 | 1.79 | AP001029.3 | −0.25 | 0.40 | 0.57 | 0.66 | 0.08 | LINC00396 | −0.07 | −0.49 | 0.24 | 1.04 | 1.26 |
| BAZ1B | 0.23 | −0.25 | −0.20 | −0.18 | 0.00 | AC008467.1 | −0.08 | 0.14 | 0.26 | 0.01 | −0.06 | MIR941-1 | −0.01 | −0.69 | −0.82 | 0.04 | 0.39 |
| AC073896.3 | −0.52 | −0.47 | −0.02 | 0.00 | 0.31 | AC105402.1 | −0.91 | −1.14 | 0.71 | −0.96 | 1.35 | AP002954.1 | 0.01 | −0.53 | −2.13 | 0.03 | −0.87 |
| AC005293.1 | 0.64 | −0.57 | −0.51 | −0.80 | −0.72 | NAA11 | −0.34 | −0.54 | −0.51 | 1.13 | 0.40 | AC005014.1 | −0.01 | −0.77 | 0.71 | 0.13 | −0.82 |
| EEF1A1P24 | −1.00 | 0.49 | 1.13 | −0.20 | 0.91 | OR52L2P | −0.52 | −1.19 | −0.37 | −0.59 | −1.07 | LINC01177 | 0.07 | 0.32 | −0.70 | −0.32 | −0.92 |
| KMO | 0.68 | −0.53 | −0.77 | −0.19 | −0.92 | LINC01686 | −0.44 | −0.20 | 1.65 | 0.17 | 1.09 | LYPLA2P3 | 0.07 | 1.00 | −0.47 | −0.57 | −1.26 |
| LUM | 0.71 | −0.08 | 0.25 | −1.03 | −1.16 | SRPK2P | −0.63 | 0.67 | −1.88 | −0.12 | −2.22 | AC008869.1 | −0.04 | −0.86 | −0.50 | 0.93 | 0.42 |
| RNA5-8SP5 | −0.96 | 0.41 | −1.06 | 1.45 | −0.59 | AC132068.1 | −0.24 | −0.11 | 0.96 | −0.46 | 0.16 | AC110753.1 | −0.07 | −0.03 | 0.51 | −0.77 | −0.58 |
| AC138207.1 | 1.36 | −1.09 | −0.76 | −0.99 | −0.19 | AC118757.1 | 0.55 | −0.61 | −1.17 | 1.16 | −0.70 | OR10G2 | −0.05 | −0.69 | −0.25 | −0.46 | −0.31 |
| RMI2 | 0.40 | −0.47 | −0.05 | −0.17 | 0.06 | AC004925.1 | 0.20 | −0.15 | −0.88 | 0.70 | 0.62 | LINC01017 | 0.07 | 1.03 | −1.50 | 0.29 | −2.43 |
| LAT2 | 0.37 | −0.23 | −0.45 | −0.24 | −0.39 | FAM53B-AS1 | 0.16 | −0.15 | 0.08 | 0.06 | 0.19 | AC090502.3 | 0.07 | −0.94 | −0.10 | 0.55 | 1.04 |
| ENO3 | −0.47 | 0.03 | −0.23 | 0.12 | 0.22 | PLA2G7 | −0.22 | −0.46 | 0.43 | −0.31 | 1.17 | AC105390.1 | −0.04 | 0.29 | 0.51 | −0.80 | −1.46 |
| MIR138-1 | 1.26 | −0.07 | 0.10 | 0.13 | 0.40 | BNIP3P30 | −0.41 | 0.37 | 0.19 | 0.89 | 1.18 | AC104758.1 | −0.02 | 1.35 | −1.11 | 1.70 | −1.16 |
| RNU6-876P | 1.12 | −0.25 | −0.58 | 0.45 | −0.01 | AL353746.1 | −0.37 | −1.59 | 0.59 | −0.64 | 0.96 | NEK6 | 0.00 | −0.13 | 0.03 | −0.26 | 0.10 |
| AL121890.2 | −0.96 | 0.72 | 1.45 | −0.44 | 0.66 | AC104581.1 | −0.59 | 0.89 | 2.43 | −0.10 | 1.00 | MPI | 0.00 | 0.10 | −0.06 | 0.14 | 0.00 |
| AC010809.3 | 1.20 | 0.47 | −0.07 | 1.11 | 0.24 | RNU6-805P | −0.47 | −2.18 | 2.87 | −2.50 | 0.97 | AC018665.1 | 0.00 | −0.01 | −0.14 | 0.06 | 0.09 |
| SORCS3 | −0.81 | −0.33 | −0.58 | 0.66 | −0.16 | RPL12P8 | 0.69 | −0.73 | −1.44 | 0.02 | −0.51 | LINC00608 | −0.01 | −1.40 | 0.34 | 0.25 | 1.00 |
| ITGB3BP | 0.23 | −0.08 | −0.04 | −0.11 | −0.14 | BNIP3P1 | 0.34 | −0.79 | −0.61 | −0.69 | −0.26 | SLC38A4 | 0.00 | −0.17 | 0.10 | 0.29 | 0.28 |
| RPL29P19 | 1.16 | −1.07 | −1.70 | 0.18 | −1.07 | AC005839.1 | 0.14 | 0.08 | 0.28 | 0.21 | 0.14 | ARL2BPP2 | −0.07 | −0.70 | 0.77 | −1.35 | −0.03 |
| AC007546.1 | 0.56 | −0.10 | 0.00 | 0.10 | 0.15 | HNRNPA1P38 | −0.39 | 0.26 | −0.96 | −0.14 | −0.12 | G34192 | 0.02 | −0.18 | 0.90 | 0.16 | 0.17 |
| ATP2A3 | −0.54 | 0.12 | 0.81 | 0.16 | 0.72 | AC092017.4 | 0.52 | −0.67 | −1.16 | 0.66 | 0.11 | AC092447.10 | −0.07 | 0.09 | 0.85 | 1.91 | 1.22 |
| GPR143 | −0.52 | 0.37 | −0.19 | 0.54 | 0.02 | AL031282.1 | 0.24 | −0.16 | −0.72 | −0.09 | 0.15 | MTND1P20 | 0.06 | −0.77 | −1.48 | −1.27 | −2.41 |
| FGF13-AS1 | −1.09 | 1.08 | 0.41 | 0.97 | −0.63 | G28332 | 0.22 | −0.43 | −0.22 | −0.19 | 0.51 | RBPJ | 0.00 | 0.02 | −0.01 | 0.00 | −0.15 |
| LAMB1 | 0.27 | −0.40 | −0.08 | −0.30 | 0.09 | AC099494.1 | −0.15 | −0.03 | 0.13 | −0.06 | 0.32 | AC022107.1 | 0.01 | −0.23 | 0.32 | 0.14 | 0.14 |
| FAM85B | −0.69 | 0.71 | 0.56 | 0.46 | 0.12 | PTCHD3 | 0.41 | −1.11 | −2.23 | 1.50 | 0.93 | AC022240.1 | 0.03 | −0.23 | −0.52 | −0.14 | −2.29 |
| G29946 | 1.35 | 0.00 | −0.39 | 0.76 | 0.60 | AC005077.1 | 0.46 | −1.39 | −2.02 | −0.60 | −1.02 | SNORD114-6 | 0.02 | 0.03 | 2.55 | −0.80 | 0.94 |
| CACNA1C-AS4 | 0.54 | −0.20 | 0.04 | −0.86 | −0.51 | GPN2 | −0.05 | −0.07 | −0.16 | 0.09 | 0.05 | RNA5SP288 | 0.01 | −0.30 | 0.53 | −0.74 | −1.21 |
| DYNLL2 | −0.16 | 0.05 | 0.13 | 0.10 | 0.18 | G3900 | −0.41 | 0.10 | 1.03 | 0.92 | −0.12 | AC012574.2 | 0.07 | 0.38 | −0.60 | 0.51 | −1.74 |
| CYP4A43P | −2.15 | −0.43 | 2.29 | −1.29 | 0.35 | AC004921.1 | −0.49 | −0.99 | 0.34 | −1.77 | 0.79 | RPL17P49 | −0.07 | −0.32 | 0.96 | −0.89 | 1.76 |
| AL512329.2 | −0.87 | 0.97 | 1.83 | 0.23 | 0.88 | AC020779.1 | −0.27 | −1.07 | 0.82 | 0.01 | 1.66 | AC008808.2 | −0.07 | 0.20 | −0.91 | −0.86 | −2.83 |
| ARHGAP35 | 0.19 | 0.05 | −0.14 | 0.07 | −0.08 | GUCA1A | −0.35 | −1.51 | −1.35 | 0.27 | 0.64 | RPSAP40 | 0.07 | 0.17 | −1.20 | 0.37 | −0.39 |
| BRINP2 | −1.05 | −0.19 | −0.20 | 1.05 | 0.85 | AL049543.1 | 0.85 | −0.34 | 0.13 | −0.40 | −1.57 | AC108751.5 | 0.02 | −0.04 | −0.73 | 0.22 | −1.28 |
| AC008267.4 | −0.52 | 0.03 | 0.98 | −0.51 | 0.34 | G25511 | −0.32 | −0.05 | 1.94 | −0.07 | 0.86 | ASS1P4 | 0.07 | −1.13 | −0.90 | 0.82 | −0.07 |
| LRRC14B | −1.42 | 1.43 | 0.94 | −0.41 | 0.59 | AL353626.1 | −0.27 | 0.00 | 0.46 | −0.31 | 0.26 | AC090099.4 | −0.07 | −0.23 | 0.44 | 0.31 | 1.04 |
| LINC02482 | −1.06 | 0.80 | 1.23 | 0.09 | −0.33 | AC132192.2 | 0.23 | 0.02 | −0.78 | 0.37 | −0.66 | AC099654.1 | −0.03 | −0.09 | −1.05 | 0.16 | −1.24 |
| IFNG | 1.52 | −0.64 | −0.93 | 0.40 | 0.79 | AC023202.1 | 0.93 | −1.92 | 1.32 | −0.11 | 2.61 | FTH1P21 | −0.07 | −1.69 | 0.64 | −2.05 | 0.19 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| LINC01123 | 0.57 | −1.10 | −0.64 | 0.38 | 1.08 | MIR4728 | 0.84 | 1.44 | 0.46 | 0.97 | −0.81 | NAMPTP2 | −0.03 | −1.21 | −0.41 | 1.45 | −1.40 |
| SNHG8 | 0.36 | 0.00 | −0.21 | 0.30 | −0.44 | ARHGEF39 | 0.10 | −0.44 | −0.44 | −0.17 | −0.02 | BCAT1 | −0.01 | −0.28 | −0.06 | −0.49 | −0.10 |
| G22214 | 1.41 | −0.25 | 0.33 | 0.05 | 0.06 | AC114801.2 | 0.36 | −1.47 | 0.33 | −0.61 | 1.62 | AC025578.1 | 0.07 | 0.40 | −1.38 | 0.64 | −1.97 |
| SLC2A3 | 0.63 | −1.16 | −0.77 | −0.33 | −0.65 | RNA5SP195 | −0.15 | −0.01 | 0.37 | −0.03 | 0.37 | AP003123.1 | 0.02 | −1.26 | −1.88 | −0.41 | 0.46 |
| ANGPTL4 | 0.42 | −0.76 | −1.40 | 0.30 | 0.03 | PJA1 | 0.08 | −0.08 | −0.19 | −0.25 | −0.16 | AC244636.2 | −0.02 | −1.52 | −0.27 | −0.09 | 0.47 |
| AGO4 | −0.24 | 0.35 | 0.33 | 0.25 | −0.05 | AC126177.7 | −0.57 | 0.53 | 1.24 | −0.21 | 0.43 | BTF3P5 | −0.01 | −0.26 | −1.44 | 1.24 | −0.81 |
| ADCY3 | 0.22 | −0.19 | −0.48 | 0.12 | −0.19 | RNU105B | −0.45 | 0.45 | 1.13 | −0.66 | −0.39 | AC019155.2 | −0.02 | −0.91 | −0.38 | 1.06 | −0.31 |
| CELF5 | −0.79 | −0.60 | −0.49 | 0.15 | 0.15 | AL512625.3 | −0.29 | −0.10 | −1.02 | 0.04 | −1.98 | AL391730.1 | 0.07 | −0.52 | −1.14 | −1.02 | −2.25 |
| AL158835.1 | −0.73 | −0.44 | 0.33 | 0.15 | 0.91 | AL358937.1 | 0.49 | −1.61 | −0.43 | 0.59 | 2.30 | AL136359.1 | 0.07 | 0.02 | 0.03 | 0.31 | −1.57 |
| C8orf82 | −0.26 | 0.40 | 0.01 | 0.35 | −0.06 | SLC22A13 | 0.18 | −0.75 | −1.19 | 0.05 | −0.29 | OR10G4 | −0.02 | −0.92 | −2.24 | 1.32 | −0.06 |
| EML2 | −0.29 | 0.21 | 0.14 | 0.15 | 0.06 | LIN28AP1 | −0.61 | 0.59 | −1.33 | 1.11 | −2.13 | AC092819.1 | 0.02 | 0.20 | −1.81 | 0.01 | −2.36 |
| HFE | −0.35 | 0.01 | −0.17 | 0.11 | −0.21 | RPL23AP52 | 0.28 | 0.27 | −0.86 | 0.68 | −0.08 | PLGLB1 | 0.01 | 0.22 | 1.07 | 0.05 | 0.70 |
| EXOSC3P1 | −0.48 | 0.34 | 0.46 | −0.09 | 0.26 | AP001628.2 | −0.47 | 0.61 | 0.42 | −0.04 | −1.61 | AC079597.1 | 0.07 | 0.11 | −0.11 | 0.99 | 0.14 |
| RNA5SP403 | −1.42 | 0.91 | −0.35 | 0.83 | −0.44 | AP003041.1 | −0.30 | −0.45 | 0.18 | 0.18 | 0.96 | AC064872.1 | −0.07 | −0.05 | −0.49 | −0.76 | 0.72 |
| GLOD4 | 0.17 | −0.10 | −0.18 | 0.02 | −0.01 | PWWP2B | −0.08 | 0.13 | −0.29 | 0.17 | −0.11 | SMCR2 | −0.03 | −0.47 | −1.03 | 0.90 | −1.68 |
| IRF6 | 0.39 | 0.09 | −0.65 | −0.12 | −0.56 | OR10A3 | −0.33 | −0.49 | 0.44 | 0.23 | −0.60 | AP002383.5 | 0.02 | 0.24 | −0.22 | −0.02 | −0.09 |
| MATK | 0.66 | −0.78 | −0.86 | 0.17 | 0.39 | SNORA71B | −0.13 | 0.02 | −0.19 | −0.02 | −0.21 | OR4D7P | 0.02 | 0.06 | −1.05 | 0.18 | −0.18 |
| ODCP | 0.37 | −0.15 | −0.43 | −0.08 | −0.26 | NFE2L1 | 0.05 | −0.07 | −0.20 | −0.05 | 0.00 | LINC01363 | 0.01 | −1.72 | −1.21 | −1.52 | 0.92 |
| COX16 | 0.54 | 0.09 | −0.14 | 0.11 | −0.41 | LINC02036 | −1.46 | 0.87 | 1.51 | −1.02 | −0.04 | SUGP2 | 0.00 | −0.20 | −0.16 | −0.01 | 0.20 |
| SLC25A5P1 | −1.01 | 0.17 | 0.28 | 0.29 | 0.68 | C8orf74 | 0.19 | 0.10 | −0.13 | 0.22 | −0.33 | MTCO3P40 | −0.02 | −1.92 | 0.16 | −1.03 | 1.81 |
| BPIFC | 0.53 | 0.24 | 0.39 | 0.38 | −0.30 | PMS2P2 | 0.29 | 0.08 | −0.14 | 0.20 | 0.58 | NATP | −0.07 | −0.84 | 0.00 | 0.61 | −0.45 |
| AC100803.3 | −1.37 | 0.13 | 0.59 | 0.32 | −0.12 | MTCO1P29 | 0.33 | 0.22 | −0.06 | −0.25 | −0.07 | RNU6-945P | 0.02 | −0.36 | 1.96 | −0.91 | 1.32 |
| FCRLB | 0.68 | −0.68 | −0.44 | 0.05 | −0.13 | GS1-24F4.2 | −0.28 | −0.58 | 0.05 | −0.10 | 0.14 | SNORD114-20 | −0.01 | 0.58 | 0.72 | −0.91 | −0.98 |
| AL390718.1 | 1.64 | 0.35 | −1.14 | 0.89 | −1.14 | LINC01752 | −0.29 | −0.46 | −0.01 | 0.00 | 0.32 | AC010460.2 | −0.03 | 0.87 | −0.79 | 2.25 | −1.78 |
| NPSR1 | 1.48 | −0.85 | −2.17 | 1.23 | 0.12 | MTND5P20 | 0.67 | −1.47 | −1.81 | 0.24 | 0.68 | LINC01672 | 0.02 | −0.18 | −0.13 | −1.11 | −0.82 |
| DLX5 | 0.42 | 0.29 | −0.01 | 0.19 | −0.39 | HMGN1P2 | 0.23 | −0.51 | −0.38 | −0.44 | −0.31 | AC092723.5 | 0.02 | −0.35 | −1.42 | −0.40 | −0.10 |
| AC100827.2 | −0.57 | 0.17 | −0.09 | 0.54 | 0.49 | AL118508.4 | 0.31 | −0.55 | −0.46 | 0.77 | 0.10 | OR1P1 | −0.06 | −1.00 | −0.35 | 0.43 | −0.13 |
| AC006206.2 | −0.76 | 0.36 | 0.67 | 0.07 | −0.72 | CGREF1 | −0.13 | 0.33 | 0.73 | −0.13 | 0.25 | AL033379.1 | −0.03 | 2.29 | 0.61 | 0.25 | −0.41 |
| MT-TC | −0.78 | 0.24 | −0.53 | 0.55 | −0.18 | RNU4-7P | −0.45 | 0.59 | 0.28 | 1.08 | −0.37 | AC073488.1 | 0.06 | −0.58 | 2.22 | −1.58 | 0.35 |
| RNA5-8SP4 | −1.02 | 0.36 | −0.80 | 1.26 | −0.51 | KRTAP4-11 | −1.22 | 0.28 | 1.15 | 1.74 | −1.77 | AC004832.5 | 0.00 | −0.13 | 1.34 | −0.32 | 0.54 |
| LILRA4 | 1.31 | −1.49 | −0.34 | −0.58 | 0.48 | AC022929.2 | −0.29 | 0.42 | −0.28 | 0.08 | −0.32 | EPHA8 | −0.01 | −0.92 | −0.82 | 1.53 | 0.85 |
| AP002449.1 | 0.98 | −0.50 | −1.01 | 0.62 | −0.09 | MIR5192 | 0.21 | −0.47 | 0.19 | −0.60 | 0.41 | AL353593.1 | 0.00 | −0.15 | −0.24 | 0.24 | 0.16 |
| SLC26A10 | −0.60 | −0.17 | 0.28 | −0.04 | 0.00 | ADA2 | −0.13 | −0.17 | 0.26 | −0.02 | 0.34 | LINC00293 | 0.01 | 0.91 | −1.19 | 1.13 | −0.53 |
| AP002373.2 | −0.62 | 0.39 | 0.99 | −0.10 | −0.17 | MTND5P23 | −0.88 | 1.30 | 0.05 | 0.28 | −2.39 | AL078595.3 | −0.06 | −0.89 | 1.29 | −1.97 | 0.14 |
| NDFIP2 | 0.35 | 0.17 | −0.20 | 0.08 | −0.49 | NOL7 | 0.16 | 0.27 | −0.06 | 0.30 | −0.09 | AC245517.4 | 0.07 | −0.11 | −0.66 | −0.07 | −0.17 |
| MIF-AS1 | −0.46 | 0.37 | 0.69 | 0.23 | 0.16 | RNU6-1281P | −1.31 | 1.36 | 0.35 | 0.07 | −1.11 | RNA5SP276 | −0.06 | −0.45 | 0.60 | −0.28 | 0.79 |
| NIT1 | −0.21 | 0.13 | 0.10 | 0.05 | −0.06 | LINC00682 | 0.55 | 0.75 | −0.18 | 1.56 | −0.11 | C1QL1 | −0.01 | 0.90 | 0.48 | 0.20 | 0.76 |
| GRXCR2 | −1.03 | 0.16 | −0.49 | 0.17 | −0.36 | RN7SL507P | −0.35 | −0.50 | −0.67 | −0.63 | −0.57 | AC009117.2 | −0.01 | −0.91 | −2.36 | 0.17 | −1.58 |
| AC002401.3 | −0.86 | 0.63 | 0.67 | 0.70 | −0.14 | GBP4 | −0.17 | 0.03 | 0.27 | −0.77 | −0.31 | AL353778.1 | −0.06 | −0.18 | −0.11 | 0.27 | 0.34 |
| RNU6-1279P | −0.62 | 0.12 | −0.31 | 0.13 | −0.03 | C11orf1 | 0.12 | 0.03 | 0.11 | 0.03 | 0.04 | AL049780.1 | 0.00 | −0.14 | 0.56 | −0.06 | 0.45 |
| NFAM1 | −0.58 | −0.35 | −0.06 | −0.22 | 0.23 | AL138976.2 | 0.24 | −1.44 | 0.13 | −0.18 | 0.68 | SNORA73B | 0.00 | 0.32 | −0.59 | 0.83 | −0.64 |
| RNU6-485P | 1.31 | −0.63 | −0.55 | 0.62 | 0.58 | AC009044.1 | 0.15 | −0.65 | −0.20 | 0.04 | 0.21 | NDUFB4P1 | 0.01 | −0.24 | 1.16 | −0.25 | 0.42 |
| RNU6-787P | 1.12 | −0.85 | 1.80 | −0.32 | 0.88 | AL132838.1 | −0.30 | −0.28 | 0.61 | 0.85 | 1.73 | AP002791.1 | 0.06 | −1.13 | −0.99 | −0.21 | −1.09 |
| ATP5PBP5 | −0.87 | 1.42 | 0.23 | 0.82 | −0.28 | AC013726.1 | −0.34 | 0.56 | −0.58 | 0.46 | −0.18 | AC027701.1 | −0.04 | −0.19 | 2.12 | −0.38 | 0.29 |
| CDKN2AIPNL | 0.31 | −0.10 | 0.04 | −0.18 | −0.17 | LONP1 | 0.07 | −0.16 | −0.42 | 0.00 | 0.05 | RN7SKP106 | 0.06 | 0.47 | −1.19 | 0.92 | −1.55 |
| AC103834.1 | −0.58 | 0.31 | 0.65 | 0.11 | 0.45 | ADAM20 | −0.13 | −0.05 | 0.45 | −0.50 | 0.11 | AL353743.2 | −0.02 | −0.03 | 0.59 | 0.02 | 0.63 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC004158.1 | 0.58 | −0.35 | −0.30 | 0.27 | 0.62 | GORAB | 0.07 | 0.00 | −0.10 | 0.11 | 0.00 | AC084116.3 | 0.04 | −1.03 | −0.49 | 0.00 | 0.82 |
| AC010601.1 | −1.17 | −0.59 | −0.22 | −0.41 | −0.79 | RNU6-530P | −0.56 | 0.01 | 0.21 | −0.53 | 0.71 | IGKVID-17 | 0.06 | 0.29 | 0.30 | 0.09 | −1.54 |
| FAM20B | −0.21 | 0.01 | 0.07 | 0.05 | −0.04 | PRDM7 | 0.29 | −0.35 | −1.61 | 1.02 | −0.94 | AL732292.1 | −0.02 | 0.35 | −0.07 | −0.83 | −1.40 |
| RBM15-AS1 | −0.64 | 0.30 | 1.27 | −0.37 | 0.09 | IGLV1-51 | −0.30 | 0.84 | 0.46 | 0.31 | −0.53 | SSR1P2 | 0.02 | −0.20 | 0.52 | 1.61 | −1.36 |
| RN7SL668P | −1.38 | 0.84 | −1.11 | 1.56 | −0.90 | EIF3EP2 | 0.65 | 1.24 | −2.98 | 1.09 | −1.90 | KRT18P56 | 0.06 | −0.41 | −1.51 | 0.49 | −0.35 |
| AC091057.7 | 1.53 | −1.47 | −1.91 | −0.64 | −0.49 | AC011037.1 | 0.79 | −1.46 | 0.23 | −1.28 | −1.41 | RNF219-AS1 | −0.01 | −1.08 | 0.01 | 0.39 | 1.10 |
| AC245123.1 | −1.05 | 1.26 | 0.98 | 0.15 | −0.84 | AC079921.2 | −0.19 | 0.11 | 0.50 | −0.12 | 0.07 | MIR548A1HG | 0.01 | −0.37 | 1.52 | −0.51 | 1.05 |
| PLS1 | 0.42 | −0.16 | −0.28 | −0.14 | −0.07 | RNU2-48P | −0.44 | 0.29 | 0.27 | −0.24 | −0.68 | AC109441.1 | 0.02 | −0.77 | −0.23 | −0.61 | −0.72 |
| SEC14L6 | −1.13 | 1.53 | 1.55 | 2.46 | 0.72 | AC023830.1 | −0.14 | 0.34 | −0.40 | −0.01 | −0.70 | MTHFD2P5 | 0.06 | 1.10 | −1.31 | 1.66 | −2.02 |
| AL161773.1 | 1.06 | −1.11 | −1.91 | −0.87 | −1.50 | ABHD14A-ACY1 | 0.91 | −1.38 | −1.29 | 0.27 | −0.20 | AP005264.3 | −0.06 | 0.94 | 0.79 | −0.51 | −0.18 |
| MIR4308 | 1.73 | −1.46 | 0.18 | −0.61 | 1.80 | AC023232.1 | −1.27 | −0.65 | 0.72 | −0.94 | 0.71 | AC118653.1 | 0.04 | 0.22 | −0.68 | 1.68 | 0.17 |
| NEGR1-IT1 | −1.37 | 1.27 | 2.31 | −1.28 | −0.01 | MORC1-AS1 | 0.86 | −0.74 | −1.61 | 1.34 | −0.94 | AL359636.3 | 0.04 | 0.91 | 2.07 | −0.81 | 1.87 |
| CYB5R2 | 0.30 | −0.08 | −0.43 | −0.25 | −0.16 | HMGB3P2 | −0.52 | −0.88 | 1.06 | −0.32 | 0.86 | AL606519.1 | 0.06 | −0.53 | 0.21 | 0.09 | −0.60 |
| AL133268.4 | −0.71 | −0.24 | 0.70 | −0.14 | 0.34 | AC015969.1 | 0.50 | −0.77 | −1.78 | 0.31 | −1.41 | AC092112.1 | 0.03 | −1.19 | 0.88 | 0.51 | 3.13 |
| HGF | −0.53 | 0.18 | 0.97 | −0.35 | 0.04 | CPA1 | −0.41 | −2.56 | −0.94 | 0.72 | 2.68 | AC092709.1 | 0.06 | 0.08 | −0.84 | 1.64 | −0.34 |
| RNA5SP278 | 1.02 | 0.04 | 0.14 | −0.31 | −0.17 | AC114814.3 | 0.73 | −1.61 | −2.05 | −1.09 | −2.62 | SLC25A51P3 | 0.06 | −1.17 | 0.83 | −2.02 | 1.07 |
| MBIP | 0.28 | −0.03 | −0.26 | 0.05 | −0.27 | RN7SL781P | −0.42 | 1.39 | 0.65 | 0.14 | −0.17 | IFNA14 | 0.06 | 0.51 | −0.39 | −0.60 | −2.11 |
| MIR135B | 2.53 | −0.73 | −3.52 | −0.18 | −3.23 | CCDC174 | −0.05 | 0.04 | 0.02 | 0.04 | 0.07 | AC073912.3 | 0.01 | −0.58 | −0.03 | −0.10 | 0.75 |
| AC004223.2 | −0.59 | 0.04 | −0.16 | −0.12 | −0.21 | AC023509.6 | 0.12 | −0.23 | −0.19 | −0.13 | −0.01 | AC100775.1 | 0.06 | −1.01 | −0.80 | 1.26 | 0.69 |
| ABHD12B | −0.37 | 0.41 | 0.86 | 0.05 | 0.13 | AL627223.1 | 0.38 | 0.20 | 0.10 | 0.02 | 0.20 | AL162391.1 | 0.03 | 0.02 | −0.55 | 1.34 | −0.15 |
| LINC00930 | −1.42 | −0.14 | 0.70 | 0.60 | 1.01 | HCG4B | 0.33 | −0.10 | 0.41 | 0.01 | 0.39 | AC007253.1 | −0.04 | 0.62 | 0.20 | 1.70 | −0.35 |
| AC090579.1 | −0.66 | 0.39 | 1.51 | 0.23 | 0.68 | AC114781.2 | 0.39 | −0.32 | 0.33 | −0.39 | 0.01 | AC092573.1 | −0.02 | −0.56 | −0.01 | 2.17 | 0.06 |
| STMND1 | −1.03 | −0.14 | −0.02 | 0.45 | −0.21 | RNU6-1008P | −0.56 | −2.06 | 1.97 | −2.12 | 1.43 | GDF2 | −0.01 | 0.01 | −0.24 | 0.00 | 0.10 |
| SLN | −1.70 | −0.89 | 1.33 | −0.80 | 2.06 | FAM69A | 0.13 | −0.21 | −0.09 | −0.04 | −0.18 | GSTA9P | −0.03 | 0.11 | −0.55 | 1.35 | −1.61 |
| DNAH10 | −0.53 | 0.05 | 0.49 | 0.02 | 0.06 | SLC22A12 | −0.60 | −0.96 | 0.53 | −0.39 | −0.76 | AL365255.1 | −0.02 | −1.91 | 1.22 | −1.04 | 1.93 |
| PTGES3L | −0.81 | 0.38 | 1.41 | −0.24 | −0.08 | AP000867.2 | 0.44 | −0.43 | 0.38 | −0.59 | −0.49 | AC027807.2 | 0.01 | −0.14 | −0.71 | −0.35 | −1.27 |
| GADL1 | 0.90 | −0.14 | −1.95 | 0.77 | −0.61 | AURKAP1 | 0.52 | −0.50 | −0.43 | −0.94 | −1.78 | OR5M3 | 0.04 | −0.09 | −0.64 | 1.79 | −1.01 |
| LYSMD4 | −0.31 | 0.26 | 0.12 | 0.32 | −0.03 | AP003390.1 | 0.16 | −0.70 | −0.81 | 0.02 | 0.43 | AL358335.1 | 0.03 | 0.71 | −1.41 | 2.01 | −0.91 |
| DUX4L46 | −1.30 | 1.15 | 0.69 | 1.77 | 1.01 | AC090897.2 | 0.62 | 0.42 | −1.41 | −0.73 | −3.20 | DBT | 0.00 | 0.23 | 0.10 | 0.14 | −0.05 |
| AC079950.1 | −1.05 | 0.45 | 0.71 | 0.31 | 0.20 | SLC17A6 | 0.41 | −1.33 | −1.76 | 0.78 | −0.69 | AC116353.5 | 0.00 | −0.34 | −0.26 | 0.40 | 0.69 |
| SLC6A14 | 0.63 | −0.30 | −0.32 | −0.81 | −0.21 | AC006026.3 | −0.73 | 0.81 | 1.38 | 1.62 | 0.85 | AP000424.1 | −0.01 | −0.60 | 0.39 | −0.76 | 0.00 |
| G22812 | −0.79 | 0.27 | 0.74 | −0.13 | 0.14 | RNU6-260P | 0.55 | −0.67 | 0.22 | −0.99 | −0.94 | AC105245.1 | −0.05 | −0.17 | 0.07 | −0.31 | −1.33 |
| AL359636.2 | 1.20 | −0.96 | −0.74 | −0.69 | 0.32 | AL356967.1 | 1.15 | 0.28 | −1.22 | 1.42 | 0.35 | AC092590.1 | −0.06 | 0.10 | −0.70 | 0.06 | −0.03 |
| AL645933.2 | −0.51 | −0.20 | 0.91 | −0.10 | 0.59 | OR4N2 | −0.54 | −0.15 | −0.40 | −0.60 | −0.77 | EEF1A1P20 | −0.06 | −0.47 | 0.36 | 0.03 | −0.14 |
| LANCL1 | 0.37 | 0.05 | 0.00 | 0.00 | −0.32 | AC068993.1 | 1.03 | −0.63 | −1.47 | −0.13 | −1.40 | MYL6P2 | 0.02 | −0.62 | 1.10 | −0.88 | 0.22 |
| AARD | −0.76 | 0.81 | 1.41 | 0.99 | 0.46 | MIR1295A | −0.37 | −0.26 | 1.42 | −0.66 | 0.40 | AC093627.7 | −0.01 | −0.74 | −1.41 | 1.41 | 0.03 |
| AL121917.1 | −0.53 | 0.12 | 0.57 | −0.11 | 0.08 | DNAJC8P1 | 0.46 | 1.44 | −1.06 | 0.83 | −0.39 | AC008060.1 | 0.02 | −0.21 | 0.89 | 0.63 | 0.74 |
| RPL7AP15 | −0.76 | 0.33 | 0.07 | 0.47 | 0.73 | AC007422.2 | 0.87 | −0.34 | −1.12 | −1.10 | −0.85 | AL356863.1 | 0.03 | −0.97 | −0.76 | −1.28 | −1.05 |
| FO393419.2 | −0.40 | −0.22 | −0.30 | 0.17 | 0.19 | IFRD1 | −0.08 | 0.04 | −0.07 | −0.01 | −0.18 | PES1P1 | −0.02 | 0.39 | −0.87 | 1.69 | −0.35 |
| 5-Mar | 0.21 | −0.03 | −0.15 | 0.05 | −0.03 | FNTAP2 | −0.16 | 0.19 | −0.46 | 0.11 | −0.38 | AC090142.1 | 0.06 | −0.28 | 0.43 | 0.45 | −2.91 |
| G4061 | 0.92 | 0.32 | 0.36 | 0.01 | −1.05 | AC009310.1 | 0.53 | 0.20 | −0.28 | −0.68 | 0.88 | AC108733.1 | −0.06 | −0.05 | 0.08 | 0.62 | 1.26 |
| BIN1 | −0.34 | 0.19 | 0.14 | 0.13 | 0.07 | AC083798.1 | 0.27 | −0.48 | 0.47 | −0.02 | 0.17 | PLA2G12A | 0.00 | 0.16 | 0.23 | 0.10 | 0.07 |
| AC010900.1 | −0.57 | 0.64 | 0.33 | 0.34 | −0.43 | LINC02501 | 0.65 | −0.43 | −1.51 | 0.28 | −0.69 | LINC01981 | −0.01 | −2.30 | −1.91 | −0.38 | 0.96 |
| KRT8P29 | −0.72 | 0.07 | 0.41 | −0.06 | −0.31 | AL591926.7 | −0.82 | −0.04 | −0.88 | −0.23 | −3.42 | AC079610.1 | 0.01 | 0.62 | 0.84 | 0.14 | 0.27 |
| AC025449.1 | −0.39 | −0.12 | 0.54 | 0.22 | 0.51 | AL133399.1 | −0.41 | −0.14 | 3.00 | −0.93 | 1.73 | SLC14A2-AS1 | −0.01 | 0.51 | −1.27 | 0.36 | −1.23 |
| SLC30A2 | −0.79 | 0.23 | 1.42 | 0.81 | 0.18 | MTCO2P22 | −0.38 | −0.27 | −0.12 | 0.77 | 0.11 | AL050338.1 | −0.06 | −0.67 | −1.29 | −0.75 | 0.03 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| HNRNPAO | 0.15 | −0.06 | −0.14 | 0.07 | 0.07 | RPL12P36 | 1.02 | −0.81 | −2.72 | 0.30 | −1.66 | OR4C15 | −0.03 | 0.97 | −1.03 | 0.46 | 0.49 |
| RN7SKP118 | −1.53 | 0.81 | 0.60 | 1.28 | −0.36 | MIR548AO | 0.69 | −1.94 | 1.68 | −0.13 | 1.99 | AC007953.2 | −0.03 | −1.85 | 0.85 | −0.74 | 2.09 |
| DNAJC11 | 0.23 | −0.30 | −0.30 | −0.16 | 0.07 | MTATP6P24 | 0.68 | 0.54 | 0.77 | −0.48 | −0.61 | AC073137.1 | −0.06 | −1.22 | −1.16 | 0.52 | −0.64 |
| AC010547.1 | −0.64 | 0.46 | 0.39 | 0.46 | −0.32 | METTL21AP1 | 0.20 | 0.04 | 0.46 | −0.18 | 0.09 | AC100768.2 | −0.06 | 0.28 | 0.55 | 1.06 | 1.68 |
| AC016745.1 | −0.78 | 0.21 | 0.97 | 0.42 | 0.63 | AC024558.1 | 0.26 | −0.02 | 0.98 | −0.03 | 0.38 | AC138761.1 | −0.06 | −0.90 | −0.44 | −0.78 | 1.46 |
| SULT1C3 | −1.03 | 0.64 | | | | MIR583 | −0.39 | −0.04 | −1.19 | 0.90 | 0.47 | AC148477.3 | 0.06 | −1.32 | −0.23 | 0.27 | 0.14 |
| ARSI | −0.72 | 0.24 | −0.48 | 0.49 | −0.36 | NR2E1 | −0.36 | −0.11 | −0.92 | 0.20 | 0.12 | EIF4BP5 | 0.00 | 0.24 | −0.26 | 0.08 | −0.31 |
| AL159174.1 | −1.21 | 0.49 | 0.61 | −1.00 | −0.31 | LLPH-DT | −0.21 | −0.64 | 1.08 | −0.73 | 0.93 | PSMA8 | 0.01 | −0.54 | −1.31 | 0.13 | 0.02 |
| CLEC12B | −0.77 | 0.23 | −0.18 | 0.64 | 0.59 | AC010643.1 | −0.34 | −0.43 | −0.56 | −0.19 | 0.01 | AL049564.1 | 0.06 | 0.03 | 0.32 | −0.36 | −0.67 |
| AC096534.1 | −1.26 | −0.31 | 3.09 | −0.27 | 1.84 | AC005798.1 | −0.70 | −1.35 | −1.25 | 0.63 | −1.30 | AC111188.1 | 0.01 | −0.12 | −0.06 | 0.10 | −0.22 |
| MAP3K7 | 0.13 | −0.08 | −0.02 | −0.09 | −0.01 | AC107067.1 | −0.32 | −0.65 | 0.24 | −0.37 | 0.53 | RNU6-858P | 0.02 | 0.31 | 0.12 | −1.32 | 0.13 |
| HSD17B1P1 | −0.54 | 0.56 | 0.17 | 0.53 | 0.21 | AL137100.2 | −1.16 | 1.10 | 0.30 | 2.08 | 0.22 | RN7SKP233 | −0.06 | −0.61 | −1.83 | 1.56 | −0.90 |
| CLCN1 | 0.89 | −0.17 | −1.41 | 0.07 | −1.04 | LRRC18 | 0.24 | −0.62 | −0.11 | −0.56 | 0.70 | KDM4F | 0.05 | 0.18 | −0.87 | −0.01 | −2.27 |
| HNRNPA3P5 | 0.50 | −0.16 | −0.85 | 0.24 | −0.38 | AL161668.3 | 0.16 | 0.02 | 0.20 | −0.13 | −0.19 | AL132640.2 | −0.01 | −1.48 | −0.14 | 0.08 | 0.46 |
| AL161636.1 | −0.98 | 1.43 | 2.32 | 0.37 | −0.26 | NKX3-1 | 0.20 | −0.06 | −0.60 | 0.00 | 0.33 | G8753 | 0.00 | 0.73 | 0.90 | −0.07 | −0.02 |
| FER1L5 | −0.48 | −0.15 | 0.37 | −0.14 | 0.21 | AC007618.1 | 0.35 | −0.01 | 1.01 | −0.54 | −0.68 | AC074133.1 | −0.02 | −0.05 | −0.16 | 1.12 | 0.24 |
| AC090740.1 | −1.40 | 1.08 | 0.36 | 0.98 | −0.06 | CD320 | 0.12 | −0.12 | −0.53 | 0.04 | −0.10 | AP003084.1 | 0.00 | −0.12 | 0.61 | 0.23 | 0.90 |
| ARIH2OS | −0.42 | 0.35 | 0.52 | 0.00 | 0.15 | MIR3150BHG | 0.18 | 0.06 | −0.22 | 0.60 | 0.29 | AL132640.1 | 0.03 | 0.48 | 1.84 | −0.79 | 0.79 |
| RHOQP1 | 0.82 | −0.74 | 0.04 | −0.33 | 0.45 | ADAMTS2 | 0.16 | 0.03 | 0.69 | −0.68 | −0.32 | AC011500.2 | −0.06 | −0.73 | −1.03 | −0.58 | NA |
| SCARNA20 | −0.52 | 0.17 | 0.62 | 0.29 | −0.06 | MIR591 | 0.32 | −1.14 | −0.41 | −0.34 | −0.32 | AC066616.1 | 0.03 | −2.30 | −0.74 | −0.63 | −0.92 |
| GPR173 | −0.48 | −0.08 | 0.83 | −0.40 | 0.04 | AC110373.1 | 0.22 | −0.50 | 0.47 | −0.41 | 0.01 | LINC01337 | 0.01 | −0.60 | 0.54 | −0.02 | 0.97 |
| AC093904.4 | 1.05 | 0.37 | −0.38 | 0.22 | −0.85 | AD000864.1 | 0.28 | −1.23 | 0.57 | −0.62 | 1.08 | SEC63P2 | −0.02 | 0.49 | −1.75 | −0.96 | −1.88 |
| AL031280.1 | −0.65 | −0.03 | 0.00 | 0.21 | 0.31 | STOX1 | 0.13 | 0.41 | −0.36 | 0.37 | −0.59 | LINC00574 | −0.01 | 0.32 | −0.94 | 1.05 | 0.30 |
| RNU7-81P | 1.69 | −0.94 | 0.98 | 0.16 | −1.14 | NBEAL2 | −0.11 | 0.05 | −0.14 | 0.19 | 0.27 | DPRXP2 | 0.01 | 1.06 | −0.73 | 0.25 | −0.01 |
| LINC02325 | 0.88 | −1.08 | −1.33 | −0.22 | −0.53 | OR4C50P | 0.87 | −1.09 | −2.03 | 0.93 | −0.58 | AC093840.1 | −0.03 | −0.70 | −0.13 | 0.71 | 0.38 |
| OR52Y1P | 1.77 | −0.50 | −2.64 | −0.04 | −2.71 | AC008378.1 | 0.68 | −0.80 | −0.44 | −1.30 | −1.99 | AL358473.2 | 0.02 | −1.60 | 0.35 | −0.38 | 0.85 |
| DBF4B | −0.30 | −0.35 | 0.06 | −0.18 | 0.53 | AL390862.1 | 0.78 | −0.09 | −1.17 | 0.77 | −1.19 | AC087633.1 | −0.05 | −0.69 | 0.48 | −0.45 | −0.37 |
| IL10 | 0.82 | −0.92 | −1.68 | −0.44 | −0.14 | HIGD1AP9 | 0.71 | −0.72 | −0.89 | −0.36 | −0.44 | LINC02342 | −0.05 | 0.10 | −1.15 | 0.38 | −1.93 |
| AC011933.2 | 0.38 | −0.26 | −0.15 | −0.23 | −0.18 | MYH8 | 0.28 | −0.62 | −0.87 | 0.41 | −0.36 | LINC00207 | −0.03 | −2.25 | 0.28 | −0.32 | 1.32 |
| CDH10 | −0.95 | 0.14 | 0.65 | 0.44 | 0.32 | RD3 | −0.44 | 0.07 | −0.75 | 0.82 | 1.87 | AC092198.1 | −0.01 | 0.60 | −1.13 | 0.13 | −1.45 |
| AC108704.1 | 1.41 | −1.06 | −1.73 | −0.10 | 0.18 | AGAP6 | 0.11 | −0.02 | 0.03 | −0.08 | 0.24 | AC098976.1 | 0.03 | −0.48 | −0.87 | −1.08 | −0.50 |
| AC145207.9 | −0.57 | −0.13 | 0.85 | −0.04 | 0.74 | AC025280.1 | −0.24 | −0.23 | −1.05 | −0.92 | −1.11 | AL592182.3 | −0.01 | −1.00 | −0.59 | 0.81 | −0.84 |
| NAB2 | −0.23 | 0.25 | 0.29 | −0.02 | −0.11 | AC005725.1 | 0.22 | −0.47 | −0.27 | 0.29 | 0.14 | OGT | 0.00 | 0.20 | 0.03 | 0.16 | −0.10 |
| NLK | 0.18 | −0.20 | 0.06 | −0.27 | 0.08 | AC026979.2 | 0.22 | −0.60 | 0.38 | 0.13 | 0.30 | SLAMF6P1 | 0.05 | 0.05 | −0.03 | −0.26 | −0.32 |
| RN7SL643P | −1.71 | 1.58 | −1.67 | 2.30 | −1.37 | DCTN1-AS1 | 0.11 | −0.19 | 0.27 | −0.04 | 0.25 | AL353141.1 | −0.02 | 1.25 | 0.47 | −1.23 | −1.92 |
| AC012409.5 | −0.73 | 1.13 | −0.33 | 0.78 | −0.41 | PPM1D | 0.06 | 0.04 | 0.14 | −0.13 | −0.15 | AC104619.1 | −0.01 | 0.31 | −1.92 | 0.00 | −2.49 |
| GOLGA2P11 | −1.55 | 1.25 | 1.49 | 0.00 | 0.34 | CALY | −0.44 | 0.34 | 0.11 | 0.88 | −0.63 | LINC02211 | 0.01 | −0.45 | 0.15 | 0.13 | 0.47 |
| ALDH7A1P1 | −0.73 | 0.84 | 0.98 | 0.29 | −0.15 | AP001775.1 | 0.36 | −0.64 | −0.33 | −0.26 | 0.34 | LINC01696 | 0.03 | 0.44 | −0.24 | 0.01 | 0.41 |
| RPL10P12 | 0.63 | −0.07 | −0.19 | −0.23 | −0.07 | G33706 | −0.25 | 0.40 | 0.30 | 0.02 | 0.78 | AC090621.1 | −0.05 | −0.98 | 0.31 | 0.44 | 1.33 |
| RNF14 | −0.21 | 0.05 | 0.16 | −0.12 | −0.04 | AC013410.1 | 0.34 | −0.51 | −0.05 | 0.03 | 0.11 | AC090124.1 | −0.03 | 0.69 | −0.81 | 0.16 | −0.65 |
| RNU6-130P | 0.84 | −0.41 | 0.61 | −0.62 | 0.75 | FAM86KP | −0.39 | 0.36 | 0.84 | 0.17 | 0.06 | HNRNPA1P19 | −0.05 | −0.61 | −0.46 | −0.15 | 0.26 |
| AC006480.1 | −0.70 | −0.11 | 0.75 | −0.07 | 0.90 | SPCS2P3 | −0.66 | −0.59 | −0.01 | −0.53 | −0.22 | EEF1GP8 | −0.02 | −0.56 | −0.57 | 1.07 | −1.13 |
| MGLL | −0.41 | 0.26 | 0.37 | −0.05 | −0.07 | SMIM29 | −0.10 | 0.24 | 0.26 | 0.22 | 0.00 | CADM2-AS2 | −0.03 | −0.03 | −2.09 | 1.36 | −0.61 |
| HDGFL1 | −1.07 | −0.35 | 0.32 | 0.19 | 0.24 | AP004289.2 | −0.13 | −0.42 | −0.30 | −0.08 | 0.19 | ALG1L15P | −0.02 | −0.24 | −1.21 | 0.53 | −0.58 |
| EN1 | −0.40 | 0.71 | 0.76 | 0.08 | −0.17 | RAB23 | −0.09 | 0.05 | 0.28 | −0.43 | −0.19 | SNORD126 | −0.01 | −0.09 | 1.05 | 0.94 | 0.03 |
| STAR | −0.46 | 0.15 | 0.47 | 0.18 | 0.43 | AL355981.1 | 0.38 | 0.06 | −0.38 | −0.22 | −1.20 | CHEK2P4 | −0.05 | −1.15 | −0.23 | −1.05 | 1.87 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| LINC02515 | 0.92 | −1.36 | 0.52 | −0.20 | 0.90 | NUCB1 | −0.06 | 0.05 | −0.08 | −0.05 | −0.20 | LINC02094 | −0.02 | −0.40 | −0.32 | 0.67 | 1.26 |
| AL136454.1 | 0.55 | 0.13 | −0.53 | −0.17 | −1.01 | RN7SL174P | 0.21 | −0.44 | −0.73 | −0.58 | −0.37 | RPL35P2 | 0.00 | 0.11 | −0.19 | −0.04 | −0.23 |
| RN7SL473P | 0.46 | −0.43 | −0.10 | −0.19 | 0.33 | AC105416.1 | −1.00 | 1.16 | 1.44 | −1.36 | −0.10 | OR4C10P | 0.05 | −0.45 | −1.88 | 0.49 | −1.86 |
| SNCAIP | −0.43 | 0.25 | 0.70 | −0.16 | −0.20 | FTLP14 | 0.16 | −0.09 | 0.11 | 0.09 | 0.40 | AL117381.1 | 0.00 | 0.03 | −0.21 | 0.00 | −0.02 |
| AC114980.1 | −0.30 | 0.18 | 0.55 | 0.15 | 0.31 | AC120498.1 | −0.78 | −0.61 | −0.36 | 1.26 | −0.35 | AC012414.3 | −0.05 | −0.15 | −1.71 | 1.20 | −0.54 |
| AL136090.1 | 1.14 | −0.29 | −0.30 | 0.56 | 0.35 | NLRP3 | 0.22 | −0.91 | −0.23 | −0.29 | −0.14 | G3769 | −0.01 | −0.23 | 1.24 | 1.75 | 2.03 |
| RBMS3-AS3 | −0.67 | −0.20 | 0.69 | 0.26 | 0.11 | RP11-292F22.5 | 0.68 | −0.12 | −2.23 | −0.93 | −1.19 | RNU6-1315P | 0.01 | −0.11 | −0.62 | 1.10 | 0.21 |
| AC091516.1 | 0.72 | −0.57 | −0.50 | 0.19 | 0.42 | AC023983.1 | 0.24 | −0.26 | −0.51 | −0.02 | −1.00 | ARMCX5 | 0.00 | 0.18 | −0.05 | 0.17 | −0.08 |
| DCHS2 | −0.53 | 0.25 | 0.20 | 0.00 | −0.18 | STAT2 | 0.07 | −0.30 | −0.15 | −0.25 | −0.01 | AC106901.1 | −0.03 | −0.15 | −1.35 | 1.30 | 0.33 |
| NFATC3 | 0.15 | −0.01 | −0.05 | 0.06 | −0.05 | PPP2R2B-IT1 | −0.95 | −0.76 | 2.26 | −1.05 | 2.52 | AC008885.1 | −0.02 | −1.72 | 0.75 | 0.06 | −0.47 |
| SS18L1 | −0.25 | 0.09 | 0.16 | 0.07 | 0.12 | SLC4A2 | −0.08 | −0.09 | −0.22 | 0.02 | 0.04 | AC069185.1 | 0.00 | 0.16 | −0.02 | 0.70 | 0.30 |
| PPTC7 | 0.25 | 0.01 | −0.23 | −0.04 | −0.30 | AC096677.1 | −0.21 | −0.27 | 0.19 | 0.18 | 0.35 | AC093295.1 | −0.01 | 0.14 | −0.87 | 0.19 | −1.41 |
| AC006116.4 | −1.14 | 0.58 | 1.66 | 0.50 | 0.07 | AC090686.1 | 0.49 | −1.66 | −0.80 | 0.06 | 2.58 | LINC02313 | 0.01 | 1.44 | 0.26 | 0.99 | 0.00 |
| AL391647.1 | −1.26 | 0.60 | 1.74 | −0.47 | 0.12 | OR5M5P | −0.72 | −0.47 | −0.43 | 0.94 | −0.83 | AL390816.3 | −0.02 | −1.10 | −0.71 | −0.73 | −2.46 |
| G6692 | 1.75 | −1.59 | −2.69 | −0.67 | −2.47 | AC026254.2 | 0.52 | −0.68 | 1.03 | 0.61 | 1.27 | AC010975.2 | −0.05 | 0.09 | −0.23 | 0.29 | −2.30 |
| PTPRH | −0.53 | −0.20 | −0.06 | −0.09 | 0.26 | AC023669.1 | 1.08 | −0.60 | −2.09 | 1.02 | −0.25 | AC004386.2 | 0.05 | −0.41 | −1.01 | −0.07 | −0.83 |
| RYR3 | −0.30 | 0.33 | 0.20 | 0.34 | 0.11 | AC011603.4 | 1.14 | −1.38 | −1.21 | −0.75 | 1.05 | RPL23AP22 | 0.05 | 0.16 | 1.51 | 0.60 | −0.44 |
| GNG5 | 0.41 | −0.40 | −0.30 | −0.03 | 0.29 | ARHGDIG | −0.60 | 1.12 | −0.80 | 1.87 | 0.37 | AL161457.1 | 0.01 | 0.57 | 1.12 | 0.91 | 0.13 |
| NEDD4L | −0.36 | 0.36 | 0.06 | 0.01 | 0.04 | ENPP7P14 | −0.38 | 0.24 | 0.63 | 0.03 | 0.16 | AC022031.1 | −0.01 | −1.60 | 0.04 | −0.19 | 1.23 |
| DHRS11 | −0.28 | 0.26 | 0.14 | 0.17 | 0.15 | AC007969.2 | −0.88 | 0.45 | 0.71 | 0.01 | −0.68 | ATPAF1 | 0.00 | 0.11 | 0.03 | −0.01 | −0.08 |
| AC122718.1 | 0.40 | −0.46 | −0.62 | −0.18 | −0.11 | RSAD1 | −0.05 | −0.01 | 0.18 | 0.09 | 0.24 | SOX14 | 0.02 | −1.28 | −0.68 | −0.63 | −0.05 |
| PCNPP1 | −0.34 | 0.23 | −0.23 | 0.28 | 0.09 | C4orf33 | 0.09 | 0.09 | −0.17 | 0.13 | −0.25 | AC008740.2 | 0.02 | −1.84 | 0.54 | 0.78 | 2.16 |
| AC092140.1 | 1.14 | −0.34 | −0.95 | −0.13 | −1.41 | DENNDIA | −0.06 | 0.09 | −0.07 | 0.06 | 0.02 | LINC02027 | −0.05 | 0.03 | 0.60 | −1.19 | 0.48 |
| CENPP | 0.38 | −0.02 | −0.15 | −0.03 | −0.19 | NANOGP6 | 0.54 | −2.05 | −0.72 | −1.16 | −1.47 | LINC01065 | −0.05 | 0.32 | 0.05 | −0.64 | −1.67 |
| CCNT2 | 0.19 | −0.02 | −0.15 | −0.02 | −0.14 | AC147651.2 | −0.35 | −0.21 | 0.61 | −0.44 | 0.17 | OR4A18P | −0.05 | −0.36 | −0.20 | 1.87 | −0.39 |
| SF3A3P1 | 0.36 | −0.36 | −0.55 | 0.35 | 0.16 | AC009899.1 | 0.44 | 0.26 | −0.25 | −0.25 | −0.67 | OR7E55P | −0.02 | −0.49 | −0.26 | 0.83 | −0.69 |
| AC018946.1 | −0.44 | −0.59 | 0.07 | −0.50 | 0.49 | ANKRD34C-AS1 | −0.78 | −0.33 | −0.37 | 0.72 | 0.07 | AC120349.3 | 0.00 | −0.11 | 0.65 | 0.08 | 0.75 |
| CEP72 | −0.28 | −0.28 | −0.41 | 0.01 | 0.16 | AL139393.2 | −0.17 | 0.24 | 0.59 | 0.07 | 0.28 | RNA5SP40 | −0.05 | −0.12 | NA | −0.12 | −0.62 |
| CLDN14 | 0.79 | −0.72 | −1.17 | 0.14 | 0.17 | ART2P | 0.77 | −1.20 | 0.65 | 0.12 | 0.44 | MTCYBP17 | −0.05 | −0.50 | 0.09 | 0.32 | −0.71 |
| ANKRD13A | 0.18 | 0.01 | −0.12 | −0.03 | −0.20 | PRDM12 | −0.41 | −1.12 | −1.06 | −0.08 | 0.72 | OR8B2 | −0.03 | −1.27 | −0.48 | 0.62 | 2.58 |
| KRT18P60 | −0.66 | 0.01 | 0.43 | −0.09 | 0.10 | MTCO1P15 | −0.14 | −0.37 | 0.05 | −0.06 | 0.26 | CR382285.2 | −0.02 | −0.75 | −0.90 | 1.34 | −1.53 |
| AL162719.1 | −1.34 | −1.02 | 0.75 | −0.68 | 0.47 | HNRNPA1P28 | 0.55 | −1.33 | −1.51 | −0.63 | 0.32 | DEFA5 | 0.05 | −0.19 | 0.26 | 0.52 | 0.21 |
| RASGRP3 | 0.41 | −0.27 | −0.13 | −0.15 | −0.06 | AC016956.1 | −0.58 | 1.38 | −2.05 | 0.29 | −1.74 | AL683826.1 | 0.04 | −0.34 | −1.41 | 0.04 | −1.57 |
| RPS3AP43 | −1.11 | −0.23 | 1.67 | −0.51 | 0.79 | MTCO2P33 | 0.35 | −1.00 | −1.02 | 0.10 | 0.53 | AC072039.2 | −0.01 | 0.24 | 2.07 | 0.14 | 0.82 |
| MTUS1 | 0.20 | 0.09 | −0.20 | 0.09 | −0.13 | MDC1 | −0.05 | 0.00 | 0.01 | −0.11 | −0.04 | AC026474.1 | 0.00 | −0.25 | 0.09 | −0.05 | 0.31 |
| SIAH3 | −0.97 | 1.13 | −0.60 | 0.89 | −1.18 | RGPD4-AS1 | −0.57 | −0.07 | −0.50 | 0.63 | 1.87 | AC105446.1 | 0.02 | −0.17 | 0.28 | 0.17 | −1.01 |
| EZR | 0.31 | −0.11 | −0.68 | −0.03 | −0.52 | AL356311.1 | −0.75 | 0.34 | 1.59 | 0.30 | 0.11 | AC011005.3 | −0.05 | −1.50 | −0.41 | −1.55 | −0.26 |
| IFNA5 | −1.27 | 1.24 | 0.33 | 1.07 | −0.19 | SH3GL1 | 0.07 | 0.03 | −0.31 | −0.05 | −0.28 | EIF4A1P13 | 0.05 | −0.12 | −0.26 | 0.31 | 0.15 |
| LIVAR | 1.03 | −0.77 | −0.54 | 0.16 | −0.05 | MIR99A | −0.31 | −1.28 | 0.82 | −0.45 | 0.56 | CCNG1P1 | −0.03 | −0.97 | 0.30 | −0.30 | −0.07 |
| NUTF2P8 | −2.04 | 0.76 | 0.22 | −0.15 | −1.03 | AC022960.3 | 0.26 | −0.38 | 0.83 | 0.20 | 1.15 | AC012564.1 | 0.05 | −1.17 | −0.22 | 0.37 | 1.20 |
| HSBP1L1 | 0.25 | −0.02 | −0.19 | 0.06 | −0.11 | RN7SL338P | −0.15 | 0.11 | 0.56 | −0.32 | 0.20 | IFNA21 | −0.03 | −1.34 | −0.75 | −1.14 | 2.67 |
| AC093525.9 | −0.41 | −0.20 | 0.07 | 0.12 | 0.64 | AL591668.1 | 0.29 | −1.10 | −0.48 | 0.02 | 0.27 | AL354892.2 | 0.01 | −0.06 | 1.54 | 0.37 | 0.71 |
| NT5C3B | 0.23 | −0.06 | −0.23 | 0.00 | −0.10 | AC007160.1 | −0.49 | 1.14 | −0.87 | −0.10 | −1.06 | PDLIM1P1 | 0.01 | −0.02 | −0.35 | 0.05 | −1.16 |
| SPATA3-AS1 | 1.52 | −1.42 | −1.39 | −0.01 | −0.74 | AL133383.1 | 0.46 | −0.79 | 0.14 | 0.57 | −0.13 | NFATC2IP | 0.00 | −0.21 | −0.32 | 0.07 | 0.24 |
| GPR150 | −0.74 | −0.07 | 0.40 | −0.29 | −0.06 | RPL5P26 | 0.78 | −1.69 | −2.94 | 0.86 | 0.06 | CASC9 | −0.01 | 0.12 | −2.26 | 0.40 | −0.55 |
| METTL6 | 0.20 | −0.05 | −0.04 | 0.05 | −0.07 | RNA5SP33 | 0.18 | 0.14 | −1.08 | 0.61 | −0.14 | RAB42 | 0.00 | −0.18 | 0.96 | −0.60 | −0.33 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC087203.1 | −1.14 | 0.66 | 1.06 | 0.16 | 0.06 | RNY3P1 | −0.21 | 0.56 | 1.24 | −0.11 | −0.32 | HMGB1P12 | 0.05 | −0.45 | −1.70 | 0.87 | NA |
| AL157935.2 | −1.04 | −0.15 | 0.51 | −0.51 | −0.37 | LIPM | −0.16 | 0.52 | 1.33 | 0.70 | 0.10 | AC004946.1 | 0.03 | 1.20 | −0.72 | 0.64 | −2.36 |
| PAPOLG | 0.21 | 0.02 | 0.09 | −0.06 | −0.10 | AC100843.1 | 0.34 | 0.26 | −1.06 | 0.44 | −2.02 | OR10AH1P | −0.01 | −0.59 | −0.42 | 0.02 | −0.35 |
| RNU1-13P | −1.73 | 0.59 | −1.46 | 1.48 | −0.19 | RN7SL833P | 0.39 | −0.53 | 0.73 | −0.69 | 0.74 | CCNJP1 | −0.05 | 0.03 | −0.89 | 0.71 | −1.27 |
| LHPP | −0.20 | 0.16 | 0.16 | 0.10 | 0.05 | AC009102.3 | −0.35 | −1.24 | 0.14 | −0.65 | 1.61 | GPN3P1 | −0.05 | −0.76 | −0.33 | −0.80 | −0.55 |
| LINC01012 | −0.52 | −0.18 | −0.03 | 0.06 | 0.27 | SOCS7 | −0.05 | 0.22 | 0.03 | 0.18 | −0.04 | AC092045.1 | 0.00 | −0.05 | −0.39 | 0.00 | −0.60 |
| DUSP15 | −0.85 | 0.42 | 0.63 | 0.10 | −0.14 | RPS2P48 | −0.46 | 0.68 | −0.78 | −0.84 | −0.53 | LINC01898 | −0.02 | 0.41 | −0.23 | 0.65 | −2.27 |
| AC005622.1 | 1.11 | −0.86 | −2.26 | −0.16 | −1.91 | GLG1 | 0.05 | 0.09 | 0.16 | −0.06 | −0.08 | AL139124.1 | 0.01 | −0.85 | −1.16 | −0.04 | −0.39 |
| C1QTNF9B | −0.73 | 0.72 | 1.05 | 0.65 | 0.75 | AC007326.2 | 0.55 | −0.61 | −0.64 | 0.14 | −1.05 | RNA5SP96 | −0.03 | 1.37 | 0.53 | −0.02 | −2.36 |
| IKZF5 | −0.17 | 0.33 | 0.34 | 0.21 | 0.00 | AL021331.1 | 0.76 | 0.77 | −3.74 | 0.68 | −4.02 | AC083906.3 | −0.01 | 0.34 | 2.53 | 0.03 | 1.23 |
| ESRP2 | 0.33 | −0.19 | −0.44 | 0.15 | 0.10 | CYB561D2 | −0.12 | −0.05 | 0.00 | 0.08 | 0.16 | AC009081.1 | 0.05 | −0.48 | 0.83 | 0.73 | 1.30 |
| AC245060.2 | −0.67 | 0.60 | 0.35 | −0.25 | −0.08 | CATSPER4 | −0.33 | −0.63 | −0.65 | −0.31 | −0.74 | AC007458.1 | 0.05 | 1.07 | 0.37 | 0.93 | −1.19 |
| GON4L | −0.20 | 0.00 | 0.07 | −0.04 | 0.05 | AC008873.1 | 0.26 | −0.25 | 0.54 | −0.03 | 0.18 | DPPA3P2 | 0.02 | −0.08 | −1.37 | 1.93 | −0.87 |
| NADK | 0.23 | −0.08 | −0.26 | 0.01 | −0.08 | AL606752.1 | −0.94 | −1.12 | 0.07 | 1.38 | 1.35 | EI24P1 | 0.05 | −0.72 | −1.26 | 0.00 | −0.17 |
| AP001542.1 | 0.79 | −0.46 | 0.36 | −0.77 | −0.37 | AP000763.2 | 0.25 | −0.45 | −1.10 | −0.15 | −1.26 | AC105389.1 | −0.05 | −0.30 | 0.09 | −0.18 | 1.81 |
| DIAPH3-AS1 | 1.32 | −0.74 | −1.46 | 0.08 | −0.49 | LINC01938 | −0.53 | −1.33 | 0.95 | −1.59 | 0.28 | AC004805.2 | −0.01 | 0.04 | 0.72 | 0.11 | −0.09 |
| AC079385.1 | 0.72 | −0.65 | −0.38 | −0.09 | 0.67 | RPL7P46 | −0.11 | −0.11 | 0.18 | −0.04 | 0.11 | PPIAP4 | −0.01 | −0.19 | −0.26 | −0.26 | −0.52 |
| AL132633.1 | −1.12 | 0.35 | −1.16 | 1.38 | −0.78 | LINC01587 | −0.19 | −0.15 | −0.06 | −0.01 | 0.11 | SIGLEC10 | 0.00 | −1.14 | −0.90 | −0.34 | −0.28 |
| AC092427.1 | 0.57 | 0.03 | −0.11 | −0.97 | −1.13 | ACTL8 | 1.13 | −0.86 | −2.07 | 0.36 | −1.12 | AC007992.2 | −0.04 | −0.19 | −0.03 | −0.70 | −1.42 |
| RN7SKP116 | 0.96 | −0.06 | −0.61 | 0.23 | −0.48 | AP003121.1 | 0.55 | −0.50 | 1.50 | −0.48 | 0.23 | AC009961.3 | 0.00 | 0.14 | 0.15 | −0.05 | −0.28 |
| SNORA67 | 0.46 | 0.27 | −0.17 | 0.14 | −0.15 | PDE6G | −0.25 | 0.15 | −0.22 | 0.73 | −0.31 | LINC00308 | 0.01 | −1.64 | −1.43 | −0.78 | 1.34 |
| AC079250.1 | 0.55 | 0.19 | −0.36 | −0.04 | −0.40 | RMDN2-AS1 | 0.19 | −0.30 | −0.25 | 0.29 | −0.05 | RN7SL658P | −0.03 | −0.76 | −0.43 | 0.47 | 1.05 |
| AC239809.1 | −0.78 | 0.20 | 0.89 | 0.58 | 0.49 | OR9G1 | −0.39 | −0.30 | −1.90 | 0.13 | −1.27 | AC022819.1 | 0.00 | −0.01 | −0.11 | 0.00 | −0.07 |
| GPRC5D | 0.42 | −0.02 | −0.34 | −0.02 | 0.46 | AL663023.1 | 0.92 | −1.46 | −1.41 | −0.83 | 1.47 | RPL39P18 | −0.02 | 0.71 | −2.19 | 2.18 | 0.44 |
| KRT18P26 | −0.91 | 0.30 | 0.35 | 0.79 | 0.55 | PNPLA5 | −0.37 | 1.40 | 0.40 | 1.92 | 0.60 | IFNA13 | −0.05 | −0.58 | 1.16 | −1.55 | −0.38 |
| PGP | 0.24 | −0.29 | 0.00 | −0.10 | 0.31 | RPS27AP17 | 0.66 | 0.07 | −1.17 | 1.16 | −0.40 | IMMP1LP3 | 0.01 | 0.46 | −0.27 | −0.14 | −0.19 |
| AF212831.1 | −0.91 | 1.87 | 1.62 | 0.24 | −0.29 | AC017028.7 | 0.25 | 0.12 | −0.77 | 0.32 | 0.27 | AC091951.1 | 0.01 | −1.54 | −0.93 | −1.02 | −1.91 |
| AL035685.1 | −1.03 | 0.41 | 0.60 | 0.41 | −0.12 | AC015722.2 | −0.74 | 0.34 | −0.75 | 0.54 | −0.10 | AC138393.3 | 0.00 | 0.12 | 0.45 | −0.22 | 0.30 |
| RNU6-27P | −1.25 | −0.49 | −1.06 | 0.60 | −1.22 | AC007849.1 | 0.23 | 0.08 | 0.35 | −0.23 | 0.13 | AP000820.2 | 0.01 | 0.21 | 0.63 | −0.18 | 0.07 |
| ENSA | 0.21 | 0.07 | −0.09 | 0.12 | −0.05 | AC024084.1 | 0.32 | 0.47 | 0.10 | −0.18 | −0.33 | RN7SL594P | −0.01 | −0.62 | −0.68 | 0.19 | 0.28 |
| SNAPC3 | −0.13 | −0.04 | 0.27 | −0.12 | 0.15 | AC018371.1 | −0.66 | −0.87 | 0.08 | −0.65 | 0.04 | HSPA8P4 | 0.00 | 0.06 | 0.47 | −0.56 | −0.48 |
| RPL13AP2 | −0.84 | −1.02 | 0.15 | 0.57 | 1.03 | AC104961.1 | −0.34 | 0.99 | −1.02 | 0.24 | −1.30 | AL157937.1 | 0.02 | −0.40 | −1.46 | −0.96 | −2.76 |
| AC093382.1 | 0.54 | −0.18 | −0.63 | 0.35 | −0.20 | IGLV3-21 | 0.51 | 2.04 | 0.04 | −1.33 | −1.27 | CRYGB | 0.04 | −0.55 | 0.20 | −0.30 | 1.13 |
| 8-Mar | −0.24 | 0.30 | 0.18 | 0.16 | −0.21 | LINC01583 | −0.38 | −0.15 | −0.21 | 0.47 | 0.28 | C17orf98 | 0.02 | −0.75 | −0.23 | 0.47 | 0.63 |
| LINC02431 | −1.49 | 0.98 | 0.17 | 0.40 | −0.46 | AC090519.3 | 0.45 | −0.80 | −0.88 | 1.30 | 1.05 | AC055753.1 | 0.04 | −1.07 | 0.03 | −0.42 | 2.02 |
| LINC01792 | 1.31 | −1.58 | −0.55 | −0.87 | 0.97 | AC098848.1 | −0.20 | 0.37 | 0.70 | 0.61 | 0.28 | MRPS26 | 0.00 | −0.04 | −0.23 | 0.12 | 0.16 |
| EHD3 | 0.32 | −0.21 | −0.05 | −0.33 | 0.00 | AC091979.1 | −0.65 | −0.66 | −1.78 | 0.35 | −0.36 | H2AFZP5 | 0.03 | 0.66 | 0.16 | 1.80 | −1.15 |
| MOCS1 | −0.53 | −0.11 | 0.20 | 0.20 | 0.35 | ADGRF5 | −0.16 | 0.07 | 0.76 | −0.23 | −0.11 | RN7SKP194 | −0.04 | 0.25 | 0.57 | −0.34 | −0.34 |
| AC090360.1 | −0.42 | 0.18 | 0.72 | 0.08 | 0.41 | AL161443.1 | 0.21 | −0.26 | −0.13 | 0.32 | 0.43 | KRTAP13-3 | −0.04 | −0.52 | −1.39 | 1.30 | −1.19 |
| AC010226.1 | 0.64 | −0.46 | 0.15 | −0.28 | 0.21 | LINC02120 | 0.24 | −0.53 | 0.20 | 0.36 | 0.34 | DUXAP11 | −0.02 | −0.52 | −1.19 | 0.16 | −0.90 |
| SNRNP35 | −0.21 | 0.01 | −0.04 | 0.11 | 0.05 | G24466 | −0.33 | 0.56 | 2.15 | 0.18 | 0.71 | AC093689.1 | 0.04 | −0.53 | −0.49 | −0.47 | −0.93 |
| AP000344.2 | −1.58 | 1.24 | 0.05 | −0.73 | −0.92 | HMGB1P1 | 0.20 | −0.11 | −0.50 | 0.69 | 0.15 | AC097467.2 | 0.04 | −0.67 | −0.47 | −1.13 | −2.33 |
| AK2P2 | −1.08 | −0.94 | −0.08 | −0.28 | 0.39 | AC245140.3 | −0.29 | −0.44 | −0.29 | 1.21 | 0.32 | AC097494.1 | −0.02 | −0.51 | −1.35 | 1.28 | −0.53 |
| AC007365.1 | 0.53 | −0.02 | −0.44 | 0.26 | 0.12 | BRWD1-IT1 | −0.15 | 0.15 | 0.01 | −0.12 | −0.06 | EEF1A1P28 | 0.01 | 0.26 | −0.85 | 1.44 | 0.26 |
| AC104248.1 | −1.28 | −0.41 | 1.85 | 0.05 | 0.63 | EME1 | 0.13 | −0.57 | −0.53 | −0.28 | 0.12 | RN7SKP196 | −0.02 | 0.80 | −0.87 | 0.62 | 0.52 |
| G23772 | −1.22 | 0.71 | 1.11 | 0.00 | 0.07 | LINC01745 | 1.18 | −1.26 | −0.96 | −0.92 | −1.88 | RS1 | 0.01 | −1.28 | 0.22 | −0.56 | 0.61 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| FAUP2 | −1.25 | 0.07 | 0.29 | −0.01 | 0.69 | AL627308.1 | 0.22 | −0.40 | 0.19 | −0.12 | 0.69 | DUPD1 | 0.02 | −0.57 | −3.10 | 1.28 | −1.68 |
| NVL | −0.17 | 0.04 | 0.17 | 0.05 | 0.20 | AC021443.1 | 0.32 | −0.74 | 1.03 | 0.33 | 1.20 | AC093639.1 | 0.04 | −1.97 | 0.34 | −2.28 | 1.32 |
| OAF | 0.45 | −0.17 | −0.14 | −0.24 | −0.08 | LINC02416 | 0.68 | −0.36 | −0.69 | −0.42 | −0.15 | EDDM3DP | 0.04 | 0.55 | −0.58 | −1.72 | −1.35 |
| AL591499.1 | −1.15 | −0.63 | −0.87 | 0.52 | 0.28 | AP000777.2 | −0.46 | 0.09 | −0.75 | −0.07 | −0.53 | CLNK | 0.00 | −0.23 | 0.39 | −0.39 | 0.50 |
| BRAP | 0.16 | −0.08 | −0.19 | −0.05 | −0.11 | PROX1-AS1 | −0.26 | −0.23 | −0.82 | 0.26 | −0.73 | AL645998.1 | −0.01 | 0.59 | 1.89 | −0.06 | 0.01 |
| KRTAP10-12 | −1.29 | 0.92 | 0.00 | 1.35 | −0.88 | NDUFA5P3 | 0.87 | 0.34 | −2.18 | 1.26 | −2.31 | AC019077.1 | −0.01 | −0.80 | −0.54 | −0.53 | 0.00 |
| GPR22 | 0.43 | 0.02 | −0.02 | 0.06 | 0.12 | KIAA1257 | 0.13 | −0.06 | 0.22 | 0.14 | −0.11 | IGHVII-28-1 | −0.04 | −0.86 | −0.04 | −0.31 | −0.54 |
| CDC37L1 | 0.21 | −0.09 | −0.06 | −0.08 | −0.11 | MFGE8 | −0.08 | 0.19 | −0.22 | 0.26 | −0.11 | FIGLA | 0.01 | 1.06 | 2.12 | 1.23 | 0.78 |
| KIAA1586 | 0.30 | −0.18 | −0.07 | 0.04 | 0.05 | MTND2P21 | −0.61 | 0.46 | −0.84 | 0.74 | −0.72 | AL353194.1 | 0.00 | −0.17 | 1.10 | −0.58 | 0.36 |
| CORO1B | 0.16 | −0.07 | −0.50 | 0.09 | −0.19 | PGCP1 | −0.40 | 0.27 | −1.91 | 0.37 | −2.41 | IGKV2-10 | −0.04 | −0.23 | −0.32 | 0.03 | −0.65 |
| AP000462.1 | 0.85 | −0.33 | −0.28 | 0.03 | 0.39 | SEC62 | −0.10 | 0.07 | 0.22 | −0.20 | −0.13 | MAGEB6B | −0.04 | −0.60 | 0.37 | −0.39 | 0.06 |
| LINC00479 | −0.68 | 0.22 | 0.04 | −0.30 | −0.19 | RNU6-435P | 0.54 | −0.32 | 0.33 | 0.37 | 0.99 | AC004217.1 | −0.01 | −0.23 | −0.06 | 0.03 | −0.30 |
| MAPK6-DT | 0.97 | −0.25 | −1.30 | −0.21 | −0.61 | AC007463.1 | 0.71 | −0.09 | −1.72 | 1.65 | −2.24 | AC207130.1 | −0.01 | −0.61 | −1.06 | −0.20 | −0.04 |
| ST3GAL6 | −0.26 | 0.10 | 0.40 | −0.15 | 0.21 | RNU6-19P | 0.53 | −0.73 | 0.84 | −0.39 | 1.14 | MTCYBP27 | 0.02 | −0.77 | −0.68 | 0.98 | −1.64 |
| AL139120.1 | 0.58 | −0.03 | −0.40 | 0.04 | 0.14 | AC091493.1 | 1.31 | −0.57 | −0.79 | −0.60 | −0.80 | AL445984.1 | 0.04 | −0.91 | −0.44 | −1.23 | −0.32 |
| AL583808.3 | 1.05 | 0.26 | −0.30 | 0.10 | −0.71 | SNORA36B | −0.15 | −0.03 | 0.34 | 0.02 | 0.23 | AC005518.1 | 0.04 | −1.02 | −1.15 | −0.34 | 1.34 |
| AC023024.2 | 0.75 | −0.73 | 0.27 | −0.32 | 0.57 | AC025268.1 | 0.19 | −0.06 | −0.08 | 0.00 | −0.32 | CD83P1 | 0.04 | 0.54 | −0.38 | 0.86 | −0.59 |
| AC006441.1 | −0.39 | −0.17 | 0.28 | −0.17 | 0.51 | DPP9 | 0.08 | −0.15 | −0.56 | 0.07 | −0.07 | PARP1P1 | 0.01 | −1.04 | −0.21 | −0.36 | −0.18 |
| SMIM4 | 0.32 | −0.02 | 0.01 | −0.18 | −0.21 | FNIP1 | −0.06 | 0.14 | 0.12 | 0.04 | −0.16 | BNIP3P22 | 0.01 | −0.36 | 0.45 | −0.59 | −0.81 |
| AC115837.1 | 0.35 | −0.22 | 0.00 | 0.03 | 0.25 | RPL34P19 | 0.81 | 0.65 | −0.02 | −0.31 | 0.72 | OR52J2P | 0.04 | −1.30 | −0.34 | 0.86 | 0.47 |
| DEFB4B | 3.40 | −2.83 | −2.55 | −2.03 | −3.15 | OR10J2P | −0.46 | −0.06 | 1.39 | 0.30 | 1.06 | AC073488.9 | 0.04 | 0.24 | −0.83 | 2.55 | 0.94 |
| HSPE1 | 0.43 | −0.38 | −0.18 | −0.19 | −0.05 | FZD10 | 0.16 | 0.47 | −0.79 | 0.56 | −1.10 | PRAMEF35P | 0.04 | −1.37 | 0.14 | −1.40 | −0.15 |
| SLC45A2 | −0.65 | 0.52 | 0.42 | 0.36 | −0.21 | NFKBIA | 0.11 | −0.17 | −0.72 | 0.06 | −0.38 | AC026458.2 | −0.01 | −1.08 | 1.70 | 0.11 | 3.08 |
| POMGNT2 | −0.29 | 0.43 | 0.57 | 0.05 | 0.08 | ATG12 | −0.06 | −0.06 | 0.26 | 0.05 | 0.12 | AC009163.5 | −0.04 | 0.15 | −1.10 | 0.82 | −1.21 |
| NPAP1P3 | −1.50 | −0.43 | −0.42 | −1.70 | −1.07 | CDC37L1-DT | 0.19 | −0.03 | −0.04 | 0.37 | 0.20 | AL390726.1 | 0.04 | −0.40 | NA | −0.25 | NA |
| GAPDHP27 | −1.22 | 0.65 | 1.68 | −0.36 | 0.63 | AL671986.1 | −0.16 | 0.29 | 0.48 | −0.09 | 0.03 | AL359508.1 | −0.02 | −0.84 | −3.38 | 0.66 | −1.89 |
| AC104978.1 | 1.21 | −0.19 | −0.79 | 0.10 | 0.06 | AL160279.1 | 1.20 | −1.14 | −2.53 | −0.28 | 0.44 | AC010538.1 | 0.00 | −0.30 | −0.09 | −0.54 | 0.00 |
| SLC17A4 | −1.21 | 0.13 | −1.05 | 0.10 | −0.97 | AL118509.1 | 0.68 | 0.26 | −1.09 | 0.82 | −0.02 | HSD3BP1 | −0.01 | −0.86 | −1.23 | −0.42 | 0.02 |
| POLG | −0.20 | −0.09 | −0.19 | 0.07 | 0.12 | AC005858.3 | −1.04 | −0.64 | −0.04 | 0.61 | −0.39 | AP001153.1 | 0.04 | −0.67 | 0.11 | −0.18 | 0.26 |
| CALM3 | 0.20 | −0.20 | −0.09 | −0.26 | −0.08 | G3707 | −0.23 | 0.62 | 1.60 | 0.46 | −0.35 | MTND3P8 | 0.04 | −0.70 | −1.52 | −0.33 | −0.44 |
| AATBC | −0.45 | 0.30 | −0.13 | 0.45 | 0.06 | AC126564.1 | −0.65 | −0.98 | −1.86 | 0.35 | 2.00 | AC092284.1 | 0.02 | −0.40 | −0.15 | −0.47 | 0.89 |
| PKHD1L1 | −0.54 | 0.71 | 0.74 | 0.77 | 0.11 | AC099789.1 | 0.44 | −0.75 | −1.11 | −0.01 | 0.32 | RNU6-96P | 0.00 | −0.44 | 0.80 | −0.40 | 0.13 |
| AC007319.1 | −0.49 | 0.37 | 0.86 | 0.25 | 0.26 | SNORA24 | −0.22 | 0.42 | −0.15 | 0.29 | −0.71 | AC008267.5 | 0.02 | 0.14 | 0.14 | −1.23 | −1.81 |
| AC009948.1 | 0.26 | −0.06 | −0.10 | −0.09 | 0.07 | C2orf16 | 0.14 | −0.06 | −0.38 | 0.04 | −0.21 | AC140725.2 | −0.04 | −0.63 | −0.56 | −0.44 | −0.65 |
| AC020661.3 | 0.82 | −0.35 | −1.59 | 0.50 | −0.07 | GOLGA8EP | −0.71 | −1.78 | −0.26 | −0.49 | 0.28 | AC125238.1 | −0.04 | 0.25 | −0.68 | 0.93 | −1.22 |
| JARID2-AS1 | −0.53 | 0.37 | −0.37 | 0.20 | −0.40 | LPP-AS1 | 0.15 | −0.63 | −0.15 | −0.47 | 0.19 | AC096763.1 | −0.04 | −0.12 | 0.96 | −0.18 | 0.88 |
| RNU7-49P | 0.87 | −1.56 | −0.27 | −0.04 | −0.17 | AL162511.1 | −0.65 | 0.28 | −0.49 | −0.27 | −1.94 | AC025198.1 | 0.00 | −0.59 | −0.18 | 0.57 | 1.04 |
| SMCR8 | 0.15 | −0.07 | −0.10 | −0.06 | −0.04 | DDX10P1 | −0.12 | 0.13 | −0.01 | 0.18 | −0.01 | ISPD-AS1 | 0.00 | 0.45 | 0.26 | 0.31 | 0.01 |
| HS6ST1P1 | 0.61 | 0.09 | −0.49 | 0.05 | −0.32 | IRGM | −0.21 | −0.40 | −1.08 | 0.03 | −0.58 | MIR106B | 0.01 | 0.31 | 1.54 | −0.13 | 0.98 |
| CALCR | −1.03 | 1.30 | −0.96 | 0.80 | −0.98 | ATP8A2 | −0.19 | 0.28 | −0.09 | −0.25 | −0.93 | CLDN19 | 0.01 | −0.62 | 0.37 | 0.19 | 0.44 |
| NAALADL1 | −0.46 | −0.08 | −0.05 | 0.25 | 0.50 | AC121758.3 | −1.17 | −0.16 | 0.91 | −0.33 | 1.14 | AC090124.3 | 0.01 | 0.91 | 0.29 | −0.66 | −0.82 |
| GOLGA6L3 | −0.53 | 0.27 | 0.10 | 0.10 | −1.19 | RN7SKP72 | −0.78 | 1.06 | 0.65 | 0.43 | −0.42 | AL122008.1 | −0.01 | 0.04 | −0.68 | 0.59 | −0.67 |
| AC003991.1 | 0.53 | −0.56 | −0.60 | −0.24 | −0.72 | G16821 | −0.30 | 0.29 | −0.27 | 0.03 | −0.08 | AC091286.1 | 0.02 | −0.17 | −0.06 | −0.36 | 1.70 |
| ARMCX2 | −0.53 | 0.29 | 1.03 | −0.45 | 0.26 | AL360004.1 | −0.30 | 0.27 | −0.62 | 0.41 | −0.08 | MIR545 | 0.01 | −0.88 | −0.18 | 0.57 | −0.19 |
| LILRB2 | 0.65 | −0.97 | −0.58 | −0.85 | −0.28 | AL133330.1 | −0.12 | −0.22 | −0.09 | −0.14 | 0.24 | RN7SKP111 | 0.04 | −0.46 | −1.07 | 0.50 | 0.05 |
| AC009090.1 | −0.51 | 0.43 | 0.21 | 0.41 | −0.58 | PAXIP1-AS1 | −0.27 | 0.43 | 0.19 | −0.10 | −0.46 | C1GALT1P3 | 0.01 | −1.19 | −0.67 | 0.95 | 0.27 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| PSTPIP2 | 0.27 | −0.22 | −0.45 | 0.02 | −0.05 | AC008780.2 | −0.83 | 0.65 | −0.72 | −0.20 | −0.03 | AL162399.1 | 0.02 | −0.41 | 0.23 | −0.34 | −0.25 |
| AL592463.1 | −1.36 | 1.23 | 0.91 | 0.73 | 0.59 | AC004835.1 | −0.41 | 0.91 | −1.71 | 1.04 | −1.16 | HNRNPA1P43 | −0.01 | −0.13 | −1.31 | 0.52 | −2.05 |
| AP003032.1 | −1.27 | 1.69 | 1.23 | 1.61 | 0.82 | PRUNE1 | 0.06 | 0.09 | 0.07 | 0.00 | 0.11 | LINC00378 | 0.02 | −1.88 | −1.66 | −0.92 | 1.05 |
| LINC02081 | 1.02 | −1.53 | −1.06 | 0.02 | 0.68 | FLRT2 | −0.09 | 0.10 | 0.32 | −0.27 | −0.02 | RPSAP7 | −0.04 | −0.76 | −0.98 | 0.35 | 0.15 |
| PARP15 | 0.58 | −0.57 | −0.18 | −0.39 | 0.23 | RNU4-59P | 0.43 | 0.20 | 0.45 | −0.09 | 0.54 | MGAT4D | 0.01 | −0.66 | −0.36 | 0.43 | 0.20 |
| AC011492.1 | 0.84 | 0.01 | 0.10 | −0.36 | −0.39 | AC010878.1 | 0.66 | −0.08 | −1.43 | 0.99 | −2.15 | LINC00951 | 0.04 | −0.07 | −0.83 | 0.51 | −2.37 |
| HMGN3 | −0.23 | 0.10 | 0.25 | 0.13 | 0.10 | AF131215.6 | 0.10 | −0.12 | 0.00 | −0.19 | 0.01 | AL136363.2 | 0.04 | 0.14 | 0.50 | 0.99 | −1.17 |
| C9orf72 | 0.23 | −0.17 | −0.10 | −0.13 | −0.17 | KRTAP5-1 | 0.31 | −0.56 | −1.28 | 0.45 | −1.22 | AC004801.3 | −0.04 | 0.83 | −0.49 | −0.64 | −2.05 |
| AC069029.1 | 0.93 | 0.14 | −0.60 | 0.04 | −1.04 | MRPS30 | 0.08 | 0.01 | 0.23 | −0.06 | 0.05 | AL355836.1 | 0.04 | −0.86 | −0.94 | 1.12 | −0.15 |
| FBXO22 | 0.19 | −0.18 | −0.07 | −0.05 | 0.12 | MTND4P34 | −0.41 | −0.41 | 1.68 | 0.05 | 0.36 | AL033380.1 | −0.01 | −1.90 | 0.03 | −1.31 | −1.45 |
| AC039056.1 | 0.73 | −0.26 | −0.04 | −0.42 | −0.12 | AP002991.2 | 0.50 | −0.90 | −1.82 | −0.47 | −0.45 | H3F3C | 0.00 | 0.49 | −0.83 | 0.01 | −1.92 |
| CCDC196 | −0.43 | −0.14 | 0.64 | −0.26 | 0.54 | AC239802.2 | −0.27 | −0.04 | −0.05 | −0.10 | −0.60 | AL021877.1 | −0.01 | −1.34 | 0.70 | 0.07 | 0.69 |
| PIRT | −0.90 | 0.53 | 0.97 | 0.18 | −0.80 | AL158168.1 | 0.60 | −0.40 | −1.77 | 0.33 | −1.39 | RN7SL187P | 0.00 | −0.41 | 0.81 | −0.38 | 1.21 |
| IGKV1OR-2 | −1.04 | −0.29 | 0.16 | −0.48 | 0.61 | RNU1-42P | −0.80 | −0.03 | −0.93 | 2.67 | 1.87 | OR2W5 | −0.01 | −0.94 | −0.29 | −0.22 | −0.21 |
| CCNT2-AS1 | −0.76 | 0.11 | 1.20 | −0.26 | 0.71 | AC106799.3 | −0.38 | −0.37 | −0.79 | 0.30 | 0.19 | AC026462.4 | −0.01 | −0.65 | −0.78 | −0.20 | 0.98 |
| AL031005.1 | −0.43 | 0.48 | 0.52 | 0.03 | 0.34 | RNU6-912P | −0.68 | 0.08 | −0.27 | 0.07 | −2.15 | COX412 | 0.00 | 0.01 | 0.48 | 0.58 | 0.08 |
| AL390026.1 | 1.84 | −0.95 | −0.20 | −0.08 | −0.25 | CDC34 | −0.09 | 0.28 | 0.01 | 0.17 | −0.21 | AL158800.1 | 0.02 | 0.29 | −0.34 | 0.72 | −1.31 |
| RPL35AP32 | 0.61 | −0.50 | 0.25 | −0.51 | 0.48 | PPIAP53 | −0.22 | −0.14 | 0.83 | −0.24 | 0.52 | KAZN | 0.00 | −0.07 | −0.38 | 0.11 | −0.07 |
| KIAA0930 | 0.18 | 0.04 | −0.07 | 0.07 | −0.15 | AC124944.1 | −0.48 | 1.25 | 0.23 | −0.18 | −1.31 | OR6C65 | −0.04 | NA | 0.02 | 1.03 | 1.64 |
| AGAP11 | −1.00 | 1.07 | 1.21 | 0.36 | 0.06 | G19572 | 0.51 | −0.40 | 0.93 | −0.81 | 1.82 | AC106870.2 | 0.04 | −0.41 | 0.37 | 0.31 | −0.52 |
| HSPG2 | −0.36 | 0.14 | 0.44 | −0.05 | 0.06 | NAP1L1P2 | −0.75 | −0.21 | −0.24 | 0.70 | 0.29 | AC078845.1 | −0.01 | 0.79 | −0.08 | 0.16 | −0.62 |
| CXXC4-AS1 | −0.70 | 0.25 | −0.12 | 0.31 | −0.62 | MANSC4 | 0.30 | −0.52 | 0.63 | −0.56 | 0.83 | OTX1 | 0.00 | 0.43 | −0.02 | 0.47 | 0.14 |
| AC010894.3 | −0.34 | 0.11 | 0.45 | −0.40 | −0.08 | SNORA2 | 0.22 | −0.59 | −1.23 | −0.08 | −0.44 | AC012506.3 | 0.04 | 0.09 | −0.27 | 0.90 | −0.49 |
| AC004865.2 | −0.64 | 0.33 | 0.32 | 0.36 | 0.19 | AC106047.1 | 0.21 | 0.33 | 0.14 | 0.24 | −0.19 | OR5T3 | 0.04 | 0.17 | −1.26 | 0.66 | −0.65 |
| DLG5 | −0.23 | 0.03 | −0.21 | 0.12 | 0.12 | AL162430.2 | −0.17 | 0.11 | −0.29 | 0.20 | −0.06 | AC068944.1 | −0.01 | −0.09 | −2.41 | 0.97 | −1.29 |
| COL5A2 | 0.45 | −0.03 | 0.35 | −0.81 | −0.53 | CSTF3-DT | −0.34 | 0.95 | −2.31 | 0.96 | −2.41 | RPS3AP25 | −0.01 | 0.82 | −0.53 | 0.22 | −0.53 |
| AC106795.5 | 1.19 | −1.13 | 0.03 | 0.10 | 1.16 | AC004012.1 | −0.38 | −0.09 | 0.78 | 1.06 | 1.51 | OR5AK2 | −0.02 | −0.31 | 0.29 | 0.15 | −2.81 |
| G36319 | −0.67 | 0.32 | 0.51 | 0.27 | 0.38 | LINC01020 | 0.46 | −0.37 | −1.31 | 0.66 | −1.31 | AC114964.1 | −0.04 | 0.02 | −0.67 | 0.06 | −1.21 |
| AC106820.6 | 1.50 | −1.78 | −0.32 | 0.80 | 2.97 | ERFE | 0.18 | −0.24 | −0.70 | −0.01 | 0.08 | AC241644.2 | 0.01 | 0.44 | −1.07 | −0.12 | −0.79 |
| AC016559.2 | −0.88 | 0.66 | 0.98 | −0.09 | −0.70 | SLCO2B1 | 0.16 | −0.27 | −0.41 | −0.10 | 0.00 | AC009396.3 | 0.04 | −0.21 | −0.86 | −1.64 | −1.37 |
| AC124242.1 | −0.71 | 0.26 | 0.55 | 0.14 | −0.51 | AC055720.1 | −0.39 | 0.70 | −0.38 | 0.45 | 0.32 | RIMS2 | 0.00 | −0.26 | −0.50 | −0.49 | −0.55 |
| AL157396.1 | −1.01 | 0.26 | 0.10 | 0.17 | −0.03 | OR10AE3P | −0.69 | 0.89 | 0.82 | 1.38 | 0.75 | OR10T1P | 0.02 | 0.15 | −1.57 | 0.98 | −0.95 |
| AP003716.1 | −0.59 | 0.75 | 0.78 | 0.07 | −0.07 | AC013355.1 | 0.45 | −1.49 | −1.36 | 1.00 | −0.30 | RPS3AP41 | −0.02 | 0.14 | 1.09 | 0.10 | 0.43 |
| LINC00314 | −0.90 | 0.44 | 0.45 | −0.13 | −0.27 | PIWIL1 | −0.28 | −0.38 | −0.12 | −0.36 | 0.13 | AC002487.1 | 0.02 | 0.00 | −1.30 | 0.43 | 0.12 |
| MEN1 | 0.18 | 0.02 | −0.22 | 0.02 | −0.05 | PNOC | −0.24 | −0.50 | 1.04 | 0.09 | 0.64 | FOXK1 | 0.00 | 0.06 | −0.14 | 0.20 | −0.02 |
| MKLN1-AS | −0.41 | 0.26 | 0.57 | 0.01 | 0.33 | RPS18P12 | 0.21 | 0.24 | −0.27 | 0.59 | −0.28 | RPL21P136 | 0.00 | −0.14 | 0.03 | 0.13 | 0.01 |
| LMTK2 | 0.19 | 0.21 | −0.22 | 0.16 | −0.31 | BBX | −0.06 | 0.11 | 0.15 | 0.06 | −0.04 | AC093752.2 | 0.00 | −0.11 | 0.21 | 0.09 | 0.04 |
| NDRG3 | 0.21 | −0.02 | 0.05 | −0.03 | −0.09 | BIN2P2 | 0.74 | −1.87 | −0.41 | 0.54 | 1.25 | AC023136.1 | −0.01 | 1.04 | 0.89 | −0.49 | −0.98 |
| FIP1L1 | 0.19 | −0.16 | −0.19 | −0.17 | −0.13 | RPL7AP66 | 0.15 | 0.40 | −0.03 | 0.15 | −0.27 | NMNAT1P2 | 0.04 | −0.15 | 0.04 | −0.73 | −1.30 |
| AC011199.1 | −0.75 | −0.81 | −0.27 | 0.23 | 0.47 | GCSAML | −0.21 | 0.13 | 0.33 | −0.08 | −0.22 | KRTAP19-1 | 0.01 | 0.03 | 0.94 | −0.23 | −0.74 |
| AP002981.1 | −1.31 | 1.01 | −0.08 | 0.29 | 0.72 | AC024592.2 | −0.41 | −1.05 | −0.42 | −1.33 | −0.67 | AC003087.1 | −0.02 | −0.96 | −0.41 | 0.80 | −0.03 |
| F13A1 | −0.59 | 0.42 | 0.59 | 0.11 | 0.18 | LINC01841 | 0.44 | −0.60 | −1.55 | 0.02 | −0.44 | AC091805.2 | 0.03 | −0.69 | −0.72 | 2.38 | 0.20 |
| EHBP1 | −0.27 | 0.20 | 0.00 | 0.12 | 0.16 | AL592546.1 | 0.19 | 0.11 | 0.04 | 0.10 | 0.22 | OR7E23P | 0.03 | −0.67 | −0.77 | 0.17 | −0.40 |
| NAV2-IT1 | −1.14 | 1.20 | 0.38 | 0.39 | −0.61 | RPL12P38 | −0.30 | −0.18 | 0.07 | 0.27 | −0.11 | IGHE | 0.04 | −0.02 | 1.25 | 0.51 | 5.35 |
| AC105285.1 | −0.48 | −0.05 | 1.25 | −0.32 | 0.83 | SLC6A12 | −0.22 | −0.32 | −0.61 | 0.03 | −0.23 | AC073488.3 | 0.03 | 0.35 | −0.71 | 0.01 | −0.99 |
| AP005329.1 | 0.76 | 0.27 | −0.44 | 0.27 | −0.49 | AC009075.2 | 1.00 | −1.05 | 0.74 | −0.89 | 2.59 | AC083906.1 | 0.01 | 1.04 | 2.27 | 0.46 | 1.39 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| JMJD6 | 0.21 | −0.34 | −0.47 | −0.34 | −0.16 | AL136038.3 | 0.28 | −0.77 | −1.50 | −0.13 | −0.41 | AL133387.1 | −0.03 | −0.84 | 0.06 | −0.61 | −0.07 |
| AL672207.1 | 1.11 | −0.42 | −0.97 | −0.20 | 0.26 | AC025809.1 | −0.25 | −0.16 | 0.70 | −0.44 | 0.01 | AC092925.1 | −0.03 | −0.44 | −0.56 | 0.37 | NA |
| AC109462.1 | −1.60 | 1.07 | 0.80 | 0.94 | 1.22 | AL445183.2 | −1.09 | −0.34 | 1.19 | 0.25 | 1.84 | AC106053.1 | 0.00 | 0.04 | 0.43 | 0.31 | 0.36 |
| AC036176.2 | −0.38 | 0.14 | −0.14 | 0.12 | 0.08 | AL031600.2 | 0.28 | −0.25 | −1.47 | −0.06 | −1.05 | AC008764.4 | 0.01 | −0.19 | 0.50 | 0.50 | 1.22 |
| NRIR | 0.95 | −1.69 | −1.15 | −0.91 | 0.74 | ARHGAP11B | 0.34 | −0.02 | −1.37 | 0.17 | −0.63 | GYG1P2 | 0.03 | −0.42 | −0.21 | 0.17 | 1.12 |
| P3H4 | 0.30 | −0.18 | 0.17 | −0.35 | −0.01 | G18874 | −0.33 | −0.19 | −0.53 | 0.04 | 0.20 | G354 | 0.01 | −0.41 | 0.81 | −0.81 | −0.36 |
| FAM207A | 0.26 | −0.20 | −0.46 | −0.04 | −0.10 | AP000719.1 | 0.52 | 0.78 | −0.55 | −0.51 | −0.76 | ARL6IP1P3 | 0.03 | −0.89 | −0.61 | −0.06 | −0.66 |
| HERC5 | 0.39 | −0.44 | −0.37 | −0.20 | −0.17 | RBMX2P4 | 1.04 | −1.05 | −0.47 | 1.06 | 1.40 | AL731563.1 | 0.01 | 0.70 | −1.37 | 0.64 | −1.49 |
| CORO1C | 0.24 | −0.18 | −0.26 | −0.22 | −0.38 | AC011442.1 | −0.16 | −0.25 | −0.24 | −0.07 | 0.03 | AC243312.1 | −0.01 | −0.52 | −0.07 | −0.12 | 0.18 |
| AJ006995.1 | −0.97 | 0.57 | 1.33 | 0.21 | 0.19 | C9orf92 | −0.50 | 0.44 | −2.14 | −0.07 | −2.82 | AL139327.2 | −0.03 | 0.19 | −0.05 | 1.63 | 0.78 |
| ANXA5 | 0.33 | −0.24 | −0.25 | −0.26 | −0.28 | AL049838.1 | −0.34 | 1.96 | 0.20 | 0.93 | −0.52 | LINC01644 | −0.01 | −0.54 | −0.41 | −0.95 | 0.64 |
| MOSPD2 | −0.21 | 0.25 | 0.61 | 0.16 | 0.34 | AL359399.1 | 0.63 | −0.11 | −0.97 | 0.57 | −0.77 | IGKV1-17 | 0.03 | 1.41 | 0.89 | −0.10 | −2.97 |
| SULF1 | 0.51 | −0.31 | 0.05 | −0.44 | −0.10 | SNORD116 | 0.29 | −0.14 | −0.11 | −0.13 | 0.25 | AC090004.1 | 0.00 | 0.03 | 0.02 | 0.01 | 0.10 |
| SCRIB | −0.32 | 0.18 | −0.15 | 0.30 | 0.23 | ADARB2 | 0.24 | −0.36 | −0.56 | 0.07 | 0.49 | SCHIP1 | 0.00 | −0.25 | −1.25 | −0.54 | −0.91 |
| MPRIP-AS1 | 0.43 | −0.01 | −0.41 | −0.29 | −0.55 | LINC02247 | −0.66 | 0.29 | 1.75 | −0.29 | 0.19 | RNA5SP517 | −0.01 | −1.69 | −1.12 | −0.74 | 1.07 |
| ADAMTS8 | −0.64 | 0.51 | 1.05 | 0.67 | 0.87 | ADA | −0.10 | −0.05 | 0.28 | 0.02 | −0.04 | OR7A1P | 0.03 | 0.39 | −0.91 | 1.03 | −0.98 |
| FRMD3 | −0.37 | 0.21 | 0.59 | −0.02 | 0.01 | AC004596.1 | 0.23 | −0.46 | −0.18 | 0.27 | 0.52 | AC069540.1 | −0.02 | −0.94 | −0.16 | −0.84 | −0.77 |
| FMR1-AS1 | −0.92 | −0.32 | 2.50 | −0.52 | 1.10 | JAG2 | −0.10 | −0.04 | −0.49 | 0.33 | 0.15 | AL049733.1 | 0.00 | −0.48 | 0.08 | 0.50 | 1.23 |
| MAS1 | −0.82 | −0.47 | −0.52 | 0.30 | 0.27 | AC055811.2 | −0.38 | 1.22 | −0.35 | 1.05 | 0.05 | AC004704.1 | −0.02 | 1.65 | −1.29 | 1.75 | −2.86 |
| GSDMD | 0.33 | −0.48 | −0.56 | −0.12 | −0.08 | SOX9 | −0.15 | 0.55 | 0.31 | 0.12 | 0.12 | GSTA7P | 0.03 | −1.18 | 0.65 | −0.04 | 1.54 |
| SLC25A41 | −0.77 | −0.31 | 0.91 | 0.08 | 1.38 | AL359397.1 | 0.46 | 0.02 | −1.26 | −0.20 | −0.89 | OR8G2P | −0.03 | −1.74 | −0.54 | −0.42 | 2.23 |
| AC006333.2 | 0.36 | −0.01 | −0.14 | 0.16 | −0.42 | HOXA9 | 0.15 | 0.41 | 0.15 | 0.18 | −0.73 | LINC02296 | −0.01 | 0.16 | −1.27 | 1.05 | −3.31 |
| SLC35A1 | 0.48 | 0.09 | 0.18 | −0.07 | −0.04 | AADACL2 | −0.20 | 0.58 | 1.39 | 1.06 | 0.01 | AC005692.2 | −0.02 | 1.14 | −1.36 | 0.33 | −3.21 |
| AL365356.1 | 0.47 | −0.86 | −0.30 | −0.25 | 0.16 | PGA5 | −0.63 | 0.79 | 1.72 | −0.50 | 0.32 | AC079031.2 | 0.02 | −0.26 | −0.64 | −0.33 | 0.75 |
| IYD | −0.85 | −0.56 | 0.11 | 0.15 | 0.12 | G5708 | 0.91 | −0.54 | 0.31 | 0.00 | 0.16 | HSFX3 | 0.02 | 0.37 | −0.85 | 0.43 | −0.74 |
| CNTN1 | 0.42 | 0.06 | −0.14 | 0.32 | 0.32 | RN7SL394P | −0.97 | −0.40 | 1.06 | −1.38 | −0.73 | SNORD65 | 0.03 | 0.15 | −0.67 | 0.09 | −0.66 |
| MIR652 | 1.11 | −0.39 | 0.83 | −0.33 | 0.17 | ADM5 | −0.22 | 0.58 | 0.82 | 0.61 | 0.29 | GLULP5 | 0.02 | −0.42 | −0.49 | −1.10 | −0.37 |
| ACTN3 | −0.79 | 1.37 | 0.22 | 0.84 | −0.43 | RNU2-58P | −0.26 | −0.11 | 0.21 | 0.36 | −0.09 | LINC00305 | 0.01 | −0.54 | 0.35 | 0.48 | 1.47 |
| RNU6ATAC 16P | 0.90 | −0.84 | 0.04 | −0.39 | −0.09 | AC112191.2 | 0.30 | −0.91 | −0.46 | 0.12 | 0.47 | AC104333.4 | 0.03 | −0.04 | 0.16 | −0.38 | 0.32 |
| AL023806.3 | 0.40 | −0.51 | 0.06 | −0.06 | 0.45 | AC021321.1 | 0.25 | −0.20 | 0.13 | −0.12 | −0.05 | IL2RB | 0.00 | −0.56 | −0.37 | −0.29 | 0.33 |
| PNPLA1 | −0.44 | 0.32 | 0.91 | 0.36 | 0.29 | FZD9 | 0.29 | −0.39 | 0.10 | −0.67 | 0.70 | AP001429.1 | 0.00 | 0.01 | 0.50 | −0.05 | 0.41 |
| PMVK | 0.29 | 0.08 | −0.03 | 0.06 | −0.04 | SPACA3 | 0.74 | −1.55 | −0.76 | −0.32 | 1.25 | AC007610.3 | −0.01 | −0.96 | 0.23 | 0.18 | 0.89 |
| HNRNPA1P71 | −0.73 | 0.17 | 0.75 | 0.27 | 0.91 | AC103858.2 | 0.66 | −0.28 | 1.12 | 0.29 | 0.25 | G34374 | 0.00 | 0.77 | 0.37 | 0.26 | −0.06 |
| HBP1 | −0.23 | 0.43 | 0.36 | 0.26 | −0.15 | AP003774.2 | 1.03 | −1.03 | 0.32 | 0.59 | 0.03 | SLC6A13 | 0.00 | −1.91 | −0.24 | −0.34 | 0.99 |
| AC004945.1 | −0.82 | 0.52 | 1.01 | −0.25 | −0.44 | LINC02265 | −0.72 | 0.60 | −0.27 | −0.58 | −1.60 | AL357075.1 | −0.03 | −0.84 | 0.94 | −0.63 | 0.88 |
| MUC5AC | −1.06 | −0.67 | −0.20 | 1.08 | 0.42 | RPL21P116 | 1.11 | 0.27 | −1.89 | 1.08 | −0.28 | AC005034.5 | 0.00 | 0.02 | 0.19 | 0.33 | 0.85 |
| EIF4EP1 | 0.54 | −0.34 | −1.23 | −0.22 | −0.77 | LAMP5-AS1 | 0.93 | 0.41 | −0.79 | 0.83 | −0.46 | AC084033.2 | −0.01 | 0.41 | −1.11 | −0.02 | −1.93 |
| OBP2B | −0.88 | 0.12 | 1.47 | −0.11 | −0.13 | CROCCP5 | −0.65 | 1.69 | −1.91 | 1.60 | −2.44 | AC105094.2 | 0.01 | −0.16 | −0.54 | −0.42 | 0.24 |
| RNU6-100P | 0.96 | −0.15 | −0.33 | −0.09 | −0.02 | AC105339.4 | 0.64 | 0.43 | 1.63 | −1.13 | 0.19 | RNA5SP365 | −0.01 | 0.88 | 1.15 | 1.15 | 0.47 |
| CFAP100 | −0.59 | 0.52 | 0.89 | −0.07 | −0.07 | AL355488.1 | −0.10 | 0.09 | 0.14 | 0.05 | 0.04 | NDUFA5P12 | 0.03 | 0.43 | −0.64 | −0.31 | −2.51 |
| AC015909.3 | −1.39 | −0.17 | 0.32 | 0.08 | 0.31 | CCL13 | −0.29 | −0.12 | 1.19 | 0.33 | 0.38 | MFRP | −0.01 | 0.28 | −2.01 | 0.62 | −0.20 |
| FAM122A | −0.24 | 0.25 | 0.45 | −0.02 | 0.09 | NPM1P36 | −0.67 | 0.14 | −1.75 | 1.73 | −0.88 | AL139148.1 | −0.03 | −1.05 | 0.28 | −0.50 | 0.56 |
| AC025211.1 | 0.70 | −0.16 | −0.35 | −0.17 | −0.13 | BNIP3P40 | −0.17 | 0.05 | 0.23 | 0.08 | 0.05 | AC018731.1 | −0.03 | 0.52 | −1.30 | 0.65 | −1.49 |
| AC026202.2 | 0.62 | 0.00 | −0.65 | 0.18 | −0.45 | AL139089.1 | 0.21 | −0.05 | 0.82 | −0.16 | 0.39 | AC018558.2 | −0.02 | −0.32 | −0.28 | 0.66 | −0.87 |
| ACKR2 | 0.58 | −0.70 | −0.20 | −0.19 | 0.18 | AC004948.1 | 0.67 | −0.18 | −0.88 | 0.37 | −0.54 | IGKV2D-28 | −0.03 | 1.13 | 1.65 | 1.76 | −0.20 |
| AC103591.3 | 0.56 | −0.44 | −0.59 | −1.35 | −0.55 | RNU4-9P | 0.31 | −0.35 | −0.24 | 0.64 | 0.30 | HNRNPH3P1 | 0.03 | −0.42 | −1.11 | −0.31 | −0.35 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| MIR4441 | 0.99 | −0.57 | −1.93 | −0.14 | −1.10 | 9-Mar | −0.09 | 0.06 | 0.13 | 0.15 | 0.17 | RN7SL37P | 0.00 | −0.09 | 1.38 | −0.15 | 0.13 |
| NPM1P18 | 1.55 | −0.20 | −0.99 | 0.56 | −0.44 | AC073530.2 | 0.18 | 0.10 | 0.30 | 0.16 | 0.12 | AC027369.1 | −0.01 | −1.46 | −1.86 | 0.74 | −0.75 |
| BSPRY | 0.37 | 0.30 | 0.06 | 0.15 | −0.15 | MED18 | −0.11 | −0.47 | −0.17 | −0.24 | 0.38 | AC026410.2 | −0.02 | 0.49 | −1.10 | −0.13 | −2.25 |
| AC005104.1 | 0.87 | −0.12 | −0.53 | 0.51 | 0.19 | AC021088.1 | 0.44 | −1.21 | 1.19 | 0.38 | 0.57 | AP003393.1 | 0.00 | −0.24 | 0.09 | −0.35 | 0.07 |
| AC090970.2 | 0.83 | −0.59 | −2.43 | −0.17 | −1.39 | NPCDR1 | −0.46 | 1.84 | 0.81 | 1.09 | 0.33 | OR10J9P | 0.02 | −0.70 | 0.99 | 1.66 | 0.37 |
| ISL1 | −0.71 | 0.82 | −0.30 | 1.07 | −0.12 | EMP2 | −0.09 | 0.13 | 0.08 | 0.21 | −0.11 | AC016930.1 | −0.01 | −2.21 | −1.65 | −1.14 | −1.29 |
| PRDX1P1 | −1.32 | −0.85 | 0.09 | −0.26 | 0.80 | AC011330.1 | 0.22 | 0.19 | 0.01 | 0.76 | 0.02 | SPRYD3 | 0.00 | 0.07 | −0.03 | 0.00 | −0.12 |
| MKRN3 | −0.85 | 0.18 | 0.68 | −0.03 | −0.39 | AC135731.2 | −0.97 | 0.94 | 0.40 | 1.26 | −0.10 | AC009303.3 | 0.00 | 0.10 | −0.12 | −0.11 | −0.36 |
| AL078587.1 | −0.42 | 0.19 | 0.44 | 0.08 | 0.45 | AC090582.1 | 0.76 | 0.03 | 0.04 | 0.18 | 0.91 | MTND4P21 | −0.01 | −0.37 | −0.41 | 0.29 | −0.19 |
| RNA5SP227 | 1.47 | −0.91 | −0.62 | 0.12 | −0.32 | OR10H1 | −0.29 | −0.56 | −0.06 | 0.96 | 0.18 | HLTF | 0.00 | 0.04 | 0.14 | −0.02 | −0.03 |
| MTND5P10 | −1.01 | 0.33 | −0.34 | 0.36 | −0.50 | RNU6-742P | 0.44 | 0.94 | −0.25 | 0.61 | −1.74 | LINC02529 | −0.01 | −0.62 | −0.97 | 0.34 | 0.64 |
| AP002907.1 | 0.55 | −0.31 | −0.14 | −0.17 | −0.27 | AL390067.1 | 0.45 | 0.76 | 1.21 | 0.40 | −0.60 | PGBD4P4 | 0.02 | −0.42 | −0.57 | 1.23 | 0.36 |
| LYPLAL1 | −0.24 | 0.41 | 0.37 | 0.17 | −0.07 | LINC01391 | 0.52 | −0.72 | −0.82 | 0.73 | 0.51 | CASC10 | 0.00 | −0.09 | −0.15 | 0.14 | 0.18 |
| AL121985.1 | 0.83 | −1.32 | −0.59 | −0.77 | 0.19 | AL162426.1 | −0.92 | 0.83 | 1.36 | 0.39 | 0.03 | LINC01511 | −0.01 | −1.07 | −1.08 | 0.20 | 0.58 |
| CPLANE2 | −0.48 | 0.37 | 0.58 | 0.31 | 0.43 | AL133325.3 | −0.36 | −0.68 | −1.08 | 0.44 | 0.23 | AL512353.1 | 0.00 | −0.09 | 0.30 | 0.26 | 0.46 |
| HPGDS | −0.62 | 0.29 | 0.88 | 0.31 | 0.20 | FGF12-AS1 | −0.44 | 0.15 | 1.30 | −1.35 | 0.31 | CYCSP12 | −0.03 | −0.21 | −1.26 | −0.30 | −0.09 |
| LY96 | 0.69 | −0.04 | −0.46 | −0.22 | −0.46 | PATE4 | −0.23 | −0.60 | −0.40 | −0.32 | −0.26 | OR4A6P | −0.01 | −0.10 | 1.89 | 1.13 | −1.02 |
| KRTAP12-3 | −1.81 | 0.41 | −0.46 | 1.64 | −1.43 | AC051619.4 | −0.37 | −0.20 | 1.24 | 0.59 | 1.10 | AL353651.3 | 0.01 | −0.48 | −0.39 | −0.41 | −0.94 |
| AC091057.1 | 0.45 | −0.72 | −0.92 | −0.26 | 0.07 | JSRP1 | −0.41 | 0.32 | 0.76 | 1.56 | 0.31 | SIX3 | −0.01 | −1.04 | −0.89 | −0.06 | 0.41 |
| PGBD4 | 0.28 | −0.14 | −0.24 | −0.17 | −0.02 | OR5AN2P | 0.82 | 0.15 | −2.16 | 1.16 | −1.14 | AC087269.2 | −0.01 | −0.15 | 0.26 | −0.88 | −0.81 |
| ANAPC15 | 0.35 | −0.08 | −0.30 | 0.00 | −0.49 | ARHGAP9 | 0.15 | −0.62 | −0.15 | −0.48 | 0.14 | LMO7DN-IT1 | 0.00 | −0.10 | 0.06 | −0.11 | −0.60 |
| RPS11 | 0.33 | 0.05 | −0.01 | −0.13 | −0.39 | DUTP8 | −0.89 | −0.84 | −0.12 | 0.62 | 1.12 | PRELID3BP5 | −0.01 | −1.23 | 0.78 | −2.01 | −0.30 |
| RNU6-1216P | 1.25 | −1.44 | −1.20 | −0.57 | −0.74 | DIRC1 | −0.37 | −1.44 | −0.82 | −0.98 | −0.10 | KLRC4 | 0.01 | −1.41 | 0.41 | −0.35 | 0.11 |
| SIRPG−AS1 | 1.23 | −0.74 | −0.68 | −0.07 | 0.30 | RNU6ATAC12P | −0.64 | −0.40 | 3.06 | 0.48 | 2.38 | AC002463.1 | 0.01 | 0.03 | 0.13 | 1.33 | 0.62 |
| AC002546.1 | −0.70 | 0.52 | 0.72 | 0.40 | −0.12 | LINC01471 | −0.42 | −0.36 | −0.82 | 1.10 | −0.03 | OR4E2 | −0.01 | −1.08 | −1.14 | 0.21 | −1.49 |
| AL157407.1 | −0.87 | 0.35 | −0.39 | 0.67 | −0.18 | AC023632.5 | 0.20 | −1.68 | −0.37 | −0.01 | 0.78 | AC093714.1 | 0.01 | 0.83 | 0.05 | 0.12 | −0.54 |
| RNU6-743P | −1.21 | 1.31 | −0.83 | 1.44 | −0.75 | AC106786.2 | 0.37 | −0.13 | 0.73 | 0.42 | −0.21 | HBG1 | 0.03 | 0.25 | 0.25 | −1.08 | −0.55 |
| OCLNP1 | −0.54 | 0.68 | 0.46 | 0.50 | 0.17 | AC073343.2 | −0.25 | 0.16 | 0.67 | 0.13 | −0.80 | AC010745.5 | 0.01 | −0.58 | −0.71 | −0.61 | −0.94 |
| ABCB7 | 0.17 | 0.06 | −0.19 | 0.06 | −0.26 | CLIC2 | −0.15 | 0.11 | 0.51 | −0.09 | 0.01 | AC087645.4 | −0.02 | −0.45 | 0.64 | −1.21 | −0.05 |
| PMS2P7 | −0.62 | 0.47 | −0.29 | −0.17 | 0.03 | AL360014.1 | −0.43 | −0.08 | −0.98 | 0.69 | −0.85 | LINC01477 | 0.02 | 0.80 | 0.09 | 1.11 | 2.01 |
| FCF1P4 | −1.30 | −0.44 | 2.04 | 0.90 | 1.11 | ANKRD30BP2 | 0.65 | −0.64 | −2.03 | 1.16 | −0.25 | MTCYBP15 | −0.01 | 0.26 | 0.11 | −0.27 | −1.31 |
| BUD13P1 | −0.44 | 0.64 | 0.23 | 0.47 | −0.11 | AC023424.2 | −0.30 | 0.27 | 1.24 | −0.25 | 0.72 | AC023813.4 | 0.01 | 0.43 | 1.41 | −0.44 | 0.12 |
| CFLAR | −0.16 | 0.09 | 0.11 | −0.03 | 0.04 | RPL7P52 | −0.19 | −0.01 | 0.41 | 0.34 | 0.00 | MARCKSL1P2 | −0.01 | −0.23 | −1.67 | 0.15 | 0.85 |
| C6orf99 | −0.80 | 0.23 | −0.01 | 0.39 | −0.58 | GK2 | 1.05 | −1.33 | −2.75 | 0.28 | −0.99 | RNU6-316P | −0.02 | 0.12 | 0.97 | 0.17 | −0.43 |
| SCNM1 | 0.16 | −0.14 | −0.17 | −0.07 | −0.13 | PSPC1 | 0.07 | −0.13 | −0.26 | −0.14 | −0.12 | OSGIN1 | 0.00 | −0.31 | −0.71 | 0.10 | −0.55 |
| MRAP2 | −0.56 | 1.14 | 0.84 | 0.45 | 0.17 | AL136221.1 | 0.21 | −0.12 | 0.44 | −0.25 | −0.02 | AC005076.1 | 0.00 | −1.43 | 1.22 | −0.55 | 0.94 |
| CSF1 | −0.36 | −0.11 | 0.24 | 0.01 | 0.34 | AC004878.5 | −0.45 | −0.27 | 0.09 | −0.07 | −0.24 | AC106872.6 | 0.01 | −1.83 | 0.95 | −1.04 | 0.00 |
| AP001324.1 | 0.62 | −0.27 | 0.52 | −0.54 | −0.24 | MIR345 | −0.63 | 0.37 | −0.21 | 1.82 | 2.14 | AL133319.1 | 0.01 | −0.17 | 0.27 | 1.10 | −0.19 |
| KCND1 | −0.38 | −0.04 | 0.38 | 0.06 | 0.23 | G11276 | 0.69 | −0.68 | 0.52 | −0.39 | 0.77 | OR4A1P | 0.03 | 0.91 | 0.09 | 0.20 | 1.84 |
| NFATC4 | −0.41 | 0.10 | 0.52 | −0.22 | −0.11 | AL354877.1 | −0.46 | 0.23 | 0.29 | −0.94 | 0.46 | AC090155.1 | −0.03 | 0.38 | −0.95 | 1.27 | 0.07 |
| C18orf32 | −0.30 | 0.18 | 0.40 | −0.14 | 0.14 | PGLYRP1 | −0.20 | −0.13 | 0.05 | −0.26 | 0.61 | AC114977.1 | −0.01 | −0.03 | 1.70 | −0.70 | 0.09 |
| AC012417.1 | 1.10 | 0.30 | 0.27 | 1.29 | −0.36 | AP000911.3 | −0.29 | 0.35 | −1.54 | 0.52 | −1.36 | OR7E46P | 0.01 | −1.86 | 0.55 | 0.34 | 1.28 |
| IER2 | 0.39 | −0.12 | −0.77 | −0.21 | −0.62 | AC138646.1 | 0.71 | −1.61 | −2.04 | 0.14 | −0.67 | HOXC10 | 0.00 | 0.06 | −0.14 | −0.01 | −0.10 |
| AC243571.2 | 0.63 | 0.27 | −0.65 | 0.57 | −0.97 | AC005833.1 | −0.79 | 0.47 | 1.99 | −0.66 | 1.43 | OR1A2 | 0.03 | −0.66 | −0.21 | 1.78 | 0.82 |
| FAR2P2 | −0.91 | −0.29 | 1.96 | 0.10 | 1.36 | GABRA1 | −0.32 | −0.33 | −1.06 | 0.61 | −0.54 | MIR921 | 0.00 | −1.40 | 0.98 | −0.44 | 1.21 |
| G14029 | −1.38 | −1.10 | 0.05 | 0.16 | 0.72 | AC245884.8 | −0.15 | 0.14 | 0.81 | −0.30 | 0.21 | AL357563.1 | −0.01 | −1.20 | 2.18 | −1.24 | 2.00 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| SLC25A3P2 | −0.81 | 0.38 | 1.72 | −0.36 | 0.50 | AL662844.3 | −0.48 | −1.00 | 0.51 | 0.30 | −0.16 | ABHD10 | 0.00 | −0.03 | 0.33 | −0.15 | 0.10 |
| AC116609.1 | −1.92 | 0.38 | 1.53 | −1.19 | −0.54 | NXPH4 | −0.13 | 0.28 | 0.52 | 0.21 | −0.26 | RTP3 | 0.01 | 0.03 | 0.74 | 0.54 | 1.19 |
| CHCHD2P2 | 0.96 | −0.47 | 0.34 | −1.29 | −0.22 | GAPDHP55 | −0.38 | 2.18 | −0.30 | 1.10 | −0.42 | AC010435.1 | 0.00 | −0.53 | 0.00 | −1.01 | 0.40 |
| PPCS | 0.33 | −0.05 | −0.03 | −0.05 | −0.21 | LINC02328 | 0.20 | −0.44 | −0.65 | −0.67 | 0.15 | AC003986.2 | 0.00 | −0.25 | 0.71 | −0.54 | 0.26 |
| DNAJC19P3 | 2.23 | −2.05 | 0.51 | −0.54 | 2.53 | AC025437.3 | 0.35 | −0.66 | −0.83 | −0.31 | −0.35 | AC107027.1 | −0.02 | −0.98 | 0.74 | 0.78 | −0.47 |
| AC010245.2 | −0.44 | −0.02 | 0.63 | 0.09 | 0.53 | AC087289.2 | −0.21 | 0.46 | −0.10 | 0.45 | −0.21 | EIF3KP2 | −0.03 | −1.39 | 0.72 | 1.41 | 2.52 |
| MIR548A3 | 1.13 | 0.07 | −1.82 | 0.32 | −1.36 | AC010306.1 | −0.37 | 0.65 | 0.38 | 0.43 | −1.53 | AC095057.2 | −0.01 | −0.51 | −1.04 | 0.01 | −0.61 |
| AC073130.2 | 0.46 | −0.46 | −1.22 | −0.13 | −0.57 | AC010168.2 | −0.11 | −0.29 | −0.13 | −0.09 | 0.10 | COL5A1 | 0.00 | 0.06 | 0.70 | −0.86 | −0.31 |
| BTN3A2 | −0.25 | −0.28 | 0.55 | −0.21 | 0.63 | STX8 | −0.04 | 0.15 | 0.01 | −0.04 | −0.22 | AL590483.1 | −0.01 | 0.01 | −1.75 | 2.64 | 0.96 |
| RN7SL852P | −0.68 | −0.46 | −0.24 | −0.32 | 0.44 | AC090340.1 | −0.58 | −0.38 | −0.44 | 0.16 | 0.61 | HMGB3P11 | 0.01 | −0.98 | 1.14 | −0.65 | 0.71 |
| NMB | 0.72 | 0.21 | −0.66 | 0.12 | −0.60 | PRMT5-AS1 | 0.22 | 0.05 | −0.19 | −0.02 | 0.25 | LINC02400 | 0.01 | −0.15 | −0.59 | 0.10 | 0.10 |
| AC010327.4 | −0.58 | 0.65 | 0.93 | 0.21 | 0.46 | RNU4-88P | −0.72 | 0.87 | 2.78 | −0.77 | 1.29 | RN7SL357P | −0.03 | −0.81 | −0.47 | −1.09 | −0.21 |
| CEACAMP1 | −1.07 | −0.24 | 0.01 | 0.54 | 0.01 | AL359265.1 | −0.40 | −0.29 | 1.17 | 0.35 | 0.22 | GATA3-AS1 | 0.00 | 0.26 | 1.24 | 0.77 | 1.19 |
| HCRTR1 | −0.54 | 0.23 | 0.46 | 0.22 | 0.51 | RN7SL502P | 0.27 | −0.69 | 0.81 | −0.56 | 0.47 | GJA6P | 0.00 | −0.22 | −0.98 | 0.20 | −0.49 |
| AC090058.1 | −0.99 | −0.48 | 0.91 | 0.03 | 0.51 | AC104837.1 | 0.40 | −0.59 | −0.70 | −0.36 | −0.56 | AL138799.4 | 0.02 | 0.14 | −0.72 | 0.15 | −1.30 |
| G8340 | −0.54 | 0.31 | 0.17 | −0.34 | −0.14 | BMS1P1 | 0.19 | 0.37 | −0.25 | 0.86 | 0.05 | SCGB1D4 | 0.02 | −0.26 | −0.18 | 0.03 | 0.54 |
| SHISA8 | −1.28 | 0.44 | 1.75 | 0.26 | −0.03 | RN7SL213P | 0.44 | 0.58 | −0.29 | 0.21 | −1.82 | RPL30P5 | −0.02 | −1.02 | −1.26 | 0.17 | −0.08 |
| AL162377.1 | −0.52 | 0.83 | −0.15 | 0.13 | −0.42 | MTND6P21 | −0.37 | 0.62 | 0.11 | −0.11 | −0.10 | ACTRT1 | 0.02 | 0.95 | −1.42 | 1.86 | −0.10 |
| AC022148.2 | −1.05 | −0.15 | 0.82 | 0.66 | 0.05 | MIR3166 | 0.59 | −1.79 | −2.01 | 0.34 | −0.46 | AL050404.1 | 0.02 | −0.67 | −1.00 | −0.07 | −0.38 |
| AC092134.3 | −1.13 | −0.82 | 0.53 | −0.30 | −0.04 | AP005210.1 | 0.36 | 0.37 | 1.01 | −0.93 | 0.46 | AC087477.4 | 0.02 | −0.32 | 0.59 | 0.67 | 0.54 |
| LINC01146 | 1.17 | −1.29 | −1.75 | −0.33 | −0.92 | FAM45BP | 0.34 | −0.74 | −0.45 | −0.20 | −0.62 | AL355497.2 | 0.02 | −0.67 | −0.01 | 0.72 | 1.69 |
| AC114812.4 | 1.05 | −0.51 | −0.23 | 0.22 | 0.21 | MTCYBP24 | −0.37 | 0.89 | −0.14 | 0.27 | −0.88 | CNGA3 | 0.00 | 0.98 | −1.22 | 0.45 | −0.50 |
| KIZ-AS1 | −0.34 | 0.35 | 0.81 | 0.32 | 0.25 | G263 | 0.16 | 0.46 | −0.14 | 0.38 | −0.16 | DPRXP7 | −0.02 | −0.54 | 0.26 | −1.60 | −0.67 |
| FADS1 | −0.72 | 0.21 | 0.30 | 0.76 | 1.33 | CLCA3P | 0.24 | −0.08 | −0.43 | 0.38 | 0.12 | HTR5BP | 0.00 | −0.06 | 0.11 | −0.27 | −0.12 |
| ADCY1 | −0.38 | 0.12 | 0.36 | 0.39 | 0.00 | AL138895.2 | −0.59 | −1.53 | −1.05 | 0.17 | −1.62 | AC080013.2 | 0.00 | 1.61 | 1.64 | 0.32 | 0.07 |
| AC099791.2 | −1.01 | −0.17 | −0.73 | 0.44 | −0.87 | CPSF7 | −0.05 | 0.02 | −0.09 | 0.11 | 0.01 | IGHVIII-76-1 | −0.01 | −0.48 | 0.31 | 0.62 | −1.05 |
| MIR548U | 1.08 | −0.38 | 1.06 | −0.36 | 0.79 | FZD2 | 0.25 | 0.06 | −0.09 | 0.06 | −0.34 | FMO11P | 0.01 | −1.33 | −1.28 | 1.16 | 1.43 |
| AC007996.1 | 0.49 | −0.22 | −0.18 | 0.06 | −0.01 | SMARCAL1 | −0.04 | −0.05 | −0.04 | −0.05 | 0.03 | G3694 | 0.00 | −0.18 | 0.30 | 0.94 | 1.41 |
| ADH5 | 0.28 | −0.14 | −0.26 | −0.02 | −0.18 | SLC9B1P3 | 0.70 | 0.25 | −0.41 | 0.65 | −1.82 | AC083795.2 | −0.02 | −0.25 | −1.55 | 1.96 | −0.14 |
| GUCY1A2 | −0.49 | 0.21 | 0.78 | −0.11 | −0.44 | MICALL2 | −0.12 | −0.11 | −0.43 | 0.30 | 0.17 | DNAJA1P5 | 0.02 | 0.70 | −0.43 | 1.86 | −0.49 |
| AC073934.1 | −1.05 | 1.22 | 1.52 | −0.24 | 0.31 | LINC01618 | −0.44 | −1.13 | 1.69 | −1.17 | 0.40 | MRPL49P2 | −0.02 | 1.52 | 0.70 | −1.40 | −0.71 |
| ATP5MF | 0.26 | −0.09 | −0.37 | 0.19 | −0.12 | AC087072.2 | 0.54 | 1.34 | 0.16 | 0.19 | −0.76 | MIR3157 | 0.00 | −0.68 | 0.71 | 0.03 | 1.91 |
| AC064807.4 | 1.18 | −2.48 | 0.43 | −0.33 | 2.26 | LINC02386 | −0.34 | −0.48 | −0.46 | 0.81 | 1.28 | MED28P1 | 0.00 | −1.12 | 1.46 | −0.38 | 0.52 |
| RNA5-8SP6 | −1.12 | 0.50 | −0.24 | 0.99 | −0.26 | ST13P14 | 0.74 | 0.54 | 0.62 | −0.78 | −0.56 | AL138831.2 | −0.01 | −1.91 | −0.84 | −1.50 | 1.31 |
| Clorf167 | −1.19 | −0.95 | −0.80 | −0.12 | 0.27 | RN7SL370P | 0.17 | −0.22 | −0.03 | 0.28 | 0.43 | IGKV1OR2-118 | −0.01 | 0.55 | −1.39 | 0.61 | −0.55 |
| HERC3 | −0.16 | 0.11 | 0.07 | 0.04 | 0.07 | LINC02318 | 0.75 | −1.37 | −0.17 | 1.37 | 1.20 | AL355803.1 | 0.01 | −0.74 | 0.71 | −0.94 | 0.31 |
| SEMA6A | −0.26 | 0.41 | 0.42 | 0.16 | 0.09 | AC027287.1 | −0.69 | −0.35 | 0.16 | −1.09 | −0.67 | DKK4 | 0.00 | −0.57 | −0.85 | −0.25 | −0.01 |
| AL049812.2 | −1.56 | 2.22 | 2.86 | 0.23 | −0.43 | AC013467.2 | 0.23 | −0.42 | 0.40 | −0.20 | 0.87 | OR6C64P | −0.02 | 0.05 | −0.79 | 0.33 | −1.08 |
| AC127024.7 | −0.60 | 0.60 | −0.62 | 0.84 | 0.14 | LINC00311 | −0.19 | −0.36 | 0.24 | −0.21 | 0.50 | SGO1P2 | −0.01 | −1.01 | −1.11 | 0.60 | −0.84 |
| NAAA | −0.27 | 0.06 | 0.37 | 0.13 | 0.08 | AL590399.1 | −0.65 | −0.03 | 1.99 | −0.72 | 0.92 | AL713998.1 | 0.01 | 0.40 | −0.96 | −0.23 | −0.37 |
| SNHG6 | −0.40 | 0.43 | 0.28 | 0.35 | −0.51 | FAM9B | 0.42 | −0.04 | −2.26 | 0.48 | −0.72 | AL049775.2 | 0.00 | 0.31 | −1.35 | 0.24 | −1.55 |
| AL022323.4 | 0.35 | −0.04 | −0.25 | −0.06 | 0.01 | AC008662.1 | 0.82 | 0.38 | −1.89 | 1.07 | −0.61 | AC012569.1 | 0.00 | −0.16 | 0.08 | −0.24 | −0.10 |
| CLGN | −0.77 | 0.22 | 1.12 | 0.26 | 1.11 | LINC01833 | 0.57 | −1.66 | 0.50 | 0.40 | 0.72 | AC011357.1 | 0.01 | 0.64 | 1.24 | −0.18 | −1.66 |
| NEPRO | 0.22 | −0.04 | −0.11 | 0.01 | −0.09 | MBD3 | 0.07 | −0.06 | −0.15 | 0.10 | 0.09 | HMGN1P12 | 0.00 | 0.17 | 0.66 | −0.53 | 0.12 |
| AP001055.1 | −0.90 | 0.80 | −0.34 | 0.91 | 0.67 | ADAD1 | −0.56 | −0.42 | 1.33 | −0.72 | −1.27 | CNOT6LP1 | 0.00 | 0.07 | 0.03 | 0.01 | −0.02 |
| EIF1AY | 0.48 | −0.23 | −0.72 | −0.02 | −0.43 | RNA5SP260 | 0.15 | −0.07 | 0.12 | 0.00 | 0.11 | FP475955.3 | 0.02 | −0.68 | −0.49 | −0.39 | −0.98 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| SGIP1 | 0.37 | −0.28 | −0.06 | −0.46 | −0.43 | SLC38A11 | −0.16 | −0.18 | 0.01 | −0.03 | −0.29 | RN7SL224P | −0.01 | −0.68 | −0.99 | −0.83 | −0.07 |
| AC234782.3 | −0.89 | 0.44 | 0.39 | −0.99 | −0.41 | LINC02582 | 0.26 | −0.38 | −0.96 | 0.02 | −0.74 | ANKRD20A18P | 0.00 | −0.02 | 0.93 | −0.13 | 1.33 |
| AC107909.2 | 0.99 | −0.10 | −0.62 | 0.07 | −0.43 | AC096543.2 | −1.03 | 0.22 | −1.20 | 1.19 | −0.81 | PTCD2P1 | 0.02 | −0.67 | −0.02 | −0.44 | 1.33 |
| ODF2L | 0.19 | −0.06 | −0.07 | −0.11 | −0.07 | AC233280.19 | 0.25 | 0.01 | −0.02 | 0.44 | 0.63 | OR7E8P | 0.02 | −0.58 | 0.63 | −0.86 | 0.24 |
| FOXI3 | −0.92 | 0.49 | 1.37 | 0.20 | −0.37 | AGPAT1 | −0.09 | −0.02 | 0.21 | −0.09 | 0.20 | AC012462.2 | −0.02 | 0.07 | NA | −0.24 | −1.02 |
| AL355794.1 | 1.07 | 0.21 | −2.34 | 0.45 | −1.58 | RN7SL555P | −0.39 | −0.06 | −1.58 | 0.63 | −0.07 | AL358876.1 | 0.02 | −1.13 | −0.24 | 1.57 | −0.67 |
| G30615 | −1.44 | 0.16 | 1.84 | −1.82 | −0.50 | AC087763.1 | −0.44 | 0.36 | −0.25 | 1.10 | 0.59 | AL031736.2 | 0.01 | −1.01 | 0.32 | 0.36 | 0.42 |
| RPL21P44 | 0.49 | −0.04 | −0.47 | 0.00 | −0.36 | AC022387.1 | 0.52 | 0.22 | −0.50 | 1.29 | −0.29 | AC060765.1 | 0.01 | −0.82 | −1.41 | 0.60 | −0.99 |
| RNY4P17 | −0.74 | 0.07 | 0.47 | −0.19 | 0.20 | RNU6-987P | 0.38 | 0.34 | −0.93 | 0.70 | 0.28 | AC010928.1 | 0.00 | −0.67 | −0.61 | 0.02 | −0.04 |
| AL138955.1 | 0.66 | 0.21 | −0.26 | −0.58 | −0.66 | AL590762.3 | 0.22 | −0.47 | −1.12 | −0.12 | −0.38 | SCGB1D1 | 0.02 | −0.45 | −0.98 | 1.62 | 0.95 |
| AC037459.3 | −0.40 | 0.22 | 0.45 | −0.04 | 0.13 | AASDH | 0.05 | −0.01 | 0.16 | −0.03 | 0.12 | AL591866.1 | 0.00 | −0.42 | −0.10 | −0.18 | 0.29 |
| C1QA | −0.71 | 0.54 | 0.89 | −0.16 | −0.32 | G30323 | 0.29 | −0.07 | 0.86 | −0.77 | −0.63 | RPL17P12 | 0.01 | 1.41 | −1.47 | 0.13 | −2.84 |
| PIGG | −0.20 | 0.02 | 0.15 | 0.06 | 0.18 | BCOR | 0.06 | 0.10 | −0.02 | 0.02 | −0.20 | PKP4P1 | 0.00 | −0.22 | −1.32 | 1.18 | −1.00 |
| POLH | 0.21 | −0.15 | 0.18 | −0.18 | −0.02 | AC008966.2 | 0.25 | 0.08 | −0.20 | 0.14 | 0.05 | LINC00400 | −0.01 | −0.29 | −1.77 | 1.27 | −1.62 |
| AC006262.3 | −1.18 | 1.46 | 1.16 | 0.75 | 0.74 | KIAA0355 | −0.04 | 0.15 | 0.20 | −0.10 | −0.15 | AC004253.2 | −0.02 | 0.90 | 0.20 | 0.45 | −1.17 |
| MAGI2-AS1 | −1.56 | 0.28 | 2.78 | −1.00 | −0.13 | ARL3 | 0.08 | 0.07 | 0.35 | −0.15 | −0.05 | AC122714.2 | −0.02 | −0.39 | −0.05 | 1.82 | 1.04 |
| MAPKAPK5 | −0.14 | 0.02 | 0.09 | −0.03 | 0.06 | MIR670HG | −0.86 | −0.32 | 1.05 | −1.57 | 0.21 | SDAD1P3 | −0.01 | 1.49 | −0.82 | −0.35 | −1.57 |
| RPL7P21 | 0.68 | −0.13 | −0.25 | −0.15 | −0.45 | OR4C5 | 0.61 | −0.20 | −0.59 | −0.15 | −1.90 | AC093909.4 | 0.00 | 0.48 | −1.12 | −0.20 | −0.60 |
| CDKL1 | −0.30 | −0.01 | 0.21 | 0.19 | 0.23 | AP000692.1 | 0.14 | 0.04 | −0.13 | −0.16 | 0.18 | AL606530.1 | −0.01 | −0.42 | −0.63 | 0.45 | −1.05 |
| LINC00235 | −0.38 | 0.35 | 0.28 | 0.32 | 0.08 | CYP26A1 | −0.36 | 0.22 | −1.39 | 1.25 | −0.43 | LINC00498 | −0.01 | 0.72 | 0.15 | 0.85 | −0.33 |
| INPP5F | 0.14 | −0.02 | −0.16 | −0.02 | −0.07 | C3P1 | −0.36 | −0.56 | −1.36 | −0.11 | −1.29 | RPL23AP38 | −0.02 | −0.30 | 0.99 | −1.99 | 0.94 |
| AC108935.1 | −1.45 | −0.65 | 1.52 | −0.43 | 1.31 | AL137244.1 | −0.18 | 0.11 | 0.75 | 0.22 | 0.76 | HMGB1P30 | −0.01 | 0.25 | 0.72 | 1.40 | 0.87 |
| GLT1D1 | −0.57 | −0.25 | −0.26 | −0.06 | −0.60 | RAB28P2 | −1.51 | 0.12 | 0.75 | −0.16 | 1.40 | RN7SL175P | −0.01 | −0.74 | 1.34 | −1.02 | 0.21 |
| KLHL34 | −0.83 | −0.59 | 0.67 | −0.16 | 0.88 | SLC12A5-AS1 | −0.39 | −0.50 | −1.30 | −0.45 | −0.72 | AL445644.1 | 0.02 | −0.39 | 0.60 | 0.25 | 0.32 |
| AP002840.2 | −0.56 | 0.29 | 0.99 | 0.43 | 0.52 | SETP16 | −0.47 | 0.12 | 1.24 | 0.81 | 1.50 | AC092447.8 | −0.01 | 0.70 | −1.84 | 0.70 | −1.37 |
| RNU7-16P | 0.88 | 0.41 | −1.03 | 0.29 | −0.42 | AC110716.2 | −0.47 | 0.69 | −0.77 | 0.76 | −0.47 | CTAG2 | 0.02 | −0.29 | −0.66 | 4.00 | NA |
| RNU6-20P | −1.10 | −0.81 | 1.60 | −0.24 | 0.50 | RNA5SP250 | −1.00 | 0.65 | −0.18 | 0.95 | 0.27 | RPL6P7 | −0.01 | −1.20 | 0.90 | −0.43 | 1.19 |
| LINC02595 | 0.46 | −0.46 | −0.56 | 0.30 | 0.45 | RNU6-308P | 0.49 | −1.00 | −0.16 | 0.31 | 0.50 | AC137695.1 | 0.00 | −0.52 | 1.00 | 0.48 | −0.45 |
| MTRF1 | 0.16 | −0.14 | −0.25 | −0.05 | 0.02 | SSH1 | −0.09 | −0.15 | −0.06 | −0.07 | 0.01 | AC090503.2 | −0.02 | −1.14 | 0.95 | 0.24 | 3.55 |
| HHIP-AS1 | −1.08 | 0.79 | 1.05 | 1.31 | −0.04 | AL160408.5 | 0.29 | −0.72 | −1.53 | −1.14 | −0.31 | MRPL53 | 0.00 | −0.19 | 0.28 | −0.22 | −0.05 |
| RAB26 | −0.36 | 0.17 | −0.13 | 0.25 | 0.13 | AC009163.3 | −0.15 | 0.06 | 0.15 | 0.07 | 0.12 | AL162424.1 | 0.00 | 0.35 | 1.33 | 0.15 | 0.31 |
| MIR3118-2 | −0.81 | 0.47 | 0.37 | 0.48 | 0.25 | ASNSP1 | −0.60 | 0.20 | 0.19 | −0.86 | −0.51 | AL109653.1 | −0.02 | −0.59 | −0.96 | 1.90 | −0.27 |
| PPP1R3C | 0.57 | 0.03 | −1.01 | 0.29 | −0.39 | KCNA3 | 0.20 | −0.77 | 0.23 | −0.90 | 0.32 | AKR1B1P4 | −0.01 | 0.01 | −2.13 | 0.48 | −1.31 |
| SARIA | 0.25 | −0.12 | −0.10 | −0.14 | −0.13 | AL359762.2 | −0.64 | −1.05 | −1.18 | 0.52 | −0.51 | AC083841.4 | 0.00 | 0.27 | −1.02 | 0.45 | −0.59 |
| AC068491.1 | 1.24 | −0.20 | −2.01 | −0.57 | −1.90 | RNU6-953P | −1.05 | −0.52 | 1.88 | 0.80 | 0.95 | RNU7-11P | 0.00 | −0.30 | −0.47 | 0.14 | 1.08 |
| AC110995.1 | −0.74 | 0.34 | 0.66 | −0.68 | −0.16 | EXOC3-AS1 | 0.15 | −0.09 | 0.15 | −0.11 | 0.29 | AC093904.1 | −0.02 | −0.50 | −0.47 | −0.89 | −0.25 |
| ACOT12 | −1.08 | −1.43 | 0.93 | −0.17 | 1.37 | AC107302.1 | −1.10 | 1.21 | 0.57 | −0.63 | −1.61 | AL121956.1 | 0.01 | 0.27 | −1.41 | 0.94 | −0.41 |
| SCAP | −0.20 | 0.19 | 0.09 | 0.17 | 0.09 | NCF4-AS1 | 0.85 | −0.09 | −0.07 | 0.30 | −0.15 | ICE2P1 | 0.00 | 0.10 | −1.73 | 0.96 | −1.68 |
| RNU2-68P | 0.95 | −1.08 | 0.08 | −0.80 | −0.06 | RNU6-282P | 0.27 | 0.95 | 0.01 | 0.02 | −0.41 | DTNB | 0.00 | 0.24 | −0.17 | 0.22 | 0.08 |
| LINC00706 | 2.23 | −0.40 | −3.22 | 0.17 | −3.28 | LINC02397 | −0.27 | 0.16 | −0.68 | 0.22 | −0.19 | AP000936.1 | 0.00 | 0.48 | 0.00 | −1.13 | −0.41 |
| RNU6-116P | −1.62 | 1.30 | 0.59 | −0.08 | 0.96 | ADAMTS19-AS1 | −0.70 | 0.83 | 0.81 | 0.69 | 0.97 | AC079168.2 | 0.02 | −0.72 | 1.17 | 0.02 | −0.55 |
| AC097534.2 | −0.58 | 0.33 | 0.84 | 0.11 | 0.38 | LINC00494 | 0.45 | −0.15 | −1.09 | 0.40 | −1.98 | AC003950.1 | −0.02 | −0.64 | 0.42 | 0.32 | 0.63 |
| G28007 | −1.77 | −0.32 | 2.37 | −0.89 | 1.90 | P4HA1 | −0.07 | −0.11 | 0.39 | −0.34 | 0.04 | AL161629.1 | −0.02 | 0.55 | −1.62 | 0.67 | −2.18 |
| AC215522.2 | 0.52 | −0.92 | −1.01 | 0.13 | 0.75 | AL355312.2 | 0.18 | 0.01 | 0.01 | −0.07 | 0.02 | AC021146.11 | −0.02 | −0.89 | −0.83 | 0.39 | NA |
| C1GALT1C1 | 0.35 | −0.30 | −0.05 | −0.35 | −0.06 | LINC01572 | 0.11 | −0.12 | −0.12 | 0.17 | 0.18 | BX322562.1 | 0.00 | −0.32 | −0.59 | −0.21 | −0.07 |
| ABCC9 | −0.57 | 0.71 | 1.26 | −0.02 | −0.17 | G26247 | −0.26 | −0.10 | 0.51 | 0.86 | 0.68 | AL132709.3 | 0.00 | −0.11 | 1.21 | −0.44 | −0.01 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AC013444.1 | 0.96 | −1.19 | −0.17 | −0.52 | −0.41 | SLC44A4 | −0.22 | 0.36 | 0.16 | −0.01 | 0.12 | AL355493.2 | 0.01 | 0.17 | −0.10 | 1.81 | 0.68 |
| RNU7-3P | 1.42 | −0.19 | 0.09 | 0.42 | 0.22 | AC011753.2 | 0.13 | −0.09 | 0.08 | −0.28 | −0.16 | AC022695.2 | 0.00 | −0.59 | −1.21 | 0.85 | −2.04 |
| AL109614.1 | 0.83 | −0.29 | −0.55 | −0.03 | 0.16 | AC069061.2 | 0.66 | −1.36 | −0.64 | −0.11 | 1.17 | AL023773.1 | −0.02 | 0.30 | −0.48 | 0.49 | −0.42 |
| AC093525.6 | −0.81 | 0.63 | 1.45 | −0.49 | −0.30 | BPIFB1 | 0.42 | 0.18 | 0.12 | −0.06 | 0.10 | AL589765.6 | 0.01 | 0.91 | 0.53 | −0.22 | 0.83 |
| EMX1 | −0.51 | 0.43 | 0.37 | 0.36 | 0.50 | MIOXP1 | −0.91 | 0.76 | 0.52 | 1.65 | 1.02 | RAB3C | 0.00 | 0.01 | −0.18 | 0.30 | 0.02 |
| AL512303.1 | −0.97 | −0.03 | 0.74 | −0.11 | 1.33 | IGHM | 0.36 | 0.68 | 1.96 | −0.52 | −1.35 | ASB6 | 0.00 | 0.19 | −0.19 | 0.23 | −0.16 |
| FRAS1 | −0.46 | 0.59 | 1.07 | −0.54 | 0.02 | AC055876.2 | −0.20 | 0.39 | 0.38 | 0.07 | 0.15 | PEX5 | 0.00 | 0.02 | −0.03 | 0.11 | 0.12 |
| PRSS3P1 | −1.10 | 1.54 | −0.71 | 1.94 | 1.13 | AC008514.2 | 0.37 | −1.60 | −1.03 | −0.24 | 0.84 | AL035407.2 | 0.01 | −0.31 | −0.56 | 0.09 | −0.18 |
| RNF122 | 0.46 | −0.04 | −0.94 | −0.08 | −0.86 | SPATA25 | −0.21 | 0.10 | 0.70 | 0.28 | 0.87 | AC008958.1 | 0.00 | 0.22 | 0.00 | −0.47 | 0.15 |
| ENOSF1 | −0.24 | 0.01 | −0.03 | 0.14 | 0.26 | AC021016.2 | −0.08 | −0.24 | −0.29 | 0.14 | 0.01 | NOS2P1 | 0.00 | −0.67 | −0.28 | 0.17 | 0.52 |
| AL138831.1 | −0.82 | −0.14 | 1.94 | −0.65 | 0.49 | KARSP1 | 0.17 | 0.15 | 0.28 | 0.17 | 0.61 | AC079953.1 | 0.01 | −1.10 | −0.90 | 0.69 | 1.15 |
| HACD3 | 0.27 | −0.21 | −0.18 | −0.17 | −0.03 | RNF25 | −0.06 | 0.00 | −0.06 | 0.06 | −0.04 | OR5P2 | 0.00 | 0.84 | 0.76 | 0.16 | −0.17 |
| AC131159.2 | −0.72 | 0.27 | 0.71 | 0.07 | 0.49 | FKBP4P1 | −0.15 | 0.15 | −0.05 | 0.12 | 0.31 | AC090152.1 | 0.00 | 0.06 | −1.21 | 0.01 | −0.17 |
| AL358472.1 | 1.22 | −0.33 | −0.43 | −0.38 | −1.23 | OR10V3P | −0.35 | 0.72 | 2.18 | 0.68 | 1.92 | GAD2 | 0.00 | 0.46 | −0.95 | 0.38 | −0.77 |
| SNORA76 | −0.38 | 0.47 | 0.25 | −0.14 | −0.61 | DLGAP2-AS1 | 0.54 | −0.38 | −1.70 | −0.20 | −1.49 | EIF4A1P11 | 0.00 | −1.30 | 0.11 | −1.14 | 0.04 |
| PRADC1 | 0.36 | −0.04 | −0.19 | 0.01 | −0.31 | AC090193.2 | −0.60 | 0.67 | 0.00 | −0.37 | −0.95 | AKIRIN2P1 | −0.01 | 0.33 | 0.23 | −0.98 | −0.60 |
| AC023824.3 | −1.54 | −0.84 | −0.48 | 1.55 | 2.46 | AC004890.3 | 0.12 | −0.56 | −0.44 | −0.17 | 0.30 | AC069240.1 | 0.01 | 0.26 | 0.44 | −1.69 | −0.87 |
| BLOC1S4 | 0.31 | −0.03 | −0.23 | −0.12 | −0.19 | AC009950.1 | 0.13 | −0.43 | −0.03 | −0.10 | 0.44 | AC010857.1 | 0.01 | −0.34 | −0.76 | −0.17 | −0.65 |
| CALM2 | 0.27 | −0.22 | −0.25 | −0.04 | −0.02 | AC105180.1 | 0.52 | −1.64 | −1.93 | 0.31 | 0.04 | RN7SKP121 | 0.01 | 0.20 | −1.31 | 0.22 | −2.41 |
| DNAH14 | −0.34 | 0.23 | 0.32 | −0.04 | 0.08 | ACOD1 | 0.45 | −1.58 | 1.02 | −1.83 | 0.30 | CYP4F34P | −0.01 | −0.15 | −0.49 | 0.11 | 1.33 |
| COL6A2 | −0.37 | 0.17 | 0.68 | −0.49 | −0.18 | FLT3 | 0.19 | −0.40 | 0.11 | 0.13 | 0.63 | AL589182.2 | 0.01 | −0.34 | 1.66 | −0.96 | 1.64 |
| NCF1B | −0.81 | −0.44 | 1.08 | −0.25 | 0.07 | AC007952.4 | 0.22 | −1.12 | −0.56 | 0.00 | 0.02 | PRPS1L1 | 0.01 | 1.03 | −1.18 | 0.93 | −1.99 |
| ACVRL1 | −0.41 | 0.00 | 0.84 | −0.16 | 0.15 | MRE11P1 | −0.56 | 1.47 | −0.87 | 1.03 | −1.53 | RNU6-307P | 0.00 | 0.63 | −0.18 | 0.77 | −1.44 |
| LINC01956 | −0.80 | 0.75 | 1.16 | −0.02 | 0.38 | AC017002.5 | −0.38 | −1.23 | −1.14 | −1.17 | 0.21 | ASS1P11 | −0.01 | −0.54 | −1.03 | −0.60 | −2.87 |
| AP001636.2 | −0.61 | 0.23 | 1.07 | 0.17 | 0.47 | OR2AH1P | −0.50 | −1.08 | −0.66 | 1.00 | 0.24 | AC109811.1 | 0.00 | 0.75 | −0.63 | 0.45 | −0.80 |
| AL034405.1 | 0.94 | −1.32 | −0.64 | −0.19 | 1.12 | PPIH | 0.08 | −0.38 | −0.16 | −0.14 | 0.33 | RPL17P45 | −0.01 | −0.66 | −0.93 | 1.69 | NA |
| PPAN | 0.56 | −0.20 | −0.76 | 0.53 | −0.34 | RN7SL388P | −0.48 | 0.84 | 0.33 | 0.21 | 0.19 | AC008033.3 | 0.00 | −0.40 | −0.46 | −0.62 | −0.66 |
| AC023632.2 | −0.58 | 0.06 | 1.31 | −0.29 | 0.34 | MAGEA5 | −0.65 | 0.33 | 1.03 | −0.26 | 0.65 | NAXD | 0.00 | 0.14 | 0.03 | 0.14 | 0.00 |
| AC099542.1 | −1.06 | −0.95 | −1.18 | −0.18 | 0.58 | ITGB1BP1 | −0.06 | −0.02 | −0.06 | 0.01 | −0.02 | MIR3115 | 0.00 | −0.73 | −1.08 | −1.02 | −1.10 |
| SNORA13 | −0.53 | 0.47 | 0.08 | 0.46 | −0.65 | SPDYE20P | 0.46 | −0.52 | −0.77 | −0.03 | −0.53 | LINC02070 | 0.01 | −0.46 | 0.57 | −0.21 | 1.43 |
| AL353626.2 | −0.85 | −0.46 | 1.98 | 0.29 | 1.59 | RAC1P4 | 0.73 | 0.65 | −1.75 | 0.64 | −1.72 | AC117383.1 | 0.00 | −0.14 | 0.10 | 0.07 | 0.79 |
| SRI | 0.28 | −0.13 | −0.13 | −0.10 | −0.21 | MAF1 | 0.07 | 0.10 | −0.19 | 0.06 | −0.24 | RNU6-789P | 0.00 | −0.63 | −0.03 | −0.60 | 0.13 |
| AL049830.3 | 0.61 | −0.25 | −0.34 | −0.02 | −0.22 | AL008627.1 | −0.38 | −0.47 | 0.46 | 0.20 | 0.65 | MTND1P6 | 0.00 | −1.36 | 0.48 | 0.23 | 0.44 |
| AC073592.5 | 0.93 | 0.11 | −1.06 | −0.39 | −0.85 | PIGCP1 | 0.13 | 0.02 | 0.27 | −0.05 | −0.01 | AL356273.1 | 0.00 | −0.03 | −0.17 | −0.05 | −0.84 |
| SEMA6A-AS1 | −0.31 | 0.38 | 0.36 | 0.30 | 0.33 | MTND5P35 | −0.69 | −0.94 | −1.55 | 0.08 | −1.43 | RPSAP62 | −0.01 | 0.10 | −0.50 | −0.31 | −0.84 |
| MAP3K20 | 0.32 | −0.29 | −0.34 | −0.13 | −0.19 | KCNQ10T1 | −0.05 | 0.05 | 0.37 | −0.29 | −0.06 | RPL22P24 | 0.00 | −0.72 | −0.77 | −0.04 | −1.69 |
| ATP13A5-AS1 | −1.56 | 0.87 | 0.93 | 0.67 | 0.33 | AC046136.1 | −0.35 | 0.16 | 0.96 | −0.62 | −0.33 | AC098679.4 | 0.00 | 1.17 | 1.25 | −0.97 | −1.44 |
| CD19 | −0.59 | −0.19 | 0.60 | −0.29 | 0.56 | KCNE4 | −0.17 | −0.35 | 0.49 | −0.24 | −0.03 | AC087354.1 | −0.01 | 0.34 | 0.54 | −0.09 | −0.46 |
| CCDC78 | −0.58 | 0.10 | 0.15 | 0.30 | −0.31 | AC022447.6 | −0.88 | −0.13 | 2.44 | −0.54 | 0.70 | KRTAP10-1 | 0.01 | −0.78 | 0.78 | −1.36 | −1.05 |
| SMARCD2 | −0.15 | 0.17 | 0.09 | 0.11 | 0.07 | OR3A4P | 0.62 | −1.94 | −2.06 | 0.21 | 1.23 | SMIM5 | 0.00 | 0.22 | 0.30 | 0.46 | −0.17 |
| AC010319.5 | −1.96 | 0.96 | 1.67 | −0.42 | −0.61 | MIR3173 | 0.25 | 0.38 | −0.18 | −0.10 | −0.49 | MIR548AE1 | −0.01 | −1.08 | −1.24 | −0.04 | −1.19 |
| FAM124A | −0.37 | −0.11 | −0.02 | −0.17 | −0.15 | RN7SL269P | 0.31 | 0.03 | 0.27 | −0.53 | −0.14 | AC073488.5 | 0.01 | −0.49 | −1.68 | 0.45 | −0.29 |
| AC091132.3 | −0.59 | 0.55 | 0.82 | 0.08 | 0.30 | G33271 | 0.23 | −0.64 | −0.68 | −0.74 | −0.68 | AC119751.7 | −0.01 | −0.27 | −1.44 | 1.14 | −0.89 |
| RNU6-761P | −0.75 | 0.32 | 0.13 | 0.22 | 0.75 | AL359091.5 | −0.23 | −0.03 | 1.33 | −0.79 | −0.09 | RPL21P65 | 0.00 | −0.01 | −0.57 | 0.50 | −0.07 |
| AC074117.1 | −0.36 | 0.20 | 0.23 | 0.32 | 0.25 | GPAA1P1 | 0.69 | −0.87 | 0.48 | −0.86 | 0.76 | C2orf69P2 | 0.01 | −0.97 | −0.39 | 1.21 | 1.29 |
| AC117503.4 | 0.91 | 0.09 | 0.09 | 0.69 | −0.04 | HNRNPA1P34 | −0.32 | −0.29 | 2.00 | 0.08 | 1.27 | MYO5BP1 | 0.01 | −1.21 | 0.30 | −0.56 | 1.43 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| FSCN3 | −0.61 | 1.19 | 0.84 | 0.59 | 0.06 | AC098583.2 | −0.77 | 0.96 | −1.08 | 2.15 | −0.29 | AC007491.1 | 0.00 | −0.65 | −2.65 | 0.33 | −2.63 |
| AC008894.1 | 0.87 | −1.00 | 0.26 | −0.70 | 0.57 | LBX1 | −0.55 | −0.94 | 0.21 | 1.93 | 0.93 | LINC02221 | 0.01 | −1.74 | −0.34 | −0.32 | 0.84 |
| AL355987.5 | 1.57 | −0.56 | −0.82 | −0.04 | 0.14 | C15orf56 | 0.20 | −0.10 | −0.12 | 0.12 | 0.10 | RP11-403I13.9 | 0.00 | −0.45 | 0.55 | −0.12 | 0.97 |
| G24100 | −0.64 | −0.08 | 0.40 | 0.16 | −0.10 | RNF32 | −0.08 | 0.16 | 0.33 | 0.05 | 0.11 | AC092490.2 | 0.00 | −1.44 | −0.64 | −1.37 | −0.61 |
| AC008494.1 | −0.91 | 0.86 | 1.21 | 0.71 | 0.63 | ASS1P2 | 0.17 | 0.36 | −0.18 | 0.62 | −0.10 | AL512366.1 | 0.00 | −0.79 | −1.64 | 0.55 | −0.83 |
| DPYD-AS2 | 0.71 | −0.75 | −0.02 | −0.05 | 0.47 | GLP1R | 0.24 | 0.50 | −0.40 | 0.03 | 0.40 | OR14C36 | −0.01 | −0.34 | −0.48 | 0.89 | −0.84 |
| EFCAB5 | −0.45 | 0.29 | −0.54 | 0.17 | −0.33 | AL592310.1 | 0.20 | −0.88 | 0.84 | −0.31 | 0.80 | MTND2P22 | −0.01 | −0.56 | −0.56 | 0.85 | −0.89 |
| DTX2 | −0.36 | 0.27 | 0.23 | 0.22 | 0.22 | RNA5SP255 | −0.65 | −1.22 | 1.55 | 0.06 | 0.70 | AC015921.1 | 0.00 | 0.32 | 0.30 | 0.04 | 0.64 |
| RPS29P2 | 1.77 | 0.73 | 0.00 | 0.53 | 0.21 | PRR7 | 0.16 | −0.12 | −0.61 | 0.38 | −0.15 | APOBEC3G | 0.00 | −0.42 | 0.20 | −0.59 | 0.20 |
| C19orf12 | −0.29 | −0.11 | 0.04 | −0.11 | 0.08 | HIST2H3DP1 | −0.41 | 0.64 | 2.89 | −0.05 | 0.62 | HNRNPA3P4 | 0.00 | −0.27 | −0.68 | 0.21 | −0.58 |
| EXOSC2 | 0.17 | −0.26 | −0.33 | 0.01 | 0.03 | AC034223.1 | 0.30 | −2.09 | 1.48 | −0.52 | 0.97 | RPL23AP33 | 0.01 | −0.16 | −1.33 | 0.52 | −0.37 |
| AP003733.4 | −0.68 | 0.14 | −0.42 | 0.10 | 0.01 | LINC01958 | 0.58 | 1.58 | 0.58 | 1.70 | −1.20 | AC137579.2 | 0.00 | −0.22 | −0.01 | 1.22 | −1.68 |
| RIPK4 | 0.34 | −0.13 | −0.76 | 0.05 | −0.34 | PKD2L2 | −0.14 | −0.05 | 0.07 | −0.11 | 0.25 | AC006065.3 | −0.01 | −0.73 | NA | −0.18 | NA |
| RN7SL600P | 0.44 | −0.25 | −0.70 | −0.38 | −0.71 | RPL4P3 | 0.30 | −0.87 | −0.03 | 0.40 | 0.39 | AC090587.2 | 0.00 | −0.39 | −1.27 | 0.46 | −0.63 |
| LSM11 | 0.23 | −0.34 | −0.03 | −0.04 | 0.18 | AC073342.2 | 0.58 | 0.58 | 0.07 | −0.12 | 0.25 | CLN6 | 0.00 | −0.08 | −0.39 | 0.16 | −0.10 |
| RNU6-613P | 0.98 | −0.79 | −1.24 | −0.40 | −0.50 | MIR2278 | 0.26 | 0.20 | 0.08 | 0.32 | 0.00 | SNX18P10 | 0.00 | −0.23 | 0.44 | 0.10 | 1.16 |
| AC007991.4 | 1.87 | −2.70 | −1.89 | −1.18 | 1.96 | NENFP1 | 0.28 | 0.32 | 0.43 | 0.40 | 0.00 | AC025262.2 | 0.00 | −1.01 | 0.55 | −0.63 | 0.25 |
| ARMC2-AS1 | −0.96 | 0.59 | 0.27 | −0.01 | −0.66 | AC015845.1 | 0.16 | −0.11 | −0.28 | 0.00 | 0.03 | LINC02049 | 0.01 | −0.20 | 1.41 | −0.52 | 0.93 |
| F8 | −0.48 | 0.68 | 0.86 | 0.34 | 0.04 | AC087821.2 | −0.21 | −0.19 | 0.34 | 0.09 | 0.38 | OR8B4 | −0.01 | −0.26 | 1.60 | −0.73 | −0.51 |
| AC110921.1 | 1.05 | −0.60 | −0.95 | −0.86 | −1.31 | IGKV1D-42 | 1.01 | −0.84 | −2.10 | 1.19 | 2.00 | NSUN3 | 0.00 | −0.01 | 0.03 | 0.18 | 0.11 |
| AL021328.1 | 0.34 | −0.16 | −0.06 | −0.35 | 0.13 | AL109924.3 | −0.70 | 1.43 | −2.28 | 1.10 | −2.05 | PCDH9-AS1 | −0.01 | 0.25 | −0.13 | 2.00 | −2.06 |
| G41428 | −1.46 | −0.88 | 0.75 | −0.45 | 1.49 | AC091435.1 | −0.24 | −1.32 | −0.10 | −0.19 | 0.25 | AC080011.1 | 0.00 | −1.12 | 0.84 | 1.07 | 3.33 |
| SNORD51 | 0.97 | −0.69 | −1.03 | −0.25 | −0.07 | AC044802.1 | −0.27 | −0.86 | 0.24 | −0.62 | 0.58 | DDX39AP1 | −0.01 | 0.43 | −0.06 | 2.25 | −0.26 |
| BARHL1 | −0.86 | 0.21 | 0.09 | −0.32 | −0.01 | LINC00563 | 0.59 | −1.45 | −1.57 | 0.25 | 0.38 | PSMB7P1 | −0.01 | −0.14 | −1.03 | 1.35 | −0.15 |
| STXBP2 | −0.25 | 0.03 | −0.35 | 0.19 | −0.05 | AC244034.3 | −0.17 | 0.39 | 0.67 | −0.20 | 0.09 | NACAP7 | 0.01 | 0.80 | −0.64 | 1.74 | −1.82 |
| MAU2 | −0.20 | 0.18 | 0.13 | 0.08 | 0.00 | EEF1A1P36 | 0.50 | −0.42 | −0.46 | 0.26 | −0.23 | NAP1L1P1 | 0.00 | 0.02 | 0.02 | −0.24 | 0.06 |
| AC008013.2 | −0.89 | −0.12 | 0.74 | 0.28 | 0.11 | DGKZ | 0.06 | −0.04 | −0.27 | 0.07 | 0.09 | SLC22A16 | 0.00 | −0.11 | −1.18 | 0.98 | −0.61 |
| SLC6A15 | 0.45 | −0.47 | −0.85 | 0.33 | −0.25 | AC126365.1 | −0.64 | −0.57 | −0.54 | 0.62 | −0.93 | GRM8 | 0.00 | −0.74 | −0.81 | −0.28 | −0.01 |
| AC015726.3 | −0.64 | −0.29 | 0.49 | 0.24 | 0.85 | LINC00402 | 0.35 | −1.23 | 1.25 | −0.76 | 0.82 | AL591222.3 | −0.01 | −0.08 | −1.63 | 0.79 | −1.70 |
| RNUSB-2P | −0.73 | −0.69 | −0.16 | −0.15 | 0.22 | AC092535.1 | −0.18 | 0.12 | 0.50 | 0.07 | 0.17 | AL359075.1 | 0.00 | 0.74 | −0.47 | 1.09 | 0.13 |
| SMIM17 | −1.03 | 0.96 | 1.43 | 0.12 | 0.61 | AL512604.1 | 0.26 | −0.23 | 0.29 | 0.19 | 0.81 | RPL23AP39 | 0.01 | −0.31 | −0.47 | −0.68 | −1.43 |
| OXA1L | 0.12 | −0.06 | −0.23 | 0.04 | −0.17 | AC020891.4 | −0.38 | −0.78 | 1.65 | −0.19 | 1.26 | RNU7-108P | 0.00 | −0.45 | 0.97 | −1.03 | −0.10 |
| SNRPCP5 | −1.86 | 0.16 | 0.82 | 0.61 | 0.05 | FMO6P | −0.18 | 0.23 | 0.22 | 0.33 | 0.06 | STATH | 0.00 | −0.44 | −1.04 | −1.03 | −1.32 |
| AL035456.1 | −0.33 | 0.10 | 0.18 | −0.22 | 0.15 | RPL39P29 | −0.65 | −1.12 | −0.37 | −0.55 | −0.85 | RN7SL35P | −0.01 | 0.57 | −0.32 | −0.38 | −1.47 |
| CLCNKB | −1.06 | 0.43 | 2.19 | 0.19 | 1.33 | IL6ST | −0.11 | 0.15 | 0.28 | −0.15 | −0.09 | AL163195.3 | 0.00 | −1.71 | −0.73 | 0.01 | 1.37 |
| FAM124B | 0.51 | −0.25 | −0.09 | 0.10 | 0.08 | RPTN | 0.24 | −0.60 | −0.42 | −0.48 | −0.52 | AC079384.1 | 0.00 | −1.47 | 0.73 | −2.00 | −1.08 |
| MINOS1 | −0.33 | 0.03 | −0.10 | 0.07 | 0.07 | RNU6-46P | −0.62 | 1.61 | 2.20 | −0.74 | −0.14 | SLC26A2 | 0.00 | 0.14 | 0.33 | −0.09 | 0.30 |
| MRPS18B | 0.16 | −0.04 | −0.12 | 0.00 | −0.11 | AC004691.1 | 0.20 | −0.18 | −0.13 | −0.06 | −0.18 | OR2T12 | 0.00 | 0.25 | −0.44 | 0.43 | −1.14 |
| RNU6-11P | −1.04 | 0.17 | −1.54 | 0.55 | −0.55 | MRPL57P7 | −1.34 | 0.76 | 1.17 | −0.47 | 0.30 | LY6G6D | 0.00 | 1.25 | −0.82 | 0.13 | −1.97 |
| AC023389.2 | 0.57 | −0.04 | −0.47 | −0.09 | −0.23 | AC099499.1 | 0.68 | −1.48 | −0.61 | 0.00 | 3.39 | LINC01664 | 0.00 | −0.94 | −0.74 | −0.04 | 1.24 |
| AC008083.1 | 1.23 | −0.98 | −0.78 | −0.36 | 0.16 | LAG3 | −0.18 | −0.54 | −0.21 | −0.38 | 0.68 | AC079942.1 | 0.01 | 1.07 | −1.14 | 0.35 | −2.78 |
| CD248 | −0.62 | 0.25 | 1.59 | −0.19 | 0.00 | HSPA8P6 | −0.63 | 0.81 | −1.11 | 1.19 | 0.53 | AC131094.1 | 0.01 | 0.13 | −0.47 | −1.15 | −1.96 |
| AC116158.1 | 0.52 | −0.56 | −0.17 | −0.03 | 0.09 | NPM1P28 | −0.51 | −0.59 | 0.97 | −0.81 | 1.16 | AC117500.5 | −0.01 | −0.19 | 0.65 | −0.90 | −0.74 |
| RPS2P44 | 0.36 | −0.49 | −0.99 | −0.15 | 0.11 | AP005137.1 | 0.37 | 0.18 | 1.44 | 0.90 | 0.16 | PEX7 | 0.00 | 0.15 | 0.10 | 0.17 | 0.06 |
| MTX1P1 | 0.74 | 0.17 | −0.68 | 0.40 | −0.32 | RNU6-661P | 0.59 | −0.88 | −0.29 | 0.28 | 0.78 | LINC02603 | 0.00 | 0.71 | −0.32 | 0.48 | −1.11 |
| AC131649.1 | −1.63 | 0.25 | 1.54 | 0.02 | 0.35 | AL353796.1 | 0.13 | −0.17 | −0.08 | −0.23 | 0.06 | AC106872.7 | 0.00 | 0.64 | −0.32 | 1.41 | 0.64 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| AUTS2 | −0.18 | 0.20 | 0.17 | 0.12 | 0.17 | G15374 | −0.26 | 0.66 | 1.59 | 0.18 | 0.12 | AC020743.1 | 0.00 | 0.21 | −0.58 | 0.05 | −1.57 |
| ADGRE3 | 1.32 | −1.06 | −1.64 | 0.60 | −0.05 | KPNA7 | −0.26 | 0.23 | −0.08 | 0.10 | −0.34 | AC093801.2 | 0.01 | −1.36 | 1.18 | −1.22 | 2.55 |
| LYPLA1P3 | 1.03 | −0.12 | −0.89 | 0.32 | −0.22 | RN7SL70P | −0.42 | −0.44 | −2.29 | 1.35 | −1.13 | MAGEB18 | −0.01 | −0.70 | −0.06 | −0.33 | −1.95 |
| AC106820.3 | 0.98 | −0.23 | −2.36 | −0.43 | −1.07 | PTPRR | −0.31 | −0.03 | 0.04 | −0.12 | 0.25 | RPS26P38 | 0.01 | −0.89 | −0.09 | −0.12 | 0.58 |
| PRDM2 | 0.14 | −0.03 | −0.18 | −0.03 | −0.06 | KCNIP4 | −0.12 | 0.05 | 0.78 | −0.16 | −0.06 | AC008662.2 | −0.01 | 0.15 | 0.18 | 0.16 | −0.05 |
| AC005532.1 | −0.49 | −0.14 | 0.19 | −0.01 | −0.02 | OR8B5P | −0.66 | −1.70 | −0.31 | 0.25 | 2.57 | GMCLIP2 | 0.00 | −1.17 | 0.23 | 0.16 | 0.46 |
| DUS4L | 0.23 | −0.26 | −0.06 | 0.09 | 0.26 | SFTA2 | −0.93 | −1.56 | 0.81 | −1.78 | 2.11 | AC016717.2 | 0.00 | −0.19 | −0.40 | 0.97 | 0.63 |
| EMC3 | 0.22 | −0.06 | −0.44 | 0.00 | −0.31 | MIR4755 | 0.13 | −0.59 | 0.13 | −0.45 | 0.35 | HIGDIC | 0.00 | 0.28 | 0.34 | 0.16 | 0.84 |
| NUDT22 | −0.35 | 0.02 | −0.39 | 0.16 | 0.02 | IAPP | −0.52 | −1.60 | −0.23 | −0.06 | 1.46 | MRAP | 0.00 | 0.33 | −0.35 | 0.20 | 0.27 |
| CARD11 | 0.63 | −1.00 | 0.23 | −0.83 | 0.35 | AC007342.8 | 0.48 | −0.70 | 0.73 | 0.06 | 1.58 | AC010099.3 | −0.01 | −0.92 | −0.47 | 0.02 | NA |
| P2RY6 | 0.60 | −0.66 | −0.82 | −0.41 | −0.09 | AC079807.1 | −0.13 | 0.09 | 0.06 | −0.18 | −0.04 | AC024405.1 | 0.00 | 2.09 | −1.18 | 1.78 | −1.93 |
| RN7SL543P | −1.81 | 1.81 | 1.82 | 0.44 | 0.17 | AP005432.2 | 0.44 | 0.64 | −0.20 | 0.44 | −1.11 | AC074052.2 | −0.01 | −0.44 | −0.49 | −0.10 | −0.09 |
| PPP1R11P2 | −0.90 | 0.22 | 0.68 | −0.38 | 0.19 | RN7SL757P | −0.42 | 0.15 | 0.34 | 0.36 | 0.21 | RPL21P5 | 0.00 | −0.14 | 0.09 | −0.06 | 0.30 |
| RNU1-109P | 0.55 | −0.09 | −0.65 | −0.15 | −0.44 | FER1L6 | 0.21 | −0.29 | −0.78 | −0.33 | 0.02 | AC010247.1 | 0.00 | 0.19 | 0.21 | 0.07 | −0.15 |
| AC129502.1 | 0.49 | −0.34 | −0.37 | −0.07 | 0.19 | C9orf129 | −0.60 | 0.43 | 0.45 | −0.44 | −0.35 | LMOD2 | 0.00 | 0.31 | −0.40 | −0.37 | −0.83 |
| GBP1P1 | 0.48 | −0.37 | −0.05 | −0.42 | −0.14 | AC013470.2 | 0.44 | 0.32 | −1.34 | 0.17 | −1.16 | AC098935.2 | 0.00 | −0.52 | −0.85 | −0.52 | −0.65 |
| RPL23A | 0.36 | 0.18 | 0.04 | −0.05 | −0.51 | CACNA1A | −0.18 | −0.18 | −0.67 | −0.12 | −0.29 | MTCO1P31 | 0.00 | 0.40 | 1.14 | −0.27 | −0.87 |
| AC119744.1 | −0.92 | 0.61 | 0.54 | 0.75 | 1.24 | MIR4263 | 0.50 | −1.69 | −0.44 | −0.64 | 0.45 | RPL36AP40 | 0.00 | 1.16 | −1.64 | 1.91 | −0.77 |
| CLEC6A | 1.64 | −0.61 | −1.74 | −0.36 | −0.07 | LINC01779 | −0.81 | −0.85 | 1.66 | −0.66 | 3.36 | AC019209.1 | −0.01 | 0.13 | −0.05 | 0.51 | 0.23 |
| AC105271.1 | −1.27 | 0.67 | 1.86 | −0.52 | 0.66 | AL109615.3 | 0.29 | −0.01 | −1.02 | −0.12 | −0.32 | RN7SL623P | −0.01 | −0.17 | 0.51 | −0.08 | 0.74 |
| AC107959.3 | 1.72 | −1.12 | −3.48 | 0.43 | −1.78 | AC119428.3 | 0.65 | −0.44 | 0.26 | −0.48 | 0.17 | AC096949.1 | 0.00 | −1.52 | 0.59 | −1.04 | 2.09 |
| FTSJ3 | 0.21 | −0.21 | −0.38 | −0.11 | −0.15 | AC073082.1 | −0.44 | −0.92 | −1.77 | 0.36 | 0.20 | SLC8A2 | 0.00 | 0.01 | −0.29 | 0.31 | −0.57 |
| MTOR-AS1 | 0.41 | −0.17 | −0.59 | −0.01 | −0.15 | AL049545.1 | −1.11 | −1.00 | −0.17 | −0.30 | 1.60 | AP006259.1 | 0.00 | −0.48 | −0.36 | 0.14 | 0.62 |
| SLC11A1 | 0.62 | −1.10 | −0.95 | −0.57 | −0.93 | SNRPGP17 | −0.64 | 0.63 | 1.35 | 0.75 | 1.26 | AC006600.1 | −0.01 | 0.61 | −0.11 | 0.77 | −1.48 |
| FOXK2 | 0.21 | −0.08 | −0.41 | 0.11 | −0.15 | AC098820.3 | 0.42 | −0.10 | 0.91 | 1.20 | 1.14 | SLC25A51P1 | −0.01 | 0.79 | 0.01 | −1.09 | −0.71 |
| AC005332.1 | −0.38 | 0.18 | 0.30 | 0.26 | 0.18 | AC010401.2 | −0.63 | −0.18 | 0.21 | 0.10 | −0.44 | AIF1 | 0.00 | −0.23 | 0.46 | −0.36 | 0.03 |
| FGF18 | −0.83 | 1.09 | 0.14 | 0.30 | −1.05 | HLA-DPA2 | 0.84 | −0.81 | −0.80 | 0.00 | −0.59 | AL356321.1 | −0.01 | −0.41 | −0.87 | 1.52 | −1.86 |
| EPG5 | −0.17 | 0.13 | 0.27 | 0.07 | 0.04 | LSM6 | 0.08 | −0.06 | −0.04 | −0.21 | −0.01 | AC018880.1 | −0.01 | 0.49 | −0.29 | 0.18 | −0.65 |
| AL357936.1 | −1.15 | 0.64 | 2.81 | −0.86 | 0.07 | AC003666.1 | 0.68 | −1.20 | −2.24 | 0.30 | −0.20 | AL022337.1 | 0.00 | −1.50 | 1.74 | 0.16 | 2.61 |
| ITPKB-IT1 | −0.43 | −0.16 | 0.15 | −0.06 | 0.24 | SIRPD | −0.44 | −1.02 | −1.22 | −0.96 | −0.33 | AC104454.1 | 0.00 | −0.39 | 0.08 | −0.48 | 0.87 |
| AC040174.2 | −1.18 | 0.39 | 0.34 | −1.06 | −0.83 | LDHB | 0.21 | −0.09 | −1.33 | 0.30 | −0.32 | MTCYBP16 | 0.00 | −1.74 | −0.74 | −0.81 | −0.03 |
| RPL22P19 | −0.82 | 0.94 | 0.77 | 1.17 | 0.20 | LINC02059 | −0.74 | 0.48 | −1.18 | 0.66 | −1.72 | AL136140.1 | 0.00 | −0.90 | 1.15 | −2.14 | −0.36 |
| LY86-AS1 | −0.72 | −0.49 | 0.01 | 0.12 | 0.26 | PKD1L1 | 0.15 | −0.20 | 0.24 | −0.25 | 0.05 | MTND2P24 | 0.00 | −0.26 | 0.15 | −0.90 | 0.08 |
| EIF2S2P5 | 0.50 | −0.77 | −0.56 | −0.36 | −0.01 | MRPL15P1 | −0.42 | 0.56 | 0.23 | 0.38 | −0.48 | AC110741.2 | 0.00 | −0.40 | 0.27 | −0.39 | 0.47 |
| AL096870.2 | −0.77 | 0.31 | 1.04 | 0.29 | 0.30 | AL356417.2 | 0.48 | 1.16 | −1.83 | −2.68 | −1.03 | AC073172.2 | 0.00 | −0.46 | −1.71 | 0.30 | −2.39 |
| P2RX2 | −0.88 | 0.10 | −0.33 | 0.10 | −0.60 | RNU6-1185P | 0.25 | 0.83 | 0.04 | 0.34 | −0.36 | AL354754.1 | 0.00 | 0.70 | −2.54 | 0.27 | −1.87 |
| AL590652.1 | −0.40 | 0.44 | 0.61 | 0.33 | 0.19 | OR51B2 | −0.60 | 1.42 | −1.45 | 0.95 | −0.94 | RNA5SP238 | 0.00 | 0.11 | −0.55 | 0.29 | −0.66 |
| AL157931.2 | −1.18 | −0.15 | 0.93 | −0.22 | 2.74 | ACBD3-AS1 | 0.21 | −0.34 | 0.37 | −0.14 | 0.05 | AC068538.1 | 0.00 | −1.05 | −1.04 | −1.11 | −0.57 |
| ABCB8 | −0.26 | 0.05 | −0.18 | 0.19 | 0.12 | RPS2P36 | 0.24 | −1.16 | 0.57 | −0.32 | 1.69 | LINC02383 | 0.00 | −0.55 | 0.05 | −0.90 | −1.96 |
| AL031123.1 | −0.86 | −0.34 | −0.08 | 0.22 | 0.77 | RBM26 | −0.03 | −0.05 | −0.02 | 0.02 | 0.08 | AL133304.3 | 0.00 | 0.14 | −0.23 | −0.26 | −1.21 |
| LINC00637 | −0.86 | 0.22 | 0.48 | 0.70 | 0.96 | AC022447.4 | −1.10 | 0.92 | 2.44 | −0.30 | 0.75 | RPSAP35 | 0.00 | −0.95 | 0.17 | 0.98 | −1.38 |
| ABCA13 | 0.70 | −0.27 | −1.08 | 0.42 | −0.47 | IGHV3-33 | 1.28 | 1.39 | 1.80 | −0.93 | −2.70 | NFYB | 0.00 | −0.05 | 0.10 | −0.03 | 0.15 |
| AL136295.6 | −0.44 | −0.11 | 0.55 | 0.27 | 0.65 | AC005790.1 | −0.50 | −0.05 | −1.86 | 1.42 | 0.68 | AP005902.2 | 0.00 | 0.06 | 0.59 | −0.39 | −0.26 |
| GTF2F1 | 0.20 | −0.21 | −0.42 | −0.06 | −0.08 | G32932 | −0.88 | −0.92 | 1.18 | −0.36 | 1.18 | LINC00354 | 0.00 | −0.15 | −1.07 | −0.19 | −0.14 |
| RNA5SP48 | −1.19 | 2.10 | 0.22 | 2.17 | −0.43 | CD300A | −0.14 | −0.60 | 0.42 | −0.26 | 0.15 | AC007098.2 | 0.00 | 0.35 | −0.10 | 0.19 | 0.39 |
| DNAJB5-DT | 1.35 | −1.75 | −0.86 | −0.49 | −0.35 | AC104794.3 | −0.87 | 0.87 | −1.76 | 1.35 | 0.77 | ASS1P12 | 0.00 | −0.26 | −0.09 | −0.12 | −0.02 |

TABLE 1-continued

Differentially expressed analysis in five different comparisons: (A) non-lesional vs lesional skin at baseline; (B) baseline vs week 12 for placebo group; (C) baseline vs week12 for the nemo group; (D) placebo vs nemo groups at baseline; (E) placebo vs nemo groups at week 12. Differential expression values shown as log2 fold change (i.e.. log2FC). P-values and false discovery rates (FDRs) were calculated but not shown.

| Gene | A | B | C | D | E | Gene | A | B | C | D | E | Gene | A | B | C | D | E |
|---|---|---|---|---|---|---|---|---|---|---|---|---|---|---|---|---|---|
| MIR374A | 1.11 | −2.01 | −0.78 | 0.10 | 0.39 | LINC01977 | −0.38 | −0.75 | −0.07 | −1.11 | 0.28 | OR7E4P | 0.00 | −1.37 | 0.43 | −1.17 | 0.22 |
| AC092800.1 | 0.62 | −0.59 | −0.82 | −0.39 | −0.27 | AL592301.1 | −0.15 | 0.01 | −0.09 | 0.23 | 0.06 | AC009948.4 | 0.00 | −0.02 | 2.15 | −0.11 | 0.42 |
| LINC01107 | −0.97 | 0.22 | 1.24 | −0.21 | 0.27 | AP001412.1 | −0.39 | −0.72 | −0.55 | −0.01 | −0.21 | AC092159.4 | 0.00 | 0.54 | 1.97 | −0.03 | 0.90 |
| ASXL1 | −0.13 | −0.07 | −0.08 | −0.01 | 0.06 | SGSM3 | −0.15 | −0.57 | 0.26 | −0.44 | 0.23 | AP003399.1 | 0.00 | −1.41 | −1.72 | 0.16 | 0.69 |
| LINC00844 | −1.54 | 0.32 | 2.08 | 0.06 | −0.42 | SPHKAP | −0.29 | 0.34 | 0.45 | 0.86 | 0.50 | LINC00903 | 0.00 | 0.15 | −0.77 | 0.40 | −1.67 |
| AC105094.1 | −1.14 | 1.10 | 1.14 | 0.93 | 0.64 | NFYC | 0.04 | 0.12 | −0.13 | 0.08 | −0.14 | AC025575.1 | 0.00 | −0.06 | 1.37 | 1.26 | 1.12 |
| AC096713.1 | −1.50 | −0.04 | 2.11 | 1.51 | 0.26 | AC008728.1 | 0.60 | −1.01 | −0.33 | −0.36 | −1.96 | LINC01639 | 0.00 | −1.47 | 0.13 | −1.91 | −0.35 |
| MIR548I1 | −1.04 | −0.21 | 0.42 | −0.74 | 0.73 | KLRK1 | −0.19 | −0.27 | 0.65 | −0.53 | −0.16 | RICTOR | 0.00 | 0.15 | 0.08 | 0.02 | −0.15 |
| AL691447.2 | −0.70 | −0.71 | 0.84 | 0.21 | 0.53 | CFHR2 | 0.59 | −1.79 | −0.66 | 1.37 | 0.55 | ELMO2P1 | 0.00 | −0.01 | −1.64 | 0.51 | 1.21 |
| PIWIL4 | −0.47 | −0.04 | 0.36 | 0.02 | −0.01 | CD37 | −0.13 | −0.08 | 0.07 | −0.12 | 0.09 | GSTA5 | 0.00 | −0.90 | −0.44 | −0.78 | −0.48 |
| SLC6A1 | −0.50 | 0.31 | 0.21 | 0.46 | 0.16 | G14441 | 0.67 | −0.68 | −1.46 | 0.11 | −1.46 | PPIE | 0.00 | −0.08 | −0.22 | 0.15 | −0.05 |
| SBF2 | −0.13 | 0.17 | 0.11 | 0.05 | −0.02 | PRICKLE4 | −0.64 | 1.87 | 0.74 | 0.95 | −0.48 | GSTM2P1 | 0.00 | −0.66 | −0.64 | 1.88 | −0.12 |
| DUSP22 | −0.17 | 0.12 | −0.08 | 0.03 | −0.20 | AC079336.5 | −0.12 | −0.03 | 0.24 | −0.09 | 0.50 | LINC00561 | 0.00 | −0.23 | −1.21 | 0.65 | −0.51 |
| AL591767.1 | −0.84 | 0.50 | 0.32 | −0.14 | 0.38 | G25089 | 0.42 | 0.03 | 0.13 | −0.46 | −0.11 | AL390962.1 | 0.00 | −0.54 | −1.32 | 1.38 | 0.36 |
| SGSH | −0.23 | 0.16 | 0.12 | 0.23 | 0.16 | LINC01727 | 0.55 | 0.19 | −0.45 | −0.01 | −0.41 | RPL7P28 | 0.00 | 1.23 | −0.40 | 2.17 | 0.32 |
| AL139184.1 | 0.73 | −0.29 | −0.66 | 0.06 | −0.24 | FGL1 | 0.44 | −0.11 | −0.44 | 0.57 | 0.47 | PPP6R2P1 | 0.00 | 0.02 | −0.51 | −0.20 | −0.72 |
| AMFR | 0.24 | 0.11 | −0.11 | 0.02 | −0.20 | KRTAP12-6P | −1.20 | −0.87 | −0.28 | −0.28 | 0.62 | MORC2 | 0.00 | −0.03 | −0.15 | −0.01 | 0.02 |
| RPS15AP6 | 0.55 | −0.18 | −1.18 | 0.28 | −0.79 | KRT18P29 | 0.48 | −0.62 | −0.12 | 0.72 | 0.26 | BACE1 | 0.00 | 0.03 | 0.15 | −0.09 | −0.03 |
| AP003396.2 | 1.45 | −0.17 | −0.28 | −0.37 | −0.30 | AC092658.1 | 0.20 | −0.36 | 0.17 | −0.17 | 0.31 | AC127164.1 | 0.00 | −0.14 | 0.14 | −0.04 | 0.36 |
| AC022509.3 | −0.61 | 0.53 | −0.50 | 0.24 | −0.62 | AF213884.2 | −0.59 | 0.63 | 0.20 | 0.50 | 0.34 | CST2 | 0.00 | −1.38 | −0.43 | −0.81 | 0.03 |
| AL117339.5 | −0.49 | 0.22 | 1.21 | 0.18 | 0.83 | MIR4466 | −0.37 | 0.09 | 1.73 | −0.41 | 0.06 | | | | | | |
| SMIM3 | 0.97 | −1.64 | −1.91 | −0.24 | −1.01 | KCNH1 | 0.17 | −0.38 | −0.62 | 0.36 | −0.20 | | | | | | |

TABLE 2

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| dna packaging complex: GO | 91 | 39 | 7.17 | H2AFX; H2AFZ; HIST1H1A; HIST1H1B; HIST1H1D; HIST1H2AB; HIST1H2AE; HIST1H2AG; HIST1H2AH; HIST1H2AI; HIST1H2AL; HIST1H2BB; HIST1H2BC; HIST1H2BE; HIST1H2BF; HIST1H2BG; HIST1H2BH; HIST1H2BI; HIST1H2BJ; HIST1H2BK; HIST1H2BL; HIST1H2BM; HIST1H2BO; HIST1H3A; HIST1H3B; HIST1H3C; HIST1H3F; HIST1H3G; HIST1H3H; HIST1H3I; HIST1H3J; HIST1H4I; | 2 | 0.26 | HILS1; TNP1 | 0 | 0.00 | | 0 | 0.00 | | 0 | 0.00 | | 36 | 11.22 | H2AFX; H2AFZ; HIST1H1B; HIST1H1D; HIST1H2AB; HIST1H2AE; HIST1H2AG; HIST1H2AH; HIST1H2AI; HIST1H2AL; HIST1H2BB; HIST1H2BC; HIST1H2BD; HIST1H2BE; HIST1H2BF; HIST1H2BG; HIST1H2BI; HIST1H2BJ; HIST1H2BK; HIST1H2BL; HIST1H2BM; HIST1H2BO; HIST1H3A; HIST1H3C; HIST1H3F; HIST1H3G; HIST1H3H; HIST1H3I; HIST1H3J; HIST1H4I; HIST2H2AA3; HIST2H2BE; |
| rna pol i promoter opening | 56 | 29 | 8.67 | H2AFX; H2AFZ; HIST1H2AB; HIST1H2AE; HIST1H2AJ; HIST1H2BB; HIST1H2BC; | 0 | 0.00 | | 0 | 0.00 | | 0 | 0.00 | | 0 | 0.00 | | 27 | 13.67 | H2AFX; H2AFZ; HIST1H2AB; HIST1H2AE; HIST1H2AJ; HIST1H2BB; HIST1H2BC; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline: Up-regu-lated | A: Fold Change (FC) Up | A: Up-regulated Genes | A: Down-regu-lated | A: Fold Change (FC) | A: Down-regulated Genes | B. Differentially expressed genes significant in the baseline vs week 12 comparison only in the placebo: Up-regu-lated | B: Fold Change (FC) Up | B: Up-regulated Genes | B: Down-regu-lated | B: Fold Change (FC) | B: Down-regulated Genes | C. Differentially expressed genes significant in the baseline vs week 12 comparison only in the nemo: Up-regu-lated | C: Fold Change (FC) Up | C: Up-regulated Genes | C: Down-regu-lated | C: Fold Change (FC) | C: Down-regulated Genes |
|---|---|---|---|---|---|---|---|---|---|---|---|---|---|---|---|---|---|---|---|
| | | | | HIST1H2BE;<br>HIST1H2BF;<br>HIST1H2BG;<br>HIST1H2BH;<br>HIST1H2BI;<br>HIST1H2BJ;<br>HIST1H2BK;<br>HIST1H2BL;<br>HIST1H2BM;<br>HIST1H2BO;<br>HIST1H3A;<br>HIST1H3B;<br>HIST1H3C;<br>HIST1H3F;<br>HIST1H3G;<br>HIST1H3H;<br>HIST1H3I;<br>HIST1H3J;<br>HIST1H4I;<br>HIST1H4J;<br>HIST1H4K;<br>HIST1H4L | | | | | | | | | | | | | | | HIST1H2BD;<br>HIST1H2BE;<br>HIST1H2BF;<br>HIST1H2BG;<br>HIST1H2BI;<br>HIST1H2BJ;<br>HIST1H2BK;<br>HIST1H2BL;<br>HIST1H2BM;<br>HIST1H2BO;<br>HIST1H3A;<br>HIST1H3C;<br>HIST1H3F;<br>HIST1H3G;<br>HIST1H3H;<br>HIST1H3I;<br>HIST1H3J;<br>HIST1H4I;<br>HIST2H2AA3;<br>HIST2H2BE |
| meiotic recombination | 79 | 32 | 6.78 | BLM;<br>BRCA2;<br>H2AFX;<br>H2AFZ;<br>HIST1H2AB;<br>HIST1H2AE;<br>HIST1H2AJ;<br>HIST1H2BB;<br>HIST1H2BC;<br>HIST1H2BE;<br>HIST1H2BF;<br>HIST1H2BG;<br>HIST1H2BH;<br>HIST1H2BI;<br>HIST1H2BJ;<br>HIST1H2BK;<br>HIST1H2BL;<br>HIST1H2BM;<br>HIST1H2BO; | 0 | 0.00 | | 0 | 0.00 | | 0 | 0.00 | | 0 | 0.00 | | 30 | 10.77 | BLM;<br>BRCA2;<br>H2AFX;<br>H2AFZ;<br>HIST1H2AB;<br>HIST1H2AE;<br>HIST1H2AJ;<br>HIST1H2BB;<br>HIST1H2BC;<br>HIST1H2BD;<br>HIST1H2BE;<br>HIST1H2BF;<br>HIST1H2BG;<br>HIST1H2BI;<br>HIST1H2BJ;<br>HIST1H2BK;<br>HIST1H2BL;<br>HIST1H2BM;<br>HIST1H2BO; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L; MND1 | | | | | | | | | | | | | | | HIST1H3A; HIST1H3C; HIST1H3F; HIST1H3G; HIST1H3H; HIST1H3I; HIST1H3J; HIST1H4I; HIST2H2AA3; HIST2H2BE; MND1 |
| rho gtpase effectors | 189 | 46 | 4.07 | ACTR3; ARPC1A; BIRC5; BUB1; BUB1B; CDC20; CDCA8; CENPA; CENPE; CENPF; CENPN; DIAPH3; DYNLL1; H2AFX; H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; HIST1H4L; KIF14; | 4 | 0.25 | AR; MAST1; MYL9; RHPN2 | 0 | 0.00 | | 0 | 0.00 | | 2 | 0.27 | DLC1; RHPN2 | 43 | 6.45 | ARPC1A; AURKB; BIRC5; BUB1; BUB1B; CDC20; CDCA8; CENPA; CENPE; CENPF; DIAPH3; H2AFX; H2AFZ; HIST1H2AE; HIST1H2BB; HIST1H2BD; HIST1H2BF; HIST1H2BK; HIST1H2BM; HIST1H3A; HIST1H3I; HIST1H4I; HIST2H2BE; KIF14; KIF18A; KIF2C; KNL1; MAD2L1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | KIF18A; KIF2C; KNL1; MAD2L1; NDC80; | | | | | | | | | | | | | | | NDC80; NUF2; PLK1; SFN; SGO2; SKA1; SPC24; SPC25; |
| resolution of sister chromatid cohesion | 85 | 30 | 5.91 | BIRC5; BUB1; BUB1B; CCNB1; CCNB2; CDC20; CDCA5; CDCA8; CDK1; CENPA; CENPE; CENPF; CENPN; DYNLL1; KIF18A; KIF2C; KNL1; MAD2L1; NDC80; NUF2; PLK1; SGO2; SKA1; SPC25; TUBA1C; TUBA4A; TUBB2A; TUBB6; ZWILCH; ZWINT | 1 | 0.14 | MAST1 | 0 | 0.00 | | 0 | 0.00 | | 1 | 0.30 | DLC1 | 30 | 10.01 | AURKB; BIRC5; BUB1; BUB1B; CCNB1; CCNB2; CDC20; CDCA5; CDCA8; CDK1; CENPA; CENPE; CENPF; KIF18A; KIF2C; KNL1; MAD2L1; NDC80; NUF2; PLK1; SGO2; SKA1; SPC24; SPC25; TUBA1C; TUBA4A; TUBB2A; TUBB6; ZWILCH; ZWINT |
| amyloids | 75 | 31 | 6.92 | H2AFX; H2AFZ; HIST1H2AB; HIST1H2AE; HIST1H2AJ; HIST1H2BB; HIST1H2BC; | 2 | 0.31 | GSN; SNCA | 0 | 0.00 | | 1 | 5.57 | LYZ | 1 | 0.34 | SNCA | 28 | 10.59 | H2AFX; H2AFZ; HIST1H2AB; HIST1H2AE; HIST1H2AJ; HIST1H2BB; HIST1H2BC; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | HIST1H2BE; HIST1H2BF; HIST1H2BG; HIST1H2BH; HIST1H2BI; HIST1H2BJ; HIST1H2BK; HIST1H2BL; HIST1H2BM; HIST1H2BO; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L; LTF; LYZ | | | | | | | | | | | | | | | HIST1H2BD; HIST1H2BE; HIST1H2BF; HIST1H2BG; HIST1H2BI; HIST1H2BJ; HIST1H2BK; HIST1H2BL; HIST1H2BM; HIST1H2BO; HIST1H3A; HIST1H3C; HIST1H3F; HIST1H3G; HIST1H3H; HIST1H3I; HIST1H3J; HIST1H4I; HIST2H2AA3; HIST2H2BE; LTF |
| nuclear nucleosome: GO | 34 | 20 | 9.84 | HIST1H2BB; HIST1H2BC; HIST1H2BE; HIST1H2BF; HIST1H2BG; HIST1H2BH; HIST1H2BI; HIST1H2BJ; HIST1H2BK; HIST1H2BL; HIST1H2BM; HIST1H2BO; HIST1H3A; HIST1H3B; HIST1H3C; HIST1H3F; HIST1H3G; HIST1H3H; | 0 | 0.00 | | 0 | 0.00 | | 0 | 0.00 | | 0 | 0.00 | | 20 | 16.68 | HIST1H2BB; HIST1H2BC; HIST1H2BD; HIST1H2BE; HIST1H2BF; HIST1H2BG; HIST1H2BI; HIST1H2BJ; HIST1H2BK; HIST1H2BL; HIST1H2BM; HIST1H2BO; HIST1H3A; HIST1H3C; HIST1H3F; HIST1H3G; HIST1H3H; HIST1H3I; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | HIST1H3I;<br>HIST1H3J | | | | | | | | | | | | | | | HIST1H3J;<br>HIST2H2BE |
| protein dna complex: GO | 156 | 41 | 4.40 | CENPA;<br>GINS1;<br>H2AFX;<br>H2AFZ;<br>HIST1H1A;<br>HIST1H1B;<br>HIST1HID;<br>HIST1H2AB;<br>HIST1H2AE;<br>HIST1H2AG;<br>HIST1H2AH;<br>HIST1H2AI;<br>HIST1H2AL;<br>HIST1H2BB;<br>HIST1H2BC;<br>HIST1H2BE;<br>HIST1H2BF;<br>HIST1H2BG;<br>HIST1H2BH;<br>HIST1H2BI;<br>HIST1H2BJ;<br>HIST1H2BK;<br>HIST1H2BL;<br>HIST1H2BM;<br>HIST1H2BO;<br>HIST1H3A;<br>HIST1H3B;<br>HIST1H3C;<br>HIST1H3F;<br>HIST1H3G;<br>HIST1H3H;<br>HIST1H3I; | 3 | 0.23 | HILS1; TERT;<br>TNP1 | 0 | 0.00 | | 0 | 0.00 | | 0 | 0.00 | | 37 | 6.73 | CENPA;<br>GINS1;<br>GINS4;<br>H2AFX;<br>H2AFZ;<br>HIST1H1B;<br>HIST1H1D;<br>HIST1H2AB;<br>HIST1H2AE;<br>HIST1H2AG;<br>HIST1H2AH;<br>HIST1H2AI;<br>HIST1H2AL;<br>HIST1H2BB;<br>HIST1H2BC;<br>HIST1H2BD;<br>HIST1H2BE;<br>HIST1H2BF;<br>HIST1H2BG;<br>HIST1H2BI;<br>HIST1H2BJ;<br>HIST1H2BK;<br>HIST1H2BL;<br>HIST1H2BM;<br>HIST1H2BO;<br>HIST1H3A;<br>HIST1H3C;<br>HIST1H3F;<br>HIST1H3G;<br>HIST1H3H;<br>HIST1H3I;<br>HIST1H3J; |
| systemic lupus erythematosus | 121 | 37 | 5.12 | FCGR1A;<br>FCGR3B;<br>H2AFX;<br>H2AFZ;<br>HIST1H2AB;<br>HIST1H2AE;<br>HIST1H2AG; | 6 | 0.59 | ACTN2; C3;<br>C6; C7;<br>ELANE;<br>GRIN2A | 0 | 0.00 | | 0 | 0.00 | | 3 | 0.63 | C3; CTSG;<br>ELANE | 33 | 7.73 | H2AFX;<br>H2AFZ;<br>HIST1H2AB;<br>HIST1H2AE;<br>HIST1H2AG;<br>HIST1H2AH;<br>HIST1H2AI; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | HIST1H2AH;<br>HIST1H2AI;<br>HIST1H2AJ;<br>HIST1H2AL;<br>HIST1H2BB;<br>HIST1H2BC;<br>HIST1H2BE;<br>HIST1H2BF;<br>HIST1H2BG;<br>HIST1H2BH;<br>HIST1H2BI;<br>HIST1H2BJ;<br>HIST1H2BK;<br>HIST1H2BL;<br>HIST1H2BM;<br>HIST1H2BO;<br>HIST1H3A;<br>HIST1H3B;<br>HIST1H3C;<br>HIST1H3F;<br>HIST1H3G;<br>HIST1H3H;<br>HIST1H3I;<br>HIST1H3J;<br>HIST1H4I; | | | | | | | | | | | | | | | HIST1H2AJ;<br>HIST1H2AL;<br>HIST1H2BB;<br>HIST1H2BC;<br>HIST1H2BD;<br>HIST1H2BE;<br>HIST1H2BF;<br>HIST1H2BG;<br>HIST1H2BI;<br>HIST1H2BJ;<br>HIST1H2BK;<br>HIST1H2BL;<br>HIST1H2BM;<br>HIST1H2BO;<br>HIST1H3A;<br>HIST1H3C;<br>HIST1H3F;<br>HIST1H3G;<br>HIST1H3H;<br>HIST1H3I;<br>HIST1H3J;<br>HIST1H4I;<br>HIST2H2AA3;<br>HIST2H2BE;<br>IL10 |
| rna pol i transcription | 80 | 29 | 6.07 | H2AFX;<br>H2AFZ;<br>HIST1H2AB;<br>HIST1H2AE;<br>HIST1H2AJ;<br>HIST1H2BB;<br>HIST1H2BC;<br>HIST1H2BE;<br>HIST1H2BF;<br>HIST1H2BG;<br>HIST1H2BH;<br>HIST1H2BI;<br>HIST1H2BJ;<br>HIST1H2BK;<br>HIST1H2BL;<br>HIST1H2BM; | 0 | 0.00 | | 0 | 0.00 | | 0 | 0.00 | | 0 | 0.00 | | 27 | 9.57 | H2AFX;<br>H2AFZ;<br>HIST1H2AB;<br>HIST1H2AE;<br>HIST1H2AJ;<br>HIST1H2BB;<br>HIST1H2BC;<br>HIST1H2BD;<br>HIST1H2BE;<br>HIST1H2BF;<br>HIST1H2BG;<br>HIST1H2BI;<br>HIST1H2BJ;<br>HIST1H2BK;<br>HIST1H2BL;<br>HIST1H2BM; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | HIST1H2BO; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L | | | | | | | | | | | | | | | HIST1H2BO; HIST1H3A; HIST1H3C; HIST1H3F; HIST1H3G; HIST1H3H; HIST1H3I; HIST1H3J; HIST1H4I; HIST2H2AA3; HIST2H2BE |
| rho gtpases activate formins | 92 | 28 | 5.09 | ACTB; BIRC5; BUB1; BUB1B; CDC20; CDCA8; CENPA; CENPE; CENPF; CENPN; DIAPH3; DYNLL1; KIF18A; KIF2C; KNL1; MAD2L1; NDC80; NUF2; PLK1; SGO2; SKA1; SPC25; TUBA1C; TUBA4A; TUBB2A; TUBB6; ZWILCH; ZWINT | 1 | 0.13 | MAST1 | 0 | 0.00 | | 0 | 0.00 | | 1 | 0.28 | DLC1 | 28 | 8.63 | ACTB; AURKB; BIRC5; BUB1; BUB1B; CDC20; CDCA8; CENPA; CENPE; CENPF; DIAPH3; KIF18A; KIF2C; KNL1; MAD2L1; NDC80; NUF2; PLK1; SGO2; SKA1; SPC24; SPC25; TUBA1C; TUBA4A; TUBB2A; TUBB6; ZWILCH; ZWINT |
| meiosis | 110 | 33 | 5.02 | BRCA2; H2AFX; | 3 | 0.32 | STAG3; SYCP1; | 0 | 0.00 | | 0 | 0.00 | | 2 | 0.46 | SYCP3; SYNE1 | 30 | 7.73 | BLM; BRCA2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | H2AFZ; HIST1H2AB; HIST1H2AE; HIST1H2AJ; HIST1H2BB; HIST1H2BC; HIST1H2BE; HIST1H2BF; HIST1H2BG; HIST1H2BH; HIST1H2BI; HIST1H2BJ; HIST1H2BK; HIST1H2BL; HIST1H2BM; HIST1H2BO; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L; LMNB1; MND1 | | | SYNE1 | | | | | | | | | | | | H2AFX; H2AFZ; HIST1H2AB; HIST1H2AE; HIST1H2AJ; HIST1H2BB; HIST1H2BC; HIST1H2BD; HIST1H2BE; HIST1H2BF; HIST1H2BG; HIST1H2BI; HIST1H2BJ; HIST1H2BK; HIST1H2BL; HIST1H2BM; HIST1H2BO; HIST1H3A; HIST1H3C; HIST1H3F; HIST1H3G; HIST1H3H; HIST1H3I; HIST1H3J; HIST1H4I; HIST2H2AA3; HIST2H2BE; MND1 |
| dna packaging: GO | 168 | 44 | 4.38 | CCNB1; CDCA5; CDK1; CENPA; CENPN; CENPW; H2AFX; HIST1H1A; HIST1H1B; HIST1H1D; HIST1H2BB; | 7 | 0.49 | CHD5; H1FNT; HILS1; NAPIL2; NAPIL6; SYCP1; TSPYL2 | 0 | 0.00 | | 0 | 0.00 | | 4 | 0.60 | CENPV; NAPIL2; SYCP3; TSPYL5 | 36 | 6.08 | CDCA5; CDK1; CENPA; CENPW; H2AFX; HIST1H1B; HIST1H1D; HIST1H2BB; HIST1H2BC; HIST1H2BD; HIST1H2BE; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| Functional | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | HIST1H2BC; HIST1H2BE; HIST1H2BF; HIST1H2BG; HIST1H2BH; HIST1H2BI; HIST1H2BJ; HIST1H2BK; HIST1H2BL; HIST1H2BM; HIST1H2BO; HIST1H3A; HIST1H3B; HIST1H3C; HIST1H3F; HIST1H3G; HIST1H3H; HIST1H3I; HIST1H3J; HIST1H4I; HIST1H4J; | | | | | | | | | | | | | | | HIST1H2BF; HIST1H2BG; HIST1H2BI; HIST1H2BJ; HIST1H2BK; HIST1H2BL; HIST1H2BM; HIST1H2BO; HIST1H3A; HIST1H3C; HIST1H3F; HIST1H3G; HIST1H3H; HIST1H3I; HIST1H3J; HIST1H4I; HIST2H2BE; HMGA2; MCM2; NCAPG; NCAPH; |
| mitotic prometaphase | 161 | 34 | 3.53 | BIRC5; BUB1; BUB1B; CCNB1; CCNB2; CDC20; CDCA5; CDCA8; CDK1; CENPA; CENPE; CENPF; CENPN; DYNLL1; KIF18A; KIF2C; KNL1; MAD2L1; NCAPG; NCAPH; NDC80; | 2 | 0.15 | MAST1; PRKAR2B | 1 | 2.60 | PRKAR2B | 0 | 0.00 | | 1 | 0.16 | DLC1 | 35 | 6.16 | AURKB; BIRC5; BUB1; BUB1B; CCNB1; CCNB2; CDC20; CDCA5; CDCA8; CDK1; CENPA; CENPE; CENPF; KIF18A; KIF2C; KNL1; MAD2L1; NCAPG; NCAPH; NDC80; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | NEK2; NUF2; PLK1; SGO2; SKA1; SMC4; SPC25; TUBA1C; TUBA4A; TUBB2A; TUBB6; ZWILCH; ZWINT | | | | | | | | | | | | | | | NEK2; NUF2; PLK1; PLK4; SGO2; SKA1; SMC4; SPC24; SPC25; TUBA1C; TUBA4A; TUBB2A; TUBB6; ZWILCH; ZWINT |
| sister chromatid segregation: GO | 162 | 32 | 3.31 | BIRC5; BUB1; BUB1B; CCNB1; CDC20; CDCA5; CDCA8; CENPA; CENPE; CENPF; CENPN; CEP55; DLGAP5; KIF14; KIF18A; KIF23; KIF2C; KIF4A; MAD2L1; NCAPG; NCAPH; NDC80; NEK2; NUF2; PLK1; RACGAP1; SKA1; SMC4; SPC25; | 0 | 0.00 | | 0 | 0.00 | | 0 | 0.00 | | 0 | 0.00 | | 35 | 6.13 | BIRC5; BUB1; BUB1B; CCNB1; CDC20; CDCA5; CDCA8; CENPA; CENPE; CENPF; CEP55; DLGAP5; KIF14; KIF18A; KIF18B; KIF23; KIF2C; KIF4A; KIFC1; MAD2L1; NCAPG; NCAPH; NDC80; NEK2; NUF2; PLK1; SKA1; SMC4; SPAG5; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | TOP2A; ZWILCH; ZWINT | | | | | | | | | | | | | | | SPC24; SPC25; TOP2A; ZWILCH; ZWINT |
| packaging of telomere ends | 46 | 21 | 7.64 | H2AFX; H2AFZ; HIST1H2AB; HIST1H2AE; HIST1H2AJ; HIST1H2BB; HIST1H2BC; HIST1H2BE; HIST1H2BF; HIST1H2BG; HIST1H2BH; HIST1H2BI; HIST1H2BJ; HIST1H2BK; HIST1H2BL; HIST1H2BM; HIST1H2BO; HIST1H4I; HIST1H4J; HIST1H4K; HIST1H4L | 0 | 0.00 | | 0 | 0.00 | | 0 | 0.00 | | 0 | 0.00 | | 20 | 12.33 | H2AFX; H2AFZ; HIST1H2AB; HIST1H2AE; HIST1H2AJ; HIST1H2BB; HIST1H2BC; HIST1H2BD; HIST1H2BE; HIST1H2BF; HIST1H2BG; HIST1H2BI; HIST1H2BJ; HIST1H2BK; HIST1H2BL; HIST1H2BM; HIST1H2BO; HIST1H4I; HIST2H2AA3; HIST2H2BE |
| amplification of signal from unattached kinetochores via a mad2 inhibitory signal | 64 | 22 | 5.75 | BIRC5; BUB1; BUB1B; CDC20; CDCA8; CENPA; CENPE; CENPF; CENPN; DYNLL1; KIF18A; KIF2C; KNL1; MAD2L1; NDC80; NUF2; PLK1; | 1 | 0.18 | MAST1 | 0 | 0.00 | | 0 | 0.00 | | 1 | 0.40 | DLC1 | 22 | 9.75 | AURKB; BIRC5; BUB1; BUB1B; CDC20; CDCA8; CENPA; CENPE; CENPF; KIF18A; KIF2C; KNL1; MAD2L1; NDC80; NUF2; PLK1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | SGO2; SKA1; SPC25; ZWILCH; ZWINT | | | | | | | | | | | | | | | SGO2; SKA1; SPC24; SPC25; ZWILCH; ZWINT |
| amplification of signal from the kinetochores | 64 | 22 | 5.75 | BIRC5; BUB1; BUB1B; CDC20; CDCA8; CENPA; CENPE; CENPF; CENPN; DYNLL1; KIF18A; KIF2C; KNL1; MAD2L1; NDC80; NUF2; PLK1; SGO2; SKA1; SPC25; ZWILCH; ZWINT | 1 | 0.18 | MAST1 | 0 | 0.00 | | 0 | 0.00 | | 1 | 0.40 | DLC1 | 22 | 9.75 | AURKB; BIRC5; BUB1; BUB1B; CDC20; CDCA8; CENPA; CENPE; CENPF; KIF18A; KIF2C; KNL1; MAD2L1; NDC80; NUF2; PLK1; SGO2; SKA1; SPC24; SPC25; ZWILCH; ZWINT |
| mitotic spindle checkpoint | 73 | 23 | 5.27 | BIRC5; BUB1; BUB1B; CDC20; CDCA8; CENPA; CENPE; CENPF; CENPN; DYNLL1; KIF18A; KIF2C; KNL1; MAD2L1; NDC80; NUF2; PLK1; SGO2; SKA1; SPC25; | 1 | 0.16 | MAST1 | 0 | 0.00 | | 0 | 0.00 | | 1 | 0.35 | DLC1 | 23 | 8.93 | AURKB; BIRC5; BUB1; BUB1B; CDC20; CDCA8; CENPA; CENPE; CENPF; KIF18A; KIF2C; KNL1; MAD2L1; NDC80; NUF2; PLK1; SGO2; SKA1; SPC24; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | UBE2C; ZWILCH; ZWINT | | | | | | | | | | | | | | | SPC25; UBE2C; ZWILCH; ZWINT |
| cell cycle | 156 | 33 | 3.54 | GINS3; H2AFZ; HIST1H2AB; HIST1H2AE; HIST1H2AJ; HIST1H2BB; HIST1H2BC; HIST1H2BE; HIST1H2BF; HIST1H2BG; HIST1H2BH; HIST1H2BI; HIST1H2BJ; HIST1H2BK; HIST1H2BL; HIST1H2BM; HIST1H2BO; HIST1H3A; HIST1H3I; HIST1H4I; HIST1H4J; HIST1H4K; HIST1H4L; KNL1; LMNB1; SGO2; TK1; TUBA1C; TUBB2A; TUBB6; UBE2N; YWHAQ; YWHAZ | 3 | 0.23 | MAST1; SYNE1; TERT | 0 | 0.00 | | 0 | 0.00 | | 3 | 0.49 | DLC1; SLC29A1; SYNE1 | 32 | 5.82 | FEN1; GINS3; GINS4; H2AFZ; HIST1H2AB; HIST1H2AE; HIST1H2AJ; HIST1H2BB; HIST1H2BC; HIST1H2BD; HIST1H2BE; HIST1H2BF; HIST1H2BG; HIST1H2BI; HIST1H2BJ; HIST1H2BK; HIST1H2BL; HIST1H2BM; HIST1H2BO; HIST1H3A; HIST1H3I; HIST1H4I; HIST2H2AA3; HIST2H2BE; KNL1; SGO2; TK1; TUBA1C; TUBB2A; TUBB6; YWHAQ; YWHAZ |
| separation of sister chromatids | 127 | 31 | 4.08 | BIRC5; BUB1; BUB1B; CDC20; CDCA5; | 1 | 0.09 | MAST1 | 0 | 0.00 | | 0 | 0.00 | | 1 | 0.20 | DLC1 | 29 | 6.48 | AURKB; BIRC5; BUB1; BUB1B; CDC20; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | CDCA8; CENPA; CENPE; CENPF; CENPN; DYNLL1; KIF18A; KIF2C; KNL1; MAD2L1; NDC80; NUF2; PLK1; PSMA5; PSMB6; PTTG1; SGO2; SKA1; SPC25; TUBA1C; TUBA4A; TUBB2A; TUBB6; UBE2C; ZWILCH; ZWINT | | | | | | | | | | | | | | | CDCA5; CDCA8; CENPA; CENPE; CENPF; KIF18A; KIF2C; KNL1; MAD2L1; NDC80; NUF2; PLK1; PTTG1; SGO2; SKA1; SPC24; SPC25; TUBA1C; TUBA4A; TUBB2A; TUBB6; UBE2C; ZWILCH; ZWINT |
| rna pol i rna pol iii and mitochondrial transcription | 112 | 29 | 4.33 | H2AFX; H2AFZ; HIST1H2AB; HIST1H2AE; HIST1H2AJ; HIST1H2BB; HIST1H2BC; HIST1H2BE; HIST1H2BF; HIST1H2BG; HIST1H2BH; HIST1H2BI; HIST1H2BJ; HIST1H2BK; HIST1H2BL; HIST1H2BM; HIST1H2BO; HIST1H3A; | 0 | 0.00 | | 0 | 0.00 | | 0 | 0.00 | | 0 | 0.00 | | 27 | 6.84 | H2AFX; H2AFZ; HIST1H2AB; HIST1H2AE; HIST1H2AJ; HIST1H2BB; HIST1H2BC; HIST1H2BD; HIST1H2BE; HIST1H2BF; HIST1H2BG; HIST1H2BI; HIST1H2BJ; HIST1H2BK; HIST1H2BL; HIST1H2BM; HIST1H2BO; HIST1H3A; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | HIST1H3B; HIST1H3C; HIST1H3F; HIST1H3G; HIST1H3H; HIST1H3I; HIST1H3J; HIST1H4I; HIST1H4J; HIST1H4K; HIST1H4L | | | | | | | | | | | | | | | HIST1H3C; HIST1H3F; HIST1H3G; HIST1H3H; HIST1H3I; HIST1H3J; HIST1H4I; HIST2H2AA3; HIST2H2BE |
| mitotic anaphase | 136 | 32 | 3.94 | BIRC5; BUB1; BUB1B; CDC20; CDCA5; CDCA8; CENPA; CENPE; CENPF; CENPN; DYNLL1; KIF18A; KIF2C; KNL1; LMNB1; MAD2L1; NDC80; NUF2; PLK1; PSMA5; PSMB6; PTTG1; SGO2; SKA1; SPC25; TUBA1C; TUBA4A; TUBB2A; TUBB6; UBE2C; ZWILCH; ZWINT | 1 | 0.09 | MAST1 | 0 | 0.00 | | 0 | 0.00 | | 1 | 0.19 | DLC1 | 29 | 6.05 | AURKB; BIRC5; BUB1; BUB1B; CDC20; CDCA5; CDCA8; CENPA; CENPE; CENPF; KIF18A; KIF2C; KNL1; MAD2L1; NDC80; NUF2; PLK1; PTTG1; SGO2; SKA1; SPC24; SPC25; TUBA1C; TUBA4A; TUBB2A; TUBB6; UBE2C; ZWILCH; ZWINT |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| mitotic metaphase and anaphase | 137 | 33 | 4.03 | BIRC5; BUB1; BUB1B; CDC20; CDCA5; CDCA8; CENPA; CENPE; CENPF; CENPN; DYNLL1; FBXO5; KIF18A; KIF2C; KNL1; LMNB1; MAD2L1; NDC80; NUF2; PLK1; PSMA5; PSMB6; PTTG1; SGO2; SKA1; SPC25; TUBA1C; TUBA4A; TUBB2A; TUBB6; UBE2C; ZWILCH; ZWINT | 1 | 0.09 | MAST1 | 0 | 0.00 | | 0 | 0.00 | | 1 | 0.19 | DLC1 | 29 | 6.00 | AURKB; BIRC5; BUB1; BUB1B; CDC20; CDCA5; CDCA8; CENPA; CENPE; CENPF; KIF18A; KIF2C; KNL1; MAD2L1; NDC80; NUF2; PLK1; PTTG1; SGO2; SKA1; SPC24; SPC25; TUBA1C; TUBA4A; TUBB2A; TUBB6; UBE2C; ZWILCH; ZWINT |
| condensed chromosome: GO | 175 | 33 | 3.16 | AURKA; BIRC5; BLM; BUB1; BUB1B; CCNB1; CDCA5; CENPA; CENPE; CENPF; CENPN; CENPW; | 4 | 0.27 | DYNC1I1; RSPH1; STAG3; SYCP1 | 0 | 0.00 | | 0 | 0.00 | | 3 | 0.44 | ADD3; CENPV; SYCP3 | 32 | 5.19 | AURKA; AURKB; BIRC5; BLM; BUB1; BUB1B; CCNB1; CDCA5; CENPA; CENPE; CENPF; CENPW; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | CHEK1; CSNK1A1; H2AFX; HJURP; KIF2C; MAD2L1; MKI67; NCAPG; NCAPH; NDC80; NEK2; NUF2; PLK1; RCC1; SKA1; SKA3; SMC4; SPC25; TOP2A; ZWILCH; ZWINT | | | | | | | | | | | | | | | CHEK1; H2AFX; KIF2C; MAD2L1; MKI67; NCAPG; NCAPH; NDC80; NEK2; NUF2; PLK1; SKA1; SKA3; SMC4; SPAG5; SPC24; SPC25; TOP2A; ZWILCH; ZWINT |
| mitotic sister chromatid segregation: GO | 86 | 20 | 3.89 | CCNB1; CDCA5; CDCA8; CENPE; CEP55; DLGAP5; KIF14; KIF18A; KIF23; KIF2C; KIF4A; MAD2L1; NCAPG; NCAPH; NDC80; NEK2; PLK1; RACGAP1; SMC4; ZWINT | 0 | 0.00 | | 0 | 0.00 | | 0 | 0.00 | | 0 | 0.00 | | 23 | 7.58 | AURKB; CCNB1; CDCA5; CDCA8; CENPE; CEP55; DLGAP5; KIF14; KIF18A; KIF18B; KIF23; KIF2C; KIF4A; KIFC1; MAD2L1; NCAPG; NCAPH; NDC80; NEK2; PLK1; SMC4; SPAG5; ZWINT |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| condensed chromosome centromeric region: GO | 87 | 23 | 4.42 | AURKA; BIRC5; BUB1; BUB1B; CCNB1; CENPA; CENPE; CENPF; CENPN; CENPW; CSNK1A1; HJURP; KIF2C; MAD2L1; NDC80; NEK2; NUF2; PLK1; SKA1; SKA3; SPC25; ZWILCH; ZWINT | 1 | 0.14 | DYNC1I1 | 0 | 0.00 | | 0 | 0.00 | | 1 | 0.29 | CENPV | 23 | 7.50 | AURKA; AURKB; BIRC5; BUB1; BUB1B; CCNB1; CENPA; CENPE; CENPF; CENPW; KIF2C; MAD2L1; NDC80; NEK2; NUF2; PLK1; SKA1; SKA3; SPAG5; SPC24; SPC25; ZWILCH; ZWINT |
| condensation of prophase chromosomes | 39 | 18 | 7.72 | CCNB1; CDK1; H2AFX; H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; HIST1H4L; PLK1; SMC4 | 0 | 0.00 | | 0 | 0.00 | | 0 | 0.00 | | 0 | 0.00 | | 16 | 11.63 | CCNB1; CDK1; H2AFX; H2AFZ; HIST1H2AE; HIST1H2BB; HIST1H2BD; HIST1H2BF; HIST1H2BK; HIST1H2BM; HIST1H3A; HIST1H3I; HIST1H4I; HIST2H2BE; PLK1; SMC4 |
| telomere maintenance | 76 | 23 | 5.06 | H2AFX; H2AFZ; HIST1H2AB; | 1 | 0.16 | TERT | 0 | 0.00 | | 0 | 0.00 | | 0 | 0.00 | | 21 | 7.84 | FEN1; H2AFX; H2AFZ; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | HIST1H2AE;<br>HIST1H2AJ;<br>HIST1H2BB;<br>HIST1H2BC;<br>HIST1H2BE;<br>HIST1H2BF;<br>HIST1H2BG;<br>HIST1H2BH;<br>HIST1H2BI;<br>HIST1H2BJ;<br>HIST1H2BK;<br>HIST1H2BL;<br>HIST1H2BM;<br>HIST1H2BO;<br>HIST1H4I;<br>HIST1H4J;<br>HIST1H4K;<br>HIST1H4L;<br>PCNA;<br>RUVBL1 | | | | | | | | | | | | | | | HIST1H2AB;<br>HIST1H2AE;<br>HIST1H2AJ;<br>HIST1H2BB;<br>HIST1H2BC;<br>HIST1H2BD;<br>HIST1H2BE;<br>HIST1H2BF;<br>HIST1H2BG;<br>HIST1H2BI;<br>HIST1H2BJ;<br>HIST1H2BK;<br>HIST1H2BL;<br>HIST1H2BM;<br>HIST1H2BO;<br>HIST1H4I;<br>HIST2H2AA3;<br>HIST2H2BE |
| chromatin assembly or disassembly: GO | 156 | 37 | 3.97 | CENPA;<br>CENPN;<br>CENPW;<br>H2AFX;<br>HIST1HIA;<br>HIST1H1B;<br>HIST1HID;<br>HIST1H2BB;<br>HIST1H2BC;<br>HIST1H2BE;<br>HIST1H2BF;<br>HIST1H2BG;<br>HIST1H2BH;<br>HIST1H2BI;<br>HIST1H2BJ;<br>HIST1H2BK;<br>HIST1H2BL;<br>HIST1H2BM;<br>HIST1H2BO;<br>HIST1H3A;<br>HIST1H3B; | 5 | 0.38 | HILS1;<br>NAP1L2;<br>NAP1L6;<br>TNP1;<br>TSPYL2 | 0 | 0.00 | | 0 | 0.00 | | 3 | 0.49 | CENPV;<br>NAPIL2;<br>TSPYL5 | 29 | 5.27 | CENPA;<br>CENPW;<br>H2AFX;<br>HIST1HIB;<br>HIST1HID;<br>HIST1H2BB;<br>HIST1H2BC;<br>HIST1H2BD;<br>HIST1H2BE;<br>HIST1H2BF;<br>HIST1H2BG;<br>HIST1H2BI;<br>HIST1H2BJ;<br>HIST1H2BK;<br>HIST1H2BL;<br>HIST1H2BM;<br>HIST1H2BO;<br>HIST1H3A;<br>HIST1H3C;<br>HIST1H3F;<br>HIST1H3G; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | HIST1H3C; HIST1H3F; HIST1H3G; HIST1H3H; HIST1H3I; HIST1H3J; HIST1H4I; HIST1H4J; HIST1H4K; HIST1H4L; HJURP; | | | | | | | | | | | | | | | HIST1H3H; HIST1H3I; HIST1H3J; HIST1H4I; HIST2H2BE; HMGA2; MCM2; NPM1 |
| cell cycle checkpoint: GO | 180 | 29 | 2.70 | AURKA; BIRC5; BLM; BUB1; BUB1B; CCNA2; CCNB1; CDC45; CDC6; CDK1; CDKN1A; CENPF; CHEK1; CLSPN; DTL; E2F7; H2AFX; HMGA2; MAD2L1; NPM1; PCNA; PLK1; PLK2; SFN; TOP2A; TP63; TTK; ZWILCH; ZWINT | 2 | 0.13 | PLK5; USP17L2 | 0 | 0.00 | | 0 | 0.00 | | 0 | 0.00 | | 31 | 4.88 | AURKA; AURKB; BIRC5; BLM; BRIP1; BUB1; BUB1B; CCNA2; CCNB1; CDC45; CDC6; CDK1; CDKN1A; CENPF; CHEK1; DTL; E2F1; E2F7; FANCI; GTSE1; H2AFX; HMGA2; MAD2L1; NPM1; PLK1; PLK2; SFN; TOP2A; TTK; ZWILCH; ZWINT |
| meiotic synapsis | 72 | 22 | 5.11 | H2AFX; H2AFZ; HIST1H2AB; HIST1H2AE; HIST1H2AJ; HIST1H2BB; | 3 | 0.49 | STAG3; SYCP1; SYNE1 | 0 | 0.00 | | 0 | 0.00 | | 2 | 0.71 | SYCP3; SYNE1 | 20 | 7.88 | H2AFX; H2AFZ; HIST1H2AB; HIST1H2AE; HIST1H2AJ; HIST1H2BB; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline: Up-regu-lated | A: Fold Change (FC) Up | A: Up-regulated Genes | A: Down-regu-lated | A: Fold Change (FC) | A: Down-regulated Genes | B. Differentially expressed genes significant in the baseline vs week 12 comparison only in the placebo: Up-regu-lated | B: Fold Change (FC) Up | B: Up-regulated Genes | B: Down-regu-lated | B: Fold Change (FC) | B: Down-regulated Genes | C. Differentially expressed genes significant in the baseline vs week 12 comparison only in the nemo: Up-regu-lated | C: Fold Change (FC) Up | C: Up-regulated Genes | C: Down-regu-lated | C: Fold Change (FC) | C: Down-regulated Genes |
|---|---|---|---|---|---|---|---|---|---|---|---|---|---|---|---|---|---|---|---|
| | | | | HIST1H2BC; HIST1H2BE; HIST1H2BF; HIST1H2BG; HIST1H2BH; HIST1H2BI; HIST1H2BJ; HIST1H2BK; HIST1H2BL; HIST1H2BM; HIST1H2BO; HIST1H4I; HIST1H4J; HIST1H4K; HIST1H4L; LMNB1 | | | | | | | | | | | | | | | HIST1H2BC; HIST1H2BD; HIST1H2BE; HIST1H2BF; HIST1H2BG; HIST1H2BI; HIST1H2BJ; HIST1H2BK; HIST1H2BL; HIST1H2BM; HIST1H2BO; HIST1H4I; HIST2H2AA3; HIST2H2BE |
| chromosome maintenance | 122 | 31 | 4.25 | CENPA; CENPN; CENPW; H2AFX; H2AFZ; HIST1H2AB; HIST1H2AE; HIST1H2AJ; HIST1H2BB; HIST1H2BC; HIST1H2BE; HIST1H2BF; HIST1H2BG; HIST1H2BH; HIST1H2BI; HIST1H2BJ; HIST1H2BK; HIST1H2BL; HIST1H2BM; HIST1H2BO; HIST1H4I; HIST1H4J; HIST1H4K; HIST1H4L; HJURP; | 4 | 0.39 | STAG3; SYCP1; SYNE1; TERT | 0 | 0.00 | | 0 | 0.00 | | 2 | 0.42 | SYCP3; SYNE1 | 25 | 5.81 | CENPA; CENPW; FEN1; H2AFX; H2AFZ; HIST1H2AB; HIST1H2AE; HIST1H2AJ; HIST1H2BB; HIST1H2BC; HIST1H2BD; HIST1H2BE; HIST1H2BF; HIST1H2BG; HIST1H2BI; HIST1H2BJ; HIST1H2BK; HIST1H2BL; HIST1H2BM; HIST1H2BO; HIST1H4I; HIST2H2AA3; HIST2H2BE; KNL1; NPM1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | KNL1; LMNB1; NPM1; OIP5; PCNA; RUVBL1 | | | | | | | | | | | | | | | |
| kinetochore: GO | 107 | 24 | 3.75 | BIRC5; BUB1; BUB1B; CCNB1; CENPA; CENPE; CENPF; CENPN; CENPW; CSNK1A1; DYNLL1; HJURP; KIF18A; KIF2C; MAD2L1; NDC80; NEK2; NUF2; PLK1; SKA1; SKA3; SPC25; ZWILCH; ZWINT | 1 | 0.11 | DYNC1I1 | 0 | 0.00 | | 0 | 0.00 | | 1 | 0.24 | CENPV | 23 | 6.10 | AURKB; BIRC5; BUB1; BUB1B; CCNB1; CENPA; CENPE; CENPF; CENPW; KIF18A; KIF2C; MAD2L1; NDC80; NEK2; NUF2; PLK1; SKA1; SKA3; SPAG5; SPC24; SPC25; ZWILCH; ZWINT |
| g2/m checkpoints | 119 | 29 | 4.08 | BLM; CCNB1; CCNB2; CDC25A; CDC25B; CDC45; CDC6; CDK1; CHEK1; CLSPN; DBF4; EXO1; H2AFX; HIST1H2BB; HIST1H2BF; HIST1H2BH; HIST1H2BK; | 0 | 0.00 | | 0 | 0.00 | | 0 | 0.00 | | 0 | 0.00 | | 24 | 5.72 | BLM; BRIP1; CCNB1; CCNB2; CDC25A; CDC25B; CDC45; CDC6; CDK1; CHEK1; EXO1; GTSE1; H2AFX; HIST1H2BB; HIST1H2BD; HIST1H2BF; HIST1H2BK; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | HIST1H2BM; HIST1H4I; HIST1H4J; HIST1H4K; HIST1H4L; MCM10; ORC1; ORC6; PSMA5; PSMB6; SFN; UBE2N | | | | | | | | | | | | | | | HIST1H2BM; HIST1H4I; HIST2H2BE; MCM2; ORC1; ORC6; SFN |
| chromosome centromeric region: GO | 158 | 30 | 3.18 | AURKA; BIRC5; BUB1; BUB1B; CCNB1; CDCA5; CDCA8; CENPA; CENPE; CENPF; CENPN; CENPW; CSNK1A1; DYNLL1; ESCO2; HJURP; KIF18A; KIF2C; MAD2L1; MKI67; NDC80; NEK2; NUF2; OIP5; PLK1; SKA1; SKA3; SPC25; ZWILCH; ZWINT | 4 | 0.30 | DYNCII1; PKHD1; STAG3; SYCP1 | 0 | 0.00 | | 0 | 0.00 | | 2 | 0.32 | CENPV; SYCP3 | 27 | 4.85 | AURKA; AURKB; BIRC5; BUB1; BUB1B; CCNB1; CDCA5; CDCA8; CENPA; CENPE; CENPF; CENPW; KIF18A; KIF2C; MAD2L1; MKI67; NDC80; NEK2; NUF2; PLK1; SKA1; SKA3; SPAG5; SPC24; SPC25; ZWILCH; ZWINT |
| aurora b pathway | 38 | 14 | 6.16 | AURKA; BIRC5; BUB1; CDCA8; | 1 | 0.31 | DES | 0 | 0.00 | | 0 | 0.00 | | 0 | 0.00 | | 14 | 10.45 | AURKA; AURKB; BIRC5; BUB1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | CENPA; KIF20A; KIF23; KIF2C; NCAPG; NCAPH; NDC80; NPM1; RACGAP1; SMC4 | | | | | | | | | | | | | | | CDCA8; CENPA; KIF20A; KIF23; KIF2C; NCAPG; NCAPH; NDC80; NPM1; SMC4 |
| foxm1 pathway | 39 | 14 | 6.01 | BIRC5; BRCA2; CCNA2; CCNB1; CCNB2; CCNE1; CDC25B; CDK1; CENPA; CENPF; FOXM1; NEK2; PLK1; TGFA | 0 | 0.00 | | 0 | 0.00 | | 0 | 0.00 | | 1 | 0.65 | ESR1 | 14 | 10.18 | AURKB; BIRC5; BRCA2; CCNA2; CCNB1; CCNB2; CDC25B; CDK1; CENPA; CENPF; FOXM1; NEK2; PLK1; TGFA |
| sister chromatid cohesion: GO | 99 | 20 | 3.38 | BIRC5; BUB1; BUB1B; CDC20; CDCA5; CDCA8; CENPA; CENPE; CENPF; CENPN; KIF18A; KIF2C; MAD2L1; NDC80; NUF2; PLK1; SKA1; SPC25; ZWILCH; ZWINT | 0 | 0.00 | | 0 | 0.00 | | 0 | 0.00 | | 0 | 0.00 | | 21 | 6.02 | AURKB; BIRC5; BUB1; BUB1B; CDC20; CDCA5; CDCA8; CENPA; CENPE; CENPF; KIF18A; KIF2C; MAD2L1; NDC80; NUF2; PLK1; SKA1; SPC24; SPC25; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | | | | | | | | | | | | | | | | ZWILCH; ZWINT |
| rna polymerase i promoter opening | 29 | 14 | 8.08 | H2AFX; H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; HIST1H4L | 0 | 0.00 | | 0 | 0.00 | | 0 | 0.00 | | 0 | 0.00 | | 12 | 11.73 | H2AFX; H2AFZ; HIST1H2AE; HIST1H2BB; HIST1H2BD; HIST1H2BF; HIST1H2BK; HIST1H2BM; HIST1H3A; HIST1H3I; HIST1H4I; HIST2H2BE |
| mitotic m m g1 phases | 162 | 31 | 3.20 | BIRC5; BUB1; BUB1B; CDC20; CDC45; CDC6; CDCA8; CENPA; CENPN; DBF4; E2F3; FBXO5; KIF18A; KIF20A; KIF23; KIF2C; MAD2L1; MCM10; NDC80; NUF2; ORC1; ORC6; PLK1; PSMA4; PSMA5; PSMB6; PSMD1; SKA1; SPC25; | 0 | 0.00 | | 0 | 0.00 | | 0 | 0.00 | | 0 | 0.00 | | 26 | 4.55 | AURKB; BIRC5; BUB1; BUB1B; CDC20; CDC45; CDC6; CDCA8; CENPA; E2F1; KIF18A; KIF20A; KIF23; KIF2C; MAD2L1; MCM2; NDC80; NUF2; ORC1; ORC6; PLK1; SKA1; SPC24; SPC25; ZWILCH; ZWINT |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | ZWILCH; ZWINT | | | | | | | | | | | | | | | |
| plk1 pathway | 43 | 15 | 5.84 | AURKA; BUB1; BUB1B; CCNB1; CDC20; CDC25B; CDK1; CENPE; CLSPN; ECT2; FBXO5; KIF20A; NDC80; PLK1; TPX2 | 1 | 0.27 | SSPO | 0 | 0.00 | | 0 | 0.00 | | 0 | 0.00 | | 14 | 9.23 | AURKA; BUB1; BUBIB; CCNB1; CDC20; CDC25B; CDK1; CENPE; ECT2; KIF20A; NDC80; PLK1; SPC24; TPX2 |
| kinesins | 43 | 14 | 5.45 | CENPE; KIF11; KIF15; KIF18A; KIF20A; KIF20B; KIF23; KIF2C; KIF4A; RACGAP1; TUBA1C; TUBA4A; TUBB2A; TUBB6 | 1 | 0.27 | KIFC2 | 0 | 0.00 | | 0 | 0.00 | | 0 | 0.00 | | 14 | 9.23 | CENPE; KIF11; KIF15; KIF18A; KIF18B; KIF20A; KIF23; KIF2C; KIF4A; KIFC1; TUBA1C; TUBA4A; TUBB2A; TUBB6 |
| dna damage/ telomere stress induced senescence | 51 | 19 | 6.23 | CCNA2; CCNE1; CDKN1A; H2AFX; H2AFZ; HIST1H1B; HIST1H1D; HIST1H2AE; HIST1H2BB; HIST1H2BF; HIST1H2BH; HIST1H2BK; | 0 | 0.00 | | 0 | 0.00 | | 0 | 0.00 | | 0 | 0.00 | | 15 | 8.34 | CCNA2; CDKN1A; H2AFX; H2AFZ; HIST1H1B; HIST1HID; HIST1H2AE; HIST1H2BB; HIST1H2BD; HIST1H2BF; HIST1H2BK; HIST1H2BM; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | HIST1H2BM; HIST1H4I; HIST1H4J; HIST1H4K; HIST1H4L; HMGA2; LMNB1 | | | | | | | | | | | | | | | HIST1H4I; HIST2H2BE; HMGA2 |
| regulation of chromosome segregation: GO | 78 | 19 | 4.08 | BUB1; BUB1B; CCNB1; CDC6; CDCA5; CENPE; CENPF; DLGAP5; ECT2; FBXO5; GEN1; KIF2C; MAD2L1; NEK2; PLK1; PTTG1; RACGAP1; TTK; UBE2C | 0 | 0.00 | | 0 | 0.00 | | 0 | 0.00 | | 0 | 0.00 | | 18 | 6.54 | AURKB; BUB1; BUB1B; CCNB1; CDC6; CDCA5; CENPE; CENPF; DLGAP5; ECT2; KIF2C; MAD2L1; NEK2; PLK1; PTTG1; SPAG5; TTK; UBE2C |
| mitotic cell cycle checkpoint: GO | 131 | 23 | 2.94 | AURKA; BLM; BUB1; BUB1B; CCNA2; CCNB1; CDK1; CDKN1A; CENPF; CLSPN; E2F7; HMGA2; MAD2L1; NPM1; PCNA; PLK1; PLK2; SFN; TOP2A; TP63; TTK; ZWILCH; ZWINT | 1 | 0.09 | USP17L2 | 0 | 0.00 | | 0 | 0.00 | | 0 | 0.00 | | 23 | 4.98 | AURKA; BLM; BUB1; BUB1B; CCNA2; CCNB1; CDK1; CDKN1A; CENPF; E2F1; E2F7; FANCI; GTSE1; HMGA2; MAD2L1; NPM1; PLK1; PLK2; SFN; TOP2A; TTK; ZWILCH; ZWINT |
| chromatin silencing: GO | 79 | 20 | 4.24 | H2AFX; H2AFZ; HIST1H2AB; | 3 | 0.45 | HDAC5; HILS1; TNP1 | 0 | 0.00 | | 0 | 0.00 | | 0 | 0.00 | | 18 | 6.46 | BEND3; H2AFX; H2AFZ; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | HIST1H2AE; HIST1H2AG; HIST1H2AH; HIST1H2AI; HIST1H2AL; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L | | | | | | | | | | | | | | | HIST1H2AB; HIST1H2AE; HIST1H2AG; HIST1H2AH; HIST1H2AI; HIST1H2AL; HIST1H3A; HIST1H3C; HIST1H3F; HIST1H3G; HIST1H3H; HIST1H3I; HIST1H3J; HIST1H4I; HIST2H2AA3 |
| activated pkn1 stimulates transcription of ar (androgen receptor) regulated genes klk2 and klk3 | 31 | 14 | 7.56 | H2AFX; H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; HIST1H4L | 1 | 0.38 | AR | 0 | 0.00 | | 0 | 0.00 | | 0 | 0.00 | | 12 | 10.98 | H2AFX; H2AFZ; HIST1H2AE; HIST1H2BB; HIST1H2BD; HIST1H2BF; HIST1H2BK; HIST1H2BM; HIST1H3A; HIST1H3I; HIST1H4I; HIST2H2BE |
| deposition of new cenpa-containing nucleosomes at the centromere | 46 | 20 | 7.28 | CENPA; CENPN; CENPW; H2AFX; H2AFZ; HIST1H2AE; HIST1H2BB; HIST1H2BF; HIST1H2BH; HIST1H2BK; | 0 | 0.00 | | 0 | 0.00 | | 0 | 0.00 | | 0 | 0.00 | | 14 | 8.63 | CENPA; CENPW; H2AFX; H2AFZ; HIST1H2AE; HIST1H2BB; HIST1H2BD; HIST1H2BF; HIST1H2BK; HIST1H2BM; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | A: Fold Change (FC) Up | A: Up-regulated Genes | A: Down-regulated | A: Fold Change (FC) | A: Down-regulated Genes | B. Differentially expressed genes significant in the baseline vs week 12 comparison only in the placebo: Up-regulated | B: Fold Change (FC) Up | B: Up-regulated Genes | B: Down-regulated | B: Fold Change (FC) | B: Down-regulated Genes | C. Differentially expressed genes significant in the baseline vs week 12 comparison only in the nemo: Up-regulated | C: Fold Change (FC) Up | C: Up-regulated Genes | C: Down-regulated | C: Fold Change (FC) | C: Down-regulated Genes |
|---|---|---|---|---|---|---|---|---|---|---|---|---|---|---|---|---|---|---|---|
| | | | | HIST1H2BM; HIST1H4I; HIST1H4J; HIST1H4K; HIST1H4L; HJURP; KNL1; NPM1; OIP5; RUVBL1 | | | | | | | | | | | | | | | HIST1H4I; HIST2H2BE; KNL1; NPM1 |
| nucleosome assembly | 46 | 20 | 7.28 | CENPA; CENPN; CENPW; H2AFX; H2AFZ; HIST1H2AE; HIST1H2BB; HIST1H2BF; HIST1H2BH; HIST1H2BK; HIST1H2BM; HIST1H4I; HIST1H4J; HIST1H4K; HIST1H4L; HJURP; KNL1; NPM1; OIP5; RUVBL1 | 0 | 0.00 | | 0 | 0.00 | | 0 | 0.00 | | 0 | 0.00 | | 14 | 8.63 | CENPA; CENPW; H2AFX; H2AFZ; HIST1H2AE; HIST1H2BB; HIST1H2BD; HIST1H2BF; HIST1H2BK; HIST1H2BM; HIST1H4I; HIST2H2BE; KNL1; NPM1 |
| dna methylation | 32 | 15 | 7.84 | H2AFX; H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; | 0 | 0.00 | | 0 | 0.00 | | 0 | 0.00 | | 0 | 0.00 | | 12 | 10.63 | H2AFX; H2AFZ; HIST1H2AE; HIST1H2BB; HIST1H2BD; HIST1H2BF; HIST1H2BK; HIST1H2BM; HIST1H3A; HIST1H3I; HIST1H4I; HIST2H2BE |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | HIST1H4L; UHRF1 | | | | | | | | | | | | | | | |
| mitotic spindle organization: GO | 64 | 17 | 4.44 | AURKA; BIRC5; CCNB1; KIF11; KIF23; KIF4A; MYBL2; NDC80; NEK2; PLK2; RACGAP1; RAN; RCC1; SPC25; STIL; TPX2; TTK | 1 | 0.18 | BIRC7 | 0 | 0.00 | | 0 | 0.00 | | 0 | 0.00 | | 16 | 7.09 | AURKA; AURKB; BIRC5; CCNB1; KIF11; KIF23; KIF4A; KIFC1; NDC80; NEK2; PLK2; RAN; SPC25; STIL; TPX2; TTK |
| sirt1 negatively regulates rrna expression | 33 | 14 | 7.10 | H2AFX; H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; HIST1H4L | 0 | 0.00 | | 0 | 0.00 | | 0 | 0.00 | | 0 | 0.00 | | 12 | 10.31 | H2AFX; H2AFZ; HIST1H2AE; HIST1H2BB; HIST1H2BD; HIST1H2BF; HIST1H2BK; HIST1H2BM; HIST1H3A; HIST1H3I; HIST1H4I; HIST2H2BE |
| transcription | 189 | 31 | 2.74 | H2AFX; H2AFZ; HIST1H2AB; HIST1H2AE; HIST1H2AJ; HIST1H2BB; HIST1H2BC; HIST1H2BE; HIST1H2BF; HIST1H2BG; HIST1H2BH; HIST1H2BI; HIST1H2BJ; | 0 | 0.00 | | 0 | 0.00 | | 0 | 0.00 | | 0 | 0.00 | | 27 | 4.05 | H2AFX; H2AFZ; HIST1H2AB; HIST1H2AE; HIST1H2AJ; HIST1H2BB; HIST1H2BC; HIST1H2BD; HIST1H2BE; HIST1H2BF; HIST1H2BG; HIST1H2BI; HIST1H2BJ; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | HIST1H2BK; HIST1H2BL; HIST1H2BM; HIST1H2BO; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L; SNRPF; SNRPG | | | | | | | | | | | | | | | HIST1H2BK; HIST1H2BL; HIST1H2BM; HIST1H2BO; HIST1H3A; HIST1H3C; HIST1H3F; HIST1H3G; HIST1H3H; HIST1H3I; HIST1H3J; HIST1H4I; HIST2H2AA3; HIST2H2BE |
| regulation of nuclear division: GO | 154 | 34 | 3.69 | ANLN; AURKA; BIRC5; BUB1; BUB1B; CALR; CCNB1; CDC20; CDC6; CDCA5; CENPE; CENPF; CHEK1; DLGAP5; EPGN; EREG; FBXO5; GEN1; IL1A; IL1B; KIF11; KIF20B; MAD2L1; NEK2; OSM; PKMYT1; PLK1; | 6 | 0.46 | BTC; EDN3; EGF; LIF; NPM2; PIWIL2 | 0 | 0.00 | | 2 | 5.43 | IL1B; OSM | 2 | 0.33 | EDN3; EGF | 24 | 4.42 | ANLN; AURKA; BIRC5; BUB1; BUB1B; CCNB1; CDC20; CDC6; CDCA5; CENPE; CENPF; CHEK1; DLGAP5; EREG; KIF11; MAD2L1; NEK2; PKMYT1; PLK1; PTTG1; TGFA; TTK; UBE2C; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | PTTG1; RANBP1; RCC1; TGFA; TTK; UBE2C; WNT5A | | | | | | | | | | | | | | | |
| mitotic prophase | 78 | 20 | 4.29 | CCNB1; CCNB2; CDK1; H2AFX; H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; HIST1H4L; LMNB1; PLK1; SMC4 | 0 | 0.00 | | 0 | 0.00 | | 0 | 0.00 | | 0 | 0.00 | | 17 | 6.18 | CCNB1; CCNB2; CDK1; H2AFX; H2AFZ; HIST1H2AE; HIST1H2BB; HIST1H2BD; HIST1H2BF; HIST1H2BK; HIST1H2BM; HIST1H3A; HIST1H3I; HIST1H4I; HIST2H2BE; PLK1; SMC4 |
| factors involved in megakaryocyte development and platelet production | 146 | 26 | 2.98 | ACTB; CAP1; CAPZA1; CENPE; HIST1H3A; HIST1H3B; HIST1H3C; HIST1H3F; HIST1H3G; HIST1H3H; HIST1H3I; HIST1H3J; IL6; KIF11; KIF15; KIF18A; KIF20A; KIF20B; KIF23; | 7 | 0.57 | GATA1; GATA5; HBB; IFNA5; KIFC2; PRKAR2B; ZFPM2 | 1 | 2.86 | PRKAR2B | 0 | 0.00 | | 2 | 0.35 | HBB; ZFPM2 | 23 | 4.47 | ACTB; CAP1; CENPE; HIST1H3A; HIST1H3C; HIST1H3F; HIST1H3G; HIST1H3H; HIST1H3I; HIST1H3J; KIF11; KIF15; KIF18A; KIF18B; KIF20A; KIF23; KIF2C; KIF4A; KIFC1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | KIF2C; KIF4A; RACGAP1; TUBA1C; TUBA4A; TUBB2A; TUBB6 | | | | | | | | | | | | | | | TUBA1C; TUBA4A; TUBB2A; TUBB6 |
| ercc6 (csb) and ehmt2 (g9a) positively regulate rrna expression | 36 | 14 | 6.51 | H2AFX; H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; HIST1H4L | 0 | 0.00 | | 0 | 0.00 | | 0 | 0.00 | | 0 | 0.00 | | 12 | 9.45 | H2AFX; H2AFZ; HIST1H2AE; HIST1H2BB; HIST1H2BD; HIST1H2BF; HIST1H2BK; HIST1H2BM; HIST1H3A; HIST1H3I; HIST1H4I; HIST2H2BE |
| homology directed repair | 90 | 21 | 3.90 | BLM; BRCA2; CCNA2; CHEK1; CLSPN; EXO1; GEN1; H2AFX; HIST1H2BB; HIST1H2BF; HIST1H2BH; HIST1H2BK; HIST1H2BM; HIST1H4I; HIST1H4J; HIST1H4K; HIST1H4L; PCNA; POLQ; TIMELESS; UBE2N | 0 | 0.00 | | 0 | 0.00 | | 0 | 0.00 | | 0 | 0.00 | | 18 | 5.67 | BLM; BRCA2; BRIP1; CCNA2; CHEK1; EXO1; FEN1; H2AFX; HIST1H2BB; HIST1H2BD; HIST1H2BF; HIST1H2BK; HIST1H2BM; HIST1H4I; HIST2H2BE; POLQ; RAD51AP1; TIMELESS |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| dna replication | 148 | 27 | 3.05 | BIRC5; BUB1; BUB1B; CCNA2; CDC20; CDCA8; CDKN1A; CENPA; CENPN; E2F3; FBXO5; KIF18A; KIF20A; KIF23; KIF2C; MAD2L1; NDC80; NUF2; PLK1; PSMA4; PSMA5; PSMB6; PSMD1; SKA1; SPC25; ZWILCH; ZWINT | 0 | 0.00 | | 0 | 0.00 | | 0 | 0.00 | | 0 | 0.00 | | 23 | 4.41 | AURKB; BIRC5; BUB1; BUB1B; CCNA2; CDC20; CDCA8; CDKN1A; CENPA; E2F1; KIF18A; KIF20A; KIF23; KIF2C; MAD2L1; NDC80; NUF2; PLK1; SKA1; SPC24; SPC25; ZWILCH; ZWINT |
| midbody: GO | 124 | 23 | 3.10 | ASPM; AURKA; BIRC5; CDCA8; CDK1; CENPE; CENPF; CEP55; ECT2; GNAI3; HSPA5; KIF14; KIF20A; KIF20B; KIF23; KIF4A; NEK2; PITPNM1; | 2 | 0.19 | PTCH1; TTC23L | 0 | 0.00 | | 0 | 0.00 | | 4 | 0.82 | MAK; PTCH1; SCCPDH; TTC23L | 21 | 4.80 | ASPM; AURKA; AURKB; BIRC5; CDCA8; CDK1; CENPE; CENPF; CEP55; ECT2; HSPA5; KIF14; KIF20A; KIF23; KIF4A; NEK2; PITPNM1; PLK1; RAN; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | PLK1; RACGAP1; RALB; RAN; SLC2A1 | | | | | | | | | | | | | | | SLC2A1; SPAG5 |
| dna integrity checkpoint: GO | 136 | 21 | 2.58 | AURKA; BLM; CCNA2; CCNB1; CDC45; CDC6; CDK1; CDKN1A; CHEK1; CLSPN; DTL; E2F7; H2AFX; HMGA2; NPM1; PCNA; PLK1; PLK2; SFN; TOP2A; TP63 | 1 | 0.09 | PLK5 | 0 | 0.00 | | 0 | 0.00 | | 0 | 0.00 | | 22 | 4.59 | AURKA; BLM; BRIP1; CCNA2; CCNB1; CDC45; CDC6; CDK1; CDKN1A; CHEK1; DTL; E2F1; E2F7; FANCI; GTSE1; H2AFX; HMGA2; NPM1; PLK1; PLK2; SFN; TOP2A |
| b-wich complex positively regulates rrna expression | 53 | 16 | 5.05 | ACTB; DDX21; H2AFX; H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; HIST1H4L | 0 | 0.00 | | 0 | 0.00 | | 0 | 0.00 | | 0 | 0.00 | | 14 | 7.49 | ACTB; DDX21; H2AFX; H2AFZ; HIST1H2AE; HIST1H2BB; HIST1H2BD; HIST1H2BF; HIST1H2BK; HIST1H2BM; HIST1H3A; HIST1H3I; HIST1H4I; HIST2H2BE |
| dna double-strand break repair | 103 | 22 | 3.57 | BLM; BRCA2; CCNA2; CHEK1; CLSPN; | 0 | 0.00 | | 0 | 0.00 | | 0 | 0.00 | | 0 | 0.00 | | 19 | 5.23 | BLM; BRCA2; BRIP1; CCNA2; CHEK1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | EXO1; GEN1; H2AFX; HIST1H2BB; HIST1H2BF; HIST1H2BH; HIST1H2BK; HIST1H2BM; HIST1H4I; HIST1H4J; HIST1H4K; HIST1H4L; KPNA2; PCNA; POLQ; TIMELESS; UBE2N | | | | | | | | | | | | | | | EXO1; FEN1; H2AFX; HIST1H2BB; HIST1H2BD; HIST1H2BF; HIST1H2BK; HIST1H2BM; HIST1H4I; HIST2H2BE; KPNA2; POLQ; RAD51AP1; TIMELESS |
| g2/m dna damage checkpoint | 63 | 17 | 4.52 | BLM; CCNB1; CDK1; CHEK1; EXO1; H2AFX; HIST1H2BB; HIST1H2BF; HIST1H2BH; HIST1H2BK; HIST1H2BM; HIST1H4I; HIST1H4J; HIST1H4K; HIST1H4L; SFN; UBE2N | 0 | 0.00 | | 0 | 0.00 | | 0 | 0.00 | | 0 | 0.00 | | 15 | 6.75 | BLM; BRIP1; CCNB1; CDK1; CHEK1; EXO1; H2AFX; HIST1H2BB; HIST1H2BD; HIST1H2BF; HIST1H2BK; HIST1H2BM; HIST1H4I; HIST2H2BE; SFN |
| prc2 methylates histones and dna | 38 | 14 | 6.16 | H2AFX; H2AFZ; HIST1H2AE; HIST1H2BB; HIST1H2BF; HIST1H2BH; HIST1H2BK; HIST1H2BM; HIST1H3A; HIST1H3I; | 0 | 0.00 | | 0 | 0.00 | | 0 | 0.00 | | 0 | 0.00 | | 12 | 8.95 | H2AFX; H2AFZ; HIST1H2AE; HIST1H2BB; HIST1H2BD; HIST1H2BF; HIST1H2BK; HIST1H2BM; HIST1H3A; HIST1H3I; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | HIST1H4I; HIST1H4J; HIST1H4K; HIST1H4L | | | | | | | | | | | | | | | HIST1H4I; HIST2H2BE |
| negative regulation of gene expression epigenetic: GO | 96 | 20 | 3.49 | H2AFX; H2AFZ; HIST1H2AB; HIST1H2AE; HIST1H2AG; HIST1H2AH; HIST1H2AI; HIST1H2AL; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L | 3 | 0.37 | HDAC5; HILS1; TNP1 | 0 | 0.00 | | 0 | 0.00 | | 0 | 0.00 | | 18 | 5.32 | BEND3; H2AFX; H2AFZ; HIST1H2AB; HIST1H2AE; HIST1H2AG; HIST1H2AH; HIST1H2AI; HIST1H2AL; HIST1H3A; HIST1H3C; HIST1H3F; HIST1H3G; HIST1H3H; HIST1H3I; HIST1H3J; HIST1H4I; HIST2H2AA3 |
| senescence-associated secretory phenotype (sasp) | 66 | 20 | 5.07 | CCNA2; CDKN1A; CXCL8; H2AFX; H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; HIST1H4L; | 0 | 0.00 | | 0 | 0.00 | | 0 | 0.00 | | 0 | 0.00 | | 15 | 6.44 | CCNA2; CDKN1A; H2AFX; H2AFZ; HIST1H2AE; HIST1H2BB; HIST1H2BD; HIST1H2BF; HIST1H2BK; HIST1H2BM; HIST1H3A; HIST1H3I; HIST1H4I; HIST2H2BE; UBE2C |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | IL1A; IL6; UBE2C | | | | | | | | | | | | | | | |
| innate immune response in mucosa: GO | 20 | 9 | 7.53 | CAMP; HIST1H2BC; HIST1H2BE; HIST1H2BF; HIST1H2BG; HIST1H2BI; HIST1H2BJ; HIST1H2BK; LTF | 1 | 0.59 | NOS2 | 0 | 0.00 | | 0 | 0.00 | | 0 | 0.00 | | 9 | 12.76 | HIST1H2BC; HIST1H2BE; HIST1H2BF; HIST1H2BG; HIST1H2BI; HIST1H2BJ; HIST1H2BK; HIST2H2BE; LTF |
| rho gtpases activate pkns | 49 | 15 | 5.12 | H2AFX; H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; HIST1H4L; SFN | 2 | 0.48 | AR; MYL9 | 0 | 0.00 | | 0 | 0.00 | | 0 | 0.00 | | 13 | 7.52 | H2AFX; H2AFZ; HIST1H2AE; HIST1H2BB; HIST1H2BD; HIST1H2BF; HIST1H2BK; HIST1H2BM; HIST1H3A; HIST1H3I; HIST1H4I; HIST2H2BE; SFN |
| negative regulation of mitotic cell cycle: GO | 186 | 26 | 2.34 | AURKA; BLM; BTG3; BUB1; BUB1B; CCNA2; CCNB1; CDK1; CDKN1A; CENPF; CHEK1; CLSPN; E2F7; HMGA2; MAD2L1; NPM1; PCNA; PLK1; | 5 | 0.32 | BCL2; DACT1; FHL1; KANK2; USP17L2 | 0 | 0.00 | | 0 | 0.00 | | 3 | 0.41 | BCL2; DACT1; FOXC1 | 25 | 3.81 | AURKA; BLM; BUB1; BUB1B; CCNA2; CCNB1; CDK1; CDKN1A; CENPF; CHEK1; E2F1; E2F7; FANCI; GTSE1; HMGA2; MAD2L1; NPM1; PLK1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | PLK2; PTTG1; SFN; TOP2A; TP63; TTK; ZWILCH; ZWINT | | | | | | | | | | | | | | | PLK2; PTTG1; SFN; TOP2A; TTK; ZWILCH; ZWINT |
| mitotic g2-g2/m phases | 137 | 23 | 2.81 | AURKA; CCNA2; CCNB1; CCNB2; CDC25A; CDC25B; CDK1; CDKN1A; CENPF; DYNLL1; E2F3; FOXM1; HMMR; MYBL2; NEK2; PLK1; PSMA5; PSMB6; TPX2; TUBA1C; TUBA4A; TUBB2A; TUBB6 | 2 | 0.17 | MAST1; PRKAR2B | 1 | 3.05 | PRKAR2B | 0 | 0.00 | | 2 | 0.37 | DLC1; SLC29A1 | 21 | 4.35 | AURKA; CCNA2; CCNB1; CCNB2; CDC25A; CDC25B; CDK1; CDKN1A; CENPF; E2F1; FOXM1; GTSE1; HMMR; NEK2; PLK1; PLK4; TPX2; TUBA1C; TUBA4A; TUBB2A; TUBB6 |
| negative regulation of cell cycle phase transition: GO | 138 | 21 | 2.55 | AURKA; BLM; BUB1; BUB1B; C10orf99; CCNA2; CCNB1; CDK1; CDKN1A; CENPF; CLSPN; E2F7; HMGA2; MAD2L1; NPM1; | 5 | 0.43 | BCL2; DACT1; FHL1; KANK2; SUSD2 | 0 | 0.00 | | 0 | 0.00 | | 3 | 0.55 | BCL2; DACTI; SUSD2 | 21 | 4.32 | AURKA; BLM; BUB1; BUB1B; C10orf99; CCNA2; CCNB1; CDK1; CDKN1A; CENPF; E2F1; E2F7; FANCI; GTSE1; HMGA2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | PCNA; PLK1; PLK2; SFN; TP63; TTK | | | | | | | | | | | | | | | MAD2L1; NPM1; PLK1; PLK2; SFN; TTK |
| spindle pole: GO | 114 | 20 | 2.94 | ASPM; AURKA; CCNB1; CDC20; CDC25B; CDC6; CENPF; CKAP2; CKAP2L; DLGAP5; FAM110C; FAM83D; KIF11; KIF20B; MAD2L1; NEK2; NPM1; PLK1; POC1A; TPX2 | 2 | 0.21 | DNAAF1; DYNC1I1 | 0 | 0.00 | | 0 | 0.00 | | 1 | 0.22 | FRY | 19 | 4.73 | ASPM; AURKA; AURKB; CCNB1; CDC20; CDC25B; CDC6; CENPF; CEP19; DLGAP5; FAM110C; KIF11; MAD2L1; NEK2; NPM1; PLK1; POC1A; SPAG5; TPX2 |
| formation of the beta-catenin: tcf transactivating complex | 43 | 15 | 5.84 | H2AFX; H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; HIST1H4L; RUVBL1 | 0 | 0.00 | | 0 | 0.00 | | 0 | 0.00 | | 0 | 0.00 | | 12 | 7.91 | H2AFX; H2AFZ; HIST1H2AE; HIST1H2BB; HIST1H2BD; HIST1H2BF; HIST1H2BK; HIST1H2BM; HIST1H3A; HIST1H3I; HIST1H4I; HIST2H2BE |
| runx1 regulates genes involved in | 43 | 15 | 5.84 | H2AFX; H2AFZ; HIST1H2AE; HIST1H2BB; | 1 | 0.27 | MYL9 | 0 | 0.00 | | 0 | 0.00 | | 0 | 0.00 | | 12 | 7.91 | H2AFX; H2AFZ; HIST1H2AE; HIST1H2BB; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| megakaryocyte differentiation and platelet function | | | | HIST1H2BF; HIST1H2BH; HIST1H2BK; HIST1H2BM; HIST1H3A; HIST1H3I; HIST1H4I; HIST1H4J; HIST1H4K; HIST1H4L; NR4A3 | | | | | | | | | | | | | | | HIST1H2BD; HIST1H2BF; HIST1H2BK; HIST1H2BM; HIST1H3A; HIST1H3I; HIST1H4I; HIST2H2BE |
| positive epigenetic regulation of rrna expression | 61 | 16 | 4.39 | ACTB; DDX21; H2AFX; H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; HIST1H4L | 0 | 0.00 | | 0 | 0.00 | | 0 | 0.00 | | 0 | 0.00 | | 14 | 6.51 | ACTB; DDX21; H2AFX; H2AFZ; HIST1H2AE; HIST1H2BB; HIST1H2BD; HIST1H2BF; HIST1H2BK; HIST1H2BM; HIST1H3A; HIST1H3I; HIST1H4I; HIST2H2BE |
| gene silencing by rna | 22 | 8 | 6.08 | H2AFX; H2AFZ; HIST1H2AE; HIST1H2BB; HIST1H2BF; HIST1H2BH; HIST1H2BK; HIST1H2BM | 0 | 0.00 | | 0 | 0.00 | | 0 | 0.00 | | 1 | 1.15 | TDRD6 | 9 | 11.60 | H2AFX; H2AFZ; HIST1H2AE; HIST1H2BB; HIST1H2BD; HIST1H2BF; HIST1H2BK; HIST1H2BM; HIST2H2BE |
| hdr through homologous recombination (hr) or single strand | 85 | 20 | 3.94 | BLM; BRCA2; CCNA2; CHEK1; CLSPN; | 0 | 0.00 | | 0 | 0.00 | | 0 | 0.00 | | 0 | 0.00 | | 16 | 5.34 | BLM; BRCA2; BRIP1; CCNA2; CHEK1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| annealing (ssa) | | | | EXO1; GEN1; H2AFX; HIST1H2BB; HIST1H2BF; HIST1H2BH; HIST1H2BK; HIST1H2BM; HIST1H4I; HIST1H4J; HIST1H4K; HIST1H4L; PCNA; TIMELESS; UBE2N | | | | | | | | | | | | | | | EXO1; H2AFX; HIST1H2BB; HIST1H2BD; HIST1H2BF; HIST1H2BK; HIST1H2BM; HIST1H4I; HIST2H2BE; RAD51AP1; TIMELESS |
| oxidative stress induced senescence | 75 | 18 | 4.02 | CBX2; E2F3; H2AFX; H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; HIST1H4L; IL6; TXN | 0 | 0.00 | | 0 | 0.00 | | 0 | 0.00 | | 0 | 0.00 | | 15 | 5.67 | CBX2; E2F1; H2AFX; H2AFZ; HIST1H2AE; HIST1H2BB; HIST1H2BD; HIST1H2BF; HIST1H2BK; HIST1H2BM; HIST1H3A; HIST1H3I; HIST1H4I; HIST2H2BE; TXN |
| processing of dna double-strand break ends | 66 | 17 | 4.31 | BLM; CCNA2; CHEK1; CLSPN; EXO1; H2AFX; HIST1H2BB; HIST1H2BF; HIST1H2BH; HIST1H2BK; HIST1H2BM; | 0 | 0.00 | | 0 | 0.00 | | 0 | 0.00 | | 0 | 0.00 | | 14 | 6.02 | BLM; BRIP1; CCNA2; CHEK1; EXO1; H2AFX; HIST1H2BB; HIST1H2BD; HIST1H2BF; HIST1H2BK; HIST1H2BM; HIST1H4I; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | HIST1H4I; HIST1H4J; HIST1H4K; HIST1H4L; TIMELESS; UBE2N | | | | | | | | | | | | | | | HIST2H2BE; TIMELESS |
| copi-dependent golgi-to-er retrograde traffic | 66 | 14 | 3.55 | CENPE; KIF11; KIF15; KIF18A; KIF20A; KIF20B; KIF23; KIF2C; KIF4A; RACGAP1; TUBA1C; TUBA4A; TUBB2A; TUBB6 | 1 | 0.18 | KIFC2 | 0 | 0.00 | | 0 | 0.00 | | 0 | 0.00 | | 14 | 6.02 | CENPE; KIF11; KIF15; KIF18A; KIF18B; KIF20A; KIF23; KIF2C; KIF4A; KIFC1; TUBA1C; TUBA4A; TUBB2A; TUBB6 |
| g2/m transition | 135 | 22 | 2.73 | AURKA; CCNA2; CCNB1; CCNB2; CDC25A; CDC25B; CDK1; CDKN1A; CENPF; DYNLL1; FOXM1; HMMR; MYBL2; NEK2; PLK1; PSMA5; PSMB6; TPX2; TUBA1C; TUBA4A; TUBB2A; TUBB6 | 2 | 0.17 | MAST1; PRKAR2B | 1 | 3.10 | PRKAR2B | 0 | 0.00 | | 2 | 0.38 | DLC1; SLC29A1 | 20 | 4.20 | AURKA; CCNA2; CCNB1; CCNB2; CDC25A; CDC25B; CDK1; CDKN1A; CENPF; FOXM1; GTSE1; HMMR; NEK2; PLK1; PLK4; TPX2; TUBA1C; TUBA4A; TUBB2A; TUBB6 |
| chromosome localization: | 57 | 14 | 4.11 | ACTR3; BIRC5; | 0 | 0.00 | | 0 | 0.00 | | 0 | 0.00 | | 0 | 0.00 | | 13 | 6.47 | BIRC5; BRCA2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| GO | | | | BRCA2; CCNB1; CDCA5; CDCA8; CENPE; CENPF; CEP55; DLGAP5; FAM83D; KIF14; KIF18A; KIF2C | | | | | | | | | | | | | | | CCNB1; CDCA5; CDCA8; CENPE; CENPF; CEP55; DLGAP5; KIF14; KIF18A; KIF2C; KIFC1 |
| negative regulation of cell division: GO | 57 | 14 | 4.11 | ASPM; BLM; BUB1; BUB1B; C10orf99; CENPF; CHEK1; E2F7; FBXO5; MAD2L1; OSM; PLK1; PTTG1; TTK | 4 | 0.83 | LIF; PTCH1; SUSD2; TXNIP | 0 | 0.00 | | 1 | 7.33 | OSM | 3 | 1.34 | PTCH1; SUSD2; TXNIP | 13 | 6.47 | ASPM; AURKB; BLM; BUB1; BUB1B; C10orf99; CENPF; CHEK1; E2F7; MAD2L1; PLK1; PTTG1; TTK |
| regulation of microtubule poly-merization or depoly-merization: GO | 164 | 24 | 2.45 | ASPM; AURKA; BIRC5; CCNB1; CKAP2; FBXO5; KIF11; KIF23; KIF4A; MYBL2; NDC80; NEK2; PLK1; PLK2; RACGAP1; RAN; RANBP1; | 6 | 0.43 | BIRC7; GAS2L2; MAP1A; MAPT; PKD1; SNCA | 0 | 0.00 | | 0 | 0.00 | | 2 | 0.31 | MAPT; SNCA | 22 | 3.80 | ASPM; AURKA; AURKB; BIRC5; CCNB1; KIF11; KIF23; KIF4A; KIFC1; NDC80; NEK2; PLK1; PLK2; RAN; SGK1; SKA1; SKA3; SPAG5; SPC25; STIL; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | RCC1; SKA1; SKA3; SPC25; STIL; TPX2; TTK | | | | | | | | | | | | | | | TPX2; TTK |
| metaphase plate congression: GO | 41 | 11 | 4.49 | BRCA2; CCNB1; CDCA5; CDCA8; CENPE; CENPF; CEP55; FAM83D; KIF14; KIF18A; KIF2C | 0 | 0.00 | | 0 | 0.00 | | 0 | 0.00 | | 0 | 0.00 | | 11 | 7.61 | BRCA2; CCNB1; CDCA5; CDCA8; CENPE; CENPF; CEP55; KIF14; KIF18A; KIF2C; KIFC1 |
| rna polymerase i chain elongation | 50 | 14 | 4.69 | H2AFX; H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; HIST1H4L | 0 | 0.00 | | 0 | 0.00 | | 0 | 0.00 | | 0 | 0.00 | | 12 | 6.81 | H2AFX; H2AFZ; HIST1H2AE; HIST1H2BB; HIST1H2BD; HIST1H2BF; HIST1H2BK; HIST1H2BM; HIST1H3A; HIST1H3I; HIST1H4I; HIST2H2BE |
| transcriptional regulation by small rnas | 50 | 14 | 4.69 | H2AFX; H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; | 0 | 0.00 | | 0 | 0.00 | | 0 | 0.00 | | 0 | 0.00 | | 12 | 6.81 | H2AFX; H2AFZ; HIST1H2AE; HIST1H2BB; HIST1H2BD; HIST1H2BF; HIST1H2BK; HIST1H2BM; HIST1H3A; HIST1H3I; HIST1H4I; HIST2H2BE |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | HIST1H4K; HIST1H4L | | | | | | | | | | | | | | | |
| spindle midzone: GO | 26 | 10 | 6.44 | AURKA; BUB1B; CDC6; CDCA8; CENPE; KIF14; KIF18A; KIF20B; PLK1; RACGAP1 | 0 | 0.00 | | 0 | 0.00 | | 0 | 0.00 | | 1 | 0.98 | CENPV | 9 | 9.82 | AURKA; AURKB; BUB1B; CDC6; CDCA8; CENPE; KIF14; KIF18A; PLK1 |
| regulation of sister chromatid segregation: GO | 61 | 15 | 4.11 | BUB1; BUB1B; CCNB1; CDC6; CDCA5; CENPE; CENPF; DLGAP5; FBXO5; GEN1; MAD2L1; PLK1; PTTG1; TTK; UBE2C | 0 | 0.00 | | 0 | 0.00 | | 0 | 0.00 | | 0 | 0.00 | | 13 | 6.04 | BUB1; BUB1B; CCNB1; CDC6; CDCA5; CENPE; CENPF; DLGAP5; MAD2L1; PLK1; PTTG1; TTK; UBE2C |
| dna repair | 34 | 9 | 4.43 | ACTB; CCNA2; HIST1H2BB; HIST1H2BF; HIST1H2BH; HIST1H2BK; HIST1H2BM; KPNA2; TIMELESS | 0 | 0.00 | | 0 | 0.00 | | 0 | 0.00 | | 0 | 0.00 | | 10 | 8.34 | ACTB; CCNA2; HIST1H2BB; HIST1H2BD; HIST1H2BF; HIST1H2BK; HIST1H2BM; HIST2H2BE; KPNA2; TIMELESS |
| cellular senescence | 118 | 25 | 3.55 | CBX2; CCNA2; CCNE1; CXCL8; E2F3; H2AFZ; | 0 | 0.00 | | 0 | 0.00 | | 0 | 0.00 | | 0 | 0.00 | | 18 | 4.33 | CBX2; CCNA2; E2F1; H2AFZ; HIST1H1B; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | HIST1H1B; HIST1HID; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; HIST1H4L; IL1A; IL6; LMNB1; TXN; UBE2C | | | | | | | | | | | | | | | HIST1H1D; HIST1H2AE; HIST1H2BB; HIST1H2BD; HIST1H2BF; HIST1H2BK; HIST1H2BM; HIST1H3A; HIST1H3I; HIST1H4I; HIST2H2BE; TXN; UBE2C |
| apc/c-mediated degradation of cell cycle proteins | 62 | 15 | 4.05 | AURKA; BUB1; BUB1B; CCNA2; CCNB1; CDC20; CDK1; FBXO5; MAD2L1; NEK2; PLK1; PSMA5; PSMB6; PTTG1; UBE2C | 0 | 0.00 | | 0 | 0.00 | | 0 | 0.00 | | 0 | 0.00 | | 13 | 5.95 | AURKA; AURKB; BUB1; BUB1B; CCNA2; CCNB1; CDC20; CDK1; MAD2L1; NEK2; PLK1; PTTG1; UBE2C |
| organ or tissue specific immune response: GO | 27 | 10 | 6.20 | CAMP; HIST1H2BC; HIST1H2BE; HIST1H2BF; HIST1H2BG; HIST1H2BI; HIST1H2BJ; HIST1H2BK; IL6; LTF | 1 | 0.44 | NOS2 | 0 | 0.00 | | 1 | 15.48 | FFAR2 | 0 | 0.00 | | 9 | 9.45 | HIST1H2BC; HIST1H2BE; HIST1H2BF; HIST1H2BG; HIST1H2BI; HIST1H2BJ; HIST1H2BK; HIST2H2BE; LTF |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| protein heterotetramerization: GO | 35 | 13 | 6.22 | HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L; RRM2 | 2 | 0.67 | LRP4; NLGN1 | 0 | 0.00 | | 0 | 0.00 | | 0 | 0.00 | | 10 | 8.10 | HIST1H3A; HIST1H3C; HIST1H3F; HIST1H3G; HIST1H3H; HIST1H3I; HIST1H3J; HIST1H4I; PDSS1; RRM2 |
| hdacs deacetylate histones | 44 | 13 | 4.94 | H2AFX; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; HIST1H4L | 0 | 0.00 | | 0 | 0.00 | | 0 | 0.00 | | 0 | 0.00 | | 11 | 7.09 | H2AFX; HIST1H2AE; HIST1H2BB; HIST1H2BD; HIST1H2BF; HIST1H2BK; HIST1H2BM; HIST1H3A; HIST1H3I; HIST1H4I; HIST2H2BE |
| cell cycle g1 s phase transition: GO | 109 | 21 | 3.22 | CCNE1; CDC25A; CDC45; CDC6; CDCA5; CDK1; CDKN1A; CDKN3; DBF4; E2F7; EIF4EBP1; FBXO5; MCM10; ORC1; ORC6; PCNA; PKMYT1; | 3 | 0.32 | CAMK2A; CDK3; ID4 | 0 | 0.00 | | 0 | 0.00 | | 1 | 0.23 | RHOU | 17 | 4.42 | CDC25A; CDC45; CDC6; CDCA5; CDK1; CDKN1A; CDKN3; E2F1; E2F7; EIF4EBP1; IQGAP3; MCM2; ORC1; ORC6; PKMYT1; PLK2; RRM2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | PLK2; RANBP1; RCC1; RRM2 | | | | | | | | | | | | | | | |
| golgi-to-er retrograde transport | 86 | 16 | 3.11 | CAP1; CENPE; DYNLL1; KIF11; KIF15; KIF18A; KIF20A; KIF20B; KIF23; KIF2C; KIF4A; RACGAP1; TUBA1C; TUBA4A; TUBB2A; TUBB6 | 1 | 0.14 | KIFC2 | 0 | 0.00 | | 0 | 0.00 | | 1 | 0.30 | DLC1 | 15 | 4.95 | CAP1; CENPE; KIF11; KIF15; KIF18A; KIF18B; KIF20A; KIF23; KIF2C; KIF4A; KIFC1; TUBA1C; TUBA4A; TUBB2A; TUBB6 |
| amyloid fiber formation | 55 | 15 | 4.56 | H2AFX; H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; HIST1H4L; LYZ | 3 | 0.64 | GSN; NAT8; TF | 0 | 0.00 | | 1 | 7.60 | LYZ | 0 | 0.00 | | 12 | 6.19 | H2AFX; H2AFZ; HIST1H2AE; HIST1H2BB; HIST1H2BD; HIST1H2BF; HIST1H2BK; HIST1H2BM; HIST1H3A; HIST1H3I; HIST1H4I; HIST2H2BE |
| tp53 regulates transcription of cell cycle genes | 37 | 11 | 4.97 | AURKA; CCNA2; CCNB1; CCNE1; CDK1; CDKN1A; E2F7; NPM1; PCNA; PLK2; | 0 | 0.00 | | 0 | 0.00 | | 0 | 0.00 | | 0 | 0.00 | | 10 | 7.66 | AURKA; CCNA2; CCNB1; CDK1; CDKN1A; E2F1; E2F7; NPM1; PLK2; SFN |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | SFN | | | | | | | | | | | | | | | |
| spindle microtubule: GO | 57 | 9 | 2.64 | AURKA; BIRC5; CDK1; KIF11; KIF18A; KIF4A; PLK1; SKA1; SKA3 | 2 | 0.41 | BIRC7; CAPN6 | 1 | 7.33 | CAPN6 | 0 | 0.00 | | 0 | 0.00 | | 12 | 5.97 | AURKA; AURKB; BIRC5; CDK1; KIF11; KIF18A; KIF18B; KIF4A; PLK1; SKA1; SKA3; SPAG5 |
| aurora a pathway | 30 | 7 | 3.90 | AURKA; BIRC5; CDC25B; CENPA; DLGAP5; RAN; TPX2 | 1 | 0.39 | CPEB1 | 0 | 0.00 | | 0 | 0.00 | | 1 | 0.85 | CPEB1 | 9 | 8.51 | AURKA; AURKB; BIRC5; CDC25B; CENPA; DLGAP5; RAN; TACC3; TPX2 |
| antimicrobial humoral response: GO | 48 | 12 | 4.18 | CAMP; HIST1H2BC; HIST1H2BE; HIST1H2BF; HIST1H2BG; HIST1H2BI; HIST1H2BJ; HIST1H2BK; IL36RN; LTF; RNASE7; SLPI | 1 | 0.25 | PLA2G6 | 1 | 8.71 | IGKV3-20 | 0 | 0.00 | | 1 | 0.53 | IGHM | 11 | 6.50 | BCL3; HIST1H2BC; HIST1H2BE; HIST1H2BF; HIST1H2BG; HIST1H2BI; HIST1H2BJ; HIST1H2BK; HIST2H2BE; LTF; SLPI |
| spindle checkpoint: GO | 23 | 7 | 5.09 | BIRC5; BUB1; BUB1B; CENPF; MAD2L1; PLK1; TTK | 0 | 0.00 | | 0 | 0.00 | | 0 | 0.00 | | 0 | 0.00 | | 8 | 9.86 | AURKB; BIRC5; BUB1; BUB1B; CENPF; MAD2L1; PLK1; TTK |
| rna polymerase i promoter clearance | 58 | 14 | 4.04 | H2AFX; H2AFZ; HIST1H2AE; HIST1H2BB; HIST1H2BF; | 0 | 0.00 | | 0 | 0.00 | | 0 | 0.00 | | 0 | 0.00 | | 12 | 5.87 | H2AFX; H2AFZ; HIST1H2AE; HIST1H2BB; HIST1H2BD; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | HIST1H2BH; HIST1H2BK; HIST1H2BM; HIST1H3A; HIST1H3I; HIST1H4I; HIST1H4J; HIST1H4K; HIST1H4L | | | | | | | | | | | | | | | HIST1H2BF; HIST1H2BK; HIST1H2BM; HIST1H3A; HIST1H3I; HIST1H4I; HIST2H2BE |
| activation of anterior hox genes in hindbrain development during early embryogenesis | 59 | 14 | 3.97 | H2AFX; H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; HIST1H4L | 1 | 0.20 | PAX6 | 0 | 0.00 | | 0 | 0.00 | | 0 | 0.00 | | 12 | 5.77 | H2AFX; H2AFZ; HIST1H2AE; HIST1H2BB; HIST1H2BD; HIST1H2BF; HIST1H2BK; HIST1H2BM; HIST1H3A; HIST1H3I; HIST1H4I; HIST2H2BE |
| activation of hox genes during differentiation | 59 | 14 | 3.97 | H2AFX; H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; HIST1H4L | 1 | 0.20 | PAX6 | 0 | 0.00 | | 0 | 0.00 | | 0 | 0.00 | | 12 | 5.77 | H2AFX; H2AFZ; HIST1H2AE; HIST1H2BB; HIST1H2BD; HIST1H2BF; HIST1H2BK; HIST1H2BM; HIST1H3A; HIST1H3I; HIST1H4I; HIST2H2BE |
| rna polymerase i transcription | 59 | 14 | 3.97 | H2AFX; H2AFZ; HIST1H2AE; HIST1H2BB; | 0 | 0.00 | | 0 | 0.00 | | 0 | 0.00 | | 0 | 0.00 | | 12 | 5.77 | H2AFX; H2AFZ; HIST1H2AE; HIST1H2BB; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | HIST1H2BF; HIST1H2BH; HIST1H2BK; HIST1H2BM; HIST1H3A; HIST1H3I; HIST1H4I; HIST1H4J; HIST1H4K; HIST1H4L | | | | | | | | | | | | | | | HIST1H2BD; HIST1H2BF; HIST1H2BK; HIST1H2BM; HIST1H3A; HIST1H3I; HIST1H4I; HIST2H2BE |
| p53 signaling pathway | 70 | 14 | 3.35 | CCNB1; CCNB2; CCND2; CCNE1; CDK1; CDKN1A; CHEK1; CYCS; PCNA; PERP; RRM2; SERPINB5; SERPINE1; SFN | 2 | 0.34 | BCL2; TIMP3 | 0 | 0.00 | | 1 | 5.97 | SERPINE1 | 1 | 0.36 | BCL2 | 13 | 5.27 | CCNB1; CCNB2; CCND2; CDK1; CDKN1A; CHEK1; CYCS; E2F1; GTSE1; IGFBP3; RRM2; SERPINB5; SFN |
| cell cycle: g2/m checkpoint | 24 | 8 | 5.58 | CCNB1; CDC25A; CDC25B; CDK1; CDKN1A; CHEK1; PLK1; YWHAQ | 0 | 0.00 | | 0 | 0.00 | | 0 | 0.00 | | 0 | 0.00 | | 8 | 9.45 | CCNB1; CDC25A; CDC25B; CDK1; CDKN1A; CHEK1; PLK1; YWHAQ |
| g2 pathway | 24 | 8 | 5.58 | CCNB1; CDC25A; CDC25B; CDK1; CDKN1A; CHEK1; PLK1; YWHAQ | 0 | 0.00 | | 0 | 0.00 | | 0 | 0.00 | | 0 | 0.00 | | 8 | 9.45 | CCNB1; CDC25A; CDC25B; CDK1; CDKN1A; CHEK1; PLK1; YWHAQ |
| mitotic dna integrity checkpoint: | 94 | 15 | 2.67 | AURKA; BLM; CCNA2; | 0 | 0.00 | | 0 | 0.00 | | 0 | 0.00 | | 0 | 0.00 | | 15 | 4.53 | AURKA; BLM: CCNA2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| GO | | | | CCNB1; CDK1; CDKN1A; CLSPN; E2F7; HMGA2; NPM1; PCNA; PLK2; SFN; TOP2A; TP63 | | | | | | | | | | | | | | | CCNB1; CDK1; CDKN1A; E2F1; E2F7; FANCI; GTSE1; HMGA2; NPM1; PLK2; SFN; TOP2A |
| norc negatively regulates rrna expression | 61 | 14 | 3.84 | H2AFX; H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; HIST1H4L | 0 | 0.00 | | 0 | 0.00 | | 0 | 0.00 | | 0 | 0.00 | | 12 | 5.58 | H2AFX; H2AFZ; HIST1H2AE; HIST1H2BB; HIST1H2BD; HIST1H2BF; HIST1H2BK; HIST1H2BM; HIST1H3A; HIST1H3I; HIST1H4I; HIST2H2BE |
| activation of e2f1 target genes at g1/s | 25 | 10 | 6.69 | CCNE1; CDC25A; CDC45; CDC6; CDK1; FBXO5; ORC1; PCNA; RRM2; TK1 | 0 | 0.00 | | 0 | 0.00 | | 0 | 0.00 | | 0 | 0.00 | | 8 | 9.07 | CDC25A; CDC45; CDC6; CDK1; E2F1; ORC1; RRM2; TK1 |
| g1/s-specific transcription | 25 | 10 | 6.69 | CCNE1; CDC25A; CDC45; CDC6; CDK1; FBXO5; ORC1; PCNA; RRM2; TK1 | 0 | 0.00 | | 0 | 0.00 | | 0 | 0.00 | | 0 | 0.00 | | 8 | 9.07 | CDC25A; CDC45; CDC6; CDK1; E2F1; ORC1; RRM2; TK1 |
| hats acetylate histones | 62 | 15 | 4.05 | ACTB; H2AFX; HIST1H2AE; HIST1H2BB; | 0 | 0.00 | | 0 | 0.00 | | 0 | 0.00 | | 0 | 0.00 | | 12 | 5.49 | ACTB; H2AFX; HIST1H2AE; HIST1H2BB; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | HIST1H2BF; HIST1H2BH; HIST1H2BK; HIST1H2BM; HIST1H3A; HIST1H3I; HIST1H4I; HIST1H4J; HIST1H4K; HIST1H4L; RUVBL1 | | | | | | | | | | | | | | | HIST1H2BD; HIST1H2BF; HIST1H2BK; HIST1H2BM; HIST1H3A; HIST1H3I; HIST1H4I; HIST2H2BE |
| chromosome telomeric region: GO | 150 | 22 | 2.45 | BLM; BRCA2; CDK1; CHEK1; H2AFX; HIST1H2BB; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L; NLRP2; ORC1; PCNA; PIF1 | 1 | 0.08 | TERT | 0 | 0.00 | | 0 | 0.00 | | 0 | 0.00 | | 19 | 3.59 | BLM; BRCA2; CDK1; CHEK1; FEN1; H2AFX; HIST1H2BB; HIST1H3A; HIST1H3C; HIST1H3F; HIST1H3G; HIST1H3H; HIST1H3I; HIST1H3J; HIST1H4I; MCM2; NLRP2; ORC1; PIF1 |
| mitotic g1-g1/s phases | 110 | 23 | 3.50 | CCNA2; CCNB1; CCND2; CCNE1; CDC25A; CDC25B; CDC45; CDC6; CDK1; CDKN1A; | 0 | 0.00 | | 0 | 0.00 | | 0 | 0.00 | | 0 | 0.00 | | 16 | 4.12 | CCNA2; CCNB1; CCND2; CDC25A; CDC25B; CDC45; CDC6; CDK1; CDKN1A; E2F1; MCM2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | DBF4; E2F3; FBXO5; MCM10; MYBL2; ORC1; ORC6; PCNA; PSMA5; PSMB6; RRM2; TK1; TOP2A | | | | | | | | | | | | | | | ORC1; ORC6; RRM2; TK1; TOP2A |
| e2f mediated regulation of dna replication | 34 | 11 | 5.41 | CCNB1; CCNE1; CDC25A; CDC45; CDC6; CDK1; FBXO5; ORC1; ORC6; PCNA; RRM2 | 0 | 0.00 | | 0 | 0.00 | | 0 | 0.00 | | 0 | 0.00 | | 9 | 7.51 | CCNB1; CDC25A; CDC45; CDC6; CDK1; E2F1; ORC1; ORC6; RRM2 |
| chromosome condensation: GO | 26 | 8 | 5.15 | CCNB1; CDCA5; CDK1; HMGA2; NCAPG; NCAPH; SMC4; TOP2A | 2 | 0.91 | HIFNT; HILS1 | 0 | 0.00 | | 0 | 0.00 | | 0 | 0.00 | | 8 | 8.73 | CCNB1; CDCA5; CDK1; HMGA2; NCAPG; NCAPH; SMC4; TOP2A |
| negative epigenetic regulation of rrna expression | 64 | 14 | 3.66 | H2AFX; H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; HIST1H4L | 0 | 0.00 | | 0 | 0.00 | | 0 | 0.00 | | 0 | 0.00 | | 12 | 5.32 | H2AFX; H2AFZ; HIST1H2AE; HIST1H2BB; HIST1H2BD; HIST1H2BF; HIST1H2BK; HIST1H2BM; HIST1H3A; HIST1H3I; HIST1H4I; HIST2H2BE |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| epigenetic regulation of gene expression | 87 | 17 | 3.27 | ACTB; DDX21; H2AFX; H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; HIST1H4L; UHRF1 | 1 | 0.14 | TET1 | 0 | 0.00 | | 0 | 0.00 | | 1 | 0.29 | TET1 | 14 | 4.56 | ACTB; DDX21; H2AFX; H2AFZ; HIST1H2AE; HIST1H2BB; HIST1H2BD; HIST1H2BF; HIST1H2BK; HIST1H2BM; HIST1H3A; HIST1H3I; HIST1H4I; HIST2H2BE |
| delta np63 pathway | 44 | 13 | 4.94 | BDKRB2; BRCA2; CCNB2; IL1A; ITGA3; KRT14; KRT5; NRG1; PERP; RAB38; SFN; TOP2A; TP63 | 1 | 0.27 | TCF7L1 | 0 | 0.00 | | 0 | 0.00 | | 1 | 0.58 | TCF7L1 | 10 | 6.44 | BDKRB2; BRCA2; CCNB2; IGFBP3; ITGA3; KRT5; NRG1; RAB38; SFN; TOP2A |
| kinesin complex: GO | 54 | 10 | 3.10 | CENPE; KIF11; KIF14; KIF15; KIF18A; KIF20A; KIF20B; KIF23; KIF2C; KIF4A | 2 | 0.44 | KIFIA; KIFC2 | 0 | 0.00 | | 0 | 0.00 | | 0 | 0.00 | | 11 | 5.78 | CENPE; KIF11; KIF14; KIF15; KIF18A; KIF18B; KIF20A; KIF23; KIF2C; KIF4A; KIFC1 |
| p73pathway | 76 | 20 | 4.40 | AEN; BAK1; BRCA2; BUB1; CCNA2; CCNB1; | 1 | 0.16 | GATA1 | 0 | 0.00 | | 1 | 5.50 | SERPINE1 | 0 | 0.00 | | 13 | 4.85 | BAK1; BRCA2; BUB1; CCNA2; CCNB1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | CDK1; CDKN1A; CHEK1; CLCA2; FBXO45; IL1RAP; IL4R; NTRK1; PLK1; S100A2; SERPINA1; SERPINE1; SFN; TP63 | | | | | | | | | | | | | | | CDK1; CDKN1A; CHEK1; CLCA2; FBXO45; PLK1; S100A2; SFN |
| chromatin silencing at rdna: GO | 35 | 12 | 5.74 | HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L | 0 | 0.00 | | 0 | 0.00 | | 0 | 0.00 | | 0 | 0.00 | | 9 | 7.29 | BEND3; HIST1H3A; HIST1H3C; HIST1H3F; HIST1H3G; HIST1H3H; HIST1H3I; HIST1H3J; HIST1H4I |
| negative regulation of protein complex disassembly: GO | 156 | 23 | 2.47 | ASPM; AURKA; BIRC5; CAPZA1; CCNB1; CKAP2; FBXO5; KIF11; KIF23; KIF4A; MYBL2; NDC80; NEK2; PLK2; RACGAP1; RAN; RANBP1; RCC1; SPC25; | 10 | 0.76 | BIRC7; CAPZA3; GAS2L2; GSN; LMOD1; MAP1A; SCIN; SLN; SPTBN4; TMOD1 | 0 | 0.00 | | 0 | 0.00 | | 4 | 0.65 | CAPZA3; LMOD1; SCIN; SPTBN4 | 19 | 3.45 | ASPM; AURKA; AURKB; BIRC5; CCNB1; KIF11; KIF23; KIF4A; KIFC1; NDC80; NEK2; PLK2; RAN; SPAG5; SPC25; STIL; TPX2; TTK; TWF1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | STIL; TPX2; TTK; TWF1 | | | | | | | | | | | | | | | |
| activation of apc/c and apc/c: cdc20 mediated degradation of mitotic proteins | 55 | 13 | 3.96 | BUB1; BUB1B; CCNA2; CCNB1; CDC20; CDK1; MAD2L1; NEK2; PLK1; PSMA5; PSMB6; PTTG1; UBE2C | 0 | 0.00 | | 0 | 0.00 | | 0 | 0.00 | | 0 | 0.00 | | 11 | 5.67 | BUB1; BUB1B; CCNA2; CCNB1; CDC20; CDK1; MAD2L1; NEK2; PLK1; PTTG1; UBE2C |
| atp generation from adp: GO | 36 | 9 | 4.18 | ENO1; GAPDH; HK2; LDHA; OGDHL; PFKFB4; PGAM1; PGK1; TPI1 | 2 | 0.66 | ALDOB; PFKFB1 | 0 | 0.00 | | 0 | 0.00 | | 2. | 1.41 | ALDOC; PFKFB1 | 9 | 7.09 | ENO1; GAPDH; HK2; LDHA; OGDHL; PFKFB4; PGAM1; PGK1; TPI1 |
| regulation of cell cycle g2 m phase transition: GO | 57 | 10 | 2.94 | BLM; CCNA2; CDK1; CENPF; CLSPN; HMGA2; KIF14; NPM1; PLK1; PRKCQ | 1 | 0.21 | FHL1 | 0 | 0.00 | | 0 | 0.00 | | 0 | 0.00 | | 11 | 5.47 | BLM; CCNA2; CDK1; CENPF; FANCI; GTSE1; HMGA2; KIF14; NPM1; PLK1; PRKCQ |
| signal transduction in response to dna damage: GO | 92 | 12 | 2.18 | AURKA; BRCA2; CCNB1; CDK1; CDKN1A; E2F7; FOXM1; NPM1; PCNA; PLK2; | 1 | 0.13 | RPS6KA6 | 0 | 0.00 | | 0 | 0.00 | | 1 | 0.28 | RPS6KA6 | 14 | 4.32 | AURKA; BCL3; BRCA2; CCNB1; CDK1; CDKN1A; E2F1; E2F7; FOXM1; GTSE1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | SFN; TP63 | | | | | | | | | | | | | | | NDRG1; NPM1; PLK2; SFN |
| positive regulation of mitotic cell cycle: GO | 118 | 25 | 3.55 | ANXA1; AURKA; BIRC5; BRCA2; CCNB1; CDC25B; CDC45; CDC6; CDCA5; CDK1; DLGAP5; EIF4EBP1; EPGN; EREG; FBXO5; GEN1; IL1A; IL1B; KIF20B; MAD2L1; PLK1; RANBP1; TGFA; UBE2C; USP2 | 4 | 0.40 | BTC; CYP1A1; EDN3; EGF | 0 | 0.00 | | 1 | 3.54 | IL1B | 3 | 0.65 | EDN3; EGF; FOXA1 | 16 | 3.85 | AURKA; BIRC5; BRCA2; CCNB1; CDC25B; CDC45; CDC6; CDCA5; CDK1; DLGAP5; EIF4EBP1; EREG; MAD2L1; PLK1; TGFA; UBE2C |
| dna replication: GO | 191 | 23 | 2.02 | BLM; BRCA2; CCNE1; CDC25A; CDC45; CDC6; CDK1; CHEK1; CLSPN; DBF4; DTL; EXO1; GINS1; GINS3; MCM10; ORC1; ORC6; PCNA; POLQ; RRM2; | 2 | 0.12 | ADRA2A; EGF | 0 | 0.00 | | 0 | 0.00 | | 2 | 0.27 | ADRA2A; EGF | 21 | 3.12 | BLM; BRCA2; BRIP1; CDC25A; CDC45; CDC6; CDK1; CHEK1; DTL; EXO1; FEN1; GINS1; GINS3; GINS4; MCM2; ORC1; ORC6; POLQ; RRM2; TIMELESS; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | TIMELESS; TOP2A; TYMP | | | | | | | | | | | | | | | TOP2A |
| cell cycle g2 m phase transition: GO | 134 | 18 | 2.25 | AURKA; BIRC5; CCNB1; CCNB2; CDC25A; CDC25B; CDK1; CDKN1A; CHEK1; DYNLL1; FOXM1; HMMR; MELK; NEK2; PKMYT1; PLK1; TPX2; TUBA4A | 3 | 0.26 | BRSK2; PRKAR2B; TUBB4A | 1 | 3.12 | PRKAR2B | 0 | 0.00 | | 3 | 0.57 | BRSK2; CDK14; FBXL7 | 17 | 3.60 | AURKA; BIRC5; CCNB1; CCNB2; CDC25A; CDC25B; CDK1; CDKN1A; CHEK1; FOXM1; HMMR; NEK2; PKMYT1; PLK1; PLK4; TPX2; TUBA4A |
| nuclear chromosome telomeric region: GO | 121 | 19 | 2.63 | BRCA2; CDK1; HIST1H2BB; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L; NLRP2; ORC1; PCNA; PIF1 | 1 | 0.10 | TERT | 0 | 0.00 | | 0 | 0.00 | | 0 | 0.00 | | 16 | 3.75 | BRCA2; CDK1; FEN1; HIST1H2BB; HIST1H3A; HIST1H3C; HIST1H3F; HIST1H3G; HIST1H3H; HIST1H3I; HIST1H3J; HIST1H4I; MCM2; NLRP2; ORC1; PIF1 |
| atr pathway | 39 | 9 | 3.86 | BRCA2; CCNA2; CDC25A; | 2 | 0.61 | PPP2R2B; SSPO | 0 | 0.00 | | 0 | 0.00 | | 0 | 0.00 | | 9 | 6.54 | BRCA2; CCNA2; CDC25A; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | CDC6; CHEK1; CLSPN; PLK1; TIMELESS; YWHAZ | | | | | | | | | | | | | | | CDC6; CHEK1; MCM2; PLK1; TIMELESS; YWHAZ |
| g2 dna damage checkpoint: GO | 30 | 8 | 4.46 | BLM; CCNA2; CDK1; CHEK1; CLSPN; DTL; HMGA2; PLK1 | 1 | 0.39 | PLK5 | 0 | 0.00 | | 0 | 0.00 | | 0 | 0.00 | | 8 | 7.56 | BLM; CCNA2; CDK1; CHEK1; DTL; FANCI; HMGA2; PLK1 |
| runx1 regulates transcription of genes involved in differentiation of hscs | 71 | 16 | 3.77 | H2AFX; H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; HIST1H4L; PSMA5; PSMB6 | 0 | 0.00 | | 0 | 0.00 | | 0 | 0.00 | | 0 | 0.00 | | 12 | 4.79 | H2AFX; H2AFZ; HIST1H2AE; HIST1H2BB; HIST1H2BD; HIST1H2BF; HIST1H2BK; HIST1H2BM; HIST1H3A; HIST1H3I; HIST1H4I; HIST2H2BE |
| nad metabolic process: GO | 49 | 12 | 4.10 | ENO1; GAPDH; HK2; KYNU; LDHA; NAMPT; PFKFB4; PGAM1; PGK1; PNP; TPI1; VCP | 5 | 1.20 | ALDOB; ASPDH; GPD1; HAAO; PFKFB1 | 1 | 8.53 | GPD1 | 0 | 0.00 | | 3 | 1.56 | ALDOC; NMNAT3; PFKFB1 | 10 | 5.79 | ENO1; GAPDH; HK2; LDHA; NAMPT; PFKFB4; PGAM1; PGK1; PNP; TPI1 |
| dna replication dependent nucleosome | 31 | 13 | 7.02 | ASF1B; HIST1H3A; HIST1H3B; | 0 | 0.00 | | 0 | 0.00 | | 0 | 0.00 | | 0 | 0.00 | | 8 | 7.32 | HIST1H3A; HIST1H3C; HIST1H3F; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| organization: GO | | | | HIST1H3C; HIST1H3F; HIST1H3G; HIST1H3H; HIST1H3I; HIST1H3J; HIST1H4I; HIST1H4J; HIST1H4K; HIST1H4L | | | | | | | | | | | | | | | HIST1H3G; HIST1H3H; HIST1H3I; HIST1H3J; HIST1H4I |
| gl/s transition | 98 | 19 | 3.24 | CCNA2; CCNB1; CCNE1; CDC25A; CDC25B; CDC45; CDC6; CDK1; CDKN1A; DBF4; FBXO5; MCM10; ORC1; ORC6; PCNA; PSMA5; PSMB6; RRM2; TK1 | 0 | 0.00 | | 0 | 0.00 | | 0 | 0.00 | | 0 | 0.00 | | 14 | 4.05 | CCNA2; CCNB1; CDC25A; CDC25B; CDC45; CDC6; CDK1; CDKN1A; E2F1; MCM2; ORC1; ORC6; RRM2; TK1 |
| histone phos-phorylation: GO | 23 | 5 | 3.64 | AURKA; CCNB1; CDK1; CHEK1; HMGA2 | 2 | 1.03 | HIPK4; PRKAA2 | 0 | 0.00 | | 0 | 0.00 | | 1 | 1.10 | PRKAA2 | 7 | 8.63 | AURKA; AURKB; CCNB1; CDK1; CHEK1; HMGA2; RPS6KA4 |
| gene silencing: GO | 185 | 21 | 1.90 | H2AFX; H2AFZ; HIST1H2AB; HIST1H2AE; HIST1H2AG; HIST1H2AH; HIST1H2AI; HIST1H2AL; | 5 | 0.32 | HDAC5; HILS1; PIWIL2; TERT; TNP1 | 0 | 0.00 | | 0 | 0.00 | | 0 | 0.00 | | 20 | 3.07 | BEND3; H2AFX; H2AFZ; HIST1H2AB; HIST1H2AE; HIST1H2AG; HIST1H2AH; HIST1H2AI; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L; RAN | | | | | | | | | | | | | | | HIST1H2AL; HIST1H3A; HIST1H3C; HIST1H3F; HIST1H3G; HIST1H3H; HIST1H3I; HIST1H3J; HIST1H4I; HIST2H2AA3; RAN; TDRD9 |
| keratinocyte differentiation: GO | 99 | 32 | 5.41 | ABCA12; ANXA1; CDH3; CERS3; CNFN; CRCT1; CSTA; DSP; EREG; HRNR; IVL; KRT16; KRT17; LCE3A; LCE3D; LCE3E; PRR9; S100A7; SFN; SPRR1A; SPRRB; SPRR2A; SPRR2B; SPRR2D; SPRR2E; SPRR2F; SPRR2G; SPRR3; SPRR4; TGM1; TP63; WNT5A | 6 | 0.72 | DNASE1L2; LCE5A; LOR; PAX6; SCEL; TXNIP | 0 | 0.00 | | 1 | 4.22 | SPRR2D | 4 | 1.03 | ACER1; KRT2; SCEL; TXNIP | 14 | 4.01 | CNFN; CSTA; DSG4; EPHA2; EREG; IVL; LCE3D; LCE3E; SFN; SPRR1A; SPRR1B; SPRR3; TGM1; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| negative regulation of mitotic nuclear division: GO | 32 | 8 | 4.18 | BUB1; BUB1B; CENPF; CHEK1; MAD2L1; PLK1; PTTG1; TTK | 0 | 0.00 | | 0 | 0.00 | | 0 | 0.00 | | 0 | 0.00 | | 8 | 7.09 | BUB1; BUB1B; CENPF; CHEK1; MAD2L1; PLK1; PTTG1; TTK |
| protein depolymerization: GO | 24 | 5 | 3.49 | CFL1; HSPA8; KIF14; KIF18A; KIF2C | 0 | 0.00 | | 0 | 0.00 | | 0 | 0.00 | | 0 | 0.00 | | 7 | 8.27 | CFL1; HSPA8; KIF14; KIF18A; KIF18B; KIF2C; SGK1 |
| condensed nuclear chromosome: GO | 76 | 12 | 2.64 | AURKA; BLM; BUB1; BUB1B; CCNB1; CENPA; CHEK1; H2AFX; NDC80; NEK2; PLK1; RCC1 | 3 | 0.47 | RSPH1; STAG3; SYCP1 | 0 | 0.00 | | 0 | 0.00 | | 2 | 0.67 | ADD3; SYCP3 | 12 | 4.48 | AURKA; AURKB; BLM; BUB1; BUB1B; CCNB1; CENPA; CHEK1; H2AFX; NDC80; NEK2; PLK1 |
| apc/c: cdc20 mediated degradation of mitotic proteins | 54 | 12 | 3.72 | BUB1; BUB1B; CCNA2; CCNB1; CDC20; CDK1; MAD2L1; NEK2; PSMA5; PSMB6; PTTG1; UBE2C | 0 | 0.00 | | 0 | 0.00 | | 0 | 0.00 | | 0 | 0.00 | | 10 | 5.25 | BUB1; BUB1B; CCNA2; CCNB1; CDC20; CDK1; MAD2L1; NEK2; PTTG1; UBE2C |
| negative regulation of chromosome segregation: GO | 25 | 7 | 4.69 | BUB1; BUB1B; CENPF; MAD2L1; PLK1; PTTG1; TTK | 0 | 0.00 | | 0 | 0.00 | | 0 | 0.00 | | 0 | 0.00 | | 7 | 7.94 | BUB1; BUB1B; CENPF; MAD2L1; PLK1; PTTG1; TTK |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| myc activ pathway | 78 | 19 | 4.08 | BIRC5; CCNB1; CCND2; CDC25A; E2F3; EIF2S1; ENO1; FOSL1; GAPDH; HSPA4; LDHA; MMP9; NME1; NPM1; ODC1; RCC1; RUVBL1; SLC2A1; TK1 | 3 | 0.45 | GPAM; KAT2A; TERT | 1 | 5.36 | GPAM | 0 | 0.00 | | 0 | 0.00 | | 12 | 4.36 | BIRC5; CCNB1; CCND2; CDC25A; ENO1; FOSL1; GAPDH; LDHA; NPM1; ODC1; SLC2A1; TK1 |
| cornified envelope: GO | 44 | 21 | 7.99 | ANXA1; CNFN; CRCT1; CSTA; DSP; IVL; LCE3A; LCE3D; LCE3E; PRR9; SPRR1A; SPRR1B; SPRR2A; SPRR2B; SPRR2D; SPRR2E; SPRR2F; SPRR2G; SPRR3; SPRR4; TGM1 | 3 | 0.80 | LCE5A; LOR; SCEL | 0 | 0.00 | | 1 | 9.50 | SPRR2D | 1 | 0.58 | SCEL | 9 | 5.80 | CNFN; CSTA; IVL; LCE3D; LCE3E; SPRR1A; SPRR1B; SPRR3; TGM1 |
| dna double strand break response | 44 | 12 | 4.56 | H2AFX; HIST1H2BB; HIST1H2BF; HIST1H2BH; HIST1H2BK; HIST1H2BM; | 0 | 0.00 | | 0 | 0.00 | | 0 | 0.00 | | 0 | 0.00 | | 9 | 5.80 | H2AFX; HIST1H2BB; HIST1H2BD; HIST1H2BF; HIST1H2BK; HIST1H2BM; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | HIST1H4I; HIST1H4J; HIST1H4K; HIST1H4L; KPNA2; UBE2N | | | | | | | | | | | | | | | HIST1H4I; HIST2H2BE; KPNA2 |
| adp metabolic process: GO | 44 | 9 | 3.42 | ENO1; GAPDH; HK2; LDHA; OGDHL; PFKFB4; PGAM1; PGK1; TPI1 | 2 | 0.54 | ALDOB; PFKFB1 | 0 | 0.00 | | 0 | 0.00 | | 2 | 1.15 | ALDOC; PFKFB1 | 9 | 5.80 | ENO1; GAPDH; HK2; LDHA; OGDHL; PFKFB4; PGAM1; PGK1; TPI1 |
| the role of gtsel in g2/m progression after g2 checkpoint | 55 | 11 | 3.35 | CCNB1; CCNB2; CDK1; CDKN1A; PLK1; PSMA5; PSMB6; TUBA1C; TUBA4A; TUBB2A; TUBB6 | 0 | 0.00 | | 0 | 0.00 | | 0 | 0.00 | | 1 | 0.46 | SLC29A1 | 10 | 5.16 | CCNB1; CCNB2; CDK1; CDKN1A; GTSE1; PLK1; TUBA1C; TUBA4A; TUBB2A; TUBB6 |
| meiotic cell cycle: GO | 164 | 19 | 1.94 | ACTR3; ASPM; AURKA; BRCA2; CDC25B; CKS2; EREG; EXO1; FBXO5; H2AFX; KIF18A; MKI67; MND1; NEK2; PLK1; PTTG1; SMC4; TOP2A; TRIP13 | 5 | 0.36 | PIWIL2; RSPH1; STAG3; SYCP1; WBP2NL | 0 | 0.00 | | 0 | 0.00 | | 1 | 0.15 | SYCP3 | 18 | 3.11 | ASPM; AURKA; BRCA2; CDC25B; CKS2; EREG; EXO1; H2AFX; KIF18A; MKI67; MND1; NEK2; PLK1; PTTG1; SMC4; TDRD9; TOP2A; TRIP13 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| hexose catabolic process: GO | 45 | 10 | 3.72 | ENO1; FUT1; FUT2; GAPDH; HK2: PFKFB4; PGAM1; PGK1; PGM2; TPI1 | 6 | 1.57 | ALDH1A1; ALDOB; FUT9; GALT; PFKFB1; PGM5 | 0 | 0.00 | | 0 | 0.00 | | 3 | 1.69 | ALDOC; PFKFB1; PGM5 | 9 | 5.67 | ENO1; FUT1; FUT2; GAPDH; HK2; PFKFB4; PGAM1; PGK1; TPI1 |
| positive regulation of cell division: GO | 120 | 23 | 3.21 | AURKA; BIRC5; CDC25B; CDC6; CDCA5; DLGAP5; ECT2; EPGN; EREG; FBXO5; IL1A; IL1B; KIF14; KIF20B; KIF23; OSM; PGF; PLK1; RACGAP1; RANBP1; TGFA; UBE2C; WNT5A | 10 | 0.98 | BTC; CXCR5; EDN3; EGF; FGF1; FGF9; NPM2; PDGFD; PIWIL2; PROK1 | 0 | 0.00 | | 2 | 6.96 | IL1B; OSM | 5 | 1.06 | CENPV; EDN3; EGF; FGF2; MDK | 15 | 3.54 | AURKA; AURKB; BIRC5; CDC25B; CDC6; CDCA5; DLGAP5; ECT2; EREG; KIF14; KIF23; PLK1; TGFA; UBE2C; WNT5A |
| signal transduction by p53 class mediator: GO | 120 | 17 | 2.37 | AEN; AURKA; BRCA2; CCNB1; CDK1; CDKN1A; E2F7; FOXM1; GREM1; IFI16; NPM1; PCNA; PERP; PLK2; PYCARD; SFN; TP63 | 5 | 0.49 | NUPR1; RPS6KA6; ZMAT1; ZMAT4; ZNF385B | 0 | 0.00 | | 0 | 0.00 | | 3 | 0.64 | RPS6KA6; ZMAT1; ZNF385D | 15 | 3.54 | AURKA; BCL3; BRCA2; CCNB1; CDK1; CDKN1A; E2F1; E2F7; FOXM1; GTSE1; IFI16; NDRG1; NPM1; PLK2; SFN |
| regulation of transcription involved in g1 s transition of mitotic cell cycle: GO | 26 | 9 | 5.79 | CCNE1; CDC45; CDC6; CDK1; E2F7; FBXO5; ORC1; PCNA; RRM2 | 0 | 0.00 | | 0 | 0.00 | | 0 | 0.00 | | 0 | 0.00 | | 7 | 7.63 | CDC45; CDC6; CDK1; E2F1; E2F7; ORC1; RRM2 |
| regulation of | 56 | 13 | 3.88 | ACP5; | 1 | 0.21 | P2RX7 | 0 | 0.00 | | 0 | 0.00 | | 0 | 0.00 | | 10 | 5.06 | ACP5; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| interleukin 1 production: GO | | | | ANXA1; CCL3; GSTP1; IFI16; IFNG; MEFV; NLRP2; PANX1; PYCARD; TRIM16; WNT5A; ZC3H12A | | | | | | | | | | | | | | | CCL20; GSTP1; IFI16; IL10; MEFV; NLRP2; PANX1; WNT5A; ZC3H12A |
| regulation of cyclin dependent protein kinase activity: GO | 93 | 13 | 2.34 | BLM; CCNA2; CCND2; CDC25A; CDC6; CDK5R1; CDKN1A; CDKN3; CKS2; PKMYT1; PLK1; SFN; UBE2C | 3 | 0.38 | C2orf40; MYOCD; PKD1 | 1 | 4.49 | C2orf40 | 0 | 0.00 | | 0 | 0.00 | | 13 | 3.96 | BLM; CCNA2; CCND2; CDC25A; CDC6; CDK5R1; CDKN1A; CDKN3; CKS2; PKMYT1; PLK1; SFN; UBE2C |
| positive regulation of cell cycle arrest: GO | 81 | 11 | 2.27 | AURKA; CCNB1; CDK1; CDK5R1; CDKN1A; E2F7; HMGA2; NPM1; PCNA; PLK2; SFN | 1 | 0.15 | RNF112 | 0 | 0.00 | | 0 | 0.00 | | 1 | 0.31 | RNF112 | 12 | 4.20 | AURKA; CCNB1; CDK1; CDK5R1; CDKN1A; E2F1; E2F7; GTSE1; HMGA2; NPM1; PLK2; SFN |
| regulation of protein complex disassembly: GO | 198 | 28 | 2.37 | ASPM; AURKA; BIRC5; CAPZA1; CCNB1; CKAP2; EIF5A; EIF5AL1; F2RL1; | 12 | 0.72 | ACTN2; BIRC7; CAPZA3; GAS2L2; GSN; LMOD1; MAP1A; PKD1; SCIN; SLN; | 0 | 0.00 | | 0 | 0.00 | | 4 | 0.51 | CAPZA3; LMOD1; SCIN; SPTBN4 | 20 | 2.86 | ASPM; AURKA; AURKB; BIRC5; CCNB1; KIF11; KIF23; KIF4A; KIFC1; NDC80; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | FBXO5; KIF11; KIF23; KIF4A; MYBL2; NDC80; NEK2; PLK1; PLK2; RACGAP1; RAN; RANBP1; RCC1; SH3BGRL3; SPC25; STIL; TPX2; TTK; TWF1 | | | SPTBN4; TMOD1 | | | | | | | | | | | | NEK2; PLK1; PLK2; RAN; SPAG5; SPC25; STIL; TPX2; TTK; TWF1 |
| nonhomologous end-joining (nhej) | 36 | 11 | 5.11 | H2AFX; HIST1H2BB; HIST1H2BF; HIST1H2BH; HIST1H2BK; HIST1H2BM; HIST1H4I; HIST1H4J; HIST1H4K; HIST1H4L; UBE2N | 0 | 0.00 | | 0 | 0.00 | | 0 | 0.00 | | 0 | 0.00 | | 8 | 6.30 | H2AFX; HIST1H2BB; HIST1H2BD; HIST1H2BF; HIST1H2BK; HIST1H2BM; HIST1H4I; HIST2H2BE |
| glucose catabolic process: GO | 27 | 7 | 4.34 | ENO1; GAPDH; HK2; PFKFB4; PGAM1; PGK1; TPI1 | 2 | 0.87 | ALDOB; PFKFB1 | 0 | 0.00 | | 0 | 0.00 | | 2 | 1.88 | ALDOC; PFKFB1 | 7 | 7.35 | ENO1; GAPDH; HK2; PFKFB4; PGAM1; PGK1; TPI1 |
| defense response to gram positive bacterium: GO | 70 | 14 | 3.35 | ACP5; C10orf99; CAMP; HIST1H2BC; HIST1H2BE; HIST1H2BF; HIST1H2BG; HIST1H2BI; HIST1H2BJ; | 3 | 0.51 | FCN2; P2RX7; SSC5D | 0 | 0.00 | | 0 | 0.00 | | 2 | 0.73 | CTSG; SSC5D | 11 | 4.46 | ACP5; C10orf99; HIST1H2BC; HIST1H2BE; HIST1H2BF; HIST1H2BG; HIST1H2BI; HIST1H2BJ; HIST1H2BK; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline: Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo: Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo: Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | HIST1H2BK; IL6; MYD88; PGLYRP2; RNASE7 | | | | | | | | | | | | | | | HIST2H2BE; MYD88 |
| mhc class ii antigen presentation | 110 | 20 | 3.04 | AP1S3; CAP1; CENPE; CTSB; CTSC; CTSL; DYNLL1; IFI30; KIF11; KIF15; KIF18A; KIF20A; KIF23; KIF2C; KIF4A; RACGAP1; TUBA1C; TUBA4A; TUBB2A; TUBB6 | 3 | 0.32 | CTSF; DNM1; DYNC1I1 | 0 | 0.00 | | 0 | 0.00 | | 1 | 0.23 | DLC1 | 14 | 3.61 | AP1S3; CAP1; CENPE; KIF11; KIF15; KIF18A; KIF20A; KIF23; KIF2C; KIF4A; TUBA1C; TUBA4A; TUBB2A; TUBB6 |
| oxidoreduction coenzyme metabolic process: GO | 97 | 16 | 2.76 | COQ2; ENO1; GAPDH; HK2; HMGCR; KYNU; LDHA; NAMPT; OGDHL; PFKFB4; PGAM1; PGK1; PGM2; PNP; TPI1; VCP | 7 | 0.85 | ALDOB; ASPDH; FMO2; GPD1; HAAO; NOX1; PFKFB1 | 1 | 4.31 | GPD1 | 0 | 0.00 | | 3 | 0.79 | ALDOC; NMNAT3; PFKFB1 | 13 | 3.80 | ENO1; GAPDH; HK2; LDHA; NAMPT; OGDHL; PDSS1; PFKFB4; PGAM1; PGK1; PNP; TKT; TPI1 |
| epidermal cell differentiation: GO | 140 | 33 | 3.94 | ABCA12; ANXA1; CDH3; CERS3; CNFN; CRCT1; CSTA; DSP; | 15 | 1.26 | ATP2B2; CLIC5; DNASE1L2; FA2H; FGFR1; GLI2; LCE5A; LOR; MCOLN3; | 0 | 0.00 | | 1 | 2.98 | SPRR2D | 11 | 2.00 | ACER1; CLIC5; FGFR1; GLI2; KRT2; PDZD7; PTCH1; PTCH2; | 16 | 3.24 | CNFN; CSTA; DSG4; EPHA2; EREG; IVL; LCE3D; LCE3E; SFN; SLC4A7; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | EREG; HRNR; IVL; KRT16; KRT17; LCE3A; LCE3D; LCE3E; PLS3; PRR9; S100A7; SFN; SPRR1A; SPRR1B; SPRR2A; SPRR2B; SPRR2D; SPRR2E; SPRR2F; SPRR2G; SPRR3; SPRR4; TGM1; TP63; WNT5A | | | PAX6; PDZD7; PTCH1; PTCH2; SCEL; TXNIP | | | | | | | | | SCEL; SLITRK6; TXNIP | | | SPRR1A; SPRR1B; SPRR3; TGM1; TMC1; WNT5A |
| g0 and early g1 | 28 | 9 | 5.38 | CCNA2; CCNE1; CDC25A; CDC25B; CDC6; CDK1; MYBL2; PCNA; TOP2A | 0 | 0.00 | | 0 | 0.00 | | 0 | 0.00 | | 0 | 0.00 | | 7 | 7.09 | CCNA2; CDC25A; CDC25B; CDC6; CDK1; E2F1; TOP2A |
| microtubule associated complex: GO | 142 | 16 | 1.89 | AURKA; BIRC5; CDCA8; CENPE; DYNLL1; KIF11; KIF14; KIF15; KIF18A; KIF20A; KIF20B; KIF23; KIF2C; | 9 | 0.75 | CCDC114; DCX; DNAH11; DNAH6; DYNCII1; KIFIA; KIFC2; MAPIA; MAPT | 0 | 0.00 | | 0 | 0.00 | | 2 | 0.36 | CCDC114; MAPT | 16 | 3.20 | AURKA; AURKB; BIRC5; CDCA8; CENPE; KIF11; KIF14; KIF15; KIF18A; KIF18B; KIF20A; KIF23; KIF2C; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | KIF4A; LRP8; MEFV | | | | | | | | | | | | | | | KIF4A; KIFC1; MEFV |
| keratinization: GO | 49 | 22 | 7.51 | ABCA12; CDH3; CNFN; HRNR; IVL; KRT16; KRT17; LCE3A; LCE3D; LCE3E; SFN; SPRR1A; SPRR1B; SPRR2A; SPRR2B; SPRR2D; SPRR2E; SPRR2F; SPRR2G; SPRR3; SPRR4; TGM1 | 2 | 0.48 | LCE5A; LOR | 0 | 0.00 | | 1 | 8.53 | SPRR2D | 1 | 0.52 | KRT2 | 9 | 5.21 | CNFN; IVL; LCE3D; LCE3E; SFN; SPRR1A; SPRR1B; SPRR3; TGM1 |
| regulation of gene silencing: GO | 49 | 11 | 3.76 | CDC45; HIST1H3A; HIST1H3B; HIST1H3C; HIST1H3F; HIST1H3G; HIST1H3H; HIST1H3I; HIST1H3J; UHRF1; ZC3H12A | 2 | 0.48 | TERT; TET1 | 0 | 0.00 | | 0 | 0.00 | | 2 | 1.04 | ESRI; TET1 | 9 | 5.21 | CDC45; HIST1H3A; HIST1H3C; HIST1H3F; HIST1H3G; HIST1H3H; HIST1H3I; HIST1H3J; ZC3H12A |
| activation of atr in response to replication stress | 39 | 10 | 4.29 | CDC25A; CDC25B; CDC45; CDC6; CHEK1; CLSPN; DBF4; | 0 | 0.00 | | 0 | 0.00 | | 0 | 0.00 | | 0 | 0.00 | | 8 | 5.82 | CDC25A; CDC25B; CDC45; CDC6; CHEK1; MCM2; ORC1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline: Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo: Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo: Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | MCM10; ORC1; ORC6 | | | | | | | | | | | | | | | ORC6 |
| mitotic spindle assembly: GO | 39 | 8 | 3.43 | BIRC5; KIF11; KIF23; KIF4A; MYBL2; NEK2; RACGAP1; TPX2 | 1 | 0.30 | BIRC7 | 0 | 0.00 | | 0 | 0.00 | | 0 | 0.00 | | 8 | 5.82 | AURKB; BIRC5; KIF11; KIF23; KIF4A; KIFC1; NEK2; TPX2 |
| positive regulation of gene expression epigenetic: GO | 75 | 15 | 3.35 | ACTB; CHEK1; DDX21; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L | 2 | 0.31 | KAT2A; TET1 | 0 | 0.00 | | 0 | 0.00 | | 1 | 0.34 | TET1 | 11 | 4.16 | ACTB; CHEK1; DDX21; HIST1H3A; HIST1H3C; HIST1H3F; HIST1H3G; HIST1H3H; HIST1H3I; HIST1H3J; HIST1H4I |
| recycling pathway of 11 | 40 | 7 | 2.93 | ACTB; KIF4A; MSN; TUBA1C; TUBA4A; TUBB2A; TUBB6 | 2 | 0.59 | DNM1; RPS6KA6 | 0 | 0.00 | | 0 | 0.00 | | 1 | 0.64 | RPS6KA6 | 8 | 5.67 | ACTB; KIF4A; MSN; RPS6KA4; TUBA1C; TUBA4A; TUBB2A; TUBB6 |
| regulation of cell cycle arrest: GO | 102 | 12 | 1.97 | AURKA; CCNB1; CDK1; CDK5R1; CDKN1A; E2F7; FOXM1; HMGA2; NPM1; PCNA; PLK2; | 3 | 0.35 | FOXE3; MLXIPL; RNF112 | 0 | 0.00 | | 0 | 0.00 | | 1 | 0.25 | RNF112 | 13 | 3.61 | AURKA; CCNB1; CDK1; CDK5R1; CDKN1A; E2F1; E2F7; FOXM1; GTSE1; HMGA2; NPM1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | SFN | | | | | | | | | | | | | | | PLK2; SFN |
| mitotic spindle: GO | 51 | 12 | 3.94 | ASPM; AURKA; CDK1; CENPE; DYNLL1; ECT2; FAM83D; KIF18A; KIF20B; KIF23; MAD2L1; RACGAP1 | 2 | 0.46 | KAT2A; PKHD1 | 0 | 0.00 | | 0 | 0.00 | | 1 | 0.50 | MAK | 9 | 5.00 | ASPM; AURKA; CDK1; CENPE; ECT2; KIF18A; KIF23; MAD2L1; SPAG5 |
| dna dependent dna replication: GO | 89 | 12 | 2.26 | BLM; BRCA2; CCNE1; CDC45; CDC6; GINS1; GINS3; MCM10; ORC1; PCNA; POLQ; TOP2A | 0 | 0.00 | | 0 | 0.00 | | 0 | 0.00 | | 0 | 0.00 | | 12 | 3.82 | BLM; BRCA2; CDC45; CDC6; FEN1; GINS1; GINS3; GINS4; MCM2; ORC1; POLQ; TOP2A |
| anaphase promoting complex dependent catabolic process: GO | 76 | 15 | 3.30 | AURKA; BUB1B; CCNB1; CDC20; CDK1; MAD2L1; PLK1; PSMA4; PSMA5; PSMB6; PSMD1; PSME3; PTTG1; UBE2C; UBE2S | 0 | 0.00 | | 0 | 0.00 | | 0 | 0.00 | | 0 | 0.00 | | 11 | 4.10 | AURKA; AURKB; BUB1B; CCNB1; CDC20; CDK1; MAD2L1; PLK1; PTTG1; UBE2C; UBE2S |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| microtubule motor activity: GO | 76 | 10 | 2.20 | CENPE; KIF11; KIF14; KIF15; KIF18A; KIF20A; KIF20B; KIF23; KIF2C; KIF4A | 5 | 0.78 | DNAH11; DNAH6; DYNC1I1; KIF1A; KIFC2 | 0 | 0.00 | | 0 | 0.00 | | 0 | 0.00 | | 11 | 4.10 | CENPE; KIF11; KIF14; KIF15; KIF18A; KIF18B; KIF20A; KIF23; KIF2C; KIF4A; KIFC1 |
| intra-golgi and retrograde golgi-to-er traffic | 133 | 16 | 2.01 | CAP1; CENPE; DYNLL1; KIF11; KIF15; KIF18A; KIF20A; KIF20B; KIF23; KIF2C; KIF4A; RACGAP1; TUBA1C; TUBA4A; TUBB2A; TUBB6 | 2 | 0.18 | KIFC2; RHOBTB3 | 0 | 0.00 | | 0 | 0.00 | | 2 | 0.38 | DLC1; RHOBTB3 | 15 | 3.20 | CAP1; CENPE; KIF11; KIF15; KIF18A; KIF18B; KIF20A; KIF23; KIF2C; KIF4A; KIFC1; TUBA1C; TUBA4A; TUBB2A; TUBB6 |
| transcriptional regulation by runx1 | 135 | 26 | 3.22 | CBX2; CCND2; CSF2; CTLA4; CTSL; H2AFX; H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; | 3 | 0.26 | GPAM; LIFR; MYL9 | 1 | 3.10 | GPAM | 1 | 3.10 | IL2RA | 0 | 0.00 | | 15 | 3.15 | CBX2; CCND2; H2AFX; H2AFZ; HIST1H2AE; HIST1H2BB; HIST1H2BD; HIST1H2BF; HIST1H2BK; HIST1H2BM; HIST1H3A; HIST1H3I; HIST1H4I; HIST2H2BE; SOCS3 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | HIST1H4K; HIST1H4L; IFNG; IL2RA; NR4A3; PSMA5; PSMB6; SERPINB1; SOCS3 | | | | | | | | | | | | | | | |
| s phase | 135 | 18 | 2.23 | CCNA2; CCNE1; CDC25A; CDC25B; CDC45; CDC6; CDCA5; CDKN1A; ESCO2; GINS1; GINS3; ORC1; ORC6; PCNA; PSMA4; PSMA5; PSMB6; PSMD1 | 0 | 0.00 | | 0 | 0.00 | | 0 | 0.00 | | 0 | 0.00 | | 15 | 3.15 | CCNA2; CDC25A; CDC25B; CDC45; CDC6; CDCA5; CDKN1A; E2F1; FEN1; GINS1; GINS3; GINS4; MCM2; ORC1; ORC6 |
| monosaccharide catabolic process: GO | 54 | 10 | 3.10 | ENO1; FUT1; FUT2; GAPDH; HK2; PFKFB4; PGAM1; PGK1; PGM2; TPI1 | 6 | 1.31 | ALDH1A1; ALDOB; FUT9; GALT; PFKFB1; PGM5 | 0 | 0.00 | | 0 | 0.00 | | 3 | 1.41 | ALDOC; PFKFB1; PGM5 | 9 | 4.73 | ENO1; FUT1; FUT2; GAPDH; HK2; PFKFB4; PGAM1; PGK1; TPI1 |
| tap63 pathway | 54 | 10 | 3.10 | AEN; CDKN1A; CLCA2; ITGA3; PERP; PLK1; S100A2; SERPINB5; | 1 | 0.22 | SSPO | 0 | 0.00 | | 0 | 0.00 | | 0 | 0.00 | | 9 | 4.73 | CDKN1A; CLCA2; IGFBP3; ITGA3; ITGB4; PLK1; S100A2; SERPINB5; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | TP63; YWHAQ | | | | | | | | | | | | | | | YWHAQ |
| cellcycle pathway | 23 | 6 | 4.37 | CCNB1; CCND2; CCNE1; CDC25A; CDK1; CDKN1A | 0 | 0.00 | | 0 | 0.00 | | 0 | 0.00 | | 0 | 0.00 | | 6 | 7.40 | CCNB1; CCND2; CDC25A; CDK1; CDKN1A; E2F1 |
| cyclins and cell cycle regulation | 23 | 6 | 4.37 | CCNB1; CCND2; CCNE1; CDC25A; CDK1; CDKN1A | 0 | 0.00 | | 0 | 0.00 | | 0 | 0.00 | | 0 | 0.00 | | 6 | 7.40 | CCNB1; CCND2; CDC25A; CDK1; CDKN1A; E2F1 |
| recruitment and atm-mediated phosphorylation of repair and signaling proteins at dna double strand breaks | 43 | 11 | 4.28 | H2AFX; HIST1H2BB; HIST1H2BF; HIST1H2BH; HIST1H2BK; HIST1H2BM; HIST1H4I; HIST1H4J; HIST1H4K; HIST1H4L; UBE2N | 0 | 0.00 | | 0 | 0.00 | | 0 | 0.00 | | 00 | 0.00 | | 8 | 5.28 | H2AFX; HIST1H2BB; HIST1H2BD; HIST1H2BF; HIST1H2BK; HIST1H2BM; HIST1H4I; HIST2H2BE |
| negative regulation of nuclear division: GO | 43 | 10 | 3.89 | BUB1; BUB1B; CENPF; CHEK1; FBXO5; MAD2L1; OSM; PLK1; PTTG1; TTK | 1 | 0.27 | LIF | 0 | 0.00 | | 1 | 9.72 | OSM | 0 | 0.00 | | 8 | 5.28 | BUB1; BUB1B; CENPF; CHEK1; MAD2L1; PLK1; PTTG1; TTK |
| spindle assembly: GO | 67 | 12 | 3.00 | ASPM; AURKA; BIRC5; FBXO5; KIF11; KIF23; KIF4A; MYBL2; NEK2; | 1 | 0.18 | BIRC7 | 0 | 0.00 | | 0 | 0.00 | | 0 | 0.00 | | 10 | 4.23 | ASPM; AURKA; AURKB; BIRC5; KIF11; KIF23; KIF4A; KIFC1; NEK2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | RACGAP1; RCC1; TPX2 | | | | | | | | | | | | | | | TPX2 |
| peptide cross linking: GO | 55 | 21 | 6.39 | ANXA1; CRCT1; CSTA; DSP; IVL; LCE3A; LCE3D; LCE3E; PRR9; SPRR1A; SPRR1B; SPRR2A; SPRR2B; SPRR2D; SPRR2E; SPRR2F; SPRR2G; SPRR3; SPRR4; TGM1; TGM2 | 4 | 0.86 | EPB42; LCE5A; LOR; NDNF | 0 | 0.00 | | 1 | 7.60 | SPRR2D | 2 | 0.92 | DCN; NDNF | 9 | 4.64 | CSTA; IVL; LCE3D; LCE3E; SPRR1A; SPRR1B; SPRR3; TGM1; TGM2 |
| nadh metabolic process: GO | 33 | 8 | 4.06 | ENO1; GAPDH; HK2; PFKFB4; PGAM1; PGK1; TPI1; VCP | 3 | 1.07 | ALDOB; GPD1; PFKFB1 | 1 | 12.66 | GPD1 | 0 | 0.00 | | 2 | 1.54 | ALDOC; PFKFB1 | 7 | 6.02 | ENO1; GAPDH; HK2; PFKFB4; PGAM1; PGK1; TPI1 |
| centrosome cycle: GO | 44 | 7 | 2.66 | AURKA; BRCA2; CDK1; KIF11; NEK2; NPM1; STIL | 0 | 0.00 | | 0 | 0.00 | | 0 | 0.00 | | 0 | 0.00 | | 8 | 5.16 | AURKA; BRCA2; CDK1; KIF11; NEK2; NPM1; PLK4; STIL |
| nucleotide phosphorylation: GO | 56 | 11 | 3.29 | CMPK2; ENO1; GAPDH; HK2; LDHA; NME1; OGDHL; PFKFB4; PGAM1; PGK1; TPI1 | 2 | 0.42 | ALDOB; PFKFB1 | 0 | 0.00 | | 0 | 0.00 | | 3 | 1.36 | AK7; ALDOC; PFKFB1 | 9 | 4.56 | ENO1; GAPDH; HK2; LDHA; OGDHL; PFKFB4; PGAM1; PGK1; TPI1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| aurka activation by tpx2 | 56 | 9 | 2.69 | AURKA; CDK1; DYNLL1; HMMR; NEK2; PLK1; TPX2; TUBA1C; TUBA4A | 2 | 0.42 | MAST1; PRKAR2B | 1 | 7.46 | PRKAR2B | 0 | 0.00 | | 1 | 0.45 | DLC1 | 9 | 4.56 | AURKA; CDK1; HMMR; NEK2; PLK1; PLK4; TPX2; TUBA1C; TUBA4A |
| response to corticosteroid: GO | 172 | 24 | 2.33 | ADCYAP1; ALPL; ANXA1; ANXA3; AREG; CCNE1; CDKN1A; FOSL1; GSTP1; HIF1A; IL1B; IL1RN; IL22; IL6; NEFL; PTAFR; PTGS2; RAN; SDC1; SOCS3; TH; TK1; UGT1A1; WNT5A | 15 | 1.03 | ABCA3; ACSBG1; ADIPOQ; ALDOB; BCL2; C3; CALCR; CDO1; HMGCS2; MSTN; NTRK3; PFKFB1; SCGB1A1; SLIT2; SLIT3 | 2 | 4.86 | ADIPOQ; HSD11B2 | 2 | 4.86 | ANXA3; IL1B | 10 | 1.48 | ABCA3; BCL2; C3; CTGF; HMGCS2; MDK; PFKFB1; SLC18A2; SLIT2; SLIT3 | 17 | 2.80 | AREG; CDKN1A; FOSL1; GSTP1; HIF1A; IL10; IL22; JUNB; PTAFR; PTGS2; RAN; SGK1; SOCS3; TH; TK1; UCN2; WNT5A |
| deubiquitination | 156 | 22 | 2.36 | ACTB; CAP1; CCNA2; CDC20; CDC25A; CDC25B; CDK1; CLSPN; H2AFX; HIF1A; HIST1H2AE; HIST1H2BB; HIST1H2BF; HIST1H2BH; HIST1H2BK; | 1 | 0.08 | AR | 0 | 0.00 | | 0 | 0.00 | | 0 | 0.00 | | 16 | 2.91 | ACTB; CAP1; CCNA2; CDC20; CDC25A; CDC25B; CDK1; H2AFX; HIF1A; HIST1H2AE; HIST1H2BB; HIST1H2BD; HIST1H2BF; HIST1H2BK; HIST1H2BM; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | HIST1H2BM; PSMA5; PSMB6; RUVBL1; TGFBR1; USP2; YOD1 | | | | | | | | | | | | | | | HIST2H2BE |
| g1 dna damage checkpoint: GO | 69 | 10 | 2.43 | AURKA; CCNB1; CDK1; CDKN1A; E2F7; NPM1; PCNA; PLK2; SFN; TP63 | 0 | 0.00 | | 0 | 0.00 | | 0 | 0.00 | | 0 | 0.00 | | 10 | 4.11 | AURKA; CCNB1; CDK1; CDKN1A; E2F1; E2F7; GTSE1; NPM1; PLK2; SFN |
| positive regulation of nuclear division: GO | 57 | 14 | 4.11 | AURKA; BIRC5; CDCA5; DLGAP5; EPGN; EREG; FBXO5; IL1A; IL1B; PLK1; RANBP1; TGFA; UBE2C; WNT5A | 5 | 1.03 | BTC; EDN3; EGF; NPM2; PIWIL2 | 0 | 0.00 | | 1 | 7.33 | IL1B | 2 | 0.89 | EDN3; EGF | 9 | 4.48 | AURKA; BIRC5; CDCA5; DLGAP5; EREG; PLK1; TGFA; UBE2C; WNT5A |
| regulation of apc/c activators between g1/s and early anaphase | 57 | 12 | 3.52 | BUB1; BUB1B; CCNA2; CCNB1; CDC20; CDK1; FBXO5; MAD2L1; PLK1; PSMA5; PSMB6; UBE2C | 0 | 0.00 | | 0 | 0.00 | | 0 | 0.00 | | 0 | 0.00 | | 9 | 4.48 | BUB1; BUB1B; CCNA2; CCNB1; CDC20; CDK1; MAD2L1; PLK1; UBE2C |
| positive regulation of mitotic nuclear division: GO | 46 | 13 | 4.73 | AURKA; BIRC5; CDCA5; DLGAP5; | 3 | 0.77 | BTC; EDN3; EGF | 0 | 0.00 | | 1 | 9.08 | IL1B | 2 | 1.10 | EDN3; EGF | 8 | 4.93 | AURKA; BIRC5; CDCA5; DLGAP5; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | EPGN; EREG; FBXO5; IL1A; IL1B; PLK1; RANBP1; TGFA; UBE2C | | | | | | | | | | | | | | | EREG; PLK1; TGFA; UBE2C |
| regulation of interleukin 1 beta production: GO | 46 | 12 | 4.37 | ACP5; CCL3; GSTP1; IFI16; IFNG; MEFV; NLRP2; PANX1; PYCARD; TRIM16; WNT5A; ZC3H12A | 1 | 0.26 | P2RX7 | 0 | 0.00 | | 0 | 0.00 | | 0 | 0.00 | | 8 | 4.93 | ACP5; GSTP1; IFI16; MEFV; NLRP2; PANX1; WNT5A; ZC3H12A |
| structural constituent of cytoskeleton: GO | 99 | 20 | 3.38 | ACTB; ACTR3; ARPC3; BFSP1; DSP; INA; KRT14; KRT16; KRT17; KRT5; KRT6B; KRT9; MSN; NDC80; NEFL; NEFM; TUBA1C; TUBA4A; TUBB2A; TUBB6 | 16 | 1.91 | ACTA1; ACTL7A; ANK2; DES; DMD; EPB42; KRT15; KRT31; LOR; MAPT; SORBS2; SPTBN4; SYNM; TLN2; TPM1; TUBB4A | 0 | 0.00 | | 0 | 0.00 | | 7 | 1.80 | ADD3; KRT2; KRT20; MAPT; SORBS2; SPTBN4; TLN2 | 12 | 3.44 | ACTB; AGRN; BFSP1; INA; KRT5; MSN; NDC80; NEFM; TUBA1C; TUBA4A; TUBB2A; TUBB6 |
| ub-specific processing proteases | 114 | 18 | 2.64 | CCNA2; CDC20; CDC25A; CDC25B; CLSPN; H2AFX; HIF1A; HIST1H2AE; HIST1H2BB; HIST1H2BF; | 1 | 0.10 | AR | 0 | 0.00 | | 0 | 0.00 | | 0 | 0.00 | | 13 | 3.23 | CCNA2; CDC20; CDC25A; CDC25B; H2AFX; HIF1A; HIST1H2AE; HIST1H2BB; HIST1H2BD; HIST1H2BF; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | HIST1H2BH; HIST1H2BK; HIST1H2BM; PSMA5; PSMB6; RUVBL1; TGFBR1; USP2 | | | | | | | | | | | | | | | HIST1H2BK; HIST1H2BM; HIST2H2BE |
| regulation of cytokinesis: GO | 59 | 10 | 2.84 | AURKA; BRCA2; CDC25B; CDC6; E2F7; ECT2; KIF14; KIF20B; KIF23; RACGAP1 | 1 | 0.20 | CXCR5 | 0 | 0.00 | | 0 | 0.00 | | 1 | 0.43 | CENPV | 9 | 4.33 | AURKA; AURKB; BRCA2; CDC25B; CDC6; E2F7; ECT2; KIF14; KIF23 |
| cellular response to radiation: GO | 132 | 16 | 2.03 | BAK1; BLM; CDC25A; CDKN1A; CHEK1; CNGB1; ECT2; EIF2S1; H2AFX; HIF1A; HYAL3; IFI16; PBK; PCNA; PTGS2; TP63 | 5 | 0.45 | CRIP1; CRY2; CRYAB; MFAP4; TRPM1 | 1 | 3.17 | CRYAB | 0 | 0.00 | | 3 | 0.58 | CRIP1; CRY2; TSPYL5 | 14 | 3.01 | AURKB; BAK1; BLM; CDC25A; CDKN1A; CHEK1; ECT2; H2AFX; HIF1A; IFI16; PBK; PTGS2; RAD51AP1; SNAI2 |
| meiotic cell cycle process: GO | 132 | 15 | 1.90 | ASPM; AURKA; BRCA2; CDC25B; CKS2; EREG; FBXO5; KIF18A; MKI67; PLK1; PTTG1; SMC4; | 2 | 0.18 | STAG3; SYCP1 | 0 | 0.00 | | 0 | 0.00 | | 1 | 0.19 | SYCP3 | 14 | 3.01 | ASPM; AURKA; BRCA2; CDC25B; CKS2; EREG; KIF18A; MKI67; PLK1; PTTG1; SMC4; TDRD9; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | TOP2A; TRIP13 | | | | | | | | | | | | | | | TOP2A; TRIP13 |
| protein localization to chromosome: GO | 37 | 7 | 3.17 | BRCA2; BUB1B; CDK1; CENPA; ESCO2; HIST1H1B; PLK1 | 1 | 0.32 | TERT | 0 | 0.00 | | 0 | 0.00 | | 1 | 0.69 | ESR1 | 7 | 5.36 | AURKB; BRCA2; BUB1B; CDK1; CENPA; HIST1H1B; PLK1 |
| e2f pathway | 74 | 15 | 3.39 | CCNA2; CCNE1; CDC25A; CDC6; CDK1; CDKN1A; E2F3; E2F7; MYBL2; ORC1; PLAU; RANBP1; RRM2; SERPINE1; TK1 | 4 | 0.64 | CES1; CES1P1; CES4A; KAT2A | 0 | 0.00 | | 1 | 5.65 | SERPINE1 | 2 | 0.69 | CES1; CES4A | 10 | 3.83 | CCNA2; CDC25A; CDC6; CDK1; CDKN1A; E2F1; E2F7; ORC1; RRM2; TK1 |
| pyruvate metabolic process: GO | 61 | 12 | 3.29 | ENO1; GAPDH; GLO1; HK2; LDHA; NR4A3; OGDHL; PFKFB4; PGAM1; PGK1; SLC16A1; TPI1 | 7 | 1.35 | ACOT12; ALDOB; CDO1; HOGA1; PCK1; PFKFB1; SLC16A8 | 0 | 0.00 | | 0 | 0.00 | | 2 | 0.83 | ALDOC; PFKFB1 | 9 | 4.18 | ENO1; GAPDH; HK2; LDHA; OGDHL; PFKFB4; PGAM1; PGK1; TPI1 |
| ribonucleoside diphosphate metabolic process: GO | 61 | 9 | 2.47 | ENO1; GAPDH; HK2; LDHA; OGDHL; PFKFB4; PGAM1; PGK1; TPI1 | 4 | 0.77 | ALDOB; DLG2; MPP2; PFKFB1 | 0 | 0.00 | | 0 | 0.00 | | 4 | 1.67 | ALDOC; DLG2; MPP2; PFKFB1 | 9 | 4.18 | ENO1; GAPDH; HK2; LDHA; OGDHL; PFKFB4; PGAM1; PGK1; TPI1 |
| tcf dependent signaling in | 118 | 19 | 2.69 | CSNK1A1; H2AFX; | 3 | 0.30 | DKK1; FZD4; LGR5 | 0 | 0.00 | | 0 | 0.00 | | 1 | 0.22 | LGR5 | 13 | 3.12 | H2AFX; H2AFZ; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| response to wnt | | | | H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; HIST1H4L; PSMA5; PSMB6; RUVBL1; WNT5A | | | | | | | | | | | | | | | HIST1H2AE; HIST1H2BB; HIST1H2BD; HIST1H2BF; HIST1H2BK; HIST1H2BM; HIST1H3A; HIST1H3I; HIST1H4I; HIST2H2BE; WNT5A |
| cytoskeleton dependent cytokinesis: GO | 38 | 9 | 3.96 | ACTR3; ANLN; CEP55; CKAP2; KIF20A; KIF23; KIF4A; PLK1; RACGAP1 | 0 | 0.00 | | 0 | 0.00 | | 0 | 0.00 | | 0 | 0.00 | | 7 | 5.22 | ANLN; AURKB; CEP55; KIF20A; KIF23; KIF4A; PLK1 |
| regulation of centrosome cycle: GO | 38 | 8 | 3.52 | AURKA; CHEK1; GEN1; KIF11; NEK2; NPM1; PLK2; RANBP1 | 1 | 0.31 | PKHD 1 | 0 | 0.00 | | 0 | 0.00 | | 0 | 0.00 | | 7 | 5.22 | AURKA; CHEK1; KIF11; NEK2; NPM1; PLK2; PLK4 |
| response to uv: GO | 120 | 15 | 2.09 | BAK1; BRCA2; CDC25A; CDKN1A; CHEK1; DTL; EIF2S1; HYAL3; IL12B; IVL; PBK; PCNA; PTGS2; | 4 | 0.39 | BCL2; CRIP1; ELANE; MFAP4 | 0 | 0.00 | | 0 | 0.00 | | 3 | 0.64 | BCL2; CRIP1; ELANE | 13 | 3.07 | AURKB; BAK1; BCL3; BRCA2; CDC25A; CDKN1A; CHEK1; DTL; FEN1; IVL; PBK; PTGS2; SERPINB13 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | A: Fold Change (FC) Up | A: Up-regulated Genes | A: Down-regulated | A: Fold Change (FC) | A: Down-regulated Genes | B. Differentially expressed genes significant in the baseline vs week 12 comparison only in the placebo: Up-regulated | B: Fold Change (FC) Up | B: Up-regulated Genes | B: Down-regulated | B: Fold Change (FC) | B: Down-regulated Genes | C. Differentially expressed genes significant in the baseline vs week 12 comparison only in the nemo: Up-regulated | C: Fold Change (FC) Up | C: Up-regulated Genes | C: Down-regulated | C: Fold Change (FC) | C: Down-regulated Genes |
|---|---|---|---|---|---|---|---|---|---|---|---|---|---|---|---|---|---|---|---|
| | | | | SERPINB13; TP63 | | | | | | | | | | | | | | | |
| chromatin modifying enzymes | 121 | 16 | 2.21 | ACTB; H2AFX; H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; HIST1H4L; RUVBL1 | 0 | 0.00 | | 0 | 0.00 | | 0 | 0.00 | | 0 | 0.00 | | 13 | 3.05 | ACTB; H2AFX; H2AFZ; HIST1H2AE; HIST1H2BB; HIST1H2BD; HIST1H2BF; HIST1H2BK; HIST1H2BM; HIST1H3A; HIST1H3I; HIST1H4I; HIST2H2BE |
| glycolysis | 51 | 10 | 3.28 | ENO1; GAPDH; GK; HK2: PFKFB4; PGAM1; PGK1; PKM; TPI1; TPI1P1 | 2 | 0.46 | ALDOB; PFKFB1 | 0 | 0.00 | | 0 | 0.00 | | 2 | 1.00 | ALDOC; PFKFB1 | 8 | 4.45 | ENO1; GAPDH; HK2; PFKFB4; PGAM1; PGK1; PKM; TPI1 |
| regulation of plk1 activity at g2/m transition | 64 | 9 | 2.35 | AURKA; CCNB1; CCNB2; CDK1; DYNLL1; NEK2; PLK1; TUBA1C; TUBA4A | 2 | 0.37 | MAST1; PRKAR2B | 1 | 6.53 | PRKAR2B | 0 | 0.00 | | 1 | 0.40 | DLC1 | 9 | 3.99 | AURKA; CCNB1; CCNB2; CDK1; NEK2; PLK1; PLK4; TUBA1C; TUBA4A |
| oocyte meiosis | 107 | 16 | 2.50 | AURKA; BUB1; CALML3; CALML5; CCNB1; CCNB2; CCNE1; CDC20; | 13 | 1.43 | ADCY2; ADCY5; ADCY6; ADCY8; AR; CALML6; CAMK2A; CAMK2B; CHP2; | 0 | 0.00 | | 0 | 0.00 | | 5 | 1.19 | CHP2; CPEB1; PGR; PLCZ1; RPS6KA6 | 12 | 3.18 | AURKA; BUB1; CCNB1; CCNB2; CDC20; CDK1; MAD2L1; PKMYT1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | CDK1; FBXO5; MAD2L1; PKMYT1; PLK1; PTTG1; YWHAQ; YWHAZ | | | CPEB1; PGR; RPS6KA6; STAG3 | | | | | | | | | | | | PLK1; PTTG1; YWHAQ; YWHAZ |
| e3 ubiquitin ligases ubiquitinate target proteins | 29 | 7 | 4.04 | HIST1H2BB; HIST1H2BF; HIST1H2BH; HIST1H2BK; HIST1H2BM; PCNA; UBE2N | 0 | 0.00 | | 0 | 0.00 | | 0 | 0.00 | | 0 | 0.00 | | 6 | 5.87 | HIST1H2BB; HIST1H2BD; HIST1H2BF; HIST1H2BK; HIST1H2BM; HIST2H2BE |
| negative regulation of reactive oxygen species metabolic process: GO | 40 | 6 | 2.51 | ACP5; HIF1A; HK2; MMP3; VDAC1; ZC3H12A | 6 | 1.77 | BCL2; CD34; CRYAB; PLIN5; PON3; PTGIS | 1 | 10.45 | CRYAB | 0 | 0.00 | | 5 | 3.18 | BCL2; CD34; MYCN; PON3; SLC18A2 | 7 | 4.96 | ACP5; HIF1A; HK2; IL10; MMP3; VDAC1; ZC3H12A |
| cell substrate junction assembly: GO | 40 | 5 | 2.09 | ITGA6; KRT14; KRT5; LAMB3; RHOD | 5 | 1.47 | ACTN2; ARHGAP6; BCL2; SORBS1; TNS1 | 0 | 0.00 | | 0 | 0.00 | | 2 | 1.27 | BCL2; DLC1 | 7 | 4.96 | ACTN1; COL17A1; ITGA6; ITGB4; KRT5; LAMB3; RHOD |
| apc: cdc20 mediated degradation of cell cycle proteins prior to satisfation of the cell cycle checkpoint | 52 | 10 | 3.22 | BUB1; BUB1B; CCNA2; CDC20; CDK1; MAD2L1; NEK2; PSMA5; PSMB6; UBE2C | 0 | 0.00 | | 0 | 0.00 | | 0 | 0.00 | | 0 | 0.00 | | 8 | 4.36 | BUB1; BUB1B; CCNA2; CDC20; CDK1; MAD2L1; NEK2; UBE2C |
| negative regulation of cell | 93 | 11 | 1.98 | AURKA; C10orf99; CCNB1; | 5 | 0.63 | BCL2; DACT1; FHL1; | 0 | 0.00 | | 0 | 0.00 | | 3 | 0.82 | BCL2; DACT1; SUSD2 | 11 | 3.35 | AURKA; C10orf99; CCNB1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| cycle g1 s phase transition: GO | | | | CDK1; CDKN1A; E2F7; NPM1; PCNA; PLK2; SFN; TP63 | | | KANK2; SUSD2 | | | | | | | | | | | | CDK1; CDKN1A; E2F1; E2F7; GTSE1; NPM1; PLK2; SFN |
| centriole: GO | 93 | 10 | 1.80 | AURKA; BIRC5; CEP55; HSPA6; PLA2G3; PLK2; POC1A; RAN; STIL; TOP2A | 5 | 0.63 | AGBL4; CCDC146; CROCC; DZIP1L; TSKS | 0 | 0.00 | | 0 | 0.00 | | 0 | 0.00 | | 11 | 3.35 | AURKA; BIRC5; CEP19; CEP55; PLA2G3; PLK2; PLK4; POC1A; RAN; STIL; TOP2A |
| nucleoside diphosphate metabolic process: GO | 79 | 12 | 2.54 | CMPK2; ENO1; GAPDH; HK2; LDHA; NME1; OGDHL; PFKFB4; PGAM1; PGK1; RRM2; TPI1 | 5 | 0.75 | ALDOB; DLG2; ENTPD8; MPP2; PFKFB1 | 0 | 0.00 | | 0 | 0.00 | | 5 | 1.61 | AK7; ALDOC; DLG2; MPP2; PFKFB1 | 10 | 3.59 | ENO1; GAPDH; HK2; LDHA; OGDHL; PFKFB4; PGAM1; PGK1; RRM2; TPI1 |
| microtubule binding: GO | 190 | 21 | 1.85 | BIRC5; CENPE; FAM83D; GAPDH; HOOK1; KIF11; KIF14; KIF15; KIF18A; KIF20A; KIF20B; KIF23; KIF2C; KIF4A; NEFM; PLK1; PRNP; RACGAP1; | 17 | 1.06 | CAMSAP3; CAPN6; CRYAB; DCX; DYNC1I1; GAS2L2; JAKMIP3; KIF1A; KIFC2; MAP1A; MAP1LC3C; MAP6; MAPT; SNCA; SPAG8; SYBU; TPPP | 2 | 4.40 | CAPN6; CRYAB | 0 | 0.00 | | 5 | 0.67 | JAKMIP3; MAPT; SNCA; SYBU; TPPP | 17 | 2.54 | BIRC5; CENPE; GAPDH; KIF11; KIF14; KIF15; KIF18A; KIF18B; KIF20A; KIF23; KIF2C; KIF4A; KIFC1; NDRG1; NEFM; PLK1; SKA1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | S100A8; S100A9; SKA1 | | | | | | | | | | | | | | | |
| regulation of cell cycle g1 s phase transition: GO | 140 | 18 | 2.15 | ANXA1; AURKA; C10orf99; CCNB1; CDC45; CDC6; CDK1; CDKN1A; E2F7; FAM83D; KIF14; NPM1; PCNA; PDPN; PLK2; PSME3; SFN; TP63 | 8 | 0.67 | BCL2; CYP1A1; DACT1; FHL1; KANK2; PKD1; PLK5; SUSD2 | 0 | 0.00 | | 0 | 0.00 | | 3 | 0.54 | BCL2; DACT1; SUSD2 | 14 | 2.84 | AURKA; C10orf99; CCNB1; CDC45; CDC6; CDK1; CDKN1A; E2F1; E2F7; GTSE1; KIF14; NPM1; PLK2; SFN |
| recruitment of numa to mitotic centrosomes | 66 | 9 | 2.28 | CCNB1; CDK1; DYNLL1; NEK2; PLK1; TUBA1C; TUBA4A; TUBB2A; TUBB6 | 2 | 0.36 | MAST1; PRKAR2B | 1 | 6.33 | PRKAR2B | 0 | 0.00 | | 1 | 0.38 | DLC1 | 9 | 3.87 | CCNB1; CDK1; NEK2; PLK1; PLK4; TUBA1C; TUBA4A; TUBB2A; TUBB6 |
| regulation of proteasomal ubiquitin dependent protein catabolic process: GO | 141 | 15 | 1.78 | AURKA; BUB1; BUB1B; CCNB1; CENPF; CSNK1A1; DLGAP5; FBXO5; GEN1; MAD2L1; PBK; PLK1; PLK2; TTK; VCP | 2 | 0.17 | CLU; SVIP | 0 | 0.00 | | 0 | 0.00 | | 3 | 0.54 | CLU; PRICKLE1; SVIP | 14 | 2.82 | AURKA; BUB1; BUB1B; CCNB1; CENPF; DLGAP5; MAD2L1; PBK; PLK1; PLK2; RNF19B; TRIB1; TRIB3; TTK |
| protein ubiquitination involved in | 126 | 13 | 1.73 | AURKA; BUB1B; CCNB1; | 1 | 0.09 | RNF165 | 0 | 0.00 | | 0 | 0.00 | | 2 | 0.40 | GAN; LNX1 | 13 | 2.93 | AURKA; AURKB; BUB1B; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| ubiquitin dependent protein catabolic process: GO | | | | CDC20; CDK1; FBXO45; HERC6; MAD2L1; PLK1; PTTG1; UBA6; UBE2C; UHRF1 | | | | | | | | | | | | | | | CCNB1; CDC20; CDK1; FBXO45; HERC6; MAD2L1; PLK1; PTTG1; RNF19B; UBE2C |
| mitotic cytokinesis: GO | 31 | 8 | 4.32 | ANLN; CEP55; CKAP2; KIF20A; KIF23; KIF4A; PLK1; RACGAP1 | 0 | 0.00 | | 0 | 0.00 | | 0 | 0.00 | | 0 | 0.00 | | 6 | 5.49 | ANLN; CEP55; KIF20A; KIF23; KIF4A; PLK1 |
| p38 mk2 pathway | 21 | 5 | 3.98 | CDC25B; SFN; TH; YWHAQ; YWHAZ | 1 | 0.56 | LSP1 | 0 | 0.00 | | 0 | 0.00 | | 0 | 0.00 | | 5 | 6.75 | CDC25B; SFN; TH; YWHAQ; YWHAZ |
| resolution of d-loop structures through synthesis-dependent strand annealing (sdsa) | 21 | 3 | 2.39 | BLM; BRCA2; EXO1 | 0 | 0.00 | | 0 | 0.00 | | 0 | 0.00 | | 0 | 0.00 | | 5 | 6.75 | BLM; BRCA2; BRIP1; EXO1; RAD51AP1 |
| negative regulation of binding: GO | 128 | 12 | 1.57 | AURKA; EIF4A3; GZMA; HMGA2; HMOX1; HSPA5; IFI16; MDFI; NEK2; P2RY1; RALB; SLPI | 11 | 1.01 | ADIPOQ; CAMK1; CYP2D6; DACT1; DKK1; FRMD7; GATA1; HAND2; NOG; SLN; WFIKKN1 | 2 | 6.53 | ADIPOQ; WFIKKN1 | 0 | 0.00 | | 3 | 0.60 | CAMK1; DACT1; HAND2 | 13 | 2.88 | AURKA; AURKB; E2F1; EIF4A3; GTSE1; HMGA2; HSPA5; IFI16; IL10; MDFI; NEK2; P2RY1; SLPI |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| pathogenic *escherichia coli* infection | 55 | 10 | 3.04 | ACTB; ARPCIA; ARPC3; ARPC5L; TUBA1C; TUBA4A; TUBB2A; TUBB6; YWHAQ; YWHAZ | 1 | 0.21 | TUBB4A | 0 | 0.00 | | 0 | 0.00 | | 0 | 0.00 | | 8 | 4.12 | ACTB; ARPC1A; TUBA1C; TUBA4A; TUBB2A; TUBB6; YWHAQ; YWHAZ |
| fanconi pathway | 43 | 5 | 1.95 | BLM; BRCA2; CHEK1; H2AFX; UBE2T | 1 | 0.27 | SSPO | 0 | 0.00 | | 0 | 0.00 | | 0 | 0.00 | | 7 | 4.62 | BLM; BRCA2; BRIP1; CHEK1; FANCI; H2AFX; UBE2T |
| cytokinesis: GO | 83 | 13 | 2.62 | ACTR3; ANLN; BIRC5; BRCA2; CEP55; CKAP2; ECT2; KIF20A; KIF23; KIF4A; PLK1; RACGAP1; RALB | 2 | 0.28 | CECR2; ROPN1B | 0 | 0.00 | | 0 | 0.00 | | 1 | 0.31 | ROPN1B | 10 | 3.42 | ANLN; AURKB; BIRC5; BRCA2; CEP55; ECT2; KIF20A; KIF23; KIF4A; PLK1 |
| progesterone mediated oocyte maturation | 83 | 11 | 2.22 | BUB1; CCNA2; CCNB1; CCNB2; CDC25A; CDC25B; CDK1; GNAI3; MAD2L1; | 7 | 1.00 | ADCY2; ADCY5; ADCY6; ADCY8; CPEB1; PGR; RPS6KA6 | 0 | 0.00 | | 0 | 0.00 | | 3 | 0.92 | CPEB1; PGR; RPS6KA6 | 10 | 3.42 | BUB1; CCNA2; CCNB1; CCNB2; CDC25A; CDC25B; CDK1; MAD2L1; PKMYT1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | PKMYT1; PLK1 | | | | | | | | | | | | | | | PLK1 |
| telomere organization: GO | 98 | 16 | 2.73 | BRCA2; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L; NOP10; PCNA; PIF1 | 1 | 0.12 | TERT | 0 | 0.00 | | 0 | 0.00 | | 0 | 0.00 | | 11 | 3.18 | BRCA2; FEN1; HIST1H3A; HIST1H3C; HIST1H3F; HIST1H3G; HIST1H3H; HIST1H3I; HIST1H3J; HIST1H4I; PIF1 |
| positive regulation of cytokinesis: GO | 32 | 7 | 3.66 | CDC25B; CDC6; ECT2; KIF14; KIF20B; KIF23; RACGAP1 | 1 | 0.37 | CXCR5 | 0 | 0.00 | | 0 | 0.00 | | 1 | 0.79 | CENPV | 6 | 5.32 | AURKB; CDC25B; CDC6; ECT2; KIF14; KIF23 |
| negative regulation of response to wounding: GO | 147 | 20 | 2.28 | ACP5; ADCYAP1; F12; FOXF1; GJA1; GSTP1; HMGCR; IL12B; IL2RA; MEFV; PBK; PLAU; PLAUR; SERPINB2; SERPINE1; SERPINE2; SOCS3; THBD; UBASH3B; ZC3H12A | 11 | 0.88 | ADIPOQ; ADORA1; APOD; APOE; CD34; ELANE; KLKB1; PTGIS; SLIT2; TMPRSS6; TSPAN8 | 1 | 2.84 | ADIPOQ | 2 | 5.69 | IL2RA; SERPINE1 | 6 | 1.04 | CD34; ELANE; FGF2; PRKG1; SLIT2; TSPAN8 | 14 | 2.70 | ACP5; F12; GSTP1; IL10; MEFV; PBK; PLAT; PPARD; SERPINB2; SERPINE2; SOCS3; THBD; UBASH3B; ZC3H12A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| regulation of alcohol biosynthetic process: GO | 44 | 6 | 2.28 | CYP27B1; IFNG; IL1B; NTSR1; P2RY1; PTAFR | 6 | 1.61 | APOE; BMP5; FGF1; LHCGR; PTHIR; SNCA | 0 | 0.00 | | 1 | 9.50 | IL1B | 3 | 1.73 | ADCYAP1R1; PTH1R; SNCA | 7 | 4.51 | CYP27B1; HRH1; LPCAT1; NTSR1; P2RY1; PTAFR; SNAI2 |
| female meiotic division: GO | 22 | 6 | 4.56 | AURKA; CDC25B; EREG; FBXO5; PLK1; TRIP13 | 0 | 0.00 | | 0 | 0.00 | | 0 | 0.00 | | 0 | 0.00 | | 5 | 6.44 | AURKA; CDC25B; EREG; PLK1; TRIP13 |
| hexose metabolic process: GO | 148 | 14 | 1.58 | CHST1; ENO1; FABP5; FUT1; FUT2; GAPDH; GOT2; HK2; OAS1; PFKFB4; PGAM1; PGK1; PGM2; TPI1 | 18 | 1.43 | ADIPOQ; ALDHIA1; ALDOB; APOD; FUT9; GALT; GPD1; IRS2; LEP; NPY1R; PCK1; PDK4; PFKFB1; PGM5; PPARGC1A; RBP4; SERPINA12; TFAP2B | 2 | 5.65 | ADIPOQ; GPD1 | 0 | 0.00 | | 10 | 1.72 | ALDH5A1; ALDOC; IGFBP5; NPY1R; PDK3; PDK4; PFKFB1; PGM5; PPARGC1A; SERPINA12 | 14 | 2.68 | CHST1; ENO1; FABP5; FUT1; FUT2; GAPDH; GOT2; HK2; OAS1; PFKFB4; PGAM1; PGK1; PPARD; TPI1 |
| homologous dna pairing and strand exchange | 33 | 4 | 2.03 | BLM; BRCA2; CHEK1; EXO1 | 0 | 0.00 | | 0 | 0.00 | | 0 | 0.00 | | 0 | 0.00 | | 6 | 5.16 | BLM; BRCA2; BRIP1; CHEK1; EXO1; RAD51AP1 |
| p53 downstream pathway | 133 | 17 | 2.14 | BAK1; BCL2A1; BDKRB2; CCNB1; CDKN1A; E2F3; PCNA; PERP; PRDM1; PYCARD; | 4 | 0.35 | BCL2; DKK1; KAT2A; LIF | 0 | 0.00 | | 1 | 3.14 | SERPINE1 | 2 | 0.38 | BCL2; FOXA1 | 13 | 2.77 | BAK1; BDKRB2; CCNB1; CDKN1A; E2F1; EPHA2; IGFBP3; NDRG1; S100A2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | S100A2; SERPINB5; SERPINE1; SFN; TGFA; TNFRSF10A; TP63 | | | | | | | | | | | | | | | SERPINB5; SFN; SNAI2; TGFA |
| negative regulation of cell cycle g2 m phase transition: GO | 23 | 5 | 3.64 | BLM; CCNA2; CDK1; CLSPN; HMGA2 | 1 | 0.51 | FHL1 | 0 | 0.00 | | 0 | 0.00 | | 0 | 0.00 | | 5 | 6.16 | BLM; CCNA2; CDK1; FANCI; HMGA2 |
| carbon fixation | 23 | 4 | 2.91 | GOT2; PGK1; PKM; TPI1 | 2 | 1.03 | ALDOB; GPT | 0 | 0.00 | | 0 | 0.00 | | 2 | 2.21 | ALDOC; GPT | 5 | 6.16 | GOT2; PGK1; PKM; TKT; TPI1 |
| synthesis of dna | 102 | 13 | 2.13 | CCNA2; CDC45; CDC6; CDKN1A; GINS1; GINS3; ORC1; ORC6; PCNA; PSMA4; PSMA5; PSMB6; PSMD1 | 0 | 0.00 | | 0 | 0.00 | | 0 | 0.00 | | 0 | 0.00 | | 11 | 3.06 | CCNA2; CDC45; CDC6; CDKN1A; FEN1; GINS1; GINS3; GINS4; MCM2; ORC1; ORC6 |
| gluconeogenesis | 34 | 7 | 3.45 | ENO1; GAPDH; GOT2; PGAM1; PGK1; TPI1; TPI1P1 | 3 | 1.04 | ALDOB; PCK1; PFKFB1 | 0 | 0.00 | | 0 | 0.00 | | 2 | 1.49 | ALDOC; PFKFB1 | 6 | 5.00 | ENO1; GAPDH; GOT2; PGAM1; PGK1; TPI1 |
| negative regulation of viral genome replication: GO | 46 | 15 | 5.46 | APOBEC3A; HMGA2; IFI16; IFITM1; IFITM3; ISG15; ISG20; LTF; MX1; OAS1; OAS3; OASL; | 0 | 0.00 | | 0 | 0.00 | | 2 | 18.17 | IFITM3; ISG15 | 0 | 0.00 | | 7 | 4.32 | HMGA2; IFI16; LTF; MX1; OAS1; SLPI; ZC3H12A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | RSAD2; SLPI; ZC3H12A | | | | | | | | | | | | | | | |
| chaperonin-mediated protein folding | 46 | 10 | 3.64 | ACTB; CCNE1; CCT5; CCT6A; GNAI3; PLP2; TUBA1C; TUBA4A; TUBB2A; TUBB6 | 0 | 0.00 | | 0 | 0.00 | | 0 | 0.00 | | 1 | 0.55 | GNG11 | 7 | 4.32 | ACTB; CCT5; NOP56; TUBA1C; TUBA4A; TUBB2A; TUBB6 |
| a6b1 a6b4 integrin pathway | 46 | 6 | 2.18 | IL1A; ITGA6; LAMB3; SFN; YWHAQ; YWHAZ | 5 | 1.28 | EGF; LAMA2; LAMC3; MST1; RXRG | 0 | 0.00 | | 0 | 0.00 | | 3 | 1.66 | EGF; LAMA2; LAMC3 | 7 | 4.32 | COL17A1; ITGA6; ITGB4; LAMB3; SFN; YWHAQ; YWHAZ |
| placenta development: GO | 135 | 15 | 1.86 | CSF2; CTSB; CYP27B1; E2F7; EOMES; FOSL1; GJB2; GJB3; GJB5; HIF1A; MDFI; PHLDA2; PRDM1; PTGS2; SOCS3 | 6 | 0.52 | CDX4; LEP; LIF; PKD1; PTGIS; TTPA | 1 | 3.10 | CDKNIC | 0 | 0.00 | | 3 | 0.56 | CDX4; DCN; ESR1 | 13 | 2.73 | ASCL2; CYP27B1; E2F7; FOSL1; HIF1A; IL10; JUNB; MDFI; PHLDA2; PLK4; PPARD; PTGS2; SOCS3 |
| cell communication | 119 | 26 | 3.66 | ACTB; DSC1; DSC2; DSC3; DSG1; DSG3; GJA1; GJB2; GJB3; GJB5; GJB6; INA; ITGA6; KRT13; KRT14; KRT16; KRT17; KRT3; KRT5; KRT6A; | 24 | 2.38 | CHAD; COL11A1; COL11A2; DES; GJB4; GJC3; KRT12; KRT15; KRT31; KRT32; KRT35; KRT39; KRT40; KRT73; KRT77; | 1 | 3.51 | KRT73 | 0 | 0.00 | | 13 | 2.78 | CHAD; COL11A1; GJB4; KRT12; KRT2; KRT40; KRT77; KRT86; LAMA2; LAMC3; POTEKP; RELN; TNN | 12 | 2.86 | ACTB; COL17A1; DSC2; DSC3; DSG4; INA; ITGA6; ITGB4; KRT13; KRT5; LAMB3; LMNB2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | KRT6B; KRT9; LAMB3; LMNB1; LMNB2; TNC | | | KRT86; LAMA2; LAMB4; LAMC3; POTEKP; PRPH; RELN; TNN; TNXB | | | | | | | | | | | | |
| regulation of wound healing: GO | 120 | 18 | 2.51 | ANXA1; F12; F2RL1; GJA1; HBEGF; HMGCR; HPSE; INSL3; PLAU; PLAUR; PRKCQ; S100A9; SERPINB2; SERPINE1; SERPINE2; THBD; TNFRSF12A; UBASH3B | 10 | 0.98 | ADRA2A; APOE; CD34; ENPP4; F7; GSN; KLKB1; SCARA5; TMPRSS6; TSPAN8 | 0 | 0.00 | | 1 | 3.48 | SERPINE1 | 6 | 1.27 | ADRA2A; CD34; FGF2; PRKG1; SCARA5; TSPAN8 | 12 | 2.84 | F12; HBEGF; HPSE; PLAT; PPARD; PRKCQ; SERPINB2; SERPINE2; SOX15; THBD; UBASH3B; VAV2 |
| resolution of d-loop structures | 24 | 4 | 2.79 | BLM; BRCA2; EXO1; GEN1 | 0 | 0.00 | | 0 | 0.00 | | 0 | 0.00 | | 0 | 0.00 | | 5 | 5.91 | BLM; BRCA2; BRIP1; EXO1; RAD51AP1 |
| resolution of d-loop structures through holliday junction intermediates | 24 | 4 | 2.79 | BLM; BRCA2; EXO1; GEN1 | 0 | 0.00 | | 0 | 0.00 | | 0 | 0.00 | | 0 | 0.00 | | 5 | 5.91 | BLM; BRCA2; BRIP1; EXO1; RAD51AP1 |
| g alpha (i) signalling events | 75 | 16 | 3.57 | ANXA1; CCL21; CXCL1; CXCL10; CXCL11; CXCL13; CXCL3; CXCL6; | 4 | 0.63 | ADCY8; AGT; C3; NPY1R | 0 | 0.00 | | 0 | 0.00 | | 5 | 1.69 | C3; CXCL12; GNG11; LPAR1; NPY1R | 9 | 3.40 | CCL20; CXCL11; CXCL2; CXCL6; FPR2; NMU; PNP; RGS1; RGS20 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | CXCL8; CXCR4; FPR1; GNAI3; NMU; PNP; RGS1; RGS20 | | | | | | | | | | | | | | | |
| oogenesis: GO | 61 | 9 | 2.47 | ASPM; BRCA2; CCNB1; CDC25B; EREG; FBXO5; INSL3; PAQR5; TRIP13 | 8 | 1.55 | BCL2; INHBB; LGR5; NOBOX; NPM2; PIWIL2; TDRD5; YBX2 | 0 | 0.00 | | 0 | 0.00 | | 2 | 0.83 | BCL2; LGR5 | 8 | 3.72 | ASPM; BMPR1B; BRCA2; CCNB1; CDC25B; EREG; PAQR5; TRIP13 |
| female gamete generation: GO | 90 | 14 | 2.60 | ASPM; BRCA2; CCNB1; CDC25B; DYNLL1; EREG; FBXO5; FOSL1; IL1B; IL4R; INSL3; PAQR5; PTGS2; TRIP13 | 10 | 1.31 | BCL2; CYP17A1; INHBB; LEP; LGR5; NOBOX; NPM2; PIWIL2; TDRD5; YBX2 | 0 | 0.00 | | 1 | 4.64 | IL1B | 2 | 0.56 | BCL2; LGR5 | 10 | 3.15 | ASPM; BMPR1B; BRCA2; CCNB1; CDC25B; EREG; FOSL1; PAQR5; PTGS2; TRIP13 |
| fra pathway | 36 | 11 | 5.11 | CCNA2; FOSL1; GJA1; HMOX1; IL6; IVL; MMP1; MMP9: PLAU; PLAUR; THBD | 2 | 0.66 | LIF; MGP | 0 | 0.00 | | 0 | 0.00 | | 1 | 0.71 | DCN | 6 | 4.73 | CCNA2; FOSL1; ITGB4; IVL; JUNB; THBD |
| monosaccharide metabolic process: GO | 192 | 19 | 1.66 | CHST1; ENO1; FABP5; FUT1; FUT2; GAPDH; GOT2; GSTO1; HK2; | 22 | 1.35 | ADIPOQ; ALDH1A1; ALDOB; APOD; FUT9; GALT; GPD1; IRS2; LEP; NPY1R; | 2 | 4.35 | ADIPOQ; GPD1 | 0 | 0.00 | | 10 | 1.32 | ALDH5A1; ALDOC; IGFBP5; NPY1R; PDK3; PDK4; PFKFB1; PGM5; | 16 | 2.36 | CHST1; ENO1; FABP5; FUT1; FUT2; GAPDH; GOT2; HK2; OAS1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | OAS1; PFKFB4; PGAM1; PGK1; PGM2; SLC2A1; TPI1; UGT1A1; UGT1A10; UGT1A7 | | | OTOGL; PCK1; PDK4; PFKFB1; PGM5; PPARGC1A; RBP4; SERPINA12; TFAP2B; UGT2A1; UGT2B7; UGT3A2 | | | | | | | | | PPARGC1A; SERPINA12 | | | PFKFB4; PGAM1; PGK1; PPARD; SLC2A1; TKT; TPI1 |
| carbohydrate catabolic process: GO | 107 | 15 | 2.35 | ENO1; FUT1; FUT2; GAPDH; GK; HK2; LDHA; NEU2; OGDHL; PFKFB4; PGAM1; PGK1; PGM2; PYGL; TPI1 | 10 | 1.10 | ALDH1A1; ALDOB; FUT9; GALT; GYG2; PFKFB1; PGM5; PHKG1; PYGM; STBD1 | 0 | 0.00 | | 0 | 0.00 | | 4 | 0.95 | ALDOC; PFKFB1; PGM5; PHKG1 | 11 | 2.92 | ENO1; FUT1; FUT2; GAPDH; HK2; LDHA; OGDHL; PFKFB4; PGAM1; PGK1; TPI1 |
| cell differentiation involved in embryonic placenta development: GO | 25 | 6 | 4.02 | E2F7; EOMES; GJB5; MDFI; PRDM1; SOCS3 | 1 | 0.47 | LIF | 0 | 0.00 | | 0 | 0.00 | | 0 | 0.00 | | 5 | 5.67 | ASCL2; E2F7; MDFI; PLK4; SOCS3 |
| rho gtpases activate iqgaps | 25 | 5 | 3.35 | ACTB; TUBA1C; TUBA4A; TUBB2A; TUBB6 | 0 | 0.00 | | 0 | 0.00 | | 0 | 0.00 | | 0 | 0.00 | | 5 | 5.67 | ACTB; TUBA1C; TUBA4A; TUBB2A; TUBB6 |
| sumoylation of dna replication proteins | 25 | 5 | 3.35 | AURKA; BIRC5; CDCA8; PCNA; TOP2A | 0 | 0.00 | | 0 | 0.00 | | 0 | 0.00 | | 0 | 0.00 | | 5 | 5.67 | AURKA; AURKB; BIRC5; CDCA8; TOP2A |
| strand displacement: GO | 25 | 3 | 2.01 | BLM; BRCA2; EXO1 | 0 | 0.00 | | 0 | 0.00 | | 0 | 0.00 | | 0 | 0.00 | | 5 | 5.67 | BLM; BRCA2; BRIP1; EXO1; RAD51AP1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| foxo pathway | 49 | 8 | 2.73 | CCNB1; CSNK1A1; PLK1; RALB; RAN; SFN; YWHAQ; YWHAZ | 1 | 0.24 | MST1 | 0 | 0.00 | | 0 | 0.00 | | 0 | 0.00 | | 7 | 4.05 | CCNB1; PLK1; RAN; SFN; SGK1; YWHAQ; YWHAZ |
| interleukin-4 and 13 signaling | 92 | 22 | 4.00 | ANXA1; BIRC5; CDKN1A; CXCL8; FSCN1; HIF1A; HMOX1; HSPA8; IL13RA1; IL13RA2; IL1A; IL1B; IL4R; IL6; JAK3; LCN2; MMP1; MMP3; MMP9; PTGS2; SOCS3; STAT1 | 5 | 0.64 | BCL2; LIF; MAOA; NOS2; RORC | 0 | 0.00 | | 1 | 4.54 | IL1B | 2 | 0.55 | BCL2; RHOU | 10 | 3.08 | BIRC5; CDKN1A; HIF1A; HSPA8; IL10; IL13RA2; JUNB; MMP3; PTGS2; SOCS3 |
| dna geometric change: GO | 77 | 8 | 1.74 | ANXA1; BLM; CDC45; GINS1; HMGB3; PIF1; RUVBL1; TOP2A | 0 | 0.00 | | 0 | 0.00 | | 0 | 0.00 | | 0 | 0.00 | | 9 | 3.31 | BLM; BRIP1; CDC45; GINS1; GINS4; HMGB3; MCM2; PIF1; TOP2A |
| glycolysis/ gluconeogenesis | 63 | 10 | 2.66 | ADH7; ALDH1A3; ENO1; GAPDH; HK2; LDHA; PGAM1; PGK1; PKM; TPI1 | 4 | 0.75 | ADH1B; ADH1C; ADHFE1; ALDOB | 0 | 0.00 | | 0 | 0.00 | | 2 | 0.81 | ALDH3A2; ALDOC | 8 | 3.60 | ENO1; GAPDH; HK2; LDHA; PGAM1; PGK1; PKM; TPI1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| cell maturation: GO | 125 | 13 | 1.74 | BFSP1; BRCA2; CCL21; CCNB1; CDC25B; CDKN1A; CNTNAP2; EREG; FBXO5; GJA1; HIF1A; INSL3; TRIP13 | 13 | 1.23 | CFTR; EPB42; FGFR1; KCNIP2; LGI4; MYOC; PLP1; PTH1R; REN; SOX10; SOX8; SPTBN4; TDRD5 | 1 | 3.34 | CDKN1C | 0 | 0.00 | | 10 | 2.03 | BHLHA15; FGFR1; FOXA1; GLDN; LGI4; MYOC; NTN4; PLP1; PTH1R; SPTBN4 | 12 | 2.72 | AGRN; BFSP1; BRCA2; CCNB1; CDC25B; CDKN1A; CNTNAP2; EREG; HIF1A; RND1; SLC26A6; TRIP13 |
| learning: GO | 125 | 13 | 1.74 | CNTNAP2; EIF4A3; FOSL1; HIF1A; HMGCR; NDRG4; NLGN4X; NTSR1; PTGS2; STRA6; TH; UBA6; VDAC1 | 16 | 1.51 | ATP1A2; DKK1; DRD1; DRD4; GRIN1; GRIN2A; GRM7; NETO1; NEUROD2; NRXN1; NRXN3; PPP1R1B; PRKAR2B; RELN; SHANK1; SLC24A2 | 1 | 3.34 | PRKAR2B | 0 | 0.00 | | 2 | 0.41 | NRXN1; RELN | 12 | 2.72 | CNTNAP2; EIF4A3; FOSL1; HIF1A; HRH1; HRH2; NLGN4X; NTSR1; PTGS2; SGK1; TH; VDAC1 |
| microtubule organizing center organization: GO | 78 | 9 | 1.93 | AURKA; BRCA2; CDK1; KIF11; NEK2; NPM1; PLK1; SLC16A1; STIL | 1 | 0.15 | CROCC | 0 | 0.00 | | 0 | 0.00 | | 0 | 0.00 | | 9 | 3.27 | AURKA; BRCA2; CDK1; KIF11; NEK2; NPM1; PLK1; PLK4; STIL |
| kinase regulator activity: GO | 177 | 15 | 1.42 | CCNE1; CDK5R1; CDKN1A; CKS2; CXCL10; FLRT3; GREM1; | 13 | 0.87 | ANGPT4; CCKBR; CHAD; EGF; LRRC4C; LRRTM3; LRRTM4; MAPK8IP1; | 2 | 4.72 | CDKNIC; PRKAR2B | 1 | 2.36 | RAC2 | 11 | 1.58 | ANGPT4; CHAD; DCN; EGF; GPRC5B; LRRC15; LRRC4C; PIK3R6; | 15 | 2.40 | AFAP1L2; CDK5R1; CDKN1A; CISH; CKS2; FLRT3; GSTP1; LRRC4; LTF; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | GSTP1; LRRC4; LTF; NPM1; NRG1; RAC2; SFN; SOCS3 | | | NRG3; PODN; PPP1R1B; PRKAR2B; WNT11 | | | | | | | | | PODN; TESC; WNT11 | | | NPM1; NRG1; SFN; SOCS3; TRIB1; TRIB3 |
| cellular response to ionizing radiation: GO | 50 | 5 | 1.67 | BLM; CDKN1A; ECT2; H2AFX; IFI16 | 1 | 0.24 | CRYAB | 1 | 8.36 | CRYAB | 0 | 0.00 | | 1 | 0.51 | TSPYL5 | 7 | 3.97 | BLM; CDKN1A; ECT2; H2AFX; IFI16; RAD51AP1; SNAI2 |
| dna helicase activity: GO | 50 | 5 | 1.67 | BLM; CDC45; GINS1; PIF1; RUVBL1 | 0 | 0.00 | | 0 | 0.00 | | 0 | 0.00 | | 0 | 0.00 | | 7 | 3.97 | BLM; BRIP1; CDC45; GINS1; GINS4; MCM2; PIF1 |
| gap junction trafficking and regulation | 26 | 6 | 3.86 | ACTB; GJB2; TUBA1C; TUBA4A; TUBB2A; TUBB6 | 0 | 0.00 | | 0 | 0.00 | | 0 | 0.00 | | 0 | 0.00 | | 5 | 5.45 | ACTB; TUBA1C; TUBA4A; TUBB2A; TUBB6 |
| hif1 tfpathway | 64 | 10 | 2.61 | CXCR4; ENO1; HIF1A; HK2; HMOX1; LDHA; NPM1; PGK1; SERPINE1; SLC2A1 | 6 | 1.11 | BHLHE41; CP; LEP; NOS2; TERT; TF | 0 | 0.00 | | 1 | 6.53 | SERPINE1 | 3 | 1.19 | BHLHE41; CP; CXCL12 | 8 | 3.54 | ENO1; HIF1A; HK2; LDHA; NDRG1; NPM1; PGK1; SLC2A1 |
| response to estradiol: GO | 144 | 17 | 1.98 | ANXA1; AREG; AURKA; BRCA2; CALR; CCNA2; CCNE1; GJB2; GSTP1; H2AFZ; HIF1A; IL1B; PTGS2; | 11 | 0.90 | C3; CRYAB; CYP1A2; DRD1; GHR; LEP; MAPK15; NPY1R; PPARGC1A; PTCH1; TXNIP | 2 | 5.80 | CRYAB; GHR | 1 | 2.90 | IL1B | 10 | 1.76 | ADCYAP1R1; C3; CTGF; ESR1; FOXA1; NPY1R; PPARGC1A; PTCH1; PTGFR; TXNIP | 13 | 2.56 | AREG; AURKA; BRCA2; CCNA2; GSTP1; H2AFZ; HIF1A; IL10; PTGS2; SOCS3; TH; WNT5A; WNT7A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | SOCS3; TH; WNT5A; WNT7A | | | | | | | | | | | | | | | |
| cdc20: phospho-apc/c mediated degradation of cyclin a | 51 | 9 | 2.95 | BUB1; BUB1B; CCNA2; CDC20; CDK1; MAD2L1; PSMA5; PSMB6; UBE2C | 0 | 0.00 | | 0 | 0.00 | | 0 | 0.00 | | 0 | 0.00 | | 7 | 3.89 | BUB1; BUB1B; CCNA2; CDC20; CDK1; MAD2L1; UBE2C |
| protein tetramerization: GO | 128 | 17 | 2.22 | CDA; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L; HMGCR; RRM2; TK1; TP63 | 12 | 1.11 | ACACB; ACADL; ACTN2; DHPS; DNM1; GRIN1; LRP4; NLGN1; RXRG; SLC26A5; TRPM1; TRPM3 | 0 | 0.00 | | 0 | 0.00 | | 1 | 0.20 | ALDH5A1 | 12 | 2.66 | CDA; HIST1H3A; HIST1H3C; HIST1H3F; HIST1H3G; HIST1H3H; HIST1H3I; HIST1H3J; HIST1H4I; PDSS1; RRM2; TK1 |
| double strand break repair: GO | 145 | 17 | 1.96 | BLM; BRCA2; CDC45; CDCA5; DTX3L; ESCO2; GEN1; H2AFX; HIST1H4I; HIST1H4J; HIST1H4K; HIST1H4L; PARP9; | 1 | 0.08 | APBB1 | 0 | 0.00 | | 0 | 0.00 | | 0 | 0.00 | | 13 | 2.54 | BLM; BRCA2; BRIP1; CDC45; CDCA5; FEN1; GINS4; H2AFX; HIST1H4I; PARP9; POLQ; RAD51AP1; TRIP13 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | POLQ; TRIP13; UBE2N; VCP | | | | | | | | | | | | | | | |
| basigin interactions | 27 | 9 | 5.58 | ATP1B3; ITGA3; ITGA6; MMP1; PPIA; SLC16A1; SLC7A11; SLC7A5; SLC7A8 | 3 | 1.31 | SLC16A8; SLC7A10; SLC7A9 | 0 | 0.00 | | 0 | 0.00 | | 1 | 0.94 | ATP1B2 | 5 | 5.25 | ITGA3; ITGA6; PPIAP22; SLC7A11; SLC7A5 |
| positive regulation of fibroblast proliferation: GO | 52 | 6 | 1.93 | CCNA2; CCNB1; CDC6; CDKN1A; EREG; WNT5A | 3 | 0.68 | AGT; BTC; PDGFD | 0 | 0.00 | | 0 | 0.00 | | 3 | 1.47 | DDR2; ESR1; FBLN1 | 7 | 3.82 | CCNA2; CCNB1; CDC6; CDKN1A; E2F1; EREG; WNT5A |
| rmts methylate histone arginines | 39 | 9 | 3.86 | H2AFX; H2AFZ; HIST1H2AE; HIST1H3A; HIST1H3I; HIST1H4I; HIST1H4J; HIST1H4K; HIST1H4L | 0 | 0.00 | | 0 | 0.00 | | 0 | 0.00 | | 0 | 0.00 | | 6 | 4.36 | H2AFX; H2AFZ; HIST1H2AE; HIST1H3A; HIST1H3I; HIST1H4I |
| nuclear ubiquitin ligase complex: GO | 39 | 6 | 2.57 | BUB1B; CBX2; CDC20; RNF222; UBE2C; UBE2S | 1 | 0.30 | CBX7 | 0 | 0.00 | | 0 | 0.00 | | 1 | 0.65 | CBX7 | 6 | 4.36 | BUB1B; CBX2; CDC20; RNF222; UBE2C; UBE2S |
| positive regulation of cell cycle phase transition: GO | 66 | 12 | 3.04 | ANXA1; BIRC5; CDC45; CDC6; CDCA5; DLGAP5; FAM83D; FBXO5; | 1 | 0.18 | CYP1A1 | 0 | 0.00 | | 0 | 0.00 | | 0 | 0.00 | | 8 | 3.44 | BIRC5; CDC45; CDC6; CDCA5; DLGAP5; NPM1; PLK1; UBE2C |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | NPM1; PLK1; TP63; UBE2C | | | | | | | | | | | | | | | |
| regulation of tp53 activity through phosphorylation | 66 | 6 | 1.52 | AURKA; BLM; CCNA2; CHEK1; EXO1; TPX2 | 1 | 0.18 | PRKAA2 | 0 | 0.00 | | 0 | 0.00 | | 1 | 0.38 | PRKAA2 | 8 | 3.44 | AURKA; AURKB; BLM; BRIP1; CCNA2; CHEK1; EXO1; TPX2 |
| motor activity: GO | 130 | 12 | 1.54 | CENPE; DYNLL1; KIF11; KIF14; KIF15; KIF18A; KIF20A; KIF20B; KIF23; KIF2C; KIF4A; MYO1B | 16 | 1.45 | CGN; CGNL1; DNAH11; DNAH6; DYNC1I1; KIF1A; KIFC2; MYH11; MYH14; MYH3; MYH7B; MYL3; MYO15A; MYO1A; MYO3A; MYO5C | 0 | 0.00 | | 0 | 0.00 | | 3 | 0.59 | CGN; CGNL1; MYO5C | 12 | 2.62 | CENPE; KIF11; KIF14; KIF15; KIF18A; KIF18B; KIF20A; KIF23; KIF2C; KIF4A; KIFC1; MYO1B |
| recombinational repair: GO | 67 | 7 | 1.75 | BLM; BRCA2; CDC45; GEN1; H2AFX; POLQ; UBE2N | 0 | 0.00 | | 0 | 0.00 | | 0 | 0.00 | | 0 | 0.00 | | 8 | 3.39 | BLM; BRCA2; CDC45; FEN1; GINS4; H2AFX; POLQ; RAD51AP1 |
| monosaccharide biosynthetic process: GO | 53 | 7 | 2.21 | ENO1; GAPDH; GOT2; GSTO1; PGAM1; PGK1; TPI1 | 6 | 1.34 | ALDOB; GPD1; PCK1; PFKFB1; PPARGC1A; RBP4 | 1 | 7.88 | GPD1 | 0 | 0.00 | | 3 | 1.44 | ALDOC; PFKFB1; PPARGC1A | 7 | 3.75 | ENO1; GAPDH; GOT2; PGAM1; PGK1; TKT; TPI1 |
| glucose metabolic process: GO | 114 | 11 | 1.61 | ENO1; FABP5; GAPDH; GOT2; HK2; OAS1; | 15 | 1.55 | ADIPOQ; ALDOB; APOD; GPD1; IRS2; LEP; NPY1R; | 2 | 7.33 | ADIPOQ; GPD1 | 0 | 0.00 | | 10 | 2.23 | ALDH5A1; ALDOC; IGFBP5; NPY1R; PDK3; PDK4; | 11 | 2.74 | ENO1; FABP5; GAPDH; GOT2; HK2; OAS1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | PFKFB4; PGAM1; PGK1; PGM2; TPI1 | | | PCK1; PDK4; PFKFB1; PGM5; PPARGC1A; RBP4; SERPINA12; TFAP2B | | | | | | | | | PFKFB1; PGM5; PPARGC1A; SERPINA12 | | | PFKFB4; PGAM1; PGK1; PPARD; TPI1 |
| protease binding: GO | 98 | 20 | 3.41 | ADAMTS4; BDKRB2; BRCA2; CSTA; CSTB; DPP4; INSL3; ITGA3; LDLR; PANX1; PYCARD; SELL; SERPINA1; SERPINB13; SERPINB3; SERPINB4; SERPINB9; SERPINE1; TNFRSF10A; VCP | 8 | 0.96 | BCL2; CCBE1; CD70; ELANE; NOL3; SERPINA5; TIMP3; TIMP4 | 0 | 0.00 | | 2 | 8.53 | SERPINB9; SERPINE1 | 5 | 1.30 | BCL2; CCBE1; CD70; CHL1; ELANE | 10 | 2.89 | ADAMTS4; BDKRB2; BRCA2; CSTA; CSTB; DPP4; ITGA3; LDLR; PANX1; SERPINB13 |
| activation of the pre-replicative complex | 28 | 6 | 3.59 | CDC45; CDC6; DBF4; MCM10; ORC1; ORC6 | 0 | 0.00 | | 0 | 0.00 | | 0 | 0.00 | | 0 | 0.00 | | 5 | 5.06 | CDC45; CDC6; MCM2; ORC1; ORC6 |
| developmental maturation: GO | 184 | 16 | 1.46 | BFSP1; BRCA2; CCL21; CCNB1; CDC25B; CDK5R1; CDKN1A; CNTNAP2; EREG; FBXO5; GJA1; HIF1A; INSL3; | 22 | 1.41 | CFTR; EPB42; FGFR1; FGFR3; GRIN1; KCNIP2; LEP; LGI4; MYOC; NRXN1; PALM; PLP1; PTH1R; REN; SEZ6L; SHANK1; | 1 | 2.27 | CDKN1C | 0 | 0.00 | | 15 | 2.07 | BHLHA15; FGFR1; FOXA1; GLDN; LGI4; MYOC; NRXN1; NTN4; PALM; PLP1; PTH1R; RECK; SEZ6L; SPTBN4; ZDHHC15 | 15 | 2.31 | AGRN; BFSP1; BRCA2; CCNB1; CDC25B; CDK5R1; CDKN1A; CNTNAP2; EREG; HIF1A; RAB38; RND1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | RAB38; TRIP13; UNC13A | | | SLC17A7; SOX10; SOX8; SPTBN4; TDRD5; ZDHHC15 | | | | | | | | | | | | SLC26A6; TRIP13; UNC13A |
| humoral immune response: GO | 166 | 25 | 2.52 | CIQBP; CAMP; EBI3; EXO1; HIST1H2BC; HIST1H2BE; HIST1H2BF; HIST1H2BG; HIST1H2BI; HIST1H2BJ; HIST1H2BK; IFNE; IFNG; IGHG1; IGHG2; IGHG4; IGKC; IGKV4-1; IL36RN; IL6; LTF; RNASE7; SLPI; TNFRSF21; TREM1 | 13 | 0.92 | BCL2; C3; C4BPA; C6; C7; CFD; CFH; CLU; COLEC11; FCN2; IFNA5; MNX1; PLA2G6 | 2 | 5.03 | IGHG1; IGKV3-20 | 1 | 2.52 | TREM1 | 6 | 0.92 | BCL2; C3; CFH; CLU; IGHM; IGHV3-23 | 14 | 2.39 | BCL3; CD83; EXO1; HIST1H2BC; HIST1H2BE; HIST1H2BF; HIST1H2BG; HIST1H2BI; HIST1H2BJ; HIST1H2BK; HIST2H2BE; IFNE; LTF; SLPI |
| positive regulation of cellular protein catabolic process: GO | 185 | 21 | 1.90 | AURKA; BUB1B; CCNB1; CDC20; CDK1; CSNK1A1; CTSC; DLGAP5; FBXO5; MAD2L1; MSN; PCSK9; PLK1; PLK2; PSMA4; | 4 | 0.26 | APOE; CLU; DACTI; EGF | 0 | 0.00 | | 0 | 0.00 | | 5 | 0.69 | CLU; DACT1; ECSCR; EGF; PRICKLE1 | 15 | 2.30 | AURKA; BUB1B; CCNB1; CDC20; CDK1; DLGAP5; MAD2L1; MSN; PCSK9; PLK1; PLK2; RNF19B; TRIB1; TRIB3; UBE2C |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | PSMA5; PSMB6; PSMD1; PSME3; UBE2C; VCP | | | | | | | | | | | | | | | |
| regulation of smooth muscle cell proliferation: GO | 99 | 15 | 2.54 | EREG; HBEGF; HIF1A; HMGCR; HMOX1; IFNG; IL12B; IL6; NAMPT; NDRG4; NR4A3; ORC1; PTAFR; PTGS2; STAT1 | 9 | 1.07 | ADIPOQ; APOD; ELANE; NOX1; NPY5R; PDGFD; PPARGC1A; TPM1; VIPR2 | 1 | 4.22 | ADIPOQ | 0 | 0.00 | | 4 | 1.03 | ELANE; ESR1; IGFBP5; PPARGC1A | 10 | 2.86 | EREG; HBEGF; HIF1A; IGFBP3; NAMPT; ORC1; PPARD; PTAFR; PTGS2; TRIB1 |
| hsp90 chaperone cycle for steroid hormone receptors (shr) | 41 | 8 | 3.27 | CAP1; DYNLL1; FPR1; HSPA8; TUBA1C; TUBA4A; TUBB2A; TUBB6 | 3 | 0.86 | AR; NR3C2; PGR | 0 | 0.00 | | 0 | 0.00 | | 4 | 2.48 | DLC1; NR3C2; PGR; SLC29A1 | 6 | 4.15 | CAP1; HSPA8; TUBA1C; TUBA4A; TUBB2A; TUBB6 |
| negative regulation of tumor necrosis factor superfamily cytokine production: GO | 41 | 6 | 2.45 | ACP5; CD274; GSTP1; LTF; SLAMF1; ZC3H12A | 2 | 0.58 | ADIPOQ; CD34 | 1 | 10.19 | ADIPOQ | 0 | 0.00 | | 1 | 0.62 | CD34 | 6 | 4.15 | ACP5; BCL3; GSTP1; IL10; LTF; ZC3H12A |
| positive regulation of dna replication: GO | 84 | 16 | 3.19 | AREG; CALR; CCT2; CCT3; CCT5; CCT6A; CCT7; CDK1; CSF2; E2F7; EREG; GREM1; IL6; | 4 | 0.56 | BMP5; GLI2; MAPK15; NPM2 | 0 | 0.00 | | 0 | 0.00 | | 1 | 0.30 | GLI2 | 9 | 3.04 | AREG; AURKB; CCT2; CCT5; CDK1; E2F7; EREG; NEK2; PRKCQ |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | NEK2; PCNA; PRKCQ | | | | | | | | | | | | | | | |
| regulation of coagulation: GO | 84 | 12 | 2.39 | F12; F2RL1; HPSE; PLAU; PLAUR; PRKCQ; S100A9; SERPINB2; SERPINE1; SERPINE2; THBD; UBASH3B | 9 | 1.26 | APOE; CD34; ENPP4; F7; HS3ST5; KLKB1; SCARA5; TMPRSS6; TSPAN8 | 0 | 0.00 | | 1 | 4.97 | SERPINE1 | 4 | 1.21 | CD34; PRKG1; SCARA5; TSPAN8 | 9 | 3.04 | F12; HPSE; PLAT; PRKCQ; SERPINB2; SERPINE2; THBD; UBASH3B; VAV2 |
| intrinsic apoptotic signaling pathway in response to dna damage: GO | 69 | 10 | 2.43 | AEN; BAK1; BCL2A1; BRCA2; CDKN1A; HMOX1; IFI16; PYCARD; SFN; TP63 | 3 | 0.51 | BCL2; CRIP1; NUPR1 | 0 | 0.00 | | 0 | 0.00 | | 2 | 0.74 | BCL2; CRIP1 | 8 | 3.29 | BAK1; BCL3; BRCA2; CDKN1A; E2F1; EPHA2; IFI16; SFN |
| dna replication initiation: GO | 29 | 5 | 2.89 | CCNE1; CDC45; CDC6; MCM10; ORC1 | 0 | 0.00 | | 0 | 0.00 | | 0 | 0.00 | | 0 | 0.00 | | 5 | 4.89 | CDC45; CDC6; GINS4; MCM2; ORC1 |
| regulation of dna replication: GO | 152 | 22 | 2.42 | AREG; BLM; BRCA2; CALR; CCT2; CCT3; CCT5; CCT6A; CCT7; CDC6; CDK1; CSF2; E2F7; EREG; ESCO2; GREM1; IL6; NEK2; PCNA; PIF1; PRKCQ; S100A11 | 6 | 0.47 | BMP5; DACH1; GLI2; MAPK15; NPM2; TSPYL2 | 0 | 0.00 | | 0 | 0.00 | | 2 | 0.33 | DACH1; GLI2 | 13 | 2.43 | AREG; AURKB; BLM; BRCA2; CCT2; CCT5; CDC6; CDK1; E2F7; EREG; NEK2; PIF1; PRKCQ |
| regulation of viral genome replication: GO | 70 | 18 | 4.30 | APOBEC3A; HMGA2; IFI16; | 1 | 0.17 | BCL2 | 0 | 0.00 | | 2 | 11.94 | IFITM3; ISG15 | 1 | 0.36 | BCL2 | 8 | 3.24 | HMGA2; IFI16; LTF; MX1; OAS1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | IFITM1; IFITM3; ISG15; ISG20; LTF; MX1; OAS1; OAS3; OASL; PPIA; PPIB; RSAD2; SLPI; TOP2A; ZC3H12A | | | | | | | | | | | | | | | SLPI; TOP2A; ZC3H12A |
| response to ionizing radiation: GO | 135 | 17 | 2.11 | AEN: ANXA1; BAK1; BLM; BRCA2; CCL7; CDKN1A; CXCL10; ECT2; H2AFX; HIF1A; IFI16; IL1B; KRT14; SOCS3; THBD; TP63 | 3 | 0.26 | BCL2; CRYAB; CYP17A1 | 1 | 3.10 | CRYAB | 1 | 3.10 | IL1B | 2 | 0.38 | BCL2; TSPYL5 | 12 | 2.52 | BAK1; BLM; BRCA2; CDKN1A; ECT2; H2AFX; HIF1A; IFI16; RAD51AP1; SNAI2; SOCS3; THBD |
| microtubule organizing center part: GO | 135 | 10 | 1.24 | AURKA; BIRC5; CEP55; HSPA6; PLA2G3; PLK2; POC1A; RAN; STIL; TOP2A | 6 | 0.52 | AGBL4; ALDOB; CCDC146; CROCC; DZIPIL; TSKS | 0 | 0.00 | | 0 | 0.00 | | 0 | 0.00 | | 12 | 2.52 | AURKA; BIRC5; CEP19; CEP55; PLA2G3; PLK2; PLK4; POC1A; RAN; SPAG5; STIL; TOP2A |
| dna recombination: GO | 189 | 15 | 1.33 | BLM; BRCA2; CDC45; EXO1; GEN1; H2AFX; HMGB3; MND1; PCNA; PIF1; POLQ; | 1 | 0.06 | SYCP1 | 0 | 0.00 | | 0 | 0.00 | | 0 | 0.00 | | 15 | 2.25 | BLM; BRCA2; BRIP1; CDC45; EXO1; FEN1; GINS4; H2AFX; HMGB3; MND1; PIF1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | RUVBL1; TOP2A; TRIP13; UBE2N | | | | | | | | | | | | | | | POLQ; RAD51AP1; TOP2A; TRIP13 |
| kinase inhibitor activity: GO | 86 | 6 | 1.17 | CDKN1A; FLRT3; LRRC4; NPM1; SFN; SOCS3 | 8 | 1.10 | CHAD; LRRC4C; LRRTM3; LRRTM4; MAPK8IP1; PODN; PPP1R1B; PRKAR2B | 2 | 9.72 | CDKNIC; PRKAR2B | 0 | 0.00 | | 6 | 1.77 | CHAD; DCN; LRRC15; LRRC4C; PODN; TESC | 9 | 2.97 | CDKN1A; CISH; FLRT3; LRRC4; NPM1; SFN; SOCS3; TRIB1; TRIB3 |
| response to x ray: GO | 30 | 7 | 3.90 | ANXA1; BLM; BRCA2; CDKN1A; HIF1A; THBD; TP63 | 0 | 0.00 | | 0 | 0.00 | | 0 | 0.00 | | 0 | 0.00 | | 5 | 4.73 | BLM; BRCA2; CDKN1A; HIF1A; THBD |
| epidermal growth factor receptor binding: GO | 30 | 6 | 3.35 | AREG; EPGN; EREG; FAM83B; HBEGF; TGFA | 3 | 1.18 | BTC; EGF; ERBB4 | 0 | 0.00 | | 0 | 0.00 | | 2 | 1.69 | EGF; ERBB4 | 5 | 4.73 | AREG; EREG; HBEGF; TGFA; VAV2 |
| presynaptic phase of homologous dna pairing and strand exchange | 30 | 4 | 2.23 | BLM; BRCA2; CHEK1; EXO1 | 0 | 0.00 | | 0 | 0.00 | | 0 | 0.00 | | 0 | 0.00 | | 5 | 4.73 | BLM; BRCA2; BRIP1; CHEK1; EXO1 |
| microtubule based movement: GO | 191 | 19 | 1.66 | ACTR3; CENPE; DLGAP5; DYNLL1; HIF1A; KIF11; KIF14; KIF15; KIF18A; KIF20A; KIF20B; KIF23; | 11 | 0.68 | APBA1; CCDC114; CCDC40; DNAAF1; DNAH11; DNAH6; DYNC1I1; HYDIN; KIF1A; KIFC2; MAPT | 0 | 0.00 | | 0 | 0.00 | | 3 | 0.40 | APBA1; CCDC114; MAPT | 15 | 2.23 | CENPE; DLGAP5; HIF1A; KIF11; KIF14; KIF15; KIF18A; KIF18B; KIF20A; KIF23; KIF2C; KIF4A; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline: Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo: Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo: Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | KIF2C; KIF4A; KTN1; NEFL; NGF; NTRK1; RACGAP1 | | | | | | | | | | | | | | | KIFC1; KTN1; NGF |
| negative regulation of protein catabolic process: GO | 103 | 11 | 1.79 | BUB1; BUB1B; CENPF; LAMP3; MAD2L1; NRG1; PBK; PLK1; SERPINE2; TTK; YOD1 | 5 | 0.57 | GRIN2A; NOS2; SVIP; TIMP3; TIMP4 | 0 | 0.00 | | 1 | 4.06 | LAMP3 | 1 | 0.25 | SVIP | 10 | 2.75 | BUB1; BUB1B; CENPF; IL10; MAD2L1; NRG1; PBK; PLK1; SERPINE2; TTK |
| regulation of tp53 activity | 103 | 8 | 1.30 | AURKA; BLM; CCNA2; CDK1; CHEK1; EXO1; TPX2; USP2 | 1 | 0.11 | PRKAA2 | 0 | 0.00 | | 0 | 0.00 | | 1 | 0.25 | PRKAA2 | 10 | 2.75 | AURKA; AURKB; BLM; BRIP1; CCNA2; CDK1; CHEK1; EXO1; SGK1; TPX2 |
| centromere complex assembly: GO | 43 | 13 | 5.06 | CENPA; CENPE; CENPF; CENPN; CENPW; HIST1H4I; HIST1H4J; HIST1H4K; HIST1H4L; HJURP; NPM1; OIP5; RUVBL1 | 0 | 0.00 | | 0 | 0.00 | | 0 | 0.00 | | 1 | 0.59 | CENPV | 6 | 3.96 | CENPA; CENPE; CENPF; CENPW; HIST1H4I; NPM1 |
| regulation of proteasomal protein catabolic process: GO | 173 | 17 | 1.64 | AURKA; BUB1; BUB1B; CCNB1; CENPF; CSNK1A1; | 3 | 0.20 | CLU; PKD1; SVIP | 0 | 0.00 | | 1 | 2.42 | LAMP3 | 4 | 0.59 | CLU; ECSCR; PRICKLE1; SVIP | 14 | 2.29 | AURKA; BUB1; BUB1B; CCNB1; CENPF; DLGAP5; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | DLGAP5; FBXO5; GEN1; LAMP3; MAD2L1; PBK; PLK1; PLK2; PSME3; TTK; VCP | | | | | | | | | | | | | | | MAD2L1; PBK; PLK1; PLK2; RNF19B; TRIB1; TRIB3; TTK |
| response to purine containing compound: GO | 155 | 17 | 1.84 | AREG; CCNE1; FOSL1; FOXM1; HIF1A; IL1B; IL6; LDHA; NME1; P2RY2; PANX1; PTAFR; PTGS2; SDC1; SELL; STAT1; THBD | 20 | 1.52 | ADIPOQ; ALDOB; CASQ2; CDO1; CFTR; CYP17A1; EEF2K; GPD1; GSTM2; HMGCS2; P2RX1; P2RX6; P2RX7; PER1; PFKFB1; PLA2G5; PPARGC1A; PYGM; REN; SDC2 | 2 | 5.39 | ADIPOQ; GPD1 | 2 | 5.39 | AQP9; IL1B | 4 | 0.66 | HMGCS2; IGFBP5; PFKFB1; PPARGC1A | 13 | 2.38 | AREG; FOSL1; FOXM1; HIF1A; JUNB; LDHA; P2RY2; PANX1; PTAFR; PTGS2; SLC26A6; SLC5A5; THBD |
| I1cam interactions | 104 | 8 | 1.29 | ACTB; HSPA8; KIF4A; MSN; TUBA1C; TUBA4A; TUBB2A; TUBB6 | 8 | 0.91 | ANK2; DCX; DNM1; FGFR1; NCAM1; RPS6KA6; SCN7A; SPTBN4 | 0 | 0.00 | | 0 | 0.00 | | 5 | 1.22 | FGFR1; NCAM1; RPS6KA6; SCN7A; SPTBN4 | 10 | 2.73 | ACTB; HSPA8; KIF4A; MSN; RPS6KA4; TUBA1C; TUBA4A; TUBB2A; TUBB6; VAV2 |
| epithelial cell proliferation: GO | 88 | 10 | 1.90 | AREG; EHF; EREG; FERMT1; HMOX1; IL6; MKI67; SDR16C5; | 5 | 0.67 | ANGPT4; CD34; FABP7; LGR5; PTCH1 | 0 | 0.00 | | 0 | 0.00 | | 7 | 2.02 | ANGPT4; CD34; ESR1; IGFBP5; KRT2; LGR5; PTCH1 | 9 | 2.90 | AREG; EHF; EPHA2; EREG; FERMT1; IGFBP3; MKI67; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | TP63; WNT5A | | | | | | | | | | | | | | | PPARD; WNT5A |
| copi-independent golgi-to-er retrograde traffic | 31 | 6 | 3.24 | CAP1; DYNLL1; TUBA1C; TUBA4A; TUBB2A; TUBB6 | 0 | 0.00 | | 0 | 0.00 | | 0 | 0.00 | | 1 | 0.82 | DLC1 | 5 | 4.57 | CAP1; TUBA1C; TUBA4A; TUBB2A; TUBB6 |
| positive regulation of epidermis development: GO | 31 | 6 | 3.24 | CYP27B1; HPSE; IL20; KRT17; SFN; TRIM16 | 2 | 0.76 | PTCH1; PTCH2 | 0 | 0.00 | | 0 | 0.00 | | 2 | 1.64 | PTCH1; PTCH2 | 5 | 4.57 | CYP27B1; HPSE; IL20; PPARD; SFN |
| shc1 events in erbb4 signaling | 20 | 5 | 4.18 | CDK1; EREG; HBEGF; NRAS; NRG1 | 3 | 1.77 | BTC; ERBB4; NRG2 | 0 | 0.00 | | 0 | 0.00 | | 1 | 1.27 | ERBB4 | 4 | 5.67 | CDK1; EREG; HBEGF; NRG1 |
| anaphase promoting complex: GO | 20 | 4 | 3.35 | BUB1B; CDC20; UBE2C; UBE2S | 0 | 0.00 | | 0 | 0.00 | | 0 | 0.00 | | 0 | 0.00 | | 4 | 5.67 | BUB1B; CDC20; UBE2C; UBE2S |
| apc c cdc20 mediated degradation of cyclin b | 20 | 4 | 3.35 | CCNB1; CDC20; CDK1; UBE2C | 0 | 0.00 | | 0 | 0.00 | | 0 | 0.00 | | 0 | 0.00 | | 4 | 5.67 | CCNB1; CDC20; CDK1; UBE2C |
| carboxyterminal post-translational modifications of tubulin | 20 | 4 | 3.35 | TUBA1C; TUBA4A; TUBB2A; TUBB6 | 0 | 0.00 | | 0 | 0.00 | | 0 | 0.00 | | 0 | 0.00 | | 4 | 5.67 | TUBA1C; TUBA4A; TUBB2A; TUBB6 |
| decidualization: GO | 20 | 4 | 3.35 | CTSB; CYP27B1; GJB2; PTGS2 | 2 | 1.18 | LIF; PTGIS | 0 | 0.00 | | 0 | 0.00 | | 1 | 1.27 | ESR1 | 4 | 5.67 | CYP27B1; JUNB; PPARD; PTGS2 |
| microtubule end: GO | 20 | 2 | 1.67 | ASPM; KIF2C | 0 | 0.00 | | 0 | 0.00 | | 0 | 0.00 | | 0 | 0.00 | | 4 | 5.67 | ASPM; KIF18B; KIF2C; SPAG5 |
| peptide ligand-binding receptors | 59 | 15 | 4.25 | ANXA1; CCK; CCL21; CXCL1; CXCL10; CXCL11; | 5 | 1.00 | AGT; AGTR1; C3; NPY1R; PPOX | 0 | 0.00 | | 0 | 0.00 | | 5 | 2.15 | AGTR1; C3; CXCL12; NPY1R; PPOX | 7 | 3.36 | CCL20; CXCL11; CXCL2; CXCL6; FPR2; NMU; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | CXCL13; CXCL3; CXCL6; CXCL8; CXCR4; F2RL1; FPR1; NMU; PNP | | | | | | | | | | | | | | | PNP |
| protein folding | 45 | 7 | 2.60 | ACTB; CCNE1; PLP2; TUBA1C; TUBA4A; TUBB2A; TUBB6 | 1 | 0.26 | TUBB4A | 0 | 0.00 | | 0 | 0.00 | | 1 | 0.56 | GNG11 | 6 | 3.78 | ACTB; NOP56; TUBA1C; TUBA4A; TUBB2A; TUBB6 |
| translocation of glut4 to the plasma membrane | 45 | 7 | 2.60 | ACTB; RAB10; SFN; TUBA1C; TUBA4A; TUBB2A; TUBB6 | 1 | 0.26 | PRKAA2 | 0 | 0.00 | | 0 | 0.00 | | 1 | 0.56 | PRKAA2 | 6 | 3.78 | ACTB; SFN; TUBA1C; TUBA4A; TUBB2A; TUBB6 |
| positive regulation of telomere maintenance via telomere lengthening: GO | 32 | 7 | 3.66 | CCT2; CCT3; CCT5; CCT6A; CCT7; NEK2; PRKCQ | 1 | 0.37 | MAPK15 | 0 | 0.00 | | 0 | 0.00 | | 0 | 0.00 | | 5 | 4.43 | AURKB; CCT2; CCT5; NEK2; PRKCQ |
| regulation of double strand break repair: GO | 32 | 4 | 2.09 | CHEK1; FOXM1; HMGA2; POLQ | 0 | 0.00 | | 0 | 0.00 | | 0 | 0.00 | | 0 | 0.00 | | 5 | 4.43 | CHEK1; FOXM1; HMGA2; POLQ; RAD51AP1 |
| dna biosynthetic process: GO | 107 | 13 | 2.03 | BLM; BRCA2; CENPF; DTL; EXO1; ISG15; NOP10; PCNA; POLQ; PPIA; TK1; USP43; VCP | 2 | 0.22 | SYCP1; TERT | 0 | 0.00 | | 1 | 3.91 | ISG15 | 1 | 0.24 | CTGF | 10 | 2.65 | BLM; BRCA2; BRIP1; CENPF; DTL; EXO1; POLQ; RAD51AP1; TK1; USP43 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| glucose metabolism | 91 | 13 | 2.39 | ENO1; GAPDH; GK; GOT2; HK2; PFKFB4; PGAM1; PGK1; PGM2; PKM; PYGL; TPI1; TPI1P1 | 6 | 0.78 | ALDOB; GYG2; PCK1; PFKFB1; PHKG1; PYGM | 0 | 0.00 | | 0 | 0.00 | | 3 | 0.84 | ALDOC; PFKFB1; PHKG1 | 9 | 2.80 | ENO1; GAPDH; GOT2; HK2; PFKFB4; PGAM1; PGK1; PKM; TPI1 |
| positive regulation of smooth muscle cell proliferation: GO | 60 | 12 | 3.35 | EREG; HBEGF; HIF1A; HMGCR; HMOX1; IL6; NAMPT; NR4A3; ORC1; PTAFR; PTGS2; STAT1 | 5 | 0.98 | ELANE; NOX1; NPY5R; PDGFD; PPARGC1A | 0 | 0.00 | | 0 | 0.00 | | 2 | 0.85 | ELANE; PPARGC1A | 7 | 3.31 | EREG; HBEGF; HIF1A; NAMPT; ORC1; PTAFR; PTGS2 |
| negative regulation of cellular protein catabolic process: GO | 60 | 8 | 2.23 | BUB1; BUB1B; CENPF; LAMP3; MAD2L1; PBK; PLK1; TTK | 1 | 0.20 | SVIP | 0 | 0.00 | | 1 | 6.96 | LAMP3 | 1 | 0.42 | SVIP | 7 | 3.31 | BUB1; BUB1B; CENPF; MAD2L1; PBK; PLK1; TTK |
| positive regulation of wound healing: GO | 46 | 8 | 2.91 | ANXA1; F12; HBEGF; HPSE; INSL3; S100A9; SERPINE1; THBD | 3 | 0.77 | ADRA2A; ENPP4; F7 | 0 | 0.00 | | 1 | 9.08 | SERPINE1 | 1 | 0.55 | ADRA2A | 6 | 3.70 | F12; HBEGF; HPSE; PPARD; SOX15; THBD |
| myelin sheath: GO | 161 | 21 | 2.18 | CA2; CCT2; CCT3; CCT5; ENO1; FSCN1; GOT2; GSTO1; HSPA5; HSPA8; INA; MSN; NEFL; | 14 | 1.03 | ALB; ATP1A2; BCL2; CRYAB; DNM1; GJC3; GSN; MPZ; MYH14; PLLP; PLP1; PRX; TPPP; | 1 | 2.60 | CRYAB | 0 | 0.00 | | 7 | 1.10 | BCL2; CNRIP1; MPZ; PLLP; PLP1; PMP2; TPPP | 13 | 2.29 | CA2; CCT2; CCT5; ENO1; GOT2; HSPA5; HSPA8; INA; MSN; NDRG1; PGAM1; TKT; VDAC1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline: Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo: Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo: Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | NME1; PDIA3; PGAM1; PRDX1; SLC25A5; TAGLN3; VCP; VDAC1 | | | TUBB4A | | | | | | | | | | | | |
| how progesterone initiates the oocyte maturation | 21 | 4 | 3.19 | CAP1; CCNB1; CDK1; PAQR5 | 3 | 1.69 | ACTA1; PGR; PRKAR2B | 1 | 19.90 | PRKAR2B | 0 | 0.00 | | 1 | 1.21 | PGR | 4 | 5.40 | CAP1; CCNB1; CDK1; PAQR5 |
| sumo e3 ligases sumoylate target proteins | 76 | 11 | 2.42 | AURKA; BIRC5; BLM; CBX2; CDCA8; HIST1H4I; HIST1H4J; HIST1H4K; HIST1H4L; PCNA; TOP2A | 1 | 0.16 | MITF | 0 | 0.00 | | 0 | 0.00 | | 1 | 0.33 | MITF | 8 | 2.98 | AURKA; AURKB; BIRC5; BLM; CBX2; CDCA8; HIST1H4I; TOP2A |
| meiosis i: GO | 76 | 9 | 1.98 | AURKA; BRCA2; CDC25B; CKS2; FBXO5; PLK1; PTTG1; TOP2A; TRIP13 | 2 | 0.31 | STAG3; SYCP1 | 0 | 0.00 | | 0 | 0.00 | | 1 | 0.33 | SYCP3 | 8 | 2.98 | AURKA; BRCA2; CDC25B; CKS2; PLK1; PTTG1; TOP2A; TRIP13 |
| cell junction assembly: GO | 126 | 14 | 1.86 | ACTB; DSG1; ECT2; FBLIM1; FSCN1; GJA1; GJB2; ITGA6; JUP; KRT14; KRT5; LAMB3; RHOD; VMP1 | 9 | 0.84 | ACTN2; AMOT; ANK2; ARHGAP6; BCL2; SORBS1; TLN2; TNS1; WNT11 | 0 | 0.00 | | 0 | 0.00 | | 4 | 0.81 | BCL2; DLC1; TLN2; WNT11 | 11 | 2.48 | ACTB; ACTN1; COL17A1; ECT2; FBLIM1; ITGA6; ITGB4; KRT5; LAMB3; PKP3; RHOD |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| protein hetero-oligomerization: GO | 109 | 15 | 2.30 | CHRNA3; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L; JUP; RRM2 | 13 | 1.41 | ADIPOQ; CHRNA2; GCHFR; GLRB; HBA1; HBA2; HBB; LRP4; MAGI2; NLGN1; P2RX1; P2RX6; TNNT2 | 1 | 3.83 | ADIPOQ | 0 | 0.00 | | 3 | 0.70 | GLRB; HBA2; HBB | 10 | 2.60 | HIST1H3A; HIST1H3C; HIST1H3F; HIST1H3G; HIST1H3H; HIST1H3I; HIST1H3J; HIST1H4I; PDSS1; RRM2 |
| cellular response to extracellular stimulus: GO | 181 | 18 | 1.66 | CCNE1; CDKN1A; CYP24A1; DSC2; EIF2S1; FOSL1; GSTP1; HMOX1; HSPA5; HSPA8; IFI16; ITGA6; PCSK9; RALB; SLC2A1; TNC; UPP1; ZC3H12A | 16 | 1.04 | ALB; ALDOB; BCL2; CARTPT; FOLR1; FOLR2; INHBB; KCNB1; LEP; MAP1LC3C; MYOCD; P2RX7; PCK1; PDK4; PRKAA2; SLC1A2 | 0 | 0.00 | | 0 | 0.00 | | 4 | 0.56 | BCL2; BHLHA15; PDK4; PRKAA2 | 14 | 2.19 | BRIP1; CDKN1A; DSC2; FOSL1; GSTP1; HSPA5; HSPA8; IFI16; ITGA6; PCSK9; SLC2A1; UCN2; WNT9B; ZC3H12A |
| hdr through homologous recombination (hrr) | 47 | 6 | 2.14 | BLM; BRCA2; CHEK1; EXO1; GEN1; PCNA | 0 | 0.00 | | 0 | 0.00 | | 0 | 0.00 | | 0 | 0.00 | | 6 | 3.62 | BLM; BRCA2; BRIP1; CHEK1; EXO1; RAD51AP1 |
| regulation of chemokine production: GO | 62 | 14 | 3.78 | ADCYAP1; F2RL1; GSTP1; HIF1A; HMOX1; | 4 | 0.76 | ADIPOQ; APOD; ELANE; LPL | 2 | 13.48 | ADIPOQ; LPL | 2 | 13.48 | FFAR2; IL1B | 1 | 0.41 | ELANE | 7 | 3.20 | GSTP1; HIF1A; IL10; MEFV; P2RY2; SNAI2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | IFNG; IL1B; IL1RL1; IL4R; IL6; MEFV; P2RY2; PYCARD; WNT5A | | | | | | | | | | | | | | | WNT5A |
| mpr pathway | 34 | 7 | 3.45 | ACTR3; ARPC1A; ARPC3; CAP1; CCNB1; CDK1; PAQR5 | 3 | 1.04 | ACTA1; PGR; PRKAR2B | 1 | 12.29 | PRKAR2B | 0 | 0.00 | | 1 | 0.75 | PGR | 5 | 4.17 | ARPC1A; CAP1; CCNB1; CDK1; PAQR5 |
| response to mineralo-corticoid: GO | 34 | 6 | 2.95 | CCNE1; CDKN1A; FOSL1; NEFL; RAN; TH | 1 | 0.35 | NTRK3 | 0 | 0.00 | | 0 | 0.00 | | 2 | 1.49 | CTGF; SLC18A2 | 5 | 4.17 | CDKN1A; FOSL1; JUNB; RAN; TH |
| cyclin dependent protein kinase activity: GO | 34 | 4 | 1.97 | CCNB1; CCNB2; CDK1; CDK5R1 | 2 | 0.69 | CDK3; CDKL2 | 0 | 0.00 | | 0 | 0.00 | | 2 | 1.49 | CDK14; MAK | 5 | 4.17 | CCNB1; CCNB2; CDK1; CDK18; CDK5R1 |
| regulation of reactive oxygen species metabolic process: GO | 146 | 16 | 1.83 | ACP5; CDKN1A; F2RL1; FOXM1; GSTP1; HIF1A; HK2; IFNG; IL1B; IL6; MMP3; PLAU; PTGS2; RAC2; VDAC1; ZC3H12A | 13 | 1.05 | AGT; AGTR1; BCL2; CD34; CLU; CRYAB; FBLN5; HBB; LEP; PLIN5; PON3; PTGIS; SNCA | 1 | 2.86 | CRYAB | 2 | 5.72 | IL1B; RAC2 | 12 | 2.09 | AGTR1; BCL2; CD34; CLU; ESR1; FBLN5; HBB; MYCN; PDK3; PON3; SLC18A2; SNCA | 12 | 2.33 | ACP5; CDKN1A; FOXM1; GSTP1; HIF1A; HK2; IL10; MMP3; PTGS2; VDAC1; XDH; ZC3H12A |
| grb2 events in erbb2 signaling | 22 | 5 | 3.80 | CDK1; EREG; HBEGF; NRAS; NRG1 | 4 | 2.15 | BTC; EGF; ERBB4; NRG2 | 0 | 0.00 | | 0 | 0.00 | | 2 | 2.31 | EGF; ERBB4 | 4 | 5.16 | CDK1; EREG; HBEGF; NRG1 |
| positive regulation of alcohol | 22 | 5 | 3.80 | IFNG; IL1B; NTSR1; | 4 | 2.15 | FGF1; LHCGR; | 0 | 0.00 | | 1 | 19.00 | IL1B | 3 | 3.46 | ADCYAP1R1; PTHIR; | 4 | 5.16 | HRH1; NTSR1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| biosynthetic process: GO | | | | P2RY1; PTAFR | | | PTHIR; SNCA | | | | | | | | | SNCA | | | P2RY1; PTAFR |
| memory: GO | 94 | 6 | 1.07 | IL1B; ITGA3; KCNK10; PLK2; PTGS2; TH | 15 | 1.88 | ADCY8; CNR1; DRD1; DRD4; GRIA1; GRIN1; GRIN2A; GRM7; ITGA8; NETO1; PLA2G6; RELN; SHANK1; SLC17A7; SLC24A2 | 0 | 0.00 | | 1 | 4.45 | IL1B | 4 | 1.08 | GRIA1; KCNK2; MDK; RELN | 9 | 2.72 | FEN1; HRH1; HRH2; ITGA3; KCNK10; PLK2; PTGS2; SGK1; TH |
| histone binding: GO | 165 | 22 | 2.23 | ASF1B; CBX2; CDYL2; DTX3L; GK; H2AFX; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L; HJURP; NPM1; RCC1; UHRF1 | 9 | 0.64 | APBB1; CBX7; CHD5; FAM156A; FAM156B; HILS1; NAP1L2; NPM2; SNCA | 0 | 0.00 | | 0 | 0.00 | | 3 | 0.46 | CBX7; NAP1L2; SNCA | 13 | 2.23 | CBX2; CDYL2; H2AFX; HIST1H3A; HIST1H3C; HIST1H3F; HIST1H3G; HIST1H3H; HIST1H3I; HIST1H3J; HIST1H4I; MCM2; NPM1 |
| negative regulation of coagulation: GO | 48 | 8 | 2.79 | F12; PLAU; PLAUR; SERPINB2; SERPINE1; SERPINE2; | 6 | 1.47 | APOE; CD34; HS3ST5; KLKB1; TMPRSS6; TSPAN8 | 0 | 0.00 | | 1 | 8.71 | SERPINE1 | 3 | 1.59 | CD34; PRKG1; TSPAN8 | 6 | 3.54 | F12; PLAT; SERPINB2; SERPINE2; THBD; UBASH3B |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | THBD; UBASH3B | | | | | | | | | | | | | | | |
| response to ammonium ion: GO | 48 | 6 | 2.09 | CCNA2; CDK5R1; GNA15; HRH3; PLAU; PTAFR | 5 | 1.23 | CHRM1; CHRM2; CHRM3; CHRM4; GABRB3 | 0 | 0.00 | | 0 | 0.00 | | 3 | 1.59 | CHRM1; CHRM3; SLC18A2 | 6 | 3.54 | AGRN; CCNA2; CDK5R1; GNA15; HRH1; PTAFR |
| helicase activity: GO | 147 | 10 | 1.14 | ANXA1; BLM; CDC45; DDX21; DDX28; DDX60L; EIF4A3; GINS1; PIF1; RUVBL1 | 2 | 0.16 | CHD5; DDX25 | 0 | 0.00 | | 0 | 0.00 | | 1 | 0.17 | DDX25 | 12 | 2.31 | BLM; BRIP1; CDC45; DDX21; DDX28; DDX39A; EIF4A3; GINS1; GINS4; MCM2; PIF1; TDRD9 |
| metabolism of nucleotides | 95 | 11 | 1.94 | CDA; ENTPD7; NME1; NUDT15; PNP; POMP; RRM2; TK1; TXN; TYMP; UPP1 | 2 | 0.25 | AMPD1; UPP2 | 0 | 0.00 | | 0 | 0.00 | | 1 | 0.27 | GLRX | 9 | 2.69 | CDA; CTPS1; ENTPD7; NUDT15; PNP; RRM2; TK1; TXN; XDH |
| cellular response to inorganic substance: GO | 148 | 16 | 1.81 | BLM; CALR; CCNA2; CCNB1; ECT2; EIF2S1; EIF4A3; HIF1A; HMOX1; HSPA5; MMP3; MT2A; PPIF; PRNP; TH; WNT5A | 15 | 1.20 | CACNA1H; CHP2; CYP1A2; EEF2K; FABP4; GPLD1; GRIN1; GSN; KCNA1; KCNJ1; NEUROD2; PPARGC1A; SNCA; SYT1; TF | 0 | 0.00 | | 0 | 0.00 | | 7 | 1.20 | ACER1; CACNA1H; CHP2; GPLD1; PPARGC1A; SLC40A1; SNCA | 12 | 2.30 | BLM; CCNA2; CCNB1; ECT2; EIF4A3; HIF1A; HSPA5; JUNB; MMP3; PPIF; TH; WNT5A |
| oocyte differentiation: | 35 | 7 | 3.35 | BRCA2; CCNB1; | 6 | 2.02 | BCL2; INHBB; | 0 | 0.00 | | 0 | 0.00 | | 2 | 1.45 | BCL2; LGR5 | 5 | 4.05 | BRCA2; CCNB1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| GO | | | | CDC25B; EREG; FBXO5; INSL3; TRIP13 | | | LGR5; NPM2; TDRD5; YBX2 | | | | | | | | | | | | CDC25B; EREG; TRIP13 |
| positive regulation of protein tyrosine kinase activity: GO | 35 | 7 | 3.35 | EPGN; EREG; GREM1; HSPH1; LRP8; NRG1; TGFA | 6 | 2.02 | ADORA1; ADRA2A; AGT; EGF; RELN; SRCIN1 | 1 | 11.94 | SRCIN1 | 0 | 0.00 | | 4 | 2.90 | ADRA2A; EGF; GPRC5B; RELN | 5 | 4.05 | AFAP1L2; EREG; HSPH1; NRG1; TGFA |
| positive regulation of mitochondrial outer membrane permeabilization involved in apoptotic signaling pathway: GO | 35 | 6 | 2.87 | BAK1; DYNLL1; SFN; TP63; YWHAQ; YWHAZ | 1 | 0.34 | BCL2 | 0 | 0.00 | | 1 | 11.94 | GZMB | 1 | 0.73 | BCL2 | 5 | 4.05 | BAK1; E2F1; SFN; YWHAQ; YWHAZ |
| regulation of protein binding: GO | 167 | 12 | 1.20 | AURKA; BAK1; HSPA5; MMP9; NRG1; PLK1; PLK2; RALB; RAN; SLPI; TGFBR1; WNT5A | 15 | 1.06 | ADIPOQ; BCL2; CAMK1; CDON; DACT1; DKK1; FRMD7; GREM2; HDAC5; ICA1; NOG; PKD1; SPAG8; TERT; WFIKKN1 | 2 | 5.00 | ADIPOQ; WFIKKN1 | 0 | 0.00 | | 7 | 1.07 | ANGPT1; BCL2; CAMK1; CDON; DACT1; GREM2; ICA1 | 13 | 2.21 | AURKA; AURKB; BAK1; GTSE1; HSPA5; IL10; NRG1; PLK1; PLK2; RAN; SLPI; TRIB3; WNT5A |
| regulation of telomere maintenance via telomere lengthening: GO | 49 | 8 | 2.73 | CCT2; CCT3; CCT5; CCT6A; CCT7; NEK2; PIF1; PRKCQ | 1 | 0.24 | MAPK15 | 0 | 0.00 | | 0 | 0.00 | | 0 | 0.00 | | 6 | 3.47 | AURKB; CCT2; CCT5; NEK2; PIF1; PRKCQ |
| regulation of vasoconstriction: GO | 64 | 6 | 1.57 | BDKRB2; GJA1; HIF1A; PRKCQ; | 14 | 2.58 | ADRA1A; ADRA1B; ADRA2A; | 0 | 0.00 | | 0 | 0.00 | | 7 | 2.78 | ADRA1A; ADRA2A; AGTR1; | 7 | 3.10 | BDKRB2; HIF1A; HRH1; HRH2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | PTAFR; PTGS2 | | | AGT; AGTR1; ATP1A2; CHRM1; CHRM3; DRD1; EDN3; KCNMB4; LEP; NPY1R; P2RX1 | | | | | | | | | CHRM1; CHRM3; EDN3; NPY1R | | | PRKCQ; PTAFR; PTGS2 |
| regulation of nuclease activity: GO | 23 | 7 | 5.09 | BAK1; GZMA; HSPA5; NPM1; OAS1; OAS3; PCNA | 1 | 0.51 | NEIL1 | 0 | 0.00 | | 0 | 0.00 | | 0 | 0.00 | | 4 | 4.93 | BAK1; HSPA5; NPM1; OAS1 |
| innervation: GO | 23 | 6 | 4.37 | FBXO45; NPTX1; NTRK1; SERPINE2; SULF2; UNC13A | 4 | 2.05 | COL25A1; GABRB3; RNF165; SEMA3A | 0 | 0.00 | | 0 | 0.00 | | 1 | 1.10 | SLITRK6 | 4 | 4.93 | FBXO45; NPTX1; SERPINE2; UNC13A |
| positive regulation of chromosome segregation: GO | 23 | 5 | 3.64 | CCNB1; CDC6; DLGAP5; FBXO5; PLK1 | 0 | 0.00 | | 0 | 0.00 | | 0 | 0.00 | | 0 | 0.00 | | 4 | 4.93 | CCNB1; CDC6; DLGAP5; PLK1 |
| regulation of fibroblast proliferation: GO | 80 | 8 | 1.67 | CCNA2; CCNB1; CDC6; CDKN1A; EREG; GSTP1; IFI30; WNT5A | 6 | 0.88 | AGT; BTC; C1QL4; DACH1; NUPR1; PDGFD | 0 | 0.00 | | 0 | 0.00 | | 4 | 1.27 | DACH1; DDR2; ESR1; FBLN1 | 8 | 2.84 | CCNA2; CCNB1; CDC6; CDKN1A; E2F1; EREG; GSTP1; WNT5A |
| positive regulation of interleukin 1 production: GO | 36 | 8 | 3.72 | CCL3; IFI16; IFNG; NLRP2; PANX1; PYCARD; TRIM16; WNT5A | 1 | 0.33 | P2RX7 | 0 | 0.00 | | 0 | 0.00 | | 0 | 0.00 | | 5 | 3.94 | CCL20; IFI16; NLRP2; PANX1; WNT5A |
| pi3k events in erbb4 signaling | 36 | 4 | 1.86 | CDKN1A; EREG; HBEGF; NRG1 | 3 | 0.98 | BTC; ERBB4; NRG2 | 0 | 0.00 | | 0 | 0.00 | | 1 | 0.71 | ERBB4 | 5 | 3.94 | CDKN1A; EREG; HBEGF; NRG1; TRIB3 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| cell aging: GO | 65 | 10 | 2.57 | BRCA2; CALR; CDK1; CDKN1A; CHEK1; H2AFX; HMGA2; NPM1; SERPINE1; TP63 | 4 | 0.73 | BCL2; C2orf40; PRELP; TERT | 1 | 6.43 | C2orf40 | 1 | 6.43 | SERPINE1 | 1 | 0.39 | BCL2 | 7 | 3.05 | BRCA2; CDK1; CDKN1A; CHEK1; H2AFX; HMGA2; NPM1 |
| cellular response to uv: GO | 65 | 10 | 2.57 | BAK1; CDC25A; CDKN1A; CHEK1; EIF2S1; HYAL3; PBK; PCNA; PTGS2; TP63 | 2 | 0.36 | CRIP1; MFAP4 | 0 | 0.00 | | 0 | 0.00 | | 1 | 0.39 | CRIP1 | 7 | 3.05 | AURKB; BAK1; CDC25A; CDKN1A; CHEK1; PBK; PTGS2 |
| apc/c: cdh1 mediated degradation of cdc20 and other apc/c: cdh1 targeted proteins in late mitosis/early g1 | 50 | 7 | 2.34 | AURKA; CDC20; PLK1; PSMA5; PSMB6; PTTG1; UBE2C | 0 | 0.00 | | 0 | 0.00 | | 0 | 0.00 | | 0 | 0.00 | | 6 | 3.40 | AURKA; AURKB; CDC20; PLK1; PTTG1; UBE2C |
| non-integrin membrane-ecm interactions | 50 | 4 | 1.34 | ITGA6; LAMB3; SDC1; TNC | 3 | 0.71 | DMD; LAMA2; SDC2 | 0 | 0.00 | | 0 | 0.00 | | 4 | 2.03 | DDR2; GULP1; LAMA2; NTN4 | 6 | 3.40 | ACTN1; AGRN; ITGA6; ITGB4; LAMB3; TKT |
| glycosphingolipid biosynthesis lacto and neolacto series | 24 | 5 | 3.49 | B3GNT3; B3GNT5; FUT1; FUT2; FUT3 | 4 | 1.97 | ABO; B3GALT1; B3GALT5; FUT9 | 0 | 0.00 | | 0 | 0.00 | | 2 | 2.12 | ABO; B3GALT1 | 4 | 4.73 | B3GNT5; FUT1; FUT2; FUT3 |
| platelet degranulation | 24 | 5 | 3.49 | CAP1; HSPA5; MANF; PPIA; TOR4A | 0 | 0.00 | | 0 | 0.00 | | 0 | 0.00 | | 1 | 1.06 | SCCPDH | 4 | 4.73 | CAP1; HSPA5; TAGLN2; TOR4A |
| lens fiber cell differentiation: | 24 | 3 | 2.09 | BFSP1; SLC7A11; | 2 | 0.98 | NTRK3; TMOD1 | 0 | 0.00 | | 0 | 0.00 | | 0 | 0.00 | | 4 | 4.73 | BFSP1; EPHA2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| GO | | | | WNT7A | | | | | | | | | | | | | | | SLC7A11; WNT7A |
| sumoylation | 82 | 11 | 2.24 | AURKA; BIRC5; BLM; CBX2; CDCA8; HIST1H4I; HIST1H4J; HIST1H4K; HIST1H4L; PCNA; TOP2A | 1 | 0.14 | MITF | 0 | 0.00 | | 0 | 0.00 | | 1 | 0.31 | MITF | 8 | 2.77 | AURKA; AURKB; BIRC5; BLM; CBX2; CDCA8; HIST1H4I; TOP2A |
| embryonic placenta development: GO | 82 | 8 | 1.63 | CSF2; E2F7; EOMES; GJB5; HIF1A; MDFI; PRDM1; SOCS3 | 4 | 0.58 | CDX4; LIF; PKD1; TTPA | 1 | 5.10 | CDKNIC | 0 | 0.00 | | 1 | 0.31 | CDX4 | 8 | 2.77 | ASCL2; E2F7; HIF1A; IL10; JUNB; MDFI; PLK4; SOCS3 |
| apc c cdc20 mediated degradation of mitotic proteins | 66 | 11 | 2.79 | BUB1B; CCNB1; CDC20; CDK1; MAD2L1; PSMA4; PSMA5; PSMB6; PSMD1; PTTG1; UBE2C | 0 | 0.00 | | 0 | 0.00 | | 0 | 0.00 | | 0 | 0.00 | | 7 | 3.01 | BUB1B; CCNB1; CDC20; CDK1; MAD2L1; PTTG1; UBE2C |
| positive regulation of dna metabolic process: GO | 171 | 23 | 2.25 | ANXA3; AREG; CALR; CCT2; CCT3; CCT5; CCT6A; CCT7; CDK1; CSF2; E2F7; EREG; FOXM1; GREM1; H2AFX; IFNG; IL6; | 7 | 0.48 | APBB1; BMP5; GLI2; MAPK15; NPM2; PAK3; PPARGC1A | 0 | 0.00 | | 1 | 2.44 | ANXA3 | 3 | 0.45 | GLI2; PAK3; PPARGC1A | 13 | 2.16 | AREG; AURKB; CCT2; CCT5; CDK1; E2F7; EREG; FOXM1; H2AFX; NEK2; PFN1; PRKCQ; TOP2A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | NEK2; PCNA; PFN1; PRKCQ; TOP2A; UBE2N | | | | | | | | | | | | | | | |
| meiotic chromosome segregation: GO | 51 | 7 | 2.30 | ACTR3; BRCA2; PLK1; PTTG1; SMC4; TOP2A; TRIP13 | 2 | 0.46 | STAG3; SYCP1 | 0 | 0.00 | | 0 | 0.00 | | 0 | 0.00 | | 6 | 3.34 | BRCA2; PLK1; PTTG1; SMC4; TOP2A; TRIP13 |
| cell matrix adhesion: GO | 117 | 8 | 1.14 | CCL21; HPSE; ITGA3; ITGA6; ITGB6; LYPD3; LYPD5; RHOD | 17 | 1.71 | ACTN2; ARHGAP6; BCL2; CD34; EDA; EPDR1; FBLN5; FREM1; ITGA7; ITGA8; MUC4; OTOA; PKD1; SORBS1; TMEM8B; TNN; TNXB | 0 | 0.00 | | 0 | 0.00 | | 9 | 1.95 | BCL2; CD34; CTGF; DLC1; FBLN5; FREM1; ITGA11; TMEM8B; TNN | 10 | 2.42 | ACTN1; COL17A1; HPSE; ITGA3; ITGA6; ITGB4; ITGB6; LYPD3; LYPD5; RHOD |
| regulation of membrane permeability: GO | 67 | 9 | 2.25 | BAK1; DYNLL1; HK2; PPIF; SFN; SLC25A5; TP63; YWHAQ; YWHAZ | 3 | 0.53 | BCL2; CAMK2A; NOL3 | 0 | 0.00 | | 1 | 6.24 | GZMB | 1 | 0.38 | BCL2 | 7 | 2.96 | BAK1; E2F1; HK2; PPIF; SFN; YWHAQ; YWHAZ |
| monosaccharide transport: GO | 52 | 6 | 1.93 | FABP5; HK2; NRG1; SLC2A1; SLC2A9; SLC5A1 | 7 | 1.59 | DRD1; KLF15; SLC26A5; SLC2A4; SLC5A2; SLC5A9; SORBS1 | 0 | 0.00 | | 0 | 0.00 | | 2 | 0.98 | SLC2A12; SLC5A9 | 6 | 3.27 | FABP5; HK2; NRG1; PPARD; SLC2A1; SLC2A9 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| regulation of dna recombination: GO | 52 | 6 | 1.93 | BLM; CHEK1; IFNG; IL7R; KPNA2; POLQ | 0 | 0.00 | | 0 | 0.00 | | 1 | 8.04 | IL7R | 0 | 0.00 | | 6 | 3.27 | BLM; CHEK1; IL10; KPNA2; POLQ; RAD51AP1 |
| carbohydrate biosynthetic process: GO | 118 | 13 | 1.84 | B3GNT3; ENO1; FUT3; GAPDH; GOT2; GSTO1; HAS3; PGAM1; PGK1; PGM2; SLC2A1; ST6GALNAC1; TPI1 | 14 | 1.40 | ALDOB; B3GALT1; CHST12; GPD1; GYG2; HAS1; LEP; PCK1; PFKFB1; PGM5; PHKG1; PPARGC1A; RBP4; ST6GALNAC5 | 1 | 3.54 | GPD1 | 0 | 0.00 | | 8 | 1.72 | ALDOC; B3GALT1; CHST12; PFKFB1; PGM5; PHKG1; PPARGC1A; ST6GALNAC5 | 10 | 2.40 | ENO1; FUT3; GAPDH; GOT2; PGAM1; PGK1; SLC2A1; ST6GALNAC1; TKT; TPI1 |
| xenophagy: GO | 101 | 14 | 2.32 | EIF2S1; FCGR3B; FGFBP1; HIST1H3A; HIST1H3B; HIST1H3C; HIST1H3F; HIST1H3G; HIST1H3H; HIST1H3I; HIST1H3J; SERPINB10; TEAD4; TREM1 | 8 | 0.93 | FGF14; HCAR1; MAP1A; MSTN; MYOM1; PDK4; PHYHIP; REEP2 | 0 | 0.00 | | 1 | 4.14 | TREM1 | 3 | 0.75 | LMCD1; MYOM1; PDK4 | 9 | 2.53 | FGFBP1; HIST1H3A; HIST1H3C; HIST1H3F; HIST1H3G; HIST1H3H; HIST1H3I; HIST1H3J; TEAD4 |
| nucleobase catabolism | 25 | 6 | 4.02 | ENTPD7; NUDT15; PNP; POMP; TYMP; UPP1 | 0 | 0.00 | | 0 | 0.00 | | 0 | 0.00 | | 0 | 0.00 | | 4 | 4.54 | ENTPD7; NUDT15; PNP; XDH |
| dna strand elongation involved in dna replication: GO | 25 | 3 | 2.01 | GINS1; GINS3; PCNA | 0 | 0.00 | | 0 | 0.00 | | 0 | 0.00 | | 0 | 0.00 | | 4 | 4.54 | FEN1; GINS1; GINS3; GINS4 |
| dna synthesis involved in | 68 | 8 | 1.97 | BLM; BRCA2; DTL; | 1 | 0.17 | SYCP1 | 0 | 0.00 | | 1 | 6.15 | ISG15 | 0 | 0.00 | | 7 | 2.92 | BLM; BRCA2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| dna repair: GO | | | | EXO1; ISG15; PCNA; USP43; VCP | | | | | | | | | | | | | | | BRIP1; DTL; EXO1; RAD51AP1; USP43 |
| synapse assembly: GO | 68 | 7 | 1.72 | FBXO45; FLRT3; NLGN4X; NRG1; SDK2; WNT5A; WNT7A | 10 | 1.73 | DRD1; IL1RAPL1; LRP4; MAGI2; NLGN1; NRXN1; NRXN3; PCDHB16; PCDHB3; PCLO | 0 | 0.00 | | 0 | 0.00 | | 6 | 2.24 | NRXN1; PCDHB11; PCDHB3; PCDHB6; PCLO; SLITRK6 | 7 | 2.92 | FBXO45; FLRT3; NLGN4X; NRG1; SDK2; WNT5A; WNT7A |
| response to organo phosphorus: GO | 137 | 14 | 1.71 | AREG; FOSL1; FOXM1; IL1B; LDHA; NME1; PANX1; PTAFR; PTGS2; SDC1; SELL; STAT1; THBD; TRIM16 | 16 | 1.38 | ADIPOQ; ALDOB; CDO1; CFTR; CYP17A1; EEF2K; GPD1; HMGCS2; P2RX1; P2RX6; P2RX7; PER1; PFKFB1; PLA2G5; PYGM; REN | 2 | 6.10 | ADIPOQ; GPD1 | 2 | 6.10 | AQP9; IL1B | 4 | 0.74 | HMGCS2; IGFBP5; LPAR1; PFKFB1 | 11 | 2.28 | AREG; FOSL1; FOXM1; JUNB; LDHA; PANX1; PTAFR; PTGS2; SLC26A6; SLC5A5; THBD |
| cilium assembly | 119 | 10 | 1.41 | CCT5; CDK1; DYNLL1; KIF2C; NEK2; PLK1; TUBA1C; TUBA4A; TUBB2A; TUBB6 | 3 | 0.30 | ALB; MAST1; PRKAR2B | 1 | 3.51 | PRKAR2B | 20 | 0.00 | | 2 | 0.43 | B9D1; DLC1 | 10 | 2.38 | CCT5; CDK1; KIF2C; NEK2; PLK1; PLK4; TUBA1C; TUBA4A; TUBB2A; TUBB6 |
| nfat 3pathway | 53 | 7 | 2.21 | CSNK1A1; KPNA2; PRKCQ; RAN; SFN; YWHAQ; YWHAZ | 2 | 0.45 | BCL2; RCAN2 | 0 | 0.00 | | 0 | 0.00 | | 2 | 0.96 | BCL2; RCAN2 | 6 | 3.21 | KPNA2; PRKCQ; RAN; SFN; YWHAQ; YWHAZ |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| regulation of lymphocyte apoptotic process: GO | 53 | 7 | 2.21 | CD274; HIF1A; IDO1; JAK3; PRELID1; PRKCQ; WNT5A | 7 | 1.56 | BIRC7; GPAM; IRS2; P2RX7; PIP; RORC; TSC22D3 | 1 | 7.88 | GPAM | 0 | 0.00 | | 3 | 1.44 | PIP; SLC46A2; TSC22D3 | 6 | 3.21 | AURKB; HIF1A; IL10; PRELID1; PRKCQ; WNT5A |
| loss of proteins required for interphase microtubule organization from the centrosome | 53 | 6 | 1.89 | CDK1; DYNLL1; NEK2; PLK1; TUBA1C; TUBA4A | 2 | 0.45 | MAST1; PRKAR2B | 1 | 7.88 | PRKAR2B | 0 | 0.00 | | 1 | 0.48 | DLC1 | 6 | 3.21 | CDK1; NEK2; PLK1; PLK4; TUBA1C; TUBA4A |
| response to camp: GO | 102 | 9 | 1.48 | AREG; FOSL1; FOXM1; LDHA; NME1; PTAFR; SDC1; STAT1; THBD | 13 | 1.50 | ADIPOQ; ALDOB; CDO1; CFTR; CYP17A1; EEF2K; GPD1; HMGCS2; PER1; PFKFB1; PLA2G5; PYGM; REN | 2 | 8.19 | ADIPOQ; GPD1 | 1 | 4.10 | AQP9 | 3 | 0.75 | HMGCS2; IGFBP5; PFKFB1 | 9 | 2.50 | AREG; FOSL1; FOXM1; JUNB; LDHA; PTAFR; SLC26A6; SLC5A5; THBD |
| organic acid transmembrane transporter activity: GO | 138 | 15 | 1.82 | PDPN; SERINC2; SLC10A6; SLC16A1; SLC16A6; SLC16A9; SLC26A9; SLC2A9; SLC38A1; SLC38A5; SLC6A11; SLC7A1; SLC7A11; SLC7A5; SLC7A8 | 19 | 1.62 | ABCB11; ABCC3; OCA2; SLC10A2; SLC13A2; SLC16A11; SLC16A12; SLC16A8; SLC17A7; SLC1A2; SLC1A6; SLC1A7; SLC26A1; SLC26A5; SLC26A7; SLC6A17; SLC7A10; | 0 | 0.00 | | 1 | 3.03 | AQP9 | 4 | 0.74 | SLC13A2; SLC16A10; SLC1A6; SLC1A7 | 11 | 2.26 | SERINC2; SLC13A5; SLC16A6; SLC16A9; SLC26A6; SLC2A9; SLC38A5; SLC6A11; SLC7A1; SLC7A11; SLC7A5 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | SLC7A14; SLC7A9 | | | | | | | | | | | | |
| anchoring of the basal body to the plasma membrane | 69 | 7 | 1.70 | CDK1; DYNLL1; KIF2C; NEK2; PLK1; TUBA1C; TUBA4A | 3 | 0.51 | ALB; MAST1; PRKAR2B | 1 | 6.06 | PRKAR2B | 0 | 0.00 | | 2 | 0.74 | B9D1; DLC1 | 7 | 2.88 | CDK1; KIF2C; NEK2; PLK1; PLK4; TUBA1C; TUBA4A |
| microtubule polymerization or depolymerization: GO | 39 | 4 | 1.72 | FBXO5; KIF14; KIF18A; KIF2C | 3 | 0.91 | CRYAB; TPPP; TPPP3 | 2 | 21.43 | CRYAB; TPPP3 | 0 | 0.00 | | 1 | 0.65 | TPPP | 5 | 3.64 | KIF14; KIF18A; KIF18B; KIF2C; SGK1 |
| protein serine threonine tyrosine kinase activity: GO | 39 | 2 | 0.86 | AURKA; TTK | 3 | 0.91 | PAK3; PRKAA2; RELN | 0 | 0.00 | | 0 | 0.00 | | 3 | 1.95 | PAK3; PRKAA2; RELN | 5 | 3.64 | AURKA; AURKB; DYRK3; SGK1; TTK |
| cerebral cortex development: GO | 103 | 11 | 1.79 | ASPM; CDK5R1; CNTNAP2; EOMES; FBXO45; H2AFX; HIF1A; KIF14; LRP8; NEFL; TH | 11 | 1.26 | CDON; DCX; EMX2; FGFR1; GRIN1; HTR6; PAX6; POU3F3; RELN; SEMA3A; SLIT2 | 0 | 0.00 | | 0 | 0.00 | | 7 | 1.73 | CDON; EMX2; FGFR1; MDK; POU3F3; RELN; SLIT2 | 9 | 2.48 | ASPM; CDK5R1; CNTNAP2; FBXO45; H2AFX; HIF1A; KIF14; TACC3; TH |
| jak-stat signaling pathway | 139 | 21 | 2.53 | CCND2; CSF2; IFNE; IFNG; IL12B; IL12RB2; IL13RA1; IL13RA2; IL19; IL20; IL22; IL24; IL26; IL2RA; IL4R; IL6; IL7R; JAK3; OSM; SOCS3; STAT1 | 9 | 0.76 | CNTFR; GHR; IFNA5; IL11RA; IL5; LEP; LEPR; LIF; LIFR | 1 | 3.01 | GHR | 4 | 12.03 | IL21R; IL2RA; IL7R; OSM | 3 | 0.55 | CNTFR; IL11RA; SPRY1 | 11 | 2.24 | CCND2; CISH; IFNE; IL10; IL12RB2; IL13RA2; IL19; IL20; IL22; SOCS3; SPRY4 |
| cell junction organization: GO | 177 | 19 | 1.80 | ACTB; CDH3; CXADR; DSG1; DSP; | 14 | 0.93 | ACTN2; AMOT; ANK2; | 0 | 0.00 | | 0 | 0.00 | | 6 | 0.86 | BCL2; CADM2; CADM3; | 13 | 2.08 | ACTB; ACTN1; COL17A1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | ECT2; FBLIM1; FSCN1; GJA1; GJB2; ITGA6; JUP; KRT14; KRT5; LAMB3; NLGN4X; PERP; RHOD; VMP1 | | | ARHGAP6; BCL2; CADM2; CADM3; CAMSAP3; CDH12; CDH4; SORBS1; TLN2; TNS1; WNT11 | | | | | | | | | DLC1; TLN2; WNT11 | | | ECT2; FBLIM1; ITGA6; ITGB4; KRT5; LAMB3; NLGN4X; PKP3; RHOD; SNAI2 |
| regulation of protein import: GO | 177 | 18 | 1.70 | CDK1; CDKN1A; ECT2; GREM1; HSPA8; IL12B; IL1B; IL6; JUP; MDFI; PRDX1; PRKCQ; PTGS2; RGS20; SULF2; TGFBR1; TXN; ZC3H12A | 9 | 0.60 | APOD; CHP2; DACT1; EDA; EGF; ERBB4; LEP; NOL3; PKD1 | 0 | 0.00 | | 1 | 2.36 | IL1B | 7 | 1.00 | ANGPT1; CHP2; DACT1; EGF; ERBB4; FZD7; ZIC1 | 13 | 2.08 | BCL3; CDK1; CDKN1A; ECT2; HSPA8; IL10; MDFI; PRKCQ; PTGS2; RGS20; SNAI2; TXN; ZC3H12A |
| cellular response to biotic stimulus: GO | 158 | 24 | 2.54 | CCL3; CCR5; CD80; CLEC7A; CMPK2; CSF2; CXCL10; GSTP1; HIF1A; HSPA5; IFNG; IL12B; IL1B; IL24; IL6; P2RY2; PLAU; PLSCR3; PTAFR; | 7 | 0.52 | CPEB1; CYP17A1; HDAC5; HMGCS2; NOS2; PPARGC1A; TXNIP | 0 | 0.00 | | 2 | 5.29 | IL1B; SERPINE1 | 4 | 0.64 | CPEB1; HMGCS2; PPARGC1A; TXNIP | 12 | 2.15 | CCL20; CLEC7A; GSTP1; HIF1A; HSPA5; IL10; P2RY2; PPARD; PTAFR; SBNO2; WNT5A; ZC3H12A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | PYCARD; SERPINE1; TNIP3; WNT5A; ZC3H12A | | | | | | | | | | | | | | | |
| desmosome: GO | 26 | 8 | 5.15 | DSC1; DSC2; DSC3; DSG1; DSG3; DSP; JUP; PERP | 0 | 0.00 | | 0 | 0.00 | | 0 | 0.00 | | 0 | 0.00 | | 4 | 4.36 | DSC2; DSC3; DSG4; PKP3 |
| response to corticosterone: GO | 26 | 5 | 3.22 | CCNE1; CDKN1A; FOSL1; NEFL; TH | 1 | 0.45 | NTRK3 | 0 | 0.00 | | 0 | 0.00 | | 1 | 0.98 | SLC18A2 | 4 | 4.36 | CDKN1A; FOSL1; JUNB; TH |
| integrin cs pathway | 26 | 4 | 2.57 | ITGA3; ITGA6; ITGAX; ITGB6 | 2 | 0.91 | ITGA7; ITGA8 | 0 | 0.00 | | 0 | 0.00 | | 1 | 0.98 | ITGA11 | 4 | 4.36 | ITGA3; ITGA6; ITGB4; ITGB6 |
| response to gonadotropin: GO | 26 | 4 | 2.57 | CCNA2; FOXM1; GJB2; ITGA3 | 3 | 1.36 | CYP17A1; LHCGR; PPARGC1A | 0 | 0.00 | | 0 | 0.00 | | 1 | 0.98 | PPARGC1A | 4 | 4.36 | CCNA2; FOXM1; ITGA3; SLC5A5 |
| regulation of dna replication | 54 | 8 | 2.48 | CCNA2; CDKN1A; E2F3; MCM10; ORC1; ORC6; PSMA5; PSMB6 | 0 | 0.00 | | 0 | 0.00 | | 0 | 0.00 | | 0 | 0.00 | | 6 | 3.15 | CCNA2; CDKN1A; E2F1; MCM2; ORC1; ORC6 |
| switching of origins to a post-replicative state | 54 | 7 | 2.17 | CCNA2; CDC6; CDKN1A; ORC1; ORC6; PSMA5; PSMB6 | 0 | 0.00 | | 0 | 0.00 | | 0 | 0.00 | | 0 | 0.00 | | 6 | 3.15 | CCNA2; CDC6; CDKN1A; MCM2; ORC1; ORC6 |
| positive regulation of chromosome organization: GO | 140 | 14 | 1.67 | CCNB1; CCT2; CCT3; CCT5; CCT6A; CCT7; DLGAP5; FBXO5; | 7 | 0.59 | KAT2A; LIF; MAPK15; NAP1L2; PIWIL2; PPARGC1A; TET1 | 0 | 0.00 | | 1 | 2.98 | IL1B | 3 | 0.54 | NAP1L2; PPARGC1A; TET1 | 11 | 2.23 | AURKB; CCNB1; CCT2; CCT5; DLGAP5; HIST1H1B; NEK2; PLK1; PRKCQ; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | HIST1H1B; IL1B; NEK2; PLK1; PRKCQ; UBE2N | | | | | | | | | | | | | | | RPS6KA4; SNAI2 |
| signaling by wnt | 178 | 21 | 1.97 | CSNK1A1; H2AFX; H2AFZ; HIST1H2AE; HIST1H2BB; HIST1H2BF; HIST1H2BH; HIST1H2BK; HIST1H2BM; HIST1H3A; HIST1H3I; HIST1H4I; HIST1H4J; HIST1H4K; HIST1H4L; PSMA4; PSMA5; PSMB6; PSMD1; RUVBL1; WNT5A | 3 | 0.20 | DKK1; FZD4; LGR5 | 0 | 0.00 | | 0 | 0.00 | | 3 | 0.43 | FZD7; GNG11; LGR5 | 13 | 2.07 | H2AFX; H2AFZ; HIST1H2AE; HIST1H2BB; HIST1H2BD; HIST1H2BF; HIST1H2BK; HIST1H2BM; HIST1H3A; HIST1H3I; HIST1H4I; HIST2H2BE; WNT5A |
| gap junction trafficking | 40 | 10 | 4.18 | ACTB; GJA1; GJB2; GJB3; GJB5; GJB6; TUBA1C; TUBA4A; TUBB2A; TUBB6 | 2 | 0.59 | DNM1; GJB4 | 0 | 0.00 | | 0 | 0.00 | | 1 | 0.64 | GJB4 | 5 | 3.54 | ACTB; TUBA1C; TUBA4A; TUBB2A; TUBB6 |
| intercellular bridge: GO | 40 | 4 | 1.67 | CDCA8; CEP55; KIF23; KLK6 | 1 | 0.29 | CD34 | 0 | 0.00 | | 0 | 0.00 | | 1 | 0.64 | CD34 | 5 | 3.54 | AURKB; BCL3; CDCA8; CEP55; KIF23 |
| class a/1 (rhodopsin-like receptors) | 88 | 17 | 3.23 | ANXA1; CCK; CCL21; CXCL1; CXCL10; | 8 | 1.07 | ADRA1A; ADRB1; AGT; AGTR1; C3; NPY1R; | 0 | 0.00 | | 0 | 0.00 | | 7 | 2.02 | ADRA1A; AGTR1; C3; CXCL12; LPAR1; | 8 | 2.58 | CCL20; CXCL11; CXCL2; CXCL6; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | CXCL11; CXCL13; CXCL3; CXCL6; CXCL8; CXCR4; F2RL1; FPR1; GPR4; LTB4R; NMU; PNP | | | PLPPR1; PPOX | | | | | | | | | NPY1R; PPOX | | | FPR2; HRH1; NMU; PNP |
| cellular response to light stimulus: GO | 88 | 12 | 2.28 | BAK1; CDC25A; CDKN1A; CHEK1; CNGB1; EIF2S1; HIF1A; HYAL3; PBK; PCNA; PTGS2; TP63 | 4 | 0.54 | CRIP1; CRY2; MFAP4; TRPM1 | 0 | 0.00 | | 0 | 0.00 | | 2 | 0.58 | CRIP1; CRY2 | 8 | 2.58 | AURKB; BAK1; CDC25A; CDKN1A; CHEK1; HIF1A; PBK; PTGS2 |
| epithelial cell development: GO | 180 | 20 | 1.86 | BFSP1; CDKN1A; CXCR4; F2RL1; GDNF; GJA1; GPR4; GREM1; HIF1A; MSN; NTRK1; PRDM1; RAB25; RAP2B; SDC1; SFN; TP63; VSIG1; WNT5A; WNT7A | 18 | 1.18 | ARHGEF26; ATP2B2; BMP5; CLIC5; DACT2; DNASEIL2; FGFR1; GSTM3; HAPLN2; HYDIN; MAGI2; PAX6; PDZD7; ROS1; SLC9A4; SOX8; TMOD1; TNMD | 0 | 0.00 | | 0 | 0.00 | | 10 | 1.41 | ARHGEF26; CLIC5; ESR1; FGFR1; FOXA1; FZD7; PDZD7; SHROOM3; SLITRK6; TNMD | 13 | 2.05 | BFSP1; CDKN1A; EPHA2; HIF1A; HRH2; MSN; RAP2B; SFN; SLC4A7; TMC1; VSIG1; WNT5A; WNT7A |
| gap junction assembly | 27 | 9 | 5.58 | GJA1; GJB2; GJB3; GJB5; GJB6; | 1 | 0.44 | GJB4 | 0 | 0.00 | | 0 | 0.00 | | 1 | 0.94 | GJB4 | 4 | 4.20 | TUBA1C; TUBA4A; TUBB2A; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | TUBA1C; TUBA4A; TUBB2A; TUBB6 | | | | | | | | | | | | | | | TUBB6 |
| positive regulation of telomerase activity: GO | 27 | 4 | 2.48 | CCT2; GREM1; NEK2; PRKCQ | 1 | 0.44 | MAPK15 | 0 | 0.00 | | 0 | 0.00 | | 0 | 0.00 | | 4 | 4.20 | AURKB; CCT2; NEK2; PRKCQ |
| response to ischemia: GO | 27 | 4 | 2.48 | EIF4EBP1; HK2; PANX1; PPIF | 7 | 3.06 | BCL2; CAMK2A; EEF2K; NDNF; NOL3; PPARGC1A; SLC26A5 | 0 | 0.00 | | 0 | 0.00 | | 3 | 2.82 | BCL2; NDNF; PPARGC1A | 4 | 4.20 | EIF4EBP1; HK2; PANX1; PPIF |
| regulation of mitochondrial outer membrane permeabilization involved in apoptotic signaling pathway: GO | 41 | 7 | 2.86 | BAK1; DYNLL1; SFN; SLC25A5; TP63; YWHAQ; YWHAZ | 1 | 0.29 | BCL2 | 0 | 0.00 | | 1 | 10.19 | GZMB | 1 | 0.62 | BCL2 | 5 | 3.46 | BAK1; E2F1; SFN; YWHAQ; YWHAZ |
| signaling by ptk6 | 41 | 7 | 2.86 | CCNE1; EREG; HBEGF; HIF1A; NRAS; NRG1; SOCS3 | 3 | 0.86 | BTC; EGF; NRG2 | 0 | 0.00 | | 0 | 0.00 | | 1 | 0.62 | EGF | 5 | 3.46 | EREG; HBEGF; HIF1A; NRG1; SOCS3 |
| regulation of telomerase activity: GO | 41 | 5 | 2.04 | CCT2; GREM1; NEK2; PIF1; PRKCQ | 1 | 0.29 | MAPK15 | 0 | 0.00 | | 0 | 0.00 | | 0 | 0.00 | | 5 | 3.46 | AURKB; CCT2; NEK2; PIF1; PRKCQ |
| atf2 pathway | 56 | 9 | 2.69 | CCNA2; CSRP2; IFNG; IL6; PLAU; SELE; SERPINB5; SOCS3; TH | 4 | 0.84 | BCL2; COL24A1; NOS2; PPARGC1A | 0 | 0.00 | | 1 | 7.46 | SELE | 4 | 1.81 | BCL2; COL24A1; ESR1; PPARGC1A | 6 | 3.04 | CCNA2; CSRP2; JUNB; SERPINB5; SOCS3; TH |
| removal of licensing factors from | 56 | 8 | 2.39 | CCNA2; CDC6; CDKN1A; | 0 | 0.00 | | 0 | 0.00 | | 0 | 0.00 | | 0 | 0.00 | | 6 | 3.04 | CCNA2; CDC6; CDKN1A; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| origins | | | | MCM10; ORC1; ORC6; PSMA5; PSMB6 | | | | | | | | | | | | | | | MCM2; ORC1; ORC6 |
| synapse organization: GO | 143 | 13 | 1.52 | FBXO45; FLRT3; GDNF; LRRC4; NLGN4X; NRG1; PCDH17; SDK2; SNCB; TNC; UNC13A; WNT5A; WNT7A | 26 | 2.15 | APOE; ATP2B2; CACNA2D2; CACNB1; CTNND2; DRD1; GLRB; IL1RAPL1; LRP4; LRRTM4; MAGI2; NLGN1; NRXN1; NRXN3; PAK3; PALM; PCDHB16; PCDHB3; PCLO; PDZRN3; RELN; SEMA3E; SEZ6L; SHANK1; SNCA; SNCG | 0 | 0.00 | | 0 | 0.00 | | 16 | 2.84 | CACNA2D2; CACNB1; GLRB; NRXN1; PAK3; PALM; PCDHB11; PCDHB3; PCDHB6; PCLO; PDZRN3; RELN; SEMA3E; SEZ6L; SLITRK6; SNCA | 11 | 2.18 | AGRN; FBXO45; FLRT3; LRRC4; NLGN4X; NRG1; SDK2; SNCB; UNC13A; WNT5A; WNT7A |
| cell substrate adhesion: GO | 162 | 10 | 1.03 | CCL21; HPSE; ITGA3; ITGA6; ITGB6; KIF14; LYPD3; LYPD5; RHOD; TNFRSF12A | 22 | 1.60 | ACTN2; ARHGAP6; BCL2; CD34; EDA; EPDR1; EPHB1; FBLN5; FREM1; FZD4; ITGA7; ITGA8; MERTK; MUC4; OTOA; PKD1; RADIL; SORBS1; | 1 | 2.58 | SRCIN1 | 0 | 0.00 | | 12 | 1.88 | ANGPT1; BCL2; CD34; CTGF; DLC1; FBLN5; FREM1; FZD7; ITGA11; RADIL; TMEM8B; TNN | 12 | 2.10 | ACTN1; COL17A1; HPSE; ITGA3; ITGA6; ITGB4; ITGB6; KIF14; LYPD3; LYPD5; PPARD; RHOD |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | SRCIN1; TMEM8B; TNN; TNXB | | | | | | | | | | | | |
| zymogen activation: GO | 107 | 16 | 2.50 | BAK1; CCK; CYCS; F12; FAM162A; IFI16; IFI27; NGF; PERP; PRSS3; PYCARD; S100A8; S100A9; TNFRSF10A; TNFSF10; VCP | 3 | 0.33 | KLKB1; P2RX1; SNCA | 0 | 0.00 | | 0 | 0.00 | | 2 | 0.47 | DLC1; SNCA | 9 | 2.39 | BAK1; CYCS; F12; IFI16; IFI27; NGF; PLAT; PRSS3; XDH |
| positive regulation of ligase activity: GO | 107 | 15 | 2.35 | BUB1B; CCNB1; CDC20; CDK1; FBXO5; MAD2L1; PLK1; PSMA4; PSMA5; PSMB6; PSMD1; PSME3; UBE2C; UBE2N; UBE2S | 0 | 0.00 | | 0 | 0.00 | | 0 | 0.00 | | 0 | 0.00 | | 9 | 2.39 | BUB1B; CCNB1; CDC20; CDK1; MAD2L1; PLK1; TRIB3; UBE2C; UBE2S |
| arrhythmogenic right ventricular cardiomyopathy arvc | 73 | 8 | 1.83 | ACTB; DSC2; DSP; GJA1; ITGA3; ITGA6; ITGB6; JUP | 14 | 2.26 | ACTN2; CACNA1F; CACNA2D1; CACNA2D2; CACNB1; CTNNA3; DES; DMD; ITGA7; ITGA8; LAMA2; | 1 | 5.72 | SGCG | 0 | 0.00 | | 6 | 2.09 | CACNA2D1; CACNA2D2; CACNB1; ITGA11; LAMA2; TCF7L1 | 7 | 2.72 | ACTB; ACTN1; DSC2; ITGA3; ITGA6; ITGB4; ITGB6 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | SGCA; SGCG; TCF7L1 | | | | | | | | | | | | |
| antigen processing and presentation of peptide or polysaccharide antigen via mhc class ii: GO | 90 | 11 | 2.05 | AP1S3; CENPE; DYNLL1; IFI30; KIF11; KIF15; KIF18A; KIF23; KIF2C; KIF4A; RACGAP1 | 2 | 0.26 | CTSF; DYNC1I1 | 0 | 0.00 | | 0 | 0.00 | | 1 | 0.28 | HLA-DQB2 | 8 | 2.52 | AP1S3; CENPE; KIF11; KIF15; KIF18A; KIF23; KIF2C; KIF4A |
| I amino acid transport: GO | 57 | 8 | 2.35 | NTSR1; SERINC2; SLC38A1; SLC38A5; SLC7A1; SLC7A11; SLC7A5; SLC7A8 | 8 | 1.66 | SLC17A7; SLC1A2; SLC1A6; SLC1A7; SLC6A17; SLC7A10; SLC7A14; SLC7A9 | 0 | 0.00 | | 0 | 0.00 | | 2 | 0.89 | SLC1A6; SLC1A7 | 6 | 2.98 | NTSR1; SERINC2; SLC38A5; SLC7A1; SLC7A11; SLC7A5 |
| cell cycle: g1/s check point | 28 | 4 | 2.39 | CCNE1; CDC25A; CDK1; CDKN1A | 0 | 0.00 | | 0 | 0.00 | | 0 | 0.00 | | 0 | 0.00 | | 4 | 4.05 | CDC25A; CDK1; CDKN1A; E2F1 |
| g1 pathway | 28 | 4 | 2.39 | CCNE1; CDC25A; CDK1; CDKN1A | 0 | 0.00 | | 0 | 0.00 | | 0 | 0.00 | | 0 | 0.00 | | 4 | 4.05 | CDC25A; CDK1; CDKN1A; E2F1 |
| laminin interactions | 28 | 3 | 1.79 | ITGA6; LAMB3 | 2 | 0.84 | ITGA7; LAMA2 | 0 | 0.00 | | 0 | 0.00 | | 1 | 0.91 | LAMA2 | 4 | 4.05 | ITGA3; ITGA6; ITGB4; LAMB3 |
| osteoclast differentiation: GO | 28 | 2 | 1.20 | ACP5; GLO1 | 1 | 0.42 | GPC3 | 0 | 0.00 | | 0 | 0.00 | | 0 | 0.00 | | 4 | 4.05 | ACP5; EPHA2; JUNB; SBNO2 |
| interleukin-12 family signaling | 42 | 10 | 3.98 | CA2; CAP1; CNN2; GSTO1; IFNG; IL12RB2; | 0 | 0.00 | | 0 | 0.00 | | 0 | 0.00 | | 0 | 0.00 | | 5 | 3.38 | CA2; CAP1; IL10; IL12RB2; MSN |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | LMNB1; MSN; PPIA; STAT1 | | | | | | | | | | | | | | | |
| positive regulation of telomere maintenance: GO | 42 | 7 | 2.79 | CCT2; CCT3; CCT5; CCT6A; CCT7; NEK2; PRKCQ | 1 | 0.28 | MAPK15 | 0 | 0.00 | | 0 | 0.00 | | 0 | 0.00 | | 5 | 3.38 | AURKB; CCT2; CCT5; NEK2; PRKCQ |
| atm pathway | 42 | 6 | 2.39 | BLM; CDC25A; CDKN1A; CHEK1; H2AFX; UBE2N | 0 | 0.00 | | 0 | 0.00 | | 0 | 0.00 | | 0 | 0.00 | | 5 | 3.38 | BLM; CDC25A; CDKN1A; CHEK1; H2AFX |
| pi3k events in erbb2 signaling | 42 | 4 | 1.59 | CDKN1A; EREG; HBEGF; NRG1 | 4 | 1.12 | BTC; EGF; ERBB4; NRG2 | 0 | 0.00 | | 0 | 0.00 | | 2 | 1.21 | EGF; ERBB4 | 5 | 3.38 | CDKN1A; EREG; HBEGF; NRG1; TRIB3 |
| peptidyl serine modification: GO | 145 | 12 | 1.38 | AURKA; CCNB1; CDK1; CDK5R1; CLSPN; CSNK1A1; HMGA2; IL24; PLK1; PLK2; PRKCQ; TGFBR1 | 12 | 0.98 | BCL2; BRSK2; CAMK2A; DCX; HIPK4; MAST1; NDNF; PKD1; PRKAA2; PRKG2; SGK2; STK32A | 0 | 0.00 | | 0 | 0.00 | | 8 | 1.40 | BCL2; BRSK2; DCN; NDNF; PDK3; PRKAA2; PRKG2; STK32A | 11 | 2.15 | AURKA; AURKB; CCNB1; CDK1; CDK5R1; HMGA2; PLK1; PLK2; PRKCQ; RPS6KA4; SGK1 |
| response to reactive oxygen species: GO | 184 | 22 | 2.00 | ANXA1; AREG; BAK1; CCNA2; CDK1; CYCS; ECT2; FOSL1; GSTP1; HIF1A; HMOX1; IL1B; IL6; LDHA; MMP3; NR4A3; | 13 | 0.83 | APOD; APOE; BCL2; CRYAB; HBA1; HBA2; HBB; PDGFD; PPARGC1A; SCGB1A1; SOD3; TPM1; TXNIP | 1 | 2.27 | CRYAB | 1 | 2.27 | IL1B | 7 | 0.97 | ALDH3A2; BCL2; HBA2; HBB; PPARGC1A; SOD3; TXNIP | 13 | 2.00 | AREG; BAK1; CCNA2; CDK1; CYCS; ECT2; FOSL1; GSTP1; HIF1A; LDHA; MMP3; PPIF; TXN |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | OLR1; PPIF; PRDX1; S100A7; SDC1; TXN | | | | | | | | | | | | | | | |
| negative regulation of inflammatory response: GO | 91 | 10 | 1.84 | ACP5; ADCYAP1; FOXF1; GSTP1; IL12B; IL2RA; MEFV; PBK; SOCS3; ZC3H12A | 7 | 0.91 | ADIPOQ; ADORA1; APOD; APOE; ELANE; PTGIS; SLIT2 | 1 | 4.59 | ADIPOQ | 1 | 4.59 | IL2RA | 2 | 0.56 | ELANE; SLIT2 | 8 | 2.49 | ACP5; GSTP1; IL10; MEFV; PBK; PPARD; SOCS3; ZC3H12A |
| carbohydrate transport: GO | 91 | 7 | 1.29 | AQP3; FABP5; HK2; NRG1; SLC2A1; SLC2A9; SLC5A1 | 10 | 1.30 | AQP4; AQP7; DRD1; KLF15; SLC26A5; SLC2A4; SLC35D3; SLC5A2; SLC5A9; SORBS1 | 0 | 0.00 | | 1 | 4.59 | AQP9 | 2 | 0.56 | SLC2A12; SLC5A9 | 8 | 2.49 | AQP3; FABP5; HK2; NRG1; PPARD; SLC26A6; SLC2A1; SLC2A9 |
| gene silencing by rna: GO | 127 | 13 | 1.71 | HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L; RAN | 2 | 0.19 | PIWIL2; TERT | 0 | 0.00 | | 0 | 0.00 | | 0 | 0.00 | | 10 | 2.23 | HIST1H3A; HIST1H3C; HIST1H3F; HIST1H3G; HIST1H3H; HIST1H3I; HIST1H3J; HIST1H4I; RAN; TDRD9 |
| positive regulation of cytokine biosynthetic process: GO | 58 | 12 | 3.46 | CD3E; CD80; EBI3; EREG; HMOX1; IFNG; IL12B; IL1A; IL1B; PRKCQ; | 1 | 0.20 | ELANE | 0 | 0.00 | | 1 | 7.21 | IL1B | 1 | 0.44 | ELANE | 6 | 2.93 | BCL3; CCL20; EREG; PRKCQ; PTAFR; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | PTAFR; WNT5A | | | | | | | | | | | | | | | |
| negative regulation of wound healing: GO | 58 | 10 | 2.89 | F12; GJA1; HMGCR; PLAU; PLAUR; SERPINB2; SERPINE1; SERPINE2; THBD; UBASH3B | 5 | 1.02 | APOE; CD34; KLKB1; TMPRSS6; TSPAN8 | 0 | 0.00 | | 1 | 7.21 | SERPINE1 | 4 | 1.75 | CD34; FGF2; PRKG1; TSPAN8 | 6 | 2.93 | F12; PLAT; SERPINB2; SERPINE2; THBD; UBASH3B |
| maternal process involved in female pregnancy: GO | 58 | 8 | 2.31 | CTSB; CYP27B1; DSG1; GJB2; HIF1A; ITGA3; PRDM1; PTGS2 | 4 | 0.81 | CNR1; LIF; PLA2G6; PTGIS | 0 | 0.00 | | 0 | 0.00 | | 1 | 0.44 | ESR1 | 6 | 2.93 | CYP27B1; HIF1A; ITGA3; JUNB; PPARD; PTGS2 |
| regulation of protein tyrosine kinase activity: GO | 58 | 8 | 2.31 | EPGN; EREG; GREM1; HSPH1; LRP8; NRG1; RAP2B; TGFA | 6 | 1.22 | ADORA1; ADRA2A; AGT; EGF; RELN; SRCIN1 | 1 | 7.21 | SRCIN1 | 0 | 0.00 | | 4 | 1.75 | ADRA2A; EGF; GPRC5B; RELN | 6 | 2.93 | AFAPIL2; EREG; HSPH1; NRG1; RAP2B; TGFA |
| transport of inorganic cations/anions and amino acids/ oligopeptides | 58 | 5 | 1.44 | SLC38A1; SLC7A1; SLC7A11; SLC7A5; SLC7A8 | 3 | 0.61 | SLC1A2; SLC4A4; SLC7A9 | 0 | 0.00 | | 0 | 0.00 | | 2 | 0.88 | SLC16A10; SLC4A4 | 6 | 2.93 | SLC20A1; SLC26A6; SLC4A7; SLC7A1; SLC7A11; SLC7A5 |
| *substantia nigra* development: GO | 43 | 6 | 2.33 | ACTB; DYNLL1; HSPA5; INA; LDHA; YWHAQ | 2 | 0.55 | FGF9; PLP1 | 0 | 0.00 | | 0 | 0.00 | | 1 | 0.59 | PLP1 | 5 | 3.30 | ACTB; HSPA5; INA; LDHA; YWHAQ |
| gene and protein expression by jak-stat signaling after interleukin-12 stimulation | 29 | 8 | 4.62 | CA2; CAP1; CNN2; GSTO1; IFNG; LMNB1; MSN; PPIA | 0 | 0.00 | | 0 | 0.00 | | 0 | 0.00 | | 0 | 0.00 | | 4 | 3.91 | CA2; CAP1; IL10; MSN |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| intrinsic apoptotic signaling pathway in response to dna damage by p53 class mediator: GO | 29 | 6 | 3.46 | AEN; BRCA2; CDKN1A; IFI16; PYCARD; TP63 | 1 | 0.41 | NUPRI | 0 | 0.00 | | 0 | 0.00 | | 0 | 0.00 | | 4 | 3.91 | BCL3; BRCA2; CDKN1A; IFI16 |
| regulation of protein insertion into mitochondrial membrane involved in apoptotic signaling pathway: GO | 29 | 5 | 2.89 | DYNLL1; SFN; TP63; YWHAQ; YWHAZ | 1 | 0.41 | BCL2 | 0 | 0.00 | | 1 | 14.41 | GZMB | 1 | 0.88 | BCL2 | 4 | 3.91 | E2F1; SFN; YWHAQ; YWHAZ |
| brown fat cell differentiation: GO | 29 | 3 | 1.73 | ITGA6; LAMB3; PTGS2 | 7 | 2.85 | ADIPOQ; ADRB1; FABP4; PEX11A; PPARGC1A; RARRES2; SLC2A4 | 1 | 14.41 | ADIPOQ | 0 | 0.00 | | 2 | 1.75 | PPARGC1A; RARRES2 | 4 | 3.91 | ITGA6; LAMB3; LRG1; PTGS2 |
| dna strand elongation: GO | 29 | 3 | 1.73 | GINS1; GINS3; PCNA | 1 | 0.41 | TERT | 0 | 0.00 | | 0 | 0.00 | | 0 | 0.00 | | 4 | 3.91 | FEN1; GINS1; GINS3; GINS4 |
| regulation of defense response to virus by host: GO | 129 | 16 | 2.08 | EIF2S1; FCGR3B; FGFBP1; HIST1H3A; HIST1H3B; HIST1H3C; HIST1H3F; HIST1H3G; HIST1H3H; HIST1H3I; HIST1H3J; IL12B; SERPINB10; TEAD4; TREM1; ZC3H12A | 9 | 0.82 | FGF14; HCAR1; MAP1A; MSTN; MYOM1; PDK4; PHYHIP; REEP2; USP17L2 | 0 | 0.00 | | 1 | 3.24 | TREM1 | 3 | 0.59 | LMCD1; MYOM1; PDK4 | 10 | 2.20 | FGFBP1; HIST1H3A; HIST1H3C; HIST1H3F; HIST1H3G; HIST1H3H; HIST1H3I; HIST1H3J; TEAD4; ZC3H12A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| cellular response to starvation: GO | 111 | 11 | 1.66 | CDKN1A; DSC2; EIF2S1; HSPA5; HSPA8; IFI16; PCSK9; RALB; SLC2A1; UPP1; ZC3H12A | 8 | 0.85 | ALB; BCL2; CARTPT; INHBB; MAP1LC3C; PCK1; PDK4; PRKAA2 | 0 | 0.00 | | 0 | 0.00 | | 4 | 0.92 | BCL2; BHLHA15; PDK4; PRKAA2 | 9 | 2.30 | CDKN1A; DSC2; HSPA5; HSPA8; IFI16; PCSK9; SLC2A1; WNT9B; ZC3H12A |
| retrograde vesicle mediated transport golgi to er: GO | 76 | 8 | 1.76 | CENPE; KIF11; KIF15; KIF18A; KIF23; KIF2C; KIF4A; RACGAP1 | 0 | 0.00 | | 0 | 0.00 | | 0 | 0.00 | | 0 | 0.00 | | 7 | 2.61 | CENPE; KIF11; KIF15; KIF18A; KIF23; KIF2C; KIF4A |
| regulation of cytokine biosynthetic process: GO | 94 | 14 | 2.49 | CD3E; CD80; EBI3; EREG; HMOX1; IFNG; IL12B; IL1A; IL1B; IL6; NMI; PRKCQ; PTAFR; WNT5A | 2 | 0.25 | ELANE; INHBB | 0 | 0.00 | | 1 | 4.45 | IL1B | 1 | 0.27 | ELANE | 8 | 2.41 | BCL3; CCL20; EREG; IL10; NMI; PRKCQ; PTAFR; WNT5A |
| negative regulation of chromosome organization: GO | 94 | 8 | 1.42 | BUB1; BUB1B; CENPF; MAD2L1; PIF1; PLK1; PTTG1; TTK | 3 | 0.38 | SNCA; TET1; USP17L2 | 0 | 0.00 | | 0 | 0.00 | | 2 | 0.54 | SNCA; TET1 | 8 | 2.41 | BUB1; BUB1B; CENPF; MAD2L1; PIF1; PLK1; PTTG1; TTK |
| positive regulation of interleukin 1 beta production: GO | 30 | 8 | 4.46 | CCL3; IFI16; IFNG; NLRP2; PANX1; PYCARD; TRIM16; WNT5A | 1 | 0.39 | P2RX7 | 0 | 0.00 | | 0 | 0.00 | | 0 | 0.00 | | 4 | 3.78 | IFI16; NLRP2; PANX1; WNT5A |
| detoxification of reactive | 30 | 5 | 2.79 | CYCS; ERO1A; | 1 | 0.39 | SOD3 | 0 | 0.00 | | 0 | 0.00 | | 1 | 0.85 | SOD3 | 4 | 3.78 | CYCS; ERO1A; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| oxygen species | | | | GSTP1; PRDX1; TXN | | | | | | | | | | | | | | | GSTP1; TXN |
| maternal placenta development: GO | 30 | 5 | 2.79 | CTSB; CYP27B1; GJB2; PRDM1; PTGS2 | 2 | 0.79 | LIF; PTGIS | 0 | 0.00 | | 0 | 0.00 | | 1 | 0.85 | ESR1 | 4 | 3.78 | CYP27B1; JUNB; PPARD; PTGS2 |
| negative regulation of cellular response to insulin stimulus: GO | 30 | 4 | 2.23 | IL1B; PRKCQ; PTPRE; SOCS3 | 2 | 0.79 | ENPP1; MSTN | 0 | 0.00 | | 1 | 13.93 | IL1B | 0 | 0.00 | | 4 | 3.78 | CISH; PRKCQ; PTPRE; SOCS3 |
| protein complex involved in cell adhesion: GO | 30 | 4 | 2.23 | ITGA3; ITGA6; ITGAX; ITGB6 | 2 | 0.79 | ITGA7; ITGA8 | 0 | 0.00 | | 0 | 0.00 | | 1 | 0.85 | ITGA11 | 4 | 3.78 | ITGA3; ITGA6; ITGB4; ITGB6 |
| regulation of platelet activation: GO | 30 | 4 | 2.23 | PRKCQ; SERPINE2; THBD; UBASH3B | 1 | 0.39 | APOE | 0 | 0.00 | | 0 | 0.00 | | 1 | 0.85 | PRKG1 | 4 | 3.78 | PRKCQ; SERPINE2; THBD; UBASH3B |
| laminin binding: GO | 30 | 3 | 1.67 | ITGA3; LYPD3; LYPD5 | 2 | 0.79 | SLIT2; SSC5D | 0 | 0.00 | | 0 | 0.00 | | 4 | 3.39 | LRRC15; NTN4; SLIT2; SSC5D | 4 | 3.78 | AGRN; ITGA3; LYPD3; LYPD5 |
| ameboidal type cell migration: GO | 150 | 16 | 1.78 | ANLN; CAP1; CXCL13; DPP4; FERMT1; GDNF; GREM1; HIF1A; KRT16; PRSS3; S100A2; SCG2; SEMA4B; STAT1; TGFBR1; WNT5A | 18 | 1.42 | AMOT; EDN3; ERBB4; FOLR1; GPLD1; HAND2; MESP1; PLEKHG5; SEMA3A; SEMA3B; SEMA3D; SEMA3E; SEMA3G; SLIT2; SOX10; SOX8; TNS1; WNT11 | 0 | 0.00 | | 0 | 0.00 | | 12 | 2.03 | CENPV; EDN3; ERBB4; FGF2; GPLD1; HAND2; KRT2; MESP1; SEMA3E; SEMA4G; SLIT2; WNT11 | 11 | 2.08 | ANLN; CAP1; DPP4; FERMT1; HIF1A; PPARD; PRSS3; S100A2; S100P; SEMA4B; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| columnar cuboidal epithelial cell development: GO | 45 | 4 | 1.49 | CDKN1A; HIF1A; PRDM1; WNT5A | 7 | 1.84 | ATP2B2; BMP5; CLIC5; FGFR1; PAX6; PDZD7; ROS1 | 0 | 0.00 | | 0 | 0.00 | | 4 | 2.26 | CLIC5; FGFR1; PDZD7; SLITRK6 | 5 | 3.15 | CDKN1A; HIF1A; SLC4A7; TMC1; WNT5A |
| purine ntp dependent helicase activity: GO | 95 | 5 | 0.88 | BLM; DDX21; DDX28; EIF4A3; PIF1 | 2 | 0.25 | CHD5; DDX25 | 0 | 0.00 | | 0 | 0.00 | | 1 | 0.27 | DDX25 | 8 | 2.39 | BLM; BRIP1; DDX21; DDX28; DDX39A; EIF4A3; PIF1; TDRD9 |
| regulation of epidermis development: GO | 61 | 9 | 2.47 | AQP3; CDH3; CYP27B1; HPSE; IL20; KRT17; SFN; TP63; TRIM16 | 3 | 0.58 | KRT36; PTCH1; PTCH2 | 0 | 0.00 | | 0 | 0.00 | | 3 | 1.25 | MYCN; PTCH1; PTCH2 | 6 | 2.79 | AQP3; CYP27B1; HPSE; IL20; PPARD; SFN |
| centrosome maturation | 61 | 6 | 1.65 | CDK1; DYNLL1; NEK2; PLK1; TUBA1C; TUBA4A | 2 | 0.39 | MAST1; PRKAR2B | 1 | 6.85 | PRKAR2B | 0 | 0.00 | | 1 | 0.42 | DLC1 | 6 | 2.79 | CDK1; NEK2; PLK1; PLK4; TUBA1C; TUBA4A |
| deoxyribonuclease activity: GO | 61 | 6 | 1.65 | DNASEIL3; EXO1; GEN1; HMGA2; ISG20; NME1 | 2 | 0.39 | DNASE1L2; NEIL1 | 0 | 0.00 | | 0 | 0.00 | | 0 | 0.00 | | 6 | 2.79 | DNASE1L3; EXO1; FEN1; HMGA2; NEIL3; TREX2 |
| interleukin-7 signaling | 171 | 13 | 1.27 | CBX2; CDKN1A; EREG; HBEGF; HIST1H3A; HIST1H3I; ILIRL1; IL7R; JAK3; MYD88; NRG1; PSMA5; PSMB6 | 7 | 0.48 | BTC; EGF; FGF1; FGFR1; FGFR3; IRS2; NRG2 | 0 | 0.00 | | 1 | 2.44 | IL7R | 3 | 0.45 | EGF; FGFR1; PREX2 | 12 | 1.99 | CBX2; CDKN1A; CISH; EREG; HBEGF; HIST1H3A; HIST1H3I; IER3; MYD88; NRG1; SNAI2; TRIB3 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| collagen formation | 78 | 8 | 1.72 | CTSB; CTSL; ITGA6; LAMB3; MMP1; MMP3; MMP9; PPIB | 9 | 1.36 | COL11A1; COL11A2; COL19A1; COL21A1; COL24A1; COL25A1; COL28A1; COL9A2; PCOLCE2 | 0 | 0.00 | | 0 | 0.00 | | 6 | 1.95 | COL11A1; COL21A1; COL24A1; COL28A1; GULP1; PCOLCE | 7 | 2.54 | ADAMTS14; COL17A1; ITGA6; ITGB4; LAMB3; MMP3; P3H2 |
| negative regulation of defense response: GO | 133 | 15 | 1.89 | ACP5; ADCYAP1; CIQBP; FOXF1; GSTP1; IFI16; IL12B; IL2RA; MEFV; NMI; PBK; SERPINB4; SERPINB9; SOCS3; ZC3H12A | 7 | 0.62 | ADIPOQ; ADORA1; APOD; APOE; ELANE; PTGIS; SLIT2 | 1 | 3.14 | ADIPOQ | 2 | 6.28 | IL2RA; SERPINB9 | 2 | 0.38 | ELANE; SLIT2 | 10 | 2.13 | ACP5; GSTP1; IFI16; IL10; MEFV; NMI; PBK; PPARD; SOCS3; ZC3H12A |
| regulation of interleukin 1 secretion: GO | 31 | 8 | 4.32 | CCL3; IFNG; NLRP2; PANX1; PYCARD; TRIM16; WNT5A; ZC3H12A | 1 | 0.38 | P2RX7 | 0 | 0.00 | | 0 | 0.00 | | 0 | 0.00 | | 4 | 3.66 | NLRP2; PANX1; WNT5A; ZC3H12A |
| cellular response to glucose starvation: GO | 31 | 5 | 2.70 | HSPA5; IFI16; SLC2A1; UPP1; ZC3H12A | 2 | 0.76 | BCL2; PRKAA2 | 0 | 0.00 | | 0 | 0.00 | | 3 | 2.46 | BCL2; BHLHA15; PRKAA2 | 4 | 3.66 | HSPA5; IFI16; SLC2A1; ZC3H12A |
| nuclear envelope breakdown | 31 | 5 | 2.70 | CCNB1; CCNB2; CDK1; LMNB1; PLK1 | 0 | 0.00 | | 0 | 0.00 | | 0 | 0.00 | | 0 | 0.00 | | 4 | 3.66 | CCNB1; CCNB2; CDK1; PLK1 |
| nfat tfpathway | 46 | 7 | 2.55 | CSF2; CTLA4; FOSL1; IFNG; IL2RA; | 1 | 0.26 | IL5 | 0 | 0.00 | | 1 | 9.08 | IL2RA | 0 | 0.00 | | 5 | 3.08 | E2F1; FOSL1; JUNB; PRKCQ; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | PRKCQ; PTGS2 | | | | | | | | | | | | | | | PTGS2 |
| regulation of nf kappab import into nucleus: GO | 46 | 7 | 2.55 | GREM; IL12B; IL1B; PRDX1; PRKCQ; PTGS2; ZC3H12A | 2 | 0.51 | EDA; NOL3 | 0 | 0.00 | | 1 | 9.08 | IL1B | 0 | 0.00 | | 5 | 3.08 | BCL3; IL10; PRKCQ; PTGS2; ZC3H12A |
| negative regulation of dna binding: GO | 46 | 6 | 2.18 | GZMA; HMGA2; HMOX1; IFI16; MDFI; NEK2 | 3 | 0.77 | GATA1; HAND2; WFIKKN1 | 1 | 9.08 | WFIKKN1 | 0 | 0.00 | | 1 | 0.55 | HAND2 | 5 | 3.08 | E2F1; HMGA2; IFI16; MDFI; NEK2 |
| endodeoxy-ribonuclease activity: GO | 46 | 4 | 1.46 | DNASE1L3; EXO1; GEN1; HMGA2 | 1 | 0.26 | NEIL1 | 0 | 0.00 | | 0 | 0.00 | | 0 | 0.00 | | 5 | 3.08 | DNASE1L3; EXO1; FEN1; HMGA2; NEIL3 |
| regulation of telomere maintenance: GO | 62 | 8 | 2.16 | CCT2; CCT3; CCT5; CCT6A; CCT7; NEK2; PIF1; PRKCQ | 1 | 0.19 | MAPK15 | 0 | 0.00 | | 0 | 0.00 | | 0 | 0.00 | | 6 | 2.74 | AURKB; CCT2; CCT5; NEK2; PIF1; PRKCQ |
| response to elevated platelet cytosolic ca2+ | 97 | 8 | 1.38 | CAP1; HSPA5; MANF; PPIA; SERPINE1; SRGN; TOR4A; TUBA4A | 7 | 0.85 | ALB; CLEC3B; CLU; EGF; RARRES2; TF; TIMP3 | 1 | 4.31 | CLEC3B | 1 | 4.31 | SERPINE1 | 4 | 1.05 | CLU; EGF; RARRES2; SCCPDH | 8 | 2.34 | ACTN1; CAP1; HSPA5; LGALS3BP; PCDH7; TAGLN2; TOR4A; TUBA4A |
| regeneration: GO | 154 | 22 | 2.39 | ANXA1; ANXA3; BAK1; CCNA2; CCNB1; CCNE1; CDK1; CDKN1A; GJA1; GSTP1; KLK6; MKI67; | 13 | 1.00 | APOD; APOE; BCL2; ERBB4; F7; FOLR1; GSN; KLKB1; LIF; LIFR; MSTN; PFKFB1; TIMP3 | 0 | 0.00 | | 1 | 2.71 | ANXA3 | 6 | 0.99 | BCL2; CHL1; CXCL12; ERBB4; FZD7; PFKFB1 | 11 | 2.03 | BAK1; CCNA2; CCNB1; CDK1; CDKN1A; GSTP1; MKI67; PRKCQ; SOCS3; SOX15; WNT7A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | NEFL; NR4A3; PGF; PLAU; PRKCQ; SOCS3; SULF2; TNC; UGT1A1; WNT7A | | | | | | | | | | | | | | | |
| tissue migration: GO | 80 | 12 | 2.51 | ANLN; CXCL13; DPP4; FERMT1; FOXF1; GREM1; KRT16; PRSS3; S100A2; SCG2; STAT1; TGFBR1 | 5 | 0.74 | ACTA1; AMOT; GPLD1; PLEKHG5; SLIT2 | 0 | 0.00 | | 0 | 0.00 | | 4 | 1.27 | FGF2; GPLD1; KRT2; SLIT2 | 7 | 2.48 | ANLN; DPP4; FERMT1; PPARD; PRSS3; S100A2; S100P |
| negative regulation of the pi3k/akt network | 63 | 5 | 1.33 | EREG; HBEGF; IL1RL1; MYD88; NRG1 | 7 | 1.31 | BTC; EGF; FGF1; FGFR1; FGFR3; IRS2; NRG2 | 0 | 0.00 | | 0 | 0.00 | | 2 | 0.81 | EGF; FGFR1 | 6 | 2.70 | EREG; HBEGF; IER3; MYD88; NRG1; TRIB3 |
| regulation of t cell apoptotic process: GO | 32 | 7 | 3.66 | CD274; HIF1A; IDO1; JAK3; PRELID1; PRKCQ; WNT5A | 4 | 1.47 | GPAM; PIP; RORC; TSC22D3 | 1 | 13.06 | GPAM | 0 | 0.00 | | 3 | 2.38 | PIP; SLC46A2; TSC22D3 | 4 | 3.54 | HIF1A; PRELID1; PRKCQ; WNT5A |
| phosphatidyl-inositol 4 5 bisphosphate binding: GO | 47 | 4 | 1.42 | ADAP2; MYO1B; PFN1; TWF1 | 9 | 2.26 | ACTN2; APBA1; JPH2; KCNJ1; SCIN; SNX21; STXBP6; SYT1; TTPA | 0 | 0.00 | | 1 | 8.89 | SNX20 | 3 | 1.62 | APBA1; SCIN; STXBP6 | 5 | 3.02 | ADAP2; MARK1; MYO1B; PFN1; TWF1 |
| cell chemotaxis: GO | 155 | 29 | 3.13 | ANXA1; CCL17; CCL18; CCL21; | 7 | 0.53 | AGTR1; CCL14; EDN3; EPHB1; | 0 | 0.00 | | 5 | 13.48 | CXCL5; CXCL9; FFAR2; IL1B; TREM1 | 5 | 0.82 | AGTR1; CCL14; CXCL12; EDN3; LPAR1 | 11 | 2.01 | ARHGEF16; CCL20; CXCL11; CXCL2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | CCL22; CCL3; CCL7; CCR5; CXADR; CXCL1; CXCL10; CXCL11; CXCL13; CXCL3; CXCL5; CXCL6; CXCL9; CXCR1; CXCR4; HBEGF; IFNG; IL1B; IL6; PRKCQ; S100A12; S100A8; S100A9; SCG2; TREM1 | | | FOLR2; IL16; PLEKHG5 | | | | | | | | | | | | CXCL6; CXCR1; EPHA2; HBEGF; HRH1; IL10; PRKCQ |
| structure specific dna binding: GO | 117 | 12 | 1.72 | ACTB; BLM; GRHL3; H2AFZ; HIST1HIA; HIST1H1B; HIST1H1D; HMGA2; HMGB3; PIF1; RCC1; ZBP1 | 4 | 0.40 | GATA1; PER1; PPARGC1A; TET1 | 0 | 0.00 | | 0 | 0.00 | | 2 | 0.43 | PPARGC1A; TET1 | 9 | 2.18 | ACTB; BLM; H2AFZ; HIST1H1B; HIST1H1D; HMGA2; HMGB3; NEIL3; PIF1 |
| neural nucleus development: GO | 64 | 8 | 2.09 | ACTB; ALDH1A3; CDK5R1; DYNLL1; HSPA5; INA; LDHA; YWHAQ | 3 | 0.55 | BCL2; FGF9; PLP1 | 0 | 0.00 | | 0 | 0.00 | | 2 | 0.79 | BCL2; PLP1 | 6 | 2.66 | ACTB; CDK5R1; HSPA5; INA; LDHA; YWHAQ |
| response to interferon | 137 | 26 | 3.18 | CCL17; CCL18; | 7 | 0.60 | AQP4; CAMK2A; | 0 | 0.00 | | 2 | 6.10 | GBP1; IFITM3 | 4 | 0.74 | CCL14; HLA-DQB2; | 10 | 2.07 | CCL20; CYP27B1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| gamma: GO | | | | CCL21; CCL22; CCL3; CCL7; CYP27B1; EPRS; FCGR1A; GAPDH; GBP6; IFI30; IFITM1; IFITM3; IFNG; IL12B; KYNU; MEFV; MT2A; OAS1; OAS2; OAS3; OASL; PTAFR; STAT1; WNT5A | | | CAMK2B; CCL14; NCAM1; NOS2; SNCA | | | | | | | | | NCAM1; SNCA | | | GAPDH; GBP6; HLA-G; MEFV; OAS1; PTAFR; SLC26A6; WNT5A |
| cellular response to oxygen levels: GO | 137 | 9 | 1.10 | BDKRB2; CCNA2; CCNB1; EIF4EBP1; FAM162A; HIF1A; HMOX1; PLAU; PTGS2 | 14 | 1.21 | ANGPT4; BCL2; CPEB1; DRD1; EEF2K; HIF3A; KCND2; MYOCD; NDNF; NOX1; PPARGC1A; PTGIS; SLC2A4; TERT | 0 | 0.00 | | 0 | 0.00 | | 12 | 2.23 | ANGPT4; BCL2; CPEB1; HIF3A; KCND2; KCNK2; LPAR1; NDNF; PDK3; PPARGC1A; SLC29A1; TRPC1 | 10 | 2.07 | BDKRB2; CCNA2; CCNB1; E2F1; EIF4EBP1; HIF1A; NDRG1; PPARD; PTGS2; UCN2 |
| interferon alpha/beta signaling | 48 | 16 | 5.58 | IFI27; IFI6; IFIT3; IFITM1; IFITM3; IL6; ISG15; ISG20; MX1; OAS1; OAS2; OAS3; OASL; | 0 | 0.00 | | 0 | 0.00 | | 2 | 17.41 | IFITM3; ISG15 | 0 | 0.00 | | 5 | 2.95 | HLA-G; IFI27; MX1; OAS1; SOCS3 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | RSAD2; SOCS3; STAT1 | | | | | | | | | | | | | | | |
| regulation of protein export from nucleus: GO | 33 | 4 | 2.03 | IFI27; IL1B; SFN; TXN | 2 | 0.72 | CAMK1; RANBP3L | 0 | 0.00 | | 1 | 12.66 | IL1B | 2 | 1.54 | CAMK1; RANBP3L | 4 | 3.44 | GTSE1; IFI27; SFN; TXN |
| organ regeneration: GO | 82 | 13 | 2.65 | ANXA3; BAK1; CCNA2; CCNE1; CDK1; CDKN1A; GSTP1; MKI67; NR4A3; PGF; SOCS3; SULF2; UGT1A1 | 5 | 0.72 | F7; KLKB1; LIF; LIFR; PFKFB1 | 0 | 0.00 | | 1 | 5.10 | ANXA3 | 2 | 0.62 | CXCL12; PFKFB1 | 7 | 2.42 | BAK1; CCNA2; CDK1; CDKN1A; GSTP1; MKI67; SOCS3 |
| regulation of stat cascade: GO | 138 | 15 | 1.82 | CDK5R1; CSF2; FLRT3; IFNE; IFNG; IL12B; IL19; IL20; IL22; IL24; IL26; IL6; LRRC4; OSM; SOCS3 | 13 | 1.11 | AGT; CHAD; ERBB4; FGFR3; GHR; IFNA5; IL5; LEP; LIF; LRRC4C; LRRTM3; LRRTM4; PODN | 1 | 3.03 | GHR | 1 | 3.03 | OSM | 6 | 1.10 | CHAD; DCN; ERBB4; LRRC15; LRRC4C; PODN | 10 | 2.05 | CDK5R1; CISH; FLRT3; IFNE; IL10; IL19; IL20; IL22; LRRC4; SOCS3 |
| apc c cdh1 mediated degradation of cdc20 and other apc c cdh1 targeted proteins in late mitosis early g1 | 65 | 9 | 2.32 | AURKA; CDC20; PLK1; PSMA4; PSMA5; PSMB6; PSMD1; PTTG1; UBE2C | 0 | 0.00 | | 0 | 0.00 | | 0 | 0.00 | | 0 | 0.00 | | 6 | 2.62 | AURKA; AURKB; CDC20; PLK1; PTTG1; UBE2C |
| dna replication pre-initiation | 65 | 9 | 2.32 | CDC45; CDC6; DBF4; E2F3; MCM10; | 0 | 0.00 | | 0 | 0.00 | | 0 | 0.00 | | 0 | 0.00 | | 6 | 2.62 | CDC45; CDC6; E2F1; MCM2; ORC1; ORC6 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | ORC1; ORC6; PSMA5; PSMB6 | | | | | | | | | | | | | | | |
| m/g1 transition | 65 | 9 | 2.32 | CDC45; CDC6; DBF4; E2F3; MCM10; ORC1; ORC6; PSMA5; PSMB6 | 0 | 0.00 | | 0 | 0.00 | | 0 | 0.00 | | 0 | 0.00 | | 6 | 2.62 | CDC45; CDC6; E2F1; MCM2; ORC1; ORC6 |
| response to activity: GO | 65 | 6 | 1.54 | CDK1; HIF1A; NTRK1; PLAU; SCO2; TH | 10 | 1.82 | ADIPOQ; AGT; DRD1; GPAM; HDAC5; LEP; MSTN; PCK1; PPARGC1A; PRKAA2 | 2 | 12.86 | ADIPOQ; GPAM | 0 | 0.00 | | 2 | 0.78 | PPARGC1A; PRKAA2 | 6 | 2.62 | CDK1; HIF1A; IL10; PPARD; SCO2; TH |
| positive regulation of epithelial cell migration: GO | 101 | 13 | 2.15 | ANXA3; HBEGF; HIF1A; IFNG; INSL3; ITGA3; MMP9; PFN1; PTGS2; RAB25; WNT5A; WNT7A; ZC3H12A | 7 | 0.82 | AGT; AMOT; ANGPT4; ATOH8; CCBE1; FGFR1; GPLD1 | 0 | 0.00 | | 1 | 4.14 | ANXA3 | 7 | 1.76 | ANGPT1; ANGPT4; ATOH8; CCBE1; FGF2; FGFR1; GPLD1 | 8 | 2.25 | HBEGF; HIF1A; ITGA3; PFN1; PTGS2; WNT5A; WNT7A; ZC3H12A |
| cysteine type endopeptidase inhibitor activity: GO | 49 | 8 | 2.73 | BIRC5; CST7; CSTA; CSTB; PTTG1; SERPINB13; SERPINB3; SERPINB9 | 6 | 1.44 | BIRC7; CSTL1; NOL3; SNCA; SPOCK1; TFAP2B | 0 | 0.00 | | 1 | 8.53 | SERPINB9 | 2 | 1.04 | SNCA; SPOCK1 | 5 | 2.89 | BIRC5; CSTA; CSTB; PTTG1; SERPINB13 |
| homotypic cell cell adhesion: GO | 49 | 7 | 2.39 | ACTB; CXADR; DSC2; DSP; JUP; RAP2B; SLC7A11 | 4 | 0.96 | CTNNA3; GATA1; HBB; MYL9 | 0 | 0.00 | | 0 | 0.00 | | 1 | 0.52 | HBB | 5 | 2.89 | ACTB; ACTN1; DSC2; RAP2B; SLC7A11 |
| amino acid and oligopeptide slc | 49 | 6 | 2.05 | SLC38A1; SLC38A5; | 6 | 1.44 | SLC17A7; SLC1A2; | 0 | 0.00 | | 0 | 0.00 | | 3 | 1.56 | SLC16A10; SLC1A6; | 5 | 2.89 | SLC38A5; SLC5A5; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| transporters | | | | SLC7A1; SLC7A11; SLC7A5; SLC7A8 | | | SLC1A6; SLC1A7; SLC7A10; SLC7A9 | | | | | | | | | SLC1A7 | | | SLC7A1; SLC7A11; SLC7A5 |
| recruitment of mitotic centrosome proteins and complexes | 83 | 7 | 1.41 | CCNB1; CDK1; DYNLL1; NEK2; PLK1; TUBA1C; TUBA4A | 3 | 0.43 | MAST1; PRKAR2B; TUBB4A | 1 | 5.03 | PRKAR2B | 0 | 0.00 | | 1 | 0.31 | DLC1 | 7 | 2.39 | CCNB1; CDK1; NEK2; PLK1; PLK4; TUBA1C; TUBA4A |
| response to protozoan: GO | 20 | 5 | 4.18 | CLEC7A; IFNG; IL12B; IL4R; IL6 | 0 | 0.00 | | 0 | 0.00 | | 0 | 0.00 | | 0 | 0.00 | | 3 | 4.25 | BCL3; CLEC7A; IL10 |
| stathmin and breast cancer resistance to antimicrotubule agents | 20 | 5 | 4.18 | CCNB1; CD2; CD3E; CDK1; HSPA5 | 1 | 0.59 | PRKAR2B | 1 | 20.89 | PRKAR2B | 0 | 0.00 | | 0 | 0.00 | | 3 | 4.25 | CCNB1; CDK1; HSPA5 |
| transcriptional regulation by the ap-2 (tfap2) family of transcription factors | 20 | 4 | 3.35 | CDKN1A; MYBL2; NPM1; TGFA | 1 | 0.59 | APOE | 0 | 0.00 | | 0 | 0.00 | | 0 | 0.00 | | 3 | 4.25 | CDKN1A; NPM1; TGFA |
| dna binding bending: GO | 20 | 3 | 2.51 | HMGA2; HMGB3; TOP2A | 2 | 1.18 | CRIP1; GATA1 | 0 | 0.00 | | 0 | 0.00 | | 2 | 2.54 | CRIP1; FOXC1 | 3 | 4.25 | HMGA2; HMGB3; TOP2A |
| o-glycan biosynthesis | 20 | 3 | 2.51 | GALNT14; GALNT6; ST6GALNAC1 | 3 | 1.77 | GALNT13; GALNT8; GALNTL6 | 0 | 0.00 | | 0 | 0.00 | | 0 | 0.00 | | 3 | 4.25 | GALNT14; GALNT6; ST6GALNAC1 |
| branching involved in mammary gland duct morphogenesis: GO | 20 | 2 | 1.67 | AREG; WNT5A | 0 | 0.00 | | 0 | 0.00 | | 0 | 0.00 | | 1 | 1.27 | ESR1 | 3 | 4.25 | AREG; EPHA2; WNT5A |
| inorganic anion exchanger activity: GO | 20 | 1 | 0.84 | SLC4A8 | 3 | 1.77 | SLC22A9; SLC4A1; SLC4A4 | 0 | 0.00 | | 0 | 0.00 | | 1 | 1.27 | SLC4A4 | 3 | 4.25 | SLC26A6; SLC4A3; SLC4A7 |
| regulation of dna repair: GO | 66 | 7 | 1.77 | CHEK1; FOXM1; H2AFX; | 1 | 0.18 | APBB1 | 0 | 0.00 | | 0 | 0.00 | | 0 | 0.00 | | 6 | 2.58 | CHEK1; FOXM1; H2AFX; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | HMGA2; PCNA; POLQ; UBE2N | | | | | | | | | | | | | | | HMGA2; POLQ; RAD51AP1 |
| intraflagellar transport | 34 | 5 | 2.46 | DYNLL1; TUBA1C; TUBA4A; TUBB2A; TUBB6 | 0 | 0.00 | | 0 | 0.00 | | 0 | 0.00 | | 1 | 0.75 | DLC1 | 4 | 3.34 | TUBA1C; TUBA4A; TUBB2A; TUBB6 |
| male meiosis: GO | 34 | 3 | 1.48 | BRCA2; KIF18A; TRIP13 | 0 | 0.00 | | 0 | 0.00 | | 0 | 0.00 | | 1 | 0.75 | SYCP3 | 4 | 3.34 | BRCA2; KIF18A; TDRD9; TRIP13 |
| positive regulation of vasoconstriction: GO | 34 | 3 | 1.48 | GJA1; PTAFR; PTGS2 | 3 | 1.04 | ADRA1A; ADRA1B; NPY1R | 0 | 0.00 | | 0 | 0.00 | | 2 | 1.49 | ADRA1A; NPY1R | 4 | 3.34 | HRH1; HRH2; PTAFR; PTGS2 |
| pigment granule: GO | 102 | 14 | 2.30 | AHCY; ATP1B3; CTSB; GGH; HSPA5; HSPA8; PDIA3; PPIB; PRDX1; RAB38; RAN; SLC2A1; TH; YWHAZ | 5 | 0.58 | DCT; GCHFR; MYH11; OCA2; SYNGR1 | 0 | 0.00 | | 0 | 0.00 | | 1 | 0.25 | MYRIP | 8 | 2.22 | ANXA2P2; HSPA5; HSPA8; RAB38; RAN; SLC2A1; TH; YWHAZ |
| digestion: GO | 121 | 10 | 1.38 | ADM2; AKRIB10; HTR3A; LDLR; LIPG; NMU; PRSS3; SLC5A1; UGT1A1; VSIG1 | 19 | 1.85 | ADRA2A; AMY2B; CCKBR; CHRM1; CHRM3; GALRI; LEP; LIPH; MOGAT2; MUC4; MUC6; NPCIL1; P2RX7; PPARGC1A; RBP4; SCT; SLC26A7; | 0 | 0.00 | | 0 | 0.00 | | 8 | 1.68 | ADRA2A; AMY2B; CHRM1; CHRM3; LIPH; LIPK; LIPM; PPARGC1A | 9 | 2.11 | ADM2; AKRIB10; HRH2; LDLR; NMU; PRSS3; SLC26A6; UCN2; VSIG1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | | | | SLC9A4; SOAT2 | | | | | | | | | | | | |
| ecm-receptor interaction | 84 | 7 | 1.39 | HMMR; ITGA3; ITGA6; ITGB6; LAMB3; SDC1; TNC | 13 | 1.83 | CHAD; COL11A1; COL11A2; ITGA7; ITGA8; LAMA2; LAMB4; LAMC3; RELN; SDC2; SV2B; TNN; TNXB | 0 | 0.00 | | 0 | 0.00 | | 8 | 2.42 | CHAD; COL11A1; ITGA11; LAMA2; LAMC3; RELN; SV2B; TNN | 7 | 2.36 | AGRN; HMMR; ITGA3; ITGA6; ITGB4; ITGB6; LAMB3 |
| assembly of the pre-replicative complex | 50 | 6 | 2.01 | CDC6; E2F3; ORC1; ORC6; PSMA5; PSMB6 | 0 | 0.00 | | 0 | 0.00 | | 0 | 0.00 | | 0 | 0.00 | | 5 | 2.84 | CDC6; E2F1; MCM2; ORC1; ORC6 |
| cytoplasmic microtubule: GO | 50 | 4 | 1.34 | BIRC5; CKAP2; KIF2C; RGS20 | 2 | 0.47 | CYP2A6; REEP2 | 0 | 0.00 | | 0 | 0.00 | | 0 | 0.00 | | 5 | 2.84 | BIRC5; GTSE1; KIF18B; KIF2C; RGS20 |
| peptidase inhibitor activity: GO | 161 | 25 | 2.60 | A2ML1; BIRC5; CST7; CSTA; CSTB; NGF; PI15; PI3; PTTG1; SERPINA1; SERPINB1; SERPINB10; SERPINB13; SERPINB2; SERPINB3; SERPINB4; SERPINB5; SERPINB7; SERPINB9; SERPINE1; SERPINE2; SLPI; SPINK6; | 25 | 1.83 | AGT; AMBP; BIRC7; C3; COL28A1; CSTL1; GPC3; ITIH5; NOL3; RENBP; SERPINA12; SERPINA5; SERPINA9; SNCA; SPINK1; SPINT4; SPOCK1; SSPO; TFAP2B; TIMP3; TIMP4; WFDC10B; | 1 | 2.60 | WFIKKN1 | 2 | 5.19 | SERPINB9; SERPINE1 | 11 | 1.74 | C3; COL28A1; PI16; PZP; RECK; SERPINA12; SNCA; SPINT4; SPOCK1; WFDC13; WFDC3 | 11 | 1.94 | BIRC5; CSTA; CSTB; NGF; PTTG1; SERPINA10; SERPINB13; SERPINB2; SERPINB5; SERPINE2; SLPI |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | SPINK7; WFDC12 | | | WFDC13; WFDC3; WFIKKN1 | | | | | | | | | | | | |
| gastrin creb signalling pathway via pkc and mapk | 122 | 14 | 1.92 | BDKRB1; BDKRB2; CDK1; GNA15; GNGT2; GPR65; LPAR3; NPSR1; NTSR1; P2RY1; P2RY2; PRKCQ; PTAFR; QRFPR | 12 | 1.16 | ADRA1B; ARHGEF25; CCKBR; CHRM1; CHRM3; DGKG; EDN3; GCGR; NMUR1; PLCB4; PROK1; TAC3 | 0 | 0.00 | | 1 | 3.43 | FFAR2 | 6 | 1.25 | ARHGEF25; CHRM1; CHRM3; EDN3; PLCB4; PTGFR | 9 | 2.09 | BDKRB2; CDK1; GNA15; NTSR1; P2RY1; P2RY2; PRKCQ; PTAFR; QRFPR |
| negative regulation of viral process: GO | 85 | 18 | 3.54 | APOBEC3A; CCL3; HMGA2; IFI16; IFITM1; IFITM3; ISG15; ISG20; LTF; MX1; OAS1; OAS3; OASL; RSAD2; SLPI; STAT1; TRIM14; ZC3H12A | 2 | 0.28 | GSN; POU2F3 | 0 | 0.00 | | 2 | 9.83 | IFITM3; ISG15 | 1 | 0.30 | FBLN1 | 7 | 2.34 | HMGA2; IFI16; LTF; MX1; OAS1; SLPI; ZC3H12A |
| establishment of cell polarity: GO | 85 | 10 | 1.97 | CCL21; CENPA; FERMT1; FOXF1; FSCN1; MSN; NDC80; RAB10; WNT5A; WNT7A | 6 | 0.83 | AMOT; BRSK2; EPHB1; PAX6; PKD1; UST | 0 | 0.00 | | 0 | 0.00 | | 3 | 0.90 | BRSK2; SPRY1; UST | 7 | 2.34 | CENPA; FERMT1; MSN; NDC80; SPAG5; WNT5A; WNT7A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| pi3kci akt pathway | 35 | 4 | 1.91 | CDKN1A; SFN; YWHAQ; YWHAZ | 1 | 0.34 | SLC2A4 | 0 | 0.00 | | 0 | 0.00 | | 0 | 0.00 | | 4 | 3.24 | CDKN1A; SFN; YWHAQ; YWHAZ |
| tp53 regulates transcription of cell death genes | 35 | 4 | 1.91 | BIRC5; PERP; PRELID1; TNFRSF10A | 0 | 0.00 | | 0 | 0.00 | | 0 | 0.00 | | 0 | 0.00 | | 4 | 3.24 | BIRC5; IGFBP3; NDRG1; PRELID1 |
| fibrinolysis: GO | 21 | 5 | 3.98 | F12; PLAU; PLAUR; SERPINB2; SERPINE1 | 2 | 1.12 | KLKB1; TMPRSS6 | 0 | 0.00 | | 1 | 19.90 | SERPINE1 | 0 | 0.00 | | 3 | 4.05 | F12; PLAT; SERPINB2 |
| purinergic nucleotide receptor signaling pathway: GO | 21 | 5 | 3.98 | GPR171; GPR87; P2RY1; P2RY2; PTAFR | 3 | 1.69 | P2RX1; P2RX6; P2RX7 | 0 | 0.00 | | 0 | 0.00 | | 1 | 1.21 | P2RY4 | 3 | 4.05 | P2RY1; P2RY2; PTAFR |
| regulation of protein import into nucleus translocation: GO | 21 | 4 | 3.19 | CDK1; CDKN1A; IL6; TXN | 0 | 0.00 | | 0 | 0.00 | | 0 | 0.00 | | 0 | 0.00 | | 3 | 4.05 | CDK1; CDKN1A; TXN |
| fucosylation: GO | 21 | 3 | 2.39 | FUT1; FUT2; FUT3 | 1 | 0.56 | FUT9 | 0 | 0.00 | | 0 | 0.00 | | 0 | 0.00 | | 3 | 4.05 | FUT1; FUT2; FUT3 |
| glucose 6 phosphate metabolic process: GO | 21 | 3 | 2.39 | HK2; PGM2; TPI1 | 0 | 0.00 | | 0 | 0.00 | | 0 | 0.00 | | 0 | 0.00 | | 3 | 4.05 | HK2; TKT; TPI1 |
| hypoxia and p53 in the cardiovascular system | 21 | 2 | 1.59 | CDKN1A; HIF1A | 0 | 0.00 | | 0 | 0.00 | | 0 | 0.00 | | 0 | 0.00 | | 3 | 4.05 | CDKN1A; HIF1A; IGFBP3 |
| mrna transcription: GO | 21 | 2 | 1.59 | EREG; HIF1A | 0 | 0.00 | | 0 | 0.00 | | 0 | 0.00 | | 0 | 0.00 | | 3 | 4.05 | EREG; HIF1A; PPARD |
| regulation of telomere capping: GO | 21 | 2 | 1.59 | NEK2; PRKCQ | 1 | 0.56 | MAPK15 | 0 | 0.00 | | 0 | 0.00 | | 0 | 0.00 | | 3 | 4.05 | AURKB; NEK2; PRKCQ |
| g1/s dna damage checkpoints | 51 | 8 | 2.62 | CCNA2; CCNE1; CDC25A; | 0 | 0.00 | | 0 | 0.00 | | 0 | 0.00 | | 0 | 0.00 | | 5 | 2.78 | CCNA2; CDC25A; CDC25B; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | CDC25B; CDKN1A; CHEK1; PSMA5; PSMB6 | | | | | | | | | | | | | | | CDKN1A; CHEK1 |
| solute sodium symporter activity: GO | 51 | 5 | 1.64 | SLC10A6; SLC28A3; SLC38A1; SLC5A1; SLC6A11 | 9 | 2.08 | SLC10A2; SLC13A2; SLC1A2; SLC1A6; SLC1A7; SLC5A2; SLC5A9; SLC6A17; SLC6A2 | 0 | 0.00 | | 0 | 0.00 | | 4 | 1.99 | SLC13A2; SLC1A6; SLC1A7; SLC5A9 | 5 | 2.78 | SLC13A5; SLC20A1; SLC28A3; SLC5A5; SLC6A11 |
| toxin transport: GO | 36 | 7 | 3.25 | CCT2; CCT3; CCT5; CCT7; CD274; HSPA5; SLC7A8 | 1 | 0.33 | DNM1 | 0 | 0.00 | | 0 | 0.00 | | 0 | 0.00 | | 4 | 3.15 | CCT2; CCT5; HRH2; HSPA5 |
| amino acid transport across the plasma membrane | 36 | 6 | 2.79 | SLC38A1; SLC38A5; SLC7A1; SLC7A11; SLC7A5; SLC7A8 | 2 | 0.66 | SLC7A10; SLC7A9 | 0 | 0.00 | | 0 | 0.00 | | 1 | 0.71 | SLC16A10 | 4 | 3.15 | SLC38A5; SLC7A1; SLC7A11; SLC7A5 |
| myoblast differentiation: GO | 36 | 6 | 2.79 | CSRP2; GREM1; HMGCR; NRG1; PITX1; SDC1 | 1 | 0.33 | MYOCD | 0 | 0.00 | | 0 | 0.00 | | 0 | 0.00 | | 4 | 3.15 | CSRP2; NRG1; PITX1; SOX15 |
| pi3k plc trk pathway | 36 | 6 | 2.79 | NGF; NRAS; NTRK1; SFN; YWHAQ; YWHAZ | 1 | 0.33 | CAMK2A | 0 | 0.00 | | 0 | 0.00 | | 0 | 0.00 | | 4 | 3.15 | NGF; SFN; YWHAQ; YWHAZ |
| spindle localization: GO | 36 | 4 | 1.86 | ACTR3; ASPM; CENPA; NDC80 | 1 | 0.33 | PAX6 | 0 | 0.00 | | 0 | 0.00 | | 1 | 0.71 | SPRY1 | 4 | 3.15 | ASPM; CENPA; NDC80; SPAG5 |
| ap1 pathway | 69 | 12 | 2.91 | CDK1; CSF2; FOSL1; GJA1; HIF1A; IFNG; | 4 | 0.68 | ACTA1; AGT; FABP4; IL5 | 0 | 0.00 | | 0 | 0.00 | | 1 | 0.37 | ESR1 | 6 | 2.47 | CDK1; FOSL1; HIF1A; IL10; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | IL6; MMP1; MMP9; MT2A; PLAU; TH | | | | | | | | | | | | | | | JUNB; TH |
| mtor 4pathway | 69 | 7 | 1.70 | CCNE1; CYCS; EIF4EBP1; NRAS; SFN; YWHAQ; YWHAZ | 3 | 0.51 | EEF2K; PPARGC1A; SSPO | 0 | 0.00 | | 0 | 0.00 | | 1 | 0.37 | PPARGC1A | 6 | 2.47 | CYCS; EIF4EBP1; SFN; SGK1; YWHAQ; YWHAZ |
| chemokine receptor binding: GO | 52 | 15 | 4.83 | CCL17; CCL18; CCL21; CCL22; CCL3; CCL7; CXCL1; CXCL10; CXCL11; CXCL13; CXCL3; CXCL5; CXCL6; CXCL9; S100A14 | 1 | 0.23 | CCL14 | 0 | 0.00 | | 2 | 16.07 | CXCL5; CXCL9 | 2 | 0.98 | CCL14; CXCL12 | 5 | 2.73 | CCL20; CXCL11; CXCL2; CXCL6; S100A14 |
| intrinsic apoptotic signaling pathway by p53 class mediator: GO | 52 | 7 | 2.25 | AEN; BRCA2; CDKN1A; IFI16; PERP; PYCARD; TP63 | 4 | 0.91 | NUPR1; ZMAT1; ZMAT4; ZNF385B | 0 | 0.00 | | 0 | 0.00 | | 2 | 0.98 | ZMAT1; ZNF385D | 5 | 2.73 | BCL3; BRCA2; CDKN1A; E2F1; IFI16 |
| positive regulation of reproductive process: GO | 52 | 7 | 2.25 | AURKA; CIQBP; P2RY1; P2RY2; PLAU; PTAFR; WNT5A | 8 | 1.82 | CACNA1H; DRD4; INHBB; NPM2; NR5A1; PIWIL2; SEMA3A; ZFPM2 | 0 | 0.00 | | 0 | 0.00 | | 2 | 0.98 | CACNA1H; ZFPM2 | 5 | 2.73 | AURKA; P2RY1; P2RY2; PTAFR; WNT5A |
| cell division site: GO | 52 | 5 | 1.61 | ANLN; CEP55; ECT2; PITPNM1; RACGAP1 | 0 | 0.00 | | 0 | 0.00 | | 0 | 0.00 | | 0 | 0.00 | | 5 | 2.73 | ANLN; CEP55; ECT2; PITPNM1; PLK4 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| axis specification: GO | 87 | 6 | 1.15 | AURKA; MDFI; RGS20; STIL; WNT5A; WNT7A | 8 | 1.08 | CDX4; COBL; CXXC4; EGF; GPC3; PAX6; PTCH1; TDRD5 | 0 | 0.00 | | 0 | 0.00 | | 4 | 1.17 | CDX4; EGF; HOXD8; PTCH1 | 7 | 2.28 | AURKA; IRX4; MDFI; RGS20; STIL; WNT5A; WNT7A |
| positive regulation of protein localization to nucleus: GO | 125 | 18 | 2.41 | CCT2; CCT3; CCT5; CCT6A; CCT7; CDK1; ECT2; GREM1; IL12B; IL1B; IL6; JUP; PLK1; PRKCQ; PTGS2; SULF2; TGFBR1; ZC3H12A | 8 | 0.76 | CHP2; DACT1; EDA; EGF; ERBB4; LEP; LIF; TERT | 0 | 0.00 | | 1 | 3.34 | IL1B | 5 | 1.02 | CHP2; DACTI; EGF; ERBB4; ZIC1 | 9 | 2.04 | CCT2; CCT5; CDK1; ECT2; GTSE1; PLK1; PRKCQ; PTGS2; ZC3H12A |
| organelle biogenesis and maintenance | 165 | 11 | 1.12 | CCT5; CDK1; CYCS; DYNLL1; KIF2C; NEK2; PLK1; TUBA1C; TUBA4A; TUBB2A; TUBB6 | 6 | 0.43 | ALB; MAST1; PPARGC1A; PRKAA2; PRKAR2B; SHC2 | 1 | 2.53 | PRKAR2B | 0 | 0.00 | | 5 | 0.77 | B9D1; DLC1; PPARGC1A; PRKAA2; SHC2 | 11 | 1.89 | CCT5; CDK1; CYCS; KIF2C; NEK2; PLK1; PLK4; TUBA1C; TUBA4A; TUBB2A; TUBB6 |
| positive regulation of synaptic transmission: GO | 106 | 11 | 1.74 | ADCYAP1; CA2; IFNG; NMU; NTRK1; NTSR1; PLK2; PTGS2; SERPINE2; UNC13A; WNT7A | 19 | 2.11 | ADORA1; ADRA1A; CLSTN2; DNM1; DRD1; DRD4; GRIN1; GRIN2A; LAMA2; NETO1; NLGN1; NRXN1; RAB3B; RELN; | 0 | 0.00 | | 0 | 0.00 | | 7 | 1.68 | ADRA1A; LAMA2; NRXN1; RAB3B; RELN; RIMS1; SNCA | 8 | 2.14 | CA2; NMU; NTSR1; PLK2; PTGS2; SERPINE2; UNC13A; WNT7A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | RIMS1; SHANK1; SLC24A2; SNCA; SYT1 | | | | | | | | | | | | |
| acyl chain remodelling of pc | 22 | 4 | 3.04 | MBOAT2; PLA2G3; PLA2G4D; PLBD1 | 3 | 1.61 | PLA2G16; PLA2G5; PLA2G6 | 1 | 19.00 | PLA2G16 | 0 | 0.00 | | 0 | 0.00 | | 3 | 3.87 | LPCAT1; PLA2G3; PLA2G4D |
| establishment of epithelial cell polarity: GO | 22 | 4 | 3.04 | FERMT1; FOXF1; MSN; WNT5A | 0 | 0.00 | | 0 | 0.00 | | 0 | 0.00 | | 0 | 0.00 | | 3 | 3.87 | FERMT1; MSN; WNT5A |
| regulation of protein homodimerization activity: GO | 22 | 3 | 2.28 | BAK1; HSPA5; NRG1 | 2 | 1.07 | BCL2; ICA1 | 0 | 0.00 | | 0 | 0.00 | | 2 | 2.31 | BCL2; ICA1 | 3 | 3.87 | BAK1; HSPA5; NRG1 |
| syndecan interactions | 22 | 3 | 2.28 | ITGA6; SDC1; TNC | 1 | 0.54 | SDC2 | 0 | 0.00 | | 0 | 0.00 | | 1 | 1.15 | GULP1 | 3 | 3.87 | ACTN1; ITGA6; ITGB4 |
| mitochondrial membrane organization: GO | 88 | 10 | 1.90 | BAK1; DYNLL1; HK2; HSPA4; PPIF; SFN; SLC25A5; TP63; YWHAQ; YWHAZ | 4 | 0.54 | BCL2; CAMK2A; NOL3; SNCA | 0 | 0.00 | | 1 | 4.75 | GZMB | 2 | 0.58 | BCL2; SNCA | 7 | 2.26 | BAK1; E2F1; HK2; PPIF; SFN; YWHAQ; YWHAZ |
| response to hydrogen peroxide: GO | 107 | 14 | 2.19 | ANXA1; AREG; BAK1; CDK1; ECT2; FOSL1; HIF1A; HMOX1; IL6; LDHA; NR4A3; OLR1; PPIF; SDC1 | 7 | 0.77 | BCL2; CRYAB; HBA1; HBA2; HBB; PDGFD; TXNIP | 1 | 3.91 | CRYAB | 0 | 0.00 | | 4 | 0.95 | BCL2; HBA2; HBB; TXNIP | 8 | 2.12 | AREG; BAK1; CDK1; ECT2; FOSL1; HIF1A; LDHA; PPIF |
| positive regulation of protein modification by | 187 | 18 | 1.61 | BUB1B; CCNB1; CDC20; CDK1; FBXO5; | 4 | 0.25 | CLU; EGF; HAMP; MAPK15 | 0 | 0.00 | | 0 | 0.00 | | 5 | 0.68 | ANGPT1; CLU; EGF; PRICKLE1; TSPYL5 | 12 | 1.82 | BUB1B; CCNB1; CDC20; CDK1; FANCI; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| small protein conjugation or removal: GO | | | | HSPA5; MAD2L1; NMI; PLK1; PSMA4; PSMA5; PSMB6; PSMD1; PSME3; UBE2C; UBE2N; UBE2S; VCP | | | | | | | | | | | | | | | HSPA5; MAD2L1; NMI; PLK1; TRIB3; UBE2C; UBE2S |
| chemokine receptors bind chemokines | 53 | 18 | 5.68 | CCL17; CCL21; CCL22; CCL3; CCL7; CCR4; CCR5; CXCL1; CXCL10; CXCL11; CXCL13; CXCL3; CXCL5; CXCL6; CXCL8; CXCL9; CXCR1; CXCR4 | 1 | 0.22 | CXCR5 | 0 | 0.00 | | 2 | 15.77 | CXCL5; CXCL9 | 1 | 0.48 | CXCL12 | 5 | 2.68 | CCL20; CXCL11; CXCL2; CXCL6; CXCR1 |
| I amino acid transmembrane transporter activity: GO | 53 | 7 | 2.21 | SERINC2; SLC38A1; SLC38A5; SLC7A1; SLC7A11; SLC7A5; SLC7A8 | 8 | 1.78 | OCA2; SLC17A7; SLC1A2; SLC1A6; SLC1A7; SLC7A10; SLC7A14; SLC7A9 | 0 | 0.00 | | 0 | 0.00 | | 2 | 0.96 | SLC1A6; SLC1A7 | 5 | 2.68 | SERINC2; SLC38A5; SLC7A1; SLC7A11; SLC7A5 |
| anion cation symporter activity: GO | 53 | 2 | 0.63 | SLC10A6; SLC6A11 | 9 | 2.00 | SLC10A2; SLC13A2; SLC17A4; SLC17A7; SLC1A2; SLC1A6; | 0 | 0.00 | | 0 | 0.00 | | 4 | 1.92 | SLC13A2; SLC1A6; SLC1A7; SLC4A4 | 5 | 2.68 | SLC13A5; SLC20A1; SLC4A7; SLC5A5; SLC6A11 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | | | | SLC1A7; SLC34A3; SLC4A4 | | | | | | | | | | | | |
| regulation of ligase activity: GO | 127 | 16 | 2.11 | BUB1B; CCNB1; CDC20; CDK1; FBXO5; GEN1; MAD2L1; PLK1; PSMA4; PSMA5; PSMB6; PSMD1; PSME3; UBE2C; UBE2N; UBE2S | 0 | 0.00 | | 0 | 0.00 | | 0 | 0.00 | | 0 | 0.00 | | 9 | 2.01 | BUB1B; CCNB1; CDC20; CDK1; MAD2L1; PLK1; TRIB3; UBE2C; UBE2S |
| intrinsic apoptotic signaling pathway: GO | 147 | 14 | 1.59 | AEN; BAK1; BCL2A1; BRCA2; CDKN1A; CHAC1; CYCS; HMOX1; IFI16; MELK; PERP; PYCARD; SFN; TP63 | 14 | 1.12 | ATP2A1; BCL2; BRSK2; CASP12; CLU; CRIP1; LGALS12; MAPT; NOL3; NUPR1; PRODH; ZMAT1; ZMAT4; ZNF385B | 0 | 0.00 | | 0 | 0.00 | | 9 | 1.56 | BCL2; BRSK2; CASP12; CLU; CRIP1; MAPT; PRODH; ZMAT1; ZNF385D | 10 | 1.93 | BAK1; BCL3; BRCA2; CDKN1A; CYCS; E2F1; EPHA2; IFI16; SFN; TRIB3 |
| loss of nlp from mitotic centrosomes | 71 | 6 | 1.41 | CDK1; DYNLL1; NEK2; PLK1; TUBA1C; TUBA4A | 3 | 0.50 | MAST1; PRKAR2B; TUBB4A | 1 | 5.89 | PRKAR2B | 0 | 0.00 | | 1 | 0.36 | DLC1 | 6 | 2.40 | CDK1; NEK2; PLK1; PLK4; TUBA1C; TUBA4A |
| neuromuscular junction: GO | 54 | 6 | 1.86 | CDK5R1; CXADR; NRG1; PRKCQ; | 7 | 1.53 | DES; LRP4; P2RX7; PDZRN3; PPP1R9A; | 0 | 0.00 | | 0 | 0.00 | | 2 | 0.94 | PDZRN3; SPOCK1 | 5 | 2.63 | CDK5R1; NRG1; PRKCQ; SERPINE2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline: Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo: Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo: Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | SERPINE2; UNC13A | | | SPOCK1; SYNGR1 | | | | | | | | | | | | UNC13A |
| metabolism of vitamins and cofactors | 148 | 12 | 1.36 | ACP5; AKRIB10; GSTO1; LDLR; LRP8; MTHFD2; NAMPT; PARP9; PTGS2; SDC1; SLC2A1; SLC52A2 | 12 | 0.96 | ACACB; ALDH1L1; APOE; ENPP1; FOLR1; GPC3; GPC6; PTGIS; RBP4; SDC2; SLC19A3; TTPA | 0 | 0.00 | | 0 | 0.00 | | 4 | 0.69 | AOX1; ENPP3; NMNAT3; SLC19A3 | 10 | 1.92 | ACP5; AGRN; AKRIB10; LDLR; NAMPT; PARP9; PDSS1; PTGS2; SLC2A1; SLC52A2 |
| exploration behavior: GO | 23 | 3 | 2.18 | DPP4; EIF4A3; ITGA3 | 0 | 0.00 | | 0 | 0.00 | | 0 | 0.00 | | 2 | 2.21 | CHL1; LSAMP | 3 | 3.70 | DPP4; EIF4A3; ITGA3 |
| p53hypoxia pathway | 23 | 3 | 2.18 | CDKN1A; CSNK1A1; HIF1A | 0 | 0.00 | | 0 | 0.00 | | 0 | 0.00 | | 0 | 0.00 | | 3 | 3.70 | CDKN1A; HIF1A; IGFBP3 |
| prl signaling events pathway | 23 | 3 | 2.18 | CCNA2; CCNE1; CDKN1A | 1 | 0.51 | AGT | 0 | 0.00 | | 0 | 0.00 | | 0 | 0.00 | | 3 | 3.70 | CCNA2; CDKN1A; PTP4A1 |
| platelet aggregation: GO | 38 | 3 | 1.32 | ACTB; RAP2B; SLC7A11 | 3 | 0.93 | GATA1; HBB; MYL9 | 0 | 0.00 | | 0 | 0.00 | | 1 | 0.67 | HBB | 4 | 2.98 | ACTB; ACTN1; RAP2B; SLC7A11 |
| positive regulation of peptidase activity: GO | 149 | 20 | 2.25 | BAK1; CCK; CYCS; FAM162A; IFI16; IFI27; MEFV; NGF; NLRP2; PERP; PRELID1; PSME3; PYCARD; S100A8; S100A9; SERPINB3; SOX7; TNFRSF10A; | 5 | 0.40 | ACVR1C; GSN; P2RX1; PCOLCE2; SNCA | 1 | 2.80 | ACVR1C | 0 | 0.00 | | 5 | 0.85 | CTGF; DLC1; FBLN1; PCOLCE; SNCA | 10 | 1.90 | BAK1; CYCS; IFI16; IFI27; MEFV; NGF; NLRP2; PRELID1; SOX7; XDH |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | TNFSF10; VCP | | | | | | | | | | | | | | | |
| leading edge membrane: GO | 129 | 10 | 1.30 | CFL1; CNTNAP2; DPP4; FERMT1; NME1; NRG1; PDPN; PLEK2; SLC39A6; TWF1 | 8 | 0.73 | ADORA1; GRIA1; ITGA8; KCNA2; PALM; PDE9A; SLC1A2; TPM1 | 0 | 0.00 | | 0 | 0.00 | | 5 | 0.98 | DLC1; GRIA1; PALM; PDE9A; TESC | 9 | 1.98 | CFL1; CNTNAP2; DPP4; EPHA2; FERMT1; NRG1; PLEK2; SPRY4; TWF1 |
| eph-ephrin signaling | 55 | 6 | 1.83 | ACTB; ACTR3; ARPC1A; MMP9; PSENEN; SHB | 3 | 0.64 | EPHB6; MYL9; SDC2 | 0 | 0.00 | | 0 | 0.00 | | 0 | 0.00 | | 5 | 2.58 | ACTB; ARPC1A; EPHA2; SHB; VAV2 |
| regulation of dna biosynthetic process: GO | 91 | 11 | 2.02 | CCT2; CCT3; CCT5; CCT6A; CCT7; CDKN1A; GJA1; GREM1; NEK2; PIF1; PRKCQ | 4 | 0.52 | ADIPOQ; DACH1; MAPK15; PAK3 | 1 | 4.59 | ADIPOQ | 0 | 0.00 | | 3 | 0.84 | DACH1; KCNK2; PAK3 | 7 | 2.18 | AURKB; CCT2; CCT5; CDKN1A; NEK2; PIF1; PRKCQ |
| orc1 removal from chromatin | 73 | 9 | 2.06 | CCNA2; CDC6; CDKN1A; ORC1; ORC6; PSMA4; PSMA5; PSMB6; PSMD1 | 0 | 0.00 | | 0 | 0.00 | | 0 | 0.00 | | 0 | 0.00 | | 6 | 2.33 | CCNA2; CDC6; CDKN1A; MCM2; ORC1; ORC6 |
| clathrin-mediated endocytosis | 73 | 7 | 1.60 | ACTB; ACTR3; ARPCA; HSPA8; LDLR; STON2; WNT5A | 6 | 0.97 | AGTR1; EGF; FZD4; SYT1; SYT9; TF | 0 | 0.00 | | 0 | 0.00 | | 2 | 0.70 | AGTR1; EGF | 6 | 2.33 | ACTB; ARPC1A; HSPA8; LDLR; STON2; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| interleukin-10 signaling | 39 | 13 | 5.58 | CCL3; CSF2; CXCL1; CXCL10; CXCL3; CXCL8; FPR1; IL1A; IL1B; ILIR2; IL1RN; IL6; PTGS2 | 1 | 0.30 | LIF | 0 | 0.00 | | 1 | 10.72 | IL1B | 0 | 0.00 | | 4 | 2.91 | CCL20; CXCL2; IL10; PTGS2 |
| hindbrain morphogenesis: GO | 39 | 4 | 1.72 | HSPA5; KIF14; SERPINE2; WNT7A | 4 | 1.21 | ATP2B2; CBLN1; GLI2; NRXN1 | 0 | 0.00 | | 0 | 0.00 | | 3 | 1.95 | DLC1; GLI2; NRXN1 | 4 | 2.91 | HSPA5; KIF14; SERPINE2; WNT7A |
| homologous chromosome segregation: GO | 39 | 4 | 1.72 | BRCA2; PLK1; PTTG1; TRIP13 | 2 | 0.61 | STAG3; SYCP1 | 0 | 0.00 | | 0 | 0.00 | | 0 | 0.00 | | 4 | 2.91 | BRCA2; PLK1; PTTG1; TRIP13 |
| intrinsic pathway for apoptosis | 39 | 4 | 1.72 | BAK1; CYCS; DYNLL1; SFN | 1 | 0.30 | BCL2 | 0 | 0.00 | | 1 | 10.72 | GZMB | 3 | 1.95 | BCL2; CTSG; DLC1 | 4 | 2.91 | BAK1; CYCS; E2F1; SFN |
| negative chemotaxis: GO | 39 | 4 | 1.72 | FLRT3; NRG1; SEMA4B; WNT5A | 10 | 3.03 | NRG3; PLXNA3; PLXNA4; SEMA3A; SEMA3B; SEMA3D; SEMA3E; SEMA3G; SLIT2; SLIT3 | 0 | 0.00 | | 0 | 0.00 | | 5 | 3.26 | PLXNA4; SEMA3E; SEMA4G; SLIT2; SLIT3 | 4 | 2.91 | FLRT3; NRG1; SEMA4B; WNT5A |
| pallium development: GO | 151 | 16 | 1.77 | ANXA3; ASPM; CDK5R1; CNTNAP2; EOMES; FBXO45; H2AFX; HIF1A; KIF14; LRP8; NEFL; NME1; NR4A3; RAN; TH; UBA6 | 19 | 1.48 | BCAN; CDON; CYP17A1; DCX; DRD1; EMX2; FEZF2; FGFR1; GRIN1; HTR6; ID4; KCNA1; LMX1A; PAX6; | 0 | 0.00 | | 1 | 2.77 | ANXA3 | 7 | 1.18 | CDON; EMX2; FGFR1; MDK; POU3F3; RELN; SLIT2 | 10 | 1.88 | ASPM; CDK5R1; CNTNAP2; FBXO45; H2AFX; HIF1A; KIF14; RAN; TACC3; TH |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | PLXNA3; POU3F3; RELN; SEMA3A; SLIT2 | | | | | | | | | | | | |
| regulation of dna binding: GO | 92 | 11 | 2.00 | GZMA; HJURP; HMGA2; HMOX1; IFI16; MDFI; MMP9; NEK2; NME1; PLAUR; TXN | 7 | 0.90 | EGF; GATA1; HAND2; KAT2A; LIF; MYOCD; WFIKKN1 | 1 | 4.54 | WFIKKN1 | 0 | 0.00 | | 2 | 0.55 | EGF; HAND2 | 7 | 2.16 | BCL3; E2F1; HMGA2; IFI16; MDFI; NEK2; TXN |
| positive regulation of interleukin 1 secretion: GO | 24 | 7 | 4.88 | CCL3; IFNG; NLRP2; PANX1; PYCARD; TRIM16; WNT5A | 1 | 0.49 | P2RX7 | 0 | 0.00 | | 0 | 0.00 | | 0 | 0.00 | | 3 | 3.54 | NLRP2; PANX1; WNT5A |
| alpha tubulin binding: GO | 24 | 5 | 3.49 | ARL4C; FAM110C; HSPH1; RACGAP1; SNCB | 3 | 1.47 | NCALD; PPARGC1A; SNCA | 0 | 0.00 | | 0 | 0.00 | | 3 | 3.18 | NCALD; PPARGC1A; SNCA | 3 | 3.54 | FAM110C; HSPH1; SNCB |
| positive regulation of coagulation: GO | 24 | 5 | 3.49 | F12; HPSE; S100A9; SERPINE1; THBD | 2 | 0.98 | ENPP4; F7 | 0 | 0.00 | | 1 | 17.41 | SERPINE1 | 0 | 0.00 | | 3 | 3.54 | F12; HPSE; THBD |
| interconversion of nucleotide di- and triphosphates | 24 | 3 | 2.09 | NME1; RRM2; TXN | 0 | 0.00 | | 0 | 0.00 | | 0 | 0.00 | | 1 | 1.06 | GLRX | | 3.54 | CTPS1; RRM2; TXN |
| regulation of tp53 degradation | 24 | 3 | 2.09 | CCNA2; CDK1; USP2 | 0 | 0.00 | | 0 | 0.00 | | 0 | 0.00 | | 0 | 0.00 | | 3 | 3.54 | CCNA2; CDK1; SGK1 |
| regulation of tp53 expression and degradation | 24 | 3 | 2.09 | CCNA2; CDK1; USP2 | 0 | 0.00 | | 0 | 0.00 | | 0 | 0.00 | | 0 | 0.00 | | 3 | 3.54 | CCNA2; CDK1; SGK1 |
| dna secondary structure binding: GO | 24 | 2 | 1.39 | BLM; HMGB3 | 0 | 0.00 | | 0 | 0.00 | | 0 | 0.00 | | 0 | 0.00 | | 3 | 3.54 | BLM; HMGB3; NEIL3 |
| establishment of spindle | 24 | 2 | 1.39 | CENPA; NDC80 | 1 | 0.49 | PAX6 | 0 | 0.00 | | 0 | 0.00 | | 1 | 1.06 | SPRY1 | 3 | 3.54 | CENPA; NDC80; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| orientation: GO | | | | | | | | | | | | | | | | | | | SPAG5 |
| organic anion transmembrane transporter activity: GO | 172 | 14 | 1.36 | PDPN; SERINC2; SLC10A6; SLC16A1; SLC16A6; SLC16A9; SLC26A9; SLC38A1; SLC38A5; SLC6A11; SLC7A1; SLC7A11; SLC7A5; SLC7A8 | 26 | 1.78 | ABCB11; ABCC3; CFTR; OCA2; SLC10A2; SLC13A2; SLC16A11; SLC16A12; SLC16A8; SLC17A7; SLC1A2; SLC1A6; SLC1A7; SLC22A17; SLC22A9; SLC26A1; SLC26A5; SLC26A7; SLC4A1; SLC4A4; SLC6A17; SLC7A10; SLC7A14; SLC7A9; SLCO4C1; SLCO5A1 | 0 | 0.00 | | 1 | 2.43 | AQP9 | 6 | 0.89 | SLC13A2; SLC16A10; SLC1A6; SLC1A7; SLC22A17; SLC4A4 | 11 | 1.81 | SERINC2; SLC13A5; SLC16A6; SLC16A9; SLC26A6; SLC38A5; SLC4A7; SLC6A11; SLC7A1; SLC7A11; SLC7A5 |
| germ cell development: GO | 193 | 14 | 1.21 | ASPM; BRCA2; CCNB1; CDC25B; EREG; FBXO5; HOOK1; INSL3; PAQR5; PLA2G3; PRDM1; RAN; TRIP13; TXNDC8 | 22 | 1.34 | BCL2; CAPZA3; CELF4; CFTR; CHD5; DDX25; H1FNT; HILS1; INHBB; LGR5; NOBOX; NPM2; OCA2; PIWIL2; PRSS42; RSPH1; SPAG6; | 0 | 0.00 | | 0 | 0.00 | | 5 | 0.66 | BCL2; CAPZA3; DDX25; LGR5; SYCP3 | 12 | 1.76 | ASPM; BMPRIB; BRCA2; CCNB1; CDC25B; EREG; PAQR5; PLA2G3; PTCHD3; RAN; SLC26A6; TRIP13 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | SYCP1; TDRD5; TNP1; YBX2; ZBTB16 | | | | | | | | | | | | |
| wnt signaling pathway | 74 | 7 | 1.58 | ACTB; CCND2; FOSL1; GAPDH; PPP2R2C; RAC2; RUVBL1 | 5 | 0.80 | CAMK2B; CHP2; DAAM2; PLCB4; PPP2R2B | 0 | 0.00 | | 1 | 5.65 | RAC2 | 3 | 1.03 | CHP2; PLCB4; RHOU | 6 | 2.30 | ACTB; CCND2; FOSL1; GAPDH; PPARD; PPP2R2C |
| morphogenesis of an epithelial sheet: GO | 40 | 6 | 2.51 | FLRT3; HBEGF; MMP12; TBX20; WNT5A; WNT7A | 0 | 0.00 | | 0 | 0.00 | | 0 | 0.00 | | 1 | 0.64 | SCNN1B | 4 | 2.84 | FLRT3; HBEGF; WNT5A; WNT7A |
| negative regulation of stress activated protein kinase signaling cascade: GO | 40 | 6 | 2.51 | F2RL1; FOXM1; GSTP1; HSPH1; PBK; SERPINB3 | 4 | 1.18 | AMBP; DACT1; MAPK8IP1; PER1 | 0 | 0.00 | | 0 | 0.00 | | 1 | 0.64 | DACT1 | 4 | 2.84 | FOXM1; GSTP1; HSPH1; PBK |
| cytoplasmic sequestering of protein: GO | 40 | 4 | 1.67 | HK2; HSPA5; MDFI; PDIA3 | 2 | 0.59 | GRIK5; PKD1 | 0 | 0.00 | | 0 | 0.00 | | 0 | 0.00 | | 4 | 2.84 | HK2; HSPA5; IL10; MDFI |
| regulation of insulin receptor signaling pathway: GO | 40 | 4 | 1.67 | IL1B; PRKCQ; PTPRE; SOCS3 | 4 | 1.18 | ENPP1; LEP; MSTN; SERPINA12 | 0 | 0.00 | | 1 | 10.45 | IL1B | 1 | 0.64 | SERPINA12 | 4 | 2.84 | CISH; PRKCQ; PTPRE; SOCS3 |
| rna secondary structure unwinding: GO | 40 | 3 | 1.26 | DDX21; DDX28; EIF4A3 | 1 | 0.29 | DDX25 | 0 | 0.00 | | 0 | 0.00 | | 1 | 0.64 | DDX25 | 4 | 2.84 | DDX21; DDX28; DDX39A; EIF4A3 |
| ecadherin stabilization pathway | 40 | 2 | 0.84 | AQP3; ENAH | 2 | 0.59 | CAMSAP3; EGF | 0 | 0.00 | | 0 | 0.00 | | 1 | 0.64 | EGF | 4 | 2.84 | ACTN1; AQP3; ENAH; EPHA2 |
| positive regulation of dna | 57 | 8 | 2.35 | CCT2; CCT3; CCT5; | 2 | 0.41 | MAPK15; PAK3 | 0 | 0.00 | | 0 | 0.00 | | 1 | 0.45 | PAK3 | 5 | 2.49 | AURKB; CCT2; CCT5; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| biosynthetic process: GO | | | | CCT6A; CCT7; GREM1; NEK2; PRKCQ | | | | | | | | | | | | | | | NEK2; PRKCQ |
| cell-cell communication | 75 | 6 | 1.34 | ACTB; FBLIM1; ITGA6; JUP; KRT17; LAMB3 | 5 | 0.79 | CADM2; CDH12; CDH4; CLDN16; KRT15 | 0 | 0.00 | | 0 | 0.00 | | 1 | 0.34 | CADM2 | 6 | 2.27 | ACTB; ACTN1; FBLIM1; ITGA6; ITGB4; LAMB3 |
| maintenance of location in cell: GO | 94 | 8 | 1.42 | ASPM; HK2; HSPA5; JUP; MDFI; PDIA3 SRGN; TWF1 | 12 | 1.51 | ALB; APOE; ATP2A1; GRIK5; GSN; NR5A1; PKD1; SCIN; SHANK1; SPTBN4; SYNE1; TLN2 | 0 | 0.00 | | 0 | 0.00 | | 4 | 1.08 | SCIN; SPTBN4; SYNE1; TLN2 | 7 | 2.11 | ASPM; BCL3; HK2; HSPA5; IL10; MDFI; TWF1 |
| nucleoside triphosphate metabolic process: GO | 196 | 18 | 1.54 | ADCYAP1; CMPK2; COX7B; CYCS; ENO1; GAPDH; GNAI3; HK2; HSPA8; LDHA; NME1; NUDT15; OGDHL; PFKFB4; PGAM1; PGK1; TPI1; VCP | 8 | 0.48 | ALDOB; ATP1A2; ATP6V0A4; ATP6V1B1; ENPP1; MYH3; PFKFB1; SNCA | 0 | 0.00 | | 0 | 0.00 | | 6 | 0.78 | AK7; ALDOC; ATP6V0A4; ENPP3; PFKFB1; SNCA | 12 | 1.74 | CYCS; ENO1; GAPDH; HK2; HSPA8; LDHA; NUDT15; OGDHL; PFKFB4; PGAM1; PGK1; TPI1 |
| hdms demethylate histones | 25 | 6 | 4.02 | HIST1H3A; HIST1H3I; HIST1H4I; HIST1H4J; HIST1H4K; HIST1H4L | 0 | 0.00 | | 0 | 0.00 | | 0 | 0.00 | | 0 | 0.00 | | 3 | 3.40 | HIST1H3A; HIST1H3I; HIST1H4I |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| secretory granule organization: GO | 25 | 5 | 3.35 | PLA2G3; RAB38; SERPINE2; SRGN; TXNDC8 | 0 | 0.00 | | 0 | 0.00 | | 0 | 0.00 | | 0 | 0.00 | | 3 | 3.40 | PLA2G3; RAB38; SERPINE2 |
| phosphatidyl-choline acyl chain remodeling: GO | 25 | 4 | 2.68 | MBOAT2; PLA2G3; PLA2G4D; PLBD1 | 3 | 1.42 | PLA2G16; PLA2G5; PLA2G6 | 1 | 16.72 | PLA2G16 | 0 | 0.00 | | 0 | 0.00 | | 3 | 3.40 | LPCAT1; PLA2G3; PLA2G4D |
| regulation of fibroblast growth factor receptor signaling pathway: GO | 25 | 4 | 2.68 | DUSP6; FGFBP1; SULF2; WNT5A | 2 | 0.94 | HHIP; NOG | 0 | 0.00 | | 0 | 0.00 | | 1 | 1.02 | SPRY1 | 3 | 3.40 | DUSP6; FGFBP1; WNT5A |
| eph-ephrin mediated repulsion of cells | 25 | 3 | 2.01 | ACTB; MMP9; PSENEN | 1 | 0.47 | EPHB6 | 0 | 0.00 | | 0 | 0.00 | | 0 | 0.00 | | 3 | 3.40 | ACTB; EPHA2; VAV2 |
| insulin glucose pathway | 25 | 3 | 2.01 | SFN; YWHAQ; YWHAZ | 1 | 0.47 | SLC2A4 | 0 | 0.00 | | 0 | 0.00 | | 1 | 1.02 | ASIP | 3 | 3.40 | SFN; YWHAQ; YWHAZ |
| response to elevated platelet cytosolic ca2 | 25 | 3 | 2.01 | CFL1; PFN1; SERPINA1 | 2 | 0.94 | ACTN2; CFD | 0 | 0.00 | | 0 | 0.00 | | 0 | 0.00 | | 3 | 3.40 | CFL1; PFN1; PPIAP22 |
| mammary gland development: GO | 114 | 8 | 1.17 | AREG; BRCA2; FOXF1; HIF1A; HK2; NME1; NRG1; WNT5A | 8 | 0.83 | ATP2B2; CDO1; EGF; ERBB4; GLI2; IRS2; NRG3; PTCH1 | 0 | 0.00 | | 0 | 0.00 | | 7 | 1.56 | EGF; ERBB4; ESR1; GLI2; IGFBP5; PTCH1; SLC29A1 | 8 | 1.99 | AREG; BRCA2; EPHA2; HIF1A; HK2; NRG1; WNT5A; XDH |
| establishment or maintenance of cell polarity: GO | 134 | 13 | 1.62 | ACTR3; CAP1; CCL21; CENPA; FERMT1; FOXF1; FSCN1; KIF2C; MSN; | 8 | 0.70 | AMOT; BRSK2; DLG2; EPHB1; PAX6; PKD1; UST; WNT11 | 0 | 0.00 | | 0 | 0.00 | | 5 | 0.95 | BRSK2; DLG2; SPRY1; UST; WNT11 | 9 | 1.90 | CAP1; CENPA; FERMT1; KIF2C; MSN; NDC80; SPAG5; WNT5A; WNT7A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | NDC80; RAB10; WNT5A; WNT7A | | | | | | | | | | | | | | | |
| coated vesicle membrane: GO | 134 | 8 | 1.00 | AP1S3; AREG; FCGR1A; HBEGF; HSPA8; LDLR; TGFA; WNT5A | 9 | 0.79 | CD207; CLVS1; CLVS2; FOLR1; FZD4; GRIA1; NCALD; SLC17A7; SYT1 | 0 | 0.00 | | 0 | 0.00 | | 6 | 1.14 | CD207; CNIH3; GRIA1; HLA-DQB2; NCALD; SLC18A2 | 9 | 1.90 | APIS3; AREG; HBEGF; HLA-G; HSPA8; LDLR; SLC18A3; TGFA; WNT5A |
| rho gtpase binding: GO | 76 | 3 | 0.66 | DIAPH3; ECT2; PFN1 | 4 | 0.62 | DAAM2; NOX1; PAK3; STXBP6 | 0 | 0.00 | | 0 | 0.00 | | 2 | 0.67 | PAK3; STXBP6 | 6 | 2.24 | ARHGEF16; CDC42EP1; DIAPH3; ECT2; IQGAP3; PFN1 |
| positive regulation of proteasomal protein catabolic process: GO | 95 | 7 | 1.23 | AURKA; CSNK1A1; DLGAP5; FBXO5; PLK1; PLK2; VCP | 1 | 0.12 | CLU | 0 | 0.00 | | 0 | 0.00 | | 3 | 0.80 | CLU; ECSCR; PRICKLE1 | 7 | 2.09 | AURKA; DLGAP5; PLK1; PLK2; RNF19B; TRIB1; TRIB3 |
| assembly of collagen fibrils and other multimeric structures | 41 | 7 | 2.86 | CTSB; CTSL; ITGA6; LAMB3; MMP1; MMP3; MMP9 | 2 | 0.58 | COL24A1; COL9A2 | 0 | 0.00 | | 0 | 0.00 | | 2 | 1.24 | COL24A1; GULP1 | 4 | 2.77 | ITGA6; ITGB4; LAMB3; MMP3 |
| negative regulation of blood pressure: GO | 41 | 5 | 2.04 | ADM2; BDKRB1; BDKRB2; NTSR1; PTAFR | 6 | 1.73 | ADIPOQ; ADORA1; ADRA1A; ADRB1; CNR1; NOS2 | 1 | 10.19 | ADIPOQ | 0 | 0.00 | | 1 | 0.62 | ADRA1A | 4 | 2.77 | ADM2; BDKRB2; NTSR1; PTAFR |
| regulation of oxidative stress induced cell death: GO | 41 | 5 | 2.04 | HIF1A; HSPH1; MMP3; NR4A3; TXN | 2 | 0.58 | NOL3; NOX1 | 0 | 0.00 | | 0 | 0.00 | | 0 | 0.00 | | 4 | 2.77 | HIF1A; HSPH1; MMP3; TXN |
| negative regulation | 41 | 1 | 0.41 | CYP27B1 | 5 | 1.44 | ACADL; | 0 | 0.00 | | 0 | 0.00 | | 1 | 0.62 | SERPINA12 | 4 | 2.77 | CYP27B1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| of lipid biosynthetic process: GO | | | | | | | APOC1; APOE; BMP5; SERPINA12 | | | | | | | | | | | | LPCAT1; SNAI2; TRIB3 |
| cell adhesion molecule binding: GO | 176 | 16 | 1.52 | ADAM23; CALR; CDK5R1; CXADR; DSP; ESM1; ICAM3; ITGA3; ITGA6; ITGB6; JUP; MSN; NLGN4X; SELL; TRPC4; WISP1 | 20 | 1.34 | ACTN2; ADAM11; ADAM22; CADM2; CADM3; CDHR5; CTNNA3; EDIL3; FBLN5; FCER2; FGFR1; NLGN1; NRXN1; NRXN3; PTPRT; SLC14A2; TNN; TNXB; TSPAN8; WISP2 | 0 | 0.00 | | 0 | 0.00 | | 14 | 2.02 | ADAM22; CADM2; CADM3; CPE; CTGF; EDIL3; FBLN1; FBLN5; FGFR1; NRXN1; PTPRT; TNN; TSPAN8; WISP2 | 11 | 1.77 | ACTN1; ADAM23; CDK5R1; ICAM5; ITGA3; ITGA6; ITGB6; MSN; NDRG1; NLGN4X; PKP3 |
| vitamin metabolic process: GO | 115 | 13 | 1.89 | ACP5; CYP24A1; CYP27B1; CYP4F11; GSTO1; LRAT; MTHFD2; NAMPT; PRSS3; PTGS2; SLC2A1; TCN1; VNN3 | 9 | 0.92 | ACACB; ALDH1L1; CYP1A1; CYP4F12; ENPP1; FOLR1; PTGIS; SLC19A3; TTPA | 0 | 0.00 | | 0 | 0.00 | | 4 | 0.88 | AOX1; CYP3A4; CYP4F12; SLC19A3 | 8 | 1.97 | ACP5; CYP27B1; LRAT; NAMPT; PPARD; PRSS3; PTGS2; SLC2A1 |
| vascular process in circulatory system: GO | 156 | 13 | 1.39 | ADCYAP1; BDKRB2; F2RL1; GJA1; HIF1A; HMGCR; HMOX1; HTR7; | 24 | 1.82 | ADCY6; ADORA1; ADRA1A; ADRA1B; ADRA2A; ADRB1; AGT; AGTR1; | 0 | 0.00 | | 0 | 0.00 | | 12 | 1.95 | ADRA1A; ADRA2A; AGTR1; ANGPT1; CHRM1; CHRM3; EDN3; | 10 | 1.82 | BDKRB2; HIF1A; HRH1; HRH2; P2RY1; P2RY2; PPARD; PRKCQ; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | P2RY1; P2RY2; PRKCQ; PTAFR; PTGS2 | | | AMOT; APOE; ATP1A2; CHRM1; CHRM3; DRD1; EDN3; EPHX2; HBB; KCNMB4; LEP; NOS2; NPY1R; P2RX1; PLA2G6; SLIT2 | | | | | | | | | FOXC1; HBB; NPY1R; PRKG1; SLIT2 | | | PTAFR; PTGS2 |
| regulation of signal transduction by p53 class mediator: GO | 156 | 8 | 0.86 | AURKA; BDKRB2; BLM; CDK5R1; CHEK1; EXO1; TP63; TPX2 | 3 | 0.23 | CHD5; HIPK4; PRKAA2 | 0 | 0.00 | | 0 | 0.00 | | 1 | 0.16 | PRKAA2 | 10 | 1.82 | AURKA; AURKB; BDKRB2; BLM; BRIP1; CDK5R1; CHEK1; EXO1; SNAI2; TPX2 |
| regulation of leukocyte apoptotic process: GO | 77 | 11 | 2.39 | ANXA1; CCL21; CD274; HCAR2; HIF1A; IDO1; JAK3; NR4A3; PRELID1; PRKCQ; WNT5A | 8 | 1.23 | BIRC7; GPAM; IRS2; MERTK; P2RX7; PIP; RORC; TSC22D3 | 1 | 5.43 | GPAM | 1 | 5.43 | HCAR2 | 4 | 1.32 | CXCL12; PIP; SLC46A2; TSC22D3 | 6 | 2.21 | AURKB; HIF1A; IL10; PRELID1; PRKCQ; WNT5A |
| amino acid transmembrane transporter activity: GO | 77 | 9 | 1.96 | PDPN; SERINC2; SLC38A1; SLC38A5; SLC6A11; SLC7A1; SLC7A11; SLC7A5; SLC7A8 | 10 | 1.53 | OCA2; SLC16A12; SLC17A7; SLC1A2; SLC1A6; SLC1A7; SLC6A17; SLC7A10; SLC7A14; SLC7A9 | 0 | 0.00 | | 0 | 0.00 | | 3 | 0.99 | SLC16A10; SLC1A6; SLC1A7 | 6 | 2.21 | SERINC2; SLC38A5; SLC6A11; SLC7A1; SLC7A11; SLC7A5 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| gland morphogenesis: GO | 96 | 9 | 1.57 | AREG; IL6; MKI67; MSN; SERPINB5; TGM2; TNC; TP63; WNT5A | 11 | 1.35 | BCL2; CRIP1; EDA; FGFR1; GLI2; ID4; NOG; NRG3; PAX6; PTCH1; SEMA3A | 0 | 0.00 | | 0 | 0.00 | | 9 | 2.38 | BCL2; CRIP1; ESR1; FGFR1; FOXA1; GDF7; GLI2; IGFBP5; PTCH1 | 7 | 2.07 | AREG; EPHA2; MKI67; MSN; SERPINB5; TGM2; WNT5A |
| cyclin a: cdk2-associated events at s phase entry | 59 | 7 | 1.99 | CCNA2; CCNE1; CDC25A; CDC25B; CDKN1A; PSMA5; PSMB6 | 0 | 0.00 | | 0 | 0.00 | | 0 | 0.00 | | 0 | 0.00 | | 5 | 2.40 | CCNA2; CDC25A; CDC25B; CDKN1A; E2F1 |
| blastocyst development: GO | 59 | 5 | 1.42 | BRCA2; EOMES; GINS1; NEK2; TGFBR1 | 1 | 0.20 | TET1 | 0 | 0.00 | | 0 | 0.00 | | 1 | 0.43 | TET1 | 5 | 2.40 | BRCA2; GINS1; GINS4; JUNB; NEK2 |
| kinase activator activity: GO | 59 | 5 | 1.42 | CDK5R1; CDKN1A; GREM1; LTF; NRG1 | 4 | 0.80 | ANGPT4; EGF; NRG3; WNT11 | 0 | 0.00 | | 0 | 0.00 | | 4 | 1.72 | ANGPT4; EGF; GPRC5B; WNT11 | 5 | 2.40 | AFAP1L2; CDK5R1; CDKN1A; LTF; NRG1 |
| cellular response to interferon gamma: GO | 116 | 21 | 3.03 | CCL17; CCL18; CCL21; CCL22; CCL3; CCL7; EPRS; FCGR1A; GAPDH; GBP6; IFI30; IFNG; IL12B; MT2A; OAS1; OAS2; OAS3; OASL; PTAFR; STAT1; WNT5A | 6 | 0.61 | AQP4; CAMK2A; CAMK2B; CCL14; NCAM1; NOS2 | 0 | 0.00 | | 1 | 3.60 | GBP1 | 3 | 0.66 | CCL14; HLA-DQB2; NCAM1 | 8 | 1.96 | CCL20; GAPDH; GBP6; HLA-G; OAS1; PTAFR; SLC26A6; WNT5A |
| morphogenesis of a polarized | 26 | 6 | 3.86 | FOXF1; GRHL3; | 0 | 0.00 | | 0 | 0.00 | | 0 | 0.00 | | 0 | 0.00 | | 3 | 3.27 | MSN; WNT5A; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| epithelium: GO | | | | MSN; RAB10; TP63; WNT5A | | | | | | | | | | | | | | | WNT9B |
| positive regulation of vascular endothelial growth factor production: GO | 26 | 6 | 3.86 | HIF1A; HPSE; IL1A; IL1B; PTGS2; SULF2 | 3 | 1.36 | C3; CCBE1; NOX1 | 0 | 0.00 | | 1 | 16.07 | IL1B | 2 | 1.95 | C3; CCBE1 | 3 | 3.27 | HIF1A; HPSE; PTGS2 |
| heparan sulfate heparin hs gag metabolism | 26 | 4 | 2.57 | HPSE; HS3ST1; HS3ST3A1; HS3ST3B1 | 6 | 2.72 | BCAN; GPC2; GXYLT2; HPSE2; HS3ST2; HS3ST6 | 0 | 0.00 | | 0 | 0.00 | | 3 | 2.93 | GPC2; GXYLT2; HPSE2 | 3 | 3.27 | HPSE; HS3ST1; HS3ST3A1 |
| regulation of keratinocyte proliferation: GO | 26 | 4 | 2.57 | CDH3; SFN; TGM1; TP63 | 0 | 0.00 | | 0 | 0.00 | | 0 | 0.00 | | 0 | 0.00 | | 3 | 3.27 | SFN; SNAI2; TGM1 |
| mesodermal cell differentiation: GO | 26 | 3 | 1.93 | FOXF1; HMGA2; ITGA3 | 1 | 0.45 | ITGA8 | 0 | 0.00 | | 0 | 0.00 | | 0 | 0.00 | | 3 | 3.27 | HMGA2; ITGA3; ITGB4 |
| protein k11 linked ubiquitination: GO | 26 | 3 | 1.93 | UBE2C; UBE2S; UBE2T | 0 | 0.00 | | 0 | 0.00 | | 0 | 0.00 | | 0 | 0.00 | | 3 | 3.27 | UBE2C; UBE2S; UBE2T |
| regulation of cell cycle checkpoint: GO | 26 | 3 | 1.93 | CCNB1; GEN1; MAD2L1 | 0 | 0.00 | | 0 | 0.00 | | 0 | 0.00 | | 0 | 0.00 | | 3 | 3.27 | CCNB1; MAD2L1; NDRG1 |
| regulation of p38mapk cascade: GO | 26 | 2 | 1.29 | HSPH1; ZC3H12A | 2 | 0.91 | LEP; PER1 | 0 | 0.00 | | 0 | 0.00 | | 0 | 0.00 | | | 3.27 | HSPH1; XDH; ZC3H12A |
| regulation of heart growth: GO | 42 | 6 | 2.39 | CCNB1; CDK1; DUSP6; GJA1; NRG1; TBX20 | 8 | 2.25 | ACACB; ERBB4; FGF9; FGFR1; NKX2-5; NOG; RBP4; TBX5 | 0 | 0.00 | | 0 | 0.00 | | 4 | 2.42 | ERBB4; FGF2; FGFR1; KCNK2 | 4 | 2.70 | CCNB1; CDK1; DUSP6; NRG1 |
| organic acid binding: GO | 200 | 16 | 1.34 | CRABP2; FABP5; FABP6; GOT2; HSPA8; LRAT; PYGL; S100A8; | 23 | 1.36 | ACOX2; ALAS2; ALB; ANXA13; APOC1; FABP4; FOLR1; FOLR2; | 1 | 2.09 | ADIPOQ; | 2 | 4.18 | SELE; TDO2 | 9 | 1.14 | ACOX2; ALDH5A1; ANXA9; GLRB; LPAR1; P4HTM; PMP2; SCIN; | 12 | 1.70 | AGRN; CRABP2; FABP5; GLDC; GOT2; HSPA8; LRAT; MARK1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | S100A9; SELE; ST8SIA2; TDO2; TH; UGT1A1; UGT1A10; UGT1A7 | | | GCHFR; GLRB; GRIN1; GRM7; JPH2; NOS2; OXER1; P4HTM; PCK1; SCIN; SERPINA5; SNCA; SYT1; UGT2B7 | | | | | | | | | SNCA | | | NAGS; PPARD; ST8SIA2; TH |
| response to vitamin: GO | 97 | 12 | 2.07 | ACP5; ALPL; AQP3; CCNE1; CXCL10; CYP24A1; CYP27B1; GSTP1; IL1B; KYNU; PTGS2; TNC | 7 | 0.85 | CYP1A1; F7; FOLR1; FOLR2; GSN; LEP; TIMP3 | 0 | 0.00 | | 1 | 4.31 | IL1B | 0 | 0.00 | | 7 | 2.05 | ACP5; AQP3; BRIP1; CYP27B1; GSTP1; PPARD; PTGS2 |
| cellular response to mechanical stimulus: GO | 78 | 11 | 2.36 | BAK1; CHEK1; CNN2; CTSB; GJA1; HIF1A; IL13RA2; IL1B; MYD88; PTGS2; TNFRSF10A | 2 | 0.30 | AGT; ATP1A2 | 0 | 0.00 | | 1 | 5.36 | IL1B | 0 | 0.00 | | 6 | 2.18 | BAK1; CHEK1; HIF1A; IL13RA2; MYD88; PTGS2 |
| clathrin coated vesicle membrane: GO | 78 | 6 | 1.29 | AP1S3; FCGR1A; HBEGF; HSPA8; LDLR; WNT5A | 7 | 1.06 | CD207; CLVS1; CLVS2; FZD4; NCALD; SLC17A7; SYT1 | 0 | 0.00 | | 0 | 0.00 | | 4 | 1.30 | CD207; HLA-DQB2; NCALD; SLC18A2 | 6 | 2.18 | AP1S3; HBEGF; HSPA8; LDLR; SLC18A3; WNT5A |
| negative regulation of protein binding: GO | 78 | 4 | 0.86 | AURKA; HSPA5; RALB; SLPI | 7 | 1.06 | ADIPOQ; CAMK1; DACTI; DKK1; FRMD7; | 2 | 10.72 | ADIPOQ; WFIKKN1 | 0 | 0.00 | | 2 | 0.65 | CAMK1; DACT1 | 6 | 2.18 | AURKA; AURKB; GTSE1; HSPA5; IL10; SLPI |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | NOG; WFIKKN1 | | | | | | | | | | | | |
| response to carbohydrate: GO | 158 | 14 | 1.48 | ACP5; CLEC7A; CTSB; GJA1; GJB6; GSTP1; HIF1A; IL1B; LDHA; NME1; PLAU; PRKCQ; PTGS2; TH | 15 | 1.12 | ACVR1C; ADIPOQ; ALDOB; COLEC12; GPAM; GPLD1; GRIK5; HMGCS2; IRS2; KCNB1; LEP; LPL; MLXIPL; PPARGC1A; TXNIP | 4 | 10.58 | ACVR1C; ADIPOQ; GPAM; LPL | 1 | 2.64 | IL1B | 7 | 1.13 | CTGF; GPLD1; HMGCS2; PDK3; PPARGC1A; SLC29A1; TXNIP | 10 | 1.79 | ACP5; CLEC7A; GSTP1; HIF1A; LDHA; PPARD; PRKCQ; PTGS2; SLC26A6; TH |
| cyclin e associated events during g1/s transition | 60 | 7 | 1.95 | CCNA2; CCNE1; CDC25A; CDC25B; CDKN1A; PSMA5; PSMB6 | 0 | 0.00 | | 0 | 0.00 | | 0 | 0.00 | | 0 | 0.00 | | 5 | 2.36 | CCNA2; CDC25A; CDC25B; CDKN1A; E2F1 |
| digestive system process: GO | 60 | 4 | 1.12 | LDLR; NMU; SLC5A1; VSIG1 | 14 | 2.75 | ADRA2A; CCKBR; CHRM1; CHRM3; LEP; MOGAT2; MUC4; MUC6; NPCIL1; RBP4; SCT; SLC26A7; SLC9A4; SOAT2 | 0 | 0.00 | | 0 | 0.00 | | 3 | 1.27 | ADRA2A; CHRM1; CHRM3 | 5 | 2.36 | HRH2; LDLR; NMU; SLC26A6; VSIG1 |
| platelet activation: GO | 138 | 10 | 1.21 | ACTB; GNA15; IL6; P2RY1; PDPN; PRKCQ; RAC2; RAP2B; | 7 | 0.60 | ADRA2A; DGKG; GATA1; HBB; MERTK; MYL9; P2RX1 | 0 | 0.00 | | 2 | 6.06 | LCP2; RAC2 | 3 | 0.55 | ADRA2A; HBB; PIK3R6 | 9 | 1.85 | ACTB; ACTN1; GNA15; P2RY1; PRKCQ; RAP2B; SLC7A11; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | SLC7A11; YWHAZ | | | | | | | | | | | | | | | VAV2; YWHAZ |
| regulation of tumor necrosis factor superfamily cytokine production: GO | 98 | 13 | 2.22 | ACP5; CCL3; CD2; CD274; GSTP1; IFNG; IL12B; LTF; PTAFR; PYCARD; SASH3; SLAMF1; ZC3H12A | 3 | 0.36 | ADIPOQ; CD34; CLU | 1 | 4.26 | ADIPOQ | 0 | 0.00 | | 4 | 1.04 | ANGPT1; CD34; CLU; ZBTB20 | 7 | 2.03 | ACP5; BCL3; GSTP1; IL10; LTF; PTAFR; ZC3H12A |
| g alpha q signalling events | 118 | 13 | 1.84 | BDKRB1; BDKRB2; GNA15; GNGT2; GPR65; LPAR3; NPSR1; NTSR1; P2RY1; P2RY2; PRKCQ; PTAFR; QRFPR | 12 | 1.20 | ADRA1B; ARHGEF25; CCKBR; CHRM1; CHRM3; DGKG; EDN3; GCGR; NMUR1; PLCB4; PROK1; TAC3 | 0 | 0.00 | | 1 | 3.54 | FFAR2 | 6 | 1.29 | ARHGEF25; CHRM1; CHRM3; EDN3; PLCB4; PTGFR | 8 | 1.92 | BDKRB2; GNA15; NTSR1; P2RY1; P2RY2; PRKCQ; PTAFR; QRFPR |
| chemokine activity: GO | 43 | 14 | 5.45 | CCL17; CCL18; CCL21; CCL22; CCL3; CCL7; CXCL1; CXCL10; CXCL11; CXCL13; CXCL3; CXCL5; CXCL6; CXCL9 | 1 | 0.27 | CCL14 | 0 | 0.00 | | 2 | 19.44 | CXCL5; CXCL9 | 2 | 1.18 | CCL14; CXCL12 | 4 | 2.64 | CCL20; CXCL11; CXCL2; CXCL6 |
| regulation of epidermal cell | 43 | 6 | 2.33 | AQP3; CYP27B1; | 3 | 0.82 | KRT36; PTCH1; | 0 | 0.00 | | 0 | 0.00 | | 3 | 1.77 | MYCN; PTCH1; | 4 | 2.64 | AQP3; CYP27B1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| differentiation: GO | | | | IL20; SFN; TP63; TRIM16 | | | PTCH2 | | | | | | | | | PTCH2 | | | IL20; SFN |
| monocarboxylic acid transmembrane transporter activity: GO | 43 | 5 | 1.95 | SLC10A6; SLC16A1; SLC16A6; SLC16A9; SLC6A11 | 6 | 1.65 | ABCB11; ABCC3; SLC10A2; SLC16A11; SLC16A12; SLC16A8 | 0 | 0.00 | | 0 | 0.00 | | 0 | 0.00 | | 4 | 2.64 | SLC16A6; SLC16A9; SLC26A6; SLC6A11 |
| positive regulation of leukocyte apoptotic process: GO | 27 | 6 | 3.72 | ANXA1; HCAR2; IDO1; NR4A3; PRELID1; WNT5A | 1 | 0.44 | P2RX7 | 0 | 0.00 | | 1 | 15.48 | HCAR2 | 0 | 0.00 | | 3 | 3.15 | IL10; PRELID1; WNT5A |
| purinergic receptor signaling pathway: GO | 27 | 5 | 3.10 | GPR171; GPR87; P2RY1; P2RY2; PTAFR | 5 | 2.18 | ADCY5; ADORA1; P2RX1; P2RX6; P2RX7 | 0 | 0.00 | | 0 | 0.00 | | 1 | 0.94 | P2RY4 | 3 | 3.15 | P2RY1; P2RY2; PTAFR |
| regulation of keratinocyte differentiation: GO | 27 | 5 | 3.10 | AQP3; CYP27B1; IL20; TP63; TRIM16 | 1 | 0.44 | KRT36 | 0 | 0.00 | | 0 | 0.00 | | 0 | 0.00 | | 3 | 3.15 | AQP3; CYP27B1; IL20 |
| eating behavior: GO | 27 | 4 | 2.48 | CCK; NMU; P2RY1; TH | 2 | 0.87 | LEP; NPY5R | 0 | 0.00 | | 0 | 0.00 | | 0 | 0.00 | | 3 | 3.15 | NMU; P2RY1; TH |
| negative regulation of lymphocyte apoptotic process: GO | 27 | 4 | 2.48 | HIF1A; IDO1; JAK3; PRKCQ | 5 | 2.18 | GPAM; IRS2; PIP; RORC; TSC22D3 | 1 | 15.48 | GPAM | 0 | 0.00 | | 3 | 2.82 | PIP: SLC46A2; TSC22D3 | 3 | 3.15 | AURKB; HIF1A; PRKCQ |
| positive regulation of heart growth: GO | 27 | 4 | 2.48 | CCNB1; CDK1; NRG1; TBX20 | 5 | 2.18 | ACACB; ERBB4; FGF9; FGFR1; TBX5 | 0 | 0.00 | | 0 | 0.00 | | 3 | 2.82 | ERBB4; FGF2; FGFR1 | 3 | 3.15 | CCNB1; CDK1; NRG1 |
| chemorepellent activity: GO | 27 | 3 | 1.86 | FLRT3; NRG1; SEMA4B | 6 | 2.62 | NRG3; SEMA3A; SEMA3B; SEMA3D; SEMA3E; SEMA3G | 0 | 0.00 | | 0 | 0.00 | | 2 | 1.88 | SEMA3E; SEMA4G | 3 | 3.15 | FLRT3; NRG1; SEMA4B |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| cyclin d associated events in g1 | 27 | 3 | 1.86 | CCND2; CDKN1A; E2F3 | 0 | 0.00 | | 0 | 0.00 | | 0 | 0.00 | | 0 | 0.00 | | 3 | 3.15 | CCND2; CDKN1A; E2F1 |
| sex chromosome: GO | 27 | 3 | 1.86 | ESCO2; H2AFX; H2AFZ | 0 | 0.00 | | 0 | 0.00 | | 0 | 0.00 | | 0 | 0.00 | | 3 | 3.15 | H2AFX; H2AFZ; PLK4 |
| lens development in camera type eye: GO | 61 | 6 | 1.65 | BFSP1; GJA1; SLC7A11; TGFBR1; WNT5A; WNT7A | 8 | 1.55 | BCAR3; CDON; CRYAB; FOXE3; NTRK3; PAX6; SOX1; TMOD1 | 1 | 6.85 | CRYAB | 0 | 0.00 | | 3 | 1.25 | BCAR3; CDON; SLITRK6 | 5 | 2.32 | BFSP1; EPHA2; SLC7A11; WNT5A; WNT7A |
| protein tyrosine phosphatase activity: GO | 99 | 8 | 1.35 | CDC25A; CDC25B; CDKN3; DUSP14; DUSP6; DUSP9; PTPRE; UBASH3B | 2 | 0.24 | PTPRQ; PTPRT | 0 | 0.00 | | 0 | 0.00 | | 1 | 0.26 | PTPRT | 7 | 2.01 | CDC25A; CDC25B; CDKN3; DUSP6; PTP4A1; PTPRE; UBASH3B |
| solute cation symporter activity: GO | 99 | 6 | 1.01 | SLC10A6; SLC28A3; SLC2A9; SLC38A1; SLC5A1; SLC6A11 | 13 | 1.55 | SLC10A2; SLC13A2; SLC17A4; SLC17A7; SLC1A2; SLC1A6; SLC1A7; SLC34A3; SLC4A4; SLC5A2; SLC5A9; SLC6A17; SLC6A2 | 0 | 0.00 | | 0 | 0.00 | | 6 | 1.54 | SLC13A2; SLC1A6; SLC1A7; SLC2A12; SLC4A4; SLC5A9 | 7 | 2.01 | SLC13A5; SLC20A1; SLC28A3; SLC2A9; SLC4A7; SLC5A5; SLC6A11 |
| phospholipase c activating g protein coupled receptor signaling pathway: GO | 80 | 9 | 1.88 | FPR1; GNA15; HOMER1; HRH3; LPAR3; LTB4R; P2RY1; | 16 | 2.36 | ACTN2; ADRA1A; ADRA1B; ADRA2A; AGT; AGTR1; CCKBR; CHRM1; | 0 | 0.00 | | 0 | 0.00 | | 9 | 2.86 | ADRA1A; ADRA2A; AGTR1; CHRM1; CHRM3; ESR1; LPAR1; | 6 | 2.13 | GNA15; HOMER1; HRH1; P2RY1; P2RY2; TGM2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | P2RY2; TGM2 | | | CHRM2; CHRM3; CHRM4; DRD1; GALR1; LHCGR; NMUR1; PTHIR | | | | | | | | | P2RY4; PTH1R | | | |
| ras protein signal transduction: GO | 140 | 9 | 1.08 | CCNA2; CDKN1A; CFL1; DOK3; NRAS; PLK2; RALB; RAP2B; RHOD | 7 | 0.59 | ADRA2A; AGTR1; ARHGAP6; MRAS; ROPN1B; SHC2; SHC3 | 0 | 0.00 | | 0 | 0.00 | | 7 | 1.27 | ADRA2A; AGTR1; FGF2; MRAS; RHOU; ROPN1B; SHC2 | 9 | 1.82 | CCNA2; CDC42EP1; CDKN1A; CFL1; DOK3; IQGAP3; PLK2; RAP2B; RHOD |
| pi3k/akt activation | 161 | 11 | 1.14 | CBX2; CDKN1A; EREG; HBEGF; ILIRL1; MYD88; NGF; NRG1; NTRK1; PSMA5; PSMB6 | 7 | 0.51 | BTC; EGF; FGF1; FGFR1; FGFR3; IRS2; NRG2 | 0 | 0.00 | | 0 | 0.00 | | 3 | 0.47 | EGF; FGFR1; PREX2 | 10 | 1.76 | CBX2; CDKN1A; EREG; HBEGF; IER3; MYD88; NGF; NRG1; SNAI2; TRIB3 |
| regulation of vasodilation: GO | 44 | 8 | 3.04 | ADCYAP1; F2RL1; GJA1; HMGCR; HMOX1; P2RY1; P2RY2; PTAFR | 8 | 2.15 | ADCY6; ADORA1; ADRA2A; AGT; AGTR1; EPHX2; NOS2; PLA2G6 | 0 | 0.00 | | 0 | 0.00 | | 2 | 1.15 | ADRA2A; AGTR1 | 4 | 2.58 | P2RY1; P2RY2; PPARD; PTAFR |
| membrane disassembly: GO | 44 | 4 | 1.52 | CCNB1; CCNB2; CDK1; PLK1 | 0 | 0.00 | | 0 | 0.00 | | 0 | 0.00 | | 0 | 0.00 | | 4 | 2.58 | CCNB1; CCNB2; CDK1; PLK1 |
| bicarbonate transport: GO | 44 | 3 | 1.14 | CA2; SLC26A9; SLC4A8 | 13 | 3.49 | CA1; CA3; CA6; CFTR; HBA1; HBA2; HBB; RHAG; SLC26A1; | 0 | 0.00 | | 0 | 0.00 | | 6 | 3.46 | CA1; CA3; CA6; HBA2; HBB; SLC4A4 | 4 | 2.58 | CA2; SLC26A6; SLC4A3; SLC4A7 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | SLC26A5; SLC26A7; SLC4A1; SLC4A4 | | | | | | | | | | | | |
| negative regulation of stat cascade: GO | 44 | 3 | 1.14 | FLRT3; LRRC4; SOCS3 | 5 | 1.34 | CHAD; LRRC4C; LRRTM3; LRRTM4; PODN | 0 | 0.00 | | 0 | 0.00 | | 5 | 2.89 | CHAD; DCN; LRRC15; LRRC4C; PODN | 4 | 2.58 | CISH; FLRT3; LRRC4; SOCS3 |
| cellular protein complex disassembly: GO | 120 | 10 | 1.39 | CFL1; GADD45GIP1; HSPA8; KIF14; KIF18A; KIF2C; MRPL13; MRPL36; MRPL51; NRG1 | 0 | 0.00 | | 0 | 0.00 | | 0 | 0.00 | | 0 | 0.00 | | 8 | 1.89 | CFL1; HSPA8; KIF14; KIF18A; KIF18B; KIF2C; NRG1; SGK1 |
| regulation of interleukin 6 production: GO | 100 | 16 | 2.68 | ADCYAP1; EREG; F2RL1; IFNG; IL1B; IL36A; IL36B; IL36RN; IL6; MYD88; PTAFR; PYCARD; SLAMF1; TNFSF9; WNT5A; ZC3H12A | 2 | 0.24 | P2RX7; PAEP | 0 | 0.00 | | 1 | 4.18 | IL1B | 1 | 0.25 | ZBTB20 | 7 | 1.99 | AFAPIL2; EREG; IL10; MYD88; PTAFR; WNT5A; ZC3H12A |
| organic acid transmembrane transport: GO | 100 | 9 | 1.51 | SLC16A1; SLC16A6; SLC2A9; SLC38A1; SLC38A5; SLC7A1; SLC7A11; SLC7A5; SLC7A8 | 13 | 1.53 | ACACB; PRKAA2; SLC16A11; SLC16A12; SLC16A8; SLC17A7; SLC1A2; SLC1A6; SLC1A7; | 0 | 0.00 | | 1 | 4.18 | AQP9 | 4 | 1.02 | PRKAA2; SLC16A10; SLC1A6; SLC1A7 | 7 | 1.99 | SLC13A5; SLC16A6; SLC2A9; SLC38A5; SLC7A1; SLC7A11; SLC7A5 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | SLC6A17; SLC7A10; SLC7A14; SLC7A9 | | | | | | | | | | | | |
| regulation of fat cell differentiation: GO | 100 | 4 | 0.67 | IL6; PTGS2; WNT5A; ZC3H12A | 14 | 1.65 | ADIPOQ; CIQL4; ENPP1; FRZB; ID4; LEP; LGALS12; PTPRQ; RARRES2; RORC; RUNXIT1; WIF1; ZBTB16; ZFPM2 | 1 | 4.18 | ADIPOQ | 0 | 0.00 | | 4 | 1.02 | RARRES2; RUNX1T1; SULT1E1; ZFPM2 | 7 | 1.99 | E2F1; PPARD; PTGS2; SNAI2; TRIB3; WNT5A; ZC3H12A |
| regulation of defense response to virus: GO | 183 | 19 | 1.74 | AP1S3; CIQBP; EIF2S1; FCGR3B; FGFBP1; HIST1H3A; HIST1H3B; HIST1H3C; HIST1H3F; HIST1H3G; HIST1H3H; HIST1H3I; HIST1H3J; IL12B; IL2RA; SERPINB10; TEAD4; TREM1; ZC3H12A | 9 | 0.58 | FGF14; HCAR1; MAP1A; MSTN; MYOM1; PDK4; PHYHIP; REEP2; USP17L2 | 0 | 0.00 | | 2 | 4.57 | IL2RA; TREM1 | 3 | 0.42 | LMCD1; MYOM1; PDK4 | 11 | 1.70 | AP1S3; FGFBP1; HIST1H3A; HIST1H3C; HIST1H3F; HIST1H3G; HIST1H3H; HIST1H3I; HIST1H3J; TEAD4; ZC3H12A |
| replication fork: GO | 62 | 7 | 1.89 | CDC45; CHEK1; H2AFX; MCM10; | 0 | 0.00 | | 0 | 0.00 | | 0 | 0.00 | | 0 | 0.00 | | 5 | 2.29 | CDC45; CHEK1; GINS4; H2AFX; PIF1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | PCNA; PIF1; UHRF1 | | | | | | | | | | | | | | | |
| myc repress pathway | 62 | 4 | 1.08 | CDKN1A; ITGA6; S100A7; WNT5A | 4 | 0.76 | BCL2; CLU; DKK1; HMGCS2 | 0 | 0.00 | | 0 | 0.00 | | 3 | 1.23 | BCL2; CLU; HMGCS2 | 5 | 2.29 | CDKN1A; ITGA6; ITGB4; NDRG1; WNT5A |
| response to transition metal nanoparticle: GO | 141 | 18 | 2.14 | ACP5; CA2; CCNB1; CCNE1; CDK1; EIF2S1; GGH; GSTP1; HMOX1; HSPA5; IL1A; KRT14; MT2A; PRNP; PTGS2; S100A8; TH; TK1 | 20 | 1.67 | ABCC8; ALB; ALDOB; ANK2; APBB1; BCL2; CP; CRIP1; CYBRD1; CYP17A1; CYP1A1; D2HGDH; GRIN1; HAAO; HAMP; P2RX7; SLC30A10; SNCA; SOD3; TF | 0 | 0.00 | | 1 | 2.96 | AQP9 | 8 | 1.44 | BCL2; CP; CRIP1; CYBRD1; SLC18A2; SLC40A1; SNCA; SOD3 | 9 | 1.81 | ACP5; CA2; CCNB1; CDK1; GSTP1; HSPA5; PTGS2; TH; TK1 |
| symporter activity: GO | 141 | 9 | 1.07 | SLC10A6; SLC16A1; SLC16A6; SLC16A9; SLC28A3; SLC2A9; SLC38A1; SLC5A1; SLC6A11 | 18 | 1.51 | SLC10A2; SLC13A2; SLC15A5; SLC16A11; SLC16A12; SLC16A8; SLC17A4; SLC17A7; SLC1A2; SLC1A6; SLC1A7; SLC24A2; SLC34A3; SLC4A4; SLC5A2; SLC5A9; | 0 | 0.00 | | 0 | 0.00 | | 7 | 1.26 | SLC13A2; SLC1A6; SLC1A7; SLC2A12; SLC46A2; SLC4A4; SLC5A9 | 9 | 1.81 | SLC13A5; SLC16A6; SLC16A9; SLC20A1; SLC28A3; SLC2A9; SLC4A7; SLC5A5; SLC6A11 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | | | | SLC6A17; SLC6A2 | | | | | | | | | | | | |
| single stranded dna binding: GO | 81 | 8 | 1.65 | ANXA1; BLM; BRCA2; C19orf33; CDC45; MCM10; NME1; SUB1 | 1 | 0.15 | CRY2 | 0 | 0.00 | | 0 | 0.00 | | 2 | 0.63 | CRY2; IGHM | 6 | 2.10 | BLM; BRCA2; CDC45; NEIL3; RAD51AP1; SUB1 |
| ter calcium pathway | 28 | 5 | 2.99 | CSF2; FOSL1; IFNG; IL2RA; PTGS2 | 1 | 0.42 | RCAN2 | 0 | 0.00 | | 1 | 14.92 | IL2RA | 1 | 0.91 | RCAN2 | 3 | 3.04 | FOSL1; JUNB; PTGS2 |
| atpase regulator activity: GO | 28 | 4 | 2.39 | ATP1B3; GRPEL2; HSPH1; PFN1 | 1 | 0.42 | BRSK2 | 0 | 0.00 | | 0 | 0.00 | | 2 | 1.81 | ATP1B2; BRSK2 | 3 | 3.04 | GRPEL2; HSPH1; PFN1 |
| protein localization to cytoskeleton: GO | 28 | 4 | 2.39 | AURKA; FAM83D; KIF20B; STIL | 0 | 0.00 | | 0 | 0.00 | | 0 | 0.00 | | 0 | 0.00 | | 3 | 3.04 | AURKA; SPAG5; STIL |
| hdr through single strand annealing (ssa) | 28 | 2 | 1.20 | BLM; EXO1 | 0 | 0.00 | | 0 | 0.00 | | 0 | 0.00 | | 0 | 0.00 | | 3 | 3.04 | BLM; BRIP1; EXO1 |
| mammary gland duct morphogenesis: GO | 28 | 2 | 1.20 | AREG; WNT5A | 2 | 0.84 | GLI2; PTCH1 | 0 | 0.00 | | 0 | 0.00 | | 3 | 2.72 | ESRI; GLI2; PTCH1 | 3 | 3.04 | AREG; EPHA2; WNT5A |
| negative regulation of cytokine biosynthetic process: GO | 28 | 2 | 1.20 | IL6; NMI | 2 | 0.84 | ELANE; INHBB | 0 | 0.00 | | 0 | 0.00 | | 1 | 0.91 | ELANE | 3 | 3.04 | BCL3; IL10; NMI |
| placenta blood vessel development: GO | 28 | 2 | 1.20 | FOSL1; SOCS3 | 1 | 0.42 | PKD1 | 0 | 0.00 | | 0 | 0.00 | | 0 | 0.00 | | 3 | 3.04 | FOSL1; JUNB; SOCS3 |
| negative regulation of multi organism process: GO | 142 | 24 | 2.83 | APOBEC3A; CIQBP; CAMP; CCL3; HMGA2; IFI16; IFITM1; IFITM3; IFNG; IL12B; IL2RA; | 4 | 0.33 | ACVR1C; ELANE; GSN; POU2F3 | 1 | 2.94 | ACVR1C | 3 | 8.83 | IFITM3; IL2RA; ISG15 | 3 | 0.54 | CTSG; ELANE; FBLN1 | 9 | 1.80 | HMGA2; IFI16; IL10; LTF; MX1; OAS1; SLPI; TRIB1; ZC3H12A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | ISG15; ISG20; LTF; MX1; OAS1; OAS3; OASL; PRDM1; RSAD2; SLPI; STAT1; TRIM14; ZC3H12A | | | | | | | | | | | | | | | |
| digestive system development: GO | 142 | 11 | 1.30 | CCNB1; CDKN1A; FOXE1; FOXF1; HIF1A; ITGA6; PRDM1; STRA6; TK1; TP63; WNT5A | 23 | 1.91 | ALX4; BCL2; CCDC40; CCKBR; CLDN18; COBL; CYP1A1; DACT1; DNAAF1; FGF9; GATA1; GATA5; GLI2; HMGCS2; MYOCD; PCSK5; PKD1; PKDCC; RARRES2; SCT; SOX10; TCF21; WNT11 | 1 | 2.94 | CDKN1C | 0 | 0.00 | | 9 | 1.61 | ALX4; BCL2; CLDN18; DACT1; GLI2; HMGCS2; RARRES2; SHOX2; WNT11 | 9 | 1.80 | CCNB1; CDKN1A; FOXE1; HIF1A; HRH2; ITGA6; ITGB4; TK1; WNT5A |
| receptor regulator activity: GO | 45 | 9 | 3.35 | ADH7; CXCL13; GREM1; IL1RN; IL36RN; NRG1; PCSK9; WNT5A; WNT7A | 6 | 1.57 | ACTN2; AGT; ANGPT4; DKK1; EGF; NRG3 | 0 | 0.00 | | 0 | 0.00 | | 2 | 1.13 | ANGPT4; EGF | 4 | 2.52 | NRG1; PCSK9; WNT5A; WNT7A |
| scaffold protein binding: GO | 45 | 7 | 2.60 | DSP; GJA1; KRT5; | 5 | 1.31 | CACNA1H; KRT15; | 0 | 0.00 | | 1 | 9.29 | TREM1 | 2 | 1.13 | CACNA1G; CACNA1H | 4 | 2.52 | KRT5; NLGN4X; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | NLGN4X; P2RY1; PANX1; TREM1 | | | LRP4; NLGN1; SHANK1 | | | | | | | | | | | | P2RY1; PANX1 |
| oxidoreductase activity acting on the aldehyde or oxo group of donors: GO | 45 | 6 | 2.23 | ADH7; AKRIB10; ALDHIA3; ALDH4A1; GAPDH; OGDHL | 2 | 0.52 | ALDH1A1; ALDH1L1 | 0 | 0.00 | | 0 | 0.00 | | 3 | 1.69 | ALDH3A2; ALDH5A1; AOX1 | 4 | 2.52 | AKR1B10; GAPDH; OGDHL; XDH |
| clathrin coated endocytic vesicle: GO | 63 | 6 | 1.59 | AP1S3; CTLA4; FCGR1A; HBEGF; LDLR; WNT5A | 5 | 0.94 | CD207; CLVS1; CLVS2; FZD4; SFTPC | 0 | 0.00 | | 0 | 0.00 | | 2 | 0.81 | CD207; HLA-DQB2 | 5 | 2.25 | AP1S3; HBEGF; LDLR; SFTPA2; WNT5A |
| carbon oxygen lyase activity: GO | 63 | 4 | 1.06 | CA2; ENO1; HMGA2; POLQ | 5 | 0.94 | CA1; CA11; CA3; CA6; NEIL1 | 0 | 0.00 | | 0 | 0.00 | | 4 | 1.61 | CA1; CA11; CA3; CA6 | 5 | 2.25 | CA2; ENO1; HMGA2; NEIL3; POLQ |
| hypertrophic cardiomyopathy hcm | 82 | 5 | 1.02 | ACTB; IL6; ITGA3; ITGA6; ITGB6 | 17 | 2.45 | CACNA1F; CACNA2D1; CACNA2D2; CACNB1; DES; DMD; ITGA7; ITGA8; LAMA2; MYL3; PRKAA2; SGCA; SGCG; TNNC1; TNNT2; TPM1; TPM2 | 1 | 5.10 | SGCG | 0 | 0.00 | | 7 | 2.17 | CACNA2D1; CACNA2D2; CACNB1; ITGA11; LAMA2; PRKAA2; TNNC1 | 6 | 2.07 | ACTB; ITGA3; ITGA6; ITGB4; ITGB6; TPM4 |
| regulation of protein ubiquitination involved in ubiquitin dependent protein catabolic | 102 | 13 | 2.13 | BUB1B; CCNB1; CDC20; CDK1; FBXO5; MAD2L1; PLK1; PSMA4; | 2 | 0.23 | CLU; EGF | 0 | 0.00 | | 0 | 0.00 | | 2 | 0.50 | CLU; EGF | 7 | 1.95 | BUB1B; CCNB1; CDC20; CDK1; MAD2L1; PLK1; UBE2C |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| process: GO | | | | PSMA5; PSMB6; PSMD1; PSME3; UBE2C | | | | | | | | | | | | | | | |
| response to arsenic containing substance: GO | 29 | 6 | 3.46 | CDKN1A; GSTO1; HMOX1; NEFL; PPIF; ZC3H12A | 1 | 0.41 | CYP1A1 | 0 | 0.00 | | 0 | 0.00 | | 0 | 0.00 | | 3 | 2.93 | CDKN1A; PPIF: ZC3H12A |
| positive regulation of cardiac muscle tissue development: GO | 29 | 5 | 2.89 | CCNB1; CDK1; GREM1; NRG1; TBX20 | 5 | 2.03 | ERBB4; FGF9; FGFR1; MYOCD; TBX5 | 0 | 0.00 | | 0 | 0.00 | | 3 | 2.63 | ERBB4; FGF2; FGFR1 | 3 | 2.93 | CCNB1; CDK1; NRG1 |
| regulation of cardiac muscle cell proliferation: GO | 29 | 5 | 2.89 | CCNB1; CDK1; GJA1; NRG1; TBX20 | 7 | 2.85 | ERBB4; FGF9; FGFR1; NKX2-5; NOG; RBP4; TBX5 | 0 | 0.00 | | 0 | 0.00 | | 4 | 3.50 | ERBB4; FGF2; FGFR1; KCNK2 | 3 | 2.93 | CCNB1; CDK1; NRG1 |
| establishment of endothelial barrier: GO | 29 | 4 | 2.31 | F2RL1; MSN; RAP2B; WNT7A | 0 | 0.00 | | 0 | 0.00 | | 0 | 0.00 | | 0 | 0.00 | | 3 | 2.93 | MSN; RAP2B; WNT7A |
| positive regulation of smooth muscle contraction: GO | 29 | 4 | 2.31 | NMU; PROK2; PTAFR; PTGS2 | 4 | 1.63 | ADRA1A; ADRA1B; CHRM3; MYOCD | 0 | 0.00 | | 0 | 0.00 | | 2 | 1.75 | ADRA1A; CHRM3 | 3 | 2.93 | NMU; PTAFR; PTGS2 |
| ubiquitin like protein conjugating enzyme activity: GO | 29 | 4 | 2.31 | UBE2C; UBE2N; UBE2S; UBE2T | 0 | 0.00 | | 0 | 0.00 | | 0 | 0.00 | | 0 | 0.00 | | 3 | 2.93 | UBE2C; UBE2S; UBE2T |
| maintenance of protein localization in organelle: GO | 29 | 3 | 1.73 | HK2; HSPA5; PDIA3 | 3 | 1.22 | GRIK5; NR5A1; SYNE1 | 0 | 0.00 | | 0 | 0.00 | | 1 | 0.88 | SYNE1 | 3 | 2.93 | BCL3; HK2; HSPA5 |
| signaling by robo receptor | 29 | 3 | 1.73 | CAP1; ENAH; PFN1 | 2 | 0.81 | MAST1; SLIT2 | 0 | 0.00 | | 0 | 0.00 | | 1 | 0.88 | SLIT2 | 3 | 2.93 | CAP1; ENAH; PFN1 |
| cellular response to estradiol stimulus: GO | 29 | 2 | 1.15 | CCNA2; H2AFZ | 1 | 0.41 | PPARGC1A | 0 | 0.00 | | 0 | 0.00 | | 2 | 1.75 | ESR1; PPARGC1A | 3 | 2.93 | CCNA2; H2AFZ; IL10 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| chemokine mediated signaling pathway: GO | 64 | 18 | 4.71 | CCL17; CCL18; CCL21; CCL22; CCL3; CCL7; CCR4; CCR5; CXCL1; CXCL10; CXCL11; CXCL13; CXCL3; CXCL5; CXCL6; CXCL9; CXCR1; CXCR4 | 2 | 0.37 | CCL14; CXCR5 | 0 | 0.00 | | 2 | 13.06 | CXCL5; CXCL9 | 2 | 0.79 | CCL14; CXCL12 | 5 | 2.22 | CCL20; CXCL11; CXCL2; CXCL6; CXCR1 |
| mesoderm morphogenesis: GO | 64 | 7 | 1.83 | EOMES; FOXF1; HMGA2; ITGA3; NR4A3; TBX20; WNT5A | 4 | 0.74 | DKK1; ITGA8; NOG; WNT11 | 0 | 0.00 | | 0 | 0.00 | | 3 | 1.19 | CHRD; FOXC1; WNT11 | 5 | 2.22 | EPHA2; HMGA2; ITGA3; ITGB4; WNT5A |
| clathrin coated endocytic vesicle membrane: GO | 46 | 5 | 1.82 | AP1S3; FCGR1A; HBEGF; LDLR; WNT5A | 4 | 1.03 | CD207; CLVS1; CLVS2; FZD4 | 0 | 0.00 | | 0 | 0.00 | | 2 | 1.10 | CD207; HLA-DQB2 | 4 | 2.47 | AP1S3; HBEGF; LDLR; WNT5A |
| cerebellar cortex development: GO | 46 | 4 | 1.46 | HSPA5; KIF14; SERPINE2; WNT7A | 6 | 1.54 | ATP2B2; CBLN1; GLI2; NEUROD2; NRXN1; SEZ6L | 0 | 0.00 | | 0 | 0.00 | | 4 | 2.21 | GLI2; MDK; NRXN1; SEZ6L | 4 | 2.47 | HSPA5; KIF14; SERPINE2; WNT7A |
| positive regulation of fat cell differentiation: GO | 46 | 2 | 0.73 | PTGS2; ZC3H12A | 4 | 1.03 | FRZB; RARRES2; WIF1; ZBTB16 | 0 | 0.00 | | 0 | 0.00 | | 2 | 1.10 | RARRES2; SULT1E1 | 4 | 2.47 | PPARD; PTGS2; SNAI2; ZC3H12A |
| er to golgi anterograde transport | 103 | 9 | 1.46 | AREG; CAP1; CTSC; DYNLL1; TGFA; | 3 | 0.34 | ANK2; FOLR1; TRAPPC6A | 0 | 0.00 | | 0 | 0.00 | | 2 | 0.49 | DLC1; TRAPPC6A | 7 | 1.93 | AREG; CAP1; TGFA; TUBA1C; TUBA4A; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | TUBA1C; TUBA4A; TUBB2A; TUBB6 | | | | | | | | | | | | | | | TUBB2A; TUBB6 |
| regulation of synapse organization: GO | 103 | 8 | 1.30 | CDC20; FLRT3; LRRC4; NTRK1; PCDH17; TPBG; WNT5A; WNT7A | 24 | 2.75 | APOE; CAMK1; CAMK2B; CBLN1; CLSTN2; DKK1; EEF2K; EPHB1; GRIN1; LRP4; LRRN1; LRRTM3; MAGI2; NEUROD2; NLGN1; NRXN1; NRXN3; NTRK3; PPP1R9A; RELN; SIX1; SLITRK2; SLITRK4; SLITRK5 | 0 | 0.00 | | 0 | 0.00 | | 6 | 1.48 | CAMK1; LRRN1; NRXN1; RELN; SLITRK4; SLITRK6 | 7 | 1.93 | AGRN; CDC20; FLRT3; LRRC4; TPBG; WNT5A; WNT7A |
| regulation of cell size: GO | 166 | 11 | 1.11 | AQP3; CDK5R1; CRABP2; HIF1A; IL7R; LPAR3; MSN; NRG1; SEMA4B; TNFRSF12A; WNT5A | 17 | 1.21 | AMOT; APOE; AQP4; AQP7; ATP2B2; CDH4; MAPT; NTRK3; P2RX7; PLXNA3; PLXNA4; SEMA3A; SEMA3B; SEMA3D; SEMA3E; | 0 | 0.00 | | 2 | 5.03 | AQP9; IL7R | 5 | 0.77 | CXCL12; MAPT; PLXNA4; SEMA3E; SEMA4G | 10 | 1.71 | AQP3; CDK5R1; CRABP2; HIF1A; IQGAP3; MSN; NRG1; SEMA4B; VAV2; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | SEMA3G; SLC26A5 | | | | | | | | | | | | |
| small cell lung cancer | 84 | 7 | 1.39 | CCNE1; CYCS; E2F3; ITGA3; ITGA6; LAMB3; PTGS2 | 6 | 0.84 | BCL2; LAMA2; LAMB4; LAMC3; NOS2; RXRG | 0 | 0.00 | | 0 | 0.00 | | 3 | 0.91 | BCL2; LAMA2; LAMC3 | 6 | 2.03 | CYCS; E2F1; ITGA3; ITGA6; LAMB3; PTGS2 |
| palate development: GO | 84 | 5 | 1.00 | FOXE1; PAK1IP1; TGFBR1; WNT5A; WNT7A | 12 | 1.69 | ALX1; ALX4; COL11A2; GABRB3; HAND2; MEOX2; OSR1; OSR2; PKDCC; TCF21; WFIKKN1; WNT11 | 1 | 4.97 | WFIKKN1 | 0 | 0.00 | | 8 | 2.42 | ALX4; BNC2; FRAS1; HAND2; MEOX2; OSR1; PRRX1; WNT11 | 6 | 2.03 | FOXE1; MMP25; SNAI2; WNT5A; WNT7A; WNT9B |
| heterochromatin: GO | 65 | 6 | 1.54 | CBX2; ESCO2; H2AFZ; HIST1H1B; HMGA2; UHRF1 | 2 | 0.36 | CBX7; CHD5 | 0 | 0.00 | | 0 | 0.00 | | 2 | 0.78 | CBX7; FOXC1 | 5 | 2.18 | BEND3; CBX2; H2AFZ; HIST1H1B; HMGA2 |
| histone exchange: GO | 47 | 11 | 3.92 | CENPA; CENPN; CENPW; HIST1H4I; HIST1H4J; HIST1H4K; HIST1H4L; HJURP; NPM1; OIP5; RUVBL1 | 2 | 0.50 | CHD5; TNP1 | 0 | 0.00 | | 0 | 0.00 | | 1 | 0.54 | SYCP3 | 4 | 2.41 | CENPA; CENPW; HIST1H4I; NPM1 |
| tissue regeneration: GO | 47 | 7 | 2.49 | ANXA1; CCNB1; GJA1; KLK6; PLAU; PRKCQ; WNT7A | 5 | 1.26 | APOD; ERBB4; GSN; MSTN; TIMP3 | 0 | 0.00 | | 0 | 0.00 | | 2 | 1.08 | ERBB4; FZD7 | 4 | 2.41 | CCNB1; PRKCQ; SOX15; WNT7A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| cellular response to calcium ion: GO | 47 | 3 | 1.07 | ECT2; PPIF; WNT5A | 5 | 1.26 | CHP2; EEF2K; GPLD1; NEUROD2; SYT1 | 0 | 0.00 | | 0 | 0.00 | | 3 | 1.62 | ACER1; CHP2; GPLD1 | 4 | 2.41 | ECT2; JUNB; PPIF; WNT5A |
| slc-mediated transmembrane transport | 146 | 9 | 1.03 | SLC16A1; SLC2A1; SLC2A9; SLC38A1; SLC39A6; SLC7A1; SLC7A11; SLC7A5; SLC7A8 | 10 | 0.81 | ALB; CP; SLC14A1; SLC1A2; SLC27A6; SLC30A10; SLC4A4; SLC5A9; SLC7A9; SLCO4C1 | 1 | 2.86 | SLC27A6 | 0 | 0.00 | | 9 | 1.57 | CP; RHBG; SLC14A1; SLC16A10; SLC29A1; SLC2A12; SLC40A1; SLC4A4; SLC5A9 | 9 | 1.75 | SLC13A5; SLC20A1; SLC26A6; SLC2A1; SLC2A9; SLC4A7; SLC7A1; SLC7A11; SLC7A5 |
| euchromatin: GO | 30 | 5 | 2.79 | CBX2; H2AFZ; HIST1H1A; HIST1H1D; UHRF1 | 1 | 0.39 | PPARGC1A | 0 | 0.00 | | 0 | 0.00 | | 1 | 0.85 | PPARGC1A | 3 | 2.84 | CBX2; H2AFZ; HIST1H1D |
| kinesin binding: GO | 30 | 4 | 02.23 | ACTB; FAM83D; KTN1; LRP8 | 5 | 1.97 | ATCAY; CROCC; MAPK8IP1; SNCA; SYBU | 0 | 0.00 | | 0 | 0.00 | | 2 | 1.69 | SNCA; SYBU | 3 | 2.84 | ACTB; KIF18B; KTN1 |
| nucleosomal dna binding: GO | 30 | 4 | 2.23 | ACTB; H2AFZ; HMGA2; RCC1 | 0 | 0.00 | | 0 | 0.00 | | 0 | 0.00 | | 0 | 0.00 | | 3 | 2.84 | ACTB; H2AFZ; HMGA2 |
| cerebellar cortex morphogenesis: GO | 30 | 3 | 1.67 | KIF14; SERPINE2; WNT7A | 4 | 1.57 | ATP2B2; CBLN1; GLI2; NRXN1 | 0 | 0.00 | | 0 | 0.00 | | 2 | 1.69 | GLI2; NRXN1 | 3 | 2.84 | KIF14; SERPINE2; WNT7A |
| modulation of excitatory postsynaptic potential: GO | 30 | 3 | 1.67 | EIF4A3; NLGN4X; WNT7A | 9 | 3.54 | CELF4; DRD4; GRIN1; NETO1; NLGN1; NRXN1; RELN; RIMS1; SHANK1 | 0 | 0.00 | | 0 | 0.00 | | 3 | 2.54 | NRXN1; RELN; RIMS1 | 3 | 2.84 | EIF4A3; NLGN4X; WNT7A |
| phosphatidyl-glycerol | 30 | 2 | 1.12 | PLA2G3; PLA2G4D | 2 | 0.79 | PLA2G5; PLA2G6 | 0 | 0.00 | | 0 | 0.00 | | 0 | 0.00 | | 3 | 2.84 | LPCAT1; PLA2G3; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| metabolic process: GO | | | | | | | | | | | | | | | | | | | PLA2G4D |
| neuron maturation: GO | 30 | 1 | 0.56 | CNTNAP2 | 4 | 1.57 | KCNIP2; LGI4; MYOC; SPTBN4 | 1 | 13.93 | CDKN1C | 0 | 0.00 | | 5 | 4.23 | GLDN; LGI4; MYOC; NTN4; SPTBN4 | 3 | 2.84 | AGRN; CNTNAP2; RND1 |
| regulation of ph: GO | 85 | 6 | 1.18 | ATP12A; CA2; RAB38; RHCG SLC26A9; SLC4A8 | 16 | 2.22 | ATP6V0A4; ATP6V0E2; ATP6V1B1; BCL2; CFTR; NOX1; PDK4; SLC17A7; SLC26A1; SLC26A5; SLC26A7; SLC4A1; SLC4A4; SLC9A2; SLC9A4; TTPA | 0 | 0.00 | | 0 | 0.00 | | 6 | 1.79 | ATP6V0A4; ATP6V0E2; BCL2; PDK4; SLC4A4; SLC9A2 | 6 | 2.00 | CA2; RAB38; RHCG; SLC26A6; SLC4A3; SLC4A7 |
| erbb1 downstream pathway | 105 | 10 | 1.59 | ACTR3; ARPC3; DIAPH3; DUSP6; NRAS; SFN; SH2D2A; STAT1; YWHAQ; YWHAZ | 2 | 0.22 | EGF; MYLPF | 0 | 0.00 | | 0 | 0.00 | | 1 | 0.24 | EGF | 7 | 1.89 | DIAPH3; DUSP6; RPS6KA4; SFN; VAV2; YWHAQ; YWHAZ |
| rna helicase activity: GO | 66 | 3 | 0.76 | DDX21; DDX28; EIF4A3 | 1 | 0.18 | DDX25 | 0 | 0.00 | | 0 | 0.00 | | 1 | 0.38 | DDX25 | 5 | 2.15 | DDX21; DDX28; DDX39A; EIF4A3; TDRD9 |
| growth factor receptor binding: GO | 126 | 23 | 3.05 | AREG; CSF2; EPGN; EREG; ESM1; FAM83B; FLRT3; GREM1; HBEGF; | 11 | 1.03 | BTC; EGF; ERBB4; FGF1; FGF14; FGF17; FGF22; FGF9; IL37; IL5; PDGFD | 0 | 0.00 | | 1 | 3.32 | IL1B | 4 | 0.81 | EGF; ERBB4; FGF2; FGF22 | 8 | 1.80 | AREG; EREG; FLRT3; HBEGF; IL10; IL36G; TGFA; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | IL12B; IL1A; IL1B; ILIF10; IL1RAP; IL1RN; IL36A; IL36B; IL36G; IL36RN; IL6; PYCARD; TGFA; TYMP | | | | | | | | | | | | | | | VAV2 |
| protein stabilization: GO | 126 | 17 | 2.26 | ATP1B3; CALR; CCT2; CCT3; CCT5; CCT6A; CCT7; CDKN1A; DSC3; DSG1; FKBPL; GAPDH; HIST1H1B; IFI30; PFN1; PPIB; USP2 | 4 | 0.37 | ANK2; CLU; GPIHBP1; PPARGC1A | 0 | 0.00 | | 0 | 0.00 | | 4 | 0.81 | ATP1B2; CLU: PPARGC1A; TESC | 8 | 1.80 | CCT2; CCT5; CDKN1A; DSC3; GAPDH; GTSE1; HIST1H1B; PFN1 |
| regulation of reproductive process: GO | 126 | 12 | 1.59 | ASPM; AURKA; CIQBP; CALR; CDC20; FBXO5; OSM; P2RY1; P2RY2; PLAU; PTAFR; WNT5A | 14 | 1.31 | ACVR1C; CACNA1H; CNR1; DRD4; INHBB; LIF; NPM2; NR5A1; NUPR1; PIWIL2; SEMA3A; SPINK1; TEKT3; ZFPM2 | 1 | 3.32 | ACVR1C | 1 | 3.32 | OSM | 3 | 0.60 | CACNA1H; ESR1; ZFPM2 | 8 | 1.80 | ASPM; AURKA; CDC20; P2RY1; P2RY2; PTAFR; SERPINA10; WNT5A |
| regulation of symbiosis encompassing mutualism through parasitism: GO | 191 | 29 | 2.54 | APOBEC3A; CAMP; CCL3; CFL1; F2RL1; HMGA2; IFI16; IFITM1; IFITM3; IFNG; IL12B; | 7 | 0.43 | APOE; BCL2; ELANE; GSN; HS3ST5; POU2F3; TMPRSS2 | 0 | 0.00 | | 3 | 6.56 | IFITM3; ISG15; LAMP3 | 4 | 0.53 | BCL2; CTSG; ELANE; FBLN1 | 11 | 1.63 | CFL1; HMGA2; IFI16; IL10; LTF; MX1; OAS1; PFN1; SLPI; TOP2A; ZC3H12A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | ISG15; ISG20; LAMP3; LTF; MX1; OAS1; OAS3; OASL; PFN1; PPIA; PPIB; RSAD2; SLPI; STAT1; TAP2; TOP2A; TRIM14; ZC3H12A | | | | | | | | | | | | | | | |
| dna replication independent nucleosome organization: GO | 48 | 12 | 4.18 | ASF1B; CENPA; CENPN; CENPW; HIST1H4I; HIST1H4J; HIST1H4K; HIST1H4L; HJURP; NPM1; OIP5; RUVBL1 | 0 | 0.00 | | 0 | 0.00 | | 0 | 0.00 | | 0 | 0.00 | | 4 | 2.36 | CENPA; CENPW; HIST1H4I; NPM1 |
| fructose and mannose metabolism | 48 | 5 | 1.74 | AKRIB10; HK2; PFKFB4; PGM2; TPI1 | 2 | 0.49 | ALDOB; PFKFB1 | 0 | 0.00 | | 0 | 0.00 | | 2 | 1.06 | ALDOC; PFKFB1 | 4 | 2.36 | AKR1B10; HK2; PFKFB4; TPI1 |
| visual behavior: GO | 48 | 3 | 1.05 | HIF1A; HMGCR; NDRG4 | 7 | 1.72 | ATP1A2; DRD1; GRIN1; GRIN2A; NETO1; PPP1R1B; SLC1A2 | 0 | 0.00 | | 0 | 0.00 | | 0 | 0.00 | | 4 | 2.36 | HIF1A; HRH1; HRH2; SGK1 |
| midbrain development: GO | 86 | 7 | 1.36 | ACTB; DYNLL1; HSPA5; INA; LDHA; WNT5A; YWHAQ | 6 | 0.82 | DKK1; FGF9; FGFR1; KAT2A; LMXIA; PLP1 | 0 | 0.00 | | 0 | 0.00 | | 3 | 0.89 | FGFR1; GDF7; PLP1 | 6 | 1.98 | ACTB; HSPA5; INA; LDHA; WNT5A; YWHAQ |
| response to starvation: | 148 | 13 | 1.47 | ADCYAP1; CDKN1A; | 13 | 1.04 | ALB; ALDOB; | 0 | 0.00 | | 0 | 0.00 | | 8 | 1.37 | BCL2; BHLHA15; | 9 | 1.72 | CDKN1A; DSC2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| GO | | | | DSC2; EIF2S1; HSPA5; HSPA8; IFI16; PCSK9; RALB; SLC2A1; UGT1A1; UPP1; ZC3H12A | | | BCL2; CARTPT; GCGR; HMGCS2; INHBB; MAP1LC3C; PCK1; PDK4; PFKFB1; PPARGC1A; PRKAA2 | | | | | | | | | HMGCS2; PDK4; PFKFB1; PPARGC1A; PRKAA2; SLC18A2 | | | HSPA5; HSPA8; IFI16; PCSK9; SLC2A1; WNT9B; ZC3H12A |
| regulation of vascular endothelial growth factor production: GO | 31 | 7 | 3.78 | HIF1A; HPSE; IL1A; IL1B; IL6; PTGS2; SULF2 | 3 | 1.14 | C3; CCBE1; NOX1 | 0 | 0.00 | | 1 | 13.48 | IL1B | 2 | 1.64 | C3; CCBE1 | 3 | 2.74 | HIF1A; HPSE; PTGS2 |
| l alpha amino acid transmembrane transport: GO | 31 | 5 | 2.70 | SLC38A1; SLC7A1; SLC7A11; SLC7A5; SLC7A8 | 5 | 1.90 | SLC17A7; SLC1A2; SLC1A6; SLC1A7; SLC7A14 | 0 | 0.00 | | 0 | 0.00 | | 2 | 1.64 | SLC1A6; SLC1A7 | 3 | 2.74 | SLC7A1; SLC7A11; SLC7A5 |
| cellular senescence: GO | 31 | 4 | 2.16 | CALR; CDKN1A; H2AFX; HMGA2 | 1 | 0.38 | C2orf40 | 1 | 13.48 | C2orf40 | 0 | 0.00 | | 0 | 0.00 | | 3 | 2.74 | CDKN1A; H2AFX; HMGA2 |
| fat soluble vitamin metabolic process: GO | 31 | 4 | 2.16 | CYP24A1; CYP27B1; CYP4F11; LRAT | 3 | 1.14 | CYP1A1; CYP4F12; TTPA | 0 | 0.00 | | 0 | 0.00 | | 2 | 1.64 | CYP3A4; CYP4F12 | 3 | 2.74 | CYP27B1; LRAT; PPARD |
| negative regulation of response to oxidative stress: GO | 31 | 4 | 2.16 | HIF1A; HSPH1; NR4A3; TXN | 1 | 0.38 | NOL3 | 0 | 0.00 | | 0 | 0.00 | | 0 | 0.00 | | 3 | 2.74 | HIF1A; HSPH1; TXN |
| nuclear heterochromatin: GO | 31 | 4 | 2.16 | ESCO2; H2AFZ; HIST1H1B; UHRF1 | 0 | 0.00 | | 0 | 0.00 | | 0 | 0.00 | | 1 | 0.82 | FOXC1 | 3 | 2.74 | BEND3; H2AFZ; HIST1H1B |
| embryonic axis specification: GO | 31 | 3 | 1.62 | STIL; WNT5A; WNT7A | 4 | 1.52 | COBL; CXXC4; PTCH1; TDRD5 | 0 | 0.00 | | 0 | 0.00 | | 2 | 1.64 | HOXD8; PTCH1 | 3 | 2.74 | STIL; WNT5A; WNT7A |
| regulation of | 31 | 3 | 1.62 | GEN1; NPM1; | 1 | 0.38 | PKHD1 | 0 | 0.00 | | 0 | 0.00 | | 0 | 0.00 | | 3 | 2.74 | NPM1; PLK2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| centrosome duplication: GO | | | | PLK2 | | | | | | | | | | | | | | | PLK4 |
| centrosome duplication: GO | 31 | 2 | 1.08 | BRCA2; STIL | 0 | 0.00 | | 0 | 0.00 | | 0 | 0.00 | | 0 | 0.00 | | 3 | 2.74 | BRCA2; PLK4; STIL |
| fanconi anemia pathway | 31 | 2 | 1.08 | BRCA2; UBE2T | 0 | 0.00 | | 0 | 0.00 | | 0 | 0.00 | | 0 | 0.00 | | 3 | 2.74 | BRCA2; FANCI; UBE2T |
| p75 ntr pathway | 67 | 6 | 1.50 | CYCS; MMP3; MYD88; NGF; NTRK1; PSENEN | 0 | 0.00 | | 0 | 0.00 | | 0 | 0.00 | | 0 | 0.00 | | 5 | 2.12 | CYCS; E2F1; MMP3; MYD88; NGF |
| positive regulation of leukocyte migration: GO | 107 | 24 | 3.75 | BDKRB1; CIQBP; CALR; CCL21; CCL3; CCL7; CXCL1; CXCL10; CXCL11; CXCL13; CXCL3; CXCL5; CXCL6; CXCL9; F2RL1; IL1B; IL6; PTAFR; PYCARD; RAC2; S100A14; S100A7; SERPINE1; WNT5A | 4 | 0.44 | EDN3; F7; PDGFD; RARRES2 | 0 | 0.00 | | 5 | 19.53 | CXCL5; CXCL9; IL1B; RAC2; SERPINE1 | 3 | 0.71 | CXCL12; EDN3; RARRES2 | 7 | 1.86 | CCL20; CXCL11; CXCL2; CXCL6; PTAFR; S100A14; WNT5A |
| metalloendo-peptidase activity: GO | 107 | 10 | 1.56 | ADAM23; ADAMDEC1; ADAMTS4; CLCA2; KLK7; MMP1; MMP10; MMP12; | 6 | 0.66 | ADAM11; ADAM22; ADAM33; ADAMTS10; ADAMTS16; ADAMTS19 | 0 | 0.00 | | 0 | 0.00 | | 4 | 0.95 | ADAM22; ADAM33; ADAMTS10; MMP27 | 7 | 1.86 | ADAM19; ADAM23; ADAMTS14; ADAMTS4; CLCA2; MMP25; MMP3 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | MMP3; MMP9 | | | | | | | | | | | | | | | |
| positive regulation of mitochondrion organization: GO | 149 | 19 | 2.13 | BAK1; CIQBP; DYNLL1; FAM162A; HIF1A; ITGAX; MMP9; NRG1; PLAUR; PPIF; PYCARD; RAC2; RUVBL1; SFN: TNFSF10; TP63; UGCG; YWHAQ; YWHAZ | 8 | 0.63 | BCL2; CDKL2; HSPA1L; KAT2A; MYBPC1; NMUR1; PLA2G6; PPARGC1A | 0 | 0.00 | | 2 | 5.61 | GZMB; RAC2 | 4 | 0.68 | BCL2; DCN; PPARGC1A; RHOU | 9 | 1.71 | BAK1; E2F1; HIF1A; MPV17L2; NRG1; PPIF; SFN; YWHAQ; YWHAZ |
| response to fungus: GO | 49 | 12 | 4.10 | BAK1; C10orf99; CAMP; CLEC6A; CLEC7A; COTL1; IL36RN; IL6; LTF; S100A12; S100A8; S100A9 | 3 | 0.72 | DCD; ELANE; HAMP | 0 | 0.00 | | 1 | 8.53 | COTL1 | 3 | 1.56 | CTSG; DCD; ELANE | 4 | 2.31 | BAK1; C10orf99; CLEC7A; LTF |
| response to gamma radiation: GO | 49 | 8 | 2.73 | BAK1; BRCA2; CCL7; CXCL10; H2AFX; IL1B; SOCS3; TP63 | 2 | 0.48 | BCL2; CRYAB | 1 | 8.53 | CRYAB | 1 | 8.53 | IL1B | 2 | 1.04 | BCL2; TSPYL5 | 4 | 2.31 | BAK1; BRCA2; H2AFX; SOCS3 |
| cellular response to fatty acid: GO | 49 | 6 | 2.05 | CCNB1; IL1B; NME1; PTAFR; TNC; ZC3H12A | 5 | 1.20 | ADCY6; HMGCS2; PDK4; PPARGC1A; PRKAA2 | 0 | 0.00 | | 2 | 17.06 | FFAR2; IL1B | 9 | 4.67 | DGAT2; HMGCS2; P2RY4; PDK3; PDK4; PPARGC1A; | 4 | 2.31 | CCNB1; E2F1; PTAFR; ZC3H12A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | | | | | | | | | | PRKAA2; PTGDR; PTGFR | | | |
| ribosome assembly: GO | 49 | 5 | 1.71 | C1QBP; DDX28; EIF6; NIP7; NPM1 | 0 | 0.00 | | 0 | 0.00 | | 0 | 0.00 | | 0 | 0.00 | | | 2.31 | DDX28; EIF6; MPV17L2; NPM1 |
| insulin receptor pathway in cardiac myocytes | 49 | 4 | 1.37 | CAP1; SFN; YWHAQ; YWHAZ | 4 | 0.96 | IRS2; IRS4; SLC2A4; SORBS1 | 0 | 0.00 | | 0 | 0.00 | | 0 | 0.00 | | 4 | 2.31 | CAP1; SFN; YWHAQ; YWHAZ |
| regulation of smooth muscle cell migration: GO | 49 | 4 | 1.37 | NDRG4; P2RY2; PLAU; SERPINE1 | 6 | 1.44 | ADIPOQ; BCL2; PDGFD; PPARGC1A; SLIT2; TPM1 | 1 | 8.53 | ADIPOQ | 1 | 8.53 | SERPINE1 | 5 | 2.59 | BCL2; IGFBP5; LPAR1; PPARGC1A; SLIT2 | 4 | 2.31 | IGFBP3; P2RY2; PPARD; TRIB1 |
| extracellular matrix binding: GO | 49 | 3 | 1.02 | ITGA3; LYPD3; LYPD5 | 3 | 0.72 | COL11A1; SLIT2; SSC5D | 0 | 0.00 | | 0 | 0.00 | | 7 | 3.63 | COL11A1; DCN; FBLN2; LRRC15; NTN4; SLIT2; SSC5D | 4 | 2.31 | AGRN; ITGA3; LYPD3; LYPD5 |
| atp dependent chromatin remodeling: GO | 68 | 12 | 2.95 | ACTB; CENPA; CENPN; CENPW; HIST1H4I; HIST1H4J; HIST1H4K; HIST1H4L; HJURP; NPM1; OIP5; RUVBL1 | 3 | 0.52 | CECR2; CHD5; TNP1 | 0 | 0.00 | | 0 | 0.00 | | 1 | 0.37 | SYCP3 | 5 | 2.09 | ACTB; CENPA; CENPW; HIST1H4I; NPM1 |
| copi-mediated anterograde transport | 68 | 6 | 1.48 | CAP1; DYNLL1; TUBA1C; TUBA4A; TUBB2A; TUBB6 | 2 | 0.35 | ANK2; FOLR1 | 0 | 0.00 | | 0 | 0.00 | | 1 | 0.37 | DLC1 | 5 | 2.09 | CAP1; TUBA1C; TUBA4A; TUBB2A; TUBB6 |
| rho gtpase cycle | 68 | 5 | 1.23 | ARAP2; DEPDC1B; DEPDC7; | 3 | 0.52 | ARHGEF26; FAM13A; MCF2L | 0 | 0.00 | | 0 | 0.00 | | 3 | 1.12 | ARHGEF26; DLC1; RHOU | 5 | 2.09 | ARHGAP11A; DEPDC1B; ECT2; LRG1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | ECT2; RACGAP1 | | | | | | | | | | | | | | | VAV2 |
| phosphatidyl-inositol bisphosphate binding: GO | 68 | 4 | 0.98 | ADAP2; MYO1B; PFN1; TWF1 | 11 | 1.91 | ACTN2; APBA1; CLVS1; CLVS2; JPH2; KCNJ1; SCIN; SNX21; STXBP6; SYT1; TTPA | 0 | 0.00 | | 1 | 6.15 | SNX20 | 3 | 1.12 | APBA1; SCIN; STXBP6 | 5 | 2.09 | ADAP2; MARK1; MYO1B; PFN1; TWF1 |
| positive regulation of carbohydrate metabolic process: GO | 68 | 4 | 0.98 | HIF1A; NTSR1; P2RY1; PTAFR | 14 | 2.43 | EGF; GPD1; GPLD1; IRS2; KAT2A; LHCGR; MLXIPL; P2RX7; PFKFB1; PPARGC1A; PRKAA2; PTH1R; SNCA; SORBS1 | 1 | 6.15 | GPD1 | 0 | 0.00 | | 9 | 3.36 | ADCYAP1R1; DGAT2; EGF; GPLD1; PFKFB1; PPARGC1A; PRKAA2; PTH1R; SNCA | 5 | 2.09 | HIF1A; HRH1; NTSR1; P2RY1; PTAFR |
| formation of primary germ layer: GO | 108 | 10 | 1.55 | EOMES; FOXF1; HMGA2; ITGA3; LAMB3; MMP9; NR4A3; SOX7; TBX20; WNT5A | 8 | 0.87 | ATOH8; COL11A1; DKK1; ITGA7; ITGA8; NANOG; NOG; WNT11 | 0 | 0.00 | | 0 | 0.00 | | 5 | 1.18 | ATOH8; CHRD; COL11A1; FOXC1; WNT11 | 7 | 1.84 | EPHA2; HMGA2; ITGA3; ITGB4; LAMB3; SOX7; WNT5A |
| platelet activation signaling and aggregation | 194 | 16 | 1.38 | CAP1; CFL1; GNA15; GNAI3; GNGT2; HSPA5; P2RY1; PFN1; PPIA; PRKCQ; RAC2; | 8 | 0.49 | ACTN2; ADRA2A; ALB; CFD; CLU; DGKG; EGF; TF | 0 | 0.00 | | 3 | 6.46 | LCP2; RAC2; SERPINE1 | 5 | 0.65 | ADRA2A; CLU; EGF; GNG11; PIK3R6 | 11 | 1.61 | ACTN1; CAP1; CFL1; GNA15; HSPA5; P2RY1; PFN1; PPLAP22; PRKCQ; TUBA4A; YWHAZ |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | SERPINA1; SERPINE1; SRGN; TUBA4A; YWHAZ | | | | | | | | | | | | | | | |
| binding bridging: GO | 172 | 13 | 1.26 | ADAP2; ANXA1; CSTA; DSP; FLRT3; FSCN1; HOMER1; IVL; NEFL; SH2D2A; SHB; SPRR1A; SPRR1B | 14 | 0.96 | ANK2; ARHGAP6; COL11A1; COL11A2; COL19A1; GAS2L2; GRB14; IRS4; LOR; MAPK8IP1; SORBS1; SORBS2; TNNT2; TRDN | 0 | 0.00 | | 0 | 0.00 | | 3 | 0.44 | COL11A1; SORBS2; TRDN | 10 | 1.65 | ADAP2; AFAPIL2; BCL3; CSTA; FLRT3; HOMER1; IVL; SHB; SPRR1A; SPRR1B |
| pkmts methylate histone lysines | 32 | 6 | 3.14 | HIST1H3A; HIST1H3I; HIST1H4I; HIST1H4J; HIST1H4K; HIST1H4L | 0 | 0.00 | | 0 | 0.00 | | 0 | 0.00 | | 0 | 0.00 | | 3 | 2.66 | HIST1H3A; HIST1H3I; HIST1H4I |
| cellular response to alkaloid: GO | 32 | 5 | 2.61 | BLM; CCNA2; NTRK1; PLAU; TH | 3 | 1.11 | CASQ2; GSTM2; PPARGC1A | 0 | 0.00 | | 0 | 0.00 | | 1 | 0.79 | PPARGC1A | 3 | 2.66 | BLM; CCNA2; TH |
| receptor activator activity: GO | 32 | 5 | 2.61 | CXCL13; GREM1; NRG1; WNT5A; WNT7A | 5 | 1.84 | ACTN2; AGT; ANGPT4; EGF; NRG3 | 0 | 0.00 | | 0 | 0.00 | | 2 | 1.59 | ANGPT4; EGF | 3 | 2.66 | NRG1; WNT5A; WNT7A |
| rho pathway | 32 | 5 | 2.61 | ACTR3; ARPC1A; ARPC3; CFL1; PFN1 | 2 | 0.74 | ARHGAP6; GSN | 0 | 0.00 | | 0 | 0.00 | | 0 | 0.00 | | 3 | 2.66 | ARPCIA; CFL1; PFN1 |
| negative regulation of cyclin dependent protein kinase activity: GO | 32 | 3 | 1.57 | CDKN1A; PLK1; UBE2C | 2 | 0.74 | C2orf40; MYOCD | 1 | 13.06 | C2orf40 | 0 | 0.00 | | 0 | 0.00 | | 3 | 2.66 | CDKN1A; PLK1; UBE2C |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| positive regulation of cyclin dependent protein kinase activity: GO | 32 | 3 | 1.57 | CCND2; CDC6; CDKN1A | 1 | 0.37 | PKD1 | 0 | 0.00 | | 0 | 0.00 | | 0 | 0.00 | | 3 | 2.66 | CCND2; CDC6; CDKN1A |
| atp dependent dna helicase activity: GO | 32 | 2 | 1.05 | BLM; PIF1 | 0 | 0.00 | | 0 | 0.00 | | 0 | 0.00 | | 0 | 0.00 | | 3 | 2.66 | BLM; BRIP1; PIF1 |
| regulation of mitochondrion organization: GO | 195 | 22 | 1.89 | BAK1; C1QBP; DYNLL1; FAM162A; HIF1A; ITGAX; MMP9; NRG1; PLAUR; PPIF; PRELID1; PYCARD; RAC2; RUVBL1; SFN; SLC25A5; TNFSF10; TP63; UGCG; VDAC1; YWHAQ; YWHAZ | 9 | 0.54 | BCL2; CDKL2; HSPA1L; KAT2A; MYBPC1; NMUR1; NOL3; PLA2G6; PPARGC1A | 0 | 0.00 | | 2 | 4.29 | GZMB; RAC2 | 4 | 0.52 | BCL2; DCN; PPARGC1A; RHOU | 11 | 1.60 | BAK1; E2F1; HIF1A; MPV17L2; NRG1; PPIF; PRELID1; SFN; VDAC1; YWHAQ; YWHAZ |
| glycosaminoglycan binding: GO | 195 | 19 | 1.63 | CIQBP; CCL7; CXCL10; CXCL11; CXCL13; CXCL6; FGFBP1; HABP2; HBEGF; HMMR; LIPG; LTF; NELL2; PGF; PGLYRP2; | 29 | 1.75 | ABI3BP; APOE; BCAN; CCDC80; CFH; CLEC3B; COL25A1; ELANE; FGF1; FGF14; FGF9; FGFR1; GREM2; HAPLN2; LIPH; LPL; | 2 | 4.29 | CLEC3B; LPL | 0 | 0.00 | | 22 | 2.87 | ABI3BP; CCDC80; CFH; CHRD; CTGF; CTSG; DCN; DPYSL3; ELANE; FGF2; FGFR1; GREM2; IGHM; LIPH; MDK; NDNF; PCOLCE; PTCH1; | 11 | 1.60 | AGRN; CXCL11; CXCL6; FGFBP1; HAPLN3; HBEGF; HMMR; LTF; NELL2; SERPINA10; SERPINE2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | RNASE7; SELL; SERPINE2; WISP1 | | | MSTN; NDNF; PCOLCE2; PLA2G5; PRELP; PTCH1; SERPINA5; SLIT2; SLIT3; SOD3; TNXB; VIT; WISP2 | | | | | | | | | SLIT2; SLIT3; SOD3; WISP2 | | | |
| negative regulation of epithelial cell proliferation: GO | 109 | 9 | 1.38 | BRCA2; EREG; GJA1; IL26; SCG2; SFN; STAT1; TGFBR1; WNT5A | 8 | 0.87 | A4GNT; APOE; ATOH8; GDF5; GPC3; PAX6; PTCH1; TNMD | 1 | 3.83 | CDKN1C | 0 | 0.00 | | 3 | 0.70 | ATOH8; PTCH1; TNMD | 7 | 1.82 | BRCA2; EREG; PPARD; SFN; SNAI2; WNT5A; XDH |
| blood microparticle: GO | 130 | 12 | 1.54 | ACTB; HSPA6; HSPA8; IGHG1; IGHG2; IGHG4; IGKC; IGKV4-1; MSN; PFN1; SLC2A1; YWHAZ | 20 | 1.82 | ACTA1; AGT; ALB; AMBP; APOE; C3; C4BPA; CFH; CLU; CP; FCN2; GSN; HBA1; HBA2; HBB; HSPA1L; PON1; SLC4A1; TF; ZNF559-ZNF177 | 2 | 6.43 | IGHG1; IGKV3-20 | 0 | 0.00 | | 9 | 1.76 | C3; CFH; CLU; CP; HBA2; HBB; IGHM; IGHV3-23; PZP | 8 | 1.75 | ACTB; ANGPTL4; HSPA8; LGALS3BP; MSN; PFN1; SLC2A1; YWHAZ |
| transport to the golgi and subsequent modification | 130 | 10 | 1.29 | AREG; CAP1; CTSC; DYNLL1; ST8SIA2; TGFA; TUBA1C; TUBA4A; TUBB2A; TUBB6 | 3 | 0.27 | ANK2; FOLR1; TRAPPC6A | 0 | 0.00 | | 0 | 0.00 | | 2 | 0.39 | DLC1; TRAPPC6A | 8 | 1.75 | AREG; CAP1; ST8SIA2; TGFA; TUBA1C; TUBA4A; TUBB2A; TUBB6 |
| sodium ion transmembrane | 130 | 8 | 1.03 | ATP12A; ATP1B3; | 21 | 1.91 | ABCB11; ATP1A2; | 0 | 0.00 | | 0 | 0.00 | | 10 | 1.95 | ATP1B2; NALCN; | 8 | 1.75 | KCNK1; SCNN1D; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| transporter activity: GO | | | | KCNK1; SLC10A6; SLC28A3; SLC38A1; SLC5A1; SLC6A11 | | | FXYD2; NALCN; SCN7A; SLC10A2; SLC13A2; SLC17A4; SLC17A7; SLC1A2; SLC1A6; SLC1A7; SLC24A2; SLC34A3; SLC4A4; SLC5A2; SLC5A9; SLC6A17; SLC6A2; SLC9A2; SLC9A4 | | | | | | | | | SCN7A; SCNN1B; SLC13A2; SLC1A6; SLC1A7; SLC4A4; SLC5A9; SLC9A2 | | | SLC13A5; SLC20A1; SLC28A3; SLC4A7; SLC5A5; SLC6A11 |
| positive regulation of lipid transport: GO | 50 | 7 | 2.34 | ABCA12; IL1B; LIPG; LRAT; NTSR1; P2RY2; PRELID1 | 8 | 1.89 | ADIPOQ; APOE; CYP4A11; GALR1; P2RX7; PLA2G6; PON1; PTCH1 | 1 | 8.36 | ADIPOQ | 1 | 8.36 | IL1B | 2 | 1.02 | CYP4A11; PTCH1 | 4 | 2.27 | LRAT; NTSR1; P2RY2; PRELID1 |
| response to nicotine: GO | 50 | 7 | 2.34 | CHRNA3; CHRNA6; HMOX1; KCNK1; NTRK1; SLC7A11; TH | 5 | 1.18 | ATP1A2; BCL2; CHRNA2; CNR1; DRD1 | 0 | 0.00 | | 0 | 0.00 | | 1 | 0.51 | BCL2 | 4 | 2.27 | CHRNA6; KCNK1; SLC7A11; TH |
| negative regulation of dna replication: GO | 50 | 5 | 1.67 | BLM; BRCA2; CDC6; PIF1; S100A11 | 2 | 0.47 | MAPK15; TSPYL2 | 0 | 0.00 | | 0 | 0.00 | | 0 | 0.00 | | 4 | 2.27 | BLM; BRCA2; CDC6; PIF1 |
| negative regulation of nucleocytoplasmic transport: GO | 69 | 3 | 0.73 | MDFI; TXN; ZC3H12A | 2 | 0.34 | APOD; PKD1 | 0 | 0.00 | | 0 | 0.00 | | 1 | 0.37 | ANGPT1 | 5 | 2.05 | IL10; MDFI; SNAI2; TXN; ZC3H12A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| serine type endopeptidase inhibitor activity: GO | 89 | 18 | 3.38 | A2ML1; PI3; SERPINA1; SERPINB1; SERPINB10; SERPINB13; SERPINB2; SERPINB3; SERPINB4; SERPINB5; SERPINB7; SERPINB9; SERPINE1; SERPINE2; SLPI; SPINK6; SPINK7; WFDC12 | 13 | 1.72 | AGT; AMBP; COL28A1; ITIH5; SERPINA12; SERPINA5; SERPINA9; SPINK1; SPINT4; SPOCK1; WFDC13; WFDC3; WFIKKN1 | 1 | 4.70 | WFIKKN1 | 2 | 9.39 | SERPINB9; SERPINE1 | 8 | 2.28 | COL28A1; PZP; RECK; SERPINA12; SPINT4; SPOCK1; WFDC13; WFDC3 | 6 | 1.91 | SERPINA10; SERPINB13; SERPINB2; SERPINB5; SERPINE2; SLPI |
| signaling by erbb4 | 89 | 7 | 1.32 | CDK1; CDKN1A; EREG; HBEGF; NRAS; NRG1; PSENEN | 6 | 0.80 | BTC; EGF; ERBB4; GHR; NRG2; PGR | 1 | 4.70 | GHR | 0 | 0.00 | | 5 | 1.43 | CXCL12; EGF; ERBB4; ESR1; PGR | 6 | 1.91 | CDK1; CDKN1A; EREG; HBEGF; NRG1; TRIB3 |
| dilated cardio-myopathy | 89 | 4 | 0.75 | ACTB; ITGA3; ITGA6; ITGB6 | 21 | 2.78 | ADCY2; ADCY5; ADCY6; ADCY8; ADRB1; CACNA1F; CACNA2D1; CACNA2D2; CACNB1; DES; DMD; ITGA7; ITGA8; LAMA2; MYL3; SGCA; SGCG; TNNC1; TNNT2; TPM1; TPM2 | 1 | 4.70 | SGCG | 0 | 0.00 | | 6 | 1.71 | CACNA2D1; CACNA2D2; CACNB1; ITGA11; LAMA2; TNNC1 | 6 | 1.91 | ACTB; ITGA3; ITGA6; ITGB4; ITGB6; TPM4 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| clathrin coated vesicle: GO | 152 | 9 | 0.99 | AP1S3; CTLA4; FCGR1A; HBEGF; HSPA8; LDLR; MALL; STON2; WNT5A | 11 | 0.85 | CD207; CLVS1; CLVS2; FOLR1; FZD4; MLC1; NCALD; SFTPC; SLC17A7; SLC2A4; SYT1 | 0 | 0.00 | | 0 | 0.00 | | 6 | 1.00 | CD207; FCHO1; HLA-DQB2; NCALD; SLC18A2; STEAP2 | 9 | 1.68 | APIS3; HBEGF; HSPA8; LDLR; MALL; SFTPA2; SLC18A3; STON2; WNT5A |
| peptidase regulator activity: GO | 196 | 29 | 2.48 | AZMLT; BIRC5; CST7; CSTA; CSTB; CTSC; NGF; PI15; PI3; PSME3; PTTG1; PYCARD; SERPINA1; SERPINB1; SERPINB10; SERPINB13; SERPINB2; SERPINB3; SERPINB4; SERPINB5; SERPINB7; SERPINB9; SERPINE1; SERPINE2; SLPI; SPINK6; SPINK7; VCP; WFDC12 | 26 | 1.57 | AGT; AMBP; BIRC7; C3; COL28A1; CSTL1; GPC3; ITIH5; NOL3; PCOLCE2; RENBP; SERPINA12; SERPINA5; SERPINA9; SNCA; SPINK1; SPINT4; SPOCK1; SSPO; TFAP2B; TIMP3; TIMP4; WFDC10B; WFDC13; WFDC3; WFIKKN1 | 1 | 2.13 | WFIKKN1 | 2 | 4.26 | SERPINB9; SERPINE1 | 13 | 1.69 | C3; COL28A1; FBLN1; PCOLCE; PI16; PZP; RECK; SERPINA12; SNCA; SPINT4; SPOCK1; WFDC13; WFDC3 | 11 | 1.59 | BIRC5; CSTA; CSTB; NGF; PTTG1; SERPINA10; SERPINB13; SERPINB2; SERPINB5; SERPINE2; SLPI |
| response to vitamin d: GO | 33 | 8 | 4.06 | ALPL; AQP3; CXCL10; CYP24A1; CYP27B1; IL1B; PTGS2; TNC | 0 | 0.00 | | 0 | 0.00 | | 1 | 12.66 | IL1B | 0 | 0.00 | | 3 | 2.58 | AQP3; CYP27B1; PTGS2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| neutral amino acid transport: GO | 33 | 5 | 2.54 | SERINC2; SLC38A1; SLC38A5; SLC7A5; SLC7A8 | 3 | 1.07 | SLC6A17; SLC7A10; SLC7A9 | 0 | 0.00 | | 0 | 0.00 | | 0 | 0.00 | | 3 | 2.58 | SERINC2; SLC38A5; SLC7A5 |
| formation of fibrin clot (clotting cascade) | 33 | 4 | 2.03 | CIQBP; F12; SERPINE2; THBD | 5 | 1.79 | F10; F7; KLKB1; SERPINA5; TF | 0 | 0.00 | | 0 | 0.00 | | 0 | 0.00 | | 3 | 2.58 | F12; SERPINE2; THBD |
| regulation of sensory perception: GO | 33 | 4 | 2.03 | CCK; CCL3; NTSR1; PTAFR | 4 | 1.43 | ADORA1; FGFR1; GRIN2A; TMEM100 | 0 | 0.00 | | 0 | 0.00 | | 1 | 0.77 | FGFR1 | 3 | 2.58 | IL10; NTSR1; PTAFR |
| dicarboxylic acid transmembrane transporter activity: GO | 33 | 2 | 1.01 | SLC26A9; SLC7A11 | 8 | 2.86 | SLC13A2; SLC17A7; SLC1A2; SLC1A6; SLC1A7; SLC26A1; SLC26A5; SLC26A7 | 0 | 0.00 | | 0 | 0.00 | | 3 | 2.31 | SLC13A2; SLC1A6; SLC1A7 | 3 | 2.58 | SLC13A5; SLC26A6; SLC7A11 |
| cdc42 pathway | 70 | 5 | 1.20 | ACTR3; ARPC3; CFL1; DIAPH3; ENAH | 1 | 0.17 | PAX6 | 0 | 0.00 | | 0 | 0.00 | | 0 | 0.00 | | 5 | 2.03 | CFL1; DIAPH3; ENAH; IQGAP3; VAV2 |
| regulation of synapse assembly: GO | 70 | 5 | 1.20 | FLRT3; NTRK1; TPBG; WNT5A; WNT7A | 17 | 2.87 | CBLN1; CLSTN2; DKK1; EEF2K; EPHB1; GRIN1; LRRN1; LRRTM3; NLGN1; NRXN1; NRXN3; NTRK3; PPP1R9A; SIX1; SLITRK2; | 0 | 0.00 | | 0 | 0.00 | | 4 | 1.45 | LRRN1; NRXN1; SLITRK4; SLITRK6 | 5 | 2.03 | AGRN; FLRT3; TPBG; WNT5A; WNT7A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | SLITRK4; SLITRK5 | | | | | | | | | | | | |
| associative learning: GO | 70 | 4 | 0.96 | EIF4A3; HIF1A; HMGCR; NDRG4 | 11 | 1.85 | ATP1A2; DRD1; DRD4; GRIN1; GRIN2A; GRM7; NETO1; NEUROD2; PPPIRIB; RELN; SHANK1 | 0 | 0.00 | | 0 | 0.00 | | 1 | 0.36 | RELN | 5 | 2.03 | EIF4A3; HIF1A; HRH1; HRH2; SGK1 |
| positive regulation of alpha beta t cell activation: GO | 51 | 12 | 3.94 | ANXA1; CD3E; CD80; EBI3; HSPH1; IFNG; IL12B; IL4R; IL6; PNP; PRKCQ; SASH3 | 1 | 0.23 | ZBTB16 | 0 | 0.00 | | 0 | 0.00 | | 0 | 0.00 | | 4 | 2.22 | CD83; HSPH1; PNP; PRKCQ |
| regulation of interleukin 12 production: GO | 51 | 10 | 3.28 | ACP5; CIQBP; IDO1; IFNG; IL12B; JAK3; MEFV; SLAMF1; TNFRSF9; TNFSF9 | 0 | 0.00 | | 0 | 0.00 | | 0 | 0.00 | | 0 | 0.00 | | 4 | 2.22 | ACP5; HLA-G; IL10; MEFV |
| interaction with symbiont: GO | 51 | 8 | 2.62 | CAMP; CCL3; CFL1; HMGA2; LTF; PPIB; TREM1; ZC3H12A | 3 | 0.69 | APOE; ELANE; POU2F3 | 0 | 0.00 | | 1 | 8.19 | TREM1 | 2 | 1.00 | CTSG; ELANE | 4 | 2.22 | CFL1; HMGA2; LTF; ZC3H12A |
| sulfotransferase activity: GO | 51 | 5 | 1.64 | CHST1; HS3ST1; HS3ST3A1; HS3ST3B1; SULT2B1 | 11 | 2.54 | CHST12; CHST5; GAL3ST1; HS3ST2; HS3ST5; HS3ST6; HS6ST3; SULT1A2; | 0 | 0.00 | | 0 | 0.00 | | 5 | 2.49 | CHST12; DSEL; GAL3ST4; SULT1E1; UST | 4 | 2.22 | CHST1; HS3ST1; HS3ST3A1; SULT2B1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | SULT1C3; UST; WSCD1 | | | | | | | | | | | | |
| p75 ntr receptor-mediated signalling | 51 | 4 | 1.31 | ECT2; MYD88; NGF; PSENEN | 2 | 0.46 | ARHGEF26; MCF2L | 0 | 0.00 | | 0 | 0.00 | | 1 | 0.50 | ARHGEF26 | 4 | 2.22 | ECT2; MYD88; NGF; VAV2 |
| response to alkaloid: GO | 132 | 15 | 1.90 | BLM; CCNA2; CHRNA3; CHRNA6; HIF1A; HMOX1; HOMER1; HTR3A; IL1B; IL6; KCNK1; NTRK1; PLAU; SLC7A11; TH | 13 | 1.16 | ATP1A2; BCL2; CASQ2; CHRNA2; CNR1; DRD1; DRD4; GRIN1; GSTM2; HDAC5; PPARGC1A; SDC2; SNCA | 0 | 0.00 | | 1 | 3.17 | IL1B | 4 | 0.77 | BCL2; PPARGC1A; SLC18A2; SNCA | 8 | 1.72 | BLM; CCNA2; CHRNA6; HIF1A; HOMER1; KCNK1; SLC7A11; TH |
| regulation of response to dna damage stimulus: GO | 132 | 7 | 0.89 | CHEK1; FOXM1; H2AFX; HMGA2; PCNA; POLQ; UBE2N | 2 | 0.18 | APBB1; CLU | 0 | 0.00 | | 0 | 0.00 | | 2 | 0.38 | CLU; CXCL12 | 8 | 1.72 | CHEK1; FOXM1; H2AFX; HMGA2; IER3; POLQ; RAD51AP1; SNAI2 |
| activation of cysteine type endopeptidase activity: GO | 91 | 14 | 2.57 | BAK1; CCK; CYCS; FAM162A; IFI16; IFI27; NGF; PERP; PYCARD; S100A8; S100A9; TNFRSF10A; TNFSF10; VCP | 2 | 0.26 | P2RX1; SNCA | 0 | 0.00 | | 0 | 0.00 | | 2 | 0.56 | DLC1; SNCA | 6 | 1.87 | BAK1; CYCS; IFI16; IFI27; NGF; XDH |
| cellular monovalent inorganic cation homeostasis: GO | 91 | 6 | 1.10 | ATP12A; ATP1B3; CA2; RAB38; SLC26A9; SLC4A8 | 17 | 2.20 | AGT; ATP1A2; ATP6V0A4; ATP6V0E2; ATP6V1B1; | 0 | 0.00 | | 0 | 0.00 | | 5 | 1.40 | ATP1B2; ATP6V0A4; ATP6V0E2; BCL2; SLC4A4 | 6 | 1.87 | CA2; RAB38; SGK1; SLC26A6; SLC4A3; SLC4A7 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | | | | BCL2; CFTR; NOX1; SGK2; SLC17A7; SLC26A1; SLC26A5; SLC26A7; SLC4A1; SLC4A4; TFAP2B; TTPA | | | | | | | | | | | | |
| basement membrane: GO | 91 | 5 | 0.92 | GSTO1; ITGA6; LAD1; LAMB3; TNC | 10 | 1.30 | ALB; CCDC80; COL28A1; FGF9; FREM1; LAMA2; LAMB4; LAMC3; SMOC1; TIMP3 | 0 | 0.00 | | 0 | 0.00 | | 9 | 2.51 | CCDC80; COL28A1; FBLN1; FRAS1; FREM1; LAMA2; LAMC3; NTN4; VWC2 | 6 | 1.87 | AGRN; ANXA2P2; COL17A1; ITGA6; LAD1; LAMB3 |
| positive regulation of stat cascade: GO | 71 | 11 | 2.59 | CSF2; IFNG; IL12B; IL19; IL20; IL22; IL24; IL26; IL6; OSM; SOCS3 | 6 | 1.00 | ERBB4; FGFR3; GHR; IL5; LEP; LIF | 1 | 5.89 | GHR | 1 | 5.89 | OSM | 1 | 0.36 | ERBB4 | 5 | 2.00 | IL10; IL19; IL20; IL22; SOCS3 |
| sensory perception of pain: GO | 71 | 10 | 2.36 | ADCYAP1; BDKRB1; IL12B; NMU; NTRK1; NTSR1; P2RY1; P2RY2; PROK2; PTGS2 | 11 | 1.83 | ADORA1; CNR1; DLG2; EPHB1; GRIN1; GRIN2A; KCNA1; KCNA2; KCND2; NPY1R; P2RX7 | 0 | 0.00 | | 0 | 0.00 | | 3 | 1.07 | DLG2; KCND2; NPY1R | 5 | 2.00 | NMU; NTSR1; P2RY1; P2RY2; PTGS2 |
| regulation of cellular ph: GO | 71 | 4 | 0.94 | CA2; RAB38; SLC26A9; SLC4A8 | 13 | 2.16 | ATP6V0A4; ATP6V0E2; ATP6V1B1; BCL2; CFTR; NOX1; | 0 | 0.00 | | 0 | 0.00 | | 4 | 1.43 | ATP6V0A4; ATP6V0E2; BCL2; SLC4A4 | 5 | 2.00 | CA2; RAB38; SLC26A6; SLC4A3; SLC4A7 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | A: Fold Change (FC) Up | A: Up-regulated Genes | A: Down-regulated | A: Fold Change (FC) | A: Down-regulated Genes | B. Differentially expressed genes significant in the baseline vs week 12 comparison only in the placebo: Up-regulated | B: Fold Change (FC) Up | B: Up-regulated Genes | B: Down-regulated | B: Fold Change (FC) | B: Down-regulated Genes | C. Differentially expressed genes significant in the baseline vs week 12 comparison only in the nemo: Up-regulated | C: Fold Change (FC) Up | C: Up-regulated Genes | C: Down-regulated | C: Fold Change (FC) | C: Down-regulated Genes |
|---|---|---|---|---|---|---|---|---|---|---|---|---|---|---|---|---|---|---|---|
| | | | | | | | SLC17A7; SLC26A1; SLC26A5; SLC26A7; SLC4A1; SLC4A4; TTPA | | | | | | | | | | | | |
| regulation of nitric oxide biosynthetic process: GO | 52 | 6 | 1.93 | ACP5; IFNG; IL1B; IL6; PTGS2; ZC3H12A | 5 | 1.13 | AGT; CD34; CLU; HBB; PTGIS | 0 | 0.00 | | 1 | 8.04 | IL1B | 4 | 1.95 | CD34; CLU; ESR1; HBB | 4 | 2.18 | ACP5; IL10; PTGS2; ZC3H12A |
| n rage signals death through jnk | 52 | 2 | 0.64 | ECT2; NGF | 3 | 0.68 | ARHGEF26; MCF2L; OBSCN | 0 | 0.00 | | 0 | 0.00 | | 1 | 0.49 | ARHGEF26 | 4 | 2.18 | ARHGEF16; ECT2; NGF; VAV2 |
| positive regulation of erbb signaling pathway: GO | 34 | 5 | 2.46 | EPGN; EREG; MMP9; PLAUR; TGFA | 4 | 1.39 | ADORA1; ADRA2A; AGT; EGF | 0 | 0.00 | | 0 | 0.00 | | 3 | 2.24 | ADRA2A; EGF; ESR1 | 3 | 2.50 | AFAP1L2; EREG; TGFA |
| negative regulation of epithelial cell apoptotic process: GO | 34 | 3 | 1.48 | SCG2; SERPINB13; SERPINE1 | 1 | 0.35 | NDNF | 0 | 0.00 | | 1 | 12.29 | SERPINE1 | 2 | 1.49 | ANGPT1; NDNF | 3 | 2.50 | ANGPTL4; IL10; SERPINB13 |
| positive regulation of protein localization to cell periphery: GO | 34 | 2 | 0.98 | IFNG; ITGA3 | 4 | 1.39 | ANXA13; DPP10; NRXN1; SORBS1 | 0 | 0.00 | | 0 | 0.00 | | 1 | 0.75 | NRXN1 | 3 | 2.50 | ARHGEF16; EPHA2; ITGA3 |
| regulation of transcription factor import into nucleus: GO | 92 | 8 | 1.46 | GREM1; IL12B; IL1B; MDFI; PRDX1; PRKCQ; PTGS2; ZC3H12A | 3 | 0.38 | EDA; NOL3; PKD1 | 0 | 0.00 | | 1 | 4.54 | IL1B | 0 | 0.00 | | 6 | 1.85 | BCL3; IL10; MDFI; PRKCQ; PTGS2; ZC3H12A |
| myeloid leukocyte differentiation: GO | 92 | 7 | 1.27 | ACP5; CSF2; F2RL1; GLO1; IFI16; MMP9; TNFSF9 | 2 | 0.26 | GATA1; GPC3 | 0 | 0.00 | | 0 | 0.00 | | 0 | 0.00 | | 6 | 1.85 | ACP5; DHRS2; EPHA2; IFI16; JUNB; SBNO2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| response to calcium ion: GO | 113 | 8 | 1.18 | AQP3; ECT2; HOMER1; IL6; PPIF; S100A16; SDC1; WNT5A | 13 | 1.36 | CASQ2; CHP2; D2HGDH; EEF2K; GPLD1; GRIN1; KCNIP2; KCNMB4; NEUROD2; P2RX7; SYT1; TNNT2; TXNIP | 0 | 0.00 | | 0 | 0.00 | | 5 | 1.12 | ACER1; CHP2; GPLD1; TRPC1; TXNIP | 7 | 1.76 | AQP3; ECT2; HOMER1; JUNB; PPIF; S100A16; WNT5A |
| positive regulation of anion transport: GO | 53 | 7 | 2.21 | CCK; GDNF; IL1B; NTSR1; P2RY2; PRELID1; PTAFR | 8 | 1.78 | APOE; CFTR; CYP4A11; DRD4; P2RX7; PCP4; PLA2G6; RAB3B | 0 | 0.00 | | 1 | 7.88 | IL1B | 3 | 1.44 | CXCL12; CYP4A11; RAB3B | 4 | 2.14 | NTSR1; P2RY2; PRELIDI; PTAFR |
| visual photo-transduction | 53 | 5 | 1.58 | AKRIB10; LDLR; LRP8; RDH16; SDC1 | 5 | 1.11 | APOE; GPC3; GPC6; RBP4; SDC2 | 0 | 0.00 | | 0 | 0.00 | | 0 | 0.00 | | 4 | 2.14 | AGRN; AKR1B10; LDLR; RDH16 |
| mammary gland epithelium development: GO | 53 | 4 | 1.26 | AREG; FOXF1; HIF1A; WNT5A | 3 | 0.67 | ERBB4; GLI2; PTCH1 | 0 | 0.00 | | 0 | 0.00 | | 4 | 1.92 | ERBB4; ESR1; GLI2; PTCH1 | 4 | 2.14 | AREG; EPHA2; HIF1A; WNT5A |
| positive regulation of synapse assembly: GO | 53 | 4 | 1.26 | FLRT3; NTRK1; TPBG; WNT7A | 13 | 2.89 | CBLN1; CLSTN2; EEF2K; EPHB1; LRRN1; LRRTM3; NLGN1; NRXN1; NRXN3; NTRK3; SLITRK2; SLITRK4; SLITRK5 | 0 | 0.00 | | 10 | 0.00 | | 4 | 1.92 | LRRN1; NRXN1; SLITRK4; SLITRK6 | 4 | 2.14 | AGRN; FLRT3; TPBG; WNT7A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| regulation of protein kinase b signaling: GO | 114 | 11 | 1.61 | C1QBP; CCL21; CCL3; FAM110C; HBEGF; HPSE; IL26; IL6; NRG1; TGFBR1; TXN | 7 | 0.72 | F10; F7; LEP; MAGI2; MSTN; MYOC; PKHD1 | 0 | 0.00 | | 0 | 0.00 | | 4 | 0.89 | ANGPT1; IGFBP5; MYOC; TSPYL5 | 7 | 1.74 | EPHA2; FAM110C; HBEGF; HPSE; NRG1; TXN; XDH |
| cellular metabolic compound salvage: GO | 35 | 5 | 2.39 | CDA; PNP; TK1; TYMP; UPP1 | 3 | 1.01 | AMPD1; BHMT2; UPP2 | 0 | 0.00 | | 0 | 0.00 | | 0 | 0.00 | | 3 | 2.43 | CDA; PNP; TK1 |
| negative regulation of smooth muscle cell proliferation: GO | 35 | 4 | 1.91 | HMOX1; IFNG; IL12B; NDRG4 | 5 | 1.69 | ADIPOQ; APOD; PPARGC1A; TPM1; VIPR2 | 1 | 11.94 | ADIPOQ | 0 | 0.00 | | 3 | 2.18 | ESR1; IGFBP5; PPARGC1A | 3 | 2.43 | IGFBP3; PPARD; TRIB1 |
| protein k63 linked ubiquitination: GO | 35 | 4 | 1.91 | UBE2F; UBE2N; UBE2S; UBE2T | 0 | 0.00 | | 0 | 0.00 | | 0 | 0.00 | | 0 | 0.00 | | 3 | 2.43 | UBE2F; UBE2S; UBE2T |
| regulation of dendritic spine development: GO | 54 | 5 | 1.55 | CDK5R1; CFL1; LRP8; NRG1; PLK2 | 12 | 2.62 | APOE; CAMK1; CAMK2B; EEF2K; FOXO6; NLGN1; PAK3; PALM; PPP1R9A; RELN; SHANK1; SRCIN1 | 1 | 7.74 | SRCIN1 | 0 | 0.00 | | 6 | 2.82 | CAMK1; FOXO6; LPAR1; PAK3; PALM; RELN | 4 | 2.10 | CDK5R1; CFL1; NRG1; PLK2 |
| regulation of cellular response to insulin stimulus: GO | 54 | 4 | 1.24 | IL1B; PRKCQ; PTPRE; SOCS3 | 6 | 1.31 | ENPP1; GPLD1; LEP; MSTN; RARRES2; SERPINA12 | 0 | 0.00 | | 1 | 7.74 | IL1B | 3 | 1.41 | GPLD1; RARRES2; SERPINA12 | 4 | 2.10 | CISH; PRKCQ; PTPRE; SOCS3 |
| neuron neuron synaptic transmission: | 54 | 3 | 0.93 | TH; UNC13A; VDAC1 | 11 | 2.40 | DNM1; DRD1; DRD4; GLRB; | 0 | 0.00 | | 0 | 0.00 | | 3 | 1.41 | CNIH3; GLRB; SNCA | 4 | 2.10 | DLGAP2; TH; UNC13A; VDAC1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| GO | | | | | | | GRIK5; GRIN1; P2RX1; SHC3; SLC17A7; SLC6A2; SNCA | | | | | | | | | | | | |
| protein dephosphorylation: GO | 181 | 12 | 1.11 | CDC25A; CDC25B; CDKN3; CYCS; DLGAP5; DUSP14; DUSP6; DUSP9; PPP4R1; PTPRE; UBASH3B; UBLCP1 | 5 | 0.33 | BCL2; DUSP27; MYH3; PTPRQ; PTPRT | 0 | 0.00 | | 0 | 0.00 | | 2 | 0.28 | BCL2; PTPRT | 10 | 1.57 | CDC25A; CDC25B; CDKN3; CYCS; DLGAP5; DUSP6; PPP4R1; PTP4A1; PTPRE; UBASH3B |
| regulation of lymphocyte migration: GO | 36 | 9 | 4.18 | CCL21; CCL3; CCL7; CXCL10; CXCL13; MSN; PYCARD; S100A7; WNT5A | 1 | 0.33 | APOD | 0 | 0.00 | | 0 | 0.00 | | 1 | 0.71 | CXCL12 | 3 | 2.36 | CCL20; MSN; WNT5A |
| nuclear signaling by erbb4 | 36 | 4 | 1.86 | EREG; HBEGF; NRG1; PSENEN | 5 | 1.64 | BTC; ERBB4; GHR; NRG2; PGR | 1 | 11.61 | GHR | 0 | 0.00 | | 4 | 2.82 | CXCL12; ERBB4; ESR1; PGR | 3 | 2.36 | EREG; HBEGF; NRG1 |
| phosphoinositide 3 kinase pathway | 36 | 4 | 1.86 | NR4A3; SFN; YWHAQ; YWHAZ | 0 | 0.00 | | 0 | 0.00 | | 0 | 0.00 | | 0 | 0.00 | | 3 | 2.36 | SFN; YWHAQ; YWHAZ |
| retinoid metabolism and transport | 36 | 4 | 1.86 | AKRIB10; LDLR; LRP8; SDC1 | 5 | 1.64 | APOE; GPC3; GPC6; RBP4; SDC2 | 0 | 0.00 | | 0 | 0.00 | | 0 | 0.00 | | 3 | 2.36 | AGRN; AKRIB10; LDLR |
| frizzled binding: GO | 36 | 2 | 0.93 | WNT5A; WNT7A | 2 | 0.66 | MYOC; WNT11 | 0 | 0.00 | | 0 | 0.00 | | 3 | 2.12 | FZD7; MYOC; WNT11 | 3 | 2.36 | WNT5A; WNT7A; WNT9B |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| lyase activity: GO | 160 | 8 | 0.84 | AMD1; CA2; ENO1; GLO1; HAL; HMGA2; ODC1; POLQ | 16 | 1.18 | ADCY2; ADCY5; ADCY6; ADCY8; ALDOB; CA1; CA11; CA3; CA6; CRY2; CYP17A1; DDTL; HMGCLL1; HOGA1; NEIL1; PCK1 | 0 | 0.00 | | 0 | 0.00 | | 8 | 1.27 | ALDOC; CA1; CA11; CA3; CA6; CENPV; CRY2; HDC | 9 | 1.60 | CA2; ENO1; GADL1; GLDC; HMGA2; NEIL3; ODC1; POLQ; SCLY |
| apoptotic mitochondrial changes: GO | 55 | 8 | 2.43 | BAK1; BCL2A1; CCK; GGCT; HK2; IFI6; PPIF; SFN | 6 | 1.29 | ATP2A1; BCL2; CAMK2A; CLU; ERBB4; NOL3 | 0 | 0.00 | | 0 | 0.00 | | 3 | 1.39 | BCL2; CLU; ERBB4 | 4 | 2.06 | BAK1; HK2; PPIF; SFN |
| endothelial cell migration: GO | 55 | 8 | 2.43 | CXCL13; DPP4; GREM1; PRSS3; S100A2; SCG2; STAT1; TGFBR1 | 4 | 0.86 | AMOT; GPLD1; PLEKHG5; SLIT2 | 0 | 0.00 | | 0 | 0.00 | | 3 | 1.39 | FGF2; GPLD1; SLIT2 | 4 | 2.06 | DPP4; PRSS3; S100A2; S100P |
| cellular response to corticosteroid stimulus: GO | 55 | 6 | 1.83 | ADCYAP1; ANXA1; GSTP1; IL6; RAN; UGT1A1 | 2 | 0.43 | HMGCS2; MSTN | 0 | 0.00 | | 0 | 0.00 | | 1 | 0.46 | HMGCS2 | 4 | 2.06 | GSTP1; RAN; SGK1; UCN2 |
| epithelial to mesenchymal transition: GO | 55 | 6 | 1.83 | EOMES; FAM83D; HIF1A; HMGA2; TGFBR1; WNT5A | 6 | 1.29 | AMELX; GSC; NOG; PAX3; TMEM100; WNT11 | 0 | 0.00 | | 0 | 0.00 | | 1 | 0.46 | WNT11 | 4 | 2.06 | HIF1A; HMGA2; SNAI2; WNT5A |
| microtubule bundle formation: GO | 55 | 3 | 0.91 | KIF20A; PLA2G3; PLK1 | 10 | 2.15 | CAPN6; CCDC114; CCDC40; DNAAF1; GAS2L2; | 2 | 15.20 | CAPN6; TPPP3 | 0 | 0.00 | | 3 | 1.39 | CCDC114; SPEF2; TPPP | 4 | 2.06 | KIF20A; NAV1; PLA2G3; PLK1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | HYDIN; RSPH1; SPEF2; TPPP; TPPP3 | | | | | | | | | | | | |
| interferon signaling | 183 | 28 | 2.56 | EIF4A3; EIF4G2; FCGR1A; GBP6; HERC6; IFI27; IFI30; IFI6; IFIT3; IFITM1; IFITM3; IFNG; IL6; ISG15; ISG20; KPNA2; MT2A; MX1; OAS1; OAS2; OAS3; OASL; PTAFR; RSAD2; SOCS3; STAT1; TRIM14; UBE2N | 6 | 0.39 | CAMK2A; CAMK2B; CES1; IFNA5; NCAM1; TRIM2 | 0 | 0.00 | | 3 | 6.85 | GBP1; IFITM3; ISG15 | 3 | 0.42 | CES1; NCAM1; TRIM2 | 10 | 1.55 | EIF4A3; GBP6; HERC6; HLA-G; IFI27; KPNA2; MX1; OAS1; PTAFR; SOCS3 |
| receptor metabolic process: GO | 75 | 4 | 0.89 | CXCR1; NRG1; PCSK9; RAB31 | 6 | 0.94 | CALCR; DNM1; GHR; GPRASP1; GRIA1; SNCA | 1 | 5.57 | GHR | 0 | 0.00 | | 3 | 1.02 | GPRASP1; GRIA1; SNCA | 5 | 1.89 | CXCR1; IL10; NRG1; PCSK9; RAB31 |
| monocarboxylic acid transport: GO | 117 | 10 | 1.43 | ANXA1; BDKRB2; FABP6; GOT2; SLC10A6; SLC16A1; SLC16A6; SLC16A9; SLC6A11; TRPC4 | 18 | 1.82 | ABCB11; ABCC3; ABCD2; ACACB; ALB; APBA1; APOE; DRD4; LEP; NOS2; PLA2G5; PRKAA2; SLC10A2; SLC16A11; SLC16A12; | 2 | 7.14 | ABCD2; SLC27A6 | 1 | 3.57 | AQP9 | 2 | 0.43 | APBA1; PRKAA2 | 7 | 1.70 | BDKRB2; GOT2; PPARD; SLC16A6; SLC16A9; SLC26A6; SLC6A11 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | | | | SLC16A8; SLC22A9; SLC27A6 | | | | | | | | | | | | |
| regulation of epithelial cell migration: GO | 162 | 15 | 1.55 | ANXA3; CXCL13; HBEGF; HIF1A; IFNG; INSL3; ITGA3; MMP9; PFN1; PTGS2; RAB25; SH3BGRL3; WNT5A; WNT7A; ZC3H12A | 12 | 0.87 | AGT; AMOT; ANGPT4; APOE; ATOH8; CCBE1; FGF1; FGFR1; GPLD1; HDAC5; SEMA3A; SLIT2 | 0 | 0.00 | | 1 | 2.58 | ANXA3 | 9 | 1.41 | ANGPT1; ANGPT4; ATOH8; CCBE1; DCN; FGF2; FGFR1; GPLD1; SLIT2 | 9 | 1.58 | EPHA2; HBEGF; HIF1A; ITGA3; PFN1; PTGS2; WNT5A; WNT7A; ZC3H12A |
| positive regulation of nucleocytoplasmic transport: GO | 118 | 13 | 1.84 | CDK1; ECT2; GREM1; IL12B; IL1B; IL6; JUP; PRKCQ; PTGS2; SFN; SULF2; TGFBR1; ZC3H12A | 8 | 0.80 | CAMK1; CHP2; DACTI; EDA; EGF; ERBB4; LEP: RANBP3L | 0 | 0.00 | | 1 | 3.54 | IL1B | 7 | 1.51 | CAMK1; CHP2; DACT1; EGF; ERBB4; RANBP3L; ZIC1 | 7 | 1.68 | CDK1; ECT2; GTSE1; PRKCQ; PTGS2; SFN; ZC3H12A |
| nuclear periphery: GO | 118 | 10 | 1.42 | BLM; CENPF; CENPW; CFL1; EBNA1BP2; KIF4A; LMNB1; LMNB2; RUVBL1; UHRF1 | 5 | 0.50 | MAPT; PHACTR3; RUNX1T1; SORBS1; SPTBN4 | 0 | 0.00 | | 0 | 0.00 | | 4 | 0.86 | MAPT; PHACTR3; RUNX1T1; SPTBN4 | 7 | 1.68 | BLM; CENPF; CENPW; CFL1; EBNA1BP2; KIF4A; LMNB2 |
| monovalent inorganic cation homeostasis: GO | 118 | 7 | 0.99 | ATP12A; ATP1B3; CA2; RAB38; RHCG; SLC26A9; SLC4A8 | 23 | 2.30 | AGT; ATP1A2; ATP6V0A4; ATP6V0E2; ATP6V1B1; BCL2; CFTR; CYP4A11; | 0 | 0.00 | | 0 | 0.00 | | 11 | 2.37 | ATP1B2; ATP6V0A4; ATP6V0E2; BCL2; CYP4A11; CYP4F12; PDK4; | 7 | 1.68 | CA2; RAB38; RHCG; SGK1; SLC26A6; SLC4A3; SLC4A7 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | A: Fold Change (FC) Up | A: Up-regulated Genes | A: Down-regulated | A: Fold Change (FC) | A: Down-regulated Genes | B. Differentially expressed genes significant in the baseline vs week 12 comparison only in the placebo: Up-regulated | B: Fold Change (FC) Up | B: Up-regulated Genes | B: Down-regulated | B: Fold Change (FC) | B: Down-regulated Genes | C. Differentially expressed genes significant in the baseline vs week 12 comparison only in the nemo: Up-regulated | C: Fold Change (FC) Up | C: Up-regulated Genes | C: Down-regulated | C: Fold Change (FC) | C: Down-regulated Genes |
|---|---|---|---|---|---|---|---|---|---|---|---|---|---|---|---|---|---|---|---|
| | | | | | | | CYP4F12; NOX1; PDK4; SCN7A; SGK2; SLC17A7; SLC26A1; SLC26A5; SLC26A7; SLC4A1; SLC4A4; SLC9A2; SLC9A4; TFAP2B; TTPA | | | | | | | | | SCN7A; SCNN1B; SLC4A4; SLC9A2 | | | |
| il23 pathway | 37 | 12 | 5.43 | CD3E; CXCL1; CXCL9; IFNG; IL12B; IL19; IL1B; IL24; IL6; ITGA3; SOCS3; STAT1 | 1 | 0.32 | NOS2 | 0 | 0.00 | | 2 | 22.59 | CXCL9; IL1B | 0 | 0.00 | | 3 | 2.30 | IL19; ITGA3; SOCS3 |
| embryo implantation: GO | 37 | 6 | 2.71 | IL1B; MMP9; PLAU; PTGS2; SERPINE2; VMP1 | 6 | 1.91 | IL11RA; LIF; PCSK5; PTGIS; SCGB1A1; TRO | 0 | 0.00 | | 1 | 11.29 | IL1B | 3 | 2.06 | FBLN1; IL11RA; RECK | 3 | 2.30 | PPARD; PTGS2; SERPINE2 |
| il-2 receptor beta chain in t cell activation | 37 | 5 | 2.26 | IL2RA; JAK3; NMI; PPIA; SOCS3 | 1 | 0.32 | BCL2 | 0 | 0.00 | | 1 | 11.29 | IL2RA | 1 | 0.69 | BCL2 | 3 | 2.30 | E2F1; NMI; SOCS3 |
| positive regulation of organ growth: GO | 37 | 5 | 2.26 | CCNB1; CDK1; NRG1; SASH3; TBX20 | 6 | 1.91 | ACACB; CACNA2D2; ERBB4; FGF9; FGFR1; TBX5 | 0 | 0.00 | | 0 | 0.00 | | 4 | 2.75 | CACNA2D2; ERBB4; FGF2; FGFR1 | 3 | 2.30 | CCNB1; CDK1; NRG1 |
| negative regulation of axon extension: GO | 37 | 3 | 1.36 | CDK5R1; SEMA4B; WNT5A | 6 | 1.91 | PLXNA3; SEMA3A; SEMA3B; SEMA3D; | 0 | 0.00 | | 0 | 0.00 | | 2 | 1.37 | SEMA3E; SEMA4G | 3 | 2.30 | CDK5R1; SEMA4B; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | SEMA3E; SEMA3G | | | | | | | | | | | | |
| beta catenin nuc pathway | 76 | 5 | 1.10 | CCND2; MMP9; SFN; YWHAQ; YWHAZ | 9 | 1.40 | AR; CDX4; DKK1; MITF; SP5; SSPO; TCF7L1; TERT; TLE2 | 0 | 0.00 | | 0 | 0.00 | | 6 | 2.01 | CACNA1G; CDX4; MITF; SP5; TCF7L1; TLE2 | 5 | 1.87 | CCND2; SFN; SNAI2; YWHAQ; YWHAZ |
| unfolded protein binding: GO | 97 | 13 | 2.24 | CALR; CCT2; CCT3; CCT5; CCT6A; CCT7; GRPEL2; HSPA5; HSPA6; HSPA8; NPM1; PPIA; PPIB | 4 | 0.49 | CRYAB; DNAJB8; GRXCR2; HSPA1L | 1 | 4.31 | CRYAB | 0 | 0.00 | | 0 | 0.00 | | 6 | 1.75 | CCT2; CCT5; GRPEL2; HSPA5; HSPA8; NPM1 |
| camera type eye morphogenesis: GO | 97 | 8 | 1.38 | ALDH1A3; BAK1; FJX1; HIF1A; SDK2; STRA6; TH; WNT5A | 11 | 1.34 | BCAR3; CDON; EPHB1; FOXE3; FOXN4; PAX6; RBP4; RORB; SOX1; SOX8; TFAP2B | 0 | 0.00 | | 0 | 0.00 | | 3 | 0.79 | BCAR3; CDON; TSPAN12 | 6 | 1.75 | BAK1; EPHA2; HIF1A; SDK2; TH; WNT5A |
| negative regulation of cell growth: GO | 163 | 11 | 1.13 | BDKRB1; CDA; CDK5R1; CDKN1A; CYP27B1; ENO1; GJA1; GREM1; SEMA4B; SERPINE2; WNT5A | 19 | 1.38 | AGT; APBB1; BCL2; CRYAB; ENPP1; FHL1; FRZB; PLXNA3; SCGB3A1; SEMA3A; SEMA3B; SEMA3D; SEMA3E; SEMA3G; | 1 | 2.56 | CRYAB | 0 | 0.00 | | 6 | 0.94 | BCL2; SEMA3E; SEMA4G; SLIT2; SLIT3; WNT11 | 9 | 1.57 | CDA; CDK5R1; CDKN1A; CYP27B1; ENO1; PPARD; SEMA4B; SERPINE2; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | SLIT2; SLIT3; TRO; TSPYL2; WNT11 | | | | | | | | | | | | |
| cofactor catabolic process: GO | 20 | 6 | 5.02 | ACOT7; CYP4F11; HMOX1; HMOX2; UGT1A1; VCP | 3 | 1.77 | ALDH1L1; AMBP; ASPDH | 0 | 0.00 | | 0 | 0.00 | | 0 | 0.00 | | 2 | 2.84 | ACOT7; HMOX2 |
| lamellar body: GO | 20 | 5 | 4.18 | ABCA12; CKAP4; KLK5; KLK7; LAMP3 | 3 | 1.77 | ABCA3; NAPSA; SFTPC | 0 | 0.00 | | 1 | 20.89 | LAMP3 | 1 | 1.27 | ABCA3 | 2 | 2.84 | CKAP4; SFTPA2 |
| epiboly: GO | 20 | 3 | 2.51 | HBEGF; MMP12; WNT7A | 0 | 0.00 | | 0 | 0.00 | | 0 | 0.00 | | 1 | 1.27 | SCNN1B | 2 | 2.84 | HBEGF; WNT7A |
| heparan sulfate biosynthesis | 20 | 3 | 2.51 | HS3ST1; HS3ST3A1; HS3ST3B1 | 4 | 2.36 | EXTL1; HS3ST2; HS3ST5; HS6ST3 | 0 | 0.00 | | 0 | 0.00 | | 0 | 0.00 | | 2 | 2.84 | HS3ST1; HS3ST3A1 |
| monosaccharide transmembrane transporter activity: GO | 20 | 3 | 2.51 | SLC2A1; SLC2A9; SLC5A1 | 3 | 1.77 | SLC2A4; SLC5A2; SLC5A9 | 0 | 0.00 | | 0 | 0.00 | | 2 | 2.54 | SLC2A12; SLC5A9 | 2 | 2.84 | SLC2A1; SLC2A9 |
| regulation of icosanoid secretion: GO | 20 | 3 | 2.51 | IL1B; NTSR1; P2RY2 | 3 | 1.77 | CYP4A11; P2RX7; PLA2G6 | 0 | 0.00 | | 1 | 20.89 | IL1B | 1 | 1.27 | CYP4A11 | 2 | 2.84 | NTSR1; P2RY2 |
| activation of bh3-only proteins | 20 | 2 | 1.67 | DYNLL1; SFN | 1 | 0.59 | BCL2 | 0 | 0.00 | | 0 | 0.00 | | 2 | 2.54 | BCL2; DLC1 | 2 | 2.84 | E2F1; SFN |
| activation of protein kinase b activity: GO | 20 | 2 | 1.67 | TXN; WNT5A | 2 | 1.18 | ADRA2A; NTRK3 | 0 | 0.00 | | 0 | 0.00 | | 1 | 1.27 | ADRA2A | 2 | 2.84 | TXN; WNT5A |
| carbohydrate phosphorylation: GO | 20 | 2 | 1.67 | HK2; PFKFB4 | 1 | 0.59 | PFKFB1 | 0 | 0.00 | | 0 | 0.00 | | 1 | 1.27 | PFKFB1 | 2 | 2.84 | HK2; PFKFB4 |
| common pathway of fibrin clot formation | 20 | 2 | 1.67 | SERPINE2; THBD | 2 | 1.18 | F10; SERPINA5 | 0 | 0.00 | | 0 | 0.00 | | 0 | 0.00 | | 2 | 2.84 | SERPINE2; THBD |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| dorsal ventral axis specification: GO | 20 | 2 | 1.67 | MDFI; RGS20 | 3 | 1.77 | CXXC4; EGF; PAX6 | 0 | 0.00 | | 0 | 0.00 | | 1 | 1.27 | EGF | 2 | 2.84 | MDFI; RGS20 |
| endoplasmic reticulum calcium ion homeostasis: GO | 20 | 2 | 1.67 | BAK1; TGM2 | 2 | 1.18 | ATP2A1; BCL2 | 0 | 0.00 | | 0 | 0.00 | | 1 | 1.27 | BCL2 | 2 | 2.84 | BAK1; TGM2 |
| hyaluronic acid binding: GO | 20 | 2 | 1.67 | C1QBP; HMMR | 2 | 1.18 | BCAN; HAPLN2 | 0 | 0.00 | | 0 | 0.00 | | 0 | 0.00 | | 2 | 2.84 | HAPLN3; HMMR |
| m band: GO | 20 | 2 | 1.67 | ENO1; MYOM3 | 5 | 2.95 | ANK2; CMYA5; MYOM1; MYOM2; OBSCN | 0 | 0.00 | | 0 | 0.00 | | 2 | 2.54 | MYOM1; MYOM2 | 2 | 2.84 | ENO1; MYOM3 |
| negative regulation of muscle contraction: GO | 20 | 2 | 1.67 | PTGS2; ZC3H12A | 4 | 2.36 | ADORA1; ADRA2A; ATP1A2; ATP2A1 | 0 | 0.00 | | 0 | 0.00 | | 2 | 2.54 | ADRA2A; PRKG1 | 2 | 2.84 | PTGS2; ZC3H12A |
| response to nitric oxide: GO | 20 | 2 | 1.67 | CCNA2; MMP3 | 0 | 0.00 | | 0 | 0.00 | | 0 | 0.00 | | 0 | 0.00 | | 2 | 2.84 | CCNA2; MMP3 |
| role of brca1, brca2 and atr in cancer susceptibility | 20 | 2 | 1.67 | BRCA2; CHEK1 | 0 | 0.00 | | 0 | 0.00 | | 0 | 0.00 | | 0 | 0.00 | | 2 | 2.84 | BRCA2; CHEK1 |
| synaptonemal complex organization: GO | 20 | 2 | 1.67 | PLK1; TRIP13 | 2 | 1.18 | STAG3; SYCP1 | 0 | 0.00 | | 0 | 0.00 | | 0 | 0.00 | | 2 | 2.84 | PLK1; TRIP13 |
| positive regulation of protein kinase b signaling: GO | 77 | 11 | 2.39 | C1QBP; CCL21; CCL3; FAM110C; HBEGF; HPSE; IL26; IL6; NRG1; TGFBR1; TXN | 4 | 0.61 | F10; F7; LEP; MYOC | 0 | 0.00 | | 0 | 0.00 | | 4 | 1.32 | ANGPT1; IGFBP5; MYOC; TSPYL5 | 5 | 1.84 | FAM110C; HBEGF; HPSE; NRG1; TXN |
| dna dependent atpase activity: GO | 77 | 5 | 1.09 | ANXA1; BLM; PIF1; POLQ; TOP2A | 0 | 0.00 | | 0 | 0.00 | | 0 | 0.00 | | 0 | 0.00 | | 5 | 1.84 | BLM; BRIP1; PIF1; POLQ; TOP2A |
| glycoprotein binding: GO | 98 | 7 | 1.20 | CALR; CTSB; HSPA5; | 12 | 1.44 | AGR3; CFH; DMD; F7; | 0 | 0.00 | | 0 | 0.00 | | 6 | 1.56 | CFH; FGFR1; GPC2; | 6 | 1.74 | AGRN; BMPR1B; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | ITGA3; LDLR; SDC1; SERPINA1 | | | FCN2; FGFR1; GPC2; GPC3; GPC6; HPSE2; PIP; SLIT2 | | | | | | | | | HPSE2; PIP; SLIT2 | | | HSPA5; ITGA3; LDLR; PLAT |
| ammonium ion metabolic process: GO | 164 | 13 | 1.33 | AKRIB10; AMD1; FABP5; MBOAT2; ODC1; PLA2G3; PLA2G4D; PLBD1; SGPP2; SMOX; SNCB; SRM; TH | 16 | 1.15 | ACADL; ATP2B2; CHPT1; CRAT; DHPS; DMGDH; DRD1; DRD4; GPLD1; GRIN2A; MAOA; PLA2G16; PLA2G5; PLA2G6; PON1; SNCA | 1 | 2.55 | PLA2G16 | 0 | 0.00 | | 5 | 0.77 | ACER1; DMGDH; GPLD1; HDC; SNCA | 9 | 1.56 | AKRIB10; FABP5; LPCAT1; ODC1; PLA2G3; PLA2G4D; SMOX; SNCB; TH |
| pip3 activates akt signaling | 164 | 9 | 0.92 | CBX2; CDKN1A; EREG; HBEGF; IL1RL1; MYD88; NRG1; PSMA5; PSMB6 | 7 | 0.50 | BTC; EGF; FGF1; FGFR1; FGFR3; IRS2; NRG2 | 0 | 0.00 | | 0 | 0.00 | | 3 | 0.46 | EGF; FGFR1; PREX2 | 9 | 1.56 | CBX2; CDKN1A; EREG; HBEGF; IER3; MYD88; NRG1; SNAI2; TRIB3 |
| role of lat2/ntal/lab on calcium mobilization | 164 | 9 | 0.92 | CBX2; CDKN1A; EREG; HBEGF; IL1RL1; MYD88; NRG1; PSMA5; PSMB6 | 7 | 0.50 | BTC; EGF; FGF1; FGFR1; FGFR3; IRS2; NRG2 | 0 | 0.00 | | 0 | 0.00 | | 4 | 0.62 | EGF; FGFR1; MS4A2; PREX2 | 9 | 1.56 | CBX2; CDKN1A; EREG; HBEGF; IER3; MYD88; NRG1; SNAI2; TRIB3 |
| il2rb pathway | 38 | 5 | 2.20 | IL2RA; JAK3; NMI; PPIA; SOCS3 | 1 | 0.31 | BCL2 | 0 | 0.00 | | 1 | 11.00 | IL2RA | 1 | 0.67 | BCL2 | 3 | 2.24 | E2F1; NMI; SOCS3 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| nucleoid: GO | 38 | 5 | 2.20 | DDX28; LRRC59; SLC25A5; TOP2A; VDAC1 | 1 | 0.31 | TERT | 0 | 0.00 | | 0 | 0.00 | | 0 | 0.00 | | 3 | 2.24 | DDX28; TOP2A; VDAC1 |
| cytosolic sensors of pathogen-associated dna | 38 | 4 | 1.76 | IFI16; MYD88; POLR3G; S100A12 | 0 | 0.00 | | 0 | 0.00 | | 0 | 0.00 | | 0 | 0.00 | | 3 | 2.24 | IFI16; MYD88; POLR3G |
| erbb2 signaling pathway: GO | 38 | 4 | 1.76 | EREG; HBEGF; NRAS; NRG1 | 5 | 1.55 | BTC; EGF; ERBB4; MYOC; NRG2 | 0 | 0.00 | | 0 | 0.00 | | 3 | 2.01 | EGF; ERBB4; MYOC | 3 | 2.24 | EREG; HBEGF; NRG1 |
| erbb4 pathway | 38 | 3 | 1.32 | EREG; HBEGF; NRG1 | 4 | 1.24 | BTC; ERBB4; NRG2; NRG3 | 0 | 0.00 | | 0 | 0.00 | | 1 | 0.67 | ERBB4 | 3 | 2.24 | EREG; HBEGF; NRG1 |
| regulation of dna dependent dna replication: GO | 38 | 3 | 1.32 | BLM; BRCA2; E2F7 | 2 | 0.62 | BMP5; DACH1 | 0 | 0.00 | | 0 | 0.00 | | 1 | 0.67 | DACH1 | 3 | 2.24 | BLM; BRCA2; E2F7 |
| bone mineralization: GO | 38 | 2 | 0.88 | CYP27B1; PTGS2 | 7 | 2.17 | CLEC3B; FGFR3; GPC3; LEP; PKDCC; PTH1R; WNT11 | 1 | 11.00 | CLEC3B | 0 | 0.00 | | 2 | 1.34 | PTH1R; WNT11 | 3 | 2.24 | CYP27B1; PTGS2; SBNO2 |
| negative regulation of transcription factor import into nucleus: GO | 38 | 2 | 0.88 | MDFI; ZC3H12A | 1 | 0.31 | PKD1 | 0 | 0.00 | | 0 | 0.00 | | 0 | 0.00 | | 3 | 2.24 | IL10; MDFI; ZC3H12A |
| p38 alpha beta downstream pathway | 38 | 2 | 0.88 | EIF4EBP1; PTGS2 | 3 | 0.93 | MITF; NOS2; PPARGC1A | 0 | 0.00 | | 0 | 0.00 | | 3 | 2.01 | ESR1; MITF; PPARGC1A | 3 | 2.24 | EIF4EBP1; PTGS2; RPS6KA4 |
| negative regulation of apoptotic signaling pathway: GO | 187 | 24 | 2.15 | BDKRB2; CSF2; GDNF; GSTP1; HIF1A; HMOX1; HSPH1; IFI6; IL19; IL1A; IL1B; ITGA6; MMP9; | 9 | 0.57 | AR; BCL2; BMP5; CLU; GATA1; MAPK8IP1; NOG; NOL3; TERT | 0 | 0.00 | | 2 | 4.47 | IL1B; SERPINE1 | 4 | 0.54 | BCL2; CLU; CREB3L1; CXCL12 | 10 | 1.52 | BDKRB2; GSTP1; HIF1A; HSPH1; IL19; ITGA6; NRG1; PPIF; PRELID1; SNAI2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | NRG1; PLAUR; PPIF; PRELID1; PSME3; SCG2; SERPINE1; SLC25A5; TGFBR1; TNFRSF10A; TNFSF10 | | | | | | | | | | | | | | | |
| cellular response to reactive oxygen species: GO | 99 | 9 | 1.52 | ANXA1; CCNA2; CDK1; ECT2; HIF1A; IL6; MMP3; PPIF; PRDX1 | 3 | 0.36 | PDGFD; SOD3; TPM1 | 0 | 0.00 | | 0 | 0.00 | | 1 | 0.26 | SOD3 | 6 | 1.72 | CCNA2; CDK1; ECT2; HIF1A; MMP3; PPIF |
| pyrimidine metabolism | 99 | 9 | 1.52 | CDA; CMPK2; NME1; PNP; POLR3G; RRM2; TK1; TYMP; UPP1 | 2 | 0.24 | ENTPD8; UPP2 | 0 | 0.00 | | 0 | 0.00 | | 0 | 0.00 | | 6 | 1.72 | CDA; CTPS1; PNP; POLR3G; RRM2; TK1 |
| perikaryon: GO | 99 | 7 | 1.18 | CCK; CNTNAP2; GOT2; KCNK1; NELL2; NTSR1; TH | 14 | 1.67 | CAMK2B; CTNND2; GRIK3; GRIK5; ITGA8; KCNA1; KCNA2; KCNB1; KCNB2; KCND2; PCSK2; PDE11A; PDE9A; TMEM100 | 0 | 0.00 | | 0 | 0.00 | | 4 | 1.03 | ESR1; GRIK3; KCND2; PDE9A | 6 | 1.72 | CNTNAP2; GOT2; KCNK1; NELL2; NTSR1; TH |
| metencephalon development: GO | 99 | 6 | 1.01 | CDK5R1; HSPA5; KIF14; NLGN4X; SERPINE2; | 12 | 1.43 | ATP2B2; BCL2; CBLN1; FZD4; GLI2; GRIN1; | 0 | 0.00 | | 0 | 0.00 | | 7 | 1.80 | BCL2; GLI2; LPAR1; MDK; NRXN1; PPARGC1A; | 6 | 1.72 | CDK5R1; HSPA5; KIF14; NLGN4X; SERPINE2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | WNT7A | | | KAT2A; LMX1A; NEUROD2; NRXN1; PPARGC1A; SEZ6L | | | | | | | | | SEZ6L | | | WNT7A |
| ruffle membrane: GO | 78 | 5 | 1.07 | CFL1; FERMT1; NME1; PDPN; TWF1 | 2 | 0.30 | PDE9A; TPM1 | 0 | 0.00 | | 0 | 0.00 | | 3 | 0.98 | DLC1; PDE9A; TESC | 5 | 1.82 | CFL1; EPHA2; FERMT1; SPRY4; TWF1 |
| regulation of leukocyte migration: GO | 143 | 28 | 3.28 | ANXA1; BDKRB1; C1QBP; CALR; CCL21; CCL3; CCL7; CXCL1; CXCL10; CXCL11; CXCL13; CXCL3; CXCL5; CXCL6; CXCL9; F2RL1; GREM1; HMOX1; IL1B; IL6; MSN; PTAFR; PYCARD; RAC2; S100A14; S100A7; SERPINE1; WNT5A | 8 | 0.66 | ADORA1; APOD; BMP5; EDN3; F7; PDGFD; RARRES2; SLIT2 | 0 | 0.00 | | 5 | 14.61 | CXCL5; CXCL9; IL1B; RAC2; SERPINE1 | 4 | 0.71 | CXCL12; EDN3; RARRES2; SLIT2 | 8 | 1.59 | CCL20; CXCL11; CXCL2; CXCL6; MSN; PTAFR; S100A14; WNT5A |
| mitochondrial transport: GO | 143 | 14 | 1.64 | BAK1; DYNLL1; HK2; HSPA4; PPIF; SFN; SLC25A5; TIMM13; | 5 | 0.41 | ACACB; BCL2; CAMK2A; NOL3; PRKAA2 | 0 | 0.00 | | 1 | 2.92 | GZMB | 3 | 0.53 | BCL2; BHLHA15; PRKAA2 | 8 | 1.59 | BAK1; E2F1; HK2; PPIF; SFN; VDAC1; YWHAQ; YWHAZ |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | TIMM23; TIMM8B; TP63; VDAC1; YWHAQ; YWHAZ | | | | | | | | | | | | | | | |
| isoprenoid metabolic process: GO | 121 | 15 | 2.07 | ADH7; AKRIB10; ALDH1A3; COQ2; CRABP2; HMGCR; IL1B; LRAT; LRP8; SDC1; SDR16C5; STRA6; TH; UGT1A1; UGT1A7 | 16 | 1.56 | ALDH1A1; APOE; AWAT2; CYP1A1; CYP1A2; CYP2C9; CYP2D6; GPC2; GPC3; GPC6; HMGCS2; LPL; PECR; RARRES2; RBP4; SDC2 | 1 | 3.45 | LPL | 1 | 3.45 | IL1B | 6 | 1.26 | ALDH3A2; CYP3A4; DGAT2; GPC2; HMGCS2; RARRES2 | 7 | 1.64 | AGRN; AKR1B10; CRABP2; LRAT; PDSS1; PPARD; TH |
| amino acid transport: GO | 121 | 11 | 1.52 | NTSR1; PDPN; SERINC2; SLC38A1; SLC38A5; SLC6A11; SLC7A1; SLC7A11; SLC7A5; SLC7A8; TRPC4 | 15 | 1.46 | APBA1; FOLR1; FOLR2; OCA2; RIMS1; SLC16A12; SLC17A7; SLC1A2; SLC1A6; SLC1A7; SLC6A17; SLC7A10; SLC7A14; SLC7A9; SYT1 | 0 | 0.00 | | 0 | 0.00 | | 5 | 1.05 | APBA1; RIMS1; SLC16A10; SLC1A6; SLC1A7 | 7 | 1.64 | NTSR1; SERINC2; SLC38A5; SLC6A11; SLC7A1; SLC7A11; SLC7A5 |
| alcohol catabolic process: GO | 58 | 7 | 2.02 | ADH7; AKR1B10; CYP24A1; CYP27B1; GK; NTSR1; TPI1 | 2 | 0.41 | APOE; DMGDH | 0 | 0.00 | | 0 | 0.00 | | 1 | 0.44 | DMGDH | 4 | 1.96 | AKR1B10; CYP27B1; NTSR1; TPI1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| lipid particle: GO | 58 | 5 | 1.44 | CKAP4; GAPDH; PITPNM1; RSAD2; VCP | 7 | 1.42 | CIDEC; FABP4; GOS2; HSD17B13; PLIN1; PLIN4; PLIN5 | 2 | 14.41 | CIDEC; PLIN4 | 0 | 0.00 | | 2 | 0.88 | DGAT2; SCCPDH | 4 | 1.96 | CKAP4; GAPDH; LPCAT1; PITPNM1 |
| regulation of cartilage development: GO | 58 | 4 | 1.15 | GREM1; PTHLH; TGFBR1; WNT5A | 11 | 2.24 | CHADL; FRZB; GDF5; GLI2; LEP; NOG; PKDCC; SCIN; SOX5; WNT11; ZBTB16 | 0 | 0.00 | | 0 | 0.00 | | 5 | 2.19 | CTGF; GLI2; SCIN; SHOX2; WNT11 | 4 | 1.96 | BMPR1B; PTHLH; SNAI2; WNT5A |
| morphogenesis of a branching structure: GO | 166 | 15 | 1.51 | AREG; BAK1; FOXF1; GDNF; GREM1; IL6; PGF; PRDM1; SOCS3; TBX20; TGM2; TIMELESS; TNC; TP63; WNT5A | 18 | 1.28 | ADAMTS16; BCL2; EGF; FGF1; FGFR1; GLI2; GPC3; HHIP; NOG; PKD1; PTCH1; SEMA3A; SEMA3E; SIX1; SLIT2; SOX10; SOX8; TCF21 | 0 | 0.00 | | 0 | 0.00 | | 13 | 1.99 | BCL2; EGF; ESR1; FGF2; FGFR1; FOXA1; GDF7; GLI2; MYCN; PTCH1; SEMA3E; SLIT2; SPRY1 | 9 | 1.54 | AREG; BAK1; EPHA2; IL10; SOCS3; TGM2; TIMELESS; WNT5A; WNT9B |
| retinoic acid metabolic process: GO | 21 | 6 | 4.78 | ADH7; ALDH1A3; CRABP2; LRAT; UGT1A1; UGT1A7 | 1 | 0.56 | CYP1A1 | 0 | 0.00 | | 0 | 0.00 | | 0 | 0.00 | | 2 | 2.70 | CRABP2; LRAT |
| antigen presentation folding assembly and peptide loading of class i mhc | 21 | 4 | 3.19 | CALR; HSPA5; PDIA3; TAP2 | 0 | 0.00 | | 0 | 0.00 | | 0 | 0.00 | | 0 | 0.00 | | 2 | 2.70 | HLA-G; HSPA5 |
| gamma-hexachloro-cyclohexane | 21 | 3 | 2.39 | ACP5; ALPL; CYP4F11 | 6 | 3.37 | ACP6; CYP3A5; CYP4F12; | 0 | 0.00 | | 0 | 0.00 | | 5 | 6.05 | ACP6; CYP3A4; CYP3A5; | 2 | 2.70 | ACP5; DHRS2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| degradation | | | | | | | CYP4F8; PON1; PON3 | | | | | | | | | CYP4F12; PON3 | | | |
| mast cell activation: GO | 21 | 3 | 2.39 | NR4A3; PLA2G3; S100A12 | 0 | 0.00 | | 0 | 0.00 | | 1 | 19.90 | LCP2 | 0 | 0.00 | | 2 | 2.70 | NDRG1; PLA2G3 |
| nucleobase containing small molecule interconversion: GO | 21 | 3 | 2.39 | NME1; RRM2; TXN | 0 | 0.00 | | 0 | 0.00 | | 0 | 0.00 | | 2 | 2.42 | AK7; GLRX | 2 | 2.70 | RRM2; TXN |
| acidic amino acid transport: GO | 21 | 2 | 1.59 | NTSR1; SLC7A11 | 4 | 2.25 | SLC17A7; SLC1A2; SLC1A6; SLC1A7 | 0 | 0.00 | | 0 | 0.00 | | 2 | 2.42 | SLC1A6; SLC1A7 | 2 | 2.70 | NTSR1; SLC7A11 |
| b cell homeostasis: GO | 21 | 2 | 1.59 | BAK1; HIF1A | 1 | 0.56 | BCL2 | 0 | 0.00 | | 0 | 0.00 | | 1 | 1.21 | BCL2 | 2 | 2.70 | BAK1; HIF1A |
| hedgehog 2pathway | 21 | 2 | 1.59 | PTHLH; STIL | 6 | 3.37 | BOC; CDON; GLI2; HHIP; PTCH1; PTCH2 | 0 | 0.00 | | 0 | 0.00 | | 4 | 4.84 | CDON; GLI2; PTCH1; PTCH2 | 2 | 2.70 | PTHLH; STIL |
| mating behavior: GO | 21 | 2 | 1.59 | SERPINE2; TH | 3 | 1.69 | DRD1; GRIN1; PPP1RIB | 0 | 0.00 | | 0 | 0.00 | | 0 | 0.00 | | 2 | 2.70 | SERPINE2; TH |
| membrane protein ectodomain proteolysis: GO | 21 | 2 | 1.59 | PRKCQ; PSENEN | 1 | 0.56 | P2RX7 | 0 | 0.00 | | 0 | 0.00 | | 0 | 0.00 | | 2 | 2.70 | ADAM19; PRKCQ |
| mitochondria pathway | 21 | 2 | 1.59 | BAK1; CYCS | 1 | 0.56 | BCL2 | 0 | 0.00 | | 0 | 0.00 | | 1 | 1.21 | BCL2 | 2 | 2.70 | BAK1; CYCS |
| negative regulation of peptidyl serine phosphorylation: GO | 21 | 2 | 1.59 | BAK1; BDKRB2 | 3 | 1.69 | DKK1; DMD; MLXIPL | 0 | 0.00 | | 0 | 0.00 | | 0 | 0.00 | | 2 | 2.70 | BAK1; BDKRB2 |
| positive regulation of neuroblast proliferation: GO | 21 | 2 | 1.59 | ASPM; HIF1A | 3 | 1.69 | DCT; PAX6; SOX10 | 0 | 0.00 | | 0 | 0.00 | | 0 | 0.00 | | 2 | 2.70 | ASPM; HIF1A |
| preribosome large subunit precursor: GO | 21 | 2 | 1.59 | EBNA1BP2; EIF6 | 0 | 0.00 | | 0 | 0.00 | | 0 | 0.00 | | 0 | 0.00 | | 2 | 2.70 | EBNA1BP2; EIF6 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| sialylation: GO | 21 | 2 | 1.59 | ST6GALNAC1; ST8SIA2 | 2 | 1.12 | ST6GAL2; ST6GALNAC5 | 0 | 0.00 | | 0 | 0.00 | | 1 | 1.21 | ST6GALNAC5 | 2 | 2.70 | ST6GALNAC1; ST8SIA2 |
| basal lamina: GO | 21 | 1 | 0.80 | LAMB3 | 1 | 0.56 | LAMA2 | 0 | 0.00 | | 0 | 0.00 | | 1 | 1.21 | LAMA2 | 2 | 2.70 | AGRN; LAMB3 |
| cell aggregation: GO | 21 | 1 | 0.80 | WNT7A | 4 | 2.25 | ALX1; COL11A1; MGP; PKD1 | 0 | 0.00 | | 0 | 0.00 | | 3 | 3.63 | COL11A1; CTGF; MYCN | 2 | 2.70 | BMPR1B; WNT7A |
| response to immobilization stress: GO | 21 | 1 | 0.80 | TH | 3 | 1.69 | CYP1A1; CYP1A2; REN | 0 | 0.00 | | 0 | 0.00 | | 0 | 0.00 | | 2 | 2.70 | TH; UCN2 |
| vegfr2 mediated vascular permeability | 21 | 1 | 0.80 | JUP | 0 | 0.00 | | 0 | 0.00 | | 0 | 0.00 | | 0 | 0.00 | | 2 | 2.70 | TRIB3; VAV2 |
| negative regulation of protein complex assembly: GO | 100 | 7 | 1.17 | CAPZA1; EIF4EBP1; KIF14; MEFV; PFN1; TBX20; TWF1 | 13 | 1.53 | CLU; DACT1; DKK1; FHOD3; GSN; LMOD1; SCIN; SLIT2; SNCA; SPTBN4; SVIP; TMOD1 | 0 | 0.00 | | 0 | 0.00 | | 9 | 2.29 | CAPZA3; CLU; DACT1; LMOD1; SCIN; SLIT2; SNCA; SPTBN4; SVIP | 6 | 1.70 | EIF4EBP1; KIF14; MEFV; PFN1; SGK1; TWF1 |
| regulation of meiotic cell cycle: GO | 39 | 6 | 2.57 | ASPM; CALR; CDC20; FBX05; OSM; WNT5A | 3 | 0.91 | LIF; NPM2; PIWIL2 | 0 | 0.00 | | 1 | 10.72 | OSM | 0 | 0.00 | | 3 | 2.18 | ASPM; CDC20; WNT5A |
| p53-independent dna damage response | 39 | 5 | 2.15 | CDC25A; CDC25B; CHEK1; PSMA5; PSMB6 | 0 | 0.00 | | 0 | 0.00 | | 0 | 0.00 | | 0 | 0.00 | | 3 | 2.18 | CDC25A; CDC25B; CHEK1 |
| p53-independent g1/s dna damage checkpoint | 39 | 5 | 2.15 | CDC25A; CDC25B; CHEK1; PSMA5; PSMB6 | 0 | 0.00 | | 0 | 0.00 | | 0 | 0.00 | | 0 | 0.00 | | 3 | 2.18 | CDC25A; CDC25B; CHEK1 |
| regulation of cell adhesion mediated by integrin: GO | 39 | 5 | 2.15 | CCL21; CXCL13; DPP4; PLAU; SERPINE1 | 0 | 0.00 | | 0 | 0.00 | | 1 | 10.72 | SERPINE1 | 1 | 0.65 | TESC | 3 | 2.18 | DPP4; EPHA2; SNAI2 |
| ubiquitin mediated | 39 | 5 | 2.15 | CDC25A; | 0 | 0.00 | | 0 | 0.00 | | 0 | 0.00 | | 0 | 0.00 | | 3 | 2.18 | CDC25A; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| degradation of phosphorylated cdc25a | | | | CDC25B; CHEK1; PSMA5; PSMB6 | | | | | | | | | | | | | | | CDC25B; CHEK1 |
| metabolism of fat-soluble vitamins | 39 | 4 | 1.72 | AKRIB10; LDLR; LRP8; SDC1 | 6 | 1.82 | APOE; GPC3; GPC6; RBP4; SDC2; TTPA | 0 | 0.00 | | 0 | 0.00 | | 0 | 0.00 | | 3 | 2.18 | AGRN; AKRIB10; LDLR |
| cellular response to estrogen stimulus: GO | 39 | 3 | 1.29 | CCNA2; H2AFZ; SERPINB9 | 2 | 0.61 | PPARGC1A; UGT3A2 | 0 | 0.00 | | 1 | 10.72 | SERPINB9 | 2 | 1.30 | ESR1; PPARGC1A | 3 | 2.18 | CCNA2; H2AFZ; IL10 |
| constitutive signaling by aberrant pi3k in cancer | 39 | 3 | 1.29 | EREG; HBEGF; NRG1 | 7 | 2.12 | BTC; EGF; FGF1; FGFR1; FGFR3; IRS2; NRG2 | 0 | 0.00 | | 0 | 0.00 | | 2 | 1.30 | EGF; FGFR1 | 3 | 2.18 | EREG; HBEGF; NRG1 |
| g1 phase | 39 | 3 | 1.29 | CCND2; CDKN1A; E2F3 | 0 | 0.00 | | 0 | 0.00 | | 0 | 0.00 | | 0 | 0.00 | | 3 | 2.18 | CCND2; CDKN1A; E2F1 |
| lactation: GO | 39 | 3 | 1.29 | HIF1A; HK2; NME1 | 3 | 0.91 | ATP2B2; CDO1; ERBB4 | 0 | 0.00 | | 0 | 0.00 | | 2 | 1.30 | ERBB4; SLC29A1 | 3 | 2.18 | HIF1A; HK2; XDH |
| base excision repair: GO | 39 | 2 | 0.86 | HMGA2; POLQ | 1 | 0.30 | NEIL1 | 0 | 0.00 | | 0 | 0.00 | | 0 | 0.00 | | 3 | 2.18 | HMGA2; NEIL3; POLQ |
| mammary gland morphogenesis: GO | 39 | 2 | 0.86 | AREG; WNT5A | 3 | 0.91 | GLI2; NRG3; PTCH1 | 0 | 0.00 | | 0 | 0.00 | | 4 | 2.61 | ESR1; GLI2; IGFBP5; PTCH1 | 3 | 2.18 | AREG; EPHA2; WNT5A |
| positive regulation of leukocyte chemotaxis: GO | 79 | 21 | 4.45 | C1QBP; CALR; CCL21; CCL3; CCL7; CXCL1; CXCL10; CXCL11; CXCL13; CXCL3; CXCL5; CXCL6; CXCL9; F2RL1; IL1B; IL6; RAC2; S100A14; S100A7; | 3 | 0.45 | EDN3; F7; RARRES2 | 0 | 0.00 | | 5 | 26.45 | CXCL5; CXCL9; IL1B; RAC2; SERPINE1 | 3 | 0.96 | CXCL12; EDN3; RARRES2 | 5 | 1.79 | CXCL11; CXCL2; CXCL6; S100A14; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | SERPINE1; WNT5A | | | | | | | | | | | | | | | |
| chromatin dna binding: GO | 79 | 8 | 1.69 | ACTB; GRHL3; H2AFZ; HIST1H1A; HIST1H1B; HIST1H1D; HMGA2; RCC1 | 3 | 0.45 | GATA1; PER1; PPARGC1A | 0 | 0.00 | | 0 | 0.00 | | 1 | 0.32 | PPARGC1A | 5 | 1.79 | ACTB; H2AFZ; HIST1H1B; HIST1H1D; HMGA2 |
| regulation of interleukin 8 production: GO | 59 | 8 | 2.27 | ANXA1; CAMP; CD2; F2RL1; IL1B; PYCARD; SERPINE1; WNT5A | 3 | 0.60 | ADIPOQ; ELANE; SSC5D | 1 | 7.08 | ADIPOQ | 3 | 21.25 | FFAR2; IL1B; SERPINE1 | 2 | 0.86 | ELANE; SSC5D | 4 | 1.92 | AFAP1L2; BCL3; IL10; WNT5A |
| tp53 regulates metabolic genes | 59 | 7 | 1.99 | COX7B; CYCS; PRDX1; SCO2; SFN; TIGAR; TXN | 1 | 0.20 | PRKAA2 | 0 | 0.00 | | 1 | 7.08 | TIGAR | 1 | 0.43 | PRKAA2 | 4 | 1.92 | CYCS; SCO2; SFN; TXN |
| double stranded rna binding: GO | 59 | 6 | 1.70 | DDX21; MSN; OAS1; OAS2; OAS3; OASL | 0 | 0.00 | | 0 | 0.00 | | 0 | 0.00 | | 0 | 0.00 | | 4 | 1.92 | ACTN1; DDX21; MSN; OAS1 |
| negative regulation of synaptic transmission: GO | 59 | 5 | 1.42 | EIF4A3; NLGN4X; PCDH17; PLK2; PTGS2 | 12 | 2.40 | ADIPOQ; ADORA1; CELF4; DRD1; GRIA1; GRID2IP; GRIK3; NPY5R; PLA2G6; PPP1R9A; SLC24A2; SNCA | 1 | 7.08 | ADIPOQ | 0 | 0.00 | | 4 | 1.72 | GRIA1; GRID2IP; GRIK3; SNCA | 4 | 1.92 | EIF4A3; NLGN4X; PLK2; PTGS2 |
| regulation of response to oxidative stress: GO | 59 | 5 | 1.42 | HIF1A; HSPH1; MMP3; NR4A3; TXN | 4 | 0.80 | FBLN5; NOL3; NOX1; SNCA | 0 | 0.00 | | 0 | 0.00 | | 2 | 0.86 | FBLN5; SNCA | 4 | 1.92 | HIF1A; HSPH1; MMP3; TXN |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| integrin binding: GO | 101 | 9 | 1.49 | ADAM23; CALR; CXADR; ESM1; ICAM3; ITGA3; ITGA6; ITGB6; WISP1 | 10 | 1.17 | ACTN2; ADAM11; ADAM22; EDIL3; FBLN5; FCER2; TNN; TNXB; TSPAN8; WISP2 | 0 | 0.00 | | 0 | 0.00 | | 8 | 2.01 | ADAM22; CTGF; EDIL3; FBLN1; FBLN5; TNN; TSPAN8; WISP2 | 6 | 1.68 | ACTN1; ADAM23; ICAM5; ITGA3; ITGA6; ITGB6 |
| fat cell differentiation: GO | 101 | 6 | 0.99 | HMGA2; ITGA6; LAMB3; NR4A3; PTGS2; STEAP4 | 12 | 1.40 | ADIPOQ; ADRB1; FABP4; GDF10; ID4; INHBB; PEX11A; PPARGC1A; RARRES2; SLC2A4; SOX8; TFAP2B | 1 | 4.14 | ADIPOQ | 1 | 4.14 | FFAR2 | 2 | 0.50 | PPARGC1A; RARRES2 | 6 | 1.68 | HMGA2; ITGA6; LAMB3; LRG1; PTGS2; SNAI2 |
| slc mediated transmembrane transport | 123 | 9 | 1.22 | HK2; RHCG; SLC10A6; SLC26A9; SLC28A3; SLC38A5; SLC4A8; SLC5A1; SLC6A11 | 18 | 1.73 | RHAG; SLC13A2; SLC14A2; SLC16A8; SLC17A7; SLC1A6; SLC1A7; SLC24A2; SLC26A1; SLC26A7; SLC2A4; SLC34A3; SLC4A1; SLC5A2; SLC6A2; SLC7A10; SLC9A2; SLC9A4 | 0 | 0.00 | | 0 | 0.00 | | 5 | 1.03 | SLC13A2; SLC18A2; SLCIA6; SLC1A7; SLC9A2 | 7 | 1.61 | HK2; RHCG; SLC28A3; SLC38A5; SLC4A3; SLC5A5; SLC6A11 |
| osteoblast differentiation: GO | 123 | 7 | 0.95 | ALPL; CCL3; CYP24A1; DDX21; | 12 | 1.15 | AMELX; BMP3; FGF9; GDF10; GLI2; | 0 | 0.00 | | 0 | 0.00 | | 12 | 2.48 | CHRD; CREB3L1; ESR1; GLI2; | 7 | 1.61 | DDX21; EPHA2; IGFBP3; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | GJA1; PTHLH; TNC | | | LRRC17; MYOC; NOG; PCP4; PTH1R; SOX8; WNT11 | | | | | | | | | IGFBP5; ITGA11; LRRC17; MYOC; PTH1R; SHOX2; TMEM119; WNT11 | | | JUNB; PTHLH; SNAI2; TPM4 |
| reg gr pathway | 80 | 12 | 2.51 | CDK5R1; CDKN1A; CSF2; IFNG; IL6; KRT14; KRT17; KRT5; MMP1; SELE; SFN; STAT1 | 1 | 0.15 | IL5 | 0 | 0.00 | | 1 | 5.22 | SELE | 0 | 0.00 | | 5 | 1.77 | CDK5R1; CDKN1A; KRT5; SFN; SGK1 |
| response to fatty acid: GO | 80 | 8 | 1.67 | CCL21; CCNB1; IL1B; NME1; PTAFR; PTGS2; TNC; ZC3H12A | 7 | 1.03 | ADCY6; ADIPOQ; HMGCS2; PDK4; PON1; PPARGC1A; PRKAA2 | 1 | 5.22 | ADIPOQ | 2 | 10.45 | FFAR2; IL1B | 10 | 3.18 | CTGF; DGAT2; HMGCS2; P2RY4; PDK3; PDK4; PPARGC1A; PRKAA2; PTGDR; PTGFR | 5 | 1.77 | CCNB1; E2F1; PTAFR; PTGS2; ZC3H12A |
| regulation of release of cytochrome c from mitochondria: GO | 40 | 8 | 3.35 | BAK1; FAM162A; MMP9; PLAUR; PPIF; PRELID1; PYCARD; TNFSF10 | 2 | 0.59 | NOL3; PLA2G6 | 0 | 0.00 | | 0 | 0.00 | | 0 | 0.00 | | 3 | 2.13 | BAK1; PPIF; PRELID1 |
| ncam1 interactions | 40 | 4 | 1.67 | ARTN; GDNF; PRNP; ST8SIA2 | 5 | 1.47 | CACNA1H; CACNB1; COL9A2; GFRA1; NCAM1 | 0 | 0.00 | | 0 | 0.00 | | 5 | 3.18 | CACNA1G; CACNA1H; CACNB1; GULP1; NCAM1 | 3 | 2.13 | AGRN; ARTN; ST8SIA2 |
| chrebp2 pathway | 40 | 3 | 1.26 | PPP2R2C; YWHAQ; YWHAZ | 4 | 1.18 | ML XIPL; PPP2R2B; PRKAA2; PRKAR2B | 1 | 10.45 | PRKAR2B | 0 | 0.00 | | 1 | 0.64 | PRKAA2 | 3 | 2.13 | PPP2R2C; YWHAQ; YWHAZ |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| peptide hormone metabolism | 40 | 3 | 1.26 | DPP4; ERO1A; SPC25 | 4 | 1.18 | AGT; INHBB; PAX6; REN | 0 | 0.00 | | 0 | 0.00 | | 2 | 1.27 | CPE; CTSG | 3 | 2.13 | DPP4; ERO1A; SPC25 |
| exonuclease activity active with either ribo or deoxyribonucleic acids and producing 5 phospho-monoesters: GO | 40 | 2 | 0.84 | EXO1; ISG20 | 0 | 0.00 | | 0 | 0.00 | | 0 | 0.00 | | 0 | 0.00 | | 3 | 2.13 | EXO1; FEN1; TREX2 |
| negative regulation of fat cell differentiation: GO | 40 | 2 | 0.84 | IL6; WNT5A | 6 | 1.77 | ADIPOQ; C1QL4; ENPP1; ID4; RUNXIT1; ZFPM2 | 1 | 10.45 | ADIPOQ | 0 | 0.00 | | 2 | 1.27 | RUNX1T1; ZFPM2 | 3 | 2.13 | E2F1; TRIB3; WNT5A |
| gab1 signalosome | 169 | 9 | 0.89 | CBX2; CDKN1A; EREG; HBEGF; IL1RL1; MYD88; NRG1; PSMA5; PSMB6 | 7 | 0.49 | BTC; EGF; FGF1; FGFR1; FGFR3; IRS2; NRG2 | 0 | 0.00 | | 0 | 0.00 | | 3 | 0.45 | EGF; FGFR1; PREX2 | 9 | 1.51 | CBX2; CDKN1A; EREG; HBEGF; IER3; MYD88; NRG1; SNAI2; TRIB3 |
| positive regulation of cellular amide metabolic process: GO | 102 | 11 | 1.80 | C1QBP; DEFB103A; DEFB103B; EIF4A3; EIF5A; EIF5AL1; IL6; KRT17; NPM1; PTAFR; ZC3H12A | 7 | 0.81 | APOE; CLU; CPEB1; LRRTM3; PIWIL2; PLA2G6; SAMD4A | 0 | 0.00 | | 0 | 0.00 | | 4 | 1.00 | CLU; CPEB1; ESR1; RBMS3 | 6 | 1.67 | BCL3; EIF4A3; MPV17L2; NPM1; PTAFR; ZC3H12A |
| glycan structures - biosynthesis 1 | 102 | 7 | 1.15 | CHST1; GALNT14; GALNT6; HS3ST1; HS3ST3A1; | 10 | 1.16 | A4GNT; CHST12; EXTL 1; GALNT13; GALNT8; | 0 | 0.00 | | 0 | 0.00 | | 2 | 0.50 | CHST12; UST | 6 | 1.67 | CHST1; GALNT14; GALNT6; HS3ST1; HS3ST3A1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | HS3ST3B1; ST6GALNAC1 | | | GALNTL6; HS3ST2; HS3ST5; HS6ST3; UST | | | | | | | | | | | | ST6GALNAC1 |
| transcriptional repressor activity rna polymerase ii core promoter proximal region sequence specific binding: GO | 102 | 4 | 0.66 | HMGA2; IFI16; MXD1; PRDM1 | 8 | 0.93 | BHLHE41; DACH1; GATA1; MLXIPL; TBX15; TCF21; ZFPM2; ZNF536 | 0 | 0.00 | | 0 | 0.00 | | 5 | 1.25 | BHLHE41; DACH1; TBX15; ZBTB20; ZFPM2 | 6 | 1.67 | ASCL2; HMGA2; IFI16; KLF16; MXD1; SNAI2 |
| regulation of neurological system process: GO | 60 | 8 | 2.23 | CCK; CCL3; IFNG; IL6; NRG1; NTSR1; PTAFR; TNFRSF21 | 6 | 1.18 | ADORA1; AGT; CARTPT; FGFR1; GRIN2A; TMEM100 | 0 | 0.00 | | 0 | 0.00 | | 1 | 0.42 | FGFR1 | 4 | 1.89 | IL10; NRG1; NTSR1; PTAFR |
| glycolipid biosynthetic process: GO | 60 | 7 | 1.95 | B3GNT5; CWH43; PIGW; PLAUR; ST6GALNAC1; ST8SIA2; UGCG | 2 | 0.39 | GAL3ST1; ST6GALNAC5 | 0 | 0.00 | | 0 | 0.00 | | 2 | 0.85 | GAL3ST4; ST6GALNAC5 | 4 | 1.89 | B3GNT5; PIGW; ST6GALNAC1; ST8SIA2 |
| regulation of osteoclast differentiation: GO | 60 | 7 | 1.95 | CA2; CCL3; IFNG; IL12B; IL20; LTF; UBASH3B | 4 | 0.79 | CARTPT; CLDN18; LRRC17; MITF | 0 | 0.00 | | 0 | 0.00 | | 3 | 1.27 | CLDN18; LRRC17; MITF | 4 | 1.89 | CA2; IL20; LTF; UBASH3B |
| cellular response to hydrogen peroxide: GO | 60 | 6 | 1.67 | ANXA1; CDK1; ECT2; HIF1A; IL6; PPIF | 1 | 0.20 | PDGFD | 0 | 0.00 | | 0 | 0.00 | | 0 | 0.00 | | 4 | 1.89 | CDK1; ECT2; HIF1A; PPIF |
| pi3k/akt signaling in cancer | 60 | 4 | 1.12 | CDKN1A; EREG; HBEGF; NRG1 | 7 | 1.38 | BTC; EGF; FGF1; FGFR1; FGFR3; IRS2; NRG2 | 0 | 0.00 | | 0 | 0.00 | | 2 | 0.85 | EGF; FGFR1 | 4 | 1.89 | CDKN1A; EREG; HBEGF; NRG1 |
| benzene containing compound metabolic | 22 | 6 | 4.56 | GOT2; IDO1; KYNU; TDO2; TH; | 6 | 3.22 | CYP17A1; CYP4B1; GSTM2; | 0 | 0.00 | | 1 | 19.00 | TDO2 | 2 | 2.31 | CYP4B1; PON3 | 2 | 2.58 | GOT2; TH |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| process: GO | | | | UGT1A1 | | | GSTM3; HAAO; PON3 | | | | | | | | | | | | |
| regulation of interleukin 17 production: GO | 22 | 6 | 4.56 | IFNG; IL12B; IL36RN; MYD88; PRKCQ; PRNP | 0 | 0.00 | | 0 | 0.00 | | 0 | 0.00 | | 0 | 0.00 | | 2 | 2.58 | MYD88; PRKCQ |
| release of cytochrome c from mitochondria: GO | 22 | 6 | 4.56 | BAK1; BCL2A1; CCK; GGCT; IFI6; SFN | 2 | 1.07 | BCL2; CLU | 0 | 0.00 | | 0 | 0.00 | | 2 | 2.31 | BCL2; CLU | 2 | 2.58 | BAK1; SFN |
| transferase activity transferring amino acyl groups: GO | 22 | 5 | 3.80 | CHAC1; CHAC2; GGCT; TGM1; TGM2 | 2 | 1.07 | EPB42; GGT7 | 0 | 0.00 | | 0 | 0.00 | | 0 | 0.00 | | 2 | 2.58 | TGM1; TGM2 |
| wide pore channel activity: GO | 22 | 5 | 3.80 | GJA1; GJB2; GJB3; PANX1; VDAC1 | 0 | 0.00 | | 0 | 0.00 | | 1 | 19.00 | AQP9 | 0 | 0.00 | | 2 | 2.58 | PANX1; VDAC1 |
| glycosamino-glycan degradation | 22 | 4 | 3.04 | HPSE; HS3ST3A1; HS3ST3B1; HYAL3 | 2 | 1.07 | HPSE2; IDUA | 0 | 0.00 | | 0 | 0.00 | | 1 | 1.15 | HPSE2 | 2 | 2.58 | HPSE; HS3ST3A1 |
| neuroactive ligand receptor interaction | 22 | 4 | 3.04 | CHRNA3; CHRNA6; CHRNA9; PRSS3 | 1 | 0.54 | CHRNA2 | 0 | 0.00 | | 0 | 0.00 | | 0 | 0.00 | | 2 | 2.58 | CHRNA6; PRSS3 |
| phosphatidyl-ethanolamine acyl chain remodeling: GO | 22 | 4 | 3.04 | MBOAT2; PLA2G3; PLA2G4D; PLBD1 | 3 | 1.61 | PLA2G16; PLA2G5; PLA2G6 | 1 | 19.00 | PLA2G16 | 0 | 0.00 | | 0 | 0.00 | | 2 | 2.58 | PLA2G3; PLA2G4D |
| raf-independent mapk1/3 activation | 22 | 4 | 3.04 | CDK1; DUSP6; DUSP9; IL6 | 0 | 0.00 | | 0 | 0.00 | | 0 | 0.00 | | 0 | 0.00 | | 2 | 2.58 | CDK1; DUSP6 |
| regulation of response to interferon gamma: GO | 22 | 4 | 3.04 | IFNG; PARP9; SOCS3; STAT1 | 0 | 0.00 | | 0 | 0.00 | | 0 | 0.00 | | 0 | 0.00 | | 2 | 2.58 | PARP9; SOCS3 |
| association of | 22 | 3 | 2.28 | CCNE1; | 0 | 0.00 | | 0 | 0.00 | | 0 | 0.00 | | 0 | 0.00 | | 2 | 2.58 | CCT5; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| tric/cct with target proteins during biosynthesis | | | | CCT5; CCT6A | | | | | | | | | | | | | | | NOP56 |
| detection of mechanical stimulus involved in sensory perception: GO | 22 | 3 | 2.28 | CHRNA9; NTRK1; SERPINE2 | 5 | 2.68 | ATP2B2; COL11A1; KCNA1; PDZD7; TMC2 | 0 | 0.00 | | 0 | 0.00 | | 3 | 3.46 | COL11A1; PDZD7; PIEZO2 | 2 | 2.58 | SERPINE2; TMC1 |
| ovarian tumor domain proteases | 22 | 3 | 2.28 | CAP1; CDK1; YOD1 | 0 | 0.00 | | 0 | 0.00 | | 0 | 0.00 | | 0 | 0.00 | | 2 | 2.58 | CAP1; CDK1 |
| regulation of cellular respiration: GO | 22 | 3 | 2.28 | HIF1A; PRELID1; VCP | 3 | 1.61 | NOS2; PPARGC1A; SNCA | 0 | 0.00 | | 0 | 0.00 | | 2 | 2.31 | PPARGC1A; SNCA | 2 | 2.58 | HIF1A; PRELID1 |
| regulation of epidermal growth factor activated receptor activity: GO | 22 | 3 | 2.28 | EPGN; EREG; TGFA | 3 | 1.61 | ADORA1; ADRA2A; EGF | 0 | 0.00 | | 0 | 0.00 | | 2 | 2.31 | ADRA2A; EGF | 2 | 2.58 | EREG; TGFA |
| regulation of hair cycle: GO | 22 | 3 | 2.28 | CDH3; HPSE; KRT17 | 3 | 1.61 | FA2H; PER1; TERT | 0 | 0.00 | | 0 | 0.00 | | 0 | 0.00 | | 2 | 2.58 | HPSE; TRPV3 |
| regulation of osteoblast proliferation: GO | 22 | 3 | 2.28 | GREM1; HPSE; LTF | 3 | 1.61 | BCL2; GATA1; SOX8 | 0 | 0.00 | | 0 | 0.00 | | 2 | 2.31 | BCL2; TMEM119 | 2 | 2.58 | HPSE; LTF |
| rho gtpases activate wasps and waves | 22 | 3 | 2.28 | ACTB; ACTR3; ARPC1A | 0 | 0.00 | | 0 | 0.00 | | 0 | 0.00 | | 0 | 0.00 | | 2 | 2.58 | ACTB; ARPC1A |
| somatic stem cell division: GO | 22 | 3 | 2.28 | ASPM; RAB10; WNT7A | 3 | 1.61 | DCT; FGFR1; SOX5 | 0 | 0.00 | | 0 | 0.00 | | 2 | 2.31 | FGFR1; FZD7 | 2 | 2.58 | ASPM; WNT7A |
| anion anion antiporter activity: GO | 22 | 2 | 1.52 | SLC26A9; SLC7A11 | 5 | 2.68 | SLC22A9; SLC26A1; SLC26A5; SLC26A7; SLC4A1 | 0 | 0.00 | | 0 | 0.00 | | 0 | 0.00 | | 2 | 2.58 | SLC26A6; SLC7A11 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| class b/2 (secretin family receptors) | 22 | 2 | 1.52 | PTHLH; WNT5A | 1 | 0.54 | FZD4 | 0 | 0.00 | | 0 | 0.00 | | 2 | 2.31 | FZD7; GNG11 | 2 | 2.58 | PTHLH; WNT5A |
| embryonic placenta morphogenesis: GO | 22 | 2 | 1.52 | GJB5; SOCS3 | 0 | 0.00 | | 1 | 19.00 | CDKN1C | 0 | 0.00 | | 0 | 0.00 | | 2 | 2.58 | IL10; SOCS3 |
| ferrous iron binding: GO | 22 | 2 | 1.52 | ACP5; TH | 4 | 2.15 | CDO1; HAAO; SNCA; TF | 0 | 0.00 | | 0 | 0.00 | | 1 | 1.15 | SNCA | 2 | 2.58 | ACP5; TH |
| plasma lipoprotein clearance | 22 | 2 | 1.52 | LDLR; PCSK9 | 3 | 1.61 | APOC1; APOE; SOAT2 | 0 | 0.00 | | 0 | 0.00 | | 0 | 0.00 | | 2 | 2.58 | LDLR; PCSK9 |
| positive regulation of transcription from rna polymerase ii promoter in response to stress: GO | 22 | 2 | 1.52 | HIF1A; HSPA5 | 0 | 0.00 | | 0 | 0.00 | | 0 | 0.00 | | 1 | 1.15 | CREB3L1 | 2 | 2.58 | HIF1A; HSPA5 |
| epha-mediated growth cone collapse | 22 | 1 | 0.76 | SHB | 1 | 0.54 | MYL9 | 0 | 0.00 | | 0 | 0.00 | | 0 | 0.00 | | 2 | 2.58 | EPHA2; SHB |
| regulation of generation of precursor metabolites and energy: GO | 81 | 7 | 1.45 | GADD45GIP1; HIF1A; PGAM1; PHLDA2; PPIF; PRELID1; VCP | 11 | 1.60 | ENPP1; GCGR; GPD1; IRS2; MLXIPL; NOS2; P2RX7; PPARGC1A; PRKAA2; SNCA; SORBS1 | 1 | 5.16 | GPD1 | 0 | 0.00 | | 3 | 0.94 | PPARGC1A; PRKAA2; SNCA | 5 | 1.75 | HIF1A; PGAM1; PHLDA2; PPIF; PRELID1 |
| negative regulation of intrinsic apoptotic signaling pathway: GO | 81 | 6 | 1.24 | BDKRB2; HIF1A; HSPH1; MMP9; PLAUR; PPIF | 4 | 0.58 | BCL2; CLU; MAPK8IP1; NOL3 | 0 | 0.00 | | 0 | 0.00 | | 4 | 1.25 | BCL2; CLU; CREB3L1; CXCL12 | 5 | 1.75 | BDKRB2; HIF1A; HSPH1; PPIF; SNAI2 |
| endocytic vesicle membrane: GO | 147 | 11 | 1.25 | ANXA3; AP1S3; | 15 | 1.20 | ATP6V0A4; ATP6V0E2; | 1 | 2.84 | GRIA4 | 2 | 5.69 | ANXA3; RAC2 | 7 | 1.21 | ATP6V0A4; ATP6V0E2; | 8 | 1.54 | AP1S3; HBEGF; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | FCGR1A; HBEGF; LDLR; RAB10; RAB31; RAB38; RAC2; WNT5A; WNT7A | | | CAMK2A; CAMK2B; CD207; CLVS1; CLVS2; COLEC12; FZD4; GRIA1; GRIA2; GRIA4; MARCO; PTCH1; RAB9B | | | | | | | | | CD207; GRIA1; GRIA2; HLA-DQB2; PTCH1 | | | HLA-G; LDLR; RAB31; RAB38; WNT5A; WNT7A |
| negative regulation of cellular catabolic process: GO | 147 | 8 | 0.91 | BUB1; BUB1B; CENPF; LAMP3; MAD2L1; PBK; PLK1; TTK | 14 | 1.12 | ACACB; APOC1; BCL2; CNR1; GPLD1; LEP; LEPR; NRBP2; PLIN5; PPARGC1A; SNCA; SVIP; TIMP3; TIMP4 | 0 | 0.00 | | 1 | 2.84 | LAMP3 | 5 | 0.86 | BCL2; GPLD1; PPARGC1A; SNCA; SVIP | 8 | 1.54 | BUB1; BUB1B; CENPF; IL10; MAD2L1; PBK; PLK1; TTK |
| negative regulation of catabolic process: GO | 193 | 13 | 1.13 | BUB1; BUB1B; CENPF; HCAR2; IL1B; LAMP3; MAD2L1; NRG1; PBK; PLK1; SERPINE2; TTK; YOD1 | 18 | 1.10 | ACACB; ADORA1; ADRA2A; APOC1; BCL2; CNR1; GPLD1; GRIN2A; LEP; LEPR; NOS2; NRBP2; PLIN5; PPARGC1A; SNCA; SVIP; TIMP3; TIMP4 | 0 | 0.00 | | 3 | 6.50 | HCAR2; IL1B; LAMP3 | 6 | 0.79 | ADRA2A; BCL2; GPLD1; PPARGC1A; SNCA; SVIP | 10 | 1.47 | BUB1; BUB1B; CENPF; IL10; MAD2L1; NRG1; PBK; PLK1; SERPINE2; TTK |
| positive regulation of binding: GO | 125 | 10 | 1.34 | ENO1; HMGA2; MMP9; | 9 | 0.85 | DACT1; EGF; HAND2; KAT2A; | 0 | 0.00 | | 0 | 0.00 | | 3 | 0.61 | DACT1; EGF; HAND2 | 7 | 1.59 | ENO1; HMGA2; PLK2; RAN; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline: Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo: Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo: Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | NME1; PLAUR; PLK2; RALB; RAN; TXN; WNT5A | | | MYOCD; PKD1; PON1; SPAG8; TERT | | | | | | | | | | | | TRIB3; TXN; WNT5A |
| signaling by erbb2 | 103 | 6 | 0.97 | CDK1; CDKN1A; EREG; HBEGF; NRAS; NRG1 | 9 | 1.03 | ADCY2; ADCY5; ADCY6; ADCY8; BTC; EGF; ERBB4; NRG2; PRKAR2B | 1 | 4.06 | PRKAR2B | 0 | 0.00 | | 3 | 0.74 | EGF; ERBB4; PDE1A | 6 | 1.65 | CDK1; CDKN1A; EREG; HBEGF; NRG1; TRIB3 |
| er nongenomic pathway | 41 | 6 | 2.45 | GNA15; GNAI3; HBEGF; MMP9; MSN; NRAS | 1 | 0.29 | GNAZ | 0 | 0.00 | | 0 | 0.00 | | 1 | 0.62 | ESR1 | 3 | 2.07 | GNA15; HBEGF; MSN |
| cellular component disassembly involved in execution phase of apoptosis: GO | 41 | 4 | 1.63 | CLSPN; DNASE1L3; PRKCQ; TOP2A | 2 | 0.58 | ACVR1C; CECR2 | 1 | 10.19 | ACVR1C | 0 | 0.00 | | 0 | 0.00 | | 3 | 2.07 | DNASE1L3; PRKCQ; TOP2A |
| mitotic recombination: GO | 41 | 4 | 1.63 | BRCA2; GEN1; PCNA; TOP2A | 0 | 0.00 | | 0 | 0.00 | | 0 | 0.00 | | 0 | 0.00 | | 3 | 2.07 | BRCA2; FEN1; TOP2A |
| phosphatase complex: GO | 41 | 4 | 1.63 | CYCS; PPP2R2C; PPP4R1; PPP4R4 | 1 | 0.29 | PPP2R2B | 0 | 0.00 | | 0 | 0.00 | | 0 | 0.00 | | 3 | 2.07 | CYCS; PPP2R2C; PPP4R1 |
| regulation of actin dynamics for phagocytic cup formation | 41 | 4 | 1.63 | ACTB; ACTR3; ARPC1A; FCGR1A | 0 | 0.00 | | 0 | 0.00 | | 0 | 0.00 | | 1 | 0.62 | SLC29A1 | 3 | 2.07 | ACTB; ARPC1A; VAV2 |
| neuropeptide receptor activity: GO | 41 | 3 | 1.22 | NPSR1; NTSR1; QRFPR | 6 | 1.73 | GALR1; NMUR1; NPY1R; NPY5R; NPY6R; SORCS1 | 0 | 0.00 | | 0 | 0.00 | | 1 | 0.62 | NPY1R | 3 | 2.07 | NTSR1; QRFPR; SORCS2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| positive regulation of stem cell proliferation: GO | 61 | 7 | 1.92 | ASPM; FOXF1; HIF1A; HMGA2; STAT1; TP63; WNT5A | 8 | 1.55 | DCT; FGF9; FGFR1; IRS2; PAX6; SIX1; SOX10; TERT | 0 | 0.00 | | 0 | 0.00 | | 5 | 2.08 | CHRD; FGFR1; MYCN; PRRX1; SHOX2 | 4 | 1.86 | ASPM; HIF1A; HMGA2; WNT5A |
| phosphatidyl-choline metabolic process: GO | 61 | 5 | 1.37 | FABP5; MBOAT2; PLA2G3; PLA2G4D; PLBD1 | 6 | 1.16 | CHPT1; GPLD1; PLA2G16; PLA2G5; PLA2G6; PON1 | 1 | 6.85 | PLA2G16 | 0 | 0.00 | | 1 | 0.42 | GPLD1 | 4 | 1.86 | FABP5; LPCAT1; PLA2G3; PLA2G4D |
| response to osmotic stress: GO | 61 | 4 | 1.10 | BDKRB2; HIF1A; SLC2A1; TH | 3 | 0.58 | PCP4; SLC2A4; TSC22D3 | 0 | 0.00 | | 1 | 6.85 | AQP9 | 1 | 0.42 | TSC22D3 | 4 | 1.86 | BDKRB2; HIF1A; SLC2A1; TH |
| interferon gamma signaling | 82 | 13 | 2.65 | FCGR1A; GBP6; IFI30; IFNG; MT2A; OAS1; OAS2; OAS3; OASL; PTAFR; SOCS3; STAT1; TRIM14 | 5 | 0.72 | CAMK2A; CAMK2B; CES1; NCAM1; TRIM2 | 0 | 0.00 | | 1 | 5.10 | GBP1 | 3 | 0.93 | CES1; NCAM1; TRIM2 | 5 | 1.73 | GBP6; HLA-G; OAS1; PTAFR; SOCS3 |
| cellular response to interleukin 1: GO | 82 | 12 | 2.45 | CCL17; CCL18; CCL21; CCL22; CCL3; CCL7; HIF1A; HYAL3; IL6; P2RY2; PYCARD; ZC3H12A | 2 | 0.29 | CCL14; PTGIS | 0 | 0.00 | | 0 | 0.00 | | 1 | 0.31 | CCL14 | 5 | 1.73 | CCL20; HIF1A; P2RY2; RPS6KA4; ZC3H12A |
| neddylation | 126 | 9 | 1.20 | BIRC5; DTL; HIF1A; KBTBD8; LRR1; PSMA5; PSMB6; | 2 | 0.19 | HIF3A; ZBTB16 | 0 | 0.00 | | 0 | 0.00 | | 2 | 0.40 | GAN; HIF3A | 7 | 1.58 | BIRC5; CISH; DTL; HIF1A; LRR1; SOCS3; UBE2F |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | SOCS3; UBE2F | | | | | | | | | | | | | | | |
| negative regulation of dna metabolic process: GO | 104 | 9 | 1.45 | BLM; BRCA2; CDC6; GJA1; GZMA; HMGA2; PIF1; POLQ; S100A11 | 4 | 0.45 | ADIPOQ; DACH1; MAPK15; TSPYL2 | 1 | 4.02 | ADIPOQ | 0 | 0.00 | | 2 | 0.49 | DACH1; KCNK2 | 6 | 1.64 | BLM; BRCA2; CDC6; HMGA2; PIF1; POLQ |
| attenuation phase | 23 | 5 | 3.64 | FPR1; HSPA6; HSPA8; HSPH1; TNFRSF21 | 0 | 0.00 | | 0 | 0.00 | | 0 | 0.00 | | 1 | 1.10 | SLC29A1 | 2 | 2.47 | HSPA8; HSPH1 |
| response to auditory stimulus: GO | 23 | 5 | 3.64 | CNTNAP2; CXCL10; HIF1A; IL6; STRA6 | 2 | 1.03 | NRXN1; SLC26A5 | 0 | 0.00 | | 0 | 0.00 | | 2 | 2.21 | NRXN1; SLITRK6 | 2 | 2.47 | CNTNAP2; HIF1A |
| retinoic acid binding: GO | 23 | 5 | 3.64 | CRABP2; LRAT; UGT1A1; UGT1A10; UGT1A7 | 2 | 1.03 | SERPINA5; UGT2B7 | 0 | 0.00 | | 0 | 0.00 | | 0 | 0.00 | | 2 | 2.47 | CRABP2; LRAT |
| acyl chain remodelling of pe | 23 | 4 | 2.91 | MBOAT2; PLA2G3; PLA2G4D; PLBD1 | 3 | 1.54 | PLA2G16; PLA2G5; PLA2G6 | 1 | 18.17 | PLA2G16 | 0 | 0.00 | | 0 | 0.00 | | 2 | 2.47 | PLA2G3; PLA2G4D |
| positive regulation of filopodium assembly: GO | 23 | 4 | 2.91 | CCL21; FSCN1; PRKCQ; TGFBR1 | 3 | 1.54 | ESPN; NLGN1; PALM | 0 | 0.00 | | 0 | 0.00 | | 2 | 2.21 | DPYSL3; PALM | 2 | 2.47 | AGRN; PRKCQ |
| positive regulation of osteoclast differentiation: GO | 23 | 4 | 2.91 | CA2; IFNG; IL12B; IL20 | 0 | 0.00 | | 0 | 0.00 | | 0 | 0.00 | | 0 | 0.00 | | 2 | 2.47 | CA2; IL20 |
| ephb-mediated forward signaling | 23 | 3 | 2.18 | ACTB; ACTR3; ARPC1A | 2 | 1.03 | EPHB6; SDC2 | 0 | 0.00 | | 0 | 0.00 | | 0 | 0.00 | | 2 | 2.47 | ACTB; ARPC1A |
| gamma tubulin binding: GO | 23 | 3 | 2.18 | BRCA2; NME1; RACGAP1 | 0 | 0.00 | | 0 | 0.00 | | 0 | 0.00 | | 0 | 0.00 | | 2 | 2.47 | BRCA2; NDRG1 |
| negative regulation of cartilage | 23 | 3 | 2.18 | GREM1; PTHLH; | 7 | 3.59 | CHADL; FRZB; GDF5; | 0 | 0.00 | | 0 | 0.00 | | 2 | 2.21 | GLI2; WNT11 | 2 | 2.47 | PTHLH; SNAI2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| development: GO | | | | TGFBR1 | | | GLI2; LEP; NOG; WNT11 | | | | | | | | | | | | |
| nuclear euchromatin: GO | 23 | 3 | 2.18 | H2AFZ; HIST1H1A; HIST1H1D | 1 | 0.51 | PPARGC1A | 0 | 0.00 | | 0 | 0.00 | | 1 | 1.10 | PPARGC1A | 2 | 2.47 | H2AFZ; HIST1H1D |
| regulation of superoxide metabolic process: GO | 23 | 3 | 2.18 | ACP5; F2RL1; GSTP1 | 3 | 1.54 | AGT; FBLN5; PON3 | 0 | 0.00 | | 0 | 0.00 | | 2 | 2.21 | FBLN5; PON3 | 2 | 2.47 | ACP5; GSTP1 |
| response to increased oxygen levels: GO | 23 | 3 | 2.18 | CDKN1A; PLAU; WNT5A | 2 | 1.03 | CYP1A1; NOX1 | 0 | 0.00 | | 0 | 0.00 | | 0 | 0.00 | | 2 | 2.47 | CDKN1A; WNT5A |
| snorna binding: GO | 23 | 3 | 2.18 | DDX21; ISG20; NOP10 | 0 | 0.00 | | 0 | 0.00 | | 0 | 0.00 | | 0 | 0.00 | | 2 | 2.47 | DDX21; NOP56 |
| establishment of mitotic spindle localization: GO | 23 | 2 | 1.46 | CENPA; NDC80 | 1 | 0.51 | PAX6 | 0 | 0.00 | | 0 | 0.00 | | 1 | 1.10 | SPRY1 | 2 | 2.47 | CENPA; NDC80 |
| growth hormone receptor signaling | 23 | 2 | 1.46 | SOCS3; STAT1 | 2 | 1.03 | GHR; IRS2 | 1 | 18.17 | GHR | 0 | 0.00 | | 0 | 0.00 | | 2 | 2.47 | CISH; SOCS3 |
| negative regulation of steroid metabolic process: GO | 23 | 2 | 1.46 | CYP27B1; UGT1A1 | 2 | 1.03 | APOE; BMP5 | 0 | 0.00 | | 0 | 0.00 | | 0 | 0.00 | | 2 | 2.47 | CYP27B1; SNAI2 |
| synaptic vesicle recycling: GO | 23 | 2 | 1.46 | STON2; WNT7A | 2 | 1.03 | SNCA; SYT1 | 0 | 0.00 | | 0 | 0.00 | | 1 | 1.10 | SNCA | 2 | 2.47 | STON2; WNT7A |
| cell substrate adherens junction assembly: GO | 23 | 1 | 0.73 | RHOD | 4 | 2.05 | ACTN2; ARHGAP6; BCL2; SORBS1 | 0 | 0.00 | | 0 | 0.00 | | 2 | 2.21 | BCL2; DLC1 | 2 | 2.47 | ACTN1; RHOD |
| cellular response to epidermal growth factor stimulus: GO | 23 | 1 | 0.73 | GSTP1 | 0 | 0.00 | | 0 | 0.00 | | 0 | 0.00 | | 0 | 0.00 | | 2 | 2.47 | GSTP1; SNAI2 |
| mitogen activated protein kinase binding: GO | 23 | 1 | 0.73 | PTAFR | 1 | 0.51 | PLCB4 | 0 | 0.00 | | 0 | 0.00 | | 1 | 1.10 | PLCB4 | 2 | 2.47 | PTAFR; RPS6KA4 |
| cmyb pathway | 83 | 7 | 1.41 | CCNB1; CDKN1A; H2AFZ; | 5 | 0.71 | BCL2; CA1; CD34; ELANE; | 0 | 0.00 | | 1 | 5.03 | LYZ | 4 | 1.22 | BCL2; CA1; CD34; ELANE | 5 | 1.71 | CCNB1; CDKN1A; H2AFZ; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | HSPA8; LYZ; NRAS; PTGS2 | | | GATA1 | | | | | | | | | | | | HSPA8; PTGS2 |
| damaged dna binding: GO | 62 | 4 | 1.08 | H2AFX; PCNA; POLQ; TP63 | 2 | 0.38 | CRY2; NEIL1 | 0 | 0.00 | | 0 | 0.00 | | 1 | 0.41 | CRY2 | 4 | 1.83 | FEN1; H2AFX; NEIL3; POLQ |
| negative regulation of cytokine production: GO | 196 | 27 | 2.31 | ACP5; ANXA1; CIQBP; CD274; CDH3; F2RL1; GSTP1; HMOX1; IDO1; IFNG; IL12B; IL1RL1; IL36RN; IL6; ISG15; JAK3; LTF; MEFV; NMI; PGLYRP2; PRNP; PYCARD; SLAMF1; SRGN; TNFRSF21; TNFRSF9; ZC3H12A | 8 | 0.48 | ADIPOQ; APOD; CD34; ELANE; INHBB; SCGB1A1; SSC5D; WNT11 | 1 | 2.13 | ADIPOQ | 2 | 4.26 | GBP1; ISG15 | 6 | 0.78 | ANGPT1; CD34; ELANE; FBLN1; SSC5D; WNT11 | 10 | 1.45 | ACP5; BCL3; CD83; GSTP1; IL10; LTF; MEFV; NMI; RPS6KA4; ZC3H12A |
| upa upar pathway | 42 | 9 | 3.59 | FPR1; FPR3; ITGA3; MMP12; MMP3; MMP9; PLAU; PLAUR; SERPINE1 | 3 | 0.84 | ELANE; GPLD1; PDGFD | 0 | 0.00 | | 1 | 9.95 | SERPINE1 | 3 | 1.81 | CTSG; ELANE; GPLD1 | 3 | 2.03 | FPR2; ITGA3; MMP3 |
| ribosome binding: GO | 42 | 7 | 2.79 | C1QBP; EIF2S1; EIF5A; EIF5AL1; | 1 | 0.28 | CPEB1 | 0 | 0.00 | | 0 | 0.00 | | 1 | 0.60 | CPEB1 | 3 | 2.03 | EIF6; HSPA5; ZC3H12A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | EIF6; HSPA5; ZC3H12A | | | | | | | | | | | | | | | |
| cdt1 association with the cdc6: orc: origin complex | 42 | 5 | 1.99 | CDC6; ORC1; ORC6; PSMA5; PSMB6 | 0 | 0.00 | | 0 | 0.00 | | 0 | 0.00 | | 0 | 0.00 | | 3 | 2.03 | CDC6; ORC1; ORC6 |
| cellular iron ion homeostasis: GO | 42 | 5 | 1.99 | HIF1A; HMOX1; HMOX2; LCN2; LTF | 8 | 2.25 | ALAS2; CP; CYBRD1; HAMP; SCARA5; SLC22A17; TF; TMPRSS6 | 0 | 0.00 | | 0 | 0.00 | | 5 | 3.02 | CP; CYBRD1; SCARA5; SLC22A17; SLC40A1 | 3 | 2.03 | HIF1A; HMOX2; LTF |
| genitalia development: GO | 42 | 5 | 1.99 | BAK1; GJB2; STRA6; TP63; WNT5A | 5 | 1.40 | BMP5; LHCGR; MERTK; PKD1; RBP4 | 0 | 0.00 | | 0 | 0.00 | | 1 | 0.60 | ESR1 | 3 | 2.03 | BAK1; WNT5A; WNT9B |
| negative regulation of leukocyte apoptotic process: GO | 42 | 5 | 1.99 | CCL21; HIF1A; IDO1; JAK3; PRKCQ | 6 | 1.69 | GPAM; IRS2; MERTK; PIP; RORC; TSC22D3 | 1 | 9.95 | GPAM | 0 | 0.00 | | 4 | 2.42 | CXCL12; PIP; SLC46A2; TSC22D3 | 3 | 2.03 | AURKB; HIF1A; PRKCQ |
| regulation of chondrocyte differentiation: GO | 42 | 3 | 1.20 | GREM1; PTHLH; TGFBR1 | 7 | 1.97 | CHADL; GDF5; GLI2; PKDCC; SCIN; SOX5; ZBTB16 | 0 | 0.00 | | 0 | 0.00 | | 4 | 2.42 | CTGF; GLI2; SCIN; SHOX2 | 3 | 2.03 | BMPR1B; PTHLH; SNAI2 |
| neuron migration: GO | 105 | 9 | 1.43 | ASPM; CCK; CCR4; CDK5R1; CXCR4; FBXO45; GJA1; ITGA3; TBX20 | 15 | 1.69 | DCLK1; DCX; DRD1; DRGX; FEZF2; FGFR1; GFRA3; MAPT; NDNF; NTRK3; PAX6; RELN; SEMA3A; SOX1; SPOCK1 | 0 | 0.00 | | 0 | 0.00 | | 9 | 2.18 | CHL1; CXCL12; DCLK1; FGFR1; MAPT; NDNF; PRKG1; RELN; SPOCK1 | 6 | 1.62 | ASPM; CDK5R1; FBXO45; ITGA3; MARK1; NAV1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| amino acid binding: GO | 105 | 4 | 0.64 | GOT2; HSPA8; TDO2; TH | 12 | 1.35 | ALAS2; ANXA13; FOLR1; FOLR2; GCHFR; GLRB; GRIN1; GRM7; JPH2; NOS2; SCIN; SYT1 | 0 | 0.00 | | 1 | 3.98 | TDO2 | 3 | 0.73 | ANXA9; GLRB; SCIN | 6 | 1.62 | GLDC; GOT2; HSPA8; MARK1; NAGS; TH |
| antigen processing and presentation of peptide antigen: GO | 173 | 20 | 1.93 | AP1S3; CALR; CENPE; DYNLL1; FCGR1A; IFI30; KIF11; KIF15; KIF18A; KIF23; KIF2C; KIF4A; PDIA3; PSMA4; PSMA5; PSMB6; PSMD1; PSME3; RACGAP1; TAP2 | 3 | 0.20 | CD207; CTSF; DYNC1I1 | 0 | 0.00 | | 0 | 0.00 | | 3 | 0.44 | ABCB5; CD207; HLA-DQB2 | 9 | 1.48 | AP1S3; CENPE; HLA-G; KIF11; KIF15; KIF18A; KIF23; KIF2C; KIF4A |
| downstream signaling events of b cell receptor (bcr) | 173 | 10 | 0.97 | CBX2; CDKN1A; EREG; HBEGF; IL1RL1; MYD88; NRAS; NRG1; PSMA5; PSMB6 | 7 | 0.48 | BTC; EGF; FGF1; FGFR1; FGFR3; IRS2; NRG2 | 0 | 0.00 | | 0 | 0.00 | | 3 | 0.44 | EGF; FGFR1; PREX2 | 9 | 1.48 | CBX2; CDKN1A; EREG; HBEGF; IER3; MYD88; NRG1; SNAI2; TRIB3 |
| positive regulation of developmental | 150 | 10 | 1.12 | CCNB1; CDK1; CRABP2; | 20 | 1.57 | ACACB; BCL2; C3; CACNA2D2; | 2 | 5.57 | GHR; GPAM | 0 | 0.00 | | 11 | 1.86 | BCL2; C3; CACNA2D2; CXCL12; | 8 | 1.51 | AGRN; CCNB1; CDK1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| growth: GO | | | | LPAR3; NRG1; PPIB; SASH3; TBX20; TNFRSF12A; UNC13A | | | CDH4; CPNE9; DIO3; ERBB4; FGF9; FGFR1; GHR; GPAM; LEP; MAPT; NTRK3; RIMS1; SPTBN4; SYT1; SYT17; TBX5 | | | | | | | | | ERBB4; FGF2; FGFR1; MAPT; RIMS1; SPTBN4; SYT17 | | | CRABP2; NRG1; PPARD; SOX15; UNC13A |
| response to insulin: GO | 197 | 11 | 0.93 | EIF4EBP1; GGH; GSTP1; HIF1A; IL6; NAMPT; PCSK9; PRKCQ; RAB10; RAB31; SOCS3 | 24 | 1.44 | ABCC8; ADIPOQ; ALDOB; ATP6V0A4; ATP6V0E2; ATP6V1B1; CPEB1; DRD1; EEF2K; ENPP1; GPAM; GPLD1; HDAC5; HMGCS2; INHBB; IRS2; IRS4; LEP; PCK1; PDK4; PFKFB1; SLC2A4; SORBS1 | 4 | 8.49 | ACVR1C; ADIPOQ; GPAM; HSD11B2 | 0 | 0.00 | | 7 | 0.90 | ATP6V0A4; ATP6V0E2; CPEB1; GPLD1; HMGCS2; PDK4; PFKFB1 | 10 | 1.44 | EIF4EBP1; GSTP1; HIF1A; IL10; NAMPT; PCSK9; PRKCQ; RAB31; SOCS3; TRIB3 |
| positive regulation of reactive oxygen species metabolic process: GO | 84 | 9 | 1.79 | CDKN1A; F2RL1; GSTP1; IFNG; IL1B; IL6; PLAU; PTGS2; ZC3H12A | 6 | 0.84 | AGT; AGTR1; CLU; HBB; LEP; SNCA | 0 | 0.00 | | 1 | 4.97 | IL1B | 5 | 1.51 | AGTR1; CLU; ESR1; HBB; SNCA | 5 | 1.69 | CDKN1A; GSTP1; PTGS2; XDH; ZC3H12A |
| water soluble vitamin | 84 | 9 | 1.79 | ACP5; GSTO1; | 6 | 0.84 | ACACB; ALDH1L1; | 0 | 0.00 | | 0 | 0.00 | | 2 | 0.60 | AOX1; SLC19A3 | 5 | 1.69 | ACP5; NAMPT; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| metabolic process: GO | | | | MTHFD2; NAMPT; PRSS3; PTGS2; SLC2A1; TCN1; VNN3 | | | ENPP1; FOLR1; PTGIS; SLC19A3 | | | | | | | | | | | | PRSS3; PTGS2; SLC2A1 |
| ephrin receptor signaling pathway: GO | 84 | 8 | 1.59 | ACTB; ACTR3; ARPC1A; ARPC3; CDK5R1; MMP9; NTRK1; PSENEN | 8 | 1.12 | DNM1; EPHA6; EPHB1; EPHB6; GRIN1; NTRK3; PAK3; SDC2 | 0 | 0.00 | | 0 | 0.00 | | 2 | 0.60 | EFNB3; PAK3 | 5 | 1.69 | ACTB; ARPC1A; CDK5R1; EPHA2; VAV2 |
| sodium ion transmembrane transport: GO | 84 | 3 | 0.60 | ATP12A; ATP1B3; KCNK1 | 12 | 1.69 | ABCB11; ATP1A2; FXYD2; NALCN; SCN7A; SLC17A4; SLC17A7; SLC24A2; SLC34A3; SLC4A4; SLC9A2; SLC9A4 | 0 | 0.00 | | 0 | 0.00 | | 6 | 1.81 | ATP1B2; NALCN; SCN7A; SCNN1B; SLC4A4; SLC9A2 | 5 | 1.69 | KCNK1; SCNN1D; SLC20A1; SLC4A7; SLC5A5 |
| actin based cell projection: GO | 174 | 11 | 1.06 | ARL4C; CA2; CXADR; ENAH; FSCN1; ITGA3; MSN; MYO1B; PDPN; PLS3; TWF1 | 24 | 1.63 | ACTA1; ACTN2; ADCY6; AOC3; APBB1; ATP6V1B1; CDHR5; CLIC5; DMD; EPHB1; ESPN; GRXCR2; MUC20; MYO15A; MYO1A; MYO3A; | 1 | 2.40 | SRCIN1 | 0 | 0.00 | | 5 | 0.73 | ANGPT1; CLIC5; FOXA1; MUC20; PALM | 9 | 1.47 | CA2; ENAH; ITGA3; MSN; MYO1B; S100P; SLC4A7; TMC1; TWF1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | | | | NLGN1; PALM; PCDH15; PPPIR9A; SLC10A2; SRCIN1; TMC2; TSPEAR | | | | | | | | | | | | |
| heparin binding: GO | 151 | 14 | 1.55 | CCL7; CXCL10; CXCL11; CXCL13; CXCL6; FGFBP1; HBEGF; LIPG; LTF; NELL2; PGF; SELL; SERPINE2; WISP1 | 26 | 2.03 | ABI3BP; APOE; CCDC80; CFH; CLEC3B; COL25A1; ELANE; FGF1; FGF14; FGF9; FGFR1; GREM2; LIPH; LPL; MSTN; NDNF; PCOLCE2; PLA2G5; PRELP; PTCH1; SERPINA5; SLIT2; SLIT3; SOD3; TNXB; WISP2 | 2 | 5.54 | CLEC3B; LPL | 0 | 0.00 | | 19 | 3.20 | ABI3BP; CCDC80; CFH; CHRD; CTGF; CTSG; ELANE; FGF2; FGFR1; GREM2; LIPH; MDK; NDNF; PCOLCE; PTCH1; SLIT2; SLIT3; SOD3; WISP2 | 8 | 1.50 | CXCL11; CXCL6; FGFBP1; HBEGF; LTF; NELL2; SERPINA10; SERPINE2 |
| drug binding: GO | 106 | 14 | 2.21 | CHRNA3; CXCR4; FKBPL; FSCN1; GSTP1; IL2RA; MT2A; NAMPT; PNP; PPIF; PYGL; TOP2A; TTC9; | 18 | 2.00 | ALB; ATP1A2; CHRM1; CHRM2; CHRM3; CHRNA2; CNR1; CYP2C9; CYP2D6; CYP4B1; DRD1; DRD4; FOLR1; | 0 | 0.00 | | 1 | 3.94 | IL2RA | 6 | 1.44 | CHRM1; CHRM3; CYP4B1; FKBP7; GLRB; SLC18A2 | 6 | 1.61 | GSTP1; NAMPT; PNP; PPARD; PPIF; TOP2A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | UGT1A7 | | | FOLR2; GLRB; NPC1L1; P2RX1; PYGM | | | | | | | | | | | | |
| ion channel binding: GO | 106 | 7 | 1.11 | BAK1; HOMER1; PANX1; PRNP; RIMS3; VDAC1; YWHAQ | 9 | 1.00 | ABCC8; ACTN2; ANK2; FHL1; KCNB1; KCNIP2; PKD1; PPP1R9A; TRDN | 0 | 0.00 | | 0 | 0.00 | | 4 | 0.96 | ABCC9; HRC; TRDN; TRPC1 | 6 | 1.61 | ACTN1; BAK1; HOMER1; PANX1; VDAC1; YWHAQ |
| monocarboxylic acid binding: GO | 63 | 10 | 2.66 | CRABP2; FABP5; FABP6; LRAT; PYGL; S100A8; S100A9; UGT1A1; UGT1A10; UGT1A7 | 8 | 1.50 | ACOX2; ALB; APOC1; FABP4; OXER1; SERPINA5; SNCA; UGT2B7 | 0 | 0.00 | | 0 | 0.00 | | 4 | 1.61 | ACOX2; LPAR1; PMP2; SNCA | 4 | 1.80 | CRABP2; FABP5; LRAT; PPARD |
| oligosaccharide metabolic process: GO | 63 | 5 | 1.33 | FUT3; NEU2; SLC2A1; ST6GALNAC1; ST8SIA2 | 4 | 0.75 | B3GALT1; IDUA; ST6GAL2; ST6GALNAC5 | 0 | 0.00 | | 0 | 0.00 | | 3 | 1.21 | B3GALT1; GAL3ST4; ST6GALNAC5 | 4 | 1.80 | FUT3; SLC2A1; ST6GALNAC1; ST8SIA2 |
| peptidyl threonine modification: GO | 43 | 5 | 1.95 | CDK1; CDK5R1; CHEK1; MYLK2; TGFBR1 | 1 | 0.27 | BCL2 | 0 | 0.00 | | 0 | 0.00 | | 1 | 0.59 | BCL2 | 3 | 1.98 | CDK1; CDK5R1; CHEK1 |
| positive regulation of muscle contraction: GO | 43 | 5 | 1.95 | GSTO1; NMU; PROK2; PTAFR; PTGS2 | 5 | 1.37 | ADRA1A; ADRA1B; ATP2A1; CHRM3; MYOCD | 0 | 0.00 | | 0 | 0.00 | | 3 | 1.77 | ADRA1A; CHRM3; CTGF | 3 | 1.98 | NMU; PTAFR; PTGS2 |
| regulation of nucleoside metabolic process: GO | 43 | 5 | 1.95 | GADD45GIP1; HIF1A; PGAM1; PPIF; VCP | 6 | 1.65 | GPD1; MLXIPL; P2RX7; PPARGC1A; | 1 | 9.72 | GPD1 | 0 | 0.00 | | 3 | 1.77 | PPARGC1A; PRKAA2; SNCA | 3 | 1.98 | HIF1A; PGAM1; PPIF |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | | | | PRKAA2; SNCA | | | | | | | | | | | | |
| carbohydrate transporter activity: GO | 43 | 4 | 1.56 | AQP3; SLC2A1; SLC2A9; SLC5A1 | 5 | 1.37 | AQP4; AQP7; SLC2A4; SLC5A2; SLC5A9 | 0 | 0.00 | | 1 | 9.72 | AQP9 | 2 | 1.18 | SLC2A12; SLC5A9 | 3 | 1.98 | AQP3; SLC2A1; SLC2A9 |
| intraspecies interaction between organisms: GO | 43 | 4 | 1.56 | CNTNAP2; IL1B; NLGN4X; TH | 6 | 1.65 | DRD1; DRD4; GRIN1; NRXN1; NRXN3; SHANK1 | 0 | 0.00 | | 1 | 9.72 | IL1B | 1 | 0.59 | NRXN1 | 3 | 1.98 | CNTNAP2; NLGN4X; TH |
| negative regulation of myeloid leukocyte differentiation: GO | 43 | 4 | 1.56 | CCL3; LTF; NME1; UBASH3B | 4 | 1.10 | ADIPOQ; CARTPT; CLDN18; LRRC17 | 1 | 9.72 | ADIPOQ | 0 | 0.00 | | 2 | 1.18 | CLDN18; LRRC17 | 3 | 1.98 | LTF; TRIB1; UBASH3B |
| positive regulation of mrna metabolic process: GO | 43 | 3 | 1.17 | CCNB1; HSPA8; ZC3H12A | 1 | 0.27 | CELF4 | 0 | 0.00 | | 0 | 0.00 | | 0 | 0.00 | | 3 | 1.98 | CCNB1; HSPA8; ZC3H12A |
| labyrinthine layer development: GO | 43 | 2 | 0.78 | GJB5; SOCS3 | 1 | 0.27 | CDX4 | 0 | 0.00 | | 0 | 0.00 | | 1 | 0.59 | CDX4 | 3 | 1.98 | IL10; JUNB; SOCS3 |
| regulation of t cell migration: GO | 24 | 6 | 4.18 | CCL21; CXCL10; CXCL13; PYCARD; S100A7; WNT5A | 1 | 0.49 | APOD | 0 | 0.00 | | 0 | 0.00 | | 1 | 1.06 | CXCL12 | 2 | 2.36 | CCL20; WNT5A |
| ribonucleoside catabolic process: GO | 24 | 5 | 3.49 | AHCY; APOBEC3A; CDA; PNP; UPP1 | 1 | 0.49 | ENPP4 | 0 | 0.00 | | 0 | 0.00 | | 0 | 0.00 | | 2 | 2.36 | CDA; PNP |
| cellular response to toxic substance: GO | 24 | 4 | 2.79 | HIF1A; HSPA5; IL1B; RAB10 | 3 | 1.47 | CRIP1; CYP17A1; PPP1R9A | 0 | 0.00 | | 1 | 17.41 | IL1B | 1 | 1.06 | CRIP1 | 2 | 2.36 | HIF1A; HSPA5 |
| embryonic camera type eye morphogenesis: GO | 24 | 4 | 2.79 | ALDH1A3; STRA6; TH; WNT5A | 1 | 0.49 | PAX6 | 0 | 0.00 | | 0 | 0.00 | | 0 | 0.00 | | 2 | 2.36 | TH; WNT5A |
| regulation of | 24 | 4 | 2.79 | CDH3; | 2 | 0.98 | CD34; | 0 | 0.00 | | 0 | 0.00 | | 2 | 2.12 | CD34; | 2 | 2.36 | HIF1A; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| transforming growth factor beta production: GO | | | | HIF1A; PTGS2; SERPINB7 | | | WNT11 | | | | | | | | | WNT11 | | | PTGS2 |
| skeletal muscle tissue regeneration: GO | 24 | 4 | 2.79 | ANXA1; GJA1; PLAU; WNT7A | 1 | 0.49 | MSTN | 0 | 0.00 | | 0 | 0.00 | | 1 | 1.06 | FZD7 | 2 | 2.36 | SOX15; WNT7A |
| actin monomer binding: GO | 24 | 3 | 2.09 | PFN1; TMSB10; TWF1 | 4 | 1.97 | MYL3; MYL4; PKNOX2 | 0 | 0.00 | | 0 | 0.00 | | 0 | 0.00 | | 2 | 2.36 | PFN1; TWF1 |
| adp signalling through p2ry1 | 24 | 3 | 2.09 | GNA15; GNGT2; P2RY1 | 0 | 0.00 | | 0 | 0.00 | | 0 | 0.00 | | 1 | 1.06 | GNG11 | 2 | 2.36 | GNA15; P2RY1 |
| carbohydrate transmembrane transport: GO | 24 | 3 | 2.09 | SLC2A1; SLC2A9; SLC5A1 | 3 | 1.47 | SLC2A4; SLC5A2; SLC5A9 | 0 | 0.00 | | 0 | 0.00 | | 2 | 2.12 | SLC2A12; SLC5A9 | 2 | 2.36 | SLC2A1; SLC2A9 |
| glycosphingolipid biosynthetic process: GO | 24 | 3 | 2.09 | ST6GALNAC1; ST8SIA2; UGCG | 2 | 0.98 | GAL3ST1; ST6GALNAC5 | 0 | 0.00 | | 0 | 0.00 | | 1 | 1.06 | ST6GALNAC5 | 2 | 2.36 | ST6GALNAC1; ST8SIA2 |
| negative regulation of osteoclast differentiation: GO | 24 | 3 | 2.09 | CCL3; LTF; UBASH3B | 3 | 1.47 | CARTPT; CLDN18; LRRC17 | 0 | 0.00 | | 0 | 0.00 | | 2 | 2.12 | CLDN18; LRRC17 | 2 | 2.36 | LTF; UBASH3B |
| positive regulation of g1 s transition of mitotic cell cycle: GO | 24 | 3 | 2.09 | ANXA1; CDC45; CDC6 | 1 | 0.49 | CYP1A1 | 0 | 0.00 | | 0 | 0.00 | | 0 | 0.00 | | 2 | 2.36 | CDC45; CDC6 |
| protein lipid complex binding: GO | 24 | 3 | 2.09 | LDLR; LRP8; PCSK9 | 4 | 1.97 | APOE; COLEC12; GPIHBP1; MAPT | 0 | 0.00 | | 0 | 0.00 | | 1 | 1.06 | MAPT | 2 | 2.36 | LDLR; PCSK9 |
| apoptotic nuclear changes: GO | 24 | 2 | 1.39 | DNASE1L3; TOP2A | 2 | 0.98 | ACVR1C; CECR2 | 1 | 17.41 | ACVR1C | 0 | 0.00 | | 0 | 0.00 | | 2 | 2.36 | DNASE1L3; TOP2A |
| cerebellar purkinje cell layer development: GO | 24 | 2 | 1.39 | HSPA5; KIF14 | 2 | 0.98 | ATP2B2; SEZ6L | 0 | 0.00 | | 0 | 0.00 | | 1 | 1.06 | SEZ6L | 2 | 2.36 | HSPA5; KIF14 |
| dopamine metabolic process: GO | 24 | 2 | 1.39 | SNCB; TH | 5 | 2.46 | DRD1; DRD4; GRIN2A; MAOA; SNCA | 0 | 0.00 | | 0 | 0.00 | | 1 | 1.06 | SNCA | 2 | 2.36 | SNCB; TH |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| neuropeptide receptor binding: GO | 24 | 2 | 1.39 | ADCYAP1; NMU | 3 | 1.47 | CCKBR; EDN3; SHANK1 | 1 | 17.41 | MRAP2 | 0 | 0.00 | | 2 | 2.12 | ASIP; EDN3 | 2 | 2.36 | NMU; UCN2 |
| neurotransmitter transporter activity: GO | 24 | 2 | 1.39 | GABRQ; SLC6A11 | 2 | 0.98 | SLC6A17; SLC6A2 | 0 | 0.00 | | 0 | 0.00 | | 0 | 0.00 | | 2 | 2.36 | SLC18A3; SLC6A11 |
| positive regulation of insulin secretion involved in cellular response to glucose stimulus: GO | 24 | 2 | 1.39 | HIF1A; VSNL1 | 3 | 1.47 | CFTR; GPLD1; PLA2G6 | 0 | 0.00 | | 0 | 0.00 | | 1 | 1.06 | GPLD1 | 2 | 2.36 | HIF1A; VSNL1 |
| positive regulation of peptidyl threonine phosphorylation: GO | 24 | 2 | 1.39 | PLK1; WNT5A | 1 | 0.49 | EGF | 0 | 0.00 | | 0 | 0.00 | | 1 | 1.06 | EGF | 2 | 2.36 | PLK1; WNT5A |
| ammonium transmembrane transport: GO | 24 | 1 | 0.70 | RHCG | 3 | 1.47 | ACACB; PRKAA2; RHAG | 0 | 0.00 | | 0 | 0.00 | | 2 | 2.12 | PRKAA2; RHBG | 2 | 2.36 | RHCG; SLC18A3 |
| growth factor activity: GO | 152 | 17 | 1.87 | AREG; ARTN; CSF2; CXCL1; EPGN; EREG; GDNF; HBEGF; IL12B; IL6; MANF; NGF; NRG1; OSM; PGF; TGFA; TYMP | 24 | 1.86 | AGT; AMELX; BMP3; BMP5; BTC; DKK1; EGF; FGF1; FGF14; FGF17; FGF22; FGF9; GDF10; GDF5; IL34; IL5; INHBB; LEP; LIF; MSTN; NRG2; NRG3; PDGFD; PROK1 | 0 | 0.00 | | 1 | 2.75 | OSM | 8 | 1.34 | CDNF; CTGF; CXCL12; EGF; FGF2; FGF22; GDF7; MDK | 8 | 1.49 | AREG; ARTN; EREG; HBEGF; IL10; NGF; NRG1; TGFA |
| ruffle: GO | 152 | 11 | 1.21 | CFL1; FERMT1; FSCN1; KIF18A; | 7 | 0.54 | AMOT; ARHGEF26; COBL; GSN; PDE9A; | 0 | 0.00 | | 1 | 2.75 | SAMSN1 | 5 | 0.84 | ARHGEF26; DLC1; PDE9A; TESC; TLN2 | 8 | 1.49 | ACTN1; CFL1; EPHA2; FERMT1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | MEFV; NME1; PDPN; S100A11; SAMSN1; TNFRSF12A; TWF1 | | | TLN2; TPM1 | | | | | | | | | | | | KIF18A; MEFV; SPRY4; TWF1 |
| response to heat: GO | 85 | 12 | 2.36 | CDKN1A; CXCL10; EIF2S1; HMOX1; HSPA6; IL1A; IL1B; IL6; MKI67; OSM; PRKCQ; SOCS3 | 4 | 0.56 | FGF1; HSPB7; MSTN; SCARA5 | 0 | 0.00 | | 2 | 9.83 | IL1B; OSM | 3 | 0.90 | CRNN; CXCL12; SCARA5 | 5 | 1.67 | CDKN1A; MKI67; PRKCQ; SOCS3; TRPV3 |
| cell surface interactions at the vascular wall | 107 | 20 | 3.13 | ATP1B3; CD2; CXADR; ITGA3; ITGA6; ITGAX; MMP1; NRAS; OLR1; PPIA; SDC1; SELE; SELL; SLC16A1; SLC7A11; SLC7A5; SLC7A8; THBD; TNFRSF10A; TREM1 | 7 | 0.77 | ANGPT4; GRB14; MERTK; SDC2; SLC16A8; SLC7A10; SLC7A9 | 0 | 0.00 | | 2 | 7.81 | SELE; TREM1 | 6 | 1.42 | ANGPT1; ANGPT4; ATP1B2; IGHM; JAM2; TSPAN7 | 6 | 1.59 | ITGA3; ITGA6; PPIAP22; SLC7A11; SLC7A5; THBD |
| response to interleukin 1: GO | 107 | 15 | 2.35 | ANXA1; CCL17; CCL18; CCL21; CCL22; CCL3; CCL7; HIF1A; HYAL3; IL6; MYD88; | 3 | 0.33 | CCL14; PTGIS; SNCA | 0 | 0.00 | | 1 | 3.91 | SELE | 2 | 0.47 | CCL14; SNCA | 6 | 1.59 | CCL20; HIF1A; MYD88; P2RY2; RPS6KA4; ZC3H12A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | P2RY2; PYCARD; SELE; ZC3H12A | | | | | | | | | | | | | | | |
| response to type i interferon: GO | 64 | 14 | 3.66 | IFI27; IFI6; IFIT3; IFITM1; IFITM3; ISG15; ISG20; MX1; OAS1; OAS2; OAS3; OASL; RSAD2; STAT1 | 1 | 0.18 | IFNA5 | 0 | 0.00 | | 2 | 13.06 | IFITM3; ISG15 | 0 | 0.00 | | 4 | 1.77 | HLA-G; IFI27; MX1; OAS1 |
| hedgehog 'off' state | 64 | 7 | 1.83 | CSNK1A1; PSMA5; PSMB6; TUBA1C; TUBA4A; TUBB2A; TUBB6 | 2 | 0.37 | ADCY8; PRKAR2B | 1 | 6.53 | PRKAR2B | 0 | 0.00 | | 0 | 0.00 | | 4 | 1.77 | TUBA1C; TUBA4A; TUBB2A; TUBB6 |
| rb 1pathway | 64 | 6 | 1.57 | CCNA2; CCND2; CCNE1; CDKN1A; CSF2; E2F3 | 4 | 0.74 | CKM; GSC; MITF; PAX3 | 0 | 0.00 | | 0 | 0.00 | | 1 | 0.40 | MITF | 4 | 1.77 | CCNA2; CCND2; CDKN1A; E2F1 |
| regulation of reactive oxygen species biosynthetic process: GO | 64 | 6 | 1.57 | ACP5; IFNG; IL1B; IL6; PTGS2; ZC3H12A | 6 | 1.11 | AGT; CD34; CLU; HBB; PTGIS; SNCA | 0 | 0.00 | | 1 | 6.53 | IL1B | 6 | 2.38 | CD34; CLU; ESR1; HBB; SLC18A2; SNCA | 4 | 1.77 | ACP5; IL10; PTGS2; ZC3H12A |
| terminal bouton: GO | 64 | 6 | 1.57 | ADCYAP1; CCK; NMU; NTSR1; SNCB; TH | 9 | 1.66 | ADORA1; DRD4; GRIA4; GRIK3; GRIK5; GRIN1; SNCA; SYNGR1; SYT1 | 1 | 6.53 | GRIA4 | 0 | 0.00 | | 4 | 1.59 | ESR1; GRIK3; SLC18A2; SNCA | 4 | 1.77 | NMU; NTSR1; SNCB; TH |
| positive regulation | 130 | 14 | 1.80 | ADM2; | 11 | 1.00 | ANGPT4; | 0 | 0.00 | | 3 | 9.64 | ANXA3; | 6 | 1.17 | ANGPT4; C3; | 7 | 1.53 | ADM2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| of vasculature development: GO | | | | ANXA3; GREM1; HIF1A; HMOX1; IL1A; IL1B; NTRK1; PGF; PTGS2; SERPINB7; SERPINE1; WNT5A; ZC3H12A | | | ASB4; C3; C6; CCBE1; CD34; FGF1; MYOCD; PDGFD; PTGIS; TMEM100 | | | | | | IL1B; SERPINE1 | | | CCBE1; CD34; FGF2; PIK3R6 | | | ANGPTL4; HIF1A; LRG1; PTGS2; WNT5A; ZC3H12A |
| regulation of stem cell proliferation: GO | 86 | 7 | 1.36 | ASPM; FOXF1; HIF1A; HMGA2; STAT1; TP63; WNT5A | 9 | 1.23 | DCT; FGF9; FGFR1; IRS2; PAX6; SIX1; SOX10; TERT; WNT11 | 0 | 0.00 | | 0 | 0.00 | | 7 | 2.07 | CHRD; FBLN1; FGFR1; MYCN; PRRX1; SHOX2; WNT11 | 5 | 1.65 | ASPM; HIF1A; HMGA2; SNAI2; WNT5A |
| nucleotide binding domain leucine rich repeat containing receptor nlr signaling pathways | 44 | 5 | 1.90 | MEFV; PANX1; PYCARD; TXN; UBE2N | 3 | 0.80 | BCL2; P2RX7; TXNIP | 0 | 0.00 | | 0 | 0.00 | | 2 | 1.15 | BCL2; TXNIP | 3 | 1.93 | MEFV; PANX1; TXN |
| endothelial cell development: GO | 44 | 4 | 1.52 | F2RL1; MSN; RAP2B; WNT7A | 4 | 1.07 | ARHGEF26; GSTM3; HAPLN2; TNMD | 0 | 0.00 | | 0 | 0.00 | | 2 | 1.15 | ARHGEF26; TNMD | 3 | 1.93 | MSN; RAP2B; WNT7A |
| protein tyrosine serine threonine phosphatase activity: GO | 44 | 4 | 1.52 | CDKN3; DUSP14; DUSP6; DUSP9 | 1 | 0.27 | DUSP27 | 0 | 0.00 | | 0 | 0.00 | | 0 | 0.00 | | 3 | 1.93 | CDKN3; DUSP6; PTP4A1 |
| actin filament bundle organization: GO | 44 | 3 | 1.14 | FSCN1; MYO1B; RHOD | 2 | 0.54 | ESPN; SORBS1 | 0 | 0.00 | | 0 | 0.00 | | 1 | 0.58 | DPYSL3 | 3 | 1.93 | ACTN1; MYO1B; RHOD |
| glycine, serine and threonine metabolism | 44 | 3 | 1.14 | AKRIB10; GARS; TARS | 4 | 1.07 | ALAS2; AOC3; DMGDH; MAOA | 0 | 0.00 | | 0 | 0.00 | | 3 | 1.73 | DMGDH; GAMT; GATM | 3 | 1.93 | AKRIB10; GLDC; TARS |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| response to ketone: GO | 177 | 17 | 1.61 | CALR; CCL21; CCNE1; CDKN1A; DSG1; FOSL1; GJB2; IL1B; IL6; MSN; NEFL; NME1; PTAFR; SOCS3; TH; TK1; WNT5A | 15 | 1.00 | ADCY2; ADCY5; ADCY6; C3; CATSPERG; F7; GHR; HMGCS2; MSTN; NTRK3; PRKAA2; SLIT2; SLIT3; TXNIP; UGT3A2 | 1 | 2.36 | GHR | 1 | 2.36 | IL1B | 9 | 1.29 | C3; CATSPERG; HMGCS2; P2RY4; PRKAA2; SLC18A2; SLIT2; SLIT3; TXNIP | 9 | 1.44 | CDKN1A; FOSL1; JUNB; MSN; PTAFR; SOCS3; TH; TK1; WNT5A |
| regulation of anion transport: GO | 131 | 13 | 1.66 | CA2; CCK; CHRNA3; CHRNA6; GDNF; HRH3; IL1B; LRRC8D; NTSR1; P2RY2; PRELID1; PTAFR; VDAC1 | 24 | 2.16 | ADORA1; ANO9; APOE; ATP1A2; CFTR; CLCNKA; CLCNKB; CNR1; CRY2; CYP4A11; DRD1; DRD4; GRM7; IRS2; KCNA2; LEP; NPY5R; P2RX7; PCP4; PLA2G6; RAB3B; ROS1; SNCA; SNCG | 0 | 0.00 | | 1 | 3.19 | IL1B | 7 | 1.36 | ANO9; CLCN4; CRY2; CXCL12; CYP4A11; RAB3B; SNCA | 7 | 1.52 | CA2; CHRNA6; NTSR1; P2RY2; PRELID1; PTAFR; VDAC1 |
| glycan structures - biosynthesis 2 | 65 | 6 | 1.54 | B3GNT3; B3GNT5; FUT1; FUT2; FUT3; UGCG | 5 | 0.91 | ABO; B3GALT1; B3GALT5; FUT9; ST6GALNAC5 | 0 | 0.00 | | 0 | 0.00 | | 3 | 1.17 | ABO; B3GALT1; ST6GALNAC5 | 4 | 1.75 | B3GNT5; FUT1; FUT2; FUT3 |
| nerve development: GO | 65 | 6 | 1.54 | FBXO45; NPTX1; NTRK1; SERPINE2; SULF2; UNC13A | 11 | 2.00 | COL25A1; DRGX; EPHB1; GABRB3; KCNA2; PLXNA3; PLXNA4; | 0 | 0.00 | | 0 | 0.00 | | 3 | 1.17 | LPAR1; PLXNA4; SLITRK6 | 4 | 1.75 | FBXO45; NPTX1; SERPINE2; UNC13A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | | | | PRX; RNF165; SEMA3A; SIX1 | | | | | | | | | | | | |
| pip3 signaling in cardiac myoctes | 65 | 6 | 1.54 | EBP; IFI27; NOLC1; SFN; YWHAQ; YWHAZ | 5 | 0.91 | ERBB4; IRS2; IRS4; PAK3; SLC2A4 | 0 | 0.00 | | 0 | 0.00 | | 2 | 0.78 | ERBB4; PAK3 | 4 | 1.75 | IFI27; SFN; YWHAQ; YWHAZ |
| positive regulation of endothelial cell migration: GO | 65 | 5 | 1.29 | ANXA3; PTGS2; WNT5A; WNT7A; ZC3H12A | 7 | 1.27 | AGT; AMOT; ANGPT4; ATOH8; CCBE1; FGFR1; GPLD1 | 0 | 0.00 | | 1 | 6.43 | ANXA3 | 7 | 2.74 | ANGPT1; ANGPT4; ATOH8; CCBE1; FGF2; FGFR1; GPLD1 | 4 | 1.75 | PTGS2; WNT5A; WNT7A; ZC3H12A |
| transferase activity transferring sulfur containing groups: GO | 65 | 5 | 1.29 | CHST1; HS3ST1; HS3ST3A1; HS3ST3B1; SULT2B1 | 11 | 2.00 | CHST12; CHST5; GAL3ST1; HS3ST2; HS3ST5; HS3ST6; HS6ST3; SULT1A2; SULT1C3; UST; WSCD1 | 0 | 0.00 | | 0 | 0.00 | | 5 | 1.95 | CHST12; DSEL; GAL3ST4; SULTIE1; UST | 4 | 1.75 | CHST1; HS3ST1; HS3ST3A1; SULT2B1 |
| acid secretion: GO | 65 | 4 | 1.03 | ANXA1; BDKRB2; NMU; TRPC4 | 15 | 2.72 | ABCB11; APBA1; CCKBR; DRD4; LEP; NOS2; PLA2G5; RIMS1; SLC17A7; SLC1A2; SLC1A6; SLC1A7; SLC26A7; SLC9A4; SYT1 | 0 | 0.00 | | 1 | 6.43 | AQP9 | 4 | 1.56 | APBA1; RIMS1; SLC1A6; SLC1A7 | 4 | 1.75 | BDKRB2; HRH2; NMU; SLC26A6 |
| cellular response to interleukin 4: GO | 25 | 4 | 2.68 | HSPA5; IL24; IL4R; JAK3 | 0 | 0.00 | | 0 | 0.00 | | 0 | 0.00 | | 0 | 0.00 | | 2 | 2.27 | HSPA5; MCM2 |
| regulation of | 25 | 4 | 2.68 | IL1RL1; IL4R; | 2 | 0.94 | MUC5B; | 0 | 0.00 | | 0 | 0.00 | | 1 | 1.02 | SNCA | 2 | 2.27 | WNT5A; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| macrophage activation: GO | | | | WNT5A; ZC3H12A | | | SNCA | | | | | | | | | | | | ZC3H12A |
| fluid transport: GO | 25 | 3 | 2.01 | AQP3; CSF2; PDPN | 3 | 1.42 | AQP4; AQP7; SLC14A1 | 0 | 0.00 | | 1 | 16.72 | AQP9 | 1 | 1.02 | SLC14A1 | 2 | 2.27 | AQP3; SLC26A6 |
| cysteine metabolism | 25 | 2 | 1.34 | GOT2; LDHA | 2 | 0.94 | CDO1; CHST5 | 0 | 0.00 | | 0 | 0.00 | | 1 | 1.02 | GAL3ST4 | 2 | 2.27 | GOT2; LDHA |
| dynein binding: GO | 25 | 2 | 1.34 | CENPF; RAN | 2 | 0.94 | DNAAF1; SNCA | 0 | 0.00 | | 0 | 0.00 | | 1 | 1.02 | SNCA | 2 | 2.27 | CENPF; RAN |
| hdac classiii pathway | 25 | 2 | 1.34 | CDKN1A; TUBB2A | 1 | 0.47 | PPARGC1A | 0 | 0.00 | | 0 | 0.00 | | 2 | 2.03 | HOXA10; PPARGC1A | 2 | 2.27 | CDKN1A; TUBB2A |
| met activates ptk2 signaling | 25 | 2 | 1.34 | ITGA3; LAMB3 | 2 | 0.94 | COL24A1; LAMA2 | 0 | 0.00 | | 0 | 0.00 | | 3 | 3.05 | COL24A1; GULP1; LAMA2 | 2 | 2.27 | ITGA3; LAMB3 |
| urea cycle and metabolism of amino groups | 25 | 2 | 1.34 | ODC1; SRM | 1 | 0.47 | CKM | 0 | 0.00 | | 0 | 0.00 | | 2 | 2.03 | GAMT; GATM | 2 | 2.27 | NAGS; ODC1 |
| chaperone mediated protein folding: GO | 45 | 7 | 2.60 | CALR; CCT2; FKBPL; HSPA8; HSPH1; PPIB; TTC9 | 2 | 0.52 | CLU; DNAJB8 | 0 | 0.00 | | 0 | 0.00 | | 2 | 1.13 | CLU; FKBP7 | 3 | 1.89 | CCT2; HSPA8; HSPH1 |
| nucleosome binding: GO | 45 | 5 | 1.86 | ACTB; H2AFZ; HMGA2; RCC1; UHRF1 | 0 | 0.00 | | 0 | 0.00 | | 0 | 0.00 | | 0 | 0.00 | | 3 | 1.89 | ACTB; H2AFZ; HMGA2 |
| o acyltransferase activity: GO | 45 | 4 | 1.49 | AGPAT5; LRAT; MBOAT2; PIGW | 9 | 2.36 | AWAT1; AWAT2; CRAT; DGAT2L6; GPAM; MOGAT1; MOGAT2; PNPLA3; SOAT2 | 1 | 9.29 | GPAM | 0 | 0.00 | | 2 | 1.13 | DGAT2; PNPLA3 | 3 | 1.89 | LPCAT1; LRAT; PIGW |
| cargo recognition for clathrin-mediated endocytosis | 45 | 3 | 1.12 | LDLR; STON2; WNT5A | 6 | 1.57 | AGTR1; EGF; FZD4; SYT1; SYT9; TF | 0 | 0.00 | | 0 | 0.00 | | 2 | 1.13 | AGTR1; EGF | 3 | 1.89 | LDLR; STON2; WNT5A |
| regulation of establishment | 45 | 3 | 1.12 | IFNG; ITGA3; LYPLA1 | 6 | 1.57 | ANXA13; AR; DPP10; | 0 | 0.00 | | 0 | 0.00 | | 2 | 1.13 | LRRC15; NRXN1 | 3 | 1.89 | ARHGEF16; EPHA2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| of protein localization to plasma membrane: GO | | | | | | | NRXN1; PKDCC; SORBS1 | | | | | | | | | | | | ITGA3 |
| ilk pathway | 45 | 2 | 0.74 | AURKA; RUVBL1 | 3 | 0.79 | MYL9; PPP1R14A; TNS1 | 0 | 0.00 | | 0 | 0.00 | | 0 | 0.00 | | 3 | 1.89 | ACTN1; AURKA; TACC3 |
| positive regulation of interleukin 6 production: GO | 66 | 13 | 3.30 | ADCYAP1; EREG; F2RL1; IFNG; IL1B; IL36A; IL36B; IL6; MYD88; PTAFR; PYCARD; TNFSF9; WNT5A | 2 | 0.36 | P2RX7; PAEP | 0 | 0.00 | | 1 | 6.33 | IL1B | 1 | 0.38 | ZBTB20 | 4 | 1.72 | EREG; MYD88; PTAFR; WNT5A |
| integrin1 pathway | 66 | 7 | 1.77 | ITGA3; ITGA6; LAMB3; PLAU; PLAUR; TGM2; TNC | 5 | 0.89 | COL11A1; COL11A2; ITGA7; ITGA8; LAMA2 | 0 | 0.00 | | 0 | 0.00 | | 5 | 1.92 | COL11A1; ITGA11; JAM2; LAMA2; MDK | 4 | 1.72 | ITGA3; ITGA6; LAMB3; TGM2 |
| amino acid transmembrane transport: GO | 66 | 6 | 1.52 | SLC38A1; SLC38A5; SLC7A1; SLC7A11; SLC7A5; SLC7A8 | 9 | 1.61 | SLC16A12; SLC17A7; SLC1A2; SLC1A6; SLC1A7; SLC6A17; SLC7A10; SLC7A14; SLC7A9 | 0 | 0.00 | | 0 | 0.00 | | 3 | 1.15 | SLC16A10; SLC1A6; SLC1A7 | 4 | 1.72 | SLC38A5; SLC7A1; SLC7A11; SLC7A5 |
| rough endoplasmic reticulum: GO | 66 | 5 | 1.27 | LRAT; PCSK9; SLC7A11; TP63; ZC3H12A | 7 | 1.25 | ALDOB; CFTR; MPZ; MYOC; NAT8L; SCGB1A1; SNCA | 0 | 0.00 | | 0 | 0.00 | | 5 | 1.92 | ADCYAP1R1; MPZ; MYOC; SNCA; TRAM1L1 | 4 | 1.72 | LRAT; PCSK9; SLC7A11; ZC3H12A |
| positive regulation of response to wounding: GO | 156 | 22 | 2.36 | ANXA1; CCL18; CCL3; CCL7; | 13 | 0.98 | ADRA2A; AGT; AGTR1; C3; CCL14; | 1 | 2.68 | LPL | 4 | 10.72 | FFAR2; IL1B; OSM; SERPINE1 | 5 | 0.81 | ADRA2A; AGTR1; C3; CCL14; | 8 | 1.45 | F12; HBEGF; HPSE; PPARD; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | F12; HBEGF; HPSE; IDO1; IL12B; IL1B; ILIRL1; IL6; INSL3; OSM; PTGS2; S100A12; S100A8; S100A9; SERPINE1; THBD; TLR10; WNT5A | | | CNR1; ENPP4; F7; FABP4; KLKB1; LPL; NPY5R; NTRK3 | | | | | | | | | GPRC5B | | | PTGS2; SOX15; THBD; WNT5A |
| regulation of carbohydrate metabolic process: GO | 156 | 10 | 1.07 | HIF1A; IL6; NTSR1; P2RY1; PGAM1; PHLDA2; PTAFR; UGT1A1; UGT1A10; UGT1A7 | 24 | 1.82 | ACACB; ADIPOQ; EGF; ENPP1; GCGR; GPD1; GPLD1; IRS2; KAT2A; LEP; LEPR; LHCGR; MLXIPL; MST1; P2RX7; PDK4; PFKFB1; PPARGC1A; PRKAA2; PTHIR; RORC; SERPINA12; SNCA; SORBS1 | 2 | 5.36 | ADIPOQ; GPD1 | 0 | 0.00 | | 13 | 2.12 | ADCYAP1R1; DGAT2; EGF; GPLD1; IGFBP5; PDK3; PDK4; PFKFB1; PPARGC1A; PRKAA2; PTH1R; SERPINA12; SNCA | 8 | 1.45 | HIF1A; HRH1; IGFBP3; NTSR1; P2RY1; PGAM1; PHLDA2; PTAFR |
| negative regulation of protein modification by small protein conjugation or removal: GO | 133 | 14 | 1.76 | BUB1B; CCNB1; CDC20; CDK1; FBXO5; ISG15; MAD2L1; PSMA4; | 0 | 0.00 | | 0 | 0.00 | | 1 | 3.14 | ISG15 | 0 | 0.00 | | 7 | 1.49 | BUB1B; CCNB1; CDC20; CDK1; MAD2L1; RNF222; UBE2C |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | PSMA5; PSMB6; PSMD1; PSME3; RNF222; UBE2C | | | | | | | | | | | | | | | |
| ribonucleoprotein complex binding: GO | 88 | 10 | 1.90 | C1QBP; EIF2S1; EIF4A3; EIF5A; EIF5AL1; EIF6; HSPA5; NME1; NPM1; ZC3H12A | 1 | 0.13 | CPEB1 | 0 | 0.00 | | 0 | 0.00 | | 1 | 0.29 | CPEB1 | 5 | 1.61 | EIF4A3; EIF6; HSPA5; NPM1; ZC3H12A |
| positive regulation of lymphocyte migration: GO | 26 | 8 | 5.15 | CCL21; CCL3; CCL7; CXCL10; CXCL13; PYCARD; S100A7; WNT5A | 0 | 0.00 | | 0 | 0.00 | | 0 | 0.00 | | 1 | 0.98 | CXCL12 | 2 | 2.18 | CCL20; WNT5A |
| positive regulation of release of cytochrome c from mitochondria: GO | 26 | 7 | 4.51 | BAK1; FAM162A; MMP9; PLAUR; PPIF; PYCARD; TNFSF10 | 1 | 0.45 | PLA2G6 | 0 | 0.00 | | 0 | 0.00 | | 0 | 0.00 | | 2 | 2.18 | BAK1; PPIF |
| developmental programmed cell death: GO | 26 | 5 | 3.22 | BAK1; DNASE1L3; IL1A; IL1B; NTRK1 | 3 | 1.36 | CRYAB; HAND2; NKX2-5 | 1 | 16.07 | CRYAB | 1 | 16.07 | IL1B | 1 | 0.98 | HAND2 | 2 | 2.18 | BAK1; DNASE1L3 |
| positive regulation of nf kappab import into nucleus: GO | 26 | 5 | 3.22 | GREM1; IL12B; IL1B; PRKCQ; PTGS2 | 1 | 0.45 | EDA | 0 | 0.00 | | 1 | 16.07 | IL1B | 0 | 0.00 | | 2 | 2.18 | PRKCQ; PTGS2 |
| negative regulation of response to biotic stimulus: GO | 26 | 4 | 2.57 | C1QBP; IL2RA; LTF; PRDM1 | 0 | 0.00 | | 0 | 0.00 | | 1 | 16.07 | IL2RA | 0 | 0.00 | | 2 | 2.18 | LTF; TRIB1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| response to copper ion: GO | 26 | 4 | 2.57 | CDK1; IL1A; PRNP; TK1 | 4 | 1.82 | ALDOB; CP; SNCA; SOD3 | 0 | 0.00 | | 0 | 0.00 | | 3 | 2.93 | CP; SNCA; SOD3 | 2 | 2.18 | CDK1; TK1 |
| cargo concentration in the er | 26 | 3 | 1.93 | AREG; CTSC; TGFA | 1 | 0.45 | FOLR1 | 0 | 0.00 | | 0 | 0.00 | | 0 | 0.00 | | 2 | 2.18 | AREG; TGFA |
| cyclin dependent protein serine threonine kinase regulator activity: GO | 26 | 3 | 1.93 | CCNE1; CDKN1A; CKS2 | 0 | 0.00 | | 1 | 16.07 | CDKN1C | 0 | 0.00 | | 0 | 0.00 | | 2 | 2.18 | CDKN1A; CKS2 |
| ganglioside metabolic process: GO | 26 | 3 | 1.93 | NEU2; ST6GALNAC1; ST8SIA2 | 1 | 0.45 | ST6GALNAC5 | 0 | 0.00 | | 0 | 0.00 | | 1 | 0.98 | ST6GALNAC5 | 2 | 2.18 | ST6GALNAC1; ST8SIA2 |
| glycosaminoglycan biosynthesis heparan sulfate | 26 | 3 | 1.93 | HS3ST1; HS3ST3A1; HS3ST3B1 | 4 | 1.82 | EXTL1; HS3ST2; HS3ST5; HS6ST3 | 0 | 0.00 | | 0 | 0.00 | | 0 | 0.00 | | 2 | 2.18 | HS3ST1; HS3ST3A1 |
| modulation by symbiont of host cellular process: GO | 26 | 3 | 1.93 | KPNA2; SERPINB9; ZC3H12A | 1 | 0.45 | NTRK3 | 0 | 0.00 | | 1 | 16.07 | SERPINB9 | 0 | 0.00 | | 2 | 2.18 | KPNA2; ZC3H12A |
| oxidoreductase activity acting on single donors with incorporation of molecular oxygen: GO | 26 | 3 | 1.93 | IDO1; PTGS2; TDO2 | 2 | 0.91 | CDO1; HAAO | 0 | 0.00 | | 1 | 16.07 | TDO2 | 0 | 0.00 | | 2 | 2.18 | HPDL; PTGS2 |
| regulation of endoplasmic reticulum unfolded protein response: GO | 26 | 3 | 1.93 | BAK1; HSPA5; SDF2L1 | 0 | 0.00 | | 0 | 0.00 | | 0 | 0.00 | | 0 | 0.00 | | 2 | 2.18 | BAK1; HSPA5 |
| regulation of extracellular matrix organization: GO | 26 | 3 | 1.93 | DPP4; FSCN1; HSPA8 | 3 | 1.36 | AGT; CHADL; PHLDB1 | 0 | 0.00 | | 0 | 0.00 | | 1 | 0.98 | DDR2 | 2 | 2.18 | DPP4; HSPA8 |
| regulation of fatty acid transport: GO | 26 | 3 | 1.93 | IL1B; NTSR1; P2RY2 | 4 | 1.82 | CYP4A11; IRS2; P2RX7; PLA2G6 | 0 | 0.00 | | 1 | 16.07 | IL1B | 1 | 0.98 | CYP4A11 | 2 | 2.18 | NTSR1; P2RY2 |
| dopaminergic | 26 | 2 | 1.29 | HIF1A; | 1 | 0.45 | LMX1A | 0 | 0.00 | | 0 | 0.00 | | 1 | 0.98 | FOXA1 | 2 | 2.18 | HIF1A; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| neuron differentiation: GO | | | | WNT5A | | | | | | | | | | | | | | | WNT5A |
| endoribonuclease activity producing 5 phosphomono esters: GO | 26 | 2 | 1.29 | EXO1; RPP40 | 0 | 0.00 | | 0 | 0.00 | | 0 | 0.00 | | 0 | 0.00 | | 2 | 2.18 | EXO1; FEN1 |
| recombination | 26 | 2 | 1.29 | BLM; BRCA2 | 0 | 0.00 | | 0 | 0.00 | | 0 | 0.00 | | 0 | 0.00 | | 2 | 2.18 | BLM; BRCA2 |
| il8 cxcr1 pathway | 26 | 2 | 1.29 | CXCR1; GNA15 | 1 | 0.45 | DNM1 | 0 | 0.00 | | 0 | 0.00 | | 1 | 0.98 | PIK3R6 | 2 | 2.18 | CXCR1; GNA15 |
| influence of ras and rho proteins on g1 to s transition | 26 | 2 | 1.29 | CCNE1; CDKN1A | 0 | 0.00 | | 0 | 0.00 | | 0 | 0.00 | | 0 | 0.00 | | 2 | 2.18 | CDKN1A; E2F1 |
| intestinal absorption: GO | 26 | 2 | 1.29 | LDLR; SLC5A1 | 5 | 2.27 | ADRA2A; LEP; MOGAT2; NPC1L1; SOAT2 | 0 | 0.00 | | 0 | 0.00 | | 1 | 0.98 | ADRA2A | 2 | 2.18 | LDLR; SLC26A6 |
| negative regulation of endothelial cell apoptotic process: GO | 26 | 2 | 1.29 | SCG2; SERPINE1 | 1 | 0.45 | NDNF | 0 | 0.00 | | 1 | 16.07 | SERPINE1 | 2. | 1.95 | ANGPT1; NDNF | 2 | 2.18 | ANGPTL4; IL10 |
| polyol biosynthetic process: GO | 26 | 2 | 1.29 | CYP27B1; PTAFR | 2 | 0.91 | LEP; PCK1 | 0 | 0.00 | | 0 | 0.00 | | 3 | 2.93 | ACER1; CYP3A4; FGF2 | 2 | 2.18 | CYP27B1; PTAFR |
| raccycd pathway | 26 | 2 | 1.29 | CCNE1; CDKN1A | 0 | 0.00 | | 0 | 0.00 | | 0 | 0.00 | | 0 | 0.00 | | 2 | 2.18 | CDKN1A; E2F1 |
| regulation of oxidative stress induced intrinsic apoptotic signaling pathway: GO | 26 | 2 | 1.29 | HIF1A; HSPH1 | 2 | 0.91 | NOL3; NOX1 | 0 | 0.00 | | 0 | 0.00 | | 0 | 0.00 | | 2 | 2.18 | HIF1A; HSPH1 |
| ammonium transmembrane transporter activity: GO | 26 | 1 | 0.64 | RHCG | 2 | 0.91 | RHAG; SLC6A2 | 0 | 0.00 | | 0 | 0.00 | | 2 | 1.95 | RHBG; SLC18A2 | 2 | 2.18 | RHCG; SLC18A3 |
| negative regulation | 26 | 1 | 0.64 | BDKRB2 | 0 | 0.00 | | 0 | 0.00 | | 0 | 0.00 | | 0 | 0.00 | | 2 | 2.18 | BDKRB2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| of signal transduction by p53 class mediator: GO | | | | | | | | | | | | | | | | | | | SNAI2 |
| cellular response to alcohol: GO | 111 | 12 | 1.81 | BLM; CCL7; CCNA2; CYP24A1; H2AFZ; IL6; JUP; LRP8; MSN; PTAFR; TNC; UGT1A1 | 6 | 0.64 | GPLD1; MLC1; MSTN; PPARGC1A; PTCH1; RORC | 0 | 0.00 | | 0 | 0.00 | | 4 | 0.92 | ESR1; GPLD1; PPARGC1A; PTCH1 | 6 | 1.53 | BLM; CCNA2; H2AFZ; IL10; MSN; PTAFR |
| regulation of alpha beta t cell activation: GO | 67 | 13 | 3.25 | ANXA1; CD3E; CD80; EBI3; HSPH1; IFNG; IL12B; IL4R; IL6; JAK3; PNP; PRKCQ; SASH3 | 1 | 0.18 | ZBTB16 | 0 | 0.00 | | 0 | 0.00 | | 0 | 0.00 | | 4 | 1.69 | CD83; HSPH1; PNP; PRKCQ |
| er to golgi transport vesicle: GO | 67 | 5 | 1.25 | AREG; CTSC; PCSK9; SERPINA1; TGFA | 2 | 0.35 | FOLR1; GRIA1 | 0 | 0.00 | | 0 | 0.00 | | 3 | 1.14 | CNIH3; GRIA1; HLA-DQB2 | 4 | 1.69 | AREG; HLA-G; PCSK9; TGFA |
| telomerase pathway | 67 | 4 | 1.00 | BLM; IFNG; MXD1; PIF1 | 2 | 0.35 | EGF; TERT | 0 | 0.00 | | 0 | 0.00 | | 2 | 0.76 | EGF; ESR1 | 4 | 1.69 | BLM; E2F1; MXD1; PIF1 |
| actin filament: GO | 67 | 3 | 0.75 | FERMT1; MYO1B; RAC2 | 10 | 1.76 | ACTA1; ACTN2; AMOT; ARHGAP6; COBL; ESPN; GAS2; MYO1A; MYO3A; TPM1 | 0 | 0.00 | | 1 | 6.24 | RAC2 | 1 | 0.38 | DPYSL3 | 4 | 1.69 | ACTN1; FERMT1; MYO1B; TPM4 |
| lymphocyte migration: GO | 46 | 10 | 3.64 | ARTN; CCL17; CCL18; CCL21; CCL22; CCL3; | 1 | 0.26 | CCL14 | 0 | 0.00 | | 0 | 0.00 | | 1 | 0.55 | CCL14 | 3 | 1.85 | ARTN; CCL20; CXCL11 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | CXCL10; CXCL11; CXCL13; GPR15 | | | | | | | | | | | | | | | |
| apc/c: cdc20 mediated degradation of securin | 46 | 5 | 1.82 | CDC20; PSMA5; PSMB6; PTTG1; UBE2C | 0 | 0.00 | | 0 | 0.00 | | 0 | 0.00 | | 0 | 0.00 | | 3 | 1.85 | CDC20; PTTG1; UBE2C |
| ribosomal large subunit biogenesis: GO | 46 | 4 | 1.46 | DDX28; EBNA1BP2; EIF6; RPL26L1 | 0 | 0.00 | | 0 | 0.00 | | 0 | 0.00 | | 0 | 0.00 | | 3 | 1.85 | DDX28; EBNA1BP2; EIF6 |
| endoribonuclease activity: GO | 46 | 3 | 1.09 | EXO1; RPP40; ZC3H12A | 0 | 0.00 | | 0 | 0.00 | | 0 | 0.00 | | 0 | 0.00 | | 3 | 1.85 | EXO1; FEN1; ZC3H12A |
| Ikb1 pathway | 46 | 3 | 1.09 | SFN; YWHAQ; YWHAZ | 3 | 0.77 | BRSK2; MAPT; PRKAA2 | 0 | 0.00 | | 0 | 0.00 | | 4 | 2.21 | BRSK2; ESR1; MAPT; PRKAA2 | 3 | 1.85 | SFN; YWHAQ; YWHAZ |
| transport of glucose and other sugars bile salts and organic acids metal ions and amine compounds | 89 | 8 | 1.50 | RHCG; SLC10A6; SLC16A1; SLC2A1; SLC2A9; SLC39A6; SLC5A1; SLC6A11 | 9 | 1.19 | CP; RHAG; SLC13A2; SLC14A1; SLC14A2; SLC16A8; SLC2A4; SLC5A2; SLC6A2 | 0 | 0.00 | | 0 | 0.00 | | 6 | 1.71 | CP; SLC13A2; SLC14A1; SLC18A2; SLC2A12; SLC40A1 | 5 | 1.59 | RHCG; SLC13A5; SLC2A1; SLC2A9; SLC6A11 |
| dorsal ventral pattern formation: GO | 89 | 6 | 1.13 | DUSP6; GREM1; MDFI; RGS20; TBX20; WNT7A | 14 | 1.86 | CXXC4; DSCAML1; EGF; FOXN4; GLI2; GREM2; GSC; HHIP; LRP4; NOG; PAX6; PTCH1; SOX1; SP8 | 0 | 0.00 | | 0 | 0.00 | | 6 | 1.71 | CHRD; EGF; FOXA1; GLI2; GREM2; PTCH1 | 5 | 1.59 | BMPR1B; DUSP6; MDFI; RGS20; WNT7A |
| protein sumoylation: GO | 112 | 6 | 0.90 | BIRC5; BLM; CBX2; CDCA8; PCNA; TOP2A | 1 | 0.11 | MITF | 0 | 0.00 | | 0 | 0.00 | | 1 | 0.23 | MITF | 6 | 1.52 | AURKB; BIRC5; BLM; CBX2; CDCA8; TOP2A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| maintenance of location: GO | 135 | 14 | 1.74 | ASPM; CALR; HK2; HSPA5; IL1B; JUP; LTBP1; MDFI; PDIA3; S100A7; S100A8; S100A9; SRGN; TWF1 | 18 | 1.57 | ACVR1C; ALB; APOE; ATP2A1; CASQ2; ENPP1; FITM2; GRIK5; GSN; NR5A1; PKD1; PLIN5; SCIN; SHANK1; SLC17A7; SPTBN4; SYNE1; TLN2 | 1 | 3.10 | ACVR1C | 2 | 6.19 | FFAR2; IL1B | 6 | 1.13 | DGAT2; SCIN; SLC18A2; SPTBN4; SYNE1; TLN2 | 7 | 1.47 | ASPM; BCL3; HK2; HSPA5; IL10; MDFI; TWF1 |
| sodium ion transport: GO | 135 | 7 | 0.87 | ATP12A; ATP1B3; KCNK1; SLC10A6; SLC38A1; SLC4A8; SLC5A1 | 16 | 1.40 | ABCB11; ATP1A2; FXYD2; NALCN; SCN7A; SLC10A2; SLC13A2; SLC17A4; SLC17A7; SLC24A2; SLC34A3; SLC4A4; SLC5A2; SLC5A9; SLC9A2; SLC9A4 | 0 | 0.00 | | 0 | 0.00 | | 8 | 1.51 | ATP1B2; NALCN; SCN7A; SCNN1B; SLC13A2; SLC4A4; SLC5A9; SLC9A2 | 7 | 1.47 | KCNK1; SCNN1D; SGK1; SLC13A5; SLC20A1; SLC4A7; SLC5A5 |
| filopodium: GO | 90 | 9 | 1.67 | ARL4C; CXADR; ENAH; FSCN1; ITGA3; MSN; MYO1B; PDPN; TWF1 | 10 | 1.31 | ACTA1; ACTN2; APBB1; DMD; EPHB1; MYO3A; NLGN1; PALM; PPP1R9A; SRCIN1 | 1 | 4.64 | SRCIN1 | 0 | 0.00 | | 1 | 0.28 | PALM | 5 | 1.58 | ENAH; ITGA3; MSN; MYO1B; TWF1 |
| golgi lumen: GO | 90 | 8 | 1.49 | DEFB103A; | 19 | 2.49 | BCAN; F10; | 0 | 0.00 | | 1 | 4.64 | DEFB4A | 6 | 1.69 | DCN; GPC2; | 5 | 1.58 | AGRN; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | DEFB103B; DEFB4A; HS3ST1; NGF; SDC1; WNT5A; WNT7A | | | F7; GPC2; GPC3; GPC6; LHB; MUC16; MUC20; MUC4; MUC5AC; MUC5B; MUC6; MUC7; MUCL1; PCSK5; PRELP; SDC2; SOD3 | | | | | | | | | MUC20; MUC7; MUCL1; SOD3 | | | HS3ST1; NGF; WNT5A; WNT7A |
| metabolism of water-soluble vitamins and cofactors | 90 | 7 | 1.30 | GSTO1; MTHFD2; NAMPT; PARP9; PTGS2; SLC2A1; SLC52A2 | 6 | 0.79 | ACACB; ALDH1L1; ENPP1; FOLR1; PTGIS; SLC19A3 | 0 | 0.00 | | 0 | 0.00 | | 3 | 0.85 | AOX1; ENPP3; SLC19A3 | 5 | 1.58 | NAMPT; PARP9; PTGS2; SLC2A1; SLC52A2 |
| positive regulation of blood circulation: GO | 90 | 6 | 1.12 | ADCYAP1; F2RL1; GJA1; HMOX1; PTAFR; PTGS2 | 12 | 1.57 | ADRA1A; ADRA1B; ADRA2A; ADRB1; AGT; EDN3; EPHX2; NKX2-5; NOS2; NPY IR; PLA2G6; TPM1 | 0 | 0.00 | | 0 | 0.00 | | 6 | 1.69 | ADRA1A; ADRA2A; CTGF; EDN3; HRC; NPY1R | 5 | 1.58 | HRH1; HRH2; PPARD; PTAFR; PTGS2 |
| antiviral mechanism by ifn-stimulated genes | 47 | 6 | 2.14 | HERC6; ISG15; KPNA2; MX1; STAT1; UBE2N | 0 | 0.00 | | 0 | 0.00 | | 1 | 8.89 | ISG15 | 0 | 0.00 | | 3 | 1.81 | HERC6; KPNA2; MX1 |
| isg15 antiviral mechanism | 47 | 6 | 2.14 | HERC6; ISG15; KPNA2; MX1; STAT1; UBE2N | 0 | 0.00 | | 0 | 0.00 | | 1 | 8.89 | ISG15 | 0 | 0.00 | | 3 | 1.81 | HERC6; KPNA2; MX1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| regulation of cardiac muscle tissue development: GO | 47 | 6 | 2.14 | CCNB1; CDK1; GJA1; GREM1; NRG1; TBX20 | 10 | 2.51 | DKK1; ERBB4; FGF9; FGFR1; JPH2; MYOCD; NKX2-5; NOG; RBP4; TBX5 | 0 | 0.00 | | 0 | 0.00 | | 5 | 2.70 | ERBB4; FGF2; FGFR1; KCNK2; PRICKLE1 | 3 | 1.81 | CCNB1; CDK1; NRG1 |
| response to progesterone: GO | 47 | 5 | 1.78 | CCNE1; DSG1; FOSL1; GJB2; SOCS3 | 3 | 0.75 | C3; CATSPERG; TXNIP | 0 | 0.00 | | 0 | 0.00 | | 3 | 1.62 | C3; CATSPERG; TXNIP | 3 | 1.81 | FOSL1; JUNB; SOCS3 |
| il6 7 pathway | 47 | 4 | 1.42 | IL6; PTPRE; SOCS3; STAT1 | 1 | 0.25 | MITF | 0 | 0.00 | | 0 | 0.00 | | 1 | 0.54 | MITF | 3 | 1.81 | JUNB; PTPRE; SOCS3 |
| positive regulation of myeloid leukocyte differentiation: GO | 47 | 4 | 1.42 | CA2; IFNG; IL12B; IL20 | 3 | 0.75 | IL34; IL5; LIF | 0 | 0.00 | | 0 | 0.00 | | 1 | 0.54 | TESC | 3 | 1.81 | CA2; IL20; TRIB1 |
| type ii diabetes mellitus | 47 | 3 | 1.07 | HK2; PKM; SOCS3 | 5 | 1.26 | ABCC8; ADIPOQ; IRS2; IRS4; SLC2A4 | 1 | 8.89 | ADIPOQ | 0 | 0.00 | | 1 | 0.54 | CACNA1G | 3 | 1.81 | HK2; PKM; SOCS3 |
| neurotransmitter release cycle | 47 | 2 | 0.71 | HSPA8; SLC6A11 | 9 | 2.26 | APBA1; MAOA; RIMS1; SLC17A7; SLC1A2; SLCIA6; SLC1A7; SYN2; SYT1 | 0 | 0.00 | | 0 | 0.00 | | 7 | 3.78 | ALDH5A1; APBA1; RIMS1; SLC18A2; SLC1A6; SLC1A7; SYN2 | 3 | 1.81 | HSPA8; SLC18A3; SLC6A11 |
| rho protein signal transduction: GO | 47 | 2 | 0.71 | CFL1; RHOD | 4 | 1.00 | ADRA2A; AGTR1; ARHGAP6; ROPN1B | 0 | 0.00 | | 0 | 0.00 | | 3 | 1.62 | ADRA2A; AGTR1; ROPN1B | 3 | 1.81 | CDC42EP1; CFL1; RHOD |
| negative regulation of intracellular transport: GO | 136 | 11 | 1.35 | FOXF1; GSTO1; HMOX1; IL13RA2; LYPLA1; MDFI; | 13 | 1.13 | ADIPOQ; ANXA13; APOD; BCL2; CASQ2; CRYAB; GSTM2; | 2 | 6.15 | ADIPOQ; CRYAB | 0 | 0.00 | | 5 | 0.93 | ANGPT1; BCL2; MAPT; SVIP; TRDN | 7 | 1.46 | IL10; IL13RA2; MDFI; NTSR1; SNAI2; TXN; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | NTSR1; SLC25A5; TXN; YOD1; ZC3H12A | | | MAPT; PKD1; PKDCC; SVIP; TRDN; USP17L2 | | | | | | | | | | | | ZC3H12A |
| negative regulation of cytoplasmic transport: GO | 113 | 7 | 1.04 | GSTO1; LYPLA1; MDFI; NTSR1; TXN; YOD1; ZC3H12A | 9 | 0.94 | ANXA13; APOD; BCL2; CASQ2; GSTM2; PKD1; PKDCC; SVIP; TRDN | 0 | 0.00 | | 0 | 0.00 | | 4 | 0.90 | ANGPT1; BCL2; SVIP; TRDN | 6 | 1.51 | IL10; MDFI; NTSR1; SNAI2; TXN; ZC3H12A |
| positive regulation of cd4 positive alpha beta t cell activation: GO | 27 | 8 | 4.96 | ANXA1; CD80; IFNG; IL12B; IL4R; IL6; PRKCQ; SASH3 | 0 | 0.00 | | 0 | 0.00 | | 0 | 0.00 | | 0 | 0.00 | | 2 | 2.10 | CD83; PRKCQ |
| aromatic amino acid family metabolic process: GO | 27 | 5 | 3.10 | IDO1; IL4I1; KYNU; TDO2; TH | 2 | 0.87 | DCT; HAAO | 0 | 0.00 | | 1 | 15.48 | TDO2 | 0 | 0.00 | | 2 | 2.10 | HPDL; TH |
| hsf1-dependent transactivation | 27 | 5 | 3.10 | FPR1; HSPA6; HSPA8; HSPH1; TNFRSF21 | 0 | 0.00 | | 0 | 0.00 | | 0 | 0.00 | | 1 | 0.94 | SLC29A1 | 2 | 2.10 | HSPA8; HSPH1 |
| positive regulation of acute inflammatory response: GO | 27 | 5 | 3.10 | F12; IL1B; IL6; OSM; PTGS2 | 4 | 1.75 | C3; CNR1; KLKB1; NPY5R | 0 | 0.00 | | 3 | 46.43 | FFAR2; IL1B; OSM | 1 | 0.94 | C3 | 2 | 2.10 | F12; PTGS2 |
| pyrimidine nucleoside biosynthetic process: GO | 27 | 5 | 3.10 | CDA; NME1; TK1; TYMP; UPP1 | 1 | 0.44 | UPP2 | 0 | 0.00 | | 0 | 0.00 | | 0 | 0.00 | | 2 | 2.10 | CDA; TK1 |
| negative regulation of production of molecular mediator of immune response: GO | 27 | 4 | 2.48 | HMOX1; IL13RA2; JAK3; SLAMF1 | 0 | 0.00 | | 0 | 0.00 | | 0 | 0.00 | | 1 | 0.94 | ANGPT1 | 2 | 2.10 | IL10; IL13RA2 |
| positive regulation of organic acid transport: GO | 27 | 4 | 2.48 | CCK; IL1B; NTSR1; P2RY2 | 3 | 1.31 | CYP4A11; P2RX7; PLA2G6 | 0 | 0.00 | | 1 | 15.48 | IL1B | 1 | 0.94 | CYP4A11 | 2 | 2.10 | NTSR1; P2RY2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| axis elongation: GO | 27 | 3 | 1.86 | AREG; TNC; WNT5A | 3 | 1.31 | FGF1; MAGI2; WNT11 | 0 | 0.00 | | 0 | 0.00 | | | 2.82 | ESR1; SPRY1; WNT11 | 2 | 2.10 | AREG; WNT5A |
| establishment or maintenance of epithelial cell apical basal polarity: GO | 27 | 3 | 1.86 | FOXF1; MSN; WNT5A | 2 | 0.87 | DLG2; WNT11 | 0 | 0.00 | | 0 | 0.00 | | 2 | 1.88 | DLG2; WNT11 | 2 | 2.10 | MSN; WNT5A |
| ncam signaling for neurite out growth | 27 | 3 | 1.86 | ARTN; CDK1; GDNF | 3 | 1.31 | CACNB1; NCAM1; SPTBN4 | 0 | 0.00 | | 0 | 0.00 | | 4 | 3.76 | CACNAIG; CACNB1; NCAM1; SPTBN4 | 2 | 2.10 | ARTN; CDK1 |
| amine compound slc transporters | 27 | 2 | 1.24 | RHCG; SLC6A11 | 4 | 1.75 | RHAG; SLC14A1; SLC14A2; SLC6A2 | 0 | 0.00 | | 0 | 0.00 | | 2 | 1.88 | SLC14A1; SLC18A2 | 2 | 2.10 | RHCG; SLC6A11 |
| cell proliferation in forebrain: GO | 27 | 2 | 1.24 | KIF14; WNT7A | 5 | 2.18 | DCT; EMX2; FABP7; FGFR1; POU3F3 | 0 | 0.00 | | 0 | 0.00 | | 3 | 2.82 | EMX2; FGFR1; POU3F3 | 2 | 2.10 | KIF14; WNT7A |
| cerebral cortex radially oriented cell migration: GO | 27 | 2 | 1.24 | CDK5R1; FBXO45 | 3 | 1.31 | DCX; POU3F3; RELN | 0 | 0.00 | | 0 | 0.00 | | 2 | 1.88 | POU3F3; RELN | 2 | 2.10 | CDK5R1; FBXO45 |
| dopamine receptor signaling pathway: GO | 27 | 2 | 1.24 | GNA15; GNAI3 | 5 | 2.18 | ADCY5; ADCY6; DRD1; DRD4; RGS9 | 0 | 0.00 | | 0 | 0.00 | | 0 | 0.00 | | 2 | 2.10 | GNA15; KLF16 |
| nadp metabolic process: GO | 27 | 2 | 1.24 | PGM2; TPI1 | 3 | 1.31 | ASPDH; FMO2; NOX1 | 0 | 0.00 | | 0 | 0.00 | | 0 | 0.00 | | 2 | 2.10 | TKT; TPI1 |
| negative regulation of axon guidance: GO | 27 | 2 | 1.24 | SEMA4B; WNT5A | 7 | 3.06 | PLXNA3; SEMA3A; SEMA3B; SEMA3D; SEMA3E; SEMA3G; SLIT2 | 0 | 0.00 | | 0 | 0.00 | | 3 | 2.82 | SEMA3E; SEMA4G; SLIT2 | 2 | 2.10 | SEMA4B; WNT5A |
| phosphatidylserine metabolic process: GO | 27 | 2 | 1.24 | PLA2G4D; SERINC2 | 2 | 0.87 | PLA2G16; PLA2G5 | 1 | 15.48 | PLA2G16 | 0 | 0.00 | | 0 | 0.00 | | 2 | 2.10 | PLA2G4D; SERINC2 |
| regulation | 27 | 2 | 1.24 | RGS20; | 2 | 0.87 | DACT1; EGF | 0 | 0.00 | | 0 | 0.00 | | 3 | 2.82 | DACTI; EGF; | 2 | 2.10 | RGS20; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| of catenin import into nucleus: GO | | | | SULF2 | | | | | | | | | | | | FZD7 | | | SNAI2 |
| reproductive behavior: GO | 27 | 2 | 1.24 | SERPINE2; TH | 4 | 1.75 | DRD1; GRIN1; NPAS1; PPP1R1B | 0 | 0.00 | | 0 | 0.00 | | 0 | 0.00 | | 2 | 2.10 | SERPINE2; TH |
| sulfur compound transmembrane transporter activity: GO | 27 | 2 | 1.24 | SLC26A9; SLC7A11 | 5 | 2.18 | SLC19A3; SLC26A1; SLC26A5; SLC26A7; SLC7A9 | 0 | 0.00 | | 0 | 0.00 | | 1 | 0.94 | SLC19A3 | 2 | 2.10 | SLC26A6; SLC7A11 |
| fibronectin binding: GO | 27 | 1 | 0.62 | ITGA3 | 3 | 1.31 | CCDC80; MYOC; SSC5D | 0 | 0.00 | | 0 | 0.00 | | 7 | 6.59 | CCDC80; CTGF; FBLN1; IGFBP5; LRRC15; MYOC; SSC5D | 2 | 2.10 | IGFBP3; ITGA3 |
| histone h3 k4 methylation: GO | 27 | 1 | 0.62 | HIST1H1D | 0 | 0.00 | | 0 | 0.00 | | 0 | 0.00 | | 0 | 0.00 | | 2 | 2.10 | BEND3; HIST1HID |
| resolution of abasic sites (ap sites) | 27 | 1 | 0.62 | PCNA | 0 | 0.00 | | 0 | 0.00 | | 0 | 0.00 | | 0 | 0.00 | | 2 | 2.10 | FEN1; NEIL3 |
| regulation of synaptic plasticity: GO | 137 | 5 | 0.61 | CDC20; PLK2; PTGS2; SERPINE2; UNC13A | 27 | 2.33 | ADORA1; AGT; APOE; ATP2B2; BCAN; CAMK2A; CAMK2B; CNTN4; DRD1; FGF14; GRIA1; GRID2IP; GRIN1; GRIN2A; KCNB1; NCAM1; NETO1; NEUROD2; | 0 | 0.00 | | 0 | 0.00 | | 6 | 1.11 | GRIA1; GRID2IP; NCAM1; RELN; RIMS1; SNCA | 7 | 1.45 | CDC20; HRH1; HRH2; PLK2; PTGS2; SERPINE2; UNC13A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline: Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo: Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo: Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | | | | NLGN1; PPP1R9A; RELN; RIMS1; SHISA6; SHISA8; SLC24A2; SNCA; SYNGR1 | | | | | | | | | | | | |
| complement and coagulation cascades | 69 | 8 | 1.94 | BDKRB1; BDKRB2; F12; PLAU; PLAUR; SERPINA1; SERPINE1; THBD | 10 | 1.71 | C3; C4BPA; C6; C7; CFD; CFH; F10; F7; KLKB1; SERPINA5 | 0 | 0.00 | | 1 | 6.06 | SERPINE1 | 2 | 0.74 | C3; CFH | 4 | 1.64 | BDKRB2; F12; PLAT; THBD |
| cellular response to carbohydrate stimulus: GO | 69 | 7 | 1.70 | CLEC7A; GJB6; HIF1A; IL1B; NME1; PLAU; TH | 7 | 1.20 | COLEC12; GRIK5; IRS2; KCNB1; LEP; MLXIPL; PPARGC1A | 0 | 0.00 | | 1 | 6.06 | IL1B | 3 | 1.10 | PDK3; PPARGC1A; SLC29A1 | 4 | 1.64 | CLEC7A; HIF1A; SLC26A6; TH |
| phase1 functionalization of compounds | 69 | 7 | 1.70 | ADH7; CYP24A1; CYP27B1; CYP2S1; CYP4F11; PTGS2; SMOX | 20 | 3.42 | ADH1B; ADH1C; ALDH1A1; CYP17A1; CYP1A1; CYP1A2; CYP21A2; CYP2A6; CYP2C9; CYP2D6; CYP2J2; CYP2W1; CYP3A5; CYP4A11; CYP4B1; CYP4F12; CYP4F8; FMO2; MAOA; PTGIS | 0 | 0.00 | | 0 | 0.00 | | 6 | 2.21 | CYP2W1; CYP3A4; CYP3A5; CYP4A11; CYP4B1; CYP4F12 | 4 | 1.64 | CYP27B1; CYP2S1; PTGS2; SMOX |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| regulation of dendrite development: GO | 114 | 7 | 1.03 | CDC20; CDK5R1; CFL1; CHRNA3; LRP8; NRG1; PLK2 | 17 | 1.76 | APOE; BMP5; CAMK1; CAMK2B; COBL; EEF2K; FOXO6; GRIN1; ILIRAPL1; NLGN1; PAK3; PALM; PPP1R9A; RELN; SDC2; SHANK1; SRCIN1 | 1 | 3.67 | SRCIN1 | 0 | 0.00 | | 6 | 1.34 | CAMK1; FOXO6; LPAR1; PAK3; PALM; RELN | 6 | 1.49 | CDC20; CDK5R1; CFL1; NRG1; PLK2; SGK1 |
| positive regulation of chemokine production: GO | 48 | 11 | 3.83 | ADCYAP1; HIF1A; HMOX1; IFNG; IL1B; ILIRL1; IL4R; IL6; P2RY2; PYCARD; WNT5A | 2 | 0.49 | ADIPOQ; LPL | 2 | 17.41 | ADIPOQ; LPL | 2 | 17.41 | FFAR2; IL1B | 0 | 0.00 | | 3 | 1.77 | HIF1A; P2RY2; WNT5A |
| nuclear inner membrane: GO | 48 | 4 | 1.39 | FAM169A; IFI27; LMNB1; LMNB2 | 3 | 0.74 | P2RX1; P2RX6; P2RX7 | 0 | 0.00 | | 0 | 0.00 | | 0 | 0.00 | | 3 | 1.77 | FAM169A; IFI27; LMNB2 |
| purine containing compound catabolic process: GO | 48 | 3 | 1.05 | AHCY; NUDT15; PNP | 3 | 0.74 | ENPP4; PDE11A; PDE9A | 0 | 0.00 | | 0 | 0.00 | | 2 | 1.06 | AOX1; PDE9A | 3 | 1.77 | NUDT15; PNP; XDH |
| negative regulation of response to dna damage stimulus: GO | 48 | 2 | 0.70 | HMGA2; POLQ | 1 | 0.25 | CLU | 0 | 0.00 | | 0 | 0.00 | | 2 | 1.06 | CLU; CXCL12 | 3 | 1.77 | HMGA2; POLQ; SNAI2 |
| negative regulation of intracellular protein transport: GO | 92 | 5 | 0.91 | LYPLA1; MDFI; TXN; YOD1; ZC3H12A | 7 | 0.90 | ADIPOQ; ANXA13; APOD; PKD1; PKDCC; SVIP; USP17L2 | 1 | 4.54 | ADIPOQ | 0 | 0.00 | | 2 | 0.55 | ANGPT1; SVIP | 5 | 1.54 | IL10; MDFI; SNAI2; TXN; ZC3H12A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| endonuclease activity: GO | 115 | 7 | 1.02 | DNASE1L3; EXO1; GEN1; HMGA2; RNASE7; RPP40; ZC3H12A | 2 | 0.21 | DNASE1L2; NEIL1 | 0 | 0.00 | | 0 | 0.00 | | 0 | 0.00 | | 6 | 1.48 | DNASE1L3; EXO1; FEN1; HMGA2; NEIL3; ZC3H12A |
| positive regulation of apoptotic signaling pathway: GO | 162 | 21 | 2.17 | BAK1; CTSC; DYNLL1; FAM162A; IL19; MMP9; OSM; PDIA3; PLAUR; PPIF; PYCARD; S100A8; S100A9; SFN; TGFBR1; TNFRSF10A; TNFRSF12A; TNFSF10; TP63; YWHAQ; YWHAZ | 9 | 0.66 | AGT; BCL2; CLU; G0S2; GSN; INHBB; NOX1; PLA2G6; TIMP3 | 0 | 0.00 | | 2 | 5.16 | GZMB; OSM | 2 | 0.31 | BCL2; CLU | 8 | 1.40 | BAK1; BMPRIB; E2F1; IL19; PPIF; SFN; YWHAQ; YWHAZ |
| neural precursor cell proliferation: GO | 70 | 7 | 1.67 | ARTN; ASPM; KIF14; MELK; RAB10; RACGAP1; WNT7A | 10 | 1.69 | DCT; EMX2; EPHB1; FABP7; FGFR1; HHIP; ID4; KCNA1; POU3F3; SOX5 | 0 | 0.00 | | 0 | 0.00 | | 3 | 1.09 | EMX2; FGFR1; POU3F3 | 4 | 1.62 | ARTN; ASPM; KIF14; WNT7A |
| antiporter activity: GO | 70 | 5 | 1.20 | SLC26A9; SLC7A1; SLC7A11; SLC7A5; SLC7A8 | 11 | 1.85 | SLC22A9; SLC24A2; SLC26A1; SLC26A5; SLC26A7; SLC4A1; SLC7A10; SLC7A14; SLC7A9; SLC9A2; SLC9A4 | 0 | 0.00 | | 0 | 0.00 | | 2 | 0.73 | CLCN4; SLC9A2 | 4 | 1.62 | SLC26A6; SLC7A1; SLC7A11; SLC7A5 |
| endothelial cell | 70 | 5 | 1.20 | F2RL1; MSN; | 7 | 1.18 | ARHGEF26; | 0 | 0.00 | | 0 | 0.00 | | 3 | 1.09 | ARHGEF26; | 4 | 1.62 | MSN; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| differentiation: GO | | | | NRG1; RAP2B; WNT7A | | | GSTM3; HAPLN2; MESP1; SCUBE1; TMEM100; TNMD | | | | | | | | | MESP1; TNMD | | | NRG1; RAP2B; WNT7A |
| regulation of neural precursor cell proliferation: GO | 70 | 5 | 1.20 | ADCYAP1; ASPM; HIF1A; IL1B; WNT5A | 6 | 1.01 | CDON; DCT; EGF; GLI2; PAX6; SOX10 | 0 | 0.00 | | 1 | 5.97 | IL1B | 3 | 1.09 | CDON; EGF; GLI2 | 4 | 1.62 | ASPM; HIF1A; SHCBP1; WNT5A |
| dicarboxylic acid transport: GO | 70 | 4 | 0.96 | NTSR1; PDPN; SLC26A9; SLC7A11 | 13 | 2.19 | APBA1; FOLR1; FOLR2; RIMS1; SLC13A2; SLC17A7; SLC1A2; SLC1A6; SLC1A7; SLC26A1; SLC26A5; SLC26A7; SYT1 | 0 | 0.00 | | 0 | 0.00 | | 5 | 1.81 | APBA1; RIMS1; SLC13A2; SLC1A6; SLC1A7 | 4 | 1.62 | NTSR1; SLC13A5; SLC26A6; SLC7A11 |
| positive regulation of cell cycle g1 s phase transition: GO | 28 | 5 | 2.99 | ANXA1; CDC45; CDC6; FAM83D; TP63 | 1 | 0.42 | CYP1A1 | 0 | 0.00 | | 0 | 0.00 | | 0 | 0.00 | | 2 | 2.03 | CDC45; CDC6 |
| regulation of meiotic nuclear division: GO | 28 | 5 | 2.99 | CALR; CDC20; FBXO5; OSM; WNT5A | 3 | 1.26 | LIF; NPM2; PIWIL2 | 0 | 0.00 | | 1 | 14.92 | OSM | 0 | 0.00 | | 2 | 2.03 | CDC20; WNT5A |
| quinone metabolic process: GO | 28 | 4 | 2.39 | AKR1B10; COQ2; CYP4F11; HMGCR | 0 | 0.00 | | 0 | 0.00 | | 0 | 0.00 | | 0 | 0.00 | | 2 | 2.03 | AKR1B10; PDSS1 |
| cadherin binding: GO | 28 | 3 | 1.79 | CDK5R1; JUP; TRPC4 | 2 | 0.84 | CTNNA3; PTPRT | 0 | 0.00 | | 0 | 0.00 | | 1 | 0.91 | PTPRT | 2 | 2.03 | CDK5R1; NDRG1 |
| glutamate metabolic | 28 | 3 | 1.79 | ALDH4A1; GOT2; HAL | 1 | 0.42 | PRODH | 0 | 0.00 | | 0 | 0.00 | | 2 | 1.81 | ALDH5A1; PRODH | 2 | 2.03 | GOT2; NAGS |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| process: GO | | | | | | | | | | | | | | | | | | | |
| negative regulators of ddx58/ifih1 signaling | 28 | 3 | 1.79 | CAP1; HERC6; ISG15 | 0 | 0.00 | | 0 | 0.00 | | 1 | 14.92 | ISG15 | 0 | 0.00 | | 2 | 2.03 | CAP1; HERC6 |
| actions of nitric oxide in the heart | 28 | 2 | 1.20 | BDKRB2; SLC7A1 | 3 | 1.26 | ACTA1; CHRM1; PRKAR2B | 1 | 14.92 | PRKAR2B | 0 | 0.00 | | 1 | 0.91 | CHRM1 | 2 | 2.03 | BDKRB2; SLC7A1 |
| lysosome vesicle biogenesis | 28 | 2 | 1.20 | AP1S3; HSPA8 | 0 | 0.00 | | 0 | 0.00 | | 0 | 0.00 | | 0 | 0.00 | | 2 | 2.03 | AP1S3; HSPA8 |
| peptide antigen binding: GO | 28 | 2 | 1.20 | SLC7A5; SLC7A8 | 1 | 0.42 | SLC7A9 | 0 | 0.00 | | 0 | 0.00 | | 0 | 0.00 | | 2 | 2.03 | HLA-G; SLC7A5 |
| regulation of anion transmembrane transport: GO | 28 | 2 | 1.20 | PTAFR; VDAC1 | 5 | 2.11 | ANO9; CFTR; CLCNKA; CLCNKB; IRS2 | 0 | 0.00 | | 0 | 0.00 | | 2 | 1.81 | ANO9; CLCN4 | 2 | 2.03 | PTAFR; VDAC1 |
| regulation of neuroblast proliferation: GO | 28 | 2 | 1.20 | ASPM; HIF1A | 3 | 1.26 | DCT; PAX6; SOX10 | 0 | 0.00 | | 0 | 0.00 | | 0 | 0.00 | | 2 | 2.03 | ASPM; HIF1A |
| somatic diversification of immunoglobulins: GO | 28 | 2 | 1.20 | EXO1; POLQ | 0 | 0.00 | | 0 | 0.00 | | 0 | 0.00 | | 0 | 0.00 | | 2 | 2.03 | EXO1; POLQ |
| auditory receptor cell differentiation: GO | 28 | 1 | 0.60 | PLS3 | 5 | 2.11 | ATP2B2; CLIC5; FGFR1; MCOLN3; PDZD7 | 0 | 0.00 | | 0 | 0.00 | | 4 | 3.63 | CLIC5; FGFR1; PDZD7; SLITRK6 | 2 | 2.03 | SLC4A7; TMC1 |
| lamellipodium assembly: GO | 28 | 1 | 0.60 | RHOD | 0 | 0.00 | | 0 | 0.00 | | 0 | 0.00 | | 0 | 0.00 | | 2 | 2.03 | RHOD; VAV2 |
| positive regulation of cartilage development: GO | 28 | 1 | 0.60 | WNT5A | 4 | 1.69 | GDF5; PKDCC; SOX5; ZBTB16 | 0 | 0.00 | | 0 | 0.00 | | 0 | 0.00 | | 2 | 2.03 | BMPR1B; WNT5A |
| response to epidermal growth factor: GO | 28 | 1 | 0.60 | GSTP1 | 0 | 0.00 | | 0 | 0.00 | | 0 | 0.00 | | 0 | 0.00 | | 2 | 2.03 | GSTP1; SNAI2 |
| sh2 domain binding: GO | 28 | 1 | 0.60 | SIT1 | 0 | 0.00 | | 0 | 0.00 | | 0 | 0.00 | | 1 | 0.91 | DLC1 | 2 | 2.03 | AFAP1L2; SHCBP1 |
| positive regulation | 139 | 12 | 1.44 | CRABP2; | 8 | 0.68 | BCL2; CDH4; | 0 | 0.00 | | 0 | 0.00 | | 5 | 0.91 | BCL2; | 7 | 1.43 | CRABP2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| of cell growth: GO | | | | HBEGF; HIST1H1B; KRT17; LPAR3; NRG1; S100A8; S100A9; SFN; TGFBR1; TNFRSF12A; UNC13A | | | CPNE9; MAPT; NTRK3; RIMS1; SYT1; SYT17 | | | | | | | | | CXCL12; MAPT; RIMS1; SYT17 | | | HBEGF; HIST1H1B; NRG1; SFN; SGK1; UNC13A |
| appendage development: GO | 163 | 10 | 1.03 | BAK1; CRABP2; GJA1; GREM1; ITGA6; PITX1; SALL3; TP63; WNT5A; WNT7A | 25 | 1.81 | AFF3; ALX1; ALX4; DKK1; FGF9; FGFR1; GDF5; GLI2; GPC3; HAND2; LRP4; MEOX2; MYH3; NOG; OSR1; OSR2; PCSK5; PKDCC; PTCH1; RNF165; SMOC1; SP8; TBX5; TFAP2B; ZBTB16 | 0 | 0.00 | | 0 | 0.00 | | 15 | 2.34 | AFF3; ALX4; B9D1; FGFR1; FRAS1; GLI2; HAND2; HOXA10; MEOX2; MYCN; OSR1; PRRX1; PTCH1; RECK; SHOX2 | 8 | 1.39 | BAK1; BMPR1B; CRABP2; ITGA6; ITGB4; PITX1; WNT5A; WNT7A |
| transcriptional repressor activity rna polymerase ii transcription regulatory region sequence specific binding: GO | 163 | 6 | 0.62 | E2F7; HMGA2; IFI16; ISX; MXD1; PRDM1 | 14 | 1.01 | BACH2; BHLHE41; DACH1; FEZF2; FOXD3; GATA1; MITF; MLXIPL; PAX6; TBX15; TCF21; ZBTB16; ZFPM2; | 0 | 0.00 | | 0 | 0.00 | | 7 | 1.09 | BACH2; BHLHE41; DACH1; MITF; TBX15; ZBTB20; ZFPM2 | 8 | 1.39 | ASCL2; E2F7; HMGA2; IFI16; KLF16; MXD1; PPARD; SNAI2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | ZNF536 | | | | | | | | | | | | |
| regulation of leukocyte chemotaxis: GO | 93 | 22 | 3.96 | C1QBP; CALR; CCL21; CCL3; CCL7; CXCL1; CXCL10; CXCL11; CXCL13; CXCL3; CXCL5; CXCL6; CXCL9; F2RL1; GREM1; IL1B; IL6; RAC2; S100A14; S100A7; SERPINE1; WNT5A | 4 | 0.51 | EDN3; F7; RARRES2; SLIT2 | 0 | 0.00 | | 5 | 22.47 | CXCL5; CXCL9; IL1B; RAC2; SERPINE1 | 4 | 1.09 | CXCL12; EDN3; RARRES2; SLIT2 | 5 | 1.52 | CXCL11; CXCL2; CXCL6; S100A14; WNT5A |
| regulation of interferon gamma production: GO | 93 | 19 | 3.42 | CIQBP; CD2; CD274; CD3E; EBI3; IL12B; IL12RB2; IL1B; IL1RL1; IL36RN; ISG15; PGLYRP2; PRNP; PYCARD; SASH3; SLAMF1; TNFSF9; WNT5A; ZC3H12A | 1 | 0.13 | SCGB1A1 | 0 | 0.00 | | 2 | 8.99 | IL1B; ISG15 | 0 | 0.00 | | 5 | 1.52 | BCL3; IL10; IL12RB2; WNT5A; ZC3H12A |
| monooxygenase activity: GO | 93 | 9 | 1.62 | CH25H; CYP24A1; CYP27B1; CYP27C1; | 22 | 2.79 | AGMO; CMAHP; CYP17A1; CYP1A1; | 0 | 0.00 | | 0 | 0.00 | | 8 | 2.19 | CMAHP; CYP2W1; CYP3A4; CYP3A5; | 5 | 1.52 | CYP27B1; CYP27C1; CYP2S1; SQLE; TH |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | CYP2S1; CYP4F11; CYP4F22; SQLE; TH | | | CYP1A2; CYP21A2; CYP2A6; CYP2C9; CYP2D6; CYP2J2; CYP2W1; CYP3A5; CYP4A11; CYP4B1; CYP4F12; CYP4F8; CYP4X1; CYP4Z1; FMO2; FMO5; NOS2; PTGIS | | | | | | | | | CYP4A11; CYP4B1; CYP4F12; FMO5 | | | |
| cytokine production: GO | 116 | 16 | 2.31 | EOMES; F2RL1; HIF1A; IDO1; IL12B; IL12RB2; IL19; IL1B; PNP; PTAFR; PTGS2; S100A12; S100A8; S100A9; SLAMF1; TREM1 | 8 | 0.81 | AGT; FABP4; GPAM; KLRF2; LEP; NOS2; PCSK5; WNT11 | 1 | 3.60 | GPAM | 3 | 10.81 | IL1B; LCP2; TREM1 | 2 | 0.44 | KLRF2; WNT11 | 6 | 1.47 | HIF1A; IL12RB2; IL19; PNP; PTAFR; PTGS2 |
| postreplication repair: GO | 49 | 7 | 2.39 | DTL; ISG15; PCNA; UBE2F; UBE2N; USP43; VCP | 0 | 0.00 | | 0 | 0.00 | | 1 | 8.53 | ISG15 | 0 | 0.00 | | 3 | 1.74 | DTL; UBE2F; USP43 |
| gdp binding: GO | 49 | 6 | 2.05 | GNAI3; RAB10; RAB31; RALB; RAN; RAP2B | 3 | 0.72 | PCK1; RAB3B; RAB9B | 0 | 0.00 | | 0 | 0.00 | | 1 | 0.52 | RAB3B | 3 | 1.74 | RAB31; RAN; RAP2B |
| negative regulation of i | 49 | 6 | 2.05 | GSTP1; IL1RL1; | 2 | 0.48 | ADIPOQ; PER1 | 1 | 8.53 | ADIPOQ | 0 | 0.00 | | 1 | 0.52 | ESR1 | 3 | 1.74 | GSTP1; IL10; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| kappab kinase nf kappab signaling: GO | | | | PYCARD; STAT1; TNIP3; ZC3H12A | | | | | | | | | | | | | | | ZC3H12A |
| regulation of synaptic transmission glutamatergic: GO | 49 | 5 | 1.71 | ADCYAP1; NTRK1; PTGS2; SERPINE2; UNC13A | 12 | 2.89 | ADORA1; ATP1A2; CNR1; DKK1; DRD1; GRIK3; GRM7; NLGN1; NRXN1; PLA2G6; RELN; SYT1 | 0 | 0.00 | | 0 | 0.00 | | 3 | 1.56 | GRIK3; NRXN1; RELN | 3 | 1.74 | PTGS2; SERPINE2; UNC13A |
| transport of inorganic cations anions and amino acids oligopeptides | 49 | 3 | 1.02 | SLC26A9; SLC38A5; SLC4A8 | 11 | 2.65 | SLC17A7; SLC1A6; SLC1A7; SLC24A2; SLC26A1; SLC26A7; SLC34A3; SLC4A1; SLC7A10; SLC9A2; SLC9A4 | 0 | 0.00 | | 0 | 0.00 | | 3 | 1.56 | SLC1A6; SLC1A7; SLC9A2 | 3 | 1.74 | SLC38A5; SLC4A3; SLC5A5 |
| cellular response to camp: GO | 49 | 1 | 0.34 | PTAFR | 4 | 0.96 | ADIPOQ; CFTR; EEF2K; GPD1 | 2 | 17.06 | ADIPOQ; GPD1 | 1 | 8.53 | AQP9 | 1 | 0.52 | IGFBP5 | 3 | 1.74 | PTAFR; SLC26A6; SLC5A5 |
| acute inflammatory response: GO | 71 | 11 | 2.59 | BDKRB2; F12; HIF1A; IL1A; IL1B; IL1RN; IL22; IL6; S100A8; SERPINA1; UGT1A1 | 4 | 0.66 | ADRA2A; ELANE; KLKB1; NUPRI | 0 | 0.00 | | 1 | 5.89 | IL1B | 2 | 0.72 | ADRA2A; ELANE | 4 | 1.60 | BDKRB2; F12; HIF1A; IL22 |
| regulation of biomineral tissue development: GO | 71 | 7 | 1.65 | CCL3; CYP27B1; GJA1; GREM1; HIF1A; LTF; SRGN | 8 | 1.33 | AMELX; ENPP1; GATA1; MGP; OSR1; OSR2; P2RX7; | 0 | 0.00 | | 0 | 0.00 | | 3 | 1.07 | DDR2; OSR1; TMEM119 | 4 | 1.60 | BMPR1B; CYP27B1; HIF1A; LTF |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | | | | PKDCC | | | | | | | | | | | | |
| multi organism behavior: GO | 71 | 6 | 1.41 | CNTNAP2; GCNT4; IL1B; NLGN4X; SERPINE2; TH | 10 | 1.66 | CNTFR; DACH1; DRD1; DRD4; GRIN1; HAND2; NRXN1; NRXN3; PPP1RIB; SHANK1 | 0 | 0.00 | | 1 | 5.89 | IL1B | 4 | 1.43 | CNTFR; DACH1; HAND2; NRXN1 | 4 | 1.60 | CNTNAP2; NLGN4X; SERPINE2; TH |
| golgi cisterna membrane: GO | 71 | 5 | 1.18 | FUT1; FUT2; FUT3; PITPNM1; PSENEN | 3 | 0.50 | ABO; FUT9; ST6GAL2 | 0 | 0.00 | | 0 | 0.00 | | 2 | 0.72 | ABO; GAL3ST4 | 4 | 1.60 | FUT1; FUT2; FUT3; PITPNM1 |
| exonuclease activity: GO | 71 | 4 | 0.94 | AEN; EXO1; ISG20; ZC3H12A | 2 | 0.33 | ENPP1; EXD3 | 0 | 0.00 | | 0 | 0.00 | | 2 | 0.72 | ENPP3; EXD3 | 4 | 1.60 | EXO1; FEN1; TREX2; ZC3H12A |
| response to nutrient: GO | 188 | 21 | 1.87 | ACP5; AHCY; ALPL; AQP3; BRCA2; CCNE1; CD3E; CXCL10; CYP24A1; CYP27B1; GSTP1; HMGCR; HMOX1; IL1B; KYNU; LDHA; LIPG; PTGS2; SLC16A1; TNC; UGT1A1 | 15 | 0.94 | ADIPOQ; ALB; CNR1; CP; CYP1A1; F7; FOLR1; FOLR2; GCGR; GSN; HMGCS2; LEP; MAPT; TIMP3; TTPA | 1 | 2.22 | ADIPOQ | 1 | 2.22 | IL1B | 3 | 0.41 | CP; HMGCS2; MAPT | 9 | 1.36 | ACP5; AQP3; BRCA2; BRIP1; CYP27B1; GSTP1; LDHA; PPARD; PTGS2 |
| cellular response to acid chemical: GO | 164 | 9 | 0.92 | CCNB1; HIF1A; IL1B; KRT13; NME1; PTAFR; TNC; WNT5A; ZC3H12A | 16 | 1.15 | ADCY6; CPEB1; FOLR1; FOLR2; FZD4; HMGCS2; LEP; LTK; | 0 | 0.00 | | 2 | 5.10 | FFAR2; IL1B | 14 | 2.17 | CPEB1; DGAT2; FZD7; HMGCS2; OSR1; P2RY4; PDK3; PDK4; | 8 | 1.38 | CCNB1; E2F1; HIF1A; KRT13; PTAFR; WNT5A; WNT9B; ZC3H12A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | | | | NTRK3; OSR1; PDGFD; PDK4; PPARGC1A; PRKAA2; RORB; WNT11 | | | | | | | | | PPARGC1A; PRKAA2; PTGDR; PTGFR; TESC; WNT11 | | | |
| hyaluronan metabolic process: GO | 29 | 5 | 2.89 | HAS3; HMMR; HYAL3; IL1B; MKI67 | 2 | 0.81 | HAS1; ITIH5 | 0 | 0.00 | | 1 | 14.41 | IL1B | 1 | 0.88 | FGF2 | 2 | 1.96 | HMMR; MKI67 |
| response to interleukin 4: GO | 29 | 5 | 2.89 | CTSB; HSPA5; IL24; IL4R; JAK3 | 0 | 0.00 | | 0 | 0.00 | | 0 | 0.00 | | 0 | 0.00 | | 2 | 1.96 | HSPA5; MCM2 |
| dna damage bypass | 29 | 4 | 2.31 | DTL; ISG15; PCNA; USP43 | 0 | 0.00 | | 0 | 0.00 | | 1 | 14.41 | ISG15 | 0 | 0.00 | | 2 | 1.96 | DTL; USP43 |
| fear response: GO | 29 | 4 | 2.31 | ADCYAP1; CCK; DPP4; VDAC1 | 6 | 2.44 | ADRB1; BCL2; DRD1; DRD4; GRM7; NEUROD2 | 0 | 0.00 | | 0 | 0.00 | | 2 | 1.75 | BCL2; MDK | 2 | 1.96 | DPP4; VDAC1 |
| neuroblast proliferation: GO | 29 | 4 | 2.31 | ARTN; ASPM; RAB10; RACGAP1 | 6 | 2.44 | DCT; FGFR1; HHIP; ID4; KCNA1; SOX5 | 0 | 0.00 | | 0 | 0.00 | | 1 | 0.88 | FGFR1 | 2 | 1.96 | ARTN; ASPM |
| positive regulation of interleukin 10 production: GO | 29 | 4 | 2.31 | CD274; IL12B; PYCARD; SASH3 | 1 | 0.41 | CD34 | 0 | 0.00 | | 0 | 0.00 | | 1 | 0.88 | CD34 | 2 | 1.96 | BCL3; CD83 |
| regulation of myelination: GO | 29 | 4 | 2.31 | IFNG; KIF14; NRG1; TNFRSF21 | 1 | 0.41 | TG | 0 | 0.00 | | 0 | 0.00 | | 0 | 0.00 | | 2 | 1.96 | KIF14; NRG1 |
| axon cytoplasm: GO | 29 | 3 | 1.73 | HIF1A; KIF4A; NEFL | 1 | 0.41 | KIF1A | 0 | 0.00 | | 0 | 0.00 | | 0 | 0.00 | | 2 | 1.96 | HIF1A; KIF4A |
| cyclin dependent protein kinase holoenzyme complex: GO | 29 | 3 | 1.73 | CCND2; CCNE1; CDKN1A | 0 | 0.00 | | 0 | 0.00 | | 0 | 0.00 | | 1 | 0.88 | CDK 14 | 2 | 1.96 | CCND2; CDKN1A |
| fatty acid binding: GO | 29 | 3 | 1.73 | FABP5; S100A8; | 6 | 2.44 | ACOX2; ALB; APOC1; | 0 | 0.00 | | 0 | 0.00 | | 4 | 3.50 | ACOX2; LPAR1; | 2 | 1.96 | FABP5; PPARD |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | S100A9 | | | FABP4; OXER1; SNCA | | | | | | | | | PMP2; SNCA | | | |
| phospho-lipase a2 activity: GO | 29 | 3 | 1.73 | PLA2G3; PLA2G4D; PLBD1 | 4 | 1.63 | PLA2G16; PLA2G5; PLA2G6; PNPLA3 | 1 | 14.41 | PLA2G16 | 0 | 0.00 | | 1 | 0.88 | PNPLA3 | 2 | 1.96 | PLA2G3; PLA2G4D |
| reelin pathway | 29 | 3 | 1.73 | CDK5R1; ITGA3; LRP8 | 4 | 1.63 | GRIN2A; MAPK8IP1; MAPT; RELN | 0 | 0.00 | | 0 | 0.00 | | 2 | 1.75 | MAPT; RELN | 2. | 1.96 | CDK5R1; ITGA3 |
| regulation of interleukin 4 production: GO | 29 | 3 | 1.73 | CD3E; PRKCQ; SASH3 | 1 | 0.41 | SCGB1A1 | 0 | 0.00 | | 0 | 0.00 | | 0 | 0.00 | | 2 | 1.96 | CD83; PRKCQ |
| stem cell division: GO | 29 | 3 | 1.73 | ASPM; RAB10; WNT7A | 4 | 1.63 | DCT; FGFR1; SOX5; ZBTB16 | 0 | 0.00 | | 0 | 0.00 | | 2 | 1.75 | FGFR1; FZD7 | 2 | 1.96 | ASPM; WNT7A |
| embryonic hindlimb morphogenesis: GO | 29 | 2 | 1.15 | PITX1; WNT7A | 6 | 2.44 | AFF3; ALX4; GPC3; OSR1; OSR2; ZBTB16 | 0 | 0.00 | | 0 | 0.00 | | 3 | 2.63 | AFF3; ALX4; OSR1 | 2 | 1.96 | PITX1; WNT7A |
| protein import into nucleus translocation: GO | 29 | 2 | 1.15 | IFNG; RAN | 0 | 0.00 | | 0 | 0.00 | | 0 | 0.00 | | 0 | 0.00 | | 2 | 1.96 | BCL3; RAN |
| rna stabilization: GO | 29 | 2 | 1.15 | GDNF; MYD88 | 0 | 0.00 | | 0 | 0.00 | | 0 | 0.00 | | 0 | 0.00 | | 2 | 1.96 | E2F1; MYD88 |
| signaling by retinoic acid | 29 | 2 | 1.15 | RDH16; SDR16C5 | 4 | 1.63 | ADHIC; ALDHIA1; FABP4; PDK4 | 0 | 0.00 | | 0 | 0.00 | | 2 | 1.75 | PDK3; PDK4 | 2 | 1.96 | PPARD; RDH16 |
| ether lipid metabolism | 29 | 1 | 0.58 | PLA2G3 | 3 | 1.22 | CHPT1; PLA2G5; PLA2G6 | 0 | 0.00 | | 0 | 0.00 | | 0 | 0.00 | | 2 | 1.96 | LPCAT1; PLA2G3 |
| regulation of pten gene transcription | 29 | 1 | 0.58 | CBX2 | 0 | 0.00 | | 0 | 0.00 | | 0 | 0.00 | | 0 | 0.00 | | 2 | 1.96 | CBX2; SNAI2 |
| regulation of vascular permeability: GO | 29 | 1 | 0.58 | BDKRB2 | 2 | 0.81 | AMOT; SLIT2 | 0 | 0.00 | | 0 | 0.00 | | 2 | 1.75 | ANGPT1; SLIT2 | 2 | 1.96 | BDKRB2; HRH1 |
| sodium channel regulator activity: GO | 29 | 1 | 0.58 | PCSK9 | 4 | 1.63 | AGT; FXYD2; GPLD1; SGK2 | 0 | 0.00 | | 0 | 0.00 | | 1 | 0.88 | GPLD1 | 2 | 1.96 | PCSK9; SGK1 |
| cellular response | 141 | 7 | 0.83 | EIF4EBP1; | 19 | 1.59 | ADIPOQ; | 2 | 5.93 | ADIPOQ; | 0 | 0.00 | | 6 | 1.08 | ATP6V0A4; | 7 | 1.41 | EIF4EBP1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| to insulin stimulus: GO | | | | GSTP1; HIF1A; NAMPT; PCSK9; RAB10; RAB31 | | | ALDOB; ATP6V0A4; ATP6V0E2; ATP6V1B1; CPEB1; DRD1; EEF2K; ENPP1; GPAM; GPLD1; HDAC5; HMGCS2; INHBB; IRS2; IRS4; PDK4; SLC2A4; SORBS1 | | | GPAM | | | | | | ATP6V0E2; CPEB1; GPLD1; HMGCS2; PDK4 | | | GSTP1; HIF1A; NAMPT; PCSK9; RAB31; TRIB3 |
| positive regulation of calcium ion transport into cytosol: GO | 50 | 8 | 2.68 | BAK1; BDKRB1; CXCL10; CXCL11; CXCL9; GSTO1; NPSR1; NTSR1 | 6 | 1.42 | DRD1; GSTM2; JPH2; P2RX7; SNCA; TRDN | 0 | 0.00 | | 1 | 8.36 | CXCL9 | 4 | 2.03 | ADCYAP1R1; SNCA; TRDN; TRPC1 | 3 | 1.70 | BAK1; CXCL11; NTSR1 |
| endoderm formation: GO | 50 | 6 | 2.01 | EOMES; HMGA2; LAMB3; MMP9; SOX7; TBX20 | 5 | 1.18 | COL11A1; DKK1; ITGA7; NANOG; NOG | 0 | 0.00 | | 0 | 0.00 | | 1 | 0.51 | COL11A1 | 3 | 1.70 | HMGA2; LAMB3; SOX7 |
| cell cell adherens junction: GO | 50 | 5 | 1.67 | CDH3; DSC2; DSP; GJA1; JUP | 7 | 1.65 | CADM2; CADM3; CAMSAP3; CTNNA3; DES; PGM5; SORBS1 | 0 | 0.00 | | 0 | 0.00 | | 3 | 1.52 | CADM2; CADM3; PGM5 | 3 | 1.70 | ACTN1; DSC2; NDRG1 |
| fas signaling pathway | 50 | 5 | 1.67 | BAK1; CSNK1A1; IL1A; PFN1; TPX2 | 1 | 0.24 | MAPK8IP1 | 0 | 0.00 | | 0 | 0.00 | | 0 | 0.00 | | 3 | 1.70 | BAK1; PFN1; TPX2 |
| lymphocyte homeostasis: GO | 50 | 5 | 1.67 | BAK1; CCNB2; | 3 | 0.71 | BCL2; CACNAIF; | 0 | 0.00 | | 1 | 8.36 | IL2RA | 3 | 1.52 | BCL2; SLC40A1; | 3 | 1.70 | BAK1; CCNB2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | HIF1A; IL2RA; JAK3 | | | P2RX7 | | | | | | | | | SLC46A2 | | | HIF1A |
| organic hydroxy compound catabolic process: GO | 72 | 7 | 1.63 | ADH7; AKRIB10; CYP24A1; CYP27B1; GK; NTSR1; TPI1 | 7 | 1.15 | ACADL; APOE; CYP4A11; CYP4F12; DIO3; DMGDH; MAOA | 0 | 0.00 | | 0 | 0.00 | | 3 | 1.06 | CYP4A11; CYP4F12; DMGDH | 4 | 1.58 | AKR1B10; CYP27B1; NTSR1; TPI1 |
| regulation of organ growth: GO | 72 | 7 | 1.63 | CCNB1; CDK1; DUSP6; GJA1; NRG1; SASH3; TBX20 | 9 | 1.47 | ACACB; CACNA2D2; ERBB4; FGF9; FGFR1; NKX2-5; NOG; RBP4; TBX5 | 0 | 0.00 | | 0 | 0.00 | | 6 | 2.12 | CACNA2D2; ERBB4; FGF2; FGFR1; FOXC1; KCNK2 | 4 | 1.58 | CCNB1; CDK1; DUSP6; NRG1 |
| activation of gtpase activity: GO | 72 | 5 | 1.16 | CCL21; CXCL13; ECT2; GPR65; WNT5A | 3 | 0.49 | NTRK3; SGSM1; SYDE2 | 0 | 0.00 | | 0 | 0.00 | | 2 | 0.71 | SGSM1; SYDE2 | 4 | 1.58 | ARHGEF16; ECT2; EPHA2; WNT5A |
| positive regulation of chemotaxis: GO | 118 | 23 | 3.26 | ARTN; C1QBP; CALR; CCL21; CCL3; CCL7; CXCL1; CXCL10; CXCL11; CXCL13; CXCL3; CXCL5; CXCL6; CXCL9; F2RL1; IL1B; IL6; RAC2; S100A14; S100A7; SCG2; SERPINE1; WNT5A | 8 | 0.80 | EDN3; F7; FGFR1; IL16; NTRK3; PDGFD; RARRES2; SLIT2 | 0 | 0.00 | | 5 | 17.71 | CXCL5; CXCL9; IL1B; RAC2; SERPINE1 | 7 | 1.51 | CXCL12; EDN3; FGF2; FGFR1; LPARI; RARRES2; SLIT2 | 6 | 1.44 | ARTN; CXCL11; CXCL2; CXCL6; S100A14; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| regulation of establishment of protein localization to mitochondrion: GO | 118 | 11 | 1.56 | DYNLL1; HSPH1; ITGAX; NRG1; RAC2; RUVBL1; SFN; TP63; UGCG; YWHAQ; YWHAZ | 6 | 0.60 | BCL2; CDKL2; HSPAIL; KAT2A; MYBPC1; NMUR1 | 0 | 0.00 | | 2 | 7.08 | GZMB; RAC2 | 2 | 0.43 | BCL2; RHOU | 6 | 1.44 | E2F1; HSPH1; NRG1; SFN; YWHAQ; YWHAZ |
| regulation of epithelial cell differentiation: GO | 118 | 10 | 1.42 | AQP3; CYP27B1; GDNF; IFNG; IL1B; IL20; SFN; STAT1; TP63; TRIM16 | 13 | 1.30 | ADIPOQ; ATOH8; BCL2; FOXE3; FRZB; KRT36; LIF; MESP1; OSR1; PAX6; PTCH1; PTCH2; TMEM100 | 1 | 3.54 | ADIPOQ | 1 | 3.54 | IL1B | 7 | 1.51 | ATOH8; BCL2; MESP1; MYCN; OSR1; PTCH1; PTCH2 | 6 | 1.44 | AQP3; CYP27B1; IL20; SFN; WNT9B; XDH |
| nuclear matrix: GO | 95 | 8 | 1.41 | BLM; CENPF; CENPW; CFL1; KIF4A; LMNB1; RUVBL1; UHRF1 | 4 | 0.50 | PHACTR3; RUNXIT1; SORBS1; SPTBN4 | 0 | 0.00 | | 0 | 0.00 | IL1B | 3 | 0.80 | PHACTR3; RUNX1T1; SPTBN4 | 5 | 1.49 | BLM; CENPF; CENPW; CFL1; KIF4A |
| excitatory synapse: GO | 190 | 12 | 1.06 | CDK5R1; CHRNA3; FBXO45; HOMER1; ITGA3; LRP8; LRRC4; NETO2; NLGN4X; P2RY1; RGS20; SH2D5 | 36 | 2.24 | ANKS1B; BCAS1; CAMK2A; CAMK2B; CHRM1; CHRM4; CLSTN2; CNKSR2; CPEB1; CTNND2; DCLK1; DLG2; DLGAP1; EEF2K; GRIA1; | 1 | 2.20 | SRCIN1 | 0 | 0.00 | | 13 | 1.74 | ADD3; CHRM1; CNKSR2; CPEB1; DCLK1; DLG2; GRIA1; MAPT; PALM; PCLO; PLCB4; PTCH1; SPOCK1 | 9 | 1.34 | CDK5R1; DLGAP2; FBXO45; HOMER1; ITGA3; LRRC4; NLGN4X; P2RY1; RGS20 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | GRIK5; GRIN1; GRIN2A; ITGA8; LRP4; MAGI2; MAPT; NETO1; NLGN1; P2RX6; PALM; PCLO; PLCB4; PPP1R9A; PTCH1; SHANK1; SLC17A7; SPOCK1; SRCIN1; | | | | | | | | | | | | |
| signaling by the b cell receptor (bcr) | 190 | 10 | 0.88 | CBX2; CDKN1A; EREG; HBEGF; IL1RL1; MYD88; NRAS; NRG1; PSMA5; PSMB6 | 7 | 0.43 | BTC; EGF; FGF1; FGFR1; FGFR3; IRS2; NRG2 | 0 | 0.00 | | 0 | 0.00 | | 5 | 0.67 | EGF; FGFR1; IGHM; PREX2; TRPC1 | 9 | 1.34 | CBX2; CDKN1A; EREG; HBEGF; IER3; MYD88; NRG1; SNAI2; TRIB3 |
| connective tissue development: GO | 190 | 9 | 0.79 | GPR4; HIF1A; HMGA2; HYAL3; NAMPT; PITX1; SULF2; WNT5A; WNT7A | 29 | 1.80 | ALX1; AMELX; BMP3; BMP5; CD34; COL11A1; COL11A2; CRIP1; FGF9; FGFR1; FGFR3; GDF5; GLI2; GPLD1; HAND2; HMGCS2; ID4; LEP; MGP; NOG; | 0 | 0.00 | | 0 | 0.00 | | 19 | 2.54 | CD34; COL11A1; CRIP1; CTGF; DGAT2; FGF2; FGFR1; FOXA1; GLI2; GPLD1; HAND2; HMGCS2; MYCN; OSR1; PPARGC1A; PRRX1; PTHIR; SHOX2; | 9 | 1.34 | BMPR1B; HIF1A; HMGA2; NAMPT; PITX1; PPARD; SNAI2; WNT5A; WNT7A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | OSR1; OSR2; PKD1; PPARGC1A; PTH1R; RORC; SOX8; TNMD; ZBTB16 | | | | | | | | | TNMD | | | |
| glycosamino-glycan metabolism | 119 | 10 | 1.41 | B3GNT3; CEMIP; CHST1; HAS3; HMMR; HPSE; HS3ST1; HS3ST3A1; HS3ST3B1; SDC1 | 17 | 1.69 | BCAN; CHST12; CHST5; GPC2; GPC3; GPC6; GXYLT2; HAS1; HPSE2; HS3ST2; HS3ST5; HS3ST6; HS6ST3; IDUA; PRELP; SDC2; UST | 0 | 0.00 | | 0 | 0.00 | | 7 | 1.49 | CHST12; DCN; DSEL; GPC2; GXYLT2; HPSE2; UST | 6 | 1.43 | AGRN; CHST1; HMMR; HPSE; HS3ST1; HS3ST3A1 |
| regulation of lipid biosynthetic process: GO | 119 | 6 | 0.84 | ANXA1; CYP27B1; IFNG; IL1B; LDLR; PTGS2 | 22 | 2.18 | ACADL; APOC1; APOE; BMP5; C3; CYP17A1; FGF1; FITM2; GPAM; GPLD1; HSD17B13; LEP; MLXIPL; NR5A1; PDK4; PLA2G6; PLIN5; PPARGC1A; PRKAA2; SERPINA12; SORBS1; THRSP | 2 | 7.02 | GPAM; THRSP | 1 | 3.51 | IL1B | 7 | 1.49 | C3; DGAT2; GPLD1; PDK4; PPARGC1A; PRKAA2; SERPINA12 | 6 | 1.43 | CYP27B1; LDLR; LPCAT1; PTGS2; SNAI2; TRIB3 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| cellular transition metal ion homeostasis: GO | 73 | 11 | 2.52 | HIF1A; HMOX1; HMOX2; LCN2; LTF; MT2A; PRNP; S100A8; S100A9; SCO2; SLC39A6 | 8 | 1.29 | ALAS2; CP; CYBRD1; HAMP; SCARA5; SLC22A17; TF; TMPRSS6 | 0 | 0.00 | | 0 | 0.00 | | 5 | 1.74 | CP; CYBRD1; SCARA5; SLC22A17; SLC40A1 | 4 | 1.55 | HIF1A; HMOX2; LTF; SCO2 |
| positive regulation of protein binding: GO | 73 | 5 | 1.15 | MMP9; PLK2; RALB; RAN; WNT5A | 4 | 0.65 | DACT1; PKD1; SPAG8; TERT | 0 | 0.00 | | 0 | 0.00 | | 1 | 0.35 | DACT1 | 4 | 1.55 | PLK2; RAN; TRIB3; WNT5A |
| drug metabolism other enzymes | 51 | 7 | 2.30 | CDA; TK1; TYMP; UGT1A1; UGT1A10; UGT1A7; UPP1 | 6 | 1.39 | CES1; CYP2A6; CYP3A5; UGT2A1; UGT2B7; UPP2 | 0 | 0.00 | | 0 | 0.00 | | 3 | 1.49 | CES1; CYP3A4; CYP3A5 | 3 | 1.67 | CDA; TK1; XDH |
| ddx58/ifih1-mediated induction of interferon-alpha/beta | 51 | 6 | 1.97 | CAP1; HERC6; IL6; ISG15; MYD88; S100A12 | 0 | 0.00 | | 0 | 0.00 | | 1 | 8.19 | ISG15 | 0 | 0.00 | | 3 | 1.67 | CAP1; HERC6; MYD88 |
| glutathione metabolism | 51 | 6 | 1.97 | GGCT; GSTO1; GSTP1; ODC1; RRM2; SRM | 6 | 1.39 | GGT7; GSTA3; GSTM2; GSTM3; GSTM5; GSTT2 | 0 | 0.00 | | 0 | 0.00 | | 1 | 0.50 | GSTM5 | 3 | 1.67 | GSTP1; ODC1; RRM2 |
| transferase activity transferring pentosyl groups: GO | 51 | 5 | 1.64 | NAMPT; PARP9; PNP; TYMP; UPP1 | 3 | 0.69 | ART5; GXYLT2; UPP2 | 0 | 0.00 | | 0 | 0.00 | | 1 | 0.50 | GXYLT2 | 3 | 1.67 | NAMPT; PARP9; PNP |
| negative regulation of erk1 and erk2 cascade: GO | 51 | 2 | 0.66 | DUSP6; GSTP1 | 6 | 1.39 | ADIPOQ; C1QL4; LIF; RPS6KA6; TIMP3; WNK2 | 1 | 8.19 | ADIPOQ | 1 | 8.19 | GBP1 | 3 | 1.49 | FBLN1; RPS6KA6; SPRY1 | 3 | 1.67 | DUSP6; GSTP1; SPRY4 |
| positive regulation of | 30 | 7 | 3.90 | ANXA1; CD3E; CD80; | 0 | 0.00 | | 0 | 0.00 | | 1 | 13.93 | IL1B | 0 | 0.00 | | 2 | 1.89 | CD83; PRKCQ |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| interleukin 2 production: GO | | | | IL1A; IL1B; PRKCQ; SASH3 | | | | | | | | | | | | | | | |
| negative regulation of muscle cell apoptotic process: GO | 30 | 5 | 2.79 | ADCYAP1; HMGCR; HMOX1; NRG1; ZC3H12A | 5 | 1.97 | HAND2; LIFR; MYOCD; NKX2-5; NOL3 | 0 | 0.00 | | 0 | 0.00 | | 1 | 0.85 | HAND2 | 2 | 1.89 | NRG1; ZC3H12A |
| neurotransmitter binding: GO | 30 | 5 | 2.79 | CHRNA3; CHRNA6; CHRNA9; HTR3A; SLC6A11 | 4 | 1.57 | CHRM3; CHRNA2; GRIN1; HTR3E | 0 | 0.00 | | 0 | 0.00 | | 1 | 0.85 | CHRM3 | 2 | 1.89 | CHRNA6; SLC6A11 |
| positive regulation of vasodilation: GO | 30 | 5 | 2.79 | ADCYAP1; F2RL1; GJA1; HMOX1; PTAFR | 5 | 1.97 | ADRA2A; AGT; EPHX2; NOS2; PLA2G6 | 0 | 0.00 | | 0 | 0.00 | | 1 | 0.85 | ADRA2A | 2 | 1.89 | PPARD; PTAFR |
| il2 stat5 pathway | 30 | 4 | 2.23 | CCNA2; CCND2; IL2RA; JAK3 | 1 | 0.39 | BCL2 | 0 | 0.00 | | 1 | 13.93 | IL2RA | 1 | 0.85 | BCL2 | 2 | 1.89 | CCNA2; CCND2 |
| response to atp: GO | 30 | 4 | 2.23 | IL1B; PANX1; PTGS2; SELL | 3 | 1.18 | P2RX1; P2RX6; P2RX7 | 0 | 0.00 | | 1 | 13.93 | IL1B | 0 | 0.00 | | 2 | 1.89 | PANX1; PTGS2 |
| signal amplification | 30 | 4 | 2.23 | GNA15; GNAI3; GNGT2; P2RY1 | 0 | 0.00 | | 0 | 0.00 | | 0 | 0.00 | | 1 | 0.85 | GNG11 | 2 | 1.89 | GNA15; P2RY1 |
| huntington's disease | 30 | 3 | 1.67 | CALML3; GAPDH; TGM2 | 1 | 0.39 | CALML6 | 0 | 0.00 | | 0 | 0.00 | | 0 | 0.00 | | 2 | 1.89 | GAPDH; TGM2 |
| organic acid sodium symporter activity: GO | 30 | 3 | 1.67 | SLC10A6; SLC38A1; SLC6A11 | 5 | 1.97 | SLC10A2; SLC13A2; SLCIA2; SLC1A6; SLC1A7 | 0 | 0.00 | | 0 | 0.00 | | 3 | 2.54 | SLC13A2; SLC1A6; SLC1A7 | 2 | 1.89 | SLC13A5; SLC6A11 |
| regulation of dendritic spine morphogenesis: GO | 30 | 3 | 1.67 | CDK5R1; CFL1; LRP8 | 7 | 2.75 | CAMK2B; EEF2K; NLGN1; PAK3; PPP1R9A; RELN; | 1 | 13.93 | SRCIN1 | 0 | 0.00 | | 2 | 1.69 | PAK3; RELN | 2 | 1.89 | CDK5R1; CFL1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | | | | SRCIN1 | | | | | | | | | | | | |
| acetylgalacto-saminyl-transferase activity: GO | 30 | 2 | 1.12 | GALNT14; GALNT6 | 5 | 1.97 | ABO; B4GALNT2; GALNT13; GALNT8; GALNTL6 | 0 | 0.00 | | 0 | 0.00 | | 1 | 0.85 | ABO | 2 | 1.89 | GALNT14; GALNT6 |
| intrinsic apoptotic signaling pathway in response to endoplasmic reticulum stress: GO | 30 | 2 | 1.12 | BAK1; CHAC1 | 4 | 1.57 | ATP2A1; BCL2; BRSK2; CASP12 | 0 | 0.00 | | 0 | 0.00 | | 3 | 2.54 | BCL2; BRSK2; CASP12 | 2 | 1.89 | BAK1; TRIB3 |
| lumenal side of membrane: GO | 30 | 2 | 1.12 | CALR; HSPA8 | 0 | 0.00 | | 0 | 0.00 | | 0 | 0.00 | | 1 | 0.85 | HLA-DQB2 | 2 | 1.89 | HLA-G; HSPA8 |
| no1 pathway | 30 | 2 | 1.12 | BDKRB2; SLC7A1 | 4 | 1.57 | ACTA1; CHRM1; PRKAR2B; PRKG2 | 1 | 13.93 | PRKAR2B | 0 | 0.00 | | 3 | 2.54 | CHRM1; PRKG1; PRKG2 | 2 | 1.89 | BDKRB2; SLC7A1 |
| phosphatidic acid metabolic process: GO | 30 | 2 | 1.12 | AGPAT5; PLA2G4D | 3 | 1.18 | GPAM; GPD1; PLA2G5 | 2 | 27.86 | GPAM; GPD1 | 0 | 0.00 | | 0 | 0.00 | | 2 | 1.89 | LPCAT1; PLA2G4D |
| positive regulation of mrna processing: GO | 30 | 2 | 1.12 | CCNB1; HSPA8 | 1 | 0.39 | CELF4 | 0 | 0.00 | | 0 | 0.00 | | 0 | 0.00 | | 2 | 1.89 | CCNB1; HSPA8 |
| protein serine threonine kinase inhibitor activity: GO | 30 | 2 | 1.12 | CDKN1A; SFN | 2 | 0.79 | PPP1R1B; PRKAR2B | 2 | 27.86 | CDKNIC; PRKAR2B | 0 | 0.00 | | 0 | 0.00 | | 2 | 1.89 | CDKN1A; SFN |
| synthesis of pa | 30 | 2 | 1.12 | AGPAT5; PLA2G4D | 4 | 1.57 | ACP6; GPAM; GPD1; PLA2G5 | 2 | 27.86 | GPAM; GPD1 | 0 | 0.00 | | 1 | 0.85 | ACP6 | 2 | 1.89 | LPCAT1; PLA2G4D |
| adipose tissue development: GO | 30 | 1 | 0.56 | NAMPT | 5 | 1.97 | HMGCS2; LEP; PPARGC1A; RORC; SOX8 | 0 | 0.00 | | 0 | 0.00 | | 3 | 2.54 | DGAT2; HMGCS2; PPARGC1A | 2 | 1.89 | NAMPT; PPARD |
| nf kappab binding: GO | 30 | 1 | 0.56 | NPM1 | 0 | 0.00 | | 0 | 0.00 | | 0 | 0.00 | | 0 | 0.00 | | 2 | 1.89 | NPM1; PPARD |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| intermediate filament: GO | 167 | 24 | 2.40 | BFSP1; CSNK1A1; DSP; GJA1; INA; JUP; KRT13; KRT14; KRT16; KRT17; KRT24; KRT3; KRT5; KRT6A; KRT6B; KRT6C; KRT75; KRT76; KRT9; LMNB1; LMNB2; NEFL; NEFM; NME1 | 26 | 1.84 | DES; KRT12; KRT15; KRT31; KRT32; KRT35; KRT36; KRT38; KRT39; KRT40; KRT72; KRT73; KRT77; KRT86; KRTAP10-11; KRTAP10-12; KRTAP10-8; KRTAP11-1; KRTAP12-3; KRTAP3-2; KRTAP3-3; KRTAP5-7; PCP4; PRPH; SYNM; UPP2 | 2 | 5.00 | KRT72; KRT73 | 0 | 0.00 | | 9 | 1.37 | KRT12; KRT2; KRT20; KRT23; KRT28; KRT40; KRT77; KRT86; KRTAP16-1 | 8 | 1.36 | BFSP1; DLGAP2; INA; KRT13; KRT24; KRT5; LMNB2; NEFM |
| modification of morphology or physiology of other organism: GO | 96 | 12 | 2.09 | CAMP; CCL3; CFL1; HMGA2; KPNA2; LTF; PPIB; RNASE7; S100A12; SERPINB9; TREM1; ZC3H12A | 7 | 0.86 | ALB; APOE; DCD; ELANE; HAMP; NTRK3; POU2F3 | 0 | 0.00 | | 2 | 8.71 | SERPINB9; TREM1 | 3 | 0.79 | CTSG; DCD; ELANE | 5 | 1.48 | CFL1; HMGA2; KPNA2; LTF; ZC3H12A |
| chromatin remodeling: GO | 143 | 15 | 1.76 | ACTB; CENPA; CENPN; CENPW; CHEK1; HIST1H4I; HIST1H4J; HIST1H4K; | 7 | 0.58 | CECR2; CHD5; HDAC5; HILS1; KAT2A; NPM2; TNP1 | 0 | 0.00 | | 0 | 0.00 | | 4 | 0.71 | CENPV; ESR1; FOXA1; SYCP3 | 7 | 1.39 | ACTB; CENPA; CENPW; CHEK1; HIST1H4I; HMGA2; NPM1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | HIST1H4L; HJURP; HMGA2; NPM1; OIP5; RUVBL1; TP63 | | | | | | | | | | | | | | | |
| negative regulation of ion transport: GO | 120 | 11 | 1.53 | ADCYAP1; GSTO1; HRH3; IL1B; MMP9; NTSR1; PCSK9; PPIF; PTGS2; SERPINE2; YWHAQ | 24 | 2.36 | ACTN2; ADORA1; ADRA2A; AGT; ANO9; APOE; ATP1A2; BCL2; BEST3; CASQ2; CNR1; DRD4; GRM7; GSTM2; HAMP; IRS2; LEP; NPY5R; PLCB4; SLC26A5; SLN; SNCA; SPINK1; TRDN | 0 | 0.00 | | 1 | 3.48 | IL1B | 6 | 1.27 | ADRA2A; ANO9; BCL2; PLCB4; SNCA; TRDN | 6 | 1.42 | NTSR1; PCSK9; PPIF; PTGS2; SERPINE2; YWHAQ |
| negative regulation of lipid metabolic process: GO | 74 | 6 | 1.36 | CYP27B1; HCAR2; IL1B; UGT1A1; UGT1A10; UGT1A7 | 12 | 1.91 | ACACB; ACADL; ADORA1; ADRA2A; APOC1; APOD; APOE; BMP5; CNR1; GPLD1; PLIN5; SERPINA12 | 0 | 0.00 | | 2 | 11.29 | HCAR2; IL1B | 5 | 1.72 | ADRA2A; DGAT2; ESR1; GPLD1; SERPINA12 | 4 | 1.53 | CYP27B1; LPCAT1; SNAI2; TRIB3 |
| antigen binding: GO | 97 | 16 | 2.76 | CD1B; HSPA8; IGHG1; IGHG2; IGHG4; IGKC; | 2 | 0.24 | FCN2; SLC7A9 | 2 | 8.62 | IGHG1; IGKV3-20 | 1 | 4.31 | IL7R | 2 | 0.52 | IGHM; IGHV3-23 | 5 | 1.46 | HLA-G; HSPA8; LILRA1; RAET1L; SLC7A5 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | IGKV4-1; IL7R; RAET1E; RAET1L; SLAMF1; SLC7A5; SLC7A8; ULBP1; ULBP2; ULBP3 | | | | | | | | | | | | | | | |
| negative regulation of extrinsic apoptotic signaling pathway: GO | 97 | 16 | 2.76 | CSF2; GDNF; GSTP1; HMOX1; IFI6; IL19; IL1A; IL1B; ITGA6; NRG1; PSME3; SCG2; SERPINE1; TGFBR1; TNFRSF10A; TNFSF10 | 6 | 0.73 | AR; BCL2; BMP5; GATA1; NOL3; TERT | 0 | 0.00 | | 2 | 8.62 | IL1B; SERPINE1 | 1 | 0.26 | BCL2 | 5 | 1.46 | GSTP1; IL19; ITGA6; NRG1; SNAI2 |
| regulation of calcium ion import: GO | 97 | 10 | 1.73 | BDKRB1; CCL3; CXCL10; CXCL11; CXCL9; GSTO1; HOMER1; NPSR1; NTSR1; UBASH3B | 12 | 1.46 | ANK2; ATP1A2; CASQ2; DMD; DRD1; EGF; GSTM2; JPH2; SLN; SNCA; SPINK1; TRDN | 0 | 0.00 | | 1 | 4.31 | CXCL9 | 6 | 1.57 | CXCL12; EGF; HRC; SNCA; TRDN; TRPC1 | 5 | 1.46 | CXCL11; HOMER1; NTSR1; TRPV3; UBASH3B |
| regulation of stress activated protein kinase signaling cascade: GO | 193 | 19 | 1.65 | CCL21; F2RL1; FOXM1; GREM1; GSTP1; HMGCR; HSPH1; IL1A; IL1B; IL26; MDFI; PBK; | 11 | 0.67 | AMBP; BIRC7; DACT1; EPHB1; FZD4; FZD8; LEP; MAPK8IP1; NOX1; PER1; TNXB | 0 | 0.00 | | 1 | 2.17 | IL1B | 3 | 0.39 | CTGF; DACT1; FZD7 | 9 | 1.32 | FOXM1; GSTP1; HSPH1; MDFI; PBK; WNT5A; WNT7A; XDH; ZC3H12A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | PRDX1; PYCARD; SERPINB3; SLAMF1; WNT5A; WNT7A; ZC3H12A | | | | | | | | | | | | | | | |
| positive regulation of calcium ion import: GO | 52 | 8 | 2.57 | BDKRB1; CCL3; CXCL10; CXCL11; CXCL9; GSTO1; NPSR1; NTSR1 | 5 | 1.13 | DRD1; GSTM2; JPH2; SNCA; TRDN | 0 | 0.00 | | 1 | 8.04 | CXCL9 | 4 | 1.95 | CXCL12; SNCA; TRDN; TRPC1 | 3 | 1.64 | CXCL11; NTSR1; TRPV3 |
| execution phase of apoptosis: GO | 52 | 4 | 1.29 | CLSPN; DNASE1L3; PRKCQ; TOP2A | 3 | 0.68 | ACVR1C; CECR2; CIDEC | 2 | 16.07 | ACVR1C; CIDEC | 0 | 0.00 | | 0 | 0.00 | | 3 | 1.64 | DNASE1L3; PRKCQ; TOP2A |
| phospholipid transport: GO | 52 | 4 | 1.29 | ABCA12; LDLR; PITPNM1; PRELID1 | 4 | 0.91 | ABCA2; APOC1; APOE; P2RX7 | 0 | 0.00 | | 0 | 0.00 | | 0 | 0.00 | | 3 | 1.64 | LDLR; PITPNM1; PRELID1 |
| presynaptic membrane: GO | 52 | 3 | 0.97 | FBXO45; FOSL1; UNC13A | 15 | 3.40 | ADORA1; APBB1; CAMK2A; GRIK4; GRIK5; GRIN2A; GRM7; KCNA1; KCNA2; KCTD16; KCTD8; NRXN1; RIMS1; SYT1; UNC13C | 0 | 0.00 | | 0 | 0.00 | | 2 | 0.98 | NRXN1; RIMS1 | 3 | 1.64 | FBXO45; FOSL1; UNC13A |
| er to golgi transport vesicle membrane: GO | 52 | 2 | 0.64 | AREG; TGFA | 2 | 0.45 | FOLR1; GRIA1 | 0 | 0.00 | | 0 | 0.00 | | 3 | 1.47 | CNIH3; GRIA1; HLA-DQB2 | 3 | 1.64 | AREG; HLA-G; TGFA |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| regulation of ossification: GO | 169 | 13 | 1.29 | AREG; CCL3; CYP27B1; GJA1; GREM1; HIF1A; IFITM1; IL6; LTF; P2RY2; SRGN; TP63; WNT5A | 20 | 1.40 | BCL2; ENPP1; FGFR1; GATA1; GDF10; HAND2; HEMGN; ID4; LRP4; MGP; NOG; OSR1; OSR2; OSTN; P2RX7; PKDCC; PTCH1; RORB; SMOC1; ZBTB16 | 0 | 0.00 | | 0 | 0.00 | | 9 | 1.35 | BCL2; CHRD; DDR2; FGFR1; HAND2; IGFBP5; OSR1; PTCH1; TMEM119 | 8 | 1.34 | AREG; BMPRB; CYP27B1; HIF1A; LTF; P2RY2; SNAI2; WNT5A |
| oxidoreductase activity acting on paired donors with incorporation or reduction of molecular oxygen: GO | 145 | 12 | 1.38 | CH25H; CYP24A1; CYP27B1; CYP27C1; CYP2S1; CYP4F11; CYP4F22; HMOX1; HMOX2; PTGS2; SQLE; TH | 29 | 2.36 | AGMO; CMAHP; CYGB; CYP17A1; CYP1A1; CYP1A2; CYP21A2; CYP2A6; CYP2C9; CYP2D6; CYP2G1P; CYP2J2; CYP2W1; CYP3A5; CYP4A11; CYP4B1; CYP4F12; CYP4F8; CYP4X1; CYP4Z1; CYP4Z2P; FADS2; FMO2; FMO5; NOS2; P4HTM; | 0 | 0.00 | | 0 | 0.00 | | 10 | 1.75 | CMAHP; CYP2W1; CYP3A4; CYP3A5; CYP4A11; CYP4B1; CYP4F12; FMO5; P4HTM; TET1 | 7 | 1.37 | CYP27B1; CYP27C1; CYP2S1; HMOX2; PTGS2; SQLE; TH |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | PTGIS; SCD5; TET1 | | | | | | | | | | | | |
| gastrulation: GO | 145 | 10 | 1.15 | EOMES; FOXF1; HMGA2; ITGA3; LAMB3; MMP9; NR4A3; SOX7; TBX20; WNT5A | 11 | 0.90 | AMOT; ATOH8; COL11A1; DKK1; GSC; ITGA7; ITGA8; MESP1; NANOG; NOG; WNT11 | 0 | 0.00 | | 0 | 0.00 | | 6 | 1.05 | ATOH8; CHRD; COL11A1; FOXC1; MESP1; WNT11 | 7 | 1.37 | EPHA2; HMGA2; ITGA3; ITGB4; LAMB3; SOX7; WNT5A |
| cartilage development: GO | 145 | 7 | 0.81 | HIF1A; HMGA2; HYAL3; PITX1; SULF2; WNT5A; WNT7A | 20 | 1.63 | ALX1; AMELX; BMP3; BMP5; COL11A1; COL11A2; FGF9; FGFR1; FGFR3; GDF5; GLI2; GPLD1; HAND2; MGP; NOG; OSR1; OSR2; PKD1; PTHIR; ZBTB16 | 0 | 0.00 | | 0 | 0.00 | | 12 | 2.10 | COL11A1; CTGF; FGF2; FGFR1; GLI2; GPLD1; HAND2; MYCN; OSR1; PRRX1; PTHIR; SHOX2 | 7 | 1.37 | BMPR1B; HIF1A; HMGA2; PITX1; SNAI2; WNT5A; WNT7A |
| phospholipase c activity: GO | 31 | 3 | 1.62 | BDKRB2; CCR5; PDIA3 | 6 | 2.28 | ADORA1; CCKBR; CHRM1; CHRM3; PLCB4; PLCH2 | 0 | 0.00 | | 0 | 0.00 | | 4 | 3.28 | CHRM1; CHRM3; PLCB4; PLCZ1 | 2 | 1.83 | BDKRB2; PLCD4 |
| basal plasma membrane: GO | 31 | 2 | 1.08 | CLCA2; ITGA6 | 5 | 1.90 | CD34; MUC20; MYO1A; SLC16A8; TF | 0 | 0.00 | | 0 | 0.00 | | 2. | 1.64 | CD34; MUC20 | 2 | 1.83 | CLCA2; ITGA6 |
| embryonic forelimb morphogenesis: GO | 31 | 2 | 1.08 | CRABP2; WNT7A | 4 | 1.52 | ALX4; OSR1; OSR2; TBX5 | 0 | 0.00 | | 0 | 0.00 | | 4 | 3.28 | ALX4; OSR1; RECK; SHOX2 | 2 | 1.83 | CRABP2; WNT7A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| met promotes cell motility | 31 | 2 | 1.08 | ITGA3; LAMB3 | 2 | 0.76 | COL24A1; LAMA2 | 0 | 0.00 | | 0 | 0.00 | | 3 | 2.46 | COL24A1; GULP1; LAMA2 | 2 | 1.83 | ITGA3; LAMB3 |
| positive regulation of response to cytokine stimulus: GO | 31 | 2 | 1.08 | HIF1A; WNT5A | 0 | 0.00 | | 0 | 0.00 | | 0 | 0.00 | | 0 | 0.00 | | 2 | 1.83 | HIF1A; WNT5A |
| regulation of muscle tissue development: GO | 98 | 9 | 1.54 | CCNB1; CDK1; CENPF; GJA1; GREMI; HMGCR; NRG1; TBX20; USP2 | 16 | 1.93 | BCL2; CDON; DKK1; ERBB4; FGF9; FGFR1; JPH2; MSTN; MYOCD; NKX2-5; NOG; PPARGC1A; RBP4; SIX1; TBX5; TSC22D3 | 0 | 0.00 | | 0 | 0.00 | | 11 | 2.85 | BCL2; CDON; ERBB4; FGF2; FGFR1; IGFBP5; KCNK2; PPARGC1A; PRICKLE1; SHOX2; TSC22D3 | 5 | 1.45 | CCNB1; CDK1; CENPF; NRG1; SOX15 |
| gap junction | 98 | 8 | 1.37 | CDK1; CSNK1A1; GNAI3; NRAS; TUBA1C; TUBA4A; TUBB2A; TUBB6 | 11 | 1.32 | ADCY2; ADCY5; ADCY6; ADCY8; ADRB1; DRD1; EGF; PDGFD; PLCB4; PRKG2; TUBB4A | 0 | 0.00 | | 0 | 0.00 | | 5 | 1.30 | EGF; LPAR1; PLCB4; PRKG1; PRKG2 | 5 | 1.45 | CDK1; TUBA1C; TUBA4A; TUBB2A; TUBB6 |
| regulation of extent of cell growth: GO | 98 | 7 | 1.20 | CDK5R1; CRABP2; LPAR3; NRG1; SEMA4B; TNFRSF12A; WNT5A | 11 | 1.32 | APOE; CDH4; MAPT; NTRK3; PLXNA3; PLXNA4; SEMA3A; SEMA3B; SEMA3D; SEMA3E; SEMA3G | 0 | 0.00 | | 0 | 0.00 | | 5 | 1.30 | CXCL12; MAPT; PLXNA4; SEMA3E; SEMA4G | 5 | 1.45 | CDK5R1; CRABP2; NRG1; SEMA4B; WNT5A |
| positive | 75 | 6 | 1.34 | HIF1A; IFNG; | 2 | 0.31 | PRKAA2; | 0 | 0.00 | | 0 | 0.00 | | 3 | 1.02 | DCN; | 4 | 1.51 | HIF1A; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| regulation of autophagy: GO | | | | MEFV; PLK2; RALB; ZC3H12A | | | SVIP | | | | | | | | | PRKAA2; SVIP | | | MEFV; PLK2; ZC3H12A |
| neural crest cell differentiation: GO | 75 | 4 | 0.89 | GDNF; HIF1A; NRG1; SEMA4B | 13 | 2.04 | EDN3; ERBB4; FOLR1; FRZB; GSC; HAND2; SEMA3A; SEMA3B; SEMA3D; SEMA3E; SEMA3G; SOX10; SOX8 | 0 | 0.00 | | 0 | 0.00 | | 6 | 2.03 | EDN3; ERBB4; FOXC1; HAND2; SEMA3E; SEMA4G | 4 | 1.51 | HIF1A; NRG1; SEMA4B; SNAI2 |
| homophilic cell adhesion via plasma membrane adhesion molecules: GO | 146 | 10 | 1.15 | CDH26; CDH3; DSC1; DSC2; DSC3; DSG1; DSG3; MPZL2; PCDH17; SDK2 | 40 | 3.23 | CADM3; CDH12; CDH19; CDH20; CDH22; CDH4; CDHR1; CDHR4; CDHR5; CLSTN2; DSCAML1; FAT3; PCDH11X; PCDH11Y; PCDH15; PCDH19; PCDH9; PCDHA10; PCDHA13; PCDHA4; PCDHA6; PCDHAC1; PCDHB15; PCDHB16; PCDHB3; PCDHB8; PCDHGA2; | 0 | 0.00 | | 0 | 0.00 | | 21 | 3.65 | CADM2; CADM3; CDH20; CDH22; CDHR4; FAT3; PCDH18; PCDH19; PCDHB11; PCDHB12; PCDHB3; PCDHB6; PCDHGA2; PCDHGA4; PCDHGA5; PCDHGA6; PCDHGA7; PCDHGA8; PCDHGB1; PCDHGB2; PTPRT | 7 | 1.36 | CDH26; DSC2; DSC3; DSG4; MPZL2; PCDH7; SDK2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | PCDHGA3; PCDHGA4; PCDHGA5; PCDHGA6; PCDHGA7; | | | | | | | | | | | | |
| epidermal growth factor receptor signaling pathway: GO | 53 | 6 | 1.89 | AREG; EREG; FAM83A; FAM83B; HBEGF; NRAS | 3 | 0.67 | BTC; EGF; SHC3 | 0 | 0.00 | | 0 | 0.00 | | 1 | 0.48 | EGF | 3 | 1.61 | AREG; EREG; HBEGF |
| regulation of hsf1-mediated heat shock response | 53 | 6 | 1.89 | HSPA4; HSPA5; HSPA6; HSPA8; HSPH1; TNFRSF21 | 0 | 0.00 | | 0 | 0.00 | | 0 | 0.00 | | 0 | 0.00 | | 3 | 1.61 | HSPA5; HSPA8; HSPH1 |
| negative regulation of protein polymerization: GO | 53 | 3 | 0.95 | CAPZA1; PFN1; TWF1 | 9 | 2.00 | CAPZA3; FHOD3; GSN; LMOD1; SCIN; SLIT2; SNCA; SPTBN4; TMOD1 | 0 | 0.00 | | 0 | 0.00 | | 6 | 2.88 | CAPZA3; LMOD1; SCIN; SLIT2; SNCA; SPTBN4 | 3 | 1.61 | PFN1; SGK1; TWF1 |
| integrin cell surface interactions | 99 | 6 | 1.01 | ICAM3; ITGA3; ITGA6; ITGAX; ITGB6; TNC | 4 | 0.48 | COL9A2; ITGA7; ITGA8; LAMA2 | 0 | 0.00 | | 0 | 0.00 | | 4 | 1.03 | GULP1; ITGA11; JAM2; LAMA2 | 5 | 1.43 | AGRN; ITGA3; ITGA6; ITGB4; ITGB6 |
| nuclear envelope organization: GO | 76 | 4 | 0.88 | CCNB1; CCNB2; CDK1; PLK1 | 0 | 0.00 | | 0 | 0.00 | | 0 | 0.00 | | 0 | 0.00 | | 4 | 1.49 | CCNB1; CCNB2; CDK1; PLK1 |
| phenol containing compound metabolic process: GO | 76 | 4 | 0.88 | FOXE1; GCNT4; SNCB; TH | 14 | 2.17 | ATP2B2; BCL2; CYP17A1; DCT; DIO3; DRD1; DRD4; GRIN2A; HAND2; MAOA; OCA2; SNCA; SULT1A2; TG | 0 | 0.00 | | 0 | 0.00 | | 6 | 2.01 | ASIP; BCL2; HAND2; HDC; SNCA; TRPC1 | 4 | 1.49 | FOXE1; SLC5A5; SNCB; TH |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| positive regulation of transmembrane transport: GO | 123 | 11 | 1.50 | ATP1B3; BDKRB1; CA2; CCL3; CXCL10; CXCL11; CXCL9; GSTO1; NPSR1; NTSR1; PTAFR | 16 | 1.53 | ACTN2; ANK2; CACNA2D1; CFTR; DMD; DRD1; DRD4; EDN3; FGF14; GSTM2; JPH2; P2RX7; RELN; SNCA; TRDN; WNK2 | 0 | 0.00 | | 1 | 3.40 | CXCL9 | 10 | 2.07 | ATP1B2; CACNA2D1; CXCL12; EDN3; GLRX; RELN; SNCA; TESC; TRDN; TRPC1 | 6 | 1.38 | CA2; CXCL11; NTSR1; PTAFR; SLC26A6; TRPV3 |
| extracellular matrix component: GO | 123 | 6 | 0.82 | GSTO1; ITGA6; LAD1; LAMB3; LTBP1; TNC | 20 | 1.92 | ADAMTS10; ALB; CCDC80; COL11A1; COL11A2; COL28A1; ELN; FBLN5; FGF9; FREM1; LAMA2; LAMB4; LAMC3; MFAP4; MFAP5; MUC5AC; SMOC1; SNCA; TIMP3; TNXB | 0 | 0.00 | | 0 | 0.00 | | 15 | 3.10 | ADAMTS10; CCDC80; COL11A1; COL28A1; DCN; ELN; FBLN1; FBLN5; FRAS1; FREM1; LAMA2; LAMC3; NTN4; SNCA; VWC2 | 6 | 1.38 | AGRN; ANXA2P2; COL17A1; ITGA6; LAD1; LAMB3 |
| negative regulation of signal transduction in absence of ligand: GO | 32 | 6 | 3.14 | CSF2; GDNF; IFI6; IL1A; IL1B; NRG1 | 3 | 1.11 | BCL2; GATA1; TERT | 0 | 0.00 | | 1 | 13.06 | IL1B | 1 | 0.79 | BCL2 | 2 | 1.77 | NRG1; SNAI2 |
| deaminase activity: GO | 32 | 4 | 2.09 | APOBEC3A; APOBEC3B; CDA; ZBP1 | 2 | 0.74 | ADAD2; AMPD1 | 0 | 0.00 | | 0 | 0.00 | | 0 | 0.00 | | 2 | 1.77 | APOBEC3B; CDA |
| positive regulation | 32 | 4 | 2.09 | FOXM1; H2AFX; | 1 | 0.37 | APBB1 | 0 | 0.00 | | 0 | 0.00 | | 0 | 0.00 | | 2 | 1.77 | FOXM1; H2AFX |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| of dna repair: GO | | | | PCNA; UBE2N | | | | | | | | | | | | | | | |
| hif2pathway | 32 | 3 | 1.57 | PGK1; SERPINE1; SLC2A1 | 0 | 0.00 | | 0 | 0.00 | | 1 | 13.06 | SERPINE1 | 0 | 0.00 | | 2 | 1.77 | PGK1; SLC2A1 |
| negative regulation of blood circulation: GO | 32 | 3 | 1.57 | HIF1A; HMGCR; ZC3H12A | 5 | 1.84 | ADORA1; ADRA1A; ATP1A2; LEP; SPTBN4 | 0 | 0.00 | | 0 | 0.00 | | 2 | 1.59 | ADRA1A; SPTBN4 | 2 | 1.77 | HIF1A; ZC3H12A |
| o linked glycosylation of mucins | 32 | 3 | 1.57 | GALNT14; GALNT6; GCNT4 | 8 | 2.95 | GALNT13; GALNT8; GALNTL6; MUC16; MUC4; MUC5AC; MUC5B; MUC7 | 0 | 0.00 | | 0 | 0.00 | | 1 | 0.79 | MUC7 | 2 | 1.77 | GALNT14; GALNT6 |
| sugar transmembrane transporter activity: GO | 32 | 3 | 1.57 | SLC2A1; SLC2A9; SLC5A1 | 3 | 1.11 | SLC2A4; SLC5A2; SLC5A9 | 0 | 0.00 | | 0 | 0.00 | | 2 | 1.59 | SLC2A12; SLC5A9 | 2 | 1.77 | SLC2A1; SLC2A9 |
| a band: GO | 32 | 2 | 1.05 | ENO1; MYOM3 | 8 | 2.95 | ANK2; ATP2A1; CMYA5; MYL3; MYL4; MYOM1; MYOM2; OBSCN | 0 | 0.00 | | 0 | 0.00 | | 2 | 1.59 | MYOM1; MYOM2 | 2 | 1.77 | ENO1; MYOM3 |
| activation of jun kinase activity: GO | 32 | 2 | 1.05 | MDFI; WNT5A | 1 | 0.37 | BIRC7 | 0 | 0.00 | | 0 | 0.00 | | 0 | 0.00 | | 2 | 1.77 | MDFI; WNT5A |
| carboxy lyase activity: GO | 32 | 2 | 1.05 | AMD1; ODC1 | 1 | 0.37 | PCK1 | 0 | 0.00 | | 0 | 0.00 | | 1 | 0.79 | HDC | 2 | 1.77 | GADL1; ODC1 |
| endonuclease activity active with either ribo or deoxyribonucleic acids and producing 5 | 32 | 2 | 1.05 | EXO1; RPP40 | 0 | 0.00 | | 0 | 0.00 | | 0 | 0.00 | | 0 | 0.00 | | 2 | 1.77 | EXO1; FEN1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| phospho-monoesters: GO | | | | | | | | | | | | | | | | | | | |
| regulation of bone resorption: GO | 32 | 2 | 1.05 | CA2; UBASH3B | 4 | 1.47 | CARTPT; CLDN18; P2RX7; PDK4 | 0 | 0.00 | | 0 | 0.00 | | 2 | 1.59 | CLDN18; PDK4 | 2 | 1.77 | CA2; UBASH3B |
| regulation of fatty acid biosynthetic process: GO | 32 | 2 | 1.05 | ANXA1; PTGS2 | 5 | 1.84 | ACADL; APOC1; MLXIPL; PDK4; PRKAA2 | 0 | 0.00 | | 0 | 0.00 | | 2 | 1.59 | PDK4; PRKAA2 | 2 | 1.77 | PTGS2; TRIB3 |
| telomere maintenance via recombination: GO | 32 | 2 | 1.05 | BRCA2; PCNA | 0 | 0.00 | | 0 | 0.00 | | 0 | 0.00 | | 0 | 0.00 | | 2 | 1.77 | BRCA2; FEN1 |
| agrin in postsynaptic differentiation | 32 | 1 | 0.52 | NRG1 | 7 | 2.58 | ACTA1; CHRM1; DMD; LAMA2; NRG2; NRG3; PAK3 | 0 | 0.00 | | 0 | 0.00 | | 3 | 2.38 | CHRM1; LAMA2; PAK3 | 2 | 1.77 | AGRN; NRG1 |
| phos-phatidylserine binding: GO | 32 | 1 | 0.52 | HSPA8 | 4 | 1.47 | ANXA13; JPH2; SCIN; SYT1 | 0 | 0.00 | | 0 | 0.00 | | 2 | 1.59 | ANXA9; SCIN | 2 | 1.77 | HSPA8; MARK1 |
| protein-protein interactions at synapses | 32 | 1 | 0.52 | HOMER1 | 5 | 1.84 | APBA1; GRIN2A; NLGN1; SYT1; SYT9 | 0 | 0.00 | | 0 | 0.00 | | 1 | 0.79 | APBA1 | 2 | 1.77 | HOMER1; LRFN4 |
| sodium channel activity: GO | 32 | 1 | 0.52 | KCNK1 | 2 | 0.74 | NALCN; SCN7A | 0 | 0.00 | | 0 | 0.00 | | 3 | 2.38 | NALCN; SCN7A; SCNN1B | 2 | 1.77 | KCNK1; SCNN1D |
| response to zinc ion: GO | 54 | 7 | 2.17 | ACP5; CA2; GGH; KRT14; MT2A; S100A8; TH | 7 | 1.53 | ABCC8; ALDOB; CRIP1; D2HGDH; HAAO; P2RX7; SLC30A10 | 0 | 0.00 | | 0 | 0.00 | | 2 | 0.94 | CRIP1; SLC18A2 | 3 | 1.58 | ACP5; CA2; TH |
| sterol homeostasis: GO | 54 | 5 | 1.55 | LDLR; LIPG; MALL; PCSK9; PLSCR3 | 7 | 1.53 | ABCA2; APOE; EPHX2; FABP4; | 1 | 7.74 | LPL | 0 | 0.00 | | 1 | 0.47 | DGAT2 | 3 | 1.58 | LDLR; MALL; PCSK9 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | | | | GPIHBP1; LPL; SOAT2 | | | | | | | | | | | | |
| fcgamma receptor (fcgr) dependent phagocytosis | 54 | 4 | 1.24 | ACTB; ACTR3; ARPC1A; FCGR1A | 0 | 0.00 | | 0 | 0.00 | | 0 | 0.00 | | 1 | 0.47 | SLC29A1 | 3 | 1.58 | ACTB; ARPC1A; VAV2 |
| actin filament bundle: GO | 54 | 3 | 0.93 | CNN2; FBLIM1; FSCN1 | 9 | 1.97 | ACTA1; AMOT; CRYAB; GAS2L2; MYH14; MYL9; PGM5; SORBS1; TPM1 | 1 | 7.74 | CRYAB | 0 | 0.00 | | 1 | 0.47 | PGM5 | 3 | 1.58 | ACTN1; FBLIM1; TPM4 |
| fatty acid transport: GO | 54 | 3 | 0.93 | ANXA1; BDKRB2; GOT2 | 10 | 2.18 | ABCD2; ACACB; APOE; DRD4; LEP; NOS2; PLA2G5; PRKAA2; SLC22A9; SLC27A6 | 2 | 15.48 | ABCD2; SLC27A6 | 0 | 0.00 | | 1 | 0.47 | PRKAA2 | 3 | 1.58 | BDKRB2; GOT2; PPARD |
| sperm flagellum: GO | 54 | 3 | 0.93 | ENKUR; RAN; TXNDC8 | 6 | 1.31 | CATSPERG; GSTM3; ODF3; RSPH1; SPEF2; TEKT3 | 0 | 0.00 | | 0 | 0.00 | | 3 | 1.41 | CATSPERG; SPATA6; SPEF2 | 3 | 1.58 | PTCHD3; RAN; SLC26A6 |
| positive regulation of multi organism process: GO | 148 | 17 | 1.92 | AURKA; C1QBP; CFL1; DEFB103A; DEFB103B; F2RL1; IFNG; KLK5; KLK7; P2RY1; P2RY2; PFN1; PLAU; PPIA; PPIB; PTAFR; | 8 | 0.64 | APOE; CACNA1H; DRD4; FCER2; INHBB; NOS2; TMPRSS2; USP17L2 | 0 | 0.00 | | 0 | 0.00 | | 1 | 0.17 | CACNA1H | 7 | 1.34 | AURKA; CFL1; P2RY1; P2RY2; PFN1; PTAFR; TOP2A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | TOP2A | | | | | | | | | | | | | | | |
| iron ion binding: GO | 148 | 12 | 1.36 | ACP5; CALR; CH25H; CYP24A1; CYP27B1; CYP27C1; CYP2S1; CYP4F11; CYP4F22; LCN2; LTF; TH | 32 | 2.55 | AGMO; CDO1; CYGB; CYP17A1; CYP1A1; CYP1A2; CYP21A2; CYP2A6; CYP2C9; CYP2D6; CYP2G1P; CYP2J2; CYP2W1; CYP3A5; CYP4A11; CYP4B1; CYP4F12; CYP4F8; CYP4X1; CYP4Z1; CYP4Z2P; FA2H; HAAO; HBA1; HBA2; HBB; NOS2; P4HTM; PTGIS; SNCA; TET1; TF | 0 | 0.00 | | 0 | 0.00 | | 12 | 2.06 | AOX1; CYP2W1; CYP3A4; CYP3A5; CYP4A11; CYP4B1; CYP4F12; HBA2; HBB; P4HTM; SNCA; TET1 | 7 | 1.34 | ACP5; CYP27B1; CYP27C1; CYP2S1; LTF; TH; XDH |
| amine metabolic process: GO | 124 | 12 | 1.62 | AMD1; FABP5; IDO1; KYNU; MBOAT2; ODC1; PLA2G3; PLA2G4D; PLBD1; SMOX; SRM; TDO2 | 14 | 1.33 | AOC3; CHPT1; CYP1A1; DHPS; DMGDH; GPLD1; HAAO; INMT; MAOA; PLA2G16; PLA2G5; PLA2G6; | 1 | 3.37 | PLA2G16 | 1 | 3.37 | TDO2 | 3 | 0.61 | DMGDH; GPLD1; HDC | 6 | 1.37 | FABP5; LPCAT1; ODC1; PLA2G3; PLA2G4D; SMOX |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | | | | PON1; SULT1A2 | | | | | | | | | | | | |
| chaperone binding: GO | 77 | 8 | 1.74 | BAK1; BIRC5; CALR; CTSC; GRPEL2; HSPA5; PRNP; SDF2L1 | 6 | 0.92 | ALB; ATP1A2; CLU; CP; DNAJB8; TG | 0 | 0.00 | | 0 | 0.00 | | 2 | 0.66 | CLU; CP | 4 | 1.47 | BAK1; BIRC5; GRPEL2; HSPA5 |
| erbb signaling pathway: GO | 77 | 7 | 1.52 | AREG; EREG; FAM83A; FAM83B; HBEGF; NRAS; NRG1 | 6 | 0.92 | BTC; EGF; ERBB4; MYOC; NRG2; SHC3 | 0 | 0.00 | | 0 | 0.00 | | 3 | 0.99 | EGF; ERBB4; MYOC | 4 | 1.47 | AREG; EREG; HBEGF; NRG1 |
| positive regulation of myeloid cell differentiation: GO | 77 | 6 | 1.30 | CA2; HIF1A; IFNG; IL12B; IL20; ISG15 | 6 | 0.92 | GATA1; IL34; IL5; LEP; LIF; SCIN | 0 | 0.00 | | 1 | 5.43 | ISG15 | 2 | 0.66 | SCIN; TESC | 4 | 1.47 | CA2; HIF1A; IL20; TRIB1 |
| positive regulation of calcium ion transport: GO | 101 | 12 | 1.99 | BAK1; BDKRB1; CCL3; CXCL10; CXCL11; CXCL9; GSTO1; HOMER1; JAK3; LPAR3; NPSR1; NTSR1 | 12 | 1.40 | ANK2; ATP2B2; CACNA2D1; CAMK2A; CLDN16; DRD1; FGF14; GSTM2; JPH2; P2RX7; SNCA; TRDN | 0 | 0.00 | | 1 | 4.14 | CXCL9 | 6 | 1.51 | ADCYAP1R1; CACNA2D1; CXCL12; SNCA; TRDN; TRPC1 | 5 | 1.40 | BAK1; CXCL11; HOMER1; NTSR1; TRPV3 |
| positive regulation of protein import: GO | 101 | 12 | 1.99 | CDK1; ECT2; GREM1; IL12B; IL1B; IL6; JUP; PRKCQ; PTGS2; SULF2; TGFBR1; ZC3H12A | 6 | 0.70 | CHP2; DACT1; EDA; EGF; ERBB4; LEP | 0 | 0.00 | | 1 | 4.14 | IL1B | 5 | 1.26 | CHP2; DACT1; EGF; ERBB4; ZIC1 | 5 | 1.40 | CDK1; ECT2; PRKCQ; PTGS2; ZC3H12A |
| terpenoid | 101 | 12 | 1.99 | ADH7; | 15 | 1.75 | ALDH1A1; | 1 | 4.14 | LPL | 1 | 4.14 | IL1B | 5 | 1.26 | ALDH3A2; | 5 | 1.40 | AGRN; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | | | | | | B. Differentially expressed genes significant in the baseline vs week 12 comparison only in the placebo Up-regulated | | | | | | C. Differentially expressed genes significant in the baseline vs week 12 comparison only in the nemo Up-regulated | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| metabolic process: GO | | | | AKRIB10; ALDHIA3; CRABP2; IL1B; LRAT; LRP8; SDC1; SDR16C5; STRA6; UGT1A1; UGT1A7 | | | APOE; AWAT2; CYP1A1; CYP1A2; CYP2C9; CYP2D6; GPC2; GPC3; GPC6; LPL; PECR; RARRES2; RBP4; SDC2 | | | | | | | | | CYP3A4; DGAT2; GPC2; RARRES2 | | | AKRIB10; CRABP2; LRAT; PPARD |
| histone deacetylase binding: GO | 101 | 6 | 0.99 | CDC20; HIF1A; HIST1H1B; KPNA2; PRDM1; TOP2A | 6 | 0.70 | BHLHE41; DACT1; HDAC5; KAT2A; MYOCD; TCF21 | 0 | 0.00 | | 0 | 0.00 | | 3 | 0.75 | BHLHE41; DACT1; HOXA10 | 5 | 1.40 | CDC20; HIF1A; HIST1H1B; KPNA2; TOP2A |
| positive regulation of leukocyte differentiation: GO | 125 | 16 | 2.14 | ANXA1; CA2; CD80; IFNG; IL12B; IL1B; IL20; IL2RA; IL36B; IL4R; IL6; IL 7R; PNP; PRDM1; SASH3; TNFSF9 | 6 | 0.57 | FLT3LG; GLI2; IL34; IL5; LIF; ZBTB16 | 0 | 0.00 | | 3 | 10.03 | IL1B; IL2RA; IL7R | 3 | 0.61 | GLI2; PIK3R6; TESC | 6 | 1.36 | CA2; CD83; HLA-G; IL20; PNP; TRIB1 |
| negative regulation of protein serine threonine kinase activity: GO | 125 | 12 | 1.61 | CDKN1A; DUSP14; DUSP6; DUSP9; GSTP1; HMGCR; IL1B; PLK1; PYCARD; SERPINB3; SFN; UBE2C | 7 | 0.66 | ADIPOQ; APOE; C2orf40; MAPK8IP1; MYOCD; PPP1R1B; PRKAR2B | 4 | 13.37 | ADIPOQ; C2orf40; CDKN1C; PRKAR2B | 1 | 3.34 | IL1B | 1 | 0.20 | SPRY1 | 6 | 1.36 | CDKN1A; DUSP6; GSTP1; PLK1; SFN; UBE2C |
| negative regulation of interferon gamma production: GO | 33 | 8 | 4.06 | C1QBP; CD274; IL1RL1; IL36RN; PGLYRP2; | 1 | 0.36 | SCGB1A1 | 0 | 0.00 | | 0 | 0.00 | | 0 | 0.00 | | 2 | 1.72 | IL10; ZC3H12A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | PRNP; SLAMF1; ZC3H12A | | | | | | | | | | | | | | | |
| cellular response to heat: GO | 33 | 7 | 3.55 | CDKN1A; CXCL10; EIF2S1; HMOX1; HSPA6; IL1A; MKI67 | 2 | 0.72 | FGF1; SCARA5 | 0 | 0.00 | | 0 | 0.00 | | 1 | 0.77 | SCARA5 | 2 | 1.72 | CDKN1A; MKI67 |
| hydrolase activity acting on carbon nitrogen but not peptide bonds in cyclic amidines: GO | 33 | 5 | 2.54 | APOBEC3A; APOBEC3B; CDA; MTHFD2; ZBP1 | 2 | 0.72 | ADAD2; AMPD1 | 0 | 0.00 | | 0 | 0.00 | | 0 | 0.00 | | 2 | 1.72 | APOBEC3B; CDA |
| binding of sperm to zona pellucida: GO | 33 | 4 | 2.03 | CCT2; CCT3; CCT5; CCT7 | 1 | 0.36 | HSPA1L | 0 | 0.00 | | 0 | 0.00 | | 0 | 0.00 | | 2 | 1.72 | CCT2; CCT5 |
| embryonic eye morphogenesis: GO | 33 | 4 | 2.03 | ALDH1A3; STRA6; TH; WNT5A | 1 | 0.36 | PAX6 | 0 | 0.00 | | 0 | 0.00 | | 0 | 0.00 | | 2 | 1.72 | TH; WNT5A |
| phosphatidyl-inositol 3 4 5 trisphosphate binding: GO | 33 | 4 | 2.03 | ADAP2; ARAP2; MYO1B; RACGAP1 | 1 | 0.36 | JPH2 | 0 | 0.00 | | 0 | 0.00 | | 0 | 0.00 | | 2 | 1.72 | ADAP2; MYO1B |
| smooth endoplasmic reticulum: GO | 33 | 4 | 2.03 | CALR; HSPA5; PPIB; TH | 3 | 1.07 | ALDOB; PLCB4; SVIP | 0 | 0.00 | | 0 | 0.00 | | 2 | 1.54 | PLCB4; SVIP | 2 | 1.72 | HSPA5; TH |
| axo dendritic transport: GO | 33 | 3 | 1.52 | HIF1A; KIF4A; NEFL | 3 | 1.07 | APBA1; KIFIA; MAPT | 0 | 0.00 | | 0 | 0.00 | | 2 | 1.54 | APBA1; MAPT | 2 | 1.72 | HIF1A; KIF4A |
| b cell proliferation: GO | 33 | 3 | 1.52 | CD79A; IFNE; IL7R | 2 | 0.72 | BCL2; IFNA5 | 0 | 0.00 | | 1 | 12.66 | IL7R | 1 | 0.77 | BCL2 | 2 | 1.72 | IFNE; IL10 |
| deoxyribo-nucleotide metabolic process: GO | 33 | 3 | 1.52 | CMPK2; NUDT15; RRM2 | 1 | 0.36 | NEIL1 | 0 | 0.00 | | 0 | 0.00 | | 0 | 0.00 | | 2 | 1.72 | NUDT15; RRM2 |
| negative regulation of interleukin 6 production: GO | 33 | 3 | 1.52 | IL36RN; SLAMF1; ZC3H12A | 0 | 0.00 | | 0 | 0.00 | | 0 | 0.00 | | 0 | 0.00 | | 2 | 1.72 | IL10; ZC3H12A |
| neuron recognition: | 33 | 3 | 1.52 | CDK5R1; | 4 | 1.43 | CNR1; | 0 | 0.00 | | 0 | 0.00 | | 1 | 0.77 | EFNB3 | 2 | 1.72 | CDK5R1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| GO | | | | CNTNAP2; CXCR4 | | | CNTN4; FEZF2; SEMA3A | | | | | | | | | | | | CNTNAP2 |
| regulation of cell aging: GO | 33 | 3 | 1.52 | FOXM1; HMGA2; TP63 | 1 | 0.36 | TERT | 0 | 0.00 | | 0 | 0.00 | | 0 | 0.00 | | 2 | 1.72 | FOXM1; HMGA2 |
| regulation of response to reactive oxygen species: GO | 33 | 3 | 1.52 | HSPH1; NR4A3; TXN | 2 | 0.72 | FBLN5; SNCA | 0 | 0.00 | | 0 | 0.00 | | 2 | 1.54 | FBLN5; SNCA | 2 | 1.72 | HSPH1; TXN |
| adherens junction assembly: GO | 33 | 2 | 1.01 | JUP; RHOD | 4 | 1.43 | ACTN2; ARHGAP6; BCL2; SORBS1 | 0 | 0.00 | | 0 | 0.00 | | 2 | 1.54 | BCL2; DLC1 | 2 | 1.72 | ACTN1; RHOD |
| hdac classii pathway | 33 | 2 | 1.01 | RAN; TUBB2A | 2 | 0.72 | GATA1; HDAC5 | 0 | 0.00 | | 0 | 0.00 | | 1 | 0.77 | ESR1 | 2 | 1.72 | RAN; TUBB2A |
| il3 pathway | 33 | 2 | 1.01 | OSM; YWHAZ | 0 | 0.00 | | 0 | 0.00 | | 1 | 12.66 | OSM | 0 | 0.00 | | 2 | 1.72 | CISH; YWHAZ |
| nuclear receptors in lipid metabolism and toxicity | 33 | 2 | 1.01 | CYP24A1; CYP27B1 | 7 | 2.50 | ABCB11; ABCC3; ABCD2; CYP1A2; CYP2C9; CYP4A11; CYP4B1 | 1 | 12.66 | ABCD2 | 0 | 0.00 | | 3 | 2.31 | CYP3A4; CYP4A11; CYP4B1 | 2 | 1.72 | CYP27B1; PPARD |
| regulation of nucleotide catabolic process: GO | 33 | 2 | 1.01 | HIF1A; PGAM1 | 5 | 1.79 | GPD1; MLXIPL; P2RX7; PPARGC1A; PRKAA2 | 1 | 12.66 | GPD1 | 0 | 0.00 | | 2 | 1.54 | PPARGC1A; PRKAA2 | 2 | 1.72 | HIF1A; PGAM1 |
| synaptonemal complex: GO | 33 | 2 | 1.01 | BLM; PLK1 | 2 | 0.72 | STAG3; SYCP1 | 0 | 0.00 | | 0 | 0.00 | | 1 | 0.77 | SYCP3 | 2 | 1.72 | BLM; PLK1 |
| negative regulation of protein kinase b signaling: GO | 33 | 0 | 0.00 | | 3 | 1.07 | MAGI2; MSTN; PKHD1 | 0 | 0.00 | | 0 | 0.00 | | 0 | 0.00 | | 2 | 1.72 | EPHA2; XDH |
| positive regulation of muscle tissue development: GO | 55 | 8 | 2.43 | CCNB1; CDK1; GJA1; GREMI; HMGCR; NRG1; | 8 | 1.72 | BCL2; CDON; ERBB4; FGF9; FGFR1; MYOCD; PPARGC1A; | 0 | 0.00 | | 0 | 0.00 | | 7 | 3.23 | BCL2; CDON; ERBB4; FGF2; FGFR1; PPARGC1A; SHOX2 | 3 | 1.55 | CCNB1; CDK1; NRG1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | TBX20; USP2 | | | TBX5 | | | | | | | | | | | | |
| cdt1 association with the cdc6 orc origin complex | 55 | 7 | 2.13 | CDC6; ORC1; ORC6; PSMA4; PSMA5; PSMB6; PSMD1 | 0 | 0.00 | | 0 | 0.00 | | 0 | 0.00 | | 0 | 0.00 | | 3 | 1.55 | CDC6; ORC1; ORC6 |
| phagocytic vesicle membrane: GO | 55 | 5 | 1.52 | ANXA3; RAB10; RAB31; RAB38; RAC2 | 3 | 0.64 | ATP6V0A4; ATP6V0E2; RAB9B | 0 | 0.00 | | 2 | 15.20 | ANXA3; RAC2 | 2 | 0.92 | ATP6V0A4; ATP6V0E2 | 3 | 1.55 | HLA-G; RAB31; RAB38 |
| positive regulation of epithelial cell differentiation: GO | 55 | 5 | 1.52 | CYP27B1; GDNF; IL20; SFN; TRIM16 | 9 | 1.93 | ADIPOQ; ATOH8; BCL2; LIF; MESP1; PAX6; PTCH1; PTCH2; TMEM100 | 1 | 7.60 | ADIPOQ | 0 | 0.00 | | 5 | 2.31 | ATOH8; BCL2; MESP1; PTCH1; PTCH2 | 3 | 1.55 | CYP27B1; IL20; SFN |
| txa2pathway | 55 | 4 | 1.22 | GNA15; PRKCQ; SELE; TGM2 | 2 | 0.43 | DNM1; EGF | 0 | 0.00 | | 1 | 7.60 | SELE | 4 | 1.85 | EGF; PIK3R6; PRKG1; PTGDR | 3 | 1.55 | GNA15; PRKCQ; TGM2 |
| embryonic pattern specification: GO | 55 | 3 | 0.91 | STIL; WNT5A; WNT7A | 8 | 1.72 | COBL; CXXC4; ERBB4; MEOX2; PTCH1; SEMA3A; TDRD5; ZBTB16 | 0 | 0.00 | | 0 | 0.00 | | 4 | 1.85 | ERBB4; HOXD8; MEOX2; PTCH1 | 3 | 1.55 | STIL; WNT5A; WNT7A |
| rna phosphodiester bond hydrolysis endonucleolytic: GO | 55 | 3 | 0.91 | EXO1; RPP40; ZC3H12A | 0 | 0.00 | | 0 | 0.00 | | 0 | 0.00 | | 0 | 0.00 | | 3 | 1.55 | EXO1; FEN1; ZC3H12A |
| basal cell carcinoma | 55 | 2 | 0.61 | WNT5A; WNT7A | 8 | 1.72 | FZD4; FZD8; GLI2; HHIP; PTCH1; PTCH2; TCF7L1; | 0 | 0.00 | | 0 | 0.00 | | 6 | 2.77 | FZD7; GLI2; PTCH1; PTCH2; TCF7L1; WNT11 | 3 | 1.55 | WNT5A; WNT7A; WNT9B |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline: Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo: Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo: Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | | | | WNT11 | | | | | | | | | | | | |
| negative regulation of leukocyte differentiation: GO | 78 | 9 | 1.93 | ANXA1; CCL3; CTLA4; IL4R; JAK3; LTF; NME1; PGLYRP2; UBASH3B | 5 | 0.76 | ADIPOQ; CARTPT; CLDN18; DTX1; LRRC17 | 1 | 5.36 | ADIPOQ | 0 | 0.00 | | 2 | 0.65 | CLDN18; LRRC17 | 4 | 1.45 | HLA-G; LTF; TRIB1; UBASH3B |
| signaling by hedgehog | 78 | 7 | 1.50 | CSNK1A1; PSMA5; PSMB6; TUBA1C; TUBA4A; TUBB2A; TUBB6 | 2 | 0.30 | ADCY8; PRKAR2B | 1 | 5.36 | PRKAR2B | 0 | 0.00 | | 0 | 0.00 | | 4 | 1.45 | TUBA1C; TUBA4A; TUBB2A; TUBB6 |
| post-translational protein phosphorylation | 78 | 4 | 0.86 | CKAP4; IL6; PCSK9; TNC | 7 | 1.06 | ALB; APOE; C3; CP; GPC3; SDC2; TF | 0 | 0.00 | | 0 | 0.00 | | 3 | 0.98 | C3; CP; SPARCL1 | 4 | 1.45 | CKAP4; IGFBP3; PCSK9; SERPINA10 |
| negative regulation of cell activation: GO | 150 | 19 | 2.12 | ANXA1; CD274; CTLA4; FOXF1; HMOX1; IDO1; IL13RA2; IL2RA; IL4R; JAK3; PGLYRP2; PRDM1; PRNP; SAMSN1; SERPINE2; THBD; TNFRSF21; UBASH3B; ZC3H12A | 6 | 0.47 | APOE; CNR1; CYGB; DTX1; MERTK; SCGB1A1 | 0 | 0.00 | | 2 | 5.57 | IL2RA; SAMSN1 | 1 | 0.17 | PRKG1 | 7 | 1.32 | HLA-G; IL10; IL13RA2; SERPINE2; THBD; UBASH3B; ZC3H12A |
| peptide receptor activity: GO | 126 | 13 | 1.73 | BDKRB1; BDKRB2; CCR4; CCR5; CXCR1; | 13 | 1.22 | AGTR1; CALCR; CCKBR; CXCR5; | 0 | 0.00 | | 0 | 0.00 | | 3 | 0.60 | AGTR1; NPY1R; TSHR | 6 | 1.35 | BDKRB2; CXCR1; FPR2; NTSR1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | CXCR4; F2RL1; FPR1; FPR3; LTB4R; NPSR1; NTSR1; QRFPR | | | GALR1; GCGR; LHCGR; NMUR1; NPY1R; NPY5R; NPY6R; SORCS1; TSHR | | | | | | | | | | | | QRFPR; SORCS2 |
| positive regulation of epithelial cell proliferation: GO | 151 | 15 | 1.66 | CDH3; EPGN; HIF1A; IL6; MMP12; NME1; NR4A3; PGF; SCG2; TGFA; TGFBR1; TGM1; TP63; WNT5A; WNT7A | 7 | 0.55 | BMP5; FGF1; FGF9; FOXE3; NOG; OSR1; OSR2 | 0 | 0.00 | | 0 | 0.00 | | 5 | 0.84 | CXCL12; ESR1; FGF2; FZD7; OSR1 | 7 | 1.31 | HIF1A; IQGAP3; LRG1; TGFA; TGM1; WNT5A; WNT7A |
| signalling to p38 via rit and rin | 151 | 15 | 1.66 | ACTB; CDK1; CSF2; DUSP6; DUSP9; EREG; HBEGF; IL2RA; JAK3; NGF; NRAS; NRG1; NTRK1; PSMA5; PSMB6 | 12 | 0.94 | BTC; CNKSR2; EGF; FGF1; FGFR1; FGFR3; GFRA1; GRIN2A; IL5; IRS2; NRG2; SHC2 | 0 | 0.00 | | 1 | 2.77 | IL2RA | 5 | 0.84 | ANGPT1; CNKSR2; EGF; FGFR1; SHC2 | 7 | 1.31 | ACTB; CDK1; DUSP6; EREG; HBEGF; NGF; NRG1 |
| cortical cytoskeleton: GO | 79 | 5 | 1.06 | ANLN; CAP1; SELE; SLC2A1; TRPC4 | 11 | 1.64 | ACTN2; CAPZA3; EPB42; GSN; MYO1A; NOS2; PCLO; PPP1R9A; SLC4A1; SPTBN4; TMOD1 | 0 | 0.00 | | 1 | 5.29 | SELE | 4 | 1.29 | CAPZA3; DLC1; PCLO; SPTBN4 | 4 | 1.44 | ANLN; CAP1; SLC2A1; TPM4 |
| regulation of carbohydrate | 79 | 4 | 0.85 | IL6; NTSR1; P2RY1; | 14 | 2.09 | ADIPOQ; EGF; ENPP1; | 1 | 5.29 | ADIPOQ | 0 | 0.00 | | 7 | 2.25 | ADCYAP1R1; DGAT2; EGF; | 4 | 1.44 | HRH1; NTSR1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| biosynthetic process: GO | | | | PTAFR | | | IRS2; KAT2A; LEP; LEPR; LHCGR; MST1; PPARGC1A; PTHIR; SERPINA12; SNCA; SORBS1 | | | | | | | | | PPARGC1A; PTH1R; SERPINA12; SNCA | | | P2RY1; PTAFR |
| g alpha (q) signalling events | 56 | 6 | 1.79 | ANXA1; CCK; F2RL1; GPR4; LTB4R; NMU | 4 | 0.84 | ADRA1A; AGT; AGTR1; PPOX | 0 | 0.00 | | 0 | 0.00 | | 5 | 2.27 | ADRA1A; AGTR1; GNG11; LPAR1; PPOX | 3 | 1.52 | FPR2; HRH1; NMU |
| cellular defense response: GO | 56 | 5 | 1.49 | CCR5; CD300C; CXCL9; FOSL1; KIR2DL4 | 1 | 0.21 | LSP1 | 0 | 0.00 | | 1 | 7.46 | CXCL9 | 0 | 0.00 | | 3 | 1.52 | FOSL1; HLA-G; LGALS3BP |
| o glycan processing: GO | 56 | 5 | 1.49 | B3GNT3; B3GNT5; GALNT14; GALNT6; GCNT4 | 12 | 2.53 | A4GNT; GALNT13; GALNT8; GXYLT2; MUC16; MUC20; MUC4; MUC5AC; MUC5B; MUC6; MUC7; MUCL1 | 0 | 0.00 | | 0 | 0.00 | | 4 | 1.81 | GXYLT2; MUC20; MUC7; MUCL1 | 3 | 1.52 | B3GNT5; GALNT14; GALNT6 |
| positive regulation of response to dna damage stimulus: GO | 56 | 5 | 1.49 | FOXM1; H2AFX; HMGA2; PCNA; UBE2N | 1 | 0.21 | APBB1 | 0 | 0.00 | | 0 | 0.00 | | 0 | 0.00 | | 3 | 1.52 | FOXM1; H2AFX; HMGA2 |
| regulation of epithelial cell apoptotic process: GO | 56 | 5 | 1.49 | EIF2S1; IL6; SCG2; SERPINB13; SERPINE1 | 3 | 0.63 | GSN; NDNF; PPARGC1A | 0 | 0.00 | | 1 | 7.46 | SERPINE1 | 4 | 1.81 | ANGPT1; ECSCR; NDNF; PPARGC1A | 3 | 1.52 | ANGPTL4; IL10; SERPINB13 |
| erbb signaling pathway | 56 | 3 | 0.90 | CDKN1A; EIF4EBP1; | 5 | 1.05 | CAMK2A; CAMK2B; | 0 | 0.00 | | 0 | 0.00 | | 2 | 0.91 | PAK3; SHC2 | 3 | 1.52 | CDKN1A; EIF4EBP1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | TGFA | | | NRG3; PAK3; SHC2 | | | | | | | | | | | | TGFA |
| vasculogenesis: GO | 56 | 2 | 0.60 | FOXF1; WNT7A | 7 | 1.47 | AMOT; FZD4; MYOCD; NKX2-5; TBX5; TMEM100; ZFPM2 | 0 | 0.00 | | 0 | 0.00 | | 1 | 0.45 | ZFPM2 | 3 | 1.52 | EPHA2; JUNB; WNT7A |
| regulation of myeloid leukocyte differentiation: GO | 103 | 8 | 1.30 | CA2; CCL3; IFNG; IL12B; IL20; LTF; NME1; UBASH3B | 8 | 0.92 | ADIPOQ; CARTPT; CLDN18; IL34; IL5; LIF; LRRC17; MITF | 1 | 4.06 | ADIPOQ | 0 | 0.00 | | 4 | 0.99 | CLDN18; LRRC17; MITF; TESC | in5 | 1.38 | CA2; IL20; LTF; TRIB1; UBASH3B |
| cysteine and methionine metabolism | 34 | 6 | 2.95 | AHCY; AMD1; GOT2; IL4I1; LDHA; SRM | 2 | 0.69 | CDO1; MATIA | 0 | 0.00 | | 0 | 0.00 | | 0 | 0.00 | | 2 | 1.67 | GOT2; LDHA |
| regulation of the actin cytoskeleton by rho gtpases | 34 | 5 | 2.46 | ACTR3; CFL1; FSCN1; MYLK2; PFN1 | 1 | 0.35 | PAK3 | 0 | 0.00 | | 0 | 0.00 | | 1 | 0.75 | PAK3 | 2 | 1.67 | CFL1; PFN1 |
| establishment or maintenance of bipolar cell polarity: GO | 34 | 4 | 1.97 | FOXF1; FSCN1; MSN; WNT5A | 2 | 0.69 | DLG2; WNT11 | 0 | 0.00 | | 0 | 0.00 | | 2 | 1.49 | DLG2; WNT11 | 2 | 1.67 | MSN; WNT5A |
| metabolism of steroid hormones and vitamins a and d | 34 | 4 | 1.97 | CYP24A1; CYP27B1; LRAT; STARD4 | 4 | 1.39 | CYP17A1; CYP21A2; HSD11B1; LHB | 0 | 0.00 | | 0 | 0.00 | | 0 | 0.00 | | 2 | 1.67 | CYP27B1; LRAT |
| negative regulation of protein maturation: GO | 34 | 4 | 1.97 | BIRC5; CHAC1; SERPINE1; SERPINE2 | 4 | 1.39 | BIRC7; C4BPA; NOL3; USP17L2 | 0 | 0.00 | | 1 | 12.29 | SERPINE1 | 0 | 0.00 | | 2 | 1.67 | BIRC5; SERPINE2 |
| regulation of filopodium assembly: GO | 34 | 4 | 1.97 | CCL21; FSCN1; PRKCQ; TGFBR1 | 5 | 1.73 | ESPN; NLGN1; NRXN1; PALM; | 0 | 0.00 | | 0 | 0.00 | | 3 | 2.24 | DPYSL3; NRXN1; PALM | 2 | 1.67 | AGRN; PRKCQ |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | | | | PPP1R9A | | | | | | | | | | | | |
| response to fluid shear stress: GO | 34 | 4 | 1.97 | CA2; GJA1; PLAU; PTGS2 | 2 | 0.69 | P2RX7; PKD1 | 0 | 0.00 | | 0 | 0.00 | | 0 | 0.00 | | 2 | 1.67 | CA2; PTGS2 |
| alditol phosphate metabolic process: GO | 34 | 3 | 1.48 | GK; PLA2G4D; SERINC2 | 4 | 1.39 | ACP6; GPD1; PLA2G16; PLA2G5 | 2 | 24.58 | GPD1; PLA2G16 | 0 | 0.00 | | 1 | 0.75 | ACP6 | 2 | 1.67 | PLA2G4D; SERINC2 |
| fmlp induced chemokine gene expression in hmc-1cells | 34 | 3 | 1.48 | CAMKIG; FPR1; GNA15 | 1 | 0.35 | CAMK1 | 0 | 0.00 | | 0 | 0.00 | | 1 | 0.75 | CAMK1 | 2 | 1.67 | CAMK1G; GNA15 |
| galactose metabolism | 34 | 3 | 1.48 | AKRIB10; HK2; PGM2 | 1 | 0.35 | GALT | 0 | 0.00 | | 0 | 0.00 | | 0 | 0.00 | | 2 | 1.67 | AKRIB10; HK2 |
| negative regulation of mitochondrion organization: GO | 34 | 3 | 1.48 | PPIF; PRELID1; SLC25A5 | 2 | 0.69 | NOL3; PPARGC1A | 0 | 0.00 | | 0 | 0.00 | | 1 | 0.75 | PPARGC1A | 2 | 1.67 | PPIF; PRELID1 |
| neuro-degenerative disorders | 34 | 3 | 1.48 | GAPDH; HSPA5; PRNP | 5 | 1.73 | APBA1; APOE; BCL2; MAPT; SNCA | 0 | 0.00 | | 0 | 0.00 | | 4 | 2.99 | APBA1; BCL2; MAPT; SNCA | 2 | 1.67 | GAPDH; HSPA5 |
| membrane protein proteolysis: GO | 34 | 2 | 0.98 | PRKCQ; PSENEN | 3 | 1.04 | NAPSA; P2RX7; TMPRSS6 | 0 | 0.00 | | 0 | 0.00 | | 0 | 0.00 | | 2 | 1.67 | ADAM19; PRKCQ |
| neuron projection membrane: GO | 34 | 2 | 0.98 | CNTNAP2; NRG1 | 5 | 1.73 | ADORA1; GRIA1; ITGA8; PALM; SLC1A2 | 0 | 0.00 | | 0 | 0.00 | | 2 | 1.49 | GRIA1; PALM | 2 | 1.67 | CNTNAP2; NRG1 |
| b cell activation involved in immune response: GO | 34 | 1 | 0.49 | EXO1 | 0 | 0.00 | | 0 | 0.00 | | 0 | 0.00 | | 0 | 0.00 | | 2 | 1.67 | BCL3; EXO1 |
| camp metabolic process: GO | 34 | 1 | 0.49 | PTHLH | 5 | 1.73 | ADCY2; ADCY5; ADCY6; ADCY8; PDE11A | 0 | 0.00 | | 0 | 0.00 | | 0 | 0.00 | | 2 | 1.67 | PTHLH; UCN2 |
| lamellipodium organization: GO | 34 | 1 | 0.49 | RHOD | 0 | 0.00 | | 0 | 0.00 | | 0 | 0.00 | | 0 | 0.00 | | 2 | 1.67 | RHOD; VAV2 |
| epha fwdpathway | 34 | 0 | 0.00 | | 1 | 0.35 | EPHA6 | 0 | 0.00 | | 0 | 0.00 | | 1 | 0.75 | PIK3R6 | 2 | 1.67 | EPHA2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | | | | | | | | | | | | | | | | VAV2 |
| inner ear receptor cell development: GO | 34 | 0 | 0.00 | | 5 | 1.73 | ATP2B2; CLIC5; FGFR1; GABRB3; PDZD7 | 0 | 0.00 | | 0 | 0.00 | | 4 | 2.99 | CLIC5; FGFR1; PDZD7; SLITRK6 | 2 | 1.67 | SLC4A7; TMC1 |
| defense response to virus: GO | 152 | 27 | 2.97 | APOBEC3A; APOBEC3B; CXADR; CXCL10; CXCL9; F2RL1; IFI16; IFI44L; IFIT3; IFITM1; IFITM3; IFNE; IFNG; IL12B; IL6; ISG15; ISG20; MX1; OAS1; OAS2; OAS3; OASL; POLR3G; PYCARD; RSAD2; STAT1; ZC3H12A | 5 | 0.39 | AGBL4; BCL2; CD207; GPAM; IFNA5 | 1 | 2.75 | GPAM | 5 | 13.75 | CXCL9; GBP1; IFI44L; IFITM3; ISG15 | 3 | 0.50 | ABCC9; BCL2; CD207 | 7 | 1.31 | APOBEC3B; IFI16; IFNE; MX1; OAS1; POLR3G; ZC3H12A |
| cellular response to oxidative stress: GO | 177 | 14 | 1.32 | ANXA1; CCNA2; CDK1; ECT2; GJB2; HIF1A; HMOX1; IL6; MELK; MMP3; PPIF; PRDX1; TXNDC8; ZC3H12A | 9 | 0.60 | BCL2; MAPT; PDGFD; PPARGC1A; PRODH; RBM11; SNCA; SOD3; TPM1 | 0 | 0.00 | | 0 | 0.00 | | 6 | 0.86 | BCL2; MAPT; PPARGC1A; PRODH; SNCA; SOD3 | 8 | 1.28 | CCNA2; CDK1; DHRS2; ECT2; HIF1A; MMP3; PPIF; ZC3H12A |
| macromolecular complex disassembly: GO | 177 | 11 | 1.04 | CFL1; CSNK1A1; GADD45GIP1; HSPA8; KIF14; | 1 | 0.07 | TNP1 | 0 | 0.00 | | 0 | 0.00 | | 0 | 0.00 | | 8 | 1.28 | CFL1; HSPA8; KIF14; KIF18A; KIF18B; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | KIF18A; KIF2C; MRPL13; MRPL36; MRPL51; NRG1 | | | | | | | | | | | | | | | KIF2C; NRG1; SGK1 |
| cellular aldehyde metabolic process: GO | 80 | 6 | 1.26 | AKRIB10; ALDH1A3; GLO1; PGM2; SDR16C5; TPI1 | 4 | 0.59 | ALDH1A1; ALDOB; CACNA1H; HOGA1 | 0 | 0.00 | | 0 | 0.00 | | 2 | 0.64 | ALDH3A2; CACNA1H | 4 | 1.42 | AKRIB10; GLDC; TKT; TPI1 |
| negative regulation of transmembrane transport: GO | 80 | 6 | 1.26 | GSTO1; MMP9; NTSR1; PCSK9; PPIF; YWHAQ | 14 | 2.06 | ACTN2; ADRA2A; AGT; ANO9; ATP1A2; CASQ2; DRD4; GSTM2; HAMP; IRS2; SLC26A5; SLN; SPINK1; TRDN | 0 | 0.00 | | 0 | 0.00 | | 3 | 0.95 | ADRA2A; ANO9; TRDN | 4 | 1.42 | NTSR1; PCSK9; PPIF; YWHAQ |
| integrin mediated signaling pathway: GO | 80 | 4 | 0.84 | ITGA3; ITGA6; ITGAX; ITGB6 | 5 | 0.74 | ADAM11; ITGA7; ITGA8; PLP1; PRAM1 | 0 | 0.00 | | 0 | 0.00 | | 4 | 1.27 | CTGF; FBLN1; ITGA11; PLP1 | 4 | 1.42 | ITGA3; ITGA6; ITGB4; ITGB6 |
| tube formation: GO | 128 | 9 | 1.18 | GDNF; GREM1; GRHL3; HIF1A; KIF20B; PFN1; STIL; TGM2; WNT5A | 12 | 1.11 | ALX1; ATOH8; COBL; EDA; FOLR1; IRX1; KAT2A; NOG; OSR1; PTCH1; SIX1; SOX8 | 0 | 0.00 | | 0 | 0.00 | | 7 | 1.39 | ATOH8; DLC1; GDF7; OSR1; PRICKLE1; PTCH1; SHROOM3 | 6 | 1.33 | HIF1A; PFN1; STIL; TGM2; WNT5A; WNT9B |
| hedgehog signaling pathway | 57 | 3 | 0.88 | CSNK1A1; WNT5A; WNT7A | 6 | 1.24 | BMP5; GLI2; HHIP; PTCH1; PTCH2; WNT11 | 0 | 0.00 | | 0 | 0.00 | | 4 | 1.78 | GLI2; PTCH1; PTCH2; WNT11 | 3 | 1.49 | WNT5A; WNT7A; WNT9B |
| preribosome: GO | 57 | 2 | 0.59 | EBNA1BP2; EIF6 | 0 | 0.00 | | 0 | 0.00 | | 0 | 0.00 | | 0 | 0.00 | | 3 | 1.49 | EBNA1BP2; EIF6; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | | | | | | | | | | | | | NOP56 |
| nucleoside phosphate biosynthetic process: GO | 153 | 12 | 1.31 | ACOT7; CMPK2; GARS; KYNU; NAMPT; NME1; OAS1; OAS2; PNP; RRM2; TK1; UPP1 | 12 | 0.93 | ACACB; ADCY2; ADCY5; ADCY6; ADCY8; AMPD1; ASPDH; ATP6V0A4; ENTPD8; HAAO; SLC26A1; UPP2 | 0 | 0.00 | | 0 | 0.00 | | 3 | 0.50 | AK7; ATP6V0A4; NMNAT3 | 7 | 1.30 | ACOT7; NAMPT; OAS1; PNP; RRM2; TK1; UCN2 |
| metallopeptidase activity: GO | 178 | 14 | 1.32 | ADAM23; ADAMDEC1; ADAMTS4; CLCA2; CNDP2; CPA6; CPXM1; DPP3; KLK7; MMP1; MMP10; MMP12; MMP3; MMP9 | 10 | 0.66 | ADAM11; ADAM22; ADAM33; ADAMTS10; ADAMTS16; ADAMTS19; ADAMTSL3; AGBL1; AGBL4; TRHDE | 0 | 0.00 | | 0 | 0.00 | | 7 | 1.00 | ADAM22; ADAM33; ADAMTS10; ADAMTSL3; CPE; CPZ; MMP27 | 8 | 1.27 | ADAM19; ADAM23; ADAMTS14; ADAMTS4; CLCA2; CPA6; MMP25; MMP3 |
| programmed cell death | 129 | 13 | 1.69 | BAK1; CLSPN; CYCS; DSG3; DYNLL1; HIST1H1B; HIST1H1D; LMNB1; PSMA5; PSMB6; SFN; TNFRSF10A; TNFSF10 | 5 | 0.46 | BCL2; CES1; GAS2; GSN; MAPT | 0 | 0.00 | | 0 | 0.00 | | 5 | 0.98 | BCL2; CES1; CTSG; DLC1; MAPT | 6 | 1.32 | BAK1; CYCS; E2F1; HIST1H1B; HIST1H1D; SFN |
| inorganic anion transmembrane transporter activity: GO | 129 | 4 | 0.52 | CLCA2; GABRQ; SLC26A9; SLC4A8 | 24 | 2.19 | ANO3; ANO5; ANO9; BEST2; BEST3; | 0 | 0.00 | | 0 | 0.00 | | 5 | 0.98 | ANO9; CLCN4; CLIC5; GLRB; | 6 | 1.32 | CLCA2; SLC20A1; SLC26A6; SLC4A3; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | BEST4; CFTR; CLCNKA; CLCNKB; CLIC5; GABRA2; GABRB3; GABRG3; GABRP; GLRB; SLC17A4; SLC17A7; SLC22A9; SLC26A1; SLC26A5; SLC26A7; SLC34A3; SLC4A1; SLC4A4 | | | | | | | | | SLC4A4 | | | SLC4A7; SLC5A5 |
| lymphocyte chemotaxis: GO | 35 | 8 | 3.82 | CCL17; CCL18; CCL21; CCL22; CCL3; CXCL10; CXCL11; CXCL13 | 1 | 0.34 | CCL14 | 0 | 0.00 | | 0 | 0.00 | | 1 | 0.73 | CCL14 | 2 | 1.62 | CCL20; CXCL11 |
| beta tubulin binding: GO | 35 | 4 | 1.91 | CCT5; GJA1; RACGAP1; SNCB | 1 | 0.34 | SNCA | 0 | 0.00 | | 0 | 0.00 | | 1 | 0.73 | SNCA | 2 | 1.62 | CCT5; SNCB |
| embryonic camera type eye development: GO | 35 | 4 | 1.91 | ALDH1A3; STRA6; TH; WNT5A | 1 | 0.34 | PAX6 | 0 | 0.00 | | 0 | 0.00 | | 0 | 0.00 | | 2 | 1.62 | TH; WNT5A |
| negative regulation of innate immune response: GO | 35 | 4 | 1.91 | IFI16; NMI; SERPINB4; SERPINB9 | 0 | 0.00 | | 0 | 0.00 | | 1 | 11.94 | SERPINB9 | 0 | 0.00 | | 2 | 1.62 | IFI16; NMI |
| oxidoreductase activity acting on the aldehyde or | 35 | 4 | 1.91 | AKRIB10; ALDH1A3; ALDH4A1; GAPDH | 2 | 0.67 | ALDH1A1; ALDH1L1 | 0 | 0.00 | | 0 | 0.00 | | 2 | 1.45 | ALDH3A2; ALDH5A1 | 2 | 1.62 | AKRIB10; GAPDH |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| oxo group of donors nad or nadp as acceptor: GO | | | | | | | | | | | | | | | | | | | |
| allograft rejection | 35 | 3 | 1.43 | CD80; IFNG; IL12B | 1 | 0.34 | IL5 | 0 | 0.00 | | 1 | 11.94 | GZMB | 0 | 0.00 | | 2 | 1.62 | HLA-G; IL10 |
| bone remodeling: GO | 35 | 3 | 1.43 | ACP5; IL6; RAC2 | 1 | 0.34 | PTH1R | 0 | 0.00 | | 1 | 11.94 | RAC2 | 1 | 0.73 | PTH1R | 2 | 1.62 | ACP5; EPHA2 |
| glial cell migration: GO | 35 | 3 | 1.43 | CCL3; CDK5R1; P2RY1 | 2 | 0.67 | DCX; RELN | 0 | 0.00 | | 0 | 0.00 | | 1 | 0.73 | RELN | 2 | 1.62 | CDK5R1; P2RY1 |
| mating: GO | 35 | 3 | 1.43 | PI3; SERPINE2; TH | 4 | 1.35 | DRD1; GRIN1; P2RX1; PPP1R1B | 0 | 0.00 | | 0 | 0.00 | | 0 | 0.00 | | 2 | 1.62 | SERPINE2; TH |
| pyruvate metabolism and citric acid (tca) cycle | 35 | 3 | 1.43 | GLO1; LDHA; SLC16A1 | 1 | 0.34 | PDK4 | 0 | 0.00 | | 0 | 0.00 | | 2 | 1.45 | PDK3; PDK4 | 2 | 1.62 | LDHA; PPARD |
| arf6 pathway | 35 | 2 | 0.96 | ARAP2; GNA15 | 5 | 1.69 | AGTR1; EGF; LHCGR; TSHR; USP6 | 0 | 0.00 | | 0 | 0.00 | | 4 | 2.90 | AGTR1; EGF; GULP1; TSHR | 2 | 1.62 | EPHA2; GNA15 |
| modulation by virus of host morphology or physiology: GO | 35 | 2 | 0.96 | KPNA2; ZC3H12A | 1 | 0.34 | NTRK3 | 0 | 0.00 | | 0 | 0.00 | | 0 | 0.00 | | 2 | 1.62 | KPNA2; ZC3H12A |
| regulation of peptidyl threonine phosphorylation: GO | 35 | 2 | 0.96 | PLK1; WNT5A | 1 | 0.34 | EGF | 0 | 0.00 | | 0 | 0.00 | | 1 | 0.73 | EGF | 2 | 1.62 | PLK1; WNT5A |
| hair cell differentiation: GO | 35 | 1 | 0.48 | PLS3 | 5 | 1.69 | ATP2B2; CLIC5; FGFR1; MCOLN3; PDZD7 | 0 | 0.00 | | 0 | 0.00 | | 4 | 2.90 | CLIC5; FGFR1; PDZD7; SLITRK6 | 2 | 1.62 | SLC4A7; TMC1 |
| columnar cuboidal epithelial cell differentiation: GO | 105 | 6 | 0.96 | CDKN1A; HIF1A; PLS3; PRDM1; TP63; WNT5A | 15 | 1.69 | ATP2B2; BCL2; BMP5; CLIC5; EDN3; FGFR1; GATA5; | 0 | 0.00 | | 0 | 0.00 | | 10 | 2.42 | B9D1; BCL2; CLIC5; EDN3; FGFR1; FOXA1; MITF; | 5 | 1.35 | CDKN1A; HIF1A; SLC4A7; TMC1; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | MCOLN3; MITF; OCA2; PAX6; PDZD7; ROS1; SOX10; WNT11 | | | | | | | | | PDZD7; SLITRK6; WNT11 | | | |
| prolonged erk activation events | 154 | 15 | 1.63 | ACTB; CDK1; CSF2; DUSP6; DUSP9; EREG; HBEGF; IL2RA; JAK3; NGF; NRAS; NRG1; NTRK1; PSMA5; PSMB6 | 12 | 0.92 | BTC; CNKSR2; EGF; FGF1; FGFR1; FGFR3; GFRA1; GRIN2A; IL5; IRS2; NRG2; SHC2 | 0 | 0.00 | | 1 | 2.71 | IL2RA | 5 | 0.82 | ANGPT1; CNKSR2; EGF; FGFR1; SHC2 | 7 | 1.29 | ACTB; CDK1; DUSP6; EREG; HBEGF; NGF; NRG1 |
| calcium signaling pathway | 179 | 11 | 1.03 | BDKRB1; BDKRB2; CALML3; CALML5; GNA15; HTR7; MYLK2; NTSR1; PTAFR; SLC25A5; VDAC1 | 33 | 2.18 | ADCY2; ADCY8; ADRA1A; ADRA1B; ADRB1; AGTR1; ATP2A1; ATP2B2; CACNA1F; CACNA1H; CALML6; CAMK2A; CAMK2B; CCKBR; CHP2; CHRM1; CHRM2; CHRM3; DRD1; ERBB4; GRIN1; GRIN2A; HTR4; HTR6; | 0 | 0.00 | | 0 | 0.00 | | 15 | 2.13 | ADRA1A; AGTR1; CACNA1G; CACNA1H; CHP2; CHRM1; CHRM3; ERBB4; PDE1A; PHKG1; PLCB4; PLCZ1; PTGFR; TNNC1; TRPC1 | 8 | 1.27 | BDKRB2; GNA15; HRH1; HRH2; NTSR1; PLCD4; PTAFR; VDAC1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | LHCGR; NOS2; P2RX1; P2RX6; P2RX7; PHKG1; PLCB4; TNNC1; TNNC2 | | | | | | | | | | | | |
| myeloid cell differentiation: GO | 179 | 7 | 0.65 | ACP5; CSF2; F2RL1; GLO1; IFI16; MMP9; TNFSF9 | 6 | 0.40 | ALAS2; EPB42; GATA1; GPC3; RHAG; ZBTB16 | 1 | 2.33 | CDKN1C | 0 | 0.00 | | 0 | 0.00 | | 8 | 1.27 | ACP5; ACTN1; DHRS2; DYRK3; EPHA2; IFI16; JUNB; SBNO2 |
| cell cell recognition: GO | 58 | 6 | 1.73 | CCL21; CCT2; CCT3; CCT5; CCT7; FUT3 | 4 | 0.81 | CATSPERG; EPHB1; HSPA1L; KCNU1 | 0 | 0.00 | | 0 | 0.00 | | 1 | 0.44 | CATSPERG | 3 | 1.47 | CCT2; CCT5; FUT3 |
| regulation of smooth muscle contraction: GO | 58 | 5 | 1.44 | CHRNA3; NMU; PROK2; PTAFR; PTGS2 | 12 | 2.44 | ADORA1; ADRA1A; ADRA1B; ADRA2A; ATP1A2; CHRM1; CHRM2; CHRM3; CNN1; KCNB2; MYOCD; P2RX1 | 0 | 0.00 | | 0 | 0.00 | | 5 | 2.19 | ADRA1A; ADRA2A; CHRM1; CHRM3; PRKG1 | 3 | 1.47 | NMU; PTAFR; PTGS2 |
| cell death signalling via nrage nrif and nade | 58 | 3 | 0.87 | ECT2; NGF; PSENEN | 1 | 0.20 | OBSCN | 0 | 0.00 | | 0 | 0.00 | | 0 | 0.00 | | 3 | 1.47 | ARHGEF16; ECT2; NGF |
| cortical actin cytoskeleton: GO | 58 | 3 | 0.87 | ANLN; CAP1; SLC2A1 | 5 | 1.02 | ACTN2; GSN; MYO1A; PPP1R9A; SPTBN4 | 0 | 0.00 | | 0 | 0.00 | | 2 | 0.88 | DLC1; SPTBN4 | 3 | 1.47 | ANLN; CAP1; SLC2A1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| branching morphogenesis of an epithelial tube: GO | 130 | 10 | 1.29 | AREG; BAK1; FOXF1; GDNF; GREM1; PGF; TBX20; TIMELESS; TNC; WNT5A | 13 | 1.18 | ADAMTS16; BCL2; EGF; FGF1; GLI2; GPC3; HHIP; PKD1; PTCH1; SEMA3E; SIX1; SLIT2; TCF21 | 0 | 0.00 | | 0 | 0.00 | | 12 | 2.35 | BCL2; EGF; ESR1; FGF2; FOXA1; GDF7; GLI2; MYCN; PTCH1; SEMA3E; SLIT2; SPRY1 | 6 | 1.31 | AREG; BAK1; EPHA2; TIMELESS; WNT5A; WNT9B |
| regulation of type i interferon production: GO | 106 | 7 | 1.11 | IFI16; ISG15; MYD88; NMI; POLR3G; PYCARD; ZBP1 | 0 | 0.00 | | 0 | 0.00 | | 1 | 3.94 | ISG15 | 1 | 0.24 | ZBTB20 | 5 | 1.34 | IFI16; IL10; MYD88; NMI; POLR3G |
| ethanolamine containing compound metabolic process: GO | 82 | 5 | 1.02 | FABP5; MBOAT2; PLA2G3; PLA2G4D; PLBD1 | 7 | 1.01 | CHPT1; DMGDH; GPLD1; PLA2G16; PLA2G5; PLA2G6; PON1 | 1 | 5.10 | PLA2G16 | 0 | 0.00 | | 2 | 0.62 | DMGDH; GPLD1 | 4 | 1.38 | FABP5; LPCAT1; PLA2G3; PLA2G4D |
| positive regulation of chromatin modification: GO | 82 | 4 | 0.82 | CCNB1; HIST1H1B; IL1B; UBE2N | 6 | 0.86 | KAT2A; LIF; NAPIL2; PIWIL2; PPARGC1A; TET1 | 0 | 0.00 | | 1 | 5.10 | IL1B | 3 | 0.93 | NAP1L2; PPARGC1A; TET1 | 4 | 1.38 | CCNB1; HIST1H1B; RPS6KA4; SNAI2 |
| oxidoreductase activity acting on ch oh group of donors: GO | 131 | 8 | 1.02 | ADH7; AKR1B10; AKR1B15; HMGCR; LDHA; RDH16; SDR16C5; SDR9C7 | 10 | 0.90 | ADH1B; ADH1C; ADHFE1; D2HGDH; GPD1; HAO2; HHIP; HSD11B1; HSD17B14; LDHD | 2 | 6.38 | GPD1; HSD11B2 | 0 | 0.00 | | 3 | 0.58 | AKR1E2; ALDH3A2; AOX1 | 6 | 1.30 | AKR1B10; DHRS2; LDHA; RDH16; SDR9C7; XDH |
| positive regulation of tyrosine phosphorylation of stat3 protein: GO | 36 | 6 | 2.79 | IL12B; IL20; IL24; IL6; OSM; SOCS3 | 4 | 1.31 | FGFR3; GHR; LEP; LIF | 1 | 11.61 | GHR | 1 | 11.61 | OSM | 0 | 0.00 | | 2 | 1.58 | IL20; SOCS3 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| gmcsf pathway | 36 | 5 | 2.32 | CSF2; NRAS; OSM; STAT1; YWHAZ | 0 | 0.00 | | 0 | 0.00 | | 1 | 11.61 | OSM | 0 | 0.00 | | 2 | 1.58 | CISH; YWHAZ |
| regulation of action potential: GO | 36 | 5 | 2.32 | DSC2; DSP; IFNG; JUP; NTSR1 | 6 | 1.97 | ADRA1A; ANK2; CACNA2D1; CNR1; CTNNA3; KCNB1 | 0 | 0.00 | | 0 | 0.00 | | 2 | 1.41 | ADRA1A; CACNA2D1 | 2 | 1.58 | DSC2; NTSR1 |
| translesion synthesis: GO | 36 | 5 | 2.32 | DTL; ISG15; PCNA; USP43; VCP | 0 | 0.00 | | 0 | 0.00 | | 1 | 11.61 | ISG15 | 0 | 0.00 | | 2 | 1.58 | DTL; USP43 |
| olfactory lobe development: GO | 36 | 4 | 1.86 | EOMES; KIF14; SALL3; WNT5A | 5 | 1.64 | ERBB4; FGFR1; SEMA3A; SLIT2; SLIT3 | 0 | 0.00 | | 0 | 0.00 | | 4 | 2.82 | ERBB4; FGFR1; SLIT2; SLIT3 | 2 | 1.58 | KIF14; WNT5A |
| dna damage response detection of dna damage: GO | 36 | 3 | 1.39 | DTL; HMGA2; PCNA | 0 | 0.00 | | 0 | 0.00 | | 0 | 0.00 | | 0 | 0.00 | | 2 | 1.58 | DTL; HMGA2 |
| fmlp pathway | 36 | 3 | 1.39 | CAMK1G; FPR1; GNA15 | 1 | 0.33 | CAMK1 | 0 | 0.00 | | 0 | 0.00 | | 1 | 0.71 | CAMK1 | 2 | 1.58 | CAMK1G; GNA15 |
| activation of gene expression by srebf (srebp) | 36 | 2 | 0.93 | HMGCR; SQLE | 2 | 0.66 | ACACB; GPAM | 1 | 11.61 | GPAM | 0 | 0.00 | | 0 | 0.00 | | 2 | 1.58 | FEN1; SQLE |
| linoleic acid metabolism | 36 | 2 | 0.93 | AKR1B10; PLA2G3 | 6 | 1.97 | CYP1A2; CYP2C9; CYP2J2; CYP3A5; PLA2G5; PLA2G6 | 0 | 0.00 | | 0 | 0.00 | | 2 | 1.41 | CYP3A4; CYP3A5 | 2 | 1.58 | AKR1B10; PLA2G3 |
| reciprocal dna recombination: GO | 36 | 2 | 0.93 | TOP2A; TRIP13 | 1 | 0.33 | SYCP1 | 0 | 0.00 | | 0 | 0.00 | | 0 | 0.00 | | 2 | 1.58 | TOP2A; TRIP13 |
| interstrand cross link repair: GO | 36 | 1 | 0.46 | UBE2T | 0 | 0.00 | | 0 | 0.00 | | 0 | 0.00 | | 0 | 0.00 | | 2 | 1.58 | FANCI; UBE2T |
| positive regulation of protein acetylation: GO | 36 | 1 | 0.46 | IL1B | 6 | 1.97 | CAMK1; KAT2A; LIF; NAP1L2; PIWIL2; PPARGC1A | 0 | 0.00 | | 1 | 11.61 | IL1B | 3 | 2.12 | CAMK1; NAPIL2; PPARGC1A | 2 | 1.58 | RPS6KA4; SNAI2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| signal transduction by l1 | 36 | 0 | 0.00 | | 3 | 0.98 | FGFR1; NCAM1; RPS6KA6 | 0 | 0.00 | | 0 | 0.00 | | 3 | 2.12 | FGFR1; NCAM1; RPS6KA6 | 2 | 1.58 | RPS6KA4; VAV2 |
| positive regulation of hemopoiesis: GO | 156 | 18 | 1.93 | ANXA1; CA2; CD80; HIF1A; IFNG; IL12B; IL1B; IL20; IL2RA; IL36B; IL4R; IL6; IL7R; ISG15; PNP; PRDM1; SASH3; TNFSF9 | 9 | 0.68 | FLT3LG; GATA1; GLI2; IL34; IL5; LEP; LIF; SCIN; ZBTB16 | 0 | 0.00 | | 4 | 10.72 | IL1B; IL2RA; IL7R; ISG15 | 5 | 0.81 | FOXC1; GLI2; PIK3R6; SCIN; TESC | 7 | 1.27 | CA2; CD83; HIF1A; HLA-G; IL20; PNP; TRIB1 |
| positive regulation of peptidyl tyrosine phosphorylation: GO | 156 | 18 | 1.93 | CCK; CD3E; CD80; CSF2; EPGN; EREG; GREM1; HSPH1; IFNG; IL12B; IL20; IL24; IL6; LRP8; NRG1; OSM; SOCS3; TGFA | 16 | 1.21 | ADIPOQ; ADORA1; ADRA2A; AGT; ANGPT4; EGF; ERBB4; FGFR3; GATA1; GHR; IL5; LEP; LIF; LRP4; RELN; SRCIN1 | 3 | 8.04 | ADIPOQ; GHR; SRCIN1 | 1 | 2.68 | OSM | 7 | 1.14 | ADRA2A; ANGPT1; ANGPT4; EGF; ERBB4; GPRC5B; RELN | 7 | 1.27 | AFAP1L2; EREG; HSPH1; IL20; NRG1; SOCS3; TGFA |
| pyruvate metabolism | 59 | 5 | 1.42 | ALDH1A3; GLO1; LDHA; PKM; SLC16A1 | 6 | 1.20 | ACACB; ACOT12; LDHD; PCK1; PDK4; SLC16A8 | 0 | 0.00 | | 0 | 0.00 | | 3 | 1.29 | ALDH3A2; PDK3; PDK4 | 3 | 1.44 | LDHA; PKM; PPARD |
| regulation of atpase activity: GO | 59 | 5 | 1.42 | ATP1B3; LTF; PFN1; PPIF; UHRF1 | 10 | 2.00 | ALDOB; BRSK2; MYL3; MYL4; SLN; TNNC1; TNNT2; TNNT3; TPM1; TPM2 | 0 | 0.00 | | 0 | 0.00 | | 4 | 1.72 | ATP1B2; BRSK2; TNNC1; TNNT3 | 3 | 1.44 | LTF; PFN1; PPIF |
| chondrocyte differentiation: | 59 | 3 | 0.85 | HMGA2; SULF2; | 11 | 2.20 | AMELX; COL11A1; | 0 | 0.00 | | 0 | 0.00 | | 7 | 3.01 | COL11A1; FGFR1; GLI2; | 3 | 1.44 | BMPR1B; HMGA2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| GO | | | | WNT7A | | | FGF9; FGFR1; FGFR3; GDF5; GLI2; GPLD1; OSR1; OSR2; PTH1R | | | | | | | | | GPLD1; OSR1; PTH1R; SHOX2 | | | WNT7A |
| phosphoprotein binding: GO | 59 | 3 | 0.85 | GPRIN1; SAMSN1; SFN | 3 | 0.60 | CACNB1; SNCA; TOX3 | 0 | 0.00 | | 1 | 7.08 | SAMSN1 | 2 | 0.86 | CACNB1; SNCA | 3 | 1.44 | GPRIN1; PLAT; SFN |
| regulation of phospholipid metabolic process: GO | 59 | 2 | 0.57 | CCL21; LDLR | 4 | 0.80 | APOC1; CCKBR; ERBB4; FGFR3 | 0 | 0.00 | | 0 | 0.00 | | 3 | 1.29 | ERBB4; FGF2; PIK3R6 | 3 | 1.44 | LDLR; LPCAT1; VAV2 |
| negative regulation of cysteine type endopeptidase activity: GO | 83 | 10 | 2.02 | BIRC5; IFI16; IFI6; IL6; LAMP3; MMP9; NGF; PLAUR; SERPINB9; SFN | 5 | 0.71 | BIRC7; CRYAB; NOL3; SNCA; TFAP2B | 1 | 5.03 | CRYAB | 2 | 10.07 | LAMP3; SERPINB9 | 1 | 0.31 | SNCA | 4 | 1.37 | BIRC5; IFI16; NGF; SFN |
| negative regulation of myeloid cell differentiation: GO | 83 | 9 | 1.81 | CCL3; GPR171; HIST1H4I; HIST1H4J; HIST1H4K; HIST1H4L; LTF; NME1; UBASH3B | 5 | 0.71 | ADIPOQ; CARTPT; CLDN18; LRRC17; ZBTB16 | 1 | 5.03 | ADIPOQ | 0 | 0.00 | | 2 | 0.61 | CLDN18; LRRC17 | 4 | 1.37 | HIST1H4I; LTF; TRIB1; UBASH3B |
| phagocytic vesicle: GO | 83 | 7 | 1.41 | ANXA3; LTF; RAB10; RAB31; RAB38; RAC2; SLAMF1 | 3 | 0.43 | ATP6V0A4; ATP6V0E2; RAB9B | 0 | 0.00 | | 2 | 10.07 | ANXA3; RAC2 | 2 | 0.61 | ATP6V0A4; ATP6V0E2 | 4 | 1.37 | HLA-G; LTF; RAB31; RAB38 |
| b cell differentiation: GO | 83 | 5 | 1.01 | BAK1; CD79A; IFNE; JAK3; NTRK1 | 3 | 0.43 | BCL2; HDAC5; IFNA5 | 0 | 0.00 | | 0 | 0.00 | | 1 | 0.31 | BCL2 | 4 | 1.37 | BAK1; BCL3; IFNE; IL10 |
| mesenchymal cell differentiation: GO | 132 | 10 | 1.27 | EOMES; FAM83D; GDNF; HIF1A; | 23 | 2.06 | ALX1; AMELX; BCL2; EDN3; ERBB4; | 0 | 0.00 | | 0 | 0.00 | | 10 | 1.92 | BCL2; EDN3; ERBB4; FGFR1; FOXC1; | 6 | 1.29 | HIF1A; HMGA2; NRG1; SEMA4B; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | HMGA2; NRG1; SEMA4B; STAT1; TGFBR1; WNT5A | | | FGFR1; FOLR1; FRZB; GSC; HAND2; NOG; OSR1; PAX3; SEMA3A; SEMA3B; SEMA3D; SEMA3E; SEMA3G; SOX10; SOX8; TCF21; TMEM100; WNT11 | | | | | | | | | HAND2; OSR1; SEMA3E; SEMA4G; WNT11 | | | SNAI2; WNT5A |
| eye morphogenesis: GO | 132 | 9 | 1.14 | ALDH1A3; BAK1; FJX1; HIF1A; PRDM1; SDK2; STRA6; TH; WNT5A | 12 | 1.07 | BCAR3; CDON; EPHB1; FOXE3; FOXN4; PAX6; RBP4; RORB; SOX1; SOX8; TFAP2B; TRPM1 | 0 | 0.00 | | 0 | 0.00 | | 3 | 0.58 | BCAR3; CDON; TSPAN12 | 6 | 1.29 | BAK1; EPHA2; HIF1A; SDK2; TH; WNT5A |
| negative regulation of cellular protein localization: GO | 132 | 6 | 0.76 | HSPH1; LYPLA1; MDFI; TXN; YOD1; ZC3H12A | 10 | 0.89 | ACTN2; ADIPOQ; ANXA13; APOD; ASTN2; CLDN18; PKD1; PKDCC; SVIP; USP17L2 | 1 | 3.17 | ADIPOQ | 1 | 3.17 | GBP1 | 4 | 0.77 | ANGPT1; CLDN18; LRRC15; SVIP | 6 | 1.29 | HSPH1; IL10; MDFI; SNAI2; TXN; ZC3H12A |
| peptidyl tyrosine modification: GO | 182 | 11 | 1.01 | CSF2; EREG; HBEGF; IL12RB2; JAK3; MELK; NRG1; NTRK1; | 22 | 1.43 | BTC; EGF; EPHA6; EPHB1; ERBB4; FGF1; FGF17; FGF22; FGF9; | 1 | 2.30 | GHR | 1 | 2.30 | OSM | 7 | 0.98 | DDR2; EGF; ERBB4; FGF2; FGF22; FGFR1; RELN | 8 | 1.25 | DYRK3; EPHA2; EREG; HBEGF; IL12RB2; NRG1; TTK; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | OSM; TTK; TWF1 | | | FGFR1; FGFR3; GHR; IL5; LEP; LIF; LTK; MERTK; NRG2; NTRK3; PKDCC; RELN; ROS1 | | | | | | | | | | | | TWF1 |
| mesoderm development: GO | 108 | 8 | 1.24 | EOMES; FOXF1; HMGA2; ITGA3; NR4A3; TBX20; TP63; WNT5A | 9 | 0.98 | DKK1; FGFR1; ITGA8; MESP1; MEST; NOG; OSR1; WNT11; ZFPM2 | 0 | 0.00 | | 0 | 0.00 | | 7 | 1.65 | CHRD; FGFR1; FOXC1; MESP1; OSR1; WNT11; ZFPM2 | 5 | 1.31 | EPHA2; HMGA2; ITGA3; ITGB4; WNT5A |
| cytoskeleton dependent intracellular transport: GO | 108 | 7 | 1.08 | DYNLL1; HIF1A; KIF14; KIF23; KIF4A; NEFL; TUBA1C | 4 | 0.44 | APBA1; DYNC1I1; KIF1A; MAPT | 0 | 0.00 | | 0 | 0.00 | | 2 | 0.47 | APBA1; MAPT | 5 | 1.31 | HIF1A; KIF14; KIF23; KIF4A; TUBA1C |
| leukocyte homeostasis: GO | 60 | 9 | 2.51 | ANXA1; BAK1; CCNB2; HCAR2; HIF1A; IFNG; IL2RA; IL6; JAK3 | 3 | 0.59 | BCL2; CACNA1F; P2RX7 | 0 | 0.00 | | 2 | 13.93 | HCAR2; IL2RA | 3 | 1.27 | BCL2; SLC40A1; SLC46A2 | 3 | 1.42 | BAK1; CCNB2; HIF1A |
| uch proteinases | 60 | 7 | 1.95 | ACTB; H2AFX; HIST1H2AE; PSMA5; PSMB6; RUVBL1; TGFBR1 | 0 | 0.00 | | 0 | 0.00 | | 0 | 0.00 | | 0 | 0.00 | | 3 | 1.42 | ACTB; H2AFX; HIST1H2AE |
| stem cell proliferation: GO | 60 | 6 | 1.67 | ARTN; ASPM; RAB10; RACGAP1; STAT1; | 10 | 1.97 | CD34; DCT; FGFR1; GPC3; HAND2; HHIP; ID4; | 0 | 0.00 | | 0 | 0.00 | | 4 | 1.69 | CD34; FGFR1; HAND2; OSR1 | 3 | 1.42 | ARTN; ASPM; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | WNT5A | | | KCNA1; OSR1; SOX5 | | | | | | | | | | | | |
| forebrain cell migration: GO | 60 | 4 | 1.12 | CDK5R1; CXCR4; FBXO45; NRG1 | 12 | 2.36 | DCX; DRD1; EMX2; FEZF2; FGFR1; HTR6; NRG3; POU3F3; RELN; SEMA3A; SLIT2; SLIT3 | 0 | 0.00 | | 0 | 0.00 | | 7 | 2.96 | CXCL12; EMX2; FGFR1; POU3F3; RELN; SLIT2; SLIT3 | 3 | 1.42 | CDK5R1; FBXO45; NRG1 |
| cellular response to retinoic acid: GO | 60 | 3 | 0.84 | KRT13; TNC; WNT5A | 7 | 1.38 | FZD4; LEP; LTK; NTRK3; OSR1; RORB; WNT11 | 0 | 0.00 | | 0 | 0.00 | | 4 | 1.69 | FZD7; OSR1; TESC; WNT11 | 3 | 1.42 | KRT13; WNT5A; WNT9B |
| positive regulation of insulin secretion: GO | 60 | 3 | 0.84 | GJA1; HIF1A; VSNL1 | 5 | 0.98 | CFTR; GPLD1; IRS2; PLA2G6; RBP4 | 0 | 0.00 | | 0 | 0.00 | | 2 | 0.85 | GPLD1; MYRIP | 3 | 1.42 | HIF1A; PPARD; VSNL1 |
| formation of the cornified envelope | 37 | 10 | 4.52 | CSTA; DSG3; IVL; JUP; KRT16; KRT17; PERP; PI3; SPRR2A; SPRR2B | 2 | 0.64 | KRT15; KRT86 | 0 | 0.00 | | 0 | 0.00 | | 3 | 2.06 | CRNN; KRT23; KRT86 | 2 | 1.53 | CSTA; IVL |
| defense response to fungus: GO | 37 | 9 | 4.07 | C10orf99; CAMP; CLEC6A; COTL1; IL36RN; LTF; S100A12; S100A8; S100A9 | 3 | 0.96 | DCD; ELANE; HAMP | 0 | 0.00 | | 1 | 11.29 | COTL1 | 3 | 2.06 | CTSG; DCD; ELANE | 2 | 1.53 | C10orf99; LTF |
| regulation of cd4 positive alpha beta t cell activation: GO | 37 | 9 | 4.07 | ANXA1; CD80; IFNG; IL12B; IL4R; IL6; JAK3; PRKCQ; SASH3 | 0 | 0.00 | | 0 | 0.00 | | 0 | 0.00 | | 0 | 0.00 | | 2 | 1.53 | CD83; PRKCQ |
| positive | 37 | 8 | 3.62 | ANXA1; | 1 | 0.32 | ZBTB16 | 0 | 0.00 | | 0 | 0.00 | | 0 | 0.00 | | 2 | 1.53 | CD83; PNP |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline: Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo: Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo: Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| regulation of alpha beta t cell differentiation: GO | | | | CD80; IFNG; IL12B; IL4R; IL6; PNP; SASH3 | | | | | | | | | | | | | | | |
| regulation of granulocyte chemotaxis: GO | 37 | 8 | 3.62 | C1QBP; CCL21; CXCL1; CXCL3; IL1B; RAC2; S100A14; S100A7 | 2 | 0.64 | RARRES2; SLIT2 | 0 | 0.00 | | 2 | 22.59 | IL1B; RAC2 | 2 | 1.37 | RARRES2; SLIT2 | 2 | 1.53 | CXCL2; S100A14 |
| positive regulation of release of sequestered calcium ion into cytosol: GO | 37 | 7 | 3.17 | BDKRB1; CXCL10; CXCL11; CXCL9; GSTO1; NPSR1; NTSR1 | 5 | 1.59 | DRD1; GSTM2; JPH2; SNCA; TRDN | 0 | 0.00 | | 1 | 11.29 | CXCL9 | 3 | 2.06 | SNCA; TRDN; TRPC1 | 2 | 1.53 | CXCL11; NTSR1 |
| regulation of mast cell activation: GO | 37 | 7 | 3.17 | FOXF1; HMOX1; IL13RA2; IL4R; NR4A3; PTPRE; RAC2 | 1 | 0.32 | CNR1 | 0 | 0.00 | | 1 | 11.29 | RAC2 | 0 | 0.00 | | 2 | 1.53 | IL13RA2; PTPRE |
| pyrimidine containing compound biosynthetic process: GO | 37 | 6 | 2.71 | CDA: CMPK2; NME1; TK1; TYMP; UPP1 | 1 | 0.32 | UPP2 | 0 | 0.00 | | 0 | 0.00 | | 0 | 0.00 | | 2 | 1.53 | CDA; TK1 |
| endocrine pancreas development: GO | 37 | 4 | 1.81 | ANXA1; BAK1; IL6; WNT5A | 4 | 1.28 | BMP5; CLU; MNX1; PAX6 | 0 | 0.00 | | 0 | 0.00 | | 1 | 0.69 | CLU | 2 | 1.53 | BAK1; WNT5A |
| response to testosterone: GO | 37 | 4 | 1.81 | CALR; MSN; NME1; WNT5A | 2 | 0.64 | HMGCS2; MSTN | 0 | 0.00 | | 0 | 0.00 | | 1 | 0.69 | HMGCS2 | 2 | 1.53 | MSN; WNT5A |
| hindlimb morphogenesis: GO | 37 | 3 | 1.36 | PITX1; SALL3; WNT7A | 9 | 2.87 | AFF3; ALX4; GDF5; GPC3; OSR1; OSR2; PTCH1; TFAP2B; ZBTB16 | 0 | 0.00 | | 0 | 0.00 | | 4 | 2.75 | AFF3; ALX4; OSR1; PTCH1 | 2 | 1.53 | PITX1; WNT7A |
| nucleobase | 37 | 3 | 1.36 | CDA; IL1B; | 0 | 0.00 | | 0 | 0.00 | | 1 | 11.29 | IL1B | 1 | 0.69 | AOX1 | 2 | 1.53 | CDA; XDH |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| metabolic process: GO | | | | TYMP | | | | | | | | | | | | | | | |
| nucleoside bisphosphate metabolic process: GO | 37 | 3 | 1.36 | ACOT7; HMGCR; SULT2B1 | 4 | 1.28 | ACACB; ENPP1; SLC26A1; SULT1A2 | 0 | 0.00 | | 0 | 0.00 | | 1 | 0.69 | SULT1E1 | 2 | 1.53 | ACOT7; SULT2B1 |
| oxidoreductase activity acting on paired donors with incorporation or reduction of molecular oxygen nad ph as one donor and incorporation of one atom of oxygen: GO | 37 | 3 | 1.36 | CYP27B1; CYP4F11; SQLE | 7 | 2.23 | CYP1A1; CYP2C9; CYP4A11; CYP4F12; FMO2; FMO5; NOS2 | 0 | 0.00 | | 0 | 0.00 | | 4 | 2.75 | CYP3A4; CYP4A11; CYP4F12; FMO5 | 2 | 1.53 | CYP27B1; SQLE |
| glucose transport | 37 | 2 | 0.90 | HK2; SLC2A1 | 1 | 0.32 | SLC2A4 | 0 | 0.00 | | 0 | 0.00 | | 0 | 0.00 | | 2 | 1.53 | HK2; SLC2A1 |
| phagosome maturation: GO | 37 | 2 | 0.90 | RAB31; RAB38 | 4 | 1.28 | ATP6V0A4; ATP6V0E2; ATP6V1B1; P2RX7 | 0 | 0.00 | | 0 | 0.00 | | 2 | 1.37 | ATP6V0A4; ATP6V0E2 | 2 | 1.53 | RAB31; RAB38 |
| response to nerve growth factor: GO | 37 | 2 | 0.90 | EIF4A3; NTRK1 | 3 | 0.96 | EEF2K; KAT2A; MAGI2 | 0 | 0.00 | | 0 | 0.00 | | 0 | 0.00 | | 2 | 1.53 | E2F1; EIF4A3 |
| positive regulation of biomineral tissue development: GO | 37 | 1 | 0.45 | LTF | 5 | 1.59 | AMELX; OSR1; OSR2; P2RX7; PKDCC | 0 | 0.00 | | 0 | 0.00 | | 2 | 1.37 | OSR1; TMEM119 | 2 | 1.53 | BMPR1B; LTF |
| tp53 regulates transcription of dna repair genes | 37 | 1 | 0.45 | CHEK1 | 0 | 0.00 | | 0 | 0.00 | | 0 | 0.00 | | 0 | 0.00 | | 2 | 1.53 | CHEK1; FANCI |
| cell activation involved in immune response: GO | 133 | 14 | 1.76 | ANXA3; CCL3; CLEC7A; EOMES; EXO1; | 3 | 0.27 | IFNA5; KLRF2; RORC | 0 | 0.00 | | 1 | 3.14 | ANXA3 | 1 | 0.19 | KLRF2 | 6 | 1.28 | BCL3; CLEC7A; EXO1; IFNE; PLA2G3; SBNO2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | F2RL1; IFNE; IFNG; IL12B; IL6; NR4A3; PLA2G3; PYCARD; SLAMF1 | | | | | | | | | | | | | | | |
| activation of mapk activity: GO | 133 | 12 | 1.51 | CDK1; CXCR4; DUSP6; DUSP9; EPGN; FPR1; IL1B; LPAR3; MDFI; PROK2; TGFA; WNT5A | 11 | 0.98 | ADRA2A; BIRC7; DRD4; EGF; GHR; MUC20; NTRK3; P2RX7; PAK3; PROK1; SHC2 | 1 | 3.14 | GHR | 1 | 3.14 | IL1B | 7 | 1.34 | ADRA2A; EGF; FGF2; LPAR1; MUC20; PAK3; SHC2 | 6 | 1.28 | CDK1; DUSP6; IQGAP3; MDFI; TGFA; WNT5A |
| regulation of intrinsic apoptotic signaling pathway: GO | 133 | 10 | 1.26 | BDKRB2; HIF1A; HSPH1; IL19; MMP9; PLAUR; PPIF; PYCARD; S100A8; S100A9 | 5 | 0.44 | BCL2; CLU; MAPK8IP1; NOL3; NOX1 | 0 | 0.00 | | 0 | 0.00 | | 4 | 0.76 | BCL2; CLU; CREB3L1; CXCL12 | 6 | 1.28 | BDKRB2; HIF1A; HSPH1; IL19; PPIF; SNAI2 |
| regulation of phosphatidyl-inositol 3 kinase signaling: GO | 133 | 6 | 0.75 | CD80; EREG; F2RL1; HBEGF; NRG1; SERPINE2 | 17 | 1.51 | AGT; BTC; EGF; ERBB4; FGF1; FGF17; FGF22; FGF9; FGFR1; FGFR3; IRS2; LEP; MYOC; NRG2; PDGFD; RELN; SERPINA12 | 0 | 0.00 | | 0 | 0.00 | | 10 | 1.91 | ANGPT1; DCN; EGF; ERBB4; FGF2; FGF22; FGFR1; MYOC; RELN; SERPINA12 | 6 | 1.28 | EREG; HBEGF; IER3; NRG1; PPARD; SERPINE2 |
| tissue homeostasis: GO | 158 | 15 | 1.59 | ABCA12; ACP5; ACTB; CDH3; CNGB1; CXADR; HOMER1; | 18 | 1.34 | ALB; BCL2; CD34; CDHR1; CROCC; FLT3LG; GATA1; | 0 | 0.00 | | 2 | 5.29 | LYZ; RAC2 | 9 | 1.45 | BCL2; CD34; CTGF; FOXC1; LDB2; MAK; PIP; PTH1R; TUB | 7 | 1.26 | ACP5; ACTB; HOMER1; LPCAT1; LTF; SLC28A3; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | IGKC; LTF; LYZ; PRDX1; RAC2; SASH3; SLC28A3; VSIG1 | | | MUC4; MUC5AC; MUC6; NAPSA; NXNL2; P2RX7; PCDH15; PIP; PTH1R; RBP4; TF | | | | | | | | | | | | VSIG1 |
| regulation of peptidyl serine phosphorylation: GO | 109 | 8 | 1.23 | BAK1; BDKRB2; IFNE; IFNG; IL6; OSM; TXN; WNT5A | 11 | 1.19 | BCAR3; BCL2; CAMK1; DKK1; DMD; IFNA5; LIF; MLXIPL; NTRK3; SNCA; SPTBN4 | 0 | 0.00 | | 1 | 3.83 | OSM | 7 | 1.63 | ANGPT1; BCAR3; BCL2; CAMK1; HRC; SNCA; SPTBN4 | 5 | 1.30 | BAK1; BDKRB2; IFNE; TXN; WNT5A |
| regulation of blood pressure: GO | 159 | 10 | 1.05 | ADM2; BDKRB1; BDKRB2; F2RL1; GJA1; HMOX1; NRG1; NTSR1; PTAFR; PTGS2 | 29 | 2.15 | ADAMTS16; ADIPOQ; ADORA1; ADRA1A; ADRAIB; ADRB1; AGT; AGTR1; ATP1A2; CARTPT; CD34; CNR1; CYP4A11; CYP4F12; EDN3; EPHX2; GCGR; HBB; LEP; NCALD; NOS2; NOX1; NPY1R; P2RX1; PCSK5; REN; RENBP; TPM1; TRHDE | 2 | 5.26 | ADIPOQ; HSD11B2 | 0 | 0.00 | | 11 | 1.76 | ADRA1A; AGTR1; CD34; CORIN; CTSG; CYP4A11; CYP4F12; EDN3; HBB; NCALD; NPY1R | 7 | 1.25 | ADM2; BDKRB2; NRG1; NTSR1; PTAFR; PTGS2; SGK1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| response to ethanol: GO | 134 | 21 | 2.62 | ADCYAP1; ADH7; BAK1; CCL7; CCNE1; CDK1; CTSB; EIF4EBP1; GGH; GK; GOT2; GSTP1; HMGCR; HTR3A; IL1B; NEU2; NTRK1; S100A8; TH; TNC; UGT1A1 | 15 | 1.32 | ADIPOQ; CA3; CDO1; CNR1; DRD1; DRD4; GRIN1; GRIN2A; GSN; HMGCS2; LEP; MSTN; NTRK3; RBP4; SLC2A4 | 1 | 3.12 | ADIPOQ | 1 | 3.12 | IL1B | 3 | 0.57 | ADCYAP1R1; CA3: HMGCS2 | 6 | 1.27 | BAK1; CDK1; EIF4EBP1; GOT2; GSTP1; TH |
| hindbrain development: GO | 134 | 6 | 0.75 | CDK5R1; HSPA5; KIF14; NLGN4X; SERPINE2; WNT7A | 13 | 1.14 | ATP2B2; BCL2; CBLN1; FZD4; GLI2; GRIN1; KAT2A; LMX1A; NEUROD2; NOG; NRXN1; PPARGC1A; SEZ6L | 0 | 0.00 | | 0 | 0.00 | | 8 | 1.52 | BCL2; DLC1; GLI2; LPAR1; MDK; NRXN1; PPARGC1A; SEZ6L | 6 | 1.27 | CDK5R1; HSPA5; KIF14; NLGN4X; SERPINE2; WNT7A |
| non recombinational repair: GO | 61 | 7 | 1.92 | H2AFX; HIST1H4I; HIST1H4J; HIST1H4K; HIST1H4L; POLQ; UBE2N | 0 | 0.00 | | 0 | 0.00 | | 0 | 0.00 | | 0 | 0.00 | | 3 | 1.39 | H2AFX; HIST1H4I; POLQ |
| embryonic heart tube morphogenesis: GO | 61 | 6 | 1.65 | GJA1; HIF1A; NDRG4; STIL; TBX20; WNT5A | 7 | 1.35 | CCDC40; DNAAF1; FOLR1; FOXN4; HAND2; MESP1; | 0 | 0.00 | | 0 | 0.00 | | 2 | 0.83 | HAND2; MESP1 | 3 | 1.39 | HIF1A; STIL; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | NKX2-5 | | | | | | | | | | | | |
| class b 2 secretin family receptors | 61 | 4 | 1.10 | ADCYAP1; ADM2; GNGT2; WNT7A | 8 | 1.55 | FZD8; GCGR; PTCH1; PTCH2; PTH1R; SCT; VIPR2; WNT11 | 0 | 0.00 | | 0 | 0.00 | | 5 | 2.08 | ADCYAP1R1; PTCH1; PTCH2; PTHIR; WNT11 | 3 | 1.39 | ADM2; WNT7A; WNT9B |
| actomyosin: GO | 61 | 3 | 0.82 | CNN2; FBLIM1; FSCN1 | 8 | 1.55 | ACTA1; AMOT; GAS2L2; MYH14; MYL9; PGM5; SORBS1; TPM1 | 0 | 0.00 | | 0 | 0.00 | | 1 | 0.42 | PGM5 | 3 | 1.39 | ACTN1; FBLIM1; TPM4 |
| regulation of protein acetylation: GO | 61 | 2 | 0.55 | CHEK1; IL1B | 10 | 1.93 | CAMK1; HDAC5; KAT2A; KLF15; LIF; MYOCD; NAP1L2; PIWIL2; PPARGC1A; SNCA | 0 | 0.00 | | 1 | 6.85 | IL1B | 4 | 1.67 | CAMK1; NAP1L2; PPARGC1A; SNCA | 3 | 1.39 | CHEK1; RPS6KA4; SNAI2 |
| regulation of insulin-like growth factor (igf) transport and uptake by insulin-like growth factor binding proteins (igfbps) | 85 | 5 | 0.98 | CKAP4; IL6; MMP1; PCSK9; TNC | 7 | 0.97 | ALB; APOE; C3; CP; GPC3; SDC2; TF | 0 | 0.00 | | 0 | 0.00 | | 4 | 1.20 | C3; CP; CTSG; SPARCL1 | 4 | 1.33 | CKAP4; IGFBP3; PCSK9; SERPINA10 |
| ecadherin nascent aj pathway | 38 | 3 | 1.32 | ENAH; JUP; NME1 | 0 | 0.00 | | 0 | 0.00 | | 0 | 0.00 | | 0 | 0.00 | | 2 | 1.49 | ENAH; VAV2 |
| mesenchyme morphogenesis: GO | 38 | 3 | 1.32 | FOXF1; TBX20; WNT5A | 4 | 1.24 | ACTA1; OSR1; TMEM100; WNT11 | 0 | 0.00 | | 0 | 0.00 | | 3 | 2.01 | FOXC1; OSR1; WNT11 | 2 | 1.49 | SNAI2; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| negative regulation of type i interferon production: GO | 38 | 3 | 1.32 | ISG15; NMI; PYCARD | 0 | 0.00 | | 0 | 0.00 | | 1 | 11.00 | ISG15 | 0 | 0.00 | | 2 | 1.49 | IL10; NMI |
| g alpha (12/13) signalling events | 38 | 1 | 0.44 | ECT2 | 3 | 0.93 | ADRA1A; ARHGEF26; MCF2L | 0 | 0.00 | | 0 | 0.00 | | 3 | 2.01 | ADRA1A; ARHGEF26; GNG11 | 2 | 1.49 | ECT2; VAV2 |
| trabecula morphogenesis: GO | 38 | 1 | 0.44 | NRG1 | 2 | 0.62 | NKX2-5; RBP4 | 0 | 0.00 | | 0 | 0.00 | | 1 | 0.67 | SLC40A1 | 2 | 1.49 | NRG1; SBNO2 |
| oxidoreductase activity acting on the ch oh group of donors nad or nadp as acceptor: GO | 110 | 8 | 1.22 | ADH7; AKRIB10; AKR1B15; HMGCR; LDHA; RDH16; SDR16C5; SDR9C7 | 5 | 0.54 | ADH1B; ADHIC; GPD1; HSD11B1; HSD17B14 | 2 | 7.60 | GPD1; HSD11B2 | 0 | 0.00 | | 1 | 0.23 | AKRIE2 | 5 | 1.29 | AKRIB10; DHRS2; LDHA; RDH16; SDR9C7 |
| positive regulation of hormone secretion: GO | 110 | 7 | 1.06 | ADCYAP1; GJA1; HCAR2; HIF1A; NMU; P2RY1; VSNL1 | 13 | 1.39 | CARTPT; CFTR; EDN3; GALR1; GPLD1; ILDR1; INHBB; IRS2; LEP; LIF; PLA2G6; RBP4; SCT | 0 | 0.00 | | 1 | 3.80 | HCAR2 | 4 | 0.92 | EDN3; GPLD1; ILDR1; MYRIP | 5 | 1.29 | HIF1A; NMU; P2RY1; PPARD; VSNL1 |
| regulation of endothelial cell migration: GO | 110 | 7 | 1.06 | ANXA3; CXCL13; PTGS2; SH3BGRL3; WNT5A; WNT7A; ZC3H12A | 11 | 1.18 | AGT; AMOT; ANGPT4; APOE; ATOH8; CCBE1; FGF1; FGFR1; GPLD1; HDAC5; SLIT2 | 0 | 0.00 | | 1 | 3.80 | ANXA3 | 9 | 2.08 | ANGPT1; ANGPT4; ATOH8; CCBE1; DCN; FGF2; FGFR1; GPLD1; SLIT2 | 5 | 1.29 | EPHA2; PTGS2; WNT5A; WNT7A; ZC3H12A |
| cell recognition: GO | 135 | 14 | 1.74 | CCL21; CCT2; CCT3; CCT5; CCT7; CDK5R1; CLEC7A; | 13 | 1.14 | CADM2; CADM3; CATSPERG; CNR1; CNTN4; | 1 | 3.10 | IGHG1 | 0 | 0.00 | | 8 | 1.51 | CADM2; CADM3; CATSPERG; CNTNAP3; EFNB3; | 6 | 1.26 | CCT2; CCT5; CDK5R1; CLEC7A; CNTNAP2; FUT3 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | CNTNAP2; CXCR4; FUT3; IGHG1; IGHG2; IGHG4; IGKC | | | CNTNAP3; COLEC12; EPHB1; FCN2; FEZF2; HSPA1L; KCNU1; SEMA3A | | | | | | | | | IGHM; IGHV3-23; TUB | | | |
| cluster of actin based cell projections: GO | 135 | 6 | 0.74 | ACTR3; IDO1; KCNK1; MYO1B; PLS3; SLC5A1 | 21 | 1.84 | ATP6V0A4; CDHR5; CLIC5; CYBRD1; ESPN; FOLR1; GRXCR2; MYH14; MYO15A; MYO1A; NPC1L1; PCDH15; PDZD7; PTHIR; SCIN; SLC34A3; SLC5A2; SLC7A9; SOAT2; TMC2; TSPEAR | 0 | 0.00 | | 0 | 0.00 | | 7 | 1.32 | ADD3; ATP6V0A4; CLIC5; CYBRD1; PDZD7; PTHIR; SCIN | 6 | 1.26 | ACTN1; KCNK1; MYO1B; SLC26A6; SLC4A7; TMC1 |
| tissue remodeling: GO | 86 | 8 | 1.56 | ACP5; ANXA1; BAK1; GJAI; HIF1A; IL1A; IL6; RAC2 | 4 | 0.55 | AGT; LIF; NOL3; PTH1R | 0 | 0.00 | | 1 | 4.86 | RAC2 | 3 | 0.89 | FOXC1; IGFBP5; PTH1R | 4 | 1.32 | ACP5; BAK1; EPHA2; HIF1A |
| feeding behavior: GO | 86 | 6 | 1.17 | ADM2; CCK; NMU; P2RY1; STRA6; TH | 15 | 2.06 | AGT; CARTPT; CCKBR; CNTFR; DACH1; DRD1; GRIN1; GRM7; | 1 | 4.86 | MRAP2 | 0 | 0.00 | | 6 | 1.77 | ASIP; CNTFR; DACH1; HAND2; NEGR1; NPY1R | 4 | 1.32 | ADM2; NMU; P2RY1; TH |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | HAND2; LEP; NEGR1; NPY1R; NPY5R; NPY6R; REN | | | | | | | | | | | | |
| synaptic vesicle cycle: GO | 86 | 4 | 0.78 | STON2; TH; UNC13A; WNT7A | 13 | 1.78 | CADPS; NLGN1; NRXN1; P2RX7; PCLO; RIMS1; RPH3AL; SLC17A7; SNCA; SYT1; SYT17; SYT8; SYT9 | 0 | 0.00 | | 0 | 0.00 | | 6 | 1.77 | NRXN1; PCLO; RIMS1; SLC18A2; SNCA; SYT17 | 4 | 1.32 | STON2; TH; UNC13A; WNT7A |
| cd8 ter downstream pathway | 62 | 9 | 2.43 | CD3E; EOMES; FOSL1; IFNG; IL2RA; NRAS; PRKCQ; TNFRSF4; TNFRSF9 | 1 | 0.19 | IFNA5 | 0 | 0.00 | | 2 | 13.48 | GZMB; IL2RA | 0 | 0.00 | | 3 | 1.37 | FOSL1; JUNB; PRKCQ |
| positive regulation of actin filament polymerization: GO | 62 | 7 | 1.89 | ACTR3; ARPC1A; ARPC3; ARPC5L; CCL21; PFN1; PYCARD | 2 | 0.38 | GSN; SCIN | 0 | 0.00 | | 0 | 0.00 | | 1 | 0.41 | SCIN | 3 | 1.37 | ARPC1A; CDC42EP1; PFN1 |
| negative regulation of ossification: GO | 62 | 6 | 1.62 | AREG; CCL3; GREM1; HIF1A; P2RY2; SRGN | 10 | 1.90 | BCL2; FGFR1; GATA1; GDF10; HAND2; LRP4; NOG; OSTN; PTCH1; RORB | 0 | 0.00 | | 0 | 0.00 | | 6 | 2.46 | BCL2; CHRD; FGFR1; HAND2; IGFBP5; PTCH1 | 3 | 1.37 | AREG; HIF1A; P2RY2 |
| circadian clock | 62 | 5 | 1.35 | ARNTL2; HIF1A; | 7 | 1.33 | BHLHE41; CRY2; DBP; | 0 | 0.00 | | 1 | 6.74 | SERPINE1 | 3 | 1.23 | BHLHE41; CRY2; | 3 | 1.37 | HIF1A; NAMPT; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | NAMPT; NOCT; SERPINE1 | | | F7; KLF15; PER1; PPARGC1A | | | | | | | | | PPARGC1A | | | NOCT |
| response to dsrna: GO | 62 | 4 | 1.08 | DDX21; IFNE; NPM1; RALB | 4 | 0.76 | COLEC12; IFNA5; P2RX7; TERT | 0 | 0.00 | | 0 | 0.00 | | 1 | 0.41 | RFTN2 | 3 | 1.37 | DDX21; IFNE; NPM1 |
| signalling to ras | 161 | 16 | 1.66 | ACTB; CDK1; CSF2; DUSP6; DUSP9; EREG; HBEGF; IL2RA; JAK3; NGF; NRAS; NRG1; NTRK1; PSMA5; PSMB6; RALB | 13 | 0.95 | BTC; CNKSR2; EGF; FGF1; FGFR1; FGFR3; GFRA1; GRIN2A; IL5; IRS2; NRG2; SHC2; SHC3 | 0 | 0.00 | | 1 | 2.60 | IL2RA | 5 | 0.79 | ANGPT1; CNKSR2; EGF; FGFR1; SHC2 | 7 | 1.23 | ACTB; CDK1; DUSP6; EREG; HBEGF; NGF; NRG1 |
| leukocyte chemotaxis: GO | 111 | 23 | 3.47 | ANXA1; CCL17; CCL18; CCL21; CCL22; CCL3; CCL7; CCR5; CXADR; CXCL10; CXCL11; CXCL13; CXCL3; CXCR1; CXCR4; IFNG; IL1B; IL6; S100A12; S100A8; S100A9; SCG2; TREM1 | 4 | 0.43 | CCL14; EDN3; FOLR2; IL16 | 0 | 0.00 | | 3 | 11.29 | FFAR2; IL1B; TREM1 | 2 | 0.46 | CCL14; EDN3 | 5 | 1.28 | CCL20; CXCL11; CXCR1; HRH1; IL10 |
| detection of abiotic stimulus: GO | 111 | 11 | 1.66 | CHRNA9; CNGB1; ELOVL4; | 14 | 1.49 | ADORA1; ANO3; ATP2B2; | 0 | 0.00 | | 0 | 0.00 | | 4 | 0.92 | COL 11A1; PDZD7; PIEZO2; | 5 | 1.28 | NTSR1; PITPNM1; SERPINE2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline: Up-regu-lated | A: Fold Change (FC) Up | A: Up-regulated Genes | A: Down-regu-lated | A: Fold Change (FC) | A: Down-regulated Genes | B. Differentially expressed genes significant in the baseline vs week 12 comparison only in the placebo: Up-regu-lated | B: Fold Change (FC) Up | B: Up-regulated Genes | B: Down-regu-lated | B: Fold Change (FC) | B: Down-regulated Genes | C. Differentially expressed genes significant in the baseline vs week 12 comparison only in the nemo: Up-regu-lated | C: Fold Change (FC) Up | C: Up-regulated Genes | C: Down-regu-lated | C: Fold Change (FC) | C: Down-regulated Genes |
|---|---|---|---|---|---|---|---|---|---|---|---|---|---|---|---|---|---|---|---|
| | | | | GNGT2; JUP; NTRK1; NTSR1; PITPNM1; SDR16C5; SERPINE2; TIMELESS | | | CACNA1F; COL11A1; DRGX; EPHB1; GUCA1B; KCNA1; PDZD7; PKD1; PKD 1L2; TMC2; TRPM3 | | | | | | | | | PKD1L2 | | | TIMELESS; TMC1 |
| phosphatidyl-inositol phosphate binding: GO | 111 | 6 | 0.90 | ADAP2; ARAP2; MYO1B; PFN1; RACGAP1; TWF1 | 11 | 1.17 | ACTN2; APBA1; CLVS1; CLVS2; JPH2; KCNJ1; SCIN; SNX21; STXBP6; SYT1; TTPA | 0 | 0.00 | | 1 | 3.76 | SNX20 | 3 | 0.69 | APBA1; SCIN; STXBP6 | 5 | 1.28 | ADAP2; MARK1; MYO1B; PFN1; TWF1 |
| cis trans isomerase activity: GO | 39 | | 2.57 | FKBPL; PPIA; PPIB; PPIF; PPIL1; TTC9 | 1 | 0.30 | PPIL6 | 0 | 0.00 | | 0 | 0.00 | | 2 | 1.30 | FKBP7; PPIL6 | 2 | 1.45 | PPIF; PPIL1 |
| detection of mechanical stimulus: GO | 39 | 4 | 1.72 | CHRNA9; JUP; NTRK1; SERPINE2 | 8 | 2.42 | ANO3; ATP2B2; COL11A1; KCNA1; PDZD7; PKD1; PKD1L2; TMC2 | 0 | 0.00 | | 0 | 0.00 | | 4 | 2.61 | COL11A1; PDZD7; PIEZO2; PKD1L2 | 2 | 1.45 | SERPINE2; TMC1 |
| regulation of phospholipase c activity: GO | 39 | 4 | 1.72 | GNA15; PTAFR; SIPR4; SELE | 6 | 1.82 | ADRA1A; AGT: ARHGAP6; CALCR; FGFR1; NMUR1 | 0 | 0.00 | | 1 | 10.72 | SELE | 6 | 3.91 | ADCYAP1R; ADRA1A; ESR1; FGF2; FGFR1; LPAR1 | 2 | 1.45 | GNA15; PTAFR |
| cochlea development: GO | 39 | 3 | 1.29 | CCNA2; GRHL3; WNT5A | 8 | 2.42 | ATP2B2; FRZB; GABRB3; GLI2; NTRK3; SIX1; | 0 | 0.00 | | 0 | 0.00 | | 3 | 1.95 | GLI2; KCNK2; SLITRK6 | 2 | 1.45 | CCNA2; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | SLC26A5; SOBP | | | | | | | | | | | | |
| forelimb morphogenesis: GO | 39 | 3 | 1.29 | CRABP2; SALL3; WNT7A | 8 | 2.42 | ALX4; GDF5; OSR1; OSR2; RNF165; TBX5; TFAP2B; ZBTB16 | 0 | 0.00 | | 0 | 0.00 | | 4 | 2.61 | ALX4; OSR1; RECK; SHOX2 | 2 | 1.45 | CRABP2; WNT7A |
| nuclear replication fork: GO | 39 | 3 | 1.29 | CDC45; MCM10; PCNA | 0 | 0.00 | | 0 | 0.00 | | 0 | 0.00 | | 0 | 0.00 | | 2 | 1.45 | CDC45; GINS4 |
| regulation of mitophagy: GO | 39 | 3 | 1.29 | HIF1A; RUVBL1; VDAC1 | 1 | 0.30 | KAT2A | 0 | 0.00 | | 0 | 0.00 | | 0 | 0.00 | | 2 | 1.45 | HIF1A; VDAC1 |
| sulfur compound catabolic process: GO | 39 | 3 | 1.29 | ACOT7; AHCY; HPSE | 4 | 1.21 | BCAN; CDO1; IDUA; PRELP | 0 | 0.00 | | 0 | 0.00 | | 1 | 0.65 | DCN | 2 | 1.45 | ACOT7; HPSE |
| long term synaptic potentiation: GO | 39 | 2 | 0.86 | PLK2; SERPINE2 | 7 | 2.12 | DRD1; GRIN2A; NLGN1; RELN; RIMS1; SLC24A2; SNCA | 0 | 0.00 | | 0 | 0.00 | | 3 | 1.95 | RELN; RIMS1; SNCA | 2 | 1.45 | PLK2; SERPINE2 |
| positive regulation of neural precursor cell proliferation: GO | 39 | 2 | 0.86 | ASPM; HIF1A | 6 | 1.82 | CDON; DCT; EGF; GLI2; PAX6; SOX10 | 0 | 0.00 | | 0 | 0.00 | | 3 | 1.95 | CDON; EGF; GLI2 | 2 | 1.45 | ASPM; HIF1A |
| rab gefs exchange gtp for gdp on rabs | 39 | 2 | 0.86 | RAB10; RAB31 | 1 | 0.30 | TRAPPC6A | 0 | 0.00 | | 0 | 0.00 | | 1 | 0.65 | TRAPPC6A | 2 | 1.45 | RAB31; ST5 |
| recycling endosome membrane: GO | 39 | 2 | 0.86 | RAB10; RAP2B | 1 | 0.30 | SLC26A7 | 0 | 0.00 | | 0 | 0.00 | | 0 | 0.00 | | 2 | 1.45 | NDRG1; RAP2B |
| regulation of axon guidance: GO | 39 | 2 | 0.86 | SEMA4B; WNT5A | 9 | 2.72 | FEZF2; PLXNA3; PLXNA4; SEMA3A; SEMA3B; SEMA3D; SEMA3E; | 0 | 0.00 | | 0 | 0.00 | | 5 | 3.26 | CXCL12; PLXNA4; SEMA3E; SEMA4G; SLIT2 | 2 | 1.45 | SEMA4B; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | A: Fold Change (FC) Up | A: Up-regulated Genes | A: Down-regulated | A: Fold Change (FC) | A: Down-regulated Genes | B. Differentially expressed genes significant in the baseline vs week 12 comparison only in the placebo: Up-regulated | B: Fold Change (FC) Up | B: Up-regulated Genes | B: Down-regulated | B: Fold Change (FC) | B: Down-regulated Genes | C. Differentially expressed genes significant in the baseline vs week 12 comparison only in the nemo: Up-regulated | C: Fold Change (FC) Up | C: Up-regulated Genes | C: Down-regulated | C: Fold Change (FC) | C: Down-regulated Genes |
|---|---|---|---|---|---|---|---|---|---|---|---|---|---|---|---|---|---|---|---|
| | | | | | | | SEMA3G; SLIT2 | | | | | | | | | | | | |
| regulation of carbohydrate catabolic process: GO | 39 | 2 | 0.86 | HIF1A; PGAM1 | 5 | 1.51 | GPD1; MLXIPL; P2RX7; PPARGC1A; PRKAA2 | 1 | 10.72 | GPD1 | 0 | 0.00 | | 2 | 1.30 | PPARGC1A; PRKAA2 | 2 | 1.45 | HIF1A; PGAM1 |
| regulation of endothelial cell apoptotic process: GO | 39 | 2 | 0.86 | SCG2; SERPINE1 | 1 | 0.30 | NDNF | 0 | 0.00 | | 1 | 10.72 | SERPINE1 | 3 | 1.95 | ANGPT1; ECSCR; NDNF | 2 | 1.45 | ANGPTL4; IL10 |
| aminoglycan metabolic process: GO | 162 | 14 | 1.45 | B3GNT3; CHI3L2; CHST1; HAS3; HMMR; HPSE; HS3ST1; HS3ST3A1; HS3ST3B1; HYAL3; IL1B; MKI67; PGLYRP2; SDC1 | 18 | 1.31 | BCAN; CHST12; CHST5; EXTL1; GPC2; GPC3; GPC6; HAS1; HPSE2; HS3ST2; HS3ST5; HS3ST6; IDUA; ITIH5; NDNF; PRELP; SDC2; UST | 0 | 0.00 | | 1 | 2.58 | IL1B | 10 | 1.57 | ANGPT1; CHST12; DCN; DSEL; FGF2; FOXC1; GPC2; HPSE2; NDNF; UST | 7 | 1.23 | AGRN; CHST1; HMMR; HPSE; HS3ST1; HS3ST3A1; MKI67 |
| active ion transmembrane transporter activity: GO | 162 | 6 | 0.62 | ATP12A; ATP1B3; SLC10A6; SLC26A9; SLC6A11; SLC7A11 | 28 | 2.04 | ABCB11; ABCC3; ABCC8; ATP13A5; ATP1A2; ATP2A1; ATP2B2; ATP6V0A4; ATP6V0E2; CFTR; FXYD2; SLC10A2; SLC13A2; SLC17A4; SLC17A7; SLC1A2; | 0 | 0.00 | | 0 | 0.00 | | 12 | 1.88 | ABCC9; ATP13A4; ATP13A5; ATP1B2; ATP2C2; ATP6V0A4; ATP6V0E2; SLC13A2; SLC1A6; SLC1A7; SLC4A4; SLC9A2 | 7 | 1.23 | SLC13A5; SLC20A1; SLC26A6; SLC4A7; SLC5A5; SLC6A11; SLC7A11 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | A: Fold Change (FC) Up | A: Up-regulated Genes | A: Down-regulated | A: Fold Change (FC) | A: Down-regulated Genes | B. Differentially expressed genes significant in the baseline vs week 12 comparison only in the placebo: Up-regulated | B: Fold Change (FC) Up | B: Up-regulated Genes | B: Down-regulated | B: Fold Change (FC) | B: Down-regulated Genes | C. Differentially expressed genes significant in the baseline vs week 12 comparison only in the nemo: Up-regulated | C: Fold Change (FC) Up | C: Up-regulated Genes | C: Down-regulated | C: Fold Change (FC) | C: Down-regulated Genes |
|---|---|---|---|---|---|---|---|---|---|---|---|---|---|---|---|---|---|---|---|
| | | | | | | | SLC1A6; SLC1A7; SLC22A9; SLC24A2; SLC26A1; SLC26A5; SLC26A7; SLC34A3; SLC4A1; SLC4A4; SLC9A2; SLC9A4 | | | | | | | | | | | | |
| endothelium development: GO | 87 | 6 | 1.15 | F2RL1; GJA1; MSN; NRG1; RAP2B; WNT7A | 8 | 1.08 | ARHGEF26; CD34; GSTM3; HAPLN2; MESP1; SCUBE1; TMEM100; TNMD | 0 | 0.00 | | 0 | 0.00 | | 5 | 1.46 | ARHGEF26; CD34; MESP1; SLC40A1; TNMD | 4 | 1.30 | MSN; NRG1; RAP2B; WNT7A |
| heat shock protein binding: GO | 87 | 5 | 0.96 | BAK1; CDK1; HIF1A; HSPA6; HSPA8 | 4 | 0.54 | ADORA1; FGF1; GRXCR2; HSPA1L | 0 | 0.00 | | 1 | 4.80 | GBP1 | 1 | 0.29 | SLC18A2 | 4 | 1.30 | BAK1; CDK1; HIF1A; HSPA8 |
| organophosphate catabolic process: GO | 112 | 8 | 1.20 | LIPG; NTSR1; NUDT15; PGM2; PLA2G4D; PNP; UPP1; VCP | 8 | 0.84 | ASPDH; ENPP1; GPD1; NEIL1; PDE11A; PDE9A; PON1; UPP2 | 1 | 3.73 | GPD1 | 0 | 0.00 | | 2 | 0.45 | ENPP3; PDE9A | 5 | 1.27 | NTSR1; NUDT15; PLA2G4D; PNP; XDH |
| positive regulation of interferon gamma production: GO | 63 | 11 | 2.92 | CD2; CD3E; EBI3; IL12B; IL12RB2; IL1B; PYCARD; SASH3; SLAMF1; TNFSF9; WNT5A | 0 | 0.00 | | 0 | 0.00 | | 1 | 6.63 | IL1B | 0 | 0.00 | | 3 | 1.35 | BCL3; IL12RB2; WNT5A |
| retina homeostasis: GO | 63 | 8 | 2.12 | ACTB; CDH3; CNGB1; | 7 | 1.31 | ALB; CDHR1; CROCC; | 0 | 0.00 | | 1 | 6.63 | LYZ | 3 | 1.21 | MAK; PIP; TUB | 3 | 1.35 | ACTB; LTF; SLC28A3 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | IGKC; LTF; LYZ; PRDX1; SLC28A3 | | | NXNL2; PCDH15; PIP; TF | | | | | | | | | | | | |
| arginine and proline metabolism | 63 | 7 | 1.86 | ALDH1A3; ALDH4A1; AMD1; EPRS; GOT2; ODC1; SRM | 5 | 0.94 | AOC3; CKM; MAOA; NOS2; PRODH | 0 | 0.00 | | 0 | 0.00 | | 5 | 2.02 | ALDH3A2; ALDH5A1; GAMT; GATM; PRODH | 3 | 1.35 | GOT2; NAGS; ODC1 |
| cellular response to heat stress | 63 | 7 | 1.86 | FPR1; HSPA4; HSPA5; HSPA6; HSPA8; HSPH1; TNFRSF21 | 0 | 0.00 | | 0 | 0.00 | | 0 | 0.00 | | 1 | 0.40 | SLC29A1 | 3 | 1.35 | HSPA5; HSPA8; HSPH1 |
| cell cell contact zone: GO | 63 | 6 | 1.59 | CXADR; DSC2; DSP; GJA1; JUP; RAP2B | 6 | 1.12 | ANK2; ATP1A2; CTNNA3; DES; PCDH9; PGM5 | 0 | 0.00 | | 0 | 0.00 | | 1 | 0.40 | PGM5 | 3 | 1.35 | ACTN1; DSC2; RAP2B |
| regulation of dna templated transcription in response to stress: GO | 63 | 4 | 1.06 | CHEK1; HIF1A; HMOX1; HSPA5 | 1 | 0.19 | HIF3A | 0 | 0.00 | | 0 | 0.00 | | 2 | 0.81 | CREB3L1; HIF3A | 3 | 1.35 | CHEK1; HIF1A; HSPA5 |
| negative regulation of axonogenesis: GO | 63 | 3 | 0.80 | CDK5R1; SEMA4B; WNT5A | 8 | 1.50 | LRP4; PLXNA3; SEMA3A; SEMA3B; SEMA3D; SEMA3E; SEMA3G; SLIT2 | 0 | 0.00 | | 0 | 0.00 | | 3 | 1.21 | SEMA3E; SEMA4G; SLIT2 | 3 | 1.35 | CDK5R1; SEMA4B; WNT5A |
| modified amino acid binding: GO | 63 | 2 | 0.53 | GSTP1; HSPA8 | 8 | 1.50 | ANXA13; FOLR1; FOLR2; GSTM2; GSTM3; JPH2; SCIN; SYT1 | 0 | 0.00 | | 0 | 0.00 | | 2 | 0.81 | ANXA9; SCIN | 3 | 1.35 | GSTP1; HSPA8; MARK1 |
| magnesium ion binding: GO | 189 | 6 | 0.53 | ENO1; MTHFD2; | 8 | 0.50 | ADCY2; BRSK2; | 0 | 0.00 | | 0 | 0.00 | | 5 | 0.67 | BRSK2; PGM5; | 8 | 1.20 | DYRK3; ENO1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | NME1; PGM2; PIF1; TOP2A | | | EPHX2; MAST1; PCK1; PGM5; RPS6KA6; SNCA | | | | | | | | | RPS6KA6; SNCA; TESC | | | MARK1; PIF1; RPS6KA4; S100P; TOP2A; TREX2 |
| regulation of calcium ion transport into cytosol: GO | 88 | 9 | 1.71 | BAK1; BDKRB1; CXCL10; CXCL11; CXCL9; GSTO1; NPSR1; NTSR1; UBASH3B | 11 | 1.47 | ANK2; ATP1A2; BCL2; CASQ2; DMD; DRD1; GSTM2; JPH2; P2RX7; SNCA; TRDN | 0 | 0.00 | | 1 | 4.75 | CXCL9 | 6 | 1.73 | ADCYAP1R1; BCL2; HRC; SNCA; TRDN; TRPC1 | 4 | 1.29 | BAK1; CXCL11; NTSR1; UBASH3B |
| neuropeptide signaling pathway: GO | 88 | 8 | 1.52 | ADCYAP1; GPR1; LTB4R; NMU; NPSR1; NTSR1; PROK2; QRFPR | 10 | 1.34 | CARTPT; GALR1; GLRB; NMUR1; NPY1R; NPY5R; NPY6R; NXPH3; SORCS1; TAC3 | 0 | 0.00 | | 0 | 0.00 | | 3 | 0.87 | CPE; GLRB; NPY1R | 4 | 1.29 | NMU; NTSR1; QRFPR; SORCS2 |
| prostate cancer | 88 | 6 | 1.14 | CCNE1; CDKN1A; E2F3; GSTP1; NRAS; TGFA | 6 | 0.80 | AR; BCL2; EGF; FGFR1; PDGFD; TCF7L1 | 0 | 0.00 | | 0 | 0.00 | | 5 | 1.44 | BCL2; CREB3L1; EGF; FGFR1; TCF7L1 | 4 | 1.29 | CDKN1A; E2F1; GSTP1; TGFA |
| negative regulation of immune response: GO | 113 | 18 | 2.67 | ADCYAP1; ANXA1; FOXF1; HMOX1; IFI16; IL12B; IL13RA2; IL1RL1; IL2RA; IL4R; IL7R; JAK3; NMI; PGLYRP2; SAMSN1; | 2 | 0.21 | AMBP; C4BPA | 0 | 0.00 | | 4 | 14.79 | IL2RA; IL7R; SAMSN1; SERPINB9 | 1 | 0.22 | ANGPT1 | 5 | 1.25 | HLA-G; IFI16; IL10; IL13RA2; NMI |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | SERPINB4; SERPINB9; SLAMF1 | | | | | | | | | | | | | | | |
| bladder cancer | 40 | 7 | 2.93 | CDKN1A; E2F3; MMP1; MMP9; NRAS; PGF; TYMP | 2 | 0.59 | EGF; FGFR3 | 0 | 0.00 | | 0 | 0.00 | | 1 | 0.64 | EGF | 2 | 1.42 | CDKN1A; E2F1 |
| regulation of leukocyte degranulation: GO | 40 | 7 | 2.93 | F2RL1; FOXF1; HMOX1; IL13RA2; IL4R; PTAFR; RAC2 | 1 | 0.29 | PRAM1 | 0 | 0.00 | | 1 | 10.45 | RAC2 | 0 | 0.00 | | 2 | 1.42 | IL13RA2; PTAFR |
| glycosyl compound catabolic process: GO | 40 | 6 | 2.51 | AHCY; APOBEC3A; CDA; PNP; TYMP; UPP1 | 2 | 0.59 | ENPP4; UPP2 | 0 | 0.00 | | 0 | 0.00 | | 0 | 0.00 | | 2 | 1.42 | CDA; PNP |
| isoprenoid binding: GO | 40 | 6 | 2.51 | ADH7; CRABP2; LRAT; UGT1A1; UGT1A10; UGT1A7 | 3 | 0.88 | RBP4; SERPINA5; UGT2B7 | 0 | 0.00 | | 0 | 0.00 | | 0 | 0.00 | | 2 | 1.42 | CRABP2; LRAT |
| myeloid cell activation involved in immune response: GO | 40 | 6 | 2.51 | ANXA3; CCL3; NR4A3; PLA2G3; PYCARD; SLAMF1 | 0 | 0.00 | | 0 | 0.00 | | 1 | 10.45 | ANXA3 | 0 | 0.00 | | 2 | 1.42 | PLA2G3; SBNO2 |
| apoptotic execution phase | 40 | 5 | 2.09 | CLSPN; DSG3; HIST1H1B; HIST1H1D; LMNB1 | 3 | 0.88 | GAS2; GSN; MAPT | 0 | 0.00 | | 0 | 0.00 | | 1 | 0.64 | MAPT | 2 | 1.42 | HIST1H1B; HIST1H1D |
| endodermal cell differentiation: GO | 40 | 4 | 1.67 | EOMES; HMGA2; LAMB3; MMP9 | 3 | 0.88 | COL11A1; ITGA7; NANOG | 0 | 0.00 | | 0 | 0.00 | | 1 | 0.64 | COL11A1 | 2 | 1.42 | HMGA2; LAMB3 |
| regulation of bone remodeling: GO | 40 | 4 | 1.67 | CA2; GJA1; GREM1; | 6 | 1.77 | CARTPT; CLDN18; | 0 | 0.00 | | 0 | 0.00 | | 2 | 1.27 | CLDN18; PDK4 | 2 | 1.42 | CA2; UBASH3B |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | UBASH3B | | | LEP; LEPR; P2RX7; PDK4 | | | | | | | | | | | | |
| regulation of catecholamine secretion: GO | 40 | 4 | 1.67 | CHRNA6; GDNF; HRH3; P2RY1 | 9 | 2.65 | ADRA2A; AGT; CARTPT; CNR1; KCNA2; KCNB1; PCP4; SNCA; SNCG | 0 | 0.00 | | 0 | 0.00 | | 3 | 1.91 | ADRA2A; CXCL12; SNCA | 2 | 1.42 | CHRNA6; P2RY1 |
| slc transporter disorders | 40 | 4 | 1.67 | GK; SLC16A1; SLC2A1; SLC2A9 | 4 | 1.18 | ALB; CP; SLC4A4; SLC7A9 | 0 | 0.00 | | 0 | 0.00 | | 3 | 1.91 | CP; SLC40A1; SLC4A4 | 2 | 1.42 | SLC2A1; SLC2A9 |
| response to exogenous dsrna: GO | 40 | 3 | 1.26 | DDX21; IFNE; RALB | 2 | 0.59 | COLEC12; IFNA5 | 0 | 0.00 | | 0 | 0.00 | | 1 | 0.64 | RFTN2 | 2 | 1.42 | DDX21; IFNE |
| aldosterone regulated sodium reabsorption | 40 | 2 | 0.84 | ATP1B3; SFN | 7 | 2.06 | ATP1A2; FXYD2; HSD11B1; IRS2; IRS4; KCNJ1; NR3C2 | 1 | 10.45 | HSD11B2 | 0 | 0.00 | | 3 | 1.91 | ATP1B2; NR3C2; SCNN1B | 2 | 1.42 | SFN; SGK1 |
| catecholamine metabolic process: GO | 40 | 2 | 0.84 | SNCB; TH | 7 | 2.06 | DRD1; DRD4; GRIN2A; HAND2; MAOA; SNCA; SULT1A2 | 0 | 0.00 | | 0 | 0.00 | | 3 | 1.91 | HAND2; HDC; SNCA | 2 | 1.42 | SNCB; TH |
| somatic diversification of immune receptors: GO | 40 | 2 | 0.84 | EXO1; POLQ | 0 | 0.00 | | 0 | 0.00 | | 0 | 0.00 | | 0 | 0.00 | | 2 | 1.42 | EXO1; POLQ |
| stereocilium bundle: GO | 40 | 2 | 0.84 | IDO1; PLS3 | 8 | 2.36 | CLIC5; ESPN; GRXCR2; MYO15A; PCDH15; PDZD7; TMC2; TSPEAR | 0 | 0.00 | | 0 | 0.00 | | 2 | 1.27 | CLIC5; PDZD7 | 2 | 1.42 | SLC4A7; TMC1 |
| basement | 40 | 1 | 0.42 | LAMB3 | 4 | 1.18 | LAMA2; | 0 | 0.00 | | 0 | 0.00 | | 4 | 2.54 | LAMA2; | 2 | 1.42 | AGRN; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| membranes | | | | | | | LAMB4; LAMC3; NTN5 | | | | | | | | | LAMC3; NTN4; NTN5 | | | LAMB3 |
| regulation of axonogenesis: GO | 164 | 10 | 1.02 | CDK5R1; CRABP2; LPAR3; NEFL; NGF; NRG1; SEMA4B; TNFRSF12A; WNT5A; WNT7A | 18 | 1.29 | APOE; CDH4; FEZF2; GRIN1; LRP4; LRRC4C; MAPT; NTRK3; PLXNA3; PLXNA4; SEMA3A; SEMA3B; SEMA3D; SEMA3E; SEMA3G; SLIT2; SLIT3; UST | 0 | 0.00 | | 0 | 0.00 | | 10 | 1.55 | CXCL12; LRRC4C; MAPT; PLXNA4; SEMA3E; SEMA4G; SHOX2; SLIT2; SLIT3; UST | 7 | 1.21 | CDK5R1; CRABP2; NGF; NRG1; SEMA4B; WNT5A; WNT7A |
| cellular ketone metabolic process: GO | 64 | 9 | 2.35 | AKR1B10; COQ2; CYP4F11; GLO1; GOT2; HMGCR; IDO1; KYNU; TDO2 | 5 | 0.92 | CACNAIH; CYP17A1; CYP2W1; GPD1; LHB | 1 | 6.53 | GPD1 | 1 | 6.53 | TDO2 | 2 | 0.79 | CACNA1H; CYP2W1 | 3 | 1.33 | AKRIB10; GOT2; PDSS1 |
| iron ion homeostasis: GO | 64 | 6 | 1.57 | HIF1A; HMOX1; HMOX2; LCN2; LTF; STEAP4 | 10 | 1.84 | ALAS2; CP; CYBRD1; EPB42; HAMP; RHAG; SCARA5; SLC22A17; TF; TMPRSS6 | 0 | 0.00 | | 0 | 0.00 | | 6 | 2.38 | CP; CYBRD1; SCARA5; SLC22A17; SLC40A1; STEAP2 | 3 | 1.33 | HIF1A; HMOX2; LTF |
| peripheral nervous system development: GO | 64 | 4 | 1.05 | ARTN; GDNF; NRG1; OSM | 12 | 2.21 | ADAM22; FA2H; GFRA3; GSTM3; HAND2; HAPLN2; LAMA2; LGI4; MYOC; | 0 | 0.00 | | 1 | 6.53 | OSM | 7 | 2.78 | ADAM22; ALDH3A2; HAND2; LAMA2; LGI4; MYOC; PLXNA4 | 3 | 1.33 | ARTN; NDRG1; NRG1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | PLXNA4; SOX10; SOX8 | | | | | | | | | | | | |
| regulation of lipid transport: GO | 89 | 7 | 1.32 | ABCA12; IL1B; LIPG; LRAT; NTSR1; P2RY2; PRELID1 | 16 | 2.12 | ABCA2; ADIPOQ; AGT; AGTR1; APOC1; APOE; CYP4A11; EGF; GALR1; IRS2; LEP; P2RX7; PLA2G6; PON1; PTCH1; REN | 1 | 4.70 | ADIPOQ | 1 | 4.70 | IL1B | 4 | 1.14 | AGTR1; CYP4A11; EGF; PTCH1 | 4 | 1.27 | LRAT; NTSR1; P2RY2; PRELID1 |
| golgi cisterna: GO | 89 | 5 | 0.94 | FUT1; FUT2; FUT3; PITPNM1; PSENEN | 3 | 0.40 | ABO; FUT9; ST6GAL2 | 0 | 0.00 | | 0 | 0.00 | | 3 | 0.86 | ABO; ATL1; GAL3ST4 | 4 | 1.27 | FUT1; FUT2; FUT3; PITPNM1 |
| actin filament binding: GO | 114 | 6 | 0.88 | ACTR3; ARPC1A; ARPC3; FSCN1; MYO1B; PANX1 | 17 | 1.76 | ACTN2; CORO2B; CTNNA3; ESPN; GAS2L2; MYH11; MYH14; MYH3; MYL4; MYO1A; PKNOX2; PPPIR9A; SCIN; SYNE1; TLN2; TMOD1; TNNC1 | 0 | 0.00 | | 0 | 0.00 | | 6 | 1.34 | CORO2B; SCIN; SHROOM3; SYNE1; TLN2; TNNC1 | 5 | 1.24 | ACTN1; ARPC1A; CORO6; MYO1B; PANX1 |
| recycling e ndosome: GO | 114 | 5 | 0.73 | KCNK1; RAB10; RAN; RAP2B; ST8SIA2 | 7 | 0.72 | CFTR; DYNC1I1; GRIA1; MLC1; SLC26A7; TF; USP6 | 0 | 0.00 | | 0 | 0.00 | | 1 | 0.22 | GRIA1 | 5 | 1.24 | KCNK1; NDRG1; RAN; RAP2B; ST8SIA2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| response to temperature stimulus: GO | 140 | 15 | 1.79 | CDKN1A; CXCL10; EIF2S1; GK; HMOX1; HSPA6; IL1A; IL1B; IL6; MKI67; NTRK1; NTSR1; OSM; PRKCQ; SOCS3 | 13 | 1.10 | ADORA1; ADRB1; ANO3; DRGX; EPHB1; FGF1; HMGCS2; HSPB7; LPL; MSTN; PPARGC1A; SCARA5; TRPM3 | 1 | 2.98 | LPL | 2 | 5.97 | IL1B; OSM | 5 | 0.91 | CRNN; CXCL12; HMGCS2; PPARGC1A; SCARA5 | 6 | 1.22 | CDKN1A; MKI67; NTSR1; PRKCQ; SOCS3; TRPV3 |
| virus receptor activity: GO | 65 | 11 | 2.83 | CCR5; CD80; CXADR; CXCR4; DPP4; HYAL3; ITGB6; LDLR; SERPINB3; SLAMF1; TNFRSF4 | 1 | 0.18 | NCAM1 | 0 | 0.00 | | 0 | 0.00 | | 2 | 0.78 | EFNB3; NCAM1 | 3 | 1.31 | DPP4; ITGB6; LDLR |
| negative regulation of leukocyte proliferation: GO | 65 | 9 | 2.32 | CD274; CTLA4; GREM1; GSTP1; IDO1; IL2RA; PRDM1; PRNP; TNFRSF21 | 1 | 0.18 | SCGB1A1 | 0 | 0.00 | | 1 | 6.43 | IL2RA | 0 | 0.00 | | 3 | 1.31 | GSTP1; HLA-G; IL10 |
| il4 2pathway | 65 | 7 | 1.80 | CCL17; IGHG1; IL13RA1; IL13RA2; IL4R; JAK3; SOCS3 | 3 | 0.54 | FCER2; IL5; IRS2 | 1 | 6.43 | IGHG1 | 0 | 0.00 | | 0 | 0.00 | | 3 | 1.31 | IL10; IL13RA2; SOCS3 |
| glioma | 65 | 6 | 1.54 | CALML3; CALML5; CDKN1A; E2F3; NRAS; TGFA | 6 | 1.09 | CALML6; CAMK2A; CAMK2B; EGF; SHC2; SHC3 | 0 | 0.00 | | 0 | 0.00 | | 2 | 0.78 | EGF; SHC2 | 3 | 1.31 | CDKN1A; E2F1; TGFA |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| myeloid leukocyte mediated immunity: GO | 41 | 9 | 3.67 | ANXA3; CCL3; CXCL5; CXCL6; IL6; NR4A3; PLA2G3; SERPINB9; TREM1 | 1 | 0.29 | ELANE | 0 | 0.00 | | 4 | 40.77 | ANXA3; CXCL5; SERPINB9; TREM1 | 2 | 1.24 | CTSG; ELANE | 2 | 1.38 | CXCL6; PLA2G3 |
| negative regulation of cytokine secretion: GO | 41 | 9 | 3.67 | ANXA1; F2RL1; IL36RN; IL6; SLAMF1; SRGN; TNFRSF21; TNFRSF9; ZC3H12A | 2 | 0.58 | CD34; SSC5D | 0 | 0.00 | | 1 | 10.19 | GBP1 | 4 | 2.48 | ANGPT1; CD34; FBLN1; SSC5D | 2 | 1.38 | IL10; ZC3H12A |
| positive regulation of dna binding: GO | 41 | 5 | 2.04 | HMGA2; MMP9; NME1; PLAUR; TXN | 4 | 1.15 | EGF; HAND2; KAT2A; MYOCD | 0 | 0.00 | | 0 | 0.00 | | 2 | 1.24 | EGF; HAND2 | 2 | 1.38 | HMGA2; TXN |
| prostate gland development: GO | 41 | 5 | 2.04 | ANXA1; SERPINB5; TNC; TP63; WNT5A | 5 | 1.44 | AR; CRIP1; GLI2; ID4; NOG | 0 | 0.00 | | 0 | 0.00 | | 5 | 3.10 | CRIP1; ESR1; FOXA1; GLI2; PSAPL1 | 2 | 1.38 | SERPINB5; WNT5A |
| sumoylation of chromatin organization proteins | 41 | 5 | 2.04 | CBX2; HIST1H4I; HIST1H4J; HIST1H4K; HIST1H4L | 0 | 0.00 | | 0 | 0.00 | | 0 | 0.00 | | 0 | 0.00 | | 2 | 1.38 | CBX2; HIST1H4I |
| epithelial cell morphogenesis: GO | 41 | 4 | 1.63 | GDNF; GREM1; RAB25; VSIG1 | 3 | 0.86 | ARHGEF26; DACT2; TNMD | 0 | 0.00 | | 0 | 0.00 | | 3 | 1.86 | ARHGEF26; FZD7; TNMD | 2 | 1.38 | HRH2; VSIG1 |
| eye photoreceptor cell differentiation: GO | 41 | 3 | 1.22 | PRDM1; SDK2; TH | 4 | 1.15 | PAX6; RORB; SOX8; TRPM1 | 0 | 0.00 | | 0 | 0.00 | | 0 | 0.00 | | 2 | 1.38 | SDK2; TH |
| pituitary gland development: GO | 41 | 3 | 1.22 | ADCYAP1; PITX1; WNT5A | 3 | 0.86 | GLI2; NOG; PAX6 | 0 | 0.00 | | 0 | 0.00 | | 1 | 0.62 | GLI2 | 2 | 1.38 | PITX1; WNT5A |
| cerebral cortex cell migration: GO | 41 | 2 | 0.82 | CDK5R1; FBXO45 | 7 | 2.01 | DCX; FGFR1; HTR6; | 0 | 0.00 | | 0 | 0.00 | | 4 | 2.48 | FGFR1; POU3F3; | 2 | 1.38 | CDK5R1; FBXO45 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | POU3F3; RELN; SEMA3A; SLIT2 | | | | | | | | | RELN; SLIT2 | | | |
| epo pathway | 41 | 2 | 0.82 | SOCS3; STAT1 | 2 | 0.58 | BCL2; IRS2 | 0 | 0.00 | | 0 | 0.00 | | 1 | 0.62 | BCL2 | 2 | 1.38 | SOCS3; VAV2 |
| glutamate receptor signaling pathway: GO | 41 | 2 | 0.82 | CDK5R1; HOMER1 | 11 | 3.17 | GRIA1; GRIA2; GRIA4; GRIK3; GRIK4; GRIK5; GRIN1; GRIN2A; GRM7; KCNB1; TRPM1 | 1 | 10.19 | GRIA4 | 0 | 0.00 | | 3 | 1.86 | GRIA1; GRIA2; GRIK3 | 2 | 1.38 | CDK5R1; HOMER1 |
| serine family amino acid metabolic process: GO | 41 | 2 | 0.82 | AHCY; EIF4A3 | 3 | 0.86 | CDO1; DMGDH; GLYAT | 0 | 0.00 | | 0 | 0.00 | | 1 | 0.62 | DMGDH | 2 | 1.38 | EIF4A3; GLDC |
| female sex differentiation: GO | 115 | 8 | 1.16 | ADCYAP1; BAK1; BRCA2; CCNE1; EREG; STRA6; TP63; WNT5A | 13 | 1.33 | ACSBG1; AMHR2; BCL2; DACH1; FZD4; INHBB; LEP; MERTK; NOBOX; NR5A1; RBP4; SLIT2; SLIT3 | 0 | 0.00 | | 0 | 0.00 | | 7 | 1.55 | ADCYAP1R1; BCL2; DACH1; ESR1; FOXC1; SLIT2; SLIT3 | 5 | 1.23 | BAK1; BMPRIB; BRCA2; EREG; WNT5A |
| antigen processing: ubiquitination & proteasome degradation | 167 | 12 | 1.20 | CDC20; DTX3L; HERC6; KBTBD8; LRR1; PSMA5; PSMB6; SOCS3; UBA6; | 4 | 0.28 | DET1; TRIM50; UNKL; ZBTB16 | 0 | 0.00 | | 0 | 0.00 | | 2 | 0.30 | GAN; LONRF1 | 7 | 1.19 | CDC20; HERC6; LRR1; RNF19B; SOCS3; UBE2C; UBE2F |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline: Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo: Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo: Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | UBE2C; UBE2F; UBE2N | | | | | | | | | | | | | | | |
| asparagine n-linked glycosylation | 193 | 12 | 1.04 | AREG; CALR; CAP1; CTSC; DYNLL1; PDIA3; ST8SIA2; TGFA; TUBA1C; TUBA4A; TUBB2A; TUBB6 | 5 | 0.31 | ANK2; ASGR1; FOLR1; ST6GALNAC5; TRAPPC6A | 0 | 0.00 | | 0 | 0.00 | | 3 | 0.39 | DLC1; ST6GALNAC5; TRAPPC6A | 8 | 1.18 | AREG; CAP1; ST8SLA2; TGFA; TUBA1C; TUBA4A; TUBB2A; TUBB6 |
| spermatid differentiation: GO | 116 | 5 | 0.72 | HOOK1; PLA2G3; RAN; TRIP13; TXNDC8 | 11 | 1.12 | CAPZA3; CFTR; CHD5; DDX25; H1FNT; OCA2; RSPH1; SPAG6; SYCP1; TDRD5; TNP1 | 0 | 0.00 | | 0 | 0.00 | | 4 | 0.88 | CAPZA3; DDX25; SYCP3; TMEM119 | 5 | 1.22 | PLA2G3; PTCHD3; RAN; SLC26A6; TRIP13 |
| aminoglycan catabolic process: GO | 66 | 6 | 1.52 | CHI3L2; HMMR; HPSE; HYAL3; PGLYRP2; SDC1 | 8 | 1.43 | BCAN; GPC2; GPC3; GPC6; HPSE2; IDUA; PRELP; SDC2 | 0 | 0.00 | | 0 | 0.00 | | 4 | 1.54 | DCN; FGF2; GPC2; HPSE2 | 3 | 1.29 | AGRN; HMMR; HPSE |
| metabolism of polyamines | 66 | 6 | 1.52 | AMD1; ODC1; PSMA5; PSMB6; SMOX; SRM | 0 | 0.00 | | 0 | 0.00 | | 0 | 0.00 | | 2 | 0.77 | GAMT; GATM | 3 | 1.29 | NAGS; ODC1; SMOX |
| renal cell carcinoma | 66 | 5 | 1.27 | HIF1A; NRAS; PGF; SLC2A1; TGFA | 1 | 0.18 | PAK3 | 0 | 0.00 | | 0 | 0.00 | | 1 | 0.38 | PAK3 | 3 | 1.29 | HIF1A; SLC2A1; TGFA |
| body fluid secretion: GO | 66 | 3 | 0.76 | HIF1A; HK2; NME1 | 7 | 1.25 | ATP2B2; CDO1; CHRM1; | 0 | 0.00 | | 0 | 0.00 | | 4 | 1.54 | CHRM1; CHRM3; ERBB4; | 3 | 1.29 | HIF1A; HK2; XDH |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | | | | CHRM3; ERBB4; GUCA1B; SCT | | | | | | | | | SLC29A1 | | | |
| inclusion body: GO | 66 | 3 | 0.76 | NEFM; ORC6; SNCB | 4 | 0.72 | CLU; HSPB7; MAPT; SNCA | 0 | 0.00 | | 0 | 0.00 | | 3 | 1.15 | CLU; MAPT; SNCA | 3 | 1.29 | NEFM; ORC6; SNCB |
| somatic stem cell population maintenance: GO | 66 | 1 | 0.25 | WNT7A | 3 | 0.54 | FOXD3; NANOG; NOG | 0 | 0.00 | | 0 | 0.00 | | 2 | 0.77 | FGF2; LDB2 | 3 | 1.29 | ASCL2; WNT7A; WNT9B |
| phospholipase activity: GO | 91 | 10 | 1.84 | BDKRB2; CCR5; FAM83B; HMOX1; LIPG; LYPLA1; PDIA3; PLA2G3; PLA2G4D; PLBD1 | 14 | 1.82 | ADORA1; CCKBR; CHRM1; CHRM3; GPLD1; LIPH; LPL; PLA2G16; PLA2G5; PLA2G6; PLCB4; PLCH2; PNPLA3; PNPLA7 | 2 | 9.18 | LPL; PLA2G16 | 0 | 0.00 | | 7 | 1.95 | CHRM1; CHRM3; GPLD1; LIPH; PLCB4; PLCZ1; PNPLA3 | 4 | 1.25 | BDKRB2; PLA2G3; PLA2G4D; PLCD4 |
| canonical wnt signaling pathway: GO | 91 | 5 | 0.92 | CDH3; CSNK1A1; SDC1; WNT5A; WNT7A | 6 | 0.78 | EGF; FZD4; FZD8; NKX2-5; TCF7L1; WNT11 | 0 | 0.00 | | 0 | 0.00 | | 4 | 1.12 | EGF; FZD7; TCF7L1; WNT11 | 4 | 1.25 | SNAI2; WNT5A; WNT7A; WNT9B |
| negative regulation of mapk cascade: GO | 142 | 11 | 1.30 | DUSP14; DUSP6; DUSP9; F2RL1; FOXM1; GSTP1; HMGCR; HSPH1; IL1B; PBK; SERPINB3 | 12 | 1.00 | ADIPOQ; AMBP; APOE; C1QL4; DACT1; LIF; MAPK8IP1; P2RX7; PER1; RPS6KA6; TIMP3; WNK2 | 1 | 2.94 | ADIPOQ | 2 | 5.89 | GBP1; IL1B | 4 | 0.72 | DACT1; FBLN1; RPS6KA6; SPRY1 | 6 | 1.20 | DUSP6; FOXM1; GSTP1; HSPH1; PBK; SPRY4 |
| intermediate filament based process: GO | 42 | 12 | 4.78 | CSNK1A1; DSP; INA; KRT14; | 3 | 0.84 | DES; PRPH; SYNM | 0 | 0.00 | | 0 | 0.00 | | 1 | 0.60 | KRT20 | 2 | 1.35 | INA; NEFM |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | KRT16; KRT17; KRT3; KRT6A; KRT6C; KRT9; NEFL; NEFM | | | | | | | | | | | | | | | |
| acute phase response: GO | 42 | 8 | 3.19 | HIF1A; IL1A; IL1B; IL1RN; IL22; IL6; SERPINA1; UGT1A1 | 0 | 0.00 | | 0 | 0.00 | | 1 | 9.95 | IL1B | 0 | 0.00 | | 2 | 1.35 | HIF1A; IL22 |
| regulation of muscle cell apoptotic process: GO | 42 | 7 | 2.79 | ADCYAP1; HMGCR; HMOX1; IFNG; IL12B; NRG1; ZC3H12A | 7 | 1.97 | CAMK2A; HAND2; LIFR; LTK; MYOCD; NKX2-5; NOL3 | 0 | 0.00 | | 0 | 0.00 | | 1 | 0.60 | HAND2 | 2 | 1.35 | NRG1; ZC3H12A |
| response to electrical stimulus: GO | 42 | 5 | 1.99 | GJB6; HIF1A; IL6; NTRK1; TH | 7 | 1.97 | DCX; KCNJ3; MSTN; NEUROD2; P2RX7; PALM; PPARGC1A | 0 | 0.00 | | 0 | 0.00 | | 2 | 1.21 | PALM; PPARGC1A | 2 | 1.35 | HIF1A; TH |
| scf(skp2)-mediated degradation of p27/p21 | 42 | 5 | 1.99 | CCNA2; CCNE1; CDKN1A; PSMA5; PSMB6 | 0 | 0.00 | | 0 | 0.00 | | 0 | 0.00 | | 0 | 0.00 | | 2 | 1.35 | CCNA2; CDKN1A |
| negative regulation of actin filament polymerization: GO | 42 | 3 | 1.20 | CAPZA1; PFN1; TWF1 | 8 | 2.25 | CAPZA3; FHOD3; GSN; LMOD1; SCIN; SLIT2; SPTBN4; TMOD1 | 0 | 0.00 | | 0 | 0.00 | | 5 | 3.02 | CAPZA3; LMOD1; SCIN; SLIT2; SPTBN4 | 2 | 1.35 | PFN1; TWF1 |
| nicotinate and nicotinamide metabolism | 42 | 3 | 1.20 | NAMPT; PNP; VNN3 | 2 | 0.56 | ENPP1; FN3K | 0 | 0.00 | | 0 | 0.00 | | 4 | 2.42 | AOX1; ENPP3; FN3K; NMNAT3 | 2 | 1.35 | NAMPT; PNP |
| oxidoreductase activity | 42 | 3 | 1.20 | PRDX1; PTGS2; | 4 | 1.12 | CYGB; HBA1; HBA2; | 0 | 0.00 | | 0 | 0.00 | | 2 | 1.21 | HBA2; HBB | 2 | 1.35 | PTGS2; TXNDC17 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| acting on peroxide as acceptor: GO | | | | TXNDC17 | | | HBB | | | | | | | | | | | | |
| chromosome organization involved in meiotic cell cycle: GO | 42 | 2 | 0.80 | SMC4; TRIP13 | 2 | 0.56 | STAG3; SYCP1 | 0 | 0.00 | | 0 | 0.00 | | 0 | 0.00 | | 2 | 1.35 | SMC4; TRIP13 |
| sumoylation of dna damage response and repair proteins | 42 | 2 | 0.80 | BLM; CBX2 | 0 | 0.00 | | 0 | 0.00 | | 0 | 0.00 | | 0 | 0.00 | | 2 | 1.35 | BLM; CBX2 |
| signalling to erks | 168 | 16 | 1.59 | ACTB; CDK1; CSF2; DUSP6; DUSP9; EREG; HBEGF; IL2RA; JAK3; NGF; NRAS; NRG1; NTRK1; PSMA5; PSMB6; RALB | 13 | 0.91 | BTC; CNKSR2; EGF; FGF1; FGFR1; FGFR3; GFRA1; GRIN2A; IL5; IRS2; NRG2; SHC2; SHC3 | 0 | 0.00 | | 1 | 2.49 | IL2RA | 5 | 0.76 | ANGPT1; CNKSR2; EGF; FGFR1; SHC2 | 7 | 1.18 | ACTB; CDK1; DUSP6; EREG; HBEGF; NGF; NRG1 |
| ncam signaling for neurite out-growth | 168 | 14 | 1.39 | ACTB; CSF2; DUSP6; DUSP9; EREG; HBEGF; IL2RA; JAK3; NRAS; NRG1; PRNP; PSMA5; PSMB6; ST8SIA2 | 14 | 0.98 | BTC; CACNA1H; CNKSR2; COL9A2; EGF; FGF1; FGFR1; FGFR3; GFRA1; GRIN2A; IL5; IRS2; NRG2; SHC2 | 0 | 0.00 | | 1 | 2.49 | IL2RA | 7 | 1.06 | ANGPT1; CACNA1H; CNKSR2; EGF; FGFR1; GULP1; SHC2 | 7 | 1.18 | ACTB; AGRN; DUSP6; EREG; HBEGF; NRG1; ST8SIA2 |
| inositol lipid mediated signaling: GO | 117 | 8 | 1.14 | C1QBP; CD80; EREG; HBEGF; NGF; NRG1; NTRK1; PTAFR | 14 | 1.41 | BTC; EGF; ERBB4; FGF1; FGF17; FGF22; FGF9; FGFR1; FGFR3; GSN; | 0 | 0.00 | | 0 | 0.00 | | 6 | 1.30 | EGF; ERBB4; FGF2; FGF22; FGFR1; PREX2 | 5 | 1.21 | EREG; HBEGF; NGF; NRG1; PTAFR |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | | | | IRS2; LTK; MUC5AC; NRG2 | | | | | | | | | | | | |
| multicellular organismal response to stress: GO | 67 | 8 | 2.00 | ACP5; ADCYAP1; CCK; DPP4; DDO1; NTRK1; OSM; VDAC1 | 9 | 1.58 | ADRB1; BCL2; DRD1; DRD4; GRM7; HMGCS2; NEUROD2; RELN; SLC6A2 | 0 | 0.00 | | 1 | 6.24 | OSM | 5 | 1.90 | ADCYAP1R1; BCL2; HMGCS2; MDK; RELN | 3 | 1.27 | ACP5; DPP4; VDAC1 |
| regulation of amine transport: GO | 67 | 8 | 2.00 | CCK; CHRNA3; CHRNA6; GDNF; HRH3; IL1B; NTSR1; P2RY1 | 18 | 3.17 | ADORA1; ADRA2A; AGT; ATP1A2; CARTPT; CNR1; DRD1; DRD4; GRM7; KCNA2; KCNB1; LEP; NPY5R; P2RX7; PCP4; RAB3B; SNCA; SNCG | 0 | 0.00 | | 1 | 6.24 | IL1B | 4 | 1.52 | ADRA2A; CXCL12; RAB3B; SNCA | 3 | 1.27 | CHRNA6; NTSR1; P2RY1 |
| positive regulation of endothelial cell proliferation: GO | 67 | 5 | 1.25 | HIF1A; PGF; SCG2; TGFBR1; WNT5A | 0 | 0.00 | | 0 | 0.00 | | 0 | 0.00 | | 2 | 0.76 | CXCL12; FGF2 | 3 | 1.27 | HIF1A; LRG1; WNT5A |
| protein self association: GO | 43 | 6 | 2.33 | CTSB; CTSC; PCSK9; RSAD2; S100A7A; SLC2A1 | 2 | 0.55 | PTH1R; SVIP | 0 | 0.00 | | 0 | 0.00 | | 2 | 1.18 | PTH1R; SVIP | 2 | 1.32 | PCSK9; SLC2A1 |
| regulation of tyrosine phosphorylation of stat3 protein: GO | 43 | 6 | 2.33 | IL12B; IL20; IL24; IL6; OSM; SOCS3 | 4 | 1.10 | FGFR3; GHR; LEP; LIF | 1 | 9.72 | GHR | 1 | 9.72 | OSM | 0 | 0.00 | | 2 | 1.32 | IL20; SOCS3 |
| ceramide biosynthetic | 43 | 4 | 1.56 | CERS3; ST6GALNAC1; | 4 | 1.10 | GAL3ST1; P2RX1; | 0 | 0.00 | | 0 | 0.00 | | 1 | 0.59 | ST6GALNAC5 | 2 | 1.32 | ST6GALNAC1; ST8SIA2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| process: GO | | | | ST8SIA2; UGCG | | | P2RX7; ST6GALNAC5 | | | | | | | | | | | | |
| sperm egg recognition: GO | 43 | 4 | 1.56 | CCT2; CCT3; CCT5; CCT7 | 3 | 0.82 | CATSPERG; HSPA1L; KCNU1 | 0 | 0.00 | | 0 | 0.00 | | 1 | 0.59 | CATSPERG | 2 | 1.32 | CCT2; CCT5 |
| histone h4 acetylation: GO | 43 | 3 | 1.17 | BRCA2; RUVBL1; TRIM16 | 4 | 1.10 | APBB1; CHD5; KAT2A; PER1 | 0 | 0.00 | | 0 | 0.00 | | 0 | 0.00 | | 2 | 1.32 | BEND3; BRCA2 |
| modification by symbiont of host morphology or physiology: GO | 43 | 3 | 1.17 | KPNA2; SERPINB9; ZC3H12A | 2 | 0.55 | ALB; NTRK3 | 0 | 0.00 | | 1 | 9.72 | SERPINB9 | 0 | 0.00 | | 2 | 1.32 | KPNA2; ZC3H12A |
| regulation of interferon beta production: GO | 43 | 3 | 1.17 | NMI; POLR3G; PYCARD | 0 | 0.00 | | 0 | 0.00 | | 0 | 0.00 | | 1 | 0.59 | ZBTB20 | 2 | 1.32 | NMI; POLR3G |
| hydro lyase activity: GO | 43 | 2 | 0.78 | CA2; ENO1 | 4 | 1.10 | CA1; CA11; CA3; CA6 | 0 | 0.00 | | 0 | 0.00 | | 4 | 2.36 | CA1; CA11; CA3; CA6 | 2 | 1.32 | CA2; ENO1 |
| dna alkylation: GO | 43 | 0 | 0.00 | | 2 | 0.55 | PIWIL2; TDRD5 | 0 | 0.00 | | 0 | 0.00 | | 0 | 0.00 | | 2 | 1.32 | BEND3; TDRD9 |
| class a1 rhodopsin like receptors | 196 | 26 | 2.22 | BDKRB1; BDKRB2; CCL17; CCL22; CCL3; CCL7; CCR4; CCR5; CXCL5; CXCL9; CXCR1; FPR3; GPR65; HCAR2; HCAR3; HRH3; HTR7; INSL3; LPAR3; NPSR1; NTSR1; P2RY1; P2RY2; PTAFR; QRFPR; | 22 | 1.32 | ADORA1; ADRA1B; ADRA2A; CCKBR; CHRM1; CHRM2; CHRM3; CNR1; CXCR5; DRD1; EDN3; GALR1; HTR4; HTR6; LHB; LHCGR; NMUR1; NPY5R; OXER1; PROK1; TAC3; TSHR | 0 | 0.00 | | 5 | 10.66 | CXCL5; CXCL9; FFAR2; HCAR2; HCAR3 | 8 | 1.04 | ADRA2A; CHRM1; CHRM3; EDN3; P2RY4; PTGDR; PTGFR; TSHR | 8 | 1.16 | BDKRB2; CXCR1; HRH2; NTSR1; P2RY1; P2RY2; PTAFR; QRFPR |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | S1PR4 | | | | | | | | | | | | | | | |
| regulation of nucleotide metabolic process: GO | 196 | 17 | 1.45 | ADCYAP1; CAP1; CDA; CXCL10; CXCL11; CXCL9; GADD45GIP1; GNAI3; GPR65; GPR87; HIF1A; INSL3; PGAM1; PPIF; PTHLH; VCP; WNT5A | 28 | 1.69 | ADCY2; ADCY5; ADCY6; ADCY8; ADRA2A; ADRB1; AKAP12; APOE; CALCR; DRD1; DRD4; GALR1; GPD1; GRM7; GUCA1B; LHCGR; MLXIPL; NOS2; OSTN; OXER1; P2RX7; PALM; PPARGC1A; PRKAA2; SCT; SNCA; TSHR; VIPR2 | 2 | 4.26 | GPD1; MRAP2 | 1 | 2.13 | CXCL9 | 9 | 1.17 | ADCYAP1R1; ADRA2A; AKAP12; LPAR1; PALM; PPARGC1A; PRKAA2; SNCA; TSHR | 8 | 1.16 | CAP1; CDA; CXCL11; HIF1A; PGAM1; PPIF; PTHLH; WNT5A |
| positive regulation of cytokine secretion: GO | 93 | 18 | 3.24 | CAMP; CCL3; CD2; CD274; CLEC6A; F2RL1; IFNG; IL1A; IL1B; IL1RL1; IL26; IL4R; NLRP2; PANX1; PYCARD; SLAMF1; TRIM16; WNT5A | 4 | 0.51 | CD34; LPL; P2RX7; PAEP | 1 | 4.49 | LPL | 2 | 8.99 | FFAR2; IL1B | 1 | 0.27 | CD34 | 4 | 1.22 | IL10; NLRP2; PANX1; WNT5A |
| fc gamma r mediated phagocytosis | 93 | 7 | 1.26 | ARPC1A; ARPC3; ARPC5L; CFL1; FCGR1A; | 4 | 0.51 | DNM1; GSN; PLA2G6; SCIN | 0 | 0.00 | | 1 | 4.49 | RAC2 | 1 | 0.27 | SCIN | 4 | 1.22 | ARPC1A; CFL1; PLA2G4D; VAV2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | PLA2G4D; RAC2 | | | | | | | | | | | | | | | |
| hematopoietic progenitor cell differentiation: GO | 93 | 7 | 1.26 | AGPAT5; ANLN; ESCO2; HERC6; KRT75; STON2; TOP2A | 4 | 0.51 | BCL2; COL24A1; DACT2; GATA1 | 0 | 0.00 | | 0 | 0.00 | | 3 | 0.82 | BCL2; COL24A1; WDR78 | 4 | 1.22 | ANLN; HERC6; STON2; TOP2A |
| neural tube formation: GO | 93 | 6 | 1.08 | GRHL3; HIF1A; KIF20B; PFN1; STIL; WNT5A | 6 | 0.76 | ALX1; COBL; FOLR1; KAT2A; NOG; PTCH1 | 0 | 0.00 | | 0 | 0.00 | | 5 | 1.37 | DLC1; GDF7; PRICKLE1; PTCH1; SHROOM3 | 4 | 1.22 | HIF1A; PFN1; STIL; WNT5A |
| interferon gamma mediated signaling pathway: GO | 68 | 10 | 2.46 | FCGR1A; IFI30; IFNG; MT2A; OAS1; OAS2; OAS3; OASL; PTAFR; STAT1 | 3 | 0.52 | CAMK2A; CAMK2B; NCAM1 | 0 | 0.00 | | 1 | 6.15 | GBP1 | 2 | 0.75 | HLA-DQB2; NCAM1 | 3 | 1.25 | HLA-G; OAS1; PTAFR |
| positive regulation of axonogenesis: GO | 68 | 6 | 1.48 | CRABP2; LPAR3; NEFL; NGF; NRG1; TNFRSF12A | 4 | 0.69 | CDH4; MAPT; NTRK3; SLIT2 | 0 | 0.00 | | 0 | 0.00 | | 4 | 1.49 | CXCL12; MAPT; SHOX2; SLIT2 | 3 | 1.25 | CRABP2; NGF; NRG1 |
| viral myocarditis | 68 | 6 | 1.48 | ACTB; CD80; CXADR; CYCS; EIF4G2; RAC2 | 8 | 1.39 | DMD; LAMA2; MYH11; MYH14; MYH3; MYH7B; SGCA; SGCG | 1 | 6.15 | SGCG | 1 | 6.15 | RAC2 | 1 | 0.37 | LAMA2 | 3 | 1.25 | ACTB; CYCS; HLA-G |
| nucleoside phosphate catabolic process: GO | 68 | 4 | 0.98 | NUDT15; PNP; UPP1; VCP | 6 | 1.04 | ASPDH; ENPP1; NEIL1; PDE11A; PDE9A; UPP2 | 0 | 0.00 | | 0 | 0.00 | | 2 | 0.75 | ENPP3; PDE9A | 3 | 1.25 | NUDT15; PNP; XDH |
| positive regulation of type i interferon | 68 | 4 | 0.98 | IFI16; MYD88; POLR3G; | 0 | 0.00 | | 0 | 0.00 | | 0 | 0.00 | | 1 | 0.37 | ZBTB20 | 3 | 1.25 | IFI16; MYD88; POLR3G |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| production: GO | | | | ZBP1 | | | | | | | | | | | | | | | |
| plasma membrane receptor complex: GO | 171 | 15 | 1.47 | CD3E; CD79A; CHRNA3; CHRNA6; CHRNA9; HTR3A; IL13RA1; IL6; ITGA3; ITGA6; ITGAX; ITGB6; KCNK1; NETO2; TGFBR1 | 22 | 1.52 | ACVR1C; CHRNA2; CNTFR; DLG2; GRIA1; GRIA2; GRIA4; GRIK4; GRIK5; GRIN1; GRIN2A; HTR3E; ITGA7; ITGA8; NETO1; NLGN1; SHANK1; SHISA6; SHISA8; SORBS1; TF; VWC2L | 2 | 4.89 | ACVR1C; GRIA4 | 0 | 0.00 | | 7 | 1.04 | CNIH3; CNTFR; DLG2; GRIA1; GRIA2; ITGA11; VWC2 | 7 | 1.16 | BMPR1B; CHRNA6; ITGA3; ITGA6; ITGB4; ITGB6; KCNK1 |
| regulation of cell projection assembly: GO | 145 | 8 | 0.92 | CCL21; F2RL1; FAM110C; FSCN1; PFN1; PRKCQ; RAC2; TGFBR1 | 11 | 0.90 | ADAMTS16; COBL; ESPN; FRMD7; NLGN1; NRXN1; P2RX7; PALM; PPP1R9A; SLIT2; USP17L2 | 0 | 0.00 | | 1 | 2.88 | RAC2 | 4 | 0.70 | DPYSL3; NRXN1; PALM; SLIT2 | 6 | 1.17 | AGRN; CDC42EP1; EPHA2; FAM110C; PFN1; PRKCQ |
| myeloid leukocyte activation: GO | 94 | 10 | 1.78 | ANXA3; CCL3; CSF2; F2RL1; NR4A3; PLA2G3; PYCARD; S100A12; SLAMF1; TNFSF9 | 2 | 0.25 | CLU; SNCA | 0 | 0.00 | | 2 | 8.89 | ANXA3; LCP2 | 2 | 0.54 | CLU; SNCA | 4 | 1.21 | DHRS2; NDRG1; PLA2G3; SBNO2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| polyol metabolic process: GO | 94 | 7 | 1.25 | COQ2; CYP27B1; GK; NTSR1; PTAFR; SGPP2; TPI1 | 8 | 1.00 | LEP; MOGAT1; MOGAT2; NUDT10; NUDT11; PCK1; PLCB4; PLCH2 | 0 | 0.00 | | 0 | 0.00 | | 6 | 1.62 | ACER1; CYP3A4; DGAT2; FGF2; PLCB4; PLCZ1 | 4 | 1.21 | CYP27B1; NTSR1; PTAFR; TPI1 |
| regulation of endothelial cell proliferation: GO | 94 | 7 | 1.25 | GJA1; HIF1A; PGF; SCG2; STAT1; TGFBR1; WNT5A | 4 | 0.50 | APOE; ATOH8; LEP; TNMD | 0 | 0.00 | | 0 | 0.00 | | 5 | 1.35 | ANGPT1; ATOH8; CXCL12; FGF2; TNMD | 4 | 1.21 | HIF1A; LRG1; WNT5A; XDH |
| regulation of interleukin 10 production: GO | 44 | 8 | 3.04 | CD274; IDO1; IL12B; JAK3; PYCARD; SASH3; TNFRSF21; TNFRSF9 | 1 | 0.27 | CD34 | 0 | 0.00 | | 0 | 0.00 | | 1 | 0.58 | CD34 | 2 | 1.29 | BCL3; CD83 |
| positive regulation of receptor activity: GO | 44 | 5 | 1.90 | EPGN; EREG; GREM1; GSTO1; TGFA | 9 | 2.41 | ACTN2; ADORA1; ADRA2A; CFTR; EGF; GSTM2; JPH2; RELN; TRDN | 0 | 0.00 | | 0 | 0.00 | | 4 | 2.31 | ADRA2A; EGF; RELN; TRDN | 2 | 1.29 | EREG; TGFA |
| tumor necrosis factor receptor superfamily binding: GO | 44 | 5 | 1.90 | MYD88; NGF; STAT1; TNFSF10; TNFSF9 | 3 | 0.80 | CD70; EDA; NOL3 | 0 | 0.00 | | 0 | 0.00 | | 1 | 0.58 | CD70 | 2 | 1.29 | MYD88; NGF |
| immunoglobulin production: GO | 44 | 4 | 1.52 | EXO1; IGKV4-1; IL7R; POLQ | 0 | 0.00 | | 0 | 0.00 | | 1 | 9.50 | IL7R | 0 | 0.00 | | 2 | 1.29 | EXO1; POLQ |
| rhoa pathway | 44 | 2 | 0.76 | CFL1; MSN | 1 | 0.27 | ACTA1 | 0 | 0.00 | | 0 | 0.00 | | 0 | 0.00 | | 2 | 1.29 | CFL1; MSN |
| irs-mediated signalling | 172 | 13 | 1.26 | ACTB; CSF2; DUSP6; DUSP9; EIF4EBP1; EREG; HBEGF; | 14 | 0.96 | BTC; CNKSR2; EEF2K; EGF; FGF1; FGFR1; FGFR3; GFRA1; | 0 | 0.00 | | 1 | 2.43 | IL2RA | 6 | 0.89 | ANGPT1; CNKSR2; EGF; FGFR1; PRKAA2; SHC2 | 7 | 1.15 | ACTB; DUSP6; EIF4EBP1; EREG; HBEGF; NRG1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline: Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo: Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo: Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | IL2RA; JAK3; NRAS; NRG1; PSMA5; PSMB6 | | | GRIN2A; IL5; IRS2; NRG2; PRKAA2; SHC2 | | | | | | | | | | | | TRIB3 |
| protein tyrosine kinase activity: GO | 172 | 9 | 0.88 | CSF2; EREG; HBEGF; JAK3; MELK; NRG1; NTRK1; TTK; TWF1 | 19 | 1.30 | BTC; EGF; EPHA6; EPHB1; EPHB6; ERBB4; FGF1; FGF17; FGF22; FGF9; FGFR1; FGFR3; IL5; LTK; MERTK; NRG2; NTRK3; PKDCC; ROS1 | 0 | 0.00 | | 0 | 0.00 | | 8 | 1.18 | DDR2; EFNB3; EGF; ERBB4; FGF2; FGF22; FGFR1; PDGFRL | 7 | 1.15 | DYRK3; EPHA2; EREG; HBEGF; NRG1; TTK; TWF1 |
| negative regulation of cellular amide metabolic process: GO | 120 | 8 | 1.12 | CALR; EIF2S1; EIF4A3; EIF4EBP1; EPRS; GAPDH; RAN; ZC3H12A | 6 | 0.59 | APOE; CELF4; CLU; CPEB1; SAMD4A; ZNF540 | 0 | 0.00 | | 0 | 0.00 | | 4 | 0.85 | CLU; CPEB1; IGFBP5; ZNF540 | 5 | 1.18 | EIF4A3; EIF4EBP1; GAPDH; RAN; ZC3H12A |
| pancreatic cancer | 69 | 8 | 1.94 | BRCA2; E2F3; PGF; RAC2; RALB; STAT1; TGFA; TGFBR1 | 1 | 0.17 | EGF | 0 | 0.00 | | 1 | 6.06 | RAC2 | 1 | 0.37 | EGF | 3 | 1.23 | BRCA2; E2F1; TGFA |
| rac1 pathway | 69 | 5 | 1.21 | ACTR3; ARPC3; CDK5R1; CFL1; RACGAP1 | 1 | 0.17 | NOX1 | 0 | 0.00 | | 0 | 0.00 | | 0 | 0.00 | | 3 | 1.23 | CDK5R1; CFL1; IQGAP3 |
| adenylate cyclase activating g protein coupled receptor | 69 | 4 | 0.97 | ADCYAP1; ADM2; PTHLH; | 18 | 3.08 | ADCY2; ADCY5; ADCY6; | 0 | 0.00 | | 0 | 0.00 | | 4 | 1.47 | ADRA1A; ADRA2A; PTH1R; | 3 | 1.23 | ADM2; PTHLH; UCN2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| signaling pathway: GO | | | | S1PR4 | | | ADCY8; ADRA1A; ADRA1B; ADRA2A; ADRB1; CALCR; DRD1; GALR1; GCGR; LHCGR; OR56A1; OR56A4; OR56A5; PTH1R; TSHR | | | | | | | | | TSHR | | | |
| phosphatidyl-inositol 3 kinase activity: GO | 69 | 4 | 0.97 | CD80; EREG; HBEGF; NRG1 | 11 | 1.88 | BTC; EGF; ERBB4; FGF1; FGF17; FGF22; FGF9; FGFR1; FGFR3; IRS2; NRG2 | 0 | 0.00 | | 0 | 0.00 | | 6 | 2.21 | EGF; ERBB4; FGF2; FGF22; FGFR1; PIK3R6 | 3 | 1.23 | EREG; HBEGF; NRG1 |
| intermediate filament organization: GO | 20 | 6 | 5.02 | DSP; KRT14; KRT17; KRT9; NEFL; NEFM | 1 | 0.59 | DES | 0 | 0.00 | | 0 | 0.00 | | 1 | 1.27 | KRT20 | 1 | 1.42 | NEFM |
| regulation of lymphocyte chemotaxis: GO | 20 | 6 | 5.02 | CCL3; CCL7; CXCL10; CXCL13; S100A7; WNT5A | 0 | 0.00 | | 0 | 0.00 | | 0 | 0.00 | | 0 | 0.00 | | 1 | 1.42 | WNT5A |
| neutrophil mediated immunity: GO | 20 | 5 | 4.18 | ANXA3; CXCL5; CXCL6; IL6; TREM1 | 1 | 0.59 | ELANE | 0 | 0.00 | | 3 | 62.68 | ANXA3; CXCL5; TREM1 | 2 | 2.54 | CTSG; ELANE | 1 | 1.42 | CXCL6 |
| regulation of monocyte chemotaxis: GO | 20 | 5 | 4.18 | CXCL10; GREM1; S100A14; S100A7; SERPINE1 | 1 | 0.59 | SLIT2 | 0 | 0.00 | | 1 | 20.89 | SERPINE1 | 2 | 2.54 | CXCL12; SLIT2 | 1 | 1.42 | S100A14 |
| response to | 20 | 5 | 4.18 | IFIT3; | 0 | 0.00 | | 0 | 0.00 | | 2 | 41.79 | IFITM3; | 0 | 0.00 | | 1 | 1.42 | OAS1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| interferon alpha: GO | | | | IFITM1; IFITM3; LAMP3; OAS1 | | | | | | | | | LAMP3 | | | | | | |
| th1/th2 differentiation | 20 | 5 | 4.18 | IFNG; IL12B; IL12RB2; IL2RA; IL4R | 0 | 0.00 | | 0 | 0.00 | | 1 | 20.89 | IL2RA | 0 | 0.00 | | 1 | 1.42 | IL12RB2 |
| actiny pathway | 20 | 4 | 3.35 | ACTR3; ARPC1A; ARPC3; NTRK1 | 1 | 0.59 | ACTA1 | 0 | 0.00 | | 0 | 0.00 | | 0 | 0.00 | | 1 | 1.42 | ARPC1A |
| amine catabolic process: GO | 20 | 4 | 3.35 | IDO1; KYNU; SMOX; TDO2 | 3 | 1.77 | DHPS; DMGDH; HAAO | 0 | 0.00 | | 1 | 20.89 | TDO2 | 1 | 1.27 | DMGDH | 1 | 1.42 | SMOX |
| copper ion transport: GO | 20 | 4 | 3.35 | HEPHL1; SCO2; STEAP1B; STEAP4 | 1 | 0.59 | CP | 0 | 0.00 | | 1 | 20.89 | STEAP1B | 2 | 2.54 | CP; STEAP2 | 1 | 1.42 | SCO2 |
| pyrimidine nucleoside catabolic process: GO | 20 | 4 | 3.35 | APOBEC3A; CDA; TYMP; UPP1 | 1 | 0.59 | UPP2 | 0 | 0.00 | | 0 | 0.00 | | 0 | 0.00 | | 1 | 1.42 | CDA |
| ectoderm development: GO | 20 | 3 | 2.51 | GRHL3; ITGA6; KRT6B | 1 | 0.59 | EDA | 0 | 0.00 | | 0 | 0.00 | | 0 | 0.00 | | 1 | 1.42 | ITGA6 |
| negative regulation of cytokine production involved in immune response: GO | 20 | 3 | 2.51 | HMOX1; JAK3; SLAMF1 | 0 | 0.00 | | 0 | 0.00 | | 0 | 0.00 | | 1 | 1.27 | ANGPT1 | 1 | 1.42 | IL10 |
| negative regulation of regulated secretory pathway: GO | 20 | 3 | 2.51 | FOXF1; HMOX1; IL13RA2 | 1 | 0.59 | ADRA2A | 0 | 0.00 | | 0 | 0.00 | | 1 | 1.27 | ADRA2A | 1 | 1.42 | IL13RA2 |
| peptidyl cysteine modification: GO | 20 | 3 | 2.51 | GAPDH; S100A8; S100A9 | 2 | 1.18 | NOS2; RAB3B | 0 | 0.00 | | 0 | 0.00 | | 1 | 1.27 | RAB3B | 1 | 1.42 | GAPDH |
| reflex: GO | 20 | 3 | 2.51 | ALDH1A3; GJA1; NR4A3 | 4 | 2.36 | ADRA1A; GLRB; | 0 | 0.00 | | 0 | 0.00 | | 3 | 3.81 | ADRA1A; GLRB; | 1 | 1.42 | TMC1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | | | | SHANK1; TMC2 | | | | | | | | | SLITRK6 | | | |
| regulation of retinoic acid receptor signaling pathway: GO | 20 | 3 | 2.51 | CALR; CRABP2; TRIM16 | 1 | 0.59 | ZNF536 | 0 | 0.00 | | 0 | 0.00 | | 0 | 0.00 | | 1 | 1.42 | CRABP2 |
| biosynthesis of unsaturated fatty acids | 20 | 2 | 1.67 | ACOT7; YOD1 | 5 | 2.95 | ACOT1; ELOVL2; FADS2; PECR; SCD5 | 0 | 0.00 | | 0 | 0.00 | | 0 | 0.00 | | 1 | 1.42 | ACOT7 |
| epithelial structure maintenance: GO | 20 | 2 | 1.67 | CXADR; VSIG1 | 4 | 2.36 | CROCC; MUC4; MUC6; RBP4 | 0 | 0.00 | | 0 | 0.00 | | 1 | 1.27 | LDB2 | 1 | 1.42 | VSIG1 |
| fatty acid derivative transport: GO | 20 | 2 | 1.67 | ANXA1; BDKRB2 | 4 | 2.36 | DRD4; LEP; NOS2; PLA2G5 | 0 | 0.00 | | 0 | 0.00 | | 0 | 0.00 | | 1 | 1.42 | BDKRB2 |
| g protein beta gamma subunit complex binding: GO | 20 | 2 | 1.67 | GNA15; GNAI3 | 2 | 1.18 | ADORA1; GNAZ | 0 | 0.00 | | 0 | 0.00 | | 0 | 0.00 | | 1 | 1.42 | GNA15 |
| igf1mtor pathway | 20 | 2 | 1.67 | EIF2S1; EIF4EBP1 | 0 | 0.00 | | 0 | 0.00 | | 0 | 0.00 | | 0 | 0.00 | | 1 | 1.42 | EIF4EBP1 |
| inactivation of gsk3 by akt causes accumulation of b-catenin in alveolar macrophages | 20 | 2 | 1.67 | GJA1; MYD88 | 0 | 0.00 | | 0 | 0.00 | | 0 | 0.00 | | 0 | 0.00 | | 1 | 1.42 | MYD88 |
| lipopolysaccharide binding: GO | 20 | 2 | 1.67 | PTAFR; RNASE7 | 1 | 0.59 | P2RX7 | 0 | 0.00 | | 0 | 0.00 | | 0 | 0.00 | | 1 | 1.42 | PTAFR |
| mitochondrial genome maintenance: GO | 20 | 2 | 1.67 | PIF1; TYMP | 0 | 0.00 | | 0 | 0.00 | | 0 | 0.00 | | 0 | 0.00 | | 1 | 1.42 | PIF1 |
| natural killer cell activation involved in immune response: GO | 20 | 2 | 1.67 | IFNE; IL12B | 2 | 1.18 | IFNA5; KLRF2 | 0 | 0.00 | | 0 | 0.00 | | 1 | 1.27 | KLRF2 | 1 | 1.42 | IFNE |
| translational | 20 | 2 | 1.67 | EIF2S1; | 0 | 0.00 | | 0 | 0.00 | | 0 | 0.00 | | 0 | 0.00 | | 1 | 1.42 | EIF4EBP1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| initiation: GO | | | | EIF4EBP1 | | | | | | | | | | | | | | | |
| oxidative stress induced gene expression via nrf2 | 20 | 2 | 1.67 | HMOX1; HMOX2 | 1 | 0.59 | FXYD2 | 0 | 0.00 | | 0 | 0.00 | | 0 | 0.00 | | 1 | 1.42 | HMOX2 |
| plasma lipoprotein particle clearance: GO | 20 | 2 | 1.67 | HMOX1; LDLR | 3 | 1.77 | ADIPOQ; APOC1; APOE | 1 | 20.89 | ADIPOQ | 0 | 0.00 | | 1 | 1.27 | DGAT2 | 1 | 1.42 | LDLR |
| positive regulation of protein autophos phorylation: GO | 20 | 2 | 1.67 | GREM1; RAP2B | 1 | 0.59 | PDGFD | 0 | 0.00 | | 0 | 0.00 | | 0 | 0.00 | | 1 | 1.42 | RAP2B |
| regulation of membrane protein ectodomain proteolysis: GO | 20 | 2 | 1.67 | IFNG; IL1B | 5 | 2.95 | ADRA2A; APOE; GPLD1; TIMP3; TIMP4 | 0 | 0.00 | | 1 | 20.89 | IL1B | 2 | 2.54 | ADRA2A; GPLD1 | 1 | 1.42 | IL10 |
| response to leptin: GO | 20 | 2 | 1.67 | CCNA2; NR4A3 | 3 | 1.77 | INHBB; LEP; LEPR | 0 | 0.00 | | 0 | 0.00 | | 0 | 0.00 | | 1 | 1.42 | CCNA2 |
| triglyceride catabolic process: GO | 20 | 2 | 1.67 | FABP5; FABP6 | 5 | 2.95 | APOE; FABP4; FABP7; LPL; PNPLA3 | 1 | 20.89 | LPL | 0 | 0.00 | | 1 | 1.27 | PNPLA3 | 1 | 1.42 | FABP5 |
| ankyrin binding: GO | 20 | 1 | 0.84 | RHCG | 4 | 2.36 | OBSCN; RHAG; SLC4A1; SPTBN4 | 0 | 0.00 | | 0 | 0.00 | | 2 | 2.54 | RHBG; SPTBN4 | 1 | 1.42 | RHCG |
| apoptotic process involved in development: GO | 20 | 1 | 0.84 | BAK1 | 5 | 2.95 | CRYAB; HAND2; NKX2-5; SLIT2; SLIT3 | 1 | 20.89 | CRYAB | 0 | 0.00 | | 3 | 3.81 | HAND2; SLIT2; SLIT3 | 1 | 1.42 | BAK1 |
| axonal fasciculation: GO | 20 | 1 | 0.84 | CDK5R1 | 4 | 2.36 | CNR1; CNTN4; FEZF2; SEMA3A | 0 | 0.00 | | 0 | 0.00 | | 0 | 0.00 | | 1 | 1.42 | CDK5R1 |
| coa hydrolase activity: GO | 20 | 1 | 0.84 | ACOT7 | 2 | 1.18 | ACOT1; ACOT12 | 0 | 0.00 | | 0 | 0.00 | | 0 | 0.00 | | 1 | 1.42 | ACOT7 |
| constitutive signaling by akt1 e17k in cancer | 20 | 1 | 0.84 | CDKN1A | 0 | 0.00 | | 0 | 0.00 | | 0 | 0.00 | | 0 | 0.00 | | 1 | 1.42 | CDKN1A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| exon exon junction complex: GO | 20 | 1 | 0.84 | EIF4A3 | 0 | 0.00 | | 0 | 0.00 | | 0 | 0.00 | | 0 | 0.00 | | 1 | 1.42 | EIF4A3 |
| incretin synthesis secretion and inactivation | 20 | 1 | 0.84 | DPP4 | 2 | 1.18 | LEP; PAX6 | 0 | 0.00 | | 0 | 0.00 | | 0 | 0.00 | | 1 | 1.42 | DPP4 |
| lagging strand synthesis | 20 | 1 | 0.84 | PCNA | 0 | 0.00 | | 0 | 0.00 | | 0 | 0.00 | | 0 | 0.00 | | 1 | 1.42 | FEN1 |
| lipoprotein particle receptor binding: GO | 20 | 1 | 0.84 | PCSK9 | 4 | 2.36 | APOE; DKK1; RELN; SYT1 | 0 | 0.00 | | 0 | 0.00 | | 1 | 1.27 | RELN | 1 | 1.42 | PCSK9 |
| nerve growth factor pathway (ngf) | 20 | 1 | 0.84 | NGF | 0 | 0.00 | | 0 | 0.00 | | 0 | 0.00 | | 0 | 0.00 | | 1 | 1.42 | NGF |
| nuclear localization sequence binding: GO | 20 | 1 | 0.84 | KPNA2 | 0 | 0.00 | | 0 | 0.00 | | 0 | 0.00 | | 0 | 0.00 | | 1 | 1.42 | KPNA2 |
| pigment granule organization: GO | 20 | 1 | 0.84 | RAB38 | 2 | 1.18 | BCL2; TRAPPC6A | 0 | 0.00 | | 0 | 0.00 | | 3 | 3.81 | ASIP; BCL2; TRAPPC6A | 1 | 1.42 | RAB38 |
| purine ribonucleoside bisphosphate metabolic process: GO | 20 | 1 | 0.84 | SULT2B1 | 3 | 1.77 | ENPP1; SLC26A1; SULT1A2 | 0 | 0.00 | | 0 | 0.00 | | 1 | 1.27 | SULT1E1 | 1 | 1.42 | SULT2B1 |
| regulation of protein targeting to membrane: GO | 20 | 1 | 0.84 | CDK5R1 | 2 | 1.18 | KCNB1; USP17L2 | 0 | 0.00 | | 0 | 0.00 | | 0 | 0.00 | | 1 | 1.42 | CDK5R1 |
| regulation of receptor biosynthetic process: GO | 20 | 1 | 0.84 | HIF1A | 1 | 0.59 | ADIPOQ | 1 | 20.89 | ADIPOQ | 0 | 0.00 | | 0 | 0.00 | | 1 | 1.42 | HIF1A |
| regulation of ruffle assembly: GO | 20 | 1 | 0.84 | PFN1 | 3 | 1.77 | COBL; NLGN1; USP17L2 | 0 | 0.00 | | 0 | 0.00 | | 0 | 0.00 | | 1 | 1.42 | PFN1 |
| regulation of transcription from rna polymerase iii promoter: GO | 20 | 1 | 0.84 | POLR3G | 1 | 0.59 | AR | 0 | 0.00 | | 0 | 0.00 | | 0 | 0.00 | | 1 | 1.42 | POLR3G |
| rna polymerase iii transcription | 20 | 1 | 0.84 | POLR3G | 0 | 0.00 | | 0 | 0.00 | | 0 | 0.00 | | 0 | 0.00 | | 1 | 1.42 | POLR3G |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| initiation from type 3 promoter | | | | | | | | | | | | | | | | | | | |
| rna polymerase iii transcription termination | 20 | 1 | 0.84 | POLR3G | 0 | 0.00 | | 0 | 0.00 | | 0 | 0.00 | | 0 | 0.00 | | 1 | 1.42 | POLR3G |
| tff pathway | 20 | 1 | 0.84 | CYCS | 1 | 0.59 | GHR | 1 | 20.89 | GHR | 0 | 0.00 | | 0 | 0.00 | | 1 | 1.42 | CYCS |
| translation repressor activity: GO | 20 | 1 | 0.84 | EIF4EBP1 | 4 | 2.36 | CELF4; CPEB1; SAMD4A; ZNF540 | 0 | 0.00 | | 0 | 0.00 | | 2 | 2.54 | CPEB1; ZNF540 | 1 | 1.42 | EIF4EBP1 |
| acute myocardial infarction | 20 | 0 | 0.00 | | 2 | 1.18 | F10; F7 | 0 | 0.00 | | 0 | 0.00 | | 0 | 0.00 | | 1 | 1.42 | PLAT |
| ami pathway | 20 | 0 | 0.00 | | 2 | 1.18 | F10; F7 | 0 | 0.00 | | 0 | 0.00 | | 0 | 0.00 | | 1 | 1.42 | PLAT |
| fceri mediated $ca^{+2}$ mobilization | 20 | 0 | 0.00 | | 0 | 0.00 | | 0 | 0.00 | | 1 | 20.89 | LCP2 | 1 | 1.27 | MS4A2 | 1 | 1.42 | VAV2 |
| metanephric epithelium development: GO | 20 | 0 | 0.00 | | 4 | 2.36 | OSR1; PKD1; POU3F3; SOX8 | 0 | 0.00 | | 0 | 0.00 | | 2 | 2.54 | OSR1; POU3F3 | 1 | 1.42 | WNT9B |
| regulation of macrophage differentiation: GO | 20 | 0 | 0.00 | | 3 | 1.77 | ADIPOQ; IL34; LIF | 1 | 20.89 | ADIPOQ | 0 | 0.00 | | 0 | 0.00 | | 1 | 1.42 | TRIB1 |
| negative regulation of homotypic cell cell adhesion: GO | 95 | 11 | 1.94 | ANXA1; CD274; CTLA4; IDO1; IL2RA; IL4R; JAK3; PRNP; SERPINE2; TNFRSF21; UBASH3B | 2 | 0.25 | DTX1; SCGB1A1 | 0 | 0.00 | | 1 | 4.40 | IL2RA | 1 | 0.27 | PRKG1 | 4 | 1.19 | HLA-G; IL10; SERPINE2; UBASH3B |
| arms-mediated activation | 147 | 14 | 1.59 | ACTB; CSF2; DUSP6; DUSP9; EREG; HBEGF; IL2RA; JAK3; NGF; NRAS; NRG1; NTRK1; PSMA5; | 12 | 0.96 | BTC; CNKSR2; EGF; FGF1; FGFR1; FGFR3; GFRA1; GRIN2A; IL5; IRS2; NRG2; SHC2 | 0 | 0.00 | | 1 | 2.84 | IL2RA | 5 | 0.86 | ANGPT1; CNKSR2; EGF; FGFR1; SHC2 | 6 | 1.16 | ACTB; DUSP6; EREG; HBEGF; NGF; NRG1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | PSMB6 | | | | | | | | | | | | | | | |
| leishmania infection | 70 | 9 | 2.15 | FCGR1A; FCGR3B; IFNG; IL12B; IL1A; IL1B; MYD88; PTGS2; STAT1 | 2 | 0.34 | C3; NOS2 | 0 | 0.00 | | 1 | 5.97 | IL1B | 1 | 0.36 | C3 | 3 | 1.22 | IL10; MYD88; PTGS2 |
| regulation of acute inflammatory response: GO | 70 | 8 | 1.91 | ADCYAP1; C1QBP; F12; GSTP1; IL1B; IL6; OSM; PTGS2 | 9 | 1.52 | ADORA1; C3; C4BPA; C6; C7; CFH; CNR1; KLKB1; NPY5R | 0 | 0.00 | | 3 | 17.91 | FFAR2; IL1B; OSM | 2 | 0.73 | C3; CFH | 3 | 1.22 | F12; GSTP1; PTGS2 |
| cellular glucose homeostasis: GO | 70 | 7 | 1.67 | GJB6; HIF1A; HK2; IL1B; NME1; PLAU; TH | 6 | 1.01 | CARTPT; GRIK5; IRS2; KCNB1; MLXIPL; PPARGC1A | 0 | 0.00 | | 1 | 5.97 | IL1B | 3 | 1.09 | PDK3; PPARGC1A; SLC29A1 | 3 | 1.22 | HIF1A; HK2; TH |
| endoderm development: GO | 70 | 6 | 1.43 | EOMES; HMGA2; LAMB3; MMP9; SOX7; TBX20 | 5 | 0.84 | COL11A1; DKK1; ITGA7; NANOG; NOG | 0 | 0.00 | | 0 | 0.00 | | 1 | 0.36 | COL11A1 | 3 | 1.22 | HMGA2; LAMB3; SOX7 |
| ppar signaling pathway | 70 | 5 | 1.20 | FABP5; FABP6; GK; MMP1; OLR1 | 16 | 2.70 | ACADL; ACOX2; ADIPOQ; AQP7; CYP4A11; FABP4; FABP7; FADS2; HMGCS2; LPL; PCK1; PLIN1; RXRG; SCD5; SLC27A6; SORBS1 | 3 | 17.91 | ADIPOQ; LPL; SLC27A6 | 0 | 0.00 | | 3 | 1.09 | ACOX2; CYP4A11; HMGCS2 | 3 | 1.22 | ANGPTL4; FABP5; PPARD |
| positive regulation of transporter activity: GO | 70 | 4 | 0.96 | ATP1B3; GSTO1; NTSR1; | 14 | 2.36 | ACTN2; ANK2; CACNA2D1; | 0 | 0.00 | | 0 | 0.00 | | 6 | 2.18 | ATP1B2; CACNA2D1; GLRX; RELN; | 3 | 1.22 | NTSR1; PTAFR; SGK1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | PTAFR | | | CFTR; DMD; DRD4; FGF14; GSTM2; JPH2; PON1; RELN; SGK2; TRDN; WNK2 | | | | | | | | | TESC; TRDN | | | |
| regulation of dendrite morphogenesis: GO | 70 | 4 | 0.96 | CDK5R1; CFL1; CHRNA3; LRP8 | 10 | 1.69 | CAMK2B; EEF2K; GRIN1; ILIRAPL1; NLGN1; PAK3; PPP1R9A; RELN; SDC2; SRCIN1 | 1 | 5.97 | SRCIN1 | 0 | 0.00 | | 2 | 0.73 | PAK3; RELN | 3 | 1.22 | CDK5R1; CFL1; SGK1 |
| regulation of plasma membrane organization: GO | 70 | 4 | 0.96 | IFNG; ITGA3; LYPLA1; S100A9 | 7 | 1.18 | ANXA13; AR; DPP10; NOX1; NRXN1; PKDCC; SORBS1 | 0 | 0.00 | | 1 | 5.97 | GBP1 | 2 | 0.73 | LRRC15; NRXN1 | 3 | 1.22 | ARHGEF16; EPHA2; ITGA3 |
| semaphorin interactions | 70 | 3 | 0.72 | CDK5R1; CFL1; RAC2 | 6 | 1.01 | MYH11; MYH14; MYL9; PLXNA3; SEMA3A; SEMA3E | 0 | 0.00 | | 1 | 5.97 | RAC2 | 3 | 1.09 | DPYSL3; SEMA3E; SLC29A1 | 3 | 1.22 | CDK5R1; CFL1; RND1 |
| oxidoreductase activity acting on a sulfur group of donors: GO | 45 | 7 | 2.60 | GSTO1; IFI30; PDIA3; SH3BGRL3; TXN; TXNDC17; TXNDC8 | 0 | 0.00 | | 0 | 0.00 | | 0 | 0.00 | | 2 | 1.13 | GLRX; MSRB3 | 2 | 1.26 | TXN; TXNDC17 |
| positive regulation of interleukin 8 production: GO | 45 | 7 | 2.60 | CAMP; CD2; F2RL1; IL1B; PYCARD; SERPINE1; WNT5A | 2 | 0.52 | ADIPOQ; ELANE | 1 | 9.29 | ADIPOQ | 3 | 27.86 | FFAR2; IL1B; SERPINE1 | 1 | 0.56 | ELANE | 2 | 1.26 | AFAP1L2; WNT5A |
| antigen processing and | 45 | 6 | 2.23 | CTSB; HSPA4; | 2 | 0.52 | HSPA1L; IFNA5 | 0 | 0.00 | | 0 | 0.00 | | 0 | 0.00 | | 2 | 1.26 | HSPA5; HSPA8 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| presentation | | | | HSPA5; HSPA6; HSPA8; KIR2DL4 | | | | | | | | | | | | | | | |
| pyrimidine nucleoside metabolic process: GO | 45 | 6 | 2.23 | APOBEC3A; CDA; NME1; TK1; TYMP; UPP1 | 1 | 0.26 | UPP2 | 0 | 0.00 | | 0 | 0.00 | | 0 | 0.00 | | 2 | 1.26 | CDA; TK1 |
| positive regulation of organelle assembly: GO | 45 | 5 | 1.86 | CSF2; FSCN1; MSN; RALB; SDC1 | 1 | 0.26 | IL5 | 0 | 0.00 | | 0 | 0.00 | | 0 | 0.00 | | 2 | 1.26 | MSN; PLK4 |
| stat cascade: GO | 45 | 5 | 1.86 | JAK3; NMI; OSM; SOCS3; STAT1 | 6 | 1.57 | EGF; FGFR3; GHR; LEP; LIF; PKD1 | 1 | 9.29 | GHR | 1 | 9.29 | OSM | 1 | 0.56 | EGF | 2 | 1.26 | NMI; SOCS3 |
| phospholipid transporter activity: GO | 45 | 3 | 1.12 | PITPNM1; PLSCR3; PRELID1 | 2 | 0.52 | ANO3; ANO9 | 0 | 0.00 | | 0 | 0.00 | | 1 | 0.56 | ANO9 | 2 | 1.26 | PITPNM1; PRELID1 |
| positive regulation of actin filament bundle assembly: GO | 45 | 3 | 1.12 | GPR65; PFN1; PRKCQ | 4 | 1.05 | AMOT; MYOC; TPM1; WNT11 | 0 | 0.00 | | 0 | 0.00 | | 4 | 2.26 | CTGF; LPAR1; MYOC; WNT11 | 2 | 1.26 | PFN1; PRKCQ |
| pyridoxal phosphate binding: GO | 45 | 3 | 1.12 | GOT2; KYNU; PYGL | 5 | 1.31 | ACCSL; ALAS2; ALB; GPT; PYGM | 0 | 0.00 | | 0 | 0.00 | | 2 | 1.13 | GPT; HDC | 2 | 1.26 | GADL1; GOT2 |
| response to cocaine: GO | 45 | 3 | 1.12 | CCNA2; HOMER1; HTR3A | 5 | 1.31 | CNR1; DRD1; DRD4; HDAC5; SNCA | 0 | 0.00 | | 0 | 0.00 | | 2 | 1.13 | SLC18A2; SNCA | 2 | 1.26 | CCNA2; HOMER1 |
| clathrin derived vesicle budding | 45 | 2 | 0.74 | AP1S3; HSPA8 | 0 | 0.00 | | 0 | 0.00 | | 0 | 0.00 | | 0 | 0.00 | | 2 | 1.26 | AP1S3; HSPA8 |
| regulation of cholesterol biosynthesis by srebp (srebf) | 45 | 2 | 0.74 | HMGCR; SQLE | 2 | 0.52 | ACACB; GPAM | 1 | 9.29 | GPAM | 0 | 0.00 | | 0 | 0.00 | | 2 | 1.26 | FEN1; SQLE |
| trans-golgi network vesicle budding | 45 | 2 | 0.74 | AP1S3; HSPA8 | 0 | 0.00 | | 0 | 0.00 | | 0 | 0.00 | | 0 | 0.00 | | 2 | 1.26 | AP1S3; HSPA8 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| rhoa reg pathway | 45 | 1 | 0.37 | ECT2 | 4 | 1.05 | ARHGAP6; ARHGEF25; MCF2L; OBSCN | 0 | 0.00 | | 0 | 0.00 | | 2 | 1.13 | ARHGEF25; DLC1 | 2 | 1.26 | ECT2; VAV2 |
| igf1r signaling cascade | 174 | 13 | 1.25 | ACTB; CSF2; DUSP6; DUSP9; EIF4EBP1; EREG; HBEGF; IL2RA; JAK3; NRAS; NRG1; PSMA5; PSMB6 | 14 | 0.95 | BTC; CNKSR2; EEF2K; EGF; FGF1; FGFR1; FGFR3; GFRA1; GRIN2A; IL5; IRS2; NRG2; PRKAA2; SHC2 | 0 | 0.00 | | 1 | 2.40 | IL2RA | 6 | 0.88 | ANGPT1; CNKSR2; EGF; FGFR1; PRKAA2; SHC2 | 7 | 1.14 | ACTB; DUSP6; EIF4EBP1; EREG; HBEGF; NRG1; TRIB3 |
| irs-related events triggered by igf1r | 174 | 13 | 1.25 | ACTB; CSF2; DUSP6; DUSP9; EIF4EBP1; EREG; HBEGF; IL2RA; JAK3; NRAS; NRG1; PSMA5; PSMB6 | 14 | 0.95 | BTC; CNKSR2; EEF2K; EGF; FGF1; FGFR1; FGFR3; GFRA1; GRIN2A; IL5; IRS2; NRG2; PRKAA2; SHC2 | 0 | 0.00 | | 1 | 2.40 | IL2RA | 6 | 0.88 | ANGPT1; CNKSR2; EGF; FGFR1; PRKAA2; SHC2 | 7 | 1.14 | ACTB; DUSP6; EIF4EBP1; EREG; HBEGF; NRG1; TRIB3 |
| signaling by type 1 insulin-like growth factor 1 receptor (igf1r) | 174 | 13 | 1.25 | ACTB; CSF2; DUSP6; DUSP9; EIF4EBP1; EREG; HBEGF; IL2RA; JAK3; NRAS; NRG1; PSMA5; PSMB6 | 14 | 0.95 | BTC; CNKSR2; EEF2K; EGF; FGF1; FGFR1; FGFR3; GFRA1; GRIN2A; IL5; IRS2; NRG2; PRKAA2; SHC2 | 0 | 0.00 | | 1 | 2.40 | IL2RA | 6 | 0.88 | ANGPT1; CNKSR2; EGF; FGFR1; PRKAA2; SHC2 | 7 | 1.14 | ACTB; DUSP6; EIF4EBP1; EREG; HBEGF; NRG1; TRIB3 |
| frs2-mediated activation | 148 | 14 | 1.58 | ACTB; CSF2; DUSP6; DUSP9; EREG; HBEGF; IL2RA; JAK3; NGF; NRAS; | 12 | 0.96 | BTC; CNKSR2; EGF; FGF1; FGFR1; FGFR3; GFRA1; GRIN2A; IL5; | 0 | 0.00 | | 1 | 2.82 | IL2RA | 5 | 0.86 | ANGPT1; CNKSR2; EGF; FGFR1; SHC2 | 6 | 1.15 | ACTB; DUSP6; EREG; HBEGF; NGF; NRG1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline: Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo: Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo: Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | NRG1; NTRK1; PSMA5; PSMB6 | | | IRS2; NRG2; SHC2 | | | | | | | | | | | | |
| regulation of chromatin organization: GO | 148 | 7 | 0.79 | CCNB1; CDC45; CHEK1; HIST1H1B; IL1B; UBE2N; UHRF1 | 11 | 0.88 | CAMK1; HDAC5; KAT2A; LIF; MYOCD; NAPIL2; PIWIL2; PPARGC1A; SNCA; TET1; USP17L2 | 0 | 0.00 | | 1 | 2.82 | IL1B | 5 | 0.86 | CAMK1; NAPIL2; PPARGC1A; SNCA; TET1 | 6 | 1.15 | CCNB1; CDC45; CHEK1; HIST1H1B; RPS6KA4; SNAI2 |
| dc pathway | 21 | 5 | 3.98 | CD2; CSF2; IFNG; IL12B; ITGAX | 1 | 0.56 | IL5 | 0 | 0.00 | | 0 | 0.00 | | 0 | 0.00 | | 1 | 1.35 | IL10 |
| il12 pathway | 21 | 5 | 3.98 | CCR5; CD3E; IFNG; IL12B; IL12RB2 | 0 | 0.00 | | 0 | 0.00 | | 0 | 0.00 | | 0 | 0.00 | | 1 | 1.35 | IL12RB2 |
| adenylyltransferase activity: GO | 21 | 4 | 3.19 | OAS1; OAS2; OAS3; OASL | 0 | 0.00 | | 0 | 0.00 | | 0 | 0.00 | | 1 | 1.21 | NMNAT3 | 1 | 1.35 | OAS1 |
| dendritic cell migration: GO | 21 | 4 | 3.19 | CCL21; CCR5; CXCR1; CXCR4 | 0 | 0.00 | | 0 | 0.00 | | 0 | 0.00 | | 0 | 0.00 | | 1 | 1.35 | CXCR1 |
| mast cell granule: GO | 21 | 4 | 3.19 | ANXA1; NR4A3; PLA2G3; SRGN | 0 | 0.00 | | 0 | 0.00 | | 0 | 0.00 | | 0 | 0.00 | | 1 | 1.35 | PLA2G3 |
| metabolism of porphyrins | 21 | 4 | 3.19 | HMOX1; HMOX2; UGT1A1; UGT1A7 | 2 | 1.12 | ALAS2; PPOX | 0 | 0.00 | | 0 | 0.00 | | 1 | 1.21 | PPOX | 1 | 1.35 | HMOX2 |
| s1p meta pathway | 21 | 3 | 2.39 | GNA15; GNAI3; SIPR4 | 1 | 0.56 | GNAZ | 0 | 0.00 | | 0 | 0.00 | | 0 | 0.00 | | 1 | 1.35 | GNA15 |
| vitamin transporter activity: GO | 21 | 3 | 2.39 | PDPN; SLC2A1; STRA6 | 4 | 2.25 | FOLR1; FOLR2; RBP4; SLC19A3 | 0 | 0.00 | | 0 | 0.00 | | 1 | 1.21 | SLC19A3 | 1 | 1.35 | SLC2A1 |
| bone resorption: | 21 | 2 | 1.59 | ACP5; RAC2 | 1 | 0.56 | PTHR | 0 | 0.00 | | 1 | 19.90 | RAC2 | 1 | 1.21 | PTH1R | 1 | 1.35 | ACP5 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| GO | | | | | | | | | | | | | | | | | | | |
| cellular protein complex localization: GO | 21 | 2 | 1.59 | EXOC3L2; RAN | 1 | 0.56 | STXBP6 | 0 | 0.00 | | 0 | 0.00 | | 1 | 1.21 | STXBP6 | 1 | 1.35 | RAN |
| cobalamin metabolic process: GO | 21 | 2 | 1.59 | PRSS3; TCN1 | 0 | 0.00 | | 0 | 0.00 | | 0 | 0.00 | | 0 | 0.00 | | 1 | 1.35 | PRSS3 |
| cochlea morphogenesis: GO | 21 | 2 | 1.59 | GRHL3; WNT5A | 3 | 1.69 | FRZB; GLI2; SIX1 | 0 | 0.00 | | 0 | 0.00 | | 1 | 1.21 | GLI2 | 1 | 1.35 | WNT5A |
| deoxyribose phosphate catabolic process: GO | 21 | 2 | 1.59 | NUDT15; PGM2 | 1 | 0.56 | NEIL1 | 0 | 0.00 | | 0 | 0.00 | | 0 | 0.00 | | 1 | 1.35 | NUDT15 |
| inward rectifier potassium channel activity: GO | 21 | 2 | 1.59 | KCNJ15; KCNK1 | 3 | 1.69 | ABCC8; KCNJ1; KCNJ3 | 0 | 0.00 | | 0 | 0.00 | | 0 | 0.00 | | 1 | 1.35 | KCNK1 |
| lipid digestion: GO | 21 | 2 | 1.59 | LDLR; LIPG | 3 | 1.69 | LIPH; NPC1L1; SOAT2 | 0 | 0.00 | | 0 | 0.00 | | 3 | 3.63 | LIPH; LIPK; LIPM | 1 | 1.35 | LDLR |
| necroptotic process: GO | 21 | 2 | 1.59 | PPIF; PYGL | 0 | 0.00 | | 0 | 0.00 | | 0 | 0.00 | | 0 | 0.00 | | 1 | 1.35 | PPIF |
| negative regulation of neural precursor cell proliferation: GO | 21 | 2 | 1.59 | IL1B; WNT5A | 1 | 0.56 | PAX6 | 0 | 0.00 | | 1 | 19.90 | IL1B | 0 | 0.00 | | 1 | 1.35 | WNT5A |
| netrin1 signaling | 21 | 2 | 1.59 | PRKCQ; TRPC4 | 2 | 1.12 | SLIT3; UNC5D | 0 | 0.00 | | 0 | 0.00 | | 1 | 1.21 | SLIT3 | 1 | 1.35 | PRKCQ |
| nf-kb signaling pathway | 21 | 2 | 1.59 | IL1A; MYD88 | 0 | 0.00 | | 0 | 0.00 | | 0 | 0.00 | | 0 | 0.00 | | 1 | 1.35 | MYD88 |
| ns1 mediated effects on host pathways | 21 | 2 | 1.59 | ISG15; KPNA2 | 0 | 0.00 | | 0 | 0.00 | | 1 | 19.90 | ISG15 | 0 | 0.00 | | 1 | 1.35 | KPNA2 |
| perk regulates gene expression | 21 | 2 | 1.59 | CXCL8; HSPA5 | 0 | 0.00 | | 0 | 0.00 | | 0 | 0.00 | | 0 | 0.00 | | 1 | 1.35 | HSPA5 |
| regulation of cellular extravasation: | 21 | 2 | 1.59 | CCL21; PTAFR | 1 | 0.56 | PDGFD | 0 | 0.00 | | 0 | 0.00 | | 1 | 1.21 | CXCL12 | 1 | 1.35 | PTAFR |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| GO | | | | | | | | | | | | | | | | | | | |
| regulation of chromatin silencing: GO | 21 | 2 | 1.59 | CDC45; UHRF1 | 1 | 0.56 | TET1 | 0 | 0.00 | | 0 | 0.00 | | 1 | 1.21 | TET1 | 1 | 1.35 | CDC45 |
| regulation of dopamine secretion: GO | 21 | 2 | 1.59 | CHRNA6; GDNF | 5 | 2.81 | CNR1; KCNA2; PCP4; SNCA; SNCG | 0 | 0.00 | | 0 | 0.00 | | 2 | 2.42 | CXCL12; SNCA | 1 | 1.35 | CHRNA6 |
| regulation of striated muscle cell apoptotic process: GO | 21 | 2 | 1.59 | HMGCR; NRG1 | 6 | 3.37 | CAMK2A; HAND2; LTK; MYOCD; NKX2-5; NOL3 | 0 | 0.00 | | 0 | 0.00 | | 1 | 1.21 | HAND2 | 1 | 1.35 | NRG1 |
| s1p s1p1 pathway | 21 | 2 | 1.59 | GNAI3; PTGS2 | 1 | 0.56 | GNAZ | 0 | 0.00 | | 0 | 0.00 | | 0 | 0.00 | | 1 | 1.35 | PTGS2 |
| aquaporin-mediated transport | 21 | 1 | 0.80 | AQP3 | 3 | 1.69 | ADCY8; AQP7; PRKAR2B | 1 | 19.90 | PRKAR2B | 1 | 19.90 | AQP9 | 1 | 1.21 | GNG11 | 1 | 1.35 | AQP3 |
| cell differentiation in hindbrain: GO | 21 | 1 | 0.80 | WNT7A | 4 | 2.25 | ATP2B2; CBLN1; NOG; NRXN1 | 0 | 0.00 | | 0 | 0.00 | | 1 | 1.21 | NRXN1 | 1 | 1.35 | WNT7A |
| cellular response to virus: GO | 21 | 1 | 0.80 | ZC3H12A | 1 | 0.56 | GLI2 | 0 | 0.00 | | 0 | 0.00 | | 1 | 1.21 | GLI2 | 1 | 1.35 | ZC3H12A |
| chondrocyte development: GO | 21 | 1 | 0.80 | SULF2 | 1 | 0.56 | COL11A1 | 0 | 0.00 | | 0 | 0.00 | | 2 | 2.42 | COL11A1; SHOX2 | 1 | 1.35 | BMPR1B |
| deadenylation dependent mrna decay | 21 | 1 | 0.80 | EIF4A3 | 0 | 0.00 | | 0 | 0.00 | | 0 | 0.00 | | 0 | 0.00 | | 1 | 1.35 | EIF4A3 |
| diseases associated with glycosaminoglycan metabolism | 21 | 1 | 0.80 | SDC1 | 4 | 2.25 | GPC3; GPC6; PRELP; SDC2 | 0 | 0.00 | | 0 | 0.00 | | 1 | 1.21 | DCN | 1 | 1.35 | AGRN |
| intrinsic component of mitochondrial outer membrane: GO | 21 | 1 | 0.80 | BAK1 | 0 | 0.00 | | 0 | 0.00 | | 0 | 0.00 | | 1 | 1.21 | ARMCX3 | 1 | 1.35 | BAK1 |
| male genitalia development: GO | 21 | 1 | 0.80 | GJB2 | 2 | 1.12 | BMP5; LHCGR | 0 | 0.00 | | 0 | 0.00 | | 0 | 0.00 | | 1 | 1.35 | WNT9B |
| microfilament motor activity: GO | 21 | 1 | 0.80 | MYO1B | 3 | 1.69 | MYH14; MYH3; MYO3A | 0 | 0.00 | | 0 | 0.00 | | 0 | 0.00 | | 1 | 1.35 | MYO1B |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| nls bearing protein import into nucleus: GO | 21 | 1 | 0.80 | KPNA2 | 0 | 0.00 | | 0 | 0.00 | | 0 | 0.00 | | 0 | 0.00 | | 1 | 1.35 | KPNA2 |
| positive regulation of excitatory postsynaptic potential: GO | 21 | 1 | 0.80 | WNT7A | 8 | 4.49 | DRD4; GRIN1; NETO1; NLGN1; NRXN1; RELN; RIMS1; SHANK1 | 0 | 0.00 | | 0 | 0.00 | | 3 | 3.63 | NRXN1; RELN; RIMS1 | 1 | 1.35 | WNT7A |
| positive regulation of nitric oxide synthase activity: GO | 21 | 1 | 0.80 | HIF1A | 3 | 1.69 | APOE; FCER2; TERT | 0 | 0.00 | | 0 | 0.00 | | 1 | 1.21 | ESR1 | 1 | 1.35 | HIF1A |
| rac 1 cell motility signaling pathway | 21 | 1 | 0.80 | CDK5R1 | 0 | 0.00 | | 0 | 0.00 | | 0 | 0.00 | | 0 | 0.00 | | 1 | 1.35 | CDK5R1 |
| regulation of glial cell proliferation: GO | 21 | 1 | 0.80 | ADCYAP1 | 0 | 0.00 | | 0 | 0.00 | | 0 | 0.00 | | 0 | 0.00 | | 1 | 1.35 | ASCL2 |
| regulation of intrinsic apoptotic signaling pathway by p53 class mediator: GO | 21 | 1 | 0.80 | BDKRB2 | 0 | 0.00 | | 0 | 0.00 | | 0 | 0.00 | | 0 | 0.00 | | 1 | 1.35 | BDKRB2 |
| regulation of respiratory gaseous exchange: GO | 21 | 1 | 0.80 | NTSR1 | 4 | 2.25 | ADORA1; ATP1A2; GRIN1; NLGN1 | 0 | 0.00 | | 0 | 0.00 | | 0 | 0.00 | | 1 | 1.35 | NTSR1 |
| regulatory | 21 | 1 | 0.80 | RAN | 0 | 0.00 | | 0 | 0.00 | | 0 | 0.00 | | 0 | 0.00 | | 1 | 1.35 | RAN |
| rna pathways rho cell motility signaling pathway | 21 | 1 | 0.80 | PFN1 | 2 | 1.12 | ARHGAP6; GSN | 0 | 0.00 | | 0 | 0.00 | | 0 | 0.00 | | 1 | 1.35 | PFN1 |
| runx1 interacts with co-factors whose precise effect on runx1 targets is | 21 | 1 | 0.80 | CBX2 | 0 | 0.00 | | 0 | 0.00 | | 0 | 0.00 | | 0 | 0.00 | | 1 | 1.35 | CBX2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| not known | | | | | | | | | | | | | | | | | | | |
| signaling by scf kit | 21 | 1 | 0.80 | CDK1 | 0 | 0.00 | | 0 | 0.00 | | 0 | 0.00 | | 0 | 0.00 | | 1 | 1.35 | CDK1 |
| somatic recombination of immunoglobulin gene segments: GO | 21 | 1 | 0.80 | EXO1 | 0 | 0.00 | | 0 | 0.00 | | 0 | 0.00 | | 0 | 0.00 | | 1 | 1.35 | EXO1 |
| synaptic transmission glutamatergic: GO | 21 | 1 | 0.80 | UNC13A | 5 | 2.81 | GRIK5; GRIN1; P2RX1; SHC3; SLC17A7 | 0 | 0.00 | | 0 | 0.00 | | 1 | 1.21 | CNIH3 | 1 | 1.35 | UNC13A |
| erk1 and erk2 cascade: GO | 21 | 0 | 0.00 | | 2 | 1.12 | AGT; EGF | 0 | 0.00 | | 0 | 0.00 | | 1 | 1.21 | EGF | 1 | 1.35 | IQGAP3 |
| peripheral nervous system axon ensheathment: GO | 21 | 0 | 0.00 | | 5 | 2.81 | ADAM22; FA2H; LAMA2; LGI4; MYOC | 0 | 0.00 | | 0 | 0.00 | | 4 | 4.84 | ADAM22; LAMA2; LGI4; MYOC | 1 | 1.35 | NDRG1 |
| positive regulation of i kappab kinase nf kappab signaling: GO | 175 | 18 | 1.72 | CCL21; CLEC6A; ECT2; F2RL1; GJA1; GREM1; HMOX1; IL12B; IL1A; IL1B; LTF; MYD88; PLK2; PRKCQ; PTGS2; S100A12; TNFSF10; UBE2N | 4 | 0.27 | ADIPOQ; EDA; PELI2; PLEKHG5 | 1 | 2.39 | ADIPOQ | 1 | 2.39 | IL1B | 3 | 0.44 | GPRC5B; LPAR1; PELI2 | 7 | 1.13 | ECT2; LTF; MYD88; PLK2; PRKCQ; PTGS2; SLC20A1 |
| coenzyme binding: GO | 175 | 9 | 0.86 | ACOT7; AHCY; ALDH1A3; GAPDH; HMGCR; LDHA; OGDHL; SQLE; TH | 17 | 1.15 | ACADL; ACBD4; ACOX2; ALAS2; ASPDH; CRY2; D2HGDH; FMO2; FMO5; | 2 | 4.78 | GPD1; HSD11B2 | 0 | 0.00 | | 8 | 1.16 | ACBD4; ACOX2; ALDH5A1; AOX1; CRY2; FMO5; PPOX; PRODH | 7 | 1.13 | ACOT7; GAPDH; LDHA; OGDHL; SQLE; TH; XDH |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | GPD1; LDHD; MAOA; NOS2; NOX1; PPOX; PRODH; SOAT2 | | | | | | | | | | | | |
| extracellular matrix disassembly: GO | 71 | 8 | 1.89 | ADAMTS4; KLK7; LAMB3; MMP1; MMP10; MMP12; MMP3; MMP9 | 5 | 0.83 | BCAN; ELANE; ELN; GSN; KLKB1 | 0 | 0.00 | | 0 | 0.00 | | 4 | 1.43 | CTSG; DCN; ELANE; ELN | 3 | 1.20 | ADAMTS4; LAMB3; MMP3 |
| multicellular organismal macromolecule metabolic process: GO | 71 | 8 | 1.89 | CTSB; HIF1A; KLK6; MMP1; MMP10; MMP12; MMP3; MMP9 | 6 | 1.00 | COL11A1; COL11A2; COL19A1; COL25A1; P2RX7; TNXB | 0 | 0.00 | | 0 | 0.00 | | 2 | 0.72 | COL11A1; MMP27 | 3 | 1.20 | ADAMTS14; HIF1A; MMP3 |
| regulation of release of sequestered calcium ion into cytosol: GO | 71 | 8 | 1.89 | BDKRB1; CXCL10; CXCL11; CXCL9; GSTO1; NPSR1; NTSR1; UBASH3B | 9 | 1.50 | ANK2; ATP1A2; CASQ2; DMD; DRD1; GSTM2; JPH2; SNCA; TRDN | 0 | 0.00 | | 1 | 5.89 | CXCL9 | 4 | 1.43 | HRC; SNCA; TRDN; TRPC1 | 3 | 1.20 | CXCL11; NTSR1; UBASH3B |
| embryonic heart tube development: GO | 71 | 6 | 1.41 | GJA1; HIF1A; NDRG4; STIL; TBX20; WNT5A | 7 | 1.16 | CCDC40; DNAAF1; FOLR1; FOXN4; HAND2; MESP1; NKX2-5 | 0 | 0.00 | | 0 | 0.00 | | 3 | 1.07 | FOXC1; HAND2; MESP1 | 3 | 1.20 | HIF1A; STIL; WNT5A |
| shc1 events in egfr signaling | 149 | 13 | 1.46 | ACTB; CDK1; CSF2; DUSP6; DUSP9; EREG; HBEGF; | 12 | 0.95 | BTC; CNKSR2; EGF; FGF1; FGFR1; FGFR3; | 0 | 0.00 | | 1 | 2.80 | IL2RA | 5 | 0.85 | ANGPT1; CNKSR2; EGF; FGFR1; SHC2 | 6 | 1.14 | ACTB; CDK1; DUSP6; EREG; HBEGF; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | IL2RA; JAK3; NRAS; NRG1; PSMA5; PSMB6 | | | GFRA1; GRIN2A; IL5; IRS2; NRG2; SHC2 | | | | | | | | | | | | NRG1 |
| neurotransmitter transport: GO | 149 | 9 | 1.01 | GABRQ; HRH3; HSPA8; RIMS3; SLC38A1; SLC6A11; TH; UNC13A; WNT7A | 22 | 1.74 | APBA1; ATP1A2; CADPS; GABRA2; ICA1; NLGN1; NRXN1; NRXN3; P2RX7; PCLO; RIMS1; RPH3AL; SLC17A7; SLC6A17; SLC6A2; SNCA; SV2B; SYN2; SYT1; SYT17; SYT8; SYT9 | 0 | 0.00 | | 0 | 0.00 | | 10 | 1.71 | APBA1; ICA1; NRXN1; PCLO; RIMS1; SLC18A2; SNCA; SV2B; SYN2; SYT17 | 6 | 1.14 | HSPA8; SLC18A3; SLC6A11; TH; UNC13A; WNT7A |
| positive regulation of nucleotide metabolic process: GO | 123 | 12 | 1.63 | ADCYAP1; CAP1; CXCL10; CXCL11; CXCL9; GADD45GIP1; GPR65; HIF1A; INSL3; PTHLH; VCP; WNT5A | 21 | 2.01 | ADCY2; ADCY5; ADCY6; ADCY8; ADRB1; AKAP12; APOE; CALCR; DRD1; GPD1; GUCA1B; LHCGR; MLXIPL; NOS2; OSTN; P2RX7; PPARGC1A; PRKAA2; SCT; TSHR; VIPR2 | 2 | 6.80 | GPD1; MRAP2 | 1 | 3.40 | CXCL9 | 5 | 1.03 | ADCYAP1R1; AKAP12; PPARGC1A; PRKAA2; TSHR | 5 | 1.15 | CAP1; CXCL11; HIF1A; PTHLH; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| regulation of alpha beta t cell differentiation: GO | 46 | 9 | 3.27 | ANXA1; CD80; IFNG; IL12B; IL4R; IL6; JAK3; PNP; SASH3 | 1 | 0.26 | ZBTB16 | 0 | 0.00 | | 0 | 0.00 | | 0 | 0.00 | | 2 | 1.23 | CD83; PNP |
| positive regulation of oxidoreductase activity: GO | 46 | 6 | 2.18 | CDH3; CYP27B1; GDNF; HIF1A; IFNG; IL1B | 6 | 1.54 | AGT; AGTR1; APOE; FCER2; SNCA; TERT | 0 | 0.00 | | 1 | 9.08 | IL1B | 3 | 1.66 | AGTR1; ESR1; SNCA | 2 | 1.23 | CYP27B1; HIF1A |
| regulation of extrinsic apoptotic signaling pathway in absence of ligand: GO | 46 | 6 | 2.18 | CSF2; GDNF; IFI6; IL1A; IL1B; NRG1 | 4 | 1.03 | BCL2; FGFR1; GATA1; TERT | 0 | 0.00 | | 1 | 9.08 | IL1B | 2 | 1.10 | BCL2; FGFR1 | 2 | 1.23 | NRG1; SNAI2 |
| regulation of immunoglobulin production: GO | 46 | 6 | 2.18 | IFNG; IL13RA2; IL4R; IL6; SASH3; TNFRSF4 | 2 | 0.51 | IL5; RBP4 | 0 | 0.00 | | 0 | 0.00 | | 0 | 0.00 | | 2 | 1.23 | IL10; IL13RA2 |
| primary alcohol metabolic process: GO | 46 | 5 | 1.82 | ADH7; AKR1B10; ALDH1A3; LRAT; SDR16C5 | 6 | 1.54 | ADH1B; ADH1C; ALDH1A1; AWAT2; PECR; RBP4 | 0 | 0.00 | | 0 | 0.00 | | 2 | 1.10 | ALDH3A2; DGAT2 | 2 | 1.23 | AKR1B10; LRAT |
| syndecan 1 pathway | 46 | 5 | 1.82 | HPSE; MMP1; MMP9; PPIB; SDC1 | 3 | 0.77 | COL11A1; COL11A2; COL9A2 | 0 | 0.00 | | 0 | 0.00 | | 1 | 0.55 | COL11A1 | 2 | 1.23 | COL17A1; HPSE |
| regulation of myoblast differentiation: GO | 46 | 4 | 1.46 | CCL17; CXCL10; CXCL9; NEU2 | 6 | 1.54 | BOC; CDON; FLT3LG; MSTN; MYOCD; SOX8 | 0 | 0.00 | | 1 | 9.08 | CXCL9 | 2 | 1.10 | CDON; PRICKLE1 | 2 | 1.23 | IGFBP3; PPARD |
| secondary metabolic process: GO | 46 | 4 | 1.46 | AKR1B10; IL1B; TH; UGT1A7 | 11 | 2.82 | BCL2; CYP1A1; CYP1A2; CYP2A6; CYP2D6; CYP2W1; | 0 | 0.00 | | 1 | 9.08 | IL1B | 5 | 2.76 | ASIP; BCL2; CYP2W1; PON3; TRPC1 | 2 | 1.23 | AKR1B10; TH |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | DCT; EPHX2; FMO2; OCA2; PON3 | | | | | | | | | | | | |
| positive regulation of neuron apoptotic process: GO | 46 | 3 | 1.09 | CCL3; CDK5R1; PCSK9 | 3 | 0.77 | GRIK5; PAK3; TFAP2B | 0 | 0.00 | | 0 | 0.00 | | 1 | 0.55 | PAK3 | 2 | 1.23 | CDK5R1; PCSK9 |
| thymus development: GO | 46 | 3 | 1.09 | CCNB2; FOXE1; TGFBR1 | 3 | 0.77 | BCL2; HAND2; SIX1 | 0 | 0.00 | | 0 | 0.00 | | 3 | 1.66 | BCL2; HAND2; SLC46A2 | 2 | 1.23 | CCNB2; FOXE1 |
| anterior posterior axis specification: GO | 46 | 2 | 0.73 | AURKA; WNT5A | 3 | 0.77 | CDX4; GPC3; TDRD5 | 0 | 0.00 | | 0 | 0.00 | | 2 | 1.10 | CDX4; HOXD8 | 2 | 1.23 | AURKA; WNT5A |
| embryonic cranial skeleton morphogenesis: GO | 46 | 2 | 0.73 | EIF4A3; TGFBR1 | 3 | 0.77 | SIX1; SPEF2; TBX15 | 0 | 0.00 | | 0 | 0.00 | | 3 | 1.66 | PRRX1; SPEF2; TBX15 | 2 | 1.23 | EIF4A3; WNT9B |
| ion antiporter activity: GO | 46 | 2 | 0.73 | SLC26A9; SLC7A11 | 8 | 2.05 | SLC22A9; SLC24A2; SLC26A1; SLC26A5; SLC26A7; SLC4A1; SLC9A2; SLC9A4 | 0 | 0.00 | | 0 | 0.00 | | 1 | 0.55 | SLC9A2 | 2 | 1.23 | SLC26A6; SLC7A11 |
| protein k48 linked ubiquitination: GO | 46 | 2 | 0.73 | UBE2C; UBE2T | 0 | 0.00 | | 0 | 0.00 | | 0 | 0.00 | | 0 | 0.00 | | 2 | 1.23 | UBE2C; UBE2T |
| receptor internalization: GO | 46 | 2 | 0.73 | CXCR1; RAB31 | 5 | 1.28 | CALCR; DNM1; GHR; GRIA1; SNCA | 1 | 9.08 | GHR | 0 | 0.00 | | 2 | 1.10 | GRIA1; SNCA | 2 | 1.23 | CXCR1; RAB31 |
| regulation of chemotaxis: GO | 176 | 26 | 2.47 | ARTN; CIQBP; CALR; CCL21; CCL3; CCL7; CXCL1; CXCL10; CXCL11; CXCL13; CXCL3; CXCL5; | 18 | 1.21 | EDN3; ELANE; F7; FEZF2; FGF1; FGFR1; IL16; NTRK3; PDGFD; PLXNA3; PLXNA4; RARRES2; SEMA3A; SEMA3B; | 0 | 0.00 | | 5 | 11.87 | CXCL5; CXCL9; IL1B; RAC2; SERPINE1 | 11 | 1.59 | CXCL12; EDN3; ELANE; FGF2; FGFR1; LPAR1; PLXNA4; RARRES2; SEMA3E; SEMA4G; SLIT2 | 7 | 1.13 | ARTN; CXCL11; CXCL2; CXCL6; S100A14; SEMA4B; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | CXCL6; CXCL9; CXCR4; F2RL1; GREM1; IL1B; IL6; RAC2; S100A14; S100A7; SCG2; SEMA4B; SERPINE1; WNT5A | | | SEMA3D; SEMA3E; SEMA3G; SLIT2 | | | | | | | | | | | | |
| regulation of extrinsic apoptotic signaling pathway: GO | 150 | 19 | 2.12 | CSF2; GDNF; GSTP1; HMOX1; IFI6; IL19; IL1A; IL1B; ITGA6; NRG1; PDIA3; PSME3; PYCARD; SCG2; SERPINE1; TGFBR1; TNFRSF10A; TNFRSF12A; TNFSF10 | 10 | 0.79 | AGT; AR; BCL2; BMP5; FGFR1; GOS2; GATA1; NOL3; TERT; TIMP3 | 0 | 0.00 | | 2 | 5.57 | IL1B; SERPINE1 | 2 | 0.34 | BCL2; FGFR1 | 6 | 1.13 | BMPR1B; GSTP1; IL19; ITGA6; NRG1; SNAI2 |
| signaling by leptin | 150 | 13 | 1.45 | ACTB; CSF2; DUSP6; DUSP9; EREG; HBEGF; IL2RA; JAK3; NRAS; NRG1; PSMA5; PSMB6; SOCS3 | 12 | 0.94 | BTC; CNKSR2; EGF; FGF1; FGFR1; FGFR3; GFRA1; GRIN2A; IL5; IRS2; NRG2; SHC2 | 0 | 0.00 | | 1 | 2.79 | IL2RA | 5 | 0.85 | ANGPT1; CNKSR2; EGF; FGFR1; SHC2 | 6 | 1.13 | ACTB; DUSP6; EREG; HBEGF; NRG1; SOCS3 |
| myd88-independent tlr3/tlr4 cascade | 72 | 5 | 1.16 | CAP1; DUSP6; MYD88; | 0 | 0.00 | | 0 | 0.00 | | 0 | 0.00 | | 0 | 0.00 | | 3 | 1.18 | CAP1; DUSP6; MYD88 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | S100A12; UBE2N | | | | | | | | | | | | | | | |
| toll like receptor 3 (tlr3) cascade | 72 | 5 | 1.16 | CAP1; DUSP6; MYD88; S100A12; UBE2N | 0 | 0.00 | | 0 | 0.00 | | 0 | 0.00 | | 0 | 0.00 | | 3 | 1.18 | CAP1; DUSP6; MYD88 |
| trif-mediated tlr3/tlr4 signaling | 72 | 5 | 1.16 | CAP1; DUSP6; MYD88; S100A12; UBE2N | 0 | 0.00 | | 0 | 0.00 | | 0 | 0.00 | | 0 | 0.00 | | 3 | 1.18 | CAP1; DUSP6; MYD88 |
| adipocytokine signaling pathway | 72 | 4 | 0.93 | JAK3; PRKCQ; SLC2A1; SOCS3 | 11 | 1.80 | ACACB; ADIPOQ; IRS2; IRS4; LEP; LEPR; PCK1; PPARGC1A; PRKAA2; RXRG; SLC2A4 | 1 | 5.80 | ADIPOQ | 0 | 0.00 | | 2 | 0.71 | PPARGC1A; PRKAA2 | 3 | 1.18 | PRKCQ; SLC2A1; SOCS3 |
| biomineral tissue development: GO | 72 | 4 | 0.93 | ALPL; CYP27B1; PTGS2; SRGN | 11 | 1.80 | AMELX; ATP2B2; CLEC3B; ENPP1; FGFR3; GPC3; LEP; PKDCC; PTH1R; WDR72; WNT11 | 1 | 5.80 | CLEC3B | 0 | 0.00 | | 5 | 1.76 | DDR2; PTH1R; TMEM119; WDR72; WNT11 | 3 | 1.18 | CYP27B1; PTGS2; SBNO2 |
| platelet alpha granule: GO | 72 | 4 | 0.93 | SERPINA1; SERPINE1; SERPINE2; SRGN | 7 | 1.15 | ACTN2; ALB; CFD; CLU; EGF; SERPINA5; SNCA | 0 | 0.00 | | 1 | 5.80 | SERPINE1 | 4 | 1.41 | CLU; EGF; ISLR; SNCA | 3 | 1.18 | ACTN1; PCDH7; SERPINE2 |
| adherens junction | 72 | 3 | 0.70 | ACTB; RAC2; TGFBR1 | 7 | 1.15 | ACTN2; ACVR1C; CTNNA3; FGFR1; POTEKP; | 1 | 5.80 | ACVR1C | 1 | 5.80 | RAC2 | 3 | 1.06 | FGFR1; POTEKP; TCF7L1 | 3 | 1.18 | ACTB; ACTN1; SNAI2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | SORBS1; TCF7L1 | | | | | | | | | | | | |
| negative regulation of hemopoiesis: GO | 124 | 14 | 1.89 | ANXA1; CCL3; CTLA4; GPR171; HIST1H4I; HIST1H4J; HIST1H4K; HIST1H4L; IL4R; JAK3; LTF; NME1; PGLYRP2; UBASH3B | 6 | 0.57 | ADIPOQ; CARTPT; CLDN18; DTX1; LRRC17; ZBTB16 | 1 | 3.37 | ADIPOQ | 0 | 0.00 | | 2 | 0.41 | CLDN18; LRRC17 | 5 | 1.14 | HIST1H4I; HLA-G; LTF; TRIB1; UBASH3B |
| b cell activation: GO | 124 | 7 | 0.94 | BAK1; CD79A; EXO1; IFNE; IL7R; JAK3; NTRK1 | 4 | 0.38 | BCL2; CXCR5; HDAC5; IFNA5 | 0 | 0.00 | | 1 | 3.37 | IL7R | 1 | 0.20 | BCL2 | 5 | 1.14 | BAK1; BCL3; EXO1; IFNE; IL10 |
| limbic system development: GO | 98 | 11 | 1.88 | ALDH1A3; ANXA3; CDK5R1; CNTNAP2; KIF14; LRP8; NEFL; NME1; NR4A3; RAN; UBA6 | 13 | 1.57 | BCAN; CYP17A1; DCX; DRD1; EMX2; FEZF2; FGFR1; ID4; KCNA1; LMX1A; PLXNA3; RELN; SEMA3A | 0 | 0.00 | | 1 | 4.26 | ANXA3 | 4 | 1.04 | EMX2; FGFR1; MDK; RELN | 4 | 1.16 | CDK5R1; CNTNAP2; KIF14; RAN |
| lipid phosphorylation: GO | 98 | 4 | 0.68 | CD80; EREG; HBEGF; NRG1 | 11 | 1.32 | BTC; EGF; ERBB4; FGF1; FGF17; FGF22; FGF9; FGFR1; FGFR3; IRS2; NRG2 | 0 | 0.00 | | 0 | 0.00 | | 6 | 1.56 | EGF; ERBB4; FGF2; FGF22; FGFR1; PIK3R6 | 4 | 1.16 | EFR3B; EREG; HBEGF; NRG1 |
| regulation of myeloid cell differentiation: GO | 177 | 15 | 1.42 | CA2; CCL3; GPR171; HIF1A; HIST1H4I; | 13 | 0.87 | ADIPOQ; CARTPT; CLDN18; GATA1; IL34; | 1 | 2.36 | ADIPOQ | 1 | 2.36 | ISG15 | 6 | 0.86 | CLDN18; LRRC17; MITF; P4HTM; | 7 | 1.12 | CA2; HIF1A; HIST1H4I; IL20; LTF; TRIB1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | HIST1H4J; HIST1H4K; HIST1H4L; IFNG; IL12B; IL20; ISG15; LTF; NME1; UBASH3B | | | IL5; LEP; LIF; LRRC17; MITF; P4HTM; SCIN; ZBTB16 | | | | | | | | | SCIN; TESC | | | UBASH3B |
| mapk1/mapk3 signaling | 151 | 14 | 1.55 | ACTB; CDK1; CSF2; DUSP6; DUSP9; EREG; HBEGF; IL2RA; IL6; JAK3; NRAS; NRG1; PSMA5; PSMB6 | 12 | 0.94 | BTC; CNKSR2; EGF; FGF1; FGFR1; FGFR3; GFRA1; GRIN2A; IL5; IRS2; NRG2; SHC2 | 0 | 0.00 | | 1 | 2.77 | IL2RA | 5 | 0.84 | ANGPT1; CNKSR2; EGF; FGFR1; SHC2 | 6 | 1.13 | ACTB; CDK1; DUSP6; EREG; HBEGF; NRG1 |
| regulation of interleukin 2 production: GO | 47 | 8 | 2.85 | ANXA1; CD3E; CD80; IL1A; IL1B; PRKCQ; PRNP; SASH3 | 1 | 0.25 | CD34 | 0 | 0.00 | | 2 | 17.78 | GBP1; IL1B | 1 | 0.54 | CD34 | 2 | 1.21 | CD83; PRKCQ |
| peptidyl proline modification: GO | 47 | 6 | 2.14 | FKBPL; PPIA; PPIB; PPIF; PPIL1; TTC9 | 1 | 0.25 | PPIL6 | 0 | 0.00 | | 0 | 0.00 | | 2 | 1.08 | FKBP7; PPIL6 | 2 | 1.21 | PPIF; PPIL1 |
| protein kinase c binding: GO | 47 | 6 | 2.14 | C1QBP; DSP; NELL2; TOP2A; UGT1A10; UGT1A7 | 4 | 1.00 | DACT1; DACT2; HDAC5; LDB3 | 0 | 0.00 | | 0 | 0.00 | | 2 | 1.08 | ADD3; DACT1 | 2 | 1.21 | NELL2; TOP2A |
| regulation of organic acid transport: GO | 47 | 5 | 1.78 | CCK; HRH3; IL1B; NTSR1; P2RY2 | 10 | 2.51 | ADORA1; ATP1A2; CYP4A11; GRM7; IRS2; LEP; NPY5R; P2RX7; PLA2G6; SNCA | 0 | 0.00 | | 1 | 8.89 | IL1B | 2 | 1.08 | CYP4A11; SNCA | 2 | 1.21 | NTSR1; P2RY2 |
| response to axon injury: GO | 47 | 5 | 1.78 | CDK1; FLRT3; NEFL; | 4 | 1.00 | APOD; BCL2; FOLR1; NTRK3 | 0 | 0.00 | | 0 | 0.00 | | 4 | 2.16 | BCL2; CHL1; DPYSL3; KCNK2 | 2 | 1.21 | CDK1; FLRT3 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| mrna 3 utr binding: GO | 47 | 3 | 1.07 | NTRK1; TNC ELAVL2; SERBP1; ZC3H12A | 2 | 0.50 | CPEB1; RBM24 | 0 | 0.00 | | 0 | 0.00 | | 2 | 1.08 | CPEB1; RBMS3 | 2 | 1.21 | ELAVL2; ZC3H12A |
| negative regulation of calcium ion transport: GO | 47 | 3 | 1.07 | GSTO1; NTSR1; PTGS2 | 9 | 2.26 | ADRA2A; ATP1A2; BCL2; CASQ2; DRD4; GSTM2; SLN; SPINK1; TRDN | 0 | 0.00 | | 0 | 0.00 | | 3 | 1.62 | ADRA2A; BCL2; TRDN | 2 | 1.21 | NTSR1; PTGS2 |
| regulation of insulin secretion involved in cellular response to glucose stimulus: GO | 47 | 3 | 1.07 | HIF1A; HMGCR; VSNL1 | 8 | 2.01 | ADCY5; ADRA2A; BRSK2; CFTR; GPLD1; NRXN1; PLA2G6; SYBU | 0 | 0.00 | | 0 | 0.00 | | 5 | 2.70 | ADRA2A; BRSK2; GPLD1; NRXN1; SYBU | 2 | 1.21 | HIF1A; VSNL1 |
| autoimmune thyroid disease | 47 | 2 | 0.71 | CD80; CTLA4 | 4 | 1.00 | IFNA5; IL5; TG; TSHR | 0 | 0.00 | | 1 | 8.89 | GZMB | 1 | 0.54 | TSHR | 2 | 1.21 | HLA-G; IL10 |
| carbon carbon lyase activity: GO | 47 | 2 | 0.71 | AMD1; ODC1 | 6 | 1.51 | ALDOB; CRY2; CYP17A1; HMGCLL1; HOGA1; PCK1 | 0 | 0.00 | | 0 | 0.00 | | 3 | 1.62 | ALDOC; CRY2; HDC | 2 | 1.21 | GADL1; ODC1 |
| regulation of cofactor metabolic process: GO | 47 | 2 | 0.71 | HIF1A; PGAM1 | 7 | 1.76 | GPD1; MLXIPL; P2RX7; PDK4; PPARGC1A; PRKAA2; SNCA | 1 | 8.89 | GPD1 | 0 | 0.00 | | 5 | 2.70 | PDK3; PDK4; PPARGC1A; PRKAA2; SNCA | 2 | 1.21 | HIF1A; PGAM1 |
| hes hey pathway | 47 | 1 | 0.36 | HIF1A | 3 | 0.75 | AR; GATA1; GHR | 1 | 8.89 | GHR | 0 | 0.00 | | 0 | 0.00 | | 2 | 1.21 | E2F1; HIF1A |
| leukocyte apoptotic process: GO | 22 | 6 | 4.56 | BAK1; HCAR2; IFNG; IL2RA; | 0 | 0.00 | | 0 | 0.00 | | 2 | 37.99 | HCAR2; IL2RA | 0 | 0.00 | | 1 | 1.29 | BAK1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | IL6; TNFRSF21 | | | | | | | | | | | | | | | |
| activation of matrix metalloproteinases | 22 | 5 | 3.80 | CTSL; MMP1; MMP10; MMP3; MMP9 | 1 | 0.54 | KLKB1 | 0 | 0.00 | | 0 | 0.00 | | 1 | 1.15 | CTSG | 1 | 1.29 | MMP3 |
| actin nucleation: GO | 22 | 4 | 3.04 | ACTR3; ARPC1A; ARPC3; ARPC5L | 2 | 1.07 | GSN; SCIN | 0 | 0.00 | | 0 | 0.00 | | 1 | 1.15 | SCIN | 1 | 1.29 | ARPC1A |
| g protein coupled chemoattractant receptor activity: GO | 22 | 4 | 3.04 | CCR4; CCR5; CXCR1; CXCR4 | 1 | 0.54 | CXCR5 | 0 | 0.00 | | 0 | 0.00 | | 0 | 0.00 | | 1 | 1.29 | CXCR1 |
| metabolic disorders of biological oxidation enzymes | 22 | 4 | 3.04 | CYP24A1; CYP27B1; CYP4F22; UGT1A1 | 3 | 1.61 | CYP17A1; MAOA; MAT1A | 0 | 0.00 | | 0 | 0.00 | | 0 | 0.00 | | 1 | 1.29 | CYP27B1 |
| chemical pathway | 22 | 3 | 2.28 | CYCS; EIF2S1; STAT1 | 1 | 0.54 | BCL2 | 0 | 0.00 | | 0 | 0.00 | | 1 | 1.15 | BCL2 | 1 | 1.29 | CYCS |
| g protein alpha subunit binding: GO | 22 | 3 | 2.28 | F2RL1; LPAR3; RGS1 | 1 | 0.54 | DRD1 | 0 | 0.00 | | 0 | 0.00 | | 1 | 1.15 | LPAR1 | 1 | 1.29 | RGS1 |
| nfkb activation by nontypeable hemophilus influenzae | 22 | 3 | 2.28 | IL1B; MYD88; TGFBR1 | 0 | 0.00 | | 0 | 0.00 | | 1 | 19.00 | IL1B | 0 | 0.00 | | 1 | 1.29 | MYD88 |
| positive regulation of interleukin 4 production: GO | 22 | 3 | 2.28 | CD3E; PRKCQ; SASH3 | 0 | 0.00 | | 0 | 0.00 | | 0 | 0.00 | | 0 | 0.00 | | 1 | 1.29 | PRKCQ |
| positive regulation of nucleoside metabolic process: GO | 22 | 3 | 2.28 | GADD45GIP1; HIF1A; VCP | 5 | 2.68 | GPD1; MLXIPL; P2RX7; PPARGC1A; PRKAA2 | 1 | 19.00 | GPD1 | 0 | 0.00 | | 2 | 2.31 | PPARGC1A; PRKAA2 | 1 | 1.29 | HIF1A |
| protein disulfide oxidoreductase activity: GO | 22 | 3 | 2.28 | SH3BGRL3; TXN; TXNDC8 | 0 | 0.00 | | 0 | 0.00 | | 0 | 0.00 | | 1 | 1.15 | GLRX | 1 | 1.29 | TXN |
| regulation | 22 | 3 | 2.28 | ARTN; | 3 | 1.61 | F7; IL16; | 0 | 0.00 | | 0 | 0.00 | | 1 | 1.15 | CXCL12 | 1 | 1.29 | ARTN |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline: Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo: Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo: Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| of positive chemotaxis: GO | | | | F2RL1; SCG2 | | | NTRK3 | | | | | | | | | | | | |
| alzheimer's disease | 22 | 2 | 1.52 | GAPDH; PSENEN | 5 | 2.68 | APBB1; APOE; LPL; MAPT; SNCA | 1 | 19.00 | LPL | 0 | 0.00 | | 2 | 2.31 | MAPT; SNCA | 1 | 1.29 | GAPDH |
| anterograde axonal transport: GO | 22 | 2 | 1.52 | KIF4A; NEFL | 1 | 0.54 | KIF1A | 0 | 0.00 | | 0 | 0.00 | | 0 | 0.00 | | 1 | 1.29 | KIF4A |
| caspase cascade in apoptosis | 22 | 2 | 1.52 | LMNB1; LMNB2 | 0 | 0.00 | | 0 | 0.00 | | 1 | 19.00 | GZMB | 0 | 0.00 | | I | 1.29 | LMNB2 |
| cone pathway | 22 | 2 | 1.52 | GNGT2; LRAT | 3 | 1.61 | GUCA1B; RGS9; SLC24A2 | 0 | 0.00 | | 0 | 0.00 | | 0 | 0.00 | | 1 | 1.29 | LRAT |
| cysteine type endopeptidase inhibitor activity involved in apoptotic process: GO | 22 | 2 | 1.52 | BIRC5; SERPINB9 | 3 | 1.61 | NOL3; SNCA; TFAP2B | 0 | 0.00 | | 1 | 19.00 | SERPINB9 | 1 | 1.15 | SNCA | 1 | 1.29 | BIRC5 |
| glutathione derivative metabolic process: GO | 22 | 2 | 1.52 | GSTO1; GSTP1 | 5 | 2.68 | GSTA3; GSTM2; GSTM3; GSTM5; GSTT2B | 0 | 0.00 | | 0 | 0.00 | | 1 | 1.15 | GSTM5 | 1 | 1.29 | GSTP1 |
| host interactions with influenza factors | 22 | 2 | 1.52 | ISG15; KPNA2 | 0 | 0.00 | | 0 | 0.00 | | 1 | 19.00 | ISG15 | 0 | 0.00 | | 1 | 1.29 | KPNA2 |
| il5 pathway | 22 | 2 | 1.52 | IL1B; IL6 | 1 | 0.54 | IL5 | 0 | 0.00 | | 1 | 19.00 | IL1B | 0 | 0.00 | | 1 | 1.29 | CISH |
| modulation of transcription in other organism involved in symbiotic interaction: GO | 22 | 2 | 1.52 | CCL3; HMGA2 | 2 | 1.07 | NTRK3; POU2F3 | 0 | 0.00 | | 0 | 0.00 | | 0 | 0.00 | | 1 | 1.29 | HMGA2 |
| pdgfra pathway | 22 | 2 | 1.52 | IFNG; SHB | 0 | 0.00 | | 0 | 0.00 | | 0 | 0.00 | | 0 | 0.00 | | 1 | 1.29 | SHB |
| plc-gamma1 signalling | 22 | 2 | 1.52 | NGF; NTRK1 | 2 | 1.07 | ADCY8; PRKAR2B | 1 | 19.00 | PRKAR2B | 0 | 0.00 | | 0 | 0.00 | | 1 | 1.29 | NGF |
| positive regulation of myoblast differentiation: GO | 22 | 2 | 1.52 | CXCL9; NEU2 | 3 | 1.61 | BOC; CDON; FLT3LG | 0 | 0.00 | | 1 | 19.00 | CXCL9 | 1 | 1.15 | CDON | 1 | 1.29 | IGFBP3 |
| regulation of | 22 | 2 | 1.52 | GDNF; | 2 | 1.07 | ADIPOQ; LIF | 1 | 19.00 | ADIPOQ | 0 | 0.00 | | 0 | 0.00 | | 1 | 1.29 | WNT9B |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| metanephros development: GO | | | | STAT1 | | | | | | | | | | | | | | | |
| retina layer formation: GO | 22 | 2 | 1.52 | FJX1; SDK2 | 2 | 1.07 | FOXN4; TFAP2B | 0 | 0.00 | | 0 | 0.00 | | 1 | 1.15 | TSPAN12 | 1 | 1.29 | SDK2 |
| semaphorin receptor binding: GO | 22 | 2 | 1.52 | SEMA4B; SH3BGRL3 | 5 | 2.68 | SEMA3A; SEMA3B; SEMA3D; SEMA3E; SEMA3G | 0 | 0.00 | | 0 | 0.00 | | 2 | 2.31 | SEMA3E; SEMA4G | 1 | 1.29 | SEMA4B |
| subpallium development: GO | 22 | 2 | 1.52 | ALDH1A3; CNTNAP2 | 2 | 1.07 | DRD1; SLITRK5 | 0 | 0.00 | | 0 | 0.00 | | 0 | 0.00 | | 1 | 1.29 | CNTNAP2 |
| thromboxane signalling through tp receptor | 22 | 2 | 1.52 | GNA15; GNGT2 | 0 | 0.00 | | 0 | 0.00 | | 0 | 0.00 | | 1 | 1.15 | GNG11 | 1 | 1.29 | GNA15 |
| amino acid synthesis and interconversion (transamination) | 22 | 1 | 0.76 | SERINC2 | 2 | 1.07 | ASPA; GPT | 0 | 0.00 | | 0 | 0.00 | | 2 | 2.31 | ASPA; GPT | 1 | 1.29 | SERINC2 |
| au rich element binding: GO | 22 | 1 | 0.76 | ZC3H12A | 1 | 0.54 | CPEB1 | 0 | 0.00 | | 0 | 0.00 | | 1 | 1.15 | CPEB1 | 1 | 1.29 | ZC3H12A |
| base excision repair | 22 | 1 | 0.76 | PCNA | 0 | 0.00 | | 0 | 0.00 | | 0 | 0.00 | | 0 | 0.00 | | 1 | 1.29 | FEN1 |
| cellular response to interleukin 6: GO | 22 | 1 | 0.76 | IL6 | 2 | 1.07 | PPARGC1A; PTGIS | 0 | 0.00 | | 0 | 0.00 | | 1 | 1.15 | PPARGC1A | 1 | 1.29 | SBNO2 |
| central nervous system projection neuron axonogenesis: GO | 22 | 1 | 0.76 | FBXO45 | 7 | 3.75 | DCLK1; DCX; EPHB1; GLI2; PLXNA4; SLIT2; SPTBN4 | 0 | 0.00 | | 0 | 0.00 | | 5 | 5.77 | DCLK1; GLI2; PLXNA4; SLIT2; SPTBN4 | 1 | 1.29 | FBXO45 |
| cerebellar cortex formation: GO | 22 | 1 | 0.76 | WNT7A | 3 | 1.61 | ATP2B2; CBLN1; NRXN1 | 0 | 0.00 | | 0 | 0.00 | | 1 | 1.15 | NRXN1 | 1 | 1.29 | WNT7A |
| eicosanoid metabolism | 22 | 1 | 0.76 | PTGS2 | 3 | 1.61 | CYP2J2; EPHX2; PTGIS | 0 | 0.00 | | 0 | 0.00 | | 1 | 1.15 | PTGFR | 1 | 1.29 | PTGS2 |
| endocardial cushion morphogenesis: GO | 22 | 1 | 0.76 | TBX20 | 1 | 0.54 | TMEM100 | 0 | 0.00 | | 0 | 0.00 | | 0 | 0.00 | | 1 | 1.29 | SNAI2 |
| hydrolase activity hydrolyzing n | 22 | 1 | 0.76 | PCNA | 2 | 1.07 | ART5; NEIL1 | 0 | 0.00 | | 0 | 0.00 | | 0 | 0.00 | | 1 | 1.29 | NEIL3 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| glycosyl compounds: GO | | | | | | | | | | | | | | | | | | | |
| immunoglobulin production involved in immunoglobulin mediated immune response: GO | 22 | 1 | 0.76 | EXO1 | 0 | 0.00 | | 0 | 0.00 | | 0 | 0.00 | | 0 | 0.00 | | 1 | 1.29 | EXO1 |
| neurexins and neuroligins | 22 | 1 | 0.76 | HOMER1 | 5 | 2.68 | APBA1; GRIN2A; NLGN1; SYT1; SYT9 | 0 | 0.00 | | 0 | 0.00 | | 1 | 1.15 | APBA1 | 1 | 1.29 | HOMER1 |
| pgc1a pathway | 22 | 1 | 0.76 | CAMKIG | 6 | 3.22 | CAMK1; CAMK2A; CAMK2B; HDAC5; PPARGC1A; SLC2A4 | 0 | 0.00 | | 0 | 0.00 | | 2 | 2.31 | CAMK1; PPARGC1A | 1 | 1.29 | CAMK1G |
| positive regulation of rna splicing: GO | 22 | 1 | 0.76 | HSPA8 | 1 | 0.54 | CELF4 | 0 | 0.00 | | 0 | 0.00 | | 1 | 1.15 | RBM20 | 1 | 1.29 | HSPA8 |
| regulation of protein phosphatase type 2a activity: GO | 22 | 1 | 0.76 | PPP2R2C | 1 | 0.54 | PPP2R2B | 0 | 0.00 | | 0 | 0.00 | | 0 | 0.00 | | 1 | 1.29 | PPP2R2C |
| ribosomal large subunit assembly: GO | 22 | 1 | 0.76 | DDX28 | 0 | 0.00 | | 0 | 0.00 | | 0 | 0.00 | | 0 | 0.00 | | 1 | 1.29 | DDX28 |
| smad2/smad3: smad4 heterotrimer regulates transcription | 22 | 1 | 0.76 | SERPINE1 | 0 | 0.00 | | 0 | 0.00 | | 1 | 19.00 | SERPINE1 | 0 | 0.00 | | 1 | 1.29 | JUNB |
| telomere c-strand (lagging strand) synthesis | 22 | 1 | 0.76 | PCNA | 0 | 0.00 | | 0 | 0.00 | | 0 | 0.00 | | 0 | 0.00 | | 1 | 1.29 | FEN1 |
| traf6 mediated induction of nfkb and | 22 | 1 | 0.76 | CDK1 | 0 | 0.00 | | 0 | 0.00 | | 0 | 0.00 | | 0 | 0.00 | | 1 | 1.29 | CDK1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| map kinases upon tlr7 8 or 9 activation | | | | | | | | | | | | | | | | | | | |
| 2 iron 2 sulfur cluster binding: GO | 22 | 0 | 0.00 | | 1 | 0.54 | CMAHP | 0 | 0.00 | | 0 | 0.00 | | 2 | 2.31 | AOX1; CMAHP | 1 | 1.29 | XDH |
| interaction with host: GO | 125 | 17 | 2.28 | CCR5; CD80; CTSB; CXADR; CXCR4; DPP4; ITGB6; KPNA2; LAMP3; LDLR; PPIA; SERPINB3; SERPINB9; SLAMF1; TAP2; TNFRSF4; ZC3H12A | 3 | 0.28 | ALB; NCAM1; NTRK3 | 0 | 0.00 | | 2 | 6.69 | LAMP3; SERPINB9 | 2 | 0.41 | EFNB3; NCAM1 | 5 | 1.13 | DPP4; ITGB6; KPNA2; LDLR; ZC3H12A |
| neuron projection terminus: GO | 125 | 7 | 0.94 | ADCYAP1; CCK; FLRT3; NMU; NTSR1; SNCB; TH | 17 | 1.60 | ADORA1; CHRM1; CHRM2; CHRM3; CHRM4; DMD; DRD1; DRD4; GRIA4; GRIK3; GRIK5; GRIN1; KCNA1; KCNA2; SNCA; SYNGR1; SYT1 | 1 | 3.34 | GRIA4 | 0 | 0.00 | | 7 | 1.42 | CHRM1; CHRM3; ESR1; GRIK3; KCNK2; SLC18A2; SNCA | 5 | 1.13 | FLRT3; NMU; NTSR1; SNCB; TH |
| mapk family signaling cascades | 178 | 16 | 1.50 | ACTB; CDK1; CSF2; DUSP6; DUSP9; EREG; HBEGF; | 12 | 0.80 | BTC; CNKSR2; EGF; FGF1; FGFR1; FGFR3; | 0 | 0.00 | | 1 | 2.35 | IL2RA | 5 | 0.71 | ANGPT1; CNKSR2; EGF; FGFR1; SHC2 | 7 | 1.12 | ACTB; CDK1; DUSP6; EREG; HBEGF; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | IL2RA; IL6; JAK3; MAPK6; MMP10; NRAS; NRG1; PSMA5; PSMB6 | | | GFRA1; GRIN2A; IL5; IRS2; NRG2; SHC2 | | | | | | | | | | | | MAPK6; NRG1 |
| the citric acid (tca) cycle and respiratory electron transport | 99 | 6 | 1.01 | COX7B; CYCS; GLO1; LDHA; SCO2; SLC16A1 | 1 | 0.12 | PDK4 | 0 | 0.00 | | 0 | 0.00 | | 2 | 0.51 | PDK3; PDK4 | 4 | 1.15 | CYCS; LDHA; PPARD; SCO2 |
| hippocampus development: GO | 73 | 9 | 2.06 | ANXA3; CDK5R1; KIF14; LRP8; NEFL; NME1; NR4A3; RAN; UBA6 | 11 | 1.78 | BCAN; CYP17A1; DCX; DRD1; EMX2; FEZF2; ID4; KCNA1; LMX1A; PLXNA3; RELN | 0 | 0.00 | | 1 | 5.72 | ANXA3 | 3 | 1.04 | EMX2; MDK; RELN | 3 | 1.17 | CDK5R1; KIF14; RAN |
| cardiac muscle cell differentiation: GO | 73 | 5 | 1.15 | CALR; CCNB1; CDK1; CXADR; NRG1 | 10 | 1.62 | ACTN2; AGT; FHOD3; KAT2A; MESP1; MYH11; MYOCD; NKX2-5; SORBS2; TBX5 | 0 | 0.00 | | 0 | 0.00 | | 2 | 0.70 | MESP1; SORBS2 | 3 | 1.17 | CCNB1; CDK1; NRG1 |
| vascular endothelial growth factor receptor signaling pathway: GO | 73 | 4 | 0.92 | ACTB; PGF; SH2D2A; SHB | 1 | 0.16 | SHC2 | 0 | 0.00 | | 0 | 0.00 | | 2 | 0.70 | FOXC1; SHC2 | 3 | 1.17 | ACTB; SHB; VAV2 |
| regulation of sodium ion transport: GO | 73 | 3 | 0.69 | ATP1B3; PCSK9; SERPINE2 | 12 | 1.94 | AGT; ATP1A2; DMD; DRD4; FXYD2; | 0 | 0.00 | | 0 | 0.00 | | 5 | 1.74 | ATP1B2; GLRX; SCNN1B; SPTBN4; | 3 | 1.17 | PCSK9; SERPINE2; SGK1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | | | | NKAIN4; NKX2-5; P2RX7; PER1; SGK2; SPTBN4; WNK2 | | | | | | | | | TESC | | | |
| signaling adaptor activity: GO | 73 | 3 | 0.69 | HOMER1; SH2D2A; SHB | 5 | 0.81 | ARHGAP6; GRB14; IRS4; MAPK8IP1; SORBS1 | 0 | 0.00 | | 0 | 0.00 | | 0 | 0.00 | | 3 | 1.17 | AFAPIL2; HOMER1; SHB |
| regulation of ras protein signal transduction: GO | 179 | 9 | 0.84 | ECT2; F2RL1; FOXM1; ITGA3; KIF14; NRG1; NTRK1; PLEKHG7; RALGPS2 | 10 | 0.66 | ADRA1A; APOE; ARHGEF19; ARHGEF25; ARHGEF26; MCF2L; MYOC; OBSCN; PLEKHG5; PSD2 | 0 | 0.00 | | 0 | 0.00 | | 9 | 1.28 | ADRA1A; ARHGEF25; ARHGEF26; ARHGEF33; DLC1; LPAR1; MYOC; PREX2; SPRY1 | 7 | 1.11 | ARHGEF16; ECT2; FOXMI; ITGA3; KIF14; NRG1; VAV2 |
| nucleus organization: GO | 126 | 6 | 0.80 | CCNB1; CCNB2; CDK1; CEP55; NOLC1; PLK1 | 6 | 0.56 | CHD5; H1FNT; SYCP1; SYNE1; TNP1; WBP2NL | 0 | 0.00 | | 0 | 0.00 | | 2 | 0.40 | SYCP3; SYNE1 | 5 | 1.13 | CCNB1; CCNB2; CDK1; CEP55; PLK1 |
| cytochrome p450-arranged by substrate type | 48 | 5 | 1.74 | CYP24A1; CYP27B1; CYP2S1; CYP4F11; CYP4F22 | 12 | 2.95 | CYP17A1; CYP1A1; CYP1A2; CYP2A6; CYP2C9; CYP2J2; CYP2W1; CYP3A5; CYP4A11; CYP4B1; CYP4F12; PTGIS | 0 | 0.00 | | 0 | 0.00 | | 6 | 3.18 | CYP2W1; CYP3A4; CYP3A5; CYP4A11; CYP4B1; CYP4F12 | 2 | 1.18 | CYP27B1; CYP2S1 |
| digestive tract morphogenesis: GO | 48 | 5 | 1.74 | FOXF1; HIF1A; STRA6; TP63; | 6 | 1.47 | BCL2; DACT1; GLI2; SOX10; | 0 | 0.00 | | 0 | 0.00 | | 5 | 2.65 | BCL2; DACTI; GLI2; | 2 | 1.18 | HIF1A; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | WNT5A | | | TCF21; WNT11 | | | | | | | | | SHOX2; WNT11 | | | |
| negative regulation of t cell proliferation: GO | 48 | 5 | 1.74 | CD274; IDO1; IL2RA; PRNP; TNFRSF21 | 1 | 0.25 | SCGB1A1 | 0 | 0.00 | | 1 | 8.71 | IL2RA | 0 | 0.00 | | 2 | 1.18 | HLA-G; IL10 |
| p53-dependent g1 dna damage response | 48 | 5 | 1.74 | CCNA2; CCNE1; CDKN1A; PSMA5; PSMB6 | 0 | 0.00 | | 0 | 0.00 | | 0 | 0.00 | | 0 | 0.00 | | 2 | 1.18 | CCNA2; CDKN1A |
| p53-dependent g1/s dna damage checkpoint | 48 | 5 | 1.74 | CCNA2; CCNE1; CDKN1A; PSMA5; PSMB6 | 0 | 0.00 | | 0 | 0.00 | | 0 | 0.00 | | 0 | 0.00 | | 2 | 1.18 | CCNA2; CDKN1A |
| arf6 trafficking pathway | 48 | 4 | 1.39 | IL2RA; ITGA3; ITGA6; NME1 | 5 | 1.23 | AGTR1; ITGA7; ITGA8; SLC2A4; TSHR | 0 | 0.00 | | 1 | 8.71 | IL2RA | 4 | 2.12 | AGTR1; CPE; ITGA11; TSHR | 2 | 1.18 | ITGA3; ITGA6 |
| response to amine: GO | 48 | 4 | 1.39 | CDK1; CTSB; NME1; TH | 5 | 1.23 | DRD1; DRD4; GRIN1; GRIN2A; PPP1R1B | 0 | 0.00 | | 0 | 0.00 | | 1 | 0.53 | SLC18A2 | 2 | 1.18 | CDK1; TH |
| cardiac cell development: GO | 48 | 3 | 1.05 | CCNB1; CDK1; CXADR | 7 | 1.72 | ACTN2; AGT; FHOD3; MYH11; MYOCD; NKX2-5; SORBS2 | 0 | 0.00 | | 0 | 0.00 | | 1 | 0.53 | SORBS2 | 2 | 1.18 | CCNB1; CDK1 |
| cell projection cytoplasm: GO | 48 | 3 | 1.05 | HIF1A; KIF4A; NEFL | 2 | 0.49 | GRIK3; KIFIA | 0 | 0.00 | | 0 | 0.00 | | 1 | 0.53 | GRIK3 | 2 | 1.18 | HIF1A; KIF4A |
| copii (coat protein 2) mediated vesicle transport | 48 | 3 | 1.05 | AREG; CTSC; TGFA | 2 | 0.49 | FOLR1; TRAPPC6A | 0 | 0.00 | | 0 | 0.00 | | 1 | 0.53 | TRAPPC6A | 2 | 1.18 | AREG; TGFA |
| methylated histone binding: GO | 48 | 3 | 1.05 | CBX2; CDYL2; UHRF1 | 4 | 0.98 | CBX7; CHD5; FAM156A; FAM156B | 0 | 0.00 | | 0 | 0.00 | | 1 | 0.53 | CBX7 | 2 | 1.18 | CBX2; CDYL2 |
| positive regulation of response to | 48 | 3 | 1.05 | CYP27B1; HIF1A; RALB | 1 | 0.25 | PRKAA2 | 0 | 0.00 | | 0 | 0.00 | | 2 | 1.06 | DCN; PRKAA2 | 2 | 1.18 | CYP27B1; HIF1A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| extracellular stimulus: GO | | | | | | | | | | | | | | | | | | | |
| regulation of steroid biosynthetic process: GO | 48 | 3 | 1.05 | CYP27B1; IFNG; IL1B | 7 | 1.72 | APOE; BMP5; CYP17A1; FGF1; LEP; NR5A1; PPARGC1A | 0 | 0.00 | | 1 | 8.71 | IL1B | 1 | 0.53 | PPARGC1A | 2 | 1.18 | CYP27B1; SNAI2 |
| transition metal ion homeostasis: GO | 100 | 12 | 2.01 | HIF1A; HMOX1; HMOX2; LCN2; LTF; MT2A; PRNP; S100A8; S100A9; SCO2; SLC39A6; STEAP4 | 10 | 1.18 | ALAS2; CP; CYBRD1; EPB42; HAMP; RHAG; SCARA5; SLC22A17; TF; TMPRSS6 | 0 | 0.00 | | 0 | 0.00 | | 6 | 1.52 | CP; CYBRD1; SCARA5; SLC22A17; SLC40A1; STEAP2 | 4 | 1.13 | HIF1A; HMOX2; LTF; SCO2 |
| motile cilium: GO | 100 | 5 | 0.84 | ANXA1; ENKUR; HIF1A; RAN; TXNDC8 | 10 | 1.18 | ACTL7A; CATSPERG; GSTM3; ODF3; ROPN1B; RSPH1; SPAG6; SPEF2; TEKT3; TSGA10 | 0 | 0.00 | | 0 | 0.00 | | 4 | 1.02 | CATSPERG; ROPN1B; SPATA6; SPEF2 | 4 | 1.13 | HIF1A; PTCHD3; RAN; SLC26A6 |
| nuclear pore: GO | 74 | 5 | 1.13 | EIF5A; EIF5AL1; KPNA2; MAD2L1; RAN | 0 | 0.00 | | 0 | 0.00 | | 0 | 0.00 | | 0 | 0.00 | | 3 | 1.15 | KPNA2; MAD2L1; RAN |
| odontogenesis of dentin containing tooth: GO | 74 | 5 | 1.13 | CA2; ITGA6; PERP; TNC; TP63 | 6 | 0.96 | AMELX; EDA; GLI2; HAND2; LRP4; WDR72 | 0 | 0.00 | | 0 | 0.00 | | 4 | 1.37 | FOXC1; GLI2; HAND2; WDR72 | 3 | 1.15 | CA2; ITGA6; ITGB4 |
| microvillus: GO | 74 | 4 | 0.90 | CA2; FSCN1; MSN; PDPN | 9 | 1.43 | ADCY6; AOC3; ATP6V1B1; CDHR5; | 0 | 0.00 | | 0 | 0.00 | | 3 | 1.03 | ANGPT1; FOXA1; MUC20 | 3 | 1.15 | CA2; MSN; S100P |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| ciliary basal body: GO | 74 | 2 | 0.45 | CENPF; POC1A | 3 | 0.48 | ESPN; GRXCR2; MUC20; MYO1A; SLC10A2 AGBL4; DZIP1L; PKHD1 | 0 | 0.00 | | 0 | 0.00 | | 1 | 0.34 | B9D1 | 3 | 1.15 | CENPF; CEP19; POC1A |
| response to sterol: GO | 23 | 5 | 3.64 | ACP5; CCL3; CCR5; LRP8; TGFBR1 | 4 | 2.05 | GPLD1; MLC1; PTCH1; RORC | 0 | 0.00 | | 0 | 0.00 | | 2 | 2.21 | GPLD1; PTCH1 | 1 | 1.23 | ACP5 |
| death receptor activity: GO | 23 | 4 | 2.91 | TNFRSF10A; TNFRSF21; TNFRSF4; TNFRSF9 | 0 | 0.00 | | 0 | 0.00 | | 0 | 0.00 | | 0 | 0.00 | | 1 | 1.23 | RELT |
| inflammatory response to antigenic stimulus: GO | 23 | 4 | 2.91 | AHCY; BDKRB2; IL1B; IL2RA | 1 | 0.51 | ELANE | 0 | 0.00 | | 2 | 36.34 | IL1B; IL2RA | 1 | 1.10 | ELANE | 1 | 1.23 | BDKRB2 |
| integrin a9b1 pathway | 23 | 4 | 2.91 | CSF2; KCNJ15; TGM2; TNC | 1 | 0.51 | NOS2 | 0 | 0.00 | | 0 | 0.00 | | 0 | 0.00 | | 1 | 1.23 | TGM2 |
| cytolysis: GO | 23 | 3 | 2.18 | BAK1; GZMA; LYZ | 4 | 2.05 | ALB; C6; C7; P2RX7 | 0 | 0.00 | | 2 | 36.34 | GZMB; LYZ | 0 | 0.00 | | 1 | 1.23 | BAK1 |
| nthi pathway | 23 | 3 | 2.18 | IL1B; MYD88; TGFBR1 | 0 | 0.00 | | 0 | 0.00 | | 1 | 18.17 | IL1B | 0 | 0.00 | | 1 | 1.23 | MYD88 |
| positive regulation of receptor internalization: GO | 23 | 3 | 2.18 | GREM1; PCSK9; SELE | 2 | 1.03 | HAMP; MAGI2 | 0 | 0.00 | | 1 | 18.17 | SELE | 1 | 1.10 | ANGPT1 | 1 | 1.23 | PCSK9 |
| prostate gland morphogenesis: GO | 23 | 3 | 2.18 | SERPINB5; TNC; TP63 | 4 | 2.05 | CRIP1; GLI2; ID4; NOG | 0 | 0.00 | | 0 | 0.00 | | 4 | 4.42 | CRIP1; ESR1; FOXA1; GLI2 | 1 | 1.23 | SERPINB5 |
| protein export | 23 | 3 | 2.18 | HSPA5; SEC61G; SRP9P1 | 0 | 0.00 | | 0 | 0.00 | | 0 | 0.00 | | 0 | 0.00 | | 1 | 1.23 | HSPA5 |
| regulation of camp mediated signaling: | 23 | 3 | 2.18 | CXCL10; CXCL11; | 2 | 1.03 | ADRB1; LHCGR | 0 | 0.00 | | 1 | 18.17 | CXCL9 | 0 | 0.00 | | 1 | 1.23 | CXCL11 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func- tional | A. Non-lesional vs lesional skin at baseline Up- regu- lated | Fold Change (FC) Up | Up- regulated Genes | Down- regu- lated | Fold Change (FC) | Down- regulated Genes | B. Differentially expressed genes significant in the baseline vs week 12 comparison only in the placebo Up- regu- lated | Fold Change (FC) Up | Up- regulated Genes | Down- regu- lated | Fold Change (FC) | Down- regulated Genes | C. Differentially expressed genes significant in the baseline vs week 12 comparison only in the nemo Up- regu- lated | Fold Change (FC) Up | Up- regulated Genes | Down- regu- lated | Fold Change (FC) | Down- regulated Genes |
|---|---|---|---|---|---|---|---|---|---|---|---|---|---|---|---|---|---|---|---|
| GO | | | | CXCL9 | | | | | | | | | | | | | | | |
| regulation of ifna signaling | 23 | 3 | 2.18 | IL6; SOCS3; STAT1 | 1 | 0.51 | IFNA5 | 0 | 0.00 | | 0 | 0.00 | | 0 | 0.00 | | 1 | 1.23 | SOCS3 |
| regulation of translational elongation: GO | 23 | | 2.18 | EIF4A3; EIF5A; EIF5AL1 | 0 | 0.00 | | 0 | 0.00 | | 0 | 0.00 | | 0 | 0.00 | | 1 | 1.23 | EIF4A3 |
| termination of translesion dna synthesis | 23 | 3 | 2.18 | ISG15; PCNA; USP43 | 0 | 0.00 | | 0 | 0.00 | | 1 | 18.17 | ISG15 | 0 | 0.00 | | 1 | 1.23 | USP43 |
| alcohol transmembrane transporter activity: GO | 23 | 2 | 1.46 | ABCG4; AQP3 | 2 | 1.03 | AQP4; AQP7 | 0 | 0.00 | | 1 | 18.17 | AQP9 | 0 | 0.00 | | 1 | 1.23 | AQP3 |
| blood coagulation fibrin clot formation: GO | 23 | 2 | 1.46 | C1QBP; F12 | 3 | 1.54 | F10; F7; KLKB1 | 0 | 0.00 | | 0 | 0.00 | | 1 | 1.10 | FBLN1 | 1 | 1.23 | F12 |
| endosome lumen: GO | 23 | 2 | 1.46 | CTSB; RAB38 | 2 | 1.03 | NAPSA; SFTPC | 0 | 0.00 | | 0 | 0.00 | | 0 | 0.00 | | 1 | 1.23 | RAB38 |
| fibroblast growth factor binding: GO | 23 | 2 | 1.46 | CXCL13; FGFBP1 | 2 | 1.03 | FGFR1; FGFR3 | 0 | 0.00 | | 0 | 0.00 | | 1 | 1.10 | FGFR1 | 1 | 1.23 | FGFBP1 |
| lysosome localization: GO | 23 | 2 | 1.46 | NR4A3; PLA2G3 | 1 | 0.51 | MAP6 | 0 | 0.00 | | 0 | 0.00 | | 0 | 0.00 | | 1 | 1.23 | PLA2G3 |
| mtor pathway | 23 | 2 | 1.46 | EIF4EBP1; EIF4G2 | 0 | 0.00 | | 0 | 0.00 | | 0 | 0.00 | | 0 | 0.00 | | 1 | 1.23 | EIF4EBP1 |
| negative regulation of calcium ion import: GO | 23 | 2 | 1.46 | GSTO1; NTSR1 | 5 | 2.56 | CASQ2; GSTM2; SLN; SPINK1; TRDN | 0 | 0.00 | | 0 | 0.00 | | 1 | 1.10 | TRDN | 1 | 1.23 | NTSR1 |
| negative regulation of myoblast differentiation: GO | 23 | 2 | 1.46 | CCL17; CXCL10 | 2 | 1.03 | MSTN; SOX8 | 0 | 0.00 | | 0 | 0.00 | | 1 | 1.10 | PRICKLE1 | 1 | 1.23 | PPARD |
| neurotrophin signaling pathway: GO | 23 | 2 | 1.46 | NGF; NTRK1 | 2 | 1.03 | MAGI2; NTRK3 | 0 | 0.00 | | 0 | 0.00 | | 0 | 0.00 | | 1 | 1.23 | NGF |
| nfkb pathway | 23 | 2 | 1.46 | IL1A; MYD88 | 0 | 0.00 | | 0 | 0.00 | | 0 | 0.00 | | 0 | 0.00 | | 1 | 1.23 | MYD88 |
| positive regulation of | 23 | 2 | 1.46 | HIF1A; ISG15 | 1 | 0.51 | GATA1 | 0 | 0.00 | | 1 | 18.17 | ISG15 | 0 | 0.00 | | 1 | 1.23 | HIF1A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| erythrocyte differentiation: GO | | | | | | | | | | | | | | | | | | | |
| proximal tubule bicarbonate reclamation | 23 | 2 | 1.46 | ATP1B3; CA2 | 4 | 2.05 | ATP1A2; FXYD2; PCK1; SLC4A4 | 0 | 0.00 | | 0 | 0.00 | | 2 | 2.21 | ATP1B2; SLC4A4 | 1 | 1.23 | CA2 |
| aspartate family amino acid biosynthetic process: GO | 23 | 1 | 0.73 | GOT2 | 1 | 0.51 | BHMT2 | 0 | 0.00 | | 0 | 0.00 | | 0 | 0.00 | | 1 | 1.23 | GOT2 |
| ccr3 pathway | 23 | 1 | 0.73 | CFL1 | 1 | 0.51 | NOX1 | 0 | 0.00 | | 0 | 0.00 | | 0 | 0.00 | | 1 | 1.23 | CFL1 |
| glycosylphos-phatidyl-inositol(gpi)-anchor biosynthesis | 23 | 1 | 0.73 | PIGW | 1 | 0.51 | GPLD1 | 0 | 0.00 | | 0 | 0.00 | | 1 | 1.10 | GPLD1 | 1 | 1.23 | PIGW |
| glyoxylate metabolism and glycine degradation | 23 | 1 | 0.73 | ALDH4A1 | 1 | 0.51 | HOGA1 | 0 | 0.00 | | 0 | 0.00 | | 0 | 0.00 | | 1 | 1.23 | GLDC |
| intrinsic prothrombin activation pathway | 23 | 1 | 0.73 | F12 | 2 | 1.03 | F10; KLKB1 | 0 | 0.00 | | 0 | 0.00 | | 0 | 0.00 | | 1 | 1.23 | F12 |
| myotube cell development: GO | 23 | 1 | 0.73 | HOMER1 | 2 | 1.03 | ACTA1; C16orf89 | 0 | 0.00 | | 0 | 0.00 | | 0 | 0.00 | | 1 | 1.23 | HOMER1 |
| nfkappab canonical pathway | 23 | 1 | 0.73 | RAN | 1 | 0.51 | SSPO | 0 | 0.00 | | 0 | 0.00 | | 0 | 0.00 | | 1 | 1.23 | RAN |
| nuclear transcribed mrna poly a tail shortening: GO | 23 | 1 | 0.73 | EIF4A3 | 0 | 0.00 | | 0 | 0.00 | | 0 | 0.00 | | 0 | 0.00 | | 1 | 1.23 | EIF4A3 |
| nucleocytoplasmic transporter activity: GO | 23 | 1 | 0.73 | RAN | 0 | 0.00 | | 0 | 0.00 | | 0 | 0.00 | | 0 | 0.00 | | 1 | 1.23 | RAN |
| podosome: GO | 23 | 1 | 0.73 | FSCN1 | 1 | 0.51 | GSN | 0 | 0.00 | | 0 | 0.00 | | 1 | 1.10 | RHOU | 1 | 1.23 | TPM4 |
| receptor signaling complex scaffold activity: GO | 23 | 1 | 0.73 | CD3E | 3 | 1.54 | MAGI2; ROPN1B; SHANK1 | 0 | 0.00 | | 0 | 0.00 | | 1 | 1.10 | ROPN1B | 1 | 1.23 | CARD10 |
| regulation of isotype switching: GO | 23 | 1 | 0.73 | IFNG | 0 | 0.00 | | 0 | 0.00 | | 0 | 0.00 | | 0 | 0.00 | | 1 | 1.23 | IL10 |
| rna polymerase iii transcription initiation | 23 | 1 | 0.73 | POLR3G | 0 | 0.00 | | 0 | 0.00 | | 0 | 0.00 | | 0 | 0.00 | | 1 | 1.23 | POLR3G |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| scf dependent proteasomal ubiquitin dependent protein catabolic process: GO | 23 | 1 | 0.73 | KIF14 | 0 | 0.00 | | 0 | 0.00 | | 0 | 0.00 | | 1 | 1.10 | FBXL7 | 1 | 1.23 | KIF14 |
| xenobiotics | 23 | 1 | 0.73 | CYP2S1 | 8 | 4.10 | CYP1A1; CYP1A2; CYP2A6; CYP2C9; CYP2D6; CYP2J2; CYP2W1; CYP3A5 | 0 | 0.00 | | 0 | 0.00 | | 3 | 3.31 | CYP2W1; CYP3A4; CYP3A5 | 1 | 1.23 | CYP2S1 |
| baf type complex: GO | 23 | 0 | 0.00 | | 0 | 0.00 | | 0 | 0.00 | | 0 | 0.00 | | 0 | 0.00 | | 1 | 1.23 | DPF1 |
| myofilament: GO | 23 | 0 | 0.00 | | 11 | 5.64 | ACTA1; LMOD1; MYOM1; TMOD1; TNNC1; TNNC2; TNNI2; TNNT2; TNNT3; TPM1; TPM2 | 0 | 0.00 | | 0 | 0.00 | | 4 | 4.42 | LMOD1; MYOM1; TNNC1; TNNT3 | 1 | 1.23 | TPM4 |
| phosphoinositides and their downstream targets. | 23 | 0 | 0.00 | | 0 | 0.00 | | 0 | 0.00 | | 0 | 0.00 | | 0 | 0.00 | | 1 | 1.23 | VAV2 |
| positive regulation of cellular response to transforming growth factor beta stimulus: GO | 23 | 0 | 0.00 | | 2 | 1.03 | ITGA8; MYOCD | 1 | 18.17 | CDKNIC | 0 | 0.00 | | 0 | 0.00 | | 1 | 1.23 | LRG1 |
| ptdins pathway | 23 | 0 | 0.00 | | 0 | 0.00 | | 0 | 0.00 | | 0 | 0.00 | | 0 | 0.00 | | 1 | 1.23 | VAV2 |
| tetrapyrrole binding: GO | 127 | 12 | 1.58 | CYCS; CYP24A1; | 26 | 2.42 | AMBP; CYGB; | 0 | 0.00 | | 1 | 3.29 | TDO2 | 8 | 1.60 | CYP2W1; CYP3A4; | 5 | 1.12 | CYCS; CYP27B1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | CYP27B1; CYP27C1; CYP2S1; CYP4F11; CYP4F22; HMOX1; IDO1; PTGS2; TCN1; TDO2 | | | CYP17A1; CYP1A1; CYP1A2; CYP21A2; CYP2A6; CYP2C9; CYP2D6; CYP2G1P; CYP2J2; CYP2W1; CYP3A5; CYP4A11; CYP4B1; CYP4F12; CYP4F8; CYP4X1; CYP4Z1; CYP4Z2P; FA2H; HBA1; HBA2; HBB; NOS2; PTGIS | | | | | | | | | CYP3A5; CYP4A11; CYP4B1; CYP4F12; HBA2; HBB | | | CYP27C1; CYP2S1; PTGS2 |
| carboxylic ester hydrolase activity: GO | 127 | 8 | 1.05 | ACOT7; CA2; LIPG; LYPLA1; NLGN4X; PLA2G3; PLA2G4D; PLBD1 | 16 | 1.49 | ACOT1; ACOT12; CA1; CES1; CES4A; LIPH; LPL; NLGN1; PLA2G16; PLA2G5; PLA2G6; PNPLA3; PNPLA7; PON1; PON3; TG | 2 | 6.58 | LPL; PLA2G16 | 0 | 0.00 | | 9 | 1.80 | AADACL2; CA1; CES1; CES4A; LIPH; LIPK; LIPM; PNPLA3; PON3 | 5 | 1.12 | ACOT7; CA2; NLGN4X; PLA2G3; PLA2G4D |
| regulation of t cell differentiation: GO | 101 | 17 | 2.82 | ANXA1; CD2; CD80; CTLA4; IFNG; IL12B; IL1B; IL2RA; IL36B; IL4R; IL6; IL7R; JAK3; PNP; | 3 | 0.35 | DTX1; GLI2; ZBTB16 | 0 | 0.00 | | 3 | 12.41 | IL1B; IL2RA; IL7R | 3 | 0.75 | GLI2; PIK3R6; SLC46A2 | 4 | 1.12 | CD83; HLA-G; PNP; PRELID1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | PRELID1; SASH3; TNFSF9 | | | | | | | | | | | | | | | |
| positive regulation of cyclic nucleotide metabolic process: GO | 101 | 9 | 1.49 | ADCYAP1; CAP1; CXCL10; CXCL11; CXCL9; GPR65; INSL3; PTHLH; WNT5A | 16 | 1.87 | ADCY2; ADCY5; ADCY6; ADCY8; ADRB1; AKAP12; APOE; CALCR; DRD1; GUCA1B; LHCGR; NOS2; OSTN; SCT; TSHR; VIPR2 | 1 | 4.14 | MRAP2 | 1 | 4.14 | CXCL9 | 3 | 0.75 | ADCYAP1R1; AKAP12; TSHR | 4 | 1.12 | CAP1; CXCL11; PTHLH; WNT5A |
| vesicle lumen: GO | 101 | 6 | 0.99 | CALR; HSPH1; LTF; SERPINA1; SERPINE1; SRGN | 15 | 1.75 | ACTN2; ALB; APOE; CFD; CLEC3B; CLU; EGF; HBA1; HBA2; HBB; PCSK2; RARRES2; SCGB3A2; TF; TIMP3 | 1 | 4.14 | CLEC3B | 1 | 4.14 | SERPINE1 | 7 | 1.76 | CLU; EGF; HBA2; HBB; ISLR; RARRES2; SCGB3A2 | 4 | 1.12 | ACTN1; HSPH1; LGALS3BP; LTF |
| response to retinoic acid: GO | 101 | 5 | 0.83 | AQP3; KRT13; TNC; TRIM16; WNT5A | 12 | 1.40 | CYP17A1; DKK1; DRD1; FZD4; LEP; LTK; NTRK3; OSR1; PTCH1; RBP4; RORB; WNT11 | 0 | 0.00 | | 0 | 0.00 | | 5 | 1.26 | FZD7; OSR1; PTCH1; TESC; WNT11 | 4 | 1.12 | AQP3; KRT13; WNT5A; WNT9B |
| brush border: GO | 101 | 4 | 0.66 | ACTR3; KCNK1; MYO1B; SLC5A1 | 14 | 1.64 | ATP6V0A4; CDHR5; CYBRD1; ESPN; FOLR1; MYH14; MYOIA; | 0 | 0.00 | | 0 | 0.00 | | 5 | 1.26 | ADD3; ATP6V0A4; CYBRD1; PTH1R; SCIN | 4 | 1.12 | ACTN1; KCNK1; MYO1B; SLC26A6 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | NPC1L1; PTH1R; SCIN; SLC34A3; SLC5A2; SLC7A9; SOAT2 | | | | | | | | | | | | |
| diencephalon development: GO | 75 | 4 | 0.89 | ADCYAP1; CNTNAP2; PITX1; WNT5A | 4 | 0.63 | GLI2; NOG; PAX6; SEMA3A | 0 | 0.00 | | 0 | 0.00 | | 1 | 0.34 | GLI2 | 3 | 1.13 | CNTNAP2; PITX1; WNT5A |
| rho guanyl nucleotide exchange factor activity: GO | 75 | 2 | 0.45 | ECT2; PLEKHG7 | 6 | 0.94 | ARHGEF19; ARHGEF25; ARHGEF26; MCF2L; OBSCN; PLEKHG5 | 0 | 0.00 | | 0 | 0.00 | | 4 | 1.36 | ARHGEF25; ARHGEF26; ARHGEF33; PREX2 | 3 | 1.13 | ARHGEF16; ECT2; VAV2 |
| positive regulation of transcription factor import into nucleus: GO | 49 | 5 | 1.71 | GREM1; IL12B; IL1B; PRKCQ; PTGS2 | 1 | 0.24 | EDA | 0 | 0.00 | | 1 | 8.53 | IL1B | 0 | 0.00 | | 2 | 1.16 | PRKCQ; PTGS2 |
| regulation of mitochondrial membrane potential: GO | 49 | 5 | 1.71 | BAK1; CCK; IFI6; PRELID1; VCP | 3 | 0.72 | BCL2; MYOC; P2RX7 | 0 | 0.00 | | 0 | 0.00 | | 3 | 1.56 | BCL2; DCN; MYOC | 2 | 1.16 | BAK1; PRELID1 |
| photoreceptor cell differentiation: GO | 49 | 4 | 1.37 | CNGB1; PRDM1; SDK2; TH | 4 | 0.96 | PAX6; RORB; SOX8; TRPM1 | 0 | 0.00 | | 0 | 0.00 | | 0 | 0.00 | | 2 | 1.16 | SDK2; TH |
| protein monoubiquitination: GO | 49 | 4 | 1.37 | DTL; DTX3L; UBE2T; UHRF1 | 0 | 0.00 | | 0 | 0.00 | | 0 | 0.00 | | 0 | 0.00 | | 2 | 1.16 | DTL; UBE2T |
| g protein coupled amine receptor activity: GO | 49 | 3 | 1.02 | HRH3; HTR3A; HTR7 | 14 | 3.37 | ADRA1A; ADRA1B; ADRA2A; ADRB1; CHRM1; CHRM2; CHRM3; CHRM4; HTR3E; | 0 | 0.00 | | 0 | 0.00 | | 4 | 2.07 | ADRA1A; ADRA2A; CHRM1; CHRM3 | 2 | 1.16 | HRH1; HRH2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | | | | HTR4; HTR6; OR56A1; OR56A4; OR56A5 | | | | | | | | | | | | |
| basal part of cell: GO | 49 | 2 | 0.68 | CLCA2; ITGA6 | 6 | 1.44 | CD34; MUC20; MYO1A; PHLDB1; SLC16A8; TF | 0 | 0.00 | | 0 | 0.00 | | 2 | 1.04 | CD34; MUC20 | 2 | 1.16 | CLCA2; ITGA6 |
| mechanoreceptor differentiation: GO | 49 | 2 | 0.68 | NTRK1; PLS3 | 7 | 1.69 | ATP2B2; CLIC5; FGFR1; GABRB3; MCOLN3; NTRK3; PDZD7 | 0 | 0.00 | | 0 | 0.00 | | 4 | 2.07 | CLIC5; FGFR1; PDZD7; SLITRK6 | 2 | 1.16 | SLC4A7; TMC1 |
| inorganic anion transport: GO | 128 | 4 | 0.52 | CLCA2; GABRQ; RACGAP1; SLC26A9 | 25 | 2.30 | ANO3; ANO5; ANO9; BEST2; BEST3; BEST4; CFTR; CLCNKA; CLCNKB; CLIC5; ENPP1; GABRA2; GABRB3; GABRG3; GABRP; GLRB; NMUR1; SLC17A4; SLC17A7; SLC26A1; SLC26A5; SLC26A7; SLC34A3; SLC4A1; TG | 0 | 0.00 | | 0 | 0.00 | | 6 | 1.19 | ANO9; CLCN4; CLIC5; ENPP3; GLRB; P2RY4 | 5 | 1.11 | CLCA2; SLC20A1; SLC26A6; SLC4A3; SLC5A5 |
| lipid homeostasis: GO | 102 | 6 | 0.98 | ABCA12; LDLR; LIPG; | 14 | 1.62 | ABCA2; ACADL; | 2 | 8.19 | GPAM; LPL | 0 | 0.00 | | 3 | 0.75 | ACOX2; DGAT2; | 4 | 1.11 | ANGPTL4; LDLR; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | MALL; PCSK9; PLSCR3 | | | ACOX2; APOE; EPHX2; FABP4; FITM2; GPAM; GPIHBP1; IRS2; LPL; MLXIPL; PRKAA2; SOAT2 | | | | | | | | | PRKAA2 | | | MALL; PCSK9 |
| developmental growth involved in morphogenesis: GO | 102 | 5 | 0.82 | AREG; AURKA; FLRT3; TNC; WNT5A | 12 | 1.39 | COBL; DCLK1; DCX; FGF1; MAGI2; MAPT; MESP1; PLXNA3; SEMA3A; SLIT2; SLIT3; WNT11 | 0 | 0.00 | | 0 | 0.00 | | 8 | 1.99 | DCLK1; ESR1; MAPT; MESP1; SLIT2; SLIT3; SPRY1; WNT11 | 4 | 1.11 | AREG; AURKA; FLRT3; WNT5A |
| protein n terminus binding: GO | 102 | 5 | 0.82 | EIF5A; NTSR1; UNC13A; YWHAQ; ZWINT | 4 | 0.46 | CLU; KCNIP2; SCT; SNCA | 0 | 0.00 | | 0 | 0.00 | | 4 | 1.00 | CLU; DCN; GLRX; SNCA | 4 | 1.11 | NTSR1; UNC13A; YWHAQ; ZWINT |
| positive regulation of nf kappab transcription factor activity: GO | 129 | 14 | 1.82 | GREM1; IL1B; IL6; LTF; NPM1; NTRK1; PRKCQ; PYCARD; S100A12; S100A8; S100A9; TRIM14; UBE2N; WNT5A | 5 | 0.46 | AGT; AR; CAMK2A; CLU; EDA | 0 | 0.00 | | 1 | 3.24 | IL1B | 1 | 0.20 | CLU | 5 | 1.10 | LTF; NPM1; PRKCQ; RPS6KA4; WNT5A |
| negative regulation of cell cell adhesion: GO | 129 | 13 | 1.69 | ANXA1; CCL21; CD274; | 4 | 0.37 | ADIPOQ; B4GALNT2; DTX1; | 1 | 3.24 | ADIPOQ | 1 | 3.24 | IL2RA | 2 | 0.39 | CXCL12; PRKG1 | 5 | 1.10 | HLA-G; IL10; SERPINE2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | CTLA4; IDO1; IL1RN; IL2RA; IL4R; JAK3; PRNP; SERPINE2; TNFRSF21; UBASH3B | | | SCGB1A1 | | | | | | | | | | | | SNAI2; UBASH3B |
| acetylcholine binding: GO | 24 | 4 | 2.79 | CHRNA3; CHRNA6; CHRNA9; HTR3A | 3 | 1.47 | CHRM3; CHRNA2; HTR3E | 0 | 0.00 | | 0 | 0.00 | | 1 | 1.06 | CHRM3 | 1 | 1.18 | CHRNA6 |
| cytokines and inflammatory response | 24 | 4 | 2.79 | CSF2; IFNG; IL1A; IL6 | 1 | 0.49 | IL5 | 0 | 0.00 | | 0 | 0.00 | | 0 | 0.00 | | 1 | 1.18 | IL10 |
| negative regulation of hematopoietic progenitor cell differentiation: GO | 24 | 4 | 2.79 | HIST1H4I; HIST1H4J; HIST1H4K; HIST1H4L | 0 | 0.00 | | 0 | 0.00 | | 0 | 0.00 | | 0 | 0.00 | | 1 | 1.18 | HIST1H4I |
| negative regulation of viral transcription: GO | 24 | 4 | 2.79 | CCL3; HMGA2; IFITM3; TRIM14 | 1 | 0.49 | POU2F3 | 0 | 0.00 | | 1 | 17.41 | IFITM3 | 0 | 0.00 | | 1 | 1.18 | HMGA2 |
| regulation of amino acid transport: GO | 24 | 4 | 2.79 | CCK; HRH3; IL1B; NTSR1 | 7 | 3.44 | ADORA1; ATP1A2; GRM7; LEP; NPY5R; P2RX7; SNCA | 0 | 0.00 | | 1 | 17.41 | IL1B | 1 | 1.06 | SNCA | 1 | 1.18 | NTSR1 |
| hsf1 activation | 24 | 3 | 2.09 | HSPA6; HSPH1; TNFRSF21 | 0 | 0.00 | | 0 | 0.00 | | 0 | 0.00 | | 1 | 1.06 | SLC29A1 | 1 | 1.18 | HSPH1 |
| isoprenoid biosynthetic process: GO | 24 | 3 | 2.09 | ALDH1A3; COQ2; HMGCR | 2 | 0.98 | CYP1A1; HMGCS2 | 0 | 0.00 | | 0 | 0.00 | | 1 | 1.06 | HMGCS2 | 1 | 1.18 | PDSS1 |
| cellular response to amino acid starvation: GO | 24 | 2 | 1.39 | CDKN1A; EIF2S1 | 0 | 0.00 | | 0 | 0.00 | | 0 | 0.00 | | 0 | 0.00 | | 1 | 1.18 | CDKN1A |
| eif4 pathway | 24 | 2 | 1.39 | EIF4EBP1; EIF4G2 | 1 | 0.49 | GHR | 1 | 17.41 | GHR | 0 | 0.00 | | 0 | 0.00 | | 1 | 1.18 | EIF4EBP1 |
| extrinsic | 24 | 2 | 1.39 | ANXA1; | 1 | 0.49 | SOX10 | 0 | 0.00 | | 0 | 0.00 | | 2 | 2.12 | ALDH3A2; | 1 | 1.18 | ZC3H12A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| component of organelle membrane: GO | | | | ZC3H12A | | | | | | | | | | | | MMP27 | | | |
| glutamine family amino acid catabolic process: GO | 24 | 2 | 1.39 | ALDH4A1; GOT2 | 2 | 0.98 | NOS2; PRODH | 0 | 0.00 | | 0 | 0.00 | | 1 | 1.06 | PRODH | 1 | 1.18 | GOT2 |
| hivnef pathway | 24 | 2 | 1.39 | LMNB1; LMNB2 | 1 | 0.49 | GSN | 0 | 0.00 | | 0 | 0.00 | | 0 | 0.00 | | 1 | 1.18 | LMNB2 |
| insulin like growth factor binding: GO | 24 | 2 | 1.39 | ESM1; WISP1 | 1 | 0.49 | WISP2 | 0 | 0.00 | | 0 | 0.00 | | 3 | 3.18 | CTGF; IGFBP5; WISP2 | 1 | 1.18 | IGFBP3 |
| negative regulation of oxidoreductase activity: GO | 24 | 2 | 1.39 | CYP27B1; GZMA | 2 | 0.98 | CNR1; SNCA | 0 | 0.00 | | 0 | 0.00 | | 1 | 1.06 | SNCA | 1 | 1.18 | CYP27B1 |
| nitrogen metabolism | 24 | 2 | 1.39 | CA2; HAL | 4 | 1.97 | CA1; CA11; CA3; CA6 | 0 | 0.00 | | 0 | 0.00 | | 4 | 4.23 | CA1; CA11; CA3; CA6 | 1 | 1.18 | CA2 |
| o-linked glycosylation of mucins | 24 | 2 | 1.39 | B3GNT3; B3GNT5 | 4 | 1.97 | GALNT16; MUC20; MUC6; MUCL1 | 0 | 0.00 | | 0 | 0.00 | | 3 | 3.18 | GALNT16; MUC20; MUCL1 | 1 | 1.18 | B3GNT5 |
| photoperiodism: GO | 24 | 2 | 1.39 | NMU; USP2 | 3 | 1.47 | CRY2; DRD4; PER1 | 0 | 0.00 | | 0 | 0.00 | | 1 | 1.06 | CRY2 | 1 | 1.18 | NMU |
| regulation of eif4e and p70 s6 kinase | 24 | 2 | 1.39 | EIF4EBP1; EIF4G2 | 1 | 0.49 | GHR | 1 | 17.41 | GHR | 0 | 0.00 | | 0 | 0.00 | | 1 | 1.18 | EIF4EBP1 |
| rhodopsin pathway | 24 | 2 | 1.39 | CNGB1; LRAT | 2 | 0.98 | GUCA1B; RGS9 | 0 | 0.00 | | 0 | 0.00 | | 0 | 0.00 | | 1 | 1.18 | LRAT |
| s1p s1p2 pathway | 24 | 2 | 1.39 | GNA15; GNAI3 | 1 | 0.49 | GNAZ | 0 | 0.00 | | 0 | 0.00 | | 0 | 0.00 | | 1 | 1.18 | GNA15 |
| steroid catabolic process: GO | 24 | 2 | 1.39 | CYP24A1; CYP27B1 | 3 | 1.47 | APOE; CYP1A2; HSD17B14 | 0 | 0.00 | | 0 | 0.00 | | 1 | 1.06 | CYP3A4 | 1 | 1.18 | CYP27B1 |
| cardiac epithelial to mesenchymal transition: GO | 24 | 1 | 0.70 | TGFBR1 | 1 | 0.49 | TMEM100 | 0 | 0.00 | | 0 | 0.00 | | 0 | 0.00 | | 1 | 1.18 | SNAI2 |
| control of skeletal myogenesis by hdac & calcium/calmodulin- | 24 | 1 | 0.70 | CAMK1G | 2 | 0.98 | CAMK1; HDAC5 | 0 | 0.00 | | 0 | 0.00 | | 1 | 1.06 | CAMK1 | 1 | 1.18 | CAMK1G |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| dependent kinase (camk) | | | | | | | | | | | | | | | | | | | |
| dna directed dna polymerase activity: GO | 24 | 1 | 0.70 | POLQ | 0 | 0.00 | | 0 | 0.00 | | 0 | 0.00 | | 0 | 0.00 | | 1 | 1.18 | POLQ |
| dna polymerase | 24 | 1 | 0.70 | POLQ | 0 | 0.00 | | 0 | 0.00 | | 0 | 0.00 | | 0 | 0.00 | | 1 | 1.18 | POLQ |
| ecm pathway | 24 | 1 | 0.70 | PFN1 | 1 | 0.49 | GSN | 0 | 0.00 | | 0 | 0.00 | | 0 | 0.00 | | 1 | 1.18 | PFN1 |
| ephrin receptor binding: GO | 24 | 1 | 0.70 | CDK5R1 | 1 | 0.49 | ANKS1B | 0 | 0.00 | | 0 | 0.00 | | 1 | 1.06 | EFNB3 | 1 | 1.18 | CDK5R1 |
| gastrulation with mouth forming second: GO | 24 | 1 | 0.70 | WNT5A | 1 | 0.49 | AMOT | 0 | 0.00 | | 0 | 0.00 | | 1 | 1.06 | CHRD | 1 | 1.18 | WNT5A |
| glycosylphos phatidyl-inositol gpi anchor biosynthesis | 24 | 1 | 0.70 | PIGW | 1 | 0.49 | GPLD1 | 0 | 0.00 | | 0 | 0.00 | | 1 | 1.06 | GPLD1 | 1 | 1.18 | PIGW |
| ionotropic glutamate receptor signaling pathway: GO | 24 | 1 | 0.70 | CDK5R1 | 8 | 3.93 | GRIA1; GRIA2; GRIA4; GRIK3; GRIK4; GRIK5; GRIN1; GRIN2A | 1 | 17.41 | GRIA4 | 0 | 0.00 | | 3 | 3.18 | GRIA1; GRIA2; GRIK3 | 1 | 1.18 | CDK5R1 |
| ketone biosynthetic process: GO | 24 | 1 | 0.70 | COQ2 | 2 | 0.98 | CACNA1H; LHB | 0 | 0.00 | | 0 | 0.00 | | 1 | 1.06 | CACNA1H | 1 | 1.18 | PDSS1 |
| mapk targets/ nuclear events mediated by map kinases | 24 | 1 | 0.70 | DUSP6 | 0 | 0.00 | | 0 | 0.00 | | 0 | 0.00 | | 0 | 0.00 | | 1 | 1.18 | DUSP6 |
| mitotic g2 g2 m phases | 24 | 1 | 0.70 | PKMYT1 | 1 | 0.49 | TUBB4A | 0 | 0.00 | | 0 | 0.00 | | 0 | 0.00 | | 1 | 1.18 | PKMYT1 |
| positive regulation of dna templated transcription initiation: GO | 24 | 1 | 0.70 | FOSL1 | 2 | 0.98 | MITF; NKX2-5 | 0 | 0.00 | | 0 | 0.00 | | 1 | 1.06 | MITF | 1 | 1.18 | FOSL1 |
| regulation of execution | 24 | 1 | 0.70 | ZC3H12A | 2 | 0.98 | PTGIS; TBX5 | 0 | 0.00 | | 0 | 0.00 | | 1 | 1.06 | DLC1 | 1 | 1.18 | ZC3H12A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| phase of apoptosis: GO | | | | | | | | | | | | | | | | | | | |
| response to interleukin 6: GO | 24 | 1 | 0.70 | IL6 | 3 | 1.47 | ALDOB; PPARGC1A; PTGIS | 0 | 0.00 | | 0 | 0.00 | | 1 | 1.06 | PPARGC1A | 1 | 1.18 | SBNO2 |
| rna modification: GO | 24 | 1 | 0.70 | NOP10 | 0 | 0.00 | | 0 | 0.00 | | 0 | 0.00 | | 0 | 0.00 | | 1 | 1.18 | NOP56 |
| startle response: GO | 24 | 1 | 0.70 | NRG1 | 8 | 3.93 | DRD1; FABP7; GLRB; GRIN1; GRIN2A; KCNA1; NPAS1; NRXN1 | 0 | 0.00 | | 0 | 0.00 | | 3 | 3.18 | GLRB; NRXN1; SLITRK6 | 1 | 1.18 | NRG1 |
| sumoylation of rna binding proteins | 24 | 1 | 0.70 | CBX2 | 0 | 0.00 | | 0 | 0.00 | | 0 | 0.00 | | 0 | 0.00 | | 1 | 1.18 | CBX2 |
| b cell receptor complexes | 24 | 0 | 0.00 | | 0 | 0.00 | | 0 | 0.00 | | 0 | 0.00 | | 0 | 0.00 | | 1 | 1.18 | VAV2 |
| c21 steroid hormone metabolic process: GO | 24 | 0 | 0.00 | | 3 | 1.47 | CACNA1H; CYP17A1; LHB | 0 | 0.00 | | 0 | 0.00 | | 1 | 1.06 | CACNA1H | 1 | 1.18 | DHRS2 |
| centriolar satellite: GO | 24 | 0 | 0.00 | | 1 | 0.49 | ALDOB | 0 | 0.00 | | 0 | 0.00 | | 0 | 0.00 | | 1 | 1.18 | SPAG5 |
| epithelial cell apoptotic process: GO | 24 | 0 | 0.00 | | 1 | 0.49 | GSN | 0 | 0.00 | | 0 | 0.00 | | 0 | 0.00 | | 1 | 1.18 | E2F1 |
| regulation of anoikis: GO | 24 | 0 | 0.00 | | 2 | 0.98 | BCL2; PDK4 | 0 | 0.00 | | 0 | 0.00 | | 2 | 2.12 | BCL2; PDK4 | 1 | 1.18 | SNAI2 |
| signaling by bmp | 24 | 0 | 0.00 | | 3 | 1.47 | CHRDL1; GREM2; NOG | 0 | 0.00 | | 0 | 0.00 | | 1 | 1.06 | GREM2 | 1 | 1.18 | BMPR1B |
| vitamin binding: GO | 76 | 6 | 1.32 | ADH7; CRABP2; LRAT; OGDHL; PYGL; TCN1 | 5 | 0.78 | FOLR1; FOLR2; P4HTM; RBP4; TTPA | 0 | 0.00 | | 0 | 0.00 | | 1 | 0.33 | P4HTM | 3 | 1.12 | CRABP2; LRAT; OGDHL |
| intercalated disc: GO | 50 | 5 | 1.67 | CXADR; DSC2; DSP; GJA1; JUP | 5 | 1.18 | ANK2; ATP1A2; CTNNA3; DES; PGM5 | 0 | 0.00 | | 0 | 0.00 | | 1 | 0.51 | PGM5 | 2 | 1.13 | ACTN1; DSC2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| negative regulation of chemotaxis: GO | 50 | 4 | 1.34 | CXCL13; GREM1; SEMA4B; WNT5A | 8 | 1.89 | ELANE; PLXNA3; SEMA3A; SEMA3B; SEMA3D; SEMA3E; SEMA3G; SLIT2 | 0 | 0.00 | | 0 | 0.00 | | 4 | 2.03 | ELANE; SEMA3E; SEMA4G; SLIT2 | 2 | 1.13 | SEMA4B; WNT5A |
| protein complex localization: GO | 50 | 4 | 1.34 | BIRC5; DYNLL1; EXOC3L2; RAN | 1 | 0.24 | STXBP6 | 0 | 0.00 | | 0 | 0.00 | | 1 | 0.51 | STXBP6 | 2 | 1.13 | BIRC5; RAN |
| regulation of blood vessel endothelial cell migration: GO | 50 | 2 | 0.67 | PTGS2; SH3BGRL3 | 4 | 0.94 | AMOT; ANGPT4; APOE; HDAC5 | 0 | 0.00 | | 0 | 0.00 | | 3 | 1.52 | ANGPT1; ANGPT4; FGF2 | 2 | 1.13 | EPHA2; PTGS2 |
| signaling by ils | 103 | 17 | 2.76 | CDK1; CSF2; IL1A; IL1B; ILIR2; IL1RAP; IL1RN; IL2RA; IL6; IL7R; JAK3; MYD88; NRAS; SOCS3; STAT1; UBE2N; YWHAZ | 2 | 0.23 | IL5; PELI2 | 0 | 0.00 | | 3 | 12.17 | IL1B; IL2RA; IL7R | 1 | 0.25 | PELI2 | 4 | 1.10 | CDK1; MYD88; SOCS3; YWHAZ |
| odontogenesis: GO | 103 | 8 | 1.30 | ALPL; AQP3; CA2; ITGA6; PERP; SDC1; TNC; TP63 | 8 | 0.92 | AMELX; EDA; GLI2; HAND2; LRP4; OSR1; OSR2; WDR72 | 0 | 0.00 | | 0 | 0.00 | | 5 | 1.23 | FOXCI; GLI2; HAND2; OSR1; WDR72 | 4 | 1.10 | AQP3; CA2; ITGA6; ITGB4 |
| platelet degranulation: GO | 103 | 4 | 0.65 | SERPINA1; SERPINE1; SRGN; TUBA4A | 11 | 1.26 | ACTN2; ALB; CFD; CLEC3B; CLU; EGF; P2RX1; POTEKP; | 1 | 4.06 | CLEC3B | 1 | 4.06 | SERPINE1 | 5 | 1.23 | CLU; EGF; ISLR; POTEKP; RARRES2 | 4 | 1.10 | ACTN1; LGALS3BP; PCDH7; TUBA4A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | | | | RARRES2; TF; TIMP3 | | | | | | | | | | | | |
| ubiquitin mediated proteolysis | 130 | 7 | 0.90 | CDC20; SOCS3; UBA6; UBE2C; UBE2F; UBE2N; UBE2S | 1 | 0.09 | DET1 | 0 | 0.00 | | 0 | 0.00 | | 0 | 0.00 | | 5 | 1.09 | CDC20; SOCS3; UBE2C; UBE2F; UBE2S |
| hormone metabolic process: GO | 157 | 13 | 1.39 | ADH7; AKRIB15; ALDH1A3; CRABP2; FOXE1; GCNT4; IL1B; KLK6; LRAT; NGF; SDR16C5; UGT1A1; UGT1A7 | 19 | 1.43 | AGT; ALDH1A1; AWAT2; CACNA1H; CYP17A1; CYP1A1; CYP21A2; DIO3; HSD17B14; LEP; LHB; NR5A1; PCSK2; PCSK5; PPARGC1A; RBP4; REN; TG; UGT2B7 | 0 | 0.00 | | 1 | 2.66 | IL1B | 10 | 1.62 | CACNA1H; CORIN; CPE; CTSG; CYP3A4; DGAT2; ESR1; FOXA1; PPARGC1A; SULT1E1 | 6 | 1.08 | CRABP2; DHRS2; FOXE1; LRAT; NGF; SLC5A5 |
| positive regulation of lymphocyte differentiation: GO | 77 | 14 | 3.04 | ANXA1; CD80; IFNG; IL12B; IL1B; IL2RA; IL36B; IL4R; IL6; IL7R; PNP; PRDM1; SASH3; TNFSF9 | 3 | 0.46 | FLT3LG; GLI2; ZBTB16 | 0 | 0.00 | | 3 | 16.28 | IL1B; IL2RA; IL7R | 2 | 0.66 | GLI2; PIK3R6 | 3 | 1.10 | CD83; HLA-G; PNP |
| regulation of protein maturation: GO | 77 | 6 | 1.30 | BIRC5; CIQBP; CHAC1; F12; SERPINE1; SERPINE2 | 12 | 1.84 | BIRC7; C3; C4BPA; C6; C7; CCBE1; CFH; CLEC3B; GSN; KLKB1; NOL3; | 1 | 5.43 | CLEC3B | 1 | 5.43 | SERPINE1 | 3 | 0.99 | C3; CCBE1; CFH | 3 | 1.10 | BIRC5; F12; SERPINE2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | USP17L2 | | | | | | | | | | | | |
| bone morphogenesis: GO | 77 | 3 | 0.65 | ACP5; ALPL; LTF | 4 | 0.61 | FGFR3; FREM1; OSR2; SP5 | 0 | 0.00 | | 0 | 0.00 | | 3 | 0.99 | FREM1; SHOX2; SP5 | 3 | 1.10 | ACP5; BMPR1B; LTF |
| trans golgi network membrane: GO | 77 | 3 | 0.65 | AP1S3; MYO1B; RAB31 | 5 | 0.77 | CABP7; CLVS1; CLVS2; LGR5; RHOBTB3 | 0 | 0.00 | | 0 | 0.00 | | 3 | 0.99 | HLA-DQB2; LGR5; RHOBTB3 | 3 | 1.10 | AP1S3; MYO1B; RAB31 |
| aminoglycan biosynthetic process: GO | 104 | 8 | 1.29 | B3GNT3; CHST1; HAS3; HS3ST1; HS3ST3A1; HS3ST3B1; IL1B; SDC1 | 14 | 1.59 | BCAN; CHST12; CHST5; EXTL1; GPC2; GPC3; GPC6; HAS1; HS3ST2; HS3ST5; HS3ST6; PRELP; SDC2; UST | 0 | 0.00 | | 1 | 4.02 | IL1B | 6 | 1.47 | ANGPT1; CHST12; DCN; DSEL; GPC2; UST | 4 | 1.09 | AGRN; CHST1; HS3ST1; HS3ST3A1 |
| glycerophos-pholipid biosynthesis | 104 | 6 | 0.97 | AGPAT5; MBOAT2; PITPNM1; PLA2G3; PLA2G4D; PLBD1 | 8 | 0.91 | ACP6; CHPT1; GPAM; GPD1; PLA2G16; PLA2G5; PLA2G6; PNPLA3 | 3 | 12.05 | GPAM; GPD1; PLA2G16 | 0 | 0.00 | | 3 | 0.73 | ACP6; DGAT2; PNPLA3 | 4 | 1.09 | LPCAT1; PITPNM1; PLA2G3; PLA2G4D |
| single fertilization: GO | 104 | 5 | 0.80 | CCT2; CCT3; CCT5; CCT7; CDK1 | 10 | 1.13 | CATSPERG; GLRB; HSPA1L; KCNU1; NPM2; ROPN1B; SERPINA5; SYT8; TNP1; WBP2NL | 0 | 0.00 | | 0 | 0.00 | | 5 | 1.22 | CATSPERG; GLRB; HOXA10; PLCZ1; ROPN1B | 4 | 1.09 | CCT2; CCT5; CDK1; PLCD4 |
| stem cell differentiation: GO | 185 | 13 | 1.18 | EOMES; FAM83D; GDNF; GREM1; | 25 | 1.59 | ALX1; AMELX; BCL2; EDN3; ERBB4; | 0 | 0.00 | | 0 | 0.00 | | 11 | 1.51 | BCL2; EDN3; ERBB4; FGFR1; FOXA1; | 7 | 1.07 | HIF1A; HMGA2; NRG1; SEMA4B; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | HIF1A; HMGA2; NRG1; SEMA4B; STAT1; TGFBR1; TP63; WNT5A; WNT7A | | | FGFR1; FOLR1; FRZB; GSC; HAND2; LIF; MYOCD; NOG; OSR1; PAX3; SEMA3A; SEMA3B; SEMA3D; SEMA3E; SEMA3G; SOX10; SOX8; TCF21; TMEM100; WNT11 | | | | | | | | | FOXC1; HAND2; OSR1; SEMA3E; SEMA4G; WNT11 | | | SNAI2; WNT5A; WNT7A |
| extrinsic component of plasma membrane: GO | 131 | 11 | 1.41 | ANXA1; ENO1; GNA15; GNAI3; GNGT2; JAK3; JUP; PCSK9; RACGAP1; RGS1; SERPINE2 | 9 | 0.81 | DTNA; GNAZ; KCNIP1; MCF2L; RGS11; RGS6; RGS9; SCUBE1; TF | 1 | 3.19 | RGS11 | 0 | 0.00 | | 1 | 0.19 | GNG11 | 5 | 1.08 | ENO1; GNA15; PCSK9; RGS1; SERPINE2 |
| nfat and hypertrophy of the heart (transcription in the broken heart) | 51 | 4 | 1.31 | CALR; CAMK1G; CSNK1A1; HBEGF | 6 | 1.39 | ACTA1; AGT; CAMK1; HAND2; NKX2-5; PRKAR2B | 1 | 8.19 | PRKAR2B | 0 | 0.00 | | 3 | 1.49 | CAMK1; FGF2; HAND2 | 2 | 1.11 | CAMK1G; HBEGF |
| caspase pathway | 51 | 3 | 0.98 | CYCS; LMNB1; LMNB2 | 4 | 0.93 | ACTA1; BCL2; GAS2; GSN | 0 | 0.00 | | 1 | 8.19 | GZMB | 1 | 0.50 | BCL2 | 2 | 1.11 | CYCS; LMNB2 |
| neural crest cell migration: GO | 51 | 3 | 0.98 | GDNF; HIF1A; SEMA4B | 11 | 2.54 | EDN3; ERBB4; FOLR1; HAND2; SEMA3A; SEMA3B; SEMA3D; | 0 | 0.00 | | 0 | 0.00 | | 5 | 2.49 | EDN3; ERBB4; HAND2; SEMA3E; SEMA4G | 2 | 1.11 | HIF1A; SEMA4B |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | SEMA3E; SEMA3G; SOX10; SOX8 | | | | | | | | | | | | |
| neuron projection extension: GO | 51 | 2 | 0.66 | AURKA; FLRT3 | 7 | 1.62 | DCLK1; DCX; MAPT; PLXNA3; SEMA3A; SLIT2; SLIT3 | 0 | 0.00 | | 0 | 0.00 | | 4 | 1.99 | DCLK1; MAPT; SLIT2; SLIT3 | 2 | 1.11 | AURKA; FLRT3 |
| neuronal postsynaptic density: GO | 51 | 2 | 0.66 | HOMER1; P2RY1 | 11 | 2.54 | CAMK2A; CLSTN2; CNKSR2; DCLK1; DLG2; DLGAP1; GRIN1; GRIN2A; NLGN1; PALM; SHANK1 | 0 | 0.00 | | 0 | 0.00 | | 5 | 2.49 | ADD3; CNKSR2; DCLK1; DLG2; PALM | 2 | 1.11 | HOMER1; P2RY1 |
| ptp1b pathway | 51 | 2 | 0.66 | SOCS3; TXN | 4 | 0.93 | EGF; LEP; LEPR; TRPV6 | 0 | 0.00 | | 0 | 0.00 | | 1 | 0.50 | EGF | 2 | 1.11 | SOCS3; TXN |
| natural killer cell mediated immunity: GO | 25 | 7 | 4.69 | PRDX1; RAET1E; RAET1L; SLAMF7; ULBP1; ULBP2; ULBP3 | 2 | 0.94 | CLEC2A; KLRF2 | 0 | 0.00 | | 1 | 16.72 | GZMB | 1 | 1.02 | KLRF2 | 1 | 1.13 | RAET1L |
| regulation of neutrophil chemotaxis: GO | 25 | 6 | 4.02 | C1QBP; CCL21; CXCL1; CXCL3; IL1B; RAC2 | 1 | 0.47 | SLIT2 | 0 | 0.00 | | 2 | 33.43 | IL1B; RAC2 | 1 | 1.02 | SLIT2 | 1 | 1.13 | CXCL2 |
| myeloid dendritic cell activation: GO | 25 | 4 | 2.68 | CSF2; PYCARD; SLAMF1; TNFSF9 | 0 | 0.00 | | 0 | 0.00 | | 0 | 0.00 | | 0 | 0.00 | | 1 | 1.13 | DHRS2 |
| inactivation of mapk activity: GO | 25 | 3 | 2.01 | DUSP14; DUSP6; DUSP9 | 0 | 0.00 | | 0 | 0.00 | | 0 | 0.00 | | 0 | 0.00 | | 1 | 1.13 | DUSP6 |
| negative | 25 | 3 | 2.01 | HRH3; IL1B; | 7 | 3.30 | ADORA1; | 0 | 0.00 | | 1 | 16.72 | IL1B | 2 | 2.03 | ADRA2A; | 1 | 1.13 | P2RY1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| regulation of amine transport: GO | | | | P2RY1 | | | ADRA2A; CNR1; GRM7; LEP; NPY5R; SNCA | | | | | | | | | SNCA | | | |
| negative regulation of smoothened signaling pathway: GO | 25 | 3 | 2.01 | CD3E; SALL3; SERPINE2 | 4 | 1.89 | GPC3; HHIP; PTCH1; PTCH2 | 0 | 0.00 | | 0 | 0.00 | | 3 | 3.05 | CHRD; PTCH1; PTCH2 | 1 | 1.13 | SERPINE2 |
| toll endogenous pathway | 25 | 3 | 2.01 | MYD88; S100A8; S100A9 | 0 | 0.00 | | 0 | 0.00 | | 0 | 0.00 | | 0 | 0.00 | | 1 | 1.13 | MYD88 |
| 1- and 2-methyl-naphthalene degradation | 25 | 2 | 1.34 | ADH7; ESCO2 | 4 | 1.89 | ADH1B; ADH1C; ADHFE1; PNPLA3 | 0 | 0.00 | | 0 | 0.00 | | 1 | 1.02 | PNPLA3 | 1 | 1.13 | DHRS2 |
| golgi to plasma membrane protein transport: GO | 25 | 2 | 1.34 | RAB10; RAB31 | 0 | 0.00 | | 0 | 0.00 | | 0 | 0.00 | | 0 | 0.00 | | 1 | 1.13 | RAB31 |
| neutral lipid catabolic process: GO | 25 | 2 | 1.34 | FABP5; FABP6 | 5 | 2.36 | APOE; FABP4; FABP7; LPL; PNPLA3 | 1 | 16.72 | LPL | 0 | 0.00 | | 1 | 1.02 | PNPLA3 | 1 | 1.13 | FABP5 |
| positive regulation of tissue remodeling: GO | 25 | 2 | 1.34 | CA2; IL12B | 0 | 0.00 | | 0 | 0.00 | | 0 | 0.00 | | 0 | 0.00 | | 1 | 1.13 | CA2 |
| postsynaptic membrane organization: GO | 25 | 2 | 1.34 | GDNF; LRRC4 | 7 | 3.30 | APOE; GLRB; LRP4: MAGI2; NLGN1; NRXN1; RELN | 0 | 0.00 | | 0 | 0.00 | | 3 | 3.05 | GLRB; NRXN1; RELN | 1 | 1.13 | LRRC4 |
| regulation of lamellipodium assembly: GO | 25 | 2 | 1.34 | FSCN1; RAC2 | 2 | 0.94 | FRMD7; SLIT2 | 0 | 0.00 | | 1 | 16.72 | RAC2 | 1 | 1.02 | SLIT2 | 1 | 1.13 | EPHA2 |
| cul4 ring e3 ubiquitin ligase complex: | 25 | 1 | 0.67 | DTL | 0 | 0.00 | | 0 | 0.00 | | 0 | 0.00 | | 0 | 0.00 | | 1 | 1.13 | DTL |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| GO | | | | | | | | | | | | | | | | | | | |
| effects of pip2 hydrolysis | 25 | 1 | 0.67 | PRKCQ | 1 | 0.47 | DGKG | 0 | 0.00 | | 0 | 0.00 | | 0 | 0.00 | | 1 | 1.13 | PRKCQ |
| heart trabecula morphogenesis: GO | 25 | 1 | 0.67 | NRG1 | 2 | 0.94 | NKX2-5; RBP4 | 0 | 0.00 | | 0 | 0.00 | | 0 | 0.00 | | 1 | 1.13 | NRG1 |
| membrane assembly: GO | 25 | 1 | 0.67 | NLGN4X | 5 | 2.36 | IL1RAPL1; LRP4; MAGI2; NLGN1; NRXN1 | 0 | 0.00 | | 0 | 0.00 | | 1 | 1.02 | NRXN1 | 1 | 1.13 | NLGN4X |
| neurotransmitter metabolic process: GO | 25 | 1 | 0.67 | TH | 2 | 0.94 | GCHFR; MAOA | 0 | 0.00 | | 0 | 0.00 | | 1 | 1.02 | ALDH5A1 | 1 | 1.13 | TH |
| oncogene induced senescence | 25 | 1 | 0.67 | E2F3 | 0 | 0.00 | | 0 | 0.00 | | 0 | 0.00 | | 0 | 0.00 | | 1 | 1.13 | E2F1 |
| oxidoreductase activity acting on paired donors with incorporation or reduction of molecular oxygen reduced flavin or flavoprotein as one donor and incorporation of one atom of oxygen: GO | 25 | 1 | 0.67 | CYP2S1 | 11 | 5.19 | CYP1A1; CYP1A2; CYP2A6; CYP2D6; CYP2J2; CYP3A5; CYP4B1; CYP4F12; CYP4F8; CYP4X1; CYP4Z1 | 0 | 0.00 | | 0 | 0.00 | | 4 | 4.07 | CYP3A4; CYP3A5; CYP4B1; CYP4F12 | 1 | 1.13 | CYP2S1 |
| pigment cell differentiation: GO | 25 | 1 | 0.67 | RAB38 | 5 | 2.36 | BCL2; EDN3; MITF; OCA2; SOX10 | 0 | 0.00 | | 0 | 0.00 | | 3 | 3.05 | BCL2; EDN3; MITF | 1 | 1.13 | RAB38 |
| positive regulation of blood vessel endothelial cell migration: GO | 25 | 1 | 0.67 | PTGS2 | 2 | 0.94 | AMOT; ANGPT4 | 0 | 0.00 | | 0 | 0.00 | | 3 | 3.05 | ANGPT1; ANGPT4; FGF2 | 1 | 1.13 | PTGS2 |
| positive regulation of transcription | 25 | 1 | 0.67 | HIF1A | 2 | 0.94 | PPARGC1A; RXRG | 0 | 0.00 | | 0 | 0.00 | | 1 | 1.02 | PPARGC1A | 1 | 1.13 | HIF1A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| from rna polymerase ii promoter involved in cellular response to chemical stimulus: GO | | | | | | | | | | | | | | | | | | | |
| pre-notch expression and processing | 25 | 1 | 0.67 | E2F3 | 0 | 0.00 | | 0 | 0.00 | | 0 | 0.00 | | 0 | 0.00 | | 1 | 1.13 | E2F1 |
| regulation of hormone metabolic process: GO | 25 | 1 | 0.67 | HIF1A | 3 | 1.42 | BMP5; CYP17A1; PPARGC1A | 0 | 0.00 | | 0 | 0.00 | | 1 | 1.02 | PPARGC1A | 1 | 1.13 | HIF1A |
| regulation of mrna catabolic process: GO | 25 | 1 | 0.67 | ZC3H12A | 0 | 0.00 | | 0 | 0.00 | | 0 | 0.00 | | 0 | 0.00 | | 1 | 1.13 | ZC3H12A |
| regulation of necrotic cell death: GO | 25 | 11 | 0.67 | PPIF | 1 | 0.47 | NOL3 | 0 | 0.00 | | 0 | 0.00 | | 0 | 0.00 | | 1 | 1.13 | PPIF |
| substrate dependent cell migration: GO | 25 | 1 | 0.67 | TNFRSF12A | 3 | 1.42 | FGFR1; SEMA3A; SLIT2 | 0 | 0.00 | | 0 | 0.00 | | 3 | 3.05 | FGFR1; ITGA11; SLIT2 | 1 | 1.13 | SNAI2 |
| thyroid gland development: GO | 25 | 1 | 0.67 | FOXE1 | 3 | 1.42 | NKX2-5; SIX1; TG | 0 | 0.00 | | 0 | 0.00 | | 0 | 0.00 | | 1 | 1.13 | FOXE1 |
| toll-like receptor pathway | 25 | 1 | 0.67 | MYD88 | 0 | 0.00 | | 0 | 0.00 | | 0 | 0.00 | | 0 | 0.00 | | 1 | 1.13 | MYD88 |
| transcriptional activator activity rna polymerase ii distal enhancer sequence specific binding: GO | 25 | 1 | 0.67 | SUB1 | 1 | 0.47 | MEOX2 | 0 | 0.00 | | 0 | 0.00 | | 1 | 1.02 | MEOX2 | 1 | 1.13 | SUB1 |
| vasodilation: GO | 25 | 1 | 0.67 | BDKRB2 | 5 | 2.36 | ADORA1; ADRB1; AGT; APOE; DRD1 | 0 | 0.00 | | 0 | 0.00 | | 1 | 1.02 | PRKG1 | 1 | 1.13 | BDKRB2 |
| mhc protein complex: GO | 25 | 0 | 0.00 | | 0 | 0.00 | | 0 | 0.00 | | 0 | 0.00 | | 1 | 1.02 | HLA-DQB2 | 1 | 1.13 | HLA-G |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| negative regulation of intrinsic apoptotic signaling pathway in response to dna damage: GO | 25 | 0 | 0.00 | | 1 | 0.47 | CLU | 0 | 0.00 | | 0 | 0.00 | | 2 | 2.03 | CLU; CXCL12 | 1 | 1.13 | SNAI2 |
| schwann cell development: GO | 25 | 0 | 0.00 | | 5 | 2.36 | ADAM22; FA2H; LAMA2; LGI4; MYOC | 0 | 0.00 | | 0 | 0.00 | | 4 | 4.07 | ADAM22; LAMA2; LGI4; MYOC | 1 | 1.13 | NDRG1 |
| syncytium formation: GO | 25 | 0 | 0.00 | | 2 | 0.94 | CACNA1H; CDON | 0 | 0.00 | | 0 | 0.00 | | 2 | 2.03 | CACNA1H; CDON | 1 | 1.13 | SBNO2 |
| regulation of jun kinase activity: GO | 78 | 5 | 1.07 | GSTP1; IL1B; MDFI; SERPINB3; WNT5A | 5 | 0.76 | BIRC7; FZD4; FZD8; MAPK8IP1; TNXB | 0 | 0.00 | | 1 | 5.36 | IL1B | 0 | 0.00 | | 3 | 1.09 | GSTP1; MDFI; WNT5A |
| nuclease activity: GO | 186 | 10 | 0.90 | AEN; DNASEIL3; EXO1; GEN1; HMGA2; ISG20; NME1; RNASE7; RPP40; ZC3H12A | 4 | 0.25 | DNASE1L2; ENPP1; EXD3; NEIL1 | 0 | 0.00 | | 0 | 0.00 | | 2 | 0.27 | ENPP3; EXD3 | 7 | 1.07 | DNASE1L3; EXO1; FEN1; HMGA2; NEIL3; TREX2; ZC3H12A |
| regulation of rho protein signal transduction: GO | 105 | 4 | 0.64 | ECT2; F2RL1; ITGA3; PLEKHG7 | 9 | 1.01 | ADRA1A; APOE; ARHGEF19; ARHGEF25; ARHGEF26; MCF2L; MYOC; OBSCN; PLEKHG5 | 0 | 0.00 | | 0 | 0.00 | | 8 | 1.94 | ADRA1A; ARHGEF25; ARHGEF26; ARHGEF33; DLC1; LPAR1; MYOC; PREX2 | 4 | 1.08 | ARHGEF16; ECT2; ITGA3; VAV2 |
| positive regulation of stress activated protein kinase signaling cascade: GO | 132 | 12 | 1.52 | CCL21; F2RL1; HMGCR; IL1A; IL1B; IL26; MDFI; PYCARD; SLAMF1; | 5 | 0.45 | BIRC7; FZD4; FZD8; LEP; NOX1 | 0 | 0.00 | | 1 | 3.17 | IL1B | 2 | 0.38 | CTGF; FZD7 | 5 | 1.07 | MDFI; WNT5A; WNT7A; XDH; ZC3H12A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | WNT5A; WNT7A; ZC3H12A | | | | | | | | | | | | | | | |
| regulation of response to cytokine stimulus: GO | 132 | 11 | 1.39 | F2RL1; GSTP1; HIF1A; IFNG; IL1RN; IL36RN; PARP9; PYCARD; SOCS3; STAT1; WNT5A | 6 | 0.54 | ADIPOQ; IFNA5; NOL3; PALM3; SLIT2; SLIT3 | 1 | 3.17 | ADIPOQ | 0 | 0.00 | | 4 | 0.77 | ANGPT1; PALM3; SLIT2; SLIT3 | 5 | 1.07 | GSTP1; HIF1A; PARP9; SOCS3; WNT5A |
| morphogenesis of embryonic epithelium: GO | 132 | 10 | 1.27 | ALDH1A3; GDNF; GREM1; GRHL3; HIF1A; KIF20B; PFN1; STIL; TP63; WNT5A | 11 | 0.98 | ALX1; COBL; FOLR1; GLI2; IRX1; KAT2A; NOG; OSR1; PTCH1; SIX1; SOX8 | 0 | 0.00 | | 0 | 0.00 | | 7 | 1.35 | DLC1; GDF7; GLI2; OSR1; PRICKLE1; PTCH1; SHROOM3 | 5 | 1.07 | HIF1A; PFN1; STIL; WNT5A; WNT9B |
| adult behavior: GO | 132 | 9 | 1.14 | CHRNA3; CNTNAP2; CSTB; GDNF; HOMER1; NLGN4X; NR4A3; NTSR1; PCDH17 | 23 | 2.06 | ADAM22; ATP1A2; CARTPT; DNM1; DRD1; DRD4; GLRB; GRIN1; GRM7; LEP; LGI4; MAPT; NRXN1; NRXN3; SEZ6L; SHANK1; SLC1A2; SLITRK5; SNCA; SNCG; SPTBN4; TMOD1; ZFHX2 | 0 | 0.00 | | 0 | 0.00 | | 15 | 2.89 | ADAM22; ASIP; CHL1; CXCL12; EFNB3; GLRB; LGI4; MAPT; NRXN1; PREX2; SEZ6L; SLITRK6; SNCA; SPTBN4; ZIC1 | 5 | 1.07 | CNTNAP2; CSTB; HOMER1; NLGN4X; NTSR1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| protein tyrosine kinase binding: GO | 52 | 2 | 0.64 | NRG1; PCNA | 8 | 1.82 | ANGPT4; FLT3LG; LRP4; MST1; MYOC; NRG3; SHC2; SHC3 | 0 | 0.00 | | 0 | 0.00 | | 4 | 1.95 | ANGPT1; ANGPT4; MYOC; SHC2 | 2 | 1.09 | ARHGEF16; NRG1 |
| cyclic nucleotide metabolic process: GO | 52 | 1 | 0.32 | PTHLH | 7 | 1.59 | ADCY2; ADCY5; ADCY6; ADCY8; ATP2B2; PDE11A; PDE9A | 0 | 0.00 | | 0 | 0.00 | | 1 | 0.49 | PDE9A | 2 | 1.09 | PTHLH; UCN2 |
| fceri mediated mapk activation | 160 | 12 | 1.26 | ACTB; CSF2; DUSP6; DUSP9; EREG; HBEGF; IL2RA; JAK3; NRAS; NRG1; PSMA5; PSMB6 | 12 | 0.88 | BTC; CNKSR2; EGF; FGF1; FGFR1; FGFR3; GFRA1; GRIN2A; IL5; IRS2; NRG2; SHC2 | 0 | 0.00 | | 2 | 5.22 | IL2RA; LCP2 | 6 | 0.95 | ANGPT1; CNKSR2; EGF; FGFR1; MS4A2; SHC2 | 6 | 1.06 | ACTB; DUSP6; EREG; HBEGF; NRG1; VAV2 |
| regulation of erbb signaling pathway: GO | 79 | 5 | 1.06 | EPGN; EREG; MMP9; PLAUR; TGFA | 4 | 0.60 | ADORA1; ADRA2A; AGT; EGF | 0 | 0.00 | | 0 | 0.00 | | 4 | 1.29 | ADRA2A; EGF; ESR1; SPRY1 | 3 | 1.08 | AFAP1L2; EREG; TGFA |
| jnk cascade: GO | 79 | 3 | 0.64 | DUSP9; MDFI; WNT5A | 3 | 0.45 | BIRC7; FGF14; MAPK8IP1 | 0 | 0.00 | | 0 | 0.00 | | 0 | 0.00 | | 3 | 1.08 | MDFI; TRIB1; WNT5A |
| signaling by fgfr | 133 | 5 | 0.63 | CDK1; CDKN1A; FGFBP1; FLRT3; NRAS | 11 | 0.98 | ADCY2; ADCY5; ADCY6; ADCY8; FGF1; FGF17; FGF22; FGF9; FGFR1; FGFR3; PRKAR2B | 1 | 3.14 | PRKAR2B | 0 | 0.00 | | 4 | 0.76 | FGF2; FGF22; FGFR1; PDEIA | 5 | 1.07 | CDK1; CDKN1A; FGFBP1; FLRT3; TRIB3 |
| selective expression of chemokine | 26 | 8 | 5.15 | CCL3; CCR4; CCR5; CSF2; CXCR4; | 1 | 0.45 | IL5 | 0 | 0.00 | | 0 | 0.00 | | 0 | 0.00 | | 1 | 1.09 | IL12RB2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| receptors during t-cell polarization | | | | IFNG; IL12RB2; IL4R | | | | | | | | | | | | | | | |
| il27 pathway | 26 | 7 | 4.51 | EBI3; IFNG; IL12B; IL12RB2; IL1B; IL6; STAT1 | 0 | 0.00 | | 0 | 0.00 | | 1 | 16.07 | IL1B | 0 | 0.00 | | 1 | 1.09 | IL12RB2 |
| positive regulation of neutrophil migration: GO | 26 | 6 | 3.86 | C1QBP; CCL21; CXCL1; CXCL3; IL1B; RAC2 | 0 | 0.00 | | 0 | 0.00 | | 2 | 32.15 | IL1B; RAC2 | 0 | 0.00 | | 1 | 1.09 | CXCL2 |
| interleukin 4 pathway | 26 | 4 | 2.57 | IL13RA1; IL4R; JAK3; PI3 | 0 | 0.00 | | 0 | 0.00 | | 0 | 0.00 | | 0 | 0.00 | | 1 | 1.09 | CISH |
| negative regulation of exocytosis: GO | 26 | 4 | 2.57 | ANXA1; FOXF1; HMOX1; IL13RA2 | 4 | 1.82 | ADRA2A; IL1RAPL1; SNCA; STXBP6 | 0 | 0.00 | | 0 | 0.00 | | 3 | 2.93 | ADRA2A; SNCA; STXBP6 | 1 | 1.09 | IL13RA2 |
| chemoattractant activity: GO | 26 | 3 | 1.93 | CCL3; SCG2; WNT5A | 0 | 0.00 | | 0 | 0.00 | | 0 | 0.00 | | 2 | 1.95 | CXCL12; FGF2 | 1 | 1.09 | WNT5A |
| cholesterol biosynthesis | 26 | 3 | 1.93 | EBP: HMGCR; SQLE | 0 | 0.00 | | 0 | 0.00 | | 0 | 0.00 | | 0 | 0.00 | | 1 | 1.09 | SQLE |
| negative regulation of fatty acid metabolic process: GO | 26 | 3 | 1.93 | UGT1A1; UGT1A10; UGT1A7 | 5 | 2.27 | ACACB; ACADL; APOC1; CNR1; PLIN5 | 0 | 0.00 | | 0 | 0.00 | | 1 | 0.98 | DGAT2 | 1 | 1.09 | TRIB3 |
| neuromuscular synaptic transmission: GO | 26 | 3 | 1.93 | CHRNA3; CHRNA6; MYLK2 | 3 | 1.36 | CHRM1; CHRNA2; DTNA | 0 | 0.00 | | 0 | 0.00 | | 1 | 0.98 | CHRM1 | 1 | 1.09 | CHRNA6 |
| oxidoreductase activity acting on the ch nh group of donors: GO | 26 | 3 | 1.93 | ALDH4A1; MTHFD2; SMOX | 3 | 1.36 | ALDH1L1; DMGDH; PRODH | 0 | 0.00 | | 0 | 0.00 | | 2 | 1.95 | DMGDH; PRODH | 1 | 1.09 | SMOX |
| temperature homeostasis: GO | 26 | 3 | 1.93 | IL1A; IL1B; NTSR1 | 5 | 2.27 | ACADL; ADORA1; ADRB1; | 0 | 0.00 | | 1 | 16.07 | IL1B | 1 | 0.98 | PPARGC1A | 1 | 1.09 | NTSR1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | | | | DRD1; PPARGC1A | | | | | | | | | | | | |
| translesion synthesis by y family dna polymerases bypasses lesions on dna template | 26 | 3 | 1.93 | ISG15; PCNA; USP43 | 0 | 0.00 | | 0 | 0.00 | | 1 | 16.07 | ISG15 | 0 | 0.00 | | 1 | 1.09 | USP43 |
| acylglycerol o acyltransferase activity: GO | 26 | 2 | 1.29 | AGPAT5; MBOAT2 | 5 | 2.27 | AWAT2; DGAT2L6; MOGAT1; MOGAT2; PNPLA3 | 0 | 0.00 | | 0 | 0.00 | | 2 | 1.95 | DGAT2; PNPLA3 | 1 | 1.09 | LPCAT1 |
| cellular response to vitamin: GO | 26 | 2 | 1.29 | CYP24A1; TNC | 3 | 1.36 | FOLR1; FOLR2; LEP | 0 | 0.00 | | 0 | 0.00 | | 0 | 0.00 | | 1 | 1.09 | BRIP1 |
| dna catabolic process: GO | 26 | 2 | 1.29 | DNASE1L3; ISG20 | 2 | 0.91 | CECR2; DNASE1L2 | 0 | 0.00 | | 0 | 0.00 | | 0 | 0.00 | | 1 | 1.09 | DNASE1L3 |
| g alpha z signalling events | 26 | 2 | 1.29 | GNGT2; PRKCQ | 5 | 2.27 | ADCY2; ADCY5; ADCY6; ADRA2A; GNAZ | 0 | 0.00 | | 0 | 0.00 | | 1 | 0.98 | ADRA2A | 1 | 1.09 | PRKCQ |
| generation of second messenger molecules | 26 | 2 | 1.29 | CD3E; ENAH | 0 | 0.00 | | 0 | 0.00 | | 1 | 16.07 | LCP2 | 0 | 0.00 | | 1 | 1.09 | ENAH |
| intramolecular transferase activity: GO | 26 | 2 | 1.29 | PGAM1; PGM2 | 1 | 0.45 | PGM5 | 0 | 0.00 | | 0 | 0.00 | | 1 | 0.98 | PGM5 | 1 | 1.09 | PGAM1 |
| perk regulated gene expression | 26 | 2 | 1.29 | EIF2S1; HSPA5 | 0 | 0.00 | | 0 | 0.00 | | 0 | 0.00 | | 0 | 0.00 | | 1 | 1.09 | HSPA5 |
| post translational modification synthesis of gpi anchored proteins | 26 | 2 | 1.29 | PIGW; PLAUR | 0 | 0.00 | | 0 | 0.00 | | 0 | 0.00 | | 0 | 0.00 | | 1 | 1.09 | PIGW |
| prostanoid metabolic process: GO | 26 | 2 | 1.29 | PDPN; PTGS2 | 2 | 0.91 | CYP4F8; PTGIS | 0 | 0.00 | | 0 | 0.00 | | 0 | 0.00 | | 1 | 1.09 | PTGS2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| regulation of cell fate commitment: GO | 26 | 2 | 1.29 | DUSP6; IL12B | 3 | 1.36 | DKK1; FGFR1; MESP1 | 0 | 0.00 | | 0 | 0.00 | | 4 | 3.91 | FGF2; FGFR1; FZD7; MESP1 | 1 | 1.09 | DUSP6 |
| regulation of cellular Senescence: GO | 26 | 2 | 1.29 | HMGA2; TP63 | 1 | 0.45 | TERT | 0 | 0.00 | | 0 | 0.00 | | 0 | 0.00 | | 1 | 1.09 | HMGA2 |
| regulation of neuron migration: GO | 26 | 2 | 1.29 | KIF20B; NRG1 | 5 | 2.27 | ERBB4; NRG3; RELN; SEMA3A; UNC5D | 0 | 0.00 | | 0 | 0.00 | | 2 | 1.95 | ERBB4; RELN | 1 | 1.09 | NRG1 |
| regulation of protein localization to cell surface: GO | 26 | 2 | 1.29 | ABCA12; NRG1 | 4 | 1.82 | ACTN2; ASTN2; EGF; ERBB4 | 0 | 0.00 | | 0 | 0.00 | | 2 | 1.95 | EGF; ERBB4 | 1 | 1.09 | NRG1 |
| regulation of vascular endothelial growth factor receptor signaling pathway: GO | 26 | 2 | 1.29 | HIF1A; IL1B | 2 | 0.91 | FGF9; FZD4 | 0 | 0.00 | | 1 | 16.07 | IL1B | 0 | 0.00 | | 1 | 1.09 | HIF1A |
| signaling by fgfr1 | 26 | 2 | 1.29 | FLRT3; NRAS | 2 | 0.91 | FGF1; FGFR1 | 0 | 0.00 | | 0 | 0.00 | | 1 | 0.98 | FGFR1 | 1 | 1.09 | FLRT3 |
| udp galactosyl-transferase activity: GO | 26 | 2 | 1.29 | B3GNT3; B3GNT5 | 3 | 1.36 | ABO; B3GALT1; B3GALT5 | 0 | 0.00 | | 0 | 0.00 | | 2 | 1.95 | ABO; B3GALT1 | 1 | 1.09 | B3GNT5 |
| vegfr1 pathway | 26 | 2 | 1.29 | HIF1A; PGF | 1 | 0.45 | SHC2 | 0 | 0.00 | | 0 | 0.00 | | 1 | 0.98 | SHC2 | 1 | 1.09 | HIF1A |
| a tetrasaccharide linker sequence is required for gag synthesis | 26 | 1 | 0.64 | SDC1 | 6 | 2.72 | BCAN; GPC2; GPC3; GPC6; GXYLT2; SDC2 | 0 | 0.00 | | 0 | 0.00 | | 3 | 2.93 | DCN; GPC2; GXYLT2 | 1 | 1.09 | AGRN |
| aldo keto reductase nadp activity: GO | 26 | 1 | 0.64 | AKR1B10 | 0 | 0.00 | | 0 | 0.00 | | 0 | 0.00 | | 0 | 0.00 | | 1 | 1.09 | AKR1B10 |
| fibroblast growth factor receptor binding: GO | 26 | 1 | 0.64 | FLRT3 | 5 | 2.27 | FGF1; FGF14; FGF17; FGF22; FGF9 | 0 | 0.00 | | 0 | 0.00 | | 2 | 1.95 | FGF2; FGF22 | 1 | 1.09 | FLRT3 |
| nad adp ribosyl-transferase activity: GO | 26 | 1 | 0.64 | PARP9 | 1 | 0.45 | ART5 | 0 | 0.00 | | 0 | 0.00 | | 0 | 0.00 | | 1 | 1.09 | PARP9 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| negative regulation of embryonic development: GO | 26 | 1 | 0.64 | WNT5A | 3 | 1.36 | DKK1; MESP1; RPS6KA6 | 0 | 0.00 | | 0 | 0.00 | | 3 | 2.93 | FZD7; MESP1; RPS6KA6 | 1 | 1.09 | WNT5A |
| negative regulation of telomere maintenance: GO | 26 | 1 | 0.64 | PIF1 | 0 | 0.00 | | 0 | 0.00 | | 0 | 0.00 | | 0 | 0.00 | | 1 | 1.09 | PIF1 |
| nep ns2 interacts with the cellular export machinery | 26 | 1 | 0.64 | RAN | 0 | 0.00 | | 0 | 0.00 | | 0 | 0.00 | | 0 | 0.00 | | 1 | 1.09 | RAN |
| p38 mkk3 6pathway | 26 | 1 | 0.64 | TXN | 1 | 0.45 | CAMK2B | 0 | 0.00 | | 0 | 0.00 | | 0 | 0.00 | | 1 | 1.09 | TXN |
| phagosome acidification: GO | 26 | 1 | 0.64 | RAB38 | 3 | 1.36 | ATP6V0A4; ATP6V0E2; ATP6V1B1 | 0 | 0.00 | | 0 | 0.00 | | 2 | 1.95 | ATP6V0A4; ATP6V0E2 | 1 | 1.09 | RAB38 |
| phosphatidyl-choline biosynthetic process: GO | 26 | 1 | 0.64 | FABP5 | 1 | 0.45 | CHPT1 | 0 | 0.00 | | 0 | 0.00 | | 0 | 0.00 | | 1 | 1.09 | FABP5 |
| regulation of cgmp metabolic process: GO | 26 | 1 | 0.64 | WNT5A | 4 | 1.82 | APOE; GUCA1B; NOS2; OSTN | 0 | 0.00 | | 0 | 0.00 | | 0 | 0.00 | | 1 | 1.09 | WNT5A |
| regulation of mrna 3 end processing: GO | 26 | 1 | 0.64 | CCNB1 | 0 | 0.00 | | 0 | 0.00 | | 0 | 0.00 | | 0 | 0.00 | | 1 | 1.09 | CCNB1 |
| smad2 smad3 smad4 heterotrimer regulates transcription | 26 | 1 | 0.64 | SERPINE1 | 0 | 0.00 | | 0 | 0.00 | | 1 | 16.07 | SERPINE1 | 0 | 0.00 | | 1 | 1.09 | JUNB |
| solute proton symporter activity: GO | 26 | 1 | 0.64 | SLC2A9 | 0 | 0.00 | | 0 | 0.00 | | 0 | 0.00 | | 1 | 0.98 | SLC2A12 | 1 | 1.09 | SLC2A9 |
| ventricular system development: GO | 26 | 1 | 0.64 | CENPF | 1 | 0.45 | HYDIN | 0 | 0.00 | | 0 | 0.00 | | 0 | 0.00 | | 1 | 1.09 | CENPF |
| wnt pathway | 26 | 1 | 0.64 | CSNK1A1 | 1 | 0.45 | WIF1 | 0 | 0.00 | | 0 | 0.00 | | 0 | 0.00 | | 1 | 1.09 | PPARD |
| acylglycerol homeostasis: GO | 26 | 0 | 0.00 | | 4 | 1.82 | FITM2; GPIHBP1; LPL; MLXIPL | 1 | 16.07 | LPL | 0 | 0.00 | | 1 | 0.98 | DGAT2 | 1 | 1.09 | ANGPTL4 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| nectin pathway | 26 | 0 | 0.00 | | 0 | 0.00 | | 0 | 0.00 | | 0 | 0.00 | | 0 | 0.00 | | 1 | 1.09 | VAV2 |
| rxr vdr pathway | 26 | 0 | 0.00 | | 2 | 0.91 | BCL2; RXRG | 0 | 0.00 | | 0 | 0.00 | | 1 | 0.98 | BCL2 | 1 | 1.09 | PPARD |
| synthesis of pc | 26 | 0 | 0.00 | | 1 | 0.45 | CHPT1 | 0 | 0.00 | | 0 | 0.00 | | 0 | 0.00 | | 1 | 1.09 | LPCAT1 |
| negative regulation of secretion: GO | 188 | 20 | 1.78 | ANXA1; F2RL1; FOXF1; HMGCR; HMOX1; HRH3; IL13RA2; IL1B; IL36RN; IL6; NRG1; OSM; P2RY1; RSAD2; SLAMF1; SRGN; TNFRSF21; TNFRSF9; VSNL1; ZC3H12A | 24 | 1.51 | ABCC8; ACVR1C; ADIPOQ; ADORA1; ADRA2A; CARTPT; CD34; CNR1; DRD4; EGF; GRM7; IL1RAPL1; INHBB; KCNB1; LEP; LIF; NPY1R; NPY5R; PPP1R9A; SCT; SNCA; SRCIN1; SSC5D; STXBP6 | 3 | 6.67 | ACVR1C; ADIPOQ; SRCIN1 | 3 | 6.67 | GBP1; IL1B; OSM | 9 | 1.22 | ADRA2A; ANGPT1; CD34; EGF; FBLN1; NPY1R; SNCA; SSC5D; STXBP6 | 7 | 1.06 | IL10; IL13RA2; NRG1; P2RY1; UCN2; VSNL1; ZC3H12A |
| phosphatidyl-inositol metabolic process: GO | 188 | 9 | 0.80 | CD80; CWH43; EREG; HBEGF; NRG1; PIGW; PLA2G4D; PLAUR; PLBD1 | 16 | 1.00 | BTC; EGF; ERBB4; FGF1; FGF17; FGF22; FGF9; FGFR1; FGFR3; GPLD1; IRS2; NRG2; PLA2G16; PLA2G5; PLCH2; PTPRQ | 1 | 2.22 | PLA2G16 | 0 | 0.00 | | 7 | 0.95 | EGF; ERBB4; FGF2; FGF22; FGFR1; GPLD1; PIK3R6 | 7 | 1.06 | EFR3B; EREG; HBEGF; NRG1; PIGW; PLA2G4D; PLCD4 |
| cardiac muscle tissue morphogenesis: GO | 53 | 5 | 1.58 | DSP; MYLK2; NRG1; TBX20; WNT5A | 7 | 1.56 | COL11A1; MYL3; NKX2-5; TNNC1; TNNT2; TPM1; ZFPM2 | 0 | 0.00 | | 0 | 0.00 | | 4 | 1.92 | COL11A1; FOXC1; TNNC1; ZFPM2 | 2 | 1.07 | NRG1; WNT5A |
| regulation of | 53 | 5 | 1.58 | GDNF; | 5 | 1.11 | AGT; FGFR1; | 0 | 0.00 | | 1 | 7.88 | IL1B | 4 | 1.92 | ESR1; FGFR1; | 2 | 1.07 | SNAI2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| morphogenesis of a branching structure: GO | | | | GREM1; IL1B; PGF; WNT5A | | | NOG; SIX1; SOX8 | | | | | | | | | NTN4; SHOX2 | | | WNT5A |
| nad binding: GO | 53 | 4 | 1.26 | AHCY; ALDH1A3; GAPDH; LDHA | 1 | 0.22 | GPD1 | 2 | 15.77 | GPD1; HSD11B2 | 0 | 0.00 | | 2 | 0.96 | ALDH5A1; AOX1 | 2 | 1.07 | GAPDH; LDHA |
| nfat pathway | 53 | 4 | 1.26 | CALR; CAMK1G; CSNK1A1; HBEGF | 7 | 1.56 | ACTA1; AGT; CAMK1; HAND2; LIF; NKX2-5; PRKAR2B | 1 | 7.88 | PRKAR2B | 0 | 0.00 | | 3 | 1.44 | CAMK1; FGF2; HAND2 | 2 | 1.07 | CAMK1G; HBEGF |
| positive regulation of phospholipase activity: GO | 53 | 4 | 1.26 | GNA15; PTAFR; S1PR4; SELE | 10 | 2.23 | ADRA1A; AGT; AGTR1; ARHGAP6; CALCR; CAMK2B; FGFR1; FGFR3; NMUR1; PLA2G5 | 0 | 0.00 | | 1 | 7.88 | SELE | 7 | 3.36 | ADCYAP1R1; ADRA1A; AGTR1; ESR1; FGF2; FGFR1; LPAR1 | 2 | 1.07 | GNA15; PTAFR |
| negative regulation of muscle cell differentiation: GO | 53 | 3 | 0.95 | CCL17; CXCL10; EREG | 7 | 1.56 | BHLHE41; DKK1; HDAC5; MSTN; MYOCD; NKX2-5; SOX8 | 0 | 0.00 | | 0 | 0.00 | | 3 | 1.44 | BHLHA15; BHLHE41; PRICKLE1 | 2 | 1.07 | EREG; PPARD |
| organelle transport along microtubule: GO | 53 | 3 | 0.95 | HIF1A; KIF23; NEFL | 2 | 0.45 | DYNC1I1; MAPT | 0 | 0.00 | | 0 | 0.00 | | 1 | 0.48 | MAPT | 2 | 1.07 | HIF1A; KIF23 |
| membrane lipid biosynthetic process: GO | 107 | 10 | 1.56 | B3GNT5; CERS3; CWH43; PIGW; PLAUR; SGPP2; SPTSSA; ST6GALNAC1; ST8SIA2; UGCG | 5 | 0.55 | FA2H; GAL3ST1; P2RX1; P2RX7; ST6GALNAC5 | 0 | 0.00 | | 0 | 0.00 | | 5 | 1.19 | ACER1; ALDH3A2; GAL3ST4; SPTSSB; ST6GALNAC5 | 4 | 1.06 | B3GNT5; PIGW; ST6GALNAC1; ST8SIA2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline: Up-regu-lated | A: Fold Change (FC) Up | A: Up-regulated Genes | A: Down-regu-lated | A: Fold Change (FC) | A: Down-regulated Genes | B. Differentially expressed genes significant in the baseline vs week 12 comparison only in the placebo: Up-regu-lated | B: Fold Change (FC) Up | B: Up-regulated Genes | B: Down-regu-lated | B: Fold Change (FC) | B: Down-regulated Genes | C. Differentially expressed genes significant in the baseline vs week 12 comparison only in the nemo: Up-regu-lated | C: Fold Change (FC) Up | C: Up-regulated Genes | C: Down-regu-lated | C: Fold Change (FC) | C: Down-regulated Genes |
|---|---|---|---|---|---|---|---|---|---|---|---|---|---|---|---|---|---|---|---|
| alcohol biosynthetic process: GO | 107 | 7 | 1.09 | CH25H; CYP27B1; EBP; FABP5; HMGCR; PTAFR; SQLE | 9 | 0.99 | CACNA1H; CFTR; CHPT1; HMGCS2; LEP; NPC1L1; PCK1; PLA2G5; PRKAA2 | 0 | 0.00 | | 0 | 0.00 | | 6 | 1.42 | ACER1; CACNA1H; CYP3A4; FGF2; HMGCS2; PRKAA2 | 4 | 1.06 | CYP27B1; FABP5; PTAFR; SQLE |
| electron carrier activity: GO | 107 | 6 | 0.94 | ALDH4A1; COX7B; CYCS; IDO1; RDH16; SH3BGRL3 | 6 | 0.66 | ACADL; ACOX2; COX7A1; CYP1A2; DMGDH; HAAO | 0 | 0.00 | | 0 | 0.00 | | 5 | 1.19 | ACOX2; AOX1; COX7A1; DMGDH; GLRX | 4 | 1.06 | CYCS; GLDC; RDH16; XDH |
| regulation of osteoblast differentiation: GO | 107 | 6 | 0.94 | AREG; GJA1; IFITM1; IL6; LTF; TP63 | 10 | 1.10 | FGFR1; GDF10; HAND2; HEMGN; ID4; NOG; OSTN; PTCH1; RORB; SMOC1 | 0 | 0.00 | | 0 | 0.00 | | 7 | 1.66 | CHRD; DDR2; FGFR1; HAND2; IGFBP5; PTCH1; TMEM119 | 4 | 1.06 | AREG; BMPR1B; LTF; SNAI2 |
| phosphatase regulator activity: GO | 80 | 3 | 0.63 | PPP2R2C; PPP4R1; PPP4R4 | 7 | 1.03 | ELFN2; PHACTR3; PPP1R14A; PPP1R1A; PPP1R1B; PPP2R2B; RCAN2 | 1 | 5.22 | PPP1R1A | 0 | 0.00 | | 3 | 0.95 | PHACTR3; RCAN2; TESC | 3 | 1.06 | IGFBP3; PPP2R2C; PPP4R1 |
| smad2 3nuclear pathway | 80 | 3 | 0.63 | CDKN1A; HSPA8; SERPINE1 | 5 | 0.74 | AR; GSC; IL5; KAT2A; NKX2-5 | 0 | 0.00 | | 1 | 5.22 | SERPINE1 | 1 | 0.32 | ESR1 | 3 | 1.06 | CDKN1A; HSPA8; IL10 |
| pigmentation: GO | 80 | 2 | 0.42 | RAB38; TH | 8 | 1.18 | BCL2; DCT; EDA; EDN3; MITF; OCA2; SOX10; TRAPPC6A | 0 | 0.00 | | 0 | 0.00 | | 6 | 1.91 | ASIP; BCL2; EDN3; MITF; SHROOM3; TRAPPC6A | 3 | 1.06 | RAB38; SNAI2; TH |
| actin filament organization: GO | 162 | 10 | 1.03 | ACTR3; ARPC1A; ARPC3; ARPC5L; | 15 | 1.09 | ACTA1; ARHGAP6; BCL2; COBL; ESPN; | 0 | 0.00 | | 1 | 2.58 | RAC2 | 6 | 0.94 | BCL2; DPYSL3; FRY; LMOD1; | 6 | 1.05 | ACTN1; ARPCIA; CFL1; MYO1B; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | CFL1; FSCN1; MYO1B; RAC2; RHOD; TMSB10 | | | FHOD3; GSN; LMOD1; PDLIM3; PPP1R9A; SCIN; SORBS1; SORBS2; TMOD1; TNNT2 | | | | | | | | | SCIN; SORBS2 | | | RHOD; RND1 |
| fertilization: GO | 135 | 5 | 0.62 | CCT2; CCT3; CCT5; CCT7; CDK1 | 12 | 1.05 | CATSPERG; GLRB; HSPA1L; KCNU1; NPM2; ROPN1B; SERPINA5; SPEF2; SPTBN4; SYT8; TNP1; WBP2NL | 0 | 0.00 | | 0 | 0.00 | | 7 | 1.32 | CATSPERG; GLRB; HOXA10; PLCZ1; ROPN1B; SPEF2; SPTBN4 | 5 | 1.05 | CCT2; CCT5; CDK1; PLCD4; TDRD9 |
| regulation of embryonic development: GO | 108 | 7 | 1.08 | CDK1; DUSP6; GDNF; GRHL3; IL1RN; PHLDA2; WNT5A | 14 | 1.53 | ADIPOQ; AMOT; DKK1; DMRT2; FGFR1; GATA1; LAMA2; MESP1; OSR1; OSR2; PHLDB1; RPS6KA6; SIX1; TBX18 | 1 | 3.87 | ADIPOQ | 0 | 0.00 | | 8 | 1.88 | DMRT2; FGFR1; FZD7; LAMA2; MESP1; OSR1; RPS6KA6; TBX18 | 4 | 1.05 | CDK1; DUSP6; PHLDA2; WNT5A |
| heterotypic cell cell adhesion: GO | 27 | 6 | 3.72 | CD2; DSC2; DSP; ITGAX; JUP; PERP | 2 | 0.87 | CTNNA3; ITGA7 | 0 | 0.00 | | 0 | 0.00 | | 1 | 0.94 | GLDN | 1 | 1.05 | DSC2 |
| inflam pathway | 27 | 5 | 3.10 | CSF2; IFNG; IL12B; IL1A; IL6 | 1 | 0.44 | IL5 | 0 | 0.00 | | 0 | 0.00 | | 0 | 0.00 | | 1 | 1.05 | IL10 |
| mhc protein binding: GO | 27 | 4 | 2.48 | CLEC7A; KRT17; TAP2; VCP | 0 | 0.00 | | 0 | 0.00 | | 0 | 0.00 | | 0 | 0.00 | | 1 | 1.05 | CLEC7A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| positive regulation of mesenchymal cell proliferation: GO | 27 | 4 | 2.48 | FOXF1; STAT1; TP63; WNT5A | 4 | 1.75 | FGF9; FGFR1; IRS2; SIX1 | 0 | 0.00 | | 0 | 0.00 | | 5 | 4.71 | CHRD; FGFR1; MYCN; PRRX1; SHOX2 | 1 | 1.05 | WNT5A |
| regulation of megakaryocyte differentiation: GO | 27 | 4 | 2.48 | HIST1H4I; HIST1H4J; HIST1H4K; HIST1H4L | 1 | 0.44 | SCIN | 0 | 0.00 | | 0 | 0.00 | | 2 | 1.88 | SCIN; TESC | 1 | 1.05 | HIST1H4I |
| telomere capping: GO | 27 | 4 | 2.48 | HIST1H4I; HIST1H4J; HIST1H4K; HIST1H4L | 0 | 0.00 | | 0 | 0.00 | | 0 | 0.00 | | 0 | 0.00 | | 1 | 1.05 | HIST1H4I |
| activation of phospholipase c activity: GO | 27 | 3 | 1.86 | GNA15; SIPR4; SELE | 5 | 2.18 | ADRA1A; AGT; ARHGAP6; CALCR; NMUR1 | 0 | 0.00 | | 1 | 15.48 | SELE | 3 | 2.82 | ADCYAP1R1; ADRA1A; LPAR1 | 1 | 1.05 | GNA15 |
| cytosolic trna aminoacylation | 27 | 3 | 1.86 | EPRS; GARS; TARS | 0 | 0.00 | | 0 | 0.00 | | 0 | 0.00 | | 0 | 0.00 | | 1 | 1.05 | TARS |
| glypican 1pathway | 27 | 3 | 1.86 | NRG1; PRNP; TGFBR1 | 2 | 0.87 | FGFR1; SLIT2 | 0 | 0.00 | | 0 | 0.00 | | 3 | 2.82 | FGF2; FGFR1; SLIT2 | 1 | 1.05 | NRG1 |
| regulation of cardiac muscle cell contraction: GO | 27 | 3 | 1.86 | DSC2; DSP; JUP | 3 | 1.31 | ANK2; ATP1A2; CTNNA3 | 0 | 0.00 | | 0 | 0.00 | | 0 | 0.00 | | 1 | 1.05 | DSC2 |
| site of double strand break: GO | 27 | 3 | 1.86 | ESCO2; H2AFX; VCP | 0 | 0.00 | | 0 | 0.00 | | 0 | 0.00 | | 0 | 0.00 | | 1 | 1.05 | H2AFX |
| antiviral mechanism by ifn stimulated genes | 27 | 2 | 1.24 | EIF4A3; EIF4G2 | 0 | 0.00 | | 0 | 0.00 | | 0 | 0.00 | | 0 | 0.00 | | 1 | 1.05 | EIF4A3 |
| gsk3 pathway | 27 | 2 | 1.24 | GJA1; MYD88 | 0 | 0.00 | | 0 | 0.00 | | 0 | 0.00 | | 0 | 0.00 | | 1 | 1.05 | MYD88 |
| keratan sulfate biosynthetic process: GO | 27 | 2 | 1.24 | B3GNT3; CHST1 | 2 | 0.87 | CHST5; PRELP | 0 | 0.00 | | 0 | 0.00 | | 0 | 0.00 | | 1 | 1.05 | CHST1 |
| lipoprotein metabolism | 27 | 2 | 1.24 | LDLR; SDC1 | 3 | 1.31 | ALB; APOE; LPL | 1 | 15.48 | LPL | 0 | 0.00 | | 0 | 0.00 | | 1 | 1.05 | LDLR |
| metallocarboxy- | 27 | 2 | 1.24 | CPA6; | 2 | 0.87 | AGBL1; | 0 | 0.00 | | 0 | 0.00 | | 2 | 1.88 | CPE; CPZ | 1 | 1.05 | CPA6 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| peptidase activity: GO | | | | CPXM1 | | | AGBL4 | | | | | | | | | | | | |
| negative regulation of calcium ion transmembrane transport: GO | 27 | 2 | 1.24 | GSTO1; NTSR1 | 7 | 3.06 | ADRA2A; ATP1A2; CASQ2; DRD4; GSTM2; SLN; TRDN | 0 | 0.00 | | 0 | 0.00 | | 2 | 1.88 | ADRA2A; TRDN | 1 | 1.05 | NTSR1 |
| negative regulation of fibroblast proliferation: GO | 27 | 2 | 1.24 | GSTP1; IFI30 | 3 | 1.31 | C1QL4; DACH1; NUPR1 | 0 | 0.00 | | 0 | 0.00 | | 1 | 0.94 | DACH1 | 1 | 1.05 | GSTP1 |
| neutral lipid biosynthetic process: GO | 27 | 2 | 1.24 | AGPAT5; GK | 8 | 3.50 | AGMO; GPAM; GPD1; LPL; MOGAT1; MOGAT2; PCK1; PNPLA3 | 3 | 46.43 | GPAM; GPD1; LPL | 0 | 0.00 | | 2 | 1.88 | DGAT2; PNPLA3 | 1 | 1.05 | LPCAT1 |
| protein phosphatase 2a binding: GO | 27 | 2 | 1.24 | EIF4EBP1; HMGCR | 2 | 0.87 | BCL2; MAPT | 0 | 0.00 | | 0 | 0.00 | | 2 | 1.88 | BCL2; MAPT | 1 | 1.05 | EIF4EBP1 |
| regulation of astrocyte differentiation: GO | 27 | 2 | 1.24 | IL1B; SERPINE2 | 4 | 1.75 | ID4; LIF; NOG; NTRK3 | 0 | 0.00 | | 1 | 15.48 | IL1B | 1 | 0.94 | MYCN | 1 | 1.05 | SERPINE2 |
| response to lithium ion: GO | 27 | 2 | 1.24 | CALR; PTGS2 | 3 | 1.31 | ACTA1; FABP4; TFAP2B | 0 | 0.00 | | 0 | 0.00 | | 0 | 0.00 | | 1 | 1.05 | PTGS2 |
| vasoconstriction: GO | 27 | 2 | 1.24 | BDKRB2; HTR7 | 5 | 2.18 | ADRA1A; ADRA1B; AGT; EDN3; P2RX1 | 0 | 0.00 | | 0 | 0.00 | | 2 | 1.88 | ADRA1A; EDN3 | 1 | 1.05 | BDKRB2 |
| vegf, hypoxia, and angiogenesis | 27 | 2 | 1.24 | EIF2S1; HIF1A | 0 | 0.00 | | 0 | 0.00 | | 0 | 0.00 | | 0 | 0.00 | | 1 | 1.05 | HIF1A |
| apoptotic cell clearance: GO | 27 | 1 | 0.62 | TGM2 | 3 | 1.31 | FCN2; MARCO; MERTK | 0 | 0.00 | | 0 | 0.00 | | 0 | 0.00 | | 1 | 1.05 | TGM2 |
| cargo trafficking to the periciliary membrane | 27 | 1 | 0.62 | CCT5 | 0 | 0.00 | | 0 | 0.00 | | 0 | 0.00 | | 0 | 0.00 | | 1 | 1.05 | CCT5 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| cell volume homeostasis: GO | 27 | 1 | 0.62 | AQP3 | 3 | 1.31 | AQP4; AQP7; P2RX7 | 0 | 0.00 | | 1 | 15.48 | AQP9 | 0 | 0.00 | | 1 | 1.05 | AQP3 |
| central nervous system neuron axonogenesis: GO | 27 | 1 | 0.62 | FBXO45 | 7 | 3.06 | DCLK1; DCX; EPHB1; GLI2; PLXNA4; SLIT2; SPTBN4 | 0 | 0.00 | | 0 | 0.00 | | 5 | 4.71 | DCLK1; GLI2; PLXNA4; SLIT2; SPTBN4 | 1 | 1.05 | FBXO45 |
| citrate cycle (tca cycle) | 27 | 1 | 0.62 | OGDHL | 1 | 0.44 | PCK1 | 0 | 0.00 | | 0 | 0.00 | | 0 | 0.00 | | 1 | 1.05 | OGDHL |
| erk1/erk2 mapk signaling pathway | 27 | 1 | 0.62 | NGF | 0 | 0.00 | | 0 | 0.00 | | 0 | 0.00 | | 0 | 0.00 | | 1 | 1.05 | NGF |
| granule cell survival pathway | 27 | 1 | 0.62 | CAMP | 1 | 0.44 | MAPK8IP1 | 0 | 0.00 | | 0 | 0.00 | | 0 | 0.00 | | 1 | 1.05 | CXCL2 |
| hdac pathway | 27 | 1 | 0.62 | CAMK1G | 2 | 0.87 | CAMK1; HDAC5 | 0 | 0.00 | | 0 | 0.00 | | 1 | 0.94 | CAMK1 | 1 | 1.05 | CAMK1G |
| hippo signaling: GO | 27 | 1 | 0.62 | TEAD4 | 1 | 0.44 | AMOT | 0 | 0.00 | | 0 | 0.00 | | 0 | 0.00 | | 1 | 1.05 | TEAD4 |
| hsp90 protein binding: GO | 27 | 1 | 0.62 | HIF1A | 0 | 0.00 | | 0 | 0.00 | | 1 | 15.48 | GBP1 | 0 | 0.00 | | 1 | 1.05 | HIF1A |
| interaction between l1 and ankyrins | 27 | 1 | 0.62 | ACTB | 3 | 1.31 | ANK2; SCN7A; SPTBN4 | 0 | 0.00 | | 0 | 0.00 | | 2 | 1.88 | SCN7A; SPTBN4 | 1 | 1.05 | ACTB |
| maturation of 5 8s rrna: GO | 27 | 1 | 0.62 | EIF6 | 0 | 0.00 | | 0 | 0.00 | | 0 | 0.00 | | 0 | 0.00 | | 1 | 1.05 | EIF6 |
| negative regulation of dendrite development: GO | 27 | 1 | 0.62 | PLK2 | 2 | 0.87 | APOE; NLGN1 | 0 | 0.00 | | 0 | 0.00 | | 0 | 0.00 | | 1 | 1.05 | PLK2 |
| proton transporting two sector atpase complex: GO | 27 | 1 | 0.62 | PPIF | 3 | 1.31 | ATP6V0A4; ATP6V0E2; ATP6V1B1 | 0 | 0.00 | | 0 | 0.00 | | 2 | 1.88 | ATP6V0A4; ATP6V0E2 | 1 | 1.05 | PPIF |
| regulation of endothelial cell differentiation: GO | 27 | 1 | 0.62 | IL1B | 2 | 0.87 | ATOH8; TMEM100 | 0 | 0.00 | | 1 | 15.48 | IL1B | 1 | 0.94 | ATOH8 | 1 | 1.05 | XDH |
| rna polymerase iii abortive and retractive | 27 | 1 | 0.62 | POLR3G | 0 | 0.00 | | 0 | 0.00 | | 0 | 0.00 | | 0 | 0.00 | | 1 | 1.05 | POLR3G |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| initiation | | | | | | | | | | | | | | | | | | | |
| translation initiation factor binding: GO | 27 | 1 | 0.62 | EIF4EBP1 | 0 | 0.00 | | 0 | 0.00 | | 0 | 0.00 | | | 0.00 | | 1 | 1.05 | EIF4EBP1 |
| ventricular septum morphogenesis: GO | 27 | 1 | 0.62 | WNT5A | 3 | 1.31 | NKX2-5; WNT11; ZFPM2 | 0 | 0.00 | | 0 | 0.00 | | 2 | 1.88 | WNT11; ZFPM2 | 1 | 1.05 | WNT5A |
| rab guanyl nucleotide exchange factor activity: GO | 27 | 0 | 0.00 | | 2 | 0.87 | DENND2A; RAB3IL 1 | 0 | 0.00 | | 0 | 0.00 | | 1 | 0.94 | DENND2A | 1 | 1.05 | ST5 |
| regulation of dna damage response signal transduction by p53 class mediator: GO | 27 | 0 | 0.00 | 4 | 0 | 0.00 | | 0 | 0.00 | | 0 | 0.00 | | 0 | 0.00 | | 1 | 1.05 | SNAI2 |
| cytokine receptor activity: GO | 81 | 15 | 3.10 | CCR4; CCR5; CXCR1; CXCR4; EBI3; IL12B; IL12RB2; IL13RA1; IL13RA2; IL1R2; IL1RAP; IL1RL1; IL2RA; IL4R; IL7R | 7 | 1.02 | CNTFR; CXCR5; GFRA1; GHR; IL11RA; LEPR; LIFR | 1 | 5.16 | GHR | 3 | 15.48 | IL21R; IL2RA; IL7R | 2 | 0.63 | CNTFR; IL11RA | 3 | 1.05 | CXCR1; IL12RB2; IL13RA2 |
| movement in environment of other organism involved in symbiotic interaction: GO | 81 | 13 | 2.69 | CCR5; CD80; CTSB; CXADR; CXCR4; DPP4; ITGB6; LAMP3; LDLR; PPIA; SERPINB3; SLAMF1; TNFRSF4 | 1 | 0.15 | NCAM1 | 0 | 0.00 | | 1 | 5.16 | LAMP3 | 2 | 0.63 | EFNB3; NCAM1 | 3 | 1.05 | DPP4; ITGB6; LDLR |
| molting cycle: GO | 81 | 7 | 1.45 | CDH3; FOXE1; | 8 | 1.17 | ALX4; BCL2; DKK1; | 0 | 0.00 | | 0 | 0.00 | | 6 | 1.88 | ALX4; BCL2; IGFBP5; | 3 | 1.05 | DSG4; FOXE1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | KRT14; KRT16; KRT17; PTGS2; TP63 | | | DNASE1L2; EDA; LGR5; LRP4; PTCH2 | | | | | | | | | LDB2; LGR5; PTCH2 | | | PTGS2 |
| myd88 mal cascade initiated on plasma membrane | 81 | 5 | 1.03 | CDK1; DUSP6; MYD88; S100A12; UBE2N | 1 | 0.15 | PELI2 | 0 | 0.00 | | 0 | 0.00 | | 1 | 0.31 | PELI2 | 3 | 1.05 | CDK1; DUSP6; MYD88 |
| regulation of lipase activity: GO | 81 | 5 | 1.03 | ANXA1; GNA15; PTAFR; S1PR4; SELE | 14 | 2.04 | ADRA1A; AGT; AGTR1; APOC1; ARHGAP6; CALCR; CAMK2B; FGFR1; FGFR3; GPIHBP1; NMUR1; PLA2G5; PLIN5; SNCA | 0 | 0.00 | | 1 | 5.16 | SELE | 8 | 2.51 | ADCYAP1R1; ADRA1A; AGTR1; ESR1; FGF2; FGFR1; LPAR1; SNCA | 3 | 1.05 | ANGPTL4; GNA15; PTAFR |
| proteoglycan metabolic process: GO | 81 | 3 | 0.62 | HPSE; HS3ST3B1; SULF2 | 9 | 1.31 | BCAN; CHST12; COL11A1; EXTL1; HS3ST5; HS6ST3; IDUA; NDNF; UST | 0 | 0.00 | | 0 | 0.00 | | 7 | 2.20 | CHST12; COL11A1; DCN; DSEL; GAL3ST4; NDNF; UST | 3 | 1.05 | BMPR1B; HPSE; PPARD |
| fibroblast growth factor receptor signaling pathway: GO | 81 | 2 | 0.41 | FGFBP1; FLRT3 | 8 | 1.17 | FGF1; FGF14; FGF17; FGF22; FGF9; FGFR1; FGFR3; NOG | 0 | 0.00 | | 0 | 0.00 | | 4 | 1.25 | CTGF; FGF2; FGF22; FGFR1 | 3 | 1.05 | FGFBP1; FLRT3; SHCBP1 |
| g protein coupled receptor signaling pathway coupled to cyclic nucleotide second messenger: GO | 163 | 14 | 1.44 | ADCYAP1; ADM2; ANXA1; FPR1; GNAI3; GPR1; HRH3; HTR7; INSL3; LPAR3; | 32 | 2.32 | ADCY2; ADCY5; ADCY6; ADCY8; ADORA1; ADRA1A; ADRA1B; | 0 | 0.00 | | 0 | 0.00 | | 10 | 1.56 | ADRA1A; ADRA2A; CHRM1; CHRM3; GRIK3; LPAR1; NPY1R; | 6 | 1.04 | ADM2; HRH2; P2RY1; PTHLH; RGS1; UCN2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | P2RY1; PTHLH; RGS1; S1PR4 | | | ADRA2A; ADRB1; AGT; CALCR; CHRM1; CHRM2; CHRM3; CHRM4; CNR1; DRD1; DRD4; GALR1; GCGR; GNAZ; GRIK3; GRM7; HTR4; HTR6; LHCGR; NPY1R; OR56A1; OR56A4; OR56A5; PTHIR; TSHR | | | | | | | | | PSAPL1; PTHIR; TSHR | | | |
| regulation of cytokine production involved in immune response: GO | 54 | 8 | 2.48 | F2RL1; HMOX1; JAK3; NR4A3; RSAD2; SASH3; SLAMF1; WNT5A | 0 | 0.00 | | 0 | 0.00 | | 1 | 7.74 | FFAR2 | 2 | 0.94 | ANGPT1; GPRC5B | 2 | 1.05 | IL10; WNT5A |
| scfskp2 mediated degradation of p27 p21 | 54 | 7 | 2.17 | CCNA2; CCNE1; CDKN1A; PSMA4; PSMA5; PSMB6; PSMD1 | 0 | 0.00 | | 0 | 0.00 | | 0 | 0.00 | | 0 | 0.00 | | 2 | 1.05 | CCNA2; CDKN1A |
| non small cell lung cancer | 54 | 3 | 0.93 | E2F3; NRAS; TGFA | 2 | 0.44 | EGF; RXRG | 0 | 0.00 | | 0 | 0.00 | | 1 | 0.47 | EGF | 2 | 1.05 | E2F1; TGFA |
| brush border membrane: GO | 54 | 2 | 0.62 | KCNK1; SLC5A1 | 9 | 1.97 | ATP6V0A4; CDHR5; | 0 | 0.00 | | 0 | 0.00 | | 3 | 1.41 | ATP6V0A4; CYBRD1; | 2 | 1.05 | KCNK1; SLC26A6 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | | | | CYBRD1; FOLR1; NPC1L1; PTH1R; SLC34A3; SLC5A2; SLC7A9 | | | | | | | | | PTH1R | | | |
| golgi associated vesicle biogenesis | 54 | 2 | 0.62 | AP1S3; HSPA8 | 0 | 0.00 | | 0 | 0.00 | | 0 | 0.00 | | 0 | 0.00 | | 2 | 1.05 | AP1S3; HSPA8 |
| rrna binding: GO | 54 | 2 | 0.62 | DDX21; DDX28 | 0 | 0.00 | | 0 | 0.00 | | 0 | 0.00 | | 0 | 0.00 | | 2 | 1.05 | DDX21; DDX28 |
| regulation of rna stability: GO | 136 | 11 | 1.35 | GDNF; HSPA8; MYD88; PSMA4; PSMA5; PSMB6; PSMD1; PSME3; SERBP1; YWHAZ; ZC3H12A | 2 | 0.17 | RBM24; SCGB1A1 | 0 | 0.00 | | 0 | 0.00 | | 0 | 0.00 | | 5 | 1.04 | E2F1; HSPA8; MYD88; YWHAZ; ZC3H12A |
| cell cell adhesion via plasma membrane adhesion molecules: GO | 191 | 13 | 1.14 | CDH26; CDH3; CXADR; DSC1; DSC2; DSC3; DSG1; DSG3; LGALS7B; MPZL2; PCDH17; SDK2; SELE | 47 | 2.90 | CADM3; CBLN1; CDH12; CDH19; CDH20; CDH22; CDH4; CDHR1; CDHR4; CDHR5; CLDN16; CLDN18; CLDN8; CLSTN2; DSCAML1; FAT3; IL1RAPL1; NLGN1; | 0 | 0.00 | | 1 | 2.19 | SELE | 24 | 3.19 | CADM2; CADM3; CDH20; CDH22; CDHR4; CLDN18; CLDN8; FAT3; NRXN1; PCDH18; PCDH19; PCDHB11; PCDHB12; PCDHB3; PCDHB6; PCDHGA2; PCDHGA4; PCDHGA5; | 7 | 1.04 | CDH26; DSC2; DSC3; DSG4; MPZL2; PCDH7; SDK2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | | | | NRXN1; PCDH11X; PCDH11Y; PCDH15; PCDH19; PCDH9; PCDHA10; PCDHA13; PCDHA4; PCDHA6; PCDHAC1; PCDHB15; PCDHB16; PCDHB3; | | | | | | | | | PCDHGA6; PCDHGA7; PCDHGA8; PCDHGB1; PCDHGB2; PTPRT | | | |
| activated tlr4 signalling | 109 | 6 | 0.92 | CAP1; CDK1; DUSP6; MYD88; S100A12; UBE2N | 1 | 0.11 | PELI2 | 0 | 0.00 | | 0 | 0.00 | | 1 | 0.23 | PELI2 | 4 | 1.04 | CAP1; CDK1; DUSP6; MYD88 |
| vacuolar lumen: GO | 109 | 6 | 0.92 | CTSB; HPSE; HSPA8; IFI30; RAB38; SDC1 | 11 | 1.19 | BCAN; CTSF; GPC2; GPC3; GPC6; GYG2; IDUA; NAPSA; PRELP; SDC2; SFTPC | 0 | 0.00 | | 0 | 0.00 | | 2 | 0.47 | DCN; GPC2 | 4 | 1.04 | AGRN; HPSE; HSPA8; RAB38 |
| plasma membrane raft: GO | 82 | 9 | 1.84 | ATP1B3; CTSB; HMOX1; KIF18A; LRP8; PTGS2; SELE; SLC2A1; TRPC4 | 8 | 1.15 | ATP1A2; DRD1; KCND2; LRP4; MLC1; MYO1A; PTCH1; PTGIS | 0 | 0.00 | | 2 | 10.19 | LCP2; SELE | 4 | 1.24 | ADCYAP1R1; DLC1; KCND2; PTCH1 | 3 | 1.04 | KIF18A; PTGS2; SLC2A1 |
| positive regulation of protein polymerization: GO | 82 | 7 | 1.43 | ACTR3; ARPC1A; ARPC3; ARPC5L; CCL21; PFN1; PYCARD | 4 | 0.58 | GSN; MAPT; SCIN; TPPP | 0 | 0.00 | | 0 | 0.00 | | 3 | 0.93 | MAPT; SCIN; TPPP | 3 | 1.04 | ARPC1A; CDC42EP1; PFN1 |
| positive | 82 | 6 | 1.22 | GJA1; | 6 | 0.86 | ID4; OSR1; | 0 | 0.00 | | 0 | 0.00 | | 3 | 0.93 | DDR2; OSR1; | 3 | 1.04 | BMPR1B; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| regulation of ossification: GO | | | | IFITM1; IL6; LTF; TP63; WNT5A | | | OSR2; P2RX7; PKDCC; ZBTB16 | | | | | | | | | TMEM119 | | | LTF; WNT5A |
| positive regulation of peptidyl serine phosphorylation: GO | 82 | 6 | 1.22 | IFNE; IFNG; IL6; OSM; TXN; WNT5A | 7 | 1.01 | BCAR3; BCL2; CAMK1; IFNA5; LIF; NTRK3; SNCA | 0 | 0.00 | | 1 | 5.10 | OSM | 5 | 1.55 | ANGPT1; BCAR3; BCL2; CAMK1; SNCA | 3 | 1.04 | IFNE; TXN; WNT5A |
| neutral lipid metabolic process: GO | 82 | 5 | 1.02 | AGPAT5; FABP5; FABP6; GK; PCSK9 | 16 | 2.30 | AGMO; APOC1; APOE; AWAT2; DGAT2L6; FABP4; FABP7; GPAM; GPD1; LPL; MOGAT1; MOGAT2; PCK1; PNPLA3; SNCA; TNXB | 3 | 15.29 | GPAM; GPD1; LPL | 0 | 0.00 | | 3 | 0.93 | DGAT2; PNPLA3; SNCA | 3 | 1.04 | FABP5; LPCAT1; PCSK9 |
| organophosphate ester transport: GO | 82 | 5 | 1.02 | ABCA12; GJA1; LDLR; PITPNM1; PREL1D1 | 4 | 0.58 | ABCA2; APOC1; APOE; P2RX7 | 0 | 0.00 | | 0 | 0.00 | | 0 | 0.00 | | 3 | 1.04 | LDLR; PITPNM1; PRELID1 |
| negative regulation of developmental growth: GO | 82 | 4 | 0.82 | CDK5R1; GJA1; SEMA4B; WNT5A | 13 | 1.87 | ADRB1; FGFR3; MSTN; NOG; PLXNA3; PTCH1; RBP4; SEMA3A; SEMA3B; SEMA3D; SEMA3E; SEMA3G; TBX5 | 0 | 0.00 | | 0 | 0.00 | | 4 | 1.24 | KCNK2; PTCH1; SEMA3E; SEMA4G | 3 | 1.04 | CDK5R1; SEMA4B; WNT5A |
| anchored | 137 | 14 | 1.71 | ALPL; | 24 | 2.07 | BCAN; | 1 | 3.05 | LPL | 0 | 0.00 | | 13 | 2.41 | CNTFR; | 5 | 1.03 | LY6D; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| component of membrane: GO | | | | CD177; CD2; FCGR3B; LY6D; LYPD3; LYPD5; PLAUR; PRNP; RAET1L; ULBP1; ULBP2; ULBP3; VNN3 | | | CNTFR; CNTN3; CNTN4; CP; FOLR1; FOLR2; GFRA1; GFRA3; GGT7; GP2; GPC2; GPC3; GPC6; GPIHBP1; LPL; MDGA2; NCAM1; NEGR1; OTOA; PKHD1; PRSS42; PSCA; SVIP | | | | | | | | | CNTN3; CP; GPC2; LSAMP; LYPD2; NCAM1; NEGR1; NRN1; PSCA; RECK; RHBG; SVIP | | | LYPD3; LYPD5; MMP25; RAET1L |
| adenylate cyclase modulating g protein coupled receptor signaling pathway: GO | 137 | 10 | 1.22 | ADCYAP1; ADM2; FPR1; GNAI3; HRH3; INSL3; P2RY1; PTHLH; RGS1; S1PR4 | 29 | 2.50 | ADCY2; ADCY5; ADCY6; ADCY8; ADORA1; ADRA1A; ADRA1B; ADRA2A; ADRB1; CALCR; CHRM1; CHRM2; CHRM3; CHRM4; CNR1; DRD1; DRD4; GALR1; GCGR; GNAZ; GRIK3; GRM7; LHCGR; NPY1R; | 0 | 0.00 | | 0 | 0.00 | | 10 | 1.85 | ADRA1A; ADRA2A; CHRM1; CHRM3; GRIK3; LPAR1; NPY1R; PSAPL1; PTHIR; TSHR | 5 | 1.03 | ADM2; P2RY1; PTHLH; RGS1; UCN2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | A: Fold Change (FC) Up | A: Up-regulated Genes | A: Down-regulated | A: Fold Change (FC) | A: Down-regulated Genes | B. Differentially expressed genes significant in the baseline vs week 12 comparison only in the placebo: Up-regulated | B: Fold Change (FC) Up | B: Up-regulated Genes | B: Down-regulated | B: Fold Change (FC) | B: Down-regulated Genes | C. Differentially expressed genes significant in the baseline vs week 12 comparison only in the nemo: Up-regulated | C: Fold Change (FC) Up | C: Up-regulated Genes | C: Down-regulated | C: Fold Change (FC) | C: Down-regulated Genes |
|---|---|---|---|---|---|---|---|---|---|---|---|---|---|---|---|---|---|---|---|
| | | | | | | | OR56A1; OR56A4; OR56A5; PTHIR; TSHR | | | | | | | | | | | | |
| positive regulation of calcium ion transmembrane transport: GO | 55 | 7 | 2.13 | BDKRB1; CXCL10; CXCL11; CXCL9; GSTO1; NPSR1; NTSR1 | 8 | 1.72 | ANK2; CACNA2D1; DRD1; FGF14; GSTM2; JPH2; SNCA; TRDN | 0 | 0.00 | | 1 | 7.60 | CXCL9 | 4 | 1.85 | CACNA2D1; SNCA; TRDN; TRPC1 | 2 | 1.03 | CXCL11; NTSR1 |
| il2 1pathway | 55 | 6 | 1.83 | IFNG; IL2RA; JAK3; NRAS; SOCS3; STAT1 | 2 | 0.43 | BCL2; IRS2 | 0 | 0.00 | | 1 | 7.60 | IL2RA | 1 | 0.46 | BCL2 | 2 | 1.03 | CISH; SOCS3 |
| regulation of b cell proliferation: GO | 55 | 6 | 1.83 | CDKN1A; CTLA4; PRDM1; SASH3; TNFRSF21; TNFRSF4 | 3 | 0.64 | BCL2; IL5; IRS2 | 0 | 0.00 | | 0 | 0.00 | | 1 | 0.46 | BCL2 | 2 | 1.03 | CDKN1A; IL10 |
| ammonium transport: GO | 55 | 2 | 0.61 | ADCYAP1; RHCG | 7 | 1.50 | ACACB; DRD1; P2RX1; PRKAA2; RHAG; SLC6A2; SNCA | 0 | 0.00 | | 0 | 0.00 | | 4 | 1.85 | PRKAA2; RHBG; SLC18A2; SNCA | 2 | 1.03 | RHCG; SLC18A3 |
| cranial skeletal system development: GO | 55 | 2 | 0.61 | EIF4A3; TGFBR1 | 4 | 0.86 | FREM1; SIX1; SPEF2; TBX15 | 0 | 0.00 | | 0 | 0.00 | | 4 | 1.85 | FREM1; PRRX1; SPEF2; TBX15 | 2 | 1.03 | EIF4A3; WNT9B |
| insulin pathway | 55 | 1 | 0.30 | EIF4EBP1 | 3 | 0.64 | GRB14; SLC2A4; SORBS1 | 0 | 0.00 | | 0 | 0.00 | | 0 | 0.00 | | 2 | 1.03 | EIF4EBP1; SGK1 |
| regulation of response to extracellular stimulus: GO | 165 | 8 | 0.81 | CCK; CDK5R1; CYP27B1; GAPDH; HIF1A; | 8 | 0.57 | ATP6V0E2; ATP6V1B1; CARTPT; KANK2; KAT2A; LEP; | 0 | 0.00 | | 0 | 0.00 | | 3 | 0.46 | ATP6V0E2; DCN; PRKAA2 | 6 | 1.03 | CDK5R1; CYP27B1; GAPDH; HIF1A; SNAI2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | RALB; RUVBL1; VDAC1 | | | NRBP2; PRKAA2 | | | | | | | | | | | | VDAC1 |
| metabolism of steroids | 110 | 6 | 0.91 | AKR1B10; CYP24A1; CYP27B1; EBP; HMGCR; SQLE | 9 | 0.97 | ABCB11; ABCC3; ACACB; ACOX2; ALB; CYP17A1; GPAM; HSD11B1; PTGIS | 2 | 7.60 | GPAM; HSD11B2 | 0 | 0.00 | | 1 | 0.23 | ACOX2 | 4 | 1.03 | AKR1B10; CYP27B1; FEN1; SQLE |
| purine containing compound biosynthetic process: GO | 110 | 6 | 0.91 | ACOT7; AMD1; NME1; OAS1; OAS2; PNP | 9 | 0.97 | ACACB; ADCY2; ADCY5; ADCY6; ADCY8; AMPD1; ATP6V0A4; MAT1A; SLC26A1 | 0 | 0.00 | | 0 | 0.00 | | 1 | 0.23 | ATP6V0A4 | 4 | 1.03 | ACOT7; OAS1; PNP; UCN2 |
| presynaptic process involved in synaptic transmission: GO | 110 | 4 | 0.61 | HRH3; HSPA8; UNC13A; WNT7A | 16 | 1.72 | APBA1; CADPS; NLGN1; NRXN1; NRXN3; P2RX7; PCLO; RIMS1; RPH3AL; SLC6A2; SNCA; SYN2; SYT1; SYT17; SYT8; SYT9 | 0 | 0.00 | | 0 | 0.00 | | 8 | 1.85 | APBA1; NRXN1; PCLO; RIMS1; SLC18A2; SNCA; SYN2; SYT17 | 4 | 1.03 | HSPA8; SLC18A3; UNC13A; WNT7A |
| gap junction: GO | 28 | 7 | 4.18 | DSC1; GJA1; GJB2; GJB3; GJB5; GJB6; PANX1 | 2 | 0.84 | GJB4; GJC3 | 0 | 0.00 | | 0 | 0.00 | | 1 | 0.91 | GJB4 | 1 | 1.01 | PANX1 |
| phagocytosis recognition: GO | 28 | 5 | 2.99 | CLEC7A; IGHG1; IGHG2; IGHG4; IGKC | 2 | 0.84 | COLEC12; FCN2 | 1 | 14.92 | IGHG1 | 0 | 0.00 | | 3 | 2.72 | IGHM; IGHV3-23; TUB | 1 | 1.01 | CLEC7A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| positive regulation of monooxygenase activity: GO | 28 | 5 | 2.99 | CDH3; GDNF; HIF1A; IFNG; IL1B | 3 | 1.26 | APOE; FCER2; TERT | 0 | 0.00 | | 1 | 14.92 | IL1B | 1 | 0.91 | ESR1 | 1 | 1.01 | HIF1A |
| integrin2 pathway | 28 | 4 | 2.39 | ICAM3; ITGAX; PLAU; PLAUR | 2 | 0.84 | C3; F10 | 0 | 0.00 | | 0 | 0.00 | | 1 | 0.91 | C3 | 1 | 1.01 | PLAT |
| retinol metabolic process: GO | 28 | 4 | 2.39 | ADH7; ALDH1A3; LRAT; SDR16C5 | 3 | 1.26 | ALDH1A1; AWAT2; RBP4 | 0 | 0.00 | | 0 | 0.00 | | 1 | 0.91 | DGAT2 | 1 | 1.01 | LRAT |
| bard1 pathway | 28 | 3 | 1.79 | CCNE1; NPM1; PCNA | 0 | 0.00 | | 0 | 0.00 | | 0 | 0.00 | | 0 | 0.00 | | 1 | 1.01 | NPM1 |
| epidermis morphogenesis: GO | 28 | 3 | 1.79 | FOXE1; KRT17; TP63 | 1 | 0.42 | BCL2 | 0 | 0.00 | | 0 | 0.00 | | 2 | 1.81 | BCL2; IGFBP5 | 1 | 1.01 | FOXE1 |
| heme metabolic process: GO | 28 | 3 | 1.79 | HMOX1; HMOX2; UGT1A1 | 3 | 1.26 | ALAS2; AMBP; PPOX | 0 | 0.00 | | 0 | 0.00 | | 1 | 0.91 | PPOX | 1 | 1.01 | HMOX2 |
| heparan sulfate proteoglycan metabolic process: GO | 28 | 3 | 1.79 | HPSE; HS3ST3B1; SULF2 | 3 | 1.26 | EXTL1; HS3ST5; HS6ST3 | 0 | 0.00 | | 0 | 0.00 | | 0 | 0.00 | | 1 | 1.01 | HPSE |
| histone acetyltransferase binding: GO | 28 | 3 | 1.79 | HIF1A; NR4A3; PCNA | 2 | 0.84 | MYOCD; PAX6 | 0 | 0.00 | | 0 | 0.00 | | 0 | 0.00 | | 1 | 1.01 | HIF1A |
| regulation of mrna stability by proteins that bind au rich elements | 28 | 3 | 1.79 | PSMA4; PSMD1; YWHAZ | 0 | 0.00 | | 0 | 0.00 | | 0 | 0.00 | | 0 | 0.00 | | 1 | 1.01 | YWHAZ |
| regulation of protein oligomerization: GO | 28 | 3 | 1.79 | CCK; MMP1; MMP3 | 1 | 0.42 | CLU | 0 | 0.00 | | 0 | 0.00 | | 1 | 0.91 | CLU | 1 | 1.01 | MMP3 |
| binding and uptake of ligands by scavenger receptors | 28 | 2 | 1.20 | CALR; HSPH1 | 4 | 1.69 | ALB; AMBP; APOE; COLEC12 | 0 | 0.00 | | 0 | 0.00 | | 1 | 0.91 | GULP1 | 1 | 1.01 | HSPH1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| calmodulin dependent protein kinase activity: GO | 28 | 2 | 1.20 | CAMK1G; MYLK2 | 7 | 2.95 | CAMK1; CAMK2A; CAMK2B; DCX; EEF2K; PHKG1; PNCK | 0 | 0.00 | | 0 | 0.00 | | 2 | 1.81 | CAMK1; PHKG1 | 1 | 1.01 | CAMK1G |
| lis1 pathway | 28 | 2 | 1.20 | CDK5R1; LRP8 | 2 | 0.84 | DCX; RELN | 0 | 0.00 | | 0 | 0.00 | | 1 | 0.91 | RELN | 1 | 1.01 | CDK5R1 |
| necrotic cell death: GO | 28 | 2 | 1.20 | PPIF; PYGL | 0 | 0.00 | | 0 | 0.00 | | 0 | 0.00 | | 0 | 0.00 | | 1 | 1.01 | PPIF |
| presynaptic active zone: GO | 28 | 2 | 1.20 | RIMS3; UNC13A | 6 | 2.53 | ADORA1; GRM7; PCLO; RIMS1; SLC17A7; UNC13C | 0 | 0.00 | | 0 | 0.00 | | 2 | 1.81 | PCLO; RIMS1 | 1 | 1.01 | UNC13A |
| regulation of vacuolar transport: GO | 28 | 2 | 1.20 | MSN; NDRG4 | 1 | 0.42 | ACTN2 | 0 | 0.00 | | 0 | 0.00 | | 0 | 0.00 | | 1 | 1.01 | MSN |
| erk pathway | 28 | 1 | 0.60 | NGF | 0 | 0.00 | | 0 | 0.00 | | 0 | 0.00 | | 0 | 0.00 | | 1 | 1.01 | NGF |
| fatty acyl-coa biosynthesis | 28 | 1 | 0.60 | ELOVL7 | 1 | 0.42 | ELOVL2 | 0 | 0.00 | | 0 | 0.00 | | 0 | 0.00 | | 1 | 1.01 | FEN1 |
| hsp70 protein binding: GO | 28 | 1 | 0.60 | CDK1 | 1 | 0.42 | FGF1 | 0 | 0.00 | | 0 | 0.00 | | 0 | 0.00 | | 1 | 1.01 | CDK1 |
| proteoglycan binding: GO | 28 | 1 | 0.60 | CTSB | 7 | 2.95 | CFH; FCN2; GPC2; GPC3; GPC6; HPSE2; SLIT2 | 0 | 0.00 | | 0 | 0.00 | | 4 | 3.63 | CFH; GPC2; HPSE2; SLIT2 | 1 | 1.01 | AGRN |
| regulation of sprouting angiogenesis: GO | 28 | 1 | 0.60 | PTGS2 | 1 | 0.42 | HDAC5 | 0 | 0.00 | | 0 | 0.00 | | 1 | 0.91 | FGF2 | 1 | 1.01 | PTGS2 |
| regulation of synaptic transmission gabaergic: GO | 28 | 1 | 0.60 | CA2 | 5 | 2.11 | ADORA1; ADRA1A; CNR1; NLGN1; NPY5R | 0 | 0.00 | | 0 | 0.00 | | 1 | 0.91 | ADRA1A | 1 | 1.01 | CA2 |
| smooth muscle contraction | 28 | 1 | 0.60 | ANXA1 | 5 | 2.11 | LMOD1; MYL9; SORBS1; TPM1; TPM2 | 0 | 0.00 | | 0 | 0.00 | | 1 | 0.91 | LMOD1 | 1 | 1.01 | TPM4 |
| telomeric dna binding: GO | 28 | 1 | 0.60 | PIF1 | 1 | 0.42 | TERT | 0 | 0.00 | | 0 | 0.00 | | 0 | 0.00 | | 1 | 1.01 | PIF1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| asthma | 28 | 0 | 0.00 | | 1 | 0.42 | IL5 | 0 | 0.00 | | 0 | 0.00 | | 1 | 0.91 | MS4A2 | 1 | 1.01 | IL10 |
| glyoxylate metabolic process: GO | 28 | 0 | 0.00 | | 1 | 0.42 | HOGA1 | 0 | 0.00 | | 0 | 0.00 | | 0 | 0.00 | | 1 | 1.01 | GLDC |
| long term memory: GO | 28 | 0 | 0.00 | | 6 | 2.53 | ADCY8; GRIA1; GRIN1; RELN; SHANK1; SLC17A7 | 0 | 0.00 | | 0 | 0.00 | | 2 | 1.81 | GRIA1; RELN | 1 | 1.01 | SGK1 |
| lamellipodium: GO | 166 | 13 | 1.31 | ACTR3; ARPC3; CFL1; DPP4; DYSF; ENAH; FSCN1; MEFV; PDPN; PLEK2; RAC2; SH3BGRL3; SLC39A6 | 10 | 0.71 | ACTA1; AMOT; APBB1; CTNNA3; GSN; KCNA2; PLEKHG5; PPPR9A; SORBS2; SRCIN1 | 1 | 2.52 | SRCIN1 | 1 | 2.52 | RAC2 | 3 | 0.46 | DPYSL3; SORBS2; TESC | 6 | 1.02 | CFL1; DPP4; ENAH; EPHA2; MEFV; PLEK2 |
| positive regulation of cytoskeleton organization: GO | 166 | 12 | 1.21 | ACTR3; ARPC1A; ARPC3; ARPC5L; CCL21; CCNB1; F2RL1; GPR65; PFN1; PRKCQ; PYCARD; RANBP1 | 11 | 0.78 | ACTN2; AMOT; GSN; MAPT; MYOC; NTRK3; P2RX7; PLXNA3; SCIN; TPM1; WNT11 | 0 | 0.00 | | 0 | 0.00 | | 6 | 0.92 | CTGF; LPAR1; MAPT; MYOC; SCIN; WNT11 | 6 | 1.02 | ARPC1A; CCNB1; CDC42EP1; PFN1; PLK4; PRKCQ |
| peptide ligand binding | 111 | 16 | 2.41 | BDKRB1; BDKRB2; CCL17; CCL22; CCL3; CCL7; CCR4; CCR5; CXCL5; CXCL9; CXCR1; | 8 | 0.85 | CCKBR; CXCR5; EDN3; GALR1; NMUR1; NPY5R; PROK1; TAC3 | 0 | 0.00 | | 2 | 7.53 | CXCL5; CXCL9 | 1 | 0.23 | EDN3 | 4 | 1.02 | BDKRB2; CXCR1; NTSR1; QRFPR |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | FPR3; INSL3; NPSR1; NTSR1; QRFPR | | | | | | | | | | | | | | | |
| liposaccharide metabolic process: GO | 111 | 10 | 1.51 | ARSH; B3GNT5; CWH43; GLTP; NEU2; PIGW; PLAUR; ST6GALNAC1; ST8SIA2; UGCG | 3 | 0.32 | GAL3ST1; GPLD1; ST6GALNAC5 | 0 | 0.00 | | 0 | 0.00 | | 5 | 1.14 | ALDH5A1; GAL3ST4; GPLD1; PSAPL1; ST6GALNAC5 | 4 | 1.02 | B3GNT5; PIGW; ST6GALNAC1; ST8SIA2 |
| ribonucleoprotein complex localization: GO | 111 | 4 | 0.60 | EIF4A3; EIF5A; EIF6; RAN | 1 | 0.11 | DDX25 | 0 | 0.00 | | 0 | 0.00 | | 1 | 0.23 | DDX25 | 4 | 1.02 | DDX39A; EIF4A3; EIF6; RAN |
| multicellular organismal water homeostasis: GO | 56 | 7 | 2.09 | ABCA12; AQP3; GRHL3; HRNR; KRT16; SFN; TP63 | 9 | 1.90 | ADCY2; ADCY5; ADCY6; ADCY8; AQP4; CYP4A11; CYP4F12; PRKAR2B; TFAP2B | 1 | 7.46 | PRKAR2B | 0 | 0.00 | | 3 | 1.36 | CYP4A11; CYP4F12; SCNN1B | 2 | 1.01 | AQP3; SFN |
| t cell activation involved in immune response: GO | 56 | 6 | 1.79 | EOMES; F2RL1; IFNE; IFNG; IL12B; IL6 | 2 | 0.42 | IFNA5; RORC | 0 | 0.00 | | 0 | 0.00 | | 0 | 0.00 | | 2 | 1.01 | BCL3; IFNE |
| tetrapyrrole metabolic process: GO | 56 | 5 | 1.49 | HMOX1; HMOX2; PRSS3; TCN1; UGT1A1 | 5 | 1.05 | ALAS2; AMBP; CYP1A1; CYP1A2; PPOX | 0 | 0.00 | | 0 | 0.00 | | 1 | 0.45 | PPOX | 2 | 1.01 | HMOX2; PRSS3 |
| outflow tract morphogenesis: GO | 56 | 3 | 0.90 | HIF1A; TBX20; WNT5A | 8 | 1.69 | FOLR1; HAND2; NKX2-5; NPY1R; NPY5R; SIX1; WNT11; ZFPM2 | 0 | 0.00 | | 0 | 0.00 | | 4 | 1.81 | HAND2; NPY1R; WNT11; ZFPM2 | 2 | 1.01 | HIF1A; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| p53 regulation pathway | 56 | 3 | 0.90 | CCNA2; CHEK1; CSNK1A1 | 0 | 0.00 | | 0 | 0.00 | | 0 | 0.00 | | 0 | 0.00 | | 2 | 1.01 | CCNA2; CHEK1 |
| inositol phosphate metabolic process: GO | 56 | 2 | 0.60 | NTSR1; PTAFR | 4 | 0.84 | NUDT10; NUDT11; PLCB4; PLCH2 | 0 | 0.00 | | 0 | 0.00 | | 3 | 1.36 | FGF2; PLCB4; PLCZ1 | 2 | 1.01 | NTSR1; PTAFR |
| negative regulation of cell projection organization: GO | 139 | 6 | 0.72 | CCL21; CDK5R1; ITGA3; PLK2; SEMA4B; WNT5A | 13 | 1.10 | ADCY6; APOE; LRP4; NLGN1; NRXN1; PLXNA3; SEMA3A; SEMA3B; SEMA3D; SEMA3E; SEMA3G; SLIT2; SPOCK1 | 0 | 0.00 | | 0 | 0.00 | | 7 | 1.28 | DPYSL3; LPAR1; NRXN1; SEMA3E; SEMA4G; SLIT2; SPOCK1 | 5 | 1.02 | CDK5R1; ITGA3; PLK2; SEMA4B; WNT5A |
| multicellular organism metabolic process: GO | 84 | 8 | 1.59 | CTSB; HIF1A; KLK6; MMP1; MMP10; MMP12; MMP3; MMP9 | 10 | 1.40 | ADRB1; CLIC5; COL11A1; COL11A2; COL19A1; COL25A1; GHR; P2RX7; PPARGC1A; TNXB | 1 | 4.97 | GHR | 0 | 0.00 | | 4 | 1.21 | CLIC5; COL11A1; MMP27; PPARGC1A | 3 | 1.01 | ADAMTS14; HIF1A; MMP3 |
| positive regulation of camp metabolic process: GO | 84 | 8 | 1.59 | ADCYAP1; CAP1; CXCL10; CXCL11; CXCL9; GPR65; INSL3; PTHLH | 12 | 1.69 | ADCY2; ADCY5; ADCY6; ADCY8; ADRB1; AKAP12; CALCR; DRD1; LHCGR; SCT; TSHR; VIPR2 | 1 | 4.97 | MRAP2 | 1 | 4.97 | CXCL9 | 3 | 0.91 | ADCYAP1R1; AKAP12; TSHR | 3 | 1.01 | CAP1; CXCL11; PTHLH |
| positive regulation of viral | 84 | 5 | 1.00 | CFL1; PFN1; PPIA; PPIB; TOP2A | 2 | 0.28 | APOE; TMPRSS2 | 0 | 0.00 | | 0 | 0.00 | | 0 | 0.00 | | 3 | 1.01 | CFL1; PFN1; TOP2A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| process: GO | | | | | | | | | | | | | | | | | | | |
| nkt pathway | 29 | 9 | 5.19 | CCL3; CCR4; CCR5; CSF2; CXCR4; IFNG; IL12B; IL12RB2; IL4R | 1 | 0.41 | IL5 | 0 | 0.00 | | 0 | 0.00 | | 0 | 0.00 | | 1 | 0.98 | IL12RB2 |
| glutathione conjugation | 29 | 6 | 3.46 | CHAC1; CHAC2; CNDP2; GGCT; GSTO1; GSTP1 | 4 | 1.63 | GGT7; GSTA3; GSTM3; GSTM5 | 0 | 0.00 | | 0 | 0.00 | | 1 | 0.88 | GSTM5 | 1 | 0.98 | GSTP1 |
| disulfide oxidoreductase activity: GO | 29 | 5 | 2.89 | GSTO1; PDIA3; SH3BGRL3; TXN; TXNDC8 | 0 | 0.00 | | 0 | 0.00 | | 0 | 0.00 | | 1 | 0.88 | GLRX | 1 | 0.98 | TXN |
| positive regulation of cytokine production involved in immune response: GO | 29 | 5 | 2.89 | F2RL1; NR4A3; RSAD2; SASH3; WNT5A | 0 | 0.00 | | 0 | 0.00 | | 1 | 14.41 | FFAR2 | 1 | 0.88 | GPRC5B | 1 | 0.98 | WNT5A |
| leukocyte degranulation: GO | 29 | 4 | 2.31 | ANXA3; CCL3; NR4A3; PLA2G3 | 1 | 0.41 | KLRF2 | 0 | 0.00 | | 1 | 14.41 | ANXA3 | 1 | 0.88 | KLRF2 | 1 | 0.98 | PLA2G3 |
| negative regulation of endothelial cell proliferation: GO | 29 | 4 | 2.31 | GJA1; SCG2; STAT1; TGFBR1 | 3 | 1.22 | APOE; ATOH8; TNMD | 0 | 0.00 | | 0 | 0.00 | | 2 | 1.75 | ATOH8; TNMD | 1 | 0.98 | XDH |
| t cell differentiation involved in immune response: GO | 29 | 4 | 2.31 | EOMES; IFNG; IL12B; IL6 | 1 | 0.41 | RORC | 0 | 0.00 | | 0 | 0.00 | | 0 | 0.00 | | 1 | 0.98 | BCL3 |
| g1 s transition | 29 | 3 | 1.73 | PKMYT1; PSMA4; PSMD1 | 0 | 0.00 | | 0 | 0.00 | | 0 | 0.00 | | 0 | 0.00 | | 1 | 0.98 | PKMYT1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| positive regulation of amine transport: GO | 29 | 3 | 1.73 | CCK; GDNF; NTSR1 | 6 | 2.44 | CARTPT; DRD4; KCNB1; P2RX7; PCP4; RAB3B | 0 | 0.00 | | 0 | 0.00 | | 2 | 1.75 | CXCL12; RAB3B | 1 | 0.98 | NTSR1 |
| positive regulation of viral genome replication: GO | 29 | 3 | 1.73 | PPIA; PPIB; TOP2A | 0 | 0.00 | | 0 | 0.00 | | 0 | 0.00 | | 0 | 0.00 | | 1 | 0.98 | TOP2A |
| protein export from nucleus: GO | 29 | 3 | 1.73 | CALR; EIF5A; RAN | 1 | 0.41 | PKD1 | 0 | 0.00 | | 0 | 0.00 | | 0 | 0.00 | | 1 | 0.98 | RAN |
| regulation of heart rate by cardiac conduction: GO | 29 | 3 | 1.73 | DSC2; DSP; JUP | 3 | 1.22 | ANK2; CACNA2D1; CTNNA3 | 0 | 0.00 | | 0 | 0.00 | | 2 | 1.75 | CACNA1G; CACNA2D1 | 1 | 0.98 | DSC2 |
| s1p s1p3 pathway | 29 | 3 | 1.73 | CXCR4; GNA15; GNAI3 | 1 | 0.41 | GNAZ | 0 | 0.00 | | 0 | 0.00 | | 0 | 0.00 | | 1 | 0.98 | GNA15 |
| steroid hormones | 29 | 3 | 1.73 | CYP24A1; CYP27B1; STARD4 | 4 | 1.63 | CYP17A1; CYP21A2; HSD11B1; LHB | 0 | 0.00 | | 0 | 0.00 | | 0 | 0.00 | | 1 | 0.98 | CYP27B1 |
| tak1 activates nfkb by phosphorylation and activation of ikks complex | 29 | 3 | 1.73 | MYD88; S100A12; UBE2N | 0 | 0.00 | | 0 | 0.00 | | 0 | 0.00 | | 0 | 0.00 | | 1 | 0.98 | MYD88 |
| amine ligand binding receptors | 29 | 2 | 1.15 | HRH3; HTR7 | 8 | 3.25 | ADRA1B; ADRA2A; CHRM1; CHRM2; CHRM3; DRD1; HTR4; HTR6 | 0 | 0.00 | | 0 | 0.00 | | 3 | 2.63 | ADRA2A; CHRM1; CHRM3 | 1 | 0.98 | HRH2 |
| cardiac atrium development: GO | 29 | 2 | 1.15 | TBX20; WNT5A | 4 | 1.63 | ANK2; MESP1; NKX2-5; TBX5 | 0 | 0.00 | | 0 | 0.00 | | 2 | 1.75 | MESP1; SHOX2 | 1 | 0.98 | WNT5A |
| intrinsic pathway | 29 | 2 | 1.15 | C1QBP; F12 | 2 | 0.81 | F10; KLKB1 | 0 | 0.00 | | 0 | 0.00 | | 0 | 0.00 | | 1 | 0.98 | F12 |
| negative | 29 | 2 | 1.15 | GSTO1; | 4 | 1.63 | CASQ2; | 0 | 0.00 | | 0 | 0.00 | | 2 | 1.75 | PPARGC1A; | 1 | 0.98 | PCSK9 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| regulation of receptor activity: GO | | | | PCSK9 | | | GSTM2; PPARGC1A; TRDN | | | | | | | | | TRDN | | | |
| signaling by high-kinase activity braf mutants | 29 | 2 | 1.15 | ACTB; NRAS | 1 | 0.41 | CNKSR2 | 0 | 0.00 | | 0 | 0.00 | | 1 | 0.88 | CNKSR2 | 1 | 0.98 | ACTB |
| sodium ion homeostasis: GO | 29 | 2 | 1.15 | ATP12A; ATP1B3 | 7 | 2.85 | AGT; ATP1A2; CYP4A11; CYP4F12; SCN7A; SGK2; TFAP2B | 0 | 0.00 | | 0 | 0.00 | | 5 | 4.38 | ATP1B2; CYP4A11; CYP4F12; SCN7A; SCNN1B | 1 | 0.98 | SGK1 |
| tnfr1 pathway | 29 | 2 | 1.15 | LMNB1; LMNB2 | 0 | 0.00 | | 0 | 0.00 | | 0 | 0.00 | | 0 | 0.00 | | 1 | 0.98 | LMNB2 |
| tnfr1 signaling pathway | 29 | 2 | 1.15 | LMNB1; LMNB2 | 0 | 0.00 | | 0 | 0.00 | | 0 | 0.00 | | 0 | 0.00 | | 1 | 0.98 | LMNB2 |
| vegf pathway | 29 | 2 | 1.15 | EIF2S1; HIF1A | 0 | 0.00 | | 0 | 0.00 | | 0 | 0.00 | | 0 | 0.00 | | 1 | 0.98 | HIF1A |
| benzoate degradation via coa ligation | 29 | 1 | 0.58 | ESCO2 | 2 | 0.81 | FN3K; PNPLA3 | 0 | 0.00 | | 0 | 0.00 | | 2 | 1.75 | FN3K; PNPLA3 | 1 | 0.98 | DHRS2 |
| blastocyst formation: GO | 29 | 1 | 0.58 | EOMES | 1 | 0.41 | TET1 | 0 | 0.00 | | 0 | 0.00 | | 1 | 0.88 | TET1 | 1 | 0.98 | JUNB |
| heparan sulfate/ heparin (hs-gag) metabolism | 29 | 1 | 0.58 | SDC1 | 6 | 2.44 | GPC3; GPC6; HS3ST5; HS6ST3; IDUA; SDC2 | 0 | 0.00 | | 0 | 0.00 | | 1 | 0.88 | DCN | 1 | 0.98 | AGRN |
| peptide hormone processing: GO | 29 | 1 | 0.58 | NGF | 5 | 2.03 | AGT; LHB; PCSK2; PCSK5; REN | 0 | 0.00 | | 0 | 0.00 | | 3 | 2.63 | CORIN; CPE; CTSG | 1 | 0.98 | NGF |
| positive regulation of nik nf kappab signaling: GO | 29 | 1 | 0.58 | TNFRSF10A | 0 | 0.00 | | 0 | 0.00 | | 0 | 0.00 | | 0 | 0.00 | | 1 | 0.98 | CARD10 |
| regulation of defense response to virus by virus: GO | 29 | 1 | 0.58 | AP1S3 | 0 | 0.00 | | 0 | 0.00 | | 0 | 0.00 | | 0 | 0.00 | | 1 | 0.98 | AP1S3 |
| rna polymerase | 29 | 1 | 0.58 | POLR3G | 0 | 0.00 | | 0 | 0.00 | | 0 | 0.00 | | 0 | 0.00 | | 1 | 0.98 | POLR3G |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| cyclic nucleotide biosynthetic process: GO | 29 | 0 | 0.00 | | 4 | 1.63 | ADCY2; ADCY5; ADCY6; ADCY8 | 0 | 0.00 | | 0 | 0.00 | | 0 | 0.00 | | 1 | 0.98 | UCN2 |
| phosphate transmembrane transporter activity: GO | 29 | 0 | 0.00 | | 2 | 0.81 | SLC17A7; SLC34A3 | 0 | 0.00 | | 0 | 0.00 | | 0 | 0.00 | | 1 | 0.98 | SLC20A1 |
| response to fibroblast growth factor: GO | 112 | 4 | 0.60 | CXCL13; FGFBP1; FLRT3; TNC | 10 | 1.05 | FGF1; FGF14; FGF17; FGF22; FGF9; FGFR1; FGFR3; NOG; SCGB1A1; SNCA | 0 | 0.00 | | 0 | 0.00 | | 5 | 1.13 | CTGF; FGF2; FGF22; FGFR1; SNCA | 4 | 1.01 | FGFBP1; FLRT3; SHCBP1; SNAI2 |
| regulation of cytokine secretion: GO | 140 | 26 | 3.11 | ANXA1; CAMP; CCL3; CD2; CD274; CLEC6A; F2RL1; IFNG; IL1A; IL1B; IL1RL1; IL26; IL36RN; IL4R; IL6; NLRP2; PANX1; PYCARD; SLAMF1; SRGN; TLR10; TNFRSF21; TNFRSF9; TRIM16; WNT5A; ZC3H12A | 6 | 0.51 | CD34; GPAM; LPL; P2RX7; PAEP; SSC5D | 2 | 5.97 | GPAM; LPL | 3 | 8.95 | FFAR2; GBP1; IL1B | 4 | 0.73 | ANGPT1; CD34; FBLN1; SSC5D | 5 | 1.01 | IL10; NLRP2; PANX1; WNT5A; ZC3H12A |
| ribonucleoprotein granule: GO | 140 | 7 | 0.84 | ACTB; DDX28; EIF2S1; INA; PSMA4; SNRPG; ZC3H12A | 6 | 0.51 | CPEB1; DDX25; DYNC1I1; MAPT; PIWIL2; TDRD5 | 0 | 0.00 | | 0 | 0.00 | | 4 | 0.73 | CPEB1; DDX25; MAPT; TDRD6 | 5 | 1.01 | ACTB; DDX28; INA; TDRD9; ZC3H12A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| gliogenesis: GO | 168 | 10 | 1.00 | ANXA1; AREG; CCL3; CDK5R1; GSTP1; NRG1; P2RY1; S100A8; S100A9; TRPC4 | 21 | 1.47 | ADAM22; CLU; DCX; DRD1; DTX1; FA2H; GSN; ID4; KLF15; LAMA2; LAMC3; LGI4; LIF; MYOC; OLIG1; PAX6; PLP1; PRDM8; RELN; SOX10; SOX8 | 0 | 0.00 | | 0 | 0.00 | | 9 | 1.36 | ADAM22; CLU; LAMA2; LAMC3; LGI4; LPAR1; MYOC; PLP1; RELN | 6 | 1.01 | AREG; CDK5R1; GSTP1; NDRG1; NRG1; P2RY1 |
| humoral immune response mediated by circulating immunoglobulin: GO | 57 | 7 | 2.05 | C1QBP; EXO1; IGHG1; IGHG2; IGHG4; IGKC; IGKV4-1 | 5 | 1.03 | C3; C4BPA; C6; C7; CLU | 2 | 14.66 | IGHG1; IGKV3-20 | 0 | 0.00 | | 4 | 1.78 | C3; CLU; IGHM; IGHV3-23 | 2 | 0.99 | BCL3; EXO1 |
| er-phagosome pathway | 57 | 6 | 1.76 | CALR; MYD88; PDIA3; PSMA5; PSMB6; SEC61G | 0 | 0.00 | | 0 | 0.00 | | 0 | 0.00 | | 0 | 0.00 | | 2 | 0.99 | HLA-G; MYD88 |
| mitochondrial protein import | 57 | 6 | 1.76 | COQ2; GRPEL2; TIMM13; TIMM23; TIMM8B; VDAC1 | 1 | 0.21 | LDHD | 0 | 0.00 | | 0 | 0.00 | | 0 | 0.00 | | 2 | 0.99 | GRPEL2; VDAC1 |
| regulation of glial cell differentiation: GO | 57 | 5 | 1.47 | CDK1; CXCR4; IL1B; SERPINE2; TNFRSF21 | 5 | 1.03 | ID4; LIF; NOG; NTRK3; RNF112 | 0 | 0.00 | | 1 | 7.33 | IL1B | 2 | 0.89 | MYCN; RNF112 | 2 | 0.99 | CDK1; SERPINE2 |
| regulation of viral transcription: GO | 57 | 5 | 1.47 | CCL3; HMGA2; IFITM3; PFN1; | 1 | 0.21 | POU2F3 | 0 | 0.00 | | 1 | 7.33 | IFITM3 | 0 | 0.00 | | 2 | 0.99 | HMGA2; PFN1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | TRIM14 | | | | | | | | | | | | | | | |
| acute myeloid leukemia | 57 | 3 | 0.88 | EIF4EBP1; JUP; NRAS | 3 | 0.62 | RUNX1T1; TCF7L1; ZBTB16 | 0 | 0.00 | | 0 | 0.00 | | 2 | 0.89 | RUNX1T1; TCF7L1 | 2 | 0.99 | EIF4EBP1; PPARD |
| embryonic digit morphogenesis: GO | 57 | 3 | 0.88 | GJA1; WNT5A; WNT7A | 8 | 1.66 | ALX4; GLI2; HAND2; LRP4; NOG; OSR1; OSR2; ZBTB16 | 0 | 0.00 | | 0 | 0.00 | | 6 | 2.67 | ALX4; B9D1; GLI2; HAND2; MYCN; OSR1 | 2 | 0.99 | WNT5A; WNT7A |
| main axon: GO | 57 | 3 | 0.88 | CCK; CNTNAP2; NRG1 | 11 | 2.28 | ADORA1; APBB1; DLG2; DNM1; KCNA1; KCNA2; MYOC; SLC1A2; SPOCK1; SPTBN4; TUBB4A | 0 | 0.00 | | 0 | 0.00 | | 4 | 1.78 | DLG2; MYOC; SPOCK1; SPTBN4 | 2 | 0.99 | CNTNAP2; NRG1 |
| map kinase activation in tlr cascade | 57 | 3 | 0.88 | CDK1; DUSP6; UBE2N | 0 | 0.00 | | 0 | 0.00 | | 0 | 0.00 | | 0 | 0.00 | | 2 | 0.99 | CDK1; DUSP6 |
| oligodendrocyte differentiation: GO | 57 | 3 | 0.88 | GSTP1; NRG1; TRPC4 | 10 | 2.07 | CLU; FA2H; GSN; ID4; OLIG1; PAX6; PLP1; PRDM8; SOX10; SOX8 | 0 | 0.00 | | 0 | 0.00 | | 3 | 1.34 | CLU; LPAR1; PLP1 | 2 | 0.99 | GSTP1; NRG1 |
| protein homotetra merization: GO | 57 | 3 | 0.88 | CDA; TK1; TP63 | 5 | 1.03 | ACACB; ACADL; ACTN2; DHPS; RXRG | 0 | 0.00 | | 0 | 0.00 | | 1 | 0.45 | ALDH5A1 | 2 | 0.99 | CDA; TK1 |
| dna methylation or demethylation: GO | 57 | 1 | 0.29 | APOBEC3A | 3 | 0.62 | PIWIL2; TDRD5; TET1 | 0 | 0.00 | | 0 | 0.00 | | 1 | 0.45 | TET1 | 2 | 0.99 | BEND3; TDRD9 |
| regulation of calcium ion transport: GO | 196 | 17 | 1.45 | BAK1; BDKRB1; CCL3; CXCL10; CXCL11; CXCL9; | 26 | 1.57 | ADRA2A; AGT; ANK2; ATP1A2; ATP2B2; BCL2; CACNA2D1; | 0 | 0.00 | | 1 | 2.13 | CXCL9 | 11 | 1.43 | ADCYAP1R1; ADRA2A; BCL2; CACNA2D1; CACNB1; CXCL12; | 7 | 1.01 | BAK1; CXCL11; HOMER1; NTSR1; PTGS2; TRPV3; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | CXCR4; GJA1; GSTO1; HOMER1; JAK3; LPAR3; NPSR1; NTSR1; PTGS2; TRPC4; UBASH3B | | | CACNB1; CAMK2A; CAMK2B; CASQ2; CLDN16; DMD; DRD1; DRD4; EGF; FGF14; GSTM2; JPH2; P2RX1; P2RX7; PLA2G6; SLN; SNCA; SPINK1; TRDN | | | | | | | | | EGF; HRC; SNCA; TRDN; TRPC1 | | | UBASH3B |
| skeletal system morphogenesis: GO | 196 | 7 | 0.60 | ACP5; ALPL; EIF4A3; LTF; MDFI; TGFBR1; WNT7A | 19 | 1.14 | ALX1; ALX4; COL11A1; DSCAML1; FGFR1; FGFR3; FREM1; GSC; HHIP; MGP; NOG; OSR1; OSR2; P2RX7; PKD1; SIX1; SP5; SPEF2; TBX15 | 0 | 0.00 | | 0 | 0.00 | | 13 | 1.69 | ALX4; COL11A1; CTGF; FGFR1; FREM1; HOXD8; MYCN; OSR1; PRRX1; SHOX2; SP5; SPEF2; TBX15 | 7 | 1.01 | ACP5; BMPRB; EIF4A3; LTF; MDFI; WNT7A; WNT9B |
| positive regulation of peptide secretion: GO | 85 | 6 | 1.18 | ADCYAP; GJA1; HIF1A; S100A8; S100A9; VSNL1 | 9 | 1.25 | ADORA1; CFTR; GPLD1; ILDR1; IRS2; LIF; PLA2G6; RBP4; SCT | 0 | 0.00 | | 0 | 0.00 | | 3 | 0.90 | GPLD1; ILDR1; MYRIP | 3 | 1.00 | HIF1A; PPARD; VSNL1 |
| cxcr4 pathway | 113 | 10 | 1.48 | CD3E; CFL1; CXCR4; GNAI3; ITGA3; ITGA6; MMP9; RALB; RGS1; | 4 | 0.42 | DNM1; GNAZ; ITGA7; ITGA8 | 0 | 0.00 | | 0 | 0.00 | | 3 | 0.67 | CXCL12; ITGA11; PIK3R6 | 4 | 1.00 | CFL1; ITGA3; ITGA6; RGS1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | STAT1 | | | | | | | | | | | | | | | |
| lipase activity: GO | 113 | 10 | 1.48 | BDKRB2; CCR5; FAM83B; HMOX1; LIPG; LYPLA1; PDIA3; PLA2G3; PLA2G4D; PLBD1 | 14 | 1.46 | ADORA1; CCKBR; CHRM1; CHRM3; GPLD1; LIPH; LPL; PLA2G16; PLA2G5; PLA2G6; PLCB4; PLCH2; PNPLA3; PNPLA7 | 2 | 7.40 | LPL; PLA2G16 | 0 | 0.00 | | 9 | 2.02 | CHRM1; CHRM3; GPLD1; LIPH; LIPK; LIPM; PLCB4; PLCZ1; PNPLA3 | 4 | 1.00 | BDKRB2; PLA2G3; PLA2G4D; PLCD4 |
| sh3 domain binding: GO | 113 | 7 | 1.04 | CD3E; ENAH; ENKUR; GJA1; PLSCR3; PTTG1; SH2D2A | 11 | 1.15 | ARHGAP6; DRD4; DTX1; ESPN; GRIK5; MAPK15; MAPT; PAK3; RIMS1; SH3BGRL2; SHANK1 | 0 | 0.00 | | 0 | 0.00 | | 5 | 1.12 | DPYSL3; MAPT; PAK3; RIMS1; SH3BGRL2 | 4 | 1.00 | ADAM19; AFAPIL2; ENAH; PTTG1 |
| site of polarized growth: GO | 141 | 9 | 1.07 | CDK5R1; CXADR; FLRT3; FSCN1; GPRIN1; ITGA3; KIF20B; NEFL; SNCB | 18 | 1.51 | APBB1; BOC; CLU; CNR1; COBL; CPEB1; FRMD7; MAPK8IP1; MAPT; MYH14; MYO1A; NRXN1; PCDH9; PCDHGB1; PPP1R9A; PTCH1; SNCA; TRPM1 | 0 | 0.00 | | 0 | 0.00 | | 9 | 1.62 | CLU; CPEB1; DPYSL3; FRY; MAPT; NRXN1; PCDHGB1; PTCH1; SNCA | 5 | 1.01 | CDK5R1; FLRT3; GPRIN1; ITGA3; SNCB |
| cullin ring ubiquitin ligase | 141 | 7 | 0.83 | BUB1B; CDC20; DTL; | 6 | 0.50 | ASB4; BACH2; | 0 | 0.00 | | 1 | 2.96 | KLHDC7B | 5 | 0.90 | BACH2; FBXL7; GAN; | 5 | 1.01 | BUB1B; CDC20; DTL; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| complex: GO | | | | KBTBD8; KLHDC7B; UBE2C; UBE2S | | | FBXO44; KBTBD12; KLHL31; KLHL33 | | | | | | | | | KBTBD3; KLHL31 | | | UBE2C; UBE2S |
| carbohydrate derivative catabolic process: GO | 169 | 15 | 1.49 | AHCY; APOBEC3A; CDA; CHI3L2; HMMR; HPSE; HYAL3; NEU2; NUDT15; PGLYRP2; PGM2; PNP; SDC1; TYMP; UPP1 | 16 | 1.12 | BCAN; ENPP4; GALT; GPC2; GPC3; GPC6; GPD1; HPSE2; IDUA; NEIL1; PDE11A; PDE9A; PRELP; RENBP; SDC2; UPP2 | 1 | 2.47 | GPD1 | 0 | 0.00 | | 5 | 0.75 | DCN; FGF2; GPC2; HPSE2; PDE9A | 6 | 1.01 | AGRN; CDA; HMMR; HPSE; NUDT15; PNP |
| regulation of neutrophil migration: GO | 30 | 6 | 3.35 | C1QBP; CCL21; CXCL1; CXCL3; IL1B; RAC2 | 1 | 0.39 | SLIT2 | 0 | 0.00 | | 2 | 27.86 | IL1B; RAC2 | 1 | 0.85 | SLIT2 | 1 | 0.95 | CXCL2 |
| signal transduction through il1r | 30 | 6 | 3.35 | IL1A; IL1B; IL1RAP; IL1RN; IL6; MYD88 | 0 | 0.00 | | 0 | 0.00 | | 1 | 13.93 | IL1B | 0 | 0.00 | | 1 | 0.95 | MYD88 |
| acetylcholine receptor activity: GO | 30 | 5 | 2.79 | CHRNA3; CHRNA6; CHRNA9; HRH3; HTR3A | 6 | 2.36 | CHRM1; CHRM2; CHRM3; CHRM4; CHRNA2; HTR3E | 0 | 0.00 | | 0 | 0.00 | | 3 | 2.54 | ANXA9; CHRM1; CHRM3 | 1 | 0.95 | CHRNA6 |
| keratinization | 30 | 5 | 2.79 | CSTA; DSG3; JUP; PERP; PI3 | 2 | 0.79 | KRT15; KRT86 | 0 | 0.00 | | 0 | 0.00 | | 3 | 2.54 | CRNN; KRT23; KRT86 | 1 | 0.95 | CSTA |
| regulation of mast cell activation involved in immune response: GO | 30 | 5 | 2.79 | FOXF1; HMOX1; IL13RA2; IL4R; RAC2 | 0 | 0.00 | | 0 | 0.00 | | 1 | 13.93 | RAC2 | 0 | 0.00 | | 1 | 0.95 | IL13RA2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| negative regulation of b cell activation: GO | 30 | 4 | 2.23 | CTLA4; PRDM1; SAMSN1; TNFRSF21 | 0 | 0.00 | | 0 | 0.00 | | 1 | 13.93 | SAMSN1 | 0 | 0.00 | | 1 | 0.95 | IL10 |
| phenylalanine metabolism | 30 | 4 | 2.23 | ALDH1A3; ESCO2; GOT2; IL4I1 | 3 | 1.18 | AOC3; MAOA; PNPLA3 | 0 | 0.00 | | 0 | 0.00 | | 1 | 0.85 | PNPLA3 | 1 | 0.95 | GOT2 |
| pyrimidine ribonucleoside metabolic process: GO | 30 | 4 | 2.23 | APOBEC3A; CDA; NME1; UPP1 | 1 | 0.39 | UPP2 | 0 | 0.00 | | 0 | 0.00 | | 0 | 0.00 | | 1 | 0.95 | CDA |
| adherens junctions interactions | 30 | 3 | 1.67 | ACTB; CDH3; JUP | 3 | 1.18 | CADM2; CDH12; CDH4 | 0 | 0.00 | | 0 | 0.00 | | 1 | 0.85 | CADM2 | 1 | 0.95 | ACTB |
| glutamate metabolism | 30 | 3 | 1.67 | ALDH4A1; EPRS; GOT2 | 1 | 0.39 | GPT | 0 | 0.00 | | 0 | 0.00 | | 2 | 1.69 | ALDH5A1; GPT | 1 | 0.95 | GOT2 |
| heterotrimeric g protein complex: GO | 30 | 3 | 1.67 | GNA15; GNAI3; GNGT2 | 4 | 1.57 | GNAZ; RGS11; RGS6; RGS9 | 1 | 13.93 | RGS11 | 0 | 0.00 | | 1 | 0.85 | GNG11 | 1 | 0.95 | GNA15 |
| limonene and pinene degradation | 30 | 3 | 1.67 | ALDH1A3; ESCO2; YOD1 | 2 | 0.79 | CYP2C9; PNPLA3 | 0 | 0.00 | | 0 | 0.00 | | 2 | 1.69 | ALDH3A2; PNPLA3 | 1 | 0.95 | DHRS2 |
| organellar large ribosomal subunit: GO | 30 | 3 | 1.67 | MRPL13; MRPL36; MRPL51 | 0 | 0.00 | | 0 | 0.00 | | 0 | 0.00 | | 0 | 0.00 | | 1 | 0.95 | MPV17L2 |
| positive regulation of glial cell differentiation: GO | 30 | 3 | 1.67 | CXCR4; IL1B; SERPINE2 | 2 | 0.79 | LIF; RNF112 | 0 | 0.00 | | 1 | 13.93 | IL1B | 1 | 0.85 | RNF112 | 1 | 0.95 | SERPINE2 |
| ww domain binding: GO | 30 | 3 | 1.67 | ENAH; KIF20B; TP63 | 5 | 1.97 | ATCAY; TCEAL2; TCEAL5; TCEAL6; WBP2NL | 0 | 0.00 | | 0 | 0.00 | | 2 | 1.69 | SCNN1B; TCEAL2 | 1 | 0.95 | ENAH |
| adp binding: GO | 30 | 2 | 1.12 | P2RY1; VCP | 2 | 0.79 | ACTA1; MYO3A | 0 | 0.00 | | 0 | 0.00 | | 0 | 0.00 | | 1 | 0.95 | P2RY1 |
| cdc42 reg pathway | 30 | 2 | 1.12 | NME1; RACGAP1 | 3 | 1.18 | ARHGEF25; BCAR3; MCF2L | 0 | 0.00 | | 0 | 0.00 | | 2 | 1.69 | ARHGEF25; BCAR3 | 1 | 0.95 | VAV2 |
| extension of telomeres | 30 | 2 | 1.12 | PCNA; RUVBL1 | 1 | 0.39 | TERT | 0 | 0.00 | | 0 | 0.00 | | 0 | 0.00 | | 1 | 0.95 | FEN1 |
| eye photoreceptor | 30 | 2 | 1.12 | PRDM1; TH | 3 | 1.18 | PAX6; RORB; | 0 | 0.00 | | 0 | 0.00 | | 0 | 0.00 | | 1 | 0.95 | TH |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| cell development: GO | | | | | | | TRPM1 | | | | | | | | | | | | |
| fas signaling pathway (cd95) | 30 | 2 | 1.12 | LMNB1; LMNB2 | 0 | 0.00 | | 0 | 0.00 | | 0 | 0.00 | | 0 | 0.00 | | 1 | 0.95 | LMNB2 |
| galactosyl-transferase activity: GO | 30 | 2 | 1.12 | B3GNT3; B3GNT5 | 3 | 1.18 | ABO; B3GALT1; B3GALT5 | 0 | 0.00 | | 0 | 0.00 | | 2 | 1.69 | ABO; B3GALT1 | 1 | 0.95 | B3GNT5 |
| glycan structures - degradation | 30 | 2 | 1.12 | HPSE; NEU2 | 2 | 0.79 | HPSE2; IDUA | 0 | 0.00 | | 0 | 0.00 | | 1 | 0.85 | HPSE2 | 1 | 0.95 | HPSE |
| keratan sulfate biosynthesis | 30 | 2 | 1.12 | B3GNT3; CHST1 | 2 | 0.79 | CHST5; PRELP | 0 | 0.00 | | 0 | 0.00 | | 0 | 0.00 | | 1 | 0.95 | CHST1 |
| map2k and mapk activation | 30 | 2 | 1.12 | ACTB; NRAS | 1 | 0.39 | CNKSR2 | 0 | 0.00 | | 0 | 0.00 | | 1 | 0.85 | CNKSR2 | 1 | 0.95 | ACTB |
| mismatch repair: GO | 30 | 2 | 1.12 | EXO1; PCNA | 0 | 0.00 | | 0 | 0.00 | | 0 | 0.00 | | 0 | 0.00 | | 1 | 0.95 | EXO1 |
| multicellular organism aging: GO | 30 | 2 | 1.12 | TH; TP63 | 4 | 1.57 | NR5A1; RNF165; SLC1A2; SPEF2 | 0 | 0.00 | | 0 | 0.00 | | 1 | 0.85 | SPEF2 | 1 | 0.95 | TH |
| phospholipid catabolic process: GO | 30 | 2 | 1.12 | LIPG; PLA2G4D | 0 | 0.00 | | 0 | 0.00 | | 0 | 0.00 | | 0 | 0.00 | | 1 | 0.95 | PLA2G4D |
| positive regulation of smooth muscle cell migration: GO | 30 | 2 | 1.12 | P2RY2; PLAU | 2 | 0.79 | BCL2; PDGFD | 0 | 0.00 | | 0 | 0.00 | | 2 | 1.69 | BCL2; LPAR1 | 1 | 0.95 | P2RY2 |
| protein kinase c activating g protein coupled receptor signaling pathway: GO | 30 | 2 | 1.12 | BDKRB1; CCK | 2 | 0.79 | CHRM1; DGKG | 0 | 0.00 | | 0 | 0.00 | | 1 | 0.85 | CHRM1 | 1 | 0.95 | CISH |
| ran gtpase binding: GO | 30 | 2 | 1.12 | BIRC5; RANBP1 | 1 | 0.39 | RANBP3L | 0 | 0.00 | | 0 | 0.00 | | 1 | 0.85 | RANBP3L | 1 | 0.95 | BIRC5 |
| traf6 mediated irf7 activation | 30 | 2 | 1.12 | IL6; MYD88 | 1 | 0.39 | IFNA5 | 0 | 0.00 | | 0 | 0.00 | | 0 | 0.00 | | 1 | 0.95 | MYD88 |
| aminosugars metabolism | 30 | 1 | 0.56 | HK2 | 1 | 0.39 | RENBP | 0 | 0.00 | | 0 | 0.00 | | 0 | 0.00 | | 1 | 0.95 | HK2 |
| bicellular | 30 | 1 | 0.56 | ECT2 | 1 | 0.39 | WNT11 | 0 | 0.00 | | 0 | 0.00 | | 1 | 0.85 | WNT11 | 1 | 0.95 | ECT2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| tight junction assembly: GO | | | | | | | | | | | | | | | | | | | |
| membrane biogenesis: GO | 30 | 1 | 0.56 | NLGN4X | 6 | 2.36 | IL1RAPL1; LRP4; MAGI2; NLGN1; NRXN1; PEX11A | 0 | 0.00 | | 0 | 0.00 | | 1 | 0.85 | NRXN1 | 1 | 0.95 | NLGN4X |
| negative regulation of tor signaling: GO | 30 | 1 | 0.56 | HIF1A | 1 | 0.39 | PRKAA2 | 0 | 0.00 | | 0 | 0.00 | | 1 | 0.85 | PRKAA2 | 1 | 0.95 | HIF1A |
| compound transmembrane transporter activity: GO | 30 | 1 | 0.56 | SLC28A3 | 0 | 0.00 | | 0 | 0.00 | | 0 | 0.00 | | 1 | 0.85 | SLC29A1 | 1 | 0.95 | SLC28A3 |
| positive regulation of histone methylation: GO | 30 | 1 | 0.56 | HIST1H1B | 1 | 0.39 | TET1 | 0 | 0.00 | | 0 | 0.00 | | 1 | 0.85 | TET1 | 1 | 0.95 | HIST1H1B |
| positive regulation of interferon beta production: GO | 30 | 1 | 0.56 | POLR3G | 0 | 0.00 | | 0 | 0.00 | | 0 | 0.00 | | 1 | 0.85 | ZBTB20 | 1 | 0.95 | POLR3G |
| regulation of transcription from rna polymerase ii promoter in response to hypoxia: GO | 30 | 1 | 0.56 | HIF1A | 1 | 0.39 | HIF3A | 0 | 0.00 | | 0 | 0.00 | | 1 | 0.85 | HIF3A | 1 | 0.95 | HIF1A |
| response to amphetamine: GO | 30 | 1 | 0.56 | TH | 5 | 1.97 | DRD1; DRD4; GRIN1; GRIN2A; PPP1R1B | 0 | 0.00 | | 0 | 0.00 | | 1 | 0.85 | SLC18A2 | 1 | 0.95 | TH |
| retinoic acid pathway | 30 | 1 | 0.56 | CDK1 | 1 | 0.39 | RXRG | 0 | 0.00 | | 0 | 0.00 | | 0 | 0.00 | | 1 | 0.95 | CDK1 |
| synapsis: GO | 30 | 1 | 0.56 | TRIP13 | 2 | 0.79 | STAG3; SYCP1 | 0 | 0.00 | | 0 | 0.00 | | 0 | 0.00 | | 1 | 0.95 | TRIP13 |
| transcriptional activity of | 30 | 1 | 0.56 | SERPINE1 | 0 | 0.00 | | 0 | 0.00 | | 1 | 13.93 | SERPINE1 | 0 | 0.00 | | 1 | 0.95 | JUNB |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| smad2/smad3: smad4 heterotrimer | | | | | | | | | | | | | | | | | | | |
| transport of vitamins nucleosides and related molecules | 30 | 1 | 0.56 | SLC28A3 | 3 | 1.18 | ALB; SLC27A6; SLCO4C1 | 1 | 13.93 | SLC27A6 | 0 | 0.00 | | 1 | 0.85 | SLC29A1 | 1 | 0.95 | SLC28A3 |
| schwann cell differentiation: GO | 30 | 0 | 0.00 | | 5 | 1.97 | ADAM22; FA2H; LAMA2; LGI4; MYOC | 0 | 0.00 | | 0 | 0.00 | | 4 | 3.39 | ADAM22; LAMA2; LGI4; MYOC | 1 | 0.95 | NDRG1 |
| small subunit processome: GO | 30 | 0 | 0.00 | | 0 | 0.00 | | 0 | 0.00 | | 0 | 0.00 | | 0 | 0.00 | | 1 | 0.95 | NOP56 |
| endoplasmic reticulum golgi intermediate compartment membrane: GO | 58 | 5 | 1.44 | AREG; CTSC; SERPINA1; TGFA; VMP1 | 3 | 0.61 | FOLR1; GRIA1; NAT8 | 0 | 0.00 | | 0 | 0.00 | | 2 | 0.88 | CNIH3; GRIA1 | 2 | 0.98 | AREG; TGFA |
| positive regulation of osteoblast differentiation: GO | 58 | 5 | 1.44 | GJA1; IFITM1; IL6; LTF; TP63 | 1 | 0.20 | ID4 | 0 | 0.00 | | 0 | 0.00 | | 2 | 0.88 | DDR2; TMEM119 | 2 | 0.98 | BMPR1B; LTF |
| negative regulation of cation transmembrane transport: GO | 58 | 4 | 1.15 | GSTO1; MMP9; NTSR1; PCSK9 | 10 | 2.03 | ACTN2; ADRA2A; AGT; ATP1A2; CASQ2; DRD4; GSTM2; HAMP; SLN; TRDN | 0 | 0.00 | | 0 | 0.00 | | 2 | 0.88 | ADRA2A; TRDN | 2 | 0.98 | NTSR1; PCSK9 |
| lysine degradation | 58 | 3 | 0.87 | AKR1B10; ALDH1A3; OGDHL | 0 | 0.00 | | 0 | 0.00 | | 0 | 0.00 | | 1 | 0.44 | ALDH3A2 | 2 | 0.98 | AKR1B10; OGDHL |
| notch pathway | 58 | 3 | 0.87 | CDKN1A; ENO1; PSENEN | 4 | 0.81 | DNM1; DTX1; MFAP5; SSPO | 0 | 0.00 | | 0 | 0.00 | | 1 | 0.44 | LNX1 | 2 | 0.98 | CDKN1A; ENO1 |
| signaling by met | 58 | 3 | 0.87 | ITGA3; LAMB3; NRAS | 3 | 0.61 | COL24A1; LAMA2; MUC20 | 0 | 0.00 | | 0 | 0.00 | | 4 | 1.75 | COL24A1; GULP1; LAMA2; | 2 | 0.98 | ITGA3; LAMB3 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | | | | | | | | | | MUC20 | | | |
| positive regulation of phosphatidyl-inositol 3 kinase signaling: GO | 58 | 2 | 0.58 | F2RL1; NRG1 | 8 | 1.63 | AGT; ERBB4; FGFR1; LEP; MYOC; PDGFD; RELN; SERPINA12 | 0 | 0.00 | | 0 | 0.00 | | 7 | 3.07 | ANGPT1; DCN; ERBB4; FGFR1; MYOC; RELN; SERPINA12 | 2 | 0.98 | NRG1; PPARD |
| steroid hormone receptor activity: GO | 58 | 2 | 0.58 | NR4A3; PAQR5 | 8 | 1.63 | AR; ESRRG; NR3C2; NR5A1; PGR; RORB; RORC; RXRG | 0 | 0.00 | | 0 | 0.00 | | 5 | 2.19 | ESR1; ESRRG; NR2F1; NR3C2; PGR | 2 | 0.98 | PAQR5; PPARD |
| pi3k cascade | 58 | 1 | 0.29 | EIF4EBP1 | 7 | 1.42 | CAB39L; EEF2K; FGF1; FGFR1; FGFR3; IRS2; PRKAA2 | 0 | 0.00 | | 0 | 0.00 | | 2 | 0.88 | FGFR1; PRKAA2 | 2 | 0.98 | EIF4EBP1; TRIB3 |
| regulation of cellular amine metabolic process: GO | 86 | 7 | 1.36 | LDLR; ODC1; PSMA4; PSMA5; PSMB6; PSMD1; PSME3 | 5 | 0.69 | APOC1; ATCAY; DRD1; DRD4; SNCA | 0 | 0.00 | | 0 | 0.00 | | 1 | 0.30 | SNCA | 3 | 0.99 | LDLR; LPCAT1; ODC1 |
| lysosomal lumen: GO | 86 | 5 | 0.97 | CTSB; HPSE; HSPA8; IFI30; SDC1 | 9 | 1.23 | BCAN; CTSF; GPC2; GPC3; GPC6; GYG2; IDUA; PRELP; SDC2 | 0 | 0.00 | | 0 | 0.00 | | 2 | 0.59 | DCN; GPC2 | 3 | 0.99 | AGRN; HPSE; HSPA8 |
| toll like receptor 4 (tlr4) cascade | 86 | 5 | 0.97 | CAP1; DUSP6; MYD88; S100A12; UBE2N | 1 | 0.14 | PELI2 | 0 | 0.00 | | 0 | 0.00 | | 1 | 0.30 | PELI2 | 3 | 0.99 | CAP1; DUSP6; MYD88 |
| postsynaptic membrane: GO | 198 | 11 | 0.93 | CHRNA3; CHRNA6; CHRNA9; FBXO45; GABRQ; HOMER1; HTR3A; LRRC4; | 46 | 2.74 | ANK2; ANKS1B; APBB1; CBLN1; CHRM1; CHRM2; CHRM3; CHRM4; | 2 | 4.22 | GRIA4; SRCIN1 | 0 | 0.00 | | 15 | 1.92 | CHRM1; CHRM3; CNIH3; CNKSR2; CPEB1; DLG2; GLRB; GRIA1; GRIA2; | 7 | 1.00 | CHRNA6; DLGAP2; FBXO45; HOMER1; LRRC4; NLGN4X; P2RY1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | NLGN4X; P2RY1; SH2D5 | | | CHRNA2; CLSTN2; CNKSR2; CPEB1; DLG2; DLGAP1; DMD; GABRA2; GABRB3; GABRG3; GABRP; GLRB; GRIA1; GRIA2; GRIA4; GRID2IP; GRIK3; GRIK4; GRIK5; GRIN1; GRIN2A; GRM7; ILIRAPL1; KCNB1; | | | | | | | | | GRID2IP; GRIK3; KCND2; LRRC4C; SSPN; SYNE1 | | | |
| regulation of receptor activity: GO | 114 | 10 | 1.47 | EPGN; EREG; GREM1; GSTO1; NETO2; P2RY1; PCSK9; PLAU; SERPINE1; TGFA | 15 | 1.55 | ACTN2; ADORA1; ADRA2A; CASQ2; CFTR; DMD; EGF; GSTM2; JPH2; NLGN1; NRXN1; PPARGC1A; RELN; SHANK1; TRDN | 0 | 0.00 | | 1 | 3.67 | SERPINE1 | 8 | 1.78 | ADRA2A; CNIH3; EGF; HRC; NRXN1; PPARGC1A; RELN; TRDN | 4 | 0.99 | EREG; P2RY1; PCSK9; TGFA |
| negative regulation of establishment of protein | 199 | 18 | 1.51 | ANXA1; F2RL1; HMGCR; HSPH1; IL1B; | 16 | 0.95 | ABCC8; ACVR1C; ADIPOQ; ADRA2A; | 3 | 6.30 | ACVR1C; ADIPOQ; SRCIN1 | 2 | 4.20 | GBP1; IL1B | 7 | 0.89 | ADRA2A; ANGPT1; CD34; FBLN1; | 7 | 1.00 | HSPH1; IL10; MDFI; SNAI2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| localization: GO | | | | IL36RN; IL6; LYPLA1; MDFI; RSAD2; SLAMF1; SRGN; TNFRSF21; TNFRSF9; TXN; VSNL1; YOD1; ZC3H12A | | | ANXA13; APOD; CD34; DRD4; INHBB; KCNB1; PKD1; PKDCC; SRCIN1; SSC5D; SVIP; USP17L2 | | | | | | | | | LRRC15; SSC5D; SVIP | | | TXN; VSNL1; ZC3H12A |
| neuron projection guidance: GO | 199 | 9 | 0.76 | ARTN; CDK5R1; ENAH; FLRT3; NR4A3; NRAS; NTRK1; PRKCQ; WNT5A | 25 | 1.48 | BOC; CDH4; CNTN4; DRGX; EPHB1; FEZF2; GFRA3; GLI2; LAMA2; LMXIA; NCAM1; NOG; NRXN1; NRXN3; PAX6; PLXNA3; PLXNA4; RELN; RNF165; SEMA3A; SEMA3B; SLIT2; SLIT3; SPTBN4; UNC5D | 0 | 0.00 | | 0 | 0.00 | | 14 | 1.79 | CHL1; CXCL 12; EFNB3; GDF7; GLI2; LAMA2; NCAM1; NRXN1; NTN4; PLXNA4; RELN; SLIT2; SLIT3; SPTBN4 | 7 | 1.00 | ARTN; BMPR1B; CDK5R1; ENAH; FLRT3; PRKCQ; WNT5A |
| cell cortex part: GO | 115 | 8 | 1.16 | ANLN; CAP1; EXOC3L2; RAB10; RALB; SELE; SLC2A1; TRPC4 | 14 | 1.44 | ACTN2; CAPZA3; EPB42; GSN; HAMP; MYO1A; NOS2; PCLO; PHLDB1; PPP1R9A; | 0 | 0.00 | | 1 | 3.63 | SELE | 6 | 1.33 | CAPZA3; DLC1; MYRIP; PCLO; SPTBN4; STXBP6 | 4 | 0.99 | ANLN; CAP1; SLC2A1; TPM4 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | SLC4A1; SPTBN4; STXBP6; TMOD1 | | | | | | | | | | | | |
| coenzyme biosynthetic process: GO | 115 | 7 | 1.02 | ACOT7; COQ2; ELOVL7; KYNU; MTHFD2; NAMPT; PNP | 10 | 1.03 | ACACB; ACOT1; ACOT12; ACSBG1; ACSF2; ASPDH; ELOVL2; HAAO; MAT1A; SCD5 | 0 | 0.00 | | 0 | 0.00 | | 1 | 0.22 | NMNAT3 | 4 | 0.99 | ACOT7; NAMPT; PDSS1; PNP |
| fc gamma receptor signaling pathway: GO | 87 | 10 | 1.92 | ACTB; ACTR3; ARPC1A; ARPC3; FCGR1A; IGHG1; IGHG2; IGHG4; IGKC; IGKV4-1 | 1 | 0.14 | PLA2G6 | 2 | 9.61 | IGHG1; IGKV3-20 | 0 | 0.00 | | 1 | 0.29 | IGHV3-23 | 3 | 0.98 | ACTB; ARPC1A; VAV2 |
| b cell mediated immunity: GO | 87 | 9 | 1.73 | C1QBP; EXO1; IGHG1; IGHG2; IGHG4; IGKC; ; IGKV4-1 IL13RA2; IL4R | 5 | 0.68 | C3; C4BPA; C6; C7; CLU | 2 | 9.61 | IGHG1; IGKV3-20 | 0 | 0.00 | | 4 | 1.17 | C3; CLU; IGHM; IGHV3-23 | 3 | 0.98 | BCL3; EXO1; IL13RA2 |
| ensheathment of neurons: GO | 87 | 4 | 0.77 | CXCR4; KLK6; NRG1; TNFRSF21 | 14 | 1.90 | ACSBG1; ADAM22; ANK2; CLU; FA2H: GAL3ST1; GJC3; ID4; LAMA2; LGI4; MYOC; PLLP; PLP1; | 0 | 0.00 | | 0 | 0.00 | | 8 | 2.34 | ADAM22; CLU; LAMA2; LGI4; LPAR1; MYOC; PLLP; PLP1 | 3 | 0.98 | NDRG1; NRG1; PPARD |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | | | | PRX | | | | | | | | | | | | |
| regulation of monooxygenase activity: GO | 59 | 7 | 1.99 | CDH3; CYP27B1; GDNF; HIF1A; IFNG; IL1B; LYPLA1 | 9 | 1.80 | APOE; CNR1; CYGB; FCER2; GCHFR; LEP; PRKG2; SNCA; TERT | 0 | 0.00 | | 1 | 7.08 | IL1B | 3 | 1.29 | ESR1; PRKG2; SNCA | 2 | 0.96 | CYP27B1; HIF1A |
| tyrosine metabolism | 59 | 6 | 1.70 | ADH7; ALDH1A3; ESCO2; GOT2; IL4I1; TH | 7 | 1.40 | ADH1B; ADH1C; ADHFE1; AOC3; DCT; MAOA; PNPLA3 | 0 | 0.00 | | 0 | 0.00 | | 2 | 0.86 | AOX1; PNPLA3 | 2 | 0.96 | GOT2; TH |
| organic hydroxy compound transmembrane transporter activity: GO | 59 | 5 | 1.42 | ABCG4; AQP3; SLC10A6; SLC16A1; SLC16A6 | 9 | 1.80 | ABCB11; ABCC3; AQP4; AQP7; SLC10A2; SLC16A11; SLC16A12; SLC16A8; SLC6A2 | 0 | 0.00 | | 1 | 7.08 | AQP9 | 1 | 0.43 | SLC18A2 | 2 | 0.96 | AQP3; SLC16A6 |
| positive regulation of lipid biosynthetic process: GO | 59 | 5 | 1.42 | ANXA1; IFNG; IL1B; LDLR; PTGS2 | 11 | 2.20 | APOE; CYP17A1; FGF1; GPAM; GPLD1; HSD17B13; MLXIPL; PLA2G6; PLIN5; PPARGC1A; SORBS1 | 1 | 7.08 | GPAM | 1 | 7.08 | IL1B | 3 | 1.29 | DGAT2; GPLD1; PPARGC1A | 2 | 0.96 | LDLR; PTGS2 |
| peptidyl lysine methylation: GO | 59 | 1 | 0.28 | HIST1H1D | 1 | 0.20 | CHD5 | 0 | 0.00 | | 0 | 0.00 | | 0 | 0.00 | | 2 | 0.96 | BEND3; HIST1H1D |
| pyrimidine containing compound catabolic process: GO | 31 | 4 | 2.16 | APOBEC3A; CDA; TYMP; UPP1 | 2 | 0.76 | NEIL1; UPP2 | 0 | 0.00 | | 0 | 0.00 | | 0 | 0.00 | | 1 | 0.91 | CDA |
| vitamin transport: GO | 31 | 4 | 2.16 | PDPN; SLC2A1; STRA6; TCN1 | 4 | 1.52 | FOLR1; FOLR2; SLC19A3; | 0 | 0.00 | | 0 | 0.00 | | 1 | 0.82 | SLC19A3 | 1 | 0.91 | SLC2A1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | TTPA | | | | | | | | | | | | |
| cop9 signalosome: GO | 31 | 3 | 1.62 | DYNLL1; HSPA5; HSPA6 | 3 | 1.14 | AMOT; HSPA1L; TMOD1 | 0 | 0.00 | | 0 | 0.00 | | 0 | 0.00 | | 1 | 0.91 | HSPA5 |
| dendritic cell differentiation: GO | 31 | 3 | 1.62 | CSF2; F2RL1; TNFSF9 | 1 | 0.38 | GATA1 | 0 | 0.00 | | 0 | 0.00 | | 0 | 0.00 | | 1 | 0.91 | DHRS2 |
| er nucleus signaling pathway: GO | 31 | 3 | 1.62 | CALR; EIF2S1; HSPA5 | 0 | 0.00 | | 0 | 0.00 | | 0 | 0.00 | | 0 | 0.00 | | 1 | 0.91 | HSPA5 |
| immunological synapse: GO | 31 | 3 | 1.62 | CD3E; GZMA; PRKCQ | 0 | 0.00 | | 0 | 0.00 | | 1 | 13.48 | GZMB | 0 | 0.00 | | 1 | 0.91 | PRKCQ |
| lipopolysaccharide mediated signaling pathway: GO | 31 | 3 | 1.62 | CCL3; IL1B; PTAFR | 0 | 0.00 | | 0 | 0.00 | | 1 | 13.48 | IL1B | 0 | 0.00 | | 1 | 0.91 | PTAFR |
| negative regulation of mapk pathway | 31 | 3 | 1.62 | DUSP6; DUSP9; NRAS | 0 | 0.00 | | 0 | 0.00 | | 0 | 0.00 | | 0 | 0.00 | | 1 | 0.91 | DUSP6 |
| positive regulation of fatty acid metabolic process: GO | 31 | 3 | 1.62 | ANXA1; NR4A3; PTGS2 | 6 | 2.28 | ABCD2; ADIPOQ; IRS2; MLXIPL; PLIN5; PPARGC1A | 2 | 26.96 | ABCD2; ADIPOQ | 0 | 0.00 | | 1 | 0.82 | PPARGC1A | 1 | 0.91 | PTGS2 |
| cellular response to dsrna: GO | 31 | 2 | 1.08 | NPM1; RALB | 3 | 1.14 | COLEC12; P2RX7; TERT | 0 | 0.00 | | 0 | 0.00 | | 0 | 0.00 | | 1 | 0.91 | NPM1 |
| erk1 erk2 mapk pathway | 31 | 2 | 1.08 | DUSP6; DUSP9 | 1 | 0.38 | EEF2K | 0 | 0.00 | | 0 | 0.00 | | 0 | 0.00 | | 1 | 0.91 | DUSP6 |
| insulin receptor binding: GO | 31 | 2 | 1.08 | DOK3; INSL3 | 4 | 1.52 | ENPP1; IRS2; IRS4; SORBS1 | 0 | 0.00 | | 0 | 0.00 | | 1 | 0.82 | DOK6 | 1 | 0.91 | DOK3 |
| negative regulation of dna biosynthetic process: GO | 31 | 2 | 1.08 | GJA1; PIF1 | 2 | 0.76 | ADIPOQ; DACH1 | 1 | 13.48 | ADIPOQ | 0 | 0.00 | | 2 | 1.64 | DACH1; KCNK2 | 1 | 0.91 | PIF1 |
| regulation of gastrulation: GO | 31 | 2 | 1.08 | DUSP6; IL1RN | 7 | 2.66 | ADIPOQ; DKK1; FGFR1; MESP1; OSR1; OSR2; PHLDB1 | 1 | 13.48 | ADIPOQ | 0 | 0.00 | | 4 | 3.28 | FGFR1; FZD7; MESP1; OSR1 | 1 | 0.91 | DUSP6 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| steroid hydroxylase activity: GO | 31 | 2 | 1.08 | CH25H; CYP2S1 | 8 | 3.04 | CYP17A1; CYP1A1; CYP21A2; CYP2A6; CYP2C9; CYP2D6; CYP2J2; CYP2W1 | 0 | 0.00 | | 0 | 0.00 | | 2 | 1.64 | CYP2W1; CYP3A4 | 1 | 0.91 | CYP2S1 |
| aggresome: GO | 31 | 1 | 0.54 | ORC6 | 2 | 0.76 | CLU; HSPB7 | 0 | 0.00 | | 0 | 0.00 | | 1 | 0.82 | CLU | 1 | 0.91 | ORC6 |
| alanine and aspartate metabolism | 31 | 1 | 0.54 | GOT2 | 3 | 1.14 | ASPA; CRAT; GPT | 0 | 0.00 | | 0 | 0.00 | | 2 | 1.64 | ASPA; GPT | 1 | 0.91 | GOT2 |
| dna polymerase activity: GO | 31 | 1 | 0.54 | POLQ | 1 | 0.38 | TERT | 0 | 0.00 | | 0 | 0.00 | | 0 | 0.00 | | 1 | 0.91 | POLQ |
| e box binding: GO | 31 | 1 | 0.54 | ARNTL2 | 6 | 2.28 | ATOH8; BHLHE41; HAND2; NEUROD2; PER1; TCF21 | 0 | 0.00 | | 0 | 0.00 | | 3 | 2.46 | ATOH8; BHLHE41; HAND2 | 1 | 0.91 | ASCL2 |
| establishment of protein localization to vacuole: GO | 31 | 1 | 0.54 | HSPA8 | 0 | 0.00 | | 0 | 0.00 | | 0 | 0.00 | | 0 | 0.00 | | 1 | 0.91 | HSPA8 |
| fatty acyl coa binding: GO | 31 | 1 | 0.54 | ACOT7 | 4 | 1.52 | ACADL; ACBD4; ACOX2; SOAT2 | 0 | 0.00 | | 0 | 0.00 | | 2 | 1.64 | ACBD4; ACOX2 | 1 | 0.91 | ACOT7 |
| macrophage activation: GO | 31 | 1 | 0.54 | CSF2 | 2 | 0.76 | CLU; SNCA | 0 | 0.00 | | 0 | 0.00 | | 2 | 1.64 | CLU; SNCA | 1 | 0.91 | SBNO2 |
| oligodendrocyte development: GO | 31 | 1 | 0.54 | GSTP1 | 6 | 2.28 | CLU; FA2H; GSN; ID4; PLP1; PRDM8 | 0 | 0.00 | | 0 | 0.00 | | 3 | 2.46 | CLU; LPAR1; PLP1 | 1 | 0.91 | GSTP1 |
| phenol containing compound biosynthetic process: GO | 31 | 1 | 0.54 | TH | 4 | 1.52 | DCT; HAND2; OCA2; SNCA | 0 | 0.00 | | 0 | 0.00 | | 5 | 4.10 | ASIP; HAND2; HDC; SNCA; TRPC1 | 1 | 0.91 | TH |
| positive regulation of dendrite morphogenesis: GO | 31 | 1 | 0.54 | LRP8 | 5 | 1.90 | CAMK2B; EEF2K; ILIRAPL1; PAK3; RELN | 0 | 0.00 | | 0 | 0.00 | | 2 | 1.64 | PAK3; RELN | 1 | 0.91 | SGK1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| regulation of actin cytoskeleton reorganization: GO | 31 | 1 | 0.54 | RHOD | 2 | 0.76 | NTRK3; SEMA3E | 0 | 0.00 | | 0 | 0.00 | | 1 | 0.82 | SEMA3E | 1 | 0.91 | RHOD |
| regulation of dna templated transcription initiation: GO | 31 | 1 | 0.54 | FOSL1 | 2 | 0.76 | MITF; NKX2-5 | 0 | 0.00 | | 0 | 0.00 | | 1 | 0.82 | MITF | 1 | 0.91 | FOSL1 |
| regulation of triglyceride metabolic process: GO | 31 | 1 | 0.54 | LDLR | 7 | 2.66 | C3; FITM2; GPAM; GPLD1; PLIN5; SERPINA12; THRSP | 2 | 26.96 | GPAM; THRSP | 0 | 0.00 | | 5 | 4.10 | C3; DGAT2; ESR1; GPLD1; SERPINA12 | 1 | 0.91 | LDLR |
| skeletal muscle contraction: GO | 31 | 1 | 0.54 | HOMER1 | 6 | 2.28 | MYH14; MYH3; TNNC1; TNNC2; TNNI2; TNNT3 | 0 | 0.00 | | 0 | 0.00 | | 2 | 1.64 | TNNC1; TNNT3 | 1 | 0.91 | HOMER1 |
| myosin pathway | 31 | 0 | 0.00 | | 1 | 0.38 | ARHGEF19 | 0 | 0.00 | | 0 | 0.00 | | 0 | 0.00 | | 1 | 0.91 | ARHGEF16 |
| regulation of intrinsic apoptotic signaling pathway in response to dna damage: GO | 31 | 0 | 0.00 | | 1 | 0.38 | CLU | 0 | 0.00 | | 0 | 0.00 | | 2 | 1.64 | CLU; CXCL12 | 1 | 0.91 | SNAI2 |
| regulation of microtubule polymerization: GO | 31 | 0 | 0.00 | | 2 | 0.76 | MAPT; SNCA | 0 | 0.00 | | 0 | 0.00 | | 2 | 1.64 | MAPT; SNCA | 1 | 0.91 | SGK1 |
| isomerase activity: GO | 144 | 12 | 1.39 | EBP; FKBPL; PDIA3; PGAM1; PGM2; PPIA; PPIB; PPIF; PPIL1; TOP2A; TPI1; TTC9 | 5 | 0.41 | DCT; PGM5; PPIL6; PTGIS; RENBP | 0 | 0.00 | | 0 | 0.00 | | 4 | 0.71 | DSEL; FKBP7; PGM5; PPIL6 | 5 | 0.98 | PGAM1; PPIF; PPIL1; TOP2A; TPI1 |
| regulation of muscle contraction: GO | 144 | 11 | 1.28 | CHRNA3; DSC2; DSP; GSTO1; JUP; | 30 | 2.46 | ADORA1; ADRA1A; ADRA1B; | 0 | 0.00 | | 0 | 0.00 | | 10 | 1.76 | ADRA1A; ADRA2A; CHRM1; | 5 | 0.98 | DSC2; NMU; PTAFR; PTGS2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | MYLK2; NMU; PROK2; PTAFR; PTGS2; ZC3H12A | | | ADRA2A; ANK2; ATP1A2; ATP2A1; CASQ2; CHRM1; CHRM2; CHRM3; CNN1; CTNNA3; DMD; GSTM2; HSPB6; KCNA1; KCNB2; MYBPH; MYL3; MYL9; MYOCD; NKX2-5; P2RX1; TNNC1; TNNC2; TNNI2; TNNT2; TNNT3; TPM1 | | | | | | | | | CHRM3; CTGF; HRC; HSPB6; PRKG1; TNNC1; TNNT3 | | | ZC3H12A |
| male sex differentiation: GO | 144 | 8 | 0.93 | ASPM; GJB2; INSL3; KIF18A; NTRK1; SDC1; TGFBR1; WNT5A | 13 | 1.07 | AMHR2; BCL2; BMP5; CYP17A1; FGF9; GATA1; LHB; LHCGR; NR5A1; NUPR1; REN; SOX8; TCF21 | 0 | 0.00 | | 0 | 0.00 | | 3 | 0.53 | BCL2; ESR1; HOXA10 | 5 | 0.98 | ASPM; KIF18A; SOX15; WNT5A; WNT9B |
| neural tube development: GO | 144 | 6 | 0.70 | GRHL3; HIF1A; KIF20B; PFN1; STIL; WNT5A | 13 | 1.07 | ALX1; CECR2; COBL; DACT1; FOLR1; GLI2; | 0 | 0.00 | | 0 | 0.00 | | 10 | 1.76 | CHRD; DACT1; DLC1; FOXA1; GDF7; GLI2; | 5 | 0.98 | EPHA2; HIF1A; PFN1; STIL; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline: Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo: Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo: Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | | | | GSC; KAT2A; NOG; PAX6; PKD1; PTCH1; SALL2 | | | | | | | | | PRICKLE1; PTCH1; SALL2; SHROOM3 | | | |
| sterol metabolic process: GO | 116 | 6 | 0.87 | CH25H; EBP; HMGCR; LDLR; PCSK9; SQLE | 12 | 1.22 | APOC1; APOE; CFTR; CYP17A1; CYP21A2; HMGCS2; LEP; LEPR; NPC1L1; PON1; PRKAA2; SOAT2 | 0 | 0.00 | | 0 | 0.00 | | 2 | 0.44 | HMGCS2; PRKAA2 | 4 | 0.98 | LDLR; PCSK9; PPARD; SQLE |
| phase i - functional-ization of compounds | 88 | 6 | 1.14 | CYP24A1; CYP27B1; CYP2S1; CYP4F11; CYP4F22; SMOX | 21 | 2.82 | ADH1B; ADH1C; ALDH1A1; AOC3; CES1; CYP17A1; CYP1A1; CYP1A2; CYP2A6; CYP2C9; CYP2J2; CYP2W1; CYP3A5; CYP4A11; CYP4B1; CYP4F12; FMO2; FMO5; MAOA; MARC1; PTGIS | 0 | 0.00 | | 0 | 0.00 | | 11 | 3.18 | ALDH3A2; CES1; CYP2W1; CYP3A4; CYP3A5; CYP4A11; CYP4B1; CYP4F12; FMO5; MARC2; SLC29A1 | 3 | 0.97 | CYP27B1; CYP2S1; SMOX |
| regulation of gliogenesis: GO | 88 | 6 | 1.14 | ADCYAP1; CDK1; CXCR4; IL1B; SERPINE2; TNFRSF21 | 7 | 0.94 | ID4; LIF; NOG; NTRK3; RNF112; SOX10; SOX8 | 0 | 0.00 | | 1 | 4.75 | IL1B | 2 | 0.58 | MYCN; RNF112 | 3 | 0.97 | ASCL2; CDK1; SERPINE2 |
| ribonuclease activity: GO | 88 | 5 | 0.95 | EXO1; ISG20; RNASE7; | 0 | 0.00 | | 0 | 0.00 | | 0 | 0.00 | | 0 | 0.00 | | 3 | 0.97 | EXO1; FEN1; ZC3H12A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | RPP40; ZC3H12A | | | | | | | | | | | | | | | |
| pdz domain binding: GO | 88 | 3 | 0.57 | CXADR; GJA1; KIF14 | 13 | 1.74 | ADRB1; APBA1; ATP2B2; CFTR; CXXC4; DTNA; FZD4; FZD8; GRIA1; GRIK5; GRM7; NLGN1; SDC2 | 0 | 0.00 | | 0 | 0.00 | | 6 | 1.73 | APBA1; FZD7; GRIA1; LNX1; LPAR1; SNTB1 | 3 | 0.97 | ARHGEF16; KIF14; SLC26A6 |
| transcription factor activity rna polymerase ii distal enhancer sequence specific binding: GO | 88 | 3 | 0.57 | FOXF1; HIF1A; SUB1 | 8 | 1.07 | BACH2; BHLHE41; GATA5; MEOX2; NKX2-5; NR5A1; SOX10; ZBTB16 | 0 | 0.00 | | 0 | 0.00 | | 4 | 1.15 | BACH2; BHLHE41; FOXC1; MEOX2 | 3 | 0.97 | HIF1A; SNAI2; SUB1 |
| nod like signaling receptor pathway | 60 | 7 | 1.95 | CARD6; CCL7; CXCL1; IL1B; IL6; MEFV; PYCARD | 0 | 0.00 | | 0 | 0.00 | | 1 | 6.96 | IL1B | 0 | 0.00 | | 2 | 0.95 | CXCL2; MEFV |
| regulation of tissue remodeling: GO | 60 | 5 | 1.39 | CA2; GJA1; GREM1; IL12B; UBASH3B | 7 | 1.38 | AGT; CARTPT; CLDN18; LEP; LEPR; P2RX7; PDK4 | 0 | 0.00 | | 0 | 0.00 | | 2 | 0.85 | CLDN18; PDK4 | 2 | 0.95 | CA2: UBASH3B |
| cargo receptor activity: GO | 60 | 4 | 1.12 | LDLR; LRP8; OLR1; TMPRSS4 | 11 | 2.16 | ASGR1; COLEC12; ENPP1; FOLR1; FOLR2; ILDR1; MARCO; SCARA5; SSC5D; SUSD2; | 0 | 0.00 | | 1 | 6.96 | TMPRSS4 | 5 | 2.12 | ENPP3; ILDR1; SCARA5; SSC5D; SUSD2 | 2 | 0.95 | LDLR; LGALS3BP |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | TMPRSS2 | | | | | | | | | | | | |
| mtor signaling pathway | 60 | 4 | 1.12 | EIF4EBP1; EIF4G2; HIF1A; PGF | 3 | 0.59 | CAB39L; PRKAA2; RPS6KA6 | 0 | 0.00 | | 0 | 0.00 | | 2 | 0.85 | PRKAA2; RPS6KA6 | 2 | 0.95 | EIF4EBP1; HIF1A |
| ovarian follicle development: GO | 60 | 3 | 0.84 | ADCYAP1; CCNE1; EREG | 3 | 0.59 | BCL2; INHBB; NOBOX | 0 | 0.00 | | 0 | 0.00 | | 3 | 1.27 | BCL2; ESR1; FOXC1 | 2 | 0.95 | BMPR1B; EREG |
| positive regulation of jun kinase activity: GO | 60 | 3 | 0.84 | IL1B; MDFI; WNT5A | 3 | 0.59 | BIRC7; FZD4; FZD8 | 0 | 0.00 | | 1 | 6.96 | IL1B | 0 | 0.00 | | 2 | 0.95 | MDFI; WNT5A |
| somitogenesis: GO | 60 | 3 | 0.84 | FOXF1; RGS20; WNT5A | 4 | 0.79 | COBL; DKK1; KAT2A; MEOX2 | 0 | 0.00 | | 0 | 0.00 | | 2 | 0.85 | FOXC1; MEOX2 | 2 | 0.95 | RGS20; WNT5A |
| termination of rna polymerase ii transcription: GO | 60 | 3 | 0.84 | EIF4A3; SNRPF; SNRPG | 0 | 0.00 | | 0 | 0.00 | | 0 | 0.00 | | 0 | 0.00 | | 2 | 0.95 | DDX39A; EIF4A3 |
| neuroepithelial cell differentiation: GO | 60 | 1 | 0.28 | PLS3 | 11 | 2.16 | ATP2B2; BCL2; CLIC5; EDN3; FGFR1; MCOLN3; MITF; OCA2; PDZD7; SOX10; WNT11 | 0 | 0.00 | | 0 | 0.00 | | 9 | 3.81 | B9D1; BCL2; CLIC5; EDN3; FGFR1; MITF; PDZD7; SLITRK6; WNT11 | 2 | 0.95 | SLC4A7; TMC1 |
| grb2 events in egfr signaling | 145 | 12 | 1.38 | ACTB; CSF2; DUSP6; DUSP9; EREG; HBEGF; IL2RA; JAK3; NRAS; NRG1; PSMA5; PSMB6 | 12 | 0.98 | BTC; CNKSR2; EGF; FGF1; FGFR1; FGFR3; GFRA1; GRIN2A; IL5; IRS2; NRG2; SHC2 | 0 | 0.00 | | 1 | 2.88 | IL2RA | 5 | 0.88 | ANGPT1; CNKSR2; EGF; FGFR1; SHC2 | 5 | 0.98 | ACTB; DUSP6; EREG; HBEGF; NRG1 |
| raf/map kinase cascade | 145 | 12 | 1.38 | ACTB; CSF2; DUSP6; DUSP9; EREG; HBEGF; IL2RA; JAK3; NRAS; NRG1; | 12 | 0.98 | BTC; CNKSR2; EGF; FGF1; FGFR1; FGFR3; GFRA1; GRIN2A; IL5; | 0 | 0.00 | | 1 | 2.88 | IL2RA | 5 | 0.88 | ANGPT1; CNKSR2; EGF; FGFR1; SHC2 | 5 | 0.98 | ACTB; DUSP6; EREG; HBEGF; NRG1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | A: Fold Change (FC) Up | A: Up-regulated Genes | A: Down-regulated | A: Fold Change (FC) | A: Down-regulated Genes | B. Differentially expressed genes significant in the baseline vs week 12 comparison only in the placebo: Up-regulated | B: Fold Change (FC) Up | B: Up-regulated Genes | B: Down-regulated | B: Fold Change (FC) | B: Down-regulated Genes | C. Differentially expressed genes significant in the baseline vs week 12 comparison only in the nemo: Up-regulated | C: Fold Change (FC) Up | C: Up-regulated Genes | C: Down-regulated | C: Fold Change (FC) | C: Down-regulated Genes |
|---|---|---|---|---|---|---|---|---|---|---|---|---|---|---|---|---|---|---|---|
| | | | | PSMA5; PSMB6 | | | IRS2; NRG2; SHC2 | | | | | | | | | | | | |
| sos-mediated signalling | 145 | 12 | 1.38 | ACTB; CSF2; DUSP6; DUSP9; EREG; HBEGF; IL2RA; JAK3; NRAS; NRG1; PSMA5; PSMB6 | 12 | 0.98 | BTC; CNKSR2; EGF; FGF1; FGFR1; FGFR3; GFRA1; GRIN2A; IL5; IRS2; NRG2; SHC2 | 0 | 0.00 | | 1 | 2.88 | IL2RA | 5 | 0.88 | ANGPT1; CNKSR2; EGF; FGFR1; SHC2 | 5 | 0.98 | ACTB; DUSP6; EREG; HBEGF; NRG1 |
| regulation of organelle assembly: GO | 145 | 8 | 0.92 | CSF2; FSCN1; MSN; NPM1; PLK1; PLK2; RALB; SDC1 | 3 | 0.24 | ADAMTS16; GSN; IL5 | 0 | 0.00 | | 0 | 0.00 | | 0 | 0.00 | | 5 | 0.98 | MSN; NPM1; PLK1; PLK2; PLK4 |
| ccr chemokine receptor binding: GO | 32 | 7 | 3.66 | CCL17; CCL18; CCL21; CCL22; CCL3; CCL7; CXCL13 | 1 | 0.37 | CCL14 | 0 | 0.00 | | 0 | 0.00 | | 1 | 0.79 | CCL14 | 1 | 0.89 | CCL20 |
| il1r pathway | 32 | 6 | 3.14 | IL1A; IL1B; IL1RAP; IL1RN; IL6; MYD88 | 0 | 0.00 | | 0 | 0.00 | | 1 | 13.06 | IL1B | 0 | 0.00 | | 1 | 0.89 | MYD88 |
| immunoregulatory interactions between a lymphoid and a non lymphoid cell | 32 | 6 | 3.14 | CD3E; KIR2DL4; RAETE; ULBP1; ULBP2; ULBP3 | 1 | 0.37 | CD34 | 0 | 0.00 | | 0 | 0.00 | | 1 | 0.79 | CD34 | 1 | 0.89 | LILRA1 |
| cellular carbohydrate catabolic process: GO | 32 | 4 | 2.09 | GK; PGM2; PYGL; TPI1 | 4 | 1.47 | GYG2; PHKG1; PYGM; STBD1 | 0 | 0.00 | | 0 | 0.00 | | 1 | 0.79 | PHKG1 | 1 | 0.89 | TPI1 |
| regulation of actin filament based movement: GO | 32 | 4 | 2.09 | DSC2; DSP; JUP; MYLK2 | 5 | 1.84 | ANK2; ATP1A2; CTNNA3; TNNC1; TNNT2 | 0 | 0.00 | | 0 | 0.00 | | 1 | 0.79 | TNNC1 | 1 | 0.89 | DSC2 |
| alanine aspartate | 32 | 3 | 1.57 | ALDH4A1; | 2 | 0.74 | ASPA; GPT | 0 | 0.00 | | 0 | 0.00 | | 3 | 2.38 | ALDH5A1; | 1 | 0.89 | GOT2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| and glutamate metabolism | | | | GOT2; IL4I1 | | | | | | | | | | | | ASPA; GPT | | | |
| aminoacyl-trna biosynthesis | 32 | 3 | 1.57 | EPRS; GARS; TARS | 0 | 0.00 | | 0 | 0.00 | | 0 | 0.00 | | 0 | 0.00 | | 1 | 0.89 | TARS |
| gpi anchor metabolic process: GO | 32 | 3 | 1.57 | CWH43; PIGW; PLAUR | 1 | 0.37 | GPLD1 | 0 | 0.00 | | 0 | 0.00 | | 1 | 0.79 | GPLD1 | 1 | 0.89 | PIGW |
| negative regulation of jnk cascade: GO | 32 | 3 | 1.57 | F2RL1; GSTP1; SERPINB3 | 4 | 1.47 | AMBP; DACT1; MAPK8IP1; PER1 | 0 | 0.00 | | 0 | 0.00 | | 1 | 0.79 | DACT1 | 1 | 0.89 | GSTP1 |
| response to dexamethasone: GO | 32 | 3 | 1.57 | IL1B; IL6; PTAFR | 1 | 0.37 | MSTN | 0 | 0.00 | | 1 | 13.06 | IL1B | 0 | 0.00 | | 1 | 0.89 | PTAFR |
| syndecan 4 pathway | 32 | 3 | 1.57 | CXCR4; MMP9; TNC | 1 | 0.37 | FGFR1 | 0 | 0.00 | | 0 | 0.00 | | 5 | 3.97 | CXCL12; FGF2; FGFR1; FZD7; MDK | 1 | 0.89 | ACTN1 |
| alpha synuclein pathway | 32 | 2 | 1.05 | KLK6; TH | 1 | 0.37 | SNCA | 0 | 0.00 | | 0 | 0.00 | | 1 | 0.79 | SNCA | 1 | 0.89 | TH |
| endocardial cushion development: GO | 32 | 2 | 1.05 | FOXF1; TBX20 | 2 | 0.74 | TBX5; TMEM100 | 0 | 0.00 | | 0 | 0.00 | | 0 | 0.00 | | 1 | 0.89 | SNAI2 |
| keratan sulfate metabolic process: GO | 32 | 2 | 1.05 | B3GNT3; CHST1 | 2 | 0.74 | CHST5; PRELP | 0 | 0.00 | | 0 | 0.00 | | 0 | 0.00 | | 1 | 0.89 | CHST1 |
| latent infection of homo sapiens with mycobacterium tuberculosis | 32 | 2 | 1.05 | CAMP; LTF | 4 | 1.47 | ATP6V0A4; ATP6V1B1; NOS2; TF | 0 | 0.00 | | 0 | 0.00 | | 1 | 0.79 | ATP6V0A4 | 1 | 0.89 | LTF |
| myd88 dependent toll like receptor signaling pathway: GO | 32 | 2 | 1.05 | MYD88; TLR10 | 0 | 0.00 | | 0 | 0.00 | | 0 | 0.00 | | 0 | 0.00 | | 1 | 0.89 | MYD88 |
| patterning of blood vessels: GO | 32 | 2 | 1.05 | BAK1; TBX20 | 1 | 0.37 | SEMA3E | 0 | 0.00 | | 0 | 0.00 | | 1 | 0.79 | SEMA3E | 1 | 0.89 | BAK1 |
| regulation of organ formation: GO | 32 | 2 | 1.05 | GDNF; WNT5A | 7 | 2.58 | DKK1; FGF1; FGFR1; HAND2; MESP1; SIX1; | 0 | 0.00 | | 0 | 0.00 | | 4 | 3.18 | FGFR1; HAND2; MESP1; SPRY1 | 1 | 0.89 | WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | TBX5 | | | | | | | | | | | | |
| salivary gland development: GO | 32 | 2 | 1.05 | IL6; TGM2 | 4 | 1.47 | EDA; FGFR1; PAX6; SEMA3A | 0 | 0.00 | | 0 | 0.00 | | 1 | 0.79 | FGFR1 | 1 | 0.89 | TGM2 |
| sulfur compound transport: GO | 32 | 2 | 1.05 | RACGAP1; SLC26A9 | 5 | 1.84 | SLC19A3; SLC26A1; SLC26A5; SLC26A7; SLC7A9 | 0 | 0.00 | | 0 | 0.00 | | 1 | 0.79 | SLC19A3 | 1 | 0.89 | SLC26A6 |
| thiolester hydrolase activity: GO | 32 | 2 | 1.05 | ACOT7; LYPLA1 | 2 | 0.74 | ACOT1; ACOT12 | 0 | 0.00 | | 0 | 0.00 | | 0 | 0.00 | | 1 | 0.89 | ACOT7 |
| wnt noncanonical pathway | 32 | 2 | 1.05 | CSNK1A1; WNT5A | 1 | 0.37 | CAMK2A | 0 | 0.00 | | 0 | 0.00 | | 1 | 0.79 | FZD7 | 1 | 0.89 | WNT5A |
| blood vessel remodeling: GO | 32 | 1 | 0.52 | BAK1 | 3 | 1.11 | AGT; LIF; NOL3 | 0 | 0.00 | | 0 | 0.00 | | 1 | 0.79 | FOXC1 | 1 | 0.89 | BAK1 |
| ca2+ pathway | 32 | 1 | 0.52 | WNT5A | 1 | 0.37 | FZD4 | 0 | 0.00 | | 0 | 0.00 | | 1 | 0.79 | GNG11 | 1 | 0.89 | WNT5A |
| integrin a4b1 pathway | 32 | 1 | 0.52 | YWHAZ | 0 | 0.00 | | 0 | 0.00 | | 0 | 0.00 | | 2 | 1.59 | JAM2; MDK | 1 | 0.89 | YWHAZ |
| negative regulation of response to extracellular stimulus: GO | 32 | 1 | 0.52 | CCK | 4 | 1.47 | CARTPT; KANK2; LEP; NRBP2 | 0 | 0.00 | | 0 | 0.00 | | 0 | 0.00 | | 1 | 0.89 | SNAI2 |
| positive regulation of lipid kinase activity: GO | 32 | 1 | 0.52 | CCL21 | 2 | 0.74 | ERBB4; FGFR3 | 0 | 0.00 | | 0 | 0.00 | | 2 | 1.59 | ERBB4; FGF2 | 1 | 0.89 | VAV2 |
| positive regulation of sodium ion transport: GO | 32 | 1 | 0.52 | ATP1B3 | 5 | 1.84 | DMD; DRD4; NKX2-5; SGK2; WNK2 | 0 | 0.00 | | 0 | 0.00 | | 3 | 2.38 | ATP1B2; GLRX; TESC | 1 | 0.89 | SGK1 |
| sema4d in semaphorin signaling | 32 | 1 | 0.52 | RAC2 | 3 | 1.11 | MYH11; MYH14; MYL9 | 0 | 0.00 | | 1 | 13.06 | RAC2 | 0 | 0.00 | | 1 | 0.89 | RND1 |
| somatic cell dna recombination: GO | 32 | 1 | 0.52 | EXO1 | 0 | 0.00 | | 0 | 0.00 | | 0 | 0.00 | | 0 | 0.00 | | 1 | 0.89 | EXO1 |
| trna transport: GO | 32 | 1 | 0.52 | RAN | 0 | 0.00 | | 0 | 0.00 | | 0 | 0.00 | | 0 | 0.00 | | 1 | 0.89 | RAN |
| degradation of the extracellular matrix | 89 | 8 | 1.50 | CTSB; CTSL; LAMB3; MMP1; MMP10; MMP12; | 3 | 0.40 | COL9A2; ELANE; KLKB1 | 0 | 0.00 | | 0 | 0.00 | | 4 | 1.14 | CTSG; DCN; ELANE; GULP1 | 3 | 0.96 | LAMB3; MMP25; MMP3 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | MMP3; MMP9 | | | | | | | | | | | | | | | |
| establishment of localization by movement along microtubule: GO | 89 | 5 | 0.94 | DYNLL1; HIF1A; KIF23; KIF4A; NEFL | 4 | 0.53 | APBA1; DYNC1I1; KIF1A; MAPT | 0 | 0.00 | | 0 | 0.00 | | 2 | 0.57 | APBA1; MAPT | 3 | 0.96 | HIF1A; KIF23; KIF4A |
| cellular amino acid biosynthetic process: GO | 89 | 4 | 0.75 | AHCY; ALDH4A1; GOT2; MTHFD2 | 6 | 0.80 | ASPA; BHMT2; CARNS1; CDO1; DHPS; GPT | 0 | 0.00 | | 0 | 0.00 | | 4 | 1.14 | ASPA; GAMT; GATM; GPT | 3 | 0.96 | GADL1; GOT2; NAGS |
| establishment of protein localization to plasma membrane: GO | 89 | 3 | 0.56 | JUP; RAB10; RAB31 | 8 | 1.06 | ACTN2; ANK2; KCNB1; KCNB2; PALM; PRKG2; PTCH1; SPTBN4 | 0 | 0.00 | | 0 | 0.00 | | 5 | 1.43 | PALM; PRKG2; PTCH1; SPTBN4; TESC | 3 | 0.96 | EFR3B; PKP3; RAB31 |
| core promoter binding: GO | 146 | 7 | 0.80 | E2F3; E2F7; H2AFZ; HMGA2; IFI16; NR4A3; STAT1 | 8 | 0.65 | CALCOCO1; GATA1; HDAC5; MYOCD; PAX6; SOX1; SOX8; TFAP2B | 0 | 0.00 | | 0 | 0.00 | | 1 | 0.17 | ESR1 | 5 | 0.97 | E2F1; E2F7; H2AFZ; HMGA2; IFI16 |
| production of molecular mediator of immune response: GO | 61 | 6 | 1.65 | EXO1; IGKV4-1; IL7R; POLQ; SLAMF1; TREM1 | 0 | 0.00 | | 0 | 0.00 | | 2 | 13.70 | IL7R; TREM1 | 0 | 0.00 | | 2 | 0.93 | EXO1; POLQ |
| cardiac ventricle morphogenesis: GO | 61 | 5 | 1.37 | DSP; FOXF1; HIF1A; NRG1; TBX20 | 11 | 2.13 | COL11A1; HAND2; MESP1; MYL3; NKX2-5; NPY5R; TBX5; TNNC1; | 0 | 0.00 | | 0 | 0.00 | | 7 | 2.92 | COL11A1; CPE; FOXC1; HAND2; MESP1; TNNC1; ZFPM2 | 2 | 0.93 | HIF1A; NRG1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | TNNT2; TPM1; ZFPM2 | | | | | | | | | | | | |
| negative regulation of nucleotide metabolic process: GO | 61 | 4 | 1.10 | CDA; GNAI3; GPR87; PPIF | 8 | 1.55 | ADRA2A; DRD4; GALR1; GRM7; MLXIPL; PALM; PPARGC1A; SNCA | 0 | 0.00 | | 0 | 0.00 | | 5 | 2.08 | ADRA2A; LPAR1; PALM; PPARGC1A; SNCA | 2 | 0.93 | CDA; PPIF |
| negative regulation of transporter activity: GO | 61 | 4 | 1.10 | GSTO1; MMP9; PCSK9; PPIF | 12 | 2.32 | ACTN2; ADRA2A; AGT; ANO9; ATP1A2; CASQ2; DRD4; GSTM2; HAMP; SLN; SNCA; TRDN | 0 | 0.00 | | 0 | 0.00 | | 4 | 1.67 | ADRA2A; ANO9; SNCA; TRDN | 2 | 0.93 | PCSK9; PPIF |
| transferase activity transferring alkyl or aryl other than methyl groups: GO | 61 | 4 | 1.10 | COQ2; GSTO1; GSTP1; SRM | 9 | 1.74 | CLIC5; DHPS; GSTA3; GSTM2; GSTM3; GSTM5; GSTT2; GSTT2B; MAT1A | 0 | 0.00 | | 0 | 0.00 | | 2 | 0.83 | CLIC5; GSTM5 | 2 | 0.93 | GSTP1; PDSS1 |
| metal cluster binding: GO | 61 | 1 | 0.27 | RSAD2 | 1 | 0.19 | CMAHP | 0 | 0.00 | | 0 | 0.00 | | 2 | 0.83 | AOX1; CMAHP | 2 | 0.93 | BRIP1; XDH |
| leukocyte mediated immunity: GO | 175 | 27 | 2.58 | ANXA3; C1QBP; CCL3; CTSC; CXCL5; CXCL6; EXO1; IGHG1; IGHG2; IGHG4; IGKC; IGKV4-1; | 8 | 0.54 | C3; C4BPA; C6; C7; CLEC2A; CLU; ELANE; KLRF2 | 2 | 4.78 | IGHG1; IGKV3-20 | 5 | 11.94 | ANXA3; CXCL5; GZMB; SERPINB9; TREM1 | 7 | 1.02 | C3; CLU; CTSG; ELANE; IGHM; IGHV3-23; KLRF2 | 6 | 0.97 | BCL3; CXCL6; EXO1; IL13RA2; PLA2G3; RAET1L |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | IL13RA2; IL4R; IL6; NR4A3; PLA2G3; PRDX1; RAET1E; RAET1L; SERPINB9; SLAMF1; SLAMF7; TREM1; ULBP1; ULBP2; ULBP3 | | | | | | | | | | | | | | | |
| phagocytosis: GO | 175 | 17 | 1.63 | ACTB; ACTR3; ANXA1; ANXA3; ARPC1A; ARPC3; CEACAM4; CLEC7A; CSNK1A1; FCGR1A; IGHG1; IGHG2; IGHG4; IGKC; IGKV4-1; SLAMF1; TGM2 | 9 | 0.61 | ADORA1; COLEC12; ELANE; FCN2; GSN; MARCO; MERTK; P2RX7; PLA2G6 | 2 | 4.78 | IGHG1; IGKV3-20 | 1 | 2.39 | ANXA3 | 5 | 0.73 | ELANE; GULP1; IGHM; IGHV3-23; TUB | 6 | 0.97 | ACTB; ARPC1A; CLEC7A; ICAM5; TGM2; VAV2 |
| anion channel activity: GO | 90 | 5 | 0.93 | CLCA2; GABRQ; LRRC8D; SLC26A9; VDAC1 | 19 | 2.49 | ANO3; ANO5; ANO9; BEST2; BEST3; BEST4; CFTR; CLCNKA; CLCNKB; CLIC5; GABRA2; | 0 | 0.00 | | 0 | 0.00 | | 4 | 1.13 | ANO9; CLCN4; CLIC5; GLRB | 3 | 0.95 | CLCA2; SLC26A6; VDAC1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | GABRB3; GABRG3; GABRP; GLRB; SLC17A7; SLC26A1; SLC26A5; SLC26A7 | | | | | | | | | | | | |
| membrane lipid metabolic process: GO | 176 | 15 | 1.43 | ARSH; B3GNT5; CERS3; CWH43; GLTP; NEU2; PIGW; PLAUR; SERINC2; SGPP2; SPTSSA; ST6GALNAC1; ST8SIA2; TH; UGCG | 7 | 0.47 | AGMO; FA2H; GAL3ST1; GPLD1; P2RX1; P2RX7; ST6GALNAC5 | 0 | 0.00 | | 0 | 0.00 | | 8 | 1.15 | ACER1; ALDH3A2; ALDH5A1; GAL3ST4; GPLD1; PSAPL1; SPTSSB; ST6GALNAC5 | 6 | 0.97 | B3GNT5; PIGW; SERINC2; ST6GALNAC1; ST8SIA2; TH |
| endocrine system development: GO | 119 | 9 | 1.27 | ADCYAP1; ANXA1; BAK1; FOXE1; IL6; PITX1; STRA6; TGFBR1; WNT5A | 13 | 1.29 | BMP5; CLU; CYP17A1; GCM2; GLI2; MNX1; NKX2-5; NOG; NR5A1; PAX6; SIX1; TG; WNT11 | 1 | 3.51 | CDKN1C | 0 | 0.00 | | 4 | 0.85 | CLU; GLI2; MDK; WNT11 | 4 | 0.95 | BAK1; FOXE1; PITX1; WNT5A |
| positive regulation of interleukin 12 production: GO | 33 | 4 | 2.03 | IDO1; IFNG; IL12B; TNFSF9 | 0 | 0.00 | | 0 | 0.00 | | 0 | 0.00 | | 0 | 0.00 | | 1 | 0.86 | HLA-G |
| signal transduction in absence of ligand: GO | 33 | 4 | 2.03 | BAK1; BCL2A1; IL1A; IL1B | 1 | 0.36 | BCL2 | 0 | 0.00 | | 1 | 12.66 | IL1B | 1 | 0.77 | BCL2 | 1 | 0.86 | BAK1 |
| bmal1 clock npas2 activates circadian expression | 33 | 3 | 1.52 | ARNTL2; NAMPT; SERPINE1 | 6 | 2.15 | BHLHE41; CRY2; DBP; F7; PER1; PPARGC1A | 0 | 0.00 | | 1 | 12.66 | SERPINE1 | 3 | 2.31 | BHLHE41; CRY2; PPARGC1A | 1 | 0.86 | NAMPT |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| death pathway | 33 | 3 | 1.52 | CYCS; TNFRSF10A; TNFSF10 | 2 | 0.72 | BCL2; GAS2 | 0 | 0.00 | | 0 | 0.00 | | 1 | 0.77 | BCL2 | 1 | 0.86 | CYCS |
| snrna binding: GO | 33 | 3 | 1.52 | DDX21; EIF5A; ISG20 | 0 | 0.00 | | 0 | 0.00 | | 0 | 0.00 | | 0 | 0.00 | | 1 | 0.86 | DDX21 |
| glutathione transferase activity: GO | 33 | 2 | 1.01 | GSTO1; GSTP1 | 7 | 2.50 | CLIC5; GSTA3; GSTM2; GSTM3; GSTM5; GSTT2; GSTT2B | 0 | 0.00 | | 0 | 0.00 | | 2 | 1.54 | CLIC5; GSTM5 | 1 | 0.86 | GSTP1 |
| il8 cxcr2 pathway | 33 | 2 | 1.01 | GNA15; RAC2 | 1 | 0.36 | DNM1 | 0 | 0.00 | | 1 | 12.66 | RAC2 | 1 | 0.77 | PIK3R6 | 1 | 0.86 | GNA15 |
| mitochondrion localization: GO | 33 | 2 | 1.01 | HIF1A; NEFL | 6 | 2.15 | ALB; ATCAY; ATP2A1; KAT2A; MAPT; PLIN5 | 0 | 0.00 | | 0 | 0.00 | | 2 | 1.54 | BHLHA15; MAPT | 1 | 0.86 | HIF1A |
| negative regulation of actin filament depolymerization: GO | 33 | 2 | 1.01 | CAPZA1; TWF1 | 6 | 2.15 | CAPZA3; GSN; LMOD1; SCIN; SPTBN4; TMOD1 | 0 | 0.00 | | 0 | 0.00 | | 4 | 3.08 | CAPZA3; LMOD1; SCIN; SPTBN4 | 1 | 0.86 | TWF1 |
| paradoxical activation of raf signaling by kinase inactive braf | 33 | 2 | 1.01 | ACTB; NRAS | 1 | 0.36 | CNKSR2 | 0 | 0.00 | | 0 | 0.00 | | 1 | 0.77 | CNKSR2 | 1 | 0.86 | ACTB |
| regulation of lamellipodium organization: GO | 33 | 2 | 1.01 | FSCN1; RAC2 | 2 | 0.72 | FRMD7; SLIT2 | 0 | 0.00 | | 1 | 12.66 | RAC2 | 1 | 0.77 | SLIT2 | 1 | 0.86 | EPHA2 |
| rna phosphodiester bond hydrolysis exonucleolytic: GO | 33 | 2 | 1.01 | ISG20; ZC3H12A | 0 | 0.00 | | 0 | 0.00 | | 0 | 0.00 | | 0 | 0.00 | | 1 | 0.86 | ZC3H12A |
| signaling by moderate kinase activity braf | 33 | 2 | 1.01 | ACTB; NRAS | 1 | 0.36 | CNKSR2 | 0 | 0.00 | | 0 | 0.00 | | 1 | 0.77 | CNKSR2 | 1 | 0.86 | ACTB |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| mutants | | | | | | | | | | | | | | | | | | | |
| axoneme assembly: GO | 33 | 1 | 0.51 | PLA2G3 | 6 | 2.15 | CCDC114; CCDC40; DNAAF1; HYDIN; RSPH1; SPEF2 | 0 | 0.00 | | 0 | 0.00 | | 2 | 1.54 | CCDC114; SPEF2 | 1 | 0.86 | PLA2G3 |
| protein destabilization: GO | 33 | 1 | 0.51 | PLK1 | 2 | 0.72 | GSN; SNCA | 0 | 0.00 | | 0 | 0.00 | | 1 | 0.77 | SNCA | 1 | 0.86 | PLK1 |
| regulation of glycogen metabolic process: GO | 33 | 1 | 0.51 | PHLDA2 | 4 | 1.43 | ENPP1; GCGR; IRS2; SORBS1 | 0 | 0.00 | | 0 | 0.00 | | 0 | 0.00 | | 1 | 0.86 | PHLDA2 |
| renal water homeostasis: GO | 33 | 1 | 0.51 | AQP3 | 9 | 3.22 | ADCY2; ADCY5; ADCY6; ADCY8; AQP4; CYP4A11; CYP4F12; PRKAR2B; TFAP2B | 1 | 12.66 | PRKAR2B | 0 | 0.00 | | 2 | 1.54 | CYP4A11; CYP4F12 | 1 | 0.86 | AQP3 |
| transcriptional activation of mitochondrial biogenesis | 33 | 1 | 0.51 | CYCS | 2 | 0.72 | PPARGC1A; SHC2 | 0 | 0.00 | | 0 | 0.00 | | 2 | 1.54 | PPARGC1A; SHC2 | 1 | 0.86 | CYCS |
| translation regulator activity: GO | 33 | 1 | 0.51 | EIF4EBP1 | 4 | 1.43 | CELF4; CPEB1; SAMD4A; ZNF540 | 0 | 0.00 | | 0 | 0.00 | | 2 | 1.54 | CPEB1; ZNF540 | 1 | 0.86 | EIF4EBP1 |
| mrna 3'-end processing | 33 | 0 | 0.00 | | 0 | 0.00 | | 0 | 0.00 | | 0 | 0.00 | | 0 | 0.00 | | 1 | 0.86 | DDX39A |
| ubiquitin like protein conjugating enzyme binding: GO | 33 | 0 | 0.00 | | 0 | 0.00 | | 0 | 0.00 | | 0 | 0.00 | | 0 | 0.00 | | 1 | 0.86 | RNF19B |
| mapk6/mapk4 signaling | 62 | 5 | 1.35 | CDK1; MAPK6; MMP10; | 0 | 0.00 | | 0 | 0.00 | | 0 | 0.00 | | 0 | 0.00 | | 2 | 0.91 | CDK1; MAPK6 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | PSMA5; PSMB6 | | | | | | | | | | | | | | | |
| myd88 cascade initiated on plasma membrane | 62 | 4 | 1.08 | DUSP6; MYD88; S100A12; UBE2N | 1 | 0.19 | PELI2 | 0 | 0.00 | | 0 | 0.00 | | 1 | 0.41 | PELI2 | 2 | 0.91 | DUSP6; MYD88 |
| toll like receptor 10 (tlr10) cascade | 62 | 4 | 1.08 | DUSP6; MYD88; S100A12; UBE2N | 1 | 0.19 | PELI2 | 0 | 0.00 | | 0 | 0.00 | | 1 | 0.41 | PELI2 | 2 | 0.91 | DUSP6; MYD88 |
| toll like receptor 5 (tlr5) cascade | 62 | 4 | 1.08 | DUSP6; MYD88; S100A12; UBE2N | 1 | 0.19 | PELI2 | 0 | 0.00 | | 0 | 0.00 | | 1 | 0.41 | PELI2 | 2 | 0.91 | DUSP6; MYD88 |
| positive regulation of dendrite development: GO | 62 | 2 | 0.54 | LRP8; NRG1 | 14 | 2.66 | APOE; BMP5; CAMK1; CAMK2B; COBL; EEF2K; FOXO6; ILIRAPL1; NLGN1; PAK3; PALM; PPP1R9A; RELN; SHANK1 | 0 | 0.00 | | 0 | 0.00 | | 6 | 2.46 | CAMK1; FOXO6; LPAR1; PAK3; PALM; RELN | 2 | 0.91 | NRG1; SGK1 |
| protein localization to cell periphery: GO | 148 | 7 | 0.79 | ABCA12; ATP1B3; JUP; P2RY1; PIGW; RAB10; RAB31 | 12 | 0.96 | ACTN2; ADIPOQ; ANK2; CALCR; DPP10; DPP6; KCNB1; KCNB2; PALM; PRKG2; PTCH1; SPTBN4 | 1 | 2.82 | ADIPOQ | 0 | 0.00 | | 7 | 1.20 | DPP6; PALM; PRKG2; PTCH1; SPTBN4; TESC; TUB | 5 | 0.96 | EFR3B; P2RY1; PIGW; PKP3; RAB31 |
| glycosyl compound biosynthetic process: GO | 91 | 7 | 1.29 | ACOT7; AMD1; CDA; NME1; TK1; TYMP; UPP1 | 5 | 0.65 | ACACB; ATP6V0A4; MAT1A; SLC26A1; | 0 | 0.00 | | 0 | 0.00 | | 1 | 0.28 | ATP6V0A4 | 3 | 0.93 | ACOT7; CDA; TK1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | | | | UPP2 | | | | | | | | | | | | |
| protein o linked glycosylation: GO | 91 | 6 | 1.10 | B3GNT3; B3GNT5; GALNT14; GALNT6; GCNT4; SDF2L1 | 13 | 1.69 | A4GNT; GALNT13; GALNT8; GXYLT2; MUC16; MUC20; MUC4; MUC5AC; MUC5B; MUC6; MUC7; MUCL1; TET1 | 0 | 0.00 | | 0 | 0.00 | | 5 | 1.40 | GXYLT2; MUC20; MUC7; MUCL1; TET1 | 3 | 0.93 | B3GNT5; GALNT14; GALNT6 |
| acetyltransferase activity: GO | 91 | 2 | 0.37 | BRCA2; ESCO2 | 5 | 0.65 | CRAT; KAT2A; MOGAT2; NAT8; NAT8L | 0 | 0.00 | | 0 | 0.00 | | 0 | 0.00 | | 3 | 0.93 | BRCA2; LPCAT1; NAGS |
| oxidoreductase complex: GO | 91 | 2 | 0.37 | OGDHL; RRM2 | 3 | 0.39 | GPD1; NOX1; SNCA | 1 | 4.59 | GPD1 | 0 | 0.00 | | 1 | 0.28 | SNCA | | 0.93 | GLDC; OGDHL; RRM2 |
| golgi stack: GO | 120 | 6 | 0.84 | FUT1; FUT2; FUT3; PITPNM1; PSENEN; SULF2 | 4 | 0.39 | ABO; FUT9; ICA1; ST6GAL2 | 0 | 0.00 | | 0 | 0.00 | | 4 | 0.85 | ABO; ATL1; GAL3ST4; ICA1 | 4 | 0.95 | FUT1; FUT2; FUT3; PITPNM1 |
| embryonic skeletal system development: GO | 120 | 5 | 0.70 | EIF4A3; MDFI; SULF2; TGFBR1; WNT5A | 16 | 1.57 | ALX1; ALX4; COL11A1; DMRT2; DSCAML1; FGF9; GSC; NOG; OSR1; OSR2; PCSK5; RBP4; SIX1; SPEF2; TBX15; WNT11 | 0 | 0.00 | | 0 | 0.00 | | 10 | 2.12 | ALX4; COL11A1; DMRT2; MYCN; OSR1; PRRX1; SHOX2; SPEF2; TBX15; WNT11 | 4 | 0.95 | EIF4A3; MDFI; WNT5A; WNT9B |
| cell redox homeostasis: GO | 63 | 7 | 1.86 | CAMP; IL6; LTF; PDIA3; | 1 | 0.19 | NOS2 | 0 | 0.00 | | 0 | 0.00 | | 1 | 0.40 | GLRX | 2 | 0.90 | LTF; TXN |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | SH3BGRL3; TXN; TXNDC8 | | | | | | | | | | | | | | | |
| retinol metabolism | 63 | 6 | 1.59 | ADH7; LRAT; RDH16; UGT1A1; UGT1A10; UGT1A7 | 12 | 2.25 | ADH1B; ADH1C; ALDH1A1; AWAT2; CYP1A1; CYP1A2; CYP2A6; CYP2C9; CYP3A5; CYP4A11; UGT2A1; UGT2B7 | 0 | 0.00 | | 0 | 0.00 | | 4 | 1.61 | CYP3A4; CYP3A5; CYP4A11; DGAT2 | 2 | 0.90 | LRAT; RDH16 |
| endothelin pathway | 63 | 4 | 1.06 | GNA15; GNAI3; MMP1; PRKCQ | 6 | 1.12 | ADCY2; ADCY5; ADCY6; ADCY8; EDN3; GNAZ | 0 | 0.00 | | 0 | 0.00 | | 1 | 0.40 | EDN3 | 2 | 0.90 | GNA15; PRKCQ |
| glutamine family amino acid metabolic process: GO | 63 | 4 | 1.06 | ALDH4A1; GGH; GOT2; HAL | 2 | 0.37 | NOS2; PRODH | 0 | 0.00 | | 0 | 0.00 | | 2 | 0.81 | ALDH5A1; PRODH | 2 | 0.90 | GOT2; NAGS |
| protein polymerization: GO | 63 | 4 | 1.06 | FBXO5; NEFL; UBE2C; UBE2S | 6 | 1.12 | ARHGAP6; CASQ2; COBL; GSN; TPPP; TPPP3 | 1 | 6.63 | TPPP3 | 0 | 0.00 | | 1 | 0.40 | TPPP | 2 | 0.90 | UBE2C; UBE2S |
| post translational protein modification | 63 | 3 | 0.80 | GALNT14; GALNT6; GCNT4 | 8 | 1.50 | GALNT13; GALNT8; GALNTL6; MUC16; MUC4; MUC5AC; MUC5B; MUC7 | 0 | 0.00 | | 0 | 0.00 | | 1 | 0.40 | MUC7 | 2 | 0.90 | GALNT14; GALNT6 |
| protein serine threonine phosphatase activity: GO | 63 | 3 | 0.80 | CDKN3; CYCS; UBLCP1 | 1 | 0.19 | MYH3 | 0 | 0.00 | | 0 | 0.00 | | 0 | 0.00 | | 2 | 0.90 | CDKN3; CYCS |
| rna polymerase | 63 | 2 | 0.53 | ACTB; | 5 | 0.94 | BACH2; | 0 | 0.00 | | 0 | 0.00 | | 2 | 0.81 | BACH2; | 2 | 0.90 | ACTB; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| ii distal enhancer sequence specific dna binding: GO | | | | H2AFZ | | | MEOX2; NR5A1; SOX10; ZBTB16 | | | | | | | | | MEOX2 | | | H2AFZ |
| cardiocyte differentiation: GO | 92 | 7 | 1.27 | CALR; CCNB1; CDK1; CXADR; EOMES; GREM1; NRG1 | 12 | 1.54 | ACTN2; AGT; FHOD3; FOLR1; HAND2; KAT2A; MESP1; MYH11; MYOCD; NKX2-5; SORBS2; TBX5 | 0 | 0.00 | | 0 | 0.00 | | 3 | 0.83 | HAND2; MESP1; SORBS2 | 3 | 0.92 | CCNB1; CDK1; NRG1 |
| regulation of insulin secretion | 92 | 6 | 1.09 | DPP4; GNA15; GNAI3; GNGT2; SLC25A5; SLC2A1 | 11 | 1.41 | ABCC8; ADCY5; ADCY6; ADCY8; ADRA2A; CHRM3; KCNB1; LEP; NALCN; PAX6; PRKAR2B | 1 | 4.54 | PRKAR2B | 0 | 0.00 | | 4 | 1.10 | ADRA2A; CHRM3; GNG11; NALCN | 3 | 0.92 | DPP4; GNA15; SLC2A1 |
| glycerophos-pholipid metabolism | 92 | 5 | 0.91 | AKRIB10; ESCO2; LYPLA1; MBOAT2; PLA2G3 | 7 | 0.90 | CHPT1; DGKG; GPAM; GPD1; PLA2G5; PLA2G6; PNPLA3 | 2 | 9.08 | GPAM; GPD1 | 0 | 0.00 | | 1 | 0.28 | PNPLA3 | 3 | 0.92 | AKRIB10; LPCAT1; PLA2G3 |
| hormone activity: GO | 92 | 5 | 0.91 | ADCYAP1; ADM2; CCK; INSL3; PTHLH | 10 | 1.28 | ADIPOQ; AGT; EDN3; HAMP; INHBB; LEP; LHB; OSTN; SCT; TG | 1 | 4.54 | ADIPOQ | 0 | 0.00 | | 1 | 0.28 | PNPLA3 EDN3 | 3 | 0.92 | ADM2; PTHLH; UCN2 |
| leukocyte mediated cytotoxicity: GO | 34 | 9 | 4.43 | CTSC; PRDX1; RAET1E; | 3 | 1.04 | CLEC2A; ELANE; KLRF2 | 0 | 0.00 | | 2 | 24.58 | GZMB; TREM1 | 3 | 2.24 | CTSG; ELANE; KLRF2 | 1 | 0.83 | RAET1L |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | RAET1L; SLAMF7; TREM1; ULBP1; ULBP2; ULBP3 | | | | | | | | | | | | | | | |
| il1 pathway | 34 | 7 | 3.45 | IL1A; IL1B; IL1R2; IL1RAP; IL1RN; MYD88; UBE2N | 0 | 0.00 | | 0 | 0.00 | | 1 | 12.29 | IL1B | 0 | 0.00 | | 1 | 0.83 | MYD88 |
| ascorbate and aldarate metabolism | 34 | 5 | 2.46 | AKR1B10; ALDH1A3; UGT1AI; UGT1A10; UGT1A7 | 2 | 0.69 | UGT2A1; UGT2B7 | 0 | 0.00 | | 0 | 0.00 | | 1 | 0.75 | ALDH3A2 | 1 | 0.83 | AKR1B10 |
| regulation of mesenchymal cell proliferation: GO | 34 | 4 | 1.97 | FOXF1; STAT1; TP63; WNT5A | 5 | 1.73 | FGF9; FGFR1; IRS2; SIX1; WNT11 | 0 | 0.00 | | 0 | 0.00 | | 6 | 4.48 | CHRD; FGFR1; MYCN; PRRX1; SHOX2; WNT11 | 1 | 0.83 | WNT5A |
| cd4 positive alpha beta t cell activation: GO | 34 | 3 | 1.48 | IL12B; IL6; RSAD2 | 1 | 0.35 | RORC | 0 | 0.00 | | 0 | 0.00 | | 0 | 0.00 | | 1 | 0.83 | BCL3 |
| cortical cytoskeleton organization: GO | 34 | 3 | 1.48 | CALR; KIF23; RACGAP1 | 1 | 0.35 | NLGN1 | 0 | 0.00 | | 0 | 0.00 | | 0 | 0.00 | | 1 | 0.83 | KIF23 |
| il2 pi3k pathway | 34 | 3 | 1.48 | IL2RA; JAK3; UGCG | 2 | 0.69 | BCL2; TERT | 0 | 0.00 | | 1 | 12.29 | IL2RA | 1 | 0.75 | BCL2 | 1 | 0.83 | E2F1 |
| t cell homeostasis: GO | 34 | 3 | 1.48 | CCNB2; IL2RA; JAK3 | 3 | 1.04 | BCL2; CACNA1F; P2RX7 | 0 | 0.00 | | 1 | 12.29 | IL2RA | 2 | 1.49 | BCL2; SLC46A2 | 1 | 0.83 | CCNB2 |
| carbohydrate derivative transporter activity: GO | 34 | 2 | 0.98 | GLTP; SLC28A3 | 0 | 0.00 | | 0 | 0.00 | | | 0.00 | | 1 | 0.75 | SLC29A1 | 1 | 0.83 | SLC28A3 |
| cell-cell junction organization | 34 | 2 | 0.98 | ACTB; JUP | 4 | 1.39 | CADM2; CDH12; | 0 | 0.00 | | 0 | 0.00 | | 1 | 0.75 | CADM2 | 1 | 0.83 | ACTB |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| forebrain neuron development: GO | 34 | 2 | 0.98 | SALL3; WNT5A | 9 | 3.12 | CDH4; CLDN16 DCX; DRD1; FEZF2; FGFR1; PLXNA3; SEMA3A; SLIT2; SLIT3; SOX1 | 0 | 0.00 | | 0 | 0.00 | | 3 | 2.24 | FGFR1; SLIT2; SLIT3 | 1 | 0.83 | WNT5A |
| mapk trk pathway | 34 | 2 | 0.98 | CDK5R1; NRAS | 0 | 0.00 | | 0 | 0.00 | | 0 | 0.00 | | 0 | 0.00 | | 1 | 0.83 | CDK5R1 |
| negative regulation of muscle tissue development: GO | 34 | 2 | 0.98 | GJA1; USP2 | 7 | 2.43 | DKK1; MSTN; MYOCD; NOG; RBP4; TBX5; TSC22D3 | 0 | 0.00 | | 0 | 0.00 | | 4 | 2.99 | IGFBP5; KCNK2; PRICKLE1; TSC22D3 | 1 | 0.83 | SOX15 |
| positive regulation of dendritic spine development: GO | 34 | 2 | 0.98 | LRP8; NRG1 | 11 | 3.82 | APOE; CAMK1; CAMK2B; EEF2K; FOXO6; NLGN1; PAK3; PALM; PPP1R9A; RELN; SHANK1 | 0 | 0.00 | | 0 | 0.00 | | 6 | 4.48 | CAMK1; FOXO6; LPAR1; PAK3; PALM; RELN | 1 | 0.83 | NRG1 |
| protein kinase b signaling: GO | 34 | 2 | 0.98 | CCL3; IL1B | 2 | 0.69 | MERTK; TMEM100 | 0 | 0.00 | | 1 | 12.29 | IL1B | 0 | 0.00 | | 1 | 0.83 | EPHA2 |
| proteoglycans | 34 | 2 | 0.98 | ESM1; SRGN | 7 | 2.43 | BCAN; CHAD; CHADL; HAPLN2; PODN; PRELP; SPOCK1 | 0 | 0.00 | | 0 | 0.00 | | 4 | 2.99 | CHAD; DCN; PODN; SPOCK1 | 1 | 0.83 | HAPLN3 |
| regulation of protein autophos-phorylation: GO | 34 | 2 | 0.98 | GREM1; RAP2B | 4 | 1.39 | ADIPOQ; EEF2K; ENPP1; PDGFD | 1 | 12.29 | ADIPOQ | 0 | 0.00 | | 0 | 0.00 | | 1 | 0.83 | RAP2B |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| regulation of type i interferon mediated signaling pathway: GO | 34 | 2 | 0.98 | STAT1; WNT5A | 1 | 0.35 | IFNA5 | 0 | 0.00 | | 0 | 0.00 | | 0 | 0.00 | | 1 | 0.83 | WNT5A |
| response to iron ion: GO | 34 | 2 | 0.98 | CCNB1; HMOX1 | 7 | 2.43 | APBB1; BCL2; CYBRD1; CYP1A1; HAMP; SNCA; TF | 0 | 0.00 | | 0 | 0.00 | | 4 | 2.99 | BCL2; CYBRD1; SLC40A1; SNCA | 1 | 0.83 | CCNB1 |
| brain morpho-genesis: GO | 34 | 1 | 0.49 | WNT5A | 2 | 0.69 | DKK1; SPEF2 | 0 | 0.00 | | 0 | 0.00 | | 2 | 1.49 | GDF7; SPEF2 | 1 | 0.83 | WNT5A |
| channel inhibitor activity: GO | 34 | 1 | 0.49 | PCSK9 | 4 | 1.39 | AMBP; BCL2; CFTR; HAMP | 0 | 0.00 | | 0 | 0.00 | | 2 | 1.49 | BCL2; KCNK2 | 1 | 0.83 | PCSK9 |
| chondroitin sulfate/dermatan sulfate metabolism | 34 | 1 | 0.49 | SDC1 | 6 | 2.08 | CHST12; GPC3; GPC6; IDUA; SDC2; UST | 0 | 0.00 | | 0 | 0.00 | | 4 | 2.99 | CHST12; DCN; DSEL; UST | 1 | 0.83 | AGRN |
| regulation of digestive system process: GO | 34 | 1 | 0.49 | ISX | 3 | 1.04 | HAMP; LEP; SCT | 0 | 0.00 | | 0 | 0.00 | | 0 | 0.00 | | 1 | 0.83 | SGK1 |
| vesicle docking involved in exocytosis: GO | 34 | 1 | 0.49 | UNC13A | 2 | 0.69 | CFTR; KCNB1 | 0 | 0.00 | | 0 | 0.00 | | 0 | 0.00 | | 1 | 0.83 | UNC13A |
| wnt signaling pathway calcium modulating pathway: GO | 34 | 1 | 0.49 | WNT5A | 3 | 1.04 | CAMK2A; FZD4; WNT11 | 0 | 0.00 | | 0 | 0.00 | | 1 | 0.75 | WNT11 | 1 | 0.83 | WNT5A |
| platelet derived growth factor receptor signaling pathway: GO | 34 | 0 | 0.00 | | 2 | 0.69 | PDGFD; TXNIP | 0 | 0.00 | | 0 | 0.00 | | 2 | 1.49 | PDGFRL; TXNIP | 1 | 0.83 | PLAT |
| leukocyte transendothelial migration | 121 | 7 | 0.97 | ACTB; CXCL13; CXCR4; GNAI3; MMP9; MSN; RAC2 | 9 | 0.88 | ACTN2; CLDN16; CLDN18; CLDN8; CTNNA3; MYL9; MYLPF; | 0 | 0.00 | | 1 | 3.45 | RAC2 | 5 | 1.05 | CLDN18; CLDN8; CXCL12; JAM2; POTEKP | 4 | 0.94 | ACTB; ACTN1; MSN; VAV2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | | | | NOX1; POTEKP | | | | | | | | | | | | |
| steroid hormone mediated signaling pathway: GO | 121 | 5 | 0.69 | CALR; CCNE1; NR4A3; PAQR5; RAN | 12 | 1.17 | AR; CALCOCO1; ESRRG; NR3C2; NR5A1; PGR; PPARGC1A; RHOXF1; RORB; RORC; RXRG; SCGB2A1 | 0 | 0.00 | | 0 | 0.00 | | 6 | 1.26 | ESR1; ESRRG; NR2F1; NR3C2; PGR; PPARGC1A | 4 | 0.94 | PAQR5; PPARD; RAN; SGK1 |
| positive regulation of protein complex assembly: GO | 179 | 16 | 1.50 | ACTR3; ARPC1A; ARPC3; ARPC5L; CCK; CCL21; CSF2; CXCL13; FOSL1; FSCN1; MMP1; MMP3; MSN; PFN1; PYCARD; VCP | 7 | 0.46 | GSN; IL5; MAPT; MITF; NKX2-5; SCIN; TPPP | 0 | 0.00 | | 0 | 0.00 | | 4 | 0.57 | MAPT; MITF; SCIN; TPPP | 6 | 0.95 | ARPC1A; CDC42EP1; FOSL1; MMP3; MSN; PFN1 |
| lymphocyte activation involved in immune response: GO | 93 | 7 | 1.26 | EOMES; EXO1; F2RL1; IFNE; IFNG; IL12B; IL6 | 3 | 0.38 | IFNA5; KLRF2; RORC | 0 | 0.00 | | 0 | 0.00 | | 1 | 0.27 | KLRF2 | 3 | 0.91 | BCL3; EXO1; IFNE |
| embryonic skeletal system morphogenesis: GO | 93 | 3 | 0.54 | EIF4A3; MDFI; TGFBR1 | 11 | 1.40 | ALX1; ALX4; COL11A1; DSCAML1; GSC; NOG; OSR1; OSR2; SIX1; SPEF2; TBX15 | 0 | 0.00 | | 0 | 0.00 | | 8 | 2.19 | ALX4; COL11A1; MYCN; OSR1; PRRX1; SHOX2; SPEF2; TBX15 | 3 | 0.91 | EIF4A3; MDFI; WNT9B |
| regulation of | 64 | 5 | 1.31 | ANXA1; | 11 | 2.03 | ADRA1A; | 0 | 0.00 | | 1 | 6.53 | SELE | 8 | 3.18 | ADCYAP1R1; | 2 | 0.89 | GNA15; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| phospholipase activity: GO | | | | GNA15; PTAFR; SIPR4; SELE | | | AGT; AGTR1; ARHGAP6; CALCR; CAMK2B; FGFR1; FGFR3; NMUR1; PLA2G5; SNCA | | | | | | | | | ADRA1A; AGTR1; ESR1; FGF2; FGFR1; LPAR1; SNCA | | | PTAFR |
| integration of energy metabolism | 122 | 6 | 0.82 | DPP4; GNA15; GNAI3; GNGT2; SLC25A5; SLC2A1 | 17 | 1.64 | ABCC8; ACACB; ADCY2; ADCY5; ADCY6; ADCY8; ADRA2A; CHRM3; GCGR; KCNB1; LEP; MLXIPL; NALCN; PAX6; PFKFB1; PRKAA2; PRKAR2B | 1 | 3.43 | PRKAR2B | 0 | 0.00 | | 6 | 1.25 | ADRA2A; CHRM3; GNG11; NALCN; PFKFB1; PRKAA2 | 4 | 0.93 | DPP4; GNA15; SLC2A1; TKT |
| chemokine signaling pathway | 180 | 24 | 2.23 | CCL17; CCL18; CCL21; CCL22; CCL3; CCL7; CCR4; CCR5; CXCL1; CXCL10; CXCL11; CXCL13; CXCL3; CXCL5; CXCL6; CXCL9; CXCR1; CXCR4; | 9 | 0.59 | ADCY2; ADCY5; ADCY6; ADCY8; CCL14; CXCR5; PLCB4; SHC2; SHC3 | 0 | 0.00 | | 3 | 6.96 | CXCL5; CXCL9; RAC2 | 5 | 0.71 | CCL14; CXCL12; GNG11; PLCB4; SHC2 | 6 | 0.95 | CCL20; CXCL11; CXCL2; CXCL6; CXCR1; VAV2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | GNAI3; GNGT2; JAK3; NRAS; RAC2; STAT1 | | | | | | | | | | | | | | | |
| prion diseases | 35 | 5 | 2.39 | HSPA5; IL1A; IL1B; IL6; PRNP | 3 | 1.01 | C6; C7; NCAM1 | 0 | 0.00 | | 1 | 11.94 | IL1B | 1 | 0.73 | NCAM1 | 1 | 0.81 | HSPA5 |
| neuron apoptotic process: GO | 35 | 4 | 1.91 | FAM162A; GAPDH; TNFRSF21; TP63 | 1 | 0.34 | BCL2 | 0 | 0.00 | | 0 | 0.00 | | 1 | 0.73 | BCL2 | 1 | 0.81 | GAPDH |
| mitotic g1 g1 s phases | 35 | 3 | 1.43 | PKMYT1; PSMA4; PSMD1 | 0 | 0.00 | | 0 | 0.00 | | 0 | 0.00 | | 0 | 0.00 | | 1 | 0.81 | PKMYT1 |
| multivesicular body: GO | 35 | 3 | 1.43 | CD79A; GJA1; LRAT | 3 | 1.01 | NAPSA; SFTPC; SLC2A4 | 0 | 0.00 | | 0 | 0.00 | | 1 | 0.73 | SLC40A1 | 1 | 0.81 | LRAT |
| one carbon metabolic process: GO | 35 | | 1.43 | AHCY; CA2; MTHFD2 | 5 | 1.69 | ALDH1L1; CA1; CA3; CA6; MAT1A | 0 | 0.00 | | 0 | 0.00 | | 3 | 2.18 | CA1; CA3; CA6 | 1 | 0.81 | CA2 |
| porphyrin containing compound metabolic process: GO | 35 | 3 | 1.43 | HMOX1; HMOX2; UGT1A1 | 5 | 1.69 | ALAS2; AMBP; CYP1A1; CYP1A2; PPOX | 0 | 0.00 | | 0 | 0.00 | | 1 | 0.73 | PPOX | 1 | 0.81 | HMOX2 |
| positive chemotaxis: GO | 35 | 3 | 1.43 | CCL3; SCG2; WNT5A | 0 | 0.00 | | | 0.00 | | 0 | 0.00 | | 3 | 2.18 | ANGPT1; CXCL12; FGF2 | 1 | 0.81 | WNT5A |
| rna polymerase ii activating transcription factor binding: GO | 35 | 3 | 1.43 | EOMES; IFI27; TBX20 | 1 | 0.34 | BHLHE41 | 0 | 0.00 | | 0 | 0.00 | | 1 | 0.73 | BHLHE41 | 1 | 0.81 | IFI27 |
| adrenergic | 35 | 2 | 0.96 | CAMP; GNA15 | 2 | 0.67 | AR; KCNJ3 | 0 | 0.00 | | 0 | 0.00 | | 0 | 0.00 | | 1 | 0.81 | GNA15 |
| frs2 mediated cascade | 35 | 2 | 0.96 | CDK1; NRAS | 6 | 2.02 | FGF1; FGF17; FGF22; FGF9; FGFR1; FGFR3 | 0 | 0.00 | | 0 | 0.00 | | 3 | 2.18 | FGF2; FGF22; FGFR1 | 1 | 0.81 | CDK1 |
| g alpha i pathway | 35 | 2 | 0.96 | PI3; RGS20 | 2 | 0.67 | KCNJ3; PLCB4 | 0 | 0.00 | | 0 | 0.00 | | 1 | 0.73 | PLCB4 | 1 | 0.81 | RGS20 |
| neuromuscular | 35 | 2 | 0.96 | TNC; | 4 | 1.35 | CACNA2D2; | 0 | 0.00 | | 0 | 0.00 | | 3 | 2.18 | CACNA2D2; | 1 | 0.81 | UNC13A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| junction development: GO | | | | UNC13A | | | CACNB1; LRP4; PDZRN3 | | | | | | | | | CACNB1; PDZRN3 | | | |
| positive regulation of axon extension: GO | 35 | 2 | 0.96 | NRG1; TNFRSF12A | 3 | 1.01 | CDH4; MAPT; NTRK3 | 0 | 0.00 | | 0 | 0.00 | | 2 | 1.45 | CXCL12; MAPT | 1 | 0.81 | NRG1 |
| positive regulation of cation channel activity: GO | 35 | 2 | 0.96 | GSTO1; NTSR1 | 7 | 2.36 | ACTN2; ANK2; CACNA2D1; FGF14; GSTM2; JPH2; TRDN | 0 | 0.00 | | 0 | 0.00 | | 2 | 1.45 | CACNA2D1; TRDN | 1 | 0.81 | NTSR1 |
| rab geranyl-geranylation | 35 | 2 | 0.96 | RAB10; RAB31 | 1 | 0.34 | RAB3B | 0 | 0.00 | | 0 | 0.00 | | 1 | 0.73 | RAB3B | 1 | 0.81 | RAB31 |
| regulation of multicellular organismal metabolic process: GO | 35 | 2 | 0.96 | IL6; SERPINB7 | 3 | 1.01 | AMELX; CYGB; MFAP4 | 0 | 0.00 | | 0 | 0.00 | | 1 | 0.73 | CTGF | 1 | 0.81 | PPARD |
| actin polymerization or depolymerization: GO | 35 | 1 | 0.48 | CFL1 | 3 | 1.01 | ARHGAP6; COBL; GSN | 0 | 0.00 | | 0 | 0.00 | | 0 | 0.00 | | 1 | 0.81 | CFL1 |
| agr pathway | 35 | 1 | 0.48 | NRG1 | 7 | 2.36 | ACTA1; CHRM1; DMD; LAMA2; NRG2; NRG3; PAK3 | 0 | 0.00 | | 0 | 0.00 | | 3 | 2.18 | CHRM1; LAMA2; PAK3 | 1 | 0.81 | NRG1 |
| clathrin mediated endocytosis: GO | 35 | 1 | 0.48 | STON2 | 3 | 1.01 | DNM1; SNCA; SYT1 | 0 | 0.00 | | 0 | 0.00 | | 2 | 1.45 | FCHO1; SNCA | 1 | 0.81 | STON2 |
| dendritic shaft: GO | 35 | 1 | 0.48 | NTSR1 | 4 | 1.35 | DRD1; GRM7; NLGN1; PRKAR2B | 1 | 11.94 | PRKAR2B | 0 | 0.00 | | 2 | 1.45 | CNIH3; LPAR1 | 1 | 0.81 | NTSR1 |
| hiv nef pathway | 35 | 1 | 0.48 | CYCS | 1 | 0.34 | BCL2 | 0 | 0.00 | | 0 | 0.00 | | 1 | 0.73 | BCL2 | 1 | 0.81 | CYCS |
| mitochondrial translation termination | 35 | 1 | 0.48 | MRPL13 | 0 | 0.00 | | 0 | 0.00 | | 0 | 0.00 | | 0 | 0.00 | | 1 | 0.81 | BRIP1 |
| positive regulation of viral | 35 | 1 | 0.48 | PFN1 | 0 | 0.00 | | 0 | 0.00 | | 0 | 0.00 | | 0 | 0.00 | | 1 | 0.81 | PFN1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| transcription: GO | | | | | | | | | | | | | | | | | | | |
| regulation of sodium ion transmembrane transporter activity: GO | 35 | 1 | 0.48 | PCSK9 | 6 | 2.02 | AGT; ATP1A2; DMD; DRD4; FXYD2; WNK2 | 0 | 0.00 | | 0 | 0.00 | | 2 | 1.45 | GLRX; TESC | 1 | 0.81 | PCSK9 |
| transcription elongation factor complex: GO | 35 | 1 | 0.48 | ELL2 | 0 | 0.00 | | 0 | 0.00 | | 0 | 0.00 | | 0 | 0.00 | | 1 | 0.81 | ELL2 |
| vesicle cytoskeletal trafficking: GO | 35 | 1 | 0.48 | KIF23 | 1 | 0.34 | DYNC1I1 | 0 | 0.00 | | 0 | 0.00 | | 0 | 0.00 | | 1 | 0.81 | KIF23 |
| calcium channel regulator activity: GO | 35 | 0 | 0.00 | | 5 | 1.69 | AMBP; GRM7; NRXN1; NRXN3; SGK2 | 0 | 0.00 | | 0 | 0.00 | | 2 | 1.45 | NRXN1; PRKG1 | 1 | 0.81 | SGK1 |
| regulation of glucose metabolic process: GO | 94 | 3 | 0.53 | IL6; PGAM1; PHLDA2 | 16 | 2.01 | ACACB; ADIPOQ; ENPP1; GCGR; GPLD1; IRS2; KAT2A; LEP; LEPR; MST1; PDK4; PFKFB1; PPARGC1A; RORC; SERPINA12; SORBS1 | 1 | 4.45 | ADIPOQ | 0 | 0.00 | | 8 | 2.16 | DGAT2; GPLD1; IGFBP5; PDK3; PDK4; PFKFB1; PPARGC1A; SERPINA12 | 3 | 0.91 | IGFBP3; PGAM1; PHLDA2 |
| response to topologically incorrect protein: GO | 152 | 16 | 1.76 | BAK1; CALR; CHAC1; EIF2S1; F12; HSPA4; HSPA5; HSPA6; HSPA8; HSPH1; IFNG; MANF; SDF2L1; SEC61G; | 6 | 0.47 | CASP12; CLU; HSPA1L; HSPB3; HSPB7; TSPYL2 | 0 | 0.00 | | 0 | 0.00 | | 4 | 0.67 | BHLHA15; CASP12; CLU; CREB3L1 | 5 | 0.93 | BAK1; F12; HSPA5; HSPA8; HSPH1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | VCP; YOD1 | | | | | | | | | | | | | | | |
| interleukin receptor shc signaling | 152 | 12 | 1.32 | ACTB; CSF2; DUSP6; DUSP9; EREG; HBEGF; IL2RA; JAK3; NRAS; NRG1; PSMA5; PSMB6 | 12 | 0.93 | BTC; CNKSR2; EGF; FGF1; FGFR1; FGFR3; GFRA1; GRIN2A; IL5; IRS2; NRG2; SHC2 | 0 | 0.00 | | 1 | 2.75 | IL2RA | 5 | 0.84 | ANGPT1; CNKSR2; EGF; FGFR1; SHC2 | 5 | 0.93 | ACTB; DUSP6; EREG; HBEGF; NRG1 |
| mesenchyme development: GO | 181 | 12 | 1.11 | EOMES; FAM83D; FOXF1; GDNF; HIF1A; HMGA2; NRG1; SEMA4B; STAT1; TBX20; TGFBR1; WNT5A | 30 | 1.96 | ACTA1; ALX1; AMELX; BCL2; EDN3; ERBB4; FGF9; FGFR1; FOLR1; FRZB; GSC; HAND2; MESP1; NKX2-5; NOG; OSR1; PAX3; SEMA3A; SEMA3B; SEMA3D; SEMA3E; SEMA3G; SIX1; SOX10; SOX8; TBX5; TCF21; TMEM100; WNT11; ZFPM2 | 0 | 0.00 | | 0 | 0.00 | | 13 | 1.82 | BCL2; BNC2; EDN3; ERBB4; FGFR1; FOXC1; HAND2; MESP1; OSR1; SEMA3E; SEMA4G; WNT11; ZFPM2 | 6 | 0.94 | HIF1A; HMGA2; NRG1; SEMA4B; SNAI2; WNT5A |
| antigen processing-cross presentation | 65 | 8 | 2.06 | CALR; CTSL; FCGR1A; MYD88; PDIA3; PSMA5; PSMB6; SEC61G | 0 | 0.00 | | 0 | 0.00 | | 0 | 0.00 | | 0 | 0.00 | | 2 | 0.87 | HLA-G; MYD88 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| cellular response to drug: GO | 65 | 7 | 1.80 | CD69; HIF1A; IL1B; MT2A; NME1; PRNP; TH | 6 | 1.09 | ADIPOQ; GPLD1; NOS2; PPP1R14A; PRKAA2; REN | 1 | 6.43 | ADIPOQ | 1 | 6.43 | IL1B | 3 | 1.17 | GPLD1; PRKAA2; SLC18A2 | 2 | 0.87 | HIF1A; TH |
| lysophospholipid pathway | 65 | 6 | 1.54 | GNA15; GNAI3; HBEGF; IL6; LPAR3; MMP9 | 7 | 1.27 | ADCY2; ADCY5; ADCY6; ADCY8; ADRA1B; GNAZ; MAPT | 0 | 0.00 | | 0 | 0.00 | | 2 | 0.78 | LPAR1; MAPT | 2 | 0.87 | GNA15; HBEGF |
| adenylate cyclase inhibiting g protein coupled receptor signaling pathway: GO | 65 | 5 | 1.29 | GNAI3; HRH3; INSL3; P2RY1; RGS1 | 15 | 2.72 | ADCY2; ADCY5; ADCY6; ADCY8; ADORA1; ADRA2A; CHRM1; CHRM2; CHRM3; CHRM4; DRD4; GNAZ; GRIK3; GRM7; NPY1R | 0 | 0.00 | | 0 | 0.00 | | 7 | 2.74 | ADRA2A; CHRM1; CHRM3; GRIK3; LPAR1; NPY1R; PSAPL1 | 2 | 0.87 | P2RY1; RGS1 |
| adherens junction organization: GO | 65 | 4 | 1.03 | CDH3; DSP; JUP; RHOD | 8 | 1.45 | ACTN2; ARHGAP6; BCL2; CADM2; CADM3; CDH12; CDH4; SORBS1 | 0 | 0.00 | | 0 | 0.00 | | 4 | 1.56 | BCL2; CADM2; CADM3; DLC1 | 2 | 0.87 | ACTN1; RHOD |
| positive regulation of lipase activity: GO | 65 | 4 | 1.03 | GNA15; PTAFR; SIPR4; SELE | 12 | 2.18 | ADRA1A; AGT; AGTR1; ARHGAP6; CALCR; CAMK2B; FGFR1; | 0 | 0.00 | | 1 | 6.43 | SELE | 7 | 2.74 | ADCYAP1R1; ADRA1A; AGTR1; ESR1; FGF2; FGFR1; LPAR1 | 2 | 0.87 | GNA15; PTAFR |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | | | | FGFR3; GPIHBP1; NMUR1; PLA2G5; PLIN5 | | | | | | | | | | | | |
| coated pit: GO | 65 | 3 | 0.77 | AP1S3; LDLR; SELE | 3 | 0.54 | CDHR5; SLC2A4; TF | 0 | 0.00 | | 1 | 6.43 | SELE | 1 | 0.39 | FCHO1 | 2 | 0.87 | AP1S3; LDLR |
| lysosomal transport: GO | 65 | 3 | 0.77 | HOOK1; HSPA8; PCSK9 | 2 | 0.36 | GPRASP1; PCDHGA3 | 0 | 0.00 | | 0 | 0.00 | | 1 | 0.39 | GPRASP1 | 2 | 0.87 | HSPA8; PCSK9 |
| membrane docking: GO | 65 | 3 | 0.77 | MSN; NDRG4; UNC13A | 4 | 0.73 | CFTR; KCNB1; SYT1; TSNARE1 | 0 | 0.00 | | 0 | 0.00 | | 0 | 0.00 | | 2 | 0.87 | MSN; UNC13A |
| multi organism localization: GO | 65 | 3 | 0.77 | KPNA2; RAN; TAP2 | 1 | 0.18 | VPS37D | 0 | 0.00 | | 0 | 0.00 | | 0 | 0.00 | | 2 | 0.87 | KPNA2; RAN |
| hdac classi pathway | 65 | 2. | 0.51 | MXD1; RAN | | 0.54 | GATA1; HDAC5; SSPO | 0 | 0.00 | | 0 | 0.00 | | 0 | 0.00 | | 2 | 0.87 | MXD1; RAN |
| protein c terminus binding: GO | 182 | 8 | 0.74 | CDC20; CENPF; DYNLL1; MKI67; NEFL; SDC1; TOP2A; YWHAQ | 12 | 0.78 | ATP2B2; CALCOCO1; DNM1; FBLN5; HSPB7; NEIL1; PPP1R9A; RBFOX1; SHANK1; SLC4A1; SYT1; ZBTB16 | 0 | 0.00 | | 0 | 0.00 | | 3 | 0.42 | CTGF; FBLN1; FBLN5 | 6 | 0.93 | CDC20; CENPF; MKI67; SDCBP2; TOP2A; YWHAQ |
| downstream signaling of activated fgfr | 95 | 3 | 0.53 | CDK1; CDKN1A; NRAS | 11 | 1.37 | ADCY2; ADCY5; ADCY6; ADCY8; FGF1; FGF17; FGF22; FGF9; FGFR1; FGFR3; PRKAR2B | 1 | 4.40 | PRKAR2B | 0 | 0.00 | | 4 | 1.07 | FGF2; FGF22; FGFR1; PDE1A | 3 | 0.90 | CDK1; CDKN1A; TRIB3 |
| cell communication | 36 | 5 | 2.32 | CXADR; | 4 | 1.31 | ANK2; | 0 | 0.00 | | 0 | 0.00 | | 2 | 1.41 | ATP1B2; | 1 | 0.79 | DSC2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| involved in cardiac conduction: GO | | | | DSC2; DSP; GJA1; JUP | | | ATP1A2; CASQ2; CTNNA3 | | | | | | | | | CACNA1G | | | |
| synaptic transmission cholinergic: GO | 36 | 5 | 2.32 | CHRNA3; CHRNA6; CHRNA9; HRH3; HTR3A | 7 | 2.29 | APOE; CHRM1; CHRM2; CHRM3; CHRM4; CHRNA2; HTR3E | 0 | 0.00 | | 0 | 0.00 | | 2 | 1.41 | CHRM1; CHRM3 | 1 | 0.79 | CHRNA6 |
| import into cell: GO | 36 | 4 | 1.86 | NTSR1; SLC38A1; STEAP1B; STEAP4 | 5 | 1.64 | ATP1A2; FXYD2; SLC6A2; SNCA; TF | 0 | 0.00 | | 1 | 11.61 | STEAP1B | 2 | 1.41 | SNCA; STEAP2 | 1 | 0.79 | NTSR1 |
| cdk-mediated phosphorylation and removal of cdc6 | 36 | 3 | 1.39 | CDC6; PSMA5; PSMB6 | 0 | 0.00 | | 0 | 0.00 | | 0 | 0.00 | | 0 | 0.00 | | 1 | 0.79 | CDC6 |
| negative regulation of epithelial cell differentiation: GO | 36 | 3 | 1.39 | IFNG; STAT1; TP63 | 3 | 0.98 | FOXE3; FRZB; OSR1 | 0 | 0.00 | | 0 | 0.00 | | 1 | 0.71 | OSR1 | 1 | 0.79 | XDH |
| regulation of receptor internalization: GO | 36 | 3 | 1.39 | GREM1; PCSK9; SELE | 3 | 0.98 | DKK1; HAMP; MAGI2 | 0 | 0.00 | | 1 | 11.61 | SELE | 1 | 0.71 | ANGPT1 | 1 | 0.79 | PCSK9 |
| g alpha (s) signalling events | 36 | 2 | 0.93 | GNAI3; PTHLH | 2 | 0.66 | ADCY8; ADRB1 | 0 | 0.00 | | 0 | 0.00 | | 1 | 0.71 | GNG11 | 1 | 0.79 | PTHLH |
| glycerolipid catabolic process: GO | 36 | 2 | 0.93 | FABP5; FABP6 | 5 | 1.64 | APOE; FABP4; FABP7; LPL; PNPLA3 | 1 | 11.61 | LPL | 0 | 0.00 | | 1 | 0.71 | PNPLA3 | 1 | 0.79 | FABP5 |
| muscle contraction | 36 | 2 | 0.93 | ANXA1; KCNK1 | 1 | 0.33 | FXYD2 | 0 | 0.00 | | 0 | 0.00 | | 1 | 0.71 | TRPC1 | 1 | 0.79 | KCNK1 |
| palmitoyl-transferase activity: GO | 36 | 2 | 0.93 | LRAT; SPTSSA | 3 | 0.98 | ZDHHC11; ZDHHC11B; ZDHHC15 | 0 | 0.00 | | 0 | 0.00 | | 3 | 2.12 | SPTSSB; ZDHHC11; ZDHHC15 | 1 | 0.79 | LRAT |
| regulation of erythrocyte differentiation: | 36 | 2 | 0.93 | HIF1A; ISG15 | 2 | 0.66 | GATA1; P4HTM | 0 | 0.00 | | 1 | 11.61 | ISG15 | 1 | 0.71 | P4HTM | 1 | 0.79 | HIF1A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| GO | | | | | | | | | | | | | | | | | | | |
| collagen biosynthesis and modifying enzymes | 36 | 1 | 0.46 | PPIB | 3 | 0.98 | COL24A1; COL9A2; PCOLCE2 | 0 | 0.00 | | | 0.00 | | 2 | 1.41 | COL24A1; GULP1 | 1 | 0.79 | P3H2 |
| developmental pigmentation: GO | 36 | 1 | 0.46 | RAB38 | 6 | 1.97 | BCL2; DCT; EDN3; MITF; OCA2; SOX10 | 0 | 0.00 | | 0 | 0.00 | | 3 | 2.12 | BCL2; EDN3; MITF | 1 | 0.79 | RAB38 |
| mitochondrial translation elongation | 36 | 1 | 0.46 | MRPL13 | 0 | 0.00 | | 0 | 0.00 | | 0 | 0.00 | | 0 | 0.00 | | 1 | 0.79 | BRIP1 |
| posttranscriptional gene silencing: GO | 36 | 1 | 0.46 | RAN | 1 | 0.33 | TERT | 0 | 0.00 | | 0 | 0.00 | | 0 | 0.00 | | 1 | 0.79 | RAN |
| protein lipid complex: GO | 36 | 1 | 0.46 | LDLR | 6 | 1.97 | APOC1; APOE; CLU; GPIHBP1; LPL; PON1 | 1 | 11.61 | LPL | 0 | 0.00 | | 1 | 0.71 | CLU | 1 | 0.79 | LDLR |
| regulation of transcription regulatory region dna binding: GO | 36 | 1 | 0.46 | HMGA2 | 4 | 1.31 | GATA1; HAND2; KAT2A; LIF | 0 | 0.00 | | 0 | 0.00 | | 1 | 0.71 | HAND2 | 1 | 0.79 | HMGA2 |
| semaphorin plexin signaling pathway: GO | 36 | 1 | 0.46 | SEMA4B | 7 | 2.29 | PLXNA3; PLXNA4; SEMA3A; SEMA3B; SEMA3D; SEMA3E; SEMA3G | 0 | 0.00 | | 0 | 0.00 | | 3 | 2.12 | PLXNA4; SEMA3E; SEMA4G | 1 | 0.79 | SEMA4B |
| signal sequence binding: GO | 36 | 1 | 0.46 | KPNA2 | 1 | 0.33 | KCNIP2 | 0 | 0.00 | | 0 | 0.00 | | 0 | 0.00 | | 1 | 0.79 | KPNA2 |
| regulation of tyrosine phosphorylation of stat protein: GO | 66 | 8 | 2.03 | CSF2; IFNG; IL12B; IL20; IL24; IL6; OSM; SOCS3 | 5 | 0.89 | ERBB4; FGFR3; GHR; LEP; LIF | 1 | 6.33 | GHR | 1 | 6.33 | OSM | 1 | 0.38 | ERBB4 | 2 | 0.86 | IL20; SOCS3 |
| regulation of cardiac muscle contraction: GO | 66 | 5 | 1.27 | DSC2; DSP; GSTO1; JUP; ZC3H12A | 10 | 1.79 | ADORA1; ADRA1A; ADRA1B; ANK2; ATP1A2; | 0 | 0.00 | | 0 | 0.00 | | 3 | 1.15 | ADRA1A; CTGF; HRC | 2 | 0.86 | DSC2; ZC3H12A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | CASQ2; CTNNA3; DMD; GSTM2; NKX2-5 | | | | | | | | | | | | |
| positive regulation of neuron death: GO | 66 | 4 | 1.01 | CCL3; CDK5R1; EIF2S1; PCSK9 | 5 | 0.89 | APOE; CLU; GRIK5; PAK3; TFAP2B | 0 | 0.00 | | 0 | 0.00 | | 2 | 0.77 | CLU; PAK3 | 2 | 0.86 | CDK5R1; PCSK9 |
| forebrain generation of neurons: GO | 66 | 3 | 0.76 | ASPM; SALL3; WNT5A | 12 | 2.15 | DCT; DCX; DRD1; ERBB4; FEZF2; FGFR1; PAX6; PLXNA3; SEMA3A; SLIT2; SLIT3; SOX1 | 0 | 0.00 | | 0 | 0.00 | | 4 | 1.54 | ERBB4; FGFR1; SLIT2; SLIT3 | 2 | 0.86 | ASPM; WNT5A |
| regulation of transporter activity: GO | 183 | 9 | 0.82 | ATP1B3; GSTO1; HOMER1; MMP9; NETO2; NTSR1; PCSK9; PPIF; PTAFR | 32 | 2.06 | ACTN2; ADRA2A; AGT; ANK2; ANO9; ATP1A2; BCL2; CACNA2D1; CACNB1; CASQ2; CFTR; DMD; DRD4; FGF14; FHL1; FXYD2; GSTM2; HAMP; JPH2; KCNIP2; NLGN1; NRXN1; PLA2G6; PON1; PPARGC1A; RELN; SGK2; | 0 | 0.00 | | 0 | 0.00 | | 15 | 2.08 | ADRA2A; ANO9; ATP1B2; BCL2; CACNA2D1; CACNB1; CNIH3; GLRX; HRC; NRXN1; PPARGC1A; RELN; SNCA; TESC; TRDN | 6 | 0.93 | HOMER1; NTSR1; PCSK9; PPIF; PTAFR; SGK1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline<br>Up-regulated | Fold Change (FC) Up | Up-regulated Genes | Down-regulated | Fold Change (FC) | Down-regulated Genes | B. Differentially expressed genes significant in the baseline vs week 12 comparison only in the placebo<br>Up-regulated | Fold Change (FC) Up | Up-regulated Genes | Down-regulated | Fold Change (FC) | Down-regulated Genes | C. Differentially expressed genes significant in the baseline vs week 12 comparison only in the nemo<br>Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | | | | SHANK1; SLN; SNCA; TRDN; WNK2 | | | | | | | | | | | | |
| endoplasmic reticulum golgi intermediate compartment: GO | 96 | 7 | 1.22 | AREG; CTSC; GJB2; HSPA5; SERPINA1; TGFA; VMP1 | 4 | 0.49 | ATP2A1; FOLR1; GRIA1; NAT8 | 0 | 0.00 | | 0 | 0.00 | | 2 | 0.53 | CNIH3; GRIA1 | 3 | 0.89 | AREG; HSPA5; TGFA |
| regulation of cellular response to transforming growth factor beta stimulus: GO | 96 | 4 | 0.70 | HSPA5; ITGA3; LTBP1; TGFBR1 | 5 | 0.61 | FOLR1; ITGA8; MYOCD; SKOR1; SKOR2 | 1 | 4.35 | CDKN1C | 0 | 0.00 | | 0 | 0.00 | | 3 | 0.89 | HSPA5; ITGA3; LRG1 |
| water homeostasis: GO | 67 | 7 | 1.75 | ABCA12; AQP3; GRHL3; HRNR; KRT16; SFN; TP63 | 10 | 1.76 | ADCY2; ADCY5; ADCY6; ADCY8; AQP4; AQP7; CYP4A11; CYP4F12; PRKAR2B; TFAP2B | 1 | 6.24 | PRKAR2B | 1 | 6.24 | AQP9 | 3 | 1.14 | CYP4A11; CYP4F12; SCNN1B | 2 | 0.85 | AQP3; SFN |
| glycosphingolipid metabolic process: GO | 67 | 6 | 1.50 | ARSH; GLTP; NEU2; ST6GALNAC ST8SIA2; UGCG | 2 | 0.35 | GAL3ST1; ST6GALNAC5 | 0 | 0.00 | | 0 | 0.00 | | 3 | 1.14 | ALDH5A1; PSAPL1; ST6GALNAC5 | 2 | 0.85 | ST6GALNAC1; ST8SIA2 |
| traf6 mediated induction of nfkb and map kinases upon tlr7/8 or 9 activation | 67 | 4 | 1.00 | DUSP6; MYD88; S100A12; UBE2N | 1 | 0.18 | PELI2 | 0 | 0.00 | | 0 | 0.00 | | 1 | 0.38 | PELI2 | 2 | 0.85 | DUSP6; MYD88 |
| regulation of cell junction assembly: GO | 67 | | 0.75 | GJA1; GREM1; RHOD | 4 | 0.70 | AGT; APOD; ARHGAP6; MYOC | 0 | 0.00 | | 0 | 0.00 | | 2 | 0.76 | DLC1; MYOC | 2 | 0.85 | RHOD; SNAI2 |
| anchored component of plasma membrane: GO | 37 | 5 | 2.26 | CD2; LYPD3; ULBP1; ULBP2; ULBP3 | 8 | 2.55 | CP; FOLR1; FOLR2; GGT7; GPC3; GPIHBP1; PKHD1; | 0 | 0.00 | | 0 | 0.00 | | 2 | 1.37 | CP; RHBG | 1 | 0.77 | LYPD3 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | | | | PRSS42 | | | | | | | | | | | | |
| graft versus host disease | 37 | 5 | 2.26 | CD80; IFNG; IL1A; IL1B; IL6 | 0 | 0.00 | | 0 | 0.00 | | 2 | 22.59 | GZMB; IL1B | 0 | 0.00 | | 1 | 0.77 | HLA-G |
| response to ph: GO | 37 | 4 | 1.81 | CA2; GJAI; GPR4; GPR65 | 6 | 1.91 | ABCC8; GPLD1; NOX1; PCK1; TG; TTPA | 0 | 0.00 | | 0 | 0.00 | | 2 | 1.37 | ACER1; GPLD1 | 1 | 0.77 | CA2 |
| extrinsic apoptotic signaling pathway via death domain receptors: GO | 37 | 3 | 1.36 | NGF; TNFRSF10A; TNFRSF9 | 1 | 0.32 | BCL2 | 0 | 0.00 | | 0 | 0.00 | | 1 | 0.69 | BCL2 | 1 | 0.77 | NGF |
| fbx17 down-regulates aurka during mitotic entry and in early mitosis | 37 | 3 | 1.36 | AURKA; PSMA5; PSMB6 | 0 | 0.00 | | 0 | 0.00 | | 0 | 0.00 | | 0 | 0.00 | | 1 | 0.77 | AURKA |
| gpvi-mediated activation cascade | 37 | 3 | 1.36 | CSF2; IL2RA; JAK3 | 1 | 0.32 | IL5 | 0 | 0.00 | | 2 | 22.59 | IL2RA; LCP2 | 1 | 0.69 | PIK3R6 | 1 | 0.77 | VAV2 |
| positive regulation of b cell proliferation: GO | 37 | 3 | 1.36 | CDKN1A; SASH3; TNFRSF4 | 3 | 0.96 | BCL2; IL5; IRS2 | 0 | 0.00 | | 0 | 0.00 | | 1 | 0.69 | BCL2 | 1 | 0.77 | CDKN1A |
| regulation of ornithine decarboxylase (odc) | 37 | 3 | 1.36 | ODC1; PSMA5; PSMB6 | 0 | 0.00 | | 0 | 0.00 | | 0 | 0.00 | | 0 | 0.00 | | 1 | 0.77 | ODC1 |
| collagen fibril organization: GO | 37 | 2 | 0.90 | GREM1; TGFBR1 | 5 | 1.59 | COL11A1; COL11A2; DPT; TNXA; TNXB | 0 | 0.00 | | 0 | 0.00 | | 4 | 2.75 | COL11A1; DDR2; DPT; FOXC1 | 1 | 0.77 | ADAMTS14 |
| glandular epithelial cell differentiation: GO | 37 | 2 | 0.90 | TP63; WNT5A | 2 | 0.64 | BMP5; PAX6 | 0 | 0.00 | | 0 | 0.00 | | 1 | 0.69 | FOXA1 | 1 | 0.77 | WNT5A |
| glutamate receptor binding: GO | 37 | 2 | 0.90 | HOMER1; NETO2 | 5 | 1.59 | CAMK2A; DLG2; GRIN1; | 0 | 0.00 | | 0 | 0.00 | | 2 | 1.37 | DLG2; ESR1 | 1 | 0.77 | HOMER1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | NETO1; SHANK1 | | | | | | | | | | | | |
| regulation of membrane lipid distribution: GO | 37 | 2 | 0.90 | PLSCR3; PRELID1 | 3 | 0.96 | ANO3; ANO9; P2RX7 | 0 | 0.00 | | 0 | 0.00 | | 1 | 0.69 | ANO9 | 1 | 0.77 | PRELID1 |
| rna polymerase ii transcribes snrna genes | 37 | 2 | 0.90 | ELL2; NABP1 | 0 | 0.00 | | 0 | 0.00 | | 0 | 0.00 | | 0 | 0.00 | | 1 | 0.77 | ELL2 |
| signaling by fgfr2 | 37 | 2 | 0.90 | FGFBP1; NRAS | 1 | 0.32 | FGF1 | 0 | 0.00 | | 0 | 0.00 | | 0 | 0.00 | | 1 | 0.77 | FGFBP1 |
| signaling by ras mutants | 37 | 2 | 0.90 | ACTB; NRAS | 1 | 0.32 | CNKSR2 | 0 | 0.00 | | 0 | 0.00 | | 1 | 0.69 | CNKSR2 | 1 | 0.77 | ACTB |
| toll pathway | 37 | 2 | 0.90 | MYD88; TLR10 | 0 | 0.00 | | 0 | 0.00 | | 0 | 0.00 | | 0 | 0.00 | | 1 | 0.77 | MYD88 |
| amyotrophic lateral sclerosis als | 37 | 1 | 0.45 | CYCS | 6 | 1.91 | CHP2; GRIA1; GRIA2; GRIN1; GRIN2A; PRPH | 0 | 0.00 | | 0 | 0.00 | | 3 | 2.06 | CHP2; GRIA1; GRIA2 | 1 | 0.77 | CYCS |
| mitochondrial translation initiation | 37 | 1 | 0.45 | MRPL13 | 0 | 0.00 | | 0 | 0.00 | | 0 | 0.00 | | 0 | 0.00 | | 1 | 0.77 | BRIP1 |
| negative regulation of gliogenesis: GO | 37 | 1 | 0.45 | ADCYAPI | 3 | 0.96 | ID4; NOG; NTRK3 | 0 | 0.00 | | 0 | 0.00 | | 1 | 0.69 | MYCN | 1 | 0.77 | ASCL2 |
| negative regulation of osteoblast differentiation: GO | 37 | 1 | 0.45 | AREG | 7 | 2.23 | FGFR1; GDF10; HAND2; NOG; OSTN; PTCH1; RORB | 0 | 0.00 | | 0 | 0.00 | | 5 | 3.43 | CHRD; FGFR1; HAND2; IGFBP5; PTCH1 | 1 | 0.77 | AREG |
| pi 3k cascade | 37 | 1 | 0.45 | CDKN1A | 3 | 0.96 | FGF17; FGF22; FGF9 | 0 | 0.00 | | 0 | 0.00 | | 2 | 1.37 | FGF2; FGF22 | 1 | 0.77 | CDKN1A |
| rna polymerase ii transcription termination | 37 | 1 | 0.45 | SNRPF | 0 | 0.00 | | 0 | 0.00 | | 0 | 0.00 | | 0 | 0.00 | | 1 | 0.77 | DDX39A |
| rna polymerase iii transcription | 37 | 1 | 0.45 | POLR3G | 0 | 0.00 | | 0 | 0.00 | | 0 | 0.00 | | 0 | 0.00 | | 1 | 0.77 | POLR3G |
| synthesis of | 37 | 1 | 0.45 | ST8SIA2 | 1 | 0.32 | ST6GALNAC5 | 0 | 0.00 | | 0 | 0.00 | | 1 | 0.69 | ST6GALNAC5 | 1 | 0.77 | ST8SIA2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| substrates in n-glycan biosythesis | | | | | | | | | | | | | | | | | | | |
| transcriptional activity of smad2 smad3 smad4 heterotrimer | 37 | 1 | 0.45 | SERPINE1 | 0 | 0.00 | | 0 | 0.00 | | 1 | 11.29 | SERPINE1 | 0 | 0.00 | | 1 | 0.77 | JUNB |
| tricarboxylic acid metabolic process: GO | 37 | 1 | 0.45 | OGDHL | 1 | 0.32 | GHR | 1 | 11.29 | GHR | 0 | 0.00 | | 0 | 0.00 | | 1 | 0.77 | OGDHL |
| par1 pathway | 37 | 0 | 0.00 | | 1 | 0.32 | ARHGEF19 | 0 | 0.00 | | 0 | 0.00 | | 0 | 0.00 | | 1 | 0.77 | ARHGEF16 |
| regulation of lymphocyte differentiation: GO | 126 | 19 | 2.52 | ANXA1; CD2; CD80; CTLA4; IFNG; IL12B; IL1B; IL2RA; IL36B; IL4R; IL6; IL7R; JAK3; PGLYRP2; PNP; PRDM1; PRELID1; SASH3; TNFSF9 | 4 | 0.37 | DTX1; FLT3LG; GLI2; ZBTB16 | 0 | 0.00 | | 3 | 9.95 | IL1B; IL2RA; IL7R | 3 | 0.60 | GLI2; PIK3R6; SLC46A2 | 4 | 0.90 | CD83; HLA-G; PNP; PRELID1 |
| nuclear transcription factor complex: GO | 126 | 2 | 0.27 | GTF3C6; HIF1A | 4 | 0.37 | KAT2A; NKX2-5; NR5A1; SOX8 | 0 | 0.00 | | 0 | 0.00 | | 0 | 0.00 | | 4 | 0.90 | ASCL2; E2F1; HIF1A; SOX15 |
| regulation of production of molecular mediator of immune response: GO | 97 | 17 | 2.93 | DEFB103A; DEFB103B; F2RL1; HMOX1; IFNG; IL13RA2; IL4R; IL6; JAK3; KLK5; KLK7; NR4A3; RSAD2; SASH3; SLAMF1; | 2 | 0.24 | IL5; RBP4 | 0 | 0.00 | | 1 | 4.31 | FFAR2 | 2 | 0.52 | ANGPT1; GPRC5B | 3 | 0.88 | IL10; IL13RA2; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | TNFRSF4; WNT5A | | | | | | | | | | | | | | | |
| alcohol binding: GO | 97 | 5 | 0.86 | ADAP2; ADH7; CRABP2; LRAT; TRPC4 | 11 | 1.34 | ALDOB; ANXA13; APOC1; APOD; APOE; GPR12; PTCH1; RBP4; RORC; SERPINA5; SOAT2 | 0 | 0.00 | | 0 | 0.00 | | 5 | 1.31 | GPR12; IGHM; PMP2; PTCH1; TRPC1 | 3 | 0.88 | ADAP2; CRABP2; LRAT |
| hepaticobiliary system development: GO | 127 | 8 | 1.05 | ANXA1; CCNE1; E2F7; MKI67; PCSK9; SULF2; TK1; UGT1A1 | 10 | 0.93 | ALDOB; CCDC40; COBL; CP; CYP1A1; DBP; DNAAF1; HMGCS2; KLKB1; PKD1 | 0 | 0.00 | | 0 | 0.00 | | 2 | 0.40 | CP; HMGCS2 | 4 | 0.89 | E2F7; MKI67; PCSK9; TK1 |
| retina development in camera type eye: GO | 127 | 3 | 0.40 | FJX1; HIF1A; SDK2 | 13 | 1.21 | CDON; DRD4; FOXN4; FZD4; LAMC3; LIF; MERTK; PAX6; RBP4; RORB; SLC17A7; SOX8; TFAP2B | 0 | 0.00 | | 0 | 0.00 | | 4 | 0.80 | CDON; LAMC3; TSPAN12; TUB | 4 | 0.89 | BMPR1B; HIF1A; LPCAT1; SDK2 |
| phase ii conjugation | 68 | 8 | 1.97 | AHCY; CNDP2; GGCT; GSTO1; GSTP1; SULT2B1; UGT1A1; UGT1A7 | 9 | 1.56 | CYP1A2; GGT7; GLYAT; GSTA3; GSTM5; MAT1A; SULT1A2; UGT2A1; UGT2B7 | 0 | 0.00 | | 0 | 0.00 | | 2 | 0.75 | GSTM5; SULT1E1 | 2 | 0.83 | GSTP1; SULT2B1 |
| myd88 | 68 | 4 | 0.98 | DUSP6; | 1 | 0.17 | PELI2 | 0 | 0.00 | | 0 | 0.00 | | 1 | 0.37 | PELI2 | 2 | 0.83 | DUSP6; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| dependent cascade initiated on endosome | | | | MYD88; S100A12; UBE2N | | | | | | | | | | | | | | | MYD88 |
| toll like receptor 7/8 (tlr7/8) cascade | 68 | 4 | 0.98 | DUSP6; MYD88; S100A12; UBE2N | 1 | 0.17 | PELI2 | 0 | 0.00 | | 0 | 0.00 | | 1 | 0.37 | PELI2 | 2 | 0.83 | DUSP6; MYD88 |
| transferase activity transferring hexosyl groups: GO | 186 | 16 | 1.44 | B3GNT3; B3GNT5; FUT1; FUT2; FUT3; GALNT14; GALNT6; GCNT4; HAS3; PYGL; SDF2L1; TYMP; UGCG; UGT1A1; UGT1A10; UGT1A7 | 16 | 1.01 | A4GNT; ABO; B3GALT1; B3GALT5; B4GALNT2; EXTL1; FUT9; GALNT13; GALNT8; GALNTL6; GYG2; HAS1; PYGM; UGT2A1; UGT2B7; UGT3A2 | 0 | 0.00 | | 0 | 0.00 | | 2 | 0.27 | ABO; B3GALT1 | 6 | 0.91 | B3GNT5; FUT1; FUT2; FUT3; GALNT14; GALNT6 |
| regulation of neuron apoptotic process: GO | 186 | 13 | 1.17 | CCL3; CDK5R1; GDNF; HIF1A; HMOX1; KIF14; NEFL; NGF; NR4A3; NTRK1; PCSK9; SNCB; TP63 | 19 | 1.21 | APOE; BCL2; CNTFR; GABRB3; GDF5; GRIK5; GRIN1; KCNB1; NDNF; NRBP2; PAK3; PCP4; PPARGC1A; SIX1; SNCA; TFAP2B; TOX3; TRIM2; VSTM2L | 0 | 0.00 | | 0 | 0.00 | | 11 | 1.50 | ANGPT1; BCL2; CHL1; CNTFR; ESR1; MDK; NDNF; PAK3; PPARGC1A; SNCA; TRIM2 | 6 | 0.91 | CDK5R1; HIF1A; KIF14; NGF; PCSK9; SNCB |
| interleukin-2 family signaling | 157 | 12 | 1.28 | ACTB; CSF2; DUSP6; DUSP9; | 12 | 0.90 | BTC; CNKSR2; EGF; FGF1; | 0 | 0.00 | | 1 | 2.66 | IL2RA | 5 | 0.81 | ANGPT1; CNKSR2; EGF; FGFR1; | 5 | 0.90 | ACTB; DUSP6; EREG; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | EREG; HBEGF; IL2RA; JAK3; NRAS; NRG1; PSMA5; PSMB6 | | | FGFR1; FGFR3; GFRA1; GRIN2A; IL5; IRS2; NRG2; SHC2 | | | | | | | | | SHC2 | | | HBEGF; NRG1 |
| vegfr2 mediated cell proliferation | 157 | 12 | 1.28 | ACTB; CSF2; DUSP6; DUSP9; EREG; HBEGF; IL2RA; JAK3; NRAS; NRG1; PSMA5; PSMB6 | 12 | 0.90 | BTC; CNKSR2; EGF; FGF1; FGFR1; FGFR3; GFRA1; GRIN2A; IL5; IRS2; NRG2; SHC2 | 0 | 0.00 | | 1 | 2.66 | IL2RA | 5 | 0.81 | ANGPT1; CNKSR2; EGF; FGFR1; SHC2 | 5 | 0.90 | ACTB; DUSP6; EREG; HBEGF; NRG1 |
| monocyte chemotaxis: GO | 38 | 9 | 3.96 | ANXA1; CCL17; CCL18; CCL21; CCL22; CCL3; CCL7; IL6; S100A12 | 2 | 0.62 | CCL14; FOLR2 | 0 | 0.00 | | 0 | 0.00 | | 1 | 0.67 | CCL14 | 1 | 0.75 | CCL20 |
| il1 signaling | 38 | 7 | 3.08 | IL1A; IL1B; IL1R2; IL1RAP; IL1RN; MYD88; UBE2N | 1 | 0.31 | PELI2 | 0 | 0.00 | | 1 | 11.00 | IL1B | 1 | 0.67 | PELI2 | 1 | 0.75 | MYD88 |
| cellular response to nutrient: GO | 38 | 4 | 1.76 | CCNE1; CYP24A1; HMOX1; TNC | 3 | 0.93 | FOLR1; FOLR2; LEP | 0 | 0.00 | | 0 | 0.00 | | 0 | 0.00 | | 1 | 0.75 | BRIP1 |
| cytokine secretion: GO | 38 | 4 | 1.76 | F2RL1; PNP; S100A12; TREM1 | 5 | 1.55 | AGT; GPAM; KLRF2; LEP; NOS2 | 1 | 11.00 | GPAM | 2 | 21.99 | LCP2; TREM1 | 1 | 0.67 | KLRF2 | 1 | 0.75 | PNP |
| positive regulation of calcium mediated signaling: GO | 38 | 4 | 1.76 | CCL3; CD3E; GSTO1; NRG1 | 5 | 1.55 | CHP2; GSTM2; JPH2; NEUROD2; TRDN | 0 | 0.00 | | 0 | 0.00 | | 3 | 2.01 | CHP2; LMCD1; TRDN | 1 | 0.75 | NRG1 |
| regulation of membrane | 38 | 4 | 1.76 | CCK; GJA1; IFI6; NTSR1 | 4 | 1.24 | BCL2; FHL1; MYOC; | 0 | 0.00 | | 0 | 0.00 | | 4 | 2.67 | BCL2; CACNA1G; | 1 | 0.75 | NTSR1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| depolarization: GO | | | | | | | P2RX7 | | | | | | | | | DCN; MYOC | | | |
| photoreceptor cell development: GO | 38 | 3 | 1.32 | CNGB1; PRDM1; TH | 3 | 0.93 | PAX6; RORB; TRPM1 | 0 | 0.00 | | 0 | 0.00 | | 0 | 0.00 | | 1 | 0.75 | TH |
| positive regulation of small gtpase mediated signal transduction: GO | 38 | 3 | 1.32 | F2RL1; NRG1; NTRK1 | 4 | 1.24 | CDON; FRMD7; MCF2L; RELN | 0 | 0.00 | | 0 | 0.00 | | 3 | 2.01 | CDON; LPAR1; RELN | 1 | 0.75 | NRG1 |
| activation of adenylate cyclase activity: GO | 38 | 2 | 0.88 | ADCYAP1; CAP1 | 10 | 3.10 | ADCY2; ADCY5; ADCY6; ADCY8; ADRB1; CALCR; DRD1; LHCGR; TSHR; VIPR2 | 0 | 0.00 | | 0 | 0.00 | | 1 | 0.67 | TSHR | 1 | 0.75 | CAP1 |
| o-linked glycosylation | 38 | 2 | 0.88 | B3GNT3; B3GNT5 | 4 | 1.24 | GALNT16; MUC20; MUC6; MUCL1 | 0 | 0.00 | | 0 | 0.00 | | 3 | 2.01 | GALNT16; MUC20; MUCL1 | 1 | 0.75 | B3GNT5 |
| peptidyl asparagine modification: GO | 38 | 2 | 0.88 | ST6GALNAC1; VCP | 2 | 0.62 | ST6GAL2; ST6GALNAC5 | 0 | 0.00 | | 0 | 0.00 | | 1 | 0.67 | ST6GALNAC5 | 1 | 0.75 | ST6GALNAC1 |
| protein trimerization: GO | 38 | 2 | 0.88 | NELL2; TNFRSF9 | 3 | 0.93 | ADIPOQ; HSF4; SCARA5 | 1 | 11.00 | ADIPOQ | 0 | 0.00 | | 1 | 0.67 | SCARA5 | 1 | 0.75 | NELL2 |
| transcription from rna polymerase iii promoter: GO | 38 | 2 | 0.88 | GTF3C6; POLR3G | 0 | 0.00 | | 0 | 0.00 | | 0 | 0.00 | | 0 | 0.00 | | 1 | 0.75 | POLR3G |
| anatomical structure maturation: GO | 38 | 1 | 0.44 | CDK5R1 | 3 | 0.93 | FGFR3; GRIN1; LEP | 0 | 0.00 | | 0 | 0.00 | | 1 | 0.67 | RECK | 1 | 0.75 | CDK5R1 |
| apical junction assembly: GO | 38 | 1 | 0.44 | ECT2 | 1 | 0.31 | WNT11 | 0 | 0.00 | | 0 | 0.00 | | 1 | 0.67 | WNT11 | 1 | 0.75 | ECT2 |
| ph reduction: GO | 38 | 1 | 0.44 | RAB38 | 5 | 1.55 | ATP6V0A4; ATP6V0E2; ATP6V1B1; SLC17A7; TTPA | 0 | 0.00 | | 0 | 0.00 | | 2 | 1.34 | ATP6V0A4; ATP6V0E2 | 1 | 0.75 | RAB38 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| rac1 reg pathway | 38 | 1 | 0.44 | RACGAP1 | 1 | 0.31 | ARHGEF25 | 0 | 0.00 | | 0 | 0.00 | | 2 | 1.34 | ARHGEF25; PREX2 | 1 | 0.75 | VAV2 |
| substrate adhesion dependent cell spreading: GO | 38 | 1 | 0.44 | KIF14 | 5 | 1.55 | FZD4; ITGA8; MERTK; RADIL; SRCIN1 | 1 | 11.00 | SRCIN1 | 0 | 0.00 | | 2 | 1.34 | FZD7; RADIL | 1 | 0.75 | KIF14 |
| actin myosin filament sliding: GO | 38 | 0 | 0.00 | | 16 | 4.97 | ACTA1; ACTN2; DES; DMD; MYBPC1; MYH3; MYL3; MYL4; TMOD1; TNNC1; TNNC2; TNNI2; TNNT2; TNNT3; TPM1; TPM2 | 0 | 0.00 | | 0 | 0.00 | | 2 | 1.34 | TNNC1; TNNT3 | 1 | 0.75 | TPM4 |
| integrin pathway | 38 | 0 | 0.00 | | 3 | 0.93 | ACTA1; ACTN2; TNS1 | 0 | 0.00 | | 0 | 0.00 | | 0 | 0.00 | | 1 | 0.75 | ACTN1 |
| spleen development: GO | 38 | 0 | 0.00 | | 4 | 1.24 | BCL2; EPB42; NKX2-5; TCF21 | 0 | 0.00 | | 0 | 0.00 | | 2 | 1.34 | BCL2; SLC40A1 | 1 | 0.75 | BCL3 |
| pdgfrb pathway | 128 | 7 | 0.92 | ACTR3; ARPC3; NRAS; SFN; STAT1; YWHAQ; YWHAZ | 2 | 0.18 | MYOCD; PPP2R2B | 0 | 0.00 | | 0 | 0.00 | | 1 | 0.20 | PIK3R6 | 4 | 0.89 | SFN; VAV2; YWHAQ; YWHAZ |
| granulocyte migration: GO | 69 | 15 | 3.64 | ANXA1; CCL17; CCL18; CCL22; CCL3; CCL7; CXADR; CXCL3; IFNG; IL1B; S100A12; S100A8; | 2 | 0.34 | CCL14; EDN3 | 0 | 0.00 | | 2 | 12.11 | IL1B; TREM1 | 2 | 0.74 | CCL14; EDN3 | 2 | 0.82 | CCL20; HRH1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | S100A9; SCG2; TREM1 | | | | | | | | | | | | | | | |
| ammonium ion binding: GO | 69 | 6 | 1.46 | AMD1; CHRNA3; CHRNA6; CHRNA9; HTR3A; TH | 11 | 1.88 | ALDOB; ANXA13; APOC1; CHRM3; CHRNA2; DRD1; DRD4; GPR12; HTR3E; MAOA; SERPINA5 | 0 | 0.00 | | 0 | 0.00 | | 3 | 1.10 | CHRM3; GPR12; IGHM | 2 | 0.82 | CHRNA6; TH |
| muscle organ morphogenesis: GO | 69 | 5 | 1.21 | DSP; MYLK2; NRG1; TBX20; WNT5A | 9 | 1.54 | COL11A1; GSC; LIF; MYL3; NKX2-5; TNNC1; TNNT2; TPM1; ZFPM2 | 0 | 0.00 | | 0 | 0.00 | | 5 | 1.84 | COL11A1; FOXC1; SHOX2; TNNC1; ZFPM2 | 2 | 0.82 | NRG1; WNT5A |
| pancreas development: GO | 69 | 5 | 1.21 | ANXA1; BAK1; FOXF1; IL6; WNT5A | 6 | 1.03 | BMP5; CCDC40; CLU; DNAAF1; MNX1; PAX6 | 0 | 0.00 | | 0 | 0.00 | | 1 | 0.37 | CLU | 2 | 0.82 | BAK1; WNT5A |
| myd88: mal cascade initiated on plasma membrane | 69 | 4 | 0.97 | DUSP6; MYD88; S100A12; UBE2N | 1 | 0.17 | PELI2 | 0 | 0.00 | | 0 | 0.00 | | 1 | 0.37 | PELI2 | 2 | 0.82 | DUSP6; MYD88 |
| toll like receptor tlr6: tlr2 cascade | 69 | 4 | 0.97 | DUSP6; MYD88; S100A12; UBE2N | 1 | 0.17 | PELI2 | 0 | 0.00 | | 0 | 0.00 | | 1 | 0.37 | PELI2 | 2 | 0.82 | DUSP6; MYD88 |
| epithelial cell signaling in *helicobacter pylori* infection | 69 | 3 | 0.73 | CXCL1; CXCR1; HBEGF | 4 | 0.68 | ATP6V0A4; ATP6V0E2; ATP6V1B1; IGSF5 | 0 | 0.00 | | 0 | 0.00 | | 3 | 1.10 | ATP6V0A4; ATP6V0E2; JAM2 | 2 | 0.82 | CXCR1; HBEGF |
| melanoma | 69 | 3 | 0.73 | CDKN1A; E2F3; NRAS | 9 | 1.54 | EGF; FGF1; FGF14; FGF17; | 0 | 0.00 | | 0 | 0.00 | | 5 | 1.84 | EGF; FGF2; FGF22; FGFR1; MITF | 2 | 0.82 | CDKN1A; E2F1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | FGF22; FGF9; FGFR1; MITF; PDGFD | | | | | | | | | | | | |
| skin epidermis development: GO | 69 | 3 | 0.73 | FOXE1; KRT17; TP63 | 7 | 1.20 | ALX4; BCL2; DKK1; DNASE1L2; EDA; LGR5; LRP4 | 0 | 0.00 | | 0 | 0.00 | | 5 | 1.84 | ALX4; BCL2; IGFBP5; LDB2; LGR5 | 2 | 0.82 | DSG4; FOXE1 |
| negative regulation of dephosphorylation: GO | 69 | 2 | 0.49 | PKMYT1; PPP4R4 | 7 | 1.20 | CAMSAP3; CRY2; DLG2; ELFN2; PCDH11X; SLC7A14; TSKS | 0 | 0.00 | | 1 | 6.06 | SPOCD1 | 2 | 0.74 | CRY2; DLG2 | 2 | 0.82 | LMTK3; PKMYT1 |
| smad binding: GO | 69 | 2 | 0.49 | HMGA2; TGFBR1 | 6 | 1.03 | MAGI2; MYOCD; PAX6; RANBP3L; SKOR1; SKOR2 | 0 | 0.00 | | 0 | 0.00 | | 1 | 0.37 | RANBP3L | 2 | 0.82 | BMPR1B; HMGA2 |
| renal system process: GO | 99 | 6 | 1.01 | AQP3; CHRNA3; F2RL1; GJA1; ITGA3; SULF2 | 20 | 2.38 | ADCY2; ADCY5; ADCY6; ADCY8; ADORA1; ADRA1A; AGT; AGTR1; AQP4; BCL2; BTC; CD34; CYP4A11; CYP4F12; GSN; HBB; PCSK5; PRKAR2B; REN; TFAP2B | 3 | 12.66 | HSD11B2; IGKV3-20; PRKAR2B | 0 | 0.00 | | 7 | 1.80 | ADRA1A; AGTR1; BCL2; CD34; CYP4A11; CYP4F12; HBB | 3 | 0.86 | AQP3; ITGA3; SGK1 |
| chloride transport: GO | 99 | 3 | 0.51 | CLCA2; GABRQ; SLC26A9 | 21 | 2.50 | ANO3; ANO5; ANO9; BEST2; BEST3; BEST4; | 0 | 0.00 | | 0 | 0.00 | | 5 | 1.28 | ANO9; CLCN4; CLIC5; GLRB; P2RY4 | 3 | 0.86 | CLCA2; SLC26A6; SLC4A3 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | | | | CFTR; CLCNKA; CLCNKB; CLIC5; GABRA2; GABRB3; GABRG3; GABRP; GLRB; NMUR1; SLC17A7; SLC26A1; SLC26A5; SLC26A7; SLC4A1 | | | | | | | | | | | | |
| host interactions of hiv factors | 129 | 11 | 1.43 | AP1S3; NPM1; PPIA; PSMA4; PSMA5; PSMB6; PSMD1; RAN; RANBP1; RCC1; SLC25A5 | 0 | 0.00 | | 0 | 0.00 | | 0 | 0.00 | | 0 | 0.00 | | 4 | 0.88 | AP1S3; NPM1; PPIAP22; RAN |
| apoptotic cleavage of cellular proteins | 39 | 6 | 2.57 | CLSPN; DSG1; DSG3; DSP; LMNB1; PRKCQ | 3 | 0.91 | GAS2; GSN; MAPT | 0 | 0.00 | | 0 | 0.00 | | 1 | 0.65 | MAPT | 1 | 0.73 | PRKCQ |
| post-translational modification: synthesis of gpi-anchored proteins | 39 | 6 | 2.57 | ALPL; FCGR3B; PIGW; PLAUR; ULBP2; VNN3 | 2 | 0.61 | FOLR1; PSCA | 0 | 0.00 | | 0 | 0.00 | | 3 | 1.95 | LSAMP; PSCA; RECK | 1 | 0.73 | PIGW |
| il 2 signaling | 39 | 5 | 2.15 | CDK1; CSF2; IL2RA; JAK3; NRAS | 1 | 0.30 | IL5 | 0 | 0.00 | | 1 | 10.72 | IL2RA | 0 | 0.00 | | 1 | 0.73 | CDK1 |
| scf-beta-trcp mediated degradation of emi1 | 39 | 4 | 1.72 | CDC20; FBXO5; PSMA5; PSMB6 | 0 | 0.00 | | 0 | 0.00 | | 0 | 0.00 | | 0 | 0.00 | | 1 | 0.73 | CDC20 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| androgen receptor binding: GO | 39 | 3 | 1.29 | CALR; CCNE1; RAN | 2 | 0.61 | PPARGC1A; TCF21 | 0 | 0.00 | | 0 | 0.00 | | 1 | 0.65 | PPARGC1A | 1 | 0.73 | RAN |
| carboxypeptidase activity: GO | 39 | 3 | 1.29 | CNDP2; CPA6; CPXM1 | 2 | 0.61 | AGBL1; AGBL4 | 0 | 0.00 | | 0 | 0.00 | | 2 | 1.30 | CPE; CPZ | 1 | 0.73 | CPA6 |
| cysteine type endopeptidase regulator activity involved in apoptotic process: GO | 39 | 3 | 1.29 | BIRC5; PYCARD; SERPINB9 | 3 | 0.91 | NOL3; SNCA; TFAP2B | 0 | 0.00 | | 1 | 10.72 | SERPINB9 | 1 | 0.65 | SNCA | 1 | 0.73 | BIRC5 |
| phototransduction: GO | 39 | 3 | 1.29 | CNGB1; GNGT2; PITPNM1 | 1 | 0.30 | GUCA1B | 0 | 0.00 | | 0 | 0.00 | | 0 | 0.00 | | 1 | 0.73 | PITPNM1 |
| regulation of glycoprotein metabolic process: GO | 39 | 3 | 1.29 | CCL21; HBEGF; JAK3 | 3 | 0.91 | BCL2; GATA1; ITM2A | 0 | 0.00 | | 0 | 0.00 | | 2 | 1.30 | BCL2; ITM2A | 1 | 0.73 | HBEGF |
| golgi to plasma membrane transport: GO | 39 | 2 | 0.86 | RAB10; RAB31 | 1 | 0.30 | STXBP6 | 0 | 0.00 | | 0 | 0.00 | | 2 | 1.30 | STEAP2; STXBP6 | 1 | 0.73 | RAB31 |
| regulation of lipid storage: GO | 39 | 2 | 0.86 | IL6; ZC3H12A | 7 | 2.12 | ACACB; C3; FITM2; LEP; LPL; MEST; PLIN5 | 1 | 10.72 | LPL | 0 | 0.00 | | 1 | 0.65 | C3 | 1 | 0.73 | ZC3H12A |
| 4 iron 4 sulfur cluster binding: GO | 39 | 1 | 0.43 | RSAD2 | 0 | 0.00 | | 0 | 0.00 | | 0 | 0.00 | | 0 | 0.00 | | 1 | 0.73 | BRIP1 |
| igf1 pathway | 39 | 1 | 0.43 | YWHAZ | 1 | 0.30 | IRS2 | 0 | 0.00 | | 0 | 0.00 | | 0 | 0.00 | | 1 | 0.73 | YWHAZ |
| regulation of b cell mediated immunity: GO | 39 | 1 | 0.43 | IFNG | 3 | 0.91 | C3; C4BPA; FCER2 | 0 | 0.00 | | 0 | 0.00 | | 1 | 0.65 | C3 | 1 | 0.73 | IL10 |
| regulation of phosphatidyl inositol 3 kinase activity: GO | 39 | 1 | 0.43 | CCL21 | 3 | 0.91 | CCKBR; ERBB4; FGFR3 | 0 | 0.00 | | 0 | 0.00 | | 3 | 1.95 | ERBB4; FGF2; PIK3R6 | 1 | 0.73 | VAV2 |
| rrna modification in the nucleus and cytosol | 39 | 1 | 0.43 | UTP11 | 0 | 0.00 | | 0 | 0.00 | | 0 | 0.00 | | 0 | 0.00 | | 1 | 0.73 | NOP56 |
| scavenger receptor | 39 | 1 | 0.43 | TMPRSS4 | 7 | 2.12 | COLEC12; | 0 | 0.00 | | 1 | 10.72 | TMPRSS4 | 4 | 2.61 | ENPP3; | 1 | 0.73 | LGALS3BP |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| activity: GO | | | | | | | ENPP1; MARCO; SCARA5; SSC5D; SUSD2; TMPRSS2 | | | | | | | | | SCARA5; SSC5D; SUSD2 | | | |
| purine metabolism | 159 | 6 | 0.63 | NME1; PKM; PNP; POLR3G; RRM2; TYMP | 9 | 0.67 | ADCY2; ADCY5; ADCY6; ADCY8; AMPD1; ENPP1; ENTPD8; PDE11A; PDE9A | 0 | 0.00 | | 0 | 0.00 | | 4 | 0.64 | AK7; ENPP3; PDE1A; PDE9A | 5 | 0.89 | PKM; PNP; POLR3G; RRM2; XDH |
| negative regulation of protein secretion: GO | 100 | 13 | 2.18 | ANXA1; F2RL1; HMGCR; IL1B; IL36RN; IL6; RSAD2; SLAMF1; SRGN; TNFRSF21; TNFRSF9; VSNL1; ZC3H12A | 9 | 1.06 | ABCC8; ACVR1C; ADRA2A; CD34; DRD4; INHBB; KCNB1; SRCIN1; SSC5D | 2 | 8.36 | ACVR1C; SRCIN1 | 2 | 8.36 | GBP1; IL1B | 5 | 1.27 | ADRA2A; ANGPT1; CD34; FBLN1; SSC5D | 3 | 0.85 | IL10; VSNL1; ZC3H12A |
| dicarboxylic acid metabolic process: GO | 100 | 6 | 1.00 | ALDH4A1; GOT2; HAL; KYNU; MTHFD2; TH | 11 | 1.30 | ADHFE1; ALDH1L1; ASPA; CYP17A1; D2HGDH; FOLR1; GHR; HAAO; HOGA1; PCK1; PRODH | 1 | 4.18 | GHR | 0 | 0.00 | | 4 | 1.02 | ALDH5A1; ASPA; NMNAT3; PRODH | 3 | 0.85 | GOT2; NAGS; TH |
| stress activated protein kinase signaling cascade: GO | 100 | 3 | 0.50 | DUSP9; MDFI; WNT5A | 5 | 0.59 | AGT; BIRC7; CRYAB; FGF14; MAPK8IP1 | 1 | 4.18 | CRYAB | 0 | 0.00 | | 0 | 0.00 | | 3 | 0.85 | MDFI; TRIB1; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| synaptic vesicle localization: GO | 100 | 3 | 0.50 | STON2; UNC13A; WNT7A | 12 | 1.42 | CADPS; NLGN1; NRXN1; P2RX7; PCLO; RIMS1; RPH3AL; SNCA; SYT1; SYT17; SYT8; SYT9 | 0 | 0.00 | | 0 | 0.00 | | 5 | 1.27 | NRXN1; PCLO; RIMS1; SNCA; SYT17 | 3 | 0.85 | STON2; UNC13A; WNT7A |
| rna polymerase ii transcription factor complex: GO | 100 | 1 | 0.17 | HIF1A | 3 | 0.35 | KAT2A; NKX2-5; NR5A1 | 0 | 0.00 | | 0 | 0.00 | | 0 | 0.00 | | 3 | 0.85 | ASCL2; E2F1; HIF1A |
| toll like receptor 2 (tlr2) cascade | 70 | 4 | 0.96 | DUSP6; MYD88; S100A12; UBE2N | 1 | 0.17 | PELI2 | 0 | 0.00 | | 0 | 0.00 | | 1 | 0.36 | PELI2 | 2 | 0.81 | DUSP6; MYD88 |
| toll like receptor 9 (tlr9) cascade | 70 | 4 | 0.96 | DUSP6; MYD88; S100A12; UBE2N | 1 | 0.17 | PELI2 | 0 | 0.00 | | 0 | 0.00 | | 1 | 0.36 | PELI2 | 2 | 0.81 | DUSP6; MYD88 |
| toll like receptor tlr1: tlr2 cascade | 70 | 4 | 0.96 | DUSP6; MYD88; S100A12; UBE2N | 1 | 0.17 | PELI2 | 0 | 0.00 | | 0 | 0.00 | | 1 | 0.36 | PELI2 | 2 | 0.81 | DUSP6; MYD88 |
| central nervous system neuron development: GO | 70 | 3 | 0.72 | FBXO45; SALL3; WNT5A | 15 | 2.53 | DCLK1; DCX; DRD1; EPHB1; FEZF2; FGFR1; GLI2; LEP; PLXNA3; PLXNA4; SEMA3A; SLIT2; SLIT3; SOX1; SPTBN4 | 0 | 0.00 | | 0 | 0.00 | | 7 | 2.54 | DCLK1; FGFR1; GLI2; PLXNA4; SLIT2; SLIT3; SPTBN4 | 2 | 0.81 | FBXO45; WNT5A |
| inositol phosphate metabolism | 70 | 1 | 0.24 | TPI1 | 3 | 0.51 | FN3K; PLCB4; PLCH2 | 0 | 0.00 | | 0 | 0.00 | | 3 | 1.09 | FN3K; PLCB4; PLCZ1 | 2 | 0.81 | PLCD4; TPI1 |
| mrna 3 end | 70 | 1 | 0.24 | EIF4A3 | 0 | 0.00 | | 0 | 0.00 | | 0 | 0.00 | | 0 | 0.00 | | 2 | 0.81 | DDX39A; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| processing: GO | | | | | | | | | | | | | | | | | | | EIF4A3 |
| negative regulation of neuron apoptotic process: GO | 130 | 9 | 1.16 | GDNF; HIF1A; HMOX1; KIF14; NEFL; NGF; NR4A3; NTRK1; SNCB | 15 | 1.36 | APOE; BCL2; CNTFR; GABRB3; GDF5; GRIN1; NDNF; NRBP2; PCP4; PPARGC1A; SIX1; SNCA; TFAP2B; TOX3; VSTM2L | 0 | 0.00 | | 0 | 0.00 | | 8 | 1.56 | ANGPT1; BCL2; CHL1; CNTFR; MDK; NDNF; PPARGC1A; SNCA | 4 | 0.87 | HIF1A; KIF14; NGF; SNCB |
| cellular hormone metabolic process: GO | 101 | 9 | 1.49 | ADH7; AKR1B15; ALDH1A3; CRABP2; IL1B; LRAT; SDR16C5; UGT1A1; UGT1A7 | 11 | 1.28 | ALDH1A1; AWAT2; CACNA1H; CYP17A1; CYP1A1; CYP21A2; HSD17B14; LHB; PPARGC1A; RBP4; UGT2B7 | 0 | 0.00 | | 1 | 4.14 | IL1B | 6 | 1.51 | CACNA1H; CYP3A4; DGAT2; ESR1; PPARGC1A; SULT1E1 | 3 | 0.84 | CRABP2; DHRS2; LRAT |
| melanogenesis | 101 | 6 | 0.99 | CALML3; CALML5; GNAI3; NRAS; WNT5A; WNT7A | 14 | 1.64 | ADCY2; ADCY5; ADCY6; ADCY8; CALML6; CAMK2A; CAMK2B; DCT; FZD4; FZD8; MITF; PLCB4; TCF7L1; WNT11 | 0 | 0.00 | | 0 | 0.00 | | 7 | 1.76 | ASIP; CREB3L1; FZD7; MITF; PLCB4; TCF7L1; WNT11 | 3 | 0.84 | WNT5A; WNT7A; WNT9B |
| sphingolipid metabolic process: GO | 131 | 11 | 1.41 | ARSH; CERS3; GLTP; NEU2; SERINC2; | 5 | 0.45 | FA2H; GAL3ST1; P2RX1; P2RX7; | 0 | 0.00 | | 0 | 0.00 | | 6 | 1.16 | ACER1; ALDH3A2; ALDH5A1; PSAPL1; | 4 | 0.87 | SERINC2; ST6GALNAC1; ST8SIA2; TH |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | SGPP2; SPTSSA; ST6GALNAC1; ST8SIA2; TH; UGCG | | | ST6GALNAC5 | | | | | | | | | SPTSSB; ST6GALNAC5 | | | |
| maintenance of cell number: GO | 131 | 3 | 0.38 | ASPM; EOMES; WNT7A | 7 | 0.63 | FOXD3; LIF; NANOG; NOG; PIWIL2; TET1 | 0 | 0.00 | | 0 | 0.00 | | 6 | 1.16 | FGF2; FGFR1; FZD7; LDB2; PRRX1; TET1 | 4 | 0.87 | ASCL2; ASPM; WNT7A; WNT9B |
| collagen degradation | 40 | 7 | 2.93 | CTSB; CTSL; MMP1; MMP10; MMP12; MMP3; MMP9 | 1 | 0.29 | COL9A2 | 0 | 0.00 | | 0 | 0.00 | | 1 | 0.64 | GULP1 | 1 | 0.71 | MMP3 |
| lung alveolus development: GO | 40 | 5 | 2.09 | ABCA12; FOXF1; PDPN; STRA6; WNT5A | 4 | 1.18 | LIF; MYOCD; PKDCC; TCF21 | 0 | 0.00 | | 0 | 0.00 | | 2 | 1.27 | FOXA1; IGFBP5 | 1 | 0.71 | WNT5A |
| regulation of hematopoietic progenitor cell differentiation: GO | 40 | 4 | 1.67 | HIST1H4I; HIST1H4J; HIST1H4K; HIST1H4L | 1 | 0.29 | SCIN | 0 | 0.00 | | 0 | 0.00 | | 3 | 1.91 | FOXC1; SCIN; TESC | 1 | 0.71 | HIST1H4I |
| response to cadmium ion: GO | 40 | 4 | 1.67 | CDK1; HMOX1; PCNA; PRNP | 4 | 1.18 | CYP1A2; GPAM; GSN; HAAO | 1 | 10.45 | GPAM | 0 | 0.00 | | 0 | 0.00 | | 1 | 0.71 | CDK1 |
| sterol biosynthetic process: GO | 40 | 4 | 1.67 | CH25H; EBP; HMGCR; SQLE | 4 | 1.18 | CFTR; HMGCS2; NPC1L1; PRKAA2 | 0 | 0.00 | | 0 | 0.00 | | 2 | 1.27 | HMGCS2; PRKAA2 | 1 | 0.71 | SQLE |
| triglyceride biosynthesis | 40 | 4 | 1.67 | AGPAT5; ELOVL4; ELOVL7; GK | 6 | 1.77 | AGMO; ELOVL2; GPAM; GPD1; MOGAT1; MOGAT2 | 2 | 20.89 | GPAM; GPD1 | 0 | 0.00 | | 1 | 0.64 | DGAT2 | 1 | 0.71 | LPCAT1 |
| auf1 (hnrnp d0) | 40 | 3 | 1.26 | HSPA8; | 0 | 0.00 | | 0 | 0.00 | | 0 | 0.00 | | 0 | 0.00 | | 1 | 0.71 | HSPA8 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| binds and destabilizes mrna | | | | PSMA5; PSMB6 | | | | | | | | | | | | | | | |
| bile acid biosynthesis | 40 | 3 | 1.26 | ADH7; AKR1B10; ALDH1A3 | 4 | 1.18 | ADH1B; ADH1C; ADHFE1; SOAT2 | 0 | 0.00 | | 0 | 0.00 | | 1 | 0.64 | ALDH3A2 | 1 | 0.71 | AKRIB10 |
| positive regulation of atpase activity: GO | 40 | 3 | 1.26 | ATP1B3; PFN1; UHRF1 | 5 | 1.47 | ALDOB; MYL3; MYL4; TNNT2; TPM1 | 0 | 0.00 | | 0 | 0.00 | | 1 | 0.64 | ATP1B2 | 1 | 0.71 | PFN1 |
| aminopeptidase activity: GO | 40 | 2 | 0.84 | DPP3; DPP4 | 3 | 0.88 | DPP10; DPP6; TRHDE | 0 | 0.00 | | 0 | 0.00 | | 1 | 0.64 | DPP6 | 1 | 0.71 | DPP4 |
| androgen receptor signaling pathway: GO | 40 | 2 | 0.84 | CCNE1; RAN | 3 | 0.88 | AR; PPARGC1A; SCGB2A1 | 0 | 0.00 | | 0 | 0.00 | | 1 | 0.64 | PPARGC1A | 1 | 0.71 | RAN |
| cap-dependent translation initiation | 40 | 2 | 0.84 | EIF4EBP1; RPL22L1 | 0 | 0.00 | | 0 | 0.00 | | 0 | 0.00 | | 0 | 0.00 | | 1 | 0.71 | EIF4EBP1 |
| eukaryotic translation initiation | 40 | 2 | 0.84 | EIF4EBP1; RPL22L1 | 0 | 0.00 | | 0 | 0.00 | | 0 | 0.00 | | 0 | 0.00 | | 1 | 0.71 | EIF4EBP1 |
| long chain fatty acid transport: GO | 40 | 2 | 0.84 | ANXA1; BDKRB2 | 7 | 2.06 | ABCD2; ACACB; APOE; DRD4; PLA2G5; PRKAA2; SLC27A6 | 2 | 20.89 | ABCD2; SLC27A6 | 0 | 0.00 | | 1 | 0.64 | PRKAA2 | 1 | 0.71 | BDKRB2 |
| muscle fiber development: GO | 40 | 2 | 0.84 | CXADR; HOMER1 | 6 | 1.77 | ACTA1; C16orf89; CACNA2D2; DMD; MYH11; WFIKKN1 | 1 | 10.45 | WFIKKN1 | 0 | 0.00 | | 1 | 0.64 | CACNA2D2 | 1 | 0.71 | HOMER1 |
| negative regulation of bmp signaling pathway: GO | 40 | 2 | 0.84 | GREM1; WNT5A | 7 | 2.06 | CHRDL1; DKK1; GREM2; NOG; SKOR1; TMPRSS6; VWC2L | 0 | 0.00 | | 0 | 0.00 | | 3 | 1.91 | CHRD; GREM2; VWC2 | 1 | 0.71 | WNT5A |
| propanoate | 40 | 2 | 0.84 | ALDH1A3; | 3 | 0.88 | ACACB; | 0 | 0.00 | | 0 | 0.00 | | 2 | 1.27 | ACSS3; | 1 | 0.71 | LDHA |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| metabolism | | | | LDHA | | | ACADL; ACSS3 | | | | | | | | | ALDH3A2 | | | |
| hnf3a pathway | 40 | 1 | 0.42 | SERPINA1 | 2 | 0.59 | AR; SCGB1A1 | 0 | 0.00 | | 0 | 0.00 | | 2 | 1.27 | ESR1; FOXA1 | 1 | 0.71 | SFTPA2 |
| ion gated channel activity: GO | 40 | 1 | 0.42 | CLCA2 | 7 | 2.06 | ANO3; ANO5; ANO9; KCNMB4; KCNT2; KCNU1; TRPM3 | 0 | 0.00 | | 0 | 0.00 | | 2 | 1.27 | ANO9; KCNT2 | 1 | 0.71 | CLCA2 |
| negative regulation of small gtpase mediated signal transduction: GO | 40 | 1 | 0.42 | ITGA3 | 3 | 0.88 | ADRA1A; MYOC; SLIT2 | 0 | 0.00 | | 0 | 0.00 | | 5 | 3.18 | ADRA1A; DLC1; MYOC; SLIT2; SPRY1 | 1 | 0.71 | ITGA3 |
| p75 ntr receptor mediated signalling | 40 | 0 | 0.00 | | 1 | 0.29 | OBSCN | 0 | 0.00 | | 0 | 0.00 | | 0 | 0.00 | | 1 | 0.71 | ARHGEF16 |
| transport of mature mrna derived from an intron-containing transcript | 40 | 0 | 0.00 | | 0 | 0.00 | | 0 | 0.00 | | 0 | 0.00 | | 0 | 0.00 | | 1 | 0.71 | DDX39A |
| metabolism of xenobiotics by cytochrome p450 | 71 | 8 | 1.89 | ADH7; ALDH1A3; CYP2S1; GSTO1; GSTP1; UGT1A1; UGT1A10; UGT1A7 | 14 | 2.33 | ADH1B; ADH1C; ADHFE1; CYP1A1; CYP1A2; CYP2C9; CYP3A5; GSTA3; GSTM2; GSTM3; GSTM5; GSTT2; UGT2A1; UGT2B7 | 0 | 0.00 | | 0 | 0.00 | | 3 | 1.07 | CYP3A4; CYP3A5; GSTM5 | 2 | 0.80 | CYP2S1; GSTP1 |
| pyrimidine containing | 71 | 7 | 1.65 | APOBEC3A; CDA; | 3 | 0.50 | NEIL1; SLC19A3; | 0 | 0.00 | | 0 | 0.00 | | 1 | 0.36 | SLC19A3 | 2 | 0.80 | CDA; TK1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline: Up-regu-lated | A: Fold Change (FC) Up | A: Up-regulated Genes | A: Down-regu-lated | A: Fold Change (FC) | A: Down-regulated Genes | B. Differentially expressed genes significant in the baseline vs week 12 comparison only in the placebo: Up-regu-lated | B: Fold Change (FC) Up | B: Up-regulated Genes | B: Down-regu-lated | B: Fold Change (FC) | B: Down-regulated Genes | C. Differentially expressed genes significant in the baseline vs week 12 comparison only in the nemo: Up-regu-lated | C: Fold Change (FC) Up | C: Up-regulated Genes | C: Down-regu-lated | C: Fold Change (FC) | C: Down-regulated Genes |
|---|---|---|---|---|---|---|---|---|---|---|---|---|---|---|---|---|---|---|---|
| compound metabolic process: GO | | | | CMPK2; NME1; TK1; TYMP; UPP1 | | | UPP2 | | | | | | | | | | | | |
| sphingolipid biosynthetic process: GO | 71 | 6 | 1.41 | CERS3; SGPP2; SPTSSA; ST6GALNAC1; ST8SIA2; UGCG | 5 | 0.83 | FA2H; GAL3ST1; P2RX1; P2RX7; ST6GALNAC5 | 0 | 0.00 | | 0 | 0.00 | | 4 | 1.43 | ACER1; ALDH3A2; SPTSSB; ST6GALNAC5 | 2 | 0.80 | ST6GALNAC1; ST8SIA2 |
| detoxification: GO | 71 | 5 | 1.18 | GSTO1; PRDX1; PTGS2; S100A9; TXNDC17 | 9 | 1.50 | ALB; APOE; CYGB; GSTM2; GSTM3; HBA1; HBA2; HBB; SOD3 | 0 | 0.00 | | 0 | 0.00 | | 3 | 1.07 | HBA2; HBB; SOD3 | 2 | 0.80 | PTGS2; TXNDC17 |
| long-term depression | 71 | 4 | 0.94 | GNAI3; NRAS; PLA2G3; PPP2R2C | 9 | 1.50 | GNAZ; GRIA1; GRIA2; NOS2; PLA2G5; PLA2G6; PLCB4; PPP2R2B; PRKG2 | 0 | 0.00 | | 0 | 0.00 | | 5 | 1.79 | GRIA1; GRIA2; PLCB4; PRKG1; PRKG2 | 2 | 0.80 | PLA2G3; PPP2R2C |
| single organism membrane budding: GO | 71 | 4 | 0.94 | AREG; CTSC; SERPINA1; TGFA | 3 | 0.50 | FOLR1; GRIA1; TRAPPC6A | 0 | 0.00 | | 0 | 0.00 | | 3 | 1.07 | CNIH3; GRIA1; TRAPPC6A | 2 | 0.80 | AREG; TGFA |
| nfkb and map kinases activation mediated by tlr4 signaling repertoire | 71 | 3 | 0.71 | CDK1; DUSP6; S100A12 | 0 | 0.00 | | 0 | 0.00 | | 0 | 0.00 | | 0 | 0.00 | | 2 | 0.80 | CDK1; DUSP6 |
| interleukin-17 signaling | 191 | 15 | 1.31 | ACTB; CDK1; CSF2; DUSP6; DUSP9; EREG; HBEGF; IL2RA; IL6; JAK3; NRAS; NRG1; | 12 | 0.74 | BTC; CNKSR2; EGF; FGF1; FGFR1; FGFR3; GFRA1; GRIN2A; IL5; IRS2; NRG2; | 0 | 0.00 | | 1 | 2.19 | IL2RA | 5 | 0.67 | ANGPT1; CNKSR2; EGF; FGFR1; SHC2 | 6 | 0.89 | ACTB; CDK1; DUSP6; EREG; HBEGF; NRG1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | PSMA5; PSMB6; UBE2N | | | SHC2 | | | | | | | | | | | | |
| tight junction | 132 | 5 | 0.63 | ACTB; GNAI3; NRAS; PPP2R2C; PRKCQ | 19 | 1.70 | ACTN2; CGN; CLDN16; CLDN18; CLDN8; CTNNA3; IGSF5; MAGI2; MRAS; MYH11; MYH14; MYH3; MYH7B; MYL9; MYLPF; POTEKP; PPP2R2B; RAB3B; TJP3 | 0 | 0.00 | | 0 | 0.00 | | 8 | 1.54 | CGN; CLDN18; CLDN8; JAM2; MRAS; POTEKP; RAB3B; TJP3 | 4 | 0.86 | ACTB; ACTN1; PPP2R2C; PRKCQ |
| regulation of sequestering of calcium ion: GO | 102 | 11 | 1.80 | BDKRB1; CCL21; CCL3; CCR5; CXCL10; CXCL11; CXCL9; GSTO1; NPSR1; NTSR1; UBASH3B | 11 | 1.27 | ANK2; ATP1A2; CASQ2; DMD; DRD1; GSTM2; JPH2; NOL3; P2RX7; SNCA; TRDN | 0 | 0.00 | | 1 | 4.10 | CXCL9 | 5 | 1.25 | FGF2; HRC; SNCA; TRDN; TRPC1 | 3 | 0.83 | CXCL11; NTSR1; UBASH3B |
| toll-like receptors cascades | 102 | 9 | 1.48 | CAP1; CTSB; CTSL; DUSP6; MYD88; S100A12; S100A8; S100A9; UBE2N | 1 | 0.12 | PELI2 | 0 | 0.00 | | 0 | 0.00 | | 1 | 0.25 | PELI2 | 3 | 0.83 | CAP1; DUSP6; MYD88 |
| cardiac chamber morphogenesis: GO | 102 | 6 | 0.98 | DSP; FOXF1; HIF1A; NRG1; | 13 | 1.50 | COL11A1; HAND2; MESP1; | 0 | 0.00 | | 0 | 0.00 | | 9 | 2.24 | COL11A1; CPE; FOXC1; HAND2; | 3 | 0.83 | HIF1A; NRG1; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | TBX20; WNT5A | | | MYL3; NKX2-5; NPY5R; RBP4; TBX5; TNNC1; TNNT2; TPM1; WNT11; ZFPM2 | | | | | | | | | MESP1; SHOX2; TNNC1; WNT11; ZFPM2 | | | |
| integrin signaling pathway | 102 | 4 | 0.66 | ACTR3; ITGA3; ITGA6; MYLK2 | 9 | 1.04 | ACTA1; ACTN2; ITGA7; ITGA8; MAPK8IP1; MRAS; PAK3; TLN2; TNS1 | 0 | 0.00 | | 0 | 0.00 | | 4 | 1.00 | ITGA11; MRAS; PAK3; TLN2 | 3 | 0.83 | ACTN1; ITGA3; ITGA6 |
| regulation of protein polymerization: GO | 162 | 9 | 0.93 | ACTR3; ARPC1A; ARPC3; ARPC5L; CAPZA1; CCL21; PFN1; PYCARD; TWF1 | 13 | 0.95 | CAPZA3; FHOD3; GSN; LMOD1; MAPT; PAK3; PPP1R9A; SCIN; SLIT2; SNCA; SPTBN4; TMOD1; TPPP | 0 | 0.00 | | 0 | 0.00 | | 9 | 1.41 | CAPZA3; LMOD1; MAPT; PAK3; SCIN; SLIT2; SNCA; SPTBN4; TPPP | 5 | 0.88 | ARPCA; CDC42EP1; PFN1; SGK1; TWF1 |
| negative regulation of map kinase activity: GO | 72 | 7 | 1.63 | DUSP14; DUSP6; DUSP9; GSTP1; HMGCR; IL1B; SERPINB3 | 3 | 0.49 | ADIPOQ; APOE; MAPK8IP1 | 1 | 5.80 | ADIPOQ | 1 | 5.80 | IL1B | 1 | 0.35 | SPRY1 | 2 | 0.79 | DUSP6; GSTP1 |
| cell cell junction assembly: GO | 72 | 6 | 1.39 | DSG1; ECT2; FSCN1; GJA1; GJB2; JUP | 4 | 0.66 | AMOT; ANK2; TLN2; WNT11 | 0 | 0.00 | | 0 | 0.00 | | 2 | 0.71 | TLN2; WNT11 | 2 | 0.79 | ECT2; PKP3 |
| negative regulation of hormone secretion: GO | 72 | 5 | 1.16 | HMGCR; IL1B; IL6; OSM; VSNL1 | 11 | 1.80 | ABCC8; ACVR1C; ADIPOQ; ADORA1; ADRA2A; | 2 | 11.61 | ACVR1C; ADIPOQ | 2 | 11.61 | IL1B; OSM | 2 | 0.71 | ADRA2A; NPY1R | 2 | 0.79 | UCN2; VSNL1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | CARTPT; INHBB; KCNB1; LEP; LIF; NPY1R | | | | | | | | | | | | |
| regulation of steroid metabolic process: GO | 72 | 4 | 0.93 | CYP27B1; IFNG; IL1B; UGT1A1 | 14 | 2.29 | ACADL; AGT; AGTR1; APOC1; APOE; BMP5; CYP17A1; EPHX2; FGF1; LEP; NR5A1; PPARGC1A; RORC; SERPINA12 | 0 | 0.00 | | 1 | 5.80 | IL1B | 4 | 1.41 | AGTR1; DGAT2; PPARGC1A; SERPINA12 | 2 | 0.79 | CYP27B1; SNAI2 |
| transcriptional regulation by runx3 | 72 | 4 | 0.93 | CDKN1A; PSMA5; PSMB6; TEAD4 | 1 | 0.16 | RORC | 0 | 0.00 | | 0 | 0.00 | | 1 | 0.35 | CTGF | 2 | 0.79 | CDKN1A; TEAD4 |
| vesicle coating: GO | 72 | 4 | 0.93 | AREG; CTSC; SERPINA1; TGFA | 3 | 0.49 | FOLR1; GRIA1; TRAPPC6A | 0 | 0.00 | | 0 | 0.00 | | 4 | 1.41 | CNIH3; FCHO1; GRIA1; TRAPPC6A | 2 | 0.79 | AREG; TGFA |
| glial cell development: GO | 72 | 3 | 0.70 | GSTP1; S100A8; S100A9 | 12 | 1.97 | ADAM22; CLU; DRD1; FA2H; GSN; ID4; LAMA2; LAMC3; LGI4; MYOC; PLP1; PRDM8 | 0 | 0.00 | | 0 | 0.00 | | 8 | 2.82 | ADAM22; CLU; LAMA2; LAMC3; LGI4; LPAR1; MYOC; PLP1 | 2 | 0.79 | GSTP1; NDRG1 |
| regulation of actin filament bundle assembly: GO | 72 | 3 | 0.70 | GPR65; PFN1; PRKCQ | 8 | 1.31 | AMOT; ARHGAP6; FRMD7; MYOC; PPP1R9A; SHANK1; TPM1; WNT11 | 0 | 0.00 | | 0 | 0.00 | | 5 | 1.76 | CTGF; DLC1; LPAR1; MYOC; WNT11 | 2 | 0.79 | PFN1; PRKCQ |
| regulation of cellular response to | 72 | 2 | 0.46 | HSPA8; HSPH1 | 5 | 0.82 | CAMK2A; CAMK2B; CD34; | 1 | 5.80 | CRYAB | 0 | 0.00 | | 1 | 0.35 | CD34 | 2 | 0.79 | HSPA8; HSPH1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| heat: GO | | | | | | | CRYAB; HSPA1L | | | | | | | | | | | | |
| porphyrin and chlorophyll metabolism | 41 | 6 | 2.45 | EPRS; HMOX1; HMOX2; UGT1A1; UGT1A10; UGT1A7 | 5 | 1.44 | ALAS2; CP; PPOX; UGT2A1; UGT2B7 | 0 | 0.00 | | 0 | 0.00 | | 2 | 1.24 | CP; PPOX | 1 | 0.69 | HMOX2 |
| type i diabetes mellitus | 41 | 5 | 2.04 | CD80; IFNG; IL12B; IL1A; IL1B | 1 | 0.29 | ICA1 | 0 | 0.00 | | 2 | 20.39 | GZMB; IL1B | 3 | 1.86 | CPE; HLA-DQB2; ICA1 | 1 | 0.69 | HLA-G |
| amb2 neutrophils pathway | 41 | 4 | 1.63 | IL6; MMP9; PLAU; PLAUR | 1 | 0.29 | MST1 | 0 | 0.00 | | 0 | 0.00 | | 2 | 1.24 | CTGF; JAM2 | 1 | 0.69 | PLAT |
| il 3 5 and gm csf signaling | 41 | 4 | 1.63 | CSF2; IL2RA; JAK3; YWHAZ | 1 | 0.29 | IL5 | 0 | 0.00 | | 1 | 10.19 | IL2RA | 0 | 0.00 | | 1 | 0.69 | YWHAZ |
| negative regulation of response to cytokine stimulus: GO | 41 | 4 | 1.63 | F2RL1; GSTP1; IL1RN; IL36RN | 5 | 1.44 | ADIPOQ; NOL3; PALM3; SLIT2; SLIT3 | 1 | 10.19 | ADIPOQ | 0 | 0.00 | | 3 | 1.86 | PALM3; SLIT2; SLIT3 | 1 | 0.69 | GSTP1 |
| autodegradation of cdh1 by cdh1: apc/c | 41 | 3 | 1.22 | PSMA5; PSMB6; UBE2C | 0 | 0.00 | | 0 | 0.00 | | 0 | 0.00 | | 0 | 0.00 | | 1 | 0.69 | UBE2C |
| cytoplasmic translation: GO | 41 | 3 | 1.22 | EIF4EBP1; RPL22L1; RPL26L1 | 0 | 0.00 | | 0 | 0.00 | | 0 | 0.00 | | 0 | 0.00 | | 1 | 0.69 | EIF4EBP1 |
| histone h3 acetylation: GO | 41 | 2 | 0.82 | BRCA2; TRIM16 | 2 | 0.58 | KAT2A; PER1 | 0 | 0.00 | | 0 | 0.00 | | 0 | 0.00 | | 1 | 0.69 | BRCA2 |
| regulation of water balance by renal aquaporins | 41 | 2 | 0.82 | AQP3; GNGT2 | 6 | 1.73 | ADCY2; ADCY5; ADCY6; ADCY8; AQP4; PRKAR2B | 1 | 10.19 | PRKAR2B | 0 | 0.00 | | 1 | 0.62 | GNG11 | 1 | 0.69 | AQP3 |
| bmp pathway | 41 | 1 | 0.41 | GREM1 | 2 | 0.58 | CHRDL1; NOG | 0 | 0.00 | | 0 | 0.00 | | 1 | 0.62 | CHRD | 1 | 0.69 | BMPR1B |
| multicellular organismal movement: | 41 | 1 | 0.41 | HOMER1 | 6 | 1.73 | MYH14; MYH3; TNNC1; | 0 | 0.00 | | 0 | 0.00 | | 2 | 1.24 | TNNC1; TNNT3 | 1 | 0.69 | HOMER1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| GO | | | | | | | TNNC2; TNNI2; TNNT3 | | | | | | | | | | | | |
| positive regulation of phospholipid metabolic process: GO | 41 | 1 | 0.41 | CCL21 | 2 | 0.58 | ERBB4; FGFR3 | 0 | 0.00 | | 0 | 0.00 | | 2 | 1.24 | ERBB4; FGF2 | 1 | 0.69 | VAV2 |
| regulation of nik nf kappab signaling: GO | 41 | 1 | 0.41 | TNFRSF10A | 0 | 0.00 | | 0 | 0.00 | | 0 | 0.00 | | 0 | 0.00 | | 1 | 0.69 | CARD10 |
| regulation of polysaccharide metabolic process: GO | 41 | 1 | 0.41 | PHLDA2 | 5 | 1.44 | EGF; ENPP1; GCGR; IRS2; SORBS1 | 0 | 0.00 | | 0 | 0.00 | | 1 | 0.62 | EGF | 1 | 0.69 | PHLDA2 |
| receptor clustering: GO | 41 | 0 | 0.00 | | 9 | 2.59 | APOE; DLG2; GLRB; GRIK5; LRP4; MAGI2; NLGN1; NRXN1; RELN | 0 | 0.00 | | 0 | 0.00 | | 4 | 2.48 | DLG2; GLRB; NRXN1; RELN | 1 | 0.69 | AGRN |
| structural constituent of muscle: GO | 41 | 0 | 0.00 | | 16 | 4.60 | ACTN2; DMD; MYBPC1; MYBPH; MYH11; MYL3; MYL9; MYLPF; MYOM1; MYOM2; OBSCN; PDLIM3; SORBS2; SYNM; TPM1; TPM2 | 0 | 0.00 | | 0 | 0.00 | | 3 | 1.86 | MYOM1; MYOM2; SORBS2 | 1 | 0.69 | TPM4 |
| voltage gated calcium channel activity: GO | 41 | 0 | 0.00 | | 8 | 2.30 | CACNA1F; CACNA1H; CACNA2D1; CACNA2D2; | 0 | 0.00 | | 0 | 0.00 | | 5 | 3.10 | CACNA1G; CACNA1H; CACNA2D1; CACNA2D2; | 1 | 0.69 | TMC1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | CACNB1; GRM7; IL1RAPL1; TMC2 | | | | | | | | | CACNB1 | | | |
| cardiac ventricle development: GO | 103 | 9 | 1.46 | DSP; FOXF1; HIF1A; LTBP1; NRG1; PRDM1; STRA6; TBX20; WNT5A | 13 | 1.49 | COL11A1; HAND2; MESP1; MYL3; MYOCD; NKX2-5; NPY5R; TBX5; TNNC1; TNNT2; TPM1; WNT11; ZFPM2 | 0 | 0.00 | | 0 | 0.00 | | 9 | 2.22 | COL11A1; CPE; FOXC1; HAND2; KCNK2; MESP1; TNNC1; WNT11; ZFPM2 | 3 | 0.83 | HIF1A; NRG1; WNT5A |
| ubiquitin like protein ligase activity: GO | 193 | 7 | 0.61 | RNF222; UBE2C; UBE2F; UBE2N; UBE2S; UBE2T; UHRF1 | 5 | 0.31 | ASB4; FBXO40; PDZRN3; PELI2; RNF165 | 0 | 0.00 | | 0 | 0.00 | | 2 | 0.26 | PDZRN3; PELI2 | 6 | 0.88 | RNF19B; RNF222; UBE2C; UBE2F; UBE2S; UBE2T |
| ceramide metabolic process: GO | 73 | 5 | 1.15 | CERS3; NEU2; ST6GALNAC1; ST8SIA2; UGCG | 4 | 0.65 | GAL3ST1; P2RX1; P2RX7; ST6GALNAC5 | 0 | 0.00 | | 0 | 0.00 | | 3 | 1.04 | ACER1; ALDH5A1; ST6GALNAC5 | 2 | 0.78 | ST6GALNAC1; ST8SIA2 |
| chronic myeloid leukemia | 73 | 4 | 0.92 | CDKN1A; E2F3; NRAS; TGFBR1 | 2 | 0.32 | SHC2; SHC3 | 0 | 0.00 | | 0 | 0.00 | | 1 | 0.35 | SHC2 | 2 | 0.78 | CDKN1A; E2F1 |
| trif mediated tlr3 signaling | 73 | 4 | 0.92 | CDK1; DUSP6; S100A12; ZBP1 | 0 | 0.00 | | 0 | 0.00 | | 0 | 0.00 | | 0 | 0.00 | | 2 | 0.78 | CDK1; DUSP6 |
| protein n linked glycosylation: GO | 73 | 3 | 0.69 | ST6GALNAC1; ST8SIA2; VCP | 3 | 0.48 | GAL3ST1; ST6GAL2; ST6GALNAC5 | 0 | 0.00 | | 0 | 0.00 | | 1 | 0.35 | ST6GALNAC5 | 2 | 0.78 | ST6GALNAC1; ST8SIA2 |
| flavin adenine dinucleotide | 73 | 1 | 0.23 | SQLE | 11 | 1.78 | ACADL; ACOX2; | 0 | 0.00 | | 0 | 0.00 | | 6 | 2.09 | ACOX2; AOX1; CRY2; | 2 | 0.78 | SQLE; XDH |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| binding: GO | | | | | | | CRY2; D2HGDH; FMO2; FMO5; LDHD; MAOA; NOS2; PPOX; PRODH | | | | | | | | | FMO5; PPOX; PRODH | | | |
| histone methylation: GO | 73 | 1 | 0.23 | HIST1H1D | 1 | 0.16 | CHD5 | 0 | 0.00 | | 0 | 0.00 | | 0 | 0.00 | | 2 | 0.78 | BEND3; HIST1H1D |
| ret signaling | 164 | 12 | 1.22 | ACTB; CSF2; DUSP6; DUSP9; EREG; HBEGF; IL2RA; JAK3; NRAS; NRG1; PSMA5; PSMB6 | 12 | 0.86 | BTC; CNKSR2; EGF; FGF1; FGFR1; FGFR3; GFRA1; GRIN2A; IL5; IRS2; NRG2; SHC2 | 0 | 0.00 | | 1 | 2.55 | IL2RA | 6 | 0.93 | ANGPT1; CNKSR2; DOK6; EGF; FGFR1; SHC2 | 5 | 0.86 | ACTB; DUSP6; EREG; HBEGF; NRG1 |
| lymphocyte mediated immunity: GO | 134 | 18 | 2.25 | C1QBP; CTSC; EXO1; IGHG1; IGHG2; IGHG4; IGKC; IGKV4-1; IL13RA2; IL4R; PRDX1; RAET1E; RAET1L; SLAMF1; SLAMF7; ULBP1; ULBP2; ULBP3 | 7 | 0.62 | C3; C4BPA; C6; C7; CLEC2A; CLU; KLRF2 | 2 | 6.24 | IGHG1; IGKV3-20 | 1 | 3.12 | GZMB | 5 | 0.95 | C3; CLU; IGHM; IGHV3-23; KLRF2 | 4 | 0.85 | BCL3; EXO1; IL13RA2; RAET1L |
| beta catenin tcf complex assembly: GO | 42 | 5 | 1.99 | HIST1H4I; HIST1H4J; HIST1H4K; HIST1H4L; RUVBL1 | 3 | 0.84 | TCF7L1; TERT; TLE2 | 0 | 0.00 | | 0 | 0.00 | | 2 | 1.21 | TCF7L1; TLE2 | 1 | 0.68 | HIST1H4I |
| excretion: GO | 42 | 4 | 1.59 | AQP3; CHRNA3; | 8 | 2.25 | ADRA1A; AQP7; | 0 | 0.00 | | 1 | 9.95 | AQP9 | 4 | 2.42 | ADRA1A; ATP6V0A4; | 1 | 0.68 | AQP3 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | HMOX1; UGT1A7 | | | ATP6V0A4; ATP6V1B1; CLCNKA; CLCNKB; CLDN16; KCNJ1 | | | | | | | | | MDK; SCNN1B | | | |
| tcptp pathway | 42 | 3 | 1.20 | JAK3; KPNA2; STAT1 | 1 | 0.28 | EGF | 0 | 0.00 | | 0 | 0.00 | | 1 | 0.60 | EGF | 1 | 0.68 | KPNA2 |
| signaling by braf and raf fusions | 42 | 2 | 0.80 | ACTB; NRAS | 1 | 0.28 | CNKSR2 | 0 | 0.00 | | 0 | 0.00 | | 1 | 0.60 | CNKSR2 | 1 | 0.68 | ACTB |
| thrombin par1 pathway | 42 | 2 | 0.80 | GNA15; GNAI3 | 2 | 0.56 | DNM1; GNAZ | 0 | 0.00 | | 0 | 0.00 | | 0 | 0.00 | | 1 | 0.68 | GNA15 |
| dendrite morphogenesis: GO | 42 | 1 | 0.40 | WNT7A | 11 | 3.09 | CTNND2; DCLK1; DCX; EPHB1; LRP4; MAP6; PAK3; SDC2; SEMA3A; SHANK1; SLITRK5 | 0 | 0.00 | | 0 | 0.00 | | 3 | 1.81 | DCLK1; PAK3; PREX2 | 1 | 0.68 | WNT7A |
| fatty acid derivative biosynthetic process: GO | 42 | 1 | 0.40 | PTGS2 | 3 | 0.84 | GGT7; PLA2G5; PTGIS | 0 | 0.00 | | 0 | 0.00 | | 0 | 0.00 | | 1 | 0.68 | PTGS2 |
| cytoplasmic side of membrane: GO | 165 | 11 | 1.12 | CD2; DSG1; GNA15; GNAI3; GNGT2; JAK3; JUP; NTSR1; RACGAP1; RGS1; TH | 8 | 0.57 | DTNA; GNAZ; KCNIP1; MCF2L; PGM5; RGS11; RGS6; RGS9 | 1 | 2.53 | RGS11 | 0 | 0.00 | | 2 | 0.31 | GNG11; PGM5 | 5 | 0.86 | GNA15; NTSR1; PTP4A1; RGS1; TH |
| non canonical wnt signaling pathway: GO | 135 | 9 | 1.12 | GRHL3; PFN1; PSMA4; PSMA5; PSMB6; PSMD1; PSME3; | 9 | 0.79 | ARHGEF19; CAMK2A; FRZB; FZD4; FZD8; GPC6; MAGI2; MYOC; WNT11 | 0 | 0.00 | | 0 | 0.00 | | 4 | 0.75 | FZD7; MYOC; PRICKLE1; WNT11 | 4 | 0.84 | PFN1; WNT5A; WNT7A; WNT9B |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | WNT5A; WNT7A | | | | | | | | | | | | | | | |
| organelle envelope lumen: GO | 74 | 5 | 1.13 | CYCS; PRELID1; TIMM13; TIMM23; TIMM8B | 3 | 0.48 | MYOC; PPOX; TXNIP | 0 | 0.00 | | 0 | 0.00 | | 4 | 1.37 | GATM; MYOC; PPOX; TXNIP | 2 | 0.77 | CYCS; PRELID1 |
| alpha amino acid biosynthetic process: GO | 74 | 4 | 0.90 | AHCY; ALDH4A1; GOT2; MTHFD2 | 3 | 0.48 | BHMT2; CARNS1; DHPS | 0 | 0.00 | | 0 | 0.00 | | 2 | 0.69 | GAMT; GATM | 2 | 0.77 | GOT2; NAGS |
| regulation of bmp signaling pathway: GO | 74 | 3 | 0.68 | GREM1; ITGA3; WNT5A | 12 | 1.91 | CHRDL1; DKK1; GDF5; GPC3; GREM2; NOG; RNF165; SKOR1; TFAP2B; TMPRSS6; VWC2L; ZNF423 | 0 | 0.00 | | 0 | 0.00 | | 4 | 1.37 | CHRD; GREM2; VWC2; ZNF423 | 2 | 0.77 | ITGA3; WNT5A |
| developmental cell growth: GO | 74 | 2 | 0.45 | AURKA; FLRT3 | 11 | 1.75 | AGT; COBL; DCLK1; DCX; MAPT; MYOCD; PLXNA3; SEMA3A; SLIT2; SLIT3; SORBS2 | 0 | 0.00 | | 0 | 0.00 | | 5 | 1.72 | DCLK1; MAPT; SLIT2; SLIT3; SORBS2 | 2 | 0.77 | AURKA; FLRT3 |
| mucopoly-saccharide metabolic process: GO | 105 | 7 | 1.12 | B3GNT3; CHST1; HAS3; HMMR; HYAL3; IL1B; MKI67 | 9 | 1.01 | BCAN; CHST12; CHST5; HAS1; IDUA; ITIH5; NDNF; PRELP; UST | 0 | 0.00 | | 1 | 3.98 | IL1B | 7 | 1.69 | ANGPT1; CHST12; DCN; DSEL; FGF2; NDNF; UST | 3 | 0.81 | CHST1; HMMR; MKI67 |
| regulation of cation transmembrane transport: GO | 196 | 14 | 1.20 | ATP1B3; BDKRB1; CXCL10; CXCL11; CXCL9; | 27 | 1.63 | ACTN2; ADRA2A; AGT; ANK2; ATP1A2; CACNA2D1; | 0 | 0.00 | | 1 | 2.13 | CXCL9 | 12 | 1.56 | ADRA2A; ATP1B2; CACNA2D1; CACNB1; DPP6; EDN3; | 6 | 0.87 | CXCL11; HOMER1; NTSR1; PCSK9; PPIF; UBASH3B |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | GSTO1; HOMER1; MMP9; NPSR1; NTSR1; PCSK9; PPIF; PRNP; UBASH3B | | | CACNB1; CASQ2; DMD; DPP10; DPP6; DRD1; DRD4; EDN3; FGF14; FHL1; FXYD2; GSTM2; HAMP; JPH2; KCNIP1; KCNIP2; PLA2G6; SLN; SNCA; TRDN; WNK2 | | | | | | | | | GLRX; HRC; SNCA; TESC; TRDN; TRPC1 | | | |
| ecm affiliated | 166 | 12 | 1.21 | ANXA1; ANXA3; CLEC17A; CLEC3A; CLEC6A; CLEC7A; GREM1; LGALS7; LGALS9B; LGALS9C; SDC1; SEMA4B | 36 | 2.56 | C1QL4; C1QTNF4; C1QTNF7; CLEC18A; CLEC2A; CLEC3B; CLEC4F; COLEC11; COLEC12; ELFN2; FCN2; FREM1; GPC2; GPC3; GPC6; GRIFIN; LGALS12; LGALS4; MUC16; MUC20; MUC4; MUC5AC; MUC5B; MUC6; MUC7; MUCL1; PLXNA3; PLXNA4; | 1 | 2.52 | CLEC3B | 1 | 2.52 | ANXA3 | 14 | 2.14 | ANXA9; C1QTNF4; C1QTNF7; CLEC12A; EMCN; FREM1; GPC2; GRIFIN; MUC20; MUC7; MUCL1; PLXNA4; SEMA3E; SEMA4G | 5 | 0.85 | CLEC7A; LGALS9B; LGALS9C; SEMA4B; SFTPA2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline: Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo: Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo: Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | | | | SDC2; SEMA3A; SEMA3B; SEMA3D; SEMA3E; | | | | | | | | | | | | |
| cxcr3 pathway | 43 | 6 | 2.33 | CXCL10; CXCL11; CXCL13; CXCL9; GNAI3; NRAS | 2 | 0.55 | DNM1; GNAZ | 0 | 0.00 | | 1 | 9.72 | CXCL9 | 0 | 0.00 | | 1 | 0.66 | CXCL11 |
| regulation of actin filament depolymerization: GO | 43 | 4 | 1.56 | CAPZA1; F2RL1; SH3BGRL3; TWF1 | 7 | 1.92 | ACTN2; CAPZA3; GSN; LMOD1; SCIN; SPTBN4; TMOD1 | 0 | 0.00 | | 0 | 0.00 | | 4 | 2.36 | CAPZA3; LMOD1; SCIN; SPTBN4 | 1 | 0.66 | TWF1 |
| sprouting angiogenesis: GO | 43 | 4 | 1.56 | E2F7; ESM1; GREM1; PGF | 4 | 1.10 | CCBE1; GPLD1; SEMA3E; SLIT2 | 0 | 0.00 | | 0 | 0.00 | | 6 | 3.55 | ANGPT1; CCBE1; FGF2; GPLD1; SEMA3E; SLIT2 | 1 | 0.66 | E2F7 |
| acetylglucos-aminyl-transferase activity: GO | 43 | 3 | 1.17 | B3GNT3; B3GNT5; GCNT4 | 2 | 0.55 | A4GNT; EXTL1 | 0 | 0.00 | | 0 | 0.00 | | 0 | 0.00 | | 1 | 0.66 | B3GNT5 |
| branching involved in ureteric bud morphogenesis: GO | 43 | 3 | 1.17 | GDNF; GREM1; PGF | 7 | 1.92 | ADAMTS16; BCL2; FGF1; GPC3; PTCH1; SIX1; TCF21 | 0 | 0.00 | | 0 | 0.00 | | 3 | 1.77 | BCL2; FGF2; PTCH1 | 1 | 0.66 | WNT9B |
| oxygen-dependent proline hydroxylation of hypoxia-inducible factor alpha | 43 | 3 | 1.17 | HIF1A; PSMA5; PSMB6 | 1 | 0.27 | HIF3A | 0 | 0.00 | | 0 | 0.00 | | 1 | 0.59 | HIF3A | 1 | 0.66 | HIF1A |
| regulation of plasma | 43 | 3 | 1.17 | HMOX1; LDLR; LIPG | 7 | 1.92 | ADIPOQ; AGT; AGTR1; | 2 | 19.44 | ADIPOQ; LPL | 0 | 0.00 | | 2 | 1.18 | AGTR1; DGAT2 | 1 | 0.66 | LDLR |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| lipoprotein particle levels: GO | | | | | | | APOC1; APOE; LPL; SOAT2 | | | | | | | | | | | | |
| trna aminoacylation | 43 | 3 | 1.17 | EPRS; GARS; TARS | 0 | 0.00 | | 0 | 0.00 | | 0 | 0.00 | | 0 | 0.00 | | 1 | 0.66 | TARS |
| g alpha1213 signalling events | 43 | 2 | 0.78 | GNGT2; RAC2 | 2 | 0.55 | ADRA1B; OBSCN | 0 | 0.00 | | 1 | 9.72 | RAC2 | 0 | 0.00 | | 1 | 0.66 | ARHGEF16 |
| intrinsic component of mitochondrial membrane: GO | 43 | 2. | 0.78 | BAK1; TIMM23 | 1 | 0.27 | PPOX | 0 | 0.00 | | 0 | 0.00 | | | 1.18 | ARMCX3; PPOX | 1 | 0.66 | BAK1 |
| nadp binding: GO | 43 | 2 | 0.78 | GAPDH; HMGCR | 5 | 1.37 | ASPDH; FMO2; FMO5; NOS2; NOX1 | 0 | 0.00 | | 0 | 0.00 | | 1 | 0.59 | FMO5 | 1 | 0.66 | GAPDH |
| oxygen binding: GO | 43 | 2 | 0.78 | TDO2; TH | 15 | 4.12 | ALB; CYGB; CYP17A1; CYP1A1; CYP1A2; CYP2C9; CYP2D6; CYP3A5; CYP4A11; CYP4B1; CYP4F12; CYP4F8; HBA1; HBA2; HBB | 0 | 0.00 | | 1 | 9.72 | TDO2 | 7 | 4.14 | CYP3A4; CYP3A5; CYP4A11; CYP4B1; CYP4F12; HBA2; HBB | 1 | 0.66 | TH |
| retina morphogenesis in camera type eye: GO | 43 | 2 | 0.78 | FJX1; SDK2 | 6 | 1.65 | CDON; FOXN4; RBP4; RORB; SOX8; TFAP2B | 0 | 0.00 | | 0 | 0.00 | | 2 | 1.18 | CDON; TSPAN12 | 1 | 0.66 | SDK2 |
| vasopressin regulated water reabsorption | 43 | 2 | 0.78 | AQP3; DYNLL1 | 3 | 0.82 | ADCY6; AQP4; DYNC1I1 | 0 | 0.00 | | 0 | 0.00 | | 1 | 0.59 | CREB3L1 | 1 | 0.66 | AQP3 |
| cellular pigmentation: GO | 43 | 1 | 0.39 | RAB38 | 2 | 0.55 | BCL2; TRAPPC6A | 0 | 0.00 | | 0 | 0.00 | | 4 | 2.36 | ASIP; BCL2; SHROOM3; TRAPPC6A | 1 | 0.66 | RAB38 |
| pcg protein | 43 | 1 | 0.39 | CBX2 | 1 | 0.27 | CBX7 | 0 | 0.00 | | 0 | 0.00 | | 1 | 0.59 | CBX7 | 1 | 0.66 | CBX2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| complex: GO | | | | | | | | | | | | | | | | | | | |
| protein localization to vacuole: GO | 43 | 1 | 0.39 | HSPA8 | 0 | 0.00 | | 0 | 0.00 | | 0 | 0.00 | | 0 | 0.00 | | 1 | 0.66 | HSPA8 |
| rna polymerase activity: GO | 43 | 1 | 0.39 | POLR3G | 1 | 0.27 | TERT | 0 | 0.00 | | 0 | 0.00 | | 0 | 0.00 | | 1 | 0.66 | POLR3G |
| stimuli-sensing channels | 43 | 1 | 0.39 | GLTP | 7 | 1.92 | BEST4; MCOLN3; NALCN; SGK2; TRPM3; TRPV6; TSC22D3 | 0 | 0.00 | | 0 | 0.00 | | 3 | 1.77 | NALCN; TRPC1; TSC22D3 | 1 | 0.66 | SGK1 |
| potassium channel regulator activity: GO | 43 | 0 | 0.00 | | 7 | 1.92 | DPP10; DPP6; DRD4; KCNIP1; KCNIP2; KCNMB4; SGK2 | 0 | 0.00 | | 0 | 0.00 | | 3 | 1.77 | ABCC9; DPP6; KCNK2 | 1 | 0.66 | SGK1 |
| vegf signaling pathway | 75 | 5 | 1.12 | NRAS; PLA2G3; PTGS2; RAC2; SH2D2A | 4 | 0.63 | CHP2; PLA2G5; PLA2G6; SHC2 | 0 | 0.00 | | 1 | 5.57 | RAC2 | 2 | 0.68 | CHP2; SHC2 | 2 | 0.76 | PLA2G3; PTGS2 |
| somite development: GO | 75 | 3 | 0.67 | FOXF1; RGS20; WNT5A | 9 | 1.42 | COBL; DKK1; FRZB; KAT2A; MEOX2; NOG; PTCH1; SIX1; WNT11 | 0 | 0.00 | | 0 | 0.00 | | 4 | 1.36 | FOXC1; MEOX2; PTCH1; WNT11 | 2 | 0.76 | RGS20; WNT5A |
| multicellular organism growth: GO | 75 | 2 | 0.45 | BRCA2; STIL | 4 | 0.63 | APBA1; KAT2A; PKDCC; SLC1A2 | 1 | 5.57 | CDKN1C | 0 | 0.00 | | 2 | 0.68 | APBA1; SLITRK6 | 2 | 0.76 | BRCA2; STIL |
| cardiac muscle tissue development: GO | 137 | 10 | 1.22 | CALR; CCNB1; CDK1; CXADR; DSP; MYLK2; NDRG4; NRG1; | 19 | 1.64 | ACTN2; AGT; COL11A1; FHOD3; KAT2A; MESP1; MYH11; MYL3; | 1 | 3.05 | SGCG | 0 | 0.00 | | 7 | 1.30 | COL11A1; FOXC1; MESP1; SGCZ; SORBS2; TNNC1; ZFPM2 | 4 | 0.83 | CCNB1; CDK1; NRG1; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | TBX20; WNT5A | | | MYOCD; NKX2-5; RBP4; SGCG; SGCZ; SORBS2; TBX5; TNNC1; TNNT2; TPM1; ZFPM2 | | | | | | | | | | | | |
| cellular carbohydrate metabolic process: GO | 137 | 10 | 1.22 | B3GNT3; COQ2; GK; HAS3; HK2; PFKFB4; PGM2; PYGL; SLC2A1; TPI1 | 13 | 1.12 | GYG2; HAS1; IDUA; LEP; MOGAT1; MOGAT2; PCK1; PFKFB1; PGM5; PHKG1; PPP1R1A; PYGM; STBD1 | 1 | 3.05 | PPP1R1A | 0 | 0.00 | | 4 | 0.74 | DGAT2; PFKFB1; PGM5; PHKG1 | 4 | 0.83 | HK2; PFKFB4; SLC2A1; TPI1 |
| ligand gated channel activity: GO | 137 | 9 | 1.10 | CHRNA3; CHRNA6; CHRNA9; CLCA2; CNGB1; GABRQ; HTR3A; KCNJ15; KCNK1 | 25 | 2.15 | ABCC8; CFTR; CHRNA2; GABRA2; GABRB3; GABRG3; GABRP; GLRB; GRIA1; GRIA2; GRIA4; GRIK3; GRIK4; GRIK5; GRIN1; GRIN2A; HTR3E; JPH2; KCNJ1; KCNJ3; NCALD; | 1 | 3.05 | GRIA4 | 0 | 0.00 | | 6 | 1.11 | GLRB; GRIA1; GRIA2; GRIK3; NCALD; SCNN1B | 4 | 0.83 | CHRNA6; CLCA2; KCNK1; SCNN1D |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | | | | P2RX1; P2RX6; P2RX7; SLC17A7 | | | | | | | | | | | | |
| organic hydroxy compound biosynthetic process: GO | 168 | 8 | 0.80 | CH25H; CYP27B1; EBP; FABP5; HMGCR; PTAFR; SQLE; TH | 15 | 1.05 | ABCB11; ACOX2; CACNA1H; CFTR; CHPT1; DCT; HAND2; HMGCS2; LEP; NPC1L1; OCA2; PCK1; PLA2G5; PRKAA2; SNCA | 0 | 0.00 | | 0 | 0.00 | | 12 | 1.81 | ACER1; ACOX2; ASIP; CACNA1H; CYP3A4; FGF2; HAND2; HDC; HMGCS2; PRKAA2; SNCA; TRPC1 | 5 | 0.84 | CYP27B1; FABP5; PTAFR; SQLE; TH |
| chemotaxis | 44 | 4 | 1.52 | ACTR3; CFL1; MYLK2; RACGAP1 | 1 | 0.27 | PAK3 | 0 | 0.00 | | 0 | 0.00 | | 1 | 0.58 | PAK3 | 1 | 0.64 | CFL1 |
| intestinal immune network for iga production | 44 | 4 | 1.52 | CD80; CXCR4; ICOS; IL6 | 1 | 0.27 | IL5 | 0 | 0.00 | | 0 | 0.00 | | 1 | 0.58 | CXCL12 | 1 | 0.64 | IL10 |
| asymmetric localization of pcp proteins | 44 | 3 | 1.14 | PSMA5; PSMB6; WNT5A | 1 | 0.27 | FZD4 | 0 | 0.00 | | 0 | 0.00 | | 1 | 0.58 | FZD7 | 1 | 0.64 | WNT5A |
| differentiation pathway in pc12 cells | 44 | 3 | 1.14 | CAMP; NTRK1; TH | 1 | 0.27 | MAPK8IP1 | 0 | 0.00 | | 0 | 0.00 | | 0 | 0.00 | | 1 | 0.64 | TH |
| exocrine system development: GO | 44 | 3 | 1.14 | IGSF3; IL6; TGM2 | 5 | 1.34 | EDA; FGFR1; PAX6; SEMA3A; SOX10 | 0 | 0.00 | | 0 | 0.00 | | 2 | 1.15 | FGFR1; FOXC1 | 1 | 0.64 | TGM2 |
| ligase activity forming carbon oxygen bonds: GO | 44 | 3 | 1.14 | EPRS; GARS; TARS | 0 | 0.00 | | 0 | 0.00 | | 0 | 0.00 | | 0 | 0.00 | | 1 | 0.64 | TARS |
| amino sugar and nucleotide sugar metabolism | 44 | 2 | 0.76 | HK2; PGM2 | 2 | 0.54 | GALT; RENBP | 0 | 0.00 | | 0 | 0.00 | | 0 | 0.00 | | 1 | 0.64 | HK2 |
| androgen and | 44 | 2 | 0.76 | SULT2B1; | 3 | 0.80 | HSD11B1; | 1 | 9.50 | HSD11B2 | 0 | 0.00 | | 1 | 0.58 | SULT1E1 | 1 | 0.64 | SULT2B1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| estrogen metabolism | | | | UGT1A1 | | | UGT2A1; UGT2B7 | | | | | | | | | | | | |
| erbb2 erbb3 pathway | 44 | 2 | 0.76 | NRAS; NRG1 | 1 | 0.27 | NRG2 | 0 | 0.00 | | 0 | 0.00 | | 0 | 0.00 | | 1 | 0.64 | NRG1 |
| ire1alpha activates chaperones | 44 | 2 | 0.76 | HSPA5; SEC61G | 1 | 0.27 | TSPYL2 | 0 | 0.00 | | 0 | 0.00 | | 0 | 0.00 | | 1 | 0.64 | HSPA5 |
| lipid digestion mobilization and transport | 44 | 2 | 0.76 | LDLR; SDC1 | 5 | 1.34 | ALB; APOE; FABP4; LPL; PLIN1 | 1 | 9.50 | LPL | 0 | 0.00 | | 0 | 0.00 | | 1 | 0.64 | LDLR |
| positive regulation of dephosphorylation: GO | 44 | 2 | 0.76 | CDCA2; IFNG | 4 | 1.07 | ADORA1; CHP2; GPLD1; MAGI2 | 0 | 0.00 | | 0 | 0.00 | | 3 | 1.73 | CHP2; DLC1; GPLD1 | 1 | 0.64 | CDCA2 |
| ventricular cardiac muscle tissue development: GO | 44 | 2 | 0.76 | DSP; NRG1 | 8 | 2.15 | COL11A1; MYL3; NKX2-5; TBX5; TNNC1; TNNT2; TPM1; ZFPM2 | 0 | 0.00 | | 0 | 0.00 | | 4 | 2.31 | COL11A1; FOXC1; TNNC1; ZFPM2 | 1 | 0.64 | NRG1 |
| 3 5 exonuclease activity: GO | 44 | 1 | 0.38 | ISG20 | 1 | 0.27 | EXD3 | 0 | 0.00 | | 0 | 0.00 | | 1 | 0.58 | EXD3 | 1 | 0.64 | TREX2 |
| endochondral bone morphogenesis: GO | 44 | 1 | 0.38 | ALPL | 1 | 0.27 | FGFR3 | 0 | 0.00 | | 0 | 0.00 | | 1 | 0.58 | SHOX2 | 1 | 0.64 | BMPR1B |
| collagens | 44 | 0 | 0.00 | | 10 | 2.68 | COL11A1; COL11A2; COL19A1; COL20A1; COL21A1; COL24A1; COL25A1; COL26A1; COL28A1; COL9A2 | 0 | 0.00 | | 0 | 0.00 | | 4 | 2.31 | COL11A1; COL21A1; COL24A1; COL28A1 | 1 | 0.64 | COL17A1 |
| pattern recognition receptor signaling pathway: GO | 107 | 8 | 1.25 | CLEC7A; CTSB; MYD88; PGLYRP2; S100A14; | 2 | 0.22 | COLEC12; MARCO | 0 | 0.00 | | 1 | 3.91 | FFAR2 | 0 | 0.00 | | 3 | 0.80 | CLEC7A; MYD88; S100A14 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | TLR10; TNIP3; UBE2N | | | | | | | | | | | | | | | |
| signaling by egfr in cancer | 107 | 3 | 0.47 | CDK1; CDKN1A; NRAS | 6 | 0.66 | ADCY2; ADCY5; ADCY6; ADCY8; EGF; PRKAR2B | 1 | 3.91 | PRKAR2B | 0 | 0.00 | | 3 | 0.71 | EGF; PDE1A; SPRY1 | 3 | 0.80 | CDK1; CDKN1A; TRIB3 |
| vesicle targeting: GO | 76 | 4 | 0.88 | AREG; CTSC; SERPINA1; TGFA | 4 | 0.62 | FOLR1; GRIA1; NLGN1; TRAPPC6A | 0 | 0.00 | | 0 | 0.00 | | 3 | 1.00 | CNIH3; GRIA1; TRAPPC6A | 2 | 0.75 | AREG; TGFA |
| insulin receptor signaling pathway: GO | 76 | 2 | 0.44 | EIF4EBP1; NAMPT | 8 | 1.24 | ATP6V0A4; ATP6V0E2; ATP6V1B1; GPLD1; IRS2; IRS4; PDK4; SORBS1 | 0 | 0.00 | | 0 | 0.00 | | 4 | 1.34 | ATP6V0A4; ATP6V0E2; GPLD1; PDK4 | 2 | 0.75 | EIF4EBP1; NAMPT |
| n acetyltransferase activity: GO | 76 | 2 | 0.44 | BRCA2; ESCO2 | 3 | 0.47 | KAT2A; NAT8; NAT8L | 0 | 0.00 | | 0 | 0.00 | | 0 | 0.00 | | 2 | 0.75 | BRCA2; NAGS |
| nuclear export: GO | 138 | 6 | 0.73 | CALR; EIF4A3; EIF5A; EIF6; RAN; RANBP1 | 2 | 0.17 | DDX25; PKD 1 | 0 | 0.00 | | 0 | 0.00 | | 1 | 0.18 | DDX25 | 4 | 0.82 | DDX39A; EIF4A3; EIF6; RAN |
| regulation of leukocyte proliferation: GO | 199 | 27 | 2.27 | ANXA1; CD274; CD3E; CD80; CDKN1A; CTLA4; EBI3; GREM1; GSTP1; IDO1; IFNG; IL12B; IL1B; IL2RA; IL6; JAK3; PNP; PRDM1; PRKCQ; PRNP; PYCARD; RAC2; | 8 | 0.47 | BCL2; DHPS; FLT3LG; GPAM; IL5; IRS2; LEP; SCGB1A1 | 1 | 2.10 | GPAM | 3 | 6.30 | IL1B; IL2RA; RAC2 | 1 | 0.13 | BCL2 | 6 | 0.85 | CDKN1A; GSTP1; HLA-G; IL10; PNP; PRKCQ |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | SASH3; SLAMF1; TNFRSF21; TNFRSF4; TNFSF9 | | | | | | | | | | | | | | | |
| positive regulation of map kinase activity: GO | 199 | 13 | 1.09 | CDK1; CXCR4; DUSP6; DUSP9; EPGN; FPR1; IL1B; LPAR3; MDFI; PROK2; S100A12; TGFA; WNT5A | 19 | 1.13 | ADRA2A; BIRC7; DIRAS2; DRD4; EDN3; EGF; ELANE; FGF1; FGFR1; FZD4; FZD8; GHR; MUC20; NTRK3; P2RX7; PAK3; PDGFD; PROK1; SHC2 | 1 | 2.10 | GHR | 1 | 2.10 | IL1B | 11 | 1.40 | ADRA2A; EDN3; EGF; ELANE; FGF2; FGFR1; LPAR1; MUC20; PAK3; PIK3R6; SHC2 | 6 | 0.85 | CDK1; DUSP6; IQGAP3; MDFI; TGFA; WNT5A |
| plasma membrane organization: GO | 199 | 10 | 0.84 | ABCA12; ATP1B3; CXCR4; DYSF; JUP; P2RY1; PIGW; PLSCR3; RAB10; RAB31 | 17 | 1.01 | ACTN2; ADIPOQ; ANK2; ANO3; ANO9; CALCR; CLU; DPP10; DPP6; FA2H; KCNB1; KCNB2; P2RX7; PALM; PRKG2; PTCH1; SPTBN4 | 1 | 2.10 | ADIPOQ | 0 | 0.00 | | 9 | 1.15 | ANO9; CLU; DPP6; PALM; PRKG2; PTCH1; SPTBN4; TESC; TUB | 6 | 0.85 | EFR3B; NDRG1; P2RY1; PIGW; PKP3; RAB31 |
| regulation of calcium ion transmembrane transport: GO | 108 | 8 | 1.24 | BDKRB1; CXCL10; CXCL11; CXCL9; GSTO1; NPSR1; NTSR1; UBASH3B | 16 | 1.75 | ADRA2A; ANK2; ATP1A2; CACNA2D1; CACNB1; CASQ2; DMD; DRD1; DRD4; | 0 | 0.00 | | 1 | 3.87 | CXCL9 | 7 | 1.65 | ADRA2A; CACNA2D1; CACNB1; HRC; SNCA; TRDN; TRPC1 | 3 | 0.79 | CXCL11; NTSR1; UBASH3B |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | FGF14; GSTM2; JPH2; PLA2G6; SLN; SNCA; TRDN | | | | | | | | | | | | |
| rna phosphodiester bond hydrolysis: GO | 108 | 5 | 0.77 | EXO1; ISG20; RNASE7; RPP40; ZC3H12A | 0 | 0.00 | | 0 | 0.00 | | 0 | 0.00 | | 0 | 0.00 | | 3 | 0.79 | EXO1; FEN1; ZC3H12A |
| dna modification: GO | 77 | 1 | 0.22 | APOBEC3A | 4 | 0.61 | NEIL1; PIWIL2; TDRD5; TET1 | 0 | 0.00 | | 0 | 0.00 | | 1 | 0.33 | TET1 | 2 | 0.74 | BEND3; TDRD9 |
| negative regulation of leukocyte mediated immunity: GO | 45 | 8 | 2.97 | FOXF1; HMOX1; IL13RA2; IL7R; JAK3; SERPINB4; SERPINB9; SLAMF1 | 1 | 0.26 | C4BPA | 0 | 0.00 | | 2 | 18.57 | IL7R; SERPINB9 | 0 | 0.00 | | 1 | 0.63 | IL13RA2 |
| alpha beta t cell differentiation: GO | 45 | 6 | 2.23 | ANXA1; EOMES; IFNG; IL12B; IL6; RSAD2 | 2 | 0.52 | BCL2; RORC | 0 | 0.00 | | 0 | 0.00 | | 1 | 0.56 | BCL2 | 1 | 0.63 | BCL3 |
| response to antibiotic: GO | 45 | 6 | 2.23 | ALPL; HSPA5; HYAL3; IL1B; IL6; RAB10 | 4 | 1.05 | AOC3; CRIP1; CYP17A1; CYP1A1 | 0 | 0.00 | | 1 | 9.29 | IL1B | 1 | 0.56 | CRIP1 | 1 | 0.63 | HSPA5 |
| smooth muscle contraction: GO | 45 | 4 | 1.49 | BDKRB2; GDNF; HTR7; SULF2 | 9 | 2.36 | ADRA1A; AGT; CHRM3; DRD1; EDN3; MYH11; NMUR1; NPY1R; PLA2G6 | 0 | 0.00 | | 0 | 0.00 | | 4 | 2.26 | ADRA1A; CHRM3; EDN3; NPY1R | 1 | 0.63 | BDKRB2 |
| nucleobase containing compound kinase activity: GO | 45 | 3 | 1.12 | CMPK2; NME1; TK1 | 2 | 0.52 | DLG2; MPP2 | 0 | 0.00 | | 0 | 0.00 | | 3 | 1.69 | AK7; DLG2; MPP2 | 1 | 0.63 | TK1 |
| positive | 45 | 3 | 1.12 | CXCR4; IL1B; | 4 | 1.05 | LIF; RNF112; | 0 | 0.00 | | 1 | 9.29 | IL1B | 1 | 0.56 | RNF112 | 1 | 0.63 | SERPINE2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| regulation of gliogenesis: GO | | | | SERPINE2 | | | SOX10; SOX8 | | | | | | | | | | | | |
| regulation of neurotransmitter secretion: GO | 45 | 3 | 1.12 | CHRNA3; RIMS3; UNC13A | 9 | 2.36 | CAMK2A; DRD4; GRIK5; KCNMB4; NLGN1; PPP1R9A; RIMS1; SNCA; SNCG | 0 | 0.00 | | 0 | 0.00 | | 2 | 1.13 | RIMS1; SNCA | 1 | 0.63 | UNC13A |
| regulation of toll like receptor signaling pathway: GO | 45 | 3 | 1.12 | F2RL1; LTF; RSAD2 | 0 | 0.00 | | 0 | 0.00 | | 0 | 0.00 | | 0 | 0.00 | | 1 | 0.63 | LTF |
| regulation of tumor necrosis factor mediated signaling pathway: GO | 45 | 3 | 1.12 | F2RL1; GSTP1; PYCARD | 2 | 0.52 | ADIPOQ; NOL3 | 1 | 9.29 | ADIPOQ | 0 | 0.00 | | 0 | 0.00 | | 1 | 0.63 | GSTP1 |
| positive regulation of adenylate cyclase activity: GO | 45 | 2 | 0.74 | ADCYAP1; CAP1 | 10 | 2.62 | ADCY2; ADCY5; ADCY6; ADCY8; ADRB1; CALCR; DRD1; LHCGR; TSHR; VIPR2 | 0 | 0.00 | | 0 | 0.00 | | 1 | 0.56 | TSHR | 1 | 0.63 | CAP1 |
| regulation of sodium ion transmembrane transport: GO | 45 | 2 | 0.74 | ATP1B3; PCSK9 | 6 | 1.57 | AGT; ATP1A2; DMD; DRD4; FXYD2; WNK2 | 0 | 0.00 | | 0 | 0.00 | | 3 | 1.69 | ATP1B2; GLRX; TESC | 1 | 0.63 | PCSK9 |
| tnf pathway | 45 | 2 | 0.74 | STAT1; TXN | 0 | 0.00 | | 0 | 0.00 | | 0 | 0.00 | | 0 | 0.00 | | 1 | 0.63 | TXN |
| keratinocyte differentiation | 45 | 1 | 0.37 | PRKCQ | 2 | 0.52 | BCL2; EGF | 0 | 0.00 | | 0 | 0.00 | | 2 | 1.13 | BCL2; EGF | 1 | 0.63 | PRKCQ |
| outer membrane: GO | 170 | 12 | 1.18 | AGPAT5; BAK1; BCL2A1; CYP27B1; GJA1; GK; | 11 | 0.76 | ACACB; BCL2; GPAM; MAOA; MYOC; P2RX1; PGR; | 1 | 2.46 | GPAM | 0 | 0.00 | | 6 | 0.90 | ARMCX3; BCL2; MYOC; PGR; SNCA; SYNE1 | 5 | 0.83 | BAK1; CYP27B1; HK2; IFI27; VDAC1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | HK2; IFI27; NME1; PRNP; RSAD2; VDAC1 | | | PPP2R2B; SNCA; SOX10; SYNE1 | | | | | | | | | | | | |
| positive regulation of inflammatory response: GO | 109 | 17 | 2.61 | CCL18; CCL3; CCL7; F12; IDO1; IL12B; IL1B; IL1RL1; IL6; OSM; PTGS2; S100A12; S100A8; S100A9; SERPINE1; TLR10; WNT5A | 9 | 0.97 | AGT; AGTR1; C3; CCL14; CNR1; FABP4; KLKB1; LPL; NPY5R | 1 | 3.83 | LPL | 4 | 15.34 | FFAR2; IL1B; OSM; SERPINE1 | 4 | 0.93 | AGTR1; C3; CCL14; GPRC5B | 3 | 0.78 | F12; PTGS2; WNT5A |
| regulation of striated muscle contraction: GO | 78 | 5 | 1.07 | DSC2; DSP; GSTO1; JUP; ZC3H12A | 14 | 2.12 | ADORA1; ADRA1A; ADRA1B; ANK2; ATP1A2; ATP2A1; CASQ2; CTNNA3; DMD; GSTM2; MYBPH; MYL3; NKX2-5; TNNT3 | 0 | 0.00 | | 0 | 0.00 | | 4 | 1.30 | ADRA1A; CTGF; HRC; TNNT3 | 2 | 0.73 | DSC2; ZC3H12A |
| arachidonic acid metabolism | 78 | 4 | 0.86 | CYP4F11; CYP4F22; PLA2G3; PTGS2 | 13 | 1.97 | CYP1A1; CYP1A2; CYP2C9; CYP2J2; CYP4A11; CYP4B1; EPHX2; GGT7; PLA2G5; PLA2G6; PON1; PON3; | 0 | 0.00 | | 0 | 0.00 | | 3 | 0.98 | CYP4A11; CYP4B1; PON3 | 2 | 0.73 | PLA2G3; PTGS2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | PTGIS | | | | | | | | | | | | |
| adult locomotory behavior: GO | 78 | 3 | 0.64 | CSTB; GDNF; NTSR1 | 14 | 2.12 | ADAM22; ATP1A2; DNM1; DRD1; DRD4; GLRB; GRIN1; LGI4; MAPT; SEZ6L; SNCA; SNCG; SPTBN4; TMOD1 | 0 | 0.00 | | 0 | 0.00 | | 13 | 4.23 | ADAM22; CHL1; CXCL12; EFNB3; GLRB; LGI4; MAPT; PREX2; SEZ6L; SLITRK6; SNCA; SPTBN4; ZIC1 | 2 | 0.73 | CSTB; NTSR1 |
| dioxygenase activity: GO | 78 | 3 | 0.64 | IDO1; PTGS2; TDO2 | 6 | 0.91 | CDO1; CYGB; HAAO; P4HTM; PHYHD1; TET1 | 0 | 0.00 | | 1 | 5.36 | TDO2 | 2 | 0.65 | P4HTM; TET1 | 2 | 0.73 | HPDL; PTGS2 |
| post golgi vesicle mediated transport: GO | 78 | 3 | 0.64 | MYO1B; RAB10; RAB31 | 1 | 0.15 | STXBP6 | 0 | 0.00 | | 0 | 0.00 | | 2 | 0.65 | STEAP2; STXBP6 | 2 | 0.73 | MYO1B; RAB31 |
| positive regulation of receptor mediated endocytosis: GO | 46 | 5 | 1.82 | CCL21; GREM1; PCSK9; SELE; SERPINE1 | 4 | 1.03 | HAMP; MAGI2; NLGN1; TF | 0 | 0.00 | | 2 | 18.17 | SELE; SERPINE1 | 1 | 0.55 | ANGPT1 | 1 | 0.62 | PCSK9 |
| regulation of endocrine process: GO | 46 | 3 | 1.09 | F2RL1; HCAR2; IL1B | 7 | 1.80 | AGT; AGTR1; GALR1; INHBB; LEP; LIF; REN | 0 | 0.00 | | 2 | 18.17 | HCAR2; IL1B | 1 | 0.55 | AGTR1 | 1 | 0.62 | UCN2 |
| srp-dependent cotranslational protein targeting to membrane | 46 | 3 | 1.09 | RPL22L1; SEC61G; SPC25 | 0 | 0.00 | | 0 | 0.00 | | 0 | 0.00 | | 0 | 0.00 | | 1 | 0.62 | SPC25 |
| keratinocyte pathway | 46 | 1 | 0.36 | PRKCQ | 2 | 0.51 | BCL2; EGF | 0 | 0.00 | | 0 | 0.00 | | 2 | 1.10 | BCL2; EGF | 1 | 0.62 | PRKCQ |
| mitochondrial biogenesis | 46 | 1 | 0.36 | CYCS | 3 | 0.77 | PPARGC1A; PRKAA2; SHC2 | 0 | 0.00 | | 0 | 0.00 | | 3 | 1.66 | PPARGC1A; PRKAA2; SHC2 | 1 | 0.62 | CYCS |
| regulation of | 46 | 1 | 0.36 | UNC13A | 12 | 3.08 | AGT; APOE; | 0 | 0.00 | | 0 | 0.00 | | 1 | 0.55 | SNCA | 1 | 0.62 | UNC13A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| neuronal synaptic plasticity: GO | | | | | | | BCAN; CAMK2A; CAMK2B; DRD1; GRIN1; NETO1; SHISA6; SHISA8; SNCA; SYNGR1 | | | | | | | | | | | | |
| respiratory gaseous exchange: GO | 46 | 1 | 0.36 | TMPRSS11D | 6 | 1.54 | CFTR; DACH1; ELN; GRIN1; SFTPC; TNNC1 | 0 | 0.00 | | 0 | 0.00 | | 3 | 1.66 | DACH1; ELN; TNNC1 | 1 | 0.62 | SFTPA2 |
| transcription factor activity direct ligand regulated sequence specific dna binding: GO | 46 | 1 | 0.36 | NR4A3 | 6 | 1.54 | AR; ESRRG; NR5A1; RORB; RORC; RXRG | 0 | 0.00 | | 0 | 0.00 | | 3 | 1.66 | ESR1; ESRRG; NR2F1 | 1 | 0.62 | PPARD |
| regulation of t cell proliferation: GO | 141 | 21 | 2.49 | ANXA1; CD274; CD3E; CD80; EBI3; IDO1; IFNG; IL12B; IL1B; IL2RA; IL6; JAK3; PNP; PRKCQ; PRNP; PYCARD; RAC2; SASH3; SLAMF1; TNFRSF21; TNFSF9 | 4 | 0.33 | DHPS; GPAM; LEP; SCGB1A1 | 1 | 2.96 | GPAM | 3 | 8.89 | IL1B; IL2RA; RAC2 | 0 | 0.00 | | 4 | 0.80 | HLA-G; IL10; PNP; PRKCQ |
| regulation of establishment of planar polarity: GO | 110 | 8 | 1.22 | GRHL3; PFN1; PSMA4; PSMA5; PSMB6; | 7 | 0.75 | ARHGEF19; DACT1; FZD4; GPC3; GPC6; MAGI2; | 0 | 0.00 | | 0 | 0.00 | | 4 | 0.92 | DACT1; FZD7; PRICKLE1; WNT11 | 3 | 0.77 | PFN1; WNT5A; WNT9B |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | PSMD1; PSME3; WNT5A | | | WNT11 | | | | | | | | | | | | |
| specification of symmetry: GO | 110 | 8 | 1.22 | FOXF1; GJA1; GREM1; HIF1A; NDRG4; STIL; TBX20; WNT5A | 11 | 1.18 | CCDC40; DAAM2; DNAAF1; DNAH11; FOLR1; FOXN4; GREM2; HAND2; MESP1; NKX2-5; PCSK5 | 0 | 0.00 | | 0 | 0.00 | | 3 | 0.69 | GREM2; HAND2; MESP1 | 3 | 0.77 | HIF1A; STIL; WNT5A |
| negative regulation of cell morphogenesis involved in differentiation: GO | 110 | 4 | 0.61 | CDK5R1; SEMA4B; STAT1; WNT5A | 11 | 1.18 | BMP5; LRP4; NLGN1; PLXNA3; SEMA3A; SEMA3B; SEMA3D; SEMA3E; SEMA3G; SLIT2; TBX5 | 0 | 0.00 | | 1 | 3.80 | GBP1 | 5 | 1.15 | FBLN1; FOXA1; SEMA3E; SEMA4G; SLIT2 | 3 | 0.77 | CDK5R1; SEMA4B; WNT5A |
| fc epsilon ri signaling pathway | 79 | 4 | 0.85 | CSF2; NRAS; PLA2G3; RAC2 | 3 | 0.45 | IL5; PLA2G5; PLA2G6 | 0 | 0.00 | | 2 | 10.58 | LCP2; RAC2 | 1 | 0.32 | MS4A2 | 2 | 0.72 | PLA2G3; VAV2 |
| regulation of translational initiation: GO | 79 | 4 | 0.85 | EIF2S1; EIF4EBP1; EIF4G2; NPM1 | 0 | 0.00 | | 0 | 0.00 | | 0 | 0.00 | | 0 | 0.00 | | 2 | 0.72 | EIF4EBP1; NPM1 |
| mapk pathway | 79 | 3 | 0.64 | MAPK6; STAT1; TGFBR1 | 1 | 0.15 | MAPK4 | 0 | 0.00 | | 0 | 0.00 | | 0 | 0.00 | | 2 | 0.72 | MAPK6; RPS6KA4 |
| ubiquitin like protein binding: GO | 111 | 7 | 1.06 | CXCR4; KIF18A; RNF222; TNIP3; TOP2A; UBE2N; VCP | 3 | 0.32 | CRY2; KCNB1; SOBP | 0 | 0.00 | | 0 | 0.00 | | 1 | 0.23 | CRY2 | 3 | 0.77 | KIF18A; RNF222; TOP2A |
| ovulation cycle: GO | 111 | 5 | 0.75 | ADCYAP1; ANXA1; | 14 | 1.49 | BCL2; CLU; FZD4; HAS1; | 0 | 0.00 | | 0 | 0.00 | | 6 | 1.37 | BCL2; CLU; ESR1; | 3 | 0.77 | BMPR1B; EREG; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | CCNE1; EREG; WNT5A | | | INHBB; LEP; LHCGR; MSTN; NOBOX; NPY5R; NR5A1; SLIT2; SLIT3; TIMP4 | | | | | | | | | FOXC1; SLIT2; SLIT3 | | | WNT5A |
| locomotory behavior: GO | 173 | 11 | 1.06 | ALDH1A3; CHRNA3; CSTB; DPP4; GDNF; IDO1; NRG1; NTSR1; TH; UBA6; USP2 | 27 | 1.84 | ADAM22; ADCY5; APBA1; ATP1A2; ATP2B2; DNM1; DRD1; DRD4; ESPN; FEZF2; FZD4; GLRB; GRIN1; KCND2; LGI4; MAPT; MCOLN3; MYO15A; NEGR1; NOVA1; NPY1R; SEZ6L; SNCA; SNCG; SOBP; SPTBN4; TMOD1 | 0 | 0.00 | | 0 | 0.00 | | 20 | 2.94 | ADAM22; APBA1; CHL1; CXCL12; EFNB3; GLRB; GPRC5B; KCND2; LGI4; LSAMP; MAPT; NEGR1; NPY1R; PREX2; SEZ6L; SLC18A2; SLITRK6; SNCA; SPTBN4; ZIC1 | 5 | 0.82 | CSTB; DPP4; NRG1; NTSR1; TH |
| neuron death: GO | 47 | 6 | 2.14 | FAM162A; GAPDH; KLK6; PLAU; TNFRSF21; TP63 | 2 | 0.50 | BCL2; MEOX2 | 0 | 0.00 | | 0 | 0.00 | | 2 | 1.08 | BCL2; MEOX2 | 1 | 0.60 | GAPDH |
| positive regulation of reactive oxygen species biosynthetic process: GO | 47 | 4 | 1.42 | IFNG; IL1B; IL6; PTGS2 | 3 | 0.75 | AGT; CLU; HBB | 0 | 0.00 | | 1 | 8.89 | IL1B | 3 | 1.62 | CLU; ESR1; HBB | 1 | 0.60 | PTGS2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| positive regulation of regulated secretory pathway: GO | 47 | 3 | 1.07 | F2RL1; IL4R; PTAFR | 5 | 1.26 | CACNA1H; KCNB1; NLGN1; SYT1; SYT9 | 0 | 0.00 | | 0 | 0.00 | | 2 | 1.08 | CACNA1G; CACNA1H | 1 | 0.60 | PTAFR |
| sterol transport: GO | 47 | 3 | 1.07 | ABCG4; LDLR; LIPG | 7 | 1.76 | ABCA2; APOC1; APOE; CFTR; CLU; NPC1L1; SOAT2 | 0 | 0.00 | | 0 | 0.00 | | 1 | 0.54 | CLU | 1 | 0.60 | LDLR |
| ecm proteoglycans | 47 | 2 | 0.71 | SERPINE1; TNC | 5 | 1.26 | COL9A2; ITGA7; LAMA2; LRP4; TNXB | 0 | 0.00 | | 1 | 8.89 | SERPINE1 | 3 | 1.62 | DCN; GULP1; LAMA2 | 1 | 0.60 | AGRN |
| negative regulation of peptide secretion: GO | 47 | 2 | 0.71 | HMGCR; VSNL1 | 7 | 1.76 | ABCC8; ACVR1C; ADRA2A; CARTPT; INHBB; KCNB1; LEP | 1 | 8.89 | ACVR1C | 0 | 0.00 | | 1 | 0.54 | ADRA2A | 1 | 0.60 | VSNL1 |
| positive regulation of pathway restricted smad protein phosphorylation: GO | 47 | 2 | 0.71 | TGFBR1; TTK | 6 | 1.51 | BMP3; BMP5; GDF10; GDF5; INHBB; MSTN | 0 | 0.00 | | 0 | 0.00 | | 1 | 0.54 | GDF7 | 1 | 0.60 | TTK |
| notch1 intracellular domain regulates transcription | 47 | 1 | 0.36 | HIF1A | 3 | 0.75 | HDAC5; KAT2A; TLE2 | 0 | 0.00 | | 0 | 0.00 | | 1 | 0.54 | TLE2 | 1 | 0.60 | HIF1A |
| regulation of lipid kinase activity: GO | 47 | 1 | 0.36 | CCL21 | 3 | 0.75 | CCKBR; ERBB4; FGFR3 | 0 | 0.00 | | 0 | 0.00 | | 3 | 1.62 | ERBB4; FGF2; PIK3R6 | 1 | 0.60 | VAV2 |
| response to glucagon: GO | 47 | 1 | 0.36 | CCNA2 | 9 | 2.26 | ADCY2; ADCY5; ADCY6; ADCY8; CDO1; GCGR; HMGCS2; | 1 | 8.89 | PRKAR2B | 0 | 0.00 | | 3 | 1.62 | GNG11; HMGCS2; PFKFB1 | 1 | 0.60 | CCNA2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | PFKFB1; PRKAR2B | | | | | | | | | | | | |
| hematopoietic cell lineage | 80 | 14 | 2.93 | CD1B; CD2; CD3E; CSF2; FCGR1A; IL1A; IL1B; IL1R2; IL2RA; IL4R; IL6; IL7R; ITGA3; ITGA6 | 5 | 0.74 | CD34; FCER2; FLT3LG; IL11RA; IL5 | 0 | 0.00 | | 3 | 15.67 | IL1B; IL2RA; IL7R | 2 | 0.64 | CD34; IL11RA | 2 | 0.71 | ITGA3; ITGA6 |
| cardiac conduction: GO | 80 | 6 | 1.26 | CXADR; DSC2; DSP; GJA1; JUP; KCNK1 | 12 | 1.77 | ANK2; ATP1A2; CACNA1F; CACNA2D1; CACNA2D2; CACNB1; CASQ2; CTNNA3; KCND2; KCNIP1; KCNIP2; SPTBN4 | 0 | 0.00 | | 0 | 0.00 | | 7 | 2.22 | ATP1B2; CACNA1G; CACNA2D1; CACNA2D2; CACNB1; KCND2; SPTBN4 | 2 | 0.71 | DSC2; KCNK1 |
| secretory granule lumen: GO | 80 | 3 | 0.63 | SERPINA1; SERPINE1; SRGN | 10 | 1.47 | ACTN2; ALB; CFD; CLEC3B; CLU; EGF; PCSK2; RARRES2; TF; TIMP3 | 1 | 5.22 | CLEC3B | 1 | 5.22 | SERPINE1 | 4 | 1.27 | CLU; EGF; ISLR; RARRES2 | 2. | 0.71 | ACTN1; LGALS3BP |
| transmembrane receptor protein kinase activity: GO | 80 | 3 | 0.63 | LTBP1; NTRK1; TGFBR1 | 12 | 1.77 | ACVR1C; AMHR2; EPHA6; EPHB1; EPHB6; ERBB4; FGFR1; FGFR3; LTK; MERTK; NTRK3; ROS1 | 1 | 5.22 | ACVR1C | 0 | 0.00 | | 5 | 1.59 | DDR2; EFNB3; ERBB4; FGFR1; PDGFRL | 2 | 0.71 | BMPR1B; EPHA2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| sensory perception of mechanical stimulus: GO | 144 | 10 | 1.16 | CHRNA9; GJB2; GJB3; GJB6; IFNG; NTRK1; SERPINE2; TH; TIMM13; TIMM8B | 32 | 2.62 | ATP2B2; ATP6V0A4; ATP6V1B1; CLIC5; COCH; COL11A1; COL11A2; DNM1; DRGX; ESPN; FGFR1; FZD4; GABRB3; GJC3; GRM7; GRXCR2; KCNA1; MYH14; MYO15A; MYO1A; MYO3A; OTOA; OTOGL; PAX3; PCDH15; PDZD7; SIX1; SLC26A5; SOBP; SPTBN4; TMC2; TSPEAR | 0 | 0.00 | | 0 | 0.00 | | 10 | 1.76 | ATP6V0A4; CLIC5; COCH; COL11A1; FGFR1; PDZD7; PIEZO2; SLITRK6; SPTBN4; TUB | 4 | 0.79 | SERPINE2; SNAI2; TH; TMC1 |
| regulation of dephosphorylation: GO | 144 | 5 | 0.58 | CDCA2; IFNG; PKMYT1; PPP2R2C; PPP4R4 | 13 | 1.07 | ADORA1; CAMSAP3; CHP2; CRY2; DLG2; ELFN2; GPLD1; MAGI2; PCDH11X; PPP1R14A; PPP2R2B; SLC7A14; TSKS | 0 | 0.00 | | 1 | 2.90 | SPOCD1 | 5 | 0.88 | CHP2; CRY2; DLC1; DLG2; GPLD1 | 4 | 0.79 | CDCA2; LMTK3; PKMYT1; PPP2R2C |
| ajdiss 2pathway | 48 | 5 | 1.74 | DSP; GDNF; | 2 | 0.49 | EGF; GFRA1 | 0 | 0.00 | | 0 | 0.00 | | 1 | 0.53 | EGF | 1 | 0.59 | MMP3 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | JUP; MMP3; NME1 | | | | | | | | | | | | | | | |
| lateral plasma membrane: GO | 48 | 5 | 1.74 | ANXA1; DSG1; GJA1; GJB2; JUP | 6 | 1.47 | ATP6V1B1; DMD; KCNB1; MYO1A; PKD1; SLC26A5 | 0 | 0.00 | | 0 | 0.00 | | 0 | 0.00 | | 1 | 0.59 | IQGAP3 |
| activation of mapkk activity: GO | 48 | 3 | 1.05 | NGF; NTRK1; TGFBR1 | 3 | 0.74 | ADORA1; CARTPT; EGF | 0 | 0.00 | | 0 | 0.00 | | 1 | 0.53 | EGF | 1 | 0.59 | NGF |
| carbohydrate derivative transport: GO | 48 | 3 | 1.05 | GJA1; GLTP; SLC28A3 | 0 | 0.00 | | 0 | 0.00 | | 0 | 0.00 | | 1 | 0.53 | SLC29A1 | 1 | 0.59 | SLC28A3 |
| face development: GO | 48 | 3 | 1.05 | ALDH1A3; STRA6; WNT5A | 3 | 0.74 | DKK1; MYH3; NOG | 0 | 0.00 | | 0 | 0.00 | | 0 | 0.00 | | 1 | 0.59 | WNT5A |
| positive regulation of intrinsic apoptotic signaling pathway: GO | 48 | 3 | 1.05 | IL19; S100A8; S100A9 | 3 | 0.74 | BCL2; CLU; NOX1 | 0 | 0.00 | | 0 | 0.00 | | 2 | 1.06 | BCL2; CLU | 1 | 0.59 | IL19 |
| regulation of lipid catabolic process: GO | 48 | 3 | 1.05 | HCAR2; IL1B; LDLR | 11 | 2.70 | ABCD2; ACACB; ADORA1; ADRA2A; APOC1; CNR1; GPLD1; IRS2; LGALS12; PLIN5; RARRES2 | 1 | 8.71 | ABCD2 | 2 | 17.41 | HCAR2; IL1B | 3 | 1.59 | ADRA2A; GPLD1; RARRES2 | 1 | 0.59 | LDLR |
| regulation of nitric oxide synthase activity: GO | 48 | 3 | 1.05 | HIF1A; IL1B; LYPLA1 | 8 | 1.97 | APOE; CNR1; CYGB; FCER2; GCHFR; LEP; PRKG2; TERT | 0 | 0.00 | | 1 | 8.71 | IL1B | 2 | 1.06 | ESR1; PRKG2 | 1 | 0.59 | HIF1A |
| cardiac septum morphogenesis: GO | 48 | 2 | 0.70 | TBX20; WNT5A | 4 | 0.98 | NKX2-5; TBX5; WNT11; | 0 | 0.00 | | 0 | 0.00 | | 2 | 1.06 | WNT11; ZFPM2 | 1 | 0.59 | WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | ZFPM2 | | | | | | | | | | | | |
| fatty acyl coa metabolic process: GO | 48 | 2 | 0.70 | ACOT7; ELOVL7 | 7 | 1.72 | ACACB; ACOT1; ACOT12; ACSBG1; ACSF2; ELOVL2; SCD5 | 0 | 0.00 | | 0 | 0.00 | | 1 | 0.53 | DGAT2 | 1 | 0.59 | ACOT7 |
| protein autoubiquitination: GO | 48 | 2 | 0.70 | UBE2T; UHRF1 | 1 | 0.25 | ASB4 | 0 | 0.00 | | 0 | 0.00 | | 0 | 0.00 | | 1 | 0.59 | UBE2T |
| ps1 pathway | 48 | 2 | 0.70 | CSNK1A1; PSENEN | 5 | 1.23 | DKK1; DKK2; DTX1; SSPO; WIFI | 0 | 0.00 | | 0 | 0.00 | | 0 | 0.00 | | 1 | 0.59 | PPARD |
| ceramide pathway | 48 | 1 | 0.35 | CYCS | 2 | 0.49 | BCL2; EGF | 0 | 0.00 | | 0 | 0.00 | | 2 | 1.06 | BCL2; EGF | 1 | 0.59 | CYCS |
| myotube differentiation: GO | 48 | 1 | 0.35 | HOMER1 | 5 | 1.23 | ACTA1; C16orf89; CACNA1H; CDON; MYEF2 | 0 | 0.00 | | 0 | 0.00 | | 2 | 1.06 | CACNA1H; CDON | 1 | 0.59 | HOMER1 |
| regulation of fatty acid metabolic process: GO | 81 | 7 | 1.45 | ANXA1; GK; NR4A3; PTGS2; UGT1A1; UGT1A10; UGT1A7 | 13 | 1.89 | ABCD2; ACACB; ACADL; ADIPOQ; APOC1; CNR1; IRS2; MLXIPL; PDK4; PLIN5; PPARGC1A; PRKAA2; SNCA | 2 | 10.32 | ABCD2; ADIPOQ | 0 | 0.00 | | 6 | 1.88 | DGAT2; PDK3; PDK4; PPARGC1A; PRKAA2; SNCA | 2 | 0.70 | PTGS2; TRIB3 |
| positive regulation of exocytosis: GO | 81 | 6 | 1.24 | F2RL1; IFNG; IL4R; PTAFR; SDC1; VSNL1 | 7 | 1.02 | CACNA1H; CFTR; KCNB1; NLGN1; PLA2G6; SYT1; SYT9 | 0 | 0.00 | | 0 | 0.00 | | 2 | 0.63 | CACNA1G; CACNA1H | 2 | 0.70 | PTAFR; VSNL1 |
| catalytic step 2 spliceosome: GO | 81 | 4 | 0.83 | EIF4A3; PPIL1; SNRPF; SNRPG | 1 | 0.15 | SNRPN | 0 | 0.00 | | 0 | 0.00 | | 1 | 0.31 | SNRPN | 2 | 0.70 | EIF4A3; PPIL1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| mapkinase signaling pathway | 81 | 3 | 0.62 | MAPK6; STAT1; TGFBR1 | 1 | 0.15 | MAPK4 | 0 | 0.00 | | 0 | 0.00 | | 0 | 0.00 | | 2 | 0.70 | MAPK6; RPS6KA4 |
| toll receptor cascades | 113 | 7 | 1.04 | CDK1; CTSB; DUSP6; MYD88; S100A12; TLR10; UBE2N | 2 | 0.21 | DNM1; PELI2 | 0 | 0.00 | | 0 | 0.00 | | 1 | 0.22 | PELI2 | 3 | 0.75 | CDK1; DUSP6; MYD88 |
| neurotrophin signaling pathway | 113 | 5 | 0.74 | CALML3; CALML5; NRAS; YWHAQ; YWHAZ | 9 | 0.94 | BCL2; CALML6; CAMK2A; CAMK2B; IRS2; IRS4; RPS6KA6; SHC2; SHC3 | 0 | 0.00 | | 0 | 0.00 | | 3 | 0.67 | BCL2; RPS6KA6; SHC2 | 3 | 0.75 | RPS6KA4; YWHAQ; YWHAZ |
| regulation of actin filament length: GO | 145 | 11 | 1.27 | ACTR3; ARPC1A; ARPC3; ARPC5L; CAPZA1; CCL21; F2RL1; PFN1; PYCARD; SH3BGRL3; TWF1 | 11 | 0.90 | ACTN2; CAPZA3; FHOD3; GSN; LMOD1; PAK3; PPP1R9A; SCIN; SLIT2; SPTBN4; TMOD1 | 0 | 0.00 | | 0 | 0.00 | | 7 | 1.23 | CAPZA3; CXCL12; LMOD1; PAK3; SCIN; SLIT2; SPTBN4 | 4 | 0.78 | ARPC1A; CDC42EP1; PFN1; TWF1 |
| transport vesicle membrane: GO | 145 | 3 | 0.35 | AREG; SYCN; TGFA | 13 | 1.06 | ABCC8; FOLR1; GRIA1; ICA1; NCALD; RPH3AL; SLC17A7; SLC6A17; SV2B; SYN2; SYNGR1; SYT1; SYT9 | 0 | 0.00 | | 0 | 0.00 | | 9 | 1.58 | CNIH3; CPE; GRIA1; HLA-DQB2; ICA1; NCALD; SLC18A2; SV2B; SYN2 | 4 | 0.78 | AREG; HLA-G; SLC18A3; TGFA |
| regulation of mrna metabolic process: GO | 114 | 4 | 0.59 | C1QBP; CCNB1; HSPA8; ZC3H12A | 4 | 0.41 | CELF4; NOVA1; RBFOX1; RBM11 | 0 | 0.00 | | 0 | 0.00 | | 0 | 0.00 | | 3 | 0.75 | CCNB1; HSPA8; ZC3H12A |
| leukocyte | 82 | 7 | 1.43 | CD79A; EBI3; | 4 | 0.58 | BCL2; CLU; | 0 | 0.00 | | 1 | 5.10 | IL7R | 2 | 0.62 | BCL2; CLU | 2 | 0.69 | IFNE; IL10 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| proliferation: GO | | | | F2RL1; IFNE; IL7R; SLAMF1; TNFRSF4 | | | IFNA5; P2RX7 | | | | | | | | | | | | |
| g alpha s signalling events | 82 | 6 | 1.22 | ADCYAP1; ADM2; GNGT2; HTR7; INSL3; NPSR1 | 15 | 2.16 | ADCY2; ADCY5; ADCY6; DRD1; GCGR; GNAZ; HTR4; HTR6; LHB; LHCGR; PDE11A; PTH1R; SCT; TSHR; VIPR2 | 0 | 0.00 | | 0 | 0.00 | | 5 | 1.55 | ADCYAP1R1; PDE1A; PTGDR; PTH1R; TSHR | 2 | 0.69 | ADM2; HRH2 |
| regulation of cation channel activity: GO | 82 | 4 | 0.82 | GSTO1; HOMER1; MMP9; NTSR1 | 14 | 2.01 | ACTN2; ANK2; CACNA2D1; CACNB1; CASQ2; DMD; DRD4; FGF14; GSTM2; HAMP; JPH2; KCNIP2; PLA2G6; TRDN | 0 | 0.00 | | 0 | 0.00 | | 4 | 1.24 | CACNA2D1; CACNB1; HRC; TRDN | 2 | 0.69 | HOMER1; NTSR1 |
| pten regulation | 82 | 3 | 0.61 | CBX2; PSMA5; PSMB6 | 0 | 0.00 | | 0 | 0.00 | | 0 | 0.00 | | 1 | 0.31 | PREX2 | 2 | 0.69 | CBX2; SNAI2 |
| natural killer cell activation: GO | 49 | 8 | 2.73 | CD2; IFNE; IL12B; SLAMF1; SLAMF7; ULBP1; ULBP2; ULBP3 | 3 | 0.72 | IFNA5; KLRF2; MERTK | 0 | 0.00 | | 1 | 8.53 | IL21R | 1 | 0.52 | KLRF2 | 1 | 0.58 | IFNE |
| cytosolic dna sensing pathway | 49 | 6 | 2.05 | CXCL10; IL1B; IL6; POLR3G; PYCARD; | 1 | 0.24 | IFNA5 | 0 | 0.00 | | 1 | 8.53 | IL1B | 0 | 0.00 | | 1 | 0.58 | POLR3G |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | ZBP1 | | | | | | | | | | | | | | | |
| protein transmembrane transport: GO | 49 | 4 | 1.37 | HSPA4; HSPA8; SEC61G; TIMM23 | 1 | 0.24 | GPIHBP1 | 0 | 0.00 | | 0 | 0.00 | | 0 | 0.00 | | 1 | 0.58 | HSPA8 |
| quaternary ammonium group binding: GO | 49 | 4 | 1.37 | CHRNA3; CHRNA6; CHRNA9; HTR3A | 8 | 1.93 | ALDOB; ANXA13; APOC1; CHRM3; CHRNA2; GPR12; HTR3E; SERPINA5 | 0 | 0.00 | | 0 | 0.00 | | 3 | 1.56 | CHRM3; GPR12; IGHM | 1 | 0.58 | CHRNA6 |
| intramolecular oxidoreductase activity: GO | 49 | 3 | 1.02 | EBP; PDIA3; TPI1 | 2 | 0.48 | DCT; PTGIS | 0 | 0.00 | | 0 | 0.00 | | 0 | 0.00 | | 1 | 0.58 | TPI1 |
| translation initiation factor activity: GO | 49 | 3 | 1.02 | EIF2S1; EIF4G2; EIF6 | 0 | 0.00 | | 0 | 0.00 | | 0 | 0.00 | | 0 | 0.00 | | 1 | 0.58 | EIF6 |
| butanoate metabolism | 49 | | 0.68 | AKR1B10; ALDH1A3 | 2 | 0.48 | ACSM5; HMGCS2 | 0 | 0.00 | | 0 | 0.00 | | 3 | 1.56 | ALDH3A2; ALDH5A1; HMGCS2 | 1 | 0.58 | AKR1B10 |
| neural retina development: GO | 49 | 2 | 0.68 | FJX1; SDK2 | 5 | 1.20 | FOXN4; RORB; SLC17A7; SOX8; TFAP2B | 0 | 0.00 | | 0 | 0.00 | | 1 | 0.52 | TSPAN12 | 1 | 0.58 | SDK2 |
| oncogenic mapk signaling | 49 | 2 | 0.68 | ACTB; NRAS | 1 | 0.24 | CNKSR2 | 0 | 0.00 | | 0 | 0.00 | | 1 | 0.52 | CNKSR2 | 1 | 0.58 | ACTB |
| regulation of adherens junction organization: GO | 49 | 2 | 0.68 | GREM1; RHOD | 3 | 0.72 | APOD; ARHGAP6; MYOC | 0 | 0.00 | | 0 | 0.00 | | 2 | 1.04 | DLC1; MYOC | 1 | 0.58 | RHOD |
| thioester biosynthetic process: GO | 49 | 2 | 0.68 | ACOT7; ELOVL7 | 7 | 1.69 | ACACB; ACOT1; ACOT12; ACSBG1; ACSF2; ELOVL2; SCD5 | 0 | 0.00 | | 0 | 0.00 | | 0 | 0.00 | | 1 | 0.58 | ACOT7 |
| transcriptional | 49 | 2 | 0.68 | PITX1; | 5 | 1.20 | MYOCD; | 0 | 0.00 | | 0 | 0.00 | | 2 | 1.04 | PRRX1; | 1 | 0.58 | PITX1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| repressor activity rna polymerase ii activating transcription factor binding: GO | | | | TBX20 | | | NKX2-5; SOX10; TFAP2B; ZFPM2 | | | | | | | | | ZFPM2 | | | |
| nuclear receptor transcription pathway | 49 | 1 | 0.34 | NR4A3 | 8 | 1.93 | AR; ESRRG; NR3C2; NR5A1; PGR; RORB; RORC; RXRG | 0 | 0.00 | | 0 | 0.00 | | 5 | 2.59 | ESR1; ESRRG; NR2F1; NR3C2; PGR | 1 | 0.58 | PPARD |
| pi3kci pathway | 49 | 1 | 0.34 | NRAS | 0 | 0.00 | | 0 | 0.00 | | 0 | 0.00 | | 1 | 0.52 | PIK3R6 | 1 | 0.58 | SGK1 |
| transforming growth factor beta receptor binding: GO | 49 | 1 | 0.34 | TGFBR1 | 6 | 1.44 | BMP3; BMP5; GDF10; GDF5; INHBB; MSTN | 0 | 0.00 | | 0 | 0.00 | | 1 | 0.52 | GDF7 | 1 | 0.58 | LRG1 |
| calmodulin binding: GO | 177 | 7 | 0.66 | ASPM; CAMKIG; CNN2; ENKUR; MYLK2; MYO1B; RGS1 | 27 | 1.80 | ATP2B2; CAMK1; CAMK2A; CAMK2B; CAMKV; CAMSAP3; CNN1; DCX; EEF2K; GRIN1; MAP6; MYH11; MYH14; MYH3; MYO15A; MYO1A; MYO3A; MYO5C; NOS2; OBSCN; PCP4; PHKG1; PLA2G6; PNCK; SYT1; TRPV6; USP6 | 0 | 0.00 | | 0 | 0.00 | | 6 | 0.86 | ADD3; CAMK1; MYO5C; PDE1A; PHKG1; SNTB1 | 5 | 0.80 | ASPM; CAMK1G; IQGAP3; MYO1B; RGS1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline: Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo: Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo: Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| keratin filament: GO | 83 | 10 | 2.02 | CSNK1A1; KRT13; KRT14; KRT3; KRT5; KRT6A; KRT6B; KRT6C; KRT75; KRT76 | 12 | 1.71 | KRT72; KRT73; KRT77; KRT86; KRTAP10-11; KRTAP10-12; KRTAP10-8; KRTAP11-1; KRTAP12-3; KRTAP3-2; KRTAP3-3; KRTAP5-7 | 2 | 10.07 | KRT72; KRT73 | 0 | 0.00 | | 4 | 1.22 | KRT2; KRT77; KRT86; KRTAP16-1 | 2 | 0.68 | KRT13; KRT5 |
| myeloid cell homeostasis: GO | 83 | 7 | 1.41 | ANXA1; BAK1; HCAR2; HMOX1; IFNG; IL6; PRDX1 | 4 | 0.57 | ALAS2; EPB42; GATA1; RHAG | 0 | 0.00 | | 1 | 5.03 | HCAR2 | 0 | 0.00 | | 2 | 0.68 | BAK1; DYRK3 |
| positive regulation of muscle cell differentiation: GO | 83 | 5 | 1.01 | CXCL9; GREM1; IL4R; NEU2; NRG1 | 8 | 1.14 | BCL2; BOC; CAMK1; CDON; FLT3LG; MESP1; MYOCD; SCGB3A1 | 0 | 0.00 | | 1 | 5.03 | CXCL9 | 5 | 1.53 | BCL2; CAMK1; CDON; MESP1; SHOX2 | 2 | 0.68 | IGFBP3; NRG1 |
| golgi organization: GO | 83 | 4 | 0.81 | CDK1; CSNK1A1; VMP1; YWHAZ | 1 | 0.14 | SYNE1 | 0 | 0.00 | | 0 | 0.00 | | 2 | 0.61 | BHLHA15; SYNE1 | 2 | 0.68 | CDK1; YWHAZ |
| parkinsons disease | 83 | 4 | 0.81 | COX7B; CYCS; SLC25A5; VDAC1 | 1 | 0.14 | COX7A1 | 0 | 0.00 | | 0 | 0.00 | | 2 | 0.61 | COX7A1; SLC18A2 | 2 | 0.68 | CYCS; VDAC1 |
| t cell receptor signaling pathway | 83 | 4 | 0.81 | CSF2; CTLA4; ICOS; NRAS | 2 | 0.28 | CHP2; IL5 | 0 | 0.00 | | 0 | 0.00 | | 1 | 0.31 | CHP2 | 2 | 0.68 | IL10; VAV2 |
| regulation of cyclic nucleotide metabolic process: GO | 147 | 11 | 1.25 | ADCYAP1; CAP1; CXCL10; CXCL11; CXCL9; | 22 | 1.77 | ADCY2; ADCY5; ADCY6; ADCY8; ADRA2A; | 1 | 2.84 | MRAP2 | 1 | 2.84 | CXCL9 | 6 | 1.04 | ADCYAP1R1; ADRA2A; AKAP12; LPAR1; PALM; TSHR | 4 | 0.77 | CAP1; CXCL11; PTHLH; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | GNAI3; GPR65; GPR87; INSL3; PTHLH; WNT5A | | | ADRB1; AKAP12; APOE; CALCR; DRD1; DRD4; GALR1; GRM7; GUCA1B; LHCGR; NOS2; OSTN; OXER1; PALM; SCT; TSHR; VIPR2 | | | | | | | | | | | | |
| organic hydroxy compound transport: GO | 147 | 8 | 0.91 | ABCG4; AQP3; FABP6; LDLR; LIPG; SLC10A6; SLC16A1; SLC16A6 | 24 | 1.93 | ABCA2; ABCB11; ABCC3; ACACB; ALB; APOC1; APOE; AQP4; AQP7; CADPS; CFTR; CLU; DRD1; NPC1L1; P2RX1; PRKAA2; RBP4; SLC10A2; SLC16A11; SLC16A12; SLC16A8; SLC6A2; SNCA; SOAT2 | 0 | 0.00 | | 1 | 2.84 | AQP9 | 4 | 0.69 | CLU; PRKAA2; SLC18A2; SNCA | 4 | 0.77 | AQP3; LDLR; SLC16A6; SLC26A6 |
| cellular carbohydrate biosynthetic process: GO | 50 | 4 | 1.34 | B3GNT3; HAS3; PGM2; SLC2A1 | 6 | 1.42 | GYG2; HAS1; LEP; PCK1; PGM5; PHKG1 | 0 | 0.00 | | 0 | 0.00 | | 2 | 1.02 | PGM5; PHKG1 | 1 | 0.57 | SLC2A1 |
| cellular response to hypoxia | 50 | 4 | 1.34 | HIF1A; HIGD1A; PSMA5; | 1 | 0.24 | HIF3A | 0 | 0.00 | | 0 | 0.00 | | 1 | 0.51 | HIF3A | 1 | 0.57 | HIF1A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | PSMB6 | | | | | | | | | | | | | | | |
| regulation of hypoxia-inducible factor (hif) by oxygen | 50 | 4 | 1.34 | HIF1A; HIGDIA; PSMA5; PSMB6 | 1 | 0.24 | HIF3A | 0 | 0.00 | | 0 | 0.00 | | 1 | 0.51 | HIF3A | 1 | 0.57 | HIF1A |
| metalloexo-peptidase activity: GO | 50 | 2 | 0.67 | CPA6; CPXM1 | 3 | 0.71 | AGBL1; AGBL4; TRHDE | 0 | 0.00 | | 0 | 0.00 | | 2 | 1.02 | CPE; CPZ | 1 | 0.57 | CPA6 |
| aerobic respiration: GO | 50 | 1 | 0.33 | OGDHL | 0 | 0.00 | | 0 | 0.00 | | 0 | 0.00 | | 0 | 0.00 | | 1 | 0.57 | OGDHL |
| angiopoietin receptor pathway | 50 | 1 | 0.33 | CDKN1A | 3 | 0.71 | AGTR1; ANGPT4; GRB14 | 0 | 0.00 | | 0 | 0.00 | | 4 | 2.03 | AGTR1; ANGPT1; ANGPT4; FGF2 | 1 | 0.57 | CDKN1A |
| arachidonic acid metabolic process: GO | 50 | 1 | 0.33 | PTGS2 | 11 | 2.60 | AWAT1; CYP1A1; CYP1A2; CYP2A6; CYP2C9; CYP2D6; CYP2J2; CYP4A11; CYP4F12; EPHX2; PTGIS | 0 | 0.00 | | 0 | 0.00 | | 2 | 1.02 | CYP4A11; CYP4F12 | 1 | 0.57 | PTGS2 |
| chloride channel complex: GO | 50 | 1 | 0.33 | GABRQ | 12 | 2.83 | BEST2; BEST3; BEST4; CFTR; CLCNKA; CLCNKB; CLIC5; GABRA2; GABRB3; GABRG3; GABRP; GLRB | 0 | 0.00 | | 0 | 0.00 | | 2 | 1.02 | CLIC5; GLRB | 1 | 0.57 | SLC26A6 |
| trans golgi network: GO | 179 | 7 | 0.65 | AP1S3; CHAC1; MYO1B; | 8 | 0.53 | CABP7; CLVS1; CLVS2; | 0 | 0.00 | | 0 | 0.00 | | 6 | 0.85 | HLA-DQB2; LGR5; NBEA; RHOBTB3; | 5 | 0.79 | AP1S3; MYO1B; RAB31; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | RAB10; RAB31; RAB38; RGS20 | | | LGR5; RBFOX1; RHOBTB3; SOD3; SYT17 | | | | | | | | | SOD3; SYT17 | | | RAB38; RGS20 |
| regulation of phosphatase activity: GO | 116 | 4 | 0.58 | IFNG; PKMYT1; PPP2R2C; PPP4R4 | 11 | 1.12 | CAMSAP3; CHP2; CRY2; DLG2; ELFN2; GPLD1; MAGI2; PCDH11X; PPP2R2B; SLC7A14; TSKS | 0 | 0.00 | | 1 | 3.60 | SPOCD1 | 4 | 0.88 | CHP2; CRY2; DLG2; GPLD1 | 3 | 0.73 | LMTK3; PKMYT1; PPP2R2C |
| ppara activates gene expression | 116 | 3 | 0.43 | HMGCR; TEAD4; TNFRSF21 | 9 | 0.92 | AGT; CYP1A1; CYP1A2; CYP4A11; CYP4B1; GOS2; HMGCS2; PEX11A; PPARGC1A | 0 | 0.00 | | 0 | 0.00 | | 5 | 1.10 | CTGF; CYP4A11; CYP4B1; HMGCS2; PPARGC1A | 3 | 0.73 | ANGPTL4; TEAD4; TRIB3 |
| regulation of muscle cell differentiation: GO | 148 | 9 | 1.02 | CCL17; CXCL10; CXCL9; EREG; FOXF1; GREM1; IL4R; NEU2; NRG1 | 15 | 1.20 | BCL2; BHLHE41; BOC; CAMK1; CDON; DKK1; FLT3LG; HDAC5; MESP1; MSTN; MYOCD; NKX2-5; RBM24; SCGB3A1; SOX8 | 0 | 0.00 | | 1 | 2.82 | CXCL9 | 8 | 1.37 | BCL2; BHLHA15; BHLHE41; CAMK1; CDON; MESP1; PRICKLE1; SHOX2 | 4 | 0.77 | EREG; IGFBP3; NRG1; PPARD |
| insulin signaling pathway | 148 | 8 | 0.90 | CALML3; CALML5; EIF4EBP1; | 14 | 1.12 | ACACB; CALML6; IRS2; IRS4; | 1 | 2.82 | PRKAR2B | 0 | 0.00 | | 4 | 0.69 | PHKG1; PPARGC1A; PRKAA2; | 4 | 0.77 | EIF4EBP1; HK2; PKM; SOCS3 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | HK2; NRAS; PKM; PYGL; SOCS3 | | | PCK1; PHKG1; PPARGC1A; PRKAA2; PRKAR2B; PYGM; SHC2; SHC3; SLC2A4; SORBS1 | | | | | | | | | SHC2 | | | |
| toll like receptor signaling pathway: GO | 84 | 5 | 1.00 | CTSB; MYD88; S100A14; TLR10; TNIP3 | 1 | 0.14 | COLEC12 | 0 | 0.00 | | 0 | 0.00 | | 0 | 0.00 | | 2 | 0.68 | MYD88; S100A14 |
| receptor signaling protein serine threonine kinase activity: GO | 84 | 2 | 0.40 | MAPK6; TGFBR1 | 5 | 0.70 | ACVR1C; AMHR2; MAPK15; MAPK4; PAK3 | 1 | 4.97 | ACVR1C | 0 | 0.00 | | 1 | 0.30 | PAK3 | 2 | 0.68 | BMPR1B; MAPK6 |
| regulation of neurotransmitter levels: GO | 180 | 9 | 0.84 | CHRNA3; GDNF; HRH3; HSPA8; RIMS3; SLC38A1; TH; UNC13A; WNT7A | 29 | 1.90 | APBA1; ATP1A2; CADPS; CAMK2A; DRD1; DRD4; GABRA2; GCHFR; GRIK5; KCNMB4; MAOA; NLGN1; NRXN1; NRXN3; P2RX7; PCLO; PPP1R9A; RAB3B; RIMS1; RPH3AL; SLC17A7; SLC6A2; SNCA; SNCG; | 0 | 0.00 | | 0 | 0.00 | | 10 | 1.41 | ALDH5A1; APBA1; NRXN1; PCLO; RAB3B; RIMS1; SLC18A2; SNCA; SYN2; SYT17 | 5 | 0.79 | HSPA8; SLC18A3; TH; UNC13A; WNT7A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | | | | SYN2; SYT1; SYT17; SYT8; SYT9 | | | | | | | | | | | | |
| negative regulation of cellular response to growth factor stimulus: GO | 117 | 7 | 1.00 | CXCL13; GREM1; HSPA5; LTBP1; SULF2; TGFBR1; WNT5A | 10 | 1.01 | AGT; CHRDL1; DKK1; GREM2; NOG; SKOR1; SKOR2; SLIT2; TMPRSS6; VWC2L | 0 | 0.00 | | 0 | 0.00 | | 6 | 1.30 | CHRD; DCN; GREM2; SLIT2; SPRY1; VWC2 | 3 | 0.73 | HSPA5; WNT5A; XDH |
| nucleotidyl-transferase activity: GO | 117 | 6 | 0.86 | OAS1; OAS2; OAS3; OASL; POLQ; POLR3G | 2 | 0.20 | GALT; TERT | 0 | 0.00 | | 0 | 0.00 | | 1 | 0.22 | NMNAT3 | 3 | 0.73 | OAS1; POLQ; POLR3G |
| neuron spine: GO | 117 | 3 | 0.43 | CDK5R1; LRRC4; NTSR1 | 18 | 1.82 | ACTN2; ADORA1; ANKS1B; APBB1; ATP1A2; DRD1; DRD4; GRIA1; GRID2IP; GRIN1; KCND2; LAMA2; NLGN1; P2RX6; PALM; PPP1R9A; PRKAR2B; SHANK1 | 1 | 3.57 | PRKAR2B | 0 | 0.00 | | 6 | 1.30 | GRIA1; GRID2IP; KCND2; LAMA2; LPAR1; PALM | 3 | 0.73 | CDK5R1; LRRC4; NTSR1 |
| copper ion binding: GO | 51 | 5 | 1.64 | HEPHL1; IL1A; PRNP; S100A12; SCO2 | 7 | 1.62 | ALB; AOC3; CP; DCT; S100A5; SNCA; SOD3 | 0 | 0.00 | | 0 | 0.00 | | 3 | 1.49 | CP; SNCA; SOD3 | 1 | 0.56 | SCO2 |
| destabilization of mrna by auf1 hnrnp d0 | 51 | 5 | 1.64 | HSPA8; PSMA4; PSMA5; PSMB6; | 0 | 0.00 | | 0 | 0.00 | | 0 | 0.00 | | 0 | 0.00 | | 1 | 0.56 | HSPA8 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | PSMD1 | | | | | | | | | | | | | | | |
| global genome nucleotide excision repair (gg-ner) | 51 | 4 | 1.31 | ACTB; PCNA; RUVBL1; UBE2N | 0 | 0.00 | | 0 | 0.00 | | 0 | 0.00 | | 0 | 0.00 | | 1 | 0.56 | ACTB |
| positive regulation of extrinsic apoptotic signaling pathway: GO | 51 | 4 | 1.31 | PDIA3; PYCARD; TNFRSF12A; TNFSF10 | 3 | 0.69 | AGT; GOS2; TIMP3 | 0 | 0.00 | | 0 | 0.00 | | 0 | 0.00 | | 1 | 0.56 | BMPR1B |
| amino acid activation: GO | 51 | 3 | 0.98 | EPRS; GARS; TARS | 0 | 0.00 | | 0 | 0.00 | | 0 | 0.00 | | 0 | 0.00 | | 1 | 0.56 | TARS |
| pcp/ce pathway | 51 | 3 | 0.98 | PSMA5; PSMB6; WNT5A | 1 | 0.23 | FZD4 | 0 | 0.00 | | 0 | 0.00 | | 1 | 0.50 | FZD7 | 1 | 0.56 | WNT5A |
| fatty acid beta oxidation: GO | 51 | 0 | 0.00 | | 6 | 1.39 | ABCD2; ACADL; ACOX2; ADIPOQ; CRAT; LEP | 2 | 16.39 | ABCD2; ADIPOQ | 0 | 0.00 | | 1 | 0.50 | ACOX2 | 1 | 0.56 | PPARD |
| ligand dependent nuclear receptor transcription coactivator activity: GO | 51 | 0 | 0.00 | | | 0.69 | ACTN2; CALCOCO1; PPARGC1A | 0 | 0.00 | | 0 | 0.00 | | 2 | 1.00 | FGF2; PPARGC1A | 1 | 0.56 | ACTN1 |
| colorectal cancer | 85 | 4 | 0.79 | BIRC5; CYCS; RAC2; TGFBR1 | 5 | 0.69 | ACVR1C; BCL2; FZD4; FZD8; TCF7L1 | 1 | 4.92 | ACVR1C | 1 | 4.92 | RAC2 | 3 | 0.90 | BCL2; FZD7; TCF7L1 | 2 | 0.67 | BIRC5; CYCS |
| regulation of lipid metabolism by peroxisome proliferator-activated receptor alpha (pparalpha) | 85 | 3 | 0.59 | HMGCR; TEAD4; TNFRSF21 | 9 | 1.25 | AGT; CYP1A1; CYP1A2; CYP4A11; CYP4B1; GOS2; HMGCS2; PEX11A; PPARGC1A | 0 | 0.00 | | 0 | 0.00 | | 5 | 1.49 | CTGF; CYP4A11; CYP4B1; HMGCS2; PPARGC1A | 2 | 0.67 | TEAD4; TRIB3 |
| collagen trimer: GO | 85 | 0 | 0.00 | | 20 | 2.78 | ADIPOQ; C1QL4; | 1 | 4.92 | ADIPOQ | 0 | 0.00 | | 9 | 2.69 | C1QTNF7; CCBE1; | 2 | 0.67 | COL17A1; SFTPA2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | C1QTNF7; CCBE1; COL11A1; COL11A2; COL19A1; COL20A1; COL21A1; COL24A1; COL25A1; COL28A1; COL9A2; COLEC11; COLEC12; EDA; EMID1; FCN2; MARCO; TNXB | | | | | | | | | COL11A1; COL21A1; COL24A1; COL28A1; DCN; EMILIN1; GLDN | | | |
| negative regulation of neuron differentiation: GO | 181 | 7 | 0.65 | ASPM; CALR; CDK5R1; IL1B; PLK2; SEMA4B; WNT5A | 20 | 1.30 | ADCY6; APOE; CNTN4; DTX1; FEZF2; ID4; LMX1A; LRP4; NLGN1; PAX6; PLXNA3; SEMA3A; SEMA3B; SEMA3D; SEMA3E; SEMA3G; SLIT2; SOX8; SPOCK1; ZNF536 | 0 | 0.00 | | 1 | 2.31 | IL1B | 6 | 0.84 | DPYSL3; LPAR1; SEMA3E; SEMA4G; SLIT2; SPOCK1 | 5 | 0.78 | ASPM; CDK5R1; PLK2; SEMA4B; WNT5A |
| positive regulation of wnt signaling pathway: GO | 150 | 11 | 1.23 | ASPM; DEPDC1B; JUP; PSMA4; PSMA5; PSMB6; PSMD1; | 7 | 0.55 | DACT1; DKK2; EDA; FGF9; GPC3; LGR5; TERT | 0 | 0.00 | | 0 | 0.00 | | 3 | 0.51 | DACT1; GPRC5B; LGR5 | 4 | 0.76 | ASPM; DEPDC1B; WNT5A; WNT7A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | PSME3; SULF2; WNT5A; WNT7A | | | | | | | | | | | | | | | |
| cellular lipid catabolic process: GO | 150 | 6 | 0.67 | AKR1B10; FABP5; FABP6; LIPG; NEU2; PLA2G4D | 13 | 1.02 | ABCD2; ACADL; ACOX2; ADIPOQ; APOE; CRAT; CYP4A11; CYP4F12; FABP4; FABP7; LEP; LPL; PNPLA3 | 3 | 8.36 | ABCD2; ADIPOQ; LPL | 0 | 0.00 | | 6 | 1.02 | ACER1; ACOX2; ALDH3A2; CYP4A11; CYP4F12; PNPLA3 | 4 | 0.76 | AKR1B10; FABP5; PLA2G4D; PPARD |
| alpha beta t cell activation: GO | 52 | 6 | 1.93 | ANXA1; EOMES; IFNG; IL12B; IL6; RSAD2 | 2 | 0.45 | BCL2; RORC | 0 | 0.00 | | 0 | 0.00 | | 1 | 0.49 | BCL2 | 1 | 0.55 | BCL3 |
| positive regulation of striated muscle cell differentiation: GO | 52 | 5 | 1.61 | CXCL9; GREM1; IL4R; NEU2; NRG1 | 5 | 1.13 | BCL2; FLT3LG; MESP1; MYOCD; SCGB3A1 | 0 | 0.00 | | 1 | 8.04 | CXCL9 | 3 | 1.47 | BCL2; MESP1; SHOX2 | 1 | 0.55 | NRG1 |
| ventricular septum development: GO | 52 | 4 | 1.29 | LTBP1; PRDM1; STRA6; WNT5A | 4 | 0.91 | NKX2-5; TBX5; WNT11; ZFPM2 | 0 | 0.00 | | 0 | 0.00 | | 2 | 0.98 | WNT11; ZFPM2 | 1 | 0.55 | WNT5A |
| iron uptake and transport | 52 | 3 | 0.97 | HMOX1; HMOX2; LCN2 | 7 | 1.59 | ATP6V0A4; ATP6V0E2; ATP6V1B1; CP; CYBRD1; SLC22A17; TF | 0 | 0.00 | | 0 | 0.00 | | 7 | 3.42 | ATP6V0A4; ATP6V0E2; CP; CYBRD1; SLC22A17; SLC40A1; STEAP2 | 1 | 0.55 | HMOX2 |
| mesonephric tubule morphogenesis: GO | 52 | 3 | 0.97 | GDNF; GREM1; PGF | 10 | 2.27 | ADAMTS16; BCL2; FGF1; GPC3; NOG; OSR1; PTCH1; SIX1; TCF21; WNT11 | 0 | 0.00 | | 0 | 0.00 | | 5 | 2.44 | BCL2; FGF2; OSR1; PTCH1; WNT11 | 1 | 0.55 | WNT9B |
| negative | 52 | 3 | 0.97 | FBXO5; OSM; | 4 | 0.91 | ACVR1C; | 1 | 8.04 | ACVR1C | 1 | 8.04 | OSM | 1 | 0.49 | ZFPM2 | 1 | 0.55 | WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| regulation of reproductive process: GO | | | | WNT5A | | | LIF; NR5A1; ZFPM2 | | | | | | | | | | | | |
| cell cell communication | 52 | 2 | 0.64 | CDH3; KIRREL2 | 5 | 1.13 | ACTN2; CLDN18; CLDN8; DSCAML1; MAGI2 | 0 | 0.00 | | 0 | 0.00 | | 2 | 0.98 | CLDN18; CLDN8 | 1 | 0.55 | COL17A1 |
| cleavage of growing transcript in the termination region | 52 | 2 | 0.64 | SNRPF; SNRPG | 0 | 0.00 | | 0 | 0.00 | | 0 | 0.00 | | 0 | 0.00 | | 1 | 0.55 | DDX39A |
| rna polymerase ii core promoter sequence specific dna binding: GO | 52 | 2 | 0.64 | H2AFZ; STAT1 | 4 | 0.91 | GATA1; PAX6; SOX8; TFAP2B | 0 | 0.00 | | 0 | 0.00 | | 0 | 0.00 | | 1 | 0.55 | H2AFZ |
| sh3 sh2 adaptor activity: GO | 52 | 2 | 0.64 | SH2D2A; SHB | 4 | 0.91 | ARHGAP6; GRB14; IRS4; SORBS1 | 0 | 0.00 | | 0 | 0.00 | | 0 | 0.00 | | 1 | 0.55 | SHB |
| intrinsic component of golgi membrane: GO | 52 | 1 | 0.32 | ST8SIA2 | 3 | 0.68 | B4GALNT2; CHST12; CHST5 | 0 | 0.00 | | 0 | 0.00 | | 2 | 0.98 | CHST12; STEAP2 | 1 | 0.55 | ST8SIA2 |
| kit pathway | 52 | 1 | 0.32 | STAT1 | 2 | 0.45 | BCL2; MITF | 0 | 0.00 | | 0 | 0.00 | | 2 | 0.98 | BCL2; MITF | 1 | 0.55 | SNAI2 |
| mechanism of gene regulation by peroxisome proliferators via ppara(alpha) | 52 | 1 | 0.32 | PTGS2 | 4 | 0.91 | LPL; NOS2; PPARGC1A; PRKAR2B | 2 | 16.07 | LPL; PRKAR2B | 0 | 0.00 | | 1 | 0.49 | PPARGC1A | 1 | 0.55 | PTGS2 |
| regulation of histone methylation: GO | 52 | 1 | 0.32 | HIST1H1B | 1 | 0.23 | TET1 | 0 | 0.00 | | 0 | 0.00 | | 1 | 0.49 | TET1 | 1 | 0.55 | HIST1H1B |
| transmission of nerve impulse: GO | 52 | 1 | 0.32 | CNTNAP2 | 11 | 2.50 | DRD1; GRM7; KCNA1; KCNA2; KCND2; KCNMB4; MYH14; | 0 | 0.00 | | 0 | 0.00 | | 3 | 1.47 | KCND2; SCN7A; SPTBN4 | 1 | 0.55 | CNTNAP2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | OTOA; P2RX1; SCN7A; SPTBN4 | | | | | | | | | | | | |
| toll-like receptor signaling pathway | 86 | 10 | 1.95 | CCL3; CD80; CXCL10; CXCL11; CXCL9; IL12B; IL1B; IL6; MYD88; STAT1 | 1 | 0.14 | IFNA5 | 0 | 0.00 | | 2 | 9.72 | CXCL9; IL1B | 0 | 0.00 | | 2 | 0.66 | CXCL11; MYD88 |
| ovulation cycle process: GO | 86 | 3 | 0.58 | ADCYAP1; CCNE1; EREG | 11 | 1.51 | BCL2; FZD4; INHBB; LEP; LHCGR; MSTN; NOBOX; NPY5R; NR5A1; SLIT2; SLIT3 | 0 | 0.00 | | 0 | 0.00 | | 5 | 1.48 | BCL2; ESR1; FOXC1; SLIT2; SLIT3 | 2 | 0.66 | BMPR1B; EREG |
| potassium channel complex: GO | 86 | 2 | 0.39 | CNTNAP2; KCNK1 | 16 | 2.19 | ABCC8; DLG2; DPP6; KCNA1; KCNA2; KCNA4; KCNB1; KCNB2; KCND2; KCNIP1; KCNIP2; KCNJ1; KCNJ3; KCNMB4; KCNT2; KCNU1 | 0 | 0.00 | | 0 | 0.00 | | 6 | 1.77 | ABCC9; DLG2; DPP6; KCND2; KCNK2; KCNT2 | 2 | 0.66 | CNTNAP2; KCNK1 |
| cofactor biosynthetic process: GO | 151 | 7 | 0.78 | ACOT7; COQ2; ELOVL7; KYNU; MTHFD2; NAMPT; PNP | 12 | 0.94 | ACACB; ACOT1; ACOT12; ACSBG1; ACSF2; ALAS2; ASPDH; | 0 | 0.00 | | 0 | 0.00 | | 2 | 0.34 | NMNAT3; PPOX | 4 | 0.75 | ACOT7; NAMPT; PDSS1; PNP |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | ELOVL2; HAAO; MAT1A; PPOX; SCD5 | | | | | | | | | | | | |
| localization within membrane: GO | 119 | 5 | 0.70 | AREG; CD2; CTSC; SERPINA1; TGFA | 13 | 1.29 | APOE; DLG2; FOLR1; GLRB; GRIA1; GRIK5; LRP4; MAGI2; NLGN1; NRXN1; REEP2; RELN; TRAPPC6A | 0 | 0.00 | | 0 | 0.00 | | 8 | 1.71 | CNIH3; DLG2; GLRB; GRIA1; NRXN1; RELN; RFTN2; TRAPPC6A | 3 | 0.71 | AGRN; AREG; TGFA |
| muscle cell development: GO | 119 | 5 | 0.70 | CCNB1; CDK1; CXADR; HOMER1; SDC1 | 23 | 2.28 | ACTA1; ACTN2; AGT; ANK2; C16orf89; CACNA2D2; CASQ2; DMD; FHOD3; LDB3; LMOD1; MYH11; MYH3; MYOCD; MYOZ1; NKX2-5; OBSCN; SGCG; SGCZ; SORBS2; TMOD1; TPM1; WFIKKN1 | 2 | 7.02 | SGCG; WFIKKN1 | 0 | 0.00 | | 4 | 0.85 | CACNA2D2; LMOD1; SGCZ; SORBS2 | 3 | 0.71 | CCNB1; CDK1; HOMER1 |
| respiratory electron transport | 87 | 3 | 0.58 | COX7B; CYCS; SCO2 | 1 | 0.14 | MTND5P10 | 0 | 0.00 | | 0 | 0.00 | | 0 | 0.00 | | 2 | 0.65 | CYCS; SCO2 |
| segmentation: GO | 87 | 3 | 0.58 | FOXF1; RGS20; WNT5A | 8 | 1.08 | COBL; DKK1; IRX1; KAT2A; | 0 | 0.00 | | 0 | 0.00 | | 4 | 1.17 | FOXC1; HOXD8; MEOX2; | 2 | 0.65 | RGS20; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | MEOX2; OSR1; SEMA3A; TDRD5 | | | | | | | | | OSR1 | | | |
| cell killing: GO | 53 | 11 | 3.47 | CAMP; CTSC; PRDX1; RAET1E; RAET1L; S100A12; SLAMF7; TREM1; ULBP1; ULBP2; ULBP3 | 6 | 1.34 | ALB; CLEC2A; DCD; ELANE; HAMP; KLRF2 | 0 | 0.00 | | 2 | 15.77 | GZMB; TREM1 | 4 | 1.92 | CTSG; DCD; ELANE; KLRF2 | 1 | 0.54 | RAET1L |
| cd8 ter pathway | 53 | 4 | 1.26 | CD3E; CD80; NRAS; PRKCQ | 1 | 0.22 | TRPV6 | 0 | 0.00 | | 1 | 7.88 | LCP2 | 0 | 0.00 | | 1 | 0.54 | PRKCQ |
| regulation of kidney development: GO | 53 | 4 | 1.26 | GDNF; GREM1; SERPINB7; STAT1 | 8 | 1.78 | ADIPOQ; AGT; LIF; NOG; OSR1; PDGFD; SIX1; SOX8 | 1 | 7.88 | ADIPOQ | 0 | 0.00 | | 1 | 0.48 | OSR1 | 1 | 0.54 | WNT9B |
| aspartate family amino acid metabolic process: GO | 53 | 2 | 0.63 | AHCY; GOT2 | 2 | 0.45 | ASPA; BHMT2 | 0 | 0.00 | | 0 | 0.00 | | 2 | 0.96 | ASPA; NMNAT3 | 1 | 0.54 | GOT2 |
| circadian regulation of gene expression: GO | 53 | 2 | 0.63 | NAMPT; USP2 | 6 | 1.34 | BHLHE41; CARTPT; CRY2; PER1; PPARGC1A; RORC | 0 | 0.00 | | 0 | 0.00 | | 3 | 1.44 | BHLHE41; CRY2; PPARGC1A | 1 | 0.54 | NAMPT |
| vibrio cholerae infection | 53 | 2 | 0.63 | ACTB; SEC61G | 4 | 0.89 | ATP6V0A4; ATP6V0E2; ATP6V1B1; CFTR | 0 | 0.00 | | 0 | 0.00 | | 2 | 0.96 | ATP6V0A4; ATP6V0E2 | 1 | 0.54 | ACTB |
| nuclear transcribed mrna catabolic process deadenylation dependent decay: GO | 53 | 1 | 0.32 | EIF4A3 | 0 | 0.00 | | 0 | 0.00 | | 0 | 0.00 | | 0 | 0.00 | | 1 | 0.54 | EIF4A3 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| smad protein signal transduction: GO | 53 | 1 | 0.32 | SUB1 | 8 | 1.78 | ATOH8; BMP3; BMP5; GDF10; GDF5; INHBB; MAGI2; MSTN | 0 | 0.00 | | 0 | 0.00 | | 2 | 0.96 | ATOH8; GDF7 | 1 | 0.54 | SUB1 |
| unsaturated fatty acid biosynthetic process: GO | 53 | 1 | 0.32 | PTGS2 | 6 | 1.34 | ELOVL2; FADS2; GGT7; PLA2G5; PTGIS; SCD5 | 0 | 0.00 | | 0 | 0.00 | | 0 | 0.00 | | 1 | 0.54 | PTGS2 |
| hormone receptor binding: GO | 152 | 9 | 0.99 | ADCYAP1; CALR; CCNE1; HIF1A; NR4A3; OASL; PCNA; PTHLH; RAN | 3 | 0.23 | LEP; PPARGC1A; TCF21 | 0 | 0.00 | | 0 | 0.00 | | 1 | 0.17 | PPARGC1A | 4 | 0.75 | HIF1A; PTHLH; RAN; UCN2 |
| lipoprotein metabolic process: GO | 120 | 9 | 1.26 | CWH43; LDLR; LYPLA1; OAS2; OLR1; PCSK9; PIGW; PLAUR; SDC1 | 6 | 0.59 | ALB; APOC1; APOE; LPL; NPC1L1; ZDHHC15 | 1 | 3.48 | LPL | 0 | 0.00 | | 1 | 0.21 | ZDHHC15 | 3 | 0.71 | LDLR; PCSK9; PIGW |
| multicellular organismal signaling: GO | 120 | 7 | 0.98 | CNTNAP2; CXADR; DSC2; DSP; GJA1; JUP; KCNK1 | 21 | 2.06 | ANK2; ATP1A2; CACNA1F; CACNA2D1; CACNA2D2; CACNB1; CASQ2; CTNNA3; DRD1; GRM7; KCNA1; KCNA2; KCND2; KCNIP1; | 0 | 0.00 | | 0 | 0.00 | | 8 | 1.69 | ATP1B2; CACNA1G; CACNA2D1; CACNA2D2; CACNB1; KCND2; SCN7A; SPTBN4 | 3 | 0.71 | CNTNAP2; DSC2; KCNK1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | | | | KCNIP2; KCNMB4; MYH14; OTOA; P2RX1; SCN7A; SPTBN4 | | | | | | | | | | | | |
| positive regulation of lipid metabolic process: GO | 120 | 7 | 0.98 | ANXA1; CCL21; IFNG; IL1B; LDLR; NR4A3; PTGS2 | 19 | 1.87 | ABCD2; ADIPOQ; AGT; AGTR1; APOC1; APOE; CYP17A1; ERBB4; FGF1; FGFR3; GPAM; GPLD1; HSD17B13; IRS2; MLXIPL; PLA2G6; PLIN5; PPARGC1A; SORBS1 | 3 | 10.45 | ABCD2; ADIPOQ; GPAM | 1 | 3.48 | IL1B | 6 | 1.27 | AGTR1; DGAT2; ERBB4; FGF2; GPLD1; PPARGC1A | 3 | 0.71 | LDLR; PTGS2; VAV2 |
| hormone mediated signaling pathway: GO | 153 | 5 | 0.55 | CALR; CCNE1; NR4A3; PAQR5; RAN | 17 | 1.31 | ADIPOQ; AR; CALCOCO1; ESRRG; GCGR; LHCGR; NR3C2; NR5A1; PGR; PPARGC1A; REN; RHOXF1; RORB; RORC; RXRG; SCGB2A1; TSHR | 1 | 2.73 | ADIPOQ | 0 | 0.00 | | 8 | 1.33 | ASIP; ESR1; ESRRG; NR2F1; NR3C2; PGR; PPARGC1A; TSHR | 4 | 0.74 | PAQR5; PPARD; RAN; SGK1 |
| regulation of oxidoreductase | 88 | 8 | 1.52 | CDH3; CYP27B1; | 11 | 1.47 | AGT; AGTR1; APOE; CNR1; | 0 | 0.00 | | 1 | 4.75 | IL1B | 4 | 1.15 | AGTR1; ESR1; | 2 | 0.64 | CYP27B1; HIF1A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| activity: GO | | | | GDNF; GZMA; HIF1A; IFNG; IL1B; LYPLA1 | | | CYGB; FCER2; GCHFR; LEP; PRKG2; SNCA; TERT | | | | | | | | | PRKG2; SNCA | | | |
| protein kinase complex: GO | 88 | 5 | 0.95 | CCND2; CCNE1; CDKN1A; PYCARD; TGFBR1 | 5 | 0.67 | ACVR1C; PHKG1; PRKAA2; PRKAR2B; SORBS1 | 2 | 9.50 | ACVR1C; PRKAR2B | 0 | 0.00 | | 3 | 0.87 | CDK14; PHKG1; PRKAA2 | 2 | 0.64 | CCND2; CDKN1A |
| long chain fatty acid metabolic process: GO | 88 | 2 | 0.38 | ACOT7; PTGS2 | 18 | 2.41 | ACADL; ACOT1; ACSBG1; AWAT1; CYP1A1; CYP1A2; CYP2A6; CYP2C9; CYP2D6; CYP2J2; CYP4A11; CYP4F12; ELOVL2; EPHX2; FADS2; PLP1; PTGIS; SLC27A6 | 1 | 4.75 | SLC27A6 | 0 | 0.00 | | 3 | 0.87 | CYP4A11; CYP4F12; PLP1 | 2 | 0.64 | ACOT7; PTGS2 |
| immunoregulatory interactions between a lymphoid and a non-lymphoid cell | 54 | 9 | 2.79 | CD1B; CXADR; FCGR1A; ICAM3; IFITM1; IFITM3; LILRA5; SELL; TREM1 | 2 | 0.44 | C3; COLEC12 | 0 | 0.00 | | 2 | 15.48 | IFITM3; TREM1 | 2 | 0.94 | C3; GULP1 | 1 | 0.53 | HLA-G |
| regulation of extrinsic apoptotic signaling pathway via death domain | 54 | 4 | 1.24 | HMOX1; SERPINE1; TNFRSF10A; TNFSF10 | 2 | 0.44 | BMP5; TIMP3 | 0 | 0.00 | | 1 | 7.74 | SERPINE1 | 0 | 0.00 | | 1 | 0.53 | BMPR1B |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| receptors: GO | | | | | | | | | | | | | | | | | | | |
| calcium dependent phospholipid binding: GO | 54 | 3 | 0.93 | ANXA1; ANXA3; DYSF | 7 | 1.53 | ANXA13; PCLO; RPH3AL; SYT1; SYT17; SYT8; SYT9 | 0 | 0.00 | | 1 | 7.74 | ANXA3 | 3 | 1.41 | ANXA9; PCLO; SYT17 | 1 | 0.53 | ANXA2P2 |
| platelet alpha granule lumen: GO | 54 | 3 | 0.93 | SERPINA1; SERPINE1; SRGN | 5 | 1.09 | ACTN2; ALB; CFD; CLU; EGF | 0 | 0.00 | | 1 | 7.74 | SERPINE1 | 3 | 1.41 | CLU; EGF; ISLR | 1 | 0.53 | ACTN1 |
| ire1 mediated unfolded protein response: GO | 54 | 2 | 0.62 | HSPA5; SEC61G | 1 | 0.22 | TSPYL2 | 0 | 0.00 | | 0 | 0.00 | | 0 | 0.00 | | 1 | 0.53 | HSPA5 |
| signaling by tgf-beta receptor complex | 54 | 2 | 0.62 | SERPINE1; TGFBR1 | 1 | 0.22 | CGN | 0 | 0.00 | | 1 | 7.74 | SERPINE1 | 1 | 0.47 | CGN | 1 | 0.53 | JUNB |
| vesicle docking: GO | 54 | 2 | 0.62 | NDRG4; UNC13A | 4 | 0.87 | CFTR; KCNB1; SYT1; TSNARE1 | 0 | 0.00 | | 0 | 0.00 | | 0 | 0.00 | | 1 | 0.53 | UNC13A |
| regulation of glucose import: GO | 54 | 1 | 0.31 | HK2 | 9 | 1.97 | ADIPOQ; ENPP1; GPC3; IRS2; LEP; OSTN; RARRES2; SLC1A2; SORBS1 | 1 | 7.74 | ADIPOQ | 0 | 0.00 | | 2 | 0.94 | ESR1; RARRES2 | 1 | 0.53 | HK2 |
| rna degradation | 54 | 1 | 0.31 | ENO1 | 0 | 0.00 | | 0 | 0.00 | | 0 | 0.00 | | 0 | 0.00 | | 1 | 0.53 | ENO1 |
| cell adhesion molecules (cams) | 122 | 12 | 1.65 | CD2; CD274; CD80; CDH3; CNTNAP2; CTLA4; ICAM3; ICOS; ITGA6; SDC1; SELE; SELL | 14 | 1.35 | CADM3; CD34; CDH4; CLDN16; CLDN18; CLDN8; ITGA8; MPZ; NCAM1; NEGR1; NLGN1; NRXN1; NRXN3; SDC2 | 0 | 0.00 | | 1 | 3.43 | SELE | 10 | 2.08 | CADM3; CD34; CLDN18; CLDN8; HLA-DQB2; JAM2; MPZ; NCAM1; NEGR1; NRXN1 | 3 | 0.70 | CNTNAP2; HLA-G; ITGA6 |
| negative | 122 | 8 | 1.10 | CCL21; | 13 | 1.26 | ADORA1; | 1 | 3.43 | GPAM | 0 | 0.00 | | 6 | 1.25 | ADRA2A; | 3 | 0.70 | NTSR1; PIF1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| regulation of homeostatic process: GO | | | | CCL3; CCR5; GSTO1; HMGCR; NTSR1; PIF1; UBASH3B | | | ADRA2A; BCL2; CARTPT; CASQ2; CLDN18; GPAM; GSTM2; JPH2; NOL3; P2RX7; TRDN; TSC22D3 | | | | | | | | | BCL2; CLDN18; FGF2; TRDN; TSC22D3 | | | UBASH3B |
| spliceosome | 122 | 6 | 0.82 | EIF4A3; HSPA6; HSPA8; PPIL1; SNRPF; SNRPG | 1 | 0.10 | HSPA1L | 0 | 0.00 | | 0 | 0.00 | | 0 | 0.00 | | 3 | 0.70 | EIF4A3; HSPA8; PPIL1 |
| phosphoric diester hydrolase activity: GO | 89 | 5 | 0.94 | BDKRB2; CCR5; FAM83B; HMOX1; PDIA3 | 11 | 1.46 | ADORA1; CCKBR; CHRM1; CHRM3; ENPP1; GPLD1; PDE11A; PDE9A; PLCB4; PLCH2; PLCXD3 | 0 | 0.00 | | 0 | 0.00 | | 8 | 2.28 | CHRM1; CHRM3; ENPP3; GPLD1; PDE1A; PDE9A; PLCB4; PLCZ1 | 2 | 0.64 | BDKRB2; PLCD4 |
| response to bmp: GO | 89 | 0 | 0.00 | | 11 | 1.46 | BMP3; BMP5; CHRDL1; GATA5; GDF10; GREM2; LRP4; NKX2-5; NOG; TMEM100; TNMD | 0 | 0.00 | | 0 | 0.00 | | 4 | 1.14 | CHRD; GDF7; GREM2; TNMD | 2 | 0.64 | BMPR1B; DSG4 |
| regulation of jnk cascade: GO | 155 | 11 | 1.19 | CCL21; F2RL1; GSTP1; IL1A; | 10 | 0.76 | AMBP; BIRC7; DACT1; | 0 | 0.00 | | 1 | 2.70 | IL1B | 3 | 0.49 | CTGF; DACT1; FZD7 | 4 | 0.73 | GSTP1; MDFI; WNT5A; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | IL1B; MDFI; PYCARD; SERPINB3; SLAMF1; WNT5A; WNT7A | | | EPHB1; FZD4; FZD8; MAPK8IP1; NOX1; PER1; TNXB | | | | | | | | | | | | WNT7A |
| detection of light stimulus: GO | 55 | 5 | 1.52 | CNGB1; ELOVL4; GNGT2; PITPNM1; SDR16C5 | 2 | 0.43 | CACNA1F; GUCA1B | 0 | 0.00 | | 0 | 0.00 | | 0 | 0.00 | | 1 | 0.52 | PITPNM1 |
| excitatory extracellular ligand gated ion channel activity: GO | 55 | 4 | 1.22 | CHRNA3; CHRNA6; CHRNA9; HTR3A | 16 | 3.43 | CHRNA2; GABRP; GLRB; GRIA1; GRIA2; GRIA4; GRIK3; GRIK4; GRIK5; GRIN1; GRIN2A; HTR3E; P2RX1; P2RX6; P2RX7; SLC17A7 | 1 | 7.60 | GRIA4 | 0 | 0.00 | | 4 | 1.85 | GLRB; GRIA1; GRIA2; GRIK3 | 1 | 0.52 | CHRNA6 |
| steroid hormone biosynthesis | 55 | 4 | 1.22 | SULT2B1; UGT1A1; UGT1A10; UGT1A7 | 7 | 1.50 | CYP17A1; CYP1A1; CYP21A2; CYP3A5; HSD11B1; UGT2A1; UGT2B7 | 1 | 7.60 | HSD11B2 | 0 | 0.00 | | 3 | 1.39 | CYP3A4; CYP3A5; SULT1E1 | 1 | 0.52 | SULT2B1 |
| regulation of phosphoprotein phosphatase activity: GO | 55 | 2 | 0.61 | PPP2R2C; PPP4R4 | 3 | 0.64 | CRY2; MAGI2; PPP2R2B | 0 | 0.00 | | 0 | 0.00 | | 1 | 0.46 | CRY2 | 1 | 0.52 | PPP2R2C |
| electron transport chain: GO | 90 | 3 | 0.56 | COX7B; CYCS; SCO2 | 4 | 0.52 | GPD1; PPARGC1A; SNCA; | 1 | 4.64 | GPD1 | 0 | 0.00 | | 3 | 0.85 | ALDH5A1; PPARGC1A; SNCA | 2 | 0.63 | CYCS; SCO2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | WDR93 | | | | | | | | | | | | |
| regulation of camp metabolic process: GO | 124 | 10 | 1.35 | ADCYAP1; CAP1; CXCL10; CXCL11; CXCL9; GNAI3; GPR65; GPR87; INSL3; PTHLH | 18 | 1.71 | ADCY2; ADCY5; ADCY6; ADCY8; ADRA2A; ADRB1; AKAP12; CALCR; DRD1; DRD4; GALR1; GRM7; LHCGR; OXER1; PALM; SCT; TSHR; VIPR2 | 1 | 3.37 | MRAP2 | 1 | 3.37 | CXCL9 | 6 | 1.23 | ADCYAP1R1; ADRA2A; AKAP12; LPAR1; PALM; TSHR | 3 | 0.69 | CAP1; CXCL11; PTHLH |
| calcium ion transmembrane transporter activity: GO | 124 | 3 | 0.40 | CHRNA9; PANX1; TRPC4 | 20 | 1.90 | ATP2A1; ATP2B2; CACNAIF; CACNA1H; CACNA2D1; CACNA2D2; CACNB1; GRIN1; GRIN2A; GRM7; ILIRAPL 1; JPH2; MCOLN3; PKD1; PKD1L2; SLC24A2; TMC2; TRPM1; TRPM3; TRPV6 | 0 | 0.00 | | 0 | 0.00 | | 8 | 1.64 | ATP2C2; CACNA1G; CACNA1H; CACNA2D1; CACNA2D2; CACNB1; PKD1L2; TRPC1 | 3 | 0.69 | PANX1; TMC1; TRPV3 |
| activating transcription factor binding: GO | 56 | 3 | 0.90 | EOMES; IFI27; TBX20 | 3 | 0.63 | ATOH8; BHLHE41; HAND2 | 0 | 0.00 | | 0 | 0.00 | | 3 | 1.36 | ATOH8; BHLHE41; HAND2 | 1 | 0.51 | IFI27 |
| hiv-i nef: negative effector | 56 | 2 | 0.60 | LMNB1; LMNB2 | 2 | 0.42 | BCL2; GSN | 0 | 0.00 | | 0 | 0.00 | | 1 | 0.45 | BCL2 | 1 | 0.51 | LMNB2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| of fas and tnf | | | | | | | | | | | | | | | | | | | |
| positive regulation of lyase activity: GO | 56 | 2 | 0.60 | ADCYAP1; CAP1 | 12 | 2.53 | ADCY2; ADCY5; ADCY6; ADCY8; ADRB1; CALCR; DRD1; GUCA1B; LHCGR; NOS2; TSHR; VIPR2 | 0 | 0.00 | | 0 | 0.00 | | 1 | 0.45 | TSHR | 1 | 0.51 | CAP1 |
| ppara pathway | 56 | 1 | 0.30 | PTGS2 | 4 | 0.84 | LPL; NOS2; PPARGC1A; PRKAR2B | 2 | 14.92 | LPL; PRKAR2B | 0 | 0.00 | | 2 | 0.91 | NR2F1; PPARGC1A | 1 | 0.51 | PTGS2 |
| carbohydrate homeostasis: GO | 157 | 13 | 1.39 | GJB6; GK; HIF1A; HK2; IL1B; IL6; NME1; OAS1; PLAU; PLSCR3; PYGL; SLC16A1; TH | 24 | 1.80 | ADIPOQ; ADRA1B; ADRA2A; CARTPT; CNR1; CRY2; DHPS; GCGR; GRIK5; IRS2; KCNB1; LEP; LEPR; MLXIPL; PAX6; PCK1; PDK4; PPARGC1A; PRKAA2; PTCH1; RBP4; RPH3AL; SLC2A4; TFAP2B | 1 | 2.66 | ADIPOQ | 2 | 5.32 | FFAR2; IL1B | 13 | 2.10 | ADRA2A; BHLHA15; CRY2; FOXA1; GPRC5B; IGFBP5; PDK3; PDK4; PPARGC1A; PRKAA2; PTCH1; SLC18A2; SLC29A1 | 4 | 0.72 | HIF1A; HK2; OAS1; TH |
| positive regulation of cell morphogenesis involved in differentiation: GO | 157 | 11 | 1.17 | C1QBP; CALR; CRABP2; GDNF; LPAR3; LRP8; NEFL; NGF; NRG1; | 12 | 0.90 | ALX1; CAMK2B; CDH4; EEF2K; IL1RAPL1; LIF; MAPT; MYOC; | 0 | 0.00 | | 0 | 0.00 | | 7 | 1.13 | CXCL12; MAPT; MYOC; PAK3; RELN; SHOX2; SLIT2 | 4 | 0.72 | CRABP2; NGF; NRG1; SGK1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | SERPINB3; TNFRSF12A | | | NTRK3; PAK3; RELN; SLIT2 | | | | | | | | | | | | |
| alpha amino acid catabolic process: GO | 91 | 8 | 1.47 | AHCY; ALDH4A1; GOT2; HAL; IDO1; IL4I1; KYNU; TDO2 | 9 | 1.17 | ALDH1L1; ASPA; CARNS1; CDO1; GPT; HAAO; HOGA1; NOS2; PRODH | 0 | 0.00 | | 1 | 4.59 | TDO2 | 4 | 1.12 | ASPA; GPT; HDC; PRODH | 2 | 0.62 | GLDC; GOT2 |
| positive regulation of cation transmembrane transport: GO | 91 | 8 | 1.47 | ATP1B3; BDKRB1; CXCL10; CXCL11; CXCL9; GSTO1; NPSR1; NTSR1 | 13 | 1.69 | ACTN2; ANK2; CACNA2D1; DMD; DRD1; DRD4; EDN3; FGF14; GSTM2; JPH2; SNCA; TRDN; WNK2 | 0 | 0.00 | | 1 | 4.59 | CXCL9 | 8 | 2.23 | ATP1B2; CACNA2D1; EDN3; GLRX; SNCA; TESC; TRDN; TRPC1 | 2 | 0.62 | CXCL11; NTSR1 |
| tcr signaling | 91 | 6 | 1.10 | CD3E; ENAH; PRKCQ; PSMA5; PSMB6; UBE2N | 0 | 0.00 | | 0 | 0.00 | | 1 | 4.59 | LCP2 | 0 | 0.00 | | 2 | 0.62 | ENAH; PRKCQ |
| regulation of glucose transport: GO | 91 | 3 | 0.55 | HK2; IL1B; NR4A3 | 10 | 1.30 | ADIPOQ; C3; ENPP1; GPC3; IRS2; LEP; OSTN; RARRES2; SLC1A2; SORBS1 | 1 | 4.59 | ADIPOQ | 1 | 4.59 | IL1B | 3 | 0.84 | C3; ESR1; RARRES2 | 2 | 0.62 | HK2; TRIB3 |
| actin filament based movement: GO | 91 | 2 | 0.37 | GJA1; MYO1B | 19 | 2.46 | ACTA1; ACTN2; ANK2; CACNA2D1; DES; DMD; MYBPC1; MYH14; MYH3; MYL3; | 0 | 0.00 | | 0 | 0.00 | | 3 | 0.84 | CACNA2D1; TNNC1; TNNT3 | 2 | 0.62 | MYO1B; TPM4 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | MYL4; TMOD1; TNNC1; TNNC2; TNNI2; TNNT2; TNNT3; TPM1; TPM2 | | | | | | | | | | | | |
| enhancer binding: GO | 91 | 2 | 0.37 | ACTB; H2AFZ | 10 | 1.30 | BACH2; FOXN4; GATA1; GATA5; MEOX2; MESP1; NR5A1; SOX10; TFAP2B; ZBTB16 | 0 | 0.00 | | 0 | 0.00 | | 3 | 0.84 | BACH2; MEOX2; MESP1 | 2 | 0.62 | ACTB; H2AFZ |
| regulation of regulated secretory pathway: GO | 125 | 8 | 1.07 | F2RL1; FOXF1; HMOX1; IL13RA2; IL4R; PTAFR; RAC2; RIMS3 | 13 | 1.23 | ADRA2A; CACNA1H; GRIK5; KCNB1; NLGN1; PRAM1; RPH3AL; SPINK1; SYT1; SYT17; SYT8; SYT9; TRPV6 | 0 | 0.00 | | 1 | 3.34 | RAC2 | 4 | 0.81 | ADRA2A; CACNA1G; CACNA1H; SYT17 | 3 | 0.68 | IL13RA2; PTAFR; SERPINA10 |
| regulation of ion homeostasis: GO | 190 | 16 | 1.41 | BAK1; BDKRB1; CA2; CCK; CCL21; CCL3; CCR5; CXCL10; CXCL11; CXCL9; GJA1; GSTO1; IFI6; NPSR1; NTSR1; | 19 | 1.18 | ADORA1; AGT; AGTR1; ANK2; ATP1A2; BCL2; CASQ2; DMD; DRD1; FHL1; GSTM2; JPH2; MYOC; NOL3; P2RX7; | 0 | 0.00 | | 1 | 2.20 | CXCL9 | 12 | 1.60 | ADCYAP1R1; AGTR1; BCL2; CACNA1G; CORIN; DCN; FGF2; HRC; MYOC; SNCA; TRDN; TRPC1 | 5 | 0.75 | BAK1; CA2; CXCL11; NTSR1; UBASH3B |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | UBASH3B | | | SLC30A10; SNCA; TRDN; WNK2 | | | | | | | | | | | | |
| endoplasmic reticulum lumen: GO | 190 | 12 | 1.06 | ARSH; CALR; CTSC; HSPA5; PDIA3; PLAUR; PPIB; PTGS2; SDF2L1; SERPINA1; WNT5A; WNT7A | 16 | 0.99 | CASQ2; CES1; COL11A1; COL11A2; COL19A1; COL20A1; COL21A1; COL24A1; COL25A1; COL28A1; COL9A2; CYP2W1; F10; F7; PDGFD; TRDN | 0 | 0.00 | | 0 | 0.00 | | 9 | 1.20 | CES1; COL11A1; COL21A1; COL24A1; COL28A1; CYP2W1; FKBP7; HRC; TRDN | 5 | 0.75 | COL17A1; HSPA5; PTGS2; WNT5A; WNT7A |
| ecm glycoproteins | 190 | 5 | 0.44 | LAMB3; LTBP1; NELL2; TNC; WISP1 | 37 | 2.30 | ABI3BP; ADIPOQ; AMELX; CILP; CILP2; COCH; DPT; EDIL3; ELN; EMID1; FBLN5; HMCN2; IGSF10; LAMA2; LAMB4; LAMC3; LGI3; LGI4; MATN4; MFAP4; MFAP5; MGP; NDNF; NTN5; PCOLCE2; RELN; SLIT2; SLIT3; SMOC1; | 2 | 4.40 | ADIPOQ; CILP | 0 | 0.00 | | 29 | 3.88 | ABI3BP; COCH; CTGF; DPT; EDIL3; ELN; EMILIN1; FBLN1; FBLN2; FBLN5; FRAS1; GLDN; HMCN2; IGFBP5; LAMA2; LAMC3; LGI4; MATN4; NDNF; NTN4; NTN5; PCOLCE; RELN; SLIT2; SLIT3; SPARCL1; SVEP1; TNN; | 5 | 0.75 | AGRN; IGFBP3; LAMB3; LRG1; NELL2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | A: Fold Change (FC) Up | A: Up-regulated Genes | A: Down-regulated | A: Fold Change (FC) | A: Down-regulated Genes | B. Differentially expressed genes significant in the baseline vs week 12 comparison only in the placebo: Up-regulated | B: Fold Change (FC) Up | B: Up-regulated Genes | B: Down-regulated | B: Fold Change (FC) | B: Down-regulated Genes | C. Differentially expressed genes significant in the baseline vs week 12 comparison only in the nemo: Up-regulated | C: Fold Change (FC) Up | C: Up-regulated Genes | C: Down-regulated | C: Fold Change (FC) | C: Down-regulated Genes |
|---|---|---|---|---|---|---|---|---|---|---|---|---|---|---|---|---|---|---|---|
| | | | | | | | SSPO; SVEP1; TNN; TNXB; TSPEAR; VIT; VWDE; WISP2 | | | | | | | | | WISP2 | | | |
| spliceosomal complex: GO | 158 | 5 | 0.53 | EIF4A3; HSPA8; PPIL1; SNRPF; SNRPG | 1 | 0.07 | SNRPN | 0 | 0.00 | | 0 | 0.00 | | 1 | 0.16 | SNRPN | 4 | 0.72 | DDX39A; EIF4A3; HSPA8; PPIL1 |
| shp2 pathway | 57 | 9 | 2.64 | GNAI3; IFNG; IL2RA; IL6; JAK3; NGF; NRAS; NTRK1; STAT1 | 3 | 0.62 | EGF; NTRK3; SDC2 | 0 | 0.00 | | 1 | 7.33 | IL2RA | 2 | 0.89 | ANGPT1; EGF | 1 | 0.50 | NGF |
| glutathione metabolic process: GO | 57 | 7 | 2.05 | CHAC1; CHAC2; CNDP2; GGCT; GLO1; GSTO1; GSTP1 | 9 | 1.86 | CLIC5; GGT7; GSTA3; GSTM2; GSTM3; GSTM5; GSTT2; GSTT2B; NAT8 | 0 | 0.00 | | 0 | 0.00 | | 3 | 1.34 | ALDH5A1; CLIC5; GSTM5 | 1 | 0.50 | GSTP1 |
| positive regulation of tumor necrosis factor superfamily cytokine production: GO | 57 | 7 | 2.05 | CCL3; CD2; IFNG; IL12B; PTAFR; PYCARD; SASH3 | 1 | 0.21 | CLU | 0 | 0.00 | | 0 | 0.00 | | 2 | 0.89 | CLU; ZBTB20 | 1 | 0.50 | PTAFR |
| autodegradation of cdh1 by cdh1 apc c | 57 | 5 | 1.47 | PSMA4; PSMA5; PSMB6; PSMD1; UBE2C | 0 | 0.00 | | 0 | 0.00 | | 0 | 0.00 | | 0 | 0.00 | | 1 | 0.50 | UBE2C |
| myosin binding: GO | 57 | 4 | 1.17 | CXCR4; PYCARD; RAB10; RAB25 | 10 | 2.07 | ACTA1; AMPD1; DMD; GSN; MYL3; MYL4; | 0 | 0.00 | | 0 | 0.00 | | 4 | 1.78 | MYOC; MYRIP; RAB3B; SPATA6 | 1 | 0.50 | IQGAP3 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | MYL9; MYOC; NPC1L1; RAB3B | | | | | | | | | | | | |
| peptide n acetyltransferase activity: GO | 57 | 1 | 0.29 | BRCA2 | 1 | 0.21 | KAT2A | 0 | 0.00 | | 0 | 0.00 | | 0 | 0.00 | | 1 | 0.50 | BRCA2 |
| proteoglycan biosynthetic process: GO | 57 | 1 | 0.29 | HS3ST3B1 | 6 | 1.24 | BCAN; CHST12; EXTL1; HS3ST5; HS6ST3; UST | 0 | 0.00 | | 0 | 0.00 | | 5 | 2.23 | CHST12; DCN; DSEL; GAL3ST4; UST | 1 | 0.50 | BMPR1B |
| fatty acid derivative metabolic process: GO | 92 | 4 | 0.73 | CYP4F22; PDPN; PLA2G3; PTGS2 | 14 | 1.80 | AWAT1; CYP1A1; CYP1A2; CYP2A6; CYP2C9; CYP2D6; CYP2J2; CYP4A11; CYP4F12; CYP4F8; EPHX2; GGT7; PLA2G5; PTGIS | 0 | 0.00 | | 0 | 0.00 | | 2 | 0.55 | CYP4A11; CYP4F12 | 2 | 0.62 | PLA2G3; PTGS2 |
| regulation of muscle system process: GO | 191 | 12 | 1.05 | CHRNA3; DSC2; DSP; GSTO1; JUP; MYLK2; NMU; NR4A3; PROK2; PTAFR; PTGS2; ZC3H12A | 37 | 2.29 | ADRA1A; ADRA1B; ADRA2A; AGT; ANK2; ATP1A2; ATP2A1; CAMK2B; CASQ2; CHRM1; CHRM2; CHRM3; CNN1; CTNNA3; DMD; GSTM2; | 0 | 0.00 | | 0 | 0.00 | | 14 | 1.86 | ADRA1A; ADRA2A; CHRM1; CHRM3; CTGF; HRC; HSPB6; IGFBP5; LMCD1; PDE9A; PPARGC1A; PRKG1; TNNC1; TNNT3 | 5 | 0.74 | DSC2; NMU; PTAFR; PTGS2; ZC3H12A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | HSPB6; KCNA1; KCNB2; MSTN; MYBPH; MYL3; MYL9; MYOCD; NKX2-5; NOL3; P2RX1; PDE9A; PPARGC1A; SLN; TNNC1; TNNC2; TNNI2; TNNT2; | | | | | | | | | | | | |
| udp glycosyl-transferase activity: GO | 126 | 10 | 1.33 | B3GNT3; B3GNT5; GALNT14; GALNT6; GCNT4; HAS3; UGCG; UGT1A1; UGT1A10; UGT1A7 | 15 | 1.40 | A4GNT; ABO; B3GALT1; B3GALT5; B4GALNT2; EXTL1; GALNT13; GALNT8; GALNTL6; GXYLT2; GYG2; HAS1; UGT2A1; UGT2B7; UGT3A2 | 0 | 0.00 | | 0 | 0.00 | | 3 | 0.60 | ABO; B3GALT1; GXYLT2 | 3 | 0.68 | B3GNT5; GALNT14; GALNT6 |
| nuclear import: GO | 126 | 9 | 1.20 | HTATIP2; IFNG; JAK3; KPNA2; PDIA3; RAN; RANBP1; SNRPF; SNRPG | 6 | 0.56 | AGT; DRD1; EGF; FGF9; GDF5; TXNIP | 0 | 0.00 | 0 | | 0.00 | | 3 | 0.60 | EGF; PRICKLE1; TXNIP | 3 | 0.68 | BCL3; KPNA2; RAN |
| phosphatidyl-inositol binding: GO | 192 | 6 | 0.52 | ADAP2; ARAP2; MYO1B; | 13 | 0.80 | ACTN2; APBA1; ARHGAP33; | 0 | 0.00 | | 1 | 2.18 | SNX20 | 4 | 0.53 | APBA1; SCIN; STXBP6; | 5 | 0.74 | ADAP2; MARK1; MYO1B; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | PFN1; RACGAP1; TWF1 | | | CLVS1; CLVS2; JPH2; KCNJ1; MCF2L; SCIN; SNX21; STXBP6; SYT1; TTPA | | | | | | | | | TUB | | | PFN1; TWF1 |
| myeloid leukocyte migration: GO | 93 | 17 | 3.06 | ANXA1; CCL17; CCL18; CCL21; CCL22; CCL3; CCL7; CXADR; CXCL3; IFNG; IL1B; IL6; S100A12; S100A8; S100A9; SCG2; TREM1 | 4 | 0.51 | CCL14; EDN3; FOLR2; MITF | 0 | 0.00 | | 2 | 8.99 | IL1B; TREM1 | 3 | 0.82 | CCL14; EDN3; MITF | 2 | 0.61 | CCL20; HRH1 |
| positive regulation of t cell proliferation: GO | 93 | 17 | 3.06 | ANXA1; CD274; CD3E; CD80; EBI3; IFNG; IL12B; IL1B; IL2RA; IL6; JAK3; PNP; PRKCQ; PYCARD; SASH3; SLAMF1; TNFSF9 | 3 | 0.38 | DHPS; GPAM; LEP | 1 | 4.49 | GPAM | 2 | 8.99 | IL1B; IL2RA | 0 | 0.00 | | 2 | 0.61 | PNP; PRKCQ |
| disorders of transmembrane transporters | 93 | 7 | 1.26 | ABCA12; GK; PSMA5; PSMB6; SLC16A1; SLC2A1; SLC2A9 | 6 | 0.76 | ABCA3; ABCB11; ALB; CP; SLC4A4; SLC7A9 | 0 | 0.00 | | 0 | 0.00 | | 4 | 1.09 | ABCA3; CP; SLC40A1; SLC4A4 | 2 | 0.61 | SLC2A1; SLC2A9 |
| antigen processing ubiquitination | 93 | 3 | 0.54 | PSMA4; PSMD1; | 5 | 0.63 | ASB11; ASB16; ASB4; | 0 | 0.00 | | 0 | 0.00 | | 0 | 0.00 | | 2 | 0.61 | ASB15; UBE2S |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| proteasome degradation | | | | UBE2S | | | FBXO44; SPSB4 | | | | | | | | | | | | |
| n acyltransferase activity: GO | 93 | 3 | 0.54 | BRCA2; CERS3; ESCO2 | 6 | 0.76 | ALAS2; GLYAT; HRASLS5; KAT2A; NAT8; NAT8L | 1 | 4.49 | HRASLS5 | 0 | 0.00 | | 0 | 0.00 | | 2 | 0.61 | BRCA2; NAGS |
| rna 3 end processing: GO | 93 | 1 | 0.18 | EIF4A3 | 0 | 0.00 | | 0 | 0.00 | | 0 | 0.00 | | 0 | 0.00 | | 2 | 0.61 | DDX39A; EIF4A3 |
| pigment metabolic process: GO | 58 | 5 | 1.44 | HMOX1; HMOX2; UGT1A1; UGT1A10; UGT1A7 | 7 | 1.42 | ALAS2; AMBP; BCL2; DCT; OCA2; PPARGC1A; PPOX | 0 | 0.00 | | 0 | 0.00 | | 5 | 2.19 | ASIP; BCL2; PPARGC1A; PPOX; TRPC1 | 1 | 0.49 | HMOX2 |
| calcium dependent protein binding: GO | 58 | 4 | 1.15 | ANXA1; ANXA3; PLSCR3; S100A11 | 7 | 1.42 | CASQ2; FCN2; NRXN1; SYT1; SYT8; TNNC1; TNNT3 | 0 | 0.00 | | 1 | 7.21 | ANXA3 | 3 | 1.31 | NRXN1; TNNC1; TNNT3 | 1 | 0.49 | S100P |
| er associated ubiquitin dependent protein catabolic process: GO | 58 | 4 | 1.15 | HSPA5; SDF2L1; VCP; YOD1 | 0 | 0.00 | | 0 | 0.00 | | 0 | 0.00 | | 0 | 0.00 | | 1 | 0.49 | HSPA5 |
| regulation of neurotransmitter transport: GO | 58 | 4 | 1.15 | CHRNA3; GDNF; RIMS3; UNC13A | 12 | 2.44 | ATP1A2; CAMK2A; DRD1; DRD4; GRIK5; KCNMB4; NLGN1; PPP1R9A; RAB3B; RIMS1; SNCA; SNCG | 0 | 0.00 | | 0 | 0.00 | | 4 | 1.75 | RAB3B; RIMS1; SLC18A2; SNCA | 1 | 0.49 | UNC13A |
| regulation of pathway restricted smad protein phosphorylation: | 58 | 3 | 0.87 | GREM1; TGFBR1; TTK | 8 | 1.63 | BMP3; BMP5; DKK1; GDF10; GDF5; INHBB; | 0 | 0.00 | | 0 | 0.00 | | 1 | 0.44 | GDF7 | 1 | 0.49 | TTK |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| GO | | | | | | | MSTN; NOG | | | | | | | | | | | | |
| nucleolar part: GO | 58 | 2 | 0.58 | NOP10; RPP40 | 1 | 0.20 | CLEC3B | 1 | 7.21 | CLEC3B | 0 | 0.00 | | 0 | 0.00 | | 1 | 0.49 | NOP56 |
| membrane depolarization: GO | 58 | 1 | 0.29 | CHRNA6 | 10 | 2.03 | ADIPOQ; ANK2; ATP1A2; BEST2; CACNA1F; CACNA1H; CACNA2D1; NALCN; P2RX7; SCN7A | 1 | 7.21 | ADIPOQ | 0 | 0.00 | | 5 | 2.19 | CACNA1G; CACNA1H; CACNA2D1; NALCN; SCN7A | 1 | 0.49 | CHRNA6 |
| fak pathway | 58 | 0 | 0.00 | | 1 | 0.20 | ACTA1 | 0 | 0.00 | | 0 | 0.00 | | 0 | 0.00 | | 1 | 0.49 | ACTN1 |
| sensory perception of taste: GO | 58 | 0 | 0.00 | | 3 | 0.61 | CA6; PIP; REEP2 | 0 | 0.00 | | 0 | 0.00 | | 3 | 1.31 | CA6; PIP; SCNN1B | 1 | 0.49 | SCNN1D |
| protein transporter activity: GO | 94 | 4 | 0.71 | AP1S3; KPNA2; SEC61G; TIMM23 | 3 | 0.38 | CALCR; GPIHBP1; MLC1 | 0 | 0.00 | | 0 | 0.00 | | 0 | 0.00 | | 2 | 0.60 | AP1S3; KPNA2 |
| natural killer cell mediated cytotoxicity | 128 | 13 | 1.70 | CSF2; FCGR3B; IFNG; KIR2DL4; NRAS; RAC2; RAET1E; RAET1L; TNFRSF10A; TNFSF10; ULBP1; ULBP2; ULBP3 | 4 | 0.37 | CHP2; IFNA5; SHC2; SHC3 | 0 | 0.00 | | 3 | 9.79 | GZMB; RAC2 LCP2; | 2 | 0.40 | CHP2; SHC2 | 3 | 0.66 | HLA-G; RAET1L; VAV2 |
| macromitophagy: GO | 128 | 9 | 1.18 | EIF2S1; FCGR3B; FGFBP1; HK2; NEFM; RIMS3; SERPINB10; SNRPF; TREM1 | 13 | 1.20 | BOC; CLVS1; GDF5; HCAR1; KRT15; KRT73; MAP1A; MSTN; MYH11; | 1 | 3.26 | KRT73 | 1 | 3.26 | TREM1 | 5 | 0.99 | AKR1E2; LMCD1; MYOM1; PRKG1; STK32A | 3 | 0.66 | FGFBP1; HK2; NEFM |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | MYOM1; OBSCN; PHYHIP; STK32A | | | | | | | | | | | | |
| fas pathway | 59 | 2 | 0.57 | LMNB1; LMNB2 | 0 | 0.00 | | 0 | 0.00 | | 0 | 0.00 | | 0 | 0.00 | | 1 | 0.48 | LMNB2 |
| late endosome: GO | 194 | 11 | 0.95 | CD79A; CXCR4; DYSF; GJA1; HSPA8; IFITM3; LDLR; LRAT; NTRK1; PCSK9; RAB31 | 7 | 0.43 | MAGI2; NAPSA; SFTPC; SLC2A4; TF; TTPA; VPS37D | 0 | 0.00 | | 1 | 2.15 | IFITM3 | 2 | 0.26 | CLCN4; SLC40A1 | 5 | 0.73 | HSPA8; LDLR; LRAT; PCSK9; RAB31 |
| striated muscle cell differentiation: GO | 162 | 7 | 0.72 | CALR; CCNB1; CDK1; CXADR; HOMER1; NRG1; SDC1 | 26 | 1.89 | ACTA1; ACTN2; AGT; C16orf89; CACNA1H; CACNA2D2; CASQ2; CDON; DMD; FHOD3; KAT2A; LDB3; LMOD1; MESP1; MYEF2; MYH11; MYH3; MYOCD; MYOZ1; NKX2-5; OBSCN; SORBS2; TBX5; TMOD1; TPM1; WFIKKN1 | 1 | 2.58 | WFIKKN1 | 0 | 0.00 | | 7 | 1.10 | CACNA1H; CACNA2D2; CDON; IGFBP5; LMOD1; MESP1; SORBS2 | 4 | 0.70 | CCNB1; CDK1; HOMER1; NRG1 |
| extrinsic component of | 95 | 6 | 1.06 | GNA15; GNAI3; | 7 | 0.87 | DTNA; GNAZ; | 1 | 4.40 | RGS11 | 0 | 0.00 | | 1 | 0.27 | GNG11 | 2 | 0.60 | GNA15; RGS1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| cytoplasmic side of plasma membrane: GO | | | | GNGT2; JAK3; RACGAP1; RGS1 | | | KCNIP1; MCF2L; RGS11; RGS6; RGS9 | | | | | | | | | | | | |
| ubiquitin like protein specific protease activity: GO | 95 | 4 | 0.70 | USP2; USP43; YOD1; ZC3H12A | 3 | 0.37 | USP17L2; USP17L7; USP6 | 0 | 0.00 | | 0 | 0.00 | | 1 | 0.27 | USP17L7 | 2 | 0.60 | USP43; ZC3H12A |
| monocarboxylic acid catabolic process: GO | 95 | 2 | 0.35 | ALDH4A1; GOT2 | 12 | 1.49 | ABCD2; ACADL; ACOX2; ADIPOQ; CRAT; CYP4A11; CYP4F12; HOGA1; IDUA; LEP; PON3; PRODH | 2 | 8.80 | ABCD2; ADIPOQ | 0 | 0.00 | | 7 | 1.87 | ACOX2; ALDH3A2; ALDH5A1; CYP4A11; CYP4F12; PON3; PRODH | 2 | 0.60 | GOT2; PPARD |
| immunoglobulin receptor binding: GO | 20 | 4 | 3.35 | IGHG1; IGHG2; IGHG4; IGKC | 0 | 0.00 | | 2 | 41.79 | IGHG1; IGKV3-20 | 0 | 0.00 | | 2 | 2.54 | IGHM; IGHV3-23 | 0 | 0.00 | |
| regulation of t cell cytokine production: GO | 20 | 3 | 2.51 | RSAD2; SASH3; SLAMF1 | 0 | 0.00 | | 0 | 0.00 | | 0 | 0.00 | | 0 | 0.00 | | 0 | 0.00 | |
| response to interferon beta: GO | 20 | 3 | 2.51 | IFITM1; IFITM3; STAT1 | 0 | 0.00 | | 0 | 0.00 | | 1 | 20.89 | IFITM3 | 0 | 0.00 | | 0 | 0.00 | |
| zinc ion homeostasis: GO | 20 | 3 | 2.51 | S100A8; S100A9; SLC39A6 | 0 | 0.00 | | 0 | 0.00 | | 0 | 0.00 | | 0 | 0.00 | | 0 | 0.00 | |
| adp signalling through p2ry12 | 20 | 2 | 1.67 | GNAI3; GNGT2 | 0 | 0.00 | | 0 | 0.00 | | 0 | 0.00 | | 1 | 1.27 | GNG11 | 0 | 0.00 | |
| assembly of the pre replicative complex | 20 | 2 | 1.67 | PSMA4; PSMD1 | 0 | 0.00 | | 0 | 0.00 | | 0 | 0.00 | | 0 | 0.00 | | 0 | 0.00 | |
| caspase activation via | 20 | 2 | 1.67 | TNFRSF10A; TNFSF10 | 0 | 0.00 | | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| extrinsic apoptotic signalling pathway | | | | | | | | | | | | | | | | | | | |
| inhibition of voltage gated ca2 channels via gbeta gamma subunits | 20 | 2 | 1.67 | GNGT2; KCNJ15 | 1 | 0.59 | KCNJ3 | 0 | 0.00 | | 0 | 0.00 | | 0 | 0.00 | | 0 | 0.00 | |
| macromolecule transmembrane transporter activity: GO | 20 | 2 | 1.67 | SEC61G; TIMM23 | 1 | 0.59 | GPIHBP1 | 0 | 0.00 | | 0 | 0.00 | | 0 | 0.00 | | 0 | 0.00 | |
| rna dependent dna biosynthetic process: GO | 20 | 2 | 1.67 | NOP10; PPIA | 1 | 0.59 | TERT | 0 | 0.00 | | 0 | 0.00 | | 0 | 0.00 | | 0 | 0.00 | |
| activin receptor signaling pathway: GO | 20 | 1 | 0.84 | TGFBR1 | 2 | 1.18 | ACVR1C; INHBB | 1 | 20.89 | ACVR1C | 0 | 0.00 | | 1 | 1.27 | GDF7 | 0 | 0.00 | |
| alkaloid biosynthesis ii | 20 | 1 | 0.84 | ESCO2 | 3 | 1.77 | AOC3; CES1; PNPLA3 | 0 | 0.00 | | 0 | 0.00 | | 2 | 2.54 | CES1; PNPLA3 | 0 | 0.00 | |
| bile acid biosynthetic process: GO | 20 | 1 | 0.84 | CH25H | 2 | 1.18 | ABCB11; ACOX2 | 0 | 0.00 | | 0 | 0.00 | | 1 | 1.27 | ACOX2 | 0 | 0.00 | |
| dna dealkylation: GO | 20 | 1 | 0.84 | APOBEC3A | 1 | 0.59 | TET1 | 0 | 0.00 | | 0 | 0.00 | | 1 | 1.27 | TET1 | 0 | 0.00 | |
| ecadherin keratinocyte pathway | 20 | 1 | 0.84 | JUP | 0 | 0.00 | | 0 | 0.00 | | 0 | 0.00 | | 0 | 0.00 | | 0 | 0.00 | |
| establishment of protein localization to golgi: GO | 20 | 1 | 0.84 | NRAS | 0 | 0.00 | | 0 | 0.00 | | 0 | 0.00 | | 0 | 0.00 | | 0 | 0.00 | |
| intramolecular oxidoreductase activity transposing s s bonds: GO | 20 | 1 | 0.84 | PDIA3 | 0 | 0.00 | | 0 | 0.00 | | 0 | 0.00 | | 0 | 0.00 | | 0 | 0.00 | |
| lymph vessel development: GO | 20 | 1 | 0.84 | PDPN | 2 | 1.18 | CCBE1; PKD1 | 0 | 0.00 | | 0 | 0.00 | | 2 | 2.54 | CCBE1; FOXC1 | 0 | 0.00 | |
| mrna splicing minor pathway | 20 | 1 | 0.84 | SNRPG | 0 | 0.00 | | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| negative regulation of antigen receptor mediated signaling pathway: GO | 20 | 1 | 0.84 | PRNP | 0 | 0.00 | | 0 | 0.00 | | 1 | 20.89 | GBP1 | 0 | 0.00 | | 0 | 0.00 | |
| negative regulation of protein localization to cell periphery: GO | 20 | 1 | 0.84 | LYPLA1 | 2 | 1.18 | ANXA13; PKDCC | 0 | 0.00 | | 1 | 20.89 | GBP1 | 1 | 1.27 | LRRC15 | 0 | 0.00 | |
| neuronal cell body membrane: GO | 20 | 1 | 0.84 | SLC4A8 | 4 | 2.36 | KCNA2; KCNB1; KCNB2; KCND2 | 0 | 0.00 | | 0 | 0.00 | | 1 | 1.27 | KCND2 | 0 | 0.00 | |
| phototransduction visible light: GO | 20 | 1 | 0.84 | CNGB1 | 0 | 0.00 | | 0 | 0.00 | | 0 | 0.00 | | 0 | 0.00 | | 0 | 0.00 | |
| positive regulation of circadian rhythm: GO | 20 | 1 | 0.84 | ARNTL2 | 3 | 1.77 | ALB; NLGN1; RORC | 0 | 0.00 | | 0 | 0.00 | | 0 | 0.00 | | 0 | 0.00 | |
| positive regulation of multicellular organismal metabolic process: GO | 20 | 1 | 0.84 | SERPINB7 | 1 | 0.59 | AMELX | 0 | 0.00 | | 0 | 0.00 | | 1 | 1.27 | CTGF | 0 | 0.00 | |
| positive regulation of natural killer cell mediated immunity: GO | 20 | 1 | 0.84 | IL12B | 0 | 0.00 | | 0 | 0.00 | | 0 | 0.00 | | 0 | 0.00 | | 0 | 0.00 | |
| protein k48 linked deubiquitination: GO | 20 | 1 | 0.84 | YOD1 | 1 | 0.59 | USP17L2 | 0 | 0.00 | | 0 | 0.00 | | 0 | 0.00 | | 0 | 0.00 | |
| muscle cell membrane | | | | | | | | | | | | | | | | | | | |
| regulation of cardiac | 20 | 1 | 0.84 | GJA1 | 2 | 1.18 | ANK2; CACNA2D1 | 0 | 0.00 | | 0 | 0.00 | | 1 | 1.27 | CACNA2D1 | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| muscle cell membrane repolarization: GO | | | | | | | | | | | | | | | | | | | |
| regulation of cholesterol efflux: GO | 20 | 1 | 0.84 | ABCA12 | 5 | 2.95 | ADIPOQ; APOE; EGF; PON1; PTCH1 | 1 | 20.89 | ADIPOQ | 0 | 0.00 | | 2 | 2.54 | EGF; PTCH1 | 0 | 0.00 | |
| regulation of establishment or maintenance of cell polarity: GO | 20 | 1 | 0.84 | KIF20B | 1 | 0.59 | GSN | 0 | 0.00 | | 0 | 0.00 | | 0 | 0.00 | | 0 | 0.00 | |
| regulation of feeding behavior: GO | 20 | 1 | 0.84 | NR4A3 | 3 | 1.77 | CNR1; DRD1; LEPR | 0 | 0.00 | | 0 | 0.00 | | 0 | 0.00 | | 0 | 0.00 | |
| regulation of synaptic vesicle exocytosis: GO | 20 | 1 | 0.84 | RIMS3 | 2 | 1.18 | GRIK5; NLGN1 | 0 | 0.00 | | 0 | 0.00 | | 0 | 0.00 | | 0 | 0.00 | |
| ruffle organization: GO | 20 | 1 | 0.84 | CCL21 | 2 | 1.18 | ARHGEF26; TPM1 | 0 | 0.00 | | 0 | 0.00 | | 1 | 1.27 | ARHGEF26 | 0 | 0.00 | |
| signaling by fgfr3 | 20 | 1 | 0.84 | NRAS | 2 | 1.18 | FGF1; FGFR3 | 0 | 0.00 | | 0 | 0.00 | | 0 | 0.00 | | 0 | 0.00 | |
| signaling by wnt in cancer | 20 | 1 | 0.84 | CSNK1A1 | 2 | 1.18 | DKK1; FZD4 | 0 | 0.00 | | 0 | 0.00 | | 0 | 0.00 | | 0 | 0.00 | |
| trachea development: GO | 20 | 1 | 0.84 | FOXF1 | 2 | 1.18 | EDA; HYDIN | 0 | 0.00 | | 0 | 0.00 | | 0 | 0.00 | | 0 | 0.00 | |
| triglyceride lipase activity: GO | 20 | 1 | 0.84 | LIPG | 2 | 1.18 | LPL; PNPLA3 | 1 | 20.89 | LPL | 0 | 0.00 | | 3 | 3.81 | LIPK; LIPM; PNPLA3 | 0 | 0.00 | |
| triglyceride metabolism | 20 | 1 | 0.84 | GK | 6 | 3.54 | AGMO; FABP4; GPAM; MOGAT1; MOGAT2; PNPLA3 | 1 | 20.89 | GPAM | 0 | 0.00 | | 2 | 2.54 | DGAT2; PNPLA3 | 0 | 0.00 | |
| trna processing | 20 | 1 | 0.84 | EPRS | 0 | 0.00 | | 0 | 0.00 | | 0 | 0.00 | | 0 | 0.00 | | 0 | 0.00 | |
| vesicle mediated transport between endosomal compartments: GO | 20 | 1 | 0.84 | HOOK1 | 0 | 0.00 | | 0 | 0.00 | | 0 | 0.00 | | 0 | 0.00 | | 0 | 0.00 | |
| adaptation of | 20 | 0 | 0.00 | | 1 | 0.59 | DNM1 | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| signaling pathway: GO | | | | | | | | | | | | | | | | | | | |
| alkali metal ion binding: GO | 20 | 0 | 0.00 | | 4 | 2.36 | ATP1A2; KCNA4; KCNJ1; SLC24A2 | 0 | 0.00 | | 0 | 0.00 | | 0 | 0.00 | | 0 | 0.00 | |
| axoneme part: GO | 20 | 0 | 0.00 | | 3 | 1.77 | CCDC114; DNAH6; HYDIN | 0 | 0.00 | | 0 | 0.00 | | 1 | 1.27 | CCDC114 | 0 | 0.00 | |
| bone growth: GO | 20 | 0 | 0.00 | | 4 | 2.36 | FGFR3; LEP; LEPR; OSTN | 0 | 0.00 | | 0 | 0.00 | | 2 | 2.54 | BNC2; DDR2 | 0 | 0.00 | |
| calcium independent cell cell adhesion via plasma membrane cell adhesion molecules: GO | 20 | 0 | 0.00 | | 3 | 1.77 | CLDN16; CLDN18; CLDN8 | 0 | 0.00 | | 0 | 0.00 | | 2 | 2.54 | CLDN18; CLDN8 | 0 | 0.00 | |
| cellular response to osmotic stress: GO | 20 | 0 | 0.00 | | 1 | 0.59 | SLC2A4 | 0 | 0.00 | | 0 | 0.00 | | 0 | 0.00 | | 0 | 0.00 | |
| dorsal spinal cord development: GO | 20 | 0 | 0.00 | | 1 | 0.59 | DRGX | 0 | 0.00 | | 0 | 0.00 | | 1 | 1.27 | GDF7 | 0 | 0.00 | |
| extracellular glutamate gated ion channel activity: GO | 20 | 0 | 0.00 | | 10 | 5.90 | GABRP; GRIA1; GRIA2; GRIA4; GRIK3; GRIK4; GRIK5; GRIN1; GRIN2A; SLC17A7 | 1 | 20.89 | GRIA4 | 0 | 0.00 | | 3 | 3.81 | GRIA1; GRIA2; GRIK3 | 0 | 0.00 | |
| genetic imprinting: GO | 20 | 0 | 0.00 | | 0 | 0.00 | | 1 | 20.89 | CDKN1C | 0 | 0.00 | | 1 | 1.27 | ASIP | 0 | 0.00 | |
| gmp metabolic process: GO | 20 | 0 | 0.00 | | 2 | 1.18 | DLG2; MPP2 | 0 | 0.00 | | 0 | 0.00 | | 2 | 2.54 | DLG2; MPP2 | 0 | 0.00 | |
| inner ear receptor stereocilium organization: GO | 20 | 0 | 0.00 | | 3 | 1.77 | ATP2B2; CLIC5; PDZD7 | 0 | 0.00 | | 0 | 0.00 | | 2 | 2.54 | CLIC5; PDZD7 | 0 | 0.00 | |
| intracellular lipid transport: GO | 20 | 0 | 0.00 | | 2 | 1.18 | ACACB; PRKAA2 | 0 | 0.00 | | 0 | 0.00 | | 1 | 1.27 | PRKAA2 | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| leukotriene biosynthetic process: GO | 20 | 0 | 0.00 | | 2 | 1.18 | GGT7; PLA2G5 | 0 | 0.00 | | 0 | 0.00 | | 0 | 0.00 | | 0 | 0.00 | |
| middle ear morphogenesis: GO | 20 | 0 | 0.00 | | 6 | 3.54 | FGFR1; GSC; NOG; OSR1; OSR2; SIX1 | 0 | 0.00 | | 0 | 0.00 | | 3 | 3.81 | FGFR1; OSR1; PRRX1 | 0 | 0.00 | |
| negative regulation of macroautophagy: GO | 20 | 0 | 0.00 | | 1 | 0.59 | NRBP2 | 0 | 0.00 | | 0 | 0.00 | | 0 | 0.00 | | 0 | 0.00 | |
| negative regulation of potassium ion transmembrane transport: GO | 20 | 0 | 0.00 | | 2 | 1.18 | ACTN2; CASQ2 | 0 | 0.00 | | 0 | 0.00 | | 0 | 0.00 | | 0 | 0.00 | |
| nucleus localization: GO | 20 | 0 | 0.00 | | 1 | 0.59 | SYNE1 | 0 | 0.00 | | 0 | 0.00 | | 1 | 1.27 | SYNE1 | 0 | 0.00 | |
| protein adp ribosylation: GO | 20 | 0 | 0.00 | | 1 | 0.59 | ART5 | 0 | 0.00 | | 0 | 0.00 | | 0 | 0.00 | | 0 | 0.00 | |
| regulation of neuron projection regeneration: GO | 20 | 0 | 0.00 | | 1 | 0.59 | NTRK3 | 0 | 0.00 | | 0 | 0.00 | | 1 | 1.27 | PRRX1 | 0 | 0.00 | |
| regulation of transcription involved in cell fate commitment: GO | 20 | 0 | 0.00 | | 3 | 1.77 | CHD5; PAX6; RORC | 0 | 0.00 | | 0 | 0.00 | | 0 | 0.00 | | 0 | 0.00 | |
| response to dietary excess: GO | 20 | 0 | 0.00 | | 6 | 3.54 | ACVR1C; ADRB1; APOE; CLIC5; LEP; PPARGC1A | 1 | 20.89 | ACVR1C | 0 | 0.00 | | 2 | 2.54 | CLIC5; PPARGC1A | 0 | 0.00 | |
| sodium independent organic anion transmembrane transporter activity: GO | 20 | 0 | 0.00 | | 3 | 1.77 | SLC22A9; SLCO4C1; SLCO5A1 | 0 | 0.00 | | 0 | 0.00 | | 0 | 0.00 | | 0 | 0.00 | |
| transcriptional regulation | 20 | 0 | 0.00 | | 2 | 1.18 | DKK1; HIF3A | 0 | 0.00 | | 0 | 0.00 | | 1 | 1.27 | HIF3A | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| of pluripotent stem cells | | | | | | | | | | | | | | | | | | | |
| voltage gated sodium channel activity: GO | 20 | 0 | 0.00 | | 1 | 0.59 | SCN7A | 0 | 0.00 | | 0 | 0.00 | | 1 | 1.27 | SCN7A | 0 | 0.00 | |
| wnt ca2 cyclic gmp pathway | 20 | 0 | 0.00 | | 3 | 1.77 | CAMK2A; CAMK2B; TF | 0 | 0.00 | | 0 | 0.00 | | 0 | 0.00 | | 0 | 0.00 | |
| regulation of mrna splicing via spliceosome: GO | 60 | 2 | 0.56 | C1QBP; HSPA8 | 3 | 0.59 | CELF4; RBFOX1; RBM11 | 0 | 0.00 | | 0 | 0.00 | | 0 | 0.00 | | 1 | 0.47 | HSPA8 |
| clathrin binding: GO | 60 | 1 | 0.28 | LDLR | 6 | 1.18 | NCALD; RPH3AL; SYT1; SYT17; SYT8; SYT9 | 0 | 0.00 | | 0 | 0.00 | | 2 | 0.85 | NCALD; SYT17 | 1 | 0.47 | LDLR |
| negative regulation of neuron death: GO | 163 | 10 | 1.03 | GDNF; HIF1A; HMOX1; IL6; KIF14; NEFL; NGF; NR4A3; NTRK1; SNCB | 16 | 1.16 | APOE; BCL2; CD34; CNTFR; GABRB3; GDF5; GRIN1; NDNF; NRBP2; PCP4; PPARGC1A; SIX1; SNCA; TFAP2B; TOX3; VSTM2L | 0 | 0.00 | | 0 | 0.00 | | 10 | 1.56 | ANGPT1; BCL2; CD34; CHL1; CNTFR; ESR1; MDK; NDNF; PPARGC1A; SNCA | 4 | 0.70 | HIF1A; KIF14; NGF; SNCB |
| divalent inorganic cation transmembrane transporter activity: GO | 163 | 6 | 0.62 | CHRNA9; NIPAL1; NIPAL4; PANX1; SLC39A6; TRPC4 | 22 | 1.59 | ATP2A1; ATP2B2; CACNA1F; CACNA1H; CACNA2D1; CACNA2D2; CACNB1; CLDN16; GRIN1; | 0 | 0.00 | | 0 | 0.00 | | 9 | 1.40 | ATP2C2; CACNA1G; CACNA1H; CACNA2D1; CACNA2D2; CACNB1; PKD1L2; SLC40A1; TRPC1 | 4 | 0.70 | NIPAL4; PANX1; TMC1; TRPV3 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | GRIN2A; GRM7; ILIRAPL1; JPH2; MCOLN3; PKD1; PKD1L2; SLC24A2; SLC30A10; TMC2; TRPM1; TRPM3; TRPV6 | | | | | | | | | | | | |
| hiv life cycle | 130 | 6 | 0.77 | CCR5; CXCR4; PPIA; RAN; RANBP1; RCC1 | 1 | 0.09 | VPS37D | 0 | 0.00 | | 0 | 0.00 | | 0 | 0.00 | | 3 | 0.65 | FEN1; PPIAP22; RAN |
| transferase activity transferring acyl groups other than amino acyl groups: GO | 196 | 9 | 0.77 | AGPAT5; BRCA2; CERS3; ELOVL7; ESCO2; LRAT; MBOAT2; PIGW; SPTSSA | 19 | 1.14 | ALAS2; AWAT1; AWAT2; CRAT; DGAT2L6; ELOVL2; GLYAT; GPAM; HRASLS5; KAT2A; MOGAT1; MOGAT2; NAT8; NAT8L; PNPLA3; SOAT2; ZDHHC11; ZDHHC11B; ZDHHC15 | 2 | 4.26 | GPAM; HRASLS5 | 0 | 0.00 | | 5 | 0.65 | DGAT2; PNPLA3; SPTSSB; ZDHHC11; ZDHHC15 | 5 | 0.72 | BRCA2; LPCAT1; LRAT; NAGS; PIGW |
| potassium channels | 96 | 4 | 0.70 | GNGT2; KCNJ15; KCNK1; KCNK10 | 11 | 1.35 | ABCC8; KCNA1; KCNA2; KCNA4; | 0 | 0.00 | | 0 | 0.00 | | 3 | 0.79 | ABCC9; KCND2; KCNK2 | 2 | 0.59 | KCNK1; KCNK10 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | KCNB1; KCNB2; KCND2; KCNH8; KCNJ1; KCNJ3; KCNMB4 | | | | | | | | | | | | |
| dna templated transcription termination: GO | 96 | 3 | 0.52 | EIF4A3; SNRPF; SNRPG | 0 | 0.00 | | 0 | 0.00 | | 0 | 0.00 | | 0 | 0.00 | | 2 | 0.59 | DDX39A; EIF4A3 |
| lipid modification: GO | 197 | 5 | 0.42 | ADH7; CD80; EREG; HBEGF; NRG1 | 25 | 1.50 | ABCD2; ACADL; ACOX2; ADIPOQ; B4GALNT2; BTC; CRAT; CYGB; EGF; EPHX2; ERBB4; FA2H; FGF1; FGF17; FGF22; FGF9; FGFR1; FGFR3; HAO2; IRS2; LEP; NRG2; PPARGC1A; PTPRQ; SOAT2 | 2 | 4.24 | ABCD2; ADIPOQ | 0 | 0.00 | | 9 | 1.16 | ACOX2; ALDH3A2; EGF; ERBB4; FGF2; FGF22; FGFR1; PIK3R6; PPARGC1A | 5 | 0.72 | EFR3B; EREG; HBEGF; NRG1; PPARD |
| collagen binding: GO | 61 | 5 | 1.37 | CTSB; ITGA3; MMP9; PPIB; SRGN | 8 | 1.55 | ABI3BP; CCBE1; CHADL; COCH; MAP1A; PCOLCE2; PODN; TNXB | 0 | 0.00 | | 0 | 0.00 | | 9 | 3.75 | ABI3BP; CCBE1; COCH; DCN; DDR2; ITGA11; LRRC15; PCOLCE; PODN | 1 | 0.46 | ITGA3 |
| influenza infection | 61 | 4 | 1.10 | CALR; ISG15; KPNA2; RPL22L1 | 0 | 0.00 | | 0 | 0.00 | | 1 | 6.85 | ISG15 | 0 | 0.00 | | 1 | 0.46 | KPNA2 |
| ar pathway | 61 | 2 | 0.55 | PA2G4; | 3 | 0.58 | AR; GSN; | 0 | 0.00 | | 0 | 0.00 | | 1 | 0.42 | MAK | 1 | 0.46 | PA2G4 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | PRDX1 | | | TMPRSS2 | | | | | | | | | | | | |
| negative regulation of nf kappab transcription factor activity: GO | 61 | 2 | 0.55 | PYCARD; ZC3H12A | 2 | 0.39 | PKHD1; PTGIS | 0 | 0.00 | | 0 | 0.00 | | 0 | 0.00 | | 1 | 0.46 | ZC3H12A |
| nucleoside monophosphate biosynthetic process: GO | 61 | 2 | 0.55 | TK1; UPP1 | 4 | 0.77 | AMPD1; ATP6V0A4; ENTPD8; UPP2 | 0 | 0.00 | | 0 | 0.00 | | 1 | 0.42 | ATP6V0A4 | 1 | 0.46 | TK1 |
| glial cell differentiation: GO | 131 | 5 | 0.64 | GSTP1; NRG1; S100A8; S100A9; TRPC4 | 20 | 1.80 | ADAM22; CLU; DRD1; DTX1; FA2H; GSN; ID4; KLF15; LAMA2; LAMC3; LGI4; LIF; MYOC; OLIG1; PAX6; PLP1; PRDM8; RELN; SOX10; SOX8 | 0 | 0.00 | | 0 | 0.00 | | 9 | 1.75 | ADAM22; CLU; LAMA2; LAMC3; LGI4; LPAR1; MYOC; PLP1; RELN | 3 | 0.65 | GSTP1; NDRG1; NRG1 |
| endoplasmic reticulum to cytosol transport: GO | 21 | 3 | 2.39 | CCL3; CCR5; VCP | 2 | 1.12 | NOL3; TRDN | 0 | 0.00 | | 0 | 0.00 | | 1 | 1.21 | TRDN | 0 | 0.00 | |
| sympathetic nervous system development: GO | 21 | 3 | 2.39 | GDNF; NTRK1; TP63 | 5 | 2.81 | GFRA3; HAND2; PLXNA4; SEMA3A; TFAP2B | 0 | 0.00 | | 0 | 0.00 | | 2 | 2.42 | HAND2; PLXNA4 | 0 | 0.00 | |
| threonine type peptidase activity: GO | 21 | 3 | 2.39 | PSMA4; PSMA5; PSMB6 | 1 | 0.56 | PRSS50 | 0 | 0.00 | | 0 | 0.00 | | 0 | 0.00 | | 0 | 0.00 | |
| drug transporter activity: GO | 21 | 2 | 1.59 | EBP: SLC38A1 | 2 | 1.12 | ABCA8; SLC19A3 | 0 | 0.00 | | 0 | 0.00 | | 2 | 2.42 | ABCB5; SLC19A3 | 0 | 0.00 | |
| glycogen metabolism | 21 | 2 | 1.59 | PGM2; PYGL | 1 | 0.56 | GYG2 | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| gtp metabolic process: GO | 21 | 2 | 1.59 | GNAI3; NME1 | 0 | 0.00 | | 0 | 0.00 | | 0 | 0.00 | | 0 | 0.00 | | 0 | 0.00 | |
| il 6 signaling pathway | 21 | 2 | 1.59 | IL6; JAK3 | 0 | 0.00 | | 0 | 0.00 | | 0 | 0.00 | | 0 | 0.00 | | 0 | 0.00 | |
| immunoglobulin binding: GO | 21 | 2 | 1.59 | FCGR1A; FCGR3B | 3 | 1.69 | AMBP; FCER2; PIP | 0 | 0.00 | | 0 | 0.00 | | 2 | 2.42 | MS4A2; PIP | 0 | 0.00 | |
| metanephric nephron morphogenesis: GO | 21 | 2 | 1.59 | GDNF; GREM1 | 2 | 1.12 | PKD1; SOX8 | 0 | 0.00 | | 0 | 0.00 | | 0 | 0.00 | | 0 | 0.00 | |
| activated tak1 mediates p38 mapk activation | 21 | 1 | 0.80 | UBE2N | 0 | 0.00 | | 0 | 0.00 | | 0 | 0.00 | | 0 | 0.00 | | 0 | 0.00 | |
| beta catenin destruction complex disassembly: GO | 21 | 1 | 0.80 | CSNK1A1 | 0 | 0.00 | | 0 | 0.00 | | 0 | 0.00 | | 0 | 0.00 | | 0 | 0.00 | |
| cell cell signaling involved in cardiac conduction: GO | 21 | 1 | 0.80 | GJA1 | 2 | 1.12 | ANK2; CASQ2 | 0 | 0.00 | | 0 | 0.00 | | 1 | 1.21 | CACNA1G | 0 | 0.00 | |
| cofactor transporter activity: GO | 21 | 1 | 0.80 | PDPN | 3 | 1.69 | FOLR1; FOLR2; SLC16A12 | 0 | 0.00 | | 0 | 0.00 | | 0 | 0.00 | | 0 | 0.00 | |
| ino80 type complex: GO | 21 | 1 | 0.80 | RUVBL1 | 0 | 0.00 | | 0 | 0.00 | | 0 | 0.00 | | 0 | 0.00 | | 0 | 0.00 | |
| mitochondrial trna aminoacylation | 21 | 1 | 0.80 | GARS | 0 | 0.00 | | 0 | 0.00 | | 0 | 0.00 | | 0 | 0.00 | | 0 | 0.00 | |
| negative regulation of organ growth: GO | 21 | 1 | 0.80 | GJA1 | 3 | 1.69 | NOG; RBP4; TBX5 | 0 | 0.00 | | 0 | 0.00 | | 1 | 1.21 | KCNK2 | 0 | 0.00 | |
| positive t cell selection: GO | 21 | 1 | 0.80 | IL6 | 1 | 0.56 | BCL2 | 0 | 0.00 | | 0 | 0.00 | | 1 | 1.21 | BCL2 | 0 | 0.00 | |
| precatalytic spliceosome: GO | 21 | 1 | 0.80 | SNRPG | 0 | 0.00 | | 0 | 0.00 | | 0 | 0.00 | | 0 | 0.00 | | 0 | 0.00 | |
| prespliceosome: GO | 21 | 1 | 0.80 | SNRPG | 1 | 0.56 | SNRPN | 0 | 0.00 | | 0 | 0.00 | | 1 | 1.21 | SNRPN | 0 | 0.00 | |
| response to thyroid hormone: GO | 21 | 1 | 0.80 | CTSB | 3 | 1.69 | GATA1; PPARGC1A; | 0 | 0.00 | | 0 | 0.00 | | 1 | 1.21 | PPARGC1A | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| acrosomal membrane: GO | 21 | 0 | 0.00 | | 2 | 1.12 | SLC26A5 SERPINA5; TEKT3 | 0 | 0.00 | | 0 | 0.00 | | 0 | 0.00 | | 0 | 0.00 | |
| actin filament polymerization: GO | 21 | 0 | 0.00 | | 3 | 1.69 | ARHGAP6; COBL; GSN | 0 | 0.00 | | 0 | 0.00 | | 0 | 0.00 | | 0 | 0.00 | |
| akt pathway | 21 | 0 | 0.00 | | 1 | 0.56 | GHR | 1 | 19.90 | GHR | 0 | 0.00 | | 0 | 0.00 | | 0 | 0.00 | |
| akt signaling pathway | 21 | 0 | 0.00 | | 1 | 0.56 | GHR | 1 | 19.90 | GHR | 0 | 0.00 | | 0 | 0.00 | | 0 | 0.00 | |
| alpha actinin binding: GO | 21 | 0 | 0.00 | | 2 | 1.12 | LDB3; SYNPO2 | 0 | 0.00 | | 0 | 0.00 | | 0 | 0.00 | | 0 | 0.00 | |
| antigen activates b cell receptor (bcr) leading to generation of second messengers | 21 | 0 | 0.00 | | 0 | 0.00 | | 0 | 0.00 | | 0 | 0.00 | | 2 | 2.42 | IGHM; TRPC1 | 0 | 0.00 | |
| ceramide signaling pathway | 21 | 0 | 0.00 | | 1 | 0.56 | BCL2 | 0 | 0.00 | | 0 | 0.00 | | 1 | 1.21 | BCL2 | 0 | 0.00 | |
| cgmp effects | 21 | 0 | 0.00 | | 4 | 2.25 | KCNMB4; PDE11A; PDE9A; PRKG2 | 0 | 0.00 | | 0 | 0.00 | | 4 | 4.84 | PDE1A; PDE9A; PRKG1; PRKG2 | 0 | 0.00 | |
| erythrocyte development: GO | 21 | 0 | 0.00 | | 3 | 1.69 | EPB42; GATA1; RHAG | 0 | 0.00 | | 0 | 0.00 | | 0 | 0.00 | | 0 | 0.00 | |
| fgfr ligand binding and activation | 21 | 0 | 0.00 | | 6 | 3.37 | FGF1; FGF17; FGF22; FGF9; FGFR1; FGFR3 | 0 | 0.00 | | 0 | 0.00 | | 3 | 3.63 | FGF2; FGF22; FGFR1 | 0 | 0.00 | |
| glutamate neurotransmitter release cycle | 21 | 0 | 0.00 | | 6 | 3.37 | RIMS1; SLC17A7; SLC1A2; SLC1A6; SLC1A7; SYT1 | 0 | 0.00 | | 0 | 0.00 | | 3 | 3.63 | RIMS1; SLC1A6; SLC1A7 | 0 | 0.00 | |
| glycoprotein complex: GO | 21 | 0 | 0.00 | | 6 | 3.37 | DMD; PGM5; SGCA; SGCG; SGCZ; SSPN | 1 | 19.90 | SGCG | 0 | 0.00 | | 4 | 4.84 | PGM5; SGCZ; SNTB1; SSPN | 0 | 0.00 | |
| histone | 21 | 0 | 0.00 | | 1 | 0.56 | KAT2A | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| deubiquitination: GO | | | | | | | | | | | | | | | | | | | |
| hydrogen exporting atpase activity: GO | 21 | 0 | 0.00 | | 2 | 1.12 | ATP6V0A4; ATP6V0E2 | 0 | 0.00 | | 0 | 0.00 | | 2 | 2.42 | ATP6V0A4; ATP6V0E2 | 0 | 0.00 | |
| left right pattern formation: GO | 21 | 0 | 0.00 | | 2 | 1.12 | DNAAF1; NKX2-5 | 0 | 0.00 | | 0 | 0.00 | | 0 | 0.00 | | 0 | 0.00 | |
| lipid translocation: GO | 21 | 0 | 0.00 | | 1 | 0.56 | P2RX7 | 0 | 0.00 | | 0 | 0.00 | | 0 | 0.00 | | 0 | 0.00 | |
| maturity onset diabetes of the young | 21 | 0 | 0.00 | | 2 | 1.12 | MNX1; PAX6 | 0 | 0.00 | | 0 | 0.00 | | 1 | 1.21 | BHLHA15 | 0 | 0.00 | |
| monoamine transport: GO | 21 | 0 | 0.00 | | 5 | 2.81 | CADPS; DRD1; P2RX1; SLC6A2; SNCA | 0 | 0.00 | | 0 | 0.00 | | 2 | 2.42 | SLC18A2; SNCA | 0 | 0.00 | |
| negative regulation of epithelial to mesenchymal transition: GO | 21 | 0 | 0.00 | | 2 | 1.12 | BMP5; TBX5 | 0 | 0.00 | | 0 | 0.00 | | 1 | 1.21 | FOXA1 | 0 | 0.00 | |
| nitric oxide signaling pathway | 21 | 0 | 0.00 | | 3 | 1.69 | GRIN1; GRIN2A; PRKAR2B | 1 | 19.90 | PRKAR2B | 0 | 0.00 | | 0 | 0.00 | | 0 | 0.00 | |
| nos1 pathway | 21 | 0 | 0.00 | | 3 | 1.69 | GRIN1; GRIN2A; PRKAR2B | 1 | 19.90 | PRKAR2B | 0 | 0.00 | | 0 | 0.00 | | 0 | 0.00 | |
| phosphatidyl-inositol dephos-phorylation: GO | 21 | 0 | 0.00 | | 1 | 0.56 | PTPRQ | 0 | 0.00 | | 0 | 0.00 | | 0 | 0.00 | | 0 | 0.00 | |
| polysaccharide binding: GO | 21 | 0 | 0.00 | | 5 | 2.81 | CLEC18A; ENPP1; FCN2; STBD1; SUSD2 | 0 | 0.00 | | 0 | 0.00 | | 2 | 2.42 | ENPP3; SUSD2 | 0 | 0.00 | |
| positive regulation of adherens junction | 21 | 0 | 0.00 | | 1 | 0.56 | MYOC | 0 | 0.00 | | 0 | 0.00 | | 1 | 1.21 | MYOC | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| organization: GO | | | | | | | | | | | | | | | | | | | |
| protein localization to cell surface: GO | 21 | 0 | 0.00 | | 4 | 2.25 | ANK2; FBLN5; GPIHBP1; WNT11 | 1 | 19.90 | MRAP2 | 0 | 0.00 | | 3 | 3.63 | ANGPT1; FBLN5; WNT11 | 0 | 0.00 | |
| r smad binding: GO | 21 | 0 | 0.00 | | 3 | 1.69 | MYOCD; PAX6; RANBP3L | 0 | 0.00 | | 0 | 0.00 | | 1 | 1.21 | RANBP3L | 0 | 0.00 | |
| regulation of mitochondrial membrane permeability involved in apoptotic process: GO | 21 | 0 | 0.00 | | 2 | 1.12 | CAMK2A; NOL3 | 0 | 0.00 | | 0 | 0.00 | | 0 | 0.00 | | 0 | 0.00 | |
| regulation of renal sodium excretion: GO | 21 | 0 | 0.00 | | 3 | 1.69 | ADORA1; AGT; AGTR1 | 0 | 0.00 | | 0 | 0.00 | | 2 | 2.42 | AGTR1; CORIN | 0 | 0.00 | |
| sex determination: GO | 21 | 0 | 0.00 | | 3 | 1.69 | FGF9; NR5A1; TCF21 | 0 | 0.00 | | 0 | 0.00 | | 1 | 1.21 | PTGDR | 0 | 0.00 | |
| signaling by hippo | 21 | 0 | 0.00 | | 2 | 1.12 | AMOT; MST1 | 0 | 0.00 | | 0 | 0.00 | | 0 | 0.00 | | 0 | 0.00 | |
| sodium independent organic anion transport: GO | 21 | 0 | 0.00 | | 4 | 2.25 | ALB; SLC22A9; SLCO4C1; SLCO5A1 | 0 | 0.00 | | 0 | 0.00 | | 0 | 0.00 | | 0 | 0.00 | |
| synthesis of bile acids and bile salts via 7alpha-hydroxy-cholesterol | 21 | 0 | 0.00 | | 3 | 1.69 | ABCB11; ACOX2; PTGIS | 0 | 0.00 | | 0 | 0.00 | | 1 | 1.21 | ACOX2 | 0 | 0.00 | |
| trefoil factors initiate mucosal healing | 21 | 0 | 0.00 | | 1 | 0.56 | GHR | 1 | 19.90 | GHR | 0 | 0.00 | | 0 | 0.00 | | 0 | 0.00 | |
| u4 u6 x u5 tri snrnp complex: GO | 21 | 0 | 0.00 | | 1 | 0.56 | SNRPN | 0 | 0.00 | | 0 | 0.00 | | 1 | 1.21 | SNRPN | 0 | 0.00 | |
| negative regulation of | 97 | 13 | 2.24 | ANXA1; C1QBP; | 1 | 0.12 | C4BPA | 0 | 0.00 | | 3 | 12.92 | IL2RA; IL7R; SERPINB9 | 1 | 0.26 | ANGPT1 | 2 | 0.58 | IL10; IL13RA2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| immune effector process: GO | | | | FOXF1; HMOX1; IL13RA2; IL2RA; IL4R; IL7R; JAK3; PGLYRP2; SERPINB4; SERPINB9; SLAMF1 | | | | | | | | | | | | | | | |
| extrinsic apoptotic signaling pathway: GO | 97 | 9 | 1.55 | BAK1; BCL2A1; IFNG; IL1A; IL1B; NGF; TNFRSF10A; TNFRSF12A; TNFRSF9 | 5 | 0.61 | BCL2; CD70; FGFR3; GOS2; P2RX7 | 0 | 0.00 | | 1 | 4.31 | IL1B | 2 | 0.52 | BCL2; CD70 | 2 | 0.58 | BAK1; NGF |
| positive regulation of transmembrane receptor protein serine threonine kinase signaling pathway: GO | 97 | 2 | 0.35 | TGFBR1; TTK | 12 | 1.46 | BMP3; BMP5; FGF9; GDF10; GDF5; GPC3; INHBB; ITGA8; MSTN; MYOCD; RNF165; ZNF423 | 1 | 4.31 | CDKN1C | 0 | 0.00 | | 2 | 0.52 | GDF7; ZNF423 | 2 | 0.58 | LRG1; TTK |
| fatty acid triacylglycerol and ketone body metabolism | 165 | 7 | 0.71 | AGPAT5; ELOVL4; ELOVL7; GK; HMGCR; TEAD4; TNFRSF21 | 13 | 0.93 | ACACB; ACADL; AGT; CYP1A1; CYP4A11; ELOVL2; GOS2; GPAM; GPD1; HMGCS2; PEX11A; PPARGC1A; PRKAA2 | 2 | 5.07 | GPAM; GPD1 | 0 | 0.00 | | 6 | 0.92 | CTGF; CYP4A11; DGAT2; HMGCS2; PPARGC1A; PRKAA2 | 4 | 0.69 | ANGPTL4; LPCAT1; TEAD4; TRIB3 |
| signal release: GO | 165 | 7 | 0.71 | ANXA1; HRH3; HSPA8; IL1RN; IL6; | 19 | 1.36 | APBA1; CADPS; CARTPT; EDN3; | 0 | 0.00 | | 0 | 0.00 | | 8 | 1.23 | APBA1; EDN3; NRXN1; PCLO; | 4 | 0.69 | HSPA8; SLC18A3; UNC13A; WNT7A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | UNC13A; WNT7A | | | FAM3B; FZD4; LEP; NLGN1; NRXN1; NRXN3; P2RX7; PCLO; RIMS1; RPH3AL; SYN2; SYT1; SYT17; SYT8; SYT9 | | | | | | | | | RIMS1; SLC18A2; SYN2; SYT17 | | | |
| sperm part: GO | 132 | 7 | 0.89 | ACRV1; CALR; CXADR; ENKUR; RACGAP1; RAN; TXNDC8 | 15 | 1.34 | CAPN11; CAPZA3; CATSPERG; GSTM3; ODF3; RSPH1; SERPINA5; SPAG8; SPEF2; SPINK1; STK31; SV2B; SYT8; TEKT3; TSKS | 0 | 0.00 | | 0 | 0.00 | | 7 | 1.35 | CAPN11; CAPZA3; CATSPERG; SPATA6; SPEF2; STK31; SV2B | 3 | 0.64 | PTCHD3; RAN; SLC26A6 |
| positive regulation of production of molecular mediator of immune response: GO | 62 | 13 | 3.51 | DEFB103A; DEFB103B; F2RL1; IFNG; IL4R; IL6; KLK5; KLK7; NR4A3; RSAD2; SASH3; TNFRSF4; WNT5A | 2 | 0.38 | IL5; RBP4 | 0 | 0.00 | | 1 | 6.74 | FFAR2 | 1 | 0.41 | GPRC5B | 1 | 0.46 | WNT5A |
| regulation of cell killing: GO | 62 | 6 | 1.62 | F2RL1; IFNG; IL12B; IL7R; SERPINB4; SERPINB9 | 4 | 0.76 | FCER2; LEP; NOS2; P2RX7 | 0 | 0.00 | | 2 | 13.48 | IL7R; SERPINB9 | 1 | 0.41 | PIK3R6 | 1 | 0.46 | IL10 |
| protein localization to | 62 | 5 | 1.35 | HK2; HSPA4; TIMM13; | 0 | 0.00 | | 0 | 0.00 | | 0 | 0.00 | | 0 | 0.00 | | 1 | 0.46 | HK2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| mitochondrion: GO | | | | TIMM23; TIMM8B | | | | | | | | | | | | | | | |
| regulation of smoothened signaling pathway: GO | 62 | 3 | 0.81 | CD3E; SALL3; SERPINE2 | 6 | 1.14 | FGF9; GLI2; GPC3; HHIP; PTCH1; PTCH2 | 0 | 0.00 | | 0 | 0.00 | | 8 | 3.28 | CHRD; FOXA1; GLI2; PRRX1; PTCH1; PTCH2; SHOX2; ZIC1 | 1 | 0.46 | SERPINE2 |
| trkr pathway | 62 | 3 | 0.81 | NGF; NRAS; NTRK1 | 5 | 0.95 | DNM1; MCF2L; NTRK3; SHC2; SHC3 | 0 | 0.00 | | 0 | 0.00 | | 1 | 0.41 | SHC2 | 1 | 0.46 | NGF |
| diseases of glycosylation | 62 | 1 | 0.27 | SDC1 | 8 | 1.52 | GALT; GPC3; GPC6; MUC20; MUC6; MUCL1; PRELP; SDC2 | 0 | 0.00 | | 0 | 0.00 | | 3 | 1.23 | DCN; MUC20; MUCL1 | 1 | 0.46 | AGRN |
| protein alkylation: GO | 98 | 1 | 0.17 | HIST1H1D | 2 | 0.24 | CHD5; RAB3B | 0 | 0.00 | | 0 | 0.00 | | 1 | 0.26 | RAB3B | 2 | 0.58 | BEND3; HIST1H1D |
| regulation of t helper 1 type immune response: GO | 22 | 6 | 4.56 | ANXA1; CD80; IL12B; IL1RL1; IL4R; JAK3 | 0 | 0.00 | | 0 | 0.00 | | 0 | 0.00 | | 0 | 0.00 | | 0 | 0.00 | |
| beta defensins | 22 | 4 | 3.04 | DEFB103A; DEFB103B; DEFB4A; DEFB4B | 1 | 0.54 | DEFB132 | 0 | 0.00 | | 1 | 19.00 | DEFB4A | 0 | 0.00 | | 0 | 0.00 | |
| regulation of alpha beta t cell proliferation: GO | 22 | 4 | 3.04 | CD3E; CD80; EBI3; IL12B | 0 | 0.00 | | 0 | 0.00 | | 0 | 0.00 | | 0 | 0.00 | | 0 | 0.00 | |
| regulation of cysteine type endopeptidase activity involved in apoptotic signaling pathway: GO | 22 | 4 | 3.04 | MMP9; PLAUR; TNFRSF10A; TNFSF10 | 1 | 0.54 | GSN | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| cellular glucuronidation: GO | 22 | 3 | 2.28 | UGT1A1; UGT1A10; UGT1A7 | 3 | 1.61 | UGT2A1; UGT2B7; UGT3A2 | 0 | 0.00 | | 0 | 0.00 | | 0 | 0.00 | | 0 | 0.00 | |
| er phagosome pathway | 22 | 3 | 2.28 | PSMA4; PSMD1; TAP2 | 0 | 0.00 | | 0 | 0.00 | | 0 | 0.00 | | 0 | 0.00 | | 0 | 0.00 | |
| glucuronidation | 22 | 3 | 2.28 | UGT1A1; UGT1A10; UGT1A7 | 2 | 1.07 | UGT2A1; UGT2B7 | 0 | 0.00 | | 0 | 0.00 | | 0 | 0.00 | | 0 | 0.00 | |
| negative regulation of alpha beta t cell activation: GO | 22 | 3 | 2.28 | ANXA1; IL4R; JAK3 | 0 | 0.00 | | 0 | 0.00 | | 0 | 0.00 | | 0 | 0.00 | | 0 | 0.00 | |
| positive regulation of protein complex disassembly: GO | 22 | 3 | 2.28 | EIF5A; EIF5AL1; F2RL1 | 2 | 1.07 | ACTN2; SLN | 0 | 0.00 | | 0 | 0.00 | | 0 | 0.00 | | 0 | 0.00 | |
| activation of nf kappab in b cells | 22 | 2 | 1.52 | PSMA4; PSMD1 | 0 | 0.00 | | 0 | 0.00 | | 0 | 0.00 | | 0 | 0.00 | | 0 | 0.00 | |
| il 2 signaling pathway | 22 | 2 | 1.52 | IL2RA; JAK3 | 0 | 0.00 | | 0 | 0.00 | | 1 | 19.00 | IL2RA | 0 | 0.00 | | 0 | 0.00 | |
| il2 pathway | 22 | 2 | 1.52 | IL2RA; JAK3 | 0 | 0.00 | | 0 | 0.00 | | 1 | 19.00 | IL2RA | 0 | 0.00 | | 0 | 0.00 | |
| il6 pathway | 22 | 2 | 1.52 | IL6; JAK3 | 0 | 0.00 | | 0 | 0.00 | | 0 | 0.00 | | 0 | 0.00 | | 0 | 0.00 | |
| m g1 transition | 22 | 2 | 1.52 | PSMA4; PSMD1 | 0 | 0.00 | | 0 | 0.00 | | 0 | 0.00 | | 0 | 0.00 | | 0 | 0.00 | |
| positive regulation of epithelial cell apoptotic process: GO | 22 | 2 | 1.52 | EIF2S1; IL6 | 2 | 1.07 | GSN; PPARGC1A | 0 | 0.00 | | 0 | 0.00 | | 2 | 2.31 | ECSCR; PPARGC1A | 0 | 0.00 | |
| positive regulation of lamellipodium organization: GO | 22 | 2 | 1.52 | FSCN1; RAC2 | 1 | 0.54 | FRMD7 | 0 | 0.00 | | 1 | 19.00 | RAC2 | 0 | 0.00 | | 0 | 0.00 | |
| positive regulation of mesonephros development: GO | 22 | 2 | 1.52 | GDNF; GREM1 | 4 | 2.15 | AGT; NOG; SIX1; SOX8 | 0 | 0.00 | | 0 | 0.00 | | 0 | 0.00 | | 0 | 0.00 | |
| positive regulation of | 22 | 2 | 1.52 | IFNG; IL1B | 7 | 3.75 | AGT; AGTR1; APOC1; | 0 | 0.00 | | 1 | 19.00 | IL1B | 2 | 2.31 | AGTR1; PPARGC1A | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| steroid metabolic process: GO | | | | | | | APOE; CYP17A1; FGF1; PPARGC1A | | | | | | | | | | | | |
| pyrimidine ribonucleotide metabolic process: GO | 22 | 2 | 1.52 | NME1; UPP1 | 1 | 0.54 | UPP2 | 0 | 0.00 | | 0 | 0.00 | | 0 | 0.00 | | 0 | 0.00 | |
| regulation of t cell mediated cytotoxicity: GO | 22 | 2 | 1.52 | IL12B; IL7R | 1 | 0.54 | P2RX7 | 0 | 0.00 | | 1 | 19.00 | IL7R | 0 | 0.00 | | 0 | 0.00 | |
| signaling by fgfr1 in disease | 22 | 2 | 1.52 | NRAS; STAT1 | 2 | 1.07 | FGF1; FGFR1 | 0 | 0.00 | | 0 | 0.00 | | 1 | 1.15 | FGFR1 | 0 | 0.00 | |
| camp binding: GO | 22 | 1 | 0.76 | CNGB1 | 2 | 1.07 | PDE11A; PRKAR2B | 1 | 19.00 | PRKAR2B | 0 | 0.00 | | 0 | 0.00 | | 0 | 0.00 | |
| cerebral cortex neuron differentiation: GO | 22 | 1 | 0.76 | EOMES | 4 | 2.15 | CHD5; DRD1; FEZF2; ID4 | 0 | 0.00 | | 0 | 0.00 | | 0 | 0.00 | | 0 | 0.00 | |
| constitutive signaling by notch1 hd + pest domain mutants | 22 | 1 | 0.76 | PSENEN | 0 | 0.00 | | 0 | 0.00 | | 0 | 0.00 | | 0 | 0.00 | | 0 | 0.00 | |
| constitutive signaling by notch1 pest domain mutants | 22 | 1 | 0.76 | PSENEN | 0 | 0.00 | | 0 | 0.00 | | 0 | 0.00 | | 0 | 0.00 | | 0 | 0.00 | |
| csk pathway | 22 | 1 | 0.76 | CD3E | 1 | 0.54 | PRKAR2B | 1 | 19.00 | PRKAR2B | 0 | 0.00 | | 0 | 0.00 | | 0 | 0.00 | |
| enos activation and regulation | 22 | 1 | 0.76 | LYPLA1 | 3 | 1.61 | CYGB; GCHFR; PRKG2 | 0 | 0.00 | | 0 | 0.00 | | 1 | 1.15 | PRKG2 | 0 | 0.00 | |
| gaba receptor activity: GO | 22 | 1 | 0.76 | GABRQ | 4 | 2.15 | GABRA2; GABRB3; GABRG3; GABRP | 0 | 0.00 | | 0 | 0.00 | | 0 | 0.00 | | 0 | 0.00 | |
| glutamine metabolic | 22 | 1 | 0.76 | GGH | 0 | 0.00 | | 0 | 0.00 | | 0 | 0.00 | | 1 | 1.15 | ALDH5A1 | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| process: GO | | | | | | | | | | | | | | | | | | | |
| her2 pathway | 22 | 1 | 0.76 | IL6 | 1 | 0.54 | ERBB4 | 0 | 0.00 | | 0 | 0.00 | | 2 | 2.31 | ERBB4; ESR1 | 0 | 0.00 | |
| macromolecular complex remodeling: GO | 22 | 1 | 0.76 | LIPG | 5 | 2.68 | AGT; AGTR1; APOC1; APOE; LPL | 1 | 19.00 | LPL | 0 | 0.00 | | 1 | 1.15 | AGTR1 | 0 | 0.00 | |
| oxidoreductase activity acting on a heme group of donors: GO | 22 | 1 | 0.76 | COX7B | 1 | 0.54 | COX7A1 | 0 | 0.00 | | 0 | 0.00 | | 1 | 1.15 | COX7A1 | 0 | 0.00 | |
| positive regulation of muscle hypertrophy: GO | 22 | 1 | 0.76 | NR4A3 | 2 | 1.07 | AGT; PDE9A | 0 | 0.00 | | 0 | 0.00 | | 1 | 1.15 | PDE9A | 0 | 0.00 | |
| protein k63 linked deubiquitination: GO | 22 | 1 | 0.76 | YOD1 | 1 | 0.54 | USP17L2 | 0 | 0.00 | | 0 | 0.00 | | 0 | 0.00 | | 0 | 0.00 | |
| regulation of appetite: GO | 22 | 1 | 0.76 | CCK | 3 | 1.61 | CARTPT; HTR4; LEP | 0 | 0.00 | | 0 | 0.00 | | 0 | 0.00 | | 0 | 0.00 | |
| regulation of b cell differentiation: GO | 22 | 1 | 0.76 | PRDM1 | 0 | 0.00 | | 0 | 0.00 | | 0 | 0.00 | | 0 | 0.00 | | 0 | 0.00 | |
| regulation of tnfr1 signaling | 22 | 1 | 0.76 | USP2 | 0 | 0.00 | | 0 | 0.00 | | 0 | 0.00 | | 0 | 0.00 | | 0 | 0.00 | |
| signaling by fgfr4 | 22 | 1 | 0.76 | NRAS | 1 | 0.54 | FGF1 | 0 | 0.00 | | 0 | 0.00 | | 0 | 0.00 | | 0 | 0.00 | |
| signaling by notch1 hd + pest domain mutants in cancer | 22 | 1 | 0.76 | PSENEN | 0 | 0.00 | | 0 | 0.00 | | 0 | 0.00 | | 0 | 0.00 | | 0 | 0.00 | |
| signaling by notch1 in cancer | 22 | 1 | 0.76 | PSENEN | 0 | 0.00 | | 0 | 0.00 | | 0 | 0.00 | | 0 | 0.00 | | 0 | 0.00 | |
| signaling by notch1 pest domain mutants in cancer | 22 | 1 | 0.76 | PSENEN | 0 | 0.00 | | 0 | 0.00 | | 0 | 0.00 | | 0 | 0.00 | | 0 | 0.00 | |
| signaling by notch2 | 22 | 1 | 0.76 | PSENEN | 0 | 0.00 | | 0 | 0.00 | | 0 | 0.00 | | 2 | 2.31 | CTSG; MDK | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| activation of nmda receptor and postsynaptic events | 22 | 0 | 0.00 | | 2 | 1.07 | ADCY8; GRIN2A | 0 | 0.00 | | 0 | 0.00 | | 0 | 0.00 | | 0 | 0.00 | |
| aorta morphogenesis: GO | 22 | 0 | 0.00 | | 2. | 1.07 | SIX1; TFAP2B | 0 | 0.00 | | 0 | 0.00 | | 0 | 0.00 | | 0 | 0.00 | |
| ciliary base: GO | 22 | 0 | 0.00 | | | 1.07 | GLI2; PRKAR2B | 1 | 19.00 | PRKAR2B | 0 | 0.00 | | 1 | 1.15 | GLI2 | 0 | 0.00 | |
| circadian repression of expression by rev erba | 22 | 0 | 0.00 | | 1 | 0.54 | PPARGC1A | 0 | 0.00 | | 0 | 0.00 | | 1 | 1.15 | PPARGC1A | 0 | 0.00 | |
| egfr interacts with phospholipase c-gamma | 22 | 0 | 0.00 | | 3 | 1.61 | ADCY8; EGF; PRKAR2B | 1 | 19.00 | PRKAR2B | 0 | 0.00 | | 1 | 1.15 | EGF | 0 | 0.00 | |
| glycosamino glycan biosynthesis chondroitin sulfate | 22 | 0 | 0.00 | | 2 | 1.07 | CHST12; UST | 0 | 0.00 | | 0 | 0.00 | | 2 | 2.31 | CHST12; UST | 0 | 0.00 | |
| histone h3 deacetylation: GO | 22 | 0 | 0.00 | | 2 | 1.07 | HDAC5; PER1 | 0 | 0.00 | | 0 | 0.00 | | 0 | 0.00 | | 0 | 0.00 | |
| hypothalamus development: GO | 22 | 0 | 0.00 | | 1 | 0.54 | SEMA3A | 0 | 0.00 | | 0 | 0.00 | | 0 | 0.00 | | 0 | 0.00 | |
| myosin filament: GO | 22 | 0 | 0.00 | | 8 | 4.29 | MYBPC1; MYBPH; MYH11; MYH14; MYH3; MYH7B; MYOM1; MYOM2 | 0 | 0.00 | | 0 | 0.00 | | 2 | 2.31 | MYOM1; MYOM2 | 0 | 0.00 | |
| nuclear transcriptional repressor complex: GO | 22 | 0 | 0.00 | | 4 | 2.15 | CHD5; PASD1; SALL2; TBX15 | 0 | 0.00 | | 0 | 0.00 | | 2 | 2.31 | SALL2; TBX15 | 0 | 0.00 | |
| peptide catabolic process: GO | 22 | 0 | 0.00 | | 1 | 0.54 | TRHDE | 0 | 0.00 | | 0 | 0.00 | | 0 | 0.00 | | 0 | 0.00 | |
| phospholipid | 22 | 0 | 0.00 | | 2 | 1.07 | EPHX2; | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| dephos-phorylation: GO | | | | | | | PTPRQ | | | | | | | | | | | | |
| positive regulation of heart rate: GO | 22 | 0 | 0.00 | | 4 | 2.15 | ADRA1A; ADRB1; EDN3; TPM1 | 0 | 0.00 | | 0 | 0.00 | | 3 | 3.46 | ADRA1A; EDN3; HRC | 0 | 0.00 | |
| positive regulation of microtubule polymerization or depolymerization: GO | 22 | 0 | 0.00 | | 1 | 0.54 | MAPT | 0 | 0.00 | | 0 | 0.00 | | 1 | 1.15 | MAPT | 0 | 0.00 | |
| regulation of androgen receptor signaling pathway: GO | 22 | 0 | 0.00 | | 1 | 0.54 | TCF21 | 0 | 0.00 | | 0 | 0.00 | | 0 | 0.00 | | 0 | 0.00 | |
| regulation of autophagy | 22 | 0 | 0.00 | | 1 | 0.54 | IFNA5 | 0 | 0.00 | | 0 | 0.00 | | 0 | 0.00 | | 0 | 0.00 | |
| regulation of cholesterol metabolic process: GO | 22 | 0 | 0.00 | | 5 | 2.68 | ACADL; APOE; EPHX2; FGF1; SERPINA12 | 0 | 0.00 | | 0 | 0.00 | | 2 | 2.31 | DGAT2; SERPINA12 | 0 | 0.00 | |
| regulation of systemic arterial blood pressure by renin angiotensin: GO | 22 | 0 | 0.00 | | 5 | 2.68 | AGT; AGTR1; NOX1; PCSK5; REN | 0 | 0.00 | | 0 | 0.00 | | 2 | 2.31 | AGTR1; CTSG | 0 | 0.00 | |
| transcription factor creb and its extracellular signals | 22 | 0 | 0.00 | | 1 | 0.54 | PRKAR2B | 1 | 19.00 | PRKAR2B | 0 | 0.00 | | 0 | 0.00 | | 0 | 0.00 | |
| wnt activated receptor activity: GO | 22 | 0 | 0.00 | | 4 | 2.15 | EGF; FRZB; FZD4; FZD8 | 0 | 0.00 | | 0 | 0.00 | | 3 | 3.46 | EGF; FZD7; TSPAN12 | 0 | 0.00 | |
| positive regulation of leukocyte proliferation: | 133 | 19 | 2.39 | ANXA1; CD274; CD3E; CD80; CDKN1A; | 7 | 0.62 | BCL2; DHPS; FLT3LG; GPAM; IL5; IRS2; LEP | 1 | 3.14 | GPAM | 2 | 6.28 | IL1B; IL2RA | 1 | 0.19 | BCL2 | 3 | 0.64 | CDKN1A; PNP; PRKCQ |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline: Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo: Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo: Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| GO | | | | EBI3; IFNG; IL12B; IL1B; IL2RA; IL6; JAK3; PNP; PRKCQ; PYCARD; SASH3; SLAMF1; TNFRSF4; TNFSF9 | | | | | | | | | | | | | | | |
| circadian rhythm: GO | 133 | 10 | 1.26 | AHCY; ARNTL2; HTR7; NAMPT; NTRK1; PROK2; SERPINE1; TH; TIMELESS; USP2 | 18 | 1.60 | ADIPOQ; BHLHE41; CARTPT; CRY2; DBP; DRD4; F7; HS3ST2; ID4; KCND2; LEP; NOS2; NTRK3; PER1; PPARGC1A; PROK1; RORB; RORC | 1 | 3.14 | ADIPOQ | 1 | 3.14 | SERPINE1 | 4 | 0.76 | BHLHE41; CRY2; KCND2; PPARGC1A | 3 | 0.64 | NAMPT; TH; TIMELESS |
| regulation of transmembrane receptor protein serine threonine kinase signaling pathway: GO | 200 | 8 | 0.67 | GREM1; HSPA5; ITGA3; LTBP1; TBX20; TGFBR1; TTK; WNT5A | 25 | 1.47 | BMP3; BMP5; CHRDL1; DACT1; DACT2; DKK1; FGF9; FOLR1; GDF10; GDF5; GPC3; GREM2; INHBB; ITGA8; MAGI2; MSTN; MYOCD; NOG; RNF165; SKOR1; SKOR2; | 1 | 2.09 | CDKN1C | 0 | 0.00 | | 6 | 0.76 | CHRD; DACT1; GDF7; GREM2; VWC2; ZNF423 | 5 | 0.71 | HSPA5; ITGA3; LRG1; TTK; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | TFAP2B; TMPRSS6; VWC2L; ZNF423 | | | | | | | | | | | | |
| negative regulation of transmembrane receptor protein serine threonine kinase signaling pathway: GO | 99 | 6 | 1.01 | GREM1; HSPA5; LTBP1; TBX20; TGFBR1; WNT5A | 10 | 1.19 | CHRDL1; DACT2; DKK1; GREM2; MAGI2; NOG; SKOR1; SKOR2; TMPRSS6; VWC2L | 0 | 0.00 | | 0 | 0.00 | | 3 | 0.77 | CHRD; GREM2; VWC2 | 2 | 0.57 | HSPA5; WNT5A |
| regulation of circadian rhythm: GO | 99 | 5 | 0.85 | ARNTL2; IL6; TIMELESS; TOP2A; USP2 | 13 | 1.55 | ADORA1; ALB; CRY2; DRD1; DRD4; KCNA2; NLGN1; PASD1; PER1; PPARGC1A; PRKAA2; RORB; RORC | 0 | 0.00 | | 0 | 0.00 | | 3 | 0.77 | CRY2; PPARGC1A; PRKAA2 | 2 | 0.57 | TIMELESS; TOP2A |
| il12 2pathway | 63 | 11 | 2.92 | CCL3; CCR5; CD3E; EOMES; GZMA; IFNG; IL12B; IL12RB2; IL1B; IL2RA; STAT1 | 1 | 0.19 | NOS2 | 0 | 0.00 | | 3 | 19.90 | GZMB; IL1B; IL2RA | 0 | 0.00 | | 1 | 0.45 | IL12RB2 |
| b cell receptor signaling pathway | 63 | 3 | 0.80 | IFITM1; NRAS; RAC2 | 1 | 0.19 | CHP2 | 0 | 0.00 | | 1 | 6.63 | RAC2 | 1 | 0.40 | CHP2 | 1 | 0.45 | VAV2 |
| cytoplasmic mrna processing body: GO | 63 | 2 | 0.53 | PSMA4; ZC3H12A | 1 | 0.19 | CPEB1 | 0 | 0.00 | | 0 | 0.00 | | 1 | 0.40 | CPEB1 | 1 | 0.45 | ZC3H12A |
| hormone binding: GO | 63 | 2 | 0.53 | ALDH1A3; CALR | 10 | 1.87 | ALDH1A1; AMHR2; AR; ATP1A2; CALCR; | 1 | 6.63 | GHR | 0 | 0.00 | | 3 | 1.21 | ESR1; PTH1R; SLC40A1 | 1 | 0.45 | UCN2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | GALR1; GCGR; GHR; LHCGR; PTH1R | | | | | | | | | | | | |
| single stranded rna binding: GO | 63 | 2 | 0.53 | ANXA1; EIF4A3 | 2 | 0.37 | CBX7; RBM11 | 0 | 0.00 | | 0 | 0.00 | | 1 | 0.40 | CBX7 | 1 | 0.45 | EIF4A3 |
| protein complex scaffold: GO | 63 | 1 | 0.27 | CD3E | | 0.75 | MAGI2; MAPK8IP1; ROPN1B; SHANK1 | 0 | 0.00 | | 0 | 0.00 | | 1 | 0.40 | ROPN1B | 1 | 0.45 | CARD10 |
| signaling by fgfr in disease | 134 | 4 | 0.50 | CDK1; CDKN1A; NRAS; STAT1 | 11 | 0.97 | ADCY2; ADCY5; ADCY6; ADCY8; FGF1; FGF17; FGF22; FGF9; FGFR1; FGFR3; PRKAR2B | 1 | 3.12 | PRKAR2B | 0 | 0.00 | | 4 | 0.76 | FGF2; FGF22; FGFR1; PDE1A | 3 | 0.63 | CDK1; CDKN1A; TRIB3 |
| homeostasis of number of cells: GO | 168 | 15 | 1.49 | ANXA1; BAK1; CCNB2; CCR4; GCNT4; HCAR2; HIF1A; HMOX1; IFNG; IL2RA; IL6; IL7R; JAK3; PRDX1; SASH3 | 8 | 0.56 | ALAS2; BCL2; CACNA1F; EPB42; FLT3LG; GATA1; P2RX7; RHAG | 0 | 0.00 | | 3 | 7.46 | HCAR2; IL2RA; IL7R | 3 | 0.45 | BCL2; SLC40A1; SLC46A2 | 4 | 0.68 | BAK1; CCNB2; DYRK3; HIF1A |
| exopeptidase activity: GO | 100 | 6 | 1.00 | CNDP2; CPA6; CPXM1; DPP3; DPP4; GGH | 6 | 0.71 | AGBL1; AGBL4; DPP10; DPP6; GGT7; TRHDE | 0 | 0.00 | | 0 | 0.00 | | 3 | 0.76 | CPE; CPZ; DPP6 | 2 | 0.57 | CPA6; DPP4 |
| estrogen metabolic process: GO | 23 | 3 | 2.18 | AKRIB15; IL1B; UGT1A1 | 1 | 0.51 | HSD17B14 | 0 | 0.00 | | 1 | 18.17 | IL1B | 1 | 1.10 | SULT1E1 | 0 | 0.00 | |
| regulation | 23 | 3 | 2.18 | CCL21; | 0 | 0.00 | | 0 | 0.00 | | 0 | 0.00 | | 1 | 1.10 | ABCB5 | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| of antigen processing and presentation: GO | | | | PYCARD; TAP2 | | | | | | | | | | | | | | | |
| regulation of syncytium formation by plasma membrane fusion: GO | 23 | 3 | 2.18 | CXCL10; CXCL9; IL4R | 3 | 1.54 | CAMK1; FLT3LG; SCGB3A1 | 0 | 0.00 | | 1 | 18.17 | CXCL9 | 1 | 1.10 | CAMK1 | 0 | 0.00 | |
| axon regeneration: GO | 23 | 2 | 1.46 | NEFL; TNC | 3 | 1.54 | APOD; BCL2; FOLR1 | 0 | 0.00 | | 0 | 0.00 | | 2 | 2.21 | BCL2; CHL1 | 0 | 0.00 | |
| cellular extravasation: GO | 23 | 2 | 1.46 | SELE; TREM1 | 1 | 0.51 | LEP | 0 | 0.00 | | 2 | 36.34 | SELE; TREM1 | 0 | 0.00 | | 0 | 0.00 | |
| ctcf pathway | 23 | 2 | 1.46 | CD79A; TGFBR1 | 0 | 0.00 | | 0 | 0.00 | | 0 | 0.00 | | 0 | 0.00 | | 0 | 0.00 | |
| ctla4 inhibitory signaling | 23 | 2 | 1.46 | CD80; CTLA4 | 0 | 0.00 | | 0 | 0.00 | | 0 | 0.00 | | 0 | 0.00 | | 0 | 0.00 | |
| ga12 pathway | 23 | 2 | 1.46 | F2RL1; NR4A3 | 1 | 0.51 | MYEF2 | 0 | 0.00 | | 0 | 0.00 | | 0 | 0.00 | | 0 | 0.00 | |
| histone monoubiquitination: GO | 23 | 2 | 1.46 | DTX3L; UHRF1 | 0 | 0.00 | | 0 | 0.00 | | 0 | 0.00 | | 0 | 0.00 | | 0 | 0.00 | |
| n-glycan trimming in the er and calnexin/calreticulin cycle | 23 | 2 | 1.46 | CALR; PDIA3 | 0 | 0.00 | | 0 | 0.00 | | 0 | 0.00 | | 0 | 0.00 | | 0 | 0.00 | |
| positive regulation of g protein coupled receptor protein signaling pathway: GO | 23 | 2 | 1.46 | KLK5; KLK6 | 1 | 0.51 | C3 | 0 | 0.00 | | 0 | 0.00 | | 1 | 1.10 | C3 | 0 | 0.00 | |
| proteasome accessory complex: GO | 23 | 2 | 1.46 | PSMD1; PSME3 | 0 | 0.00 | | 0 | 0.00 | | 0 | 0.00 | | 0 | 0.00 | | 0 | 0.00 | |
| regulation of myeloid cell apoptotic process: GO | 23 | 2 | 1.46 | ANXA1; HCAR2 | 2 | 1.03 | ADIPOQ; BCL2 | 1 | 18.17 | ADIPOQ | 1 | 18.17 | HCAR2 | 1 | 1.10 | BCL2 | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | A: Fold Change (FC) Up | A: Up-regulated Genes | A: Down-regulated | A: Fold Change (FC) | A: Down-regulated Genes | B. Differentially expressed genes significant in the baseline vs week 12 comparison only in the placebo: Up-regulated | B: Fold Change (FC) Up | B: Up-regulated Genes | B: Down-regulated | B: Fold Change (FC) | B: Down-regulated Genes | C. Differentially expressed genes significant in the baseline vs week 12 comparison only in the nemo: Up-regulated | C: Fold Change (FC) Up | C: Up-regulated Genes | C: Down-regulated | C: Fold Change (FC) | C: Down-regulated Genes |
|---|---|---|---|---|---|---|---|---|---|---|---|---|---|---|---|---|---|---|---|
| renal system process involved in regulation of systemic arterial blood pressure: GO | 23 | 2 | 1.46 | F2RL1; GJA1 | 7 | 3.59 | ADORA1; AGT; AGTR1; CYP4A11; CYP4F12; PCSK5; REN | 1 | 18.17 | HSD11B2 | 0 | 0.00 | | 3 | 3.31 | AGTR1; CYP4A11; CYP4F12 | 0 | 0.00 | |
| adrenal gland development: GO | 23 | 1 | 0.73 | STRA6 | 3 | 1.54 | CYP17A1; NR5A1; WNT11 | 1 | 18.17 | CDKN1C | 0 | 0.00 | | 2 | 2.21 | MDK; WNT11 | 0 | 0.00 | |
| aspartic type peptidase activity: GO | 23 | 1 | 0.73 | ASPRVI | 3 | 1.54 | NAPSA; PIP; REN | 0 | 0.00 | | 0 | 0.00 | | 1 | 1.10 | PIP | 0 | 0.00 | |
| endocytic recycling: GO | 23 | 1 | 0.73 | ARL4C | 0 | 0.00 | | 0 | 0.00 | | 0 | 0.00 | | 1 | 1.10 | SLC18A2 | 0 | 0.00 | |
| epithelial cell differentiation involved in kidney development: GO | 23 | 1 | 0.73 | GPR4 | 3 | 1.54 | CD34; KLF15; MAGI2 | 0 | 0.00 | | 0 | 0.00 | | 1 | 1.10 | CD34 | 0 | 0.00 | |
| gleevec pathway | 23 | 1 | 0.73 | STAT1 | 0 | 0.00 | | 0 | 0.00 | | 0 | 0.00 | | 0 | 0.00 | | 0 | 0.00 | |
| heparan sulfate proteoglycan biosynthetic process: GO | 23 | 1 | 0.73 | HS3ST3B1 | 3 | 1.54 | EXTL1; HS3ST5; HS6ST3 | 0 | 0.00 | | 0 | 0.00 | | 0 | 0.00 | | 0 | 0.00 | |
| inhibition of cellular proliferation by gleevec | 23 | 1 | 0.73 | STAT1 | 0 | 0.00 | | 0 | 0.00 | | 0 | 0.00 | | 0 | 0.00 | | 0 | 0.00 | |
| ionotropic glutamate receptor binding: GO | 23 | 1 | 0.73 | NETO2 | 3 | 1.54 | DLG2; NETO1; SHANK1 | 0 | 0.00 | | 0 | 0.00 | | 1 | 1.10 | DLG2 | 0 | 0.00 | |
| phosphatidyl-inositol 3 kinase signaling: GO | 23 | 1 | 0.73 | C1QBP | 1 | 0.51 | LTK | 0 | 0.00 | | 0 | 0.00 | | 1 | 1.10 | PREX2 | 0 | 0.00 | |
| plasma lipoprotein remodeling | 23 | 1 | 0.73 | LIPG | 4 | 2.05 | ALB; APOE; CIDEC; PCSK5 | 1 | 18.17 | CIDEC | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| regulation of cardiac muscle contraction by calcium ion signaling: GO | 23 | 1 | 0.73 | GSTO1 | 5 | 2.56 | ANK2; ATP1A2; CASQ2; DMD; GSTM2 | 0 | 0.00 | | 0 | 0.00 | | 1 | 1.10 | HRC | 0 | 0.00 | |
| role of erbb2 in signal transduction and oncology | 23 | 1 | 0.73 | IL6 | 1 | 0.51 | ERBB4 | 0 | 0.00 | | 0 | 0.00 | | 2 | 2.21 | ERBB4; ESR1 | 0 | 0.00 | |
| adrenergic receptor signaling pathway: GO | 23 | 0 | 0.00 | | 7 | 3.59 | ADRA1A; ADRA1B; ADRA2A; ADRB1; OR56A1; OR56A4; OR56A5 | 0 | 0.00 | | 0 | 0.00 | | 2 | 2.21 | ADRA1A; ADRA2A | 0 | 0.00 | |
| arf guanyl nucleotide exchange factor activity: GO | 23 | 0 | 0.00 | | 1 | 0.51 | PSD2 | 0 | 0.00 | | 0 | 0.00 | | 0 | 0.00 | | 0 | 0.00 | |
| atp synthesis | 23 | 0 | 0.00 | | 2 | 1.03 | ATP6V0A4; ATP6V1B1 | 0 | 0.00 | | 0 | 0.00 | | 1 | 1.10 | ATP6V0A4 | 0 | 0.00 | |
| acid metabolic process: GO | 23 | 0 | 0.00 | | 1 | 0.51 | GHR | 1 | 18.17 | GHR | 0 | 0.00 | | 0 | 0.00 | | 0 | 0.00 | |
| ciliary transition zone: GO | 23 | 0 | 0.00 | | 0 | 0.00 | | 0 | 0.00 | | 0 | 0.00 | | 1 | 1.10 | B9D1 | 0 | 0.00 | |
| clathrin vesicle coat: GO | 23 | 0 | 0.00 | | 1 | 0.51 | NCALD | 0 | 0.00 | | 0 | 0.00 | | 1 | 1.10 | NCALD | 0 | 0.00 | |
| collagen chain trimerization | 23 | 0 | 0.00 | | 2 | 1.03 | COL24A1; COL9A2 | 0 | 0.00 | | 0 | 0.00 | | 2 | 2.21 | COL24A1; GULP1 | 0 | 0.00 | |
| complex of collagen trimers: GO | 23 | 0 | 0.00 | | 3 | 1.54 | COL11A1; COL 11A2; TNXB | 0 | 0.00 | | 0 | 0.00 | | 2 | 2.21 | COL11A1; DCN | 0 | 0.00 | |
| cranial nerve morphogenesis: GO | 23 | 0 | 0.00 | | 6 | 3.08 | EPHB1; KCNA2; PLXNA3; PLXNA4; SEMA3A; SIX 1 | 0 | 0.00 | | 0 | 0.00 | | 1 | 1.10 | PLXNA4 | 0 | 0.00 | |
| gamma aminobutyric | 23 | 0 | 0.00 | | 3 | 1.54 | GABRA2; GABRG3; | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| acid signaling pathway: GO | | | | | | | HTR4 | | | | | | | | | | | | |
| high density lipoprotein particle: GO | 23 | 0 | 0.00 | | 5 | 2.56 | APOC1; APOE; CLU; GPIHBP1; PON1 | 0 | 0.00 | | 0 | 0.00 | | 1 | 1.10 | CLU | 0 | 0.00 | |
| igf1r pathway | 23 | 0 | 0.00 | | 1 | 0.51 | PRKAR2B | 1 | 18.17 | PRKAR2B | 0 | 0.00 | | 0 | 0.00 | | 0 | 0.00 | |
| intrinsic component of external side of plasma membrane: GO | 23 | 0 | 0.00 | | 7 | 3.59 | F10; FLT3LG; FOLR1; FOLR2; GGT7; GPIHBP1; PKHD1 | 0 | 0.00 | | 0 | 0.00 | | 0 | 0.00 | | 0 | 0.00 | |
| ligand dependent nuclear receptor binding: GO | 23 | 0 | 0.00 | | 1 | 0.51 | PPARGC1A | 0 | 0.00 | | 0 | 0.00 | | 1 | 1.10 | PPARGC1A | 0 | 0.00 | |
| multi organism organelle organization: GO | 23 | 0 | 0.00 | | 1 | 0.51 | VPS37D | 0 | 0.00 | | 0 | 0.00 | | 0 | 0.00 | | 0 | 0.00 | |
| multiple antiapoptotic pathways from igf-1r signaling lead to bad phosphorylation | 23 | 0 | 0.00 | | 1 | 0.51 | PRKAR2B | 1 | 18.17 | PRKAR2B | 0 | 0.00 | | 0 | 0.00 | | 0 | 0.00 | |
| negative regulation of blood vessel endothelial cell migration: GO | 23 | 0 | 0.00 | | 3 | 1.54 | ANGPT4; APOE; HDAC5 | 0 | 0.00 | | 0 | 0.00 | | 2 | 2.21 | ANGPT4; FGF2 | 0 | 0.00 | |
| netrin-1 signaling | 23 | 0 | 0.00 | | 1 | 0.51 | SLIT2 | 0 | 0.00 | | 0 | 0.00 | | 3 | 3.31 | NTN4; SLIT2; TRPC1 | 0 | 0.00 | |
| pigment granule localization: GO | 23 | 0 | 0.00 | | 0 | 0.00 | | 0 | 0.00 | | 0 | 0.00 | | 1 | 1.10 | ASIP | 0 | 0.00 | |
| plasma membrane fusion: GO | 23 | 0 | 0.00 | | 2 | 1.03 | ROPN1B; SERPINA5 | 0 | 0.00 | | 0 | 0.00 | | 1 | 1.10 | ROPN1B | 0 | 0.00 | |
| protein | 23 | 0 | 0.00 | | 1 | 0.51 | ZDHHC15 | 0 | 0.00 | | 0 | 0.00 | | 1 | 1.10 | ZDHHC15 | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| palmitoylation: GO | | | | | | | | | | | | | | | | | | | |
| protein targeting to plasma membrane: GO | 23 | 0 | 0.00 | | 6 | 3.08 | ANK2; KCNB1; KCNB2; PALM; PRKG2; PTCH1 | 0 | 0.00 | | 0 | 0.00 | | 4 | 4.42 | PALM; PRKG2; PTCH1; TESC | 0 | 0.00 | |
| proton transporting v type atpase complex: GO | 23 | 0 | 0.00 | | 3 | 1.54 | ATP6V0A4; ATP6V0E2; ATP6V1B1 | 0 | 0.00 | | 0 | 0.00 | | 2 | 2.21 | ATP6V0A4; ATP6V0E2 | 0 | 0.00 | |
| reactive oxygen species biosynthetic process: GO | 23 | 0 | 0.00 | | 4 | 2.05 | CYP1A1; CYP1A2; GCHFR; NOS2 | 0 | 0.00 | | 0 | 0.00 | | 0 | 0.00 | | 0 | 0.00 | |
| regulation of intracellular estrogen receptor signaling pathway: GO | 23 | 0 | 0.00 | | 1 | 0.51 | KANK2 | 0 | 0.00 | | 0 | 0.00 | | 1 | 1.10 | FOXA1 | 0 | 0.00 | |
| regulation of long term neuronal synaptic plasticity: GO | 23 | 0 | 0.00 | | 7 | 3.59 | AGT; CAMK2B; DRD1; GRIN1; NETO1; SNCA; SYNGR1 | 0 | 0.00 | | 0 | 0.00 | | 1 | 1.10 | SNCA | 0 | 0.00 | |
| regulation of transcription initiation from rna polymerase ii promoter: GO | 23 | 0 | 0.00 | | 1 | 0.51 | NKX2-5 | 0 | 0.00 | | 0 | 0.00 | | 0 | 0.00 | | 0 | 0.00 | |
| regulation of voltage gated calcium channel activity: GO | 23 | 0 | 0.00 | | 5 | 2.56 | CACNA2D1; CACNB1; DMD; DRD4; FGF14 | 0 | 0.00 | | 0 | 0.00 | | 2 | 2.21 | CACNA2D1; CACNB1 | 0 | 0.00 | |
| response to magnesium ion: GO | 23 | 0 | 0.00 | | 6 | 3.08 | C3; D2HGDH; KCNA1; KCNJ1; SLC34A3; | 0 | 0.00 | | 0 | 0.00 | | 2 | 2.21 | C3; SNCA | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | SNCA | | | | | | | | | | | | |
| rora activates circadian expression | 23 | 0 | 0.00 | | 1 | 0.51 | PPARGC1A | 0 | 0.00 | | 0 | 0.00 | | 1 | 1.10 | PPARGC1A | 0 | 0.00 | |
| spinal cord patterning: GO | 23 | 0 | 0.00 | | 5 | 2.56 | FOXN4; GLI2; PAX6; RELN; SOX1 | 0 | 0.00 | | 0 | 0.00 | | 3 | 3.31 | CHRD; GLI2; RELN | 0 | 0.00 | |
| striated muscle adaptation: GO | 23 | 0 | 0.00 | | 6 | 3.08 | ACTA1; GSN; KLF15; MSTN; MYOC; PPARGC1A | 0 | 0.00 | | 0 | 0.00 | | 2 | 2.21 | MYOC; PPARGC1A | 0 | 0.00 | |
| trabecula formation: GO | 23 | 0 | 0.00 | | 2 | 1.03 | NKX2-5; RBP4 | 0 | 0.00 | | 0 | 0.00 | | 1 | 1.10 | SLC40A1 | 0 | 0.00 | |
| tnfr2 non-canonical nf-kb pathway | 64 | 6 | 1.57 | CAP1; PSMA5; PSMB6; TNFRSF12A; TNFRSF9; TNFSF9 | 2 | 0.37 | CD70; EDA | 0 | 0.00 | | 0 | 0.00 | | 1 | 0.40 | CD70 | 1 | 0.44 | CAP1 |
| costimulation by the cd28 family | 64 | 5 | 1.31 | CD274; CD3E; CD80; CTLA4; ICOS | 0 | 0.00 | | 0 | 0.00 | | 0 | 0.00 | | 0 | 0.00 | | 1 | 0.44 | TRIB3 |
| purine nucleoside biosynthetic process: GO | 64 | 3 | 0.78 | ACOT7; AMD1; NME1 | 4 | 0.74 | ACACB; ATP6V0A4; MAT1A; SLC26A1 | 0 | 0.00 | | 0 | 0.00 | | 1 | 0.40 | ATP6V0A4 | 1 | 0.44 | ACOT7 |
| regulation of mrna stability by proteins that bind au-rich elements | 64 | 3 | 0.78 | HSPA8; PSMA5; PSMB6 | 0 | 0.00 | | 0 | 0.00 | | 0 | 0.00 | | 0 | 0.00 | | 1 | 0.44 | HSPA8 |
| histone methyltransferase complex: GO | 64 | 2 | 0.52 | ACTB; RUVBL1 | 0 | 0.00 | | 0 | 0.00 | | 0 | 0.00 | | 0 | 0.00 | | 1 | 0.44 | ACTB |
| neuron fate commitment: GO | 64 | 2 | 0.52 | NRG1; TGFBR1 | 9 | 1.66 | FEZF2; FOXN4; GLI2; MNX1; NTRK3; OLIG1; | 0 | 0.00 | | 0 | 0.00 | | 3 | 1.19 | FOXA1; GLI2; PRRX1 | 1 | 0.44 | NRG1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | PAX6; SIX1; SOX1 | | | | | | | | | | | | |
| transmembrane receptor protein tyrosine kinase activity: GO | 64 | 1 | 0.26 | NTRK1 | 10 | 1.84 | EPHA6; EPHB1; EPHB6; ERBB4; FGFR1; FGFR3; LTK; MERTK; NTRK3; ROS1 | 0 | 0.00 | | 0 | 0.00 | | 5 | 1.99 | DDR2; EFNB3; ERBB4; FGFR1; PDGFRL | 1 | 0.44 | EPHA2 |
| regulation of cell shape: GO | 135 | 8 | 0.99 | ANXA1; CCL3; CCL7; CSNK1A1; FBLIM1; IL6; MSN; PDPN | 9 | 0.79 | COCH; EPB42; GAS2; ITGA7; MYH14; PALM; SEMA3E; SLC26A5; TPM1 | 0 | 0.00 | | 0 | 0.00 | | 7 | 1.32 | COCH; DLC1; LPAR1; PALM; RHOU; SEMA3E; SHROOM3 | 3 | 0.63 | CDC42EP1; FBLIM1; MSN |
| gnrh signaling pathway | 101 | 5 | 0.83 | CALML3; CALML5; HBEGF; NRAS; PLA2G3 | 12 | 1.40 | ADCY2; ADCY5; ADCY6; ADCY8; CACNA1F; CALML6; CAMK2A; CAMK2B; LHB; PLA2G5; PLA2G6; PLCB4 | 0 | 0.00 | | 0 | 0.00 | | 1 | 0.25 | PLCB4 | 2 | 0.56 | HBEGF; PLA2G3 |
| cellular respiration: GO | 136 | 5 | 0.62 | COX7B; CYCS; NR4A3; OGDHL; SCO2 | 4 | 0.35 | CYP1A2; GPD1; PPARGC1A; SNCA | 1 | 3.07 | GPD1 | 0 | 0.00 | | 3 | 0.56 | ALDH5A1; PPARGC1A; SNCA | 3 | 0.63 | CYCS; OGDHL; SCO2 |
| phase ii - conjugation of compounds | 65 | 9 | 2.32 | CHAC1; CHAC2; CNDP2; GGCT; GSTO1; | 7 | 1.27 | ACSM5; CYP1A1; CYP1A2; GLYAT; GSTM3; | 0 | 0.00 | | 0 | 0.00 | | 0 | 0.00 | | 1 | 0.44 | GSTP1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | GSTP1; UGT1A1; UGT1A10; UGT1A7 | | | MATIA; SULT1A2 | | | | | | | | | | | | |
| regulation of cellular amino acid metabolic process: GO | 65 | 6 | 1.54 | ODC1; PSMA4; PSMA5; PSMB6; PSMD1; PSME3 | 1 | 0.18 | ATCAY | 0 | 0.00 | | 0 | 0.00 | | 0 | 0.00 | | 1 | 0.44 | ODC1 |
| rig i like receptor signaling pathway | 65 | 4 | 1.03 | CXCL10; IFNE; IL12B; ISG15 | 1 | 0.18 | IFNA5 | 0 | 0.00 | | 1 | 6.43 | ISG15 | 0 | 0.00 | | 1 | 0.44 | IFNE |
| monosaccharide binding: GO | 65 | 3 | 0.77 | CLEC17A; HK2; PYGL | 5 | 0.91 | ALDOB; CD207; COLEC11; COLEC12; P4HTM | 0 | 0.00 | | 0 | 0.00 | | 2 | 0.78 | CD207; P4HTM | 1 | 0.44 | HK2 |
| negative regulation of transforming growth factor beta receptor signaling pathway: GO | 65 | 3 | 0.77 | HSPA5; LTBP1; TGFBR1 | 2 | 0.36 | SKOR1; SKOR2 | 0 | 0.00 | | 0 | 0.00 | | 0 | 0.00 | | 1 | 0.44 | HSPA5 |
| bcr 5pathway | 65 | 2 | 0.51 | BCL2A1; CD79A | 0 | 0.00 | | 0 | 0.00 | | 0 | 0.00 | | 0 | 0.00 | | 1 | 0.44 | VAV2 |
| regulation of tor signaling: GO | 65 | 2 | 0.51 | FAM83D; HIF1A | 6 | 1.09 | HTR6; LEP; PKHD1; PRKAA2; RELN; ROS1 | 0 | 0.00 | | 0 | 0.00 | | 2 | 0.78 | PRKAA2; RELN | 1 | 0.44 | HIF1A |
| sarcoplasm: GO | 65 | 1 | 0.26 | CALR | 12 | 2.18 | ATP2A1; CACNA2D1; CAMK2B; CASQ2; GSN; GSTM2; JPH2; NOL3; PYGM; SLN; SPOCK1; TRDN | 0 | 0.00 | | 0 | 0.00 | | 4 | 1.56 | CACNA2D1; HRC; SPOCK1; TRDN | 1 | 0.44 | XDH |
| regulation | 24 | 5 | 3.49 | ANXA1; | 0 | 0.00 | | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| of type 2 immune response: GO | | | | IDO1; IL4R; IL6; RSAD2 | | | | | | | | | | | | | | | |
| disruption of cells of other organism: GO | 24 | 3 | 2.09 | CAMP; S100A12; TREM1 | 4 | 1.97 | ALB; DCD; ELANE; HAMP | 0 | 0.00 | | 1 | 17.41 | TREM1 | 3 | 3.18 | CTSG; DCD; ELANE | 0 | 0.00 | |
| indole containing compound metabolic process: GO | 24 | 3 | 2.09 | DO1; KYNU; TDO2 | 4 | 1.97 | ATP2B2; GRIN2A; HAAO; MAOA | 0 | 0.00 | | 1 | 17.41 | TDO2 | 0 | 0.00 | | 0 | 0.00 | |
| positive regulation of behavior: GO | 24 | 3 | 2.09 | GJA1; NR4A3; STRA6 | 3 | 1.47 | ALB; DRD1; NLGN1 | 0 | 0.00 | | 0 | 0.00 | | 0 | 0.00 | | 0 | 0.00 | |
| acetyl coa metabolic process: GO | 24 | 2 | 1.39 | KYNU; TDO2 | 2 | 0.98 | ACACB; ACOT12 | 0 | 0.00 | | 1 | 17.41 | TDO2 | 0 | 0.00 | | 0 | 0.00 | |
| atpase complex: GO | 24 | 2 | 1.39 | ATP12A; ATP1B3 | 3 | 1.47 | ABCA2; ATP1A2; FXYD2 | 0 | 0.00 | | 0 | 0.00 | | 1 | 1.06 | ATP1B2 | 0 | 0.00 | |
| ctcf: first multivalent nuclear factor | 24 | 2 | 1.39 | CD79A; TGFBR1 | 0 | 0.00 | | 0 | 0.00 | | 0 | 0.00 | | 0 | 0.00 | | 0 | 0.00 | |
| histone mrna metabolic process: GO | 24 | 2 | 1.39 | SNRPF; SNRPG | 0 | 0.00 | | 0 | 0.00 | | 0 | 0.00 | | 0 | 0.00 | | 0 | 0.00 | |
| negative regulation of rna splicing: GO | 24 | 2 | 1.39 | CIQBP; RPS26 | 1 | 0.49 | CELF4 | 0 | 0.00 | | 0 | 0.00 | | 0 | 0.00 | | 0 | 0.00 | |
| neuropeptide hormone activity: GO | 24 | 2 | 1.39 | ADCYAP1; CCK | 0 | 0.00 | | 0 | 0.00 | | 0 | 0.00 | | 0 | 0.00 | | 0 | 0.00 | |
| polysaccharide catabolic process: GO | 24 | 2 | 1.39 | PGM2; PYGL | 4 | 1.97 | GYG2; PHKG1; PYGM; STBD1 | 0 | 0.00 | | 0 | 0.00 | | 1 | 1.06 | PHKG1 | 0 | 0.00 | |
| regulation of thymocyte aggregation: GO | 24 | 2 | 1.39 | IL1B; IL7R | 1 | 0.49 | GLI2 | 0 | 0.00 | | 2 | 34.82 | IL1B; IL7R | 1 | 1.06 | GLI2 | 0 | 0.00 | |
| telomere maintenance via telomere | 24 | 2 | 1.39 | NOP10; PCNA | 1 | 0.49 | TERT | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| lengthening: GO | | | | | | | | | | | | | | | | | | | |
| blood vessel endothelial cell migration: GO | 24 | 1 | 0.70 | GREM1 | 3 | 1.47 | AMOT; GPLD1; SLIT2 | 0 | 0.00 | | 0 | 0.00 | | 3 | 3.18 | FGF2; GPLD1; SLIT2 | 0 | 0.00 | |
| cell cell junction organization | 24 | 1 | 0.70 | CDH3 | 2 | 0.98 | CLDN18; CLDN8 | 0 | 0.00 | | 0 | 0.00 | | 2 | 2.12 | CLDN18; CLDN8 | 0 | 0.00 | |
| cellular response to prostaglandin stimulus: GO | 24 | 1 | 0.70 | TNC | 2 | 0.98 | ADCY6; PRKAA2 | 0 | 0.00 | | 0 | 0.00 | | 4 | 4.23 | P2RY4; PRKAA2; PTGDR; PTGFR | 0 | 0.00 | |
| cholesterol efflux: GO | 24 | 1 | 0.70 | ABCG4 | 4 | 1.97 | ABCA2; APOC1; APOE; SOAT2 | 0 | 0.00 | | 0 | 0.00 | | 0 | 0.00 | | 0 | 0.00 | |
| endothelial cell proliferation: GO | 24 | 1 | 0.70 | HMOX1 | 2 | 0.98 | ANGPT4; CD34 | 0 | 0.00 | | 0 | 0.00 | | 2 | 2.12 | ANGPT4; CD34 | 0 | 0.00 | |
| forebrain regionalization: GO | 24 | 1 | 0.70 | EOMES | 3 | 1.47 | EMX2; FEZF2; PAX6 | 0 | 0.00 | | 0 | 0.00 | | 1 | 1.06 | EMX2 | 0 | 0.00 | |
| g beta gamma signalling through pi3kgamma | 24 | 1 | 0.70 | GNGT2 | 0 | 0.00 | | 0 | 0.00 | | 0 | 0.00 | | 2 | 2.12 | GNG11; PIK3R6 | 0 | 0.00 | |
| glucosamine containing compound metabolic process: GO | 24 | 1 | 0.70 | CHI3L2 | 2 | 0.98 | CHST5; RENBP | 0 | 0.00 | | 0 | 0.00 | | 0 | 0.00 | | 0 | 0.00 | |
| heart growth: GO | 24 | 1 | 0.70 | NDRG4 | 5 | 2.46 | AGT; MESP1; MYOCD; NKX2-5; SORBS2 | 0 | 0.00 | | 0 | 0.00 | | 3 | 3.18 | FOXC1; MESP1; SORBS2 | 0 | 0.00 | |
| inhibition of insulin secretion by adrenaline noradrenaline | 24 | 1 | 0.70 | GNGT2 | 3 | 1.47 | ADCY5; ADCY6; ADRA2A | 0 | 0.00 | | 0 | 0.00 | | 2 | 2.12 | ADRA2A; GNG11 | 0 | 0.00 | |
| membrane lipid catabolic process: GO | 24 | 1 | 0.70 | NEU2 | 0 | 0.00 | | 0 | 0.00 | | 0 | 0.00 | | 1 | 1.06 | ACER1 | 0 | 0.00 | |
| negative | 24 | 1 | 0.70 | CHAC1 | 0 | 0.00 | | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| regulation of notch signaling pathway: GO | | | | | | | | | | | | | | | | | | | |
| nucleotide excision repair dna gap filling: GO | 24 | 1 | 0.70 | PCNA | 0 | 0.00 | | 0 | 0.00 | | 0 | 0.00 | | 0 | 0.00 | | 0 | 0.00 | |
| nucleotide kinase activity: GO | 24 | 1 | 0.70 | CMPK2 | 2 | 0.98 | DLG2; MPP2 | 0 | 0.00 | | 0 | 0.00 | | 3 | 3.18 | AK7; DLG2; MPP2 | 0 | 0.00 | |
| nucleotide transport: GO | 24 | 1 | 0.70 | GJA1 | 1 | 0.49 | P2RX7 | 0 | 0.00 | | 0 | 0.00 | | 0 | 0.00 | | 0 | 0.00 | |
| positive regulation of b cell mediated immunity: GO | 24 | 1 | 0.70 | IFNG | 2 | 0.98 | C3; FCER2 | 0 | 0.00 | | 0 | 0.00 | | 1 | 1.06 | C3 | 0 | 0.00 | |
| positive regulation of lipid catabolic process: GO | 24 | 1 | 0.70 | IL1B | 3 | 1.47 | ABCD2; IRS2; PLIN5 | 1 | 17.41 | ABCD2 | 1 | 17.41 | IL1B | 0 | 0.00 | | 0 | 0.00 | |
| protein phosphorylated amino acid binding: GO | 24 | 1 | 0.70 | SAMSN1 | 0 | 0.00 | | 0 | 0.00 | | 1 | 17.41 | SAMSN1 | 0 | 0.00 | | 0 | 0.00 | |
| regulation of circadian sleep wake cycle: GO | 24 | 1 | 0.70 | IL6 | 5 | 2.46 | ADORA1; ALB; DRD1; KCNA2; NLGN1 | 0 | 0.00 | | 0 | 0.00 | | 0 | 0.00 | | 0 | 0.00 | |
| regulation of release of sequestered calcium ion into cytosol by sarcoplasmic reticulum: GO | 24 | 1 | 0.70 | GSTO1 | 6 | 2.95 | ANK2; ATP1A2; CASQ2; DMD; GSTM2; TRDN | 0 | 0.00 | | 0 | 0.00 | | 2 | 2.12 | HRC; TRDN | 0 | 0.00 | |
| tgf-beta receptor signaling activates smads | 24 | 1 | 0.70 | TGFBR1 | 0 | 0.00 | | 0 | 0.00 | | 0 | 0.00 | | 0 | 0.00 | | 0 | 0.00 | |
| tpo pathway | 24 | 1 | 0.70 | STAT1 | 0 | 0.00 | | 0 | 0.00 | | 0 | 0.00 | | 0 | 0.00 | | 0 | 0.00 | |
| tpo signaling pathway | 24 | 1 | 0.70 | STAT1 | 0 | 0.00 | | 0 | 0.00 | | 0 | 0.00 | | 0 | 0.00 | | 0 | 0.00 | |
| transcription cofactor | 24 | 1 | 0.70 | NR4A3 | 2 | 0.98 | PASD1; TERT | 0 | 0.00 | | 0 | 0.00 | | 1 | 1.06 | ESR1 | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| binding: GO | | | | | | | | | | | | | | | | | | | |
| trna processing in the nucleus | 24 | 1 | 0.70 | RPP40 | 0 | 0.00 | | 0 | 0.00 | | 0 | 0.00 | | 0 | 0.00 | | 0 | 0.00 | |
| cation cation antiporter activity: GO | 24 | 0 | 0.00 | | 3 | 1.47 | SLC24A2; SLC9A2; SLC9A4 | 0 | 0.00 | | 0 | 0.00 | | 1 | 1.06 | SLC9A2 | 0 | 0.00 | |
| diseases of carbohydrate metabolism | 24 | 0 | 0.00 | | 3 | 1.47 | ALDOB; GYG2; IDUA | 0 | 0.00 | | 0 | 0.00 | | 0 | 0.00 | | 0 | 0.00 | |
| endogenous sterols | 24 | 0 | 0.00 | | 3 | 1.47 | CYP17A1; CYP21A2; PTGIS | 0 | 0.00 | | 0 | 0.00 | | 0 | 0.00 | | 0 | 0.00 | |
| escrt complex: GO | 24 | 0 | 0.00 | | 1 | 0.49 | VPS37D | 0 | 0.00 | | 0 | 0.00 | | 0 | 0.00 | | 0 | 0.00 | |
| insulin receptor recycling | 24 | 0 | 0.00 | | 3 | 1.47 | ATP6V0A4; ATP6V0E2; ATP6V1B1 | 0 | 0.00 | | 0 | 0.00 | | 2 | 2.12 | ATP6V0A4; ATP6V0E2 | 0 | 0.00 | |
| oxidoreductase activity acting on the ch ch group of donors nad or nadp as acceptor: GO | 24 | 0 | 0.00 | | 1 | 0.49 | PECR | 0 | 0.00 | | 0 | 0.00 | | 0 | 0.00 | | 0 | 0.00 | |
| positive regulation of cell junction assembly: GO | 24 | 0 | 0.00 | | 2 | 0.98 | AGT; MYOC | 0 | 0.00 | | 0 | 0.00 | | 1 | 1.06 | MYOC | 0 | 0.00 | |
| positive regulation of smoothened signaling pathway: GO | 24 | 0 | 0.00 | | 2 | 0.98 | FGF9; GPC3 | 0 | 0.00 | | 0 | 0.00 | | 3 | 3.18 | FOXA1; PRRX1; SHOX2 | 0 | 0.00 | |
| protein localization to cilium: GO | 24 | 0 | 0.00 | | 0 | 0.00 | | 0 | 0.00 | | 0 | 0.00 | | 1 | 1.06 | TUB | 0 | 0.00 | |
| regulation of bad phosphorylation | 24 | 0 | 0.00 | | 2 | 0.98 | BCL2; PRKAR2B | 1 | 17.41 | PRKAR2B | 0 | 0.00 | | 1 | 1.06 | BCL2 | 0 | 0.00 | |
| regulation of histone deacetylation: GO | 24 | 0 | 0.00 | | 1 | 0.49 | USP17L2 | 0 | 0.00 | | 0 | 0.00 | | 0 | 0.00 | | 0 | 0.00 | |
| regulation of | 24 | 0 | 0.00 | | 2 | 0.98 | AMELX; | 0 | 0.00 | | 0 | 0.00 | | 1 | 1.06 | CD34 | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| odontogenesis: GO | | | | | | | CD34 | | | | | | | | | | | | |
| rna polymerase ii transcription corepressor activity: GO | 24 | 0 | 0.00 | | 4 | 1.97 | ELANE; TBX15; TBX18; TFAP2B | 0 | 0.00 | | 0 | 0.00 | | 3 | 3.18 | ELANE; TBX15; TBX18 | 0 | 0.00 | |
| signal peptide processing: GO | 24 | 0 | 0.00 | | 3 | 1.47 | F10; F7; PCSK5 | 0 | 0.00 | | 0 | 0.00 | | 0 | 0.00 | | 0 | 0.00 | |
| lipid transporter activity: GO | 102 | 7 | 1.15 | ABCA12; ABCG4; GLTP; PITPNM1; PLSCR3; PRELID1; SLC10A6 | 12 | 1.39 | ABCA3; ABCB11; ABCC3; ABCD2; ANO3; ANO9; APOD; APOE; RBP4; SLC10A2; SLC22A9; SLC27A6 | 2 | 8.19 | ABCD2; SLC27A6 | 0 | 0.00 | | 2 | 0.50 | ABCA3; ANO9 | 2 | 0.56 | PITPNM1; PRELID1 |
| response to xenobiotic stimulus: GO | 102 | 7 | 1.15 | APOBEC3A; GSTO1; GSTP1; S100A12; UGT1A1; UGT1A10; UGT1A7 | 20 | 2.31 | AOC3; CES1; CYP1A1; CYP1A2; CYP2C9; CYP2D6; CYP2J2; CYP2W1; CYP3A5; EPHX2; FMO2; GLYAT; GRIN1; GSTM2; GSTM3; PON3; RORC; SCGB1A1; SLITRK5; SULT1A2 | 0 | 0.00 | | 0 | 0.00 | | 5 | 1.25 | CES1; CYP2W1; CYP3A4; CYP3A5; PON3 | 2 | 0.56 | E2F1; GSTP1 |
| antigen processing and presentation of exogenous peptide antigen via mhc | 66 | 7 | 1.77 | FCGR1A; IFI30; PSMA4; PSMA5; PSMB6; PSMD1; | 1 | 0.18 | CD207 | 0 | 0.00 | | 0 | 0.00 | | 1 | 0.38 | CD207 | 1 | 0.43 | HLA-G |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| class i: GO activation of the mrna upon binding of the cap binding complex and eifs and subsequent binding to 43s | 66 | 3 | 0.76 | PSME3 EIF2S1; EIF4EBP1; RPS26 | 0 | 0.00 | | 0 | 0.00 | | 0 | 0.00 | | 0 | 0.00 | | 1 | 0.43 | EIF4EBP1 |
| p53 binding: GO | 66 | 3 | 0.76 | BLM; PSME3; TP63 | 5 | 0.89 | GATA1; NTRK3; ZMAT1; ZMAT4; ZNF385B | 0 | 0.00 | | 0 | 0.00 | | 2 | 0.77 | ZMAT1; ZNF385D | 1 | 0.43 | BLM |
| organ growth: GO | 66 | 2 | 0.51 | NDRG4; NLGN4X | 11 | 1.97 | ADRA1A; AGT; BCL2; FGFR3; LEP; LEPR; MESP1; MYOCD; NKX2-5; OSTN; SORBS2 | 0 | 0.00 | | 0 | 0.00 | | 9 | 3.46 | ADRA1A; BCL2; BNC2; DDR2; ESR1; FOXC1; MESP1; PSAPL1; SORBS2 | 1 | 0.43 | NLGN4X |
| transport of mature transcript to cytoplasm | 66 | 0 | 0.00 | | 0 | 0.00 | | 0 | 0.00 | | 0 | 0.00 | | 0 | 0.00 | | 1 | 0.43 | DDX39A |
| rna localization: GO | 172 | 6 | 0.58 | CCT2; EIF4A3; EIF5A; EIF5AL1; RAN; RANBP1 | 3 | 0.21 | CPEB1; DDX25; RBFOX1 | 0 | 0.00 | | 0 | 0.00 | | 3 | 0.44 | CPEB1; DDX25; RFTN2 | 4 | 0.66 | CCT2; DDX39A; EIF4A3; RAN |
| fatty acid biosynthetic process: GO | 103 | 5 | 0.81 | ACOT7; CH25H; ELOVL4; ELOVL7; PTGS2 | 13 | 1.49 | ACACB; AGMO; ELOVL2; FA2H; FADS2; GGT7; LPL; PECR; PLA2G5; | 1 | 4.06 | LPL | 0 | 0.00 | | 2 | 0.49 | PLP1; PRKAA2 | 2 | 0.55 | ACOT7; PTGS2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | PLP1; PRKAA2; PTGIS; SCD5 | | | | | | | | | | | | |
| rna polymerase ii transcription factor binding: GO | 103 | 4 | 0.65 | EOMES; IFI27; PITX1; TBX20 | 8 | 0.92 | AR; BHLHE41; DACTI; GATA1; GATA5; GSC; ID4; ZFPM2 | 0 | 0.00 | | 0 | 0.00 | | 3 | 0.74 | BHLHE41; DACT1; ZFPM2 | 2 | 0.55 | IFI27; PITX1 |
| il receptor shc signaling | 25 | 3 | 2.01 | CSF2; IL2RA; JAK3 | 1 | 0.47 | IL5 | 0 | 0.00 | | 1 | 16.72 | IL2RA | 0 | 0.00 | | 0 | 0.00 | |
| epithelial tube branching involved in lung morphogenesis: GO | 25 | 2 | 1.34 | FOXF1; TNC | 1 | 0.47 | HHIP | 0 | 0.00 | | 0 | 0.00 | | 2 | 2.03 | FOXA1; SPRY1 | 0 | 0.00 | |
| inwardly rectifying k channels | 25 | 2 | 1.34 | GNGT2; KCNJ15 | 3 | 1.42 | ABCC8; KCNJ1; KCNJ3 | 0 | 0.00 | | 0 | 0.00 | | 1 | 1.02 | ABCC9 | 0 | 0.00 | |
| ptm gamma carboxylation hypusine formation and arylsulfatase activation | 25 | 2 | 1.34 | ARSH; EIF5A | 3 | 1.42 | DHPS; F10; F7 | 0 | 0.00 | | 0 | 0.00 | | 0 | 0.00 | | 0 | 0.00 | |
| sulfur amino acid metabolism | 25 | 2 | 1.34 | AHCY; CNDP2 | 3 | 1.42 | BHMT2; CDO1; MAT1A | 0 | 0.00 | | 0 | 0.00 | | 0 | 0.00 | | 0 | 0.00 | |
| u12 type spliceosomal complex: GO | 25 | 2 | 1.34 | SNRPF; SNRPG | 0 | 0.00 | | 0 | 0.00 | | 0 | 0.00 | | 0 | 0.00 | | 0 | 0.00 | |
| very long chain fatty acid metabolic process: GO | 25 | 2 | 1.34 | ELOVL4; ELOVL7 | 6 | 2.83 | ABCD2; ACOT1; ACSBG1; CYP4F12; ELOVL2; SLC27A6 | 2 | 33.43 | ABCD2; SLC27A6 | 0 | 0.00 | | 1 | 1.02 | CYP4F12 | 0 | 0.00 | |
| detection of biotic stimulus: GO | 25 | 1 | 0.67 | PGLYRP2 | 1 | 0.47 | SSC5D | 0 | 0.00 | | 0 | 0.00 | | 1 | 1.02 | SSC5D | 0 | 0.00 | |
| drug transport: GO | 25 | 1 | 0.67 | EBP | 1 | 0.47 | ABCA8 | 0 | 0.00 | | 0 | 0.00 | | 1 | 1.02 | ABCB5 | 0 | 0.00 | |
| excitatory | 25 | 1 | 0.67 | CHRNA3 | 7 | 3.30 | ADORA1; | 0 | 0.00 | | 0 | 0.00 | | 2 | 2.03 | SLC29A1; | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| postsynaptic potential: GO | | | | | | | GRIK5; GRIN1; GRIN2A; PPPIR9A; SLC17A7; SNCA | | | | | | | | | SNCA | | | |
| glucan biosynthetic process: GO | 25 | 1 | 0.67 | PGM2 | 3 | 1.42 | GYG2; PGM5; PHKG1 | 0 | 0.00 | | 0 | 0.00 | | 2 | 2.03 | PGM5; PHKG1 | 0 | 0.00 | |
| mannosyl-transferase activity: GO | 25 | 1 | 0.67 | SDF2L1 | 0 | 0.00 | | 0 | 0.00 | | 0 | 0.00 | | 0 | 0.00 | | 0 | 0.00 | |
| myc pathway | 25 | 1 | 0.67 | RUVBL1 | 1 | 0.47 | KAT2A | 0 | 0.00 | | 0 | 0.00 | | 0 | 0.00 | | 0 | 0.00 | |
| negative regulation of striated muscle cell differentiation: GO | 25 | 1 | 0.67 | CXCL10 | 5 | 2.36 | BHLHE41; DKK1; HDAC5; MYOCD; NKX2-5 | 0 | 0.00 | | 0 | 0.00 | | 3 | 3.05 | BHLHA15; BHLHE41; PRICKLE1 | 0 | 0.00 | |
| negative regulation of toll like receptor signaling pathway: GO | 25 | 1 | 0.67 | F2RL1 | 0 | 0.00 | | 0 | 0.00 | | 0 | 0.00 | | 0 | 0.00 | | 0 | 0.00 | |
| pantothenate and coa biosynthesis | 25 | 1 | 0.67 | VNN3 | 1 | 0.47 | ENPP1 | 0 | 0.00 | | 0 | 0.00 | | 1 | 1.02 | ENPP3 | 0 | 0.00 | |
| replacement ossification: GO | 25 | 1 | 0.67 | ALPL | 1 | 0.47 | FGFR3 | 0 | 0.00 | | 0 | 0.00 | | 0 | 0.00 | | 0 | 0.00 | |
| response to prostaglandin e: GO | 25 | 1 | 0.67 | CCL21 | 2 | 0.94 | ADCY6; PRKAA2 | 0 | 0.00 | | 0 | 0.00 | | 2 | 2.03 | P2RY4; PRKAA2 | 0 | 0.00 | |
| bad pathway | 25 | 0 | 0.00 | | 2 | 0.94 | BCL2; PRKAR2B | 1 | 16.72 | PRKAR2B | 0 | 0.00 | | 1 | 1.02 | BCL2 | 0 | 0.00 | |
| chondroitin sulfate biosynthetic process: GO | 25 | 0 | 0.00 | | 2 | 0.94 | BCAN; CHST12 | 0 | 0.00 | | 0 | 0.00 | | 2 | 2.03 | CHST12; DCN | 0 | 0.00 | |
| cyclic nucleotide phospho-diesterase activity: GO | 25 | 0 | 0.00 | | 2 | 0.94 | PDE11A; PDE9A | 0 | 0.00 | | 0 | 0.00 | | 2 | 2.03 | PDE1A; PDE9A | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| ion transport by p-type atpases | 25 | 0 | 0.00 | | 1 | 0.47 | FXYD2 | 0 | 0.00 | | 0 | 0.00 | | 1 | 1.02 | ATP2C2 | 0 | 0.00 | |
| lung cell differentiation: GO | 25 | 0 | 0.00 | | 0 | 0.00 | | 0 | 0.00 | | 0 | 0.00 | | 1 | 1.02 | FOXA1 | 0 | 0.00 | |
| mcalpain pathway | 25 | 0 | 0.00 | | 3 | 1.42 | ACTA1; EGF; PRKAR2B | 1 | 16.72 | PRKAR2B | 0 | 0.00 | | 1 | 1.02 | EGF | 0 | 0.00 | |
| mitochondrial fatty acid beta-oxidation | 25 | 0 | 0.00 | | 3 | 1.42 | ACADL; ACOT12; ACSF2 | 0 | 0.00 | | 0 | 0.00 | | 0 | 0.00 | | 0 | 0.00 | |
| myosin ii complex: GO | 25 | 0 | 0.00 | | 7 | 3.30 | MYH11; MYH14; MYH3; MYL3; MYL9; MYLPF; MYOM1 | 0 | 0.00 | | 0 | 0.00 | | 1 | 1.02 | MYOM1 | 0 | 0.00 | |
| negative regulation of lipid transport: GO | 25 | 0 | 0.00 | | 4 | 1.89 | APOC1; APOE; EGF; IRS2 | 0 | 0.00 | | 0 | 0.00 | | 1 | 1.02 | EGF | 0 | 0.00 | |
| nitric oxide stimulates guanylate cyclase | 25 | 0 | 0.00 | | 5 | 2.36 | KCNMB4; NOS2; PDE11A; PDE9A; PRKG2 | 0 | 0.00 | | 0 | 0.00 | | 4 | 4.07 | PDE1A; PDE9A; PRKG1; PRKG2 | 0 | 0.00 | |
| positive regulation of calcium ion dependent exocytosis: GO | 25 | 0 | 0.00 | | 5 | 2.36 | CACNA1H; KCNB1; NLGN1; SYT1; SYT9 | 0 | 0.00 | | 0 | 0.00 | | 2 | 2.03 | CACNA1G; CACNA1H | 0 | 0.00 | |
| regulation of activin receptor signaling pathway: GO | 25 | 0 | 0.00 | | 4 | 1.89 | DACT; DACT2; FGF9; MAGI2 | 0 | 0.00 | | 0 | 0.00 | | 1 | 1.02 | DACT1 | 0 | 0.00 | |
| spectrin binding: GO | 25 | 0 | 0.00 | | 5 | 2.36 | ANK2; CAMSAP3; DYNC1I1; SLC26A5; SPTBN4 | 0 | 0.00 | | 1 | 16.72 | GBP1 | 1 | 1.02 | SPTBN4 | 0 | 0.00 | |
| neurotransmitter | 67 | 5 | 1.25 | CHRNA3; | 18 | 3.17 | CHRM1; | 1 | 6.24 | GRIA4 | 0 | 0.00 | | 6 | 2.28 | ANXA9; | 1 | 0.42 | CHRNA6 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| receptor activity: GO | | | | CHRNA6; CHRNA9; HRH3; HTR3A | | | CHRM2; CHRM3; CHRM4; CHRNA2; DRD1; DRD4; GABRA2; GABRB3; GRIA1; GRIA2; GRIA4; GRIK3; GRIK4; GRIK5; GRIN1; GRIN2A; HTR3E | | | | | | | | | CHRM1; CHRM3; GRIA1; GRIA2; GRIK3 | | | |
| organellar ribosome: GO | 67 | 4 | 1.00 | GADD45GIP1; MRPL13; MRPL36; MRPL51 | 0 | 0.00 | | 0 | 0.00 | | 0 | 0.00 | | 0 | 0.00 | | 1 | 0.42 | MPV17L2 |
| regulation of adenylate cyclase activity: GO | 67 | 4 | 1.00 | ADCYAP1; CAP1; GNAI3; GPR87 | 15 | 2.64 | ADCY2; ADCY5; ADCY6; ADCY8; ADRA2A; ADRB1; CALCR; DRD1; DRD4; GALR1; GRM7; LHCGR; PALM; TSHR; VIPR2 | 0 | 0.00 | | 0 | 0.00 | | 3 | 1.14 | ADRA2A; PALM; TSHR | 1 | 0.42 | CAP1 |
| intracellular steroid hormone receptor signaling pathway: GO | 67 | 3 | 0.75 | CALR; CCNE1; RAN | 5 | 0.88 | AR; CALCOCO1; PPARGC1A; RHOXF1; SCGB2A1 | 0 | 0.00 | | 0 | 0.00 | | 2 | 0.76 | ESR1; PPARGC1A | 1 | 0.42 | RAN |
| myosin complex: GO | 67 | 1 | 0.25 | MYO1B | 18 | 3.17 | CGN; CGNL1; MYBPC1; MYBPH; | 0 | 0.00 | | 0 | 0.00 | | 5 | 1.90 | CGN; CGNL1; MYO5C; MYOM1; | 1 | 0.42 | MYO1B |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | | | | MYH11; MYH14; MYH3; MYH7B; MYL3; MYL4; MYL9; MYLPF; MYO15A; MYO1A; MYO3A; MYO5C; MYOM1; MYOM2 | | | | | | | | | MYOM2 | | | |
| antimicrobial peptides | 26 | 7 | 4.51 | CAMP; LCN2; LYZ; PGLYRP2; PI3; S100A8; S100A9 | 3 | 1.36 | CLU; DEFB132; TF | 0 | 0.00 | | 1 | 16.07 | LYZ | 2 | 1.95 | CLU; CTSG | 0 | 0.00 | |
| regulation of t helper cell differentiation: GO | 26 | 6 | 3.86 | ANXA1; CD80; IL12B; IL4R; IL6; JAK3 | 0 | 0.00 | | 0 | 0.00 | | 0 | 0.00 | | 0 | 0.00 | | 0 | 0.00 | |
| g beta: gamma signalling through pi3kgamma | 26 | 3 | 1.93 | CSF2; IL2RA; JAK3 | 1 | 0.45 | IL5 | 0 | 0.00 | | 1 | 16.07 | IL2RA | 2 | 1.95 | GNG11; PIK3R6 | 0 | 0.00 | |
| g-protein beta: gamma signalling | 26 | 3 | 1.93 | CSF2; IL2RA; JAK3 | 1 | 0.45 | IL5 | 0 | 0.00 | | 1 | 16.07 | IL2RA | 2 | 1.95 | GNG11; PIK3R6 | 0 | 0.00 | |
| beta-alanine metabolism | 26 | 2 | 1.29 | ALDH1A3; SRM | 2 | 0.91 | ACADL; AOC3 | 0 | 0.00 | | 0 | 0.00 | | 1 | 0.98 | ALDH3A2 | 0 | 0.00 | |
| entrainment of circadian clock: GO | 26 | 2 | 1.29 | ARNTL2; USP2 | 2 | 0.91 | CRY2; PER1 | 0 | 0.00 | | 0 | 0.00 | | 1 | 0.98 | CRY2 | 0 | 0.00 | |
| glucagon type ligand receptors | 26 | 2 | 1.29 | ADCYAP1; GNGT2 | 3 | 1.36 | GCGR; SCT; VIPR2 | 0 | 0.00 | | 0 | 0.00 | | 1 | 0.98 | ADCYAP1R1 | 0 | 0.00 | |
| p38mapk pathway | 26 | 2 | 1.29 | STAT1; TGFBR1 | 0 | 0.00 | | 0 | 0.00 | | 0 | 0.00 | | 0 | 0.00 | | 0 | 0.00 | |
| positive | 26 | 2 | 1.29 | HMGCR; | 2 | 0.91 | BCL2; CDON | 0 | 0.00 | | 0 | 0.00 | | 3 | 2.93 | BCL2; CDON; | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| regulation of skeletal muscle tissue development: GO | | | | USP2 | | | | | | | | | | | | SHOX2 | | | |
| positive regulation of substrate adhesion dependent cell spreading: GO | 26 | 2 | 1.29 | C1QBP; CALR | 1 | 0.45 | MYOC | 0 | 0.00 | | 0 | 0.00 | | 1 | 0.98 | MYOC | 0 | 0.00 | |
| regulation of mesonephros development: GO | 26 | 2 | 1.29 | GDNF; GREM1 | 4 | 1.82 | AGT; NOG; SIX1; SOX8 | 0 | 0.00 | | 0 | 0.00 | | 0 | 0.00 | | 0 | 0.00 | |
| regulation of natural killer cell activation: GO | 26 | 2 | 1.29 | IL12B; PGLYRP2 | 2 | 0.91 | FLT3LG; LEP | 0 | 0.00 | | 0 | 0.00 | | 0 | 0.00 | | 0 | 0.00 | |
| regulation of viral entry into host cell: GO | 26 | 2 | 1.29 | IFITM1; IFITM3 | 3 | 1.36 | GSN; HS3ST5; TMPRSS2 | 0 | 0.00 | | 1 | 16.07 | IFITM3 | 0 | 0.00 | | 0 | 0.00 | |
| alk1 pathway | 26 | 1 | 0.64 | TGFBR1 | 0 | 0.00 | | 0 | 0.00 | | 0 | 0.00 | | 0 | 0.00 | | 0 | 0.00 | |
| calcium dependent cell cell adhesion via plasma membrane cell adhesion molecules: GO | 26 | 1 | 0.64 | DSG1 | 5 | 2.27 | CDH22; NLGN1; NRXN1; PCDHB16; PCDHB3 | 0 | 0.00 | | 0 | 0.00 | | 5 | 4.89 | CDH22; NRXN1; PCDHB11; PCDHB3; PCDHB6 | 0 | 0.00 | |
| cell junction organization | 26 | 1 | 0.64 | KRT17 | 4 | 1.82 | CLDN16; CLDN18; CLDN8; KRT15 | 0 | 0.00 | | 0 | 0.00 | | 2 | 1.95 | CLDN18; CLDN8 | 0 | 0.00 | |
| cellular response to dexamethasone stimulus: GO | 26 | 1 | 0.64 | IL6 | 1 | 0.45 | MSTN | 0 | 0.00 | | 0 | 0.00 | | 0 | 0.00 | | 0 | 0.00 | |
| cofactor transport: GO | 26 | 1 | 0.64 | PDPN | 3 | 1.36 | FOLR1; FOLR2; P2RX7 | 0 | 0.00 | | 0 | 0.00 | | 1 | 0.98 | SLC25A29 | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline: Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo: Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo: Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| g-protein mediated events | 26 | 1 | 0.64 | GNAI3 | 2 | 0.91 | ADCY8; PRKAR2B | 1 | 16.07 | PRKAR2B | 0 | 0.00 | | 0 | 0.00 | | 0 | 0.00 | |
| lipid storage: GO | 26 | 1 | 0.64 | IL1B | 4 | 1.82 | ENPP1; FITM2; PLIN5 | 1 | 16.07 | ACVR1C | 2 | 32.15 | FFAR2; IL1B | 1 | 0.98 | DGAT2 | 0 | 0.00 | |
| metal ion slc transporters | 26 | 1 | 0.64 | SLC39A6 | 2 | 0.91 | CP; SLC30A10 | 0 | 0.00 | | 0 | 0.00 | | 2 | 1.95 | CP; SLC40A1 | 0 | 0.00 | |
| microtubule polymerization: GO | 26 | 1 | 0.64 | FBXO5 | 2 | 0.91 | TPPP; TPPP3 | 1 | 16.07 | TPPP3 | 0 | 0.00 | | 1 | 0.98 | TPPP | 0 | 0.00 | |
| mll1 2 complex: GO | 26 | 1 | 0.64 | RUVBL1 | 0 | 0.00 | | 0 | 0.00 | | 0 | 0.00 | | 0 | 0.00 | | 0 | 0.00 | |
| modified amino acid transport: GO | 26 | 1 | 0.64 | PDPN | 4 | 1.82 | FOLR1; FOLR2; SLC16A12; SLC7A9 | 0 | 0.00 | | 0 | 0.00 | | 1 | 0.98 | SLC16A10 | 0 | 0.00 | |
| myocyte ad pathway | 26 | 1 | 0.64 | CAMP | 2 | 0.91 | ADRB1; KCNJ3 | 0 | 0.00 | | 0 | 0.00 | | 0 | 0.00 | | 0 | 0.00 | |
| positive regulation of potassium ion transmembrane transport: GO | 26 | 1 | 0.64 | ATP1B3 | 3 | 1.36 | ACTN2; ANK2; EDN3 | 0 | 0.00 | | 0 | 0.00 | | 2 | 1.95 | ATP1B2; EDN3 | 0 | 0.00 | |
| protein transport along microtubule: GO | 26 | 1 | 0.64 | DYNLL1 | 0 | 0.00 | | 0 | 0.00 | | 0 | 0.00 | | 0 | 0.00 | | 0 | 0.00 | |
| regulation of ryanodine sensitive calcium release channel activity: GO | 26 | 1 | 0.64 | GSTO1 | 5 | 2.27 | CASQ2; DMD; GSTM2; JPH2; TRDN | 0 | 0.00 | | 0 | 0.00 | | 2 | 1.95 | HRC; TRDN | 0 | 0.00 | |
| spliceosomal tri snrnp complex: GO | 26 | 1 | 0.64 | SNRPG | 1 | 0.45 | SNRPN | 0 | 0.00 | | 0 | 0.00 | | 1 | 0.98 | SNRPN | 0 | 0.00 | |
| transmitter gated channel activity: GO | 26 | 1 | 0.64 | CHRNA9 | 9 | 4.08 | GABRB3; GRIA1; GRIA2; GRIA4; GRIK3; | 1 | 16.07 | GRIA4 | 0 | 0.00 | | 3 | 2.93 | GRIA1; GRIA2; GRIK3 | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | GRIK4; GRIK5; GRIN1; GRIN2A | | | | | | | | | | | | |
| zinc ii ion transport: GO | 26 | 1 | 0.64 | SLC39A6 | 1 | 0.45 | SLC30A10 | 0 | 0.00 | | 0 | 0.00 | | 0 | 0.00 | | 0 | 0.00 | |
| ampa glutamate receptor complex: GO | 26 | 0 | 0.00 | | 6 | 2.72 | GRIA1; GRIA2; GRIA4; SHISA6; SHISA8; VWC2L | 1 | 16.07 | GRIA4 | 0 | 0.00 | | 4 | 3.91 | CNIH3; GRIA1; GRIA2; VWC2 | 0 | 0.00 | |
| carm1 and regulation of the estrogen receptor | 26 | 0 | 0.00 | | 2 | 0.91 | HDAC5; PPARGC1A | 0 | 0.00 | | 0 | 0.00 | | 2 | 1.95 | ESR1; PPARGC1A | 0 | 0.00 | |
| gh pathway | 26 | 0 | 0.00 | | 2 | 0.91 | GHR; SLC2A4 | 1 | 16.07 | GHR | 0 | 0.00 | | 0 | 0.00 | | 0 | 0.00 | |
| growth hormone signaling pathway | 26 | 0 | 0.00 | | 2 | 0.91 | GHR; SLC2A4 | 1 | 16.07 | GHR | 0 | 0.00 | | 0 | 0.00 | | 0 | 0.00 | |
| mrna splice site selection: GO | 26 | 0 | 0.00 | | 2 | 0.91 | CELF4; NOL3 | 0 | 0.00 | | 0 | 0.00 | | 0 | 0.00 | | 0 | 0.00 | |
| negative regulation of glial cell differentiation: GO | 26 | 0 | 0.00 | | 3 | 1.36 | ID4; NOG; NTRK3 | 0 | 0.00 | | 0 | 0.00 | | 1 | 0.98 | MYCN | 0 | 0.00 | |
| neuropeptides vip and pacap inhibit the apoptosis of activated t cells | 26 | 0 | 0.00 | | 2 | 0.91 | PRKAR2B; VIPR2 | 1 | 16.07 | PRKAR2B | 0 | 0.00 | | 0 | 0.00 | | 0 | 0.00 | |
| platelet calcium homeostasis | 26 | 0 | 0.00 | | 4 | 1.82 | ATP2A1; ATP2B2; P2RX1; P2RX7 | 0 | 0.00 | | 0 | 0.00 | | 0 | 0.00 | | 0 | 0.00 | |
| protein dealkylation: GO | 26 | 0 | 0.00 | | 1 | 0.45 | HSF4 | 0 | 0.00 | | 0 | 0.00 | | 0 | 0.00 | | 0 | 0.00 | |
| regulation of actin nucleation: GO | 26 | 0 | 0.00 | | 2 | 0.91 | GSN; SCIN | 0 | 0.00 | | 0 | 0.00 | | 1 | 0.98 | SCIN | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| regulation of excretion: GO | 26 | 0 | 0.00 | | 3 | 1.36 | ADORA1; AGT; AGTR1 | 0 | 0.00 | | 0 | 0.00 | | 2 | 1.95 | AGTR1; CORIN | 0 | 0.00 | |
| sarcomere organization: GO | 26 | 0 | 0.00 | | 8 | 3.63 | ACTN2; CASQ2; FHOD3; LDB3; MYH3; NKX2-5; OBSCN; TPM1 | 0 | 0.00 | | 0 | 0.00 | | 0 | 0.00 | | 0 | 0.00 | |
| tetrapyrrole biosynthetic process: GO | 26 | 0 | 0.00 | | 2 | 0.91 | ALAS2; PPOX | 0 | 0.00 | | 0 | 0.00 | | 1 | 0.98 | PPOX | 0 | 0.00 | |
| vip pathway | 26 | 0 | 0.00 | | 2 | 0.91 | PRKAR2B; VIPR2 | 1 | 16.07 | PRKAR2B | 0 | 0.00 | | 0 | 0.00 | | 0 | 0.00 | |
| cardiac chamber development: GO | 140 | 9 | 1.08 | DSP; FOXF1; HIF1A; LTBP1; NRG1; PRDM1; STRA6; TBX20; WNT5A | 16 | 1.35 | ANK2; COL11A1; HAND2; MESP1; MYL3; MYOCD; NKX2-5; NPY5R; PCSK5; RBP4; TBX5; TNNC1; TNNT2; TPM1; WNT11; ZFPM2 | 0 | 0.00 | | 0 | 0.00 | | 10 | 1.81 | COL11A1; CPE; FOXC1; HAND2; KCNK2; MESP1; SHOX2; TNNC1; WNT11; ZFPM2 | 3 | 0.61 | HIF1A; NRG1; WNT5A |
| exocytic vesicle: GO | 140 | 3 | 0.36 | STON2; TH; VDAC1 | 21 | 1.77 | ABCC8; ANXA13; APBA1; DNM1; GABRA2; GRIA1; GRIN1; GRIN2A; ICA1; LGI3; NPY1R; RAB3B; SLC17A7; | 0 | 0.00 | | 0 | 0.00 | | 12 | 2.18 | APBA1; DPYSL3; GRIA1; ICA1; NPY1R; RAB3B; SLC18A2; SLC40A1; SNCA; SV2B; SYN2; SYT17 | 3 | 0.61 | STON2; TH; VDAC1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | SLC6A17; SNCA; SV2B; SYN2; SYNGR1; SYT1; SYT17; SYT9 | | | | | | | | | | | | |
| interleukin-1 family signaling | 68 | 8 | 1.97 | IL1A; IL1B; IL1R2; IL1RN; MYD88; PSMA5; PSMB6; UBE2N | 1 | 0.17 | PELI2 | 0 | 0.00 | | 1 | 6.15 | IL1B | 1 | 0.37 | PELI2 | 1 | 0.42 | MYD88 |
| erythrocyte homeostasis: GO | 68 | 2 | 0.49 | HMOX1; PRDX1 | 4 | 0.69 | ALAS2; EPB42; GATA1; RHAG | 0 | 0.00 | | 0 | 0.00 | | 0 | 0.00 | | 1 | 0.42 | DYRK3 |
| smoothened signaling pathway: GO | 68 | 2 | 0.49 | FOXF1; STIL | 8 | 1.39 | BOC; CDON; DISP2; GLI2; GPC2; HHIP; PAX6; PTCH1 | 0 | 0.00 | | 0 | 0.00 | | 5 | 1.87 | B9D1; CDON; GLI2; GPC2; PTCH1 | 1 | 0.42 | STIL |
| class i mhc mediated antigen processing presentation | 106 | 4 | 0.63 | PSMA4; PSMD1; TAP2; UBE2S | 6 | 0.67 | ASB11; ASB16; ASB4; CD207; FBXO44; SPSB4 | 0 | 0.00 | | 0 | 0.00 | | 1 | 0.24 | CD207 | 2 | 0.54 | ASB15; UBE2S |
| tca cycle and respiratory electron transport | 106 | 4 | 0.63 | COX7B; CYCS; LDHA; SLC16A1 | 5 | 0.56 | ADHFE1; D2HGDH; MTND5P10; PDK4: SLC16A8 | 0 | 0.00 | | 0 | 0.00 | | 2 | 0.48 | PDK3; PDK4 | 2 | 0.54 | CYCS; LDHA |
| signaling by notch | 106 | 3 | 0.47 | E2F3; HIF1A; PSENEN | 5 | 0.56 | ATP2A1; DTX1; HDAC5; KAT2A; TLE2 | 0 | 0.00 | | 0 | 0.00 | | 3 | 0.72 | CTSG; MDK; TLE2 | 2 | 0.54 | E2F1; HIF1A |
| organelle disassembly: GO | 176 | 10 | 0.95 | CDK1; EIF2S1; FCGR3B; FGFBP1; HK2; NEFM; RIMS3; | 15 | 1.01 | BOC; CLVS1; GDF5; HCAR1; KRT15; KRT73; MAP1A; | 1 | 2.37 | KRT73 | 1 | 2.37 | TREM1 | 6 | 0.87 | AKR1E2; LMCD1; MYOM1; PPARGC1A; PRKG1; STK32A | 4 | 0.64 | CDK1; FGFBP1; HK2; NEFM |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | SERPINB10; SNRPF; TREM1 | | | MAPILC3C; MSTN; MYH11; MYOM1; OBSCN; PHYHIP; PPARGC1A; STK32A | | | | | | | | | | | | |
| positive regulation of activated t cell proliferation: GO | 27 | 6 | 3.72 | IL12B; IL2RA; JAK3; PYCARD; SLAMF1; TNFSF9 | 1 | 0.44 | GPAM | 1 | 15.48 | GPAM | 1 | 15.48 | IL2RA | 0 | 0.00 | | 0 | 0.00 | |
| pentose and glucuronate interconversions | 27 | 3 | 1.86 | UGT1A1; UGT1A10; UGT1A7 | 2 | 0.87 | UGT2A1; UGT2B7 | 0 | 0.00 | | 0 | 0.00 | | 0 | 0.00 | | 0 | 0.00 | |
| uronic acid metabolic process: GO | 27 | 3 | 1.86 | UGT1A1; UGT1A10; UGT1A7 | 3 | 1.31 | UGT2A1; UGT2B7; UGT3A2 | 0 | 0.00 | | 0 | 0.00 | | 0 | 0.00 | | 0 | 0.00 | |
| folic acid containing compound metabolic process: GO | 27 | 2 | 1.24 | GGH; MTHFD2 | 2 | 0.87 | ALDH1L1; FOLR1 | 0 | 0.00 | | 0 | 0.00 | | 0 | 0.00 | | 0 | 0.00 | |
| il4receptor in b lyphocytes | 27 | 2 | 1.24 | IL4R; JAK3 | 2 | 0.87 | BCL2; IRS2 | 0 | 0.00 | | 0 | 0.00 | | 1 | 0.94 | BCL2 | 0 | 0.00 | |
| negative regulation of lyase activity: GO | 27 | 2 | 1.24 | GNAI3; GPR87 | 5 | 2.18 | ADRA2A; DRD4; GALR1; GRM7; PALM | 0 | 0.00 | | 0 | 0.00 | | 2 | 1.88 | ADRA2A; PALM | 0 | 0.00 | |
| regulation of oligodendrocyte differentiation: GO | 27 | 2 | 1.24 | CXCR4; TNFRSF21 | 1 | 0.44 | ID4 | 0 | 0.00 | | 0 | 0.00 | | 0 | 0.00 | | 0 | 0.00 | |
| autophagosome membrane: GO | 27 | 1 | 0.62 | VMP1 | 1 | 0.44 | MAP1LC3C | 0 | 0.00 | | 0 | 0.00 | | 0 | 0.00 | | 0 | 0.00 | |
| developmental induction: GO | 27 | 1 | 0.62 | GDNF | 4 | 1.75 | FGF1; FGFR1; SIX1; SOX8 | 0 | 0.00 | | 0 | 0.00 | | 2 | 1.88 | FGFR1; SPRY1 | 0 | 0.00 | |
| egf signaling pathway | 27 | 1 | 0.62 | STAT1 | 1 | 0.44 | EGF | 0 | 0.00 | | 0 | 0.00 | | 1 | 0.94 | EGF | 0 | 0.00 | |
| g protein beta gamma | 27 | 1 | 0.62 | GNGT2 | 0 | 0.00 | | 0 | 0.00 | | 0 | 0.00 | | 2 | 1.88 | GNG11; PIK3R6 | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| signalling | | | | | | | | | | | | | | | | | | | |
| nucleotide binding domain leucine rich repeat containing receptor signaling pathway: GO | 27 | 1 | 0.62 | UBE2N | 0 | 0.00 | | 0 | 0.00 | | 0 | 0.00 | | 0 | 0.00 | | 0 | 0.00 | |
| positive regulation of phosphatase activity: GO | 27 | 1 | 0.62 | IFNG | 3 | 1.31 | CHP2; GPLD1; MAGI2 | 0 | 0.00 | | 0 | 0.00 | | 2 | 1.88 | CHP2; GPLD1 | 0 | 0.00 | |
| regulation of erad pathway: GO | 27 | 1 | 0.62 | YOD1 | 2 | 0.87 | BRSK2; SVIP | 0 | 0.00 | | 0 | 0.00 | | 2 | 1.88 | BRSK2; SVIP | 0 | 0.00 | |
| regulation of fatty acid oxidation: GO | 27 | 1 | 0.62 | NR4A3 | 8 | 3.50 | ABCD2; ACACB; ACADL; CNR1; IRS2; PDK4; PLIN5; PPARGC1A | 1 | 15.48 | ABCD2 | 0 | 0.00 | | 3 | 2.82 | DGAT2; PDK4; PPARGC1A | 0 | 0.00 | |
| regulation of t cell receptor signaling pathway: GO | 27 | 1 | 0.62 | PRNP | 1 | 0.44 | CACNA1F | 0 | 0.00 | | 1 | 15.48 | GBP1 | 0 | 0.00 | | 0 | 0.00 | |
| ribonucleoside triphosphate biosynthetic process: GO | 27 | 1 | 0.62 | NME1 | 1 | 0.44 | ATP6V0A4 | 0 | 0.00 | | 0 | 0.00 | | 1 | 0.94 | ATP6V0A4 | | 0.00 | |
| selenocysteine synthesis | 27 | 1 | 0.62 | RPL22L1 | 0 | 0.00 | | 0 | 0.00 | | 0 | 0.00 | | 0 | 0.00 | | 0 | 0.00 | |
| she mediated cascade | 27 | 1 | 0.62 | NRAS | 6 | 2.62 | FGF1; FGF17; FGF22; FGF9; FGFR1; FGFR3 | 0 | 0.00 | | 0 | 0.00 | | 3 | 2.82 | FGF2; FGF22; FGFR1 | 0 | 0.00 | |
| steroid dehydrogenase activity: GO | 27 | 1 | 0.62 | AKR1B15 | 2 | 0.87 | HSD11B1; HSD17B14 | 1 | 15.48 | HSD11B2 | 0 | 0.00 | | 0 | 0.00 | | 0 | 0.00 | |
| viral mrna translation | 27 | 1 | 0.62 | RPL22L1 | 0 | 0.00 | | 0 | 0.00 | | 0 | 0.00 | | 0 | 0.00 | | 0 | 0.00 | |
| angiotensin ii mediated activation of jnk pathway | 27 | 0 | 0.00 | | 2 | 0.87 | AGT; AGTR1 | 0 | 0.00 | | 0 | 0.00 | | 1 | 0.94 | AGTR1 | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| via pyk2 dependent signaling | | | | | | | | | | | | | | | | | | | |
| bhlh transcription factor binding: GO | 27 | 0 | 0.00 | | 3 | 1.31 | BHLHE41; TCF21; TSC22D3 | 0 | 0.00 | | 0 | 0.00 | | 2 | 1.88 | BHLHE41; TSC22D3 | 0 | 0.00 | |
| calcium activated cation channel activity: GO | 27 | 0 | 0.00 | | 4 | 1.75 | KCNMB4; KCNT2; KCNU1; TRPM3 | 0 | 0.00 | | 0 | 0.00 | | 1 | 0.94 | KCNT2 | 0 | 0.00 | |
| creb pathway | 27 | 0 | 0.00 | | 3 | 1.31 | CAMK2A; CAMK2B; PRKAR2B | 1 | 15.48 | PRKAR2B | 0 | 0.00 | | 0 | 0.00 | | 0 | 0.00 | |
| glutamate receptor activity: GO | 27 | 0 | 0.00 | | 9 | 3.93 | GRIA1; GRIA2; GRIA4; GRIK3; GRIK4; GRIK5; GRIN1; GRIN2A; GRM7 | 1 | 15.48 | GRIA4 | 0 | 0.00 | | 3 | 2.82 | GRIA1; GRIA2; GRIK3 | 0 | 0.00 | |
| glutamate secretion: GO | 27 | 0 | 0.00 | | 7 | 3.06 | APBA1; RIMS1; SLC17A7; SLC1A2; SLCIA6; SLC1A7; SYT1 | 0 | 0.00 | | 0 | 0.00 | | 4 | 3.76 | APBA1; RIMS1; SLC1A6; SLC1A7 | 0 | 0.00 | |
| motor neuron axon guidance: GO | 27 | 0 | 0.00 | | 6 | 2.62 | NOG; PLXNA3; PLXNA4; RNF165; SEMA3A; SLIT2 | 0 | 0.00 | | 0 | 0.00 | | 2 | 1.88 | PLXNA4; SLIT2 | 0 | 0.00 | |
| neuronal action potential: GO | 27 | 0 | 0.00 | | 8 | 3.50 | DRD1; KCNA1; KCNA2; KCND2; KCNMB4; MYH14; | 0 | 0.00 | | 0 | 0.00 | | 2 | 1.88 | KCND2; SCN7A | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | P2RX1; SCN7A | | | | | | | | | | | | |
| positive regulation of tor signaling: GO | 27 | 0 | 0.00 | | 3 | 1.31 | HTR6; LEP; RELN | 0 | 0.00 | | 0 | 0.00 | | 1 | 0.94 | RELN | 0 | 0.00 | |
| regulation of endoplasmic reticulum stress induced intrinsic apoptotic signaling pathway: GO | 27 | 0 | 0.00 | | 0 | 0.00 | | 0 | 0.00 | | 0 | 0.00 | | 1 | 0.94 | CREB3L1 | 0 | 0.00 | |
| regulation of fibroblast migration: GO | 27 | 0 | 0.00 | | 2 | 0.87 | CYGB; HAS1 | 0 | 0.00 | | 0 | 0.00 | | 2 | 1.88 | DDR2; FGF2 | 0 | 0.00 | |
| rna polymerase ii repressing transcription factor binding: GO | 27 | 0 | 0.00 | | 1 | 0.44 | GSC | 0 | 0.00 | | 0 | 0.00 | | 0 | 0.00 | | 0 | 0.00 | |
| trans golgi network transport vesicle: GO | 27 | 0 | 0.00 | | 2 | 0.87 | NCALD; SLC2A4 | 0 | 0.00 | | 0 | 0.00 | | 2 | 1.88 | NCALD; STEAP2 | 0 | 0.00 | |
| cell surface receptor signaling pathway involved in cell cell signaling: GO | 69 | 3 | 0.73 | CHRNA3; CHRNA6; CHRNA9 | 12 | 2.05 | ADORA1; CHRNA2; DRD4; GABRA2; GABRB3; GLI2; GRIK5; GRIN1; GRIN2A; PPP1R9A; SLC17A7; SNCA | 0 | 0.00 | | 0 | 0.00 | | 4 | 1.47 | ANXA9; GLI2; SLC29A1; SNCA | 1 | 0.41 | CHRNA6 |
| respiratory electron transport atp synthesis by chemiosmotic coupling and heat production by | 69 | 2 | 0.49 | COX7B; CYCS | 1 | 0.17 | MTND5P10 | 0 | 0.00 | | 0 | 0.00 | | 0 | 0.00 | | 1 | 0.41 | CYCS |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| uncoupling proteins | | | | | | | | | | | | | | | | | | | |
| vegfr1 2 pathway | 69 | 2 | 0.49 | SH2D2A; SHB | 1 | 0.17 | PRKAA2 | 0 | 0.00 | | 0 | 0.00 | | 1 | 0.37 | PRKAA2 | 1 | 0.41 | SHB |
| transcription elongation from rna polymerase ii promoter: GO | 69 | 1 | 0.24 | ELL2 | 0 | 0.00 | | 0 | 0.00 | | 0 | 0.00 | | 0 | 0.00 | | 1 | 0.41 | ELL2 |
| i kappab kinase nf kappab signaling: GO | 69 | 0 | 0.00 | | 0 | 0.00 | | 0 | 0.00 | | 0 | 0.00 | | 0 | 0.00 | | 1 | 0.41 | BCL3 |
| adaptive immune response based on somatic recombination of immune receptors built from immunoglobulin superfamily domains: GO | 142 | 16 | 1.89 | C1QBP; CTSC; CXCL13; EBI3; EXO1; IGHG1; IGHG2; IGHG4; IGKC; IGKV4-1; IL12B; IL13RA2; IL4R; IL6; RAET1E; SLAMF1 | 6 | 0.50 | C3; C4BPA; C6; C7; CLU; RORC | 2 | 5.89 | IGHG1; IGKV3-20 | 0 | 0.00 | | 4 | 0.72 | C3; CLU; IGHM; IGHV3-23 | 3 | 0.60 | BCL3; EXO1; IL13RA2 |
| cell cycle arrest: GO | 142 | 11 | 1.30 | CALR CDKN1A; CDKN3; EIF4G2; GADD45GIP1; IFNG; IL12B; KIF20B; PA2G4; PRNP; TGFBR1 | 8 | 0.66 | APBB1; CAB39L; GAS2; GAS2L2; HEPACAM; MAGI2; PKD1; PRKAA2 | 1 | 2.94 | CDKNIC | 0 | 0.00 | | 1 | 0.18 | PRKAA2 | 3 | 0.60 | CDKN1A; CDKN3; PA2G4 |
| erad pathway: GO | 70 | 4 | 0.96 | HSPA5; SDF2L1; VCP; YOD1 | 1 | 0.17 | BRSK2 | 0 | 0.00 | | 0 | 0.00 | | 1 | 0.36 | BRSK2 | 1 | 0.41 | HSPA5 |
| cardiac muscle contraction | 70 | 2 | 0.48 | ATP1B3; COX7B | 12 | 2.02 | ATP1A2; CACNA1F; | 0 | 0.00 | | 0 | 0.00 | | 6 | 2.18 | ATP1B2; CACNA2D1; | 1 | 0.41 | TPM4 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | CACNA2D1; CACNA2D2; CACNB1; COX7A1; FXYD2; MYL3; TNNC1; TNNT2; TPM1; TPM2 | | | | | | | | | CACNA2D2; CACNB1; COX7A1; TNNC1 | | | |
| lipid oxidation: GO | 70 | 1 | 0.24 | ADH7 | 9 | 1.52 | ABCD2; ACADL; ACOX2; ADIPOQ; CRAT; CYGB; HAO2; LEP; PPARGC1A | 2 | 11.94 | ABCD2; ADIPOQ | 0 | 0.00 | | 3 | 1.09 | ACOX2; ALDH3A2; PPARGC1A | 1 | 0.41 | PPARD |
| defensins | 28 | 4 | 2.39 | DEFB103A; DEFB103B; DEFB4A; DEFB4B | 1 | 0.42 | DEFB132 | 0 | 0.00 | | 1 | 14.92 | DEFB4A | 0 | 0.00 | | 0 | 0.00 | |
| antigen processing cross presentation | 28 | | 1.79 | PSMA4; PSMD1; TAP2 | 1 | 0.42 | CD207 | 0 | 0.00 | | 0 | 0.00 | | 1 | 0.91 | CD207 | 0 | 0.00 | |
| flavonoid metabolic process: GO | 28 | 3 | 1.79 | UGT1A1; UGT1A10; UGT1A7 | 5 | 2.11 | CYP1A1; PPARGC1A; UGT2A1; UGT2B7; UGT3A2 | 0 | 0.00 | | 0 | 0.00 | | 1 | 0.91 | PPARGC1A | 0 | 0.00 | |
| potassium ion import: GO | 28 | 3 | 1.79 | ATP12A; ATP1B3; KCNJ15 | 4 | 1.69 | ATP1A2; FXYD2; KCNJ1; KCNJ3 | 0 | 0.00 | | 0 | 0.00 | | 2 | 1.81 | ABCC9; ATP1B2 | 0 | 0.00 | |
| proteasome pathway | 28 | 3 | 1.79 | PSMA4; PSMA5; PSMB6 | 0 | 0.00 | | 0 | 0.00 | | 0 | 0.00 | | 0 | 0.00 | | 0 | 0.00 | |
| pyrimidine nucleotide biosynthetic process: GO | 28 | 3 | 1.79 | CMPK2; NME1; UPP1 | 1 | 0.42 | UPP2 | 0 | 0.00 | | 0 | 0.00 | | 0 | 0.00 | | 0 | 0.00 | |
| t cell mediated | 28 | 3 | 1.79 | CTSC; | 0 | 0.00 | | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| immunity: GO | | | | RAET1E; SLAMF1 | | | | | | | | | | | | | | | |
| downstream signaling events of b cell receptor bcr | 28 | 2 | 1.20 | PSMA4; PSMD1 | 0 | 0.00 | | 0 | 0.00 | | 0 | 0.00 | | 0 | 0.00 | | 0 | 0.00 | |
| metanephros morphogenesis: GO | 28 | 2 | 1.20 | GDNF; GREM1 | 2 | 0.84 | PKD1; SOX8 | 0 | 0.00 | | 0 | 0.00 | | 1 | 0.91 | FRAS1 | 0 | 0.00 | |
| response to growth hormone: GO | 28 | 2 | 1.20 | JAK3; TRIM16 | 3 | 1.26 | F7; GHR; HMGCS2 | 1 | 14.92 | GHR | 0 | 0.00 | | 2 | 1.81 | HMGCS2; IGFBP5 | 0 | 0.00 | |
| trail pathway | 28 | 2 | 1.20 | TNFRSF10A; TNFSF10 | 0 | 0.00 | | 0 | 0.00 | | 0 | 0.00 | | 0 | 0.00 | | 0 | 0.00 | |
| aquaporin mediated transport | 28 | 1 | 0.60 | GNGT2 | 4 | 1.69 | ADCY2; ADCY5; ADCY6; AQP4 | 0 | 0.00 | | 0 | 0.00 | | 0 | 0.00 | | 0 | 0.00 | |
| cardiac muscle cell contraction: GO | 28 | 1 | 0.60 | GJA1 | 2 | 0.84 | ANK2; CACNA2D1 | 0 | 0.00 | | 0 | 0.00 | | 1 | 0.91 | CACNA2D1 | 0 | 0.00 | |
| cell fate commitment involved in formation of primary germ layer: GO | 28 | 1 | 0.60 | EOMES | 1 | 0.42 | NANOG | 0 | 0.00 | | 0 | 0.00 | | 0 | 0.00 | | 0 | 0.00 | |
| formation of incision complex in gg-ner | 28 | 1 | 0.60 | UBE2N | 0 | 0.00 | | 0 | 0.00 | | 0 | 0.00 | | 0 | 0.00 | | 0 | 0.00 | |
| intracellular ligand gated ion channel activity: GO | 28 | 1 | 0.60 | CNGB1 | 2 | 0.84 | CFTR; JPH2 | 0 | 0.00 | | 0 | 0.00 | | 0 | 0.00 | | 0 | 0.00 | |
| mrna splicing - minor pathway | 28 | 1 | 0.60 | SNRPF | 0 | 0.00 | | 0 | 0.00 | | 0 | 0.00 | | 0 | 0.00 | | 0 | 0.00 | |
| negative regulation of cell matrix adhesion: GO | 28 | 1 | 0.60 | SERPINE1 | 4 | 1.69 | APOD; ARHGAP6; MYOC; SEMA3E | 0 | 0.00 | | 1 | 14.92 | SERPINE1 | 3 | 2.72 | DLC1; MYOC; SEMA3E | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| negative regulation of intracellular steroid hormone receptor signaling pathway: GO | 28 | 1 | 0.60 | CALR | 4 | 1.69 | CRY2; KANK2; PER1; TCF21 | 0 | 0.00 | | 0 | 0.00 | | 1 | 0.91 | CRY2 | 0 | 0.00 | |
| nonsense mediated decay (nmd) independent of the exon junction complex (ejc) | 28 | 1 | 0.60 | RPL22L1 | 0 | 0.00 | | 0 | 0.00 | | 0 | 0.00 | | 0 | 0.00 | | 0 | 0.00 | |
| pdgf signaling pathway | 28 | 1 | 0.60 | STAT1 | 0 | 0.00 | | 0 | 0.00 | | 0 | 0.00 | | 0 | 0.00 | | 0 | 0.00 | |
| pre auto-phagosomal structure: GO | 28 | 1 | 0.60 | VMP1 | 1 | 0.42 | STBD1 | 0 | 0.00 | | 0 | 0.00 | | 0 | 0.00 | | 0 | 0.00 | |
| regulation of macrophage derived foam cell differentiation: GO | 28 | 1 | 0.60 | CSF2 | 4 | 1.69 | ADIPOQ; AGT; AGTR1; LPL | 2 | 29.85 | ADIPOQ; LPL | 0 | 0.00 | | 1 | 0.91 | AGTR1 | 0 | 0.00 | |
| regulation of rhodopsin mediated signaling pathway: GO | 28 | 1 | 0.60 | CNGB1 | 1 | 0.42 | GUCA1B | 0 | 0.00 | | 0 | 0.00 | | 0 | 0.00 | | 0 | 0.00 | |
| regulation of the force of heart contraction: GO | 28 | 1 | 0.60 | IFNG | 5 | 2.11 | ADRA1A; ADRB1; ATP1A2; MYL3; MYL4 | 0 | 0.00 | | 0 | 0.00 | | 1 | 0.91 | ADRA1A | 0 | 0.00 | |
| smooth muscle cell differentiation: GO | 28 | 1 | 0.60 | FOXF1 | 4 | 1.69 | ITGA8; MESP1; MYOCD; SIX1 | 0 | 0.00 | | 0 | 0.00 | | 1 | 0.91 | MESP1 | 0 | 0.00 | |
| tnf signaling | 28 | 1 | 0.60 | USP2 | 0 | 0.00 | | 0 | 0.00 | | 0 | 0.00 | | 0 | 0.00 | | 0 | 0.00 | |
| trna modification in the nucleus and cytosol | 28 | 1 | 0.60 | EPRS | 0 | 0.00 | | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| chondroitin sulfate biosynthesis | 28 | 0 | 0.00 | | 3 | 1.26 | BCAN; CHST12; UST | 0 | 0.00 | | 0 | 0.00 | | 3 | 2.72 | CHST12; DCN; UST | 0 | 0.00 | |
| dorso-ventral axis formation | 28 | 0 | 0.00 | | 3 | 1.26 | CPEB1; ERBB4; PIWIL2 | 0 | 0.00 | | 0 | 0.00 | | 2 | 1.81 | CPEB1; ERBB4 | 0 | 0.00 | |
| muscle hypertrophy: GO | 28 | 0 | 0.00 | | 6 | 2.53 | AGT; KLF15; LEP; MYOC; MYOCD; SORBS2 | 0 | 0.00 | | 0 | 0.00 | | 2 | 1.81 | MYOC; SORBS2 | 0 | 0.00 | |
| myogenesis | 28 | 0 | 0.00 | | 3 | 1.26 | BOC; CDH4; CDON | 0 | 0.00 | | 0 | 0.00 | | 1 | 0.91 | CDON | 0 | 0.00 | |
| peptidyl glutamic acid modification: GO | 28 | 0 | 0.00 | | 4 | 1.69 | AGBL1; AGBL4; F10; F7 | 0 | 0.00 | | 0 | 0.00 | | 0 | 0.00 | | 0 | 0.00 | |
| ribonucleotide catabolic process: GO | 28 | 0 | 0.00 | | 2 | 0.84 | PDE11A; PDE9A | 0 | 0.00 | | 0 | 0.00 | | 1 | 0.91 | PDE9A | 0 | 0.00 | |
| tight junction interactions | 28 | 0 | 0.00 | | 3 | 1.26 | CLDN16; CLDN18; CLDN8 | 0 | 0.00 | | 0 | 0.00 | | 2 | 1.81 | CLDN18; CLDN8 | 0 | 0.00 | |
| cellular amino acid catabolic process: GO | 108 | 8 | 1.24 | AHCY; ALDH4A1; GOT2; HAL; IDO1; IL4I1; KYNU; TDO2 | 9 | 0.98 | ALDHIL1; ASPA; CARNS1; CDO1; GPT; HAAO; HOGA1; NOS2; PRODH | 0 | 0.00 | | 1 | 3.87 | TDO2 | 5 | 1.18 | ALDH5A1; ASPA; GPT; HDC; PRODH | 2 | 0.53 | GLDC; GOT2 |
| steroid biosynthetic process: GO | 108 | 6 | 0.93 | AKR1B15; CH25H; CYP27B1; EBP; HMGCR; SQLE | 12 | 1.31 | ABCB11; ACOX2; CACNA1H; CFTR; CYP17A1; CYP21A2; HMGCS2; HSD11B1; HSD17B14; LHB; NPC1L1; PRKAA2 | 1 | 3.87 | HSD11B2 | 0 | 0.00 | | 5 | 1.18 | ACOX2; CACNA1H; CYP3A4; HMGCS2; PRKAA2 | 2 | 0.53 | CYP27B1; SQLE |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| positive regulation of adaptive immune response: GO | 71 | 9 | 2.12 | ANXA1; CD80; IFNG; IL12B; IL1B; PRKCQ; PYCARD; RSAD2; SASH3 | 3 | 0.50 | C3; FCER2; P2RX7 | 0 | 0.00 | | 1 | 5.89 | IL1B | 1 | 0.36 | C3 | 1 | 0.40 | PRKCQ |
| unfolded protein response (upr) | 71 | 4 | 0.94 | CALR; CXCL8; HSPA5; SEC61G | 1 | 0.17 | TSPYL2 | 0 | 0.00 | | 0 | 0.00 | | 0 | 0.00 | | 1 | 0.40 | HSPA5 |
| cellular response to ketone: GO | 71 | 2 | 0.47 | IL6; MSN | 6 | 1.00 | ADCY2; ADCY5; ADCY6; MSTN; PRKAA2; UGT3A2 | 0 | 0.00 | | 0 | 0.00 | | 2 | 0.72 | P2RY4; PRKAA2 | 1 | 0.40 | MSN |
| tgf-beta signaling pathway | 71 | 2 | 0.47 | IFNG; LTBP1 | 7 | 1.16 | ACVR1C; AMHR2; BMP5; GDF5; ID4; INHBB; NOG | 1 | 5.89 | ACVR1C | 0 | 0.00 | | 3 | 1.07 | CHRD; DCN; GDF7 | 1 | 0.40 | BMPR1B |
| swi snf superfamily type complex: GO | 71 | 1 | 0.24 | RUVBL1 | 3 | 0.50 | CECR2; CHD5; SALL2 | 0 | 0.00 | | 0 | 0.00 | | 1 | 0.36 | SALL2 | 1 | 0.40 | DPF1 |
| mrna binding: GO | 145 | 8 | 0.92 | C1QBP; CALR; EIF4A3; ELAVL2; MRPL13; RPS26; SERBP1; ZC3H12A | 6 | 0.49 | CELF4; CPEB1; NOVA1; PIWIL2; RBFOX1; RBM24 | 0 | 0.00 | | 0 | 0.00 | | 2 | 0.35 | CPEB1; RBMS3 | 3 | 0.59 | EIF4A3; ELAVL2; ZC3H12A |
| negative regulation of t cell differentiation: GO | 29 | 4 | 2.31 | ANXA1; CTLA4; IL4R; JAK3 | 1 | 0.41 | DTX1 | 0 | 0.00 | | 0 | 0.00 | | 0 | 0.00 | | 0 | 0.00 | |
| multi organism membrane organization: GO | 29 | 3 | 1.73 | CCR5; CXCR4; PPLA | 1 | 0.41 | VPS37D | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| negative regulation of leukocyte migration: GO | 29 | 3 | 1.73 | CCL21; GREM1; HMOX1 | 4 | 1.63 | ADORA1; APOD; BMP5; SLIT2 | 0 | 0.00 | | 0 | 0.00 | | 2 | 1.75 | CXCL12; SLIT2 | 0 | 0.00 | |
| positive regulation of myotube differentiation: GO | 29 | 3 | 1.73 | CXCL9; IL4R; NEU2 | 3 | 1.22 | BCL2; FLT3LG; SCGB3A1 | 0 | 0.00 | | 1 | 14.41 | CXCL9 | 2 | 1.75 | BCL2; SHOX2 | 0 | 0.00 | |
| tumor necrosis factor receptor binding: GO | 29 | 3 | 1.73 | STAT1; TNFSF10; TNFSF9 | 2 | 0.81 | CD70; EDA | 0 | 0.00 | | 0 | 0.00 | | 1 | 0.88 | CD70 | 0 | 0.00 | |
| bile acid and bile salt transport: GO | 29 | 2 | 1.15 | FABP6; SLC10A6 | 4 | 1.63 | ABCB11; ABCC3; ALB; SLC10A2 | 0 | 0.00 | | 1 | 14.41 | AQP9 | 0 | 0.00 | | 0 | 0.00 | |
| muscle adaptation: GO | 29 | 2 | 1.15 | HMOX1; IL1B | 6 | 2.44 | ACTA1; GSN; KLF15; MSTN; MYOC; PPARGC1A | 0 | 0.00 | | 1 | 14.41 | IL1B | 2 | 1.75 | MYOC; PPARGC1A | 0 | 0.00 | |
| response to pain: GO | 29 | 2 | 1.15 | NTRK1; OSM | 2 | 0.81 | RELN; SLC6A2 | 0 | 0.00 | | 1 | 14.41 | OSM | 1 | 0.88 | RELN | 0 | 0.00 | |
| thyroid cancer | 29 | 2 | 1.15 | NRAS; NTRK1 | 2 | 0.81 | RXRG; TCF7L1 | 0 | 0.00 | | 0 | 0.00 | | 1 | 0.88 | TCF7L1 | 0 | 0.00 | |
| bioactive peptide induced signaling pathway | 29 | 1 | 0.58 | STAT1 | 1 | 0.41 | AGT | 0 | 0.00 | | | 0.00 | | 0 | 0.00 | | 0 | 0.00 | |
| creb phosphorylation through the activation of ras | 29 | 1 | 0.58 | NEFL | 6 | 2.44 | ACTN2; CAMK2A; CAMK2B; GRIN1; GRIN2A; RPS6KA6 | 0 | 0.00 | | 0 | 0.00 | | 1 | 0.88 | RPS6KA6 | 0 | 0.00 | |
| dual incision in gg-ner | 29 | 1 | 0.58 | PCNA | 0 | 0.00 | | 0 | 0.00 | | 0 | 0.00 | | 0 | 0.00 | | 0 | 0.00 | |
| eukaryotic translation elongation | 29 | 1 | 0.58 | RPL22L1 | 0 | 0.00 | | 0 | 0.00 | | 0 | 0.00 | | 0 | 0.00 | | 0 | 0.00 | |
| hydrogen peroxide metabolic process: | 29 | 1 | 0.58 | PRDX1 | 6 | 2.44 | CYP1A1; CYP1A2; | 0 | 0.00 | | 0 | 0.00 | | 2 | 1.75 | HBA2; HBB | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| GO | | | | | | | HBA1; HBA2; HBB; NOX1 | | | | | | | | | | | | |
| induction of apoptosis through dr3 and dr4/5 death receptors | 29 | 1 | 0.58 | TNFSF10 | 2 | 0.81 | BCL2; GAS2 | 0 | 0.00 | | 0 | 0.00 | | 1 | 0.88 | BCL2 | 0 | 0.00 | |
| mannosylation: GO | 29 | 1 | 0.58 | SDF2L1 | 0 | 0.00 | | 0 | 0.00 | | 0 | 0.00 | | 0 | 0.00 | | 0 | 0.00 | |
| nod1/2 signaling pathway | 29 | 1 | 0.58 | UBE2N | 0 | 0.00 | | 0 | 0.00 | | 0 | 0.00 | | 0 | 0.00 | | 0 | 0.00 | |
| positive regulation of calcium ion transmembrane transporter activity: GO | 29 | 1 | 0.58 | GSTO1 | 6 | 2.44 | ANK2; CACNA2D1; FGF14; GSTM2; JPH2; TRDN | 0 | 0.00 | | 0 | 0.00 | | 2 | 1.75 | CACNA2D1; TRDN | 0 | 0.00 | |
| positive regulation of embryonic development: GO | 29 | 1 | 0.58 | GDNF | 6 | 2.44 | AMOT; DMRT2; OSR1; OSR2; PHLDB1; SIX1 | 0 | 0.00 | | 0 | 0.00 | | 2 | 1.75 | DMRT2; OSR1 | 0 | 0.00 | |
| regulation of membrane repolarization: GO | 29 | 1 | 0.58 | GJA1 | 3 | 1.22 | ANK2; CACNA2D1; CASQ2 | 0 | 0.00 | | 0 | 0.00 | | 1 | 0.88 | CACNA2D1 | 0 | 0.00 | |
| regulation of neurotransmitter receptor activity: GO | 29 | 1 | 0.58 | NETO2 | 5 | 2.03 | NLGN1; NRXN1; PPARGC1A; RELN; SHANK1 | 0 | 0.00 | | 0 | 0.00 | | 4 | 3.50 | CNIH3; NRXN1; PPARGC1A; RELN | 0 | 0.00 | |
| regulation of synaptic vesicle transport: GO | 29 | 1 | 0.58 | RIMS3 | 5 | 2.03 | DNM1; FGF14; GRIK5; NLGN1; SNCA | 0 | 0.00 | | 0 | 0.00 | | 1 | 0.88 | SNCA | 0 | 0.00 | |
| replisome: GO | 29 | 1 | 0.58 | PCNA | 0 | 0.00 | | 0 | 0.00 | | 0 | 0.00 | | 0 | 0.00 | | 0 | 0.00 | |
| response to isoquinoline alkaloid: GO | 29 | 1 | 0.58 | IL1B | 3 | 1.22 | CNR1; DRD1; GRIN1 | 0 | 0.00 | | 1 | 14.41 | IL1B | 0 | 0.00 | | 0 | 0.00 | |
| signaling by | 29 | 1 | 0.58 | STAT1 | 4 | 1.63 | FGF1; FGF17; | 0 | 0.00 | | 0 | 0.00 | | 2 | 1.75 | FGF2; FGFR1 | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| fgfr1 mutants | | | | | | | FGF9; FGFR1 | | | | | | | | | | | | |
| u2 type spliceosomal complex: GO | 29 | 1 | 0.58 | SNRPG | 1 | 0.41 | SNRPN | 0 | 0.00 | | 0 | 0.00 | | 1 | 0.88 | SNRPN | 0 | 0.00 | |
| actinin binding: GO | 29 | 0 | 0.00 | | 2 | 0.81 | LDB3; SYNPO2 | 0 | 0.00 | | 0 | 0.00 | | 0 | 0.00 | | 0 | 0.00 | |
| chondroitin sulfate proteoglycan biosynthetic process: GO | 29 | 0 | 0.00 | | 2 | 0.81 | BCAN; CHST12 | 0 | 0.00 | | 0 | 0.00 | | 2 | 1.75 | CHST12; DCN | 0 | 0.00 | |
| neuron fate specification: GO | 29 | 0 | 0.00 | | 6 | 2.44 | GLI2; MNX1; NTRK3; PAX6; SIX1; SOX1 | 0 | 0.00 | | 0 | 0.00 | | 2 | 1.75 | FOXA1; GLI2 | 0 | 0.00 | |
| phosphatidyl-inositol 3 phosphate binding: GO | 29 | 0 | 0.00 | | 2 | 0.81 | JPH2; SNX21 | 0 | 0.00 | | 1 | 14.41 | SNX20 | 0 | 0.00 | | 0 | 0.00 | |
| regulation of heart morphogenesis: GO | 29 | 0 | 0.00 | | 5 | 2.03 | DKK1; HAND2; MESP1; SIX1; TBX5 | 0 | 0.00 | | 0 | 0.00 | | 3 | 2.63 | FOXC1; HAND2; MESP1 | 0 | 0.00 | |
| s acyltransferase activity: GO | 29 | 0 | 0.00 | | 3 | 1.22 | ZDHHC11; ZDHHC11B; ZDHHC15 | 0 | 0.00 | | 0 | 0.00 | | 2 | 1.75 | ZDHHC11; ZDHHC15 | 0 | 0.00 | |
| solute cation antiporter activity: GO | 29 | 0 | 0.00 | | 3 | 1.22 | SLC24A2; SLC9A2; SLC9A4 | 0 | 0.00 | | 0 | 0.00 | | 1 | 0.88 | SLC9A2 | 0 | 0.00 | |
| trafficking of ampa receptors | 29 | 0 | 0.00 | | 5 | 2.03 | CAMK2A; CAMK2B; GRIA1; GRIA2; GRIA4 | 1 | 14.41 | GRIA4 | 0 | 0.00 | | 3 | 2.63 | GRIA1; GRIA2; TSPAN7 | 0 | 0.00 | |
| wnt protein binding: GO | 29 | 0 | 0.00 | | 5 | 2.03 | EGF; FRZB; FZD4; FZD8; WIF1 | 0 | 0.00 | | 0 | 0.00 | | 2 | 1.75 | EGF; FZD7 | 0 | 0.00 | |
| regulation of exocytosis: GO | 180 | 13 | 1.21 | ANXA1; F2RL1; FOXF1; HMOX1; IFNG; | 21 | 1.38 | ADRA2A; CACNA1H; CFTR; GRIK5; IL1RAPL1; | 0 | 0.00 | | 1 | 2.32 | RAC2 | 8 | 1.13 | ADRA2A; CACNAIG; CACNA1H; PCLO; RAB3B; | 4 | 0.63 | IL13RA2; PTAFR; SERPINA10; VSNL1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | IL13RA2; IL4R; PTAFR; RAC2; RALB; RIMS3; SDC1; VSNL1 | | | KCNB1; LGI3; NLGN1; PCLO; PLA2G6; PRAM1; RAB3B; RPH3AL; SNCA; SPINK1; STXBP6; SYT1; SYT17; SYT8; SYT9; TRPV6 | | | | | | | | | SNCA; STXBP6; SYT17 | | | |
| drug metabolism cytochrome p450 | 72 | 7 | 1.63 | ADH7; ALDH1A3; GSTO1; GSTP1; UGT1A1; UGT1A10; UGT1A7 | 17 | 2.79 | ADH1B; ADH1C; CYP1A2; CYP2A6; CYP2C9; CYP2D6; CYP3A5; FMO2; FMO5; GSTA3; GSTM2; GSTM3; GSTM5; GSTT2; MAOA; UGT2A1; UGT2B7 | 0 | 0.00 | | 0 | 0.00 | | 5 | 1.76 | AOX1; CYP3A4; CYP3A5; FMO5; GSTM5 | 1 | 0.39 | GSTP1 |
| diseases of metabolism | 72 | 4 | 0.93 | CYP24A1; CYP27B1; CYP4F22; UGT1A1 | 7 | 1.15 | ABCA3; ALDOB; CYP17A1; GYG2; IDUA; MAOA; MAT1A | 0 | 0.00 | | 0 | 0.00 | | 1 | 0.35 | ABCA3 | 1 | 0.39 | CYP27B1 |
| selenoamino acid metabolism | 72 | 3 | 0.70 | AHCY; EPRS; RPL22L1 | 2 | 0.33 | GGT7; MAT1A | 0 | 0.00 | | 0 | 0.00 | | 0 | 0.00 | | 1 | 0.39 | SCLY |
| signaling by notch1 | 72 | 2 | 0.46 | HIF1A; PSENEN | 4 | 0.66 | DTX1; HDAC5; KAT2A; TLE2 | 0 | 0.00 | | 0 | 0.00 | | 1 | 0.35 | TLE2 | 1 | 0.39 | HIF1A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| actin mediated cell contraction: GO | 72 | 1 | 0.23 | GJA1 | 18 | 2.95 | ACTA1; ACTN2; ANK2; CACNA2D1; DES; DMD; MYBPC1; MYH3; MYL3; MYL4; TMOD1; TNNC1; TNNC2; TNNI2; TNNT2; TNNT3; TPM1; TPM2 | 0 | 0.00 | | 0 | 0.00 | | 3 | 1.06 | CACNA2D1; TNNC1; TNNT3 | 1 | 0.39 | TPM4 |
| vascular smooth muscle contraction | 110 | 5 | 0.76 | CALML3; CALML5; MYLK2; PLA2G3; PRKCQ | 17 | 1.82 | ADCY2; ADCY5; ADCY6; ADCY8; ADRA1A; ADRA1B; AGTR1; CACNA1F; CALML6; CYP4A11; KCNMB4; MYH11; MYL9; PLA2G5; PLA2G6; PLCB4; PPP1R14A | 0 | 0.00 | | 0 | 0.00 | | 5 | 1.15 | ADRA1A; AGTR1; CYP4A11; PLCB4; PRKG1 | 2 | 0.52 | PLA2G3; PRKCQ |
| membrane budding: GO | 110 | 4 | 0.61 | AREG; CTSC; SERPINA1; TGFA | 5 | 0.54 | FOLR1; GRIA1; P2RX7; TRAPPC6A; VPS37D | 0 | 0.00 | | 0 | 0.00 | | 4 | 0.92 | CNIH3; FCHO1; GRIA1; TRAPPC6A | 2 | 0.52 | AREG; TGFA |
| protein modification by small protein | 110 | 4 | 0.61 | USP2; USP43; YOD1; ZC3H12A | 4 | 0.43 | KAT2A; USP17L2; USP17L7; | 0 | 0.00 | | 0 | 0.00 | | 1 | 0.23 | USP17L7 | 2 | 0.52 | USP43; ZC3H12A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| removal: GO | | | | | | | USP6 | | | | | | | | | | | | |
| positive regulation of immunoglobulin production: GO | 30 | 5 | 2.79 | IFNG; IL4R; IL6; SASH3; TNFRSF4 | 2 | 0.79 | IL5; RBP4 | 0 | 0.00 | | 0 | 0.00 | | 0 | 0.00 | | 0 | 0.00 | |
| phosphatidyl-inositol 3 kinase binding: GO | 30 | 2 | 1.12 | FAM83A; FAM83B | 2 | 0.79 | IRS2; IRS4 | 0 | 0.00 | | 0 | 0.00 | | 1 | 0.85 | ESR1 | 0 | 0.00 | |
| activated notch1 transmits signal to the nucleus | 30 | 1 | 0.56 | PSENEN | 1 | 0.39 | DTX1 | 0 | 0.00 | | 0 | 0.00 | | 0 | 0.00 | | 0 | 0.00 | |
| activation of kainate receptors upon glutamate binding | 30 | 1 | 0.56 | GNGT2 | 4 | 1.57 | GRIK3; GRIK4; GRIK5; NCALD | 0 | 0.00 | | 0 | 0.00 | | 3 | 2.54 | GNG11; GRIK3; NCALD | 0 | 0.00 | |
| ephrinb rev pathway | 30 | 1 | 0.56 | CXCR4 | 2 | 0.79 | DNM1; EPHB1 | 0 | 0.00 | | 0 | 0.00 | | 0 | 0.00 | | 0 | 0.00 | |
| eukaryotic translation termination | 30 | 1 | 0.56 | RPL22L1 | 0 | 0.00 | | 0 | 0.00 | | 0 | 0.00 | | 0 | 0.00 | | 0 | 0.00 | |
| homeostasis of number of cells within a tissue: GO | 30 | 1 | 0.56 | SASH3 | 4 | 1.57 | BCL2; FLT3LG; GATA1; P2RX7 | 0 | 0.00 | | 0 | 0.00 | | 1 | 0.85 | BCL2 | 0 | 0.00 | |
| myd88 independent toll like receptor signaling pathway: GO | 30 | 1 | 0.56 | TNIP3 | 0 | 0.00 | | 0 | 0.00 | | 0 | 0.00 | | 0 | 0.00 | | 0 | 0.00 | |
| negative regulation of potassium ion transport: GO | 30 | 1 | 0.56 | ADCYAP1 | 3 | 1.18 | ACTN2; CASQ2; PLCB4 | 0 | 0.00 | | 0 | 0.00 | | 1 | 0.85 | PLCB4 | 0 | 0.00 | |
| positive regulation of multicellular organism growth: GO | 30 | 1 | 0.56 | PPIB | 5 | 1.97 | BCL2; DIO3; GHR; GPAM; SPTBN4 | 2 | 27.86 | GHR; GPAM | 0 | 0.00 | | 2 | 1.69 | BCL2; SPTBN4 | 0 | 0.00 | |
| regulation of | 30 | 1 | 0.56 | GK | 0 | 0.00 | | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| glucokinase by glucokinase regulatory protein | | | | | | | | | | | | | | | | | | | |
| rna polymerase binding: GO | 30 | 1 | 0.56 | PPIB | 1 | 0.39 | GSG1 | 0 | 0.00 | | 0 | 0.00 | | 0 | 0.00 | | 0 | 0.00 | |
| superoxide metabolic process: GO | 30 | 1 | 0.56 | PRDX1 | 3 | 1.18 | NOS2; NOX1; SOD3 | 0 | 0.00 | | 0 | 0.00 | | 1 | 0.85 | SOD3 | 0 | 0.00 | |
| synthesis of bile acids and bile salts | 30 | 1 | 0.56 | CH25H | 3 | 1.18 | ABCB11; ACOX2; PTGIS | 0 | 0.00 | | 0 | 0.00 | | 1 | 0.85 | ACOX2 | 0 | 0.00 | |
| thyroid hormone receptor binding: GO | 30 | 1 | 0.56 | OASL | 0 | 0.00 | | 0 | 0.00 | | 0 | 0.00 | | 0 | 0.00 | | 0 | 0.00 | |
| androgen metabolic process: GO | 30 | 0 | 0.00 | | 3 | 1.18 | CYP17A1; PPARGC1A; UGT2B7 | 0 | 0.00 | | 0 | 0.00 | | 3 | 2.54 | CYP3A4; ESR1; PPARGC1A | 0 | 0.00 | |
| cellular response to vascular endothelial growth factor stimulus: GO | 30 | 0 | 0.00 | | 0 | 0.00 | | 0 | 0.00 | | 0 | 0.00 | | 1 | 0.85 | FOXC1 | 0 | 0.00 | |
| cilium movement: GO | 30 | 0 | 0.00 | | 5 | 1.97 | CCDC114; CCDC40; DNAAF1; DNAH11; HYDIN | 0 | 0.00 | | 0 | 0.00 | | 1 | 0.85 | CCDC114 | 0 | 0.00 | |
| egfr downregulation | 30 | 0 | 0.00 | | 1 | 0.39 | EGF | 0 | 0.00 | | 0 | 0.00 | | 2 | 1.69 | EGF; SPRY1 | 0 | 0.00 | |
| leukotriene metabolic process: GO | 30 | 0 | 0.00 | | 4 | 1.57 | CYP4A11; CYP4F12; GGT7; PLA2G5 | 0 | 0.00 | | 0 | 0.00 | | 2 | 1.69 | CYP4A11; CYP4F12 | 0 | 0.00 | |
| multivesicular body organization: GO | 30 | 0 | 0.00 | | 1 | 0.39 | VPS37D | 0 | 0.00 | | 0 | 0.00 | | 0 | 0.00 | | 0 | 0.00 | |
| photoreceptor connecting cilium: GO | 30 | 0 | 0.00 | | 1 | 0.39 | PCDHB15 | 0 | 0.00 | | 0 | 0.00 | | 0 | 0.00 | | 0 | 0.00 | |
| saga type | 30 | 0 | 0.00 | | 1 | 0.39 | KAT2A | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| complex: GO | | | | | | | | | | | | | | | | | | | |
| signaling pathway from g-protein families | 30 | 0 | 0.00 | | 1 | 0.39 | PRKAR2B | 1 | 13.93 | PRKAR2B | 0 | 0.00 | | 0 | 0.00 | | 0 | 0.00 | |
| transferrin endocytosis and recycling | 30 | 0 | 0.00 | | 4 | 1.57 | ATP6V0A4; ATP6V0E2; ATP6V1B1; TF | 0 | 0.00 | | 0 | 0.00 | | 3 | 2.54 | ATP6V0A4; ATP6V0E2; STEAP2 | 0 | 0.00 | |
| lymphocyte costimulation: GO | 73 | 7 | 1.60 | CCL21; CD274; CD3E; CD80; CTLA4; DPP4; ICOS | 1 | 0.16 | PAK3 | 0 | 0.00 | | 0 | 0.00 | | 3 | 1.04 | EFNB3; HLA-DQB2; PAK3 | 1 | 0.39 | DPP4 |
| downstream ter signaling | 73 | 5 | 1.15 | CD3E; PRKCQ; PSMA5; PSMB6; UBE2N | 0 | 0.00 | | 0 | 0.00 | | 0 | 0.00 | | 0 | 0.00 | | 1 | 0.39 | PRKCQ |
| extracellular matrix structural constituent: GO | 73 | 0 | 0.00 | | 15 | 2.42 | AMELX; BCAN; COL11A1; COL11A2; COL 19A1; COL24A1; COL9A2; ELN; HAPLN2; MFAP5; MGP; MUC4; MUC5AC; MUC6; PRELP | 0 | 0.00 | | 0 | 0.00 | | 5 | 1.74 | COL11A1; COL24A1; ELN; FBLN1; FBLN2 | 1 | 0.39 | HAPLN3 |
| fatty acid catabolic process: GO | 73 | 0 | 0.00 | | 8 | 1.29 | ABCD2; ACADL; ACOX2; ADIPOQ; CRAT; CYP4A11; CYP4F12; LEP | 2 | 11.45 | ABCD2; ADIPOQ | 0 | 0.00 | | 4 | 1.39 | ACOX2; ALDH3A2; CYP4A11; CYP4F12 | 1 | 0.39 | PPARD |
| nucleotide | 111 | 3 | 0.45 | BRCA2; | 1 | 0.11 | NEIL1 | 0 | 0.00 | | 0 | 0.00 | | 0 | 0.00 | | 2 | 0.51 | BRCA2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| excision repair: GO | | | | PCNA; UBE2N | | | | | | | | | | | | | | | NEIL3 |
| ribonucleoprotein complex subunit organization: GO | 183 | 7 | 0.64 | C1QBP; DDX28; EIF6; NIP7; NPM1; SNRPF; SNRPG | 3 | 0.19 | CELF4; NOL3; TDRD5 | 0 | 0.00 | | 0 | 0.00 | | 0 | 0.00 | | 4 | 0.62 | DDX28; EIF6; MPV17L2; NPM1 |
| bone development: GO | 148 | 6 | 0.68 | ACP5; ALPL; LTF; PLS3; PPIB; SULF2 | 8 | 0.64 | CHAD; FGFR3; FREM1; LEP; LRRC17; MYOC; OSR2; SP5 | 0 | 0.00 | | 0 | 0.00 | | 7 | 1.20 | CHAD; ESR1; FREM1; LRRC17; MYOC; SHOX2; SP5 | 3 | 0.57 | ACP5; BMPR1B; LTF |
| hydrolase activity acting on glycosyl bonds: GO | 112 | 6 | 0.90 | CHI3L2; HPSE; HYAL3; LYZ; NEU2; PCNA | 8 | 0.84 | AMY2B; ART5; HPSE2; IDUA; MACROD1; MACROD2; NEIL1; OTOGL | 0 | 0.00 | | 1 | 3.73 | LYZ | 4 | 0.91 | ACER1; AMY2B; HPSE2; MACROD2 | 2 | 0.51 | HPSE; NEIL3 |
| nephron development: GO | 112 | 6 | 0.90 | GDNF; GPR4; GREM1; ITGA3; PGF; SULF2 | 18 | 1.90 | ADAMTS16; BCL2; CD34; FGF1; GPC3; IRX1; KLF15; MAGI2; NOG; OSR1; PKD1; POU3F3; PTCH1; SIX1; SOX8; TCF21; TFAP2B; WNT11 | 0 | 0.00 | | 0 | 0.00 | | 8 | 1.81 | ANGPT1; BCL2; CD34; FGF2; OSR1; POU3F3; PTCH1; WNT11 | 2 | 0.51 | ITGA3; WNT9B |
| regulation of calcium mediated signaling: GO | 74 | 5 | 1.13 | CCL3; CD3E; GSTO1; NRG1; PRNP | 10 | 1.59 | CASQ2; CHP2; DMD; DRD4; GSTM2; JPH2; NEUROD2; RCAN2; TMEM100; TRDN | 0 | 0.00 | | 1 | 5.65 | GBP1 | 5 | 1.72 | CHP2; HRC; LMCD1; RCAN2; TRDN | 1 | 0.38 | NRG1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| negative regulation of vasculature development: GO | 74 | 4 | 0.90 | CXCL10; GPR4; SERPINE1; STAT1 | 7 | 1.12 | AGT; AMOT; ANGPT4; HDAC5; LIF; SEMA3E; TNMD | 0 | 0.00 | | 1 | 5.65 | SERPINE1 | 6 | 2.06 | ANGPT4; DCN; ECSCR; FOXC1; SEMA3E; TNMD | 1 | 0.38 | XDH |
| actomyosin structure organization: GO | 74 | 3 | 0.68 | CNN2; KIF23; RACGAPI | 16 | 2.55 | ACTA1; ACTN2; CASQ2; CNN1; FHOD3; LDB3; LMOD1; MYH11; MYH14; MYH3; MYOZ1; NKX2-5; OBSCN; SORBS1; TMOD1; TPM1 | 0 | 0.00 | | 0 | 0.00 | | 1 | 0.34 | LMOD1 | 1 | 0.38 | KIF23 |
| calcium ion regulated exocytosis: GO | 74 | 2 | 0.45 | RIMS3; UNC13A | 11 | 1.75 | CADPS; NLGN1; P2RX7; PCLO; RIMS1; RPH3AL; SCIN; SYT1; SYT17; SYT8; SYT9 | 0 | 0.00 | | 0 | 0.00 | | 4 | 1.37 | PCLO; RIMS1; SCIN; SYT17 | 1 | 0.38 | UNC13A |
| avb3 integrin pathway | 74 | 1 | 0.23 | SDC1 | 4 | 0.64 | COL11A1; COL11A2; COL9A2; EDIL3 | 0 | 0.00 | | 0 | 0.00 | | 3 | 1.03 | COL11A1; EDIL3; FGF2 | 1 | 0.38 | COL17A1 |
| snrna metabolic process: GO | 74 | 1 | 0.23 | ELL2 | 0 | 0.00 | | 0 | 0.00 | | 0 | 0.00 | | 0 | 0.00 | | 1 | 0.38 | ELL2 |
| transcriptional repressor complex: GO | 74 | 1 | 0.23 | DEPDC1 | 7 | 1.12 | CHD5; ELANE; GATA1; PASD1; SALL2; | 0 | 0.00 | | 0 | 0.00 | | 3 | 1.03 | ELANE; SALL2; TBX15 | 1 | 0.38 | DEPDC1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | | | | TBX15; ZBTB16 | | | | | | | | | | | | |
| phagocytosis engulfment: GO | 31 | 5 | 2.70 | FCGR1A; IGHG1; IGHG2; IGHG4; IGKC | 1 | 0.38 | GSN | 1 | 13.48 | IGHG1 | 0 | 0.00 | | 3 | 2.46 | GULP1; IGHM; IGHV3-23 | 0 | 0.00 | |
| positive regulation of t cell mediated immunity: GO | 31 | 4 | 2.16 | IL12B; IL1B; RSAD2; SASH3 | 1 | 0.38 | P2RX7 | 0 | 0.00 | | 1 | 13.48 | IL1B | 0 | 0.00 | | 0 | 0.00 | |
| glucuronosyl-transferase activity: GO | 31 | 3 | 1.62 | UGT1A1; UGT1A10; UGT1A7 | 3 | 1.14 | UGT2A1; UGT2B7; UGT3A2 | 0 | 0.00 | | 0 | 0.00 | | 0 | 0.00 | | 0 | 0.00 | |
| atp hydrolysis coupled transmembrane transport: GO | 31 | 2 | 1.08 | ATP12A; ATP1B3 | 5 | 1.90 | ATP1A2; ATP6V0A4; ATP6V0E2; ATP6V1B1; FXYD2 | 0 | 0.00 | | 0 | 0.00 | | 3 | 2.46 | ATP1B2; ATP6V0A4; ATP6V0E2 | 0 | 0.00 | |
| avb3 opn pathway | 31 | 2 | 1.08 | MMP9; PLAU | 1 | 0.38 | GSN | 0 | 0.00 | | 0 | 0.00 | | 0 | 0.00 | | 0 | 0.00 | |
| neuron projection regeneration: GO | 31 | 2 | 1.08 | NEFL; TNC | 4 | 1.52 | APOD; APOE; BCL2; FOLR1 | 0 | 0.00 | | 0 | 0.00 | | 2 | 1.64 | BCL2; CHL1 | 0 | 0.00 | |
| ar nongenomic pathway | 31 | 1 | 0.54 | GNAI3 | 2 | 0.76 | AR; GNAZ | 0 | 0.00 | | 0 | 0.00 | | 0 | 0.00 | | 0 | 0.00 | |
| cytoplasmic stress granule: GO | 31 | 1 | 0.54 | EIF2S1 | 0 | 0.00 | | 0 | 0.00 | | 0 | 0.00 | | 0 | 0.00 | | 0 | 0.00 | |
| egf pathway | 31 | 1 | 0.54 | STAT1 | 1 | 0.38 | EGF | 0 | 0.00 | | 0 | 0.00 | | 1 | 0.82 | EGF | 0 | 0.00 | |
| negative regulators of rig i mda5 signaling | 31 | 1 | 0.54 | ISG15 | 0 | 0.00 | | 0 | 0.00 | | 1 | 13.48 | ISG15 | 0 | 0.00 | | 0 | 0.00 | |
| p38 alpha beta pathway | 31 | 1 | 0.54 | RALB | 1 | 0.38 | PAK3 | 0 | 0.00 | | 0 | 0.00 | | 2 | 1.64 | PAK3; PRKG1 | 0 | 0.00 | |
| regulation of gluconeogenesis: GO | 31 | 1 | 0.54 | IL6 | 7 | 2.66 | ADIPOQ; KAT2A; LEP; LEPR; MST1; PPARGC1A; SERPINA12 | 1 | 13.48 | ADIPOQ | 0 | 0.00 | | 3 | 2.46 | DGAT2; PPARGC1A; SERPINA12 | 0 | 0.00 | |
| syndecan 2 pathway | 31 | 1 | 0.54 | CSF2 | 1 | 0.38 | SDC2 | 0 | 0.00 | | 0 | 0.00 | | 0 | 0.00 | | 0 | 0.00 | |
| demethylase | 31 | 0 | 0.00 | | 2 | 0.76 | CYP1A1; | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| activity: GO | | | | | | | | | | | | | | | | | | | |
| positive regulation of bmp signaling pathway: GO | 31 | 0 | 0.00 | | 4 | 1.52 | CYP1A2 GDF5; GPC3; RNF165; ZNF423 | 0 | 0.00 | | 0 | 0.00 | | 1 | 0.82 | ZNF423 | 0 | 0.00 | |
| retrograde transport at the trans-golgi-network | 31 | 0 | 0.00 | | 1 | 0.38 | RHOBTB3 | 0 | 0.00 | | 0 | 0.00 | | 1 | 0.82 | RHOBTB3 | 0 | 0.00 | |
| walking behavior: GO | 31 | 0 | 0.00 | | 4 | 1.52 | DRD1; GLRB; MAPT; SPTBN4 | 0 | 0.00 | | 0 | 0.00 | | 5 | 4.10 | EFNB3; GLRB; MAPT; SPTBN4; ZIC1 | 0 | 0.00 | |
| voltage gated ion channel activity: GO | 184 | 6 | 0.55 | CNGB1; HTR3A; KCNJ15; KCNK1; KCNK10; VDAC1 | 30 | 1.92 | ABCC8; CACNA1F; CACNA1H; CACNA2D1; CACNA2D2; CACNB1; CLCNKA; CLCNKB; CLIC5; GRIN1; GRM7; IL1RAPL1; KCNA1; KCNA2; KCNA4; KCNB1; KCNB2; KCND2; KCNH8; KCNIP1; KCNIP2; KCNJ1; KCNJ3; KCNK12; KCNT2; KCNU1; | 0 | 0.00 | | 0 | 0.00 | | 13 | 1.80 | CACNA1G; CACNA1H; CACNA2D1; CACNA2D2; CACNB1; CLCN4; CLIC5; KCND2; KCNK12; KCNK2; KCNT2; NALCN; SCN7A | 4 | 0.62 | KCNK1; KCNK10; TMC1; VDAC1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | | | | NALCN; NOX1; SCN7A; TMC2 | | | | | | | | | | | | |
| g alpha i signalling events | 113 | 14 | 2.07 | BDKRB1; BDKRB2; CCR4; CCR5; CXCL5; CXCL9; CXCR1; FPR3; GNGT2; HCAR2; HCAR3; HRH3; LPAR3; S1PR4 | 16 | 1.67 | ADCY2; ADCY5; ADCY6; ADORA1; ADRA2A; CHRM2; CNR1; CXCR5; GALR1; GNAZ; NMUR1; NPY5R; OXER1; RGS11; RGS6; RGS9 | 1 | 3.70 | RGS11 | 4 | 14.79 | CXCL5; CXCL9; HCAR2; HCAR3 | 2 | 0.45 | ADRA2A; P2RY4 | 2 | 0.50 | BDKRB2; CXCR1 |
| positive regulation of endocytosis: GO | 113 | 10 | 1.48 | CALR; CCL21; F2RL1; GREMI; IL1B; PCSK9; PYCARD; SELE; SERPINE1; WNT5A | 9 | 0.94 | C3; EEF2K; GPC3; HAMP; MAGI2; MERTK; NLGN1; SNCA; TF | 0 | 0.00 | | 3 | 11.09 | IL1B; SELE; SERPINE1 | 4 | 0.90 | ANGPT1; C3; SNCA; TUB | 2 | 0.50 | PCSK9; WNT5A |
| cellular response to topologically incorrect protein: GO | 113 | 9 | 1.33 | BAK1; CALR; EIF2S1; HSPA5; IFNG; SDF2L1; SEC61G; VCP; YOD1 | 2 | 0.21 | CASP12; TSPYL2 | 0 | 0.00 | | 0 | 0.00 | | 3 | 0.67 | BHLHA15; CASP12; CREB3L1 | 2<br>2 | 0.50 | BAK1; HSPA5 |
| potassium channel activity: GO | 113 | 5 | 0.74 | CNGB1; HTR3A; KCNJ15; KCNK1; KCNK10 | 16 | 1.67 | ABCC8; KCNA1; KCNA2; KCNA4; KCNB1; KCNB2; | 0 | 0.00 | | 0 | 0.00 | | 5 | 1.12 | ABCC9; KCND2; KCNK12; KCNK2; KCNT2 | 2 | 0.50 | KCNK1; KCNK10 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | KCND2; KCNH8; KCNIP1; KCNIP2; KCNJ1; KCNJ3; KCNK12; KCNMB4; KCNT2; KCNU1 | | | | | | | | | | | | |
| protein acetylation: GO | 113 | 4 | 0.59 | BRCA2; ESCO2; RUVBL1; TRIM16 | 7 | 0.73 | APBB1; CHD5; KAT2A; NAT8; NUPR1; PCK1; PER1 | 0 | 0.00 | | 0 | 0.00 | | 0 | 0.00 | | 2 | 0.50 | BEND3; BRCA2 |
| extracellular ligand gated ion channel activity: GO | 75 | 5 | 1.12 | CHRNA3; CHRNA6; CHRNA9; GABRQ; HTR3A | 19 | 2.99 | CHRNA2; GABRA2; GABRB3; GABRG3; GABRP; GLRB; GRIA1; GRIA2; GRIA4; GRIK3; GRIK4; GRIK5; GRIN1; GRIN2A; HTR3E; P2RX1; P2RX6; P2RX7; SLC17A7 | 1 | 5.57 | GRIA4 | 0 | 0.00 | | 4 | 1.36 | GLRB; GRIA1; GRIA2; GRIK3 | 1 | 0.38 | CHRNA6 |
| respiratory chain: GO | 75 | 3 | 0.67 | COX7B; CYCS; HIGD1A | 2 | 0.31 | COX7A1; SNCA | 0 | 0.00 | | 0 | 0.00 | | 2 | 0.68 | COX7A1; SNCA | 1 | 0.38 | CYCS |
| secretory granule membrane: GO | 75 | 2 | 0.45 | LAMP3; SYCN | 8 | 1.26 | ABCA3; ICA1; RPH3AL; | 0 | 0.00 | | 1 | 5.57 | LAMP3 | 5 | 1.69 | ABCA3; CPE; ICA1; MYRIP; | 1 | 0.38 | PCDH7 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | | | | SERPINA5; SNCA; SYT1; SYT9; TEKT3 | | | | | | | | | SNCA | | | |
| ciliary plasm: GO | 75 | 1 | 0.22 | CENPF | 8 | 1.26 | CCDC40; DNAAF1; DNAH6; GLI2; HYDIN; MAPT; SPAG6 | 0 | 0.00 | | 0 | 0.00 | | 3 | 1.02 | CCDC114; GLI2; MAPT | 1 | 0.38 | CENPF |
| nucleobase containing compound transport: GO | 185 | 7 | 0.63 | EIF4A3; EIF5A; EIF5AL1; GJA1; RAN; RANBP1; SLC28A3 | 4 | 0.26 | CPEB1; DDX25; P2RX7; RBFOX1 | 0 | 0.00 | | 0 | 0.00 | | 4 | 0.55 | CPEB1; DDX25; RFTN2; SLC29A1 | 4 | 0.61 | DDX39A; EIF4A3; RAN; SLC28A3 |
| protein import: GO | 150 | 8 | 0.89 | HSPA4; IFNG; JAK3; KPNA2; PDIA3; RAN; RANBP1; TIMM23 | 9 | 0.71 | AGT; APOE; CLU; DRD1; EGF; FGF9; GDF5; GPIHBP1; TXNIP | 0 | 0.00 | | 0 | 0.00 | | 4 | 0.68 | CLU; EGF; PRICKLE1; TXNIP | 3 | 0.57 | BCL3; KPNA2; RAN |
| heart valve development: GO | 32 | 3 | 1.57 | PRDM1; STRA6; TBX20 | 1 | 0.37 | TBX5 | 0 | 0.00 | | 0 | 0.00 | | 1 | 0.79 | SHOX2 | 0 | 0.00 | |
| embryonic digestive tract development: GO | 32 | 2 | 1.05 | FOXF1; STRA6 | 7 | 2.58 | FGF9; GLI2; PCSK5; PKDCC; RARRES2; SCT; TCF21 | 0 | 0.00 | | 0 | 0.00 | | 3 | 2.38 | GLI2; RARRES2; SHOX2 | 0 | 0.00 | |
| metanephric nephron development: GO | 32 | 2 | 1.05 | GDNF; GREM1 | 7 | 2.58 | CD34; IRX1; OSR1; PKD1; SOX8; TCF21; TFAP2B | 0 | 0.00 | | 0 | 0.00 | | 2 | 1.59 | CD34; OSR1 | 0 | 0.00 | |
| negative regulation of anion transport: GO | 32 | 2 | 1.05 | HRH3; IL1B | 9 | 3.32 | ADORA1; ANO9; APOE; CNR1; GRM7; IRS2; LEP; NPY5R; SNCA | 0 | 0.00 | | 1 | 13.06 | IL1B | 2 | 1.59 | ANO9; SNCA | 0 | 0.00 | |
| negative | 32 | 2 | 1.05 | GSTO1; | 5 | 1.84 | CASQ2; | 0 | 0.00 | | 0 | 0.00 | | 1 | 0.79 | TRDN | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| regulation of cation channel activity: GO | | | | MMP9 | | | DRD4; GSTM2; HAMP; TRDN | | | | | | | | | | | | |
| proximal distal pattern formation: GO | 32 | 2 | 1.05 | GREM1; TP63 | 5 | 1.84 | GLI2; IRX1; LRP4; OSR1; SP8 | 0 | 0.00 | | 0 | 0.00 | | 3 | 2.38 | GLI2; HOXA10; OSR1 | 0 | 0.00 | |
| cytoplasmic pattern recognition receptor signaling pathway: GO | 32 | 1 | 0.52 | UBE2N | 0 | 0.00 | | 0 | 0.00 | | 0 | 0.00 | | 0 | 0.00 | | 0 | 0.00 | |
| global genome nucleotide excision repair: GO | 32 | 1 | 0.52 | UBE2N | 0 | 0.00 | | 0 | 0.00 | | 0 | 0.00 | | 0 | 0.00 | | 0 | 0.00 | |
| pdgf pathway | 32 | 1 | 0.52 | STAT1 | 0 | 0.00 | | 0 | 0.00 | | 0 | 0.00 | | 0 | 0.00 | | 0 | 0.00 | |
| rna polymerase ii transcription coactivator activity: GO | 32 | 1 | 0.52 | TBX20 | 3 | 1.11 | MYOCD; TFAP2B; ZFPM2 | 0 | 0.00 | | 0 | 0.00 | | 2 | 1.59 | PRRX1; ZFPM2 | 0 | 0.00 | |
| at1r pathway | 32 | 0 | 0.00 | | 2 | 0.74 | AGT; AGTR1 | 0 | 0.00 | | 0 | 0.00 | | 1 | 0.79 | AGTR1 | 0 | 0.00 | |
| glucagon signaling in metabolic regulation | 32 | 0 | 0.00 | | 6 | 2.21 | ADCY2; ADCY5; ADCY6; ADCY8; GCGR; PRKAR2B | 1 | 13.06 | PRKAR2B | 0 | 0.00 | | 1 | 0.79 | GNG11 | 0 | 0.00 | |
| netrin pathway | 32 | 0 | 0.00 | | 1 | 0.37 | CAMK2A | 0 | 0.00 | | 0 | 0.00 | | 0 | 0.00 | | 0 | 0.00 | |
| neural tube patterning: GO | 32 | 0 | 0.00 | | 4 | 1.47 | GLI2; GSC; PAX6; PTCH1 | 0 | 0.00 | | 0 | 0.00 | | 3 | 2.38 | FOXA1; GLI2; PTCH1 | 0 | 0.00 | |
| scf ubiquitin ligase complex: GO | 32 | 0 | 0.00 | | 1 | 0.37 | FBXO44 | 0 | 0.00 | | 0 | 0.00 | | 1 | 0.79 | FBXL7 | 0 | 0.00 | |
| regulation of b cell activation: GO | 114 | 13 | 1.91 | CDKN1A; CTLA4; IFNG; IGHG1; IGHG2; IGHG4; IGKC; IL6; PRDM1; | 3 | 0.31 | BCL2; IL5; IRS2 | 1 | 3.67 | IGHG1 | 1 | 3.67 | SAMSN1 | 3 | 0.67 | BCL2; IGHM; IGHV3-23 | 2 | 0.50 | CDKN1A; IL10 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | SAMSN1; SASH3; TNFRSF21; TNFRSF4 | | | | | | | | | | | | | | | |
| regulation of receptor mediated endocytosis: GO | 76 | 5 | 1.10 | CCL21; GREM1; PCSK9; SELE; SERPINE1 | 6 | 0.93 | APOC1; DKK1; HAMP; MAGI2; NLGN1; TF | 0 | 0.00 | | 2 | 11.00 | SELE; SERPINE1 | 1 | 0.33 | ANGPT1 | 1 | 0.37 | PCSK9 |
| oxidative phosphory-lation: GO | 76 | 2 | 0.44 | COX7B; CYCS | 1 | 0.16 | SNCA | 0 | 0.00 | | 0 | 0.00 | | 1 | 0.33 | SNCA | 1 | 0.37 | CYCS |
| positive regulation of immune effector process: GO | 151 | 22 | 2.44 | ANXA1; CD80; DEFB103A; DEFB103B; F2RL1; FOXF1; HMOX1; IFNG; IL12B; IL13RA2; IL1B; IL4R; IL6; KLK5; KLK7; NR4A3; PTAFR; RAC2; RSAD2; SASH3; TNFRSF4; WNT5A | 8 | 0.63 | C3; C6; FCER2; IL5; NOS2; P2RX7; RBP4; USP17L2 | 0 | 0.00 | | 3 | 8.30 | FFAR2; IL1B; RAC2 | 2 | 0.34 | C3; GPRC5B | 3 | 0.56 | IL13RA2; PTAFR; WNT5A |
| regulation of leukocyte mediated immunity: GO | 151 | 17 | 1.88 | F2RL1; FOXF1; HMOX1; IFNG; IL12B; IL13RA2; IL1B; IL4R; IL7R; JAK3; PTAFR; RAC2; RSAD2; | 7 | 0.55 | C3; C4BPA; FCER2; LEP; NOS2; P2RX7; PRAM1 | 0 | 0.00 | | 4 | 11.07 | IL1B; IL 7R; RAC2; SERPINB9 | 2 | 0.34 | C3; PIK3R6 | 3 | 0.56 | IL10; IL13RA2; PTAFR |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | SASH3; SERPINB4; SERPINB9; SLAMF1 | | | | | | | | | | | | | | | |
| protein localization to nucleus: GO | 151 | 7 | 0.78 | CALR; IFNG; JAK3; KPNA2; PDIA3; RAN; RANBP1 | 10 | 0.78 | AGT; DRD1; EGF; FGF9; GDF5; NR5A1; SIX1; SYNE1; TXNIP; ZBTB16 | 0 | 0.00 | | 0 | 0.00 | | 4 | 0.67 | EGF; PRICKLE1; SYNE1; TXNIP | 3 | 0.56 | BCL3; KPNA2; RAN |
| negative regulation of wnt signaling pathway: GO | 187 | 10 | 0.89 | CSNK1A1; GREM1; MDFI; PSMA4; PSMA5; PSMB6; PSMD1; PSME3; RGS20; WNT5A | 18 | 1.14 | APOE; CXXC4; DACT1; DKK1; DKK2; FGF9; FRZB; GPC3; GSC; LRP4; MESP1; NKX2-5; NOG; SOX10; TBX18; TLE2; WIF1; WNT11 | 0 | 0.00 | | 0 | 0.00 | | 6 | 0.82 | DACT1; MESP1; PRICKLE1; TBX18; TLE2; WNT11 | 4 | 0.61 | MDFI; RGS20; SNAI2; WNT5A |
| il12 stat4 pathway | 33 | 4 | 2.03 | CD3E; CD80; IFNG; IL2RA | 0 | 0.00 | | 0 | 0.00 | | 1 | 12.66 | IL2RA | 0 | 0.00 | | 0 | 0.00 | |
| cross-presentation of soluble exogenous antigens (endosomes) | 33 | 3 | 1.52 | FCGR1A; PSMA5; PSMB6 | 0 | 0.00 | | 0 | 0.00 | | 0 | 0.00 | | 0 | 0.00 | | 0 | 0.00 | |
| atpase activity coupled to transmembrane movement of ions phosphorylative mechanism: GO | 33 | 2 | 1.01 | ATP12A; ATP1B3 | 5 | 1.79 | ABCB11; ATP1A2; ATP2A1; ATP2B2; FXYD2 | 0 | 0.00 | | 0 | 0.00 | | 2 | 1.54 | ATP1B2; ATP2C2 | 0 | 0.00 | |
| ncadherin pathway | 33 | 2 | 1.01 | GJA1; JUP | 4 | 1.43 | CNR1; FGFR1; GRIA2; GSN | 0 | 0.00 | | 0 | 0.00 | | 2 | 1.54 | FGFR1; GRIA2 | 0 | 0.00 | |
| formation of a | 33 | 1 | 0.51 | RPL22L1 | 0 | 0.00 | | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| pool of free 40s subunits | | | | | | | | | | | | | | | | | | | |
| global genomic ner gg ner | 33 | 1 | 0.51 | PCNA | 0 | 0.00 | | 0 | 0.00 | | 0 | 0.00 | | 0 | 0.00 | | 0 | 0.00 | |
| interactions of vpr with host cellular proteins | 33 | 1 | 0.51 | SLC25A5 | 0 | 0.00 | | 0 | 0.00 | | 0 | 0.00 | | 0 | 0.00 | | 0 | 0.00 | |
| photoreceptor cell maintenance: GO | 33 | 1 | 0.51 | CNGB1 | 4 | 1.43 | CDHR1; CROCC; NXNL2; PCDH15 | 0 | 0.00 | | 0 | 0.00 | | 2 | 1.54 | MAK; TUB | 0 | 0.00 | |
| positive regulation of epithelial to mesenchymal transition: GO | 33 | 1 | 0.51 | SERPINB3 | 1 | 0.36 | ALX1 | 0 | 0.00 | | 0 | 0.00 | | 0 | 0.00 | | 0 | 0.00 | |
| positive regulation of notch signaling pathway: GO | 33 | 1 | 0.51 | TP63 | 1 | 0.36 | MESP1 | 0 | 0.00 | | 0 | 0.00 | | 1 | 0.77 | MESP1 | 0 | 0.00 | |
| protein localization to golgi apparatus: GO | 33 | 1 | 0.51 | NRAS | 0 | 0.00 | | 0 | 0.00 | | 0 | 0.00 | | 0 | 0.00 | | 0 | 0.00 | |
| spinal cord motor neuron differentiation: GO | 33 | 1 | 0.51 | TBX20 | 5 | 1.79 | GLI2; MDGA2; MNX1; PAX6; PTCH1 | 0 | 0.00 | | 0 | 0.00 | | 2 | 1.54 | GLI2; PTCH1 | 0 | 0.00 | |
| calcium ion regulated exocytosis of neurotransmitter: GO | 33 | 0 | 0.00 | | 5 | 1.79 | RPH3AL; SYT1; SYT17; SYT8; SYT9 | 0 | 0.00 | | 0 | 0.00 | | 1 | 0.77 | SYT17 | 0 | 0.00 | |
| cardiac conduction | 33 | 0 | 0.00 | | 1 | 0.36 | FXYD2 | 0 | 0.00 | | 0 | 0.00 | | 1 | 0.77 | TRPC1 | 0 | 0.00 | |
| dag and ip3 signaling | 33 | 0 | 0.00 | | 5 | 1.79 | ADCY2; ADCY5; ADCY6; ADCY8; PRKAR2B | 1 | 12.66 | PRKAR2B | 0 | 0.00 | | 1 | 0.77 | PDE1A | 0 | 0.00 | |
| nucleotide sugar metabolic | 33 | 0 | 0.00 | | 3 | 1.07 | B4GALNT2; GALT; | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| process: GO | | | | | | | RENBP | | | | | | | | | | | | |
| peroxisome organization: GO | 33 | 0 | 0.00 | | 1 | 0.36 | PEX11A | 0 | 0.00 | | 0 | 0.00 | | 0 | 0.00 | | 0 | 0.00 | |
| phosphatase inhibitor activity: GO | 33 | 0 | 0.00 | | 5 | 1.79 | ELFN2; PHACTR3; PPP1R14A; PPP1R1A; PPP1R1B | 1 | 12.66 | PPP1R1A | 0 | 0.00 | | 2 | 1.54 | PHACTR3; TESC | 0 | 0.00 | |
| positive regulation of glucose metabolic process: GO | 33 | 0 | 0.00 | | 5 | 1.79 | GPLD1; IRS2; KAT2A; PPARGC1A; SORBS1 | 0 | 0.00 | | 0 | 0.00 | | 3 | 2.31 | DGAT2; GPLD1; PPARGC1A | 0 | 0.00 | |
| regulation of protein deacetylation: GO | 33 | 0 | 0.00 | | 1 | 0.36 | USP17L2 | 0 | 0.00 | | 0 | 0.00 | | 1 | 0.77 | FRY | 0 | 0.00 | |
| signaling of hepatocyte growth factor receptor | 33 | 0 | 0.00 | | 1 | 0.36 | ACTA1 | 0 | 0.00 | | 0 | 0.00 | | 0 | 0.00 | | 0 | 0.00 | |
| calcium ion transmembrane transport: GO | 152 | 6 | 0.66 | CCL21; CCL3; CCR5; CHRNA9; PANX1; TRPC4 | 23 | 1.79 | ATP2A1; ATP2B2; CACNA1F; CACNA1H; CACNA2D1; CACNA2D2; CACNB1; GRIN1; GRIN2A; GRM7; ILIRAPL1; JPH2; MCOLN3; NOL3; P2RX7; PKD1; PKD1L2; SLC24A2; TMC2; TRDN; TRPM1; | 0 | 0.00 | | 0 | 0.00 | | 10 | 1.67 | ATP2C2; CACNA1G; CACNA1H; CACNA2D1; CACNA2D2; CACNB1; FGF2; PKD1L2; TRDN; TRPC1 | 3 | 0.56 | PANX1; TMC1; TRPV3 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | TRPM3; TRPV6 | | | | | | | | | | | | |
| polysaccharide metabolic process: GO | 77 | 5 | 1.09 | B3GNT3; CHST1; HAS3; PGM2; PYGL | 7 | 1.07 | GYG2; HAS1; PGM5; PHKG1; PPP1R1A; PYGM; STBD1 | 1 | 5.43 | PPPIRIA | 0 | 0.00 | | 2 | 0.66 | PGM5; PHKG1 | 1 | 0.37 | CHST1 |
| autophagosome: GO | 77 | 4 | 0.87 | IL1B; MEFV; RALB; VMP1 | 1 | 0.15 | MAP1LC3C | 0 | 0.00 | | 1 | 5.43 | IL1B | 0 | 0.00 | | 1 | 0.37 | MEFV |
| renal tubule development: GO | 77 | 4 | 0.87 | GDNF; GREM1; PGF; STAT1 | 16 | 2.45 | ADAMTS16; BCL2; FGF1; GPC3; IRX1; LGR5; NOG; OSR1; PKD1; POU3F3; PTCH1; SIX1; SOX8; TCF21; TFAP2B; WNT11 | 0 | 0.00 | | 0 | 0.00 | | 7 | 2.31 | BCL2; FGF2; LGR5; OSR1; POU3F3; PTCH1; WNT11 | 1 | 0.37 | WNT9B |
| thioester metabolic process: GO | 77 | 4 | 0.87 | ACOT7; ELOVL7; KYNU; TDO2 | 9 | 1.38 | ACACB; ACOT1; ACOT12; ACSBG1; ACSF2; ELOVL2; GLYAT; GPAM; SCD5 | 1 | 5.43 | GPAM | 1 | 5.43 | TDO2 | 1 | 0.33 | DGAT2 | 1 | 0.37 | ACOT7 |
| beta-catenin independent wnt signaling | 77 | 3 | 0.65 | PSMA5; PSMB6; WNT5A | 1 | 0.15 | FZD4 | 0 | 0.00 | | 0 | 0.00 | | 2 | 0.66 | FZD7; GNG11 | 1 | 0.37 | WNT5A |
| inner mitochondrial membrane protein complex: GO | 77 | 2 | 0.43 | PPIF; TIMM23 | 1 | 0.15 | SNCA | 0 | 0.00 | | 0 | 0.00 | | 1 | 0.33 | SNCA | 1 | 0.37 | PPIF |
| tumor necrosis factor mediated signaling pathway: GO | 116 | 13 | 1.88 | PSMA4; PSMA5; PSMB6; PSMD1; PSME3; PYCARD; STAT1; | 3 | 0.31 | CD70; CLDN18; EDA | 0 | 0.00 | | 0 | 0.00 | | 2 | 0.44 | CD70; CLDN18 | 2 | 0.49 | RELT; TXNDC17 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | TNFRSF10A; TNFRSF12A; TNFRSF21; TNFRSF4; TNFRSF9; TXNDC17 | | | | | | | | | | | | | | | |
| primary immunodeficiency | 34 | 6 | 2.95 | CD3E; CD79A; ICOS; IL7R; JAK3; TAP2 | 0 | 0.00 | | 0 | 0.00 | | 1 | 12.29 | IL7R | 0 | 0.00 | | 0 | 0.00 | |
| negative regulation of extrinsic apoptotic signaling pathway via death domain receptors: GO | 34 | 4 | 1.97 | HMOX1; SERPINE1; TNFRSF10A; TNFSF10 | 1 | 0.35 | BMP5 | 0 | 0.00 | | 1 | 12.29 | SERPINE1 | 0 | 0.00 | | 0 | 0.00 | |
| negative regulation of lymphocyte mediated immunity: GO | 34 | 4 | 1.97 | IL7R; SERPINB4; SERPINB9; SLAMF1 | 1 | 0.35 | C4BPA | 0 | 0.00 | | 2 | 24.58 | IL7R; SERPINB9 | 0 | 0.00 | | 0 | 0.00 | |
| coreceptor activity: GO | 34 | 3 | 1.48 | CCR5; CD80; CXCR4 | 2 | 0.69 | GPC6; IGSF1 | 0 | 0.00 | | 0 | 0.00 | | 0 | 0.00 | | 0 | 0.00 | |
| histone ubiquitination: GO | 34 | 3 | 1.48 | DTX3L; UBE2N; UHRF1 | 0 | 0.00 | | 0 | 0.00 | | 0 | 0.00 | | 0 | 0.00 | | 0 | 0.00 | |
| regulation of natural killer cell mediated immunity: GO | 34 | 3 | 1.48 | IL12B; SERPINB4; SERPINB9 | 1 | 0.35 | LEP | 0 | 0.00 | | 1 | 12.29 | SERPINB9 | 1 | 0.75 | PIK3R6 | 0 | 0.00 | |
| cell differentiation involved in kidney development: GO | 34 | 2 | 0.98 | GPR4; STAT1 | 7 | 2.43 | CD34; KLF15; MAGI2; OSR1; POU3F3; PTCH1; TCF21 | 0 | 0.00 | | 0 | 0.00 | | 4 | 2.99 | CD34; OSR1; POU3F3; PTCH1 | 0 | 0.00 | |
| degradation of dvl | 34 | 2 | 0.98 | PSMA5; PSMB6 | 0 | 0.00 | | 0 | 0.00 | | 0 | 0.00 | | 0 | 0.00 | | 0 | 0.00 | |
| folate biosynthesis | 34 | 2 | 0.98 | ALPL; GGH | 0 | 0.00 | | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| pteridine containing compound metabolic process: GO | 34 | 2 | 0.98 | GGH; MTHFD2 | 2 | 0.69 | ALDH1L1; FOLR1 | 0 | 0.00 | | 0 | 0.00 | | 0 | 0.00 | | 0 | 0.00 | |
| response to prostaglandin: GO | 34 | 2 | 0.98 | CCL21; TNC | 3 | 1.04 | ADCY6; HMGCS2; PRKAA2 | 0 | 0.00 | | 0 | 0.00 | | 5 | 3.74 | HMGCS2; P2RY4; PRKAA2; PTGDR; PTGFR | 0 | 0.00 | |
| t cell proliferation: GO | 34 | 2 | 0.98 | EBI3; TNFRSF4 | 1 | 0.35 | P2RX7 | 0 | 0.00 | | 0 | 0.00 | | 0 | 0.00 | | 0 | 0.00 | |
| bcr pathway | 34 | 1 | 0.49 | CD79A | 0 | 0.00 | | 0 | 0.00 | | 0 | 0.00 | | 0 | 0.00 | | 0 | 0.00 | |
| gap-filling dna repair synthesis and ligation in tc-ner | 34 | 1 | 0.49 | PCNA | 0 | 0.00 | | 0 | 0.00 | | 0 | 0.00 | | 0 | 0.00 | | 0 | 0.00 | |
| lung epithelium development: GO | 34 | 1 | 0.49 | STRA6 | 1 | 0.35 | PKD1 | 0 | 0.00 | | 0 | 0.00 | | 1 | 0.75 | FOXA1 | 0 | 0.00 | |
| negative regulation of mrna metabolic process: GO | 34 | 1 | 0.49 | C1QBP | 1 | 0.35 | CELF4 | 0 | 0.00 | | 0 | 0.00 | | 0 | 0.00 | | 0 | 0.00 | |
| negative regulation of response to endoplasmic reticulum stress: GO | 34 | 1 | 0.49 | YOD1 | 1 | 0.35 | SVIP | 0 | 0.00 | | 0 | 0.00 | | 2 | 1.49 | CREB3L1; SVIP | 0 | 0.00 | |
| organ formation: GO | 34 | 1 | 0.49 | TP63 | | 1.39 | FOLR1; GLI2; MESP1; NOG | 0 | 0.00 | | 0 | 0.00 | | 2 | 1.49 | GLI2; MESP1 | 0 | 0.00 | |
| protein lipid complex subunit organization: GO | 34 | 1 | 0.49 | LIPG | 7 | 2.43 | AGT; AGTR1; APOC1; APOE; LPL; PCDHGA3; SOAT2 | 1 | 12.29 | LPL | 0 | 0.00 | | 1 | 0.75 | AGTR1 | 0 | 0.00 | |
| regulation of autophagosome assembly: GO | 34 | 1 | 0.49 | RALB | 0 | 0.00 | | 0 | 0.00 | | 0 | 0.00 | | 0 | 0.00 | | 0 | 0.00 | |
| regulation of | 34 | 1 | 0.49 | C1QBP | 5 | 1.73 | C3; C4BPA; | 0 | 0.00 | | 0 | 0.00 | | 2 | 1.49 | C3; CFH | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| protein activation cascade: GO | | | | | | | C6; C7; CFH | | | | | | | | | | | | |
| response to monoamine: GO | 34 | 1 | 0.49 | NR4A3 | 5 | 1.73 | ADCY6; ADIPOQ; DRD1; PPARGC1A; SNCA | 1 | 12.29 | ADIPOQ | 0 | 0.00 | | 2 | 1.49 | PPARGC1A; SNCA | 0 | 0.00 | |
| wnt beta catenin pathway | 34 | 1 | 0.49 | CSNK1A1 | 5 | 1.73 | CXXC4; DACT1; DKK1; DKK2; WIF1 | 0 | 0.00 | | 0 | 0.00 | | 1 | 0.75 | DACT1 | 0 | 0.00 | |
| beta amyloid binding: GO | 34 | 0 | 0.00 | | 5 | 1.73 | APBA1; APBB1; APOE; COL25A1; ITM2A | 0 | 0.00 | | 0 | 0.00 | | 2 | 1.49 | APBA1; ITM2A | 0 | 0.00 | |
| cd40pathwaymap | 34 | 0 | 0.00 | | 2 | 0.69 | MAPK8IP1; SYT1 | 0 | 0.00 | | 0 | 0.00 | | 0 | 0.00 | | 0 | 0.00 | |
| delayed rectifier potassium channel activity: GO | 34 | 0 | 0.00 | | 6 | 2.08 | KCNA1; KCNA2; KCNA4; KCNB1; KCNB2; KCND2 | 0 | 0.00 | | 0 | 0.00 | | 1 | 0.75 | KCND2 | 0 | 0.00 | |
| gpcr pathway | 34 | 0 | 0.00 | | 1 | 0.35 | PRKAR2B | 1 | 12.29 | PRKAR2B | 0 | 0.00 | | 0 | 0.00 | | 0 | 0.00 | |
| positive regulation of blood pressure: GO | 34 | 0 | 0.00 | | 9 | 3.12 | ADIPOQ; ADORA1; ADRA1A; ADRAIB; ADRB1; AGT; CARTPT; CNR1; TPM1 | 2 | 24.58 | ADIPOQ; HSD11B2 | 0 | 0.00 | | 1 | 0.75 | ADRA1A | 0 | 0.00 | |
| regulation of alternative mrna splicing via spliceosome: GO | 34 | 0 | 0.00 | 4 | 3 | 1.04 | CELF4; RBFOX1; RBM11 | 0 | 0.00 | | 0 | 0.00 | | 0 | 0.00 | | 0 | 0.00 | |
| starch and sucrose metabolism | 78 | 6 | 1.29 | HK2; PGM2; PYGL; UGT1A1; UGT1A10; | 5 | 0.76 | AMY2B; ENPP1; PYGM; UGT2A1; | 0 | 0.00 | | 0 | 0.00 | | 2 | 0.65 | AMY2B; ENPP3 | 1 | 0.36 | HK2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | UGT1A7 | | | UGT2B7 | | | | | | | | | | | | |
| transcriptional repressor activity rna polymerase ii transcription factor binding: GO | 78 | 3 | 0.64 | EOMES; PITX1; TBX20 | 9 | 1.36 | BHLHE41; ELANE; MYOCD; NKX2-5; SOX10; TBX15; TBX18; TFAP2B; ZFPM2 | 0 | 0.00 | | 0 | 0.00 | | 6 | 1.95 | BHLHE41; ELANE; PRRX1; TBX15; TBX18; ZFPM2 | 1 | 0.36 | PITX1 |
| peroxisome | 78 | 1 | 0.21 | PRDX1 | 8 | 1.21 | ABCD2; ACOX2; CRAT; EPHX2; HAO2; NOS2; PECR; PEX11A | 1 | 5.36 | ABCD2 | 0 | 0.00 | | 1 | 0.33 | ACOX2 | 1 | 0.36 | XDH |
| positive regulation of canonical wnt signaling pathway: GO | 117 | 9 | 1.29 | ASPM; JUP; PSMA4; PSMA5; PSMB6; PSMD1; PSME3; SULF2; WNT7A | 4 | 0.40 | DKK2; EDA; FGF9; LGR5 | 0 | 0.00 | | 0 | 0.00 | | 2 | 0.43 | GPRC5B; LGR5 | 2 | 0.48 | ASPM; WNT7A |
| protein phosphatase binding: GO | 117 | 6 | 0.86 | EIF4EBP1; HMGCR; JAK3; JUP; NEK2; VCP | 10 | 1.01 | BCL2; DRD1; HSF4; IRS2; KAT2A; MAPT; MYOZ2; PHACTR3; PPP1R9A; ROS1 | 0 | 0.00 | | 0 | 0.00 | | 3 | 0.65 | BCL2; MAPT; PHACTR3 | 2 | 0.48 | EIF4EBP1; NEK2 |
| positive regulation of b cell activation: GO | 79 | 10 | 2.12 | CDKN1A; IFNG; IGHG1; IGHG2; IGHG4; IGKC; IL6; PRDM1; SASH3; TNFRSF4 | 3 | 0.45 | BCL2; IL5; IRS2 | 1 | 5.29 | IGHG1 | 0 | 0.00 | | 3 | 0.96 | BCL2; IGHM; IGHV3-23 | 1 | 0.36 | CDKN1A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| steroid hormone receptor binding: GO | 79 | 5 | 1.06 | CALR; CCNE1; NR4A3; PCNA; RAN | 2 | 0.30 | PPARGC1A; TCF21 | 0 | 0.00 | | 0 | 0.00 | | 1 | 0.32 | PPARGC1A | 1 | 0.36 | RAN |
| dendrite development: GO | 79 | 2 | 0.42 | UBA6; WNT7A | 13 | 1.94 | CTNND2; DCLK1; DCX; EPHB1; FEZF2; LRP4; MAP6; PAK3; RELN; SDC2; SEMA3A; SHANK1; SLITRK5 | 0 | 0.00 | | 0 | 0.00 | | 5 | 1.61 | DCLK1; PAK3; PREX2; PRKG1; RELN | 1 | 0.36 | WNT7A |
| transcriptional regulation of white adipocyte differentiation | 79 | 0 | 0.00 | | 9 | 1.34 | ADIPOQ; EBF1; FABP4; LEP; LPL; PCK1; PLIN1; PPARGC1A; SLC2A4 | 2 | 10.58 | ADIPOQ; LPL | 0 | 0.00 | | 2 | 0.64 | EBF1; PPARGC1A | 1 | 0.36 | ANGPTL4 |
| negative regulation of adaptive immune response: GO | 35 | 6 | 2.87 | IL1RL1; IL4R; IL7R; JAK3; SAMSN1; SLAMF1 | 1 | 0.34 | C4BPA | 0 | 0.00 | | 2 | 23.88 | IL7R; SAMSN1 | 0 | 0.00 | | 0 | 0.00 | |
| death receptor signalling | 35 | 3 | 1.43 | TNFRSF10A; TNFSF10; USP2 | 0 | 0.00 | | 0 | 0.00 | | 0 | 0.00 | | 0 | 0.00 | | 0 | 0.00 | |
| erbb1 receptor proximal pathway | 35 | 3 | 1.43 | GNAI3; NRAS; STAT1 | 2 | 0.67 | EGF; GSN | 0 | 0.00 | | 0 | 0.00 | | 1 | 0.73 | EGF | 0 | 0.00 | |
| bile acid metabolic process: GO | 35 | 2 | 0.96 | CH25H; FABP6 | 3 | 1.01 | ABCB11; ACOX2; LEP | 0 | 0.00 | | 0 | 0.00 | | 1 | 0.73 | ACOX2 | 0 | 0.00 | |
| coronary vasculature development: GO | 35 | 2 | 0.96 | LTBP1; PRDM1 | 5 | 1.69 | GPC3; HAND2; MESP1; PCSK5; TBX5 | 0 | 0.00 | | 0 | 0.00 | | 3 | 2.18 | HAND2; MESP1; PRICKLE1 | 0 | 0.00 | |
| endoplasmic reticulum organization: GO | 35 | 2 | 0.96 | RAB10; VMP1 | 2 | 0.67 | REEP2; TRDN | 0 | 0.00 | | 0 | 0.00 | | 2 | 1.45 | ATL1; TRDN | 0 | 0.00 | |
| p38 mapk signaling pathway | 35 | 2 | 0.96 | STAT1; TGFBR1 | 0 | 0.00 | | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| post translational protein modification: GO | 35 | 2 | 0.96 | ARSH; ESCO2 | 3 | 1.01 | AGBL1; AGBL4; FN3K | 0 | 0.00 | | 0 | 0.00 | | 1 | 0.73 | FN3K | 0 | 0.00 | |
| regulation of activated pak-2p34 by proteasome mediated degradation | 35 | 2 | 0.96 | PSMA5; PSMB6 | 0 | 0.00 | | 0 | 0.00 | | 0 | 0.00 | | 0 | 0.00 | | 0 | 0.00 | |
| regulation of renal system process: GO | 35 | 2 | 0.96 | F2RL1; GJA1 | 4 | 1.35 | ADIPOQ; ADORA1; AGT; AGTR1 | 1 | 11.94 | ADIPOQ | 0 | 0.00 | | 2 | 1.45 | AGTR1; CORIN | 0 | 0.00 | |
| vif-mediated degradation of apobec3g | 35 | 2 | 0.96 | PSMA5; PSMB6 | 0 | 0.00 | | 0 | 0.00 | | 0 | 0.00 | | 0 | 0.00 | | 0 | 0.00 | |
| cd40 pathway | 35 | 1 | 0.48 | JAK3 | 1 | 0.34 | C4BPA | 0 | 0.00 | | 0 | 0.00 | | 0 | 0.00 | | 0 | 0.00 | |
| cyclic nucleotide binding: GO | 35 | 1 | 0.48 | CNGB1 | 3 | 1.01 | PDE11A; PRKAR2B; PRKG2 | 1 | 11.94 | PRKAR2B | 0 | 0.00 | | 2 | 1.45 | PRKG1; PRKG2 | 0 | 0.00 | |
| dual incision in tc-ner | 35 | 1 | 0.48 | PCNA | 0 | 0.00 | | 0 | 0.00 | | 0 | 0.00 | | 0 | 0.00 | | 0 | 0.00 | |
| head morphogenesis: GO | 35 | 1 | 0.48 | STRA6 | 3 | 1.01 | DKK1; MYH3; NOG | 0 | 0.00 | | 0 | 0.00 | | 0 | 0.00 | | 0 | 0.00 | |
| post nmda receptor activation events | 35 | 1 | 0.48 | NEFL | 7 | 2.36 | ACTN2; ADCY8; CAMK2A; CAMK2B; GRIN1; GRIN2A; RPS6KA6 | 0 | 0.00 | | 0 | 0.00 | | 1 | 0.73 | RPS6KA6 | 0 | 0.00 | |
| carm er pathway | 35 | 0 | 0.00 | | 2 | 0.67 | HDAC5; PPARGC1A | 0 | 0.00 | | 0 | 0.00 | | 2 | 1.45 | ESR1; PPARGC1A | 0 | 0.00 | |
| negative regulation of endocytosis: GO | 35 | 0 | 0.00 | | 2 | 0.67 | ADIPOQ; APOC1 | 1 | 11.94 | ADIPOQ | 0 | 0.00 | | 0 | 0.00 | | 0 | 0.00 | |
| photoreceptor inner segment: GO | 35 | 0 | 0.00 | | 4 | 1.35 | CROCC; DNM1; GUCA1B; RGS9 | 0 | 0.00 | | 0 | 0.00 | | 1 | 0.73 | MAK | 0 | 0.00 | |
| positive | 35 | 0 | 0.00 | | 5 | 1.69 | ADRA1A; | 0 | 0.00 | | 0 | 0.00 | | 4 | 2.90 | ADRA1A; | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| regulation of heart contraction: GO | | | | | | | ADRB1; EDN3; NKX2-5; TPM1 | | | | | | | | | CTGF; EDN3; HRC | | | |
| regulation of systemic arterial blood pressure by hormone: GO | 35 | 0 | 0.00 | | 6 | 2.02 | AGT; AGTR1; EDN3; NOX1; PCSK5; REN | 1 | 11.94 | HSD11B2 | 0 | 0.00 | | 4 | 2.90 | AGTR1; CORIN; CTSG; EDN3 | 0 | 0.00 | |
| sarcoplasmic reticulum membrane: GO | 35 | 0 | 0.00 | | 6 | 2.02 | ATP2A1; CAMK2B; CASQ2; JPH2; SLN; TRDN | 0 | 0.00 | | 0 | 0.00 | | 2 | 1.45 | HRC; TRDN | 0 | 0.00 | |
| ear development: GO | 191 | 9 | 0.79 | ALDH1A3; CCNA2; CHRNA9; GJB6; GRHL3; NR4A3; PLS3; STRA6; WNT5A | 25 | 1.54 | ATP2B2; ATP6V1B1; BCL2; CLIC5; COL11A1; FGF9; FGFR1; FRZB; GABRB3; GLI2; GSC; ITGA8; LGR5; MCOLN3; MYO15A; NOG; NTRK3; OSR1; OSR2; PCDH15; PDZD7; PTPRQ; SIX1; SLC26A5; SOBP | 0 | 0.00 | | 0 | 0.00 | | 12 | 1.60 | BCL2; CLIC5; COL11A1; FGFR1; GLI2; KCNK2; LGR5; OSR1; PDZD7; PRRX1; SLITRK6; ZIC1 | 4 | 0.59 | CCNA2; SLC4A7; TMC1; WNT5A |
| negative regulation of canonical wnt signaling pathway: GO | 156 | 9 | 0.97 | CSNK1A1; GREM1; PSMA4; PSMA5; PSMB6; PSMD1; PSME3; RGS20; | 14 | 1.06 | APOE; DACT1; DKK1; DKK2; FRZB; GPC3; LRP4; MESP1; NKX2-5; NOG; SOX10; | 0 | 0.00 | | 0 | 0.00 | | 6 | 0.98 | DACT1; MESP1; PRICKLE1; TBX18; TLE2; WNT11 | 3 | 0.55 | RGS20; SNAI2; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | WNT5A | | | TBX18; TLE2; WNT11 | | | | | | | | | | | | |
| regulation of adaptive immune response: GO | 119 | 15 | 2.11 | ANXA1; CD80; IFNG; IL12B; IL1B; ILIRL1; IL4R; IL7R; JAK3; PRKCQ; PYCARD; RSAD2; SAMSN1; SASH3; SLAMF1 | 4 | 0.40 | C3; C4BPA; FCER2; P2RX7 | 0 | 0.00 | | 3 | 10.54 | IL1B; IL7R; SAMSN1 | 1 | 0.21 | C3 | 2 | 0.48 | IL10; PRKCQ |
| lysosome | 119 | 5 | 0.70 | ACP5; AP1S3; CTSB; CTSC; LAMP3 | 5 | 0.50 | ABCA2; ATP6V0A4; CTSF; IDUA; NAPSA | 0 | 0.00 | | 1 | 3.51 | LAMP3 | 3 | 0.64 | ATP6V0A4; CTSG; PSAPL1 | 2 | 0.48 | ACP5; AP1S3 |
| i band: GO | 119 | 2 | 0.28 | HOMER1; JUP | 21 | 2.08 | ACTN2; ADRA1A; ANK2; ATP2A1; CASQ2; CRYAB; DES; DMD; FHOD3; JPH2; KY; LDB3; MYL3; MYL9; MYOZ2; OBSCN; PDLIM3; PGM5; SLC4A1; SORBS2; SYNPO2 | 1 | 3.51 | CRYAB | 0 | 0.00 | | 4 | 0.85 | ADRA1A; HRC; PGM5; SORBS2 | 2 | 0.48 | ACTN1; HOMER1 |
| beta catenin binding: GO | 80 | 3 | 0.63 | CXADR; RGS20; TRPC4 | 9 | 1.33 | AR; CALCOCO1; CDHR5; CTNNA3; CTNND2; DACT1; | 0 | 0.00 | | 0 | 0.00 | | 4 | 1.27 | DACT1; ESR1; PTPRT; TCF7L1 | 1 | 0.35 | RGS20 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | | | | DACT2; PTPRT; TCF7L1 | | | | | | | | | | | | |
| metanephros development: GO | 80 | 3 | 0.63 | GDNF; GREM1; STAT1 | 15 | 2.21 | ADIPOQ; BCL2; CD34; GPC3; IRX1; ITGA8; OSR1; OSR2; PKD1; POU3F3; PTCH1; SIX1; SOX8; TCF21; TFAP2B | 1 | 5.22 | ADIPOQ | 0 | 0.00 | | 7 | 2.22 | BCL2; CD34; FRAS1; OSR1; POU3F3; PTCH1; SPRY1 | 1 | 0.35 | WNT9B |
| ncrna transcription: GO | 80 | 3 | 0.63 | ELL2; GTF3C6; NPM3 | 0 | 0.00 | | 0 | 0.00 | | 0 | 0.00 | | 0 | 0.00 | | 1 | 0.35 | ELL2 |
| peptidase activator activity: GO | 36 | 4 | 1.86 | CTSC; PSME3; PYCARD; VCP | 1 | 0.33 | PCOLCE2 | 0 | 0.00 | | 0 | 0.00 | | 2 | 1.41 | FBLN1; PCOLCE | 0 | 0.00 | |
| polyubiquitin binding: GO | 36 | 2 | 0.93 | TNIP3; VCP | 0 | 0.00 | | 0 | 0.00 | | 0 | 0.00 | | 0 | 0.00 | | 0 | 0.00 | |
| regulation of sterol transport: GO | 36 | 2 | 0.93 | ABCA12; LIPG | 8 | 2.62 | ABCA2; ADIPOQ; APOC1; APOE; EGF; LEP; PON1; PTCH1 | 1 | 11.61 | ADIPOQ | 0 | 0.00 | | 2 | 1.41 | EGF; PTCH1 | 0 | 0.00 | |
| t cell selection: GO | 36 | 2 | 0.93 | CD3E; IL6 | 1 | 0.33 | BCL2 | 0 | 0.00 | | 0 | 0.00 | | 1 | 0.71 | BCL2 | 0 | 0.00 | |
| ubiquitin-dependent degradation of cyclin d | 36 | 2 | 0.93 | PSMA5; PSMB6 | 0 | 0.00 | | 0 | 0.00 | | 0 | 0.00 | | 0 | 0.00 | | 0 | 0.00 | |
| ubiquitin-dependent degradation of cyclin d1 | 36 | 2 | 0.93 | PSMA5; PSMB6 | 0 | 0.00 | | 0 | 0.00 | | 0 | 0.00 | | 0 | 0.00 | | 0 | 0.00 | |
| alk in cardiac myocytes | 36 | 1 | 0.46 | TGFBR1 | 3 | 0.98 | BMP5; NKX2-5; NOG | 0 | 0.00 | | 0 | 0.00 | | 1 | 0.71 | CHRD | 0 | 0.00 | |
| alk pathway | 36 | 1 | 0.46 | TGFBR1 | 3 | 0.98 | BMP5; | 0 | 0.00 | | 0 | 0.00 | | 1 | 0.71 | CHRD | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| camp mediated signaling: GO | 36 | 1 | 0.46 | ADCYAP1 | 5 | 1.64 | NKX2-5; NOG ADCY2; ADCY5; ADCY6; ADCY8; PCLO | 0 | 0.00 | | 0 | 0.00 | | 2 | 1.41 | ADCYAP1R1; PCLO | 0 | 0.00 | |
| cardiac muscle cell action potential: GO | 36 | 1 | 0.46 | GJA1 | 4 | 1.31 | ANK2; ATP1A2; CACNA2D1; DMD | 0 | 0.00 | | 0 | 0.00 | | 2. | 1.41 | CACNA1G; CACNA2D1 | 0 | 0.00 | |
| 113a-mediated translational silencing of ceruloplasmin expression | 36 | 1 | 0.46 | RPL22L1 | 0 | 0.00 | | 0 | 0.00 | | 0 | 0.00 | | 0 | 0.00 | | 0 | 0.00 | |
| pip3 signaling in b lymphocytes | 36 | 1 | 0.46 | NR4A3 | 0 | 0.00 | | 0 | 0.00 | | 0 | 0.00 | | 0 | 0.00 | | 0 | 0.00 | |
| virion assembly: GO | 36 | 1 | 0.46 | PPLA | 2 | 0.66 | APOE; VPS37D | 0 | 0.00 | | 0 | 0.00 | | 0 | 0.00 | | 0 | 0.00 | |
| axon extension: GO | 36 | 0 | 0.00 | | 6 | 1.97 | DCLK1; DCX; MAPT; SEMA3A; SLIT2; SLIT3 | 0 | 0.00 | | 0 | 0.00 | | 4 | 2.82 | DCLK1; MAPT; SLIT2; SLIT3 | 0 | 0.00 | |
| negative regulation of fgfr signaling | 36 | 0 | 0.00 | | 6 | 1.97 | FGF1; FGF17; FGF22; FGF9; FGFR1; FGFR3 | 0 | 0.00 | | 0 | 0.00 | | 3 | 2.12 | FGF2; FGF22; FGFR1 | 0 | 0.00 | |
| negative regulation of histone modification: GO | 36 | 0 | 0.00 | | 2 | 0.66 | SNCA; USP17L2 | 0 | 0.00 | | 0 | 0.00 | | 1 | 0.71 | SNCA | 0 | 0.00 | |
| peptide hormone binding: GO | 36 | 0 | 0.00 | | 5 | 1.64 | CALCR; GALR1; GCGR; GHR; PTH1R | 1 | 11.61 | GHR | 0 | 0.00 | | 2 | 1.41 | PTH1R; SLC40A1 | 0 | 0.00 | |
| regulation of complement cascade | 36 | 0 | 0.00 | | 5 | 1.64 | C3; C4BPA; C6; CFH; CLU | 0 | 0.00 | | 0 | 0.00 | | 3 | 2.12 | C3; CFH; CLU | 0 | 0.00 | |
| regulation of | 193 | 21 | 1.82 | ADCYAP1; | 20 | 1.22 | ADCY5; | 0 | 0.00 | | 1 | 2.17 | IL1B | 12 | 1.58 | ADRA1A; | 4 | 0.59 | BDKRB2; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| cytosolic calcium ion concentration: GO | | | | BDKRB1; BDKRB2; CCL21; CCL3; CCR4; CCR5; CHRNA9; CXCL13; CXCR4; F2RL1; GJA1; GNA15; IL1B; JAK3; LPAR3; P2RY1; P2RY2; PROK2; S1PR4; TRPC4 | | | ADRA1A; ADRA1B; AGTR1; ATP1A2; ATP2B2; CACNA2D1; CALCR; CCKBR; DRD1; GALR1; JPH2; NOL3; NPY1R; P2RX7; PKD1; PLA2G6; PTHIR; TRDN; TRPM1 | | | | | | | | | AGTR1; CACNA2D1; ESR1; FGF2; HRC; LPAR1; NPY1R; P2RY4; PTH1R; TRDN; TRPC1 | | | GNA15; P2RY1; P2RY2 |
| regulation of peptide secretion: GO | 193 | 12 | 1.04 | ADCYAP1; GJA1; HIF1A; HMGCR; IFNG; IL1B; S100A8; S100A9; SLC16A1; SLC25A5; SLC2A1; VSNL1 | 26 | 1.59 | ABCC8; ACVR1C; ADCY5; ADORA1; ADRA2A; BRSK2; CACNA2D2; CARTPT; CFTR; CNR1; GPLD1; ICA1; ILDR1; INHBB; IRS2; KCNB1; LEP; LIF; NOS2; NRXN1; PLA2G6; RBP4; SCT; SYBU; SYT9; TFAP2B | 1 | 2.17 | ACVR1C | 2 | 4.33 | FFAR2; IL1B | 9 | 1.18 | ADRA2A; BRSK2; CACNA2D2; GPLD1; ICA1; ILDR1; MYRIP; NRXN1; SYBU | 4 | 0.59 | HIF1A; PPARD; SLC2A1; VSNL1 |
| respiratory system development: GO | 193 | 10 | 0.87 | ABCA12; ALDH1A3; EIF4EBP1; FOXF1; | 26 | 1.59 | CCDC40; CP; CYP1A2; DNAAF1; EDA; FGF1; | 0 | 0.00 | | 0 | 0.00 | | 12 | 1.58 | CP; CTGF; FGFR1; FOXA1; GLI2; HMGCS2; | 4 | 0.59 | EIF4EBP1; ITGA3; TIMELESS; WNT5A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | ITGA3; PDPN; STRA6; TIMELESS; TNC; WNT5A | | | FGF9; FGFR1; GLI2; GPC3; HHIP; HMGCS2; HSD11B1; HYDIN; LIF; MYOCD; NOG; PKD1; PKDCC; RBP4; SIX1; SPEF2; TBX5; TCF21; WNT11; ZFPM2 | | | | | | | | | IGFBP5; MYCN; SPEF2; SPRY1; WNT11; ZFPM2 | | | |
| apical junction complex: GO | 120 | 6 | 0.84 | CLDN24; CXADR; ECT2; JUP; RAP2B; TGFBR1 | 11 | 1.08 | AMOT; CAMSAP3; CGN; CGNL1; CLDN16; CLDN18; CLDN8; IGSF5; MAGI2; SORBS1; TJP3 | 0 | 0.00 | | 0 | 0.00 | | 8 | 1.69 | ADCYAP1R1; CGN; CGNL1; CLDN18; CLDN8; JAM2; SHROOM3; TJP3 | 2 | 0.47 | ECT2; RAP2B |
| organelle fusion: GO | 120 | 5 | 0.70 | BAK1; BCL2A1; CDK1; DYSF; GNAI3 | 7 | 0.69 | PCDHGA3; RPH3AL; SYT1; SYT17; SYT8; SYT9; TSNARE1 | 0 | 0.00 | | 0 | 0.00 | | 1 | 0.21 | SYT17 | 2 | 0.47 | BAK1; CDK1 |
| intrinsic component of endoplasmic reticulum membrane: GO | 120 | 4 | 0.56 | CALR; ELOVL4; HSPA5; TAP2 | 1 | 0.10 | FITM2 | 0 | 0.00 | | 0 | 0.00 | | 2 | 0.42 | DGAT2; HLA-DQB2 | 2 | 0.47 | HLA-G; HSPA5 |
| channel regulator activity: GO | 120 | 1 | 0.14 | PCSK9 | 17 | 1.67 | AGT; AMBP; BCL2; CFTR; DPP10; DPP6; DRD4; FXYD2; GPLD1; GRM7; | 0 | 0.00 | | 0 | 0.00 | | 8 | 1.69 | ABCC9; BCL2; CNIH3; DPP6; GPLD1; KCNK2; NRXN1; PRKG1 | 2 | 0.47 | PCSK9; SGK1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | HAMP; KCNIP1; KCNIP2; KCNMB4; NRXN1; NRXN3; SGK2 | | | | | | | | | | | | |
| kidney morphogenesis: GO | 81 | 4 | 0.83 | GCNT4; GDNF; GREM1; PGF | 13 | 1.89 | ADAMTS16; BCL2; FGF1; GPC3; IRX1; NOG; OSR1; PKD1; PTCH1; SIX1; SOX8; TCF21; WNT11 | 0 | 0.00 | | 0 | 0.00 | | 6 | 1.88 | BCL2; FGF2; FRAS1; OSR1; PTCH1; WNT11 | 1 | 0.35 | WNT9B |
| regulation of lyase activity: GO | 81 | 4 | 0.83 | ADCYAP1; CAP1; GNAI3; GPR87 | 17 | 2.48 | ADCY2; ADCY5; ADCY6; ADCY8; ADRA2A; ADRB1; CALCR; DRD1; DRD4; GALR1; GRM7; GUCA1B; LHCGR; NOS2; PALM; TSHR; VIPR2 | 0 | 0.00 | | 0 | 0.00 | | 3 | 0.94 | ADRA2A; PALM; TSHR | 1 | 0.35 | CAP1 |
| regulation of systemic arterial blood pressure: GO | 81 | 3 | 0.62 | F2RL1; GJA1; NTSR1 | 15 | 2.18 | ADAMTS16; ADORA1; ADRA1A; ADRA1B; ADRB1; AGT; AGTR1; CYP4A11; CYP4F12; EDN3; NCALD; NOX1; PCSK5; REN; | 1 | 5.16 | HSD11B2 | 0 | 0.00 | | 8 | 2.51 | ADRA1A; AGTR1; CORIN; CTSG; CYP4A11; CYP4F12; EDN3; NCALD | 1 | 0.35 | NTSR1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline: Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo: Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo: Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| | | | | | | | TPM1 | | | | | | | | | | | | |
| positive regulation of erk1 and erk2 cascade: GO | 158 | 18 | 1.91 | ADCYAP1; CCL17; CCL18; CCL21; CCL22; CCL3; CCL7; F2RL1; HMGCR; IL1B; IL26; IL6; NDRG4; NTRK1; P2RY1; PYCARD; S100A7; SLAMF1 | 8 | 0.60 | ADRA1A; C3; CCL14; ERBB4; FGF1; FGFR3; PDGFD; PLA2G5 | 0 | 0.00 | | 1 | 2.64 | IL1B | 8 | 1.29 | ADRA1A; ANGPT1; C3; CCL14; CTGF; ERBB4; ESR1; FGF2 | 3 | 0.54 | CCL20; P2RY1; ST5 |
| growth factor binding: GO | 121 | 11 | 1.52 | CXCL13; ESM1; FGFBP1; IL1RN; IL2RA; IL36RN; LTBP1; NTRK1; TGFBR1; TRIM16; WISP1 | 9 | 0.88 | ACVR1C; FGFBP2; FGFR1; FGFR3; GHR; IL1RAPL1; LIFR; NTRK3; WISP2 | 2 | 6.91 | ACVR1C; GHR | 1 | 3.45 | IL2RA | 5 | 1.05 | CTGF; FGFBP2; FGFR1; IGFBP5; WISP2 | 2 | 0.47 | FGFBP1; IGFBP3 |
| alzheimers disease | 121 | 6 | 0.83 | CALML3; CALML5; CDK5R1; COX7B; CYCS; IL1B | 8 | 0.78 | ATP2A1; CACNA1F; CALML6; CHP2; COX7A1; GRIN1; GRIN2A; PLCB4 | 0 | 0.00 | | 1 | 3.45 | IL1B | 3 | 0.63 | CHP2; COX7A1; PLCB4 | 2 | 0.47 | CDK5R1; CYCS |
| negative regulation of lymphocyte differentiation: GO | 37 | 5 | 2.26 | ANXA1; CTLA4; IL4R; JAK3; PGLYRP2 | 1 | 0.32 | DTX1 | 0 | 0.00 | | 0 | 0.00 | | 0 | 0.00 | | 0 | 0.00 | |
| gaba b receptor | 37 | 3 | 1.36 | GNAI3; | 5 | 1.59 | ADCY2; | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| activation | | | | GNGT2; KCNJ15 | | | ADCY5; ADCY6; ADCY8; KCNJ3 | | | | | | | | | | | | |
| heterophilic cell cell adhesion via plasma membrane cell adhesion molecules: GO | 37 | 3 | 1.36 | CXADR; LGALS7B; SELE | 7 | 2.23 | CADM2; CADM3; CBLN1; CDH4; IL1RAPL1; NLGN1; NRXN1 | 0 | 0.00 | | 1 | 11.29 | SELE | 3 | 2.06 | CADM2; CADM3; NRXN1 | 0 | 0.00 | |
| astrocyte differentiation: GO | 37 | 2 | 0.90 | S100A8; S100A9 | 6 | 1.91 | DRD1; LAMC3; LIF; PAX6; PLP1; SOX8 | 0 | 0.00 | | 0 | 0.00 | | 2 | 1.37 | LAMC3; PLP1 | 0 | 0.00 | |
| insulin secretion: GO | 37 | 2 | 0.90 | ANXA1; IL1RN | 3 | 0.96 | FAM3B; LEP; PCLO | 0 | 0.00 | | 0 | 0.00 | | 2 | 1.37 | PCLO; SLC18A2 | 0 | 0.00 | |
| mitochondrial transmembrane transport: GO | 37 | 2 | 0.90 | HSPA4; TIMM23 | 2 | 0.64 | ACACB; PRKAA2 | 0 | 0.00 | | 0 | 0.00 | | 1 | 0.69 | PRKAA2 | 0 | 0.00 | |
| phospho-transferase activity phosphate group as acceptor: GO | 37 | 2 | 0.90 | CMPK2; NME1 | 2 | 0.64 | DLG2; MPP2 | 0 | 0.00 | | 0 | 0.00 | | 3 | 2.06 | AK7; DLG2; MPP2 | 0 | 0.00 | |
| polysome: GO | 37 | 2 | 0.90 | CALR; EIF2S1 | 1 | 0.32 | PIWIL2 | 0 | 0.00 | | 0 | 0.00 | | 0 | 0.00 | | 0 | 0.00 | |
| spliceosomal snrnp assembly: GO | 37 | 2 | 0.90 | SNRPF; SNRPG | 0 | 0.00 | | 0 | 0.00 | | 0 | 0.00 | | 0 | 0.00 | | 0 | 0.00 | |
| vpu mediated degradation of cd4 | 37 | 2 | 0.90 | PSMA5; PSMB6 | 0 | 0.00 | | 0 | 0.00 | | 0 | 0.00 | | 0 | 0.00 | | 0 | 0.00 | |
| activation of nmda receptor upon glutamate binding and postsynaptic events | 37 | 1 | 0.45 | NEFL | 10 | 3.19 | ACTN2; ADCY8; CAMK2A; CAMK2B; GRIA1; GRIA2; GRIA4; | 1 | 11.29 | GRIA4 | 0 | 0.00 | | 3 | 2.06 | GRIA1; GRIA2; RPS6KA6 | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | | | | GRIN1; GRIN2A; RPS6KA6 | | | | | | | | | | | | |
| ga13 pathway | 37 | 1 | 0.45 | PI3 | 1 | 0.32 | BCL2 | 0 | 0.00 | | 0 | 0.00 | | 1 | 0.69 | BCL2 | 0 | 0.00 | |
| gtp hydrolysis and joining of the 60s ribosomal subunit | 37 | 1 | 0.45 | RPL22L1 | 0 | 0.00 | | 0 | 0.00 | | 0 | 0.00 | | 0 | 0.00 | | 0 | 0.00 | |
| negative regulation of endothelial cell migration: GO | 37 | 1 | 0.45 | CXCL13 | 4 | 1.28 | ANGPT4; APOE; HDAC5; SLIT2 | 0 | 0.00 | | 0 | 0.00 | | 4 | 2.75 | ANGPT4; DCN; FGF2; SLIT2 | 0 | 0.00 | |
| negative regulation of peptidyl tyrosine phosphorylation: GO | 37 | 1 | 0.45 | SAMSN1 | 2 | 0.64 | SPINK1; SRCIN1 | 1 | 11.29 | SRCIN1 | 1 | 11.29 | SAMSN1 | 0 | 0.00 | | 0 | 0.00 | |
| positive regulation of glucose transport: GO | 37 | 1 | 0.45 | NR4A3 | 7 | 2.23 | ADIPOQ; C3; GPC3; IRS2; RARRES2; SLC1A2; SORBS1 | 1 | 11.29 | ADIPOQ | 0 | 0.00 | | 2 | 1.37 | C3; RARRES2 | 0 | 0.00 | |
| positive regulation of potassium ion transport: GO | 37 | 1 | 0.45 | ATP1B3 | 9 | 2.87 | ABCC8; ACTN2; ADORA1; ADRA2A; ANK2; DPP6; DRD1; EDN3; FHL1 | 0 | 0.00 | | 0 | 0.00 | | 4 | 2.75 | ADRA2A; ATP1B2; DPP6; EDN3 | 0 | 0.00 | |
| regulation of muscle hypertrophy: GO | 37 | 1 | 0.45 | NR4A3 | 3 | 0.96 | AGT; MSTN; PDE9A | 0 | 0.00 | | 0 | 0.00 | | 3 | 2.06 | IGFBP5; LMCD1; PDE9A | 0 | 0.00 | |
| cellular response to glucagon stimulus: GO | 37 | 0 | 0.00 | | 6 | 1.91 | ADCY2; ADCY5; ADCY6; ADCY8; GCGR; PRKAR2B | 1 | 11.29 | PRKAR2B | 0 | 0.00 | | 1 | 0.69 | GNG11 | 0 | 0.00 | |
| p38 mapk pathway | 37 | 0 | 0.00 | | 2 | 0.64 | EEF2K; MYEF2 | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| peroxisomal lipid metabolism | 37 | 0 | 0.00 | | 5 | 1.59 | ACBD4; ACOX2; CRAT; HAO2; PECR | 0 | 0.00 | | 0 | 0.00 | | 3 | 2.06 | ACBD4; ACOX2; ALDH3A2 | 0 | 0.00 | |
| regulation of dna templated transcription elongation: GO | 37 | 0 | 0.00 | | 1 | 0.32 | TCEA3 | 0 | 0.00 | | 0 | 0.00 | | 1 | 0.69 | TCEA3 | 0 | 0.00 | |
| snap receptor activity: GO | 37 | 0 | 0.00 | | 1 | 0.32 | TSNARE1 | 0 | 0.00 | | 0 | 0.00 | | 0 | 0.00 | | 0 | 0.00 | |
| snare interactions in vesicular transport | 37 | 0 | 0.00 | | 1 | 0.32 | TSNARE1 | 0 | 0.00 | | 0 | 0.00 | | 0 | 0.00 | | 0 | 0.00 | |
| positive regulation of leukocyte mediated immunity: GO | 82 | 8 | 1.63 | F2RL1; IFNG; IL12B; IL1B; IL4R; PTAFR; RSAD2; SASH3 | 4 | 0.58 | C3; FCER2; NOS2; P2RX7 | 0 | 0.00 | | 1 | 5.10 | IL1B | 1 | 0.31 | C3 | 1 | 0.35 | PTAFR |
| cardiac septum development: GO | 82 | 5 | 1.02 | LTBP1; PRDM1; STRA6; TBX20; WNT5A | 6 | 0.86 | ANK2; NKX2-5; PCSK5; TBX5; WNT11; ZFPM2 | 0 | 0.00 | | 0 | 0.00 | | 2 | 0.62 | WNT11; ZFPM2 | 1 | 0.35 | WNT5A |
| lipoprotein biosynthetic process: GO | 82 | 4 | 0.82 | CWH43; OAS2; PIGW; PLAUR | 2 | 0.29 | APOE; ZDHHC15 | 0 | 0.00 | | 0 | 0.00 | | 1 | 0.31 | ZDHHC15 | 1 | 0.35 | PIGW |
| methyltransferase complex: GO | 82 | 4 | 0.82 | ACTB; RUVBL1; SNRPF; SNRPG | 0 | 0.00 | | 0 | 0.00 | | 0 | 0.00 | | 0 | 0.00 | | 1 | 0.35 | ACTB |
| regulation of heart rate: GO | 82 | 4 | 0.82 | DSC2; DSP; GJA1; JUP | 12 | 1.73 | ADRA1A; ADRB1; AGT; ANK2; CACNA2D1; CASQ2; CTNNA3; DMD; EDN3; SEMA3A; SPTBN4; TPM1 | 0 | 0.00 | | 0 | 0.00 | | 6 | 1.86 | ADRA1A; CACNAIG; CACNA2D1; EDN3; HRC; SPTBN4 | 1 | 0.35 | DSC2 |
| major pathway | 82 | 3 | 0.61 | RPL22L1; | 0 | 0.00 | | 0 | 0.00 | | 0 | 0.00 | | 0 | 0.00 | | 1 | 0.35 | NOP56 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| of rrna processing in the nucleolus and cytosol | | | | RPP40; UTP11 | | | | | | | | | | | | | | | |
| phosphatidyl-inositol signaling system | 82 | 2 | 0.41 | CALML3; CALML5 | 4 | 0.58 | CALML6; DGKG; FN3K; PLCB4 | 0 | 0.00 | | 0 | 0.00 | | 3 | 0.93 | FN3K; PLCB4; PLCZ1 | 1 | 0.35 | PLCD4 |
| coated membrane: GO | 82 | 1 | 0.20 | APIS3 | 2 | 0.29 | DNM1; NCALD | 0 | 0.00 | | 0 | 0.00 | | 1 | 0.31 | NCALD | 1 | 0.35 | AP1S3 |
| regulation of calcium ion dependent exocytosis: GO | 82 | 1 | 0.20 | RIMS3 | 12 | 1.73 | ADRA2A; CACNA1H; GRIK5; KCNB1; NLGN1; RPH3AL; SPINK1; SYT1; SYT17; SYT8; SYT9; TRPV6 | 0 | 0.00 | | 0 | 0.00 | | 4 | 1.24 | ADRA2A; CACNA1G; CACNA1H; SYT17 | 1 | 0.35 | SERPINA10 |
| regulation of g protein coupled receptor protein signaling pathway: GO | 122 | 6 | 0.82 | ADCYAP1; CNGB1; KLK5; KLK6; RGS1; RGS20 | 13 | 1.26 | ADRA2A; C3; DNM1; GPRASP1; GUCA1B; KCTD16; KCTD8; PALM; RGS11; RGS6; RGS9; RPH3AL; SNCA | 1 | 3.43 | RGS11 | 0 | 0.00 | | 5 | 1.04 | ADRA2A; C3; GPRASP1; PALM; SNCA | 2 | 0.46 | RGS1; RGS20 |
| diabetes pathways | 122 | 4 | 0.55 | CALR; EIF2S1; HSPA5; MMP1 | 3 | 0.29 | LEP; PCSK2; TSPYL2 | 0 | 0.00 | | 0 | 0.00 | | 3 | 0.62 | CPE; CTSG; IGFBP5 | 2 | 0.46 | HSPA5; IGFBP3 |
| infectious disease | 196 | 13 | 1.11 | AP1S3; CALR; CXCR4; HBEGF; ISG15; KPNA2; NPM1; PPIA; | 2 | 0.12 | SYT1; TF | 0 | 0.00 | | 1 | 2.13 | ISG15 | 1 | 0.13 | SLC29A1 | 4 | 0.58 | AP1S3; HBEGF; KPNA2; NPM1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | PSMA5; PSMB6; RANBP1; RPL22L1; SLC25A5 | | | | | | | | | | | | | | | |
| drug metabolic process: GO | 38 | 3 | 1.32 | UGT1A1; UGT1A10; UGT1A7 | 11 | 3.42 | CYP1A1; CYP1A2; CYP2A6; CYP2C9; CYP2D6; CYP3A5; CYP4B1; CYP4F12; EPHX2; FMO2; FMO5 | 0 | 0.00 | | 0 | 0.00 | | 5 | 3.34 | CYP3A4; CYP3A5; CYP4B1; CYP4F12; FMO5 | 0 | 0.00 | |
| positive regulation of cell killing: GO | 38 | 3 | 1.32 | F2RL1; IFNG; IL12B | 3 | 0.93 | FCER2; NOS2; P2RX7 | 0 | 0.00 | | 0 | 0.00 | | 0 | 0.00 | | 0 | 0.00 | |
| defective cftr causes cystic fibrosis | 38 | 2 | 0.88 | PSMA5; PSMB6 | 0 | 0.00 | | 0 | 0.00 | | 0 | 0.00 | | 0 | 0.00 | | 0 | 0.00 | |
| degradation of axin | 38 | 2. | 0.88 | PSMA5; PSMB6 | 0 | 0.00 | | 0 | 0.00 | | 0 | 0.00 | | 0 | 0.00 | | 0 | 0.00 | |
| degradation of gli1 by the proteasome | 38 | 2 | 0.88 | PSMA5; PSMB6 | 0 | 0.00 | | 0 | 0.00 | | 0 | 0.00 | | 0 | 0.00 | | 0 | 0.00 | |
| hh mutants that don't undergo autocatalytic processing are degraded by erad | 38 | 2 | 0.88 | PSMA5; PSMB6 | 0 | 0.00 | | 0 | 0.00 | | 0 | 0.00 | | 0 | 0.00 | | 0 | 0.00 | |
| regulation of runx3 expression and activity | 38 | 2 | 0.88 | PSMA5; PSMB6 | 0 | 0.00 | | 0 | 0.00 | | 0 | 0.00 | | 0 | 0.00 | | 0 | 0.00 | |
| amino sugar metabolic process: GO | 38 | 1 | 0.44 | CHI3L2 | 4 | 1.24 | B4GALNT2; CHST5; FN3K; RENBP | 0 | 0.00 | | 0 | 0.00 | | 1 | 0.67 | FN3K | 0 | 0.00 | |
| estrogen receptor | 38 | 1 | 0.44 | PCNA | 1 | 0.31 | PPARGC1A | 0 | 0.00 | | 0 | 0.00 | | 1 | 0.67 | PPARGC1A | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| binding: GO | | | | | | | | | | | | | | | | | | | |
| regulation of antigen receptor mediated signaling pathway: GO | 38 | 1 | 0.44 | PRNP | 1 | 0.31 | CACNA1F | 0 | 0.00 | | 1 | 11.00 | GBP1 | 0 | 0.00 | | 0 | 0.00 | |
| cis golgi network: GO | 38 | 0 | 0.00 | | 0 | 0.00 | | 0 | 0.00 | | 0 | 0.00 | | 1 | 0.67 | CTGF | 0 | 0.00 | |
| negative regulation of g protein coupled receptor protein signaling pathway: GO | 38 | 0 | 0.00 | | 6 | 1.86 | ADRA2A; DNM1; GPRASP1; PALM; RPH3AL; SNCA | 0 | 0.00 | | 0 | 0.00 | | 4 | 2.67 | ADRA2A; GPRASP1; PALM; SNCA | 0 | 0.00 | |
| oxidoreductase activity acting on paired donors with incorporation or reduction of molecular oxygen 2 oxoglutarate as one donor and incorporation of one atom each of oxygen into both donors: GO | 38 | 0 | 0.00 | | 2 | 0.62 | P4HTM; TET1 | 0 | 0.00 | | 0 | 0.00 | | 2 | 1.34 | P4HTM; TET1 | 0 | 0.00 | |
| rac gtpase binding: GO | 38 | 0 | 0.00 | | 1 | 0.31 | NOX1 | 0 | 0.00 | | 0 | 0.00 | | 0 | 0.00 | | 0 | 0.00 | |
| voltage gated calcium channel complex: GO | 38 | 0 | 0.00 | | 8 | 2.48 | CACNA1F; CACNA1H; CACNA2D1; CACNA2D2; CACNB1; CASQ2; CATSPERG; TRDN | 0 | 0.00 | | 0 | 0.00 | | 7 | 4.68 | CACNA1G; CACNA1H; CACNA2D1; CACNA2D2; CACNB1; CATSPERG; TRDN | 0 | 0.00 | |
| nik nf kappab | 83 | 6 | 1.21 | PSMA4; | 0 | 0.00 | | 0 | 0.00 | | 0 | 0.00 | | 0 | 0.00 | | 1 | 0.34 | CARD10 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| signaling: GO | | | | PSMA5; PSMB6; PSMD1; PSME3; TNFRSF10A | | | | | | | | | | | | | | | |
| translation factor activity rna binding: GO | 83 | 6 | 1.21 | EEF1B2; EIF2S1; EIF4G2; EIF5A; EIF5AL1; EIF6 | 2 | 0.28 | CPEB1; EEF2K | 0 | 0.00 | | 0 | 0.00 | | 1 | 0.31 | CPEB1 | 1 | 0.34 | EIF6 |
| acetyltransferase complex: GO | 83 | 2 | 0.40 | ACTB; RUVBL1 | 1 | 0.14 | KAT2A | 0 | 0.00 | | 0 | 0.00 | | 0 | 0.00 | | 1 | 0.34 | ACTB |
| fatty acid metabolism | 161 | 6 | 0.62 | ADH7; ALDH1A3; CYP4F11; CYP4F22; ELOVL7; PTGS2 | 28 | 2.05 | ACACB; ACADL; ACBD4; ACOT12; ACOX2; ACSF2; ADH1B; ADH1C; ADHFE1; CRAT; CYP1A1; CYP1A2; CYP2C9; CYP2J2; CYP4A11; CYP4B1; CYP4F12; CYP4F8; ELOVL2; EPHX2; FADS2; HAO2; PECR; PON1; PON3; PRKAA2; PTGIS; THRSP | 1 | 2.60 | THRSP | 0 | 0.00 | | 8 | 1.26 | ACBD4; ACOX2; ALDH3A2; CYP4A11; CYP4B1; CYP4F12; PON3; PRKAA2 | 3 | 0.53 | FEN1; PPARD; PTGS2 |
| regulation of striated | 84 | 6 | 1.20 | CXCL10; CXCL9; | 10 | 1.40 | BCL2; BHLHE41; | 0 | 0.00 | | 1 | 4.97 | CXCL9 | 6 | 1.81 | BCL2; BHLHA15; | 1 | 0.34 | NRG1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| muscle cell differentiation: GO | | | | GREM1; IL4R; NEU2; NRG1 | | | DKK1; FLT3LG; HDAC5; MESP1; MYOCD; NKX2-5; RBM24; SCGB3A1 | | | | | | | | | BHLHE41; MESP1; PRICKLE1; SHOX2 | | | |
| dna templated transcription elongation: GO | 84 | 1 | 0.20 | ELL2 | 0 | 0.00 | | 0 | 0.00 | | 0 | 0.00 | | 0 | 0.00 | | 1 | 0.34 | ELL2 |
| regulation of activated t cell proliferation: GO | 39 | 9 | 3.86 | CD274; IDO1; IL12B; IL2RA; JAK3; PRNP; PYCARD; SLAMF1; TNFSF9 | 1 | 0.30 | GPAM | 1 | 10.72 | GPAM | 1 | 10.72 | IL2RA | 0 | 0.00 | | 0 | 0.00 | |
| positive regulation of response to biotic stimulus: GO | 39 | 6 | 2.57 | DEFB103A; DEFB103B; F2RL1; IL12B; KLK5; KLK7 | 1 | 0.30 | USP17L2 | 0 | 0.00 | | 0 | 0.00 | | 0 | 0.00 | | 0 | 0.00 | |
| degradation of gli2 by the proteasome | 39 | 3 | 1.29 | CSNK1A1; PSMA5; PSMB6 | 0 | 0.00 | | 0 | 0.00 | | 0 | 0.00 | | 0 | 0.00 | | 0 | 0.00 | |
| gli3 is processed to gli3r by the proteasome | 39 | 3 | 1.29 | CSNK1A1; PSMA5; PSMB6 | 0 | 0.00 | | 0 | 0.00 | | 0 | 0.00 | | 0 | 0.00 | | 0 | 0.00 | |
| sphingolipid de novo biosynthesis | 39 | 3 | 1.29 | CERS3; SGPP2; SPTSSA | 1 | 0.30 | FA2H | 0 | 0.00 | | 0 | 0.00 | | 3 | 1.95 | ACER1; ALDH3A2; PLPP3 | 0 | 0.00 | |
| hh mutants abrogate ligand secretion | 39 | 2 | 0.86 | PSMA5; PSMB6 | 0 | 0.00 | | 0 | 0.00 | | 0 | 0.00 | | 0 | 0.00 | | 0 | 0.00 | |
| nucleoside triphosphate biosynthetic process: GO | 39 | 2 | 0.86 | CMPK2; NME1 | 1 | 0.30 | ATP6V0A4 | 0 | 0.00 | | 0 | 0.00 | | 2 | 1.30 | AK7; ATP6V0A4 | 0 | 0.00 | |
| regulation of substrate | 39 | 2 | 0.86 | C1QBP; CALR | 1 | 0.30 | MYOC | 0 | 0.00 | | 1 | 10.72 | GBP1 | 2 | 1.30 | FBLN1; MYOC | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| adhesion dependent cell spreading: GO | | | | | | | | | | | | | | | | | | | |
| trivalent inorganic cation transport: GO | 39 | 2 | 0.86 | STEAP1B; STEAP4 | 4 | 1.21 | ATP6V0A4; ATP6V0E2; ATP6V1B1; TF | 0 | 0.00 | | 1 | 10.72 | STEAP1B | 3 | 1.95 | ATP6V0A4; ATP6V0E2; STEAP2 | 0 | 0.00 | |
| endosome to lysosome transport: GO | 39 | 1 | 0.43 | HOOK1 | 2 | 0.61 | GPRASP1; PCDHGA3 | 0 | 0.00 | | 0 | 0.00 | | 1 | 0.65 | GPRASP1 | 0 | 0.00 | |
| ligase activity forming carbon sulfur bonds: GO | 39 | 1 | 0.43 | UBA6 | 5 | 1.51 | ACSBG1; ACSF2; ACSM5; ACSS3; SLC27A6 | 1 | 10.72 | SLC27A6 | 0 | 0.00 | | 1 | 0.65 | ACSS3 | 0 | 0.00 | |
| nucleotide excision repair dna incision: GO | 39 | 1 | 0.43 | PCNA | 0 | 0.00 | | 0 | 0.00 | | 0 | 0.00 | | 0 | 0.00 | | 0 | 0.00 | |
| peptidyl tyrosine autophos-phorylation: GO | 39 | 1 | 0.43 | JAK3 | 1 | 0.30 | ROS1 | 0 | 0.00 | | 0 | 0.00 | | 0 | 0.00 | | 0 | 0.00 | |
| positive regulation of cell matrix adhesion: GO | 39 | 1 | 0.43 | CCL21 | 1 | 0.30 | MYOC | 0 | 0.00 | | 0 | 0.00 | | 1 | 0.65 | MYOC | 0 | 0.00 | |
| ret pathway | 39 | 1 | 0.43 | GDNF | 2 | 0.61 | GFRA1; IRS2 | 0 | 0.00 | | 0 | 0.00 | | 1 | 0.65 | DOK6 | 0 | 0.00 | |
| transition metal ion transmembrane transporter activity: GO | 39 | 1 | 0.43 | SLC39A6 | 2 | 0.61 | SLC30A10; TF | 0 | 0.00 | | 0 | 0.00 | | 2 | 1.30 | ATP2C2; SLC40A1 | 0 | 0.00 | |
| autophagosome organization: GO | 39 | 0 | 0.00 | | 1 | 0.30 | MAP1LC3C | 0 | 0.00 | | 0 | 0.00 | | 0 | 0.00 | | 0 | 0.00 | |
| cytoplasmic microtubule organization: GO | 39 | 0 | 0.00 | | 1 | 0.30 | TRDN | 0 | 0.00 | | 0 | 0.00 | | 1 | 0.65 | TRDN | 0 | 0.00 | |
| fc epsilon receptor i signaling in mast cells | 39 | 0 | 0.00 | | 0 | 0.00 | | 0 | 0.00 | | 0 | 0.00 | | 1 | 0.65 | MS4A2 | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| jnk mapk pathway | 39 | 0 | 0.00 | | 1 | 0.30 | MYEF2 | 0 | 0.00 | | 0 | 0.00 | | 0 | 0.00 | | 0 | 0.00 | |
| membrane depolarization during action potential: GO | 39 | 0 | 0.00 | | 7 | 2.12 | ANK2; ATP1A2; CACNA1F; CACNA1H; CACNA2D1; NALCN; SCN7A | 0 | 0.00 | | 0 | 0.00 | | 5 | 3.26 | CACNA1G; CACNA1H; CACNA2D1; NALCN; SCN7A | 0 | 0.00 | |
| processing of capped intron-containing pre-mrna | 124 | 2 | 0.27 | HSPA8; SNRPF | 1 | 0.10 | PPIL6 | 0 | 0.00 | | 0 | 0.00 | | 1 | 0.20 | PPIL6 | 2. | 0.46 | DDX39A; HSPA8 |
| fc receptor signaling pathway: GO | 198 | 19 | 1.61 | ACTB; ACTR3; ARPC1A; ARPC3; FCGR1A; IGHG1; IGHG2; IGHG4; IGKC; IGKV4-1; NR4A3; NRAS; PRKCQ; PSMA4; PSMA5; PSMB6; PSMD1; PSME3; UBE2N | 1 | 0.06 | PLA2G6 | 2 | 4.22 | IGHG1; IGKV3-20 | 1 | 2.11 | LCP2 | 2 | 0.26 | IGHV3-23; MS4A2 | 4 | 0.57 | ACTB; ARPC1A; PRKCQ; VAV2 |
| dna templated transcription initiation: GO | 199 | 8 | 0.67 | E2F3; HIST1H4I; HIST1H4J; HIST1H4K; HIST1H4L; NR4A3; POLR3G; TEAD4 | 11 | 0.65 | AR; DACH1; ESRRG; NR3C2; NR5A1; PGR; PPARGC1A; RORB; RORC; RXRG; TBX5 | 0 | 0.00 | | 0 | 0.00 | | 8 | 1.02 | CTGF; DACH1; ESR1; ESRRG; NR2F1; NR3C2; PGR; PPARGC1A | 4 | 0.57 | HIST1H4I; POLR3G; PPARD; TEAD4 |
| tryptophan metabolism | 85 | 8 | 1.57 | ALDH1A3; CYP4F11; | 8 | 1.11 | AOC3; CYP1A1; | 0 | 0.00 | | 1 | 4.92 | TDO2 | 4 | 1.20 | ALDH3A2; AOX1; | 1 | 0.33 | OGDHL |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline: Up-regu-lated | A: Fold Change (FC) Up | A: Up-regulated Genes | A: Down-regu-lated | A: Fold Change (FC) | A: Down-regulated Genes | B. Differentially expressed genes significant in the baseline vs week 12 comparison only in the placebo: Up-regu-lated | B: Fold Change (FC) Up | B: Up-regulated Genes | B: Down-regu-lated | B: Fold Change (FC) | B: Down-regulated Genes | C. Differentially expressed genes significant in the baseline vs week 12 comparison only in the nemo: Up-regu-lated | C: Fold Change (FC) Up | C: Up-regulated Genes | C: Down-regu-lated | C: Fold Change (FC) | C: Down-regulated Genes |
|---|---|---|---|---|---|---|---|---|---|---|---|---|---|---|---|---|---|---|---|
| | | | | IDO1; IL4I1; KYNU; OGDHL; TDO2; UHRF1 | | | CYP1A2; CYP4F12; CYP4F8; HAAO; INMT; MAOA | | | | | | | | | CYP4F12; LNX1 | | | |
| voltage gated potassium channel activity: GO | 85 | 4 | 0.79 | CNGB1; HTR3A; KCNJ15; KCNK1 | 13 | 1.80 | ABCC8; KCNA1; KCNA2; KCNA4; KCNB1; KCNB2; KCND2; KCNH8; KCNIP2; KCNJ1; KCNJ3; KCNT2; KCNU1 | 0 | 0.00 | | 0 | 0.00 | | 3 | 0.90 | KCND2; KCNK2; KCNT2 | 1 | 0.33 | KCNK1 |
| transcription factor activity rna polymerase ii transcription factor binding: GO | 125 | 4 | 0.54 | EOMES; HIF1A; PITX1; TBX20 | 11 | 1.04 | BHLHE41; ELANE; LIF; MYOCD; NKX2-5; PPARGC1A; SOX10; TBX15; TBX18; TFAP2B; ZFPM2 | 0 | 0.00 | | 0 | 0.00 | | 7 | 1.42 | BHLHE41; ELANE; PPARGC1A; PRRX1; TBX15; TBX18; ZFPM2 | 2 | 0.45 | HIF1A; PITX1 |
| autonomic nervous system development: GO | 40 | 3 | 1.26 | GDNF; NTRK1; TP63 | 9 | 2.65 | GFRA3; HAND2; PLXNA3; PLXNA4; SEMA3A; SIX1; SOX10; SOX8; TFAP2B | 0 | 0.00 | | 0 | 0.00 | | 2 | 1.27 | HAND2; PLXNA4 | 0 | 0.00 | |
| ifng pathway | 40 | 3 | 1.26 | IFNG; IL1B; STAT1 | 2 | 0.59 | CAMK2A; CAMK2B | 0 | 0.00 | | 1 | 10.45 | IL1B | 0 | 0.00 | | 0 | 0.00 | |
| positive regulation of kidney | 40 | 3 | 1.26 | GDNF; GREM1; SERPINB7 | 7 | 2.06 | ADIPOQ; AGT; LIF; NOG; | 1 | 10.45 | ADIPOQ | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| development: GO | | | | | | | PDGFD; SIX1; SOX8 | | | | | | | | | | | | |
| b cell antigen receptor | 40 | 2 | 0.84 | PI3; PRDX1 | 0 | 0.00 | | 0 | 0.00 | | 0 | 0.00 | | 0 | 0.00 | | 0 | 0.00 | |
| bile acid and bile salt metabolism | 40 | 2 | 0.84 | CH25H; FABP6 | 6 | 1.77 | ABCB11; ABCC3; ACOX2; ALB; PTGIS; SLC10A2 | 0 | 0.00 | | 0 | 0.00 | | 1 | 0.64 | ACOX2 | 0 | 0.00 | |
| stabilization of p53 | 40 | 2 | 0.84 | PSMA5; PSMB6 | 0 | 0.00 | | 0 | 0.00 | | 0 | 0.00 | | 0 | 0.00 | | 0 | 0.00 | |
| sulfur amino acid metabolic process: GO | 40 | 2 | 0.84 | AHCY; CNDP2 | 3 | 0.88 | BHMT2; CDO1; MAT1A | 0 | 0.00 | | 0 | 0.00 | | 0 | 0.00 | | 0 | 0.00 | |
| anion homeostasis: GO | 40 | 1 | 0.42 | LIPG | 8 | 2.36 | APOE; ENPP1; GCM2; GPAM; MLXIPL; PRKAA2; SLC34A3; TFAP2B | 1 | 10.45 | GPAM | 0 | 0.00 | | 2 | 1.27 | DGAT2; PRKAA2 | 0 | 0.00 | |
| ephb fwd pathway | 40 | 1 | 0.42 | NRAS | 4 | 1.18 | DNM1; EPHB1; GRIA1; TF | 0 | 0.00 | | 0 | 0.00 | | 2 | 1.27 | EFNB3; GRIA1 | 0 | 0.00 | |
| nonsense mediated decay (nmd) enhanced by the exon junction complex (ejc) | 40 | 1 | 0.42 | RPL22L1 | 0 | 0.00 | | 0 | 0.00 | | 0 | 0.00 | | 0 | 0.00 | | 0 | 0.00 | |
| nonsense-mediated decay (nmd) | 40 | 1 | 0.42 | RPL22L1 | 0 | 0.00 | | 0 | 0.00 | | 0 | 0.00 | | 0 | 0.00 | | 0 | 0.00 | |
| oxidative phosphorylation | 40 | 1 | 0.42 | ATP12A | 4 | 1.18 | ATP6V0A4; ATP6V0E2; ATP6V1B1; COX7A1 | 0 | 0.00 | | 0 | 0.00 | | 3 | 1.91 | ATP6V0A4; ATP6V0E2; COX7A1 | 0 | 0.00 | |
| regulation of vacuole | 40 | 1 | 0.42 | RALB | 0 | 0.00 | | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| organization: GO | | | | | | | | | | | | | | | | | | | |
| transcription-coupled nucleotide excision repair (tc-ner) | 40 | 1 | 0.42 | PCNA | 0 | 0.00 | | 0 | 0.00 | | 0 | 0.00 | | 0 | 0.00 | | 0 | 0.00 | |
| myeloid cell development: GO | 40 | 0 | 0.00 | | 3 | 0.88 | EPB42; GATA1; RHAG | 0 | 0.00 | | 0 | 0.00 | | 0 | 0.00 | | 0 | 0.00 | |
| protein kinase a binding: GO | 40 | 0 | 0.00 | | 4 | 1.18 | AKAP12; DACT1; DACT2; PRKAR2B | 1 | 10.45 | PRKAR2B | 0 | 0.00 | | 3 | 1.91 | AKAP12; DACT1; MYRIP | 0 | 0.00 | |
| purine nucleoside monophosphate biosynthetic process: GO | 40 | 0 | 0.00 | | 2 | 0.59 | AMPD1; ATP6V0A4 | 0 | 0.00 | | 0 | 0.00 | | 1 | 0.64 | ATP6V0A4 | 0 | 0.00 | |
| sperm motility: GO | 40 | 0 | 0.00 | | 5 | 1.47 | CCDC40; DNAH11; ROPN1B; TEKT3; TNP1 | 0 | 0.00 | | 0 | 0.00 | | 1 | 0.64 | ROPN1B | 0 | 0.00 | |
| sterol binding: GO | 40 | 0 | 0.00 | | 5 | 1.47 | APOD; APOE; PTCH1; RORC; SOAT2 | 0 | 0.00 | | 0 | 0.00 | | 2 | 1.27 | PMP2; PTCH1 | 0 | 0.00 | |
| skeletal muscle organ development: GO | 126 | 6 | 0.80 | CTSB; EOMES; HOMER1; MYLK2; PITX1; STRA6 | 16 | 1.50 | ACTA1; C16orf89; CDON; CNTFR; COL19A1; DMD; KLHL31; MEOX2; MYH14; MYL3; MYLPF; NUPR1; SIX1; SOX8; SRPK3; TCF21 | 0 | 0.00 | | 0 | 0.00 | | 7 | 1.41 | CDON; CNTFR; DCN; HLF; IGFBP5; KLHL31; MEOX2 | 2 | 0.45 | HOMER1; PITX1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| microbody: GO | 126 | 1 | 0.13 | HMGCR | 9 | 0.84 | ABCD2; ACOX2; CRAT; EPHX2; HAO2; NOS2; PECR; PEX11A; SERHL2 | 1 | 3.32 | ABCD2 | 0 | 0.00 | | 2 | 0.40 | ACOX2; ALDH3A2 | 2 | 0.45 | TKT; XDH |
| cytokine binding: GO | 86 | 14 | 2.72 | CCR5; CXCR1; CXCR4; GREM1; IL12B; ILIRL1; IL1RN; IL2RA; IL36RN; LTBP1; PLP2; TGFBR1; TNFRSF9; TRIM16 | 8 | 1.10 | CNTFR; ELANE; FZD4; GDF5; GREM2; IL1RAPL1; LIFR; NOG | 0 | 0.00 | | 2 | 9.72 | GBP1; IL2RA | 4 | 1.18 | CHRD; CNTFR; ELANE; GREM2 | 1 | 0.33 | CXCR1 |
| protein activation cascade: GO | 86 | 7 | 1.36 | C1QBP; F12; IGHG1; IGHG2; IGHG4; IGKC; IGKV4-1 | 12 | 1.65 | C3; C4BPA; C6; C7; CFD; CFH; CLU; COLEC11; F10; F7; FCN2; KLKB1 | 2 | 9.72 | IGHG1; IGKV3-20 | 0 | 0.00 | | 6 | 1.77 | C3; CFH; CLU; FBLN1; IGHM; IGHV3-23 | 1 | 0.33 | F12 |
| post embryonic development: GO | 86 | 3 | 0.58 | BAK1; PRDM1; TGFBR1 | 4 | 0.55 | ALX4; BCL2; CYP1A2; SCUBE1 | 0 | 0.00 | | 0 | 0.00 | | 4 | 1.18 | ALDH5A1; ALX4; BCL2; SLC18A2 | 1 | 0.33 | BAK1 |
| receptor signaling protein activity: GO | 164 | 9 | 0.92 | ADCYAP1; CD3E; FCGR1A; FLRT3; IFITM1; IL1RL1; IL4R; MAPK6; TGFBR1 | 11 | 0.79 | ACVR1C; ADRB1; AMHR2; DCLK1; ERBB4; GNAZ; JPH2; KCNH8; MAPK15; MAPK4; PAK3 | 1 | 2.55 | ACVR1C | 0 | 0.00 | | 3 | 0.46 | DCLK1; ERBB4; PAK3 | 3 | 0.52 | BMPR1B; FLRT3; MAPK6 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| central nervous system neuron differentiation: GO | 164 | 6 | 0.61 | EOMES; FBXO45; SALL3; TBX20; WNT5A; WNT7A | 29 | 2.09 | ATP2B2; CBLN1; CHD5; DCLK1; DCX; DRD1; EPHB1; ERBB4; FEZF2; FGFR1; FOXN4; GLI2; ID4; LEP; LMX1A; MDGA2; MNX1; NRXN1; PAX6; PLXNA3; PLXNA4; PTCH1; SEMA3A; SLIT2; SLIT3; SOX1; SPOCK1; SPTBN4; UNC5D | 0 | 0.00 | | 0 | 0.00 | | 12 | 1.86 | DCLK1; ERBB4; FGFR1; GDF7; GLI2; NRXN1; PLXNA4; PTCH1; SLIT2; SLIT3; SPOCK1; SPTBN4 | 3 | 0.52 | FBXO45; WNT5A; WNT7A |
| membrane invagination: GO | 41 | 5 | 2.04 | FCGR1A; IGHG1; IGHG2; IGHG4; IGKC | 1 | 0.29 | GSN | 1 | 10.19 | IGHG1 | 0 | 0.00 | | 3 | 1.86 | GULP1; IGHM; IGHV3-23 | 0 | 0.00 | |
| calcium ion import into cytosol: GO | 41 | 3 | 1.22 | CCL21; CCL3; CCR5 | 4 | 1.15 | JPH2; NOL3; P2RX7; TRDN | 0 | 0.00 | | 0 | 0.00 | | 2 | 1.24 | FGF2; TRDN | 0 | 0.00 | |
| detection of visible light: GO | 41 | 3 | 1.22 | CNGB1; ELOVL4; SDR16C5 | 1 | 0.29 | CACNA1F | 0 | 0.00 | | 0 | 0.00 | | 0 | 0.00 | | 0 | 0.00 | |
| polysaccharide biosynthetic process: GO | 41 | 3 | 1.22 | B3GNT3; HAS3; PGM2 | 4 | 1.15 | GYG2; HAS1; PGM5; PHKG1 | 0 | 0.00 | | 0 | 0.00 | | 2 | 1.24 | PGM5; PHKG1 | 0 | 0.00 | |
| response to cold: GO | 41 | 3 | 1.22 | CXCL10; GK; IL6 | 3 | 0.86 | ADRB1; LPL; PPARGC1A | 1 | 10.19 | LPL | 0 | 0.00 | | 1 | 0.62 | PPARGC1A | 0 | 0.00 | |
| signaling by | 41 | 3 | 1.22 | CD79A; | 0 | 0.00 | | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| the b cell receptor bcr | | | | PSMA4; PSMD1 | | | | | | | | | | | | | | | |
| aorta development: GO | 41 | 2 | 0.82 | LTBP1; PRDM1 | 2 | 0.58 | SIX1; TFAP2B | 0 | 0.00 | | 0 | 0.00 | | 1 | 0.62 | PRICKLE1 | 0 | 0.00 | |
| histidine metabolism | 41 | 2 | 0.82 | ALDH1A3; HAL | 3 | 0.86 | AOC3; ASPA; MAOA | 0 | 0.00 | | 0 | 0.00 | | 3 | 1.86 | ALDH3A2; ASPA; HDC | 0 | 0.00 | |
| nik --> noncanonical nf-kb signaling | 41 | 2 | 0.82 | PSMA5; PSMB6 | 0 | 0.00 | | 0 | 0.00 | | 0 | 0.00 | | 0 | 0.00 | | 0 | 0.00 | |
| cranial nerve development: GO | 41 | 1 | 0.41 | NTRK1 | 7 | 2.01 | DRGX; EPHB1; KCNA2; PLXNA3; PLXNA4; SEMA3A; SIX1 | 0 | 0.00 | | 0 | 0.00 | | 3 | 1.86 | LPAR1; PLXNA4; SLITRK6 | 0 | 0.00 | |
| erbb1 internalization pathway | 41 | 1 | 0.41 | NRAS | 2 | 0.58 | DNM1; EGF | 0 | 0.00 | | 0 | 0.00 | | 1 | 0.62 | EGF | 0 | 0.00 | |
| regulation of insulin secretion by glucagon like peptide1 | 41 | 1 | 0.41 | GNGT2 | 5 | 1.44 | ADCY5; ADCY6; ADCY8; KCNB1; PRKAR2B | 1 | 10.19 | PRKAR2B | 0 | 0.00 | | 1 | 0.62 | GNG11 | 0 | 0.00 | |
| regulation of potassium ion transmembrane transporter activity: GO | 41 | 1 | 0.41 | ATP1B3 | 4 | 1.15 | ACTN2; ANK2; CASQ2; FHL1 | 0 | 0.00 | | 0 | 0.00 | | 1 | 0.62 | ATP1B2 | 0 | 0.00 | |
| detection of chemical stimulus involved in sensory perception of taste: GO | 41 | 0 | 0.00 | | 2 | 0.58 | CA6; PIP | 0 | 0.00 | | 0 | 0.00 | | 2 | 1.24 | CA6; PIP | 0 | 0.00 | |
| negative regulation of stem cell | 41 | 0 | 0.00 | | 3 | 0.86 | BMP5; MSTN; TBX5 | 0 | 0.00 | | 0 | 0.00 | | 2 | 1.24 | FOXA1; PRICKLE1 | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| differentiation: GO | | | | | | | | | | | | | | | | | | | |
| voltage gated potassium channels | 41 | 0 | 0.00 | | 7 | 2.01 | KCNA1; KCNA2; KCNA4; KCNB1; KCNB2; KCND2; KCNH8 | 0 | 0.00 | | 0 | 0.00 | | 1 | 0.62 | KCND2 | 0 | 0.00 | |
| negative regulation of sequence specific dna binding transcription factor activity: GO | 127 | 5 | 0.66 | HMOX1; PRNP; PYCARD; TNFRSF4; ZC3H12A | 4 | 0.37 | HAND2; PKHD1; PTCH1; PTGIS | 0 | 0.00 | | 0 | 0.00 | | 3 | 0.60 | ESR1; HAND2; PTCH1 | 2 | 0.45 | TRIB1; ZC3H12A |
| regulation of cellular ketone metabolic process: GO | 165 | 13 | 1.32 | ANXA1; GK; NR4A3; ODC1; PSMA4; PSMA5; PSMB6; PSMD1; PSME3; PTGS2; UGT1A1; UGT1A10; UGT1A7 | 16 | 1.14 | ABCD2; ACACB; ACADL; ADIPOQ; APOC1; ATCAY; BMP5; CNR1; IRS2; KAT2A; MLXIPL; PDK4; PLIN5; PPARGC1A; PRKAA2; SNCA | 2 | 5.07 | ABCD2; ADIPOQ | 0 | 0.00 | | 6 | 0.92 | DGAT2; PDK3; PDK4; PPARGC1A; PRKAA2; SNCA | 3 | 0.52 | ODC1; PTGS2; TRIB3 |
| regulation of cell matrix adhesion: GO | 87 | 5 | 0.96 | CCL21; GREM1; PLAU; RHOD; SERPINE1 | 5 | 0.68 | APOD; ARHGAP6; BCL2; MYOC; SEMA3E | 0 | 0.00 | | 1 | 4.80 | SERPINE1 | 4 | 1.17 | BCL2; DLC1; MYOC; SEMA3E | 1 | 0.33 | RHOD |
| steroid binding: GO | 87 | 4 | 0.77 | FABP6; PAQR5; PYGL; UGT1A1 | 12 | 1.63 | ALDH1A1; APOD; APOE; AR; ATP1A2; CYP21A2; ESRRG; NR3C2; PGR; | 1 | 4.80 | HSD11B2 | 0 | 0.00 | | 8 | 2.34 | CYP3A4; ESR1; ESRRG; NR3C2; PGR; PMP2; PTCH1; | 1 | 0.33 | PAQR5 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | | | | PTCH1; RORC; SOAT2 | | | | | | | | | SULT1E1 | | | |
| endocytosis | 128 | 7 | 0.92 | ARAP2; CCR5; CXCR4; HSPA6; HSPA8; IL2RA; NTRK1 | 7 | 0.65 | ADRB1; EGF; ERBB4; FGFR3; HSPA1L; PSD2; VPS37D | 0 | 0.00 | | 1 | 3.26 | IL2RA | 2 | 0.40 | EGF; ERBB4 | 2 | 0.44 | HLA-G; HSPA8 |
| integrin3 pathway | 42 | 4 | 1.59 | PLAU; PLAUR; SDC1; TNC | 1 | 0.28 | EDIL3 | 0 | 0.00 | | 0 | 0.00 | | 1 | 0.60 | EDIL3 | 0 | 0.00 | |
| dectin-1 mediated noncanonical nf-kb signaling | 42 | 2 | 0.80 | PSMA5; PSMB6 | 0 | 0.00 | | 0 | 0.00 | | 0 | 0.00 | | 0 | 0.00 | | 0 | 0.00 | |
| hedgehog ligand biogenesis | 42 | 2 | 0.80 | PSMA5; PSMB6 | 0 | 0.00 | | 0 | 0.00 | | 0 | 0.00 | | 0 | 0.00 | | 0 | 0.00 | |
| negative regulation of cyclic nucleotide metabolic process: GO | 42 | 2 | 0.80 | GNAI3; GPR87 | 5 | 1.40 | ADRA2A; DRD4; GALR1; GRM7; PALM | 0 | 0.00 | | 0 | 0.00 | | 3 | 1.81 | ADRA2A; LPAR1; PALM | 0 | 0.00 | |
| signaling by fgfr mutants | 42 | 2 | 0.80 | NRAS; STAT1 | 6 | 1.69 | FGF1; FGF17; FGF22; FGF9; FGFR1; FGFR3 | 0 | 0.00 | | 0 | 0.00 | | 3 | 1.81 | FGF2; FGF22; FGFR1 | 0 | 0.00 | |
| biopeptides pathway | 42 | 1 | 0.40 | STAT1 | 4 | 1.12 | AGT; CAMK2A; CAMK2B; MAPT | 0 | 0.00 | | 0 | 0.00 | | 1 | 0.60 | MAPT | 0 | 0.00 | |
| ciliary tip: GO | 42 | 1 | 0.40 | DYNLL1 | 1 | 0.28 | GLI2 | 0 | 0.00 | | 0 | 0.00 | | 1 | 0.60 | GLI2 | 0 | 0.00 | |
| dynein complex: GO | 42 | 1 | 0.40 | DYNLL1 | 4 | 1.12 | CCDC114; DNAH11; DNAH6; DYNC1I1 | 0 | 0.00 | | 0 | 0.00 | | 1 | 0.60 | CCDC114 | 0 | 0.00 | |
| hnf3b pathway | 42 | 1 | 0.40 | FOXF1 | 4 | 1.12 | ABCC8; ALB; ALDOB; PCK1 | 0 | 0.00 | | 0 | 0.00 | | 1 | 0.60 | FOXA1 | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| metabolism of non coding rna | 42 | 1 | 0.40 | SNRPG | 0 | 0.00 | | 0 | 0.00 | | 0 | 0.00 | | 0 | 0.00 | | 0 | 0.00 | |
| negative regulation of gtpase activity: GO | 42 | 1 | 0.40 | ADCYAP1 | 3 | 0.84 | AMOT; SLIT2; USP17L2 | 0 | 0.00 | | 0 | 0.00 | | 2 | 1.21 | SLIT2; SPRY1 | 0 | 0.00 | |
| xbp1(s) activates chaperone genes | 42 | 1 | 0.40 | SEC61G | 1 | 0.28 | TSPYL2 | 0 | 0.00 | | 0 | 0.00 | | 0 | 0.00 | | 0 | 0.00 | |
| cell fate determination: GO | 42 | 0 | 0.00 | | 6 | 1.69 | DSCAML1; FEZF2; MESP1; PAX6; PTCH1; PTCH2 | 0 | 0.00 | | 0 | 0.00 | | 4 | 2.42 | MESP1; PRRX1; PTCH1; PTCH2 | 0 | 0.00 | |
| chondroitin sulfate proteoglycan metabolic process: GO | 42 | 0 | 0.00 | | 4 | 1.12 | BCAN; CHST12; IDUA; NDNF | 0 | 0.00 | | 0 | 0.00 | | 4 | 2.42 | CHST12; DCN; DSEL; NDNF | 0 | 0.00 | |
| nadh dehydrogenase complex: GO | 42 | 0 | 0.00 | | 1 | 0.28 | SNCA | 0 | 0.00 | | 0 | 0.00 | | 1 | 0.60 | SNCA | 0 | 0.00 | |
| hydrolase activity hydrolyzing o glycosyl compounds: GO | 88 | 5 | 0.95 | CHI3L2; HPSE; HYAL3; LYZ; NEU2 | 4 | 0.54 | AMY2B; HPSE2; IDUA; OTOGL | 0 | 0.00 | | 1 | 4.75 | LYZ | 3 | 0.87 | ACER1; AMY2B; HPSE2 | 1 | 0.32 | HPSE |
| regulation of protein targeting to mitochondrion: GO | 88 | 5 | 0.95 | ITGAX; NRG1; RAC2; RUVBL1; UGCG | 5 | 0.67 | CDKL2; HSPA1L; KAT2A; MYBPC1; NMUR1 | 0 | 0.00 | | 1 | 4.75 | RAC2 | 1 | 0.29 | RHOU | 1 | 0.32 | NRG1 |
| rrna processing in the nucleus and cytosol | 88 | 3 | 0.57 | RPL22L1; RPP40; UTP11 | 0 | 0.00 | | 0 | 0.00 | | 0 | 0.00 | | 0 | 0.00 | | 1 | 0.32 | NOP56 |
| syntaxin binding: GO | 88 | 1 | 0.19 | UNC13A | 7 | 0.94 | ABCC8; RPH3AL; SYBU; SYT1; SYT17; SYT8; SYT9 | 0 | 0.00 | | 0 | 0.00 | | 2 | 0.58 | SYBU; SYT17 | 1 | 0.32 | UNC13A |
| voltage | 129 | 4 | 0.52 | CNGB1; | 23 | 2.10 | ABCC8; | 0 | 0.00 | | 0 | 0.00 | | 8 | 1.58 | CACNA1G; | 2 | 0.44 | KCNK1; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| gated cation channel activity: GO | | | | HTR3A; KCNJ15; KCNK1 | | | CACNA1F; CACNA1H; CACNA2D1; CACNA2D2; CACNB1; GRIN1; GRM7; IL1RAPL1; KCNA1; KCNA2; KCNA4; KCNB1; KCNB2; KCND2; KCNH8; KCNIP2; KCNJ1; KCNJ3; KCNT2; KCNU1; NOX1; TMC2 | | | | | | | | | CACNA1H; CACNA2D1; CACNA2D2; CACNB1; KCND2; KCNK2; KCNT2 | | | TMC1 |
| mesonephros development: GO | 89 | 4 | 0.75 | GDNF; GREM1; PGF; SDC1 | 17 | 2.25 | ADAMTS16; BCL2; FGF1; FGFR1; GPC3; NOG; OSR1; OSR2; PKD1; PTCH1; REN; SIM1; SIX1; SLIT2; TCF21; WNT11; ZBTB16 | 0 | 0.00 | | 0 | 0.00 | | 10 | 2.85 | BCL2; FGF2; FGFR1; FOXC1; OSR1; PTCH1; SIM1; SLIT2; SPRY1; WNT11 | 1 | 0.32 | WNT9B |
| defense response to gram negative bacterium: GO | 43 | 8 | 3.11 | CAMP; IL12B; IL6; PYCARD; RNASE7; S100A7; SERPINE1; TREM1 | 3 | 0.82 | FCN2; NOS2; SSC5D | 0 | 0.00 | | 2 | 19.44 | SERPINE1; TREM1 | 2 | 1.18 | IGHM; SSC5D | 0 | 0.00 | |
| pyrimidine | 43 | 4 | 1.56 | CMPK2; | 2 | 0.55 | NEIL1; UPP2 | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| nucleotide metabolic process: GO | | | | NME1; TYMP; UPP1 | | | | | | | | | | | | | | | |
| hedgehog 'on' state | 43 | 3 | 1.17 | CSNK1A1; PSMA5; PSMB6 | 0 | 0.00 | | 0 | 0.00 | | 0 | 0.00 | | 0 | 0.00 | | 0 | 0.00 | |
| body morphogenesis: GO | 43 | 1 | 0.39 | STRA6 | 6 | 1.65 | CDON; DKK1; GPC3; GREM2; MYH3; NOG | 0 | 0.00 | | 0 | 0.00 | | 2 | 1.18 | CDON; GREM2 | 0 | 0.00 | |
| cytosolic small ribosomal subunit: GO | 43 | 1 | 0.39 | RPS26 | 2 | 0.55 | HBA1; HBA2 | 0 | 0.00 | | 0 | 0.00 | | 1 | 0.59 | HBA2 | 0 | 0.00 | |
| plc beta mediated events | 43 | 1 | 0.39 | GNAI3 | 7 | 1.92 | ADCY2; ADCY5; ADCY6; ADCY8; GNAZ; PLCB4; PRKAR2B | 1 | 9.72 | PRKAR2B | 0 | 0.00 | | 2 | 1.18 | PDE1A; PLCB4 | 0 | 0.00 | |
| activation of chaperone genes by xbpls | 43 | 0 | 0.00 | | 1 | 0.27 | TSPYL2 | 0 | 0.00 | | 0 | 0.00 | | 0 | 0.00 | | 0 | 0.00 | |
| endocrine process: GO | 43 | 0 | 0.00 | | 7 | 1.92 | AGT; AGTR1; EDN3; FZD4; NOX1; PCSK5; REN | 1 | 9.72 | HSD11B2 | 0 | 0.00 | | 4 | 2.36 | AGTR1; CORIN; CTSG; EDN3 | 0 | 0.00 | |
| pigment biosynthetic process: GO | 43 | 0 | 0.00 | | 4 | 1.10 | ALAS2; DCT; OCA2; PPOX | 0 | 0.00 | | 0 | 0.00 | | 3 | 1.77 | ASIP; PPOX; TRPC1 | 0 | 0.00 | |
| protein deacetylase activity: GO | 43 | 0 | 0.00 | | 1 | 0.27 | HDAC5 | 0 | 0.00 | | 0 | 0.00 | | 0 | 0.00 | | 0 | 0.00 | |
| trna binding: GO | 43 | 0 | 0.00 | | 1 | 0.27 | TERT | 0 | 0.00 | | 0 | 0.00 | | 0 | 0.00 | | 0 | 0.00 | |
| cell growth: GO | 130 | 5 | 0.64 | AURKA; FLRT3; IL6; IL7R; NDRG4 | 20 | 1.82 | ACTA1; ADRA1A; AGT; AR; ATP6V0E2; BCL2; COBL; DCLK1; DCX; MAPT; MYOCD; | 0 | 0.00 | | 1 | 3.21 | IL7R | 10 | 1.95 | ADRA1A; ATP6V0E2; BCL2; DCLK1; MAPT; NDNF; SLIT2; SLIT3; SORBS2; | 2 | 0.44 | AURKA; FLRT3 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | | | | NDNF; NUPR1; PLXNA3; ROS1; SEMA3A; SLIT2; SLIT3; SORBS2; TNN | | | | | | | | | TNN | | | |
| nephron epithelium development: GO | 90 | 3 | 0.56 | GDNF; GREM1; PGF | 18 | 2.36 | ADAMTS16; BCL2; CD34; FGF1; GPC3; IRX1; KLF15; MAGI2; NOG; OSR1; PKD1; POU3F3; PTCH1; SIX1; SOX8; TCF21; TFAP2B; WNT11 | 0 | 0.00 | | 0 | 0.00 | | 7 | 1.98 | BCL2; CD34; FGF2; OSR1; POU3F3; PTCH1; WNT11 | 1 | 0.32 | WNT9B |
| glycosphingolipid metabolism | 44 | 4 | 1.52 | ARSH; GLTP; NEU2; UGCG | 1 | 0.27 | GAL3ST1 | 0 | 0.00 | | 0 | 0.00 | | 0 | 0.00 | | 0 | 0.00 | |
| abc transporters | 44 | 3 | 1.14 | ABCA12; ABCG4; TAP2 | 11 | 2.95 | ABCA10; ABCA2; ABCA3; ABCA6; ABCA8; ABCA9; ABCB11; ABCC3; ABCC8; ABCD2; CFTR | 1 | 9.50 | ABCD2 | 0 | 0.00 | | 3 | 1.73 | ABCA3; ABCB5; ABCC9 | 0 | 0.00 | |
| regulation of ras by gaps | 44 | 3 | 1.14 | NRAS; PSMA5; PSMB6 | 0 | 0.00 | | 0 | 0.00 | | 0 | 0.00 | | 0 | 0.00 | | 0 | 0.00 | |
| guanosine containing compound metabolic process: GO | 44 | 2 | 0.76 | GNAI3; NME1 | 2 | 0.54 | DLG2; MPP2 | 0 | 0.00 | | 0 | 0.00 | | 2 | 1.15 | DLG2; MPP2 | 0 | 0.00 | |
| t cell signal | 44 | 2 | 0.76 | CTLA4; | 1 | 0.27 | PAK3 | 0 | 0.00 | | 1 | 9.50 | LCP2 | 1 | 0.58 | PAK3 | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| transduction | | | | PRDX1 | | | | | | | | | | | | | | | |
| cyclic nucleotide mediated signaling: GO | 44 | 1 | 0.38 | ADCYAP1 | 7 | 1.88 | ADCY2; ADCY5; ADCY6; ADCY8; APOE; PCLO; PDE9A | 0 | 0.00 | | 0 | 0.00 | | 4 | 2.31 | ADCYAP1R1; PCLO; PDE9A; PRKG1 | 0 | 0.00 | |
| transcription coupled ner tc ner | 44 | 1 | 0.38 | PCNA | 0 | 0.00 | | 0 | 0.00 | | 0 | 0.00 | | 0 | 0.00 | | 0 | 0.00 | |
| manganese ion binding: GO | 44 | 0 | 0.00 | | 3 | 0.80 | ADCY2; PCK1; SLC24A2 | 0 | 0.00 | | 0 | 0.00 | | 0 | 0.00 | | 0 | 0.00 | |
| negative regulation of erbb signaling pathway: GO | 44 | 0 | 0.00 | | 1 | 0.27 | EGF | 0 | 0.00 | | 0 | 0.00 | | 2 | 1.15 | EGF; SPRY1 | 0 | 0.00 | |
| synthesis of pips at the plasma membrane | 44 | 0 | 0.00 | | 1 | 0.27 | PLEKHA6 | 0 | 0.00 | | 0 | 0.00 | | 2 | 1.15 | PIK3R6; PLEKHA6 | 0 | 0.00 | |
| vesicle coat: GO | 44 | 0 | 0.00 | | 1 | 0.27 | NCALD | 0 | 0.00 | | 0 | 0.00 | | 1 | 0.58 | NCALD | 0 | 0.00 | |
| antigen processing and presentation of peptide antigen via mhc class i: GO | 91 | 10 | 1.84 | CALR; FCGR1A; IFI30; PDIA3; PSMA4; PSMA5; PSMB6; PSMD1; PSME3; TAP2 | 1 | 0.13 | CD207 | 0 | 0.00 | | 0 | 0.00 | | 2 | 0.56 | ABCB5; CD207 | 1 | 0.31 | HLA-G |
| inner ear morphogenesis: GO | 91 | 5 | 0.92 | ALDH1A3; CHRNA9; GRHL3; NR4A3; WNT5A | 14 | 1.82 | ATP2B2; ATP6V1B1; CLIC5; COL11A1; FGF9; FGFR1; FRZB; GLI2; ITGA8; MYO15A; PDZD7; PTPRQ; SIX1; SOBP | 0 | 0.00 | | 0 | 0.00 | | 8 | 2.23 | CLIC5; COL11A1; FGFR1; GLI2; PDZD7; PRRX1; SLITRK6; ZIC1 | 1 | 0.31 | WNT5A |
| large ribosomal | 91 | 5 | 0.92 | MRPL13; | 0 | 0.00 | | 0 | 0.00 | | 0 | 0.00 | | 0 | 0.00 | | 1 | 0.31 | MPV17L2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| subunit: GO | | | | MRPL36; MRPL51; RPL22L1; RPL26L1 | | | | | | | | | | | | | | | |
| regulation of rna splicing: GO | 91 | 3 | 0.55 | C1QBP; HSPA8; RPS26 | 4 | 0.52 | AFF2; CELF4; RBFOX1; RBM11 | 0 | 0.00 | | 0 | 0.00 | | 1 | 0.28 | RBM20 | 1 | 0.31 | HSPA8 |
| proteasome | 45 | 8 | 2.97 | IFNG; POMP; PSMA4; PSMA5; PSMB6; PSMC1P4; PSMD1; PSME3 | 0 | 0.00 | | 0 | 0.00 | | 0 | 0.00 | | 0 | 0.00 | | 0 | 0.00 | |
| protein targeting to mitochondrion: GO | 45 | 4 | 1.49 | HSPA4; TIMM13; TIMM23; TIMM8B | 0 | 0.00 | | 0 | 0.00 | | 0 | 0.00 | | 0 | 0.00 | | 0 | 0.00 | |
| activation of nf-kappab in b cells | 45 | 2 | 0.74 | PSMA5; PSMB6 | 0 | 0.00 | | 0 | 0.00 | | 0 | 0.00 | | 0 | 0.00 | | 0 | 0.00 | |
| lung morpho-genesis: GO | 45 | 2 | 0.74 | FOXF1; TNC | 4 | 1.05 | HHIP; LIF; NOG; TCF21 | 0 | 0.00 | | 0 | 0.00 | | 2 | 1.13 | FOXA1; SPRY1 | 0 | 0.00 | |
| non membrane spanning protein tyrosine kinase activity: GO | 45 | 2 | 0.74 | JAK3; MELK | 1 | 0.26 | PKDCC | 0 | 0.00 | | 0 | 0.00 | | 0 | 0.00 | | 0 | 0.00 | |
| t tubule: GO | 45 | 1 | 0.37 | DYSF | 6 | 1.57 | ADRA1A; ANK2; ATP1A2; CACNA2D1; KCNJ3; SLC2A4 | 0 | 0.00 | | 0 | 0.00 | | 3 | 1.69 | ADRA1A; CACNA2D1; ESR1 | 0 | 0.00 | |
| thymocyte aggregation: GO | 45 | 1 | 0.37 | CD3E | 2 | 0.52 | BCL2; FZD8 | 0 | 0.00 | | 0 | 0.00 | | 2 | 1.13 | BCL2; FZD7 | 0 | 0.00 | |
| ventral spinal cord development: GO | 45 | 1 | 0.37 | TBX20 | 8 | 2.10 | FOXN4; GLI2; MDGA2; MNX1; PAX6; PTCH1; | 0 | 0.00 | | 0 | 0.00 | | 3 | 1.69 | GLI2; PTCH1; RELN | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | RELN; SOX1 | | | | | | | | | | | | |
| microbody lumen: GO | 45 | 0 | 0.00 | | 3 | 0.79 | ACOX2; CRAT; HAO2 | 0 | 0.00 | | 0 | 0.00 | | 1 | 0.56 | ACOX2 | 0 | 0.00 | |
| negative regulation of chromatin modification: GO | 45 | 0 | 0.00 | | 3 | 0.79 | SNCA; TET1; USP17L2 | 0 | 0.00 | | 0 | 0.00 | | 2 | 1.13 | SNCA; TET1 | 0 | 0.00 | |
| regulation of systemic arterial blood pressure mediated by a chemical signal: GO | 45 | 0 | 0.00 | | 10 | 2.62 | ADRA1A; ADRA1B; ADRB1; AGT; AGTR1; EDN3; NOX1; PCSK5; REN; TPM1 | 1 | 9.29 | HSD11B2 | 0 | 0.00 | | 5 | 2.82 | ADRA1A; AGTR1; CORIN; CTSG; EDN3 | 0 | 0.00 | |
| amide transport: GO | 92 | 8 | 1.46 | ABCA12; ANXA1; AQP3; IL1RN; IL6; PDPN; SLC38A1; TAP2 | 11 | 1.41 | AQP7; CARTPT; EDN3; FAM3B; FOLR1; FOLR2; LEP; PCLO; SLC14A1; SLC14A2; SLC15A5 | 0 | 0.00 | | 1 | 4.54 | AQP9 | 4 | 1.10 | EDN3; PCLO; SLC14A1; SLC18A2 | 1 | 0.31 | AQP3 |
| pml body: GO | 92 | 3 | 0.55 | BLM; ISG20; TRIM16 | 4 | 0.51 | PPARGC1A; SPTBN4; TERT; ZBTB16 | 0 | 0.00 | | 0 | 0.00 | | 2 | 0.55 | PPARGC1A; SPTBN4 | 1 | 0.31 | BLM |
| reactive oxygen species metabolic process: GO | 92 | 2 | 0.36 | IL19; PRDX1 | 13 | 1.67 | BCL2; CYP1A1; CYP1A2; EPHX2; GCHFR; HBA1; HBA2; HBB; NOS2; NOX1; P2RX7; PDK4; SOD3 | 0 | 0.00 | | 0 | 0.00 | | 7 | 1.93 | AOX1; BCL2; CTGF; HBA2; HBB; PDK4; SOD3 | 1 | 0.31 | IL19 |
| met pathway | 92 | 1 | 0.18 | EIF4EBP1 | 2 | 0.26 | ACTA1; MUC20 | 0 | 0.00 | | 0 | 0.00 | | 1 | 0.28 | MUC20 | 1 | 0.31 | EIF4EBP1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| oxidoreductase activity acting on nad p h: GO | 92 | 1 | 0.18 | TXNDC17 | 2 | 0.26 | NOX1; WDR93 | 0 | 0.00 | | 0 | 0.00 | | 0 | 0.00 | | 1 | 0.31 | TXNDC17 |
| negative regulation of carbohydrate metabolic process: GO | 46 | 4 | 1.46 | IL6; UGT1A1; UGT1A10; UGT1A7 | 6 | 1.54 | ADIPOQ; ENPP1; LEPR; MST1; PPARGC1A; SERPINA12 | 1 | 9.08 | ADIPOQ | 0 | 0.00 | | 2 | 1.10 | PPARGC1A; SERPINA12 | 0 | 0.00 | |
| positive regulation of phagocytosis: GO | 46 | 4 | 1.46 | CALR; F2RL1; IL1B; PYCARD | 2 | 0.51 | C3; MERTK | 0 | 0.00 | | 1 | 9.08 | IL1B | 2 | 1.10 | C3; TUB | 0 | 0.00 | |
| ionotropic glutamate receptor complex: GO | 46 | 1 | 0.36 | NETO2 | 14 | 3.59 | DLG2; GRIA1; GRIA2; GRIA4; GRIK4; GRIK5; GRIN1; GRIN2A; NETO1; NLGN1; SHANK1; SHISA6; SHISA8; VWC2L | 1 | 9.08 | GRIA4 | 0 | 0.00 | | 5 | 2.76 | CNIH3; DLG2; GRIA1; GRIA2; VWC2 | 0 | 0.00 | |
| clathrin coat: GO | 46 | 0 | 0.00 | | 1 | 0.26 | NCALD | 0 | 0.00 | | 0 | 0.00 | | 1 | 0.55 | NCALD | 0 | 0.00 | |
| myofibril assembly: GO | 46 | 0 | 0.00 | | 13 | 3.33 | ACTA1; ACTN2; CASQ2; FHOD3; LDB3; LMOD1; MYH11; MYH3; MYOZ1; NKX2-5; OBSCN; TMOD1; TPM1 | 0 | 0.00 | | 0 | 0.00 | | 1 | 0.55 | LMOD1 | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| mitochondrial membrane part: GO | 134 | 4 | 0.50 | BAK1; COX7B; PPIF; TIMM23 | 4 | 0.35 | COX7A1; PPOX; SNCA; SOX10 | 0 | 0.00 | | 0 | 0.00 | | 4 | 0.76 | ARMCX3; COX7A1; PPOX; SNCA | 2 | 0.42 | BAK1; PPIF |
| neuromuscular process: GO | 93 | 5 | 0.90 | ALDH1A3; NEFL; NR4A3; NRG1; STRA6 | 13 | 1.65 | ADCY5; ATP2B2; CLIC5; DRD1; FABP7; GLRB; GRIN1; GRIN2A; KCNA1; NPAS1; NRXN1; PCDH15; SHANK1 | 0 | 0.00 | | 0 | 0.00 | | 4 | 1.09 | CLIC5; GLRB; NRXN1; SLITRK6 | 1 | 0.30 | NRG1 |
| tcr pathway | 93 | 4 | 0.72 | CD3E; CD80; NRAS; PRKCQ | 1 | 0.13 | TRPV6 | 0 | 0.00 | | 1 | 4.49 | LCP2 | 0 | 0.00 | | 1 | 0.30 | PRKCQ |
| rrna processing | 93 | 3 | 0.54 | RPL22L1; RPP40; UTP11 | 0 | 0.00 | | 0 | 0.00 | | 0 | 0.00 | | 0 | 0.00 | | 1 | 0.30 | NOP56 |
| mrna splicing - major pathway | 93 | 2 | 0.36 | HSPA8; SNRPF | 1 | 0.13 | PPIL6 | 0 | 0.00 | | 0 | 0.00 | | 1 | 0.27 | PPIL6 | 1 | 0.30 | HSPA8 |
| macromolecule methylation: GO | 173 | 1 | 0.10 | HIST1H1D | 4 | 0.27 | CHD5; PIWIL2; RAB3B; TDRD5 | 0 | 0.00 | | 0 | 0.00 | | 1 | 0.15 | RAB3B | 3 | 0.49 | BEND3; HIST1H1D; TDRD9 |
| fc epsilon receptor signaling pathway: GO | 135 | 11 | 1.36 | IGKC; IGKV4-1; NR4A3; NRAS; PRKCQ; PSMA4; PSMA5; PSMB6; PSMD1; PSME3; UBE2N | 0 | 0.00 | | 1 | 3.10 | IGKV3-20 | 1 | 3.10 | LCP2 | 2 | 0.38 | IGHV3-23; MS4A2 | 2 | 0.42 | PRKCQ; VAV2 |
| positive | 94 | 5 | 0.89 | C1QBP; | 6 | 0.75 | ABI3BP; | 0 | 0.00 | | 0 | 0.00 | | 8 | 2.16 | ABI3BP; | 1 | 0.30 | ITGA3 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| regulation of cell substrate adhesion: GO | | | | CALR; CCL21; FOXF1; ITGA3 | | | CCDC80; EDIL3; MYOC; NDNF; VIT | | | | | | | | | CCDC80; EDIL3; FBLN1; FBLN2; MYOC; NDNF; VWC2 | | | |
| glomerulus development: GO | 47 | 2 | 0.71 | GPR4; SULF2 | 6 | 1.51 | BCL2; CD34; KLF15; MAGI2; OSR1; TCF21 | 0 | 0.00 | | 0 | 0.00 | | 4 | 2.16 | ANGPT1; BCL2; CD34; OSR1 | 0 | 0.00 | |
| hedgehog gli pathway | 47 | 2 | 0.71 | CSNK1A1; GNAI3 | 4 | 1.00 | GLI2; GNAZ; PTCH1; SSPO | 0 | 0.00 | | 0 | 0.00 | | 2 | 1.08 | GLI2; PTCH1 | 0 | 0.00 | |
| regulation of pten stability and activity | 47 | | 0.71 | PSMA5; PSMB6 | 0 | 0.00 | | 0 | 0.00 | | 0 | 0.00 | | 1 | 0.54 | PREX2 | 0 | 0.00 | |
| regulation of skeletal muscle tissue development: GO | 47 | 2 | 0.71 | HMGCR; USP2 | 7 | 1.76 | BCL2; CDON; DKK1; MSTN; MYOCD; SIX1; TSC22D3 | 0 | 0.00 | | 0 | 0.00 | | 4 | 2.16 | BCL2; CDON; SHOX2; TSC22D3 | 0 | 0.00 | |
| hormone biosynthetic process: GO | 47 | 1 | 0.36 | AKR1B15 | 7 | 1.76 | CACNA1H; CYP17A1; CYP21A2; DIO3; HSD17B14; LHB; TG | 0 | 0.00 | | 0 | 0.00 | | 1 | 0.54 | CACNA1H | 0 | 0.00 | |
| complement cascade | 47 | 0 | 0.00 | | 8 | 2.01 | C3; C4BPA; C6; C7; CFD; CFH; CLU; FCN2 | 0 | 0.00 | | 0 | 0.00 | | 3 | 1.62 | C3; CFH; CLU | 0 | 0.00 | |
| striated muscle contraction: GO | 95 | 4 | 0.70 | CXCR4; GJA1; HOMER1; MYLK2 | 17 | 2.11 | ANK2; ATP1A2; CACNA2D1; CASQ2; DMD; DTNA; MYH14; MYH3; MYL3; MYL4; NKX2-5; | 0 | 0.00 | | 0 | 0.00 | | 3 | 0.80 | CACNA2D1; TNNC1; TNNT3 | 1 | 0.30 | HOMER1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | TNNC1; TNNC2; TNNI2; TNNT2; TNNT3; TPM1 | | | | | | | | | | | | |
| b cell receptor signaling pathway: GO | 48 | 6 | 2.09 | CD79A; CTLA4; IGHG1; IGHG2; IGHG4; IGKC | 1 | 0.25 | BCL2 | 1 | 8.71 | IGHG1 | 0 | 0.00 | | 3 | 1.59 | BCL2; IGHM; IGHV3-23 | 0 | 0.00 | |
| cajal body: GO | 48 | 4 | 1.39 | ISG20; NOLC1; NOP10; OIP5 | 2 | 0.49 | ANKS1B; HSPB7 | 0 | 0.00 | | 0 | 0.00 | | 0 | 0.00 | | 0 | 0.00 | |
| golgi associated vesicle membrane: GO | 48 | 2 | 0.70 | CNGB1; GJA1 | 3 | 0.74 | CFTR; NCALD; PKD1 | 0 | 0.00 | | 0 | 0.00 | | 1 | 0.53 | NCALD | 0 | 0.00 | |
| positive regulation of stem cell differentiation: GO | 48 | 1 | 0.35 | SERPINB3 | 4 | 0.98 | ALX1; NKX2-5; SOX5; TBX5 | 0 | 0.00 | | 0 | 0.00 | | 1 | 0.53 | FOXC1 | 0 | 0.00 | |
| phosphatidyl-inositol 3 phosphate biosynthetic process: GO | 48 | 0 | 0.00 | | 7 | 1.72 | FGF1; FGF17; FGF22; FGF9; FGFR1; FGFR3; IRS2 | 0 | 0.00 | | 0 | 0.00 | | 3 | 1.59 | FGF2; FGF22; FGFR1 | 0 | 0.00 | |
| regulation of t cell mediated immunity: GO | 49 | 6 | 2.05 | IL12B; IL1B; IL7R; RSAD2; SASH3; SLAMF1 | 1 | 0.24 | P2RX7 | 0 | 0.00 | | 2 | 17.06 | IL1B; IL7R | 0 | 0.00 | | 0 | 0.00 | |
| neurotransmitter receptors and postsynaptic signal transmission | 49 | 1 | 0.34 | GNAI3 | 4 | 0.96 | ADCY8; GRIK3; GRIN2A; NCALD | 0 | 0.00 | | 0 | 0.00 | | 4 | 2.07 | GNG11; GRIK3; NCALD; TSPAN7 | 0 | 0.00 | |
| cellular response to amino acid stimulus: GO | 49 | 0 | 0.00 | | 5 | 1.20 | CPEB1; FOLR1; FOLR2; HMGCS2; PDGFD | 0 | 0.00 | | 0 | 0.00 | | 2 | 1.04 | CPEB1; HMGCS2 | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| regulation of humoral immune response: GO | 50 | 6 | 2.01 | C1QBP; CXCL13; DEFB103A; DEFB103B; KLK5; KLK7 | 6 | 1.42 | C3; C4BPA; C6; C7; CFH; FCER2 | 0 | 0.00 | | 0 | 0.00 | | 2 | 1.02 | C3; CFH | 0 | 0.00 | |
| neuromuscular process controlling balance: GO | 50 | 3 | 1.00 | ALDH1A3; NEFL; NR4A3 | 6 | 1.42 | ADCY5; ATP2B2; CLIC5; NRXN1; PCDH15; SHANK1 | 0 | 0.00 | | 0 | 0.00 | | 2 | 1.02 | CLIC5; NRXN1 | 0 | 0.00 | |
| skeletal muscle cell differentiation: GO | 50 | 2 | 0.67 | EOMES; MYLK2 | 3 | 0.71 | CDON; NUPR1; SOX8 | 0 | 0.00 | | 0 | 0.00 | | 2 | 1.02 | CDON; HLF | 0 | 0.00 | |
| lytic vacuole organization: GO | 50 | 1 | 0.33 | HOOK1 | 3 | 0.71 | CLVS1; CLVS2; P2RX7 | 0 | 0.00 | | 0 | 0.00 | | 0 | 0.00 | | 0 | 0.00 | |
| negative regulation of cell substrate adhesion: GO | 50 | 1 | 0.33 | SERPINE1 | 6 | 1.42 | APOD; ARHGAP6; FZD4; MYOC; SEMA3E; SPOCK1 | 0 | 0.00 | | 2 | 16.72 | GBP1; SERPINE1 | 6 | 3.05 | DLC1; FBLN1; FZD7; MYOC; SEMA3E; SPOCK1 | 0 | 0.00 | |
| phosphatidyl-inositol kinase activity: GO | 50 | 0 | 0.00 | | 7 | 1.65 | FGF1; FGF17; FGF22; FGF9; FGFR1; FGFR3; IRS2 | 0 | 0.00 | | 0 | 0.00 | | 3 | 1.52 | FGF2; FGF22; FGFR1 | 0 | 0.00 | |
| regulation of cilium assembly: GO | 50 | 0 | 0.00 | | 1 | 0.24 | ADAMTS16 | 0 | 0.00 | | 0 | 0.00 | | 0 | 0.00 | | 0 | 0.00 | |
| core promoter sequence specific dna binding: GO | 98 | 3 | 0.51 | H2AFZ; NR4A3; STAT1 | 6 | 0.72 | GATA1; MYOCD; PAX6; SOX1; SOX8; TFAP2B | 0 | 0.00 | | 0 | 0.00 | | 1 | 0.26 | ESR1 | 1 | 0.29 | H2AFZ |
| cellular modified amino acid biosynthetic process: GO | 51 | 6 | 1.97 | AHCY; CHAC1; CHAC2; CNDP2; GGCT; | 4 | 0.93 | CKM; DHPS; GGT7; MAT1A | 0 | 0.00 | | 0 | 0.00 | | 2 | 1.00 | GAMT; GATM | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | MTHFD2 | | | | | | | | | | | | | | | |
| artery morphogenesis: GO | 51 | 4 | 1.31 | FOXF1; PRDM1; STRA6; TGFBR1 | 7 | 1.62 | APOE; FOLR1; HAND2; MYOCD; SIX1; TFAP2B; WNT11 | 0 | 0.00 | | 0 | 0.00 | | 4 | 1.99 | FOXC1; HAND2; PRRX1; WNT11 | 0 | 0.00 | |
| gaba receptor activation | 51 | 3 | 0.98 | GNAI3; GNGT2; KCNJ15 | 8 | 1.85 | ADCY2; ADCY5; ADCY6; ADCY8; GABRA2; GABRB3; GABRG3; KCNJ3 | 0 | 0.00 | | 0 | 0.00 | | 0 | 0.00 | | 0 | 0.00 | |
| cation transporting atpase activity: GO | 51 | 2 | 0.66 | ATP12A; ATP1B3 | 8 | 1.85 | ABCB11; ATP13A5; ATP1A2; ATP2A1; ATP2B2; ATP6V0A4; ATP6V0E2; FXYD2 | 0 | 0.00 | | 0 | 0.00 | | 6 | 2.99 | ATP13A4; ATP13A5; ATP1B2; ATP2C2; ATP6V0A4; ATP6V0E2 | 0 | 0.00 | |
| demethylation: GO | 51 | 1 | 0.33 | APOBEC3A | 7 | 1.62 | CYP1A1; CYP1A2; CYP2C9; CYP2D6; CYP3A5; HSF4; TET1 | 0 | 0.00 | | 0 | 0.00 | | 3 | 1.49 | CYP3A4; CYP3A5; TET1 | 0 | 0.00 | |
| ligase activity forming carbon nitrogen bonds: GO | 51 | 1 | 0.33 | MTHFD2 | 4 | 0.93 | ACACB; CARNS1; RIMKLA; TTLL10 | 0 | 0.00 | | 0 | 0.00 | | 0 | 0.00 | | 0 | 0.00 | |
| negative regulation of epithelial cell migration: GO | 51 | 1 | 0.33 | CXCL13 | 5 | 1.16 | ANGPT4; APOE; HDAC5; SEMA3A; SLIT2 | 0 | 0.00 | | 0 | 0.00 | | 4 | 1.99 | ANGPT4; DCN; FGF2; SLIT2 | 0 | 0.00 | |
| negative regulation of | 51 | 0 | 0.00 | | 5 | 1.16 | BCL2; LEP; LEPR; | 0 | 0.00 | | 0 | 0.00 | | 2 | 1.00 | BCL2; SNCA | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| autophagy: GO | | | | | | | NRBP2; SNCA | | | | | | | | | | | | |
| phospholipase c mediated cascade | 51 | 0 | 0.00 | | 11 | 2.54 | ADCY2; ADCY5; ADCY6; ADCY8; FGF1; FGF17; FGF22; FGF9; FGFR1; FGFR3; PRKAR2B | 1 | 8.19 | PRKAR2B | 0 | 0.00 | | 4 | 1.99 | FGF2; FGF22; FGFR1; PDE1A | 0 | 0.00 | |
| snare complex: GO | 51 | 0 | 0.00 | | 2 | 0.46 | SYT1; TSNARE1 | 0 | 0.00 | | 0 | 0.00 | | 0 | 0.00 | | 0 | 0.00 | |
| huntingtons disease | 141 | 4 | 0.47 | COX7B; CYCS; SLC25A5; VDAC1 | 4 | 0.33 | COX7A1; GRIN1; PLCB4; PPARGC1A | 0 | 0.00 | | 0 | 0.00 | | 4 | 0.72 | COX7A1; CREB3L1; PLCB4; PPARGC1A | 2 | 0.40 | CYCS; VDAC1 |
| nonsense mediated decay enhanced by the exon junction complex | 99 | 3 | 0.51 | EIF4A3; RPL26L1; RPS26 | 1 | 0.12 | FAM153A | 0 | 0.00 | | 0 | 0.00 | | 0 | 0.00 | | 1 | 0.29 | EIF4A3 |
| hydrolase activity acting on carbon nitrogen but not peptide bonds: GO | 142 | 7 | 0.82 | APOBEC3A; APOBEC3B; CDA; MTHFD2; PGLYRP2; VNN3; ZBP1 | 4 | 0.33 | ADAD2; AMPD1; ASPA; HDAC5 | 0 | 0.00 | | 0 | 0.00 | | 3 | 0.54 | ACER1; ASPA; DPYSL3 | 2 | 0.40 | APOBEC3B; CDA |
| response to transforming growth factor beta: GO | 142 | 3 | 0.35 | TGFBR1; WNT5A; WNT7A | 9 | 0.75 | AMHR2; CGN; CLEC3B; GDF10; GDF5; MSTN; PDGFD; PPARGC1A; SOX5 | 1 | 2.94 | CLEC3B | 0 | 0.00 | | 2 | 0.36 | CGN; PPARGC1A | 2 | 0.40 | WNT5A; WNT7A |
| regulation of leukocyte mediated cytotoxicity: GO | 52 | 5 | 1.61 | F2RL1; IL12B; IL7R; SERPINB4; SERPINB9 | 3 | 0.68 | LEP; NOS2; P2RX7 | 0 | 0.00 | | 2 | 16.07 | IL7R; SERPINB9 | 1 | 0.49 | PIK3R6 | 0 | 0.00 | |
| cytosolic | 52 | 3 | 0.97 | CCL21; | 7 | 1.59 | ADRA1A; | 0 | 0.00 | | 0 | 0.00 | | 5 | 2.44 | ADRA1A; | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| calcium ion transport: GO | | | | CCL3; CCR5 | | | CACNA2D1; JPH2; NOL3; P2RX7; TRDN; TRPM1 | | | | | | | | | CACNA2D1; CTGF; FGF2; TRDN | | | |
| cell differentiation in spinal cord: GO | 52 | 1 | 0.32 | TBX20 | 7 | 1.59 | FOXN4; GLI2; MDGA2; MNX1; PAX6; PTCH1; SOX1 | 0 | 0.00 | | 0 | 0.00 | | 3 | 1.47 | GDF7; GLI2; PTCH1 | 0 | 0.00 | |
| endometrial cancer | 52 | 1 | 0.32 | NRAS | 3 | 0.68 | CTNNA3; EGF; TCF7L1 | 0 | 0.00 | | 0 | 0.00 | | 2 | 0.98 | EGF; TCF7L1 | 0 | 0.00 | |
| ras pathway | 52 | 1 | 0.32 | NRAS | 1 | 0.23 | CAMK2B | 0 | 0.00 | | 0 | 0.00 | | 0 | 0.00 | | 0 | 0.00 | |
| spliceosomal complex assembly: GO | 52 | 1 | 0.32 | SNRPG | 2 | 0.45 | CELF4; NOL3 | 0 | 0.00 | | 0 | 0.00 | | 0 | 0.00 | | 0 | 0.00 | |
| ar tf pathway | 52 | 0 | 0.00 | | 4 | 0.91 | AR; PDE9A; RXRG; TMPRSS2 | 0 | 0.00 | | 0 | 0.00 | | 1 | 0.49 | PDE9A | 0 | 0.00 | |
| taste transduction | 52 | 0 | 0.00 | | 3 | 0.68 | ADCY6; ADCY8; KCNB1 | 0 | 0.00 | | 0 | 0.00 | | 2 | 0.98 | PDE1A; SCNN1B | 0 | 0.00 | |
| translational initiation: GO | 143 | 6 | 0.70 | EIF2S1; EIF4EBP1; EIF4G2; EIF6; RPL26L1; RPS26 | 0 | 0.00 | | 0 | 0.00 | | 0 | 0.00 | | 0 | 0.00 | | 2 | 0.40 | EIF4EBP1; EIF6 |
| protein acylation: GO | 143 | 5 | 0.59 | BRCA2; ESCO2; OAS2; RUVBL1; TRIM16 | 8 | 0.66 | APBB1; CHD5; KAT2A; NAT8; NUPR1; PCK1; PER1; ZDHHC15 | 0 | 0.00 | | 0 | 0.00 | | 1 | 0.18 | ZDHHC15 | 2 | 0.40 | BEND3; BRCA2 |
| transmembrane receptor protein serine threonine kinase signaling pathway: GO | 183 | 3 | 0.27 | LTBP1; SUB1; TGFBR1 | 17 | 1.10 | ACVR1C; AMHR2; ATOH8; BMP3; BMP5; CGN; CHRDL1; GDF10; | 1 | 2.28 | ACVR1C | 0 | 0.00 | | 5 | 0.69 | ATOH8; CGN; CHRD; GDF7; GREM2 | 3 | 0.46 | BMPR1B; DSG4; SUB1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | GDF5; GREM2; INHBB; LRP4; MAGI2; MSTN; NKX2-5; NOG; TMEM100 | | | | | | | | | | | | |
| autodegradation of the e3 ubiquitin ligase cop1 | 53 | 4 | 1.26 | PSMA4; PSMA5; PSMB6; PSMD1 | 0 | 0.00 | | 0 | 0.00 | | 0 | 0.00 | | 0 | 0.00 | | 0 | 0.00 | |
| abc transporter disorders | 53 | 3 | 0.95 | ABCA12; PSMA5; PSMB6 | 2 | 0.45 | ABCA3; ABCB11 | 0 | 0.00 | | 0 | 0.00 | | 1 | 0.48 | ABCA3 | 0 | 0.00 | |
| fceri mediated nf-kb activation | 53 | 3 | 0.95 | PSMA5; PSMB6; UBE2N | 0 | 0.00 | | 0 | 0.00 | | 0 | 0.00 | | 1 | 0.48 | MS4A2 | 0 | 0.00 | |
| iron ion transport: GO | 53 | 2 | 0.63 | STEAP1B; STEAP4 | 5 | 1.11 | ATP6V0A4; ATP6V0E2; ATP6V1B1; SCARA5; TF | 0 | 0.00 | | 1 | 7.88 | STEAP1B | 5 | 2.40 | ATP6V0A4; ATP6V0E2; SCARA5; SLC40A1; STEAP2 | 0 | 0.00 | |
| regulation of postsynaptic membrane potential: GO | 53 | 2 | 0.63 | ADCYAP1; CHRNA3 | 11 | 2.45 | ADORA1; DRD4; FGF14; GABRB3; GRIK5; GRIN1; GRIN2A; PPPIR9A; SCN7A; SLC17A7; SNCA | 0 | 0.00 | | 0 | 0.00 | | 3 | 1.44 | SCN7A; SLC29A1; SNCA | 0 | 0.00 | |
| valine, leucine and isoleucine degradation | 53 | 2 | 0.63 | ALDH1A3; ESCO2 | 3 | 0.67 | ACADL; HMGCS2; PNPLA3 | 0 | 0.00 | | 0 | 0.00 | | 4 | 1.92 | ALDH3A2; AOX1; HMGCS2; PNPLA3 | 0 | 0.00 | |
| nuclear speck: GO | 185 | 4 | 0.36 | CSNK1A1; EIF4A3; | 8 | 0.51 | AFF2; APBB1; | 0 | 0.00 | | 0 | 0.00 | | 4 | 0.55 | ATOH8; GLI2; HIF3A; | 3 | 0.46 | EIF4A3; HIF1A; |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | HIF1A; IFI16 | | | ATOH8; GLI2; HIF3A; MEOX2; RBM11; ZBTB16 | | | | | | | | | MEOX2 | | | IFI16 |
| actin cytoskeleton reorganization: GO | 54 | 4 | 1.24 | ANXA1; CXADR; GPR65; S100A9 | 2 | 0.44 | BRSK2; GSN | 0 | 0.00 | | 0 | 0.00 | | 2 | 0.94 | BRSK2; FRY | 0 | 0.00 | |
| regulation of myotube differentiation: GO | 54 | 4 | 1.24 | CXCL10; CXCL9; IL4R; NEU2 | 8 | 1.75 | BCL2; BHLHE41; FLT3LG; HDAC5; MYOCD; NKX2-5; RBM24; SCGB3A1 | 0 | 0.00 | | 1 | 7.74 | CXCL9 | 4 | 1.88 | BCL2; BHLHA15; BHLHE41; SHOX2 | 0 | 0.00 | |
| degradation of beta-catenin by the destruction complex | 54 | 3 | 0.93 | CSNK1A1; PSMA5; PSMB6 | 0 | 0.00 | | 0 | 0.00 | | 0 | 0.00 | | 0 | 0.00 | | 0 | 0.00 | |
| regulation of intracellular steroid hormone receptor signaling pathway: GO | 54 | 1 | 0.31 | CALR | 4 | 0.87 | CRY2; KANK2; PER1; TCF21 | 0 | 0.00 | | 0 | 0.00 | | 2 | 0.94 | CRY2; FOXA1 | 0 | 0.00 | |
| deacetylase activity: GO | 54 | 0 | 0.00 | | 4 | 0.87 | CES1; HDAC5; MACROD1; MACROD2 | 0 | 0.00 | | 0 | 0.00 | | 2 | 0.94 | CES1; MACROD2 | 0 | 0.00 | |
| potassium ion transport: GO | 146 | 7 | 0.80 | ATP12A; ATP1B3; CNGB1; HTR3A; KCNJ15; KCNK1; KCNK10 | 19 | 1.54 | ABCC8; ATP1A2; FXYD2; KCNA1; KCNA2; KCNA4; KCNB1; KCNB2; KCND2; | 0 | 0.00 | | 0 | 0.00 | | 6 | 1.04 | ABCC9; ATP1B2; KCND2; KCNK12; KCNK2; KCNT2 | 2 | 0.39 | KCNK1; KCNK10 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | KCNH8; KCNIP1; KCNIP2; KCNJ1; KCNJ3; KCNK12; KCNMB4; KCNT2; KCNU1; SLC24A2 | | | | | | | | | | | | |
| fgf pathway | 55 | 4 | 1.22 | MMP9; PLAU; PLAUR; STAT1 | 8 | 1.72 | CAMK2A; FGF1; FGF17; FGF9; FGFR1; FGFR3; NCAM1; SDC2 | 0 | 0.00 | | 0 | 0.00 | | 3 | 1.39 | FGF2; FGFR1; NCAM1 | 0 | 0.00 | |
| peptide secretion: GO | 55 | 3 | 0.91 | ANXA1; IL1RN; IL6 | 5 | 1.07 | CARTPT; EDN3; FAM3B; LEP; PCLO | 0 | 0.00 | | 0 | 0.00 | | 3 | 1.39 | EDN3; PCLO; SLC18A2 | 0 | 0.00 | |
| tgfbr pathway | 55 | 1 | 0.30 | TGFBR1 | 2 | 0.43 | CAMK2A; DACT2 | 0 | 0.00 | | 0 | 0.00 | | 1 | 0.46 | CTGF | 0 | 0.00 | |
| exocytic vesicle membrane: GO | 55 | 0 | 0.00 | | 9 | 1.93 | ABCC8; ICA1; SLC17A7; SLC6A17; SV2B; SYN2; SYNGR1; SYT1; SYT9 | 0 | 0.00 | | 0 | 0.00 | | 4 | 1.85 | ICA1; SLC18A2; SV2B; SYN2 | 0 | 0.00 | |
| repressing transcription factor binding: GO | 55 | 0 | 0.00 | | 2 | 0.43 | GSC; HDAC5 | 0 | 0.00 | | 0 | 0.00 | | 0 | 0.00 | | 0 | 0.00 | |
| transition metal ion transport: GO | 104 | 7 | 1.13 | HEPHL1; SCO2; SLC39A6; STEAP1B; STEAP4; TCN1; TRPC4 | 7 | 0.79 | ATP6V0A4; ATP6V0E2; ATP6V1B1; CP; SCARA5; SLC30A10; TF | 0 | 0.00 | | 1 | 4.02 | STEAP1B | 8 | 1.95 | ATP2C2; ATP6V0A4; ATP6V0E2; CP; SCARA5; SLC40A1; STEAP2; TRPC1 | 1 | 0.27 | SCO2 |
| mitochondrial | 104 | 4 | 0.64 | PPIF; | 1 | 0.11 | SNCA | 0 | 0.00 | | 0 | 0.00 | | 1 | 0.24 | SNCA | 1 | 0.27 | PPIF |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| protein complex: GO | | | | TIMM13; TIMM23; TIMM8B | | | | | | | | | | | | | | | |
| unsaturated fatty acid metabolic process: GO | 104 | 2 | 0.32 | PDPN; PTGS2 | 17 | 1.93 | AWAT1; CYP1A1; CYP1A2; CYP2A6; CYP2C9; CYP2D6; CYP2J2; CYP4A11; CYP4F12; CYP4F8; ELOVL2; EPHX2; FADS2; GGT7; PLA2G5; PTGIS; SCD5 | 0 | 0.00 | | 0 | 0.00 | | 2 | 0.49 | CYP4A11; CYP4F12 | 1 | 0.27 | PTGS2 |
| protein autophos phorylation: GO | 188 | 7 | 0.62 | AURKA; EIF2S1; JAK3; MELK; MYLK2; NEK2; NTRK1 | 15 | 0.94 | CAMK2A; CAMK2B; DCX; EEF2K; EPHB1; ERBB4; FGFR1; FGFR3; HIPK4; MAPK15; MYO3A; NTRK3; PRKG2; ROS1; WNK2 | 0 | 0.00 | | 0 | 0.00 | | 5 | 0.68 | DDR2; ERBB4; FGFR1; MAK; PRKG2 | 3 | 0.45 | AURKA; AURKB; NEK2 |
| rna modification: GO | 105 | 1 | 0.16 | NOP10 | 0 | 0.00 | | 0 | 0.00 | | 0 | 0.00 | | 0 | 0.00 | | 1 | 0.27 | NOP56 |
| glucan metabolic process: GO | 56 | 2 | 0.60 | PGM2; PYGL | 6 | 1.26 | GYG2; PGM5; PHKG1; PPP1R1A; PYGM; STBD1 | 1 | 7.46 | PPP1R1A | 0 | 0.00 | | 2 | 0.91 | PGM5; PHKG1 | 0 | 0.00 | |
| regulation | 56 | 2 | 0.60 | ANXA1; | 4 | 0.84 | GRIK5; | 0 | 0.00 | | 0 | 0.00 | | 2 | 0.91 | SGSM1; | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| of vesicle fusion: GO | | | | SLAMF1 | | | SGSM1; STXBP6; SYT1 | | | | | | | | | STXBP6 | | | |
| calcium channel complex: GO | 56 | 1 | 0.30 | TRPC4 | 9 | 1.90 | ATP2A1; CACNA1F; CACNA1H; CACNA2D1; CACNA2D2; CACNB1; CASQ2; CATSPERG; TRDN | 0 | 0.00 | | 0 | 0.00 | | 7 | 3.18 | CACNA1G; CACNA1H; CACNA2D1; CACNA2D2; CACNB1; CATSPERG; TRDN | 0 | 0.00 | |
| oxidoreductase activity acting on the ch ch group of donors: GO | 56 | 0 | 0.00 | | 4 | 0.84 | ACADL; ACOX2; PECR; PPOX | 0 | 0.00 | | 0 | 0.00 | | 2 | 0.91 | ACOX2; PPOX | 0 | 0.00 | |
| anterior posterior pattern specification: GO | 189 | 5 | 0.44 | AURKA; FOXF1; RGS20; TGFBR1; WNT5A | 18 | 1.12 | ALX1; ALX4; CDON; CDX4; COBL; DKK1; EMX2; FEZF2; GLI2; GPC3; KAT2A; MEOX2; NOG; OSR1; PAX6; PCSK5; TDRD5; ZBTB16 | 0 | 0.00 | | 0 | 0.00 | | 10 | 1.34 | ALX4; CDON; CDX4; EMX2; FOXC1; GLI2; HOXA10; HOXD8; MEOX2; OSR1 | 3 | 0.45 | AURKA; RGS20; WNT5A |
| innate immune response activating cell surface receptor signaling pathway: GO | 106 | 10 | 1.58 | CLEC6A; CLEC7A; ICAM3; NRAS; PSMA4; PSMA5; PSMB6; PSMD1; PSME3; UBE2N | 1 | 0.11 | PAK3 | 0 | 0.00 | | 1 | 3.94 | FFAR2 | 1 | 0.24 | PAK3 | 1 | 0.27 | CLEC7A |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| early endosome membrane: GO | 106 | 3 | 0.47 | ANXA1; FCGR1A; NTRK1 | 7 | 0.78 | CD207; CFTR; CLVS1; CLVS2; DKK1; EPHB1; SNX21 | 0 | 0.00 | | 1 | 3.94 | SNX20 | 2 | 0.48 | CD207; CLCN4 | 1 | 0.27 | HLA-G |
| microbody membrane: GO | 57 | 1 | 0.29 | HMGCR | 3 | 0.62 | ABCD2; PECR; PEX11A | 1 | 7.33 | ABCD2 | 0 | 0.00 | | 1 | 0.45 | ALDH3A2 | 0 | 0.00 | |
| formation of the ternary complex and subsequently the 43s complex | 58 | 2 | 0.58 | EIF2S1; RPS26 | 0 | 0.00 | | 0 | 0.00 | | 0 | 0.00 | | 0 | 0.00 | | 0 | 0.00 | |
| endosome organization: GO | 58 | 1 | 0.29 | HOOK1 | 2 | 0.41 | DNM1; VPS37D | 0 | 0.00 | | 0 | 0.00 | | 0 | 0.00 | | 0 | 0.00 | |
| transcription initiation from rna polymerase ii promoter: GO | 151 | 3 | 0.33 | E2F3; NR4A3; TEAD4 | 11 | 0.86 | AR; DACH1; ESRRG; NR3C2; NR5A1; PGR; PPARGC1A; RORB; RORC; RXRG; TBX5 | 0 | 0.00 | | 0 | 0.00 | | 8 | 1.35 | CTGF; DACH1; ESR1; ESRRG; NR2F1; NR3C2; PGR; PPARGC1A | 2 | 0.38 | PPARD; TEAD4 |
| regulation of stem cell differentiation: GO | 108 | 5 | 0.77 | GDNF; GREM1; HMGA2; SERPINB3; TGFBR1 | 7 | 0.76 | ALX1; BMP5; MSTN; NKX2-5; PHLDB1; SOX5; TBX5 | 0 | 0.00 | | 0 | 0.00 | | 3 | 0.71 | FOXA1; FOXC1; PRICKLE1 | 1 | 0.26 | HMGA2 |
| response to amino acid: GO | 108 | 2 | 0.31 | GSTP1; IL6 | 13 | 1.42 | ALDOB; CDO1; CPEB1; DRD1; FOLR1; FOLR2; GLRB; GSN; HMGCS2; PDGFD; PPARGC1A; SLC1A2; | 0 | 0.00 | | 0 | 0.00 | | 5 | 1.18 | CPEB1; CTGF; GLRB; HMGCS2; PPARGC1A | 1 | 0.26 | GSTP1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | | | | TIMP3 | | | | | | | | | | | | |
| cytosolic large ribosomal subunit: GO | 59 | 2 | 0.57 | RPL22L1; RPL26L1 | 0 | 0.00 | | 0 | 0.00 | | 0 | 0.00 | | 0 | 0.00 | | 0 | 0.00 | |
| small nuclear ribonucleoprotein complex: GO | 59 | 2 | 0.57 | SNRPF; SNRPG | 1 | 0.20 | SNRPN | 0 | 0.00 | | 0 | 0.00 | | 1 | 0.43 | SNRPN | 0 | 0.00 | |
| histone deacetylase complex: GO | 59 | 0 | 0.00 | | 4 | 0.80 | CHD5; HDAC5; SALL2; ZNF541 | 0 | 0.00 | | 0 | 0.00 | | 1 | 0.43 | SALL2 | 0 | 0.00 | |
| regulation of endocytosis: GO | 194 | 11 | 0.95 | CALR; CCL21; F2RL1; GREM1; IL1B; PCSK9; PYCARD; SELE; SERPINE1; STON2; WNT5A | 13 | 0.79 | ADIPOQ; APOC1; C3; C4BPA; DKK1; EEF2K; GPC3; HAMP; MAGI2; MERTK; NLGN1; SNCA; TF | 1 | 2.15 | ADIPOQ | 3 | 6.46 | IL1B; SELE; SERPINE1 | 4 | 0.52 | ANGPT1; C3; SNCA; TUB | 3 | 0.44 | PCSK9; STON2; WNT5A |
| cul3 ring ubiquitin ligase complex: GO | 60 | 2 | 0.56 | KBTBD8; KLHDC7B | 4 | 0.79 | BACH2; KBTBD12; KLHL31; KLHL33 | 0 | 0.00 | | 1 | 6.96 | KLHDC7B | 4 | 1.69 | BACH2; GAN; KBTBD3; KLHL31 | 0 | 0.00 | |
| regulation of potassium ion transmembrane transport: GO | 60 | 2 | 0.56 | ATP1B3; PRNP | 9 | 1.77 | ACTN2; ANK2; CASQ2; DPP10; DPP6; EDN3; FHL1; KCNIP1; KCNIP2 | 0 | 0.00 | | 0 | 0.00 | | 3 | 1.27 | ATP1B2; DPP6; EDN3 | 0 | 0.00 | |
| regulation of lymphocyte mediated immunity: GO | 110 | 9 | 1.37 | IFNG; IL12B; IL1B; IL7R; RSAD2; SASH3; SERPINB4; SERPINB9; SLAMF1 | 5 | 0.54 | C3; C4BPA; FCER2; LEP; P2RX7 | 0 | 0.00 | | 3 | 11.40 | IL1B; IL7R; SERPINB9 | 2 | 0.46 | C3; PIK3R6 | 1 | 0.26 | IL10 |
| protein | 110 | 7 | 1.06 | ANXA1; | 10 | 1.07 | AGT; CBLN1; | 1 | 3.80 | GPAM | 2 | 7.60 | LCP2; | 3 | 0.69 | KLRF2; | 1 | 0.26 | PNP |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| secretion: GO | | | | F2RL1; IL1RN; PNP; S100A12; SCG2; TREM1 | | | FAM3B; GPAM; KLRF2; LEP; NOS2; PCLO; PCSK5; SNCG | | | | | | TREM1 | | | PCLO; SLC18A2 | | | |
| notch signaling pathway: GO | 110 | 5 | 0.76 | CHAC1; IL2RA; PERP; PSENEN; TP63 | 7 | 0.75 | ANGPT4; DTX1; FCER2; MESP1; TIMP4; TMEM100; ZNF423 | 0 | 0.00 | | 1 | 3.80 | IL2RA | 6 | 1.39 | ANGPT4; FOXA1; FOXC1; MDK; MESP1; ZNF423 | 1 | 0.26 | SNAI2 |
| ear morphogenesis: GO | 111 | 6 | 0.90 | ALDH1A3; CHRNA9; GJB6; GRHL3; NR4A3; WNT5A | 18 | 1.91 | ATP2B2; ATP6V1B1; CLIC5; COL11A1; FGF9; FGFR1; FRZB; GLI2; GSC; ITGA8; MYO15A; NOG; OSR1; OSR2; PDZD7; PTPRQ; SIX1; SOBP | 0 | 0.00 | | 0 | 0.00 | | 9 | 2.06 | CLIC5; COL11A1; FGFR1; GLI2; OSR1; PDZD7; PRRX1; SLITRK6; ZIC1 | 1 | 0.26 | WNT5A |
| calcium ion import: GO | 61 | 4 | 1.10 | CCL21; CCL3; CCR5; TRPC4 | 6 | 1.16 | ATP2A1; CACNA1H; JPH2; NOL3; P2RX7; TRDN | 0 | 0.00 | | 0 | 0.00 | | 4 | 1.67 | CACNA1G; CACNA1H; FGF2; TRDN | 0 | 0.00 | |
| sulfur compound biosynthetic process: GO | 196 | 13 | 1.11 | ACOT7; AHCY; AMD1; B3GNT3; CHAC1; CHAC2; CHST1; CNDP2; ELOVL7; GGCT; | 25 | 1.50 | ACACB; ACOT1; ACOT12; ACSBG1; ACSF2; BCAN; BHMT2; CDO1; CHST12; CHST5; | 0 | 0.00 | | 0 | 0.00 | | 6 | 0.78 | ANGPT1; CHST12; DCN; DSEL; GSTM5; UST | 3 | 0.43 | ACOT7; CHST1; GSTP1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | GSTO1; GSTP1; HS3ST3B1 | | | ELOVL2; EXTL1; GGT7; GSTA3; GSTM2; GSTM3; GSTM5; GSTT2B; HS3ST5; HS6ST3; MAT1A; PRELP; SCD5; SLC26A1; UST | | | | | | | | | | | | |
| cytosolic transport: GO | 196 | 4 | 0.34 | HOOK1; STON2; UNC13A; WNT7A | 14 | 0.84 | CADPS; DENND2A; NLGN1; P2RX7; PCLO; RAB9B; RHOBTB3; RIMS1; RPH3AL; SNCA; SYT1; SYT17; SYT8; SYT9 | 0 | 0.00 | | 0 | 0.00 | | 6 | 0.78 | DENND2A; PCLO; RHOBTB3; RIMS1; SNCA; SYT17 | 3 | 0.43 | STON2; UNC13A; WNT7A |
| rab gtpase binding: GO | 112 | 0 | 0.00 | | 6 | 0.63 | MLPH; NPC1L1; RHOBTB3; RIMS1; RPH3AL; SGSM1 | 0 | 0.00 | | 0 | 0.00 | | 4 | 0.91 | MYRIP; RHOBTB3; RIMS1; SGSM1 | 1 | 0.25 | NDRG1 |
| regulation of behavior: GO | 62 | 4 | 1.08 | GJA1; IL6; NR4A3; STRA6 | 9 | 1.71 | ADORA1; ALB; CNR1; DRD1; KCNA2; LEPR; NLGN1; NRXN1; RELN | 0 | 0.00 | | 0 | 0.00 | | 3 | 1.23 | MDK; NRXN1; RELN | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| regulation of notch signaling pathway: GO | 62 | 2 | 0.54 | CHAC1; TP63 | 2 | 0.38 | DTX1; MESP1 | 0 | 0.00 | | 0 | 0.00 | | 1 | 0.41 | MESP1 | 0 | 0.00 | |
| era genomic pathway | 62 | 1 | 0.27 | PCNA | 5 | 0.95 | ABCA3; APBB1; C3; CALCOCO1; PGR | 0 | 0.00 | | 0 | 0.00 | | 4 | 1.64 | ABCA3; C3; ESR1; PGR | 0 | 0.00 | |
| regulation of multicellular organism growth: GO | 62 | 1 | 0.27 | PPIB | 10 | 1.90 | ADRB1; BCL2; CACNA2D2; DIO3; GDF5; GHR; GPAM; NPY1R; PTCH1; SPTBN4 | 2 | 13.48 | GHR; GPAM | 0 | 0.00 | | 6 | 2.46 | BCL2; CACNA2D2; GAMT; NPY1R; PTCH1; SPTBN4 | 0 | 0.00 | |
| regulation of muscle adaptation: GO | 62 | 1 | 0.27 | NR4A3 | 6 | 1.14 | AGT; CAMK2B; NOL3; PDE9A; PPARGC1A; TNNC1 | 0 | 0.00 | | 0 | 0.00 | | 5 | 2.05 | IGFBP5; LMCD1; PDE9A; PPARGC1A; TNNC1 | 0 | 0.00 | |
| cysteine type peptidase activity: GO | 157 | 8 | 0.85 | CTSB; CTSC; PDIA3; PYCARD; USP2; USP43; YOD1; ZC3H12A | 7 | 0.53 | CAPN11; CAPN6; CASP12; CTSF; USP17L2; USP17L7; USP6 | 1 | 2.66 | CAPN6 | 0 | 0.00 | | 3 | 0.49 | CAPN11; CASP12; USP17L7 | 2 | 0.36 | USP43; ZC3H12A |
| cation channel complex: GO | 157 | 3 | 0.32 | CNTNAP2; KCNK1; TRPC4 | 26 | 1.95 | ABCC8; ATP2A1; CACNA1F; CACNA1H; CACNA2D1; CACNA2D2; CACNB1; CASQ2; CATSPERG; DLG2; DPP6; KCNA1; KCNA2; KCNA4; | 0 | 0.00 | | 0 | 0.00 | | 15 | 2.43 | ABCC9; CACNA1G; CACNA1H; CACNA2D1; CACNA2D2; CACNB1; CATSPERG; DLG2; DPP6; KCND2; KCNK2; KCNT2; SCN7A; SCNN1B; | 2 | 0.36 | CNTNAP2; KCNK1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | KCNB1; KCNB2; KCND2; KCNIP1; KCNIP2; KCNJ1; KCNJ3; KCNMB4; KCNT2; KCNU1; SCN7A; TRDN | | | | | | | | | TRDN | | | |
| glycerolipid metabolism | 63 | 5 | 1.33 | ADH7; ALDH1A3; GK; LIPG; MBOAT2 | 8 | 1.50 | ADH1B; ADH1C; ADHFE1; AWAT2; DGKG; GPAM; LPL; PNPLA3 | 2 | 13.27 | GPAM; LPL | 0 | 0.00 | | 3 | 1.21 | ALDH3A2; DGAT2; PNPLA3 | 0 | 0.00 | |
| regulation of apoptosis | 63 | 4 | 1.06 | PSMA4; PSMA5; PSMB6; PSMD1 | 0 | 0.00 | | 0 | 0.00 | | 0 | 0.00 | | 0 | 0.00 | | 0 | 0.00 | |
| regulation of epithelial to mesenchymal transition: GO | 63 | 3 | 0.80 | GREM1; SERPINB3; TGFBR1 | 4 | 0.75 | ALX1; BMP5; PHLDB1; TBX5 | 0 | 0.00 | | 0 | 0.00 | | 1 | 0.40 | FOXA1 | 0 | 0.00 | |
| atpase coupled ion transmembrane transporter activity: GO | 63 | 2 | 0.53 | ATP12A; ATP1B3 | 11 | 2.06 | ABCB11; ABCC3; ABCC8; ATP13A5; ATP1A2; ATP2A1; ATP2B2; ATP6V0A4; ATP6V0E2; CFTR; FXYD2 | 0 | 0.00 | | 0 | 0.00 | | 7 | 2.82 | ABCC9; ATP13A4; ATP13A5; ATP1B2; ATP2C2; ATP6V0A4; ATP6V0E2 | 0 | 0.00 | |
| intron containing pre mrna | 63 | 1 | 0.27 | SNRPG | 0 | 0.00 | | 0 | 0.00 | | 0 | 0.00 | | 0 | 0.00 | | 0 | 0.00 | |
| retrograde transport | 63 | 0 | 0.00 | | 3 | 0.56 | DENND2A; | 0 | 0.00 | | 0 | 0.00 | | 2 | 0.81 | DENND2A; | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| endosome to golgi: GO | | | | | | | RAB9B; RHOBTB3 | | | | | | | | | RHOBTB3 | | | |
| er to golgi vesicle mediated transport: GO | 158 | 6 | 0.64 | AREG; CTSC; DYNLL1; SERPINA1; TGFA; VCP | 9 | 0.67 | ANK2; DYNC1I1; F10; F7; FOLR1; GRIA1; NRBP2; SPTBN4; TRAPPC6A | 0 | 0.00 | | 0 | 0.00 | | 4 | 0.64 | CNIH3; GRIA1; SPTBN4; TRAPPC6A | 2 | 0.36 | AREG; TGFA |
| ion channel transport | 114 | 4 | 0.59 | ATP12A; ATP1B3; GLTP; HTR3A | 16 | 1.66 | ATP1A2; ATP2A1; ATP2B2; ATP6V0E2; BEST4; FXYD2; GABRA2; GABRB3; GABRG3; GLRB; MCOLN3; NALCN; SGK2; TRPM3; TRPV6; TSC22D3 | 0 | 0.00 | | 0 | 0.00 | | 7 | 1.56 | ATP1B2; ATP2C2; ATP6V0E2; GLRB; NALCN; TRPC1; TSC22D3 | 1 | 0.25 | SGK1 |
| hydrogen transport: GO | 114 | 3 | 0.44 | ATP12A; COX7B; SLC2A9 | 9 | 0.93 | ADHFE1; ATP1A2; ATP6V0A4; ATP6V0E2; ATP6V1B1; COX7A1; NOX1; SLC9A2; SLC9A4 | 0 | 0.00 | | 0 | 0.00 | | 5 | 1.11 | ATP6V0A4; ATP6V0E2; COX7A1; SLC2A12; SLC9A2 | 1 | 0.25 | SLC2A9 |
| organic acid catabolic process: GO | 200 | 8 | 0.67 | AHCY; ALDH4A1; GOT2; HAL; IDO1; IL4I1; KYNU; TDO2 | 21 | 1.24 | ABCD2; ACADL; ACOX2; ADIPOQ; ALDHIL1; ASPA; | 2 | 4.18 | ABCD2; ADIPOQ | 1 | 2.09 | TDO2 | 10 | 1.27 | ACOX2; ALDH3A2; ALDH5A1; ASPA; CYP4A11; CYP4F12; | 3 | 0.43 | GLDC; GOT2; PPARD |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | | | | CARNS1; CDO1; CRAT; CYP4A11; CYP4F12; GPT; HAAO; HOGA1; IDUA; LEP; NOS2; PON1; PON3; PRODH; RENBP | | | | | | | | | GPT; HDC; PON3; PRODH | | | |
| monocarboxylic acid biosynthetic process: GO | 159 | 7 | 0.74 | ACOT7; ALDH1A3; CH25H; ELOVL4; ELOVL7; IDO1; PTGS2 | 20 | 1.48 | ABCB11; ACACB; ACOX2; AGMO; BCAN; CHST12; CYP1A1; ELOVL2; FA2H; FADS2; GGT7; HOGA1; LPL; PECR; PLA2G5; PLP1; PRKAA2; PTGIS; SCD5; UST | 1 | 2.63 | LPL | 0 | 0.00 | | 7 | 1.12 | ACOX2; CHST12; DCN; DSEL; PLP1; PRKAA2; UST | 2 | 0.36 | ACOT7; PTGS2 |
| phosphatase binding: GO | 159 | 7 | 0.74 | CTSC; EIF4EBP1; HMGCR; JAK3; JUP; NEK2; VCP | 15 | 1.11 | BCL2; CRY2; DRD1; ELFN2; HSF4; IRS2; KAT2A; MAGI2; MAPT; MYOZ2; PHACTR3; PPP1R32; PPP1R9A; ROS1; SPTBN4 | 0 | 0.00 | | 0 | 0.00 | | 6 | 0.96 | BCL2; CRY2; MAPT; PHACTR3; PPP1R32; SPTBN4 | 2 | 0.36 | EIF4EBP1; NEK2 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| late phase of hiv life cycle | 115 | 4 | 0.58 | PPIA; RAN; RANBP1; RCC1 | 1 | 0.10 | VPS37D | 0 | 0.00 | | 0 | 0.00 | | 0 | 0.00 | | 1 | 0.25 | RAN |
| complement activation: GO | 65 | 6 | 1.54 | C1QBP; IGHG1; IGHG2; IGHG4; IGKC; IGKV4-1 | 9 | 1.63 | C3; C4BPA; C6; C7; CFD; CFH; CLU; COLEC11; FCN2 | 2 | 12.86 | IGHG1; IGKV3-20 | 0 | 0.00 | | 5 | 1.95 | C3; CFH; CLU; IGHM; IGHV3-23 | 0 | 0.00 | |
| bcr signaling pathway | 65 | 1 | 0.26 | CD79A | 1 | 0.18 | BCL2 | 0 | 0.00 | | 0 | 0.00 | | 1 | 0.39 | BCL2 | 0 | 0.00 | |
| photoreceptor outer segment: GO | 65 | 1 | 0.26 | CNGB1 | 5 | 0.91 | CDHR1; GUCA1B; MERTK; PCDH15; RGS9 | 0 | 0.00 | | 0 | 0.00 | | 2 | 0.78 | MAK; MYRIP | 0 | 0.00 | |
| regulation of calcium ion transmembrane transporter activity: GO | 65 | 1 | 0.26 | GSTO1 | 14 | 2.54 | ADRA2A; ANK2; ATP1A2; CACNA2D1; CACNB1; CASQ2; DMD; DRD4; FGF14; GSTM2; JPH2; PLA2G6; SLN; TRDN | 0 | 0.00 | | 0 | 0.00 | | 5 | 1.95 | ADRA2A; CACNA2D1; CACNB1; HRC; TRDN | 0 | 0.00 | |
| regulation of cardiac conduction: GO | 65 | 1 | 0.26 | ATP1B3 | 10 | 1.82 | AGT; ANK2; ATP1A2; ATP2A1; ATP2B2; CASQ2; FXYD2; FXYD6; NKX2-5; TRDN | 0 | 0.00 | | 0 | 0.00 | | 7 | 2.74 | ABCC9; ATP1B2; CORIN; FXYD6; HRC; TRDN; TRPC1 | 0 | 0.00 | |
| single organism membrane fusion: GO | 116 | 4 | 0.58 | BAK1; BCL2A1; DYSF; GNAI3 | 8 | 0.81 | ROPN1B; RPH3AL; SERPINA5; SYT1; SYT17; SYT8; SYT9; | 0 | 0.00 | | 0 | 0.00 | | 2 | 0.44 | ROPN1B; SYT17 | 1 | 0.24 | BAK1 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | TSNARE1 | | | | | | | | | | | | |
| rna polymerase complex: GO | 116 | 1 | 0.14 | POLR3G | 3 | 0.31 | KAT2A; PPARGC1A; TERT | 0 | 0.00 | | 0 | 0.00 | | 1 | 0.22 | PPARGC1A | 1 | 0.24 | POLR3G |
| intracellular receptor signaling pathway: GO | 161 | 6 | 0.62 | CALR; CCNE1; CYP24A1; NR4A3; RAN; UBE2N | 11 | 0.81 | AR; CALCOCO1; CRY2; ESRRG; NR5A1; PPARGC1A; RHOXF1; RORB; RORC; RXRG; SCGB2A1 | 0 | 0.00 | | 0 | 0.00 | | 6 | 0.95 | CRY2; ESR1; ESRRG; NR2F1; PDK3; PPARGC1A | 2 | 0.35 | PPARD; RAN |
| nuclear transcribed mrna catabolic process nonsense mediated decay: GO | 117 | 3 | 0.43 | EIF4A3; RPL26L1; RPS26 | 0 | 0.00 | | 0 | 0.00 | | 0 | 0.00 | | 0 | 0.00 | | 1 | 0.24 | EIF4A3 |
| regulation of phagocytosis: GO | 66 | 4 | 1.01 | CALR; F2RL1; IL1B; PYCARD | 4 | 0.72 | ADIPOQ; C3; C4BPA; MERTK | 1 | 6.33 | ADIPOQ | 1 | 6.33 | IL1B | 2 | 0.77 | C3; TUB | 0 | 0.00 | |
| cell fate specification: GO | 66 | 1 | 0.25 | EOMES | 11 | 1.97 | CDON; GLI2; GSC; MNX1; NANOG; NTRK3; PAX6; PTCH1; PTCH2; SIX1; SOX1 | 0 | 0.00 | | 0 | 0.00 | | 5 | 1.92 | CDON; FOXA1; GLI2; PTCH1; PTCH2 | 0 | 0.00 | |
| small ribosomal subunit: GO | 66 | 1 | 0.25 | RPS26 | 2 | 0.36 | HBA1; HBA2 | 0 | 0.00 | | 0 | 0.00 | | 1 | 0.38 | HBA2 | 0 | 0.00 | |
| pi metabolism | 66 | 0 | 0.00 | | 1 | 0.18 | PLEKHA6 | 0 | 0.00 | | 0 | 0.00 | | 2 | 0.77 | PIK3R6; PLEKHA6 | 0 | 0.00 | |
| phosphatidyl-inositol biosynthetic process: GO | 118 | 3 | 0.43 | CWH43; PIGW; PLAUR | 7 | 0.70 | FGF1; FGF17; FGF22; FGF9; FGFR1; FGFR3; IRS2 | 0 | 0.00 | | 0 | 0.00 | | 4 | 0.86 | FGF2; FGF22; FGFR1; PIK3R6 | 1 | 0.24 | PIGW |
| positive regulation of | 67 | 5 | 1.25 | IFNG; IL12B; IL1B; RSAD2; | 3 | 0.53 | C3; FCER2; P2RX7 | 0 | 0.00 | | 1 | 6.24 | IL1B | 1 | 0.38 | C3 | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| lymphocyte mediated immunity: GO | | | | SASH3 | | | | | | | | | | | | | | | |
| long-term potentiation | 67 | 2 | 0.50 | CALML3; NRAS | 11 | 1.94 | ADCY8; CALML6; CAMK2A; CAMK2B; GRIA1; GRIA2; GRIN1; GRIN2A; PLCB4; PPP1R1A; RPS6KA6 | 1 | 6.24 | PPP1R1A | 0 | 0.00 | | 4 | 1.52 | GRIA1; GRIA2; PLCB4; RPS6KA6 | 0 | 0.00 | |
| macromolecule deacylation: GO | 67 | 1 | 0.25 | LYPLA1 | 2 | 0.35 | HDAC5; PER1 | 0 | 0.00 | | 0 | 0.00 | | 0 | 0.00 | | 0 | 0.00 | |
| abc-family proteins mediated transport | 68 | 3 | 0.74 | ABCA12; PSMA5; PSMB6 | 5 | 0.87 | ABCA2; ABCA3; ABCA8; ABCC3; ABCD2 | 1 | 6.15 | ABCD2 | 0 | 0.00 | | 2 | 0.75 | ABCA3; ABCB5 | 0 | 0.00 | |
| energy reserve metabolic process: GO | 68 | 2 | 0.49 | PGM2; PYGL | 8 | 1.39 | GYG2; LEP; LEPR; PGM5; PHKG1; PPP1R1A; PYGM; STBD1 | 2 | 12.29 | MRAP2; PPPIRIA | 0 | 0.00 | | 2 | 0.75 | PGM5; PHKG1 | 0 | 0.00 | |
| rig i mda5 mediated induction of ifn alpha beta pathways | 68 | 2 | 0.49 | ISG15; S100A12 | 1 | 0.17 | IFNA5 | 0 | 0.00 | | 1 | 6.15 | ISG15 | 0 | 0.00 | | 0 | 0.00 | |
| regulation of cell substrate adhesion: GO | 165 | 10 | 1.01 | C1QBP; CALR; CCL21; FOXF1; GREM1; ITGA3; PLAU; RAC2; RHOD; SERPINE1 | 12 | 0.86 | ABI3BP; APOD; ARHGAP6; BCL2; CCDC80; EDIL3; FZD4; MYOC; NDNF; SEMA3E; | 0 | 0.00 | | 3 | 7.60 | GBP1; RAC2; SERPINE1 | 13 | 2.00 | ABI3BP; BCL2; CCDC80; DLC1; EDIL3; FBLN1; FBLN2; FZD7; MYOC; NDNF; | 2 | 0.34 | ITGA3; RHOD |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | SPOCK1; VIT | | | | | | | | | SEMA3E; SPOCK1; VWC2 | | | |
| peptide transport: GO | 69 | 4 | 0.97 | ANXA1; IL1RN; IL6; TAP2 | 6 | 1.03 | CARTPT; EDN3; FAM3B; LEP; PCLO; SLC15A5 | 0 | 0.00 | | 0 | 0.00 | | 3 | 1.10 | EDN3; PCLO; SLC18A2 | 0 | 0.00 | |
| thiol dependent ubiquitin specific protease activity: GO | 69 | 2 | 0.49 | USP2; YOD1 | 2. | 0.34 | USP17L2; USP6 | 0 | 0.00 | | 0 | 0.00 | | 0 | 0.00 | | 0 | 0.00 | |
| protein localization to endoplasmic reticulum: GO | 122 | 6 | 0.82 | HSPA5; PDIA3; RAB10; RPL26L1; RPS26; SEC61G | 2 | 0.19 | ANK2; GRIK5 | 0 | 0.00 | | 0 | 0.00 | | 0 | 0.00 | | 1 | 0.23 | HSPA5 |
| kidney epithelium development: GO | 122 | 4 | 0.55 | GDNF; GREM1; PGF; SDC1 | 21 | 2.03 | ADAMTS16; BCL2; CD34; FGF1; FGFR1; GPC3; IRX1; KLF15; MAGI2; NOG; OSR1; PKD1; POU3F3; PTCH1; SIM1; SIX1; SLIT2; SOX8; TCF21; TFAP2B; WNT11 | 0 | 0.00 | | 0 | 0.00 | | 12 | 2.50 | BCL2; CD34; FGF2; FGFR1; FOXC1; OSR1; POU3F3; PTCH1; SIM1; SLIT2; SPRY1; WNT11 | 1 | 0.23 | WNT9B |
| snare binding: GO | 122 | 2 | 0.27 | EXOC3L2; UNC13A | 8 | 0.77 | ABCC8; RPH3AL; SYBU; SYT1; SYT17; SYT8; SYT9; TSNARE1 | 0 | 0.00 | | 0 | 0.00 | | 2 | 0.42 | SYBU; SYT17 | 1 | 0.23 | UNC13A |
| atpase binding: GO | 71 | 4 | 0.94 | ATP1B3; RALB; SDF2L1; | 9 | 1.50 | ALDOB; ANK2; AR; ATP6V0A4; | 0 | 0.00 | | 0 | 0.00 | | 7 | 2.51 | ATP1B2; ATP6V0A4; BRSK2; | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | SLC26A9 | | | BRSK2; DRD1; PGR; SLN; SVIP | | | | | | | | | ESR1; HRC; PGR; SVIP | | | |
| t cell differentiation: GO | 123 | 8 | 1.09 | ANXA1; CD3E; EOMES; IFNG; IL12B; IL6; IL7R; RSAD2 | 5 | 0.48 | BCL2; FZD8; LEP; LEPR; RORC | 0 | 0.00 | | 1 | 3.40 | IL7R | 2 | 0.41 | BCL2; FZD7 | 1 | 0.23 | BCL3 |
| sarcolemma: GO | 124 | 4 | 0.54 | ANXA1; CTSB; DYSF; PRKCQ | 22 | 2.09 | ABCC8; ADCY6; ADRA1A; ANK2; ATP1A2; CACNA2D1; CACNB1; CHRM4; DES; DMD; DTNA; KCNB1; KCNJ3; LAMA2; PDE9A; PGM5; SGCA; SGCG; SGCZ; SLC27A6; SLC2A4; SSPN | 2 | 6.74 | SGCG; SLC27A6 | 0 | 0.00 | | 11 | 2.25 | ABCC9; ADRA1A; CACNA2D1; CACNB1; ESR1; LAMA2; PDE9A; PGM5; SGCZ; SNTB1; SSPN | 1 | 0.23 | PRKCQ |
| transcription coupled nucleotide excision repair: GO | 72 | 1 | 0.23 | PCNA | 0 | 0.00 | | 0 | 0.00 | | 0 | 0.00 | | 0 | 0.00 | | 0 | 0.00 | |
| fcer1 pathway | 72 | 0 | 0.00 | | 0 | 0.00 | | 0 | 0.00 | | 1 | 5.80 | LCP2 | 1 | 0.35 | MS4A2 | 0 | 0.00 | |
| proteasome complex: GO | 74 | 6 | 1.36 | PSMA4; PSMA5; PSMB6; PSMD1; PSME3; VCP | 0 | 0.00 | | 0 | 0.00 | | 0 | 0.00 | | 0 | 0.00 | | 0 | 0.00 | |
| clec7a (dectin-1) signaling | 74 | 5 | 1.13 | IL1B; PSMA5; PSMB6; PYCARD; | 0 | 0.00 | | 0 | 0.00 | | 1 | 5.65 | IL1B | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | UBE2N | | | | | | | | | | | | | | | |
| hormone transport: GO | 74 | 3 | 0.68 | ANXA1; IL1RN; IL6 | 7 | 1.12 | CARTPT; EDN3; FAM3B; FZD4; LEP; PCLO; SLC22A9 | 0 | 0.00 | | 0 | 0.00 | | 4 | 1.37 | EDN3; PCLO; SLC16A10; SLC18A2 | 0 | 0.00 | |
| artery development: GO | 75 | 5 | 1.12 | FOXF1; LTBP1; PRDM1; STRA6; TGFBR1 | 7 | 1.10 | APOE; FOLR1; HAND2; MYOCD; SIX1; TFAP2B; WNT11 | 0 | 0.00 | | 0 | 0.00 | | 5 | 1.69 | FOXC1; HAND2; PRICKLE1; PRRX1; WNT11 | 0 | 0.00 | |
| ciliary membrane: GO | 76 | 1 | 0.22 | CNGB1 | 8 | 1.24 | CDHR1; CYS1; DRD1; GUCA1B; HHIP; PKD1; PTCH1; RGS9 | 0 | 0.00 | | 0 | 0.00 | | 2 | 0.67 | CYS1; PTCH1 | 0 | 0.00 | |
| opioid signalling | 78 | 2 | 0.43 | GNAI3; GNGT2 | 8 | 1.21 | ADCY2; ADCY5; ADCY6; ADCY8; GNAZ; PLCB4; PPP1R1B; PRKAR2B | 1 | 5.36 | PRKAR2B | 0 | 0.00 | | 3 | 0.98 | GNG11; PDE1A; PLCB4 | 0 | 0.00 | |
| golgi associated vesicle: GO | 79 | 2 | 0.42 | CNGB1; GJA1 | 4 | 0.60 | CFTR; NCALD; PKD1; SLC2A4 | 0 | 0.00 | | 0 | 0.00 | | 2 | 0.64 | NCALD; STEAP2 | 0 | 0.00 | |
| neurotransmitter receptor binding and downstream transmission in the postsynaptic cell | 134 | 7 | 0.87 | CHRNA3; CHRNA6; CHRNA9; GNAI3; GNGT2; KCNJ15; NEFL | 22 | 1.94 | ACTN2; ADCY2; ADCY5; ADCY6; ADCY8; CAMK2A; CAMK2B; CHRNA2; GABRA2; GABRB3; | 1 | 3.12 | GRIA4 | 0 | 0.00 | | 6 | 1.14 | GNG11; GRIA1; GRIA2; GRIK3; NCALD; RPS6KA6 | 1 | 0.21 | CHRNA6 |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline: Up-regulated | Fold Change (FC) Up | Up-regulated Genes | Down-regulated | Fold Change (FC) | Down-regulated Genes | B. Differentially expressed genes significant in the baseline vs week 12 comparison only in the placebo: Up-regulated | Fold Change (FC) Up | Up-regulated Genes | Down-regulated | Fold Change (FC) | Down-regulated Genes | C. Differentially expressed genes significant in the baseline vs week 12 comparison only in the nemo: Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | | | | GABRG3; GRIA1; GRIA2; GRIA4; GRIK3; GRIK4; GRIK5; GRIN1; GRIN2A; KCNJ3; NCALD; RPS6KA6 | | | | | | | | | | | | |
| cysteine type endopeptidase activity: GO | 81 | 5 | 1.03 | CTSB; CTSC; PDIA3; PYCARD; USP2 | 5 | 0.73 | CAPN11; CAPN6; CASP12; CTSF; USP6 | 1 | 5.16 | CAPN6 | 0 | 0.00 | | 2 | 0.63 | CAPN11; CASP12 | 0 | 0.00 | |
| regulation of potassium ion transport: GO | 81 | 3 | 0.62 | ADCYAP1; ATP1B3; PRNP | 14 | 2.04 | ABCC8; ACTN2; ADORA1; ADRA2A; ANK2; CASQ2; DPP10; DPP6; DRD1; EDN3; FHL1 KCNIP1; KCNIP2; PLCB4 | 0 | 0.00 | | 0 | 0.00 | | 5 | 1.57 | ADRA2A; ATP1B2; DPP6; EDN3; PLCB4 | 0 | 0.00 | |
| odorant binding: GO | 82 | 0 | 0.00 | | 5 | 0.72 | OBP2A; OR10Q1; OR14A16; OR9I1; OR9Q2 | 0 | 0.00 | | 0 | 0.00 | | 0 | 0.00 | | 0 | 0.00 | |
| heart process: GO | 83 | 3 | 0.60 | CXCR4; GJA1; MYLK2 | 15 | 2.13 | ANK2; ATP1A2; CACNA2D1; CASQ2; DMD; MYL3; MYL4; NKX2-5; SGCG; SGCZ; | 1 | 5.03 | SGCG | 0 | 0.00 | | 4 | 1.22 | CACNA2D1; SGCZ; TNNC1; TRDN | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Func-tional | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes | Up-regu-lated | Fold Change (FC) Up | Up-regulated Genes | Down-regu-lated | Fold Change (FC) | Down-regulated Genes |
| | | | | | | | TNNC1; TNNI2; TNNT2; TPM1; TRDN | | | | | | | | | | | | |
| hydrogen ion transmembrane transport: GO | 83 | 2 | 0.40 | ATP12A; COX7B | 7 | 1.00 | ATP1A2; ATP6V0A4; ATP6V0E2; ATP6V1B1; COX7A1; SLC9A2; SLC9A4 | 0 | 0.00 | | 0 | 0.00 | | 4 | 1.22 | ATP6V0A4; ATP6V0E2; COX7A1; SLC9A2 | 0 | 0.00 | |
| calcium mediated signaling: GO | 84 | 5 | 1.00 | CCL3; CCR5; CXCR4; GSTO1; SELE | 11 | 1.54 | AGTR1; ANK2; ATP1A2; CASQ2; DMD; DRD1; GSTM2; NCALD; NMUR1; PPP1R9A; RCAN2 | 0 | 0.00 | | 1 | 4.97 | SELE | 6 | 1.81 | AGTR1; BHLHA15; HRC; NCALD; PTGFR; RCAN2 | 0 | 0.00 | |
| hydrolase activity acting on carbon nitrogen but not peptide bonds in linear amides: GO | 84 | 2 | 0.40 | PGLYRP2; VNN3 | 2 | 0.28 | ASPA; HDAC5 | 0 | 0.00 | | 0 | 0.00 | | 2 | 0.60 | ACER1; ASPA | 0 | 0.00 | |
| t cell receptor signaling pathway: GO | 139 | 10 | 1.20 | CD3E; IFNG; PRKCQ; PSMA4; PSMA5; PSMB6; PSMD1; PSME3; TNFRSF21; UBE2N | 1 | 0.08 | PAK3 | 0 | 0.00 | | 1 | 3.01 | LCP2 | 2 | 0.37 | HLA-DQB2; PAK3 | 1 | 0.20 | PRKCQ |
| sphingolipid metabolism | 85 | 7 | 1.38 | ARSH; CERS3; GLTP; NEU2; | 2 | 0.28 | FA2H; GAL3ST1 | 0 | 0.00 | | 0 | 0.00 | | 3 | 0.90 | ACER1; ALDH3A2; PLPP3 | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | SGPP2; SPTSSA; UGCG | | | | | | | | | | | | | | | |
| platelet homeostasis | 85 | 2 | 0.39 | GNGT2; LRP8 | 9 | 1.25 | ATP2A1; ATP2B2; KCNMB4; NOS2; P2RX1; P2RX7; PDE11A; PDE9A; PRKG2 | 0 | 0.00 | | 0 | 0.00 | | 5 | 1.49 | GNG11; PDE1A; PDE9A; PRKG1; PRKG2 | 0 | 0.00 | |
| rna polymerase ii transcription cofactor activity: GO | 85 | 1 | 0.20 | TBX20 | 8 | 1.11 | ELANE; MYOCD; NKX2-5; PPARGC1A; TBX15; TBX18; TFAP2B; ZFPM2 | 0 | 0.00 | | 0 | 0.00 | | 6 | 1.79 | ELANE; PPARGC1A; PRRX1; TBX15; TBX18; ZFPM2 | 0 | 0.00 | |
| acrosomal vesicle: GO | 86 | 6 | 1.17 | ACRV1; CALR; CXADR; ENKUR; RACGAP1; TXNDC8 | 10 | 1.37 | CAPN11; CAPZA3; SERPINA5; SPAG8; SPINK1; STK31; SV2B; SYT8; TEKT3; TSKS | 0 | 0.00 | | 0 | 0.00 | | 4 | 1.18 | CAPN11; CAPZA3; STK31; SV2B | 0 | 0.00 | |
| membrane fusion: GO | 141 | 7 | 0.83 | BAK1; BCL2A1; CCR5; CXCR4; DYSF; GNAI3; PPIA | 9 | 0.75 | RIMS1; ROPN1B; RPH3AL; SERPINA5; SYT1; SYT17; SYT8; SYT9; TSNARE1 | 0 | 0.00 | | 0 | 0.00 | | 3 | 0.54 | RIMS1; ROPN1B; SYT17 | 1 | 0.20 | BAK1 |
| c-type lectin receptors (clrs) | 90 | 7 | 1.30 | ICAM3; IL1B; NRAS; PSMA5; PSMB6; PYCARD; UBE2N | 3 | 0.39 | MUC20; MUC6; MUCL1 | 0 | 0.00 | | 1 | 4.64 | IL1B | 2 | 0.56 | MUC20; MUCL1 | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | | | | | | B. Differentially expressed genes significant in the baseline vs week 12 comparison only in the placebo Up-regulated | | | | | | C. Differentially expressed genes significant in the baseline vs week 12 comparison only in the nemo Up-regulated | | | | | |
|---|---|---|---|---|---|---|---|---|---|---|---|---|---|---|---|---|---|---|---|
| | | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| organelle membrane fusion: GO | 90 | 2 | 0.37 | DYSF; GNAI3 | 6 | 0.79 | RPH3AL; SYT1; SYT17; SYT8; SYT9; TSNARE1 | 0 | 0.00 | | 0 | 0.00 | | 1 | 0.28 | SYT17 | 0 | 0.00 | |
| mrna splicing | 146 | 3 | 0.34 | HSPA8; SNRPF; SNRPG | 1 | 0.08 | PPIL6 | 0 | 0.00 | | 0 | 0.00 | | 1 | 0.17 | PPIL6 | 1 | 0.19 | HSPA8 |
| translational termination: GO | 91 | 4 | 0.74 | GADD45GIP1; MRPL13; MRPL36; MRPL51 | 0 | 0.00 | | 0 | 0.00 | | 0 | 0.00 | | 0 | 0.00 | | 0 | 0.00 | |
| late endosome membrane: GO | 92 | 2 | 0.36 | IFITM3; NTRK1 | 1 | 0.13 | VPS37D | 0 | 0.00 | | 1 | 4.54 | IFITM3 | 1 | 0.28 | CLCN4 | 0 | 0.00 | |
| action potential: GO | 92 | 1 | 0.18 | GJA1 | 16 | 2.05 | ANK2; ATP1A2; CACNA1F; CACNA1H; CACNA2D1; DMD; DRD1; KCNA1; KCNA2; KCNB1; KCND2; KCNMB4; MYH14; NALCN; P2RX1; SCN7A | 0 | 0.00 | | 0 | 0.00 | | 6 | 1.66 | CACNA1G; CACNA1H; CACNA2D1; KCND2; NALCN; SCN7A | 0 | 0.00 | |
| microbody part: GO | 92 | 1 | 0.18 | HMGCR | 6 | 0.77 | ABCD2; ACOX2; CRAT; HAO2; PECR; PEX11A | 1 | 4.54 | ABCD2 | 0 | 0.00 | | 2 | 0.55 | ACOX2; ALDH3A2 | 0 | 0.00 | |
| dna directed rna polymerase ii holoenzyme: GO | 92 | 0 | 0.00 | | 2 | 0.26 | KAT2A; PPARGC1A | 0 | 0.00 | | 0 | 0.00 | | 1 | 0.28 | PPARGC1A | 0 | 0.00 | |
| srp dependent cotranslational protein targeting to membrane | 93 | 3 | 0.54 | RPL26L1; RPS26; SRP9P1 | 1 | 0.13 | FAM153A | 0 | 0.00 | | 0 | 0.00 | | 0 | 0.00 | | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Func-tional | A. Non-lesional vs lesional skin at baseline: Up-regu-lated | Fold Change (FC) Up | Up-regulated Genes | Down-regu-lated | Fold Change (FC) | Down-regulated Genes | B. Differentially expressed genes significant in the baseline vs week 12 comparison only in the placebo: Up-regu-lated | Fold Change (FC) Up | Up-regulated Genes | Down-regu-lated | Fold Change (FC) | Down-regulated Genes | C. Differentially expressed genes significant in the baseline vs week 12 comparison only in the nemo: Up-regu-lated | Fold Change (FC) Up | Up-regulated Genes | Down-regu-lated | Fold Change (FC) | Down-regulated Genes |
|---|---|---|---|---|---|---|---|---|---|---|---|---|---|---|---|---|---|---|---|
| rna pol ii transcription | 93 | 2 | 0.36 | SNRPF; SNRPG | 0 | 0.00 | | 0 | 0.00 | | 0 | 0.00 | | 0 | 0.00 | | 0 | 0.00 | |
| transforming growth factor beta receptor signaling pathway: GO | 94 | 1 | 0.18 | TGFBR1 | 5 | 0.63 | AMHR2; CGN; GDF10; GDF5; MSTN | 0 | 0.00 | | 0 | 0.00 | | 1 | 0.27 | CGN | 0 | 0.00 | |
| second messenger mediated signaling: GO | 151 | 7 | 0.78 | ADCYAP1; CCL3; CCR5; CXCR4; FPR1; GSTO1; SELE | 22 | 1.72 | ADCY2; ADCY5; ADCY6; ADCY8; AGT; AGTR1; ANK2; APOE; ATP1A2; CASQ2; DMD; DRD1; EDN3; GSTM2; NCALD; NDNF; NMUR1; NOS2; PCLO; PDE9A; PPP1R9A; RCAN2 | 0 | 0.00 | | 1 | 2.77 | SELE | 12 | 2.02 | ADCYAP1R1; AGTR1; BHLHA15; EDN3; HRC; NCALD; NDNF; PCLO; PDE9A; PRKG1; PTGFR; RCAN2 | 1 | 0.19 | HRH1 |
| ribosomal subunit: GO | 157 | 6 | 0.64 | MRPL13; MRPL36; MRPL51; RPL22L1; RPL26L1; RPS26 | 2 | 0.15 | HBA1; HBA2 | 0 | 0.00 | | 0 | 0.00 | | 1 | 0.16 | HBA2 | 1 | 0.18 | MPV17L2 |
| spinal cord development: GO | 101 | 2 | 0.33 | NEFL; TBX20 | 13 | 1.52 | DRGX; FOXN4; GLI2; MDGA2; MNX1; NOG; NOVA1; PAX6; PKD1; PTCH1; RELN; SLIT2; | 0 | 0.00 | | 0 | 0.00 | | 7 | 1.76 | CHRD; GDF7; GLI2; PTCH1; RELN; SLIT2; ZIC1 | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| | | | | | | | SOX1 | | | | | | | | | | | | |
| establishment of protein localization to endoplasmic reticulum: GO | 103 | 4 | 0.65 | RAB10; RPL26L1; RPS26; SEC61G | 0 | 0.00 | | 0 | 0.00 | | 0 | 0.00 | | 0 | 0.00 | | 0 | 0.00 | |
| mitochondrial translation: GO | 104 | 4 | 0.64 | GADD45GIP1; MRPL13; MRPL36; MRPL51 | 0 | 0.00 | | 0 | 0.00 | | 0 | 0.00 | | 0 | 0.00 | | 0 | 0.00 | |
| trna processing: GO | 104 | 1 | 0.16 | RPP40 | 0 | 0.00 | | 0 | 0.00 | | 0 | 0.00 | | 0 | 0.00 | | 0 | 0.00 | |
| trna metabolic process: GO | 164 | 5 | 0.51 | EPRS; GARS; GTF3C6; RPP40; TARS | 0 | 0.00 | | 0 | 0.00 | | 0 | 0.00 | | 0 | 0.00 | | 1 | 0.17 | TARS |
| cilium organization: GO | 164 | 3 | 0.31 | CNGB1; DYNLL1; PLA2G3 | 9 | 0.65 | CCDC114; CCDC40; DMD; DNAAF1; DZIP1L; HYDIN; PKHD1; RSPH1; SPEF2 | 0 | 0.00 | | 0 | 0.00 | | 4 | 0.62 | B9D1; CCDC114; SPATA6; SPEF2 | 1 | 0.17 | PLA2G3 |
| translational elongation: GO | 108 | 7 | 1.08 | EEF1B2; EIF5A; EIF5AL1; GADD45GIP1; MRPL13; MRPL36; MRPL51 | 1 | 0.11 | EEF2K | 0 | 0.00 | | 0 | 0.00 | | 0 | 0.00 | | 0 | 0.00 | |
| influenza life cycle | 168 | 5 | 0.50 | CALR; RAN; RPL22L1; RPL26L1; RPS26 | 1 | 0.07 | FAM153A | 0 | 0.00 | | 0 | 0.00 | | 0 | 0.00 | | 1 | 0.17 | RAN |
| cytosolic ribosome: GO | 110 | 3 | 0.46 | RPL22L1; RPL26L1; RPS26 | 4 | 0.43 | APOD; HBA1; HBA2; PPARGC1A | 0 | 0.00 | | 0 | 0.00 | | 2 | 0.46 | HBA2; PPARGC1A | 0 | 0.00 | |
| atpase activity coupled to movement of | 113 | 5 | 0.74 | ABCA12; ABCG4; ATP12A; | 18 | 1.88 | ABCA10; ABCA2; ABCA3; | 1 | 3.70 | ABCD2 | 0 | 0.00 | | 9 | 2.02 | ABCA3; ABCB5; ABCC9; | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| substances: GO | | | | ATP1B3; TAP2 | | | ABCA6; ABCA8; ABCA9; ABCB11; ABCC3; ABCC8; ABCD2; ATP13A5; ATP1A2; ATP2A1; ATP2B2; ATP6V0A4; ATP6V0E2; CFTR; FXYD2 | | | | | | | | | ATP13A4; ATP13A5; ATP1B2; ATP2C2; ATP6V0A4; ATP6V0E2 | | | |
| s adenosyl-methionine dependent methyltransferase activity: GO | 113 | 0 | 0.00 | | 3 | 0.31 | BHMT2; INMT; METTL7B | 0 | 0.00 | | 0 | 0.00 | | 1 | 0.22 | GAMT | 0 | 0.00 | |
| peptide chain elongation | 114 | 3 | 0.44 | RPL22L1; RPL26L1; RPS26 | 1 | 0.10 | FAM153A | 0 | 0.00 | | 0 | 0.00 | | 0 | 0.00 | | 0 | 0.00 | |
| cilium morphogenesis: GO | 181 | 3 | 0.28 | ACTR3; DYNLL1; PLA2G3 | 11 | 0.72 | CCDC114; CCDC40; DMD; DNAAF1; DZIP1L; GSN; HYDIN; PKHD1; RSPH1; SPEF2; TEKT3 | 0 | 0.00 | | 0 | 0.00 | | 4 | 0.56 | B9D1; CCDC114; SPATA6; SPEF2 | 1 | 0.16 | PLA2G3 |
| antigen receptor mediated signaling pathway: GO | 182 | 16 | 1.47 | CD3E; CD79A; CTLA4; IFNG; IGHG1; IGHG2; IGHG4; IGKC; PRKCQ; | 2 | 0.13 | BCL2; PAK3 | 1 | 2.30 | IGHG1 | 1 | 2.30 | LCP2 | 6 | 0.84 | BCL2; HLA-DQB2; IGHM; IGHV3-23; PAK3; RFTN2 | 1 | 0.16 | PRKCQ |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. of Functional | A. Non-lesional vs lesional skin at baseline Up-regulated | Fold Change (FC) Up | Up-regulated Genes | Down-regulated | Fold Change (FC) | Down-regulated Genes | B. Differentially expressed genes significant in the baseline vs week 12 comparison only in the placebo Up-regulated | Fold Change (FC) Up | Up-regulated Genes | Down-regulated | Fold Change (FC) | Down-regulated Genes | C. Differentially expressed genes significant in the baseline vs week 12 comparison only in the nemo Up-regulated | Fold Change (FC) Up | Up-regulated Genes | Down-regulated | Fold Change (FC) | Down-regulated Genes |
|---|---|---|---|---|---|---|---|---|---|---|---|---|---|---|---|---|---|---|---|
| | | | | PSMA4; PSMA5; PSMB6; PSMD1; PSME3; TNFRSF21; UBE2N | | | | | | | | | | | | | | | |
| nonmotile primary cilium: GO | 129 | 1 | 0.13 | CNGB1 | 7 | 0.64 | CDHR1; DRD1; GUCA1B; MERTK; PCDH15; PCDHB15; RGS9 | 0 | 0.00 | | 0 | 0.00 | | 3 | 0.59 | B9D1; MAK; MYRIP | 0 | 0.00 | |
| 3 utr mediated translational regulation | 130 | 3 | 0.39 | EIF2S1; RPL26L1; RPS26 | 1 | 0.09 | FAM153A | 0 | 0.00 | | 0 | 0.00 | | 0 | 0.00 | | 0 | 0.00 | |
| multi organism metabolic process: GO | 136 | 2 | 0.25 | RPL26L1; RPS26 | 0 | 0.00 | | 0 | 0.00 | | 0 | 0.00 | | 0 | 0.00 | | 0 | 0.00 | |
| influenza viral rna transcription and replication | 145 | 3 | 0.35 | RPL22L1; RPL26L1; RPS26 | 1 | 0.08 | FAM153A | 0 | 0.00 | | 0 | 0.00 | | 0 | 0.00 | | 0 | 0.00 | |
| vacuole organization: GO | 154 | 1 | 0.11 | HOOK1 | 6 | 0.46 | CLVS1; CLVS2; DNM1; MAPILC3C; P2RX7; VPS37D | 0 | 0.00 | | 0 | 0.00 | | 0 | 0.00 | | 0 | 0.00 | |
| protein targeting to membrane: GO | 155 | 2 | 0.22 | RPL26L1; RPS26 | 7 | 0.53 | ADORA1; ANK2; KCNB1; KCNB2; PALM; PRKG2; PTCH1 | 0 | 0.00 | | 0 | 0.00 | | 5 | 0.82 | PALM; PRKG2; PTCH1; TESC; TRAM1L1 | 0 | 0.00 | |
| transferase activity transferring one carbon | 180 | 1 | 0.09 | PRDM1 | 6 | 0.39 | ALDH1L1; BHMT2; INMT; METTL7B; | 1 | 2.32 | NSUN7 | 0 | 0.00 | | 2 | 0.28 | GAMT; GATM | 0 | 0.00 | |

TABLE 2-continued

Functional enrichment analysis for the up (or down)-regulated identified in the three differential analysis: (A) non-lesional vs lesional skin at baseline; (B) differentially expressed genes significant in the baseline vs week 12 comparison only in the placebo but not the nemo group; (C) differentially expressed genes significant in the baseline vs week 12 comparison only in the nemo but not the placebo group.

| | No. | A. Non-lesional vs lesional skin at baseline | | | | | | B. Differentially expressed genes significant in the baseline vs week 12 comparison only in the placebo | | | | | | C. Differentially expressed genes significant in the baseline vs week 12 comparison only in the nemo | | | | | |
|---|---|---|---|---|---|---|---|---|---|---|---|---|---|---|---|---|---|---|---|
| | of Functional | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes | Up-regulated | Fold Change (FC) Up | Up-regulated Genes | Down-regulated | Fold Change (FC) | Down-regulated Genes |
| groups: GO | | | | | | | NSUN7; PRDM8 | | | | | | | | | | | | |
| primary cilium: GO | 193 | 4 | 0.35 | CNGB1; CSNK1A1; DYNLL1; RAB10 | 14 | 0.86 | ADCY5; CDHR1; CYS1; DNAH11; DRD1; GLI2; GUCA1B; MERTK; PCDH15; PCDHB15; PKD1; PKHD1; PTCH1; RGS9 | 0 | 0.00 | | 0 | 0.00 | | 6 | 0.79 | B9D1; CYS1; GLI2; MAK; MYRIP; PTCH1 | 0 | 0.00 | |

TABLE 3

| Gene expression modules in non-lesional and lesional PN skin. | | | | | | |
|---|---|---|---|---|---|---|
| Mod-ules | Funs | p | FDR | NumFunGenes | NumInfFunGenes | FC |
| 0 | AXONEMAL_DYNEIN_COMPLEX | 5.27E−06 | 9.53E−02 | 14 | 12 | 3.10 |
| 1 | CYTOPLASM | 1.34E−73 | 2.42E−69 | 7621 | 1782 | 1.36 |
| 1 | CYTOPLASMIC_PART | 1.23E−64 | 1.11E−60 | 5674 | 1393 | 1.42 |
| 1 | INTRACELLULAR_PART | 1.01E−63 | 6.06E−60 | 9973 | 2155 | 1.25 |
| 1 | INTRACELLULAR | 5.92E−63 | 2.68E−59 | 10121 | 2177 | 1.25 |
| 1 | CELLULAR_COMPONENT | 9.00E−57 | 3.26E−53 | 12285 | 2505 | 1.18 |
| 1 | INTRACELLULAR_ORGANELLE | 1.09E−48 | 2.98E−45 | 8727 | 1886 | 1.25 |
| 1 | CELL | 1.32E−48 | 2.98E−45 | 11128 | 2290 | 1.19 |
| 1 | CELL_PART | 1.32E−48 | 2.98E−45 | 11128 | 2290 | 1.19 |
| 1 | ORGANELLE | 3.68E−48 | 7.40E−45 | 8751 | 1888 | 1.25 |
| 1 | INTRACELLULAR_MEMBRANE_BOUNDED_ORGANELLE | 4.18E−46 | 7.57E−43 | 8011 | 1750 | 1.27 |
| 2 | EXTRACELLULAR_REGION | 8.88E−92 | 1.61E−87 | 1185 | 452 | 2.54 |
| 2 | EXTRACELLULAR_REGION_PART | 1.10E−71 | 9.93E−68 | 704 | 298 | 2.82 |
| 2 | EXTRACELLULAR_MATRIX | 1.92E−63 | 1.16E−59 | 335 | 181 | 3.60 |
| 2 | SINGLE_MULTICELLULAR_ORGANISM_PROCESS | 3.32E−55 | 1.50E−51 | 3749 | 883 | 1.57 |
| 2 | MULTICELLULAR_ORGANISMAL_PROCESS | 5.43E−52 | 1.96E−48 | 3869 | 894 | 1.54 |
| 2 | PROTEINACEOUS_EXTRACELLULAR_MATRIX | 9.42E−51 | 2.84E−47 | 285 | 150 | 3.51 |
| 2 | CELL_PERIPHERY | 2.70E−50 | 6.99E−47 | 2912 | 716 | 1.64 |
| 2 | PLASMA_MEMBRANE | 8.12E−49 | 1.84E−45 | 2839 | 698 | 1.64 |
| 2 | EXTRACELLULAR_SPACE | 8.11E−48 | 1.63E−44 | 481 | 202 | 2.80 |
| 2 | SYSTEM_DEVELOPMENT | 8.31E−46 | 1.50E−42 | 2502 | 626 | 1.67 |
| 3 | INTRACELLULAR_PART | 2.40E−76 | 4.34E−72 | 9973 | 1888 | 1.31 |
| 3 | INTRACELLULAR_ORGANELLE_PART | 2.11E−74 | 1.91E−70 | 5734 | 1249 | 1.50 |
| 3 | ORGANELLE_PART | 2.57E−73 | 1.55E−69 | 5810 | 1258 | 1.49 |
| 3 | INTRACELLULAR | 3.79E−73 | 1.71E−69 | 10121 | 1899 | 1.30 |
| 3 | INTRACELLULAR_ORGANELLE | 4.23E−67 | 1.53E−63 | 8727 | 1683 | 1.33 |
| 3 | ORGANELLE | 2.50E−66 | 7.53E−63 | 8751 | 1684 | 1.33 |
| 3 | CELL | 2.39E−63 | 5.40E−60 | 11128 | 2006 | 1.24 |
| 3 | CELL_PART | 2.39E−63 | 5.40E−60 | 11128 | 2006 | 1.24 |
| 3 | INTRACELLULAR_MEMBRANE_BOUNDED_ORGANELLE | 6.38E−62 | 1.28E−58 | 8011 | 1561 | 1.34 |
| 3 | MEMBRANE_BOUNDED_ORGANELLE | 2.79E−61 | 5.05E−58 | 8039 | 1563 | 1.34 |
| 4 | GENERIC_TRANSCRIPTION_PATHWAY | 4.80E−06 | 8.67E−02 | 380 | 62 | 1.77 |
| 5 | EPIDERMIS_DEVELOPMENT | 1.93E−14 | 3.50E−10 | 208 | 45 | 3.61 |
| 5 | KERATINOCYTE_DIFFERENTIATION | 7.85E−12 | 7.10E−08 | 72 | 23 | 5.34 |
| 5 | EPIDERMAL_CELL_DIFFERENTIATION | 3.09E−11 | 1.86E−07 | 83 | 24 | 4.83 |
| 5 | KERATINIZATION | 3.82E−10 | 1.73E−06 | 31 | 14 | 7.54 |
| $ | EPITHELIAL_CELL_DIFFERENTIATION | 4.53E−09 | 1.64E−05 | 198 | 35 | 2.95 |
| 5 | TISSUE_DEVELOPMENT | 2.31E−08 | 6.95E−05 | 907 | 96 | 1.77 |
| 5 | LIPID_METABOLIC_PROCESS | 1.49E−07 | 3.85E−04 | 841 | 88 | 1.75 |
| 5 | EPITHELIUM_DEVELOPMENT | 1.12E−06 | 2.27E−03 | 447 | 53 | 1.98 |
| 5 | MEMBRANE_LIPID_METABOLIC_PROCESS | 1.21E−06 | 2.27E−03 | 137 | 24 | 2.93 |
| 5 | REGULATION_OF_TRANSCRIPTION_DNA_DEPENDENT | 1.25E−06 | 2.27E−03 | 2399 | 197 | 1.37 |
| 6 | CELL_CYCLE | 1.60E−98 | 2.89E−94 | 1094 | 218 | 5.13 |
| 6 | CELL_CYCLE_PROCESS | 3.00E−91 | 2.71E−87 | 849 | 187 | 5.67 |
| 6 | NUCLEAR_PART | 9.69E−73 | 5.84E−69 | 2752 | 303 | 2.83 |
| 6 | MITOTIC_CELL_CYCLE | 1.43E−71 | 6.48E−68 | 483 | 128 | 6.82 |
| 6 | DNA_METABOLIC_PROCESS | 2.40E−70 | 8.70E−67 | 671 | 147 | 5.64 |
| 6 | NUCLEUS | 2.63E−69 | 7.92E−66 | 5004 | 416 | 2.14 |
| 6 | NON_MEMBRANE_BOUNDED_ORGANELLE | 6.32E−69 | 1.43E−65 | 3274 | 327 | 2.57 |
| 6 | INTRACELLULAR_NON_MEMBRANE_BOUNDED_ORGANELLE | 6.32E−69 | 1.43E−65 | 3274 | 327 | 2.57 |
| 6 | CHROMOSOME | 4.37E−66 | 8.01E−63 | 560 | 131 | 6.02 |
| 6 | NUCLEAR_LUMEN | 4.43E−66 | 8.01E−63 | 2459 | 275 | 2.88 |
| 7 | NUCLEAR_PART | 1.91E−06 | 1.76E−02 | 2752 | 120 | 1.50 |
| 7 | RNA_PROCESSING | 1.95E−06 | 1.76E−02 | 578 | 38 | 2.26 |
| 7 | NUCLEAR_LUMEN | 5.11E−06 | 3.08E−02 | 2459 | 108 | 1.51 |
| 7 | RNA_SPLICING | 1.29E−05 | 5.84E−02 | 295 | 23 | 2.68 |
| 8 | IMMUNE_SYSTEM_PROCESS | 4.40E−56 | 7.96E−52 | 1322 | 150 | 4.27 |
| 8 | IMMUNE_RESPONSE | 1.98E−51 | 1.79E−47 | 762 | 111 | 5.49 |
| 8 | REGULATION_OF_IMMUNE_SYSTEM_PROCESS | 1.48E−45 | 8.94E−42 | 727 | 102 | 5.28 |
| 8 | DEFENSE_RESPONSE. | 2.74E−43 | 1.24E−39 | 801 | 104 | 4.89 |
| 8 | REGULATION_OF_IMMUNE_RESPONSE | 1.18E−42 | 4.27E−39 | 446 | 79 | 6.67 |
| 8 | LEUKOCYTE_ACTIVATION | 1.30E−41 | 3.93E−38 | 270 | 63 | 8.79 |
| 8 | CELL_ACTIVATION | 1.01E−39 | 2.61E−36 | 447 | 76 | 6.40 |
| 8 | LYMPHOCYTE_ACTIVATION | 1.12E−37 | 2.52E−34 | 224 | 55 | 9.25 |
| 8 | RESPONSE_TO_STIMULUS | 6.74E−37 | 1.36E−33 | 4756 | 257 | 2.03 |
| 8 | REGULATION_OF_LYMPHOCYTE_ACTIVATION | 3.99E−36 | 7.22E−33 | 228 | 54 | 8.92 |

TABLE 4

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| dna packaging complex: GO | 87 | 35 | 7.54E−25 | 2.81E−21 | 8.80 | CENPA; H2AFX; H2AFZ; HISTIH1A; HIST1H1B; HIST1H2AB; HISTIH2AE; HIST1H2AG; HIST1H2AH; HIST1H2AI; HIST1H2AL; HIST1H2BB; HIST1H2BE; HIST1H2BF; HIST1H2BG; HIST1H2BH; HIST1H2BI; HIST1H2BJ; HIST1H2BL; HIST1H2BM; HIST1H2BO; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L; LTF; LYZ |
| amyloids | 66 | 29 | 3.65E−22 | 5.43E−19 | 9.61 | H2AFX; H2AFZ; HIST1H2AB; HIST1H2AE; HIST1H2AJ; HIST1H2BB; HIST1H2BE; HIST1H2BF; HIST1H2BG; HIST1H2BH; HIST1H2BI; HIST1H2BJ; HIST1H2BL; HIST1H2BM; HIST1H2BO; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L |
| rna pol i promoter opening | 56 | 27 | 4.38E−22 | 5.43E−19 | 10.54 | H2AFX; H2AFZ; HIST1H2AB; HIST1H2AE; HIST1H2AJ; HIST1H2BB; HIST1H2BE; HIST1H2BF; HIST1H2BG; HIST1H2BH; HIST1H2BI; HIST1H2BJ; HIST1H2BL; HIST1H2BM; HIST1H2BO; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4K; HIST1H4L; MND1 |
| meiotic recombination | 77 | 29 | 6.81E−20 | 6.33E−17 | 8.24 | BLM; H2AFX; H2AFZ; HIST1H2AB; HIST1H2AE; HIST1H2AJ; HIST1H2BB; HIST1H2BE; HIST1H2BF; HIST1H2BG; HIST1H2BH; HIST1H2BI; HIST1H2BJ; HIST1H2BL; HIST1H2BM; HIST1H2BO; HIST1H3A; HIST1H3B; HIST1H3C; HIST1H3F; HIST1H3G; HIST1H3H; HIST1H3I; HIST1H3J; HIST1H4I; HIST1H4J; HIST1H4L; IFNG |
| systemic lupus erythematosus | 118 | 34 | 8.57E−19 | 6.37E−16 | 6.30 | CD80; FCGR1A; H2AFX; H2AFZ; HIST1H2AB; HIST1H2AE; HIST1H2AG; HIST1H2AH; HIST1H2AI; HIST1H2AJ; HIST1H2AL; HIST1H2BB; HIST1H2BE; HIST1H2BF; HIST1H2BG; HIST1H2BH; HIST1H2BI; HIST1H2BJ; HIST1H2BL; HIST1H2BM; HIST1H2BO; HIST1H3A; HIST1H3B; HIST1H3C; HIST1H3F; HIST1H3G; HIST1H3H; HIST1H3I; HIST1H3J; HIST1H4I; HIST1H4J; HIST1H4K; OIP5; TOP2A |
| dna packaging: GO | 163 | 38 | 2.29E−17 | 1.42E−14 | 5.10 | ASF1B; CCNB1; CDCA5; CDK1; CENPA; CENPN; CENPW; H2AFX; HISTIH1A; HIST1H1B; HIST1H2BB; HIST1H2BE; HIST1H2BF; HIST1H2BG; HIST1H2BH; HIST1H2BI; HIST1H2BJ; HIST1H2BL; HIST1H2BM; HIST1H2BO; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L; HJURP; HMGA2; NCAPG; NCAPH; HIST1H4L |
| rna pol i transcription | 80 | 27 | 3.35E−17 | 1.78E−14 | 7.38 | H2AFX; H2AFZ; HIST1H2AB; HIST1H2AE; HIST1H2AJ; HIST1H2BB; HIST1H2BE; HIST1H2BF; HIST1H2BG; HIST1H2BH; HIST1H2BI; HIST1H2BJ; HIST1H2BL; HIST1H2BM; HIST1H2BO; HIST1H3A; HIST1H3B; HIST1H3C; HIST1H3F; HIST1H3G; HIST1H3H; HIST1H3I; HIST1H3J; HIST1H4I; HIST1H4J; HIST1H4K; |
| protein dna complex: GO | 150 | 36 | 5.76E−17 | 2.68E−14 | 5.25 | CDC45; CENPA; H2AFX; H2AFZ; HISTIH1A; HIST1H1B; HIST1H2AB; HIST1H2AE; HIST1H2AG; HIST1H2AH; HIST1H2AI; HIST1H2AL; HIST 1H2BB; HIST1H2BE; HIST1H2BF; HIST1H2BG; HIST1H2BH; HIST1H2BI; HIST1H2BJ; HIST1H2BL; HIST1H2BM; HIST1H2BO; HIST1H3A; HIST1H3B; HIST1H3C; HIST1H3F; HIST1H3G; HIST1H3H; HIST1H3I; HIST1H3J; HIST1H4I]; HIST1H4J; HIST1H4K; HIST1H4L; HMGA2; PCNA |
| nuclear nucleosome: GO | 32 | 18 | 8.14E−17 | 3.36E−14 | 12.30 | HIST1H2BB; HIST1H2BE; HIST1H2BF; HIST1H2BG; HIST1H2BH; HIST1H2BI; HIST1H2BJ; HIST1H2BL; HIST1H2BM; HIST1H2BO; HIST1H3A; HIST1H3B; |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| | | | | | | HIST1H3C; HIST1H3F; HIST1H3G; HIST1H3H; HIST1H3I; HIST1H3J HIST1H4K; HIST1H4L; LMNB1; MND1 |
| meiosis | 106 | 30 | 1.59E−16 | 5.93E−14 | 6.19 | BLM; H2AFX; H2AFZ; HIST1H2AB; HIST1H2AE; HIST1H2AJ; HIST1H2BB; HIST1H2BE; HIST1H2BF; HIST1H2BG; HIST1H2BH; HIST1H2BI; HIST1H2BJ; HIST1H2BL; HIST1H2BM; HIST1H2BO; HIST1H3A; HIST1H3B; HIST1H3C; HIST1H3F; HIST1H3G; HIST1H3H; HIST1H3I; HIST1H3J; HIST1H4I; HIST1H4J; |
| defense response to bacterium: GO | 162 | 35 | 5.02E−15 | 1.61E−12 | 4.72 | ACP5; C10orf99; CAMP; CXCL13; CXCL6; DEFB103A; DEFB103B; DEFB4A; GBP6; HIST1H2BE; HIST1H2BF; HIST1H2BG; HIST1H2BI; HIST1H2BJ; IFNE; IFNG; IGHG4; IL12B; IL6; ISG15; LTF; LYZ; MYD88; PGL YRP2; PYCARD; RNASE7; S100A12; S100A14; S100A7; S100A8; S100A9; SERPINE1; SLPI; TREM1; WFDC12 |
| keratinization: GO | 49 | 20 | 5.19E−15 | 1.61E−12 | 8.93 | CDH3; CNFN; HRNR; IVL; KRT16; KRT17; LCE3A; LCE3D; LCE3E; SFN; SPRR1A; SPRR1B; SPRR2A; SPRR2B; SPRR2D; SPRR2E; SPRR2F; SPRR2G; SPRR3; TGMI |
| resolution of sister chromatid cohesion | 82 | 25 | 7.24E−15 | 2.07E−12 | 6.67 | BIRC5; BUB1; BUB1B; CCNB1; CCNB2; CDC20; CDCA5; CDCA8; CDK1; CENPA; CENPE; CENPN; KIF18A; KIF2C; MAD2L1; NDC80; NUF2; PLK1; SKA1; SPC25; TUBA1C; TUBB2A; TUBB6; ZWILCH; ZWINT |
| packaging of telomere ends | 46 | 19 | 1.87E−14 | 4.97E−12 | 9.03 | H2AFX; H2AFZ; HIST1H2AB; HIST1H2AE; HIST1H2AJ; HIST1H2BB; HIST1H2BE; HIST1H2BF; HIST1H2BG; HIST1H2BH; HIST1H2BI; HIST1H2BJ; HIST1H2BL; HIST1H2BM; HIST1H2BO; HIST1H4I; HIST1H4J; HIST1H4K; HIST1H4L |
| cytokine activity: GO | 174 | 35 | 4.95E−14 | 1.23E−11 | 4.40 | AREG; C10orf99; CCL18; CCL22; CCL3; CCL7; CSF2; CXCL1; CXCL10; CXCL11; CXCL13; CXCL3; CXCL5; CXCL6; CXCL9; EBI3; IFNE; IFNG; IL12B; IL19; IL1B; IL20; IL22; IL24; IL26; IL36A; IL36G; IL36RN; IL6; NAMPT; OSM; TNFSF10; TNFSF9; WNT5A; WNT7A |
| rho gtpase effectors | 185 | 36 | 6.34E−14 | 1.47E−11 | 4.26 | BIRC5; BUB1; BUB1B; CDC20; CDCA8; CENPA; CENPE; CENPN; H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L; KIF14; KIF18A; KIF2C; MAD2L1; NDC80; NUF2; PLK1; SFN; SKA1; SPC25; TUBA1C; TUBB2A; TUBB6; ZWILCH; ZWINT |
| cornified envelope: GO | 44 | 18 | 1.09E−13 | 2.39E−11 | 8.95 | CNFN; CRCT1; CSTA; IVL; LCE3A; LCE3D; LCE3E; PRR9; SPRR1A; SPRR1B; SPRR2A; SPRR2B; SPRR2D; SPRR2E; SPRR2F; SPRR2G; SPRR3; TGM1 |
| chromatin assembly or disassembly: GO | 153 | 32 | 1.88E−13 | 3.88E−11 | 4.57 | ASF1B; CENPA; CENPN; CENPW; H2AFX; HISTIH1A; HISTIH1B; HIST1H2BB; HIST1H2BE; HIST1H2BF; HIST1H2BG; HIST 1H2BH; HIST1H2BI; HIST1H2BJ; HIST1H2BL; HIST1H2BM; HIST1H2BO; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L; HJURP; HMGA2; OIP5 |
| rna pol i rna pol iii and mitochondrial transcription | 112 | 27 | 3.68E−13 | 7.20E−11 | 5.27 | H2AFX; H2AFZ; HIST1H2AB; HIST1H2AE; HIST1H2AJ; HIST1H2BB; HIST1H2BE; HIST1H2BF; HIST1H2BG; HIST1H2BH; HIST1H2BI; HIST1H2BJ; HIST1H2BL; HIST1H2BM; HIST1H2BO; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L |
| keratinocyte differentiation: GO | 99 | 25 | 8.57E−13 | 1.59E−10 | 5.52 | CDH3; CNFN; CRCT1; CSTA; HRNR; IVL; KRT16; KRT17; LCE3A; LCE3D; LCE3E; PRR9; S100A7; SFN; SPRR1A; SPRR1B; SPRR2A; SPRR2B; SPRR2D; SPRR2E; SPRR2F; SPRR2G; SPRR3; TGM1; WNT5A |
| condensation of prophase chromosomes | 38 | 16 | 1.41E−12 | 2.49E−10 | 9.21 | CCNB1; CDK1; H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L; PLK1 |
| peptide cross linking: GO | 53 | 18 | 4.74E−12 | 8.02E−10 | 7.43 | CRCT1; CSTA; IVL; LCE3A; LCE3D; LCE3E; PRR9; SPRR1A; SPRR1B; SPRR2A; |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| | | | | | | SPRR2B; SPRR2D; SPRR2E; SPRR2F; SPRR2G; SPRR3; TGM1; TGM2 |
| chromosome maintenance | 119 | 26 | 1.12E−11 | 1.81E−09 | 4.78 | CENPA; CENPN; CENPW; H2AFX; H2AFZ; HIST1H2AB; HIST1H2AE; HIST1H2AJ; HIST1H2BB; HIST1H2BE; HIST1H2BF; HIST1H2BG; HIST1H2BH; HIST1H2BI; HIST1H2BJ; HIST1H2BL; HIST1H2BM; HIST1H2BO; HIST1H4I; HIST1H4J; HIST1H4K; HIST1H4L; HJURP; LMNB1; OIP5; PCNA |
| meiotic synapsis | 70 | 20 | 1.25E−11 | 1.94E−09 | 6.25 | H2AFX; H2AFZ; HIST1H2AB; HIST1H2AE; HIST1H2AJ; HIST1H2BB; HIST1H2BE; HIST1H2BF; HIST1H2BG; HIST1H2BH; HIST1H2BI; HIST1H2BJ; HIST1H2BL; HIST1H2BM; HIST1H2BO; HIST1H4I; HIST1H4J; HIST1H4K; HIST1H4L; LMNB1 |
| dna methylation | 32 | 14 | 1.77E−11 | 2.63E−09 | 9.57 | H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L; UHRF1 |
| mitotic anaphase | 132 | 27 | 2.35E−11 | 3.36E−09 | 4.47 | BIRC5; BUB1; BUB1B; CDC20; CDCA5; CDCA8; CENPA; CENPE; CENPN; KIF18A; KIF2C; LMNB1; MAD2L1; NDC80; NUF2; PLK1; PSMA5; PSMB6; PTTG1; SKA1; SPC25; TUBA1C; TUBB2A; TUBB6; UBE2C; ZWILCH; ZWINT |
| separation of sister chromatids | 123 | 26 | 2.47E−11 | 3.41E−09 | 4.62 | BIRC5; BUB1; BUB1B; CDC20; CDCA5; CDCA8; CENPA; CENPE; CENPN; KIF18A; KIF2C; MAD2L1; NDC80; NUF2; PLK1; PSMA5; PSMB6; PTTG1; SKA1; SPC25; TUBA1C; TUBB2A; TUBB6; UBE2C; ZWILCH; ZWINT |
| mitotic metaphase and anaphase | 133 | 27 | 2.83E−11 | 3.75E−09 | 4.44 | BIRC5; BUB1; BUB1B; CDC20; CDCA5; CDCA8; CENPA; CENPE; CENPN; KIF18A; KIF2C; LMNB1; MAD2L1; NDC80; NUF2; PLK1; PSMA5; PSMB6; PTTG1; SKA1; SPC25; TUBA1C; TUBB2A; TUBB6; UBE2C; ZWILCH; ZWINT |
| deposition of new cenpa-containing nucleosomes at the centromere | 45 | 16 | 3.08E−11 | 3.82E−09 | 7.78 | CENPA; CENPN; CENPW; H2AFX; H2AFZ; HIST1H2AE; HIST1H2BB; HIST1H2BF; HIST1H2BH; HIST1H2BM; HIST1H4I; HIST 1H4J; HIST 1H4K; HIST1H4L; HJURP; OIP5 |
| nucleosome assembly | 45 | 16 | 3.08E−11 | 3.82E−09 | 7.78 | CENPA; CENPN; CENPW; H2AFX; H2AFZ; HIST1H2AE; HIST1H2BB; HIST1H2BF; HIST1H2BH; HIST1H2BM; HIST1H4I; HIST 1H4J; HIST 1H4K; HIST1H4L; HJURP; OIP5 |
| g2/m checkpoints | 118 | 25 | 5.57E−11 | 6.68E−09 | 4.63 | BLM; CCNB1; CCNB2; CDC25A; CDC25B; CDC45; CDC6; CDK1; CLSPN; EXO1; H2AFX; HIST1H2BB; HIST1H2BF; HIST1H2BH; HIST1H2BM; HIST1H4I; HIST1H4J; HIST1H4K; HIST1H4L; MCM10; ORC1; ORC6; PSMA5; PSMB6; SFN |
| rna polymerase i promoter opening | 29 | 13 | 6.17E−11 | 7.18E−09 | 9.80 | H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L |
| telomere maintenance | 76 | 20 | 6.60E−11 | 7.39E−09 | 5.75 | H2AFX; H2AFZ; HIST1H2AB; HIST1H2AE; HIST1H2AJ; HIST1H2BB; HIST1H2BE; HIST1H2BF; HIST1H2BG; HIST1H2BH; HIST1H2BI; HIST1H2BJ; HIST1H2BL; HIST1H2BM; HIST1H2BO; HIST1H4I; HIST1H4J; HIST1H4K; HIST1H4L; PCNA |
| kinetochores via a mad2 inhibitory signal | 61 | 18 | 6.95E−11 | 7.39E−09 | 6.45 | BIRC5; BUB1; BUB1B; CDC20; CDCA8; CENPA; CENPE; CENPN; KIF18A; KIF2C; MAD2L1; NDC80; NUF2; PLK1; SKA1; SPC25; ZWILCH; ZWINT |
| amplification of signal from the kinetochores | 61 | 18 | 6.95E−11 | 7.39E−09 | 6.45 | BIRC5; BUB1; BUB1B; CDC20; CDCA8; CENPA; CENPE; CENPN; KIF18A; KIF2C; MAD2L1; NDC80; NUF2; PLK1; SKA1; SPC25; ZWILCH; ZWINT |
| sister chromatid segregation: GO | 159 | 29 | 8.51E−11 | 8.79E−09 | 3.99 | BIRC5; BUB1; BUB1B; CCNB1; CDC20; CDCA5; CDCA8; CENPA; CENPE; CENPN; CEP55; DLGAP5; KIF14; KIF18A; KIF23; KIF2C; KIF4A; MAD2L1; NCAPG; NCAPH; NDC80; NEK2; NUF2; PLK1; SKA1; SPC25; TOP2A; ZWILCH; ZWINT |
| interferon alpha/beta signaling | 48 | 16 | 9.52E−11 | 9.58E−09 | 7.29 | IFI27; IFI6; IFIT3; IFITM1; IFITM3; IL6; ISG15; ISG20; MX1; OAS1; OAS2; OAS3; OASL; RSAD2; SOCS3; STAT1 |
| condensed chromosome centromeric region: GO | 86 | 21 | 1.06E−10 | 1.02E−08 | 5.34 | AURKA; BIRC5; BUB1; BUB1B; CCNB1; CENPA; CENPE; CENPN; CENPW; HJURP; KIF2C; MAD2L1; NDC80; NEK2; NUF2; PLK1; SKA1; SKA3; SPC25; ZWILCH; ZWINT |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| mitotic spindle checkpoint | 70 | 19 | 1.07E−10 | 1.02E−08 | 5.94 | BIRC5; BUB1; BUB1B; CDC20; CDCA8; CENPA; CENPE; CENPN; KIF18A; KIF2C; MAD2L1; NDC80; NUF2; PLK1; SKA1; SPC25; UBE2C; ZWILCH; ZWINT |
| chromatin silencing: GO | 78 | 20 | 1.10E−10 | 1.03E−08 | 5.61 | H2AFX; H2AFZ; HIST1H2AB; HIST1H2AE; HIST1H2AG; HIST1H2AH; HIST1H2AI; HIST 1H2AL; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L |
| rho gtpases activate formins | 88 | 21 | 1.69E−10 | 1.50E−08 | 5.22 | BIRC5; BUB1; BUB1B; CDC20; CDCA8; CENPA; CENPE; CENPN; KIF18A; KIF2C; MAD2L1; NDC80; NUF2; PLK1; SKA1; SPC25; TUBA1C; TUBB2A; TUBB6; ZWILCH; ZWINT |
| activated pkn1 stimulates transcription of ar (androgen receptor) regulated genes klk2 and klk3 | 31 | 13 | 1.73E−10 | 1.50E−08 | 9.17 | H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L |
| dna replication dependent nucleosome organization: GO | 31 | 13 | 1.73E−10 | 1.50E−08 | 9.17 | ASF1B; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L |
| dna damage/telomere stress induced senescence | 51 | 16 | 2.69E−10 | 2.27E−08 | 6.86 | CCNA2; CCNE1; H2AFX; H2AFZ; HIST1H1B; HIST1H2AE; HIST1H2BB; HIST1H2BF; HIST1H2BH; HIST1H2BM; HIST1H4I; HIST1H4J; HIST1H4K; HIST1H4L; HMGA2; LMNB1 |
| mitotic prometaphase | 158 | 28 | 3.56E−10 | 2.88E−08 | 3.88 | BIRC5; BUB1; BUB1B; CCNB1; CCNB2; CDC20; CDCA5; CDCA8; CDK1; CENPA; CENPE; CENPN; KIF18A; KIF2C; MAD2L1; NCAPG; NCAPH; NDC80; NEK2; NUF2; PLK1; SKA1; SPC25; TUBA1C; TUBB2A; TUBB6; ZWILCH; ZWINT |
| negative regulation of viral genome replication: GO | 45 | 15 | 3.56E−10 | 2.88E−08 | 7.29 | APOBEC3A; HMGA2; IFI16; IFITM1; IFITM3; ISG15; ISG20; LTF; MX1; OAS1; OAS3; OASL; RSAD2; SLPI; ZC3H12A |
| cell cycle | 148 | 27 | 3.67E−10 | 2.90E−08 | 3.99 | GINS3; H2AFZ; HIST1H2AB; HIST1H2AE; HIST1H2AJ; HIST1H2BB; HIST1H2BE; HIST1H2BF; HIST1H2BG; HIST1H2BH; HIST1H2BI; HIST1H2BJ; HIST1H2BL; HIST1H2BM; HIST1H2BO; HIST1H3A; HIST1H3I; HIST1H4I; HIST1H4J; HIST1H4K; HIST1H4L; LMNB1; TK1; TUBA1C; TUBB2A; TUBB6; YWHAQ |
| sirt1 negatively regulates rrna expression | 33 | 13 | 4.46E−10 | 3.45E−08 | 8.61 | H2AFX; H2AFZ; HIST1H2AE; HIST1H2BB; HIST1H2BF; HIST1H2BH; HIST1H2BM; HIST1H3A; HIST1H4I; HIST1H4I; HIST1H4J; HIST1H4K; HIST1H4L |
| positive regulation of leukocyte chemotaxis: GO | 76 | 19 | 5.04E−10 | 3.83E−08 | 5.47 | C1QBP; CALR; CCL3; CCL7; CXCL1; CXCL10; CXCL11; CXCL13; CXCL3; CXCL5; CXCL6; CXCL9; IL1B; IL6; RAC2; S100A14; S100A7; SERPINE1; WNT5A |
| nuclear chromosome segregation: GO | 196 | 31 | 8.18E−10 | 6.08E−08 | 3.46 | BIRC5; BUB1; BUB1B; CCNB1; CDC20; CDCA5; CDCA8; CENPA; CENPE; CENPN; CEP55; DLGAP5; KIF14; KIF18A; KIF23; KIF2C; KIF4A; MAD2L1; NCAPG; NCAPH; NDC80; NEK2; NUF2; PLK1; PTTG1; SKA1; SPC25; TOP2A; TRIP13; ZWILCH; ZWINT |
| protein heterotetramerization: GO | 35 | 13 | 1.06E−09 | 7.74E−08 | 8.12 | HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L; RRM2 |
| condensed chromosome: GO | 167 | 28 | 1.33E−09 | 9.45E−08 | 3.67 | AURKA; BIRC5; BLM; BUB1; BUB1B; CCNB1; CDCA5; CENPA; CENPE; CENPN; CENPW; H2AFX; HJURP; KIF2C; MAD2L1; NCAPG; NCAPH; NDC80; NEK2; NUF2; PLK1; RCC1; SKA1; SKA3; SPC25; TOP2A; ZWILCH; ZWINT |
| epidermal cell differentiation: GO | 136 | 25 | 1.35E−09 | 9.45E−08 | 4.02 | CDH3; CNFN; CRCT1; CSTA; HRNR; IVL; KRT16; KRT17; LCE3A; LCE3D; LCE3E; PRR9; S100A7; SFN; SPRR1A; SPRR1B; SPRR2A; SPRR2B; SPRR2D; SPRR2E; SPRR2F; SPRR2G; SPRR3; TGM1; WNT5A |
| chemokine receptors bind chemokines | 49 | 15 | 1.39E−09 | 9.55E−08 | 6.69 | CCL22; CCL3; CCL7; CCR4; CCR5; CXCL1; CXCL10; CXCL11; CXCL13; CXCL3; CXCL5; CXCL6; CXCL8; CXCL9; CXCR4 |
| ercc6 (csb) and ehmt2 (g9a) positively regulate rrna expression | 36 | 13 | 1.60E−09 | 1.08E−07 | 7.90 | H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L |
| defense response to virus: GO | 138 | 25 | 1.85E−09 | 1.22E−07 | 3.96 | APOBEC3A; APOBEC3B; CXCL10; CXCL9; IFI16; IFI44L; IFIT3; IFITM1; IFITM3; |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| | | | | | | IFNE; IFNG; IL12B; IL6; ISG15; ISG20; MX1; OAS1; OAS2; OAS3; OASL; POLR3G; PYCARD; RSAD2; STAT1; ZC3H12A |
| plk1 pathway | 43 | 14 | 1.90E−09 | 1.22E−07 | 7.12 | AURKA; BUB1; BUB1B; CCNB1; CDC20; CDC25B; CDK1; CENPE; CLSPN; ECT2; KIF20A; NDC80; PLK1; TPX2 |
| runx1 regulates genes involved in megakaryocyte differentiation and platelet function | 43 | 14 | 1.90E−09 | 1.22E−07 | 7.12 | H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L; NR4A3 |
| mitotic m m g1 phases | 159 | 27 | 1.93E−09 | 1.22E−07 | 3.71 | BIRC5; BUB1; BUB1B; CDC20; CDC45; CDC6; CDCA8; CENPA; CENPN; KIF18A; KIF20A; KIF23; KIF2C; MAD2L1; MCM10; NDC80; NUF2; ORC1; ORC6; PLK1; PSMA4; PSMA5; PSMB6; SKA1; SPC25; ZWILCH; ZWINT |
| senescence-associated secretory phenotype (sasp) | 66 | 17 | 2.36E−09 | 1.47E−07 | 5.63 | CCNA2; CXCL8; H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L; IL6; UBE2C |
| prc2 methylates histones and dna | 38 | 13 | 3.46E−09 | 2.11E−07 | 7.48 | H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L |
| transcriptional regulation by runx1 | 132 | 24 | 3.55E−09 | 2.13E−07 | 3.98 | CBX2; CSF2; CTLA4; CTSL; H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L; IFNG; IL2RA; NR4A3; PSMA5; PSMB6; SERPINB1; SOCS3 |
| positive regulation of leukocyte migration: GO | 104 | 21 | 4.47E−09 | 2.62E−07 | 4.42 | C1QBP; CALR; CCL3; CCL7; CXCL1; CXCL10; CXCL11; CXCL 13; CXCL3; CXCL5; CXCL6; CXCL9; IL1B; IL6; PTAFR; PYCARD; RAC2; S100A14; S100A7; SERPINE1; WNT5A |
| mitotic prophase | 77 | 18 | 4.51E−09 | 2.62E−07 | 5.11 | CCNB1; CCNB2; CDK1; H2AFX; H2AFZ; HIST1H2AE; HIST1H2BB; HIST1H2BF; HIST1H2BH; HIST1H2BM; HIST1H3A; HIST1H3I; HIST1H4I; HIST 1H4J; HIST1H4K; HIST1H4L; LMNB1; PLK1 |
| negative regulation of gene expression epigenetic: GO | 95 | 20 | 4.74E−09 | 2.71E−07 | 4.60 | H2AFX; H2AFZ; HIST1H2AB; HIST1H2AE; HIST1H2AG; HIST1H2AH; HIST1H2AI; HIST1H2AL; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L |
| negative regulation of multi organism process: GO | 134 | 24 | 4.85E−09 | 2.73E−07 | 3.92 | APOBEC3A; C1QBP; CAMP; CCL3; HMGA2; IFI16; IFITM1; IFITM3; IFNG; IL12B; IL2RA; ISG15; ISG20; LTF; MX1; OAS1; OAS3; OASL; PRDM1; RSAD2; SLPI; STAT1; TRIM14; ZC3H12A |
| regulation of viral genome replication: GO | 69 | 17 | 4.96E−09 | 2.75E−07 | 5.39 | APOBEC3A; HMGA2; IFI16; IFITM1; IFITM3; ISG15; ISG20; LTF; MX1; OAS1; OAS3; OASL; PPIB; RSAD2; SLPI; TOP2A; ZC3H12A |
| chromosome centromeric region: GO | 156 | 26 | 5.69E−09 | 3.08E−07 | 3.64 | AURKA; BIRC5; BUB1; BUB1B; CCNB1; CDCA5; CDCA8; CENPA; CENPE; CENPN; CENPW; ESCO2; HJURP; KIF18A; KIF2C; MAD2L1; NDC80; NEK2; NUF2; OIP5; PLK1; SKA1; SKA3; SPC25; ZWILCH; ZWINT |
| transcription | 189 | 29 | 5.72E−09 | 3.08E−07 | 3.36 | H2AFX; H2AFZ; HIST1H2AB; HIST1H2AE; HIST1H2AJ; HIST1H2BB; HIST1H2BE; HIST1H2BF; HIST1H2BG; HIST1H2BH; HIST1H2BI; HIST1H2BJ; HIST1H2BL; HIST1H2BM; HIST1H2BO; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L; SNRPF; SNRPG |
| kinetochore: GO | 106 | 21 | 6.41E−09 | 3.41E−07 | 4.33 | BIRC5; BUB1; BUB1B; CCNB1; CENPA; CENPE; CENPN; CENPW; HJURP; KIF18A; KIF2C; MAD2L1; NDC80; NEK2; NUF2; PLK1; SKA1; SKA3; SPC25; ZWILCH; ZWINT |
| mitotic spindle organization: GO | 62 | 16 | 6.57E−09 | 3.44E−07 | 5.64 | AURKA; BIRC5; CCNB1; KIF11; KIF23; KIF4A; MYBL2; NDC80; NEK2; PLK2; RAN; RCC1; SPC25; STIL; TPX2; TTK |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| amyloid fiber formation | 47 | 14 | 7.06E−09 | 3.65E−07 | 6.51 | H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L; LYZ |
| regulation of nuclear division: GO | 148 | 25 | 8.27E−09 | 4.22E−07 | 3.69 | AURKA; BIRC5; BUB1; BUB1B; CALR; CCNB1; CDC20; CDC6; CDCA5; CENPE; DLGAP5; EPGN; IL1B; KIF11; MAD2L1; NEK2; OSM; PKMYT1; PLK1; PTTG1; RCC1; TGFA; TTK; UBE2C; WNT5A |
| regulation of leukocyte chemotaxis: GO | 90 | 19 | 1.07E−08 | 5.31E−07 | 4.62 | C1QBP; CALR; CCL3; CCL7; CXCL1; CXCL 10; CXCL11; CXCL 13; CXCL3; CXCL5; CXCL6; CXCL9; IL1B; IL6; RAC2; S100A14; S100A7; SERPINE1; WNT5A |
| negative regulation of viral process: GO | 81 | 18 | 1.07E−08 | 5.31E−07 | 4.86 | APOBEC3A; CCL3; HMGA2; IFI16; IFITM1; IFITM3; ISG15; ISG20; LTF; MX1; OAS1; OAS3; OASL; RSAD2; SLPI; STAT1; TRIM14; ZC3H12A |
| rho gtpases activate pkns | 49 | 14 | 1.29E−08 | 6.26E−07 | 6.25 | H2AFX; H2AFZ; HIST1H2AE; HIST1H2BB; HIST1H2BF; HIST1H2BH; HIST1H2BM; HIST1H3A; HIST1H3I; HIST1H4I;HIST1H4J; HIST1H4K; HIST1H4L; SFN |
| chromatin silencing at rdna: GO | 35 | 12 | 1.30E−08 | 6.26E−07 | 7.50 | HIST1H3A; HIST1H3B; HIST1H3C; HIST1H3F; HIST1H3G; HIST1H3H; HIST1H3I; HIST1H3J; HIST1H4I]; HIST1H4J; HIST1H4K; HIST1H4L |
| formation of the beta-catenin:tcf transactivating complex | 43 | 13 | 1.92E−08 | 9.15E−07 | 6.61 | H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L |
| chemokine mediated signaling pathway: GO | 59 | 15 | 2.35E−08 | 1.11E−06 | 5.56 | CXCL3; CXCL5; CXCL6; CXCL9; CXCR4 CCL18; CCL22; CCL3; CCL7; CCR4; CCR5; CXCL1; CXCL10; CXCL11; CXCL13; |
| mitotic sister chromatid segregation: GO | 85 | 18 | 2.40E−08 | 1.12E−06 | 4.63 | CCNB1; CDCA5; CDCA8; CENPE; CEP55; DLGAP5; KIF14; KIF18A; KIF23; KIF2C; KIF4A; MAD2L1; NCAPG; NCAPH; NDC80; NEK2; PLK1; ZWINT |
| foxm1 pathway | 38 | 12 | 3.74E−08 | 1.72E−06 | 6.91 | BIRC5; CCNA2; CCNB1; CCNB2; CCNE1; CDC25B; CDK1; CENPA; FOXM1; NEK2; PLK1; TGFA |
| sister chromatid cohesion: GO | 97 | 19 | 3.89E−08 | 1.75E−06 | 4.28 | BIRC5; BUB1; BUB1B; CDC20; CDCA5; CDCA8; CENPA; CENPE; CENPN; KIF18A; KIF2C; MAD2L1; NDC80; NUF2; PLK1; SKA1; SPC25; ZWILCH; ZWINT |
| b-wich complex positively regulates rrna expression | 53 | 14 | 3.91E−08 | 1.75E−06 | 5.78 | DDX21; H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L |
| response to type i interferon: GO | 54 | 14 | 5.08E−08 | 2.25E−06 | 5.67 | IFI27; IFI6; IFIT3; IFITM1; IFITM3; ISG15; ISG20; MX1; OAS1; OAS2; OAS3; OASL; RSAD2; STAT1 |
| chemokine activity: GO | 39 | 12 | 5.20E−08 | 2.28E−06 | 6.73 | CCL18; CCL22; CCL3; CCL7; CXCL1; CXCL10; CXCL11; CXCL13; CXCL3; CXCL5; CXCL6; CXCL9 |
| chemokine receptor binding: GO | 48 | 13 | 8.32E−08 | 3.60E−06 | 5.92 | CCL18; CCL22; CCL3; CCL7; CXCL1; CXCL10; CXCL11; CXCL13; CXCL3; CXCL5; CXCL6; CXCL9; S100A14 |
| response to interferon gamma: GO | 133 | 22 | 9.03E−08 | 3.86E−06 | 3.62 | CCL18; CCL22; CCL3; CCL7; CYP27B1; FCGR1A; GAPDH; GBP6; IFI30; IFITM1; IFITM3; IFNG; IL12B; KYNU; MEFV; OAS1; OAS2; OAS3; OASL; PTAFR; STAT1; WNT5A |
| dna replication | 144 | 23 | 9.21E−08 | 3.89E−06 | 3.49 | BIRC5; BUB1; BUB1B; CCNA2; CDC20; CDCA8; CENPA; CENPN; KIF18A; KIF20A; KIF23; KIF2C; MAD2L1; NDC80; NUF2; PLK1; PSMA4; PSMA5; PSMB6; SKA1; SPC25; ZWILCH; ZWINT |
| cell chemotaxis: GO | 145 | 23 | 1.05E−07 | 4.39E−06 | 3.47 | CCL18; CCL22; CCL3; CCL7; CCR5; CXCL1; CXCL10; CXCL11; CXCL13; CXCL3; CXCL5; CXCL6; CXCL9; CXCR4; HBEGF; IFNG; IL1B; IL6; PRKCQ; S100A12; S100A8; S100A9; TREM1 |
| positive regulation of chemotaxis: GO | 114 | 20 | 1.22E−07 | 5.04E−06 | 3.84 | ARTN; C1QBP; CALR; CCL3; CCL7; CXCL1; CXCL10; CXCL11; CXCL13; CXCL3; CXCL5; CXCL6; CXCL9; IL1B; IL6; RAC2; S100A14; S100A7; SERPINE1; WNT5A |
| il23 pathway | 35 | 11 | 1.40E−07 | 5.66E−06 | 6.87 | CD3E; CXCL1; CXCL9; IFNG; IL12B; IL19; IL1B; IL24; IL6; SOCS3; STAT1 |
| rna polymerase i chain elongation | 50 | 13 | 1.41E−07 | 5.66E−06 | 5.69 | H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| transcriptional regulation by small rnas | 50 | 13 | 1.41E−07 | 5.66E−06 | 5.69 | H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L |
| regulation of interferon gamma production: GO | 87 | 17 | 1.98E−07 | 7.83E−06 | 4.27 | C1QBP; CD2; CD274; CD3E; EBI3; IL12B; IL12RB2; IL1B; IL36RN; ISG15; PGLYRP2; PYCARD; SASH3; SLAMF1; TNFSF9; WNT5A; ZC3H12A |
| interferon signaling | 173 | 25 | 2.00E−07 | 7.83E−06 | 3.16 | EIF4A3; FCGR1A; GBP6; HERC6; IFI27; IFI30; IFI6; IFIT3; IFITM1; IFITM3; IFNG; IL6; ISG15; ISG20; KPNA2; MX1; OAS1; OAS2; OAS3; OASL; PTAFR; RSAD2; SOCS3; STAT1; TRIM14 |
| cellular senescence | 118 | 20 | 2.20E−07 | 8.51E−06 | 3.71 | CBX2; CCNA2; CCNE1; CXCL8; H2AFZ; HIST1H1B; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L; IL6; LMNB1; UBE2C |
| regulation of leukocyte migration: GO | 140 | 22 | 2.30E−07 | 8.77E−06 | 3.44 | C1QBP; CALR; CCL3; CCL7; CXCL1; CXCL 10; CXCL11; CXCL 13; CXCL3; CXCL5; CXCL6; CXCL9; HMOX1; IL1B; IL6; PTAFR; PYCARD; RAC2; S100A14; S100A7; SERPINE1; WNT5A |
| hdacs deacetylate histones | 44 | 12 | 2.31E−07 | 8.77E−06 | 5.96 | H2AFX; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L |
| interleukin-4 and 13 signaling | 88 | 17 | 2.36E−07 | 8.86E−06 | 4.22 | BIRC5; CXCL8; FSCN1; HIF1A; HMOX1; HSPA8; IL13RA1; IL1B; IL4R; IL6; JAK3; LCN2; MMP1; MMP3; MMP9; SOCS3; STAT1 |
| response to fungus: GO | 37 | 11 | 2.66E−07 | 9.73E−06 | 6.50 | BAK1; C10orf99; CAMP; CLEC7A; COTL1; IL36RN; IL6; LTF; S100A12; S100A8; S100A9 |
| apc/c-mediated degradation of cell cycle proteins | 61 | 14 | 2.67E−07 | 9.73E−06 | 5.02 | AURKA; BUB1; BUB1B; CCNA2; CCNB1; CDC20; CDK1; MAD2L1; NEK2; PLK1; PSMA5; PSMB6; PTTG1; UBE2C |
| positive epigenetic regulation of rrna expression | 61 | 14 | 2.67E−07 | 9.73E−06 | 5.02 | DDX21; H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L |
| runx1 regulates transcription of genes involved in differentiation of hses | 70 | 15 | 2.74E−07 | 9.89E−06 | 4.69 | H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L; PSMA5; PSMB6 |
| aurora b pathway | 38 | 11 | 3.61E−07 | 1.29E−05 | 6.33 | AURKA; BIRC5; BUB1; CDCA8; CENPA; KIF20A; KIF23; KIF2C; NCAPG; NCAPH; NDC80 |
| activation of apc/c and apc/c:cdc20 mediated degradation of mitotic proteins | 54 | 13 | 3.77E−07 | 1.34E−05 | 5.26 | BUB1; BUB1B; CCNA2; CCNB1; CDC20; CDK1; MAD2L1; NEK2; PLK1; PSMA5; PSMB6; PTTG1; UBE2C |
| g2/m dna damage checkpoint | 63 | 14 | 4.09E−07 | 1.44E−05 | 4.86 | BLM; CCNB1; CDK1; EXO1; H2AFX; HIST1H2BB; HIST1H2BF; HIST1H2BH; HIST1H2BM; HIST1H4I; HIST1H4J; HIST1H4K; HIST1H4L; SFN |
| activation of e2f1 target genes at g1/s | 25 | 9 | 4.70E−07 | 1.62E−05 | 7.87 | CCNE1; CDC25A; CDC45; CDC6; CDK1; ORC1; PCNA; RRM2; TK1 |
| g1/s-specific transcription | 25 | 9 | 4.70E−07 | 1.62E−05 | 7.87 | CCNE1; CDC25A; CDC45; CDC6; CDK1; ORC1; PCNA; RRM2; TK1 |
| p73pathway | 74 | 15 | 5.90E−07 | 1.99E−05 | 4.43 | AEN; BAK1; BUB1; CCNA2; CCNB1; CDK1; CLCA2; FBXO45; IL4R; NTRK1; PLK1; S100A2; SERPINA1; SERPINE1; SFN |
| hindbrain development during early embryogenesis | 56 | 13 | 5.95E−07 | 1.99E−05 | 5.08 | H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L |
| activation of hox genes during differentiation | 56 | 13 | 5.95E−07 | 1.99E−05 | 5.08 | H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L |
| regulation of symbiosis encompassing mutualism through parasitism: GO | 184 | 25 | 6.61E−07 | 2.19E−05 | 2.97 | APOBEC3A; CAMP; CCL3; HMGA2; IFI16; IFITM1; IFITM3; IFNG; IL12B; ISG15; ISG20; LAMP3; LTF; MX1; OAS1; OAS3; OASL; PPIB; RSAD2; SLPI; STAT1; TAP2; TOP2A; TRIM14; ZC3H12A |
| oxidative stress induced senescence | 75 | 15 | 7.08E−07 | 2.33E−05 | 4.37 | CBX2; H2AFX; H2AFZ; HIST1H2AE; HIST 1H2BB; HIST 1H2BF; HIST1H2BH; HIST1H2BM; HIST1H3A; HIST1H3I; HIST1H4I; HIST1H4J; HIST1H4K; HIST1H4L; IL6 |
| processing of dna double-strand break | 66 | 14 | 7.52E−07 | 2.45E−05 | 4.64 | BLM; CCNA2; CLSPN; EXO1; H2AFX; HIST1H2BB; HIST 1H2BF; HIST1H2BH; |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| ends | | | | | | HIST1H2BM; HIST1H4I; HIST1H4J; HIST1H4K; HIST1H4L; TIMELESS |
| nad metabolic process: GO | 49 | 12 | 8.32E−07 | 2.69E−05 | 5.36 | ENO1; GAPDH; HK2; KYNU; LDHA; NAMPT; PFKFB4; PGAM1; PGK1; PNP; TPI1; VCP |
| kinesins | 41 | 11 | 8.45E−07 | 2.71E−05 | 5.87 | CENPE; ; KIF15; KIF18A; KIF20A; KIF23; KIF2C; KIF4A; TUBA1C; TUBB2A; TUBB6 |
| rna polymerase i promoter clearance | 58 | 13 | 9.18E−07 | 2.92E−05 | 4.90 | H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L |
| antimicrobial humoral response: GO | 34 | 10 | 9.94E−07 | 3.10E−05 | 6.43 | CAMP; HIST1H2BE; HIST1H2BF; HIST1H2BG; HIST1H2BI; HIST1H2BJ; IL36RN; LTF; RNASE7; SLPI |
| replication | 34 | 10 | 9.94E−07 | 3.10E−05 | 6.43 | CCNB1; CCNE1; CDC25A; CDC45; CDC6; CDK1; ORC1; ORC6; PCNA; RRM2 |
| nkt pathway | 27 | 9 | 1.00E−06 | 3.10E−05 | 7.29 | CCL3; CCR4; CCR5; CSF2; CXCR4; IFNG; IL12B; IL12RB2; IL4R |
| regulation of chromosome segregation: GO | 77 | 15 | 1.01E−06 | 3.11E−05 | 4.26 | BUB1; BUB1B; CCNB1; CDC6; CDCA5; CENPE; DLGAP5; ECT2; KIF2C; MAD2L1; NEK2; PLK1; PTTG1; TTK; UBE2C |
| rna polymerase i transcription | 59 | 13 | 1.13E−06 | 3.45E−05 | 4.82 | H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L |
| mitotic g1-g1/s phases | 109 | 18 | 1.25E−06 | 3.77E−05 | 3.61 | CCNA2; CCNB1; CCNE1; CDC25A; CDC25B; CDC45; CDC6; CDK1; MCM10; MYBL2; ORC1; ORC6; PCNA; PSMA5; PSMB6; RRM2; TK1; TOP2A |
| g0 and early g1 | 28 | 9 | 1.42E−06 | 4.21E−05 | 7.03 | CCNA2; CCNE1; CDC25A; CDC25B; CDC6; CDK1; MYBL2; PCNA; TOP2A |
| regulation of interleukin 1 beta production: GO | 43 | 11 | 1.42E−06 | 4.21E−05 | 5.59 | ACP5; CCL3; GSTP1; IFI16; IFNG; MEFV; NLRP2; PYCARD; TRIM16; WNT5A; ZC3H12A |
| positive regulation of t cell proliferation: GO | 89 | 16 | 1.43E−06 | 4.21E−05 | 3.93 | CD274; CD3E; CD80; EBI3; IFNG; IL12B; IL1B; IL2RA; IL6; JAK3; PNP; PRKCQ; PYCARD; SASH3; SLAMF1; TNFSF9 |
| factors involved in megakaryocyte development and platelet production | 133 | 20 | 1.59E−06 | 4.65E−05 | 3.29 | CENPE; HIST1H3A; HIST1H3B; HIST1H3C; HIST1H3F; HIST1H3G; HIST1H3H; HIST1H3I; HIST1H3J; IL6; KIF11; KIF15; KIF18A; KIF20A; KIF23; KIF2C; KIF4A; TUBA1C; TUBB2A; TUBB6 |
| jak-stat signaling pathway | 122 | 19 | 1.64E−06 | 4.77E−05 | 3.41 | IL4R; IL6; IL7R; JAK3; OSM; SOCS3; STAT1<br>CSF2; IFNE; IFNG; IL12B; IL12RB2; IL13RA1; IL19; IL20; IL22; IL24; IL26; IL2RA; |
| homology directed repair | 90 | 16 | 1.67E−06 | 4.81E−05 | 3.89 | BLM; CCNA2; CLSPN; EXO1; H2AFX; HIST1H2BB; HIST1H2BF; HIST1H2BH; HIST1H2BM; HIST1H4I; HIST1H4J; HIST1H4K; HIST1H4L; PCNA; POLQ; TIMELESS |
| nore negatively regulates rrna expression | 61 | 13 | 1.70E−06 | 4.86E−05 | 4.66 | H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L |
| response: GO | 22 | 8 | 1.78E−06 | 5.04E−05 | 7.95 | CAMP; HIST1H2BE; HIST1H2BF; HIST1H2BG; HIST1H2BI; HIST1H2BJ; IL6; LTF |
| apc/c:cdc20 mediated degradation of mitotic proteins | 53 | 12 | 2.06E−06 | 5.80E−05 | 4.95 | BUB1; BUB1B; CCNA2; CCNB1; CDC20; CDK1; MAD2L1; NEK2; PSMA5; PSMB6; PTTG1; UBE2C |
| dna double-strand break repair | 103 | 17 | 2.41E−06 | 6.68E−05 | 3.61 | BLM; CCNA2; CLSPN; EXO1; H2AFX; HIST1H2BB; HIST1H2BF; HIST1H2BH; HIST1H2BM; HIST1H4I; HIST1H4J; HIST1H4K; HIST1H4L; KPNA2; PCNA; POLQ; TIMELESS |
| leukocyte chemotaxis: GO | 103 | 17 | 2.41E−06 | 6.68E−05 | 3.61 | CCL18; CCL22; CCL3; CCL7; CCR5; CXCL 10; CXCL11; CXCL 13; CXCL3; CXCR4; IFNG; IL1B; IL6; S100A12; S100A8; S100A9; TREM1 |
| negative epigenetic regulation of rrna expression | 64 | 13 | 3.02E−06 | 8.32E−05 | 4.44 | H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L |
| positive regulation of cell division: GO | 105 | 17 | 3.16E−06 | 8.65E−05 | 3.54 | AURKA; BIRC5; CDC25B; CDC6; CDCA5; DLGAP5; ECT2; EPGN; IL1B; KIF14; KIF23; OSM; PGF; PLK1; TGFA; UBE2C; WNT5A |
| humoral immune response: GO | 128 | 19 | 3.44E−06 | 9.33E−05 | 3.25 | C1QBP; CAMP; EBI3; EXO1; HIST1H2BE; HIST1H2BF; HIST1H2BG; HIST1H2BI; HIST1H2BJ; IFNE; IFNG; IGHG4; IL36RN; IL6; LTF; RNASE7; SLPI; TNFRSF21; TREM1 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| cellular response to biotic stimulus: GO | 152 | 21 | 3.65E−06 | 9.83E−05 | 3.02 | CCL3; CCR5; CD80; CLEC7A; CMPK2; CSF2; CXCL10; GSTP1; HIF1A; IFNG; IL12B; IL1B; IL24; IL6; PLAU; PTAFR; PYCARD; SERPINE1; TNIP3; WNT5A; ZC3H12A |
| regulation of gene silencing: GO | 47 | 11 | 3.70E−06 | 9.90E−05 | 5.12 | CDC45; HIST1H3A; HIST1H3B; HIST1H3C; HIST1H3F; HIST1H3G; HIST1H3H; HIST1H3I; HIST1H3J; UHRF1; ZC3H12A |
| hdr through homologous recombination (hr) or single strand annealing (ssa) | 85 | 15 | 3.74E−06 | 9.94E−05 | 3.86 | BLM; CCNA2; CLSPN; EXO1; H2AFX; HIST1H2BB; HIST1H2BF; HIST1H2BH; HIST1H2BM; HIST1H4I; HIST1H4J; HIST1H4K; HIST1H4L; PCNA; TIMELESS |
| selective expression of chemokine receptors during t-cell polarization | 24 | 8 | 3.80E−06 | 1.00E−04 | 7.29 | CCL3; CCR4; CCR5; CSF2; CXCR4; IFNG; IL12RB2; IL4R |
| g1/s transition | 97 | 16 | 4.64E−06 | 1.22E−04 | 3.61 | CCNA2; CCNB1; CCNE1; CDC25A; CDC25B; CDC45; CDC6; CDK1; MCM10; ORC1; ORC6; PCNA; PSMA5; PSMB6; RRM2; TK1 |
| regulation of cytokine secretion: GO | 134] | 19 | 4.88E−06 | 1.27E−04 | 3.17 | CAMP; CCL3; CD2; CD274; IFNG; IL1B; IL26; IL36RN; IL4R; IL6; NLRP2; PYCARD; SLAMF1; SRGN; TNFRSF21; TNFRSF9; TRIM16; WNT5A; ZC3H12A |
| epigenetic regulation of gene expression | 87 | 15 | 5.06E−06 | 1.31E−04 | 3.77 | DDX21; H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L; UHRF1 |
| spindle midzone: GO | 25 | 8 | 5.39E−06 | 1.38E−04 | 7.00 | AURKA; BUB1B; CDC6; CDCA8; CENPE; KIF14; KIF18A; PLK1 |
| defense response to gram positive bacterium: GO | 58 | 12 | 5.67E−06 | 1.44E−04 | 4.52 | ACP5; C10orf99; CAMP; HIST1H2BE; HIST1H2BF; HIST1H2BG; HIST1H2BI; HIST1H2BJ; IL6; MYD88; PGLYRP2; RNASE7 |
| nuclear chromosome telomeric region: GO | 121 | 18 | 5.85E−06 | 1.48E−04 | 3.25 | CDK1; HIST1H2BB; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L; NLRP2; ORC1; PCNA; PIF1 |
| regulation of t cell proliferation: GO | 134 | 19 | 6.85E−06 | 1.72E−04 | 3.10 | CD274; CD3E; CD80; EBI3; IDO1; IFNG; IL12B; IL1B; IL2RA; IL6; JAK3; PNP; PRKCQ; PYCARD; RAC2; SASH3; SLAMF1; TNFRSF21; TNFSF9 |
| response to ethanol: GO | 123 | 18 | 7.41E−06 | 1.85E−04 | 3.20 | ADCYAP1; ADH7; BAK1; CCL7; CCNE1; CDK1; CTSB; EIF4EBP1; GGH; GK; GOT2; GSTP1; HTR3A; IL1B; NEU2; NTRK1; S100A8; TNC |
| defense response to fungus: GO | 26 | 8 | 7.52E−06 | 1.86E−04 | 6.73 | C10orf99; CAMP; COTL1; IL36RN; LTF; S100A12; S100A8; S100A9 |
| chromosome telomeric region: GO | 147 | 20 | 7.68E−06 | 1.89E−04 | 2.98 | BLM; CDK1; H2AFX; HIST1H2BB; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L; NLRP2; ORC1; PCNA; PIF1 |
| negative regulation of cytokine production: GO | 185 | 23 | 8.19E−06 | 2.00E−04 | 2.72 | ACP5; C1QBP; CD274; CDH3; GSTP1; HMOX1; IDO1; IFNG; IL12B; IL36RN; IL6; ISG15; JAK3; LTF; MEFV; NMI; PGLYRP2; PYCARD; SLAMF1; SRGN; TNFRSF21; TNFRSF9; ZC3H12A |
| histone binding: GO | 160 | 21 | 8.30E−06 | 2.02E−04 | 2.87 | ASF1B; CBX2; CDYL2; DTX3L; GK; H2AFX; HIST1H3A; HIST1H3B; HIST1H3C; HIST1H3F; HIST1H3G; HIST1H3H; HIST1H3I; HIST1H3J; HIST1H4I]; HIST1H4J; HIST1H4K; HIST1H4L; HJURP; RCC1; UHRF1 |
| cellular response to interferon gamma: GO | 113 | 17 | 8.82E−06 | 2.13E−04 | 3.29 | CCL18; CCL22; CCL3; CCL7; FCGR1A; GAPDH; GBP6; IFI30; IFNG; IL12B; OAS1; OAS2; OAS3; OASL; PTAFR; STAT1; WNT5A |
| hats acetylate histones | 61 | 12 | 9.85E−06 | 2.35E−04 | 4.30 | H2AFX; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L |
| regulation of sister chromatid segregation: GO | 61 | 12 | 9.85E−06 | 2.35E−04 | 4.30 | BUB1; BUB1B; CCNB1; CDC6; CDCA5; CENPE; DLGAP5; MAD2L1; PLK1; PTTG1; TTK; UBE2C |
| centromere complex assembly: GO | 43 | 10 | 1.04E−05 | 2.45E−04 | 5.09 | CENPA; CENPE; CENPN; CENPW; HIST1H4I; HIST1H4J; HIST1H4K; HIST1H4L; HJURP; OIP5 |
| regulation of interleukin 1 production: GO | 52 | 11 | 1.06E−05 | 2.49E−04 | 4.63 | ACP5; CCL3; GSTP1; IFI16; IFNG; MEFV; NLRP2; PYCARD; TRIM16; WNT5A; ZC3H12A |
| atp generation from adp: GO | 35 | 9 | 1.12E−05 | 2.63E−04 | 5.62 | ENO1; GAPDH; HK2; LDHA; OGDHL; PFKFB4; PGAM1; PGK1; TPI1 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| regulation of leukocyte proliferation: GO | 189 | 23 | 1.17E−05 | 2.72E−04 | 2.66 | CD274; CD3E; CD80; CTLA4; EBI3; GSTP1; IDO1; IFNG; IL12B; IL1B; IL2RA; IL6; JAK3; PNP; PRDM1; PRKCQ; PYCARD; RAC2; SASH3; SLAMF1; TNFRSF21; TNFRSF4; TNFSF9 |
| cell killing: GO | 44 | 10 | 1.29E−05 | 2.96E−04 | 4.97 | CAMP; CTSC; PRDX1; RAETIL; S100A12; SLAMF7; TREM1; ULBP1; ULBP2; ULBP3 |
| dna double strand break response | 44 | 10 | 1.29E−05 | 2.96E−04 | 4.97 | H2AFX; HIST1H2BB; HIST1H2BF; HIST1H2BH; HIST1H2BM; HIST1H4I; HIST1H4J; HIST1H4K; HIST1H4L; KPNA2 |
| cell cycle checkpoint: GO | 178 | 22 | 1.38E−05 | 3.16E−04 | 2.70 | AURKA; BIRC5; BLM; BUB1; BUB1B; CCNA2; CCNB1; CDC45; CDC6; CDK1; CLSPN; H2AFX; HMGA2; MAD2L1; PCNA; PLK1; PLK2; SFN; TOP2A; TTK; ZWILCH; ZWINT |
| positive regulation of gene expression epigenetic: GO | 73 | 13 | 1.39E−05 | 3.16E−04 | 3.89 | DDX21; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L |
| fra pathway | 36 | 9 | 1.44E−05 | 3.23E−04 | 5.47 | CCNA2; FOSL1; HMOX1; IL6; IVL; MMP1; MMP9; PLAU; PLAUR |
| nonhomologous end-joining (nhej) | 36 | 9 | 1.44E−05 | 3.23E−04 | 5.47 | H2AFX; HIST1H2BB; HIST1H2BF; HIST1H2BH; HIST1H2BM; HIST1H4I; HIST1H4J; HIST1H4K; HIST1H4L |
| peptide ligand-binding receptors | 54 | 11 | 1.55E−05 | 3.46E−04 | 4.45 | CCK; CXCL1; CXCL10; CXCL11; CXCL13; CXCL3; CXCL6; CXCL8; CXCR4; FPR1; PNP |
| hexose catabolic process: GO | 45 | 10 | 1.60E−05 | 3.54E−04 | 4.86 | ENO1; FUT1; FUT2; GAPDH; HK2; PFKFB4; PGAM1; PGK1; PGM2; TPI1 |
| anaphase promoting complex dependent catabolic process: GO | 74 | 13 | 1.62E−05 | 3.55E−04 | 3.84 | AURKA; BUB1B; CCNB1; CDC20; CDK1; MAD2L1; PLK1; PSMA4; PSMA5; PSMB6; PTTG1; UBE2C; UBE2S |
| mitotic cell cycle checkpoint: GO | 130 | 18 | 1.62E−05 | 3.55E−04 | 3.03 | AURKA; BLM; BUB1; BUB1B; CCNA2; CCNB1; CDK1; CLSPN; HMGA2; MAD2L1; PCNA; PLK1; PLK2; SFN; TOP2A; TTK; ZWILCH; ZWINT |
| regulation of chemotaxis: GO | 168 | 21 | 1.78E−05 | 3.87E−04 | 2.73 | ARTN; C1QBP; CALR; CCL3; CCL7; CXCL1; CXCL10; CXCL11; CXCL13; CXCL3; CXCL5; CXCL6; CXCL9; CXCR4; IL1B; IL6; RAC2; S100A14; S100A7; SERPINE1; WNT5A |
| nucleotide phosphorylation: GO | 55 | 11 | 1.87E−05 | 4.04E−04 | 4.37 | CMPK2; ENO1; GAPDH; HK2; LDHA; NME1; OGDHL; PFKFB4; PGAM1; PGK1; TPI1 |
| cell cycle g1 s phase transition: GO | 108 | 16 | 1.91E−05 | 4.09E−04 | 3.24 | CCNE1; CDC25A; CDC45; CDC6; CDCA5; CDK1; CDKN3; EIF4EBP1; MCM10; ORC1; ORC6; PCNA; PKMYT1; PLK2; RCC1; RRM2 |
| mhc class ii antigen presentation | 108 | 16 | 1.91E−05 | 4.09E−04 | 3.24 | AP1S3; CENPE; CTSB; CTSC; CTSL; IFI30; KIF11; KIF15; KIF18A; KIF20A; KIF23; KIF2C; KIF4A; TUBA1C; TUBB2A; TUBB6 |
| regulation of t cell differentiation: GO | 97 | 15 | 1.99E−05 | 4.23E−04 | 3.38 | CD2; CD80; CTLA4; IFNG; IL12B; IL1B; IL2RA; IL4R; IL6; IL7R; JAK3; PNP; PRELID1; SASH3; TNFSF9 |
| gene silencing by rna | 22 | 7 | 2.06E−05 | 4.35E−04 | 6.96 | H2AFX; H2AFZ; HIST1H2AE; HIST1H2BB; HIST1H2BF; HIST1H2BH; HIST1H2BM |
| regulation of apc/c activators between g1/s and early anaphase | 56 | 11 | 2.24E−05 | 4.68E−04 | 4.30 | BUB1; BUB1B; CCNA2; CCNB1; CDC20; CDK1; MAD2L1; PLK1; PSMA5; PSMB6; UBE2C |
| regulation of chemokine production: GO | 56 | 11 | 2.24E−05 | 4.68E−04 | 4.30 | ADCYAP1; GSTP1; HIF1A; HMOX1; IFNG; IL1B; IL4R; IL6; MEFV; PYCARD; WNT5A |
| interleukin-10 signaling | 38 | 9 | 2.32E−05 | 4.82E−04 | 5.18 | CCL3; CSF2; CXCL1; CXCL 10; CXCL3; CXCL8; FPR1; IL1B; IL6 |
| g2/m transition | 134 | 18 | 2.47E−05 | 5.08E−04 | 2.94 | AURKA; CCNA2; CCNB1; CCNB2; CDC25A; CDC25B; CDK1; FOXMI; HMMR; MYBL2; NEK2; PLK1; PSMA5; PSMB6; TPX2; TUBA1C; TUBB2A; TUBB6 |
| midbody: GO | 122 | 17 | 2.49E−05 | 5.08E−04 | 3.05 | ASPM; AURKA; BIRC5; CDCA8; CDK1; CENPE; CEP55; ECT2; KIF14; KIF20A; KIF23; KIF4A; NEK2; PITPNM1; PLK1; RALB; RAN |
| regulation of lymphocyte differentiation: GO | 122 | 17 | 2.49E−05 | 5.08E−04 | 3.05 | CD2; CD80; CTLA4; IFNG; IL12B; IL1B; IL2RA; IL4R; IL6; IL7R; JAK3; PGLYRP2; PNP; PRDM1; PRELID1; SASH3; TNFSF9 |
| regulation of microtubule polymerization | 159 | 20 | 2.51E−05 | 5.09E−04 | 2.75 | ASPM; AURKA; BIRC5; CCNB1; KIF11; KIF23; KIF4A; MYBL2; NDC80; NEK2; |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| or depolymerization: GO | | | | | | PLK1; PLK2; RAN; RCC1; SKA1; SKA3; SPC25; STIL; TPX2; TTK |
| serine hydrolase activity: GO | 185 | 22 | 2.55E−05 | 5.16E−04 | 2.60 | CPXM1; CTSB; CTSC; F12; GZMA; HABP2; IGHG4; KLK10; KLK13; KLK6; LTF; MMP1; MMP12; MMP3; MMP9; PCSK9; PLAU; PRSS22; PRSS27; PRSS3; TMPRSS11D; TMPRSS4 |
| regulation of gene expression epigenetic: GO | 199 | 23 | 2.72E−05 | 5.47E−04 | 2.53 | DDX21; H2AFX; H2AFZ; HIST1H2AB; HIST1H2AE; HIST1H2AG; HIST1H2AH; HIST1H2AI; HIST1H2AL; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L; IFI16; RAN |
| leukocyte mediated immunity: GO | 160 | 20 | 2.75E−05 | 5.50E−04 | 2.73 | C1QBP; CCL3; CTSC; CXCL5; CXCL6; EXO1; IGHG4; IL4R; IL6; NR4A3; PLA2G3; PRDX1; RAETIL; SERPINB9; SLAMF1; SLAMF7; TREM1; ULBP1; ULBP2; ULBP3 |
| antimicrobial peptides | 23 | 7 | 2.86E−05 | 5.68E−04 | 6.66 | CAMP; LCN2; LYZ; PGLYRP2; PI3; S100A8; S100A9 |
| carbohydrate catabolic process: GO | 100 | 15 | 2.89E−05 | 5.72E−04 | 3.28 | ENO1; FUT1; FUT2; GAPDH; GK; HK2; LDHA; NEU2; OGDHL; PFKFB4; PGAM1; PGK1; PGM2; PYGL; TPI1 |
| rmts methylate histone arginines | 39 | 9 | 2.91E−05 | 5.72E−04 | 5.05 | H2AFX; H2AFZ; HIST1H2AE; HIST1H3A; HIST1H3I; HIST1H4I; HIST1H4J; HIST1H4K; HIST1H4L |
| dna replication independent nucleosome organization: GO | 48 | 10 | 2.93E−05 | 5.73E−04 | 4.56 | ASF1B; CENPA; CENPN; CENPW; HIST1H4I; HIST1H4J; HIST1H4K; HIST1H4L; HJURP; OIP5 |
| mitotic g2-g2/m phases | 136 | 18 | 3.03E−05 | 5.90E−04 | 2.89 | AURKA; CCNA2; CCNB1; CCNB2; CDC25A; CDC25B; CDK1; FOXMI; HMMR; MYBL2; NEK2; PLK1; PSMA5; PSMB6; TPX2; TUBA1C; TUBB2A; TUBB6 |
| peptidase regulator activity: GO | 174 | 21 | 3.04E−05 | 5.90E−04 | 2.64 | A2ML1; BIRC5; CST7; CSTA; CSTB; CTSC; PI15; PI3; PTTG1; PYCARD; SERPINA1; SERPINB1; SERPINB13; SERPINB3; SERPINB4; SERPINB9; SERPINE1; SLPI; SPINK6; VCP; WFDC12 |
| pyruvate metabolic process: GO | 58 | 11 | 3.17E−05 | 6.11E−04 | 4.15 | ENO1; GAPDH; HK2; LDHA; NR4A3; OGDHL; PFKFB4; PGAM1; PGK1; SLC16A1; TPI1 |
| g alpha (i) signalling events | 69 | 12 | 3.65E−05 | 7.00E−04 | 3.80 | CXCL1; CXCL10; CXCL11; CXCL13; CXCL3; CXCL6; CXCL8; CXCR4; FPR1; PNP; RGS1; RGS20 |
| positive regulation of interferon gamma production: GO | 59 | 11 | 3.75E−05 | 7.16E−04 | 4.08 | CD2; CD3E; EBI3; IL12B; IL12RB2; IL1B; PYCARD; SASH3; SLAMF1; TNFSF9; WNT5A |
| positive regulation of mitotic cell cycle: GO | 114 | 16 | 3.81E−05 | 7.22E−04 | 3.07 | AURKA; BIRC5; CCNB1; CDC25B; CDC45; CDC6; CDCA5; CDK1; DLGAP5; EIF4EBP1; EPGN; IL1B; MAD2L1; PLK1; TGFA; UBE2C |
| leukocyte mediated cytotoxicity: GO | 32 | 8 | 4.08E−05 | 7.67E−04 | 5.47 | CTSC; PRDX1; RAETIL; SLAMF7; TREM1; ULBP1; ULBP2; ULBP3 |
| peptidase inhibitor activity: GO | 139 | 18 | 4.08E−05 | 7.67E−04 | 2.83 | A2ML1; BIRC5; CST7; CSTA; CSTB; PI15; PI3; PTTG1; SERPINA1; SERPINB1; SERPINB13; SERPINB3; SERPINB4; SERPINB9; SERPINE1; SLPI; SPINK6; WFDC12 |
| positive regulation of leukocyte proliferation: GO | 127 | 17 | 4.22E−05 | 7.88E−04 | 2.93 | CD274; CD3E; CD80; EBI3; IFNG; IL12B; IL1B; IL2RA; IL6; JAK3; PNP; PRKCQ; PYCARD; SASH3; SLAMF1; TNFRSF4; TNFSF9 |
| positive regulation of alpha beta t cell activation: GO | 50 | 10 | 4.26E−05 | 7.89E−04 | 4.37 | CD3E; CD80; EBI3; IFNG; IL12B; IL4R; IL6; PNP; PRKCQ; SASH3 |
| production: GO | 50 | 10 | 4.26E−05 | 7.89E−04 | 4.37 | ACP5; C1QBP; IDO1; IFNG; IL12B; JAK3; MEFV; SLAMF1; TNFRSF9; TNFSF9 |
| gene silencing: GO | 178 | 21 | 4.28E−05 | 7.89E−04 | 2.58 | H2AFX; H2AFZ; HIST1H2AB; HIST1H2AE; HIST1H2AG; HIST 1H2AH; HIST1H2AI; HIST 1H2AL; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L; RAN |
| apc:cdc20 mediated degradation of cell cycle proteins prior to satisfation of the cell cycle checkpoint | 51 | 10 | 5.10E−05 | 9.26E−04 | 4.29 | BUB1; BUB1B; CCNA2; CDC20; CDK1; MAD2L1; NEK2; PSMA5; PSMB6; UBE2C |
| glycolysis | 51 | 10 | 5.10E−05 | 9.26E−04 | 4.29 | ENO1; GAPDH; GK; HK2; PFKFB4; PGAM1; PGK1; PKM; TPI1; TPIIP1 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| positive regulation of cytokine biosynthetic process: GO | 51 | 10 | 5.10E−05 | 9.26E−04 | 4.29 | CD3E; CD80; EBI3; HMOX1; IFNG; IL12B; IL1B; PRKCQ; PTAFR; WNT5A |
| il12 2pathway | 61 | 11 | 5.19E−05 | 9.30E−04 | 3.94 | CCL3; CCR5; CD3E; EOMES; GZMA; IFNG; IL12B; IL12RB2; IL1B; IL2RA; STAT1 |
| nadh metabolic process: GO | 33 | 8 | 5.19E−05 | 9.30E−04 | 5.30 | ENO1; GAPDH; HK2; PFKFB4; PGAM1; PGK1; TPI1; VCP |
| chromosome condensation: GO | 25 | 7 | 5.22E−05 | 9.30E−04 | 6.12 | CCNB1; CDCA5; CDK1; HMGA2; NCAPG; NCAPH; TOP2A |
| il27 pathway | 25 | 7 | 5.22E−05 | 9.30E−04 | 6.12 | EBI3; IFNG; IL12B; IL12RB2; IL1B; IL6; STAT1 |
| tef dependent signaling in response to wnt | 117 | 16 | 5.26E−05 | 9.32E−04 | 2.99 | H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L; PSMA5; PSMB6; WNT5A |
| positive regulation of chemokine production: GO | 42 | 9 | 5.48E−05 | 9.65E−04 | 4.69 | ADCYAP1; HIF1A; HMOX1; IFNG; IL1B; IL4R; IL6; PYCARD; WNT5A |
| regulation of protein complex disassembly: GO | 195 | 22 | 5.75E−05 | 1.01E−03 | 2.47 | ASPM; AURKA; BIRC5; CCNB1; EIF5A; EIF5AL1; KIF11; KIF23; KIF4A; MYBL2; NDC80; NEK2; PLK1; PLK2; RAN; RCC1; SH3BGRL3; SPC25; STIL; TPX2; TTK; TWF1 |
| division: GO | 52 | 10 | 6.09E−05 | 1.06E−03 | 4.21 | AURKA; BIRC5; CDCA5; DLGAP5; EPGN; IL1B; PLK1; TGFA; UBE2C; WNT5A |
| adp metabolic process: GO | 43 | 9 | 6.67E−05 | 1.15E−03 | 4.58 | ENO1; GAPDH; HK2; LDHA; OGDHL; PFKFB4; PGAM1; PGK1; TPI1 |
| positive regulation of mitotic nuclear division: GO | 43 | 9 | 6.67E−05 | 1.15E−03 | 4.58 | AURKA; BIRC5; CDCA5; DLGAP5; EPGN; IL1B; PLK1; TGFA; UBE2C |
| recruitment and atm-mediated phosphorylation of repair and signaling proteins at dna double strand breaks | 43 | 9 | 6.67E−05 | 1.15E−03 | 4.58 | H2AFX; HIST1H2BB; HIST1H2BF; HIST1H2BH; HIST1H2BM; HIST1H4I; HIST1H4J; HIST1H4K; HIST1H4L |
| positive regulation of lymphocyte migration: GO | 26 | 7 | 6.90E−05 | 1.17E−03 | 5.89 | CCL3; CCL7; CXCL 10; CXCL13; PYCARD; S100A7; WNT5A |
| positive regulation of release of cytochrome c from mitochondria: GO | 26 | 7 | 6.90E−05 | 1.17E−03 | 5.89 | BAK1; FAM162A; MMP9; PLAUR; PPIF; PYCARD; TNFSF10 |
| regulation of transcription involved in g1 s transition of mitotic cell cycle: GO | 26 | 7 | 6.90E−05 | 1.17E−03 | 5.89 | CCNE1; CDC45; CDC6; CDK1; ORC1; PCNA; RRM2 |
| oxidoreduction coenzyme metabolic process: GO | 96 | 14 | 7.06E−05 | 1.19E−03 | 3.19 | ENO1; GAPDH; HK2; KYNU; LDHA; NAMPT; OGDHL; PFKFB4; PGAM1; PGK1; PGM2; PNP; TPI1; VCP |
| negative regulation of immune response: GO | 108 | 15 | 7.26E−05 | 1.22E−03 | 3.04 | ADCYAP1; FOXF1; HMOX1; IFI16; IL12B; IL2RA; IL4R; IL7R; JAK3; NMI; PGLYRP2; SAMSN1; SERPINB4; SERPINB9; SLAMF1 |
| positive regulation of lymphocyte differentiation: GO | 74 | 12 | 7.49E−05 | 1.25E−03 | 3.55 | CD80; IFNG; IL12B; IL1B; IL2RA; IL4R; IL6; IL7R; PNP; PRDM1; SASH3; TNFSF9 |
| regulation of cysteine type endopeptidase activity: GO | 199 | 22 | 7.82E−05 | 1.30E−03 | 2.42 | BAK1; BIRC5; CCK; CYCS; FAM162A; IFI16; IFI27; IFI6; IL6; LAMP3; MEFV; MMP9; NLRP2; PLAUR; PYCARD; S100A8; S100A9; SERPINB9; SFN; SOX7; TNFSF10; VCP |
| defense response to gram negative bacterium: GO | 35 | 8 | 8.19E−05 | 1.36E−03 | 5.00 | CAMP; IL12B; IL6; PYCARD; RNASE7; S100A7; SERPINE1; TREM1 |
| granulocyte migration: GO | 64 | 11 | 8.23E−05 | 1.36E−03 | 3.76 | CCL18; CCL22; CCL3; CCL7; CXCL3; IFNG; IL1B; S100A12; S100A8; S100A9; TREM1 |
| chromosome localization: GO | 54 | 10 | 8.54E−05 | 1.40E−03 | 4.05 | BIRC5; CCNB1; CDCA5; CDCA8; CENPE; CEP55; DLGAP5; KIF14; KIF18A; KIF2C |
| monosaccharide catabolic process: GO | 54 | 10 | 8.54E−05 | 1.40E−03 | 4.05 | ENO1; FUT1; FUT2; GAPDH; HK2; PFKFB4; PGAM1; PGK1; PGM2; TPI1 |
| telomere organization: GO | 98 | 14 | 8.90E−05 | 1.45E−03 | 3.12 | HIST1H3A; HIST1H3B; HIST1H3C; HIST1H3F; HIST1H3G; HIST1H3H; HIST1H3I; HIST1H3J; HIST1H4I;HIST1H4J; HIST1H4K; HIST1H4L; PCNA; PIF1 |
| glucose catabolic process: GO | 27 | 7 | 9.00E−05 | 1.46E−03 | 5.67 | ENO1; GAPDH; HK2; PFKFB4; PGAM1; PGK1; TPI1 |
| positive regulation of cd4 positive alpha beta t cell activation: GO | 27 | 7 | 9.00E−05 | 1.46E−03 | 5.67 | CD80; IFNG; IL12B; IL4R; IL6; PRKCQ; SASH3 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| copi-dependent golgi-to-er retrograde traffic | 65 | 11 | 9.53E−05 | 1.52E−03 | 3.70 | CENPE; KIF11; KIF15; KIF18A; KIF20A; KIF23; KIF2C; KIF4A; TUBA1C; TUBB2A; TUBB6 |
| positive regulation of stat cascade: GO | 65 | 11 | 9.53E−05 | 1.52E−03 | 3.70 | CSF2; IFNG; IL12B; IL19; IL20; IL22; IL24; IL26; IL6; OSM; SOCS3 |
| activation: GO | 65 | 11 | 9.53E−05 | 1.52E−03 | 3.70 | CD3E; CD80; EBI3; IFNG; IL12B; IL4R; IL6; JAK3; PNP; PRKCQ; SASH3 |
| spindle pole: GO | 111 | 15 | 9.99E−05 | 1.59E−03 | 2.96 | ASPM; AURKA; CCNB1; CDC20; CDC25B; CDC6; CKAP2L; DLGAP5; FAM110C; KIF11; MAD2L1; NEK2; PLK1; POC1A; TPX2 |
| negative regulation of cell division: GO | 55 | 10 | 1.00E−04 | 1.59E−03 | 3.98 | ASPM; BLM; BUB1; BUB1B; C10orf99; MAD2L1; OSM; PLK1; PTTG1; TTK |
| proliferation: GO | 36 | 8 | 1.02E−04 | 1.59E−03 | 4.86 | CD274; IDO1; IL12B; IL2RA; JAK3; PYCARD; SLAMF1; TNFSF9 |
| regulation of cd4 positive alpha beta t cell activation: GO | 36 | 8 | 1.02E−04 | 1.59E−03 | 4.86 | CD80; IFNG; IL12B; IL4R; IL6; JAK3; PRKCQ; SASH3 |
| genes | 36 | 8 | 1.02E−04 | 1.59E−03 | 4.86 | AURKA; CCNA2; CCNB1; CCNE1; CDK1; PCNA; PLK2; SFN |
| glucose metabolism | 88 | 13 | 1.07E−04 | 1.67E−03 | 3.23 | ENO1; GAPDH; GK; GOT2; HK2; PFKFB4; PGAM1; PGK1; PGM2; PKM; PYGL; TPI1; TPI1P1 |
| regulation of lymphocyte chemotaxis: GO | 20 | 6 | 1.09E−04 | 1.69E−03 | 6.56 | CCL3; CCL7; CXCL 10; CXCL13; S100A7; WNT5A |
| positive regulation of inflammatory response: GO | 101 | 14 | 1.24E−04 | 1.91E−03 | 3.03 | CCL18; CCL3; CCL7; F12; IDO1; IL12B; IL1B; IL6; OSM; S100A12; S100A8; S100A9; SERPINE1; WNT5A |
| formation of the cornified envelope | 37 | 8 | 1.25E−04 | 1.91E−03 | 4.73 | CSTA; DSG3; IVL; KRT16; KRT17; PI3; SPRR2A; SPRR2B |
| natural killer cell activation: GO | 37 | 8 | 1.25E−04 | 1.91E−03 | 4.73 | CD2; IFNE; IL12B; SLAMF1; SLAMF7; ULBP1; ULBP2; ULBP3 |
| upa upar pathway | 37 | 8 | 1.25E−04 | 1.91E−03 | 4.73 | FPR1; FPR3; MMP12; MMP3; MMP9; PLAU; PLAUR; SERPINE1 |
| nucleoside diphosphate metabolic process: GO | 78 | 12 | 1.27E−04 | 1.93E−03 | 3.36 | CMPK2; ENO1; GAPDH; HK2; LDHA; NME1; OGDHL; PFKFB4; PGAM1; PGK1; RRM2; TPI1 |
| positive regulation of cytokine secretion: GO | 90 | 13 | 1.36E−04 | 2.05E−03 | 3.16 | CAMP; CCL3; CD2; CD274; IFNG; IL1B; IL26; IL4R; NLRP2; PYCARD; SLAMF1; TRIM16; WNT5A |
| histone exchange: GO | 47 | 9 | 1.39E−04 | 2.09E−03 | 4.19 | CENPA; CENPN; CENPW; HIST1H4I; HIST1H4J; HIST1H4K; HIST1H4L; HJURP; OIP5 |
| serine type endopeptidase inhibitor activity: GO | 79 | 12 | 1.44E−04 | 2.16E−03 | 3.32 | A2ML1; PI3; SERPINA1; SERPINB1; SERPINB13; SERPINB3; SERPINB4; SERPINB9; SERPINE1; SLPI; SPINK6; WFDC12 |
| negative regulation of protein complex disassembly: GO | 153 | 18 | 1.45E−04 | 2.16E−03 | 2.57 | ASPM; AURKA; BIRC5; CCNB1; KIF11; KIF23; KIF4A; MYBL2; NDC80; NEK2; PLK2; RAN; RCC1; SPC25; STIL; TPX2; TTK; TWF1 |
| positive regulation of interleukin 1 beta production: GO | 29 | 7 | 1.48E−04 | 2.20E−03 | 5.28 | CCL3; IFI16; IFNG; NLRP2; PYCARD; TRIM16; WNT5A |
| regulation of production of molecular mediator of immune response: GO | 91 | 13 | 1.52E−04 | 2.25E−03 | 3.12 | DEFB103A; DEFB103B; HMOX1; IFNG; IL4R; IL6; JAK3; NR4A3; RSAD2; SASH3; SLAMF1; TNFRSF4; WNT5A |
| regulation of tumor necrosis factor superfamily cytokine production: GO | 91 | 13 | 1.52E−04 | 2.25E−03 | 3.12 | ACP5; CCL3; CD2; CD274; GSTP1; IFNG; IL12B; LTF; PTAFR; PYCARD; SASH3; SLAMF1; ZC3H12A |
| class a/1 (rhodopsin-like receptors) | 80 | 12 | 1.63E−04 | 2.39E−03 | 3.28 | CCK; CXCL1; CXCL10; CXCL11; CXCL13; CXCL3; CXCL6; CXCL8; CXCR4; FPR1; LTB4R; PNP |
| condensed nuclear chromosome: GO | 69 | 11 | 1.67E−04 | 2.44E−03 | 3.49 | AURKA; BLM; BUB1; BUB1B; CCNB1; CENPA; H2AFX; NDC80; NEK2; PLK1; RCC1 |
| activation of atr in response to replication stress | 39 | 8 | 1.85E−04 | 2.66E−03 | 4.49 | CDC25A; CDC25B; CDC45; CDC6; CLSPN; MCM10; ORC1; ORC6 |
| immunity: GO | 39 | 8 | 1.85E−04 | 2.66E−03 | 4.49 | CCL3; CXCL5; CXCL6; IL6; NR4A3; PLA2G3; SERPINB9; TREM1 |
| molecular mediator of immune response: GO | 59 | 10 | 1.86E−04 | 2.66E−03 | 3.71 | DEFB103A; DEFB103B; IFNG; IL4R; IL6; NR4A3; RSAD2; SASH3; TNFRSF4; WNT5A |
| aurora a pathway | 30 | 7 | 1.86E−04 | 2.66E−03 | 5.10 | AURKA; BIRC5; CDC25B; CENPA; DLGAP5; RAN; TPX2 |
| regulation of interleukin 1 secretion: GO | 30 | 7 | 1.86E−04 | 2.66E−03 | 5.10 | CCL3; IFNG; NLRP2; PYCARD; TRIM16; WNT5A; ZC3H12A |
| regulation of t cell apoptotic process: GO | 30 | 7 | 1.86E−04 | 2.66E−03 | 5.10 | CD274; HIF1A; IDO1; JAK3; PRELID1; PRKCQ; WNT5A |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| oocyte meiosis | 105 | 14 | 1.90E−04 | 2.70E−03 | 2.92 | AURKA; BUB1; CALML3; CALML5; CCNB1; CCNB2; CCNE1; CDC20; CDK1; MAD2L1; PKMYT1; PLK1; PTTG1; YWHAQ |
| release of cytochrome c from mitochondria: GO | 22 | 6 | 1.97E−04 | 2.79E−03 | 5.96 | BAK1; BCL2A1; CCK; GGCT; IFI6; SFN |
| interferon gamma signaling | 82 | 12 | 2.07E−04 | 2.93E−03 | 3.20 | FCGR1A; GBP6; IFI30; IFNG; OAS1; OAS2; OAS3; OASL; PTAFR; SOCS3; STAT1; TRIM14 |
| chemokine signaling pathway | 171 | 19 | 2.09E−04 | 2.95E−03 | 2.43 | CCL18; CCL22; CCL3; CCL7; CCR4; CCR5; CXCL1; CXCL10; CXCL11; CXCL13; CXCL3; CXCL5; CXCL6; CXCL9; CXCR4; GNGT2; JAK3; RAC2; STAT1 |
| protein heterooligomerization: GO | 106 | 14 | 2.10E−04 | 2.95E−03 | 2.89 | CHRNA3; HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L; RRM2 |
| regulation of interleukin 6 production: GO | 94 | 13 | 2.13E−04 | 2.98E−03 | 3.02 | ADCYAP1; IFNG; IL1B; IL36A; IL36RN; IL6; MYD88; PTAFR; PYCARD; SLAMF1; TNFSF9; WNT5A; ZC3H12A |
| glycolysis / gluconeogenesis | 60 | 10 | 2.14E−04 | 2.99E−03 | 3.64 | ADH7; ALDH1A3; ENO1; GAPDH; HK2; LDHA; PGAM1; PGK1; PKM; TPI1 |
| regulation of release of cytochrome c from mitochondria: GO | 40 | 8 | 2.24E−04 | 3.10E−03 | 4.37 | BAK1; FAM162A; MMP9; PLAUR; PPIF; PRELID1; PYCARD; TNFSF10 |
| cdc20:phospho-apc/c mediated degradation of cyclin a | 50 | 9 | 2.29E−04 | 3.17E−03 | 3.94 | BUB1; BUB1B; CCNA2; CDC20; CDK1; MAD2L1; PSMA5; PSMB6; UBE2C |
| response to vitamin d: GO | 31 | 7 | 2.32E−04 | 3.20E−03 | 4.94 | ALPL; AQP3; CXCL10; CYP24A1; CYP27B1; IL1B; TNC |
| positive regulation of immune effector process: GO | 146 | 17 | 2.43E−04 | 3.34E−03 | 2.55 | CD80; DEFB103A; DEFB103B; FOXF1; HMOX1; IFNG; IL12B; IL1B; IL4R; IL6; NR4A3; PTAFR; RAC2; RSAD2; SASH3; TNFRSF4; WNT5A |
| immunity: GO | 23 | 6 | 2.57E−04 | 3.49E−03 | 5.70 | PRDX1; RAETIL; SLAMF7; ULBP1; ULBP2; ULBP3 |
| nucleobase catabolism | 23 | 6 | 2.57E−04 | 3.49E−03 | 5.70 | ENTPD7; NUDT15; PNP; POMP; TYMP; UPP1 |
| spindle checkpoint: GO | 23 | 6 | 2.57E−04 | 3.49E−03 | 5.70 | BIRC5; BUB1; BUB1B; MAD2L1; PLK1; TTK |
| cysteine type endopeptidase inhibitor activity: GO | 41 | 8 | 2.68E−04 | 3.61E−03 | 4.27 | BIRC5; CST7; CSTA; CSTB; PTTG1; SERPINB13; SERPINB3; SERPINB9 |
| metaphase plate congression: GO | 41 | 8 | 2.68E−04 | 3.61E−03 | 4.27 | CCNB1; CDCA5; CDCA8; CENPE; CEP55; KIF14; KIF18A; KIF2C |
| e2f pathway | 73 | 11 | 2.79E−04 | 3.75E−03 | 3.30 | CCNA2; CCNE1; CDC25A; CDC6; CDK1; MYBL2; ORC1; PLAU; RRM2; SERPINE1; TK1 |
| gluconeogenesis | 32 | 7 | 2.87E−04 | 3.84E−03 | 4.78 | ENO1; GAPDH; GOT2; PGAMI; PGK1; TPI1; TPI1P1 |
| protease binding: GO | 97 | 13 | 2.93E−04 | 3.89E−03 | 2.93 | ADAMTS4; CSTA; CSTB; LDLR; PYCARD; SELL; SERPINA1; SERPINB13; SERPINB3; SERPINB4; SERPINB9; SERPINE1; VCP |
| regulation of cytokine biosynthetic process: GO | 85 | 12 | 2.93E−04 | 3.89E−03 | 3.09 | CD3E; CD80; EBI3; HMOX1; IFNG; IL12B; IL1B; IL6; NMI; PRKCQ; PTAFR; WNT5A |
| response to reactive oxygen species: GO | 176 | 19 | 3.04E−04 | 4.03E−03 | 2.36 | AREG; BAK1; CCNA2; CDK1; CYCS; ECT2; FOSL1; GSTP1; HIF1A; HMOX1; IL1B; IL6; LDHA; MMP3; NR4A3; OLR1; PPIF; PRDX1; S100A7 |
| kinesin complex: GO | 52 | 9 | 3.12E−04 | 4.12E−03 | 3.78 | CENPE; KIF11; KIF14; KIF15; KIF18A; KIF20A; KIF23; KIF2C; KIF4A |
| production: GO | 42 | 8 | 3.19E−04 | 4.20E−03 | 4.17 | CD274; IDO1; IL12B; JAK3; PYCARD; SASH3; TNFRSF21; TNFRSF9 |
| positive regulation of interleukin 6 production: GO | 63 | 10 | 3.25E−04 | 4.25E−03 | 3.47 | ADCYAP1; IFNG; IL1B; IL36A; IL6; MYD88; PTAFR; PYCARD; TNFSF9; WNT5A |
| myeloid leukocyte migration: GO | 86 | 12 | 3.27E−04 | 4.27E−03 | 3.05 | CCL18; CCL22; CCL3; CCL7; CXCL3; IFNG; IL1B; IL6; S100A12; S100A8; S100A9; TREM1 |
| cell cycle: g2/m checkpoint | 24 | 6 | 3.32E−04 | 4.27E−03 | 5.47 | CCNB1; CDC25A; CDC25B; CDK1; PLK1; YWHAQ |
| g2 pathway | 24 | 6 | 3.32E−04 | 4.27E−03 | 5.47 | CCNB1; CDC25A; CDC25B; CDK1; PLK1; YWHAQ |
| positive regulation of activated t cell proliferation: GO | 24 | 6 | 3.32E−04 | 4.27E−03 | 5.47 | IL12B; IL2RA; JAK3; PYCARD; SLAMF1; TNFSF9 |
| positive regulation of interleukin 1 secretion: GO | 24 | 6 | 3.32E−04 | 4.27E−03 | 5.47 | CCL3; IFNG; NLRP2; PYCARD; TRIM16; WNT5A |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| cytokine production: GO | 111 | 14 | 3.42E−04 | 4.39E−03 | 2.76 | EOMES; HIF1A; IDO1; IL12B; IL12RB2; IL19; IL1B; PNP; PTAFR; S100A12; S100A8; S100A9; SLAMF1; TREM1 |
| negative regulation of cell cycle phase transition: GO | 137 | 16 | 3.46E−04 | 4.42E−03 | 2.55 | AURKA; BLM; BUB1; BUB1B; C10orf99; CCNA2; CCNB1; CDK1; CL SPN; HMGA2; MAD2L1; PCNA; PLK1; PLK2; SFN; TTK |
| dna repair | 33 | 7 | 3.51E−04 | 4.48E−03 | 4.64 | CCNA2; HIST1H2BB; HIST1H2BF; HIST1H2BH; HIST1H2BM; KPNA2; TIMELESS |
| sumo e3 ligases sumoylate target proteins | 75 | 11 | 3.56E−04 | 4.52E−03 | 3.21 | AURKA; BIRC5; BLM; CBX2; CDCA8; HIST1H4I; HIST1H4J; HIST1H4K; HIST1H4L; PCNA; TOP2A |
| apc c cdc20 mediated degradation of mitotic proteins | 64 | 10 | 3.71E−04 | 4.69E−03 | 3.42 | BUB1B; CCNB1; CDC20; CDK1; MAD2L1; PSMA4; PSMA5; PSMB6; PTTG1; UBE2C |
| lymphocyte migration: GO | 43 | 8 | 3.78E−04 | 4.77E−03 | 4.07 | ARTN; CCL18; CCL22; CCL3; CXCL 10; CXCL11; CXCL 13; GPR15 |
| mye activ pathway | 76 | 11 | 4.00E−04 | 5.03E−03 | 3.17 | BIRC5; CCNB1; CDC25A; ENO1; FOSL1; GAPDH; LDHA; MMP9; NME1; RCC1; TK1 |
| ub-specific processing proteases | 113 | 14 | 4.13E−04 | 5.17E−03 | 2.71 | CCNA2; CDC20; CDC25A; CDC25B; CLSPN; H2AFX; HIF1A; HIST1H2AE; HIST1H2BB; HIST1H2BF; HIST1H2BH; HIST1H2BM; PSMA5; PSMB6 |
| the role of gtsel in g2/m progression after g2 checkpoint | 54 | 9 | 4.19E−04 | 5.22E−03 | 3.64 | CCNB1; CCNB2; CDK1; PLK1; PSMA5; PSMB6; TUBA1C; TUBB2A; TUBB6 |
| spindle assembly: GO | 65 | 10 | 4.22E−04 | 5.22E−03 | 3.36 | ASPM; AURKA; BIRC5; KIF11; KIF23; KIF4A; MYBL2; NEK2; RCC1; TPX2 |
| hdms demethylate histones | 25 | 6 | 4.22E−04 | 5.22E−03 | 5.25 | HIST1H3A; HIST1H3I; HIST1H4I]; HIST1H4J; HIST1H4K; HIST1H4L |
| negative regulation of chromosome segregation: GO | 25 | 6 | 4.22E−04 | 5.22E−03 | 5.25 | BUB1; BUB 1B; MAD2L1; PLK1; PTTG1; TTK |
| positive regulation of interleukin 1 production: GO | 34 | 7 | 4.27E−04 | 5.26E−03 | 4.50 | CCL3; IFI16; IFNG; NLRP2; PYCARD; TRIM16; WNT5A |
| zymogen activation: GO | 101 | 13 | 4.38E−04 | 5.38E−03 | 2.81 | BAK1; CCK; CYCS; F12; FAM162A; IFI16; IFI27; PRSS3; PYCARD; S100A8; S100A9; TNFSF10; VCP |
| regulation of alpha beta t cell differentiation: GO | 44 | 8 | 4.46E−04 | 5.46E−03 | 3.98 | CD80; IFNG; IL12B; IL4R; IL6; JAK3; PNP; SASH3 |
| growth factor receptor binding: GO | 114 | 14 | 4.52E−04 | 5.50E−03 | 2.69 | AREG; CSF2; EPGN; ESM1; HBEGF; IL12B; IL1B; IL36A; IL36G; IL36RN; IL6; PYCARD; TGFA; TYMP |
| negative regulation of defense response: GO | 127 | 15 | 4.53E−04 | 5.50E−03 | 2.58 | ACP5; ADCYAP1; C1QBP; FOXF1; GSTP1; IFI16; IL12B; IL2RA; MEFV; NMI; PBK; SERPINB4; SERPINB9; SOCS3; ZC3H12A |
| positive regulation of response to wounding: GO | 141 | 16 | 4.80E−04 | 5.81E−03 | 2.48 | CCL18; CCL3; CCL7; F12; HBEGF; HPSE; IDO1; IL12B; IL1B; IL6; OSM; S100A12; S100A8; S100A9; SERPINE1; WNT5A |
| regulation of granulocyte chemotaxis: GO | 35 | 7 | 5.16E−04 | 6.23E−03 | 4.37 | C1QBP; CXCL1; CXCL3; IL1B; RAC2; S100A14; S100A7 |
| negative regulation of mitotic cell cycle: GO | 184 | 19 | 5.34E−04 | 6.43E−03 | 2.26 | AURKA; BLM; BUB1; BUB1B; CCNA2; CCNB1; CDK1; CLSPN; HMGA2; MAD2L1; PCNA; PLK1; PLK2; PTTG1; SFN; TOP2A; TTK; ZWILCH; ZWINT |
| spindle microtubule: GO | 56 | 9 | 5.55E−04 | 6.66E−03 | 3.51 | AURKA; BIRC5; CDK1; KIF11; KIF18A; KIF4A; PLK1; SKA1; SKA3 |
| positive regulation of alpha beta t cell differentiation: GO | 36 | 7 | 6.19E−04 | 7.38E−03 | 4.25 | CD80; IFNG; IL12B; IL4R; IL6; PNP; SASH3 |
| regulation of lymphocyte migration: GO | 36 | 7 | 6.19E−04 | 7.38E−03 | 4.25 | CCL3; CCL7; CXCL 10; CXCL13; PYCARD; S100A7; WNT5A |
| glutathione conjugation | 27 | 6 | 6.61E−04 | 7.85E−03 | 4.86 | CHAC1; CHAC2; CNDP2; GGCT; GSTO1; GSTP1 |
| s phase | 132 | 15 | 6.84E−04 | 8.11E−03 | 2.49 | CCNA2; CCNE1; CDC25A; CDC25B; CDC45; CDC6; CDCA5; ESCO2; GINS3; ORC1; ORC6; PCNA; PSMA4; PSMA5; PSMB6 |
| sumoylation | 81 | 11 | 7.00E−04 | 8.26E−03 | 2.97 | AURKA; BIRC5; BLM; CBX2; CDCA8; HIST1H4I; HIST1H4J; HIST1H4K; HIST1H4L; PCNA; TOP2A |
| mitotic spindle assembly: GO | 37 | 7 | 7.37E−04 | 8.65E−03 | 4.14 | BIRC5; KIF11; KIF23; KIF4A; MYBL2; NEK2; TPX2 |
| secretion: GO | 37 | 7 | 7.37E−04 | 8.65E−03 | 4.14 | IL36RN; IL6; SLAMF1; SRGN; TNFRSF21; TNFRSF9; ZC3H12A |
| dna integrity checkpoint: GO | 134 | 15 | 8.02E−04 | 9.38E−03 | 2.45 | AURKA; BLM; CCNA2; CCNB1; CDC45; CDC6; CDK1; CLSPN; H2AFX; HMGA2; |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| | | | | | | PCNA; PLK1; PLK2; SFN; TOP2A |
| positive regulation of peptidase activity: GO | 148 | 16 | 8.21E−04 | 9.57E−03 | 2.36 | BAK1; CCK; CYCS; FAM162A; IFI16; IFI27; MEFV; NLRP2; PRELID1; PYCARD; S100A8; S100A9; SERPINB3; SOX7; TNFSF10; VCP |
| positive regulation of smooth muscle cell proliferation: GO | 59 | 9 | 8.24E−04 | 9.57E−03 | 3.34 | HBEGF; HIF1A; HMOX1; IL6; NAMPT; NR4A3; ORC1; PTAFR; STAT1 |
| interaction with host: GO | 121 | 14 | 8.30E−04 | 9.62E−03 | 2.53 | CCR5; CD80; CTSB; CXCR4; ITGB6; KPNA2; LAMP3; LDLR; SERPINB3; SERPINB9; SLAMF1; TAP2; TNFRSF4; ZC3H12A |
| ribonucleoside diphosphate metabolic process: GO | 60 | 9 | 9.34E−04 | 1.08E−02 | 3.28 | ENO1; GAPDH; HK2; LDHA; OGDHL; PFKFB4; PGAM1; PGK1; TPI1 |
| production: GO | 20 | 5 | 9.60E−04 | 1.10E−02 | 5.47 | IFNG; IL12B; IL36RN; MYD88; PRKCQ |
| response to interferon alpha: GO | 20 | 5 | 9.60E−04 | 1.10E−02 | 5.47 | IFIT3; IFITM1; IFITM3; LAMP3; OAS1 |
| g2 dna damage checkpoint: GO | 29 | 6 | 9.92E−04 | 1.14E−02 | 4.52 | BLM; CCNA2; CDK1; CLSPN; HMGA2; PLK1 |
| drug binding: GO | 97 | 12 | 9.96E−04 | 1.14E−02 | 2.71 | CHRNA3; CXCR4; FKBPL; FSCN1; GSTP1; IL2RA; NAMPT; PNP; PPIF; PYGL; TOP2A; UGT1A7 |
| golgi-to-er retrograde transport | 85 | 11 | 1.06E−03 | 1.20E−02 | 2.83 | CENPE; KIF11; KIF15; KIF18A; KIF20A; KIF23; KIF2C; KIF4A; TUBA1C; TUBB2A; TUBB6 |
| toll-like receptor signaling pathway | 73 | 10 | 1.08E−03 | 1.23E−02 | 3.00 | CCL3; CD80; CXCL10; CXCL11; CXCL9; IL12B; IL1B; IL6; MYD88; STAT1 |
| mitotic spindle: GO | 50 | 8 | 1.09E−03 | 1.23E−02 | 3.50 | ASPM; AURKA; CDK1; CENPE; ECT2; KIF18A; KIF23; MAD2L1 |
| regulation of smooth muscle cell proliferation: GO | 98 | 12 | 1.09E−03 | 1.23E−02 | 2.68 | HBEGF; HIF1A; HMOX1; IFNG; IL12B; IL6; NAMPT; NDRG4; NR4A3; ORC1; PTAFR; STAT1 |
| modification of morphology or physiology of other organism: GO | 86 | 11 | 1.17E−03 | 1.31E−02 | 2.80 | CAMP; CCL3; HMGA2; KPNA2; LTF; PPIB; RNASE7; S100A12; SERPINB9; TREM1; ZC3H12A |
| virus receptor activity: GO | 62 | 9 | 1.19E−03 | 1.33E−02 | 3.17 | CCR5; CD80; CXCR4; HYAL3; ITGB6; LDLR; SERPINB3; SLAMF1; TNFRSF4 |
| positive regulation of epidermis development: GO | 30 | 6 | 1.20E−03 | 1.34E−02 | 4.37 | CYP27B1; HPSE; IL20; KRT17; SFN; TRIM16 |
| il12 pathway | 21 | 5 | 1.22E−03 | 1.36E−02 | 5.21 | CCR5; CD3E; IFNG; IL12B; IL12RB2 |
| transferase activity transferring amino acyl groups: GO | 21 | 5 | 1.22E−03 | 1.36E−02 | 5.21 | CHAC1; CHAC2; GGCT; TGM1; TGM2 |
| protein tetramerization: GO | 126 | 14 | 1.24E−03 | 1.37E−02 | 2.43 | HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L; RRM2; TK1 |
| division: GO | 41 | 7 | 1.40E−03 | 1.55E−02 | 3.73 | BUB1; BUB1B; MAD2L1; OSM; PLK1; PTTG1; TTK |
| cd8 ter downstream pathway | 52 | 8 | 1.42E−03 | 1.56E−02 | 3.36 | CD3E; EOMES; FOSL1; IFNG; IL2RA; PRKCQ; TNFRSF4; TNFRSF9 |
| negative regulation of interferon gamma production: GO | 31 | 6 | 1.44E−03 | 1.57E−02 | 4.23 | C1QBP; CD274; IL36RN; PGLYRP2; SLAMF1; ZC3H12A |
| pkmts methylate histone lysines | 31 | 6 | 1.44E−03 | 1.57E−02 | 4.23 | HIST1H3A; HIST1H3I; HIST1H4I; HIST1H4J; HIST1H4K; HIST1H4L |
| positive regulation of protein secretion: GO | 185 | 18 | 1.45E−03 | 1.58E−02 | 2.13 | CAMP; CCL3; CD2; CD274; HIF1A; IFNG; IL1B; IL26; IL4R; IL6; NLRP2; PRKCQ; PYCARD; SLAMF1; TNFRSF4; TRIM16; VSNL1; WNT5A |
| hematopoietic cell lineage | 76 | 10 | 1.49E−03 | 1.62E−02 | 2.88 | CD1B; CD2; CD3E; CSF2; FCGR1A; IL1B; IL2RA; IL4R; IL6; IL7R |
| cell communication | 115 | 13 | 1.51E−03 | 1.64E−02 | 2.47 | DSC2; DSG3; GJB2; GJB6; INA; KRT16; KRT17; KRT6A; KRT6B; KRT9; LMNB1; LMNB2; TNC |
| regulation of adaptive immune response: GO | 115 | 13 | 1.51E−03 | 1.64E−02 | 2.47 | CD80; IFNG; IL12B; IL1B; IL4R; IL7R; JAK3; PRKCQ; PYCARD; RSAD2; SAMSN1; SASH3; SLAMF1 |
| leukocyte apoptotic process: GO | 22 | 5 | 1.53E−03 | 1.65E−02 | 4.97 | BAK1; IFNG; IL2RA; IL6; TNFRSF21 |
| response to vitamin: GO | 89 | 11 | 1.55E−03 | 1.67E−02 | 2.70 | ACP5; ALPL; AQP3; CCNE1; CXCL10; CYP24A1; CYP27B1; GSTP1; IL1B; KYNU; TNC |
| intermediate filament based process: GO | 42 | 7 | 1.62E−03 | 1.74E−02 | 3.64 | INA; KRT16; KRT17; KRT6A; KRT6C; KRT9; NEFM |
| response to nutrient: GO | 173 | 17 | 1.71E−03 | 1.82E−02 | 2.15 | ACP5; AHCY; ALPL; AQP3; CCNE1; CD3E; CXCL10; CYP24A1; CYP27B1; GSTP1; |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| | | | | | | HMOX1; IL1B; KYNU; LDHA; LIPG; SLC16A1; TNC |
| lymphocyte chemotaxis: GO | 32 | 6 | 1.71E−03 | 1.82E−02 | 4.10 | CCL18; CCL22; CCL3; CXCL10; CXCL11; CXCL13 |
| negative regulation of mitotic nuclear division: GO | 32 | 6 | 1.71E−03 | 1.82E−02 | 4.10 | BUB1; BUB1B; MAD2L1; PLK1; PTTG1; TTK |
| organism involved in symbiotic interaction: GO | 78 | 10 | 1.82E−03 | 1.93E−02 | 2.80 | CCR5; CD80; CTSB; CXCR4; ITGB6; LAMP3; LDLR; SERPINB3; SLAMF1; TNFRSF4 |
| monocarboxylic acid binding: GO | 54 | 8 | 1.83E−03 | 1.93E−02 | 3.24 | CRABP2; FABP5; FABP6; PYGL; S100A8; S100A9; UGT1A10; UGT1A7 |
| activation of cysteine type endopeptidase activity: GO | 91 | 11 | 1.86E−03 | 1.96E−02 | 2.64 | BAK1; CCK; CYCS; FAM162A; IFI16; IFI27; PYCARD; S100A8; S100A9; TNFSF10; VCP |
| regulation of cyclin dependent protein kinase activity: GO | 91 | 11 | 1.86E−03 | 1.96E−02 | 2.64 | BLM; CCNA2; CDC25A; CDC6; CDK5R1; CDKN3; CKS2; PKMYT1; PLK1; SFN; UBE2C |
| negative regulation of leukocyte mediated immunity: GO | 43 | 7 | 1.87E−03 | 1.96E−02 | 3.56 | FOXF1; HMOX1; IL7R; JAK3; SERPINB4; SERPINB9; SLAMF1 |
| ap1 pathway | 66 | 9 | 1.87E−03 | 1.96E−02 | 2.98 | CDK1; CSF2; FOSL1; HIF1A; IFNG; IL6; MMP1; MMP9; PLAU |
| negative regulation of cell cycle g2 m phase transition: GO | 23 | 5 | 1.90E−03 | 1.97E−02 | 4.75 | BLM; CCNA2; CDK1; CLSPN; HMGA2 |
| regulation of nuclease activity: GO | 23 | 5 | 1.90E−03 | 1.97E−02 | 4.75 | BAK1; GZMA; OAS1; OAS3; PCNA |
| response to auditory stimulus: GO | 23 | 5 | 1.90E−03 | 1.97E−02 | 4.75 | CNTNAP2; CXCL10; HIF1A; IL6; STRA6 |
| regulation of leukocyte mediated immunity: GO | 146 | 15 | 1.93E−03 | 1.99E−02 | 2.25 | FOXF1; HMOX1; FNG; IL12B; IL1B; IL4R; IL7R; JAK3; PTAFR; RAC2; RSAD2; SASH3; SERPINB4; SERPINB9; SLAMF1 |
| monosaccharide metabolic process: GO | 175 | 17 | 1.93E−03 | 1.99E−02 | 2.12 | CHST1; ENO1; FABP5; FUT1; FUT2; GAPDH; GOT2; GSTO1; HK2; OAS1; PFKFB4; PGAM1; PGK1; PGM2; TPI1; UGT1A10; UGT1A7 |
| signaling by wnt | 175 | 17 | 1.93E−03 | 1.99E−02 | 2.12 | H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L; PSMA4; PSMA5; PSMB6; WNT5A |
| negative regulation of response to wounding: GO | 132 | 14 | 1.94E−03 | 1.99E−02 | 2.32 | ACP5; ADCYAP1; F12; FOXF1; GSTP1; IL12B; IL2RA; MEFV; PBK; PLAU; PLAUR; SERPINE1; SOCS3; ZC3H12A |
| dna replication: GO | 190 | 18 | 1.96E−03 | 2.00E−02 | 2.07 | BLM; CCNE1; CDC25A; CDC45; CDC6; CDK1; CLSPN; EXO1; GINS3; MCM10; ORC1; ORC6; PCNA; POLQ; RRM2; TIMELESS; TOP2A; TYMP |
| response to hydrogen peroxide: GO | 105 | 12 | 2.00E−03 | 2.04E−02 | 2.50 | AREG; BAK1; CDK1; ECT2; FOSL1; HIF1A; HMOX1; IL6; LDHA; NR4A3; OLR1; PPIF |
| cytokine receptor activity: GO | 79 | 10 | 2.00E−03 | 2.04E−02 | 2.77 | CCR4; CCR5; CXCR4; EBI3; IL12B; IL12RB2; IL13RA1; IL2RA; IL4R; IL7R |
| negative regulation of immune effector process: GO | 92 | 11 | 2.04E−03 | 2.06E−02 | 2.61 | C1QBP; FOXF1; HMOX1; IL2RA; IL4R; IL7R; JAK3; PGLYRP2; SERPINB4; SERPINB9; SLAMF1 |
| glycosaminoglycan binding: GO | 176 | 17 | 2.06E−03 | 2.08E−02 | 2.11 | C1QBP; CCL7; CXCL10; CXCL11; CXCL13; CXCL6; FGFBP1; HABP2; HBEGF; HMMR; LIPG; LTF; NELL2; PGF; PGLYRP2; RNASE7; SELL |
| apoptotic mitochondrial changes: GO | 55 | 8 | 2.06E−03 | 2.08E−02 | 3.18 | BAK1; BCL2A1; CCK; GGCT; HK2; IFI6; PPIF; SFN |
| chromatin modifying enzymes | 119 | 13 | 2.07E−03 | 2.08E−02 | 2.39 | H2AFX; H2AFZ; HIST1H2AE; HIST1H2BB; HIST1H2BF; HIST1H2BH; HIST1H2BM; HIST1H3A; HIST1H3I; HIST1H4I; HIST1H4J; HIST1H4K; HIST1H4L |
| regulation of stat cascade: GO | 119 | 13 | 2.07E−03 | 2.08E−02 | 2.39 | CDK5R1; CSF2; IFNE; IFNG; IL12B; IL19; IL20; IL22; IL24; IL26; IL6; OSM; SOCS3 |
| cell cycle g2 m phase transition: GO | 133 | 14 | 2.09E−03 | 2.09E−02 | 2.30 | AURKA; BIRC5; CCNB1; CCNB2; CDC25A; CDC25B; CDK1; FOXM1; HMMR; MELK; NEK2; PKMYT1; PLK1; TPX2 |
| mitotic dna integrity checkpoint: GO | 93 | 11 | 2.22E−03 | 2.21E−02 | 2.59 | AURKA; BLM; CCNA2; CCNB1; CDK1; CLSPN; HMGA2; PCNA; PLK2; SFN; TOP2A |
| structural constituent of cytoskeleton: GO | 93 | 11 | 2.22E−03 | 2.21E−02 | 2.59 | BFSP1; INA; KRT16; KRT17; KRT6B; KRT9; NDC80; NEFM; TUBA1C; TUBB2A; TUBB6 |
| positive regulation of leukocyte | 120 | 13 | 2.23E−03 | 2.21E−02 | 2.37 | CD80; IFNG; IL12B; IL1B; IL20; IL2RA; IL4R; IL6; IL7R; PNP; PRDM1; SASH3; |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| differentiation: GO | | | | | | TNFSF9 |
| response to alkaloid: GO | 120 | 13 | 2.23E−03 | 2.21E−02 | 2.37 | BLM; CCNA2; CHRNA3; CHRNA6; HIF1A; HMOX1; HOMER1; HTR3A; IL1B; IL6; NTRK1; PLAU; SLC7A11 |
| atp dependent chromatin remodeling: GO | 68 | 9 | 2.32E−03 | 2.26E−02 | 2.89 | CENPA; CENPN; CENPW; HIST1H4I; HIST1H4J; HIST1H4K; HIST1H4L; HJURP; OIP5 |
| interferon gamma mediated signaling pathway: GO | 68 | 9 | 2.32E−03 | 2.26E−02 | 2.89 | FCGR1A; IFI30; IFNG; OAS1; OAS2; OAS3; OASL; PTAFR; STAT1 |
| regulation of cell cycle g2 m phase transition: GO | 56 | 8 | 2.32E−03 | 2.26E−02 | 3.12 | BLM; CCNA2; CDK1; CLSPN; HMGA2; KIF14; PLK1; PRKCQ |
| gap junction assembly | 24 | 5 | 2.32E−03 | 2.26E−02 | 4.56 | GJB2; GJB6; TUBA1C; TUBB2A; TUBB6 |
| regulation of neutrophil chemotaxis: GO | 24 | 5 | 2.32E−03 | 2.26E−02 | 4.56 | C1QBP; CXCL1; CXCL3; IL1B; RAC2 |
| regulation of t cell migration: GO | 24 | 5 | 2.32E−03 | 2.26E−02 | 4.56 | CXCL10; CXCL13; PYCARD; S100A7; WNT5A |
| monocyte chemotaxis: GO | 34 | 6 | 2.38E−03 | 2.30E−02 | 3.86 | CCL18; CCL22; CCL3; CCL7; IL6; S100A12 |
| positive regulation of tyrosine phosphorylation of stat3 protein: GO | 34 | 6 | 2.38E−03 | 2.30E−02 | 3.86 | IL12B; IL20; IL24; IL6; OSM; SOCS3 |
| gene silencing by rna: GO | 121 | 13 | 2.41E−03 | 2.32E−02 | 2.35 | HIST1H3A; HIST1H3B; HIST1H3C; HIST1H3F; HIST1H3G; HIST1H3H; HIST1H3I; HIST1H3J; HIST1H4I; HIST1H4J; HIST1H4K; HIST1H4L; RAN |
| homeostasis: GO | 69 | 9 | 2.57E−03 | 2.48E−02 | 2.85 | HIF1A; HMOX1; HMOX2; LCN2; LTF; S100A8; S100A9; SCO2; SLC39A6 |
| class a1 rhodopsin like receptors | 136 | 14 | 2.58E−03 | 2.48E−02 | 2.25 | CCL22; CCL3; CCL7; CCR4; CCR5; CXCL5; CXCL9; FPR3; GPR65; HCAR3; HRH3; HTR7; PTAFR; SIPR4 |
| phase ii - conjugation of compounds | 57 | 8 | 2.61E−03 | 2.49E−02 | 3.07 | CHAC1; CHAC2; CNDP2; GGCT; GSTO1; GSTP1; UGT1A10; UGT1A7 |
| regulation of epidermis development: GO | 57 | 8 | 2.61E−03 | 2.49E−02 | 3.07 | AQP3; CDH3; CYP27B1; HPSE; IL20; KRT17; SFN; TRIM16 |
| progesterone mediated oocyte maturation | 82 | 10 | 2.66E−03 | 2.54E−02 | 2.67 | BUB1; CCNA2; CCNB1; CCNB2; CDC25A; CDC25B; CDK1; MAD2L1; PKMYT1; PLK1 |
| positive regulation of hemopoiesis: GO | 151 | 15 | 2.69E−03 | 2.56E−02 | 2.17 | CD80; HIF1A; IFNG; IL12B; IL1B; IL20; IL2RA; IL4R; IL6; IL7R; ISG15; PNP; PRDM1; SASH3; TNFSF9 |
| negative regulation of cell cycle process: GO | 196 | 18 | 2.76E−03 | 2.62E−02 | 2.01 | AURKA; BLM; BUB1; BUB1B; C10orf99; CCNA2; CCNB1; CDK1; CLSPN; HMGA2; MAD2L1; OSM; PCNA; PLK1; PLK2; PTTG1; SFN; TTK |
| acetylcholine receptor activity: GO | 25 | 5 | 2.82E−03 | 2.63E−02 | 4.37 | CHRNA3; CHRNA6; CHRNA9; HRH3; HTR3A |
| basigin interactions | 25 | 5 | 2.82E−03 | 2.63E−02 | 4.37 | ATP1B3; MMP1; SLC16A1; SLC7A11; SLC7A5 |
| neurotransmitter binding: GO | 25 | 5 | 2.82E−03 | 2.63E−02 | 4.37 | CHRNA3; CHRNA6; CHRNA9; HTR3A; SLC6A11 |
| migration: GO | 25 | 5 | 2.82E−03 | 2.63E−02 | 4.37 | C1QBP; CXCL1; CXCL3; IL1B; RAC2 |
| differentiation: GO | 25 | 5 | 2.82E−03 | 2.63E−02 | 4.37 | CD80; IL12B; IL4R; IL6; JAK3 |
| sumoylation of dna replication proteins | 25 | 5 | 2.82E−03 | 2.63E−02 | 4.37 | AURKA; BIRC5; CDCA8; PCNA; TOP2A |
| p53 signaling pathway | 70 | 9 | 2.84E−03 | 2.65E−02 | 2.81 | CCNB1; CCNB2; CCNE1; CDK1; CYCS; PCNA; RRM2; SERPINE1; SFN |
| response to estrogen: GO | 197 | 18 | 2.91E−03 | 2.71E−02 | 2.00 | AREG; AURKA; CALR; CCNA2; CCNE1; CYP27B1; GJB2; GSTP1; H2AFZ; HIF1A; HMOX1; IL1B; IL4R; LDHA; SERPINB9; SOCS3; WNT5A; WNT7A |
| microtubule associated complex: GO | 138 | 14 | 2.95E−03 | 2.73E−02 | 2.22 | AURKA; BIRC5; CDCA8; CENPE; KIF11; KIF14; KIF15; KIF18A; KIF20A; KIF23; KIF2C; KIF4A; LRP8; MEFV |
| regeneration: GO | 138 | 14 | 2.95E−03 | 2.73E−02 | 2.22 | BAK1; CCNA2; CCNB1; CCNE1; CDK1; GSTP1; KLK6; NR4A3; PGF; PLAU; PRKCQ; SOCS3; TNC; WNT7A |
| factor superfamily cytokine production: GO | 36 | 6 | 3.22E−03 | 2.96E−02 | 3.64 | ACP5; CD274; GSTP1; LTF; SLAMF1; ZC3H12A |
| protein localization to chromosome: GO | 36 | 6 | 3.22E−03 | 2.96E−02 | 3.64 | BUB1B; CDK1; CENPA; ESCO2; HIST1H1B; PLK1 |
| regulation of mast cell activation: GO | 36 | 6 | 3.22E−03 | 2.96E−02 | 3.64 | FOXF1; HMOX1; IL4R; NR4A3; PTPRE; RAC2 |
| positive regulation of cytokinesis: GO | 26 | 5 | 3.38E−03 | 3.10E−02 | 4.21 | CDC25B; CDC6; ECT2; KIF14; KIF23 |
| cellular modified amino acid metabolic | 200 | 18 | 3.43E−03 | 3.13E−02 | 1.97 | AHCY; ALDH4A1; CHAC1; CHAC2; CNDP2; EIF4A3; FOXE1; GCNT4; GGCT; |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| process: GO | | | | | | GGH; GOT2; GSTO1; GSTP1; IDO1; KYNU; PLA2G4D; TDO2; VNN3 |
| growth factor activity: GO | 126 | 13 | 3.44E−03 | 3.14E−02 | 2.26 | AREG; ARTN; CSF2; CXCL1; EPGN; HBEGF; IL12B; IL6; MANF; OSM; PGF; TGFA; TYMP |
| deubiquitination | 155 | 14 | 3.46E−03 | 3.14E−02 | 2.12 | CCNA2; CDC20; CDC25A; CDC25B; CDK1; CLSPN; H2AFX; HIF1A; HISTIH2AE; HIST1H2BB; HIST1H2BF; HIST 1H2BH; HIST1H2BM; PSMA5; PSMB6 |
| negative regulation of inflammatory response: GO | 85 | 10 | 3.47E−03 | 3.15E−02 | 2.57 | ACP5; ADCYAP1; FOXF1; GSTP1; IL12B; IL2RA; MEFV; PBK; SOCS3; ZC3H12A |
| interaction with symbiont: GO | 48 | 7 | 3.59E−03 | 3.25E−02 | 3.19 | CAMP; CCL3; HMGA2; LTF; PPIB; TREM1; ZC3H12A |
| microtubule motor activity: GO | 73 | 9 | 3.80E−03 | 3.42E−02 | 2.70 | CENPE; KIF11; KIF14; KIF15; KIF18A; KIF20A; KIF23; KIF2C; KIF4A |
| reg gr pathway | 73 | 9 | 3.80E−03 | 3.42E−02 | 2.70 | CDK5R1; CSF2; IFNG; IL6; KRT17; MMP1; SELE; SFN; STAT1 |
| hexose metabolic process: GO | 142 | 14 | 3.83E−03 | 3.44E−02 | 2.16 | CHST1; ENO1; FABP5; FUT1; FUT2; GAPDH; GOT2; HK2; OAS1; PFKFB4; PGAM1; PGK1; PGM2; TPI1 |
| response to corticosteroid: GO | 157 | 15 | 3.91E−03 | 3.50E−02 | 2.09 | ADCYAP1; ALPL; AREG; CCNE1; FOSL1; GSTP1; HIF1A; IL1B; IL22; IL6; PTAFR; RAN; SOCS3; TK1; WNT5A |
| carbohydrate biosynthetic process: GO | 114 | 12 | 4.00E−03 | 3.57E−02 | 2.30 | B3GNT3; ENO1; FUT3; GAPDH; GOT2; GSTO1; HAS3; PGAM1; PGK1; PGM2; ST6GALNAC1; TPI1 |
| regulation of tyrosine phosphorylation of stat protein: GO | 6 | 8 | 4.02E−03 | 3.59E−02 | 2.87 | CSF2; IFNG; IL12B; IL20; IL24; IL6; OSM; SOCS3 |
| apc/c:cdh1 mediated degradation of cdc20 and other apc/c:cdh1 targeted proteins in late mitosis/early g1 | 49 | 7 | 4.05E−03 | 3.60E−02 | 3.12 | AURKA; CDC20; PLK1; PSMA5; PSMB6; PTTG1; UBE2C |
| double strand break repair: GO | 143 | 14 | 4.09E−03 | 3.63E−02 | 2.14 | BLM; CDC45; CDCA5; DTX3L; ESCO2; H2AFX; HIST1H4I; HIST1H4J; HIST1H4K; HIST1H4L; PARP9; POLQ; TRIP13; VCP |
| cell surface interactions at the vascular wall | 101 | 11 | 4.27E−03 | 3.78E−02 | 2.38 | ATP1B3; CD2; ITGAX; MMP1; OLR1; SELE; SELL; SLC16A1; SLC7A11; SLC7A5; TREM1 |
| positive regulation of mitochondrion organization: GO | 144 | 14 | 4.35E−03 | 3.84E−02 | 2.13 | BAK1; C1QBP; FAM162A; HIF1A; ITGAX; MMP9; PLAUR; PPIF; PYCARD; RAC2; SFN; TNFSF10; UGCG; YWHAQ |
| dna dependent dna replication: GO | 88 | 10 | 4.48E−03 | 3.94E−02 | 2.49 | BLM; CCNE1; CDC45; CDC6; GINS3; MCM10; ORC1; PCNA; POLQ; TOP2A |
| regulation of dna binding: GO | 88 | 10 | 4.48E−03 | 3.94E−02 | 2.49 | GZMA; HJURP; HMGA2; HMOX1; IFI16; MDFI; MMP9; NEK2; NME1; PLAUR |
| regulation of lymphocyte apoptotic process: GO | 50 | 7 | 4.55E−03 | 3.99E−02 | 3.06 | CD274; HIF1A; IDO1; JAK3; PRELID1; PRKCQ; WNT5A |
| positive regulation of ligase activity: GO | 102 | 11 | 4.61E−03 | 4.03E−02 | 2.36 | BUB1B; CCNB1; CDC20; CDK1; MAD2L1; PLK1; PSMA4; PSMA5; PSMB6; UBE2C; UBE2S |
| positive regulation of apoptotic signaling pathway: GO | 160 | 15 | 4.67E−03 | 4.08E−02 | 2.05 | BAK1; CTSC; FAM162A; IL19; MMP9; OSM; PLAUR; PPIF; PYCARD; S100A8; S100A9; SFN; TNFRSF12A; TNFSF10; YWHAQ |
| activation of the pre-replicative complex | 28 | 5 | 4.74E−03 | 4.11E−02 | 3.91 | CDC45; CDC6; MCM10; ORC1; ORC6 |
| dna replication initiation: GO | 28 | 5 | 4.74E−03 | 4.11E−02 | 3.91 | CNE1; CDC45; CDC6; MCM10; ORC1 |
| positive regulation of immunoglobulin production: GO | 28 | 5 | 4.74E−03 | 4.11E−02 | 3.91 | IFNG; IL4R; IL6; SASH3; TNFRSF4 |
| nucleoside triphosphate metabolic process: GO | 191 | 17 | 4.82E−03 | 4.17E−02 | 1.95 | ADCYAP1; CMPK2; COX7B; CYCS; ENO1; GAPDH; HK2; HSPA8; LDHA; NME1; NUDT15; OGDHL; PFKFB4; PGAM1; PGK1; TPI1; VCP |
| antigen binding: GO | 89 | 10 | 4.86E−03 | 4.18E−02 | 2.46 | CD1B; HSPA8; IGHG4; IL7R; RAETIL; SLAMF1; SLC7A5; ULBP1; ULBP2; ULBP3 |
| atr pathway | 39 | 6 | 4.89E−03 | 4.18E−02 | 3.36 | CCNA2; CDC25A; CDC6; CLSPN; PLK1; TIMELESS |
| cytosolic dna sensing pathway | 39 | 6 | 4.89E−03 | 4.18E−02 | 3.36 | CXCL10; IL1B; IL6; POLR3G; PYCARD; ZBP1 |
| nuclear ubiquitin ligase complex: GO | 39 | 6 | 4.89E−03 | 4.18E−02 | 3.36 | BUB1B; CBX2; CDC20; RNF222; UBE2C; UBE2S |
| positive regulation of interleukin 8 production: GO | 39 | 6 | 4.89E−03 | 4.18E−02 | 3.36 | CAMP; CD2; IL1B; PYCARD; SERPINE1; WNT5A |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| apc c cdh1 mediated degradation of cdc20 and other apc c cdh1 targeted proteins in late mitosis early g1 | 63 | 8 | 4.92E−03 | 4.20E−02 | 2.78 | AURKA; CDC20; PLK1; PSMA4; PSMA5; PSMB6; PTTG1; UBE2C |
| response to interleukin 1: GO | 103 | 11 | 4.97E−03 | 4.23E−02 | 2.34 | CCL18; CCL22; CCL3; CCL7; HIF1A; HYAL3; IL6; MYD88; PYCARD; SELE; ZC3H12A |
| immunoregulatory interactions between a lymphoid and a non-lymphoid cell | 51 | 7 | 5.09E−03 | 4.30E−02 | 3.00 | CD1B; FCGR1A; IFITM1; IFITM3; LILRA5; SELL; TREM1 |
| monosaccharide biosynthetic process: GO | 51 | 7 | 5.09E−03 | 4.30E−02 | 3.00 | ENO1; GAPDH; GOT2; GSTO1; PGAM1; PGK1; TPI1 |
| regulation of cytokine production involved in immune response: GO | 51 | 7 | 5.09E−03 | 4.30E−02 | 3.00 | HMOX1; JAK3; NR4A3; RSAD2; SASH3; SLAMF1; WNT5A |
| regulation of dna replication: GO | 147 | 14 | 5.23E−03 | 4.41E−02 | 2.08 | AREG; BLM; CALR; CCT5; CDC6; CDK1; CSF2; ESCO2; IL6; NEK2; PCNA; PIF1; PRKCQ; S100A11 |
| cell activation involved in immune response: GO | 118 | 12 | 5.29E−03 | 4.45E−02 | 2.22 | CCL3; CLEC7A; EOMES; EXO1; IFNE; IFNG; IL12B; IL6; NR4A3; PLA2G3; PYCARD; SLAMF1 |
| hif1 tfpathway | 64 | 8 | 5.43E−03 | 4.56E−02 | 2.73 | CXCR4; ENO1; HIF1A; HK2; HMOX1; LDHA; PGK1; SERPINE1 |
| biological oxidations | 178 | 16 | 5.47E−03 | 4.58E−02 | 1.97 | ADH7; AHCY; CHAC1; CHAC2; CNDP2; CYP24A1; CYP27B1; CYP2S1; CYP4F11; CYP4F22; GGCT; GSTO1; GSTP1; SMOX; UGT1A10; UGT1A7 |
| ccr chemokine receptor binding: GO | 29 | 5 | 5.56E−03 | 4.62E−02 | 3.77 | CCL18; CCL22; CCL3; CCL7; CXCL13 |
| proteins | 29 | 5 | 5.56E−03 | 4.62E−02 | 3.77 | HIST1H2BB; HIST1H2BF; HIST1H2BH; HIST1H2BM; PCNA |
| regulation of neutrophil migration: GO | 29 | 5 | 5.56E−03 | 4.62E−02 | 3.77 | C1QBP; CXCL1; CXCL3; IL1B; RAC2 |
| collagen degradation | 40 | 6 | 5.56E−03 | 4.62E−02 | 3.28 | CTSB; CTSL; MMP1; MMP12; MMP3; MMP9 |
| cellular response to interleukin 1: GO | 78 | 9 | 5.93E−03 | 4.92E−02 | 2.52 | CCL18; CCL22; CCL3; CCL7; HIF1A; HYAL3; IL6; PYCARD; ZC3H12A |
| centriole: GO | 92 | 10 | 6.16E−03 | 5.09E−02 | 2.38 | AURKA; BIRC5; CEP55; HSPA6; PLA2G3; PLK2; POC1A; RAN; STIL; TOP2A |
| intermediate filament: GO | 150 | 14 | 6.25E−03 | 5.14E−02 | 2.04 | BFSP1; INA; KRT16; KRT17; KRT24; KRT6A; KRT6B; KRT6C; KRT75; KRT9; LMNB1; LMNB2; NEFM; NME1 |
| positive regulation of peptidyl tyrosine phosphorylation: GO | 150 | 14 | 6.25E−03 | 5.14E−02 | 2.04 | CCK; CD3E; CD80; CSF2; EPGN; IFNG; IL12B; IL20; IL24; IL6; LRP8; OSM; SOCS3; TGFA |
| interleukin-12 family signaling | 41 | 6 | 6.30E−03 | 5.16E−02 | 3.20 | CNN2; GSTO1; IFNG; IL12RB2; LMNB1; STAT1 |
| regulation of tyrosine phosphorylation of stat3 protein: GO | 41 | 6 | 6.30E−03 | 5.16E−02 | 3.20 | IL12B; IL20; IL24; IL6; OSM; SOCS3 |
| negative regulation of cysteine type endopeptidase activity: GO | 79 | 9 | 6.46E−03 | 5.23E−02 | 2.49 | BIRC5; IFI16; IFI6; IL6; LAMP3; MMP9; PLAUR; SERPINB9; SFN |
| acute phase response: GO | 30 | 5 | 6.46E−03 | 5.23E−02 | 3.64 | HIF1A; IL1B; IL22; IL6; SERPINA1 |
| mitotic cytokinesis: GO | 30 | 5 | 6.46E−03 | 5.23E−02 | 3.64 | CEP55; KIF20A; KIF23; KIF4A; PLK1 |
| positive regulation of interleukin 2 production: GO | 30 | 5 | 6.46E−03 | 5.23E−02 | 3.64 | CD3E; CD80; IL1B; PRKCQ; SASH3 |
| synaptic transmission cholinergic: GO | 30 | 5 | 6.46E−03 | 5.23E−02 | 3.64 | CHRNA3; CHRNA6; CHRNA9; HRH3; HTR3A |
| lymphocyte mediated immunity: GO | 121 | 12 | 6.46E−03 | 5.23E−02 | 2.17 | C1QBP; CTSC; EXO1; IGHG4; IL4R; PRDX1; RAETIL; SLAMF1; SLAMF7; ULBP1; ULBP2; ULBP3 |
| negative regulation of protein secretion: GO | 93 | 10 | 6.64E−03 | 5.33E−02 | 2.35 | IL1B; IL36RN; IL6; RSAD2; SLAMF1; SRGN; TNFRSF21; TNFRSF9; VSNL1; ZC3H12A |
| activation of matrix metalloproteinases | 20 | 4 | 6.71E−03 | 5.33E−02 | 4.37 | CTSL; MMP1; MMP3; MMP9 |
| amine catabolic process: GO | 20 | 4 | 6.71E−03 | 5.33E−02 | 4.37 | IDO1; KYNU; SMOX; TDO2 |
| anaphase promoting complex: GO | 20 | 4 | 6.71E−03 | 5.33E−02 | 4.37 | BUB1B; CDC20; UBE2C; UBE2S |
| cofactor catabolic process: GO | 20 | 4 | 6.71E−03 | 5.33E−02 | 4.37 | CYP4F11; HMOX1; HMOX2; VCP |
| copper ion transport: GO | 20 | 4 | 6.71E−03 | 5.33E−02 | 4.37 | HEPHL1; SCO2; STEAP1B; STEAP4 |
| positive regulation of coagulation: GO | 20 | 4 | 6.71E−03 | 5.33E−02 | 4.37 | F12; HPSE; S100A9; SERPINE1 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| regulation of monocyte chemotaxis: GO | 20 | 4 | 6.71E−03 | 5.33E−02 | 4.37 | CXCL10; S100A14; S100A7; SERPINE1 |
| positive regulation of cellular protein catabolic process: GO | 182 | 16 | 6.76E−03 | 5.36E−02 | 1.92 | AURKA; BUB1B; CCNB1; CDC20; CDK1; CTSC; DLGAP5; MAD2L1; PCSK9; PLK1; PLK2; PSMA4; PSMA5; PSMB6; UBE2C; VCP |
| regulation of defense response to virus by host: GO | 122 | 12 | 6.90E−03 | 5.46E−02 | 2.15 | FGFBP1; HIST1H3A; HIST1H3B; HIST1H3C; HIST1H3F; HIST1H3G; HIST1H3H; HIST1H3I; HIST1H3J; IL12B; TREM1; ZC3H12A |
| response to estradiol: GO | 137 | 13 | 7.01E−03 | 5.53E−02 | 2.08 | AREG; AURKA; CALR; CCNA2; CCNE1; GJB2; GSTP1; H2AFZ; HIF1A; IL1B; SOCS3; WNT5A; WNT7A |
| factor superfamily cytokine production: GO | 54 | 7 | 7.02E−03 | 5.53E−02 | 2.83 | CCL3; CD2; IFNG; IL12B; PTAFR; PYCARD; SASH3 |
| glucose metabolic process: GO | 108 | 11 | 7.10E−03 | 5.56E−02 | 2.23 | ENO1; FABP5; GAPDH; GOT2; HK2; OAS1; PFKFB4; PGAM1; PGK1; PGM2; TPI1 |
| oxidoreductase activity acting on the aldehyde or oxo group of donors: GO | 42 | 6 | 7.11E−03 | 5.56E−02 | 3.12 | ADH7; AKR1B10; ALDH1A3; ALDH4A1; GAPDH; OGDHL |
| receptor regulator activity: GO | 42 | 6 | 7.11E−03 | 5.56E−02 | 3.12 | ADH7; CXCL 13; IL36RN; PCSK9; WNT5A; WNT7A |
| response to ammonium ion: GO | 42 | 6 | 7.11E−03 | 5.56E−02 | 3.12 | CCNA2; CDK5R1; GNA15; HRH3; PLAU; PTAFR |
| antigen processing and presentation of peptide antigen: GO | 168 | 15 | 7.30E−03 | 5.69E−02 | 1.95 | AP1S3; CALR; CENPE; FCGR1A; IFI30; KIF11; KIF15; KIF18A; KIF23; KIF2C; KIF4A; PSMA4; PSMA5; PSMB6; TAP2 |
| nuclear envelope breakdown | 31 | 5 | 7.47E−03 | 5.81E−02 | 3.53 | CCNB1; CCNB2; CDK1; LMNB1; PLK1 |
| positive regulation of dna replication: GO | 81 | 9 | 7.60E−03 | 5.91E−02 | 2.43 | AREG; CALR; CCT5; CDK1; CSF2; IL6; NEK2; PCNA; PRKCQ |
| transition metal ion homeostasis: GO | 95 | 10 | 7.71E−03 | 5.96E−02 | 2.30 | HIF1A; HMOX1; HMOX2; LCN2; LTF; S100A8; S100A9; SCO2; SLC39A6; STEAP4 |
| xenophagy: GO | 95 | 10 | 7.71E−03 | 5.96E−02 | 2.30 | FGFBP1; HIST1H3A; HIST1H3B; HIST1H3C; HIST1H3F; HIST1H3G; HIST1H3H; HIST1H3I; HIST1H3J; TREM1 |
| removal of licensing factors from origins | 55 | | 7.77E−03 | 5.99E−02 | 2.78 | CCNA2; CDC6; MCM10; ORC1; ORC6; PSMA5; PSMB6 |
| microtubule binding: GO | 185 | 16 | 7.88E−03 | 6.05E−02 | 1.89 | BIRC5; CENPE; GAPDH; KIF11; KIF14; KIF15; KIF18A; KIF20A; KIF23; KIF2C; KIF4A; NEFM; PLK1; S100A8; S100A9; SKA1 |
| multi multicellular organism process: GO | 185 | 16 | 7.88E−03 | 6.05E−02 | 1.89 | ADCYAP1; CTSB; CYP27B1; FOSL1; GJB2; HIF1A; IDO1; IL1B; MMP9; NAMPT; PGF; PLAU; PRDM1; PTAFR; TK1; VMP1 |
| nfat tfpathway | 43 | 6 | 7.99E−03 | 6.13E−02 | 3.05 | CSF2; CTLA4; FOSL1; IFNG; IL2RA; PRKCQ |
| adenylyltransferase activity: GO | 21 | 4 | 8.05E−03 | 6.13E−02 | 4.17 | OAS1; OAS2; OAS3; OASL |
| carbon fixation | 21 | 4 | 8.05E−03 | 6.13E−02 | 4.17 | GOT2; PGK1; PKM; TPI1 |
| female meiotic division: GO | 21 | 4 | 8.05E−03 | 6.13E−02 | 4.17 | AURKA; CDC25B; PLK1; TRIP13 |
| glycosaminoglycan degradation | 21 | 4 | 8.05E−03 | 6.13E−02 | 4.17 | HPSE; HS3ST3A1; HS3ST3B1; HYAL3 |
| positive regulation of adaptive immune response: GO | 69 | 8 | 8.57E−03 | 6.46E−02 | 2.54 | CD80; IFNG; IL12B; IL1B; PRKCQ; PYCARD; RSAD2; SASH3 |
| aurka activation by tpx2 | 56 | 7 | 8.57E−03 | 6.46E−02 | 2.73 | AURKA; CDK1; HMMR; NEK2; PLK1; TPX2; TUBA1C |
| cysteine and methionine metabolism | 32 | 5 | 8.58E−03 | 6.46E−02 | 3.42 | AHCY; GOT2; IL4I1; LDHA; SRM |
| negative regulation of adaptive immune response: GO | 32 | 5 | 8.58E−03 | 6.46E−02 | 3.42 | IL4R; IL7R; JAK3; SAMSN1; SLAMF1 |
| primary immunodeficiency | 32 | 5 | 8.58E−03 | 6.46E−02 | 3.42 | CD3E; ICOS; IL7R; JAK3; TAP2 |
| ubiquitin dependent protein catabolic process: GO | 126 | 12 | 8.87E−03 | 6.66E−02 | 2.08 | AURKA; BUB1B; CCNB1; CDC20; CDK1; FBXO45; HERC6; MAD2L1; PLK1; PTTG1; UBE2C; UHRF1 |
| negative regulation of cell activation: GO | 141 | 13 | 8.88E−03 | 6.66E−02 | 2.02 | CD274; CTLA4; FOXF1; HMOX1; IDO1; IL2RA; IL4R; JAK3; PGLYRP2; PRDM1; SAMSN1; TNFRSF21; ZC3H12A |
| negative regulation of dna binding: GO | 44 | 6 | 8.95E−03 | 6.70E−02 | 2.98 | GZMA; HMGA2; HMOX1; IFI16; MDFI; NEK2 |
| peptide ligand binding receptors | 70 | 8 | 9.34E−03 | 6.97E−02 | 2.50 | CCL22; CCL3; CCL7; CCR4; CCR5; CXCL5; CXCL9; FPR3 |
| positive regulation of erk1 and erk2 cascade: GO | 142 | 13 | 9.40E−03 | 7.01E−02 | 2.00 | ADCYAP1; CCL18; CCL22; CCL3; CCL7; IL1B; IL26; IL6; NDRG4; NTRK1; PYCARD; S100A7; SLAMF1 |
| acute inflammatory response: GO | 57 | 7 | 9.44E−03 | 7.02E−02 | 2.69 | F12; HIF1A; IL1B; IL22; IL6; S100A8; SERPINA1 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| benzene containing compound metabolic process: GO | 22 | 4 | 9.57E−03 | 7.02E−02 | 3.98 | GOT2; IDO1; KYNU; TDO2 |
| integrin a9b1 pathway | 22 | 4 | 9.57E−03 | 7.02E−02 | 3.98 | CSF2; KCNJ15; TGM2; TNC |
| protein depolymerization: GO | 22 | 4 | 9.57E−03 | 7.02E−02 | 3.98 | HSPA8; KIF14; KIF18A; KIF2C |
| proliferation: GO | 22 | 4 | 9.57E−03 | 7.02E−02 | 3.98 | CD3E; CD80; EBI3; IL12B |
| regulation of response to interferon gamma: GO | 22 | 4 | 9.57E−03 | 7.02E−02 | 3.98 | IFNG; PARP9; SOCS3; STAT1 |
| regulation of t helper 1 type immune response: GO | 22 | 4 | 9.57E−03 | 7.02E−02 | 3.98 | CD80; IL12B; IL4R; JAK3 |
| ribonucleoside catabolic process: GO | 22 | 4 | 9.57E−03 | 7.02E−02 | 3.98 | AHCY; APOBEC3A; PNP; UPP1 |
| regulation of mitochondrion organization: GO | 190 | 16 | 1.01E−02 | 7.37E−02 | 1.84 | BAK1; C1QBP; FAM162A; HIF1A; ITGAX; MMP9; PLAUR; PPIF; PRELID1; PYCARD; RAC2; SFN; SLC25A5; TNFSF10; UGCG; YWHAQ |
| regulation of protein ubiquitination involved in ubiquitin dependent protein catabolic process: GO | 99 | 10 | 1.02E−02 | 7.47E−02 | 2.21 | BUB1B; CCNB1; CDC20; CDK1; MAD2L1; PLK1; PSMA4; PSMA5; PSMB6; UBE2C |
| synthesis of dna | 99 | 10 | 1.02E−02 | 7.47E−02 | 2.21 | CCNA2; CDC45; CDC6; GINS3; ORC1; ORC6; PCNA; PSMA4; PSMA5; PSMB6 |
| leukocyte homeostasis: GO | 58 | 7 | 1.04E−02 | 7.52E−02 | 2.64 | BAK1; CCNB2; HIF1A; IFNG; IL2RA; IL6; JAK3 |
| p450 | 58 | 7 | 1.04E−02 | 7.52E−02 | 2.64 | ADH7; ALDH1A3; CYP2S1; GSTO1; GSTP1; UGT1A10; UGT1A7 |
| negative regulation of cellular protein catabolic process: GO | 58 | 7 | 1.04E−02 | 7.52E−02 | 2.64 | BUB1; BUB1B; LAMP3; MAD2L1; PBK; PLK1; TTK |
| positive regulation of cellular amide metabolic process: GO | 100 | 10 | 1.10E−02 | 7.92E−02 | 2.19 | C1QBP; DEFB103A; DEFB103B; EIF4A3; EIF5A; EIF5AL1; IL6; KRT17; PTAFR; ZC3H12A |
| regulation of defense response to virus: GO | 176 | 15 | 1.10E−02 | 7.92E−02 | 1.86 | AP1S3; C1QBP; FGFBP1; HIST1H3A; HIST1H3B; HIST1H3C; HIST1H3F; HIST1H3G; HIST1H3H; HIST1H3i; HIST1H3J; IL12B; IL2RA; TREM1; ZC3H12A |
| meiotic cell cycle: GO | 145 | 13 | 1.11E−02 | 7.92E−02 | 1.96 | ASPM; AURKA; CDC25B; CKS2; EXO1; H2AFX; KIF18A; MND1; NEK2; PLK1; PTTG1; TOP2A; TRIP13 |
| g alpha i signalling events | 86 | 9 | 1.12E−02 | 7.92E−02 | 2.29 | CCR4; CCR5; CXCL5; CXCL9; FPR3; GNGT2; HCAR3; HRH3; S1PR4 |
| tetrapyrrole binding: GO | 115 | 11 | 1.12E−02 | 7.92E−02 | 2.09 | CYCS; CYP24A1; CYP27B1; CYP27C1; CYP2S1; CYP4F11; CYP4F22; HMOX1; IDO1; TCN1; TDO2 |
| attenuation phase | 23 | 4 | 1.13E−02 | 7.92E−02 | 3.80 | FPR1; HSPA6; HSPA8; TNFRSF21 |
| cell differentiation involved in embryonic placenta development: GO | 23 | 4 | 1.13E−02 | 7.92E−02 | 3.80 | EOMES; MDFI; PRDM1; SOCS3 |
| cellcycle pathway | 23 | 4 | 1.13E−02 | 7.92E−02 | 3.80 | CCNB1; CCNE1; CDC25A; CDK1 |
| cyclins and cell cycle regulation | 23 | 4 | 1.13E−02 | 7.92E−02 | 3.80 | CCNB1; CCNE1; CDC25A; CDK1 |
| histone phosphorylation: GO | 23 | 4 | 1.13E−02 | 7.92E−02 | 3.80 | AURKA; CCNB1; CDK1; HMGA2 |
| inflam pathway | 23 | 4 | 1.13E−02 | 7.92E−02 | 3.80 | CSF2; IFNG; IL12B; IL6 |
| interleukin 4 pathway | 23 | 4 | 1.13E−02 | 7.92E−02 | 3.80 | IL13RA1; IL4R; JAK3; PI3 |
| myeloid dendritic cell activation: GO | 23 | 4 | 1.13E−02 | 7.92E−02 | 3.80 | CSF2; PYCARD; SLAMF1; TNFSF9 |
| positive regulation of chromosome segregation: GO | 23 | 4 | 1.13E−02 | 7.92E−02 | 3.80 | CCNB1; CDC6; DLGAP5; PLK1 |
| response: GO | 23 | 4 | 1.13E−02 | 7.92E−02 | 3.80 | IDO1; IL4R; IL6; RSAD2 |
| response to sterol: GO | 23 | 4 | 1.13E−02 | 7.92E−02 | 3.80 | ACP5; CCL3; CCR5; LRP8 |
| nod like receptor signaling pathway | 59 | 7 | 1.14E−02 | 7.98E−02 | 2.59 | CARD6; CCL7; CXCL1; IL1B; IL6; MEFV; PYCARD |
| signaling by ils | 101 | 10 | 1.17E−02 | 8.20E−02 | 2.17 | CDK1; CSF2; IL1B; IL2RA; IL6; IL7R; JAK3; MYD88; SOCS3; STAT1 |
| organ regeneration: GO | 73 | 8 | 1.19E−02 | 8.35E−02 | 2.40 | BAK1; CCNA2; CCNE1; CDK1; GSTP1; NR4A3; PGF; SOCS3 |
| cellular response to fatty acid: GO | 47 | 6 | 1.23E−02 | 8.60E−02 | 2.79 | CCNB1; IL1B; NME1; PTAFR; TNC; ZC3H12A |
| negative regulation of leukocyte | 60 | 7 | 1.24E−02 | 8.66E−02 | 2.55 | CD274; CTLA4; GSTP1; IDO1; IL2RA; PRDM1; TNFRSF21 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| proliferation: GO | | | | | | |
| regulation of meiotic cell cycle: GO | 35 | 5 | 1.26E−02 | 8.75E−02 | 3.12 | ASPM; CALR; CDC20; OSM; WNT5A |
| negative regulation of hemopoiesis: GO | 117 | 11 | 1.27E−02 | 8.80E−02 | 2.06 | CCL3; CTLA4; HIST1H4I; HIST1H4J; HIST1H4K; HIST1H4L; IL4R; JAK3; LTF; NME1; PGLYRP2 |
| peptide or polysaccharide antigen via mhc class ii: GO | 88 | 9 | 1.29E−02 | 8.92E−02 | 2.24 | AP1S3; CENPE; IFI30; KIF11; KIF15; KIF18A; KIF23; KIF2C; KIF4A |
| process: GO | 74 | 8 | 1.29E−02 | 8.93E−02 | 2.36 | CD274; HIF1A; IDO1; JAK3; NR4A3; PRELID1; PRKCQ; WNT5A |
| aromatic amino acid family metabolic process: GO | 24 | 5 | 1.31E−02 | 8.96E−02 | 3.64 | IDO1; IL4I1; KYNU; TDO2 |
| ascorbate and aldarate metabolism | 24 | 4 | 1.31E−02 | 8.96E−02 | 3.64 | AKR1B10; ALDH1A3; UGT1A10; UGT1A7 |
| death: GO | 24 | 4 | 1.31E−02 | 8.96E−02 | 3.64 | BAK1; DNASEIL3; IL1B; NTRK1 |
| glycosphingolipid biosynthesis lacto and neolacto series | 24 | 4 | 1.31E−02 | 8.96E−02 | 3.64 | B3GNT3; FUT1; FUT2; FUT3 |
| negative regulation of hematopoietic progenitor cell differentiation: GO | 24 | 4 | 1.31E−02 | 8.96E−02 | 3.64 | HIST1H4I; HIST1H4J; HIST1H4K; HIST1H4L |
| transcription: GO | 24 | 4 | 1.31E−02 | 8.96E−02 | 3.64 | CCL3; HMGA2; IFITM3; TRIM14 |
| regulation of meiotic nuclear division: GO | 24 | 4 | 1.31E−02 | 8.96E−02 | 3.64 | CALR; CDC20; OSM; WNT5A |
| foxo pathway | 48 | 6 | 1.36E−02 | 9.25E−02 | 2.73 | CCNB1; PLK1; RALB; RAN; SFN; YWHAQ |
| immunity: GO | 48 | 6 | 1.36E−02 | 9.25E−02 | 2.73 | IL12B; IL1B; IL7R; RSAD2; SASH3; SLAMF1 |
| response to gamma radiation: GO | 48 | 6 | 1.36E−02 | 9.25E−02 | 2.73 | BAK1; CCL7; CXCL10; H2AFX; IL1B; SOCS3 |
| pallium development: GO | 134 | 12 | 1.41E−02 | 9.55E−02 | 1.96 | ASPM; CDK5R1; CNTNAP2; EOMES; FBXO45; H2AFX; HIF1A; KIF14; LRP8; NME1; NR4A3; RAN |
| gap junction trafficking | 36 | 5 | 1.42E−02 | 9.55E−02 | 3.04 | GJB2; GJB6; TUBA1C; TUBB2A; TUBB6 |
| glycosyl compound catabolic process: GO | 36 | 5 | 1.42E−02 | 9.55E−02 | 3.04 | AHCY; APOBEC3A; PNP; TYMP; UPP1 |
| negative regulation of reactive oxygen species metabolic process: GO | 36 | 5 | 1.42E−02 | 9.55E−02 | 3.04 | ACP5; HIF1A; HK2; MMP3; ZC3H12A |
| heparin binding: GO | 135 | 12 | 1.49E−02 | 1.00E−01 | 1.94 | CCL7; CXCL10; CXCL11; CXCL 13; CXCL6; FGFBP1; HBEGF; LIPG; LTF; NELL2; PGF; SELL |
| gap junction trafficking and regulation | 25 | 4 | 1.52E−02 | 1.01E−01 | 3.50 | GJB2; TUBA1C; TUBB2A; TUBB6 |
| metabolism | 25 | 4 | 1.52E−02 | 1.01E−01 | 3.50 | HPSE; HS3ST1; HS3ST3A1; HS3ST3B1 |
| positive regulation of leukocyte apoptotic process: GO | 25 | 4 | 1.52E−02 | 1.01E−01 | 3.50 | IDO1; NR4A3; PRELID1; WNT5A |
| differentiation: GO | 25 | 4 | 1.52E−02 | 1.01E−01 | 3.50 | AQP3; CYP27B1; IL20; TRIM16 |
| ter calcium pathway | 25 | 4 | 1.52E−02 | 1.01E−01 | 3.50 | CSF2; FOSL1; IFNG; IL2RA |
| cytoskeleton dependent cytokinesis: GO | 37 | 5 | 1.59E−02 | 1.05E−01 | 2.96 | CEP55; KIF20A; KIF23; KIF4A; PLK1 |
| pyrimidine containing compound biosynthetic process: GO | 37 | 5 | 1.59E−02 | 1.05E−01 | 2.96 | CMPK2; NME1; TK1; TYMP; UPP1 |
| gl/s dna damage checkpoints | 50 | 6 | 1.65E−02 | 1.09E−01 | 2.62 | CCNA2; CCNE1; CDC25A; CDC25B; PSMA5; PSMB6 |
| metabolism of nucleotides | 92 | 9 | 1.69E−02 | 1.12E−01 | 2.14 | ENTPD7; NME1; NUDT15; PNP; POMP; RRM2; TK1; TYMP; UPP1 |
| regulation of ligase activity: GO | 122 | 11 | 1.70E−02 | 1.12E−01 | 1.97 | BUB1B; CCNB1; CDC20; CDK1; MAD2L1; PLK1; PSMA4; PSMA5; PSMB6; UBE2C; UBE2S |
| antigen processing-cross presentation | 64 | 7 | 1.74E−02 | 1.14E−01 | 2.39 | CALR; CTSL; FCGR1A; MYD88; PSMA5; PSMB6; SEC61G |
| dna replication pre-initiation | 64 | 7 | 1.74E−02 | 1.14E−01 | 2.39 | CDC45; CDC6; MCM10; ORC1; ORC6; PSMA5; PSMB6 |
| m/g1 transition | 64 | 7 | 1.74E−02 | 1.14E−01 | 2.39 | CDC45; CDC6; MCM10; ORC1; ORC6; PSMA5; PSMB6 |
| response: GO | 64 | 7 | 1.74E−02 | 1.14E−01 | 2.39 | ADCYAP1; C1QBP; F12; GSTP1; IL1B; IL6; OSM |
| transition | 64 | 7 | 1.74E−02 | 1.14E−01 | 2.39 | AURKA; CCNB1; CCNB2; CDK1; NEK2; PLK1; TUBA1C |
| negative regulation of lymphocyte | 26 | 4 | 1.75E−02 | 1.14E−01 | 3.36 | HIF1A; IDO1; JAK3; PRKCQ |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| apoptotic process: GO | | | | | | |
| negative regulation of response to biotic stimulus: GO | 26 | 4 | 1.75E−02 | 1.14E−01 | 3.36 | C1QBP; IL2RA; LTF; PRDM1 |
| positive regulation of acute inflammatory response: GO | 26 | 4 | 1.75E−02 | 1.14E−01 | 3.36 | F12; IL1B; IL6; OSM |
| regulation of reactive oxygen species metabolic process: GO | 138 | 12 | 1.75E−02 | 1.14E−01 | 1.90 | ACP5; FOXM1; GSTP1; HIF1A; HK2; IFNG; IL1B; IL6; MMP3; PLAU; RAC2; ZC3H12A |
| drug metabolism other enzymes | 38 | 5 | 1.77E−02 | 1.15E−01 | 2.88 | TK1; TYMP; UGT1A10; UGT1A7; UPP1 |
| post-translational modification: synthesis of gpi-anchored proteins | 38 | 5 | 1.77E−02 | 1.15E−01 | 2.88 | ALPL; PIGW; PLAUR; ULBP2; VNN3 |
| alcohol catabolic process: GO | 51 | 6 | 1.81E−02 | 1.17E−01 | 2.57 | ADH7; AKR1B10; CYP24A1; CYP27B1; GK; TPI1 |
| production: GO | 51 | 6 | 1.81E−02 | 1.17E−01 | 2.57 | CAMP; CD2; IL1B; PYCARD; SERPINE1; WNT5A |
| process: GO | 51 | 6 | 1.81E−02 | 1.17E−01 | 2.57 | CCK; CCL3; IFNG; IL6; PTAFR; TNFRSF21 |
| positive regulation of cell cycle arrest: GO | 79 | 8 | 1.87E−02 | 1.20E−01 | 2.21 | AURKA; CCNB1; CDK1; CDK5R1; HMGA2; PCNA; PLK2; SFN |
| response to heat: GO | 79 | 8 | 1.87E−02 | 1.20E−01 | 2.21 | CXCL10; HMOX1; HSPA6; IL1B; IL6; OSM; PRKCQ; SOCS3 |
| positive regulation of cell cycle phase transition: GO | 65 | 7 | 1.88E−02 | 1.21E−01 | 2.36 | BIRC5; CDC45; CDC6; CDCA5; DLGAP5; PLK1; UBE2C |
| negative regulation of secretion: GO | 172 | 14 | 1.94E−02 | 1.24E−01 | 1.78 | FOXF1; HMOX1; HRH3; IL1B; IL36RN; IL6; OSM; RSAD2; SLAMF1; SRGN; TNFRSF21; TNFRSF9; VSNL1; ZC3H12A |
| myeloid cell activation involved in immune response: GO | 39 | 5 | 1.97E−02 | 1.25E−01 | 2.80 | CCL3; NR4A3; PLA2G3; PYCARD; SLAMF1 |
| positive regulation of wound healing: GO | 39 | 5 | 1.97E−02 | 1.25E−01 | 2.80 | F12; HBEGF; HPSE; S100A9; SERPINE1 |
| differentiation: GO | 39 | 5 | 1.97E−02 | 1.25E−01 | 2.80 | AQP3; CYP27B1; IL20; SFN; TRIM16 |
| degranulation: GO | 39 | 5 | 1.97E−02 | 1.25E−01 | 2.80 | FOXF1; HMOX1; IL4R; PTAFR; RAC2 |
| hsf1-dependent transactivation | 27 | 4 | 1.99E−02 | 1.25E−01 | 3.24 | FPR1; HSPA6; HSPA8; TNFRSF21 |
| immunoregulatory interactions between a lymphoid and a non lymphoid cell | 27 | 4 | 1.99E−02 | 1.25E−01 | 3.24 | CD3E; ULBP1; ULBP2; ULBP3 |
| mhc protein binding: GO | | | 1.99E−02 | 1.25E−01 | 3.24 | CLEC7A; KRT17; TAP2; VCP |
| phenylalanine metabolism | 27 | 4 | 1.99E−02 | 1.25E−01 | 3.24 | ALDH1A3; ESCO2; GOT2; IL4I1 |
| positive regulation of interleukin 10 | 27 | 4 | 1.99E−02 | 1.25E−01 | 3.24 | CD274; IL12B; PYCARD; SASH3 |
| production: GO | | 4 | | | | |
| positive regulation of monooxygenase activity: GO | 27 | 4 | 1.99E−02 | 1.25E−01 | 3.24 | CDH3; HIF1A; IFNG; IL1B |
| process: GO | 27 | 4 | 1.99E−02 | 1.25E−01 | 3.24 | NME1; TK1; TYMP; UPP1 |
| regulation of megakaryocyte differentiation: GO | 27 | 4 | 1.99E−02 | 1.25E−01 | 3.24 | HIST1H4I; HIST1H4J; HIST1H4K; HIST1H4L |
| telomere capping: GO | 27 | 4 | 1.99E−02 | 1.25E−01 | 3.24 | HIST1H4I; HIST1H4J; HIST1H4K; HIST1H4L |
| centrosomes | 66 | 7 | 2.04E−02 | 1.27E−01 | 2.32 | CCNB1; CDK1; NEK2; PLK1; TUBA1C; TUBB2A; TUBB6 |
| structure specific dna binding: GO | 110 | 10 | 2.04E−02 | 1.27E−01 | 1.99 | ZBP1BLM; GRHL3; H2AFZ; HIST1H1A; HISTIH1B; HMGA2; HMGB3; PIF1; RCC1; |
| cerebral cortex development: GO | 95 | 9 | 2.05E−02 | 1.28E−01 | 2.07 | ASPM; CDK5R1; CNTNAP2; EOMES; FBXO45; H2AFX; HIF1A; KIF14; LRP8 |
| cellular response to radiation: GO | 126 | 11 | 2.11E−02 | 1.31E−01 | 1.91 | BAK1; BLM; CDC25A; CNGB1; ECT2; H2AFX; HIF1A; HYAL3; IFI16; PBK; PCNA |
| positive regulation of epithelial cell proliferation: GO | 142 | 12 | 2.14E−02 | 1.33E−01 | 1.85 | CDH3; EPGN; HIF1A; IL6; MMP12; NME1; NR4A3; PGF; TGFA; TGM1; WNT5A; WNT7A |
| limbic system development: GO | 81 | 8 | 2.15E−02 | 1.33E−01 | 2.16 | ALDH1A3; CDK5R1; CNTNAP2; KIF14; LRP8; NME1; NR4A3; RAN |
| cdt1 association with the ede6 ore origin complex | 53 | 6 | 2.16E−02 | 1.33E−01 | 2.48 | CDC6; ORC1; ORC6; PSMA4; PSMA5; PSMB6 |
| regulation of cytokinesis: GO | 53 | 6 | 2.16E−02 | 1.33E−01 | 2.48 | AURKA; CDC25B; CDC6; ECT2; KIF14; KIF23 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| regulation of dna replication | 53 | 6 | 2.16E−02 | 1.33E−01 | 2.48 | CCNA2; MCM10; ORC1; ORC6; PSMA5; PSMB6 |
| state | 53 | 6 | 2.16E−02 | 1.33E−01 | 2.48 | CCNA2; CDC6; ORC1; ORC6; PSMA5; PSMB6 |
| cellular iron ion homeostasis: GO | 40 | 5 | 2.18E−02 | 1.34E−01 | 2.73 | HIF1A; HMOX1; HMOX2; LCN2; LTF |
| process: GO | 40 | 5 | 2.18E−02 | 1.34E−01 | 2.73 | ADCYAP1; HMOX1; IFNG; IL12B; ZC3H12A |
| tissue regeneration: GO | 40 | 5 | 2.18E−02 | 1.34E−01 | 2.73 | CCNB1; KLK6; PLAU; PRKCQ; WNT7A |
| meiosis i: GO | 67 | 7 | 2.20E−02 | 1.34E−01 | 2.28 | AURKA; CDC25B; CKS2; PLK1; PTTG1; TOP2A; TRIP13 |
| positive regulation of nf kappab transcription factor activity: GO | 127 | 11 | 2.23E−02 | 1.36E−01 | 1.89 | IL1B; IL6; LTF; NTRK1; PRKCQ; PYCARD; S100A12; S100A8; S100A9; TRIM14; WNT5A |
| carbohydrate derivative catabolic process: GO | 159 | 13 | 2.25E−02 | 1.37E−01 | 1.79 | AHCY; APOBEC3A; CHI3L2; HMMR; HPSE; HYAL3; NEU2; NUDT15; PGLYRP2; PGM2; PNP; TYMP; UPP1 |
| myelin sheath: GO | 159 | 13 | 2.25E−02 | 1.37E−01 | 1.79 | CCT5; ENO1; FSCN1; GOT2; GSTO1; HSPA8; INA; NME1; PGAMI; PRDX1; SLC25A5; TAGLN3; VCP |
| gene and protein expression by jak-stat signaling after interleukin-12 stimulation | 28 | 4 | 2.26E−02 | 1.37E−01 | 3.12 | CNN2; GSTO1; IFNG; LMNB1 |
| response to interleukin 4: GO | 28 | 4 | 2.26E−02 | 1.37E−01 | 3.12 | CTSB; IL24; IL4R; JAK3 |
| t cell differentiation involved in immune response: GO | 28 | 4 | 2.26E−02 | 1.37E−01 | 3.12 | EOMES; IFNG; IL12B; IL6 |
| cytokinesis: GO | 82 | 8 | 2.29E−02 | 1.39E−01 | 2.13 | BIRC5; CEP55; ECT2; KIF20A; KIF23; KIF4A; PLK1; RALB |
| regulation of cell cycle arrest: GO | 97 | 9 | 2.32E−02 | 1.40E−01 | 2.03 | AURKA; CCNB1; CDK1; CDK5R1; FOXM1; HMGA2; PCNA; PLK2; SFN |
| placenta development: GO | 128 | 11 | 2.34E−02 | 1.41E−01 | 1.88 | CSF2; CTSB; CYP27B1; EOMES; FOSL1; GJB2; HIF1A; MDFI; PHLDA2; PRDM1; SOCS3 |
| glutathione metabolic process: GO | 54 | 6 | 2.35E−02 | 1.41E−01 | 2.43 | CHAC1; CHAC2; CNDP2; GGCT; GSTO1; GSTP1 |
| multicellular organismal macromolecule metabolic process: GO | 68 | 7 | 2.36E−02 | 1.42E−01 | 2.25 | CTSB; HIF1A; KLK6; MMP1; MMP12; MMP3; MMP9 |
| assembly of collagen fibrils and other multimeric structures | 41 | 5 | 2.41E−02 | 1.43E−01 | 2.67 | CTSB; CTSL; MMP1; MMP3; MMP9 |
| cdt1 association with the ede6:ore:origin complex | 41 | 5 | 2.41E−02 | 1.43E−01 | 2.67 | CDC6; ORC1; ORC6; PSMA5; PSMB6 |
| hsp90 chaperone cycle for steroid hormone receptors (shr) | 41 | 5 | 2.41E−02 | 1.43E−01 | 2.67 | FPR1; HSPA8; TUBA1C; TUBB2A; TUBB6 |
| proteasome | 41 | 5 | 2.41E−02 | 1.43E−01 | 2.67 | IFNG; POMP; PSMA4; PSMA5; PSMB6 |
| process: GO | 41 | 5 | 2.41E−02 | 1.43E−01 | 2.67 | APOBEC3A; NME1; TK1; TYMP; UPP1 |
| ribosome binding: GO | 41 | 5 | 2.41E−02 | 1.43E−01 | 2.67 | C1QBP; EIF5A; EIF5AL1; EIF6; ZC3H12A |
| proteins | 41 | 5 | 2.41E−02 | 1.43E−01 | 2.67 | CBX2; HIST1H4I; HIST1H4J; HIST1H4K; HIST1H4L |
| tumor necrosis factor mediated signaling pathway: GO | 113 | 10 | 2.42E−02 | 1.43E−01 | 1.94 | PSMA4; PSMA5; PSMB6; PYCARD; STAT1; TNFRSF12A; TNFRSF21; TNFRSF4; TNFRSF9; TXNDC17 |
| alpha amino acid catabolic process: GO | 83 | 8 | 2.45E−02 | 1.45E−01 | 2.11 | AHCY; ALDH4A1; GOT2; HAL; IDO1; IL4I1; KYNU; TDO2 |
| monooxygenase activity: GO | 83 | 8 | 2.45E−02 | 1.45E−01 | 2.11 | CH25H; CYP24A1; CYP27B1; CYP27C1; CYP2S1; CYP4F11; CYP4F22; SQLE |
| tryptophan metabolism | 83 | 8 | 2.45E−02 | 1.45E−01 | 2.11 | ALDH1A3; CYP4F11; IDO1; IL4I1; KYNU; OGDHL; TDO2; UHRF1 |
| intrinsic apoptotic signaling pathway in response to dna damage: GO | 69 | 7 | 2.54E−02 | 1.48E−01 | 2.22 | AEN; BAK1; BCL2A1; HMOX1; IFI16; PYCARD; SFN |
| process: GO | 29 | 4 | 2.55E−02 | 1.48E−01 | 3.02 | GK; PGM2; PYGL; TPII |
| euchromatin: GO | 29 | 4 | 2.55E−02 | 1.48E−01 | 3.02 | CBX2; H2AFZ; HIST1H1A; UHRF1 |
| hyaluronan metabolic process: GO | 29 | 4 | 2.55E−02 | 1.48E−01 | 3.02 | HAS3; HMMR; HYAL3; IL1B |
| maternal placenta development: GO | 29 | 4 | 2.55E−02 | 1.48E−01 | 3.02 | CTSB; CYP27B1; GJB2; PRDM1 |
| activation: GO | 29 | 4 | 2.55E−02 | 1.48E−01 | 3.02 | CTLA4; PRDM1; SAMSN1; TNFRSF21 |
| negative regulation of cellular response | 29 | 4 | 2.55E−02 | 1.48E−01 | 3.02 | IL1B; PRKCQ; PTPRE; SOCS3 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| to insulin stimulus: GO | | | | | | |
| production involved in immune response: GO | 29 | 4 | 2.55E−02 | 1.48E−01 | 3.02 | NR4A3; RSAD2; SASH3; WNT5A |
| regulation of mast cell activation involved in immune response: GO | 29 | 4 | 2.55E−02 | 1.48E−01 | 3.02 | FOXF1; HMOX1; IL4R; RAC2 |
| substance: GO | 29 | 4 | 2.55E−02 | 1.48E−01 | 3.02 | GSTO1; HMOX1; PPIF; ZC3H12A |
| phase ii conjugation | 55 | 6 | 2.55E−02 | 1.48E−01 | 2.39 | AHCY; CNDP2; GGCT; GSTO1; GSTP1; UGT1A7 |
| negative regulation of apoptotic signaling pathway: GO | 179 | 14 | 2.64E−02 | 1.53E−01 | 1.71 | CSF2; GSTP1; HIF1A; HMOX1; IFI6; IL19; IL1B; MMP9; PLAUR; PPIF; PRELID1; SERPINE1; SLC25A5; TNFSF10 |
| alpha beta t cell differentiation: GO | 42 | 5 | 2.65E−02 | 1.53E−01 | 2.60 | EOMES; IFNG; IL12B; IL6; RSAD2 |
| protein self association: GO | 42 | 5 | 2.65E−02 | 1.53E−01 | 2.60 | CTSB; CTSC; PCSK9; RSAD2; S100A7A |
| stat cascade: GO | 42 | 5 | 2.65E−02 | 1.53E−01 | 2.60 | JAK3; NMI; OSM; SOCS3; STAT1 |
| homeostasis of number of cells: GO | 163 | 13 | 2.69E−02 | 1.55E−01 | 1.74 | BAK1; CCNB2; CCR4; GCNT4; HIF1A; HMOX1; IFNG; IL2RA; IL6; IL7R; JAK3; PRDX1; SASH3 |
| orc1 removal from chromatin | 70 | 7 | 2.73E−02 | 1.56E−01 | 2.19 | CCNA2; CDC6; ORC1; ORC6; PSMA4; PSMA5; PSMB6 |
| intra-golgi and retrograde golgi-to-er traffic | 131 | 11 | 2.73E−02 | 1.56E−01 | 1.84 | CENPE; KIF11; KIF15; KIF18A; KIF20A; KIF23; KIF2C; KIF4A; TUBA1C; TUBB2A; TUBB6 |
| modification by small protein conjugation or removal: GO | 131 | 11 | 2.73E−02 | 1.56E−01 | 1.84 | BUB1B; CCNB1; CDC20; CDK1; ISG15; MAD2L1; PSMA4; PSMA5; PSMB6; RNF222; UBE2C |
| atf2 pathway | 56 | 6 | 2.76E−02 | 1.58E−01 | 2.34 | CCNA2; IFNG; IL6; PLAU; SELE; SOCS3 |
| shp2 pathway | 56 | 6 | 2.76E−02 | 1.58E−01 | 2.34 | IFNG; IL2RA; IL6; JAK3; NTRK1; STAT1 |
| response to mechanical stimulus: GO | 197 | 15 | 2.79E−02 | 1.59E−01 | 1.67 | BAK1; CCNB1; CHRNA9; CNN2; CNTNAP2; CTSB; CXCL10; FOSL1; HIF1A; IL1B; IL6; MYD88; NTRK1; STRA6; TNC |
| positive regulation of dna metabolic process: GO | 164 | 13 | 2.81E−02 | 1.60E−01 | 1.73 | AREG; CALR; CCT5; CDK1; CSF2; FOXM1; H2AFX; IFNG; IL6; NEK2; PCNA; PRKCQ; TOP2A |
| cellular response to alkaloid: GO | 30 | 4 | 2.85E−02 | 1.61E−01 | 2.92 | BLM; CCNA2; NTRK1; PLAU |
| detoxification of reactive oxygen species | 30 | 4 | 2.85E−02 | 1.61E−01 | 2.92 | CYCS; ERO1A; GSTP1; PRDX1 |
| binding: GO | 30 | 4 | 2.85E−02 | 1.61E−01 | 2.92 | AREG; EPGN; HBEGF; TGFA |
| isoprenoid binding: GO | 30 | 4 | 2.85E−02 | 1.61E−01 | 2.92 | ADH7; CRABP2; UGT1A10; UGT1A7 |
| regulation of vascular endothelial growth factor production: GO | 30 | 4 | 2.85E−02 | 1.61E−01 | 2.92 | HIF1A; HPSE; IL1B; IL6 |
| regulation of peptidyl tyrosine phosphorylation: GO | 198 | 15 | 2.90E−02 | 1.64E−01 | 1.66 | CCK; CD3E; CD80; CSF2; EPGN; IFNG; IL12B; IL20; IL24; IL6; LRP8; OSM; SAMSN1; SOCS3; TGFA |
| positive regulation of oxidoreductase activity: GO | 43 | 5 | 2.91E−02 | 1.64E−01 | 2.54 | CDH3; CYP27B1; HIF1A; IFNG; IL1B |
| terpenoid metabolic process: GO | 86 | 8 | 2.96E−02 | 1.67E−01 | 2.03 | ADH7; AKR1B10; ALDH1A3; CRABP2; IL1B; LRP8; STRA6; UGT1A7 |
| response to purine containing compound: GO | 149 | 12 | 2.99E−02 | 1.68E−01 | 1.76 | AREG; CCNE1; FOSL1; FOXM1; HIF1A; IL1B; IL6; LDHA; NME1; PTAFR; SELL; STAT1 |
| positive regulation of stem cell proliferation: GO | 57 | 6 | 2.99E−02 | 1.68E−01 | 2.30 | ASPM; FOXF1; HIF1A; HMGA2; STAT1; WNT5A |
| pigment granule: GO | 102 | 5 | 3.09E−02 | 1.73E−01 | 1.93 | AHCY; ATP1B3; CTSB; GGH; HSPA8; PPIB; PRDX1; RAB38; RAN |
| negative regulation of leukocyte differentiation: GO | 72 | 7 | 3.13E−02 | 1.75E−01 | 2.13 | CCL3; CTLA4; IL4R; JAK3; LTF; NME1; PGLYRP2 |
| mediator: GO | 118 | 10 | 3.15E−02 | 1.75E−01 | 1.85 | AEN; AURKA; CCNB1; CDK1; FOXM1; IFI16; PCNA; PLK2; PYCARD; SFN |
| iron ion binding: GO | 134 | 11 | 3.16E−02 | 1.75E−01 | 1.80 | ACP5; CALR; CH25H; CYP24A1; CYP27B1; CYP27C1; CYP2S1; CYP4F11; CYP4F22; LCN2; LTF |
| response to ionizing radiation: GO | 134 | 11 | 3.16E−02 | 1.75E−01 | 1.80 | AEN; BAK1; BLM; CCL7; CXCL10; ECT2; H2AFX; HIF1A; IFI16; IL1B; SOCS3 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| centrosome cycle: GO | 44 | 5 | 3.18E−02 | 1.75E−01 | 2.49 | AURKA; CDK1; KIF11; NEK2; STIL |
| neuron death: GO | 44 | 5 | 3.18E−02 | 1.75E−01 | 2.49 | FAM162A; GAPDH; KLK6; PLAU; TNFRSF21 |
| positive regulation of reproductive process: GO | 44 | 5 | 3.18E−02 | 1.75E−01 | 2.49 | AURKA; C1QBP; PLAU; PTAFR; WNT5A |
| production: GO | 44 | 5 | 3.18E−02 | 1.75E−01 | 2.49 | IFNG; IL4R; IL6; SASH3; TNFRSF4 |
| response to nicotine: GO | 44 | 5 | 3.18E−02 | 1.75E−01 | 2.49 | CHRNA3; CHRNA6; HMOX1; NTRK1; SLC7A11 |
| t cell activation involved in immune response: GO | 44 | 5 | 3.18E−02 | 1.75E−01 | 2.49 | EOMES; IFNE; IFNG; IL12B; IL6 |
| nuclear heterochromatin: GO | 31 | 4 | 3.19E−02 | 1.75E−01 | 2.82 | ESCO2; H2AFZ; HIST1H1B; UHRF1 |
| porphyrin and chlorophyll metabolism | 31 | 4 | 3.19E−02 | 1.75E−01 | 2.82 | HMOX1; HMOX2; UGT1A10; UGT1A7 |
| positive regulation of t cell mediated immunity: GO | 31 | 4 | 3.19E−02 | 1.75E−01 | 2.82 | IL12B; IL1B; RSAD2; SASH3 |
| cyclin a:cdk2-associated events at s phase entry | 58 | 6 | 3.22E−02 | 1.77E−01 | 2.26 | CCNA2; CCNE1; CDC25A; CDC25B; PSMA5; PSMB6 |
| stress: GO | 58 | 6 | 3.22E−02 | 1.77E−01 | 2.26 | ACP5; ADCYAP1; CCK; IDO1; NTRK1; OSM |
| cellular response to alcohol: GO | 103 | 9 | 3.27E−02 | 1.79E−01 | 1.91 | BLM; CCL7; CCNA2; CYP24A1; H2AFZ; IL6; LRP8; PTAFR; TNC |
| myeloid leukocyte activation: GO | 88 | 8 | 3.34E−02 | 1.82E−01 | 1.99 | CCL3; CSF2; NR4A3; PLA2G3; PYCARD; S100A12; SLAMF1; TNFSF9 |
| retrograde vesicle mediated transport golgi to er: GO | 73 | 7 | 3.34E−02 | 1.82E−01 | 2.10 | CENPE; KIF11; KIF15; KIF18A; KIF23; KIF2C; KIF4A |
| securin | 45 | 5 | 3.47E−02 | 1.87E−01 | 2.43 | CDC20; PSMA5; PSMB6; PTTG1; UBE2C |
| chaperonin-mediated protein folding | 45 | 5 | 3.47E−02 | 1.87E−01 | 2.43 | CCNE1; CCT5; TUBA1C; TUBB2A; TUBB6 |
| positive regulation of calcium ion transport into cytosol: GO | 45 | 5 | 3.47E−02 | 1.87E−01 | 2.43 | BAK1; CXCL10; CXCL11; CXCL9; GSTO1 |
| regulation of nf kappab import into nucleus: GO | 45 | 5 | 3.47E−02 | 1.87E−01 | 2.43 | IL12B; IL1B; PRDX1; PRKCQ; ZC3H12A |
| cellular ketone metabolic process: GO | 59 | 6 | 3.47E−02 | 1.87E−01 | 2.22 | AKR1B10; CYP4F11; GOT2; IDO1; KYNU; TDO2 |
| cyclin e associated events during g1/s transition | 59 | 6 | 3.47E−02 | 1.87E−01 | 2.22 | CCNA2; CCNE1; CDC25A; CDC25B; PSMA5; PSMB6 |
| drug metabolism cytochrome p450 | 59 | 6 | 3.47E−02 | 1.87E−01 | 2.22 | ADH7; ALDH1A3; GSTO1; GSTP1; UGT1A10; UGT1A7 |
| tp53 regulates metabolic genes | 59 | 6 | 3.47E−02 | 1.87E−01 | 2.22 | COX7B; CYCS; PRDX1; SCO2; SFN; TIGAR |
| anchored component of membrane: GO | 120 | 10 | 3.48E−02 | 1.88E−01 | 1.82 | ALPL; CD177; CD2; LY6D; PLAUR; RAETIL; ULBP1; ULBP2; ULBP3; VNN3 |
| amino acid transport across the plasma membrane | 32 | 4 | 3.54E−02 | 1.89E−01 | 2.73 | SLC38A5; SLC7A1; SLC7A11; SLC7A5 |
| embryo implantation: GO | 32 | 4 | 3.54E−02 | 1.89E−01 | 2.73 | IL1B; MMP9; PLAU; VMP1 |
| graft versus host disease | 32 | 4 | 3.54E−02 | 1.89E−01 | 2.73 | CD80; IFNG; IL1B; IL6 |
| il12 stat4 pathway | 32 | 4 | 3.54E−02 | 1.89E−01 | 2.73 | CD3E; CD80; IFNG; IL2RA |
| negative regulation of lymphocyte mediated immunity: GO | 32 | 4 | 3.54E−02 | 1.89E−01 | 2.73 | IL7R; SERPINB4; SERPINB9; SLAMF1 |
| positive regulation of interleukin 12 production: GO | 32 | 4 | 3.54E−02 | 1.89E−01 | 2.73 | IDO1; IFNG; IL12B; TNFSF9 |
| digestion: GO | 89 | 8 | 3.54E−02 | 1.89E−01 | 1.97 | ADM2; AKR1B10; HTR3A; LDLR; LIPG; PRSS3; SLC5A1; VSIG1 |
| regulation of coagulation: GO | 74 | 7 | 3.57E−02 | 1.90E−01 | 2.07 | F12; HPSE; PLAU; PLAUR; PRKCQ; S100A9; SERPINE1 |
| acyl chain remodelling of pc | 20 | 3 | 3.63E−02 | 1.90E−01 | 3.28 | PLA2G3; PLA2G4D; PLBD1 |
| carboxyterminal post-translational modifications of tubulin | 20 | 3 | 3.63E−02 | 1.90E−01 | 3.28 | TUBA1C; TUBB2A; TUBB6 |
| cytokines and inflammatory response | 20 | 3 | 3.63E−02 | 1.90E−01 | 3.28 | CSF2; IFNG; IL6 |
| epiboly: GO | 20 | 3 | 3.63E−02 | 1.90E−01 | 3.28 | HBEGF; MMP12; WNT7A |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| degradation | 20 | 3 | 3.63E−02 | 1.90E−01 | 3.28 | ACP5; ALPL; CYP4F11 |
| intermediate filament organization: GO | 20 | 3 | 3.63E−02 | 1.90E−01 | 3.28 | KRT17; KRT9; NEFM |
| peptidyl cysteine modification: GO | 20 | 3 | 3.63E−02 | 1.90E−01 | 3.28 | GAPDH; S100A8; S100A9 |
| phosphatidylethanolamine acyl chain remodeling: GO | 20 | 3 | 3.63E−02 | 1.90E−01 | 3.28 | PLA2G3; PLA2G4D; PLBD1 |
| protein lipid complex binding: GO | 20 | 3 | 3.63E−02 | 1.90E−01 | 3.28 | LDLR; LRP8; PCSK9 |
| response to interferon beta: GO | 20 | 3 | 3.63E−02 | 1.90E−01 | 3.28 | IFITM1; IFITM3; STAT1 |
| cellular response to inorganic substance: GO | 137 | 11 | 3.63E−02 | 1.90E−01 | 1.76 | WNT5A |
| regulation of lymphocyte mediated immunity: GO | 105 | 9 | 3.64E−02 | 1.90E−01 | 1.87 | BLM; CALR; CCNA2; CCNB1; ECT2; EIF4A3; HIF1A; HMOX1; MMP3; PPIF; IFNG; IL12B; IL1B; IL7R; RSAD2; SASH3; SERPINB4; SERPINB9; SLAMF1 |
| motor activity: GO | 121 | 10 | 3.66E−02 | 1.91E−01 | 1.81 | CENPE; KIF11; KIF14; KIF15; KIF18A; KIF20A; KIF23; KIF2C; KIF4A; MYO1B |
| clathrin coated endocytic vesicle: GO | 60 | 6 | 3.73E−02 | 1.95E−01 | 2.19 | AP1S3; CTLA4; FCGR1A; HBEGF; LDLR; WNT5A |
| clathrin coated endocytic vesicle membrane: GO | 46 | 5 | 3.77E−02 | 1.96E−01 | 2.38 | AP1S3; FCGR1A; HBEGF; LDLR; WNT5A |
| type | 46 | 5 | 3.77E−02 | 1.96E−01 | 2.38 | CYP24A1; CYP27B1; CYP2S1; CYP4F11; CYP4F22 |
| protein kinase c binding: GO | 46 | 5 | 3.77E−02 | 1.96E−01 | 2.38 | C1QBP; NELL2; TOP2A; UGT1A10; UGT1A7 |
| regulation of wound healing: GO | 106 | 9 | 3.83E−02 | 1.99E−01 | 1.86 | F12; HBEGF; HPSE; PLAU; PLAUR; PRKCQ; S100A9; SERPINE1; TNFRSF12A |
| aminoglycan metabolic process: GO | 155 | 12 | 3.88E−02 | 2.01E−01 | 1.69 | B3GNT3; CHI3L2; CHST1; HAS3; HMMR; HPSE; HS3ST1; HS3ST3A1; HS3ST3B1; HYAL3; IL1B; PGLYRP2 |
| oxidoreductase activity acting on the aldehyde or oxo group of donors nad or nadp as acceptor: GO | 33 | 4 | 3.91E−02 | 2.02E−01 | 2.65 | AKR1B10; ALDH1A3; ALDH4A1; GAPDH |
| positive regulation of erbb signaling pathway: GO | 33 | 4 | 3.91E−02 | 2.02E−01 | 2.65 | EPGN; MMP9; PLAUR; TGFA |
| intermediate filament cytoskeleton: GO | 189 | 14 | 3.93E−02 | 2.03E−01 | 1.62 | LMNB1; LMNB2; NEFM; NME1 |
| negative regulation of extrinsic apoptotic signaling pathway: GO | 91 | 8 | 3.97E−02 | 2.05E−01 | 1.92 | BFSP1; INA; KRT16; KRT17; KRT24; KRT6A; KRT6B; KRT6C; KRT75; KRT9; CSF2; GSTP1; HMOX1; IFI6; IL19; IL1B; SERPINE1; TNFSF10 |
| iron ion homeostasis: GO | 61 | 6 | 4.00E−02 | 2.06E−01 | 2.15 | HIF1A; HMOX1; HMOX2; LCN2; LTF; STEAP4 |
| non recombinational repair: GO | 61 | 6 | 4.00E−02 | 2.06E−01 | 2.15 | H2AFX; HIST1H4I; HIST1H4J; HIST1H4K; HIST1H4L; POLQ |
| organic acid transmembrane transporter activity: GO | 123 | 10 | 4.03E−02 | 2.06E−01 | 1.78 | SLC16A1; SLC16A6; SLC16A9; SLC26A9; SLC2A9; SLC38A5; SLC6A11; SLC7A1; SLC7A11; SLC7A5 |
| cellular response to extracellular stimulus: GO | 173 | 13 | 4.08E−02 | 2.06E−01 | 1.64 | TNC; UPP1; ZC3H12A |
| genes | 47 | 5 | 4.09E−02 | 2.06E−01 | 2.33 | CCNE1; CYP24A1; DSC2; FOSL1; GSTP1; HMOX1; HSPA8; IFI16; PCSK9; RALB; HER C6; ISG15; KPNA2; MX1; STAT1 |
| fructose and mannose metabolism | 47 | 5 | 4.09E−02 | 2.06E−01 | 2.33 | AKR1B10; HK2; PFKFB4; PGM2; TPI1 |
| glutathione metabolism | 47 | 5 | 4.09E−02 | 2.06E−01 | 2.33 | GGCT; GSTO1; GSTP1; RRM2; SRM |
| isg15 antiviral mechanism | 47 | 5 | 4.09E−02 | 2.06E−01 | 2.33 | HERC6; ISG15; KPNA2; MX1; STAT1 |
| import: GO | 47 | 5 | 4.09E−02 | 2.06E−01 | 2.33 | CCL3; CXCL 10; CXCL11; CXCL9; GSTO1 |
| production: GO | 47 | 5 | 4.09E−02 | 2.06E−01 | 2.33 | CD3E; CD80; IL1B; PRKCQ; SASH3 |
| acyl chain remodelling of pe | 21 | 5 | 4.13E−02 | 2.06E−01 | 3.12 | PLA2G3; PLA2G4D; PLBD1 |
| cytolysis: GO | 21 | 5 | 4.13E−02 | 2.06E−01 | 3.12 | BAK1; GZMA; LYZ |
| transport: GO | 21 | 5 | 4.13E−02 | 2.06E−01 | 3.12 | CCL3; CCR5; VCP |
| fucosylation: GO | 21 | 3 | 4.13E−02 | 2.06E−01 | 3.12 | FUT1; FUT2; FUT3 |
| g protein coupled chemoattractant receptor activity: GO | 21 | 3 | 4.13E−02 | 2.06E−01 | 3.12 | CCR4; CCR5; CXCR4 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| process: GO | 21 | 3 | 4.13E−02 | 2.06E−01 | 3.12 | ST6GALNAC1; ST8S1A2; UGCG |
| lens fiber cell differentiation: GO | 21 | 3 | 4.13E−02 | 2.06E−01 | 3.12 | BFSP1; SLC7A11; WNT7A |
| mast cell activation: GO | 21 | 3 | 4.13E−02 | 2.06E−01 | 3.12 | NR4A3; PLA2G3; S100A12 |
| mast cell granule: GO | 21 | 3 | 4.13E−02 | 2.06E−01 | 3.12 | NR4A3; PLA2G3; SRGN |
| p38 mk2 pathway | 21 | 3 | 4.13E−02 | 2.06E−01 | 3.12 | CDC25B; SFN; YWHAQ |
| positive regulation of alcohol biosynthetic process: GO | 21 | 3 | 4.13E−02 | 2.06E−01 | 3.12 | IFNG; IL1B; PTAFR |
| signaling: GO | 21 | 3 | 4.13E−02 | 2.06E−01 | 3.12 | CXCL10; CXCL11; CXCL9 |
| regulation of macrophage activation: GO | 21 | 3 | 4.13E−02 | 2.06E−01 | 3.12 | IL4R; WNTSA; ZC3H12A |
| positive regulation of calcium ion transport: GO | 92 | 8 | 4.20E−02 | 2.09E−01 | 1.90 | BAK1; CCL3; CXCL 10; CXCL11; CXCL9; GSTO1; HOMER1; JAK3 |
| vitamin metabolic process: GO | 108 | 9 | 4.25E−02 | 2.11E−01 | 1.82 | ACP5; CYP24A1; CYP27B1; CYP4F11; GSTO1; NAMPT; PRSS3; TCN1; VNN3 |
| transferase activity transferring hexosyl groups: GO | 174 | 13 | 4.25E−02 | 2.11E−01 | 1.63 | B3GNT3; FUT1; FUT2; FUT3; GALNT6; GCNT4; HAS3; PYGL; SDF2L1; TYMP; UGCG; UGT1A10; UGT1A7 |
| glycosphingolipid metabolic process: GO | 62 | 6 | 4.29E−02 | 2.12E−01 | 2.12 | ARSH; GLTP; NEU2; ST6GALNAC1; ST8S1A2; UGCG |
| replication fork: GO | 62 | 6 | 4.29E−02 | 2.12E−01 | 2.12 | CDC45; H2AFX; MCM10; PCNA; PIF1; UHRF1 |
| positive regulation of protein kinase b signaling: GO | 77 | 7 | 4.30E−02 | 2.12E−01 | 1.99 | C1QBP; CCL3; FAM110C; HBEGF; HPSE; IL26; IL6 |
| tissue migration: GO | 77 | 7 | 4.30E−02 | 2.12E−01 | 1.99 | CXCL13; FERMT1; FOXF1; KRT16; PRSS3; S100A2; STAT1 |
| activity: GO | 34 | 4 | 4.31E−02 | 2.12E−01 | 2.57 | CCNB1; CCNB2; CDK1; CDK5R1 |
| negative regulation of lymphocyte differentiation: GO | 34 | 4 | 4.31E−02 | 2.12E−01 | 2.57 | CTLA4; IL4R; JAK3; PGLYRP2 |
| positive regulation of release of sequestered calcium ion into cytosol: GO | 34 | 4 | 4.31E−02 | 2.12E−01 | 2.57 | CXCL10; CXCL11; CXCL9; GSTO1 |
| regulation of proteasomal ubiquitin dependent protein catabolic process: GO | 141 | 11 | 4.34E−02 | 2.13E−01 | 1.71 | AURKA; BUB1; BUB1B; CCNB1; DLGAP5; MAD2L1; PBK; PLK1; PLK2; TTK; VCP |
| negative regulation of binding: GO | 125 | 10 | 4.42E−02 | 2.16E−01 | 1.75 | AURKA; EIF4A3; GZMA; HMGA2; HMOX1; IFI16; MDFI; NEK2; RALB; SLPI |
| negative regulation of i kappab kinase nf kappab signaling: GO | 48 | 5 | 4.42E−02 | 2.16E−01 | 2.28 | GSTP1; PYCARD; STAT1; TNIP3; ZC3H12A |
| postreplication repair: GO | 48 | 5 | 4.42E−02 | 2.16E−01 | 2.28 | ISG15; PCNA; UBE2F; USP43; VCP |
| regulation of mitochondrial membrane potential: GO | 48 | 5 | 4.42E−02 | 2.16E−01 | 2.28 | BAK1; CCK; IFI6; PRELID1; VCP |
| regulation of nitric oxide biosynthetic process: GO | 48 | 5 | 4.42E−02 | 2.16E−01 | 2.28 | ACP5; IFNG; IL1B; IL6; ZC3H12A |
| regulation of b cell activation: GO | 109 | 9 | 4.46E−02 | 2.18E−01 | 1.81 | CTLA4; IFNG; IGHG4; IL6; PRDM1; SAMSN1; SASH3; TNFRSF21; TNFRSF4 |
| carbohydrate homeostasis: GO | 142 | 11 | 4.53E−02 | 2.21E−01 | 1.69 | GJB6; GK; HIF1A; HK2; IL1B; IL6; NME1; OAS1; PLAU; PYGL; SLC16A1 |
| female gamete generation: GO | 78 | 7 | 4.56E−02 | 2.21E−01 | 1.96 | ASPM; CCNB1; CDC25B; FOSL1; IL1B; IL4R; TRIP13 |
| microtubule organizing center organization: GO | 78 | 7 | 4.56E−02 | 2.21E−01 | 1.96 | AURKA; CDK1; KIF11; NEK2; PLK1; SLC16A1; STIL |
| process: GO | 78 | 7 | 4.56E−02 | 2.21E−01 | 1.96 | CTSB; HIF1A; KLK6; MMP1; MMP12; MMP3; MMP9 |
| negative regulation of myeloid cell differentiation: GO | 78 | 7 | 4.56E−02 | 2.21E−01 | 1.96 | CCL3; HIST1H4I; HIST1H4J; HIST1H4K; HIST1H4L; LTF; NME1 |
| cellular glucose homeostasis: GO | 63 | 6 | 4.59E−02 | 2.22E−01 | 2.08 | GJB6; HIF1A; HK2; IL1B; NME1; PLAU |
| organic hydroxy compound catabolic process: GO | 63 | 6 | 4.59E−02 | 2.22E−01 | 2.08 | ADH7; AKR1B10; CYP24A1; CYP27B1; GK; TPI1 |
| phospholipase c activating g protein coupled receptor signaling pathway: GO | 63 | 6 | 4.59E−02 | 2.22E−01 | 2.08 | FPR1; GNA15; HOMER1; HRH3; LTB4R; TGM2 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| embryonic camera type eye morphogenesis: GO | 22 | 3 | 4.67E−02 | 2.22E−01 | 2.98 | ALDH1A3; STRA6; WNT5A |
| polarity: GO | 22 | 3 | 4.67E−02 | 2.22E−01 | 2.98 | FERMT1; FOXF1; WNT5A |
| indole containing compound metabolic process: GO | 22 | 3 | 4.67E−02 | 2.22E−01 | 2.98 | IDO1; KYNU; TDO2 |
| inflammatory response to antigenic stimulus: GO | 22 | 3 | 4.67E−02 | 2.22E−01 | 2.98 | AHCY; IL1B; IL2RA |
| metabolic disorders of biological oxidation enzymes | 22 | 3 | 4.67E−02 | 2.22E−01 | 2.98 | CYP24A1; CYP27B1; CYP4F22 |
| positive regulation of interleukin 4 production: GO | 22 | 3 | 4.67E−02 | 2.22E−01 | 2.98 | CD3E; PRKCQ; SASH3 |
| raf-independent mapk1/3 activation | 22 | 3 | 4.67E−02 | 2.22E−01 | 2.98 | CDK1; DUSP9; IL6 |
| regulation of cellular respiration: GO | 22 | 3 | 4.67E−02 | 2.22E−01 | 2.98 | HIF1A; PRELID1; VCP |
| regulation of cysteine type endopeptidase activity involved in apoptotic signaling pathway: GO | 22 | 3 | 4.67E−02 | 2.22E−01 | 2.98 | MMP9; PLAUR; TNFSF10 |
| regulation of hair cycle: GO | 22 | 3 | 4.67E−02 | 2.22E−01 | 2.98 | CDH3; HPSE; KRT17 |
| cellular response to reactive oxygen species: GO | 94 | 8 | 4.68E−02 | 2.23E−01 | 1.86 | CCNA2; CDK1; ECT2; HIF1A; IL6; MMP3; PPIF; PRDX1 |
| cellular metabolic compound salvage: GO | 35 | 4 | 4.73E−02 | 2.24E−01 | 2.50 | PNP; TK1; TYMP; UPP1 |
| cellular response to nutrient: GO | 35 | 4 | 4.73E−02 | 2.24E−01 | 2.50 | CCNE1; CYP24A1; HMOX1; TNC |
| negative regulation of innate immune response: GO | 35 | 4 | 4.73E−02 | 2.24E−01 | 2.50 | IFI16; NMI; SERPINB4; SERPINB9 |
| negative regulation of smooth muscle cell proliferation: GO | 35 | 4 | 4.73E−02 | 2.24E−01 | 2.50 | HMOX1; IFNG; IL12B; NDRG4 |
| alpha beta t cell activation: GO | 49 | 5 | 4.78E−02 | 2.25E−01 | 2.23 | EOMES; IFNG; IL12B; IL6; RSAD2 |
| assembly of the pre-replicative complex | 19 | 5 | 4.78E−02 | 2.25E−01 | 2.23 | CDC6; ORC1; ORC6; PSMA5; PSMB6 |
| cellular modified amino acid biosynthetic process: GO | 49 | 5 | 4.78E−02 | 2.25E−01 | 2.23 | AHCY; CHAC1; CHAC2; CNDP2; GGCT |
| lymphocyte homeostasis: GO | 49 | 5 | 4.78E−02 | 2.25E−01 | 2.23 | BAK1; CCNB2; HIF1A; IL2RA; JAK3 |
| regulation of dna recombination: GO | 49 | 5 | 4.78E−02 | 2.25E−01 | 2.23 | BLM; IFNG; IL7R; KPNA2; POLQ |
| positive regulation of leukocyte mediated immunity: GO | 79 | 7 | 4.84E−02 | 2.27E−01 | 1.94 | IFNG; IL12B; IL1B; IL4R; PTAFR; RSAD2; SASH3 |
| programmed cell death | 127 | 10 | 4.84E−02 | 2.27E−01 | 1.72 | BAK1; CLSPN; CYCS; DSG3; HISTIH1B; LMNB1; PSMA5; PSMB6; SFN; TNFSF10 |
| stimulus: GO | 64 | 6 | 4.90E−02 | 2.29E−01 | 2.05 | CLEC7A; GJB6; HIF1A; IL1B; NME1; PLAU |
| hippocampus development: GO | 64 | 6 | 4.90E−02 | 2.29E−01 | 2.05 | CDK5R1; KIF14; LRP8; NME1; NR4A3; RAN |
| phase1 functionalization of compounds | 64 | 6 | 4.90E−02 | 2.29E−01 | 2.05 | ADH7; CYP24A1; CYP27B1; CYP2S1; CYP4F11; SMOX |
| response to carbohydrate: GO | 144 | 11 | 4.93E−02 | 2.30E−01 | 1.67 | ACP5; CLEC7A; CTSB; GJB6; GSTP1; HIF1A; IL1B; LDHA; NME1; PLAU; PRKCQ |
| pyrimidine metabolism | 95 | 8 | 4.93E−02 | 2.30E−01 | 1.84 | CMPK2; NME1; PNP; POLR3G; RRM2; TK1; TYMP; UPP1 |
| transferase activity transferring pentosyl groups: GO | 50 | 5 | 5.14E−02 | 2.39E−01 | 2.19 | NAMPT; PARP9; PNP; TYMP; UPP1 |
| regulation of reproductive process: GO | 112 | 9 | 5.16E−02 | 2.39E−01 | 1.76 | ASPM; AURKA; C1QBP; CALR; CDC20; OSM; PLAU; PTAFR; WNT5A |
| membrane: GO | 36 | 4 | 5.17E−02 | 2.39E−01 | 2.43 | CD2; ULBP1; ULBP2; ULBP3 |
| cis trans isomerase activity: GO | 36 | 4 | 5.17E−02 | 2.39E−01 | 2.43 | FKBPL; PPIB; PPIF; PPIL1 |
| excretion: GO | 36 | 4 | 5.17E−02 | 2.39E−01 | 2.43 | AQP3; CHRNA3; HMOX1; UGT1A7 |
| translesion synthesis: GO | 36 | 4 | 5.17E−02 | 2.39E−01 | 2.43 | ISG15; PCNA; USP43; VCP |
| metalloendopeptidase activity: GO | 96 | 8 | 5.19E−02 | 2.39E−01 | 1.82 | ADAM23; ADAMDEC1; ADAMTS4; CLCA2; MMP1; MMP12; MMP3; MMP9 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| heterochromatin: GO | 65 | 6 | 5.22E−02 | 2.39E−01 | 2.02 | CBX2; ESCO2; H2AFZ; HIST1H1B; HMGA2; UHRF1 |
| permeability: GO | 65 | 6 | 5.22E−02 | 2.39E−01 | 2.02 | BAK1; HK2; PPIF; SFN; SLC25A5; YWHAQ |
| cargo concentration in the er | 23 | 3 | 5.24E−02 | 2.39E−01 | 2.85 | AREG; CTSC; TGFA |
| death receptor activity: GO | 23 | 3 | 5.24E−02 | 2.39E−01 | 2.85 | TNFRSF21; TNFRSF4; TNFRSF9 |
| ganglioside metabolic process: GO | 23 | 3 | 5.24E−02 | 2.39E−01 | 2.85 | NEU2; ST6GALNACI; ST8S1A2 |
| il receptor she signaling | 23 | 3 | 5.24E−02 | 2.39E−01 | 2.85 | CSF2; IL2RA; JAK3 |
| remodeling: GO | 23 | 3 | 5.24E−02 | 2.39E−01 | 2.85 | PLA2G3; PLA2G4D; PLBD1 |
| positive regulation of myotube differentiation: GO | 23 | 3 | 5.24E−02 | 2.39E−01 | 2.85 | CXCL9; IL4R; NEU2 |
| positive regulation of osteoclast differentiation: GO | 23 | 3 | 5.24E−02 | 2.39E−01 | 2.85 | IFNG; IL12B; IL20 |
| elongation: GO | 23 | 3 | 5.24E−02 | 2.39E−01 | 2.85 | EIF4A3; EIF5A; EIF5AL1 |
| secretory granule organization: GO | 23 | 3 | 5.24E−02 | 2.39E−01 | 2.85 | PLA2G3; RAB38; SRGN |
| termination of translesion dna synthesis | 23 | 3 | 5.24E−02 | 2.39E−01 | 2.85 | ISG15; PCNA; USP43 |
| organic acid binding: GO | 180 | 13 | 5.32E−02 | 2.42E−01 | 1.58 | CRABP2; FABP5; FABP6; GOT2; HSPA8; PYGL; S100A8; S100A9; SELE; ST8S1A2; TDO2; UGT1A10; UGT1A7 |
| maintenance of location: GO | 130 | 10 | 5.52E−02 | 2.51E−01 | 1.68 | ASPM; CALR; HK2; IL1B; MDFI; S100A7; S100A8; S100A9; SRGN; TWF1 |
| ddx58/ifih1-mediated induction of interferon-alpha/beta | 51 | 5 | 5.53E−02 | 2.51E−01 | 2.14 | HERC6; IL6; ISG15; MYD88; S100A12 |
| regulation of b cell proliferation: GO | 51 | 5 | 5.53E−02 | 2.51E−01 | 2.14 | CTLA4; PRDM1; SASH3; TNFRSF21; TNFRSF4 |
| metallopeptidase activity: GO | 164 | 12 | 5.56E−02 | 2.52E−01 | 1.60 | ADAM23; ADAMDEC1; ADAMTS4; CLCA2; CNDP2; CPA6; CPXM1; DPP3; MMP1; MMP12; MMP3; MMP9 |
| il 2 signaling | 37 | 4 | 5.63E−02 | 2.54E−01 | 2.36 | CDK1; CSF2; IL2RA; JAK3 |
| il-2 receptor beta chain in t cell activation | 37 | 4 | 5.63E−02 | 2.54E−01 | 2.36 | IL2RA; JAK3; NMI; SOCS3 |
| binding: GO | 37 | 4 | 5.63E−02 | 2.54E−01 | 2.36 | CHRNA3; CHRNA6; CHRNA9; HTR3A |
| regulation of centrosome cycle: GO | 37 | 4 | 5.63E−02 | 2.54E−01 | 2.36 | AURKA; KIF11; NEK2; PLK2 |
| modification by small protein conjugation or removal: GO | 182 | 13 | 5.72E−02 | 2.57E−01 | 1.56 | BUB1B; CCNB1; CDC20; CDK1; MAD2L1; NMI; PLK1; PSMA4; PSMA5; PSMB6; UBE2C; UBE2S; VCP |
| cellular response to light stimulus: GO | 82 | 7 | 5.72E−02 | 2.57E−01 | 1.87 | BAK1; CDC25A; CNGB1; HIF1A; HYAL3; PBK; PCNA |
| somatic recombination of immune receptors built from immunoglobulin superfamily domains: GO | 131 | 10 | 5.76E−02 | 2.58E−01 | 1.67 | C1QBP; CTSC; CXCL13; EBI3; EXO1; IGHG4; IL12B; IL4R; IL6; SLAMF1 |
| p53 downstream pathway | 131 | 10 | 5.76E−02 | 2.58E−01 | 1.67 | BAK1; BCL2A1; CCNB1; PCNA; PRDM1; PYCARD; S100A2; SERPINE1; SFN; TGFA |
| response to organophosphorus: GO | 131 | 10 | 5.76E−02 | 2.58E−01 | 1.67 | AREG; FOSL1; FOXMI; IL1B; LDHA; NME1; PTAFR; SELL; STAT1; TRIM16 |
| pi3kgamma | 24 | 3 | 5.84E−02 | 2.59E−01 | 2.73 | CSF2; IL2RA; JAK3 |
| g-protein beta: gamma signalling | 24 | 3 | 5.84E−02 | 2.59E−01 | 2.73 | CSF2; IL2RA; JAK3 |
| glutamate metabolic process: GO | 24 | 3 | 5.84E−02 | 2.59E−01 | 2.73 | ALDH4A1; GOT2; HAL |
| integrin2 pathway | 24 | 3 | 5.84E−02 | 2.59E−01 | 2.73 | TGAX; PLAU; PLAUR |
| molecular mediator of immune response: GO | 24 | 3 | 5.84E−02 | 2.59E−01 | 2.73 | HMOX1; JAK3; SLAMF1 |
| regulation of amino acid transport: GO | 24 | 3 | 5.84E−02 | 2.59E−01 | 2.73 | CCK; HRH3; IL1B |
| proliferation: GO | 24 | 3 | 5.84E−02 | 2.59E−01 | 2.73 | CDH3; SFN; TGM1 |
| response to gonadotropin: GO | 24 | 3 | 5.84E−02 | 2.59E−01 | 2.73 | CCNA2; FOXM1; GJB2 |
| rho gtpases activate iqgaps | 24 | 3 | 5.84E−02 | 2.59E−01 | 2.73 | TUBA1C; TUBB2A; TUBB6 |
| dna synthesis involved in dna repair: GO | 67 | 6 | 5.90E−02 | 2.61E−01 | 1.96 | BLM; EXO1; ISG15; PCNA; USP43; VCP |
| pyrimidine containing compound | 67 | 6 | 5.90E−02 | 2.61E−01 | 1.96 | APOBEC3A; CMPK2; NME1; TK1; TYMP; UPP1 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| metabolic process: GO | | | | | | |
| multicellular organismal water homeostasis: GO | 52 | 5 | 5.93E−02 | 2.62E−01 | 2.10 | AQP3; GRHL3; HRNR; KRT16; SFN |
| nfat 3pathway | 52 | 5 | 5.93E−02 | 2.62E−01 | 2.10 | KPNA2; PRKCQ; RAN; SFN; YWHAQ |
| process: GO | 149 | 11 | 6.02E−02 | 2.66E−01 | 1.61 | CMPK2; GARS; KYNU; NAMPT; NME1; OAS1; OAS2; PNP; RRM2; TK1; UPP1 |
| amb2 neutrophils pathway | 38 | 4 | 6.12E−02 | 2.66E−01 | 2.30 | IL6; MMP9; PLAU; PLAUR |
| dna | 38 | 4 | 6.12E−02 | 2.66E−01 | 2.30 | IFI16; MYD88; POLR3G; S100A12 |
| genitalia development: GO | 38 | 4 | 6.12E−02 | 2.66E−01 | 2.30 | BAK1; GJB2; STRA6; WNT5A |
| il2rb pathway | 38 | 4 | 6.12E−02 | 2.66E−01 | 2.30 | IL2RA; JAK3; NMI; SOCS3 |
| monocarboxylic acid transmembrane transporter activity: GO | 38 | 4 | 6.12E−02 | 2.66E−01 | 2.30 | SLC16A1; SLC16A6; SLC16A9; SLC6A11 |
| p53-independent dna damage response | 38 | 4 | 6.12E−02 | 2.66E−01 | 2.30 | CDC25A; CDC25B; PSMA5; PSMB6 |
| checkpoint | 38 | 4 | 6.12E−02 | 2.66E−01 | 2.30 | CDC25A; CDC25B; PSMA5; PSMB6 |
| recycling pathway of 11 | 38 | 4 | 6.12E−02 | 2.66E−01 | 2.30 | KIF4A; TUBA1C; TUBB2A; TUBB6 |
| activity: GO | 38 | 4 | 6.12E−02 | 2.66E−01 | 2.30 | GNA15; PTAFR; SIPR4; SELE |
| type i diabetes mellitus | 38 | 4 | 6.12E−02 | 2.66E−01 | 2.30 | CD80; IFNG; IL12B; IL1B |
| ubiquitin mediated degradation of phosphorylated ede25a | 38 | 4 | 6.12E−02 | 2.66E−01 | 2.30 | CDC25A; CDC25B; PSMA5; PSMB6 |
| lymphocyte differentiation: GO | 184 | 13 | 6.13E−02 | 2.66E−01 | 1.55 | BAK1; CD3E; EOMES; IFNE; IFNG; IL12B; IL6; IL7R; JAK3; LY6D; NTRK1; RSAD2; SLAMF1 |
| amine metabolic process: GO | 116 | 9 | 6.19E−02 | 2.68E−01 | 1.70 | FABP5; IDO1; KYNU; PLA2G3; PLA2G4D; PLBD1; SMOX; SRM; TDO2 |
| glycosaminoglycan metabolism | 116 | 9 | 6.19E−02 | 2.68E−01 | 1.70 | B3GNT3; CEMIP; CHST1; HAS3; HMMR; HPSE; HS3ST1; HS3ST3A1; HS3ST3B1 |
| meiotic cell cycle process: GO | 116 | 9 | 6.19E−02 | 2.68E−01 | 1.70 | ASPM; AURKA; CDC25B; CKS2; KIF18A; PLK1; PTTG1; TOP2A; TRIP13 |
| microtubule organizing center part: GO | 133 | 10 | 6.26E−02 | 2.70E−01 | 1.64 | AURKA; BIRC5; CEP55; HSPA6; PLA2G3; PLK2; POC1A; RAN; STIL; TOP2A |
| response to temperature stimulus: GO | 133 | 10 | 6.26E−02 | 2.70E−01 | 1.64 | CXCL10; GK; HMOX1; HSPA6; IL1B; IL6; NTRK1; OSM; PRKCQ; SOCS3 |
| morphogenesis of a branching structure: GO | 150 | 11 | 6.26E−02 | 2.70E−01 | 1.60 | AREG; BAK1; FOXF1; IL6; PGF; PRDM1; SOCS3; TGM2; TIMELESS; TNC; WNT5A |
| response to topologically incorrect protein: GO | 150 | 11 | 6.26E−02 | 2.70E−01 | 1.60 | BAK1; CALR; CHAC1; F12; HSPA6; HSPA8; IFNG; MANF; SDF2L1; SEC61G; VCP |
| g1 dna damage checkpoint: GO | 68 | 6 | 6.26E−02 | 2.70E−01 | 1.93 | AURKA; CCNB1; CDK1; PCNA; PLK2; SFN |
| cellular amino acid catabolic process: GO | 100 | 8 | 6.32E−02 | 2.72E−01 | 1.75 | AHCY; ALDH4A1; GOT2; HAL; IDO1; IL4I1; KYNU; TDO2 |
| scfskp2 mediated degradation of p27 p21 | 53 | 5 | 6.34E−02 | 2.72E−01 | 2.06 | CCNA2; CCNE1; PSMA4; PSMA5; PSMB6 |
| cytokine binding: GO | 84 | 7 | 6.36E−02 | 2.73E−01 | 1.82 | CCR5; CXCR4; IL12B; IL2RA; IL36RN; TNFRSF9; TRIM16 |
| cell adhesion molecules (cams) | 117 | 9 | 6.47E−02 | 2.75E−01 | 1.68 | CD2; CD274; CD80; CDH3; CNTNAP2; CTLA4; ICOS; SELE; SELL |
| antigen processing and presentation | 25 | 3 | 6.48E−02 | 2.75E−01 | 2.62 | CTSB; HSPA6; HSPA8 |
| cellular response to interleukin 4: GO | 25 | 3 | 6.48E−02 | 2.75E−01 | 2.62 | IL24; IL4R; JAK3 |
| embryonic axis specification: GO | 25 | 3 | 6.48E−02 | 2.75E−01 | 2.62 | STIL; WNT5A; WNT7A |
| glycosaminoglycan biosynthesis heparan sulfate | 25 | 3 | 6.48E−02 | 2.75E−01 | 2.62 | HS3ST1; HS3ST3A1; HS3ST3B1 |
| positive regulation of nf kappab import into nucleus: GO | 25 | 3 | 6.48E−02 | 2.75E−01 | 2.62 | IL12B; IL1B; PRKCQ |
| positive regulation of vascular endothelial growth factor production: GO | 25 | 3 | 6.48E−02 | 2.75E−01 | 2.62 | HIF1A; HPSE; IL1B |
| potassium ion import: GO | 25 | 3 | 6.48E−02 | 2.75E−01 | 2.62 | ATP12A; ATP1B3; KCNJ15 |
| steroid hormones | 25 | 3 | 6.48E−02 | 2.75E−01 | 2.62 | CYP24A1; CYP27B1; STARD4 |
| toll endogenous pathway | 25 | 3 | 6.48E−02 | 2.75E−01 | 2.62 | MYD88; S100A8; S100A9 |
| oxidoreductase activity acting on paired | 134 | 10 | 6.52E−02 | 2.76E−01 | 1.63 | CH25H; CYP24A1; CYP27B1; CYP27C1; CYP2S1; CYP4F11; CYP4F22; HMOX1; |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| donors with incorporation or reduction of molecular oxygen: GO | | | | | | HMOX2; SQLE |
| apoptotic cleavage of cellular proteins | 39 | 4 | 6.63E−02 | 2.80E−01 | 2.24 | CLSPN; DSG3; LMNB1; PRKCQ |
| negative regulation of coagulation: GO | 39 | 4 | 6.63E−02 | 2.80E−01 | 2.24 | F12; PLAU; PLAUR; SERPINE1 |
| positive regulation of dna binding: GO | 39 | 4 | 6.63E−02 | 2.80E−01 | 2.24 | HMGA2; MMP9; NME1; PLAUR |
| regulation of insulin receptor signaling pathway: GO | 39 | 4 | 6.63E−02 | 2.80E−01 | 2.24 | IL1B; PRKCQ; PTPRE; SOCS3 |
| leishmania infection | 69 | 6 | 6.64E−02 | 2.80E−01 | 1.90 | FCGR1A; IFNG; IL12B; IL1B; MYD88; STAT1 |
| regulation of myeloid cell differentiation: GO | 169 | 12 | 6.68E−02 | 2.81E−01 | 1.55 | CCL3; HIF1A; HIST1H4I; HIST1H4J; HIST1H4K; HIST1H4L; IFNG; IL12B; IL20; ISG15; LTF; NME1 |
| establishment of cell polarity: GO | 85 | 7 | 6.70E−02 | 2.82E−01 | 1.80 | CENPA; FERMT1; FOXF1; FSCN1; NDC80; WNT5A; WNT7A |
| endoplasmic reticulum golgi intermediate compartment membrane: GO | 54 | 5 | 6.78E−02 | 2.84E−01 | 2.02 | AREG; CTSC; SERPINA1; TGFA; VMP1 |
| il2 1pathway | 54 | 5 | 6.78E−02 | 2.84E−01 | 2.02 | IFNG; IL2RA; JAK3; SOCS3; STAT1 |
| neural nucleus development: GO | 54 | 5 | 6.78E−02 | 2.84E−01 | 2.02 | ALDH1A3; CDK5R1; INA; LDHA; YWHAQ |
| tap63 pathway | 54 | 5 | 6.78E−02 | 2.84E−01 | 2.02 | AEN; CLCA2; PLK1; S100A2; YWHAQ |
| cellular response to oxidative stress: GO | 170 | 12 | 6.92E−02 | 2.89E−01 | 1.54 | CCNA2; CDK1; ECT2; GJB2; HIF1A; HMOX1; IL6; MELK; MMP3; PPIF; PRDX1; ZC3H12A |
| ribonucleoprotein complex binding: GO | 86 | 7 | 7.05E−02 | 2.92E−01 | 1.78 | C1QBP; EIF4A3; EIF5A; EIF5AL1; EIF6; NME1; ZC3H12A |
| activation of phospholipase c activity: GO | 26 | 3 | 7.14E−02 | 2.92E−01 | 2.52 | GNA15; S1PR4; SELE |
| heterotypic cell cell adhesion: GO | 26 | 3 | 7.14E−02 | 2.92E−01 | 2.52 | CD2; DSC2; ITGAX |
| modulation by symbiont of host cellular process: GO | 26 | 3 | 7.14E−02 | 2.92E−01 | 2.52 | KPNA2; SERPINB9; ZC3H12A |
| epithelium: GO | 26 | 3 | 7.14E−02 | 2.92E−01 | 2.52 | FOXF1; GRHL3; WNT5A |
| differentiation: GO | 26 | 3 | 7.14E−02 | 2.92E−01 | 2.52 | CTLA4; IL4R; JAK3 |
| phospholipase a2 activity: GO | 26 | 3 | 7.14E−02 | 2.92E−01 | 2.52 | PLA2G3; PLA2G4D; PLBD1 |
| protein k11 linked ubiquitination: GO | 26 | 3 | 7.14E−02 | 2.92E−01 | 2.52 | UBE2C; UBE2S; UBE2T |
| sex chromosome: GO | 26 | 3 | 7.14E−02 | 2.92E−01 | 2.52 | ESCO2; H2AFX; H2AFZ |
| polymerases bypasses lesions on dna template | 26 | 3 | 7.14E−02 | 2.92E−01 | 2.52 | ISG15; PCNA; USP43 |
| apoptotic execution phase | 40 | 4 | 7.16E−02 | 2.92E−01 | 2.19 | CLSPN; DSG3; HIST1H1B; LMNB1 |
| bladder cancer | 40 | 4 | 7.16E−02 | 2.92E−01 | 2.19 | MMP1; MMP9; PGF; TYMP |
| cellular component disassembly involved in execution phase of apoptosis: GO | 40 | 4 | 7.16E−02 | 2.92E−01 | 2.19 | CLSPN; DNASEIL3; PRKCQ; TOP2A |
| glycosphingolipid metabolism | 40 | 4 | 7.16E−02 | 2.92E−01 | 2.19 | ARSH; GL TP; NEU2; UGCG |
| intercellular bridge: GO | 40 | 4 | 7.16E−02 | 2.92E−01 | 2.19 | CDCA8; CEP55; KIF23; KLK6 |
| production | 40 | 4 | 7.16E−02 | 2.92E−01 | 2.19 | CD80; CXCR4; ICOS; IL6 |
| morphogenesis of an epithelial sheet: GO | 40 | 4 | 7.16E−02 | 2.92E−01 | 2.19 | HBEGF; MMP12; WNT5A; WNT7A |
| negative regulation of stress activated protein kinase signaling cascade: GO | 40 | 4 | 7.16E−02 | 2.92E−01 | 2.19 | FOXM1; GSTP1; PBK; SERPINB3 |
| regulation of hematopoietic progenitor cell differentiation: GO | 40 | 4 | 7.16E−02 | 2.92E−01 | 2.19 | HIST1H4I; HIST1H4J; HIST1H4K; HIST1H4L |
| response to electrical stimulus: GO | 40 | 4 | 7.16E−02 | 2.92E−01 | 2.19 | GJB6; HIF1A; IL6; NTRK1 |
| regulation of proteasomal protein catabolic process: GO | 171 | 12 | 7.16E−02 | 2.92E−01 | 1.53 | AURKA; BUB1; BUB1B; CCNB1; DLGAP5; LAMP3; MAD2L1; PBK; PLK1; PLK2; TTK; VCP |
| complement and coagulation cascades | 55 | 5 | 7.23E−02 | 2.94E−01 | 1.99 | F12; PLAU; PLAUR; SERPINA1; SERPINE1 |
| maternal process involved in female | 55 | 5 | 7.23E−02 | 2.94E−01 | 1.99 | CTSB; CYP27B1; GJB2; HIF1A; PRDM1 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| pregnancy: GO | | | | | | |
| differentiation: GO | 55 | 5 | 7.23E−02 | 2.94E−01 | 1.99 | CCL3; IFNG; IL12B; IL20; LTF |
| retina homeostasis: GO | 55 | 5 | 7.23E−02 | 2.94E−01 | 1.99 | CDH3; CNGB1; LTF; LYZ; PRDX1 |
| regulation of response to cytokine stimulus: GO | 120 | 9 | 7.34E−02 | 2.98E−01 | 1.64 | GSTP1; HIF1A; IFNG; IL36RN; PARP9; PYCARD; SOCS3; STAT1; WNT5A |
| regulation of stress activated protein kinase signaling cascade: GO | 190 | 13 | 7.50E−02 | 3.04E−01 | 1.50 | FOXM1; GSTP1; IL1B; IL26; MDFI; PBK; PRDX1; PYCARD; SERPINB3; SLAMF1; WNT5A; WNT7A; ZC3H12A |
| liposaccharide metabolic process: GO | 104 | 8 | 7.59E−02 | 3.08E−01 | 1.68 | ARSH; GLTP; NEU2; PIGW; PLAUR; ST6GALNACI; ST8S1A2; UGCG |
| regulation of cell cycle g1 s phase transition: GO | 138 | 10 | 7.63E−02 | 3.09E−01 | 1.58 | AURKA; C10orf99; CCNB1; CDC45; CDC6; CDK1; KIF14; PCNA; PLK2; SFN |
| er-phagosome pathway | 56 | 5 | 7.69E−02 | 3.10E−01 | 1.95 | CALR; MYD88; PSMA5; PSMB6; SEC61G |
| glycolipid biosynthetic process: GO | 56 | 5 | 7.69E−02 | 3.10E−01 | 1.95 | PIGW; PLAUR; ST6GALNACI; ST8S1A2; UGCG |
| neurotransmitter receptor activity: GO | 56 | 5 | 7.69E−02 | 3.10E−01 | 1.95 | CHRNA3; CHRNA6; CHRNA9; HRH3; HTR3A |
| negative regulation of leukocyte apoptotic process: GO | 41 | 4 | 7.71E−02 | 3.10E−01 | 2.13 | HIF1A; IDO1; JAK3; PRKCQ |
| regulation of mitochondrial outer membrane permeabilization involved in apoptotic signaling pathway: GO | 41 | 4 | 7.71E−02 | 3.10E−01 | 2.13 | BAK1; SFN; SLC25A5; YWHAQ |
| p27/p21 | 41 | 4 | 7.71E−02 | 3.10E−01 | 2.13 | CCNA2; CCNE1; PSMA5; PSMB6 |
| signaling by ptk6 | 41 | 4 | 7.71E−02 | 3.10E−01 | 2.13 | CCNE1; HBEGF; HIF1A; SOCS3 |
| axis elongation: GO | 27 | 3 | 7.84E−02 | 3.12E−01 | 2.43 | AREG; TNC; WNT5A |
| fat soluble vitamin metabolic process: GO | 27 | 3 | 7.84E−02 | 3.12E−01 | 2.43 | CYP24A1; CYP27B1; CYP4F11 |
| fatty acid binding: GO | 27 | 3 | 7.84E−02 | 3.12E−01 | 2.43 | FABP5; S100A8; S100A9 |
| positive regulation of mesenchymal cell proliferation: GO | 27 | 3 | 7.84E−02 | 3.12E−01 | 2.43 | FOXF1; STAT1; WNT5A |
| pyrimidine containing compound catabolic process: GO | 27 | 3 | 7.84E−02 | 3.12E−01 | 2.43 | APOBEC3A; TYMP; UPP1 |
| regulation of protein oligomerization: GO | 27 | 3 | 7.84E−02 | 3.12E−01 | 2.43 | CCK; MMP1; MMP3 |
| response to ischemia: GO | 27 | 3 | 7.84E−02 | 3.12E−01 | 2.43 | EIF4EBP1; HK2; PPIF |
| site of double strand break: GO | 27 | 3 | 7.84E−02 | 3.12E−01 | 2.43 | ESCO2; H2AFX; VCP |
| chromatin remodeling: GO | 139 | 10 | 7.92E−02 | 3.15E−01 | 1.57 | CENPA; CENPN; CENPW; HIST1H4I; HIST1H4J; HIST1H4K; HIST1H4L; HJURP; HMGA2; OIP5 |
| dna biosynthetic process: GO | 105 | 8 | 7.93E−02 | 3.15E−01 | 1.67 | BLM; EXO1; ISG15; PCNA; POLQ; TK1; USP43; VCP |
| positive regulation of binding: GO | 122 | 9 | 7.97E−02 | 3.16E−01 | 1.61 | ENO1; HMGA2; MMP9; NME1; PLAUR; PLK2; RALB; RAN; WNT5A |
| antigen processing and presentation of peptide antigen via mhc class i: GO | 89 | 7 | 8.15E−02 | 3.23E−01 | 1.72 | CALR; FCGR1A; IFI30; PSMA4; PSMA5; PSMB6; TAP2 |
| transport: GO | 89 | 7 | 8.15E−02 | 3.23E−01 | 1.72 | SLC16A1; SLC16A6; SLC2A9; SLC38A5; SLC7A1; SLC7A11; SLC7A5 |
| tyrosine metabolism | 57 | 5 | 8.17E−02 | 3.23E−01 | 1.92 | ADH7; ALDH1A3; ESCO2; GOT2; IL4I1 |
| chromatin dna binding: GO | 73 | 6 | 8.26E−02 | 3.25E−01 | 1.80 | GRHL3; H2AFZ; HISTIH1A; HIST1H1B; HMGA2; RCC1 |
| transport of glucose and other sugars bile salts and organic acids metal ions and amine compounds | 73 | 6 | 8.26E−02 | 3.25E−01 | 1.80 | RHCG; SLC16A1; SLC2A9; SLC39A6; SLC5A1; SLC6A11 |
| transporters | 42 | 4 | 8.28E−02 | 3.25E−01 | 2.08 | SLC38A5; SLC7A1; SLC7A11; SLC7A5 |
| beta catenin tcf complex assembly: GO | 42 | 4 | 8.28E−02 | 3.25E−01 | 2.08 | HIST1H4I; HIST1H4J; HIST1H4K; HIST1H4L |
| chaperone mediated protein folding: GO | 42 | 4 | 8.28E−02 | 3.25E−01 | 2.08 | CALR; FKBPL; HSPA8; PPIB |
| cxcr3 pathway | 42 | 4 | 8.28E−02 | 3.25E−01 | 2.08 | CXCL10; CXCL11; CXCL13; CXCL9 |
| process: GO | 42 | 4 | 8.28E−02 | 3.25E−01 | 2.08 | HIF1A; PGAM1; PPIF; VCP |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| isoprenoid metabolic process: GO | 106 | 8 | 8.28E−02 | 3.25E−01 | 1.65 | ADH7; AKR1B10; ALDH1A3; CRABP2; IL1B; LRP8; STRA6; UGT1A7 |
| differentiation: GO | 106 | 8 | 8.28E−02 | 3.25E−01 | 1.65 | AQP3; CYP27B1; IFNG; IL1B; IL20; SFN; STAT1; TRIM16 |
| positive regulation of protein localization to nucleus: GO | 123 | 9 | 8.29E−02 | 3.25E−01 | 1.60 | CCT5; CDK1; ECT2; IL12B; IL1B; IL6; PLK1; PRKCQ; ZC3H12A |
| peptidyl serine modification: GO | 141 | 10 | 8.53E−02 | 3.29E−01 | 1.55 | AURKA; CCNB1; CDK1; CDK5R1; CLSPN; HMGA2; IL24; PLK1; PLK2; PRKCQ |
| negative regulation of homotypic cell cell adhesion: GO | 90 | 7 | 8.54E−02 | 3.29E−01 | 1.70 | CD274; CTLA4; IDO1; IL2RA; IL4R; JAK3; TNFRSF21 |
| signal transduction in response to dna damage: GO | 90 | 7 | 8.54E−02 | 3.29E−01 | 1.70 | AURKA; CCNB1; CDK1; FOXM1; PCNA; PLK2; SFN |
| cell cycle: g1/s check point | 28 | 3 | 8.57E−02 | 3.29E−01 | 2.34 | CCNE1; CDC25A; CDK1 |
| g1 pathway | 28 | 3 | 8.57E−02 | 3.29E−01 | 2.34 | CCNE1; CDC25A; CDK1 |
| histone acetyltransferase binding: GO | 28 | 3 | 8.57E−02 | 3.29E−01 | 2.34 | HIF1A; NR4A3; PCNA |
| il2 stat5 pathway | 28 | 3 | 8.57E−02 | 3.29E−01 | 2.34 | CCNA2; IL2RA; JAK3 |
| I alpha amino acid transmembrane transport: GO | 28 | 3 | 8.57E−02 | 3.29E−01 | 2.34 | SLC7A1; SLC7A11; SLC7A5 |
| metabolism of steroid hormones and vitamins a and d | 28 | 3 | 8.57E−02 | 3.29E−01 | 2.34 | CYP24A1; CYP27B1; STARD4 |
| negative regulation of muscle cell apoptotic process: GO | 28 | 3 | 8.57E−02 | 3.29E−01 | 2.34 | ADCYAP1; HMOX1; ZC3H12A |
| positive regulation of vasodilation: GO | 28 | 3 | 8.57E−02 | 3.29E−01 | 2.34 | ADCYAP1; HMOX1; PTAFR |
| proteasome pathway | 28 | 3 | 8.57E−02 | 3.29E−01 | 2.34 | PSMA4; PSMA5; PSMB6 |
| process: GO | 28 | 3 | 8.57E−02 | 3.29E−01 | 2.34 | CMPK2; NME1; UPP1 |
| pyrimidine ribonucleoside metabolic process: GO | 28 | 3 | 8.57E−02 | 3.29E−01 | 2.34 | APOBEC3A; NME1; UPP1 |
| production: GO | 28 | 3 | 8.57E−02 | 3.29E−01 | 2.34 | CD3E; PRKCQ; SASH3 |
| regulation of myelination: GO | 28 | 3 | 8.57E−02 | 3.29E−01 | 2.34 | IFNG; KIF14; TNFRSF21 |
| regulation of sensory perception: GO | 28 | 3 | 8.57E−02 | 3.29E−01 | 2.34 | CCK; CCL3; PTAFR |
| syndecan 4 pathway | 28 | 3 | 8.57E−02 | 3.29E−01 | 2.34 | CXCR4; MMP9; TNC |
| natural killer cell mediated cytotoxicity | 107 | 8 | 8.64E−02 | 3.31E−01 | 1.64 | CSF2; IFNG; RAC2; RAETIL; TNFSF10; ULBP1; ULBP2; ULBP3 |
| peroxide: GO | 58 | 5 | 8.67E−02 | 3.31E−01 | 1.89 | CDK1; ECT2; HIF1A; IL6; PPIF |
| double stranded rna binding: GO | 58 | 5 | 8.67E−02 | 3.31E−01 | 1.89 | DDX21; OAS1; OAS2; OAS3; OASL |
| lipid particle: GO | 58 | 5 | 8.67E−02 | 3.31E−01 | 1.89 | CKAP4; GAPDH; PITPNM1; RSAD2; VCP |
| production of molecular mediator of immune response: GO | 58 | 5 | 8.67E−02 | 3.31E−01 | 1.89 | EXO1; IL7R; POLQ; SLAMF1; TREM1 |
| regulation of monooxygenase activity: GO | 58 | 5 | 8.67E−02 | 3.31E−01 | 1.89 | CDH3; CYP27B1; HIF1A; IFNG; IL1B |
| golgi lumen: GO | 74 | 6 | 8.70E−02 | 3.32E−01 | 1.77 | DEFB103A; DEFB103B; DEFB4A; HS3ST1; WNT5A; WNT7A |
| regulation of extrinsic apoptotic signaling pathway: GO | 142 | 10 | 8.84E−02 | 3.36E−01 | 1.54 | CSF2; GSTP1; HMOX1; IFI6; IL19; IL1B; PYCARD; SERPINE1; TNFRSF12A; TNFSF10 |
| digestive tract morphogenesis: GO | 43 | 4 | 8.87E−02 | 3.36E−01 | 2.03 | FOXF1; HIF1A; STRA6; WNT5A |
| oxidoreductase activity acting on a sulfur group of donors: GO | 43 | 4 | 8.87E−02 | 3.36E−01 | 2.03 | GSTO1; IFI30; SH3BGRL3; TXNDC17 |
| protein folding | 43 | 4 | 8.87E−02 | 3.36E−01 | 2.03 | CCNE1; TUBA1C; TUBB2A; TUBB6 |
| process: GO | 43 | 4 | 8.87E−02 | 3.36E−01 | 2.03 | CMPK2; NME1; TYMP; UPP1 |
| process: GO | 43 | 4 | 8.87E−02 | 3.36E−01 | 2.03 | CYP27B1; IFNG; IL1B; PTAFR |
| sulfotransferase activity: GO | 43 | 4 | 8.87E−02 | 3.36E−01 | 2.03 | CHST1; HS3ST1; HS3ST3A1; HS3ST3B1 |
| membrane | 43 | 4 | 8.87E−02 | 3.36E−01 | 2.03 | SFN; TUBA1C; TUBB2A; TUBB6 |
| negative regulation of protein serine | 125 | 9 | 8.97E−02 | 3.39E−01 | 1.57 | DUSP14; DUSP9; GSTP1; IL1B; PLK1; PYCARD; SERPINB3; SFN; UBE2C |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| threonine kinase activity: GO | | | | | | |
| positive regulation of vasculature development: GO | 125 | 9 | 8.97E−02 | 3.39E−01 | 1.57 | ADM2; HIF1A; HMOX1; IL1B; NTRK1; PGF; SERPINE1; WNT5A; ZC3H12A |
| positive regulation of nucleotide metabolic process: GO | 108 | 8 | 9.01E−02 | 3.40E−01 | 1.62 | ADCYAP1; CXCL10; CXCL11; CXCL9; GPR65; HIF1A; VCP; WNT5A |
| stimulus: GO | 75 | 6 | 9.15E−02 | 3.44E−01 | 1.75 | BAK1; CNN2; CTSB; HIF1A; IL1B; MYD88 |
| clathrin coated vesicle membrane: GO | 75 | 6 | 9.15E−02 | 3.44E−01 | 1.75 | AP1S3; FCGR1A; HBEGF; HSPA8; LDLR; WNT5A |
| positive regulation of autophagy: GO | 75 | 6 | 9.15E−02 | 3.44E−01 | 1.75 | HIF1A; IFNG; MEFV; PLK2; RALB; ZC3H12A |
| activation: GO | 75 | 6 | 9.15E−02 | 3.44E−01 | 1.75 | IFNG; IGHG4; IL6; PRDM1; SASH3; TNFRSF4 |
| metabolism | 29 | 3 | 9.33E−02 | 3.45E−01 | 2.26 | ALDH4A1; GOT2; IL4I1 |
| deaminase activity: GO | 29 | 3 | 9.33E−02 | 3.45E−01 | 2.26 | APOBEC3A; APOBEC3B; ZBP1 |
| dna damage bypass | 29 | 3 | 9.33E−02 | 3.45E−01 | 2.26 | ISG15; PCNA; USP43 |
| endocrine pancreas development: GO | 29 | 3 | 9.33E−02 | 3.45E−01 | 2.26 | BAK1; IL6; WNT5A |
| activity: GO | 29 | 3 | 9.33E−02 | 3.45E−01 | 2.26 | HRH3; HTR3A; HTR7 |
| intrinsic apoptotic signaling pathway in response to dna damage by p53 class mediator: GO | 29 | 3 | 9.33E−02 | 3.45E−01 | 2.26 | AEN; IFI16; PYCARD |
| leukocyte degranulation: GO | 29 | 3 | 9.33E−02 | 3.45E−01 | 2.26 | CCL3; NR4A3; PLA2G3 |
| modulation of excitatory postsynaptic potential: GO | 29 | 3 | 9.33E−02 | 3.45E−01 | 2.26 | EIF4A3; NLGN4X; WNT7A |
| negative regulation of interleukin 6 production: GO | 29 | 3 | 9.33E−02 | 3.45E−01 | 2.26 | IL36RN; SLAMF1; ZC3H12A |
| nucleosomal dna binding: GO | 29 | 3 | 9.33E−02 | 3.45E−01 | 2.26 | H2AFZ; HMGA2; RCC1 |
| pituitary gland development: GO | 29 | 3 | 9.33E−02 | 3.45E−01 | 2.26 | ADCYAP1; PITX1; WNT5A |
| protein export from nucleus: GO | 29 | 3 | 9.33E−02 | 3.45E−01 | 2.26 | CALR; EIF5A; RAN |
| response to exogenous dsrna: GO | 29 | 3 | 9.33E−02 | 3.45E−01 | 2.26 | DDX21; IFNE; RALB |
| signal transduction through il1r | 29 | 3 | 9.33E−02 | 3.45E−01 | 2.26 | IL1B; IL6; MYD88 |
| binding: GO | 29 | 3 | 9.33E−02 | 3.45E−01 | 2.26 | STAT1; TNFSF10; TNFSF9 |
| ubiquitin like protein conjugating enzyme activity: GO | 29 | 3 | 9.33E−02 | 3.45E−01 | 2.26 | UBE2C; UBE2S; UBE2T |
| negative regulation of cell cycle g1 s phase transition: GO | 92 | 7 | 9.36E−02 | 3.45E−01 | 1.66 | AURKA; C10orf99; CCNB1; CDK1; PCNA; PLK2; SFN |
| negative regulation of chromosome organization: GO | 92 | 7 | 9.36E−02 | 3.45E−01 | 1.66 | BUB1; BUB1B; MAD2L1; PIF1; PLK1; PTTG1; TTK |
| delta np63 pathway | 44 | 4 | 9.49E−02 | 3.48E−01 | 1.99 | CCNB2; RAB38; SFN; TOP2A |
| il6 7 pathway | 44 | 4 | 9.49E−02 | 3.48E−01 | 1.99 | IL6; PTPRE; SOCS3; STAT1 |
| membrane disassembly: GO | 44 | 4 | 9.49E−02 | 3.48E−01 | 1.99 | CCNB1; CCNB2; CDK1; PLK1 |
| nuclear inner membrane: GO | 44 | 4 | 9.49E−02 | 3.48E−01 | 1.99 | FAM169A; IFI27; LMNB1; LMNB2 |
| nucleosome binding: GO | 44 | 4 | 9.49E−02 | 3.48E−01 | 1.99 | H2AFZ; HMGA2; RCC1; UHRF1 |
| response to antibiotic: GO | 44 | 4 | 9.49E−02 | 3.48E−01 | 1.99 | ALPL; HYAL3; IL1B; IL6 |
| tumor necrosis factor receptor superfamily binding: GO | 44 | 4 | 9.49E−02 | 3.48E−01 | 1.99 | MYD88; STAT1; TNFSF10; TNFSF9 |
| tissue homeostasis: GO | 144 | 10 | 9.50E−02 | 3.48E−01 | 1.52 | ACP5; CDH3; CNGB1; HOMER1; LTF; LYZ; PRDX1; RAC2; SASH3; VSIG1 |
| axis specification: GO | 76 | 6 | 9.62E−02 | 3.51E−01 | 1.73 | AURKA; MDFI; RGS20; STIL; WNT5A; WNT7A |
| regulation of fibroblast proliferation: GO | 76 | 6 | 9.62E−02 | 3.51E−01 | 1.73 | CCNA2; CCNB1; CDC6; GSTP1; IFI30; WNT5A |
| response to fatty acid: GO | 76 | 6 | 9.62E−02 | 3.51E−01 | 1.73 | CCNB1; IL1B; NME1; PTAFR; TNC; ZC3H12A |
| deoxyribonuclease activity: GO | 60 | 5 | 9.71E−02 | 3.53E−01 | 1.82 | DNASEIL3; EXO1; HMGA2; ISG20; NME1 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| neural precursor cell proliferation: GO | 60 | 5 | 9.71E−02 | 3.53E−01 | 1.82 | ARTN; ASPM; KIF14; MELK; WNT7A |
| regulation of amine transport: GO | 60 | 5 | 9.71E−02 | 3.53E−01 | 1.82 | CCK; CHRNA3; CHRNA6; HRH3; IL1B |
| regulation of cell killing: GO | 60 | 5 | 9.71E−02 | 3.53E−01 | 1.82 | IFNG; IL12B; IL7R; SERPINB4; SERPINB9 |
| regulation of reactive oxygen species biosynthetic process: GO | 60 | 5 | 9.71E−02 | 3.53E−01 | 1.82 | ACP5; IFNG; IL1B; IL6; ZC3H12A |
| endocrine system development: GO | 93 | 7 | 9.78E−02 | 3.55E−01 | 1.65 | ADCYAP1; BAK1; FOXE1; IL6; PITX1; STRA6; WNT5A |
| huntington's disease | 30 | 3 | 1.01E−01 | 3.63E−01 | 2.19 | CALML3; GAPDH; TGM2 |
| nitrogen but not peptide bonds in cyclic amidines: GO | 30 | 3 | 1.01E−01 | 3.63E−01 | 2.19 | APOBEC3A; APOBEC3B; ZBP1 |
| keratinization | 30 | 3 | 1.01E−01 | 3.63E−01 | 2.19 | CSTA; DSG3; PI3 |
| lipopolysaccharide mediated signaling pathway: GO | 30 | 3 | 1.01E−01 | 3.63E−01 | 2.19 | CCL3; IL1B; PTAFR |
| negative regulation of extrinsic apoptotic signaling pathway via death domain receptors: GO | 30 | 3 | 1.01E−01 | 3.63E−01 | 2.19 | HMOX1; SERPINE1; TNFSF10 |
| receptor activator activity: GO | 30 | 3 | 1.01E−01 | 3.63E−01 | 2.19 | CXCL13; WNT5A; WNT7A |
| response to dexamethasone: GO | 30 | 3 | 1.01E−01 | 3.63E−01 | 2.19 | IL1B; IL6; PTAFR |
| cellular defense response: GO | 45 | 4 | 1.01E−01 | 3.63E−01 | 1.94 | CCR5; CD300C; CXCL9; FOSL1 |
| meiotic chromosome segregation: GO | 45 | 4 | 1.01E−01 | 3.63E−01 | 1.94 | PLK1; PTTG1; TOP2A; TRIP13 |
| proliferation: GO | 45 | 4 | 1.01E−01 | 3.63E−01 | 1.94 | CD274; IDO1; IL2RA; TNFRSF21 |
| peptidyl proline modification: GO | 45 | 4 | 1.01E−01 | 3.63E−01 | 1.94 | FKBPL; PPIB; PPIF; PPIL1 |
| intrinsic apoptotic signaling pathway: GO | 146 | 10 | 1.02E−01 | 3.65E−01 | 1.50 | AEN; BAK1; BCL2A1; CHAC1; CYCS; HMOX1; IFI16; MELK; PYCARD; SFN |
| circadian clock | 61 | 5 | 1.03E−01 | 3.67E−01 | 1.79 | ARNTL2; HIF1A; NAMPT; NOCT; SERPINE1 |
| response to activity: GO | 61 | 5 | 1.03E−01 | 3.67E−01 | 1.79 | CDK1; HIF1A; NTRK1; PLAU; SCO2 |
| activation of mapk activity: GO | 129 | 9 | 1.04E−01 | 3.72E−01 | 1.53 | CDK1; CXCR4; DUSP9; EPGN; FPR1; IL1B; MDFI; TGFA; WNT5A |
| collagen formation | 78 | 6 | 1.06E−01 | 3.77E−01 | 1.68 | CTSB; CTSL; MMP1; MMP3; MMP9; PPIB |
| embryonic placenta development: GO | 78 | 6 | 1.06E−01 | 3.77E−01 | 1.68 | CSF2; EOMES; HIF1A; MDFI; PRDM1; SOCS3 |
| plasma membrane raft: GO | 78 | 6 | 1.06E−01 | 3.77E−01 | 1.68 | ATP1B3; CTSB; HMOX1; KIF18A; LRP8; SELE |
| response: GO | 46 | 4 | 1.08E−01 | 3.81E−01 | 1.90 | C1QBP; CXCL13; DEFB103A; DEFB103B |
| response to progesterone: GO | 46 | 4 | 1.08E−01 | 3.81E−01 | 1.90 | CCNE1; FOSL1; GJB2; SOCS3 |
| syndecan 1 pathway | 46 | 4 | 1.08E−01 | 3.81E−01 | 1.90 | HPSE; MMP1; MMP9; PPIB |
| nanoparticle: GO | 130 | 9 | 1.08E−01 | 3.81E−01 | 1.51 | ACP5; CCNB1; CCNE1; CDK1; GGH; GSTP1; HMOX1; S100A8; TK1 |
| mesoderm morphogenesis: GO | 62 | 5 | 1.08E−01 | 3.81E−01 | 1.76 | EOMES; FOXF1; HMGA2; NR4A3; WNT5A |
| regulation of neural precursor cell proliferation: GO | 62 | 5 | 1.08E−01 | 3.81E−01 | 1.76 | ADCYAP1; ASPM; HIF1A; IL1B; WNT5A |
| water homeostasis: GO | 62 | 5 | 1.08E−01 | 3.81E−01 | 1.76 | AQP3; GRHL3; HRNR; KRT16; SFN |
| activation: GO | 31 | 3 | 1.09E−01 | 3.81E−01 | 2.12 | IL12B; IL6; RSAD2 |
| starvation: GO | 31 | 3 | 1.09E−01 | 3.81E−01 | 2.12 | IFI16; UPP1; ZC3H12A |
| cellular response to heat: GO | 31 | 3 | 1.09E−01 | 3.81E−01 | 2.12 | CXCL10; HMOX1; HSPA6 |
| cellular senescence: GO | 31 | 3 | 1.09E−01 | 3.81E−01 | 2.12 | CALR; H2AFX; HMGA2 |
| traffic | 31 | 3 | 1.09E−01 | 3.81E−01 | 2.12 | TUBA1C; TUBB2A; TUBB6 |
| embryonic eye morphogenesis: GO | 31 | 3 | 1.09E−01 | 3.81E−01 | 2.12 | ALDH1A3; STRA6; WNT5A |
| galactose metabolism | 31 | 3 | 1.09E−01 | 3.81E−01 | 2.12 | AKR1B10; HK2; PGM2 |
| ilir pathway | 31 | 3 | 1.09E−01 | 3.81E−01 | 2.12 | IL1B; IL6; MYD88 |
| immunological synapse: GO | 31 | 3 | 1.09E−01 | 3.81E−01 | 2.12 | CD3E; GZMA; PRKCQ |
| negative regulation of signal transduction in absence of ligand: GO | 31 | 3 | 1.09E−01 | 3.81E−01 | 2.12 | CSF2; IFI6; IL1B |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| olfactory lobe development: GO | 31 | 3 | 1.09E−01 | 3.81E−01 | 2.12 | EOMES; KIF14; WNT5A |
| oocyte differentiation: GO | 31 | 3 | 1.09E−01 | 3.81E−01 | 2.12 | CCNB1; CDC25B; TRIP13 |
| phototransduction: GO | 31 | 3 | 1.09E−01 | 3.81E−01 | 2.12 | CNGB1; GNGT2; PITPNM1 |
| positive regulation of dna repair: GO | 31 | 3 | 1.09E−01 | 3.81E−01 | 2.12 | FOXM1; H2AFX; PCNA |
| retinoid metabolism and transport | 31 | 3 | 1.09E−01 | 3.81E−01 | 2.12 | AKR1B10; LDLR; LRP8 |
| ligand: GO | 31 | 3 | 1.09E−01 | 3.81E−01 | 2.12 | BAK1; BCL2A1; IL1B |
| negative regulation of ion transport: GO | 113 | 8 | 1.10E−01 | 3.83E−01 | 1.55 | ADCYAP1; GSTO1; HRH3; IL1B; MMP9; PCSK9; PPIF; YWHAQ |
| lymphocyte activation involved in immune response: GO | 79 | 6 | 1.11E−01 | 3.85E−01 | 1.66 | EOMES; EXO1; IFNE; IFNG; IL12B; IL6 |
| positive regulation of reactive oxygen species metabolic process: GO | 79 | 6 | 1.11E−01 | 3.85E−01 | 1.66 | GSTP1; IFNG; IL1B; IL6; PLAU; ZC3H12A |
| regulation of generation of precursor metabolites and energy: GO | 79 | 6 | 1.11E−01 | 3.85E−01 | 1.66 | HIF1A; PGAM1; PHLDA2; PPIF; PRELID1; VCP |
| aminoglycan catabolic process: GO | 63 | 5 | 1.14E−01 | 3.93E−01 | 1.74 | CHI3L2; HMMR; HPSE; HYAL3; PGL YRP2 |
| glycan structures - biosynthesis 2 | 63 | 5 | 1.14E−01 | 3.93E−01 | 1.74 | B3GNT3; FUT1; FUT2; FUT3; UGCG |
| hedgehog 'off' state | 63 | 5 | 1.14E−01 | 3.93E−01 | 1.74 | PSMA5; PSMB6; TUBA1C; TUBB2A; TUBB6 |
| regulation of biomineral tissue development: GO | 63 | 5 | 1.14E−01 | 3.93E−01 | 1.74 | CCL3; CYP27B1; HIF1A; LTF; SRGN |
| starch and sucrose metabolism | 63 | 5 | 1.14E−01 | 3.93E−01 | 1.74 | HK2; PGM2; PYGL; UGT1A10; UGT1A7 |
| tnfr2 non-canonical nf-kb pathway | 63 | 5 | 1.14E−01 | 3.93E−01 | 1.74 | PSMA5; PSMB6; TNFRSF12A; TNFRSF9; TNFSF9 |
| endoderm formation: GO | 47 | 4 | 1.14E−01 | 3.93E−01 | 1.86 | EOMES; HMGA2; MMP9; SOX7 |
| excitatory extracellular ligand gated ion channel activity: GO | 47 | 4 | 1.14E−01 | 3.93E−01 | 1.86 | CHRNA3; CHRNA6; CHRNA9; HTR3A |
| I amino acid transmembrane transporter activity: GO | 47 | 4 | 1.14E−01 | 3.93E−01 | 1.86 | SLC38A5; SLC7A1; SLC7A11; SLC7A5 |
| p53-dependent g1 dna damage response | 47 | 4 | 1.14E−01 | 3.93E−01 | 1.86 | CCNA2; CCNE1; PSMA5; PSMB6 |
| checkpoint | 47 | 4 | 1.14E−01 | 3.93E−01 | 1.86 | CCNA2; CCNE1; PSMA5; PSMB6 |
| regulation of myotube differentiation: GO | 47 | 4 | 1.14E−01 | 3.93E−01 | 1.86 | CXCL10; CXCL9; IL4R; NEU2 |
| positive regulation of homeostatic process: GO | 186 | 12 | 1.15E−01 | 3.95E−01 | 1.41 | BAK1; CCT5; CXCL 10; CXCL11; CXCL9; GSTO1; HIF1A; IL1B; ISG15; NEK2; PRKCQ; VSNL1 |
| response to camp: GO | 97 | 7 | 1.16E−01 | 3.97E−01 | 1.58 | AREG; FOSL1; FOXM1; LDHA; NME1; PTAFR; STAT1 |
| regulation of stem cell proliferation: GO | 80 | 6 | 1.16E−01 | 3.97E−01 | 1.64 | ASPM; FOXF1; HIF1A; HMGA2; STAT1; WNT5A |
| bone remodeling: GO | 32 | 3 | 1.18E−01 | 4.00E−01 | 2.05 | ACP5; IL6; RAC2 |
| cross-presentation of soluble exogenous antigens (endosomes) | 32 | 3 | 1.18E−01 | 4.00E−01 | 2.05 | FCGR1A; PSMA5; PSMB6 |
| lactation: GO | 32 | 3 | 1.18E−01 | 4.00E−01 | 2.05 | HIF1A; HK2; NME1 |
| maturation: GO | 32 | 3 | 1.18E−01 | 4.00E−01 | 2.05 | BIRC5; CHAC1; SERPINE1 |
| neuron recognition: GO | 32 | 3 | 1.18E−01 | 4.00E−01 | 2.05 | CDK5R1; CNTNAP2; CXCR4 |
| maintenance via telomere lengthening: GO | 32 | 3 | 1.18E−01 | 4.00E−01 | 2.05 | CCT5; NEK2; PRKCQ |
| repair: GO | 32 | 3 | 1.18E−01 | 4.00E−01 | 2.05 | FOXM1; HMGA2; POLQ |
| response to mineralocorticoid: GO | 32 | 3 | 1.18E−01 | 4.00E−01 | 2.05 | CCNE1; FOSL1; RAN |
| exogenous peptide antigen via mhc class i: GO | 64 | 5 | 1.20E−01 | 4.06E−01 | 1.71 | FCGR1A; IFI30; PSMA4; PSMA5; PSMB6 |
| costimulation by the cd28 family | 64 | 5 | 1.20E−01 | 4.06E−01 | 1.71 | CD274; CD3E; CD80; CTLA4; ICOS |
| extracellular matrix disassembly: GO | 64 | 5 | 1.20E−01 | 4.06E−01 | 1.71 | ADAMTS4; MMP1; MMP12; MMP3; MMP9 |
| positive regulation of lymphocyte | 64 | 5 | 1.20E−01 | 4.06E−01 | 1.71 | IFNG; IL12B; IL1B; RSAD2; SASH3 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| mediated immunity: GO | | | | | | |
| ppar signaling pathway | 64 | 5 | 1.20E−01 | 4.06E−01 | 1.71 | FABP5; FABP6; GK; MMP1; OLR1 |
| process: GO | 81 | 6 | 1.21E−01 | 4.10E−01 | 1.62 | ACP5; GSTO1; NAMPT; PRSS3; TCN1; VNN3 |
| replication: GO | 48 | 4 | 1.21E−01 | 4.10E−01 | 1.82 | BLM; CDC6; PIF1; S100A11 |
| negative regulation of wound healing: GO | 48 | 4 | 1.21E−01 | 4.10E−01 | 1.82 | F12; PLAU; PLAUR; SERPINE1 |
| visual phototransduction | 48 | 4 | 1.21E−01 | 4.10E−01 | 1.82 | AKR1B10; LDLR; LRP8; RDH16 |
| microtubule based movement: GO | 188 | 12 | 1.22E−01 | 4.11E−01 | 1.40 | CENPE; DLGAP5; HIF1A; KIF11; KIF14; KIF15; KIF18A; KIF20A; KIF23; KIF2C; KIF4A; NTRK1 |
| positive regulation of nucleocytoplasmic transport: GO | 116 | 8 | 1.23E−01 | 4.14E−01 | 1.51 | CDK1; ECT2; IL12B; IL1B; IL6; PRKCQ; SFN; ZC3H12A |
| signalling to ras | 152 | 10 | 1.24E−01 | 4.17E−01 | 1.44 | CDK1; CSF2; DUSP9; HBEGF; IL2RA; JAK3; NTRK1; PSMA5; PSMB6; RALB |
| positive regulation of protein import: GO | 99 | 7 | 1.25E−01 | 4.19E−01 | 1.55 | CDK1; ECT2; IL12B; IL1B; IL6; PRKCQ; ZC3H12A |
| cell aging: GO | 65 | 5 | 1.26E−01 | 4.19E−01 | 1.68 | CALR; CDK1; H2AFX; HMGA2; SERPINE1 |
| cellular response to uv: GO | 65 | 5 | 1.26E−01 | 4.19E−01 | 1.68 | BAK1; CDC25A; HYAL3; PBK; PCNA |
| regulation of dna repair: GO | 65 | 5 | 1.26E−01 | 4.19E−01 | 1.68 | FOXM1; H2AFX; HMGA2; PCNA; POLQ |
| allograft rejection | 33 | 3 | 1.26E−01 | 4.19E−01 | 1.99 | CD80; IFNG; IL12B |
| bmal1 clock npas2 activates circadian expression | 33 | 3 | 1.26E−01 | 4.19E−01 | 1.99 | ARNTL2; NAMPT; SERPINE1 |
| process: GO | 33 | 3 | 1.26E−01 | 4.19E−01 | 1.99 | CMPK2; NUDT15; RRM2 |
| development: GO | 33 | 3 | 1.26E−01 | 4.19E−01 | 1.99 | ALDH1A3; STRA6; WNT5A |
| establishment or maintenance of bipolar cell polarity: GO | 33 | 3 | 1.26E−01 | 4.19E−01 | 1.99 | FOXF1; FSCN1; WNT5A |
| il2 pi3k pathway | 33 | 3 | 1.26E−01 | 4.19E−01 | 1.99 | IL2RA; JAK3; UGCG |
| positive regulation of organ growth: GO | 33 | 3 | 1.26E−01 | 4.19E−01 | 1.99 | CCNB1; CDK1; SASH3 |
| protein k63 linked ubiquitination: GO | 33 | 3 | 1.26E−01 | 4.19E−01 | 1.99 | UBE2F; UBE2S; UBE2T |
| regulation of natural killer cell mediated immunity: GO | 33 | 3 | 1.26E−01 | 4.19E−01 | 1.99 | IL12B; SERPINB4; SERPINB9 |
| nucleus: GO | 33 | 3 | 1.26E−01 | 4.19E−01 | 1.99 | IFI27; IL1B; SFN |
| snrna binding: GO | 33 | 3 | 1.26E−01 | 4.19E−01 | 1.99 | DDX21; EIF5A; ISG20 |
| degradation of the extracellular matrix | 82 | 6 | 1.27E−01 | 4.20E−01 | 1.60 | CTSB; CTSL; MMP1; MMP12; MMP3; MMP9 |
| regulation of oxidoreductase activity: GO | 82 | 6 | 1.27E−01 | 4.20E−01 | 1.60 | CDH3; CYP27B1; GZMA; HIF1A; IFNG; IL1B |
| response to ketone: GO | 171 | 11 | 1.27E−01 | 4.20E−01 | 1.41 | CALR; CCNE1; FOSL1; GJB2; IL1B; IL6; NME1; PTAFR; SOCS3; TK1; WNT5A |
| cellular response to corticosteroid stimulus: GO | 49 | 4 | 1.28E−01 | 4.21E−01 | 1.79 | ADCYAP1; GSTP1; IL6; RAN |
| cellular response to hypoxia | 49 | 4 | 1.28E−01 | 4.21E−01 | 1.79 | HIF1A; HIGD1A; PSMA5; PSMB6 |
| class b 2 secretin family receptors | 49 | 4 | 1.28E−01 | 4.21E−01 | 1.79 | ADCYAP1; ADM2; GNGT2; WNT7A |
| destabilization of mrna by auf1 hnrnp do | 49 | 4 | 1.28E−01 | 4.21E−01 | 1.79 | HSPA8; PSMA4; PSMA5; PSMB6 |
| monosaccharide transport: GO | 49 | 4 | 1.28E−01 | 4.21E−01 | 1.79 | FABP5; HK2; SLC2A9; SLC5A1 |
| positive regulation of epithelial cell differentiation: GO | 49 | 4 | 1.28E−01 | 4.21E−01 | 1.79 | CYP27B1; IL20; SFN; TRIM16 |
| positive regulation of fibroblast proliferation: GO | 49 | 4 | 1.28E−01 | 4.21E−01 | 1.79 | CCNA2; CCNB1; CDC6; WNT5A |
| positive regulation of phospholipase activity: GO | 49 | 4 | 1.28E−01 | 4.21E−01 | 1.79 | GNA15; PTAFR; SIPR4; SELE |
| regulation of hypoxia-inducible factor (hif) by oxygen | 49 | 4 | 1.28E−01 | 4.21E−01 | 1.79 | HIF1A; HIGD1A; PSMA5; PSMB6 |
| regulation of telomere maintenance via | 49 | 4 | 1.28E−01 | 4.21E−01 | 1.79 | CCT5; NEK2; PIF1; PRKCQ |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| telomere lengthening: GO | | | | | | |
| retinol metabolism | 49 | 4 | 1.28E−01 | 4.21E−01 | 1.79 | ADH7; RDH16; UGT1A10; UGT1A7 |
| regulation of tp53 activity through phosphorylation | 66 | 5 | 1.32E−01 | 4.32E−01 | 1.66 | AURKA; BLM; CCNA2; EXO1; TPX2 |
| epithelial cell proliferation: GO | 83 | 6 | 1.32E−01 | 4.32E−01 | 1.58 | AREG; EHF; FERMT1; HMOX1; IL6; WNT5A |
| coreceptor activity: GO | 34 | 3 | 1.35E−01 | 4.38E−01 | 1.93 | CCR5; CD80; CXCR4 |
| segregation: GO | 34 | 3 | 1.35E−01 | 4.38E−01 | 1.93 | PLK1; PTTG1; TRIP13 |
| intraflagellar transport | 34 | 3 | 1.35E−01 | 4.38E−01 | 1.93 | TUBA1C; TUBB2A; TUBB6 |
| metabolism of fat-soluble vitamins | 34 | 3 | 1.35E−01 | 4.38E−01 | 1.93 | AKR1B10; LDLR; LRP8 |
| negative regulation of mitochondrion organization: GO | 34 | 3 | 1.35E−01 | 4.38E−01 | 1.93 | PPIF; PRELID1; SLC25A5 |
| neuron apoptotic process: GO | 34 | 3 | 1.35E−01 | 4.38E−01 | 1.93 | FAM162A; GAPDH; TNFRSF21 |
| regulation of mesenchymal cell proliferation: GO | 34 | 3 | 1.35E−01 | 4.38E−01 | 1.93 | FOXF1; STAT1; WNT5A |
| t cell homeostasis: GO | 34 | 3 | 1.35E−01 | 4.38E−01 | 1.93 | CCNB2; IL2RA; JAK3 |
| aminoglycan biosynthetic process: GO | 101 | 7 | 1.35E−01 | 4.38E−01 | 1.52 | B3GNT3; CHST1; HAS3; HS3ST1; HS3ST3A1; HS3ST3B1; IL1B |
| negative regulation of dna metabolic process: GO | 101 | 7 | 1.35E−01 | 4.38E−01 | 1.52 | BLM; CDC6; GZMA; HMGA2; PIF1; POLQ; S100A11 |
| negative regulation of protein catabolic process: GO | 101 | 7 | 1.35E−01 | 4.38E−01 | 1.52 | BUB1; BUB1B; LAMP3; MAD2L1; PBK; PLK1; TTK |
| positive regulation of epithelial cell migration: GO | 101 | 7 | 1.35E−01 | 4.38E−01 | 1.52 | HBEGF; HIF1A; IFNG; MMP9; WNT5A; WNT7A; ZC3H12A |
| radiation: GO | 50 | 4 | 1.36E−01 | 4.38E−01 | 1.75 | BLM; ECT2; H2AFX; IFI16 |
| fgf pathway | 50 | 4 | 1.36E−01 | 4.38E−01 | 1.75 | MMP9; PLAU; PLAUR; STAT1 |
| organic hydroxy compound transmembrane transporter activity: GO | 50 | 4 | 1.36E−01 | 4.38E−01 | 1.75 | ABCG4; AQP3; SLC16A1; SLC16A6 |
| cilium assembly | 119 | 8 | 1.36E−01 | 4.40E−01 | 1.47 | CCT5; CDK1; KIF2C; NEK2; PLK1; TUBA1C; TUBB2A; TUBB6 |
| regulation of anion transport: GO | 119 | 8 | 1.36E−01 | 4.40E−01 | 1.47 | CCK; CHRNA3; CHRNA6; HRH3; IL1B; LRRC8D; PRELID1; PTAFR |
| regulation of protein import: GO | 174 | 11 | 1.38E−01 | 4.45E−01 | 1.38 | CDK1; ECT2; HSPA8; IL12B; IL1B; IL6; MDFI; PRDX1; PRKCQ; RGS20; ZC3H12A |
| er to golgi transport vesicle: GO | 67 | 5 | 1.38E−01 | 4.45E−01 | 1.63 | AREG; CTSC; PCSK9; SERPINA1; TGFA |
| hormone metabolic process: GO | 138 | 9 | 1.41E−01 | 4.53E−01 | 1.43 | ADH7; AKR1B15; ALDH1A3; CRABP2; FOXE1; GCNT4; IL1B; KLK6; UGT1A7 |
| response to uv: GO | 120 | 8 | 1.41E−01 | 4.53E−01 | 1.46 | BAK1; CDC25A; HYAL3; IL12B; IVL; PBK; PCNA; SERPINB13 |
| ammonium ion binding: GO | 51 | 4 | 1.43E−01 | 4.53E−01 | 1.72 | CHRNA3; CHRNA6; CHRNA9; HTR3A |
| execution phase of apoptosis: GO | 51 | 4 | 1.43E−01 | 4.53E−01 | 1.72 | CLSPN; DNASEIL3; PRKCQ; TOP2A |
| development: GO | 51 | 4 | 1.43E−01 | 4.53E−01 | 1.72 | AREG; FOXF1; HIF1A; WNT5A |
| transport: GO | 51 | 4 | 1.43E−01 | 4.53E−01 | 1.72 | CCK; IL1B; PRELID1; PTAFR |
| positive regulation of calcium ion transmembrane transport: GO | 51 | 4 | 1.43E−01 | 4.53E−01 | 1.72 | CXCL10; CXCL11; CXCL9; GSTO1 |
| regulation of leukocyte mediated cytotoxicity: GO | 51 | 4 | 1.43E−01 | 4.53E−01 | 1.72 | IL12B; IL7R; SERPINB4; SERPINB9 |
| phospholipase activity: GO | 85 | 6 | 1.43E−01 | 4.53E−01 | 1.54 | CCR5; HMOX1; LIPG; PLA2G3; PLA2G4D; PLBD1 |
| cdk-mediated phosphorylation and removal of cdc6 | 35 | 3 | 1.44E−01 | 4.53E−01 | 1.87 | CDC6; PSMA5; PSMB6 |
| cochlea development: GO | 35 | 3 | 1.44E−01 | 4.53E−01 | 1.87 | CCNA2; GRHL3; WNT5A |
| gmcsf pathway | 35 | 3 | 1.44E−01 | 4.53E−01 | 1.87 | CSF2; OSM; STAT1 |
| gpvi-mediated activation cascade | 35 | 3 | 1.44E−01 | 4.53E−01 | 1.87 | CSF2; IL2RA; JAK3 |
| donors with incorporation or reduction | 35 | 3 | 1.44E−01 | 4.53E−01 | 1.87 | CYP27B1; CYP4F11; SQLE |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| of molecular oxygen nad p h as one donor and incorporation of one atom of oxygen: GO | | | | | | |
| outer membrane permeabilization involved in apoptotic signaling pathway: GO | 35 | 3 | 1.44E−01 | 4.53E−01 | 1.87 | BAK1; SFN; YWHAQ |
| positive regulation of protein tyrosine kinase activity: GO | 35 | 3 | 1.44E−01 | 4.53E−01 | 1.87 | EPGN; LRP8; TGFA |
| amino acid transmembrane transporter activity: GO | 68 | 5 | 1.45E−01 | 4.53E−01 | 1.61 | SLC38A5; SLC6A11; SLC7A1; SLC7A11; SLC7A5 |
| formation of primary germ layer: GO | 103 | 7 | 1.46E−01 | 4.53E−01 | 1.49 | EOMES; FOXF1; HMGA2; MMP9; NR4A3; SOX7; WNT5A |
| alcohol transmembrane transporter activity: GO | 20 | 2 | 1.46E−01 | 4.53E−01 | 2.19 | ABCG4; AQP3 |
| anion anion antiporter activity: GO | 20 | 2 | 1.46E−01 | 4.53E−01 | 2.19 | SLC26A9; SLC7A11 |
| atpase complex: GO | 20 | 2 | 1.46E−01 | 4.53E−01 | 2.19 | ATP12A; ATP1B3 |
| b cell homeostasis: GO | 20 | 2 | 1.46E−01 | 4.53E−01 | 2.19 | BAK1; HIF1A |
| bone resorption: GO | 20 | 2 | 1.46E−01 | 4.53E−01 | 2.19 | ACP5; RAC2 |
| carbohydrate phosphorylation: GO | 20 | 2 | 1.46E−01 | 4.53E−01 | 2.19 | HK2; PFKFB4 |
| cysteine type endopeptidase inhibitor activity involved in apoptotic process: GO | 20 | 2 | 1.46E−01 | 4.53E−01 | 2.19 | BIRC5; SERPINB9 |
| dorsal ventral axis specification: GO | 20 | 2 | 1.46E−01 | 4.53E−01 | 2.19 | MDFI; RGS20 |
| endoplasmic reticulum calcium ion homeostasis: GO | 20 | 2 | 1.46E−01 | 4.53E−01 | 2.19 | BAK1; TGM2 |
| er phagosome pathway | 20 | 2 | 1.46E−01 | 4.53E−01 | 2.19 | PSMA4; TAP2 |
| estrogen metabolic process: GO | 20 | 2 | 1.46E−01 | 4.53E−01 | 2.19 | AKR1B15; IL1B |
| glucagon type ligand receptors | 20 | 2 | 1.46E−01 | 4.53E−01 | 2.19 | ADCYAP1; GNGT2 |
| glycogen metabolism | 20 | 2 | 1.46E−01 | 4.53E−01 | 2.19 | PGM2; PYGL |
| how progesterone initiates the oocyte maturation | 20 | 2 | 1.46E−01 | 4.53E−01 | 2.19 | CCNB1; CDK1 |
| il5 pathway | 20 | 2 | 1.46E−01 | 4.53E−01 | 2.19 | IL1B; IL6 |
| microtubule end: GO | 20 | 2 | 1.46E−01 | 4.53E−01 | 2.19 | ASPM; KIF2C |
| mitochondrial genome maintenance: GO | 20 | 2 | 1.46E−01 | 4.53E−01 | 2.19 | PIF1; TYMP |
| monosaccharide transmembrane transporter activity: GO | 20 | 2 | 1.46E−01 | 4.53E−01 | 2.19 | SLC2A9; SLC5A1 |
| necroptotic process: GO | 20 | 2 | 1.46E−01 | 4.53E−01 | 2.19 | PPIF; PYGL |
| negative regulation of alpha beta t cell activation: GO | 20 | 2 | 1.46E−01 | 4.53E−01 | 2.19 | IL4R; JAK3 |
| negative regulation of neural precursor cell proliferation: GO | 20 | 2 | 1.46E−01 | 4.53E−01 | 2.19 | IL1B; WNT5A |
| neutral lipid catabolic process: GO | 20 | 2 | 1.46E−01 | 4.53E−01 | 2.19 | FABP5; FABP6 |
| involved in cellular response to glucose stimulus: GO | 20 | 2 | 1.46E−01 | 4.53E−01 | 2.19 | HIF1A; VSNL1 |
| positive regulation of lamellipodium organization: GO | 20 | 2 | 1.46E−01 | 4.53E−01 | 2.19 | FSCN1; RAC2 |
| regulation of membrane protein ectodomain proteolysis: GO | 20 | 2 | 1.46E−01 | 4.53E−01 | 2.19 | IFNG; IL1B |
| she1 events in erbb4 signaling | 20 | 2 | 1.46E−01 | 4.53E−01 | 2.19 | CDK1; HBEGF |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| skeletal muscle tissue regeneration: GO | 20 | 2 | 1.46E−01 | 4.53E−01 | 2.19 | PLAU; WNT7A |
| subpallium development: GO | 20 | 2 | 1.46E−01 | 4.53E−01 | 2.19 | ALDH1A3; CNTNAP2 |
| receptor | 20 | 2 | 1.46E−01 | 4.53E−01 | 2.19 | GNA15; GNGT2 |
| transcriptional regulation by the ap-2 (tfap2) family of transcription factors | 20 | 2 | 1.46E−01 | 4.53E−01 | 2.19 | MYBL2; TGFA |
| signalling to erks | 158 | 10 | 1.48E−01 | 4.58E−01 | 1.38 | CDK1; CSF2; DUSP9; HBEGF; IL2RA; JAK3; NTRK1; PSMA5; PSMB6; RALB |
| cellular hormone metabolic process: GO | 86 | 6 | 1.49E−01 | 4.60E−01 | 1.53 | ADH7; AKR1B15; ALDH1A3; CRABP2; IL1B; UGT1A7 |
| phase i - functionalization of compounds | 86 | 6 | 1.49E−01 | 4.60E−01 | 1.53 | CYP24A1; CYP27B1; CYP2S1; CYP4F11; CYP4F22; SMOX |
| regulation of cytosolic calcium ion concentration: GO | 17 | 11 | 1.50E−01 | 4.62E−01 | 1.36 | ADCYAP1; CCL3; CCR4; CCR5; CHRNA9; CXCL13; CXCR4; GNA15; IL1B; JAK3; S1PR4 |
| epithelial to mesenchymal transition: GO | 52 | 4 | 1.51E−01 | 4.62E−01 | 1.68 | EOMES; HIF1A; HMGA2; WNT5A |
| l amino acid transport: GO | 52 | 4 | 1.51E−01 | 4.62E−01 | 1.68 | SLC38A5; SLC7A1; SLC7A11; SLC7A5 |
| regulation of glial cell differentiation: GO | 52 | 4 | 1.51E−01 | 4.62E−01 | 1.68 | CDK1; CXCR4; IL1B; TNFRSF21 |
| production: GO | 104 | 7 | 1.51E−01 | 4.62E−01 | 1.47 | IFI16; ISG15; MYD88; NMI; POLR3G; PYCARD; ZBP1 |
| slc mediated transmembrane transport | 104 | 7 | 1.51E−01 | 4.62E−01 | 1.47 | HK2; RHCG; SLC26A9; SLC38A5; SLC4A8; SLC5A1; SLC6A11 |
| protein stabilization: GO | 122 | 8 | 1.51E−01 | 4.62E−01 | 1.43 | ATP1B3; CALR; CCT5; FKBPL; GAPDH; HIST1H1B; IFI30; PPIB |
| anchoring of the basal body to the plasma membrane | 69 | 5 | 1.51E−01 | 4.62E−01 | 1.58 | CDK1; KIF2C; NEK2; PLK1; TUBA1C |
| mtor 4pathway | 69 | 5 | 1.51E−01 | 4.62E−01 | 1.58 | CCNE1; CYCS; EIF4EBP1; SFN; YWHAQ |
| pancreatic cancer | 69 | 5 | 1.51E−01 | 4.62E−01 | 1.58 | PGF; RAC2; RALB; STAT1; TGFA |
| positive regulation of peptidyl serine phosphorylation: GO | 69 | 5 | 1.51E−01 | 4.62E−01 | 1.58 | IFNE; IFNG; IL6; OSM; WNT5A |
| stimulus: GO | 36 | 3 | 1.53E−01 | 4.66E−01 | 1.82 | CCNA2; H2AFZ; SERPINB9 |
| fbx17 down-regulates aurka during mitotic entry and in early mitosis | 36 | 3 | 1.53E−01 | 4.66E−01 | 1.82 | AURKA; PSMA5; PSMB6 |
| peptidase activator activity: GO | 36 | 3 | 1.53E−01 | 4.66E−01 | 1.82 | CTSC; PYCARD; VCP |
| phosphoinositide 3 kinase pathway | 36 | 3 | 1.53E−01 | 4.66E−01 | 1.82 | NR4A3; SFN; YWHAQ |
| pi3k plc trk pathway | 36 | 3 | 1.53E−01 | 4.66E−01 | 1.82 | NTRK1; SFN; YWHAQ |
| response to testosterone: GO | 36 | 3 | 1.53E−01 | 4.66E−01 | 1.82 | CALR; NME1; WNT5A |
| spindle localization: GO | 36 | 3 | 1.53E−01 | 4.66E−01 | 1.82 | ASPM; CENPA; NDC80 |
| signalling to p38 via rit and rin | 141 | 9 | 1.55E−01 | 4.67E−01 | 1.40 | CDK1; CSF2; DUSP9; HBEGF; IL2RA; JAK3; NTRK1; PSMA5; PSMB6 |
| positive regulation of cyclic nucleotide metabolic process: GO | 87 | 6 | 1.55E−01 | 4.67E−01 | 1.51 | ADCYAP1; CXCL10; CXCL11; CXCL9; GPR65; WNT5A |
| response to calcium ion: GO | 105 | 7 | 1.56E−01 | 4.67E−01 | 1.46 | AQP3; ECT2; HOMER1; IL6; PPIF; S100A16; WNT5A |
| leukocyte proliferation: GO | 70 | 5 | 1.58E−01 | 4.67E−01 | 1.56 | EBI3; IFNE; IL7R; SLAMF1; TNFRSF4 |
| secretion: GO | 70 | 5 | 1.58E−01 | 4.67E−01 | 1.56 | ADCYAP1; HIF1A; S100A8; S100A9; VSNL1 |
| embryonic heart tube morphogenesis: GO | 53 | 4 | 1.58E−01 | 4.67E−01 | 1.65 | HIF1A; NDRG4; STIL; WNT5A |
| endothelial cell migration: GO | 53 | 4 | 1.58E−01 | 4.67E−01 | 1.65 | CXCL13; PRSS3; S100A2; STAT1 |
| lens development in camera type eye: GO | 53 | 4 | 1.58E−01 | 4.67E−01 | 1.65 | BFSP1; SLC7A11; WNT5A; WNT7A |
| microtubule organization from the centrosome | 53 | 4 | 1.58E−01 | 4.67E−01 | 1.65 | CDK1; NEK2; PLK1; TUBA1C |
| nad binding: GO | 53 | 4 | 1.58E−01 | 4.67E−01 | 1.65 | AHCY; ALDH1A3; GAPDH; LDHA |
| oogenesis: GO | 53 | 4 | 1.58E−01 | 4.67E−01 | 1.65 | ASPM; CCNB1; CDC25B; TRIP13 |
| pathogenic escherichia coli infection | 53 | 4 | 1.58E−01 | 4.67E−01 | 1.65 | TUBA1C; TUBB2A; TUBB6; YWHAQ |
| regulation of cellular response to insulin stimulus: GO | 53 | 4 | 1.58E−01 | 4.67E−01 | 1.65 | IL1B; PRKCQ; PTPRE; SOCS3 |
| tetrapyrrole metabolic process: GO | 53 | 4 | 1.58E−01 | 4.67E−01 | 1.65 | HMOX1; HMOX2; PRSS3; TCN1 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| antigen presentation folding assembly and peptide loading of class i mhc | 21 | 2 | 1.59E−01 | 4.67E−01 | 2.08 | CALR; TAP2 |
| association of tric/cct with target proteins during biosynthesis | 21 | 2 | 1.59E−01 | 4.67E−01 | 2.08 | CCNE1; CCT5 |
| b cell proliferation: GO | 21 | 2 | 1.59E−01 | 4.67E−01 | 2.08 | IFNE; IL7R |
| cell proliferation in forebrain: GO | 21 | 2 | 1.59E−01 | 4.67E−01 | 2.08 | KIF14; WNT7A |
| dendritic cell migration: GO | 21 | 2 | 1.59E−01 | 4.67E−01 | 2.08 | CCR5; CXCR4 |
| process: GO | 21 | 2 | 1.59E−01 | 4.67E−01 | 2.08 | NUDT15; PGM2 |
| detection of mechanical stimulus involved in sensory perception: GO | 21 | 2 | 1.59E−01 | 4.67E−01 | 2.08 | CHRNA9; NTRK1 |
| endosome lumen: GO | 21 | 2 | 1.59E−01 | 4.67E−01 | 2.08 | CTSB; RAB38 |
| glutamine family amino acid catabolic process: GO | 21 | 2 | 1.59E−01 | 4.67E−01 | 2.08 | ALDH4A1; GOT2 |
| process: GO | 21 | 2 | 1.59E−01 | 4.67E−01 | 2.08 | GSTO1; GSTP1 |
| growth hormone receptor signaling | 21 | 2 | 1.59E−01 | 4.67E−01 | 2.08 | SOCS3; STAT1 |
| il 2 signaling pathway | 21 | 2 | 1.59E−01 | 4.67E−01 | 2.08 | IL2RA; JAK3 |
| il 6 signaling pathway | 21 | 2 | 1.59E−01 | 4.67E−01 | 2.08 | IL6; JAK3 |
| il2 pathway | 21 | 2 | 1.59E−01 | 4.67E−01 | 2.08 | IL2RA; JAK3 |
| innervation: GO | 21 | 2 | 1.59E−01 | 4.67E−01 | 2.08 | FBXO45; NTRK1 |
| mitochondria pathway | 21 | 2 | 1.59E−01 | 4.67E−01 | 2.08 | BAK1; CYCS |
| negative regulation of osteoclast differentiation: GO | 21 | 2 | 1.59E−01 | 4.67E−01 | 2.08 | CCL3; LTF |
| negative regulation of oxidoreductase activity: GO | 21 | 2 | 1.59E−01 | 4.67E−01 | 2.08 | CYP27B1; GZMA |
| ns1 mediated effects on host pathways | 21 | 2 | 1.59E−01 | 4.67E−01 | 2.08 | ISG15; KPNA2 |
| nucleobase containing small molecule interconversion: GO | 21 | 2 | 1.59E−01 | 4.67E−01 | 2.08 | NME1; RRM2 |
| plasma lipoprotein clearance | 21 | 2 | 1.59E−01 | 4.67E−01 | 2.08 | LDLR; PCSK9 |
| positive regulation of nucleoside metabolic process: GO | 21 | 2 | 1.59E−01 | 4.67E−01 | 2.08 | HIF1A; VCP |
| preribosome large subunit precursor: GO | 21 | 2 | 1.59E−01 | 4.67E−01 | 2.08 | EBNA1BP2; EIF6 |
| regulation of protein import into nucleus translocation: GO | 21 | 2 | 1.59E−01 | 4.67E−01 | 2.08 | CDK1; IL6 |
| regulation of telomere capping: GO | 21 | 2 | 1.59E−01 | 4.67E−01 | 2.08 | NEK2; PRKCQ |
| synthesis-dependent strand annealing (sdsa) | 21 | 2 | 1.59E−01 | 4.67E−01 | 2.08 | BLM; EXO1 |
| s1p meta pathway | 21 | 2 | 1.59E−01 | 4.67E−01 | 2.08 | GNA15; SIPR4 |
| traf6 mediated irf7 activation | 21 | 2 | 1.59E−01 | 4.67E−01 | 2.08 | IL6; MYD88 |
| mapk1/mapk3 signaling | 142 | 9 | 1.59E−01 | 4.67E−01 | 1.39 | CDK1; CSF2; DUSP9; HBEGF; IL2RA; IL6; JAK3; PSMA5; PSMB6 |
| organization: GO | 88 | 6 | 1.61E−01 | 4.72E−01 | 1.49 | BAK1; HK2; PPIF; SFN; SLC25A5; YWHAQ |
| response to xenobiotic stimulus: GO | 88 | 6 | 1.61E−01 | 4.72E−01 | 1.49 | APOBEC3A; GSTO1; GSTP1; S100A12; UGT1A10; UGT1A7 |
| plasma membrane receptor complex: GO | 161 | 10 | 1.61E−01 | 4.72E−01 | 1.36 | CD3E; CHRNA3; CHRNA6; CHRNA9; HTR3A; IL13RA1; IL6; ITGAX; ITGB6; NETO2 |
| positive regulation of endocytosis: GO | 106 | 7 | 1.62E−01 | 4.73E−01 | 1.44 | CALR; IL1B; PCSK9; PYCARD; SELE; SERPINE1; WNT5A |
| carboxypeptidase activity: GO | 37 | 3 | 1.63E−01 | 4.74E−01 | 1.77 | CNDP2; CPA6; CPXMI |
| cysteine type endopeptidase regulator activity involved in apoptotic process: GO | 37 | 3 | 1.63E−01 | 4.74E−01 | 1.77 | BIRC5; PYCARD; SERPINB9 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| cytokine secretion: GO | 37 | 3 | 1.63E−01 | 4.74E−01 | 1.77 | PNP; S100A12; TREM1 |
| microtubule polymerization or depolymerization: GO | 37 | 3 | 1.63E−01 | 4.74E−01 | 1.77 | KIF14; KIF18A; KIF2C |
| positive regulation of calcium mediated signaling: GO | 37 | 3 | 1.63E−01 | 4.74E−01 | 1.77 | CCL3; CD3E; GSTO1 |
| positive regulation of response to biotic stimulus: GO | 37 | 3 | 1.63E−01 | 4.74E−01 | 1.77 | DEFB103A; DEFB103B; IL12B |
| sle transporter disorders | 37 | 3 | 1.63E−01 | 4.74E−01 | 1.77 | GK; SLC16A1; SLC2A9 |
| endocytic vesicle membrane: GO | 143 | 9 | 1.64E−01 | 4.77E−01 | 1.38 | AP1S3; FCGR1A; HBEGF; LDLR; RAB31; RAB38; RAC2; WNT5A; WNT7A |
| lymphocyte costimulation: GO | 71 | 5 | 1.65E−01 | 4.78E−01 | 1.54 | CD274; CD3E; CD80; CTLA4; ICOS |
| positive regulation of camp metabolic process: GO | 71 | 5 | 1.65E−01 | 4.78E−01 | 1.54 | ADCYAP1; CXCL10; CXCL11; CXCL9; GPR65 |
| regulation of insulin-like growth factor (igf) transport and uptake by insulin-like growth factor binding proteins (igfbps) | 71 | 5 | 1.65E−01 | 4.78E−01 | 1.54 | CKAP4; IL6; MMP1; PCSK9; TNC |
| vitamin binding: GO | 71 | 5 | 1.65E−01 | 4.78E−01 | 1.54 | ADH7; CRABP2; OGDHL; PYGL; TCN1 |
| olfactory transduction | 54 | 4 | 1.66E−01 | 4.81E−01 | 1.62 | CALML3; CALML5; CLCA2; CNGB1 |
| rig i like receptor signaling pathway | 54 | 4 | 1.66E−01 | 4.81E−01 | 1.62 | CXCL10; IFNE; IL12B; ISG15 |
| txa2pathway | 54 | 4 | 1.66E−01 | 4.81E−01 | 1.62 | GNA15; PRKCQ; SELE; TGM2 |
| regulation of transcription factor import into nucleus: GO | 89 | 6 | 1.67E−01 | 4.81E−01 | 1.47 | IL12B; IL1B; MDFI; PRDX1; PRKCQ; ZC3H12A |
| regulation of receptor activity: GO | 107 | 7 | 1.67E−01 | 4.81E−01 | 1.43 | EPGN; GSTO1; NETO2; PCSK9; PLAU; SERPINE1; TGFA |
| dna recombination: GO | 182 | 11 | 1.71E−01 | 4.81E−01 | 1.32 | BLM; CDC45; EXO1; H2AFX; HMGB3; MND1; PCNA; PIF1; POLQ; TOP2A; TRIP13 |
| acetyl coa metabolic process: GO | 22 | 2 | 1.72E−01 | 4.81E−01 | 1.99 | KYNU; TDO2 |
| adp signalling through p2ry1 | 22 | 2 | 1.72E−01 | 4.81E−01 | 1.99 | GNA15; GNGT2 |
| caspase cascade in apoptosis | 22 | 2 | 1.72E−01 | 4.81E−01 | 1.99 | LMNB1; LMNB2 |
| cellular extravasation: GO | 22 | 2 | 1.72E−01 | 4.81E−01 | 1.99 | SELE; TREM1 |
| cellular response to toxic substance: GO | 22 | 2 | 1.72E−01 | 4.81E−01 | 1.99 | HIF1A; IL1B |
| chemical pathway | 22 | 2 | 1.72E−01 | 4.81E−01 | 1.99 | CYCS; STAT1 |
| chemoattractant activity: GO | 22 | 2 | 1.72E−01 | 4.81E−01 | 1.99 | CCL3; WNT5A |
| glucuronosyltransferase activity: GO | 22 | 2 | 1.72E−01 | 4.81E−01 | 1.99 | UGT1A10; UGT1A7 |
| grb2 events in erbb2 signaling | 22 | 2 | 1.72E−01 | 4.81E−01 | 1.99 | CDK1; HBEGF |
| host interactions with influenza factors | 22 | 2 | 1.72E−01 | 4.81E−01 | 1.99 | ISG15; KPNA2 |
| il6 pathway | 22 | 2 | 1.72E−01 | 4.81E−01 | 1.99 | IL6; JAK3 |
| intrinsic pathway | 22 | 2 | 1.72E−01 | 4.81E−01 | 1.99 | C1QBP; F12 |
| inwardly rectifying k channels | 22 | 2 | 1.72E−01 | 4.81E−01 | 1.99 | GNGT2; KCNJ15 |
| organism involved in symbiotic interaction: GO | 22 | 2 | 1.72E−01 | 4.81E−01 | 1.99 | CCL3; HMGA2 |
| transmission: GO | 22 | 2 | 1.72E−01 | 4.81E−01 | 1.99 | CHRNA3; CHRNA6 |
| nfkb activation by nontypeable hemophilus influenzae | 22 | 2 | 1.72E−01 | 4.81E−01 | 1.99 | IL1B; MYD88 |
| nuclear euchromatin: GO | 22 | 2 | 1.72E−01 | 4.81E−01 | 1.99 | H2AFZ; HIST1H1A |
| pdgfra pathway | 22 | 2 | 1.72E−01 | 4.81E−01 | 1.99 | IFNG; SHB |
| polysaccharide catabolic process: GO | 22 | 2 | 1.72E−01 | 4.81E−01 | 1.99 | PGM2; PYGL |
| positive regulation of peptidyl threonine phosphorylation: GO | 22 | 2 | 1.72E−01 | 4.81E−01 | 1.99 | PLK1; WNT5A |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| positive regulation of protein complex disassembly: GO | 22 | 2 | 1.72E−01 | 4.81E−01 | 1.99 | EIF5A; EIF5AL1 |
| positive regulation of substrate adhesion dependent cell spreading: GO | 22 | 2 | 1.72E−01 | 4.81E−01 | 1.99 | C1QBP; CALR |
| pyrimidine ribonucleotide metabolic process: GO | 22 | 2 | 1.72E−01 | 4.81E−01 | 1.99 | NME1; UPP1 |
| regulation of epidermal growth factor activated receptor activity: GO | 22 | 2 | 1.72E−01 | 4.81E−01 | 1.99 | EPGN; TGFA |
| assembly: GO | 22 | 2 | 1.72E−01 | 4.81E−01 | 1.99 | FSCN1; RAC2 |
| regulation of osteoblast proliferation: GO | 22 | 2 | 1.72E−01 | 4.81E−01 | 1.99 | HPSE; LTF |
| regulation of superoxide metabolic process: GO | 22 | 2 | 1.72E−01 | 4.81E−01 | 1.99 | ACP5; GSTP1 |
| cytotoxicity: GO | 22 | 2 | 1.72E−01 | 4.81E−01 | 1.99 | IL12B; IL7R |
| somatic stem cell division: GO | 22 | 2 | 1.72E−01 | 4.81E−01 | 1.99 | ASPM; WNT7A |
| activity: GO | 72 | 5 | 1.72E−01 | 4.81E−01 | 1.52 | DUSP14; DUSP9; GSTP1; IL1B; SERPINB3 |
| polysaccharide metabolic process: GO | 72 | 5 | 1.72E−01 | 4.81E−01 | 1.52 | B3GNT3; CHST1; HAS3; PGM2; PYGL |
| binding: GO | 72 | 5 | 1.72E−01 | 4.81E−01 | 1.52 | MMP9; PLK2; RALB; RAN; WNT5A |
| regulation of protein maturation: GO | 72 | 5 | 1.72E−01 | 4.81E−01 | 1.52 | BIRC5; C1QBP; CHAC1; F12; SERPINE1 |
| androgen receptor binding: GO | 38 | 3 | 1.72E−01 | 4.81E−01 | 1.73 | CALR; CCNE1; RAN |
| bile acid biosynthesis | 38 | 3 | 1.72E−01 | 4.81E−01 | 1.73 | ADH7; AKR1B10; ALDH1A3 |
| endodermal cell differentiation: GO | 38 | 3 | 1.72E−01 | 4.81E−01 | 1.73 | EOMES; HMGA2; MMP9 |
| integrin3 pathway | 38 | 3 | 1.72E−01 | 4.81E−01 | 1.73 | PLAU; PLAUR; TNC |
| lung alveolus development: GO | 38 | 3 | 1.72E−01 | 4.81E−01 | 1.73 | FOXF1; STRA6; WNT5A |
| negative regulation of type i interferon production: GO | 38 | 3 | 1.72E−01 | 4.81E−01 | 1.73 | ISG15; NMI; PYCARD |
| nucleoid: GO | 38 | 3 | 1.72E−01 | 4.81E−01 | 1.73 | LRRC59; SLC25A5; TOP2A |
| regulation of cell adhesion mediated by integrin: GO | 38 | 3 | 1.72E−01 | 4.81E−01 | 1.73 | CXCL13; PLAU; SERPINE1 |
| regulation of plasma lipoprotein particle levels: GO | 38 | 3 | 1.72E−01 | 4.81E−01 | 1.73 | HMOX1; LDLR; LIPG |
| response to cadmium ion: GO | 38 | 3 | 1.72E−01 | 4.81E−01 | 1.73 | CDK1; HMOX1; PCNA |
| emil | 38 | 3 | 1.72E−01 | 4.81E−01 | 1.73 | CDC20; PSMA5; PSMB6 |
| cellular response to starvation: GO | 108 | 7 | 1.73E−01 | 4.82E−01 | 1.42 | DSC2; HSPA8; IFI16; PCSK9; RALB; UPP1; ZC3H12A |
| organophosphate catabolic process: GO | 108 | 7 | 1.73E−01 | 4.82E−01 | 1.42 | LIPG; NUDT15; PGM2; PLA2G4D; PNP; UPP1; VCP |
| regulation of calcium ion import: GO | 90 | 6 | 1.73E−01 | 4.83E−01 | 1.46 | CCL3; CXCL 10; CXCL11; CXCL9; GSTO1; HOMER1 |
| positive regulation of multi organism process: GO | 145 | 9 | 1.74E−01 | 4.83E−01 | 1.36 | AURKA; C1QBP; DEFB103A; DEFB 103B; IFNG; PLAU; PPIB; PTAFR; TOP2A |
| prolonged erk activation events | 145 | 9 | 1.74E−01 | 4.83E−01 | 1.36 | CDK1; CSF2; DUSP9; HBEGF; IL2RA; JAK3; NTRK1; PSMA5; PSMB6 |
| diencephalon development: GO | 55 | 4 | 1.74E−01 | 4.84E−01 | 1.59 | ADCYAP1; CNTNAP2; PITX1; WNT5A |
| positive regulation of response to dna damage stimulus: GO | 55 | 4 | 1.74E−01 | 4.84E−01 | 1.59 | FOXM1; H2AFX; HMGA2; PCNA |
| digestive system development: GO | 127 | 8 | 1.77E−01 | 4.90E−01 | 1.38 | CCNB1; FOXE1; FOXF1; HIF1A; PRDM1; STRA6; TK1; WNT5A |
| gastrin creb signalling pathway via pkc and mapk | 91 | 6 | 1.80E−01 | 4.97E−01 | 1.44 | CDK1; GNA15; GNGT2; GPR65; PRKCQ; PTAFR |
| mrna | 39 | 3 | 1.82E−01 | 4.97E−01 | 1.68 | HSPA8; PSMA5; PSMB6 |
| il 3 5 and gm csf signaling | 39 | 3 | 1.82E−01 | 4.97E−01 | 1.68 | CSF2; IL2RA; JAK3 |
| intrinsic pathway for apoptosis | 39 | 3 | 1.82E−01 | 4.97E−01 | 1.68 | BAK1; CYCS; SFN |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| negative regulation of myeloid leukocyte differentiation: GO | 39 | 3 | 1.82E−01 | 4.97E−01 | 1.68 | CCL3; LTF; NME1 |
| nuclear replication fork: GO | 39 | 3 | 1.82E−01 | 4.97E−01 | 1.68 | CDC45; MCM10; PCNA |
| protein tyrosine serine threonine phosphatase activity: GO | 39 | 3 | 1.82E−01 | 4.97E−01 | 1.68 | CDKN3; DUSP14; DUSP9 |
| response to cold: GO | 39 | 3 | 1.82E−01 | 4.97E−01 | 1.68 | CXCL10; GK; IL6 |
| autodegradation of cdh1 by cdh1 ape c | 56 | 4 | 1.82E−01 | 4.97E−01 | 1.56 | PSMA4; PSMA5; PSMB6; UBE2C |
| glutamine family amino acid metabolic process: GO | 56 | 4 | 1.82E−01 | 4.97E−01 | 1.56 | ALDH4A1; GGH; GOT2; HAL |
| negative regulation of ossification: GO | 56 | 4 | 1.82E−01 | 4.97E−01 | 1.56 | AREG; CCL3; HIF1A; SRGN |
| pancreas development: GO | 56 | 4 | 1.82E−01 | 4.97E−01 | 1.56 | BAK1; FOXF1; IL6; WNT5A |
| process: GO | 56 | 4 | 1.82E−01 | 4.97E−01 | 1.56 | FABP5; PLA2G3; PLA2G4D; PLBD1 |
| pigment metabolic process: GO | 56 | 4 | 1.82E−01 | 4.97E−01 | 1.56 | HMOX1; HMOX2; UGT1A10; UGT1A7 |
| stem cell proliferation: GO | 56 | 4 | 1.82E−01 | 4.97E−01 | 1.56 | ARTN; ASPM; STAT1; WNT5A |
| actin monomer binding: GO | 23 | 2 | 1.85E−01 | 4.97E−01 | 1.90 | TMSB10; TWF1 |
| apoptotic nuclear changes: GO | 23 | 2 | 1.85E−01 | 4.97E−01 | 1.90 | DNASEIL3; TOP2A |
| transport: GO | 23 | 2 | 1.85E−01 | 4.97E−01 | 1.90 | SLC2A9; SLC5A1 |
| ctla4 inhibitory signaling | 23 | 2 | 1.85E−01 | 4.97E−01 | 1.90 | CD80; CTLA4 |
| cysteine metabolism | 23 | 2 | 1.85E−01 | 4.97E−01 | 1.90 | GOT2; LDHA |
| dna secondary structure binding: GO | 23 | 2 | 1.85E−01 | 4.97E−01 | 1.90 | BLM; HMGB3 |
| epithelial tube branching involved in lung morphogenesis: GO | 23 | 2 | 1.85E−01 | 4.97E−01 | 1.90 | FOXF1; TNC |
| establishment of mitotic spindle localization: GO | 23 | 2 | 1.85E−01 | 4.97E−01 | 1.90 | CENPA; NDC80 |
| fibroblast growth factor binding: GO | 23 | 2 | 1.85E−01 | 4.97E−01 | 1.90 | CXCL13; FGFBP1 |
| fluid transport: GO | 23 | 2 | 1.85E−01 | 4.97E−01 | 1.90 | AQP3; CSF2 |
| g alpha z signalling events | 23 | 2 | 1.85E−01 | 4.97E−01 | 1.90 | GNGT2; PRKCQ |
| histone monoubiquitination: GO | 23 | 2 | 1.85E−01 | 4.97E−01 | 1.90 | DTX3L; UHRF1 |
| intestinal absorption: GO | 23 | 2 | 1.85E−01 | 4.97E−01 | 1.90 | LDLR; SLC5A1 |
| lysosome localization: GO | 23 | 2 | 1.85E−01 | 4.97E−01 | 1.90 | NR4A3; PLA2G3 |
| transport: GO | 23 | 2 | 1.85E−01 | 4.97E−01 | 1.90 | HRH3; IL1B |
| nthi pathway | 23 | 2 | 1.85E−01 | 4.97E−01 | 1.90 | IL1B; MYD88 |
| positive regulation of erythrocyte differentiation: GO | 23 | 2 | 1.85E−01 | 4.97E−01 | 1.90 | HIF1A; ISG15 |
| assembly: GO | 23 | 2 | 1.85E−01 | 4.97E−01 | 1.90 | FSCN1; PRKCQ |
| positive regulation of receptor internalization: GO | 23 | 2 | 1.85E−01 | 4.97E−01 | 1.90 | PCSK9; SELE |
| prl signaling events pathway | 23 | 2 | 1.85E−01 | 4.97E−01 | 1.90 | CCNA2; CCNE1 |
| ptm gamma carboxylation hypusine formation and arylsulfatase activation | 23 | 2 | 1.85E−01 | 4.97E−01 | 1.90 | ARSH; EIF5A |
| regulation of antigen processing and presentation: GO | 23 | 2 | 1.85E−01 | 4.97E−01 | 1.90 | PYCARD; TAP2 |
| regulation of fibroblast growth factor receptor signaling pathway: GO | 23 | 2 | 1.85E−01 | 4.97E−01 | 1.90 | FGFBP1; WNT5A |
| proliferation: GO | 23 | 2 | 1.85E−01 | 4.97E−01 | 1.90 | ASPM; HIF1A |
| regulation of thymocyte aggregation: GO | 23 | 2 | 1.85E−01 | 4.97E−01 | 1.90 | IL1B; IL7R |
| response to increased oxygen levels: GO | 23 | 2 | 1.85E−01 | 4.97E−01 | 1.90 | PLAU; WNT5A |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| snorna binding: GO | 23 | 2 | 1.85E−01 | 4.97E−01 | 1.90 | DDX21; ISG20 |
| nuclear pore: GO | 74 | 5 | 1.86E−01 | 5.00E−01 | 1.48 | EIF5A; EIF5AL1; KPNA2; MAD2L1; RAN |
| endoplasmic reticulum golgi intermediate compartment: GO | 92 | 6 | 1.86E−01 | 5.00E−01 | 1.43 | AREG; CTSC; GJB2; SERPINA1; TGFA; VMP1 |
| neuron migration: GO | 92 | 6 | 1.86E−01 | 5.00E−01 | 1.43 | ASPM; CCK; CCR4; CDK5R1; CXCR4; FBXO45 |
| process: GO | 129 | 8 | 1.87E−01 | 5.02E−01 | 1.36 | B3GNT3; GK; HAS3; HK2; PFKFB4; PGM2; PYGL; TPI1 |
| g protein coupled receptor signaling pathway coupled to cyclic nucleotide second messenger: GO | 129 | 8 | 1.87E−01 | 5.02E−01 | 1.36 | ADCYAP1; ADM2; FPR1; GPR1; HRH3; HTR7; RGS1; SIPR4 |
| glycerolipid metabolism | 57 | 4 | 1.91E−01 | 5.09E−01 | 1.53 | ADH7; ALDH1A3; GK; LIPG |
| activity: GO | 57 | 4 | 1.91E−01 | 5.09E−01 | 1.53 | GSTO1; MMP9; PCSK9; PPIF |
| positive regulation of lipase activity: GO | 57 | 4 | 1.91E−01 | 5.09E−01 | 1.53 | GNA15; PTAFR; SIPR4; SELE |
| pyruvate metabolism | 57 | 4 | 1.91E−01 | 5.09E−01 | 1.53 | ALDH1A3; LDHA; PKM; SLC16A1 |
| regulation of atpase activity: GO | 57 | 4 | 1.91E−01 | 5.09E−01 | 1.53 | ATP1B3; LTF; PPIF; UHRF1 |
| regulation of viral transcription: GO | 57 | 4 | 1.91E−01 | 5.09E−01 | 1.53 | CCL3; HMGA2; IFITM3; TRIM14 |
| transferase activity transferring sulfur containing groups: GO | 57 | 4 | 1.91E−01 | 5.09E−01 | 1.53 | CHST1; HS3ST1; HS3ST3A1; HS3ST3B1 |
| autodegradation of cdh1 by cdh1:apc/c | 40 | 3 | 1.92E−01 | 5.09E−01 | 1.64 | PSMA5; PSMB6; UBE2C |
| ifng pathway | 40 | 3 | 1.92E−01 | 5.09E−01 | 1.64 | IFNG; IL1B; STAT1 |
| nicotinate and nicotinamide metabolism | 40 | 3 | 1.92E−01 | 5.09E−01 | 1.64 | NAMPT; PNP; VNN3 |
| polysaccharide biosynthetic process: GO | 40 | 3 | 1.92E−01 | 5.09E−01 | 1.64 | B3GNT3; HAS3; PGM2 |
| positive regulation of mrna metabolic process: GO | 40 | 3 | 1.92E−01 | 5.09E−01 | 1.64 | CCNB1; HSPA8; ZC3H12A |
| differentiation: GO | 40 | 3 | 1.92E−01 | 5.09E−01 | 1.64 | CXCL10; CXCL9; NEU2 |
| regulation of vasodilation: GO | 40 | 3 | 1.92E−01 | 5.09E−01 | 1.64 | ADCYAP1; HMOX1; PTAFR |
| response to cocaine: GO | 40 | 3 | 1.92E−01 | 5.09E−01 | 1.64 | CCNA2; HOMER1; HTR3A |
| secondary metabolic process: GO | 40 | 3 | 1.92E−01 | 5.09E−01 | 1.64 | AKR1B10; IL1B; UGT1A7 |
| substantia nigra development: GO | 40 | 3 | 1.92E−01 | 5.09E−01 | 1.64 | INA; LDHA; YWHAQ |
| protein tyrosine phosphatase activity: GO | 93 | 6 | 1.93E−01 | 5.10E−01 | 1.41 | CDC25A; CDC25B; CDKN3; DUSP14; DUSP9; PTPRE |
| positive regulation of stress activated protein kinase signaling cascade: GO | 130 | 8 | 1.93E−01 | 5.10E−01 | 1.35 | IL1B; IL26; MDFI; PYCARD; SLAMF1; WNT5A; WNT7A; ZC3H12A |
| chaperone binding: GO | 75 | 5 | 1.93E−01 | 5.10E−01 | 1.46 | BAK1; BIRC5; CALR; CTSC; SDF2L1 |
| negative regulation of transmembrane transport: GO | 75 | 5 | 1.93E−01 | 5.10E−01 | 1.46 | GSTO1; MMP9; PCSK9; PPIF; YWHAQ |
| positive regulation of myeloid cell differentiation: GO | 75 | 5 | 1.93E−01 | 5.10E−01 | 1.46 | HIF1A; IFNG; IL12B; IL20; ISG15 |
| alpha tubulin binding: GO | 24 | 2 | 1.98E−01 | 5.13E−01 | 1.82 | FAM110C; SNCB |
| beta-alanine metabolism | 24 | 2 | 1.98E−01 | 5.13E−01 | 1.82 | ALDH1A3; SRM |
| cellular response to vitamin: GO | 24 | 2 | 1.98E−01 | 5.13E−01 | 1.82 | CYP24A1; TNC |
| dna catabolic process: GO | 24 | 2 | 1.98E−01 | 5.13E−01 | 1.82 | DNASEIL3; ISG20 |
| establishment of spindle orientation: GO | 24 | 2 | 1.98E−01 | 5.13E−01 | 1.82 | CENPA; NDC80 |
| formation of fibrin clot (clotting cascade) | 24 | 2 | 1.98E−01 | 5.13E−01 | 1.82 | C1QBP; F12 |
| gap junction: GO | 24 | 2 | 1.98E−01 | 5.13E−01 | 1.82 | GJB2; GJB6 |
| histone mrna metabolic process: GO | 24 | 2 | 1.98E−01 | 5.13E−01 | 1.82 | SNRPF; SNRPG |
| hivnef pathway | 24 | 2 | 1.98E−01 | 5.13E−01 | 1.82 | LMNB1; LMNB2 |
| hsf1 activation | 24 | 2 | 1.98E−01 | 5.13E−01 | 1.82 | HSPA6; TNFRSF21 |
| insulin glucose pathway | 24 | 2 | 1.98E−01 | 5.13E−01 | 1.82 | SFN; YWHAQ |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| interconversion of nucleotide di- and triphosphates | 24 | 2 | 1.98E−01 | 5.13E−01 | 1.82 | NME1; RRM2 |
| negative regulation of fatty acid metabolic process: GO | 24 | 2 | 1.98E−01 | 5.13E−01 | 1.82 | UGT1A10; UGT1A7 |
| donors with incorporation of molecular oxygen: GO | 24 | 2 | 1.98E−01 | 5.13E−01 | 1.82 | IDO1; TDO2 |
| positive regulation of g1 s transition of mitotic cell cycle: GO | 24 | 2 | 1.98E−01 | 5.13E−01 | 1.82 | CDC45; CDC6 |
| regulation of tp53 degradation | 24 | 2 | 1.98E−01 | 5.13E−01 | 1.82 | CCNA2; CDK1 |
| degradation | 24 | 2 | 1.98E−01 | 5.13E−01 | 1.82 | CCNA2; CDK1 |
| regulation of transforming growth factor beta production: GO | 24 | 2 | 1.98E−01 | 5.13E−01 | 1.82 | CDH3; HIF1A |
| regulation of type i interferon mediated signaling pathway: GO | 24 | 2 | 1.98E−01 | 5.13E−01 | 1.82 | STAT1; WNT5A |
| regulation of viral entry into host cell: GO | 24 | 2 | 1.98E−01 | 5.13E−01 | 1.82 | IFITM1; IFITM3 |
| resolution of d-loop structures | 24 | 2 | 1.98E−01 | 5.13E−01 | 1.82 | BLM; EXO1 |
| resolution of d-loop structures through holliday junction intermediates | 24 | 2 | 1.98E−01 | 5.13E−01 | 1.82 | BLM; EXO1 |
| response to corticosterone: GO | 24 | 2 | 1.98E−01 | 5.13E−01 | 1.82 | CCNE1; FOSL1 |
| response to pain: GO | 24 | 2 | 1.98E−01 | 5.13E−01 | 1.82 | NTRK1; OSM |
| coated vesicle membrane: GO | 131 | 8 | 1.98E−01 | 5.14E−01 | 1.34 | AP1S3; AREG; FCGR1A; HBEGF; HSPA8; LDLR; TGFA; WNT5A |
| regulation of intrinsic apoptotic signaling pathway: GO | 131 | 8 | 1.98E−01 | 5.14E−01 | 1.34 | HIF1A; IL19; MMP9; PLAUR; PPIF; PYCARD; S100A8; S100A9 |
| mapk family signaling cascades | 169 | 10 | 1.99E−01 | 5.15E−01 | 1.29 | CDK1; CSF2; DUSP9; HBEGF; IL2RA; IL6; JAK3; MAPK6; PSMA5; PSMB6 |
| transport: GO | 58 | 4 | 1.99E−01 | 5.15E−01 | 1.51 | SLC38A5; SLC7A1; SLC7A11; SLC7A5 |
| g alpha s signalling events | 58 | 4 | 1.99E−01 | 5.15E−01 | 1.51 | ADCYAP1; ADM2; GNGT2; HTR7 |
| oligosaccharide metabolic process: GO | 58 | 4 | 1.99E−01 | 5.15E−01 | 1.51 | FUT3; NEU2; ST6GALNAC1; ST8S1A2 |
| dna geometric change: GO | 76 | 5 | 2.01E−01 | 5.17E−01 | 1.44 | BLM; CDC45; HMGB3; PIF1; TOP2A |
| hydrolase activity hydrolyzing o glycosyl compounds: GO | 76 | 5 | 2.01E−01 | 5.17E−01 | 1.44 | CHI3L2; HPSE; HYAL3; LYZ; NEU2 |
| regulation of jun kinase activity: GO | 76 | 5 | 2.01E−01 | 5.17E−01 | 1.44 | GSTP1; IL1B; MDFI; SERPINB3; WNT5A |
| carbohydrate transporter activity: GO | 41 | 3 | 2.02E−01 | 5.18E−01 | 1.60 | AQP3; SLC2A9; SLC5A1 |
| ceramide biosynthetic process: GO | 41 | 3 | 2.02E−01 | 5.18E−01 | 1.60 | ST6GALNAC1; ST8S1A2; UGCG |
| cytoplasmic translation: GO | 41 | 3 | 2.02E−01 | 5.18E−01 | 1.60 | EIF4EBP1; RPL22L1; RPL26L1 |
| er nongenomic pathway | 41 | 3 | 2.02E−01 | 5.18E−01 | 1.60 | GNA15; HBEGF; MMP9 |
| modification by symbiont of host morphology or physiology: GO | 41 | 3 | 2.02E−01 | 5.18E−01 | 1.60 | KPNA2; SERPINB9; ZC3H12A |
| positive regulation of phagocytosis: GO | 41 | 3 | 2.02E−01 | 5.18E−01 | 1.60 | CALR; IL1B; PYCARD |
| pyridoxal phosphate binding: GO | 41 | 3 | 2.02E−01 | 5.18E−01 | 1.60 | GOT2; KYNU; PYGL |
| regulation of oxidative stress induced cell death: GO | 41 | 3 | 2.02E−01 | 5.18E−01 | 1.60 | HIF1A; MMP3; NR4A3 |
| regulation of telomerase activity: GO | 41 | 3 | 2.02E−01 | 5.18E−01 | 1.60 | NEK2; PIF1; PRKCQ |
| sterol transport: GO | 41 | 3 | 2.02E−01 | 5.18E−01 | 1.60 | ABCG4; LDLR; LIPG |
| signaling: GO | 113 | 7 | 2.02E−01 | 5.18E−01 | 1.35 | C1QBP; CCL3; FAM110C; HBEGF; HPSE; IL26; IL6 |
| detection of abiotic stimulus: GO | 95 | 6 | 2.06E−01 | 5.26E−01 | 1.38 | CHRNA9; CNGB1; GNGT2; NTRK1; PITPNM1; TIMELESS |
| pathway: GO | 95 | 6 | 2.06E−01 | 5.26E−01 | 1.38 | BAK1; BCL2A1; IFNG; IL1B; TNFRSF12A; TNFRSF9 |
| cargo receptor activity: GO | 59 | 4 | 2.08E−01 | 5.28E−01 | 1.48 | LDLR; LRP8; OLR1; TMPRSS4 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| collagen binding: GO | 59 | 4 | 2.08E−01 | 5.28E−01 | 1.48 | CTSB; MMP9; PPIB; SRGN |
| uch proteinases | 59 | 4 | 2.08E−01 | 5.28E−01 | 1.48 | H2AFX; HIST1H2AE; PSMA5; PSMB6 |
| signaling by hedgehog | 77 | 5 | 2.08E−01 | 5.28E−01 | 1.42 | PSMA5; PSMB6; TUBA1C; TUBB2A; TUBB6 |
| steroid hormone receptor binding: GO | 77 | 5 | 2.08E−01 | 5.28E−01 | 1.42 | CALR; CCNE1; NR4A3; PCNA; RAN |
| udp glycosyltransferase activity: GO | 114 | 7 | 2.09E−01 | 5.28E−01 | 1.34 | B3GNT3; GALNT6; GCNT4; HAS3; UGCG; UGT1A10; UGT1A7 |
| positive regulation of i kappab kinase nf kappab signaling: GO | 171 | 10 | 2.09E−01 | 5.28E−01 | 1.28 | ECT2; HMOX1; IL12B; IL1B; LTF; MYD88; PLK2; PRKCQ; S100A12; TNFSF10 |
| organic anion transmembrane transporter activity: GO | 152 | 9 | 2.10E−01 | 5.28E−01 | 1.29 | SLC16A1; SLC16A6; SLC16A9; SLC26A9; SLC38A5; SLC6A11; SLC7A1; SLC7A11; SLC7A5 |
| ruffle: GO | 152 | 9 | 2.10E−01 | 5.28E−01 | 1.29 | FERMT1; FSCN1; KIF18A; MEFV; NME1; S100A11; SAMSN1; TNFRSF12A; TWF1 |
| establishment or maintenance of cell polarity: GO | 133 | 8 | 2.10E−01 | 5.28E−01 | 1.32 | CENPA; FERMT1; FOXF1; FSCN1; KIF2C; NDC80; WNT5A; WNT7A |
| 1-and 2-methylnaphthalene degradation | 25 | 2 | 2.11E−01 | 5.28E−01 | 1.75 | ADH7; ESCO2 |
| cerebral cortex radially oriented cell migration: GO | 25 | 2 | 2.11E−01 | 5.28E−01 | 1.75 | CDK5R1; FBXO45 |
| dna strand elongation involved in dna replication: GO | 25 | 2 | 2.11E−01 | 5.28E−01 | 1.75 | GINS3; PCNA |
| embryonic hindlimb morphogenesis: GO | 25 | 2 | 2.11E−01 | 5.28E−01 | 1.75 | PITX1; WNT7A |
| fear response: GO | 25 | 2 | 2.11E−01 | 5.28E−01 | 1.75 | ADCYAP1; CCK |
| inactivation of mapk activity: GO | 25 | 2 | 2.11E−01 | 5.28E−01 | 1.75 | DUSP14; DUSP9 |
| mesodermal cell differentiation: GO | 25 | 2 | 2.11E−01 | 5.28E−01 | 1.75 | FOXF1; HMGA2 |
| metallocarboxypeptidase activity: GO | 25 | 2 | 2.11E−01 | 5.28E−01 | 1.75 | CPA6; CPXMI |
| negative regulation of exocytosis: GO | 25 | 2 | 2.11E−01 | 5.28E−01 | 1.75 | FOXF1; HMOX1 |
| oxidoreductase activity acting on the ch nh group of donors: GO | 25 | 2 | 2.11E−01 | 5.28E−01 | 1.75 | ALDH4A1; SMOX |
| positive regulation of heart growth: GO | 25 | 2 | 2.11E−01 | 5.28E−01 | 1.75 | CCNB1; CDK1 |
| translocation: GO | 25 | 2 | 2.11E−01 | 5.28E−01 | 1.75 | IFNG; RAN |
| regulation of oligodendrocyte differentiation: GO | 25 | 2 | 2.11E−01 | 5.28E−01 | 1.75 | CXCR4; TNFRSF21 |
| regulation of vascular endothelial growth factor receptor signaling pathway: GO | 25 | 2 | 2.11E−01 | 5.28E−01 | 1.75 | HIF1A; IL1B |
| response to copper ion: GO | 25 | 2 | 2.11E−01 | 5.28E−01 | 1.75 | CDK1; TK1 |
| retinol metabolic process: GO | 25 | 2 | 2.11E−01 | 5.28E−01 | 1.75 | ADH7; ALDH1A3 |
| sodium ion homeostasis: GO | 25 | 2 | 2.11E−01 | 5.28E−01 | 1.75 | ATP12A; ATP1B3 |
| strand displacement: GO | 25 | 2 | 2.11E−01 | 5.28E−01 | 1.75 | BLM; EXO1 |
| sulfur amino acid metabolism | 25 | 2 | 2.11E−01 | 5.28E−01 | 1.75 | AHCY; CNDP2 |
| sulfur compound transmembrane transporter activity: GO | 25 | 2 | 2.11E−01 | 5.28E−01 | 1.75 | SLC26A9; SLC7A11 |
| u12 type spliceosomal complex: GO | 25 | 2 | 2.11E−01 | 5.28E−01 | 1.75 | SNRPF; SNRPG |
| peptide receptor activity: GO | 96 | 6 | 2.13E−01 | 5.28E−01 | 1.37 | CCR4; CCR5; CXCR4; FPR1; FPR3; LTB4R |
| regulation of myeloid leukocyte differentiation: GO | 96 | 6 | 2.13E−01 | 5.28E−01 | 1.37 | CCL3; IFNG; IL12B; IL20; LTF; NME1 |
| regulation of peptidyl serine phosphorylation: GO | 96 | 6 | 2.13E−01 | 5.28E−01 | 1.37 | BAK1; IFNE; IFNG; IL6; OSM; WNT5A |
| atm pathway | 42 | 3 | 2.13E−01 | 5.28E−01 | 1.56 | BLM; CDC25A; H2AFX |
| glycine, serine and threonine metabolism | 42 | 3 | 2.13E−01 | 5.28E−01 | 1.56 | AKR 1B10; GARS; TARS |
| intraspecies interaction between | 42 | 3 | 2.13E−01 | 5.28E−01 | 1.56 | CNTNAP2; IL1B; NLGN4X |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| organisms: GO | | | | | | |
| oxygen-dependent proline hydroxylation of hypoxia-inducible factor alpha | 42 | 3 | 2.13E−01 | 5.28E−01 | 1.56 | HIF1A; PSMA5; PSMB6 |
| positive regulation of telomere maintenance: GO | 42 | 3 | 2.13E−01 | 5.28E−01 | 1.56 | CCT5; NEK2; PRKCQ |
| primary alcohol metabolic process: GO | 42 | 3 | 2.13E−01 | 5.28E−01 | 1.56 | ADH7; AKR1B10; ALDH1A3 |
| production: GO | 42 | 3 | 2.13E−01 | 5.28E−01 | 1.56 | NMI; POLR3G; PYCARD |
| teptp pathway | 42 | 3 | 2.13E−01 | 5.28E−01 | 1.56 | JAK3; KPNA2; STAT1 |
| positive regulation of transmembrane transport: GO | 115 | 7 | 2.15E−01 | 5.33E−01 | 1.33 | ATP1B3; CCL3; CXCL10; CXCL11; CXCL9; GSTO1; PTAFR |
| positive regulation of cell growth: GO | 134 | 8 | 2.15E−01 | 5.34E−01 | 1.31 | CRABP2; HBEGF; HIST1H1B; KRT17; S100A8; S100A9; SFN; TNFRSF12A |
| arginine and proline metabolism | 60 | 4 | 2.16E−01 | 5.35E−01 | 1.46 | ALDH1A3; ALDH4A1; GOT2; SRM |
| cell redox homeostasis: GO | 60 | 4 | 2.16E−01 | 5.35E−01 | 1.46 | CAMP; IL6; LTF; SH3BGRL3 |
| il4 2pathway | 60 | 4 | 2.16E−01 | 5.35E−01 | 1.46 | IL13RA1; IL4R; JAK3; SOCS3 |
| regulation of phospholipase activity: GO | 60 | 4 | 2.16E−01 | 5.35E−01 | 1.46 | GNA15; PTAFR; SIPR4; SELE |
| activation of innate immune response: GO | 192 | 11 | 2.17E−01 | 5.36E−01 | 1.25 | CLEC7A; CTSB; IFI16; MYD88; PGLYRP2; PSMA4; PSMA5; PSMB6; PYCARD; S100A14; TNIP3 |
| negative regulation of establishment of protein localization: GO | 192 | 11 | 2.17E−01 | 5.36E−01 | 1.25 | IL1B; IL36RN; IL6; MDFI; RSAD2; SLAMF1; SRGN; TNFRSF21; TNFRSF9; VSNL1; ZC3H12A |
| ion: GO | 97 | 6 | 2.19E−01 | 5.41E−01 | 1.35 | CCL3; CCR5; CXCL10; CXCL11; CXCL9; GSTO1 |
| toll-like receptors cascades | 97 | 6 | 2.19E−01 | 5.41E−01 | 1.35 | CTSB; CTSL; MYD88; S100A12; S100A8; S100A9 |
| transition metal ion transport: GO | 97 | 6 | 2.19E−01 | 5.41E−01 | 1.35 | HEPHL1; SCO2; SLC39A6; STEAP1B; STEAP4; TCN1 |
| nuclear periphery: GO | 116 | 7 | 2.21E−01 | 5.41E−01 | 1.32 | BLM; CENPW; EBNA1BP2; KIF4A; LMNB1; LMNB2; UHRF1 |
| positive regulation of chromosome organization: GO | 135 | 8 | 2.21E−01 | 5.41E−01 | 1.30 | CCNB1; CCT5; DLGAP5; HISTIH1B; IL1B; NEK2; PLK1; PRKCQ |
| asymmetric localization of pcp proteins | 43 | 3 | 2.23E−01 | 5.41E−01 | 1.53 | PSMA5; PSMB6; WNT5A |
| columnar cuboidal epithelial cell development: GO | 43 | 3 | 2.23E−01 | 5.41E−01 | 1.53 | HIF1A; PRDM1; WNT5A |
| fanconi pathway | 43 | 3 | 2.23E−01 | 5.41E−01 | 1.53 | BLM; H2AFX; UBE2T |
| immunoglobulin production: GO | 43 | 3 | 2.23E−01 | 5.41E−01 | 1.53 | EXO1; IL7R; POLQ |
| negative regulation of carbohydrate metabolic process: GO | 43 | 3 | 2.23E−01 | 5.41E−01 | 1.53 | IL6; UGT1A10; UGT1A7 |
| transport of inorganic cations anions and amino acids oligopeptides | 43 | 3 | 2.23E−01 | 5.41E−01 | 1.53 | SLC26A9; SLC38A5; SLC4A8 |
| tissue remodeling: GO | 79 | 5 | 2.23E−01 | 5.41E−01 | 1.38 | ACP5; BAK1; HIF1A; IL6; RAC2 |
| regulation of nucleotide metabolic process: GO | 174 | 10 | 2.24E−01 | 5.41E−01 | 1.26 | ADCYAP1; CXCL10; CXCL11; CXCL9; GPR65; HIF1A; PGAM1; PPIF; VCP; WNT5A |
| antigen processing cross presentation | 26 | 2 | 2.24E−01 | 5.41E−01 | 1.68 | PSMA4; TAP2 |
| stimulus: GO | 26 | 2 | 2.24E−01 | 5.41E−01 | 1.68 | CCNA2; H2AFZ |
| cerebellar cortex morphogenesis: GO | 26 | 2 | 2.24E−01 | 5.41E−01 | 1.68 | KIF14; WNT7A |
| cyclin dependent protein serine threonine kinase regulator activity: GO | 26 | 2 | 2.24E−01 | 5.41E−01 | 1.68 | CCNE1; CKS2 |
| desmosome: GO | 26 | 2 | 2.24E−01 | 5.41E−01 | 1.68 | DSC2; DSG3 |
| endoribonuclease activity producing 5 phosphomonoesters: GO | 26 | 2 | 2.24E−01 | 5.41E−01 | 1.68 | EXO1; RPP40 |
| establishment or maintenance of epithelial cell apical basal polarity: GO | 26 | 2 | 2.24E−01 | 5.41E−01 | 1.68 | FOXF1; WNT5A |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| integrin cs pathway | 26 | 2 | 2.24E−01 | 5.41E−01 | 1.68 | ITGAX; ITGB6 |
| intramolecular transferase activity: GO | 26 | 2 | 2.24E−01 | 5.41E−01 | 1.68 | PGAM1; PGM2 |
| keratan sulfate biosynthetic process: GO | 26 | 2 | 2.24E−01 | 5.41E−01 | 1.68 | B3GNT3; CHST1 |
| ncam signaling for neurite out growth | 26 | 2 | 2.24E−01 | 5.41E−01 | 1.68 | ARTN; CDK1 |
| negative regulation of fibroblast proliferation: GO | 26 | 2 | 2.24E−01 | 5.41E−01 | 1.68 | GSTP1; IFI30 |
| phagocytosis recognition: GO | 26 | 2 | 2.24E−01 | 5.41E−01 | 1.68 | CLEC7A; IGHG4 |
| polyol biosynthetic process: GO | 26 | 2 | 2.24E−01 | 5.41E−01 | 1.68 | CYP27B1; PTAFR |
| post translational modification synthesis of gpi anchored proteins | 26 | 2 | 2.24E−01 | 5.41E−01 | 1.68 | PIGW; PLAUR |
| regulation of cardiac muscle cell proliferation: GO | 26 | 2 | 2.24E−01 | 5.41E−01 | 1.68 | CCNB1; CDK1 |
| regulation of cell cycle checkpoint: GO | 26 | 2 | 2.24E−01 | 5.41E−01 | 1.68 | CCNB1; MAD2L1 |
| regulation of endoplasmic reticulum unfolded protein response: GO | 26 | 2 | 2.24E−01 | 5.41E−01 | 1.68 | BAK1; SDF2L1 |
| regulation of extracellular matrix organization: GO | 26 | 2 | 2.24E−01 | 5.41E−01 | 1.68 | FSCN1; HSPA8 |
| activation: GO | 26 | 2 | 2.24E−01 | 5.41E−01 | 1.68 | IL12B; PGLYRP2 |
| response to growth hormone: GO | 26 | 2 | 2.24E−01 | 5.41E−01 | 1.68 | JAK3; TRIM16 |
| steroid hydroxylase activity: GO | 26 | 2 | 2.24E−01 | 5.41E−01 | 1.68 | CH25H; CYP2S1 |
| vegfr1 pathway | 26 | 2 | 2.24E−01 | 5.41E−01 | 1.68 | HIF1A; PGF |
| centrosome maturation | 61 | 4 | 2.25E−01 | 5.42E−01 | 1.43 | CDK1; NEK2; PLK1; TUBA1C |
| extracellular ligand gated ion channel activity: GO | 61 | 4 | 2.25E−01 | 5.42E−01 | 1.43 | CHRNA3; CHRNA6; CHRNA9; HTR3A |
| influenza infection | 61 | 4 | 2.25E−01 | 5.42E−01 | 1.43 | CALR; ISG15; KPNA2; RPL22L1 |
| mapk6/mapk4 signaling | 61 | 4 | 2.25E−01 | 5.42E−01 | 1.43 | CDK1; MAPK6; PSMA5; PSMB6 |
| regulation of epithelial cell migration: GO | 155 | 9 | 2.26E−01 | 5.43E−01 | 1.27 | CXCL13; HBEGF; HIF1A; IFNG; MMP9; SH3BGRL3; WNT5A; WNT7A; ZC3H12A |
| histone deacetylase binding: GO | 98 | 6 | 2.26E−01 | 5.44E−01 | 1.34 | CDC20; HIF1A; HIST1H1B; KPNA2; PRDM1; TOP2A |
| branching morphogenesis of an epithelial tube: GO | 117 | 7 | 2.27E−01 | 5.45E−01 | 1.31 | AREG; BAK1; FOXF1; PGF; TIMELESS; TNC; WNT5A |
| learning: GO | 117 | 7 | 2.27E−01 | 5.45E−01 | 1.31 | CNTNAP2; EIF4A3; FOSL1; HIF1A; NDRG4; NLGN4X; STRA6 |
| ligand gated channel activity: GO | 117 | 7 | 2.27E−01 | 5.45E−01 | 1.31 | CHRNA3; CHRNA6; CHRNA9; CLCA2; CNGB1; HTR3A; KCNJ15 |
| calcium mediated signaling: GO | 80 | 5 | 2.31E−01 | 5.53E−01 | 1.37 | CCL3; CCR5; CXCR4; GSTO1; SELE |
| single stranded dna binding: GO | 80 | 5 | 2.31E−01 | 5.53E−01 | 1.37 | BLM; CDC45; MCM10; NME1; SUB1 |
| gastrin-creb signalling pathway via pkc and mapk | 195 | 11 | 2.32E−01 | 5.54E−01 | 1.23 | CCK; CSF2; DUSP9; HBEGF; IL2RA; JAK3; LTB4R; MMP1; MMP3; PSMA5; PSMB6 |
| glycan structures - biosynthesis 1 | 99 | 6 | 2.33E−01 | 5.56E−01 | 1.33 | CHST1; GALNT6; HS3ST1; HS3ST3A1; HS3ST3B1; ST6GALNAC1 |
| detection of light stimulus: GO | 44 | 3 | 2.34E−01 | 5.56E−01 | 1.49 | CNGB1; GNGT2; PITPNM1 |
| endoribonuclease activity: GO | 44 | 3 | 2.34E−01 | 5.56E−01 | 1.49 | EXO1; RPP40; ZC3H12A |
| assembly: GO | 44 | 3 | 2.34E−01 | 5.56E−01 | 1.49 | CSF2; FSCN1; RALB |
| positive regulation of reactive oxygen species biosynthetic process: GO | 44 | 3 | 2.34E−01 | 5.56E−01 | 1.49 | IFNG; IL1B; IL6 |
| activity: GO | 44 | 3 | 2.34E−01 | 5.56E−01 | 1.49 | EPGN; GSTO1; TGFA |
| response to axon injury: GO | 44 | 3 | 2.34E−01 | 5.56E−01 | 1.49 | CDK1; NTRK1; TNC |
| t cell differentiation: GO | 118 | 7 | 2.34E−01 | 5.56E−01 | 1.30 | CD3E; EOMES; IFNG; IL12B; IL6; IL7R; RSAD2 |
| cellular response to heat stress | 62 | 4 | 2.34E−01 | 5.56E−01 | 1.41 | FPR1; HSPA6; HSPA8; TNFRSF21 |
| endoderm development: GO | 62 | 4 | 2.34E−01 | 5.56E−01 | 1.41 | EOMES; HMGA2; MMP9; SOX7 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| regulation of telomere maintenance: GO | 62 | 4 | 2.34E−01 | 5.56E−01 | 1.41 | CCT5; NEK2; PIF1; PRKCQ |
| cytosolic trna aminoacylation | 27 | 2 | 2.38E−01 | 5.58E−01 | 1.62 | GARS; TARS |
| disulfide oxidoreductase activity: GO | 27 | 2 | 2.38E−01 | 5.58E−01 | 1.62 | GSTO1; SH3BGRL3 |
| heparan sulfate proteoglycan metabolic process: GO | 27 | 2 | 2.38E−01 | 5.58E−01 | 1.62 | HPSE; HS3ST3B1 |
| heterotrimeric g protein complex: GO | 27 | 2 | 2.38E−01 | 5.58E−01 | 1.62 | GNA15; GNGT2 |
| il4receptor in b lyphocytes | 27 | 2 | 2.38E−01 | 5.58E−01 | 1.62 | IL4R; JAK3 |
| lis1 pathway | 27 | 2 | 2.38E−01 | 5.58E−01 | 1.62 | CDK5R1; LRP8 |
| mammary gland duct morphogenesis: GO | 27 | 2 | 2.38E−01 | 5.58E−01 | 1.62 | AREG; WNT5A |
| muscle adaptation: GO | 27 | 2 | 2.38E−01 | 5.58E−01 | 1.62 | HMOX1; IL1B |
| nadp metabolic process: GO | 27 | 2 | 2.38E−01 | 5.58E−01 | 1.62 | PGM2; TPI1 |
| necrotic cell death: GO | 27 | 2 | 2.38E−01 | 5.58E−01 | 1.62 | PPIF; PYGL |
| negative regulation of cytokine biosynthetic process: GO | 27 | 2 | 2.38E−01 | 5.58E−01 | 1.62 | IL6; NMI |
| neuroblast proliferation: GO | 27 | 2 | 2.38E−01 | 5.58E−01 | 1.62 | ARTN; ASPM |
| o linked glycosylation of mucins | 27 | 2 | 2.38E−01 | 5.58E−01 | 1.62 | GALNT6; GCNT4 |
| phospholipid catabolic process: GO | 27 | 2 | 2.38E−01 | 5.58E−01 | 1.62 | LIPG; PLA2G4D |
| placenta blood vessel development: GO | 27 | 2 | 2.38E−01 | 5.58E−01 | 1.62 | FOSL1; SOCS3 |
| positive regulation of glial cell differentiation: GO | 27 | 2 | 2.38E−01 | 5.58E−01 | 1.62 | CXCR4; IL1B |
| positive regulation of organic acid transport: GO | 27 | 2 | 2.38E−01 | 5.58E−01 | 1.62 | CCK; IL1B |
| activity: GO | 27 | 2 | 2.38E−01 | 5.58E−01 | 1.62 | NEK2; PRKCQ |
| quinone metabolic process: GO | 27 | 2 | 2.38E−01 | 5.58E−01 | 1.62 | AKR1B10; CYP4F11 |
| immunoglobulins: GO | 27 | 2 | 2.38E−01 | 5.58E−01 | 1.62 | EXO1; POLQ |
| synaptonemal complex: GO | 27 | 2 | 2.38E−01 | 5.58E−01 | 1.62 | BLM; PLK1 |
| t cell mediated immunity: GO | | | 2.38E−01 | 5.58E−01 | 1.62 | CTSC; SLAMF1 |
| inner ear morphogenesis: GO | 81 | 5 | 2.39E−01 | 5.58E−01 | 1.35 | ALDH1A3; CHRNA9; GRHL3; NR4A3; WNT5A |
| phagocytic vesicle: GO | 81 | 5 | 2.39E−01 | 5.58E−01 | 1.35 | LTF; RAB31; RAB38; RAC2; SLAMF1 |
| regulation of calcium ion transport into cytosol: GO | 81 | 5 | 2.39E−01 | 5.58E−01 | 1.35 | BAK1; CXCL10; CXCL11; CXCL9; GSTO1 |
| sphingolipid metabolism | 81 | 5 | 2.39E−01 | 5.58E−01 | 1.35 | ARSH; GLTP; NEU2; SPTSSA; UGCG |
| arms-mediated activation | 138 | 8 | 2.39E−01 | 5.58E−01 | 1.27 | CSF2; DUSP9; HBEGF; IL2RA; JAK3; NTRK1; PSMA5; PSMB6 |
| isomerase activity: GO | 138 | 8 | 2.39E−01 | 5.58E−01 | 1.27 | FKBPL; PGAMI; PGM2; PPIB; PPIF; PPIL1; TOP2A; TPI1 |
| circadian rhythm: GO | 119 | 7 | 2.40E−01 | 5.60E−01 | 1.29 | AHCY; ARNTL2; HTR7; NAMPT; NTRK1; SERPINE1; TIMELESS |
| growth factor binding: GO | 119 | 7 | 2.40E−01 | 5.60E−01 | 1.29 | CXCL13; ESM1; FGFBP1; IL2RA; IL36RN; NTRK1; TRIM16 |
| er to golgi anterograde transport | 100 | 6 | 2.40E−01 | 5.60E−01 | 1.31 | AREG; CTSC; TGFA; TUBA1C; TUBB2A; TUBB6 |
| bonds: GO | 100 | 6 | 2.40E−01 | 5.60E−01 | 1.31 | CHI3L2; HPSE; HYAL3; LYZ; NEU2; PCNA |
| cellular response to drug: GO | 63 | 4 | 2.43E−01 | 5.63E−01 | 1.39 | CD69; HIF1A; IL1B; NME1 |
| embryonic heart tube development: GO | 63 | 4 | 2.43E−01 | 5.63E−01 | 1.39 | HIF1A; NDRG4; STIL; WNT5A |
| integrin1 pathway | 63 | 4 | 2.43E−01 | 5.63E−01 | 1.39 | PLAU; PLAUR; TGM2; TNC |
| endodeoxyribonuclease activity: GO | 45 | 3 | 2.44E−01 | 5.63E−01 | 1.46 | DNASEIL3; EXO1; HMGA2 |
| nucleobase containing compound kinase activity: GO | 45 | 3 | 2.44E−01 | 5.63E−01 | 1.46 | CMPK2; NME1; TK1 |
| platelet alpha granule lumen: GO | 45 | 3 | 2.44E−01 | 5.63E−01 | 1.46 | SERPINA1; SERPINE1; SRGN |
| positive regulation of myeloid leukocyte differentiation: GO | 45 | 3 | 2.44E−01 | 5.63E−01 | 1.46 | IFNG; IL12B; IL20 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| positive regulation of neuron apoptotic process: GO | 45 | 3 | 2.44E−01 | 5.63E−01 | 1.46 | CCL3; CDK5R1; PCSK9 |
| positive regulation of receptor mediated endocytosis: GO | 45 | 3 | 2.44E−01 | 5.63E−01 | 1.46 | PCSK9; SELE; SERPINE1 |
| positive regulation of response to extracellular stimulus: GO | 45 | 3 | 2.44E−01 | 5.63E−01 | 1.46 | CYP27B1; HIF1A; RALB |
| positive regulation of striated muscle cell differentiation: GO | 45 | 3 | 2.44E−01 | 5.63E−01 | 1.46 | CXCL9; IL4R; NEU2 |
| regulation of extrinsic apoptotic signaling pathway in absence of ligand: GO | 45 | 3 | 2.44E−01 | 5.63E−01 | 1.46 | CSF2; IFI6; IL1B |
| process: GO | 45 | 3 | 2.44E−01 | 5.63E−01 | 1.46 | CYP27B1; IFNG; IL1B |
| response to amine: GO | 45 | 3 | 2.44E−01 | 5.63E−01 | 1.46 | CDK1; CTSB; NME1 |
| srp-dependent cotranslational protein targeting to membrane | 45 | 3 | 2.44E−01 | 5.63E−01 | 1.46 | RPL22L1; SEC61G; SPC25 |
| frs2-mediated activation | 139 | 8 | 2.45E−01 | 5.64E−01 | 1.26 | CSF2; DUSP9; HBEGF; IL2RA; JAK3; NTRK1; PSMA5; PSMB6 |
| hormone receptor binding: GO | 139 | 8 | 2.45E−01 | 5.64E−01 | 1.26 | ADCYAP1; CALR; CCNE1; HIF1A; NR4A3; OASL; PCNA; RAN |
| myeloid cell homeostasis: GO | 82 | 5 | 2.47E−01 | 5.67E−01 | 1.33 | BAK1; HMOX1; IFNG; IL6; PRDX1 |
| regulation of gliogenesis: GO | 82 | 5 | 2.47E−01 | 5.67E−01 | 1.33 | ADCYAP1; CDK1; CXCR4; IL1B; TNFRSF21 |
| regulation of ph: GO | 82 | 5 | 2.47E−01 | 5.67E−01 | 1.33 | ATP12A; RAB38; RHCG; SLC26A9; SLC4A8 |
| vesicle lumen: GO | 82 | 5 | 2.47E−01 | 5.67E−01 | 1.33 | CALR; LTF; SERPINA1; SERPINE1; SRGN |
| negative regulation of cell adhesion: GO | 198 | 11 | 2.47E−01 | 5.67E−01 | 1.21 | ACP5; ADAMDECI; CD274; CTLA4; IDO1; IL2RA; IL4R; JAK3; SERPINE1; TNC; TNFRSF21 |
| ear morphogenesis: GO | 101 | 6 | 2.47E−01 | 5.68E−01 | 1.30 | ALDH1A3; CHRNA9; GJB6; GRHL3; NR4A3; WNT5A |
| process: GO | 101 | 6 | 2.47E−01 | 5.68E−01 | 1.30 | B3GNT3; CHST1; HAS3; HMMR; HYAL3; IL1B |
| response to starvation: GO | 140 | 8 | 2.51E−01 | 5.70E−01 | 1.25 | ADCYAP1; DSC2; HSPA8; IFI16; PCSK9; RALB; UPP1; ZC3H12A |
| shel events in egfr signaling | 140 | 8 | 2.51E−01 | 5.70E−01 | 1.25 | CDK1; CSF2; DUSP9; HBEGF; IL2RA; JAK3; PSMA5; PSMB6 |
| a band: GO | 28 | 2 | 2.51E−01 | 5.70E−01 | 1.56 | ENO1; MYOM3 |
| bard1 pathway | 28 | 2 | 2.51E−01 | 5.70E−01 | 1.56 | CCNE1; PCNA |
| epidermis morphogenesis: GO | 28 | 2 | 2.51E−01 | 5.70E−01 | 1.56 | FOXE1; KRT17 |
| g1 s transition | 28 | 2 | 2.51E−01 | 5.70E−01 | 1.56 | PKMYT1; PSMA4 |
| glycan structures - degradation | 28 | 2 | 2.51E−01 | 5.70E−01 | 1.56 | HPSE; NEU2 |
| hdr through single strand annealing (ssa) | 28 | 2 | 2.51E−01 | 5.70E−01 | 1.56 | BLM; EXO1 |
| heme metabolic process: GO | 28 | 2 | 2.51E−01 | 5.70E−01 | 1.56 | HMOX1; HMOX2 |
| keratan sulfate biosynthesis | 28 | 2 | 2.51E−01 | 5.70E−01 | 1.56 | B3GNT3; CHST1 |
| lysosome vesicle biogenesis | 28 | 2 | 2.51E−01 | 5.70E−01 | 1.56 | AP1S3; HSPA8 |
| male meiosis: GO | 28 | 2 | 2.51E−01 | 5.70E−01 | 1.56 | KIF18A; TRIP13 |
| negative regulation of epithelial cell apoptotic process: GO | 28 | 2 | 2.51E−01 | 5.70E−01 | 1.56 | SERPINB13; SERPINE1 |
| signaling | 28 | 2 | 2.51E−01 | 5.70E−01 | 1.56 | HERC6; ISG15 |
| process: GO | 28 | 2 | 2.51E−01 | 5.70E−01 | 1.56 | PLA2G3; PLA2G4D |
| positive regulation of cardiac muscle tissue development: GO | 28 | 2 | 2.51E−01 | 5.70E−01 | 1.56 | CCNB1; CDK1 |
| positive regulation of cell cycle g1 s phase transition: GO | 28 | 2 | 2.51E−01 | 5.70E−01 | 1.56 | CDC45; CDC6 |
| protein localization to cytoskeleton: GO | 28 | 2 | 2.51E−01 | 5.70E−01 | 1.56 | AURKA; STIL |
| proteoglycans | 28 | 2 | 2.51E−01 | 5.70E−01 | 1.56 | ESM1; SRGN |
| signal amplification | 28 | 2 | 2.51E−01 | 5.70E−01 | 1.56 | GNA15; GNGT2 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| vitamin transport: GO | 28 | 2 | 2.51E−01 | 5.70E−01 | 1.56 | STRA6; TCN1 |
| secondary active transmembrane transporter activity: GO | 199 | 11 | 2.52E−01 | 5.70E−01 | 1.21 | SLC16A1; SLC16A6; SLC16A9; SLC26A9; SLC2A9; SLC4A8; SLC5A1; SLC6A11; SLC7A1; SLC7A11; SLC7A5 |
| detoxification: GO | 64 | 4 | 2.52E−01 | 5.70E−01 | 1.37 | GSTO1; PRDX1; S100A9; TXNDC17 |
| metabolism of polyamines | 64 | 4 | 2.52E−01 | 5.70E−01 | 1.37 | PSMA5; PSMB6; SMOX; SRM |
| adhesion: GO | 121 | 7 | 2.53E−01 | 5.72E−01 | 1.27 | CD274; CTLA4; IDO1; IL2RA; IL4R; JAK3; TNFRSF21 |
| regulation of ossification: GO | 160 | 9 | 2.54E−01 | 5.72E−01 | 1.23 | AREG; CCL3; CYP27B1; HIF1A; IFITM1; IL6; LTF; SRGN; WNT5A |
| recruitment of mitotic centrosome proteins and complexes | 83 | 5 | 2.55E−01 | 5.72E−01 | 1.32 | CCNB1; CDK1; NEK2; PLK1; TUBA1C |
| pattern recognition receptor signaling pathway: GO | 102 | 6 | 2.55E−01 | 5.72E−01 | 1.29 | CLEC7A; CTSB; MYD88; PGLYRP2; S100A14; TNIP3 |
| regulation of tp53 activity | 102 | 6 | 2.55E−01 | 5.72E−01 | 1.29 | AURKA; BLM; CCNA2; CDK1; EXO1; TPX2 |
| copii (coat protein 2) mediated vesicle transport | 46 | 3 | 2.55E−01 | 5.72E−01 | 1.43 | AREG; CTSC; TGFA |
| phosphatidylinositol 4 5 bisphosphate binding: GO | 46 | 3 | 2.55E−01 | 5.72E−01 | 1.43 | ADAP2; MYO1B; TWF1 |
| regulation of organic acid transport: GO | 46 | 3 | 2.55E−01 | 5.72E−01 | 1.43 | CCK; HRH3; IL1B |
| ribosomal large subunit biogenesis: GO | 46 | 3 | 2.55E−01 | 5.72E−01 | 1.43 | EBNA1BP2; EIF6; RPL26L1 |
| sterol homeostasis: GO | 46 | 3 | 2.55E−01 | 5.72E−01 | 1.43 | LDLR; LIPG; PCSK9 |
| type ii diabetes mellitus | 46 | 3 | 2.55E−01 | 5.72E−01 | 1.43 | HK2; PKM; SOCS3 |
| signaling by leptin | 141 | 8 | 2.57E−01 | 5.77E−01 | 1.24 | CSF2; DUSP9; HBEGF; IL2RA; JAK3; PSMA5; PSMB6; SOCS3 |
| antiporter activity: GO | 65 | 4 | 2.61E−01 | 5.84E−01 | 1.35 | SLC26A9; SLC7A1; SLC7A11; SLC7A5 |
| lysophospholipid pathway | 65 | 4 | 2.61E−01 | 5.84E−01 | 1.35 | GNA15; HBEGF; IL6; MMP9 |
| p75 ntr pathway | 65 | 4 | 2.61E−01 | 5.84E−01 | 1.35 | CYCS; MMP3; MYD88; NTRK1 |
| recombinational repair: GO | 65 | 4 | 2.61E−01 | 5.84E−01 | 1.35 | BLM; CDC45; H2AFX; POLQ |
| telomerase pathway | 65 | 4 | 2.61E−01 | 5.84E−01 | 1.35 | BLM; IFNG; MXD1; PIF1 |
| membrane lipid biosynthetic process: GO | 103 | 6 | 2.62E−01 | 5.84E−01 | 1.27 | PIGW; PLAUR; SPTSSA; ST6GALNACI; ST8S1A2; UGCG |
| heat shock protein binding: GO | 84 | 5 | 2.63E−01 | 5.84E−01 | 1.30 | BAK1; CDK1; HIF1A; HSPA6; HSPA8 |
| ribonuclease activity: GO | 84 | 5 | 2.63E−01 | 5.84E−01 | 1.30 | EXO1; ISG20; RNASE7; RPP40; ZC3H12A |
| ameboidal type cell migration: GO | 142 | 8 | 2.63E−01 | 5.84E−01 | 1.23 | CXCL13; FERMT1; HIF1A; KRT16; PRSS3; S100A2; STAT1; WNT5A |
| mitochondrial transport: GO | 142 | 8 | 2.63E−01 | 5.84E−01 | 1.23 | BAK1; HK2; PPIF; SFN; SLC25A5; TIMM13; TIMM8B; YWHAQ |
| axon cytoplasm: GO | 29 | 2 | 2.65E−01 | 5.84E−01 | 1.51 | HIF1A; KIF4A |
| bile acid metabolic process: GO | 29 | 2 | 2.65E−01 | 5.84E−01 | 1.51 | CH25H; FABP6 |
| dendritic cell differentiation: GO | 29 | 2 | 2.65E−01 | 5.84E−01 | 1.51 | CSF2; TNFSF9 |
| dna strand elongation: GO | 29 | 2 | 2.65E−01 | 5.84E−01 | 1.51 | GINS3; PCNA |
| embryonic forelimb morphogenesis: GO | 29 | 2 | 2.65E−01 | 5.84E−01 | 1.51 | CRABP2; WNT7A |
| glutamate metabolism | 29 | 2 | 2.65E−01 | 5.84E−01 | 1.51 | ALDH4A1; GOT2 |
| organization: GO | 29 | 2 | 2.65E−01 | 5.84E−01 | 1.51 | CCR5; CXCR4 |
| circulation: GO | 29 | 2 | 2.65E−01 | 5.84E−01 | 1.51 | HIF1A; ZC3H12A |
| activity: GO | 29 | 2 | 2.65E−01 | 5.84E−01 | 1.51 | GSTO1; PCSK9 |
| neutral amino acid transport: GO | 29 | 2 | 2.65E−01 | 5.84E−01 | 1.51 | SLC38A5; SLC7A5 |
| processing: GO | 29 | 2 | 2.65E−01 | 5.84E−01 | 1.51 | CCNB1; HSPA8 |
| positive regulation of viral genome replication: GO | 29 | 2 | 2.65E−01 | 5.84E−01 | 1.51 | PPIB; TOP2A |
| reelin pathway | 29 | 2 | 2.65E−01 | 5.84E−01 | 1.51 | CDK5R1; LRP8 |
| regulation of protein insertion into mitochondrial membrane involved in | 29 | 2 | 2.65E−01 | 5.84E−01 | 1.51 | SFN; YWHAQ |

TABLE 4-continued

| Functional enrichment for genes dysregulated in both PN and psoriatic lesional skin. | | | | | | |
|---|---|---|---|---|---|---|
| | Num_Fun_genes | Common pso and PN (up) Num_IntFun_genes | Common pso and PN (up) p | Common pso and PN (up) FDR | Common pso and PN (up) FC | Common pso and PN (up) genes |
| apoptotic signaling pathway: GO | | | | | | |
| response to atp: GO | 29 | 2 | 2.65E−01 | 5.84E−01 | 1.51 | IL1B; SELL |
| s1p s1p3 pathway | 29 | 2 | 2.65E−01 | 5.84E−01 | 1.51 | CXCR4; GNA15 |
| stem cell division: GO | 29 | 2 | 2.65E−01 | 5.84E−01 | 1.51 | ASPM; WNT7A |
| tak1 activates nfkb by phosphorylation and activation of ikks complex | 29 | 2 | 2.65E−01 | 5.84E−01 | 1.51 | MYD88; S100A12 |
| tnfr1 pathway | 29 | 2 | 2.65E−01 | 5.84E−01 | 1.51 | LMNB1; LMNB2 |
| tnfr1 signaling pathway | 29 | 2 | 2.65E−01 | 5.84E−01 | 1.51 | LMNB1; LMNB2 |
| cellular response to calcium ion: GO | 47 | 3 | 2.66E−01 | 5.84E−01 | 1.40 | ECT2; PPIF; WNT5A |
| (hrr) | 47 | 3 | 2.66E−01 | 5.84E−01 | 1.40 | BLM; EXO1; PCNA |
| methylated histone binding: GO | | | 2.66E−01 | 5.84E−01 | 1.40 | CBX2; CDYL2; UHRF1 |
| phospholipid transport: GO | | | 2.66E−01 | 5.84E−01 | 1.40 | LDLR; PITPNM1; PRELID1 |
| positive regulation of transcription factor import into nucleus: GO | 47 | 3 | 2.66E−01 | 5.84E−01 | 1.40 | IL12B; IL1B; PRKCQ |
| purine containing compound catabolic process: GO | 47 | 3 | 2.66E−01 | 5.84E−01 | 1.40 | AHCY; NUDT15; PNP |
| neddylation | 123 | 7 | 2.67E−01 | 5.85E−01 | 1.24 | BIRC5; HIF1A; KBTBD8; PSMA5; PSMB6; SOCS3; UBE2F |
| electron carrier activity: GO | 104 | 6 | 2.69E−01 | 5.90E−01 | 1.26 | ALDH4A1; COX7B; CYCS; IDO1; RDH16; SH3BGRL3 |
| lipase activity: GO | 104 | 6 | 2.69E−01 | 5.90E−01 | 1.26 | CCR5; HMOX1; LIPG; PLA2G3; PLA2G4D; PLBD1 |
| phosphorylation | 66 | 4 | 2.70E−01 | 5.91E−01 | 1.33 | CKAP4; IL6; PCSK9; TNC |
| regulation of synapse assembly: GO | 66 | 4 | 2.70E−01 | 5.91E−01 | 1.33 | NTRK1; TPBG; WNT5A; WNT7A |
| synapse assembly: GO | 66 | 4 | 2.70E−01 | 5.91E−01 | 1.33 | FBXO45; NLGN4X; WNT5A; WNT7A |
| positive regulation of cation transmembrane transport: GO | 85 | 5 | 2.71E−01 | 5.92E−01 | 1.29 | ATP1B3; CXCL10; CXCL11; CXCL9; GSTO1 |
| regulation of protein binding: GO | 163 | 9 | 2.71E−01 | 5.93E−01 | 1.21 | AURKA; BAK1; MMP9; PLK1; PLK2; RALB; RAN; SLPI; WNT5A |
| cell recognition: GO | 124 | 7 | 2.73E−01 | 5.97E−01 | 1.23 | CCT5; CDK5R1; CLEC7A; CNTNAP2; CXCR4; FUT3; IGHG4 |
| process: GO | 48 | 3 | 2.76E−01 | 5.97E−01 | 1.37 | B3GNT3; HAS3; PGM2 |
| embryonic pattern specification: GO | 48 | 3 | 2.76E−01 | 5.97E−01 | 1.37 | STIL; WNT5A; WNT7A |
| face development: GO | 48 | 3 | 2.76E−01 | 5.97E−0 | 1.37 | ALDH1A3; STRA6; WNT5A |
| gdp binding: GO | 48 | 3 | 2.76E−01 | 5.97E−01 | 1.37 | RAB31; RALB; RAN |
| humoral immune response mediated by circulating immunoglobulin: GO | 48 | 3 | 2.76E−01 | 5.97E−01 | 1.37 | C1QBP; EXO1; IGHG4 |
| positive regulation of intrinsic apoptotic signaling pathway: GO | 48 | 3 | 2.76E−01 | 5.97E−01 | 1.37 | IL19; S100A8; S100A9 |
| positive regulation of lipid transport: GO | 48 | 3 | 2.76E−01 | 5.97E−01 | 1.37 | IL1B; LIPG; PRELID1 |
| regulation of behavior: GO | 48 | 3 | 2.76E−01 | 5.97E−01 | 1.37 | IL6; NR4A3; STRA6 |
| migration: GO | 48 | 3 | 2.76E−01 | 5.97E−01 | 1.37 | NDRG4; PLAU; SERPINE1 |
| mammary gland development: GO | 105 | 6 | 2.76E−01 | 5.97E−01 | 1.25 | AREG; FOXF1; HIF1A; HK2; NME1; WNT5A |
| oh group of donors nad or nadp as acceptor: GO | 105 | 6 | 2.76E−01 | 5.97E−01 | 1.25 | ADH7; AKR1B10; AKR1B15; LDHA; RDH16; SDR9C7 |
| antigen processing: ubiquitination & proteasome degradation | 164 | 9 | 2.77E−01 | 5.97E−01 | 1.20 | CDC20; DTX3L; HERC6; KBTBD8; PSMA5; PSMB6; SOCS3; UBE2C; UBE2F |
| atp hydrolysis coupled transmembrane transport: GO | 30 | 2 | 2.79E−01 | 5.97E−01 | 1.46 | ATP12A; ATP1B3 |
| development: GO | 30 | 2 | 2.79E−01 | 5.97E−01 | 1.46 | FOXF1; STRA6 |
| fas signaling pathway ( cd95 ) | 30 | 2 | 2.79E−01 | 5.97E−01 | 1.46 | LMNB1; LMNB2 |
| glutathione transferase activity: GO | 30 | 2 | 2.79E−01 | 5.97E−01 | 1.46 | GSTO1; GSTP1 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| response to endoplasmic reticulum stress: GO | 30 | 2 | 2.79E−01 | 5.97E−01 | 1.46 | BAK1; CHAC1 |
| latent infection of homo sapiens with mycobacterium tuberculosis | 30 | 2 | 2.79E−01 | 5.97E−01 | 1.46 | CAMP; LTF |
| limonene and pinene degradation | 30 | 2 | 2.79E−01 | 5.97E−01 | 1.46 | ALDH1A3; ESCO2 |
| lumenal side of membrane: GO | 30 | 2 | 2.79E−01 | 5.97E−01 | 1.46 | CALR; HSPA8 |
| mismatch repair: GO | 30 | 2 | 2.79E−01 | 5.97E−01 | 1.46 | EXO1; PCNA |
| transport: GO | 30 | 2 | 2.79E−01 | 5.97E−01 | 1.46 | HRH3; IL1B |
| negative regulation of response to oxidative stress: GO | 30 | 2 | 2.79E−01 | 5.97E−01 | 1.46 | HIF1A; NR4A3 |
| nuclear receptors in lipid metabolism and toxicity | 30 | 2 | 2.79E−01 | 5.97E−01 | 1.46 | CYP24A1; CYP27B1 |
| phagocytosis engulfment: GO | 30 | 2 | 2.79E−01 | 5.97E−01 | 1.46 | FCGR1A; IGHG4 |
| positive regulation of response to cytokine stimulus: GO | 30 | 2 | 2.79E−01 | 5.97E−01 | 1.46 | HIF1A; WNT5A |
| presynaptic phase of homologous dna pairing and strand exchange | 30 | 2 | 2.79E−01 | 5.97E−01 | 1.46 | BLM; EXO1 |
| adhesion: GO | 30 | 2 | 2.79E−01 | 5.97E−01 | 1.46 | ITGAX; ITGB6 |
| regulation of dendritic spine morphogenesis: GO | 30 | 2 | 2.79E−01 | 5.97E−01 | 1.46 | CDK5R1; LRP8 |
| organization: GO | 30 | 2 | 2.79E−01 | 5.97E−01 | 1.46 | FSCN1; RAC2 |
| response to x ray: GO | 30 | 2 | 2.79E−01 | 5.97E−01 | 1.46 | BLM; HIF1A |
| carbohydrate transport: GO | 86 | | 2.79E−01 | 5.97E−01 | 1.27 | AQP3; FABP5; HK2; SLC2A9; SLC5A1 |
| b cell differentiation: GO | 67 | 4 | 2.79E−01 | 5.97E−01 | 1.31 | BAK1; IFNE; JAK3; NTRK1 |
| interleukin-1 family signaling | 67 | 4 | 2.79E−01 | 5.97E−01 | 1.31 | IL1B; MYD88; PSMA5; PSMB6 |
| secretion: GO | 67 | 4 | 2.79E−01 | 5.97E−01 | 1.31 | IL1B; IL6; OSM; VSNL1 |
| process: GO | 67 | 4 | 2.79E−01 | 5.97E−01 | 1.31 | NUDT15; PNP; UPP1; VCP |
| positive regulation of type i interferon production: GO | 67 | 4 | 2.79E−01 | 5.97E−01 | 1.31 | IFI16; MYD88; POLR3G; ZBP1 |
| regulation of release of sequestered calcium ion into cytosol: GO | 67 | 4 | 2.79E−01 | 5.97E−01 | 1.31 | CXCL10; CXCL11; CXCL9; GSTO1 |
| host interactions of hiv factors | 125 | 7 | 2.80E−01 | 5.98E−01 | 1.22 | AP1S3; PSMA4; PSMA5; PSMB6; RAN; RCC1; SLC25A5 |
| organelle biogenesis and maintenance | 165 | 9 | 2.83E−01 | 6.04E−01 | 1.19 | CCT5; CDK1; CYCS; KIF2C; NEK2; PLK1; TUBA1C; TUBB2A; TUBB6 |
| response to insulin: GO | 185 | 10 | 2.83E−01 | 6.05E−01 | 1.18 | EIF4EBP1; GGH; GSTP1; HIF1A; IL6; NAMPT; PCSK9; PRKCQ; RAB31; SOCS3 |
| b cell activation: GO | 106 | 6 | 2.84E−01 | 6.06E−01 | 1.24 | BAK1; EXO1; IFNE; IL7R; JAK3; NTRK1 |
| sphingolipid metabolic process: GO | 126 | 7 | 2.87E−01 | 6.07E−01 | 1.21 | ARSH; GLTP; NEU2; SPTSSA; ST6GALNACI; ST8S1A2; UGCG |
| 7transport to the golgi and subsequent modification | 126 | 7 | 2.87E−01 | 6.07E−01 | 1.21 | AREG; CTSC; ST8S1A2; TGFA; TUBA1C; TUBB2A; TUBB6 |
| c5ellular monovalent inorganic cation homeostasis: GO | 87 | 5 | 2.87E−01 | 6.07E−01 | 1.26 | ATP12A; ATP1B3; RAB38; SLC26A9; SLC4A8 |
| disorders of transmembrane transporters | 87 | 5 | 2.87E−01 | 6.07E−01 | 1.26 | GK; PSMA5; PSMB6; SLC16A1; SLC2A9 |
| g alpha q signalling events | 87 | 5 | 2.87E−01 | 6.07E−01 | 1.26 | GNA15; GNGT2; GPR65; PRKCQ; PTAFR |
| myeloid leukocyte differentiation: GO | 87 | 5 | 2.87E−01 | 6.07E−01 | 1.26 | ACP5; CSF2; IFI16; MMP9; TNFSF9 |
| ligase cop1 | 49 | 3 | 2.87E−01 | 6.07E−01 | 1.34 | PSMA4; PSMA5; PSMB6 |
| copper ion binding: GO | 49 | 3 | 2.87E−01 | 6.07E−01 | 1.34 | HEPHL1; S100A12; SCO2 |
| cytoplasmic microtubule: GO | 49 | 3 | 2.87E−01 | 6.07E−01 | 1.34 | BIRC5; KIF2C; RGS20 |
| dna helicase activity: GO | 49 | 3 | 2.87E−01 | 6.07E−01 | 1.34 | BLM; CDC45; PIF1 |

TABLE 4-continued

| Functional enrichment for genes dysregulated in both PN and psoriatic lesional skin. | | | | | | |
|---|---|---|---|---|---|---|
| | Num_Fun_genes | Common pso and PN (up) Num_IntFun_genes | Common pso and PN (up) p | Common pso and PN (up) FDR | Common pso and PN (up) FC | Common pso and PN (up) genes |
| o glycan processing: GO | 49 | 3 | 2.87E−01 | 6.07E−01 | 1.34 | B3GNT3; GALNT6; GCNT4 |
| positive regulation of extrinsic apoptotic signaling pathway: GO | 49 | 3 | 2.87E−01 | 6.07E−01 | 1.34 | PYCARD; TNFRSF12A; TNFSF10 |
| protein monoubiquitination: GO | 49 | 3 | 2.87E−01 | 6.07E−01 | 1.34 | DTX3L; UBE2T; UHRF1 |
| regulation of extrinsic apoptotic signaling pathway via death domain receptors: GO | 49 | 3 | 2.87E−01 | 6.07E−01 | 1.34 | HMOX1; SERPINE1; TNFSF10 |
| regulation of morphogenesis of a branching structure: GO | 49 | 3 | 2.87E−01 | 6.07E−01 | 1.34 | IL1B; PGF; WNT5A |
| ventricular septum development: GO | 49 | 3 | 2.87E−01 | 6.07E−01 | 1.34 | PRDM1; STRA6; WNT5A |
| negative regulation of lipid metabolic process: GO | 68 | 4 | 2.89E−01 | 6.09E−01 | 1.29 | CYP27B1; IL1B; UGT1A10; UGT1A7 |
| sphingolipid biosynthetic process: GO | 68 | 4 | 2.89E−01 | 6.09E−01 | 1.29 | SPTSSA; ST6GALNAC1; ST8S1A2; UGCG |
| regulation of exocytosis: GO | 166 | 9 | 2.89E−01 | 6.10E−01 | 1.19 | FOXF1; HMOX1; IFNG; IL4R; PTAFR; RAC2; RALB; RIMS3; VSNL1 |
| monocarboxylic acid transport: GO | 107 | 6 | 2.91E−01 | 6.12E−01 | 1.23 | FABP6; GOT2; SLC16A1; SLC16A6; SLC16A9; SLC6A11 |
| alditol phosphate metabolic process: GO | 31 | 2 | 2.92E−01 | 6.12E−01 | 1.41 | GK; PLA2G4D |
| atp dependent dna helicase activity: GO | 31 | 2 | 2.92E−01 | 6.12E−01 | 1.41 | BLM; PIF1 |
| atpase activity coupled to transmembrane movement of ions phosphorylative mechanism: GO | 31 | 2 | 2.92E−01 | 6.12E−01 | 1.41 | ATP12A; ATP1B3 |
| avb3 opn pathway | 31 | 2 | 2.92E−01 | 6.12E−01 | 1.41 | MMP9; PLAU |
| dicarboxylic acid transmembrane transporter activity: GO | 31 | 2 | 2.92E−01 | 6.12E−01 | 1.41 | SLC26A9; SLC7A11 |
| glycerolipid catabolic process: GO | 31 | 2 | 2.92E−01 | 6.12E−01 | 1.41 | FABP5; FABP6 |
| hindlimb morphogenesis: GO | 31 | 2 | 2.92E−01 | 6.12E−01 | 1.41 | PITX1; WNT7A |
| keratan sulfate metabolic process: GO | 31 | 2 | 2.92E−01 | 6.12E−01 | 1.41 | B3GNT3; CHST1 |
| negative regulation of cation channel activity: GO | 31 | 2 | 2.92E−01 | 6.12E−01 | 1.41 | GSTO1; MMP9 |
| negative regulation of epithelial cell differentiation: GO | 31 | 2 | 2.92E−01 | 6.12E−01 | 1.41 | IFNG; STAT1 |
| positive chemotaxis: GO | 31 | 2 | 2.92E−01 | 6.12E−01 | 1.41 | CCL3; WNT5A |
| salivary gland development: GO | | 2 | 2.92E−01 | 6.12E−01 | 1.41 | IL6; TGM2 |
| activity: GO | 31 | 2 | 2.92E−01 | 6.12E−01 | 1.41 | SLC2A9; SLC5A1 |
| epithelial cell development: GO | 167 | 9 | 2.95E−01 | 6.17E−01 | 1.18 | BFSP1; CXCR4; HIF1A; NTRK1; PRDM1; SFN; VSIG1; WNT5A; WNT7A |
| camera type eye morphogenesis: GO | 88 | 5 | 2.95E−01 | 6.17E−01 | 1.24 | ALDH1A3; BAK1; HIF1A; STRA6; WNT5A |
| exonuclease activity: GO | 69 | 4 | 2.98E−01 | 6.20E−01 | 1.27 | AEN; EXO1; ISG20; ZC3H12A |
| multi organism behavior: GO | 69 | 4 | 2.98E−01 | 6.20E−01 | 1.27 | CNTNAP2; GCNT4; IL1B; NLGN4X |
| neutral lipid metabolic process: GO | 69 | 4 | 2.98E−01 | 6.20E−01 | 1.27 | FABP5; FABP6; GK; PCSK9 |
| artery morphogenesis: GO | 50 | 3 | 2.98E−01 | 6.20E−01 | 1.31 | FOXF1; PRDM1; STRA6 |
| cell division site: GO | 50 | 3 | 2.98E−01 | 6.20E−01 | 1.31 | CEP55; ECT2; PITPNM1 |
| iron uptake and transport | 50 | 3 | 2.98E−01 | 6.20E−01 | 1.31 | HMOX1; HMOX2; LCN2 |
| pcp/ce pathway | 50 | 3 | 2.98E−01 | 6.20E−01 | 1.31 | PSMA5; PSMB6; WNT5A |
| assembly: GO | 50 | 3 | 2.98E−01 | 6.20E−01 | 1.31 | NTRK1; TPBG; WNT7A |
| regulation of epithelial cell apoptotic process: GO | 50 | 3 | 2.98E−01 | 6.20E−01 | 1.31 | IL6; SERPINB 13; SERPINE1 |
| response to dsrna: GO | 50 | 3 | 2.98E−01 | 6.20E−01 | 1.31 | DDX21; IFNE; RALB |
| response to zinc ion: GO | 50 | 3 | 2.98E−01 | 6.20E−01 | 1.31 | ACP5; GGH; S100A8 |
| binding bridging: GO | 168 | 9 | 3.01E−01 | 6.25E−01 | 1.17 | ADAP2; CSTA; FSCN1; HOMER1; IVL; SH2D2A; SHB; SPRR1A; SPRR1B |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| interleukin-7 signaling | 168 | 9 | 3.01E−01 | 6.25E−01 | 1.17 | CBX2; HBEGF; HIST1H3A; HIST1H3I; IL7R; JAK3; MYD88; PSMA5; PSMB6 |
| sulfur compound biosynthetic | 189 | 10 | 3.06E−01 | 6.29E−01 | 1.16 | HS3ST3B1AHCY; B3GNT3; CHAC1; CHAC2; CHST1; CNDP2; GGCT; GSTO1; GSTP1; |
| process: GO | | | | | | |
| activation of jun kinase activity: GO | 32 | 2 | 3.06E−01 | 6.29E−01 | 1.37 | MDFI; WNT5A |
| aminoacyl-trna biosynthesis | 32 | 2 | 3.06E−01 | 6.29E−01 | 1.37 | GARS; TARS |
| endonuclease activity active with either ribo or deoxyribonucleic acids and producing 5 phosphomonoesters: GO | 32 | 2 | 3.06E−01 | 6.29E−01 | 1.37 | EXO1; RPP40 |
| gpi anchor metabolic process: GO | 32 | 2 | 3.06E−01 | 6.29E−01 | 1.37 | PIGW; PLAUR |
| heart valve development: GO | 32 | 2 | 3.06E−01 | 6.29E−01 | 1.37 | PRDM1; STRA6 |
| hif2pathway | 32 | 2 | 3.06E−01 | 6.29E−01 | 1.37 | PGK1; SERPINE1 |
| i18 cxcr2 pathway | 32 | 2 | 3.06E−01 | 6.29E−01 | 1.37 | GNA15; RAC2 |
| linoleic acid metabolism | 32 | 2 | 3.06E−01 | 6.29E−01 | 1.37 | AKR1B10; PLA2G3 |
| mpr pathway | 32 | 2 | 3.06E−01 | 6.29E−01 | 1.37 | CCNB1; CDK1 |
| negative regulation of cyclin dependent protein kinase activity: GO | 32 | 2 | 3.06E−01 | 6.29E−01 | 1.37 | PLK1; UBE2C |
| negative regulation of jnk cascade: GO | 32 | 2 | 3.06E−01 | 6.29E−01 | 1.37 | GSTP1; SERPINB3 |
| prion diseases | 32 | 2 | 3.06E−01 | 6.29E−01 | 1.37 | IL1B; IL6 |
| protein kinase b signaling: GO | 32 | 2 | 3.06E−01 | 6.29E−01 | 1.37 | CCL3; IL1B |
| regulation of cell aging: GO | 32 | 2 | 3.06E−01 | 6.29E−01 | 1.37 | FOXM1; HMGA2 |
| process: GO | 32 | 2 | 3.06E−01 | 6.29E−01 | 1.37 | HIF1A; PGAMI |
| regulation of peptidyl threonine phosphorylation: GO | 32 | 2 | 3.06E−01 | 6.29E−01 | 1.37 | PLK1; WNT5A |
| response to iron ion: GO | 32 | 2 | 3.06E−01 | 6.29E−01 | 1.37 | CCNB1; HMOX1 |
| smooth endoplasmic reticulum: GO | 32 | 2 | 3.06E−01 | 6.29E−01 | 1.37 | CALR; PPIB |
| adenylate cyclase modulating g protein coupled receptor signaling pathway: GO | 109 | 6 | 3.06E−01 | 6.29E−01 | 1.20 | ADCYAP1; ADM2; FPR1; HRH3; RGS1; SIPR4 |
| membrane lipid metabolic process: GO | 169 | 9 | 3.07E−01 | 6.29E−01 | 1.16 | ARSH; GLTP; NEU2; PIGW; PLAUR; SPTSSA; ST6GALNAC1; ST8S1A2; UGCG |
| activation of gtpase activity: GO | 70 | 4 | 3.07E−01 | 6.29E−01 | 1.25 | CXCL13; ECT2; GPR65; WNT5A |
| atpase binding: GO | 70 | 4 | 3.07E−01 | 6.29E−01 | 1.25 | ATP1B3; RALB; SDF2L1; SLC26A9 |
| ceramide metabolic process: GO | 70 | 4 | 3.07E−01 | 6.29E−01 | 1.25 | NEU2; ST6GALNACI; ST8S1A2; UGCG |
| golgi cisterna membrane: GO | 70 | 4 | 3.07E−01 | 6.29E−01 | 1.25 | FUT1; FUT2; FUT3; PITPNM1 |
| vesicle coating: GO | 70 | 4 | 3.07E−01 | 6.29E−01 | 1.25 | AREG; CTSC; SERPINA1; TGFA |
| ammonium ion metabolic process: GO | 149 | 8 | 3.08E−01 | 6.29E−01 | 1.17 | AKR1B10; FABP5; PLA2G3; PLA2G4D; PLBD1; SMOX; SNCB; SRM |
| actin filament bundle: GO | 51 | 3 | 3.09E−01 | 6.30E−01 | 1.29 | CNN2; FBLIM1; FSCN1 |
| adenylate cyclase activating g protein coupled receptor signaling pathway: GO | 51 | 3 | 3.09E−01 | 6.30E−01 | 1.29 | ADCYAP1; ADM2; S1PR4 |
| caspase pathway | 51 | 3 | 3.09E−01 | 6.30E−01 | 1.29 | CYCS; LMNB1; LMNB2 |
| digestive system process: GO | 51 | 3 | 3.09E−01 | 6.30E−01 | 1.29 | LDLR; SLC5A1; VSIG1 |
| intrinsic apoptotic signaling pathway by p53 class mediator: GO | 51 | 3 | 3.09E−01 | 6.30E−01 | 1.29 | AEN; IFI16; PYCARD |
| somitogenesis: GO | 51 | 3 | 3.09E−01 | 6.30E−01 | 1.29 | FOXF1; RGS20; WNT5A |
| unfolded protein binding: GO | 90 | 5 | 3.12E−01 | 6.35E−01 | 1.21 | CALR; CCT5; HSPA6; HSPA8; PPIB |
| cell maturation: GO | 110 | 6 | 3.14E−01 | 6.38E−01 | 1.19 | BFSP1; CCNB1; CDC25B; CNTNAP2; HIF1A; TRIP13 |
| endonuclease activity: GO | 110 | 6 | 3.14E−01 | 6.38E−01 | 1.19 | DNASEIL3; EXO1; HMGA2; RNASE7; RPP40; ZC3H12A |
| homeostasis: GO | 110 | 6 | 3.14E−01 | 6.38E−01 | 1.19 | ATP12A; ATP1B3; RAB38; RHCG; SLC26A9; SLC4A8 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| transport: GO | 130 | 7 | 3.14E−01 | 6.39E−01 | 1.18 | ABCG4; AQP3; FABP6; LDLR; LIPG; SLC16A1; SLC16A6 |
| loss of nlp from mitotic centrosomes | 71 | 4 | 3.17E−01 | 6.43E−01 | 1.23 | CDK1; NEK2; PLK1; TUBA1C |
| single organism membrane budding: GO | 71 | 4 | 3.17E−01 | 6.43E−01 | 1.23 | AREG; CTSC; SERPINA1; TGFA |
| kinase regulator activity: GO | 171 | 9 | 3.19E−01 | 6.43E−01 | 1.15 | CCNE1; CDK5R1; CKS2; CXCL10; GSTP1; LTF; RAC2; SFN; SOCS3 |
| regulation of peptide secretion: GO | 171 | 9 | 3.19E−01 | 6.43E−01 | 1.15 | ADCYAP1; HIF1A; IFNG; IL1B; S100A8; S100A9; SLC16A1; SLC25A5; VSNL1 |
| adrenergic | 33 | 2 | 3.20E−01 | 6.43E−01 | 1.33 | CAMP; GNA15 |
| axo dendritic transport: GO | 33 | 2 | 3.20E−01 | 6.43E−01 | 1.33 | HIF1A; KIF4A |
| death pathway | 33 | 2 | 3.20E−01 | 6.43E−01 | 1.33 | CYCS; TNFSF10 |
| degradation of dvl | 33 | 2 | 3.20E−01 | 6.43E−01 | 1.33 | PSMA5; PSMB6 |
| folate biosynthesis | 33 | 2 | 3.20E−01 | 6.43E−01 | 1.33 | ALPL; GGH |
| glial cell migration: GO | 33 | 2 | 3.20E−01 | 6.43E−01 | 1.33 | CCL3; CDK5R1 |
| hdac classii pathway | 33 | 2 | 3.20E−01 | 6.43E−01 | 1.33 | RAN; TUBB2A |
| exchange | 33 | 2 | 3.20E−01 | 6.43E−01 | 1.33 | BLM; EXO1 |
| il1 pathway | 33 | 2 | 3.20E−01 | 6.43E−01 | 1.33 | IL1B; MYD88 |
| phosphatidylinositol 3 4 5 trisphosphate binding: GO | 33 | 2 | 3.20E−01 | 6.43E−01 | 1.33 | ADAP2; MYO1B |
| positive regulation of neural precursor cell proliferation: GO | 33 | 2 | 3.20E−01 | 6.43E−01 | 1.33 | ASPM; HIF1A |
| secretion: GO | 33 | 2 | 3.20E−01 | 6.43E−01 | 1.33 | CHRNA6; HRH3 |
| rna phosphodiester bond hydrolysis exonucleolytic: GO | 33 | 2 | 3.20E−01 | 6.43E−01 | 1.33 | ISG20; ZC3H12A |
| rna polymerase ii activating transcription factor binding: GO | 33 | 2 | 3.20E−01 | 6.43E−01 | 1.33 | EOMES; IFI27 |
| gland morphogenesis: GO | 91 | 5 | 3.20E−01 | 6.43E−01 | 1.20 | AREG; IL6; TGM2; TNC; WNT5A |
| maintenance of location in cell: GO | 91 | 5 | 3.20E−01 | 6.43E−01 | 1.20 | ASPM; HK2; MDFI; SRGN; TWF1 |
| regulation of hsf1-mediated heat shock response | 52 | 3 | 3.20E−01 | 6.43E−01 | 1.26 | HSPA6; HSPA8; TNFRSF21 |
| cellular response to oxygen levels: GO | 131 | 7 | 3.21E−01 | 6.44E−01 | 1.17 | CCNA2; CCNB1; EIF4EBP1; FAM162A; HIF1A; HMOX1; PLAU |
| stimulus: GO | 131 | 7 | 3.21E−01 | 6.44E−01 | 1.17 | CHRNA9; GJB2; GJB6; IFNG; NTRK1; TIMM13; TIMM8B |
| cellular response to topologically incorrect protein: GO | 111 | 6 | 3.21E−01 | 6.44E−01 | 1.18 | BAK1; CALR; IFNG; SDF2L1; SEC61G; VCP |
| lipoprotein metabolic process: GO | 111 | 6 | 3.21E−01 | 6.44E−01 | 1.18 | LDLR; OAS2; OLR1; PCSK9; PIGW; PLAUR |
| ubiquitin like protein binding: GO | 111 | 6 | 3.21E−01 | 6.44E−01 | 1.18 | CXCR4; KIF18A; RNF222; TNIP3; TOP2A; VCP |
| cellular response to steroid hormone stimulus: GO | 192 | 10 | 3.23E−01 | 6.48E−01 | 1.14 | ADCYAP1; CALR; CCNA2; CCNE1; GSTP1; H2AFZ; IL6; NR4A3; RAN; SERPINB9 |
| protein dephosphorylation: GO | 172 | 8 | 3.25E−01 | 6.51E−01 | 1.14 | CDC25A; CDC25B; CDKN3; CYCS; DLGAP5; DUSP14; DUSP9; PPP4R1; PTPRE |
| downstream ter signaling | 72 | 4 | 3.26E−01 | 6.52E−01 | 1.21 | CD3E; PRKCQ; PSMA5; PSMB6 |
| proteasome complex: GO | 72 | 4 | 3.26E−01 | 6.52E−01 | 1.21 | PSMA4; PSMA5; PSMB6; VCP |
| regulation of lipase activity: GO | 72 | 4 | 3.26E−01 | 6.52E−01 | 1.21 | GNA15; PTAFR; SIPR4; SELE |
| regulation of jnk cascade: GO | 152 | 8 | 3.27E−01 | 6.53E−01 | 1.15 | GSTP1; IL1B; MDFI; PYCARD; SERPINB3; SLAMF1; WNT5A; WNT7A |
| cxcr4 pathway | 112 | 6 | 3.29E−01 | 6.57E−01 | 1.17 | CD3E; CXCR4; MMP9; RALB; RGS1; STAT1 |
| protein sumoylation: GO | 112 | 6 | 3.29E−01 | 6.57E−01 | 1.17 | BIRC5; BLM; CBX2; CDCA8; PCNA; TOP2A |
| cd8 ter pathway | 53 | 3 | 3.31E−01 | 6.57E−01 | 1.24 | CD3E; CD80; PRKCQ |
| epidermal growth factor receptor signaling pathway: GO | 53 | 3 | 3.31E−01 | 6.57E−01 | 1.24 | AREG; FAM83A; HBEGF |
| microtubule bundle formation: GO | 53 | 3 | 3.31E−01 | 6.57E−01 | 1.24 | KIF20A; PLA2G3; PLK1 |
| development: GO | 53 | 3 | 3.31E−01 | 6.57E−01 | 1.24 | CDK5R1; LRP8; PLK2 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| rna phosphodiester bond hydrolysis endonucleolytic: GO | 53 | 3 | 3.31E−01 | 6.57E−01 | 1.24 | EXO1; RPP40; ZC3H12A |
| peptidyl tyrosine modification: GO | 173 | 9 | 3.31E−01 | 6.57E−01 | 1.14 | CSF2; HBEGF; IL12RB2; JAK3; MELK; NTRK1; OSM; TTK; TWF1 |
| astrocyte differentiation: GO | 34 | 2 | 3.33E−01 | 6.57E−01 | 1.29 | S100A8; S100A9 |
| autoimmune thyroid disease | 34 | 2 | 3.33E−01 | 6.57E−01 | 1.29 | CD80; CTLA4 |
| cortical cytoskeleton organization: GO | 34 | 2 | 3.33E−01 | 6.57E−01 | 1.29 | CALR; KIF23 |
| fmlp induced chemokine gene expression in hmc-1 cells | 34 | 2 | 3.33E−01 | 6.57E−01 | 1.29 | FPR1; GNA15 |
| frizzled binding: GO | 34 | 2 | 3.33E−01 | 6.57E−01 | 1.29 | WNT5A; WNT7A |
| gaba b receptor activation | 34 | 2 | 3.33E−01 | 6.57E−01 | 1.29 | GNGT2; KCNJ15 |
| hindbrain morphogenesis: GO | 34 | 2 | 3.33E−01 | 6.57E−01 | 1.29 | KIF14; WNT7A |
| histone ubiquitination: GO | 34 | 2 | 3.33E−01 | 6.57E−01 | 1.29 | DTX3L; UHRF1 |
| import into cell: GO | 34 | 2 | 3.33E−01 | 6.57E−01 | 1.29 | STEAP1B; STEAP4 |
| mitotic g1 g1 s phases | 34 | 2 | 3.33E−01 | 6.57E−01 | 1.29 | PKMYT1; PSMA4 |
| modulation by virus of host morphology or physiology: GO | 34 | 2 | 3.33E−01 | 6.57E−01 | 1.29 | KPNA2; ZC3H12A |
| negative regulation of blood pressure: GO | 34 | 2 | 3.33E−01 | 6.57E−01 | 1.29 | ADM2; PTAFR |
| photoreceptor cell development: GO | 34 | 2 | 3.33E−01 | 6.57E−01 | 1.29 | CNGB1; PRDM1 |
| proliferation: GO | 34 | 2 | 3.33E−01 | 6.57E−01 | 1.29 | SASH3; TNFRSF4 |
| reciprocal dna recombination: GO | 34 | 2 | 3.33E−01 | 6.57E−01 | 1.29 | TOP2A; TRIP13 |
| regulation of activated pak-2p34 by proteasome mediated degradation | 34 | 2 | 3.33E−01 | 6.57E−01 | 1.29 | PSMA5; PSMB6 |
| regulation of filopodium assembly: GO | 34 | 2 | 3.33E−01 | 6.57E−01 | 1.29 | FSCN1; PRKCQ |
| t cell proliferation: GO | 34 | 2 | 3.33E−01 | 6.57E−01 | 1.29 | EBI3; TNFRSF4 |
| vif-mediated degradation of apobec3g | 34 | 2 | 3.33E−01 | 6.57E−01 | 1.29 | PSMA5; PSMB6 |
| activity: GO | 194 | 10 | 3.35E−01 | 6.59E−01 | 1.13 | CDK1; CXCR4; DUSP9; EPGN; FPR1; IL1B; MDFI; S100A12; TGFA; WNT5A |
| clec7a (dectin-1) signaling | 73 | 4 | 3.36E−01 | 6.59E−01 | 1.20 | IL1B; PSMA5; PSMB6; PYCARD |
| organelle envelope lumen: GO | 73 | 4 | 3.36E−01 | 6.59E−01 | 1.20 | CYCS; PRELID1; TIMM13; TIMM8B |
| positive regulation of exocytosis: GO | 73 | 4 | 3.36E−01 | 6.59E−01 | 1.20 | IFNG; IL4R; PTAFR; VSNL1 |
| nuclear matrix: GO | 93 | 5 | 3.37E−01 | 6.62E−01 | 1.18 | BLM; CENPW; KIF4A; LMNB1; UHRF1 |
| positive regulation of protein complex assembly: GO | 174 | 9 | 3.38E−01 | 6.62E−01 | 1.13 | CCK; CSF2; CXCL13; FOSL1; FSCN1; MMP1; MMP3; PYCARD; VCP |
| regulation of ion homeostasis: GO | 174 | 9 | 3.38E−01 | 6.62E−01 | 1.13 | BAK1; CCK; CCL3; CCR5; CXCL10; CXCL11; CXCL9; GSTO1; IFI6 |
| infectious disease | 195 | 10 | 3.41E−01 | 6.68E−01 | 1.12 | AP1S3; CALR; CXCR4; HBEGF; ISG15; KPNA2; PSMA5; PSMB6; RPL22L1; SLC25A5 |
| forebrain cell migration: GO | 54 | 3 | 3.42E−01 | 6.70E−01 | 1.21 | CDK5R1; CXCR4; FBXO45 |
| phagocytic vesicle membrane: GO | 54 | 3 | 3.42E−01 | 6.70E−01 | 1.21 | RAB31; RAB38; RAC2 |
| transport of inorganic cations/anions and amino acids/oligopeptides | 54 | 3 | 3.42E−01 | 6.70E−01 | 1.21 | SLC7A1; SLC7A11; SLC7A5 |
| process: GO | 175 | 9 | 3.44E−01 | 6.71E−01 | 1.12 | CCL3; CDK5R1; HIF1A; HMOX1; KIF14; NR4A3; NTRK1; PCSK9; SNCB |
| pathway: GO | 114 | 6 | 3.44E−01 | 6.71E−01 | 1.15 | FOXF1; HMOX1; IL4R; PTAFR; RAC2; RIMS3 |
| cellular aldehyde metabolic process: GO | 74 | 4 | 3.45E−01 | 6.71E−01 | 1.18 | AKR1B10; ALDH1A3; PGM2; TPI1 |
| nuclear envelope organization: GO | 74 | 4 | 3.45E−01 | 6.71E−01 | 1.18 | CCNB1; CCNB2; CDK1; PLK1 |
| process: GO | 74 | 4 | 3.45E−01 | 6.71E−01 | 1.18 | GK; NR4A3; UGT1A10; UGT1A7 |
| cardiac ventricle development: GO | 94 | 5 | 3.45E−01 | 6.71E−01 | 1.16 | FOXF1; HIF1A; PRDM1; STRA6; WNT5A |
| positive regulation of proteasomal protein catabolic process: GO | 94 | 5 | 3.45E−01 | 6.71E−01 | 1.16 | AURKA; DLGAP5; PLK1; PLK2; VCP |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| steroid metabolic process: GO | 196 | 10 | 3.47E−01 | 6.71E−01 | 1.12 | AKR1B10; AKR1B15; CH25H; CYP24A1; CYP27B1; FABP6; IL1B; LDLR; PCSK9; SQLE |
| beta tubulin binding: GO | 35 | 2 | 3.47E−01 | 6.71E−01 | 1.25 | CCT5; SNCB |
| bile acid and bile salt metabolism | 35 | 2 | 3.47E−01 | 6.71E−01 | 1.25 | CH25H; FABP6 |
| fmlp pathway | 35 | 2 | 3.47E−01 | 6.71E−01 | 1.25 | FPR1; GNA15 |
| forelimb morphogenesis: GO | 35 | 2 | 3.47E−01 | 6.71E−01 | 1.25 | CRABP2; WNT7A |
| g alpha i pathway | 35 | 2 | 3.47E−01 | 6.71E−01 | 1.25 | PI3; RGS20 |
| phagosome maturation: GO | 35 | 2 | 3.47E−01 | 6.71E−01 | 1.25 | RAB31; RAB38 |
| pi3kci akt pathway | 35 | 2 | 3.47E−01 | 6.71E−01 | 1.25 | SFN; YWHAQ |
| porphyrin containing compound metabolic process: GO | 35 | 2 | 3.47E−01 | 6.71E−01 | 1.25 | HMOX1; HMOX2 |
| modification: GO | 35 | 2 | 3.47E−01 | 6.71E−01 | 1.25 | ARSH; ESCO2 |
| cycle | 35 | 2 | 3.47E−01 | 6.71E−01 | 1.25 | LDHA; SLC16A1 |
| regulation of substrate adhesion dependent cell spreading: GO | 35 | 2 | 3.47E−01 | 6.71E−01 | 1.25 | C1QBP; CALR |
| response to nerve growth factor: GO | 35 | 2 | 3.47E−01 | 6.71E−01 | 1.25 | EIF4A3; NTRK1 |
| t cell selection: GO | 35 | 2 | 3.47E−01 | 6.71E−01 | 1.25 | CD3E; IL6 |
| toxin transport: GO | 35 | 2 | 3.47E−01 | 6.71E−01 | 1.25 | CCT5; CD274 |
| genes | 35 | 2 | 3.47E−01 | 6.71E−01 | 1.25 | BIRC5; PRELID1 |
| cyclin d | 35 | 2 | 3.47E−01 | 6.71E−01 | 1.25 | PSMA5; PSMB6 |
| cyclin d1 | 35 | 2 | 3.47E−01 | 6.71E−01 | 1.25 | PSMA5; PSMB6 |
| gastrulation: GO | 135 | 7 | 3.50E−01 | 6.75E−01 | 1.13 | EOMES; FOXF1; HMGA2; MMP9; NR4A3; SOX7; WNT5A |
| adult behavior: GO | 115 | 6 | 3.52E−01 | 6.79E−01 | 1.14 | CHRNA3; CNTNAP2; CSTB; HOMER1; NLGN4X; NR4A3 |
| negative regulation of cellular amide metabolic process: GO | 115 | 6 | 3.52E−01 | 6.79E−01 | 1.14 | CALR; EIF4A3; EIF4EBP1; GAPDH; RAN; ZC3H12A |
| body fluid secretion: GO | 55 | 3 | 3.53E−01 | 6.80E−01 | 1.19 | HIF1A; HK2; NME1 |
| negative regulation of cation transmembrane transport: GO | 55 | 3 | 3.53E−01 | 6.80E−01 | 1.19 | GSTO1; MMP9; PCSK9 |
| positive regulation of lipid biosynthetic process: GO | 55 | 3 | 3.53E−01 | 6.80E−01 | 1.19 | IFNG; IL1B; LDLR |
| dna dependent atpase activity: GO | 75 | 4 | 3.54E−01 | 6.82E−01 | 1.17 | BLM; PIF1; POLQ; TOP2A |
| midbrain development: GO | 75 | 4 | 3.54E−01 | 6.82E−01 | 1.17 | INA; LDHA; WNT5A; YWHAQ |
| grb2 events in egfr signaling | 136 | 7 | 3.57E−01 | 6.85E−01 | 1.13 | CSF2; DUSP9; HBEGF; IL2RA; JAK3; PSMA5; PSMB6 |
| raf/map kinase cascade | 136 | 7 | 3.57E−01 | 6.85E−01 | 1.13 | CSF2; DUSP9; HBEGF; IL2RA; JAK3; PSMA5; PSMB6 |
| sos-mediated signalling | 136 | 7 | 3.57E−01 | 6.85E−01 | 1.13 | CSF2; DUSP9; HBEGF; IL2RA; JAK3; PSMA5; PSMB6 |
| nucleotidyltransferase activity: GO | 116 | 6 | 3.60E−01 | 6.88E−01 | 1.13 | OAS1; OAS2; OAS3; OASL; POLQ; POLR3G |
| cellular response to acid chemical: GO | 157 | 8 | 3.60E−01 | 6.88E−01 | 1.11 | CCNB1; HIF1A; IL1B; NME1; PTAFR; TNC; WNT5A; ZC3H12A |
| dna damage response detection of dna damage: GO | 36 | 2 | 3.61E−01 | 6.88E−01 | 1.21 | HMGA2; PCNA |
| drug metabolic process: GO | 36 | 2 | 3.61E−01 | 6.88E−01 | 1.21 | UGT1A10; UGT1A7 |
| glutamate receptor binding: GO | 36 | 2 | 3.61E−01 | 6.88E−01 | 1.21 | HOMER1; NETO2 |
| negative regulation of axon extension: GO | 36 | 2 | 3.61E−01 | 6.88E−01 | 1.21 | CDK5R1; WNT5A |
| nucleobase metabolic process: GO | 36 | 2 | 3.61E−01 | 6.88E−01 | 1.21 | IL1B; TYMP |
| polyubiquitin binding: GO | 36 | 2 | 3.61E−01 | 6.88E−01 | 1.21 | TNIP3; VCP |
| protein trimerization: GO | 36 | 2 | 3.61E−01 | 6.88E−01 | 1.21 | NELL2; TNFRSF9 |
| regulation of action potential: GO | 36 | 2 | 3.61E−01 | 6.88E−01 | 1.21 | DSC2; IFNG |
| differentiation: GO | 36 | 2 | 3.61E−01 | 6.88E−01 | 1.21 | HIF1A; ISG15 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| (odc) | 36 | 2 | 3.61E−01 | 6.88E−01 | 1.21 | PSMA5; PSMB6 |
| regulation of receptor internalization: GO | 36 | 2 | 3.61E−01 | 6.88E−01 | 1.21 | PCSK9; SELE |
| vpu mediated degradation of cd4 | 36 | 2 | 3.61E−01 | 6.88E−01 | 1.21 | PSMA5; PSMB6 |
| exopeptidase activity: GO | 96 | 5 | 3.62E−01 | 6.91E−01 | 1.14 | CNDP2; CPA6; CPXM1; DPP3; GGH |
| t cell receptor signaling pathway: GO | 137 | 7 | 3.64E−01 | 6.92E−01 | 1.12 | CD3E; IFNG; PRKCQ; PSMA4; PSMA5; PSMB6; TNFRSF21 |
| ethanolamine containing compound metabolic process: GO | 76 | 4 | 3.64E−01 | 6.92E−01 | 1.15 | FABP5; PLA2G3; PLA2G4D; PLBD1 |
| keratin filament: GO | 76 | 4 | 3.64E−01 | 6.92E−01 | 1.15 | KRT6A; KRT6B; KRT6C; KRT75 |
| regulation of striated muscle cell differentiation: GO | 76 | 4 | 3.64E−01 | 6.92E−01 | 1.15 | CXCL10; CXCL9; IL4R; NEU2 |
| vesicle targeting: GO | 76 | 4 | 3.64E−01 | 6.92E−01 | 1.15 | AREG; CTSC; SERPINA1; TGFA |
| negative regulation of synaptic transmission: GO | 56 | 3 | 3.64E−01 | 6.92E−01 | 1.17 | EIF4A3; NLGN4X; PLK2 |
| signaling by vegf | 199 | 10 | 3.64E−01 | 6.92E−01 | 1.10 | CSF2; DUSP9; HBEGF; IL2RA; JAK3; PGF; PSMA5; PSMB6; SH2D2A; SHB |
| antigen receptor mediated signaling pathway: GO | 179 | 9 | 3.69E−01 | 7.00E−01 | 1.10 | CD3E; CTLA4; IFNG; IGHG4; PRKCQ; PSMA4; PSMA5; PSMB6; TNFRSF21 |
| nuclease activity: GO | 179 | 9 | 3.69E−01 | 7.00E−01 | 1.10 | AEN; DNASEIL3; EXO1; HMGA2; ISG20; NME1; RNASE7; RPP40; ZC3H12A |
| specification of symmetry: GO | 97 | 5 | 3.71E−01 | 7.02E−01 | 1.13 | FOXF1; HIF1A; NDRG4; STIL; WNT5A |
| ncam signaling for neurite out-growth | 159 | 8 | 3.73E−01 | 7.02E−01 | 1.10 | CSF2; DUSP9; HBEGF; IL2RA; JAK3; PSMA5; PSMB6; ST8S1A2 |
| autophagosome: GO | 77 | 4 | 3.73E−01 | 7.02E−01 | 1.14 | IL1B; MEFV; RALB; VMP1 |
| b cell mediated immunity: GO | 77 | 4 | 3.73E−01 | 7.02E−01 | 1.14 | C1QBP; EXO1; IGHG4; IL4R |
| cmyb pathway | 77 | 4 | 3.73E−01 | 7.02E−01 | 1.14 | CCNB1; H2AFZ; HSPA8; LYZ |
| anterior posterior axis specification: GO | 37 | 2 | 3.74E−0 | 7.02E−01 | 1.18 | AURKA; WNT5A |
| cerebral cortex cell migration: GO | 37 | 2 | 3.74E−01 | 7.02E−01 | 1.18 | CDK5R1; FBXO45 |
| defective cftr causes cystic fibrosis | 37 | 2 | 3.74E−01 | 7.02E−01 | 1.18 | PSMA5; PSMB6 |
| degradation of axin | 37 | 2 | 3.74E−01 | 7.02E−01 | 1.18 | PSMA5; PSMB6 |
| degradation of gli1 by the proteasome | 37 | 2 | 3.74E−01 | 7.02E−01 | 1.18 | PSMA5; PSMB6 |
| detection of mechanical stimulus: GO | 37 | 2 | 3.74E−01 | 7.02E−01 | 1.18 | CHRNA9; NTRK1 |
| autocatalytic processing are degraded by erad | 37 | 2 | 3.74E−01 | 7.02E−01 | 1.18 | PSMA5; PSMB6 |
| mesenchyme morphogenesis: GO | 37 | 2 | 3.74E−01 | 7.02E−01 | 1.18 | FOXF1; WNT5A |
| peptidyl asparagine modification: GO | 37 | 2 | 3.74E−01 | 7.02E−01 | 1.18 | ST6GALNACI; VCP |
| phosphotransferase activity phosphate group as acceptor: GO | 37 | 2 | 3.74E−01 | 7.02E−01 | 1.18 | CMPK2; NME1 |
| positive regulation of cell killing: GO | 37 | 2 | 3.74E−01 | 7.02E−01 | 1.18 | IFNG; IL12B |
| regulation of glycoprotein metabolic process: GO | 37 | 2 | 3.74E−01 | 7.02E−01 | 1.18 | HBEGF; JAK3 |
| regulation of heart growth: GO | 37 | 2 | 3.74E−01 | 7.02E−01 | 1.18 | CCNB1; CDK1 |
| depolarization: GO | 37 | 2 | 3.74E−01 | 7.02E−01 | 1.18 | CCK; IFI6 |
| activity | 37 | 2 | 3.74E−01 | 7.02E−01 | 1.18 | PSMA5; PSMB6 |
| regulation of water balance by renal aquaporins | 37 | 2 | 3.74E−01 | 7.02E−01 | 1.18 | AQP3; GNGT2 |
| spliceosomal snrnp assembly: GO | 37 | 2 | 3.74E−01 | 7.02E−01 | 1.18 | SNRPF; SNRPG |
| trivalent inorganic cation transport: GO | 37 | 2 | 3.74E−01 | 7.02E−01 | 1.18 | STEAP1B; STEAP4 |
| biomineral tissue development: GO | 57 | 3 | 3.75E−01 | 7.02E−01 | 1.15 | ALPL; CYP27B1; SRGN |
| phosphoprotein binding: GO | 57 | 3 | 3.75E−01 | 7.02E−01 | 1.15 | GPRIN1; SAMSN1; SFN |
| positive regulation of dna biosynthetic | 57 | 3 | 3.75E−01 | 7.02E−01 | 1.15 | CCT5; NEK2; PRKCQ |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| process: GO | | | | | | |
| positive regulation of osteoblast differentiation: GO | 57 | 3 | 3.75E−01 | 7.02E−01 | 1.15 | IFITM1; IL6; LTF |
| second messenger mediated signaling: GO | 139 | 7 | 3.78E−01 | 7.07E−01 | 1.10 | ADCYAP1; CCL3; CCR5; CXCR4; FPR1; GSTO1; SELE |
| the citric acid (tca) cycle and respiratory electron transport | 98 | 5 | 3.79E−01 | 7.09E−01 | 1.12 | COX7B; CYCS; LDHA; SCO2; SLC16A1 |
| outer membrane: GO | 160 | 8 | 3.80E−01 | 7.10E−01 | 1.09 | BAK1; BCL2A1; CYP27B1; GK; HK2; IFI27; NME1; RSAD2 |
| endoplasmic reticulum lumen: GO | 181 | 9 | 3.81E−01 | 7.12E−01 | 1.09 | ARSH; CALR; CTSC; PLAUR; PPIB; SDF2L1; SERPINA1; WNT5A; WNT7A |
| regulation of calcium ion transport: GO | 181 | 9 | 3.81E−01 | 7.12E−01 | 1.09 | BAK1; CCL3; CXCL10; CXCL11; CXCL9; CXCR4; GSTO1; HOMER1; JAK3 |
| alzheimers disease | 119 | 6 | 3.83E−01 | 7.13E−01 | 1.10 | CALML3; CALML5; CDK5R1; COX7B; CYCS; IL1B |
| regulation of erbb signaling pathway: GO | 78 | 4 | 3.83E−01 | 7.13E−01 | 1.12 | EPGN; MMP9; PLAUR; TGFA |
| negative regulation of mapk cascade: GO | 140 | 7 | 3.85E−01 | 7.13E−01 | 1.09 | DUSP14; DUSP9; FOXM1; GSTP1; IL1B; PBK; SERPINB3 |
| actomyosin: GO | 58 | 3 | 3.86E−01 | 7.13E−01 | 1.13 | CNN2; FBLIM1; FSCN1 |
| lysine degradation | 58 | 3 | 3.86E−01 | 7.13E−01 | 1.13 | AKR1B10; ALDH1A3; OGDHL |
| neuropeptide signaling pathway: GO | 58 | 3 | 3.86E−01 | 7.13E−01 | 1.13 | ADCYAP1; GPR1; LTB4R |
| regulation of protein tyrosine kinase activity: GO | 58 | 3 | 3.86E−01 | 7.13E−01 | 1.13 | EPGN; LRP8; TGFA |
| stress: GO | 58 | 3 | 3.86E−01 | 7.13E−01 | 1.13 | HIF1A; MMP3; NR4A3 |
| terminal bouton: GO | 58 | 3 | 3.86E−01 | 7.13E−01 | 1.13 | ADCYAP1; CCK; SNCB |
| transferase activity transferring alkyl or aryl other than methyl groups: GO | 58 | 3 | 3.86E−01 | 7.13E−01 | 1.13 | GSTO1; GSTP1; SRM |
| reabsorption | 38 | 2 | 3.87E−01 | 7.13E−01 | 1.15 | ATP1B3; SFN |
| degradation of gli2 by the proteasome | 38 | 2 | 3.87E−01 | 7.13E−01 | 1.15 | PSMA5; PSMB6 |
| proteasome | 38 | 2 | 3.87E−01 | 7.13E−01 | 1.15 | PSMA5; PSMB6 |
| pathway: GO | 38 | 2 | 3.87E−01 | 7.13E−01 | 1.15 | CDK5R1; HOMER1 |
| hh mutants abrogate ligand secretion | 38 | 2 | 3.87E−01 | 7.13E−01 | 1.15 | PSMA5; PSMB6 |
| histidine metabolism | 38 | 2 | 3.87E−01 | 7.13E−01 | 1.15 | ALDH1A3; HAL |
| il1 signaling | 38 | 2 | 3.87E−01 | 7.13E−01 | 1.15 | IL1B; MYD88 |
| mammary gland morphogenesis: GO | 38 | 2 | 3.87E−01 | 7.13E−01 | 1.15 | AREG; WNT5A |
| negative regulation of transcription factor import into nucleus: GO | 38 | 2 | 3.87E−01 | 7.13E−01 | 1.15 | MDFI; ZC3H12A |
| oxidoreductase activity acting on peroxide as acceptor: GO | 38 | 2 | 3.87E−01 | 7.13E−01 | 1.15 | PRDX1; TXNDC17 |
| peptide hormone metabolism | 38 | 2 | 3.87E−01 | 7.13E−01 | 1.15 | ERO1A; SPC25 |
| protein serine threonine tyrosine kinase activity: GO | 38 | 2 | 3.87E−01 | 7.13E−01 | 1.15 | AURKA; TTK |
| regulation of carbohydrate catabolic process: GO | 38 | 2 | 3.87E−01 | 7.13E−01 | 1.15 | HIF1A; PGAM1 |
| regulation of lipid storage: GO | 38 | 2 | 3.87E−01 | 7.13E−01 | 1.15 | IL6; ZC3H12A |
| rna secondary structure unwinding: GO | 38 | 2 | 3.87E−01 | 7.13E−01 | 1.15 | DDX21; EIF4A3 |
| sterol biosynthetic process: GO | 38 | 2 | 3.87E−01 | 7.13E−01 | 1.15 | CH25H; SQLE |
| sulfur compound catabolic process: GO | 38 | 2 | 3.87E−01 | 7.13E−01 | 1.15 | AHCY; HPSE |
| transcription from rna polymerase iii promoter: GO | 38 | 2 | 3.87E−01 | 7.13E−01 | 1.15 | GTF3C6; POLR3G |
| interleukin-17 signaling | 182 | 9 | 3.88E−01 | 7.13E−01 | 1.08 | CDK1; CSF2; DUSP9; HBEGF; IL2RA; IL6; JAK3; PSMA5; PSMB6 |
| regulation of synapse organization: GO | 99 | 5 | 3.88E−01 | 7.13E−01 | 1.10 | CDC20; NTRK1; TPBG; WNT5A; WNT7A |
| eye morphogenesis: GO | 120 | 6 | 3.90E−01 | 7.18E−01 | 1.09 | ALDH1A3; BAK1; HIF1A; PRDM1; STRA6; WNT5A |

TABLE 4-continued

| Functional enrichment for genes dysregulated in both PN and psoriatic lesional skin. | | | | | | |
|---|---|---|---|---|---|---|
| | Num_Fun_genes | Common pso and PN (up) Num_IntFun_genes | Common pso and PN (up) p | Common pso and PN (up) FDR | Common pso and PN (up) FC | Common pso and PN (up) genes |
| macromitophagy: GO | 120 | 6 | 3.90E−01 | 7.18E−01 | 1.09 | FGFBP1; HK2; NEFM; RIMS3; SNRPF; TREM1 |
| negative regulation of intrinsic apoptotic signaling pathway: GO | 79 | 4 | 3.92E−01 | 7.20E−01 | 1.11 | HIF1A; MMP9; PLAUR; PPIF |
| positive regulation of ossification: GO | 79 | 4 | 3.92E−01 | 7.20E−01 | 1.11 | IFITM1; IL6; LTF; WNT5A |
| toll like receptor signaling pathway: GO | 79 | 4 | 3.92E−01 | 7.20E−01 | 1.11 | CTSB; MYD88; S100A14; TNIP3 |
| 11cam interactions | 100 | 5 | 3.96E−01 | 7.26E−01 | 1.09 | HSPA8; KIF4A; TUBA1C; TUBB2A; TUBB6 |
| mtor signaling pathway | 59 | 3 | 3.97E−01 | 7.27E−01 | 1.11 | EIF4EBP1; HIF1A; PGF |
| activity: GO | 59 | 3 | 3.97E−01 | 7.27E−01 | 1.11 | IL1B; MDFI; WNT5A |
| regulation of phagocytosis: GO | 59 | 3 | 3.97E−01 | 7.27E−01 | 1.11 | CALR; IL1B; PYCARD |
| regulation of vasoconstriction: GO | 59 | 3 | 3.97E−01 | 7.27E−01 | 1.11 | HIF1A; PRKCQ; PTAFR |
| nuclear import: GO | 121 | 6 | 3.98E−01 | 7.29E−01 | 1.08 | IFNG; JAK3; KPNA2; RAN; SNRPF; SNRPG |
| insulin signaling pathway | 142 | 7 | 3.99E−01 | 7.29E−01 | 1.08 | CALML3; CALML5; EIF4EBP1; HK2; PKM; PYGL; SOCS3 |
| metabolism of vitamins and cofactors | 142 | 7 | 3.99E−01 | 7.29E−01 | 1.08 | ACP5; AKR1B10; GSTO1; LDLR; LRP8; NAMPT; PARP9 |
| negative regulation of cellular catabolic process: GO | 142 | 7 | 3.99E−01 | 7.29E−01 | 1.08 | BUB1; BUB1B; LAMP3; MAD2L1; PBK; PLK1; TTK |
| irs-mediated signalling | 163 | 8 | 4.00E−01 | 7.29E−01 | 1.07 | CSF2; DUSP9; EIF4EBP1; HBEGF; IL2RA; JAK3; PSMA5; PSMB6 |
| b cell antigen receptor | 39 | 2 | 4.01E−01 | 7.29E−01 | 1.12 | PI3; PRDX1 |
| base excision repair: GO | 39 | 2 | 4.01E−01 | 7.29E−01 | 1.12 | HMGA2; POLQ |
| exocrine system development: GO | 39 | 2 | 4.01E−01 | 7.29E−01 | 1.12 | IL6; TGM2 |
| ncam1 interactions | 39 | 2 | 4.01E−01 | 7.29E−01 | 1.12 | ARTN; ST8S1A2 |
| negative regulation of fat cell differentiation: GO | 39 | 2 | 4.01E−01 | 7.29E−01 | 1.12 | IL6; WNT5A |
| nucleoside triphosphate biosynthetic process: GO | 39 | 2 | 4.01E−01 | 7.29E−01 | 1.12 | CMPK2; NME1 |
| process: GO | 39 | 2 | 4.01E−01 | 7.29E−01 | 1.12 | AHCY; EIF4A3 |
| somatic diversification of immune receptors: GO | 39 | 2 | 4.01E−01 | 7.29E−01 | 1.12 | EXO1; POLQ |
| stabilization of p53 | 39 | 2 | 4.01E−01 | 7.29E−01 | 1.12 | PSMA5; PSMB6 |
| regulation of cellular amine metabolic process: GO | 80 | 4 | 4.02E−01 | 7.30E−01 | 1.09 | LDLR; PSMA4; PSMA5; PSMB6 |
| female sex differentiation: GO | 101 | 5 | 4.04E−01 | 7.34E−01 | 1.08 | ADCYAP1; BAK1; CCNE1; STRA6; WNT5A |
| mesoderm development: GO | 101 | 5 | 4.04E−01 | 7.34E−01 | 1.08 | EOMES; FOXF1; HMGA2; NR4A3; WNT5A |
| negative regulation of neuron apoptotic process: GO | 122 | 6 | 4.06E−01 | 7.34E−01 | 1.08 | HIF1A; HMOX1; KIF14; NR4A3; NTRK1; SNCB |
| spliceosome | 122 | 6 | 4.06E−01 | 7.34E−01 | 1.08 | EIF4A3; HSPA6; HSPA8; PPIL1; SNRPF; SNRPG |
| interleukin receptor she signaling | 143 | 7 | 4.06E−01 | 7.34E−01 | 1.07 | CSF2; DUSP9; HBEGF; IL2RA; JAK3; PSMA5; PSMB6 |
| carbon oxygen lyase activity: GO | 60 | 3 | 4.08E−01 | 7.34E−01 | 1.09 | ENO1; HMGA2; POLQ |
| regulation of apoptosis | 60 | 3 | 4.08E−01 | 7.34E−01 | 1.09 | PSMA4; PSMA5; PSMB6 |
| rough endoplasmic reticulum: GO | 60 | 3 | 4.08E−01 | 7.34E−01 | 1.09 | PCSK9; SLC7A11; ZC3H12A |
| termination of rna polymerase ii transcription: GO | 60 | 3 | 4.08E−01 | 7.34E−01 | 1.09 | EIF4A3; SNRPF; SNRPG |
| catalytic step 2 spliceosome: GO | 81 | 4 | 4.11E−01 | 7.34E−01 | 1.08 | EIF4A3; PPIL1; SNRPF; SNRPG |
| molting cycle: GO | 81 | 4 | 4.11E−01 | 7.34E−01 | 1.08 | CDH3; FOXE1; KRT16; KRT17 |
| excitatory synapse: GO | 186 | 9 | 4.13E−01 | 7.34E−01 | 1.06 | CDK5R1; CHRNA3; FBXO45; HOMER1; LRP8; NETO2; NLGN4X; RGS20; SH2D5 |
| regulation of cation transmembrane transport: GO | 186 | 9 | 4.13E−01 | 7.34E−01 | 1.06 | ATP1B3; CXCL10; CXCL11; CXCL9; GSTO1; HOMER1; MMP9; PCSK9; PPIF |
| alcohol biosynthetic process: GO | 102 | 5 | 4.13E−01 | 7.34E−01 | 1.07 | CH25H; CYP27B1; FABP5; PTAFR; SQLE |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| positive regulation of synaptic transmission: GO | 102 | 5 | 4.13E−01 | 7.34E−01 | 1.07 | ADCYAP1; IFNG; NTRK1; PLK2; WNT7A |
| vacuolar lumen: GO | 102 | 5 | 4.13E−01 | 7.34E−01 | 1.07 | CTSB; HPSE; HSPA8; IFI30; RAB38 |
| igf1r signaling cascade | 165 | 8 | 4.13E−01 | 7.34E−01 | 1.06 | CSF2; DUSP9; EIF4EBP1; HBEGF; IL2RA; JAK3; PSMA5; PSMB6 |
| irs-related events triggered by igf1r | 165 | 8 | 4.13E−01 | 7.34E−01 | 1.06 | CSF2; DUSP9; EIF4EBP1; HBEGF; IL2RA; JAK3; PSMA5; PSMB6 |
| signaling by type 1 insulin-like growth factor 1 receptor (igf1r) | 165 | 8 | 4.13E−01 | 7.34E−01 | 1.06 | CSF2; DUSP9; EIF4EBP1; HBEGF; IL2RA; JAK3; PSMA5; PSMB6 |
| pathway: GO | 40 | 2 | 4.14E−01 | 7.34E−01 | 1.09 | CCNE1; RAN |
| calcium ion import into cytosol: GO | 40 | 2 | 4.14E−01 | 7.34E−01 | 1.09 | CCL3; CCR5 |
| cap-dependent translation initiation | 40 | 2 | 4.14E−01 | 7.34E−01 | 1.09 | EIF4EBP1; RPL22L1 |
| cerebellar cortex development: GO | 40 | 2 | 4.14E−01 | 7.34E−01 | 1.09 | KIF14; WNT7A |
| cytoplasmic sequestering of protein: GO | 40 | 2 | 4.14E−01 | 7.34E−01 | 1.09 | HK2; MDFI |
| eukaryotic translation initiation | 40 | 2 | 4.14E−01 | 7.34E−01 | 1.09 | EIF4EBP1; RPL22L1 |
| exonuclease activity active with either ribo or deoxyribonucleic acids and producing 5 phosphomonoesters: GO | 40 | 2 | 4.14E−01 | 7.34E−01 | 1.09 | EXO1; ISG20 |
| membrane invagination: GO | 40 | 2 | 4.14E−01 | 7.34E−01 | 1.09 | FCGR1A; IGHG4 |
| negative regulation of response to cytokine stimulus: GO | 40 | 2 | 4.14E−01 | 7.34E−01 | 1.09 | GSTP1; IL36RN |
| nik -- >noncanonical nf-kb signaling | 40 | 2 | 4.14E−01 | 7.34E−01 | 1.09 | PSMA5; PSMB6 |
| positive regulation of atpase activity: GO | 40 | 2 | 4.14E−01 | 7.34E−01 | 1.09 | ATP1B3; UHRF1 |
| propanoate metabolism | 40 | 2 | 4.14E−01 | 7.34E−01 | 1.09 | ALDH1A3; LDHA |
| prostate gland development: GO | 40 | 2 | 4.14E−01 | 7.34E−01 | 1.09 | TNC; WNT5A |
| sulfur amino acid metabolic process: GO | 40 | 2 | 4.14E−01 | 7.34E−01 | 1.09 | AHCY; CNDP2 |
| cell surface receptor signaling pathway involved in cell cell signaling: GO | 61 | 3 | 4.19E−01 | 7.34E−01 | 1.08 | CHRNA3; CHRNA6; CHRNA9 |
| inclusion body: GO | 61 | 3 | 4.19E−01 | 7.34E−01 | 1.08 | NEFM; ORC6; SNCB |
| regulation of cellular amino acid metabolic process: GO | 61 | 3 | 4.19E−01 | 7.34E−01 | 1.08 | PSMA4; PSMA5; PSMB6 |
| developmental maturation: GO | 166 | 8 | 4.20E−01 | 7.34E−01 | 1.05 | BFSP1; CCNB1; CDC25B; CDK5R1; CNTNAP2; HIF1A; RAB38; TRIP13 |
| actiny pathway | 20 | 1 | 4.20E−01 | 7.34E−01 | 1.09 | NTRK1 |
| activation of bh3-only proteins | 20 | 1 | 4.20E−01 | 7.34E−01 | 1.09 | ISFN |
| activation of nf kappab in b cells | 20 | 1 | 4.20E−01 | 7.34E−01 | 1.09 | PSMA4 |
| alkaloid biosynthesis ii | 20 | 1 | 4.20E−01 | 7.34E−01 | 1.09 | ESCO2 |
| au rich element binding: GO | 20 | 1 | 4.20E−01 | 7.34E−01 | 1.09 | ZC3H12A |
| base excision repair | 20 | 1 | 4.20E−01 | 7.34E−01 | 1.09 | PCNA |
| cellular response to interleukin 6: GO | 20 | 1 | 4.20E−01 | 7.34E−01 | 1.09 | IL6 |
| csk pathway | 20 | 1 | 4.20E−01 | 7.34E−01 | 1.09 | CD3E |
| dopamine metabolic process: GO | 20 | 1 | 4.20E−01 | 7.34E−01 | 1.09 | SNCB |
| eating behavior: GO | 20 | 1 | 4.20E−01 | 7.34E−01 | 1.09 | CCK |
| embryonic placenta morphogenesis: GO | 20 | 1 | 4.20E−01 | 7.34E−01 | 1.09 | SOCS3 |
| exon exon junction complex: GO | 20 | 1 | 4.20E−01 | 7.34E−01 | 1.09 | EIF4A3 |
| second: GO | 20 | 1 | 4.20E−01 | 7.34E−01 | 1.09 | WNT5A |
| heart growth: GO | 20 | 1 | 4.20E−01 | 7.34E−01 | 1.09 | NDRG4 |
| hedgehog 2pathway | 20 | 1 | 4.20E−01 | 7.34E−01 | 1.09 | STIL |
| igf1mtor pathway | 20 | 1 | 4.20E−01 | 7.34E−01 | 1.09 | EIF4EBP1 |
| lagging strand synthesis | 20 | 1 | 4.20E−01 | 7.34E−01 | 1.09 | PCNA |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| m g1 transition | 20 | 1 | 4.20E−01 | 7.34E−01 | 1.09 | PSMA4 |
| macromolecule transmembrane transporter activity: GO | 20 | 1 | 4.20E−01 | 7.34E−01 | 1.09 | SEC61G |
| mrna transcription: GO | 20 | 1 | 4.20E−01 | 7.34E−01 | 1.09 | HIF1A |
| negative regulation of steroid metabolic process: GO | 20 | 1 | 4.20E−01 | 7.34E−01 | 1.09 | CYP27B1 |
| negative regulation of translational initiation: GO | 20 | 1 | 4.20E−01 | 7.34E−01 | 1.09 | EIF4EBP1 |
| netrin1 signaling | 20 | 1 | 4.20E−01 | 7.34E−01 | 1.09 | PRKCQ |
| binding: GO | 20 | 1 | 4.20E−01 | 7.34E−01 | 1.09 | KPNA2 |
| pigment granule organization: GO | 20 | 1 | 4.20E−01 | 7.34E−01 | 1.09 | RAB38 |
| positive regulation of g protein coupled receptor protein signaling pathway: GO | 20 | 1 | 4.20E−01 | 7.34E−01 | 1.09 | KLK6 |
| positive regulation of nitric oxide synthase activity: GO | 20 | 1 | 4.20E−01 | 7.34E−01 | 1.09 | HIF1A |
| remodeling: GO | 20 | 1 | 4.20E−01 | 7.34E−01 | 1.09 | IL12B |
| positive regulation of transcription from rna polymerase ii promoter in response to stress: GO | 20 | 1 | 4.20E−01 | 7.34E−01 | 1.09 | HIF1A |
| positive t cell selection: GO | 20 | 1 | 4.20E−01 | 7.34E−01 | 1.09 | IL6 |
| activity: GO | 20 | 1 | 4.20E−01 | 7.34E−01 | 1.09 | SH3BGRL3 |
| purinergic nucleotide receptor signaling pathway: GO | 20 | 1 | 4.20E−01 | 7.34E−01 | 1.09 | PTAFR |
| rac 1 cell motility signaling pathway | 20 | 1 | 4.20E−01 | 7.34E−01 | 1.09 | CDK5R1 |
| regulation of protein targeting to membrane: GO | 20 | 1 | 4.20E−01 | 7.34E−01 | 1.09 | CDK5R1 |
| regulation of receptor biosynthetic process: GO | 20 | 1 | 4.20E−01 | 7.34E−01 | 1.09 | HIF1A |
| exocytosis: GO | 20 | 1 | 4.20E−01 | 7.34E−01 | 1.09 | RIMS3 |
| regulation of transcription from rna polymerase iii promoter: GO | 20 | 1 | 4.20E−01 | 7.34E−01 | 1.09 | POLR3G |
| rna polymerase iii transcription initiation from type 3 promoter | 20 | 1 | 4.20E−01 | 7.34E−01 | 1.09 | POLR3G |
| termination | 20 | 1 | 4.20E−01 | 7.34E−01 | 1.09 | POLR3G |
| somatic recombination of immunoglobulin gene segments: GO | 20 | 1 | 4.20E−01 | 7.34E−01 | 1.09 | EXO1 |
| tff pathway | 20 | 1 | 4.20E−01 | 7.34E−01 | 1.09 | CYCS |
| traf6 mediated induction of nfkb and map kinases upon tlr7 8 or 9 activation | 20 | 1 | 4.20E−01 | 7.34E−01 | 1.09 | CDK1 |
| translation repressor activity: GO | 20 | 1 | 4.20E−01 | 7.34E−01 | 1.09 | EIF4EBP1 |
| xenobiotics | 20 | 1 | 4.20E−01 | 7.34E−01 | 1.09 | CYP2S1 |
| lysosomal lumen: GO | 82 | 4 | 4.21E−01 | 7.34E−01 | 1.07 | CTSB; HPSE; HSPA8; IFI30 |
| clathrin coated vesicle: GO | 145 | 7 | 4.21E−01 | 7.34E−01 | 1.06 | AP1S3; CTLA4; FCGR1A; HBEGF; HSPA8; LDLR; WNT5A |
| positive regulation of wnt signaling pathway: GO | 145 | 7 | 4.21E−01 | 7.34E−01 | 1.06 | ASPM; DEPDC1B; PSMA4; PSMA5; PSMB6; WNT5A; WNT7A |
| oxidoreductase activity acting on ch oh group of donors: GO | 124 | 6 | 4.21E−01 | 7.35E−01 | 1.06 | ADH7; AKR1B10; AKR1B15; LDHA; RDH16; SDR9C7 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| symporter activity: GO | 124 | 6 | 4.21E−01 | 7.35E−01 | 1.06 | SLC16A1; SLC16A6; SLC16A9; SLC2A9; SLC5A1; SLC6A11 |
| bicarbonate transport: GO | 41 | 2 | 4.27E−01 | 7.40E−01 | 1.07 | SLC26A9; SLC4A8 |
| cardiac cell development: GO | 41 | 2 | 4.27E−01 | 7.40E−01 | 1.07 | CCNB1; CDK1 |
| signaling | 41 | 2 | 4.27E−01 | 7.40E−01 | 1.07 | PSMA5; PSMB6 |
| epo pathway | 41 | 2 | 4.27E−01 | 7.40E−01 | 1.07 | SOCS3; STAT1 |
| g alpha1213 signalling events | 46 | 2 | 4.27E−01 | 7.40E−01 | 1.07 | GNGT2; RAC2 |
| hedgehog ligand biogenesis | 41 | 2 | 4.27E−01 | 7.40E−01 | 1.07 | PSMA5; PSMB6 |
| lung morphogenesis: GO | 41 | 2 | 4.27E−01 | 7.40E−01 | 1.07 | FOXF1; TNC |
| mitotic recombination: GO | 41 | 2 | 4.27E−01 | 7.40E−01 | 1.07 | PCNA; TOP2A |
| phosphatase complex: GO | 41 | 2 | 4.27E−01 | 7.40E−01 | 1.07 | CYCS; PPP4R1 |
| positive regulation of gliogenesis: GO | 41 | 2 | 4.27E−01 | 7.40E−01 | 1.07 | CXCR4; IL1B |
| regulation of toll like receptor signaling pathway: GO | 41 | 2 | 4.27E−01 | 7.40E−01 | 1.07 | LTF; RSAD2 |
| steroid hormone biosynthesis | 41 | 2 | 4.27E−01 | 7.40E−01 | 1.07 | UGT1A10; UGT1A7 |
| sumoylation of dna damage response and repair proteins | 41 | 2 | 4.27E−01 | 7.40E−01 | 1.07 | BLM; CBX2 |
| damaged dna binding: GO | 62 | 3 | 4.29E−01 | 7.40E−01 | 1.06 | H2AFX; PCNA; POLQ |
| endothelin pathway | 62 | 3 | 4.29E−01 | 7.40E−01 | 1.06 | GNA15; MMP1; PRKCQ |
| mitochondrion: GO | 62 | 3 | 4.29E−01 | 7.40E−01 | 1.06 | HK2; TIMM13; TIMM8B |
| contraction: GO | 62 | 3 | 4.29E−01 | 7.40E−01 | 1.06 | DSC2; GSTO1; ZC3H12A |
| secretory granule lumen: GO | 62 | 3 | 4.29E−01 | 7.40E−01 | 1.06 | SERPINA1; SERPINE1; SRGN |
| sensory perception of pain: GO | 62 | 3 | 4.29E−01 | 7.40E−01 | 1.06 | ADCYAP1; IL12B; NTRK1 |
| viral myocarditis | 62 | 3 | 4.29E−01 | 7.40E−01 | 1.06 | CD80; CYCS; RAC2 |
| migration: GO | 104 | 5 | 4.30E−01 | 7.40E−01 | 1.05 | CXCL13; SH3BGRL3; WNT5A; WNT7A; ZC3H12A |
| cardiocyte differentiation: GO | 83 | 4 | 4.30E−01 | 7.40E−01 | 1.05 | CALR; CCNB1; CDK1; EOMES |
| membrane: GO | 126 | 6 | 4.37E−01 | 7.40E−01 | 1.04 | ENO1; GNA15; GNGT2; JAK3; PCSK9; RGS1 |
| regulation of cyclic nucleotide metabolic process: GO | 126 | 6 | 4.37E−01 | 7.40E−01 | 1.04 | ADCYAP1; CXCL10; CXCL11; CXCL9; GPR65; WNT5A |
| transport: GO | 21 | 1 | 4.38E−01 | 7.40E−01 | 1.04 | RHCG |
| ammonium transmembrane transporter activity: GO | 21 | 1 | 4.38E−01 | 7.40E−01 | 1.04 | RHCG |
| aquaporin-mediated transport | 21 | 1 | 4.38E−01 | 7.40E−01 | 1.04 | AQP3 |
| camp binding: GO | 21 | 1 | 4.38E−01 | 7.40E−01 | 1.04 | CNGB1 |
| cell cell junction organization | 21 | 1 | 4.38E−01 | 7.40E−01 | 1.04 | CDH3 |
| cellular protein complex localization: GO | 21 | 1 | 4.38E−01 | 7.40E−01 | 1.04 | RAN |
| cellular response to virus: GO | 21 | 1 | 4.38E−01 | 7.40E−01 | 1.04 | ZC3H12A |
| development: GO | 21 | 1 | 4.38E−01 | 7.40E−01 | 1.04 | KIF14 |
| deadenylation dependent mrna decay | 21 | 1 | 4.38E−01 | 7.40E−01 | 1.04 | EIF4A3 |
| g protein alpha subunit binding: GO | 21 | 1 | 4.38E−01 | 7.40E−01 | 1.04 | RGS1 |
| glucosamine containing compound metabolic process: GO | 21 | 1 | 4.38E−01 | 7.40E−01 | 1.04 | CHI3L2 |
| glutamine metabolic process: GO | 21 | 1 | 4.38E−01 | 7.40E−01 | 1.04 | GGH |
| gtp metabolic process: GO | 21 | 1 | 4.38E−01 | 7.40E−01 | 1.04 | NME1 |
| system | 21 | 1 | 4.38E−01 | 7.40E−01 | 1.04 | HIF1A |
| immunoglobulin production involved in immunoglobulin mediated immune response: GO | 21 | 1 | 4.38E−01 | 7.40E−01 | 1.04 | EXO1 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| intrinsic component of mitochondrial outer membrane: GO | 21 | 1 | 4.38E−01 | 7.40E−01 | 1.04 | BAK1 |
| membrane lipid catabolic process: GO | 21 | 1 | 4.38E−01 | 7.40E−01 | 1.04 | NEU2 |
| proteolysis: GO | 21 | 1 | 4.38E−01 | 7.40E−01 | 1.04 | PRKCQ |
| mitochondrial trna aminoacylation | 21 | 1 | 4.38E−01 | 7.40E−01 | 1.04 | GARS |
| negative regulation of peptidyl serine phosphorylation: GO | 21 | 1 | 4.38E−01 | 7.40E−01 | 1.04 | BAK1 |
| neuropeptide receptor binding: GO | 21 | 1 | 4.38E−01 | 7.40E−01 | 1.04 | ADCYAPI |
| nf-kb signaling pathway | 21 | 1 | 4.38E−01 | 7.40E−01 | 1.04 | MYD88 |
| nucleus: GO | 21 | 1 | 4.38E−01 | 7.40E−01 | 1.04 | KPNA2 |
| oxidoreductase activity acting on a heme group of donors: GO | 21 | 1 | 4.38E−01 | 7.40E−01 | 1.04 | COX7B |
| perk regulates gene expression | 21 | 1 | 4.38E−01 | 7.40E−01 | 1.04 | CXCL8 |
| positive regulation of excitatory postsynaptic potential: GO | 21 | 1 | 4.38E−01 | 7.40E−01 | 1.04 | WNT7A |
| hypertrophy: GO | 21 | 1 | 4.38E−01 | 7.40E−01 | 1.04 | NR4A3 |
| positive regulation of rna splicing: GO | 21 | 1 | 4.38E−01 | 7.40E−01 | 1.04 | HSPA8 |
| precatalytic spliceosome: GO | 21 | 1 | 4.38E−01 | 7.40E−01 | 1.04 | SNRPG |
| prespliceosome: GO | 21 | 1 | 4.38E−01 | 7.40E−01 | 1.04 | SNRPG |
| regulation of cellular extravasation: GO | 21 | 1 | 4.38E−01 | 7.40E−01 | 1.04 | PTAFR |
| regulation of glial cell proliferation: GO | 21 | 1 | 4.38E−01 | 7.40E−01 | 1.04 | ADCYAP1 |
| regulation of isotype switching: GO | 21 | 1 | 4.38E−01 | 7.40E−01 | 1.04 | IFNG |
| regulation of positive chemotaxis: GO | 21 | 1 | 4.38E−01 | 7.40E−01 | 1.04 | ARTN |
| regulatory rna pathways | 21 | 1 | 4.38E−01 | 7.40E−01 | 1.04 | RAN |
| response to thyroid hormone: GO | 21 | 1 | 4.38E−01 | 7.40E−01 | 1.04 | CTSB |
| precise effect on runx1 targets is not known | 21 | 1 | 4.38E−01 | 7.40E−01 | 1.04 | CBX2 |
| signaling by fgfr1 in disease | 21 | 1 | 4.38E−01 | 7.40E−01 | 1.04 | STAT1 |
| signaling by sef kit | 21 | 1 | 4.38E−01 | 7.40E−01 | 1.04 | CDK1 |
| regulation of camp metabolic process: GO | 105 | 5 | 4.38E−01 | 7.40E−01 | 1.04 | ADCYAP1; CXCL10; CXCL11; CXCL9; GPR65 |
| protein o linked glycosylation: GO | 84 | 4 | 4.39E−01 | 7.40E−01 | 1.04 | B3GNT3; GALNT6; GCNT4; SDF2L1 |
| abc transporters | 42 | 2 | 4.40E−01 | 7.40E−01 | 1.04 | ABCG4; TAP2 |
| hedgehog ’on’ state | 42 | 2 | 4.40E−01 | 7.40E−01 | 1.04 | PSMA5; PSMB6 |
| phospholipid transporter activity: GO | 42 | 2 | 4.40E−01 | 7.40E−01 | 1.04 | PITPNM1; PRELID1 |
| dephosphorylation: GO | 42 | 2 | 4.40E−01 | 7.40E−01 | 1.04 | CDCA2; IFNG |
| contraction: GO | 42 | 2 | 4.40E−01 | 7.40E−01 | 1.04 | GSTO1; PTAFR |
| positive regulation of regulated secretory pathway: GO | 42 | 2 | 4.40E−01 | 7.40E−01 | 1.04 | IL4R; PTAFR |
| regulation of insulin secretion involved in cellular response to glucose stimulus: GO | 42 | 2 | 4.40E−01 | 7.40E−01 | 1.04 | HIF1A; VSNL1 |
| regulation of lipid catabolic process: GO | 42 | 2 | 4.40E−01 | 7.40E−01 | 1.04 | IL1B; LDLR |
| regulation of sodium ion transmembrane transport: GO | 42 | 2 | 4.40E−01 | 7.40E−01 | 1.04 | ATP1B3; PCSK9 |
| associative learning: GO | 63 | 3 | 4.40E−01 | 7.40E−01 | 1.04 | EIF4A3; HIF1A; NDRG4 |
| hormone activity: GO | 63 | 3 | 4.40E−01 | 7.40E−01 | 1.04 | ADCYAP1; ADM2; CCK |
| platelet alpha granule: GO | 63 | 3 | 4.40E−01 | 7.40E−01 | 1.04 | SERPINA1; SERPINE1; SRGN |
| rb 1pathway | 63 | 3 | 4.40E−01 | 7.40E−01 | 1.04 | CCNA2; CCNE1; CSF2 |

TABLE 4-continued

| Functional enrichment for genes dysregulated in both PN and psoriatic lesional skin. | | | | | | |
|---|---|---|---|---|---|---|
| | Num_Fun_genes | Common pso and PN (up) Num_IntFun_genes | Common pso and PN (up) p | Common pso and PN (up) FDR | Common pso and PN (up) FC | Common pso and PN (up) genes |
| regulation of mrna stability by proteins that bind au-rich elements | 63 | 3 | 4.40E−01 | 7.40E−01 | 1.04 | HSPA8; PSMA5; PSMB6 |
| interleukin-2 family signaling | 148 | 7 | 4.42E−01 | 7.41E−01 | 1.03 | CSF2; DUSP9; HBEGF; IL2RA; JAK3; PSMA5; PSMB6 |
| regulation of carbohydrate metabolic process: GO | 148 | 7 | 4.42E−01 | 7.41E−01 | 1.03 | HIF1A; IL6; PGAM1; PHLDA2; PTAFR; UGT1A10; UGT1A7 |
| vegfr2 mediated cell proliferation | 148 | 7 | 4.42E−01 | 7.41E−01 | 1.03 | CSF2; DUSP9; HBEGF; IL2RA; JAK3; PSMA5; PSMB6 |
| endocytosis | 127 | 6 | 4.44E−01 | 7.41E−01 | 1.03 | CCR5; CXCR4; HSPA6; HSPA8; IL2RA; NTRK1 |
| rna phosphodiester bond hydrolysis: GO | 106 | 5 | 4.46E−01 | 7.41E−01 | 1.03 | EXO1; ISG20; RNASE7; RPP40; ZC3H12A |
| metencephalon development: GO | 85 | 4 | 4.49E−01 | 7.41E−01 | 1.03 | CDK5R1; KIF14; NLGN4X; WNT7A |
| regulation of circadian rhythm: GO | 85 | 4 | 4.49E−01 | 7.41E−01 | 1.03 | ARNTL2; IL6; TIMELESS; TOP2A |
| cardiac muscle cell differentiation: GO | 64 | 3 | 4.51E−01 | 7.41E−01 | 1.03 | CALR; CCNB1; CDK1 |
| coated pit: GO | 64 | 3 | 4.51E−01 | 7.41E−01 | 1.03 | AP1S3; LDLR; SELE |
| glioma | 64 | 3 | 4.51E−01 | 7.41E−01 | 1.03 | CALML3; CALML5; TGFA |
| multi organism localization: GO | 64 | 3 | 4.51E−01 | 7.41E−01 | 1.03 | KPNA2; RAN; TAP2 |
| activity: GO | 43 | 2 | 4.53E−01 | 7.41E−01 | 1.02 | B3GNT3; GCNT4 |
| metabolism | 43 | 2 | 4.53E−01 | 7.41E−01 | 1.02 | HK2; PGM2 |
| balance: GO | 43 | 2 | 4.53E−01 | 7.41E−01 | 1.02 | ALDH1A3; NR4A3 |
| neurotransmitter release cycle | 43 | 2 | 4.53E−01 | 7.41E−01 | 1.02 | HSPA8; SLC6A11 |
| peptidyl threonine modification: GO | 43 | 2 | 4.53E−01 | 7.41E−01 | 1.02 | CDK1; CDK5R1 |
| regulation of actin filament depolymerization: GO | 43 | 2 | 4.53E−01 | 7.41E−01 | 1.02 | SH3BGRL3; TWF1 |
| regulation of cardiac muscle tissue development: GO | 43 | 2 | 4.53E−01 | 7.41E−01 | 1.02 | CCNB1; CDK1 |
| regulation of ras by gaps | 43 | 2 | 4.53E−01 | 7.41E−01 | 1.02 | PSMA5; PSMB6 |
| solute sodium symporter activity: GO | 43 | 2 | 4.53E−01 | 7.41E−01 | 1.02 | SLC5A1; SLC6A11 |
| sprouting angiogenesis: GO | 43 | 2 | 4.53E−01 | 7.41E−01 | 1.02 | ESM1; PGF |
| trna aminoacylation | 43 | 2 | 4.53E−01 | 7.41E−01 | 1.02 | GARS; TARS |
| regulation of establishment of planar polarity: GO | 107 | 5 | 4.55E−01 | 7.41E−01 | 1.02 | GRHL3; PSMA4; PSMA5; PSMB6; WNT5A |
| aldo keto reductase nadp activity: GO | 22 | 1 | 4.55E−01 | 7.41E−01 | 0.99 | AKRIB10 |
| alzheimer's disease | 22 | 1 | 4.55E−01 | 7.41E−01 | 0.99 | GAPDH |
| anterograde axonal transport: GO | 22 | 1 | 4.55E−01 | 7.41E−01 | 0.99 | KIF4A |
| aspartate family amino acid biosynthetic process: GO | 22 | 1 | 4.55E−01 | 7.41E−01 | 0.99 | GOT2 |
| axon regeneration: GO | 22 | 1 | 4.55E−01 | 7.41E−01 | 0.99 | TNC |
| cellular response to epidermal growth factor stimulus: GO | 22 | 1 | 4.55E−01 | 7.41E−01 | 0.99 | GSTPJ |
| central nervous system projection neuron axonogenesis: GO | 22 | 1 | 4.55E−01 | 7.41E−01 | 0.99 | FBXO45 |
| class b/2 (secretin family receptors) | 22 | 1 | 4.55E−01 | 7.41E−01 | 0.99 | WNT5A |
| e box binding: GO | 22 | 1 | 4.55E−01 | 7.41E−01 | 0.99 | ARNTL2 |
| endothelial cell proliferation: GO | 22 | 1 | 4.55E−01 | 7.41E−01 | 0.99 | HMOX1 |
| epha-mediated growth cone collapse | 22 | 1 | 4.55E−01 | 7.41E−01 | 0.99 | SHB |
| ferrous iron binding: GO | 22 | 1 | 4.55E−01 | 7.41E−01 | 0.99 | ACP5 |
| pi3kgamma | 22 | 1 | 4.55E−01 | 7.41E−01 | 0.99 | GNGT2 |
| ga12 pathway | 22 | 1 | 4.55E−01 | 7.41E−01 | 0.99 | NR4A3 |
| heparan sulfate proteoglycan | 22 | 1 | 4.55E−01 | 7.41E−01 | 0.99 | HS3ST3B1 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| biosynthetic process: GO | | | | | | |
| her2 pathway | 22 | 1 | 4.55E−01 | 7.41E−01 | 0.99 | IL6 |
| hydrolase activity hydrolyzing n glycosyl compounds: GO | 22 | 1 | 4.55E−01 | 7.41E−01 | 0.99 | PCNA |
| inhibition of insulin secretion by adrenaline noradrenaline | 22 | 1 | 4.55E−01 | 7.41E−01 | 0.99 | GNGT2 |
| binding: GO | 22 | 1 | 4.55E−01 | 7.41E−01 | 0.99 | NETO2 |
| lipoprotein metabolism | 22 | 1 | 4.55E−01 | 7.41E−01 | 0.99 | LDLR |
| import: GO | 22 | 1 | 4.55E−01 | 7.41E−01 | 0.99 | GSTO1 |
| negative regulation of endothelial cell apoptotic process: GO | 22 | 1 | 4.55E−01 | 7.41E−01 | 0.99 | SERPINE1 |
| negative regulation of myoblast differentiation: GO | 22 | 1 | 4.55E−01 | 7.41E−01 | 0.99 | CXCL10 |
| neurexins and neuroligins | 22 | 1 | 4.55E−01 | 7.41E−01 | 0.99 | HOMER1 |
| nitrogen metabolism | 22 | 1 | 4.55E−01 | 7.41E−01 | 0.99 | HAL |
| ovarian tumor domain proteases | 22 | 1 | 4.55E−01 | 7.41E−01 | 0.99 | CDK1 |
| oxidoreductase activity acting on paired donors with incorporation or reduction of molecular oxygen reduced flavin or flavoprotein as one donor and incorporation of one atom of oxygen: GO | 22 | 1 | 4.55E−01 | 7.41E−01 | 0.99 | CYP2S1 |
| p53hypoxia pathway | 22 | 1 | 4.55E−01 | 7.41E−01 | 0.99 | HIF1A |
| platelet degranulation | 22 | 1 | 4.55E−01 | 7.41E−01 | 0.99 | MANF |
| plc-gammal signalling | 22 | 1 | 4.55E−01 | 7.41E−01 | 0.99 | NTRK1 |
| positive regulation of b cell mediated immunity: GO | 22 | 1 | 4.55E−01 | 7.41E−01 | 0.99 | IFNG |
| positive regulation of dna templated transcription initiation: GO | 22 | 1 | 4.55E−01 | 7.41E−01 | 0.99 | FOSL1 |
| positive regulation of epithelial cell apoptotic process: GO | 22 | 1 | 4.55E−01 | 7.41E−01 | 0.99 | IL6 |
| prostate gland morphogenesis: GO | 22 | 1 | 4.55E−01 | 7.41E−01 | 0.99 | TNC |
| proximal tubule bicarbonate reclamation | 22 | 1 | 4.55E−01 | 7.41E−01 | 0.99 | ATP1B3 |
| regulation of b cell differentiation: GO | 22 | 1 | 4.55E−01 | 7.41E−01 | 0.99 | PRDM1 |
| regulation of protein homodimerization activity: GO | 22 | 1 | 4.55E−01 | 7.41E−01 | 0.99 | BAK1 |
| regulation of rhodopsin mediated signaling pathway: GO | 22 | 1 | 4.55E−01 | 7.41E−01 | 0.99 | CNGB1 |
| response to elevated platelet cytosolic ca2 | 22 | 1 | 4.55E−01 | 7.41E−01 | 0.99 | SERPINA1 |
| response to interleukin 6: GO | 22 | 1 | 4.55E−01 | 7.41E−01 | 0.99 | IL6 |
| semaphorin receptor binding: GO | 22 | 1 | 4.55E−01 | 7.41E−01 | 0.99 | SH3BGRL3 |
| smad2/smad3:smad4 heterotrimer regulates transcription | 22 | 1 | 4.55E−01 | 7.41E−01 | 0.99 | SERPINE1 |
| syndecan interactions | 22 | 1 | 4.55E−01 | 7.41E−01 | 0.99 | TNC |
| synthesis | 22 | 1 | 4.55E−01 | 7.41E−01 | 0.99 | PCNA |
| temperature homeostasis: GO | 22 | 1 | 4.55E−01 | 7.41E−01 | 0.99 | IL1B |
| thyroid gland development: GO | 22 | 1 | 4.55E−01 | 7.41E−01 | 0.99 | FOXE1 |
| transcription cofactor binding: GO | 22 | 1 | 4.55E−01 | 7.41E−01 | 0.99 | NR4A3 |

TABLE 4-continued

| Functional enrichment for genes dysregulated in both PN and psoriatic lesional skin. | | | | | | |
|---|---|---|---|---|---|---|
| | Num_Fun_genes | Common pso and PN (up) Num_IntFun_genes | Common pso and PN (up) p | Common pso and PN (up) FDR | Common pso and PN (up) FC | Common pso and PN (up) genes |
| transcriptional activator activity rna polymerase ii distal enhancer sequence specific binding: GO | 22 | 1 | 4.55E−01 | 7.41E−01 | 0.99 | SUB 1 |
| regulation of transporter activity: GO | 172 | 8 | 4.60E−01 | 7.45E−01 | 1.02 | ATP1B3; GSTO1; HOMER1; MMP9; NETO2; PCSK9; PPIF; PTAFR |
| feeding behavior: GO | 65 | 3 | 4.61E−01 | 7.45E−01 | 1.01 | ADM2; CCK; STRA6 |
| intracellular steroid hormone receptor signaling pathway: GO | 65 | 3 | 4.61E−01 | 7.45E−01 | 1.01 | CALR; CCNE1; RAN |
| pip3 signaling in cardiac myoctes | 65 | 3 | 4.61E−01 | 7.45E−01 | 1.01 | IFI27; SFN; YWHAQ |
| positive regulation of endothelial cell migration: GO | 65 | 3 | 4.61E−01 | 7.45E−01 | 1.01 | WNT5A; WNT7A; ZC3H12A |
| positive regulation of endothelial cell proliferation: GO | 65 | 3 | 4.61E−01 | 7.45E−01 | 1.01 | HIF1A; PGF; WNT5A |
| positive regulation of neuron death: GO | 65 | 3 | 4.61E−01 | 7.45E−01 | 1.01 | CCL3; CDK5R1; PCSK9 |
| protein activation cascade: GO | 65 | 3 | 4.61E−01 | 7.45E−01 | 1.01 | C1QBP; F12; IGHG4 |
| regulation of organ growth: GO | 65 | 3 | 4.61E−01 | 7.45E−01 | 1.01 | CCNB1; CDK1; SASH3 |
| process: GO | 65 | 3 | 4.61E−01 | 7.45E−01 | 1.01 | CYP27B1; IFNG; IL1B |
| somite development: GO | 65 | 3 | 4.61E−01 | 7.45E−01 | 1.01 | FOXF1; RGS20; WNT5A |
| extracellular matrix organization | 194 | 9 | 4.63E−01 | 7.45E−01 | 1.01 | CTSB; CTSL; MMP1; MMP12; MMP3; MMP9; PPIB; SERPINE1; TNC |
| cytoskeleton dependent intracellular transport: GO | 108 | 5 | 4.63E−01 | 7.45E−01 | 1.01 | HIF1A; KIF14; KIF23; KIF4A; TUBA1C |
| fceri mediated mapk activation | 151 | 7 | 4.63E−01 | 7.45E−01 | 1.01 | CSF2; DUSP9; HBEGF; IL2RA; JAK3; PSMA5; PSMB6 |
| actin filament bundle organization: GO | 44 | 2 | 4.65E−01 | 7.45E−01 | 0.99 | FSCN1; MYO1B |
| activation of nf-kappab in b cells | 44 | 2 | 4.65E−01 | 7.45E−01 | 0.99 | PSMA5; PSMB6 |
| cargo recognition for clathrin-mediated endocytosis | 44 | 2 | 4.65E−01 | 7.45E−01 | 0.99 | LDLR; WNT5A |
| differentiation pathway in pc12 cells | 44 | 2 | 4.65E−01 | 7.45E−01 | 0.99 | CAMP; NTRK1 |
| gaba receptor activation | 44 | 2 | 4.65E−01 | 7.45E−01 | 0.99 | GNGT2; KCNJ15 |
| ion antiporter activity: GO | 44 | 2 | 4.65E−01 | 7.45E−01 | 0.99 | SLC26A9; SLC7A11 |
| ligase activity forming carbon oxygen bonds: GO | 44 | 2 | 4.65E−01 | 7.45E−01 | 0.99 | GARS; TARS |
| nfat and hypertrophy of the heart (transcription in the broken heart) | 44 | 2 | 4.65E−01 | 7.45E−01 | 0.99 | CALR; HBEGF |
| repeat containing receptor nlr signaling pathways | 44 | 2 | 4.65E−01 | 7.45E−01 | 0.99 | MEFV; PYCARD |
| positive regulation of actin filament bundle assembly: GO | 44 | 2 | 4.65E−01 | 7.45E−01 | 0.99 | GPR65; PRKCQ |
| secretion: GO | 44 | 2 | 4.65E−01 | 7.45E−01 | 0.99 | CHRNA3; RIMS3 |
| regulation of tumor necrosis factor mediated signaling pathway: GO | 44 | 2 | 4.65E−01 | 7.45E−01 | 0.99 | GSTP1; PYCARD |
| scaffold protein binding: GO | 44 | 2 | 4.65E−01 | 7.45E−01 | 0.99 | NLGN4X; TREM1 |
| t cell signal transduction | 44 | 2 | 4.65E−01 | 7.45E−01 | 0.99 | CTLA4; PRDX1 |
| ear development: GO | 173 | 8 | 4.66E−01 | 7.45E−01 | 1.01 | ALDH1A3; CCNA2; CHRNA9; GJB6; GRHL3; NR4A3; STRA6; WNT5A |
| potassium ion transport: GO | 130 | 6 | 4.67E−01 | 7.45E−01 | 1.01 | ATP12A; ATPIB3; CNGB1; HTR3A; KCNJ15; KCNK10 |
| regulation of rna stability: GO | 130 | 6 | 4.67E−01 | 7.45E−01 | 1.01 | HSPA8; MYD88; PSMA4; PSMA5; PSMB6; ZC3H12A |
| regulation of cellular ketone metabolic process: GO | 152 | 7 | 4.70E−01 | 7.45E−01 | 1.01 | GK; NR4A3; PSMA4; PSMA5; PSMB6; UGT1A10; UGT1A7 |
| inositol lipid mediated signaling: GO | 109 | 5 | 4.71E−01 | 7.45E−01 | 1.00 | C1QBP; CD80; HBEGF; NTRK1; PTAFR |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| cell junction organization | 23 | 1 | 4.72E−01 | 7.45E−01 | 0.95 | KRT17 |
| dna directed dna polymerase activity: GO | 23 | 1 | 4.72E−01 | 7.45E−01 | 0.95 | POLQ |
| pathway: GO | 23 | 1 | 4.72E−01 | 7.45E−01 | 0.95 | GNA15 |
| effects of pip2 hydrolysis | 23 | 1 | 4.72E−01 | 7.45E−01 | 0.95 | PRKCQ |
| ephrin receptor binding: GO | 23 | 1 | 4.72E−01 | 7.45E−01 | 0.95 | CDK5R1 |
| excitatory postsynaptic potential: GO | 23 | 1 | 4.72E−01 | 7.45E−01 | 0.95 | CHRNA3 |
| extrinsic component of organelle membrane: GO | 23 | 1 | 4.72E−01 | 7.45E−01 | 0.95 | ZC3H12A |
| gamma tubulin binding: GO | 23 | 1 | 4.72E−01 | 7.45E−01 | 0.95 | NME1 |
| gleevec pathway | 23 | 1 | 4.72E−01 | 7.45E−01 | 0.95 | STAT1 |
| glycosylphosphatidylinositol(gpi)-anchor biosynthesis | 23 | 1 | 4.72E−01 | 7.45E−01 | 0.95 | PIGW |
| gleevec | 23 | 1 | 4.72E−01 | 7.45E−01 | 0.95 | STAT1 |
| insulin like growth factor binding: GO | 23 | 1 | 4.72E−01 | 7.45E−01 | 0.95 | ESM1 |
| ionotropic glutamate receptor signaling pathway: GO | 23 | 1 | 4.72E−01 | 7.45E−01 | 0.95 | CDK5R1 |
| binding: GO | 23 | 1 | 4.72E−01 | 7.45E−01 | 0.95 | PTAFR |
| mtor pathway | 23 | 1 | 4.72E−01 | 7.45E−01 | 0.95 | EIF4EBP1 |
| n-glycan trimming in the er and calnexin/calreticulin cycle | 23 | 1 | 4.72E−01 | 7.45E−01 | 0.95 | CALR |
| negative regulation of smoothened signaling pathway: GO | 23 | 1 | 4.72E−01 | 7.45E−01 | 0.95 | CD3E |
| neurotrophin signaling pathway: GO | 23 | 1 | 4.72E−01 | 7.45E−01 | 0.95 | NTRK1 |
| nfkappab canonical pathway | 23 | 1 | 4.72E−01 | 7.45E−01 | 0.95 | RAN |
| nfkb pathway | 23 | 1 | 4.72E−01 | 7.45E−01 | 0.95 | MYD88 |
| nuclear transcribed mrna poly a tail shortening: GO | 23 | 1 | 4.72E−01 | 7.45E−01 | 0.95 | EIF4A3 |
| activity: GO | 23 | 1 | 4.72E−01 | 7.45E−01 | 0.95 | RAN |
| o-linked glycosylation of mucins | 23 | 1 | 4.72E−01 | 7.45E−01 | 0.95 | B3GNT3 |
| signaling: GO | 23 | 1 | 4.72E−01 | 7.45E−01 | 0.95 | C1QBP |
| pigment cell differentiation: GO | 23 | 1 | 4.72E−01 | 7.45E−01 | 0.95 | RAB38 |
| podosome: GO | 23 | 1 | 4.72E−01 | 7.45E−01 | 0.95 | FSCN1 |
| protein export | 23 | 1 | 4.72E−01 | 7.45E−01 | 0.95 | SEC61G |
| receptor signaling complex scaffold activity: GO | 23 | 1 | 4.72E−01 | 7.45E−01 | 0.95 | CD3E |
| regulation of cardiac muscle contraction by calcium ion signaling: GO | 23 | 1 | 4.72E−01 | 7.45E−01 | 0.95 | GSTO1 |
| regulation of cell fate commitment: GO | 23 | 1 | 4.72E−01 | 7.45E−01 | 0.95 | IL12B |
| apoptosis: GO | 23 | 1 | 4.72E−01 | 7.45E−01 | 0.95 | ZC3H12A |
| response to lithium ion: GO | 23 | 1 | 4.72E−01 | 7.45E−01 | 0.95 | CALR |
| rna polymerase iii transcription initiation | 23 | 1 | 4.72E−01 | 7.45E−01 | 0.95 | POLR3G |
| role of erbb2 in signal transduction and oncology | 23 | 1 | 4.72E−01 | 7.45E−01 | 0.95 | IL6 |
| scf dependent proteasomal ubiquitin dependent protein catabolic process: GO | 23 | 1 | 4.72E−01 | 7.45E−01 | 0.95 | KIF14 |
| signaling by fgfr1 mutants | 23 | 1 | 4.72E−01 | 7.45E−01 | 0.95 | STAT1 |
| synaptic vesicle recycling: GO | 23 | 1 | 4.72E−01 | 7.45E−01 | 0.95 | WNT7A |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| zinc ii ion transport: GO | 23 | 1 | 4.72E−01 | 7.45E−01 | 0.95 | SLC39A6 |
| renal cell carcinoma | 66 | 3 | 4.72E−01 | 7.45E−01 | 0.99 | HIF1A; PGF; TGFA |
| cartilage development: GO | 131 | 6 | 4.75E−01 | 7.49E−01 | 1.00 | HIF1A; HMGA2; HYAL3; PITX1; WNT5A; WNT7A |
| vegfa-vegfr2 pathway | 196 | 9 | 4.75E−01 | 7.50E−01 | 1.00 | CSF2; DUSP9; HBEGF; IL2RA; JAK3; PSMA5; PSMB6; SH2D2A; SHB |
| c-type lectin receptors (clrs) | 88 | 4 | 4.76E−01 | 7.50E−01 | 0.99 | IL1B; PSMA5; PSMB6; PYCARD |
| golgi cisterna: GO | 88 | 4 | 4.76E−01 | 7.50E−01 | 0.99 | FUT1; FUT2; FUT3; PITPNM1 |
| perikaryon: GO | 88 | 4 | 4.76E−01 | 7.50E−01 | 0.99 | CCK; CNTNAP2; GOT2; NELL2 |
| clathrin derived vesicle budding | 45 | 2 | 4.78E−01 | 7.50E−01 | 0.97 | AP1S3; HSPA8 |
| non membrane spanning protein tyrosine kinase activity: GO | 45 | 2 | 4.78E−01 | 7.50E−01 | 0.97 | JAK3; MELK |
| photoreceptor cell differentiation: GO | 45 | 2 | 4.78E−01 | 7.50E−01 | 0.97 | CNGB1; PRDM1 |
| protein targeting to mitochondrion: GO | 45 | 2 | 4.78E−01 | 7.50E−01 | 0.97 | TIMM13; TIMM8B |
| trans-golgi network vesicle budding | 45 | 2 | 4.78E−01 | 7.50E−01 | 0.9 | AP1S3; HSPA8 |
| visual behavior: GO | 45 | 2 | 4.78E−01 | 7.50E−01 | 0.97 | HIF1A; NDRG4 |
| regulation of g protein coupled receptor protein signaling pathway: GO | 110 | 5 | 4.80E−01 | 7.50E−01 | 0.99 | ADCYAP1; CNGB1; KLK6; RGS1; RGS20 |
| skeletal muscle organ development: GO | 110 | 5 | 4.80E−01 | 7.50E−01 | 0.99 | CTSB; EOMES; HOMER1; PITX1; STRA6 |
| actin filament: GO | 67 | 3 | 4.82E−01 | 7.50E−01 | 0.98 | FERMT1; MYO1B; RAC2 |
| binding: GO | 67 | 3 | 4.82E−01 | 7.50E−01 | 0.98 | ADAP2; MYO1B; TWF1 |
| non canonical wnt signaling pathway: GO | 132 | 6 | 4.82E−01 | 7.50E−01 | 0.99 | GRHL3; PSMA4; PSMA5; PSMB6; WNT5A; WNT7A |
| aquaporin mediated transport | 24 | 1 | 4.88E−01 | 7.50E−01 | 0.91 | GNGT2 |
| cardiac atrium development: GO | 24 | 1 | 4.88E−01 | 7.50E−01 | 0.91 | WNT5A |
| cellular response to dexamethasone stimulus: GO | 24 | 1 | 4.88E−01 | 7.50E−01 | 0.91 | IL6 |
| stimulus: GO | | | 4.88E−01 | 7.50E−01 | 0.91 | TNC |
| detection of biotic stimulus: GO | 24 | 1 | 4.88E−01 | 7.50E−01 | 0.91 | PGLYRP2 |
| dna polymerase | 24 | 1 | 4.88E−01 | 7.50E−01 | 0.91 | POLQ |
| dynein binding: GO | 24 | 1 | 4.88E−01 | 7.50E−01 | 0.91 | RAN |
| eif4 pathway | 24 | 1 | 4.88E−01 | 7.50E−01 | 0.91 | EIF4EBP1 |
| entrainment of circadian clock: GO | 24 | 1 | 4.88E−01 | 7.50E−01 | 0.91 | ARNTL2 |
| eph-ephrin mediated repulsion of cells | 24 | 1 | 4.88E−01 | 7.50E−01 | 0.9 | MMP9 |
| glucan biosynthetic process: GO | 24 | 1 | 4.88E−01 | 7.50E−01 | 0.91 | PGM2 |
| glycosylphosphatidylinositol gpi anchor biosynthesis | 24 | 1 | 4.88E−01 | 7.50E−01 | 0.91 | PIGW |
| hdac classiii pathway | 24 | 1 | 4.88E−01 | 7.50E−01 | 0.91 | TUBB2A |
| hsp90 protein binding: GO | 24 | 1 | 4.88E−01 | 7.50E−01 | 0.91 | HIF1A |
| isoprenoid biosynthetic process: GO | 24 | 1 | 4.88E−01 | 7.50E−01 | 0.91 | ALDH1A3 |
| mitotic g2 g2 m phases | 24 | 1 | 4.88E−01 | 7.50E−01 | 0.91 | PKMYT1 |
| negative regulation of notch signaling pathway: GO | 24 | 1 | 4.88E−01 | 7.50E−01 | 0.91 | CHAC1 |
| negative regulation of rna splicing: GO | 24 | 1 | 4.88E−01 | 7.50E−01 | 0.91 | C1QBP |
| negative regulation of striated muscle cell differentiation: GO | 24 | 1 | 4.88E−01 | 7.50E−01 | 0.91 | CXCL10 |
| filling: GO | 24 | 1 | 4.88E−01 | 7.50E−01 | 0.91 | PCNA |
| nucleotide kinase activity: GO | 24 | 1 | 4.88E−01 | 7.50E−01 | 0.91 | CMPK2 |
| pantothenate and coa biosynthesis | 24 | 1 | 4.88E−01 | 7.50E−01 | 0.91 | VNN3 |
| phagosome acidification: GO | 24 | 1 | 4.88E−01 | 7.50E−01 | 0.91 | RAB38 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| process: GO | 24 | 1 | 4.88E−01 | 7.50E−01 | 0.91 | FABP5 |
| positive regulation of cartilage development: GO | 24 | 1 | 4.88E−01 | 7.50E−01 | 0.91 | WNT5A |
| rna polymerase ii promoter involved in cellular response to chemical stimulus: GO | 24 | 1 | 4.88E−01 | 7.50E−01 | 0.91 | HIF1A |
| binding: GO | 24 | 1 | 4.88E−01 | 7.50E−01 | 0.91 | SAMSN1 |
| proteoglycan binding: GO | 24 | 1 | 4.88E−01 | 7.50E−01 | 0.91 | CTSB |
| regulation of cgmp metabolic process: GO | 24 | 1 | 4.88E−01 | 7.50E−01 | 0.91 | WNT5A |
| regulation of eif4e and p70 s6 kinase | 24 | 1 | 4.88E−01 | 7.50E−01 | 0.91 | EIF4EBP1 |
| regulation of mrna catabolic process: GO | 24 | 1 | 4.88E−01 | 7.50E−01 | 0.91 | ZC3H12A |
| regulation of necrotic cell death: GO | 24 | 1 | 4.88E−01 | 7.50E−01 | 0.91 | PPIE |
| regulation of neurotransmitter receptor activity: GO | 24 | 1 | 4.88E−01 | 7.50E−01 | 0.91 | NETO2 |
| calcium ion into cytosol by sarcoplasmic reticulum: GO | 24 | 1 | 4.88E−01 | 7.50E−01 | 0.91 | GSTO1 |
| s1p s1p2 pathway | 24 | 1 | 4.88E−01 | 7.50E−01 | 0.91 | GNA15 |
| steroid dehydrogenase activity: GO | 24 | 1 | 4.88E−01 | 7.50E−01 | 0.91 | AKR1B15 |
| sumoylation of rna binding proteins | 24 | 1 | 4.88E−01 | 7.50E−01 | 0.91 | CBX2 |
| telomere maintenance via telomere lengthening: GO | 24 | 1 | 4.88E−01 | 7.50E−01 | 0.91 | PCNA |
| tpo pathway | 24 | 1 | 4.88E−01 | 7.50E−01 | 0.91 | STAT1 |
| tpo signaling pathway | 24 | 1 | 4.88E−01 | 7.50E−01 | 0.91 | STAT1 |
| transmitter gated channel activity: GO | 24 | 1 | 4.88E−01 | 7.50E−01 | 0.91 | CHRNA9 |
| trna processing in the nucleus | 24 | 1 | 4.88E−01 | 7.50E−01 | 0.91 | RPP40 |
| groups | 24 | 1 | 4.88E−01 | 7.50E−01 | 0.91 | SRM |
| vasoconstriction: GO | 24 | 1 | 4.88E−01 | 7.50E−01 | 0.91 | HTR7 |
| a6b1 a6b4 integrin pathway | 46 | 2 | 4.90E−01 | 7.50E−01 | 0.95 | SFN; YWHAQ |
| butanoate metabolism | 46 | 2 | 4.90E−01 | 7.50E−01 | 0.95 | AKR1B10; ALDH1A3 |
| homotypic cell cell adhesion: GO | 46 | 2 | 4.90E−01 | 7.50E−01 | 0.95 | DSC2; SLC7A11 |
| lkb1 pathway | 46 | 2 | 4.90E−01 | 7.50E−01 | 0.95 | SFN; YWHAQ |
| negative regulation of reproductive process: GO | 46 | 2 | 4.90E−01 | 7.50E−01 | 0.95 | OSM; WNT5A |
| nfat pathway | 46 | 2 | 4.90E−01 | 7.50E−01 | 0.95 | CALR; HBEGF |
| protein k48 linked ubiquitination: GO | 46 | 2 | 4.90E−01 | 7.50E−01 | 0.95 | UBE2C; UBE2T |
| process: GO | 46 | 2 | 4.90E−01 | 7.50E−01 | 0.95 | HIF1A; PGAM1 |
| regulation of pten stability and activity | 46 | 2 | 4.90E−01 | 7.50E−01 | 0.95 | PSMA5; PSMB6 |
| regulation of synaptic transmission glutamatergic: GO | 46 | 2 | 4.90E−01 | 7.50E−01 | 0.95 | ADCYAP1; NTRK1 |
| sperm flagellum: GO | 46 | 2 | 4.90E−01 | 7.50E−01 | 0.95 | ENKUR; RAN |
| thymus development: GO | 46 | 2 | 4.90E−01 | 7.50E−01 | 0.95 | CCNB2; FOXE1 |
| negative regulation of neuron death: GO | 155 | 7 | 4.91E−01 | 7.50E−01 | 0.99 | HIF1A; HMOX1; IL6; KIF14; NR4A3; NTRK1; SNCB |
| ret signaling | 155 | 7 | 4.91E−01 | 7.50E−01 | 0.99 | CSF2; DUSP9; HBEGF; IL2RA; JAK3; PSMA5; PSMB6 |
| process: GO | 68 | 3 | 4.92E−01 | 7.50E−01 | 0.96 | AHCY; ALDH4A1; GOT2 |
| copi-mediated anterograde transport | 68 | 3 | 4.92E−01 | 7.50E−01 | 0.96 | TUBA1C; TUBB2A; TUBB6 |
| diseases of metabolism | 68 | 3 | 4.92E−01 | 7.50E−01 | 0.96 | CYP24A1; CYP27B1; CYP4F22 |
| phenol containing compound metabolic | 68 | 3 | 4.92E−01 | 7.50E−01 | 0.96 | FOXE1; GCNT4; SNCB |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| process: GO | | | | | | |
| regulation of cellular ph: GO | 68 | 3 | 4.92E−01 | 7.50E−01 | 0.96 | RAB38; SLC26A9; SLC4A8 |
| wnt signaling pathway | 68 | 3 | 4.92E−01 | 7.50E−01 | 0.96 | FOSL1; GAPDH; RAC2 |
| cellular process involved in reproduction in multicellular organism: GO | 199 | 9 | 4.94E−01 | 7.50E−01 | 0.99 | ASPM; CCNB1; CDC25B; FOSL1; IL1B; PLA2G3; PRDM1; RAN; TRIP13 |
| insulin receptor signalling cascade | 199 | 9 | 4.94E−01 | 7.50E−01 | 0.99 | CDK1; CSF2; DUSP9; EIF4EBP1; HBEGF; IL2RA; JAK3; PSMA5; PSMB6 |
| gap junction | 90 | 4 | 4.94E−01 | 7.50E−01 | 0.97 | CDK1; TUBA1C; TUBB2A; TUBB6 |
| lipid transporter activity: GO | 90 | 4 | 4.94E−01 | 7.50E−01 | 0.97 | ABCG4; GLTP; PITPNM1; PRELID1 |
| process: GO | 90 | 4 | 4.94E−01 | 7.50E−01 | 0.97 | CCT5; NEK2; PIF1; PRKCQ |
| ter signaling | 90 | 4 | 4.94E−01 | 7.50E−01 | 0.97 | CD3E; PRKCQ; PSMA5; PSMB6 |
| amino acid transport: GO | 112 | 5 | 4.96E−01 | 7.50E−01 | 0.98 | SLC38A5; SLC6A11; SLC7A1; SLC7A11; SLC7A5 |
| positive regulation of canonical wnt signaling pathway: GO | 112 | 5 | 4.96E−01 | 7.50E−01 | 0.98 | ASPM; PSMA4; PSMA5; PSMB6; WNT7A |
| cellular response to insulin stimulus: GO | 134 | 6 | 4.97E−01 | 7.50E−01 | 0.98 | EIF4EBP1; GSTP1; HIF1A; NAMPT; PCSK9; RAB31 |
| slc-mediated transmembrane transport | 134 | 6 | 4.97E−01 | 7.50E−01 | 0.98 | SLC16A1; SLC2A9; SLC39A6; SLC7A1; SLC7A11; SLC7A5 |
| b cell receptor signaling pathway: GO | 47 | 2 | 5.02E−01 | 7.50E−01 | 0.93 | CTLA4; IGHG4 |
| cell projection cytoplasm: GO | 47 | 2 | 5.02E−01 | 7.50E−01 | 0.93 | HIF1A; KIF4A |
| ecm proteoglycans | 47 | 2 | 5.02E−01 | 7.50E−01 | 0.93 | SERPINE1; TNC |
| metalloexopeptidase activity: GO | 47 | 2 | 5.02E−01 | 7.50E−01 | 0.93 | CPA6; CPXM1 |
| activity: GO | 47 | 2 | 5.02E−01 | 7.50E−01 | 0.93 | HIF1A; IL1B |
| regulation of postsynaptic membrane potential: GO | 47 | 2 | 5.02E−01 | 7.50E−01 | 0.93 | ADCYAP1; CHRNA3 |
| ribosome assembly: GO | 47 | 2 | 5.02E−01 | 7.50E−01 | 0.93 | C1QBP; EIF6 |
| adipocytokine signaling pathway | 69 | 3 | 5.03E−01 | 7.50E−01 | 0.95 | JAK3; PRKCQ; SOCS3 |
| glial cell development: GO | 69 | 3 | 5.03E−01 | 7.50E−01 | 0.95 | GSTP1; S100A8; S100A9 |
| negative regulation of vasculature development: GO | 69 | 3 | 5.03E−01 | 7.50E−01 | 0.95 | CXCL10; SERPINE1; STAT1 |
| activity: GO | 69 | 3 | 5.03E−01 | 7.50E−01 | 0.95 | ATP1B3; GSTO1; PTAFR |
| unfolded protein response (upr) | 69 | 3 | 5.03E−01 | 7.50E−01 | 0.95 | CALR; CXCL8; SEC61G |
| vegf signaling pathway | 69 | 3 | 5.03E−01 | 7.50E−01 | 0.95 | PLA2G3; RAC2; SH2D2A |
| extrinsic component of cytoplasmic side of plasma membrane: GO | 91 | 4 | 5.03E−01 | 7.50E−01 | 0.96 | GNA15; GNGT2; JAK3; RGS1 |
| process: GO | 91 | 4 | 5.03E−01 | 7.50E−01 | 0.96 | NME1; TK1; TYMP; UPP1 |
| hematopoietic progenitor cell differentiation: GO | 91 | 4 | 5.03E−01 | 7.50E−01 | 0.96 | ESCO2; HERC6; KRT75; TOP2A |
| polyol metabolic process: GO | 91 | 4 | 5.03E−01 | 7.50E−01 | 0.96 | CYP27B1; GK; PTAFR; TPI1 |
| proliferation: GO | 91 | 4 | 5.03E−01 | 7.50E−01 | 0.96 | HIF1A; PGF; STAT1; WNT5A |
| regulation of dendrite development: GO | 113 | 5 | 5.04E−01 | 7.50E−01 | 0.97 | CDC20; CDK5R1; CHRNA3; LRP8; PLK2 |
| regulation of establishment of protein localization to mitochondrion: GO | 113 | 5 | 5.04E−01 | 7.50E−01 | 0.97 | ITGAX; RAC2; SFN; UGCG; YWHAQ |
| adherens junctions interactions | 25 | 1 | 5.04E−01 | 7.50E−01 | 0.87 | CDH3 |
| bile acid and bile salt transport: GO | 25 | 1 | 5.04E−01 | 7.50E−01 | 0.87 | FABP6 |
| blastocyst formation: GO | 25 | 1 | 5.04E−01 | 7.50E−01 | 0.87 | EOMES |
| ether lipid metabolism | 25 | 1 | 5.04E−01 | 7.50E−01 | 0.87 | PLA2G3 |
| g protein beta gamma signalling | 25 | 1 | 5.04E−01 | 7.50E−01 | 0.87 | GNGT2 |
| golgi to plasma membrane protein transport: GO | 25 | 1 | 5.04E−01 | 7.50E−01 | 0.87 | RAB31 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| gsk3 pathway | 25 | 1 | 5.04E−01 | 7.50E−01 | 0.87 | MYD88 |
| il8 cxcr1 pathway | 25 | 1 | 5.04E−01 | 7.50E−01 | 0.87 | GNA15 |
| intracellular ligand gated ion channel activity: GO | 25 | 1 | 5.04E−01 | 7.50E−01 | 0.87 | CNGB1 |
| lipid storage: GO | 25 | 1 | 5.04E−01 | 7.50E−01 | 0.87 | IL1B |
| mannosyltransferase activity: GO | 25 | 1 | 5.04E−01 | 7.50E−01 | 0.87 | SDF2L1 |
| membrane assembly: GO | 25 | 1 | 5.04E−01 | 7.50E−01 | 0.87 | NLGN4X |
| metal ion slc transporters | 25 | 1 | 5.04E−01 | 7.50E−01 | 0.87 | SLC39A6 |
| myocyte ad pathway | 25 | 1 | 5.04E−01 | 7.50E−01 | 0.87 | CAMP |
| nad adp ribosyltransferase activity: GO | 25 | 1 | 5.04E−01 | 7.50E−01 | 0.87 | PARP9 |
| process: GO | 25 | 1 | 5.04E−01 | 7.50E−01 | 0.87 | PLA2G4D |
| positive regulation of multicellular organism growth: GO | 25 | 1 | 5.04E−01 | 7.50E−01 | 0.87 | PPIB |
| positive regulation of potassium ion transmembrane transport: GO | 25 | 1 | 5.04E−01 | 7.50E−01 | 0.87 | ATP1B3 |
| proton transporting two sector atpase complex: GO | 25 | 1 | 5.04E−01 | 7.50E−01 | 0.87 | PPIF |
| pathway: GO | 25 | 1 | 5.04E−01 | 7.50E−01 | 0.87 | PTAFR |
| regulation of anion transmembrane transport: GO | 25 | 1 | 5.04E−01 | 7.50E−01 | 0.87 | PTAFR |
| differentiation: GO | 25 | 1 | 5.04E−01 | 7.50E−01 | 0.87 | IL1B |
| regulation of fatty acid transport: GO | 25 | 1 | 5.04E−01 | 7.50E−01 | 0.87 | IL1B |
| process: GO | 25 | 1 | 5.04E−01 | 7.50E−01 | 0.87 | HIF1A |
| regulation of ryanodine sensitive calcium release channel activity: GO | 25 | 1 | 5.04E−01 | 7.50E−01 | 0.87 | GSTO1 |
| regulation of the force of heart contraction: GO | 25 | 1 | 5.04E−01 | 7.50E−01 | 0.87 | IFNG |
| replacement ossification: GO | 25 | 1 | 5.04E−01 | 7.50E−01 | 0.87 | ALPL |
| response to isoquinoline alkaloid: GO | 25 | 1 | 5.04E−01 | 7.50E−01 | 0.87 | IL1B |
| smad2 smad3 smad4 heterotrimer regulates transcription | 25 | 1 | 5.04E−01 | 7.50E−01 | 0.87 | SERPINE1 |
| solute proton symporter activity: GO | 25 | 1 | 5.04E−01 | 7.50E−01 | 0.87 | SLC2A9 |
| substrate dependent cell migration: GO | 25 | 1 | 5.04E−01 | 7.50E−01 | 0.87 | TNFRSF12A |
| synapsis: GO | 25 | 1 | 5.04E−01 | 7.50E−01 | 0.87 | TRIP13 |
| toll-like receptor pathway | 25 | 1 | 5.04E−01 | 7.50E−01 | 0.87 | MYD88 |
| udp galactosyltransferase activity: GO | 25 | 1 | 5.04E−01 | 7.50E−01 | 0.87 | B3GNT3 |
| negative regulation of intracellular transport: GO | 135 | 6 | 5.05E−01 | 7.51E−01 | 0.97 | FOXF1; GSTO1; HMOX1; MDFI; SLC25A5; ZC3H12A |
| cullin ring ubiquitin ligase complex: GO | 136 | 6 | 5.12E−01 | 7.57E−01 | 0.96 | BUB1B; CDC20; KBTBD8; KLHDC7B; UBE2C; UBE2S |
| glycoprotein binding: GO | 92 | 4 | 5.12E−01 | 7.57E−01 | 0.95 | CALR; CTSB; LDLR; SERPINA1 |
| neural tube formation: GO | 92 | 4 | 5.12E−01 | 7.57E−01 | 0.95 | GRHL3; HIF1A; STIL; WNT5A |
| activity: GO | 92 | 4 | 5.12E−01 | 7.57E−01 | 0.95 | BLM; DDX21; EIF4A3; PIF1 |
| arachidonic acid metabolism | 70 | 3 | 5.13E−01 | 7.57E−01 | 0.94 | CYP4F11; CYP4F22; PLA2G3 |
| cell cell junction assembly: GO | 70 | 3 | 5.13E−01 | 7.57E−01 | 0.94 | ECT2; FSCN1; GJB2 |
| morphogenesis: GO | 70 | 3 | 5.13E−01 | 7.57E−01 | 0.94 | CDK5R1; CHRNA3; LRP8 |
| polymerase ii distal enhancer sequence specific binding: GO | 70 | 3 | 5.13E−01 | 7.57E−01 | 0.94 | FOXF1; HIF1A; SUB1 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| ajdiss 2pathway | 48 | 2 | 5.14E−01 | 7.57E−01 | 0.91 | MMP3; NME1 |
| arf6 trafficking pathway | 48 | 2 | 5.14E−01 | 7.57E−01 | 0.91 | IL2RA; NME1 |
| cajal body: GO | 48 | 2 | 5.14E−01 | 7.57E−01 | 0.91 | ISG20; OIP5 |
| negative regulation of response to dna damage stimulus: GO | 48 | 2 | 5.14E−01 | 7.57E−01 | 0.91 | HMGA2; POLQ |
| presynaptic membrane: GO | 48 | 2 | 5.14E−01 | 7.57E−01 | 0.91 | FBXO45; FOSL1 |
| protein autoubiquitination: GO | 48 | 2 | 5.14E−01 | 7.57E−01 | 0.91 | UBE2T; UHRF1 |
| actions of nitric oxide in the heart | 26 | 1 | 5.20E−01 | 7.57E−01 | 0.84 | SLC7A1 |
| genes | 26 | 1 | 5.20E−01 | 7.57E−01 | 0.84 | EIF4A3 |
| apoptotic cell clearance: GO | 26 | 1 | 5.20E−01 | 7.57E−01 | 0.84 | TGM2 |
| pathway | 26 | 1 | 5.20E−01 | 7.57E−01 | 0.84 | STAT1 |
| cell fate commitment involved in formation of primary germ layer: GO | 26 | 1 | 5.20E−01 | 7.57E−01 | 0.84 | EOMES |
| cell volume homeostasis: GO | 26 | 1 | 5.20E−01 | 7.57E−01 | 0.84 | AQP3 |
| central nervous system neuron axonogenesis: GO | 26 | 1 | 5.20E−01 | 7.57E−01 | 0.84 | FBXO45 |
| cholesterol biosynthesis | 26 | 1 | 5.20E−01 | 7.57E−01 | 0.84 | SQLE |
| downstream signaling events of b cell receptor ber | 26 | 1 | 5.20E−01 | 7.57E−01 | 0.84 | PSMA4 |
| molecules | 26 | 1 | 5.20E−01 | 7.57E−01 | 0.84 | CD3E |
| homologous recombination | 26 | 1 | 5.20E−01 | 7.57E−01 | 0.84 | BLM |
| influence of ras and rho proteins on gl to s transition | 26 | 1 | 5.20E−01 | 7.57E−01 | 0.84 | CCNE1 |
| negative regulation of calcium ion transmembrane transport: GO | 26 | 1 | 5.20E−01 | 7.57E−01 | 0.84 | GSTO1 |
| negative regulation of embryonic development: GO | 26 | 1 | 5.20E−01 | 7.57E−01 | 0.84 | WNT5A |
| steroid hormone receptor signaling pathway: GO | 26 | 1 | 5.20E−01 | 7.57E−01 | 0.84 | CALR |
| negative regulation of telomere maintenance: GO | 26 | 1 | 5.20E−01 | 7.57E−01 | 0.84 | PIF1 |
| nep ns2 interacts with the cellular export machinery | 26 | 1 | 5.20E−01 | 7.57E−01 | 0.84 | RAN |
| neutral lipid biosynthetic process: GO | 26 | 1 | 5.20E−01 | 7.57E−01 | 0.84 | GK |
| p38mapk pathway | 26 | 1 | 5.20E−01 | 7.57E−01 | 0.84 | STAT1 |
| transport: GO | 26 | 1 | 5.20E−01 | 7.57E−01 | 0.84 | CCK |
| positive regulation of fatty acid metabolic process: GO | 26 | 1 | 5.20E−01 | 7.57E−01 | 0.84 | NR4A3 |
| methylation: GO | 26 | 1 | 5.20E−01 | 7.57E−01 | 0.84 | HIST1H1B |
| activity: GO | 26 | 1 | 5.20E−01 | 7.57E−01 | 0.84 | IFNG |
| protein kinase c activating g protein coupled receptor signaling pathway: GO | 26 | 1 | 5.20E−01 | 7.57E−01 | 0.84 | CCK |
| protein phosphatase 2a binding: GO | 26 | 1 | 5.20E−01 | 7.57E−01 | 0.84 | EIF4EBP1 |
| raceyed pathway | 26 | 1 | 5.20E−01 | 7.57E−01 | 0.84 | CCNE1 |
| regulation of cardiac muscle cell contraction: GO | 26 | 1 | 5.20E−01 | 7.57E−01 | 0.84 | DSC2 |
| regulation of cellular senescence: GO | 26 | 1 | 5.20E−01 | 7.57E−01 | 0.84 | HMGA2 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| regulation of endothelial cell differentiation: GO | 26 | 1 | 5.20E−01 | 7.57E−01 | 0.84 | IL1B |
| regulation of fatty acid oxidation: GO | 26 | 1 | 5.20E−01 | 7.57E−01 | 0.84 | NR4A3 |
| regulation of mrna 3 end processing: GO | 26 | 1 | 5.20E−01 | 7.57E−01 | 0.84 | CCNB1 |
| regulation of mrna stability by proteins that bind au rich elements | 26 | 1 | 5.20E−01 | 7.57E−01 | 0.84 | PSMA4 |
| regulation of oxidative stress induced intrinsic apoptotic signaling pathway: GO | 26 | 1 | 5.20E−01 | 7.57E−01 | 0.84 | HIF1A |
| regulation of p38mapk cascade: GO | 26 | 1 | 5.20E−01 | 7.57E−01 | 0.84 | ZC3H12A |
| response to epidermal growth factor: GO | 26 | 1 | 5.20E−01 | 7.57E−01 | 0.84 | GSTP1 |
| spliceosomal tri snrnp complex: GO | 26 | 1 | 5.20E−01 | 7.57E−01 | 0.84 | SNRPG |
| superoxide metabolic process: GO | 26 | 1 | 5.20E−01 | 7.57E−01 | 0.84 | PRDX1 |
| synthesis of pa | 26 | 1 | 5.20E−01 | 7.57E−01 | 0.84 | PLA2G4D |
| translation initiation factor binding: GO | 26 | 1 | 5.20E−01 | 7.57E−01 | 0.84 | EIF4EBP1 |
| ventricular septum morphogenesis: GO | 26 | 1 | 5.20E−01 | 7.57E−01 | 0.84 | WNT5A |
| beta catenin nuc pathway | 71 | 3 | 5.23E−01 | 7.61E−01 | 0.92 | MMP9; SFN; YWHAQ |
| clathrin-mediated endocytosis | 71 | 3 | 5.23E−01 | 7.61E−01 | 0.92 | HSPA8; LDLR; WNT5A |
| protein n linked glycosylation: GO | 71 | 3 | 5.23E−01 | 7.61E−01 | 0.92 | ST6GALNACI; ST8S1A2; VCP |
| cation transporting atpase activity: GO | 49 | 2 | 5.26E−01 | 7.64E−01 | 0.89 | ATP12A; ATP1B3 |
| fas signaling pathway | 49 | 2 | 5.26E−01 | 7.64E−01 | 0.89 | BAK1; TPX2 |
| myocytes | 49 | 2 | 5.26E−01 | 7.64E−01 | 0.89 | SFN; YWHAQ |
| negative regulation of chemotaxis: GO | | | 5.26E−01 | 7.64E−01 | 0.89 | CXCL13; WNT5A |
| protein transmembrane transport: GO | 49 | 2 | 5.26E−01 | 7.64E−01 | 0.89 | HSPA8; SEC61G |
| positive regulation of developmental growth: GO | 138 | 6 | 5.27E−01 | 7.64E−01 | 0.95 | CCNB1; CDK1; CRABP2; PPIB; SASH3; TNFRSF12A |
| lysosome | 116 | 5 | 5.28E−01 | 7.64E−01 | 0.94 | ACP5; AP1S3; CTSB; CTSC; LAMP3 |
| dicarboxylic acid metabolic process: GO | 94 | 4 | 5.30E−01 | 7.64E−01 | 0.93 | ALDH4A1; GOT2; HAL; KYNU |
| acrosomal vesicle: GO | 72 | 3 | 5.33E−01 | 7.64E−01 | 0.91 | ACRV1; CALR; ENKUR |
| bone morphogenesis: GO | 72 | 3 | 5.33E−01 | 7.64E−01 | 0.91 | ACP5; ALPL; LTF |
| signaling: GO | 72 | 3 | 5.33E−01 | 7.64E−01 | 0.91 | CCL3; CD3E; GSTO1 |
| contraction: GO | 72 | 3 | 5.33E−01 | 7.64E−01 | 0.91 | DSC2; GSTO1; ZC3H12A |
| signaling adaptor activity: GO | 72 | 3 | 5.33E−01 | 7.64E−01 | 0.91 | HOMER1; SH2D2A; SHB |
| trif mediated tlr3 signaling | 72 | 3 | 5.33E−01 | 7.64E−01 | 0.91 | CDK1; S100A12; ZBP1 |
| cellular lipid catabolic process: GO | 139 | 6 | 5.34E−01 | 7.64E−01 | 0.94 | AKR1B10; FABP5; FABP6; LIPG; NEU2; PLA2G4D |
| synapse organization: GO | 139 | 6 | 5.34E−01 | 7.64E−01 | 0.94 | FBXO45; NLGN4X; SNCB; TNC; WNT5A; WNT7A |
| alanine and aspartate metabolism | 27 | 1 | 5.35E−01 | 7.64E−01 | 0.81 | GOT2 |
| autophagosome membrane: GO | 27 | 1 | 5.35E−01 | 7.64E−01 | 0.81 | VMP1 |
| binding and uptake of ligands by scavenger receptors | 27 | 1 | 5.35E−01 | 7.64E−01 | 0.81 | CALR |
| membrane | 27 | 1 | 5.35E−01 | 7.64E−01 | 0.81 | CCT5 |
| citrate cycle (tca cycle) | 27 | 1 | 5.35E−01 | 7.64E−01 | 0.81 | OGDHL |
| egf signaling pathway | 27 | 1 | 5.35E−01 | 7.64E−01 | 0.81 | STAT1 |
| ephrinb rev pathway | 27 | 1 | 5.35E−01 | 7.64E−01 | 0.81 | CXCR4 |
| eye photoreceptor cell development: GO | 27 | 1 | 5.35E−01 | 7.64E−01 | 0.81 | PRDM1 |
| folic acid containing compound metabolic process: GO | 27 | 1 | 5.35E−01 | 7.64E−01 | 0.81 | GGH |
| granule cell survival pathway | 27 | 1 | 5.35E−01 | 7.64E−01 | 0.81 | CAMP |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| hsp70 protein binding: GO | 27 | 1 | 5.35E−01 | 7.64E−01 | 0.81 | CDK1 |
| maturation of 5 8s rrna: GO | 27 | 1 | 5.35E−01 | 7.64E−01 | 0.81 | EIF6 |
| negative regulation of axon guidance: GO | 27 | 1 | 5.35E−01 | 7.64E−01 | 0.81 | WNT5A |
| negative regulation of dendrite development: GO | 27 | 1 | 5.35E−01 | 7.64E−01 | 0.81 | PLK2 |
| negative regulation of endothelial cell proliferation: GO | 27 | 1 | 5.35E−01 | 7.64E−01 | 0.81 | STAT1 |
| osteoclast differentiation: GO | 27 | 1 | 5.35E−01 | 7.64E−01 | 0.81 | ACP5 |
| peptide antigen binding: GO | 27 | 1 | 5.35E−01 | 7.64E−01 | 0.81 | SLC7A5 |
| presynaptic active zone: GO | 27 | 1 | 5.35E−01 | 7.64E−01 | 0.81 | RIMS3 |
| nucleus: GO | 27 | 1 | 5.35E−01 | 7.64E−01 | 0.81 | RGS20 |
| regulation of macrophage derived foam cell differentiation: GO | 27 | 1 | 5.35E−01 | 7.64E−01 | 0.81 | CSF2 |
| regulation of triglyceride metabolic process: GO | 27 | 1 | 5.35E−01 | 7.64E−01 | 0.81 | LDLR |
| resolution of abasic sites (ap sites) | 27 | 1 | 5.35E−01 | 7.64E−01 | 0.81 | PCNA |
| ribonucleoside triphosphate biosynthetic process: GO | 27 | 1 | 5.35E−01 | 7.64E−01 | 0.81 | NME1 |
| rna polymerase iii abortive and retractive initiation | 27 | 1 | 5.35E−01 | 7.64E−01 | 0.81 | POLR3G |
| rna stabilization: GO | 27 | 1 | 5.35E−01 | 7.64E−01 | 0.81 | MYD88 |
| selenocysteine synthesis | 27 | 1 | 5.35E−01 | 7.64E−01 | 0.81 | RPL22L1 |
| sh2 domain binding: GO | 27 | 1 | 5.35E−01 | 7.64E−01 | 0.81 | SIT1 |
| synthesis of bile acids and bile salts | 27 | 1 | 5.35E−01 | 7.64E−01 | 0.81 | CH25H |
| vegf, hypoxia, and angiogenesis | 27 | 1 | 5.35E−01 | 7.64E−01 | 0.81 | HIF1A |
| viral mrna translation | 27 | 1 | 5.35E−01 | 7.64E−01 | 0.81 | RPL22L1 |
| carboxylic ester hydrolase activity: GO | 117 | 2 | 5.36E−01 | 7.65E−01 | 0.93 | LIPG; NLGN4X; PLA2G3; PLA2G4D; PLBD1 |
| postsynaptic membrane: GO | 184 | 8 | 5.38E−01 | 7.65E−01 | 0.95 | CHRNA3; CHRNA6; CHRNA9; FBXO45; HOMER1; HTR3A; NLGN4X; SH2D5 |
| abc transporter disorders | 50 | 2 | 5.38E−01 | 7.65E−01 | 0.87 | PSMA5; PSMB6 |
| ammonium transport: GO | 50 | 2 | 5.38E−01 | 7.65E−01 | 0.87 | ADCYAP1; RHCG |
| cell cell adherens junction: GO | 50 | 2 | 5.38E−01 | 7.65E−01 | 0.87 | CDH3; DSC2 |
| cell cell recognition: GO | 50 | 2 | 5.38E−01 | 7.65E−01 | 0.87 | CCT5; FUT3 |
| iron ion transport: GO | 50 | 2 | 5.38E−01 | 7.65E−01 | 0.87 | STEAP1B; STEAP4 |
| p75 ntr receptor-mediated signalling | 50 | 2 | 5.38E−01 | 7.65E−01 | 0.87 | ECT2; MYD88 |
| positive regulation of muscle tissue development: GO | 50 | 2 | 5.38E−01 | 7.65E−01 | 0.87 | CCNB1; CDK1 |
| protein complex localization: GO | 50 | 2 | 5.38E−01 | 7.65E−01 | 0.87 | BIRC5; RAN |
| rna polymerase ii core promoter sequence specific dna binding: GO | 50 | 2 | 5.38E−01 | 7.65E−01 | 0.87 | H2AFZ; STAT1 |
| gnrh signaling pathway | 95 | 4 | 5.38E−01 | 7.65E−01 | 0.92 | CALML3; CALML5; HBEGF; PLA2G3 |
| regulation of extent of cell growth: GO | 95 | 4 | 5.38E−01 | 7.65E−01 | 0.92 | CDK5R1; CRABP2; TNFRSF12A; WNT5A |
| transcriptional repressor activity rna polymerase ii core promoter proximal region sequence specific binding: GO | 95 | 4 | 5.38E−01 | 7.65E−01 | 0.92 | HMGA2; IFI16; MXD1; PRDMI |
| regulation of cell size: GO | 162 | 7 | 5.39E−01 | 7.66E−01 | 0.94 | AQP3; CDK5R1; CRABP2; HIF1A; IL7R; TNFRSF12A; WNT5A |
| fc epsilon ri signaling pathway | 73 | 3 | 5.43E−01 | 7.67E−01 | 0.90 | CSF2; PLA2G3; RAC2 |
| regulation of receptor mediated | 73 | 3 | 5.43E−01 | 7.67E−01 | 0.90 | PCSK9; SELE; SERPINE1 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| endocytosis: GO | | | | | | |
| vascular endothelial growth factor receptor signaling pathway: GO | 73 | 3 | 5.43E−01 | 7.67E−01 | 0.90 | PGF; SH2D2A; SHB |
| activity: GO | 73 | 3 | 5.43E−01 | 7.67E−01 | 0.90 | CNGB1; HTR3A; KCNJ15 |
| cellular protein complex disassembly: GO | 118 | 5 | 5.44E−01 | 7.67E−01 | 0.93 | HSPA8; KIF14; KIF18A; KIF2C; MRPL51 |
| developmental growth involved in morphogenesis: GO | 96 | 4 | 5.47E−01 | 7.67E−01 | 0.91 | AREG; AURKA; TNC; WNT5A |
| melanogenesis | 96 | 4 | 5.47E−01 | 7.67E−01 | 0.91 | CALML3; CALML5; WNT5A; WNT7A |
| response to retinoic acid: GO | 96 | 4 | 5.47E−01 | 7.67E−01 | 0.91 | AQP3; TNC; TRIM16; WNT5A |
| actin cytoskeleton reorganization: GO | 51 | 2 | 5.49E−01 | 7.67E−01 | 0.86 | GPR65; S100A9 |
| amino acid activation: GO | 51 | 2 | 5.49E−01 | 7.67E−01 | 0.86 | GARS; TARS |
| cytosolic calcium ion transport: GO | 51 | 2 | 5.49E−01 | 7.67E−01 | 0.86 | CCL3; CCR5 |
| neuromuscular junction: GO | 51 | 2 | 5.49E−01 | 7.67E−01 | 0.86 | CDK5R1; PRKCQ |
| sh3 sh2 adaptor activity: GO | 51 | 2 | 5.49E−01 | 7.67E−01 | 0.86 | SH2D2A; SHB |
| activation of kainate receptors upon glutamate binding | 28 | 1 | 5.50E−01 | 7.67E−01 | 0.78 | GNGT2 |
| aggresome: GO | 28 | 1 | 5.50E−01 | 7.67E−01 | 0.78 | ORC6 |
| atpase regulator activity: GO | 28 | 1 | 5.50E−01 | 7.67E−01 | 0.78 | ATP1B3 |
| benzoate degradation via coa ligation | 28 | 1 | 5.50E−01 | 7.67E−01 | 0.78 | ESCO2 |
| binding of sperm to zona pellucida: GO | 28 | 1 | 5.50E−01 | 7.67E−01 | 0.78 | CCT5 |
| cadherin binding: GO | 28 | 1 | 5.50E−01 | 7.67E−01 | 0.78 | CDK5R1 |
| forebrain neuron development: GO | 28 | 1 | 5.50E−01 | 7.67E−01 | 0.78 | WNT5A |
| frs2 mediated cascade | 28 | 1 | 5.50E−01 | 7.67E−01 | 0.78 | CDK1 |
| homeostasis of number of cells within a tissue: GO | 28 | 1 | 5.50E−01 | 7.67E−01 | 0.78 | SASH3 |
| hydrogen peroxide metabolic process: GO | 28 | 1 | 5.50E−01 | 7.67E−01 | 0.78 | PRDX1 |
| macrophage activation: GO | 28 | 1 | 5.50E−01 | 7.67E−01 | 0.78 | CSF2 |
| maintenance of protein localization in organelle: GO | 28 | 1 | 5.50E−01 | 7.67E−01 | 0.78 | HK2 |
| mrna splicing - minor pathway | 28 | 1 | 5.50E−01 | 7.67E−01 | 0.78 | SNRPF |
| adhesion: GO | 28 | 1 | 5.50E−01 | 7.67E−01 | 0.78 | SERPINE1 |
| neuron maturation: GO | 28 | 1 | 5.50E−01 | 7.67E−01 | 0.78 | CNTNAP2 |
| no1 pathway | 28 | 1 | 5.50E−01 | 7.67E−01 | 0.78 | SLC7A1 |
| independent of the exon junction complex (ejc) | 28 | 1 | 5.50E−01 | 7.67E−01 | 0.78 | RPL22L1 |
| olfactory receptor activity: GO | 28 | 1 | 5.50E−01 | 7.67E−01 | 0.78 | OR2I1P |
| activity: GO | 28 | 1 | 5.50E−01 | 7.67E−01 | 0.78 | SLC6A11 |
| pdgf signaling pathway | 28 | 1 | 5.50E−01 | 7.67E−01 | 0.78 | STAT1 |
| phosphatidic acid metabolic process: GO | 28 | 1 | 5.50E−01 | 7.67E−01 | 0.78 | PLA2G4D |
| positive regulation of calcium ion transmembrane transporter activity: GO | 28 | 1 | 5.50E−01 | 7.67E−01 | 0.78 | GSTO1 |
| positive regulation of smooth muscle contraction: GO | 28 | 1 | 5.50E−01 | 7.67E−01 | 0.78 | PTAFR |
| pre autophagosomal structure: GO | 28 | 1 | 5.50E−01 | 7.67E−01 | 0.78 | VMP1 |
| protein lipid complex: GO | 28 | 1 | 5.50E−01 | 7.67E−01 | 0.78 | LDLR |
| regulation of heart rate by cardiac conduction: GO | 28 | 1 | 5.50E−01 | 7.67E−01 | 0.78 | DSC2 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| regulation of platelet activation: GO | 28 | 1 | 5.50E−01 | 7.67E−01 | 0.78 | PRKCQ |
| regulation of vacuolar transport: GO | 28 | 1 | 5.50E−01 | 7.67E−01 | 0.78 | NDRG4 |
| skeletal muscle contraction: GO | 28 | 1 | 5.50E−01 | 7.67E−01 | 0.78 | HOMER1 |
| smooth muscle cell differentiation: GO | 28 | 1 | 5.50E−01 | 7.67E−01 | 0.78 | FOXF1 |
| sodium channel regulator activity: GO | 28 | 1 | 5.50E−01 | 7.67E−01 | 0.78 | PCSK9 |
| telomeric dna binding: GO | 28 | 1 | 5.50E−01 | 7.67E−01 | 0.78 | PIF1 |
| trail pathway | 28 | 1 | 5.50E−01 | 7.67E−01 | 0.78 | TNFSF10 |
| u2 type spliceosomal complex: GO | 28 | 1 | 5.50E−01 | 7.67E−01 | 0.78 | SNRPG |
| localization within membrane: GO | 119 | 5 | 5.51E−01 | 7.69E−01 | 0.92 | AREG; CD2; CTSC; SERPINA1; TGFA |
| osteoblast differentiation: GO | 119 | 5 | 5.51E−01 | 7.69E−01 | 0.92 | ALPL; CCL3; CYP24A1; DDX21; TNC |
| artery development: GO | 74 | 3 | 5.52E−01 | 7.69E−01 | 0.89 | FOXF1; PRDM1; STRA6 |
| dorsal ventral pattern formation: GO | 74 | 3 | 5.52E−01 | 7.69E−01 | 0.89 | MDFI; RGS20; WNT7A |
| organophosphate ester transport: GO | 74 | 3 | 5.52E−01 | 7.69E−01 | 0.89 | LDLR; PITPNM1; PRELID1 |
| respiratory chain: GO | 74 | 3 | 5.52E−01 | 7.69E−01 | 0.89 | COX7B; CYCS; HIGD1A |
| protein tyrosine kinase activity: GO | 164 | 7 | 5.53E−01 | 7.69E−01 | 0.93 | CSF2; HBEGF; JAK3; MELK; NTRK1; TTK; TWF1 |
| system: GO | 142 | 6 | 5.55E−01 | 7.70E−01 | 0.92 | ADCYAP1; HIF1A; HMOX1; HTR7; PRKCQ; PTAFR |
| steroid biosynthetic process: GO | 97 | 4 | 5.56E−01 | 7.70E−01 | 0.90 | AKR1B15; CH25H; CYP27B1; SQLE |
| process: GO | 187 | 8 | 5.57E−01 | 7.70E−01 | 0.94 | BUB1; BUB1B; IL1B; LAMP3; MAD2L1; PBK; PLK1; TTK |
| germ cell development: GO | 165 | 7 | 5.59E−01 | 7.70E−01 | 0.93 | ASPM; CCNB1; CDC25B; PLA2G3; PRDM1; RAN; TRIP13 |
| aspartate family amino acid metabolic process: GO | 52 | 2 | 5.61E−01 | 7.70E−01 | 0.84 | AHCY; GOT2 |
| cleavage of growing transcript in the termination region | 52 | 2 | 5.61E−01 | 7.70E−01 | 0.84 | SNRPF; SNRPG |
| complement activation: GO | 52 | 2 | 5.61E−01 | 7.70E−01 | 0.84 | C1QBP; IGHG4 |
| membrane: GO | 52 | 2 | 5.61E−01 | 7.70E−01 | 0.84 | AREG; TGFA |
| fceri mediated nf-kb activation | 52 | 2 | 5.61E−01 | 7.70E−01 | 0.84 | PSMA5; PSMB6 |
| g alpha (q) signalling events | 52 | 2 | 5.61E−01 | 7.70E−01 | 0.84 | CCK; LTB4R |
| hedgehog signaling pathway | 52 | 2 | 5.61E−01 | 7.70E−01 | 0.84 | WNT5A; WNT7A |
| hormone binding: GO | 52 | 2 | 5.61E−01 | 7.70E−01 | 0.84 | ALDH1A3; CALR |
| secretion: GO | 52 | 2 | 5.61E−01 | 7.70E−01 | 0.84 | HIF1A; VSNL1 |
| positive regulation of muscle cell differentiation: GO | 75 | | 5.62E−01 | 7.70E−01 | 0.87 | CXCL9; IL4R; NEU2 |
| late endosome: GO | 188 | 8 | 5.63E−01 | 7.70E−01 | 0.93 | CXCR4; DYSF; HSPA8; IFITM3; LDLR; NTRK1; PCSK9; RAB31 |
| organic acid catabolic process: GO | 188 | 8 | 5.63E−01 | 7.70E−01 | 0.93 | AHCY; ALDH4A1; GOT2; HAL; IDO1; IL4I1; KYNU; TDO2 |
| glycerophospholipid biosynthesis | 98 | 4 | 5.64E−01 | 7.70E−01 | 0.89 | PITPNM1; PLA2G3; PLA2G4D; PLBD1 |
| potassium channel activity: GO | 98 | 4 | 5.64E−01 | 7.70E−01 | 0.89 | CNGB1; HTR3A; KCNJ15; KCNK10 |
| activity: GO | 29 | 1 | 5.64E−01 | 7.70E−01 | 0.75 | GALNT6 |
| aminosugars metabolism | 29 | 1 | 5.64E−01 | 7.70E−01 | 0.75 | HK2 |
| bicellular tight junction assembly: GO | | 1 | 5.64E−01 | 7.70E−01 | 0.75 | ECT2 |
| cell differentiation involved in kidney development: GO | 29 | 1 | 5.64E−01 | 7.70E−01 | 0.75 | STAT1 |
| cyclin dependent protein kinase holoenzyme complex: GO | 29 | 1 | 5.64E−01 | 7.70E−01 | 0.75 | CCNE1 |
| dual incision in gg-ner | 29 | 1 | 5.64E−01 | 7.70E−01 | 0.75 | PCNA |
| establishment of endothelial barrier: GO | 29 | 1 | 5.64E−01 | 7.70E−01 | 0.75 | WNT7A |
| eukaryotic translation elongation | 29 | 1 | 5.64E−01 | 7.70E−01 | 0.75 | RPL22L1 |
| galactosyltransferase activity: GO | 29 | 1 | 5.64E−01 | 7.70E−01 | 0.75 | B3GNT3 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| induction of apoptosis through dr3 and dr4/5 death receptors | 29 | 1 | 5.64E−01 | 7.70E−01 | 0.75 | TNFSF10 |
| kinesin binding: GO | 29 | 1 | 5.64E−01 | 7.70E−01 | 0.75 | LRP8 |
| mannosylation: GO | 29 | 1 | 5.64E−01 | 7.70E−01 | 0.75 | SDF2L1 |
| myd88 independent toll like receptor signaling pathway: GO | 29 | 1 | 5.64E−01 | 7.70E−01 | 0.75 | TNIP3 |
| migration: GO | 29 | 1 | 5.64E−01 | 7.70E−01 | 0.75 | HMOX1 |
| negative regulation of potassium ion transport: GO | 29 | 1 | 5.64E−01 | 7.70E−01 | 0.75 | ADCYAP1 |
| neuron projection regeneration: GO | 29 | 1 | 5.64E−01 | 7.70E−01 | 0.75 | TNC |
| patterning of blood vessels: GO | 29 | 1 | 5.64E−01 | 7.70E−01 | 0.75 | BAK1 |
| binding: GO | 29 | 1 | 5.64E−01 | 7.70E−01 | 0.75 | FAM83A |
| phosphatidylserine binding: GO | 29 | 1 | 5.64E−01 | 7.70E−01 | 0.75 | HSPA8 |
| positive regulation of interferon beta production: GO | 29 | 1 | 5.64E−01 | 7.70E−01 | 0.75 | POLR3G |
| positive regulation of smooth muscle cell migration: GO | 29 | 1 | 5.64E−01 | 7.70E−01 | 0.75 | PLAU |
| vasoconstriction: GO | 29 | 1 | 5.64E−01 | 7.70E−01 | 0.75 | PTAFR |
| organization: GO | 29 | 1 | 5.64E−01 | 7.70E−01 | 0.75 | LIPG |
| regulation of defense response to virus by virus: GO | 29 | 1 | 5.64E−01 | 7.70E−01 | 0.75 | AP1S3 |
| regulation of dna templated transcription initiation: GO | 29 | 1 | 5.64E−01 | 7.70E−01 | 0.75 | FOSL1 |
| regulation of pten gene transcription | 29 | 1 | 5.64E−01 | 7.70E−01 | 0.75 | CBX2 |
| transport: GO | 29 | 1 | 5.64E−01 | 7.70E−01 | 0.75 | RIMS3 |
| replisome: GO | 29 | 1 | 5.64E−01 | 7.70E−01 | 0.75 | PCNA |
| retinoic acid pathway | 29 | 1 | 5.64E−01 | 7.70E−01 | 0.75 | CDK1 |
| rna polymerase | 29 | 1 | 5.64E−01 | 7.70E−01 | 0.75 | POLR3G |
| signaling by retinoic acid | 29 | 1 | 5.64E−01 | 7.70E−01 | 0.75 | RDH16 |
| syndecan 2 pathway | 29 | 1 | 5.64E−01 | 7.70E−01 | 0.75 | CSF2 |
| thyroid cancer | 29 | 1 | 5.64E−01 | 7.70E−01 | 0.75 | NTRK1 |
| thyroid hormone receptor binding: GO | 29 | 1 | 5.64E−01 | 7.70E−01 | 0.75 | OASL |
| vegf pathway | 29 | 1 | 5.64E−01 | 7.70E−01 | 0.75 | HIF1A |
| neurotransmitter receptor binding and downstream transmission in the postsynaptic cell | 121 | 5 | 5.67E−01 | 7.73E−01 | 0.90 | CHRNA3; CHRNA6; CHRNA9; GNGT2; KCNJ15 |
| nucleus organization: GO | 121 | 5 | 5.67E−01 | 7.73E−01 | 0.90 | CCNB1; CCNB2; CDK1; CEP55; PLK1 |
| asparagine n-linked glycosylation | 189 | 8 | 5.69E−01 | 7.74E−01 | 0.93 | AREG; CALR; CTSC; ST8S1A2; TGFA; TUBA1C; TUBB2A; TUBB6 |
| helicase activity: GO | 144 | 6 | 5.69E−01 | 7.74E−01 | 0.91 | BLM; CDC45; DDX21; DDX60L; EIF4A3; PIFI |
| beta-catenin independent wnt signaling | 76 | 3 | 5.71E−01 | 7.74E−01 | 0.86 | PSMA5; PSMB6; WNT5A |
| binding: GO | 53 | 2 | 5.72E−01 | 7.74E−01 | 0.83 | EOMES; IFI27 |
| basal cell carcinoma | 53 | 2 | 5.72E−01 | 7.74E−01 | 0.83 | WNT5A; WNT7A |
| cardiac ventricle morphogenesis: GO | 53 | 2 | 5.72E−01 | 7.74E−01 | 0.83 | FOXF1; HIF1A |
| degradation of beta-catenin by the destruction complex | 53 | 2 | 5.72E−01 | 7.74E−01 | 0.83 | PSMA5; PSMB6 |
| forebrain generation of neurons: GO | 53 | 2 | 5.72E−01 | 7.74E−01 | 0.83 | ASPM; WNT5A |
| glucan metabolic process: GO | 53 | 2 | 5.72E−01 | 7.74E−01 | 0.83 | PGM2; PYGL |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| main axon: GO | 53 | 2 | 5.72E−01 | 7.74E−01 | 0.83 | CCK; CNTNAP2 |
| myosin binding: GO | 53 | 2 | 5.72E−01 | 7.74E−01 | 0.83 | CXCR4; PYCARD |
| microtubule: GO | 53 | 2 | 5.72E−01 | 7.74E−01 | 0.83 | HIF1A; KIF23 |
| outflow tract morphogenesis: GO | 53 | 2 | 5.72E−01 | 7.74E−01 | 0.83 | HIF1A; WNT5A |
| valine, leucine and isoleucine degradation | 53 | 2 | 5.72E−01 | 7.74E−01 | 0.83 | ALDH1A3; ESCO2 |
| vasculogenesis: GO | 53 | 2 | 5.72E−01 | 7.74E−01 | 0.83 | FOXF1; WNT7A |
| integrin binding: GO | 99 | 4 | 5.72E−01 | 7.74E−01 | 0.88 | ADAM23; CALR; ESM1; ITGB6 |
| negative regulation of protein complex assembly: GO | 99 | 4 | 5.72E−01 | 7.74E−01 | 0.88 | EIF4EBP1; KIF14; MEFV; TWF1 |
| adipose tissue development: GO | 30 | 1 | 5.78E−01 | 7.74E−01 | 0.73 | NAMPT |
| adp binding: GO | 30 | 1 | 5.78E−01 | 7.74E−01 | 0.73 | VCP |
| blood vessel remodeling: GO | 30 | 1 | 5.78E−01 | 7.74E−01 | 0.73 | BAK1 |
| cdc42 reg pathway | 30 | 1 | 5.78E−01 | 7.74E−01 | 0.73 | NME1 |
| cellular response to dsrna: GO | 30 | 1 | 5.78E−01 | 7.74E−01 | 0.73 | RALB |
| dna polymerase activity: GO | 30 | 1 | 5.78E−01 | 7.74E−01 | 0.73 | POLQ |
| endocardial cushion development: GO | 30 | 1 | 5.78E−01 | 7.74E−01 | 0.73 | FOXF1 |
| eukaryotic translation termination | 30 | 1 | 5.78E−01 | 7.74E−01 | 0.73 | RPL22L1 |
| extension of telomeres | 30 | 1 | 5.78E−01 | 7.74E−01 | 0.73 | PCNA |
| fanconi anemia pathway | 30 | 1 | 5.78E−01 | 7.74E−01 | 0.73 | UBE2T |
| differentiation: GO | 30 | 1 | 5.78E−01 | 7.74E−01 | 0.73 | WNT5A |
| membrane biogenesis: GO | 30 | 1 | 5.78E−01 | 7.74E−01 | 0.73 | NLGN4X |
| myd88 dependent toll like receptor signaling pathway: GO | 30 | 1 | 5.78E−01 | 7.74E−01 | 0.73 | MYD88 |
| negative regulation of dna biosynthetic process: GO | 30 | 1 | 5.78E−01 | 7.74E−01 | 0.73 | PIF1 |
| negative regulation of response to extracellular stimulus: GO | 30 | 1 | 5.78E−01 | 7.74E−01 | 0.73 | CCK |
| negative regulation of tor signaling: GO | 30 | 1 | 5.78E−01 | 7.74E−01 | 0.73 | HIF1A |
| signaling | 30 | 1 | 5.78E−01 | 7.74E−01 | 0.73 | ISG15 |
| neuron projection membrane: GO | 30 | 1 | 5.78E−01 | 7.74E−01 | 0.73 | CNTNAP2 |
| oligodendrocyte development: GO | 30 | 1 | 5.78E−01 | 7.74E−01 | 0.73 | GSTP1 |
| organellar large ribosomal subunit: GO | 30 | 1 | 5.78E−01 | 7.74E−01 | 0.73 | MRPL51 |
| phospholipase c activity: GO | 30 | 1 | 5.78E−01 | 7.74E−01 | 0.73 | CCR5 |
| photoreceptor cell maintenance: GO | 30 | 1 | 5.78E−01 | 7.74E−01 | 0.73 | CNGB1 |
| transport: GO | 30 | 1 | 5.78E−01 | 7.74E−01 | 0.73 | ATP1B3 |
| protein serine threonine kinase inhibitor activity: GO | 30 | | 5.78E−01 | 7.74E−01 | 0.73 | SFN |
| ran gtpase binding: GO | 30 | 1 | 5.78E−01 | 7.74E−01 | 0.73 | BIRC5 |
| regulation of centrosome duplication: GO | 30 | 1 | 5.78E−01 | 7.74E−01 | 0.73 | PLK2 |
| regulation of glucokinase by glucokinase regulatory protein | 30 | 1 | 5.78E−01 | 7.74E−01 | 0.73 | GK |
| regulation of gluconeogenesis: GO | 30 | 1 | 5.78E−01 | 7.74E−01 | 0.73 | IL6 |
| regulation of organ formation: GO | 30 | 1 | 5.78E−01 | 7.74E−01 | 0.73 | WNT5A |
| cascade: GO | 30 | 1 | 5.78E−01 | 7.74E−01 | 0.73 | C1QBP |
| regulation of transcription from rna polymerase ii promoter in response to hypoxia: GO | 30 | 1 | 5.78E−01 | 7.74E−01 | 0.73 | HIF1A |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| renal water homeostasis: GO | 30 | 1 | 5.78E−01 | 7.74E−01 | 0.73 | AQP3 |
| rna polymerase binding: GO | 30 | 1 | 5.78E−01 | 7.74E−01 | 0.73 | PPIB |
| sulfur compound transport: GO | 30 | 1 | 5.78E−01 | 7.74E−01 | 0.73 | SLC26A9 |
| transcriptional activity of smad2/smad3:smad4 heterotrimer | 30 | 1 | 5.78E−01 | 7.74E−01 | 0.73 | SERPINE1 |
| organelle disassembly: GO | 168 | 7 | 5.79E−01 | 7.74E−01 | 0.91 | CDK1; FGFBP1; HK2; NEFM; RIMS3; SNRPF; TREM1 |
| amide transport: GO | 77 | 3 | 5.81E−01 | 7.75E−01 | 0.85 | AQP3; IL6; TAP2 |
| anion channel activity: GO | 77 | 3 | 5.81E−01 | 7.75E−01 | 0.85 | CLCA2; LRRC8D; SLC26A9 |
| cardiac septum development: GO | 77 | 3 | 5.81E−01 | 7.75E−01 | 0.85 | PRDM1; STRA6; WNT5A |
| erbb signaling pathway: GO | 77 | 3 | 5.81E−01 | 7.75E−01 | 0.85 | AREG; FAM83A; HBEGF |
| binding: GO | 77 | 3 | 5.81E−01 | 7.75E−01 | 0.85 | AURKA; RALB; SLPI |
| segmentation: GO | 77 | 3 | 5.81E−01 | 7.75E−01 | 0.85 | FOXF1; RGS20; WNT5A |
| trans golgi network membrane: GO | 77 | 3 | 5.81E−01 | 7.75E−01 | 0.85 | AP1S3; MYO1B; RAB31 |
| mesenchymal cell differentiation: GO | 123 | 5 | 5.82E−01 | 7.76E−01 | 0.89 | EOMES; HIF1A; HMGA2; STAT1; WNT5A |
| blastocyst development: GO | 54 | 2 | 5.83E−01 | 7.76E−01 | 0.81 | EOMES; NEK2 |
| eph-ephrin signaling | 54 | 2 | 5.83E−01 | 7.76E−01 | 0.81 | MMP9; SHB |
| golgi associated vesicle biogenesis | 54 | 2 | 5.83E−01 | 7.76E−01 | 0.81 | AP1S3; HSPA8 |
| contraction: GO | 54 | 2 | 5.83E−01 | 7.76E−01 | 0.81 | CHRNA3; PTAFR |
| ion channel binding: GO | 101 | 4 | 5.89E−01 | 7.81E−01 | 0.87 | BAK1; HOMER1; RIMS3; YWHAQ |
| development: GO | 101 | 4 | 5.89E−01 | 7.81E−01 | 0.87 | CDK1; GRHL3; PHLDA2; WNT5A |
| cell junction assembly: GO | 124 | 5 | 5.89E−01 | 7.81E−01 | 0.88 | ECT2; FBLIM1; FSCN1; GJB2; VMP1 |
| jnk cascade: GO | 78 | 3 | 5.90E−01 | 7.81E−01 | 0.84 | DUSP9; MDFI; WNT5A |
| lipoprotein biosynthetic process: GO | 78 | 3 | 5.90E−01 | 7.81E−01 | 0.84 | OAS2; PIGW; PLAUR |
| positive regulation of chromatin modification: GO | 78 | 3 | 5.90E−01 | 7.81E−01 | 0.84 | CCNB1; HIST1H1B; IL1B |
| ruffle membrane: GO | 78 | 3 | 5.90E−01 | 7.81E−01 | 0.84 | FERMT1; NME1; TWF1 |
| alpha synuclein pathway | 31 | 1 | 5.92E−01 | 7.81E−01 | 0.71 | KLK6 |
| basal plasma membrane: GO | 31 | 1 | 5.92E−01 | 7.81E−01 | 0.71 | CLCA2 |
| brain morphogenesis: GO | 31 | 1 | 5.92E−01 | 7.81E−01 | 0.71 | WNT5A |
| centrosome duplication: GO | 31 | 1 | 5.92E−01 | 7.81E−01 | 0.71 | STIL |
| cop9 signalosome: GO | 31 | 1 | 5.92E−01 | 7.81E−01 | 0.71 | HSPA6 |
| detection of visible light: GO | 31 | 1 | 5.92E−01 | 7.81E−01 | 0.71 | CNGB1 |
| egf pathway | 31 | 1 | 5.92E−01 | 7.81E−01 | 0.71 | STAT1 |
| er nucleus signaling pathway: GO | 31 | 1 | 5.92E−01 | 7.81E−01 | 0.71 | CALR |
| erk1 erk2 mapk pathway | 31 | 1 | 5.92E−01 | 7.81E−01 | 0.71 | DUSP9 |
| establishment of protein localization to vacuole: GO | 31 | 1 | 5.92E−01 | 7.81E−01 | 0.71 | HSPA8 |
| il3 pathway | 31 | 1 | 5.92E−01 | 7.81E−01 | 0.71 | OSM |
| insulin receptor binding: GO | 31 | 1 | 5.92E−01 | 7.81E−01 | 0.71 | DOK3 |
| mating: GO | 31 | 1 | 5.92E−01 | 7.81E−01 | 0.71 | PI3 |
| negative regulation of mapk pathway | 31 | 1 | 5.92E−01 | 7.81E−01 | 0.71 | DUSP9 |
| p38 alpha beta pathway | 31 | 1 | 5.92E−01 | 7.81E−01 | 0.71 | RALB |
| positive regulation of dendrite morphogenesis: GO | 31 | 1 | 5.92E−01 | 7.81E−01 | 0.71 | LRP8 |
| regulation of actin filament based movement: GO | 31 | 1 | 5.92E−01 | 7.81E−01 | 0.71 | DSC2 |
| regulation of sterol transport: GO | 31 | 1 | 5.92E−01 | 7.81E−01 | 0.71 | LIPG |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| somatic cell dna recombination: GO | 31 | 1 | 5.92E−01 | 7.81E−01 | 0.71 | EXO1 |
| translation regulator activity: GO | 31 | 1 | 5.92E−01 | 7.81E−01 | 0.71 | EIF4EBP1 |
| adenylate cyclase inhibiting g protein coupled receptor signaling pathway: GO | 55 | 2 | 5.93E−01 | 7.82E−01 | 0.80 | HRH3; RGS1 |
| erbb signaling pathway | 55 | 2 | 5.93E−01 | 7.82E−01 | 0.80 | EIF4EBP1; TGFA |
| ovarian follicle development: GO | 55 | 2 | 5.93E−01 | 7.82E−01 | 0.80 | ADCYAP1; CCNE1 |
| peptide transport: GO | 55 | 2 | 5.93E−01 | 7.82E−01 | 0.80 | IL6; TAP2 |
| transport: GO | 55 | 2 | 5.93E−01 | 7.82E−01 | 0.80 | CHRNA3; RIMS3 |
| leading edge membrane: GO | 125 | 5 | 5.97E−01 | 7.85E−01 | 0.87 | CNTNAP2; FERMT1; NME1; SLC39A6; TWF1 |
| male sex differentiation: GO | 125 | 5 | 5.97E−01 | 7.85E−01 | 0.87 | ASPM; GJB2; KIF18A; NTRK1; WNT5A |
| tube formation: GO | 125 | 5 | 5.97E−01 | 7.85E−01 | 0.87 | GRHL3; HIF1A; STIL; TGM2; WNT5A |
| innate immune response activating cell surface receptor signaling pathway: GO | 102 | 4 | 5.97E−01 | 7.85E−01 | 0.86 | CLEC7A; PSMA4; PSMA5; PSMB6 |
| regulation of calcium ion transmembrane transport: GO | 102 | 4 | 5.97E−01 | 7.85E−01 | 0.86 | CXCL10; CXCL11; CXCL9; GSTO1 |
| cell adhesion molecule binding: GO | 171 | 7 | 5.98E−01 | 7.86E−01 | 0.90 | ADAM23; CALR; CDK5R1; ESM1; ITGB6; NLGN4X; SELL |
| cell junction organization: GO | 171 | 7 | 5.98E−01 | 7.86E−01 | 0.90 | CDH3; ECT2; FBLIM1; FSCN1; GJB2; NLGN4X; VMP1 |
| parkinsons disease | 79 | 3 | 5.99E−01 | 7.86E−01 | 0.83 | COX7B; CYCS; SLC25A5 |
| protein folding: GO | 194 | 8 | 5.99E−01 | 7.86E−01 | 0.90 | CALR; CCT5; FKBPL; HSPA6; HSPA8; PPIB; PPIF; PPIL1 |
| cardiac muscle tissue development: GO | 126 | 5 | 6.04E−01 | 7.86E−01 | 0.87 | CALR; CCNB1; CDK1; NDRG4; WNT5A |
| chondrocyte differentiation: GO | 56 | 2 | 6.04E−01 | 7.86E−01 | 0.78 | HMGA2; WNT7A |
| cul3 ring ubiquitin ligase complex: GO | 56 | 2 | 6.04E−01 | 7.86E−01 | 0.78 | KBTBD8; KLHDC7B |
| embryonic digit morphogenesis: GO | 56 | 2 | 6.04E−01 | 7.86E−01 | 0.78 | WNT5A; WNT7A |
| hiv-i nef: negative effector of fas and tnf | 56 | 2 | 6.04E−01 | 7.86E−01 | 0.78 | LMNB1; LMNB2 |
| kinase activator activity: GO | 56 | 2 | 6.04E−01 | 7.86E−01 | 0.78 | CDK5R1; LTF |
| mitochondrial protein import | 56 | 2 | 6.04E−01 | 7.86E−01 | 0.78 | TIMM13; TIMM8B |
| vascular smooth muscle contraction | 103 | 4 | 6.05E−01 | 7.86E−01 | 0.85 | CALML3; CALML5; PLA2G3; PRKCQ |
| basolateral plasma membrane: GO | 195 | 8 | 6.05E−01 | 7.86E−01 | 0.90 | AQP3; ATP12A; CLCA2; LDLR; NDRG4; RHCG; SLC2A9; TGFA |
| regulated exocytosis: GO | 195 | 9 | 6.05E−01 | 7.86E−01 | 0.90 | CCL3; NR4A3; PLA2G3; RAB31; RIMS3; SERPINA1; SERPINE1; SRGN |
| axoneme assembly: GO | 32 | 1 | 6.05E−01 | 7.86E−01 | 0.68 | PLA2G3 |
| b cell activation involved in immune response: GO | 32 | 1 | 6.05E−01 | 7.86E−01 | 0.68 | EXO1 |
| ca2+ pathway | 32 | 1 | 6.05E−01 | 7.86E−01 | 0.68 | WNT5A |
| cd40 pathway | 32 | 1 | 6.05E−01 | 7.86E−01 | 0.68 | JAK3 |
| cyclic nucleotide binding: GO | 32 | 1 | 6.05E−01 | 7.86E−01 | 0.68 | CNGB1 |
| hnf3b pathway | 32 | 1 | 6.05E−01 | 7.86E−01 | 0.68 | FOXF1 |
| lung epithelium development: GO | 32 | 1 | 6.05E−01 | 7.86E−01 | 0.68 | STRA6 |
| mitochondrion localization: GO | 32 | 1 | 6.05E−01 | 7.86E−01 | 0.68 | HIF1A |
| negative regulation of endothelial cell migration: GO | 32 | 1 | 6.05E−01 | 7.86E−01 | 0.68 | CXCL13 |
| pdgf pathway | 32 | 1 | 6.05E−01 | 7.86E−01 | 0.68 | STAT1 |
| positive regulation of cyclin dependent protein kinase activity: GO | 32 | 1 | 6.05E−01 | 7.86E−01 | 0.68 | CDC6 |
| protein-protein interactions at synapses | 32 | 1 | 6.05E−01 | 7.86E−01 | 0.68 | HOMER1 |
| process: GO | 32 | 1 | 6.05E−01 | 7.86E−01 | 0.68 | PHLDA2 |
| regulation of multicellular organismal metabolic process: GO | 32 | 1 | 6.05E−01 | 7.86E−01 | 0.68 | IL6 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| regulation of response to reactive oxygen species: GO | 32 | 1 | 6.05E−01 | 7.86E−01 | 0.68 | NR4A3 |
| regulation of the actin cytoskeleton by rho gtpases | 32 | 1 | 6.05E−01 | 7.86E−01 | 0.68 | FSCN1 |
| response to ph: GO | 32 | 1 | 6.05E−01 | 7.86E−01 | 0.68 | GPR65 |
| sema4d in semaphorin signaling | 32 | 1 | 6.05E−01 | 7.86E−01 | 0.68 | RAC2 |
| recombination: GO | 32 | 1 | 6.05E−01 | 7.86E−01 | 0.68 | PCNA |
| trna transport: GO | 32 | 1 | 6.05E−01 | 7.86E−01 | 0.68 | RAN |
| wnt noncanonical pathway | 32 | 1 | 6.05E−01 | 7.86E−01 | 0.68 | WNT5A |
| cysteine type endopeptidase activity: GO | 80 | 3 | 6.08E−01 | 7.88E−01 | 0.82 | CTSB; CTSC; PYCARD |
| myd88 mal cascade initiated on plasma membrane | 80 | 3 | 6.08E−01 | 7.88E−01 | 0.82 | CDK1; MYD88; S100A12 |
| nik nf kappab signaling: GO | 80 | 3 | 6.08E−01 | 7.88E−01 | 0.82 | PSMA4; PSMA5; PSMB6 |
| regulation of cation channel activity: GO | 80 | 3 | 6.08E−01 | 7.88E−01 | 0.82 | GSTO1; HOMER1; MMP9 |
| t cell receptor signaling pathway | 80 | 3 | 6.08E−01 | 7.88E−01 | 0.82 | CSF2; CTLA4; ICOS |
| axon part: GO | 196 | 8 | 6.11E−01 | 7.92E−01 | 0.89 | ADCYAP1; AURKA; CCK; CNTNAP2; HIF1A; KIF4A; SNCB; TPX2 |
| epithelium: GO | 127 | 5 | 6.11E−01 | 7.92E−01 | 0.86 | ALDH1A3; GRHL3; HIF1A; STIL; WNT5A |
| ion channel transport | 104 | 4 | 6.13E−01 | 7.92E−01 | 0.84 | ATP12A; ATP1B3; GLTP; HTR3A |
| metabolism of steroids | 104 | 4 | 6.13E−01 | 7.92E−01 | 0.84 | AKR1B10; CYP24A1; CYP27B1; SQLE |
| differentiation: GO | 104 | 4 | 6.13E−01 | 7.92E−01 | 0.84 | AREG; IFITM1; IL6; LTF |
| transport | 104 | 4 | 6.13E−01 | 7.92E−01 | 0.84 | COX7B; CYCS; LDHA; SLC16A1 |
| post translational protein modification | 57 | 2 | 6.14E−01 | 7.92E−01 | 0.77 | GALNT6; GCNT4 |
| preribosome: GO | 57 | 2 | 6.14E−01 | 7.92E−01 | 0.77 | EBNA1BP2; EIF6 |
| regulation of mrna splicing via spliceosome: GO | 57 | 2 | 6.14E−01 | 7.92E−01 | 0.77 | C1QBP; HSPA8 |
| palate development: GO | 81 | 3 | 6.17E−01 | 7.92E−01 | 0.81 | FOXE1; WNT5A; WNT7A |
| circulation: GO | 81 | 3 | 6.17E−01 | 7.92E−01 | 0.81 | ADCYAP1; HMOX1; PTAFR |
| pten regulation | 81 | 3 | 6.17E−01 | 7.92E−01 | 0.81 | CBX2; PSMA5; PSMB6 |
| regulation of insulin secretion | 81 | 3 | 6.17E−01 | 7.92E−01 | 0.81 | GNA15; GNGT2; SLC25A5 |
| regulation of lipid transport: GO | 81 | 3 | 6.17E−01 | 7.92E−01 | 0.81 | IL1B; LIPG; PRELID1 |
| activity: GO | 33 | 1 | 6.18E−01 | 7.92E−01 | 0.66 | ADCYAP1 |
| camp mediated signaling: GO | 33 | 1 | 6.18E−01 | 7.92E−01 | 0.66 | ADCYAP1 |
| carbohydrate derivative transporter activity: GO | 33 | 1 | 6.18E−01 | 7.92E−01 | 0.66 | GLTP |
| formation of a pool of free 40s subunits | 33 | 1 | 6.18E−01 | 7.92E−01 | 0.66 | RPL22L1 |
| global genomic ner gg ner | 33 | 1 | 6.18E−01 | 7.92E−01 | 0.66 | PCNA |
| proteins | 33 | 1 | 6.18E−01 | 7.92E−01 | 0.66 | SL C25A5 |
| mapk trk pathway | 33 | 1 | 6.18E−01 | 7.92E−01 | 0.66 | CDK5R1 |
| myoblast differentiation: GO | 33 | 1 | 6.18E−01 | 7.92E−01 | 0.66 | PITX1 |
| negative regulation of actin filament depolymerization: GO | 33 | 1 | 6.18E−01 | 7.92E−01 | 0.66 | TWF1 |
| nuclear signaling by erbb4 | 33 | 1 | 6.18E−01 | 7.92E−01 | 0.66 | HBEGF |
| one carbon metabolic process: GO | 33 | 1 | 6.18E−01 | 7.92E−01 | 0.66 | AHCY |
| positive regulation of dendritic spine development: GO | 33 | 1 | 6.18E−01 | 7.92E−01 | 0.66 | LRP8 |
| positive regulation of epithelial to mesenchymal transition: GO | 33 | 1 | 6.18E−01 | 7.92E−01 | 0.66 | SERPINB3 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| transport: GO | 33 | 1 | 6.18E−01 | 7.92E−01 | 0.66 | NR4A3 |
| protein destabilization: GO | 33 | 1 | 6.18E−01 | 7.92E−01 | 0.66 | PLK1 |
| pteridine containing compound metabolic process: GO | 33 | 1 | 6.18E−01 | 7.92E−01 | 0.66 | GGH |
| regulation of sodium ion transmembrane transporter activity: GO | 33 | 1 | 6.18E−01 | 7.92E−01 | 0.66 | PCSK9 |
| regulation of transcription regulatory region dna binding: GO | 33 | 1 | 6.18E−01 | 7.92E−01 | 0.66 | HMGA2 |
| response to monoamine: GO | 33 | 1 | 6.18E−01 | 7.92E−01 | 0.66 | NR4A3 |
| transcriptional activation of mitochondrial biogenesis | 33 | 1 | 6.18E−01 | 7.92E−01 | 0.66 | CYCS |
| erbb1 downstream pathway | 105 | 4 | 6.21E−01 | 7.95E−01 | 0.83 | SFN; SH2D2A; STAT1; YWHAQ |
| connective tissue development: GO | 175 | 7 | 6.23E−01 | 7.98E−01 | 0.87 | HIF1A; HMGA2; HYAL3; NAMPT; PITX1; WNT5A; WNT7A |
| positive regulation of cell morphogenesis involved in differentiation: GO | 152 | 6 | 6.24E−01 | 7.98E−01 | 0.86 | C1QBP; CALR; CRABP2; LRP8; SERPINB3; TNFRSF12A |
| cellular response to retinoic acid: GO | 58 | 2 | 6.25E−01 | 7.99E−01 | 0.75 | TNC; WNT5A |
| er associated ubiquitin dependent protein catabolic process: GO | 58 | 2 | 6.25E−01 | 7.99E−01 | 0.75 | SDF2L1; VCP |
| rig i mda5 mediated induction of ifn alpha beta pathways | 58 | 2 | 6.25E−01 | 7.99E−01 | 0.75 | ISG15; S100A12 |
| platelet activation: GO | 129 | 5 | 6.25E−01 | 7.99E−01 | 0.85 | GNA15; IL6; PRKCQ; RAC2; SLC7A11 |
| ubiquitin mediated proteolysis | 129 | 5 | 6.25E−01 | 7.99E−01 | 0.85 | CDC20; SOCS3; UBE2C; UBE2F; UBE2S |
| neuromuscular process: GO | 82 | 3 | 6.25E−01 | 7.99E−01 | 0.80 | ALDH1A3; NR4A3; STRA6 |
| binding: GO | 82 | 3 | 6.25E−01 | 7.99E−01 | 0.80 | EIF5A; EIF5AL1; EIF6 |
| negative regulation of epithelial cell proliferation: GO | 106 | 4 | 6.28E−01 | 7.99E−01 | 0.83 | IL26; SFN; STAT1; WNT5A |
| sterol metabolic process: GO | 106 | 4 | 6.28E−01 | 7.99E−01 | 0.83 | CH25H; LDLR; PCSK9; SQLE |
| bone mineralization: GO | 34 | 1 | 6.31E−01 | 7.99E−01 | 0.64 | CYP27B1 |
| catecholamine metabolic process: GO | 34 | 1 | 6.31E−01 | 7.99E−01 | 0.64 | SNCB |
| channel inhibitor activity: GO | 34 | 1 | 6.31E−01 | 7.99E−01 | 0.64 | PCSK9 |
| death receptor signalling | 34 | 1 | 6.31E−01 | 7.99E−01 | 0.64 | TNFSF10 |
| developmental pigmentation: GO | 34 | 1 | 6.31E−01 | 7.99E−01 | 0.64 | RAB38 |
| gap-filling dna repair synthesis and ligation in te-ner | 34 | 1 | 6.31E−01 | 7.99E−01 | 0.64 | PCNA |
| heterophilic cell cell adhesion via plasma membrane cell adhesion molecules: GO | 34 | 1 | 6.31E−01 | 7.99E−01 | 0.64 | SELE |
| ion gated channel activity: GO | 34 | 1 | 6.31E−01 | 7.99E−01 | 0.64 | CLCA2 |
| transport | 34 | 1 | 6.31E−01 | 7.99E−01 | 0.64 | LDLR |
| membrane protein proteolysis: GO | 34 | 1 | 6.31E−01 | 7.99E−01 | 0.64 | PRKCQ |
| muscle fiber development: GO | 34 | 1 | 6.31E−01 | 7.99E−01 | 0.64 | HOMER1 |
| negative regulation of gliogenesis: GO | 34 | 1 | 6.31E−01 | 7.99E−01 | 0.64 | ADCYAP1 |
| negative regulation of mrna metabolic process: GO | 34 | 1 | 6.31E−01 | 7.99E−01 | 0.64 | C1QBP |
| neurodegenerative disorders | 34 | 1 | 6.31E−01 | 7.99E−01 | 0.64 | GAPDH |
| development: GO | 34 | 1 | 6.31E−01 | 7.99E−01 | 0.64 | TNC |
| palmitoyltransferase activity: GO | 34 | 1 | 6.31E−01 | 7.99E−01 | 0.64 | SPTSSA |
| pip3 signaling in b lymphocytes | 34 | 1 | 6.31E−01 | 7.99E−01 | 0.64 | NR4A3 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| positive regulation of cation channel activity: GO | 34 | 1 | 6.31E−01 | 7.99E−01 | 0.64 | GSTO1 |
| positive regulation of protein localization to cell periphery: GO | 34 | 1 | 6.31E−01 | 7.99E−01 | 0.64 | IFNG |
| assembly: GO | 34 | 1 | 6.31E−01 | 7.99E−01 | 0.64 | RALB |
| response to fluid shear stress: GO | 34 | 1 | 6.31E−01 | 7.99E−01 | 0.64 | PLAU |
| response to prostaglandin: GO | 34 | 1 | 6.31E−01 | 7.99E−01 | 0.64 | TNC |
| wnt signaling pathway calcium modulating pathway: GO | 34 | 1 | 6.31E−01 | 7.99E−01 | 0.64 | WNT5A |
| cardiac chamber development: GO | 130 | 5 | 6.32E−01 | 8.00E−01 | 0.84 | FOXF1; HIF1A; PRDM1; STRA6; WNT5A |
| pathway: GO | 130 | 5 | 6.32E−01 | 8.00E−01 | 0.84 | NR4A3; PRKCQ; PSMA4; PSMA5; PSMB6 |
| process: GO | 83 | 3 | 6.34E−01 | 8.00E−01 | 0.79 | AHCY; ALDH4A1; GOT2 |
| ecm-receptor interaction | 83 | 3 | 6.34E−01 | 8.00E−01 | 0.79 | HMMR; ITGB6; TNC |
| ephrin receptor signaling pathway: GO | 83 | 3 | 6.34E−01 | 8.00E−01 | 0.79 | CDK5R1; MMP9; NTRK1 |
| regulation of protein targeting to mitochondrion: GO | 83 | 3 | 6.34E−01 | 8.00E−01 | 0.79 | ITGAX; RAC2; UGCG |
| ca2+ | 83 | 3 | 6.34E−01 | 8.00E−01 | 0.79 | MANF; SERPINE1; SRGN |
| calcium ion import: GO | 59 | 2 | 6.34E−01 | 8.00E−01 | 0.74 | CCL3; CCR5 |
| cytosolic large ribosomal subunit: GO | 59 | 2 | 6.34E−01 | 8.00E−01 | 0.74 | RPL22L1; RPL26L1 |
| fas pathway | 59 | 2 | 6.34E−01 | 8.00E−01 | 0.74 | LMNB1; LMNB2 |
| modified amino acid binding: GO | 59 | 2 | 6.34E−01 | 8.00E−01 | 0.74 | GSTP1; HSPA8 |
| nerve development: GO | 59 | 2 | 6.34E−01 | 8.00E−01 | 0.74 | FBXO45; NTRK1 |
| protein serine threonine phosphatase activity: GO | 59 | 2 | 6.34E−01 | 8.00E−01 | 0.74 | CDKN3; CYCS |
| complex: GO | 59 | 2 | 6.34E−01 | 8.00E−01 | 0.74 | SNRPF; SNRPG |
| purine containing compound biosynthetic process: GO | 107 | 4 | 6.36E−01 | 8.00E−01 | 0.82 | NME1; OAS1; OAS2; PNP |
| gliogenesis: GO | 154 | 6 | 6.37E−01 | 8.00E−01 | 0.85 | AREG; CCL3; CDK5R1; GSTP1; S100A8; S100A9 |
| purine metabolism | 154 | 6 | 6.37E−01 | 8.00E−01 | 0.85 | NME1; PKM; PNP; POLR3G; RRM2; TYMP |
| regulation of cell substrate adhesion: GO | 154 | 6 | 6.37E−01 | 8.00E−01 | 0.85 | C1QBP; CALR; FOXF1; PLAU; RAC2; SERPINE1 |
| neurotransmitter transport: GO | 131 | 5 | 6.39E−01 | 8.00E−01 | 0.83 | HRH3; HSPA8; RIMS3; SLC6A11; WNT7A |
| regulation of response to dna damage stimulus: GO | 131 | 5 | 6.39E−01 | 8.00E−01 | 0.83 | FOXM1; H2AFX; HMGA2; PCNA; POLQ |
| canonical wnt signaling pathway: GO | 84 | 3 | 6.42E−01 | 8.00E−01 | 0.78 | CDH3; WNT5A; WNT7A |
| potassium channels | 84 | 3 | 6.42E−01 | 8.00E−01 | 0.78 | GNGT2; KCNJ15; KCNK10 |
| amino sugar metabolic process: GO | 35 | 1 | 6.43E−01 | 8.00E−01 | 0.62 | CHI3L2 |
| anatomical structure maturation: GO | 35 | 1 | 6.43E−01 | 8.00E−01 | 0.62 | CDK5R1 |
| arf6 pathway | 35 | 1 | 6.43E−01 | 8.00E−01 | 0.62 | GNA15 |
| development: GO | 35 | 1 | 6.43E−01 | 8.00E−01 | 0.62 | NTRK1 |
| cell communication involved in cardiac conduction: GO | 35 | 1 | 6.43E−01 | 8.00E−01 | 0.62 | DSC2 |
| coronary vasculature development: GO | 35 | 1 | 6.43E−01 | 8.00E−01 | 0.62 | PRDM1 |
| dual incision in tc-ner | 35 | 1 | 6.43E−01 | 8.00E−01 | 0.62 | PCNA |
| endoplasmic reticulum organization: GO | 35 | 1 | 6.43E−01 | 8.00E−01 | 0.62 | VMP1 |
| erbb1 receptor proximal pathway | 35 | 1 | 6.43E−01 | 8.00E−01 | 0.62 | STAT1 |
| ga13 pathway | 35 | 1 | 6.43E−01 | 8.00E−01 | 0.62 | PI3 |
| glucose transport | 35 | 1 | 6.43E−01 | 8.00E−01 | 0.62 | HK2 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| head morphogenesis: GO | 35 | 1 | 6.43E−01 | 8.00E−01 | 0.62 | STRA6 |
| hiv nef pathway | 35 | 1 | 6.43E−01 | 8.00E−01 | 0.62 | CYCS |
| hnf3a pathway | 35 | 1 | 6.43E−01 | 8.00E−01 | 0.62 | SERPINA1 |
| negative regulation of osteoblast differentiation: GO | 35 | 1 | 6.43E−01 | 8.00E−01 | 0.62 | AREG |
| p38 mapk signaling pathway | 35 | 1 | 6.43E−01 | 8.00E−01 | 0.62 | STAT1 |
| platelet aggregation: GO | 35 | 1 | 6.43E−01 | 8.00E−01 | 0.62 | SLC7A11 |
| polysome: GO | 35 | 1 | 6.43E−01 | 8.00E−01 | 0.62 | CALR |
| positive regulation of axon extension: GO | 35 | 1 | 6.43E−01 | 8.00E−01 | 0.62 | TNFRSF12A |
| positive regulation of biomineral tissue development: GO | 35 | 1 | 6.43E−01 | 8.00E−01 | 0.62 | LTF |
| posttranscriptional gene silencing: GO | 35 | 1 | 6.43E−01 | 8.00E−01 | 0.62 | RAN |
| rab geranylgeranylation | 35 | 1 | 6.43E−01 | 8.00E−01 | 0.62 | RAB31 |
| regulation of endothelial cell apoptotic process: GO | 35 | 1 | 6.43E−01 | 8.00E−01 | 0.62 | SERPINE1 |
| distribution: GO | 35 | 1 | 6.43E−01 | 8.00E−01 | 0.62 | PRELID1 |
| stereocilium bundle: GO | 35 | 1 | 6.43E−01 | 8.00E−01 | 0.62 | IDO1 |
| vesicle cytoskeletal trafficking: GO | 35 | 1 | 6.43E−01 | 8.00E−01 | 0.62 | KIF23 |
| atpase activity coupled to movement of substances: GO | 108 | 4 | 6.44E−01 | 8.00E−01 | 0.81 | ABCG4; ATP12A; ATP1B3; TAP2 |
| membrane budding: GO | 108 | 4 | 6.44E−01 | 8.00E−01 | 0.81 | AREG; CTSC; SERPINA1; TGFA |
| toll receptor cascades | 108 | 4 | 6.44E−01 | 8.00E−01 | 0.81 | CDK1; CTSB; MYD88; S100A12 |
| cardiac muscle contraction | 60 | 2 | 6.44E−01 | 8.00E−01 | 0.73 | ATP1B3; COX7B |
| monosaccharide binding: GO | 60 | 2 | 6.44E−01 | 8.00E−01 | 0.73 | HK2; PYGL |
| negative regulation of nf kappab transcription factor activity: GO | 60 | 2 | 6.44E−01 | 8.00E−01 | 0.73 | PYCARD; ZC3H12A |
| nucleoside monophosphate biosynthetic process: GO | 60 | 2 | 6.44E−01 | 8.00E−01 | 0.73 | TK1; UPP1 |
| organ growth: GO | 60 | 2 | 6.44E−01 | 8.00E−01 | 0.73 | NDRG4; NLGN4X |
| development: GO | 60 | 2 | 6.44E−01 | 8.00E−01 | 0.73 | ARTN; OSM |
| protein polymerization: GO | 60 | 2 | 6.44E−01 | 8.00E−01 | 0.73 | UBE2C; UBE2S |
| aggregation | 179 | 7 | 6.47E−01 | 8.02E−01 | 0.86 | GNA15; GNGT2; PRKCQ; RAC2; SERPINA1; SERPINE1; SRGN |
| colorectal cancer | 85 | 3 | 6.51E−01 | 8.02E−01 | 0.77 | BIRC5; CYCS; RAC2 |
| ensheathment of neurons: GO | 85 | 3 | 6.51E−01 | 8.02E−01 | 0.77 | CXCR4; KLK6; TNFRSF21 |
| prostate cancer | 85 | 3 | 6.51E−01 | 8.02E−01 | 0.77 | CCNE1; GSTP1; TGFA |
| regulation of mrna metabolic process: GO | 109 | 4 | 6.51E−01 | 8.02E−01 | 0.80 | C1QBP; CCNB1; HSPA8; ZC3H12A |
| localization: GO | 109 | 4 | 6.51E−01 | 8.02E−01 | 0.80 | EIF4A3; EIF5A; EIF6; RAN |
| hydrolase activity acting on carbon nitrogen but not peptide bonds: GO | 133 | 5 | 6.53E−01 | 8.02E−01 | 0.82 | APOBEC3A; APOBEC3B; PGLYRP2; VNN3; ZBP1 |
| atpase coupled ion transmembrane transporter activity: GO | 61 | 2 | 6.54E−01 | 8.02E−01 | 0.72 | ATP12A; ATP1B3 |
| b cell receptor signaling pathway | 61 | 2 | 6.54E−01 | 8.02E−01 | 0.72 | IFITM1; RAC2 |
| central nervous system neuron development: GO | 61 | 2 | 6.54E−01 | 8.02E−01 | 0.72 | FBXO45; WNT5A |
| myc repress pathway | 61 | 2 | 6.54E−01 | 8.02E−01 | 0.72 | S100A7; WNT5A |
| negative regulation of axonogenesis: GO | 61 | 2 | 6.54E−01 | 8.02E−01 | 0.72 | CDK5R1; WNT5A |
| network | 61 | 2 | 6.54E−01 | 8.02E−01 | 0.72 | HBEGF; MYD88 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| phosphatidylinositol 3 kinase activity: GO | 61 | 2 | 6.54E−01 | 8.02E−01 | 0.72 | CD80; HBEGF |
| regulation of dna templated transcription in response to stress: GO | 61 | 2 | 6.54E−01 | 8.02E−01 | 0.72 | HIF1A; HMOX1 |
| (srebp) | 36 | 1 | 6.55E−01 | 8.02E−01 | 0.61 | SQLE |
| amyotrophic lateral sclerosis als | 36 | 1 | 6.55E−01 | 8.02E−01 | 0.61 | CYCS |
| branching involved in ureteric bud morphogenesis: GO | 36 | 1 | 6.55E−01 | 8.02E−01 | 0.61 | PGF |
| chromosome organization involved in meiotic cell cycle: GO | 36 | 1 | 6.55E−01 | 8.02E−01 | 0.61 | TRIP13 |
| enzymes | 36 | 1 | 6.55E−01 | 8.02E−01 | 0.61 | PPIB |
| interstrand cross link repair: GO | 36 | 1 | 6.55E−01 | 8.02E−01 | 0.61 | UBE2T |
| 113a-mediated translational silencing of ceruloplasmin expression | 36 | 1 | 6.55E−01 | 8.02E−01 | 0.61 | RPL22L1 |
| multicellular organismal movement: GO | 36 | 1 | 6.55E−01 | 8.02E−01 | 0.61 | HOMER1 |
| negative regulation of bmp signaling pathway: GO | 36 | 1 | 6.55E−01 | 8.02E−01 | 0.61 | WNT5A |
| 0-linked glycosylation | 36 | 1 | 6.55E−01 | 8.02E−01 | 0.61 | B3GNT3 |
| oxidative phosphorylation | 36 | 1 | 6.55E−01 | 8.02E−01 | 0.61 | ATP12A |
| oxygen binding: GO | 36 | 1 | 6.55E−01 | 8.02E−01 | 0.61 | TDO2 |
| ph reduction: GO | 36 | 1 | 6.55E−01 | 8.02E−01 | 0.61 | RAB38 |
| pi3k events in erbb4 signaling | 36 | 1 | 6.55E−01 | 8.02E−01 | 0.61 | HBEGF |
| positive regulation of potassium ion transport: GO | 36 | 1 | 6.55E−01 | 8.02E−01 | 0.61 | ATP1B3 |
| acetylation: GO | 36 | 1 | 6.55E−01 | 8.02E−01 | 0.61 | IL1B |
| positive regulation of small gtpase mediated signal transduction: GO | 36 | 1 | 6.55E−01 | 8.02E−01 | 0.61 | NTRK1 |
| immunity: GO | 36 | 1 | 6.55E−01 | 8.02E−01 | 0.61 | IFNG |
| regulation of insulin secretion by glucagon like peptide1 | 36 | 1 | 6.55E−01 | 8.02E−01 | 0.61 | GNGT2 |
| regulation of muscle hypertrophy: GO | 36 | 1 | 6.55E−01 | 8.02E−01 | 0.61 | NR4A3 |
| signal sequence binding: GO | 36 | 1 | 6.55E−01 | 8.02E−01 | 0.61 | KPNA2 |
| signaling by fgfr mutants | 36 | 1 | 6.55E−01 | 8.02E−01 | 0.61 | STAT1 |
| signaling by fgfr2 | 36 | 1 | 6.55E−01 | 8.02E−01 | 0.61 | FGFBP1 |
| sperm egg recognition: GO | 36 | 1 | 6.55E−01 | 8.02E−01 | 0.61 | CCT5 |
| biosythesis | 36 | 1 | 6.55E−01 | 8.02E−01 | 0.61 | ST8S1A2 |
| toll pathway | 36 | 1 | 6.55E−01 | 8.02E−01 | 0.61 | MYD88 |
| transcriptional activity of smad2 smad3 smad4 heterotrimer | 36 | 1 | 6.55E−01 | 8.02E−01 | 0.61 | SERPINE1 |
| tricarboxylic acid metabolic process: GO | 36 | 1 | 6.55E−01 | 8.02E−01 | 0.61 | OGDHL |
| regulation of response to extracellular stimulus: GO | 157 | 6 | 6.55E−01 | 8.02E−01 | 0.84 | CCK; CDK5R1; CYP27B1; GAPDH; HIF1A; RALB |
| sperm part: GO | 110 | 4 | 6.58E−01 | 8.04E−01 | 0.80 | ACRV1; CALR; ENKUR; RAN |
| development of primary sexual characteristics: GO | 181 | 7 | 6.59E−01 | 8.04E−01 | 0.85 | ADCYAP1; ASPM; CBX2; CCNE1; KIF18A; NTRK1; WNT5A |
| respiratory system development: GO | 181 | 7 | 6.59E−01 | 8.04E−01 | 0.85 | ALDH1A3; EIF4EBP1; FOXF1; STRA6; TIMELESS; TNC; WNT5A |
| alcohol binding: GO | 86 | 3 | 6.59E−01 | 8.04E−01 | 0.76 | ADAP2; ADH7; CRABP2 |
| motile cilium: GO | 86 | 3 | 6.59E−01 | 8.04E−01 | 0.76 | ENKUR; HIF1A; RAN |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| respiratory electron transport | 86 | 3 | 6.59E−01 | 8.04E−01 | 0.76 | COX7B; CYCS; SCO2 |
| solute cation symporter activity: GO | 86 | 3 | 6.59E−01 | 8.04E−01 | 0.76 | SLC2A9; SLC5A1; SLC6A11 |
| membrane fusion: GO | 134 | 5 | 6.59E−01 | 8.05E−01 | 0.82 | BAK1; BCL2A1; CCR5; CXCR4; DYSF |
| regulation of muscle contraction: GO | 134 | 5 | 6.59E−01 | 8.05E−01 | 0.82 | CHRNA3; DSC2; GSTO1; PTAFR; ZC3H12A |
| pi3k/akt activation | 158 | 6 | 6.62E−01 | 8.07E−01 | 0.83 | CBX2; HBEGF; MYD88; NTRK1; PSMA5; PSMB6 |
| cytoplasmic mrna processing body: GO | 62 | 2 | 6.63E−01 | 8.07E−01 | 0.71 | PSMA4; ZC3H12A |
| energy reserve metabolic process: GO | 62 | 2 | 6.63E−01 | 8.07E−01 | 0.71 | PGM2; PYGL |
| membrane | 62 | 2 | 6.63E−01 | 8.07E−01 | 0.71 | MYD88; S100A12 |
| toll like receptor 10 (tlr10) cascade | 62 | 2 | 6.63E−01 | 8.07E−01 | 0.71 | MYD88; S100A12 |
| toll like receptor 5 (tlr5) cascade | 62 | 2 | 6.63E−01 | 8.07E−01 | 0.71 | MYD88; S100A12 |
| sh3 domain binding: GO | 111 | 4 | 6.65E−01 | 8.07E−01 | 0.79 | CD3E; ENKUR; PTTG1; SH2D2A |
| cellular respiration: GO | 135 | 5 | 6.66E−01 | 8.07E−01 | 0.81 | COX7B; CYCS; NR4A3; OGDHL; SCO2 |
| anion homeostasis: GO | 37 | 1 | 6.66E−0 | 8.07E−01 | 0.59 | LIPG |
| apical junction assembly: GO | 37 | 1 | 6.66E−01 | 8.07E−01 | 0.59 | ECT2 |
| constitutive signaling by aberrant pi3k in cancer | 37 | 1 | 6.66E−01 | 8.07E−01 | 0.59 | HBEGF |
| cranial nerve development: GO | 37 | 1 | 6.66E−01 | 8.07E−01 | 0.59 | NTRK1 |
| erbb4 pathway | 37 | 1 | 6.66E−01 | 8.07E−01 | 0.59 | HBEGF |
| extrinsic apoptotic signaling pathway via death domain receptors: GO | 37 | 1 | 6.66E−01 | 8.07E−01 | 0.59 | TNFRSF9 |
| gtp hydrolysis and joining of the 60s ribosomal subunit | 37 | 1 | 6.66E−01 | 8.07E−01 | 0.59 | RPL22L1 |
| long term synaptic potentiation: GO | 37 | 1 | 6.66E−01 | 8.07E−01 | 0.59 | PLK2 |
| negative regulation of peptidyl tyrosine phosphorylation: GO | 37 | 1 | 6.66E−01 | 8.07E−01 | 0.59 | SAMSN1 |
| regulation of axon guidance: GO | 37 | 1 | 6.66E−01 | 8.07E−01 | 0.59 | WNT5A |
| rna polymerase ii transcribes snrna genes | 37 | 1 | 6.66E−01 | 8.07E−01 | 0.59 | NABP1 |
| termination | 37 | 1 | 6.66E−01 | 8.07E−01 | 0.59 | SNRPF |
| rna polymerase iii transcription | 37 | 1 | 6.66E−01 | 8.07E−01 | 0.59 | POLR3G |
| transition metal ion transmembrane transporter activity: GO | 37 | 1 | 6.66E−01 | 8.07E−01 | 0.59 | SLC39A6 |
| positive regulation of cell substrate adhesion: GO | 87 | 3 | 6.67E−01 | 8.07E−01 | 0.75 | C1QBP; CALR; FOXF1 |
| regulation of glucose transport: GO | 87 | 3 | 6.67E−01 | 8.07E−01 | 0.75 | HK2; IL1B; NR4A3 |
| regulation of endocytosis: GO | 183 | 7 | 6.70E−01 | 8.11E−01 | 0.84 | CALR; IL1B; PCSK9; PYCARD; SELE; SERPINE1; WNT5A |
| nuclear export: GO | 136 | 5 | 6.73E−01 | 8.13E−01 | 0.80 | CALR; EIF4A3; EIF5A; EIF6; RAN |
| leukocyte transendothelial migration | 112 | 4 | 6.73E−01 | 8.13E−01 | 0.78 | CXCL13; CXCR4; MMP9; RAC2 |
| positive regulation of lipid metabolic process: GO | 112 | 4 | 6.73E−01 | 8.13E−01 | 0.78 | IFNG; IL1B; LDLR; NR4A3 |
| process: GO | 112 | 4 | 6.73E−01 | 8.13E−01 | 0.78 | CYP27B1; IFNG; IL1B; LDLR |
| steroid hormone mediated signaling pathway: GO | 112 | 4 | 6.73E−01 | 8.13E−01 | 0.78 | CALR; CCNE1; NR4A3; RAN |
| filopodium: GO | 88 | 3 | 6.75E−01 | 8.15E−01 | 0.75 | FSCN1; MYO1B; TWF1 |
| glycerophospholipid metabolism | 88 | 3 | 6.75E−01 | 8.15E−01 | 0.75 | AKR1B10; ESCO2; PLA2G3 |
| aminopeptidase activity: GO | 38 | 1 | 6.78E−01 | 8.15E−01 | 0.58 | DPP3 |
| biopeptides pathway | 38 | 1 | 6.78E−01 | 8.15E−01 | 0.58 | STAT1 |
| ecadherin nascent aj pathway | 38 | 1 | 6.78E−01 | 8.15E−01 | 0.58 | NME1 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| erbb2 signaling pathway: GO | 38 | 1 | 6.78E−01 | 8.15E−01 | 0.58 | HBEGF |
| estrogen receptor binding: GO | 38 | 1 | 6.78E−01 | 8.15E−01 | 0.58 | PCNA |
| eye photoreceptor cell differentiation: GO | 38 | 1 | 6.78E−01 | 8.15E−01 | 0.58 | PRDM1 |
| g alpha (12/13) signalling events | 38 | 1 | 6.78E−01 | 8.15E−01 | 0.58 | ECT2 |
| negative chemotaxis: GO | 38 | 1 | 6.78E−01 | 8.15E−01 | 0.58 | WNT5A |
| p38 alpha beta downstream pathway | 38 | 1 | 6.78E−01 | 8.15E−01 | 0.58 | EIF4EBP1 |
| regulation of dna dependent dna replication: GO | 38 | 1 | 6.78E−01 | 8.15E−01 | 0.58 | BLM |
| scavenger receptor activity: GO | 38 | 1 | 6.78E−01 | 8.15E−01 | 0.58 | TMPRSS4 |
| substrate adhesion dependent cell spreading: GO | 38 | 1 | 6.78E−01 | 8.15E−01 | 0.58 | KIF14 |
| core promoter binding: GO | 137 | 5 | 6.79E−01 | 8.16E−01 | 0.80 | H2AFZ; HMGA2; IFI16; NR4A3; STAT1 |
| lysosomal transport: GO | 64 | 2 | 6.81E−01 | 8.19E−01 | 0.68 | HSPA8; PCSK9 |
| rna helicase activity: GO | 64 | 2 | 6.81E−01 | 8.19E−01 | 0.68 | DDX21; EIF4A3 |
| smoothened signaling pathway: GO | 64 | 2 | 6.81E−01 | 8.19E−01 | 0.68 | FOXF1; STIL |
| establishment of localization by movement along microtubule: GO | 89 | 3 | 6.83E−01 | 8.19E−01 | 0.74 | HIF1A; KIF23; KIF4A |
| metabolism of water-soluble vitamins and cofactors | 89 | 3 | 6.83E−01 | 8.19E−01 | 0.74 | GSTO1; NAMPT; PARP9 |
| platelet degranulation: GO | 89 | 3 | 6.83E−01 | 8.19E−01 | 0.74 | SERPINA1; SERPINE1; SRGN |
| differentiation: GO | 138 | 5 | 6.85E−01 | 8.22E−01 | 0.79 | CXCL10; CXCL9; FOXF1; IL4R; NEU2 |
| sodium ion transmembrane transporter activity: GO | 114 | 4 | 6.86E−01 | 8.22E−01 | 0.77 | ATP12A; ATP1B3; SLC5A1; SLC6A11 |
| transmission across chemical synapses | 186 | 7 | 6.87E−01 | 8.22E−01 | 0.82 | CHRNA3; CHRNA6; CHRNA9; GNGT2; HSPA8; KCNJ15; SLC6A11 |
| 4 iron 4 sulfur cluster binding: GO | 39 | 1 | 6.89E−01 | 8.22E−01 | 0.56 | RSAD2 |
| chrebp2 pathway | 39 | 1 | 6.89E−01 | 8.22E−01 | 0.56 | YWHAQ |
| ecadherin stabilization pathway | 39 | 1 | 6.89E−01 | 8.22E−01 | 0.56 | AQP3 |
| epithelial cell morphogenesis: GO | 39 | 1 | 6.89E−01 | 8.22E−01 | 0.56 | VSIG1 |
| golgi to plasma membrane transport: GO | 39 | 1 | 6.89E−01 | 8.22E−01 | 0.56 | RAB31 |
| negative regulation of lipid biosynthetic process: GO | 39 | 1 | 6.89E−01 | 8.22E−01 | 0.56 | CYP27B1 |
| incision: GO | 39 | 1 | 6.89E−01 | 8.22E−01 | 0.56 | PCNA |
| autophosphorylation: GO | 39 | 1 | 6.89E−01 | 8.22E−01 | 0.56 | JAK3 |
| positive regulation of pathway restricted smad protein phosphorylation: GO | 39 | 1 | 6.89E−01 | 8.22E−01 | 0.56 | TTK |
| rab gefs exchange gtp for gdp on rabs | 39 | 1 | 6.89E−01 | 8.22E−01 | 0.56 | RAB31 |
| regulation of mitophagy: GO | 39 | 1 | 6.89E−01 | 8.22E−01 | 0.56 | HIF1A |
| signaling by the b cell receptor bcr | 39 | 1 | 6.89E−01 | 8.22E−01 | 0.56 | PSMA4 |
| sphingolipid de novo biosynthesis | 39 | 1 | 6.89E−01 | 8.22E−01 | 0.56 | SPTSSA |
| thrombin par1 pathway | 39 | 1 | 6.89E−01 | 8.22E−01 | 0.56 | GNA15 |
| triglyceride biosynthesis | 39 | 1 | 6.89E−01 | 8.22E−01 | 0.56 | GK |
| electron transport chain: GO | 90 | 3 | 6.90E−01 | 8.22E−01 | 0.73 | COX7B; CYCS; SCO2 |
| abc-family proteins mediated transport | 65 | 2 | 6.90E−01 | 8.22E−01 | 0.67 | PSMA5; PSMB6 |
| hdac classi pathway | 65 | 2 | 6.90E−01 | 8.22E−01 | 0.67 | MXD1; RAN |
| positive regulation of carbohydrate metabolic process: GO | 65 | 2 | 6.90E−01 | 8.22E−01 | 0.67 | HIF1A; PTAFR |
| mesenchyme development: GO | 163 | 6 | 6.91E−01 | 8.23E−01 | 0.80 | EOMES; FOXF1; HIF1A; HMGA2; STAT1; WNT5A |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| receptor signaling protein activity: GO | 163 | 6 | 6.91E−01 | 8.23E−01 | 0.80 | ADCYAP1; CD3E; FCGR1A; IFITM1; IL4R; MAPK6 |
| lamellipodium: GO | 164 | 6 | 6.97E−01 | 8.26E−01 | 0.80 | DYSF; FSCN1; MEFV; RAC2; SH3BGRL3; SLC39A6 |
| phagocytosis: GO | 164 | 6 | 6.97E−01 | 8.26E−01 | 0.80 | CEACAM4; CLEC7A; FCGR1A; IGHG4; SLAMF1; TGM2 |
| columnar cuboidal epithelial cell differentiation: GO | 91 | 3 | 6.98E−01 | 8.26E−01 | 0.72 | HIF1A; PRDM1; WNT5A |
| large ribosomal subunit: GO | 91 | 3 | 6.98E−01 | 8.26E−01 | 0.72 | MRPL51; RPL22L1; RPL26L1 |
| lipid homeostasis: GO | 91 | 3 | 6.98E−01 | 8.26E−01 | 0.72 | LDLR; LIPG; PCSK9 |
| odontogenesis: GO | 91 | 3 | 6.98E−01 | 8.26E−01 | 0.72 | ALPL; AQP3; TNC |
| ecm affiliated | 140 | 5 | 6.98E−01 | 8.26E−01 | 0.78 | CLEC3A; CLEC7A; LGALS7; LGALS9B; LGALS9C |
| homophilic cell adhesion via plasma membrane adhesion molecules: GO | 140 | 5 | 6.98E−01 | 8.26E−01 | 0.78 | CDH26; CDH3; DSC2; DSG3; MPZL2 |
| regulation of chromatin organization: GO | 140 | 5 | 6.98E−01 | 8.26E−01 | 0.78 | CCNB1; CDC45; HIST1H1B; IL1B; UHRF1 |
| traf6 mediated induction of nfkb and map kinases upon tlr7/8 or 9 activation | 66 | 2 | 6.99E−01 | 8.26E−01 | 0.66 | MYD88; S100A12 |
| aorta development: GO | 40 | 1 | 6.99E−01 | 8.26E−01 | 0.55 | PRDM1 |
| cyclic nucleotide mediated signaling: GO | 40 | 1 | 6.99E−01 | 8.26E−01 | 0.55 | ADCYAP1 |
| histone h3 acetylation: GO | 40 | 1 | 6.99E−01 | 8.26E−01 | 0.55 | TRIM16 |
| hydro lyase activity: GO | 40 | 1 | 6.99E−01 | 8.26E−01 | 0.55 | ENO1 |
| labyrinthine layer development: GO | 40 | 1 | 6.99E−01 | 8.26E−01 | 0.55 | SOCS3 |
| enhanced by the exon junction complex (ejc) | 40 | 1 | 6.99E−01 | 8.26E−01 | 0.55 | RPL22L1 |
| nonsense-mediated decay (nmd) | 40 | 1 | 6.99E−01 | 8.26E−01 | 0.55 | RPL22L1 |
| positive regulation of adenylate cyclase activity: GO | 40 | 1 | 6.99E−01 | 8.26E−01 | 0.55 | ADCYAP1 |
| regulation of actin dynamics for phagocytic cup formation | 40 | 1 | 6.99E−01 | 8.26E−01 | 0.55 | FCGR1A |
| regulation of polysaccharide metabolic process: GO | 40 | 1 | 6.99E−01 | 8.26E−01 | 0.55 | PHLDA2 |
| regulation of potassium ion transmembrane transporter activity: GO | 40 | 1 | 6.99E−01 | 8.26E−01 | 0.55 | ATP1B3 |
| regulation of vacuole organization: GO | 40 | 1 | 6.99E−01 | 8.26E−01 | 0.55 | RALB |
| skeletal muscle cell differentiation: GO | 40 | 1 | 6.99E−01 | 8.26E−01 | 0.55 | EOMES |
| transcription-coupled nucleotide excision repair (tc-ner) | 40 | 1 | 6.99E−01 | 8.26E−01 | 0.55 | PCNA |
| vasopressin regulated water reabsorption | 40 | 1 | 6.99E−01 | 8.26E−01 | 0.55 | AQP3 |
| organelle fusion: GO | 116 | 4 | 7.00E−01 | 8.26E−01 | 0.75 | BAK1; BCL2A1; CDK1; DYSF |
| protein phosphatase binding: GO | 116 | 4 | 7.00E−01 | 8.26E−01 | 0.75 | EIF4EBP1; JAK3; NEK2; VCP |
| core promoter sequence specific dna binding: GO | 92 | 3 | 7.05E−01 | 8.31E−01 | 0.71 | H2AFZ; NR4A3; STAT1 |
| fc gamma r mediated phagocytosis | 92 | 3 | 7.05E−01 | 8.31E−01 | 0.71 | FCGR1A; PLA2G4D; RAC2 |
| pml body: GO | 92 | 3 | 7.05E−01 | 8.31E−01 | 0.71 | BLM; ISG20; TRIM16 |
| process: GO | 92 | 3 | 7.05E−01 | 8.31E−01 | 0.71 | IL6; PGAMI; PHLDA2 |
| hindbrain development: GO | 117 | 4 | 7.07E−01 | 8.32E−01 | 0.75 | CDK5R1; KIF14; NLGN4X; WNT7A |
| negative regulation of homeostatic process: GO | 117 | 4 | 7.07E−01 | 8.32E−01 | 0.75 | CCL3; CCR5; GSTO1; PIF1 |
| dicarboxylic acid transport: GO | 67 | 2 | 7.07E−01 | 8.32E−01 | 0.65 | SLC26A9; SLC7A11 |
| epithelial cell signaling in helicobacter | 67 | 2 | 7.07E−01 | 8.32E−01 | 0.65 | CXCL1; HBEGF |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| pylori infection | | | | | | |
| erythrocyte homeostasis: GO | 67 | 2 | 7.07E−01 | 8.32E−01 | 0.65 | HMOX1; PRDX1 |
| myd88 dependent cascade initiated on endosome | 67 | 2 | 7.07E−01 | 8.32E−01 | 0.65 | MYD88; S100A12 |
| respiratory electron transport atp synthesis by chemiosmotic coupling and heat production by uncoupling proteins | 67 | 2 | 7.07E−01 | 8.32E−01 | 0.65 | COX7B; CYCS |
| toll like receptor 7/8 (tlr7/8) cascade | 67 | 2 | 7.07E−01 | 8.32E−01 | 0.65 | MYD88; S100A12 |
| calcium signaling pathway | 166 | 6 | 7.08E−01 | 8.33E−01 | 0.79 | CALML3; CALML5; GNA15; HTR7; PTAFR; SLC25A5 |
| complex: GO | 41 | 1 | 7.09E−01 | 8.33E−01 | 0.53 | NETO2 |
| metabolism of non coding rna | 41 | 1 | 7.09E−01 | 8.33E−01 | 0.53 | SNRPG |
| negative regulation of stat cascade: GO | 41 | 1 | 7.09E−01 | 8.33E−01 | 0.53 | SOCS3 |
| regulation of endocrine process: GO | 41 | 1 | 7.09E−01 | 8.33E−01 | 0.53 | IL1B |
| xbp1(s) activates chaperone genes | 41 | 1 | 7.09E−01 | 8.33E−01 | 0.53 | SEC61G |
| regulation of organelle assembly: GO | 142 | 5 | 7.10E−01 | 8.33E−01 | 0.77 | CSF2; FSCN1; PLK1; PLK2; RALB |
| cardiac chamber morphogenesis: GO | 93 | 3 | 7.12E−01 | 8.35E−01 | 0.71 | FOXF1; HIF1A; WNT5A |
| memory: GO | 93 | 3 | 7.12E−01 | 8.35E−01 | 0.71 | IL1B; KCNK10; PLK2 |
| ter pathway | 93 | 3 | 7.12E−01 | 8.35E−01 | 0.71 | CD3E; CD80; PRKCQ |
| contractile fiber: GO | 191 | 7 | 7.13E−01 | 8.36E−01 | 0.80 | CDK5R1; ENO1; HOMER1; IDO1; MYOM3; SCO2; TWF1 |
| arrhythmogenic right ventricular cardiomyopathy arve | 68 | 2 | 7.16E−01 | 8.38E−01 | 0.64 | DSC2; ITGB6 |
| positive regulation of axonogenesis: GO | 68 | 2 | 7.16E−01 | 8.38E−01 | 0.64 | CRABP2; TNFRSF12A |
| renal tubule development: GO | 68 | 2 | 7.16E−01 | 8.38E−01 | 0.64 | PGF; STAT1 |
| rho gtpase cycle | 68 | 2 | 7.16E−01 | 8.38E−01 | 0.64 | DEPDC1B; ECT2 |
| fc receptor signaling pathway: GO | 192 | 7 | 7.18E−01 | 8.39E−01 | 0.80 | FCGR1A; IGHG4; NR4A3; PRKCQ; PSMA4; PSMA5; PSMB6 |
| dendrite morphogenesis: GO | 42 | 1 | 7.19E−01 | 8.39E−01 | 0.52 | WNT7A |
| histone h4 acetylation: GO | 42 | 1 | 7.19E−01 | 8.39E−01 | 0.52 | TRIM16 |
| hormone biosynthetic process: GO | 42 | 1 | 7.19E−01 | 8.39E−01 | 0.52 | AKR1B15 |
| myotube differentiation: GO | 42 | 1 | 7.19E−01 | 8.39E−01 | 0.52 | HOMER1 |
| negative regulation of actin filament polymerization: GO | 42 | 1 | 7.19E−01 | 8.39E−01 | 0.52 | TWF1 |
| negative regulation of gtpase activity: GO | 42 | 1 | 7.19E−01 | 8.39E−01 | 0.52 | ADCYAP1 |
| pi3k events in erbb2 signaling | 42 | 1 | 7.19E−01 | 8.39E−01 | 0.52 | HBEGF |
| smooth muscle contraction: GO | 42 | 1 | 7.19E−01 | 8.39E−01 | 0.52 | HTR7 |
| stimuli-sensing channels | 42 | 1 | 7.19E−01 | 8.39E−01 | 0.52 | GLTP |
| regulated sequence specific dna binding: GO | 42 | 1 | 7.19E−01 | 8.39E−01 | 0.52 | NR4A3 |
| secretion: GO | 94 | 3 | 7.19E−01 | 8.39E−01 | 0.70 | ADCYAP1; HIF1A; VSNL1 |
| protein transporter activity: GO | 94 | 3 | 7.19E−01 | 8.39E−01 | 0.70 | AP1S3; KPNA2; SEC61G |
| golgi stack: GO | 119 | 4 | 7.19E−01 | 8.39E−01 | 0.74 | FUT1; FUT2; FUT3; PITPNM1 |
| myd88:mal cascade initiated on plasma membrane | 69 | 2 | 7.24E−01 | 8.41E−01 | 0.63 | MYD88; S100A12 |
| negative regulation of nucleocytoplasmic transport: GO | 69 | 2 | 7.24E−01 | 8.41E−01 | 0.63 | MDFI; ZC3H12A |
| nfkb and map kinases activation mediated by tlr4 signaling repertoire | 69 | 2 | 7.24E−01 | 8.41E−01 | 0.63 | CDK1; S100A12 |
| regulation of sodium ion transport: GO | 69 | 2 | 7.24E−01 | 8.41E−01 | 0.63 | ATP1B3; PCSK9 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| semaphorin interactions | 69 | 2 | 7.24E−01 | 8.41E−01 | 0.63 | CDK5R1; RAC2 |
| skin epidermis development: GO | 69 | 2 | 7.24E−01 | 8.41E−01 | 0.63 | FOXE1; KRT17 |
| toll like receptor 9 (tlr9) cascade | 69 | 2 | 7.24E−01 | 8.41E−01 | 0.63 | MYD88; S100A12 |
| toll like receptor tlr6:tlr2 cascade | 69 | 2 | 7.24E−01 | 8.41E−01 | 0.63 | MYD88; S100A12 |
| vegfr1 2 pathway | 69 | 2 | 7.24E−01 | 8.41E−01 | 0.63 | SH2D2A; SHB |
| stem cell differentiation: GO | 169 | 6 | 7.25E−01 | 8.41E−01 | 0.78 | EOMES; HIF1A; HMGA2; STAT1; WNT5A; WNT7A |
| amino acid binding: GO | 95 | 3 | 7.26E−01 | 8.41E−01 | 0.69 | GOT2; HSPA8; TDO2 |
| integrin cell surface interactions | 95 | 3 | 7.26E−01 | 8.41E−01 | 0.69 | ITGAX; ITGB6; TNC |
| protein localization to nucleus: GO | 145 | 5 | 7.27E−01 | 8.41E−01 | 0.75 | CALR; IFNG; JAK3; KPNA2; RAN |
| transcriptional activator activity rna polymerase ii core promoter proximal region sequence specific binding: GO | 194 | 7 | 7.29E−01 | 8.41E−01 | 0.79 | EHF; FOSL1; HIF1A; HMGA2; MYBL2; NR4A3; PITX1 |
| 3 5 exonuclease activity: GO | 43 | 1 | 7.29E−01 | 8.41E−01 | 0.51 | ISG20 |
| body morphogenesis: GO | 43 | 1 | 7.29E−01 | 8.41E−01 | 0.51 | STRA6 |
| carbohydrate derivative transport: GO | 43 | 1 | 7.29E−01 | 8.41E−01 | 0.51 | GLTP |
| cellular pigmentation: GO | 43 | 1 | 7.29E−01 | 8.41E−01 | 0.51 | RAB38 |
| endochondral bone morphogenesis: GO | 43 | 1 | 7.29E−01 | 8.41E−01 | 0.51 | ALPL |
| endothelial cell development: GO | 43 | 1 | 7.29E−01 | 8.41E−01 | 0.51 | WNT7A |
| hes hey pathway | 43 | 1 | 7.29E−01 | 8.41E−01 | 0.51 | HIF1A |
| intrinsic component of mitochondrial membrane: GO | 43 | 1 | 7.29E−01 | 8.41E−01 | 0.51 | BAK1 |
| irel alpha activates chaperones | 43 | 1 | 7.29E−01 | 8.41E−01 | 0.51 | SEC61G |
| mechanoreceptor differentiation: GO | 43 | 1 | 7.29E−01 | 8.41E−01 | 0.51 | NTRK1 |
| nadp binding: GO | 43 | 1 | 7.29E−01 | 8.41E−01 | 0.51 | GAPDH |
| peg protein complex: GO | 43 | 1 | 7.29E−01 | 8.41E−01 | 0.51 | CBX2 |
| peptide secretion: GO | 43 | 1 | 7.29E−01 | 8.41E−01 | 0.51 | IL6 |
| positive regulation of fat cell differentiation: GO | 43 | 1 | 7.29E−01 | 8.41E−01 | 0.51 | ZC3H12A |
| protein localization to vacuole: GO | 43 | 1 | 7.29E−01 | 8.41E−01 | 0.51 | HSPA8 |
| rna polymerase activity: GO | 43 | 1 | 7.29E−01 | 8.41E−01 | 0.51 | POLR3G |
| transcriptional repressor activity rna polymerase ii activating transcription factor binding: GO | 43 | 1 | 7.29E−01 | 8.41E−01 | 0.51 | PITX1 |
| transmission of nerve impulse: GO | 43 | 1 | 7.29E−01 | 8.41E−01 | 0.51 | CNTNAP2 |
| actomyosin structure organization: GO | 70 | 2 | 7.32E−01 | 8.43E−01 | 0.62 | CNN2; KIF23 |
| erad pathway: GO | 70 | 2 | 7.32E−01 | 8.43E−01 | 0.62 | SDF2L1; VCP |
| regulation of plasma membrane organization: GO | 70 | 2 | 7.32E−01 | 8.43E−01 | 0.62 | IFNG; S100A9 |
| toll like receptor 2 (tlr2) cascade | 70 | 2 | 7.32E−01 | 8.43E−01 | 0.62 | MYD88; S100A12 |
| toll like receptor tlr1:tlr2 cascade | 70 | 2 | 7.32E−01 | 8.43E−01 | 0.62 | MYD88; S100A12 |
| sodium ion transport: GO | 121 | 4 | 7.32E−01 | 8.43E−01 | 0.72 | ATP12A; ATP1B3; SLC4A8; SLC5A1 |
| termination: GO | 96 | 3 | 7.33E−01 | 8.44E−01 | 0.68 | EIF4A3; SNRPF; SNRPG |
| regulation of fat cell differentiation: GO | 96 | 3 | 7.33E−01 | 8.44E−01 | 0.68 | IL6; WNT5A; ZC3H12A |
| cell growth: GO | 122 | 4 | 7.38E−01 | 8.45E−01 | 0.72 | AURKA; IL6; IL7R; NDRG4 |
| cardiac septum morphogenesis: GO | 44 | 1 | 7.38E−01 | 8.45E−01 | 0.50 | WNT5A |
| guanosine containing compound metabolic process: GO | 44 | 1 | 7.38E−01 | 8.45E−01 | 0.50 | NME1 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| keratinocyte differentiation | 44 | 1 | 7.38E−01 | 8.45E−01 | 0.50 | PRKCQ |
| mesonephric tubule morphogenesis: GO | 44 | 1 | 7.38E−01 | 8.45E−01 | 0.50 | PGF |
| negative regulation of calcium ion transport: GO | 44 | 1 | 7.38E−01 | 8.45E−01 | 0.50 | GSTO1 |
| secretion: GO | 44 | 1 | 7.38E−01 | 8.45E−01 | 0.50 | VSNL1 |
| nuclear receptor transcription pathway | 44 | 1 | 7.38E−01 | 8.45E−01 | 0.50 | NR4A3 |
| o acyltransferase activity: GO | 44 | 1 | 7.38E−01 | 8.45E−01 | 0.50 | PIGW |
| receptor internalization: GO | 44 | 1 | 7.38E−01 | 8.45E−01 | 0.50 | RAB31 |
| respiratory gaseous exchange: GO | 44 | 1 | 7.38E−01 | 8.45E−01 | 0.50 | TMPRSS11D |
| response to glucagon: GO | 44 | 1 | 7.38E−01 | 8.45E−01 | 0.50 | CCNA2 |
| rhoa reg pathway | 44 | 1 | 7.38E−01 | 8.45E−01 | 0.50 | ECT2 |
| smad protein signal transduction: GO | 44 | 1 | 7.38E−01 | 8.45E−01 | 0.50 | SUB1 |
| thymocyte aggregation: GO | 44 | 1 | 7.38E−01 | 8.45E−01 | 0.50 | CD3E |
| transcription coupled ner te ner | 44 | 1 | 7.38E−01 | 8.45E−01 | 0.50 | PCNA |
| cell-cell communication | 71 | 2 | 7.39E−01 | 8.45E−01 | 0.62 | FBLIM1; KRT17 |
| myd88-independent tlr3/tlr4 cascade | 71 | 2 | 7.39E−01 | 8.45E−01 | 0.62 | MYD88; S100A12 |
| regulation of actin filament bundle assembly: GO | 71 | 2 | 7.39E−01 | 8.45E−01 | 0.62 | GPR65; PRKCQ |
| selenoamino acid metabolism | 71 | 2 | 7.39E−01 | 8.45E−01 | 0.62 | AHCY; RPL22L1 |
| toll like receptor 3 (tlr3) cascade | 71 | 2 | 7.39E−01 | 8.45E−01 | 0.62 | MYD88; S100A12 |
| transcriptional regulation by runx3 | 71 | 2 | 7.39E−01 | 8.45E−01 | 0.62 | PSMA5; PSMB6 |
| trif-mediated tlr3/tlr4 signaling | 71 | 2 | 7.39E−01 | 8.45E−01 | 0.62 | MYD88; S100A12 |
| fat cell differentiation: GO | 97 | 3 | 7.40E−01 | 8.45E−01 | 0.68 | HMGA2; NR4A3; STEAP4 |
| negative regulation of neuron differentiation: GO | 172 | 6 | 7.41E−01 | 8.46E−01 | 0.76 | ASPM; CALR; CDK5R1; IL1B; PLK2; WNT5A |
| dna binding transcription factor activity: GO | 123 | 4 | 7.44E−01 | 8.50E−01 | 0.71 | HMOX1; PYCARD; TNFRSF4; ZC3H12A |
| spermatid differentiation: GO | 98 | 3 | 7.47E−01 | 8.50E−01 | 0.67 | PLA2G3; RAN; TRIP13 |
| stress activated protein kinase signaling cascade: GO | 98 | 3 | 7.47E−01 | 8.50E−01 | 0.67 | DUSP9; MDFI; WNT5A |
| kidney morphogenesis: GO | 72 | 2 | 7.47E−01 | 8.50E−01 | 0.61 | GCNT4; PGF |
| polymerase ii transcription factor binding: GO | 72 | 2 | 7.47E−01 | 8.50E−01 | 0.61 | EOMES; PITX1 |
| morphogenesis: GO | 45 | 1 | 7.48E−01 | 8.50E−01 | 0.49 | EIF4A3 |
| ilk pathway | 45 | 1 | 7.48E−01 | 8.50E−01 | 0.49 | AURKA |
| keratinocyte pathway | 45 | 1 | 7.48E−01 | 8.50E−01 | 0.49 | PRKCQ |
| mrna 3 utr binding: GO | 45 | 1 | 7.48E−01 | 8.50E−01 | 0.49 | ZC3H12A |
| negative regulation of epithelial cell migration: GO | 45 | 1 | 7.48E−01 | 8.50E−01 | 0.49 | CXCL13 |
| regulation of cholesterol biosynthesis by srebp (srebf) | 45 | 1 | 7.48E−01 | 8.50E−01 | 0.49 | SQLE |
| regulation of establishment of protein localization to plasma membrane: GO | 45 | 1 | 7.48E−01 | 8.50E−01 | 0.49 | IFNG |
| t tubule: GO | 45 | 1 | 7.48E−01 | 8.50E−01 | 0.49 | DYSF |
| 6tnf pathway | 45 | 1 | 7.48E−01 | 8.50E−01 | 0.49 | STAT1 |
| c7oenzyme binding: GO | 174 | 6 | 7.51E−01 | 8.53E−01 | 0.75 | AHCY; ALDH1A3; GAPDH; LDHA; OGDHL; SQLE |
| energy derivation by oxidation of organic | 199 | 7 | 7.53E−01 | 8.55E−01 | 0.77 | COX7B; CYCS; NR4A3; OGDHL; PGM2; PYGL; SCO2 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| compounds: GO | | | | | | |
| protein secretion: GO | 99 | 3 | 7.53E−01 | 8.55E−01 | 0.66 | PNP; S100A12; TREM1 |
| rna polymerase ii transcription factor binding: GO | 99 | 3 | 7.53E−01 | 8.55E−01 | 0.66 | EOMES; IFI27; PITX1 |
| insulin receptor signaling pathway: GO | 73 | 2 | 7.54E−01 | 8.55E−01 | 0.60 | EIF4EBP1; NAMPT |
| receptor metabolic process: GO | 73 | 2 | 7.54E−01 | 8.55E−01 | 0.60 | PCSK9; RAB31 |
| steroid binding: GO | 73 | 2 | 7.54E−01 | 8.55E−01 | 0.60 | FABP6; PYGL |
| thioester metabolic process: GO | 73 | 2 | 7.54E−01 | 8.55E−01 | 0.60 | KYNU; TDO2 |
| anion cation symporter activity: GO | 46 | 1 | 7.56E−01 | 8.56E−01 | 0.48 | SLC6A11 |
| golgi associated vesicle membrane: GO | 46 | 1 | 7.56E−01 | 8.56E−01 | 0.48 | CNGB1 |
| mitochondrial biogenesis | 46 | 1 | 7.56E−01 | 8.56E−01 | 0.48 | CYCS |
| notch1 intracellular domain regulates transcription | 46 | 1 | 7.56E−01 | 8.56E−01 | 0.48 | HIF1A |
| positive regulation of stem cell differentiation: GO | 46 | 1 | 7.56E−01 | 8.56E−01 | 0.48 | SERPINB3 |
| regulation of histone methylation: GO | 46 | 1 | 7.56E−01 | 8.56E−01 | 0.48 | HIST1H1B |
| presynaptic process involved in synaptic transmission: GO | 100 | 3 | 7.59E−01 | 8.59E−01 | 0.66 | HRH3; HSPA8; WNT7A |
| protein n terminus binding: GO | 100 | 3 | 7.59E−01 | 8.59E−01 | 0.66 | EIF5A; YWHAQ; ZWINT |
| active ion transmembrane transporter activity: GO | 151 | 5 | 7.60E−01 | 8.60E−01 | 0.72 | ATP12A; ATP1B3; SLC26A9; SLC6A11; SLC7A11 |
| hypertrophic cardiomyopathy hcm | 74 | 2 | 7.61E−01 | 8.61E−01 | 0.59 | IL6; ITGB6 |
| activation of mapkk activity: GO | 47 | 1 | 7.65E−01 | 8.63E−01 | 0.4 | NTRKI |
| cardiac muscle tissue morphogenesis: GO | 47 | 1 | 7.65E−01 | 8.63E−01 | 0.47 | WNT5A |
| cell cell communication | 47 | 1 | 7.65E−01 | 8.63E−01 | 0.47 | CDH3 |
| activity: GO | 47 | 1 | 7.65E−01 | 8.63E−01 | 0.47 | TPI1 |
| neural crest cell migration: GO | 47 | 1 | 7.65E−01 | 8.63E−01 | 0.47 | HIF1A |
| regulation of blood vessel endothelial cell migration: GO | 47 | | 7.65E−01 | 8.63E−01 | 0.47 | SH3BGRL3 |
| regulation of kidney development: GO | 47 | 1 | 7.65E−01 | 8.63E−01 | 0.47 | STAT1 |
| negative regulation of canonical wnt signaling pathway: GO | 152 | 5 | 7.65E−01 | 8.63E−01 | 0.72 | PSMA4; PSMA5; PSMB6; RGS20; WNT5A |
| neuron projection guidance: GO | 177 | 6 | 7.65E−01 | 8.63E−01 | 0.74 | ARTN; CDK5R1; NR4A3; NTRK1; PRKCQ; WNT5A |
| process: GO | 177 | 6 | 7.65E−01 | 8.63E−01 | 0.74 | CD80; HBEGF; PIGW; PLA2G4D; PLAUR; PLBD1 |
| trans golgi network: GO | 177 | 6 | 7.65E−01 | 8.63E−01 | 0.74 | AP1S3; CHAC1; MYO1B; RAB31; RAB38; RGS20 |
| class i mhc mediated antigen processing presentation | 101 | 3 | 7.66E−01 | 8.63E−01 | 0.65 | PSMA4; TAP2; UBE2S |
| rho guanyl nucleotide exchange factor activity: GO | 75 | 2 | 7.68E−01 | 8.65E−01 | 0.58 | ECT2; PLEKHG7 |
| cell fate commitment: GO | 178 | 6 | 7.70E−01 | 8.67E−01 | 0.74 | EOMES; IL6; PITX1; PRDM1; WNT5A; WNT7A |
| cysteine type peptidase activity: GO | 153 | 5 | 7.70E−01 | 8.67E−01 | 0.71 | CTSB; CTSC; PYCARD; USP43; ZC3H12A |
| ovulation cycle: GO | 102 | 3 | 7.72E−01 | 8.67E−01 | 0.64 | ADCYAP1; CCNE1; WNT5A |
| response to fibroblast growth factor: GO | 102 | 3 | 7.72E−01 | 8.67E−01 | 0.64 | CXCL13; FGFBP1; TNC |
| hiv life cycle | 128 | 4 | 7.72E−01 | 8.67E−01 | 0.68 | CCR5; CXCR4; RAN; RCC1 |
| basal part of cell: GO | 48 | 1 | 7.73E−01 | 8.67E−01 | 0.46 | CLCA2 |
| brush border membrane: GO | 48 | 1 | 7.73E−01 | 8.67E−01 | 0.46 | SLC5A1 |
| cellular response to camp: GO | 48 | 1 | 7.73E−01 | 8.67E−01 | 0.46 | PTAFR |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| ceramide pathway | 48 | 1 | 7.73E−01 | 8.67E−01 | 0.46 | CYCS |
| membrane: GO | 48 | 1 | 7.73E−01 | 8.67E−01 | 0.46 | ST8S1A2 |
| lateral plasma membrane: GO | 48 | 1 | 7.73E−01 | 8.67E−01 | 0.46 | GJB2 |
| negative regulation of cell substrate adhesion: GO | 48 | 1 | 7.73E−01 | 8.67E−01 | 0.46 | SERPINE1 |
| neuron projection extension: GO | 48 | 1 | 7.73E−01 | 8.67E−01 | 0.46 | AURKA |
| translation initiation factor activity: GO | 48 | 1 | 7.73E−01 | 8.67E−01 | 0.46 | EIF6 |
| vibrio cholerae infection | 48 | 1 | 7.73E−01 | 8.67E−01 | 0.46 | SEC61G |
| oxidative phosphorylation: GO | 76 | 2 | 7.75E−01 | 8.68E−01 | 0.58 | COX7B; CYCS |
| regulation of carbohydrate biosynthetic process: GO | 76 | 2 | 7.75E−01 | 8.68E−01 | 0.58 | IL6; PTAFR |
| transport: GO | 76 | 2 | 7.75E−01 | 8.68E−01 | 0.58 | ATP12A; ATP1B3 |
| pathway: GO | 154 | 5 | 7.75E−01 | 8.68E−01 | 0.71 | CALR; CCNE1; CYP24A1; NR4A3; RAN |
| blood microparticle: GO | 103 | 3 | 7.78E−01 | 8.71E−01 | 0.64 | HSPA6; HSPA8; IGHG4 |
| cell cell adhesion via plasma membrane adhesion molecules: GO | 180 | 6 | 7.79E−01 | 8.71E−01 | 0.73 | CDH26; CDH3; DSC2; DSG3; MPZL2; SELE |
| negative regulation of wnt signaling pathway: GO | 180 | 6 | 7.79E−01 | 8.71E−01 | 0.73 | MDFI; PSMA4; PSMA5; PSMB6; RGS20; WNT5A |
| regulation of muscle system process: GO | 180 | 6 | 7.79E−01 | 8.71E−01 | 0.73 | CHRNA3; DSC2; GSTO1; NR4A3; PTAFR; ZC3H12A |
| appendage development: GO | 155 | 5 | 7.80E−01 | 8.71E−01 | 0.71 | BAK1; CRABP2; PITX1; WNT5A; WNT7A |
| regulation of signal transduction by p53 class mediator: GO | 155 | 5 | 7.80E−01 | 8.71E−01 | 0.71 | AURKA; BLM; CDK5R1; EXO1; TPX2 |
| aerobic respiration: GO | 49 | 1 | 7.81E−01 | 8.71E−01 | 0.45 | OGDHL |
| expression: GO | 49 | 1 | 7.81E−01 | 8.71E−01 | 0.45 | NAMPT |
| demethylation: GO | 49 | 1 | 7.81E−01 | 8.71E−01 | 0.45 | APOBEC3A |
| dna methylation or demethylation: GO | 49 | 1 | 7.81E−01 | 8.71E−01 | 0.45 | APOBEC3A |
| intercalated disc: GO | 49 | 1 | 7.81E−01 | 8.71E−01 | 0.45 | DSC2 |
| non-integrin membrane-ecm interactions | 49 | 1 | 7.81E−01 | 8.71E−01 | 0.45 | TNC |
| positive regulation of lyase activity: GO | 49 | 1 | 7.81E−01 | 8.71E−01 | 0.45 | ADCYAP1 |
| ptp1b pathway | 49 | 1 | 7.81E−01 | 8.71E−01 | 0.45 | SOCS3 |
| dioxygenase activity: GO | 77 | 2 | 7.82E−01 | 8.71E−01 | 0.57 | IDO1; TDO2 |
| proteoglycan metabolic process: GO | 77 | 2 | 7.82E−01 | 8.71E−01 | 0.57 | HPSE; HS3ST3B1 |
| smad2 3nuclear pathway | 77 | 2 | 7.82E−01 | 8.71E−01 | 0.57 | HSPA8; SERPINE1 |
| mitochondrial protein complex: GO | 104 | 3 | 7.83E−01 | 8.73E−01 | 0.63 | PPIF; TIMM13; TIMM8B |
| er to golgi vesicle mediated transport: GO | 156 | 5 | 7.85E−01 | 8.74E−01 | 0.70 | AREG; CTSC; SERPINA1; TGFA; VCP |
| organic hydroxy compound biosynthetic process: GO | 156 | 5 | 7.85E−01 | 8.74E−01 | 0.70 | CH25H; CYP27B1; FABP5; PTAFR; SQLE |
| regulation of axonogenesis: GO | 156 | 5 | 7.85E−01 | 8.74E−01 | 0.70 | CDK5R1; CRABP2; TNFRSF12A; WNT5A; WNT7A |
| transport: GO | 78 | 2 | 7.88E−01 | 8.75E−01 | 0.56 | ATP12A; COX7B |
| ovulation cycle process: GO | 78 | 2 | 7.88E−01 | 8.75E−01 | 0.56 | ADCYAP1; CCNE1 |
| post golgi vesicle mediated transport: GO | 78 | 2 | 7.88E−01 | 8.75E−01 | 0.56 | MYO1B; RAB31 |
| transport: GO | 78 | 2 | 7.88E−01 | 8.75E−01 | 0.56 | ADCYAP1; ATP1B3 |
| binding: GO | 50 | 1 | 7.89E−01 | 8.75E−01 | 0.44 | DYSF |
| cell fate specification: GO | 50 | 1 | 7.89E−01 | 8.75E−01 | 0.44 | EOMES |
| fatty acid transport: GO | 50 | 1 | 7.89E−01 | 8.75E−01 | 0.44 | GOT2 |
| negative regulation of erk1 and erk2 cascade: GO | 50 | 1 | 7.89E−01 | 8.75E−01 | 0.44 | GSTP1 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| neuronal postsynaptic density: GO | 50 | 1 | 7.89E−01 | 8.75E−01 | 0.44 | HOMER1 |
| regulation of pathway restricted smad protein phosphorylation: GO | 50 | 1 | 7.89E−01 | 8.75E−01 | 0.44 | TTK |
| spliceosomal complex: GO | 157 | 5 | 7.90E−01 | 8.76E−01 | 0.70 | EIF4A3; HSPA8; PPIL1; SNRPF; SNRPG |
| skeletal system morphogenesis: GO | 183 | 6 | 7.93E−01 | 8.79E−01 | 0.72 | ACP5; ALPL; EIF4A3; LTF; MDFI; WNT7A |
| regulation of cell shape: GO | 132 | 4 | 7.93E−01 | 8.80E−01 | 0.66 | CCL3; CCL7; FBLIM1; IL6 |
| integrin mediated signaling pathway: GO | 79 | 2 | 7.94E−01 | 8.80E−01 | 0.55 | ITGAX; ITGB6 |
| mapk pathway | 79 | 2 | 7.94E−01 | 8.80E−01 | 0.55 | MAPK6; STAT1 |
| post embryonic development: GO | 79 | 2 | 7.94E−01 | 8.80E−01 | 0.55 | BAK1; PRDMI |
| phosphatase binding: GO | 158 | 5 | 7.94E−01 | 8.80E−01 | 0.69 | CTSC; EIF4EBP1; JAK3; NEK2; VCP |
| global genome nucleotide excision repair (gg-ner) | 51 | 1 | 7.96E−01 | 8.80E−01 | 0.43 | PCNA |
| negative regulation of muscle cell differentiation: GO | 51 | 1 | 7.96E−01 | 8.80E−01 | 0.43 | CXCL10 |
| regulation of glucose import: GO | 51 | 1 | 7.96E−01 | 8.80E−01 | 0.43 | HK2 |
| regulation of intracellular steroid hormone receptor signaling pathway: GO | 51 | 1 | 7.96E−01 | 8.80E−01 | 0.43 | CALR |
| regulation of tissue remodeling: GO | 51 | 1 | 7.96E−01 | 8.80E−01 | 0.43 | IL12B |
| steroid hormone receptor activity: GO | 51 | 1 | 7.96E−01 | 8.80E−01 | 0.43 | NR4A3 |
| cytoplasmic side of membrane: GO | 159 | 5 | 7.99E−01 | 8.83E−01 | 0.69 | CD2; GNA15; GNGT2; JAK3; RGS1 |
| activated tlr4 signalling | 107 | 3 | 8.00E−01 | 8.83E−01 | 0.61 | CDK1; MYD88; S100A12 |
| negative regulation of cell morphogenesis involved in differentiation: GO | 107 | 3 | 8.00E−01 | 8.83E−01 | 0.61 | CDK5R1; STAT1; WNT5A |
| major pathway of rrna processing in the nucleolus and cytosol | 80 | 2 | 8.01E−01 | 8.83E−01 | 0.55 | RPL22L1; RPP40 |
| nerna transcription: GO | 80 | 2 | 8.01E−01 | 8.83E−01 | 0.55 | GTF3C6; NPM3 |
| negative regulation of developmental growth: GO | 80 | 2 | 8.01E−01 | 8.83E−01 | 0.55 | CDK5R1; WNT5A |
| phosphatidylinositol signaling system | 80 | 2 | 8.01E−01 | 8.83E−01 | 0.55 | CALML3; CALML5 |
| central nervous system neuron differentiation: GO | 134 | 4 | 8.03E−01 | 8.84E−01 | 0.65 | EOMES; FBXO45; WNT5A; WNT7A |
| ribonucleoprotein granule: GO | 134 | 4 | 8.03E−01 | 8.84E−01 | 0.65 | INA; PSMA4; SNRPG; ZC3H12A |
| kit pathway | 52 | 1 | 8.04E−01 | 8.84E−01 | 0.42 | STAT1 |
| nrage signals death through jnk | 52 | 1 | 8.04E−01 | 8.84E−01 | 0.42 | ECT2 |
| oligodendrocyte differentiation: GO | 52 | 1 | 8.04E−01 | 8.84E−01 | 0.42 | GSTP1 |
| protein tyrosine kinase binding: GO | 52 | 1 | 8.04E−01 | 8.84E−01 | 0.42 | PCNA |
| regulation of vesicle fusion: GO | 52 | 1 | 8.04E−01 | 8.84E−01 | 0.42 | SLAMF1 |
| spliceosomal complex assembly: GO | 52 | 1 | 8.04E−01 | 8.84E−01 | 0.42 | SNRPG |
| hydrogen transport: GO | 108 | 3 | 8.05E−01 | 8.85E−01 | 0.61 | ATP12A; COX7B; SLC2A9 |
| inorganic anion transmembrane transporter activity: GO | 108 | 3 | 8.05E−01 | 8.85E−01 | 0.61 | CLCA2; SLC26A9; SLC4A8 |
| muscle cell development: GO | 108 | 3 | 8.05E−01 | 8.85E−01 | 0.61 | CCNB1; CDK1; HOMER1 |
| translational elongation: GO | 108 | 3 | 8.05E−01 | 8.85E−01 | 0.61 | EIF5A; EIF5AL1; MRPL51 |
| mapkinase signaling pathway | 81 | 2 | 8.07E−01 | 8.86E−01 | 0.54 | MAPK6; STAT1 |
| methyltransferase complex: GO | 81 | 2 | 8.07E−01 | 8.86E−01 | 0.54 | SNRPF; SNRPG |
| pip3 activates akt signaling | 161 | 5 | 8.08E−01 | 8.87E−01 | 0.68 | CBX2; HBEGF; MYD88; PSMA5; PSMB6 |
| mobilization | 161 | 5 | 8.08E−01 | 8.87E−01 | 0.68 | CBX2; HBEGF; MYD88; PSMA5; PSMB6 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| cranial skeletal system development: GO | 53 | 1 | 8.11E−01 | 8.88E−01 | 0.41 | EIF4A3 |
| fcgamma receptor (fcgr) dependent phagocytosis | 53 | 1 | 8.11E−01 | 8.88E−01 | 0.41 | FCGR1A |
| response: GO | 53 | 1 | 8.11E−01 | 8.88E−01 | 0.41 | SEC61G |
| negative regulation of protein polymerization: GO | 53 | 1 | 8.11E−01 | 8.88E−01 | 0.41 | TWF1 |
| non small cell lung cancer | 53 | 1 | 8.11E−01 | 8.88E−01 | 0.41 | TGFA |
| process deadenylation dependent decay: GO | 53 | 1 | 8.11E−01 | 8.88E−01 | 0.41 | EIF4A3 |
| regulation of multicellular organism growth: GO | 53 | 1 | 8.11E−01 | 8.88E−01 | 0.41 | PPIB |
| single organism membrane fusion: GO | 109 | 3 | 8.11E−01 | 8.88E−01 | 0.60 | BAK1; BCL2A1; DYSF |
| voltage gated cation channel activity: GO | 109 | 3 | 8.11E−01 | 8.88E−01 | 0.60 | CNGB1; HTR3A; KCNJ15 |
| nitrogen but not peptide bonds in linear amides: GO | 82 | 2 | 8.12E−01 | 8.89E−01 | 0.53 | PGLYRP2; VNN3 |
| platelet homeostasis | 82 | 2 | 8.12E−01 | 8.89E−01 | 0.53 | GNGT2; LRP8 |
| binding: GO | 110 | 3 | 8.16E−01 | 8.91E−01 | 0.60 | ADAP2; MYO1B; TWF1 |
| pathway: GO | 137 | 4 | 8.17E−01 | 8.91E−01 | 0.64 | CALR; CCNE1; NR4A3; RAN |
| site of polarized growth: GO | 137 | 4 | 8.17E−01 | 8.91E−01 | 0.64 | CDK5R1; FSCN1; GPRIN1; SNCB |
| calcium dependent protein binding: GO | 54 | 1 | 8.17E−01 | 8.91E−01 | 0.40 | S100A11 |
| clathrin binding: GO | 54 | 1 | 8.17E−01 | 8.91E−01 | 0.40 | LDLR |
| membrane depolarization: GO | 54 | 1 | 8.17E−01 | 8.91E−01 | 0.40 | CHRNA6 |
| proteoglycan biosynthetic process: GO | 54 | 1 | 8.17E−01 | 8.91E−01 | 0.40 | HS3ST3B1 |
| regulation of cartilage development: GO | 54 | 1 | 8.17E−01 | 8.91E−01 | 0.40 | WNT5A |
| rna degradation | 54 | 1 | 8.17E−01 | 8.91E−01 | 0.40 | ENO1 |
| rna polymerase ii distal enhancer sequence specific dna binding: GO | 54 | 1 | 8.17E−01 | 8.91E−01 | 0.40 | H2AFZ |
| rrna binding: GO | 54 | 1 | 8.17E−01 | 8.91E−01 | 0.40 | DDX21 |
| signaling by tgf-beta receptor complex | 54 | 1 | 8.17E−01 | 8.91E−01 | 0.40 | SERPINE1 |
| vesicle docking: GO | 54 | 1 | 8.17E−01 | 8.91E−01 | 0.40 | NDRG4 |
| pathway: GO | 83 | 2 | 8.18E−01 | 8.91E−01 | 0.53 | FCGR1A; IGHG4 |
| golgi organization: GO | 83 | 2 | 8.18E−01 | 8.91E−01 | 0.53 | CDK1; VMP1 |
| kinase inhibitor activity: GO | 83 | 2 | 8.18E−01 | 8.91E−01 | 0.53 | SFN; SOCS3 |
| integration of energy metabolism | 111 | 3 | 8.21E−01 | 8.94E−01 | 0.59 | GNA15; GNGT2; SLC25A5 |
| ubiquitin like protein ligase activity: GO | 190 | 6 | 8.22E−01 | 8.94E−01 | 0.69 | RNF222; UBE2C; UBE2F; UBE2S; UBE2T; UHRF1 |
| neural tube development: GO | 138 | 4 | 8.22E−01 | 8.94E−01 | 0.63 | GRHL3; HIF1A; STIL; WNT5A |
| ras protein signal transduction: GO | 138 | 4 | 8.22E−01 | 8.94E−01 | 0.63 | CCNA2; DOK3; PLK2; RALB |
| positive regulation of viral process: GO | 84 | 2 | 8.24E−01 | 8.94E−01 | 0.52 | PPIB; TOP2A |
| regulation of cell matrix adhesion: GO | 84 | 2 | 8.24E−01 | 8.94E−01 | 0.52 | PLAU; SERPINE1 |
| small cell lung cancer | 84 | 2 | 8.24E−01 | 8.94E−01 | 0.52 | CCNE1; CYCS |
| toll like receptor 4 (tlr4) cascade | 84 | 2 | 8.24E−01 | 8.94E−01 | 0.52 | MYD88; S100A12 |
| insulin pathway | 55 | 1 | 8.24E−01 | 8.94E−01 | 0.40 | EIF4EBP1 |
| negative regulation of nucleotide metabolic process: GO | 55 | 1 | 8.24E−01 | 8.94E−01 | 0.40 | PPIF |
| notch pathway | 55 | 1 | 8.24E−01 | 8.94E−01 | 0.40 | ENO1 |
| photoreceptor outer segment: GO | 55 | 1 | 8.24E−01 | 8.94E−01 | 0.40 | CNGB1 |
| pi3k cascade | 55 | 1 | 8.24E−01 | 8.94E−01 | 0.40 | EIF4EBP1 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| coenzyme biosynthetic process: GO | 112 | 3 | 8.26E−01 | 8.95E−01 | 0.59 | KYNU; NAMPT; PNP |
| development: GO | 112 | 3 | 8.26E−01 | 8.95E−01 | 0.59 | EIF4A3; MDFI; WNT5A |
| negative regulation of cytoplasmic transport: GO | 112 | 3 | 8.26E−01 | 8.95E−01 | 0.59 | GSTO1; MDFI; ZC3H12A |
| cell cycle arrest: GO | 139 | 4 | 8.26E−01 | 8.96E−01 | 0.63 | CALR; CDKN3; IFNG; IL12B |
| calmodulin binding: GO | 166 | 5 | 8.29E−01 | 8.97E−01 | 0.66 | ASPM; CNN2; ENKUR; MYO1B; RGS1 |
| gab1 signalosome | 166 | 5 | 8.29E−01 | 8.97E−01 | 0.66 | CBX2; HBEGF; MYD88; PSMA5; PSMB6 |
| regulation of neurotransmitter levels: GO | 166 | 5 | 8.29E−01 | 8.97E−01 | 0.66 | CHRNA3; HRH3; HSPA8; RIMS3; WNT7A |
| process: GO | 85 | 2 | 8.29E−01 | 8.97E−01 | 0.51 | CYP4F22; PLA2G3 |
| nonsense mediated decay enhanced by the exon junction complex | 85 | 2 | 8.29E−01 | 8.97E−01 | 0.51 | EIF4A3; RPL26L1 |
| phosphoric diester hydrolase activity: GO | 85 | 2 | 8.29E−01 | 8.97E−01 | 0.51 | CCR5; HMOX1 |
| signaling by erbb4 | 85 | 2 | 8.29E−01 | 8.97E−01 | 0.51 | CDK1; HBEGF |
| initiation: GO | 192 | 6 | 8.29E−01 | 8.97E−01 | 0.68 | HIST1H4I; HIST1H4J; HIST1H4K; HIST1H4L; NR4A3; POLR3G |
| inositol phosphate metabolic process: GO | 56 | 1 | 8.30E−01 | 8.97E−01 | 0.39 | PTAFR |
| p53 regulation pathway | 56 | 1 | 8.30E−01 | 8.97E−01 | 0.39 | CCNA2 |
| protein homotetramerization: GO | 56 | 1 | 8.30E−01 | 8.97E−01 | 0.39 | TK1 |
| neurotrophin signaling pathway | 113 | 3 | 8.30E−01 | 8.97E−01 | 0.58 | CALML3; CALML5; YWHAQ |
| assembly: GO | 140 | 4 | 8.31E−01 | 8.97E−01 | 0.62 | FAM110C; FSCN1; PRKCQ; RAC2 |
| process: GO | 86 | 2 | 8.34E−01 | 9.00E−01 | 0.51 | IL19; PRDX1 |
| cytosol | 86 | 2 | 8.34E−01 | 9.00E−01 | 0.51 | RPL22L1; RPP40 |
| striated muscle contraction: GO | 86 | 2 | 8.34E−01 | 9.00E−01 | 0.51 | CXCR4; HOMER1 |
| bone development: GO | 141 | 4 | 8.35E−01 | 9.00E−01 | 0.62 | ACP5; ALPL; LTF; PPIB |
| mrna binding: GO | 141 | 4 | 8.35E−01 | 9.00E−01 | 0.62 | C1QBP; CALR; EIF4A3; ZC3H12A |
| neuron projection terminus: GO | 114 | 3 | 8.35E−01 | 9.00E−01 | 0.58 | ADCYAP1; CCK; SNCB |
| acute myeloid leukemia | 57 | 1 | 8.36E−01 | 9.00E−01 | 0.38 | EIF4EBP1 |
| nade | 57 | 1 | 8.36E−01 | 9.00E−01 | 0.38 | ECT2 |
| era genomic pathway | 57 | 1 | 8.36E−01 | 9.00E−01 | 0.38 | PCNA |
| map kinase activation in tlr cascade | 57 | 1 | 8.36E−01 | 9.00E−01 | 0.38 | CDK1 |
| regulation of phospholipid metabolic process: GO | 57 | 1 | 8.36E−01 | 9.00E−01 | 0.38 | LDLR |
| signal release: GO | 142 | 4 | 8.39E−01 | 9.02E−01 | 0.62 | HRH3; HSPA8; IL6; WNT7A |
| chloride transport: GO | 87 | 2 | 8.39E−01 | 9.02E−01 | 0.50 | CLCA2; SLC26A9 |
| protein kinase complex: GO | 87 | 2 | 8.39E−01 | 9.02E−01 | 0.50 | CCNE1; PYCARD |
| regulation of rna splicing: GO | 87 | 2 | 8.39E−01 | 9.02E−01 | 0.50 | C1QBP; HSPA8 |
| single fertilization: GO | 87 | 2 | 8.39E−01 | 9.02E−01 | 0.50 | CCT5; CDK1 |
| regulation of heart contraction: GO | 195 | 6 | 8.40E−01 | 9.03E−01 | 0.67 | ATP1B3; DSC2; GSTO1; HBEGF; IFNG; ZC3H12A |
| hormone transport: GO | 58 | 1 | 8.42E−01 | 9.03E−01 | 0.38 | IL6 |
| myosin complex: GO | 58 | 1 | 8.42E−01 | 9.03E−01 | 0.38 | MYO1B |
| nucleolar part: GO | 58 | 1 | 8.42E−01 | 9.03E−01 | 0.38 | RPP40 |
| pi3k/akt signaling in cancer | 58 | 1 | 8.42E−01 | 9.03E−01 | 0.38 | HBEGF |
| regulation of potassium ion transmembrane transport: GO | 58 | 1 | 8.42E−01 | 9.03E−01 | 0.38 | ATP1B3 |
| regulation of smoothened signaling pathway: GO | 58 | 1 | 8.42E−01 | 9.03E−01 | 0.38 | CD3E |
| response to osmotic stress: GO | 58 | 1 | 8.42E−01 | 9.03E−01 | 0.38 | HIF1A |
| downstream signaling events of b cell | 170 | 5 | 8.44E−01 | 9.05E−01 | 0.64 | CBX2; HBEGF; MYD88; PSMA5; PSMB6 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| receptor (bcr) | | | | | | |
| antigen processing ubiquitination proteasome degradation | 88 | 2 | 8.44E−01 | 9.05E−01 | 0.50 | PSMA4; UBE2S |
| morphogenesis: GO | 88 | 2 | 8.44E−01 | 9.05E−01 | 0.50 | EIF4A3; MDFI |
| transcriptional repressor activity rna polymerase ii transcription regulatory region sequence specific binding: GO | 144 | 4 | 8.47E−01 | 9.07E−01 | 0.61 | HMGA2; IFI16; MXD1; PRDMI |
| ar pathway | 59 | 1 | 8.48E−01 | 9.07E−01 | 0.37 | PRDX1 |
| positive regulation of actin filament polymerization: GO | 59 | 1 | 8.48E−01 | 9.07E−01 | 0.37 | PYCARD |
| activity: GO | 59 | 1 | 8.48E−01 | 9.07E−01 | 0.37 | ADCYAP1 |
| regulation of muscle adaptation: GO | 59 | 1 | 8.48E−01 | 9.07E−01 | 0.37 | NR4A3 |
| polymerase ii transcription factor binding: GO | 117 | 3 | 8.48E−01 | 9.07E−01 | 0.56 | EOMES; HIF1A; PITX1 |
| late endosome membrane: GO | 89 | 2 | 8.49E−01 | 9.08E−01 | 0.49 | IFITM3; NTRK1 |
| oxidoreductase complex: GO | 89 | 2 | 8.49E−01 | 9.08E−01 | 0.49 | OGDHL; RRM2 |
| rrna processing | 89 | 2 | 8.49E−01 | 9.08E−01 | 0.49 | RPL22L1; RPP40 |
| protein import: GO | 145 | 4 | 8.51E−01 | 9.09E−01 | 0.60 | IFNG; JAK3; KPNA2; RAN |
| hepaticobiliary system development: GO | 118 | 3 | 8.53E−01 | 9.11E−01 | 0.56 | CCNE1; PCSK9; TK1 |
| muscle organ morphogenesis: GO | 60 | 1 | 8.54E−01 | 9.11E−01 | 0.36 | WNT5A |
| pathway: GO | 60 | 1 | 8.54E−01 | 9.11E−01 | 0.36 | CHAC1 |
| basement membrane: GO | 90 | 2 | 8.54E−01 | 9.11E−01 | 0.49 | GSTO1; TNC |
| process: GO | 90 | 2 | 8.54E−01 | 9.11E−01 | 0.49 | ALDH4A1; GOT2 |
| development: GO | 90 | 2 | 8.54E−01 | 9.11E−01 | 0.49 | CCNB1; CDK1 |
| disassembly: GO | 173 | 5 | 8.55E−01 | 9.12E−01 | 0.63 | HSPA8; KIF14; KIF18A; KIF2C; MRPL51 |
| myeloid cell differentiation: GO | 173 | 5 | 8.55E−01 | 9.12E−01 | 0.63 | ACP5; CSF2; IFI16; MMP9; TNFSF9 |
| glial cell differentiation: GO | 119 | 3 | 8.57E−01 | 9.13E−01 | 0.55 | GSTP1; S100A8; S100A9 |
| striated muscle cell differentiation: GO | 147 | 4 | 8.58E−01 | 9.13E−01 | 0.60 | CALR; CCNB1; CDK1; HOMER1 |
| lipid phosphorylation: GO | 91 | 2 | 8.59E−01 | 9.13E−01 | 0.48 | CD80; HBEGF |
| cell cell contact zone: GO | 61 | 1 | 8.59E−01 | 9.13E−01 | 0.36 | DSC2 |
| metal cluster binding: GO | 61 | 1 | 8.59E−01 | 9.13E−01 | 0.36 | RSAD2 |
| positive regulation of dendrite development: GO | 61 | 1 | 8.59E−01 | 9.13E−01 | 0.36 | LRP8 |
| regulation of protein acetylation: GO | 61 | 1 | 8.59E−01 | 9.13E−01 | 0.36 | IL1B |
| single stranded rna binding: GO | 61 | 1 | 8.59E−01 | 9.13E−01 | 0.36 | EIF4A3 |
| maintenance: GO | 61 | 1 | 8.59E−01 | 9.13E−01 | 0.36 | WNT7A |
| trkr pathway | 61 | 1 | 8.59E−01 | 9.13E−01 | 0.36 | NTRK1 |
| sarcolemma: GO | 120 | 3 | 8.61E−01 | 9.15E−01 | 0.55 | CTSB; DYSF; PRKCQ |
| negative regulation of intracellular protein transport: GO | 92 | 2 | 8.63E−01 | 9.16E−01 | 0.48 | MDFI; ZC3H12A |
| renal system process: GO | 92 | 2 | 8.63E−01 | 9.16E−01 | 0.48 | AQP3; CHRNA3 |
| ubiquitin like protein specific protease activity: GO | 92 | 2 | 8.63E−01 | 9.16E−01 | 0.48 | USP43; ZC3H12A |
| long-term depression | 62 | 1 | 8.64E−01 | 9.16E−01 | 0.35 | PLA2G3 |
| processing of capped intron containing pre mrna | 62 | 1 | 8.64E−01 | 9.16E−01 | 0.35 | SNRPG |
| regulation of calcium ion transmembrane | 62 | 1 | 8.64E−01 | 9.16E−01 | 0.35 | GSTO1 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| transporter activity: GO | | | | | | |
| regulation of epithelial to mesenchymal transition: GO | 62 | 1 | 8.64E−01 | 9.16E−01 | 0.35 | SERPINB3 |
| regulation of ras protein signal transduction: GO | 176 | 5 | 8.65E−01 | 9.17E−01 | 0.62 | ECT2; FOXM1; KIF14; NTRK1; PLEKHG7 |
| brush border: GO | 93 | 2 | 8.67E−01 | 9.18E−01 | 0.47 | MYO1B; SLC5A1 |
| mrna splicing - major pathway | 93 | 2 | 8.67E−01 | 9.18E−01 | 0.47 | HSPA8; SNRPF |
| rna pol ii transcription | 93 | 2 | 8.67E−01 | 9.18E−01 | 0.47 | SNRPF; SNRPG |
| stimulus: GO | 93 | 2 | 8.67E−01 | 9.18E−01 | 0.47 | CNGB1; OR2I1P |
| maintenance of cell number: GO | 122 | 3 | 8.68E−01 | 9.18E−01 | 0.54 | ASPM; EOMES; WNT7A |
| activation of the mrna upon binding of the cap binding complex and eifs and subsequent binding to 43s | 63 | 1 | 8.69E−01 | 9.18E−01 | 0.35 | EIF4EBP1 |
| adherens junction organization: GO | 63 | 1 | 8.69E−01 | 9.18E−01 | 0.35 | CDH3 |
| long-term potentiation | 63 | 1 | 8.69E−01 | 9.18E−01 | 0.35 | CALML3 |
| tooth: GO | 63 | 1 | 8.69E−01 | 9.18E−01 | 0.35 | TNC |
| protein complex scaffold: GO | 63 | 1 | 8.69E−01 | 9.18E−01 | 0.35 | CD3E |
| regulation of cardiac conduction: GO | 63 | 1 | 8.69E−01 | 9.18E−01 | 0.35 | ATP1B3 |
| sarcoplasm: GO | 63 | 1 | 8.69E−01 | 9.18E−01 | 0.35 | CALR |
| transmembrane receptor protein tyrosine kinase activity: GO | 63 | 1 | 8.69E−01 | 9.18E−01 | 0.35 | NTRK1 |
| cluster of actin based cell projections: GO | 123 | 3 | 8.72E−01 | 9.21E−01 | 0.53 | IDO1; MYO1B; SLC5A1 |
| p53 binding: GO | 64 | 1 | 8.74E−01 | 9.22E−01 | 0.34 | BLM |
| process: GO | 64 | 1 | 8.74E−01 | 9.22E−01 | 0.34 | NME1 |
| regulation of tor signaling: GO | 64 | 1 | 8.74E−01 | 9.22E−01 | 0.34 | HIF1A |
| locomotory behavior: GO | 152 | 4 | 8.76E−01 | 9.24E−01 | 0.58 | ALDH1A3; CHRNA3; CSTB; IDO1 |
| ber 5pathway | 65 | 1 | 8.78E−01 | 9.26E−01 | 0.34 | BCL2A1 |
| ciliary membrane: GO | 65 | 1 | 8.78E−01 | 9.26E−01 | 0.34 | CNGB1 |
| membrane docking: GO | 65 | 1 | 8.78E−01 | 9.26E−01 | 0.34 | NDRG4 |
| influenza life cycle | 154 | 4 | 8.82E−01 | 9.29E−01 | 0.57 | CALR; RAN; RPL22L1; RPL26L1 |
| lyase activity: GO | 154 | 4 | 8.82E−01 | 9.29E−01 | 0.57 | ENO1; HAL; HMGA2; POLQ |
| regulation of bmp signaling pathway: GO | 66 | 1 | 8.83E−01 | 9.29E−01 | 0.33 | WNT5A |
| tgf-beta signaling pathway | 66 | 1 | 8.83E−01 | 9.29E−01 | 0.33 | IFNG |
| magnesium ion binding: GO | 183 | 5 | 8.87E−01 | 9.33E−01 | 0.60 | ENO1; NME1; PGM2; PIF1; TOP2A |
| dephosphorylation: GO | 67 | 1 | 8.87E−01 | 9.33E−01 | 0.33 | PKMYT1 |
| organellar ribosome: GO | 67 | 1 | 8.87E−01 | 9.33E−01 | 0.33 | MRPL51 |
| smad binding: GO | 67 | 1 | 8.87E−01 | 9.33E−01 | 0.33 | HMGA2 |
| negative regulation of cell growth: GO | 156 | 4 | 8.89E−01 | 9.34E−01 | 0.56 | CDK5R1; CYP27B1; ENO1; WNT5A |
| pdgfrb pathway | 128 | 3 | 8.90E−01 | 9.34E−01 | 0.51 | SFN; STAT1; YWHAQ |
| notch signaling pathway: GO | 99 | 2 | 8.91E−01 | 9.34E−01 | 0.44 | CHAC1; IL2RA |
| signaling by erbb2 | 99 | 2 | 8.91E−01 | 9.34E−01 | 0.44 | CDK1; HBEGF |
| cellular response to ketone: GO | 68 | 1 | 8.91E−01 | 9.34E−01 | 0.32 | IL6 |
| dna modification: GO | 68 | 1 | 8.91E−01 | 9.34E−01 | 0.32 | APOBEC3A |
| inositol phosphate metabolism | 68 | 1 | 8.91E−01 | 9.34E−01 | 0.32 | TPI1 |
| microvillus: GO | 68 | 1 | 8.91E−01 | 9.34E−01 | 0.32 | FSCN1 |
| rac1 pathway | 68 | 1 | 8.91E−01 | 9.34E−01 | 0.32 | CDK5R1 |
| secretory granule membrane: GO | 68 | 1 | 8.91E−01 | 9.34E−01 | 0.32 | LAMP3 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| actin filament organization: GO | 157 | 4 | 8.92E−01 | 9.34E−01 | 0.56 | FSCN1; MYO1B; RAC2; TMSB10 |
| cell substrate adhesion: GO | 157 | 4 | 8.92E−01 | 9.34E−01 | 0.56 | HPSE; ITGB6; KIF14; TNFRSF12A |
| protein autophosphorylation: GO | 185 | 5 | 8.92E−01 | 9.35E−01 | 0.59 | AURKA; JAK3; MELK; NEK2; NTRK1 |
| peptide chain elongation | 100 | 2 | 8.94E−01 | 9.36E−01 | 0.44 | RPL22L1; RPL26L1 |
| voltage gated ion channel activity: GO | 158 | 4 | 8.94E−01 | 9.36E−01 | 0.55 | CNGB1; HTR3A; KCNJ15; KCNK10 |
| developmental cell growth: GO | 69 | 1 | 8.96E−01 | 9.37E−01 | 0.32 | AURKA |
| endothelial cell differentiation: GO | 69 | 1 | 8.96E−01 | 9.37E−01 | 0.32 | WNT7A |
| lipid oxidation: GO | 69 | 1 | 8.96E−01 | 9.37E−01 | 0.32 | ADH7 |
| fatty acid metabolism | 159 | 4 | 8.97E−01 | 9.38E−01 | 0.55 | ADH7; ALDH1A3; CYP4F11; CYP4F22 |
| signaling by the b cell receptor (bcr) | 187 | 5 | 8.98E−01 | 9.39E−01 | 0.58 | CBX2; HBEGF; MYD88; PSMA5; PSMB6 |
| calcium ion regulated exocytosis: GO | 70 | 1 | 8.99E−01 | 9.39E−01 | 0.31 | RIMS3 |
| metanephros development: GO | 70 | 1 | 8.99E−01 | 9.39E−01 | 0.31 | STAT1 |
| mrna 3 end processing: GO | 70 | 1 | 8.99E−01 | 9.39E−01 | 0.31 | EIF4A3 |
| neural crest cell differentiation: GO | 70 | 1 | 8.99E−01 | 9.39E−01 | 0.31 | HIF1A |
| glycerolipid biosynthetic process: GO | 188 | 5 | 9.00E−01 | 9.40E−01 | 0.58 | FABP5; GK; PIGW; PLA2G4D; PLAUR |
| regulation of stem cell differentiation: GO | 102 | 2 | 9.01E−01 | 9.40E−01 | 0.43 | HMGA2; SERPINB3 |
| response to amino acid: GO | 102 | 2 | 9.01E−01 | 9.40E−01 | 0.43 | GSTP1; IL6 |
| mitochondrial membrane part: GO | 132 | 3 | 9.02E−01 | 9.40E−01 | 0.50 | BAK1; COX7B; PPIF |
| specification: GO | 161 | 4 | 9.03E−01 | 9.40E−01 | 0.54 | AURKA; FOXF1; RGS20; WNT5A |
| positive regulation of cytoskeleton organization: GO | 161 | 4 | 9.03E−01 | 9.40E−01 | 0.54 | CCNB1; GPR65; PRKCQ; PYCARD |
| adherens junction | 71 | 1 | 9.03E−01 | 9.40E−01 | 0.31 | RAC2 |
| adult locomotory behavior: GO | 71 | 1 | 9.03E−01 | 9.40E−01 | 0.31 | CSTB |
| multicellular organism growth: GO | 71 | 1 | 9.03E−01 | 9.40E−01 | 0.31 | STIL |
| n acetyltransferase activity: GO | 71 | 1 | 9.03E−01 | 9.40E−01 | 0.31 | ESCO2 |
| regulation of lyase activity: GO | 71 | 1 | 9.03E−01 | 9.40E−01 | 0.31 | ADCYAPI |
| signaling by notch1 | 71 | 1 | 9.03E−01 | 9.40E−01 | 0.31 | HIF1A |
| establishment of protein localization to endoplasmic reticulum: GO | 103 | 2 | 9.04E−01 | 9.41E−01 | 0.42 | RPL26L1; SEC61G |
| cardiac conduction: GO | 72 | 1 | 9.07E−01 | 9.41E−01 | 0.30 | DSC2 |
| ciliary basal body: GO | 72 | 1 | 9.07E−01 | 9.41E−01 | 0.30 | POC1A |
| flavin adenine dinucleotide binding: GO | 72 | 1 | 9.07E−01 | 9.41E−01 | 0.30 | SQLE |
| opioid signalling | 72 | 1 | 9.07E−01 | 9.41E−01 | 0.30 | GNGT2 |
| regulation of calcium ion dependent exocytosis: GO | 72 | 1 | 9.07E−01 | 9.41E−01 | 0.30 | RIMS3 |
| heat: GO | 72 | 1 | 9.07E−01 | 9.41E−01 | 0.30 | HSPA8 |
| transcription coupled nucleotide excision repair: GO | 72 | 1 | 9.07E−01 | 9.41E−01 | 0.30 | PCNA |
| transcriptional repressor complex: GO | 72 | 1 | 9.07E−01 | 9.41E−01 | 0.30 | DEPDC1 |
| regulation of rho protein signal transduction: GO | 104 | 2 | 9.07E−01 | 9.42E−01 | 0.42 | ECT2; PLEKHG7 |
| huntingtons disease | 134 | 3 | 9.08E−01 | 9.42E−01 | 0.49 | COX7B; CYCS; SLC25A5 |
| early endosome membrane: GO | 105 | 2 | 9.10E−01 | 9.44E−01 | 0.42 | FCGR1A; NTRK1 |
| trna metabolic process: GO | 164 | 4 | 9.11E−01 | 9.44E−01 | 0.53 | GARS; GTF3C6; RPP40; TARS |
| negative regulation of cell projection organization: GO | 136 | 3 | 9.13E−01 | 9.47E−01 | 0.48 | CDK5R1; PLK2; WNT5A |
| fibroblast growth factor receptor | 74 | 1 | 9.14E−01 | 9.47E−01 | 0.30 | FGFBP1 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| signaling pathway: GO | | | | | | |
| heart morphogenesis: GO | 194 | 5 | 9.15E−01 | 9.48E−01 | 0.56 | FOXF1; HIF1A; NDRG4; STIL; WNT5A |
| multicellular organismal signaling: GO | 107 | 2 | 9.16E−01 | 9.49E−01 | 0.41 | CNTNAP2; DSC2 |
| negative regulation of cellular response to growth factor stimulus: GO | 107 | 2 | 9.16E−01 | 9.49E−01 | 0.41 | CXCL13; WNT5A |
| protein modification by small protein removal: GO | 107 | 2 | 9.16E−01 | 9.49E−01 | 0.41 | USP43; ZC3H12A |
| regulation of heart rate: GO | 75 | 1 | 9.17E−01 | 9.49E−01 | 0.29 | DSC2 |
| protein acylation: GO | 138 | 3 | 9.18E−01 | 9.50E−01 | 0.48 | ESCO2; OAS2; TRIM16 |
| regulation of dephosphorylation: GO | 138 | 3 | 9.18E−01 | 9.50E−01 | 0.48 | CDCA2; IFNG; PKMYT1 |
| cytosolic ribosome: GO | 108 | 2 | 9.19E−01 | 9.50E−01 | 0.40 | RPL22L1; RPL26L1 |
| plasma membrane organization: GO | 196 | 5 | 9.19E−01 | 9.50E−01 | 0.56 | ATP1B3; CXCR4; DYSF; PIGW; RAB31 |
| peroxisome | 76 | 1 | 9.20E−01 | 9.51E−01 | 0.29 | PRDX1 |
| rho gtpase binding: GO | 76 | 1 | 9.20E−01 | 9.51E−01 | 0.29 | ECT2 |
| process: GO | 109 | 2 | 9.22E−01 | 9.51E−01 | 0.40 | PIGW; PLAUR |
| protein acetylation: GO | 109 | 2 | 9.22E−01 | 9.51E−01 | 0.40 | ESCO2; TRIM16 |
| rna localization: GO | 169 | 4 | 9.22E−01 | 9.51E−01 | 0.52 | EIF4A3; EIF5A; EIF5AL1; RAN |
| transport: GO | 140 | 3 | 9.23E−01 | 9.51E−01 | 0.47 | CCL3; CCR5; CHRNA9 |
| cortical cytoskeleton: GO | 77 | 1 | 9.23E−01 | 9.51E−01 | 0.28 | SELE |
| dendrite development: GO | 77 | 1 | 9.23E−01 | 9.51E−01 | 0.28 | WNT7A |
| golgi associated vesicle: GO | 77 | 1 | 9.23E−01 | 9.51E−01 | 0.28 | CNGB1 |
| heart process: GO | 77 | 1 | 9.23E−01 | 9.51E−01 | 0.28 | CXCR4 |
| inner mitochondrial membrane protein complex: GO | 77 | 1 | 9.23E−01 | 9.51E−01 | 0.28 | PPIF |
| cell cortex part: GO | 110 | 2 | 9.24E−01 | 9.52E−01 | 0.40 | RALB; SELE |
| phosphatase regulator activity: GO | 78 | 1 | 9.26E−01 | 9.53E−01 | 0.28 | PPP4R1 |
| pigmentation: GO | 78 | 1 | 9.26E−01 | 9.53E−01 | 0.28 | RAB38 |
| regulation of lipid metabolism by peroxisome proliferator-activated receptor alpha (pparalpha) | 78 | 1 | 9.26E−01 | 9.53E−01 | 0.28 | TNFRSF21 |
| regulation of translational initiation: GO | 78 | 1 | 9.26E−01 | 9.53E−01 | 0.28 | EIF4EBPJ |
| transmembrane receptor protein kinase activity: GO | 78 | 1 | 9.26E−01 | 9.53E−01 | 0.28 | NTRK1 |
| inorganic anion transport: GO | 111 | 2 | 9.27E−01 | 9.53E−01 | 0.39 | CLCA2; SLC26A9 |
| recycling endosome: GO | 111 | 2 | 9.27E−01 | 9.53E−01 | 0.39 | RAN; ST8S1A2 |
| regulation of phosphatase activity: GO | 111 | 2 | 9.27E−01 | 9.53E−01 | 0.39 | IFNG; PKMYT1 |
| regulation of actin filament length: GO | 142 | 3 | 9.28E−01 | 9.53E−01 | 0.46 | PYCARD; SH3BGRL3; TWF1 |
| regulation of blood pressure: GO | 142 | 3 | 9.28E−01 | 9.53E−01 | 0.46 | ADM2; HMOX1; PTAFR |
| translational initiation: GO | 142 | 3 | 9.28E−01 | 9.53E−01 | 0.46 | EIF4EBP1; EIF6; RPL26L1 |
| beta catenin binding: GO | 79 | 1 | 9.29E−01 | 9.53E−01 | 0.28 | RGS20 |
| nephron epithelium development: GO | 79 | 1 | 9.29E−01 | 9.53E−01 | 0.28 | PGF |
| positive regulation of protein polymerization: GO | 79 | 1 | 9.29E−01 | 9.53E−01 | 0.28 | PYCARD |
| potassium channel complex: GO | 79 | 1 | 9.29E−01 | 9.53E−01 | 0.28 | CNTNAP2 |
| srp dependent cotranslational protein targeting to membrane | 79 | 1 | 9.29E−01 | 9.53E−01 | 0.28 | RPL26L1 |
| actin filament binding: GO | 112 | 2 | 9.29E−01 | 9.53E−01 | 0.39 | FSCN1; MYO1B |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| cell matrix adhesion: GO | 112 | 2 | 9.29E−01 | 9.53E−01 | 0.39 | HPSE; ITGB6 |
| dilated cardiomyopathy | 80 | 1 | 9.31E−01 | 9.55E−01 | 0.27 | ITGB6 |
| mesonephros development: GO | 80 | 1 | 9.31E−01 | 9.55E−01 | 0.27 | PGF |
| late phase of hiv life cycle | 114 | 2 | 9.34E−01 | 9.56E−01 | 0.38 | RAN; RCC1 |
| nuclear transcription factor complex: GO | 114 | 2 | 9.34E−01 | 9.56E−01 | 0.38 | GTF3C6; HIF1A |
| mrna splicing | 145 | 3 | 9.34E−01 | 9.56E−01 | 0.45 | HSPA8; SNRPF; SNRPG |
| coated membrane: GO | 81 | 1 | 9.34E−01 | 9.56E−01 | 0.27 | AP1S3 |
| enhancer binding: GO | 81 | 1 | 9.34E−01 | 9.56E−01 | 0.27 | H2AFZ |
| fertilization: GO | 115 | 2 | 9.36E−01 | 9.58E−01 | 0.38 | CCT5; CDK1 |
| synaptic vesicle cycle: GO | 82 | 1 | 9.37E−01 | 9.58E−01 | 0.27 | WNT7A |
| protein localization to cell periphery: GO | 147 | 3 | 9.38E−01 | 9.59E−01 | 0.45 | ATP1B3; PIGW; RAB31 |
| diabetes pathways | 116 | 2 | 9.38E−01 | 9.59E−01 | 0.38 | CALR; MMPI |
| actin filament based movement: GO | 83 | 1 | 9.39E−01 | 9.59E−01 | 0.26 | MYO1B |
| receptor signaling protein serine threonine kinase activity: GO | 83 | 1 | 9.39E−01 | 9.59E−01 | 0.26 | MAPK6 |
| cofactor biosynthetic process: GO | 148 | 3 | 9.40E−01 | 9.60E−01 | 0.44 | KYNU; NAMPT; PNP |
| intrinsic component of endoplasmic reticulum membrane: GO | 117 | 2 | 9.40E−01 | 9.60E−01 | 0.37 | CALR; TAP2 |
| nuclear transcribed mrna catabolic process nonsense mediated decay: GO | 117 | 2 | 9.40E−01 | 9.60E−01 | 0.37 | EIF4A3; RPL26L1 |
| pdz domain binding: GO | 84 | 1 | 9.41E−01 | 9.61E−01 | 0.26 | KIF14 |
| transport: GO | 180 | 4 | 9.43E−01 | 9.62E−01 | 0.49 | EIF4A3; EIF5A; EIF5AL 1; RAN |
| ribonucleoprotein complex subunit organization: GO | 181 | 4 | 9.45E−01 | 9.64E−01 | 0.48 | C1QBP; EIF6; SNRPF; SNRPG |
| acetyltransferase activity: GO | 86 | 1 | 9.46E−01 | 9.64E−01 | 0.25 | ESCO2 |
| downstream signaling of activated fgfr | 86 | 1 | 9.46E−01 | 9.64E−01 | 0.25 | CDK1 |
| endothelium development: GO | 86 | 1 | 9.46E−01 | 9.64E−01 | 0.25 | WNT7A |
| organelle membrane fusion: GO | 86 | 1 | 9.46E−01 | 9.64E−01 | 0.25 | DYSF |
| extracellular matrix component: GO | 120 | 2 | 9.46E−01 | 9.64E−01 | 0.36 | GSTO1; TNC |
| n acyltransferase activity: GO | 87 | 1 | 9.48E−01 | 9.65E−01 | 0.25 | ESCO2 |
| h: GO | 87 | 1 | 9.48E−01 | 9.65E−01 | 0.25 | TXNDC17 |
| positive regulation of transmembrane receptor protein serine threonine kinase signaling pathway: GO | 87 | 1 | 9.48E−01 | 9.65E−01 | 0.25 | TTK |
| process: GO | 153 | 3 | 9.49E−01 | 9.65E−01 | 0.43 | ALDH1A3; CH25H; IDO1 |
| protein localization to endoplasmic reticulum: GO | 122 | 2 | 9.50E−01 | 9.66E−01 | 0.36 | RPL26L1; SEC61G |
| signaling by fgfr | 123 | 2 | 9.52E−01 | 9.67E−01 | 0.36 | CDK1; FGFBP1 |
| establishment of protein localization to plasma membrane: GO | 89 | 1 | 9.52E−01 | 9.67E−01 | 0.25 | RAB31 |
| rna polymerase ii transcription factor complex: GO | 89 | 1 | 9.52E−01 | 9.67E−01 | 0.25 | HIF1A |
| processing of capped intron-containing pre-mrna | 124 | 2 | 9.53E−01 | 9.68E−01 | 0.35 | HSPA8; SNRPF |
| regulation of phosphatidylinositol 3 kinase signaling: GO | 124 | 2 | 9.53E−01 | 9.68E−01 | 0.35 | CD80; HBEGF |
| signaling by fgfr in disease | 124 | 2 | 9.53E−01 | 9.68E−01 | 0.35 | CDK1; STAT1 |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| ribosomal subunit: GO | 156 | 3 | 9.53E−01 | 9.68E−01 | 0.42 | MRPL51; RPL22L1; RPL26L1 |
| translational termination: GO | 91 | 1 | 9.55E−01 | 9.70E−01 | 0.24 | MRPL51 |
| met pathway | 92 | 1 | 9.57E−01 | 9.71E−01 | 0.24 | EIF4EBP1 |
| negative regulation of transmembrane receptor protein serine threonine kinase signaling pathway: GO | 92 | 1 | 9.57E−01 | 9.71E−01 | 0.24 | WNT5A |
| rna 3 end processing: GO | 92 | 1 | 9.57E−01 | 9.71E−01 | 0.24 | EIF4A3 |
| calcium ion transport: GO | 192 | 4 | 9.60E−01 | 9.74E−01 | 0.46 | CCL3; CCR5; CHRNA9; CYP27B1 |
| transport vesicle membrane: GO | 130 | 2 | 9.62E−01 | 9.75E−01 | 0.34 | AREG; TGFA |
| synaptic vesicle localization: GO | 96 | 1 | 9.63E−01 | 9.76E−01 | 0.23 | WNT7A |
| replication | 131 | 2 | 9.63E−01 | 9.76E−01 | 0.33 | RPL22L1; RPL26L1 |
| actin based cell projection: GO | 164 | 3 | 9.64E−01 | 9.76E−01 | 0.40 | FSCN1; MYO1B; TWF1 |
| negative regulation of cellular protein localization: GO | 132 | 2 | 9.65E−01 | 9.77E−01 | 0.33 | MDFI; ZC3H12A |
| regulation of synaptic plasticity: GO | 132 | 2 | 9.65E−01 | 9.77E−01 | 0.33 | CDC20; PLK2 |
| focal adhesion | 197 | 4 | 9.66E−01 | 9.77E−01 | 0.44 | ITGB6; PGF; RAC2; TNC |
| structural constituent of ribosome: GO | 198 | 4 | 9.67E−01 | 9.78E−01 | 0.44 | MRPL51; RPL22L1; RPL26L1; SLC25A5 |
| fatty acid biosynthetic process: GO | 100 | 1 | 9.69E−01 | 9.80E−01 | 0.22 | CH25H |
| response to transforming growth factor beta: GO | 136 | 2 | 9.69E−01 | 9.80E−01 | 0.32 | WNT5A; WNT7A |
| nephron development: GO | 101 | 1 | 9.70E−01 | 9.81E−01 | 0.22 | PGF |
| mitochondrial translation: GO | 104 | 1 | 9.73E−01 | 9.83E−01 | 0.21 | MRPL51 |
| signaling by egfr in cancer | 104 | 1 | 9.73E−01 | 9.83E−01 | 0.21 | CDK1 |
| trna processing: GO | 104 | 1 | 9.73E−01 | 9.83E−01 | 0.21 | RPP40 |
| signaling by notch | 105 | 1 | 9.75E−01 | 9.84E−01 | 0.21 | HIF1A |
| protein c terminus binding: GO | 177 | 3 | 9.77E−01 | 9.86E−01 | 0.37 | CDC20; TOP2A; YWHAQ |
| ppara activates gene expression | 109 | 1 | 9.78E−01 | 9.87E−01 | 0.20 | TNFRSF21 |
| kidney epithelium development: GO | 110 | 1 | 9.79E−01 | 9.88E−01 | 0.20 | PGF |
| nuclear speck: GO | 181 | 3 | 9.79E−01 | 9.88E−01 | 0.36 | EIF4A3; HIF1A; IFI16 |
| channel regulator activity: GO | 111 | 1 | 9.80E−01 | 9.88E−01 | 0.20 | PCSK9 |
| nucleotide excision repair: GO | 111 | 1 | 9.80E−01 | 9.88E−01 | 0.20 | PCNA |
| neuron spine: GO | 112 | 1 | 9.81E−01 | 9.88E−01 | 0.20 | CDK5R1 |
| nonmotile primary cilium: GO | 112 | 1 | 9.81E−01 | 9.88E−01 | 0.20 | CNGB1 |
| calcium ion transmembrane transporter activity: GO | 113 | 1 | 9.82E−01 | 9.88E−01 | 0.19 | CHRNA9 |
| eye: GO | 113 | 1 | 9.82E−01 | 9.88E−01 | 0.19 | HIF1A |
| divalent inorganic cation transmembrane transporter activity: GO | 150 | 2 | 9.82E−01 | 9.88E−01 | 0.29 | CHRNA9; SLC39A6 |
| i band: GO | 114 | 1 | 9.82E−01 | 9.89E−01 | 0.19 | HOMER1 |
| rna polymerase complex: GO | 115 | 1 | 9.83E−01 | 9.89E−01 | 0.19 | POLR3G |
| transferase activity transferring acyl groups other than amino acyl groups: GO | 187 | 3 | 9.83E−01 | 9.89E−01 | 0.35 | ESCO2; PIGW; SPTSSA |
| 3 utr mediated translational regulation | 116 | 1 | 9.84E−01 | 9.89E−01 | 0.19 | RPL26L1 |
| apical junction complex: GO | 116 | 1 | 9.84E−01 | 9.89E−01 | 0.19 | ECT2 |
| phosphatidylinositol binding: GO | 188 | 3 | 9.84E−01 | 9.89E−01 | 0.35 | ADAP2; MYO1B; TWF1 |
| lipid modification: GO | 189 | 3 | 9.84E−01 | 9.89E−01 | 0.35 | ADH7; CD80; HBEGF |
| tight junction | 119 | 1 | 9.86E−01 | 9.90E−01 | 0.18 | PRKCQ |

TABLE 4-continued

Functional enrichment for genes dysregulated in both PN and psoriatic lesional skin.

| | Num_Fun_genes | Common pso and PN (up) Num_IntFun_genes | Common pso and PN (up) p | Common pso and PN (up) FDR | Common pso and PN (up) FC | Common pso and PN (up) genes |
|---|---|---|---|---|---|---|
| regulation of protein polymerization: GO | 158 | 2 | 9.86E−01 | 9.91E−01 | 0.28 | PYCARD; TWF1 |
| fatty acid triacylglycerol and ketone body metabolism | 159 | 2 | 9.87E−01 | 9.91E−01 | 0.28 | GK; TNFRSF21 |
| transcription corepressor activity: GO | 194 | 3 | 9.87E−01 | 9.91E−01 | 0.34 | C1QBP; ENO1; MXD1 |
| cilium organization: GO | 160 | 2 | 9.87E−01 | 9.91E−01 | 0.27 | CNGB1; PLA2G3 |
| regulation of actin cytoskeleton | 200 | 3 | 9.89E−01 | 9.93E−01 | 0.33 | ITGAX; ITGB6; RAC2 |
| sensory perception of light stimulus: GO | 167 | 2 | 9.90E−01 | 9.93E−01 | 0.26 | CDH3; CNGB1 |
| ecm glycoproteins | 170 | 2 | 9.91E−01 | 9.94E−01 | 0.26 | NELL2; TNC |
| multi organism metabolic process: GO | 136 | 1 | 9.93E−01 | 9.95E−01 | 0.16 | RPL26L1 |
| cation channel complex: GO | 142 | 1 | 9.94E−01 | 9.97E−01 | 0.15 | CNTNAP2 |
| protein serine threonine kinase signaling pathway: GO | 183 | 2 | 9.95E−01 | 9.97E−01 | 0.24 | TTK; WNT5A |
| transcription initiation from rna polymerase ii promoter: GO | 145 | 1 | 9.95E−01 | 9.97E−01 | 0.15 | NR4A3 |
| protein targeting to membrane: GO | 153 | 1 | 9.96E−01 | 9.98E−01 | 0.14 | RPL26L1 |
| transmembrane receptor protein serine threonine kinase signaling pathway: GO | 164 | 1 | 9.98E−01 | 9.99E−01 | 0.13 | SUB1 |
| transferase activity transferring one carbon groups: GO | 169 | 1 | 9.98E−01 | 9.99E−01 | 0.13 | PRDM1 |
| primary cilium: GO | 175 | 1 | 9.99E−01 | 9.99E−01 | 0.12 | CNGB1 |
| cilium morphogenesis: GO | 176 | 1 | 9.99E−01 | 9.99E−01 | 0.12 | PLA2G3 |
| cytosolic transport: GO | 190 | 1 | 9.99E−01 | 9.99E−01 | 0.12 | WNT7A |

TABLE 5

Transcription Factors with binding sites enriched in: (A) genes up-regulated in lesional skin at baseline; (B) genes down-regulated in lesional skin by week 12 in the placebo group; (C) genes down-regulated in lesional skin by week 12 in the nemo group.

| | Motif | SEQ ID NO | A. Genes up-regulated in lesional skin at baseline p-value | FDR | B. Genes down-regulated in lesional skin by week 12 in the placebo group p-value | FDR | C. Genes down-regulated in lesional skin by week 12 in the nemo group p-value | FDR |
|---|---|---|---|---|---|---|---|---|
| EGR4_HUMAN.H10MO.D | GGSGGYRGGGM | 15 | 4.49E-06 | 2.87E-03 | 1.04E-01 | 1.00E+00 | 1.23E-08 | 7.88E-06 |
| FLI1_HUMAN.H10MO.A | RCMGGAAGYGGSK | 16 | 9.46E-06 | 6.04E-03 | 1.80E-02 | 1.00E+00 | 5.33E-04 | 2.90E-01 |
| ETV1_HUMAN.H10MO.B | SSVGRCMGGAAGYRVVSSBSSS | 17 | 1.29E-05 | 8.24E-03 | 9.56E-02 | 1.00E+00 | 8.00E-06 | 5.11E-03 |
| ELF3_HUMAN.H10MO.D | GGSAAACAGGAARY | 18 | 2.56E-05 | 1.63E-02 | 1.11E-02 | 9.99E-01 | 1.04E-02 | 9.99E-01 |
| SP2_HUMAN.H10MO.C | GGSSVGGGGGCGGGGCCDGSGS | 19 | 2.69E-05 | 1.71E-02 | 1.42E-01 | 1.00E+00 | 2.22E-08 | 1.43E-05 |
| KLF16_HUMAN.H10MO.D | GGGGGYGKGKBGGGGGGGG | 20 | 4.47E-05 | 2.83E-02 | 3.66E-01 | 1.00E+00 | 1.99E-05 | 1.27E-02 |
| CTCFL_HUMAN.H10MO.A | YBRCCASYAGRKGGCRSYV | 21 | 1.56E-04 | 9.50E-02 | 4.24E-01 | 1.00E+00 | 6.82E-08 | 4.37E-05 |
| STAT3_HUMAN.H10MO.A | YTTCCYGGAAR | 22 | 2.24E-04 | 1.34E-01 | 1.48E-01 | 1.00E+00 | 2.52E-05 | 1.60E-02 |
| ETS2_HUMAN.H10MO.C | VMVGGAAGTKS | 23 | 2.41E-04 | 1.43E-01 | 2.07E-01 | 1.00E+00 | 1.78E-03 | 6.80E-01 |
| SP4_HUMAN.H10MO.D | GGGGGCGGGGCCKGGGSSGGGS | 24 | 2.60E-04 | 1.54E-01 | 4.53E-01 | 1.00E+00 | 4.51E-08 | 2.89E-05 |
| ARNT2_HUMAN.H10MO.D | GNCGTGGSASRC | 25 | 3.75E-04 | 2.14E-01 | 2.15E-01 | 1.00E+00 | 4.28E-06 | 2.74E-03 |
| GABP1_HUMAN.H10MO.C | CCGGAAGTGV | 26 | 4.38E-04 | 2.45E-01 | 1.47E-03 | 6.11E-01 | 3.31E-06 | 2.12E-03 |
| GLIS3_HUMAN.H10MO.D | GYGGGGGGTM | 27 | 4.50E-04 | 2.51E-01 | 7.71E-03 | 9.93E-01 | 7.17E-07 | 4.60E-04 |
| ZIC2_HUMAN.H10MO.C | KGGGTGGTC | 28 | 7.49E-04 | 3.81E-01 | 5.86E-01 | 1.00E+00 | 1.84E-03 | 6.92E-01 |
| KLF15_HUMAN.H10MO.D | RSMKGGGAGDKGGGGSS | 29 | 9.72E-04 | 4.64E-01 | 8.37E-01 | 1.00E+00 | 5.35E-05 | 3.37E-02 |
| ZIC1_HUMAN.H10MO.B | KGGGWGGTS | 30 | 9.92E-04 | 4.71E-01 | 5.41E-01 | 1.00E+00 | 4.30E-04 | 2.41E-01 |
| TBX1_HUMAN.H10MO.D | GGGYGGGYAGGGGTGGGMDD | 31 | 1.02E-03 | 4.79E-01 | 1.28E-01 | 1.00E+00 | 1.81E-04 | 1.09E-01 |
| ETV7_HUMAN.H10MO.D | KCMHCAGGAAGTRACDY | 32 | 1.12E-03 | 5.13E-01 | 3.32E-03 | 8.81E-01 | 3.62E-03 | 9.02E-01 |
| TFDP1_HUMAN.H10MO.D | SSSVSSGSGSVRGGGGCGGGRV | 33 | 1.12E-03 | 5.14E-01 | 1.74E-01 | 1.00E+00 | 9.75E-07 | 6.25E-04 |
| FOXJ2_HUMAN.H10MO.C | TGTTTRTTTW | 34 | 1.19E-03 | 5.34E-01 | 4.46E-02 | 1.00E+00 | 5.94E-01 | 1.00E+00 |
| GABPA_HUMAN.H10MO.A | SVRCCGGAAGTGV | 35 | 1.32E-03 | 5.71E-01 | 3.84E-02 | 1.00E+00 | 3.86E-03 | 9.16E-01 |
| FOSL2_HUMAN.H10MO.A | RTGACTCABHN | 36 | 1.40E-03 | 5.91E-01 | 4.99E-02 | 1.00E+00 | 3.27E-03 | 8.77E-01 |
| TBX15_HUMAN.H10MO.D | GGGGGGGGGGGGGTGGGDR | 37 | 1.48E-03 | 6.13E-01 | 3.32E-01 | 1.00E+00 | 4.93E-04 | 2.71E-01 |
| PTF1A_HUMAN.H10MO.C | CRGGRAAHWSMACASSTGYSC | 38 | 1.57E-03 | 6.34E-01 | 1.17E-02 | 9.99E-01 | 2.42E-03 | 7.88E-01 |
| NR4A3_HUMAN.H10MO.D | CAAAGGTCAS | 39 | 1.61E-03 | 6.43E-01 | 8.22E-02 | 1.00E+00 | 1.76E-02 | 1.00E+00 |
| KLF1_HUMAN.H10MO.C | CAGGGTGKGGC | 40 | 2.12E-03 | 7.42E-01 | 2.11E-01 | 1.00E+00 | 2.16E-05 | 1.38E-02 |
| PURA_HUMAN.H10MO.D | GGWRKKGGDGGGCVKGG | 41 | 2.18E-03 | 7.53E-01 | 8.04E-02 | 1.00E+00 | 8.60E-06 | 5.50E-03 |
| ZN143_HUMAN.H10MO.A | GCRWKGCATKMTGGGARDTVBH | 42 | 2.54E-03 | 8.03E-01 | 2.92E-01 | 1.00E+00 | 2.79E-02 | 1.00E+00 |
| E2F1_HUMAN.H10MO.A | DDNDGGCGSGAAAV | 43 | 2.77E-03 | 8.31E-01 | 7.28E-02 | 1.00E+00 | 7.45E-06 | 4.76E-03 |
| ZKSC1_HUMAN.H10MO.C | CCYGGCACAYAGTAGGTSCTCA | 44 | 2.84E-03 | 8.38E-01 | 2.58E-01 | 1.00E+00 | 1.56E-03 | 6.32E-01 |

TABLE 5-continued

Transcription Factors with binding sites enriched in: (A) genes up-regulated in lesional skin at baseline; (B) genes down-regulated in lesional skin by week 12 in the placebo group; (C) genes down-regulated in lesional skin by week 12 in the nemo group.

| | Motif | SEQ ID NO | A. Genes up-regulated in lesional skin at baseline p-value | A. FDR | B. Genes down-regulated in lesional skin by week 12 in the placebo group p-value | B. FDR | C. Genes down-regulated in lesional skin by week 12 in the nemo group p-value | C. FDR |
|---|---|---|---|---|---|---|---|---|
| SP3_HUMAN.H10MO.B | SGVVGGGGGCGGGGCBRGSS | 45 | 2.96E-03 | 8.50E-01 | 2.17E-01 | 1.00E+00 | 1.15E-06 | 7.37E-04 |
| AP2B_HUMAN.H10MO.B | GCCYGVGGGS | 46 | 3.35E-03 | 8.83E-01 | 1.82E-02 | 1.00E+00 | 2.62E-05 | 1.67E-02 |
| REST_HUMAN.H10MO.A | TTCAGCACCAYGGACAGCKCCM | 47 | 3.35E-03 | 8.83E-01 | 1.94E-02 | 1.00E+00 | 1.54E-04 | 9.43E-02 |
| ZFX_HUMAN.H10MO.C | SVGSSSSSCAGGCCBVGSC | 48 | 3.53E-03 | 8.96E-01 | 3.38E-01 | 1.00E+00 | 1.37E-08 | 8.78E-06 |
| RHXF1_HUMAN.H10MO.D | NRGGGATYADS | 49 | 4.05E-03 | 9.26E-01 | 4.29E-01 | 1.00E+00 | 3.95E-03 | 9.20E-01 |
| KLF12_HUMAN.H10MO.D | DDGGGCGTGGYH | 50 | 4.07E-03 | 9.26E-01 | 4.94E-02 | 1.00E+00 | 4.36E-07 | 2.80E-04 |
| NR1H4_HUMAN.H10MO.C | RRGGTCADTGACCT | 51 | 4.08E-03 | 9.27E-01 | 2.85E-02 | 1.00E+00 | 1.05E-02 | 9.99E-01 |
| PROX1_HUMAN.H10MO.D | KGGKARGGCGKSKKGGG | 52 | 4.19E-03 | 9.32E-01 | 7.95E-01 | 1.00E+00 | 1.90E-02 | 1.00E+00 |
| BHE40_HUMAN.H10MO.A | KCACGTGAS | 53 | 4.50E-03 | 9.44E-01 | 6.18E-01 | 1.00E+00 | 1.11E-04 | 6.86E-02 |
| ERG_HUMAN.H10MO.B | RRACCGGAARTSV | 54 | 5.14E-03 | 9.63E-01 | 2.06E-02 | 1.00E+00 | 2.78E-04 | 1.63E-01 |
| ERR1_HUMAN.H10MO.D | GSCCAAGGTCASVS | 55 | 5.16E-03 | 9.63E-01 | 1.40E-01 | 1.00E+00 | 3.19E-05 | 2.03E-02 |
| AP2C_HUMAN.H10MO.A | VTGSCCTGRGGSHR | 56 | 5.46E-03 | 9.70E-01 | 3.01E-02 | 1.00E+00 | 9.33E-06 | 5.97E-03 |
| SP1_HUMAN.H10MO.C | GGGRRGGGGGCGGGGCSDG | 57 | 5.46E-03 | 9.70E-01 | 3.22E-01 | 1.00E+00 | 2.66E-06 | 1.71E-03 |
| P53_HUMAN.H10MO.B | RGRCATGTCTGGRCATGYCH | 58 | 5.50E-03 | 9.71E-01 | 3.42E-01 | 1.00E+00 | 5.51E-02 | 1.00E+00 |
| ETV5_HUMAN.H10MO.D | GHCAGGAAGWAAY | 59 | 5.80E-03 | 9.76E-01 | 4.40E-01 | 1.00E+00 | 5.09E-02 | 1.00E+00 |
| COE1_HUMAN.H10MO.A | DRKYCCCWGGGGAVH | 60 | 6.10E-03 | 9.80E-01 | 7.75E-01 | 1.00E+00 | 6.31E-02 | 1.00E+00 |
| MAZ_HUMAN.H10MO.A | GGGMGGGGSSGGGGGGGGGGG | 61 | 6.26E-03 | 9.82E-01 | 9.26E-01 | 1.00E+00 | 2.38E-04 | 1.42E-01 |
| NR2E1_HUMAN.H10MO.D | DMTTGACTTWTTGACTT | 62 | 6.80E-03 | 9.87E-01 | 2.00E-01 | 1.00E+00 | 6.61E-01 | 1.00E+00 |
| HXB1_HUMAN.H10MO.D | TGATKGATGG | 63 | 7.12E-03 | 9.90E-01 | 2.31E-01 | 1.00E+00 | 1.26E-02 | 1.00E+00 |
| FOXK1_HUMAN.H10MO.D | KRTTGKGTSSGT | 64 | 7.44E-03 | 9.92E-01 | 2.20E-02 | 1.00E+00 | 4.65E-02 | 1.00E+00 |
| ZN350_HUMAN.H10MO.C | ASGGGVVGCARDNVTTTGKKGCCC | 65 | 7.73E-03 | 9.93E-01 | 1.31E-01 | 1.00E+00 | 3.07E-06 | 1.96E-03 |
| NR6A1_HUMAN.H10MO.B | AAGKTCAAGKTCA | 66 | 7.74E-03 | 9.93E-01 | 1.11E-01 | 1.00E+00 | 2.77E-01 | 1.00E+00 |
| ESR2_HUMAN.H10MO.A | VRGGTCASKSTGACCTKR | 67 | 8.00E-03 | 9.94E-01 | 8.44E-03 | 9.96E-01 | 3.47E-04 | 1.99E-01 |
| ZEP2_HUMAN.H10MO.D | GGYDGGGWAACCSS | 68 | 1.23E-02 | 1.00E+00 | 4.50E-01 | 1.00E+00 | 2.21E-05 | 1.41E-02 |
| GLI1_HUMAN.H10MO.C | BTGGGTGGTCY | 69 | 1.28E-02 | 1.00E+00 | 4.55E-01 | 1.00E+00 | 4.21E-03 | 9.33E-01 |
| KLF4_HUMAN.H10MO.A | DGGGYGKGGC | 70 | 1.31E-02 | 1.00E+00 | 8.83E-01 | 1.00E+00 | 8.53E-04 | 4.21E-01 |
| E2F4_HUMAN.H10MO.A | NDDKGGCGSGAAAN | 71 | 1.34E-02 | 1.00E+00 | 2.12E-02 | 1.00E+00 | 1.91E-06 | 1.22E-03 |
| STA5B_HUMAN.H10MO.C | YTTCTKRGAAR | 72 | 1.46E-02 | 1.00E+00 | 1.02E-01 | 1.00E+00 | 9.71E-01 | 1.00E+00 |
| EVI1_HUMAN.H10MO.B | WAGAYAAGATAANAKA | 73 | 1.53E-02 | 1.00E+00 | 5.81E-02 | 1.00E+00 | 6.43E-01 | 1.00E+00 |
| JUN_HUMAN.H10MO.A | VTGAGTCAB | 74 | 1.56E-02 | 1.00E+00 | 8.17E-02 | 1.00E+00 | 1.31E-01 | 1.00E+00 |
| P73_HUMAN.H10MO.A | RGRCATGYYTGGRCWTGYYB | 75 | 1.59E-02 | 1.00E+00 | 8.32E-02 | 1.00E+00 | 9.67E-03 | 9.98E-01 |

TABLE 5-continued

Transcription Factors with binding sites enriched in: (A) genes up-regulated in lesional skin at baseline; (B) genes down-regulated in lesional skin by week 12 in the placebo group; (C) genes down-regulated in lesional skin by week 12 in the nemo group.

| | Motif | SEQ ID NO | A. Genes up-regulated in lesional skin at baseline p-value | A. FDR | B. Genes down-regulated in lesional skin by week 12 in the placebo group p-value | B. FDR | C. Genes down-regulated in lesional skin by week 12 in the nemo group p-value | C. FDR |
|---|---|---|---|---|---|---|---|---|
| ZN148_HUMAN.H10MO.D | KGRGKGGGGGAGGGG | 76 | 1.65E-02 | 1.00E+00 | 2.59E-01 | 1.00E+00 | 1.84E-03 | 6.93E-01 |
| ETV6_HUMAN.H10MO.D | WVCCGGAAGTR | 77 | 1.73E-02 | 1.00E+00 | 4.27E-01 | 1.00E+00 | 5.98E-03 | 9.78E-01 |
| STAT4_HUMAN.H10MO.D | YTTCYYRGAAR | 78 | 1.75E-02 | 1.00E+00 | 3.33E-01 | 1.00E+00 | 9.63E-01 | 1.00E+00 |
| GCR_HUMAN.H10MO.S | AGAACAK | 79 | 1.85E-02 | 1.00E+00 | 1.14E-01 | 1.00E+00 | 5.10E-01 | 1.00E+00 |
| ETS1_HUMAN.H10MO.C | ACMGGAAGT | 80 | 1.89E-02 | 1.00E+00 | 2.20E-02 | 1.00E+00 | 1.46E-02 | 1.00E+00 |
| NR2C2_HUMAN.H10MO.A | RGGTCARAGGTCA | 81 | 1.96E-02 | 1.00E+00 | 7.99E-02 | 1.00E+00 | 6.39E-02 | 1.00E+00 |
| TGIF1_HUMAN.H10MO.D | TGTSAGGTGTCASCTK | 82 | 2.02E-02 | 1.00E+00 | 6.31E-02 | 1.00E+00 | 1.30E-01 | 1.00E+00 |
| TEAD1_HUMAN.H10MO.D | YACATTCCWSMKSH | 83 | 2.04E-02 | 1.00E+00 | 7.54E-01 | 1.00E+00 | 3.54E-01 | 1.00E+00 |
| ESR1_HUMAN.H10MO.S | RGGTCASVSTGACCTGRS | 84 | 2.06E-02 | 1.00E+00 | 1.60E-01 | 1.00E+00 | 1.55E-04 | 9.44E-02 |
| EGR1_HUMAN.H10MO.A | GGGRDGYGKGGGHGGGRG | 85 | 2.07E-02 | 1.00E+00 | 5.95E-01 | 1.00E+00 | 2.20E-02 | 1.00E+00 |
| PPARG_HUMAN.H10MO.S | MAWAGGTCA | 86 | 2.12E-02 | 1.00E+00 | 6.65E-01 | 1.00E+00 | 9.30E-02 | 1.00E+00 |
| FOXD3_HUMAN.H10MO.D | TGTTTGTTT | 87 | 2.13E-02 | 1.00E+00 | 4.40E-01 | 1.00E+00 | 3.42E-01 | 1.00E+00 |
| TFE2_HUMAN.H10MO.C | AMCAGATGBYC | 88 | 2.13E-02 | 1.00E+00 | 1.89E-01 | 1.00E+00 | 5.02E-02 | 1.00E+00 |
| HSF1_HUMAN.H10MO.A | RGAANVTTCYAGAA | 89 | 2.29E-02 | 1.00E+00 | 3.28E-01 | 1.00E+00 | 3.54E-01 | 1.00E+00 |
| GRHL1_HUMAN.H10MO.D | AACCGGTTTDDC | 90 | 2.33E-02 | 1.00E+00 | 5.03E-01 | 1.00E+00 | 3.21E-01 | 1.00E+00 |
| RREB1_HUMAN.H10MO.D | DKGKKKGKGGKTGKTTTGG GKT | 91 | 2.43E-02 | 1.00E+00 | 8.68E-01 | 1.00E+00 | 1.15E-02 | 9.99E-01 |
| IRF9_HUMAN.H10MO.C | GAAAGCGAAAYT | 92 | 2.52E-02 | 1.00E+00 | 6.42E-01 | 1.00E+00 | 8.00E-02 | 1.00E+00 |
| MAFA_HUMAN.H10MO.D | STGCTGACBMYGCAGYHTY CV | 93 | 2.57E-02 | 1.00E+00 | 6.63E-01 | 1.00E+00 | 1.13E-02 | 9.99E-01 |
| AP2A_HUMAN.H10MO.C | ATKSCCTGRGGSHAD | 94 | 2.58E-02 | 1.00E+00 | 6.38E-03 | 9.83E-01 | 3.82E-04 | 2.17E-01 |
| NR1H2_HUMAN.H10MO.D | TAAAGGTCAAAGGTCAACK | 95 | 2.86E-02 | 1.00E+00 | 7.42E-02 | 1.00E+00 | 7.76E-01 | 1.00E+00 |
| THB_HUMAN.H10MO.S | SGTSAGGTCA | 96 | 2.95E-02 | 1.00E+00 | 1.02E-01 | 1.00E+00 | 1.01E-02 | 9.98E-01 |
| MAFG_HUMAN.H10MO.C | AAAANTGCTGASTCAGCAD WW | 97 | 2.96E-02 | 1.00E+00 | 1.58E-01 | 1.00E+00 | 6.50E-03 | 9.85E-01 |
| PLAG1_HUMAN.H10MO.D | GGRGGSMHNWVKAGGGG | 98 | 2.98E-02 | 1.00E+00 | 3.23E-01 | 1.00E+00 | 1.66E-02 | 1.00E+00 |
| SOX13_HUMAN.H10MO.D | YATTGTTY | 99 | 3.01E-02 | 1.00E+00 | 1.27E-01 | 1.00E+00 | 9.42E-01 | 1.00E+00 |
| GLIS2_HUMAN.H10MO.D | CKTCGCGGGGGGTM | 100 | 3.01E-02 | 1.00E+00 | 4.98E-01 | 1.00E+00 | 2.72E-06 | 1.74E-03 |
| PLAL1_HUMAN.H10MO.D | CRGGGGGCCC | 101 | 3.17E-02 | 1.00E+00 | 7.94E-02 | 1.00E+00 | 2.94E-05 | 1.87E-02 |
| THB_HUMAN.H10MO.C | GRSSYSASVTSAGGTCA | 102 | 3.28E-02 | 1.00E+00 | 1.60E-01 | 1.00E+00 | 9.81E-03 | 9.98E-01 |
| WT1_HUMAN.H10MO.D | GMGGGGGCGKGGG | 103 | 3.32E-02 | 1.00E+00 | 5.20E-01 | 1.00E+00 | 1.92E-07 | 1.23E-04 |
| NF2L2_HUMAN.H10MO.D | VRTGACTCAGCA | 104 | 3.36E-02 | 1.00E+00 | 2.71E-01 | 1.00E+00 | 5.57E-01 | 1.00E+00 |
| GLI2_HUMAN.H10MO.B | GTGGGTGGTCY | 105 | 3.42E-02 | 1.00E+00 | 5.91E-01 | 1.00E+00 | 7.68E-02 | 1.00E+00 |
| KAISO_HUMAN.H10MO.S | YTSGCRGGARKH | 106 | 3.43E-02 | 1.00E+00 | 1.10E-01 | 1.00E+00 | 8.80E-04 | 4.31E-01 |
| CTCF_HUMAN.H10MO.A | YKRCCASYAGRKGGCRSYV B | 107 | 3.57E-02 | 1.00E+00 | 6.52E-01 | 1.00E+00 | 9.69E-05 | 6.02E-02 |

TABLE 5-continued

Transcription Factors with binding sites enriched in: (A) genes up-regulated in lesional skin at baseline; (B) genes down-regulated in lesional skin by week 12 in the placebo group; (C) genes down-regulated in lesional skin by week 12 in the nemo group.

| | Motif | SEQ ID NO | A. Genes up-regulated in lesional skin at baseline p-value | A. FDR | B. Genes down-regulated in lesional skin by week 12 in the placebo group p-value | B. FDR | C. Genes down-regulated in lesional skin by week 12 in the nemo group p-value | C. FDR |
|---|---|---|---|---|---|---|---|---|
| STAT1_HUMAN.H10MO.S | SDYTTCCRGGAAAYS | 108 | 3.58E-02 | 1.00E+00 | 9.95E-03 | 9.98E-01 | 2.50E-01 | 1.00E+00 |
| FOXF1_HUMAN.H10MO.D | WTGTTTATTTW | 109 | 3.58E-02 | 1.00E+00 | 1.47E-01 | 1.00E+00 | 5.56E-01 | 1.00E+00 |
| THAP1_HUMAN.H10MO.D | SGCCGCCATSTYGGSYBCGGGC | 110 | 3.60E-02 | 1.00E+00 | 6.55E-01 | 1.00E+00 | 1.54E-05 | 9.83E-03 |
| STAT6_HUMAN.H10MO.C | TTCYYHGGAAWYY | 111 | 3.63E-02 | 1.00E+00 | 1.89E-01 | 1.00E+00 | 8.22E-01 | 1.00E+00 |
| STA5A_HUMAN.H10MO.B | YTTCYKRGAAW | 112 | 3.68E-02 | 1.00E+00 | 6.05E-01 | 1.00E+00 | 9.58E-01 | 1.00E+00 |
| PLAG1_HUMAN.H10MO.S | ARDGGGGGSHBYM | 113 | 3.84E-02 | 1.00E+00 | 1.52E-03 | 6.22E-01 | 8.94E-05 | 5.57E-02 |
| USF1_HUMAN.H10MO.A | GGTCACGTGR | 114 | 3.91E-02 | 1.00E+00 | 6.44E-01 | 1.00E+00 | 1.23E-02 | 1.00E+00 |
| JUND_HUMAN.H10MO.A | RRTGAGTCAYH | 115 | 4.03E-02 | 1.00E+00 | 7.86E-02 | 1.00E+00 | 4.54E-01 | 1.00E+00 |
| ERF_HUMAN.H10MO.D | WASAKKWSKTWSGRBAYTTC | 116 | 4.15E-02 | 1.00E+00 | 5.07E-01 | 1.00E+00 | 5.67E-01 | 1.00E+00 |
| INSM1_HUMAN.H10MO.C | TGTMAGGGGGCR | 117 | 4.16E-02 | 1.00E+00 | 2.51E-01 | 1.00E+00 | 1.60E-04 | 9.73E-02 |
| ZN219_HUMAN.H10MO.D | GDGGGGGGYGGA | 118 | 4.26E-02 | 1.00E+00 | 5.14E-01 | 1.00E+00 | 1.33E-03 | 5.73E-01 |
| SNAI1_HUMAN.H10MO.C | SCAGGTGK | 119 | 4.39E-02 | 1.00E+00 | 1.64E-01 | 1.00E+00 | 4.93E-02 | 1.00E+00 |
| CLOCK_HUMAN.H10MO.D | GGDBKGGDGRSRCGKGTRGK | 120 | 4.44E-02 | 1.00E+00 | 2.04E-01 | 1.00E+00 | 2.85E-03 | 8.39E-01 |
| PAX5_HUMAN.H10MO.A | SSVDRVKCAGCSRAGCGTGAC | 121 | 4.54E-02 | 1.00E+00 | 9.05E-01 | 1.00E+00 | 8.12E-03 | 9.95E-01 |
| GATA2_HUMAN.H10MO.A | RSAGATAAGVV | 122 | 4.66E-02 | 1.00E+00 | 5.61E-02 | 1.00E+00 | 7.71E-01 | 1.00E+00 |
| HXA1_HUMAN.H10MO.C | TKGATGGATG | 123 | 4.70E-02 | 1.00E+00 | 2.56E-01 | 1.00E+00 | 1.81E-01 | 1.00E+00 |
| SPDEF_HUMAN.H10MO.D | RWCCMGGAWGWAGT | 124 | 4.84E-02 | 1.00E+00 | 3.22E-01 | 1.00E+00 | 4.86E-01 | 1.00E+00 |
| MYF6_HUMAN.H10MO.C | GCAGSTG | 125 | 4.98E-02 | 1.00E+00 | 2.55E-02 | 1.00E+00 | 5.17E-04 | 2.82E-01 |
| MYBB_HUMAN.H10MO.D | TRSMGGTTRW | 126 | 4.99E-02 | 1.00E+00 | 3.61E-01 | 1.00E+00 | 3.66E-01 | 1.00E+00 |
| YBOX1_HUMAN.H10MO.D | BSKGATTSSCY | 127 | 5.14E-02 | 1.00E+00 | 2.80E-01 | 1.00E+00 | 7.56E-03 | 9.92E-01 |
| NR2C1_HUMAN.H10MO.C | GSYVAGAGGTCAB | 128 | 5.15E-02 | 1.00E+00 | 5.68E-01 | 1.00E+00 | 4.05E-03 | 9.25E-01 |
| ETV4_HUMAN.H10MO.B | SAGGAAGT | 129 | 5.21E-02 | 1.00E+00 | 4.30E-02 | 1.00E+00 | 3.09E-02 | 1.00E+00 |
| NKX21_HUMAN.H10MO.D | STCAAGKGCH | 130 | 5.26E-02 | 1.00E+00 | 2.96E-01 | 1.00E+00 | 7.86E-03 | 9.94E-01 |
| SP1_HUMAN.H10MO.S | GGGGGCGGGGC | 131 | 5.31E-02 | 1.00E+00 | 8.37E-01 | 1.00E+00 | 1.70E-03 | 6.64E-01 |
| ZEB1_HUMAN.H10MO.B | NVCAGGTRDRN | 132 | 5.33E-02 | 1.00E+00 | 9.06E-02 | 1.00E+00 | 3.14E-02 | 1.00E+00 |
| PAX2_HUMAN.H10MO.S | SMRTGAC | 133 | 5.38E-02 | 1.00E+00 | 7.95E-02 | 1.00E+00 | 4.30E-03 | 9.36E-01 |
| ZIC3_HUMAN.H10MO.C | BGGGTGGYC | 134 | 5.39E-02 | 1.00E+00 | 4.11E-01 | 1.00E+00 | 8.70E-03 | 9.96E-01 |
| IKZF1_HUMAN.H10MO.C | BTGGGARR | 135 | 5.43E-02 | 1.00E+00 | 3.93E-01 | 1.00E+00 | 2.10E-01 | 1.00E+00 |
| P73_HUMAN.H10MO.S | GGGRCADGYYYB | 136 | 5.62E-02 | 1.00E+00 | 2.14E-01 | 1.00E+00 | 3.07E-01 | 1.00E+00 |
| HXB3_HUMAN.H10MO.D | YTAATTASYTTTTW | 137 | 5.92E-02 | 1.00E+00 | 1.90E-01 | 1.00E+00 | 9.03E-01 | 1.00E+00 |
| E2F6_HUMAN.H10MO.C | NKGGCGGGARRG | 138 | 5.95E-02 | 1.00E+00 | 5.51E-01 | 1.00E+00 | 1.99E-04 | 1.20E-01 |
| NR1I3_HUMAN.H10MO.C | RRGGTCARVRRAGTTCAD | 139 | 6.07E-02 | 1.00E+00 | 1.25E-01 | 1.00E+00 | 7.36E-02 | 1.00E+00 |

TABLE 5-continued

Transcription Factors with binding sites enriched in: (A) genes up-regulated in lesional skin at baseline; (B) genes down-regulated in lesional skin by week 12 in the placebo group; (C) genes down-regulated in lesional skin by week 12 in the nemo group.

| | | SEQ ID | A. Genes up-regulated in lesional skin at baseline | | B. Genes down-regulated in lesional skin by week 12 in the placebo group | | C. Genes down-regulated in lesional skin by week 12 in the nemo group | |
|---|---|---|---|---|---|---|---|---|
| | Motif | NO | p-value | FDR | p-value | FDR | p-value | FDR |
| SOX18_HUMAN.H10MO.D | SHWHVMWTTGTTBTYKTCC | 140 | 6.17E-02 | 1.00E+00 | 1.15E-01 | 1.00E+00 | 4.08E-01 | 1.00E+00 |
| ATF3_HUMAN.H10MO.A | RTGACKYMA | 141 | 6.27E-02 | 1.00E+00 | 3.40E-01 | 1.00E+00 | 2.08E-02 | 1.00E+00 |
| NRL_HUMAN.H10MO.D | TGCTGACKYWR | 142 | 6.27E-02 | 1.00E+00 | 3.12E-02 | 1.00E+00 | 6.19E-03 | 9.81E-01 |
| HBP1_HUMAN.H10MO.D | AYYCATTGA | 143 | 6.27E-02 | 1.00E+00 | 8.14E-01 | 1.00E+00 | 4.82E-01 | 1.00E+00 |
| FOXC1_HUMAN.H10MO.C | CDWTGTTTACTTWRG | 144 | 6.31E-02 | 1.00E+00 | 7.54E-02 | 1.00E+00 | 8.11E-01 | 1.00E+00 |
| EVX2_HUMAN.H10MO.A | TTTTATKRCHYH | 145 | 6.39E-02 | 1.00E+00 | 5.56E-01 | 1.00E+00 | 8.82E-01 | 1.00E+00 |
| PAX8_HUMAN.H10MO.D | BTVAYTSRMGYRKR | 146 | 6.42E-02 | 1.00E+00 | 1.01E-01 | 1.00E+00 | 3.25E-03 | 8.76E-01 |
| GLI3_HUMAN.H10MO.B | BTGGGTGGTCY | 147 | 6.57E-02 | 1.00E+00 | 6.05E-02 | 1.00E+00 | 2.39E-01 | 1.00E+00 |
| ATF6A_HUMAN.H10MO.B | GKGSTGACGTGG | 148 | 6.66E-02 | 1.00E+00 | 4.95E-03 | 9.58E-01 | 1.12E-04 | 6.91E-02 |
| PO2F3_HUMAN.H10MO.D | DTYATGCWWAWTTR | 149 | 6.80E-02 | 1.00E+00 | 5.34E-01 | 1.00E+00 | 7.88E-01 | 1.00E+00 |
| COT1_HUMAN.H10MO.S | GKBCAAAGGTCA | 150 | 6.83E-02 | 1.00E+00 | 4.86E-01 | 1.00E+00 | 6.50E-03 | 9.85E-01 |
| PAX5_HUMAN.H10MO.S | GGCTGAGS | 151 | 6.83E-02 | 1.00E+00 | 4.36E-01 | 1.00E+00 | 2.01E-02 | 1.00E+00 |
| ZSCA4_HUMAN.H10MO.D | AGTGTGTGCACT | 152 | 7.02E-02 | 1.00E+00 | 1.00E-01 | 1.00E+00 | 1.13E-01 | 1.00E+00 |
| DLX5_HUMAN.H10MO.D | AATTWDNBDTAATT | 153 | 7.03E-02 | 1.00E+00 | 1.83E-01 | 1.00E+00 | 9.06E-01 | 1.00E+00 |
| NDF1_HUMAN.H10MO.C | CGGCAGRTGKSC | 154 | 7.08E-02 | 1.00E+00 | 1.61E-01 | 1.00E+00 | 1.15E-02 | 9.99E-01 |
| SNAI2_HUMAN.H10MO.C | BCAGGTG | 155 | 7.09E-02 | 1.00E+00 | 2.24E-02 | 1.00E+00 | 1.42E-02 | 1.00E+00 |
| BCL6B_HUMAN.H10MO.D | HYGCTTTCKAG | 156 | 7.31E-02 | 1.00E+00 | 6.76E-01 | 1.00E+00 | 6.09E-01 | 1.00E+00 |
| HXD10_HUMAN.H10MO.D | TGCTTTAATT | 157 | 7.31E-02 | 1.00E+00 | 2.72E-02 | 1.00E+00 | 1.64E-01 | 1.00E+00 |
| TWST1_HUMAN.H10MO.D | MCCCAGGTGK | 158 | 7.46E-02 | 1.00E+00 | 7.92E-02 | 1.00E+00 | 6.41E-02 | 1.00E+00 |
| ELK1_HUMAN.H10MO.A | RCCGGAAGT | 159 | 7.64E-02 | 1.00E+00 | 2.33E-02 | 1.00E+00 | 1.19E-02 | 1.00E+00 |
| REL_HUMAN.H10MO.C | DKGGRNWTTCCM | 160 | 7.67E-02 | 1.00E+00 | 1.53E-02 | 1.00E+00 | 1.09E-02 | 9.99E-01 |
| GATA5_HUMAN.H10MO.D | WVANWGATAAYTYRRHK | 161 | 7.67E-02 | 1.00E+00 | 6.12E-01 | 1.00E+00 | 9.64E-01 | 1.00E+00 |
| PAX4_HUMAN.H10MO.D | TWAYTAATTMRH | 162 | 7.71E-02 | 1.00E+00 | 3.52E-01 | 1.00E+00 | 9.50E-01 | 1.00E+00 |
| GATA6_HUMAN.H10MO.S | NWGATAA | 163 | 7.98E-02 | 1.00E+00 | 4.72E-01 | 1.00E+00 | 7.90E-01 | 1.00E+00 |
| SOX2_HUMAN.H10MO.B | CCWTTGTYATGCAAAW | 164 | 7.98E-02 | 1.00E+00 | 9.27E-02 | 1.00E+00 | 5.38E-01 | 1.00E+00 |
| TBR1_HUMAN.H10MO.D | RAAGGTGTGAAAW | 165 | 8.07E-02 | 1.00E+00 | 2.38E-01 | 1.00E+00 | 1.55E-01 | 1.00E+00 |
| FOS_HUMAN.H10MO.A | RTGAGTCAYYN | 166 | 8.16E-02 | 1.00E+00 | 1.11E-01 | 1.00E+00 | 2.24E-01 | 1.00E+00 |
| CDX1_HUMAN.H10MO.C | HTTTATGD | 167 | 8.19E-02 | 1.00E+00 | 4.59E-01 | 1.00E+00 | 9.42E-01 | 1.00E+00 |
| NFKB2_HUMAN.H10MO.D | GRAATBYCCCT | 168 | 8.25E-02 | 1.00E+00 | 2.23E-01 | 1.00E+00 | 6.58E-01 | 1.00E+00 |
| PBX3_HUMAN.H10MO.B | YBYTGATTGRYTGR | 169 | 8.29E-02 | 1.00E+00 | 3.40E-01 | 1.00E+00 | 2.24E-02 | 1.00E+00 |
| ELF5_HUMAN.H10MO.D | AHMAGGAWRTW | 170 | 8.52E-02 | 1.00E+00 | 6.23E-01 | 1.00E+00 | 9.39E-01 | 1.00E+00 |
| BATF_HUMAN.H10MO.S | MTGAGTCAKW | 171 | 8.71E-02 | 1.00E+00 | 2.82E-01 | 1.00E+00 | 2.50E-01 | 1.00E+00 |
| TAL1_HUMAN.H10MO.A | CTGKNNNNNDSWGATAAGV | 172 | 8.96E-02 | 1.00E+00 | 7.32E-01 | 1.00E+00 | 2.89E-01 | 1.00E+00 |
| KLF8_HUMAN.H10MO.C | CAGGGKGTG | 173 | 8.97E-02 | 1.00E+00 | 7.76E-01 | 1.00E+00 | 2.96E-05 | 1.88E-02 |

TABLE 5-continued

Transcription Factors with binding sites enriched in: (A) genes up-regulated in lesional skin at baseline; (B) genes down-regulated in lesional skin by week 12 in the placebo group; (C) genes down-regulated in lesional skin by week 12 in the nemo group.

| | Motif | SEQ ID NO | A. Genes up-regulated in lesional skin at baseline p-value | A. FDR | B. Genes down-regulated in lesional skin by week 12 in the placebo group p-value | B. FDR | C. Genes down-regulated in lesional skin by week 12 in the nemo group p-value | C. FDR |
|---|---|---|---|---|---|---|---|---|
| MESP1_HUMAN.H10MO.D | VCAGGTGKKBD | 174 | 9.10E-02 | 1.00E+00 | 1.97E-02 | 1.00E+00 | 1.04E-01 | 1.00E+00 |
| TBX21_HUMAN.H10MO.D | RAGGTGTGAAWT | 175 | 9.33E-02 | 1.00E+00 | 8.12E-01 | 1.00E+00 | 4.73E-01 | 1.00E+00 |
| FOXB1_HUMAN.H10MO.D | RTMAATRTTTACATAAB | 176 | 9.40E-02 | 1.00E+00 | 2.84E-01 | 1.00E+00 | 8.86E-01 | 1.00E+00 |
| PBX1_HUMAN.H10MO.B | WAWTTGATTGATGDB | 177 | 9.41E-02 | 1.00E+00 | 7.30E-01 | 1.00E+00 | 7.34E-01 | 1.00E+00 |
| RFX5_HUMAN.H10MO.A | STCMBCWGTTGCYRGGVAR A | 178 | 9.87E-02 | 1.00E+00 | 8.11E-01 | 1.00E+00 | 4.14E-02 | 1.00E+00 |
| HEY2_HUMAN.H10MO.D | GKBGGCWCGTGGCHTBV | 179 | 9.90E-02 | 1.00E+00 | 4.57E-01 | 1.00E+00 | 1.90E-03 | 7.04E-01 |
| SPIC_HUMAN.H10MO.D | KVDRRWGGGKDRG | 180 | 9.96E-02 | 1.00E+00 | 2.26E-01 | 1.00E+00 | 1.97E-01 | 1.00E+00 |
| USF2_HUMAN.H10MO.A | GGGTCACGTGRBSVSSSSB | 181 | 9.99E-02 | 1.00E+00 | 7.04E-01 | 1.00E+00 | 1.29E-04 | 7.91E-02 |
| ESR1_HUMAN.H10MO.A | MMAGGTCASVVTGHCCH | 182 | 1.01E-01 | 1.00E+00 | 2.56E-01 | 1.00E+00 | 2.82E-02 | 1.00E+00 |
| SPZ1_HUMAN.H10MO.D | CGGCKGWWACMBYGGG | 183 | 1.01E-01 | 1.00E+00 | 4.53E-01 | 1.00E+00 | 1.91E-04 | 1.15E-01 |
| E4F1_HUMAN.H10MO.D | YGTKACGTC | 184 | 1.02E-01 | 1.00E+00 | 3.11E-01 | 1.00E+00 | 1.73E-02 | 1.00E+00 |
| IRF2_HUMAN.H10MO.C | SGAAAGYGAAASYR | 185 | 1.02E-01 | 1.00E+00 | 7.97E-01 | 1.00E+00 | 5.33E-01 | 1.00E+00 |
| ATF1_HUMAN.H10MO.B | NRTGACGTMAK | 186 | 1.06E-01 | 1.00E+00 | 5.40E-02 | 1.00E+00 | 4.46E-01 | 1.00E+00 |
| NFIL3_HUMAN.H10MO.C | RTTAYGTAAYKYMB | 187 | 1.08E-01 | 1.00E+00 | 6.01E-02 | 1.00E+00 | 9.98E-01 | 1.00E+00 |
| TBX5_HUMAN.H10MO.D | AGGTGTGA | 188 | 1.08E-01 | 1.00E+00 | 4.72E-01 | 1.00E+00 | 5.27E-02 | 1.00E+00 |
| GLIS1_HUMAN.H10MO.D | TCGTGGGGGGTMD | 189 | 1.09E-01 | 1.00E+00 | 3.95E-01 | 1.00E+00 | 8.83E-04 | 4.32E-01 |
| HES7_HUMAN.H10MO.D | TGGCACGTGCCG | 190 | 1.12E-01 | 1.00E+00 | 4.82E-01 | 1.00E+00 | 6.54E-04 | 3.42E-01 |
| GSC2_HUMAN.H10MO.D | RKMGGRTTRGB | 191 | 1.12E-01 | 1.00E+00 | 2.14E-02 | 1.00E+00 | 2.54E-03 | 8.04E-01 |
| CREM_HUMAN.H10MO.C | CRVTGACGTCA | 192 | 1.12E-01 | 1.00E+00 | 4.95E-01 | 1.00E+00 | 1.92E-01 | 1.00E+00 |
| RXRA_HUMAN.H10MO.C | MWSTRGGDCAAAGGTCA | 193 | 1.12E-01 | 1.00E+00 | 5.60E-01 | 1.00E+00 | 2.36E-01 | 1.00E+00 |
| BARX1_HUMAN.H10MO.D | TAATYGNTWTTTAATKG | 194 | 1.13E-01 | 1.00E+00 | 9.42E-01 | 1.00E+00 | 8.56E-01 | 1.00E+00 |
| SMAD1_HUMAN.H10MO.D | RSCCTGTCTGCC | 195 | 1.13E-01 | 1.00E+00 | 3.22E-01 | 1.00E+00 | 3.83E-01 | 1.00E+00 |
| TGIF2_HUMAN.H10MO.D | DTGACAGCTGT | 196 | 1.13E-01 | 1.00E+00 | 3.57E-01 | 1.00E+00 | 5.10E-01 | 1.00E+00 |
| MLXPL_HUMAN.H10MO.D | GCAYGKGVCAMCSBCGTGB | 197 | 1.14E-01 | 1.00E+00 | 1.88E-01 | 1.00E+00 | 2.85E-02 | 1.00E+00 |
| NFYA_HUMAN.H10MO.A | YRRCCAATSAGMR | 198 | 1.15E-01 | 1.00E+00 | 1.93E-01 | 1.00E+00 | 3.68E-02 | 1.00E+00 |
| KLF6_HUMAN.H10MO.D | GGGGGCKG | 199 | 1.15E-01 | 1.00E+00 | 5.15E-01 | 1.00E+00 | 4.61E-05 | 2.91E-02 |
| NFAT5_HUMAN.H10MO.D | SYGGAAAANTYCMTK | 200 | 1.16E-01 | 1.00E+00 | 9.93E-03 | 9.98E-01 | 2.40E-01 | 1.00E+00 |
| NANOG_HUMAN.H10MO.S | KTTAATGG | 201 | 1.17E-01 | 1.00E+00 | 4.41E-01 | 1.00E+00 | 6.16E-01 | 1.00E+00 |
| CR3L1_HUMAN.H10MO.D | GCCACGTGGCA | 202 | 1.17E-01 | 1.00E+00 | 5.82E-01 | 1.00E+00 | 3.39E-03 | 8.86E-01 |
| PO6F1_HUMAN.H10MO.D | CATAAWTTATGCR | 203 | 1.18E-01 | 1.00E+00 | 1.88E-01 | 1.00E+00 | 7.40E-01 | 1.00E+00 |
| EGR2_HUMAN.H10MO.C | DGMGTGGGCGG | 204 | 1.18E-01 | 1.00E+00 | 3.23E-01 | 1.00E+00 | 4.66E-03 | 9.50E-01 |
| ZIC4_HUMAN.H10MO.D | DCRCAGCGGGGGGTC | 205 | 1.19E-01 | 1.00E+00 | 5.33E-01 | 1.00E+00 | 3.01E-04 | 1.75E-01 |
| NFKB1_HUMAN.H10MO.B | GGGRAAKYCCC | 206 | 1.19E-01 | 1.00E+00 | 2.81E-01 | 1.00E+00 | 1.49E-04 | 9.13E-02 |
| NR1I2_HUMAN.H10MO.C | DDRGGTYAANNRAGTTCAB | 207 | 1.20E-01 | 1.00E+00 | 3.97E-01 | 1.00E+00 | 3.72E-01 | 1.00E+00 |

TABLE 5-continued

Transcription Factors with binding sites enriched in: (A) genes up-regulated in lesional skin at baseline; (B) genes down-regulated in lesional skin by week 12 in the placebo group; (C) genes down-regulated in lesional skin by week 12 in the nemo group.

| | Motif | SEQ ID NO | A. Genes up-regulated in lesional skin at baseline p-value | FDR | B. Genes down-regulated in lesional skin by week 12 in the placebo group p-value | FDR | C. Genes down-regulated in lesional skin by week 12 in the nemo group p-value | FDR |
|---|---|---|---|---|---|---|---|---|
| OLIG2_HUMAN.H10MO.D | RCCATATGKTT | 208 | 1.21E-01 | 1.00E+00 | 1.23E-01 | 1.00E+00 | 9.80E-01 | 1.00E+00 |
| SOX5_HUMAN.H10MO.C | YATTGTTW | 209 | 1.22E-01 | 1.00E+00 | 5.13E-02 | 1.00E+00 | 7.61E-01 | 1.00E+00 |
| NFIA_HUMAN.H10MO.C | TTGGCHNRNWGCCAR | 210 | 1.22E-01 | 1.00E+00 | 3.90E-01 | 1.00E+00 | 8.99E-02 | 1.00E+00 |
| HXC13_HUMAN.H10MO.D | DDTTTTACKAG | 211 | 1.22E-01 | 1.00E+00 | 5.19E-01 | 1.00E+00 | 9.75E-01 | 1.00E+00 |
| ESR2_HUMAN.H10MO.S | RGGTCAS | 212 | 1.23E-01 | 1.00E+00 | 4.32E-01 | 1.00E+00 | 3.52E-02 | 1.00E+00 |
| BCL6_HUMAN.H10MO.C | DARDRCTTTCYWGGAA | 213 | 1.24E-01 | 1.00E+00 | 1.64E-01 | 1.00E+00 | 5.90E-01 | 1.00E+00 |
| ZN524_HUMAN.H10MO.D | GGGTDCRAGGGTTCGAGK | 214 | 1.24E-01 | 1.00E+00 | 4.51E-02 | 1.00E+00 | 8.09E-04 | 4.04E-01 |
| ELF2_HUMAN.H10MO.C | VRRVSCGGAAGYRSVRS | 215 | 1.26E-01 | 1.00E+00 | 6.92E-01 | 1.00E+00 | 3.99E-02 | 1.00E+00 |
| MYOD1_HUMAN.H10MO.C | SCASCTGTY | 216 | 1.26E-01 | 1.00E+00 | 1.14E-01 | 1.00E+00 | 1.50E-03 | 6.18E-01 |
| HXA9_HUMAN.H10MO.D | TGACAGTTTWAYGR | 217 | 1.26E-01 | 1.00E+00 | 3.57E-01 | 1.00E+00 | 8.17E-01 | 1.00E+00 |
| EVX1_HUMAN.H10MO.D | TDHTWDTWTGTTTACTTAWM | 218 | 1.29E-01 | 1.00E+00 | 1.32E-01 | 1.00E+00 | 8.92E-01 | 1.00E+00 |
| FUBP1_HUMAN.H10MO.D | TYGTNTTTTTTT | 219 | 1.31E-01 | 1.00E+00 | 1.39E-01 | 1.00E+00 | 7.37E-01 | 1.00E+00 |
| TGIF1_HUMAN.H10MO.S | NTGACAG | 220 | 1.31E-01 | 1.00E+00 | 4.46E-01 | 1.00E+00 | 6.64E-02 | 1.00E+00 |
| SMAD4_HUMAN.H10MO.C | STGTCTSDCACCT | 221 | 1.31E-01 | 1.00E+00 | 7.74E-01 | 1.00E+00 | 1.32E-01 | 1.00E+00 |
| COT1_HUMAN.H10MO.B | CAAAGGTCA | 222 | 1.32E-01 | 1.00E+00 | 4.73E-01 | 1.00E+00 | 2.33E-03 | 7.75E-01 |
| TLX1_HUMAN.H10MO.S | YGBYAAKRWGS | 223 | 1.32E-01 | 1.00E+00 | 5.01E-01 | 1.00E+00 | 5.65E-02 | 1.00E+00 |
| TFCP2_HUMAN.H10MO.D | SCCTGMNCDSRCCRGA | 224 | 1.33E-01 | 1.00E+00 | 1.24E-01 | 1.00E+00 | 1.29E-02 | 1.00E+00 |
| HMX1_HUMAN.H10MO.D | DTTAATTGHTTTTTAAT | 225 | 1.33E-01 | 1.00E+00 | 1.11E-01 | 1.00E+00 | 9.82E-01 | 1.00E+00 |
| PRGR_HUMAN.H10MO.S | AGAACAB | 226 | 1.33E-01 | 1.00E+00 | 4.61E-01 | 1.00E+00 | 8.34E-01 | 1.00E+00 |
| SCRT1_HUMAN.H10MO.D | KCAACAGGTGGTH | 227 | 1.33E-01 | 1.00E+00 | 3.83E-01 | 1.00E+00 | 1.32E-01 | 1.00E+00 |
| FOSL1_HUMAN.H10MO.A | DRTGACTCATN | 228 | 1.35E-01 | 1.00E+00 | 2.62E-01 | 1.00E+00 | 1.72E-02 | 1.00E+00 |
| DUXA_HUMAN.H10MO.D | TGATTARRTYA | 229 | 1.36E-01 | 1.00E+00 | 3.10E-01 | 1.00E+00 | 8.46E-01 | 1.00E+00 |
| RORA_HUMAN.H10MO.B | WWAWBTAGGTCA | 230 | 1.37E-01 | 1.00E+00 | 1.62E-01 | 1.00E+00 | 6.08E-02 | 1.00E+00 |
| HXB8_HUMAN.H10MO.C | TTGATTAATKV | 231 | 1.38E-01 | 1.00E+00 | 6.03E-01 | 1.00E+00 | 9.36E-01 | 1.00E+00 |
| PRRX1_HUMAN.H10MO.D | TAAYCTG | 232 | 1.38E-01 | 1.00E+00 | 5.88E-01 | 1.00E+00 | 8.75E-01 | 1.00E+00 |
| IRX2_HUMAN.H10MO.D | RCDKGKBDKGDCRKGTDVK | 233 | 1.40E-01 | 1.00E+00 | 3.87E-02 | 1.00E+00 | 8.97E-04 | 4.37E-01 |
| OTX1_HUMAN.H10MO.D | AGGATTAV | 234 | 1.40E-01 | 1.00E+00 | 9.96E-02 | 1.00E+00 | 3.87E-01 | 1.00E+00 |
| ATF7_HUMAN.H10MO.D | KRTGACGTCAT | 235 | 1.41E-01 | 1.00E+00 | 7.07E-02 | 1.00E+00 | 4.18E-01 | 1.00E+00 |
| HXB7_HUMAN.H10MO.C | TTGATTRATK | 236 | 1.43E-01 | 1.00E+00 | 7.31E-01 | 1.00E+00 | 9.98E-01 | 1.00E+00 |
| FOXH1_HUMAN.H10MO.A | TGTGGATTSNR | 237 | 1.45E-01 | 1.00E+00 | 2.78E-01 | 1.00E+00 | 9.05E-01 | 1.00E+00 |
| HESX1_HUMAN.H10MO.D | ABSYGGCWMRTRRMMT | 238 | 1.45E-01 | 1.00E+00 | 1.21E-01 | 1.00E+00 | 3.55E-02 | 1.00E+00 |
| COT2_HUMAN.H10MO.A | CARAGGTCARRGD | 239 | 1.45E-01 | 1.00E+00 | 9.19E-01 | 1.00E+00 | 4.96E-01 | 1.00E+00 |
| BMAL1_HUMAN.H10MO.C | KGRACACGTGACYC | 240 | 1.46E-01 | 1.00E+00 | 1.75E-01 | 1.00E+00 | 1.61E-02 | 1.00E+00 |

TABLE 5-continued

Transcription Factors with binding sites enriched in: (A) genes up-regulated in lesional skin at baseline; (B) genes down-regulated in lesional skin by week 12 in the placebo group; (C) genes down-regulated in lesional skin by week 12 in the nemo group.

| | Motif | SEQ ID NO | A. Genes up-regulated in lesional skin at baseline p-value | A. FDR | B. Genes down-regulated in lesional skin by week 12 in the placebo group p-value | B. FDR | C. Genes down-regulated in lesional skin by week 12 in the nemo group p-value | C. FDR |
|---|---|---|---|---|---|---|---|---|
| AP2D_HUMAN.H10MO.D | CGCCYGVGGCSCGT | 241 | 1.47E-01 | 1.00E+00 | 8.27E-01 | 1.00E+00 | 2.46E-05 | 1.57E-02 |
| HEN1_HUMAN.H10MO.C | BGGGKMKCAGCTGCGKCCYY | 242 | 1.48E-01 | 1.00E+00 | 6.13E-01 | 1.00E+00 | 2.95E-04 | 1.72E-01 |
| NFAC1_HUMAN.H10MO.S | HGGAAAWTTCCAT | 243 | 1.48E-01 | 1.00E+00 | 7.70E-02 | 1.00E+00 | 7.96E-01 | 1.00E+00 |
| CEBPE_HUMAN.H10MO.A | TTKCGHAATMTB | 244 | 1.51E-01 | 1.00E+00 | 1.93E-02 | 1.00E+00 | 8.01E-01 | 1.00E+00 |
| CRX_HUMAN.H10MO.C | VRGATTAR | 245 | 1.52E-01 | 1.00E+00 | 3.50E-01 | 1.00E+00 | 2.23E-01 | 1.00E+00 |
| EHF_HUMAN.H10MO.S | MWACCMGGAARTA | 246 | 1.52E-01 | 1.00E+00 | 1.62E-01 | 1.00E+00 | 2.76E-01 | 1.00E+00 |
| FOXD1_HUMAN.H10MO.D | CWWTGTTTACHTWVR | 247 | 1.52E-01 | 1.00E+00 | 7.26E-01 | 1.00E+00 | 9.21E-01 | 1.00E+00 |
| ZBT7A_HUMAN.H10MO.D | MKCWSKGGGTNBMCBAG | 248 | 1.56E-01 | 1.00E+00 | 1.76E-01 | 1.00E+00 | 3.53E-02 | 1.00E+00 |
| PRDM4_HUMAN.H10MO.D | KBGGGGGGCCTTGAAA | 249 | 1.57E-01 | 1.00E+00 | 4.43E-01 | 1.00E+00 | 2.98E-01 | 1.00E+00 |
| NFAC1_HUMAN.H10MO.A | MMATGGAAAWTT | 250 | 1.58E-01 | 1.00E+00 | 2.83E-01 | 1.00E+00 | 9.44E-01 | 1.00E+00 |
| VDR_HUMAN.H10MO.B | RRGGTCASNGRGKTCA | 251 | 1.58E-01 | 1.00E+00 | 1.07E-01 | 1.00E+00 | 4.88E-03 | 9.56E-01 |
| ID4_HUMAN.H10MO.D | DNCAGGTGYNV | 252 | 1.60E-01 | 1.00E+00 | 1.10E-01 | 1.00E+00 | 2.26E-02 | 1.00E+00 |
| ALX1_HUMAN.H10MO.B | RTAATTRVATTA | 253 | 1.60E-01 | 1.00E+00 | 2.77E-01 | 1.00E+00 | 9.93E-01 | 1.00E+00 |
| TF65_HUMAN.H10MO.A | GGGRMTTTCCM | 254 | 1.61E-01 | 1.00E+00 | 4.79E-02 | 1.00E+00 | 1.81E-02 | 1.00E+00 |
| PAX3_HUMAN.H10MO.D | GWTAATYGATTAW | 255 | 1.63E-01 | 1.00E+00 | 3.68E-01 | 1.00E+00 | 9.98E-01 | 1.00E+00 |
| FIGLA_HUMAN.H10MO.D | DHMCAGGTGKT | 256 | 1.65E-01 | 1.00E+00 | 1.47E-01 | 1.00E+00 | 3.53E-01 | 1.00E+00 |
| NFAC3_HUMAN.H10MO.B | TGGAAAAHY | 257 | 1.65E-01 | 1.00E+00 | 3.06E-01 | 1.00E+00 | 3.12E-01 | 1.00E+00 |
| FOXC2_HUMAN.H10MO.D | GTTTGTTTWSHYAGR | 258 | 1.67E-01 | 1.00E+00 | 4.78E-02 | 1.00E+00 | 5.37E-01 | 1.00E+00 |
| FOSB_HUMAN.H10MO.C | GRTGACTCABH | 259 | 1.68E-01 | 1.00E+00 | 3.44E-01 | 1.00E+00 | 4.85E-01 | 1.00E+00 |
| TLX1_HUMAN.H10MO.D | YYGGYAMBDDGCCAAGR | 260 | 1.68E-01 | 1.00E+00 | 3.46E-01 | 1.00E+00 | 5.62E-01 | 1.00E+00 |
| ELF1_HUMAN.H10MO.A | GAACCMGGAAGTGS | 261 | 1.71E-01 | 1.00E+00 | 5.25E-01 | 1.00E+00 | 8.15E-03 | 9.95E-01 |
| TBX3_HUMAN.H10MO.D | AGKWAGRSAMTTAGGTSWKAARAA | 262 | 1.71E-01 | 1.00E+00 | 7.65E-01 | 1.00E+00 | 1.43E-01 | 1.00E+00 |
| HTF4_HUMAN.H10MO.B | VNSCAGGTGBG | 263 | 1.71E-01 | 1.00E+00 | 1.59E-01 | 1.00E+00 | 1.06E-02 | 9.99E-01 |
| MEOX1_HUMAN.H10MO.D | GGTAATTAGBGKHAWW | 264 | 1.77E-01 | 1.00E+00 | 1.18E-01 | 1.00E+00 | 9.81E-01 | 1.00E+00 |
| NROB1_HUMAN.H10MO.D | GMGKGGGASR | 265 | 1.78E-01 | 1.00E+00 | 3.56E-01 | 1.00E+00 | 9.16E-04 | 4.44E-01 |
| GATA6_HUMAN.H10MO.B | DDVAGATAAGAWAR | 266 | 1.78E-01 | 1.00E+00 | 2.69E-01 | 1.00E+00 | 9.12E-01 | 1.00E+00 |
| RARG_HUMAN.H10MO.C | GGRGKTCRVCNRVAGGTCAV | 267 | 1.80E-01 | 1.00E+00 | 4.51E-01 | 1.00E+00 | 2.24E-03 | 7.63E-01 |
| HXC8_HUMAN.H10MO.D | YTTSATTRATDSSC | 268 | 1.83E-01 | 1.00E+00 | 8.95E-01 | 1.00E+00 | 7.36E-01 | 1.00E+00 |
| DLX6_HUMAN.H10MO.D | TAATTANNNHWWWWW | 269 | 1.84E-01 | 1.00E+00 | 9.34E-02 | 1.00E+00 | 1.00E+00 | 1.00E+00 |
| HMX3_HUMAN.H10MO.D | NNTTAATTGST | 270 | 1.85E-01 | 1.00E+00 | 7.07E-01 | 1.00E+00 | 9.90E-01 | 1.00E+00 |
| STAT2_HUMAN.H10MO.B | TYASTTTCNBTTYCH | 271 | 1.86E-01 | 1.00E+00 | 4.30E-01 | 1.00E+00 | 9.15E-01 | 1.00E+00 |
| NFYC_HUMAN.H10MO.B | YAGCCAATSAGVGS | 272 | 1.88E-01 | 1.00E+00 | 3.23E-01 | 1.00E+00 | 2.24E-03 | 7.62E-01 |
| HXD8_HUMAN.H10MO.D | WAATWTGCAYN | 273 | 1.88E-01 | 1.00E+00 | 6.84E-01 | 1.00E+00 | 9.66E-01 | 1.00E+00 |

TABLE 5-continued

Transcription Factors with binding sites enriched in: (A) genes up-regulated in lesional skin at baseline; (B) genes down-regulated in lesional skin by week 12 in the placebo group; (C) genes down-regulated in lesional skin by week 12 in the nemo group.

| | | SEQ ID | A. Genes up-regulated in lesional skin at baseline | | B. Genes down-regulated in lesional skin by week 12 in the placebo group | | C. Genes down-regulated in lesional skin by week 12 in the nemo group | |
|---|---|---|---|---|---|---|---|---|
| | Motif | NO | p-value | FDR | p-value | FDR | p-value | FDR |
| GFI1_HUMAN.H10MO.C | GCWSTGATTT | 274 | 1.90E-01 | 1.00E+00 | 1.87E-01 | 1.00E+00 | 7.03E-01 | 1.00E+00 |
| EMX1_HUMAN.H10MO.D | TAATTAGYTAAW | 275 | 1.91E-01 | 1.00E+00 | 5.91E-01 | 1.00E+00 | 9.99E-01 | 1.00E+00 |
| SRF_HUMAN.H10MO.A | MTTBKCCTTMTWTGGCCW | 276 | 1.93E-01 | 1.00E+00 | 2.10E-01 | 1.00E+00 | 8.40E-01 | 1.00E+00 |
| PITX1_HUMAN.H10MO.D | DGGATTAAVGG | 277 | 1.96E-01 | 1.00E+00 | 6.47E-03 | 9.84E-01 | 4.06E-02 | 1.00E+00 |
| MEIS1_HUMAN.H10MO.C | TGACAGBTTWAHG | 278 | 1.98E-01 | 1.00E+00 | 6.26E-01 | 1.00E+00 | 3.61E-01 | 1.00E+00 |
| TEAD3_HUMAN.H10MO.D | GAHATTYYWGCYBYW | 279 | 2.00E-01 | 1.00E+00 | 6.70E-01 | 1.00E+00 | 9.03E-01 | 1.00E+00 |
| PPARD_HUMAN.H10MO.D | YAGGNBAAAGGTCA | 280 | 2.01E-01 | 1.00E+00 | 1.41E-01 | 1.00E+00 | 3.41E-02 | 1.00E+00 |
| PAX2_HUMAN.H10MO.D | RHTCAGTSAYGMGTGAYW | 281 | 2.02E-01 | 1.00E+00 | 6.37E-02 | 1.00E+00 | 4.88E-01 | 1.00E+00 |
| ZN423_HUMAN.H10MO.D | GRCACCCWAGGGTGC | 282 | 2.05E-01 | 1.00E+00 | 4.44E-01 | 1.00E+00 | 2.92E-02 | 1.00E+00 |
| MEOX2_HUMAN.H10MO.D | TTAATKAYBWT | 283 | 2.09E-01 | 1.00E+00 | 6.51E-01 | 1.00E+00 | 9.89E-01 | 1.00E+00 |
| MITF_HUMAN.H10MO.C | RWCATGTGMB | 284 | 2.11E-01 | 1.00E+00 | 9.39E-02 | 1.00E+00 | 2.17E-01 | 1.00E+00 |
| SOX8_HUMAN.H10MO.D | WSACTGMAATTGATKY | 285 | 2.16E-01 | 1.00E+00 | 8.95E-01 | 1.00E+00 | 8.67E-01 | 1.00E+00 |
| EOMES_HUMAN.H10MO.D | RRGAGGTGWKAA | 286 | 2.16E-01 | 1.00E+00 | 3.76E-01 | 1.00E+00 | 1.40E-01 | 1.00E+00 |
| PO3F2_HUMAN.H10MO.D | AWWATTYATG | 287 | 2.16E-01 | 1.00E+00 | 7.21E-01 | 1.00E+00 | 9.95E-01 | 1.00E+00 |
| HIC1_HUMAN.H10MO.C | GGGKTGCCC | 288 | 2.17E-01 | 1.00E+00 | 8.29E-01 | 1.00E+00 | 5.99E-02 | 1.00E+00 |
| TBP_HUMAN.H10MO.C | RRTATAWAWDS | 289 | 2.18E-01 | 1.00E+00 | 3.51E-01 | 1.00E+00 | 9.93E-01 | 1.00E+00 |
| TAL1_HUMAN.H10MO.S | GAACAGATGGTC | 290 | 2.21E-01 | 1.00E+00 | 3.41E-01 | 1.00E+00 | 6.70E-01 | 1.00E+00 |
| ZEP1_HUMAN.H10MO.D | TGGGAAATCCCB | 291 | 2.21E-01 | 1.00E+00 | 9.62E-01 | 1.00E+00 | 7.52E-01 | 1.00E+00 |
| PO4F1_HUMAN.H10MO.D | CATTAATTATTCAT | 292 | 2.23E-01 | 1.00E+00 | 1.43E-01 | 1.00E+00 | 7.23E-01 | 1.00E+00 |
| SMRC1_HUMAN.H10MO.D | SBVTGAGTCAB | 293 | 2.24E-01 | 1.00E+00 | 6.98E-02 | 1.00E+00 | 6.32E-02 | 1.00E+00 |
| NANOG_HUMAN.H10MO.A | YYWTTGWNATGCAAATK | 294 | 2.24E-01 | 1.00E+00 | 6.70E-01 | 1.00E+00 | 7.41E-01 | 1.00E+00 |
| HXB13_HUMAN.H10MO.D | DDTTTTAYKRG | 295 | 2.25E-01 | 1.00E+00 | 4.85E-01 | 1.00E+00 | 9.80E-01 | 1.00E+00 |
| MEIS3_HUMAN.H10MO.D | DKTGACAGSTK | 296 | 2.25E-01 | 1.00E+00 | 1.77E-01 | 1.00E+00 | 3.38E-01 | 1.00E+00 |
| MAFB_HUMAN.H10MO.D | WGCTGACDS | 297 | 2.30E-01 | 1.00E+00 | 6.57E-01 | 1.00E+00 | 3.33E-01 | 1.00E+00 |
| MZF1_HUMAN.H10MO.D | RGDGGGGAW | 298 | 2.30E-01 | 1.00E+00 | 2.80E-02 | 1.00E+00 | 2.81E-02 | 1.00E+00 |
| GATA4_HUMAN.H10MO.B | RSWGATAAV | 299 | 2.30E-01 | 1.00E+00 | 3.33E-01 | 1.00E+00 | 9.50E-01 | 1.00E+00 |
| FOXI1_HUMAN.H10MO.B | YTBTGATTGGYY | 300 | 2.32E-01 | 1.00E+00 | 8.26E-01 | 1.00E+00 | 3.37E-01 | 1.00E+00 |
| MAFK_HUMAN.H10MO.S | TGCTGAGTCA | 301 | 2.34E-01 | 1.00E+00 | 1.79E-01 | 1.00E+00 | 2.20E-01 | 1.00E+00 |
| GSX1_HUMAN.H10MO.D | TAATTAGNDDTTAAT | 302 | 2.35E-01 | 1.00E+00 | 6.51E-01 | 1.00E+00 | 9.89E-01 | 1.00E+00 |
| GATA3_HUMAN.H10MO.C | WVAGATAAVAW | 303 | 2.36E-01 | 1.00E+00 | 5.49E-01 | 1.00E+00 | 9.97E-01 | 1.00E+00 |
| E2F2_HUMAN.H10MO.B | GGCGCGAAAC | 304 | 2.37E-01 | 1.00E+00 | 3.12E-01 | 1.00E+00 | 2.54E-03 | 8.04E-01 |
| SRBP1_HUMAN.H10MO.B | GGTGGGGTGAB | 305 | 2.37E-01 | 1.00E+00 | 4.93E-01 | 1.00E+00 | 5.14E-02 | 1.00E+00 |
| NOBOX_HUMAN.H10MO.C | HTAATTRSY | 306 | 2.39E-01 | 1.00E+00 | 4.39E-01 | 1.00E+00 | 9.89E-01 | 1.00E+00 |
| PROP1_HUMAN.H10MO.D | RASHAATTAAHATVR | 307 | 2.39E-01 | 1.00E+00 | 3.36E-01 | 1.00E+00 | 6.49E-01 | 1.00E+00 |

TABLE 5-continued

Transcription Factors with binding sites enriched in: (A) genes up-regulated in lesional skin at baseline; (B) genes down-regulated in lesional skin by week 12 in the placebo group; (C) genes down-regulated in lesional skin by week 12 in the nemo group.

| | | | A. Genes up-regulated in lesional skin at baseline | | B. Genes down-regulated in lesional skin by week 12 in the placebo group | | C. Genes down-regulated in lesional skin by week 12 in the nemo group | |
|---|---|---|---|---|---|---|---|---|
| | Motif | SEQ ID NO | p-value | FDR | p-value | FDR | p-value | FDR |
| KLF14_HUMAN.H10MO.D | DRGKGGGCGTGGY | 308 | 2.39E-01 | 1.00E+00 | 5.96E-01 | 1.00E+00 | 1.72E-05 | 1.10E-02 |
| NR4A2_HUMAN.H10MO.C | AAAGGTCAS | 309 | 2.40E-01 | 1.00E+00 | 6.77E-01 | 1.00E+00 | 2.14E-01 | 1.00E+00 |
| MYCN_HUMAN.H10MO.B | CCACGTGS | 310 | 2.41E-01 | 1.00E+00 | 9.27E-01 | 1.00E+00 | 1.43E-01 | 1.00E+00 |
| MEIS2_HUMAN.H10MO.B | TTGACAGBTGTCM | 311 | 2.41E-01 | 1.00E+00 | 4.72E-01 | 1.00E+00 | 8.33E-01 | 1.00E+00 |
| THA_HUMAN.H10MO.C | RGGTCABYTSAGGTCAK | 312 | 2.42E-01 | 1.00E+00 | 3.02E-01 | 1.00E+00 | 1.86E-02 | 1.00E+00 |
| PPARG_HUMAN.H10MO.A | AWBTRGGKCAAAGGKCA | 313 | 2.43E-01 | 1.00E+00 | 5.82E-01 | 1.00E+00 | 7.60E-01 | 1.00E+00 |
| TFEB_HUMAN.H10MO.C | RGTCACGTG | 314 | 2.43E-01 | 1.00E+00 | 3.75E-01 | 1.00E+00 | 1.19E-01 | 1.00E+00 |
| E2F8_HUMAN.H10MO.D | TTTRGMGGGAAW | 315 | 2.43E-01 | 1.00E+00 | 2.93E-01 | 1.00E+00 | 3.49E-01 | 1.00E+00 |
| VAX2_HUMAN.H10MO.D | CACTAATTAVSYTWWH | 316 | 2.45E-01 | 1.00E+00 | 3.76E-02 | 1.00E+00 | 9.91E-01 | 1.00E+00 |
| TFE3_HUMAN.H10MO.C | RGTCAYGTGV | 317 | 2.45E-01 | 1.00E+00 | 5.30E-01 | 1.00E+00 | 4.20E-01 | 1.00E+00 |
| RFX1_HUMAN.H10MO.C | GTTGCYAGGSAA | 318 | 2.48E-01 | 1.00E+00 | 1.54E-01 | 1.00E+00 | 9.21E-03 | 9.97E-01 |
| LHX2_HUMAN.H10MO.D | YRSDTTYAATWAG | 319 | 2.49E-01 | 1.00E+00 | 1.56E-01 | 1.00E+00 | 9.33E-01 | 1.00E+00 |
| CEBPZ_HUMAN.H10MO.D | DCTSATTGGCT | 320 | 2.50E-01 | 1.00E+00 | 8.80E-01 | 1.00E+00 | 5.08E-01 | 1.00E+00 |
| ITF2_HUMAN.H10MO.B | VCAGGTGCD | 321 | 2.52E-01 | 1.00E+00 | 3.22E-02 | 1.00E+00 | 1.08E-02 | 9.99E-01 |
| SCRT2_HUMAN.H10MO.D | RWGCAACAGGTGK | 322 | 2.53E-01 | 1.00E+00 | 7.50E-01 | 1.00E+00 | 1.96E-01 | 1.00E+00 |
| NFAC4_HUMAN.H10MO.C | DGGAAAAYTW | 323 | 2.54E-01 | 1.00E+00 | 5.79E-01 | 1.00E+00 | 7.26E-01 | 1.00E+00 |
| ZN282_HUMAN.H10MO.D | MGKRTTRTGGGARA | 324 | 2.55E-01 | 1.00E+00 | 8.76E-01 | 1.00E+00 | 2.89E-01 | 1.00E+00 |
| EGR1_HUMAN.H10MO.S | BGCGKGGGCGG | 325 | 2.56E-01 | 1.00E+00 | 3.12E-01 | 1.00E+00 | 7.01E-07 | 4.49E-04 |
| EMX2_HUMAN.H10MO.D | TAATTAGYDWAW | 326 | 2.58E-01 | 1.00E+00 | 6.68E-01 | 1.00E+00 | 9.99E-01 | 1.00E+00 |
| MYBA_HUMAN.H10MO.D | HRACCGTTAAM | 327 | 2.59E-01 | 1.00E+00 | 2.45E-01 | 1.00E+00 | 2.94E-01 | 1.00E+00 |
| ELK3_HUMAN.H10MO.D | VMCHGGAARTSC | 328 | 2.60E-01 | 1.00E+00 | 5.23E-01 | 1.00E+00 | 3.71E-05 | 2.35E-02 |
| MAFF_HUMAN.H10MO.A | AWWWHTGCTGASTCAGCAWWWW | 329 | 2.61E-01 | 1.00E+00 | 3.38E-01 | 1.00E+00 | 6.70E-01 | 1.00E+00 |
| BSH_HUMAN.H10MO.D | YVATTAACBMATTA | 330 | 2.61E-01 | 1.00E+00 | 4.36E-01 | 1.00E+00 | 9.99E-01 | 1.00E+00 |
| HAND1_HUMAN.H10MO.D | GBRTCTGGMWTT | 331 | 2.63E-01 | 1.00E+00 | 1.35E-01 | 1.00E+00 | 6.90E-02 | 1.00E+00 |
| P63_HUMAN.H10MO.A | RRRCAWGYCTGGRCWTGYH | 332 | 2.65E-01 | 1.00E+00 | 5.16E-01 | 1.00E+00 | 1.39E-01 | 1.00E+00 |
| HXA10_HUMAN.H10MO.C | KATRRTTTATGW | 333 | 2.66E-01 | 1.00E+00 | 4.73E-01 | 1.00E+00 | 1.00E+00 | 1.00E+00 |
| ERR3_HUMAN.H10MO.B | TCAAGGTCA | 334 | 2.66E-01 | 1.00E+00 | 2.93E-01 | 1.00E+00 | 2.09E-01 | 1.00E+00 |
| GBX1_HUMAN.H10MO.D | BTAATTRRYNHWWWWWW | 335 | 2.70E-01 | 1.00E+00 | 4.01E-01 | 1.00E+00 | 9.95E-01 | 1.00E+00 |
| EGR3_HUMAN.H10MO.D | WGAGTGGGYGT | 336 | 2.71E-01 | 1.00E+00 | 3.89E-01 | 1.00E+00 | 1.95E-02 | 1.00E+00 |
| TBX2_HUMAN.H10MO.D | TGVMWWCABAGGTGTGARRHGYSMC | 337 | 2.72E-01 | 1.00E+00 | 3.84E-01 | 1.00E+00 | 5.50E-01 | 1.00E+00 |
| HXB2_HUMAN.H10MO.D | WAGAAYVTTCTAGAA | 338 | 2.74E-01 | 1.00E+00 | 3.35E-02 | 1.00E+00 | 8.40E-01 | 1.00E+00 |
| BHE41_HUMAN.H10MO.D | WSVRKSYCACGTGMWGRRRV | 339 | 2.75E-01 | 1.00E+00 | 6.39E-01 | 1.00E+00 | 1.15E-03 | 5.22E-01 |

TABLE 5-continued

Transcription Factors with binding sites enriched in: (A) genes up-regulated in lesional skin at baseline; (B) genes down-regulated in lesional skin by week 12 in the placebo group; (C) genes down-regulated in lesional skin by week 12 in the nemo group.

| | Motif | SEQ ID NO | A. Genes up-regulated in lesional skin at baseline p-value | A. FDR | B. Genes down-regulated in lesional skin by week 12 in the placebo group p-value | B. FDR | C. Genes down-regulated in lesional skin by week 12 in the nemo group p-value | C. FDR |
|---|---|---|---|---|---|---|---|---|
| PRDM1_HUMAN.H10MO.C | RAAAGTGAAAGTGA | 340 | 2.75E-01 | 1.00E+00 | 2.06E-01 | 1.00E+00 | 8.31E-01 | 1.00E+00 |
| GBX2_HUMAN.H10MO.D | BTAATTRSYBHHWWWWW | 341 | 2.75E-01 | 1.00E+00 | 2.96E-01 | 1.00E+00 | 9.97E-01 | 1.00E+00 |
| ISL2_HUMAN.H10MO.D | YVYTAAKTGCW | 342 | 2.75E-01 | 1.00E+00 | 5.10E-01 | 1.00E+00 | 9.96E-01 | 1.00E+00 |
| LMX1A_HUMAN.H10MO.D | TAATTAATTWKKTWATTWW | 343 | 2.77E-01 | 1.00E+00 | 6.15E-01 | 1.00E+00 | 7.14E-01 | 1.00E+00 |
| ZN740_HUMAN.H10MO.D | DKKGGGGGGGHRDK | 344 | 2.77E-01 | 1.00E+00 | 6.84E-01 | 1.00E+00 | 6.64E-03 | 9.86E-01 |
| ZN652_HUMAN.H10MO.D | AARGGGTTAAW | 345 | 2.79E-01 | 1.00E+00 | 2.22E-01 | 1.00E+00 | 8.59E-01 | 1.00E+00 |
| PKNX2_HUMAN.H10MO.D | DKGRCRGGTGKSA | 346 | 2.80E-01 | 1.00E+00 | 4.41E-01 | 1.00E+00 | 1.93E-02 | 1.00E+00 |
| OLIG3_HUMAN.H10MO.D | ACCATATGKTB | 347 | 2.80E-01 | 1.00E+00 | 9.55E-01 | 1.00E+00 | 9.93E-01 | 1.00E+00 |
| ARNT_HUMAN.H10MO.B | BYRCGTGC | 348 | 2.80E-01 | 1.00E+00 | 7.42E-01 | 1.00E+00 | 5.66E-03 | 9.74E-01 |
| ZN384_HUMAN.H10MO.C | GSAAAAAVYMKS | 349 | 2.81E-01 | 1.00E+00 | 5.43E-01 | 1.00E+00 | 9.31E-01 | 1.00E+00 |
| HXA11_HUMAN.H10MO.D | TWAADTTTTAYGR | 350 | 2.85E-01 | 1.00E+00 | 3.69E-01 | 1.00E+00 | 6.94E-01 | 1.00E+00 |
| LHX8_HUMAN.H10MO.D | YRYTRATTRCMATTAATT | 351 | 2.86E-01 | 1.00E+00 | 8.85E-01 | 1.00E+00 | 9.76E-01 | 1.00E+00 |
| DBP_HUMAN.H10MO.B | VTTATGYAABM | 352 | 2.89E-01 | 1.00E+00 | 6.30E-01 | 1.00E+00 | 1.00E+00 | 1.00E+00 |
| E2F5_HUMAN.H10MO.B | SGCGCSAAAH | 353 | 2.92E-01 | 1.00E+00 | 8.71E-01 | 1.00E+00 | 1.89E-03 | 7.02E-01 |
| GATA1_HUMAN.H10MO.A | CTGBNNVVBRSAGATAAGR | 354 | 2.94E-01 | 1.00E+00 | 1.80E-01 | 1.00E+00 | 6.46E-01 | 1.00E+00 |
| STAT1_HUMAN.H10MO.A | YCMTTTCCHGGAAAWCHCATKM | 355 | 2.95E-01 | 1.00E+00 | 3.25E-01 | 1.00E+00 | 5.00E-01 | 1.00E+00 |
| LHX6_HUMAN.H10MO.D | VYTAATTAGYRYTAATTA | 356 | 2.96E-01 | 1.00E+00 | 2.74E-01 | 1.00E+00 | 9.93E-01 | 1.00E+00 |
| SOX15_HUMAN.H10MO.D | CWTTGTT | 357 | 3.00E-01 | 1.00E+00 | 3.67E-02 | 1.00E+00 | 7.29E-01 | 1.00E+00 |
| RELB_HUMAN.H10MO.C | RGGGRMTTTCCM | 358 | 3.00E-01 | 1.00E+00 | 3.34E-03 | 8.83E-01 | 2.24E-03 | 7.62E-01 |
| KLF13_HUMAN.H10MO.D | DRGKGGGCGKD | 359 | 3.00E-01 | 1.00E+00 | 5.08E-01 | 1.00E+00 | 2.38E-05 | 1.52E-02 |
| GMEB2_HUMAN.H10MO.D | NBKTACGTVRN | 360 | 3.04E-01 | 1.00E+00 | 4.93E-01 | 1.00E+00 | 7.71E-01 | 1.00E+00 |
| ZN784_HUMAN.H10MO.D | DMGGTAGGTRV | 361 | 3.05E-01 | 1.00E+00 | 5.97E-01 | 1.00E+00 | 1.53E-01 | 1.00E+00 |
| MNT_HUMAN.H10MO.D | RKRRRDKVAGGKGDDR | 362 | 3.07E-01 | 1.00E+00 | 6.97E-01 | 1.00E+00 | 1.35E-01 | 1.00E+00 |
| SRBP2_HUMAN.H10MO.B | VSGTGGGGWGABG | 363 | 3.07E-01 | 1.00E+00 | 5.97E-01 | 1.00E+00 | 1.81E-01 | 1.00E+00 |
| FOXF2_HUMAN.H10MO.D | TGTTTACHTWD | 364 | 3.08E-01 | 1.00E+00 | 3.26E-01 | 1.00E+00 | 9.21E-01 | 1.00E+00 |
| DLX4_HUMAN.H10MO.D | TAATTASNBHWWWWWD | 365 | 3.09E-01 | 1.00E+00 | 4.79E-01 | 1.00E+00 | 9.53E-01 | 1.00E+00 |
| SOX10_HUMAN.H10MO.D | BCWTTGT | 366 | 3.12E-01 | 1.00E+00 | 2.14E-01 | 1.00E+00 | 9.36E-01 | 1.00E+00 |
| GSX2_HUMAN.H10MO.D | YTAATTRSHWWTTAAT | 367 | 3.17E-01 | 1.00E+00 | 4.23E-01 | 1.00E+00 | 8.77E-01 | 1.00E+00 |
| CR3L2_HUMAN.H10MO.D | TGATGACGTGGCA | 368 | 3.17E-01 | 1.00E+00 | 6.77E-01 | 1.00E+00 | 1.81E-02 | 1.00E+00 |
| ZSC16_HUMAN.H10MO.D | RRGGTGYTCTGTTAACAMTW | 369 | 3.20E-01 | 1.00E+00 | 8.84E-01 | 1.00E+00 | 9.03E-01 | 1.00E+00 |
| BACH1_HUMAN.H10MO.A | TGCTGAGTCABSS | 370 | 3.21E-01 | 1.00E+00 | 2.33E-01 | 1.00E+00 | 1.05E-03 | 4.89E-01 |
| PO3F1_HUMAN.H10MO.C | VATKSWWATGCAAW | 371 | 3.21E-01 | 1.00E+00 | 3.23E-01 | 1.00E+00 | 9.56E-01 | 1.00E+00 |
| CREB3_HUMAN.H10MO.D | KGRTGACGTGGCA | 372 | 3.22E-01 | 1.00E+00 | 2.17E-01 | 1.00E+00 | 4.02E-03 | 9.24E-01 |

TABLE 5-continued

Transcription Factors with binding sites enriched in: (A) genes up-regulated in lesional skin at baseline; (B) genes down-regulated in lesional skin by week 12 in the placebo group; (C) genes down-regulated in lesional skin by week 12 in the nemo group.

| | Motif | SEQ ID NO | A. Genes up-regulated in lesional skin at baseline p-value | A. FDR | B. Genes down-regulated in lesional skin by week 12 in the placebo group p-value | B. FDR | C. Genes down-regulated in lesional skin by week 12 in the nemo group p-value | C. FDR |
|---|---|---|---|---|---|---|---|---|
| ZBTB6_HUMAN.H10MO.D | VGRTGATRGAGCC | 373 | 3.22E-01 | 1.00E+00 | 2.43E-01 | 1.00E+00 | 3.92E-02 | 1.00E+00 |
| NFYB_HUMAN.H10MO.A | YRRCCAATSAGMR | 374 | 3.22E-01 | 1.00E+00 | 4.92E-01 | 1.00E+00 | 1.47E-01 | 1.00E+00 |
| ANDR_HUMAN.H10MO.A | DGBACABHCTGTTCYHK | 375 | 3.22E-01 | 1.00E+00 | 6.71E-02 | 1.00E+00 | 7.18E-01 | 1.00E+00 |
| MAX_HUMAN.H10MO.A | RGYCACGTGST | 376 | 3.29E-01 | 1.00E+00 | 7.93E-01 | 1.00E+00 | 5.17E-01 | 1.00E+00 |
| PDX1_HUMAN.H10MO.C | RGTAATTAG | 377 | 3.31E-01 | 1.00E+00 | 8.19E-01 | 1.00E+00 | 9.79E-01 | 1.00E+00 |
| TBX4_HUMAN.H10MO.D | RAGGTGTGAWAWNTVACACC | 378 | 3.32E-01 | 1.00E+00 | 4.40E-02 | 1.00E+00 | 5.46E-01 | 1.00E+00 |
| BARH1_HUMAN.H10MO.D | TAAWYGBYBHTAA | 379 | 3.33E-01 | 1.00E+00 | 7.48E-01 | 1.00E+00 | 9.99E-01 | 1.00E+00 |
| TEF_HUMAN.H10MO.D | TGTTTATGTAAMTK | 380 | 3.34E-01 | 1.00E+00 | 2.63E-01 | 1.00E+00 | 9.21E-01 | 1.00E+00 |
| RXRB_HUMAN.H10MO.C | TSAGGTCASR | 381 | 3.38E-01 | 1.00E+00 | 1.94E-01 | 1.00E+00 | 3.78E-01 | 1.00E+00 |
| NDF2_HUMAN.H10MO.D | DBSRTATGDTS | 382 | 3.40E-01 | 1.00E+00 | 8.01E-01 | 1.00E+00 | 8.65E-01 | 1.00E+00 |
| MECP2_HUMAN.H10MO.C | SCCGGRR | 383 | 3.42E-01 | 1.00E+00 | 7.43E-01 | 1.00E+00 | 2.20E-06 | 1.41E-03 |
| ZBT49_HUMAN.H10MO.D | NBSNTAATTRV | 384 | 3.42E-01 | 1.00E+00 | 3.34E-01 | 1.00E+00 | 9.92E-01 | 1.00E+00 |
| HIC2_HUMAN.H10MO.D | HCRTGCCAGVN | 385 | 3.42E-01 | 1.00E+00 | 7.67E-01 | 1.00E+00 | 3.68E-02 | 1.00E+00 |
| CDX2_HUMAN.H10MO.C | WTTTATRD | 386 | 3.43E-01 | 1.00E+00 | 4.38E-01 | 1.00E+00 | 9.89E-01 | 1.00E+00 |
| FOXQ1_HUMAN.H10MO.C | HATTGTTTATTT | 387 | 3.43E-01 | 1.00E+00 | 3.77E-01 | 1.00E+00 | 7.16E-01 | 1.00E+00 |
| RARA_HUMAN.H10MO.C | RGGTCANSRRVAGGTCA | 388 | 3.44E-01 | 1.00E+00 | 4.58E-01 | 1.00E+00 | 6.90E-02 | 1.00E+00 |
| NFAC2_HUMAN.H10MO.B | TGGAAAAWY | 389 | 3.45E-01 | 1.00E+00 | 4.70E-01 | 1.00E+00 | 2.70E-01 | 1.00E+00 |
| ZN232_HUMAN.H10MO.D | TGTTAAAYGTAGATTAAGY | 390 | 3.48E-01 | 1.00E+00 | 4.25E-01 | 1.00E+00 | 9.71E-01 | 1.00E+00 |
| FOXA1_HUMAN.H10MO.A | WTRTTTACWYWDB | 391 | 3.49E-01 | 1.00E+00 | 9.52E-02 | 1.00E+00 | 7.79E-01 | 1.00E+00 |
| HME2_HUMAN.H10MO.D | NNTRRTTARNB | 392 | 3.50E-01 | 1.00E+00 | 7.27E-01 | 1.00E+00 | 7.68E-01 | 1.00E+00 |
| FOXO1_HUMAN.H10MO.C | DDBTTGTTTWBWWTTT | 393 | 3.51E-01 | 1.00E+00 | 1.53E-01 | 1.00E+00 | 5.41E-01 | 1.00E+00 |
| LHX9_HUMAN.H10MO.D | YTAATTAGYNHWWWWWD | 394 | 3.54E-01 | 1.00E+00 | 4.83E-01 | 1.00E+00 | 9.99E-01 | 1.00E+00 |
| DMBX1_HUMAN.H10MO.D | YMMTWWWAAYCYAATTAABD | 395 | 3.56E-01 | 1.00E+00 | 4.84E-01 | 1.00E+00 | 9.97E-01 | 1.00E+00 |
| HXA5_HUMAN.H10MO.D | YTRATTAATG | 396 | 3.57E-01 | 1.00E+00 | 7.36E-01 | 1.00E+00 | 9.77E-01 | 1.00E+00 |
| JDP2_HUMAN.H10MO.D | BGATGACGTCAY | 397 | 3.59E-01 | 1.00E+00 | 3.85E-02 | 1.00E+00 | 8.70E-01 | 1.00E+00 |
| ATOH1_HUMAN.H10MO.D | YRMCATATGYY | 398 | 3.60E-01 | 1.00E+00 | 3.70E-01 | 1.00E+00 | 8.28E-01 | 1.00E+00 |
| PITX2_HUMAN.H10MO.D | TKGGATTAVH | 399 | 3.62E-01 | 1.00E+00 | 3.72E-01 | 1.00E+00 | 7.59E-01 | 1.00E+00 |
| PAX7_HUMAN.H10MO.D | TAATYGATTAW | 400 | 3.63E-01 | 1.00E+00 | 7.73E-01 | 1.00E+00 | 1.00E+00 | 1.00E+00 |
| NKX28_HUMAN.H10MO.C | TTCAAGKRC | 401 | 3.64E-01 | 1.00E+00 | 4.46E-02 | 1.00E+00 | 6.09E-01 | 1.00E+00 |
| NR1I2_HUMAN.H10MO.S | RAGTTCAB | 402 | 3.66E-01 | 1.00E+00 | 6.02E-01 | 1.00E+00 | 7.54E-01 | 1.00E+00 |
| HXA13_HUMAN.H10MO.C | GDTTTTATTGG | 403 | 3.68E-01 | 1.00E+00 | 2.39E-01 | 1.00E+00 | 9.47E-01 | 1.00E+00 |
| NFE2_HUMAN.H10MO.B | RSVATGACTCAGCA | 404 | 3.72E-01 | 1.00E+00 | 1.17E-01 | 1.00E+00 | 3.61E-01 | 1.00E+00 |
| DLX3_HUMAN.H10MO.C | GMTAATTRSW | 405 | 3.75E-01 | 1.00E+00 | 8.33E-01 | 1.00E+00 | 9.98E-01 | 1.00E+00 |

TABLE 5-continued

Transcription Factors with binding sites enriched in: (A) genes up-regulated in lesional skin at baseline; (B) genes down-regulated in lesional skin by week 12 in the placebo group; (C) genes down-regulated in lesional skin by week 12 in the nemo group.

| | Motif | SEQ ID NO | A. Genes up-regulated in lesional skin at baseline p-value | FDR | B. Genes down-regulated in lesional skin by week 12 in the placebo group p-value | FDR | C. Genes down-regulated in lesional skin by week 12 in the nemo group p-value | FDR |
|---|---|---|---|---|---|---|---|---|
| IRX3_HUMAN.H10MO.D | WNWCATGTWMT | 406 | 3.76E-01 | 1.00E+00 | 8.76E-01 | 1.00E+00 | 9.83E-01 | 1.00E+00 |
| HNF6_HUMAN.H10MO.C | WWTATTGATTTWDH | 407 | 3.76E-01 | 1.00E+00 | 3.48E-01 | 1.00E+00 | 9.85E-01 | 1.00E+00 |
| ZN639_HUMAN.H10MO.D | SRVKGCGCATGCGCAGVRVS | 408 | 3.76E-01 | 1.00E+00 | 7.02E-01 | 1.00E+00 | 5.57E-05 | 3.51E-02 |
| KLF3_HUMAN.H10MO.D | HRCYWGGGTGKGGCT | 409 | 3.77E-01 | 1.00E+00 | 5.85E-01 | 1.00E+00 | 2.61E-01 | 1.00E+00 |
| PPARA_HUMAN.H10MO.C | RGGTCARAGGTCA | 410 | 3.79E-01 | 1.00E+00 | 4.65E-01 | 1.00E+00 | 6.51E-02 | 1.00E+00 |
| PO5F1_HUMAN.H10MO.A | CYWTTSWTATGCAAAT | 411 | 3.81E-01 | 1.00E+00 | 2.97E-01 | 1.00E+00 | 9.32E-01 | 1.00E+00 |
| TFDP1_HUMAN.H10MO.S | AWWKRGCGGGAAAY | 412 | 3.82E-01 | 1.00E+00 | 4.91E-01 | 1.00E+00 | 2.14E-01 | 1.00E+00 |
| TEAD4_HUMAN.H10MO.A | RCATTCCWGVSMT | 413 | 3.84E-01 | 1.00E+00 | 5.91E-01 | 1.00E+00 | 2.81E-01 | 1.00E+00 |
| RUNX1_HUMAN.H10MO.A | BYTGTGGTTWB | 414 | 3.85E-01 | 1.00E+00 | 5.50E-01 | 1.00E+00 | 1.53E-01 | 1.00E+00 |
| ZN713_HUMAN.H10MO.D | RWAGAARAADGVSANGMAA | 415 | 3.85E-01 | 1.00E+00 | 4.54E-01 | 1.00E+00 | 9.36E-01 | 1.00E+00 |
| HIF1A_HUMAN.H10MO.A | SBSTACGTGCSB | 416 | 3.86E-01 | 1.00E+00 | 8.22E-01 | 1.00E+00 | 1.02E-03 | 4.79E-01 |
| AHR_HUMAN.H10MO.B | DTYGCGTGM | 417 | 3.86E-01 | 1.00E+00 | 8.77E-01 | 1.00E+00 | 2.82E-02 | 1.00E+00 |
| NKX23_HUMAN.H10MO.D | BTYAAGTGGKW | 418 | 3.89E-01 | 1.00E+00 | 2.95E-01 | 1.00E+00 | 6.16E-01 | 1.00E+00 |
| RARG_HUMAN.H10MO.S | RAGGTCA | 419 | 3.91E-01 | 1.00E+00 | 2.17E-01 | 1.00E+00 | 1.38E-01 | 1.00E+00 |
| EHF_HUMAN.H10MO.C | RRAVVAGGAARTRRRRR | 420 | 3.92E-01 | 1.00E+00 | 5.94E-01 | 1.00E+00 | 9.16E-01 | 1.00E+00 |
| TBX20_HUMAN.H10MO.D | AGGTGTGAAGGTGTGAA | 421 | 3.96E-01 | 1.00E+00 | 5.16E-01 | 1.00E+00 | 3.50E-01 | 1.00E+00 |
| P5F1B_HUMAN.H10MO.D | DMATTTGCATATTYAW | 422 | 3.96E-01 | 1.00E+00 | 9.82E-01 | 1.00E+00 | 9.98E-01 | 1.00E+00 |
| HSF2_HUMAN.H10MO.A | VGAABRTTCTAGAA | 423 | 4.01E-01 | 1.00E+00 | 7.43E-01 | 1.00E+00 | 6.68E-01 | 1.00E+00 |
| BARH2_HUMAN.H10MO.D | VYTAAWYGNTSHWWWWHR | 424 | 4.05E-01 | 1.00E+00 | 7.72E-01 | 1.00E+00 | 9.78E-01 | 1.00E+00 |
| MYC_HUMAN.H10MO.A | GASCACGTGGY | 425 | 4.08E-01 | 1.00E+00 | 3.80E-01 | 1.00E+00 | 3.72E-03 | 9.08E-01 |
| RFX4_HUMAN.H10MO.D | SGTTGCCATGGYWAC | 426 | 4.09E-01 | 1.00E+00 | 3.81E-01 | 1.00E+00 | 5.86E-01 | 1.00E+00 |
| TF2LX_HUMAN.H10MO.D | GACAGCTGTCATWRY | 427 | 4.10E-01 | 1.00E+00 | 8.68E-01 | 1.00E+00 | 9.55E-01 | 1.00E+00 |
| PRD14_HUMAN.H10MO.C | RRGTTAGRGACCYR | 428 | 4.16E-01 | 1.00E+00 | 4.72E-01 | 1.00E+00 | 2.08E-01 | 1.00E+00 |
| MEF2D_HUMAN.H10MO.C | GCTATTTWTAGV | 429 | 4.19E-01 | 1.00E+00 | 5.16E-01 | 1.00E+00 | 8.27E-01 | 1.00E+00 |
| SHOX_HUMAN.H10MO.D | YTAATTRRYTWWWWWWD | 430 | 4.20E-01 | 1.00E+00 | 4.81E-01 | 1.00E+00 | 9.98E-01 | 1.00E+00 |
| NKX62_HUMAN.H10MO.D | NDTTAATKASN | 431 | 4.21E-01 | 1.00E+00 | 6.70E-01 | 1.00E+00 | 9.99E-01 | 1.00E+00 |
| PO3F4_HUMAN.H10MO.D | TMATTTGCATAATTWAW | 432 | 4.21E-01 | 1.00E+00 | 6.92E-01 | 1.00E+00 | 9.84E-01 | 1.00E+00 |
| IRF1_HUMAN.H10MO.A | RAAASNGAAAGTGAAASTRR | 433 | 4.23E-01 | 1.00E+00 | 8.25E-01 | 1.00E+00 | 7.47E-01 | 1.00E+00 |
| DRGX_HUMAN.H10MO.D | TAATYTAATTA | 434 | 4.24E-01 | 1.00E+00 | 2.16E-01 | 1.00E+00 | 9.99E-01 | 1.00E+00 |
| VSX1_HUMAN.H10MO.D | TAATTAGCHWWWWW | 435 | 4.27E-01 | 1.00E+00 | 8.96E-01 | 1.00E+00 | 1.00E+00 | 1.00E+00 |
| ZBED1_HUMAN.H10MO.D | YATGTCGCGAYAK | 436 | 4.30E-01 | 1.00E+00 | 6.22E-01 | 1.00E+00 | 4.59E-02 | 1.00E+00 |
| XBP1_HUMAN.H10MO.C | GACGTGKCMTWW | 437 | 4.33E-01 | 1.00E+00 | 6.91E-02 | 1.00E+00 | 5.02E-02 | 1.00E+00 |
| NR1D1_HUMAN.H10MO.C | AWAARTAGGTCARW | 438 | 4.33E-01 | 1.00E+00 | 6.45E-01 | 1.00E+00 | 7.85E-01 | 1.00E+00 |

TABLE 5-continued

Transcription Factors with binding sites enriched in: (A) genes up-regulated in lesional skin at baseline; (B) genes down-regulated in lesional skin by week 12 in the placebo group; (C) genes down-regulated in lesional skin by week 12 in the nemo group.

| | Motif | SEQ ID NO | A. Genes up-regulated in lesional skin at baseline p-value | FDR | B. Genes down-regulated in lesional skin by week 12 in the placebo group p-value | FDR | C. Genes down-regulated in lesional skin by week 12 in the nemo group p-value | FDR |
|---|---|---|---|---|---|---|---|---|
| NKX25_HUMAN.H10MO.C | TYAAGTG | 439 | 4.36E-01 | 1.00E+00 | 3.83E-01 | 1.00E+00 | 2.83E-01 | 1.00E+00 |
| ZN589_HUMAN.H10MO.D | CCMASGGKWWYWRCCS | 440 | 4.38E-01 | 1.00E+00 | 6.29E-02 | 1.00E+00 | 2.46E-01 | 1.00E+00 |
| SMAD3_HUMAN.H10MO.C | STGTCTGKCY | 441 | 4.39E-01 | 1.00E+00 | 4.66E-01 | 1.00E+00 | 5.26E-02 | 1.00E+00 |
| MEF2C_HUMAN.H10MO.C | DKCTATTTTTRGM | 442 | 4.40E-01 | 1.00E+00 | 8.91E-01 | 1.00E+00 | 8.38E-01 | 1.00E+00 |
| RFX2_HUMAN.H10MO.C | SSSSCSGTTGCCATGGMRACSG | 443 | 4.40E-01 | 1.00E+00 | 3.75E-01 | 1.00E+00 | 5.42E-04 | 2.93E-01 |
| HMBX1_HUMAN.H10MO.D | DVCTRGTTAMN | 444 | 4.43E-01 | 1.00E+00 | 6.95E-01 | 1.00E+00 | 7.74E-01 | 1.00E+00 |
| OTX2_HUMAN.H10MO.C | KHDMWVGGATTARRK | 445 | 4.46E-01 | 1.00E+00 | 8.03E-02 | 1.00E+00 | 9.67E-02 | 1.00E+00 |
| RXRG_HUMAN.H10MO.B | GGTCAAAGGTCAH | 446 | 4.46E-01 | 1.00E+00 | 6.99E-01 | 1.00E+00 | 2.08E-01 | 1.00E+00 |
| CEBPB_HUMAN.H10MO.A | KATTGCRYAAYH | 447 | 4.47E-01 | 1.00E+00 | 3.26E-02 | 1.00E+00 | 7.67E-01 | 1.00E+00 |
| HMGA2_HUMAN.H10MO.D | AATWWYSSSSAATAT | 448 | 4.49E-01 | 1.00E+00 | 5.57E-01 | 1.00E+00 | 9.97E-01 | 1.00E+00 |
| MAFK_HUMAN.H10MO.A | RAAWNTGCTGASTCAGCAWWWW | 449 | 4.49E-01 | 1.00E+00 | 2.43E-01 | 1.00E+00 | 9.52E-01 | 1.00E+00 |
| HXD4_HUMAN.H10MO.D | TTAATTGW | 450 | 4.50E-01 | 1.00E+00 | 6.20E-01 | 1.00E+00 | 8.19E-01 | 1.00E+00 |
| CREB5_HUMAN.H10MO.D | RRTGACGTMAT | 451 | 4.50E-01 | 1.00E+00 | 3.90E-02 | 1.00E+00 | 9.19E-01 | 1.00E+00 |
| RX_HUMAN.H10MO.D | TTAATTRRYWA | 452 | 4.53E-01 | 1.00E+00 | 1.28E-01 | 1.00E+00 | 1.00E+00 | 1.00E+00 |
| ENOA_HUMAN.H10MO.A | SRSCAYGTGKSHR | 453 | 4.53E-01 | 1.00E+00 | 4.14E-01 | 1.00E+00 | 5.07E-01 | 1.00E+00 |
| PRGR_HUMAN.H10MO.C | RGAACANYCTGTH | 454 | 4.55E-01 | 1.00E+00 | 7.73E-01 | 1.00E+00 | 5.28E-01 | 1.00E+00 |
| NR5A2_HUMAN.H10MO.C | YYCAAGGYYA | 455 | 4.59E-01 | 1.00E+00 | 7.30E-01 | 1.00E+00 | 1.70E-02 | 1.00E+00 |
| FOXP2_HUMAN.H10MO.A | BTGTTTACN | 456 | 4.62E-01 | 1.00E+00 | 3.53E-01 | 1.00E+00 | 9.63E-01 | 1.00E+00 |
| ONEC2_HUMAN.H10MO.D | DKSWTKWTATKGATTTTTYYT | 457 | 4.63E-01 | 1.00E+00 | 9.52E-01 | 1.00E+00 | 7.47E-01 | 1.00E+00 |
| LMX1B_HUMAN.H10MO.D | TAATTAAHWVMYTWWWWW | 458 | 4.63E-01 | 1.00E+00 | 7.52E-01 | 1.00E+00 | 8.16E-01 | 1.00E+00 |
| HEY1_HUMAN.H10MO.D | KGRCACGTGBCK | 459 | 4.65E-01 | 1.00E+00 | 5.13E-01 | 1.00E+00 | 1.57E-02 | 1.00E+00 |
| NKX61_HUMAN.H10MO.D | WWTTAATKASBTTTWAWTD | 460 | 4.66E-01 | 1.00E+00 | 4.91E-01 | 1.00E+00 | 9.38E-01 | 1.00E+00 |
| DPRX_HUMAN.H10MO.D | VSGGATTADCB | 461 | 4.68E-01 | 1.00E+00 | 3.50E-01 | 1.00E+00 | 7.34E-01 | 1.00E+00 |
| HXB6_HUMAN.H10MO.D | AWTGATTKATGMM | 462 | 4.68E-01 | 1.00E+00 | 9.44E-01 | 1.00E+00 | 9.15E-01 | 1.00E+00 |
| HXA2_HUMAN.H10MO.D | NGTAATTARBD | 463 | 4.72E-01 | 1.00E+00 | 8.33E-01 | 1.00E+00 | 1.00E+00 | 1.00E+00 |
| PBX2_HUMAN.H10MO.C | KRAWKTGATTGATKS | 464 | 4.78E-01 | 1.00E+00 | 4.58E-01 | 1.00E+00 | 9.79E-01 | 1.00E+00 |
| RFX3_HUMAN.H10MO.B | BGTTRCCATGGYRA | 465 | 4.83E-01 | 1.00E+00 | 6.30E-02 | 1.00E+00 | 2.08E-01 | 1.00E+00 |
| PO4F3_HUMAN.H10MO.D | TCATTAATTATKCAT | 466 | 4.84E-01 | 1.00E+00 | 6.49E-01 | 1.00E+00 | 9.35E-01 | 1.00E+00 |
| PRRX2_HUMAN.H10MO.C | YTAATTR | 467 | 4.84E-01 | 1.00E+00 | 6.71E-01 | 1.00E+00 | 1.00E+00 | 1.00E+00 |
| ZBT18_HUMAN.H10MO.D | TCCAGATGTTBVSS | 468 | 4.86E-01 | 1.00E+00 | 6.66E-01 | 1.00E+00 | 5.70E-02 | 1.00E+00 |
| TF7L1_HUMAN.H10MO.D | WDRDDMWWCGGGGMGV | 469 | 4.89E-01 | 1.00E+00 | 5.84E-01 | 1.00E+00 | 1.90E-02 | 1.00E+00 |
| SPIB_HUMAN.H10MO.B | ARAAASMGGAAS | 470 | 4.91E-01 | 1.00E+00 | 7.16E-01 | 1.00E+00 | 9.89E-01 | 1.00E+00 |
| PAX1_HUMAN.H10MO.D | YSGTCACGCWTGANTGV | 471 | 4.92E-01 | 1.00E+00 | 2.46E-01 | 1.00E+00 | 2.23E-01 | 1.00E+00 |

TABLE 5-continued

Transcription Factors with binding sites enriched in: (A) genes up-regulated in lesional skin at baseline; (B) genes down-regulated in lesional skin by week 12 in the placebo group; (C) genes down-regulated in lesional skin by week 12 in the nemo group.

| | | SEQ ID | A. Genes up-regulated in lesional skin at baseline | | B. Genes down-regulated in lesional skin by week 12 in the placebo group | | C. Genes down-regulated in lesional skin by week 12 in the nemo group | |
|---|---|---|---|---|---|---|---|---|
| | Motif | NO | p-value | FDR | p-value | FDR | p-value | FDR |
| PHX2A_HUMAN.H10MO.D | TAATYTAATTA | 472 | 4.94E-01 | 1.00E+00 | 6.73E-01 | 1.00E+00 | 9.99E-01 | 1.00E+00 |
| HME1_HUMAN.H10MO.D | VCTAATTRSYHAWWWWW | 473 | 4.98E-01 | 1.00E+00 | 1.74E-01 | 1.00E+00 | 1.00E+00 | 1.00E+00 |
| FEV_HUMAN.H10MO.C | CAGGAARTDA | 474 | 4.99E-01 | 1.00E+00 | 9.55E-01 | 1.00E+00 | 7.24E-01 | 1.00E+00 |
| OVOL1_HUMAN.H10MO.C | KGTAACKGT | 475 | 5.04E-01 | 1.00E+00 | 7.84E-01 | 1.00E+00 | 7.53E-01 | 1.00E+00 |
| SOX4_HUMAN.H10MO.C | CSCTTTGTTCTC | 476 | 5.08E-01 | 1.00E+00 | 1.96E-01 | 1.00E+00 | 4.94E-01 | 1.00E+00 |
| VSX2_HUMAN.H10MO.D | TAATTAGCTHW | 477 | 5.09E-01 | 1.00E+00 | 5.91E-01 | 1.00E+00 | 9.68E-01 | 1.00E+00 |
| CEBPA_HUMAN.H10MO.A | DRTTGTGCAAYHW | 478 | 5.10E-01 | 1.00E+00 | 5.72E-01 | 1.00E+00 | 9.56E-01 | 1.00E+00 |
| HXC12_HUMAN.H10MO.D | DTTTTAYKACYT | 479 | 5.10E-01 | 1.00E+00 | 4.71E-01 | 1.00E+00 | 9.90E-01 | 1.00E+00 |
| ZBTB4_HUMAN.H10MO.D | CCTAGATGGCAGGTGGG | 480 | 5.11E-01 | 1.00E+00 | 7.54E-01 | 1.00E+00 | 6.31E-02 | 1.00E+00 |
| CXXC1_HUMAN.H10MO.D | CGKTGKY | 481 | 5.16E-01 | 1.00E+00 | 3.20E-01 | 1.00E+00 | 1.79E-04 | 1.08E-01 |
| NFIC_HUMAN.H10MO.A | HYYTGGCWSNVDKCCMR | 482 | 5.18E-01 | 1.00E+00 | 6.70E-01 | 1.00E+00 | 3.05E-01 | 1.00E+00 |
| PEBB_HUMAN.H10MO.C | TYTGTGGTYWB | 483 | 5.19E-01 | 1.00E+00 | 3.87E-01 | 1.00E+00 | 5.80E-01 | 1.00E+00 |
| CEBPD_HUMAN.H10MO.B | RRTKDBGCAAT | 484 | 5.19E-01 | 1.00E+00 | 5.29E-01 | 1.00E+00 | 8.93E-01 | 1.00E+00 |
| SHOX2_HUMAN.H10MO.D | YTAATTRRYYHWWWWWD | 485 | 5.19E-01 | 1.00E+00 | 5.79E-01 | 1.00E+00 | 1.00E+00 | 1.00E+00 |
| MNX1_HUMAN.H10MO.D | MBATTTDHWTHWCYHYTHH | 486 | 5.21E-01 | 1.00E+00 | 8.74E-01 | 1.00E+00 | 8.10E-01 | 1.00E+00 |
| SOX17_HUMAN.H10MO.D | CAAMAATNHHCATTGTCS | 487 | 5.25E-01 | 1.00E+00 | 2.83E-01 | 1.00E+00 | 9.35E-01 | 1.00E+00 |
| JUNB_HUMAN.H10MO.C | GBVTGAGTCAY | 488 | 5.25E-01 | 1.00E+00 | 1.21E-01 | 1.00E+00 | 5.11E-01 | 1.00E+00 |
| LEF1_HUMAN.H10MO.C | CTTTGWW | 489 | 5.28E-01 | 1.00E+00 | 8.95E-02 | 1.00E+00 | 9.62E-01 | 1.00E+00 |
| ELK4_HUMAN.H10MO.A | ACCGGAAGTRN | 490 | 5.33E-01 | 1.00E+00 | 6.78E-01 | 1.00E+00 | 1.94E-01 | 1.00E+00 |
| ASCL2_HUMAN.H10MO.D | KKGRGYRGSTGGKK | 491 | 5.33E-01 | 1.00E+00 | 5.33E-01 | 1.00E+00 | 2.62E-01 | 1.00E+00 |
| HNF1B_HUMAN.H10MO.B | RGTTAATRWTTAAC | 492 | 5.35E-01 | 1.00E+00 | 3.34E-01 | 1.00E+00 | 9.81E-01 | 1.00E+00 |
| FOXA2_HUMAN.H10MO.A | TGTTTACWYWG | 493 | 5.36E-01 | 1.00E+00 | 3.80E-01 | 1.00E+00 | 6.41E-01 | 1.00E+00 |
| NR2F6_HUMAN.H10MO.D | RGGWCAAAGKTCANNKRR | 494 | 5.40E-01 | 1.00E+00 | 5.42E-01 | 1.00E+00 | 7.64E-01 | 1.00E+00 |
| BC11A_HUMAN.H10MO.C | RAAAGAGGAAGTGARAV | 495 | 5.40E-01 | 1.00E+00 | 8.26E-01 | 1.00E+00 | 9.47E-01 | 1.00E+00 |
| HXD13_HUMAN.H10MO.D | TTTATTAGRGA | 496 | 5.43E-01 | 1.00E+00 | 4.03E-01 | 1.00E+00 | 6.13E-01 | 1.00E+00 |
| ZN333_HUMAN.H10MO.D | SKATAATGA | 497 | 5.43E-01 | 1.00E+00 | 6.74E-01 | 1.00E+00 | 9.25E-01 | 1.00E+00 |
| SPI1_HUMAN.H10MO.A | RRAAAGAGGAAGTGARA | 498 | 5.44E-01 | 1.00E+00 | 1.69E-01 | 1.00E+00 | 6.06E-01 | 1.00E+00 |
| HXD9_HUMAN.H10MO.D | ARWTTNATKD | 499 | 5.45E-01 | 1.00E+00 | 8.95E-01 | 1.00E+00 | 9.99E-01 | 1.00E+00 |
| NR1I3_HUMAN.H10MO.S | RAGKTCAB | 500 | 5.52E-01 | 1.00E+00 | 5.89E-01 | 1.00E+00 | 7.59E-01 | 1.00E+00 |
| CEBPG_HUMAN.H10MO.C | ATTDTGCAATCTB | 501 | 5.54E-01 | 1.00E+00 | 9.55E-02 | 1.00E+00 | 9.67E-01 | 1.00E+00 |
| NR4A1_HUMAN.H10MO.C | VAAGGTCAS | 502 | 5.55E-01 | 1.00E+00 | 9.65E-01 | 1.00E+00 | 4.36E-01 | 1.00E+00 |
| ONEC3_HUMAN.H10MO.D | TATYGATTTTTT | 503 | 5.59E-01 | 1.00E+00 | 2.09E-01 | 1.00E+00 | 9.89E-01 | 1.00E+00 |
| SMAD2_HUMAN.H10MO.C | TGTCTGDCACCT | 504 | 5.59E-01 | 1.00E+00 | 5.00E-01 | 1.00E+00 | 4.43E-01 | 1.00E+00 |
| GATA1_HUMAN.H10MO.S | DSAGATAAGR | 505 | 5.62E-01 | 1.00E+00 | 1.76E-01 | 1.00E+00 | 9.96E-01 | 1.00E+00 |

TABLE 5-continued

Transcription Factors with binding sites enriched in: (A) genes up-regulated in lesional skin at baseline; (B) genes down-regulated in lesional skin by week 12 in the placebo group; (C) genes down-regulated in lesional skin by week 12 in the nemo group.

| | | | A. Genes up-regulated in lesional skin at baseline | | B. Genes down-regulated in lesional skin by week 12 in the placebo group | | C. Genes down-regulated in lesional skin by week 12 in the nemo group | |
|---|---|---|---|---|---|---|---|---|
| | Motif | SEQ ID NO | p-value | FDR | p-value | FDR | p-value | FDR |
| IRF3_HUMAN.H10MO.C | GGAAAGBGAAASBRRRA | 506 | 5.63E-01 | 1.00E+00 | 6.41E-01 | 1.00E+00 | 7.95E-01 | 1.00E+00 |
| HES5_HUMAN.H10MO.D | YGGCACGTGYCR | 507 | 5.63E-01 | 1.00E+00 | 6.40E-01 | 1.00E+00 | 2.43E-02 | 1.00E+00 |
| NR2E3_HUMAN.H10MO.C | AAAGTCAAAAGTCA | 508 | 5.63E-01 | 1.00E+00 | 6.81E-01 | 1.00E+00 | 4.67E-01 | 1.00E+00 |
| PAX6_HUMAN.H10MO.D | TSAWGCGTRAA | 509 | 5.68E-01 | 1.00E+00 | 8.00E-01 | 1.00E+00 | 9.77E-01 | 1.00E+00 |
| SOX1_HUMAN.H10MO.D | DATSAATGTTATTSAT | 510 | 5.69E-01 | 1.00E+00 | 7.26E-01 | 1.00E+00 | 8.92E-01 | 1.00E+00 |
| PIT1_HUMAN.H10MO.C | YTMATGAATATWY | 511 | 5.73E-01 | 1.00E+00 | 9.81E-01 | 1.00E+00 | 9.94E-01 | 1.00E+00 |
| PHX2B_HUMAN.H10MO.D | TAATYTAATTA | 512 | 5.74E-01 | 1.00E+00 | 8.68E-01 | 1.00E+00 | 9.98E-01 | 1.00E+00 |
| ARI5B_HUMAN.H10MO.C | DBYKDGTATTSKR | 513 | 5.77E-01 | 1.00E+00 | 3.09E-01 | 1.00E+00 | 4.47E-01 | 1.00E+00 |
| PKNX1_HUMAN.H10MO.D | VRVTTGAYTGATK | 514 | 5.78E-01 | 1.00E+00 | 4.32E-01 | 1.00E+00 | 8.59E-01 | 1.00E+00 |
| TFAP4_HUMAN.H10MO.C | RYCAGCTGYGG | 515 | 5.81E-01 | 1.00E+00 | 3.83E-01 | 1.00E+00 | 7.12E-03 | 9.90E-01 |
| NKX22_HUMAN.H10MO.D | KTYAAGTRSTTD | 516 | 5.81E-01 | 1.00E+00 | 7.73E-01 | 1.00E+00 | 9.88E-01 | 1.00E+00 |
| ISX_HUMAN.H10MO.D | YTAATTRGHTWWWWWW | 517 | 5.84E-01 | 1.00E+00 | 6.65E-01 | 1.00E+00 | 1.00E+00 | 1.00E+00 |
| ETV2_HUMAN.H10MO.D | YNYKRTTTYND | 518 | 5.88E-01 | 1.00E+00 | 6.92E-01 | 1.00E+00 | 8.70E-01 | 1.00E+00 |
| GCM2_HUMAN.H10MO.D | BATGCGGGTAB | 519 | 5.88E-01 | 1.00E+00 | 1.78E-01 | 1.00E+00 | 5.38E-05 | 3.39E-02 |
| COT2_HUMAN.H10MO.S | VAGGTCAARGGTCAM | 520 | 5.92E-01 | 1.00E+00 | 7.49E-01 | 1.00E+00 | 5.03E-02 | 1.00E+00 |
| VAX1_HUMAN.H10MO.D | RSTAATTAGBSTWAWTWW | 521 | 5.93E-01 | 1.00E+00 | 5.21E-01 | 1.00E+00 | 9.84E-01 | 1.00E+00 |
| MLX_HUMAN.H10MO.D | YGATCACGTGN | 522 | 5.99E-01 | 1.00E+00 | 8.87E-01 | 1.00E+00 | 2.66E-01 | 1.00E+00 |
| RARA_HUMAN.H10MO.S | SAGGTCA | 523 | 5.99E-01 | 1.00E+00 | 6.05E-01 | 1.00E+00 | 4.27E-01 | 1.00E+00 |
| MYOG_HUMAN.H10MO.D | TRACAGCTGCWGC | 524 | 6.05E-01 | 1.00E+00 | 2.74E-01 | 1.00E+00 | 2.63E-01 | 1.00E+00 |
| MSX1_HUMAN.H10MO.D | TAATTGSWWKTTAATTGS | 525 | 6.08E-01 | 1.00E+00 | 4.55E-01 | 1.00E+00 | 9.85E-01 | 1.00E+00 |
| HLTF_HUMAN.H10MO.D | KANKGCTGSMAM | 526 | 6.09E-01 | 1.00E+00 | 8.30E-01 | 1.00E+00 | 1.31E-01 | 1.00E+00 |
| BPTF_HUMAN.H10MO.D | KKTBTTGTKKKS | 527 | 6.17E-01 | 1.00E+00 | 1.84E-01 | 1.00E+00 | 9.23E-01 | 1.00E+00 |
| FOXD2_HUMAN.H10MO.D | WAWGTAAATRTTWWYTTAA | 528 | 6.25E-01 | 1.00E+00 | 6.39E-01 | 1.00E+00 | 9.12E-01 | 1.00E+00 |
| BRCA1_HUMAN.H10MO.D | BKTSKGTTG | 529 | 6.26E-01 | 1.00E+00 | 8.73E-01 | 1.00E+00 | 8.75E-01 | 1.00E+00 |
| FOXP3_HUMAN.H10MO.D | AATKTGWTT | 530 | 6.26E-01 | 1.00E+00 | 9.58E-01 | 1.00E+00 | 9.76E-01 | 1.00E+00 |
| GSC_HUMAN.H10MO.D | ADSGGATTARB | 531 | 6.27E-01 | 1.00E+00 | 1.45E-03 | 6.06E-01 | 5.11E-01 | 1.00E+00 |
| HNF4A_HUMAN.H10MO.A | RRGKBCAAAGTYCA | 532 | 6.29E-01 | 1.00E+00 | 6.44E-01 | 1.00E+00 | 3.27E-01 | 1.00E+00 |
| PO3F3_HUMAN.H10MO.D | WWWAWTTATGCWWATTW | 533 | 6.31E-01 | 1.00E+00 | 7.97E-01 | 1.00E+00 | 9.47E-01 | 1.00E+00 |
| NKX32_HUMAN.H10MO.C | AGYTAAGTGGV | 534 | 6.34E-01 | 1.00E+00 | 5.60E-01 | 1.00E+00 | 5.96E-01 | 1.00E+00 |
| BATF3_HUMAN.H10MO.D | HHTYRYTTACGK | 535 | 6.34E-01 | 1.00E+00 | 3.32E-01 | 1.00E+00 | 8.26E-01 | 1.00E+00 |
| UNC4_HUMAN.H10MO.D | TAATTTAATTA | 536 | 6.34E-01 | 1.00E+00 | 2.13E-01 | 1.00E+00 | 1.00E+00 | 1.00E+00 |
| FOXA3_HUMAN.H10MO.C | HTRTTTRYTTWBY | 537 | 6.38E-01 | 1.00E+00 | 5.28E-01 | 1.00E+00 | 8.44E-01 | 1.00E+00 |
| HXD3_HUMAN.H10MO.D | NGKTAATTAGK | 538 | 6.39E-01 | 1.00E+00 | 2.97E-01 | 1.00E+00 | 9.95E-01 | 1.00E+00 |
| NFIA_HUMAN.H10MO.S | MTTGGCW | 539 | 6.45E-01 | 1.00E+00 | 3.59E-01 | 1.00E+00 | 6.30E-01 | 1.00E+00 |

TABLE 5-continued

Transcription Factors with binding sites enriched in: (A) genes up-regulated in lesional skin at baseline; (B) genes down-regulated in lesional skin by week 12 in the placebo group; (C) genes down-regulated in lesional skin by week 12 in the nemo group.

| | Motif | SEQ ID NO | A. Genes up-regulated in lesional skin at baseline p-value | FDR | B. Genes down-regulated in lesional skin by week 12 in the placebo group p-value | FDR | C. Genes down-regulated in lesional skin by week 12 in the nemo group p-value | FDR |
|---|---|---|---|---|---|---|---|---|
| HINFP_HUMAN.H10MO.C | DMSHHMGCGGACGTTV | 540 | 6.54E-01 | 1.00E+00 | 6.72E-02 | 1.00E+00 | 8.80E-03 | 9.97E-01 |
| VENTX_HUMAN.H10MO.D | YVYTAATYGSTTHHHWWTT | 541 | 6.58E-01 | 1.00E+00 | 5.95E-01 | 1.00E+00 | 8.24E-01 | 1.00E+00 |
| TCF7_HUMAN.H10MO.C | ASWWCAAAGSRB | 542 | 6.61E-01 | 1.00E+00 | 6.55E-01 | 1.00E+00 | 9.81E-01 | 1.00E+00 |
| LBX2_HUMAN.H10MO.D | RYTAATTRGBY | 543 | 6.63E-01 | 1.00E+00 | 2.32E-01 | 1.00E+00 | 9.96E-01 | 1.00E+00 |
| PITX3_HUMAN.H10MO.D | RGGGDWTWAAGGGATTAR | 544 | 6.64E-01 | 1.00E+00 | 7.46E-01 | 1.00E+00 | 9.66E-01 | 1.00E+00 |
| HES1_HUMAN.H10MO.D | VMGVCACGMGMCM | 545 | 6.65E-01 | 1.00E+00 | 6.20E-01 | 1.00E+00 | 1.24E-02 | 1.00E+00 |
| HXC6_HUMAN.H10MO.D | ATGATTTATTACTTT | 546 | 6.68E-01 | 1.00E+00 | 5.83E-01 | 1.00E+00 | 5.64E-01 | 1.00E+00 |
| BATF_HUMAN.H10MO.A | ABTYYYRDWATGASTCAK | 547 | 6.69E-01 | 1.00E+00 | 8.32E-01 | 1.00E+00 | 9.55E-01 | 1.00E+00 |
| ZBT7B_HUMAN.H10MO.D | SSCSGTTGCCATGGVRACSGS | 548 | 6.70E-01 | 1.00E+00 | 7.09E-01 | 1.00E+00 | 4.95E-04 | 2.72E-01 |
| MUSC_HUMAN.H10MO.D | CAGAAGACGGCATACGAB | 549 | 6.71E-01 | 1.00E+00 | 3.76E-01 | 1.00E+00 | 7.83E-01 | 1.00E+00 |
| ESX1_HUMAN.H10MO.D | RYTAATTRGYNHWWWTW | 550 | 6.78E-01 | 1.00E+00 | 5.18E-01 | 1.00E+00 | 1.00E+00 | 1.00E+00 |
| FOXM1_HUMAN.H10MO.D | BTTGWKTGWTTWY | 551 | 6.78E-01 | 1.00E+00 | 4.15E-01 | 1.00E+00 | 7.33E-01 | 1.00E+00 |
| HSFY1_HUMAN.H10MO.D | WWTCGAACGWWW | 552 | 6.79E-01 | 1.00E+00 | 3.94E-02 | 1.00E+00 | 9.30E-01 | 1.00E+00 |
| E2F7_HUMAN.H10MO.D | WWDGGCGCGAAAM | 553 | 6.79E-01 | 1.00E+00 | 3.36E-01 | 1.00E+00 | 1.27E-01 | 1.00E+00 |
| MYB_HUMAN.H10MO.C | CAGTTRD | 554 | 6.79E-01 | 1.00E+00 | 8.63E-01 | 1.00E+00 | 8.25E-01 | 1.00E+00 |
| ARI3A_HUMAN.H10MO.S | AATTAAA | 555 | 6.79E-01 | 1.00E+00 | 7.45E-01 | 1.00E+00 | 1.00E+00 | 1.00E+00 |
| MTF1_HUMAN.H10MO.C | MGKGCCGTGTGCAAARS | 556 | 6.80E-01 | 1.00E+00 | 5.10E-01 | 1.00E+00 | 6.53E-02 | 1.00E+00 |
| FOXO3_HUMAN.H10MO.B | KRYTTGTTTWCMK | 557 | 6.80E-01 | 1.00E+00 | 9.48E-01 | 1.00E+00 | 9.90E-01 | 1.00E+00 |
| ARI3A_HUMAN.H10MO.D | RATTAAWBRRWATCAAAWTWWA | 558 | 6.82E-01 | 1.00E+00 | 9.17E-01 | 1.00E+00 | 9.46E-01 | 1.00E+00 |
| THA_HUMAN.H10MO.S | BTSAGGTCAS | 559 | 6.84E-01 | 1.00E+00 | 7.26E-01 | 1.00E+00 | 4.21E-01 | 1.00E+00 |
| MAF_HUMAN.H10MO.B | KTGCTGAC | 560 | 6.85E-01 | 1.00E+00 | 5.90E-01 | 1.00E+00 | 7.92E-01 | 1.00E+00 |
| NF2L1_HUMAN.H10MO.C | NATGACD | 561 | 6.85E-01 | 1.00E+00 | 1.06E-01 | 1.00E+00 | 5.08E-01 | 1.00E+00 |
| STF1_HUMAN.H10MO.B | YCAAGGYCA | 562 | 6.91E-01 | 1.00E+00 | 7.42E-01 | 1.00E+00 | 1.94E-01 | 1.00E+00 |
| P63_HUMAN.H10MO.S | GRRCWTGTCYS | 563 | 7.01E-01 | 1.00E+00 | 1.05E-01 | 1.00E+00 | 4.92E-02 | 1.00E+00 |
| SRY_HUMAN.H10MO.B | YWTTGTTTH | 564 | 7.12E-01 | 1.00E+00 | 9.33E-01 | 1.00E+00 | 9.66E-01 | 1.00E+00 |
| GCM1_HUMAN.H10MO.D | HWVATGCKGGYMBK | 565 | 7.14E-01 | 1.00E+00 | 8.45E-01 | 1.00E+00 | 2.58E-01 | 1.00E+00 |
| HLF_HUMAN.H10MO.C | GRTTRYGTAAYMS | 566 | 7.20E-01 | 1.00E+00 | 9.62E-01 | 1.00E+00 | 9.96E-01 | 1.00E+00 |
| PO2F2_HUMAN.H10MO.D | WMATTTGCATAWTYAW | 567 | 7.20E-01 | 1.00E+00 | 9.38E-01 | 1.00E+00 | 9.96E-01 | 1.00E+00 |
| VDR_HUMAN.H10MO.S | GRGKTCA | 568 | 7.25E-01 | 1.00E+00 | 6.33E-01 | 1.00E+00 | 2.91E-01 | 1.00E+00 |
| PPARA_HUMAN.H10MO.S | RAGGTCA | 569 | 7.25E-01 | 1.00E+00 | 7.65E-01 | 1.00E+00 | 5.21E-01 | 1.00E+00 |
| RUNX3_HUMAN.H10MO.C | NTYTGTGGTTW | 570 | 7.26E-01 | 1.00E+00 | 4.49E-01 | 1.00E+00 | 9.34E-01 | 1.00E+00 |
| ALX4_HUMAN.H10MO.D | TAATYTAATTAR | 571 | 7.27E-01 | 1.00E+00 | 5.04E-01 | 1.00E+00 | 1.00E+00 | 1.00E+00 |
| EPAS1_HUMAN.H10MO.D | GTGHRTRCGTGKG | 572 | 7.27E-01 | 1.00E+00 | 4.14E-01 | 1.00E+00 | 4.96E-03 | 9.59E-01 |

TABLE 5-continued

Transcription Factors with binding sites enriched in: (A) genes up-regulated in lesional skin at baseline; (B) genes down-regulated in lesional skin by week 12 in the placebo group; (C) genes down-regulated in lesional skin by week 12 in the nemo group.

| | Motif | SEQ ID NO | A. Genes up-regulated in lesional skin at baseline p-value | A. FDR | B. Genes down-regulated in lesional skin by week 12 in the placebo group p-value | B. FDR | C. Genes down-regulated in lesional skin by week 12 in the nemo group p-value | C. FDR |
|---|---|---|---|---|---|---|---|---|
| ATF2_HUMAN.H10MO.B | VTGACGTMA | 573 | 7.29E-01 | 1.00E+00 | 2.47E-01 | 1.00E+00 | 2.64E-01 | 1.00E+00 |
| FOXJ3_HUMAN.H10MO.A | TTGTTTATKKTTW | 574 | 7.29E-01 | 1.00E+00 | 1.32E-01 | 1.00E+00 | 8.06E-01 | 1.00E+00 |
| NKX31_HUMAN.H10MO.C | WWTAAGTATWTWW | 575 | 7.31E-01 | 1.00E+00 | 2.79E-01 | 1.00E+00 | 9.71E-01 | 1.00E+00 |
| MBD2_HUMAN.H10MO.B | SSGKCCGGMGR | 576 | 7.35E-01 | 1.00E+00 | 2.56E-01 | 1.00E+00 | 3.79E-06 | 2.42E-03 |
| HNF4G_HUMAN.H10MO.C | VRGKNCAAAGKYCA | 577 | 7.35E-01 | 1.00E+00 | 5.81E-01 | 1.00E+00 | 5.49E-01 | 1.00E+00 |
| TYY2_HUMAN.H10MO.D | AWAATGGCGGH | 578 | 7.38E-01 | 1.00E+00 | 5.86E-01 | 1.00E+00 | 1.07E-01 | 1.00E+00 |
| BARX2_HUMAN.H10MO.D | TYRWTAATKR | 579 | 7.42E-01 | 1.00E+00 | 2.83E-01 | 1.00E+00 | 9.99E-01 | 1.00E+00 |
| HNF1A_HUMAN.H10MO.A | RGTTAATMWTTAMCM | 580 | 7.49E-01 | 1.00E+00 | 3.25E-01 | 1.00E+00 | 9.91E-01 | 1.00E+00 |
| MAFG_HUMAN.H10MO.S | MATGACT | 581 | 7.56E-01 | 1.00E+00 | 5.47E-01 | 1.00E+00 | 7.62E-01 | 1.00E+00 |
| DLX1_HUMAN.H10MO.D | WWWWWTATGSTAATTA | 582 | 7.60E-01 | 1.00E+00 | 5.55E-01 | 1.00E+00 | 8.77E-01 | 1.00E+00 |
| GCR_HUMAN.H10MO.A | RGRACABKSTGTYCY | 583 | 7.62E-01 | 1.00E+00 | 8.41E-01 | 1.00E+00 | 8.90E-01 | 1.00E+00 |
| NRF1_HUMAN.H10MO.A | SYGCGCMTGCGCRSBGSS | 584 | 7.64E-01 | 1.00E+00 | 8.11E-01 | 1.00E+00 | 1.35E-06 | 8.62E-04 |
| FOXG1_HUMAN.H10MO.D | DTTGTTTAYDTWTDTTT | 585 | 7.70E-01 | 1.00E+00 | 2.22E-01 | 1.00E+00 | 6.43E-01 | 1.00E+00 |
| MIXL1_HUMAN.H10MO.D | GBTAATTARAT | 586 | 7.70E-01 | 1.00E+00 | 1.04E-01 | 1.00E+00 | 9.96E-01 | 1.00E+00 |
| IRF4_HUMAN.H10MO.C | RRRGRGGAASTGARAS | 587 | 7.70E-01 | 1.00E+00 | 7.37E-01 | 1.00E+00 | 2.51E-01 | 1.00E+00 |
| SOX11_HUMAN.H10MO.D | AACAMTGMMATTGTTB | 588 | 7.71E-01 | 1.00E+00 | 9.97E-01 | 1.00E+00 | 9.99E-01 | 1.00E+00 |
| NGN2_HUMAN.H10MO.D | AMCATATGYYWHH | 589 | 7.71E-01 | 1.00E+00 | 2.73E-02 | 1.00E+00 | 9.99E-01 | 1.00E+00 |
| LHX3_HUMAN.H10MO.C | AAAATTAATTARY | 590 | 7.74E-01 | 1.00E+00 | 5.05E-01 | 1.00E+00 | 1.00E+00 | 1.00E+00 |
| PO6F2_HUMAN.H10MO.D | KWTAATKAGST | 591 | 7.77E-01 | 1.00E+00 | 9.52E-01 | 1.00E+00 | 9.88E-01 | 1.00E+00 |
| SOX3_HUMAN.H10MO.D | WSAATGBWATTSW | 592 | 7.79E-01 | 1.00E+00 | 7.13E-01 | 1.00E+00 | 9.40E-01 | 1.00E+00 |
| MEF2B_HUMAN.H10MO.D | TGTTRCTATWWATAGC | 593 | 7.79E-01 | 1.00E+00 | 7.90E-01 | 1.00E+00 | 9.83E-01 | 1.00E+00 |
| AIRE_HUMAN.H10MO.C | HTTGGWWWWAWTGGDTWH | 594 | 7.80E-01 | 1.00E+00 | 7.86E-01 | 1.00E+00 | 9.97E-01 | 1.00E+00 |
| GFI1B_HUMAN.H10MO.C | WGCAGTGATTT | 595 | 7.80E-01 | 1.00E+00 | 9.63E-01 | 1.00E+00 | 9.94E-01 | 1.00E+00 |
| BHE22_HUMAN.H10MO.D | AVCATATGTTTTT | 596 | 7.81E-01 | 1.00E+00 | 3.51E-01 | 1.00E+00 | 1.00E+00 | 1.00E+00 |
| PO2F1_HUMAN.H10MO.B | HATGCAAAT | 597 | 7.82E-01 | 1.00E+00 | 5.31E-01 | 1.00E+00 | 9.90E-01 | 1.00E+00 |
| RORG_HUMAN.H10MO.C | DWAWGTRGGTCAG | 598 | 7.83E-01 | 1.00E+00 | 4.66E-01 | 1.00E+00 | 9.62E-01 | 1.00E+00 |
| TYY1_HUMAN.H10MO.A | CAARATGGCGGC | 599 | 7.84E-01 | 1.00E+00 | 5.94E-01 | 1.00E+00 | 9.92E-01 | 1.00E+00 |
| IRF5_HUMAN.H10MO.D | KAAAGGRAARCMAAAWSWGA | 600 | 7.86E-01 | 1.00E+00 | 7.64E-01 | 1.00E+00 | 7.65E-01 | 1.00E+00 |
| TBX19_HUMAN.H10MO.D | WWTTCRCACVTAGGTGTGAAWW | 601 | 7.93E-01 | 1.00E+00 | 7.59E-01 | 1.00E+00 | 1.00E+00 | 1.00E+00 |
| HMX2_HUMAN.H10MO.D | DTTAAKTGNTT | 602 | 7.95E-01 | 1.00E+00 | 9.73E-01 | 1.00E+00 | 1.00E+00 | 1.00E+00 |
| CREB1_HUMAN.H10MO.A | TKACGTCAYYN | 603 | 8.01E-01 | 1.00E+00 | 6.69E-01 | 1.00E+00 | 8.64E-01 | 1.00E+00 |
| RARB_HUMAN.H10MO.D | SAGGTCAVVVV | 604 | 8.09E-01 | 1.00E+00 | 3.90E-01 | 1.00E+00 | 1.98E-01 | 1.00E+00 |
| FOXO6_HUMAN.H10MO.D | WWSWTGTTTACRT | 605 | 8.11E-01 | 1.00E+00 | 5.16E-01 | 1.00E+00 | 9.93E-01 | 1.00E+00 |

TABLE 5-continued

Transcription Factors with binding sites enriched in: (A) genes up-regulated in lesional skin at baseline; (B) genes down-regulated in lesional skin by week 12 in the placebo group; (C) genes down-regulated in lesional skin by week 12 in the nemo group.

| Motif | | SEQ ID NO | A. Genes up-regulated in lesional skin at baseline p-value | FDR | B. Genes down-regulated in lesional skin by week 12 in the placebo group p-value | FDR | C. Genes down-regulated in lesional skin by week 12 in the nemo group p-value | FDR |
|---|---|---|---|---|---|---|---|---|
| KAISO_HUMAN.H10MO.A | GYTCTCGCGAGRBYBVGGS | 606 | 8.12E-01 | 1.00E+00 | 3.15E-01 | 1.00E+00 | 6.06E-05 | 3.81E-02 |
| NOTO_HUMAN.H10MO.D | RTTAATTAGNT | 607 | 8.18E-01 | 1.00E+00 | 6.01E-01 | 1.00E+00 | 1.00E+00 | 1.00E+00 |
| DDIT3_HUMAN.H10MO.C | GGGGATTGCAYBB | 608 | 8.26E-01 | 1.00E+00 | 3.36E-01 | 1.00E+00 | 6.62E-02 | 1.00E+00 |
| RAX2_HUMAN.H10MO.D | YTAATTARATWA | 609 | 8.33E-01 | 1.00E+00 | 6.73E-01 | 1.00E+00 | 1.00E+00 | 1.00E+00 |
| TF7L2_HUMAN.H10MO.A | KBYCTTTGAWSTB | 610 | 8.34E-01 | 1.00E+00 | 9.27E-01 | 1.00E+00 | 9.95E-01 | 1.00E+00 |
| ARX_HUMAN.H10MO.D | YTAATYTAATTAR | 611 | 8.38E-01 | 1.00E+00 | 9.03E-01 | 1.00E+00 | 1.00E+00 | 1.00E+00 |
| ZBTB4_HUMAN.H10MO.S | CAATRGCGDTKGYGR | 612 | 8.41E-01 | 1.00E+00 | 5.91E-01 | 1.00E+00 | 5.40E-02 | 1.00E+00 |
| ERR2_HUMAN.H10MO.A | YCAAGGTCA | 613 | 8.42E-01 | 1.00E+00 | 3.55E-01 | 1.00E+00 | 5.21E-01 | 1.00E+00 |
| HXC11_HUMAN.H10MO.D | DTTTWAYGACY | 614 | 8.42E-01 | 1.00E+00 | 7.24E-01 | 1.00E+00 | 9.96E-01 | 1.00E+00 |
| LHX4_HUMAN.H10MO.D | DNRYTAATTRN | 615 | 8.43E-01 | 1.00E+00 | 2.59E-01 | 1.00E+00 | 1.00E+00 | 1.00E+00 |
| FOXL1_HUMAN.H10MO.D | TKTTTGTTTRTTTAYWTTT | 616 | 8.43E-01 | 1.00E+00 | 4.21E-01 | 1.00E+00 | 8.37E-01 | 1.00E+00 |
| HXD11_HUMAN.H10MO.D | DWTTTATKRHN | 617 | 8.51E-01 | 1.00E+00 | 7.84E-01 | 1.00E+00 | 9.99E-01 | 1.00E+00 |
| FOXJ3_HUMAN.H10MO.S | TKKTTWWTGTTTA | 618 | 8.61E-01 | 1.00E+00 | 4.31E-01 | 1.00E+00 | 8.51E-01 | 1.00E+00 |
| RUNX2_HUMAN.H10MO.B | YTGTGGTTDGK | 619 | 8.62E-01 | 1.00E+00 | 6.40E-01 | 1.00E+00 | 5.57E-01 | 1.00E+00 |
| SOX21_HUMAN.H10MO.D | RAACAATGKYAKTGTT | 620 | 8.63E-01 | 1.00E+00 | 6.68E-01 | 1.00E+00 | 9.99E-01 | 1.00E+00 |
| DLX2_HUMAN.H10MO.D | ATAATTRB | 621 | 8.65E-01 | 1.00E+00 | 9.31E-01 | 1.00E+00 | 1.00E+00 | 1.00E+00 |
| ISL1_HUMAN.H10MO.D | SYTAATR | 622 | 8.67E-01 | 1.00E+00 | 6.86E-01 | 1.00E+00 | 9.98E-01 | 1.00E+00 |
| E2F3_HUMAN.H10MO.B | SSCGCSAAAC | 623 | 8.75E-01 | 1.00E+00 | 9.77E-01 | 1.00E+00 | 2.29E-04 | 1.36E-01 |
| PO4F2_HUMAN.H10MO.D | YATTAATGAGYTK | 624 | 8.78E-01 | 1.00E+00 | 3.40E-01 | 1.00E+00 | 9.96E-01 | 1.00E+00 |
| HXA7_HUMAN.H10MO.D | VMTCRATMGATTGGM | 625 | 8.80E-01 | 1.00E+00 | 3.09E-01 | 1.00E+00 | 9.52E-01 | 1.00E+00 |
| IRF7_HUMAN.H10MO.C | GAAASYGAAA | 626 | 8.83E-01 | 1.00E+00 | 9.45E-01 | 1.00E+00 | 9.44E-01 | 1.00E+00 |
| ALX3_HUMAN.H10MO.D | TAATYTAATTA | 627 | 8.85E-01 | 1.00E+00 | 5.22E-01 | 1.00E+00 | 1.00E+00 | 1.00E+00 |
| ZKSC3_HUMAN.H10MO.D | TYCGAGGCTAG | 628 | 8.85E-01 | 1.00E+00 | 6.47E-02 | 1.00E+00 | 2.09E-01 | 1.00E+00 |
| ZN410_HUMAN.H10MO.D | TATTATGGGATGK | 629 | 8.88E-01 | 1.00E+00 | 7.98E-01 | 1.00E+00 | 9.69E-01 | 1.00E+00 |
| MGAP_HUMAN.H10MO.D | AGGTGTGAAWTTTCAC | 630 | 8.98E-01 | 1.00E+00 | 8.39E-01 | 1.00E+00 | 1.00E+00 | 1.00E+00 |
| OLIG1_HUMAN.H10MO.D | AMCATATGTTTTTY | 631 | 8.98E-01 | 1.00E+00 | 8.26E-01 | 1.00E+00 | 1.00E+00 | 1.00E+00 |
| CUX1_HUMAN.H10MO.C | RBRSBDATCGATSK | 632 | 9.00E-01 | 1.00E+00 | 2.03E-01 | 1.00E+00 | 9.97E-01 | 1.00E+00 |
| CPEB1_HUMAN.H10MO.D | TTTTTATTYTTTTTTTT | 633 | 9.02E-01 | 1.00E+00 | 7.57E-01 | 1.00E+00 | 9.55E-01 | 1.00E+00 |
| HSF4_HUMAN.H10MO.D | TRGAABVTTCTAGAA | 634 | 9.06E-01 | 1.00E+00 | 5.87E-01 | 1.00E+00 | 9.42E-01 | 1.00E+00 |
| HMGA1_HUMAN.H10MO.D | NWATTTT | 635 | 9.10E-01 | 1.00E+00 | 8.55E-01 | 1.00E+00 | 9.94E-01 | 1.00E+00 |
| CDC5L_HUMAN.H10MO.D | GBGWKTTAAYRTAWY | 636 | 9.14E-01 | 1.00E+00 | 1.68E-01 | 1.00E+00 | 1.00E+00 | 1.00E+00 |
| MEF2A_HUMAN.H10MO.A | DKCTATTTTTRGM | 637 | 9.23E-01 | 1.00E+00 | 7.31E-01 | 1.00E+00 | 9.85E-01 | 1.00E+00 |
| SUH_HUMAN.H10MO.C | SYGTGRGAAMN | 638 | 9.25E-01 | 1.00E+00 | 1.24E-01 | 1.00E+00 | 9.64E-01 | 1.00E+00 |
| BRAC_HUMAN.H10MO.D | RSAWWGTGACACCTAGGTG | 639 | 9.30E-01 | 1.00E+00 | 8.40E-01 | 1.00E+00 | 9.50E-01 | 1.00E+00 |

TABLE 5-continued

Transcription Factors with binding sites enriched in: (A) genes up-regulated in lesional skin at baseline; (B) genes down-regulated in lesional skin by week 12 in the placebo group; (C) genes down-regulated in lesional skin by week 12 in the nemo group.

| | Motif | SEQ ID NO | A. Genes up-regulated in lesional skin at baseline p-value | A. FDR | B. Genes down-regulated in lesional skin by week 12 in the placebo group p-value | B. FDR | C. Genes down-regulated in lesional skin by week 12 in the nemo group p-value | C. FDR |
|---|---|---|---|---|---|---|---|---|
| | TGAAAT | | | | | | | |
| SOX7_HUMAN.H10MO.D | AACAMTGMAATTGTTY | 640 | 9.31E-01 | 1.00E+00 | 9.99E-01 | 1.00E+00 | 1.00E+00 | 1.00E+00 |
| FOXO4_HUMAN.H10MO.C | TTGTTTAYK | 641 | 9.31E-01 | 1.00E+00 | 4.60E-01 | 1.00E+00 | 9.48E-01 | 1.00E+00 |
| CUX2_HUMAN.H10MO.D | DATCRATWHDDTTATCGATYA | 642 | 9.34E-01 | 1.00E+00 | 4.81E-01 | 1.00E+00 | 9.99E-01 | 1.00E+00 |
| HXD12_HUMAN.H10MO.D | DDTTTTAHKRN | 643 | 9.35E-01 | 1.00E+00 | 9.39E-01 | 1.00E+00 | 9.99E-01 | 1.00E+00 |
| ETV3_HUMAN.H10MO.D | KWMRTTTGCACTTC | 644 | 9.40E-01 | 1.00E+00 | 1.41E-01 | 1.00E+00 | 9.77E-01 | 1.00E+00 |
| ZFHX3_HUMAN.H10MO.D | ATTAWTAATTA | 645 | 9.44E-01 | 1.00E+00 | 6.89E-01 | 1.00E+00 | 1.00E+00 | 1.00E+00 |
| CENPB_HUMAN.H10MO.D | TTCGTWSBAHGCGGGWW | 646 | 9.44E-01 | 1.00E+00 | 9.87E-01 | 1.00E+00 | 3.76E-02 | 1.00E+00 |
| BHE23_HUMAN.H10MO.D | RRSRTRTGKTDB | 647 | 9.48E-01 | 1.00E+00 | 6.47E-01 | 1.00E+00 | 9.81E-01 | 1.00E+00 |
| IRF8_HUMAN.H10MO.D | GRGRAAVTGAAASYR | 648 | 9.55E-01 | 1.00E+00 | 8.92E-01 | 1.00E+00 | 9.85E-01 | 1.00E+00 |
| MSX2_HUMAN.H10MO.D | TAATTDK | 649 | 9.61E-01 | 1.00E+00 | 6.99E-01 | 1.00E+00 | 9.37E-01 | 1.00E+00 |
| SOX9_HUMAN.H10MO.B | YCCATTGTTYT | 650 | 9.68E-01 | 1.00E+00 | 5.15E-01 | 1.00E+00 | 9.91E-01 | 1.00E+00 |
| BHA15_HUMAN.H10MO.D | BDCCATATGKT | 651 | 9.81E-01 | 1.00E+00 | 7.94E-01 | 1.00E+00 | 9.98E-01 | 1.00E+00 |
| HXC10_HUMAN.H10MO.D | WWWWWWWNNWTTTWATKRC | 652 | 9.83E-01 | 1.00E+00 | 6.76E-01 | 1.00E+00 | 9.97E-01 | 1.00E+00 |
| MCR_HUMAN.H10MO.D | HAGDMCWGGTTGWDGTR | 653 | 9.91E-01 | 1.00E+00 | 9.73E-01 | 1.00E+00 | 9.97E-01 | 1.00E+00 |
| HOMEZ_HUMAN.H10MO.D | WWWAATCGTTTTYTW | 654 | 9.97E-01 | 1.00E+00 | 9.75E-01 | 1.00E+00 | 9.88E-01 | 1.00E+00 |

Table 5 discloses SEQ ID NOS 15-444, 558, and 445-557, respectively, in order of appearance.

The invention claimed is:

1. A method of treating prurigo nodularis (PN) in a subject, comprising administering to a subject with PN an anti-IL-31RA antibody (i) at an initial dose of 60 mg of the anti-IL-31RA antibody followed by subsequent serial doses of 30 mg once every 4 weeks if the subject weighs less than 90 kg, or (ii) at an initial dose of 60 mg of the anti-IL-31RA antibody followed by subsequent serial doses of 60 mg once every 4 weeks if the subject weighs 90 kg or more, wherein the subject differentially expresses at least three genes selected from KRT6C, DEFB4A, KRT16, LCE5A, AQP7, IL36A, IL36G, IL19, IL20, IL22, IL24, and IL26 compared to a reference level of expression for the at least three genes, wherein the reference level is the level of expression in a person that does not have PN, wherein the anti-IL-31RA antibody comprises a heavy chain variable region comprising a HCDR1 comprising SEQ ID NO: 8, a HCDR2 comprising SEQ ID NO: 9, and a HCDR3 comprising SEQ ID NO: 10, and a light chain variable region comprising a LCDR1 comprising SEQ ID NO: 12, a LCDR2 comprising SEQ ID NO: 13, and a LCDR3 comprising SEQ ID NO: 14.

2. A method of normalizing differentially expressed genes (DEGs) in a subject with PN, comprising administering to a subject with prurigo nodularis (PN) an anti-IL-31RA antibody (i) at an initial dose of 60 mg of the anti-IL-31RA antibody followed by subsequent serial doses of 30 mg once every 4 weeks if the subject weighs less than 90 kg, or (ii) at an initial dose of 60 mg of the anti-IL-31RA antibody followed by subsequent serial doses of 60 mg once every 4 weeks if the subject weighs 90 kg or more, wherein the subject differentially expresses at least three genes selected from KRT6C, DEFB4A, KRT16, LCE5A, AQP7, IL36A, IL36G, IL19, IL20, IL22, IL24, and IL26 compared to a reference level of expression for the at least three genes and wherein administration of the anti-IL-31RA antibody normalizes the expression level of the at least one gene, wherein the reference level is the level of expression in a person that does not have PN, and wherein normalization is determined about 4 weeks after the initial dose of the anti-IL-31RA antibody, wherein the anti-IL-31RA antibody comprises a heavy chain variable region comprising a HCDR1 comprising SEQ ID NO: 8, a HCDR2 comprising SEQ ID NO: 9, and a HCDR3 comprising SEQ ID NO: 10, and a light chain variable region comprising a LCDR1 comprising SEQ ID NO: 12, a LCDR2 comprising SEQ ID NO: 13, and a LCDR3 comprising SEQ ID NO: 14.

3. The method of claim 1, wherein differential expression of the at least one gene was determined by RT-qPCR, RT-PCR, RNA-seq, Northern blotting, Serial Analysis of Gene Expression (SAGE), or DNA or RNA microarrays; or wherein differential expression of the at least one gene was determined at protein level by Western blotting, ELISA, surface plasmon resonance, or mass spectrometry.

4. The method of claim 1, wherein at least four of KRT6C, DEFB4A, KRT16, LCE5A, AQP7, IL36A, IL36G, IL19, IL20, IL22, IL24, and IL26 are differentially expressed.

5. The method of claim 1, wherein KRT6C, DEFB4A, KRT16, LCE5A, AQP7, IL36A, IL36G, IL19, IL20, IL22, IL24, and IL26 are differentially expressed.

6. The method of claim 1, wherein KRT6C, DEFB4A, and/or KRT16 are overexpressed compared to a reference level of expression.

7. The method of claim 1, wherein LCE5A and/or AQP7 are under expressed compared to a reference level of expression.

8. The method of claim 1, wherein the subject possesses a PN skin gene ontology selected from a cornified envelope, epidermal-cell differentiation, keratinization, peptidase regulatory activity, interleukin-4 and interleukin-13 signaling, interferon alpha/beta signaling, response to interferon gamma, IL23 pathway, and mitotic metaphase and anaphase.

9. The method of claim 1, wherein the anti-IL-31RA antibody is administered subcutaneously.

10. The method of claim 1, wherein the anti-IL-31RA antibody is administered at an initial dose of 60 mg of the anti-IL-31RA antibody followed by 60 mg once every 4 weeks if the subject weighs 90 kg or more.

11. The method of claim 1, wherein the anti-IL-31RA antibody is administered at an initial dose of 60 mg of the anti-IL-31RA antibody followed by 30 mg once every 4 weeks if the subject weighs less than 90 kg.

12. The method of claim 1, wherein pruritus scoring is improved in the subject.

13. The method of claim 1, wherein the HCDR1 consists of the amino acid sequence of SEQ ID NO: 8, the HCDR2 consists of the amino acid sequence of SEQ ID NO: 9, and the HCDR3 consists of the amino acid sequence of SEQ ID NO: 10, the LCDR1 consists of the amino acid sequence of SEQ ID NO: 12, the LCDR2 consists of the amino acid sequence of SEQ ID NO: 13, and the LCDR3 consists of the amino acid sequence of SEQ ID NO: 14.

14. The method of claim 1, wherein the anti-IL-31RA antibody is nemolizumab or a fragment or variant thereof.

15. The method of claim 14, wherein the anti-IL-31RA antibody is nemolizumab.

16. A method of determining whether a subject with prurigo nodularis (PN) is responding to treatment with an anti-IL-31RA antibody, comprising detecting in a post-treatment sample obtained from a subject with PN about 4 weeks after administration of at least one dose of an anti-IL-31RA antibody the expression level of at least three differentially expressed genes (DEGs) selected from KRT6C, DEFB4A, KRT16, LCE5A, AQP7, IL36A, IL36G, IL19, IL20, IL22, IL24, and IL26, and comparing the expression level of the DEGs to a baseline level of expression, wherein the baseline level of gene expression is from a sample from the same individual before treatment was commenced; wherein the at least one dose is 60 mg of the anti-IL-31RA antibody, wherein the anti-IL-31RA antibody comprises a heavy chain variable region comprising a HCDR1 comprising SEQ ID NO: 8, a HCDR2 comprising SEQ ID NO: 9, and a HCDR3 comprising SEQ ID NO: 10, and a light chain variable region comprising a LCDR1 comprising SEQ ID NO: 12, a LCDR2 comprising SEQ ID NO: 13, and a LCDR3 comprising SEQ ID NO: 14, and wherein the anti-IL-31RA antibody is administered (i) at an initial dose of 60 mg of the anti-IL-31RA antibody followed by subsequent serial doses of 30 mg once every 4 weeks if the subject weighs less than 90 kg, or (ii) at an initial dose of 60 mg of the anti-IL-31RA antibody followed by subsequent serial doses of 60 mg once every 4 weeks if the subject weighs 90 kg or more.

17. A method of treating prurigo nodularis (PN) in a subject, comprising administering to a subject with PN an anti-IL-31RA antibody (i) at an initial dose of 60 mg of the anti-IL-31RA antibody followed by subsequent serial doses of 30 mg once every 4 weeks if the subject weighs less than 90 kg, or (ii) at an initial dose of 60 mg of the anti-IL-31RA antibody followed by subsequent serial doses of 60 mg once every 4 weeks if the subject weighs 90 kg or more, wherein treatment with the anti-IL-31RA antibody results in at least one of the following relative to (i) a control plasma sample obtained from an individual or individuals without PN or (ii) a plasma sample obtained from the subject prior to administration of the anti-IL-31RA antibody:

(a) an inhibition of a STAT3 pathway;
(b) an inhibition of a STAT5b pathway;
(c) a downregulation of IL-6 or an IL-6 pathway;
(d) a downregulation of VEGF or a VEGF pathway;
(e) a decrease in TGFB1 pathway activation, or
(f) a combination thereof;

wherein the anti-IL-31RA antibody comprises a heavy chain variable region comprising a HCDR1 comprising SEQ ID NO: 8, a HCDR2 comprising SEQ ID NO: 9, and a HCDR3 comprising SEQ ID NO: 10, and a light chain variable region comprising a LCDR1 comprising SEQ ID NO: 12, a LCDR2 comprising SEQ ID NO: 13, and a LCDR3 comprising SEQ ID NO: 14, and wherein (a) the inhibition of a STAT3 pathway; (b) the inhibition of a STAT5b pathway; (c) the downregulation of IL-6 or an IL-6 pathway; (d) the downregulation of VEGF or a VEGF pathway; (e) the decrease in TGFB1 pathway activation, or (f) the combination thereof is assessed in a plasma sample from the subject taken after about 4 weeks after the initial dose of the anti-IL-31RA antibody.

18. The method of claim 17, wherein (a) the inhibition of a STAT3 pathway; (b) the inhibition of a STAT5b pathway; (c) the downregulation of IL-6 or an IL-6 pathway; (d) the downregulation of VEGF or a VEGF pathway; (e) the decrease in TGFB1 pathway activation, or (f) the combination thereof is determined by mass spectrometry performed on one or more biological sample(s) obtained from the subject.

19. The method of claim 17, wherein the subject exhibits at least two of (a) the inhibition of a STAT3 pathway; (b) the inhibition of a STAT5b pathway; (c) the downregulation of IL-6 or an IL-6 pathway; (d) the downregulation of VEGF or a VEGF pathway; and (e) the decrease in TGFB1 pathway activation.

20. The method of claim 17, wherein at least 4 weeks after administration of the anti-IL-31RA antibody, the subject additionally exhibits at least two of (a) a decrease in migration of leukocytes or cell movement of leukocytes; (b) an inhibition of a STAT3 pathway; (c) an inhibition of a STAT5b pathway; (d) a decrease in TGFB1 pathway activation.

21. The method of claim 17, wherein the anti-IL-31RA antibody is administered subcutaneously.

22. The method of claim 17, wherein the anti-IL-31RA antibody is administered at an initial dose of 60 mg of the anti-IL-31RA antibody followed by subsequent serial doses of 60 mg once every 4 weeks if the subject weighs 90 kg or more.

23. The method of claim 17, wherein the anti-IL-31RA antibody is administered at an initial dose of 60 mg of the anti-IL-31RA antibody followed by subsequent serial doses of 60 mg once every 4 weeks if the subject weighs 90 kg or more.

24. The method of claim 17, wherein pruritus scoring is improved in the subject.

25. The method of claim 17, wherein the anti-IL-31RA antibody is nemolizumab or a fragment or variant thereof.

26. The method of claim 25, wherein the anti-IL-31RA antibody is nemolizumab.

27. A method of altering an immune response in a subject with PN, comprising administering to a subject with PN an anti-IL-31RA antibody (i) at an initial dose of 60 mg of the anti-IL-31RA antibody followed by subsequent serial doses of 30 mg once every 4 weeks if the subject weighs less than 90 kg, or (ii) at an initial dose of 60 mg of the anti-IL-31RA antibody followed by subsequent serial doses of 60 mg once every 4 weeks if the subject weighs 90 kg or more, wherein administration of the anti-IL-31RA antibody results in at least one of the following relative to (i) a control plasma sample obtained from an individual or individuals without PN or (ii) a plasma sample obtained from the subject prior to administration of the anti-IL-31RA antibody:

(a) an inhibition of a STAT3 pathway;
(b) an inhibition of a STAT5b pathway;
(c) a downregulation of IL-6 or an IL-6 pathway;
(d) a downregulation of VEGF or a VEGF pathway;
(e) a decrease in TGFB1 pathway activation, or
(f) a combination thereof;

wherein the anti-IL-31RA antibody comprises a heavy chain variable region comprising a HCDR1 comprising SEQ ID NO: 8, a HCDR2 comprising SEQ ID NO: 9, and a HCDR3 comprising SEQ ID NO: 10, and a light chain variable region comprising a LCDR1 comprising SEQ ID NO: 12, a LCDR2 comprising SEQ ID NO: 13, and a LCDR3 comprising SEQ ID NO: 14, and wherein (a) the inhibition of a STAT3 pathway; (b) the inhibition of a STAT5b pathway; (c) the downregulation of IL-6 or an IL-6 pathway; (d) the downregulation of VEGF or a VEGF pathway; (e) the decrease in TGFB1 pathway activation, or (f) the combination thereof is assessed in a plasma sample from the subject taken after about 4 weeks after the initial dose of the anti-IL-31RA antibody.

28. A method of determining whether a subject with prurigo nodularis (PN) is responding to treatment with an anti-IL-31RA antibody, comprising detecting, using mass spectroscopy, in a post-treatment plasma sample obtained from a subject with PN that has been administered at least one dose of an anti-IL-31RA antibody the amount of at least one of:

(a) an inhibition of a STAT3 pathway;
(b) an inhibition of a STAT5b pathway;
(c) a downregulation of IL-6 or an IL-6 pathway;
(d) a downregulation of VEGF or a VEGF pathway;
(e) a decrease in TGFB1 pathway activation, or
(f) a combination thereof, where the decrease or inhibition is measured relative to a baseline amount and the decrease or inhibition indicates responsiveness to treatment, wherein the baseline amount was determined from a plasma sample obtained from the same subject before treatment was commenced, and wherein treatment with the anti-IL-31RA antibody comprises administering the anti-IL-31RA antibody (i) at an initial dose of 60 mg of the anti-IL-31RA antibody followed by subsequent serial doses of 30 mg once every 4 weeks if the subject weighs less than 90 kg, or (ii) at an initial dose of 60 mg of the anti-IL-31RA antibody followed by subsequent serial doses of 60 mg once every 4 weeks if the subject weighs 90 kg or more.

* * * * *